(12) United States Patent
Jeon et al.

(10) Patent No.: US 12,209,100 B2
(45) Date of Patent: Jan. 28, 2025

(54) HETEROCYCLIC COMPOUND, ORGANIC LIGHT-EMITTING DEVICE INCLUDING HETEROCYCLIC COMPOUND, AND ELECTRONIC APPARATUS INCLUDING ORGANIC LIGHT-EMITTING DEVICE

(71) Applicants: Samsung Electronics Co., Ltd., Suwon-si (KR); Research & Business Foundation SUNGKYUNKWAN UNIVERSITY, Suwon-si (KR)

(72) Inventors: Soonok Jeon, Suwon-si (KR); Junyeob Lee, Seongnam-si (KR); Halim Lee, Seongnam-si (KR); Jihoon Kang, Suwon-si (KR); Inkoo Kim, Suwon-si (KR); Youngmo Sung, Suwon-si (KR); Joonghyuk Kim, Seoul (KR); Sangho Park, Anyang-si (KR); Soohwan Sul, Suwon-si (KR); Won-joon Son, Suwon-si (KR); Hyeonho Choi, Seoul (KR)

(73) Assignees: SAMSUNG ELECTRONICS CO., LTD., Gyeonggi-Do (KR); RESEARCH & BUSINESS FOUNDATION SUNGKYUNKWAN UNIVERSITY, Gyeonggi-Do (KR)

( * ) Notice: Subject to any disclaimer, the term of this patent is extended or adjusted under 35 U.S.C. 154(b) by 668 days.

(21) Appl. No.: 17/465,019

(22) Filed: Sep. 2, 2021

(65) Prior Publication Data
US 2023/0097695 A1 Mar. 30, 2023

(30) Foreign Application Priority Data
Feb. 22, 2021 (KR) .......................... 10-2021-0023357

(51) Int. Cl.
| | | |
|---|---|---|
| *C07D 519/00* | (2006.01) | |
| *C07D 487/14* | (2006.01) | |
| *H10K 85/60* | (2023.01) | |
| *H10K 50/11* | (2023.01) | |
| *H10K 50/12* | (2023.01) | |
| *H10K 71/00* | (2023.01) | |
| *H10K 101/00* | (2023.01) | |
| *H10K 101/10* | (2023.01) | |

(Continued)

(52) U.S. Cl.
CPC ......... *C07D 519/00* (2013.01); *C07D 487/14* (2013.01); *H10K 85/6572* (2023.02); *H10K 50/11* (2023.02); *H10K 50/121* (2023.02); *H10K 71/00* (2023.02); *H10K 2101/10* (2023.02); *H10K 2101/30* (2023.02); *H10K 2101/40* (2023.02); *H10K 2101/90* (2023.02)

(58) Field of Classification Search
None
See application file for complete search history.

(56) References Cited

U.S. PATENT DOCUMENTS

| | | |
|---|---|---|
| 6,310,360 B1 | 10/2001 | Forrest et al. |
| 6,515,298 B2 | 2/2003 | Forrest et al. |
| 6,894,307 B2 | 5/2005 | Forrest et al. |

(Continued)

FOREIGN PATENT DOCUMENTS

| | | |
|---|---|---|
| JP | 2002193952 A | 7/2002 |
| KR | 1020170025990 A | 3/2017 |

(Continued)

OTHER PUBLICATIONS

Lee, Ha Lim, et al. "Multiple-Resonance Extension and Spin-Vibronic-Coupling-Based Narrowband Blue Organic Fluorescence Emitters with Over 30% Quantum Efficiency." Advanced Materials 34.33 (2022): 2202464. (Year: 2022).*

(Continued)

*Primary Examiner* — Robert S Loewe
(74) *Attorney, Agent, or Firm* — CANTOR COLBURN LLP

(57) ABSTRACT

Provided are a heterocyclic compound represented by Formula 1-1 or 1-2, an organic light-emitting device including the heterocyclic compound, and an electronic apparatus including the organic light-emitting device:

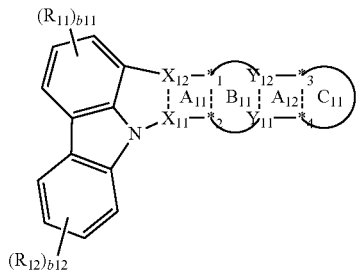

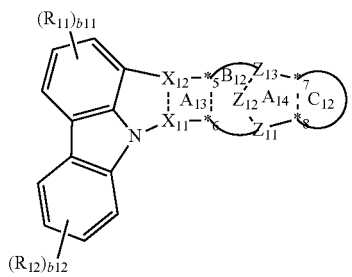

Formulae 1-1 and 1-2 may each be understood by referring to the descriptions of Formulae 1-1 and 1-2 provided herein.

20 Claims, 5 Drawing Sheets

(51) Int. Cl.
    *H10K 101/30*    (2023.01)
    *H10K 101/40*    (2023.01)

(56) References Cited

U.S. PATENT DOCUMENTS

| | | | |
|---|---|---|---|
| 8,476,823 | B2 | 7/2013 | Kuma et al. |
| 8,643,268 | B2 | 2/2014 | Ogiwara et al. |
| 9,153,790 | B2 | 10/2015 | Kuma et al. |
| 9,385,329 | B2 | 7/2016 | Li et al. |
| 9,493,698 | B2 | 11/2016 | Beers et al. |
| 9,905,779 | B2 | 2/2018 | Ogiwara et al. |
| 10,069,077 | B2 | 9/2018 | Park et al. |
| 10,090,483 | B2 | 10/2018 | Kim et al. |
| 10,249,832 | B1 | 4/2019 | Takahashi et al. |
| 10,680,181 | B2 | 6/2020 | Takahashi et al. |
| 10,957,863 | B2 | 3/2021 | Lee et al. |
| 2013/0320310 | A1* | 12/2013 | Yamamoto ......... H10K 85/6572 257/40 |
| 2017/0062718 | A1 | 3/2017 | Numata et al. |
| 2017/0077418 | A1 | 3/2017 | Stoessel et al. |
| 2017/0163010 | A1 | 6/2017 | Nakanotani et al. |
| 2018/0130959 | A1 | 5/2018 | Ogiwara et al. |
| 2019/0221747 | A1* | 7/2019 | Takahashi ............... H10K 50/11 |
| 2019/0225636 | A1 | 7/2019 | Bae et al. |
| 2019/0305229 | A1 | 10/2019 | Ihn et al. |
| 2020/0058874 | A1 | 2/2020 | Kim et al. |
| 2020/0083458 | A1 | 3/2020 | Jeon et al. |
| 2020/0144503 | A1 | 5/2020 | Hayano |
| 2020/0321537 | A1 | 10/2020 | Jeon et al. |
| 2020/0395558 | A1 | 12/2020 | Bae et al. |
| 2020/0395559 | A1 | 12/2020 | Bae et al. |
| 2020/0395560 | A1 | 12/2020 | Bae et al. |
| 2021/0053998 | A1 | 2/2021 | Kim et al. |
| 2021/0167299 | A1 | 6/2021 | Chung et al. |
| 2021/0171548 | A1 | 6/2021 | Min et al. |
| 2021/0198222 | A1 | 7/2021 | Jung et al. |
| 2021/0249610 | A1 | 8/2021 | Kim et al. |
| 2021/0265490 | A1 | 8/2021 | Duriez et al. |
| 2021/0277026 | A1 | 9/2021 | Geum et al. |
| 2022/0223804 | A1 | 7/2022 | Chung et al. |
| 2023/0034532 | A1 | 2/2023 | Jung et al. |
| 2023/0084208 | A1 | 3/2023 | Kim et al. |
| 2023/0090659 | A1 | 3/2023 | Kwon et al. |
| 2023/0097942 | A1 | 3/2023 | Kim et al. |
| 2023/0363272 | A1* | 11/2023 | Kim ..................... C07F 7/0812 |

FOREIGN PATENT DOCUMENTS

| | | |
|---|---|---|
| KR | 1020170032148 A | 3/2017 |
| KR | 1020180098809 A | 9/2018 |
| KR | 1020190089626 A | 7/2019 |
| KR | 1020200011383 A | 2/2020 |
| KR | 1020200019272 A | 2/2020 |
| KR | 1020200020538 A | 2/2020 |
| KR | 1020200047400 A | 5/2020 |
| KR | 1020200050327 A | 5/2020 |
| KR | 1020200052513 A | 5/2020 |
| KR | 1020200143235 A | 12/2020 |
| KR | 1020200143236 A | 12/2020 |
| KR | 1020200143237 A | 12/2020 |
| KR | 1020210026620 A | 3/2021 |
| KR | 1020210068994 A | 6/2021 |
| KR | 1020210084775 A | 7/2021 |
| KR | 20220005359 A | 1/2022 |
| WO | 2016158540 A1 | 10/2016 |
| WO | 2020067290 A1 | 4/2020 |

OTHER PUBLICATIONS

English Abstract of EP 3787056.
English Abstract of JP 2002-193952.
English Abstract of KR 10-2020-0047400.
English Abstract of KR 10-2021-0026620.

* cited by examiner

HETEROCYCLIC COMPOUND, ORGANIC LIGHT-EMITTING DEVICE INCLUDING HETEROCYCLIC COMPOUND, AND ELECTRONIC APPARATUS INCLUDING ORGANIC LIGHT-EMITTING DEVICE

CROSS-REFERENCE TO RELATED APPLICATION

This application claims priority under 35 U.S.C. § 119 to Korean Patent Application No. 10-2021-0023357, filed on Feb. 22, 2021, in the Korean Intellectual Property Office, the content of which is incorporated by reference herein in its entirety.

BACKGROUND

1. Field

The present disclosure relates to a heterocyclic compound, an organic light-emitting device including the heterocyclic compound, and an electronic apparatus including the organic light-emitting device.

2. Description of the Related Art

Organic light-emitting devices (OLEDs) are self-emissive devices that, as compared with conventional devices, have wide viewing angles, high contrast ratios, short response times, and excellent brightness, driving voltage, and response speed characteristics, and produce full-color images.

OLEDs include an anode, a cathode, and an organic layer between the anode and the cathode and including an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. The excitons may transition from an excited state to a ground state, thus generating light.

SUMMARY

One or more embodiments relate to a heterocyclic compound, an organic light-emitting device including the heterocyclic compound, and an electronic apparatus including the organic light-emitting device.

Additional aspects will be set forth in part in the description which follows and, in part, will be apparent from the description, or may be learned by practice of the presented embodiments of the disclosure.

According to an aspect, a heterocyclic compound may be represented by one of Formulae 11, 12, and 14 to 17:

Formula 11

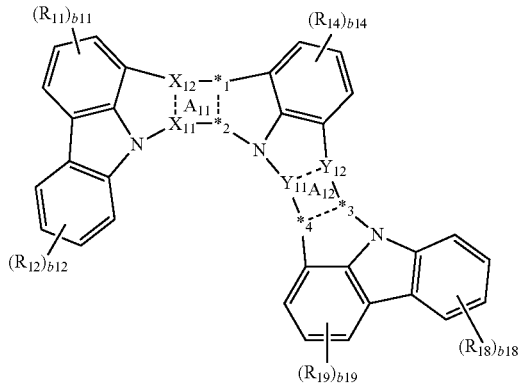

Formula 12

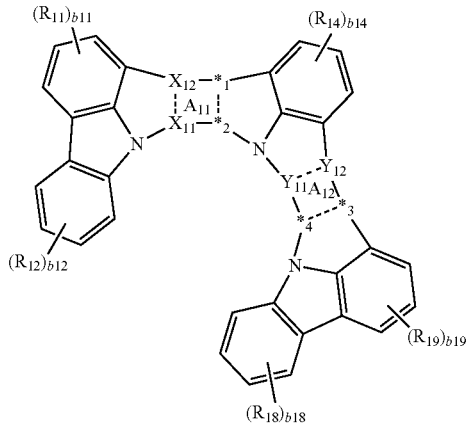

Formula 14

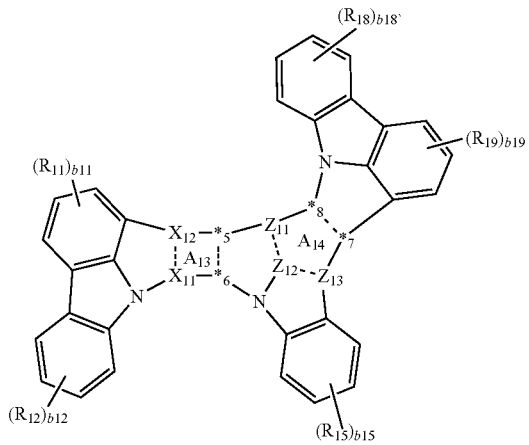

-continued

Formula 15

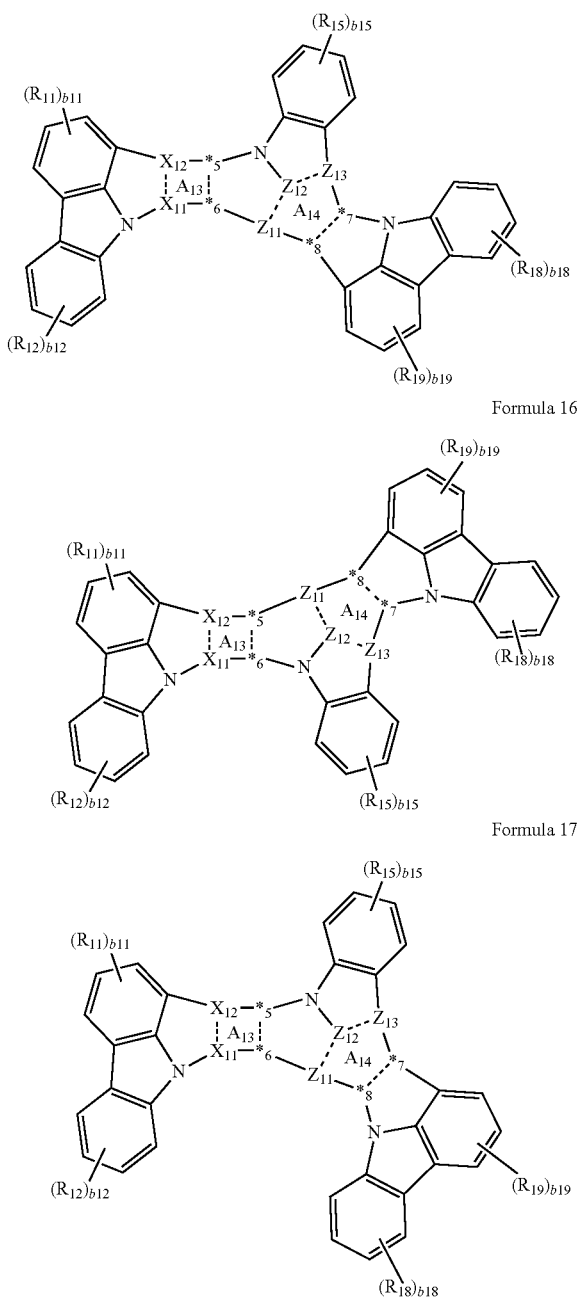

Formula 16

Formula 17 wherein, in Formulae 11, 12, and 14 to 17, $A_{11}$ and $A_{13}$ are each independently a group represented by Formula 2-1, $A_{12}$ is a group represented by Formula 2-2, $A_{14}$ is a group represented by Formula 2-3, 2-1

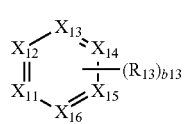

2-2

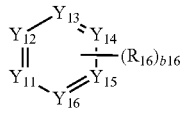

2-3

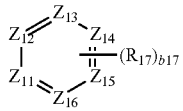

wherein, in Formulae 2-1 to 2-3, $X_{11}$ to $X_{16}$, $Y_{11}$ to $Y_{16}$, and $Z_{11}$ to $Z_{16}$ are each independently a carbon atom, any suitable two adjacent groups $X_{13}$ to $X_{16}$ may be *1 and *2 in Formulae 11 and 12 or *5 and *6 in Formulae 14 to 17, and any suitable two adjacent groups $Y_{13}$ to $Y_{16}$ may be *3 and *4 in Formulae 11 and 12, and any suitable two adjacent groups $Z_{14}$ to $Z_{16}$ may be *7 and *8 in Formulae 14 to 17, in Formula 11, ii) *1 is $X_{13}$, *2 is $X_{14}$, *3 is $Y_{14}$, and *4 is $Y_{15}$; or v) *1 is $X_{14}$, *2 is $X_{15}$, *3 is $Y_{14}$, and *4 is $Y_{15}$, in Formula 12, i) *1 is $X_{13}$, *2 is $X_{14}$, *3 is $Y_{13}$, and *4 is $Y_{14}$; ii) *1 is $X_{13}$, *2 is $X_{14}$, *3 is $Y_{14}$, and *4 is $Y_{15}$; or iv) *1 is $X_{14}$, *2 is $X_{15}$, *3 is $Y_{14}$, and *4 is $Y_{15}$, in Formula 14, i) *5 is $X_{13}$, *6 is $X_{14}$, *7 is $Z_{14}$, and *8 is $Z_{15}$; iii) *5 is $X_{14}$, *6 is $X_{15}$, *7 is $Z_{14}$, and *8 is $Z_{15}$; or iv) *5 is $X_{14}$, *6 is $X_{15}$, *7 is $Z_{15}$, and *8 is $Z_{16}$, in Formula 15, iii) *5 is $X_{14}$, *6 is $X_{15}$, *7 is $Z_{14}$, and *8 is $Z_{15}$; in Formula 16, iii) *5 is $X_{14}$, *6 is $X_{15}$, *7 is $Z_{14}$, and *8 is $Z_{15}$; or iv) *5 is $X_{14}$, *6 is $X_{15}$, *7 is $Z_{15}$, and *8 is $Z_{16}$, in Formula 17, iv) *5 is $X_{14}$, *6 is $X_{15}$, *7 is $Z_{15}$, and *8 is $Z_{16}$, $R_{11}$ to $R_{19}$ are each independently hydrogen, deuterium, —F, —Cl, —Br, —I, —$SF_5$, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkyl aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkyl heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent aromatic condensed polycyclic group, a substituted or unsubstituted monovalent aromatic condensed heteropolycyclic group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —Ge$(Q_1)(Q_2)(Q_3)$, —C$(Q_1)(Q_2)(Q_3)$, —B$(Q_1)(Q_2)$, —N$(Q_1)(Q_2)$, —P$(Q_1)(Q_2)$, —C(=O)$(Q_1)$, —S(=O)$(Q_1)$, —S(=O)$_2(Q_1)$, —P(=O)$(Q_1)(Q_2)$, or —P(=S)$(Q_1)(Q_2)$, b11, b14, and b19 are each independently 0, 1, 2, or 3,
b12, b15, and b18 are each independently 0, 1, 2, 3, or 4,
b13 and b16 are each independently 0, 1, or 2, and
b17 is 0 or 1,
wherein $Q_1$ to $Q_3$ are each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkyl aryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent aromatic condensed polycyclic group, a monovalent aromatic condensed heteropolycyclic group, a monovalent non-aromatic condensed polycyclic group, a monovalent non-aromatic condensed heteropolycyclic group, a $C_1$-$C_{60}$ alkyl group substituted with at least one deuterium, —F, a cyano group, a $C_1$-$C_{60}$ alkyl group, and a $C_6$-$C_{60}$ aryl group, and a $C_6$-$C_{60}$ aryl group substituted with at least one deuterium, —F, a cyano group, a $C_1$-$C_{60}$ alkyl group, or a $C_6$-$C_{60}$ aryl group.

According to one or more embodiments, an organic light-emitting device may include a first electrode, a second electrode, and an organic layer between the first electrode and the second electrode and including an emission layer, and the organic light-emitting device may include the heterocyclic compound.

According to an aspect of another embodiment, an electronic apparatus may include the organic light-emitting device.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
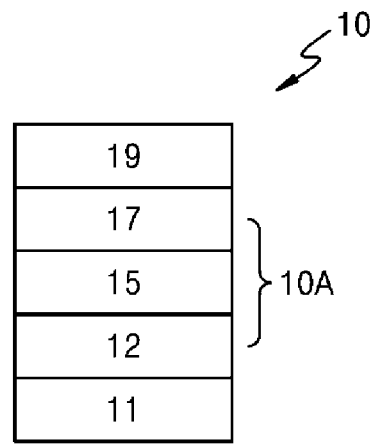
FIG. 1 illustrates a schematic view of an organic light-emitting device 1 according to an exemplary embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures It will be understood that relative terms are intended to encompass different orientations of the device in addition to the orientation depicted in the Figures For example, if the device in one of the figures is turned over, elements described as being on the "lower" side of other elements would then be oriented on "upper" sides of the other elements The exemplary term "lower," can therefore, encompasses both an orientation of "lower" and "upper," depending on the particular orientation of the figure Similarly, if the device in one of the figures is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

The heterocyclic compound may be represented by Formula 1-1 or 1-2:

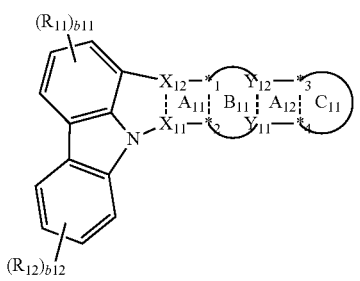

1-1

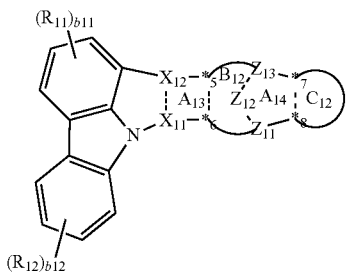

1-2 wherein, in Formulae 1-1 and 1-2, $A_{11}$ and $A_{13}$ may each independently be a group represented by Formula 2-1, $A_{12}$ may be a group represented by Formula 2-2, and $A_{14}$ may be a group represented by Formula 2-3:

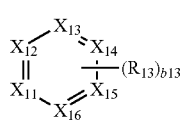

2-1

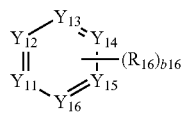

2-2

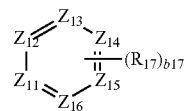

2-3 wherein, in Formula 2-1 to 2-3, $X_{11}$ to $X_{16}$, $Y_{11}$ to $Y_{16}$, and $Z_{11}$ to $Z_{16}$ may each independently be a carbon atom, any suitable two adjacent groups $X_{13}$ to $X_{16}$ may be *1 and *2 in Formula 1-1 or *5 and *6 in Formula 1-2, and any suitable two adjacent groups $Y_{13}$ to $Y_{16}$ may be *3 and *4 in Formula 1-1, and any suitable two adjacent groups $Z_{14}$ to $Z_{16}$ may be *7 and *8 in Formula 1-2.

In Formula 1-1, $B_{11}$ may be a group represented by Formula 2-4:

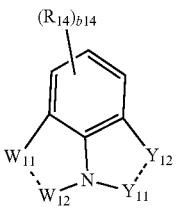

2-4 wherein, in Formula 2-4, $W_{11}$ and $W_{12}$ may each independently be a carbon atom, and $W_{11}$ and $W_{12}$ may respectively be *1 and *2 in Formula 1-1.

In Formula 1-2, $B_{12}$ may be a group represented by Formula 2-5:

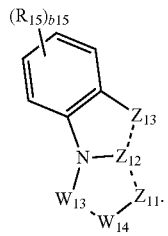

2-5

In Formula 2-5, $W_{13}$ and $W_{14}$ may each independently be a carbon atom, and $W_{13}$ and $W_{14}$ may respectively be *5 and *6 in Formula 1-2.

In Formulae 1-1 and 1-2, $C_{11}$ and $C_{12}$ may each independently be a group represented by Formula 2-6:

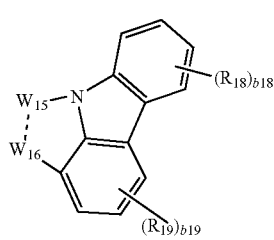

2-6 wherein, in Formula 2-6, $W_{15}$ and $W_{16}$ may each independently be a carbon atom, and $W_{15}$ and $W_{16}$ may respectively be *3 and *4 in Formula 1-1 or *7 and *8 in Formula 1-2.

In Formulae 1-1 and 1-2, $R_{11}$ to $R_{19}$ may each independently be hydrogen, deuterium, —F, —Cl, —Br, —I, —SF$_5$, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkyl aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkyl heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent aromatic condensed polycyclic group, a substituted or unsubstituted monovalent aromatic condensed heteropolycyclic group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —Ge(Q$_1$)(Q$_2$)(Q$_3$), —C(Q$_1$)(Q$_2$)(Q$_3$), —B(Q$_1$)(Q$_2$), —N(Q$_1$)(Q$_2$), —P(Q$_1$)(Q$_2$), —C(=O)(Q$_1$), —S(=O)(Q$_1$), —S(=O)$_2$(Q$_1$), —P(=O)(Q$_1$)(Q$_2$), or —P(=S)(Q$_1$)(Q$_2$), wherein Q$_1$ to Q$_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkyl aryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent aromatic condensed polycyclic group, a monovalent aromatic condensed heteropolycyclic group, a monovalent non-aromatic condensed polycyclic group, a monovalent non-aromatic condensed heteropolycyclic group, a $C_1$-$C_{60}$ alkyl group substituted with at least one deuterium, —F, a cyano group, a $C_1$-$C_{60}$ alkyl group, a $C_6$-$C_{60}$ aryl group, or any combination thereof, or a $C_6$-$C_{60}$ aryl group substituted with at least one deuterium, —F, a cyano group, a $C_1$-$C_{60}$ alkyl group, a $C_6$-$C_{60}$ aryl group, or any combination thereof.

In some embodiments, in Formulae 1-1 and 1-2, $R_{11}$ to $R_{19}$ may each independently be: hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, a $C_1$-$C_{20}$ alkenyl group, a $C_1$-$C_{20}$ alkoxy group, or a $C_1$-$C_{20}$ alkylthio group;

a $C_1$-$C_{20}$ alkyl group, a $C_1$-$C_{20}$ alkenyl group, a $C_1$-$C_{20}$ alkoxy group, or a $C_1$-$C_{20}$ alkylthio group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a ($C_1$-$C_{20}$ alkyl)cyclopentyl group, a ($C_1$-$C_{20}$ alkyl)cyclohexyl group, a ($C_1$-$C_{20}$ alkyl)cycloheptyl group, a ($C_1$-$C_{20}$ alkyl)cyclooctyl group, a ($C_1$-$C_{20}$ alkyl) adamantanyl group, a ($C_1$-$C_{20}$ alkyl) norbornanyl group, a ($C_1$-$C_{20}$ alkyl) norbornenyl group, a ($C_1$-$C_{20}$ alkyl)cyclopentenyl group, a ($C_1$-$C_{20}$ alkyl) cyclohexenyl group, a ($C_1$-$C_{20}$ alkyl)cycloheptenyl group, a ($C_1$-$C_{20}$ alkyl) bicyclo[1.1.1]pentyl group, a ($C_1$-$C_{20}$ alkyl) bicyclo[2.1.1]hexyl group, a ($C_1$-$C_{20}$ alkyl) bicyclo[2.2.1]heptyl group, a ($C_1$-$C_{20}$ alkyl) bicyclo[2.2.2]octyl group, a phenyl group, a ($C_1$-$C_{20}$ alkyl)phenyl group, a biphenyl group, a terphenyl group, a naphthyl group, a pyridinyl group, a pyrimidinyl group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl) phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, or an azadibenzothiophenyl group, each unsubstituted or substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a deuterated $C_2$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a ($C_1$-$C_{20}$ alkyl)cyclopentyl group, a ($C_1$-$C_{20}$ alkyl)cyclohexyl group, a ($C_1$-$C_{20}$ alkyl)cycloheptyl group, a ($C_1$-$C_{20}$ alkyl)cyclooctyl group, a ($C_1$-$C_{20}$ alkyl) adamantanyl group, a ($C_1$-$C_{20}$ alkyl) norbornanyl group, a ($C_1$-$C_{20}$ alkyl) norbornenyl group, a ($C_1$-$C_{20}$ alkyl)cyclopentenyl group, a ($C_1$-$C_{20}$ alkyl)cyclohexenyl group, a ($C_1$-$C_{20}$ alkyl)cycloheptenyl group, a ($C_1$-$C_{20}$ alkyl) bicyclo[1.1.1]pentyl group, a ($C_1$-$C_{20}$ alkyl) bicyclo[2.1.1]hexyl group, a ($C_1$-$C_{20}$ alkyl) bicyclo[2.2.1]heptyl group, a ($C_1$-$C_{20}$ alkyl) bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, —Si($Q_{21}$)($Q_{22}$)($Q_{23}$), —Ge($Q_{21}$)($Q_{22}$)($Q_{23}$), —C($Q_{21}$)($Q_{22}$)($Q_{23}$), —B($Q_{21}$)($Q_{22}$), —N($Q_{21}$)($Q_{22}$) or any combination thereof, or —Si($Q_1$)($Q_2$)($Q_3$), —Ge($Q_1$)($Q_2$)($Q_3$), —C($Q_1$)($Q_2$)($Q_3$), —B($Q_1$)($Q_2$), or —N($Q_1$)($Q_2$), wherein $Q_1$ to $Q_3$ and $Q_{21}$ to $Q_{23}$ may each independently be:

deuterium, —F, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, —$CD_2CDH_2$, —$CF_3$, —$CF_2H$, —$CFH_2$, —$CH_2CF_3$, —$CH_2CF_2H$, —$CH_2CFH_2$, —$CHFCH_3$, —$CHFCF_2H$, —$CHFCFH_2$, —$CHFCF_3$, —$CF_2CF_3$, —$CF_2CF_2H$, or —$CF_2CFH_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

In some embodiments, in Formulae 1-1 and 1-2, $R_{11}$ to $R_{19}$ may each independently be hydrogen, deuterium, —F, —$CH_3$, —$CD_3$, —$CD_2H$, —$CDH_2$, —$CF_3$, —$CF_2H$, —$CFH_2$, $C_2$-$C_{10}$ alkenyl group, a $C_1$-$C_{10}$ alkoxy group, a $C_1$-$C_{10}$alkylthio group, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 9-201 to 9-236, a group represented by one of Formulae 9-201 to 9-236 in which at least one hydrogen is substituted with deuterium, a group represented by one of Formulae 9-201 to 9-236 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, a group represented by one of Formulae 10-201 to 10-358, a group represented by one of Formulae 10-201 to 10-358 in which at least one hydrogen is substituted with deuterium, a group represented by one of Formulae 10-201 to 10-358 in which at least one hydrogen is substituted with —F, a group represented by one of Formulae 10-359 to 10-380, a group represented by one of Formulae 10-359 to 10-380 in which at least one hydrogen is substituted with deuterium, a group represented by one of Formulae 10-359 to 10-380 in which at least one hydrogen is substituted with —F, —Si($Q_1$)($Q_2$)($Q_3$), —Ge($Q_1$)($Q_2$)($Q_3$), —C($Q_1$)($Q_2$)($Q_3$), —B($Q_1$)($Q_2$), or —N($Q_1$)($Q_2$), wherein $Q_1$ to $Q_3$ may each independently be:

deuterium, —F, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, —$CD_2CDH_2$, —$CF_3$, —$CF_2H$, —$CFH_2$, —$CH_2CF_3$, —$CH_2CF_2H$, —$CH_2CFH_2$, —$CHFCH_3$, —$CHFCF_2H$, —$CHFCFH_2$, —$CHFCF_3$, —$CF_2CF_3$, —$CF_2CF_2H$, or —$CF_2CFH_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

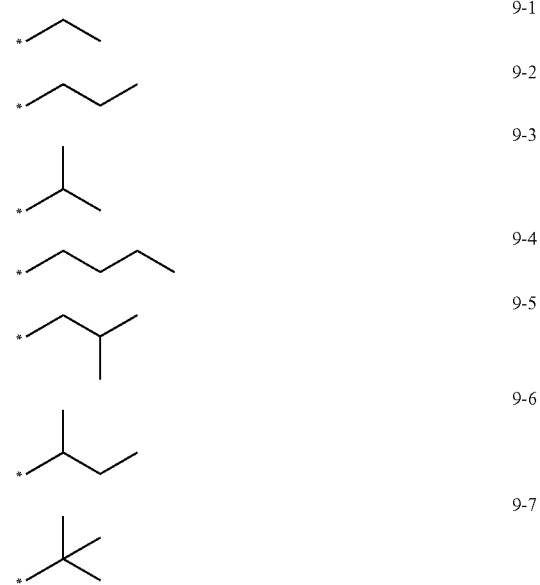

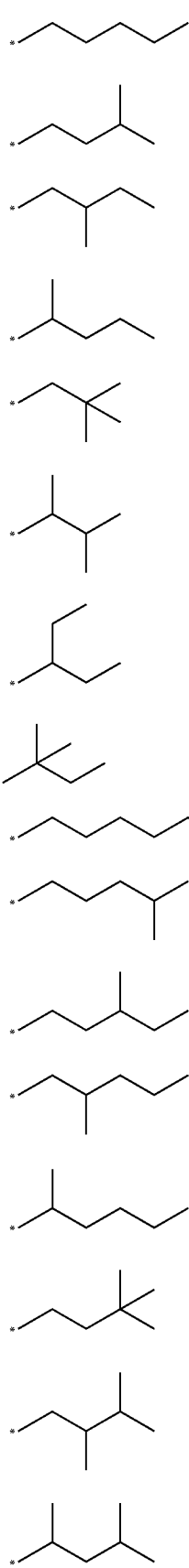
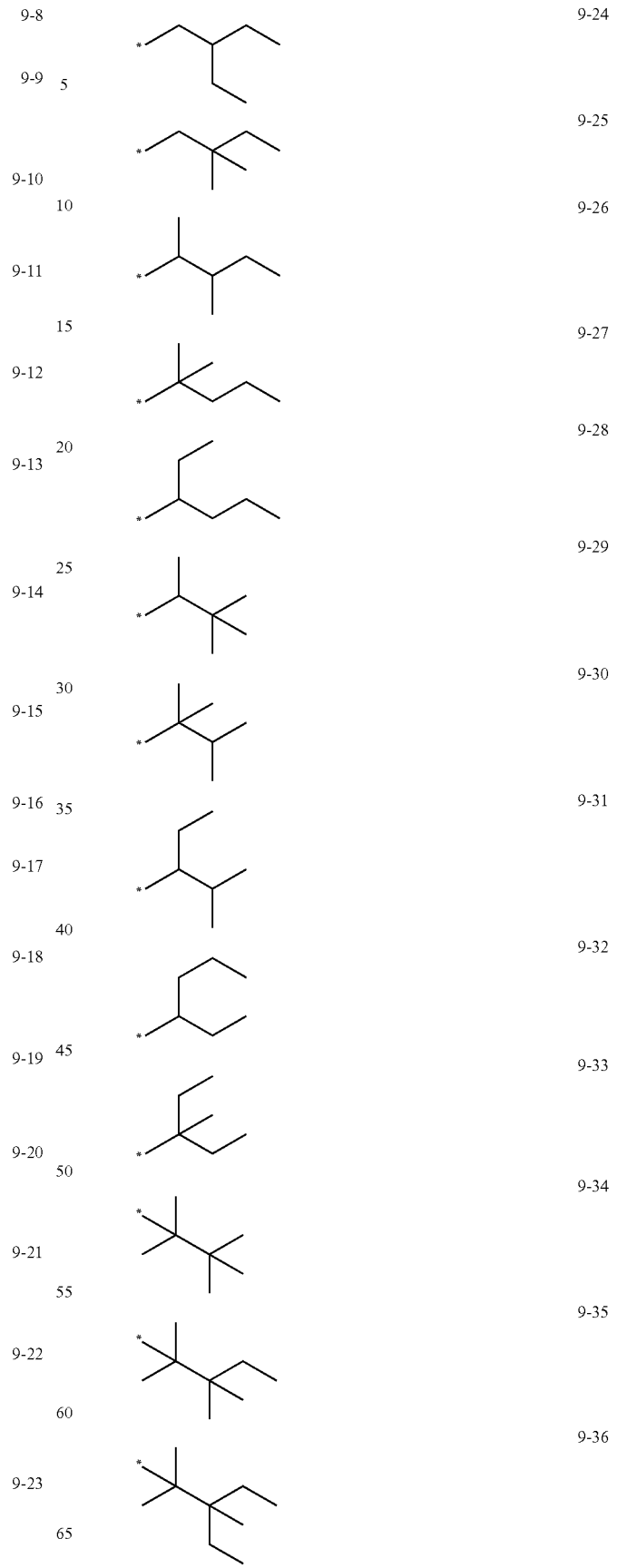

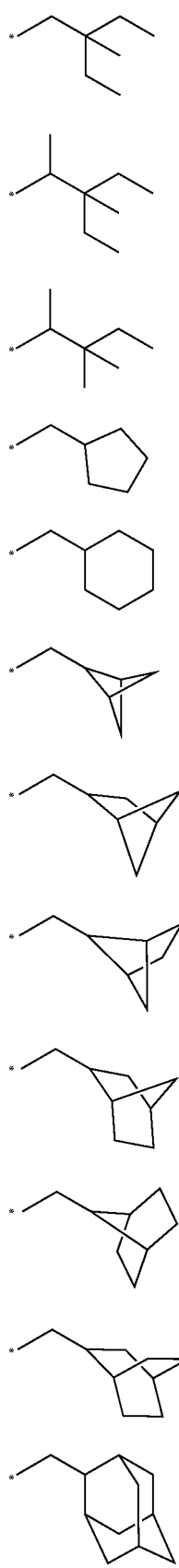
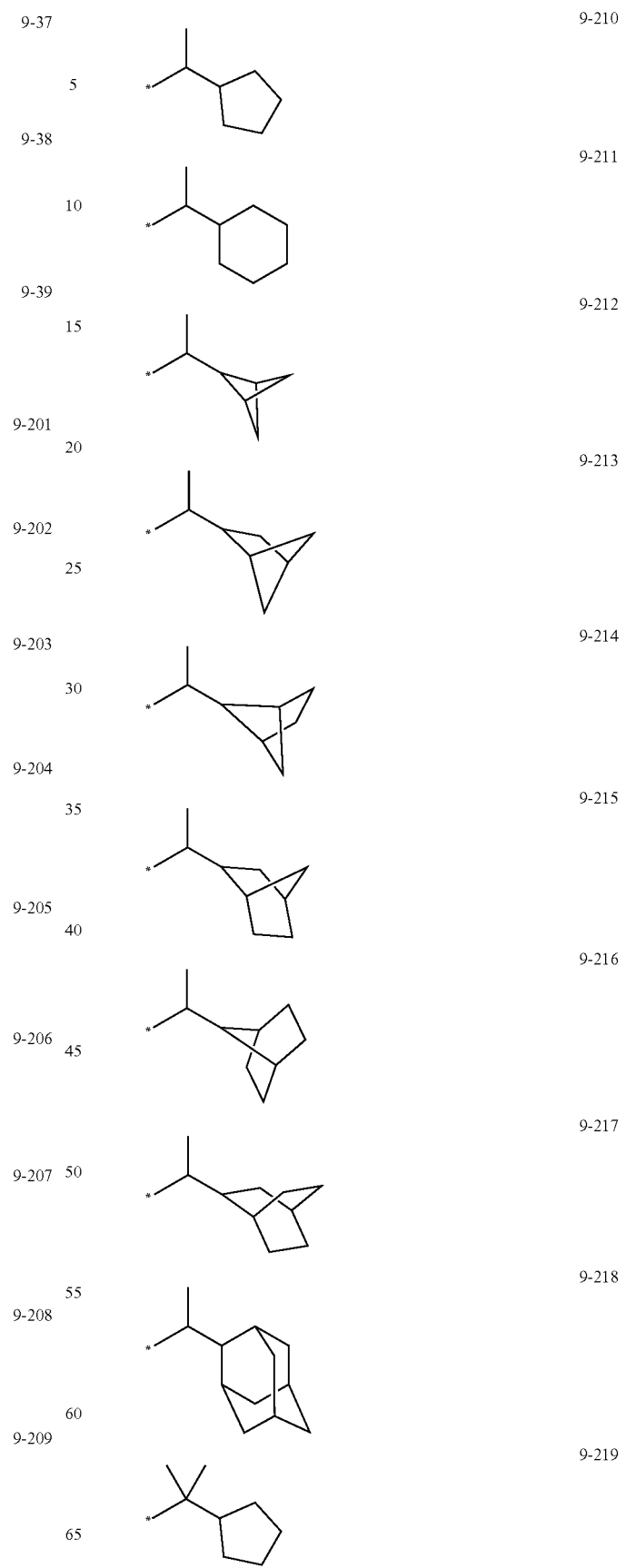

-continued 9-220
9-221
9-222
9-223
9-224
9-225
9-226
9-227
9-228
9-229

-continued 9-230
9-231
9-232
9-233
9-234
9-235
9-236
10-1
10-2
10-3
10-4
10-5

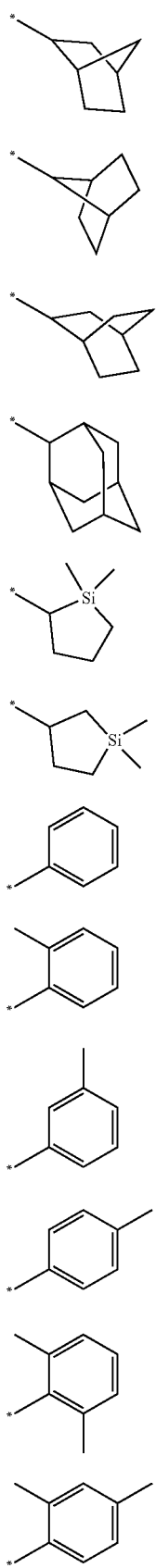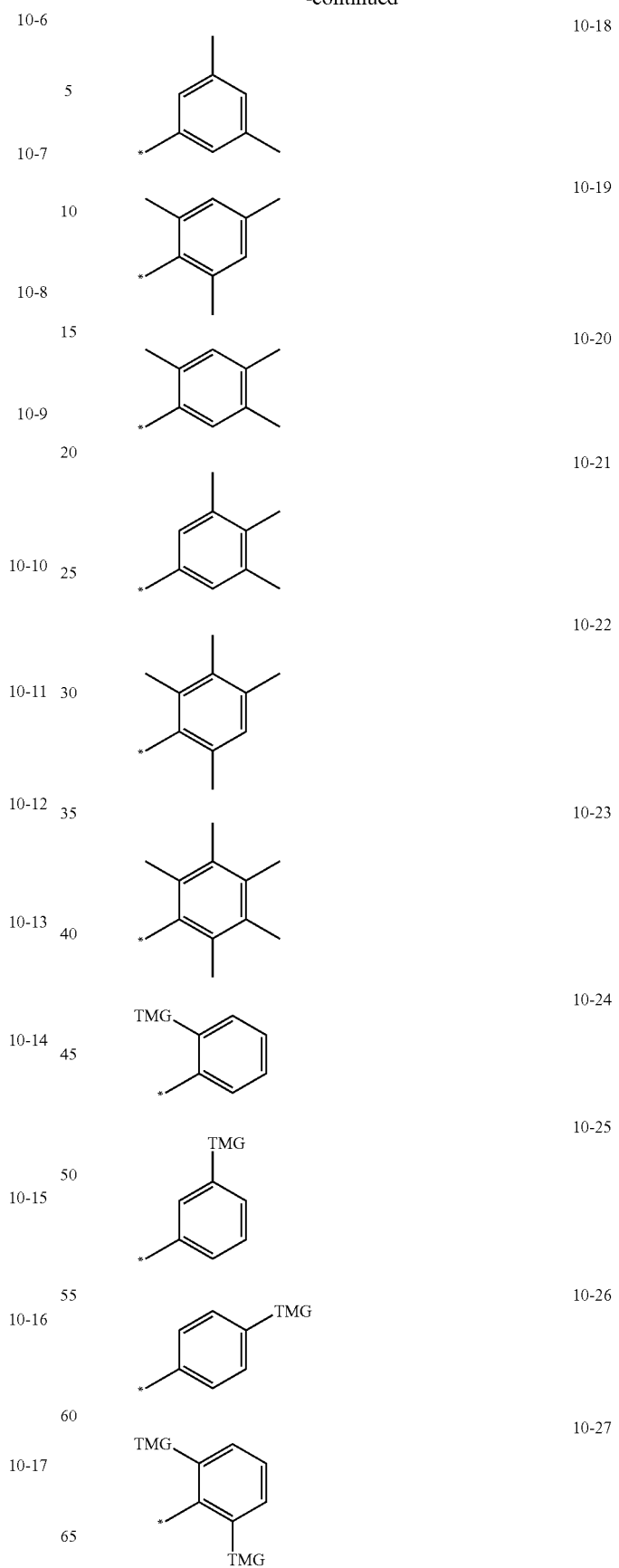

| | |
|---|---|
| 10-28 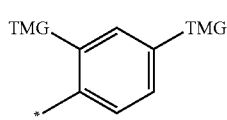 | 10-39 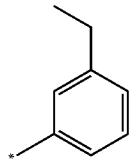 |
| 10-29 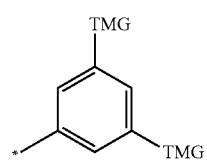 | 10-40 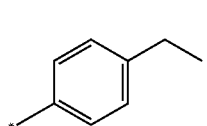 |
| 10-30 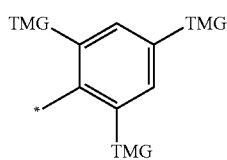 | 10-41 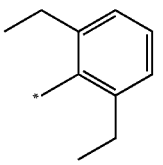 |
| 10-31 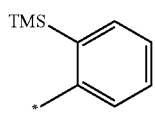 | 10-42 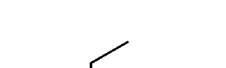 |
| 10-32 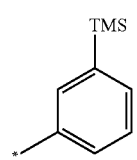 | 10-43 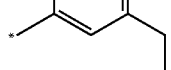 |
| 10-33 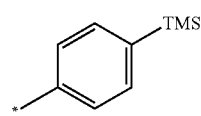 | 10-44 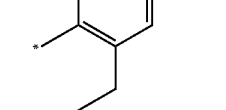 |
| 10-34 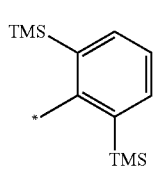 | 10-45 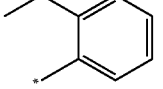 |
| 10-35 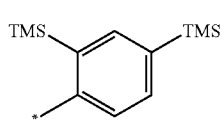 | 10-46 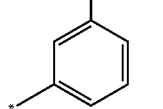 |
| 10-36 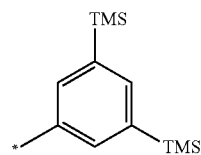 | 10-47 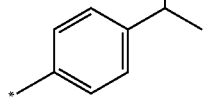 |
| 10-37 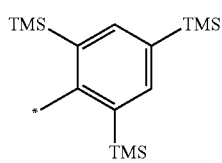 | |
| 10-38 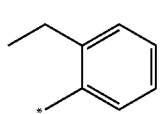 | |

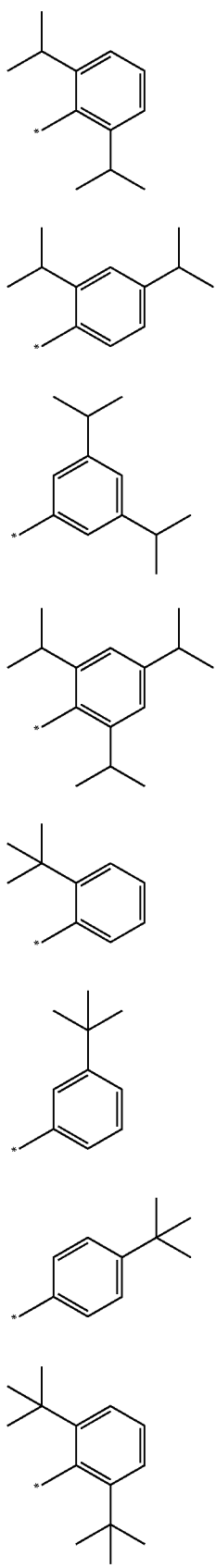
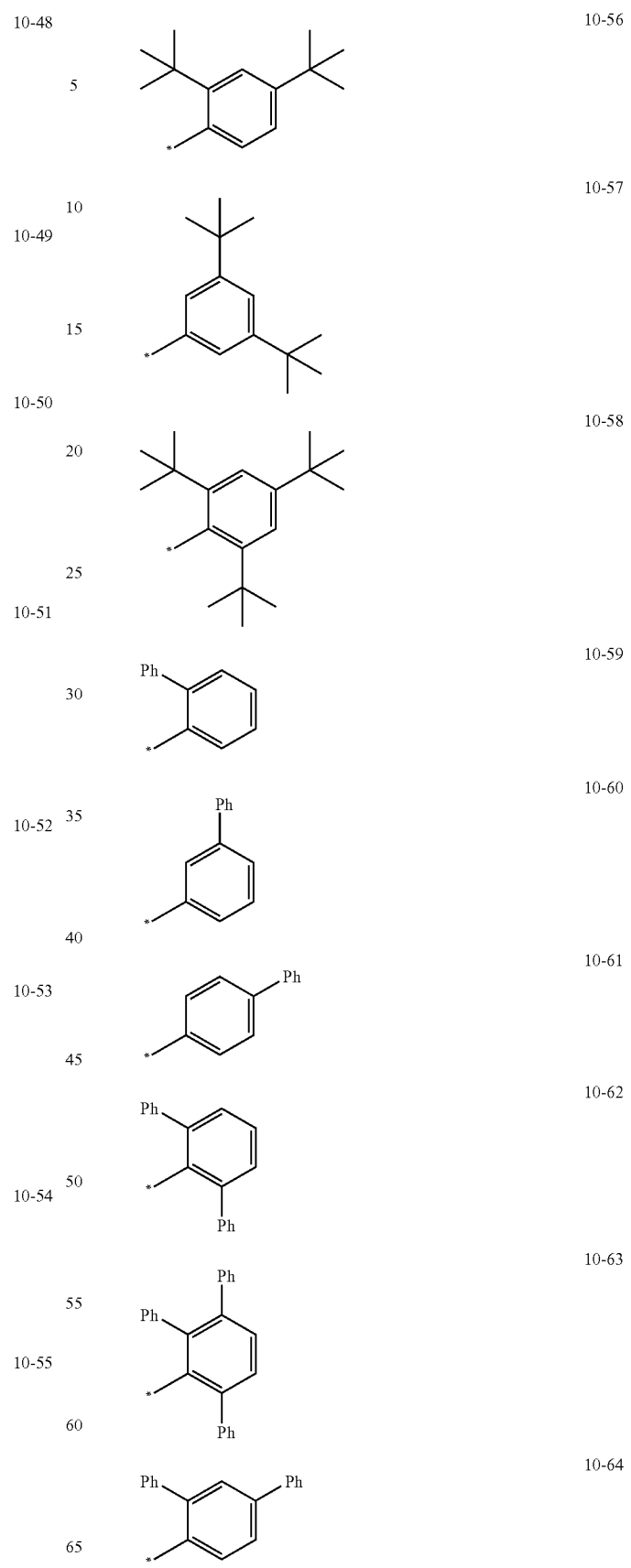

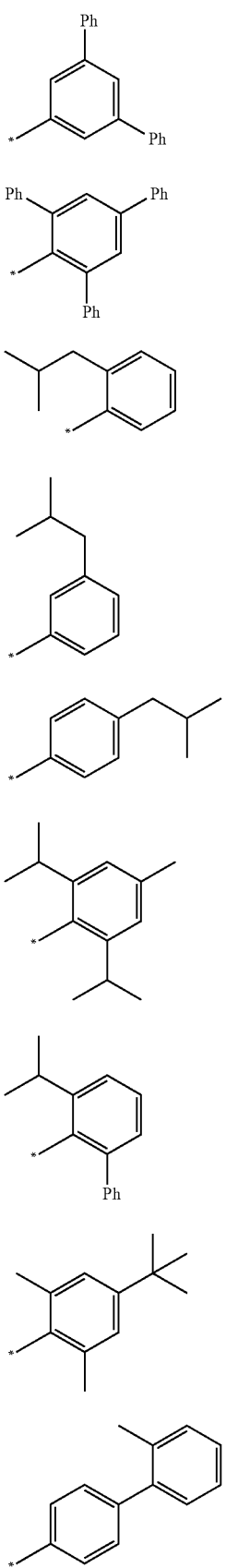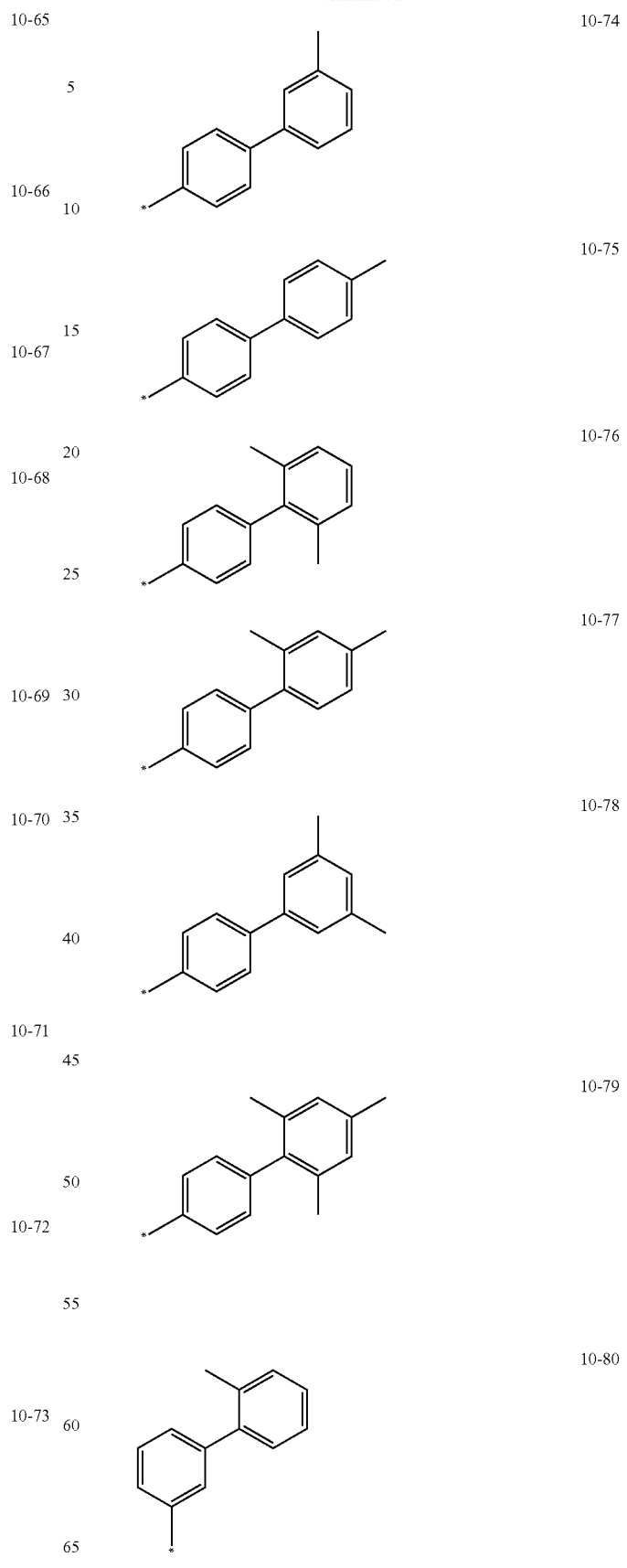

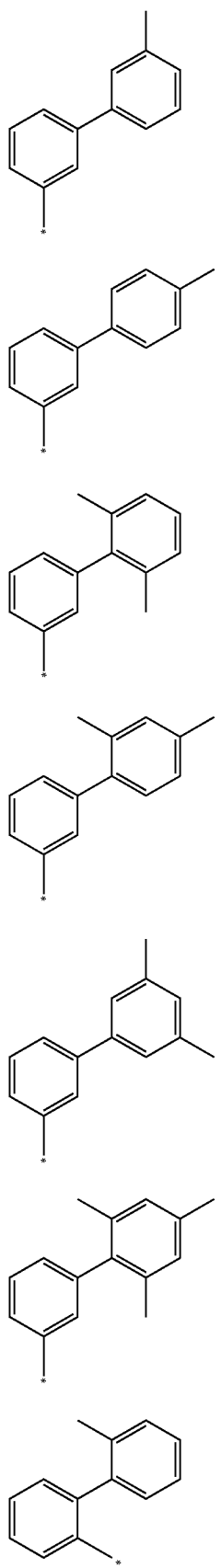
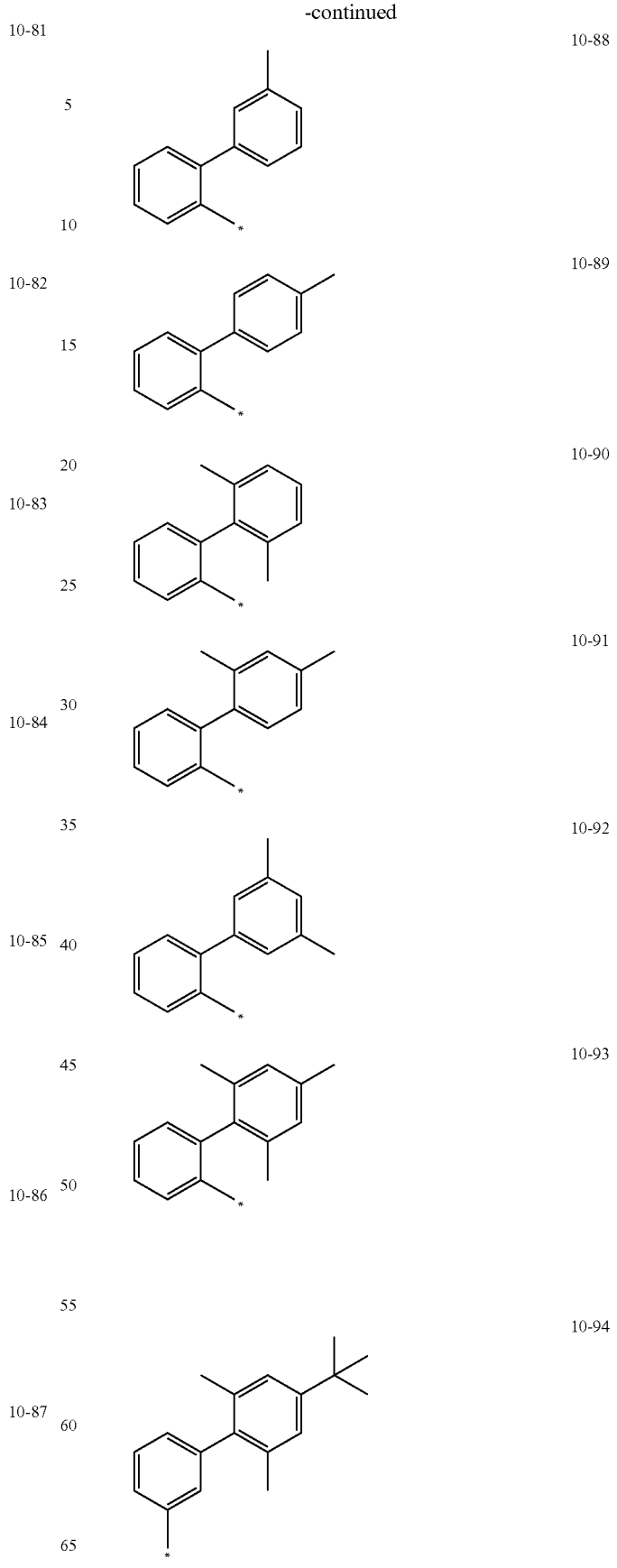

10-95 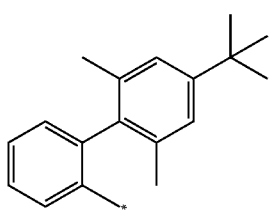
10-96 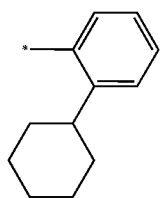
10-97 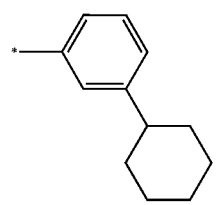
10-98 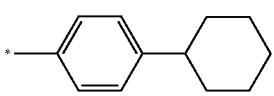
10-99 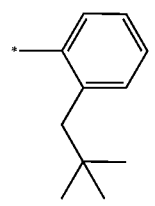
10-100 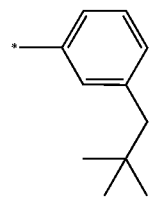
10-101 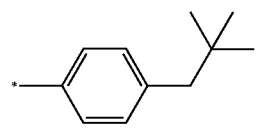
10-102 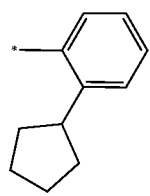
10-103 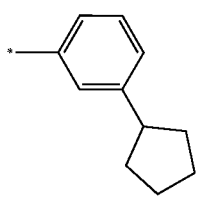
10-104 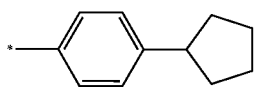
10-105 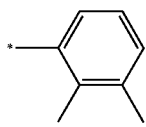
10-106
10-107 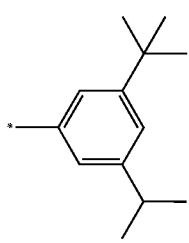
10-108 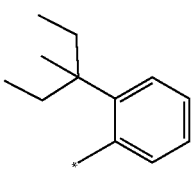
10-109 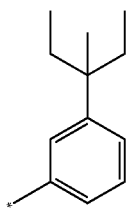
10-110 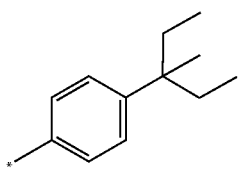

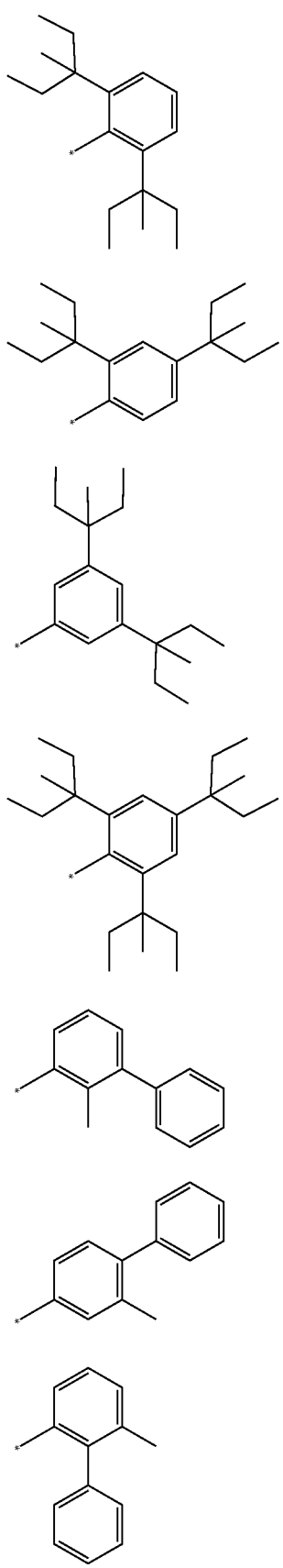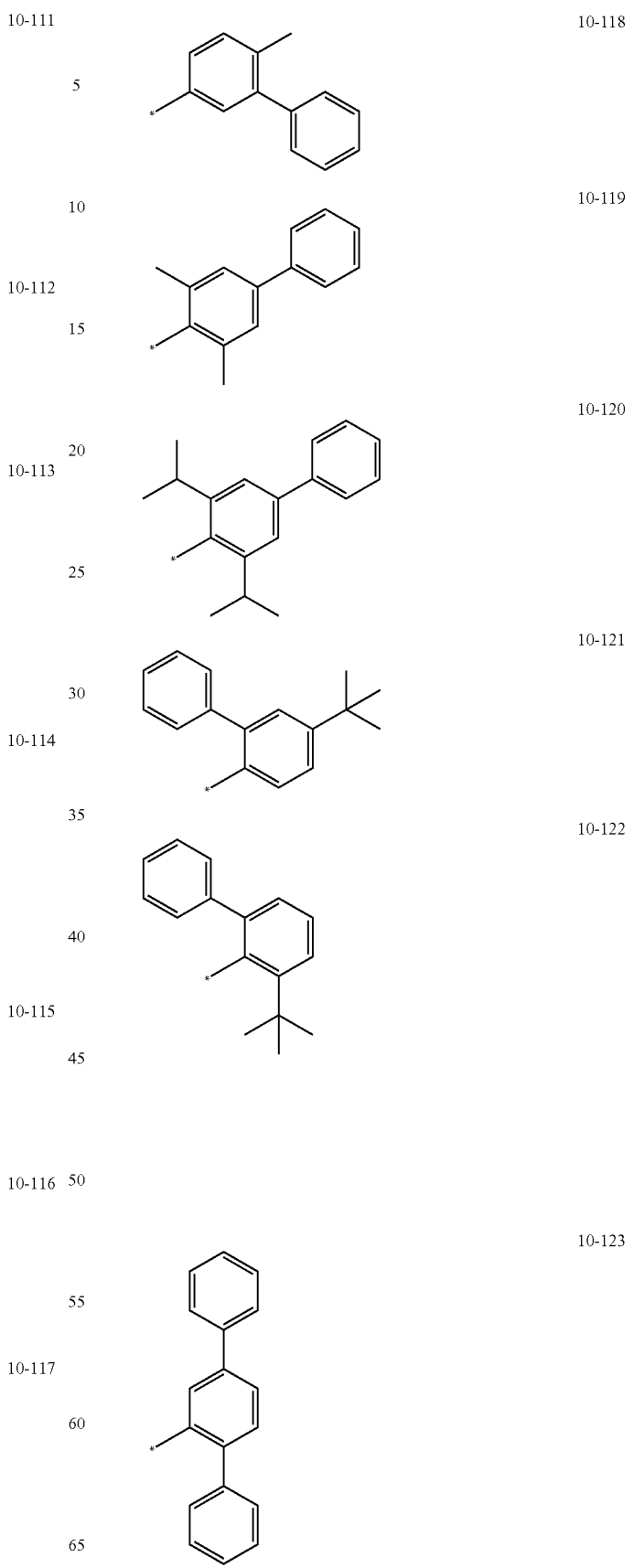

10-124 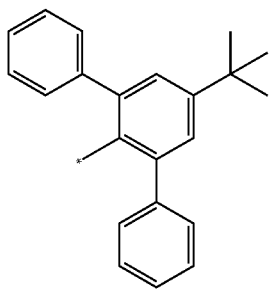
10-125 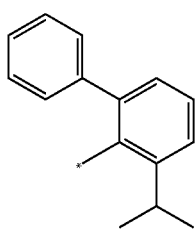
10-126 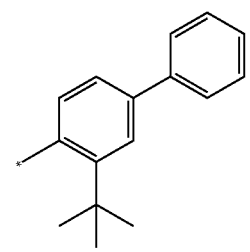
10-127 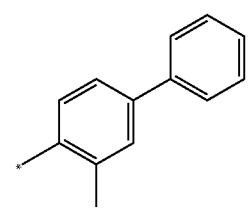
10-128 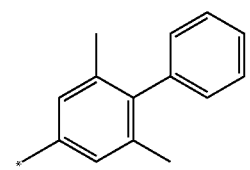
10-129 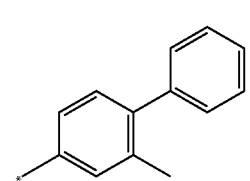
10-130 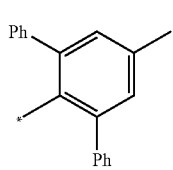
10-201 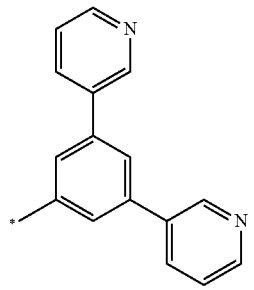
10-202 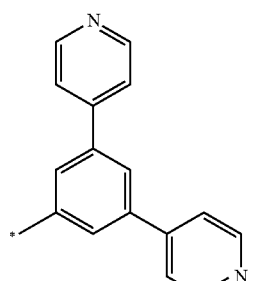
10-203 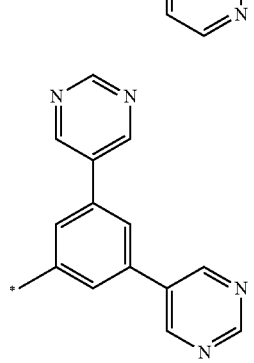
10-204 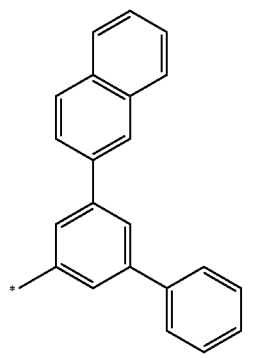
10-205 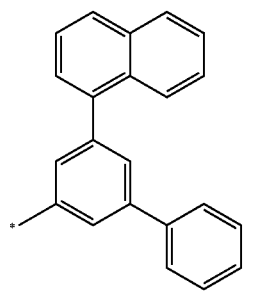

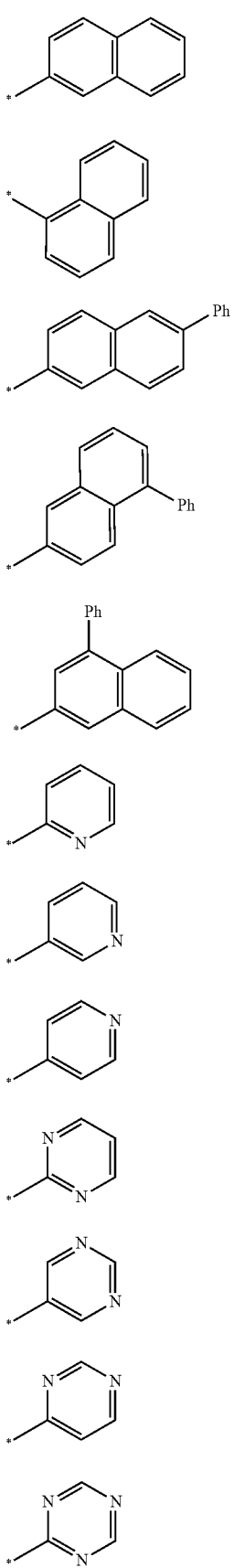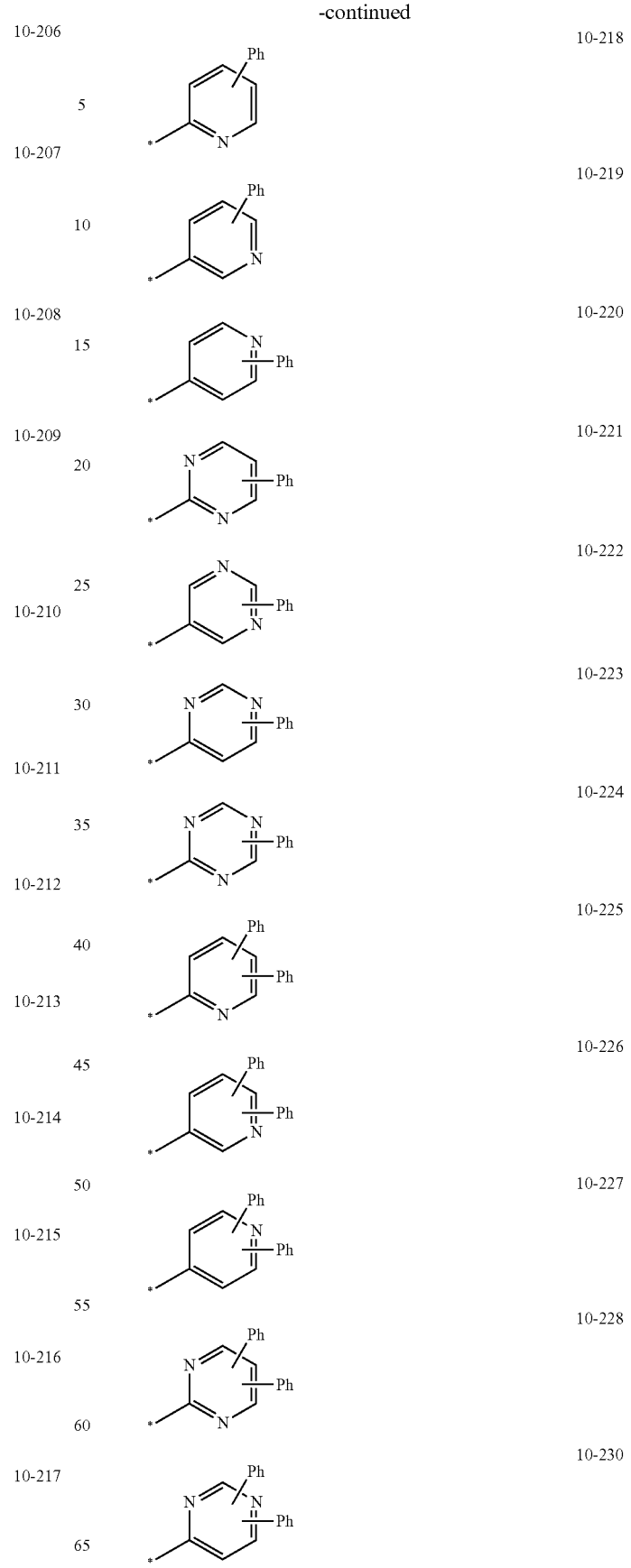

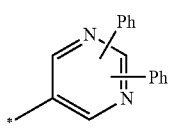

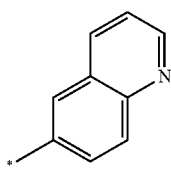
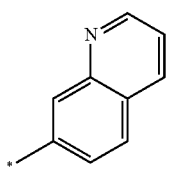
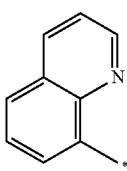
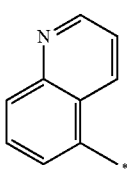
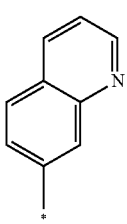
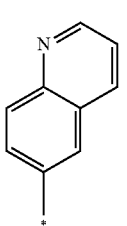
10-229

10-230
10-231

10-232
10-233
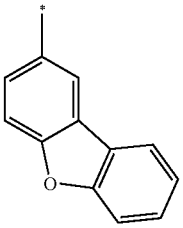
10-234
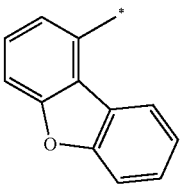
10-235
10-236
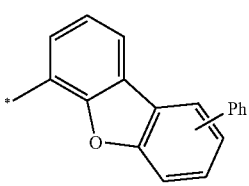
10-237

10-238
10-239
10-240
10-241
10-242
10-243
10-244
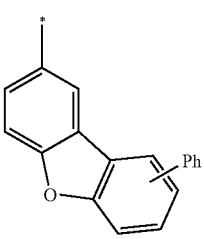

10-245
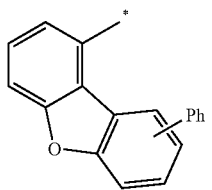
10-246
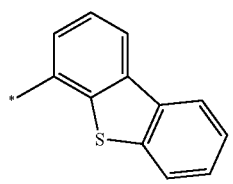
10-247
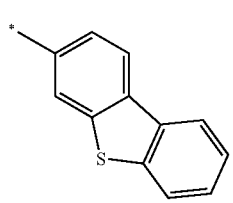
10-248
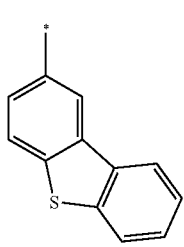
10-249
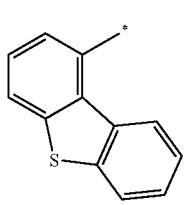
10-250
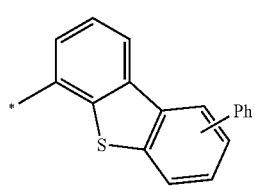
10-251
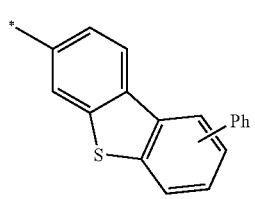
10-252
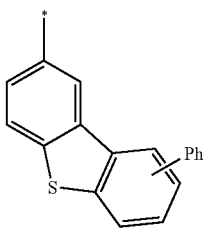
10-253
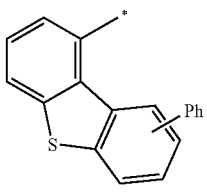
10-254
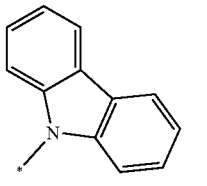
10-255
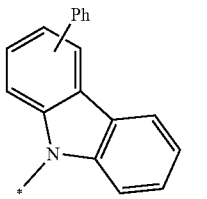
10-256
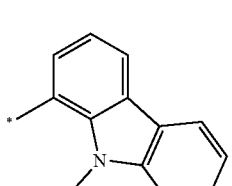
10-257
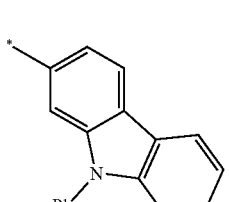
10-258
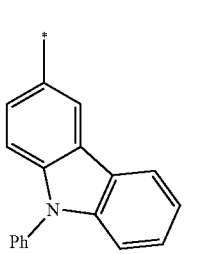

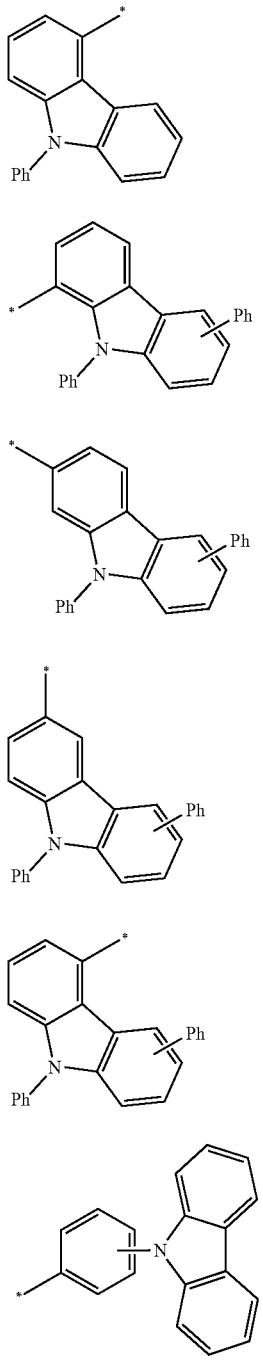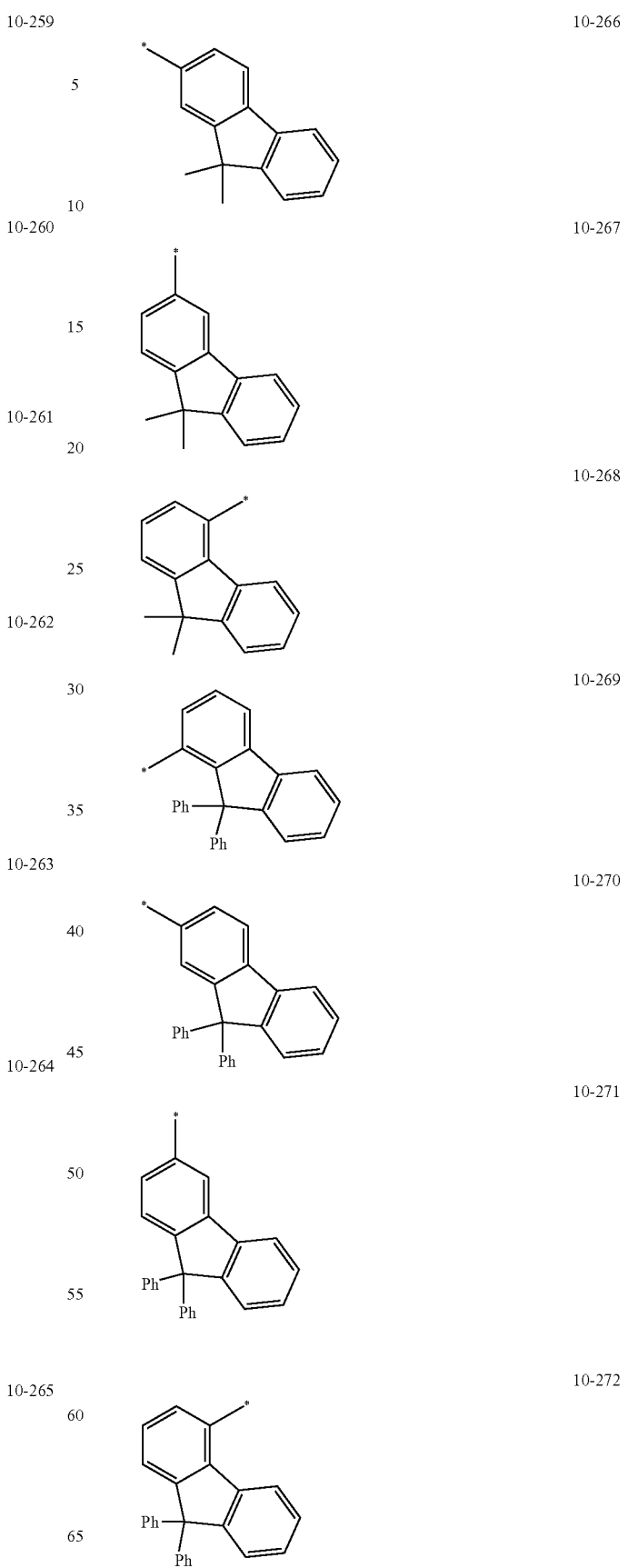

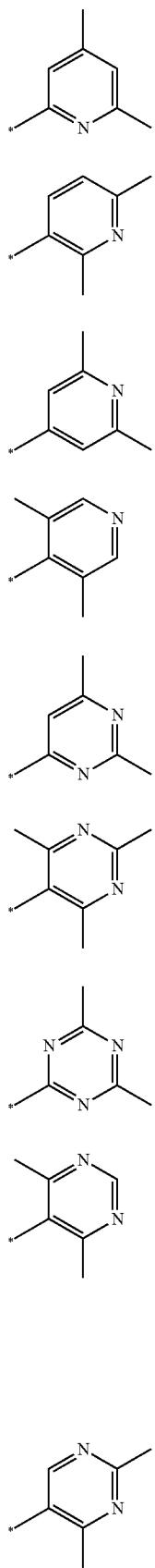
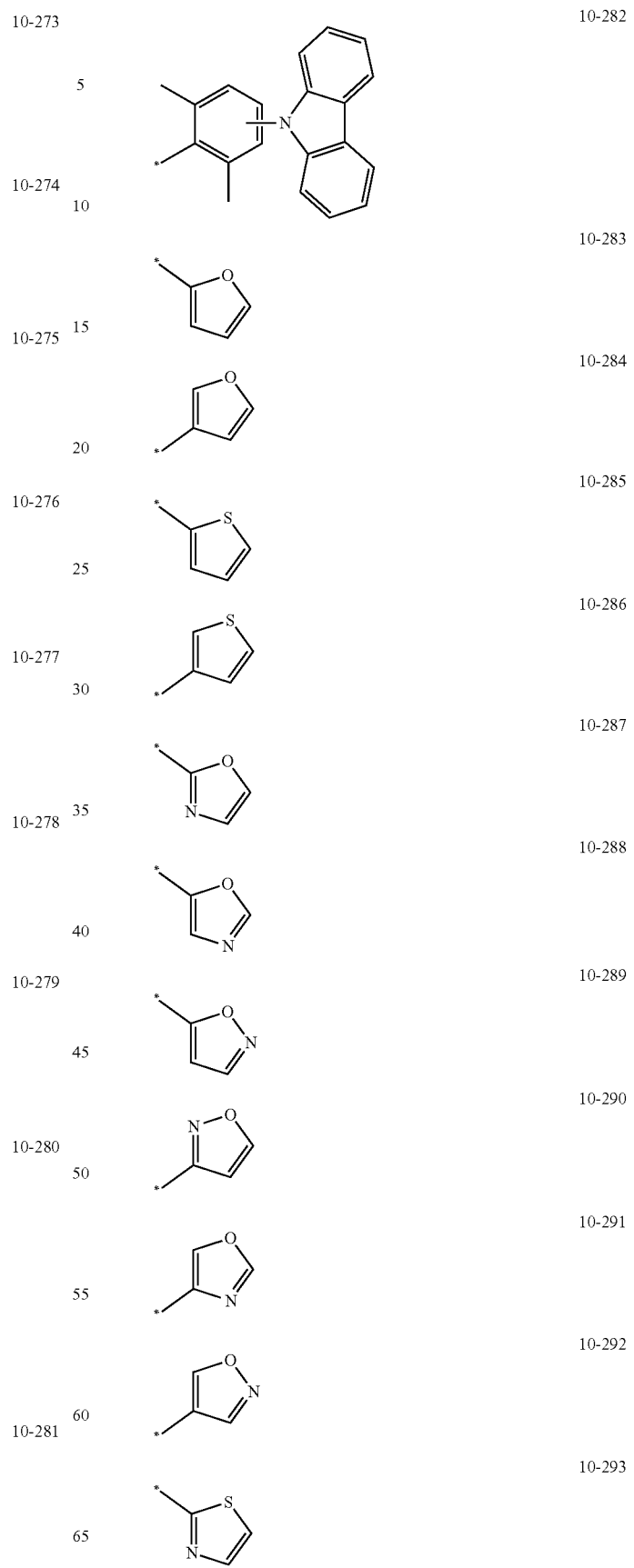

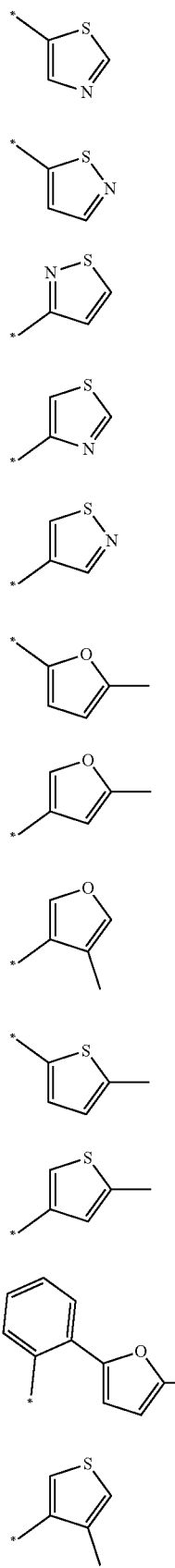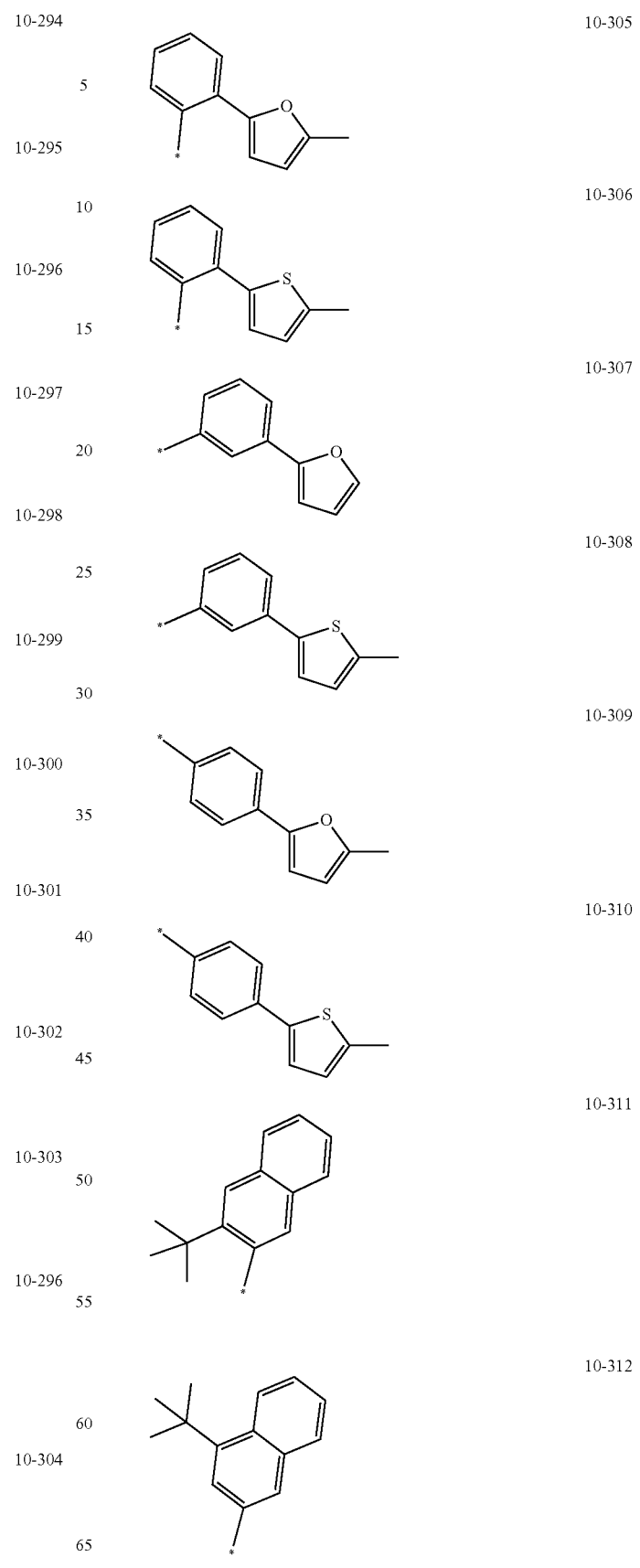

10-313 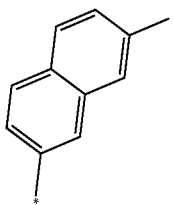
10-314 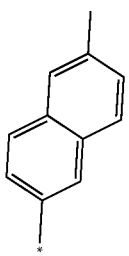
10-315 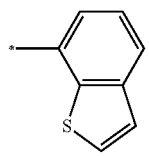
10-316 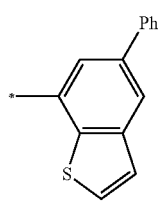
10-317 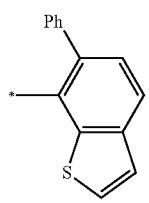
10-318 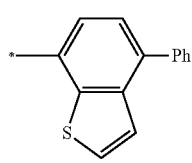
10-319 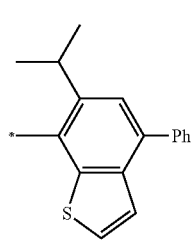
10-320 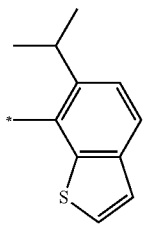
10-321 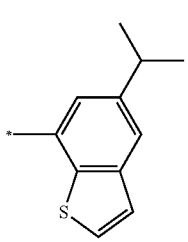
10-322 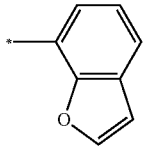
10-323 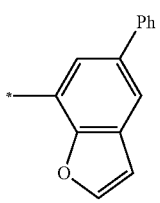
10-324 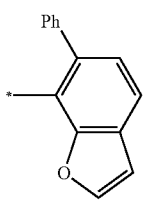
10-325 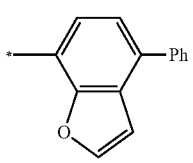
10-326 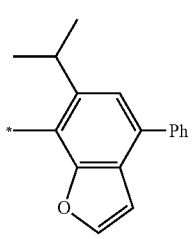

10-327 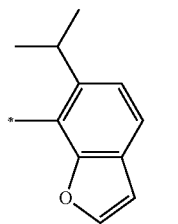
10-328 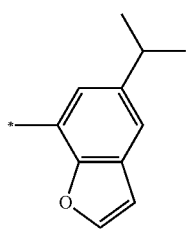
10-329 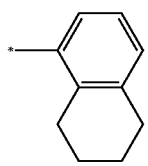
10-330 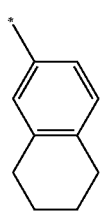
10-331 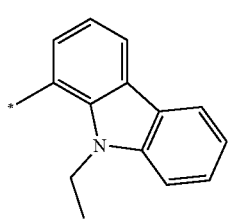
10-332 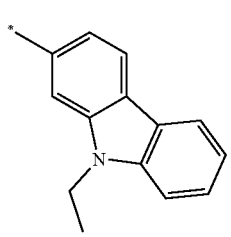
10-333 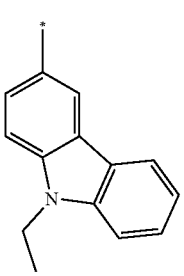
10-334 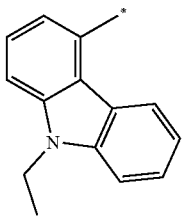
10-335 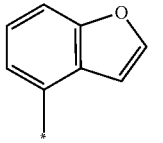
10-336 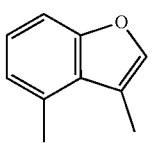
10-337 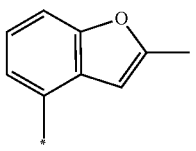
10-338 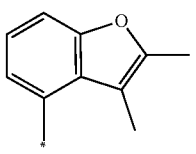
10-339 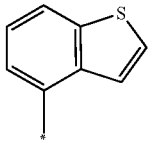
10-340 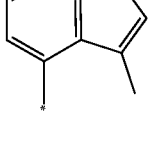
10-341
10-342

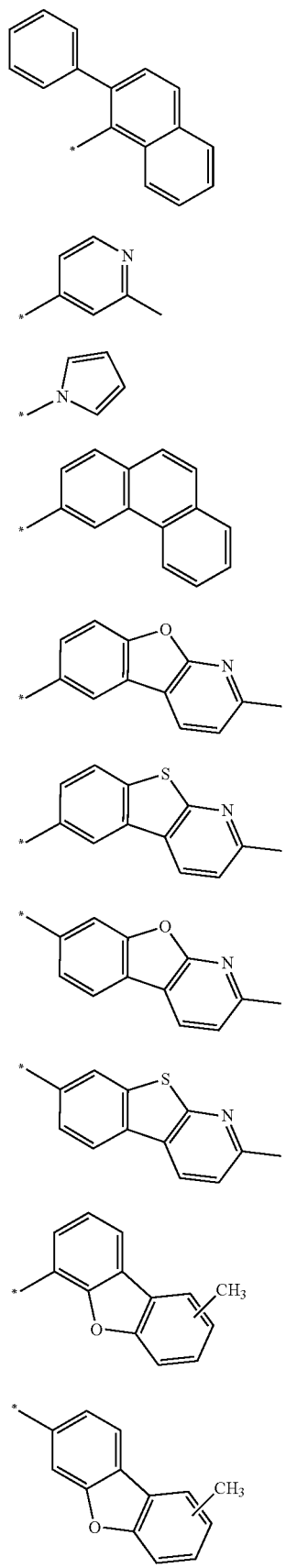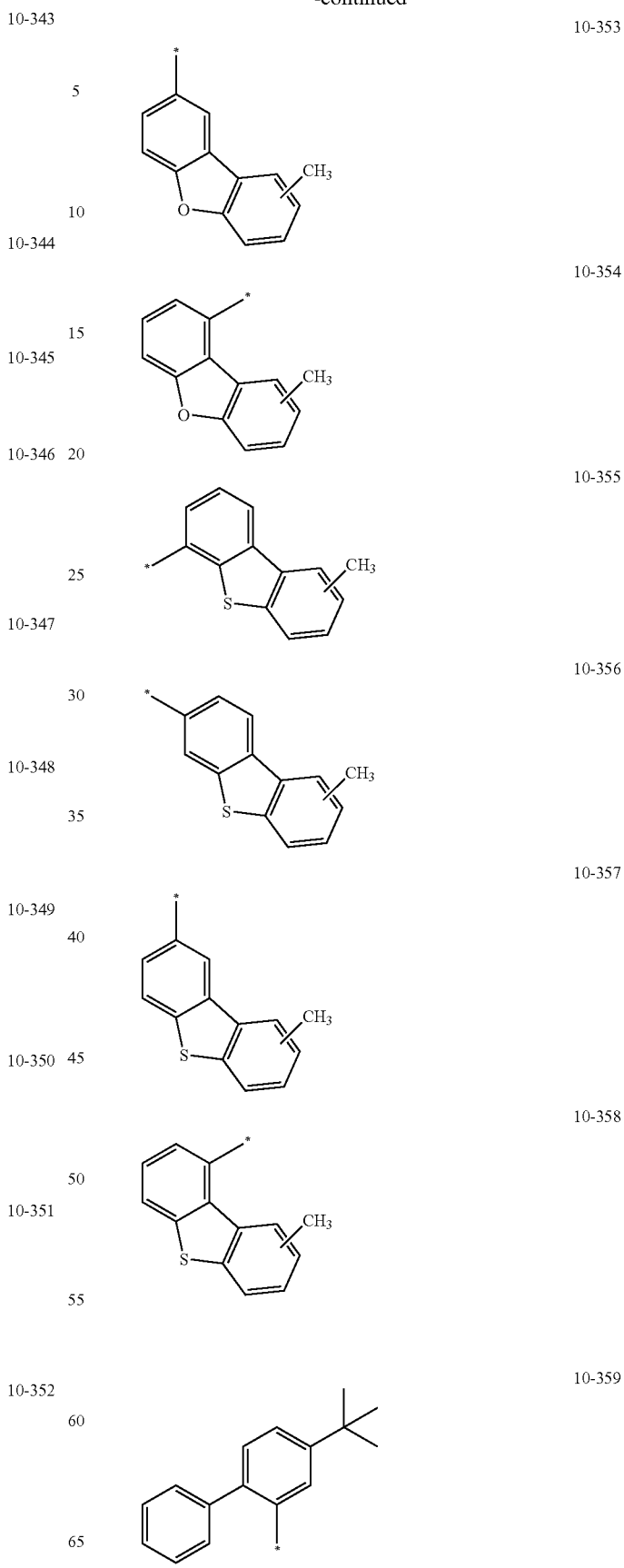

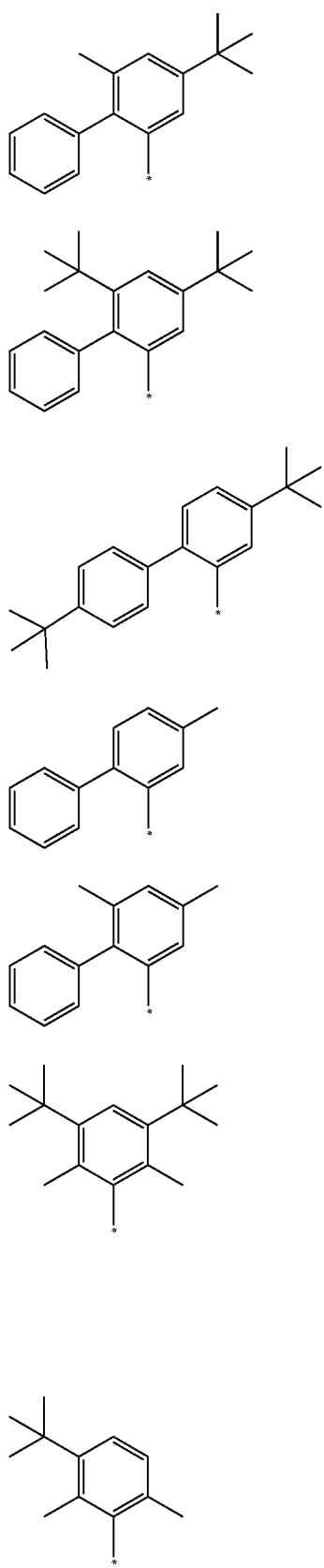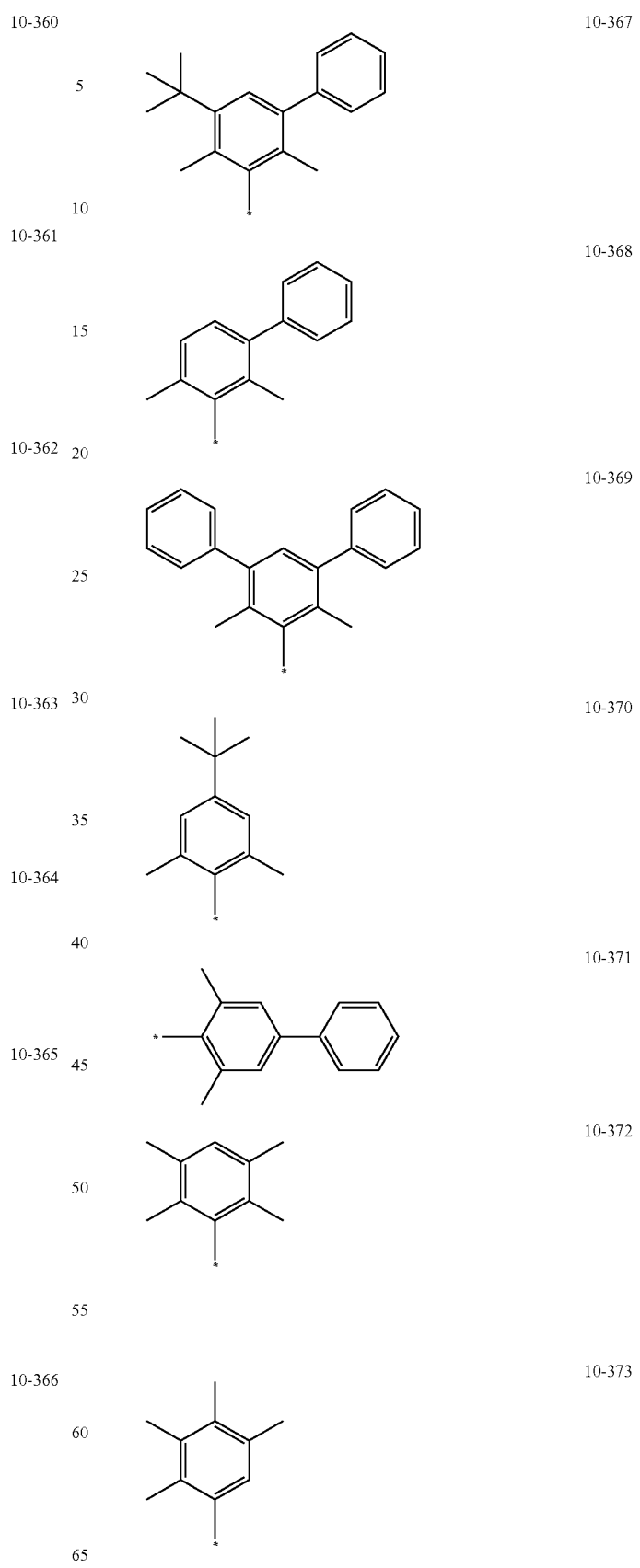

-continued 10-374 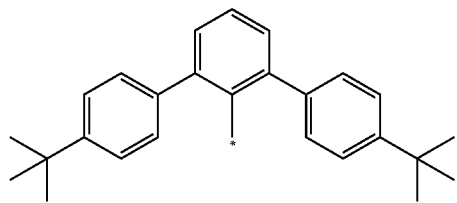

10-375 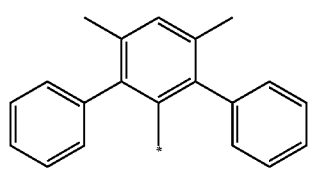

10-376 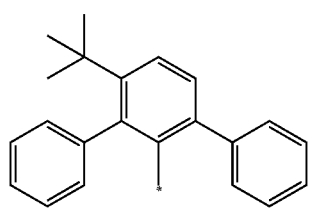

10-377 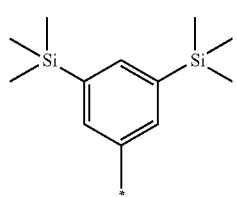

10-378 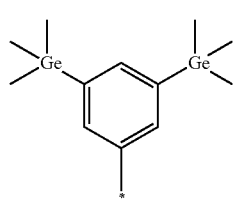

10-379 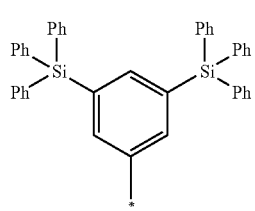

10-380 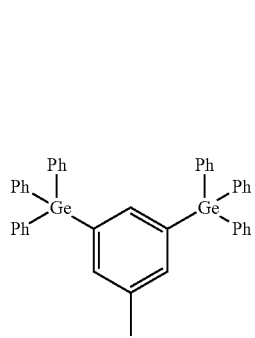

In Formulae 9-1 to 9-39, 9-201 to 9-236, 10-1 to 10-130, and 10-201 to 10-380, * indicates a binding site to an adjacent atom, "Ph" represents a phenyl group, "TMS" and "SiMe₃" each represent a trimethylsilyl group, and "TMG" and "GeMe₃" each represent a trimethylgermyl group.

The "group represented by Formulae 9-1 to 9-39 in which at least one hydrogen is substituted with deuterium" and the "group represented by Formulae 9-201 to 9-236 in which at least one hydrogen is substituted with deuterium" may each be, for example, a group represented by one of Formulae 9-501 to 9-514 and 9-601 to 9-636:

9-501 

9-502 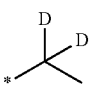

9-503 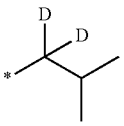

9-504 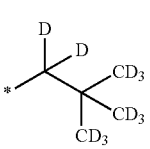

9-505 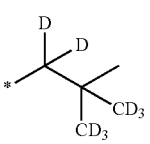

9-506 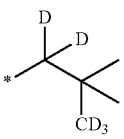

9-507 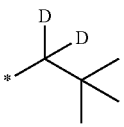

9-508 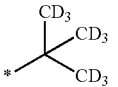

9-509 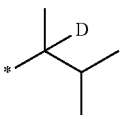

9-510 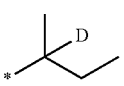

-continued
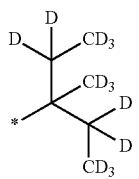
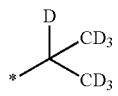
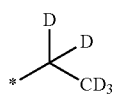
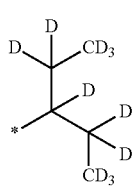
9-601
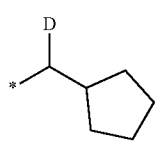
9-602
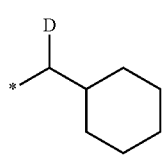
9-603
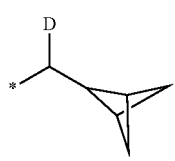
9-604
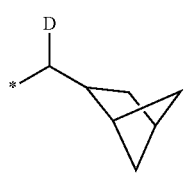
9-605
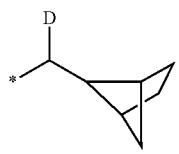
9-606
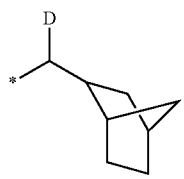
-continued
5-511
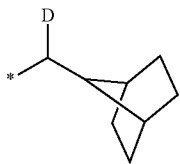
9-512
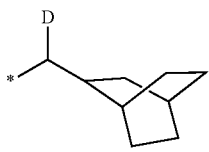
9-513
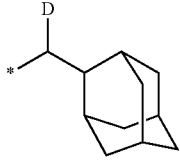
9-514
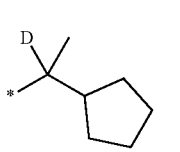
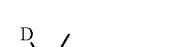
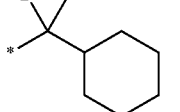
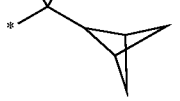
9-607
9-608
9-609
9-610
9-611
9-612
9-613
9-614
9-615
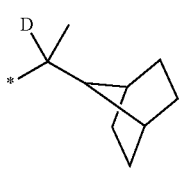
9-616

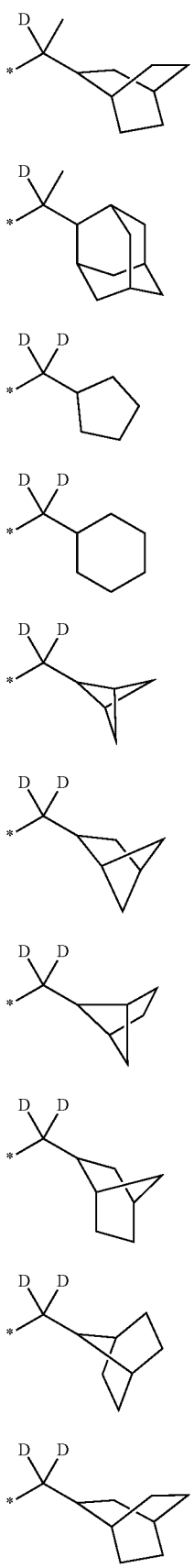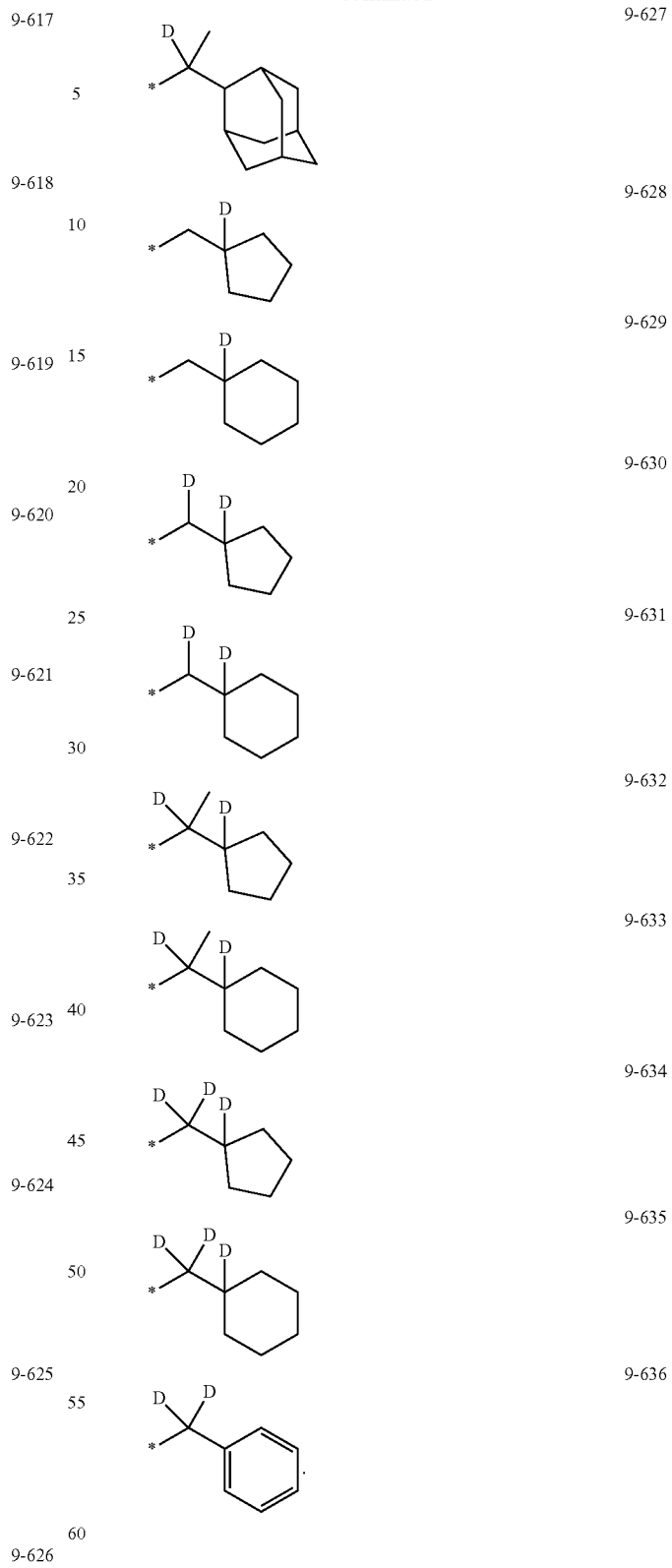
The "group represented by Formulae 9-1 to 9-39 in which at least one hydrogen is substituted with —F" and the "group represented by Formulae 9-201 to 9-236 in which at least one hydrogen is substituted with —F" may each be, for example, a group represented by one of Formulae 9-701 to 710:

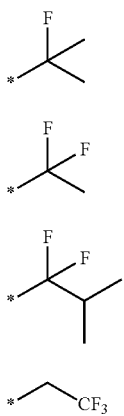
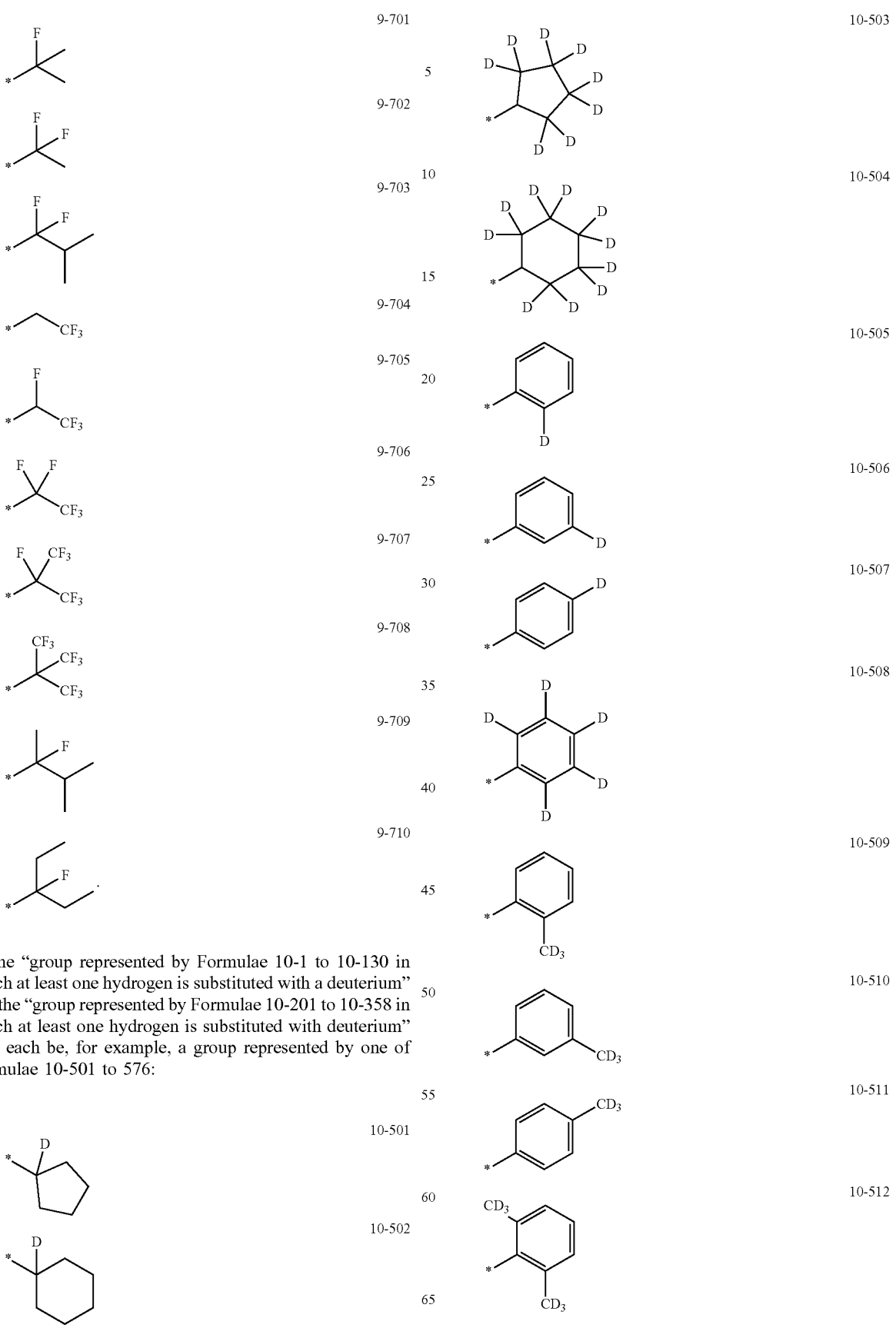
The "group represented by Formulae 10-1 to 10-130 in which at least one hydrogen is substituted with a deuterium" and the "group represented by Formulae 10-201 to 10-358 in which at least one hydrogen is substituted with deuterium" may each be, for example, a group represented by one of Formulae 10-501 to 576:
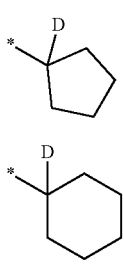

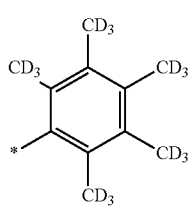
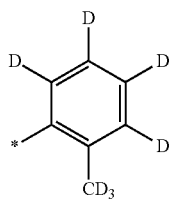

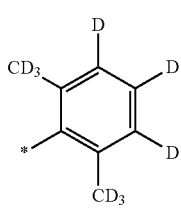
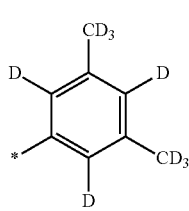
10-513
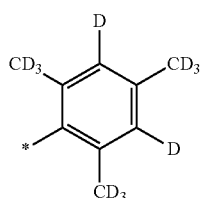
10-514
10-515
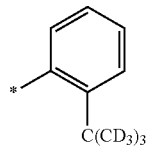
10-516
10-517
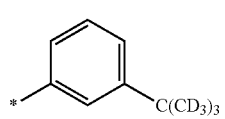
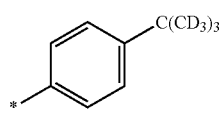
10-518
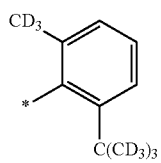
10-519
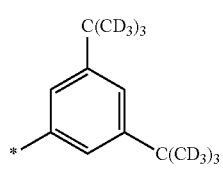
10-520
10-521
10-522
10-523
10-524
10-525
10-526
10-527
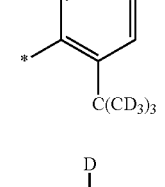
10-528
10-529
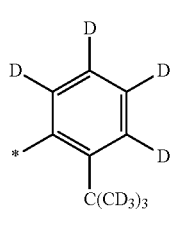

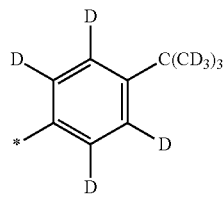
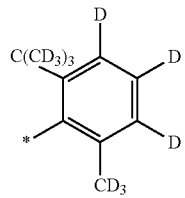
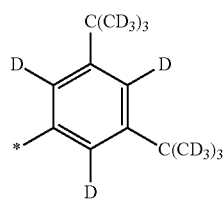
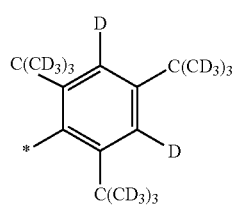
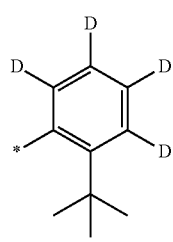
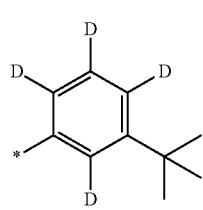
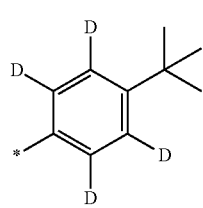
10-530
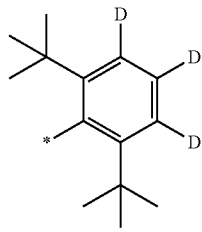
10-531
10-532
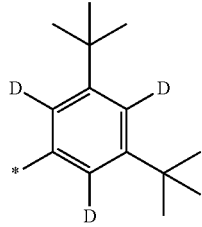
10-533
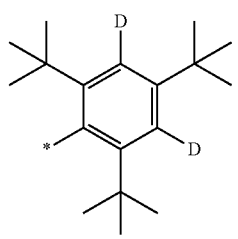
10-534
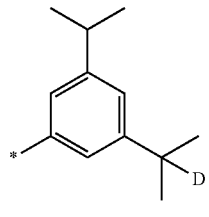
10-535
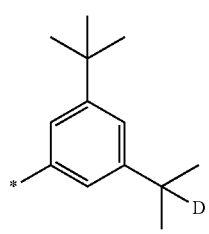
10-536
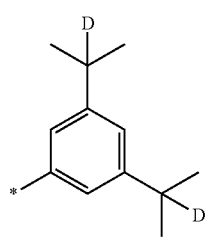
10-537
10-538
10-540
10-541
10-542
10-543
10-544
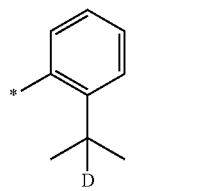

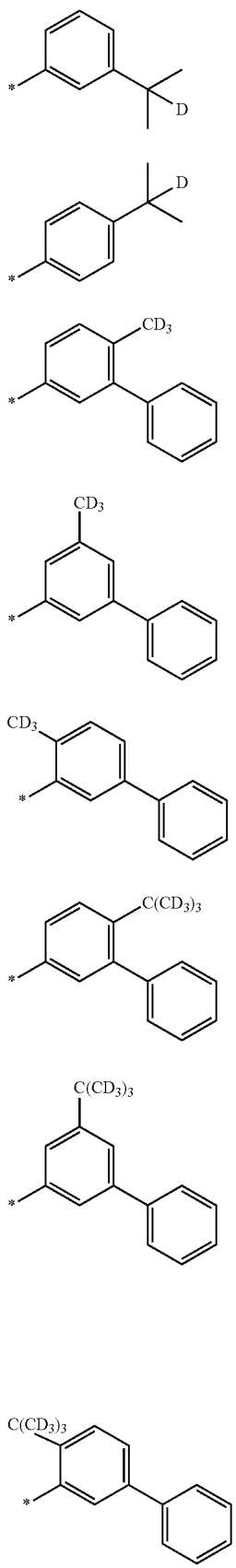
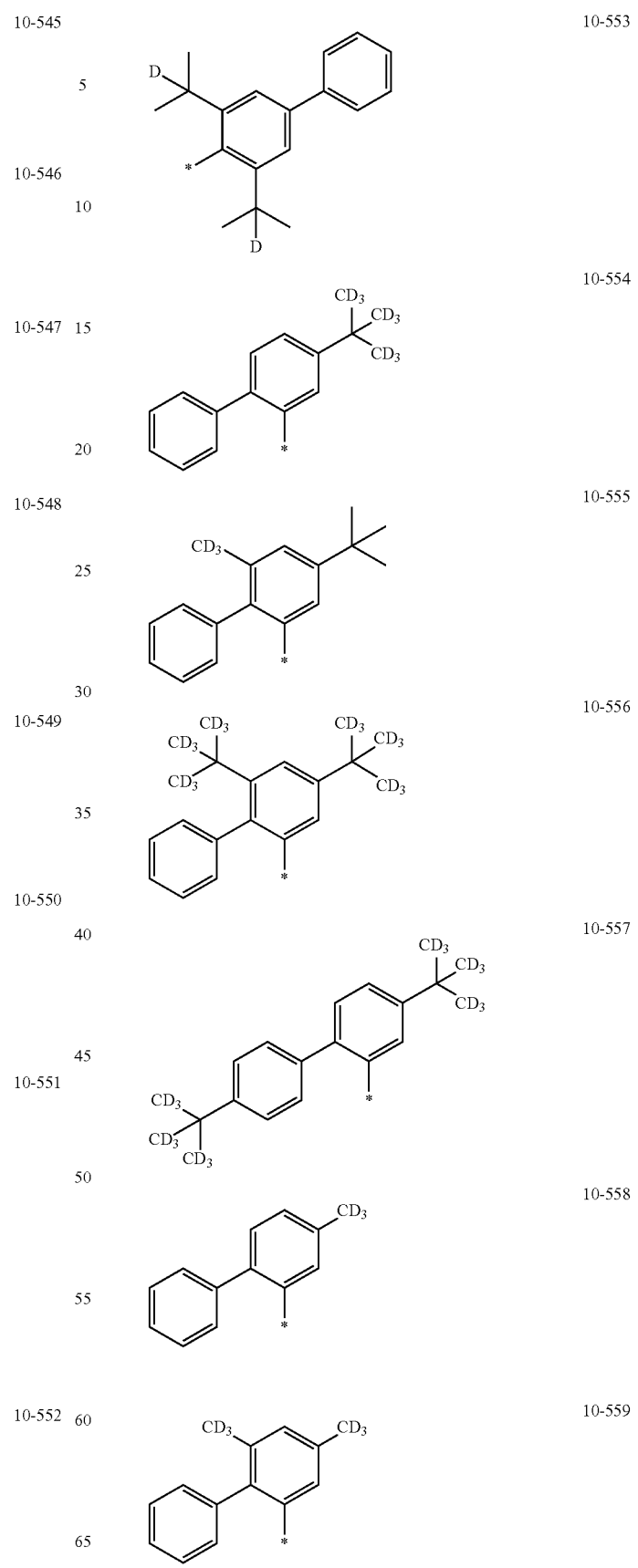

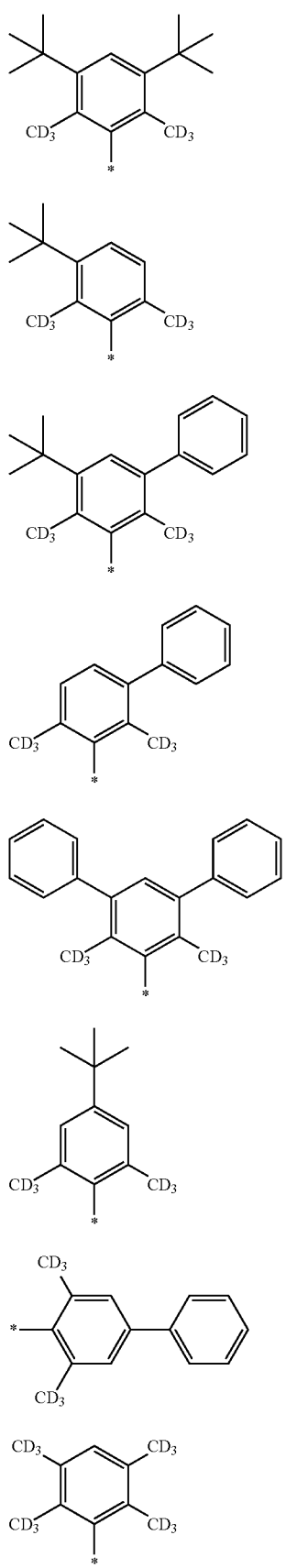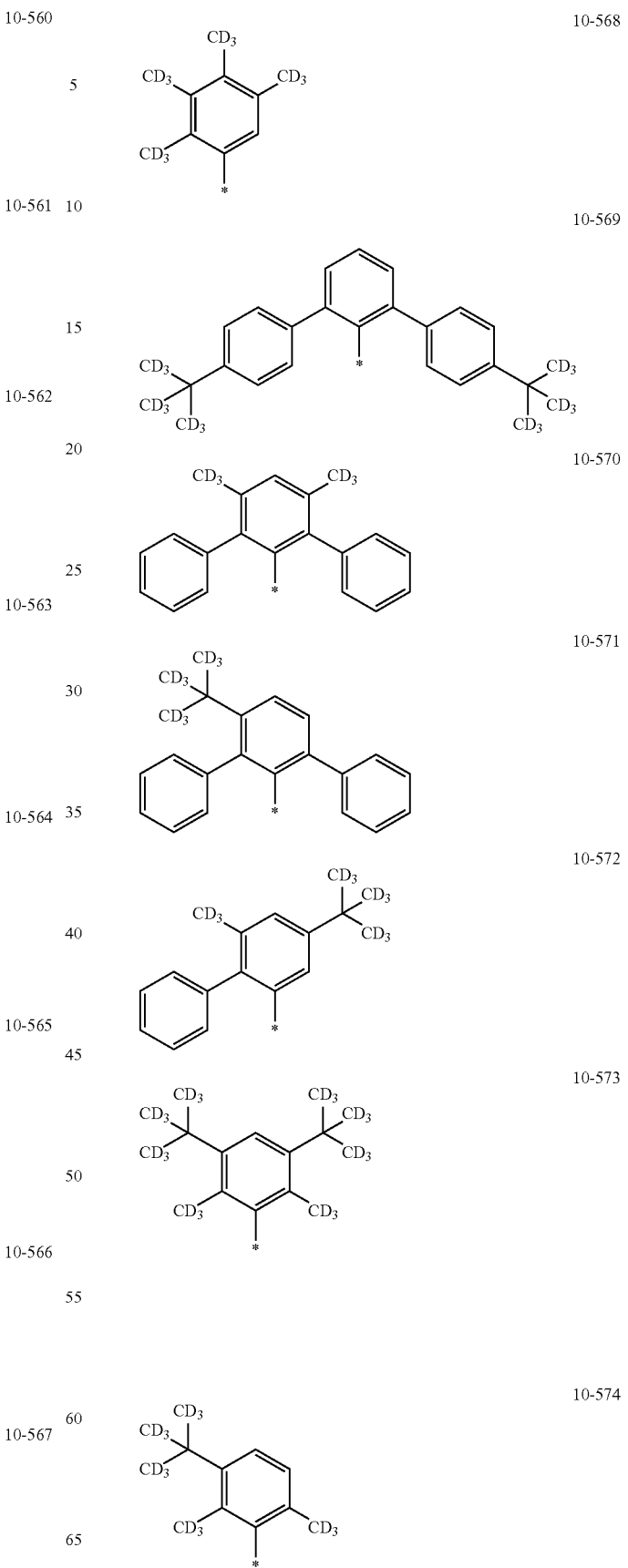

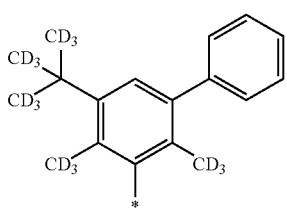
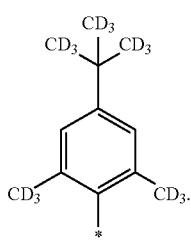
The "group represented by Formulae 10-1 to 10-130 in which at least one hydrogen is substituted with —F" and the "group represented by Formulae 10-201 to 10-358 in which at least one hydrogen is substituted with —F" may each be, for example, a group represented by one of Formulae 10-601 to 10-617:
10-601
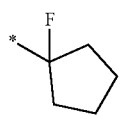
10-602
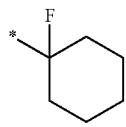
10-603
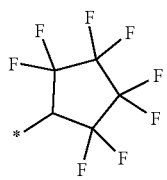
10-604
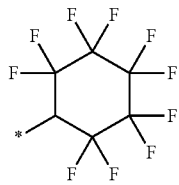
10-605
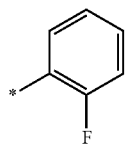
10-606
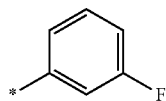
10-607
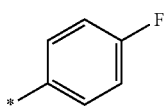
10-608
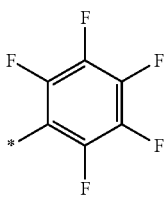
10-609
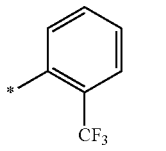
10-610
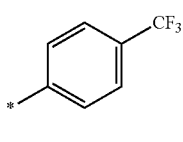
10-611

10-612
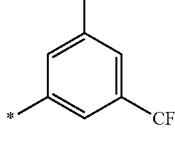
10-613
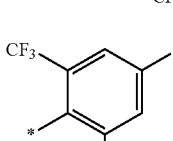
10-614
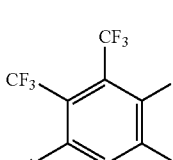
10-615
10-616

-continued 10-617

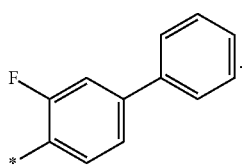

In some embodiments, in Formulae 1-1 and 1-2, $R_{11}$ to $R_{19}$ may each independently be hydrogen, deuterium, —F, —$CH_3$, —$CD_3$, —$CD_2H$, —$CDH_2$, —$CF_3$, —$CF_2H$, —$CFH_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, a group represented by one of Formulae 10-359 to 10-380, a group represented by one of Formulae 10-359 to 10-380 in which at least one hydrogen is substituted with deuterium, a group represented by one of Formulae 10-359 to 10-380 in which at least one hydrogen is substituted with —F, —$Si(Q_1)(Q_2)(Q_3)$, —$Ge(Q_1)(Q_2)(Q_3)$, —$C(Q_1)(Q_2)(Q_3)$, —$B(Q_1)(Q_2)$, or —$N(Q_1)(Q_2)$, wherein $Q_1$ to $Q_3$ may each independently be:

deuterium, —F, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, —$CD_2CDH_2$, —$CF_3$, —$CF_2H$, —$CFH_2$, —$CH_2CF_3$, —$CH_2CF_2H$, —$CH_2CFH_2$, —$CHFCH_3$, —$CHFCF_2H$, —$CHFCFH_2$, —$CHFCF_3$, —$CF_2CF_3$, —$CF_2CF_2H$, or —$CF_2CFH_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

In Formulae 1-1 and 1-2, b11 to b19 may respectively indicate the number of substitution(s) of $R_{11}$ to $R_{19}$, and b11, b14, and b19 may each independently be 0, 1, 2, or 3, b12, b15, and b18 may each independently be 0, 1, 2, 3, or 4, and b13 and b16 may each independently be 0, 1, or 2, and b17 may be 0 or 1. In Formulae 1-1 and 1-2, when b11 to b19 are each at least two, at least two $R_{11}$(s) to $R_{19}$(s) may be identical to or different from each other.

In the heterocyclic compound, in Formula 1-1, a case where $X_{14}$ may be *1, $X_{15}$ may be *2, $W_{12}$ may be *1, $W_{11}$ may be *2, $Y_{15}$ may be *3, $Y_{14}$ may be *4, $W_{16}$ may be *3, and $W_{15}$ may be *4 may be excluded.

In some embodiments, a heterocyclic compound may not be represented by Formula X:

Formula X

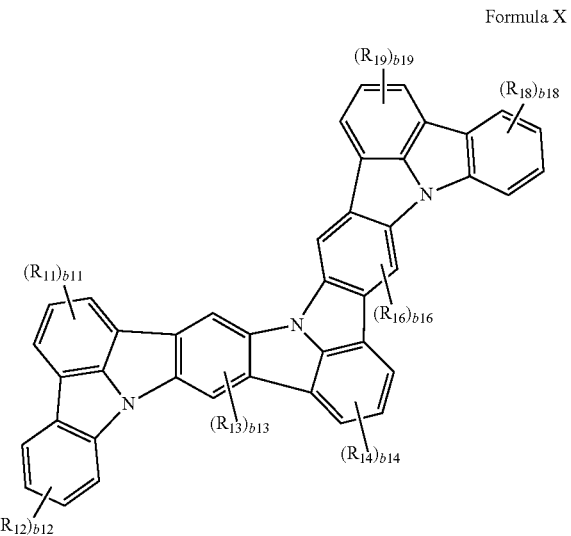

wherein, in Formula X, $R_{11}$ to $R_{14}$, $R_{16}$, $R_{18}$, $R_{19}$, b11 to b14, b16, b18, and b19 may respectively be understood by referring to the descriptions of $R_{11}$ to $R_{14}$, $R_{16}$, $R_{18}$, $R_{19}$, b11 to b14, b16, b18, and b19 provided herein.

In some embodiments, in Formula 1-1, $W_{11}$ may be *1, $W_{12}$ may be *2, $W_{15}$ may be *3, and $W_{16}$ may be *4;

in Formula 1-1, $W_{11}$ may be *1, $W_{12}$ may be *2, $W_{15}$ may be *4, and $W_{16}$ may be *3;

in Formula 1-1, $W_{11}$ may be *2, $W_{11}$ may be *1, $W_{15}$ may be *3, and $W_{16}$ may be *4;

in Formula 1-2, $W_{13}$ may be *6, $W_{14}$ may be *5, $W_{15}$ may be *8, and $W_{16}$ may be *7;

in Formula 1-2, $W_{13}$ may be *6, $W_{14}$ may be *5, $W_{15}$ may be *7, and $W_{16}$ may be *8;

in Formula 1-2, $W_{13}$ may be *5, $W_{14}$ may be *6, $W_{15}$ may be *8, and $W_{16}$ may be *7; or in Formula 1-2, $W_{13}$ may be *6, $W_{14}$ may be *6, $W_{15}$ may be *7, and $W_{16}$ may be *8.

In some embodiments, the heterocyclic compound may be represented by one of Formulae 11 to 17:

Formula 11

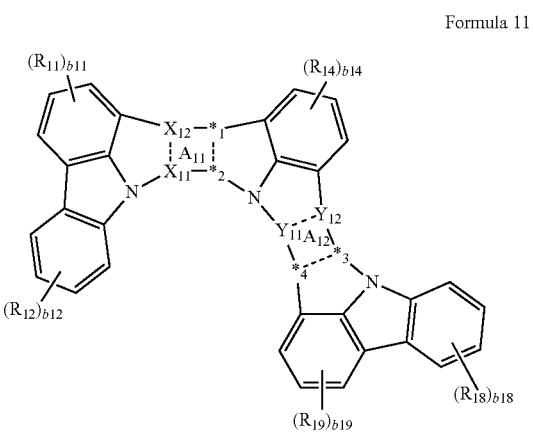

Formula 12
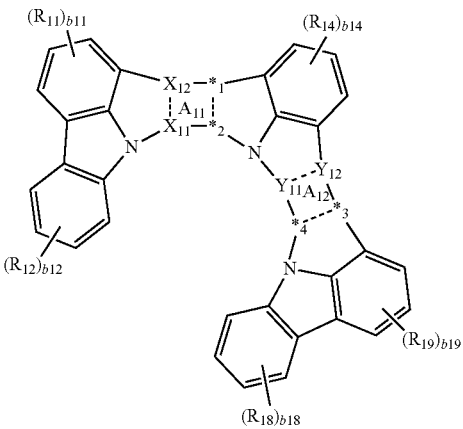
Formula 13
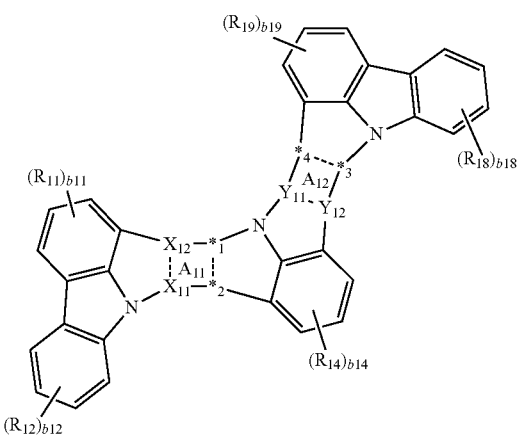
Formula 14
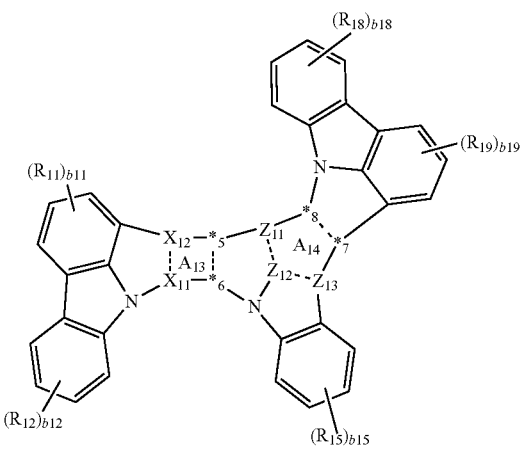
Formula 15
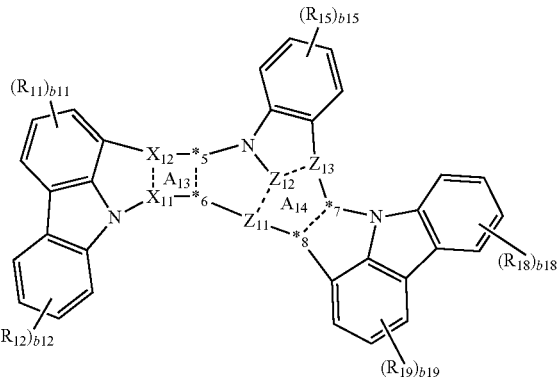
Formula 16
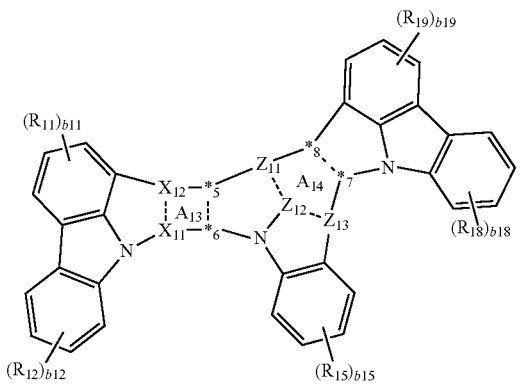
Formula 17
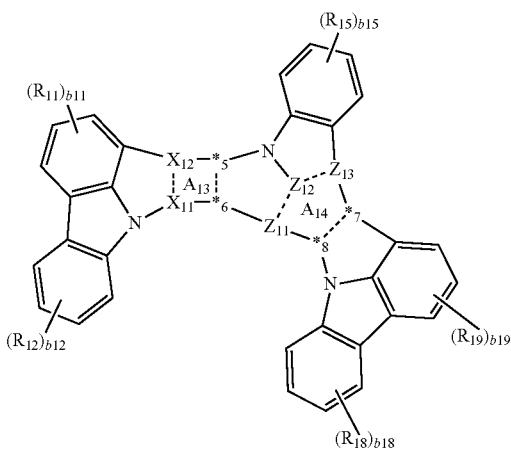
wherein, in Formulae 11 to 17, $A_{11}$ to $A_{14}$, $R_{11}$ to $R_{19}$, b11 to b19, $X_{11}$, $X_{12}$, $Y_{11}$, $Y_{12}$, and $Z_{11}$ to $Z_{13}$ may respectively be understood by referring to the descriptions of $A_{11}$ to $A_{14}$, $R_{11}$ to $R_{19}$, b11 to b19, $X_{11}$, $X_{12}$, $Y_{11}$, $Y_{12}$, and $Z_{11}$ to $Z_{13}$ provided herein.

In Formulae 11, 12, and 14 to 17, $A_{11}$ and $A_{13}$ are each independently a group represented by Formula 2-1, $A_{12}$ is a group represented by Formula 2-2, $A_{14}$ is a group represented by Formula 2-3,

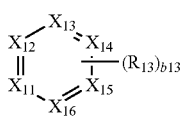

2-1

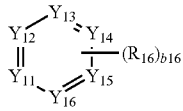

2-2

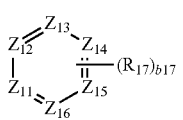

2-3 wherein, in Formulae 2-1 to 2-3, $X_{11}$ to $X_{16}$, $Y_{11}$ to $Y_{16}$, and $Z_{11}$ to $Z_{16}$ are each independently a carbon atom, any suitable two adjacent groups of $X_{13}$ to $X_{16}$ are respectively *1 and *2 in Formulae 11 and 12 or *5 and *6 in Formulae 14 to 17, any suitable two adjacent groups of $Y_{13}$ to $Y_{16}$ are respectively *3 and *4 in Formulae 11 and 12, and any suitable two adjacent groups of $Z_{14}$ to $Z_{16}$ are respectively *7 and *8 in Formulae 14 to 17.

In some embodiments, in Formula 11, i) *1 may be $X_{13}$, *2 may be $X_{14}$, *3 may be $Y_{13}$, and *4 may be $Y_{14}$; ii) *1 may be $X_{13}$, *2 may be $X_{14}$, *3 may be $Y_{14}$, and *4 may be $Y_{15}$; iii) *1 may be $X_{13}$, *2 may be $X_{14}$, *3 may be $Y_{15}$, and *4 may be $Y_{16}$; iv) *1 may be $X_{14}$, *2 may be $X_{15}$, *3 may be $Y_{13}$, and *4 may be $Y_{14}$; v) *1 may be $X_{14}$, *2 may be $X_{15}$, *3 may be $Y_{14}$, and *4 may be $Y_{15}$; vi) *1 may be $X_{14}$, *2 may be $X_{15}$, *3 may be $Y_{15}$, and *4 may be $Y_{16}$; vii) *1 may be $X_{15}$, *2 may be $X_{16}$, *3 may be $Y_{13}$, and *4 may be $Y_{14}$; viii) *1 may be $X_{15}$, *2 may be $X_{16}$, *3 may be $Y_{14}$, and *4 may be $Y_{15}$; or ix) *1 may be $X_{15}$, *2 may be $X_{16}$, *3 may be $Y_{15}$, and *4 may be $Y_{16}$.

In some embodiments, in Formula 12, i) *1 may be $X_{13}$, *2 may be $X_{14}$, *3 may be $Y_{13}$, and *4 may be $Y_{14}$; ii) *1 may be $X_{13}$, *2 may be $X_{14}$, *3 may be $Y_{14}$, and *4 may be $Y_{15}$; iii) *1 may be $X_{13}$, *2 may be $X_{14}$, *3 may be $Y_{15}$, and *4 may be $Y_{16}$; iv) *1 may be $X_{14}$, *2 may be $X_{15}$, *3 may be $Y_{14}$, and *4 may be $Y_{15}$; v) *1 may be $X_{14}$, *2 may be $X_{15}$, *3 may be $Y_{15}$, and *4 may be $Y_{16}$; or vi) *1 may be $X_{15}$, *2 may be $X_{16}$, *3 may be $Y_{15}$, and *4 may be $Y_{16}$.

In some embodiments, in Formula 13, i) *1 may be $X_{13}$, *2 may be $X_{14}$, *3 may be $Y_{13}$, and *4 may be $Y_{14}$; ii) *1 may be $X_{13}$, *2 may be $X_{14}$, *3 may be $Y_{14}$, and *4 may be $Y_{15}$; iii) *1 may be $X_{13}$, *2 may be $X_{14}$, *3 may be $Y_{15}$, and *4 may be $Y_{16}$; iv) *1 may be $X_{14}$, *2 may be $X_{15}$, *3 may be $Y_{14}$, and *4 may be $Y_{15}$; v) *1 may be $X_{15}$, *2 may be $X_{15}$, *3 may be $Y_{15}$, and *4 may be $Y_{16}$; or vi) *1 may be $X_{15}$, *2 may be $X_{16}$, *3 may be $Y_{15}$, and *4 may be $Y_{16}$.

In some embodiments, in Formula 14, i) *5 may be $X_{13}$, *6 may be $X_{14}$, *7 may be $Z_{14}$, and *8 may be $Z_{15}$; ii) *5 may be $X_{13}$, *6 may be $X_{14}$, *7 may be $Z_{15}$, and *8 may be $Z_{16}$; iii) *5 may be $X_{14}$, *6 may be $X_{15}$, *7 may be $Z_{14}$, and *8 may be $Z_{15}$; iv) *5 may be $X_{14}$, *6 may be $X_{15}$, *7 may be $Z_{15}$, and *8 may be $Z_{16}$; v) *5 may be $X_{15}$, *6 may be $X_{16}$, *7 may be $Z_{14}$, and *8 may be $Z_{15}$; or vi) *5 may be $X_{15}$, *6 may be $X_{16}$, *7 may be $Z_{15}$, and *8 may be $Z_{16}$.

In some embodiments, in Formula 15, i) *5 may be $X_{13}$, *6 may be $X_{14}$, *7 may be $Z_{14}$, and *8 may be $Z_{15}$; ii) *5 may be $X_{13}$, *6 may be $X_{14}$, *7 may be $Z_{15}$, and *8 may be $Z_{16}$; iii) *5 may be $X_{14}$, *6 may be $X_{15}$, *7 may be $Z_{14}$, and *8 may be $Z_{15}$; iv) *5 may be $X_{14}$, *6 may be $X_{15}$, *7 may be $Z_{15}$, and *8 may be $Z_{16}$; v) *5 may be $X_{15}$, *6 may be $X_{16}$, *7 may be $Z_{14}$, and *8 may be $Z_{15}$; or vi) *5 may be $X_{15}$, *6 may be $X_{16}$, *7 may be $Z_{15}$, and *8 may be $Z_{16}$.

In some embodiments, in Formula 16, i) *5 may be $X_{13}$, *6 may be $X_{14}$, *7 may be $Z_{14}$, and *8 may be $Z_{15}$; ii) *5 may be $X_{13}$, *6 may be $X_{14}$, *7 may be $Z_{15}$, and *8 may be $Z_{16}$; iii) *5 may be $X_{14}$, *6 may be $X_{15}$, *7 may be $Z_{14}$, and *8 may be $Z_{15}$; iv) *5 may be $X_{14}$, *6 may be $X_{15}$, *7 may be $Z_{15}$, and *8 may be $Z_{16}$; v) *5 may be $X_{15}$, *6 may be $X_{16}$, *7 may be $Z_{14}$, and *8 may be $Z_{15}$; or vi) *5 may be $X_{15}$, *6 may be $X_{16}$, *7 may be $Z_{15}$, and *8 may be $Z_{16}$.

In some embodiments, in Formula 17, i) *5 may be $X_{13}$, *6 may be $X_{14}$, *7 may be $Z_{14}$, and *8 may be $Z_{15}$; ii) *5 may be $X_{13}$, *6 may be $X_{14}$, *7 may be $Z_{15}$, and *8 may be $Z_{16}$; iii) *5 may be $X_{14}$, *6 may be $X_{15}$, *7 may be $Z_{14}$, and *8 may be $Z_{15}$; iv) *5 may be $X_{14}$, *6 may be $X_{15}$, *7 may be $Z_{15}$, and *8 may be $Z_{16}$; v) *5 may be $X_{15}$, *6 may be $X_{16}$, *7 may be $Z_{14}$, and *8 may be $Z_{15}$; or vi) *5 may be $X_{15}$, *6 may be $X_{16}$, *7 may be $Z_{15}$, and *8 may be $Z_{16}$.

In some embodiments, the heterocyclic compound may be represented by one of Formulae 11-1 to 11-9, 12-1 to 12-6, 13-1 to 13-5, 14-1 to 14-6, 15-1 to 15-6, 16-1 to 16-6, and 17-1 to 17-6:

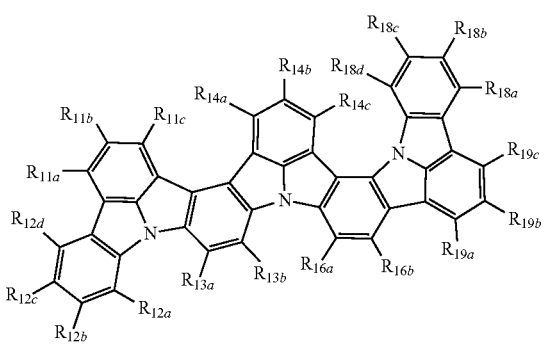

11-1

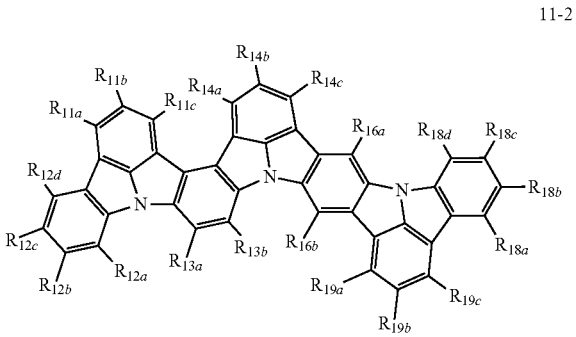

11-2

11-3
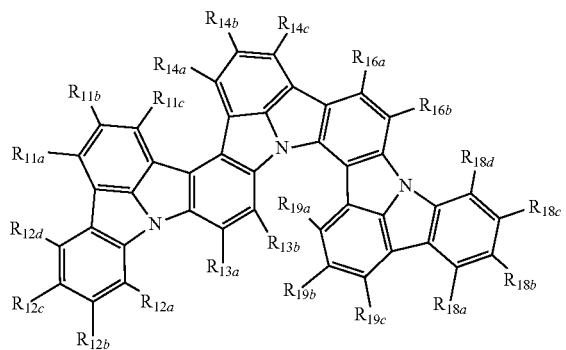
11-4
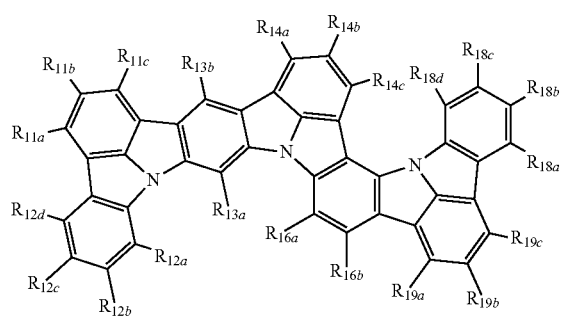
11-5
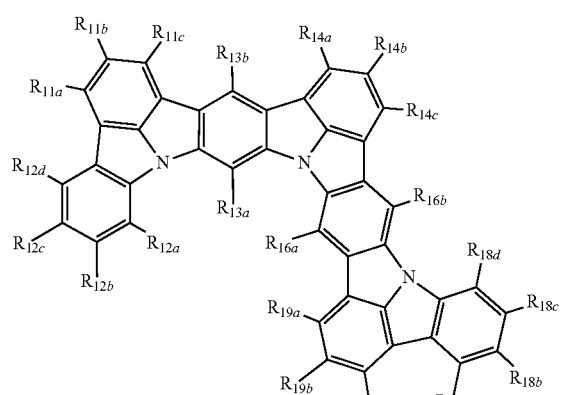
11-7
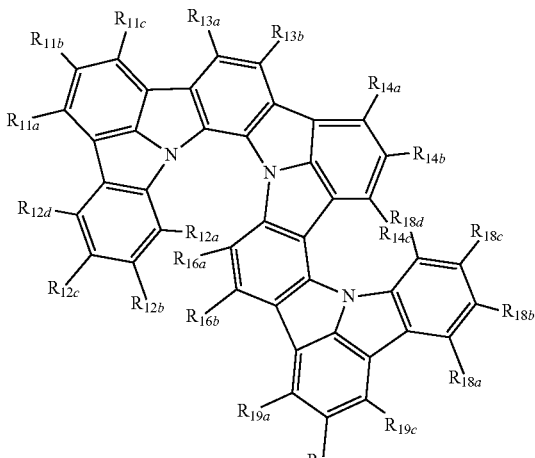
11-8
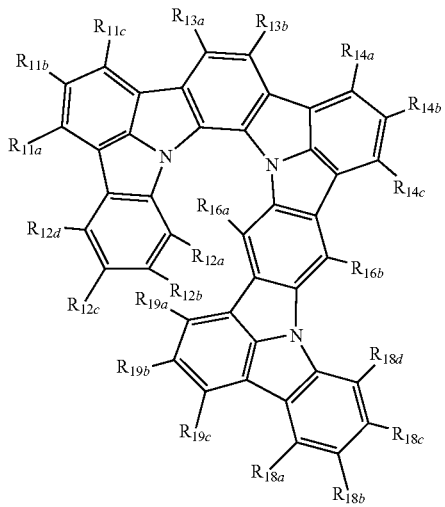
11-9
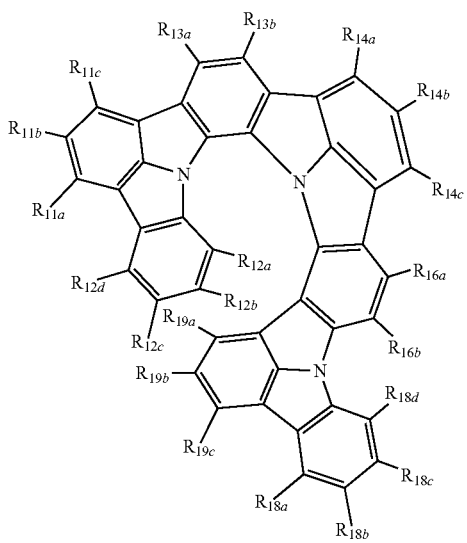

-continued
12-1
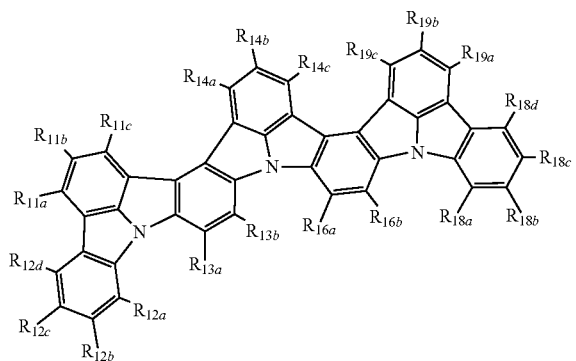
12-2
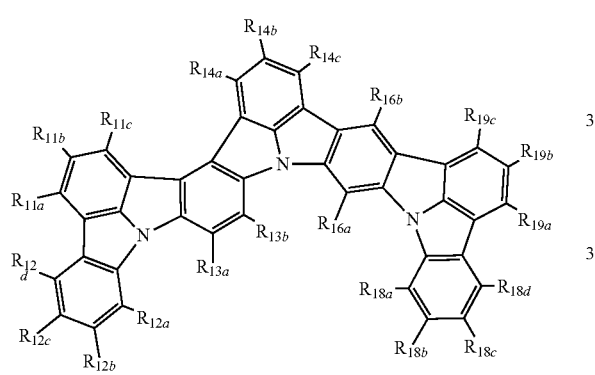
12-3
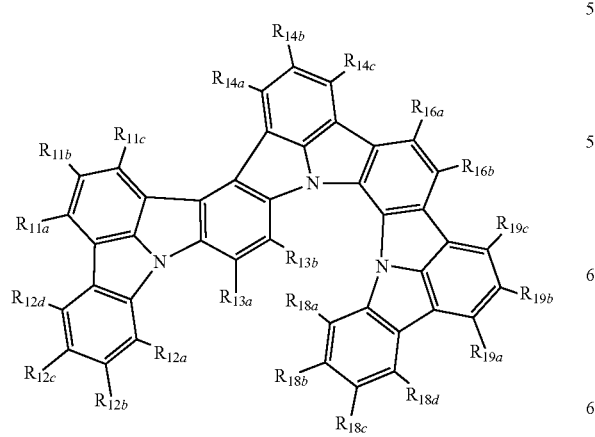
-continued
12-4
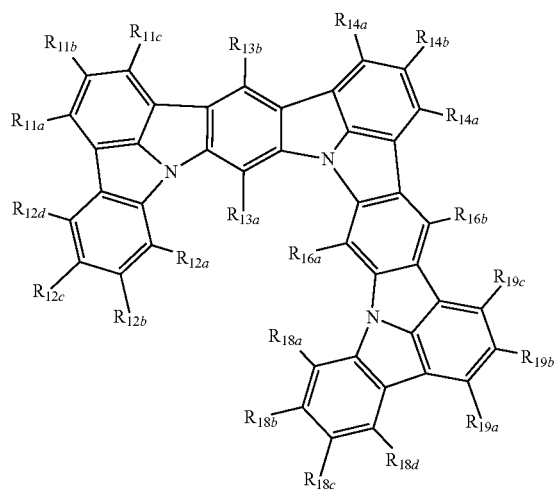
12-5
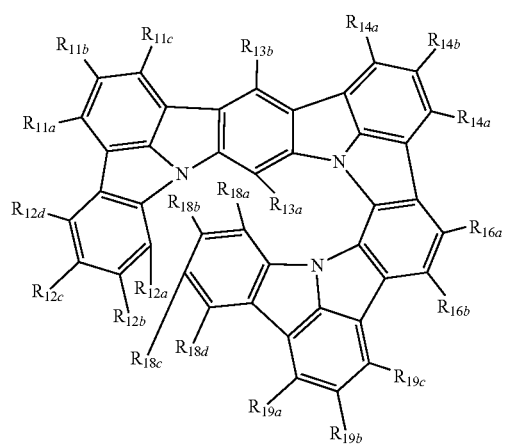
12-6
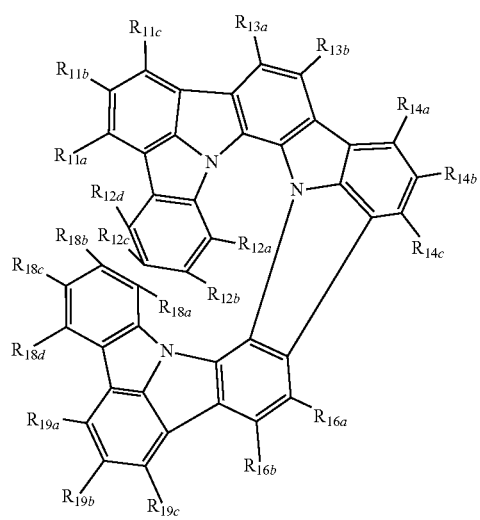

-continued
13-1
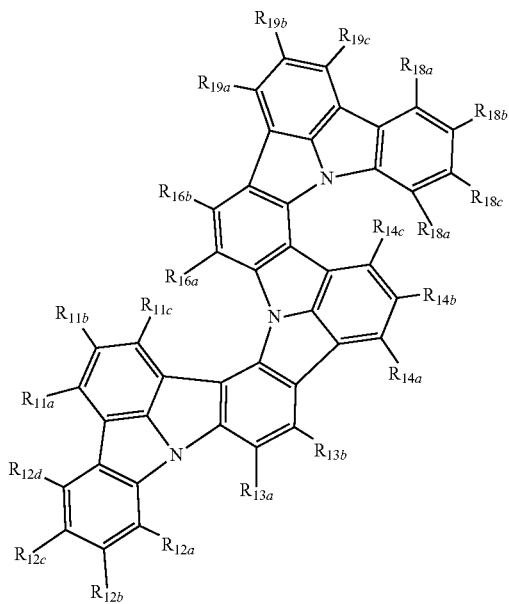
13-3
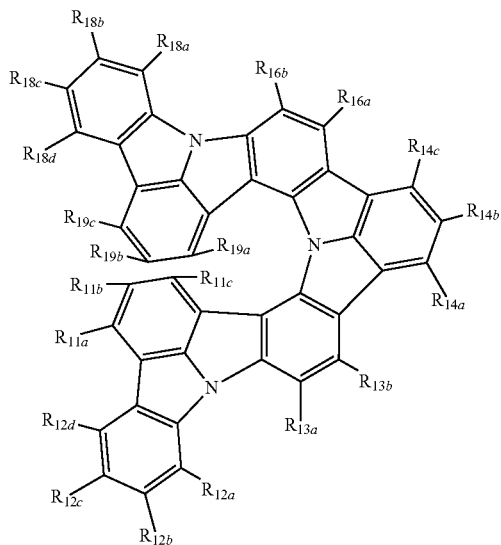
13-4
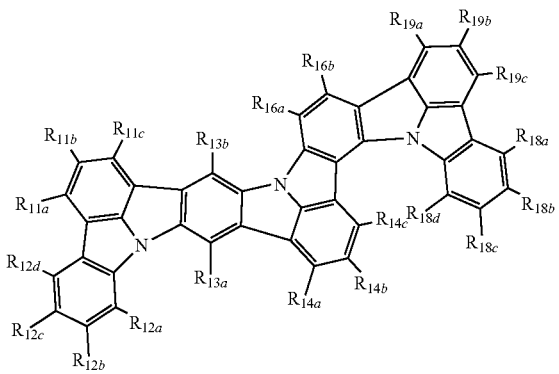
13-5
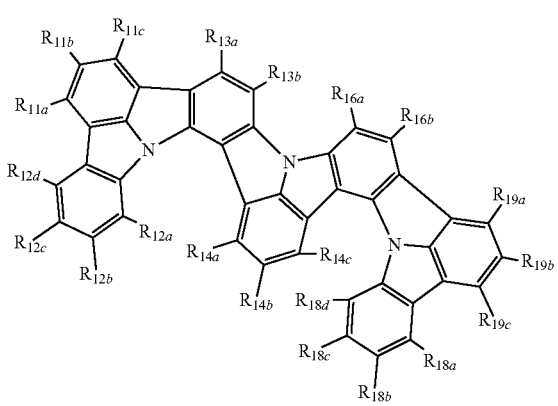

-continued
14-1
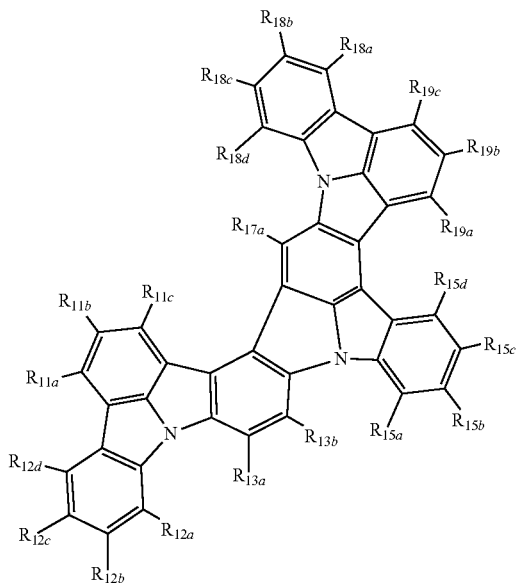
14-2
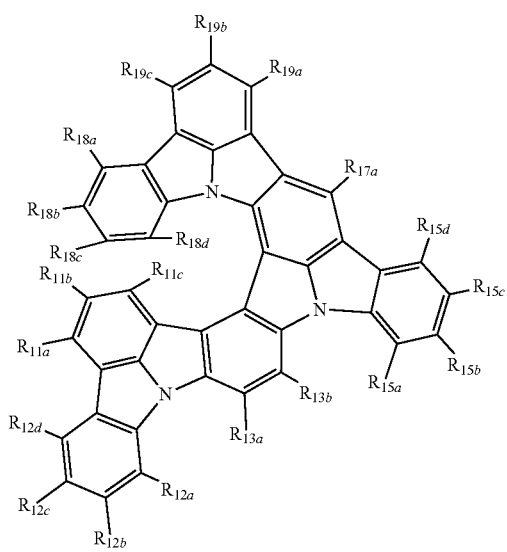
14-3
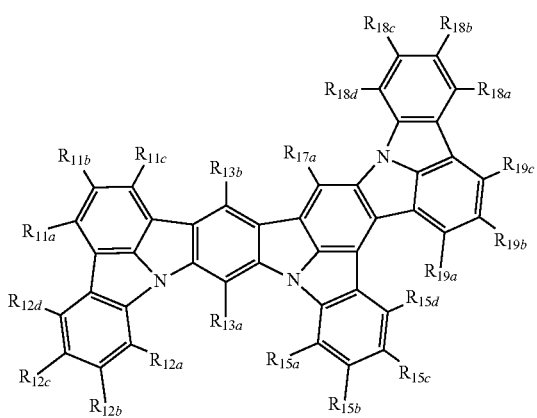
14-4
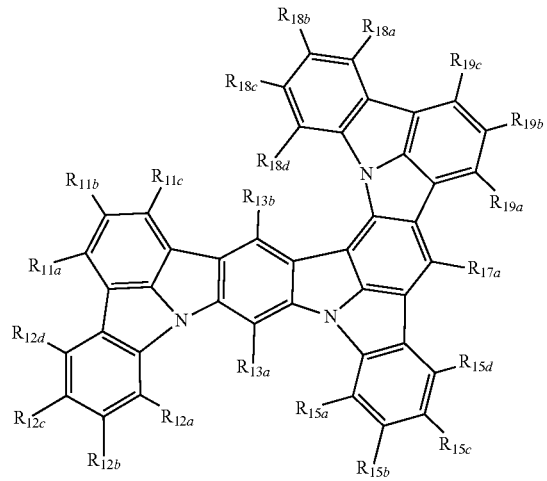
14-5
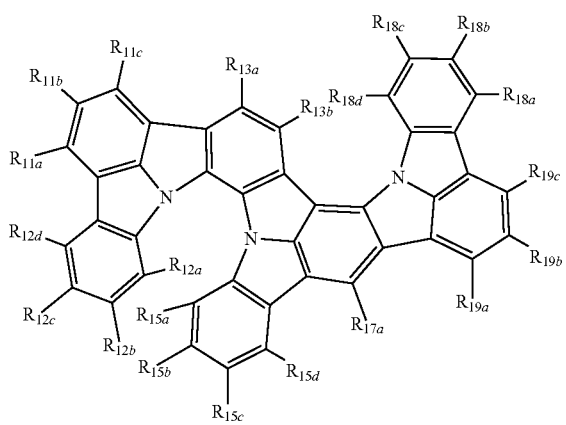
14-6
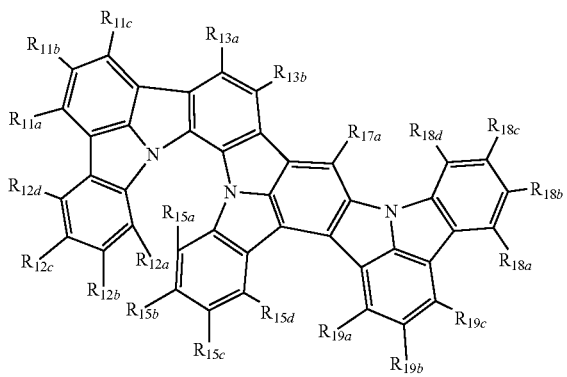

15-1
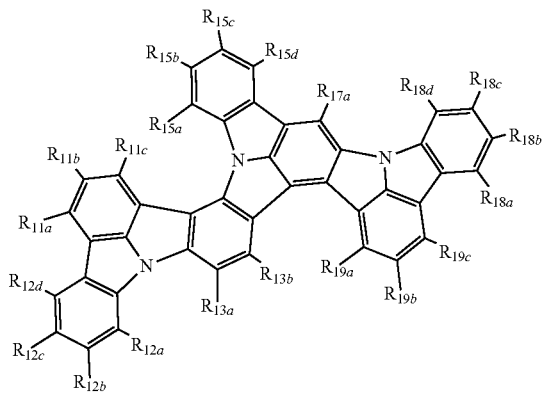
15-2
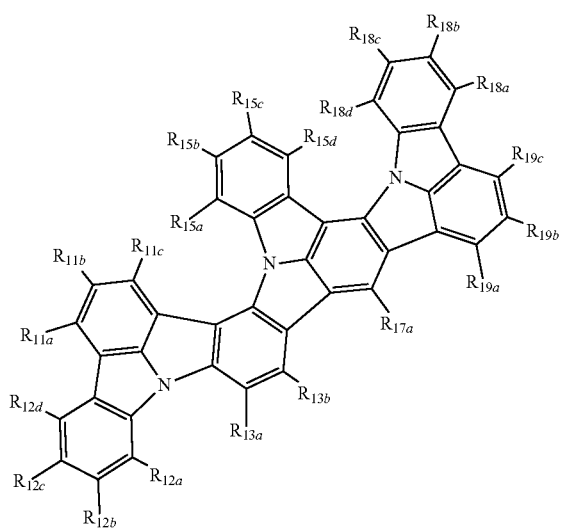
15-3
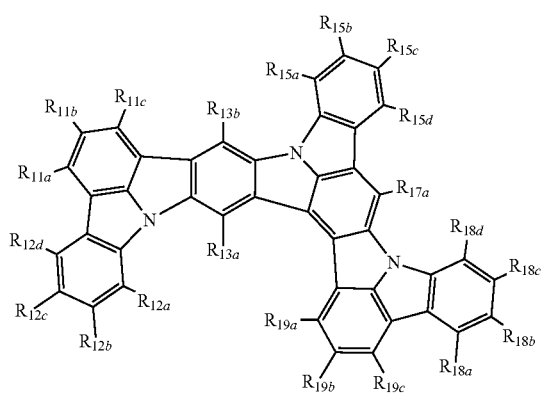
15-4
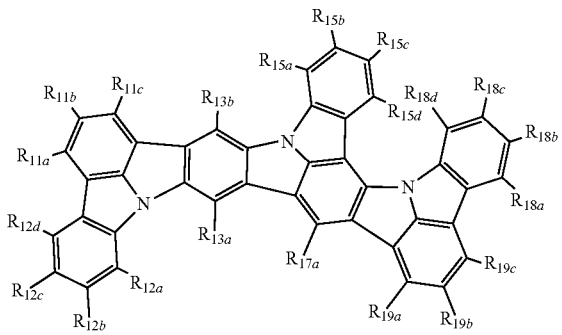
15-5
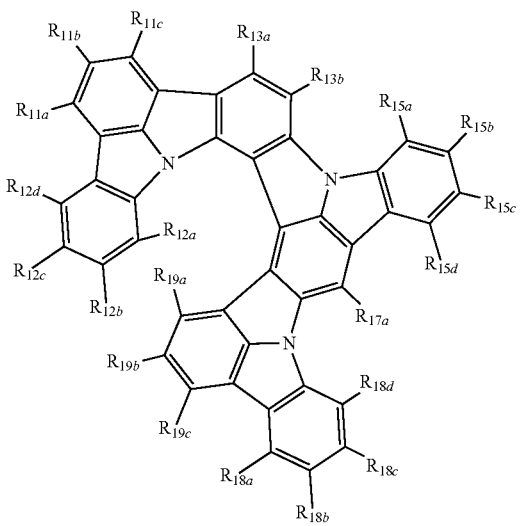
15-6
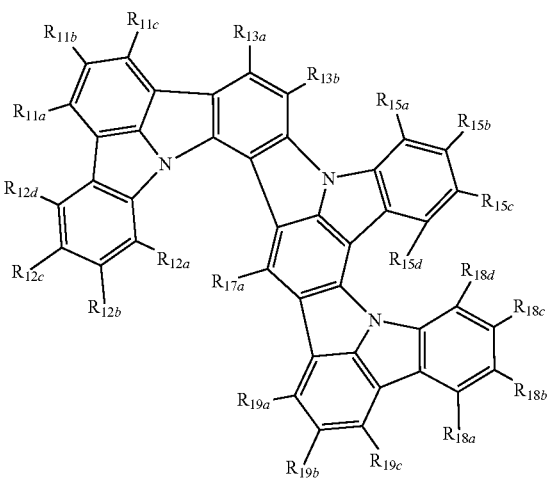

-continued
16-1
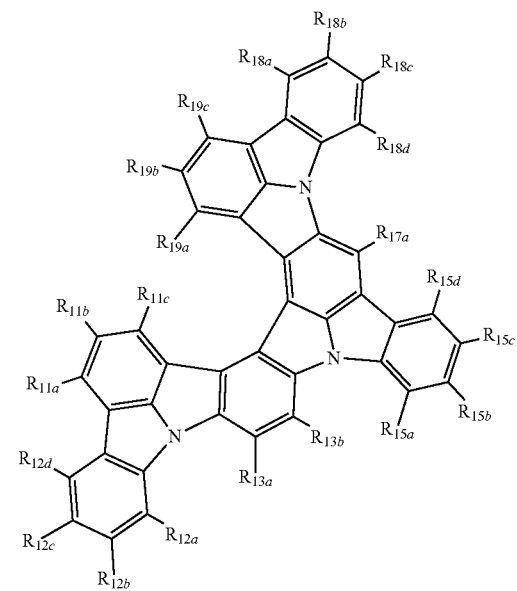
16-2
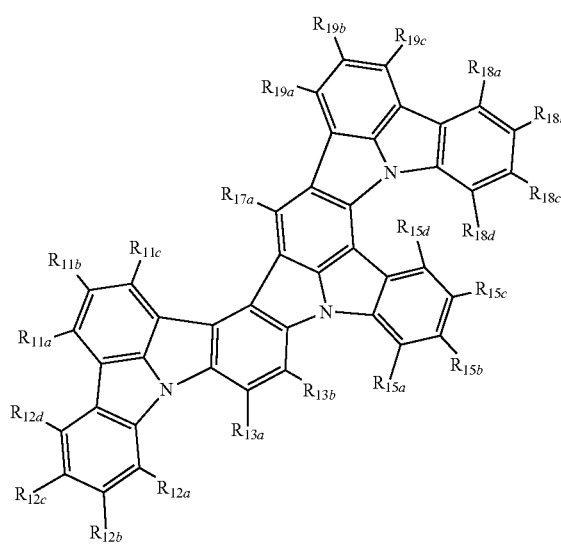
16-3
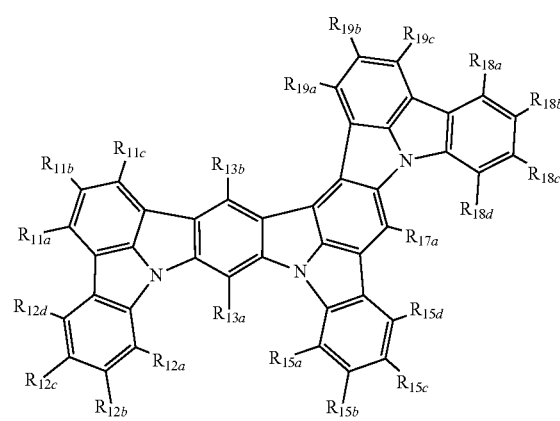
-continued
16-4
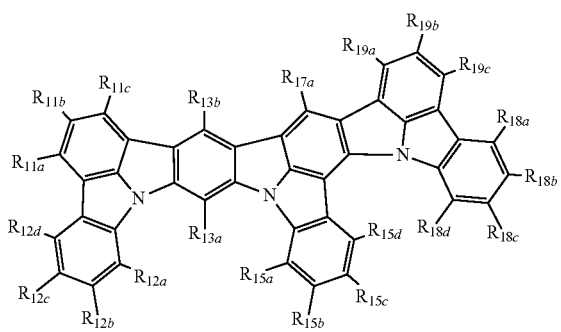
16-5
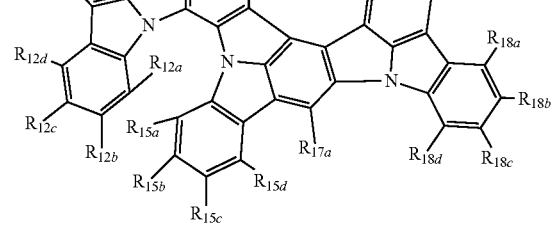
16-6
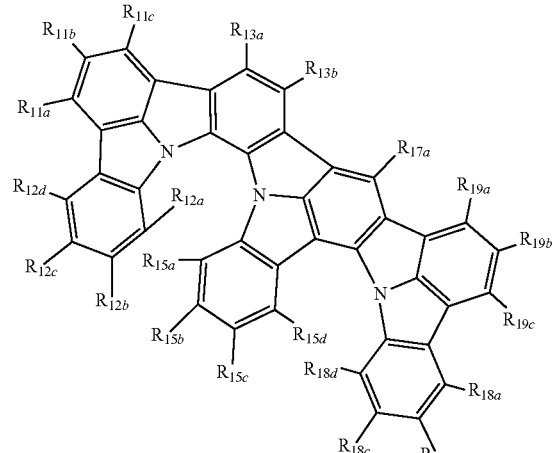

17-1
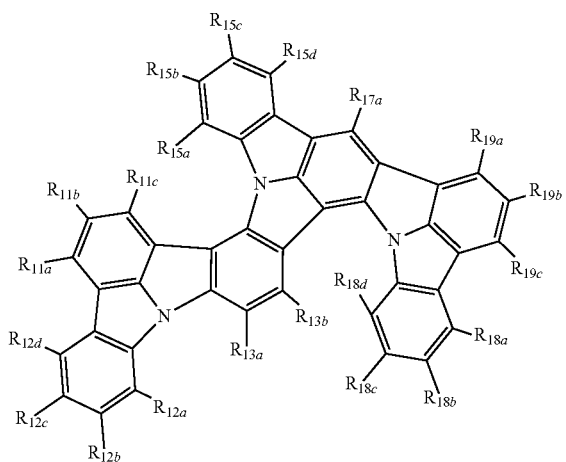
17-2
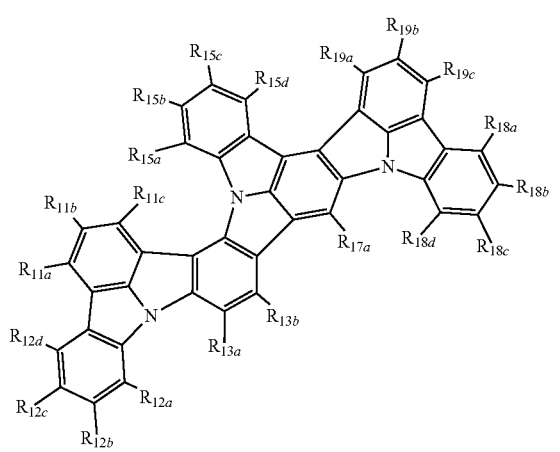
17-3
17-4
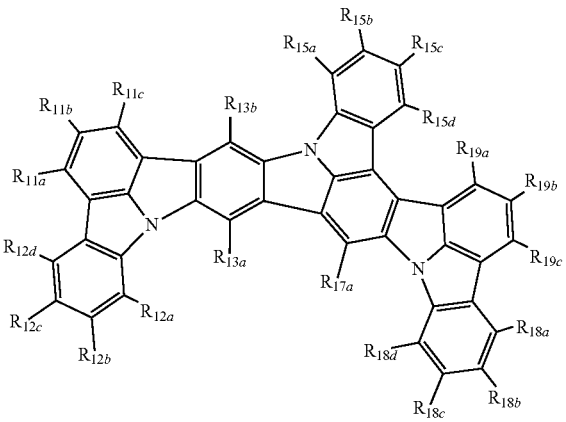
17-5
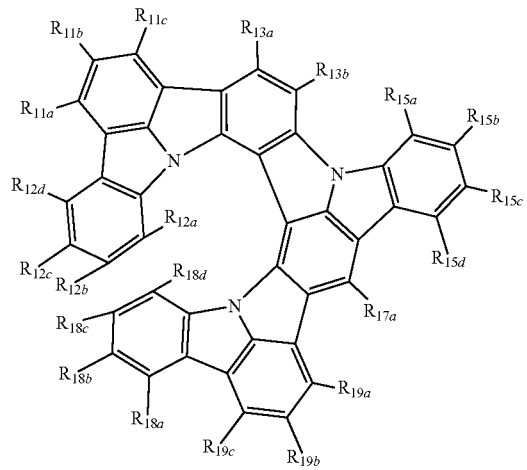
17-6
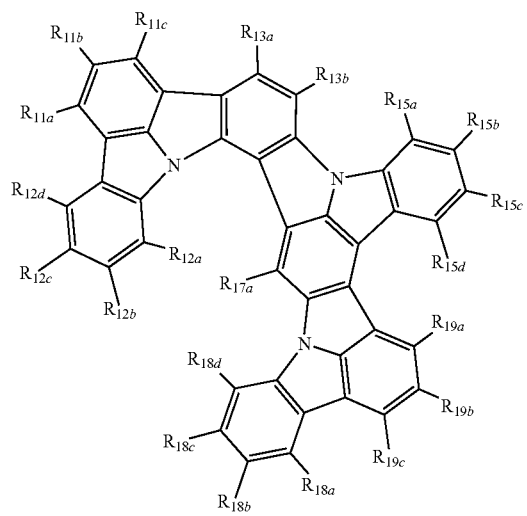
wherein, in Formulae 11-1 to 11-9, 12-1 to 12-6, 13-1 to 13-5, 14-1 to 14-6, 15-1 to 15-6, 16-1 to 16-6, and 17-1 to 17-6,
$R_{11a}$ to $R_{11c}$ may each be understood by referring to the description of $R_{11}$ provided herein,
$R_{12a}$ to $R_{12d}$ may each be understood by referring to the description of $R_{12}$ provided herein, $R_{13a}$ and $R_{13b}$ may each be understood by referring to the description of $R_{13}$ provided herein, $R_{14a}$ to $R_{14c}$ may each be understood by referring to the description of $R_{14}$ provided herein, $R_{15a}$ to $R_{15d}$ may each be understood by referring to the description of $R_{15}$ provided herein, $R_{16a}$ and $R_{16b}$ may each be understood by referring to the description of $R_{16}$ provided herein, $R_{17a}$ may be understood by referring to the description of $R_{17}$ provided herein, $R_{18a}$ to $R_{18d}$ may each be understood by referring to the description of $R_{18}$ provided herein, and $R_{19a}$ to $R_{19c}$ may each be understood by referring to the description of $R_{19}$ provided herein.

In some embodiments, at least one of $R_{11b}$, $R_{12c}$, $R_{14b}$, $R_{18b}$, and $R_{19b}$ in Formulae 11-1, 11-2, and 11-5, at least one of $R_{11b}$, $R_{12c}$, $R_{14b}$, $R_{16b}$, $R_{18b}$, and $R_{19b}$ in Formulae 11-3 and 11-6, at least one of $R_{11b}$, $R_{12c}$, $R_{14b}$, $R_{16a}$, $R_{18b}$, and $R_{19b}$ in Formula 11-4, at least one of $R_{11b}$, $R_{12c}$, $R_{13a}$, $R_{13b}$, $R_{14b}$, $R_{18b}$ and $R_{19b}$ in Formulae 11-7, 11-8, and 11-9, at least one of $R_{11b}$, $R_{12c}$, $R_{14b}$, $R_{18c}$, and $R_{19b}$ in Formulae 12-1, 12-2, and 12-4, at least one of $R_{11b}$, $R_{12c}$, $R_{14b}$, $R_{16b}$, $R_{18c}$, and $R_{19b}$ in Formula 12-3, at least one of $R_{11b}$, $R_{12c}$, $R_{14b}$, $R_{16a}$, $R_{16b}$, $R_{18c}$, and $R_{19b}$ in Formula 12-5, at least one of $R_{11b}$, $R_{12c}$, $R_{13a}$, $R_{13b}$, $R_{14b}$, $R_{16a}$, $R_{16b}$, $R_{18c}$, and $R_{19b}$ in Formulae 12-6, 13-1, and 13-3, at least one of $R_{11b}$, $R_{12c}$, $R_{13a}$, $R_{13b}$, $R_{14b}$, $R_{18c}$, and $R_{19b}$ in Formula 13-2, at least one of $R_{11b}$, $R_{12c}$, $R_{14b}$, $R_{16a}$, $R_{18c}$, and $R_{19b}$ in Formula 13-4, at least one of $R_{11b}$, $R_{12c}$, $R_{13b}$, $R_{14b}$, $R_{16a}$, $R_{18c}$, and $R_{19b}$ in Formula 13-5, at least one of $R_{11b}$, $R_{12c}$, $R_{15c}$, $R_{18b}$, and $R_{19b}$ in Formulae 14-1, 14-2, 14-3, 14-4, 15-3, 15-4, 16-1, 16-2, 16-3, 16-4, 17-3, and 17-4, at least one of $R_{11b}$, $R_{12c}$, $R_{13a}$, $R_{13b}$, $R_{15c}$, $R_{18b}$, and $R_{19b}$ in Formulae 14-5, 14-6, 16-5, and 16-6, at least one of $R_{11b}$, $R_{12c}$, $R_{13a}$, $R_{15c}$, $R_{18b}$, and $R_{19b}$ in Formulae 15-1, 15-2, 17-1, and 17-2, and at least one of $R_{11b}$, $R_{12c}$, $R_{13b}$, $R_{15c}$, $R_{18b}$, and $R_{19b}$ in Formulae 15-5, 15-6, 17-5, and 17-6 may be —$CH_3$, —$CD_3$, —$CD_2H$, —$CDH_2$, —$CF_3$, —$CF_2H$, —$CFH_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, —$Si(Q_1)(Q_2)(Q_3)$, —$Ge(Q_1)(Q_2)(Q_3)$, —$C(Q_1)(Q_2)(Q_3)$, —$B(Q_1)(Q_2)$, or —$N(Q_1)(Q_2)$, wherein $Q_1$ to $Q_3$ may each independently be:

deuterium, —F, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, —$CD_2CDH_2$, —$CF_3$, —$CF_2H$, —$CFH_2$, —$CH_2CF_3$, —$CH_2CF_2H$, —$CH_2CFH_2$, —$CHFCH_3$, —$CHFCF_2H$, —$CHFCFH_2$, —$CHFCF_3$, —$CF_2CF_3$, —$CF_2CF_2H$, or —$CF_2CFH_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

In some embodiments, at least one of $R_{11b}$, $R_{12c}$, $R_{14b}$, $R_{18b}$, and $R_{19b}$ in Formulae 11-1, 11-2, and 11-5, at least one of $R_{11b}$, $R_{12c}$, $R_{14b}$, $R_{16b}$, $R_{18b}$, and $R_{19b}$ in Formulae 11-3 and 11-6, at least one of $R_{11b}$, $R_{12c}$, $R_{14b}$, $R_{16a}$, $R_{18b}$, and $R_{19b}$ in Formula 11-4, at least one of $R_{11b}$, $R_{12c}$, $R_{13a}$, $R_{13b}$, $R_{14b}$, $R_{18b}$, and $R_{19b}$ in Formulae 11-7, 11-8, and 11-9, at least one of $R_{11b}$, $R_{12c}$, $R_{14b}$, $R_{18c}$, and $R_{19b}$ in Formulae 12-1, 12-2, and 12-4, at least one of $R_{11b}$, $R_{12c}$, $R_{14b}$, $R_{16b}$, $R_{18c}$, and $R_{19b}$ in Formula 12-3, at least one of $R_{11b}$, $R_{12c}$, $R_{14b}$, $R_{16a}$, $R_{16b}$, $R_{18c}$, and $R_{19b}$ in Formula 12-5, at least one of $R_{11b}$, $R_{12c}$, $R_{13a}$, $R_{13b}$, $R_{14b}$, $R_{16a}$, $R_{16b}$, $R_{18c}$, and $R_{19b}$ in Formulae 12-6, 13-1, and 13-3, at least one of $R_{11b}$, $R_{12c}$, $R_{13a}$, $R_{13b}$, $R_{14b}$, $R_{18c}$, and $R_{19b}$ in Formula 13-2, at least one of $R_{11b}$, $R_{12c}$, $R_{14b}$, $R_{16a}$, $R_{18c}$, and $R_{19b}$ in Formula 13-4, at least one of $R_{11b}$, $R_{12c}$, $R_{13b}$, $R_{14b}$, $R_{16a}$, $R_{18c}$, and $R_{19b}$ in Formula 13-5, at least one of $R_{11b}$, $R_{12c}$, $R_{15c}$, $R_{18b}$, and $R_{19b}$ in Formulae 14-1, 14-2, 14-3, 14-4, 15-3, 15-4, 16-1, 16-2, 16-3, 16-4, 17-3, and 17-4, at least one of $R_{11b}$, $R_{12c}$, $R_{13a}$, $R_{13b}$, $R_{15c}$, $R_{18b}$, and $R_{19b}$ in Formulae 14-5, 14-6, 16-5, and 16-6, at least one of $R_{11b}$, $R_{12c}$, $R_{13a}$, $R_{15c}$, $R_{18b}$, and $R_{19b}$ in Formulae 15-1, 15-2, 17-1, and 17-2, and at least one of $R_{11b}$, $R_{12c}$, $R_{13b}$, $R_{15c}$, $R_{18b}$, and $R_{19b}$ in Formulae 15-5, 15-6, 17-5, and 17-6 may each be Formulae A-1 to A-29, and the remaining substituents may each be hydrogen:

A-1
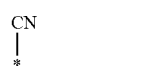

A-2
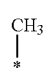

A-3
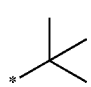

A-4
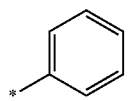

A-5
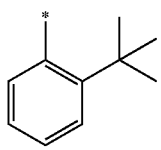

A-6
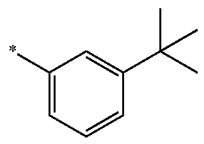

A-7
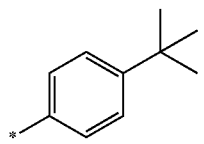

A-8
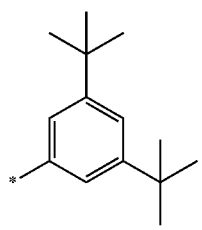

A-9
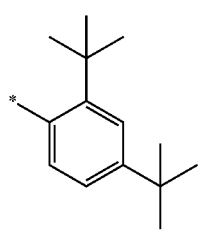

-continued

A-10
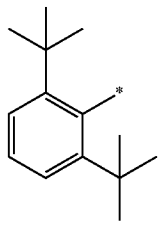

A-11
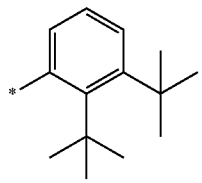

A-12
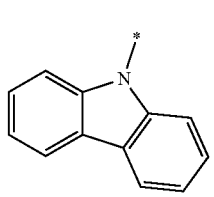

A-13
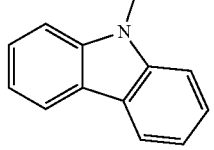

A-14
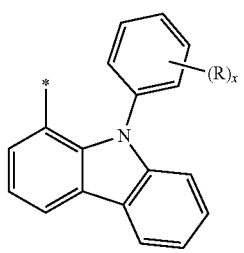

A-15
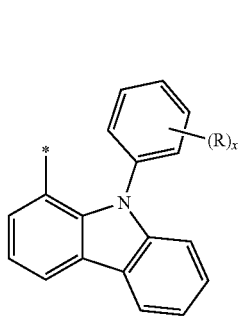

A-16
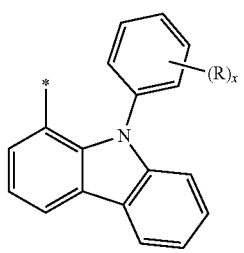

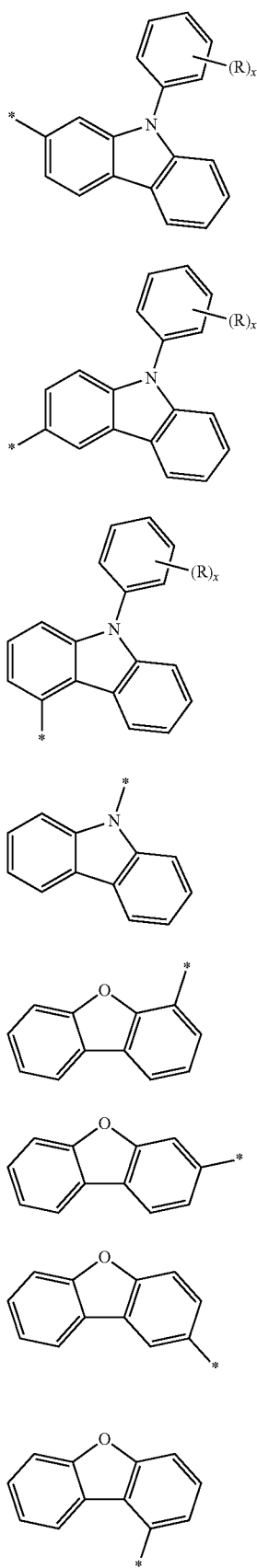

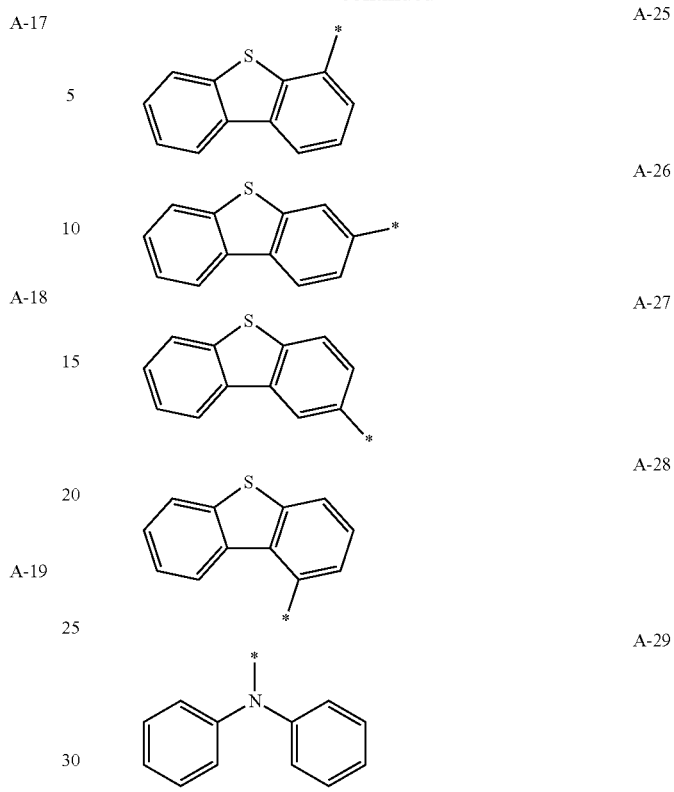

wherein, in Formulae A-1 to A-29,

R may be hydrogen, CN, a methyl group, a t-butyl group, or a phenyl group, x may be an integer from 1 to 5, and

* indicates a binding site to an adjacent atom.

In some embodiments, the heterocyclic compound may be of Groups HC1 to HC10: Group HC1

The heterocyclic compound may be represented by Formula 11-2, and substituents may be defined as shown in Table 1.

TABLE 1

| Compound No. | $R_{11b}$ | $R_{12c}$ | $R_{14b}$ | $R_{18b}$ | $R_{19b}$ |
|---|---|---|---|---|---|
| 112001 | t-Bu | t-Bu | t-Bu | t-Bu | t-Bu |
| 112002 | Ph | Ph | t-Bu | Ph | Ph |
| 112003 | t-Bu | t-Bu | H | H | H |
| 112004 | H | H | t-Bu | H | H |
| 112005 | H | H | H | t-Bu | t-Bu |
| 112006 | t-Bu | t-Bu | t-Bu | H | H |
| 112007 | H | H | t-Bu | t-Bu | t-Bu |
| 112008 | t-Bu | t-Bu | H | t-Bu | t-Bu |
| 112009 | Ph | Ph | H | H | H |
| 112010 | H | H | Ph | H | H |
| 112011 | H | H | H | Ph | Ph |
| 112012 | Ph | Ph | Ph | H | H |
| 112013 | H | H | Ph | Ph | Ph |
| 112014 | Ph | Ph | H | Ph | Ph |
| 112015 | CN | CN | H | H | H |
| 112016 | H | H | CN | H | H |
| 112017 | H | H | H | CN | CN |
| 112018 | CN | CN | CN | H | H |
| 112019 | H | H | CN | CN | CN |
| 112020 | CN | CN | H | CN | CN |
| 112021 | 9-Cbz | 9-Cbz | H | H | H |
| 112022 | H | H | 9-Cbz | H | H |

TABLE 1-continued

| Compound No. | $R_{11b}$ | $R_{12c}$ | $R_{14b}$ | $R_{18b}$ | $R_{19b}$ |
|---|---|---|---|---|---|
| 112023 | H | H | H | 9-Cbz | 9-Cbz |
| 112024 | 9-Cbz | 9-Cbz | 9-Cbz | H | H |
| 112025 | H | H | 9-Cbz | 9-Cbz | 9-Cbz |
| 112026 | 9-Cbz | 9-Cbz | H | 9-Cbz | 9-Cbz |
| 112027 | Me | Me | H | H | H |
| 112028 | H | H | Me | H | H |
| 112029 | H | H | H | Me | Me |
| 112030 | Me | Me | Me | H | H |
| 112031 | H | H | Me | Me | Me |
| 112032 | Me | Me | Me | Me | Me |
| 112033 | CD3 | CD3 | H | H | H |
| 112034 | H | H | CD3 | H | H |
| 112035 | H | H | H | CD3 | CD3 |
| 112036 | CD3 | CD3 | CD3 | H | H |
| 112037 | H | H | CD3 | CD3 | CD3 |
| 112038 | CD3 | CD3 | H | CD3 | CD3 |
| 112039 | 4-t-BuPh | 4-t-BuPh | H | H | H |
| 112040 | H | H | 4-t-BuPh | H | H |
| 112041 | H | H | H | 4-t-BuPh | 4-t-BuPh |
| 112042 | 4-t-BuPh | 4-t-BuPh | 4-t-BuPh | H | H |
| 112043 | H | H | 4-t-BuPh | 4-t-BuPh | 4-t-BuPh |
| 112044 | 4-t-BuPh | 4-t-BuPh | H | 4-t-BuPh | 4-t-BuPh |
| 112045 | 1,3-di-t-BuPh | 1,3-di-t-BuPh | H | H | H |
| 112046 | H | H | 1,3-di-t-BuPh | H | H |
| 112047 | H | H | H | 1,3-di-t-BuPh | 1,3-di-t-BuPh |
| 112048 | 1,3-di-t-BuPh | 1,3-di-t-BuPh | 1,3-di-t-BuPh | H | H |
| 112049 | H | H | 1,3-di-t-BuPh | 1,3-di-t-BuPh | 1,3-di-t-BuPh |
| 112050 | 1,3-di-t-BuPh | 1,3-di-t-BuPh | H | 1,3-di-t-BuPh | 1,3-di-t-BuPh |
| 112051 | t-Bu | t-Bu | Ph | H | H |
| 112052 | t-Bu | t-Bu | CN | H | H |
| 112053 | t-Bu | t-Bu | DPA | H | H |
| 112054 | t-Bu | t-Bu | 2-DBF | H | H |
| 112055 | t-Bu | t-Bu | 2-DBT | H | H |
| 112056 | t-Bu | t-Bu | 4-t-BuPh | H | H |
| 112057 | t-Bu | t-Bu | 1,3-di-t-BuPh | H | H |
| 112058 | t-Bu | t-Bu | 9-Cbz | H | H |
| 112059 | t-Bu | t-Bu | Ph | t-Bu | t-Bu |
| 112060 | t-Bu | t-Bu | CN | t-Bu | t-Bu |
| 112061 | t-Bu | t-Bu | DPA | t-Bu | t-Bu |
| 112062 | t-Bu | t-Bu | 2-DBF | t-Bu | t-Bu |
| 112063 | t-Bu | t-Bu | 2-DBT | t-Bu | t-Bu |
| 112064 | t-Bu | t-Bu | 4-t-BuPh | t-Bu | t-Bu |
| 112065 | t-Bu | t-Bu | 1,3-di-t-BuPh | t-Bu | t-Bu |
| 112066 | t-Bu | t-Bu | 9-Cbz | t-Bu | t-Bu |
| 112067 | t-Bu | t-Bu | t-Bu | Ph | Ph |
| 112068 | t-Bu | t-Bu | Ph | Ph | Ph |
| 112069 | t-Bu | t-Bu | CN | Ph | Ph |
| 112070 | t-Bu | t-Bu | DPA | Ph | Ph |
| 112071 | t-Bu | t-Bu | 2-DBF | Ph | Ph |
| 112072 | t-Bu | t-Bu | 2-DBT | Ph | Ph |
| 112073 | t-Bu | t-Bu | 4-t-BuPh | Ph | Ph |
| 112074 | t-Bu | t-Bu | 1,3-di-t-BuPh | Ph | Ph |
| 112075 | t-Bu | t-Bu | 9-Cbz | Ph | Ph |
| 112076 | t-Bu | t-Bu | t-Bu | CN | CN |
| 112077 | t-Bu | t-Bu | Ph | CN | CN |
| 112078 | t-Bu | t-Bu | CN | CN | CN |
| 112079 | t-Bu | t-Bu | DPA | CN | CN |
| 112080 | t-Bu | t-Bu | 2-DBF | CN | CN |
| 112081 | t-Bu | t-Bu | 2-DBT | CN | CN |
| 112082 | t-Bu | t-Bu | 4-t-BuPh | CN | CN |
| 112083 | t-Bu | t-Bu | 1,3-di-t-BuPh | CN | CN |
| 112084 | t-Bu | t-Bu | 9-Cbz | CN | CN |
| 112085 | t-Bu | t-Bu | t-Bu | 9-Cbz | 9-Cbz |
| 112086 | t-Bu | t-Bu | Ph | 9-Cbz | 9-Cbz |
| 112087 | t-Bu | t-Bu | CN | 9-Cbz | 9-Cbz |
| 112088 | t-Bu | t-Bu | DPA | 9-Cbz | 9-Cbz |
| 112089 | t-Bu | t-Bu | 2-DBF | 9-Cbz | 9-Cbz |
| 112090 | t-Bu | t-Bu | 2-DBT | 9-Cbz | 9-Cbz |
| 112091 | t-Bu | t-Bu | 4-t-BuPh | 9-Cbz | 9-Cbz |
| 112092 | t-Bu | t-Bu | 1,3-di-t-BuPh | 9-Cbz | 9-Cbz |
| 112093 | t-Bu | t-Bu | 9-Cbz | 9-Cbz | 9-Cbz |
| 112094 | t-Bu | t-Bu | t-Bu | 4-t-BuPh | 4-t-BuPh |
| 112095 | t-Bu | t-Bu | Ph | 4-t-BuPh | 4-t-BuPh |
| 112096 | t-Bu | t-Bu | CN | 4-t-BuPh | 4-t-BuPh |
| 112097 | t-Bu | t-Bu | DPA | 4-t-BuPh | 4-t-BuPh |
| 112098 | t-Bu | t-Bu | 2-DBF | 4-t-BuPh | 4-t-BuPh |
| 112099 | t-Bu | t-Bu | 2-DBT | 4-t-BuPh | 4-t-BuPh |
| 112100 | t-Bu | t-Bu | 4-t-BuPh | 4-t-BuPh | 4-t-BuPh |
| 112101 | t-Bu | t-Bu | 1,3-di-t-BuPh | 4-t-BuPh | 4-t-BuPh |
| 112102 | t-Bu | t-Bu | 9-Cbz | 4-t-BuPh | 4-t-BuPh |
| 112103 | t-Bu | t-Bu | t-Bu | 1,3-di-t-BuPh | 1,3-di-t-BuPh |
| 112104 | t-Bu | t-Bu | Ph | 1,3-di-t-BuPh | 1,3-di-t-BuPh |

TABLE 1-continued

| Compound No. | $R_{11b}$ | $R_{12c}$ | $R_{14b}$ | $R_{18b}$ | $R_{19b}$ |
|---|---|---|---|---|---|
| 112105 | t-Bu | t-Bu | CN | 1,3-di-t-BuPh | 1,3-di-t-BuPh |
| 112106 | t-Bu | t-Bu | DPA | 1,3-di-t-BuPh | 1,3-di-t-BuPh |
| 112107 | t-Bu | t-Bu | 2-DBF | 1,3-di-t-BuPh | 1,3-di-t-BuPh |
| 112108 | t-Bu | t-Bu | 2-DBT | 1,3-di-t-BuPh | 1,3-di-t-BuPh |
| 112109 | t-Bu | t-Bu | 4-t-BuPh | 1,3-di-t-BuPh | 1,3-di-t-BuPh |
| 112110 | t-Bu | t-Bu | 1,3-di-t-BuPh | 1,3-di-t-BuPh | 1,3-di-t-BuPh |
| 112111 | t-Bu | t-Bu | 9-Cbz | 1,3-di-t-BuPh | 1,3-di-t-BuPh |
| 112112 | Ph | Ph | t-Bu | H | H |
| 112113 | Ph | Ph | CN | H | H |
| 112114 | Ph | Ph | DPA | H | H |
| 112115 | Ph | Ph | 2-DBF | H | H |
| 112116 | Ph | Ph | 2-DBT | H | H |
| 112117 | Ph | Ph | 4-t-BuPh | H | H |
| 112118 | Ph | Ph | 1,3-di-t-BuPh | H | H |
| 112119 | Ph | Ph | 9-Cbz | H | H |
| 112120 | Ph | Ph | t-Bu | t-Bu | t-Bu |
| 112121 | Ph | Ph | Ph | t-Bu | t-Bu |
| 112122 | Ph | Ph | CN | t-Bu | t-Bu |
| 112123 | Ph | Ph | DPA | t-Bu | t-Bu |
| 112124 | Ph | Ph | 2-DBF | t-Bu | t-Bu |
| 112125 | Ph | Ph | 2-DBT | t-Bu | t-Bu |
| 112126 | Ph | Ph | 4-t-BuPh | t-Bu | t-Bu |
| 112127 | Ph | Ph | 1,3-di-t-BuPh | t-Bu | t-Bu |
| 112128 | Ph | Ph | 9-Cbz | t-Bu | t-Bu |
| 112129 | Ph | Ph | Ph | Ph | Ph |
| 112130 | Ph | Ph | CN | Ph | Ph |
| 112131 | Ph | Ph | DPA | Ph | Ph |
| 112132 | Ph | Ph | 2-DBF | Ph | Ph |
| 112133 | Ph | Ph | 2-DBT | Ph | Ph |
| 112134 | Ph | Ph | 4-t-BuPh | Ph | Ph |
| 112135 | Ph | Ph | 1,3-di-t-BuPh | Ph | Ph |
| 112136 | Ph | Ph | 9-Cbz | Ph | Ph |
| 112137 | Ph | Ph | t-Bu | CN | CN |
| 112138 | Ph | Ph | Ph | CN | CN |
| 112139 | Ph | Ph | CN | CN | CN |
| 112140 | Ph | Ph | DPA | CN | CN |
| 112141 | Ph | Ph | 2-DBF | CN | CN |
| 112142 | Ph | Ph | 2-DBT | CN | CN |
| 112143 | Ph | Ph | 4-t-BuPh | CN | CN |
| 112144 | Ph | Ph | 1,3-di-t-BuPh | CN | CN |
| 112145 | Ph | Ph | 9-Cbz | CN | CN |
| 112146 | Ph | Ph | t-Bu | 9-Cbz | 9-Cbz |
| 112147 | Ph | Ph | Ph | 9-Cbz | 9-Cbz |
| 112148 | Ph | Ph | CN | 9-Cbz | 9-Cbz |
| 112149 | Ph | Ph | DPA | 9-Cbz | 9-Cbz |
| 112150 | Ph | Ph | 2-DBF | 9-Cbz | 9-Cbz |
| 112151 | Ph | Ph | 2-DBT | 9-Cbz | 9-Cbz |
| 112152 | Ph | Ph | 4-t-BuPh | 9-Cbz | 9-Cbz |
| 112153 | Ph | Ph | 1,3-di-t-BuPh | 9-Cbz | 9-Cbz |
| 112154 | Ph | Ph | 9-Cbz | 9-Cbz | 9-Cbz |
| 112155 | Ph | Ph | t-Bu | 4-t-BuPh | 4-t-BuPh |
| 112156 | Ph | Ph | Ph | 4-t-BuPh | 4-t-BuPh |
| 112157 | Ph | Ph | CN | 4-t-BuPh | 4-t-BuPh |
| 112158 | Ph | Ph | DPA | 4-t-BuPh | 4-t-BuPh |
| 112159 | Ph | Ph | 2-DBF | 4-t-BuPh | 4-t-BuPh |
| 112160 | Ph | Ph | 2-DBT | 4-t-BuPh | 4-t-BuPh |
| 112161 | Ph | Ph | 4-t-BuPh | 4-t-BuPh | 4-t-BuPh |
| 112162 | Ph | Ph | 1,3-di-t-BuPh | 4-t-BuPh | 4-t-BuPh |
| 112163 | Ph | Ph | 9-Cbz | 4-t-BuPh | 4-t-BuPh |
| 112164 | Ph | Ph | t-Bu | 1,3-di-t-BuPh | 1,3-di-t-BuPh |
| 112165 | Ph | Ph | Ph | 1,3-di-t-BuPh | 1,3-di-t-BuPh |
| 112166 | Ph | Ph | CN | 1,3-di-t-BuPh | 1,3-di-t-BuPh |
| 112167 | Ph | Ph | DPA | 1,3-di-t-BuPh | 1,3-di-t-BuPh |
| 112168 | Ph | Ph | 2-DBF | 1,3-di-t-BuPh | 1,3-di-t-BuPh |
| 112169 | Ph | Ph | 2-DBT | 1,3-di-t-BuPh | 1,3-di-t-BuPh |
| 112170 | Ph | Ph | 4-t-BuPh | 1,3-di-t-BuPh | 1,3-di-t-BuPh |
| 112171 | Ph | Ph | 1,3-di-t-BuPh | 1,3-di-t-BuPh | 1,3-di-t-BuPh |
| 112172 | Ph | Ph | 9-Cbz | 1,3-di-t-BuPh | 1,3-di-t-BuPh |
| 112173 | 9-Cbz | 9-Cbz | t-Bu | H | H |
| 112174 | 9-Cbz | 9-Cbz | Ph | H | H |
| 112175 | 9-Cbz | 9-Cbz | CN | H | H |
| 112176 | 9-Cbz | 9-Cbz | DPA | H | H |
| 112177 | 9-Cbz | 9-Cbz | 2-DBF | H | H |
| 112178 | 9-Cbz | 9-Cbz | 2-DBT | H | H |
| 112179 | 9-Cbz | 9-Cbz | 4-t-BuPh | H | H |

TABLE 1-continued

| Compound No. | $R_{11b}$ | $R_{12c}$ | $R_{14b}$ | $R_{18b}$ | $R_{19b}$ |
|---|---|---|---|---|---|
| 112180 | 9-Cbz | 9-Cbz | 1,3-di-t-BuPh | H | H |
| 112181 | 9-Cbz | 9-Cbz | t-Bu | t-Bu | t-Bu |
| 112182 | 9-Cbz | 9-Cbz | Ph | t-Bu | t-Bu |
| 112183 | 9-Cbz | 9-Cbz | CN | t-Bu | t-Bu |
| 112184 | 9-Cbz | 9-Cbz | DPA | t-Bu | t-Bu |
| 112185 | 9-Cbz | 9-Cbz | 2-DBF | t-Bu | t-Bu |
| 112186 | 9-Cbz | 9-Cbz | 2-DBT | t-Bu | t-Bu |
| 112187 | 9-Cbz | 9-Cbz | 4-t-BuPh | t-Bu | t-Bu |
| 112188 | 9-Cbz | 9-Cbz | 1,3-di-t-BuPh | t-Bu | t-Bu |
| 112189 | 9-Cbz | 9-Cbz | 9-Cbz | t-Bu | t-Bu |
| 112190 | 9-Cbz | 9-Cbz | t-Bu | Ph | Ph |
| 112191 | 9-Cbz | 9-Cbz | Ph | Ph | Ph |
| 112192 | 9-Cbz | 9-Cbz | CN | Ph | Ph |
| 112193 | 9-Cbz | 9-Cbz | DPA | Ph | Ph |
| 112194 | 9-Cbz | 9-Cbz | 2-DBF | Ph | Ph |
| 112195 | 9-Cbz | 9-Cbz | 2-DBT | Ph | Ph |
| 112196 | 9-Cbz | 9-Cbz | 4-t-BuPh | Ph | Ph |
| 112197 | 9-Cbz | 9-Cbz | 1,3-di-t-BuPh | Ph | Ph |
| 112198 | 9-Cbz | 9-Cbz | 9-Cbz | Ph | Ph |
| 112199 | 9-Cbz | 9-Cbz | t-Bu | CN | CN |
| 112200 | 9-Cbz | 9-Cbz | Ph | CN | CN |
| 112201 | 9-Cbz | 9-Cbz | CN | CN | CN |
| 112202 | 9-Cbz | 9-Cbz | DPA | CN | CN |
| 112203 | 9-Cbz | 9-Cbz | 2-DBF | CN | CN |
| 112204 | 9-Cbz | 9-Cbz | 2-DBT | CN | CN |
| 112205 | 9-Cbz | 9-Cbz | 4-t-BuPh | CN | CN |
| 112206 | 9-Cbz | 9-Cbz | 1,3-di-t-BuPh | CN | CN |
| 112207 | 9-Cbz | 9-Cbz | 9-Cbz | CN | CN |
| 112208 | 9-Cbz | 9-Cbz | t-Bu | 9-Cbz | 9-Cbz |
| 112209 | 9-Cbz | 9-Cbz | Ph | 9-Cbz | 9-Cbz |
| 112210 | 9-Cbz | 9-Cbz | CN | 9-Cbz | 9-Cbz |
| 112211 | 9-Cbz | 9-Cbz | DPA | 9-Cbz | 9-Cbz |
| 112212 | 9-Cbz | 9-Cbz | 2-DBF | 9-Cbz | 9-Cbz |
| 112213 | 9-Cbz | 9-Cbz | 2-DBT | 9-Cbz | 9-Cbz |
| 112214 | 9-Cbz | 9-Cbz | 4-t-BuPh | 9-Cbz | 9-Cbz |
| 112215 | 9-Cbz | 9-Cbz | 1,3-di-t-BuPh | 9-Cbz | 9-Cbz |
| 112216 | 9-Cbz | 9-Cbz | 9-Cbz | 9-Cbz | 9-Cbz |
| 112217 | 9-Cbz | 9-Cbz | t-Bu | 4-t-BuPh | 4-t-BuPh |
| 112218 | 9-Cbz | 9-Cbz | Ph | 4-t-BuPh | 4-t-BuPh |
| 112219 | 9-Cbz | 9-Cbz | CN | 4-t-BuPh | 4-t-BuPh |
| 112220 | 9-Cbz | 9-Cbz | DPA | 4-t-BuPh | 4-t-BuPh |
| 112221 | 9-Cbz | 9-Cbz | 2-DBF | 4-t-BuPh | 4-t-BuPh |
| 112222 | 9-Cbz | 9-Cbz | 2-DBT | 4-t-BuPh | 4-t-BuPh |
| 112223 | 9-Cbz | 9-Cbz | 4-t-BuPh | 4-t-BuPh | 4-t-BuPh |
| 112224 | 9-Cbz | 9-Cbz | 1,3-di-t-BuPh | 4-t-BuPh | 4-t-BuPh |
| 112225 | 9-Cbz | 9-Cbz | 9-Cbz | 4-t-BuPh | 4-t-BuPh |
| 112226 | 9-Cbz | 9-Cbz | t-Bu | 1,3-di-t-BuPh | 1,3-di-t-BuPh |
| 112227 | 9-Cbz | 9-Cbz | Ph | 1,3-di-t-BuPh | 1,3-di-t-BuPh |
| 112228 | 9-Cbz | 9-Cbz | CN | 1,3-di-t-BuPh | 1,3-di-t-BuPh |
| 112229 | 9-Cbz | 9-Cbz | DPA | 1,3-di-t-BuPh | 1,3-di-t-BuPh |
| 112230 | 9-Cbz | 9-Cbz | 2-DBF | 1,3-di-t-BuPh | 1,3-di-t-BuPh |
| 112231 | 9-Cbz | 9-Cbz | 2-DBT | 1,3-di-t-BuPh | 1,3-di-t-BuPh |
| 112232 | 9-Cbz | 9-Cbz | 4-t-BuPh | 1,3-di-t-BuPh | 1,3-di-t-BuPh |
| 112233 | 9-Cbz | 9-Cbz | 1,3-di-t-BuPh | 1,3-di-t-BuPh | 1,3-di-t-BuPh |
| 112234 | 9-Cbz | 9-Cbz | 9-Cbz | 1,3-di-t-BuPh | 1,3-di-t-BuPh |
| 112235 | CN | CN | t-Bu | H | H |
| 112236 | CN | CN | Ph | H | H |
| 112237 | CN | CN | DPA | H | H |
| 112238 | CN | CN | 2-DBF | H | H |
| 112239 | CN | CN | 2-DBT | H | H |
| 112240 | CN | CN | 4-t-BuPh | H | H |
| 112241 | CN | CN | 1,3-di-t-BuPh | H | H |
| 112242 | CN | CN | 9-Cbz | H | H |
| 112243 | CN | CN | t-Bu | t-Bu | t-Bu |
| 112244 | CN | CN | Ph | t-Bu | t-Bu |
| 112245 | CN | CN | CN | t-Bu | t-Bu |
| 112246 | CN | CN | DPA | t-Bu | t-Bu |
| 112247 | CN | CN | 2-DBF | t-Bu | t-Bu |
| 112248 | CN | CN | 2-DBT | t-Bu | t-Bu |
| 112249 | CN | CN | 4-t-BuPh | t-Bu | t-Bu |
| 112250 | CN | CN | 1,3-di-t-BuPh | t-Bu | t-Bu |
| 112251 | CN | CN | 9-Cbz | t-Bu | t-Bu |
| 112252 | CN | CN | t-Bu | Ph | Ph |
| 112253 | CN | CN | Ph | Ph | Ph |
| 112254 | CN | CN | CN | Ph | Ph |
| 112255 | CN | CN | DPA | Ph | Ph |
| 112256 | CN | CN | 2-DBF | Ph | Ph |
| 112257 | CN | CN | 2-DBT | Ph | Ph |
| 112258 | CN | CN | 4-t-BuPh | Ph | Ph |
| 112259 | CN | CN | 1,3-di-t-BuPh | Ph | Ph |
| 112260 | CN | CN | 9-Cbz | Ph | Ph |
| 112261 | CN | CN | t-Bu | CN | CN |
| 112262 | CN | CN | Ph | CN | CN |

TABLE 1-continued

| Compound No. | $R_{11b}$ | $R_{12c}$ | $R_{14b}$ | $R_{18b}$ | $R_{19b}$ |
|---|---|---|---|---|---|
| 112263 | CN | CN | CN | CN | CN |
| 112264 | CN | CN | DPA | CN | CN |
| 112265 | CN | CN | 2-DBF | CN | CN |
| 112266 | CN | CN | 2-DBT | CN | CN |
| 112267 | CN | CN | 4-t-BuPh | CN | CN |
| 112268 | CN | CN | 1,3-di-t-BuPh | CN | CN |
| 112269 | CN | CN | 9-Cbz | CN | CN |
| 112270 | CN | CN | t-Bu | 9-Cbz | 9-Cbz |
| 112271 | CN | CN | Ph | 9-Cbz | 9-Cbz |
| 112272 | CN | CN | CN | 9-Cbz | 9-Cbz |
| 112273 | CN | CN | DPA | 9-Cbz | 9-Cbz |
| 112274 | CN | CN | 2-DBF | 9-Cbz | 9-Cbz |
| 112275 | CN | CN | 2-DBT | 9-Cbz | 9-Cbz |
| 112276 | CN | CN | 4-t-BuPh | 9-Cbz | 9-Cbz |
| 112277 | CN | CN | 1,3-di-t-BuPh | 9-Cbz | 9-Cbz |
| 112278 | CN | CN | 9-Cbz | 9-Cbz | 9-Cbz |
| 112279 | CN | CN | t-Bu | 4-t-BuPh | 4-t-BuPh |
| 112280 | CN | CN | Ph | 4-t-BuPh | 4-t-BuPh |
| 112281 | CN | CN | CN | 4-t-BuPh | 4-t-BuPh |
| 112282 | CN | CN | DPA | 4-t-BuPh | 4-t-BuPh |
| 112283 | CN | CN | 2-DBF | 4-t-BuPh | 4-t-BuPh |
| 112284 | CN | CN | 2-DBT | 4-t-BuPh | 4-t-BuPh |
| 112285 | CN | CN | 4-t-BuPh | 4-t-BuPh | 4-t-BuPh |
| 112286 | CN | CN | 1,3-di-t-BuPh | 4-t-BuPh | 4-t-BuPh |
| 112287 | CN | CN | 9-Cbz | 4-t-BuPh | 4-t-BuPh |
| 112288 | CN | CN | t-Bu | 1,3-di-t-BuPh | 1,3-di-t-BuPh |
| 112289 | CN | CN | Ph | 1,3-di-t-BuPh | 1,3-di-t-BuPh |
| 112290 | CN | CN | CN | 1,3-di-t-BuPh | 1,3-di-t-BuPh |
| 112291 | CN | CN | DPA | 1,3-di-t-BuPh | 1,3-di-t-BuPh |
| 112292 | CN | CN | 2-DBF | 1,3-di-t-BuPh | 1,3-di-t-BuPh |
| 112293 | CN | CN | 2-DBT | 1,3-di-t-BuPh | 1,3-di-t-BuPh |
| 112294 | CN | CN | 4-t-BuPh | 1,3-di-t-BuPh | 1,3-di-t-BuPh |
| 112295 | CN | CN | 1,3-di-t-BuPh | 1,3-di-t-BuPh | 1,3-di-t-BuPh |
| 112296 | CN | CN | 9-Cbz | 1,3-di-t-BuPh | 1,3-di-t-BuPh |
| 112297 | 4-t-BuPh | 4-t-BuPh | t-Bu | H | H |
| 112298 | 4-t-BuPh | 4-t-BuPh | Ph | H | H |
| 112299 | 4-t-BuPh | 4-t-BuPh | CN | H | H |
| 112300 | 4-t-BuPh | 4-t-BuPh | DPA | H | H |
| 112301 | 4-t-BuPh | 4-t-BuPh | 2-DBF | H | H |
| 112302 | 4-t-BuPh | 4-t-BuPh | 2-DBT | H | H |
| 112303 | 4-t-BuPh | 4-t-BuPh | 1,3-di-t-BuPh | H | H |
| 112304 | 4-t-BuPh | 4-t-BuPh | 9-Cbz | H | H |
| 112305 | 4-t-BuPh | 4-t-BuPh | t-Bu | t-Bu | t-Bu |
| 112306 | 4-t-BuPh | 4-t-BuPh | Ph | t-Bu | t-Bu |
| 112307 | 4-t-BuPh | 4-t-BuPh | CN | t-Bu | t-Bu |
| 112308 | 4-t-BuPh | 4-t-BuPh | DPA | t-Bu | t-Bu |
| 112309 | 4-t-BuPh | 4-t-BuPh | 2-DBF | t-Bu | t-Bu |
| 112310 | 4-t-BuPh | 4-t-BuPh | 2-DBT | t-Bu | t-Bu |
| 112311 | 4-t-BuPh | 4-t-BuPh | 4-t-BuPh | t-Bu | t-Bu |
| 112312 | 4-t-BuPh | 4-t-BuPh | 1,3-di-t-BuPh | t-Bu | t-Bu |
| 112313 | 4-t-BuPh | 4-t-BuPh | 9-Cbz | t-Bu | t-Bu |
| 112314 | 4-t-BuPh | 4-t-BuPh | t-Bu | Ph | Ph |
| 112315 | 4-t-BuPh | 4-t-BuPh | Ph | Ph | Ph |
| 112316 | 4-t-BuPh | 4-t-BuPh | CN | Ph | Ph |
| 112317 | 4-t-BuPh | 4-t-BuPh | DPA | Ph | Ph |
| 112318 | 4-t-BuPh | 4-t-BuPh | 2-DBF | Ph | Ph |
| 112319 | 4-t-BuPh | 4-t-BuPh | 2-DBT | Ph | Ph |
| 112320 | 4-t-BuPh | 4-t-BuPh | 4-t-BuPh | Ph | Ph |
| 112321 | 4-t-BuPh | 4-t-BuPh | 1,3-di-t-BuPh | Ph | Ph |
| 112322 | 4-t-BuPh | 4-t-BuPh | 9-Cbz | Ph | Ph |
| 112323 | 4-t-BuPh | 4-t-BuPh | t-Bu | CN | CN |
| 112324 | 4-t-BuPh | 4-t-BuPh | Ph | CN | CN |
| 112325 | 4-t-BuPh | 4-t-BuPh | CN | CN | CN |
| 112326 | 4-t-BuPh | 4-t-BuPh | DPA | CN | CN |
| 112327 | 4-t-BuPh | 4-t-BuPh | 2-DBF | CN | CN |
| 112328 | 4-t-BuPh | 4-t-BuPh | 2-DBT | CN | CN |
| 112329 | 4-t-BuPh | 4-t-BuPh | 4-t-BuPh | CN | CN |
| 112330 | 4-t-BuPh | 4-t-BuPh | 1,3-di-t-BuPh | CN | CN |
| 112331 | 4-t-BuPh | 4-t-BuPh | 9-Cbz | CN | CN |
| 112332 | 4-t-BuPh | 4-t-BuPh | t-Bu | 9-Cbz | 9-Cbz |
| 112333 | 4-t-BuPh | 4-t-BuPh | Ph | 9-Cbz | 9-Cbz |
| 112334 | 4-t-BuPh | 4-t-BuPh | CN | 9-Cbz | 9-Cbz |

TABLE 1-continued

| Compound No. | R$_{11b}$ | R$_{12c}$ | R$_{14b}$ | R$_{18b}$ | R$_{19b}$ |
|---|---|---|---|---|---|
| 112335 | 4-t-BuPh | 4-t-BuPh | DPA | 9-Cbz | 9-Cbz |
| 112336 | 4-t-BuPh | 4-t-BuPh | 2-DBF | 9-Cbz | 9-Cbz |
| 112337 | 4-t-BuPh | 4-t-BuPh | 2-DBT | 9-Cbz | 9-Cbz |
| 112338 | 4-t-BuPh | 4-t-BuPh | 4-t-BuPh | 9-Cbz | 9-Cbz |
| 112339 | 4-t-BuPh | 4-t-BuPh | 1,3-di-t-BuPh | 9-Cbz | 9-Cbz |
| 112340 | 4-t-BuPh | 4-t-BuPh | 9-Cbz | 9-Cbz | 9-Cbz |
| 112341 | 4-t-BuPh | 4-t-BuPh | t-Bu | 4-t-BuPh | 4-t-BuPh |
| 112342 | 4-t-BuPh | 4-t-BuPh | Ph | 4-t-BuPh | 4-t-BuPh |
| 112343 | 4-t-BuPh | 4-t-BuPh | CN | 4-t-BuPh | 4-t-BuPh |
| 112344 | 4-t-BuPh | 4-t-BuPh | DPA | 4-t-BuPh | 4-t-BuPh |
| 112345 | 4-t-BuPh | 4-t-BuPh | 2-DBF | 4-t-BuPh | 4-t-BuPh |
| 112346 | 4-t-BuPh | 4-t-BuPh | 2-DBT | 4-t-BuPh | 4-t-BuPh |
| 112347 | 4-t-BuPh | 4-t-BuPh | 4-t-BuPh | 4-t-BuPh | 4-t-BuPh |
| 112348 | 4-t-BuPh | 4-t-BuPh | 1,3-di-t-BuPh | 4-t-BuPh | 4-t-BuPh |
| 112349 | 4-t-BuPh | 4-t-BuPh | 9-Cbz | 4-t-BuPh | 4-t-BuPh |
| 112350 | 4-t-BuPh | 4-t-BuPh | t-Bu | 1,3-di-t-BuPh | 1,3-di-t-BuPh |
| 112351 | 4-t-BuPh | 4-t-BuPh | Ph | 1,3-di-t-BuPh | 1,3-di-t-BuPh |
| 112352 | 4-t-BuPh | 4-t-BuPh | CN | 1,3-di-t-BuPh | 1,3-di-t-BuPh |
| 112353 | 4-t-BuPh | 4-t-BuPh | DPA | 1,3-di-t-BuPh | 1,3-di-t-BuPh |
| 112354 | 4-t-BuPh | 4-t-BuPh | 2-DBF | 1,3-di-t-BuPh | 1,3-di-t-BuPh |
| 112355 | 4-t-BuPh | 4-t-BuPh | 2-DBT | 1,3-di-t-BuPh | 1,3-di-t-BuPh |
| 112356 | 4-t-BuPh | 4-t-BuPh | 4-t-BuPh | 1,3-di-t-BuPh | 1,3-di-t-BuPh |
| 112357 | 4-t-BuPh | 4-t-BuPh | 1,3-di-t-BuPh | 1,3-di-t-BuPh | 1,3-di-t-BuPh |
| 112358 | 4-t-BuPh | 4-t-BuPh | 9-Cbz | 1,3-di-t-BuPh | 1,3-di-t-BuPh |
| 112359 | 1,3-di-t-BuPh | 1,3-di-t-BuPh | t-Bu | H | H |
| 112360 | 1,3-di-t-BuPh | 1,3-di-t-BuPh | Ph | H | H |
| 112361 | 1,3-di-t-BuPh | 1,3-di-t-BuPh | CN | H | H |
| 112362 | 1,3-di-t-BuPh | 1,3-di-t-BuPh | DPA | H | H |
| 112363 | 1,3-di-t-BuPh | 1,3-di-t-BuPh | 2-DBF | H | H |
| 112364 | 1,3-di-t-BuPh | 1,3-di-t-BuPh | 2-DBT | H | H |
| 112365 | 1,3-di-t-BuPh | 1,3-di-t-BuPh | 4-t-BuPh | H | H |
| 112366 | 1,3-di-t-BuPh | 1,3-di-t-BuPh | 9-Cbz | H | H |
| 112367 | 1,3-di-t-BuPh | 1,3-di-t-BuPh | t-Bu | t-Bu | t-Bu |
| 112368 | 1,3-di-t-BuPh | 1,3-di-t-BuPh | Ph | t-Bu | t-Bu |
| 112369 | 1,3-di-t-BuPh | 1,3-di-t-BuPh | CN | t-Bu | t-Bu |
| 112370 | 1,3-di-t-BuPh | 1,3-di-t-BuPh | DPA | t-Bu | t-Bu |
| 112371 | 1,3-di-t-BuPh | 1,3-di-t-BuPh | 2-DBF | t-Bu | t-Bu |
| 112372 | 1,3-di-t-BuPh | 1,3-di-t-BuPh | 2-DBT | t-Bu | t-Bu |
| 112373 | 1,3-di-t-BuPh | 1,3-di-t-BuPh | 4-t-BuPh | t-Bu | t-Bu |
| 112374 | 1,3-di-t-BuPh | 1,3-di-t-BuPh | 1,3-di-t-BuPh | t-Bu | t-Bu |
| 112375 | 1,3-di-t-BuPh | 1,3-di-t-BuPh | 9-Cbz | t-Bu | t-Bu |
| 112376 | 1,3-di-t-BuPh | 1,3-di-t-BuPh | t-Bu | Ph | Ph |
| 112377 | 1,3-di-t-BuPh | 1,3-di-t-BuPh | Ph | Ph | Ph |
| 112378 | 1,3-di-t-BuPh | 1,3-di-t-BuPh | CN | Ph | Ph |
| 112379 | 1,3-di-t-BuPh | 1,3-di-t-BuPh | DPA | Ph | Ph |
| 112380 | 1,3-di-t-BuPh | 1,3-di-t-BuPh | 2-DBF | Ph | Ph |
| 112381 | 1,3-di-t-BuPh | 1,3-di-t-BuPh | 2-DBT | Ph | Ph |
| 112382 | 1,3-di-t-BuPh | 1,3-di-t-BuPh | 4-t-BuPh | Ph | Ph |
| 112383 | 1,3-di-t-BuPh | 1,3-di-t-BuPh | 1,3-di-t-BuPh | Ph | Ph |
| 112384 | 1,3-di-t-BuPh | 1,3-di-t-BuPh | 9-Cbz | Ph | Ph |
| 112385 | 1,3-di-t-BuPh | 1,3-di-t-BuPh | t-Bu | CN | CN |
| 112386 | 1,3-di-t-BuPh | 1,3-di-t-BuPh | Ph | CN | CN |
| 112387 | 1,3-di-t-BuPh | 1,3-di-t-BuPh | CN | CN | CN |
| 112388 | 1,3-di-t-BuPh | 1,3-di-t-BuPh | DPA | CN | CN |
| 112389 | 1,3-di-t-BuPh | 1,3-di-t-BuPh | 2-DBF | CN | CN |

TABLE 1-continued

| Compound No. | $R_{11b}$ | $R_{12c}$ | $R_{14b}$ | $R_{18b}$ | $R_{19b}$ |
|---|---|---|---|---|---|
| 112390 | 1,3-di-t-BuPh | 1,3-di-t-BuPh | 2-DBT | CN | CN |
| 112391 | 1,3-di-t-BuPh | 1,3-di-t-BuPh | 4-t-BuPh | CN | CN |
| 112392 | 1,3-di-t-BuPh | 1,3-di-t-BuPh | 1,3-di-t-BuPh | CN | CN |
| 112393 | 1,3-di-t-BuPh | 1,3-di-t-BuPh | 9-Cbz | CN | CN |
| 112394 | 1,3-di-t-BuPh | 1,3-di-t-BuPh | t-Bu | 9-Cbz | 9-Cbz |
| 112395 | 1,3-di-t-BuPh | 1,3-di-t-BuPh | Ph | 9-Cbz | 9-Cbz |
| 112396 | 1,3-di-t-BuPh | 1,3-di-t-BuPh | CN | 9-Cbz | 9-Cbz |
| 112397 | 1,3-di-t-BuPh | 1,3-di-t-BuPh | DPA | 9-Cbz | 9-Cbz |
| 112398 | 1,3-di-t-BuPh | 1,3-di-t-BuPh | 2-DBF | 9-Cbz | 9-Cbz |
| 112399 | 1,3-di-t-BuPh | 1,3-di-t-BuPh | 2-DBT | 9-Cbz | 9-Cbz |
| 112400 | 1,3-di-t-BuPh | 1,3-di-t-BuPh | 4-t-BuPh | 9-Cbz | 9-Cbz |
| 112401 | 1,3-di-t-BuPh | 1,3-di-t-BuPh | 1,3-di-t-BuPh | 9-Cbz | 9-Cbz |
| 112402 | 1,3-di-t-BuPh | 1,3-di-t-BuPh | 9-Cbz | 9-Cbz | 9-Cbz |
| 112403 | 1,3-di-t-BuPh | 1,3-di-t-BuPh | t-Bu | 4-t-BuPh | 4-t-BuPh |
| 112404 | 1,3-di-t-BuPh | 1,3-di-t-BuPh | Ph | 4-t-BuPh | 4-t-BuPh |
| 112405 | 1,3-di-t-BuPh | 1,3-di-t-BuPh | CN | 4-t-BuPh | 4-t-BuPh |
| 112406 | 1,3-di-t-BuPh | 1,3-di-t-BuPh | DPA | 4-t-BuPh | 4-t-BuPh |
| 112407 | 1,3-di-t-BuPh | 1,3-di-t-BuPh | 2-DBF | 4-t-BuPh | 4-t-BuPh |
| 112408 | 1,3-di-t-BuPh | 1,3-di-t-BuPh | 2-DBT | 4-t-BuPh | 4-t-BuPh |
| 112409 | 1,3-di-t-BuPh | 1,3-di-t-BuPh | 4-t-BuPh | 4-t-BuPh | 4-t-BuPh |
| 112410 | 1,3-di-t-BuPh | 1,3-di-t-BuPh | 1,3-di-t-BuPh | 4-t-BuPh | 4-t-BuPh |
| 112411 | 1,3-di-t-BuPh | 1,3-di-t-BuPh | 9-Cbz | 4-t-BuPh | 4-t-BuPh |
| 112412 | 1,3-di-t-BuPh | 1,3-di-t-BuPh | t-Bu | 1,3-di-t-BuPh | 1,3-di-t-BuPh |
| 112413 | 1,3-di-t-BuPh | 1,3-di-t-BuPh | Ph | 1,3-di-t-BuPh | 1,3-di-t-BuPh |
| 112414 | 1,3-di-t-BuPh | 1,3-di-t-BuPh | CN | 1,3-di-t-BuPh | 1,3-di-t-BuPh |
| 112415 | 1,3-di-t-BuPh | 1,3-di-t-BuPh | DPA | 1,3-di-t-BuPh | 1,3-di-t-BuPh |
| 112416 | 1,3-di-t-BuPh | 1,3-di-t-BuPh | 2-DBF | 1,3-di-t-BuPh | 1,3-di-t-BuPh |
| 112417 | 1,3-di-t-BuPh | 1,3-di-t-BuPh | 2-DBT | 1,3-di-t-BuPh | 1,3-di-t-BuPh |
| 112418 | 1,3-di-t-BuPh | 1,3-di-t-BuPh | 4-t-BuPh | 1,3-di-t-BuPh | 1,3-di-t-BuPh |
| 112419 | 1,3-di-t-BuPh | 1,3-di-t-BuPh | 1,3-di-t-BuPh | 1,3-di-t-BuPh | 1,3-di-t-BuPh |
| 112420 | 1,3-di-t-BuPh | 1,3-di-t-BuPh | 9-Cbz | 1,3-di-t-BuPh | 1,3-di-t-BuPh |

Group HC2

The heterocyclic compound may be represented by Formula 11-5, and substituents may be defined as shown in Table 2.

TABLE 2

| Compound No. | $R_{11b}$ | $R_{12c}$ | $R_{14b}$ | $R_{18b}$ | $R_{19b}$ |
|---|---|---|---|---|---|
| 115001 | t-Bu | t-Bu | t-Bu | t-Bu | t-Bu |
| 115002 | t-Bu | t-Bu | t-Bu | Ph | Ph |
| 115003 | t-Bu | t-Bu | t-Bu | 4-t-BuPh | 4-t-BuPh |
| 115004 | t-Bu | t-Bu | t-Bu | 9-Cbz | 9-Cbz |
| 115005 | t-Bu | t-Bu | Ph | t-Bu | t-Bu |
| 115006 | t-Bu | t-Bu | Ph | Ph | Ph |
| 115007 | t-Bu | t-Bu | 9-Cbz | t-Bu | t-Bu |
| 115008 | Ph | Ph | t-Bu | t-Bu | t-Bu |
| 115009 | Ph | Ph | t-Bu | Ph | Ph |
| 115010 | t-Bu | t-Bu | H | H | H |
| 115011 | H | H | t-Bu | H | H |
| 115012 | H | H | H | t-Bu | t-Bu |
| 115013 | t-Bu | t-Bu | t-Bu | H | H |
| 115014 | H | H | t-Bu | t-Bu | t-Bu |
| 115015 | t-Bu | t-Bu | H | t-Bu | t-Bu |
| 115016 | Ph | Ph | H | H | H |
| 115017 | H | H | Ph | H | H |
| 115018 | H | H | H | Ph | Ph |
| 115019 | Ph | Ph | Ph | H | H |
| 115020 | H | H | Ph | Ph | Ph |
| 115021 | Ph | Ph | H | Ph | Ph |
| 115022 | CN | CN | H | H | H |
| 115023 | H | H | CN | H | H |
| 115024 | H | H | H | CN | CN |
| 115025 | CN | CN | CN | H | H |
| 115026 | H | H | CN | CN | CN |
| 115027 | CN | CN | H | CN | CN |
| 115028 | 9-Cbz | 9-Cbz | H | H | H |
| 115029 | H | H | 9-Cbz | H | H |
| 115030 | H | H | H | 9-Cbz | 9-Cbz |
| 115031 | 9-Cbz | 9-Cbz | 9-Cbz | H | H |
| 115032 | H | H | 9-Cbz | 9-Cbz | 9-Cbz |
| 115033 | 9-Cbz | 9-Cbz | H | 9-Cbz | 9-Cbz |
| 115034 | Me | Me | H | H | H |
| 115035 | H | H | Me | H | H |
| 115036 | H | H | H | Me | Me |
| 115037 | Me | Me | Me | H | H |
| 115038 | H | H | Me | Me | Me |
| 115039 | Me | Me | H | Me | Me |
| 115040 | $CD_3$ | CD3 | H | H | H |
| 115041 | H | H | CD3 | H | H |
| 115042 | H | H | H | CD3 | CD3 |
| 115043 | CD3 | CD3 | CD3 | H | H |

TABLE 2-continued

| Compound No. | R₁₁ᵦ | R₁₂c | R₁₄ᵦ | R₁₈ᵦ | R₁₉ᵦ |
|---|---|---|---|---|---|
| 115044 | H | H | CD3 | CD3 | CD3 |
| 115045 | CD3 | CD3 | H | CD3 | CD3 |
| 115046 | 4-t-BuPh | 4-t-BuPh | H | H | H |
| 115047 | H | H | 4-t-BuPh | H | H |
| 115048 | H | H | H | 4-t-BuPh | 4-t-BuPh |
| 115049 | 4-t-BuPh | 4-t-BuPh | 4-t-BuPh | H | H |
| 115050 | H | H | 4-t-BuPh | 4-t-BuPh | 4-t-BuPh |
| 115051 | 4-t-BuPh | 4-t-BuPh | H | 4-t-BuPh | 4-t-BuPh |
| 115052 | 1,3-di-t-BuPh | 1,3-di-t-BuPh | H | H | H |
| 115053 | H | H | 1,3-di-t-BuPh | H | H |
| 115054 | H | H | H | 1,3-di-t-BuPh | 1,3-di-t-BuPh |
| 115055 | 1,3-di-t-BuPh | 1,3-di-t-BuPh | 1,3-di-t-BuPh | H | H |
| 115056 | H | H | 1,3-di-t-BuPh | 1,3-di-t-BuPh | 1,3-di-t-BuPh |
| 115057 | 1,3-di-t-BuPh | 1,3-di-t-BuPh | H | 1,3-di-t-BuPh | 1,3-di-t-BuPh |
| 115058 | t-Bu | t-Bu | Ph | H | H |
| 115059 | t-Bu | t-Bu | CN | H | H |
| 115060 | t-Bu | t-Bu | DPA | H | H |
| 115061 | t-Bu | t-Bu | 2-DBF | H | H |
| 115062 | t-Bu | t-Bu | 2-DBT | H | H |
| 115063 | t-Bu | t-Bu | 4-t-BuPh | H | H |
| 115064 | t-Bu | t-Bu | 1,3-di-t-BuPh | H | H |
| 115065 | t-Bu | t-Bu | 9-Cbz | H | H |
| 115066 | t-Bu | t-Bu | CN | t-Bu | t-Bu |
| 115067 | t-Bu | t-Bu | DPA | t-Bu | t-Bu |
| 115068 | t-Bu | t-Bu | 2-DBF | t-Bu | t-Bu |
| 115069 | t-Bu | t-Bu | 2-DBT | t-Bu | t-Bu |
| 115070 | t-Bu | t-Bu | 4-t-BuPh | t-Bu | t-Bu |
| 115071 | t-Bu | t-Bu | 1,3-di-t-BuPh | t-Bu | t-Bu |
| 115072 | t-Bu | t-Bu | CN | Ph | Ph |
| 115073 | t-Bu | t-Bu | DPA | Ph | Ph |
| 115074 | t-Bu | t-Bu | 2-DBF | Ph | Ph |
| 115075 | t-Bu | t-Bu | 2-DBT | Ph | Ph |
| 115076 | t-Bu | t-Bu | 4-t-BuPh | Ph | Ph |
| 115077 | t-Bu | t-Bu | 1,3-di-t-BuPh | Ph | Ph |
| 115078 | t-Bu | t-Bu | 9-Cbz | Ph | Ph |
| 115079 | t-Bu | t-Bu | t-Bu | CN | CN |
| 115080 | t-Bu | t-Bu | Ph | CN | CN |
| 115081 | t-Bu | t-Bu | CN | CN | CN |
| 115082 | t-Bu | t-Bu | DPA | CN | CN |
| 115083 | t-Bu | t-Bu | 2-DBF | CN | CN |
| 115084 | t-Bu | t-Bu | 2-DBT | CN | CN |
| 115085 | t-Bu | t-Bu | 4-t-BuPh | CN | CN |
| 115086 | t-Bu | t-Bu | 1,3-di-t-BuPh | CN | CN |
| 115087 | t-Bu | t-Bu | 9-Cbz | CN | CN |
| 115088 | t-Bu | t-Bu | Ph | 9-Cbz | 9-Cbz |
| 115089 | t-Bu | t-Bu | CN | 9-Cbz | 9-Cbz |
| 115090 | t-Bu | t-Bu | DPA | 9-Cbz | 9-Cbz |
| 115091 | t-Bu | t-Bu | 2-DBF | 9-Cbz | 9-Cbz |
| 115092 | t-Bu | t-Bu | 2-DBT | 9-Cbz | 9-Cbz |
| 115093 | t-Bu | t-Bu | 4-t-BuPh | 9-Cbz | 9-Cbz |
| 115094 | t-Bu | t-Bu | 1,3-di-t-BuPh | 9-Cbz | 9-Cbz |
| 115095 | t-Bu | t-Bu | 9-Cbz | 9-Cbz | 9-Cbz |
| 115096 | t-Bu | t-Bu | Ph | 4-t-BuPh | 4-t-BuPh |
| 115097 | t-Bu | t-Bu | CN | 4-t-BuPh | 4-t-BuPh |
| 115098 | t-Bu | t-Bu | DPA | 4-t-BuPh | 4-t-BuPh |
| 115099 | t-Bu | t-Bu | 2-DBF | 4-t-BuPh | 4-t-BuPh |
| 115100 | t-Bu | t-Bu | 2-DBT | 4-t-BuPh | 4-t-BuPh |
| 115101 | t-Bu | t-Bu | 4-t-BuPh | 4-t-BuPh | 4-t-BuPh |
| 115102 | t-Bu | t-Bu | 1,3-di-t-BuPh | 4-t-BuPh | 4-t-BuPh |
| 115103 | t-Bu | t-Bu | 9-Cbz | 4-t-BuPh | 4-t-BuPh |
| 115104 | t-Bu | t-Bu | t-Bu | 1,3-di-t-BuPh | 1,3-di-t-BuPh |
| 115105 | t-Bu | t-Bu | Ph | 1,3-di-t-BuPh | 1,3-di-t-BuPh |
| 115106 | t-Bu | t-Bu | CN | 1,3-di-t-BuPh | 1,3-di-t-BuPh |
| 115107 | t-Bu | t-Bu | DPA | 1,3-di-t-BuPh | 1,3-di-t-BuPh |
| 115108 | t-Bu | t-Bu | 2-DBF | 1,3-di-t-BuPh | 1,3-di-t-BuPh |
| 115109 | t-Bu | t-Bu | 2-DBT | 1,3-di-t-BuPh | 1,3-di-t-BuPh |
| 115110 | t-Bu | t-Bu | 4-t-BuPh | 1,3-di-t-BuPh | 1,3-di-t-BuPh |
| 115111 | t-Bu | t-Bu | 1,3-di-t-BuPh | 1,3-di-t-BuPh | 1,3-di-t-BuPh |
| 115112 | t-Bu | t-Bu | 9-Cbz | 1,3-di-t-BuPh | 1,3-di-t-BuPh |
| 115113 | Ph | Ph | t-Bu | H | H |
| 115114 | Ph | Ph | CN | H | H |
| 115115 | Ph | Ph | DPA | H | H |
| 115116 | Ph | Ph | 2-DBF | H | H |
| 115117 | Ph | Ph | 2-DBT | H | H |
| 115118 | Ph | Ph | 4-t-BuPh | H | H |
| 115119 | Ph | Ph | 1,3-di-t-BuPh | H | H |
| 115120 | Ph | Ph | 9-Cbz | H | H |
| 115121 | Ph | Ph | Ph | t-Bu | t-Bu |

TABLE 2-continued

| Compound No. | R$_{11b}$ | R$_{12c}$ | R$_{14b}$ | R$_{18b}$ | R$_{19b}$ |
|---|---|---|---|---|---|
| 115122 | Ph | Ph | CN | t-Bu | t-Bu |
| 115123 | Ph | Ph | DPA | t-Bu | t-Bu |
| 115124 | Ph | Ph | 2-DBF | t-Bu | t-Bu |
| 115125 | Ph | Ph | 2-DBT | t-Bu | t-Bu |
| 115126 | Ph | Ph | 4-t-BuPh | t-Bu | t-Bu |
| 115127 | Ph | Ph | 1,3-di-t-BuPh | t-Bu | t-Bu |
| 115128 | Ph | Ph | 9-Cbz | t-Bu | t-Bu |
| 115129 | Ph | Ph | Ph | Ph | Ph |
| 115130 | Ph | Ph | CN | Ph | Ph |
| 115131 | Ph | Ph | DPA | Ph | Ph |
| 115132 | Ph | Ph | 2-DBF | Ph | Ph |
| 115133 | Ph | Ph | 2-DBT | Ph | Ph |
| 115134 | Ph | Ph | 4-t-BuPh | Ph | Ph |
| 115135 | Ph | Ph | 1,3-di-t-BuPh | Ph | Ph |
| 115136 | Ph | Ph | 9-Cbz | Ph | Ph |
| 115137 | Ph | Ph | t-Bu | CN | CN |
| 115138 | Ph | Ph | Ph | CN | CN |
| 115139 | Ph | Ph | CN | CN | CN |
| 115140 | Ph | Ph | DPA | CN | CN |
| 115141 | Ph | Ph | 2-DBF | CN | CN |
| 115142 | Ph | Ph | 2-DBT | CN | CN |
| 115143 | Ph | Ph | 4-t-BuPh | CN | CN |
| 115144 | Ph | Ph | 1,3-di-t-BuPh | CN | CN |
| 115145 | Ph | Ph | 9-Cbz | CN | CN |
| 115146 | Ph | Ph | t-Bu | 9-Cbz | 9-Cbz |
| 115147 | Ph | Ph | Ph | 9-Cbz | 9-Cbz |
| 115148 | Ph | Ph | CN | 9-Cbz | 9-Cbz |
| 115149 | Ph | Ph | DPA | 9-Cbz | 9-Cbz |
| 115150 | Ph | Ph | 2-DBF | 9-Cbz | 9-Cbz |
| 115151 | Ph | Ph | 2-DBT | 9-Cbz | 9-Cbz |
| 115152 | Ph | Ph | 4-t-BuPh | 9-Cbz | 9-Cbz |
| 115153 | Ph | Ph | 1,3-di-t-BuPh | 9-Cbz | 9-Cbz |
| 115154 | Ph | Ph | 9-Cbz | 9-Cbz | 9-Cbz |
| 115155 | Ph | Ph | t-Bu | 4-t-BuPh | 4-t-BuPh |
| 115156 | Ph | Ph | Ph | 4-t-BuPh | 4-t-BuPh |
| 115157 | Ph | Ph | CN | 4-t-BuPh | 4-t-BuPh |
| 115158 | Ph | Ph | DPA | 4-t-BuPh | 4-t-BuPh |
| 115159 | Ph | Ph | 2-DBF | 4-t-BuPh | 4-t-BuPh |
| 115160 | Ph | Ph | 2-DBT | 4-t-BuPh | 4-t-BuPh |
| 115161 | Ph | Ph | 4-t-BuPh | 4-t-BuPh | 4-t-BuPh |
| 115162 | Ph | Ph | 1,3-di-t-BuPh | 4-t-BuPh | 4-t-BuPh |
| 115163 | Ph | Ph | 9-Cbz | 4-t-BuPh | 4-t-BuPh |
| 115164 | Ph | Ph | t-Bu | 1,3-di-t-BuPh | 1,3-di-t-BuPh |
| 115165 | Ph | Ph | Ph | 1,3-di-t-BuPh | 1,3-di-t-BuPh |
| 115166 | Ph | Ph | CN | 1,3-di-t-BuPh | 1,3-di-t-BuPh |
| 115167 | Ph | Ph | DPA | 1,3-di-t-BuPh | 1,3-di-t-BuPh |
| 115168 | Ph | Ph | 2-DBF | 1,3-di-t-BuPh | 1,3-di-t-BuPh |
| 115169 | Ph | Ph | 2-DBT | 1,3-di-t-BuPh | 1,3-di-t-BuPh |
| 115170 | Ph | Ph | 4-t-BuPh | 1,3-di-t-BuPh | 1,3-di-t-BuPh |
| 115171 | Ph | Ph | 1,3-di-t-BuPh | 1,3-di-t-BuPh | 1,3-di-t-BuPh |
| 115172 | Ph | Ph | 9-Cbz | 1,3-di-t-BuPh | 1,3-di-t-BuPh |
| 115173 | 9-Cbz | 9-Cbz | t-Bu | H | H |
| 115174 | 9-Cbz | 9-Cbz | Ph | H | H |
| 115175 | 9-Cbz | 9-Cbz | CN | H | H |
| 115176 | 9-Cbz | 9-Cbz | DPA | H | H |
| 115177 | 9-Cbz | 9-Cbz | 2-DBF | H | H |
| 115178 | 9-Cbz | 9-Cbz | 2-DBT | H | H |
| 115179 | 9-Cbz | 9-Cbz | 4-t-BuPh | H | H |
| 115180 | 9-Cbz | 9-Cbz | 1,3-di-t-BuPh | H | H |
| 115181 | 9-Cbz | 9-Cbz | t-Bu | t-Bu | t-Bu |
| 115182 | 9-Cbz | 9-Cbz | Ph | t-Bu | t-Bu |
| 115183 | 9-Cbz | 9-Cbz | CN | t-Bu | t-Bu |
| 115184 | 9-Cbz | 9-Cbz | DPA | t-Bu | t-Bu |
| 115185 | 9-Cbz | 9-Cbz | 2-DBF | t-Bu | t-Bu |
| 115186 | 9-Cbz | 9-Cbz | 2-DBT | t-Bu | t-Bu |
| 115187 | 9-Cbz | 9-Cbz | 4-t-BuPh | t-Bu | t-Bu |
| 115188 | 9-Cbz | 9-Cbz | 1,3-di-t-BuPh | t-Bu | t-Bu |
| 115189 | 9-Cbz | 9-Cbz | 9-Cbz | t-Bu | t-Bu |
| 115190 | 9-Cbz | 9-Cbz | t-Bu | Ph | Ph |
| 115191 | 9-Cbz | 9-Cbz | Ph | Ph | Ph |
| 115192 | 9-Cbz | 9-Cbz | CN | Ph | Ph |
| 115193 | 9-Cbz | 9-Cbz | DPA | Ph | Ph |
| 115194 | 9-Cbz | 9-Cbz | 2-DBF | Ph | Ph |
| 115195 | 9-Cbz | 9-Cbz | 2-DBT | Ph | Ph |
| 115196 | 9-Cbz | 9-Cbz | 4-t-BuPh | Ph | Ph |
| 115197 | 9-Cbz | 9-Cbz | 1,3-di-t-BuPh | Ph | Ph |
| 115198 | 9-Cbz | 9-Cbz | 9-Cbz | Ph | Ph |
| 115199 | 9-Cbz | 9-Cbz | t-Bu | CN | CN |
| 115200 | 9-Cbz | 9-Cbz | Ph | CN | CN |
| 115201 | 9-Cbz | 9-Cbz | CN | CN | CN |
| 115202 | 9-Cbz | 9-Cbz | DPA | CN | CN |
| 115203 | 9-Cbz | 9-Cbz | 2-DBF | CN | CN |
| 115204 | 9-Cbz | 9-Cbz | 2-DBT | CN | CN |
| 115205 | 9-Cbz | 9-Cbz | 4-t-BuPh | CN | CN |

TABLE 2-continued

| Compound No. | $R_{11b}$ | $R_{12c}$ | $R_{14b}$ | $R_{18b}$ | $R_{19b}$ |
|---|---|---|---|---|---|
| 115206 | 9-Cbz | 9-Cbz | 1,3-di-t-BuPh | CN | CN |
| 115207 | 9-Cbz | 9-Cbz | 9-Cbz | CN | CN |
| 115208 | 9-Cbz | 9-Cbz | t-Bu | 9-Cbz | 9-Cbz |
| 115209 | 9-Cbz | 9-Cbz | Ph | 9-Cbz | 9-Cbz |
| 115210 | 9-Cbz | 9-Cbz | CN | 9-Cbz | 9-Cbz |
| 115211 | 9-Cbz | 9-Cbz | DPA | 9-Cbz | 9-Cbz |
| 115212 | 9-Cbz | 9-Cbz | 2-dbf | 9-Cbz | 9-Cbz |
| 115213 | 9-Cbz | 9-Cbz | 2-dbt | 9-Cbz | 9-Cbz |
| 115214 | 9-Cbz | 9-Cbz | 4-t-BuPh | 9-Cbz | 9-Cbz |
| 115215 | 9-Cbz | 9-Cbz | 1,3-di-t-BuPh | 9-Cbz | 9-Cbz |
| 115216 | 9-Cbz | 9-Cbz | 9-Cbz | 9-Cbz | 9-Cbz |
| 115217 | 9-Cbz | 9-Cbz | t-Bu | 4-t-BuPh | 4-t-BuPh |
| 115218 | 9-Cbz | 9-Cbz | Ph | 4-t-BuPh | 4-t-BuPh |
| 115219 | 9-Cbz | 9-Cbz | CN | 4-t-BuPh | 4-t-BuPh |
| 115220 | 9-Cbz | 9-Cbz | DPA | 4-t-BuPh | 4-t-BuPh |
| 115221 | 9-Cbz | 9-Cbz | 2-DBF | 4-t-BuPh | 4-t-BuPh |
| 115222 | 9-Cbz | 9-Cbz | 2-DBT | 4-t-BuPh | 4-t-BuPh |
| 115223 | 9-Cbz | 9-Cbz | 4-t-BuPh | 4-t-BuPh | 4-t-BuPh |
| 115224 | 9-Cbz | 9-Cbz | 1,3-di-t-BuPh | 4-t-BuPh | 4-t-BuPh |
| 115225 | 9-Cbz | 9-Cbz | 9-Cbz | 4-t-BuPh | 4-t-BuPh |
| 115226 | 9-Cbz | 9-Cbz | t-Bu | 1,3-di-t-BuPh | 1,3-di-t-BuPh |
| 115227 | 9-Cbz | 9-Cbz | Ph | 1,3-di-t-BuPh | 1,3-di-t-BuPh |
| 115228 | 9-Cbz | 9-Cbz | CN | 1,3-di-t-BuPh | 1,3-di-t-BuPh |
| 115229 | 9-Cbz | 9-Cbz | DPA | 1,3-di-t-BuPh | 1,3-di-t-BuPh |
| 115230 | 9-Cbz | 9-Cbz | 2-DBF | 1,3-di-t-BuPh | 1,3-di-t-BuPh |
| 115231 | 9-Cbz | 9-Cbz | 2-DBT | 1,3-di-t-BuPh | 1,3-di-t-BuPh |
| 115232 | 9-Cbz | 9-Cbz | 4-t-BuPh | 1,3-di-t-BuPh | 1,3-di-t-BuPh |
| 115233 | 9-Cbz | 9-Cbz | 1,3-di-t-BuPh | 1,3-di-t-BuPh | 1,3-di-t-BuPh |
| 115234 | 9-Cbz | 9-Cbz | 9-Cbz | 1,3-di-t-BuPh | 1,3-di-t-BuPh |
| 115235 | CN | CN | t-Bu | H | H |
| 115236 | CN | CN | Ph | H | H |
| 115237 | CN | CN | DPA | H | H |
| 115238 | CN | CN | 2-DBF | H | H |
| 115239 | CN | CN | 2-DBT | H | H |
| 115240 | CN | CN | 4-t-BuPh | H | H |
| 115241 | CN | CN | 1,3-di-t-BuPh | H | H |
| 115242 | CN | CN | 9-Cbz | H | H |
| 115243 | CN | CN | t-Bu | t-Bu | t-Bu |
| 115244 | CN | CN | Ph | t-Bu | t-Bu |
| 115245 | CN | CN | CN | t-Bu | t-Bu |
| 115246 | CN | CN | DPA | t-Bu | t-Bu |
| 115247 | CN | CN | 2-DBF | t-Bu | t-Bu |
| 115248 | CN | CN | 2-DBT | t-Bu | t-Bu |
| 115249 | CN | CN | 4-t-BuPh | t-Bu | t-Bu |
| 115250 | CN | CN | 1,3-di-t-BuPh | t-Bu | t-Bu |
| 115251 | CN | CN | 9-Cbz | t-Bu | t-Bu |
| 115252 | CN | CN | t-Bu | Ph | Ph |
| 115253 | CN | CN | Ph | Ph | Ph |
| 115254 | CN | CN | CN | Ph | Ph |
| 115255 | CN | CN | DPA | Ph | Ph |
| 115256 | CN | CN | 2-DBF | Ph | Ph |
| 115257 | CN | CN | 2-DBT | Ph | Ph |
| 115258 | CN | CN | 4-t-BuPh | Ph | Ph |
| 115259 | CN | CN | 1,3-di-t-BuPh | Ph | Ph |
| 115260 | CN | CN | 9-Cbz | Ph | Ph |
| 115261 | CN | CN | t-Bu | CN | CN |
| 115262 | CN | CN | Ph | CN | CN |
| 115263 | CN | CN | CN | CN | CN |
| 115264 | CN | CN | DPA | CN | CN |
| 115265 | CN | CN | 2-DBF | CN | CN |
| 115266 | CN | CN | 2-DBT | CN | CN |
| 115267 | CN | CN | 4-t-BuPh | CN | CN |
| 115268 | CN | CN | 1,3-di-t-BuPh | CN | CN |
| 115269 | CN | CN | 9-Cbz | CN | CN |
| 115270 | CN | CN | t-Bu | 9-Cbz | 9-Cbz |
| 115271 | CN | CN | Ph | 9-Cbz | 9-Cbz |
| 115272 | CN | CN | CN | 9-Cbz | 9-Cbz |
| 115273 | CN | CN | DPA | 9-Cbz | 9-Cbz |
| 115274 | CN | CN | 2-DBF | 9-Cbz | 9-Cbz |
| 115275 | CN | CN | 2-DBT | 9-Cbz | 9-Cbz |
| 115276 | CN | CN | 4-t-BuPh | 9-Cbz | 9-Cbz |
| 115277 | CN | CN | 1,3-di-t-BuPh | 9-Cbz | 9-Cbz |
| 115278 | CN | CN | 9-Cbz | 9-Cbz | 9-Cbz |
| 115279 | CN | CN | t-Bu | 4-t-BuPh | 4-t-BuPh |
| 115280 | CN | CN | Ph | 4-t-BuPh | 4-t-BuPh |
| 115281 | CN | CN | CN | 4-t-BuPh | 4-t-BuPh |
| 115282 | CN | CN | DPA | 4-t-BuPh | 4-t-BuPh |
| 115283 | CN | CN | 2-DBF | 4-t-BuPh | 4-t-BuPh |
| 115284 | CN | CN | 2-DBT | 4-t-BuPh | 4-t-BuPh |
| 115285 | CN | CN | 4-t-BuPh | 4-t-BuPh | 4-t-BuPh |
| 115286 | CN | CN | 1,3-di-t-BuPh | 4-t-BuPh | 4-t-BuPh |
| 115287 | CN | CN | 9-Cbz | 4-t-BuPh | 4-t-BuPh |

TABLE 2-continued

| Compound No. | $R_{11b}$ | $R_{12c}$ | $R_{14b}$ | $R_{18b}$ | $R_{19b}$ |
|---|---|---|---|---|---|
| 115288 | CN | CN | t-Bu | 1,3-di-t-BuPh | 1,3-di-t-BuPh |
| 115289 | CN | CN | Ph | 1,3-di-t-BuPh | 1,3-di-t-BuPh |
| 115290 | CN | CN | CN | 1,3-di-t-BuPh | 1,3-di-t-BuPh |
| 115291 | CN | CN | DPA | 1,3-di-t-BuPh | 1,3-di-t-BuPh |
| 115292 | CN | CN | 2-DBF | 1,3-di-t-BuPh | 1,3-di-t-BuPh |
| 115293 | CN | CN | 2-DBT | 1,3-di-t-BuPh | 1,3-di-t-BuPh |
| 115294 | CN | CN | 4-t-BuPh | 1,3-di-t-BuPh | 1,3-di-t-BuPh |
| 115295 | CN | CN | 1,3-di-t-BuPh | 1,3-di-t-BuPh | 1,3-di-t-BuPh |
| 115296 | CN | CN | 9-Cbz | 1,3-di-t-BuPh | 1,3-di-t-BuPh |
| 115297 | 4-t-BuPh | 4-t-BuPh | t-Bu | H | H |
| 115298 | 4-t-BuPh | 4-t-BuPh | Ph | H | H |
| 115299 | 4-t-BuPh | 4-t-BuPh | CN | H | H |
| 115300 | 4-t-BuPh | 4-t-BuPh | DPA | H | H |
| 115301 | 4-t-BuPh | 4-t-BuPh | 2-DBF | H | H |
| 115302 | 4-t-BuPh | 4-t-BuPh | 2-DBT | H | H |
| 115303 | 4-t-BuPh | 4-t-BuPh | 1,3-di-t-BuPh | H | H |
| 115304 | 4-t-BuPh | 4-t-BuPh | 9-Cbz | H | H |
| 115305 | 4-t-BuPh | 4-t-BuPh | t-Bu | t-Bu | t-Bu |
| 115306 | 4-t-BuPh | 4-t-BuPh | Ph | t-Bu | t-Bu |
| 115307 | 4-t-BuPh | 4-t-BuPh | CN | t-Bu | t-Bu |
| 115308 | 4-t-BuPh | 4-t-BuPh | DPA | t-Bu | t-Bu |
| 115309 | 4-t-BuPh | 4-t-BuPh | 2-DBF | t-Bu | t-Bu |
| 115310 | 4-t-BuPh | 4-t-BuPh | 2-DBT | t-Bu | t-Bu |
| 115311 | 4-t-BuPh | 4-t-BuPh | 4-t-BuPh | t-Bu | t-Bu |
| 115312 | 4-t-BuPh | 4-t-BuPh | 1,3-di-t-BuPh | t-Bu | t-Bu |
| 115313 | 4-t-BuPh | 4-t-BuPh | 9-Cbz | t-Bu | t-Bu |
| 115314 | 4-t-BuPh | 4-t-BuPh | t-Bu | Ph | Ph |
| 115315 | 4-t-BuPh | 4-t-BuPh | Ph | Ph | Ph |
| 115316 | 4-t-BuPh | 4-t-BuPh | CN | Ph | Ph |
| 115317 | 4-t-BuPh | 4-t-BuPh | DPA | Ph | Ph |
| 115318 | 4-t-BuPh | 4-t-BuPh | 2-DBF | Ph | Ph |
| 115319 | 4-t-BuPh | 4-t-BuPh | 2-DBT | Ph | Ph |
| 115320 | 4-t-BuPh | 4-t-BuPh | 4-t-BuPh | Ph | Ph |
| 115321 | 4-t-BuPh | 4-t-BuPh | 1,3-di-t-BuPh | Ph | Ph |
| 115322 | 4-t-BuPh | 4-t-BuPh | 9-Cbz | Ph | Ph |
| 115323 | 4-t-BuPh | 4-t-BuPh | t-Bu | CN | CN |
| 115324 | 4-t-BuPh | 4-t-BuPh | Ph | CN | CN |
| 115325 | 4-t-BuPh | 4-t-BuPh | CN | CN | CN |
| 115326 | 4-t-BuPh | 4-t-BuPh | DPA | CN | CN |
| 115327 | 4-t-BuPh | 4-t-BuPh | 2-DBF | CN | CN |
| 115328 | 4-t-BuPh | 4-t-BuPh | 2-DBT | CN | CN |
| 115329 | 4-t-BuPh | 4-t-BuPh | 4-t-BuPh | CN | CN |
| 115330 | 4-t-BuPh | 4-t-BuPh | 1,3-di-t-BuPh | CN | CN |
| 115331 | 4-t-BuPh | 4-t-BuPh | 9-Cbz | CN | CN |
| 115332 | 4-t-BuPh | 4-t-BuPh | t-Bu | 9-Cbz | 9-Cbz |
| 115333 | 4-t-BuPh | 4-t-BuPh | Ph | 9-Cbz | 9-Cbz |
| 115334 | 4-t-BuPh | 4-t-BuPh | CN | 9-Cbz | 9-Cbz |
| 115335 | 4-t-BuPh | 4-t-BuPh | DPA | 9-Cbz | 9-Cbz |
| 115336 | 4-t-BuPh | 4-t-BuPh | 2-DBF | 9-Cbz | 9-Cbz |
| 115337 | 4-t-BuPh | 4-t-BuPh | 2-DBT | 9-Cbz | 9-Cbz |
| 115338 | 4-t-BuPh | 4-t-BuPh | 4-t-BuPh | 9-Cbz | 9-Cbz |
| 115339 | 4-t-BuPh | 4-t-BuPh | 1,3-di-t-BuPh | 9-Cbz | 9-Cbz |
| 115340 | 4-t-BuPh | 4-t-BuPh | 9-Cbz | 9-Cbz | 9-Cbz |
| 115341 | 4-t-BuPh | 4-t-BuPh | t-Bu | 4-t-BuPh | 4-t-BuPh |
| 115342 | 4-t-BuPh | 4-t-BuPh | Ph | 4-t-BuPh | 4-t-BuPh |
| 115343 | 4-t-BuPh | 4-t-BuPh | CN | 4-t-BuPh | 4-t-BuPh |
| 115344 | 4-t-BuPh | 4-t-BuPh | DPA | 4-t-BuPh | 4-t-BuPh |
| 115345 | 4-t-BuPh | 4-t-BuPh | 2-DBF | 4-t-BuPh | 4-t-BuPh |
| 115346 | 4-t-BuPh | 4-t-BuPh | 2-DBT | 4-t-BuPh | 4-t-BuPh |
| 115347 | 4-t-BuPh | 4-t-BuPh | 4-t-BuPh | 4-t-BuPh | 4-t-BuPh |
| 115348 | 4-t-BuPh | 4-t-BuPh | 1,3-di-t-BuPh | 4-t-BuPh | 4-t-BuPh |
| 115349 | 4-t-BuPh | 4-t-BuPh | 9-Cbz | 4-t-BuPh | 4-t-BuPh |
| 115350 | 4-t-BuPh | 4-t-BuPh | t-Bu | 1,3-di-t-BuPh | 1,3-di-t-BuPh |
| 115351 | 4-t-BuPh | 4-t-BuPh | Ph | 1,3-di-t-BuPh | 1,3-di-t-BuPh |
| 115352 | 4-t-BuPh | 4-t-BuPh | CN | 1,3-di-t-BuPh | 1,3-di-t-BuPh |
| 115353 | 4-t-BuPh | 4-t-BuPh | DPA | 1,3-di-t-BuPh | 1,3-di-t-BuPh |
| 115354 | 4-t-BuPh | 4-t-BuPh | 2-DBF | 1,3-di-t-BuPh | 1,3-di-t-BuPh |

TABLE 2-continued

| Compound No. | $R_{11b}$ | $R_{12c}$ | $R_{14b}$ | $R_{18b}$ | $R_{19b}$ |
|---|---|---|---|---|---|
| 115355 | 4-t-BuPh | 4-t-BuPh | 2-DBT | 1,3-di-t-BuPh | 1,3-di-t-BuPh |
| 115356 | 4-t-BuPh | 4-t-BuPh | 4-t-BuPh | 1,3-di-t-BuPh | 1,3-di-t-BuPh |
| 115357 | 4-t-BuPh | 4-t-BuPh | 1,3-di-t-BuPh | 1,3-di-t-BuPh | 1,3-di-t-BuPh |
| 115358 | 4-t-BuPh | 4-t-BuPh | 9-Cbz | 1,3-di-t-BuPh | 1,3-di-t-BuPh |
| 115359 | 1,3-di-t-BuPh | 1,3-di-t-BuPh | t-Bu | H | H |
| 115360 | 1,3-di-t-BuPh | 1,3-di-t-BuPh | Ph | H | H |
| 115361 | 1,3-di-t-BuPh | 1,3-di-t-BuPh | CN | H | H |
| 115362 | 1,3-di-t-BuPh | 1,3-di-t-BuPh | DPA | H | H |
| 115363 | 1,3-di-t-BuPh | 1,3-di-t-BuPh | 2-DBF | H | H |
| 115364 | 1,3-di-t-BuPh | 1,3-di-t-BuPh | 2-DBT | H | H |
| 115365 | 1,3-di-t-BuPh | 1,3-di-t-BuPh | 4-t-BuPh | H | H |
| 115366 | 1,3-di-t-BuPh | 1,3-di-t-BuPh | 9-Cbz | H | H |
| 115367 | 1,3-di-t-BuPh | 1,3-di-t-BuPh | t-Bu | t-Bu | t-Bu |
| 115368 | 1,3-di-t-BuPh | 1,3-di-t-BuPh | Ph | t-Bu | t-Bu |
| 115369 | 1,3-di-t-BuPh | 1,3-di-t-BuPh | CN | t-Bu | t-Bu |
| 115370 | 1,3-di-t-BuPh | 1,3-di-t-BuPh | DPA | t-Bu | t-Bu |
| 115371 | 1,3-di-t-BuPh | 1,3-di-t-BuPh | 2-DBF | t-Bu | t-Bu |
| 115372 | 1,3-di-t-BuPh | 1,3-di-t-BuPh | 2-DBT | t-Bu | t-Bu |
| 115373 | 1,3-di-t-BuPh | 1,3-di-t-BuPh | 4-t-BuPh | t-Bu | t-Bu |
| 115374 | 1,3-di-t-BuPh | 1,3-di-t-BuPh | 1,3-di-t-BuPh | t-Bu | t-Bu |
| 115375 | 1,3-di-t-BuPh | 1,3-di-t-BuPh | 9-Cbz | t-Bu | t-Bu |
| 115376 | 1,3-di-t-BuPh | 1,3-di-t-BuPh | t-Bu | Ph | Ph |
| 115377 | 1,3-di-t-BuPh | 1,3-di-t-BuPh | Ph | Ph | Ph |
| 115378 | 1,3-di-t-BuPh | 1,3-di-t-BuPh | CN | Ph | Ph |
| 115379 | 1,3-di-t-BuPh | 1,3-di-t-BuPh | DPA | Ph | Ph |
| 115380 | 1,3-di-t-BuPh | 1,3-di-t-BuPh | 2-DBF | Ph | Ph |
| 115381 | 1,3-di-t-BuPh | 1,3-di-t-BuPh | 2-DBT | Ph | Ph |
| 115382 | 1,3-di-t-BuPh | 1,3-di-t-BuPh | 4-t-BuPh | Ph | Ph |
| 115383 | 1,3-di-t-BuPh | 1,3-di-t-BuPh | 1,3-di-t-BuPh | Ph | Ph |
| 115384 | 1,3-di-t-BuPh | 1,3-di-t-BuPh | 9-Cbz | Ph | Ph |
| 115385 | 1,3-di-t-BuPh | 1,3-di-t-BuPh | t-Bu | CN | CN |
| 115386 | 1,3-di-t-BuPh | 1,3-di-t-BuPh | Ph | CN | CN |
| 115387 | 1,3-di-t-BuPh | 1,3-di-t-BuPh | CN | CN | CN |
| 115388 | 1,3-di-t-BuPh | 1,3-di-t-BuPh | DPA | CN | CN |
| 115389 | 1,3-di-t-BuPh | 1,3-di-t-BuPh | 2-DBF | CN | CN |
| 115390 | 1,3-di-t-BuPh | 1,3-di-t-BuPh | 2-DBT | CN | CN |
| 115391 | 1,3-di-t-BuPh | 1,3-di-t-BuPh | 4-t-BuPh | CN | CN |
| 115392 | 1,3-di-t-BuPh | 1,3-di-t-BuPh | 1,3-di-t-BuPh | CN | CN |
| 115393 | 1,3-di-t-BuPh | 1,3-di-t-BuPh | 9-Cbz | CN | CN |
| 115394 | 1,3-di-t-BuPh | 1,3-di-t-BuPh | t-Bu | 9-Cbz | 9-Cbz |
| 115395 | 1,3-di-t-BuPh | 1,3-di-t-BuPh | Ph | 9-Cbz | 9-Cbz |
| 115396 | 1,3-di-t-BuPh | 1,3-di-t-BuPh | CN | 9-Cbz | 9-Cbz |
| 115397 | 1,3-di-t-BuPh | 1,3-di-t-BuPh | DPA | 9-Cbz | 9-Cbz |
| 115398 | 1,3-di-t-BuPh | 1,3-di-t-BuPh | 2-DBF | 9-Cbz | 9-Cbz |
| 115399 | 1,3-di-t-BuPh | 1,3-di-t-BuPh | 2-DBT | 9-Cbz | 9-Cbz |
| 115400 | 1,3-di-t-BuPh | 1,3-di-t-BuPh | 4-t-BuPh | 9-Cbz | 9-Cbz |
| 115401 | 1,3-di-t-BuPh | 1,3-di-t-BuPh | 1,3-di-t-BuPh | 9-Cbz | 9-Cbz |
| 115402 | 1,3-di-t-BuPh | 1,3-di-t-BuPh | 9-Cbz | 9-Cbz | 9-Cbz |
| 115403 | 1,3-di-t-BuPh | 1,3-di-t-BuPh | t-Bu | 4-t-BuPh | 4-t-BuPh |
| 115404 | 1,3-di-t-BuPh | 1,3-di-t-BuPh | Ph | 4-t-BuPh | 4-t-BuPh |

TABLE 2-continued

| Compound No. | $R_{11b}$ | $R_{12c}$ | $R_{14b}$ | $R_{18b}$ | $R_{19b}$ |
|---|---|---|---|---|---|
| 115405 | 1,3-di-t-BuPh | 1,3-di-t-BuPh | CN | 4-t-BuPh | 4-t-BuPh |
| 115406 | 1,3-di-t-BuPh | 1,3-di-t-BuPh | DPA | 4-t-BuPh | 4-t-BuPh |
| 115407 | 1,3-di-t-BuPh | 1,3-di-t-BuPh | 2-DBF | 4-t-BuPh | 4-t-BuPh |
| 115408 | 1,3-di-t-BuPh | 1,3-di-t-BuPh | 2-DBT | 4-t-BuPh | 4-t-BuPh |
| 115409 | 1,3-di-t-BuPh | 1,3-di-t-BuPh | 4-t-BuPh | 4-t-BuPh | 4-t-BuPh |
| 115410 | 1,3-di-t-BuPh | 1,3-di-t-BuPh | 1,3-di-t-BuPh | 4-t-BuPh | 4-t-BuPh |
| 115411 | 1,3-di-t-BuPh | 1,3-di-t-BuPh | 9-Cbz | 4-t-BuPh | 4-t-BuPh |
| 115412 | 1,3-di-t-BuPh | 1,3-di-t-BuPh | t-Bu | 1,3-di-t-BuPh | 1,3-di-t-BuPh |
| 115413 | 1,3-di-t-BuPh | 1,3-di-t-BuPh | Ph | 1,3-di-t-BuPh | 1,3-di-t-BuPh |
| 115414 | 1,3-di-t-BuPh | 1,3-di-t-BuPh | CN | 1,3-di-t-BuPh | 1,3-di-t-BuPh |
| 115415 | 1,3-di-t-BuPh | 1,3-di-t-BuPh | DPA | 1,3-di-t-BuPh | 1,3-di-t-BuPh |
| 115416 | 1,3-di-t-BuPh | 1,3-di-t-BuPh | 2-DBF | 1,3-di-t-BuPh | 1,3-di-t-BuPh |
| 115417 | 1,3-di-t-BuPh | 1,3-di-t-BuPh | 2-DBT | 1,3-di-t-BuPh | 1,3-di-t-BuPh |
| 115418 | 1,3-di-t-BuPh | 1,3-di-t-BuPh | 4-t-BuPh | 1,3-di-t-BuPh | 1,3-di-t-BuPh |
| 115419 | 1,3-di-t-BuPh | 1,3-di-t-BuPh | 1,3-di-t-BuPh | 1,3-di-t-BuPh | 1,3-di-t-BuPh |
| 115420 | 1,3-di-t-BuPh | 1,3-di-t-BuPh | 9-Cbz | 1,3-di-t-BuPh | 1,3-di-t-BuPh |

Group HC3

The heterocyclic compound may be represented by Formula 12-1, and substituents may be defined as shown in Table 3.

TABLE 3

| Compound No. | $R_{11b}$ | $R_{12c}$ | $R_{14b}$ | $R_{18c}$ | $R_{19b}$ |
|---|---|---|---|---|---|
| 121001 | t-Bu | t-Bu | t-Bu | t-Bu | t-Bu |
| 121002 | Ph | Ph | t-Bu | Ph | Ph |
| 121003 | t-Bu | t-Bu | H | H | H |
| 121004 | H | H | t-Bu | H | H |
| 121005 | H | H | H | t-Bu | t-Bu |
| 121006 | t-Bu | t-Bu | t-Bu | H | H |
| 121007 | H | H | t-Bu | t-Bu | t-Bu |
| 121008 | t-Bu | t-Bu | H | t-Bu | t-Bu |
| 121009 | Ph | Ph | H | H | H |
| 121010 | H | H | Ph | H | H |
| 121011 | H | H | H | Ph | Ph |
| 121012 | Ph | Ph | Ph | H | H |
| 121013 | H | H | Ph | Ph | Ph |
| 121014 | Ph | Ph | H | Ph | Ph |
| 121015 | CN | CN | H | H | H |
| 121016 | H | H | CN | H | H |
| 121017 | H | H | H | CN | CN |
| 121018 | CN | CN | CN | H | H |
| 121019 | H | H | CN | CN | CN |
| 121020 | CN | CN | H | CN | CN |
| 121021 | 9-Cbz | 9-Cbz | H | H | H |
| 121022 | H | H | 9-Cbz | H | H |
| 121023 | H | H | H | 9-Cbz | 9-Cbz |
| 121024 | 9-Cbz | 9-Cbz | 9-Cbz | H | H |
| 121025 | H | H | 9-Cbz | 9-Cbz | 9-Cbz |
| 121026 | 9-Cbz | 9-Cbz | H | 9-Cbz | 9-Cbz |
| 121027 | Me | Me | H | H | H |
| 121028 | H | H | Me | H | H |
| 121029 | H | H | H | Me | Me |
| 121030 | Me | Me | Me | H | H |
| 121031 | H | H | Me | Me | Me |
| 121032 | Me | Me | H | Me | Me |
| 121033 | CD$_3$ | CD3 | H | H | H |
| 121034 | H | H | CD3 | H | H |
| 121035 | H | H | H | CD3 | CD3 |
| 121036 | CD3 | CD3 | CD3 | H | H |
| 121037 | H | H | CD3 | CD3 | CD3 |
| 121038 | CD3 | CD3 | H | CD3 | CD3 |
| 121039 | 4-t-BuPh | 4-t-BuPh | H | H | H |
| 121040 | H | H | 4-t-BuPh | H | H |
| 121041 | H | H | H | 4-t-BuPh | 4-t-BuPh |
| 121042 | 4-t-BuPh | 4-t-BuPh | 4-t-BuPh | H | H |
| 121043 | H | H | 4-t-BuPh | 4-t-BuPh | 4-t-BuPh |
| 121044 | 4-t-BuPh | 4-t-BuPh | H | 4-t-BuPh | 4-t-BuPh |
| 121045 | 1,3-di-t-BuPh | 1,3-di-t-BuPh | H | H | H |
| 121046 | H | H | 1,3-di-t-BuPh | H | H |
| 121047 | H | H | H | 1,3-di-t-BuPh | 1,3-di-t-BuPh |
| 121048 | 1,3-di-t-BuPh | 1,3-di-t-BuPh | 1,3-di-t-BuPh | H | H |
| 121049 | H | H | 1,3-di-t-BuPh | 1,3-di-t-BuPh | 1,3-di-t-BuPh |
| 121050 | 1,3-di-t-BuPh | 1,3-di-t-BuPh | H | 1,3-di-t-BuPh | 1,3-di-t-BuPh |
| 121051 | t-Bu | t-Bu | Ph | H | H |
| 121052 | t-Bu | t-Bu | CN | H | H |
| 121053 | t-Bu | t-Bu | DPA | H | H |
| 121054 | t-Bu | t-Bu | 2-DBF | H | H |
| 121055 | t-Bu | t-Bu | 2-DBT | H | H |
| 121056 | t-Bu | t-Bu | 4-t-BuPh | H | H |
| 121057 | t-Bu | t-Bu | 1,3-di-t-BuPh | H | H |
| 121058 | t-Bu | t-Bu | 9-Cbz | H | H |
| 121059 | t-Bu | t-Bu | Ph | t-Bu | t-Bu |
| 121060 | t-Bu | t-Bu | CN | t-Bu | t-Bu |
| 121061 | t-Bu | t-Bu | DPA | t-Bu | t-Bu |
| 121062 | t-Bu | t-Bu | 2-DBF | t-Bu | t-Bu |
| 121063 | t-Bu | t-Bu | 2-DBT | t-Bu | t-Bu |
| 121064 | t-Bu | t-Bu | 4-t-BuPh | t-Bu | t-Bu |
| 121065 | t-Bu | t-Bu | 1,3-di-t-BuPh | t-Bu | t-Bu |

TABLE 3-continued

| Compound No. | $R_{11b}$ | $R_{12c}$ | $R_{14b}$ | $R_{18c}$ | $R_{19b}$ |
|---|---|---|---|---|---|
| 121066 | t-Bu | t-Bu | 9-Cbz | t-Bu | t-Bu |
| 121067 | t-Bu | t-Bu | t-Bu | Ph | Ph |
| 121068 | t-Bu | t-Bu | Ph | Ph | Ph |
| 121069 | t-Bu | t-Bu | CN | Ph | Ph |
| 121070 | t-Bu | t-Bu | DPA | Ph | Ph |
| 121071 | t-Bu | t-Bu | 2-DBF | Ph | Ph |
| 121072 | t-Bu | t-Bu | 2-DBT | Ph | Ph |
| 121073 | t-Bu | t-Bu | 4-t-BuPh | Ph | Ph |
| 121074 | t-Bu | t-Bu | 1,3-di-t-BuPh | Ph | Ph |
| 121075 | t-Bu | t-Bu | 9-Cbz | Ph | Ph |
| 121076 | t-Bu | t-Bu | t-Bu | CN | CN |
| 121077 | t-Bu | t-Bu | Ph | CN | CN |
| 121078 | t-Bu | t-Bu | CN | CN | CN |
| 121079 | t-Bu | t-Bu | DPA | CN | CN |
| 121080 | t-Bu | t-Bu | 2-DBF | CN | CN |
| 121081 | t-Bu | t-Bu | 2-DBT | CN | CN |
| 121082 | t-Bu | t-Bu | 4-t-BuPh | CN | CN |
| 121083 | t-Bu | t-Bu | 1,3-di-t-BuPh | CN | CN |
| 121084 | t-Bu | t-Bu | 9-Cbz | CN | CN |
| 121085 | t-Bu | t-Bu | t-Bu | 9-Cbz | 9-Cbz |
| 121086 | t-Bu | t-Bu | Ph | 9-Cbz | 9-Cbz |
| 121087 | t-Bu | t-Bu | CN | 9-Cbz | 9-Cbz |
| 121088 | t-Bu | t-Bu | DPA | 9-Cbz | 9-Cbz |
| 121089 | t-Bu | t-Bu | 2-DBF | 9-Cbz | 9-Cbz |
| 121090 | t-Bu | t-Bu | 2-DBT | 9-Cbz | 9-Cbz |
| 121091 | t-Bu | t-Bu | 4-t-BuPh | 9-Cbz | 9-Cbz |
| 121092 | t-Bu | t-Bu | 1,3-di-t-BuPh | 9-Cbz | 9-Cbz |
| 121093 | t-Bu | t-Bu | 9-Cbz | 9-Cbz | 9-Cbz |
| 121094 | t-Bu | t-Bu | t-Bu | 4-t-BuPh | 4-t-BuPh |
| 121095 | t-Bu | t-Bu | Ph | 4-t-BuPh | 4-t-BuPh |
| 121096 | t-Bu | t-Bu | CN | 4-t-BuPh | 4-t-BuPh |
| 121097 | t-Bu | t-Bu | DPA | 4-t-BuPh | 4-t-BuPh |
| 121098 | t-Bu | t-Bu | 2-DBF | 4-t-BuPh | 4-t-BuPh |
| 121099 | t-Bu | t-Bu | 2-DBT | 4-t-BuPh | 4-t-BuPh |
| 121100 | t-Bu | t-Bu | 4-t-BuPh | 4-t-BuPh | 4-t-BuPh |
| 121101 | t-Bu | t-Bu | 1,3-di-t-BuPh | 4-t-BuPh | 4-t-BuPh |
| 121102 | t-Bu | t-Bu | 9-Cbz | 4-t-BuPh | 4-t-BuPh |
| 121103 | t-Bu | t-Bu | t-Bu | 1,3-di-t-BuPh | 1,3-di-t-BuPh |
| 121104 | t-Bu | t-Bu | Ph | 1,3-di-t-BuPh | 1,3-di-t-BuPh |
| 121105 | t-Bu | t-Bu | CN | 1,3-di-t-BuPh | 1,3-di-t-BuPh |
| 121106 | t-Bu | t-Bu | DPA | 1,3-di-t-BuPh | 1,3-di-t-BuPh |
| 121107 | t-Bu | t-Bu | 2-DBF | 1,3-di-t-BuPh | 1,3-di-t-BuPh |
| 121108 | t-Bu | t-Bu | 2-DBT | 1,3-di-t-BuPh | 1,3-di-t-BuPh |
| 121109 | t-Bu | t-Bu | 4-t-BuPh | 1,3-di-t-BuPh | 1,3-di-t-BuPh |
| 121110 | t-Bu | t-Bu | 1,3-di-t-BuPh | 1,3-di-t-BuPh | 1,3-di-t-BuPh |
| 121111 | t-Bu | t-Bu | 9-Cbz | 1,3-di-t-BuPh | 1,3-di-t-BuPh |
| 121112 | Ph | Ph | t-Bu | H | H |
| 121113 | Ph | Ph | CN | H | H |
| 121114 | Ph | Ph | DPA | H | H |
| 121115 | Ph | Ph | 2-DBF | H | H |
| 121116 | Ph | Ph | 2-DBT | H | H |
| 121117 | Ph | Ph | 4-t-BuPh | H | H |
| 121118 | Ph | Ph | 1,3-di-t-BuPh | H | H |
| 121119 | Ph | Ph | 9-Cbz | H | H |
| 121120 | Ph | Ph | t-Bu | t-Bu | t-Bu |
| 121121 | Ph | Ph | Ph | t-Bu | t-Bu |
| 121122 | Ph | Ph | CN | t-Bu | t-Bu |
| 121123 | Ph | Ph | DPA | t-Bu | t-Bu |
| 121124 | Ph | Ph | 2-DBF | t-Bu | t-Bu |
| 121125 | Ph | Ph | 2-DBT | t-Bu | t-Bu |
| 121126 | Ph | Ph | 4-t-BuPh | t-Bu | t-Bu |
| 121127 | Ph | Ph | 1,3-di-t-BuPh | t-Bu | t-Bu |
| 121128 | Ph | Ph | 9-Cbz | t-Bu | t-Bu |
| 121129 | Ph | Ph | Ph | Ph | Ph |
| 121130 | Ph | Ph | CN | Ph | Ph |
| 121131 | Ph | Ph | DPA | Ph | Ph |
| 121132 | Ph | Ph | 2-DBF | Ph | Ph |
| 121133 | Ph | Ph | 2-DBT | Ph | Ph |
| 121134 | Ph | Ph | 4-t-BuPh | Ph | Ph |
| 121135 | Ph | Ph | 1,3-di-t-BuPh | Ph | Ph |
| 121136 | Ph | Ph | 9-Cbz | Ph | Ph |
| 121137 | Ph | Ph | t-Bu | CN | CN |
| 121138 | Ph | Ph | Ph | CN | CN |
| 121139 | Ph | Ph | CN | CN | CN |
| 121140 | Ph | Ph | DPA | CN | CN |
| 121141 | Ph | Ph | 2-DBF | CN | CN |
| 121142 | Ph | Ph | 2-DBT | CN | CN |
| 121143 | Ph | Ph | 4-t-BuPh | CN | CN |
| 121144 | Ph | Ph | 1,3-di-t-BuPh | CN | CN |
| 121145 | Ph | Ph | 9-Cbz | CN | CN |
| 121146 | Ph | Ph | t-Bu | 9-Cbz | 9-Cbz |
| 121147 | Ph | Ph | Ph | 9-Cbz | 9-Cbz |
| 121148 | Ph | Ph | CN | 9-Cbz | 9-Cbz |
| 121149 | Ph | Ph | DPA | 9-Cbz | 9-Cbz |
| 121150 | Ph | Ph | 2-DBF | 9-Cbz | 9-Cbz |
| 121151 | Ph | Ph | 2-DBT | 9-Cbz | 9-Cbz |
| 121152 | Ph | Ph | 4-t-BuPh | 9-Cbz | 9-Cbz |

TABLE 3-continued

| Compound No. | $R_{11b}$ | $R_{12c}$ | $R_{14b}$ | $R_{18c}$ | $R_{19b}$ |
|---|---|---|---|---|---|
| 121153 | Ph | Ph | 1,3-di-t-BuPh | 9-Cbz | 9-Cbz |
| 121154 | Ph | Ph | 9-Cbz | 9-Cbz | 9-Cbz |
| 121155 | Ph | Ph | t-Bu | 4-t-BuPh | 4-t-BuPh |
| 121156 | Ph | Ph | Ph | 4-t-BuPh | 4-t-BuPh |
| 121157 | Ph | Ph | CN | 4-t-BuPh | 4-t-BuPh |
| 121158 | Ph | Ph | DPA | 4-t-BuPh | 4-t-BuPh |
| 121159 | Ph | Ph | 2-DBF | 4-t-BuPh | 4-t-BuPh |
| 121160 | Ph | Ph | 2-DBT | 4-t-BuPh | 4-t-BuPh |
| 121161 | Ph | Ph | 4-t-BuPh | 4-t-BuPh | 4-t-BuPh |
| 121162 | Ph | Ph | 1,3-di-t-BuPh | 4-t-BuPh | 4-t-BuPh |
| 121163 | Ph | Ph | 9-Cbz | 4-t-BuPh | 4-t-BuPh |
| 121164 | Ph | Ph | t-Bu | 1,3-di-t-BuPh | 1,3-di-t-BuPh |
| 121165 | Ph | Ph | Ph | 1,3-di-t-BuPh | 1,3-di-t-BuPh |
| 121166 | Ph | Ph | CN | 1,3-di-t-BuPh | 1,3-di-t-BuPh |
| 121167 | Ph | Ph | DPA | 1,3-di-t-BuPh | 1,3-di-t-BuPh |
| 121168 | Ph | Ph | 2-DBF | 1,3-di-t-BuPh | 1,3-di-t-BuPh |
| 121169 | Ph | Ph | 2-DBT | 1,3-di-t-BuPh | 1,3-di-t-BuPh |
| 121170 | Ph | Ph | 4-t-BuPh | 1,3-di-t-BuPh | 1,3-di-t-BuPh |
| 121171 | Ph | Ph | 1,3-di-t-BuPh | 1,3-di-t-BuPh | 1,3-di-t-BuPh |
| 121172 | Ph | Ph | 9-Cbz | 1,3-di-t-BuPh | 1,3-di-t-BuPh |
| 121173 | 9-Cbz | 9-Cbz | t-Bu | H | H |
| 121174 | 9-Cbz | 9-Cbz | Ph | H | H |
| 121175 | 9-Cbz | 9-Cbz | CN | H | H |
| 121176 | 9-Cbz | 9-Cbz | DPA | H | H |
| 121177 | 9-Cbz | 9-Cbz | 2-DBF | H | H |
| 121178 | 9-Cbz | 9-Cbz | 2-DBT | H | H |
| 121179 | 9-Cbz | 9-Cbz | 4-t-BuPh | H | H |
| 121180 | 9-Cbz | 9-Cbz | 1,3-di-t-BuPh | H | H |
| 121181 | 9-Cbz | 9-Cbz | t-Bu | t-Bu | t-Bu |
| 121182 | 9-Cbz | 9-Cbz | Ph | t-Bu | t-Bu |
| 121183 | 9-Cbz | 9-Cbz | CN | t-Bu | t-Bu |
| 121184 | 9-Cbz | 9-Cbz | DPA | t-Bu | t-Bu |
| 121185 | 9-Cbz | 9-Cbz | 2-DBF | t-Bu | t-Bu |
| 121186 | 9-Cbz | 9-Cbz | 2-DBT | t-Bu | t-Bu |
| 121187 | 9-Cbz | 9-Cbz | 4-t-BuPh | t-Bu | t-Bu |
| 121188 | 9-Cbz | 9-Cbz | 1,3-di-t-BuPh | t-Bu | t-Bu |
| 121189 | 9-Cbz | 9-Cbz | 9-Cbz | t-Bu | t-Bu |
| 121190 | 9-Cbz | 9-Cbz | t-Bu | Ph | Ph |
| 121191 | 9-Cbz | 9-Cbz | Ph | Ph | Ph |
| 121192 | 9-Cbz | 9-Cbz | CN | Ph | Ph |
| 121193 | 9-Cbz | 9-Cbz | DPA | Ph | Ph |
| 121194 | 9-Cbz | 9-Cbz | 2-DBF | Ph | Ph |
| 121195 | 9-Cbz | 9-Cbz | 2-DBT | Ph | Ph |
| 121196 | 9-Cbz | 9-Cbz | 4-t-BuPh | Ph | Ph |
| 121197 | 9-Cbz | 9-Cbz | 1,3-di-t-BuPh | Ph | Ph |
| 121198 | 9-Cbz | 9-Cbz | 9-Cbz | Ph | Ph |
| 121199 | 9-Cbz | 9-Cbz | t-Bu | CN | CN |
| 121200 | 9-Cbz | 9-Cbz | Ph | CN | CN |
| 121201 | 9-Cbz | 9-Cbz | CN | CN | CN |
| 121202 | 9-Cbz | 9-Cbz | DPA | CN | CN |
| 121203 | 9-Cbz | 9-Cbz | 2-DBF | CN | CN |
| 121204 | 9-Cbz | 9-Cbz | 2-DBT | CN | CN |
| 121205 | 9-Cbz | 9-Cbz | 4-t-BuPh | CN | CN |
| 121206 | 9-Cbz | 9-Cbz | 1,3-di-t-BuPh | CN | CN |
| 121207 | 9-Cbz | 9-Cbz | 9-Cbz | CN | CN |
| 121208 | 9-Cbz | 9-Cbz | t-Bu | 9-Cbz | 9-Cbz |
| 121209 | 9-Cbz | 9-Cbz | Ph | 9-Cbz | 9-Cbz |
| 121210 | 9-Cbz | 9-Cbz | CN | 9-Cbz | 9-Cbz |
| 121211 | 9-Cbz | 9-Cbz | DPA | 9-Cbz | 9-Cbz |
| 121212 | 9-Cbz | 9-Cbz | 2-DBF | 9-Cbz | 9-Cbz |
| 121213 | 9-Cbz | 9-Cbz | 2-DBT | 9-Cbz | 9-Cbz |
| 121214 | 9-Cbz | 9-Cbz | 4-t-BuPh | 9-Cbz | 9-Cbz |
| 121215 | 9-Cbz | 9-Cbz | 1,3-di-t-BuPh | 9-Cbz | 9-Cbz |
| 121216 | 9-Cbz | 9-Cbz | 9-Cbz | 9-Cbz | 9-Cbz |
| 121217 | 9-Cbz | 9-Cbz | t-Bu | 4-t-BuPh | 4-t-BuPh |
| 121218 | 9-Cbz | 9-Cbz | Ph | 4-t-BuPh | 4-t-BuPh |
| 121219 | 9-Cbz | 9-Cbz | CN | 4-t-BuPh | 4-t-BuPh |
| 121220 | 9-Cbz | 9-Cbz | DPA | 4-t-BuPh | 4-t-BuPh |
| 121221 | 9-Cbz | 9-Cbz | 2-DBF | 4-t-BuPh | 4-t-BuPh |
| 121222 | 9-Cbz | 9-Cbz | 2-DBT | 4-t-BuPh | 4-t-BuPh |
| 121223 | 9-Cbz | 9-Cbz | 4-t-BuPh | 4-t-BuPh | 4-t-BuPh |
| 121224 | 9-Cbz | 9-Cbz | 1,3-di-t-BuPh | 4-t-BuPh | 4-t-BuPh |
| 121225 | 9-Cbz | 9-Cbz | 9-Cbz | 4-t-BuPh | 4-t-BuPh |
| 121226 | 9-Cbz | 9-Cbz | t-Bu | 1,3-di-t-BuPh | 1,3-di-t-BuPh |
| 121227 | 9-Cbz | 9-Cbz | Ph | 1,3-di-t-BuPh | 1,3-di-t-BuPh |
| 121228 | 9-Cbz | 9-Cbz | CN | 1,3-di-t-BuPh | 1,3-di-t-BuPh |
| 121229 | 9-Cbz | 9-Cbz | DPA | 1,3-di-t-BuPh | 1,3-di-t-BuPh |
| 121230 | 9-Cbz | 9-Cbz | 2-DBF | 1,3-di-t-BuPh | 1,3-di-t-BuPh |

TABLE 3-continued

| Compound No. | R$_{11b}$ | R$_{12c}$ | R$_{14b}$ | R$_{18c}$ | R$_{19b}$ |
|---|---|---|---|---|---|
| 121231 | 9-Cbz | 9-Cbz | 2-DBT | 1,3-di-t-BuPh | 1,3-di-t-BuPh |
| 121232 | 9-Cbz | 9-Cbz | 4-t-BuPh | 1,3-di-t-BuPh | 1,3-di-t-BuPh |
| 121233 | 9-Cbz | 9-Cbz | 1,3-di-t-BuPh | 1,3-di-t-BuPh | 1,3-di-t-BuPh |
| 121234 | 9-Cbz | 9-Cbz | 9-Cbz | 1,3-di-t-BuPh | 1,3-di-t-BuPh |
| 121235 | CN | CN | t-Bu | H | H |
| 121236 | CN | CN | Ph | H | H |
| 121237 | CN | CN | DPA | H | H |
| 121238 | CN | CN | 2-DBF | H | H |
| 121239 | CN | CN | 2-DBT | H | H |
| 121240 | CN | CN | 4-t-BuPh | H | H |
| 121241 | CN | CN | 1,3-di-t-BuPh | H | H |
| 121242 | CN | CN | 9-Cbz | H | H |
| 121243 | CN | CN | t-Bu | t-Bu | t-Bu |
| 121244 | CN | CN | Ph | t-Bu | t-Bu |
| 121245 | CN | CN | CN | t-Bu | t-Bu |
| 121246 | CN | CN | DPA | t-Bu | t-Bu |
| 121247 | CN | CN | 2-DBF | t-Bu | t-Bu |
| 121248 | CN | CN | 2-DBT | t-Bu | t-Bu |
| 121249 | CN | CN | 4-t-BuPh | t-Bu | t-Bu |
| 121250 | CN | CN | 1,3-di-t-BuPh | t-Bu | t-Bu |
| 121251 | CN | CN | 9-Cbz | t-Bu | t-Bu |
| 121252 | CN | CN | t-Bu | Ph | Ph |
| 121253 | CN | CN | Ph | Ph | Ph |
| 121254 | CN | CN | CN | Ph | Ph |
| 121255 | CN | CN | DPA | Ph | Ph |
| 121256 | CN | CN | 2-DBF | Ph | Ph |
| 121257 | CN | CN | 2-DBT | Ph | Ph |
| 121258 | CN | CN | 4-t-BuPh | Ph | Ph |
| 121259 | CN | CN | 1,3-di-t-BuPh | Ph | Ph |
| 121260 | CN | CN | 9-Cbz | Ph | Ph |
| 121261 | CN | CN | t-Bu | CN | CN |
| 121262 | CN | CN | Ph | CN | CN |
| 121263 | CN | CN | CN | CN | CN |
| 121264 | CN | CN | DPA | CN | CN |
| 121265 | CN | CN | 2-DBF | CN | CN |
| 121266 | CN | CN | 2-DBT | CN | CN |
| 121267 | CN | CN | 4-t-BuPh | CN | CN |
| 121268 | CN | CN | 1,3-di-t-BuPh | CN | CN |
| 121269 | CN | CN | 9-Cbz | CN | CN |
| 121270 | CN | CN | t-Bu | 9-Cbz | 9-Cbz |
| 121271 | CN | CN | Ph | 9-Cbz | 9-Cbz |
| 121272 | CN | CN | CN | 9-Cbz | 9-Cbz |
| 121273 | CN | CN | DPA | 9-Cbz | 9-Cbz |
| 121274 | CN | CN | 2-DBF | 9-Cbz | 9-Cbz |
| 121275 | CN | CN | 2-DBT | 9-Cbz | 9-Cbz |
| 121276 | CN | CN | 4-t-BuPh | 9-Cbz | 9-Cbz |
| 121277 | CN | CN | 1,3-di-t-BuPh | 9-Cbz | 9-Cbz |
| 121278 | CN | CN | 9-Cbz | 9-Cbz | 9-Cbz |
| 121279 | CN | CN | t-Bu | 4-t-BuPh | 4-t-BuPh |
| 121280 | CN | CN | Ph | 4-t-BuPh | 4-t-BuPh |
| 121281 | CN | CN | CN | 4-t-BuPh | 4-t-BuPh |
| 121282 | CN | CN | DPA | 4-t-BuPh | 4-t-BuPh |
| 121283 | CN | CN | 2-DBF | 4-t-BuPh | 4-t-BuPh |
| 121284 | CN | CN | 2-DBT | 4-t-BuPh | 4-t-BuPh |
| 121285 | CN | CN | 4-t-BuPh | 4-t-BuPh | 4-t-BuPh |
| 121286 | CN | CN | 1,3-di-t-BuPh | 4-t-BuPh | 4-t-BuPh |
| 121287 | CN | CN | 9-Cbz | 4-t-BuPh | 4-t-BuPh |
| 121288 | CN | CN | t-Bu | 1,3-di-t-BuPh | 1,3-di-t-BuPh |
| 121289 | CN | CN | Ph | 1,3-di-t-BuPh | 1,3-di-t-BuPh |
| 121290 | CN | CN | CN | 1,3-di-t-BuPh | 1,3-di-t-BuPh |
| 121291 | CN | CN | DPA | 1,3-di-t-BuPh | 1,3-di-t-BuPh |
| 121292 | CN | CN | 2-DBF | 1,3-di-t-BuPh | 1,3-di-t-BuPh |
| 121293 | CN | CN | 2-DBT | 1,3-di-t-BuPh | 1,3-di-t-BuPh |
| 121294 | CN | CN | 4-t-BuPh | 1,3-di-t-BuPh | 1,3-di-t-BuPh |
| 121295 | CN | CN | 1,3-di-t-BuPh | 1,3-di-t-BuPh | 1,3-di-t-BuPh |
| 121296 | CN | CN | 9-Cbz | 1,3-di-t-BuPh | 1,3-di-t-BuPh |
| 121297 | 4-t-BuPh | 4-t-BuPh | t-Bu | H | H |
| 121298 | 4-t-BuPh | 4-t-BuPh | Ph | H | H |
| 121299 | 4-t-BuPh | 4-t-BuPh | CN | H | H |
| 121300 | 4-t-BuPh | 4-t-BuPh | DPA | H | H |
| 121301 | 4-t-BuPh | 4-t-BuPh | 2-DBF | H | H |
| 121302 | 4-t-BuPh | 4-t-BuPh | 2-DBT | H | H |
| 121303 | 4-t-BuPh | 4-t-BuPh | 1,3-di-t-BuPh | H | H |
| 121304 | 4-t-BuPh | 4-t-BuPh | 9-Cbz | H | H |
| 121305 | 4-t-BuPh | 4-t-BuPh | t-Bu | t-Bu | t-Bu |
| 121306 | 4-t-BuPh | 4-t-BuPh | Ph | t-Bu | t-Bu |
| 121307 | 4-t-BuPh | 4-t-BuPh | CN | t-Bu | t-Bu |
| 121308 | 4-t-BuPh | 4-t-BuPh | DPA | t-Bu | t-Bu |
| 121309 | 4-t-BuPh | 4-t-BuPh | 2-DBF | t-Bu | t-Bu |

TABLE 3-continued

| Compound No. | $R_{11b}$ | $R_{12c}$ | $R_{14b}$ | $R_{18c}$ | $R_{19b}$ |
|---|---|---|---|---|---|
| 121310 | 4-t-BuPh | 4-t-BuPh | 2-DBT | t-Bu | t-Bu |
| 121311 | 4-t-BuPh | 4-t-BuPh | 4-t-BuPh | t-Bu | t-Bu |
| 121312 | 4-t-BuPh | 4-t-BuPh | 1,3-di-t-BuPh | t-Bu | t-Bu |
| 121313 | 4-t-BuPh | 4-t-BuPh | 9-Cbz | t-Bu | t-Bu |
| 121314 | 4-t-BuPh | 4-t-BuPh | t-Bu | Ph | Ph |
| 121315 | 4-t-BuPh | 4-t-BuPh | Ph | Ph | Ph |
| 121316 | 4-t-BuPh | 4-t-BuPh | CN | Ph | Ph |
| 121317 | 4-t-BuPh | 4-t-BuPh | DPA | Ph | Ph |
| 121318 | 4-t-BuPh | 4-t-BuPh | 2-DBF | Ph | Ph |
| 121319 | 4-t-BuPh | 4-t-BuPh | 2-DBT | Ph | Ph |
| 121320 | 4-t-BuPh | 4-t-BuPh | 4-t-BuPh | Ph | Ph |
| 121321 | 4-t-BuPh | 4-t-BuPh | 1,3-di-t-BuPh | Ph | Ph |
| 121322 | 4-t-BuPh | 4-t-BuPh | 9-Cbz | Ph | Ph |
| 121323 | 4-t-BuPh | 4-t-BuPh | t-Bu | CN | CN |
| 121324 | 4-t-BuPh | 4-t-BuPh | Ph | CN | CN |
| 121325 | 4-t-BuPh | 4-t-BuPh | CN | CN | CN |
| 121326 | 4-t-BuPh | 4-t-BuPh | DPA | CN | CN |
| 121327 | 4-t-BuPh | 4-t-BuPh | 2-DBF | CN | CN |
| 121328 | 4-t-BuPh | 4-t-BuPh | 2-DBT | CN | CN |
| 121329 | 4-t-BuPh | 4-t-BuPh | 4-t-BuPh | CN | CN |
| 121330 | 4-t-BuPh | 4-t-BuPh | 1,3-di-t-BuPh | CN | CN |
| 121331 | 4-t-BuPh | 4-t-BuPh | 9-Cbz | CN | CN |
| 121332 | 4-t-BuPh | 4-t-BuPh | t-Bu | 9-Cbz | 9-Cbz |
| 121333 | 4-t-BuPh | 4-t-BuPh | Ph | 9-Cbz | 9-Cbz |
| 121334 | 4-t-BuPh | 4-t-BuPh | CN | 9-Cbz | 9-Cbz |
| 121335 | 4-t-BuPh | 4-t-BuPh | DPA | 9-Cbz | 9-Cbz |
| 121336 | 4-t-BuPh | 4-t-BuPh | 2-DBF | 9-Cbz | 9-Cbz |
| 121337 | 4-t-BuPh | 4-t-BuPh | 2-DBT | 9-Cbz | 9-Cbz |
| 121338 | 4-t-BuPh | 4-t-BuPh | 4-t-BuPh | 9-Cbz | 9-Cbz |
| 121339 | 4-t-BuPh | 4-t-BuPh | 1,3-di-t-BuPh | 9-Cbz | 9-Cbz |
| 121340 | 4-t-BuPh | 4-t-BuPh | 9-Cbz | 9-Cbz | 9-Cbz |
| 121341 | 4-t-BuPh | 4-t-BuPh | t-Bu | 4-t-BuPh | 4-t-BuPh |
| 121342 | 4-t-BuPh | 4-t-BuPh | Ph | 4-t-BuPh | 4-t-BuPh |
| 121343 | 4-t-BuPh | 4-t-BuPh | CN | 4-t-BuPh | 4-t-BuPh |
| 121344 | 4-t-BuPh | 4-t-BuPh | DPA | 4-t-BuPh | 4-t-BuPh |
| 121345 | 4-t-BuPh | 4-t-BuPh | 2-DBF | 4-t-BuPh | 4-t-BuPh |
| 121346 | 4-t-BuPh | 4-t-BuPh | 2-DBT | 4-t-BuPh | 4-t-BuPh |
| 121347 | 4-t-BuPh | 4-t-BuPh | 4-t-BuPh | 4-t-BuPh | 4-t-BuPh |
| 121348 | 4-t-BuPh | 4-t-BuPh | 1,3-di-t-BuPh | 4-t-BuPh | 4-t-BuPh |
| 121349 | 4-t-BuPh | 4-t-BuPh | 9-Cbz | 4-t-BuPh | 4-t-BuPh |
| 121350 | 4-t-BuPh | 4-t-BuPh | t-Bu | 1,3-di-t-BuPh | 1,3-di-t-BuPh |
| 121351 | 4-t-BuPh | 4-t-BuPh | Ph | 1,3-di-t-BuPh | 1,3-di-t-BuPh |
| 121352 | 4-t-BuPh | 4-t-BuPh | CN | 1,3-di-t-BuPh | 1,3-di-t-BuPh |
| 121353 | 4-t-BuPh | 4-t-BuPh | DPA | 1,3-di-t-BuPh | 1,3-di-t-BuPh |
| 121354 | 4-t-BuPh | 4-t-BuPh | 2-DBF | 1,3-di-t-BuPh | 1,3-di-t-BuPh |
| 121355 | 4-t-BuPh | 4-t-BuPh | 2-DBT | 1,3-di-t-BuPh | 1,3-di-t-BuPh |
| 121356 | 4-t-BuPh | 4-t-BuPh | 4-t-BuPh | 1,3-di-t-BuPh | 1,3-di-t-BuPh |
| 121357 | 4-t-BuPh | 4-t-BuPh | 1,3-di-t-BuPh | 1,3-di-t-BuPh | 1,3-di-t-BuPh |
| 121358 | 4-t-BuPh | 4-t-BuPh | 9-Cbz | 1,3-di-t-BuPh | 1,3-di-t-BuPh |
| 121359 | 1,3-di-t-BuPh | 1,3-di-t-BuPh | t-Bu | H | H |
| 121360 | 1,3-di-t-BuPh | 1,3-di-t-BuPh | Ph | H | H |
| 121361 | 1,3-di-t-BuPh | 1,3-di-t-BuPh | CN | H | H |
| 121362 | 1,3-di-t-BuPh | 1,3-di-t-BuPh | DPA | H | H |
| 121363 | 1,3-di-t-BuPh | 1,3-di-t-BuPh | 2-DBF | H | H |
| 121364 | 1,3-di-t-BuPh | 1,3-di-t-BuPh | 2-DBT | H | H |
| 121365 | 1,3-di-t-BuPh | 1,3-di-t-BuPh | 4-t-BuPh | H | H |
| 121366 | 1,3-di-t-BuPh | 1,3-di-t-BuPh | 9-Cbz | H | H |
| 121367 | 1,3-di-t-BuPh | 1,3-di-t-BuPh | t-Bu | t-Bu | t-Bu |
| 121368 | 1,3-di-t-BuPh | 1,3-di-t-BuPh | Ph | t-Bu | t-Bu |
| 121369 | 1,3-di-t-BuPh | 1,3-di-t-BuPh | CN | t-Bu | t-Bu |
| 121370 | 1,3-di-t-BuPh | 1,3-di-t-BuPh | DPA | t-Bu | t-Bu |
| 121371 | 1,3-di-t-BuPh | 1,3-di-t-BuPh | 2-DBF | t-Bu | t-Bu |

TABLE 3-continued

| Compound No. | $R_{11b}$ | $R_{12c}$ | $R_{14b}$ | $R_{18c}$ | $R_{19b}$ |
|---|---|---|---|---|---|
| 121372 | 1,3-di-t-BuPh | 1,3-di-t-BuPh | 2-DBT | t-Bu | t-Bu |
| 121373 | 1,3-di-t-BuPh | 1,3-di-t-BuPh | 4-t-BuPh | t-Bu | t-Bu |
| 121374 | 1,3-di-t-BuPh | 1,3-di-t-BuPh | 1,3-di-t-BuPh | t-Bu | t-Bu |
| 121375 | 1,3-di-t-BuPh | 1,3-di-t-BuPh | 9-Cbz | t-Bu | t-Bu |
| 121376 | 1,3-di-t-BuPh | 1,3-di-t-BuPh | t-Bu | Ph | Ph |
| 121377 | 1,3-di-t-BuPh | 1,3-di-t-BuPh | Ph | Ph | Ph |
| 121378 | 1,3-di-t-BuPh | 1,3-di-t-BuPh | CN | Ph | Ph |
| 121379 | 1,3-di-t-BuPh | 1,3-di-t-BuPh | DPA | Ph | Ph |
| 121380 | 1,3-di-t-BuPh | 1,3-di-t-BuPh | 2-DBF | Ph | Ph |
| 121381 | 1,3-di-t-BuPh | 1,3-di-t-BuPh | 2-DBT | Ph | Ph |
| 121382 | 1,3-di-t-BuPh | 1,3-di-t-BuPh | 4-t-BuPh | Ph | Ph |
| 121383 | 1,3-di-t-BuPh | 1,3-di-t-BuPh | 1,3-di-t-BuPh | Ph | Ph |
| 121384 | 1,3-di-t-BuPh | 1,3-di-t-BuPh | 9-Cbz | Ph | Ph |
| 121385 | 1,3-di-t-BuPh | 1,3-di-t-BuPh | t-Bu | CN | CN |
| 121386 | 1,3-di-t-BuPh | 1,3-di-t-BuPh | Ph | CN | CN |
| 121387 | 1,3-di-t-BuPh | 1,3-di-t-BuPh | CN | CN | CN |
| 121388 | 1,3-di-t-BuPh | 1,3-di-t-BuPh | DPA | CN | CN |
| 121389 | 1,3-di-t-BuPh | 1,3-di-t-BuPh | 2-DBF | CN | CN |
| 121390 | 1,3-di-t-BuPh | 1,3-di-t-BuPh | 2-DBT | CN | CN |
| 121391 | 1,3-di-t-BuPh | 1,3-di-t-BuPh | 4-t-BuPh | CN | CN |
| 121392 | 1,3-di-t-BuPh | 1,3-di-t-BuPh | 1,3-di-t-BuPh | CN | CN |
| 121393 | 1,3-di-t-BuPh | 1,3-di-t-BuPh | 9-Cbz | CN | CN |
| 121394 | 1,3-di-t-BuPh | 1,3-di-t-BuPh | t-Bu | 9-Cbz | 9-Cbz |
| 121395 | 1,3-di-t-BuPh | 1,3-di-t-BuPh | Ph | 9-Cbz | 9-Cbz |
| 121396 | 1,3-di-t-BuPh | 1,3-di-t-BuPh | CN | 9-Cbz | 9-Cbz |
| 121397 | 1,3-di-t-BuPh | 1,3-di-t-BuPh | DPA | 9-Cbz | 9-Cbz |
| 121398 | 1,3-di-t-BuPh | 1,3-di-t-BuPh | 2-DBF | 9-Cbz | 9-Cbz |
| 121399 | 1,3-di-t-BuPh | 1,3-di-t-BuPh | 2-DBT | 9-Cbz | 9-Cbz |
| 121400 | 1,3-di-t-BuPh | 1,3-di-t-BuPh | 4-t-BuPh | 9-Cbz | 9-Cbz |
| 121401 | 1,3-di-t-BuPh | 1,3-di-t-BuPh | 1,3-di-t-BuPh | 9-Cbz | 9-Cbz |
| 121402 | 1,3-di-t-BuPh | 1,3-di-t-BuPh | 9-Cbz | 9-Cbz | 9-Cbz |
| 121403 | 1,3-di-t-BuPh | 1,3-di-t-BuPh | t-Bu | 4-t-BuPh | 4-t-BuPh |
| 121404 | 1,3-di-t-BuPh | 1,3-di-t-BuPh | Ph | 4-t-BuPh | 4-t-BuPh |
| 121405 | 1,3-di-t-BuPh | 1,3-di-t-BuPh | CN | 4-t-BuPh | 4-t-BuPh |
| 121406 | 1,3-di-t-BuPh | 1,3-di-t-BuPh | DPA | 4-t-BuPh | 4-t-BuPh |
| 121407 | 1,3-di-t-BuPh | 1,3-di-t-BuPh | 2-DBF | 4-t-BuPh | 4-t-BuPh |
| 121408 | 1,3-di-t-BuPh | 1,3-di-t-BuPh | 2-DBT | 4-t-BuPh | 4-t-BuPh |
| 121409 | 1,3-di-t-BuPh | 1,3-di-t-BuPh | 4-t-BuPh | 4-t-BuPh | 4-t-BuPh |
| 121410 | 1,3-di-t-BuPh | 1,3-di-t-BuPh | 1,3-di-t-BuPh | 4-t-BuPh | 4-t-BuPh |
| 121411 | 1,3-di-t-BuPh | 1,3-di-t-BuPh | 9-Cbz | 4-t-BuPh | 4-t-BuPh |
| 121412 | 1,3-di-t-BuPh | 1,3-di-t-BuPh | t-Bu | 1,3-di-t-BuPh | 1,3-di-t-BuPh |
| 121413 | 1,3-di-t-BuPh | 1,3-di-t-BuPh | Ph | 1,3-di-t-BuPh | 1,3-di-t-BuPh |
| 121414 | 1,3-di-t-BuPh | 1,3-di-t-BuPh | CN | 1,3-di-t-BuPh | 1,3-di-t-BuPh |
| 121415 | 1,3-di-t-BuPh | 1,3-di-t-BuPh | DPA | 1,3-di-t-BuPh | 1,3-di-t-BuPh |
| 121416 | 1,3-di-t-BuPh | 1,3-di-t-BuPh | 2-DBF | 1,3-di-t-BuPh | 1,3-di-t-BuPh |
| 121417 | 1,3-di-t-BuPh | 1,3-di-t-BuPh | 2-DBT | 1,3-di-t-BuPh | 1,3-di-t-BuPh |
| 121418 | 1,3-di-t-BuPh | 1,3-di-t-BuPh | 4-t-BuPh | 1,3-di-t-BuPh | 1,3-di-t-BuPh |
| 121419 | 1,3-di-t-BuPh | 1,3-di-t-BuPh | 1,3-di-t-BuPh | 1,3-di-t-BuPh | 1,3-di-t-BuPh |
| 121420 | 1,3-di-t-BuPh | 1,3-di-t-BuPh | 9-Cbz | 1,3-di-t-BuPh | 1,3-di-t-BuPh |

Group HC4

The heterocyclic compound may be represented by Formula 12-2, and substituents may be defined as shown in Table 4.

TABLE 4

| Compound No. | $R_{11b}$ | $R_{12c}$ | $R_{14b}$ | $R_{18c}$ | $R_{19b}$ |
|---|---|---|---|---|---|
| 122001 | t-Bu | t-Bu | t-Bu | t-Bu | t-Bu |
| 122002 | Ph | Ph | t-Bu | Ph | Ph |
| 122003 | t-Bu | t-Bu | H | H | H |
| 122004 | H | H | t-Bu | H | H |
| 122005 | H | H | H | t-Bu | t-Bu |
| 122006 | t-Bu | t-Bu | t-Bu | H | H |
| 122007 | H | H | t-Bu | t-Bu | t-Bu |
| 122008 | t-Bu | t-Bu | H | t-Bu | t-Bu |
| 122009 | Ph | Ph | H | H | H |
| 122010 | H | H | Ph | H | H |
| 122011 | H | H | H | Ph | Ph |
| 122012 | Ph | Ph | Ph | H | H |
| 122013 | H | H | Ph | Ph | Ph |
| 122014 | Ph | Ph | H | Ph | Ph |
| 122015 | CN | CN | H | H | H |
| 122016 | H | H | CN | H | H |
| 122017 | H | H | H | CN | CN |
| 122018 | CN | CN | CN | H | H |
| 122019 | H | H | CN | CN | CN |
| 122020 | CN | CN | H | CN | CN |
| 122021 | 9-Cbz | 9-Cbz | H | H | H |
| 122022 | H | H | 9-Cbz | H | H |
| 122023 | H | H | H | 9-Cbz | 9-Cbz |
| 122024 | 9-Cbz | 9-Cbz | 9-Cbz | H | H |
| 122025 | H | H | 9-Cbz | 9-Cbz | 9-Cbz |
| 122026 | 9-Cbz | 9-Cbz | H | 9-Cbz | 9-Cbz |
| 122027 | Me | Me | H | H | H |
| 122028 | H | H | Me | H | H |
| 122029 | H | H | H | Me | Me |
| 122030 | Me | Me | Me | H | H |
| 122031 | H | H | Me | Me | Me |
| 122032 | Me | Me | H | Me | Me |
| 122033 | CD3 | CD3 | H | H | H |
| 122034 | H | H | CD3 | H | H |
| 122035 | H | H | H | CD3 | CD3 |
| 122036 | CD3 | CD3 | CD3 | H | H |
| 122037 | H | H | CD3 | CD3 | CD3 |
| 122038 | CD3 | CD3 | H | CD3 | CD3 |
| 122039 | 4-t-BuPh | 4-t-BuPh | H | H | H |
| 122040 | H | H | 4-t-BuPh | H | H |
| 122041 | H | H | H | 4-t-BuPh | 4-t-BuPh |
| 122042 | 4-t-BuPh | 4-t-BuPh | 4-t-BuPh | H | H |
| 122043 | H | H | 4-t-BuPh | 4-t-BuPh | 4-t-BuPh |
| 122044 | 4-t-BuPh | 4-t-BuPh | H | 4-t-BuPh | 4-t-BuPh |
| 122045 | 1,3-di-t-BuPh | 1,3-di-t-BuPh | H | H | H |
| 122046 | H | H | 1,3-di-t-BuPh | H | H |
| 122047 | H | H | H | 1,3-di-t-BuPh | 1,3-di-t-BuPh |
| 122048 | 1,3-di-t-BuPh | 1,3-di-t-BuPh | 1,3-di-t-BuPh | H | H |
| 122049 | H | H | 1,3-di-t-BuPh | 1,3-di-t-BuPh | 1,3-di-t-BuPh |
| 122050 | 1,3-di-t-BuPh | 1,3-di-t-BuPh | H | 1,3-di-t-BuPh | 1,3-di-t-BuPh |
| 122051 | t-Bu | t-Bu | Ph | H | H |
| 122052 | t-Bu | t-Bu | CN | H | H |
| 122053 | t-Bu | t-Bu | DPA | H | H |
| 122054 | t-Bu | t-Bu | 2-DBF | H | H |
| 122055 | t-Bu | t-Bu | 2-DBT | H | H |
| 122056 | t-Bu | t-Bu | 4-t-BuPh | H | H |
| 122057 | t-Bu | t-Bu | 1,3-di-t-BuPh | H | H |
| 122058 | t-Bu | t-Bu | 9-Cbz | H | H |
| 122059 | t-Bu | t-Bu | Ph | t-Bu | t-Bu |
| 122060 | t-Bu | t-Bu | CN | t-Bu | t-Bu |
| 122061 | t-Bu | t-Bu | DPA | t-Bu | t-Bu |
| 122062 | t-Bu | t-Bu | 2-DBF | t-Bu | t-Bu |
| 122063 | t-Bu | t-Bu | 2-DBT | t-Bu | t-Bu |
| 122064 | t-Bu | t-Bu | 4-t-BuPh | t-Bu | t-Bu |
| 122065 | t-Bu | t-Bu | 1,3-di-t-BuPh | t-Bu | t-Bu |
| 122066 | t-Bu | t-Bu | 9-Cbz | t-Bu | t-Bu |
| 122067 | t-Bu | t-Bu | t-Bu | Ph | Ph |
| 122068 | t-Bu | t-Bu | Ph | Ph | Ph |
| 122069 | t-Bu | t-Bu | CN | Ph | Ph |
| 122070 | t-Bu | t-Bu | DPA | Ph | Ph |
| 122071 | t-Bu | t-Bu | 2-DBF | Ph | Ph |
| 122072 | t-Bu | t-Bu | 2-DBT | Ph | Ph |
| 122073 | t-Bu | t-Bu | 4-t-BuPh | Ph | Ph |
| 122074 | t-Bu | t-Bu | 1,3-di-t-BuPh | Ph | Ph |
| 122075 | t-Bu | t-Bu | 9-Cbz | Ph | Ph |
| 122076 | t-Bu | t-Bu | t-Bu | CN | CN |
| 122077 | t-Bu | t-Bu | Ph | CN | CN |
| 122078 | t-Bu | t-Bu | CN | CN | CN |
| 122079 | t-Bu | t-Bu | DPA | CN | CN |
| 122080 | t-Bu | t-Bu | 2-DBF | CN | CN |
| 122081 | t-Bu | t-Bu | 2-DBT | CN | CN |
| 122082 | t-Bu | t-Bu | 4-t-BuPh | CN | CN |
| 122083 | t-Bu | t-Bu | 1,3-di-t-BuPh | CN | CN |
| 122084 | t-Bu | t-Bu | 9-Cbz | CN | CN |
| 122085 | t-Bu | t-Bu | t-Bu | 9-Cbz | 9-Cbz |
| 122086 | t-Bu | t-Bu | Ph | 9-Cbz | 9-Cbz |
| 122087 | t-Bu | t-Bu | CN | 9-Cbz | 9-Cbz |
| 122088 | t-Bu | t-Bu | DPA | 9-Cbz | 9-Cbz |
| 122089 | t-Bu | t-Bu | 2-DBF | 9-Cbz | 9-Cbz |
| 122090 | t-Bu | t-Bu | 2-DBT | 9-Cbz | 9-Cbz |
| 122091 | t-Bu | t-Bu | 4-t-BuPh | 9-Cbz | 9-Cbz |
| 122092 | t-Bu | t-Bu | 1,3-di-t-BuPh | 9-Cbz | 9-Cbz |
| 122093 | t-Bu | t-Bu | 9-Cbz | 9-Cbz | 9-Cbz |
| 122094 | t-Bu | t-Bu | t-Bu | 4-t-BuPh | 4-t-BuPh |
| 122095 | t-Bu | t-Bu | Ph | 4-t-BuPh | 4-t-BuPh |
| 122096 | t-Bu | t-Bu | CN | 4-t-BuPh | 4-t-BuPh |
| 122097 | t-Bu | t-Bu | DPA | 4-t-BuPh | 4-t-BuPh |
| 122098 | t-Bu | t-Bu | 2-DBF | 4-t-BuPh | 4-t-BuPh |
| 122099 | t-Bu | t-Bu | 2-DBT | 4-t-BuPh | 4-t-BuPh |

TABLE 4-continued

| Compound No. | $R_{11b}$ | $R_{12c}$ | $R_{14b}$ | $R_{18c}$ | $R_{19b}$ |
|---|---|---|---|---|---|
| 122100 | t-Bu | t-Bu | 4-t-BuPh | 4-t-BuPh | 4-t-BuPh |
| 122101 | t-Bu | t-Bu | 1,3-di-t-BuPh | 4-t-BuPh | 4-t-BuPh |
| 122102 | t-Bu | t-Bu | 9-Cbz | 4-t-BuPh | 4-t-BuPh |
| 122103 | t-Bu | t-Bu | t-Bu | 1,3-di-t-BuPh | 1,3-di-t-BuPh |
| 122104 | t-Bu | t-Bu | Ph | 1,3-di-t-BuPh | 1,3-di-t-BuPh |
| 122105 | t-Bu | t-Bu | CN | 1,3-di-t-BuPh | 1,3-di-t-BuPh |
| 122106 | t-Bu | t-Bu | DPA | 1,3-di-t-BuPh | 1,3-di-t-BuPh |
| 122107 | t-Bu | t-Bu | 2-DBF | 1,3-di-t-BuPh | 1,3-di-t-BuPh |
| 122108 | t-Bu | t-Bu | 2-DBT | 1,3-di-t-BuPh | 1,3-di-t-BuPh |
| 122109 | t-Bu | t-Bu | 4-t-BuPh | 1,3-di-t-BuPh | 1,3-di-t-BuPh |
| 122110 | t-Bu | t-Bu | 1,3-di-t-BuPh | 1,3-di-t-BuPh | 1,3-di-t-BuPh |
| 122111 | t-Bu | t-Bu | 9-Cbz | 1,3-di-t-BuPh | 1,3-di-t-BuPh |
| 122112 | Ph | Ph | t-Bu | H | H |
| 122113 | Ph | Ph | CN | H | H |
| 122114 | Ph | Ph | DPA | H | H |
| 122115 | Ph | Ph | 2-DBF | H | H |
| 122116 | Ph | Ph | 2-DBT | H | H |
| 122117 | Ph | Ph | 4-t-BuPh | H | H |
| 122118 | Ph | Ph | 1,3-di-t-BuPh | H | H |
| 122119 | Ph | Ph | 9-Cbz | H | H |
| 122120 | Ph | Ph | t-Bu | t-Bu | t-Bu |
| 122121 | Ph | Ph | Ph | t-Bu | t-Bu |
| 122122 | Ph | Ph | CN | t-Bu | t-Bu |
| 122123 | Ph | Ph | DPA | t-Bu | t-Bu |
| 122124 | Ph | Ph | 2-DBF | t-Bu | t-Bu |
| 122125 | Ph | Ph | 2-DBT | t-Bu | t-Bu |
| 122126 | Ph | Ph | 4-t-BuPh | t-Bu | t-Bu |
| 122127 | Ph | Ph | 1,3-di-t-BuPh | t-Bu | t-Bu |
| 122128 | Ph | Ph | 9-Cbz | t-Bu | t-Bu |
| 122129 | Ph | Ph | Ph | Ph | Ph |
| 122130 | Ph | Ph | CN | Ph | Ph |
| 122131 | Ph | Ph | DPA | Ph | Ph |
| 122132 | Ph | Ph | 2-DBF | Ph | Ph |
| 122133 | Ph | Ph | 2-DBT | Ph | Ph |
| 122134 | Ph | Ph | 4-t-BuPh | Ph | Ph |
| 122135 | Ph | Ph | 1,3-di-t-BuPh | Ph | Ph |
| 122136 | Ph | Ph | 9-Cbz | Ph | Ph |
| 122137 | Ph | Ph | t-Bu | CN | CN |
| 122138 | Ph | Ph | Ph | CN | CN |
| 122139 | Ph | Ph | CN | CN | CN |
| 122140 | Ph | Ph | DPA | CN | CN |
| 122141 | Ph | Ph | 2-DBF | CN | CN |
| 122142 | Ph | Ph | 2-DBT | CN | CN |
| 122143 | Ph | Ph | 4-t-BuPh | CN | CN |
| 122144 | Ph | Ph | 1,3-di-t-BuPh | CN | CN |
| 122145 | Ph | Ph | 9-Cbz | CN | CN |
| 122146 | Ph | Ph | t-Bu | 9-Cbz | 9-Cbz |
| 122147 | Ph | Ph | Ph | 9-Cbz | 9-Cbz |
| 122148 | Ph | Ph | CN | 9-Cbz | 9-Cbz |
| 122149 | Ph | Ph | DPA | 9-Cbz | 9-Cbz |
| 122150 | Ph | Ph | 2-DBF | 9-Cbz | 9-Cbz |
| 122151 | Ph | Ph | 2-DBT | 9-Cbz | 9-Cbz |
| 122152 | Ph | Ph | 4-t-BuPh | 9-Cbz | 9-Cbz |
| 122153 | Ph | Ph | 1,3-di-t-BuPh | 9-Cbz | 9-Cbz |
| 122154 | Ph | Ph | 9-Cbz | 9-Cbz | 9-Cbz |
| 122155 | Ph | Ph | t-Bu | 4-t-BuPh | 4-t-BuPh |
| 122156 | Ph | Ph | Ph | 4-t-BuPh | 4-t-BuPh |
| 122157 | Ph | Ph | CN | 4-t-BuPh | 4-t-BuPh |
| 122158 | Ph | Ph | DPA | 4-t-BuPh | 4-t-BuPh |
| 122159 | Ph | Ph | 2-DBF | 4-t-BuPh | 4-t-BuPh |
| 122160 | Ph | Ph | 2-DBT | 4-t-BuPh | 4-t-BuPh |
| 122161 | Ph | Ph | 4-t-BuPh | 4-t-BuPh | 4-t-BuPh |
| 122162 | Ph | Ph | 1,3-di-t-BuPh | 4-t-BuPh | 4-t-BuPh |
| 122163 | Ph | Ph | 9-Cbz | 4-t-BuPh | 4-t-BuPh |
| 122164 | Ph | Ph | t-Bu | 1,3-di-t-BuPh | 1,3-di-t-BuPh |
| 122165 | Ph | Ph | Ph | 1,3-di-t-BuPh | 1,3-di-t-BuPh |
| 122166 | Ph | Ph | CN | 1,3-di-t-BuPh | 1,3-di-t-BuPh |
| 122167 | Ph | Ph | DPA | 1,3-di-t-BuPh | 1,3-di-t-BuPh |
| 122168 | Ph | Ph | 2-DBF | 1,3-di-t-BuPh | 1,3-di-t-BuPh |
| 122169 | Ph | Ph | 2-DBT | 1,3-di-t-BuPh | 1,3-di-t-BuPh |
| 122170 | Ph | Ph | 4-t-BuPh | 1,3-di-t-BuPh | 1,3-di-t-BuPh |
| 122171 | Ph | Ph | 1,3-di-t-BuPh | 1,3-di-t-BuPh | 1,3-di-t-BuPh |
| 122172 | Ph | Ph | 9-Cbz | 1,3-di-t-BuPh | 1,3-di-t-BuPh |
| 122173 | 9-Cbz | 9-Cbz | t-Bu | H | H |
| 122174 | 9-Cbz | 9-Cbz | Ph | H | H |
| 122175 | 9-Cbz | 9-Cbz | CN | H | H |
| 122176 | 9-Cbz | 9-Cbz | DPA | H | H |
| 122177 | 9-Cbz | 9-Cbz | 2-DBF | H | H |

TABLE 4-continued

| Compound No. | $R_{11b}$ | $R_{12c}$ | $R_{14b}$ | $R_{18c}$ | $R_{19b}$ |
|---|---|---|---|---|---|
| 122178 | 9-Cbz | 9-Cbz | 2-DBT | H | H |
| 122179 | 9-Cbz | 9-Cbz | 4-t-BuPh | H | H |
| 122180 | 9-Cbz | 9-Cbz | 1,3-di-t-BuPh | H | H |
| 122181 | 9-Cbz | 9-Cbz | t-Bu | t-Bu | t-Bu |
| 122182 | 9-Cbz | 9-Cbz | Ph | t-Bu | t-Bu |
| 122183 | 9-Cbz | 9-Cbz | CN | t-Bu | t-Bu |
| 122184 | 9-Cbz | 9-Cbz | DPA | t-Bu | t-Bu |
| 122185 | 9-Cbz | 9-Cbz | 2-DBF | t-Bu | t-Bu |
| 122186 | 9-Cbz | 9-Cbz | 2-DBT | t-Bu | t-Bu |
| 122187 | 9-Cbz | 9-Cbz | 4-t-BuPh | t-Bu | t-Bu |
| 122188 | 9-Cbz | 9-Cbz | 1,3-di-t-BuPh | t-Bu | t-Bu |
| 122189 | 9-Cbz | 9-Cbz | 9-Cbz | t-Bu | t-Bu |
| 122190 | 9-Cbz | 9-Cbz | t-Bu | Ph | Ph |
| 122191 | 9-Cbz | 9-Cbz | Ph | Ph | Ph |
| 122192 | 9-Cbz | 9-Cbz | CN | Ph | Ph |
| 122193 | 9-Cbz | 9-Cbz | DPA | Ph | Ph |
| 122194 | 9-Cbz | 9-Cbz | 2-DBF | Ph | Ph |
| 122195 | 9-Cbz | 9-Cbz | 2-DBT | Ph | Ph |
| 122196 | 9-Cbz | 9-Cbz | 4-t-BuPh | Ph | Ph |
| 122197 | 9-Cbz | 9-Cbz | 1,3-di-t-BuPh | Ph | Ph |
| 122198 | 9-Cbz | 9-Cbz | 9-Cbz | Ph | Ph |
| 122199 | 9-Cbz | 9-Cbz | t-Bu | CN | CN |
| 122200 | 9-Cbz | 9-Cbz | Ph | CN | CN |
| 122201 | 9-Cbz | 9-Cbz | CN | CN | CN |
| 122202 | 9-Cbz | 9-Cbz | DPA | CN | CN |
| 122203 | 9-Cbz | 9-Cbz | 2-DBF | CN | CN |
| 122204 | 9-Cbz | 9-Cbz | 2-DBT | CN | CN |
| 122205 | 9-Cbz | 9-Cbz | 4-t-BuPh | CN | CN |
| 122206 | 9-Cbz | 9-Cbz | 1,3-di-t-BuPh | CN | CN |
| 122207 | 9-Cbz | 9-Cbz | 9-Cbz | CN | CN |
| 122208 | 9-Cbz | 9-Cbz | t-Bu | 9-Cbz | 9-Cbz |
| 122209 | 9-Cbz | 9-Cbz | Ph | 9-Cbz | 9-Cbz |
| 122210 | 9-Cbz | 9-Cbz | CN | 9-Cbz | 9-Cbz |
| 122211 | 9-Cbz | 9-Cbz | DPA | 9-Cbz | 9-Cbz |
| 122212 | 9-Cbz | 9-Cbz | 2-DBF | 9-Cbz | 9-Cbz |
| 122213 | 9-Cbz | 9-Cbz | 2-DBT | 9-Cbz | 9-Cbz |
| 122214 | 9-Cbz | 9-Cbz | 4-t-BuPh | 9-Cbz | 9-Cbz |
| 122215 | 9-Cbz | 9-Cbz | 1,3-di-t-BuPh | 9-Cbz | 9-Cbz |
| 122216 | 9-Cbz | 9-Cbz | 9-Cbz | 9-Cbz | 9-Cbz |
| 122217 | 9-Cbz | 9-Cbz | t-Bu | 4-t-BuPh | 4-t-BuPh |
| 122218 | 9-Cbz | 9-Cbz | Ph | 4-t-BuPh | 4-t-BuPh |
| 122219 | 9-Cbz | 9-Cbz | CN | 4-t-BuPh | 4-t-BuPh |
| 122220 | 9-Cbz | 9-Cbz | DPA | 4-t-BuPh | 4-t-BuPh |
| 122221 | 9-Cbz | 9-Cbz | 2-DBF | 4-t-BuPh | 4-t-BuPh |
| 122222 | 9-Cbz | 9-Cbz | 2-DBT | 4-t-BuPh | 4-t-BuPh |
| 122223 | 9-Cbz | 9-Cbz | 4-t-BuPh | 4-t-BuPh | 4-t-BuPh |
| 122224 | 9-Cbz | 9-Cbz | 1,3-di-t-BuPh | 4-t-BuPh | 4-t-BuPh |
| 122225 | 9-Cbz | 9-Cbz | 9-Cbz | 4-t-BuPh | 4-t-BuPh |
| 122226 | 9-Cbz | 9-Cbz | t-Bu | 1,3-di-t-BuPh | 1,3-di-t-BuPh |
| 122227 | 9-Cbz | 9-Cbz | Ph | 1,3-di-t-BuPh | 1,3-di-t-BuPh |
| 122228 | 9-Cbz | 9-Cbz | CN | 1,3-di-t-BuPh | 1,3-di-t-BuPh |
| 122229 | 9-Cbz | 9-Cbz | DPA | 1,3-di-t-BuPh | 1,3-di-t-BuPh |
| 122230 | 9-Cbz | 9-Cbz | 2-DBF | 1,3-di-t-BuPh | 1,3-di-t-BuPh |
| 122231 | 9-Cbz | 9-Cbz | 2-DBT | 1,3-di-t-BuPh | 1,3-di-t-BuPh |
| 122232 | 9-Cbz | 9-Cbz | 4-t-BuPh | 1,3-di-t-BuPh | 1,3-di-t-BuPh |
| 122233 | 9-Cbz | 9-Cbz | 1,3-di-t-BuPh | 1,3-di-t-BuPh | 1,3-di-t-BuPh |
| 122234 | 9-Cbz | 9-Cbz | 9-Cbz | 1,3-di-t-BuPh | 1,3-di-t-BuPh |
| 122235 | CN | CN | t-Bu | H | H |
| 122236 | CN | CN | Ph | H | H |
| 122237 | CN | CN | DPA | H | H |
| 122238 | CN | CN | 2-DBF | H | H |
| 122239 | CN | CN | 2-DBT | H | H |
| 122240 | CN | CN | 4-t-BuPh | H | H |
| 122241 | CN | CN | 1,3-di-t-BuPh | H | H |
| 122242 | CN | CN | 9-Cbz | H | H |
| 122243 | CN | CN | t-Bu | t-Bu | t-Bu |
| 122244 | CN | CN | Ph | t-Bu | t-Bu |
| 122245 | CN | CN | CN | t-Bu | t-Bu |
| 122246 | CN | CN | DPA | t-Bu | t-Bu |
| 122247 | CN | CN | 2-DBF | t-Bu | t-Bu |
| 122248 | CN | CN | 2-DBT | t-Bu | t-Bu |
| 122249 | CN | CN | 4-t-BuPh | t-Bu | t-Bu |
| 122250 | CN | CN | 1,3-di-t-BuPh | t-Bu | t-Bu |
| 122251 | CN | CN | 9-Cbz | t-Bu | t-Bu |
| 122252 | CN | CN | t-Bu | Ph | Ph |
| 122253 | CN | CN | Ph | Ph | Ph |
| 122254 | CN | CN | CN | Ph | Ph |
| 122255 | CN | CN | DPA | Ph | Ph |
| 122256 | CN | CN | 2-DBF | Ph | Ph |
| 122257 | CN | CN | 2-DBT | Ph | Ph |
| 122258 | CN | CN | 4-t-BuPh | Ph | Ph |
| 122259 | CN | CN | 1,3-di-t-BuPh | Ph | Ph |
| 122260 | CN | CN | 9-Cbz | Ph | Ph |
| 122261 | CN | CN | t-Bu | CN | CN |
| 122262 | CN | CN | Ph | CN | CN |
| 122263 | CN | CN | CN | CN | CN |
| 122264 | CN | CN | DPA | CN | CN |

TABLE 4-continued

| Compound No. | $R_{11b}$ | $R_{12c}$ | $R_{14b}$ | $R_{18c}$ | $R_{19b}$ |
|---|---|---|---|---|---|
| 122265 | CN | CN | 2-DBF | CN | CN |
| 122266 | CN | CN | 2-DBT | CN | CN |
| 122267 | CN | CN | 4-t-BuPh | CN | CN |
| 122268 | CN | CN | 1,3-di-t-BuPh | CN | CN |
| 122269 | CN | CN | 9-Cbz | CN | CN |
| 122270 | CN | CN | t-Bu | 9-Cbz | 9-Cbz |
| 122271 | CN | CN | Ph | 9-Cbz | 9-Cbz |
| 122272 | CN | CN | CN | 9-Cbz | 9-Cbz |
| 122273 | CN | CN | DPA | 9-Cbz | 9-Cbz |
| 122274 | CN | CN | 2-DBF | 9-Cbz | 9-Cbz |
| 122275 | CN | CN | 2-DBT | 9-Cbz | 9-Cbz |
| 122276 | CN | CN | 4-t-BuPh | 9-Cbz | 9-Cbz |
| 122277 | CN | CN | 1,3-di-t-BuPh | 9-Cbz | 9-Cbz |
| 122278 | CN | CN | 9-Cbz | 9-Cbz | 9-Cbz |
| 122279 | CN | CN | t-Bu | 4-t-BuPh | 4-t-BuPh |
| 122280 | CN | CN | Ph | 4-t-BuPh | 4-t-BuPh |
| 122281 | CN | CN | CN | 4-t-BuPh | 4-t-BuPh |
| 122282 | CN | CN | DPA | 4-t-BuPh | 4-t-BuPh |
| 122283 | CN | CN | 2-DBF | 4-t-BuPh | 4-t-BuPh |
| 122284 | CN | CN | 2-DBT | 4-t-BuPh | 4-t-BuPh |
| 122285 | CN | CN | 4-t-BuPh | 4-t-BuPh | 4-t-BuPh |
| 122286 | CN | CN | 1,3-di-t-BuPh | 4-t-BuPh | 4-t-BuPh |
| 122287 | CN | CN | 9-Cbz | 4-t-BuPh | 4-t-BuPh |
| 122288 | CN | CN | t-Bu | 1,3-di-t-BuPh | 1,3-di-t-BuPh |
| 122289 | CN | CN | Ph | 1,3-di-t-BuPh | 1,3-di-t-BuPh |
| 122290 | CN | CN | CN | 1,3-di-t-BuPh | 1,3-di-t-BuPh |
| 122291 | CN | CN | DPA | 1,3-di-t-BuPh | 1,3-di-t-BuPh |
| 122292 | CN | CN | 2-DBF | 1,3-di-t-BuPh | 1,3-di-t-BuPh |
| 122293 | CN | CN | 2-DBT | 1,3-di-t-BuPh | 1,3-di-t-BuPh |
| 122294 | CN | CN | 4-t-BuPh | 1,3-di-t-BuPh | 1,3-di-t-BuPh |
| 122295 | CN | CN | 1,3-di-t-BuPh | 1,3-di-t-BuPh | 1,3-di-t-BuPh |
| 122296 | CN | CN | 9-Cbz | 1,3-di-t-BuPh | 1,3-di-t-BuPh |
| 122297 | 4-t-BuPh | 4-t-BuPh | t-Bu | H | H |
| 122298 | 4-t-BuPh | 4-t-BuPh | Ph | H | H |
| 122299 | 4-t-BuPh | 4-t-BuPh | CN | H | H |
| 122300 | 4-t-BuPh | 4-t-BuPh | DPA | H | H |
| 122301 | 4-t-BuPh | 4-t-BuPh | 2-DBF | H | H |
| 122302 | 4-t-BuPh | 4-t-BuPh | 2-DBT | H | H |
| 122303 | 4-t-BuPh | 4-t-BuPh | 1,3-di-t-BuPh | H | H |
| 122304 | 4-t-BuPh | 4-t-BuPh | 9-Cbz | H | H |
| 122305 | 4-t-BuPh | 4-t-BuPh | t-Bu | t-Bu | t-Bu |
| 122306 | 4-t-BuPh | 4-t-BuPh | Ph | t-Bu | t-Bu |
| 122307 | 4-t-BuPh | 4-t-BuPh | CN | t-Bu | t-Bu |
| 122308 | 4-t-BuPh | 4-t-BuPh | DPA | t-Bu | t-Bu |
| 122309 | 4-t-BuPh | 4-t-BuPh | 2-DBF | t-Bu | t-Bu |
| 122310 | 4-t-BuPh | 4-t-BuPh | 2-DBT | t-Bu | t-Bu |
| 122311 | 4-t-BuPh | 4-t-BuPh | 4-t-BuPh | t-Bu | t-Bu |
| 122312 | 4-t-BuPh | 4-t-BuPh | 1,3-di-t-BuPh | t-Bu | t-Bu |
| 122313 | 4-t-BuPh | 4-t-BuPh | 9-Cbz | t-Bu | t-Bu |
| 122314 | 4-t-BuPh | 4-t-BuPh | t-Bu | Ph | Ph |
| 122315 | 4-t-BuPh | 4-t-BuPh | Ph | Ph | Ph |
| 122316 | 4-t-BuPh | 4-t-BuPh | CN | Ph | Ph |
| 122317 | 4-t-BuPh | 4-t-BuPh | DPA | Ph | Ph |
| 122318 | 4-t-BuPh | 4-t-BuPh | 2-DBF | Ph | Ph |
| 122319 | 4-t-BuPh | 4-t-BuPh | 2-DBT | Ph | Ph |
| 122320 | 4-t-BuPh | 4-t-BuPh | 4-t-BuPh | Ph | Ph |
| 122321 | 4-t-BuPh | 4-t-BuPh | 1,3-di-t-BuPh | Ph | Ph |
| 122322 | 4-t-BuPh | 4-t-BuPh | 9-Cbz | Ph | Ph |
| 122323 | 4-t-BuPh | 4-t-BuPh | t-Bu | CN | CN |
| 122324 | 4-t-BuPh | 4-t-BuPh | Ph | CN | CN |
| 122325 | 4-t-BuPh | 4-t-BuPh | CN | CN | CN |
| 122326 | 4-t-BuPh | 4-t-BuPh | DPA | CN | CN |
| 122327 | 4-t-BuPh | 4-t-BuPh | 2-DBF | CN | CN |
| 122328 | 4-t-BuPh | 4-t-BuPh | 2-DBT | CN | CN |
| 122329 | 4-t-BuPh | 4-t-BuPh | 4-t-BuPh | CN | CN |
| 122330 | 4-t-BuPh | 4-t-BuPh | 1,3-di-t-BuPh | CN | CN |
| 122331 | 4-t-BuPh | 4-t-BuPh | 9-Cbz | CN | CN |
| 122332 | 4-t-BuPh | 4-t-BuPh | t-Bu | 9-Cbz | 9-Cbz |
| 122333 | 4-t-BuPh | 4-t-BuPh | Ph | 9-Cbz | 9-Cbz |
| 122334 | 4-t-BuPh | 4-t-BuPh | CN | 9-Cbz | 9-Cbz |
| 122335 | 4-t-BuPh | 4-t-BuPh | DPA | 9-Cbz | 9-Cbz |

TABLE 4-continued

| Compound No. | $R_{11b}$ | $R_{12c}$ | $R_{14b}$ | $R_{18c}$ | $R_{19b}$ |
|---|---|---|---|---|---|
| 122336 | 4-t-BuPh | 4-t-BuPh | 2-DBF | 9-Cbz | 9-Cbz |
| 122337 | 4-t-BuPh | 4-t-BuPh | 2-DBT | 9-Cbz | 9-Cbz |
| 122338 | 4-t-BuPh | 4-t-BuPh | 4-t-BuPh | 9-Cbz | 9-Cbz |
| 122339 | 4-t-BuPh | 4-t-BuPh | 1,3-di-t-BuPh | 9-Cbz | 9-Cbz |
| 122340 | 4-t-BuPh | 4-t-BuPh | 9-Cbz | 9-Cbz | 9-Cbz |
| 122341 | 4-t-BuPh | 4-t-BuPh | t-Bu | 4-t-BuPh | 4-t-BuPh |
| 122342 | 4-t-BuPh | 4-t-BuPh | Ph | 4-t-BuPh | 4-t-BuPh |
| 122343 | 4-t-BuPh | 4-t-BuPh | CN | 4-t-BuPh | 4-t-BuPh |
| 122344 | 4-t-BuPh | 4-t-BuPh | DPA | 4-t-BuPh | 4-t-BuPh |
| 122345 | 4-t-BuPh | 4-t-BuPh | 2-DBF | 4-t-BuPh | 4-t-BuPh |
| 122346 | 4-t-BuPh | 4-t-BuPh | 2-DBT | 4-t-BuPh | 4-t-BuPh |
| 122347 | 4-t-BuPh | 4-t-BuPh | 4-t-BuPh | 4-t-BuPh | 4-t-BuPh |
| 122348 | 4-t-BuPh | 4-t-BuPh | 1,3-di-t-BuPh | 4-t-BuPh | 4-t-BuPh |
| 122349 | 4-t-BuPh | 4-t-BuPh | 9-Cbz | 4-t-BuPh | 4-t-BuPh |
| 122350 | 4-t-BuPh | 4-t-BuPh | t-Bu | 1,3-di-t-BuPh | 1,3-di-t-BuPh |
| 122351 | 4-t-BuPh | 4-t-BuPh | Ph | 1,3-di-t-BuPh | 1,3-di-t-BuPh |
| 122352 | 4-t-BuPh | 4-t-BuPh | CN | 1,3-di-t-BuPh | 1,3-di-t-BuPh |
| 122353 | 4-t-BuPh | 4-t-BuPh | DPA | 1,3-di-t-BuPh | 1,3-di-t-BuPh |
| 122354 | 4-t-BuPh | 4-t-BuPh | 2-DBF | 1,3-di-t-BuPh | 1,3-di-t-BuPh |
| 122355 | 4-t-BuPh | 4-t-BuPh | 2-DBT | 1,3-di-t-BuPh | 1,3-di-t-BuPh |
| 122356 | 4-t-BuPh | 4-t-BuPh | 4-t-BuPh | 1,3-di-t-BuPh | 1,3-di-t-BuPh |
| 122357 | 4-t-BuPh | 4-t-BuPh | 1,3-di-t-BuPh | 1,3-di-t-BuPh | 1,3-di-t-BuPh |
| 122358 | 4-t-BuPh | 4-t-BuPh | 9-Cbz | 1,3-di-t-BuPh | 1,3-di-t-BuPh |
| 122359 | 1,3-di-t-BuPh | 1,3-di-t-BuPh | t-Bu | H | H |
| 122360 | 1,3-di-t-BuPh | 1,3-di-t-BuPh | Ph | H | H |
| 122361 | 1,3-di-t-BuPh | 1,3-di-t-BuPh | CN | H | H |
| 122362 | 1,3-di-t-BuPh | 1,3-di-t-BuPh | DPA | H | H |
| 122363 | 1,3-di-t-BuPh | 1,3-di-t-BuPh | 2-DBF | H | H |
| 122364 | 1,3-di-t-BuPh | 1,3-di-t-BuPh | 2-DBT | H | H |
| 122365 | 1,3-di-t-BuPh | 1,3-di-t-BuPh | 4-t-BuPh | H | H |
| 122366 | 1,3-di-t-BuPh | 1,3-di-t-BuPh | 9-Cbz | H | H |
| 122367 | 1,3-di-t-BuPh | 1,3-di-t-BuPh | t-Bu | t-Bu | t-Bu |
| 122368 | 1,3-di-t-BuPh | 1,3-di-t-BuPh | Ph | t-Bu | t-Bu |
| 122369 | 1,3-di-t-BuPh | 1,3-di-t-BuPh | CN | t-Bu | t-Bu |
| 122370 | 1,3-di-t-BuPh | 1,3-di-t-BuPh | DPA | t-Bu | t-Bu |
| 122371 | 1,3-di-t-BuPh | 1,3-di-t-BuPh | 2-DBF | t-Bu | t-Bu |
| 122372 | 1,3-di-t-BuPh | 1,3-di-t-BuPh | 2-DBT | t-Bu | t-Bu |
| 122373 | 1,3-di-t-BuPh | 1,3-di-t-BuPh | 4-t-BuPh | t-Bu | t-Bu |
| 122374 | 1,3-di-t-BuPh | 1,3-di-t-BuPh | 1,3-di-t-BuPh | t-Bu | t-Bu |
| 122375 | 1,3-di-t-BuPh | 1,3-di-t-BuPh | 9-Cbz | t-Bu | t-Bu |
| 122376 | 1,3-di-t-BuPh | 1,3-di-t-BuPh | t-Bu | Ph | Ph |
| 122377 | 1,3-di-t-BuPh | 1,3-di-t-BuPh | Ph | Ph | Ph |
| 122378 | 1,3-di-t-BuPh | 1,3-di-t-BuPh | CN | Ph | Ph |
| 122379 | 1,3-di-t-BuPh | 1,3-di-t-BuPh | DPA | Ph | Ph |
| 122380 | 1,3-di-t-BuPh | 1,3-di-t-BuPh | 2-DBF | Ph | Ph |
| 122381 | 1,3-di-t-BuPh | 1,3-di-t-BuPh | 2-DBT | Ph | Ph |
| 122382 | 1,3-di-t-BuPh | 1,3-di-t-BuPh | 4-t-BuPh | Ph | Ph |
| 122383 | 1,3-di-t-BuPh | 1,3-di-t-BuPh | 1,3-di-t-BuPh | Ph | Ph |
| 122384 | 1,3-di-t-BuPh | 1,3-di-t-BuPh | 9-Cbz | Ph | Ph |
| 122385 | 1,3-di-t-BuPh | 1,3-di-t-BuPh | t-Bu | CN | CN |
| 122386 | 1,3-di-t-BuPh | 1,3-di-t-BuPh | Ph | CN | CN |
| 122387 | 1,3-di-t-BuPh | 1,3-di-t-BuPh | CN | CN | CN |
| 122388 | 1,3-di-t-BuPh | 1,3-di-t-BuPh | DPA | CN | CN |
| 122389 | 1,3-di-t-BuPh | 1,3-di-t-BuPh | 2-DBF | CN | CN |

TABLE 4-continued

| Compound No. | $R_{11b}$ | $R_{12c}$ | $R_{14b}$ | $R_{18c}$ | $R_{19b}$ |
| --- | --- | --- | --- | --- | --- |
| 122390 | 1,3-di-t-BuPh | 1,3-di-t-BuPh | 2-DBT | CN | CN |
| 122391 | 1,3-di-t-BuPh | 1,3-di-t-BuPh | 4-t-BuPh | CN | CN |
| 122392 | 1,3-di-t-BuPh | 1,3-di-t-BuPh | 1,3-di-t-BuPh | CN | CN |
| 122393 | 1,3-di-t-BuPh | 1,3-di-t-BuPh | 9-Cbz | CN | CN |
| 122394 | 1,3-di-t-BuPh | 1,3-di-t-BuPh | t-Bu | 9-Cbz | 9-Cbz |
| 122395 | 1,3-di-t-BuPh | 1,3-di-t-BuPh | Ph | 9-Cbz | 9-Cbz |
| 122396 | 1,3-di-t-BuPh | 1,3-di-t-BuPh | CN | 9-Cbz | 9-Cbz |
| 122397 | 1,3-di-t-BuPh | 1,3-di-t-BuPh | DPA | 9-Cbz | 9-Cbz |
| 122398 | 1,3-di-t-BuPh | 1,3-di-t-BuPh | 2-DBF | 9-Cbz | 9-Cbz |
| 122399 | 1,3-di-t-BuPh | 1,3-di-t-BuPh | 2-DBT | 9-Cbz | 9-Cbz |
| 122400 | 1,3-di-t-BuPh | 1,3-di-t-BuPh | 4-t-BuPh | 9-Cbz | 9-Cbz |
| 122401 | 1,3-di-t-BuPh | 1,3-di-t-BuPh | 1,3-di-t-BuPh | 9-Cbz | 9-Cbz |
| 122402 | 1,3-di-t-BuPh | 1,3-di-t-BuPh | 9-Cbz | 9-Cbz | 9-Cbz |
| 122403 | 1,3-di-t-BuPh | 1,3-di-t-BuPh | t-Bu | 4-t-BuPh | 4-t-BuPh |
| 122404 | 1,3-di-t-BuPh | 1,3-di-t-BuPh | Ph | 4-t-BuPh | 4-t-BuPh |
| 122405 | 1,3-di-t-BuPh | 1,3-di-t-BuPh | CN | 4-t-BuPh | 4-t-BuPh |
| 122406 | 1,3-di-t-BuPh | 1,3-di-t-BuPh | DPA | 4-t-BuPh | 4-t-BuPh |
| 122407 | 1,3-di-t-BuPh | 1,3-di-t-BuPh | 2-DBF | 4-t-BuPh | 4-t-BuPh |
| 122408 | 1,3-di-t-BuPh | 1,3-di-t-BuPh | 2-DBT | 4-t-BuPh | 4-t-BuPh |
| 122409 | 1,3-di-t-BuPh | 1,3-di-t-BuPh | 4-t-BuPh | 4-t-BuPh | 4-t-BuPh |
| 122410 | 1,3-di-t-BuPh | 1,3-di-t-BuPh | 1,3-di-t-BuPh | 4-t-BuPh | 4-t-BuPh |
| 122411 | 1,3-di-t-BuPh | 1,3-di-t-BuPh | 9-Cbz | 4-t-BuPh | 4-t-BuPh |
| 122412 | 1,3-di-t-BuPh | 1,3-di-t-BuPh | t-Bu | 1,3-di-t-BuPh | 1,3-di-t-BuPh |
| 122413 | 1,3-di-t-BuPh | 1,3-di-t-BuPh | Ph | 1,3-di-t-BuPh | 1,3-di-t-BuPh |
| 122414 | 1,3-di-t-BuPh | 1,3-di-t-BuPh | CN | 1,3-di-t-BuPh | 1,3-di-t-BuPh |
| 122415 | 1,3-di-t-BuPh | 1,3-di-t-BuPh | DPA | 1,3-di-t-BuPh | 1,3-di-t-BuPh |
| 122416 | 1,3-di-t-BuPh | 1,3-di-t-BuPh | 2-DBF | 1,3-di-t-BuPh | 1,3-di-t-BuPh |
| 122417 | 1,3-di-t-BuPh | 1,3-di-t-BuPh | 2-DBT | 1,3-di-t-BuPh | 1,3-di-t-BuPh |
| 122418 | 1,3-di-t-BuPh | 1,3-di-t-BuPh | 4-t-BuPh | 1,3-di-t-BuPh | 1,3-di-t-BuPh |
| 122419 | 1,3-di-t-BuPh | 1,3-di-t-BuPh | 1,3-di-t-BuPh | 1,3-di-t-BuPh | 1,3-di-t-BuPh |
| 122420 | 1,3-di-t-BuPh | 1,3-di-t-BuPh | 9-Cbz | 1,3-di-t-BuPh | 1,3-di-t-BuPh |

Group HC5

The heterocyclic compound may be represented by Formula 12-4, and substituents may be defined as shown in Table 5.

TABLE 5

| Compound No. | $R_{11b}$ | $R_{12c}$ | $R_{14b}$ | $R_{18c}$ | $R_{19b}$ |
| --- | --- | --- | --- | --- | --- |
| 124001 | t-Bu | t-Bu | t-Bu | t-Bu | t-Bu |
| 124002 | Ph | Ph | t-Bu | Ph | Ph |
| 124003 | t-Bu | t-Bu | H | H | H |
| 124004 | H | H | t-Bu | H | H |
| 124005 | H | H | H | t-Bu | t-Bu |
| 124006 | t-Bu | t-Bu | t-Bu | H | H |
| 124007 | H | H | t-Bu | t-Bu | t-Bu |
| 124008 | t-Bu | t-Bu | H | t-Bu | t-Bu |
| 124009 | Ph | Ph | H | H | H |
| 124010 | H | H | Ph | H | H |
| 124011 | H | H | H | Ph | Ph |
| 124012 | Ph | Ph | Ph | H | H |
| 124013 | H | H | Ph | Ph | Ph |
| 124014 | Ph | Ph | H | Ph | Ph |
| 124015 | CN | CN | H | H | H |
| 124016 | H | H | CN | H | H |
| 124017 | H | H | H | CN | CN |
| 124018 | CN | CN | CN | H | H |
| 124019 | H | H | CN | CN | CN |
| 124020 | CN | CN | H | CN | CN |
| 124021 | 9-Cbz | 9-Cbz | H | H | H |
| 124022 | H | H | 9-Cbz | H | H |
| 124023 | H | H | H | 9-Cbz | 9-Cbz |
| 124024 | 9-Cbz | 9-Cbz | 9-Cbz | H | H |
| 124025 | H | H | 9-Cbz | 9-Cbz | 9-Cbz |
| 124026 | 9-Cbz | 9-Cbz | H | 9-Cbz | 9-Cbz |
| 124027 | Me | Me | H | H | H |
| 124028 | H | H | Me | H | H |
| 124029 | H | H | H | Me | Me |
| 124030 | Me | Me | Me | H | H |
| 124031 | H | H | Me | Me | Me |
| 124032 | Me | Me | H | Me | Me |
| 124033 | CD3 | CD3 | H | H | H |
| 124034 | H | H | CD3 | H | H |
| 124035 | H | H | H | CD3 | CD3 |
| 124036 | CD3 | CD3 | CD3 | H | H |
| 124037 | H | H | CD3 | CD3 | CD3 |
| 124038 | CD3 | CD3 | H | CD3 | CD3 |
| 124039 | 4-t-BuPh | 4-t-BuPh | H | H | H |
| 124040 | H | H | 4-t-BuPh | H | H |
| 124041 | H | H | H | 4-t-BuPh | 4-t-BuPh |
| 124042 | 4-t-BuPh | 4-t-BuPh | 4-t-BuPh | H | H |

TABLE 5-continued

| Compound No. | $R_{11b}$ | $R_{12c}$ | $R_{14b}$ | $R_{18c}$ | $R_{19b}$ |
|---|---|---|---|---|---|
| 124043 | H | H | 4-t-BuPh | 4-t-BuPh | 4-t-BuPh |
| 124044 | 4-t-BuPh | 4-t-BuPh | H | 4-t-BuPh | 4-t-BuPh |
| 124045 | 1,3-di-t-BuPh | 1,3-di-t-BuPh | H | H | H |
| 124046 | H | H | 1,3-di-t-BuPh | H | H |
| 124047 | H | H | H | 1,3-di-t-BuPh | 1,3-di-t-BuPh |
| 124048 | 1,3-di-t-BuPh | 1,3-di-t-BuPh | 1,3-di-t-BuPh | H | H |
| 124049 | H | H | 1,3-di-t-BuPh | 1,3-di-t-BuPh | 1,3-di-t-BuPh |
| 124050 | 1,3-di-t-BuPh | 1,3-di-t-BuPh | H | 1,3-di-t-BuPh | 1,3-di-t-BuPh |
| 124051 | t-Bu | t-Bu | Ph | H | H |
| 124052 | t-Bu | t-Bu | CN | H | H |
| 124053 | t-Bu | t-Bu | DPA | H | H |
| 124054 | t-Bu | t-Bu | 2-DBF | H | H |
| 124055 | t-Bu | t-Bu | 2-DBT | H | H |
| 124056 | t-Bu | t-Bu | 4-t-BuPh | H | H |
| 124057 | t-Bu | t-Bu | 1,3-di-t-BuPh | H | H |
| 124058 | t-Bu | t-Bu | 9-Cbz | H | H |
| 124059 | t-Bu | t-Bu | Ph | t-Bu | t-Bu |
| 124060 | t-Bu | t-Bu | CN | t-Bu | t-Bu |
| 124061 | t-Bu | t-Bu | DPA | t-Bu | t-Bu |
| 124062 | t-Bu | t-Bu | 2-DBF | t-Bu | t-Bu |
| 124063 | t-Bu | t-Bu | 2-DBT | t-Bu | t-Bu |
| 124064 | t-Bu | t-Bu | 4-t-BuPh | t-Bu | t-Bu |
| 124065 | t-Bu | t-Bu | 1,3-di-t-BuPh | t-Bu | t-Bu |
| 124066 | t-Bu | t-Bu | 9-Cbz | t-Bu | t-Bu |
| 124067 | t-Bu | t-Bu | t-Bu | Ph | Ph |
| 124068 | t-Bu | t-Bu | Ph | Ph | Ph |
| 124069 | t-Bu | t-Bu | CN | Ph | Ph |
| 124070 | t-Bu | t-Bu | DPA | Ph | Ph |
| 124071 | t-Bu | t-Bu | 2-DBF | Ph | Ph |
| 124072 | t-Bu | t-Bu | 2-DBT | Ph | Ph |
| 124073 | t-Bu | t-Bu | 4-t-BuPh | Ph | Ph |
| 124074 | t-Bu | t-Bu | 1,3-di-t-BuPh | Ph | Ph |
| 124075 | t-Bu | t-Bu | 9-Cbz | Ph | Ph |
| 124076 | t-Bu | t-Bu | t-Bu | CN | CN |
| 124077 | t-Bu | t-Bu | Ph | CN | CN |
| 124078 | t-Bu | t-Bu | CN | CN | CN |
| 124079 | t-Bu | t-Bu | DPA | CN | CN |
| 124080 | t-Bu | t-Bu | 2-DBF | CN | CN |
| 124081 | t-Bu | t-Bu | 2-DBT | CN | CN |
| 124082 | t-Bu | t-Bu | 4-t-BuPh | CN | CN |
| 124083 | t-Bu | t-Bu | 1,3-di-t-BuPh | CN | CN |
| 124084 | t-Bu | t-Bu | 9-Cbz | CN | CN |
| 124085 | t-Bu | t-Bu | t-Bu | 9-Cbz | 9-Cbz |
| 124086 | t-Bu | t-Bu | Ph | 9-Cbz | 9-Cbz |
| 124087 | t-Bu | t-Bu | CN | 9-Cbz | 9-Cbz |
| 124088 | t-Bu | t-Bu | DPA | 9-Cbz | 9-Cbz |
| 124089 | t-Bu | t-Bu | 2-DBF | 9-Cbz | 9-Cbz |
| 124090 | t-Bu | t-Bu | 2-DBT | 9-Cbz | 9-Cbz |
| 124091 | t-Bu | t-Bu | 4-t-BuPh | 9-Cbz | 9-Cbz |
| 124092 | t-Bu | t-Bu | 1,3-di-t-BuPh | 9-Cbz | 9-Cbz |
| 124093 | t-Bu | t-Bu | 9-Cbz | 9-Cbz | 9-Cbz |
| 124094 | t-Bu | t-Bu | t-Bu | 4-t-BuPh | 4-t-BuPh |
| 124095 | t-Bu | t-Bu | Ph | 4-t-BuPh | 4-t-BuPh |
| 124096 | t-Bu | t-Bu | CN | 4-t-BuPh | 4-t-BuPh |
| 124097 | t-Bu | t-Bu | DPA | 4-t-BuPh | 4-t-BuPh |
| 124098 | t-Bu | t-Bu | 2-DBF | 4-t-BuPh | 4-t-BuPh |
| 124099 | t-Bu | t-Bu | 2-DBT | 4-t-BuPh | 4-t-BuPh |
| 124100 | t-Bu | t-Bu | 4-t-BuPh | 4-t-BuPh | 4-t-BuPh |
| 124101 | t-Bu | t-Bu | 1,3-di-t-BuPh | 4-t-BuPh | 4-t-BuPh |
| 124102 | t-Bu | t-Bu | 9-Cbz | 4-t-BuPh | 4-t-BuPh |
| 124103 | t-Bu | t-Bu | t-Bu | 1,3-di-t-BuPh | 1,3-di-t-BuPh |
| 124104 | t-Bu | t-Bu | Ph | 1,3-di-t-BuPh | 1,3-di-t-BuPh |
| 124105 | t-Bu | t-Bu | CN | 1,3-di-t-BuPh | 1,3-di-t-BuPh |
| 124106 | t-Bu | t-Bu | DPA | 1,3-di-t-BuPh | 1,3-di-t-BuPh |
| 124107 | t-Bu | t-Bu | 2-DBF | 1,3-di-t-BuPh | 1,3-di-t-BuPh |
| 124108 | t-Bu | t-Bu | 2-DBT | 1,3-di-t-BuPh | 1,3-di-t-BuPh |
| 124109 | t-Bu | t-Bu | 4-t-BuPh | 1,3-di-t-BuPh | 1,3-di-t-BuPh |
| 124110 | t-Bu | t-Bu | 1,3-di-t-BuPh | 1,3-di-t-BuPh | 1,3-di-t-BuPh |
| 124111 | t-Bu | t-Bu | 9-Cbz | 1,3-di-t-BuPh | 1,3-di-t-BuPh |
| 124112 | Ph | Ph | t-Bu | H | H |
| 124113 | Ph | Ph | CN | H | H |
| 124114 | Ph | Ph | DPA | H | H |
| 124115 | Ph | Ph | 2-DBF | H | H |
| 124116 | Ph | Ph | 2-DBT | H | H |
| 124117 | Ph | Ph | 4-t-BuPh | H | H |
| 124118 | Ph | Ph | 1,3-di-t-BuPh | H | H |
| 124119 | Ph | Ph | 9-Cbz | H | H |
| 124120 | Ph | Ph | t-Bu | t-Bu | t-Bu |
| 124121 | Ph | Ph | Ph | t-Bu | t-Bu |
| 124122 | Ph | Ph | CN | t-Bu | t-Bu |

TABLE 5-continued

| Compound No. | $R_{11b}$ | $R_{12c}$ | $R_{14b}$ | $R_{18c}$ | $R_{19b}$ |
|---|---|---|---|---|---|
| 124123 | Ph | Ph | DPA | t-Bu | t-Bu |
| 124124 | Ph | Ph | 2-DBF | t-Bu | t-Bu |
| 124125 | Ph | Ph | 2-DBT | t-Bu | t-Bu |
| 124126 | Ph | Ph | 4-t-BuPh | t-Bu | t-Bu |
| 124127 | Ph | Ph | 1,3-di-t-BuPh | t-Bu | t-Bu |
| 124128 | Ph | Ph | 9-Cbz | t-Bu | t-Bu |
| 124129 | Ph | Ph | Ph | Ph | Ph |
| 124130 | Ph | Ph | CN | Ph | Ph |
| 124131 | Ph | Ph | DPA | Ph | Ph |
| 124132 | Ph | Ph | 2-DBF | Ph | Ph |
| 124133 | Ph | Ph | 2-DBT | Ph | Ph |
| 124134 | Ph | Ph | 4-t-BuPh | Ph | Ph |
| 124135 | Ph | Ph | 1,3-di-t-BuPh | Ph | Ph |
| 124136 | Ph | Ph | 9-Cbz | Ph | Ph |
| 124137 | Ph | Ph | t-Bu | CN | CN |
| 124138 | Ph | Ph | Ph | CN | CN |
| 124139 | Ph | Ph | CN | CN | CN |
| 124140 | Ph | Ph | DPA | CN | CN |
| 124141 | Ph | Ph | 2-DBF | CN | CN |
| 124142 | Ph | Ph | 2-DBT | CN | CN |
| 124143 | Ph | Ph | 4-t-BuPh | CN | CN |
| 124144 | Ph | Ph | 1,3-di-t-BuPh | CN | CN |
| 124145 | Ph | Ph | 9-Cbz | CN | CN |
| 124146 | Ph | Ph | t-Bu | 9-Cbz | 9-Cbz |
| 124147 | Ph | Ph | Ph | 9-Cbz | 9-Cbz |
| 124148 | Ph | Ph | CN | 9-Cbz | 9-Cbz |
| 124149 | Ph | Ph | DPA | 9-Cbz | 9-Cbz |
| 124150 | Ph | Ph | 2-DBF | 9-Cbz | 9-Cbz |
| 124151 | Ph | Ph | 2-DBT | 9-Cbz | 9-Cbz |
| 124152 | Ph | Ph | 4-t-BuPh | 9-Cbz | 9-Cbz |
| 124153 | Ph | Ph | 1,3-di-t-BuPh | 9-Cbz | 9-Cbz |
| 124154 | Ph | Ph | 9-Cbz | 9-Cbz | 9-Cbz |
| 124155 | Ph | Ph | t-Bu | 4-t-BuPh | 4-t-BuPh |
| 124156 | Ph | Ph | Ph | 4-t-BuPh | 4-t-BuPh |
| 124157 | Ph | Ph | CN | 4-t-BuPh | 4-t-BuPh |
| 124158 | Ph | Ph | DPA | 4-t-BuPh | 4-t-BuPh |
| 124159 | Ph | Ph | 2-DBF | 4-t-BuPh | 4-t-BuPh |
| 124160 | Ph | Ph | 2-DBT | 4-t-BuPh | 4-t-BuPh |
| 124161 | Ph | Ph | 4-t-BuPh | 4-t-BuPh | 4-t-BuPh |
| 124162 | Ph | Ph | 1,3-di-t-BuPh | 4-t-BuPh | 4-t-BuPh |
| 124163 | Ph | Ph | 9-Cbz | 4-t-BuPh | 4-t-BuPh |
| 124164 | Ph | Ph | t-Bu | 1,3-di-t-BuPh | 1,3-di-t-BuPh |
| 124165 | Ph | Ph | Ph | 1,3-di-t-BuPh | 1,3-di-t-BuPh |
| 124166 | Ph | Ph | CN | 1,3-di-t-BuPh | 1,3-di-t-BuPh |
| 124167 | Ph | Ph | DPA | 1,3-di-t-BuPh | 1,3-di-t-BuPh |
| 124168 | Ph | Ph | 2-DBF | 1,3-di-t-BuPh | 1,3-di-t-BuPh |
| 124169 | Ph | Ph | 2-DBT | 1,3-di-t-BuPh | 1,3-di-t-BuPh |
| 124170 | Ph | Ph | 4-t-BuPh | 1,3-di-t-BuPh | 1,3-di-t-BuPh |
| 124171 | Ph | Ph | 1,3-di-t-BuPh | 1,3-di-t-BuPh | 1,3-di-t-BuPh |
| 124172 | Ph | Ph | 9-Cbz | 1,3-di-t-BuPh | 1,3-di-t-BuPh |
| 124173 | 9-Cbz | 9-Cbz | t-Bu | H | H |
| 124174 | 9-Cbz | 9-Cbz | Ph | H | H |
| 124175 | 9-Cbz | 9-Cbz | CN | H | H |
| 124176 | 9-Cbz | 9-Cbz | DPA | H | H |
| 124177 | 9-Cbz | 9-Cbz | 2-DBF | H | H |
| 124178 | 9-Cbz | 9-Cbz | 2-DBT | H | H |
| 124179 | 9-Cbz | 9-Cbz | 4-t-BuPh | H | H |
| 124180 | 9-Cbz | 9-Cbz | 1,3-di-t-BuPh | H | H |
| 124181 | 9-Cbz | 9-Cbz | t-Bu | t-Bu | t-Bu |
| 124182 | 9-Cbz | 9-Cbz | Ph | t-Bu | t-Bu |
| 124183 | 9-Cbz | 9-Cbz | CN | t-Bu | t-Bu |
| 124184 | 9-Cbz | 9-Cbz | DPA | t-Bu | t-Bu |
| 124185 | 9-Cbz | 9-Cbz | 2-DBF | t-Bu | t-Bu |
| 124186 | 9-Cbz | 9-Cbz | 2-DBT | t-Bu | t-Bu |
| 124187 | 9-Cbz | 9-Cbz | 4-t-BuPh | t-Bu | t-Bu |
| 124188 | 9-Cbz | 9-Cbz | 1,3-di-t-BuPh | t-Bu | t-Bu |
| 124189 | 9-Cbz | 9-Cbz | 9-Cbz | t-Bu | t-Bu |
| 124190 | 9-Cbz | 9-Cbz | t-Bu | Ph | Ph |
| 124191 | 9-Cbz | 9-Cbz | Ph | Ph | Ph |
| 124192 | 9-Cbz | 9-Cbz | CN | Ph | Ph |
| 124193 | 9-Cbz | 9-Cbz | DPA | Ph | Ph |
| 124194 | 9-Cbz | 9-Cbz | 2-DBF | Ph | Ph |
| 124195 | 9-Cbz | 9-Cbz | 2-DBT | Ph | Ph |
| 124196 | 9-Cbz | 9-Cbz | 4-t-BuPh | Ph | Ph |
| 124197 | 9-Cbz | 9-Cbz | 1,3-di-t-BuPh | Ph | Ph |
| 124198 | 9-Cbz | 9-Cbz | 9-Cbz | Ph | Ph |
| 124199 | 9-Cbz | 9-Cbz | t-Bu | CN | CN |
| 124200 | 9-Cbz | 9-Cbz | Ph | CN | CN |
| 124201 | 9-Cbz | 9-Cbz | CN | CN | CN |
| 124202 | 9-Cbz | 9-Cbz | DPA | CN | CN |
| 124203 | 9-Cbz | 9-Cbz | 2-DBF | CN | CN |
| 124204 | 9-Cbz | 9-Cbz | 2-DBT | CN | CN |
| 124205 | 9-Cbz | 9-Cbz | 4-t-BuPh | CN | CN |
| 124206 | 9-Cbz | 9-Cbz | 1,3-di-t-BuPh | CN | CN |
| 124207 | 9-Cbz | 9-Cbz | 9-Cbz | CN | CN |
| 124208 | 9-Cbz | 9-Cbz | t-Bu | 9-Cbz | 9-Cbz |

TABLE 5-continued

| Compound No. | $R_{11b}$ | $R_{12c}$ | $R_{14b}$ | $R_{18c}$ | $R_{19b}$ |
|---|---|---|---|---|---|
| 124209 | 9-Cbz | 9-Cbz | Ph | 9-Cbz | 9-Cbz |
| 124210 | 9-Cbz | 9-Cbz | CN | 9-Cbz | 9-Cbz |
| 124211 | 9-Cbz | 9-Cbz | DPA | 9-Cbz | 9-Cbz |
| 124212 | 9-Cbz | 9-Cbz | 2-DBF | 9-Cbz | 9-Cbz |
| 124213 | 9-Cbz | 9-Cbz | 2-DBT | 9-Cbz | 9-Cbz |
| 124214 | 9-Cbz | 9-Cbz | 4-t-BuPh | 9-Cbz | 9-Cbz |
| 124215 | 9-Cbz | 9-Cbz | 1,3-di-t-BuPh | 9-Cbz | 9-Cbz |
| 124216 | 9-Cbz | 9-Cbz | 9-Cbz | 9-Cbz | 9-Cbz |
| 124217 | 9-Cbz | 9-Cbz | t-Bu | 4-t-BuPh | 4-t-BuPh |
| 124218 | 9-Cbz | 9-Cbz | Ph | 4-t-BuPh | 4-t-BuPh |
| 124219 | 9-Cbz | 9-Cbz | CN | 4-t-BuPh | 4-t-BuPh |
| 124220 | 9-Cbz | 9-Cbz | DPA | 4-t-BuPh | 4-t-BuPh |
| 124221 | 9-Cbz | 9-Cbz | 2-DBF | 4-t-BuPh | 4-t-BuPh |
| 124222 | 9-Cbz | 9-Cbz | 2-DBT | 4-t-BuPh | 4-t-BuPh |
| 124223 | 9-Cbz | 9-Cbz | 4-t-BuPh | 4-t-BuPh | 4-t-BuPh |
| 124224 | 9-Cbz | 9-Cbz | 1,3-di-t-BuPh | 4-t-BuPh | 4-t-BuPh |
| 124225 | 9-Cbz | 9-Cbz | 9-Cbz | 4-t-BuPh | 4-t-BuPh |
| 124226 | 9-Cbz | 9-Cbz | t-Bu | 1,3-di-t-BuPh | 1,3-di-t-BuPh |
| 124227 | 9-Cbz | 9-Cbz | Ph | 1,3-di-t-BuPh | 1,3-di-t-BuPh |
| 124228 | 9-Cbz | 9-Cbz | CN | 1,3-di-t-BuPh | 1,3-di-t-BuPh |
| 124229 | 9-Cbz | 9-Cbz | DPA | 1,3-di-t-BuPh | 1,3-di-t-BuPh |
| 124230 | 9-Cbz | 9-Cbz | 2-DBF | 1,3-di-t-BuPh | 1,3-di-t-BuPh |
| 124231 | 9-Cbz | 9-Cbz | 2-DBT | 1,3-di-t-BuPh | 1,3-di-t-BuPh |
| 124232 | 9-Cbz | 9-Cbz | 4-t-BuPh | 1,3-di-t-BuPh | 1,3-di-t-BuPh |
| 124233 | 9-Cbz | 9-Cbz | 1,3-di-t-BuPh | 1,3-di-t-BuPh | 1,3-di-t-BuPh |
| 124234 | 9-Cbz | 9-Cbz | 9-Cbz | 1,3-di-t-BuPh | 1,3-di-t-BuPh |
| 124235 | CN | CN | t-Bu | H | H |
| 124236 | CN | CN | Ph | H | H |
| 124237 | CN | CN | DPA | H | H |
| 124238 | CN | CN | 2-DBF | H | H |
| 124239 | CN | CN | 2-DBT | H | H |
| 124240 | CN | CN | 4-t-BuPh | H | H |
| 124241 | CN | CN | 1,3-di-t-BuPh | H | H |
| 124242 | CN | CN | 9-Cbz | H | H |
| 124243 | CN | CN | t-Bu | t-Bu | t-Bu |
| 124244 | CN | CN | Ph | t-Bu | t-Bu |
| 124245 | CN | CN | CN | t-Bu | t-Bu |
| 124246 | CN | CN | DPA | t-Bu | t-Bu |
| 124247 | CN | CN | 2-DBF | t-Bu | t-Bu |
| 124248 | CN | CN | 2-DBT | t-Bu | t-Bu |
| 124249 | CN | CN | 4-t-BuPh | t-Bu | t-Bu |
| 124250 | CN | CN | 1,3-di-t-BuPh | t-Bu | t-Bu |
| 124251 | CN | CN | 9-Cbz | t-Bu | t-Bu |
| 124252 | CN | CN | t-Bu | Ph | Ph |
| 124253 | CN | CN | Ph | Ph | Ph |
| 124254 | CN | CN | CN | Ph | Ph |
| 124255 | CN | CN | DPA | Ph | Ph |
| 124256 | CN | CN | 2-DBF | Ph | Ph |
| 124257 | CN | CN | 2-DBT | Ph | Ph |
| 124258 | CN | CN | 4-t-BuPh | Ph | Ph |
| 124259 | CN | CN | 1,3-di-t-BuPh | Ph | Ph |
| 124260 | CN | CN | 9-Cbz | Ph | Ph |
| 124261 | CN | CN | t-Bu | CN | CN |
| 124262 | CN | CN | Ph | CN | CN |
| 124263 | CN | CN | CN | CN | CN |
| 124264 | CN | CN | DPA | CN | CN |
| 124265 | CN | CN | 2-DBF | CN | CN |
| 124266 | CN | CN | 2-DBT | CN | CN |
| 124267 | CN | CN | 4-t-BuPh | CN | CN |
| 124268 | CN | CN | 1,3-di-t-BuPh | CN | CN |
| 124269 | CN | CN | 9-Cbz | CN | CN |
| 124270 | CN | CN | t-Bu | 9-Cbz | 9-Cbz |
| 124271 | CN | CN | Ph | 9-Cbz | 9-Cbz |
| 124272 | CN | CN | CN | 9-Cbz | 9-Cbz |
| 124273 | CN | CN | DPA | 9-Cbz | 9-Cbz |
| 124274 | CN | CN | 2-DBF | 9-Cbz | 9-Cbz |
| 124275 | CN | CN | 2-DBT | 9-Cbz | 9-Cbz |
| 124276 | CN | CN | 4-t-BuPh | 9-Cbz | 9-Cbz |
| 124277 | CN | CN | 1,3-di-t-BuPh | 9-Cbz | 9-Cbz |
| 124278 | CN | CN | 9-Cbz | 9-Cbz | 9-Cbz |
| 124279 | CN | CN | t-Bu | 4-t-BuPh | 4-t-BuPh |
| 124280 | CN | CN | Ph | 4-t-BuPh | 4-t-BuPh |
| 124281 | CN | CN | CN | 4-t-BuPh | 4-t-BuPh |
| 124282 | CN | CN | DPA | 4-t-BuPh | 4-t-BuPh |
| 124283 | CN | CN | 2-DBF | 4-t-BuPh | 4-t-BuPh |
| 124284 | CN | CN | 2-DBT | 4-t-BuPh | 4-t-BuPh |
| 124285 | CN | CN | 4-t-BuPh | 4-t-BuPh | 4-t-BuPh |
| 124286 | CN | CN | 1,3-di-t-BuPh | 4-t-BuPh | 4-t-BuPh |
| 124287 | CN | CN | 9-Cbz | 4-t-BuPh | 4-t-BuPh |
| 124288 | CN | CN | t-Bu | 1,3-di-t-BuPh | 1,3-di-t-BuPh |
| 124289 | CN | CN | Ph | 1,3-di-t-BuPh | 1,3-di-t-BuPh |

TABLE 5-continued

| Compound No. | $R_{11b}$ | $R_{12c}$ | $R_{14b}$ | $R_{18c}$ | $R_{19b}$ |
|---|---|---|---|---|---|
| 124290 | CN | CN | CN | 1,3-di-t-BuPh | 1,3-di-t-BuPh |
| 124291 | CN | CN | DPA | 1,3-di-t-BuPh | 1,3-di-t-BuPh |
| 124292 | CN | CN | 2-DBF | 1,3-di-t-BuPh | 1,3-di-t-BuPh |
| 124293 | CN | CN | 2-DBT | 1,3-di-t-BuPh | 1,3-di-t-BuPh |
| 124294 | CN | CN | 4-t-BuPh | 1,3-di-t-BuPh | 1,3-di-t-BuPh |
| 124295 | CN | CN | 1,3-di-t-BuPh | 1,3-di-t-BuPh | 1,3-di-t-BuPh |
| 124296 | CN | CN | 9-Cbz | 1,3-di-t-BuPh | 1,3-di-t-BuPh |
| 124297 | 4-t-BuPh | 4-t-BuPh | t-Bu | H | H |
| 124298 | 4-t-BuPh | 4-t-BuPh | Ph | H | H |
| 124299 | 4-t-BuPh | 4-t-BuPh | CN | H | H |
| 124300 | 4-t-BuPh | 4-t-BuPh | DPA | H | H |
| 124301 | 4-t-BuPh | 4-t-BuPh | 2-DBF | H | H |
| 124302 | 4-t-BuPh | 4-t-BuPh | 2-DBT | H | H |
| 124303 | 4-t-BuPh | 4-t-BuPh | 1,3-di-t-BuPh | H | H |
| 124304 | 4-t-BuPh | 4-t-BuPh | 9-Cbz | H | H |
| 124305 | 4-t-BuPh | 4-t-BuPh | t-Bu | t-Bu | t-Bu |
| 124306 | 4-t-BuPh | 4-t-BuPh | Ph | t-Bu | t-Bu |
| 124307 | 4-t-BuPh | 4-t-BuPh | CN | t-Bu | t-Bu |
| 124308 | 4-t-BuPh | 4-t-BuPh | DPA | t-Bu | t-Bu |
| 124309 | 4-t-BuPh | 4-t-BuPh | 2-DBF | t-Bu | t-Bu |
| 124310 | 4-t-BuPh | 4-t-BuPh | 2-DBT | t-Bu | t-Bu |
| 124311 | 4-t-BuPh | 4-t-BuPh | 4-t-BuPh | t-Bu | t-Bu |
| 124312 | 4-t-BuPh | 4-t-BuPh | 1,3-di-t-BuPh | t-Bu | t-Bu |
| 124313 | 4-t-BuPh | 4-t-BuPh | 9-Cbz | t-Bu | t-Bu |
| 124314 | 4-t-BuPh | 4-t-BuPh | t-Bu | Ph | Ph |
| 124315 | 4-t-BuPh | 4-t-BuPh | Ph | Ph | Ph |
| 124316 | 4-t-BuPh | 4-t-BuPh | CN | Ph | Ph |
| 124317 | 4-t-BuPh | 4-t-BuPh | DPA | Ph | Ph |
| 124318 | 4-t-BuPh | 4-t-BuPh | 2-DBF | Ph | Ph |
| 124319 | 4-t-BuPh | 4-t-BuPh | 2-DBT | Ph | Ph |
| 124320 | 4-t-BuPh | 4-t-BuPh | 4-t-BuPh | Ph | Ph |
| 124321 | 4-t-BuPh | 4-t-BuPh | 1,3-di-t-BuPh | Ph | Ph |
| 124322 | 4-t-BuPh | 4-t-BuPh | 9-Cbz | Ph | Ph |
| 124323 | 4-t-BuPh | 4-t-BuPh | t-Bu | CN | CN |
| 124324 | 4-t-BuPh | 4-t-BuPh | Ph | CN | CN |
| 124325 | 4-t-BuPh | 4-t-BuPh | CN | CN | CN |
| 124326 | 4-t-BuPh | 4-t-BuPh | DPA | CN | CN |
| 124327 | 4-t-BuPh | 4-t-BuPh | 2-DBF | CN | CN |
| 124328 | 4-t-BuPh | 4-t-BuPh | 2-DBT | CN | CN |
| 124329 | 4-t-BuPh | 4-t-BuPh | 4-t-BuPh | CN | CN |
| 124330 | 4-t-BuPh | 4-t-BuPh | 1,3-di-t-BuPh | CN | CN |
| 124331 | 4-t-BuPh | 4-t-BuPh | 9-Cbz | CN | CN |
| 124332 | 4-t-BuPh | 4-t-BuPh | t-Bu | 9-Cbz | 9-Cbz |
| 124333 | 4-t-BuPh | 4-t-BuPh | Ph | 9-Cbz | 9-Cbz |
| 124334 | 4-t-BuPh | 4-t-BuPh | CN | 9-Cbz | 9-Cbz |
| 124335 | 4-t-BuPh | 4-t-BuPh | DPA | 9-Cbz | 9-Cbz |
| 124336 | 4-t-BuPh | 4-t-BuPh | 2-DBF | 9-Cbz | 9-Cbz |
| 124337 | 4-t-BuPh | 4-t-BuPh | 2-DBT | 9-Cbz | 9-Cbz |
| 124338 | 4-t-BuPh | 4-t-BuPh | 4-t-BuPh | 9-Cbz | 9-Cbz |
| 124339 | 4-t-BuPh | 4-t-BuPh | 1,3-di-t-BuPh | 9-Cbz | 9-Cbz |
| 124340 | 4-t-BuPh | 4-t-BuPh | 9-Cbz | 9-Cbz | 9-Cbz |
| 124341 | 4-t-BuPh | 4-t-BuPh | t-Bu | 4-t-BuPh | 4-t-BuPh |
| 124342 | 4-t-BuPh | 4-t-BuPh | Ph | 4-t-BuPh | 4-t-BuPh |
| 124343 | 4-t-BuPh | 4-t-BuPh | CN | 4-t-BuPh | 4-t-BuPh |
| 124344 | 4-t-BuPh | 4-t-BuPh | DPA | 4-t-BuPh | 4-t-BuPh |
| 124345 | 4-t-BuPh | 4-t-BuPh | 2-DBF | 4-t-BuPh | 4-t-BuPh |
| 124346 | 4-t-BuPh | 4-t-BuPh | 2-DBT | 4-t-BuPh | 4-t-BuPh |
| 124347 | 4-t-BuPh | 4-t-BuPh | 4-t-BuPh | 4-t-BuPh | 4-t-BuPh |
| 124348 | 4-t-BuPh | 4-t-BuPh | 1,3-di-t-BuPh | 4-t-BuPh | 4-t-BuPh |
| 124349 | 4-t-BuPh | 4-t-BuPh | 9-Cbz | 4-t-BuPh | 4-t-BuPh |
| 124350 | 4-t-BuPh | 4-t-BuPh | t-Bu | 1,3-di-t-BuPh | 1,3-di-t-BuPh |
| 124351 | 4-t-BuPh | 4-t-BuPh | Ph | 1,3-di-t-BuPh | 1,3-di-t-BuPh |
| 124352 | 4-t-BuPh | 4-t-BuPh | CN | 1,3-di-t-BuPh | 1,3-di-t-BuPh |
| 124353 | 4-t-BuPh | 4-t-BuPh | DPA | 1,3-di-t-BuPh | 1,3-di-t-BuPh |
| 124354 | 4-t-BuPh | 4-t-BuPh | 2-DBF | 1,3-di-t-BuPh | 1,3-di-t-BuPh |
| 124355 | 4-t-BuPh | 4-t-BuPh | 2-DBT | 1,3-di-t-BuPh | 1,3-di-t-BuPh |

TABLE 5-continued

| Compound No. | $R_{11b}$ | $R_{12c}$ | $R_{14b}$ | $R_{18c}$ | $R_{19b}$ |
|---|---|---|---|---|---|
| 124356 | 4-t-BuPh | 4-t-BuPh | 4-t-BuPh | 1,3-di-t-BuPh | 1,3-di-t-BuPh |
| 124357 | 4-t-BuPh | 4-t-BuPh | 1,3-di-t-BuPh | 1,3-di-t-BuPh | 1,3-di-t-BuPh |
| 124358 | 4-t-BuPh | 4-t-BuPh | 9-Cbz | 1,3-di-t-BuPh | 1,3-di-t-BuPh |
| 124359 | 1,3-di-t-BuPh | 1,3-di-t-BuPh | t-Bu | H | H |
| 124360 | 1,3-di-t-BuPh | 1,3-di-t-BuPh | Ph | H | H |
| 124361 | 1,3-di-t-BuPh | 1,3-di-t-BuPh | CN | H | H |
| 124362 | 1,3-di-t-BuPh | 1,3-di-t-BuPh | DPA | H | H |
| 124363 | 1,3-di-t-BuPh | 1,3-di-t-BuPh | 2-DBF | H | H |
| 124364 | 1,3-di-t-BuPh | 1,3-di-t-BuPh | 2-DBT | H | H |
| 124365 | 1,3-di-t-BuPh | 1,3-di-t-BuPh | 4-t-BuPh | H | H |
| 124366 | 1,3-di-t-BuPh | 1,3-di-t-BuPh | 9-Cbz | H | H |
| 124367 | 1,3-di-t-BuPh | 1,3-di-t-BuPh | t-Bu | t-Bu | t-Bu |
| 124368 | 1,3-di-t-BuPh | 1,3-di-t-BuPh | Ph | t-Bu | t-Bu |
| 124369 | 1,3-di-t-BuPh | 1,3-di-t-BuPh | CN | t-Bu | t-Bu |
| 124370 | 1,3-di-t-BuPh | 1,3-di-t-BuPh | DPA | t-Bu | t-Bu |
| 124371 | 1,3-di-t-BuPh | 1,3-di-t-BuPh | 2-DBF | t-Bu | t-Bu |
| 124372 | 1,3-di-t-BuPh | 1,3-di-t-BuPh | 2-DBT | t-Bu | t-Bu |
| 124373 | 1,3-di-t-BuPh | 1,3-di-t-BuPh | 4-t-BuPh | t-Bu | t-Bu |
| 124374 | 1,3-di-t-BuPh | 1,3-di-t-BuPh | 1,3-di-t-BuPh | t-Bu | t-Bu |
| 124375 | 1,3-di-t-BuPh | 1,3-di-t-BuPh | 9-Cbz | t-Bu | t-Bu |
| 124376 | 1,3-di-t-BuPh | 1,3-di-t-BuPh | t-Bu | Ph | Ph |
| 124377 | 1,3-di-t-BuPh | 1,3-di-t-BuPh | Ph | Ph | Ph |
| 124378 | 1,3-di-t-BuPh | 1,3-di-t-BuPh | CN | Ph | Ph |
| 124379 | 1,3-di-t-BuPh | 1,3-di-t-BuPh | DPA | Ph | Ph |
| 124380 | 1,3-di-t-BuPh | 1,3-di-t-BuPh | 2-DBF | Ph | Ph |
| 124381 | 1,3-di-t-BuPh | 1,3-di-t-BuPh | 2-DBT | Ph | Ph |
| 124382 | 1,3-di-t-BuPh | 1,3-di-t-BuPh | 4-t-BuPh | Ph | Ph |
| 124383 | 1,3-di-t-BuPh | 1,3-di-t-BuPh | 1,3-di-t-BuPh | Ph | Ph |
| 124384 | 1,3-di-t-BuPh | 1,3-di-t-BuPh | 9-Cbz | Ph | Ph |
| 124385 | 1,3-di-t-BuPh | 1,3-di-t-BuPh | t-Bu | CN | CN |
| 124386 | 1,3-di-t-BuPh | 1,3-di-t-BuPh | Ph | CN | CN |
| 124387 | 1,3-di-t-BuPh | 1,3-di-t-BuPh | CN | CN | CN |
| 124388 | 1,3-di-t-BuPh | 1,3-di-t-BuPh | DPA | CN | CN |
| 124389 | 1,3-di-t-BuPh | 1,3-di-t-BuPh | 2-DBF | CN | CN |
| 124390 | 1,3-di-t-BuPh | 1,3-di-t-BuPh | 2-DBT | CN | CN |
| 124391 | 1,3-di-t-BuPh | 1,3-di-t-BuPh | 4-t-BuPh | CN | CN |
| 124392 | 1,3-di-t-BuPh | 1,3-di-t-BuPh | 1,3-di-t-BuPh | CN | CN |
| 124393 | 1,3-di-t-BuPh | 1,3-di-t-BuPh | 9-Cbz | CN | CN |
| 124394 | 1,3-di-t-BuPh | 1,3-di-t-BuPh | t-Bu | 9-Cbz | 9-Cbz |
| 124395 | 1,3-di-t-BuPh | 1,3-di-t-BuPh | Ph | 9-Cbz | 9-Cbz |
| 124396 | 1,3-di-t-BuPh | 1,3-di-t-BuPh | CN | 9-Cbz | 9-Cbz |
| 124397 | 1,3-di-t-BuPh | 1,3-di-t-BuPh | DPA | 9-Cbz | 9-Cbz |
| 124398 | 1,3-di-t-BuPh | 1,3-di-t-BuPh | 2-DBF | 9-Cbz | 9-Cbz |
| 124399 | 1,3-di-t-BuPh | 1,3-di-t-BuPh | 2-DBT | 9-Cbz | 9-Cbz |
| 124400 | 1,3-di-t-BuPh | 1,3-di-t-BuPh | 4-t-BuPh | 9-Cbz | 9-Cbz |
| 124401 | 1,3-di-t-BuPh | 1,3-di-t-BuPh | 1,3-di-t-BuPh | 9-Cbz | 9-Cbz |
| 124402 | 1,3-di-t-BuPh | 1,3-di-t-BuPh | 9-Cbz | 9-Cbz | 9-Cbz |
| 124403 | 1,3-di-t-BuPh | 1,3-di-t-BuPh | t-Bu | 4-t-BuPh | 4-t-BuPh |
| 124404 | 1,3-di-t-BuPh | 1,3-di-t-BuPh | Ph | 4-t-BuPh | 4-t-BuPh |
| 124405 | 1,3-di-t-BuPh | 1,3-di-t-BuPh | CN | 4-t-BuPh | 4-t-BuPh |

TABLE 5-continued

| Compound No. | R$_{11b}$ | R$_{12c}$ | R$_{14b}$ | R$_{18c}$ | R$_{19b}$ |
|---|---|---|---|---|---|
| 124406 | 1,3-di-t-BuPh | 1,3-di-t-BuPh | DPA | 4-t-BuPh | 4-t-BuPh |
| 124407 | 1,3-di-t-BuPh | 1,3-di-t-BuPh | 2-DBF | 4-t-BuPh | 4-t-BuPh |
| 124408 | 1,3-di-t-BuPh | 1,3-di-t-BuPh | 2-DBT | 4-t-BuPh | 4-t-BuPh |
| 124409 | 1,3-di-t-BuPh | 1,3-di-t-BuPh | 4-t-BuPh | 4-t-BuPh | 4-t-BuPh |
| 124410 | 1,3-di-t-BuPh | 1,3-di-t-BuPh | 1,3-di-t-BuPh | 4-t-BuPh | 4-t-BuPh |
| 124411 | 1,3-di-t-BuPh | 1,3-di-t-BuPh | 9-Cbz | 4-t-BuPh | 4-t-BuPh |
| 124412 | 1,3-di-t-BuPh | 1,3-di-t-BuPh | t-Bu | 1,3-di-t-BuPh | 1,3-di-t-BuPh |
| 124413 | 1,3-di-t-BuPh | 1,3-di-t-BuPh | Ph | 1,3-di-t-BuPh | 1,3-di-t-BuPh |
| 124414 | 1,3-di-t-BuPh | 1,3-di-t-BuPh | CN | 1,3-di-t-BuPh | 1,3-di-t-BuPh |
| 124415 | 1,3-di-t-BuPh | 1,3-di-t-BuPh | DPA | 1,3-di-t-BuPh | 1,3-di-t-BuPh |
| 124416 | 1,3-di-t-BuPh | 1,3-di-t-BuPh | 2-DBF | 1,3-di-t-BuPh | 1,3-di-t-BuPh |
| 124417 | 1,3-di-t-BuPh | 1,3-di-t-BuPh | 2-DBT | 1,3-di-t-BuPh | 1,3-di-t-BuPh |
| 124418 | 1,3-di-t-BuPh | 1,3-di-t-BuPh | 4-t-BuPh | 1,3-di-t-BuPh | 1,3-di-t-BuPh |
| 124419 | 1,3-di-t-BuPh | 1,3-di-t-BuPh | 1,3-di-t-BuPh | 1,3-di-t-BuPh | 1,3-di-t-BuPh |
| 124420 | 1,3-di-t-BuPh | 1,3-di-t-BuPh | 9-Cbz | 1,3-di-t-BuPh | 1,3-di-t-BuPh |

Group HC6

The heterocyclic compound may be represented by Formula 14-1, and substituents may be defined as shown in Table A

TABLE 6

| Compound No. | R$_{11b}$ | R$_{12c}$ | R$_{15C}$ | R$_{18b}$ | R$_{19b}$ |
|---|---|---|---|---|---|
| 141001 | t-Bu | t-Bu | t-Bu | t-Bu | t-Bu |
| 141002 | Ph | Ph | t-Bu | Ph | Ph |
| 141003 | t-Bu | t-Bu | H | H | H |
| 141004 | H | H | t-Bu | H | H |
| 141005 | H | H | H | t-Bu | t-Bu |
| 141006 | t-Bu | t-Bu | t-Bu | H | H |
| 141007 | H | H | t-Bu | t-Bu | t-Bu |
| 141008 | t-Bu | t-Bu | H | t-Bu | t-Bu |
| 141009 | Ph | Ph | H | H | H |
| 141010 | H | H | Ph | H | H |
| 141011 | H | H | H | Ph | Ph |
| 141012 | Ph | Ph | Ph | H | H |
| 141013 | H | H | Ph | Ph | Ph |
| 141014 | Ph | Ph | H | Ph | Ph |
| 141015 | CN | CN | H | H | H |
| 141016 | H | H | CN | H | H |
| 141017 | H | H | H | CN | CN |
| 141018 | CN | CN | CN | H | H |
| 141019 | H | H | CN | CN | CN |
| 141020 | CN | CN | H | CN | CN |
| 141021 | 9-Cbz | 9-Cbz | H | H | H |
| 141022 | H | H | 9-Cbz | H | H |
| 141023 | H | H | H | 9-Cbz | 9-Cbz |
| 141024 | 9-Cbz | 9-Cbz | 9-Cbz | H | H |
| 141025 | H | H | 9-Cbz | 9-Cbz | 9-Cbz |
| 141026 | 9-Cbz | 9-Cbz | H | 9-Cbz | 9-Cbz |
| 141027 | Me | Me | H | H | H |
| 141028 | H | H | Me | H | H |
| 141029 | H | H | H | Me | Me |
| 141030 | Me | Me | Me | H | H |
| 141031 | H | H | Me | Me | Me |
| 141032 | Me | Me | H | Me | Me |
| 141033 | CD$_3$ | CD3 | H | H | H |
| 141034 | H | H | CD3 | H | H |
| 141035 | H | H | H | CD3 | CD3 |
| 141036 | CD3 | CD3 | CD3 | H | H |
| 141037 | H | H | CD3 | CD3 | CD3 |
| 141038 | CD3 | CD3 | H | CD3 | CD3 |
| 141039 | 4-t-BuPh | 4-t-BuPh | H | H | H |
| 141040 | H | H | 4-t-BuPh | H | H |
| 141041 | H | H | H | 4-t-BuPh | 4-t-BuPh |
| 141042 | 4-t-BuPh | 4-t-BuPh | 4-t-BuPh | H | H |
| 141043 | H | H | 4-t-BuPh | 4-t-BuPh | 4-t-BuPh |
| 141044 | 4-t-BuPh | 4-t-BuPh | H | 4-t-BuPh | 4-t-BuPh |
| 141045 | 1,3-di-t-BuPh | 1,3-di-t-BuPh | H | H | H |
| 141046 | H | H | 1,3-di-t-BuPh | H | H |
| 141047 | H | H | H | 1,3-di-t-BuPh | 1,3-di-t-BuPh |
| 141048 | 1,3-di-t-BuPh | 1,3-di-t-BuPh | 1,3-di-t-BuPh | H | H |
| 141049 | H | H | 1,3-di-t-BuPh | 1,3-di-t-BuPh | 1,3-di-t-BuPh |
| 141050 | 1,3-di-t-BuPh | 1,3-di-t-BuPh | H | 1,3-di-t-BuPh | 1,3-di-t-BuPh |
| 141051 | t-Bu | t-Bu | Ph | H | H |
| 141052 | t-Bu | t-Bu | CN | H | H |
| 141053 | t-Bu | t-Bu | DPA | H | H |
| 141054 | t-Bu | t-Bu | 2-DBF | H | H |
| 141055 | t-Bu | t-Bu | 2-DBT | H | H |
| 141056 | t-Bu | t-Bu | 4-t-BuPh | H | H |
| 141057 | t-Bu | t-Bu | 1,3-di-t-BuPh | H | H |
| 141058 | t-Bu | t-Bu | 9-Cbz | H | H |
| 141059 | t-Bu | t-Bu | Ph | t-Bu | t-Bu |
| 141060 | t-Bu | t-Bu | CN | t-Bu | t-Bu |
| 141061 | t-Bu | t-Bu | DPA | t-Bu | t-Bu |
| 141062 | t-Bu | t-Bu | 2-DBF | t-Bu | t-Bu |
| 141063 | t-Bu | t-Bu | 2-DBT | t-Bu | t-Bu |
| 141064 | t-Bu | t-Bu | 4-t-BuPh | t-Bu | t-Bu |
| 141065 | t-Bu | t-Bu | 1,3-di-t-BuPh | t-Bu | t-Bu |
| 141066 | t-Bu | t-Bu | 9-Cbz | t-Bu | t-Bu |
| 141067 | t-Bu | t-Bu | t-Bu | Ph | Ph |
| 141068 | t-Bu | t-Bu | Ph | Ph | Ph |

TABLE 6-continued

| Compound No. | $R_{11b}$ | $R_{12c}$ | $R_{15C}$ | $R_{18b}$ | $R_{19b}$ |
|---|---|---|---|---|---|
| 141069 | t-Bu | t-Bu | CN | Ph | Ph |
| 141070 | t-Bu | t-Bu | DPA | Ph | Ph |
| 141071 | t-Bu | t-Bu | 2-DBF | Ph | Ph |
| 141072 | t-Bu | t-Bu | 2-DBT | Ph | Ph |
| 141073 | t-Bu | t-Bu | 4-t-BuPh | Ph | Ph |
| 141074 | t-Bu | t-Bu | 1,3-di-t-BuPh | Ph | Ph |
| 141075 | t-Bu | t-Bu | 9-Cbz | Ph | Ph |
| 141076 | t-Bu | t-Bu | t-Bu | CN | CN |
| 141077 | t-Bu | t-Bu | Ph | CN | CN |
| 141078 | t-Bu | t-Bu | CN | CN | CN |
| 141079 | t-Bu | t-Bu | DPA | CN | CN |
| 141080 | t-Bu | t-Bu | 2-DBF | CN | CN |
| 141081 | t-Bu | t-Bu | 2-DBT | CN | CN |
| 141082 | t-Bu | t-Bu | 4-t-BuPh | CN | CN |
| 141083 | t-Bu | t-Bu | 1,3-di-t-BuPh | CN | CN |
| 141084 | t-Bu | t-Bu | 9-Cbz | CN | CN |
| 141085 | t-Bu | t-Bu | t-Bu | 9-Cbz | 9-Cbz |
| 141086 | t-Bu | t-Bu | Ph | 9-Cbz | 9-Cbz |
| 141087 | t-Bu | t-Bu | CN | 9-Cbz | 9-Cbz |
| 141088 | t-Bu | t-Bu | DPA | 9-Cbz | 9-Cbz |
| 141089 | t-Bu | t-Bu | 2-DBF | 9-Cbz | 9-Cbz |
| 141090 | t-Bu | t-Bu | 2-DBT | 9-Cbz | 9-Cbz |
| 141091 | t-Bu | t-Bu | 4-t-BuPh | 9-Cbz | 9-Cbz |
| 141092 | t-Bu | t-Bu | 1,3-di-t-BuPh | 9-Cbz | 9-Cbz |
| 141093 | t-Bu | t-Bu | 9-Cbz | 9-Cbz | 9-Cbz |
| 141094 | t-Bu | t-Bu | t-Bu | 4-t-BuPh | 4-t-BuPh |
| 141095 | t-Bu | t-Bu | Ph | 4-t-BuPh | 4-t-BuPh |
| 141096 | t-Bu | t-Bu | CN | 4-t-BuPh | 4-t-BuPh |
| 141097 | t-Bu | t-Bu | DPA | 4-t-BuPh | 4-t-BuPh |
| 141098 | t-Bu | t-Bu | 2-DBF | 4-t-BuPh | 4-t-BuPh |
| 141099 | t-Bu | t-Bu | 2-DBT | 4-t-BuPh | 4-t-BuPh |
| 141100 | t-Bu | t-Bu | 4-t-BuPh | 4-t-BuPh | 4-t-BuPh |
| 141101 | t-Bu | t-Bu | 1,3-di-t-BuPh | 4-t-BuPh | 4-t-BuPh |
| 141102 | t-Bu | t-Bu | 9-Cbz | 4-t-BuPh | 4-t-BuPh |
| 141103 | t-Bu | t-Bu | t-Bu | 1,3-di-t-BuPh | 1,3-di-t-BuPh |
| 141104 | t-Bu | t-Bu | Ph | 1,3-di-t-BuPh | 1,3-di-t-BuPh |
| 141105 | t-Bu | t-Bu | CN | 1,3-di-t-BuPh | 1,3-di-t-BuPh |
| 141106 | t-Bu | t-Bu | DPA | 1,3-di-t-BuPh | 1,3-di-t-BuPh |
| 141107 | t-Bu | t-Bu | 2-DBF | 1,3-di-t-BuPh | 1,3-di-t-BuPh |
| 141108 | t-Bu | t-Bu | 2-DBT | 1,3-di-t-BuPh | 1,3-di-t-BuPh |
| 141109 | t-Bu | t-Bu | 4-t-BuPh | 1,3-di-t-BuPh | 1,3-di-t-BuPh |
| 141110 | t-Bu | t-Bu | 1,3-di-t-BuPh | 1,3-di-t-BuPh | 1,3-di-t-BuPh |
| 141111 | t-Bu | t-Bu | 9-Cbz | 1,3-di-t-BuPh | 1,3-di-t-BuPh |
| 141112 | Ph | Ph | t-Bu | H | H |
| 141113 | Ph | Ph | CN | H | H |
| 141114 | Ph | Ph | DPA | H | H |
| 141115 | Ph | Ph | 2-DBF | H | H |
| 141116 | Ph | Ph | 2-DBT | H | H |
| 141117 | Ph | Ph | 4-t-BuPh | H | H |
| 141118 | Ph | Ph | 1,3-di-t-BuPh | H | H |
| 141119 | Ph | Ph | 9-Cbz | H | H |
| 141120 | Ph | Ph | t-Bu | t-Bu | t-Bu |
| 141121 | Ph | Ph | Ph | t-Bu | t-Bu |
| 141122 | Ph | Ph | CN | t-Bu | t-Bu |
| 141123 | Ph | Ph | DPA | t-Bu | t-Bu |
| 141124 | Ph | Ph | 2-DBF | t-Bu | t-Bu |
| 141125 | Ph | Ph | 2-DBT | t-Bu | t-Bu |
| 141126 | Ph | Ph | 4-t-BuPh | t-Bu | t-Bu |
| 141127 | Ph | Ph | 1,3-di-t-BuPh | t-Bu | t-Bu |
| 141128 | Ph | Ph | 9-Cbz | t-Bu | t-Bu |
| 141129 | Ph | Ph | Ph | Ph | Ph |
| 141130 | Ph | Ph | CN | Ph | Ph |
| 141131 | Ph | Ph | DPA | Ph | Ph |
| 141132 | Ph | Ph | 2-DBF | Ph | Ph |
| 141133 | Ph | Ph | 2-DBT | Ph | Ph |
| 141134 | Ph | Ph | 4-t-BuPh | Ph | Ph |
| 141135 | Ph | Ph | 1,3-di-t-BuPh | Ph | Ph |
| 141136 | Ph | Ph | 9-Cbz | Ph | Ph |
| 141137 | Ph | Ph | t-Bu | CN | CN |
| 141138 | Ph | Ph | Ph | CN | CN |
| 141139 | Ph | Ph | CN | CN | CN |
| 141140 | Ph | Ph | DPA | CN | CN |
| 141141 | Ph | Ph | 2-DBF | CN | CN |
| 141142 | Ph | Ph | 2-DBT | CN | CN |
| 141143 | Ph | Ph | 4-t-BuPh | CN | CN |
| 141144 | Ph | Ph | 1,3-di-t-BuPh | CN | CN |
| 141145 | Ph | Ph | 9-Cbz | CN | CN |
| 141146 | Ph | Ph | t-Bu | 9-Cbz | 9-Cbz |
| 141147 | Ph | Ph | Ph | 9-Cbz | 9-Cbz |
| 141148 | Ph | Ph | CN | 9-Cbz | 9-Cbz |
| 141149 | Ph | Ph | DPA | 9-Cbz | 9-Cbz |
| 141150 | Ph | Ph | 2-DBF | 9-Cbz | 9-Cbz |
| 141151 | Ph | Ph | 2-DBT | 9-Cbz | 9-Cbz |
| 141152 | Ph | Ph | 4-t-BuPh | 9-Cbz | 9-Cbz |
| 141153 | Ph | Ph | 1,3-di-t-BuPh | 9-Cbz | 9-Cbz |

TABLE 6-continued

| Compound No. | $R_{11b}$ | $R_{12c}$ | $R_{15C}$ | $R_{18b}$ | $R_{19b}$ |
|---|---|---|---|---|---|
| 141154 | Ph | Ph | 9-Cbz | 9-Cbz | 9-Cbz |
| 141155 | Ph | Ph | t-Bu | 4-t-BuPh | 4-t-BuPh |
| 141156 | Ph | Ph | Ph | 4-t-BuPh | 4-t-BuPh |
| 141157 | Ph | Ph | CN | 4-t-BuPh | 4-t-BuPh |
| 141158 | Ph | Ph | DPA | 4-t-BuPh | 4-t-BuPh |
| 141159 | Ph | Ph | 2-DBF | 4-t-BuPh | 4-t-BuPh |
| 141160 | Ph | Ph | 2-DBT | 4-t-BuPh | 4-t-BuPh |
| 141161 | Ph | Ph | 4-t-BuPh | 4-t-BuPh | 4-t-BuPh |
| 141162 | Ph | Ph | 1,3-di-t-BuPh | 4-t-BuPh | 4-t-BuPh |
| 141163 | Ph | Ph | 9-Cbz | 4-t-BuPh | 4-t-BuPh |
| 141164 | Ph | Ph | t-Bu | 1,3-di-t-BuPh | 1,3-di-t-BuPh |
| 141165 | Ph | Ph | Ph | 1,3-di-t-BuPh | 1,3-di-t-BuPh |
| 141166 | Ph | Ph | CN | 1,3-di-t-BuPh | 1,3-di-t-BuPh |
| 141167 | Ph | Ph | DPA | 1,3-di-t-BuPh | 1,3-di-t-BuPh |
| 141168 | Ph | Ph | 2-DBF | 1,3-di-t-BuPh | 1,3-di-t-BuPh |
| 141169 | Ph | Ph | 2-DBT | 1,3-di-t-BuPh | 1,3-di-t-BuPh |
| 141170 | Ph | Ph | 4-t-BuPh | 1,3-di-t-BuPh | 1,3-di-t-BuPh |
| 141171 | Ph | Ph | 1,3-di-t-BuPh | 1,3-di-t-BuPh | 1,3-di-t-BuPh |
| 141172 | Ph | Ph | 9-Cbz | 1,3-di-t-BuPh | 1,3-di-t-BuPh |
| 141173 | 9-Cbz | 9-Cbz | t-Bu | H | H |
| 141174 | 9-Cbz | 9-Cbz | Ph | H | H |
| 141175 | 9-Cbz | 9-Cbz | CN | H | H |
| 141176 | 9-Cbz | 9-Cbz | DPA | H | H |
| 141177 | 9-Cbz | 9-Cbz | 2-DBF | H | H |
| 141178 | 9-Cbz | 9-Cbz | 2-DBT | H | H |
| 141179 | 9-Cbz | 9-Cbz | 4-t-BuPh | H | H |
| 141180 | 9-Cbz | 9-Cbz | 1,3-di-t-BuPh | H | H |
| 141181 | 9-Cbz | 9-Cbz | t-Bu | t-Bu | t-Bu |
| 141182 | 9-Cbz | 9-Cbz | Ph | t-Bu | t-Bu |
| 141183 | 9-Cbz | 9-Cbz | CN | t-Bu | t-Bu |
| 141184 | 9-Cbz | 9-Cbz | DPA | t-Bu | t-Bu |
| 141185 | 9-Cbz | 9-Cbz | 2-DBF | t-Bu | t-Bu |
| 141186 | 9-Cbz | 9-Cbz | 2-DBT | t-Bu | t-Bu |
| 141187 | 9-Cbz | 9-Cbz | 4-t-BuPh | t-Bu | t-Bu |
| 141188 | 9-Cbz | 9-Cbz | 1,3-di-t-BuPh | t-Bu | t-Bu |
| 141189 | 9-Cbz | 9-Cbz | 9-Cbz | t-Bu | t-Bu |
| 141190 | 9-Cbz | 9-Cbz | t-Bu | Ph | Ph |
| 141191 | 9-Cbz | 9-Cbz | Ph | Ph | Ph |
| 141192 | 9-Cbz | 9-Cbz | CN | Ph | Ph |
| 141193 | 9-Cbz | 9-Cbz | DPA | Ph | Ph |
| 141194 | 9-Cbz | 9-Cbz | 2-DBF | Ph | Ph |
| 141195 | 9-Cbz | 9-Cbz | 2-DBT | Ph | Ph |
| 141196 | 9-Cbz | 9-Cbz | 4-t-BuPh | Ph | Ph |
| 141197 | 9-Cbz | 9-Cbz | 1,3-di-t-BuPh | Ph | Ph |
| 141198 | 9-Cbz | 9-Cbz | 9-Cbz | Ph | Ph |
| 141199 | 9-Cbz | 9-Cbz | t-Bu | CN | CN |
| 141200 | 9-Cbz | 9-Cbz | Ph | CN | CN |
| 141201 | 9-Cbz | 9-Cbz | CN | CN | CN |
| 141202 | 9-Cbz | 9-Cbz | DPA | CN | CN |
| 141203 | 9-Cbz | 9-Cbz | 2-DBF | CN | CN |
| 141204 | 9-Cbz | 9-Cbz | 2-DBT | CN | CN |
| 141205 | 9-Cbz | 9-Cbz | 4-t-BuPh | CN | CN |
| 141206 | 9-Cbz | 9-Cbz | 1,3-di-t-BuPh | CN | CN |
| 141207 | 9-Cbz | 9-Cbz | 9-Cbz | CN | CN |
| 141208 | 9-Cbz | 9-Cbz | t-Bu | 9-Cbz | 9-Cbz |
| 141209 | 9-Cbz | 9-Cbz | Ph | 9-Cbz | 9-Cbz |
| 141210 | 9-Cbz | 9-Cbz | CN | 9-Cbz | 9-Cbz |
| 141211 | 9-Cbz | 9-Cbz | DPA | 9-Cbz | 9-Cbz |
| 141212 | 9-Cbz | 9-Cbz | 2-DBF | 9-Cbz | 9-Cbz |
| 141213 | 9-Cbz | 9-Cbz | 2-DBT | 9-Cbz | 9-Cbz |
| 141214 | 9-Cbz | 9-Cbz | 4-t-BuPh | 9-Cbz | 9-Cbz |
| 141215 | 9-Cbz | 9-Cbz | 1,3-di-t-BuPh | 9-Cbz | 9-Cbz |
| 141216 | 9-Cbz | 9-Cbz | 9-Cbz | 9-Cbz | 9-Cbz |
| 141217 | 9-Cbz | 9-Cbz | t-Bu | 4-t-BuPh | 4-t-BuPh |
| 141218 | 9-Cbz | 9-Cbz | Ph | 4-t-BuPh | 4-t-BuPh |
| 141219 | 9-Cbz | 9-Cbz | CN | 4-t-BuPh | 4-t-BuPh |
| 141220 | 9-Cbz | 9-Cbz | DPA | 4-t-BuPh | 4-t-BuPh |
| 141221 | 9-Cbz | 9-Cbz | 2-DBF | 4-t-BuPh | 4-t-BuPh |
| 141222 | 9-Cbz | 9-Cbz | 2-DBT | 4-t-BuPh | 4-t-BuPh |
| 141223 | 9-Cbz | 9-Cbz | 4-t-BuPh | 4-t-BuPh | 4-t-BuPh |
| 141224 | 9-Cbz | 9-Cbz | 1,3-di-t-BuPh | 4-t-BuPh | 4-t-BuPh |
| 141225 | 9-Cbz | 9-Cbz | 9-Cbz | 4-t-BuPh | 4-t-BuPh |
| 141226 | 9-Cbz | 9-Cbz | t-Bu | 1,3-di-t-BuPh | 1,3-di-t-BuPh |
| 141227 | 9-Cbz | 9-Cbz | Ph | 1,3-di-t-BuPh | 1,3-di-t-BuPh |
| 141228 | 9-Cbz | 9-Cbz | CN | 1,3-di-t-BuPh | 1,3-di-t-BuPh |
| 141229 | 9-Cbz | 9-Cbz | DPA | 1,3-di-t-BuPh | 1,3-di-t-BuPh |
| 141230 | 9-Cbz | 9-Cbz | 2-DBF | 1,3-di-t-BuPh | 1,3-di-t-BuPh |
| 141231 | 9-Cbz | 9-Cbz | 2-DBT | 1,3-di-t-BuPh | 1,3-di-t-BuPh |

TABLE 6-continued

| Compound No. | $R_{11b}$ | $R_{12c}$ | $R_{15C}$ | $R_{18b}$ | $R_{19b}$ |
|---|---|---|---|---|---|
| 141232 | 9-Cbz | 9-Cbz | 4-t-BuPh | 1,3-di-t-BuPh | 1,3-di-t-BuPh |
| 141233 | 9-Cbz | 9-Cbz | 1,3-di-t-BuPh | 1,3-di-t-BuPh | 1,3-di-t-BuPh |
| 141234 | 9-Cbz | 9-Cbz | 9-Cbz | 1,3-di-t-BuPh | 1,3-di-t-BuPh |
| 141235 | CN | CN | t-Bu | H | H |
| 141236 | CN | CN | Ph | H | H |
| 141237 | CN | CN | DPA | H | H |
| 141238 | CN | CN | 2-DBF | H | H |
| 141239 | CN | CN | 2-DBT | H | H |
| 141240 | CN | CN | 4-t-BuPh | H | H |
| 141241 | CN | CN | 1,3-di-t-BuPh | H | H |
| 141242 | CN | CN | 9-Cbz | H | H |
| 141243 | CN | CN | t-Bu | t-Bu | t-Bu |
| 141244 | CN | CN | Ph | t-Bu | t-Bu |
| 141245 | CN | CN | CN | t-Bu | t-Bu |
| 141246 | CN | CN | DPA | t-Bu | t-Bu |
| 141247 | CN | CN | 2-DBF | t-Bu | t-Bu |
| 141248 | CN | CN | 2-DBT | t-Bu | t-Bu |
| 141249 | CN | CN | 4-t-BuPh | t-Bu | t-Bu |
| 141250 | CN | CN | 1,3-di-t-BuPh | t-Bu | t-Bu |
| 141251 | CN | CN | 9-Cbz | t-Bu | t-Bu |
| 141252 | CN | CN | t-Bu | Ph | Ph |
| 141253 | CN | CN | Ph | Ph | Ph |
| 141254 | CN | CN | CN | Ph | Ph |
| 141255 | CN | CN | DPA | Ph | Ph |
| 141256 | CN | CN | 2-DBF | Ph | Ph |
| 141257 | CN | CN | 2-DBT | Ph | Ph |
| 141258 | CN | CN | 4-t-BuPh | Ph | Ph |
| 141259 | CN | CN | 1,3-di-t-BuPh | Ph | Ph |
| 141260 | CN | CN | 9-Cbz | Ph | Ph |
| 141261 | CN | CN | t-Bu | CN | CN |
| 141262 | CN | CN | Ph | CN | CN |
| 141263 | CN | CN | CN | CN | CN |
| 141264 | CN | CN | DPA | CN | CN |
| 141265 | CN | CN | 2-DBF | CN | CN |
| 141266 | CN | CN | 2-DBT | CN | CN |
| 141267 | CN | CN | 4-t-BuPh | CN | CN |
| 141268 | CN | CN | 1,3-di-t-BuPh | CN | CN |
| 141269 | CN | CN | 9-Cbz | CN | CN |
| 141270 | CN | CN | t-Bu | 9-Cbz | 9-Cbz |
| 141271 | CN | CN | Ph | 9-Cbz | 9-Cbz |
| 141272 | CN | CN | CN | 9-Cbz | 9-Cbz |
| 141273 | CN | CN | DPA | 9-Cbz | 9-Cbz |
| 141274 | CN | CN | 2-DBF | 9-Cbz | 9-Cbz |
| 141275 | CN | CN | 2-DBT | 9-Cbz | 9-Cbz |
| 141276 | CN | CN | 4-t-BuPh | 9-Cbz | 9-Cbz |
| 141277 | CN | CN | 1,3-di-t-BuPh | 9-Cbz | 9-Cbz |
| 141278 | CN | CN | 9-Cbz | 9-Cbz | 9-Cbz |
| 141279 | CN | CN | t-Bu | 4-t-BuPh | 4-t-BuPh |
| 141280 | CN | CN | Ph | 4-t-BuPh | 4-t-BuPh |
| 141281 | CN | CN | CN | 4-t-BuPh | 4-t-BuPh |
| 141282 | CN | CN | DPA | 4-t-BuPh | 4-t-BuPh |
| 141283 | CN | CN | 2-DBF | 4-t-BuPh | 4-t-BuPh |
| 141284 | CN | CN | 2-DBT | 4-t-BuPh | 4-t-BuPh |
| 141285 | CN | CN | 4-t-BuPh | 4-t-BuPh | 4-t-BuPh |
| 141286 | CN | CN | 1,3-di-t-BuPh | 4-t-BuPh | 4-t-BuPh |
| 141287 | CN | CN | 9-Cbz | 4-t-BuPh | 4-t-BuPh |
| 141288 | CN | CN | t-Bu | 1,3-di-t-BuPh | 1,3-di-t-BuPh |
| 141289 | CN | CN | Ph | 1,3-di-t-BuPh | 1,3-di-t-BuPh |
| 141290 | CN | CN | CN | 1,3-di-t-BuPh | 1,3-di-t-BuPh |
| 141291 | CN | CN | DPA | 1,3-di-t-BuPh | 1,3-di-t-BuPh |
| 141292 | CN | CN | 2-DBF | 1,3-di-t-BuPh | 1,3-di-t-BuPh |
| 141293 | CN | CN | 2-DBT | 1,3-di-t-BuPh | 1,3-di-t-BuPh |
| 141294 | CN | CN | 4-t-BuPh | 1,3-di-t-BuPh | 1,3-di-t-BuPh |
| 141295 | CN | CN | 1,3-di-t-BuPh | 1,3-di-t-BuPh | 1,3-di-t-BuPh |
| 141296 | CN | CN | 9-Cbz | 1,3-di-t-BuPh | 1,3-di-t-BuPh |
| 141297 | 4-t-BuPh | 4-t-BuPh | t-Bu | H | H |
| 141298 | 4-t-BuPh | 4-t-BuPh | Ph | H | H |
| 141299 | 4-t-BuPh | 4-t-BuPh | CN | H | H |
| 141300 | 4-t-BuPh | 4-t-BuPh | DPA | H | H |
| 141301 | 4-t-BuPh | 4-t-BuPh | 2-DBF | H | H |
| 141302 | 4-t-BuPh | 4-t-BuPh | 2-DBT | H | H |
| 141303 | 4-t-BuPh | 4-t-BuPh | 1,3-di-t-BuPh | H | H |
| 141304 | 4-t-BuPh | 4-t-BuPh | 9-Cbz | H | H |
| 141305 | 4-t-BuPh | 4-t-BuPh | t-Bu | t-Bu | t-Bu |
| 141306 | 4-t-BuPh | 4-t-BuPh | Ph | t-Bu | t-Bu |
| 141307 | 4-t-BuPh | 4-t-BuPh | CN | t-Bu | t-Bu |
| 141308 | 4-t-BuPh | 4-t-BuPh | DPA | t-Bu | t-Bu |
| 141309 | 4-t-BuPh | 4-t-BuPh | 2-DBF | t-Bu | t-Bu |
| 141310 | 4-t-BuPh | 4-t-BuPh | 2-DBT | t-Bu | t-Bu |

TABLE 6-continued

| Compound No. | R$_{11b}$ | R$_{12c}$ | R$_{15C}$ | R$_{18b}$ | R$_{19b}$ |
|---|---|---|---|---|---|
| 141311 | 4-t-BuPh | 4-t-BuPh | 4-t-BuPh | t-Bu | t-Bu |
| 141312 | 4-t-BuPh | 4-t-BuPh | 1,3-di-t-BuPh | t-Bu | t-Bu |
| 141313 | 4-t-BuPh | 4-t-BuPh | 9-Cbz | t-Bu | t-Bu |
| 141314 | 4-t-BuPh | 4-t-BuPh | t-Bu | Ph | Ph |
| 141315 | 4-t-BuPh | 4-t-BuPh | Ph | Ph | Ph |
| 141316 | 4-t-BuPh | 4-t-BuPh | CN | Ph | Ph |
| 141317 | 4-t-BuPh | 4-t-BuPh | DPA | Ph | Ph |
| 141318 | 4-t-BuPh | 4-t-BuPh | 2-DBF | Ph | Ph |
| 141319 | 4-t-BuPh | 4-t-BuPh | 2-DBT | Ph | Ph |
| 141320 | 4-t-BuPh | 4-t-BuPh | 4-t-BuPh | Ph | Ph |
| 141321 | 4-t-BuPh | 4-t-BuPh | 1,3-di-t-BuPh | Ph | Ph |
| 141322 | 4-t-BuPh | 4-t-BuPh | 9-Cbz | Ph | Ph |
| 141323 | 4-t-BuPh | 4-t-BuPh | t-Bu | CN | CN |
| 141324 | 4-t-BuPh | 4-t-BuPh | Ph | CN | CN |
| 141325 | 4-t-BuPh | 4-t-BuPh | CN | CN | CN |
| 141326 | 4-t-BuPh | 4-t-BuPh | DPA | CN | CN |
| 141327 | 4-t-BuPh | 4-t-BuPh | 2-DBF | CN | CN |
| 141328 | 4-t-BuPh | 4-t-BuPh | 2-DBT | CN | CN |
| 141329 | 4-t-BuPh | 4-t-BuPh | 4-t-BuPh | CN | CN |
| 141330 | 4-t-BuPh | 4-t-BuPh | 1,3-di-t-BuPh | CN | CN |
| 141331 | 4-t-BuPh | 4-t-BuPh | 9-Cbz | CN | CN |
| 141332 | 4-t-BuPh | 4-t-BuPh | t-Bu | 9-Cbz | 9-Cbz |
| 141333 | 4-t-BuPh | 4-t-BuPh | Ph | 9-Cbz | 9-Cbz |
| 141334 | 4-t-BuPh | 4-t-BuPh | CN | 9-Cbz | 9-Cbz |
| 141335 | 4-t-BuPh | 4-t-BuPh | DPA | 9-Cbz | 9-Cbz |
| 141336 | 4-t-BuPh | 4-t-BuPh | 2-DBF | 9-Cbz | 9-Cbz |
| 141337 | 4-t-BuPh | 4-t-BuPh | 2-DBT | 9-Cbz | 9-Cbz |
| 141338 | 4-t-BuPh | 4-t-BuPh | 4-t-BuPh | 9-Cbz | 9-Cbz |
| 141339 | 4-t-BuPh | 4-t-BuPh | 1,3-di-t-BuPh | 9-Cbz | 9-Cbz |
| 141340 | 4-t-BuPh | 4-t-BuPh | 9-Cbz | 9-Cbz | 9-Cbz |
| 141341 | 4-t-BuPh | 4-t-BuPh | t-Bu | 4-t-BuPh | 4-t-BuPh |
| 141342 | 4-t-BuPh | 4-t-BuPh | Ph | 4-t-BuPh | 4-t-BuPh |
| 141343 | 4-t-BuPh | 4-t-BuPh | CN | 4-t-BuPh | 4-t-BuPh |
| 141344 | 4-t-BuPh | 4-t-BuPh | DPA | 4-t-BuPh | 4-t-BuPh |
| 141345 | 4-t-BuPh | 4-t-BuPh | 2-DBF | 4-t-BuPh | 4-t-BuPh |
| 141346 | 4-t-BuPh | 4-t-BuPh | 2-DBT | 4-t-BuPh | 4-t-BuPh |
| 141347 | 4-t-BuPh | 4-t-BuPh | 4-t-BuPh | 4-t-BuPh | 4-t-BuPh |
| 141348 | 4-t-BuPh | 4-t-BuPh | 1,3-di-t-BuPh | 4-t-BuPh | 4-t-BuPh |
| 141349 | 4-t-BuPh | 4-t-BuPh | 9-Cbz | 4-t-BuPh | 4-t-BuPh |
| 141350 | 4-t-BuPh | 4-t-BuPh | t-Bu | 1,3-di-t-BuPh | 1,3-di-t-BuPh |
| 141351 | 4-t-BuPh | 4-t-BuPh | Ph | 1,3-di-t-BuPh | 1,3-di-t-BuPh |
| 141352 | 4-t-BuPh | 4-t-BuPh | CN | 1,3-di-t-BuPh | 1,3-di-t-BuPh |
| 141353 | 4-t-BuPh | 4-t-BuPh | DPA | 1,3-di-t-BuPh | 1,3-di-t-BuPh |
| 141354 | 4-t-BuPh | 4-t-BuPh | 2-DBF | 1,3-di-t-BuPh | 1,3-di-t-BuPh |
| 141355 | 4-t-BuPh | 4-t-BuPh | 2-DBT | 1,3-di-t-BuPh | 1,3-di-t-BuPh |
| 141356 | 4-t-BuPh | 4-t-BuPh | 4-t-BuPh | 1,3-di-t-BuPh | 1,3-di-t-BuPh |
| 141357 | 4-t-BuPh | 4-t-BuPh | 1,3-di-t-BuPh | 1,3-di-t-BuPh | 1,3-di-t-BuPh |
| 141358 | 4-t-BuPh | 4-t-BuPh | 9-Cbz | 1,3-di-t-BuPh | 1,3-di-t-BuPh |
| 141359 | 1,3-di-t-BuPh | 1,3-di-t-BuPh | t-Bu | H | H |
| 141360 | 1,3-di-t-BuPh | 1,3-di-t-BuPh | Ph | H | H |
| 141361 | 1,3-di-t-BuPh | 1,3-di-t-BuPh | CN | H | H |
| 141362 | 1,3-di-t-BuPh | 1,3-di-t-BuPh | DPA | H | H |
| 141363 | 1,3-di-t-BuPh | 1,3-di-t-BuPh | 2-DBF | H | H |
| 141364 | 1,3-di-t-BuPh | 1,3-di-t-BuPh | 2-DBT | H | H |
| 141365 | 1,3-di-t-BuPh | 1,3-di-t-BuPh | 4-t-BuPh | H | H |
| 141366 | 1,3-di-t-BuPh | 1,3-di-t-BuPh | 9-Cbz | H | H |
| 141367 | 1,3-di-t-BuPh | 1,3-di-t-BuPh | t-Bu | t-Bu | t-Bu |
| 141368 | 1,3-di-t-BuPh | 1,3-di-t-BuPh | Ph | t-Bu | t-Bu |
| 141369 | 1,3-di-t-BuPh | 1,3-di-t-BuPh | CN | t-Bu | t-Bu |
| 141370 | 1,3-di-t-BuPh | 1,3-di-t-BuPh | DPA | t-Bu | t-Bu |
| 141371 | 1,3-di-t-BuPh | 1,3-di-t-BuPh | 2-DBF | t-Bu | t-Bu |
| 141372 | 1,3-di-t-BuPh | 1,3-di-t-BuPh | 2-DBT | t-Bu | t-Bu |

TABLE 6-continued

| Compound No. | $R_{11b}$ | $R_{12c}$ | $R_{15C}$ | $R_{18b}$ | $R_{19b}$ |
|---|---|---|---|---|---|
| 141373 | 1,3-di-t-BuPh | 1,3-di-t-BuPh | 4-t-BuPh | t-Bu | t-Bu |
| 141374 | 1,3-di-t-BuPh | 1,3-di-t-BuPh | 1,3-di-t-BuPh | t-Bu | t-Bu |
| 141375 | 1,3-di-t-BuPh | 1,3-di-t-BuPh | 9-Cbz | t-Bu | t-Bu |
| 141376 | 1,3-di-t-BuPh | 1,3-di-t-BuPh | t-Bu | Ph | Ph |
| 141377 | 1,3-di-t-BuPh | 1,3-di-t-BuPh | Ph | Ph | Ph |
| 141378 | 1,3-di-t-BuPh | 1,3-di-t-BuPh | CN | Ph | Ph |
| 141379 | 1,3-di-t-BuPh | 1,3-di-t-BuPh | DPA | Ph | Ph |
| 141380 | 1,3-di-t-BuPh | 1,3-di-t-BuPh | 2-DBF | Ph | Ph |
| 141381 | 1,3-di-t-BuPh | 1,3-di-t-BuPh | 2-DBT | Ph | Ph |
| 141382 | 1,3-di-t-BuPh | 1,3-di-t-BuPh | 4-t-BuPh | Ph | Ph |
| 141383 | 1,3-di-t-BuPh | 1,3-di-t-BuPh | 1,3-di-t-BuPh | Ph | Ph |
| 141384 | 1,3-di-t-BuPh | 1,3-di-t-BuPh | 9-Cbz | Ph | Ph |
| 141385 | 1,3-di-t-BuPh | 1,3-di-t-BuPh | t-Bu | CN | CN |
| 141386 | 1,3-di-t-BuPh | 1,3-di-t-BuPh | Ph | CN | CN |
| 141387 | 1,3-di-t-BuPh | 1,3-di-t-BuPh | CN | CN | CN |
| 141388 | 1,3-di-t-BuPh | 1,3-di-t-BuPh | DPA | CN | CN |
| 141389 | 1,3-di-t-BuPh | 1,3-di-t-BuPh | 2-DBF | CN | CN |
| 141390 | 1,3-di-t-BuPh | 1,3-di-t-BuPh | 2-DBT | CN | CN |
| 141391 | 1,3-di-t-BuPh | 1,3-di-t-BuPh | 4-t-BuPh | CN | CN |
| 141392 | 1,3-di-t-BuPh | 1,3-di-t-BuPh | 1,3-di-t-BuPh | CN | CN |
| 141393 | 1,3-di-t-BuPh | 1,3-di-t-BuPh | 9-Cbz | CN | CN |
| 141394 | 1,3-di-t-BuPh | 1,3-di-t-BuPh | t-Bu | 9-Cbz | 9-Cbz |
| 141395 | 1,3-di-t-BuPh | 1,3-di-t-BuPh | Ph | 9-Cbz | 9-Cbz |
| 141396 | 1,3-di-t-BuPh | 1,3-di-t-BuPh | CN | 9-Cbz | 9-Cbz |
| 141397 | 1,3-di-t-BuPh | 1,3-di-t-BuPh | DPA | 9-Cbz | 9-Cbz |
| 141398 | 1,3-di-t-BuPh | 1,3-di-t-BuPh | 2-DBF | 9-Cbz | 9-Cbz |
| 141399 | 1,3-di-t-BuPh | 1,3-di-t-BuPh | 2-DBT | 9-Cbz | 9-Cbz |
| 141400 | 1,3-di-t-BuPh | 1,3-di-t-BuPh | 4-t-BuPh | 9-Cbz | 9-Cbz |
| 141401 | 1,3-di-t-BuPh | 1,3-di-t-BuPh | 1,3-di-t-BuPh | 9-Cbz | 9-Cbz |
| 141402 | 1,3-di-t-BuPh | 1,3-di-t-BuPh | 9-Cbz | 9-Cbz | 9-Cbz |
| 141403 | 1,3-di-t-BuPh | 1,3-di-t-BuPh | t-Bu | 4-t-BuPh | 4-t-BuPh |
| 141404 | 1,3-di-t-BuPh | 1,3-di-t-BuPh | Ph | 4-t-BuPh | 4-t-BuPh |
| 141405 | 1,3-di-t-BuPh | 1,3-di-t-BuPh | CN | 4-t-BuPh | 4-t-BuPh |
| 141406 | 1,3-di-t-BuPh | 1,3-di-t-BuPh | DPA | 4-t-BuPh | 4-t-BuPh |
| 141407 | 1,3-di-t-BuPh | 1,3-di-t-BuPh | 2-DBF | 4-t-BuPh | 4-t-BuPh |
| 141408 | 1,3-di-t-BuPh | 1,3-di-t-BuPh | 2-DBT | 4-t-BuPh | 4-t-BuPh |
| 141409 | 1,3-di-t-BuPh | 1,3-di-t-BuPh | 4-t-BuPh | 4-t-BuPh | 4-t-BuPh |
| 141410 | 1,3-di-t-BuPh | 1,3-di-t-BuPh | 1,3-di-t-BuPh | 4-t-BuPh | 4-t-BuPh |
| 141411 | 1,3-di-t-BuPh | 1,3-di-t-BuPh | 9-Cbz | 4-t-BuPh | 4-t-BuPh |
| 141412 | 1,3-di-t-BuPh | 1,3-di-t-BuPh | t-Bu | 1,3-di-t-BuPh | 1,3-di-t-BuPh |
| 141413 | 1,3-di-t-BuPh | 1,3-di-t-BuPh | Ph | 1,3-di-t-BuPh | 1,3-di-t-BuPh |
| 141414 | 1,3-di-t-BuPh | 1,3-di-t-BuPh | CN | 1,3-di-t-BuPh | 1,3-di-t-BuPh |
| 141415 | 1,3-di-t-BuPh | 1,3-di-t-BuPh | DPA | 1,3-di-t-BuPh | 1,3-di-t-BuPh |
| 141416 | 1,3-di-t-BuPh | 1,3-di-t-BuPh | 2-DBF | 1,3-di-t-BuPh | 1,3-di-t-BuPh |
| 141417 | 1,3-di-t-BuPh | 1,3-di-t-BuPh | 2-DBT | 1,3-di-t-BuPh | 1,3-di-t-BuPh |
| 141418 | 1,3-di-t-BuPh | 1,3-di-t-BuPh | 4-t-BuPh | 1,3-di-t-BuPh | 1,3-di-t-BuPh |
| 141419 | 1,3-di-t-BuPh | 1,3-di-t-BuPh | 1,3-di-t-BuPh | 1,3-di-t-BuPh | 1,3-di-t-BuPh |
| 141420 | 1,3-di-t-BuPh | 1,3-di-t-BuPh | 9-Cbz | 1,3-di-t-BuPh | 1,3-di-t-BuPh |

Group HC7

The heterocyclic compound may be represented by Formula 14-3, and substituents may be defined as shown in Table 7.

TABLE 7

| Compound No. | $R_{11b}$ | $R_{12c}$ | $R_{15C}$ | $R_{18b}$ | $R_{19b}$ |
|---|---|---|---|---|---|
| 143001 | t-Bu | t-Bu | t-Bu | t-Bu | t-Bu |
| 143002 | Ph | Ph | t-Bu | Ph | Ph |
| 143003 | t-Bu | t-Bu | H | H | H |
| 143004 | H | H | t-Bu | H | H |
| 143005 | H | H | H | t-Bu | t-Bu |
| 143006 | t-Bu | t-Bu | t-Bu | H | H |
| 143007 | H | H | t-Bu | t-Bu | t-Bu |
| 143008 | t-Bu | t-Bu | H | t-Bu | t-Bu |
| 143009 | Ph | Ph | H | H | H |
| 143010 | H | H | Ph | H | H |
| 143011 | H | H | H | Ph | Ph |
| 143012 | Ph | Ph | Ph | H | H |
| 143013 | H | H | Ph | Ph | Ph |
| 143014 | Ph | Ph | H | Ph | Ph |
| 143015 | CN | CN | H | H | H |
| 143016 | H | H | CN | H | H |
| 143017 | H | H | H | CN | CN |
| 143018 | CN | CN | CN | H | H |
| 143019 | H | H | CN | CN | CN |
| 143020 | CN | CN | H | CN | CN |
| 143021 | 9-Cbz | 9-Cbz | H | H | H |
| 143022 | H | H | 9-Cbz | H | H |
| 143023 | H | H | H | 9-Cbz | 9-Cbz |
| 143024 | 9-Cbz | 9-Cbz | 9-Cbz | H | H |
| 143025 | H | H | 9-Cbz | 9-Cbz | 9-Cbz |
| 143026 | 9-Cbz | 9-Cbz | H | 9-Cbz | 9-Cbz |
| 143027 | Me | Me | H | H | H |
| 143028 | H | H | Me | H | H |
| 143029 | H | H | H | Me | Me |
| 143030 | Me | Me | Me | H | H |
| 143031 | H | H | Me | Me | Me |
| 143032 | Me | Me | H | Me | Me |
| 143033 | CD3 | CD3 | H | H | H |
| 143034 | H | H | CD3 | H | H |
| 143035 | H | H | H | CD3 | CD3 |
| 143036 | CD3 | CD3 | CD3 | H | H |
| 143037 | H | H | CD3 | CD3 | CD3 |
| 143038 | CD3 | CD3 | H | CD3 | CD3 |
| 143039 | 4-t-BuPh | 4-t-BuPh | H | H | H |
| 143040 | H | H | 4-t-BuPh | H | H |
| 143041 | H | H | H | 4-t-BuPh | 4-t-BuPh |
| 143042 | 4-t-BuPh | 4-t-BuPh | 4-t-BuPh | H | H |
| 143043 | H | H | 4-t-BuPh | 4-t-BuPh | 4-t-BuPh |
| 143044 | 4-t-BuPh | 4-t-BuPh | H | 4-t-BuPh | 4-t-BuPh |
| 143045 | 1,3-di-t-BuPh | 1,3-di-t-BuPh | H | H | H |
| 143046 | H | H | 1,3-di-t-BuPh | H | H |
| 143047 | H | H | H | 1,3-di-t-BuPh | 1,3-di-t-BuPh |
| 143048 | 1,3-di-t-BuPh | 1,3-di-t-BuPh | 1,3-di-t-BuPh | H | H |
| 143049 | H | H | 1,3-di-t-BuPh | 1,3-di-t-BuPh | 1,3-di-t-BuPh |
| 143050 | 1,3-di-t-BuPh | 1,3-di-t-BuPh | H | 1,3-di-t-BuPh | 1,3-di-t-BuPh |
| 143051 | t-Bu | t-Bu | Ph | H | H |
| 143052 | t-Bu | t-Bu | CN | H | H |
| 143053 | t-Bu | t-Bu | DPA | H | H |
| 143054 | t-Bu | t-Bu | 2-DBF | H | H |
| 143055 | t-Bu | t-Bu | 2-DBT | H | H |
| 143056 | t-Bu | t-Bu | 4-t-BuPh | H | H |
| 143057 | t-Bu | t-Bu | 1,3-di-t-BuPh | H | H |
| 143058 | t-Bu | t-Bu | 9-Cbz | H | H |
| 143059 | t-Bu | t-Bu | Ph | t-Bu | t-Bu |
| 143060 | t-Bu | t-Bu | CN | t-Bu | t-Bu |
| 143061 | t-Bu | t-Bu | DPA | t-Bu | t-Bu |
| 143062 | t-Bu | t-Bu | 2-DBF | t-Bu | t-Bu |
| 143063 | t-Bu | t-Bu | 2-DBT | t-Bu | t-Bu |
| 143064 | t-Bu | t-Bu | 4-t-BuPh | t-Bu | t-Bu |
| 143065 | t-Bu | t-Bu | 1,3-di-t-BuPh | t-Bu | t-Bu |
| 143066 | t-Bu | t-Bu | 9-Cbz | t-Bu | t-Bu |
| 143067 | t-Bu | t-Bu | t-Bu | Ph | Ph |
| 143068 | t-Bu | t-Bu | Ph | Ph | Ph |
| 143069 | t-Bu | t-Bu | CN | Ph | Ph |
| 143070 | t-Bu | t-Bu | DPA | Ph | Ph |
| 143071 | t-Bu | t-Bu | 2-DBF | Ph | Ph |
| 143072 | t-Bu | t-Bu | 2-DBT | Ph | Ph |
| 143073 | t-Bu | t-Bu | 4-t-BuPh | Ph | Ph |
| 143074 | t-Bu | t-Bu | 1,3-di-t-BuPh | Ph | Ph |
| 143075 | t-Bu | t-Bu | 9-Cbz | Ph | Ph |
| 143076 | t-Bu | t-Bu | t-Bu | CN | CN |
| 143077 | t-Bu | t-Bu | Ph | CN | CN |
| 143078 | t-Bu | t-Bu | CN | CN | CN |
| 143079 | t-Bu | t-Bu | DPA | CN | CN |
| 143080 | t-Bu | t-Bu | 2-DBF | CN | CN |
| 143081 | t-Bu | t-Bu | 2-DBT | CN | CN |
| 143082 | t-Bu | t-Bu | 4-t-BuPh | CN | CN |
| 143083 | t-Bu | t-Bu | 1,3-di-t-BuPh | CN | CN |
| 143084 | t-Bu | t-Bu | 9-Cbz | CN | CN |
| 143085 | t-Bu | t-Bu | t-Bu | 9-Cbz | 9-Cbz |
| 143086 | t-Bu | t-Bu | Ph | 9-Cbz | 9-Cbz |
| 143087 | t-Bu | t-Bu | CN | 9-Cbz | 9-Cbz |
| 143088 | t-Bu | t-Bu | DPA | 9-Cbz | 9-Cbz |
| 143089 | t-Bu | t-Bu | 2-DBF | 9-Cbz | 9-Cbz |
| 143090 | t-Bu | t-Bu | 2-DBT | 9-Cbz | 9-Cbz |
| 143091 | t-Bu | t-Bu | 4-t-BuPh | 9-Cbz | 9-Cbz |
| 143092 | t-Bu | t-Bu | 1,3-di-t-BuPh | 9-Cbz | 9-Cbz |
| 143093 | t-Bu | t-Bu | 9-Cbz | 9-Cbz | 9-Cbz |
| 143094 | t-Bu | t-Bu | t-Bu | 4-t-BuPh | 4-t-BuPh |
| 143095 | t-Bu | t-Bu | Ph | 4-t-BuPh | 4-t-BuPh |
| 143096 | t-Bu | t-Bu | CN | 4-t-BuPh | 4-t-BuPh |
| 143097 | t-Bu | t-Bu | DPA | 4-t-BuPh | 4-t-BuPh |
| 143098 | t-Bu | t-Bu | 2-DBF | 4-t-BuPh | 4-t-BuPh |
| 143099 | t-Bu | t-Bu | 2-DBT | 4-t-BuPh | 4-t-BuPh |

TABLE 7-continued

| Compound No. | $R_{11b}$ | $R_{12c}$ | $R_{15C}$ | $R_{18b}$ | $R_{19b}$ |
|---|---|---|---|---|---|
| 143100 | t-Bu | t-Bu | 4-t-BuPh | 4-t-BuPh | 4-t-BuPh |
| 143101 | t-Bu | t-Bu | 1,3-di-t-BuPh | 4-t-BuPh | 4-t-BuPh |
| 143102 | t-Bu | t-Bu | 9-Cbz | 4-t-BuPh | 4-t-BuPh |
| 143103 | t-Bu | t-Bu | t-Bu | 1,3-di-t-BuPh | 1,3-di-t-BuPh |
| 143104 | t-Bu | t-Bu | Ph | 1,3-di-t-BuPh | 1,3-di-t-BuPh |
| 143105 | t-Bu | t-Bu | CN | 1,3-di-t-BuPh | 1,3-di-t-BuPh |
| 143106 | t-Bu | t-Bu | DPA | 1,3-di-t-BuPh | 1,3-di-t-BuPh |
| 143107 | t-Bu | t-Bu | 2-DBF | 1,3-di-t-BuPh | 1,3-di-t-BuPh |
| 143108 | t-Bu | t-Bu | 2-DBT | 1,3-di-t-BuPh | 1,3-di-t-BuPh |
| 143109 | t-Bu | t-Bu | 4-t-BuPh | 1,3-di-t-BuPh | 1,3-di-t-BuPh |
| 143110 | t-Bu | t-Bu | 1,3-di-t-BuPh | 1,3-di-t-BuPh | 1,3-di-t-BuPh |
| 143111 | t-Bu | t-Bu | 9-Cbz | 1,3-di-t-BuPh | 1,3-di-t-BuPh |
| 143112 | Ph | Ph | t-Bu | H | H |
| 143113 | Ph | Ph | CN | H | H |
| 143114 | Ph | Ph | DPA | H | H |
| 143115 | Ph | Ph | 2-DBF | H | H |
| 143116 | Ph | Ph | 2-DBT | H | H |
| 143117 | Ph | Ph | 4-t-BuPh | H | H |
| 143118 | Ph | Ph | 1,3-di-t-BuPh | H | H |
| 143119 | Ph | Ph | 9-Cbz | H | H |
| 143120 | Ph | Ph | t-Bu | t-Bu | t-Bu |
| 143121 | Ph | Ph | Ph | t-Bu | t-Bu |
| 143122 | Ph | Ph | CN | t-Bu | t-Bu |
| 143123 | Ph | Ph | DPA | t-Bu | t-Bu |
| 143124 | Ph | Ph | 2-DBF | t-Bu | t-Bu |
| 143125 | Ph | Ph | 2-DBT | t-Bu | t-Bu |
| 143126 | Ph | Ph | 4-t-BuPh | t-Bu | t-Bu |
| 143127 | Ph | Ph | 1,3-di-t-BuPh | t-Bu | t-Bu |
| 143128 | Ph | Ph | 9-Cbz | t-Bu | t-Bu |
| 143129 | Ph | Ph | Ph | Ph | Ph |
| 143130 | Ph | Ph | CN | Ph | Ph |
| 143131 | Ph | Ph | DPA | Ph | Ph |
| 143132 | Ph | Ph | 2-DBF | Ph | Ph |
| 143133 | Ph | Ph | 2-DBT | Ph | Ph |
| 143134 | Ph | Ph | 4-t-BuPh | Ph | Ph |
| 143135 | Ph | Ph | 1,3-di-t-BuPh | Ph | Ph |
| 143136 | Ph | Ph | 9-Cbz | Ph | Ph |
| 143137 | Ph | Ph | t-Bu | CN | CN |
| 143138 | Ph | Ph | Ph | CN | CN |
| 143139 | Ph | Ph | CN | CN | CN |
| 143140 | Ph | Ph | DPA | CN | CN |
| 143141 | Ph | Ph | 2-DBF | CN | CN |
| 143142 | Ph | Ph | 2-DBT | CN | CN |
| 143143 | Ph | Ph | 4-t-BuPh | CN | CN |
| 143144 | Ph | Ph | 1,3-di-t-BuPh | CN | CN |
| 143145 | Ph | Ph | 9-Cbz | CN | CN |
| 143146 | Ph | Ph | t-Bu | 9-Cbz | 9-Cbz |
| 143147 | Ph | Ph | Ph | 9-Cbz | 9-Cbz |
| 143148 | Ph | Ph | CN | 9-Cbz | 9-Cbz |
| 143149 | Ph | Ph | DPA | 9-Cbz | 9-Cbz |
| 143150 | Ph | Ph | 2-DBF | 9-Cbz | 9-Cbz |
| 143151 | Ph | Ph | 2-DBT | 9-Cbz | 9-Cbz |
| 143152 | Ph | Ph | 4-t-BuPh | 9-Cbz | 9-Cbz |
| 143153 | Ph | Ph | 1,3-di-t-BuPh | 9-Cbz | 9-Cbz |
| 143154 | Ph | Ph | 9-Cbz | 9-Cbz | 9-Cbz |
| 143155 | Ph | Ph | t-Bu | 4-t-BuPh | 4-t-BuPh |
| 143156 | Ph | Ph | Ph | 4-t-BuPh | 4-t-BuPh |
| 143157 | Ph | Ph | CN | 4-t-BuPh | 4-t-BuPh |
| 143158 | Ph | Ph | DPA | 4-t-BuPh | 4-t-BuPh |
| 143159 | Ph | Ph | 2-DBF | 4-t-BuPh | 4-t-BuPh |
| 143160 | Ph | Ph | 2-DBT | 4-t-BuPh | 4-t-BuPh |
| 143161 | Ph | Ph | 4-t-BuPh | 4-t-BuPh | 4-t-BuPh |
| 143162 | Ph | Ph | 1,3-di-t-BuPh | 4-t-BuPh | 4-t-BuPh |
| 143163 | Ph | Ph | 9-Cbz | 4-t-BuPh | 4-t-BuPh |
| 143164 | Ph | Ph | t-Bu | 1,3-di-t-BuPh | 1,3-di-t-BuPh |
| 143165 | Ph | Ph | Ph | 1,3-di-t-BuPh | 1,3-di-t-BuPh |
| 143166 | Ph | Ph | CN | 1,3-di-t-BuPh | 1,3-di-t-BuPh |
| 143167 | Ph | Ph | DPA | 1,3-di-t-BuPh | 1,3-di-t-BuPh |
| 143168 | Ph | Ph | 2-DBF | 1,3-di-t-BuPh | 1,3-di-t-BuPh |
| 143169 | Ph | Ph | 2-DBT | 1,3-di-t-BuPh | 1,3-di-t-BuPh |
| 143170 | Ph | Ph | 4-t-BuPh | 1,3-di-t-BuPh | 1,3-di-t-BuPh |
| 143171 | Ph | Ph | 1,3-di-t-BuPh | 1,3-di-t-BuPh | 1,3-di-t-BuPh |
| 143172 | Ph | Ph | 9-Cbz | 1,3-di-t-BuPh | 1,3-di-t-BuPh |
| 143173 | 9-Cbz | 9-Cbz | t-Bu | H | H |
| 143174 | 9-Cbz | 9-Cbz | Ph | H | H |
| 143175 | 9-Cbz | 9-Cbz | CN | H | H |
| 143176 | 9-Cbz | 9-Cbz | DPA | H | H |
| 143177 | 9-Cbz | 9-Cbz | 2-DBF | H | H |

TABLE 7-continued

| Compound No. | R$_{11b}$ | R$_{12c}$ | R$_{15C}$ | R$_{18b}$ | R$_{19b}$ |
|---|---|---|---|---|---|
| 143178 | 9-Cbz | 9-Cbz | 2-DBT | H | H |
| 143179 | 9-Cbz | 9-Cbz | 4-t-BuPh | H | H |
| 143180 | 9-Cbz | 9-Cbz | 1,3-di-t-BuPh | H | H |
| 143181 | 9-Cbz | 9-Cbz | t-Bu | t-Bu | t-Bu |
| 143182 | 9-Cbz | 9-Cbz | Ph | t-Bu | t-Bu |
| 143183 | 9-Cbz | 9-Cbz | CN | t-Bu | t-Bu |
| 143184 | 9-Cbz | 9-Cbz | DPA | t-Bu | t-Bu |
| 143185 | 9-Cbz | 9-Cbz | 2-DBF | t-Bu | t-Bu |
| 143186 | 9-Cbz | 9-Cbz | 2-DBT | t-Bu | t-Bu |
| 143187 | 9-Cbz | 9-Cbz | 4-t-BuPh | t-Bu | t-Bu |
| 143188 | 9-Cbz | 9-Cbz | 1,3-di-t-BuPh | t-Bu | t-Bu |
| 143189 | 9-Cbz | 9-Cbz | 9-Cbz | t-Bu | t-Bu |
| 143190 | 9-Cbz | 9-Cbz | t-Bu | Ph | Ph |
| 143191 | 9-Cbz | 9-Cbz | Ph | Ph | Ph |
| 143192 | 9-Cbz | 9-Cbz | CN | Ph | Ph |
| 143193 | 9-Cbz | 9-Cbz | DPA | Ph | Ph |
| 143194 | 9-Cbz | 9-Cbz | 2-DBF | Ph | Ph |
| 143195 | 9-Cbz | 9-Cbz | 2-DBT | Ph | Ph |
| 143196 | 9-Cbz | 9-Cbz | 4-t-BuPh | Ph | Ph |
| 143197 | 9-Cbz | 9-Cbz | 1,3-di-t-BuPh | Ph | Ph |
| 143198 | 9-Cbz | 9-Cbz | 9-Cbz | Ph | Ph |
| 143199 | 9-Cbz | 9-Cbz | t-Bu | CN | CN |
| 143200 | 9-Cbz | 9-Cbz | Ph | CN | CN |
| 143201 | 9-Cbz | 9-Cbz | CN | CN | CN |
| 143202 | 9-Cbz | 9-Cbz | DPA | CN | CN |
| 143203 | 9-Cbz | 9-Cbz | 2-DBF | CN | CN |
| 143204 | 9-Cbz | 9-Cbz | 2-DBT | CN | CN |
| 143205 | 9-Cbz | 9-Cbz | 4-t-BuPh | CN | CN |
| 143206 | 9-Cbz | 9-Cbz | 1,3-di-t-BuPh | CN | CN |
| 143207 | 9-Cbz | 9-Cbz | 9-Cbz | CN | CN |
| 143208 | 9-Cbz | 9-Cbz | t-Bu | 9-Cbz | 9-Cbz |
| 143209 | 9-Cbz | 9-Cbz | Ph | 9-Cbz | 9-Cbz |
| 143210 | 9-Cbz | 9-Cbz | CN | 9-Cbz | 9-Cbz |
| 143211 | 9-Cbz | 9-Cbz | DPA | 9-Cbz | 9-Cbz |
| 143212 | 9-Cbz | 9-Cbz | 2-DBF | 9-Cbz | 9-Cbz |
| 143213 | 9-Cbz | 9-Cbz | 2-DBT | 9-Cbz | 9-Cbz |
| 143214 | 9-Cbz | 9-Cbz | 4-t-BuPh | 9-Cbz | 9-Cbz |
| 143215 | 9-Cbz | 9-Cbz | 1,3-di-t-BuPh | 9-Cbz | 9-Cbz |
| 143216 | 9-Cbz | 9-Cbz | 9-Cbz | 9-Cbz | 9-Cbz |
| 143217 | 9-Cbz | 9-Cbz | t-Bu | 4-t-BuPh | 4-t-BuPh |
| 143218 | 9-Cbz | 9-Cbz | Ph | 4-t-BuPh | 4-t-BuPh |
| 143219 | 9-Cbz | 9-Cbz | CN | 4-t-BuPh | 4-t-BuPh |
| 143220 | 9-Cbz | 9-Cbz | DPA | 4-t-BuPh | 4-t-BuPh |
| 143221 | 9-Cbz | 9-Cbz | 2-DBF | 4-t-BuPh | 4-t-BuPh |
| 143222 | 9-Cbz | 9-Cbz | 2-DBT | 4-t-BuPh | 4-t-BuPh |
| 143223 | 9-Cbz | 9-Cbz | 4-t-BuPh | 4-t-BuPh | 4-t-BuPh |
| 143224 | 9-Cbz | 9-Cbz | 1,3-di-t-BuPh | 4-t-BuPh | 4-t-BuPh |
| 143225 | 9-Cbz | 9-Cbz | 9-Cbz | 4-t-BuPh | 4-t-BuPh |
| 143226 | 9-Cbz | 9-Cbz | t-Bu | 1,3-di-t-BuPh | 1,3-di-t-BuPh |
| 143227 | 9-Cbz | 9-Cbz | Ph | 1,3-di-t-BuPh | 1,3-di-t-BuPh |
| 143228 | 9-Cbz | 9-Cbz | CN | 1,3-di-t-BuPh | 1,3-di-t-BuPh |
| 143229 | 9-Cbz | 9-Cbz | DPA | 1,3-di-t-BuPh | 1,3-di-t-BuPh |
| 143230 | 9-Cbz | 9-Cbz | 2-DBF | 1,3-di-t-BuPh | 1,3-di-t-BuPh |
| 143231 | 9-Cbz | 9-Cbz | 2-DBT | 1,3-di-t-BuPh | 1,3-di-t-BuPh |
| 143232 | 9-Cbz | 9-Cbz | 4-t-BuPh | 1,3-di-t-BuPh | 1,3-di-t-BuPh |
| 143233 | 9-Cbz | 9-Cbz | 1,3-di-t-BuPh | 1,3-di-t-BuPh | 1,3-di-t-BuPh |
| 143234 | 9-Cbz | 9-Cbz | 9-Cbz | 1,3-di-t-BuPh | 1,3-di-t-BuPh |
| 143235 | CN | CN | t-Bu | H | H |
| 143236 | CN | CN | Ph | H | H |
| 143237 | CN | CN | DPA | H | H |
| 143238 | CN | CN | 2-DBF | H | H |
| 143239 | CN | CN | 2-DBT | H | H |
| 143240 | CN | CN | 4-t-BuPh | H | H |
| 143241 | CN | CN | 1,3-di-t-BuPh | H | H |
| 143242 | CN | CN | 9-Cbz | H | H |
| 143243 | CN | CN | t-Bu | t-Bu | t-Bu |
| 143244 | CN | CN | Ph | t-Bu | t-Bu |
| 143245 | CN | CN | CN | t-Bu | t-Bu |
| 143246 | CN | CN | DPA | t-Bu | t-Bu |
| 143247 | CN | CN | 2-DBF | t-Bu | t-Bu |
| 143248 | CN | CN | 2-DBT | t-Bu | t-Bu |
| 143249 | CN | CN | 4-t-BuPh | t-Bu | t-Bu |
| 143250 | CN | CN | 1,3-di-t-BuPh | t-Bu | t-Bu |
| 143251 | CN | CN | 9-Cbz | t-Bu | t-Bu |
| 143252 | CN | CN | t-Bu | Ph | Ph |
| 143253 | CN | CN | Ph | Ph | Ph |
| 143254 | CN | CN | CN | Ph | Ph |
| 143255 | CN | CN | DPA | Ph | Ph |
| 143256 | CN | CN | 2-DBF | Ph | Ph |
| 143257 | CN | CN | 2-DBT | Ph | Ph |
| 143258 | CN | CN | 4-t-BuPh | Ph | Ph |
| 143259 | CN | CN | 1,3-di-t-BuPh | Ph | Ph |
| 143260 | CN | CN | 9-Cbz | Ph | Ph |
| 143261 | CN | CN | t-Bu | CN | CN |
| 143262 | CN | CN | Ph | CN | CN |
| 143263 | CN | CN | CN | CN | CN |
| 143264 | CN | CN | DPA | CN | CN |

TABLE 7-continued

| Compound No. | $R_{11b}$ | $R_{12c}$ | $R_{15C}$ | $R_{18b}$ | $R_{19b}$ |
|---|---|---|---|---|---|
| 143265 | CN | CN | 2-DBF | CN | CN |
| 143266 | CN | CN | 2-DBT | CN | CN |
| 143267 | CN | CN | 4-t-BuPh | CN | CN |
| 143268 | CN | CN | 1,3-di-t-BuPh | CN | CN |
| 143269 | CN | CN | 9-Cbz | CN | CN |
| 143270 | CN | CN | t-Bu | 9-Cbz | 9-Cbz |
| 143271 | CN | CN | Ph | 9-Cbz | 9-Cbz |
| 143272 | CN | CN | CN | 9-Cbz | 9-Cbz |
| 143273 | CN | CN | DPA | 9-Cbz | 9-Cbz |
| 143274 | CN | CN | 2-DBF | 9-Cbz | 9-Cbz |
| 143275 | CN | CN | 2-DBT | 9-Cbz | 9-Cbz |
| 143276 | CN | CN | 4-t-BuPh | 9-Cbz | 9-Cbz |
| 143277 | CN | CN | 1,3-di-t-BuPh | 9-Cbz | 9-Cbz |
| 143278 | CN | CN | 9-Cbz | 9-Cbz | 9-Cbz |
| 143279 | CN | CN | t-Bu | 4-t-BuPh | 4-t-BuPh |
| 143280 | CN | CN | Ph | 4-t-BuPh | 4-t-BuPh |
| 143281 | CN | CN | CN | 4-t-BuPh | 4-t-BuPh |
| 143282 | CN | CN | DPA | 4-t-BuPh | 4-t-BuPh |
| 143283 | CN | CN | 2-DBF | 4-t-BuPh | 4-t-BuPh |
| 143284 | CN | CN | 2-DBT | 4-t-BuPh | 4-t-BuPh |
| 143285 | CN | CN | 4-t-BuPh | 4-t-BuPh | 4-t-BuPh |
| 143286 | CN | CN | 1,3-di-t-BuPh | 4-t-BuPh | 4-t-BuPh |
| 143287 | CN | CN | 9-Cbz | 4-t-BuPh | 4-t-BuPh |
| 143288 | CN | CN | t-Bu | 1,3-di-t-BuPh | 1,3-di-t-BuPh |
| 143289 | CN | CN | Ph | 1,3-di-t-BuPh | 1,3-di-t-BuPh |
| 143290 | CN | CN | CN | 1,3-di-t-BuPh | 1,3-di-t-BuPh |
| 143291 | CN | CN | DPA | 1,3-di-t-BuPh | 1,3-di-t-BuPh |
| 143292 | CN | CN | 2-DBF | 1,3-di-t-BuPh | 1,3-di-t-BuPh |
| 143293 | CN | CN | 2-DBT | 1,3-di-t-BuPh | 1,3-di-t-BuPh |
| 143294 | CN | CN | 4-t-BuPh | 1,3-di-t-BuPh | 1,3-di-t-BuPh |
| 143295 | CN | CN | 1,3-di-t-BuPh | 1,3-di-t-BuPh | 1,3-di-t-BuPh |
| 143296 | CN | CN | 9-Cbz | 1,3-di-t-BuPh | 1,3-di-t-BuPh |
| 143297 | 4-t-BuPh | 4-t-BuPh | t-Bu | H | H |
| 143298 | 4-t-BuPh | 4-t-BuPh | Ph | H | H |
| 143299 | 4-t-BuPh | 4-t-BuPh | CN | H | H |
| 143300 | 4-t-BuPh | 4-t-BuPh | DPA | H | H |
| 143301 | 4-t-BuPh | 4-t-BuPh | 2-DBF | H | H |
| 143302 | 4-t-BuPh | 4-t-BuPh | 2-DBT | H | H |
| 143303 | 4-t-BuPh | 4-t-BuPh | 1,3-di-t-BuPh | H | H |
| 143304 | 4-t-BuPh | 4-t-BuPh | 9-Cbz | H | H |
| 143305 | 4-t-BuPh | 4-t-BuPh | t-Bu | t-Bu | t-Bu |
| 143306 | 4-t-BuPh | 4-t-BuPh | Ph | t-Bu | t-Bu |
| 143307 | 4-t-BuPh | 4-t-BuPh | CN | t-Bu | t-Bu |
| 143308 | 4-t-BuPh | 4-t-BuPh | DPA | t-Bu | t-Bu |
| 143309 | 4-t-BuPh | 4-t-BuPh | 2-DBF | t-Bu | t-Bu |
| 143310 | 4-t-BuPh | 4-t-BuPh | 2-DBT | t-Bu | t-Bu |
| 143311 | 4-t-BuPh | 4-t-BuPh | 4-t-BuPh | t-Bu | t-Bu |
| 143312 | 4-t-BuPh | 4-t-BuPh | 1,3-di-t-BuPh | t-Bu | t-Bu |
| 143313 | 4-t-BuPh | 4-t-BuPh | 9-Cbz | t-Bu | t-Bu |
| 143314 | 4-t-BuPh | 4-t-BuPh | t-Bu | Ph | Ph |
| 143315 | 4-t-BuPh | 4-t-BuPh | Ph | Ph | Ph |
| 143316 | 4-t-BuPh | 4-t-BuPh | CN | Ph | Ph |
| 143317 | 4-t-BuPh | 4-t-BuPh | DPA | Ph | Ph |
| 143318 | 4-t-BuPh | 4-t-BuPh | 2-DBF | Ph | Ph |
| 143319 | 4-t-BuPh | 4-t-BuPh | 2-DBT | Ph | Ph |
| 143320 | 4-t-BuPh | 4-t-BuPh | 4-t-BuPh | Ph | Ph |
| 143321 | 4-t-BuPh | 4-t-BuPh | 1,3-di-t-BuPh | Ph | Ph |
| 143322 | 4-t-BuPh | 4-t-BuPh | 9-Cbz | Ph | Ph |
| 143323 | 4-t-BuPh | 4-t-BuPh | t-Bu | CN | CN |
| 143324 | 4-t-BuPh | 4-t-BuPh | Ph | CN | CN |
| 143325 | 4-t-BuPh | 4-t-BuPh | CN | CN | CN |
| 143326 | 4-t-BuPh | 4-t-BuPh | DPA | CN | CN |
| 143327 | 4-t-BuPh | 4-t-BuPh | 2-DBF | CN | CN |
| 143328 | 4-t-BuPh | 4-t-BuPh | 2-DBT | CN | CN |
| 143329 | 4-t-BuPh | 4-t-BuPh | 4-t-BuPh | CN | CN |
| 143330 | 4-t-BuPh | 4-t-BuPh | 1,3-di-t-BuPh | CN | CN |
| 143331 | 4-t-BuPh | 4-t-BuPh | 9-Cbz | CN | CN |
| 143332 | 4-t-BuPh | 4-t-BuPh | t-Bu | 9-Cbz | 9-Cbz |
| 143333 | 4-t-BuPh | 4-t-BuPh | Ph | 9-Cbz | 9-Cbz |
| 143334 | 4-t-BuPh | 4-t-BuPh | CN | 9-Cbz | 9-Cbz |
| 143335 | 4-t-BuPh | 4-t-BuPh | DPA | 9-Cbz | 9-Cbz |

TABLE 7-continued

| Compound No. | $R_{11b}$ | $R_{12c}$ | $R_{15C}$ | $R_{18b}$ | $R_{19b}$ |
|---|---|---|---|---|---|
| 143336 | 4-t-BuPh | 4-t-BuPh | 2-DBF | 9-Cbz | 9-Cbz |
| 143337 | 4-t-BuPh | 4-t-BuPh | 2-DBT | 9-Cbz | 9-Cbz |
| 143338 | 4-t-BuPh | 4-t-BuPh | 4-t-BuPh | 9-Cbz | 9-Cbz |
| 143339 | 4-t-BuPh | 4-t-BuPh | 1,3-di-t-BuPh | 9-Cbz | 9-Cbz |
| 143340 | 4-t-BuPh | 4-t-BuPh | 9-Cbz | 9-Cbz | 9-Cbz |
| 143341 | 4-t-BuPh | 4-t-BuPh | t-Bu | 4-t-BuPh | 4-t-BuPh |
| 143342 | 4-t-BuPh | 4-t-BuPh | Ph | 4-t-BuPh | 4-t-BuPh |
| 143343 | 4-t-BuPh | 4-t-BuPh | CN | 4-t-BuPh | 4-t-BuPh |
| 143344 | 4-t-BuPh | 4-t-BuPh | DPA | 4-t-BuPh | 4-t-BuPh |
| 143345 | 4-t-BuPh | 4-t-BuPh | 2-DBF | 4-t-BuPh | 4-t-BuPh |
| 143346 | 4-t-BuPh | 4-t-BuPh | 2-DBT | 4-t-BuPh | 4-t-BuPh |
| 143347 | 4-t-BuPh | 4-t-BuPh | 4-t-BuPh | 4-t-BuPh | 4-t-BuPh |
| 143348 | 4-t-BuPh | 4-t-BuPh | 1,3-di-t-BuPh | 4-t-BuPh | 4-t-BuPh |
| 143349 | 4-t-BuPh | 4-t-BuPh | 9-Cbz | 4-t-BuPh | 4-t-BuPh |
| 143350 | 4-t-BuPh | 4-t-BuPh | t-Bu | 1,3-di-t-BuPh | 1,3-di-t-BuPh |
| 143351 | 4-t-BuPh | 4-t-BuPh | Ph | 1,3-di-t-BuPh | 1,3-di-t-BuPh |
| 143352 | 4-t-BuPh | 4-t-BuPh | CN | 1,3-di-t-BuPh | 1,3-di-t-BuPh |
| 143353 | 4-t-BuPh | 4-t-BuPh | DPA | 1,3-di-t-BuPh | 1,3-di-t-BuPh |
| 143354 | 4-t-BuPh | 4-t-BuPh | 2-DBF | 1,3-di-t-BuPh | 1,3-di-t-BuPh |
| 143355 | 4-t-BuPh | 4-t-BuPh | 2-DBT | 1,3-di-t-BuPh | 1,3-di-t-BuPh |
| 143356 | 4-t-BuPh | 4-t-BuPh | 4-t-BuPh | 1,3-di-t-BuPh | 1,3-di-t-BuPh |
| 143357 | 4-t-BuPh | 4-t-BuPh | 1,3-di-t-BuPh | 1,3-di-t-BuPh | 1,3-di-t-BuPh |
| 143358 | 4-t-BuPh | 4-t-BuPh | 9-Cbz | 1,3-di-t-BuPh | 1,3-di-t-BuPh |
| 143359 | 1,3-di-t-BuPh | 1,3-di-t-BuPh | t-Bu | H | H |
| 143360 | 1,3-di-t-BuPh | 1,3-di-t-BuPh | Ph | H | H |
| 143361 | 1,3-di-t-BuPh | 1,3-di-t-BuPh | CN | H | H |
| 143362 | 1,3-di-t-BuPh | 1,3-di-t-BuPh | DPA | H | H |
| 143363 | 1,3-di-t-BuPh | 1,3-di-t-BuPh | 2-DBF | H | H |
| 143364 | 1,3-di-t-BuPh | 1,3-di-t-BuPh | 2-DBT | H | H |
| 143365 | 1,3-di-t-BuPh | 1,3-di-t-BuPh | 4-t-BuPh | H | H |
| 143366 | 1,3-di-t-BuPh | 1,3-di-t-BuPh | 9-Cbz | H | H |
| 143367 | 1,3-di-t-BuPh | 1,3-di-t-BuPh | t-Bu | t-Bu | t-Bu |
| 143368 | 1,3-di-t-BuPh | 1,3-di-t-BuPh | Ph | t-Bu | t-Bu |
| 143369 | 1,3-di-t-BuPh | 1,3-di-t-BuPh | CN | t-Bu | t-Bu |
| 143370 | 1,3-di-t-BuPh | 1,3-di-t-BuPh | DPA | t-Bu | t-Bu |
| 143371 | 1,3-di-t-BuPh | 1,3-di-t-BuPh | 2-DBF | t-Bu | t-Bu |
| 143372 | 1,3-di-t-BuPh | 1,3-di-t-BuPh | 2-DBT | t-Bu | t-Bu |
| 143373 | 1,3-di-t-BuPh | 1,3-di-t-BuPh | 4-t-BuPh | t-Bu | t-Bu |
| 143374 | 1,3-di-t-BuPh | 1,3-di-t-BuPh | 1,3-di-t-BuPh | t-Bu | t-Bu |
| 143375 | 1,3-di-t-BuPh | 1,3-di-t-BuPh | 9-Cbz | t-Bu | t-Bu |
| 143376 | 1,3-di-t-BuPh | 1,3-di-t-BuPh | t-Bu | Ph | Ph |
| 143377 | 1,3-di-t-BuPh | 1,3-di-t-BuPh | Ph | Ph | Ph |
| 143378 | 1,3-di-t-BuPh | 1,3-di-t-BuPh | CN | Ph | Ph |
| 143379 | 1,3-di-t-BuPh | 1,3-di-t-BuPh | DPA | Ph | Ph |
| 143380 | 1,3-di-t-BuPh | 1,3-di-t-BuPh | 2-DBF | Ph | Ph |
| 143381 | 1,3-di-t-BuPh | 1,3-di-t-BuPh | 2-DBT | Ph | Ph |
| 143382 | 1,3-di-t-BuPh | 1,3-di-t-BuPh | 4-t-BuPh | Ph | Ph |
| 143383 | 1,3-di-t-BuPh | 1,3-di-t-BuPh | 1,3-di-t-BuPh | Ph | Ph |
| 143384 | 1,3-di-t-BuPh | 1,3-di-t-BuPh | 9-Cbz | Ph | Ph |
| 143385 | 1,3-di-t-BuPh | 1,3-di-t-BuPh | t-Bu | CN | CN |
| 143386 | 1,3-di-t-BuPh | 1,3-di-t-BuPh | Ph | CN | CN |
| 143387 | 1,3-di-t-BuPh | 1,3-di-t-BuPh | CN | CN | CN |
| 143388 | 1,3-di-t-BuPh | 1,3-di-t-BuPh | DPA | CN | CN |
| 143389 | 1,3-di-t-BuPh | 1,3-di-t-BuPh | 2-DBF | CN | CN |

TABLE 7-continued

| Compound No. | $R_{11b}$ | $R_{12c}$ | $R_{15C}$ | $R_{18b}$ | $R_{19b}$ |
|---|---|---|---|---|---|
| 143390 | 1,3-di-t-BuPh | 1,3-di-t-BuPh | 2-DBT | CN | CN |
| 143391 | 1,3-di-t-BuPh | 1,3-di-t-BuPh | 4-t-BuPh | CN | CN |
| 143392 | 1,3-di-t-BuPh | 1,3-di-t-BuPh | 1,3-di-t-BuPh | CN | CN |
| 143393 | 1,3-di-t-BuPh | 1,3-di-t-BuPh | 9-Cbz | CN | CN |
| 143394 | 1,3-di-t-BuPh | 1,3-di-t-BuPh | t-Bu | 9-Cbz | 9-Cbz |
| 143395 | 1,3-di-t-BuPh | 1,3-di-t-BuPh | Ph | 9-Cbz | 9-Cbz |
| 143396 | 1,3-di-t-BuPh | 1,3-di-t-BuPh | CN | 9-Cbz | 9-Cbz |
| 143397 | 1,3-di-t-BuPh | 1,3-di-t-BuPh | DPA | 9-Cbz | 9-Cbz |
| 143398 | 1,3-di-t-BuPh | 1,3-di-t-BuPh | 2-DBF | 9-Cbz | 9-Cbz |
| 143399 | 1,3-di-t-BuPh | 1,3-di-t-BuPh | 2-DBT | 9-Cbz | 9-Cbz |
| 143400 | 1,3-di-t-BuPh | 1,3-di-t-BuPh | 4-t-BuPh | 9-Cbz | 9-Cbz |
| 143401 | 1,3-di-t-BuPh | 1,3-di-t-BuPh | 1,3-di-t-BuPh | 9-Cbz | 9-Cbz |
| 143402 | 1,3-di-t-BuPh | 1,3-di-t-BuPh | 9-Cbz | 9-Cbz | 9-Cbz |
| 143403 | 1,3-di-t-BuPh | 1,3-di-t-BuPh | t-Bu | 4-t-BuPh | 4-t-BuPh |
| 143404 | 1,3-di-t-BuPh | 1,3-di-t-BuPh | Ph | 4-t-BuPh | 4-t-BuPh |
| 143405 | 1,3-di-t-BuPh | 1,3-di-t-BuPh | CN | 4-t-BuPh | 4-t-BuPh |
| 143406 | 1,3-di-t-BuPh | 1,3-di-t-BuPh | DPA | 4-t-BuPh | 4-t-BuPh |
| 143407 | 1,3-di-t-BuPh | 1,3-di-t-BuPh | 2-DBF | 4-t-BuPh | 4-t-BuPh |
| 143408 | 1,3-di-t-BuPh | 1,3-di-t-BuPh | 2-DBT | 4-t-BuPh | 4-t-BuPh |
| 143409 | 1,3-di-t-BuPh | 1,3-di-t-BuPh | 4-t-BuPh | 4-t-BuPh | 4-t-BuPh |
| 143410 | 1,3-di-t-BuPh | 1,3-di-t-BuPh | 1,3-di-t-BuPh | 4-t-BuPh | 4-t-BuPh |
| 143411 | 1,3-di-t-BuPh | 1,3-di-t-BuPh | 9-Cbz | 4-t-BuPh | 4-t-BuPh |
| 143412 | 1,3-di-t-BuPh | 1,3-di-t-BuPh | t-Bu | 1,3-dkt-BuPh | 1,3-di-t-BuPh |
| 143413 | 1,3-di-t-BuPh | 1,3-di-t-BuPh | Ph | 1,3-di-t-BuPh | 1,3-di-t-BuPh |
| 143414 | 1,3-di-t-BuPh | 1,3-di-t-BuPh | CN | 1,3-di-t-BuPh | 1,3-di-t-BuPh |
| 143415 | 1,3-di-t-BuPh | 1,3-di-t-BuPh | DPA | 1,3-di-t-BuPh | 1,3-di-t-BuPh |
| 143416 | 1,3-di-t-BuPh | 1,3-di-t-BuPh | 2-DBF | 1,3-di-t-BuPh | 1,3-di-t-BuPh |
| 143417 | 1,3-di-t-BuPh | 1,3-di-t-BuPh | 2-DBT | 1,3-di-t-BuPh | 1,3-di-t-BuPh |
| 143418 | 1,3-di-t-BuPh | 1,3-di-t-BuPh | 4-t-BuPh | 1,3-di-t-BuPh | 1,3-di-t-BuPh |
| 143419 | 1,3-di-t-BuPh | 1,3-di-t-BuPh | 1,3-di-t-BuPh | 1,3-di-t-BuPh | 1,3-di-t-BuPh |
| 143420 | 1,3-di-t-BuPh | 1,3-di-t-BuPh | 9-Cbz | 1,3-di-t-BuPh | 1,3-di-t-BuPh |

Group HC8

The heterocyclic compound may be represented by Formula 15-4, and substituents may be defined as shown in Table 8.

TABLE 8

| Compound No. | $R_{11b}$ | $R_{12c}$ | $R_{15C}$ | $R_{18b}$ | $R_{19b}$ |
|---|---|---|---|---|---|
| 154001 | t-Bu | t-Bu | t-Bu | t-Bu | t-Bu |
| 154002 | Ph | Ph | t-Bu | Ph | Ph |
| 154003 | t-Bu | t-Bu | H | H | H |
| 154004 | H | H | t-Bu | H | H |
| 154005 | H | H | H | t-Bu | t-Bu |
| 154006 | t-Bu | t-Bu | t-Bu | H | H |
| 154007 | H | H | t-Bu | t-Bu | t-Bu |
| 154008 | t-Bu | t-Bu | H | t-Bu | t-Bu |
| 154009 | Ph | Ph | H | H | H |
| 154010 | H | H | Ph | H | H |
| 154011 | H | H | H | Ph | Ph |
| 154012 | Ph | Ph | Ph | H | H |
| 154013 | H | H | Ph | Ph | Ph |
| 154014 | Ph | Ph | H | Ph | Ph |
| 154015 | CN | CN | H | H | H |
| 154016 | H | H | CN | H | H |
| 154017 | H | H | H | CN | CN |
| 154018 | CN | CN | CN | H | H |
| 154019 | H | H | CN | CN | CN |
| 154020 | CN | CN | H | CN | CN |

TABLE 8-continued

| Compound No. | $R_{11b}$ | $R_{12c}$ | $R_{15C}$ | $R_{18b}$ | $R_{19b}$ |
|---|---|---|---|---|---|
| 154021 | 9-Cbz | 9-Cbz | H | H | H |
| 154022 | H | H | 9-Cbz | H | H |
| 154023 | H | H | H | 9-Cbz | 9-Cbz |
| 154024 | 9-Cbz | 9-Cbz | 9-Cbz | H | H |
| 154025 | H | H | 9-Cbz | 9-Cbz | 9-Cbz |
| 154026 | 9-Cbz | 9-Cbz | H | 9-Cbz | 9-Cbz |
| 154027 | Me | Me | H | H | H |
| 154028 | H | H | Me | H | H |
| 154029 | H | H | H | Me | Me |
| 154030 | Me | Me | Me | H | H |
| 154031 | H | H | Me | Me | Me |
| 154032 | Me | Me | H | Me | Me |
| 154033 | CD$_3$ | CD3 | H | H | H |
| 154034 | H | H | CD3 | H | H |
| 154035 | H | H | H | CD3 | CD3 |
| 154036 | CD3 | CD3 | CD3 | H | H |
| 154037 | H | H | CD3 | CD3 | CD3 |
| 154038 | CD3 | CD3 | H | CD3 | CD3 |
| 154039 | 4-t-BuPh | 4-t-BuPh | H | H | H |
| 154040 | H | H | 4-t-BuPh | H | H |
| 154041 | H | H | H | 4-t-BuPh | 4-t-BuPh |
| 154042 | 4-t-BuPh | 4-t-BuPh | 4-t-BuPh | H | H |
| 154043 | H | H | 4-t-BuPh | 4-t-BuPh | 4-t-BuPh |
| 154044 | 4-t-BuPh | 4-t-BuPh | H | 4-t-BuPh | 4-t-BuPh |
| 154045 | 1,3-di-t-BuPh | 1,3-di-t-BuPh | H | H | H |
| 154046 | H | H | 1,3-di-t-BuPh | H | H |
| 154047 | H | H | H | 1,3-di-t-BuPh | 1,3-di-t-BuPh |
| 154048 | 1,3-di-t-BuPh | 1,3-di-t-BuPh | 1,3-di-t-BuPh | H | H |
| 154049 | H | H | 1,3-di-t-BuPh | 1,3-di-t-BuPh | 1,3-di-t-BuPh |
| 154050 | 1,3-di-t-BuPh | 1,3-di-t-BuPh | H | 1,3-di-t-BuPh | 1,3-di-t-BuPh |
| 154051 | t-Bu | t-Bu | Ph | H | H |
| 154052 | t-Bu | t-Bu | CN | H | H |
| 154053 | t-Bu | t-Bu | DPA | H | H |
| 154054 | t-Bu | t-Bu | 2-DBF | H | H |
| 154055 | t-Bu | t-Bu | 2-DBT | H | H |
| 154056 | t-Bu | t-Bu | 4-t-BuPh | H | H |
| 154057 | t-Bu | t-Bu | 1,3-di-t-BuPh | H | H |
| 154058 | t-Bu | t-Bu | 9-Cbz | H | H |
| 154059 | t-Bu | t-Bu | Ph | t-Bu | t-Bu |
| 154060 | t-Bu | t-Bu | CN | t-Bu | t-Bu |
| 154061 | t-Bu | t-Bu | DPA | t-Bu | t-Bu |
| 154062 | t-Bu | t-Bu | 2-DBF | t-Bu | t-Bu |
| 154063 | t-Bu | t-Bu | 2-DBT | t-Bu | t-Bu |
| 154064 | t-Bu | t-Bu | 4-t-BuPh | t-Bu | t-Bu |
| 154065 | t-Bu | t-Bu | 1,3-di-t-BuPh | t-Bu | t-Bu |
| 154066 | t-Bu | t-Bu | 9-Cbz | t-Bu | t-Bu |
| 154067 | t-Bu | t-Bu | t-Bu | Ph | Ph |
| 154068 | t-Bu | t-Bu | Ph | Ph | Ph |
| 154069 | t-Bu | t-Bu | CN | Ph | Ph |
| 154070 | t-Bu | t-Bu | DPA | Ph | Ph |
| 154071 | t-Bu | t-Bu | 2-DBF | Ph | Ph |
| 154072 | t-Bu | t-Bu | 2-DBT | Ph | Ph |
| 154073 | t-Bu | t-Bu | 4-t-BuPh | Ph | Ph |
| 154074 | t-Bu | t-Bu | 1,3-di-t-BuPh | Ph | Ph |
| 154075 | t-Bu | t-Bu | 9-Cbz | Ph | Ph |
| 154076 | t-Bu | t-Bu | t-Bu | CN | CN |
| 154077 | t-Bu | t-Bu | Ph | CN | CN |
| 154078 | t-Bu | t-Bu | CN | CN | CN |
| 154079 | t-Bu | t-Bu | DPA | CN | CN |
| 154080 | t-Bu | t-Bu | 2-DBF | CN | CN |
| 154081 | t-Bu | t-Bu | 2-DBT | CN | CN |
| 154082 | t-Bu | t-Bu | 4-t-BuPh | CN | CN |
| 154083 | t-Bu | t-Bu | 1,3-di-t-BuPh | CN | CN |
| 154084 | t-Bu | t-Bu | 9-Cbz | CN | CN |
| 154085 | t-Bu | t-Bu | t-Bu | 9-Cbz | 9-Cbz |
| 154086 | t-Bu | t-Bu | Ph | 9-Cbz | 9-Cbz |
| 154087 | t-Bu | t-Bu | CN | 9-Cbz | 9-Cbz |
| 154088 | t-Bu | t-Bu | DPA | 9-Cbz | 9-Cbz |
| 154089 | t-Bu | t-Bu | 2-DBF | 9-Cbz | 9-Cbz |
| 154090 | t-Bu | t-Bu | 2-DBT | 9-Cbz | 9-Cbz |
| 154091 | t-Bu | t-Bu | 4-t-BuPh | 9-Cbz | 9-Cbz |
| 154092 | t-Bu | t-Bu | 1,3-di-t-BuPh | 9-Cbz | 9-Cbz |
| 154093 | t-Bu | t-Bu | 9-Cbz | 9-Cbz | 9-Cbz |
| 154094 | t-Bu | t-Bu | t-Bu | 4-t-BuPh | 4-t-BuPh |
| 154095 | t-Bu | t-Bu | Ph | 4-t-BuPh | 4-t-BuPh |
| 154096 | t-Bu | t-Bu | CN | 4-t-BuPh | 4-t-BuPh |
| 154097 | t-Bu | t-Bu | DPA | 4-t-BuPh | 4-t-BuPh |
| 154098 | t-Bu | t-Bu | 2-DBF | 4-t-BuPh | 4-t-BuPh |

TABLE 8-continued

| Compound No. | $R_{11b}$ | $R_{12c}$ | $R_{15C}$ | $R_{18b}$ | $R_{19b}$ |
|---|---|---|---|---|---|
| 154099 | t-Bu | t-Bu | 2-DBT | 4-t-BuPh | 4-t-BuPh |
| 154100 | t-Bu | t-Bu | 4-t-BuPh | 4-t-BuPh | 4-t-BuPh |
| 154101 | t-Bu | t-Bu | 1,3-di-t-BuPh | 4-t-BuPh | 4-t-BuPh |
| 154102 | t-Bu | t-Bu | 9-Cbz | 4-t-BuPh | 4-t-BuPh |
| 154103 | t-Bu | t-Bu | t-Bu | 1,3-di-t-BuPh | 1,3-di-t-BuPh |
| 154104 | t-Bu | t-Bu | Ph | 1,3-di-t-BuPh | 1,3-di-t-BuPh |
| 154105 | t-Bu | t-Bu | CN | 1,3-di-t-BuPh | 1,3-di-t-BuPh |
| 154106 | t-Bu | t-Bu | DPA | 1,3-di-t-BuPh | 1,3-di-t-BuPh |
| 154107 | t-Bu | t-Bu | 2-DBF | 1,3-di-t-BuPh | 1,3-di-t-BuPh |
| 154108 | t-Bu | t-Bu | 2-DBT | 1,3-di-t-BuPh | 1,3-di-t-BuPh |
| 154109 | t-Bu | t-Bu | 4-t-BuPh | 1,3-di-t-BuPh | 1,3-di-t-BuPh |
| 154110 | t-Bu | t-Bu | 1,3-di-t-BuPh | 1,3-di-t-BuPh | 1,3-di-t-BuPh |
| 154111 | t-Bu | t-Bu | 9-Cbz | 1,3-di-t-BuPh | 1,3-di-t-BuPh |
| 154112 | Ph | Ph | t-Bu | H | H |
| 154113 | Ph | Ph | CN | H | H |
| 154114 | Ph | Ph | DPA | H | H |
| 154115 | Ph | Ph | 2-DBF | H | H |
| 154116 | Ph | Ph | 2-DBT | H | H |
| 154117 | Ph | Ph | 4-t-BuPh | H | H |
| 154118 | Ph | Ph | 1,3-di-t-BuPh | H | H |
| 154119 | Ph | Ph | 9-Cbz | H | H |
| 154120 | Ph | Ph | t-Bu | t-Bu | t-Bu |
| 154121 | Ph | Ph | Ph | t-Bu | t-Bu |
| 154122 | Ph | Ph | CN | t-Bu | t-Bu |
| 154123 | Ph | Ph | DPA | t-Bu | t-Bu |
| 154124 | Ph | Ph | 2-DBF | t-Bu | t-Bu |
| 154125 | Ph | Ph | 2-DBT | t-Bu | t-Bu |
| 154126 | Ph | Ph | 4-t-BuPh | t-Bu | t-Bu |
| 154127 | Ph | Ph | 1,3-di-t-BuPh | t-Bu | t-Bu |
| 154128 | Ph | Ph | 9-Cbz | t-Bu | t-Bu |
| 154129 | Ph | Ph | Ph | Ph | Ph |
| 154130 | Ph | Ph | CN | Ph | Ph |
| 154131 | Ph | Ph | DPA | Ph | Ph |
| 154132 | Ph | Ph | 2-DBF | Ph | Ph |
| 154133 | Ph | Ph | 2-DBT | Ph | Ph |
| 154134 | Ph | Ph | 4-t-BuPh | Ph | Ph |
| 154135 | Ph | Ph | 1,3-di-t-BuPh | Ph | Ph |
| 154136 | Ph | Ph | 9-Cbz | Ph | Ph |
| 154137 | Ph | Ph | t-Bu | CN | CN |
| 154138 | Ph | Ph | Ph | CN | CN |
| 154139 | Ph | Ph | CN | CN | CN |
| 154140 | Ph | Ph | DPA | CN | CN |
| 154141 | Ph | Ph | 2-DBF | CN | CN |
| 154142 | Ph | Ph | 2-DBT | CN | CN |
| 154143 | Ph | Ph | 4-t-BuPh | CN | CN |
| 154144 | Ph | Ph | 1,3-di-t-BuPh | CN | CN |
| 154145 | Ph | Ph | 9-Cbz | CN | CN |
| 154146 | Ph | Ph | t-Bu | 9-Cbz | 9-Cbz |
| 154147 | Ph | Ph | Ph | 9-Cbz | 9-Cbz |
| 154148 | Ph | Ph | CN | 9-Cbz | 9-Cbz |
| 154149 | Ph | Ph | DPA | 9-Cbz | 9-Cbz |
| 154150 | Ph | Ph | 2-DBF | 9-Cbz | 9-Cbz |
| 154151 | Ph | Ph | 2-DBT | 9-Cbz | 9-Cbz |
| 154152 | Ph | Ph | 4-t-BuPh | 9-Cbz | 9-Cbz |
| 154153 | Ph | Ph | 1,3-di-t-BuPh | 9-Cbz | 9-Cbz |
| 154154 | Ph | Ph | 9-Cbz | 9-Cbz | 9-Cbz |
| 154155 | Ph | Ph | t-Bu | 4-t-BuPh | 4-t-BuPh |
| 154156 | Ph | Ph | Ph | 4-t-BuPh | 4-t-BuPh |
| 154157 | Ph | Ph | CN | 4-t-BuPh | 4-t-BuPh |
| 154158 | Ph | Ph | DPA | 4-t-BuPh | 4-t-BuPh |
| 154159 | Ph | Ph | 2-DBF | 4-t-BuPh | 4-t-BuPh |
| 154160 | Ph | Ph | 2-DBT | 4-t-BuPh | 4-t-BuPh |
| 154161 | Ph | Ph | 4-t-BuPh | 4-t-BuPh | 4-t-BuPh |
| 154162 | Ph | Ph | 1,3-di-t-BuPh | 4-t-BuPh | 4-t-BuPh |
| 154163 | Ph | Ph | 9-Cbz | 4-t-BuPh | 4-t-BuPh |
| 154164 | Ph | Ph | t-Bu | 1,3-di-t-BuPh | 1,3-di-t-BuPh |
| 154165 | Ph | Ph | Ph | 1,3-di-t-BuPh | 1,3-di-t-BuPh |
| 154166 | Ph | Ph | CN | 1,3-di-t-BuPh | 1,3-di-t-BuPh |
| 154167 | Ph | Ph | DPA | 1,3-di-t-BuPh | 1,3-di-t-BuPh |
| 154168 | Ph | Ph | 2-DBF | 1,3-di-t-BuPh | 1,3-di-t-BuPh |
| 154169 | Ph | Ph | 2-DBT | 1,3-di-t-BuPh | 1,3-di-t-BuPh |
| 154170 | Ph | Ph | 4-t-BuPh | 1,3-di-t-BuPh | 1,3-di-t-BuPh |
| 154171 | Ph | Ph | 1,3-di-t-BuPh | 1,3-di-t-BuPh | 1,3-di-t-BuPh |
| 154172 | Ph | Ph | 9-Cbz | 1,3-di-t-BuPh | 1,3-di-t-BuPh |
| 154173 | 9-Cbz | 9-Cbz | t-Bu | H | H |
| 154174 | 9-Cbz | 9-Cbz | Ph | H | H |
| 154175 | 9-Cbz | 9-Cbz | CN | H | H |
| 154176 | 9-Cbz | 9-Cbz | DPA | H | H |

TABLE 8-continued

| Compound No. | $R_{11b}$ | $R_{12c}$ | $R_{15C}$ | $R_{18b}$ | $R_{19b}$ |
|---|---|---|---|---|---|
| 154177 | 9-Cbz | 9-Cbz | 2-DBF | H | H |
| 154178 | 9-Cbz | 9-Cbz | 2-DBT | H | H |
| 154179 | 9-Cbz | 9-Cbz | 4-t-BuPh | H | H |
| 154180 | 9-Cbz | 9-Cbz | 1,3-di-t-BuPh | H | H |
| 154181 | 9-Cbz | 9-Cbz | t-Bu | t-Bu | t-Bu |
| 154182 | 9-Cbz | 9-Cbz | Ph | t-Bu | t-Bu |
| 154183 | 9-Cbz | 9-Cbz | CN | t-Bu | t-Bu |
| 154184 | 9-Cbz | 9-Cbz | DPA | t-Bu | t-Bu |
| 154185 | 9-Cbz | 9-Cbz | 2-DBF | t-Bu | t-Bu |
| 154186 | 9-Cbz | 9-Cbz | 2-DBT | t-Bu | t-Bu |
| 154187 | 9-Cbz | 9-Cbz | 4-t-BuPh | t-Bu | t-Bu |
| 154188 | 9-Cbz | 9-Cbz | 1,3-di-t-BuPh | t-Bu | t-Bu |
| 154189 | 9-Cbz | 9-Cbz | 9-Cbz | t-Bu | t-Bu |
| 154190 | 9-Cbz | 9-Cbz | t-Bu | Ph | Ph |
| 154191 | 9-Cbz | 9-Cbz | Ph | Ph | Ph |
| 154192 | 9-Cbz | 9-Cbz | CN | Ph | Ph |
| 154193 | 9-Cbz | 9-Cbz | DPA | Ph | Ph |
| 154194 | 9-Cbz | 9-Cbz | 2-DBF | Ph | Ph |
| 154195 | 9-Cbz | 9-Cbz | 2-DBT | Ph | Ph |
| 154196 | 9-Cbz | 9-Cbz | 4-t-BuPh | Ph | Ph |
| 154197 | 9-Cbz | 9-Cbz | 1,3-di-t-BuPh | Ph | Ph |
| 154198 | 9-Cbz | 9-Cbz | 9-Cbz | Ph | Ph |
| 154199 | 9-Cbz | 9-Cbz | t-Bu | CN | CN |
| 154200 | 9-Cbz | 9-Cbz | Ph | CN | CN |
| 154201 | 9-Cbz | 9-Cbz | CN | CN | CN |
| 154202 | 9-Cbz | 9-Cbz | DPA | CN | CN |
| 154203 | 9-Cbz | 9-Cbz | 2-DBF | CN | CN |
| 154204 | 9-Cbz | 9-Cbz | 2-DBT | CN | CN |
| 154205 | 9-Cbz | 9-Cbz | 4-t-BuPh | CN | CN |
| 154206 | 9-Cbz | 9-Cbz | 1,3-di-t-BuPh | CN | CN |
| 154207 | 9-Cbz | 9-Cbz | 9-Cbz | CN | CN |
| 154208 | 9-Cbz | 9-Cbz | t-Bu | 9-Cbz | 9-Cbz |
| 154209 | 9-Cbz | 9-Cbz | Ph | 9-Cbz | 9-Cbz |
| 154210 | 9-Cbz | 9-Cbz | CN | 9-Cbz | 9-Cbz |
| 154211 | 9-Cbz | 9-Cbz | DPA | 9-Cbz | 9-Cbz |
| 154212 | 9-Cbz | 9-Cbz | 2-DBF | 9-Cbz | 9-Cbz |
| 154213 | 9-Cbz | 9-Cbz | 2-DBT | 9-Cbz | 9-Cbz |
| 154214 | 9-Cbz | 9-Cbz | 4-t-BuPh | 9-Cbz | 9-Cbz |
| 154215 | 9-Cbz | 9-Cbz | 1,3-di-t-BuPh | 9-Cbz | 9-Cbz |
| 154216 | 9-Cbz | 9-Cbz | 9-Cbz | 9-Cbz | 9-Cbz |
| 154217 | 9-Cbz | 9-Cbz | t-Bu | 4-t-BuPh | 4-t-BuPh |
| 154218 | 9-Cbz | 9-Cbz | Ph | 4-t-BuPh | 4-t-BuPh |
| 154219 | 9-Cbz | 9-Cbz | CN | 4-t-BuPh | 4-t-BuPh |
| 154220 | 9-Cbz | 9-Cbz | DPA | 4-t-BuPh | 4-t-BuPh |
| 154221 | 9-Cbz | 9-Cbz | 2-DBF | 4-t-BuPh | 4-t-BuPh |
| 154222 | 9-Cbz | 9-Cbz | 2-DBT | 4-t-BuPh | 4-t-BuPh |
| 154223 | 9-Cbz | 9-Cbz | 4-t-BuPh | 4-t-BuPh | 4-t-BuPh |
| 154224 | 9-Cbz | 9-Cbz | 1,3-di-t-BuPh | 4-t-BuPh | 4-t-BuPh |
| 154225 | 9-Cbz | 9-Cbz | 9-Cbz | 4-t-BuPh | 4-t-BuPh |
| 154226 | 9-Cbz | 9-Cbz | t-Bu | 1,3-di-t-BuPh | 1,3-di-t-BuPh |
| 154227 | 9-Cbz | 9-Cbz | Ph | 1,3-di-t-BuPh | 1,3-di-t-BuPh |
| 154228 | 9-Cbz | 9-Cbz | CN | 1,3-di-t-BuPh | 1,3-di-t-BuPh |
| 154229 | 9-Cbz | 9-Cbz | DPA | 1,3-di-t-BuPh | 1,3-di-t-BuPh |
| 154230 | 9-Cbz | 9-Cbz | 2-DBF | 1,3-di-t-BuPh | 1,3-di-t-BuPh |
| 154231 | 9-Cbz | 9-Cbz | 2-DBT | 1,3-di-t-BuPh | 1,3-di-t-BuPh |
| 154232 | 9-Cbz | 9-Cbz | 4-t-BuPh | 1,3-di-t-BuPh | 1,3-di-t-BuPh |
| 154233 | 9-Cbz | 9-Cbz | 1,3-di-t-BuPh | 1,3-di-t-BuPh | 1,3-di-t-BuPh |
| 154234 | 9-Cbz | 9-Cbz | 9-Cbz | 1,3-di-t-BuPh | 1,3-di-t-BuPh |
| 154235 | CN | CN | t-Bu | H | H |
| 154236 | CN | CN | Ph | H | H |
| 154237 | CN | CN | DPA | H | H |
| 154238 | CN | CN | 2-DBF | H | H |
| 154239 | CN | CN | 2-DBT | H | H |
| 154240 | CN | CN | 4-t-BuPh | H | H |
| 154241 | CN | CN | 1,3-di-t-BuPh | H | H |
| 154242 | CN | CN | 9-Cbz | H | H |
| 154243 | CN | CN | t-Bu | t-Bu | t-Bu |
| 154244 | CN | CN | Ph | t-Bu | t-Bu |
| 154245 | CN | CN | CN | t-Bu | t-Bu |
| 154246 | CN | CN | DPA | t-Bu | t-Bu |
| 154247 | CN | CN | 2-DBF | t-Bu | t-Bu |
| 154248 | CN | CN | 2-DBT | t-Bu | t-Bu |
| 154249 | CN | CN | 4-t-BuPh | t-Bu | t-Bu |
| 154250 | CN | CN | 1,3-di-t-BuPh | t-Bu | t-Bu |
| 154251 | CN | CN | 9-Cbz | t-Bu | t-Bu |
| 154252 | CN | CN | t-Bu | Ph | Ph |
| 154253 | CN | CN | Ph | Ph | Ph |
| 154254 | CN | CN | CN | Ph | Ph |

TABLE 8-continued

| Compound No. | $R_{11b}$ | $R_{12c}$ | $R_{15C}$ | $R_{18b}$ | $R_{19b}$ |
|---|---|---|---|---|---|
| 154255 | CN | CN | DPA | Ph | Ph |
| 154256 | CN | CN | 2-DBF | Ph | Ph |
| 154257 | CN | CN | 2-DBT | Ph | Ph |
| 154258 | CN | CN | 4-t-BuPh | Ph | Ph |
| 154259 | CN | CN | 1,3-di-t-BuPh | Ph | Ph |
| 154260 | CN | CN | 9-Cbz | Ph | Ph |
| 154261 | CN | CN | t-Bu | CN | CN |
| 154262 | CN | CN | Ph | CN | CN |
| 154263 | CN | CN | CN | CN | CN |
| 154264 | CN | CN | DPA | CN | CN |
| 154265 | CN | CN | 2-DBF | CN | CN |
| 154266 | CN | CN | 2-DBT | CN | CN |
| 154267 | CN | CN | 4-t-BuPh | CN | CN |
| 154268 | CN | CN | 1,3-di-t-BuPh | CN | CN |
| 154269 | CN | CN | 9-Cbz | CN | CN |
| 154270 | CN | CN | t-Bu | 9-Cbz | 9-Cbz |
| 154271 | CN | CN | Ph | 9-Cbz | 9-Cbz |
| 154272 | CN | CN | CN | 9-Cbz | 9-Cbz |
| 154273 | CN | CN | DPA | 9-Cbz | 9-Cbz |
| 154274 | CN | CN | 2-DBF | 9-Cbz | 9-Cbz |
| 154275 | CN | CN | 2-DBT | 9-Cbz | 9-Cbz |
| 154276 | CN | CN | 4-t-BuPh | 9-Cbz | 9-Cbz |
| 154277 | CN | CN | 1,3-di-t-BuPh | 9-Cbz | 9-Cbz |
| 154278 | CN | CN | 9-Cbz | 9-Cbz | 9-Cbz |
| 154279 | CN | CN | t-Bu | 4-t-BuPh | 4-t-BuPh |
| 154280 | CN | CN | Ph | 4-t-BuPh | 4-t-BuPh |
| 154281 | CN | CN | CN | 4-t-BuPh | 4-t-BuPh |
| 154282 | CN | CN | DPA | 4-t-BuPh | 4-t-BuPh |
| 154283 | CN | CN | 2-DBF | 4-t-BuPh | 4-t-BuPh |
| 154284 | CN | CN | 2-DBT | 4-t-BuPh | 4-t-BuPh |
| 154285 | CN | CN | 4-t-BuPh | 4-t-BuPh | 4-t-BuPh |
| 154286 | CN | CN | 1,3-di-t-BuPh | 4-t-BuPh | 4-t-BuPh |
| 154287 | CN | CN | 9-Cbz | 4-t-BuPh | 4-t-BuPh |
| 154288 | CN | CN | t-Bu | 1,3-di-t-BuPh | 1,3-di-t-BuPh |
| 154289 | CN | CN | Ph | 1,3-di-t-BuPh | 1,3-di-t-BuPh |
| 154290 | CN | CN | CN | 1,3-di-t-BuPh | 1,3-di-t-BuPh |
| 154291 | CN | CN | DPA | 1,3-di-t-BuPh | 1,3-di-t-BuPh |
| 154292 | CN | CN | 2-DBF | 1,3-di-t-BuPh | 1,3-di-t-BuPh |
| 154293 | CN | CN | 2-DBT | 1,3-di-t-BuPh | 1,3-di-t-BuPh |
| 154294 | CN | CN | 4-t-BuPh | 1,3-di-t-BuPh | 1,3-di-t-BuPh |
| 154295 | CN | CN | 1,3-di-t-BuPh | 1,3-di-t-BuPh | 1,3-di-t-BuPh |
| 154296 | CN | CN | 9-Cbz | 1,3-di-t-BuPh | 1,3-di-t-BuPh |
| 154297 | 4-t-BuPh | 4-t-BuPh | t-Bu | H | H |
| 154298 | 4-t-BuPh | 4-t-BuPh | Ph | H | H |
| 154299 | 4-t-BuPh | 4-t-BuPh | CN | H | H |
| 154300 | 4-t-BuPh | 4-t-BuPh | DPA | H | H |
| 154301 | 4-t-BuPh | 4-t-BuPh | 2-DBF | H | H |
| 154302 | 4-t-BuPh | 4-t-BuPh | 2-DBT | H | H |
| 154303 | 4-t-BuPh | 4-t-BuPh | 1,3-di-t-BuPh | H | H |
| 154304 | 4-t-BuPh | 4-t-BuPh | 9-Cbz | H | H |
| 154305 | 4-t-BuPh | 4-t-BuPh | t-Bu | t-Bu | t-Bu |
| 154306 | 4-t-BuPh | 4-t-BuPh | Ph | t-Bu | t-Bu |
| 154307 | 4-t-BuPh | 4-t-BuPh | CN | t-Bu | t-Bu |
| 154308 | 4-t-BuPh | 4-t-BuPh | DPA | t-Bu | t-Bu |
| 154309 | 4-t-BuPh | 4-t-BuPh | 2-DBF | t-Bu | t-Bu |
| 154310 | 4-t-BuPh | 4-t-BuPh | 2-DBT | t-Bu | t-Bu |
| 154311 | 4-t-BuPh | 4-t-BuPh | 4-t-BuPh | t-Bu | t-Bu |
| 154312 | 4-t-BuPh | 4-t-BuPh | 1,3-di-t-BuPh | t-Bu | t-Bu |
| 154313 | 4-t-BuPh | 4-t-BuPh | 9-Cbz | t-Bu | t-Bu |
| 154314 | 4-t-BuPh | 4-t-BuPh | t-Bu | Ph | Ph |
| 154315 | 4-t-BuPh | 4-t-BuPh | Ph | Ph | Ph |
| 154316 | 4-t-BuPh | 4-t-BuPh | CN | Ph | Ph |
| 154317 | 4-t-BuPh | 4-t-BuPh | DPA | Ph | Ph |
| 154318 | 4-t-BuPh | 4-t-BuPh | 2-DBF | Ph | Ph |
| 154319 | 4-t-BuPh | 4-t-BuPh | 2-DBT | Ph | Ph |
| 154320 | 4-t-BuPh | 4-t-BuPh | 4-t-BuPh | Ph | Ph |
| 154321 | 4-t-BuPh | 4-t-BuPh | 1,3-di-t-BuPh | Ph | Ph |
| 154322 | 4-t-BuPh | 4-t-BuPh | 9-Cbz | Ph | Ph |
| 154323 | 4-t-BuPh | 4-t-BuPh | t-Bu | CN | CN |
| 154324 | 4-t-BuPh | 4-t-BuPh | Ph | CN | CN |
| 154325 | 4-t-BuPh | 4-t-BuPh | CN | CN | CN |
| 154326 | 4-t-BuPh | 4-t-BuPh | DPA | CN | CN |
| 154327 | 4-t-BuPh | 4-t-BuPh | 2-DBF | CN | CN |
| 154328 | 4-t-BuPh | 4-t-BuPh | 2-DBT | CN | CN |
| 154329 | 4-t-BuPh | 4-t-BuPh | 4-t-BuPh | CN | CN |
| 154330 | 4-t-BuPh | 4-t-BuPh | 1,3-di-t-BuPh | CN | CN |
| 154331 | 4-t-BuPh | 4-t-BuPh | 9-Cbz | CN | CN |
| 154332 | 4-t-BuPh | 4-t-BuPh | t-Bu | 9-Cbz | 9-Cbz |

TABLE 8-continued

| Compound No. | $R_{11b}$ | $R_{12c}$ | $R_{15C}$ | $R_{18b}$ | $R_{19b}$ |
|---|---|---|---|---|---|
| 154333 | 4-t-BuPh | 4-t-BuPh | Ph | 9-Cbz | 9-Cbz |
| 154334 | 4-t-BuPh | 4-t-BuPh | CN | 9-Cbz | 9-Cbz |
| 154335 | 4-t-BuPh | 4-t-BuPh | DPA | 9-Cbz | 9-Cbz |
| 154336 | 4-t-BuPh | 4-t-BuPh | 2-DBF | 9-Cbz | 9-Cbz |
| 154337 | 4-t-BuPh | 4-t-BuPh | 2-DBT | 9-Cbz | 9-Cbz |
| 154338 | 4-t-BuPh | 4-t-BuPh | 4-t-BuPh | 9-Cbz | 9-Cbz |
| 154339 | 4-t-BuPh | 4-t-BuPh | 1,3-di-t-BuPh | 9-Cbz | 9-Cbz |
| 154340 | 4-t-BuPh | 4-t-BuPh | 9-Cbz | 9-Cbz | 9-Cbz |
| 154341 | 4-t-BuPh | 4-t-BuPh | t-Bu | 4-t-BuPh | 4-t-BuPh |
| 154342 | 4-t-BuPh | 4-t-BuPh | Ph | 4-t-BuPh | 4-t-BuPh |
| 154343 | 4-t-BuPh | 4-t-BuPh | CN | 4-t-BuPh | 4-t-BuPh |
| 154344 | 4-t-BuPh | 4-t-BuPh | DPA | 4-t-BuPh | 4-t-BuPh |
| 154345 | 4-t-BuPh | 4-t-BuPh | 2-DBF | 4-t-BuPh | 4-t-BuPh |
| 154346 | 4-t-BuPh | 4-t-BuPh | 2-DBT | 4-t-BuPh | 4-t-BuPh |
| 154347 | 4-t-BuPh | 4-t-BuPh | 4-t-BuPh | 4-t-BuPh | 4-t-BuPh |
| 154348 | 4-t-BuPh | 4-t-BuPh | 1,3-di-t-BuPh | 4-t-BuPh | 4-t-BuPh |
| 154349 | 4-t-BuPh | 4-t-BuPh | 9-Cbz | 4-t-BuPh | 4-t-BuPh |
| 154350 | 4-t-BuPh | 4-t-BuPh | t-Bu | 1,3-di-t-BuPh | 1,3-di-t-BuPh |
| 154351 | 4-t-BuPh | 4-t-BuPh | Ph | 1,3-di-t-BuPh | 1,3-di-t-BuPh |
| 154352 | 4-t-BuPh | 4-t-BuPh | CN | 1,3-di-t-BuPh | 1,3-di-t-BuPh |
| 154353 | 4-t-BuPh | 4-t-BuPh | DPA | 1,3-di-t-BuPh | 1,3-di-t-BuPh |
| 154354 | 4-t-BuPh | 4-t-BuPh | 2-DBF | 1,3-di-t-BuPh | 1,3-di-t-BuPh |
| 154355 | 4-t-BuPh | 4-t-BuPh | 2-DBT | 1,3-di-t-BuPh | 1,3-di-t-BuPh |
| 154356 | 4-t-BuPh | 4-t-BuPh | 4-t-BuPh | 1,3-di-t-BuPh | 1,3-di-t-BuPh |
| 154357 | 4-t-BuPh | 4-t-BuPh | 1,3-di-t-BuPh | 1,3-di-t-BuPh | 1,3-di-t-BuPh |
| 154358 | 4-t-BuPh | 4-t-BuPh | 9-Cbz | 1,3-di-t-BuPh | 1,3-di-t-BuPh |
| 154359 | 1,3-di-t-BuPh | 1,3-di-t-BuPh | t-Bu | H | H |
| 154360 | 1,3-di-t-BuPh | 1,3-di-t-BuPh | Ph | H | H |
| 154361 | 1,3-di-t-BuPh | 1,3-di-t-BuPh | CN | H | H |
| 154362 | 1,3-di-t-BuPh | 1,3-di-t-BuPh | DPA | H | H |
| 154363 | 1,3-di-t-BuPh | 1,3-di-t-BuPh | 2-DBF | H | H |
| 154364 | 1,3-di-t-BuPh | 1,3-di-t-BuPh | 2-DBT | H | H |
| 154365 | 1,3-di-t-BuPh | 1,3-di-t-BuPh | 4-t-BuPh | H | H |
| 154366 | 1,3-di-t-BuPh | 1,3-di-t-BuPh | 9-Cbz | H | H |
| 154367 | 1,3-di-t-BuPh | 1,3-di-t-BuPh | t-Bu | t-Bu | t-Bu |
| 154368 | 1,3-di-t-BuPh | 1,3-di-t-BuPh | Ph | t-Bu | t-Bu |
| 154369 | 1,3-di-t-BuPh | 1,3-di-t-BuPh | CN | t-Bu | t-Bu |
| 154370 | 1,3-di-t-BuPh | 1,3-di-t-BuPh | DPA | t-Bu | t-Bu |
| 154371 | 1,3-di-t-BuPh | 1,3-di-t-BuPh | 2-DBF | t-Bu | t-Bu |
| 154372 | 1,3-di-t-BuPh | 1,3-di-t-BuPh | 2-DBT | t-Bu | t-Bu |
| 154373 | 1,3-di-t-BuPh | 1,3-di-t-BuPh | 4-t-BuPh | t-Bu | t-Bu |
| 154374 | 1,3-di-t-BuPh | 1,3-di-t-BuPh | 1,3-di-t-BuPh | t-Bu | t-Bu |
| 154375 | 1,3-di-t-BuPh | 1,3-di-t-BuPh | 9-Cbz | t-Bu | t-Bu |
| 154376 | 1,3-di-t-BuPh | 1,3-di-t-BuPh | t-Bu | Ph | Ph |
| 154377 | 1,3-di-t-BuPh | 1,3-di-t-BuPh | Ph | Ph | Ph |
| 154378 | 1,3-di-t-BuPh | 1,3-di-t-BuPh | CN | Ph | Ph |
| 154379 | 1,3-di-t-BuPh | 1,3-di-t-BuPh | DPA | Ph | Ph |
| 154380 | 1,3-di-t-BuPh | 1,3-di-t-BuPh | 2-DBF | Ph | Ph |
| 154381 | 1,3-di-t-BuPh | 1,3-di-t-BuPh | 2-DBT | Ph | Ph |
| 154382 | 1,3-di-t-BuPh | 1,3-di-t-BuPh | 4-t-BuPh | Ph | Ph |
| 154383 | 1,3-di-t-BuPh | 1,3-di-t-BuPh | 1,3-di-t-BuPh | Ph | Ph |
| 154384 | 1,3-di-t-BuPh | 1,3-di-t-BuPh | 9-Cbz | Ph | Ph |
| 154385 | 1,3-di-t-BuPh | 1,3-di-t-BuPh | t-Bu | CN | CN |
| 154386 | 1,3-di-t-BuPh | 1,3-di-t-BuPh | Ph | CN | CN |
| 154387 | 1,3-di-t-BuPh | 1,3-di-t-BuPh | CN | CN | CN |
| 154388 | 1,3-di-t-BuPh | 1,3-di-t-BuPh | DPA | CN | CN |
| 154389 | 1,3-di-t-BuPh | 1,3-di-t-BuPh | 2-DBF | CN | CN |
| 154390 | 1,3-di-t-BuPh | 1,3-di-t-BuPh | 2-DBT | CN | CN |
| 154391 | 1,3-di-t-BuPh | 1,3-di-t-BuPh | 4-t-BuPh | CN | CN |
| 154392 | 1,3-di-t-BuPh | 1,3-di-t-BuPh | 1,3-di-t-BuPh | CN | CN |
| 154393 | 1,3-di-t-BuPh | 1,3-di-t-BuPh | 9-Cbz | CN | CN |
| 154394 | 1,3-di-t-BuPh | 1,3-di-t-BuPh | t-Bu | 9-Cbz | 9-Cbz |
| 154395 | 1,3-di-t-BuPh | 1,3-di-t-BuPh | Ph | 9-Cbz | 9-Cbz |
| 154396 | 1,3-di-t-BuPh | 1,3-di-t-BuPh | CN | 9-Cbz | 9-Cbz |
| 154397 | 1,3-di-t-BuPh | 1,3-di-t-BuPh | DPA | 9-Cbz | 9-Cbz |
| 154398 | 1,3-di-t-BuPh | 1,3-di-t-BuPh | 2-DBF | 9-Cbz | 9-Cbz |
| 154399 | 1,3-di-t-BuPh | 1,3-di-t-BuPh | 2-DBT | 9-Cbz | 9-Cbz |
| 154400 | 1,3-di-t-BuPh | 1,3-di-t-BuPh | 4-t-BuPh | 9-Cbz | 9-Cbz |
| 154401 | 1,3-di-t-BuPh | 1,3-di-t-BuPh | 1,3-di-t-BuPh | 9-Cbz | 9-Cbz |
| 154402 | 1,3-di-t-BuPh | 1,3-di-t-BuPh | 9-Cbz | 9-Cbz | 9-Cbz |
| 154403 | 1,3-di-t-BuPh | 1,3-di-t-BuPh | t-Bu | 4-t-BuPh | 4-t-BuPh |
| 154404 | 1,3-di-t-BuPh | 1,3-di-t-BuPh | Ph | 4-t-BuPh | 4-t-BuPh |
| 154405 | 1,3-di-t-BuPh | 1,3-di-t-BuPh | CN | 4-t-BuPh | 4-t-BuPh |
| 154406 | 1,3-di-t-BuPh | 1,3-di-t-BuPh | DPA | 4-t-BuPh | 4-t-BuPh |
| 154407 | 1,3-di-t-BuPh | 1,3-di-t-BuPh | 2-DBF | 4-t-BuPh | 4-t-BuPh |
| 154408 | 1,3-di-t-BuPh | 1,3-di-t-BuPh | 2-DBT | 4-t-BuPh | 4-t-BuPh |
| 154409 | 1,3-di-t-BuPh | 1,3-di-t-BuPh | 4-t-BuPh | 4-t-BuPh | 4-t-BuPh |
| 154410 | 1,3-di-t-BuPh | 1,3-di-t-BuPh | 1,3-di-t-BuPh | 4-t-BuPh | 4-t-BuPh |

TABLE 8-continued

| Compound No. | $R_{11b}$ | $R_{12c}$ | $R_{15C}$ | $R_{18b}$ | $R_{19b}$ |
|---|---|---|---|---|---|
| 154411 | 1,3-di-t-BuPh | 1,3-di-t-BuPh | 9-Cbz | 4-t-BuPh | 4-t-BuPh |
| 154412 | 1,3-di-t-BuPh | 1,3-di-t-BuPh | t-Bu | 1,3-di-t-BuPh | 1,3-di-t-BuPh |
| 154413 | 1,3-di-t-BuPh | 1,3-di-t-BuPh | Ph | 1,3-di-t-BuPh | 1,3-di-t-BuPh |
| 154414 | 1,3-di-t-BuPh | 1,3-di-t-BuPh | CN | 1,3-di-t-BuPh | 1,3-di-t-BuPh |
| 154415 | 1,3-di-t-BuPh | 1,3-di-t-BuPh | DPA | 1,3-di-t-BuPh | 1,3-di-t-BuPh |
| 154416 | 1,3-di-t-BuPh | 1,3-di-t-BuPh | 2-DBF | 1,3-di-t-BuPh | 1,3-di-t-BuPh |
| 154417 | 1,3-di-t-BuPh | 1,3-di-t-BuPh | 2-DBT | 1,3-di-t-BuPh | 1,3-di-t-BuPh |
| 154418 | 1,3-di-t-BuPh | 1,3-di-t-BuPh | 4-t-BuPh | 1,3-di-t-BuPh | 1,3-di-t-BuPh |
| 154419 | 1,3-di-t-BuPh | 1,3-di-t-BuPh | 1,3-di-t-BuPh | 1,3-di-t-BuPh | 1,3-di-t-BuPh |
| 154420 | 1,3-di-t-BuPh | 1,3-di-t-BuPh | 9-Cbz | 1,3-di-t-BuPh | 1,3-di-t-BuPh |

Group HC9

The heterocyclic compound may be represented by Formula 16-4, and substituents may be defined as shown in Table 9.

TABLE 9

| Compound No. | $R_{11b}$ | $R_{12c}$ | $R_{15C}$ | $R_{18b}$ | $R_{19b}$ |
|---|---|---|---|---|---|
| 164001 | t-Bu | t-Bu | t-Bu | t-Bu | t-Bu |
| 164002 | Ph | Ph | t-Bu | Ph | Ph |
| 164003 | t-Bu | t-Bu | H | H | H |
| 164004 | H | H | t-Bu | H | H |
| 164005 | H | H | H | t-Bu | t-Bu |
| 164006 | t-Bu | t-Bu | t-Bu | H | H |
| 164007 | H | H | t-Bu | t-Bu | t-Bu |
| 164008 | t-Bu | t-Bu | H | t-Bu | t-Bu |
| 164009 | Ph | Ph | H | H | H |
| 164010 | H | H | Ph | H | H |
| 164011 | H | H | H | Ph | Ph |
| 164012 | Ph | Ph | Ph | H | H |
| 164013 | H | H | Ph | Ph | Ph |
| 164014 | Ph | Ph | H | Ph | Ph |
| 164015 | CN | CN | H | H | H |
| 164016 | H | H | CN | H | H |
| 164017 | H | H | H | CN | CN |
| 164018 | CN | CN | CN | H | H |
| 164019 | H | H | CN | CN | CN |
| 164020 | CN | CN | H | CN | CN |
| 164021 | 9-Cbz | 9-Cbz | H | H | H |
| 164022 | H | H | 9-Cbz | H | H |
| 164023 | H | H | H | 9-Cbz | 9-Cbz |
| 164024 | 9-Cbz | 9-Cbz | 9-Cbz | H | H |
| 164025 | H | H | 9-Cbz | 9-Cbz | 9-Cbz |
| 164026 | 9-Cbz | 9-Cbz | H | 9-Cbz | 9-Cbz |
| 164027 | Me | Me | H | H | H |
| 164028 | H | H | Me | H | H |
| 164029 | H | H | H | Me | Me |
| 164030 | Me | Me | Me | H | H |
| 164031 | H | H | Me | Me | Me |
| 164032 | Me | Me | H | Me | Me |
| 164033 | CD$_3$ | CD3 | H | H | H |
| 164034 | H | H | CD3 | H | H |
| 164035 | H | H | H | CD3 | CD3 |
| 164036 | CD3 | CD3 | CD3 | H | H |
| 164037 | H | H | CD3 | CD3 | CD3 |
| 164038 | CD3 | CD3 | H | CD3 | CD3 |
| 164039 | 4-t-BuPh | 4-t-BuPh | H | H | H |
| 164040 | H | H | 4-t-BuPh | H | H |
| 164041 | H | H | H | 4-t-BuPh | 4-t-BuPh |
| 164042 | 4-t-BuPh | 4-t-BuPh | 4-t-BuPh | H | H |
| 164043 | H | H | 4-t-BuPh | 4-t-BuPh | 4-t-BuPh |
| 164044 | 4-t-BuPh | 4-t-BuPh | H | 4-t-BuPh | 4-t-BuPh |
| 164045 | 1,3-di-t-BuPh | 1,3-di-t-BuPh | H | H | H |
| 164046 | H | H | 1,3-di-t-BuPh | H | H |
| 164047 | H | H | H | 1,3-di-t-BuPh | 1,3-di-t-BuPh |
| 164048 | 1,3-di-t-BuPh | 1,3-di-t-BuPh | 1,3-di-t-BuPh | H | H |
| 164049 | H | H | 1,3-di-t-BuPh | 1,3-di-t-BuPh | 1,3-di-t-BuPh |
| 164050 | 1,3-di-t-BuPh | 1,3-di-t-BuPh | H | 1,3-di-t-BuPh | 1,3-di-t-BuPh |
| 164051 | t-Bu | t-Bu | Ph | H | H |
| 164052 | t-Bu | t-Bu | CN | H | H |
| 164053 | t-Bu | t-Bu | DPA | H | H |
| 164054 | t-Bu | t-Bu | 2-DBF | H | H |
| 164055 | t-Bu | t-Bu | 2-DBT | H | H |

TABLE 9-continued

| Compound No. | $R_{11b}$ | $R_{12c}$ | $R_{15C}$ | $R_{18b}$ | $R_{19b}$ |
|---|---|---|---|---|---|
| 164056 | t-Bu | t-Bu | 4-t-BuPh | H | H |
| 164057 | t-Bu | t-Bu | 1,3-di-t-BuPh | H | H |
| 164058 | t-Bu | t-Bu | 9-Cbz | H | H |
| 164059 | t-Bu | t-Bu | Ph | t-Bu | t-Bu |
| 164060 | t-Bu | t-Bu | CN | t-Bu | t-Bu |
| 164061 | t-Bu | t-Bu | DPA | t-Bu | t-Bu |
| 164062 | t-Bu | t-Bu | 2-DBF | t-Bu | t-Bu |
| 164063 | t-Bu | t-Bu | 2-DBT | t-Bu | t-Bu |
| 164064 | t-Bu | t-Bu | 4-t-BuPh | t-Bu | t-Bu |
| 164065 | t-Bu | t-Bu | 1,3-di-t-BuPh | t-Bu | t-Bu |
| 164066 | t-Bu | t-Bu | 9-Cbz | t-Bu | t-Bu |
| 164067 | t-Bu | t-Bu | t-Bu | Ph | Ph |
| 164068 | t-Bu | t-Bu | Ph | Ph | Ph |
| 164069 | t-Bu | t-Bu | CN | Ph | Ph |
| 164070 | t-Bu | t-Bu | DPA | Ph | Ph |
| 164071 | t-Bu | t-Bu | 2-DBF | Ph | Ph |
| 164072 | t-Bu | t-Bu | 2-DBT | Ph | Ph |
| 164073 | t-Bu | t-Bu | 4-t-BuPh | Ph | Ph |
| 164074 | t-Bu | t-Bu | 1,3-di-t-BuPh | Ph | Ph |
| 164075 | t-Bu | t-Bu | 9-Cbz | Ph | Ph |
| 164076 | t-Bu | t-Bu | t-Bu | CN | CN |
| 164077 | t-Bu | t-Bu | Ph | CN | CN |
| 164078 | t-Bu | t-Bu | CN | CN | CN |
| 164079 | t-Bu | t-Bu | DPA | CN | CN |
| 164080 | t-Bu | t-Bu | 2-DBF | CN | CN |
| 164081 | t-Bu | t-Bu | 2-DBT | CN | CN |
| 164082 | t-Bu | t-Bu | 4-t-BuPh | CN | CN |
| 164083 | t-Bu | t-Bu | 1,3-di-t-BuPh | CN | CN |
| 164084 | t-Bu | t-Bu | 9-Cbz | CN | CN |
| 164085 | t-Bu | t-Bu | t-Bu | 9-Cbz | 9-Cbz |
| 164086 | t-Bu | t-Bu | Ph | 9-Cbz | 9-Cbz |
| 164087 | t-Bu | t-Bu | CN | 9-Cbz | 9-Cbz |
| 164088 | t-Bu | t-Bu | DPA | 9-Cbz | 9-Cbz |
| 164089 | t-Bu | t-Bu | 2-DBF | 9-Cbz | 9-Cbz |
| 164090 | t-Bu | t-Bu | 2-DBT | 9-Cbz | 9-Cbz |
| 164091 | t-Bu | t-Bu | 4-t-BuPh | 9-Cbz | 9-Cbz |
| 164092 | t-Bu | t-Bu | 1,3-di-t-BuPh | 9-Cbz | 9-Cbz |
| 164093 | t-Bu | t-Bu | 9-Cbz | 9-Cbz | 9-Cbz |
| 164094 | t-Bu | t-Bu | t-Bu | 4-t-BuPh | 4-t-BuPh |
| 164095 | t-Bu | t-Bu | Ph | 4-t-BuPh | 4-t-BuPh |
| 164096 | t-Bu | t-Bu | CN | 4-t-BuPh | 4-t-BuPh |
| 164097 | t-Bu | t-Bu | DPA | 4-t-BuPh | 4-t-BuPh |
| 164098 | t-Bu | t-Bu | 2-DBF | 4-t-BuPh | 4-t-BuPh |
| 164099 | t-Bu | t-Bu | 2-DBT | 4-t-BuPh | 4-t-BuPh |
| 164100 | t-Bu | t-Bu | 4-t-BuPh | 4-t-BuPh | 4-t-BuPh |
| 164101 | t-Bu | t-Bu | 1,3-di-t-BuPh | 4-t-BuPh | 4-t-BuPh |
| 164102 | t-Bu | t-Bu | 9-Cbz | 4-t-BuPh | 4-t-BuPh |
| 164103 | t-Bu | t-Bu | t-Bu | 1,3-di-t-BuPh | 1,3-di-t-BuPh |
| 164104 | t-Bu | t-Bu | Ph | 1,3-di-t-BuPh | 1,3-di-t-BuPh |
| 164105 | t-Bu | t-Bu | CN | 1,3-di-t-BuPh | 1,3-di-t-BuPh |
| 164106 | t-Bu | t-Bu | DPA | 1,3-di-t-BuPh | 1,3-di-t-BuPh |
| 164107 | t-Bu | t-Bu | 2-DBF | 1,3-di-t-BuPh | 1,3-di-t-BuPh |
| 164108 | t-Bu | t-Bu | 2-DBT | 1,3-di-t-BuPh | 1,3-di-t-BuPh |
| 164109 | t-Bu | t-Bu | 4-t-BuPh | 1,3-di-t-BuPh | 1,3-di-t-BuPh |
| 164110 | t-Bu | t-Bu | 1,3-di-t-BuPh | 1,3-di-t-BuPh | 1,3-di-t-BuPh |
| 164111 | t-Bu | t-Bu | 9-Cbz | 1,3-di-t-BuPh | 1,3-di-t-BuPh |
| 164112 | Ph | Ph | t-Bu | H | H |
| 164113 | Ph | Ph | CN | H | H |
| 164114 | Ph | Ph | DPA | H | H |
| 164115 | Ph | Ph | 2-DBF | H | H |
| 164116 | Ph | Ph | 2-DBT | H | H |
| 164117 | Ph | Ph | 4-t-BuPh | H | H |
| 164118 | Ph | Ph | 1,3-di-t-BuPh | H | H |
| 164119 | Ph | Ph | 9-Cbz | H | H |
| 164120 | Ph | Ph | t-Bu | t-Bu | t-Bu |
| 164121 | Ph | Ph | Ph | t-Bu | t-Bu |
| 164122 | Ph | Ph | CN | t-Bu | t-Bu |
| 164123 | Ph | Ph | DPA | t-Bu | t-Bu |
| 164124 | Ph | Ph | 2-DBF | t-Bu | t-Bu |
| 164125 | Ph | Ph | 2-DBT | t-Bu | t-Bu |
| 164126 | Ph | Ph | 4-t-BuPh | t-Bu | t-Bu |
| 164127 | Ph | Ph | 1,3-di-t-BuPh | t-Bu | t-Bu |
| 164128 | Ph | Ph | 9-Cbz | t-Bu | t-Bu |
| 164129 | Ph | Ph | Ph | Ph | Ph |
| 164130 | Ph | Ph | CN | Ph | Ph |
| 164131 | Ph | Ph | DPA | Ph | Ph |
| 164132 | Ph | Ph | 2-DBF | Ph | Ph |
| 164133 | Ph | Ph | 2-DBT | Ph | Ph |

TABLE 9-continued

| Compound No. | $R_{11b}$ | $R_{12c}$ | $R_{15C}$ | $R_{18b}$ | $R_{19b}$ |
|---|---|---|---|---|---|
| 164134 | Ph | Ph | 4-t-BuPh | Ph | Ph |
| 164135 | Ph | Ph | 1,3-di-t-BuPh | Ph | Ph |
| 164136 | Ph | Ph | 9-Cbz | Ph | Ph |
| 164137 | Ph | Ph | t-Bu | CN | CN |
| 164138 | Ph | Ph | Ph | CN | CN |
| 164139 | Ph | Ph | CN | CN | CN |
| 164140 | Ph | Ph | DPA | CN | CN |
| 164141 | Ph | Ph | 2-DBF | CN | CN |
| 164142 | Ph | Ph | 2-DBT | CN | CN |
| 164143 | Ph | Ph | 4-t-BuPh | CN | CN |
| 164144 | Ph | Ph | 1,3-di-t-BuPh | CN | CN |
| 164145 | Ph | Ph | 9-Cbz | CN | CN |
| 164146 | Ph | Ph | t-Bu | 9-Cbz | 9-Cbz |
| 164147 | Ph | Ph | Ph | 9-Cbz | 9-Cbz |
| 164148 | Ph | Ph | CN | 9-Cbz | 9-Cbz |
| 164149 | Ph | Ph | DPA | 9-Cbz | 9-Cbz |
| 164150 | Ph | Ph | 2-DBF | 9-Cbz | 9-Cbz |
| 164151 | Ph | Ph | 2-DBT | 9-Cbz | 9-Cbz |
| 164152 | Ph | Ph | 4-t-BuPh | 9-Cbz | 9-Cbz |
| 164153 | Ph | Ph | 1,3-di-t-BuPh | 9-Cbz | 9-Cbz |
| 164154 | Ph | Ph | 9-Cbz | 9-Cbz | 9-Cbz |
| 164155 | Ph | Ph | t-Bu | 4-t-BuPh | 4-t-BuPh |
| 164156 | Ph | Ph | Ph | 4-t-BuPh | 4-t-BuPh |
| 164157 | Ph | Ph | CN | 4-t-BuPh | 4-t-BuPh |
| 164158 | Ph | Ph | DPA | 4-t-BuPh | 4-t-BuPh |
| 164159 | Ph | Ph | 2-DBF | 4-t-BuPh | 4-t-BuPh |
| 164160 | Ph | Ph | 2-DBT | 4-t-BuPh | 4-t-BuPh |
| 164161 | Ph | Ph | 4-t-BuPh | 4-t-BuPh | 4-t-BuPh |
| 164162 | Ph | Ph | 1,3-di-t-BuPh | 4-t-BuPh | 4-t-BuPh |
| 164163 | Ph | Ph | 9-Cbz | 4-t-BuPh | 4-t-BuPh |
| 164164 | Ph | Ph | t-Bu | 1,3-di-t-BuPh | 1,3-di-t-BuPh |
| 164165 | Ph | Ph | Ph | 1,3-di-t-BuPh | 1,3-di-t-BuPh |
| 164166 | Ph | Ph | CN | 1,3-di-t-BuPh | 1,3-di-t-BuPh |
| 164167 | Ph | Ph | DPA | 1,3-di-t-BuPh | 1,3-di-t-BuPh |
| 164168 | Ph | Ph | 2-DBF | 1,3-di-t-BuPh | 1,3-di-t-BuPh |
| 164169 | Ph | Ph | 2-DBT | 1,3-di-t-BuPh | 1,3-di-t-BuPh |
| 164170 | Ph | Ph | 4-t-BuPh | 1,3-di-t-BuPh | 1,3-di-t-BuPh |
| 164171 | Ph | Ph | 1,3-di-t-BuPh | 1,3-di-t-BuPh | 1,3-di-t-BuPh |
| 164172 | Ph | Ph | 9-Cbz | 1,3-di-t-BuPh | 1,3-di-t-BuPh |
| 164173 | 9-Cbz | 9-Cbz | t-Bu | H | H |
| 164174 | 9-Cbz | 9-Cbz | Ph | H | H |
| 164175 | 9-Cbz | 9-Cbz | CN | H | H |
| 164176 | 9-Cbz | 9-Cbz | DPA | H | H |
| 164177 | 9-Cbz | 9-Cbz | 2-DBF | H | H |
| 164178 | 9-Cbz | 9-Cbz | 2-DBT | H | H |
| 164179 | 9-Cbz | 9-Cbz | 4-t-BuPh | H | H |
| 164180 | 9-Cbz | 9-Cbz | 1,3-di-t-BuPh | H | H |
| 164181 | 9-Cbz | 9-Cbz | t-Bu | t-Bu | t-Bu |
| 164182 | 9-Cbz | 9-Cbz | Ph | t-Bu | t-Bu |
| 164183 | 9-Cbz | 9-Cbz | CN | t-Bu | t-Bu |
| 164184 | 9-Cbz | 9-Cbz | DPA | t-Bu | t-Bu |
| 164185 | 9-Cbz | 9-Cbz | 2-DBF | t-Bu | t-Bu |
| 164186 | 9-Cbz | 9-Cbz | 2-DBT | t-Bu | t-Bu |
| 164187 | 9-Cbz | 9-Cbz | 4-t-BuPh | t-Bu | t-Bu |
| 164188 | 9-Cbz | 9-Cbz | 1,3-di-t-BuPh | t-Bu | t-Bu |
| 164189 | 9-Cbz | 9-Cbz | 9-Cbz | t-Bu | t-Bu |
| 164190 | 9-Cbz | 9-Cbz | t-Bu | Ph | Ph |
| 164191 | 9-Cbz | 9-Cbz | Ph | Ph | Ph |
| 164192 | 9-Cbz | 9-Cbz | CN | Ph | Ph |
| 164193 | 9-Cbz | 9-Cbz | DPA | Ph | Ph |
| 164194 | 9-Cbz | 9-Cbz | 2-DBF | Ph | Ph |
| 164195 | 9-Cbz | 9-Cbz | 2-DBT | Ph | Ph |
| 164196 | 9-Cbz | 9-Cbz | 4-t-BuPh | Ph | Ph |
| 164197 | 9-Cbz | 9-Cbz | 1,3-di-t-BuPh | Ph | Ph |
| 164198 | 9-Cbz | 9-Cbz | 9-Cbz | Ph | Ph |
| 164199 | 9-Cbz | 9-Cbz | t-Bu | CN | CN |
| 164200 | 9-Cbz | 9-Cbz | Ph | CN | CN |
| 164201 | 9-Cbz | 9-Cbz | CN | CN | CN |
| 164202 | 9-Cbz | 9-Cbz | DPA | CN | CN |
| 164203 | 9-Cbz | 9-Cbz | 2-DBF | CN | CN |
| 164204 | 9-Cbz | 9-Cbz | 2-DBT | CN | CN |
| 164205 | 9-Cbz | 9-Cbz | 4-t-BuPh | CN | CN |
| 164206 | 9-Cbz | 9-Cbz | 1,3-di-t-BuPh | CN | CN |
| 164207 | 9-Cbz | 9-Cbz | 9-Cbz | CN | CN |
| 164208 | 9-Cbz | 9-Cbz | t-Bu | 9-Cbz | 9-Cbz |
| 164209 | 9-Cbz | 9-Cbz | Ph | 9-Cbz | 9-Cbz |
| 164210 | 9-Cbz | 9-Cbz | CN | 9-Cbz | 9-Cbz |
| 164211 | 9-Cbz | 9-Cbz | DPA | 9-Cbz | 9-Cbz |

TABLE 9-continued

| Compound No. | $R_{11b}$ | $R_{12c}$ | $R_{15C}$ | $R_{18b}$ | $R_{19b}$ |
|---|---|---|---|---|---|
| 164212 | 9-Cbz | 9-Cbz | 2-DBF | 9-Cbz | 9-Cbz |
| 164213 | 9-Cbz | 9-Cbz | 2-DBT | 9-Cbz | 9-Cbz |
| 164214 | 9-Cbz | 9-Cbz | 4-t-BuPh | 9-Cbz | 9-Cbz |
| 164215 | 9-Cbz | 9-Cbz | 1,3-di-t-BuPh | 9-Cbz | 9-Cbz |
| 164216 | 9-Cbz | 9-Cbz | 9-Cbz | 9-Cbz | 9-Cbz |
| 164217 | 9-Cbz | 9-Cbz | t-Bu | 4-t-BuPh | 4-t-BuPh |
| 164218 | 9-Cbz | 9-Cbz | Ph | 4-t-BuPh | 4-t-BuPh |
| 164219 | 9-Cbz | 9-Cbz | CN | 4-t-BuPh | 4-t-BuPh |
| 164220 | 9-Cbz | 9-Cbz | DPA | 4-t-BuPh | 4-t-BuPh |
| 164221 | 9-Cbz | 9-Cbz | 2-DBF | 4-t-BuPh | 4-t-BuPh |
| 164222 | 9-Cbz | 9-Cbz | 2-DBT | 4-t-BuPh | 4-t-BuPh |
| 164223 | 9-Cbz | 9-Cbz | 4-t-BuPh | 4-t-BuPh | 4-t-BuPh |
| 164224 | 9-Cbz | 9-Cbz | 1,3-di-t-BuPh | 4-t-BuPh | 4-t-BuPh |
| 164225 | 9-Cbz | 9-Cbz | 9-Cbz | 4-t-BuPh | 4-t-BuPh |
| 164226 | 9-Cbz | 9-Cbz | t-Bu | 1,3-di-t-BuPh | 1,3-di-t-BuPh |
| 164227 | 9-Cbz | 9-Cbz | Ph | 1,3-di-t-BuPh | 1,3-di-t-BuPh |
| 164228 | 9-Cbz | 9-Cbz | CN | 1,3-di-t-BuPh | 1,3-di-t-BuPh |
| 164229 | 9-Cbz | 9-Cbz | DPA | 1,3-di-t-BuPh | 1,3-di-t-BuPh |
| 164230 | 9-Cbz | 9-Cbz | 2-DBF | 1,3-di-t-BuPh | 1,3-di-t-BuPh |
| 164231 | 9-Cbz | 9-Cbz | 2-DBT | 1,3-di-t-BuPh | 1,3-di-t-BuPh |
| 164232 | 9-Cbz | 9-Cbz | 4-t-BuPh | 1,3-di-t-BuPh | 1,3-di-t-BuPh |
| 164233 | 9-Cbz | 9-Cbz | 1,3-di-t-BuPh | 1,3-di-t-BuPh | 1,3-di-t-BuPh |
| 164234 | 9-Cbz | 9-Cbz | 9-Cbz | 1,3-di-t-BuPh | 1,3-di-t-BuPh |
| 164235 | CN | CN | t-Bu | H | H |
| 164236 | CN | CN | Ph | H | H |
| 164237 | CN | CN | DPA | H | H |
| 164238 | CN | CN | 2-DBF | H | H |
| 164239 | CN | CN | 2-DBT | H | H |
| 164240 | CN | CN | 4-t-BuPh | H | H |
| 164241 | CN | CN | 1,3-di-t-BuPh | H | H |
| 164242 | CN | CN | 9-Cbz | H | H |
| 164243 | CN | CN | t-Bu | t-Bu | t-Bu |
| 164244 | CN | CN | Ph | t-Bu | t-Bu |
| 164245 | CN | CN | CN | t-Bu | t-Bu |
| 164246 | CN | CN | DPA | t-Bu | t-Bu |
| 164247 | CN | CN | 2-DBF | t-Bu | t-Bu |
| 164248 | CN | CN | 2-DBT | t-Bu | t-Bu |
| 164249 | CN | CN | 4-t-BuPh | t-Bu | t-Bu |
| 164250 | CN | CN | 1,3-di-t-BuPh | t-Bu | t-Bu |
| 164251 | CN | CN | 9-Cbz | t-Bu | t-Bu |
| 164252 | CN | CN | t-Bu | Ph | Ph |
| 164253 | CN | CN | Ph | Ph | Ph |
| 164254 | CN | CN | CN | Ph | Ph |
| 164255 | CN | CN | DPA | Ph | Ph |
| 164256 | CN | CN | 2-DBF | Ph | Ph |
| 164257 | CN | CN | 2-DBT | Ph | Ph |
| 164258 | CN | CN | 4-t-BuPh | Ph | Ph |
| 164259 | CN | CN | 1,3-di-t-BuPh | Ph | Ph |
| 164260 | CN | CN | 9-Cbz | Ph | Ph |
| 164261 | CN | CN | t-Bu | CN | CN |
| 164262 | CN | CN | Ph | CN | CN |
| 164263 | CN | CN | CN | CN | CN |
| 164264 | CN | CN | DPA | CN | CN |
| 164265 | CN | CN | 2-DBF | CN | CN |
| 164266 | CN | CN | 2-DBT | CN | CN |
| 164267 | CN | CN | 4-t-BuPh | CN | CN |
| 164268 | CN | CN | 1,3-di-t-BuPh | CN | CN |
| 164269 | CN | CN | 9-Cbz | CN | CN |
| 164270 | CN | CN | t-Bu | 9-Cbz | 9-Cbz |
| 164271 | CN | CN | Ph | 9-Cbz | 9-Cbz |
| 164272 | CN | CN | CN | 9-Cbz | 9-Cbz |
| 164273 | CN | CN | DPA | 9-Cbz | 9-Cbz |
| 164274 | CN | CN | 2-DBF | 9-Cbz | 9-Cbz |
| 164275 | CN | CN | 2-DBT | 9-Cbz | 9-Cbz |
| 164276 | CN | CN | 4-t-BuPh | 9-Cbz | 9-Cbz |
| 164277 | CN | CN | 1,3-di-t-BuPh | 9-Cbz | 9-Cbz |
| 164278 | CN | CN | 9-Cbz | 9-Cbz | 9-Cbz |
| 164279 | CN | CN | t-Bu | 4-t-BuPh | 4-t-BuPh |
| 164280 | CN | CN | Ph | 4-t-BuPh | 4-t-BuPh |
| 164281 | CN | CN | CN | 4-t-BuPh | 4-t-BuPh |
| 164282 | CN | CN | DPA | 4-t-BuPh | 4-t-BuPh |
| 164283 | CN | CN | 2-DBF | 4-t-BuPh | 4-t-BuPh |
| 164284 | CN | CN | 2-DBT | 4-t-BuPh | 4-t-BuPh |
| 164285 | CN | CN | 4-t-BuPh | 4-t-BuPh | 4-t-BuPh |
| 164286 | CN | CN | 1,3-di-t-BuPh | 4-t-BuPh | 4-t-BuPh |
| 164287 | CN | CN | 9-Cbz | 4-t-BuPh | 4-t-BuPh |
| 164288 | CN | CN | t-Bu | 1,3-di-t-BuPh | 1,3-di-t-BuPh |
| 164289 | CN | CN | Ph | 1,3-di-t-BuPh | 1,3-di-t-BuPh |

TABLE 9-continued

| Compound No. | $R_{11b}$ | $R_{12c}$ | $R_{15C}$ | $R_{18b}$ | $R_{19b}$ |
|---|---|---|---|---|---|
| 164290 | CN | CN | CN | 1,3-di-t-BuPh | 1,3-di-t-BuPh |
| 164291 | CN | CN | DPA | 1,3-di-t-BuPh | 1,3-di-t-BuPh |
| 164292 | CN | CN | 2-DBF | 1,3-di-t-BuPh | 1,3-di-t-BuPh |
| 164293 | CN | CN | 2-DBT | 1,3-di-t-BuPh | 1,3-di-t-BuPh |
| 164294 | CN | CN | 4-t-BuPh | 1,3-di-t-BuPh | 1,3-di-t-BuPh |
| 164295 | CN | CN | 1,3-di-t-BuPh | 1,3-di-t-BuPh | 1,3-di-t-BuPh |
| 164296 | CN | CN | 9-Cbz | 1,3-di-t-BuPh | 1,3-di-t-BuPh |
| 164297 | 4-t-BuPh | 4-t-BuPh | t-Bu | H | H |
| 164298 | 4-t-BuPh | 4-t-BuPh | Ph | H | H |
| 164299 | 4-t-BuPh | 4-t-BuPh | CN | H | H |
| 164300 | 4-t-BuPh | 4-t-BuPh | DPA | H | H |
| 164301 | 4-t-BuPh | 4-t-BuPh | 2-DBF | H | H |
| 164302 | 4-t-BuPh | 4-t-BuPh | 2-DBT | H | H |
| 164303 | 4-t-BuPh | 4-t-BuPh | 1,3-di-t-BuPh | H | H |
| 164304 | 4-t-BuPh | 4-t-BuPh | 9-Cbz | H | H |
| 164305 | 4-t-BuPh | 4-t-BuPh | t-Bu | t-Bu | t-Bu |
| 164306 | 4-t-BuPh | 4-t-BuPh | Ph | t-Bu | t-Bu |
| 164307 | 4-t-BuPh | 4-t-BuPh | CN | t-Bu | t-Bu |
| 164308 | 4-t-BuPh | 4-t-BuPh | DPA | t-Bu | t-Bu |
| 164309 | 4-t-BuPh | 4-t-BuPh | 2-DBF | t-Bu | t-Bu |
| 164310 | 4-t-BuPh | 4-t-BuPh | 2-DBT | t-Bu | t-Bu |
| 164311 | 4-t-BuPh | 4-t-BuPh | 4-t-BuPh | t-Bu | t-Bu |
| 164312 | 4-t-BuPh | 4-t-BuPh | 1,3-di-t-BuPh | t-Bu | t-Bu |
| 164313 | 4-t-BuPh | 4-t-BuPh | 9-Cbz | t-Bu | t-Bu |
| 164314 | 4-t-BuPh | 4-t-BuPh | t-Bu | Ph | Ph |
| 164315 | 4-t-BuPh | 4-t-BuPh | Ph | Ph | Ph |
| 164316 | 4-t-BuPh | 4-t-BuPh | CN | Ph | Ph |
| 164317 | 4-t-BuPh | 4-t-BuPh | DPA | Ph | Ph |
| 164318 | 4-t-BuPh | 4-t-BuPh | 2-DBF | Ph | Ph |
| 164319 | 4-t-BuPh | 4-t-BuPh | 2-DBT | Ph | Ph |
| 164320 | 4-t-BuPh | 4-t-BuPh | 4-t-BuPh | Ph | Ph |
| 164321 | 4-t-BuPh | 4-t-BuPh | 1,3-di-t-BuPh | Ph | Ph |
| 164322 | 4-t-BuPh | 4-t-BuPh | 9-Cbz | Ph | Ph |
| 164323 | 4-t-BuPh | 4-t-BuPh | t-Bu | CN | CN |
| 164324 | 4-t-BuPh | 4-t-BuPh | Ph | CN | CN |
| 164325 | 4-t-BuPh | 4-t-BuPh | CN | CN | CN |
| 164326 | 4-t-BuPh | 4-t-BuPh | DPA | CN | CN |
| 164327 | 4-t-BuPh | 4-t-BuPh | 2-DBF | CN | CN |
| 164328 | 4-t-BuPh | 4-t-BuPh | 2-DBT | CN | CN |
| 164329 | 4-t-BuPh | 4-t-BuPh | 4-t-BuPh | CN | CN |
| 164330 | 4-t-BuPh | 4-t-BuPh | 1,3-di-t-BuPh | CN | CN |
| 164331 | 4-t-BuPh | 4-t-BuPh | 9-Cbz | CN | CN |
| 164332 | 4-t-BuPh | 4-t-BuPh | t-Bu | 9-Cbz | 9-Cbz |
| 164333 | 4-t-BuPh | 4-t-BuPh | Ph | 9-Cbz | 9-Cbz |
| 164334 | 4-t-BuPh | 4-t-BuPh | CN | 9-Cbz | 9-Cbz |
| 164335 | 4-t-BuPh | 4-t-BuPh | DPA | 9-Cbz | 9-Cbz |
| 164336 | 4-t-BuPh | 4-t-BuPh | 2-DBF | 9-Cbz | 9-Cbz |
| 164337 | 4-t-BuPh | 4-t-BuPh | 2-DBT | 9-Cbz | 9-Cbz |
| 164338 | 4-t-BuPh | 4-t-BuPh | 4-t-BuPh | 9-Cbz | 9-Cbz |
| 164339 | 4-t-BuPh | 4-t-BuPh | 1,3-di-t-BuPh | 9-Cbz | 9-Cbz |
| 164340 | 4-t-BuPh | 4-t-BuPh | 9-Cbz | 9-Cbz | 9-Cbz |
| 164341 | 4-t-BuPh | 4-t-BuPh | t-Bu | 4-t-BuPh | 4-t-BuPh |
| 164342 | 4-t-BuPh | 4-t-BuPh | Ph | 4-t-BuPh | 4-t-BuPh |
| 164343 | 4-t-BuPh | 4-t-BuPh | CN | 4-t-BuPh | 4-t-BuPh |
| 164344 | 4-t-BuPh | 4-t-BuPh | DPA | 4-t-BuPh | 4-t-BuPh |
| 164345 | 4-t-BuPh | 4-t-BuPh | 2-DBF | 4-t-BuPh | 4-t-BuPh |
| 164346 | 4-t-BuPh | 4-t-BuPh | 2-DBT | 4-t-BuPh | 4-t-BuPh |
| 164347 | 4-t-BuPh | 4-t-BuPh | 4-t-BuPh | 4-t-BuPh | 4-t-BuPh |
| 164348 | 4-t-BuPh | 4-t-BuPh | 1,3-di-t-BuPh | 4-t-BuPh | 4-t-BuPh |
| 164349 | 4-t-BuPh | 4-t-BuPh | 9-Cbz | 4-t-BuPh | 4-t-BuPh |
| 164350 | 4-t-BuPh | 4-t-BuPh | t-Bu | 1,3-di-t-BuPh | 1,3-di-t-BuPh |
| 164351 | 4-t-BuPh | 4-t-BuPh | Ph | 1,3-di-t-BuPh | 1,3-di-t-BuPh |
| 164352 | 4-t-BuPh | 4-t-BuPh | CN | 1,3-di-t-BuPh | 1,3-di-t-BuPh |
| 164353 | 4-t-BuPh | 4-t-BuPh | DPA | 1,3-di-t-BuPh | 1,3-di-t-BuPh |
| 164354 | 4-t-BuPh | 4-t-BuPh | 2-DBF | 1,3-di-t-BuPh | 1,3-di-t-BuPh |
| 164355 | 4-t-BuPh | 4-t-BuPh | 2-DBT | 1,3-di-t-BuPh | 1,3-di-t-BuPh |
| 164356 | 4-t-BuPh | 4-t-BuPh | 4-t-BuPh | 1,3-di-t-BuPh | 1,3-di-t-BuPh |
| 164357 | 4-t-BuPh | 4-t-BuPh | 1,3-di-t-BuPh | 1,3-di-t-BuPh | 1,3-di-t-BuPh |
| 164358 | 4-t-BuPh | 4-t-BuPh | 9-Cbz | 1,3-di-t-BuPh | 1,3-di-t-BuPh |
| 164359 | 1,3-di-t-BuPh | 1,3-di-t-BuPh | t-Bu | H | H |
| 164360 | 1,3-di-t-BuPh | 1,3-di-t-BuPh | Ph | H | H |
| 164361 | 1,3-di-t-BuPh | 1,3-di-t-BuPh | CN | H | H |
| 164362 | 1,3-di-t-BuPh | 1,3-di-t-BuPh | DPA | H | H |
| 164363 | 1,3-di-t-BuPh | 1,3-di-t-BuPh | 2-DBF | H | H |
| 164364 | 1,3-di-t-BuPh | 1,3-di-t-BuPh | 2-DBT | H | H |
| 164365 | 1,3-di-t-BuPh | 1,3-di-t-BuPh | 4-t-BuPh | H | H |
| 164366 | 1,3-di-t-BuPh | 1,3-di-t-BuPh | 9-Cbz | H | H |
| 164367 | 1,3-di-t-BuPh | 1,3-di-t-BuPh | t-Bu | t-Bu | t-Bu |

TABLE 9-continued

| Compound No. | $R_{11b}$ | $R_{12c}$ | $R_{15C}$ | $R_{18b}$ | $R_{19b}$ |
|---|---|---|---|---|---|
| 164368 | 1,3-di-t-BuPh | 1,3-di-t-BuPh | Ph | t-Bu | t-Bu |
| 164369 | 1,3-di-t-BuPh | 1,3-di-t-BuPh | CN | t-Bu | t-Bu |
| 164370 | 1,3-di-t-BuPh | 1,3-di-t-BuPh | DPA | t-Bu | t-Bu |
| 164371 | 1,3-di-t-BuPh | 1,3-di-t-BuPh | 2-DBF | t-Bu | t-Bu |
| 164372 | 1,3-di-t-BuPh | 1,3-di-t-BuPh | 2-DBT | t-Bu | t-Bu |
| 164373 | 1,3-di-t-BuPh | 1,3-di-t-BuPh | 4-t-BuPh | t-Bu | t-Bu |
| 164374 | 1,3-di-t-BuPh | 1,3-di-t-BuPh | 1,3-di-t-BuPh | t-Bu | t-Bu |
| 164375 | 1,3-di-t-BuPh | 1,3-di-t-BuPh | 9-Cbz | t-Bu | t-Bu |
| 164376 | 1,3-di-t-BuPh | 1,3-di-t-BuPh | t-Bu | Ph | Ph |
| 164377 | 1,3-di-t-BuPh | 1,3-di-t-BuPh | Ph | Ph | Ph |
| 164378 | 1,3-di-t-BuPh | 1,3-di-t-BuPh | CN | Ph | Ph |
| 164379 | 1,3-di-t-BuPh | 1,3-di-t-BuPh | DPA | Ph | Ph |
| 164380 | 1,3-di-t-BuPh | 1,3-di-t-BuPh | 2-DBF | Ph | Ph |
| 164381 | 1,3-di-t-BuPh | 1,3-di-t-BuPh | 2-DBT | Ph | Ph |
| 164382 | 1,3-di-t-BuPh | 1,3-di-t-BuPh | 4-t-BuPh | Ph | Ph |
| 164383 | 1,3-di-t-BuPh | 1,3-di-t-BuPh | 1,3-di-t-BuPh | Ph | Ph |
| 164384 | 1,3-di-t-BuPh | 1,3-di-t-BuPh | 9-Cbz | Ph | Ph |
| 164385 | 1,3-di-t-BuPh | 1,3-di-t-BuPh | t-Bu | CN | CN |
| 164386 | 1,3-di-t-BuPh | 1,3-di-t-BuPh | Ph | CN | CN |
| 164387 | 1,3-di-t-BuPh | 1,3-di-t-BuPh | CN | CN | CN |
| 164388 | 1,3-di-t-BuPh | 1,3-di-t-BuPh | DPA | CN | CN |
| 164389 | 1,3-di-t-BuPh | 1,3-di-t-BuPh | 2-DBF | CN | CN |
| 164390 | 1,3-di-t-BuPh | 1,3-di-t-BuPh | 2-DBT | CN | CN |
| 164391 | 1,3-di-t-BuPh | 1,3-di-t-BuPh | 4-t-BuPh | CN | CN |
| 164392 | 1,3-di-t-BuPh | 1,3-di-t-BuPh | 1,3-di-t-BuPh | CN | CN |
| 164393 | 1,3-di-t-BuPh | 1,3-di-t-BuPh | 9-Cbz | CN | CN |
| 164394 | 1,3-di-t-BuPh | 1,3-di-t-BuPh | t-Bu | 9-Cbz | 9-Cbz |
| 164395 | 1,3-di-t-BuPh | 1,3-di-t-BuPh | Ph | 9-Cbz | 9-Cbz |
| 164396 | 1,3-di-t-BuPh | 1,3-di-t-BuPh | CN | 9-Cbz | 9-Cbz |
| 164397 | 1,3-di-t-BuPh | 1,3-di-t-BuPh | DPA | 9-Cbz | 9-Cbz |
| 164398 | 1,3-di-t-BuPh | 1,3-di-t-BuPh | 2-DBF | 9-Cbz | 9-Cbz |
| 164399 | 1,3-di-t-BuPh | 1,3-di-t-BuPh | 2-DBT | 9-Cbz | 9-Cbz |
| 164400 | 1,3-di-t-BuPh | 1,3-di-t-BuPh | 4-t-BuPh | 9-Cbz | 9-Cbz |
| 164401 | 1,3-di-t-BuPh | 1,3-di-t-BuPh | 1,3-di-t-BuPh | 9-Cbz | 9-Cbz |
| 164402 | 1,3-di-t-BuPh | 1,3-di-t-BuPh | 9-Cbz | 9-Cbz | 9-Cbz |
| 164403 | 1,3-di-t-BuPh | 1,3-di-t-BuPh | t-Bu | 4-t-BuPh | 4-t-BuPh |
| 164404 | 1,3-di-t-BuPh | 1,3-di-t-BuPh | Ph | 4-t-BuPh | 4-t-BuPh |
| 164405 | 1,3-di-t-BuPh | 1,3-di-t-BuPh | CN | 4-t-BuPh | 4-t-BuPh |
| 164406 | 1,3-di-t-BuPh | 1,3-di-t-BuPh | DPA | 4-t-BuPh | 4-t-BuPh |
| 164407 | 1,3-di-t-BuPh | 1,3-di-t-BuPh | 2-DBF | 4-t-BuPh | 4-t-BuPh |
| 164408 | 1,3-di-t-BuPh | 1,3-di-t-BuPh | 2-DBT | 4-t-BuPh | 4-t-BuPh |
| 164409 | 1,3-di-t-BuPh | 1,3-di-t-BuPh | 4-t-BuPh | 4-t-BuPh | 4-t-BuPh |
| 164410 | 1,3-di-t-BuPh | 1,3-di-t-BuPh | 1,3-di-t-BuPh | 4-t-BuPh | 4-t-BuPh |
| 164411 | 1,3-di-t-BuPh | 1,3-di-t-BuPh | 9-Cbz | 4-t-BuPh | 4-t-BuPh |
| 164412 | 1,3-di-t-BuPh | 1,3-di-t-BuPh | t-Bu | 1,3-di-t-BuPh | 1,3-di-t-BuPh |
| 164413 | 1,3-di-t-BuPh | 1,3-di-t-BuPh | Ph | 1,3-di-t-BuPh | 1,3-di-t-BuPh |
| 164414 | 1,3-di-t-BuPh | 1,3-di-t-BuPh | CN | 1,3-di-t-BuPh | 1,3-di-t-BuPh |
| 164415 | 1,3-di-t-BuPh | 1,3-di-t-BuPh | DPA | 1,3-di-t-BuPh | 1,3-di-t-BuPh |
| 164416 | 1,3-di-t-BuPh | 1,3-di-t-BuPh | 2-DBF | 1,3-di-t-BuPh | 1,3-di-t-BuPh |
| 164417 | 1,3-di-t-BuPh | 1,3-di-t-BuPh | 2-DBT | 1,3-di-t-BuPh | 1,3-di-t-BuPh |
| 164418 | 1,3-di-t-BuPh | 1,3-di-t-BuPh | 4-t-BuPh | 1,3-di-t-BuPh | 1,3-di-t-BuPh |
| 164419 | 1,3-di-t-BuPh | 1,3-di-t-BuPh | 1,3-di-t-BuPh | 1,3-di-t-BuPh | 1,3-di-t-BuPh |
| 164420 | 1,3-di-t-BuPh | 1,3-di-t-BuPh | 9-Cbz | 1,3-di-t-BuPh | 1,3-di-t-BuPh |

Group HC10

The heterocyclic compound may be represented by Formula 17-4, and substituents may be defined as shown in Table 10.

TABLE 10

| Compound No. | $R_{11b}$ | $R_{12c}$ | $R_{15C}$ | $R_{18b}$ | $R_{19b}$ |
|---|---|---|---|---|---|
| 174001 | t-Bu | t-Bu | t-Bu | t-Bu | t-Bu |
| 174002 | Ph | Ph | t-Bu | Ph | Ph |
| 174003 | t-Bu | t-Bu | H | H | H |
| 174004 | H | H | t-Bu | H | H |
| 174005 | H | H | H | t-Bu | t-Bu |
| 174006 | t-Bu | t-Bu | t-Bu | H | H |
| 174007 | H | H | t-Bu | t-Bu | t-Bu |
| 174008 | t-Bu | t-Bu | H | t-Bu | t-Bu |
| 174009 | Ph | Ph | H | H | H |
| 174010 | H | H | Ph | H | H |
| 174011 | H | H | H | Ph | Ph |
| 174012 | Ph | Ph | Ph | H | H |

TABLE 10-continued

| Compound No. | $R_{11b}$ | $R_{12c}$ | $R_{15C}$ | $R_{18b}$ | $R_{19b}$ |
|---|---|---|---|---|---|
| 174013 | H | H | Ph | Ph | Ph |
| 174014 | Ph | Ph | H | Ph | Ph |
| 174015 | CN | CN | H | H | H |
| 174016 | H | H | CN | H | H |
| 174017 | H | H | H | CN | CN |
| 174018 | CN | CN | CN | H | H |
| 174019 | H | H | CN | CN | CN |
| 174020 | CN | CN | H | CN | CN |
| 174021 | 9-Cbz | 9-Cbz | H | H | H |
| 174022 | H | H | 9-Cbz | H | H |
| 174023 | H | H | H | 9-Cbz | 9-Cbz |
| 174024 | 9-Cbz | 9-Cbz | 9-Cbz | H | H |
| 174025 | H | H | 9-Cbz | 9-Cbz | 9-Cbz |
| 174026 | 9-Cbz | 9-Cbz | H | 9-Cbz | 9-Cbz |
| 174027 | Me | Me | H | H | H |
| 174028 | H | H | Me | H | H |
| 174029 | H | H | H | Me | Me |
| 174030 | Me | Me | Me | H | H |
| 174031 | H | H | Me | Me | Me |
| 174032 | Me | Me | H | Me | Me |
| 174033 | CD$_3$ | CD3 | H | H | H |
| 174034 | H | H | CD3 | H | H |
| 174035 | H | H | H | CD3 | CD3 |
| 174036 | CD3 | CD3 | CD3 | H | H |
| 174037 | H | H | CD3 | CD3 | CD3 |
| 174038 | CD3 | CD3 | H | CD3 | CD3 |
| 174039 | 4-t-BuPh | 4-t-BuPh | H | H | H |
| 174040 | H | H | 4-t-BuPh | H | H |
| 174041 | H | H | H | 4-t-BuPh | 4-t-BuPh |
| 174042 | 4-t-BuPh | 4-t-BuPh | 4-t-BuPh | H | H |
| 174043 | H | H | 4-t-BuPh | 4-t-BuPh | 4-t-BuPh |
| 174044 | 4-t-BuPh | 4-t-BuPh | H | 4-t-BuPh | 4-t-BuPh |
| 174045 | 1,3-di-t-BuPh | 1,3-di-t-BuPh | H | H | H |
| 174046 | H | H | 1,3-di-t-BuPh | H | H |
| 174047 | H | H | H | 1,3-di-t-BuPh | 1,3-di-t-BuPh |
| 174048 | 1,3-di-t-BuPh | 1,3-di-t-BuPh | 1,3-di-t-BuPh | H | H |
| 174049 | H | H | 1,3-di-t-BuPh | 1,3-di-t-BuPh | 1,3-di-t-BuPh |
| 174050 | 1,3-di-t-BuPh | 1,3-di-t-BuPh | H | 1,3-di-t-BuPh | 1,3-di-t-BuPh |
| 174051 | t-Bu | t-Bu | Ph | H | H |
| 174052 | t-Bu | t-Bu | CN | H | H |
| 174053 | t-Bu | t-Bu | DPA | H | H |
| 174054 | t-Bu | t-Bu | 2-DBF | H | H |
| 174055 | t-Bu | t-Bu | 2-DBT | H | H |
| 174056 | t-Bu | t-Bu | 4-t-BuPh | H | H |
| 174057 | t-Bu | t-Bu | 1,3-di-t-BuPh | H | H |
| 174058 | t-Bu | t-Bu | 9-Cbz | H | H |
| 174059 | t-Bu | t-Bu | Ph | t-Bu | t-Bu |
| 174060 | t-Bu | t-Bu | CN | t-Bu | t-Bu |
| 174061 | t-Bu | t-Bu | DPA | t-Bu | t-Bu |
| 174062 | t-Bu | t-Bu | 2-DBF | t-Bu | t-Bu |
| 174063 | t-Bu | t-Bu | 2-DBT | t-Bu | t-Bu |
| 174064 | t-Bu | t-Bu | 4-t-BuPh | t-Bu | t-Bu |
| 174065 | t-Bu | t-Bu | 1,3-di-t-BuPh | t-Bu | t-Bu |
| 174066 | t-Bu | t-Bu | 9-Cbz | t-Bu | t-Bu |
| 174067 | t-Bu | t-Bu | t-Bu | Ph | Ph |
| 174068 | t-Bu | t-Bu | Ph | Ph | Ph |
| 174069 | t-Bu | t-Bu | CN | Ph | Ph |
| 174070 | t-Bu | t-Bu | DPA | Ph | Ph |
| 174071 | t-Bu | t-Bu | 2-DBF | Ph | Ph |
| 174072 | t-Bu | t-Bu | 2-DBT | Ph | Ph |
| 174073 | t-Bu | t-Bu | 4-t-BuPh | Ph | Ph |
| 174074 | t-Bu | t-Bu | 1,3-di-t-BuPh | Ph | Ph |
| 174075 | t-Bu | t-Bu | 9-Cbz | Ph | Ph |
| 174076 | t-Bu | t-Bu | t-Bu | CN | CN |
| 174077 | t-Bu | t-Bu | Ph | CN | CN |
| 174078 | t-Bu | t-Bu | CN | CN | CN |
| 174079 | t-Bu | t-Bu | DPA | CN | CN |
| 174080 | t-Bu | t-Bu | 2-DBF | CN | CN |
| 174081 | t-Bu | t-Bu | 2-DBT | CN | CN |
| 174082 | t-Bu | t-Bu | 4-t-BuPh | CN | CN |
| 174083 | t-Bu | t-Bu | 1,3-di-t-BuPh | CN | CN |
| 174084 | t-Bu | t-Bu | 9-Cbz | CN | CN |
| 174085 | t-Bu | t-Bu | t-Bu | 9-Cbz | 9-Cbz |
| 174086 | t-Bu | t-Bu | Ph | 9-Cbz | 9-Cbz |
| 174087 | t-Bu | t-Bu | CN | 9-Cbz | 9-Cbz |
| 174088 | t-Bu | t-Bu | DPA | 9-Cbz | 9-Cbz |
| 174089 | t-Bu | t-Bu | 2-DBF | 9-Cbz | 9-Cbz |
| 174090 | t-Bu | t-Bu | 2-DBT | 9-Cbz | 9-Cbz |

TABLE 10-continued

| Compound No. | $R_{11b}$ | $R_{12c}$ | $R_{15C}$ | $R_{18b}$ | $R_{19b}$ |
|---|---|---|---|---|---|
| 174091 | t-Bu | t-Bu | 4-t-BuPh | 9-Cbz | 9-Cbz |
| 174092 | t-Bu | t-Bu | 1,3-di-t-BuPh | 9-Cbz | 9-Cbz |
| 174093 | t-Bu | t-Bu | 9-Cbz | 9-Cbz | 9-Cbz |
| 174094 | t-Bu | t-Bu | t-Bu | 4-t-BuPh | 4-t-BuPh |
| 174095 | t-Bu | t-Bu | Ph | 4-t-BuPh | 4-t-BuPh |
| 174096 | t-Bu | t-Bu | CN | 4-t-BuPh | 4-t-BuPh |
| 174097 | t-Bu | t-Bu | DPA | 4-t-BuPh | 4-t-BuPh |
| 174098 | t-Bu | t-Bu | 2-DBF | 4-t-BuPh | 4-t-BuPh |
| 174099 | t-Bu | t-Bu | 2-DBT | 4-t-BuPh | 4-t-BuPh |
| 174100 | t-Bu | t-Bu | 4-t-BuPh | 4-t-BuPh | 4-t-BuPh |
| 174101 | t-Bu | t-Bu | 1,3-di-t-BuPh | 4-t-BuPh | 4-t-BuPh |
| 174102 | t-Bu | t-Bu | 9-Cbz | 4-t-BuPh | 4-t-BuPh |
| 174103 | t-Bu | t-Bu | t-Bu | 1,3-di-t-BuPh | 1,3-di-t-BuPh |
| 174104 | t-Bu | t-Bu | Ph | 1,3-di-t-BuPh | 1,3-di-t-BuPh |
| 174105 | t-Bu | t-Bu | CN | 1,3-di-t-BuPh | 1,3-di-t-BuPh |
| 174106 | t-Bu | t-Bu | DPA | 1,3-di-t-BuPh | 1,3-di-t-BuPh |
| 174107 | t-Bu | t-Bu | 2-DBF | 1,3-di-t-BuPh | 1,3-di-t-BuPh |
| 174108 | t-Bu | t-Bu | 2-DBT | 1,3-di-t-BuPh | 1,3-di-t-BuPh |
| 174109 | t-Bu | t-Bu | 4-t-BuPh | 1,3-di-t-BuPh | 1,3-di-t-BuPh |
| 174110 | t-Bu | t-Bu | 1,3-di-t-BuPh | 1,3-di-t-BuPh | 1,3-di-t-BuPh |
| 174111 | t-Bu | t-Bu | 9-Cbz | 1,3-di-t-BuPh | 1,3-di-t-BuPh |
| 174112 | Ph | Ph | t-Bu | H | H |
| 174113 | Ph | Ph | CN | H | H |
| 174114 | Ph | Ph | DPA | H | H |
| 174115 | Ph | Ph | 2-DBF | H | H |
| 174116 | Ph | Ph | 2-DBT | H | H |
| 174117 | Ph | Ph | 4-t-BuPh | H | H |
| 174118 | Ph | Ph | 1,3-di-t-BuPh | H | H |
| 174119 | Ph | Ph | 9-Cbz | H | H |
| 174120 | Ph | Ph | t-Bu | t-Bu | t-Bu |
| 174121 | Ph | Ph | Ph | t-Bu | t-Bu |
| 174122 | Ph | Ph | CN | t-Bu | t-Bu |
| 174123 | Ph | Ph | DPA | t-Bu | t-Bu |
| 174124 | Ph | Ph | 2-DBF | t-Bu | t-Bu |
| 174125 | Ph | Ph | 2-DBT | t-Bu | t-Bu |
| 174126 | Ph | Ph | 4-t-BuPh | t-Bu | t-Bu |
| 174127 | Ph | Ph | 1,3-di-t-BuPh | t-Bu | t-Bu |
| 174128 | Ph | Ph | 9-Cbz | t-Bu | t-Bu |
| 174129 | Ph | Ph | Ph | Ph | Ph |
| 174130 | Ph | Ph | CN | Ph | Ph |
| 174131 | Ph | Ph | DPA | Ph | Ph |
| 174132 | Ph | Ph | 2-DBF | Ph | Ph |
| 174133 | Ph | Ph | 2-DBT | Ph | Ph |
| 174134 | Ph | Ph | 4-t-BuPh | Ph | Ph |
| 174135 | Ph | Ph | 1,3-di-t-BuPh | Ph | Ph |
| 174136 | Ph | Ph | 9-Cbz | Ph | Ph |
| 174137 | Ph | Ph | t-Bu | CN | CN |
| 174138 | Ph | Ph | Ph | CN | CN |
| 174139 | Ph | Ph | CN | CN | CN |
| 174140 | Ph | Ph | DPA | CN | CN |
| 174141 | Ph | Ph | 2-DBF | CN | CN |
| 174142 | Ph | Ph | 2-DBT | CN | CN |
| 174143 | Ph | Ph | 4-t-BuPh | CN | CN |
| 174144 | Ph | Ph | 1,3-di-t-BuPh | CN | CN |
| 174145 | Ph | Ph | 9-Cbz | CN | CN |
| 174146 | Ph | Ph | t-Bu | 9-Cbz | 9-Cbz |
| 174147 | Ph | Ph | Ph | 9-Cbz | 9-Cbz |
| 174148 | Ph | Ph | CN | 9-Cbz | 9-Cbz |
| 174149 | Ph | Ph | DPA | 9-Cbz | 9-Cbz |
| 174150 | Ph | Ph | 2-DBF | 9-Cbz | 9-Cbz |
| 174151 | Ph | Ph | 2-DBT | 9-Cbz | 9-Cbz |
| 174152 | Ph | Ph | 4-t-BuPh | 9-Cbz | 9-Cbz |
| 174153 | Ph | Ph | 1,3-di-t-BuPh | 9-Cbz | 9-Cbz |
| 174154 | Ph | Ph | 9-Cbz | 9-Cbz | 9-Cbz |
| 174155 | Ph | Ph | t-Bu | 4-t-BuPh | 4-t-BuPh |
| 174156 | Ph | Ph | Ph | 4-t-BuPh | 4-t-BuPh |
| 174157 | Ph | Ph | CN | 4-t-BuPh | 4-t-BuPh |
| 174158 | Ph | Ph | DPA | 4-t-BuPh | 4-t-BuPh |
| 174159 | Ph | Ph | 2-DBF | 4-t-BuPh | 4-t-BuPh |
| 174160 | Ph | Ph | 2-DBT | 4-t-BuPh | 4-t-BuPh |
| 174161 | Ph | Ph | 4-t-BuPh | 4-t-BuPh | 4-t-BuPh |
| 174162 | Ph | Ph | 1,3-di-t-BuPh | 4-t-BuPh | 4-t-BuPh |
| 174163 | Ph | Ph | 9-Cbz | 4-t-BuPh | 4-t-BuPh |
| 174164 | Ph | Ph | t-Bu | 1,3-di-t-BuPh | 1,3-di-t-BuPh |
| 174165 | Ph | Ph | Ph | 1,3-di-t-BuPh | 1,3-di-t-BuPh |
| 174166 | Ph | Ph | CN | 1,3-di-t-BuPh | 1,3-di-t-BuPh |
| 174167 | Ph | Ph | DPA | 1,3-di-t-BuPh | 1,3-di-t-BuPh |
| 174168 | Ph | Ph | 2-DBF | 1,3-di-t-BuPh | 1,3-di-t-BuPh |

TABLE 10-continued

| Compound No. | $R_{11b}$ | $R_{12c}$ | $R_{15C}$ | $R_{18b}$ | $R_{19b}$ |
|---|---|---|---|---|---|
| 174169 | Ph | Ph | 2-DBT | 1,3-di-t-BuPh | 1,3-di-t-BuPh |
| 174170 | Ph | Ph | 4-t-BuPh | 1,3-di-t-BuPh | 1,3-di-t-BuPh |
| 174171 | Ph | Ph | 1,3-di-t-BuPh | 1,3-di-t-BuPh | 1,3-di-t-BuPh |
| 174172 | Ph | Ph | 9-Cbz | 1,3-di-t-BuPh | 1,3-di-t-BuPh |
| 174173 | 9-Cbz | 9-Cbz | t-Bu | H | H |
| 174174 | 9-Cbz | 9-Cbz | Ph | H | H |
| 174175 | 9-Cbz | 9-Cbz | CN | H | H |
| 174176 | 9-Cbz | 9-Cbz | DPA | H | H |
| 174177 | 9-Cbz | 9-Cbz | 2-DBF | H | H |
| 174178 | 9-Cbz | 9-Cbz | 2-DBT | H | H |
| 174179 | 9-Cbz | 9-Cbz | 4-t-BuPh | H | H |
| 174180 | 9-Cbz | 9-Cbz | 1,3-di-t-BuPh | H | H |
| 174181 | 9-Cbz | 9-Cbz | t-Bu | t-Bu | t-Bu |
| 174182 | 9-Cbz | 9-Cbz | Ph | t-Bu | t-Bu |
| 174183 | 9-Cbz | 9-Cbz | CN | t-Bu | t-Bu |
| 174184 | 9-Cbz | 9-Cbz | DPA | t-Bu | t-Bu |
| 174185 | 9-Cbz | 9-Cbz | 2-DBF | t-Bu | t-Bu |
| 174186 | 9-Cbz | 9-Cbz | 2-DBT | t-Bu | t-Bu |
| 174187 | 9-Cbz | 9-Cbz | 4-t-BuPh | t-Bu | t-Bu |
| 174188 | 9-Cbz | 9-Cbz | 1,3-di-t-BuPh | t-Bu | t-Bu |
| 174189 | 9-Cbz | 9-Cbz | 9-Cbz | t-Bu | t-Bu |
| 174190 | 9-Cbz | 9-Cbz | t-Bu | Ph | Ph |
| 174191 | 9-Cbz | 9-Cbz | Ph | Ph | Ph |
| 174192 | 9-Cbz | 9-Cbz | CN | Ph | Ph |
| 174193 | 9-Cbz | 9-Cbz | DPA | Ph | Ph |
| 174194 | 9-Cbz | 9-Cbz | 2-DBF | Ph | Ph |
| 174195 | 9-Cbz | 9-Cbz | 2-DBT | Ph | Ph |
| 174196 | 9-Cbz | 9-Cbz | 4-t-BuPh | Ph | Ph |
| 174197 | 9-Cbz | 9-Cbz | 1,3-di-t-BuPh | Ph | Ph |
| 174198 | 9-Cbz | 9-Cbz | 9-Cbz | Ph | Ph |
| 174199 | 9-Cbz | 9-Cbz | t-Bu | CN | CN |
| 174200 | 9-Cbz | 9-Cbz | Ph | CN | CN |
| 174201 | 9-Cbz | 9-Cbz | CN | CN | CN |
| 174202 | 9-Cbz | 9-Cbz | DPA | CN | CN |
| 174203 | 9-Cbz | 9-Cbz | 2-DBF | CN | CN |
| 174204 | 9-Cbz | 9-Cbz | 2-DBT | CN | CN |
| 174205 | 9-Cbz | 9-Cbz | 4-t-BuPh | CN | CN |
| 174206 | 9-Cbz | 9-Cbz | 1,3-di-t-BuPh | CN | CN |
| 174207 | 9-Cbz | 9-Cbz | 9-Cbz | CN | CN |
| 174208 | 9-Cbz | 9-Cbz | t-Bu | 9-Cbz | 9-Cbz |
| 174209 | 9-Cbz | 9-Cbz | Ph | 9-Cbz | 9-Cbz |
| 174210 | 9-Cbz | 9-Cbz | CN | 9-Cbz | 9-Cbz |
| 174211 | 9-Cbz | 9-Cbz | DPA | 9-Cbz | 9-Cbz |
| 174212 | 9-Cbz | 9-Cbz | 2-DBF | 9-Cbz | 9-Cbz |
| 174213 | 9-Cbz | 9-Cbz | 2-DBT | 9-Cbz | 9-Cbz |
| 174214 | 9-Cbz | 9-Cbz | 4-t-BuPh | 9-Cbz | 9-Cbz |
| 174215 | 9-Cbz | 9-Cbz | 1,3-di-t-BuPh | 9-Cbz | 9-Cbz |
| 174216 | 9-Cbz | 9-Cbz | 9-Cbz | 9-Cbz | 9-Cbz |
| 174217 | 9-Cbz | 9-Cbz | t-Bu | 4-t-BuPh | 4-t-BuPh |
| 174218 | 9-Cbz | 9-Cbz | Ph | 4-t-BuPh | 4-t-BuPh |
| 174219 | 9-Cbz | 9-Cbz | CN | 4-t-BuPh | 4-t-BuPh |
| 174220 | 9-Cbz | 9-Cbz | DPA | 4-t-BuPh | 4-t-BuPh |
| 174221 | 9-Cbz | 9-Cbz | 2-DBF | 4-t-BuPh | 4-t-BuPh |
| 174222 | 9-Cbz | 9-Cbz | 2-DBT | 4-t-BuPh | 4-t-BuPh |
| 174223 | 9-Cbz | 9-Cbz | 4-t-BuPh | 4-t-BuPh | 4-t-BuPh |
| 174224 | 9-Cbz | 9-Cbz | 1,3-di-t-BuPh | 4-t-BuPh | 4-t-BuPh |
| 174225 | 9-Cbz | 9-Cbz | 9-Cbz | 4-t-BuPh | 4-t-BuPh |
| 174226 | 9-Cbz | 9-Cbz | t-Bu | 1,3-di-t-BuPh | 1,3-di-t-BuPh |
| 174227 | 9-Cbz | 9-Cbz | Ph | 1,3-di-t-BuPh | 1,3-di-t-BuPh |
| 174228 | 9-Cbz | 9-Cbz | CN | 1,3-di-t-BuPh | 1,3-di-t-BuPh |
| 174229 | 9-Cbz | 9-Cbz | DPA | 1,3-di-t-BuPh | 1,3-di-t-BuPh |
| 174230 | 9-Cbz | 9-Cbz | 2-DBF | 1,3-di-t-BuPh | 1,3-di-t-BuPh |
| 174231 | 9-Cbz | 9-Cbz | 2-DBT | 1,3-di-t-BuPh | 1,3-di-t-BuPh |
| 174232 | 9-Cbz | 9-Cbz | 4-t-BuPh | 1,3-di-t-BuPh | 1,3-di-t-BuPh |
| 174233 | 9-Cbz | 9-Cbz | 1,3-di-t-BuPh | 1,3-di-t-BuPh | 1,3-di-t-BuPh |
| 174234 | 9-Cbz | 9-Cbz | 9-Cbz | 1,3-di-t-BuPh | 1,3-di-t-BuPh |
| 174235 | CN | CN | t-Bu | H | H |
| 174236 | CN | CN | Ph | H | H |
| 174237 | CN | CN | DPA | H | H |
| 174238 | CN | CN | 2-DBF | H | H |
| 174239 | CN | CN | 2-DBT | H | H |
| 174240 | CN | CN | 4-t-BuPh | H | H |
| 174241 | CN | CN | 1,3-di-t-BuPh | H | H |
| 174242 | CN | CN | 9-Cbz | H | H |
| 174243 | CN | CN | t-Bu | t-Bu | t-Bu |
| 174244 | CN | CN | Ph | t-Bu | t-Bu |
| 174245 | CN | CN | CN | t-Bu | t-Bu |
| 174246 | CN | CN | DPA | t-Bu | t-Bu |

TABLE 10-continued

| Compound No. | $R_{11b}$ | $R_{12c}$ | $R_{15C}$ | $R_{18b}$ | $R_{19b}$ |
|---|---|---|---|---|---|
| 174247 | CN | CN | 2-DBF | t-Bu | t-Bu |
| 174248 | CN | CN | 2-DBT | t-Bu | t-Bu |
| 174249 | CN | CN | 4-t-BuPh | t-Bu | t-Bu |
| 174250 | CN | CN | 1,3-di-t-BuPh | t-Bu | t-Bu |
| 174251 | CN | CN | 9-Cbz | t-Bu | t-Bu |
| 174252 | CN | CN | t-Bu | Ph | Ph |
| 174253 | CN | CN | Ph | Ph | Ph |
| 174254 | CN | CN | CN | Ph | Ph |
| 174255 | CN | CN | DPA | Ph | Ph |
| 174256 | CN | CN | 2-DBF | Ph | Ph |
| 174257 | CN | CN | 2-DBT | Ph | Ph |
| 174258 | CN | CN | 4-t-BuPh | Ph | Ph |
| 174259 | CN | CN | 1,3-di-t-BuPh | Ph | Ph |
| 174260 | CN | CN | 9-Cbz | Ph | Ph |
| 174261 | CN | CN | t-Bu | CN | CN |
| 174262 | CN | CN | Ph | CN | CN |
| 174263 | CN | CN | CN | CN | CN |
| 174264 | CN | CN | DPA | CN | CN |
| 174265 | CN | CN | 2-DBF | CN | CN |
| 174266 | CN | CN | 2-DBT | CN | CN |
| 174267 | CN | CN | 4-t-BuPh | CN | CN |
| 174268 | CN | CN | 1,3-di-t-BuPh | CN | CN |
| 174269 | CN | CN | 9-Cbz | CN | CN |
| 174270 | CN | CN | t-Bu | 9-Cbz | 9-Cbz |
| 174271 | CN | CN | Ph | 9-Cbz | 9-Cbz |
| 174272 | CN | CN | CN | 9-Cbz | 9-Cbz |
| 174273 | CN | CN | DPA | 9-Cbz | 9-Cbz |
| 174274 | CN | CN | 2-DBF | 9-Cbz | 9-Cbz |
| 174275 | CN | CN | 2-DBT | 9-Cbz | 9-Cbz |
| 174276 | CN | CN | 4-t-BuPh | 9-Cbz | 9-Cbz |
| 174277 | CN | CN | 1,3-di-t-BuPh | 9-Cbz | 9-Cbz |
| 174278 | CN | CN | 9-Cbz | 9-Cbz | 9-Cbz |
| 174279 | CN | CN | t-Bu | 4-t-BuPh | 4-t-BuPh |
| 174280 | CN | CN | Ph | 4-t-BuPh | 4-t-BuPh |
| 174281 | CN | CN | CN | 4-t-BuPh | 4-t-BuPh |
| 174282 | CN | CN | DPA | 4-t-BuPh | 4-t-BuPh |
| 174283 | CN | CN | 2-DBF | 4-t-BuPh | 4-t-BuPh |
| 174284 | CN | CN | 2-DBT | 4-t-BuPh | 4-t-BuPh |
| 174285 | CN | CN | 4-t-BuPh | 4-t-BuPh | 4-t-BuPh |
| 174286 | CN | CN | 1,3-di-t-BuPh | 4-t-BuPh | 4-t-BuPh |
| 174287 | CN | CN | 9-Cbz | 4-t-BuPh | 4-t-BuPh |
| 174288 | CN | CN | t-Bu | 1,3-di-t-BuPh | 1,3-di-t-BuPh |
| 174289 | CN | CN | Ph | 1,3-di-t-BuPh | 1,3-di-t-BuPh |
| 174290 | CN | CN | CN | 1,3-di-t-BuPh | 1,3-di-t-BuPh |
| 174291 | CN | CN | DPA | 1,3-di-t-BuPh | 1,3-di-t-BuPh |
| 174292 | CN | CN | 2-DBF | 1,3-di-t-BuPh | 1,3-di-t-BuPh |
| 174293 | CN | CN | 2-DBT | 1,3-di-t-BuPh | 1,3-di-t-BuPh |
| 174294 | CN | CN | 4-t-BuPh | 1,3-di-t-BuPh | 1,3-di-t-BuPh |
| 174295 | CN | CN | 1,3-di-t-BuPh | 1,3-di-t-BuPh | 1,3-di-t-BuPh |
| 174296 | CN | CN | 9-Cbz | 1,3-di-t-BuPh | 1,3-di-t-BuPh |
| 174297 | 4-t-BuPh | 4-t-BuPh | t-Bu | H | H |
| 174298 | 4-t-BuPh | 4-t-BuPh | Ph | H | H |
| 174299 | 4-t-BuPh | 4-t-BuPh | CN | H | H |
| 174300 | 4-t-BuPh | 4-t-BuPh | DPA | H | H |
| 174301 | 4-t-BuPh | 4-t-BuPh | 2-DBF | H | H |
| 174302 | 4-t-BuPh | 4-t-BuPh | 2-DBT | H | H |
| 174303 | 4-t-BuPh | 4-t-BuPh | 1,3-di-t-BuPh | H | H |
| 174304 | 4-t-BuPh | 4-t-BuPh | 9-Cbz | H | H |
| 174305 | 4-t-BuPh | 4-t-BuPh | t-Bu | t-Bu | t-Bu |
| 174306 | 4-t-BuPh | 4-t-BuPh | Ph | t-Bu | t-Bu |
| 174307 | 4-t-BuPh | 4-t-BuPh | CN | t-Bu | t-Bu |
| 174308 | 4-t-BuPh | 4-t-BuPh | DPA | t-Bu | t-Bu |
| 174309 | 4-t-BuPh | 4-t-BuPh | 2-DBF | t-Bu | t-Bu |
| 174310 | 4-t-BuPh | 4-t-BuPh | 2-DBT | t-Bu | t-Bu |
| 174311 | 4-t-BuPh | 4-t-BuPh | 4-t-BuPh | t-Bu | t-Bu |
| 174312 | 4-t-BuPh | 4-t-BuPh | 1,3-di-t-BuPh | t-Bu | t-Bu |
| 174313 | 4-t-BuPh | 4-t-BuPh | 9-Cbz | t-Bu | t-Bu |
| 174314 | 4-t-BuPh | 4-t-BuPh | t-Bu | Ph | Ph |
| 174315 | 4-t-BuPh | 4-t-BuPh | Ph | Ph | Ph |
| 174316 | 4-t-BuPh | 4-t-BuPh | CN | Ph | Ph |
| 174317 | 4-t-BuPh | 4-t-BuPh | DPA | Ph | Ph |
| 174318 | 4-t-BuPh | 4-t-BuPh | 2-DBF | Ph | Ph |
| 174319 | 4-t-BuPh | 4-t-BuPh | 2-DBT | Ph | Ph |
| 174320 | 4-t-BuPh | 4-t-BuPh | 4-t-BuPh | Ph | Ph |
| 174321 | 4-t-BuPh | 4-t-BuPh | 1,3-di-t-BuPh | Ph | Ph |
| 174322 | 4-t-BuPh | 4-t-BuPh | 9-Cbz | Ph | Ph |
| 174323 | 4-t-BuPh | 4-t-BuPh | t-Bu | CN | CN |
| 174324 | 4-t-BuPh | 4-t-BuPh | Ph | CN | CN |

TABLE 10-continued

| Compound No. | $R_{11b}$ | $R_{12c}$ | $R_{15C}$ | $R_{18b}$ | $R_{19b}$ |
|---|---|---|---|---|---|
| 174325 | 4-t-BuPh | 4-t-BuPh | CN | CN | CN |
| 174326 | 4-t-BuPh | 4-t-BuPh | DPA | CN | CN |
| 174327 | 4-t-BuPh | 4-t-BuPh | 2-DBF | CN | CN |
| 174328 | 4-t-BuPh | 4-t-BuPh | 2-DBT | CN | CN |
| 174329 | 4-t-BuPh | 4-t-BuPh | 4-t-BuPh | CN | CN |
| 174330 | 4-t-BuPh | 4-t-BuPh | 1,3-di-t-BuPh | CN | CN |
| 174331 | 4-t-BuPh | 4-t-BuPh | 9-Cbz | CN | CN |
| 174332 | 4-t-BuPh | 4-t-BuPh | t-Bu | 9-Cbz | 9-Cbz |
| 174333 | 4-t-BuPh | 4-t-BuPh | Ph | 9-Cbz | 9-Cbz |
| 174334 | 4-t-BuPh | 4-t-BuPh | CN | 9-Cbz | 9-Cbz |
| 174335 | 4-t-BuPh | 4-t-BuPh | DPA | 9-Cbz | 9-Cbz |
| 174336 | 4-t-BuPh | 4-t-BuPh | 2-DBF | 9-Cbz | 9-Cbz |
| 174337 | 4-t-BuPh | 4-t-BuPh | 2-DBT | 9-Cbz | 9-Cbz |
| 174338 | 4-t-BuPh | 4-t-BuPh | 4-t-BuPh | 9-Cbz | 9-Cbz |
| 174339 | 4-t-BuPh | 4-t-BuPh | 1,3-di-t-BuPh | 9-Cbz | 9-Cbz |
| 174340 | 4-t-BuPh | 4-t-BuPh | 9-Cbz | 9-Cbz | 9-Cbz |
| 174341 | 4-t-BuPh | 4-t-BuPh | t-Bu | 4-t-BuPh | 4-t-BuPh |
| 174342 | 4-t-BuPh | 4-t-BuPh | Ph | 4-t-BuPh | 4-t-BuPh |
| 174343 | 4-t-BuPh | 4-t-BuPh | CN | 4-t-BuPh | 4-t-BuPh |
| 174344 | 4-t-BuPh | 4-t-BuPh | DPA | 4-t-BuPh | 4-t-BuPh |
| 174345 | 4-t-BuPh | 4-t-BuPh | 2-DBF | 4-t-BuPh | 4-t-BuPh |
| 174346 | 4-t-BuPh | 4-t-BuPh | 2-DBT | 4-t-BuPh | 4-t-BuPh |
| 174347 | 4-t-BuPh | 4-t-BuPh | 4-t-BuPh | 4-t-BuPh | 4-t-BuPh |
| 174348 | 4-t-BuPh | 4-t-BuPh | 1,3-di-t-BuPh | 4-t-BuPh | 4-t-BuPh |
| 174349 | 4-t-BuPh | 4-t-BuPh | 9-Cbz | 4-t-BuPh | 4-t-BuPh |
| 174350 | 4-t-BuPh | 4-t-BuPh | t-Bu | 1,3-di-t-BuPh | 1,3-di-t-BuPh |
| 174351 | 4-t-BuPh | 4-t-BuPh | Ph | 1,3-di-t-BuPh | 1,3-di-t-BuPh |
| 174352 | 4-t-BuPh | 4-t-BuPh | CN | 1,3-di-t-BuPh | 1,3-di-t-BuPh |
| 174353 | 4-t-BuPh | 4-t-BuPh | DPA | 1,3-di-t-BuPh | 1,3-di-t-BuPh |
| 174354 | 4-t-BuPh | 4-t-BuPh | 2-DBF | 1,3-di-t-BuPh | 1,3-di-t-BuPh |
| 174355 | 4-t-BuPh | 4-t-BuPh | 2-DBT | 1,3-di-t-BuPh | 1,3-di-t-BuPh |
| 174356 | 4-t-BuPh | 4-t-BuPh | 4-t-BuPh | 1,3-di-t-BuPh | 1,3-di-t-BuPh |
| 174357 | 4-t-BuPh | 4-t-BuPh | 1,3-di-t-BuPh | 1,3-di-t-BuPh | 1,3-di-t-BuPh |
| 174358 | 4-t-BuPh | 4-t-BuPh | 9-Cbz | 1,3-di-t-BuPh | 1,3-di-t-BuPh |
| 174359 | 1,3-di-t-BuPh | 1,3-di-t-BuPh | t-Bu | H | H |
| 174360 | 1,3-di-t-BuPh | 1,3-di-t-BuPh | Ph | H | H |
| 174361 | 1,3-di-t-BuPh | 1,3-di-t-BuPh | CN | H | H |
| 174362 | 1,3-di-t-BuPh | 1,3-di-t-BuPh | DPA | H | H |
| 174363 | 1,3-di-t-BuPh | 1,3-di-t-BuPh | 2-DBF | H | H |
| 174364 | 1,3-di-t-BuPh | 1,3-di-t-BuPh | 2-DBT | H | H |
| 174365 | 1,3-di-t-BuPh | 1,3-di-t-BuPh | 4-t-BuPh | H | H |
| 174366 | 1,3-di-t-BuPh | 1,3-di-t-BuPh | 9-Cbz | H | H |
| 174367 | 1,3-di-t-BuPh | 1,3-di-t-BuPh | t-Bu | t-Bu | t-Bu |
| 174368 | 1,3-di-t-BuPh | 1,3-di-t-BuPh | Ph | t-Bu | t-Bu |
| 174369 | 1,3-di-t-BuPh | 1,3-di-t-BuPh | CN | t-Bu | t-Bu |
| 174370 | 1,3-di-t-BuPh | 1,3-di-t-BuPh | DPA | t-Bu | t-Bu |
| 174371 | 1,3-di-t-BuPh | 1,3-di-t-BuPh | 2-DBF | t-Bu | t-Bu |
| 174372 | 1,3-di-t-BuPh | 1,3-di-t-BuPh | 2-DBT | t-Bu | t-Bu |
| 174373 | 1,3-di-t-BuPh | 1,3-di-t-BuPh | 4-t-BuPh | t-Bu | t-Bu |
| 174374 | 1,3-di-t-BuPh | 1,3-di-t-BuPh | 1,3-di-t-BuPh | t-Bu | t-Bu |
| 174375 | 1,3-di-t-BuPh | 1,3-di-t-BuPh | 9-Cbz | t-Bu | t-Bu |
| 174376 | 1,3-di-t-BuPh | 1,3-di-t-BuPh | t-Bu | Ph | Ph |
| 174377 | 1,3-di-t-BuPh | 1,3-di-t-BuPh | Ph | Ph | Ph |
| 174378 | 1,3-di-t-BuPh | 1,3-di-t-BuPh | CN | Ph | Ph |
| 174379 | 1,3-di-t-BuPh | 1,3-di-t-BuPh | DPA | Ph | Ph |
| 174380 | 1,3-di-t-BuPh | 1,3-di-t-BuPh | 2-DBF | Ph | Ph |
| 174381 | 1,3-di-t-BuPh | 1,3-di-t-BuPh | 2-DBT | Ph | Ph |
| 174382 | 1,3-di-t-BuPh | 1,3-di-t-BuPh | 4-t-BuPh | Ph | Ph |
| 174383 | 1,3-di-t-BuPh | 1,3-di-t-BuPh | 1,3-di-t-BuPh | Ph | Ph |
| 174384 | 1,3-di-t-BuPh | 1,3-di-t-BuPh | 9-Cbz | Ph | Ph |
| 174385 | 1,3-di-t-BuPh | 1,3-di-t-BuPh | t-Bu | CN | CN |
| 174386 | 1,3-di-t-BuPh | 1,3-di-t-BuPh | Ph | CN | CN |
| 174387 | 1,3-di-t-BuPh | 1,3-di-t-BuPh | CN | CN | CN |
| 174388 | 1,3-di-t-BuPh | 1,3-di-t-BuPh | DPA | CN | CN |
| 174389 | 1,3-di-t-BuPh | 1,3-di-t-BuPh | 2-DBF | CN | CN |
| 174390 | 1,3-di-t-BuPh | 1,3-di-t-BuPh | 2-DBT | CN | CN |
| 174391 | 1,3-di-t-BuPh | 1,3-di-t-BuPh | 4-t-BuPh | CN | CN |
| 174392 | 1,3-di-t-BuPh | 1,3-di-t-BuPh | 1,3-di-t-BuPh | CN | CN |
| 174393 | 1,3-di-t-BuPh | 1,3-di-t-BuPh | 9-Cbz | CN | CN |
| 174394 | 1,3-di-t-BuPh | 1,3-di-t-BuPh | t-Bu | 9-Cbz | 9-Cbz |
| 174395 | 1,3-di-t-BuPh | 1,3-di-t-BuPh | Ph | 9-Cbz | 9-Cbz |
| 174396 | 1,3-di-t-BuPh | 1,3-di-t-BuPh | CN | 9-Cbz | 9-Cbz |
| 174397 | 1,3-di-t-BuPh | 1,3-di-t-BuPh | DPA | 9-Cbz | 9-Cbz |
| 174398 | 1,3-di-t-BuPh | 1,3-di-t-BuPh | 2-DBF | 9-Cbz | 9-Cbz |
| 174399 | 1,3-di-t-BuPh | 1,3-di-t-BuPh | 2-DBT | 9-Cbz | 9-Cbz |
| 174400 | 1,3-di-t-BuPh | 1,3-di-t-BuPh | 4-t-BuPh | 9-Cbz | 9-Cbz |
| 174401 | 1,3-di-t-BuPh | 1,3-di-t-BuPh | 1,3-di-t-BuPh | 9-Cbz | 9-Cbz |
| 174402 | 1,3-di-t-BuPh | 1,3-di-t-BuPh | 9-Cbz | 9-Cbz | 9-Cbz |

TABLE 10-continued

| Compound No. | $R_{11b}$ | $R_{12c}$ | $R_{15C}$ | $R_{18b}$ | $R_{19b}$ |
|---|---|---|---|---|---|
| 174403 | 1,3-di-t-BuPh | 1,3-di-t-BuPh | t-Bu | 4-t-BuPh | 4-t-BuPh |
| 174404 | 1,3-di-t-BuPh | 1,3-di-t-BuPh | Ph | 4-t-BuPh | 4-t-BuPh |
| 174405 | 1,3-di-t-BuPh | 1,3-di-t-BuPh | CN | 4-t-BuPh | 4-t-BuPh |
| 174406 | 1,3-di-t-BuPh | 1,3-di-t-BuPh | DPA | 4-t-BuPh | 4-t-BuPh |
| 174407 | 1,3-di-t-BuPh | 1,3-di-t-BuPh | 2-DBF | 4-t-BuPh | 4-t-BuPh |
| 174408 | 1,3-di-t-BuPh | 1,3-di-t-BuPh | 2-DBT | 4-t-BuPh | 4-t-BuPh |
| 174409 | 1,3-di-t-BuPh | 1,3-di-t-BuPh | 4-t-BuPh | 4-t-BuPh | 4-t-BuPh |
| 174410 | 1,3-di-t-BuPh | 1,3-di-t-BuPh | 1,3-di-t-BuPh | 4-t-BuPh | 4-t-BuPh |
| 174411 | 1,3-di-t-BuPh | 1,3-di-t-BuPh | 9-Cbz | 4-t-BuPh | 4-t-BuPh |
| 174412 | 1,3-di-t-BuPh | 1,3-di-t-BuPh | t-Bu | 1,3-di-t-BuPh | 1,3-di-t-BuPh |
| 174413 | 1,3-di-t-BuPh | 1,3-di-t-BuPh | Ph | 1,3-di-t-BuPh | 1,3-di-t-BuPh |
| 174414 | 1,3-di-t-BuPh | 1,3-di-t-BuPh | CN | 1,3-di-t-BuPh | 1,3-di-t-BuPh |
| 174415 | 1,3-di-t-BuPh | 1,3-di-t-BuPh | DPA | 1,3-di-t-BuPh | 1,3-di-t-BuPh |
| 174416 | 1,3-di-t-BuPh | 1,3-di-t-BuPh | 2-DBF | 1,3-di-t-BuPh | 1,3-di-t-BuPh |
| 174417 | 1,3-di-t-BuPh | 1,3-di-t-BuPh | 2-DBT | 1,3-di-t-BuPh | 1,3-di-t-BuPh |
| 174418 | 1,3-di-t-BuPh | 1,3-di-t-BuPh | 4-t-BuPh | 1,3-di-t-BuPh | 1,3-di-t-BuPh |
| 174419 | 1,3-di-t-BuPh | 1,3-di-t-BuPh | 1,3-di-t-BuPh | 1,3-di-t-BuPh | 1,3-di-t-BuPh |
| 174420 | 1,3-di-t-BuPh | 1,3-di-t-BuPh | 9-Cbz | 1,3-di-t-BuPh | 1,3-di-t-BuPh |

In Tables 1 to 10, "H" represents hydrogen, "CN" represents a cyano group, "Me" represents a methyl group, "t-Bu" represents a t-butyl group, "Ph" represents a phenyl group, and "4-t-BuPh", "1,3-di-t-BuPh", "9-Cbz", "DPA", "2-DBF", and "2-DBT" may be represented by as follows:

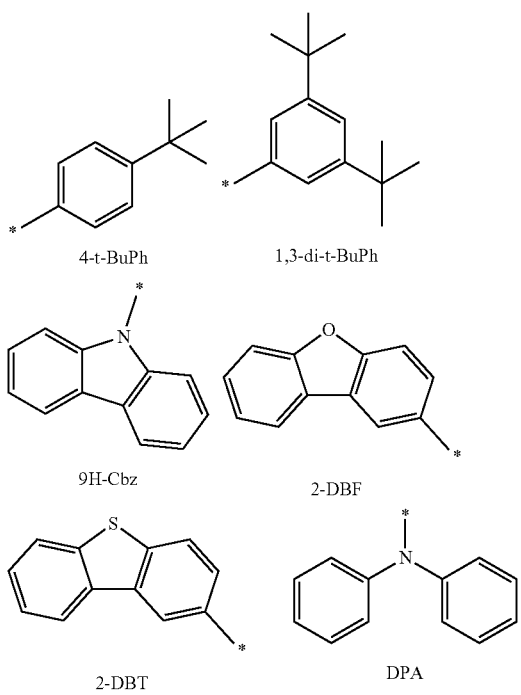

wherein, in "4-t-BuPh", "1,3-di-t-BuPh", "9-Cbz", "DPA", "2-DBF", and "2-DBT", * indicates a binding site to an adjacent atom.

In some embodiments, the heterocyclic compound may be represented by one of Formulae 11, 12, and 14 to 17, in Formula 11, ii) *1 may be $X_{13}$, *2 may be $X_{14}$, *3 may be $Y_{14}$, and *4 may be $Y_{15}$, or v) *1 may be $X_{14}$, *2 may be $X_{15}$, *3 may be $Y_{14}$, and *4 may be $Y_{15}$; in Formula 12, i) *1 may be $X_{13}$, *2 may be $X_{14}$, *3 may be $Y_{13}$, and *4 may be $Y_{14}$, ii) *1 may be $X_{13}$, *2 may be $X_{14}$, *3 may be $Y_{14}$, and *4 may be $Y_{15}$, or iv) *1 may be $X_{14}$, *2 may be $X_{15}$, *3 may be $Y_{14}$, and *4 may be $Y_{15}$; in Formula 14, i) *5 may be $X_{13}$, *6 may be $X_{14}$, *7 may be $Z_{14}$, and *8 may be $Z_{15}$, iii) *5 may be $X_{14}$, *6 may be $X_{15}$, *7 may be $Z_{14}$, and *8 may be $Z_{15}$, or iv) *5 may be $X_{14}$, *6 may be $X_{15}$, *7 may be $Z_{15}$, and *8 may be $Z_{16}$; in Formula 15, iii) *5 may be $X_{14}$, *6 may be $X_{15}$, *7 may be $Z_{14}$, and *8 may be $Z_{15}$; in Formula 16, iii) *5 may be $X_{14}$, *6 may be $X_{15}$, *7 may be $Z_{14}$, and *8 may be $Z_{15}$; or iv) *5 may be $X_{14}$, *6 may be $X_{15}$, *7 may be $Z_{15}$, and *8 may be $Z_{16}$, and in Formula 17, iv) *5 may be $X_{14}$, *6 may be $X_{15}$, *7 may be $Z_{15}$, and *8 may be $Z_{16}$.

In some embodiments, the heterocyclic compound may be represented by one of Formulae 11-2, 11-5, 12-1, 12-2, 12-4, 14-1, 14-3, 14-4, 15-3, 16-3, 16-4, and 17-4.

In some embodiments, in Formulae 11-2, 11-5, 12-1, 12-2, 12-4, 14-1, 14-3, 14-4, 15-3, 16-3, 16-4, and 17-4, Rita to $R_{11c}$, $R_{12a}$ to $R_{12d}$, $R_{13a}$ and $R_{13b}$, $R_{14a}$ to $R_{14c}$, $R_{15a}$ to $R_{15d}$, $R_{16a}$ and $R_{16b}$, $R_{17a}$, $R_{18a}$ to $R_{18d}$, and $R_{19a}$ to $R_{19c}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, a $C_1$-$C_{20}$ alkenyl group, a $C_1$-$C_{20}$ alkoxy group, or a $C_1$-$C_{20}$ alkylthio group;

a $C_1$-$C_{20}$ alkyl group, a $C_1$-$C_{20}$ alkenyl group, a $C_1$-$C_{20}$ alkoxy group, or a $C_1$-$C_{20}$ alkylthio group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a ($C_1$-$C_{20}$ alkyl)cyclopentyl group, a ($C_1$-$C_{20}$ alkyl)cyclohexyl group, a ($C_1$-$C_{20}$ alkyl)cycloheptyl group, a ($C_1$-$C_{20}$ alkyl)cyclooctyl group, a ($C_1$-$C_{20}$ alkyl) adamantanyl group, a ($C_1$-$C_{20}$ alkyl) norbornanyl group, a ($C_1$-$C_{20}$ alkyl) norbornenyl group, a ($C_1$-$C_{20}$ alkyl)cyclopentenyl group, a ($C_1$-$C_{20}$ alkyl)

cyclohexenyl group, a ($C_1$-$C_{20}$ alkyl)cycloheptenyl group, a ($C_1$-$C_{20}$ alkyl) bicyclo[1.1.1]pentyl group, a ($C_1$-$C_{20}$ alkyl) bicyclo[2.1.1]hexyl group, a ($C_1$-$C_{20}$ alkyl) bicyclo[2.2.1]heptyl group, a ($C_1$-$C_{20}$ alkyl) bicyclo[2.2.2]octyl group, a phenyl group, a ($C_1$-$C_{20}$ alkyl)phenyl group, a biphenyl group, a terphenyl group, a naphthyl group, a pyridinyl group, a pyrimidinyl group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, or an azadibenzothiophenyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a deuterated $C_2$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a ($C_1$-$C_{20}$ alkyl)cyclopentyl group, a ($C_1$-$C_{20}$ alkyl)cyclohexyl group, a ($C_1$-$C_{20}$ alkyl)cycloheptyl group, a ($C_1$-$C_{20}$ alkyl)cyclooctyl group, a ($C_1$-$C_{20}$ alkyl) adamantanyl group, a ($C_1$-$C_{20}$ alkyl) norbornanyl group, a ($C_1$-$C_{20}$ alkyl) norbornenyl group, a ($C_1$-$C_{20}$ alkyl)cyclopentenyl group, a ($C_1$-$C_{20}$ alkyl)cyclohexenyl group, a ($C_1$-$C_{20}$ alkyl)cycloheptenyl group, a ($C_1$-$C_{20}$ alkyl) bicyclo[1.1.1]pentyl group, a ($C_1$-$C_{20}$ alkyl) bicyclo[2.1.1]hexyl group, a ($C_1$-$C_{20}$ alkyl) bicyclo[2.2.1]heptyl group, a ($C_1$-$C_{20}$ alkyl) bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, or any combination thereof; or —$Si(Q_1)(Q_2)(Q_3)$, —$Ge(Q_1)(Q_2)(Q_3)$, —$C(Q_1)(Q_2)(Q_3)$, —$B(Q_1)(Q_2)$, or —$N(Q_1)(Q_2)$, wherein $Q_1$ to $Q_3$ may each independently be:

deuterium, —F, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, —$CD_2CDH_2$, —$CF_3$, —$CF_2H$, —$CFH_2$, —$CH_2CF_3$, —$CH_2CF_2H$, —$CH_2CFH_2$, —$CHFCH_3$, —$CHFCF_2H$, —$CHFCFH_2$, —$CHFCF_3$, —$CF_2CF_3$, —$CF_2CF_2H$, or —$CF_2CFH_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

In some embodiments, in Formulae 11-2, 11-5, 12-1, 12-2, 12-4, 14-1, 14-3, 14-4, 15-3, 16-3, 16-4, and 17-4, $R_{11a}$ to $R_{11c}$, $R_{12a}$ to $R_{12d}$, $R_{13a}$ and $R_{13b}$, $R_{14a}$ to $R_{14c}$, $R_{15a}$ to $R_{15d}$, $R_{16a}$ and $R_{16b}$, $R_{17a}$, $R_{18a}$ to $R_{18d}$, and $R_{19a}$ to $R_{19c}$ may each independently be hydrogen, deuterium, —F, —$CH_3$, —$CD_3$, —$CD_2H$, —$CDH_2$, —$CF_3$, —$CF_2H$, —$CFH_2$, a $C_2$-$C_{10}$ alkenyl group, a $C_1$-$C_{10}$ alkoxy group, a $C_1$-$C_{10}$ alkylthio group, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 9-201 to 9-236, a group represented by one of Formulae 9-201 to 9-236 in which at least one hydrogen is substituted with deuterium, a group represented by one of Formulae 9-201 to 9-236 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, a group represented by one of Formulae 10-201 to 10-358, a group represented by one of Formulae 10-201 to 10-358 in which at least one hydrogen is substituted with deuterium, a group represented by one of Formulae 10-201 to 10-358 in which at least one hydrogen is substituted with —F, —$Si(Q_1)(Q_2)(Q_3)$, —$Ge(Q_1)(Q_2)(Q_3)$, —$C(Q_1)(Q_2)(Q_3)$, —$B(Q_1)(Q_2)$, or —$N(Q_1)(Q_2)$, wherein $Q_1$ to $Q_3$ may each independently be:
deuterium, —F, —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, —CD$_2$CDH$_2$, —CF$_3$, —CF$_2$H, —CFH$_2$, —CH$_2$CF$_3$, —CH$_2$CF$_2$H, —CH$_2$CFH$_2$, —CHFCH$_3$, —CHFCF$_2$H, —CHFCFH$_2$, —CHFCF$_3$, —CF$_2$CF$_3$, —CF$_2$CF$_2$H, or —CF$_2$CFH$_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

In some embodiments, in Formulae 11-2, 11-5, 12-1, 12-2, 12-4, 14-1, 14-3, 14-4, 15-3, 16-3, 16-4, and 17-4, $R_{11a}$ to $R_{11c}$, $R_{12a}$ to $R_{12d}$, $R_{13a}$ and $R_{13b}$, $R_{14a}$ to $R_{14c}$, $R_{15a}$ to $R_{15d}$, $R_{16a}$ and $R_{16b}$, $R_{17a}$, $R_{18a}$ to $R_{18d}$, and $R_{19a}$ to $R_{19c}$ may each independently be hydrogen, deuterium, —F, —CH$_3$, —CD$_3$, —CD$_2$H, —CDH$_2$, —CF$_3$, —CF$_2$H, —CFH$_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, —Si($Q_1$)($Q_2$)($Q_3$), —Ge($Q_1$)($Q_2$)($Q_3$), —C($Q_1$)($Q_2$)($Q_3$), —B($Q_1$)($Q_2$), or —N($Q_1$)($Q_2$), wherein $Q_1$ to $Q_3$ may each independently be:
deuterium, —F, —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, —CD$_2$CDH$_2$, —CF$_3$, —CF$_2$H, —CFH$_2$, —CH$_2$CF$_3$, —CH$_2$CF$_2$H, —CH$_2$CFH$_2$, —CHFCH$_3$, —CHFCF$_2$H, —CHFCFH$_2$, —CHFCF$_3$, —CF$_2$CF$_3$, —CF$_2$CF$_2$H, or —CF$_2$CFH$_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

In some embodiments, in Formulae 11-2, 11-5, 12-1, 12-2, 12-4, 14-1, 14-3, 14-4, 15-3, 16-3, 16-4, and 17-4, at least one of $R_{11b}$, $R_{12c}$, $R_{14b}$, $R_{18b}$, and $R_{19b}$ in Formulae 11-2 and 11-5, at least one of $R_{11b}$, $R_{12c}$, $R_{14b}$, $R_{18c}$, and $R_{19b}$ in Formulae 12-1, 12-2, and 12-4, and at least one of $R_{11b}$, $R_{12c}$, $R_{15c}$, $R_{18b}$, and $R_{19b}$ in Formulae 14-1, 14-3, 14-4, 15-3, 16-3, 16-4, and 17-4 may be —CH$_3$, —CD$_3$, —CD$_2$H, —CDH$_2$, —CF$_3$, —CF$_2$H, —CFH$_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, —Si($Q_1$)($Q_2$)($Q_3$), —Ge($Q_1$)($Q_2$)($Q_3$), —C($Q_1$)($Q_2$)($Q_3$), —B($Q_1$)($Q_2$), or —N($Q_1$)($Q_2$), wherein $Q_1$ to $Q_3$ may each independently be:
deuterium, —F, —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, —CD$_2$CDH$_2$, —CF$_3$, —CF$_2$H, —CFH$_2$, —CH$_2$CF$_3$, —CH$_2$CF$_2$H, —CH$_2$CFH$_2$, —CHFCH$_3$, —CHFCF$_2$H, —CHFCFH$_2$, —CHFCF$_3$, —CF$_2$CF$_3$, —CF$_2$CF$_2$H, or —CF$_2$CFH$_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof, and the remaining substituents may each be hydrogen.

In some embodiments, the heterocyclic compound may be represented by Formula 11-5.

In some embodiments, the heterocyclic compound may be Group HC2, and in some embodiments, the heterocyclic compound may be Compound 115001 or 115002.

The heterocyclic compound may include three of partial structure represented by

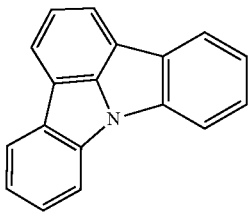 [SMILES: c1ccc2c(c1)c1cccc3c4ccccc4n2c13]

(hereinafter, referred to as an "ICz partial structure"). Accordingly, the heterocyclic compound may have improved multi-resonance characteristics, as compared with a compound including one or two of ICz partial structure. Thus, regardless of $\Delta E_{ST}$ value, a rate of reverse inter system crossing (RISC) may increase. Therefore, an organic light-emitting device including the heterocyclic compound may have improved efficiency.

In addition, as the heterocyclic compound may have improved multi-resonance characteristics, the heterocyclic compound may have a relatively small full width at half maximum (FWHM). Thus, an organic light-emitting device including the heterocyclic compound may have an improved colorimetric purity and/or conversion efficiency. For example, a FWHM of the heterocyclic compound may be smaller than 35 nm. In some embodiments, a FWHM of the heterocyclic compound may be 15 nm or less, but embodiments are not limited thereto.

The heterocyclic compound may satisfy Conditions 1 to 4:

$\Delta E_{ST} > \Delta E_{ST2} + \Delta E'_{TT}$     Condition 1

$0 \text{ eV} < \Delta E_{ST2} + \Delta E'_{TT} \leq 1.0 \text{ eV}$     Condition 2

$0 \text{ eV} < \Delta E'_{TT} \leq 0.30 \text{ eV}$     Condition 3

$\Delta E_{ST2} > 0 \text{ eV}$     Condition 4 wherein, in Conditions 1 to 4, $\Delta E_{ST}$ indicates a difference between a lowest excited singlet energy level calculated in an $S_1$ equilibrium structure of the heterocyclic compound and a lowest excited triplet energy level calculated in a $T_1$ equilibrium structure of the heterocyclic compound, $\Delta E_{ST2}$ indicates a difference between a lowest excited singlet energy level calculated in an $S_1$ equilibrium structure of the heterocyclic compound and a second lowest excited triplet energy level calculated in a $T_2$ equilibrium structure of the heterocyclic compound, and $\Delta E'_{TT}$ indicates a difference between a second lowest excited triplet energy level calculated in an $T_2$ equilibrium structure of the heterocyclic compound and a lowest excited triplet energy level calculated in a $T_2$ equilibrium structure of the heterocyclic compound.

The equilibrium structure is optimized according to the Turbomole program ([F. Furche et al. WIREsS: Comput. Mol. Sci. 4, 91-100 (2014)]) In some embodiments, structure optimization for $T_1$, $T_2$, and $S_1$ states was performed according to a time-dependent density functional theory (DFT) by using the PBE0 function under Tamm-Dancoff approximation. To obtain normal modes, frequency calculation was performed, and a lowest energy structure was identified. By using the Q-Chem program ([Y. Shao et al. Mol. Phys. 113, 184-215 (2015)]), the nonadiabatic coupling between the excited triplet state and the $T_1$ state was calculated. In addition, the spin-orbit coupling between TDDFT states was calculated by using the Q-Chem program according to one-electron Breit-Pauli spin-orbit operator. The def2-SVP basis set was used for all atoms.

In some embodiments, the heterocyclic compound may satisfy Condition 3A:

$0 \text{ eV} < \Delta E'_{TT} \leq 0.15 \text{ eV}$     Condition 3A wherein, in Condition 3A, $\Delta E'_{TT}$ may be understood by referring to the description of $\Delta E'_{TT}$ provided herein.

In general, compounds having a relatively small $\Delta E_{ST}$ value may emit thermal activated delayed fluorescence (TADF). However, even though the $\Delta E_{ST}$ value of the heterocyclic compound is relatively great, as the the heterocyclic compound may satisfy Conditions 1 to 4, the heterocyclic compound may emit TADF, and an organic light-emitting device including the heterocyclic compound may have improved efficiency.

Furthermore, by using the heterocyclic compound as a sensitizer, energy transferred to a triplet state may undergo RISC to a singlet state. Then, the singlet energy of the heterocyclic compound may be transferred to a dopant by Förster energy transfer. Thus, the organic light-emitting device may have improved efficiency and lifespan at the same time.

When heterocyclic compound serves as a dopant in an organic light-emitting device, the heterocyclic compound may emit blue light, e.g., blue light having a maximum emission wavelength of about 550 nm or less, for example, blue light having a maximum emission wavelength in a range of about 400 nm to about 500 nm, for example, about 420 nm to about 480 nm, or for example, 460 nm or less. The "maximum emission wavelength" as used herein refers to a wavelength of which the emission intensity is greatest. In other words, the "maximum emission wavelength" may be referred to as "peak emission wavelength".

When the heterocyclic compound serves as a dopant in an organic light-emitting device, CIEy of the organic light-emitting device may be about 0.07 or less, for example, about 0.061 or less.

A method of synthesizing the heterocyclic compound may be apparent to one of ordinary skill in the art by referring to Synthesis Examples provided herein.

The heterocyclic compound represented by Formula 1 may be suitable for use in an organic layer of an organic light-emitting device, e.g., as a dopant in an emission layer of the organic layer. Thus, according to another aspect, there is provided an organic light-emitting device that may include: a first electrode; a second electrode; and an organic layer between the first electrode and the second electrode, wherein the organic layer includes an emission layer and at least one of the heterocyclic compound.

Since the organic light-emitting device has an organic layer including the heterocyclic compound, the organic light-emitting device may have a low driving voltage, high efficiency, high power, high quantum efficiency, long lifespan, low roll-off, and excellent color purity.

The heterocyclic compound may be used in a pair of electrodes of an organic light-emitting device. In some embodiments, the heterocyclic compound may be included in an emission layer. In this embodiment, the heterocyclic compound may serve as a dopant and the emission layer may further include a host (that is, an amount of the heterocyclic compound may be smaller than that of the host).

As used herein, the expression the "(organic layer) includes at least one of the heterocyclic compounds" may be construed as meaning that the "(organic layer) may include one heterocyclic compound of Formula 1-1 or 1-2 or two different heterocyclic compounds of Formula 1-1 or 1-2".

For example, the organic layer may include Compound 115001 only as the heterocyclic compound. In this embodiment, Compound 115001 may be included in the emission layer of the organic light-emitting device. In some embodiments, the organic layer may include Compounds 115001 and 115002 as the heterocyclic compounds. In this embodiment, Compounds 115001 and 115002 may both be included in the same layer (for example, both Compounds 115001 and 115002 may be included in the emission layer).

The first electrode may be an anode, which is a hole injection electrode, and the second electrode may be a cathode, which is an electron injection electrode. In some embodiments, the first electrode may be a cathode, which is an electron injection electrode, and the second electrode may be an anode, which is a hole injection electrode.

For example, in the organic light-emitting device, the first electrode may be an anode, the second electrode may be a cathode, and the organic layer may further include a hole transport region between the first electrode and the emission layer and an electron transport region between the emission layer and the second electrode, wherein the hole transport region may include a hole injection layer, a hole transport layer, an electron blocking layer, or a combination thereof, and the electron transport region may include a hole blocking layer, an electron transport layer, an electron injection layer, a buffer layer, or a combination thereof.

The term "organic layer" as used herein refers to a single and/or a plurality of layers disposed between the first electrode and the second electrode in an organic light-emitting device. The "organic layer" may include not only organic compounds but also organometallic complexes including metals.

In some embodiments, the heterocyclic compound may emit fluorescence and/or delayed fluorescence. The emission layer that may emit fluorescence and/or delayed fluorescence is different from an emission layer that may emit phosphorescence.

Description of FIG. 1

FIG. 1 is a schematic view of an organic light-emitting device 10 according to an exemplary embodiment. Hereinafter a structure and a method of manufacturing the organic light-emitting device 10, according to an embodiment, will be described with reference to FIG. 1.

In FIG. 1, an organic light-emitting device 10 includes a first electrode 11, a second electrode 19 facing the first electrode 11, and an organic layer 10A between the first electrode 11 and the second electrode 19.

In FIG. 1, the organic layer 10A includes an emission layer 15, a hole transport region 12 is between the first electrode 11 and an emission layer 15, and an electron transport region 17 is between the emission layer 15 and the second electrode 19.

A substrate may be additionally disposed under the first electrode 11 or on the second electrode 19. The substrate may be a conventional substrate used in organic light-emitting devices, e.g., a glass substrate or a transparent plastic substrate, each having excellent mechanical strength, thermal stability, transparency, surface smoothness, ease of handling, and water repellency.

First Electrode 11

The first electrode 11 may be produced by depositing or sputtering, onto the substrate, a material for forming the first electrode 11. The first electrode 11 may be an anode. The material for forming the first electrode 11 may be materials with a high work function for easy hole injection.

The first electrode 11 may be a reflective electrode, a semi-transmissive electrode, or a transmissive electrode. When the first electrode 11 is a transmissive electrode, a material for forming the first electrode 11 may be indium tin oxide (ITO), indium zinc oxide (IZO), tin oxide ($SnO_2$), zinc oxide (ZnO), or any combinations thereof, but embodiments are not limited thereto. In some embodiments, when the first electrode 11 is a semi-transmissive electrode or a reflective electrode, as a material for forming the first electrode 11, at least one of magnesium (Mg), silver (Ag), aluminum (Al), aluminum-lithium (Al—Li), calcium (Ca), magnesium-indium (Mg—In), magnesium-silver (Mg—Ag), or any combination thereof may be used, but embodiments are not limited thereto.

The first electrode 11 may have a single-layered structure or a multi-layered structure including a plurality of layers.

Emission Layer 15

In some embodiments, the emission layer 15 may include the heterocyclic compound.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Figure 2A:
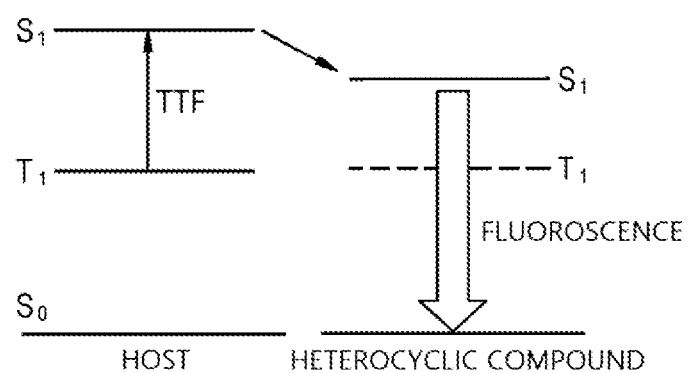
FIGS. 2A-2E illustrate the general energy transfer of the First Embodiment (FIG. 2A), the Second Embodiment (FIG. 2B), the Third Embodiment (FIG. 2C), the Fourth Embodiment (FIG. 2D), and the Fifth Embodiment (FIG. 2E)

First Embodiment—Descriptions of FIG. 2A

In the First Embodiment, the heterocyclic compound may be a fluorescence emitter. According to the First Embodiment, the emission layer may further include a host (hereinafter, referred to as 'Host A', and Host A may not be identical to the heterocyclic compound). Host A may be understood by referring to the description of the host material provided herein, but embodiments are not limited thereto. Host A may be a fluorescent host.

General energy transfer of the First Embodiment may be explained according to FIG. 2A.

Singlet excitons may be produced from Host A in the emission layer, and singlet excitons produced from Host A may be transferred to a fluorescence emitter through Förster energy transfer (FRET).

A ratio of singlet excitons produced from Host A may be 25%, and thus, 75% of triplet excitons produced from Host A may be fused to one another to be converted into singlet excitons. Thus, efficiency of the organic light-emitting device may be further improved. That is, efficiency of an organic light-emitting device may be further improved by using a triplet-triplet fusion mechanism.

According to the First Embodiment, a ratio of emission components emitted from the heterocyclic compound to the total emission components emitted from the emission layer may be about 80% or greater, for example, about 90% or greater. In some embodiments, a ratio of emission components emitted from the heterocyclic compound may be about 95% or greater to the total emission components emitted from the emission layer.

The heterocyclic compound may emit fluorescence, and the host may not emit light.

In the First Embodiment, when the emission layer further includes Host A, in addition to the heterocyclic compound, a content of the heterocyclic compound may be 50 parts by weight or less, e.g., 30 parts by weight or less, based on 100 parts by weight of the emission layer, and a content of Host A in the emission layer may be 50 parts by weight or greater, e.g., 70 parts by weight or greater, based on 100 parts by weight of the emission layer, but embodiments are not limited thereto.

In the First Embodiment, when the emission layer further includes Host A, in addition to the heterocyclic compound, Host A and the heterocyclic compound may satisfy Condition A:

$$E(H_A)_{S1} > E_{S1} \qquad \text{Condition A}$$

wherein, in Condition A,
- $E(H_A)_{S1}$ indicates a lowest excited singlet energy level of Host A, and
- $E_{S1}$ indicates a lowest excited singlet energy level of the heterocyclic compound.

Here, $E(H_A)_{S1}$ and $E_{S1}$ may be evaluated by using Gaussian according to density functional theory (DFT) method (wherein structure optimization is performed at a degree of B3LYP, and 6-31G (d,p)).

Figure 2B:
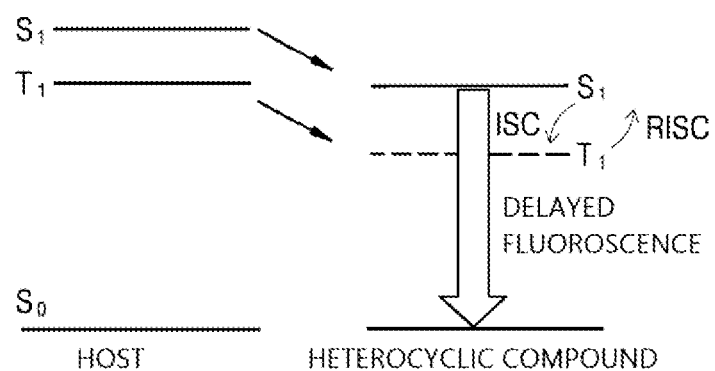

Second Embodiment—Descriptions of FIG. 2B

In the Second Embodiment, the heterocyclic compound may be a delayed fluorescence emitter. According to the Second Embodiment, the emission layer may further include a host (hereinafter, referred to as 'Host B', and Host B may not be identical to the heterocyclic compound). Host B may be understood by referring to the description of the host material provided herein, but embodiments are not limited thereto.

General energy transfer of the Second Embodiment may be explained according to FIG. 2B.

25% of singlet excitons produced from Host B in the emission layer may be transferred to a delayed fluorescence emitter through FRET. In addition, 75% of triplet excitons produced from Host B in the emission layer may be transferred to a delayed fluorescence emitter through Dexter energy transfer. Energy transferred to a triplet state of a delayed fluorescence emitter may undergo RISC to a singlet state. Accordingly, singlet excitons and triplet excitons produced from the emission layer may be transferred to the heterocyclic compound. Thus, the organic light-emitting device may have improved efficiency.

Thus, according to the Second Embodiment, a ratio of emission components emitted from the heterocyclic compound to the total emission components emitted from the emission layer may be about 80% or greater, for example, about 90% or greater. In some embodiments, a ratio of emission components emitted from the heterocyclic compound may be about 95% or greater to the total emission components emitted from the emission layer.

Here, the heterocyclic compound may emit fluorescence and/or delayed fluorescence, and the emission components of the heterocyclic compound may be a total of prompt emission components of the heterocyclic compound and delayed fluorescence components by RISC of the heterocyclic compound. In addition, Host B may not emit light.

In the Second Embodiment, when the emission layer further includes Host B, in addition to the heterocyclic compound, a content of the heterocyclic compound may be 50 parts by weight or less, e.g., 30 parts by weight or less, based on 100 parts by weight of the emission layer, and a content of Host B in the emission layer may be 50 parts by weight or greater, e.g., 70 parts by weight or greater, based on 100 parts by weight of the emission layer, but embodiments are not limited thereto.

In the Second Embodiment, when the emission layer further includes Host B, in addition to the heterocyclic compound, Host B and the heterocyclic compound may satisfy Condition B:

$$E(H_B)_{S1} > E_{S1} \qquad \text{Condition B}$$

wherein, in Condition B,
- $E(H_B)_{S1}$ indicates a lowest excited singlet energy level of Host B, and
- $E_{S1}$ indicates a lowest excited singlet energy level of the heterocyclic compound.

Here, $E(H_B)_{S1}$ and $E_{S1}$ may be evaluated by using Gaussian according to density functional theory (DFT) method (wherein structure optimization is performed at a degree of B3LYP, and 6-31G (d,p)).

Third Embodiment and Fourth Embodiment

Figure 2C:
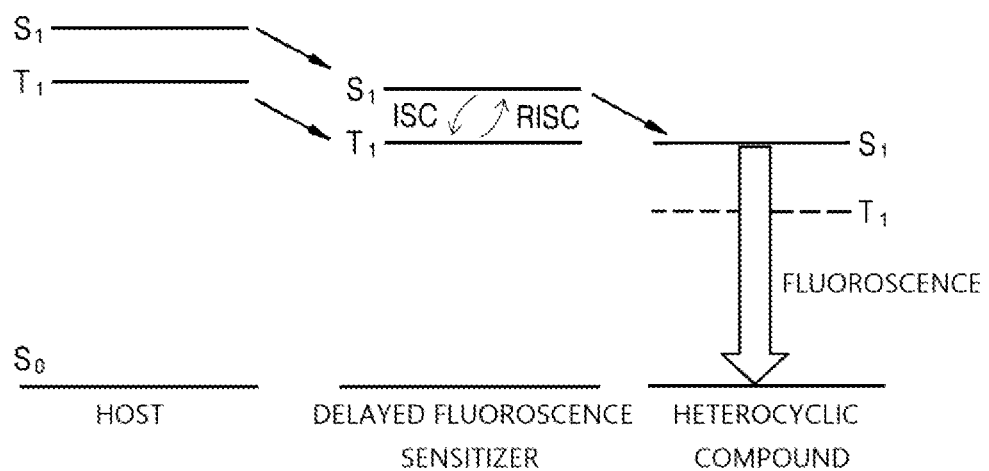

Third Embodiment—Descriptions of FIG. 2C

In the Third Embodiment, the heterocyclic compound may be used as a fluorescence emitter, and the emission layer may include a sensitizer, e.g., a delayed fluorescence sensitizer. In the Third Embodiment, the emission layer may further include a host (hereinafter, the host may be referred to as 'Host C', and Host C may not be identical to the heterocyclic compound and the sensitizer) and a sensitizer (hereinafter, the sensitizer may be referred to as 'Sensitizer A', and Sensitizer A may not be identical to Host C and the heterocyclic compound). Host C and Sensitizer A may respectively be understood by referring to the description of the host material and the sensitizer material provided herein, but embodiments are not limited thereto.

In the Third Embodiment, a ratio of emission components of the heterocyclic compound may be about 80% or greater, for example, about 90% or greater (or for example, about 95% or greater) to the total emission components emitted from the emission layer. For example, the heterocyclic compound may emit fluorescence. In addition, Host C and Sensitizer A may not each emit light.

General energy transfer of the Third Embodiment may be explained according to FIG. 2C.

Singlet and triplet excitons may be produced from Host C in the emission layer, and singlet and triplet excitons produced from Host C may be transferred to Sensitizer A and then to the heterocyclic compound through FRET. 25% of singlet excitons produced from Host C may be transferred to Sensitizer A through FRET, and energy of 75% of triplet excitons produced from Host C may be transferred to singlet and triplet states of Sensitizer A. Energy transferred to a triplet state of Sensitizer A may undergo RISC to a singlet state, and then, singlet energy of Sensitizer A may be transferred to the heterocyclic compound through FRET.

Accordingly, singlet excitons and triplet excitons produced from the emission layer may be transferred to the dopant. Thus, the organic light-emitting device may have improved efficiency. Further, energy loss of the organic light-emitting device may be significantly small. Thus, the organic light-emitting device may have improved lifespan characteristics.

In the Third Embodiment, when the emission layer further includes Host C and Sensitizer A, in addition to the heterocyclic compound, Host C and Sensitizer A may satisfy Condition C-1 and/or C-2:

$$S_1(H_C) \geq S_1(S_A) \qquad \text{Condition C-1}$$

$$S_1(S_A) \geq S_1(HC) \qquad \text{Condition C-2}$$

wherein, in Conditions C-1 and C-2,
$S_1$ ($H_C$) indicates a lowest excited singlet energy level of Host C,
$S_1$ ($S_A$) indicates a lowest excited singlet energy level of Sensitizer A, and
$S_1$ (HC) indicates a lowest excited singlet energy level of the heterocyclic compound.

$S_1$ ($H_C$), $S_1$ ($S_A$), and $S_1$ (HC) may be evaluated according to the DFT method, wherein structure optimization is performed at a degree of B3LYP, and 6-31G (d,p), for example, according to Gaussian according to DFT method.

When Host C, Sensitizer A, and the heterocyclic compound satisfy Condition C-1 and/or C-2, FRET from Sensitizer A to the heterocyclic compound may be facilitated, and accordingly, the organic light-emitting device may have improved luminescence efficiency.

Figure 2D:
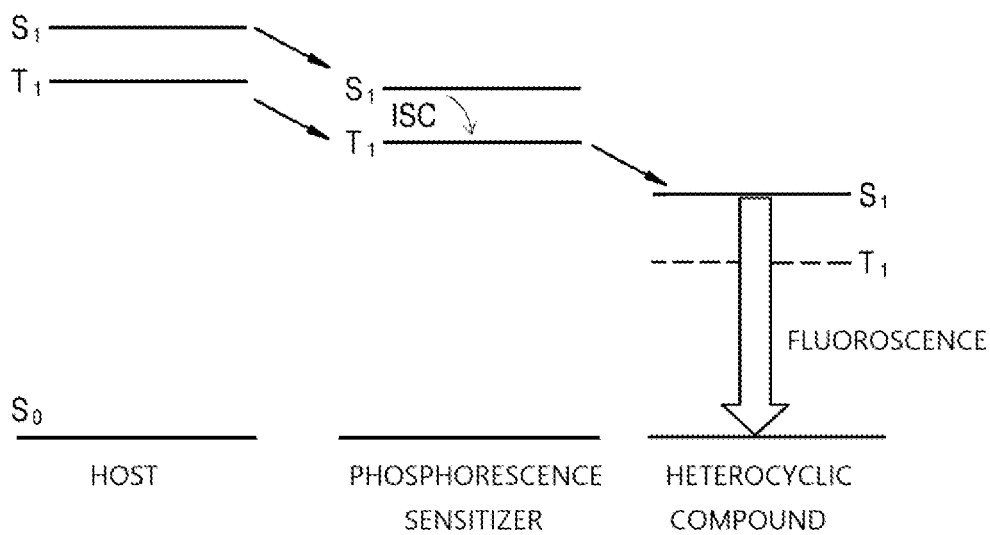

Fourth Embodiment—Descriptions of FIG. 2D

In the Fourth Embodiment, the heterocyclic compound may be used as a fluorescence emitter, and the emission layer may include a sensitizer, e.g., a phosphorescence sensitizer. In the Fourth Embodiment, the emission layer may further include a host (hereinafter, the host may be referred to as 'Host D', and Host D may not be identical to the heterocyclic compound and the sensitizer) and a sensitizer (hereinafter, the sensitizer may be referred to as 'Sensitizer B', and Sensitizer B may not be identical to Host D and the heterocyclic compound). Host D and Sensitizer B may respectively be understood by referring to the description of the host material and the sensitizer material provided herein, but embodiments are not limited thereto.

In the Fourth Embodiment, a ratio of emission components of the heterocyclic compound may be about 80% or greater, for example, about 90% or greater (or for example, about 95% or greater) to the total emission components emitted from the emission layer. For example, the heterocyclic compound may emit fluorescence. In addition, Host D and Sensitizer B may not each emit light.

General energy transfer of the Fourth Embodiment may be explained according to FIG. 2D.

75% of triplet excitons produced from Host D in the emission layer may be transferred to Sensitizer B through Dexter energy transfer, and the energy of 25% of singlet excitons produced from Host D may be transferred to singlet and triplet states of Sensitizer B. Energy transferred to a singlet state of Sensitizer B may undergo ISC to a triplet state, and then, triplet energy of Sensitizer B may be transferred to the heterocyclic compound through FRET.

Accordingly, singlet excitons and triplet excitons produced from the emission layer may be transferred to the dopant. Thus, the organic light-emitting device may have improved efficiency. Further, energy loss of the organic light-emitting device may be significantly small. Thus, the organic light-emitting device may have improved lifespan characteristics.

In the Third Embodiment, when the emission layer further includes Host D and Sensitizer B, in addition to the heterocyclic compound, Host D and Sensitizer B may satisfy Condition D-1 and/or D-2:

$$T_1(H_D) \geq T_1(S_B) \qquad \text{Condition D-1}$$

$$T_1(S_B) \geq S_1(HC) \qquad \text{Condition D-2}$$

wherein, in Conditions D-1 and D-2,
$T_1$ ($H_D$) indicates a lowest excited triplet energy level of Host D,
$T_1$ ($S_B$) indicates a lowest excited triplet energy level of Sensitizer B, and
$S_1$ (HC) indicates a lowest excited singlet energy level of the heterocyclic compound.

$T_1$ ($H_D$), $T_1$ ($S_B$), and $S_1$(HC) may be evaluated according to the DFT method, wherein structure optimization is performed at a degree of B3LYP, and 6-31G (d,p), for example, according to Gaussian according to DFT method.

When Host D, Sensitizer B, and the heterocyclic compound satisfy Condition D-1 and/or D-2, FRET from Sensitizer B to the heterocyclic compound may be facilitated, and accordingly, the organic light-emitting device may have improved luminescence efficiency.

In the Third Embodiment and the Fourth Embodiment, a content of the sensitizer in the emission layer may be in a range of about 5 percent by weight (wt %) to about 50 wt %, or for example, about 10 wt % to about 30 wt %. When the content is within this range, energy transfer in the emission layer may be effectively occurred. Thus, the organic light-emitting device may have high efficiency and long lifespan.

In the Third Embodiment and the Fourth Embodiment, a content of the heterocyclic compound in the emission layer may be in a range of about 0.01 wt % to about 15 wt %, or for example, about 0.05 wt % to about 3 wt %, but embodiments are not limited thereto.

In the Third Embodiment and the Fourth Embodiment, the heterocyclic compound may further satisfy Condition 5:

$$0\mu s < T_{decay}(HC) < 5\mu s \qquad \text{Condition 5}$$

wherein, in Condition 5, $T_{decay}$(HC) indicates a decay time of the heterocyclic compound.

The decay time of the heterocyclic compound was measured from a time-resolved photoluminescence (TRPL) spectrum at room temperature of a film (hereinafter, referred to as "Film (HC)") having a thickness of about 40 nm formed by vacuum-depositing the host and the heterocyclic compound included in the emission layer on a quartz substrate at a weight ratio of 90:10 at a vacuum pressure of $10^{-7}$ torr.

Figure 2E:
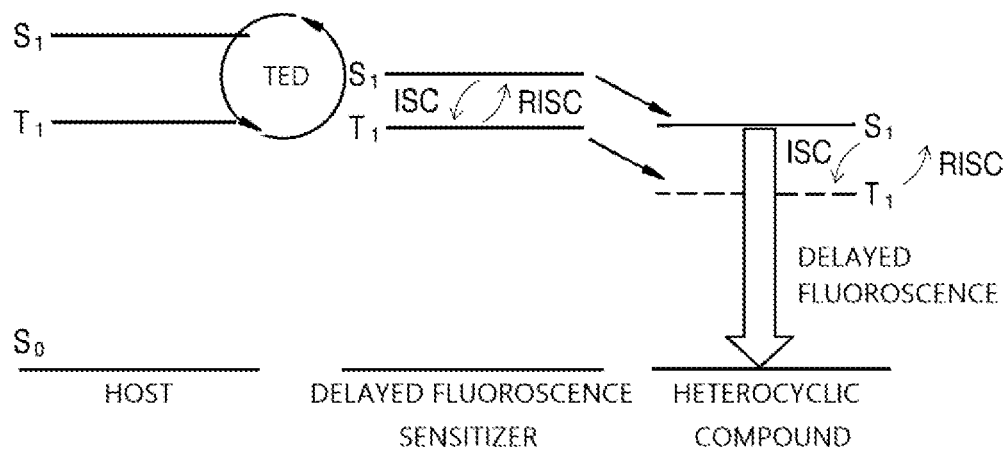

Fifth Embodiment—Descriptions of FIG. 2E

In the Fifth Embodiment, the heterocyclic compound may be used as a delayed fluorescence emitter, and the emission layer may include a sensitizer, e.g., a delayed fluorescence sensitizer. In the Fifth Embodiment, the emission layer may further include a host (hereinafter, the host may be referred to as 'Host E', and Host E may not be identical to the heterocyclic compound and the sensitizer) and a sensitizer (hereinafter, the sensitizer may be referred to as 'Sensitizer C', and Sensitizer C may not be identical to Host E and the heterocyclic compound). Host E and Sensitizer C may respectively be understood by referring to the description of the host material and the sensitizer material provided herein, but embodiments are not limited thereto.

In the Fifth Embodiment, a ratio of emission components of the heterocyclic compound may be about 80% or greater, for example, about 90% or greater (or for example, about 95% or greater) to the total emission components emitted from the emission layer. In some embodiments, the heterocyclic compound may emit fluorescence and/or delayed fluorescence. In addition, Host E and Sensitizer C may not each emit light.

Here, the heterocyclic compound may emit fluorescence and/or delayed fluorescence, and the emission components of the heterocyclic compound may be a total of prompt emission components of the heterocyclic compound and delayed fluorescence components by RISC of the heterocyclic compound.

General energy transfer of the Fifth Embodiment may be explained according to FIG. 2E.

25% of singlet excitons produced from Host E in the emission layer may be transferred to a singlet state of Sensitizer C through FRET, and the energy of 75% of triplet excitons produced from Host E may be transferred to a triplet state of Sensitizer C, and then singlet energy of Sensitizer C may be transferred to the heterocyclic compound through FRET. Subsequently, the triplet energy of Sensitizer C may be transferred to the heterocyclic compound through Dexter energy transfer. Energy transferred to a triplet state of Sensitizer C may undergo RISC to a singlet state. Further, in a case of Sensitizer C, energy of triplet excitons produced from Sensitizer C may undergo reverse transfer to Host E and then to the heterocyclic compound, thus emitting by reverse intersystem transfer.

Accordingly, singlet excitons and triplet excitons produced from the emission layer may be transferred to the dopant. Thus, the organic light-emitting device may have improved efficiency. Further, energy loss of the organic light-emitting device may be significantly small. Thus, the organic light-emitting device may have improved lifespan characteristics.

In the Fifth Embodiment, when the emission layer further includes Host E and Sensitizer C, in addition to the heterocyclic compound, Host E and Sensitizer C may satisfy Condition E-1, E-2, and/or E-3:

$S_1(H_E) \geq S_1(S_C)$   Condition E-1

$S_1(S_C) \geq S_1(HC)$   Condition E-2

$T_1(S_C) \geq T_1(HC)$   Condition E-3 wherein, in Conditions E-1, E-2, and E-3,
$S_1$ ($H_E$) indicates a lowest excited singlet energy level of Host E,
$S_1$ ($S_C$) indicates a lowest excited singlet energy level of Sensitizer C,
$S_1$ (HC) indicates a lowest excited singlet energy level of the heterocyclic compound,
$T_1$ ($S_C$) indicates a lowest excited triplet energy level of Sensitizer C, and
$T_1$ (HC) indicates a lowest excited triplet energy level of the heterocyclic compound.
$S_1$ ($H_E$), $S_1(S_C)$, $S_1$(HC), $T_1$ ($S_C$), and $T_1$ (HC) may be evaluated according to the DFT method, wherein structure optimization is performed at a degree of B3LYP, and 6-31G (d,p), for example, according to Gaussian according to DFT method.

When Host E, Sensitizer C, and the heterocyclic compound satisfy Condition E-1, E-2, and/or E-3, Dexter transfer FRET from Sensitizer C to the heterocyclic compound may be facilitated, and accordingly, the organic light-emitting device may have improved luminescence efficiency.

In the Fifth Embodiment, a content of Sensitizer C in the emission layer may be in a range of about 5 wt % to about 50 wt %, or for example, about 10 wt % to about 30 wt %. When the content is within this range, energy transfer in the emission layer may occur effectively. Thus, the organic light-emitting device may have high efficiency and long lifespan.

In the Fifth Embodiment, a content of the heterocyclic compound in the emission layer may be in a range of about 0.01 wt % to about 15 wt %, or for example, about 0.05 wt % to about 3 wt %, but embodiments are not limited thereto.

Host in Emission Layer 15

The host may not include a metal atom.

In an embodiment, the host may consist of one type of host. When the host consists of one type of host, the one type of host may be a bipolar host, an electron transporting host, or a hole transporting host described herein.

In one or more embodiments, the host may be a mixture of two or more types of hosts. In some embodiments, the host may be a mixture of an electron transporting host and a hole transporting host, a mixture of two different types of electron transporting hosts or a mixture of two different types of hole transporting hosts. The electron transporting host and the hole transporting host may respectively be understood by referring to the descriptions of the electron transporting host and the hole transporting host provided herein.

In an embodiment, the host may include an electron transporting host including at least one electron transporting moiety and a hole transporting host not including an electron transporting moiety.

The electron transporting moiety may be a cyano group, a π electron-depleted nitrogen-containing cyclic group, and a group represented by one of following Formulae:

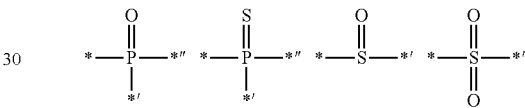

wherein, in the Formulae above, *, *', and *" may each indicate a binding site to an adjacent atom.

In an embodiment, an electron transporting host in the emission layer 15 may include at least one of a cyano group, a π electron-depleted nitrogen-containing cyclic group, or a combination thereof.

In one or more embodiments, the electron transporting host in the emission layer 15 may include at least one cyano group.

In one or more embodiments, an electron transporting host in the emission layer 15 may include a cyano group, at least one IT electron-depleted nitrogen-containing cyclic group, or a combination thereof.

In one or more embodiments, the host may include an electron transporting host and a hole transporting host, the electron transporting host may include at least one IT electron-depleted nitrogen-free cyclic group and at least one electron transporting moiety, and the hole transporting host may include at least one IT electron-depleted nitrogen-free cyclic group and may not include an electron transporting moiety.

The term "IT electron-depleted nitrogen-containing cyclic group" as used herein refers to a cyclic group having at least one *—N=*' moiety. Examples thereof may include: an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a condensed ring of at least two π electron-depleted nitrogen-containing cyclic groups.

The π electron-depleted nitrogen-free cyclic group may be a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, and a triindolobenzene group; and a condensed ring of at least two π electron-depleted nitrogen-free cyclic group, but embodiments are not limited thereto.

In some embodiments, the electron transporting host may be one of the Compounds represented by Formula E-1, and the hole transporting host may be one of the Compounds represented by Formula H-1, but embodiments are not limited thereto:

$$[Ar_{30}1]_{xb11}-[(L_{301})_{xb1}-R_{301}]_{xb21}$$ Formula E-1 wherein, in Formula E-1, $Ar_{30}1$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may each independently be a single bond, a group represented by one of following Formulae, a substituted or unsubstituted $C_5$-$C_{60}$ carbocyclic group, or a substituted or unsubstituted $C_1$-$C_{60}$ heterocyclic group, wherein in the following Formulae, *, *', and *'' may each indicate a binding site to an adjacent atom,

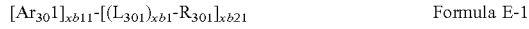

xb1 may be an integer from 1 to 5, $R_{301}$ may be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent aromatic condensed polycyclic group, a substituted or unsubstituted monovalent aromatic condensed heteropolycyclic group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), —S(=O)($Q_{301}$), —P(=O)($Q_{301}$)($Q_{302}$), or —P(=S)($Q_{301}$)($Q_{302}$), xb21 may be an integer from 1 to 5, $Q_{301}$ to $Q_{303}$ may each independently be a $C_1$-$C_{10}$ alkyl group, a $C_1$-$C_{10}$ alkoxy group, a phenyl group, a biphenyl group, a terphenyl group, or a naphthyl group, and at least one of Conditions H-1 to H-3 may be satisfied:

Condition H-1 wherein, at least one of $Ar_{30}1$, $L_{301}$, and $R_{301}$ in Formula E-1 may each independently include a π electron-depleted nitrogen-containing cyclic group, Condition H-2 wherein, $L_{301}$ in Formula E-1 may be a group represented by one of the following Formulae, and

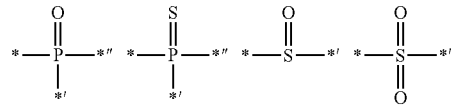

Condition H-3 wherein, $R_{301}$ in Formula E-1 may be a cyano group, —S(=O)$_2$($Q_{301}$), —S(=O)($Q_{301}$), —P(=O)($Q_{301}$)($Q_{302}$), or —P(=S)($Q_{301}$)($Q_{302}$).

$$Ar_{401}—(L_{401})_{xd1}—(Ar_{402})_{xd11}$$ Formula H-1

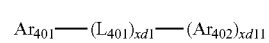

Formula 11

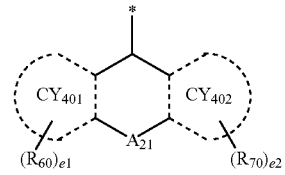

Formula 12

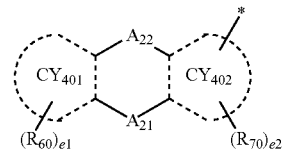

wherein, in Formulae H-1, 11, and 12, $L_{401}$ may be:

a single bond; or a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group, each unsubstituted or substituted with at least one of deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —Si($Q_{401}$)($Q_{402}$)($Q_{403}$), or any combination thereof.

xd1 may be an integer from 1 to 10, and when xd1 is 2 or greater, at least two $L_{401}$(s) may be identical to or different from each other, $Ar_{401}$ may be a group represented by Formulae 11 or 12, $Ar_{402}$ may be:

a group represented by Formulae 11 or 12, a phenyl group, a naphthyl group, a fluorenyl group, a carbazolyl group, a dibenzofuranyl group, a dibenzothiophenyl group, a biphenyl group, a terphenyl group, or a triphenylenyl group; or a phenyl group, a naphthyl group, a fluorenyl group, a carbazolyl group, a dibenzofuranyl group, a dibenzothiophenyl group, a biphenyl group, a terphenyl group, or a triphenylenyl group, each unsubstituted or substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, a terphenyl group, a triphenylenyl group, or any combination thereof, $CY_{401}$ and $CY_{402}$ may each independently be a benzene group, a naphthalene group, a fluorene group, a carbazole group, a benzocarbazole group, an indolocarbazole group, a dibenzofuran group, a dibenzothiophene group, a dibenzosilole group, a benzonaphthofuran group, a benzonapthothiophene group, or a benzonaphthosilole group, $A_{21}$ may be a single bond, O, S, N($R_{51}$), C($R_{51}$)($R_{52}$), or Si($R_{51}$)($R_{52}$), $A_{22}$ may be a single bond, O, S, N($R_{53}$), C($R_{53}$)($R_{54}$), or Si($R_{53}$)($R_{54}$), at least one of $A_{21}$, $A_{22}$, or any combination thereof in Formula 12 may not be a single bond, $R_{51}$ to $R_{54}$ and $R_{60}$ to $R_{70}$ may each independently be:

hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, or any combination thereof;

a π electron-depleted nitrogen-free cyclic group (e.g., a phenyl group, a naphthyl group, a fluorenyl group, a carbazolyl group, a dibenzofuranyl group, a dibenzothiophenyl group, a biphenyl group, a terphenyl group, and a triphenylenyl group);

a π electron-depleted nitrogen-free cyclic group (e.g., a phenyl group, a naphthyl group, a fluorenyl group, a carbazolyl group, a dibenzofuranyl group, a dibenzothiophenyl group, a biphenyl group, a terphenyl group, and a triphenylenyl group) substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, or any combination thereof, —Si($Q_{404}$)($Q_{405}$)($Q_{406}$), e1 and e2 may each independently be an integer from 0 to 10, wherein $Q_{401}$ to $Q_{406}$ may each independently be hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, a biphenyl group, a terphenyl group, or a triphenylenyl group, and

* indicates a binding site to an adjacent atom.

In some embodiments, in Formula E-1, $Ar_{301}$ and $L_{301}$ may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl) pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof, at least one of $L_{301}$ in the number of xb1 may each independently be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl) pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl) pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and $R_{301}$ may be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a tetraphenyl group, a naphthyl group, a cyano group-containing phenyl group, a cyano group-containing biphenyl group, a cyano group-containing terphenyl group, a cyano group-containing a tetraphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl) pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group, but embodiments are not limited thereto.

In some embodiments, $Ar_{30}1$ may be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, or a dibenzothiophene group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl) pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl) triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$) or —P(=O)($Q_{31}$)($Q_{32}$); or a group represented by one of Formulae 5-1 to 5-3 and 6-1 to 6-33, and $L_{301}$ may be a group represented by one of Formulae 5-1 to 5-3 and 6-1 to 6-33:

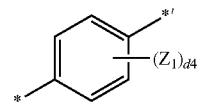

5-1


5-2


5-3

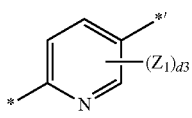 
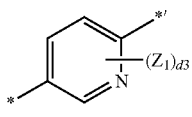 
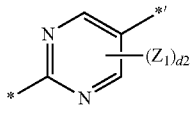 
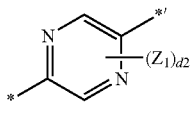 
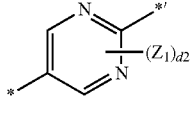 
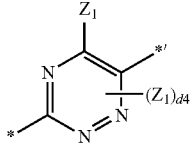 
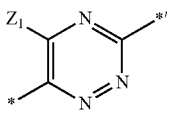 
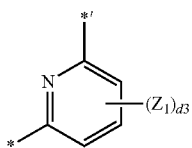 
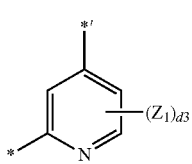 
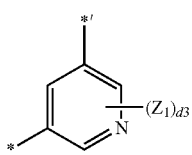 
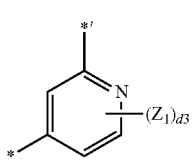 
6-1
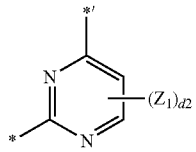
6-2

6-3

6-4

6-5

6-6
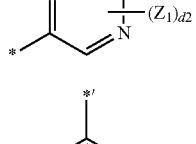
6-7
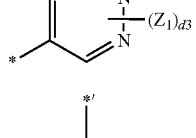
6-8
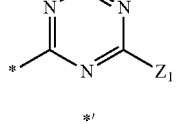
6-9
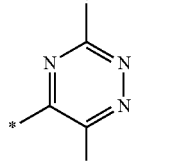
6-10
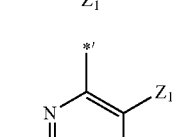
6-11
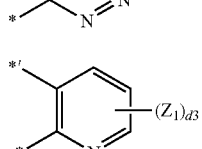

-continued

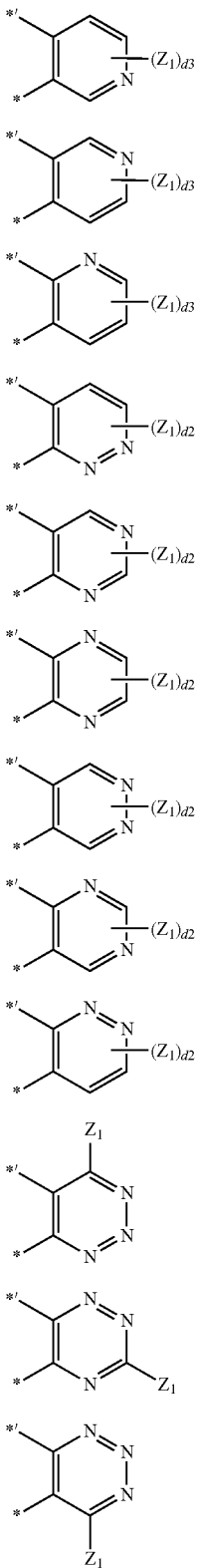

6-22
6-23
6-24
6-25
6-26
6-27
6-28
6-29
6-30
6-31
6-32
6-33 wherein, in Formulae 5-1 to 5-3 and 6-1 to 6-33, $Z_1$ may be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), d4 may be 0, 1, 2, 3, or 4, d3 may be 0, 1, 2, or 3, d2 may be 0, 1, or 2, and

* and *' each indicate a binding site to an adjacent atom.

$Q_{31}$ to $Q_{33}$ may respectively be understood by referring to the descriptions of $Q_{31}$ to $Q_{33}$ provided herein.

In one or more embodiments, $L_{301}$ may be groups represented by Formulae 5-2, 5-3, and 6-8 to 6-33.

In one or more embodiments, $R_{301}$ may be a cyano group or a group represented by Formulae 7-1 to 7-18, at least one $Ar_{402}$ in the number of xd11 may be a group represented by Formulae 7-1 to 7-18, but embodiments are not limited thereto:

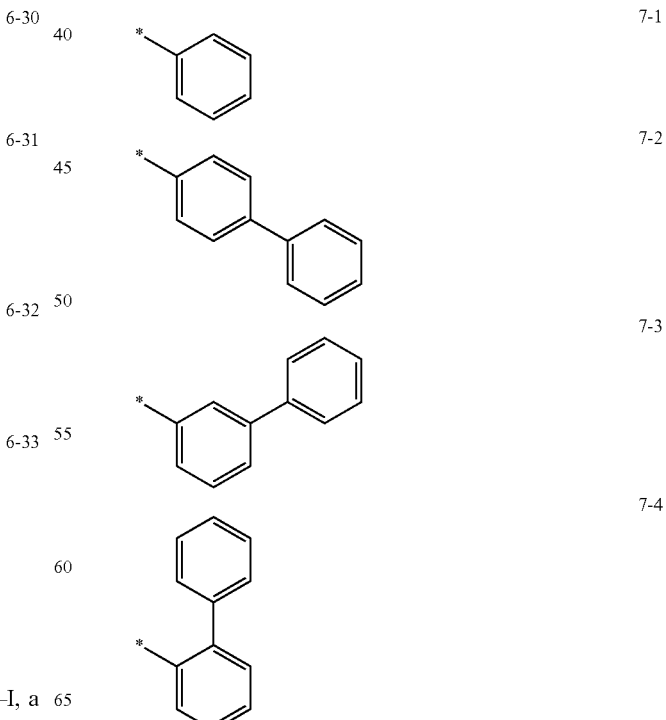

7-1
7-2
7-3
7-4

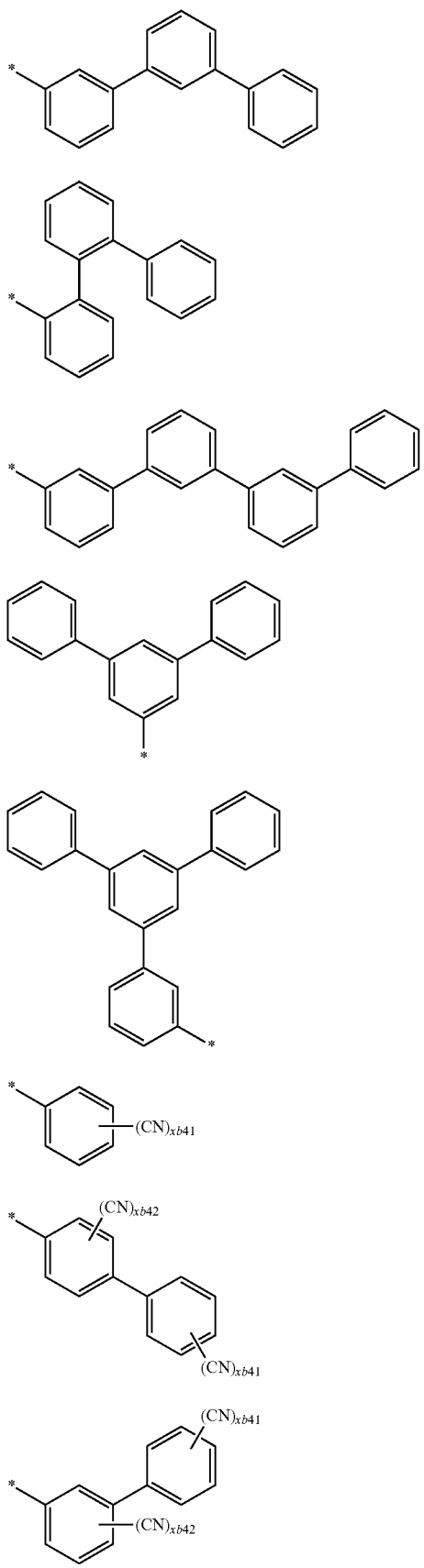
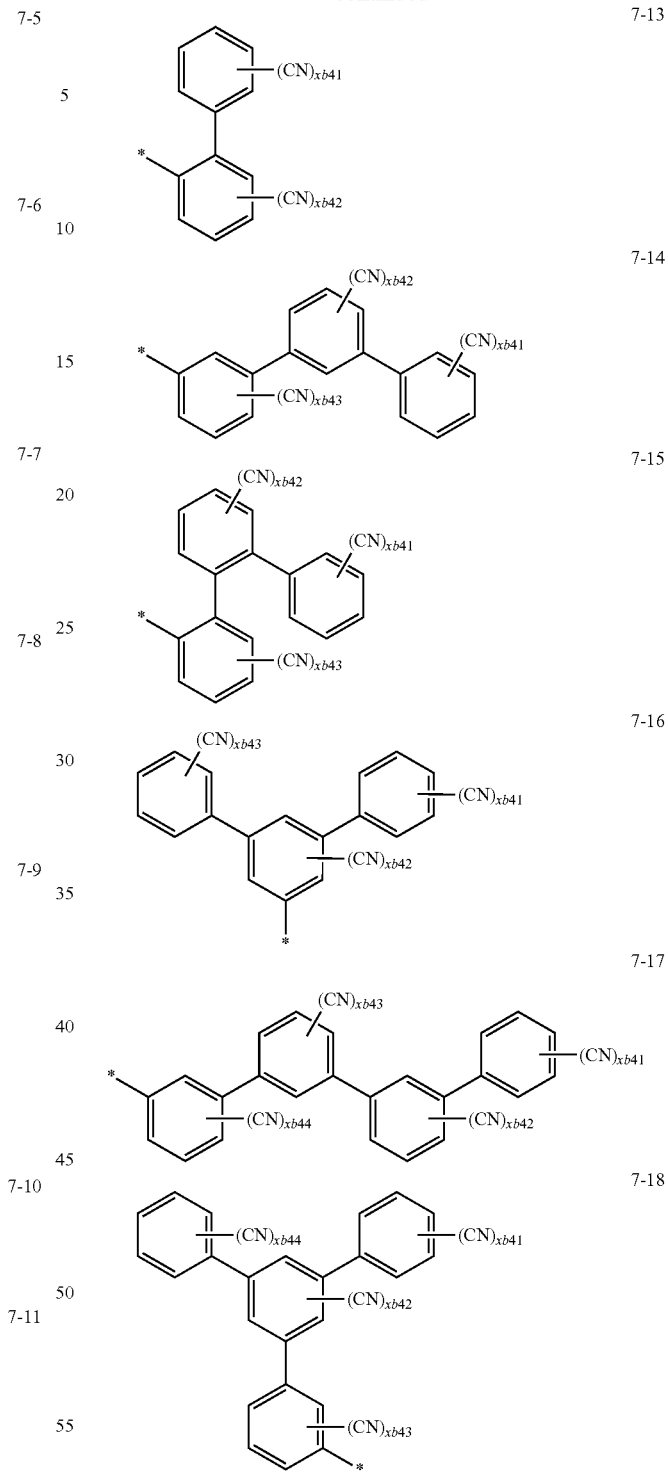
wherein, in Formulae 7-1 to 7-18,
xb41 to xb44 may each be 0, 1, or 2, provided that xb41 in Formula 7-10 may not be 0, xb41+xb42 in Formulae 7-11 to 7-13 may not be 0, xb41+xb42+xb43 in Formulae 7-14 to 7-16 may not be 0, xb41+xb42+xb43+xb44 in Formulae 7-17 and 7-18 may not be 0, and * indicates a binding site to an adjacent atom.
In Formula E-1, at least two $Ar_{301}(s)$ may be identical to or different from each other, and at least two $L_{301}(s)$ may be identical to or different from each other. In Formula H-1, at least two $L_{401}$(s) may be identical to or different from each other, and at least two $Ar_{402}$(s) may be identical to or different from each other.

In an embodiment, the electron transporting host may include i) at least one a cyano group, a pyrimidine group, a pyrazine group, a triazine group, or any combination thereof, or ii) a triphenylene group, and the hole transporting host may include a carbazole group.

In one or more embodiments, the electron transporting host may include at least one cyano group.

The electron transporting host may be, for example, one compound of Groups HE1 to HE7, but embodiments are not limited thereto:

Group HE1

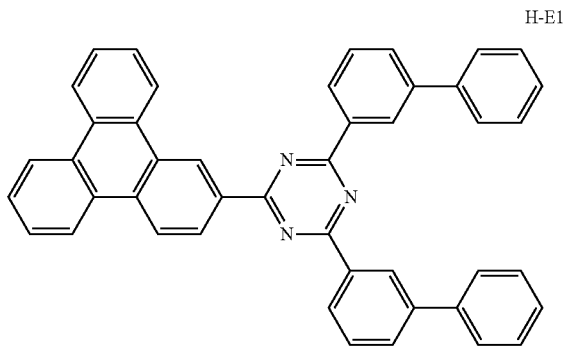

H-E1

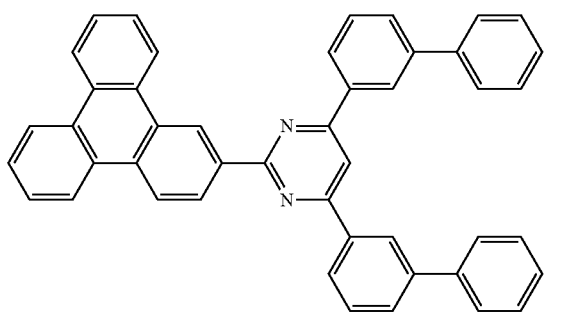

H-E2

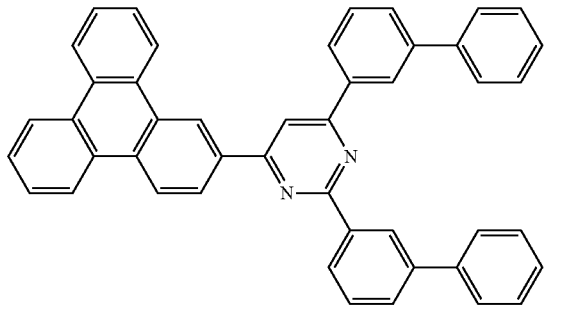

H-E3

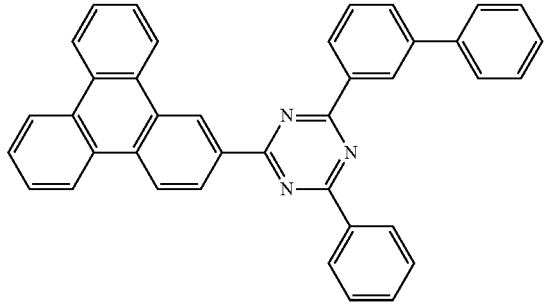

H-E4

-continued
H-E5
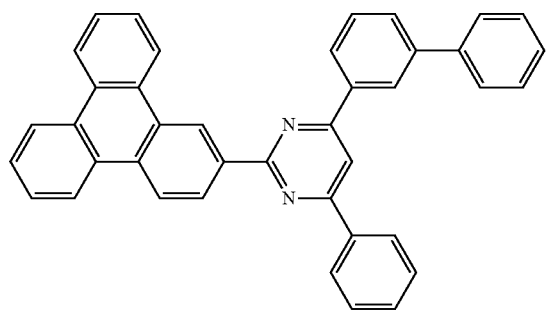
H-E6
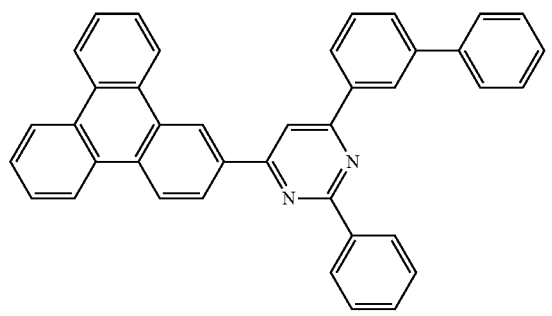
H-E7
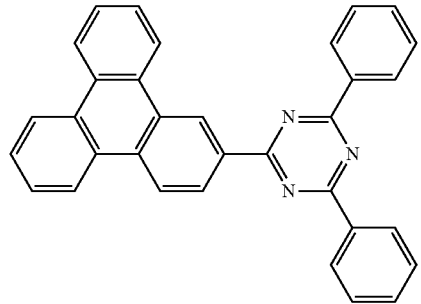
H-E8
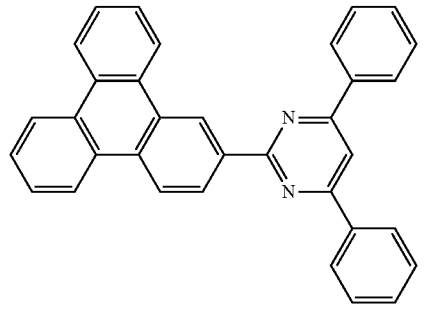
H-E9
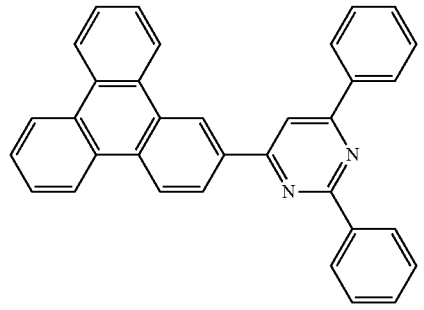

-continued
H-E10
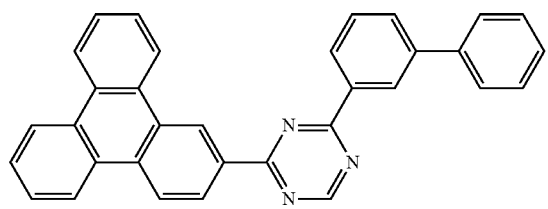
H-E11
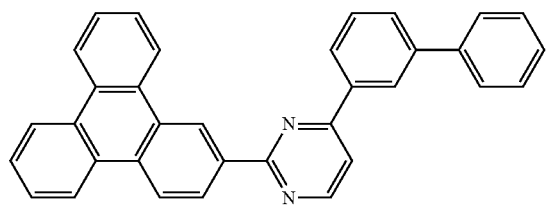
H-E12
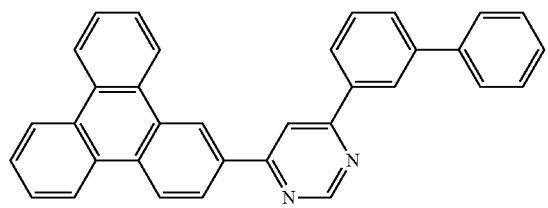
H-E13
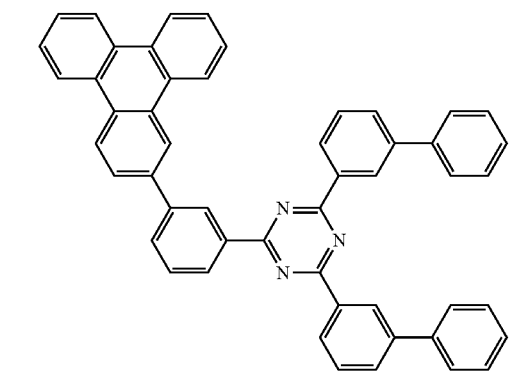
H-E14
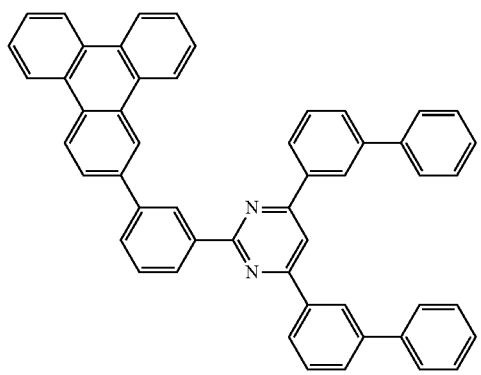

-continued
H-E15
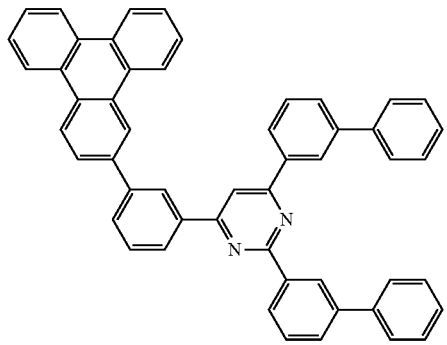
H-E16
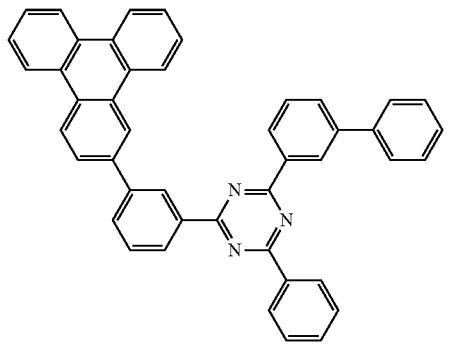
H-E17
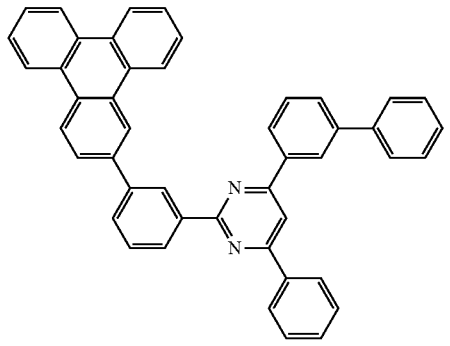
H-E18
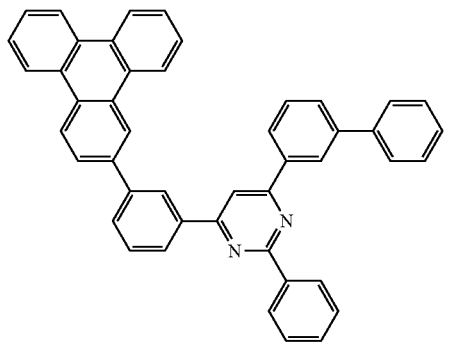

-continued
H-E19
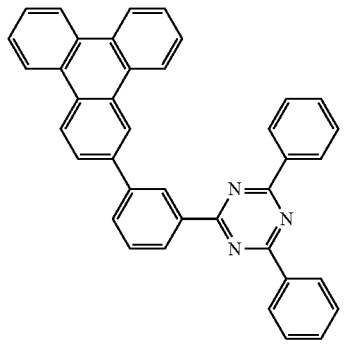
H-E20
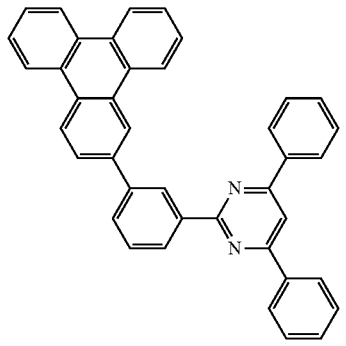
H-E21
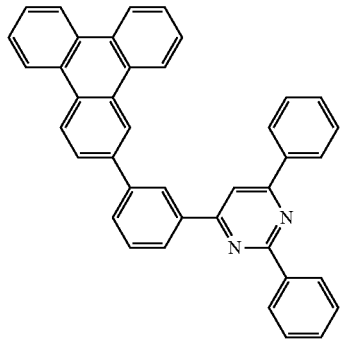
H-E22
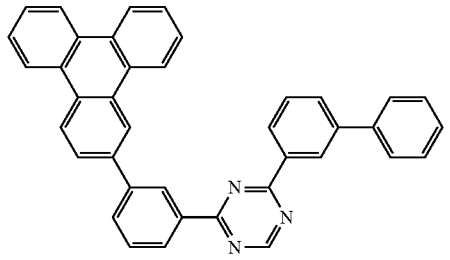
H-E23
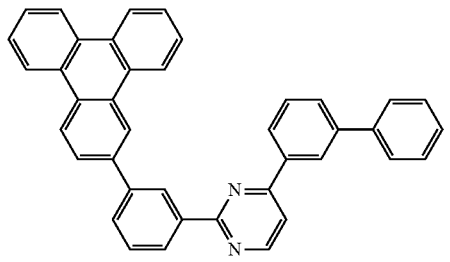

-continued
H-E24
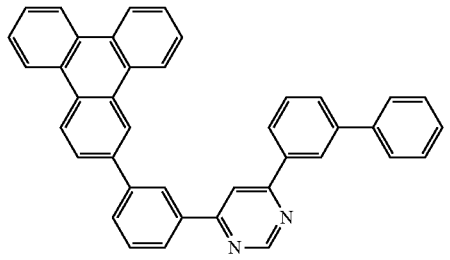
H-E25
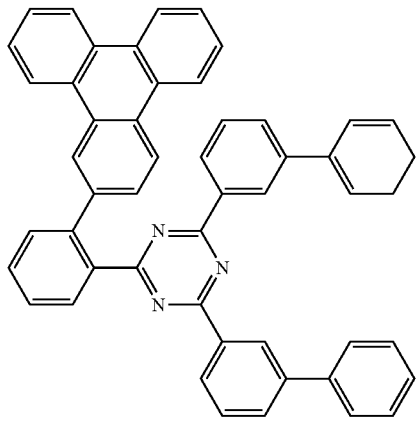
H-E26
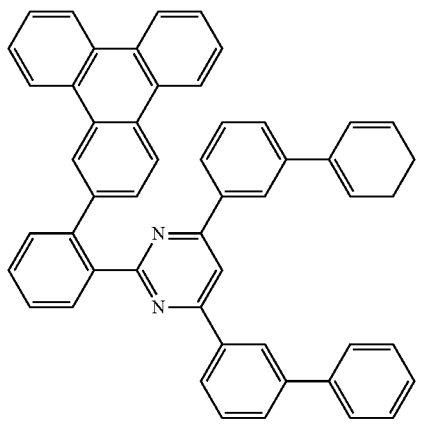
H-E27
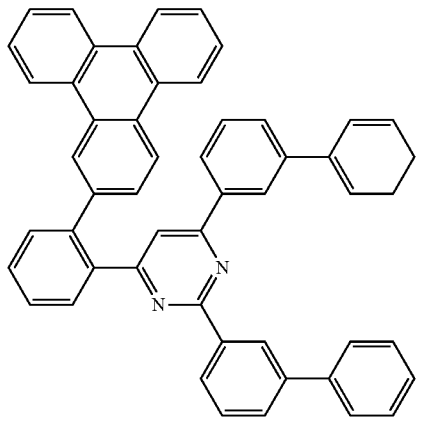

-continued
H-E28
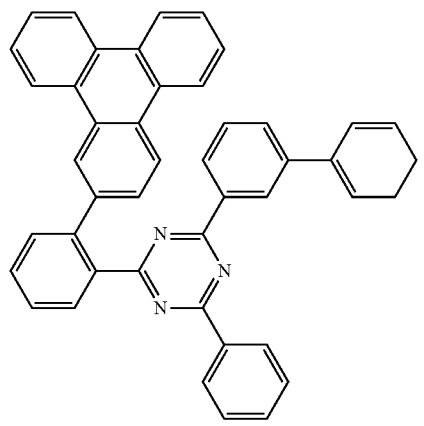
H-E29
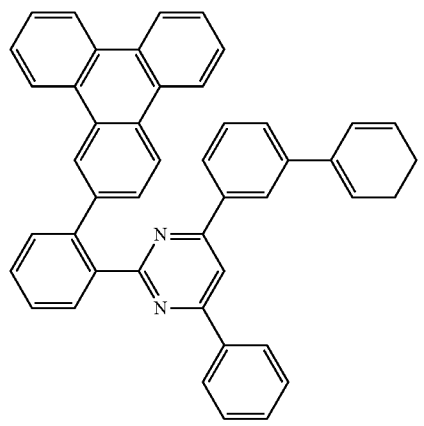
H-E30
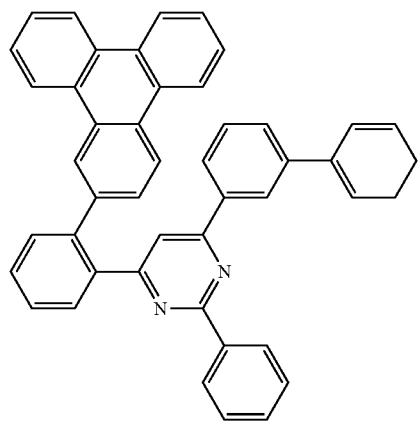

-continued
H-E31
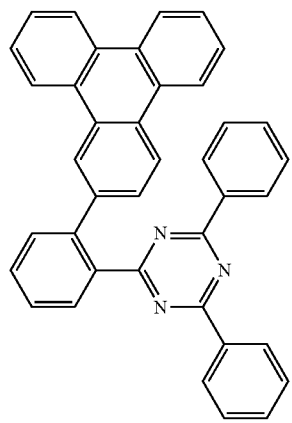
H-E32
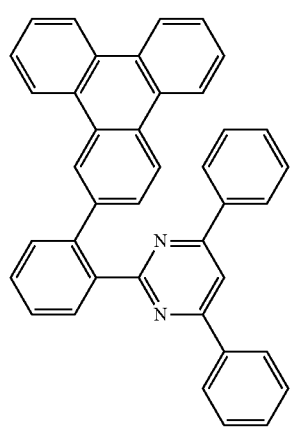
H-E33
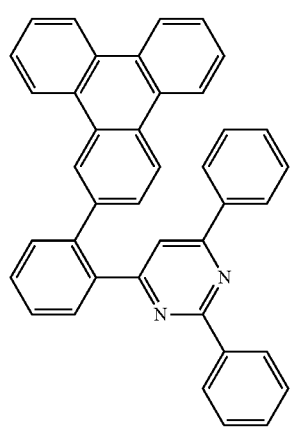
H-E34
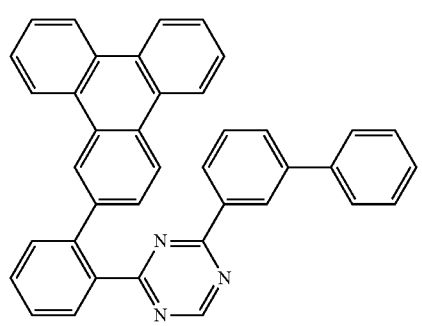

-continued

H-E35

H-E36

H-E37

-continued
H-E38
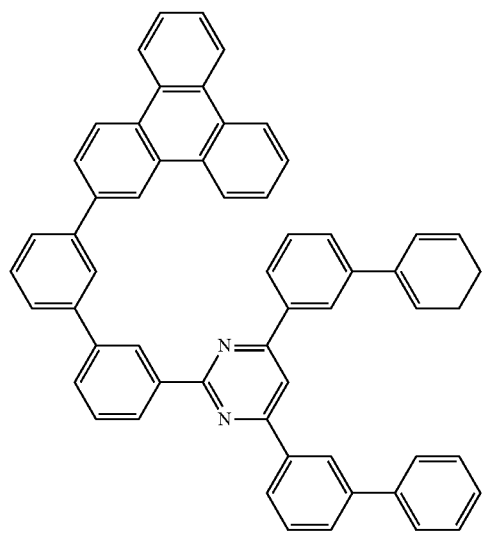
H-E39
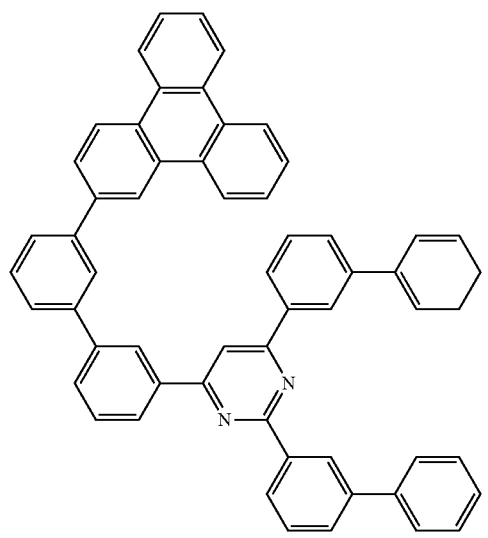
H-E40
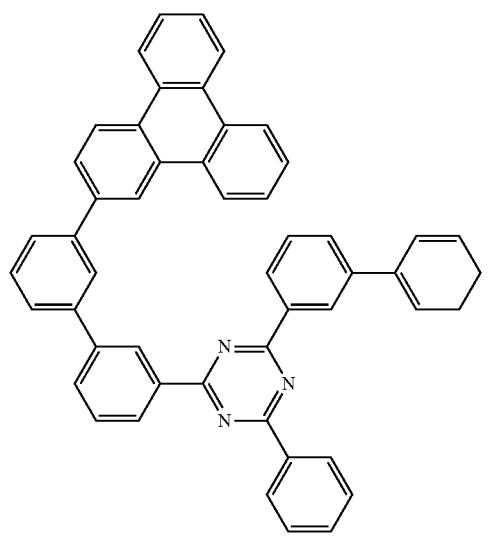

-continued
H-E41
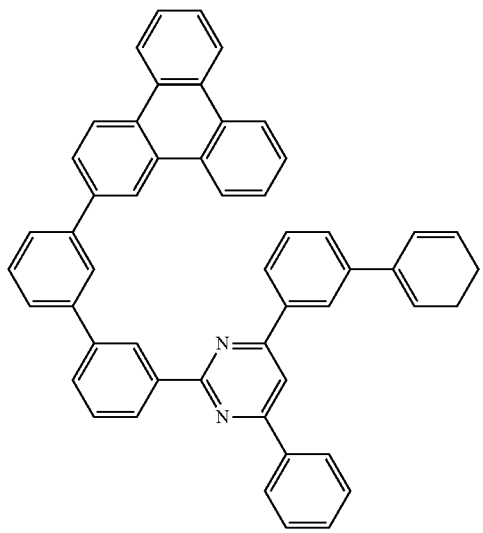
H-E42
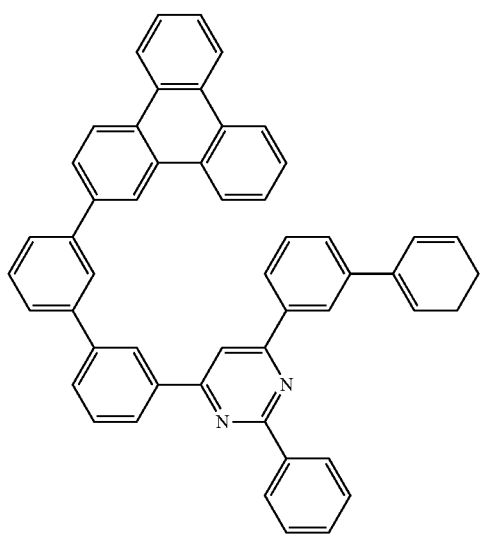
H-E43
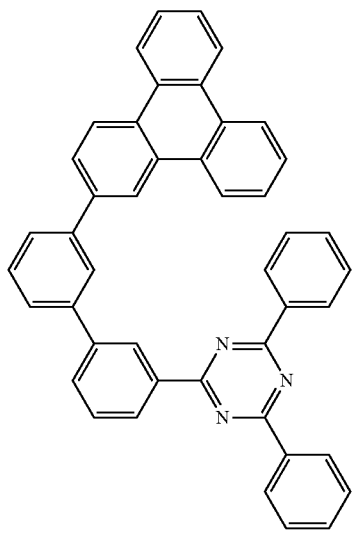

-continued
H-E44
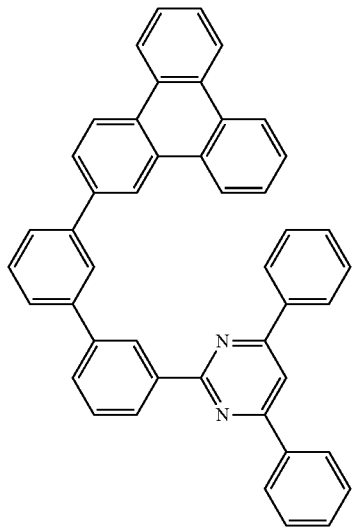
H-E45
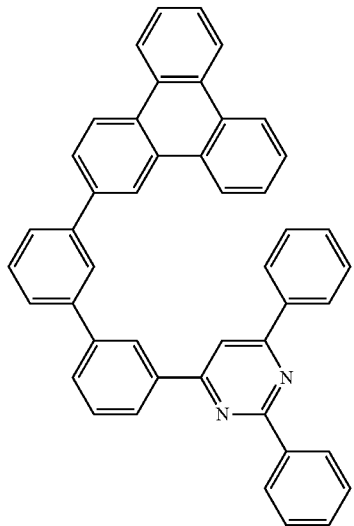
H-E46
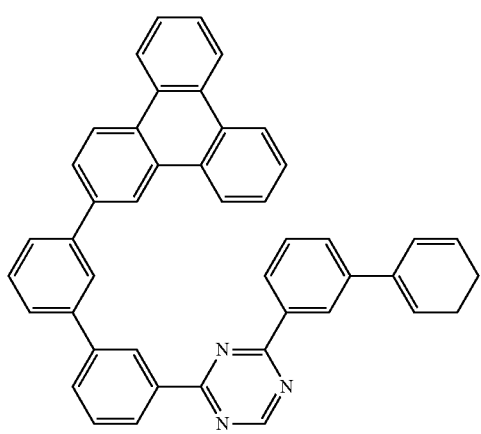

-continued
H-E47
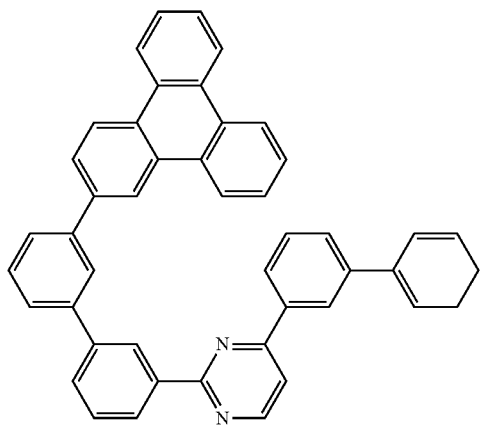
H-E48
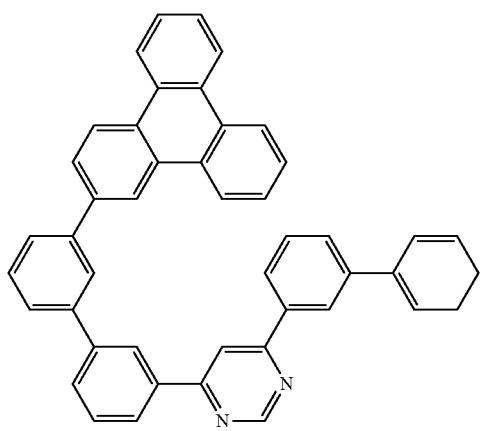
H-E49
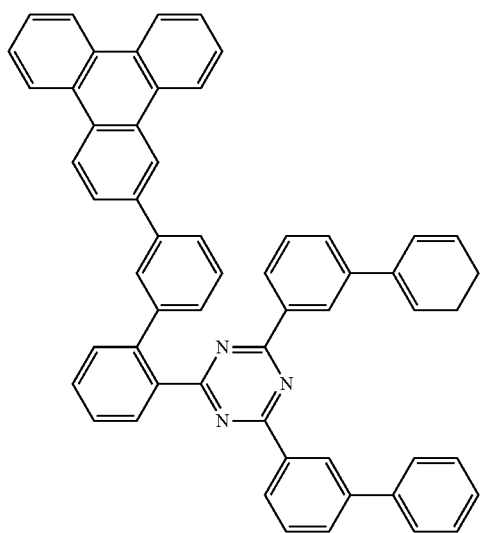

-continued
H-E50
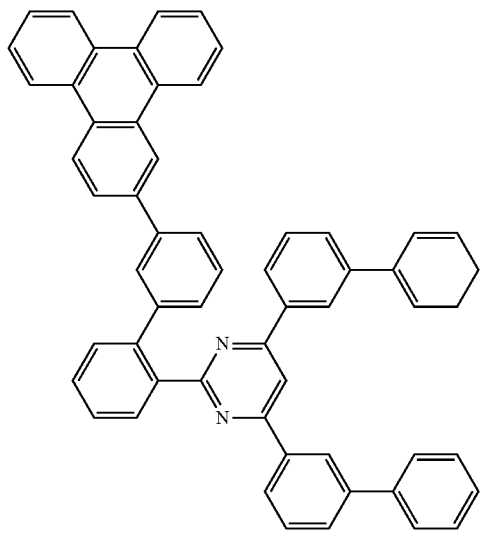
H-E51
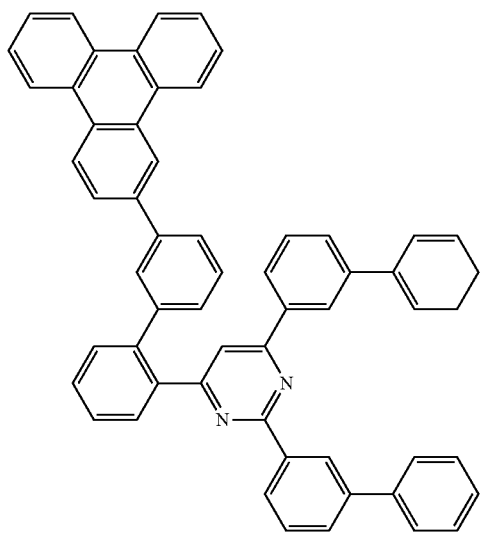
H-E52
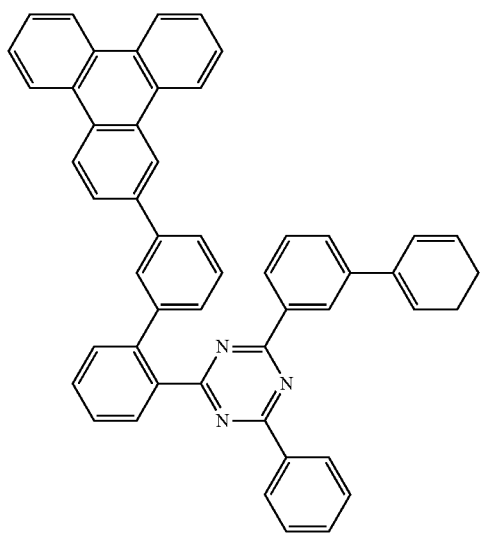

-continued
H-E53
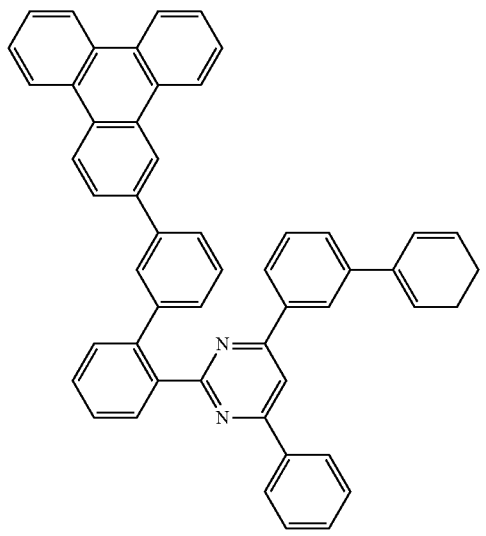
H-E54
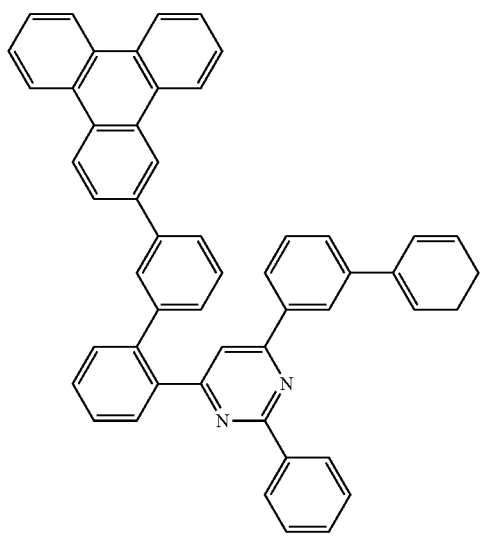
H-E55
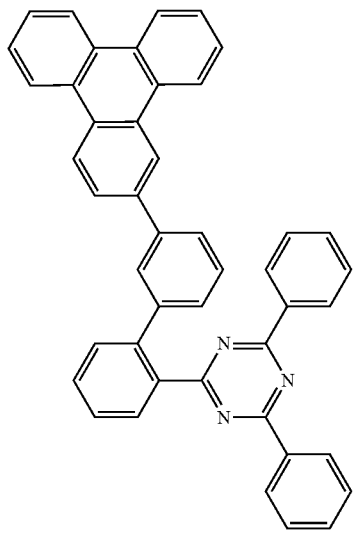

-continued
H-E56
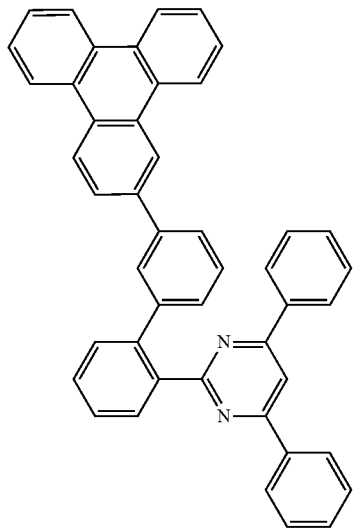
H-E57
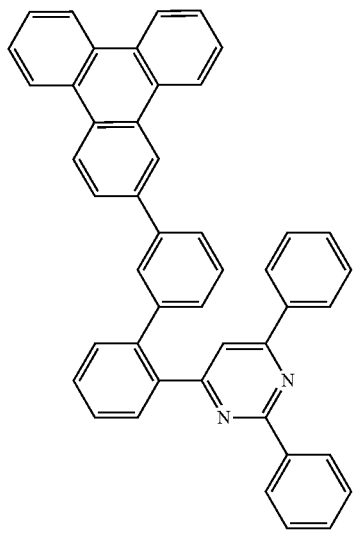
H-E58
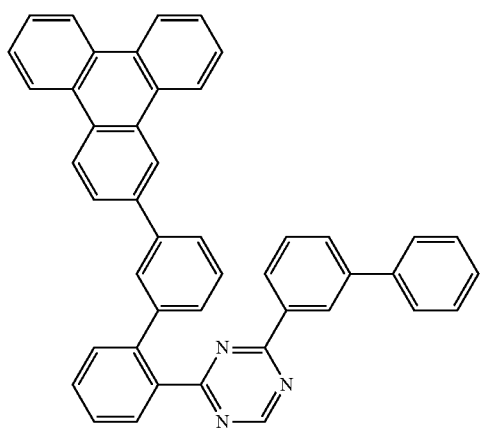

H-E59
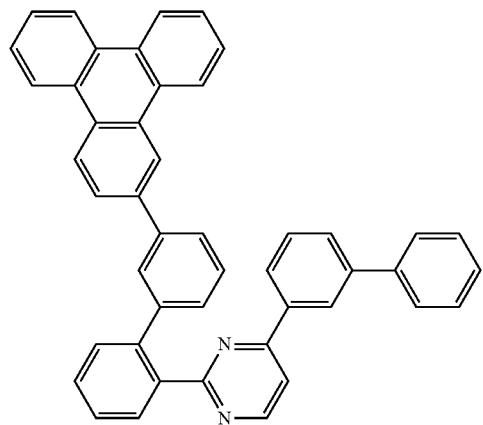
H-E60
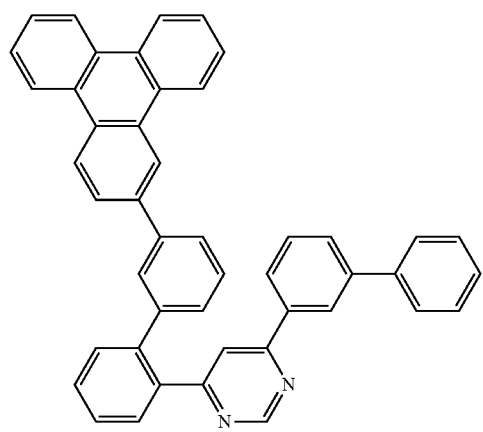
H-E61
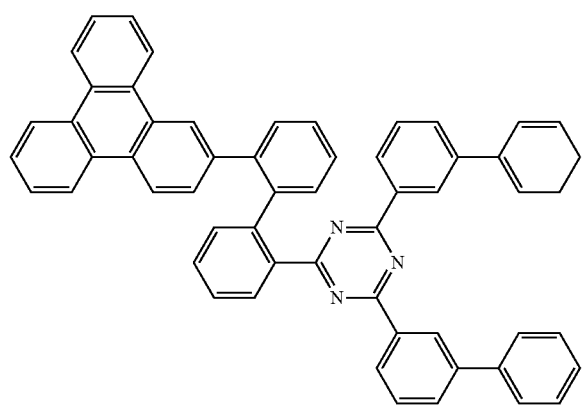

-continued
H-E62
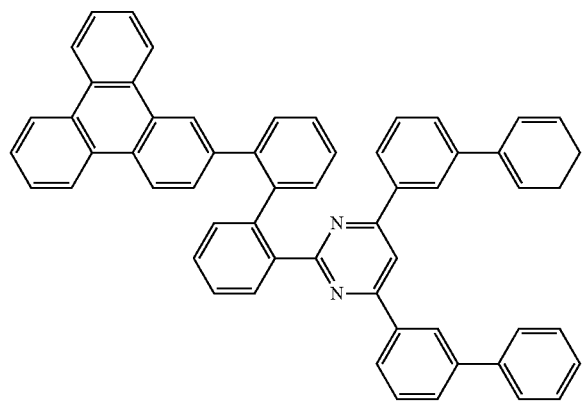
H-E63
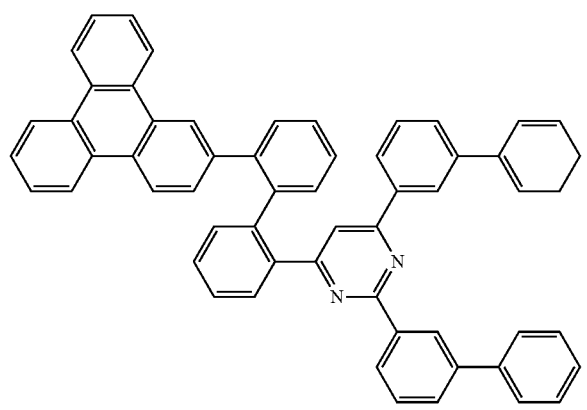
H-E64
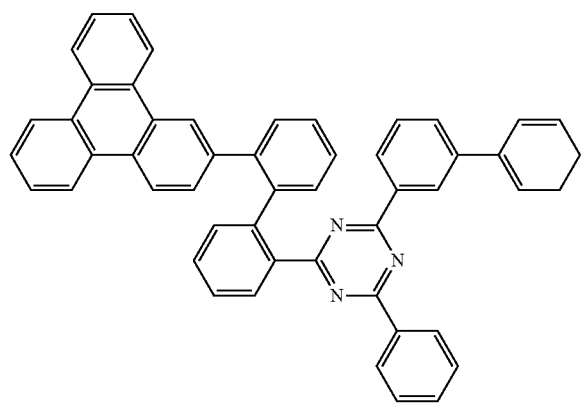

-continued
H-E65
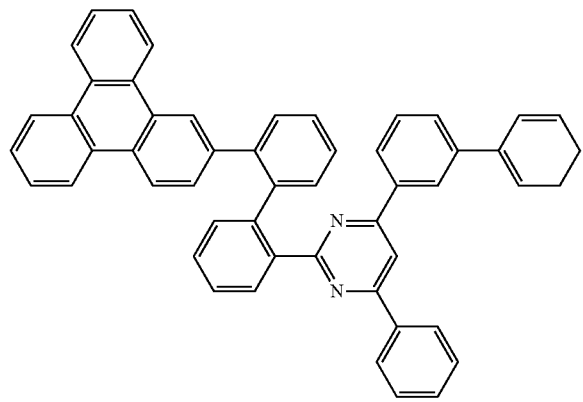
H-E66
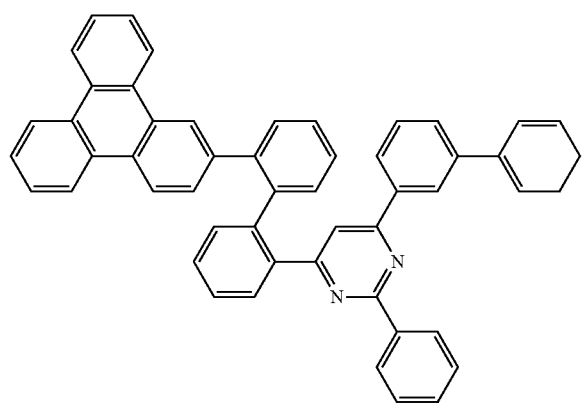
H-E67
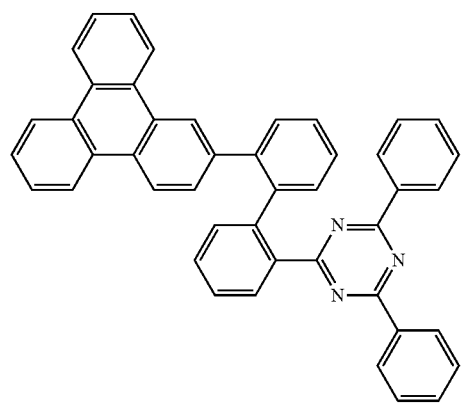
H-368
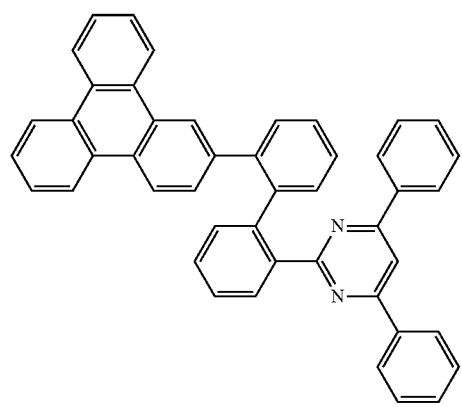

-continued
H-E69
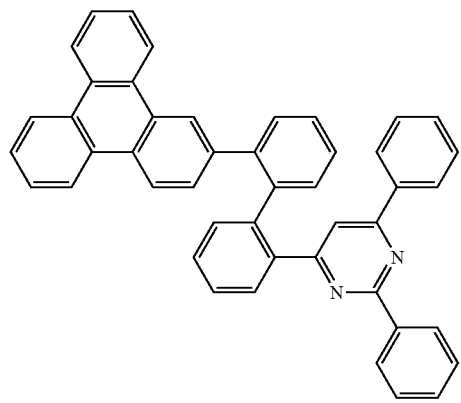
H-E70
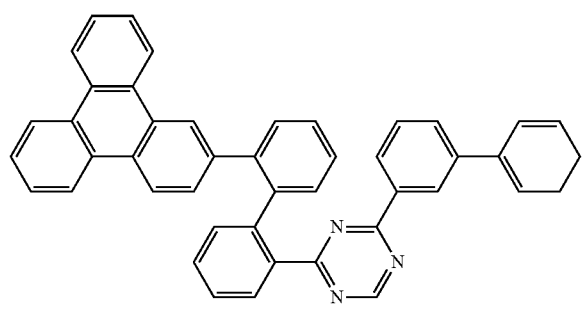
H-E71
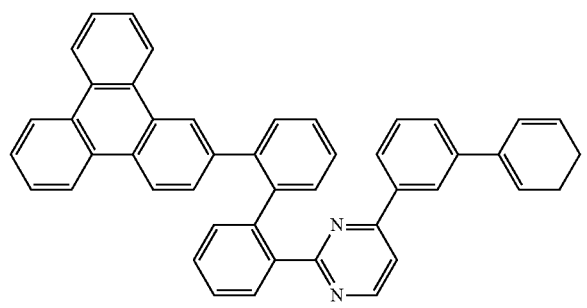
H-E72
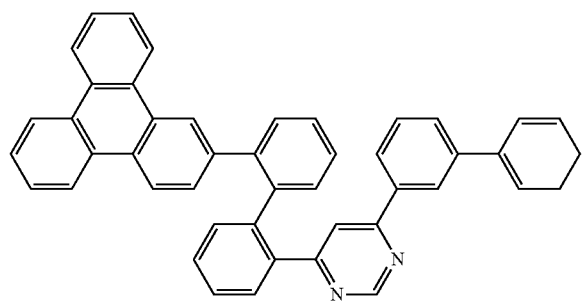

-continued
H-E73
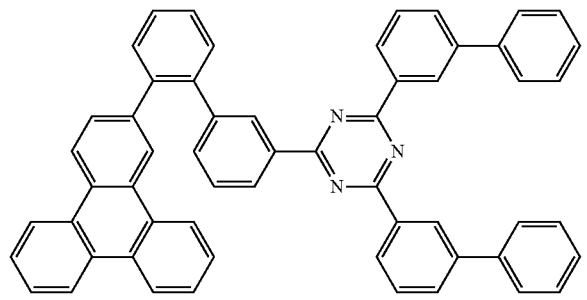
H-E74
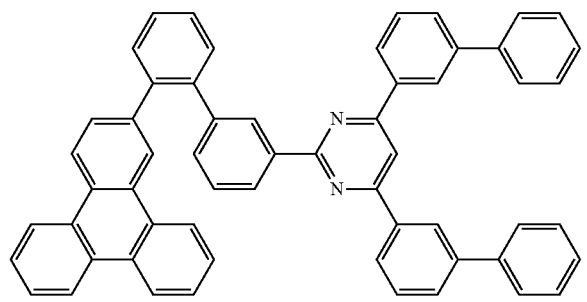
H-E75
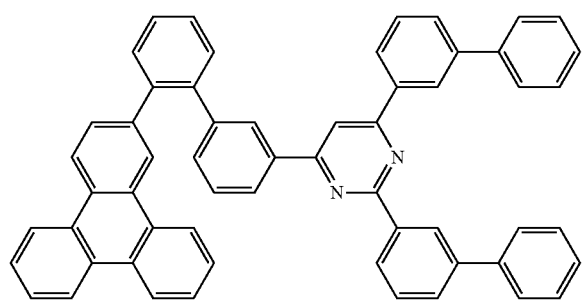
H-E76
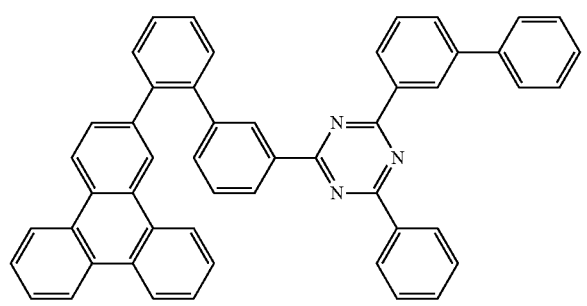
H-E77
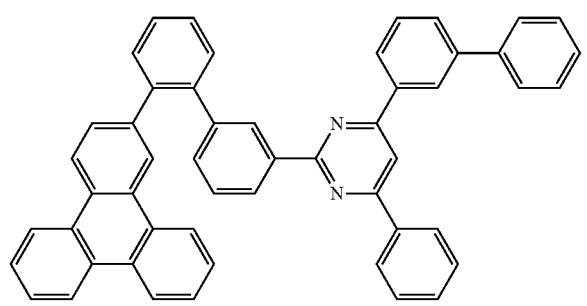

-continued
H-E78
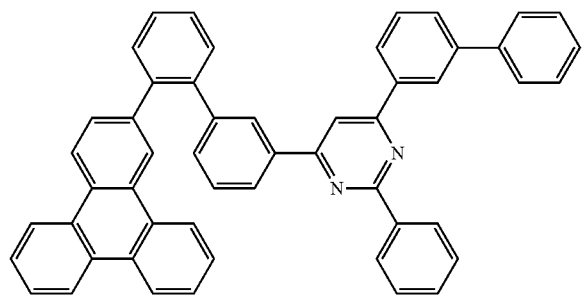
H-E79
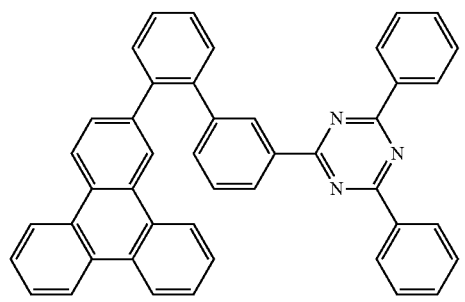
H-E80
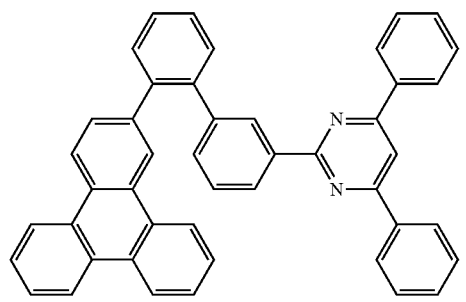
H-E81
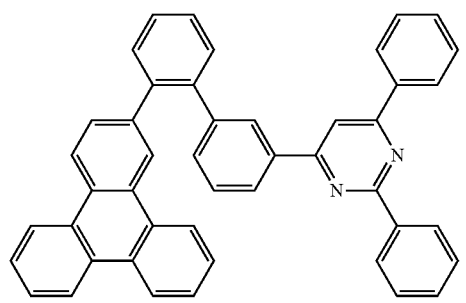
H-E82
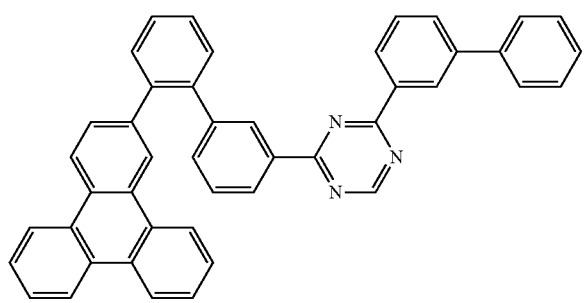

H-E83
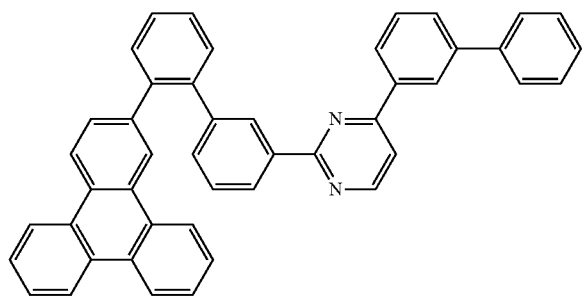
H-E84
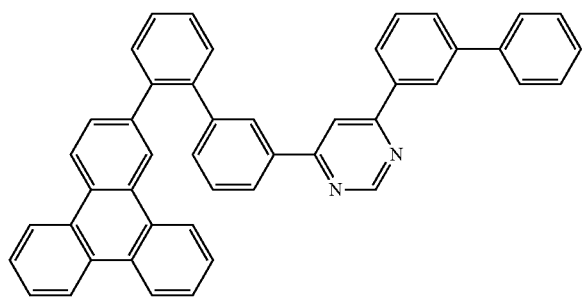
H-E(1)
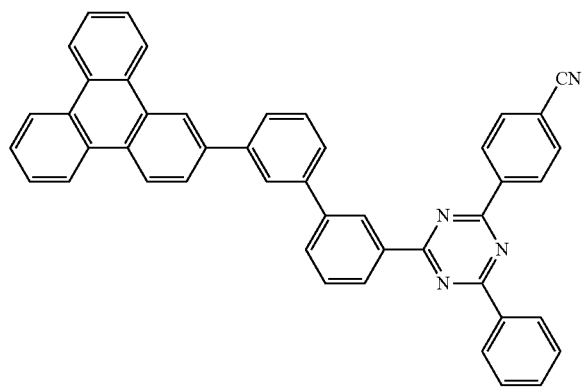
H-E(2)
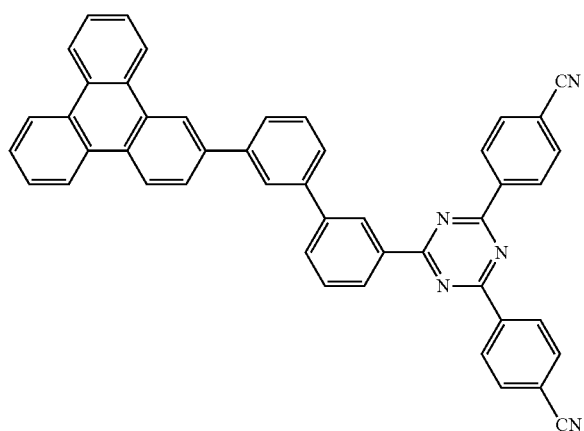

-continued
H-E(3)
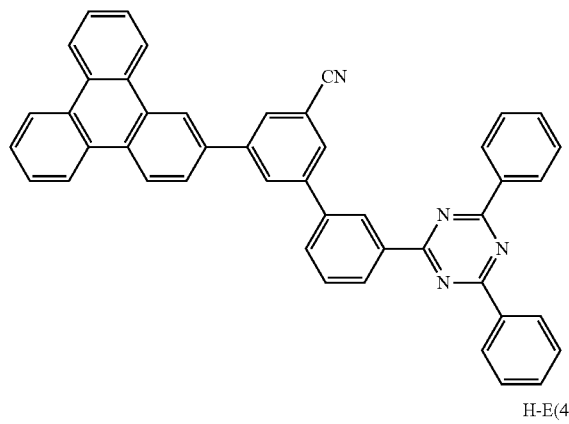
H-E(4)
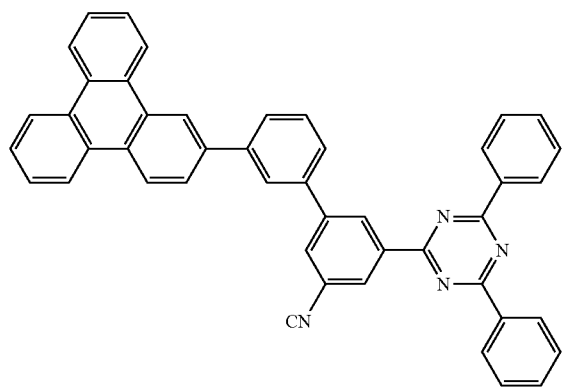
A-1
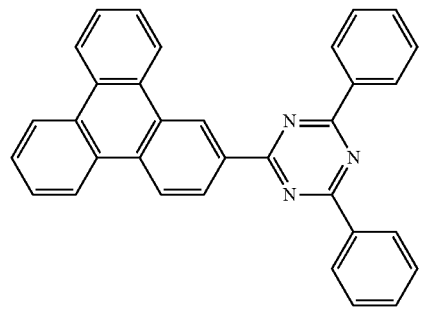
A-2
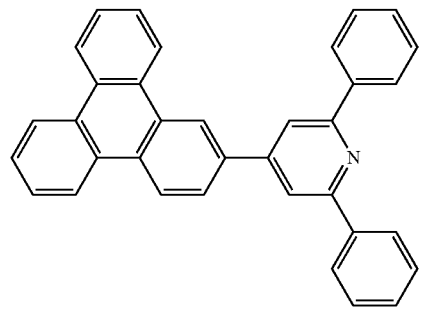

A-3
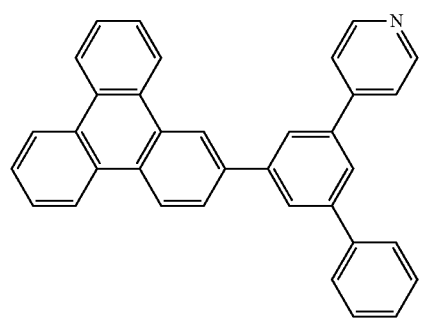
A-4
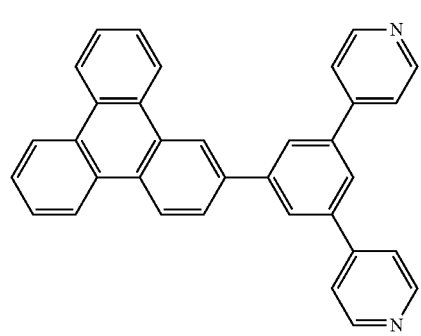
A-5
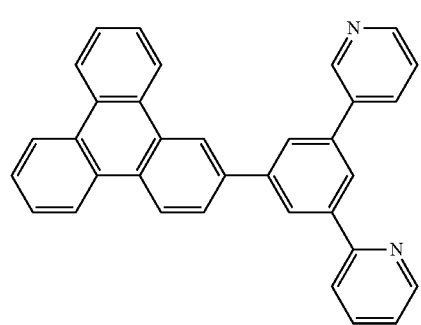
A-6

A-7

-continued
A-8
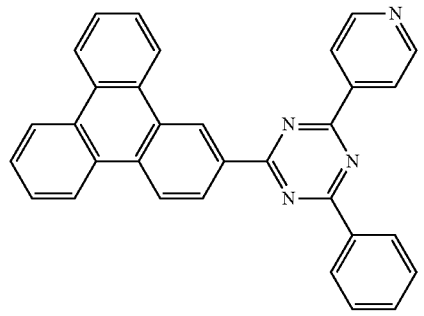
A-9
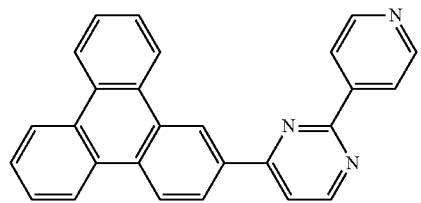
A-10
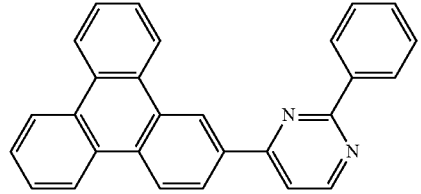
A-11
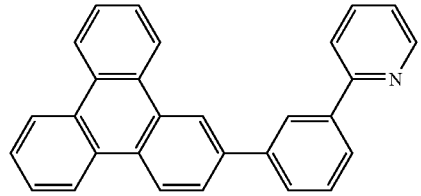
A-12
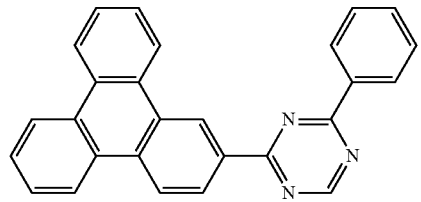
A-13
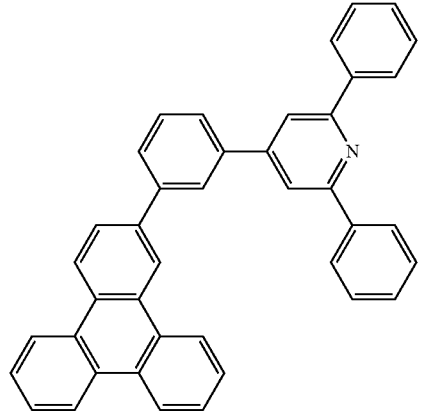

-continued
A-14
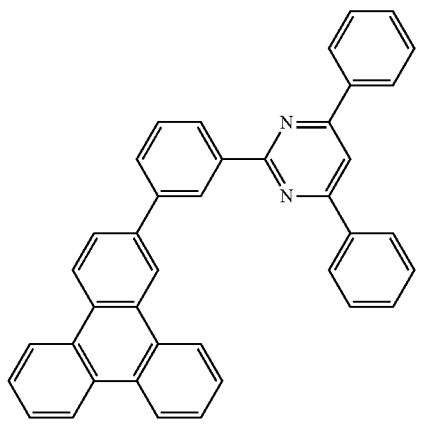
A-15
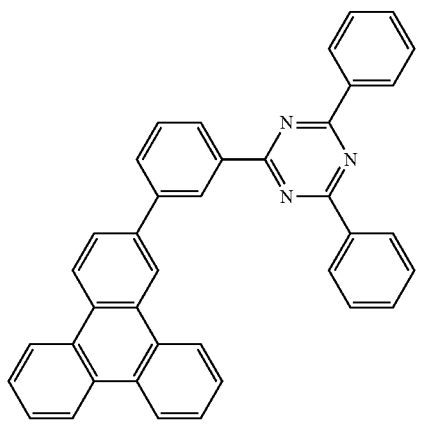
A-16
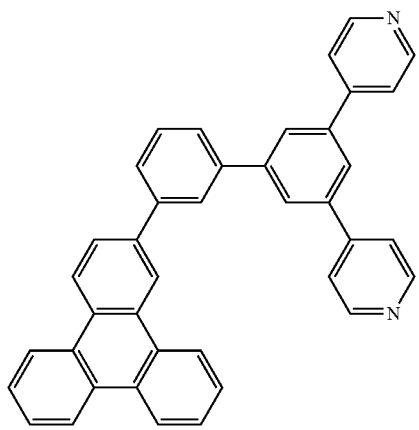

-continued
A-17
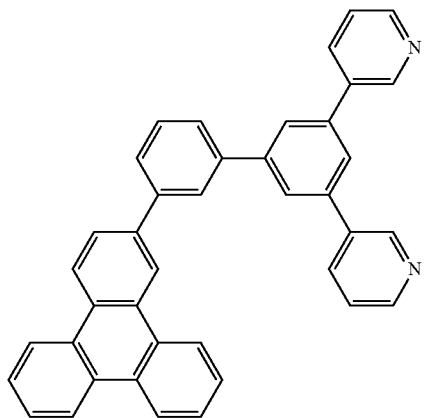
A-18
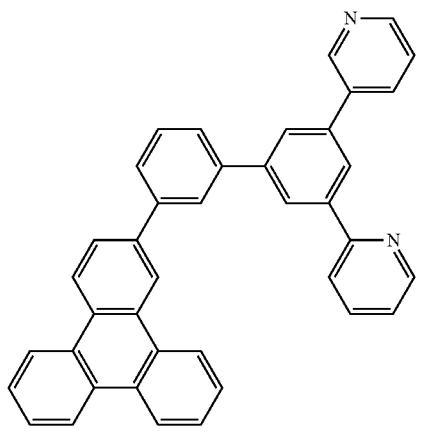
A-19
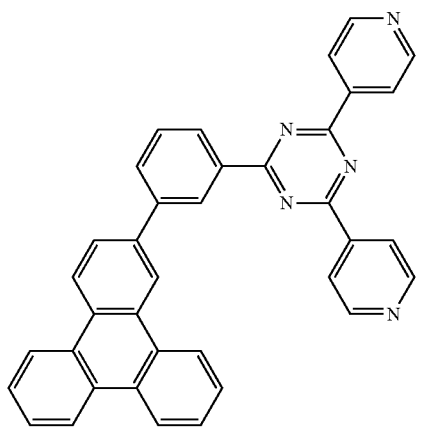

-continued
A-20
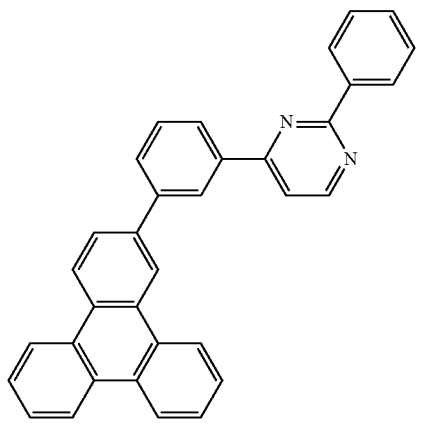
A-21
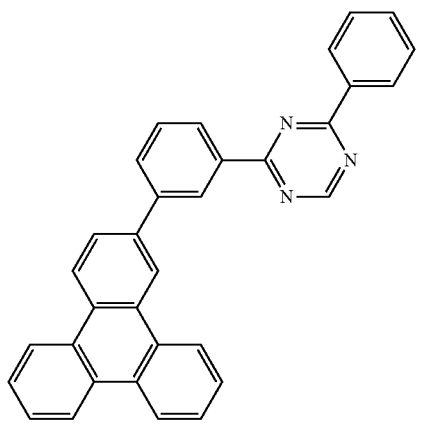
A-22
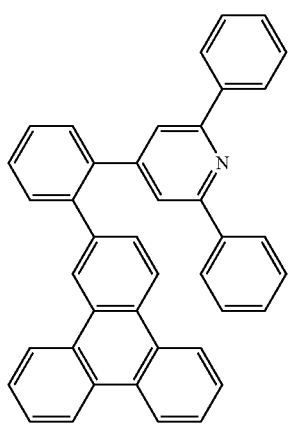

-continued
A-23
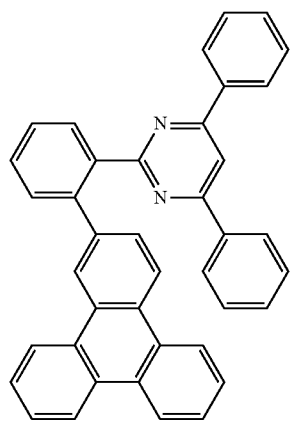
A-24
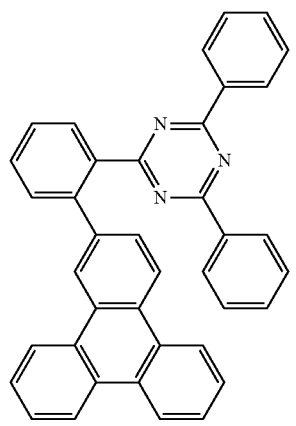
A-25
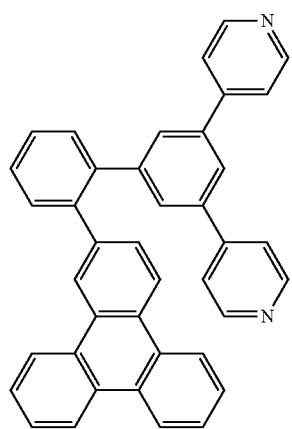

-continued
A-26
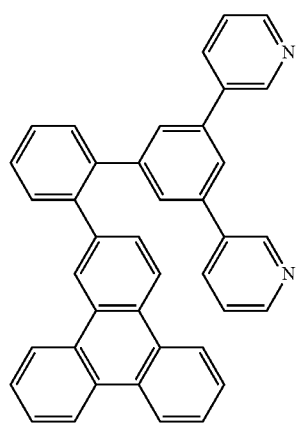
A-27
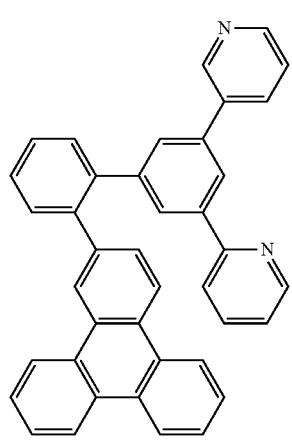
A-28
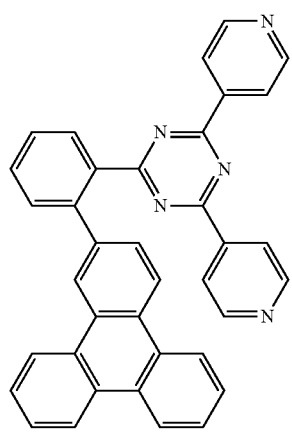

-continued
A-29
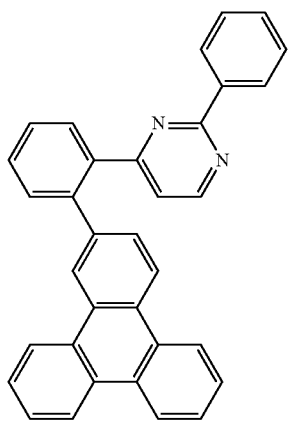
A-30
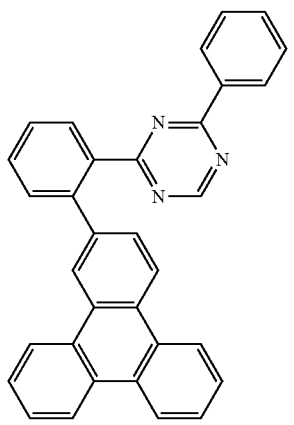
A-31
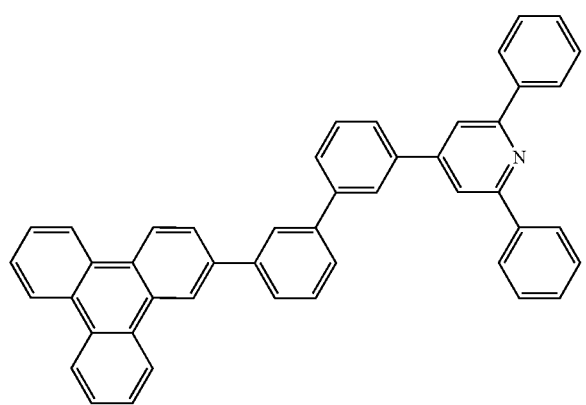

A-32
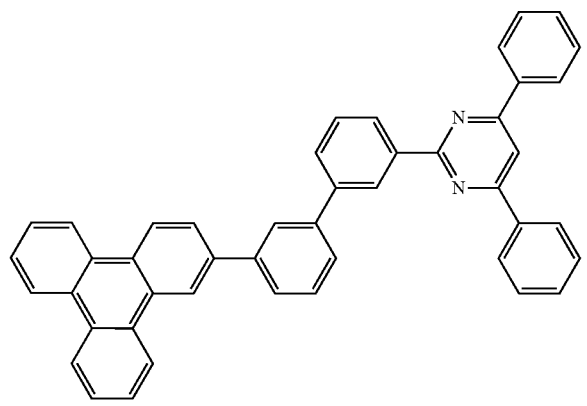
A-33
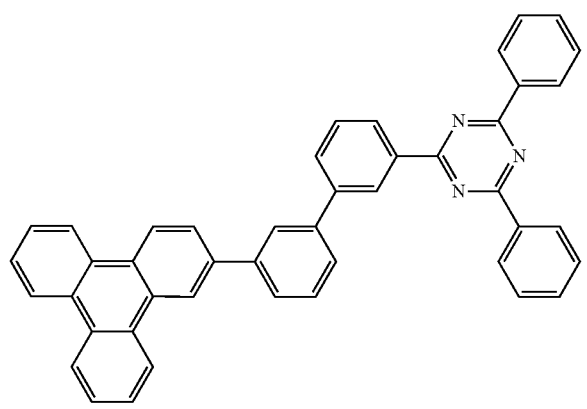
A-34
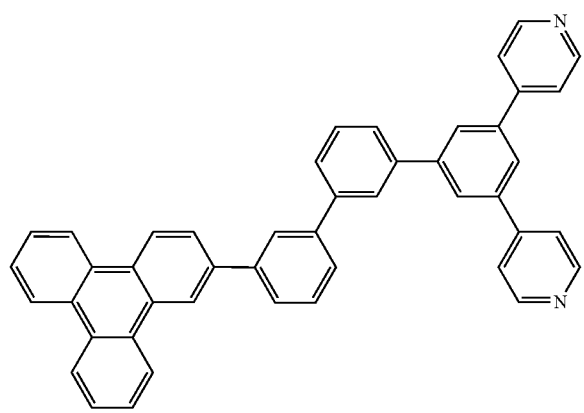

-continued
A-35
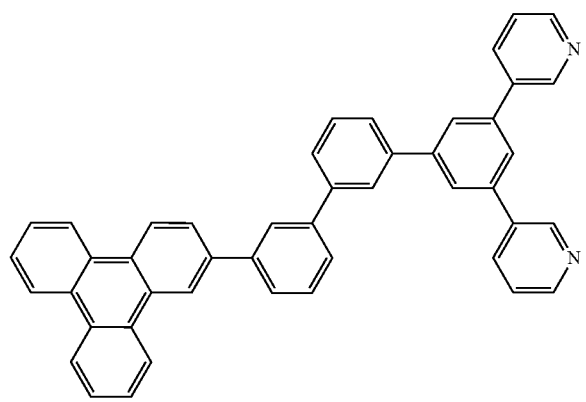
A-36
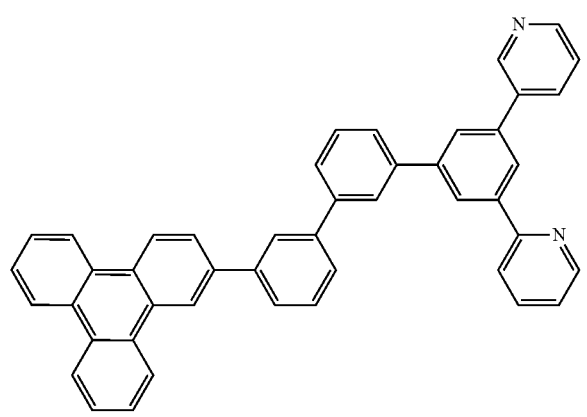
A-37
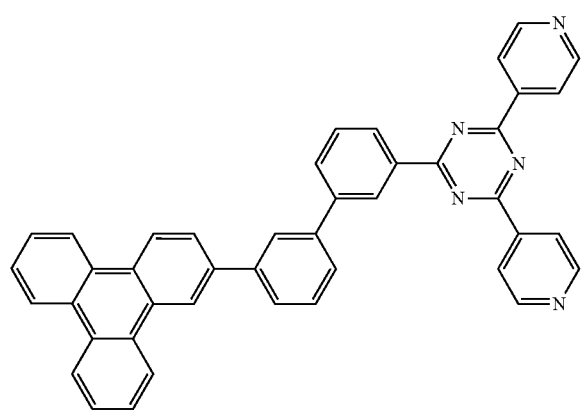

-continued
A-38
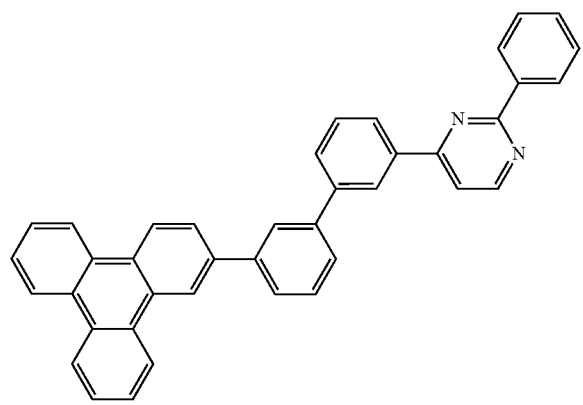
A-39
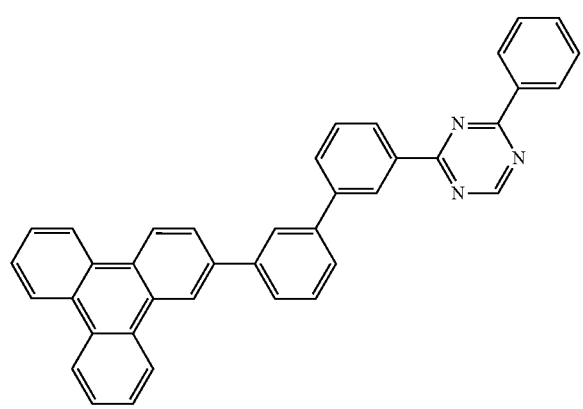
A-40
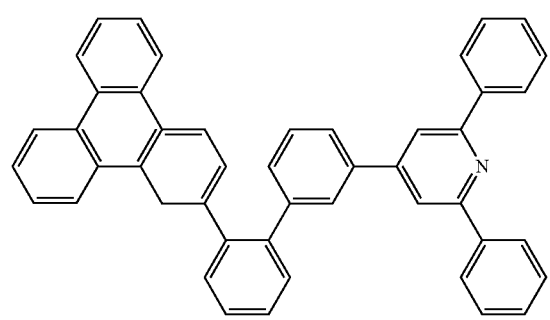
A-41
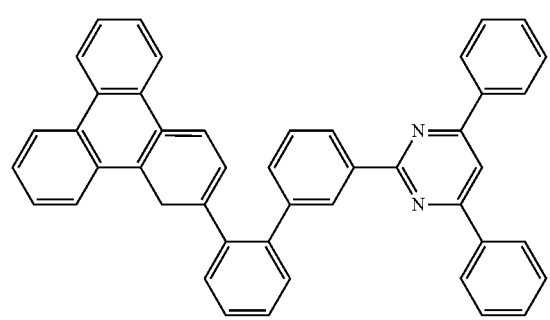

-continued
A-42
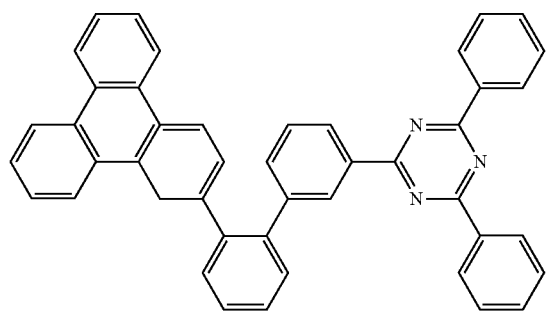
A-43
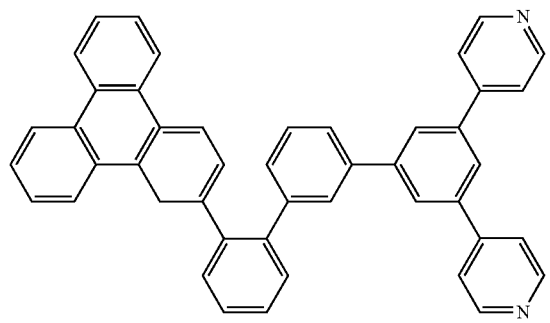
A-44
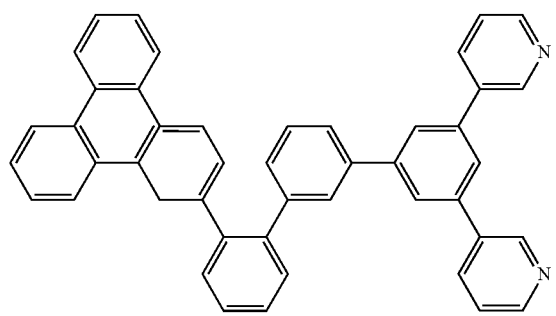
A-45
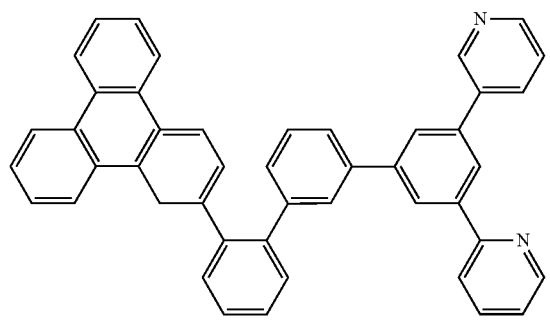

-continued
A-46
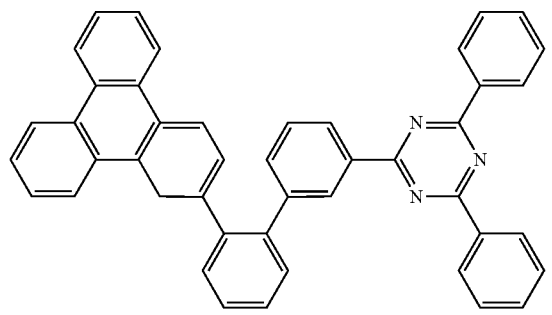
A-47
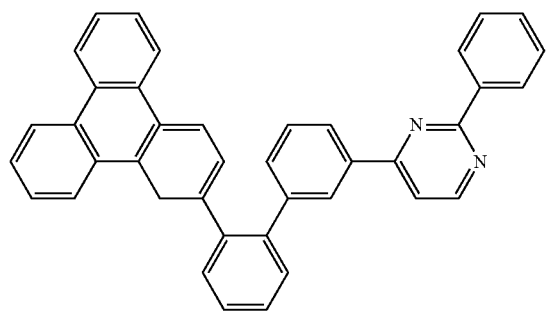
A-48
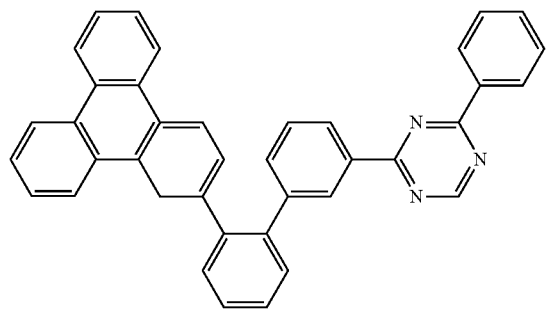
A-49
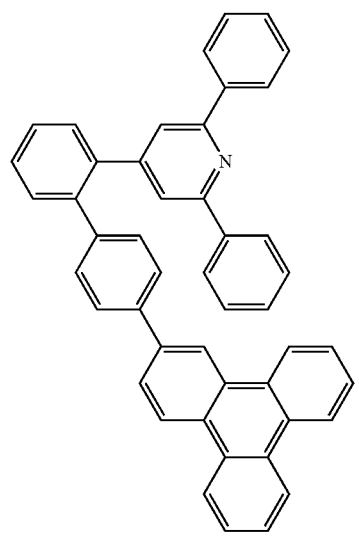

-continued
A-50
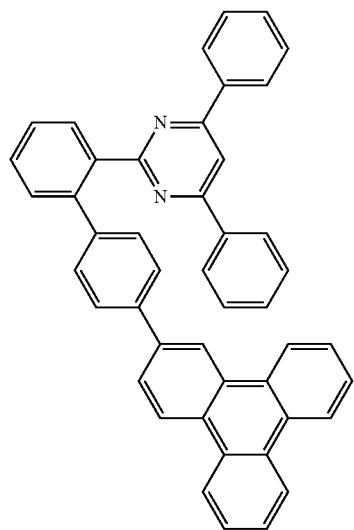
A-51
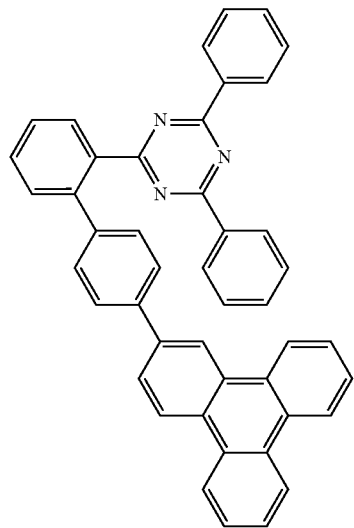
A-52
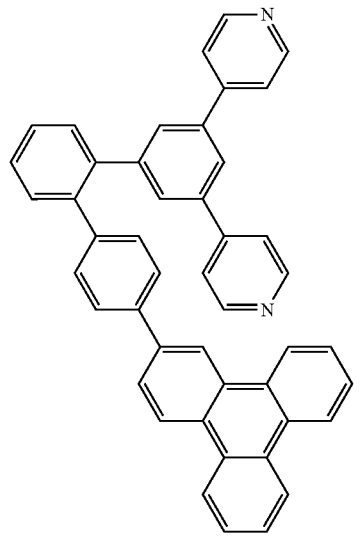

A-53
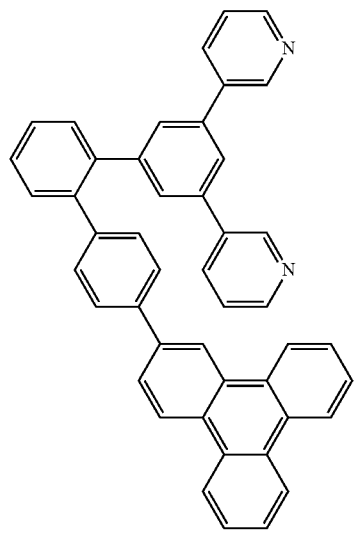
A-54
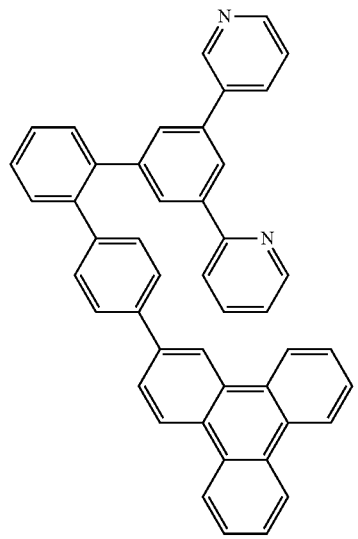
A-55
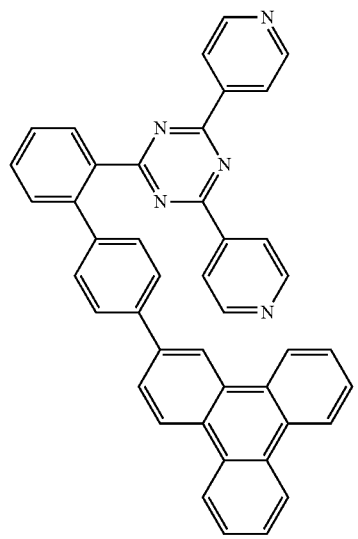

A-56
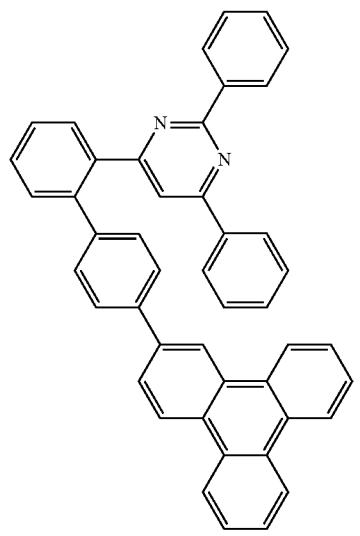
A-57
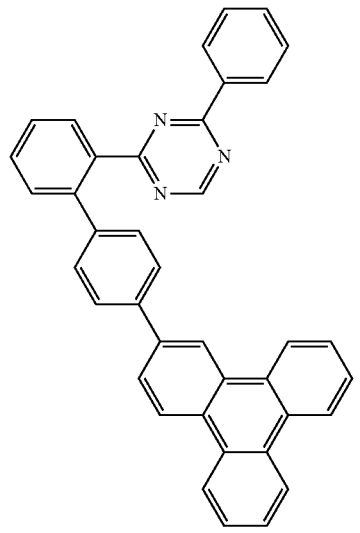
A-58
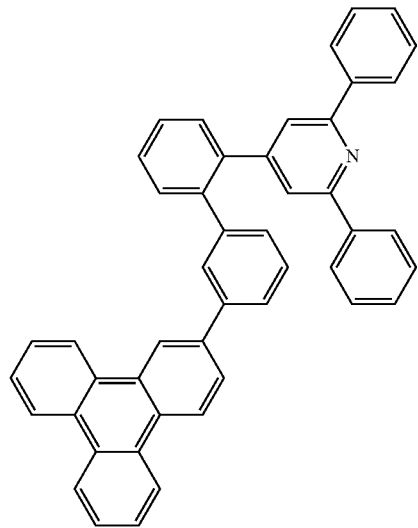

-continued
A-59
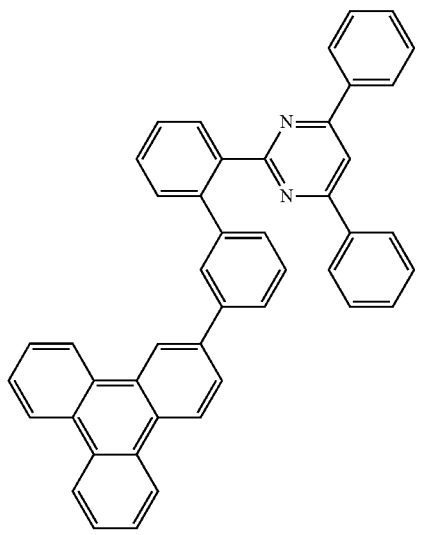
A-60
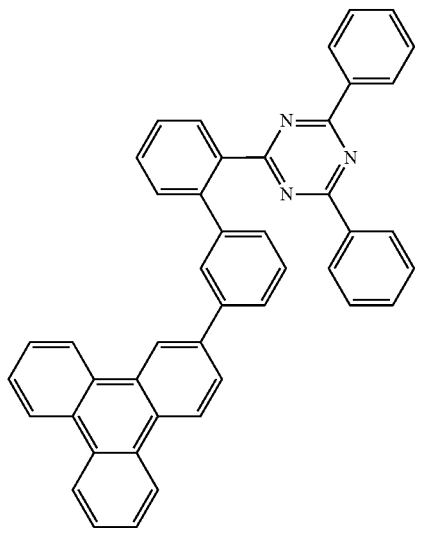
A-61
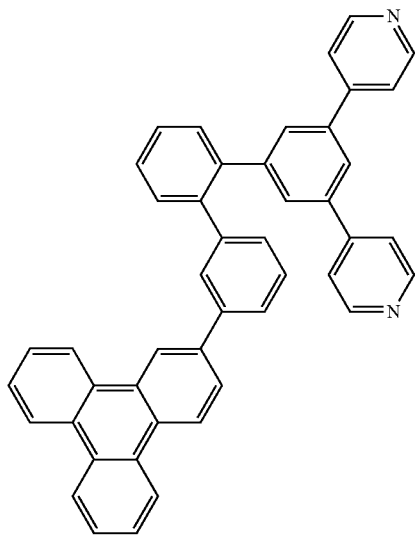

-continued
A-62
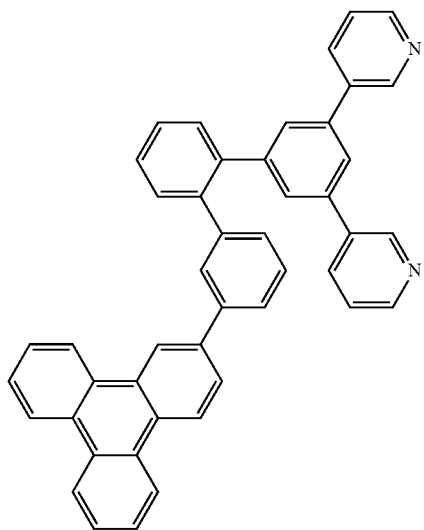
A-63
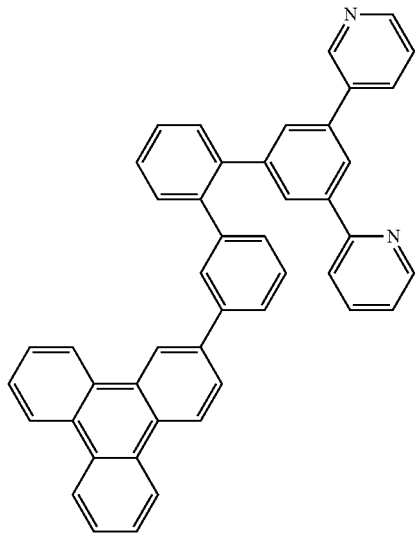
A-64
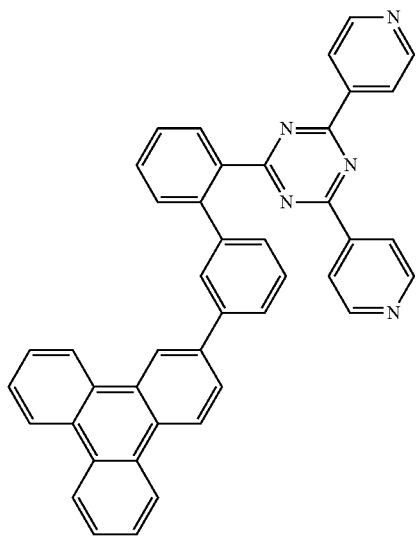

-continued
A-65
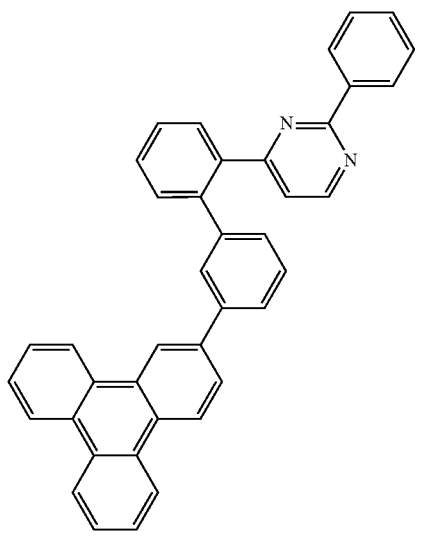
A-66
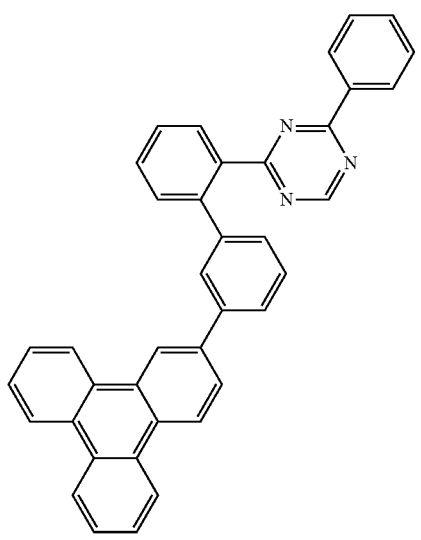
A-67
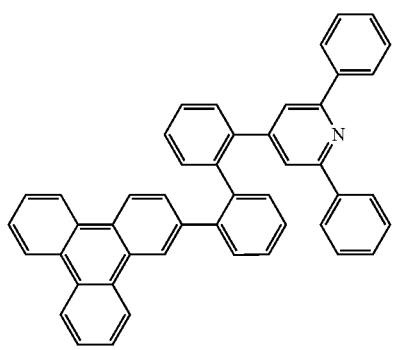

-continued
A-68
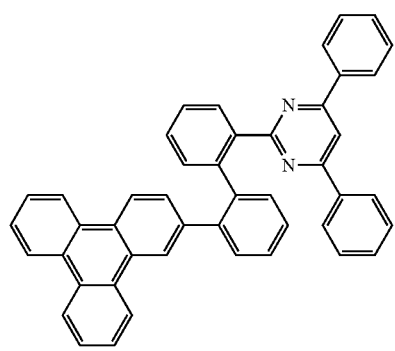
A-69
A-70
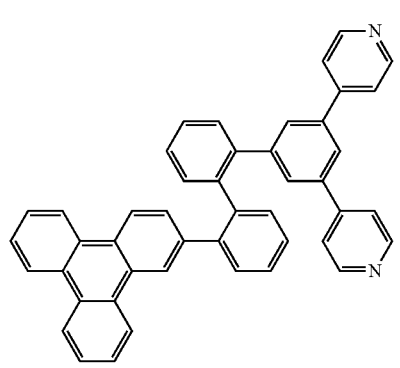
A-71
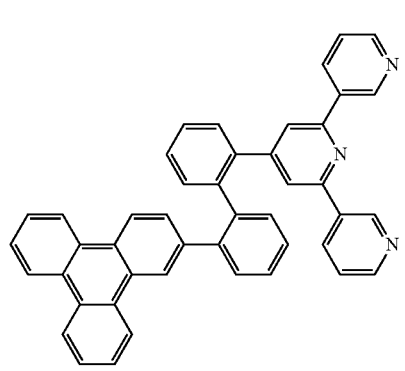

-continued
A-72
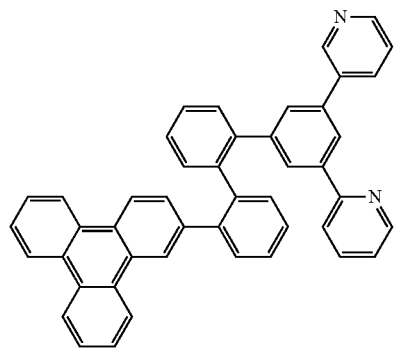
A-73
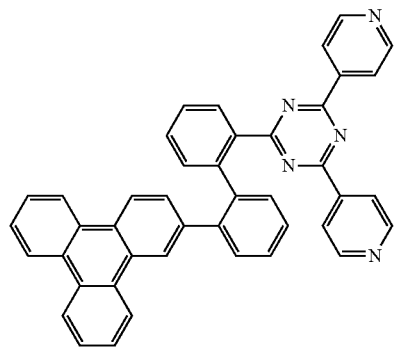
A-74
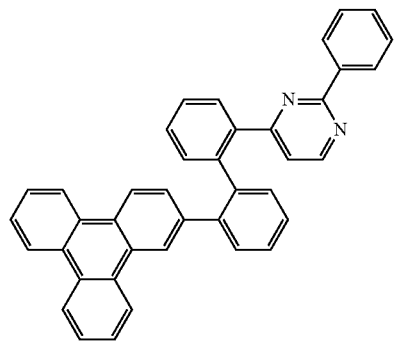
A-75
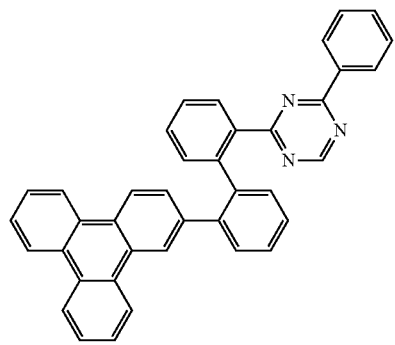

-continued
A-76
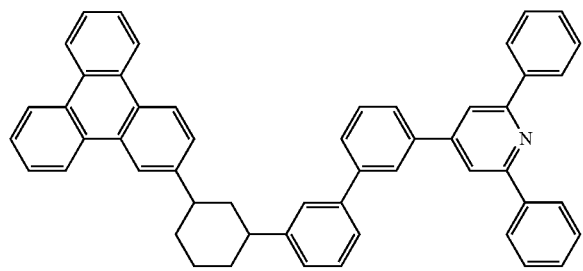
A-77
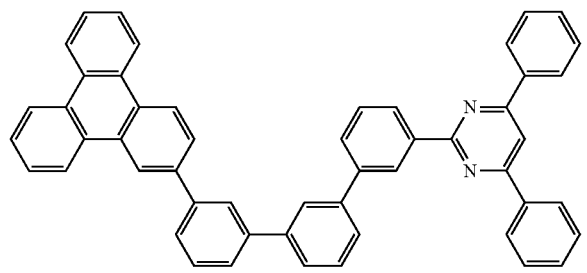
A-78
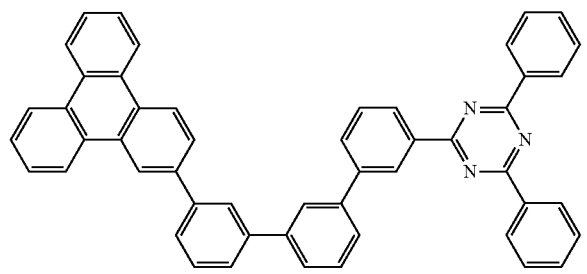
A-79
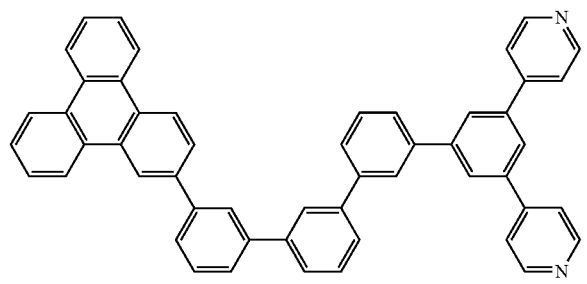
A-80
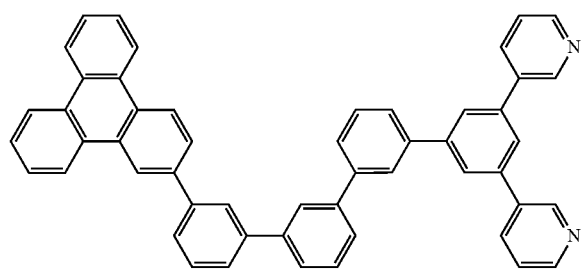

-continued
A-81
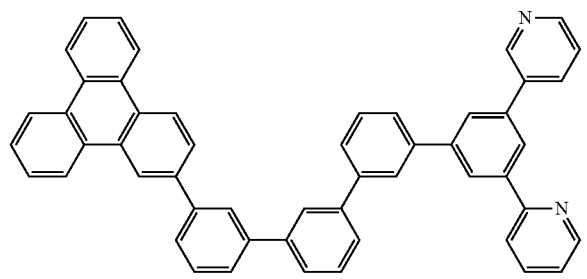
A-82
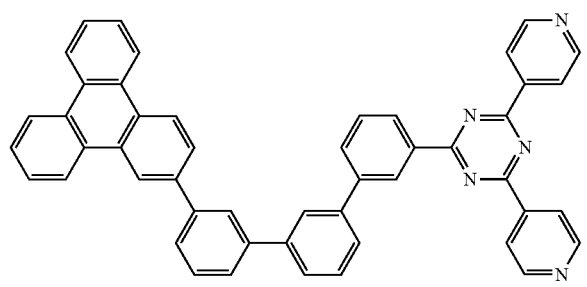
A-83
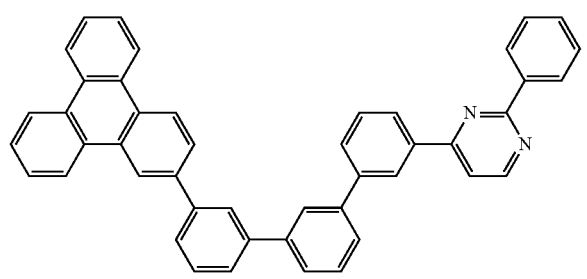
A-84
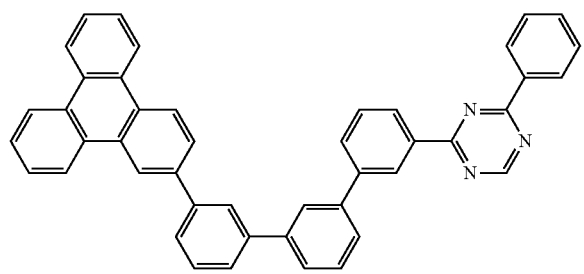

-continued
A-85
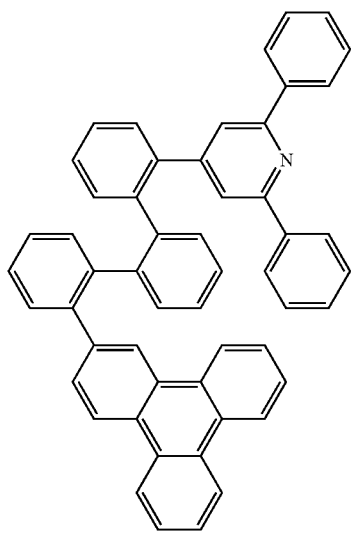
A-86
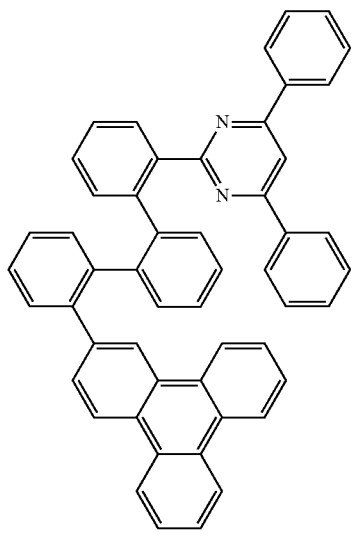
A-87
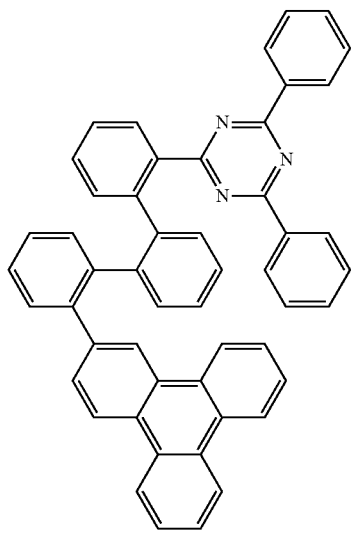

-continued
A-88
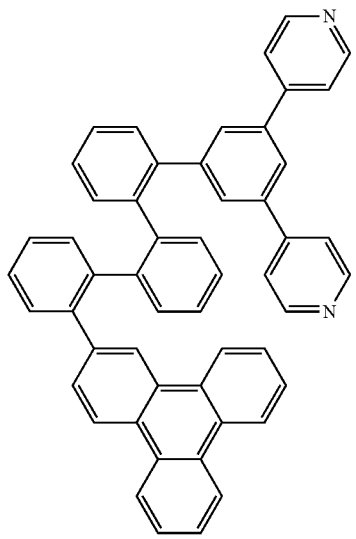
A-89
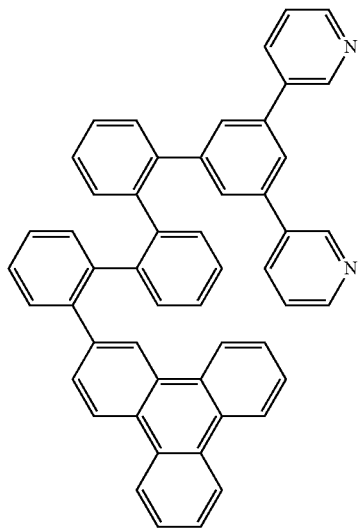
A-90
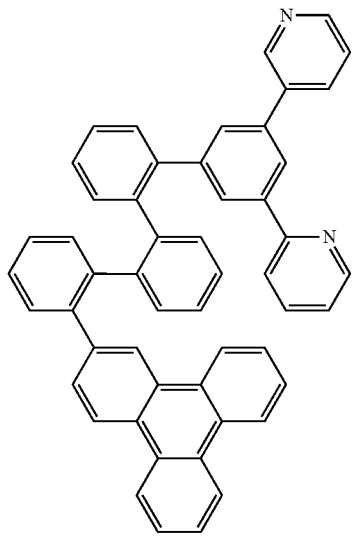

-continued
A--91
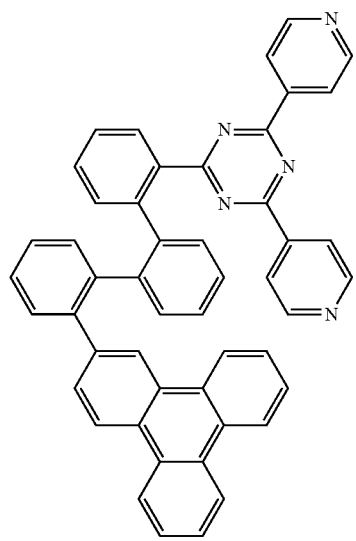
A-92
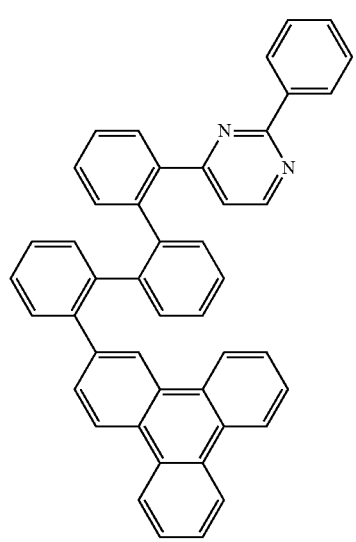
A-93
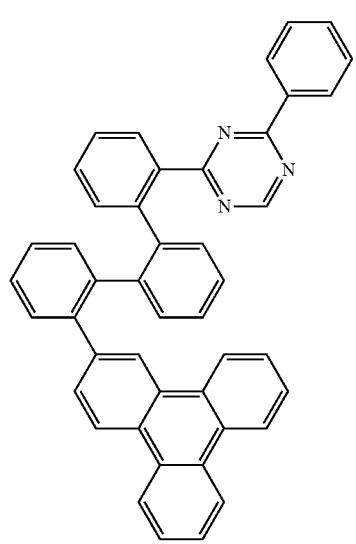

-continued
A-94
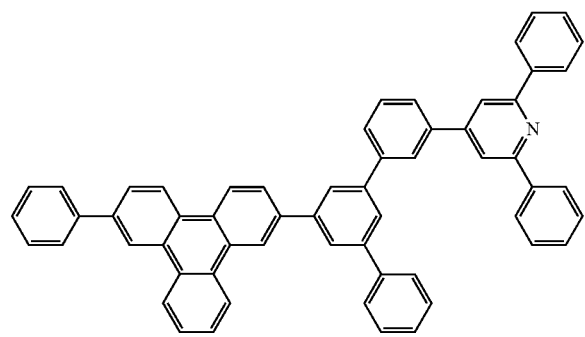
A-95
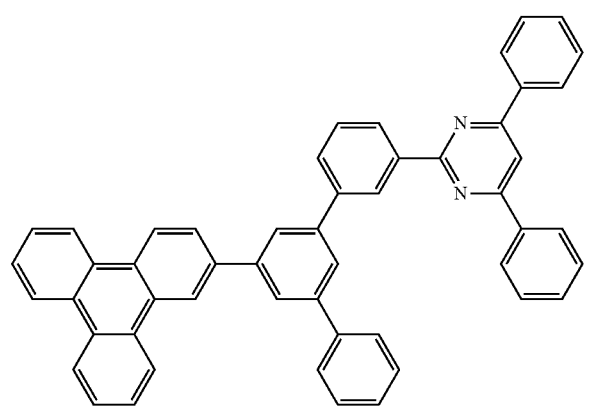
A-96
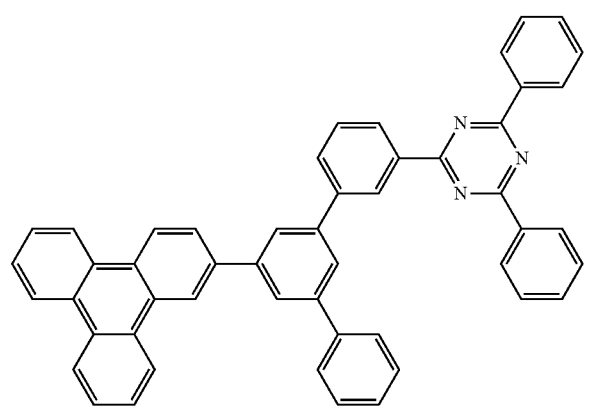
A-97
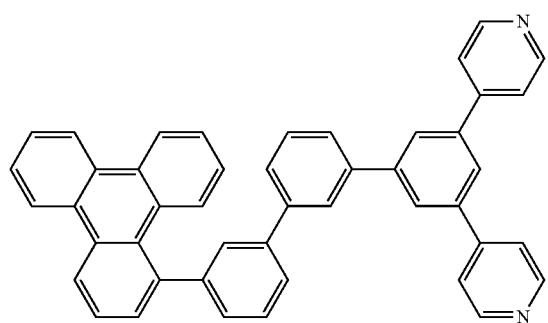

-continued
A-98
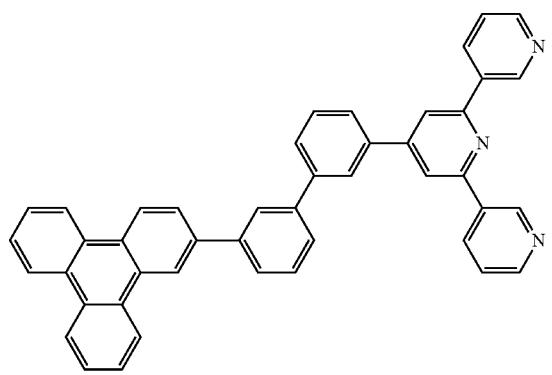
A-99
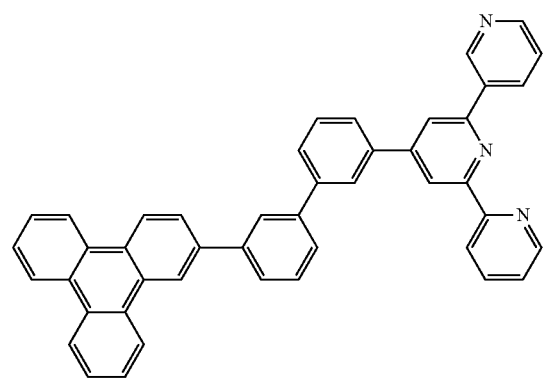
A-100
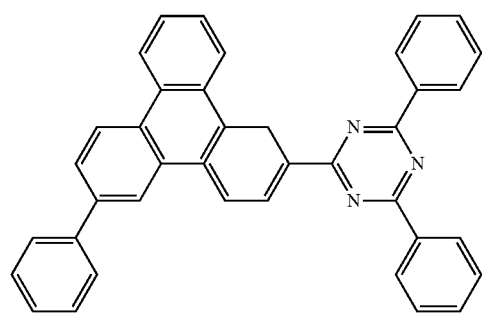
A-101
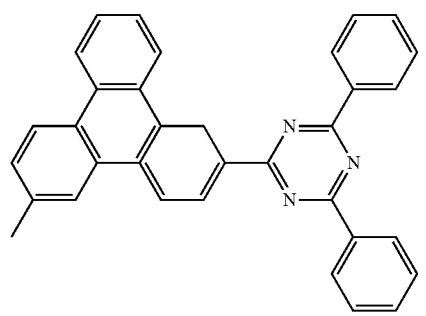

-continued
A-102
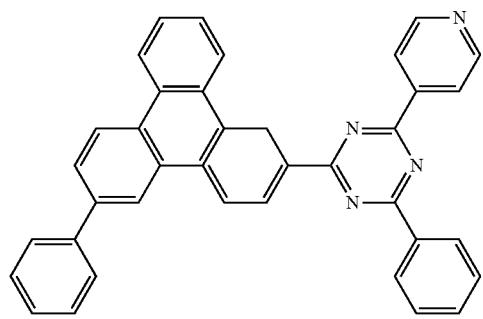
A-103
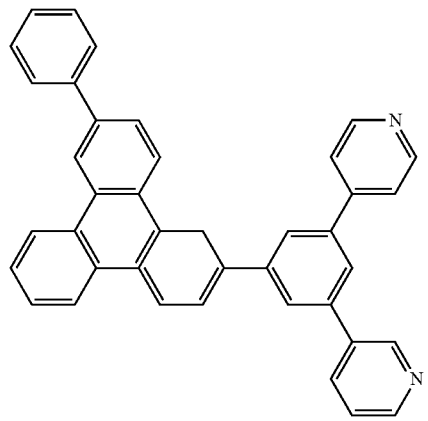
A-104
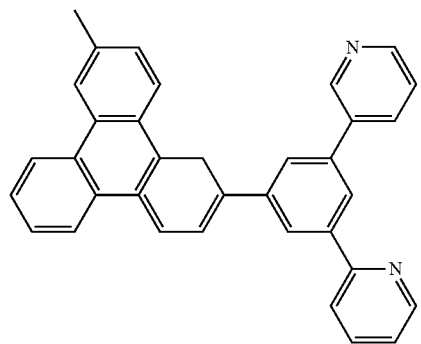
A-105
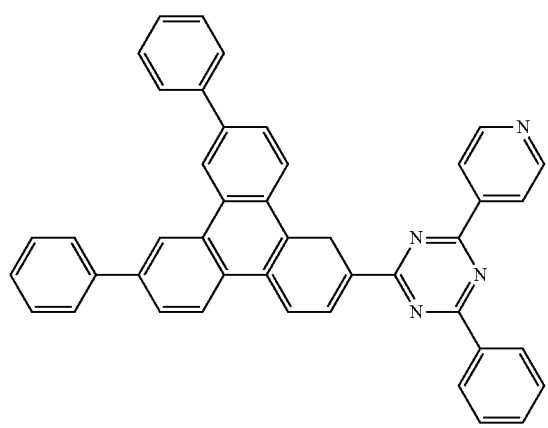

-continued
A-106
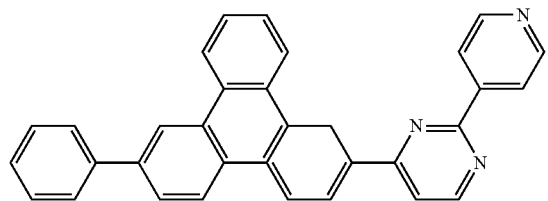
A-107
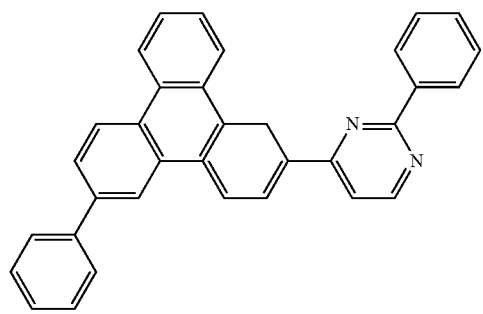
A-108
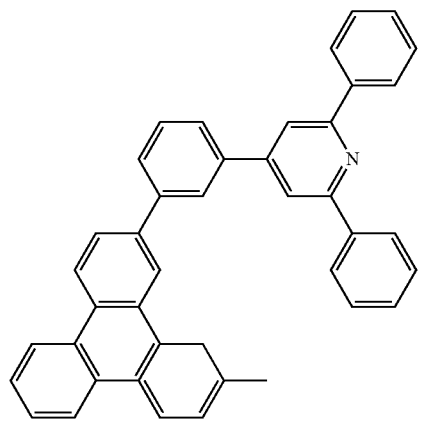
A-109
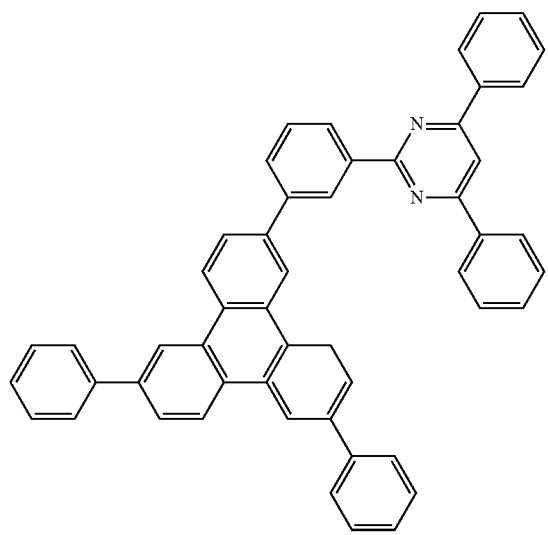

-continued
A-110
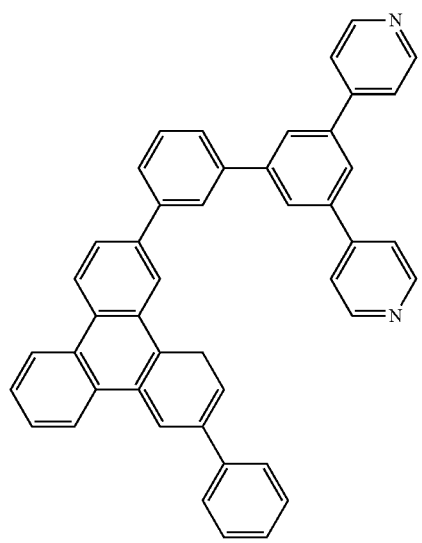
A-111
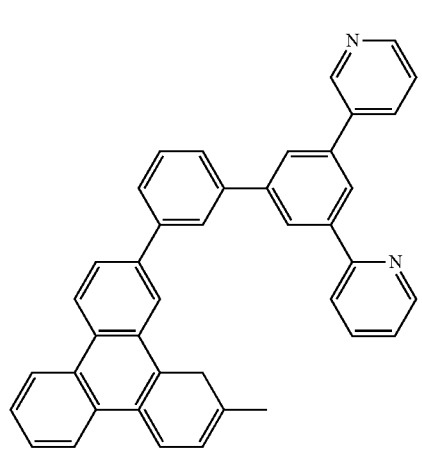
A-112
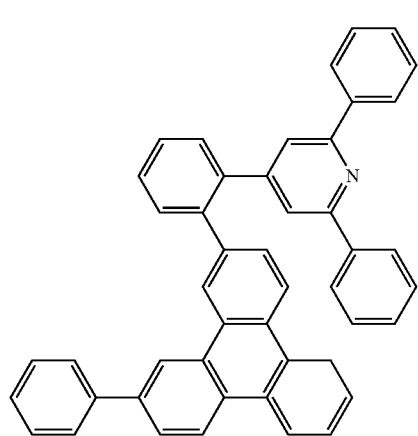

-continued
A-112
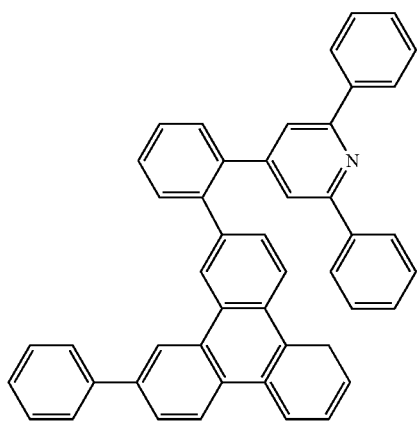
A-113
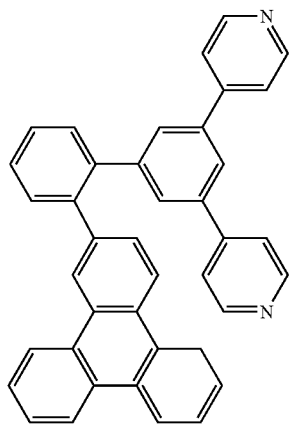
A-114
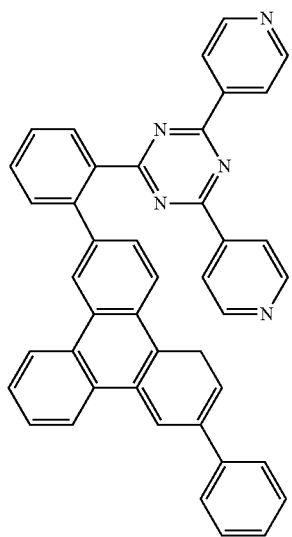

-continued
A-115
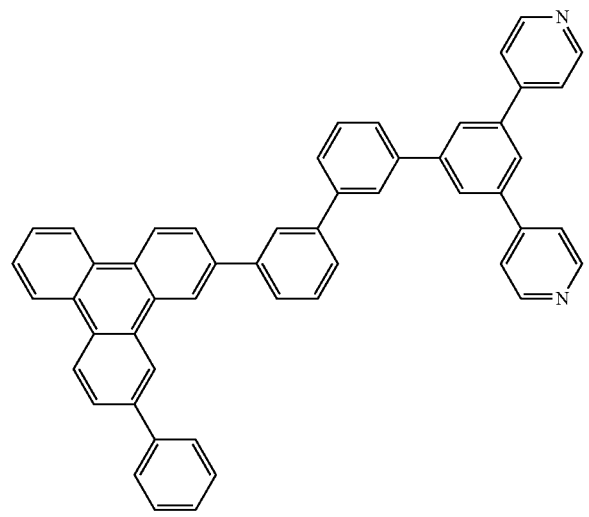
A-116
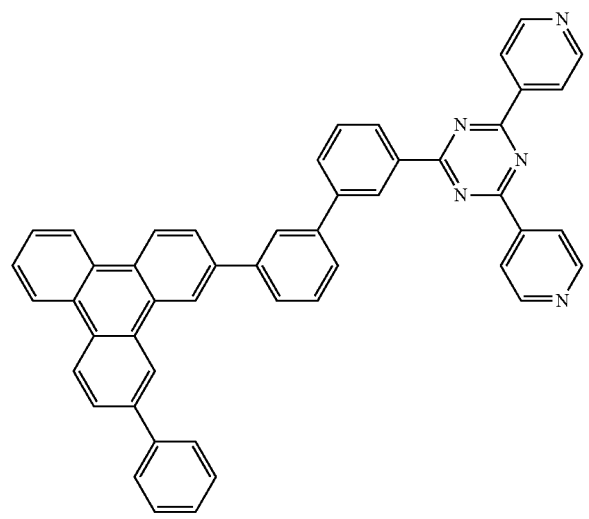
A-117
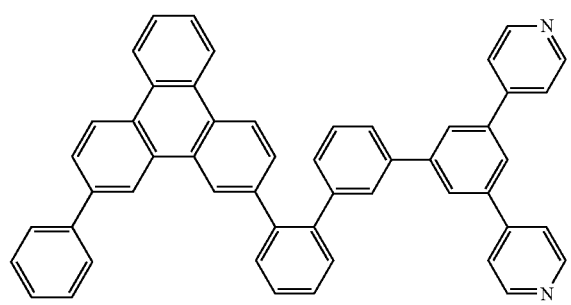

-continued
A-118
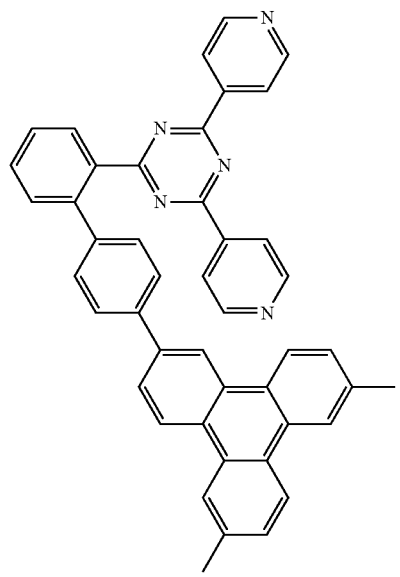
A-119
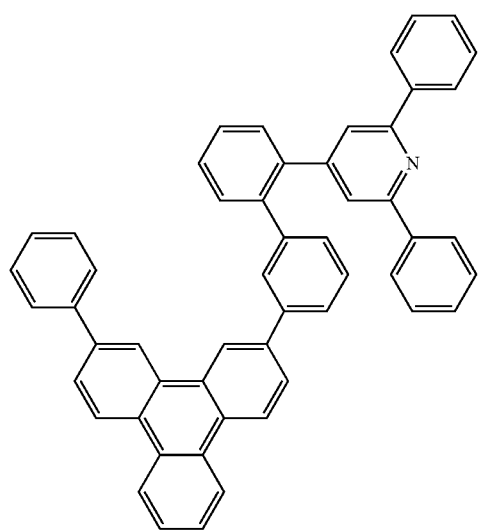
A-120
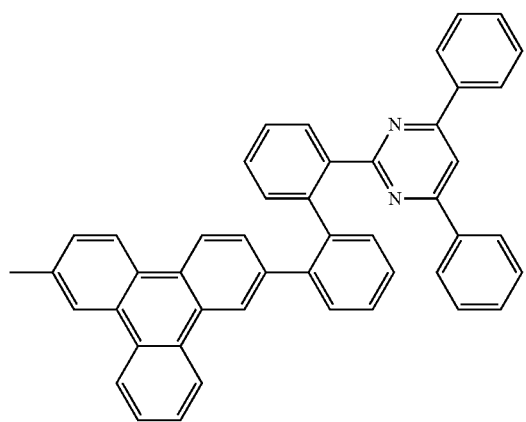

-continued
A-121
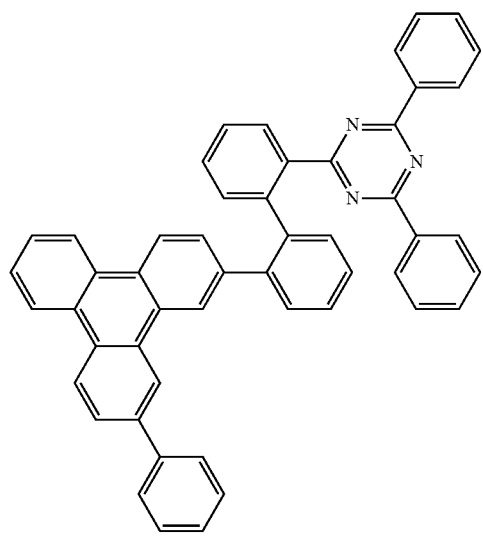
A-122
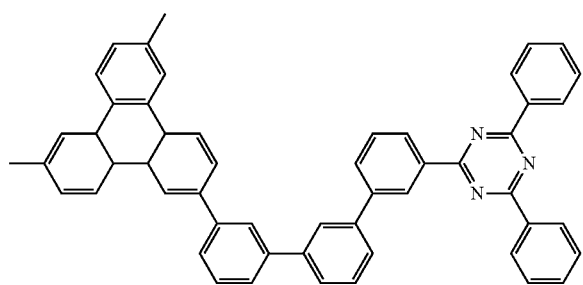
A-123
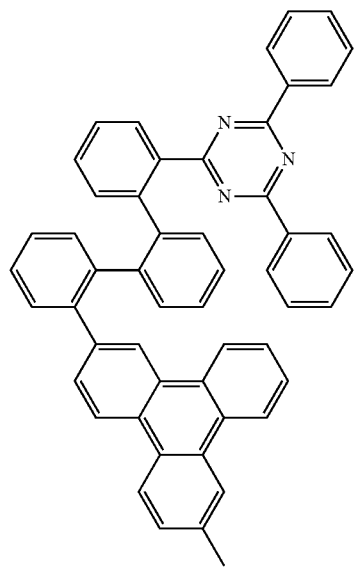

-continued
A-124
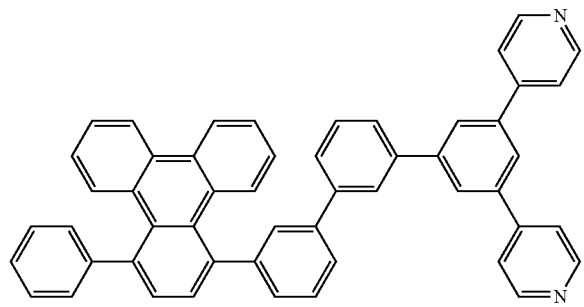
A-125
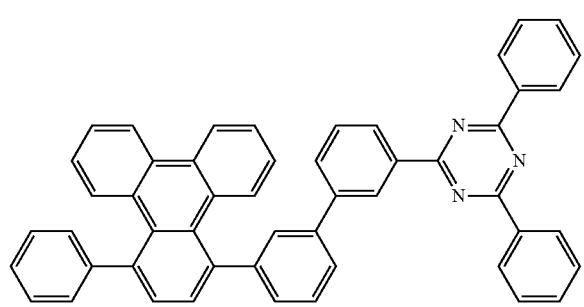
A(1)
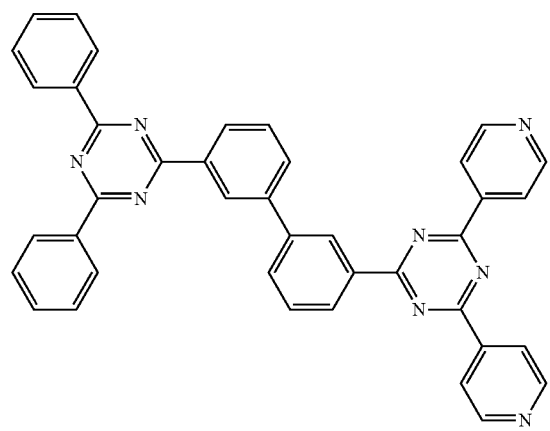
A(2)
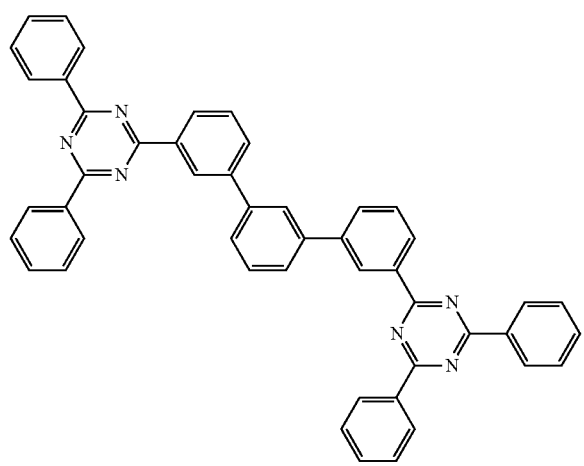

-continued
A(3)
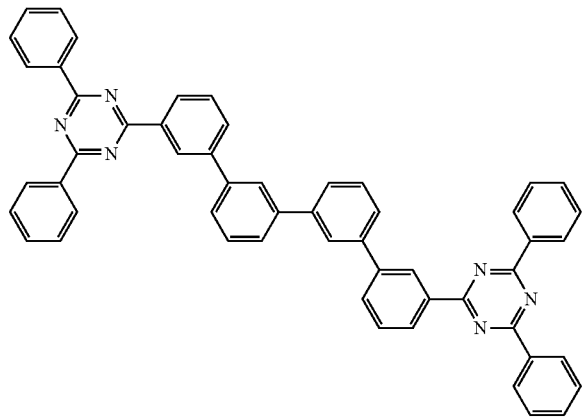
A(4)
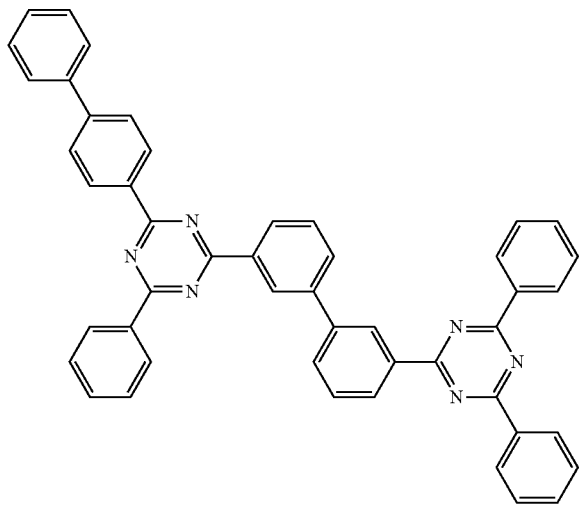
A(5)
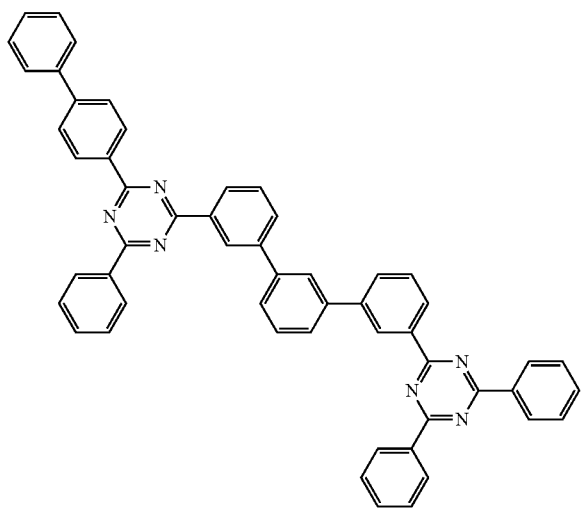

-continued
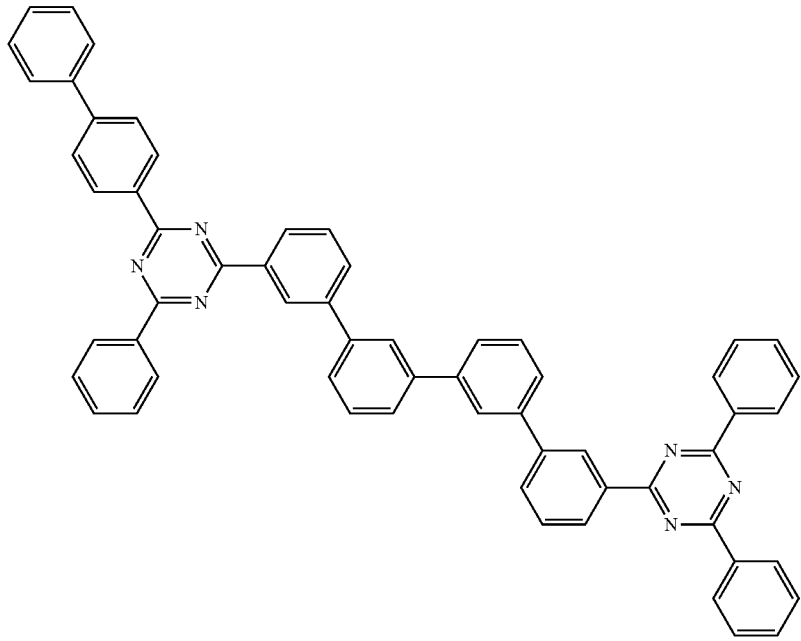
A(6)
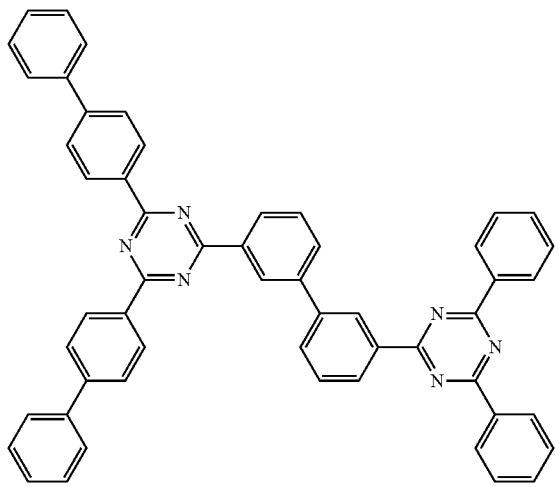
A(7)
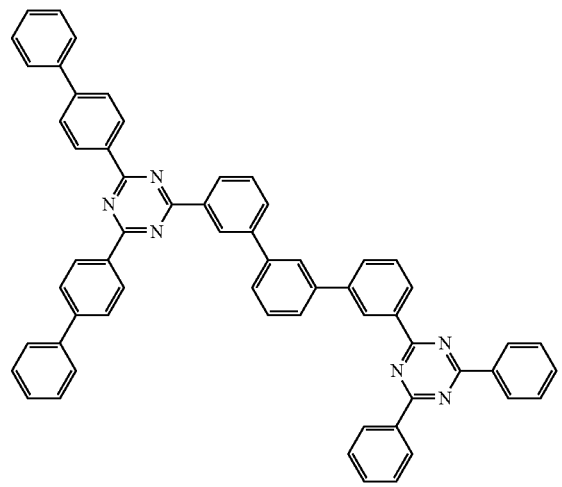
A(8)

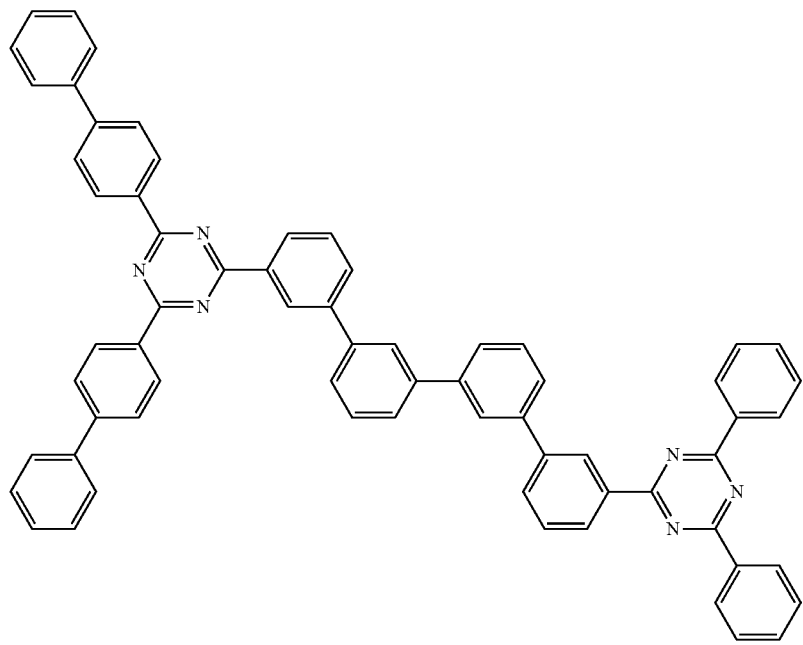
A(9)
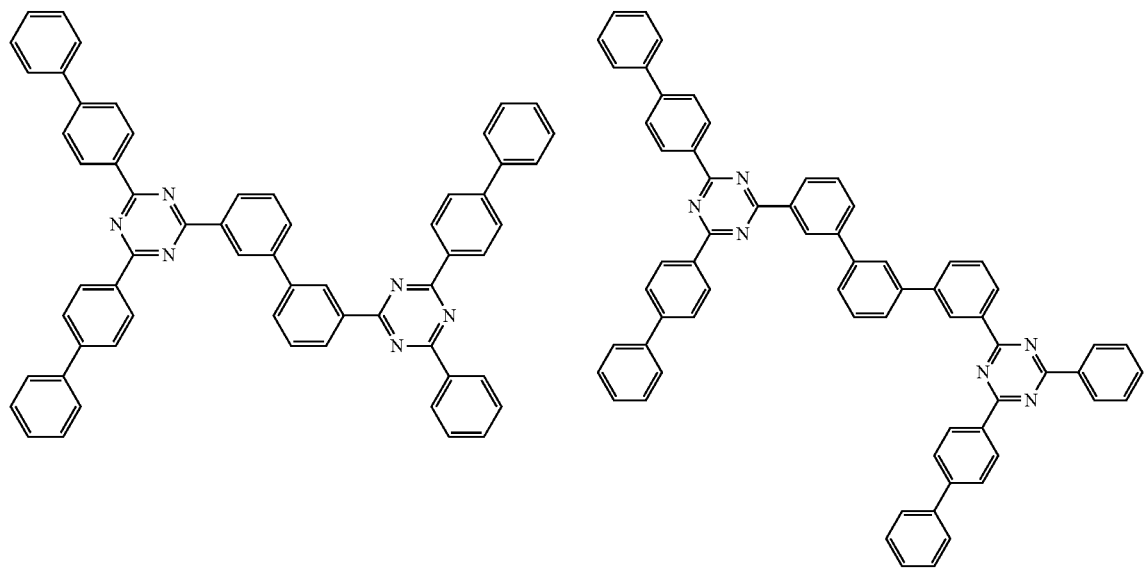
A(10) A(11)

-continued
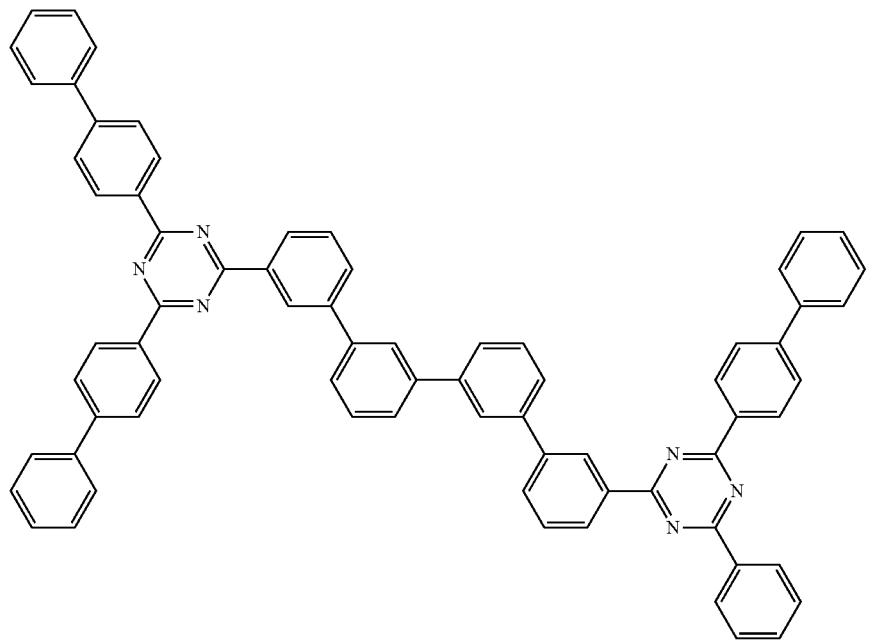
A(12)
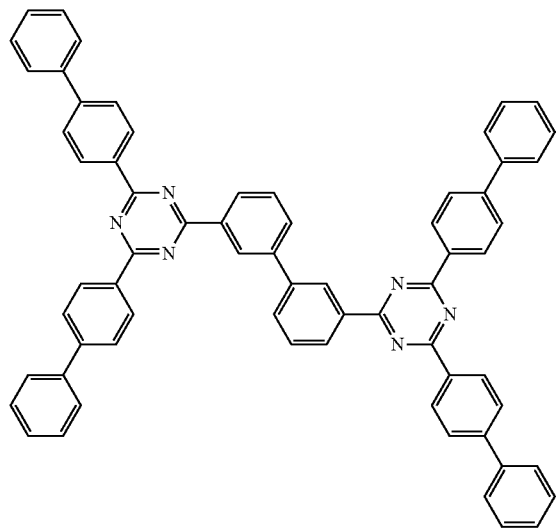
A(13)

-continued
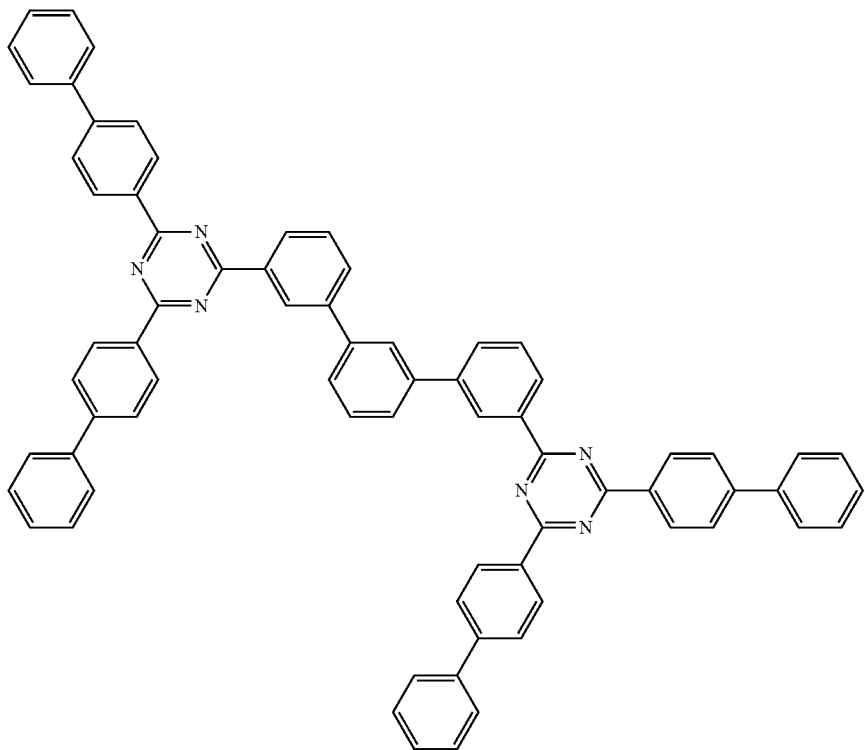
A(14)
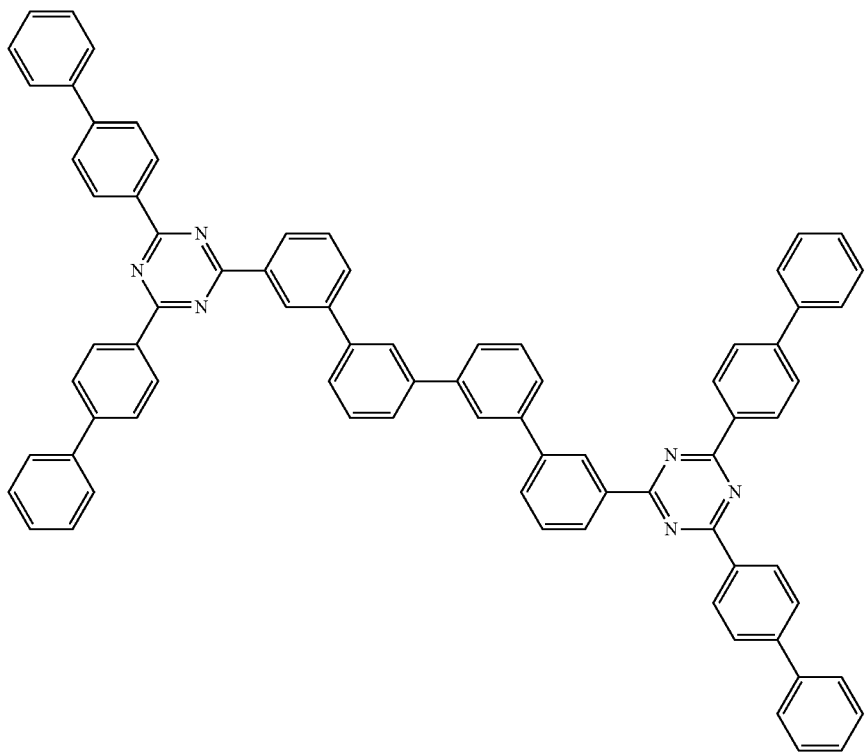
A(15)

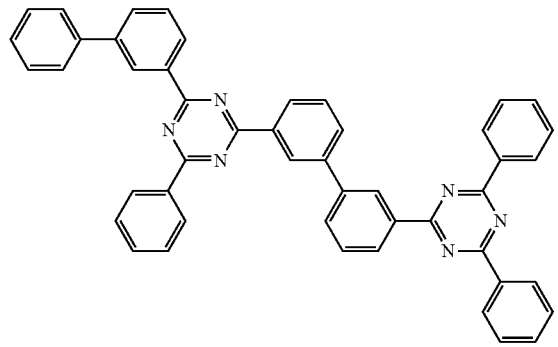
A(16)
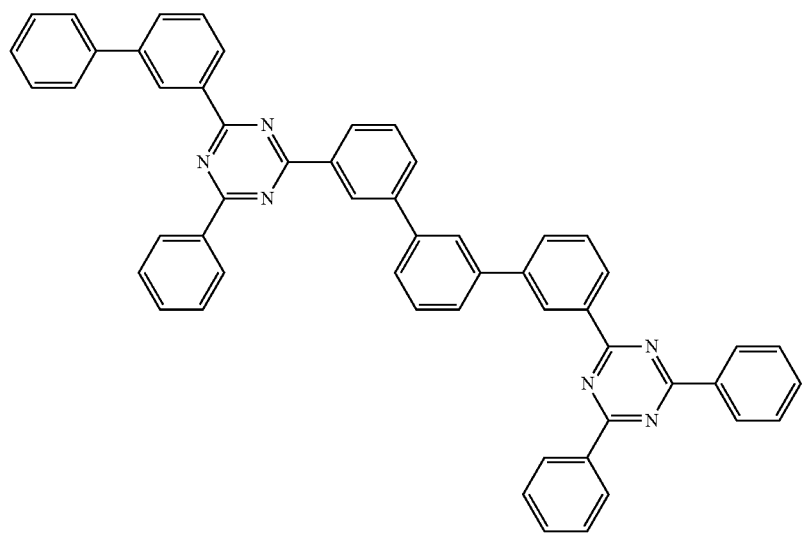
A(17)
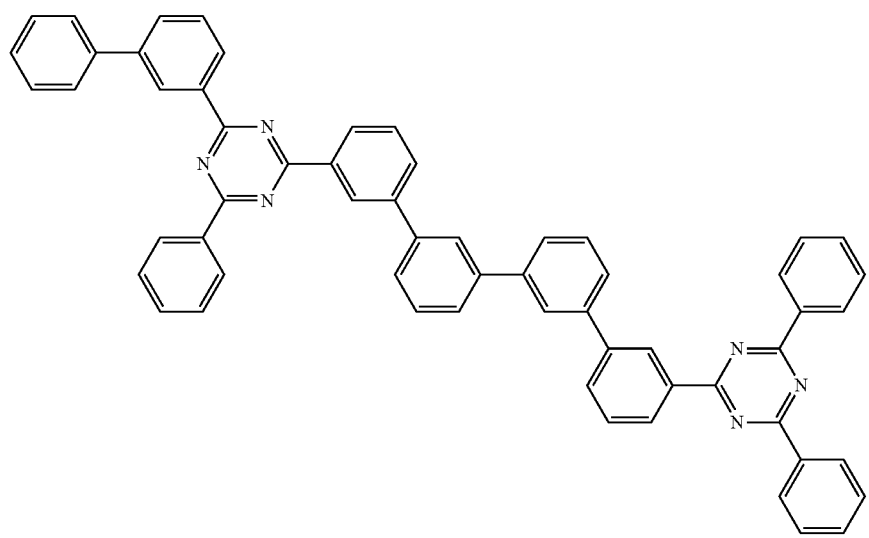
A(18)

-continued
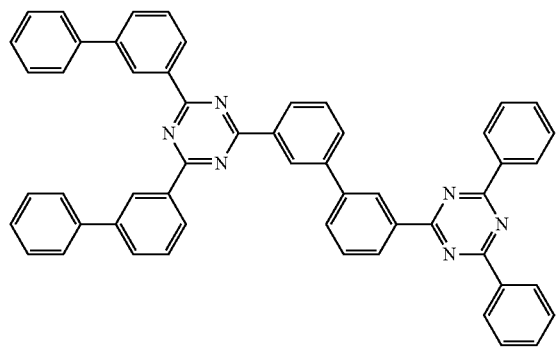
A(19)
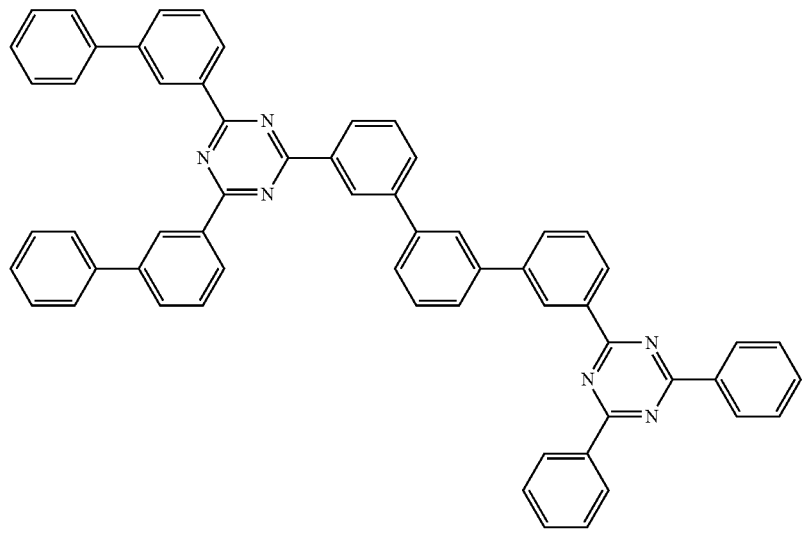
A(20)
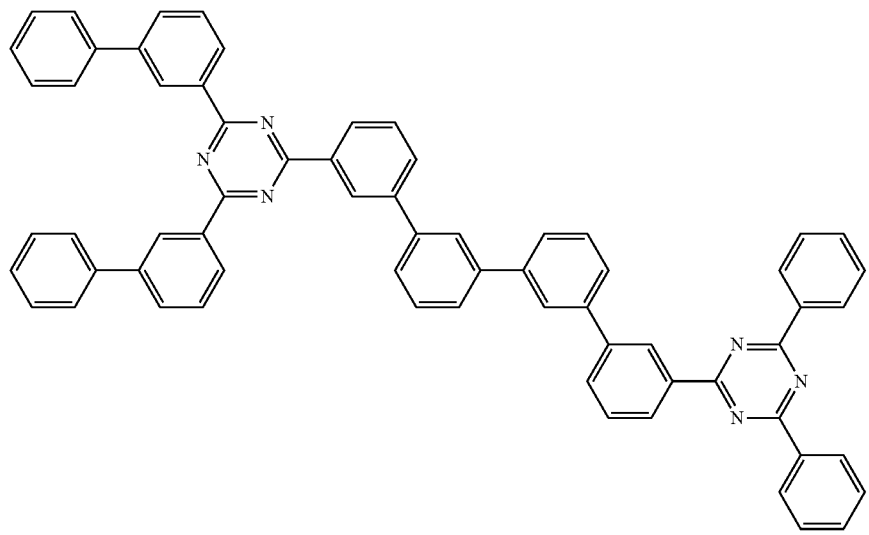
A(21)

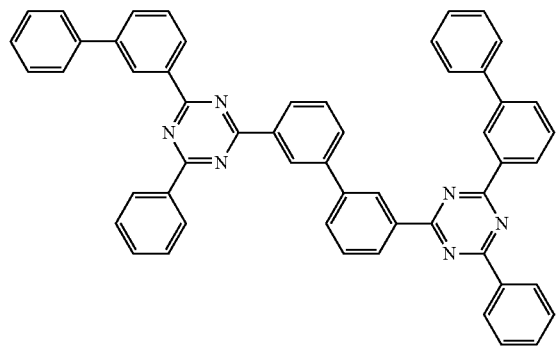
A(22)
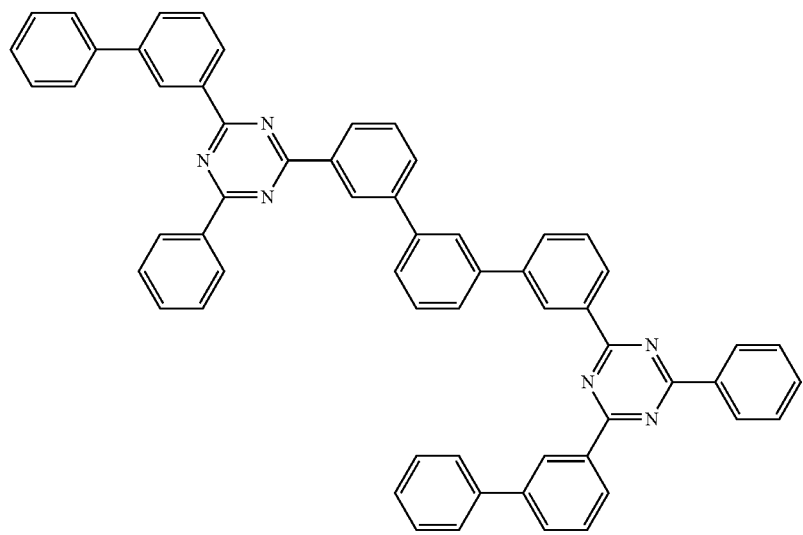
A(23)
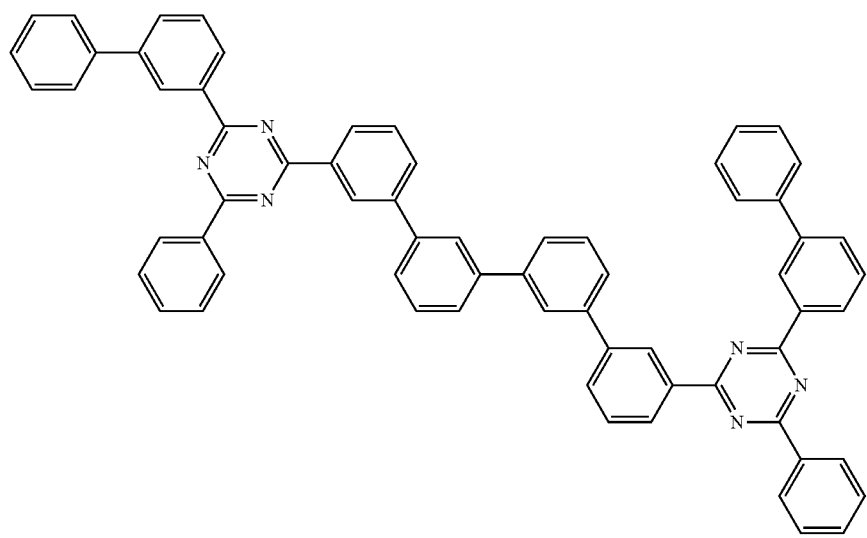
A(24)

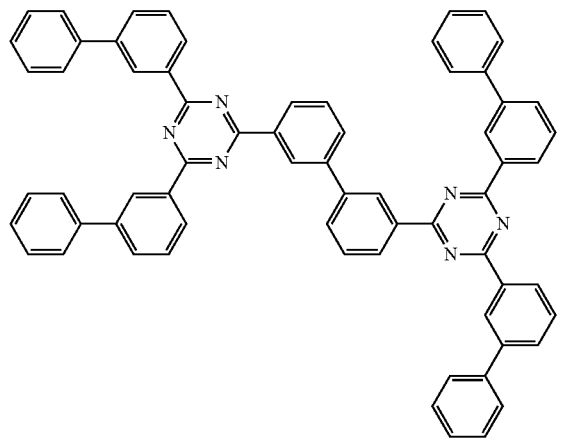
A(25)
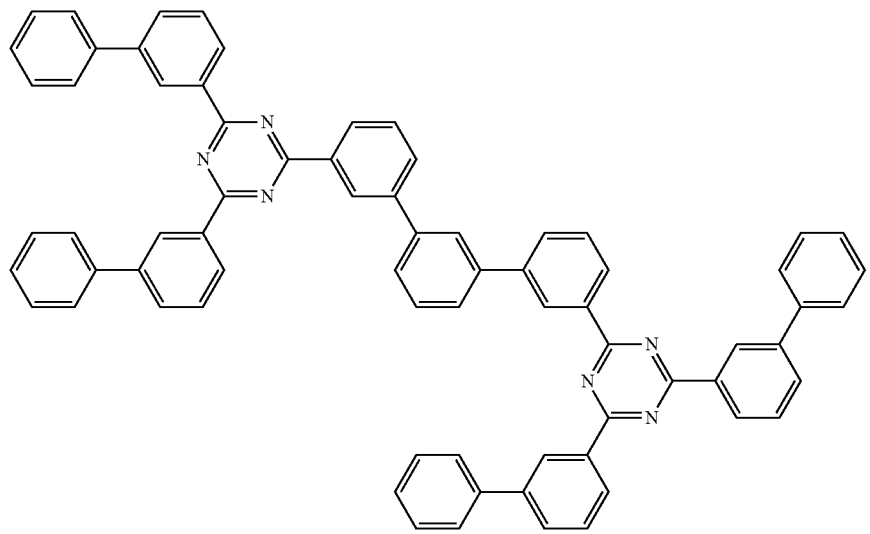
A(26)
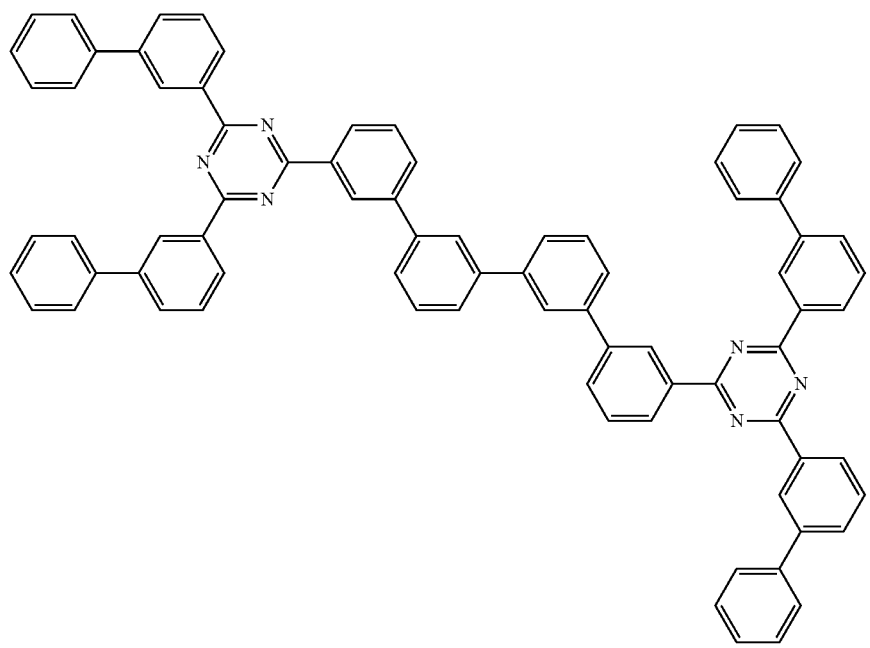
A(27)

-continued
A(28)
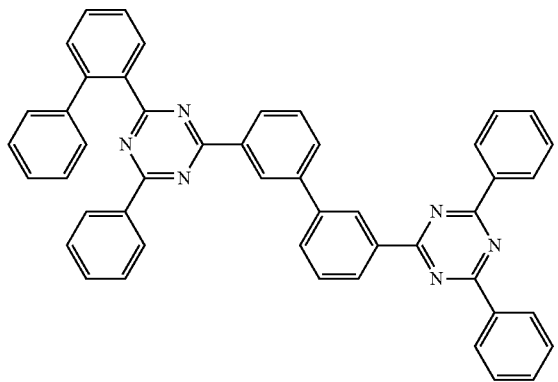
A(29)
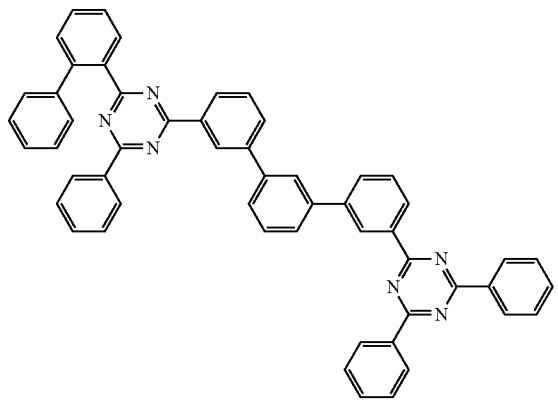
A(30)
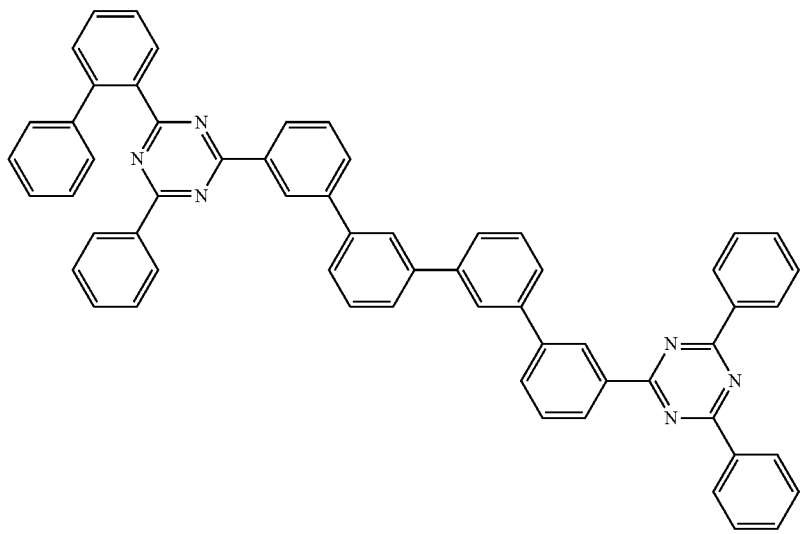
A(31)
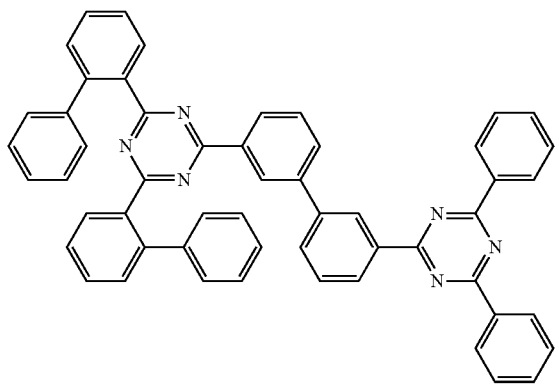
A(32)
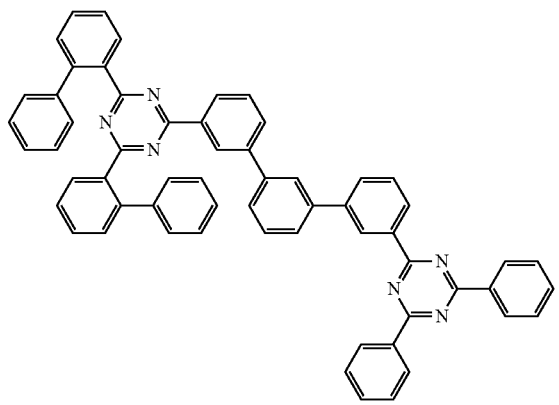

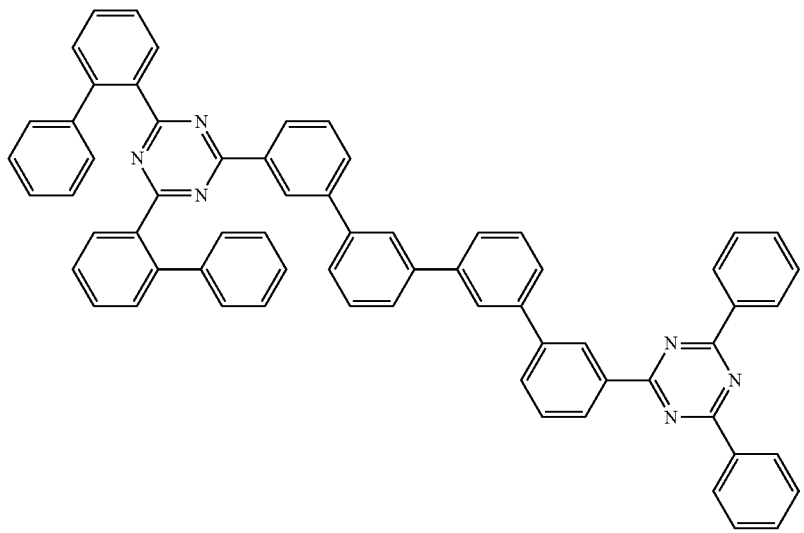
A(33)
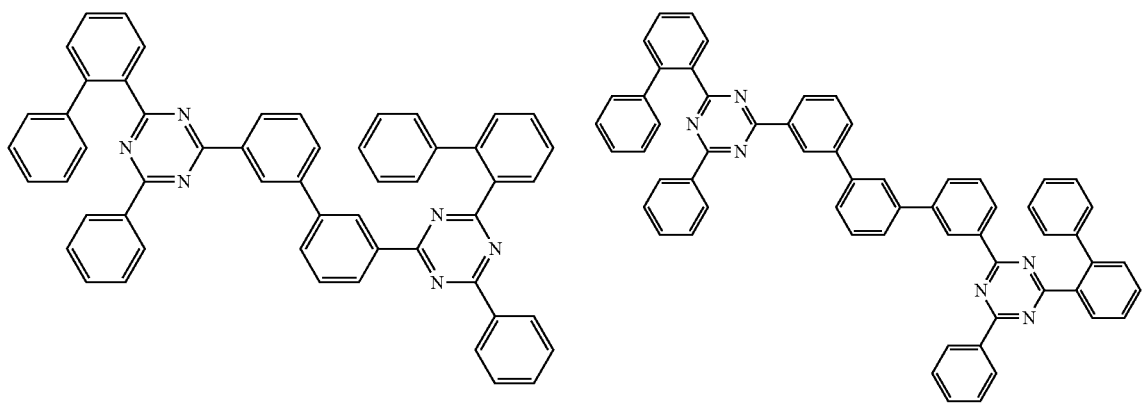
A(34)　　A(35)
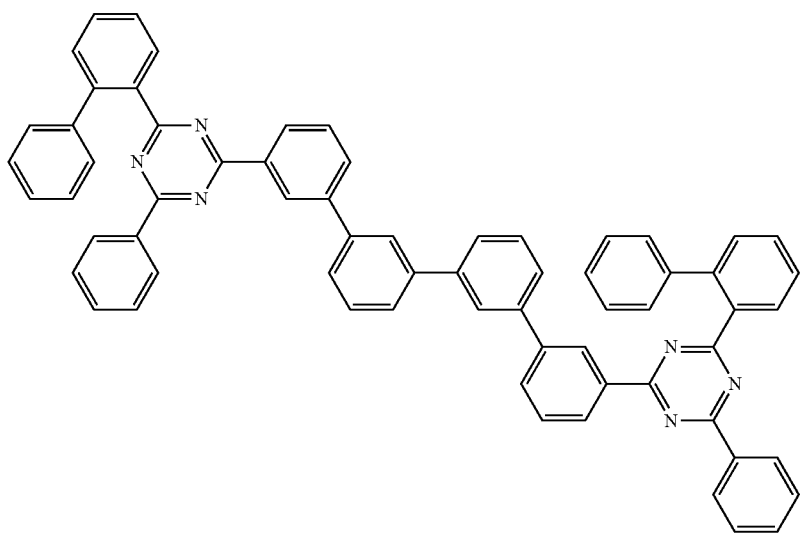
A(36)

-continued
A(37)
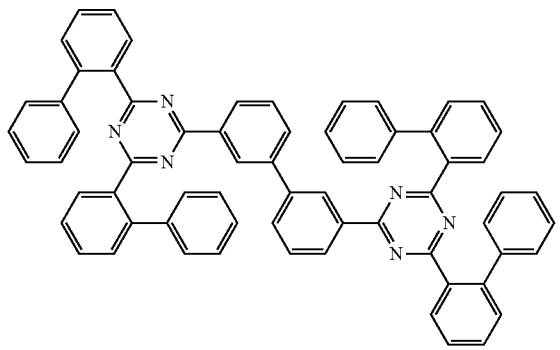
A(38)
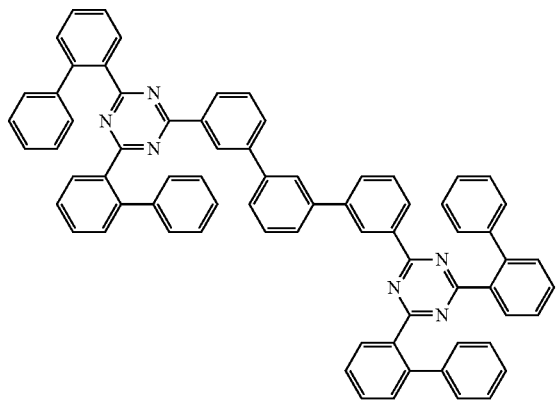
A(39)
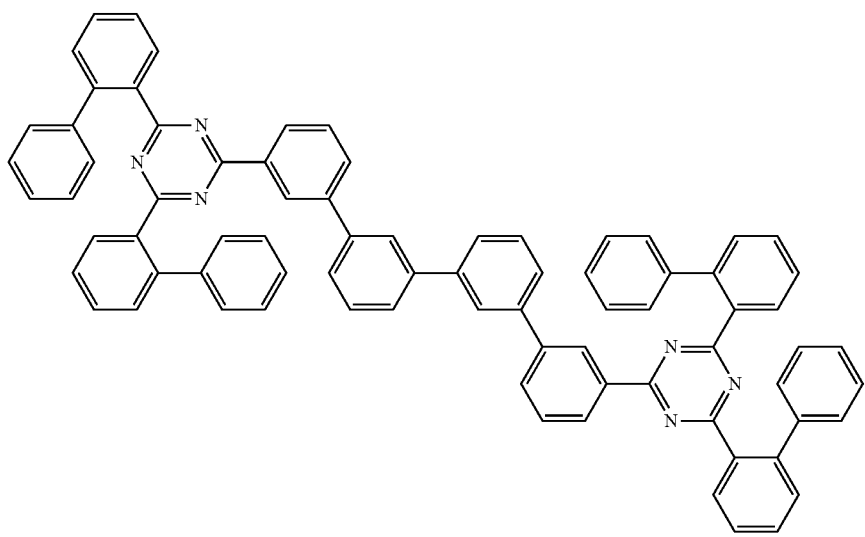
A(40)
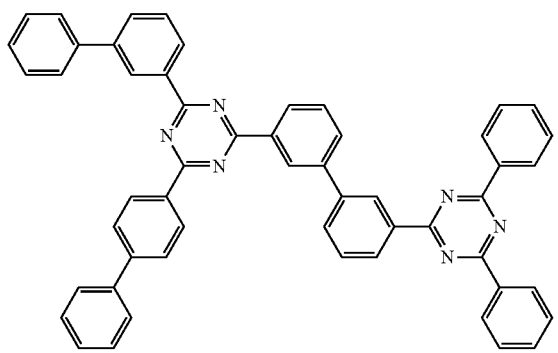

-continued
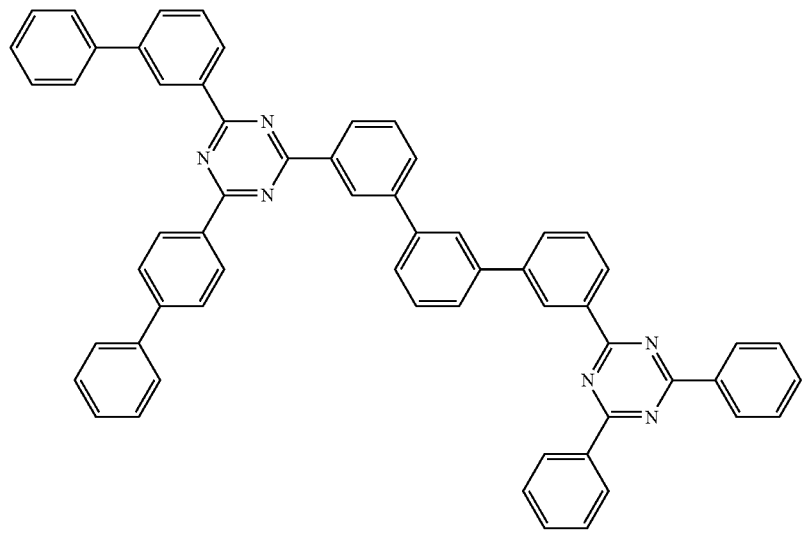
A(41)
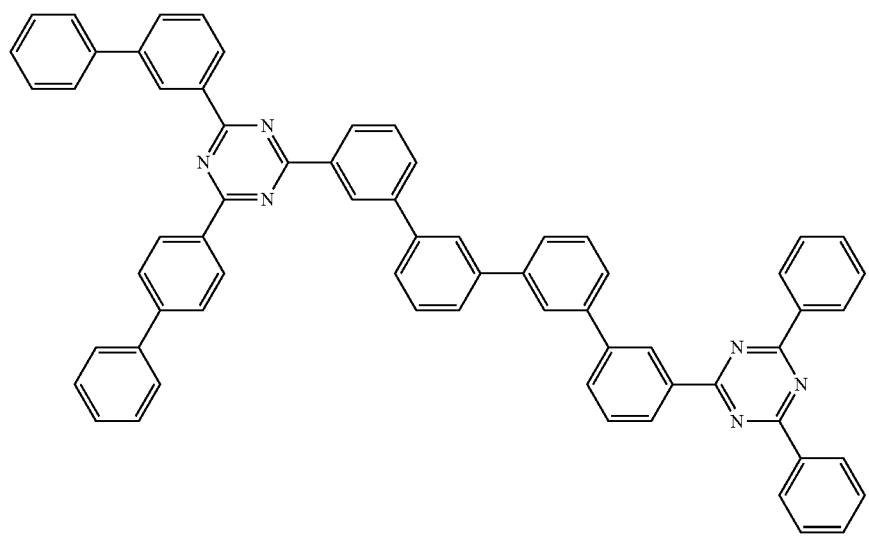
A(42)
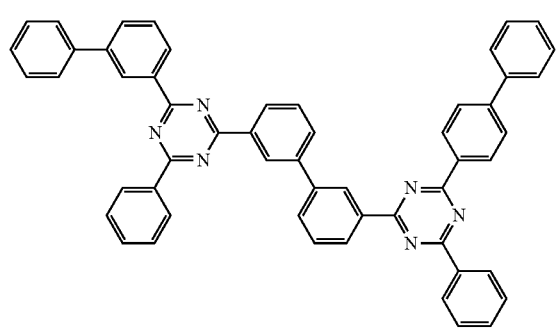
A(43)

-continued
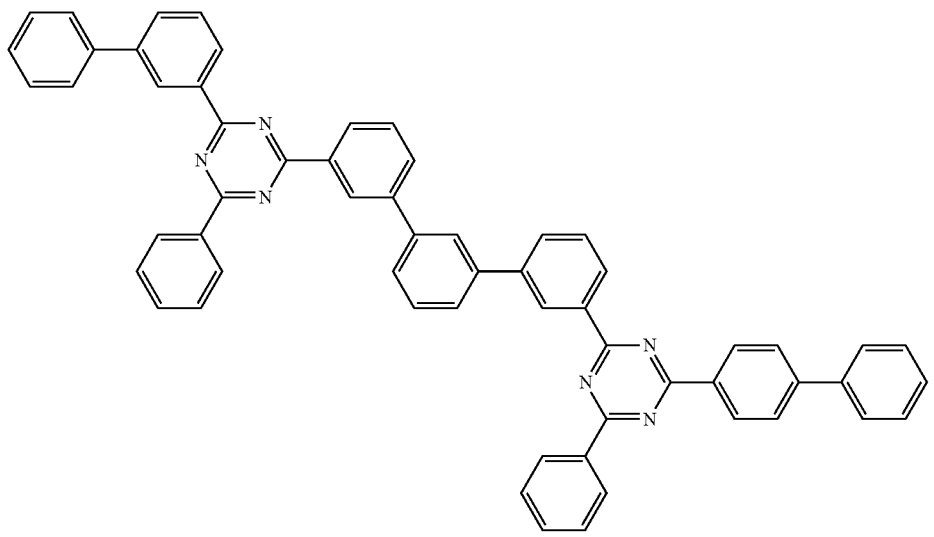
A(44)
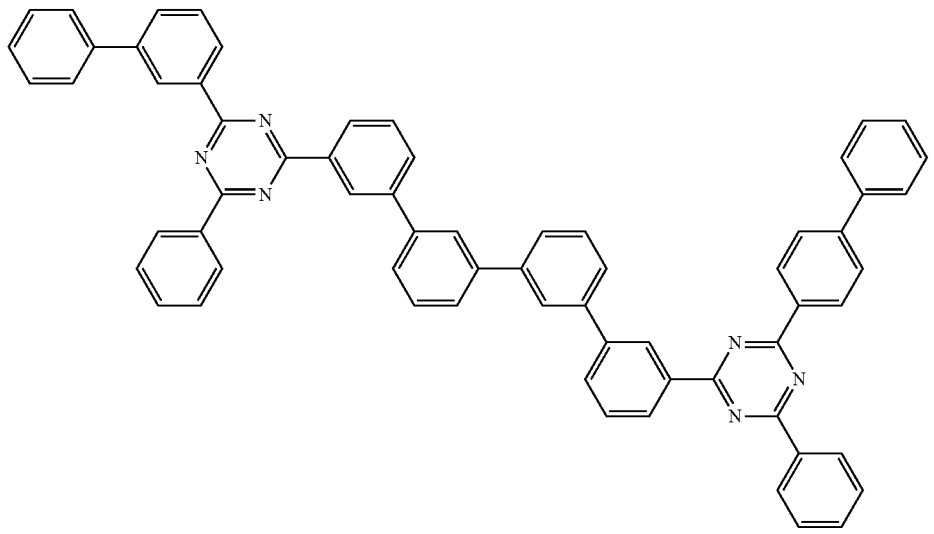
A(45)
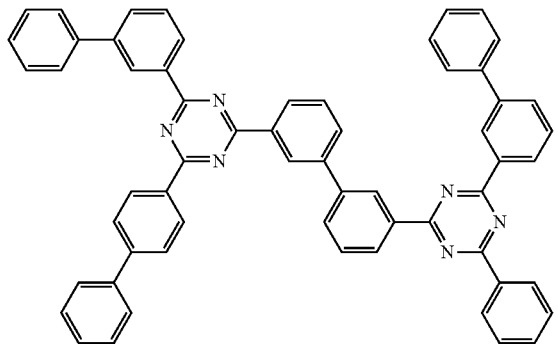
A(46)

-continued
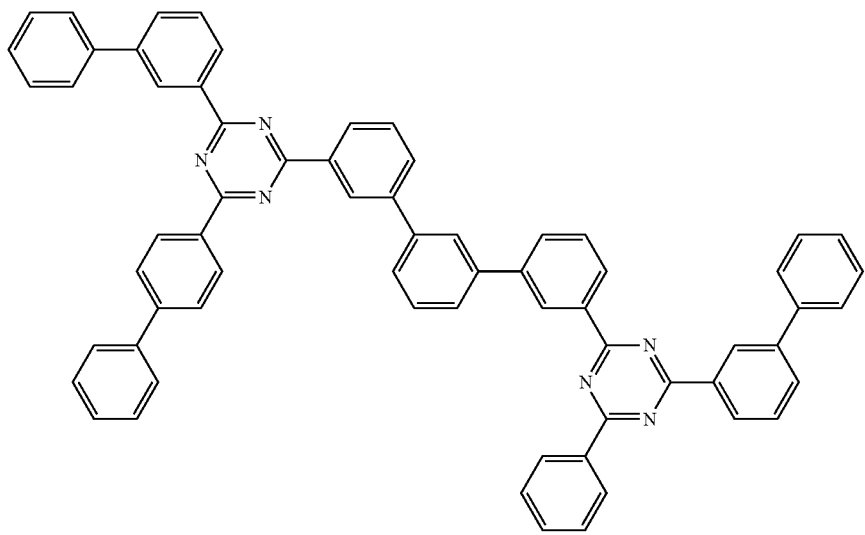
A(47)
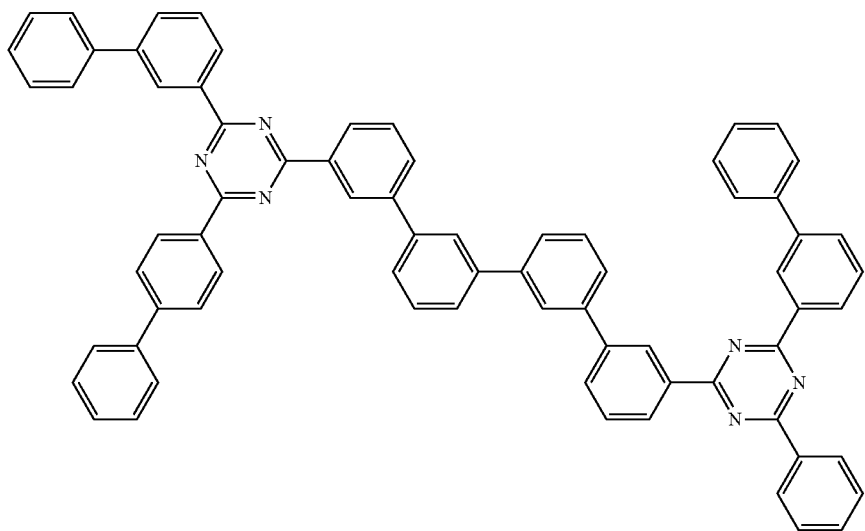
A(48)
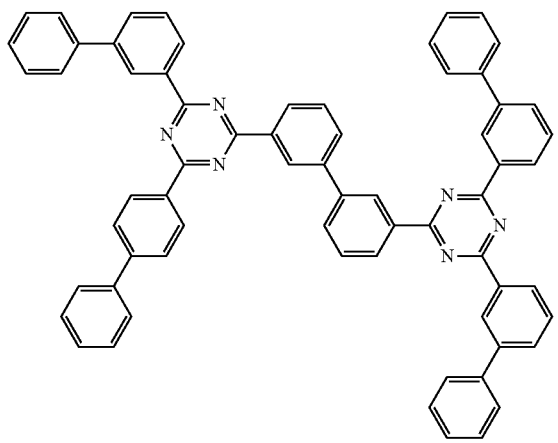
A(49)

-continued
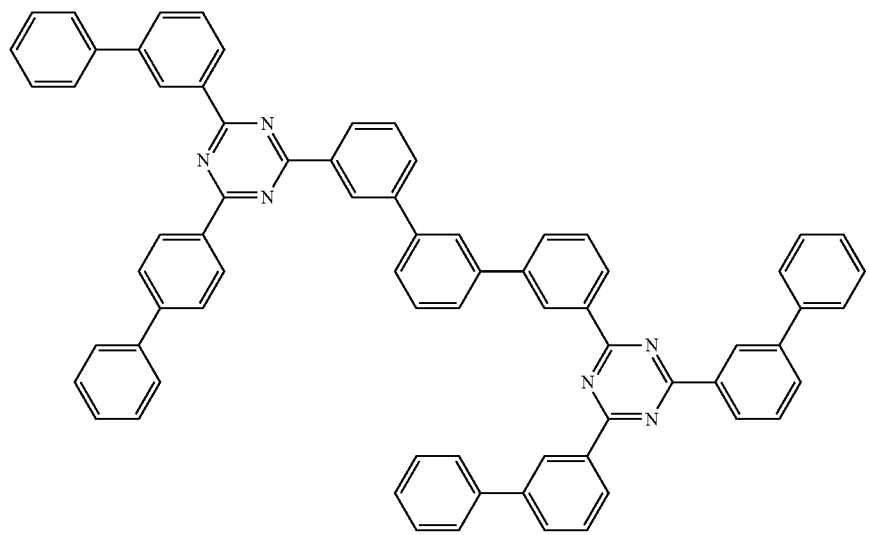
A(50)
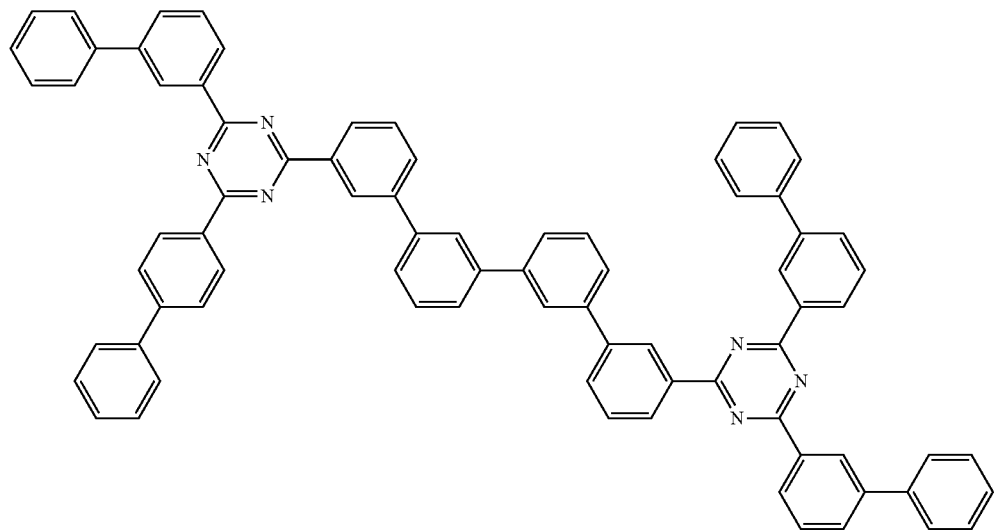
A(51)
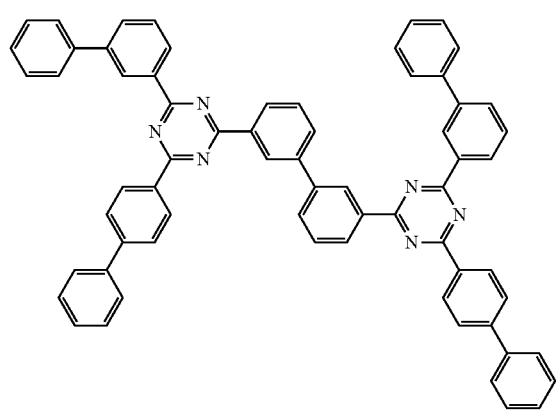
A(52)

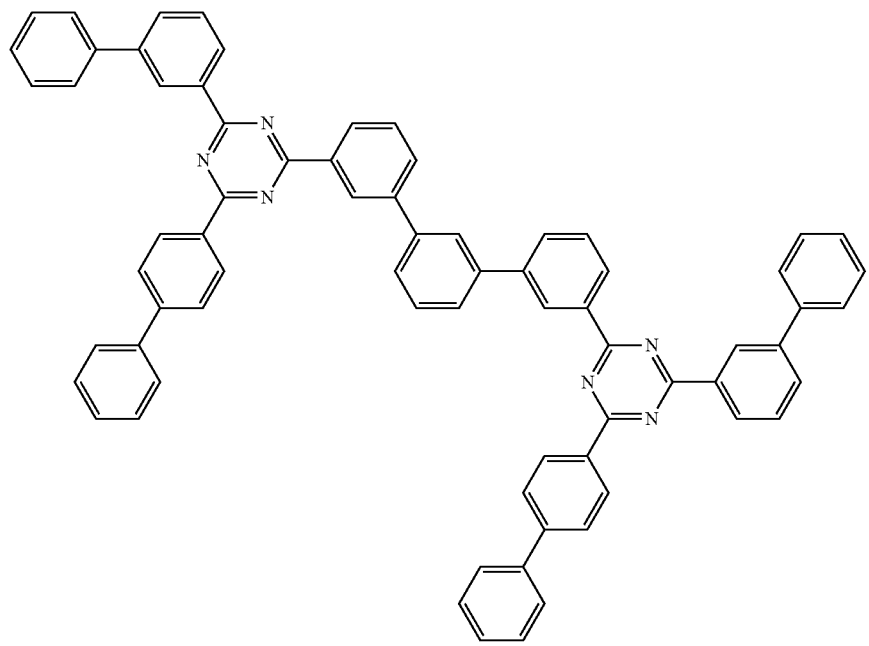
A(53)
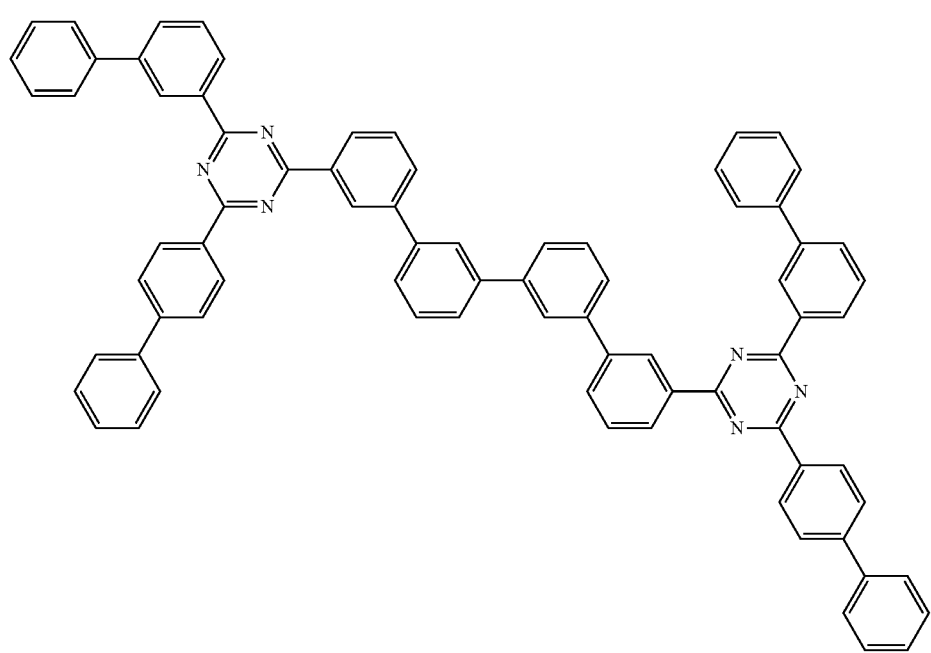
A(54)

-continued
A(55)
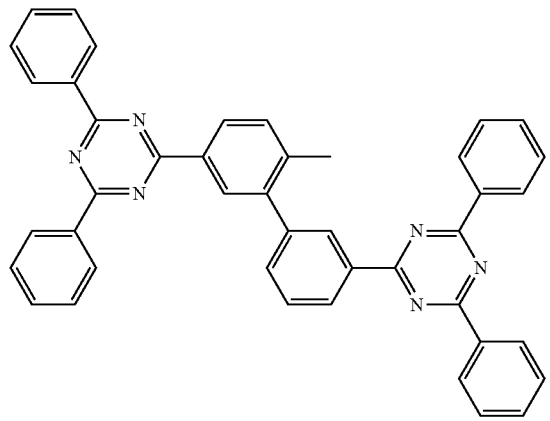
A(56)
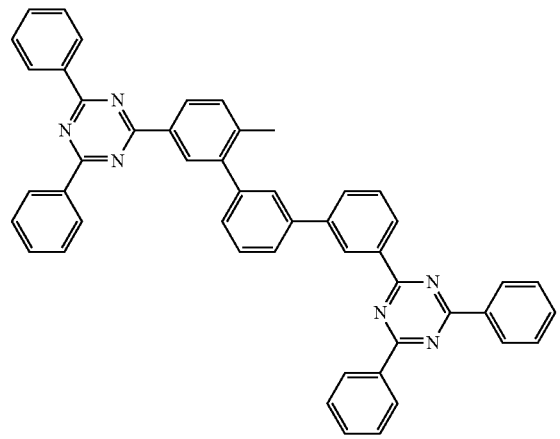
A(57)
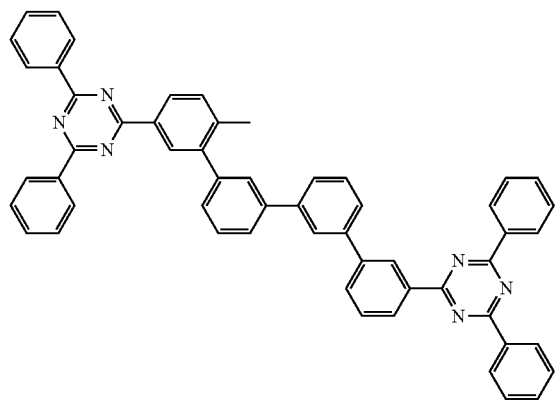
A(58)
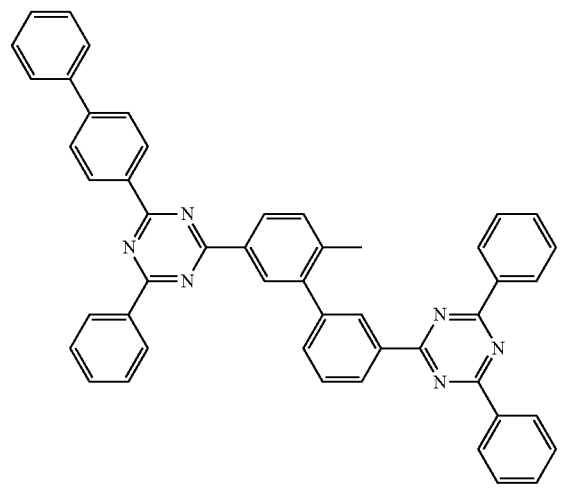
A(59)
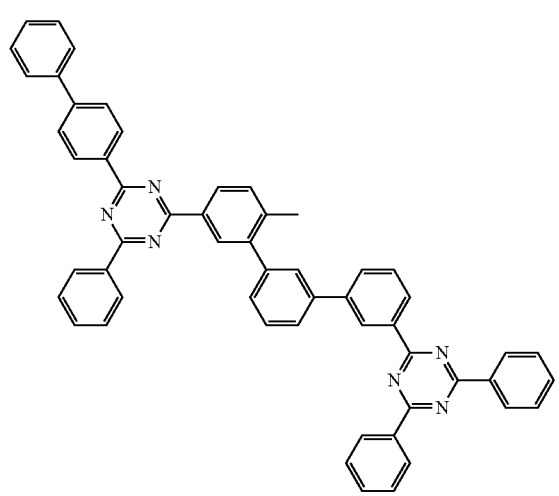

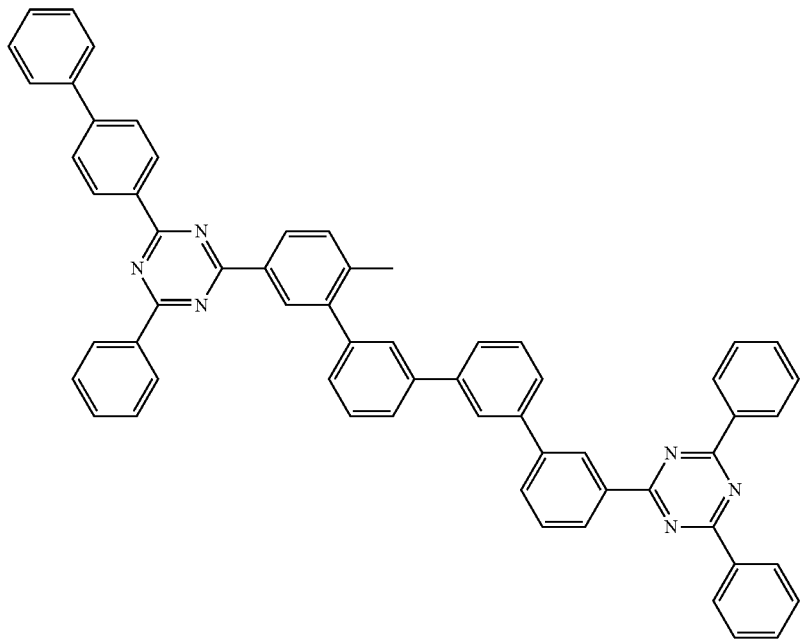
A(60)
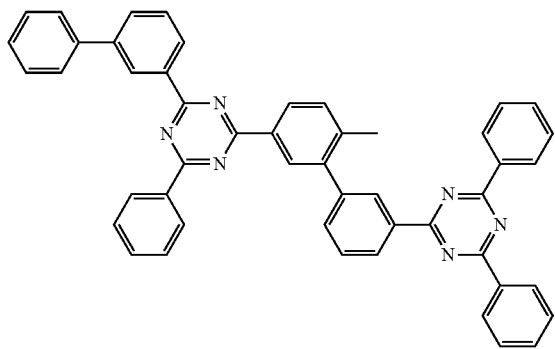
A(61)
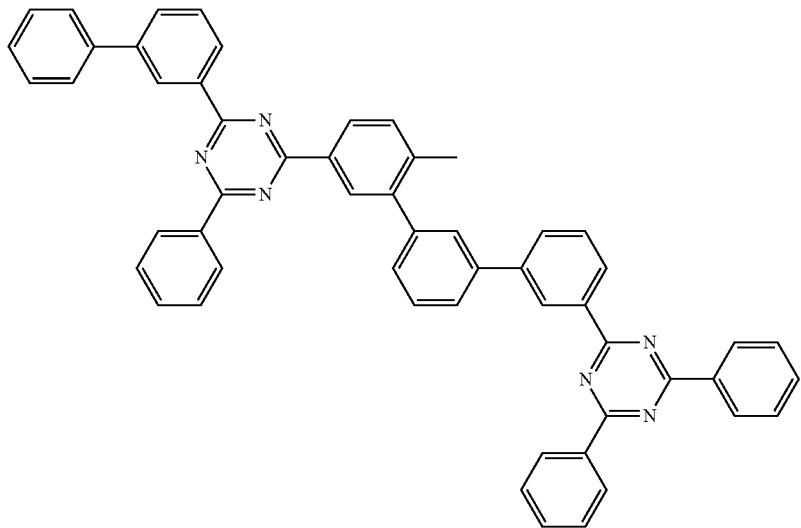
A(62)

A(63)
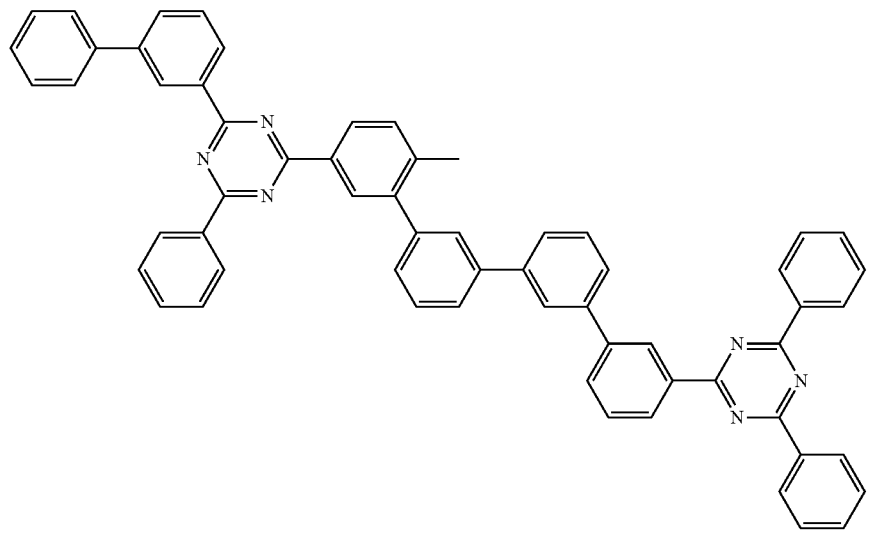
A(64)
A(65)
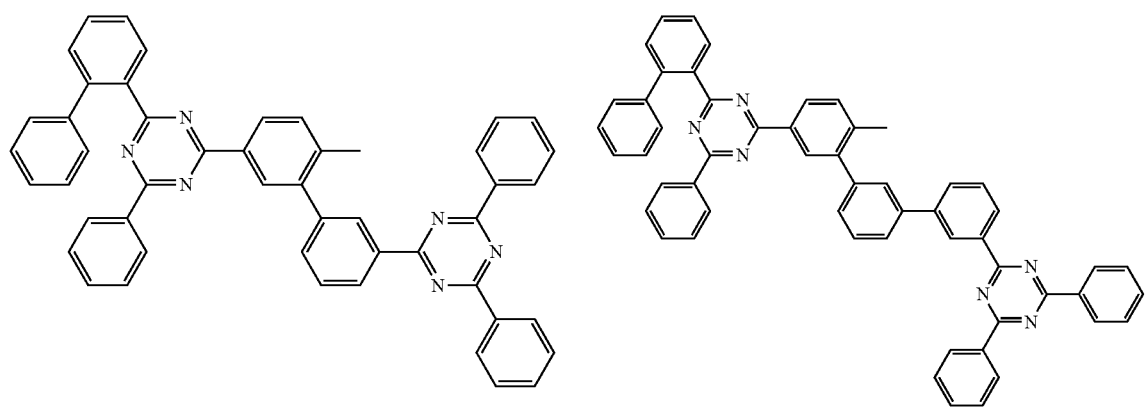
A(66)
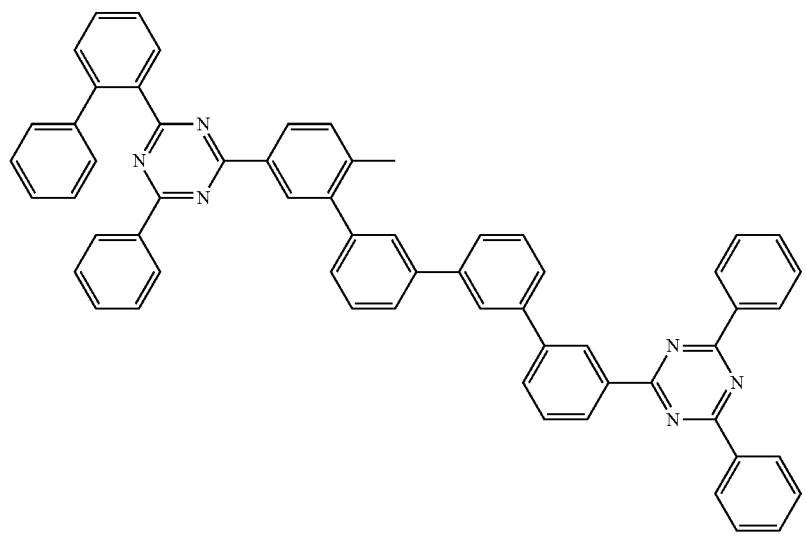

-continued
A(67)
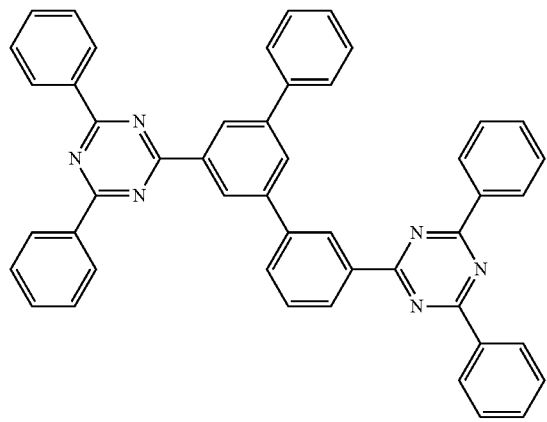
A(68)
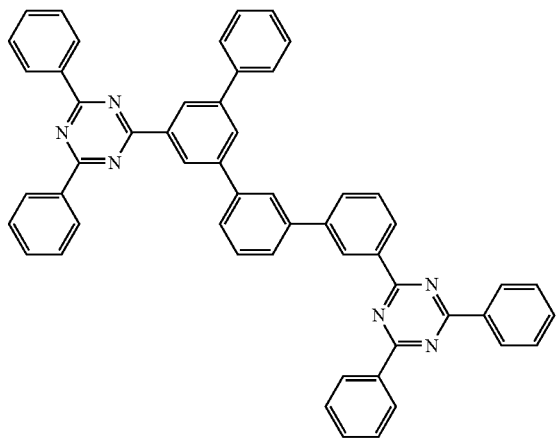
A(69)
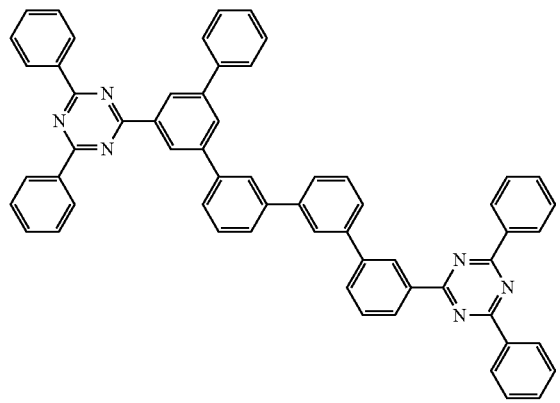
A(70)
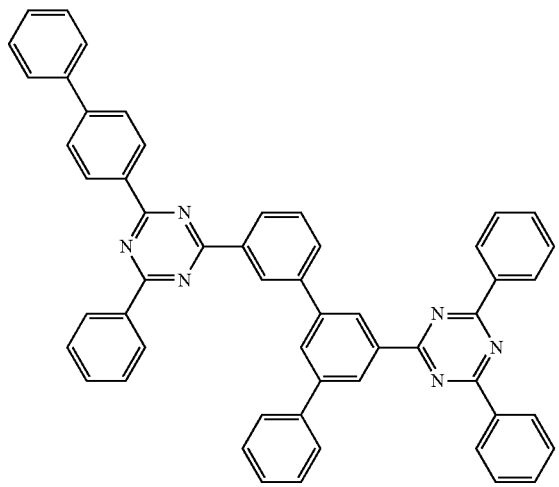
A(71)
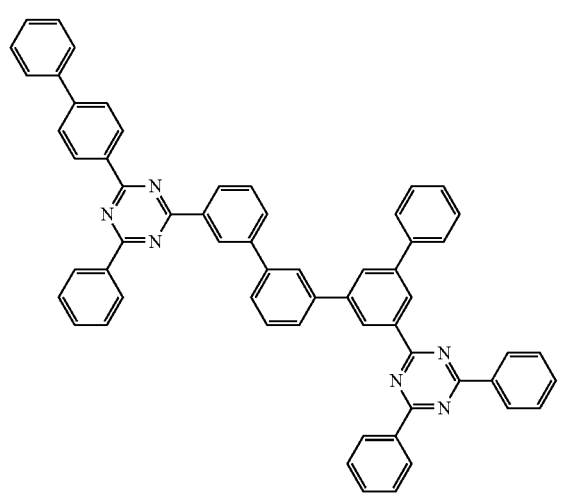

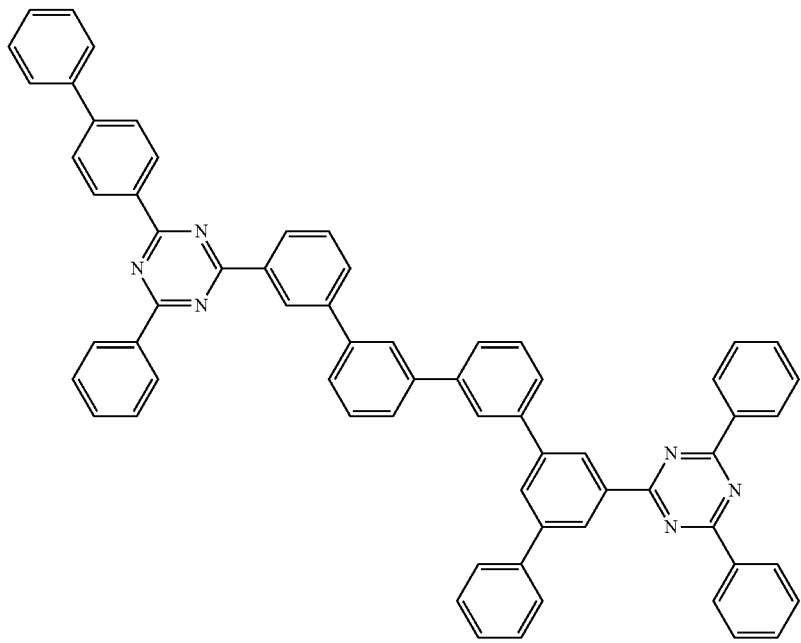
A(72)
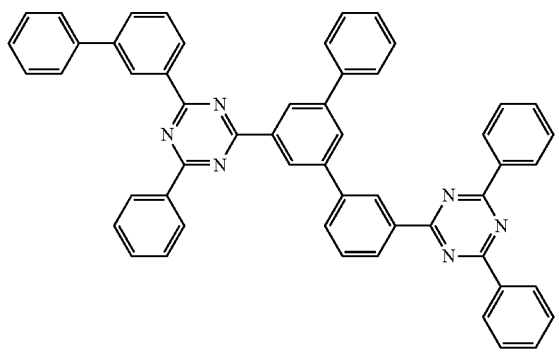
A(73)
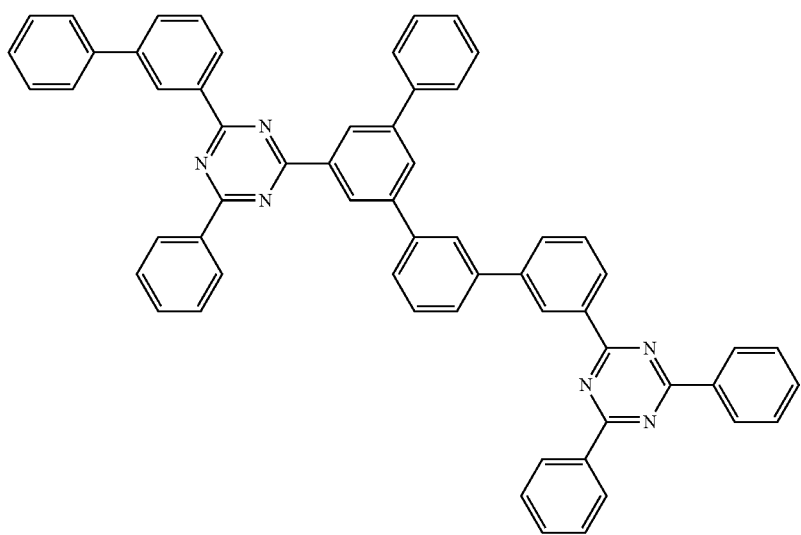
A(74)

-continued
A(75)
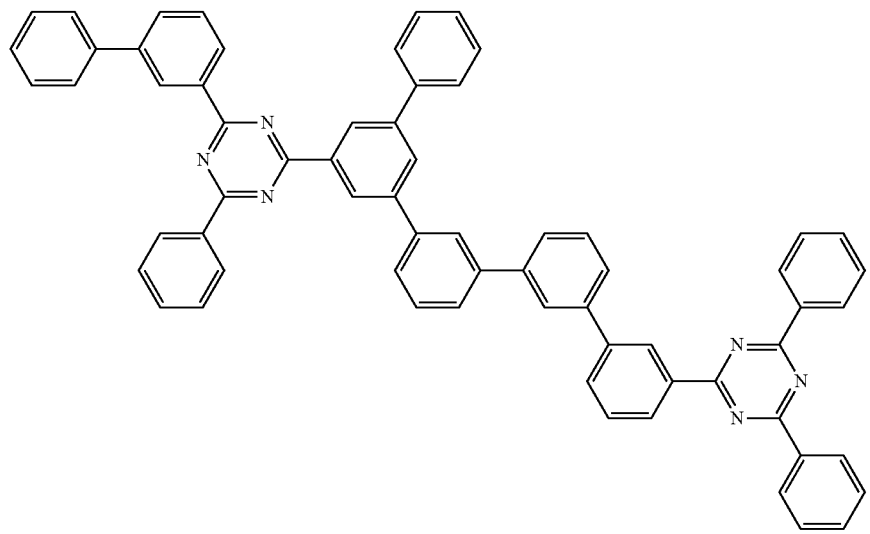
A(76)
A(77)
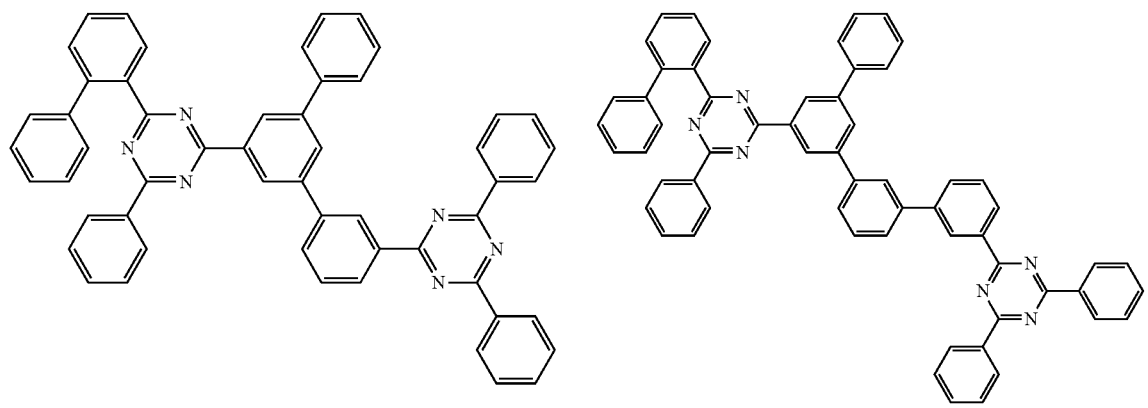
A(78)
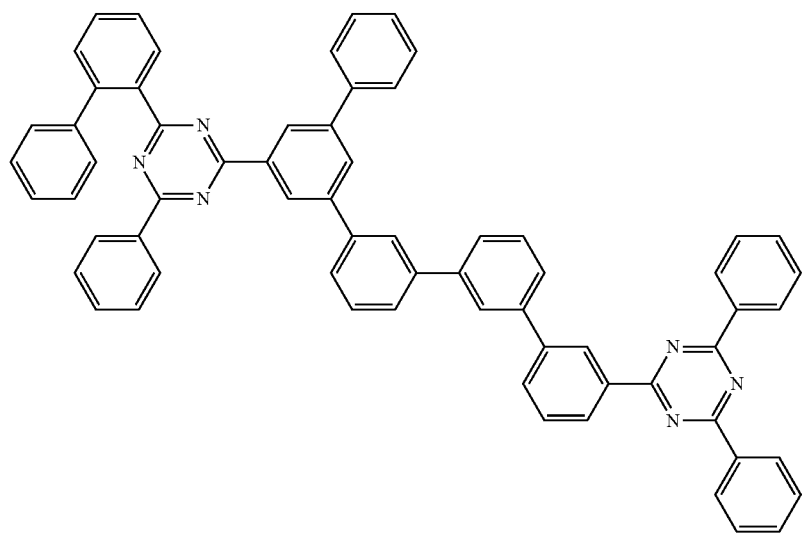

-continued
A(79)
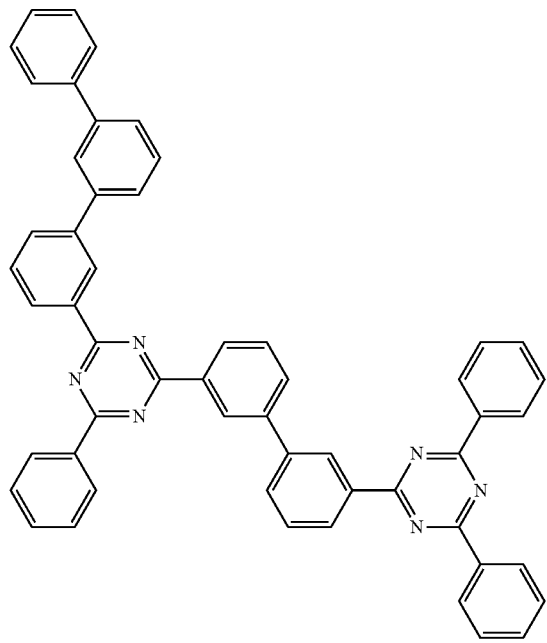
A(80)
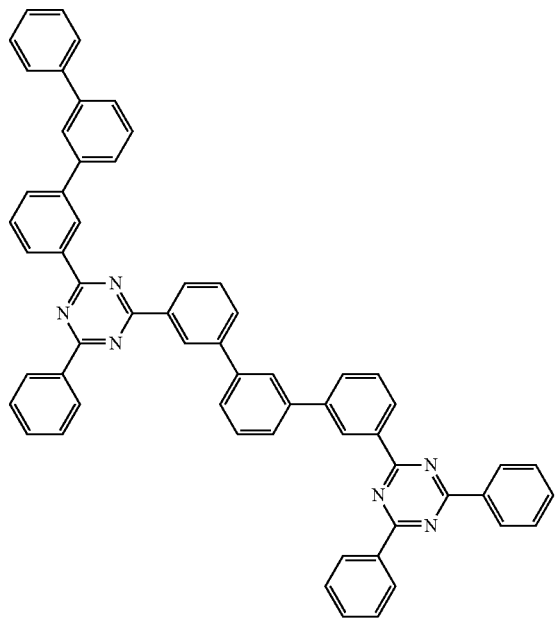
A(81)
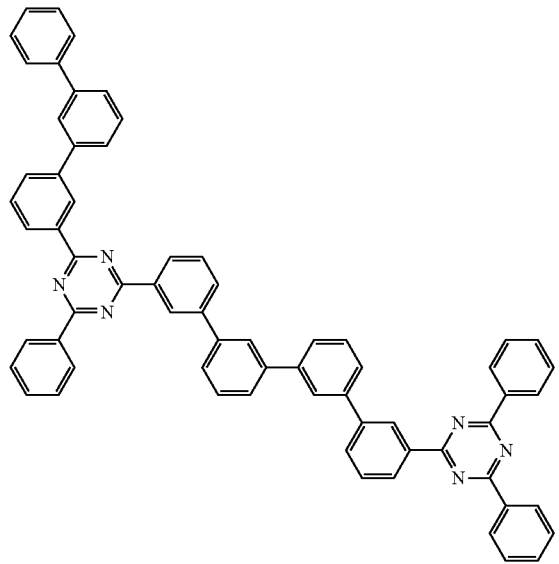
A(82)
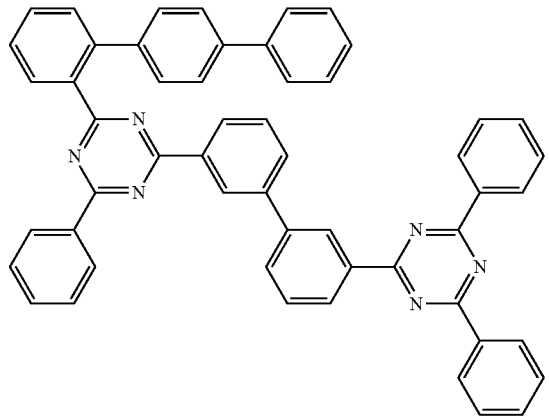

-continued
A(83)
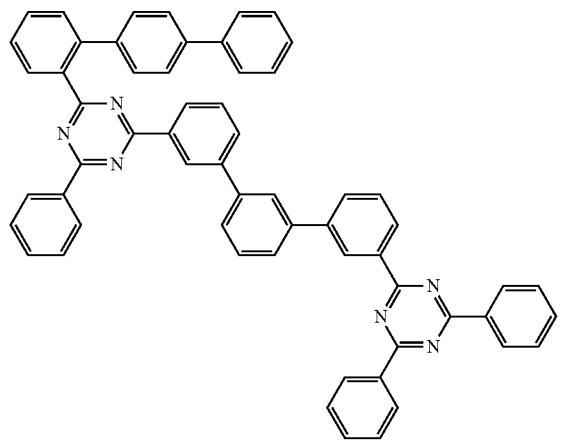
A(84)
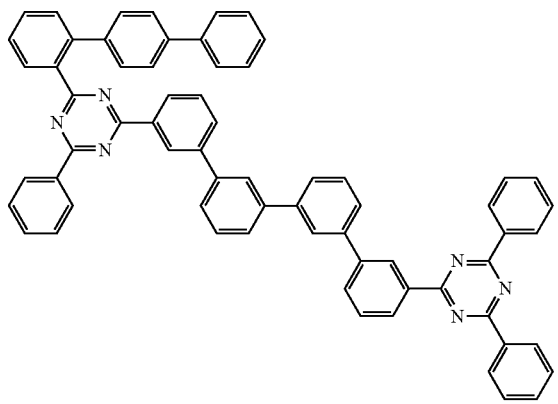
A(85)
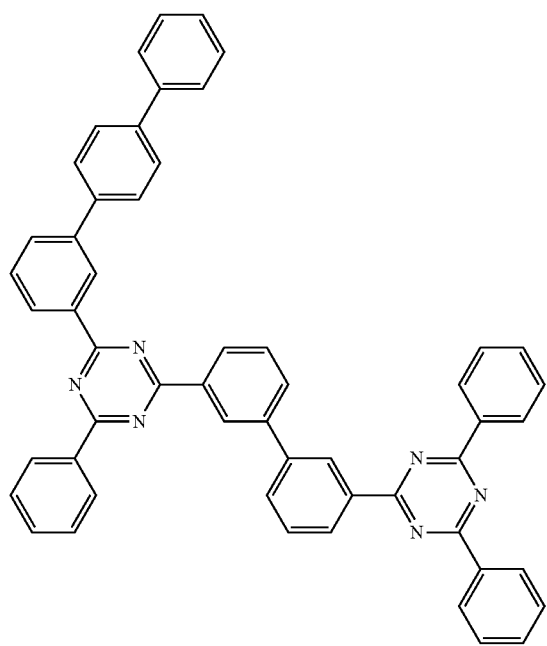
A(86)
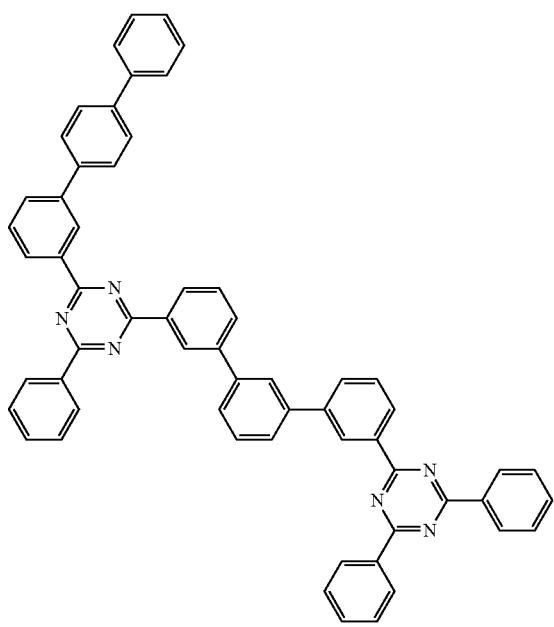

A(87)
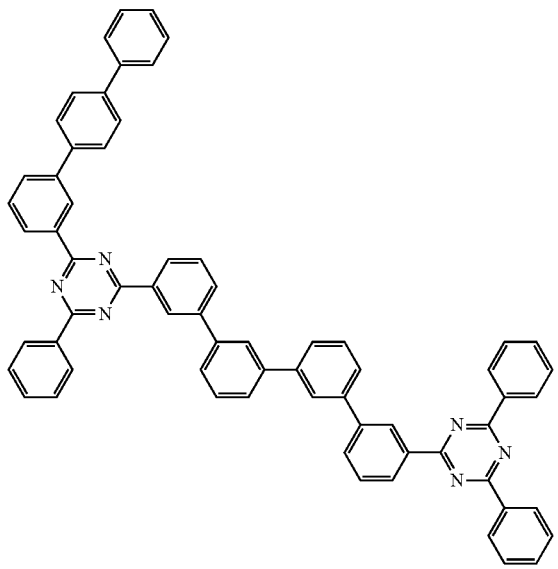
A(88)
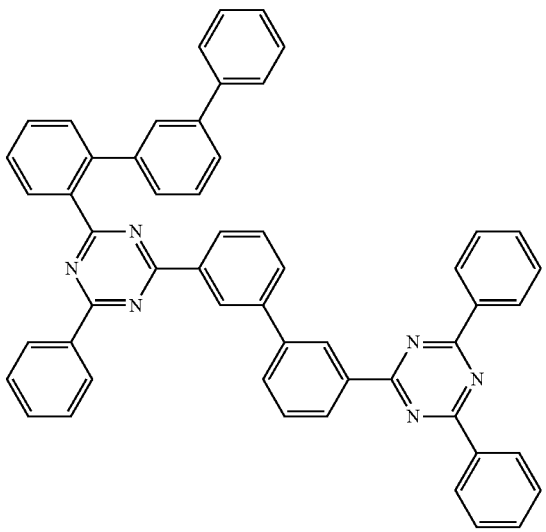
A(89)
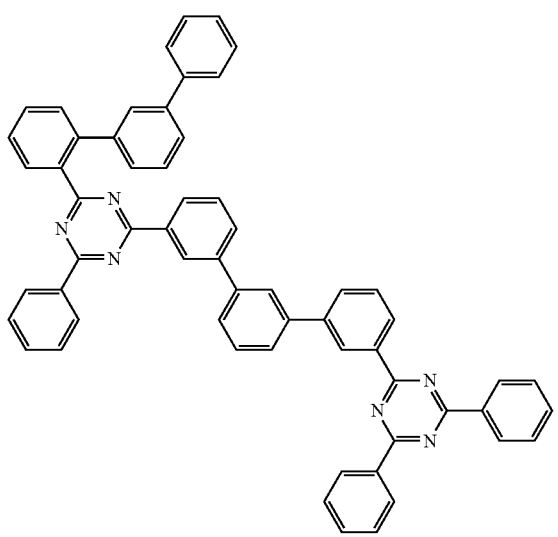
A(90)
A(91)
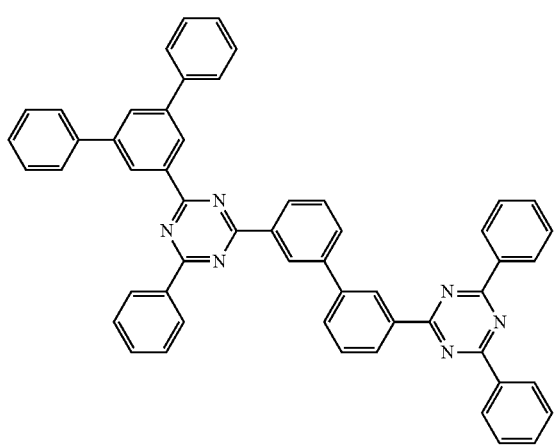

-continued
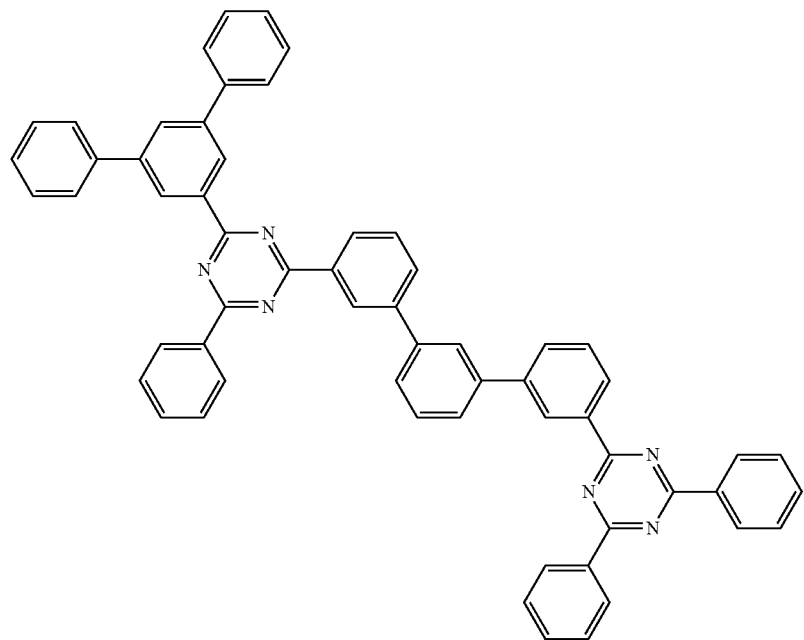
A(92)
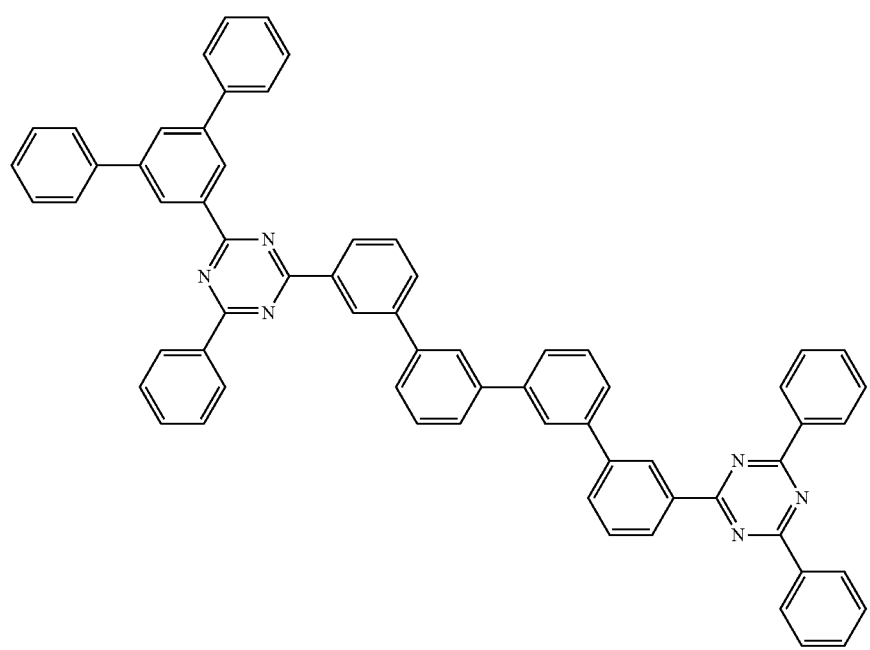
A(93)

-continued
A(94)
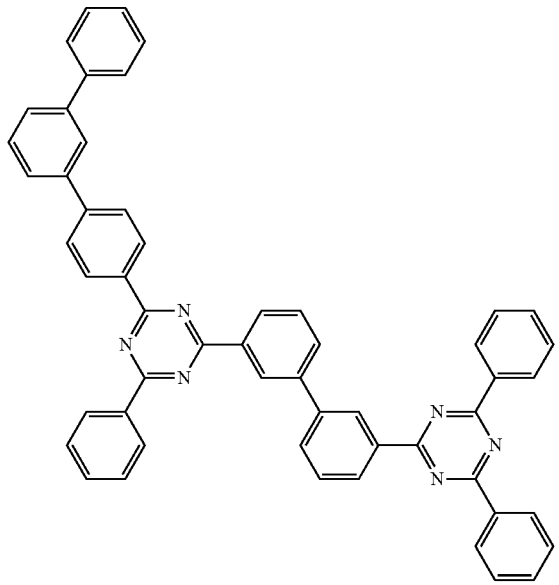
A(95)
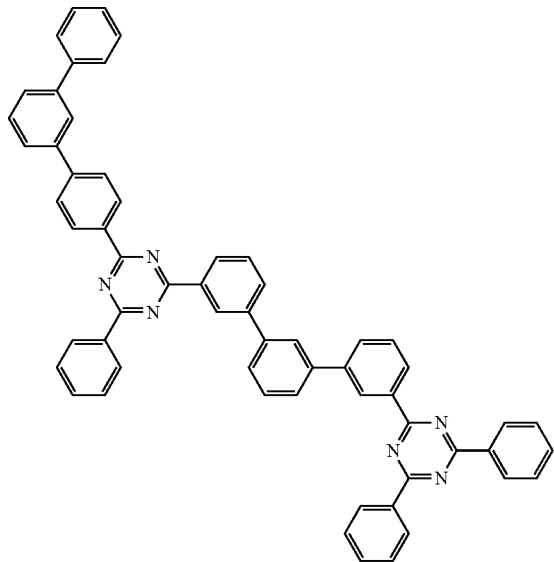
A(96)
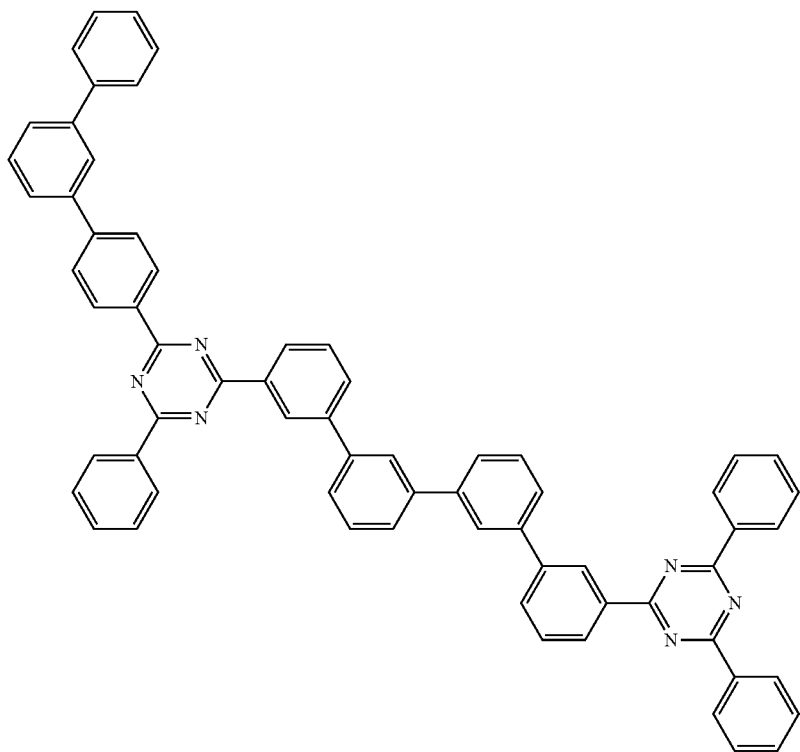

-continued
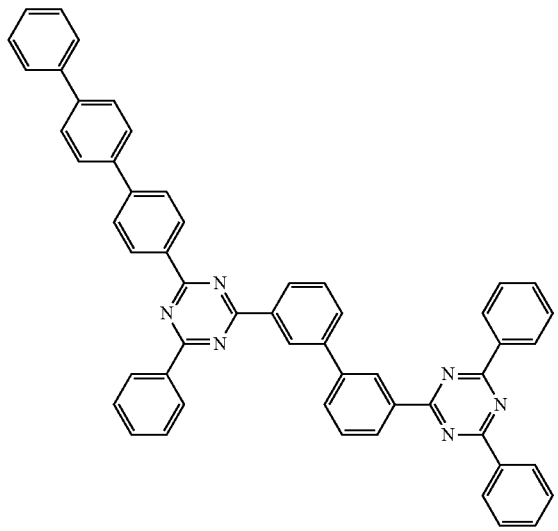
A(97)
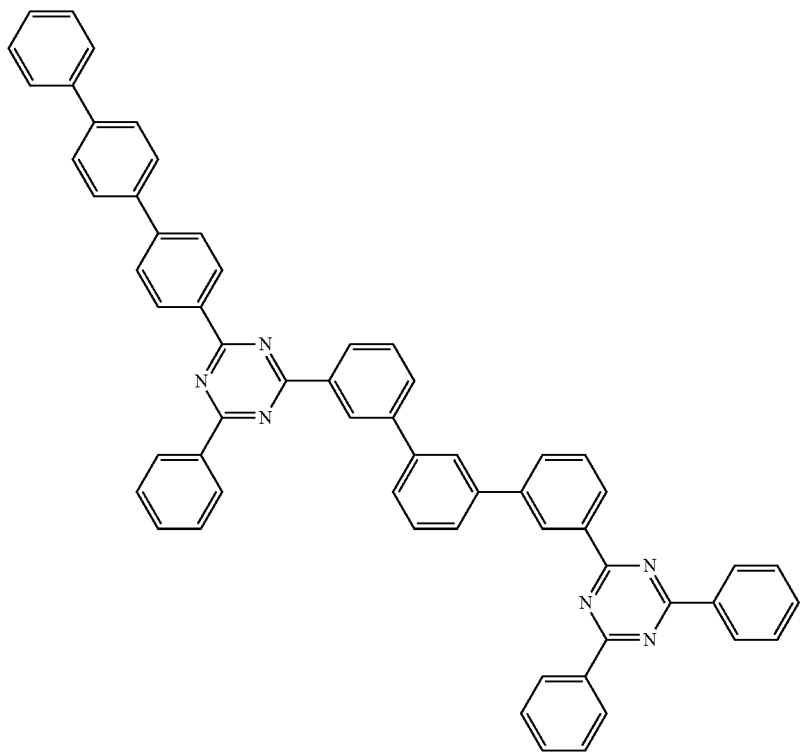
A(98)

-continued
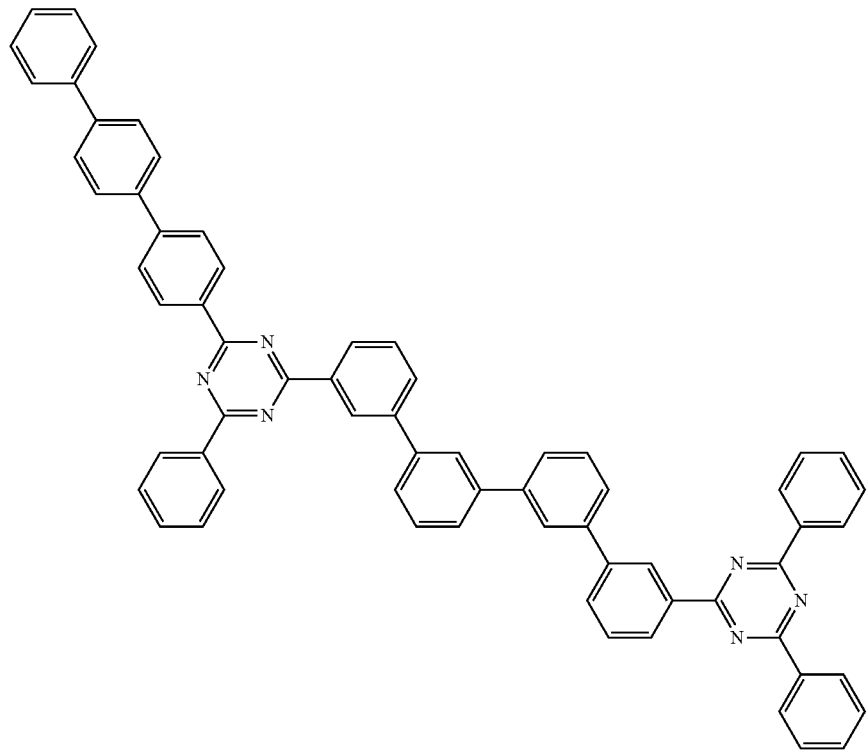
A(99)
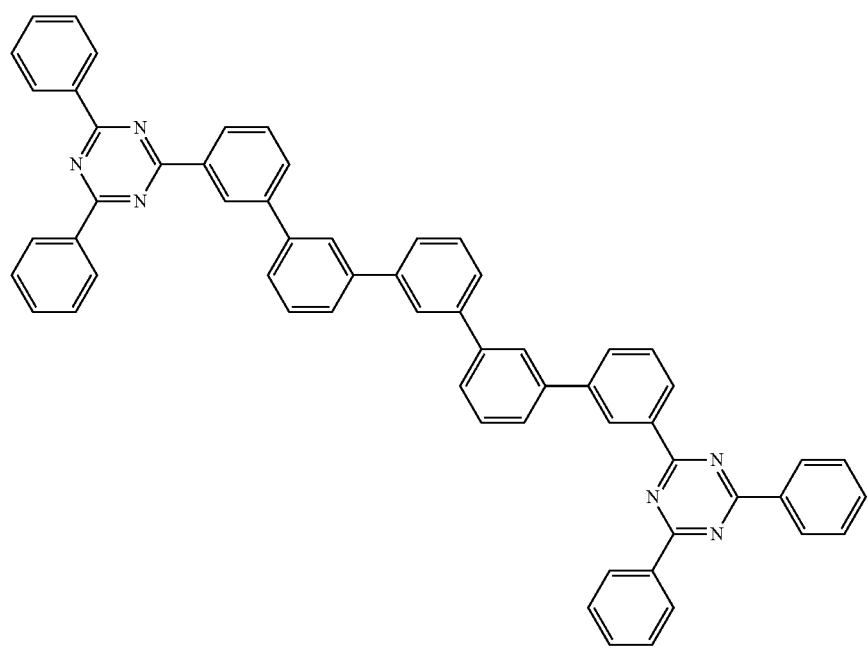
A(100)

-continued
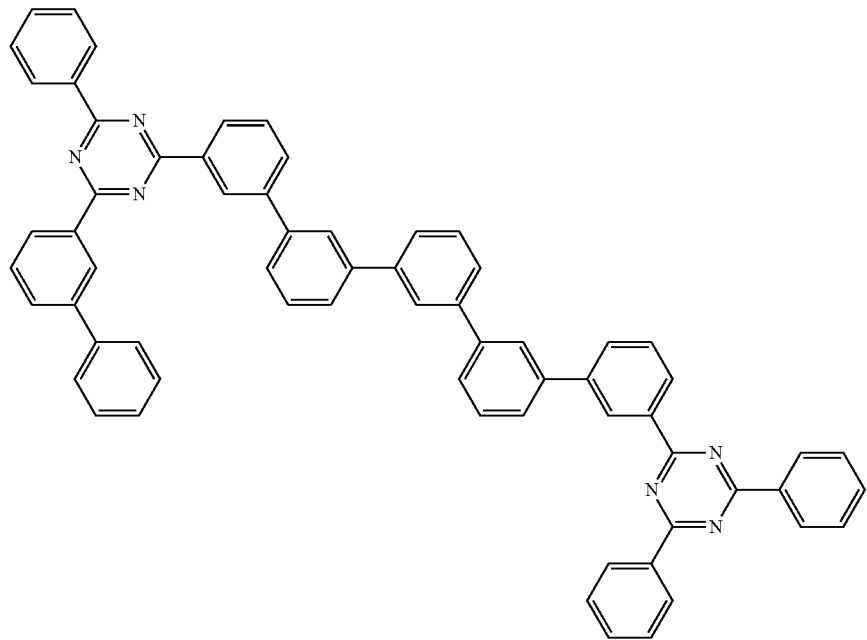
A(101)
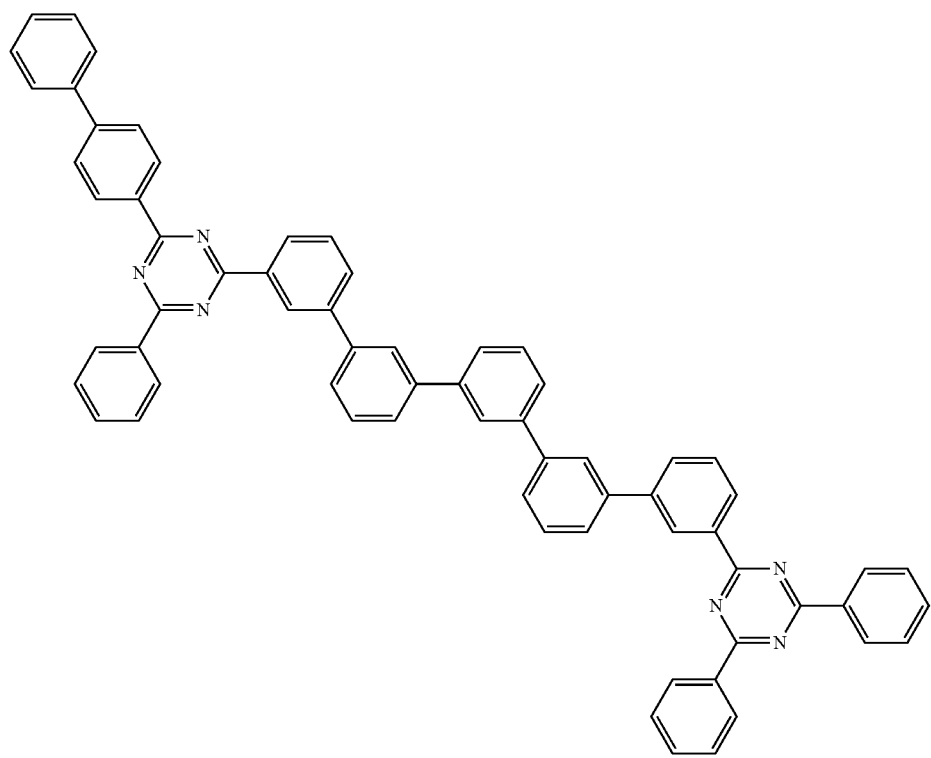
A(102)

-continued
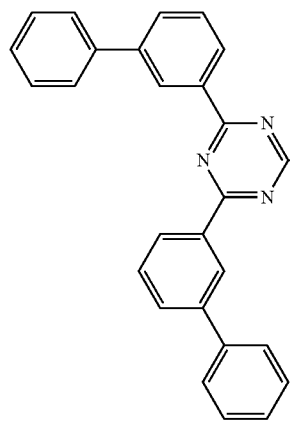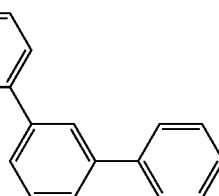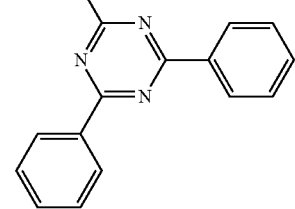
A(103)
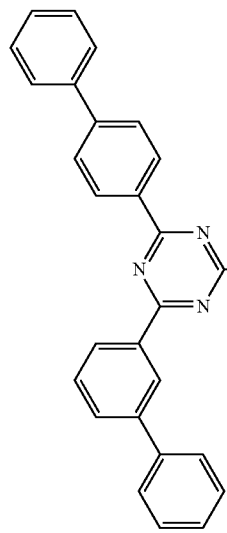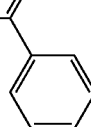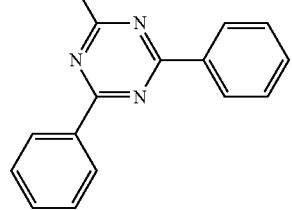
A(104)

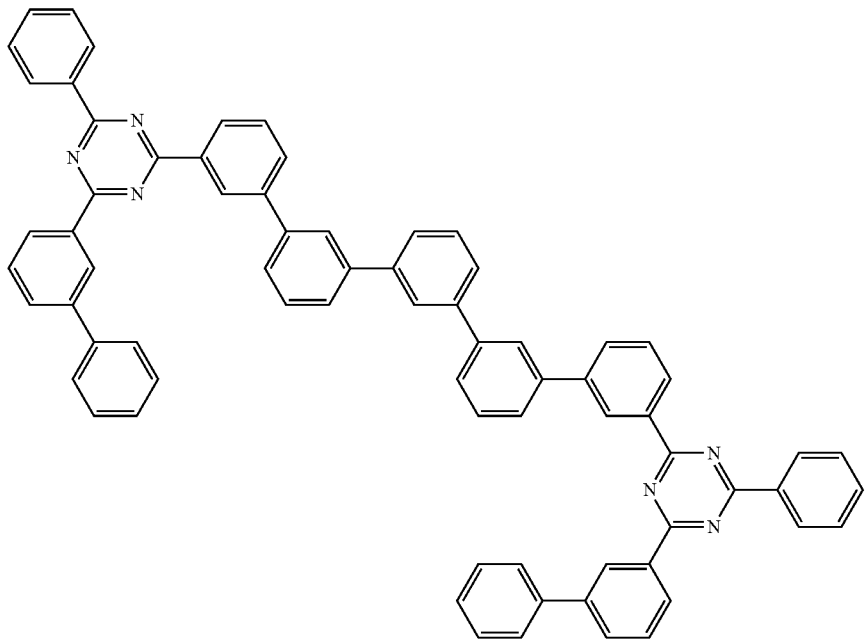
A(105)
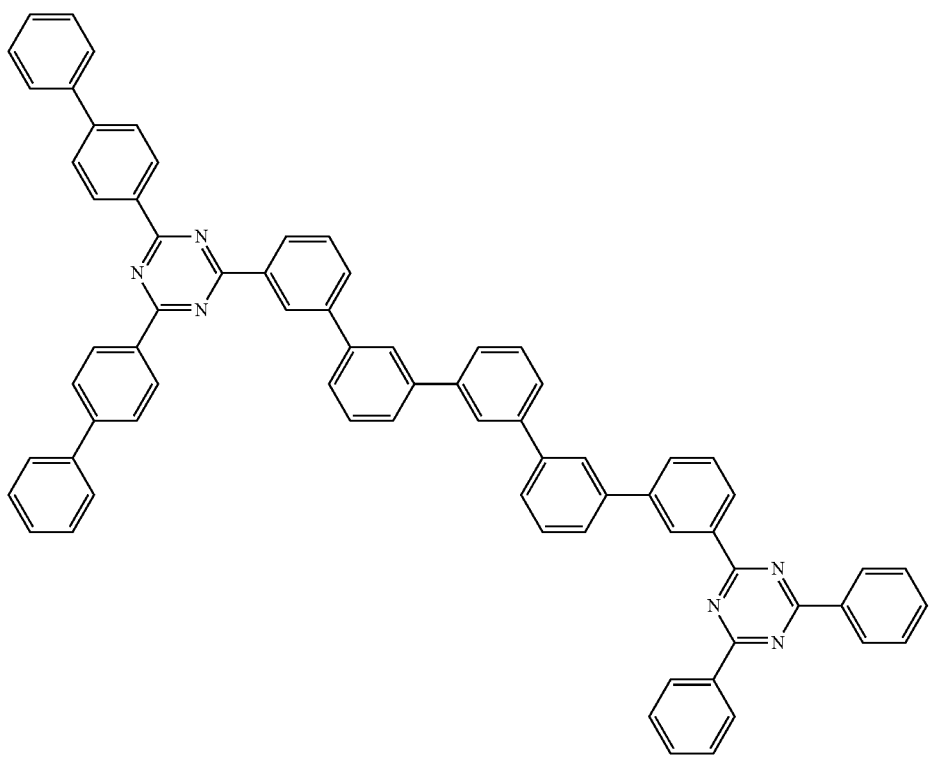
A(106)

-continued
A(107)
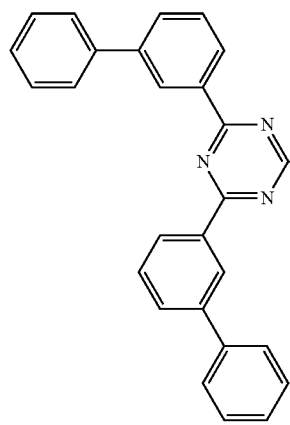
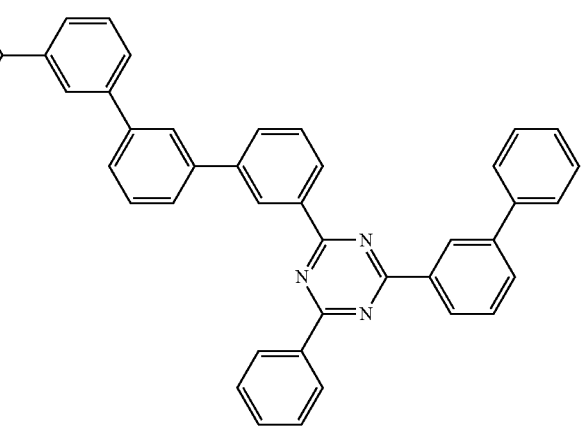
A(108)
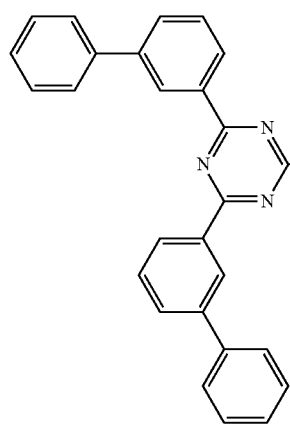
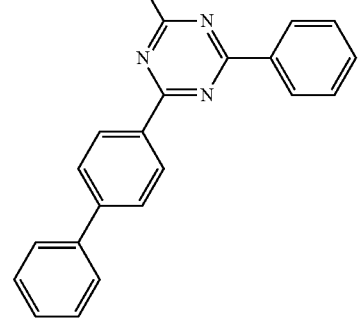

-continued
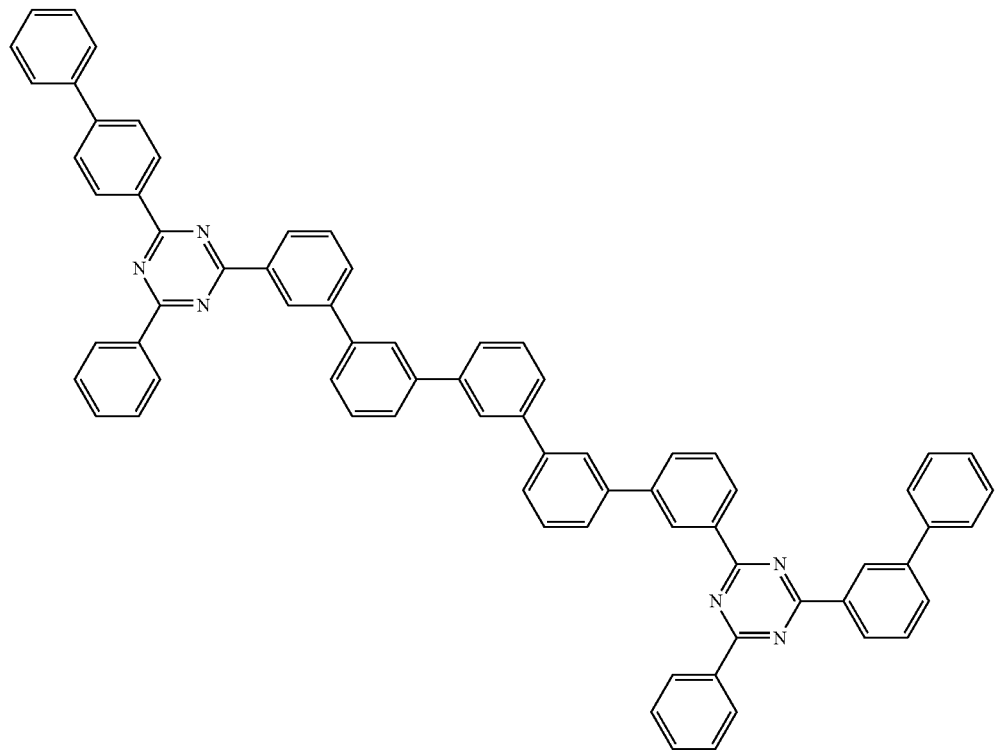
A(109)
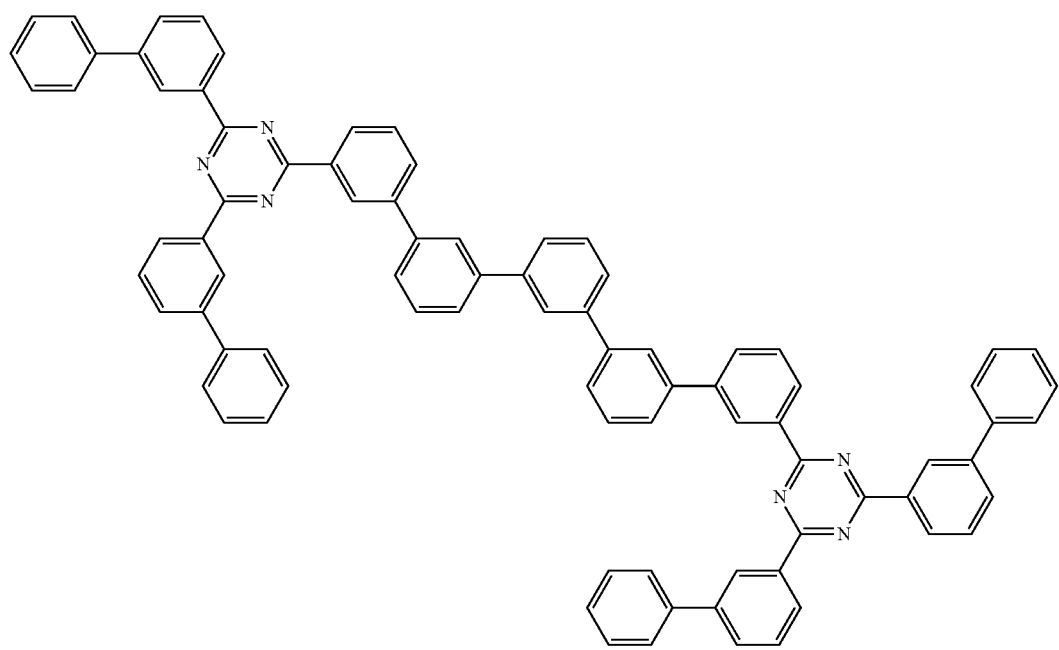
A(110)

-continued
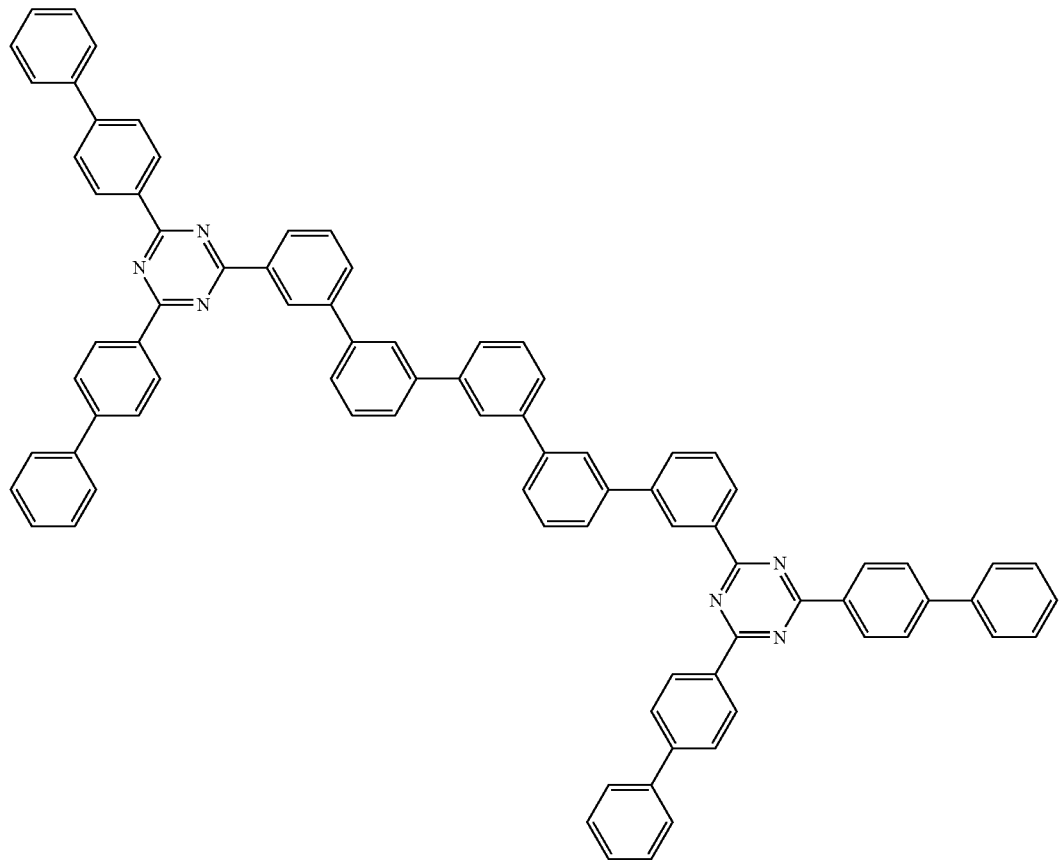
A(111)
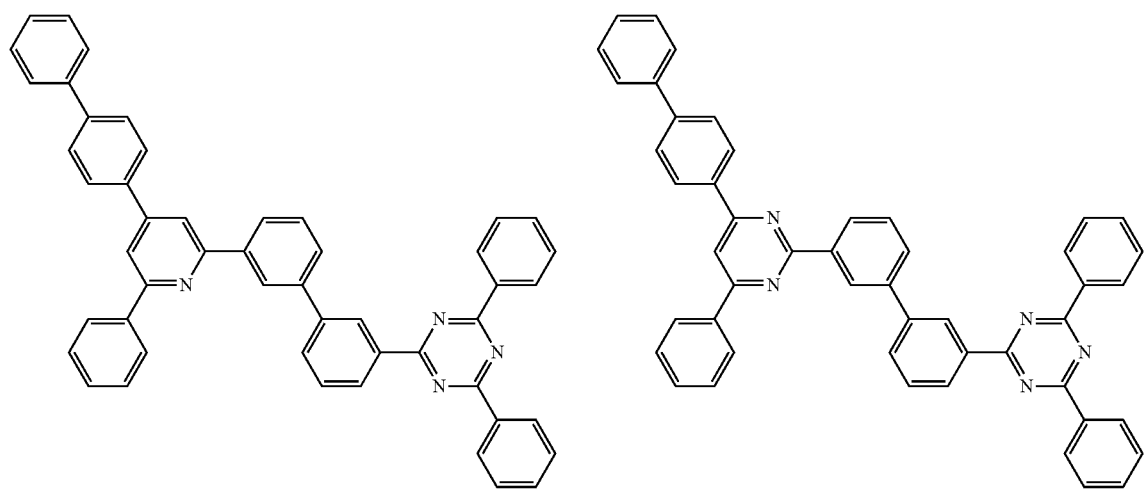
A(112)  A(113)

-continued
A(114)        A(115)
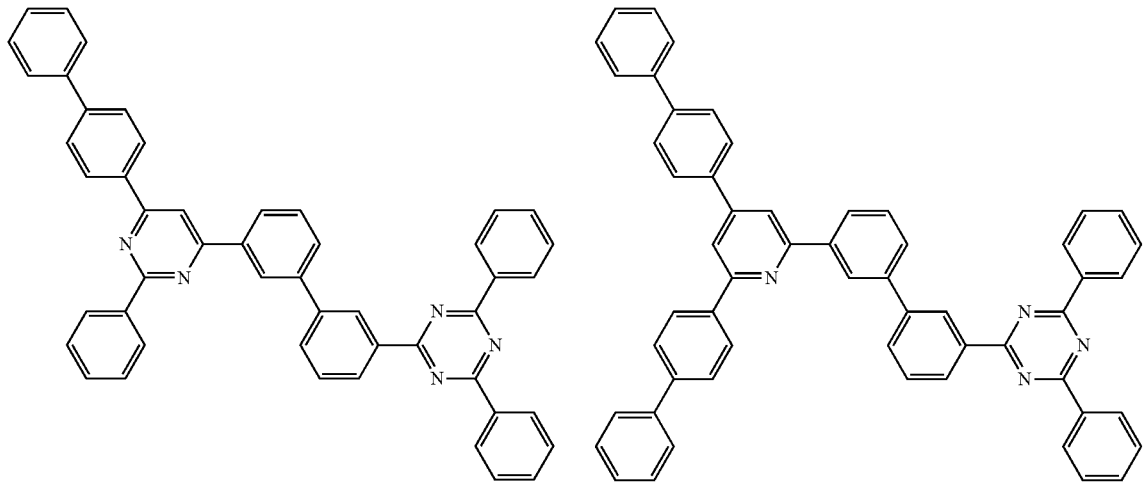
A(116)        A(117)
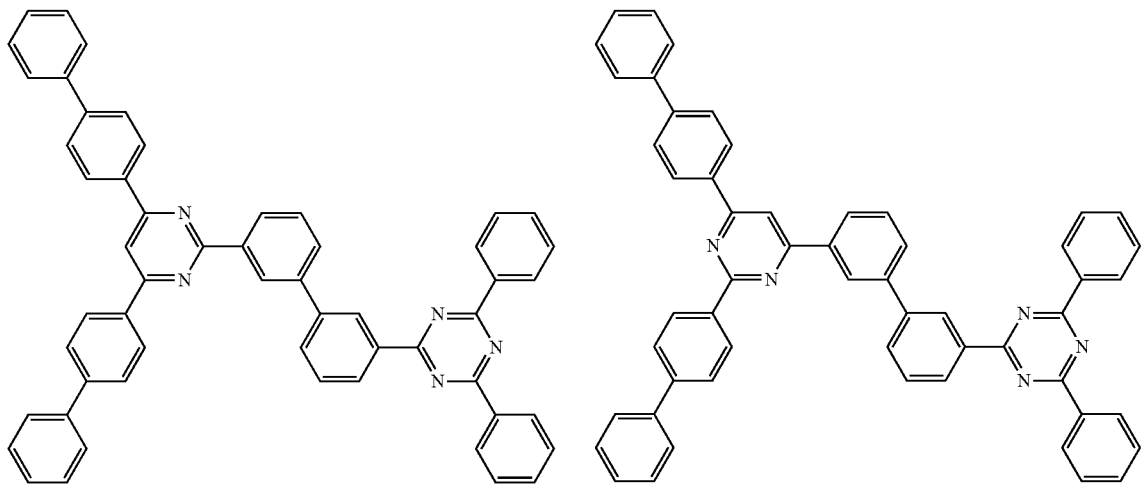
A(118)        A(119)
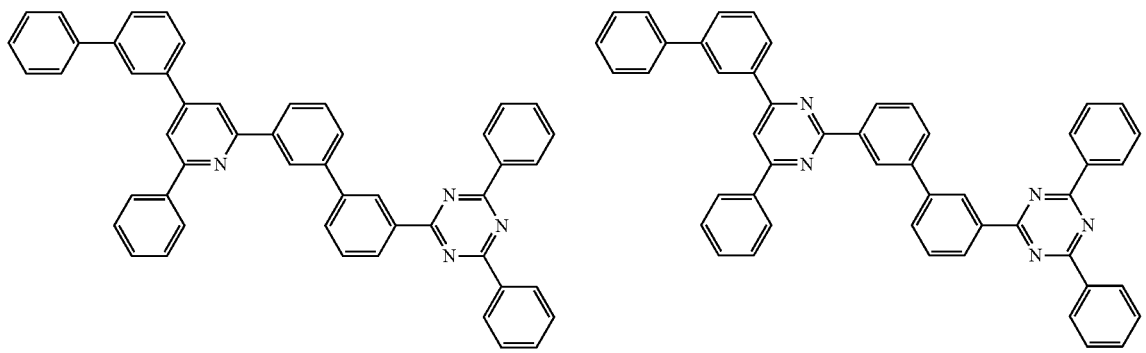

-continued
A(120)

A(121)

A(122)
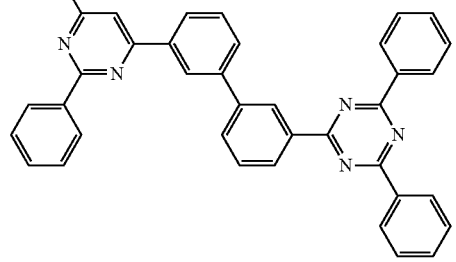
A(123)
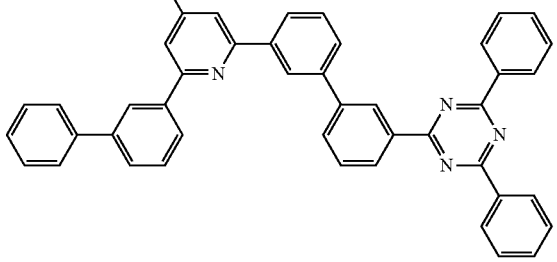
A(124)

A(125)

A(126)

A(127)

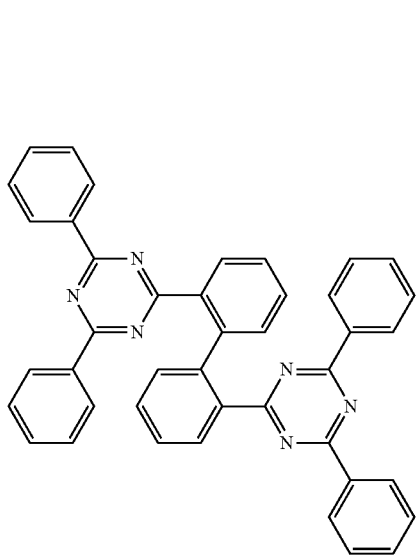
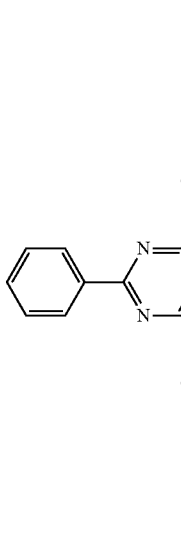
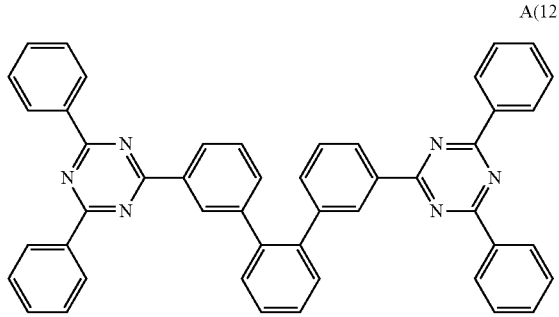
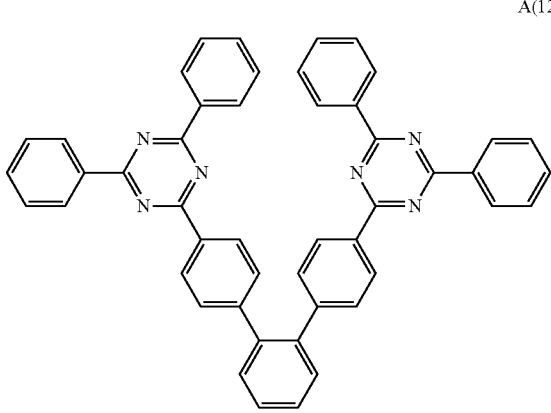

-continued
A(128)
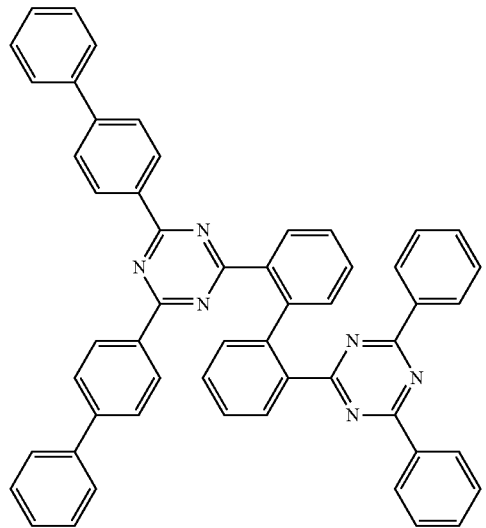
A(129)
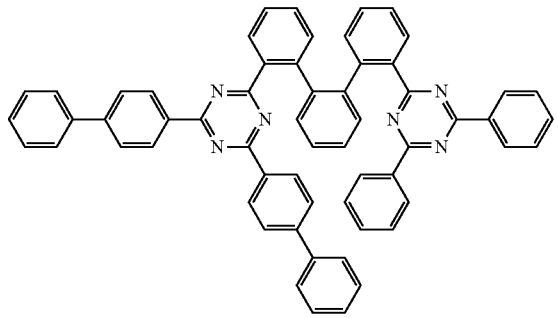
A(130)
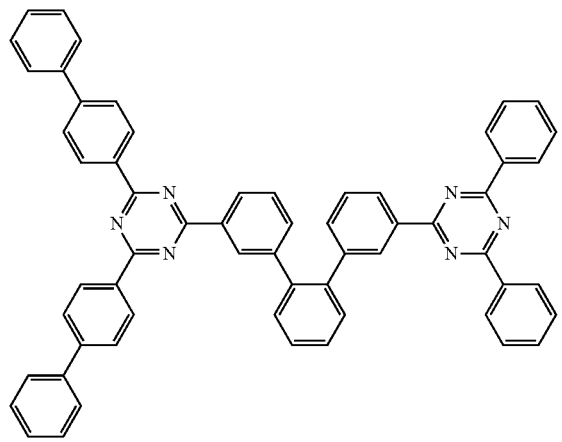
A(131)
A(132)
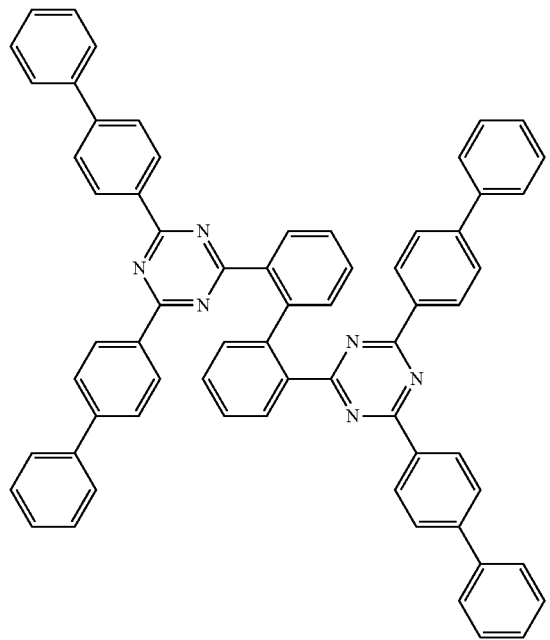

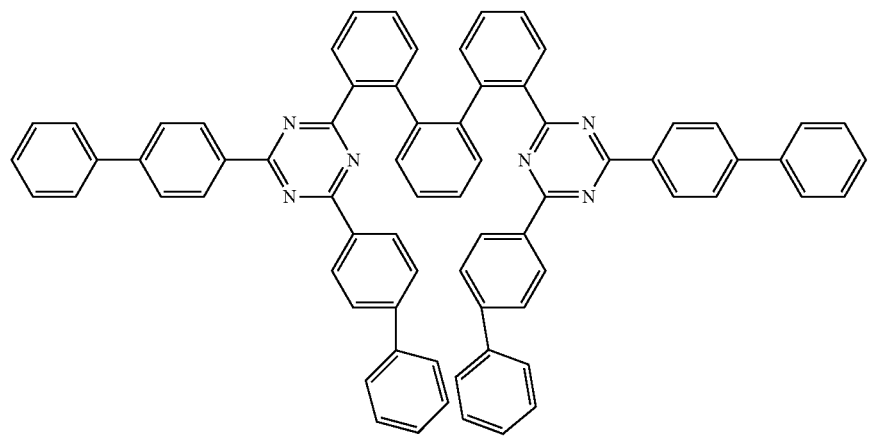
A(133)
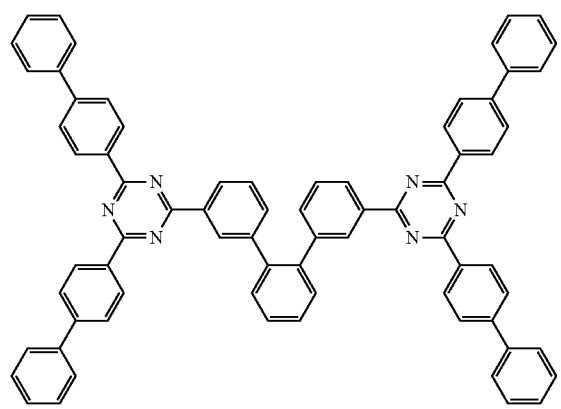
A(134)
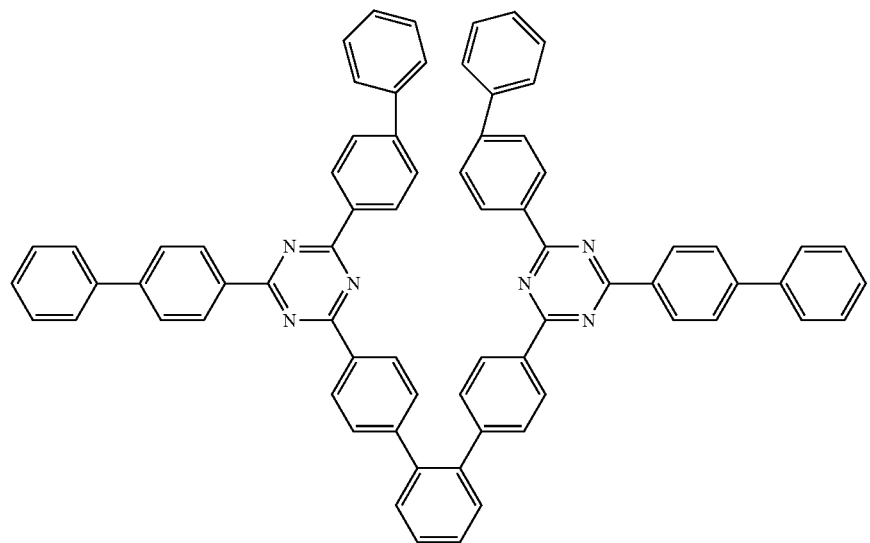
A(135)

-continued
A(136)
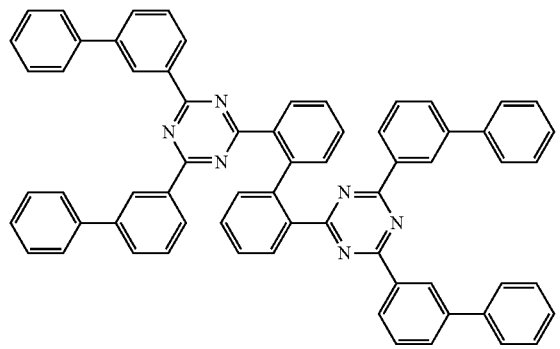
A(137)
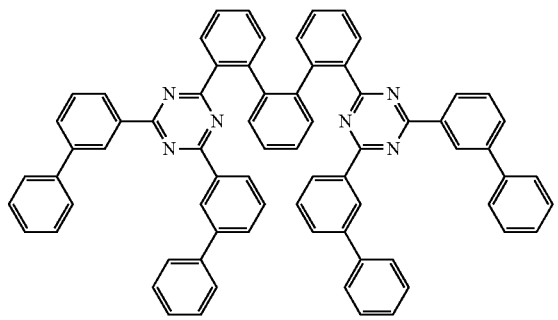
A(138)
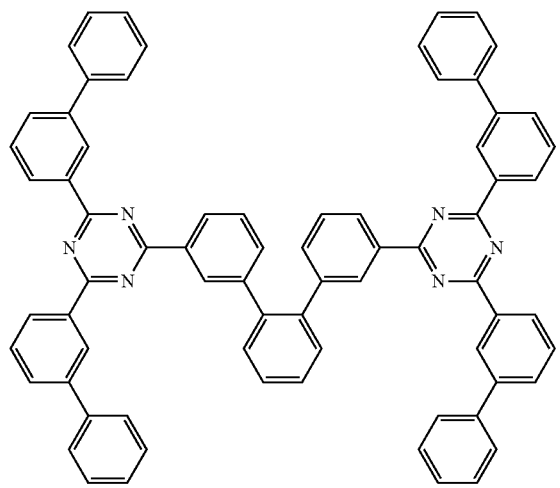
A(139)
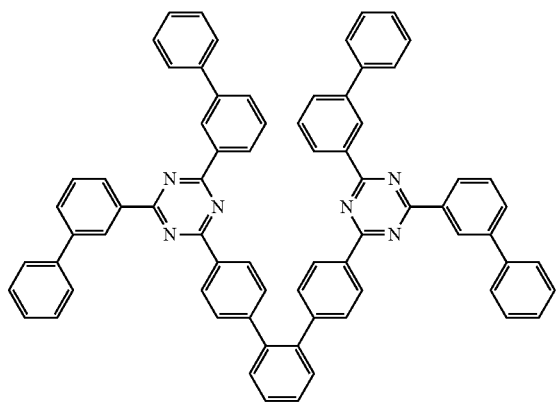
A(140)
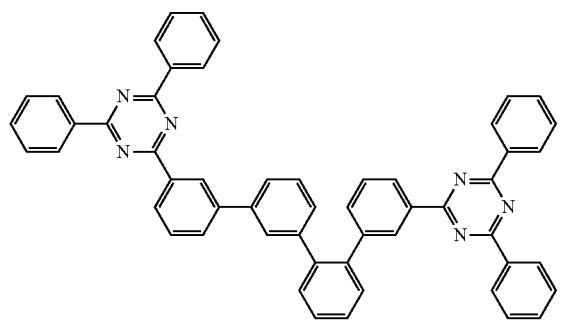
A(141)
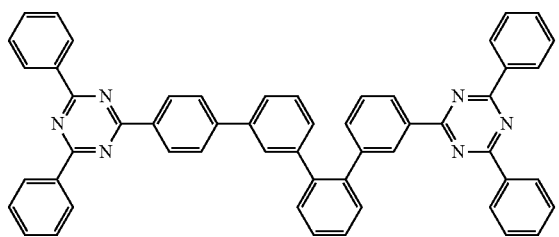

-continued
A(142)
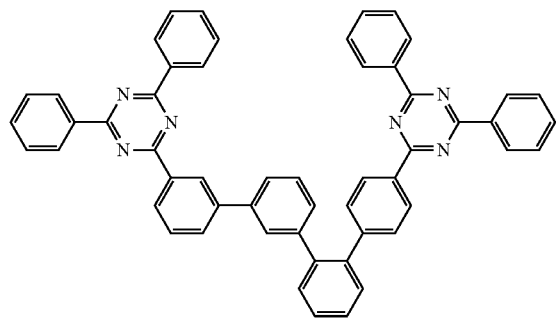
A(143)
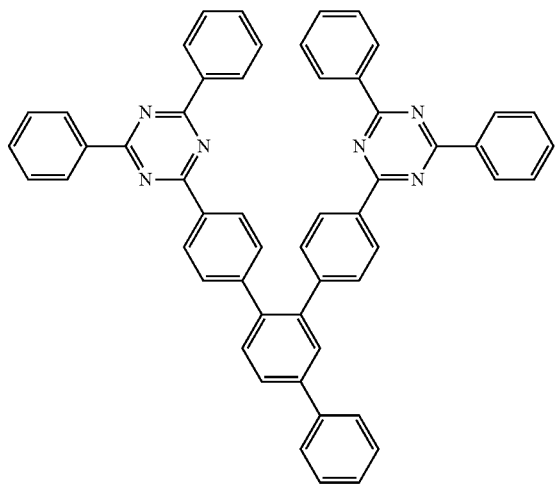
A(144)
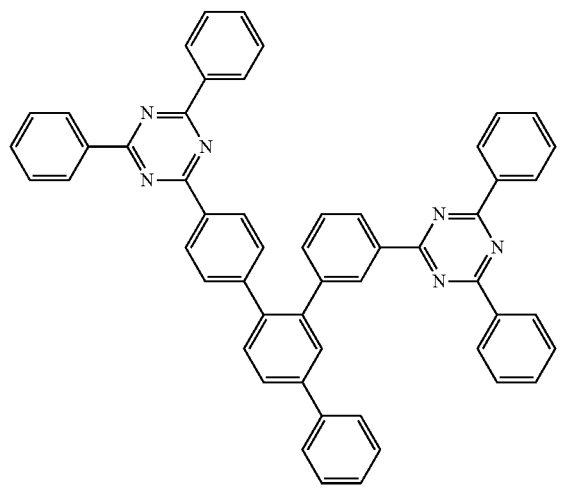
A(145)
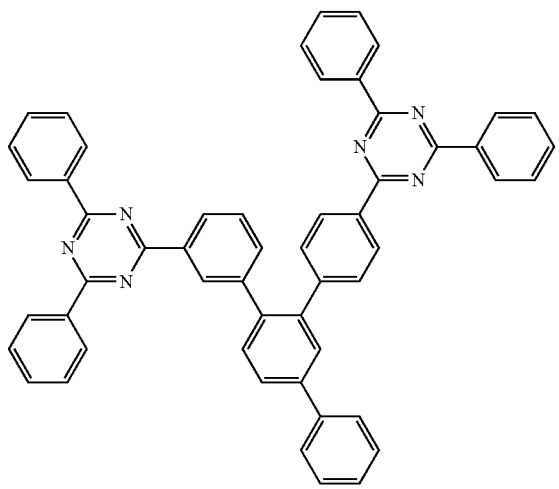
A(146)
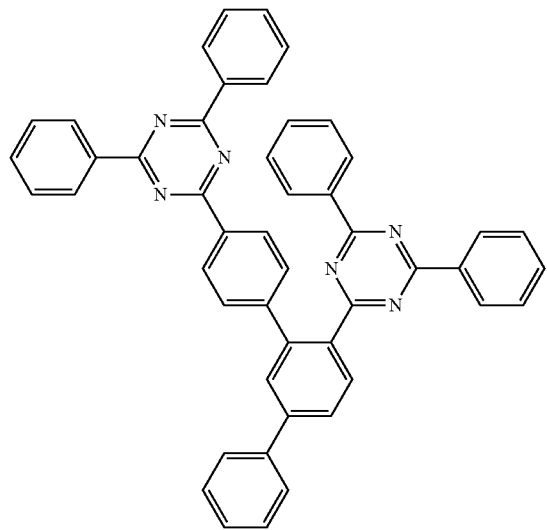
A(147)
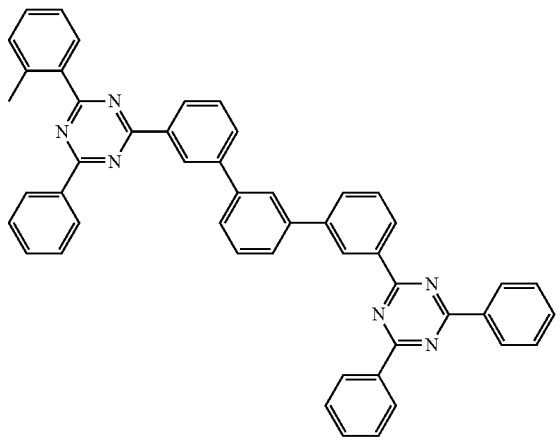

-continued
A(148)
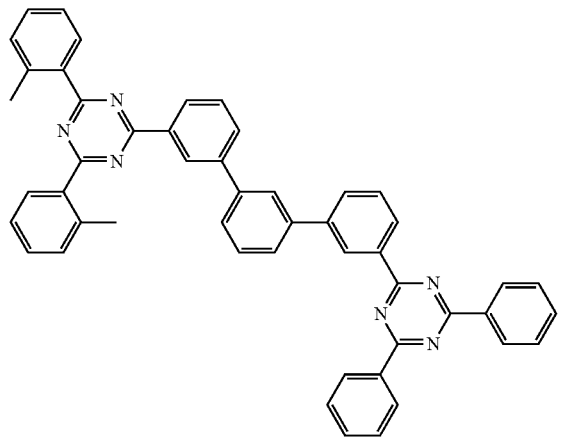
A(149)
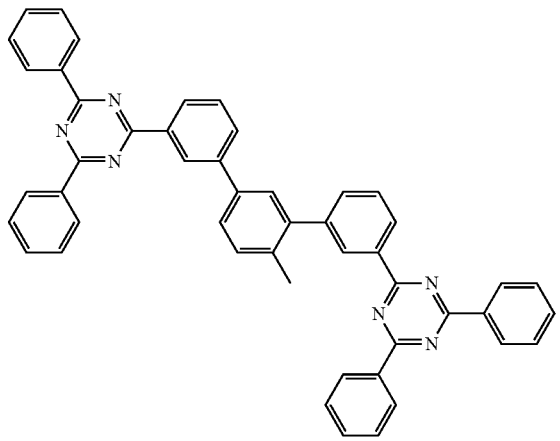
A(150)
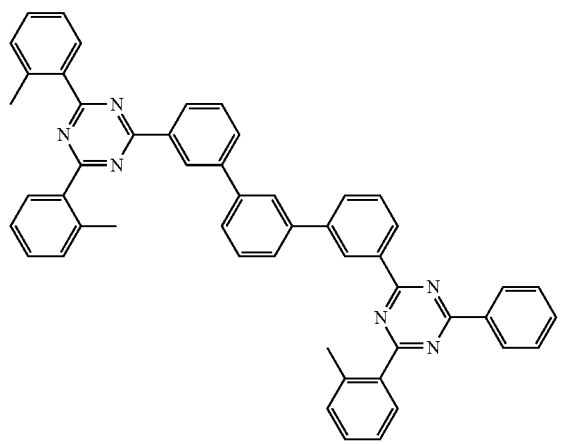
A(151)
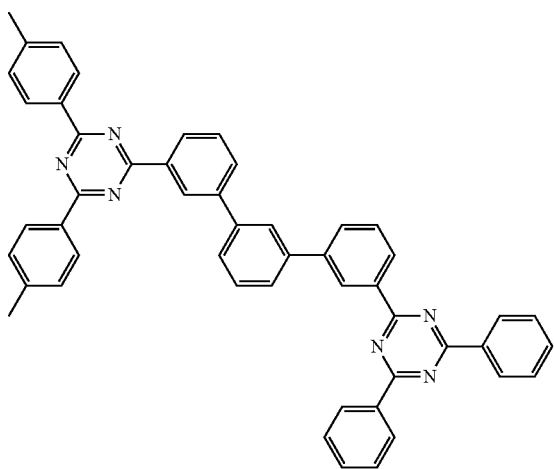
A(152)
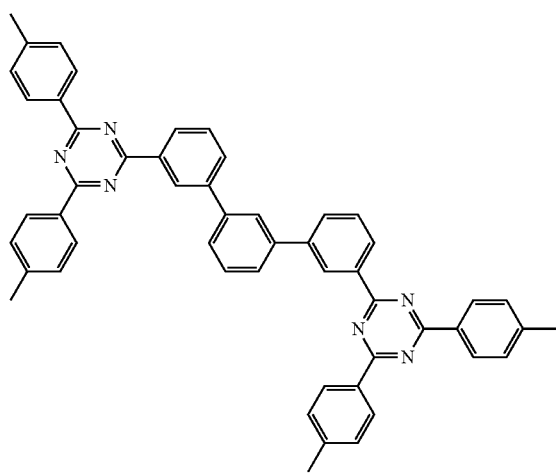
A(153)
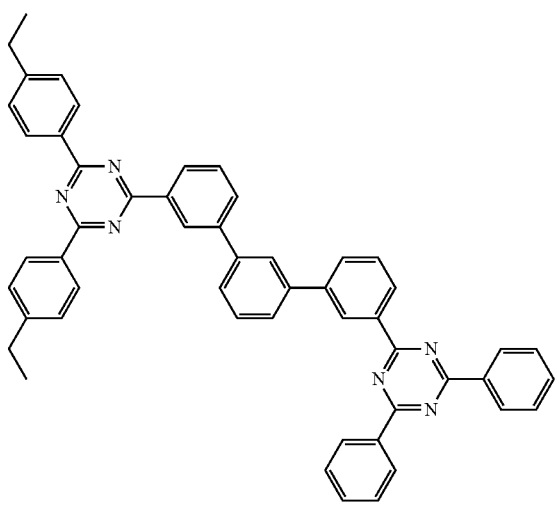

A(154)
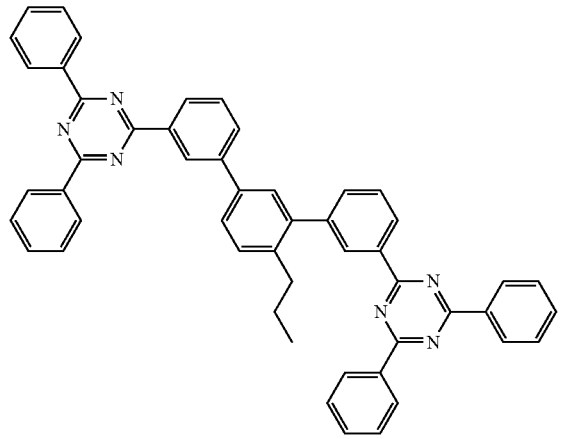
Group HE2
1
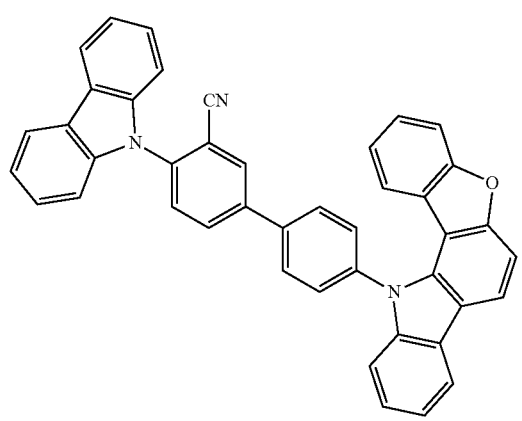
2
3
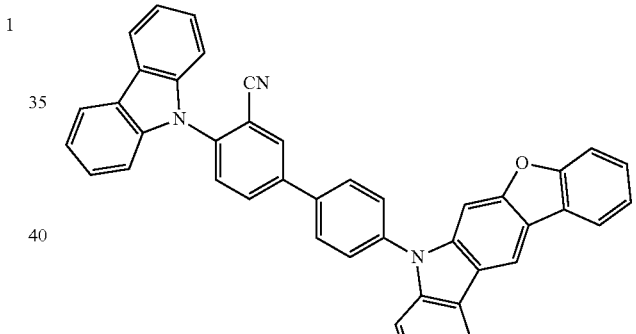
4
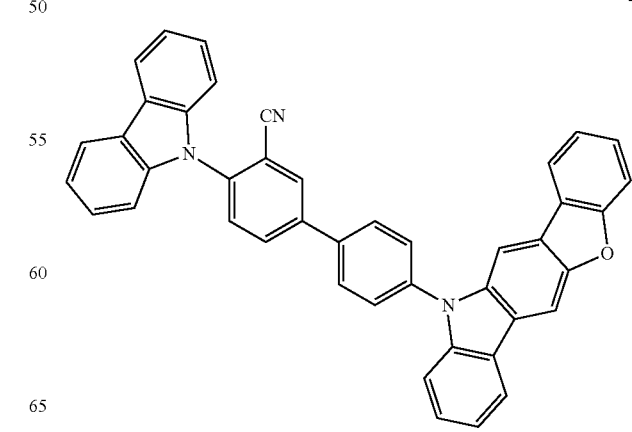

5
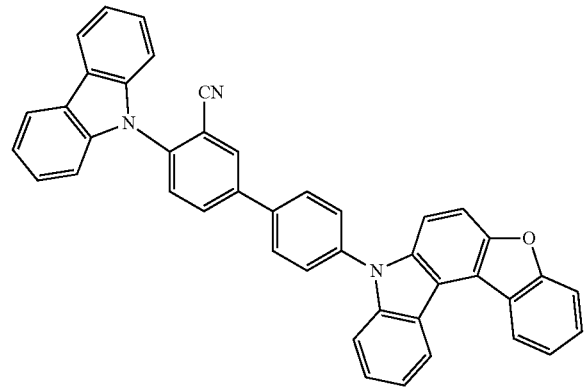
6
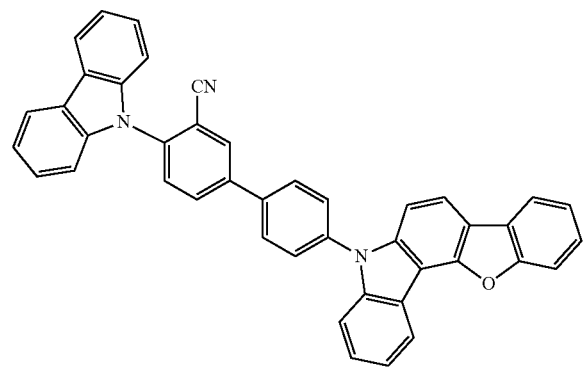
7
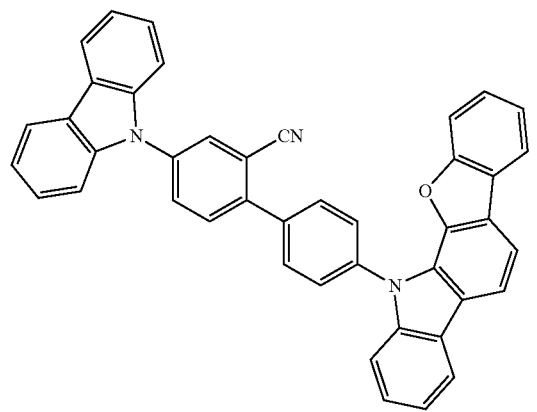
8
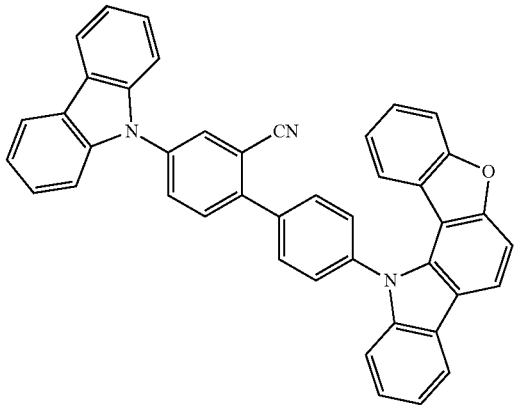
9
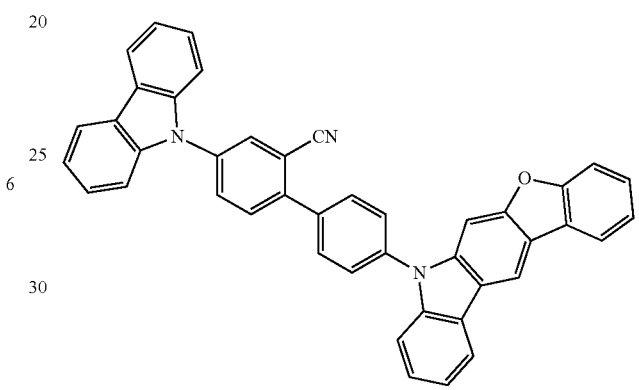
10
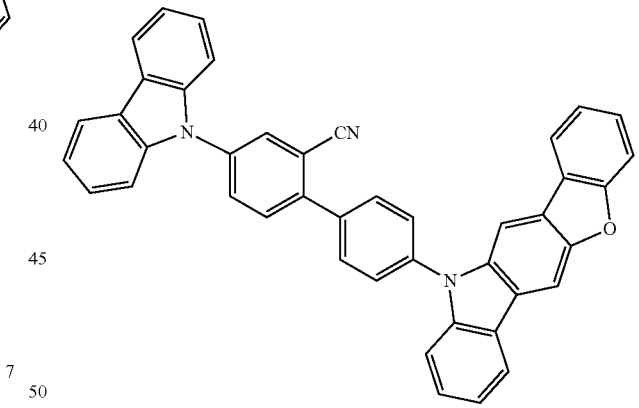
11
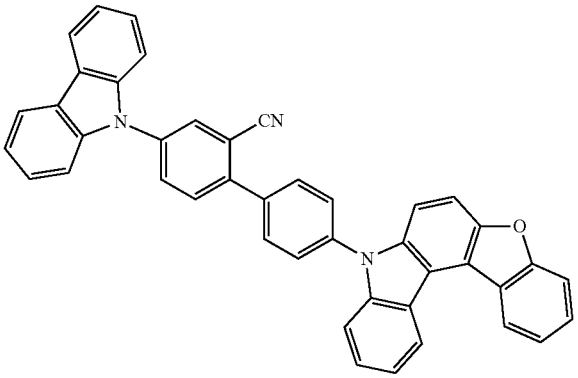

12
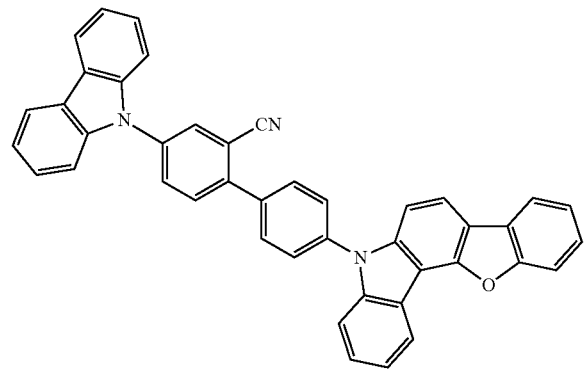
13
15
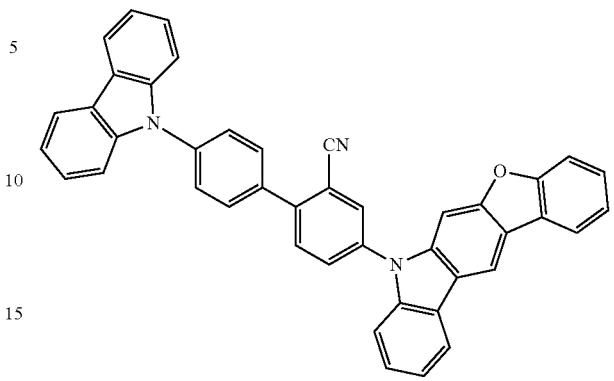
16
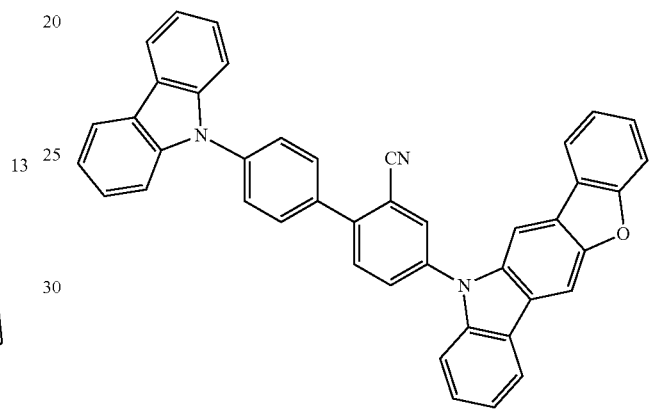
17
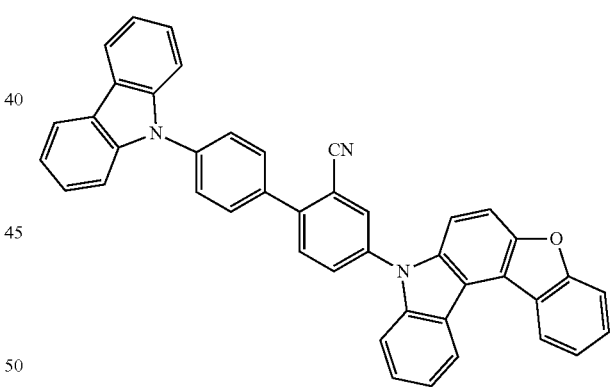
18
14
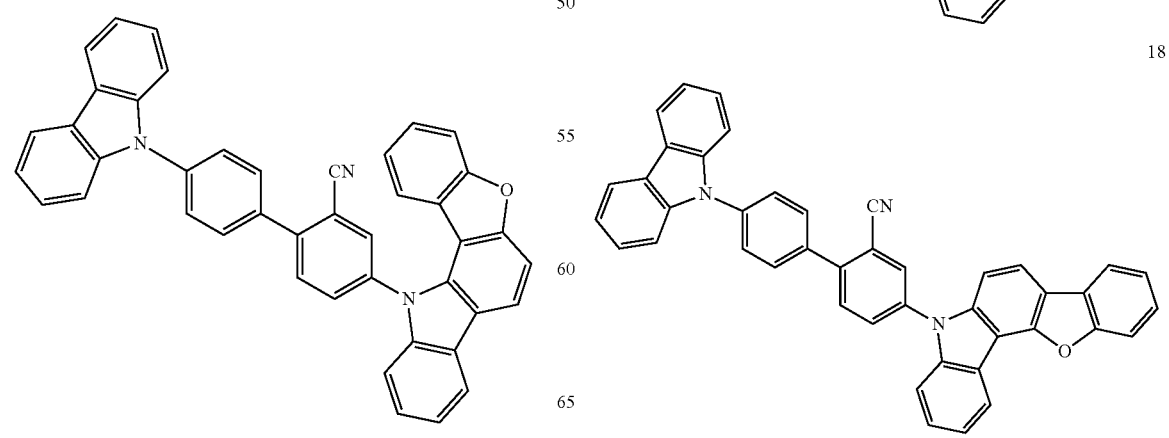

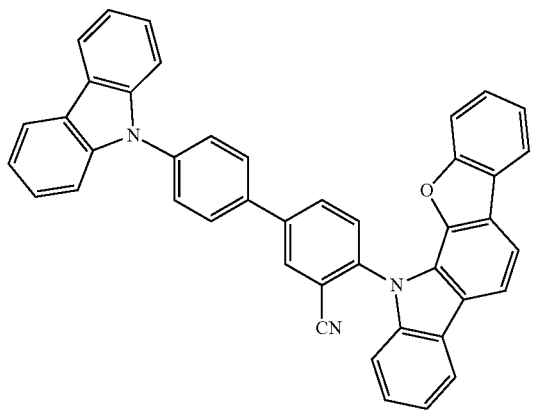
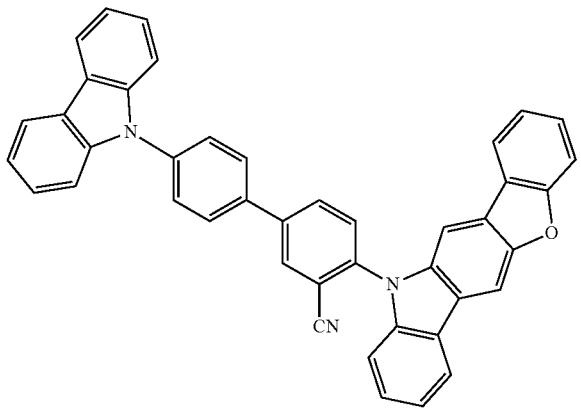
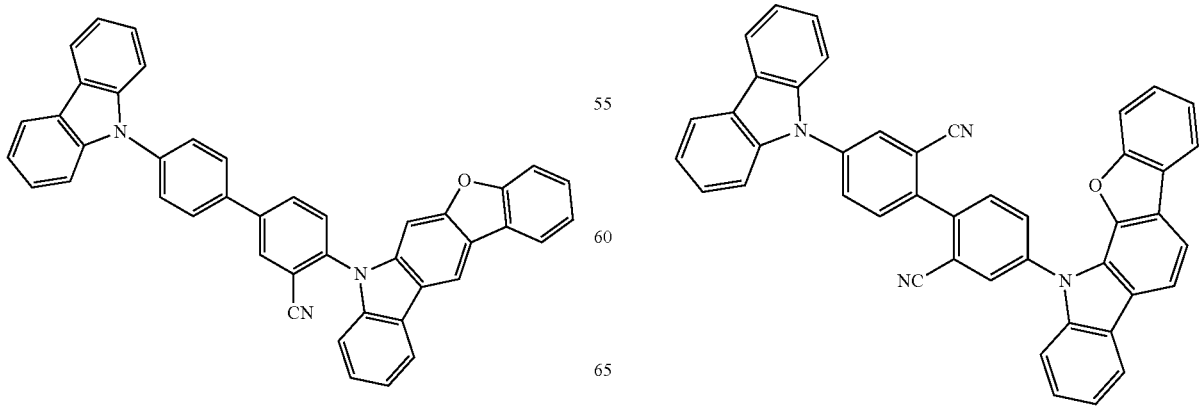

-continued
26
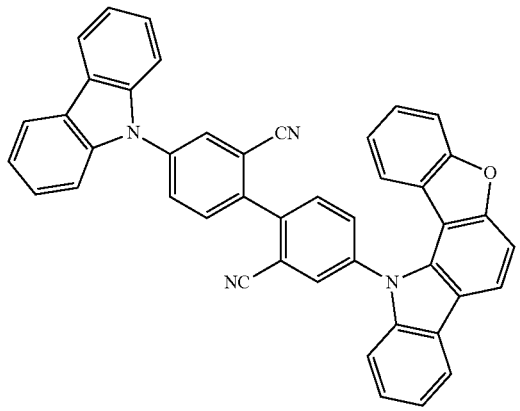
27
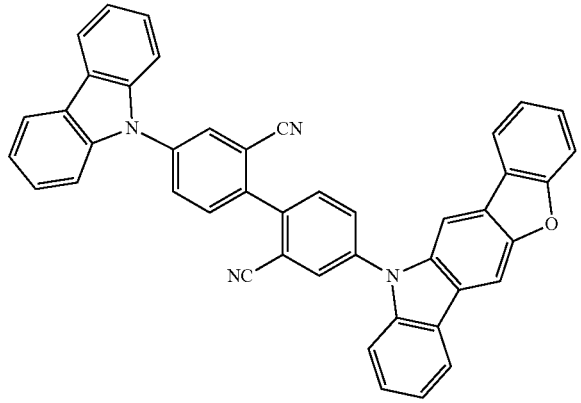
28
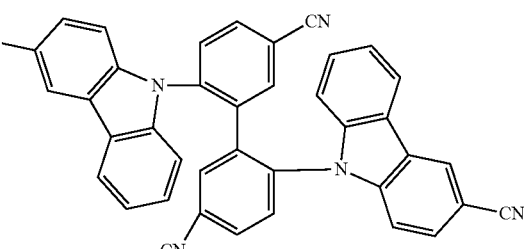
29
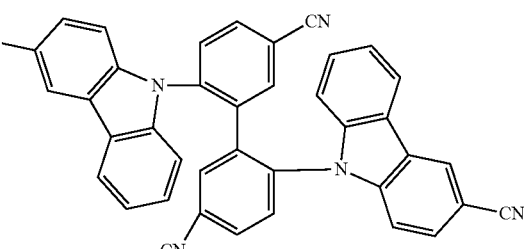
-continued
30
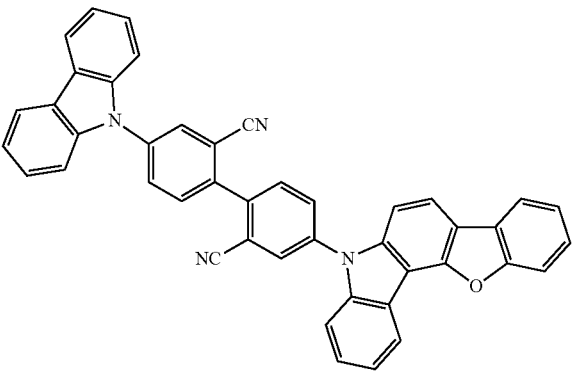
31
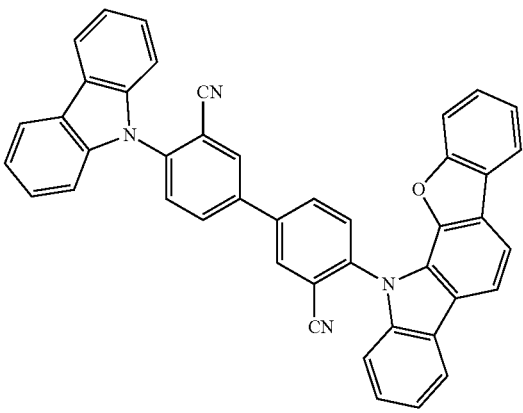
32
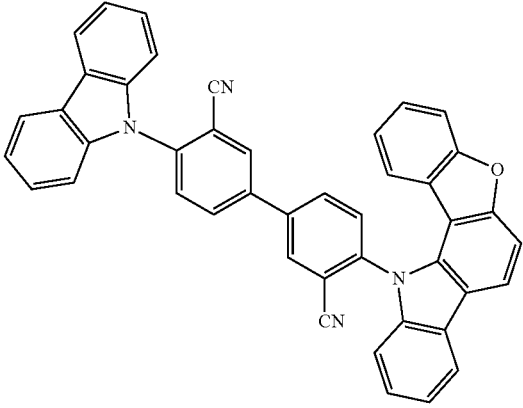
33
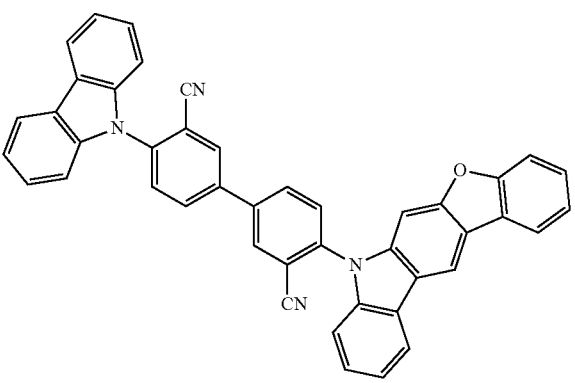

-continued
34
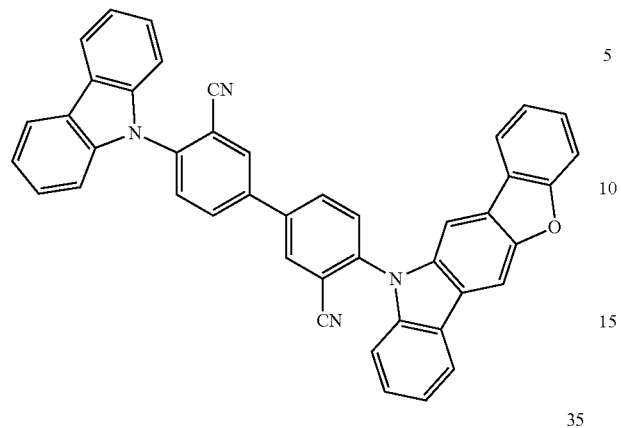
35
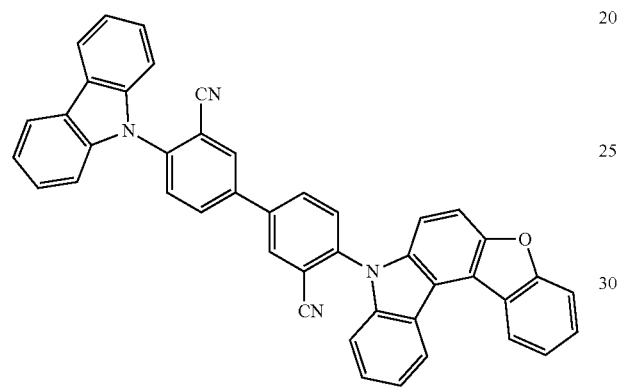
36
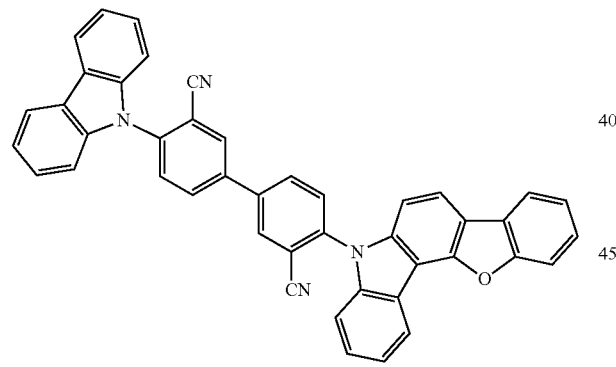
37
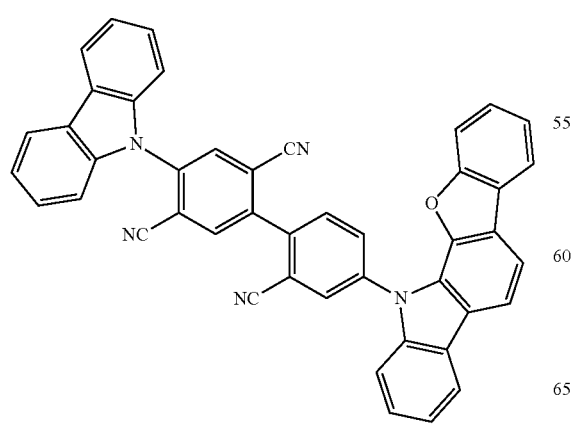
-continued
38
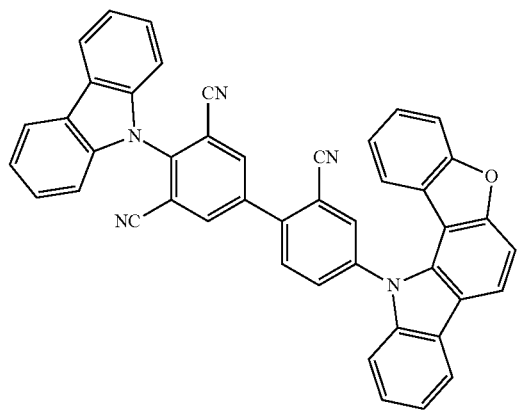
39
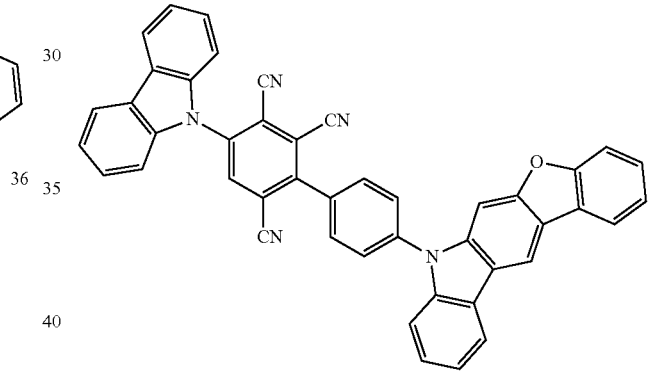
40
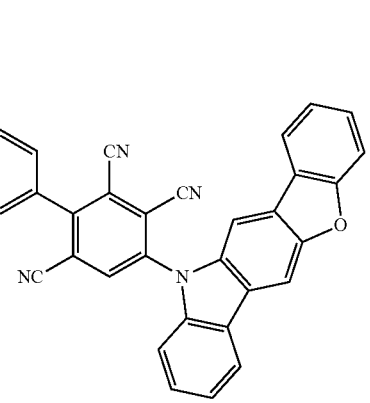

-continued
41
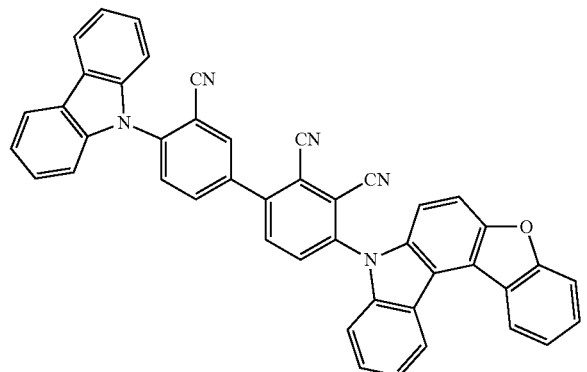
42
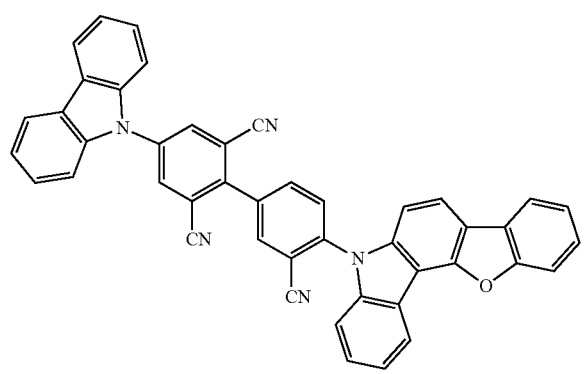
43
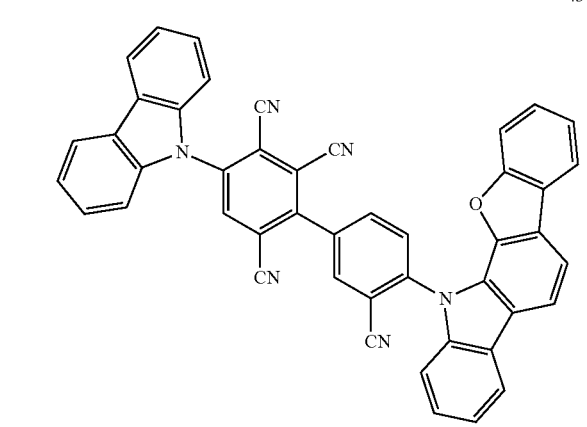
44
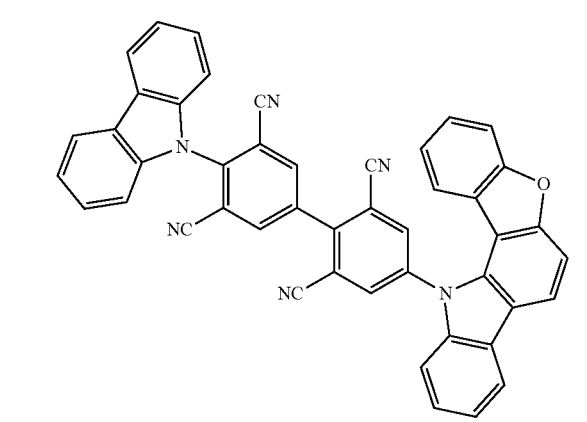
-continued
45
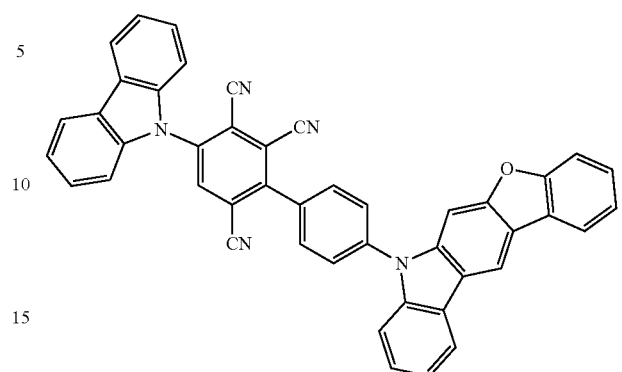
46
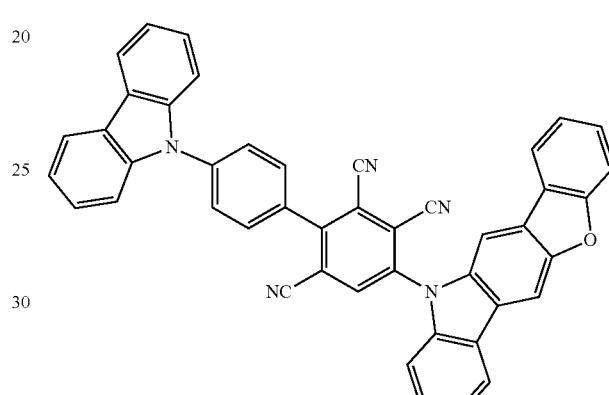
47
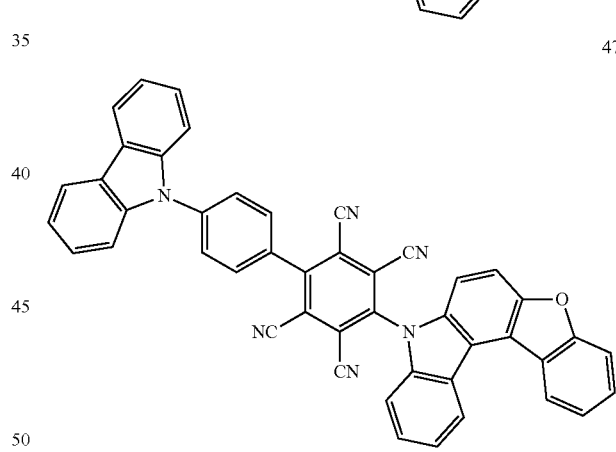
48
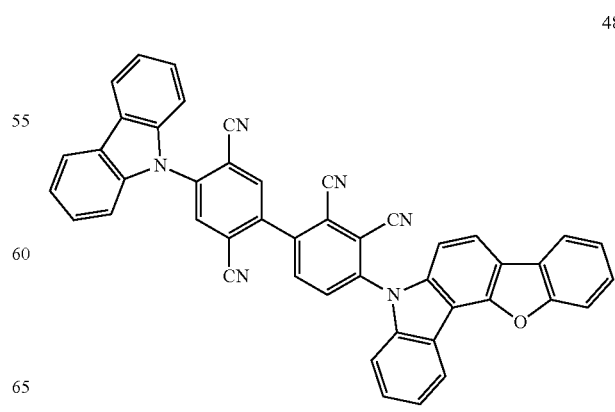

49
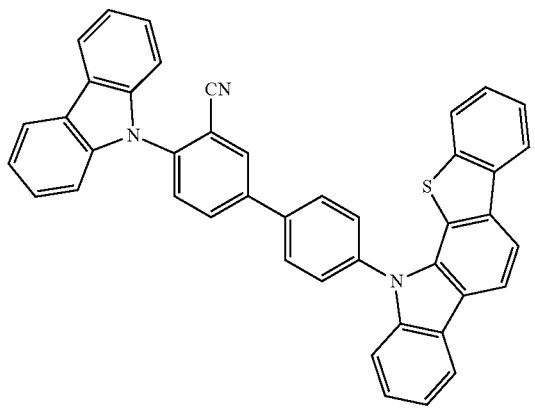
52
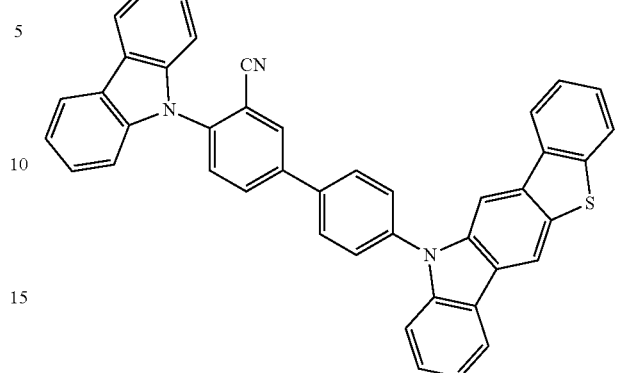
50
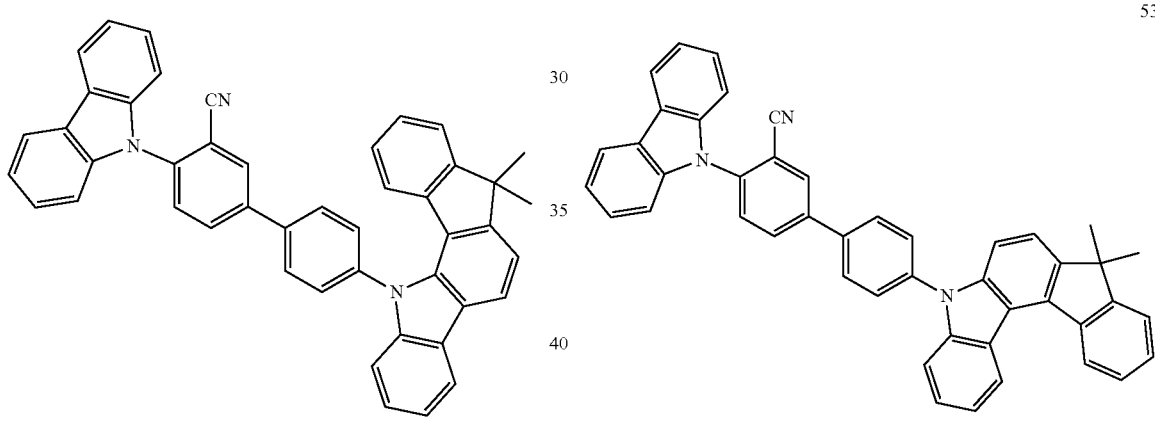
53
51
54
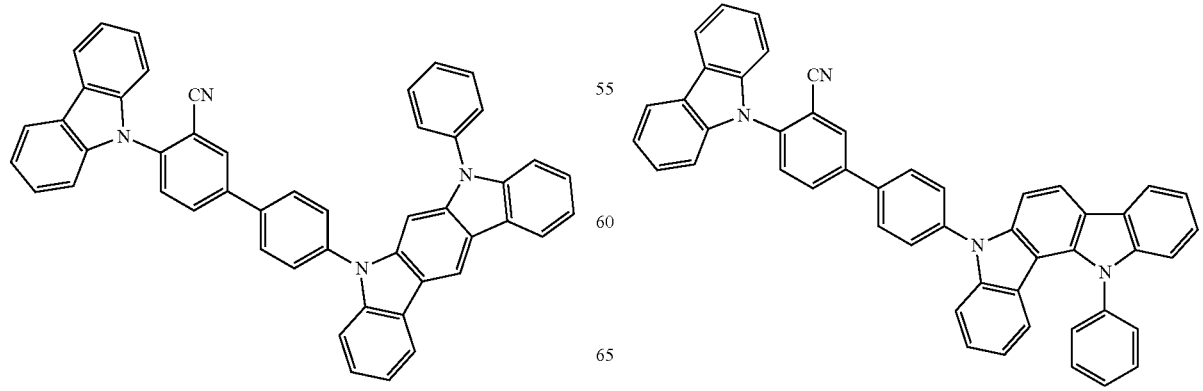

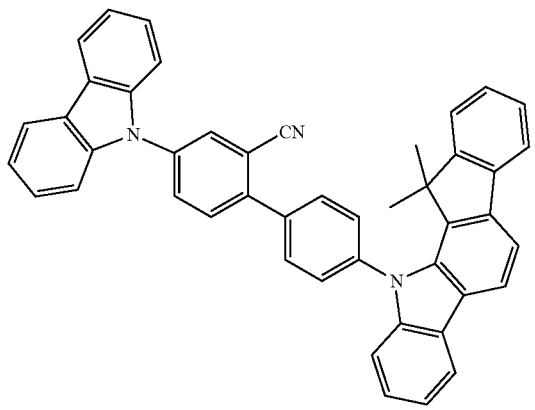
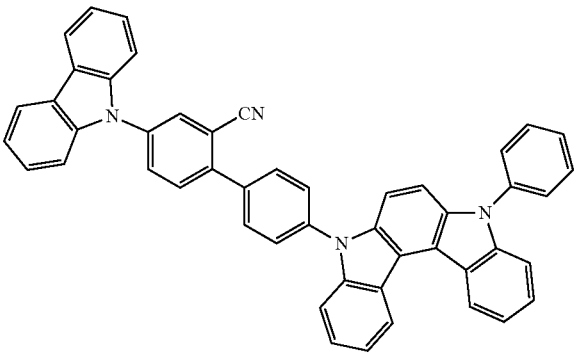
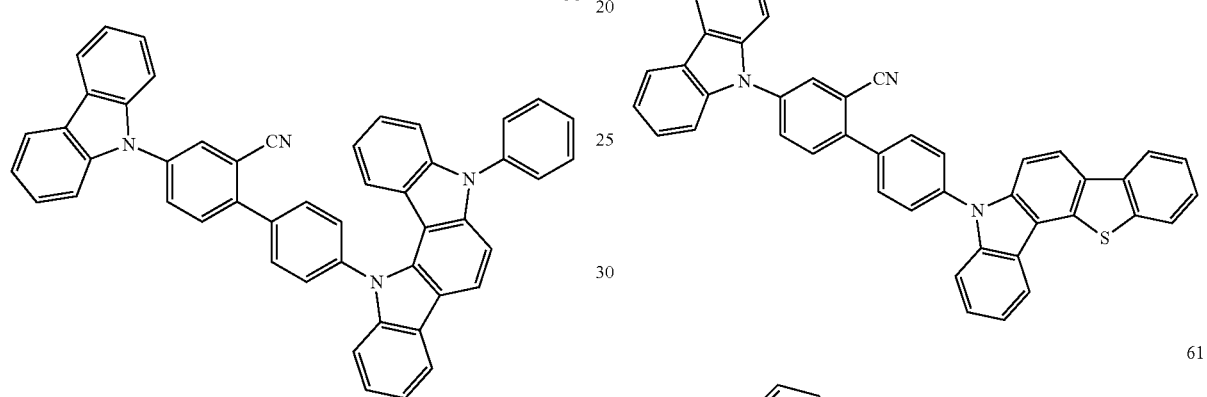
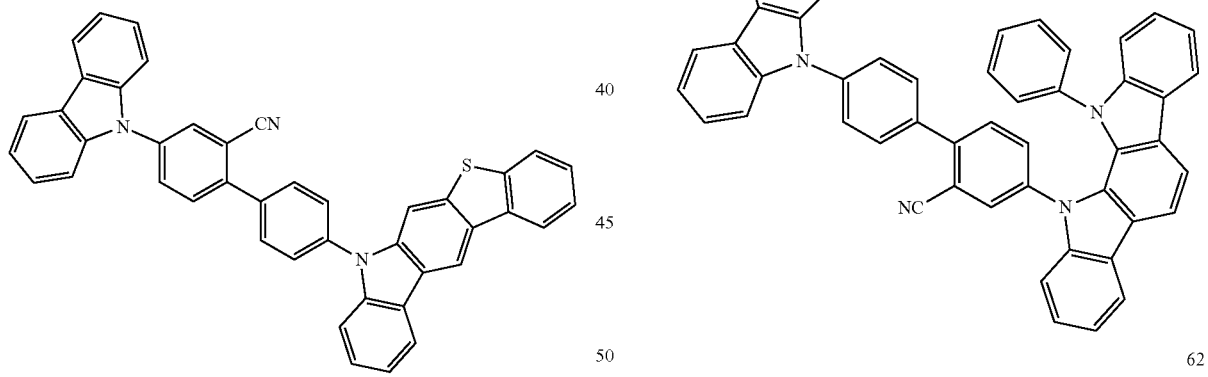
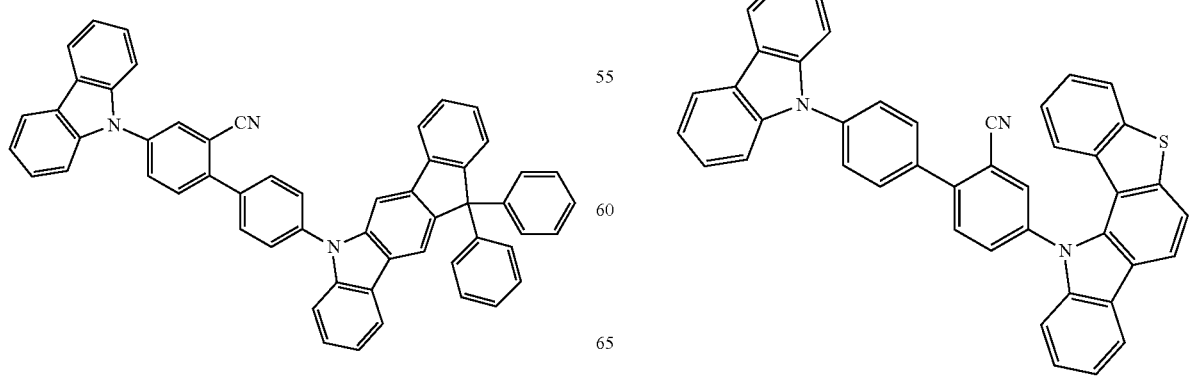

463
-continued
63
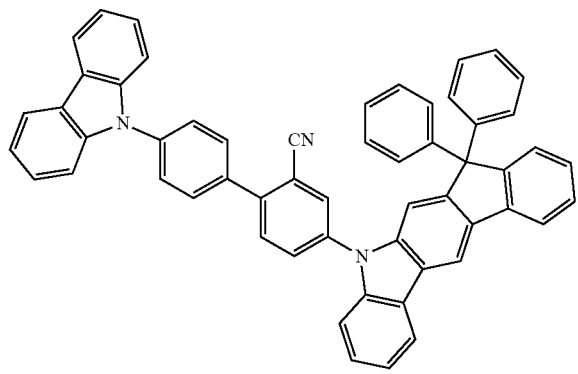
64
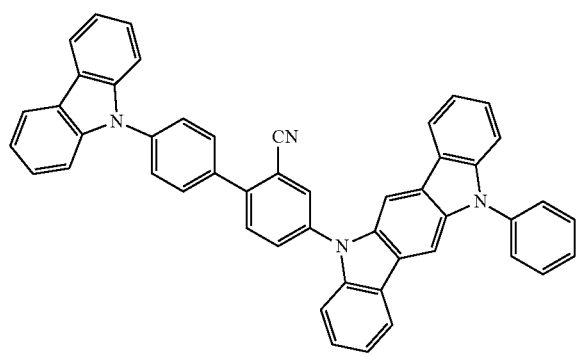
65
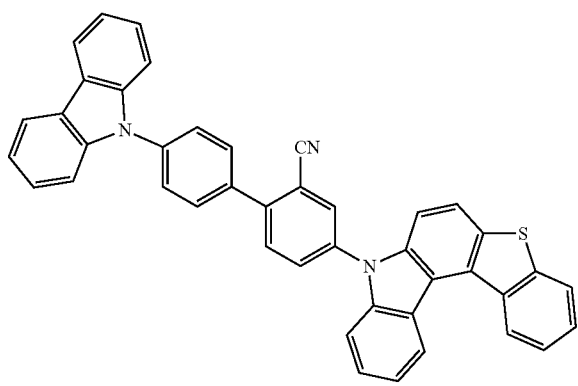
66
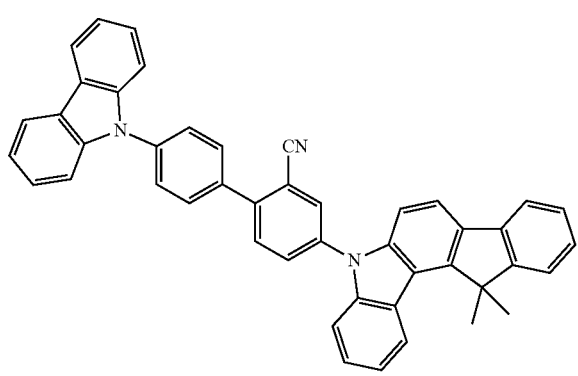
464
-continued
67
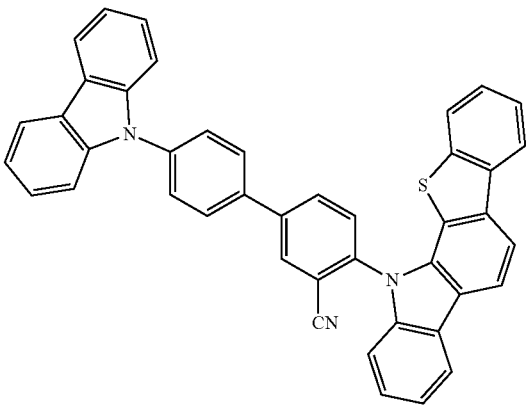
68
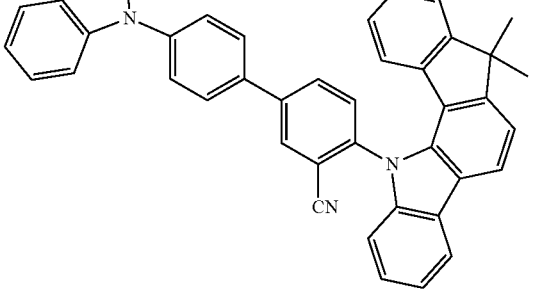
69
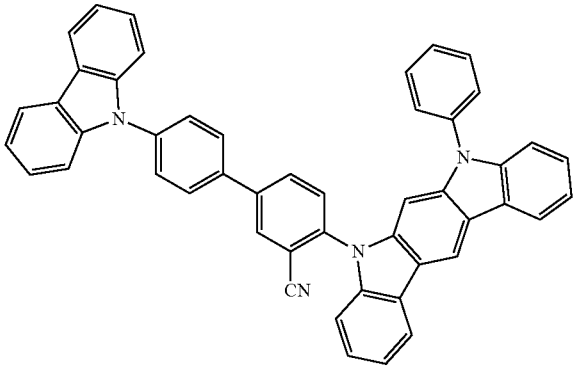

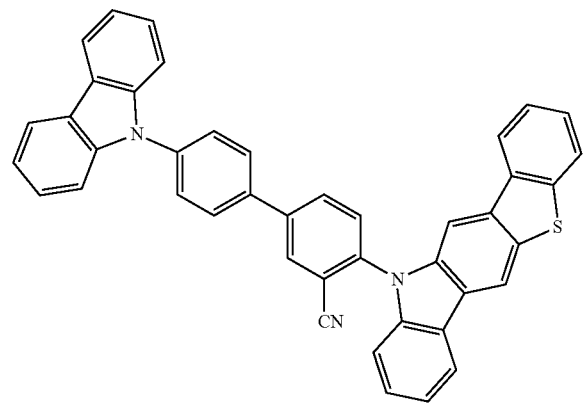
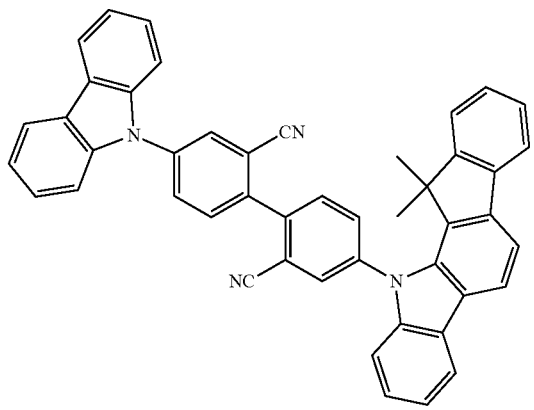
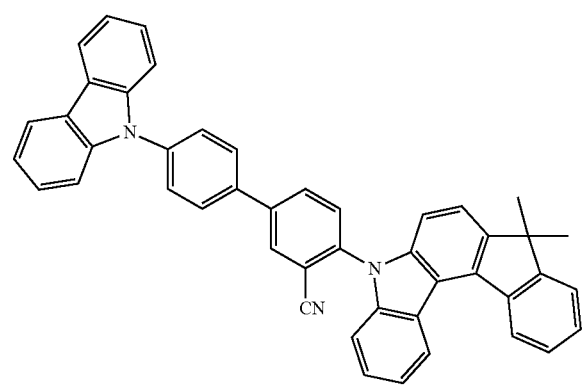
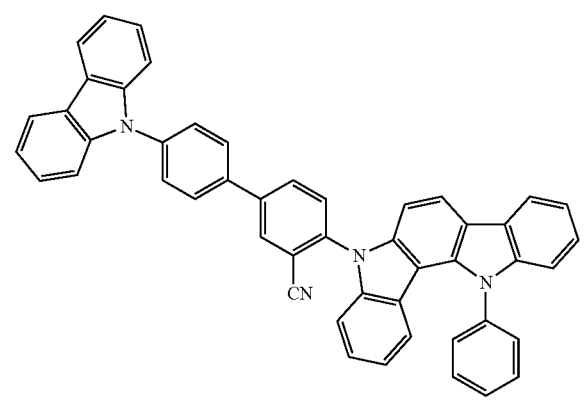
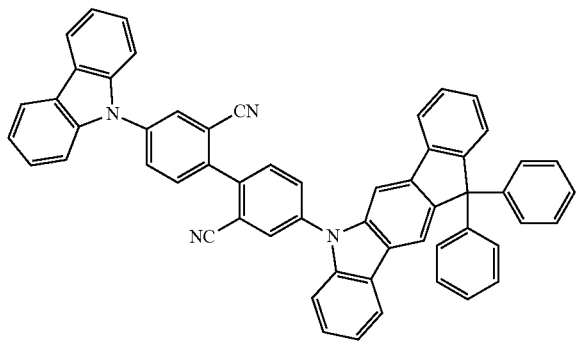

77
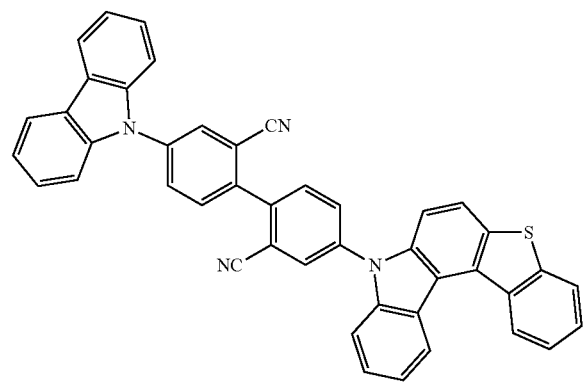
78
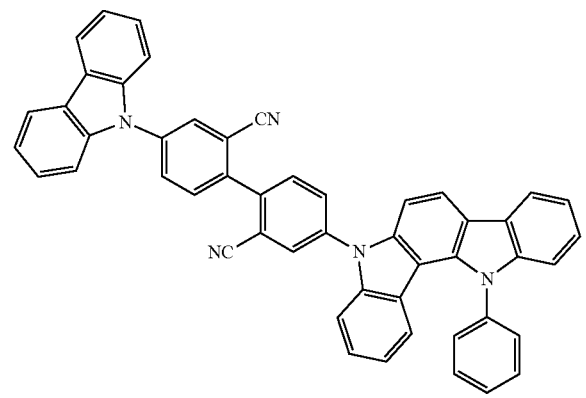
79
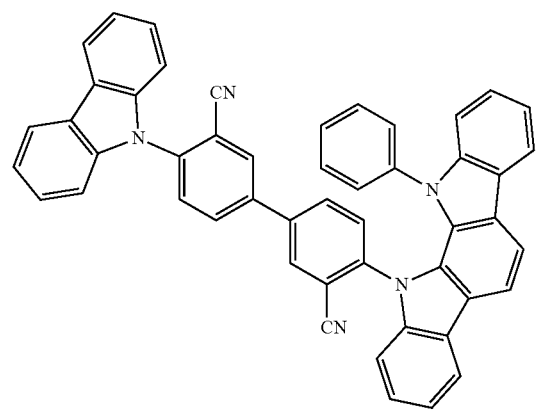
80
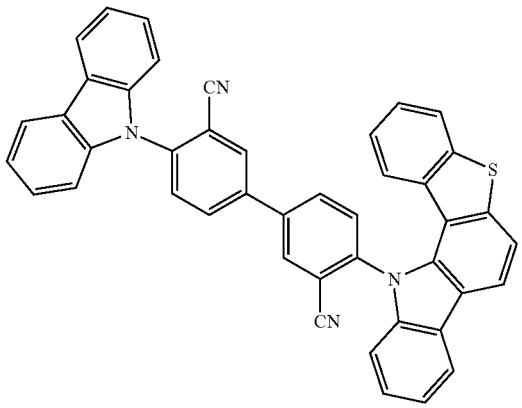
81
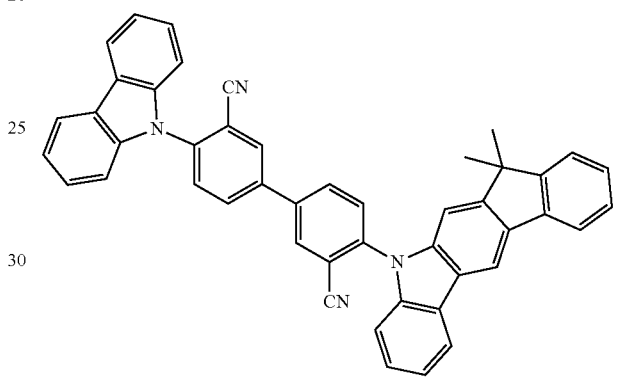
82
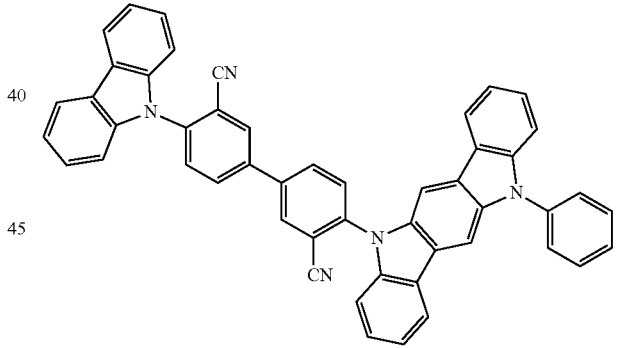
83
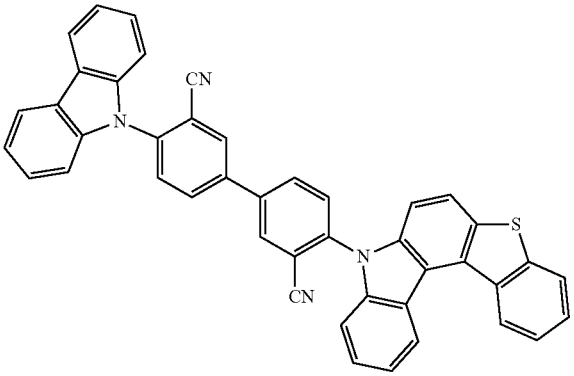

84
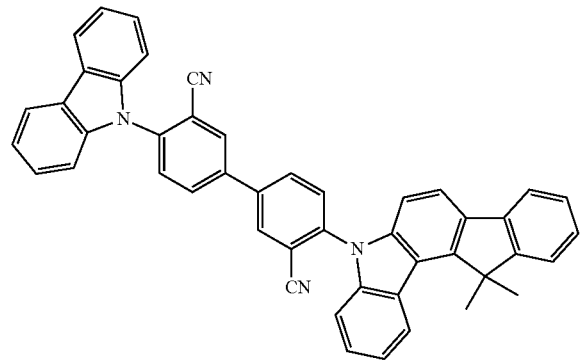
85
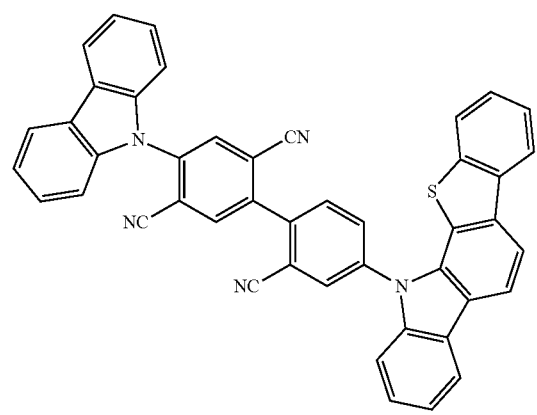
86
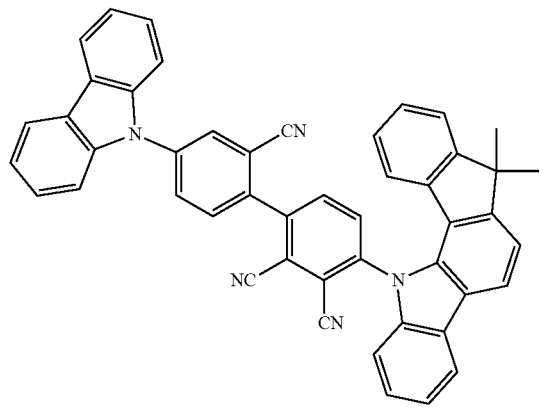
87
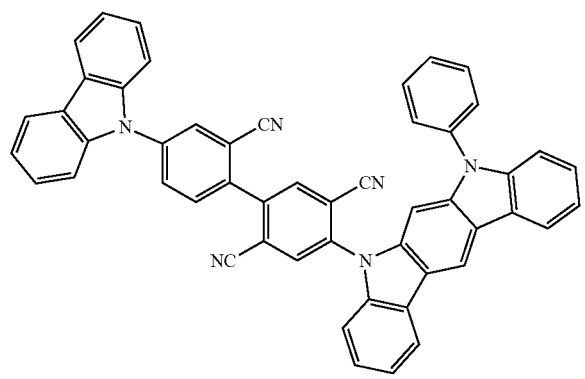
88
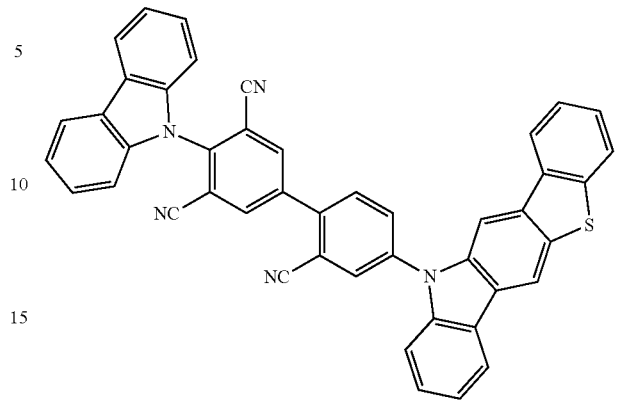
89
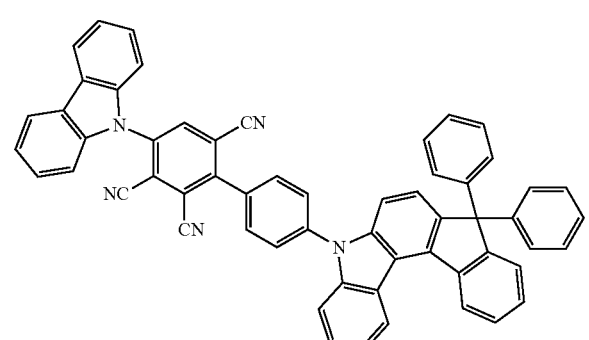
90
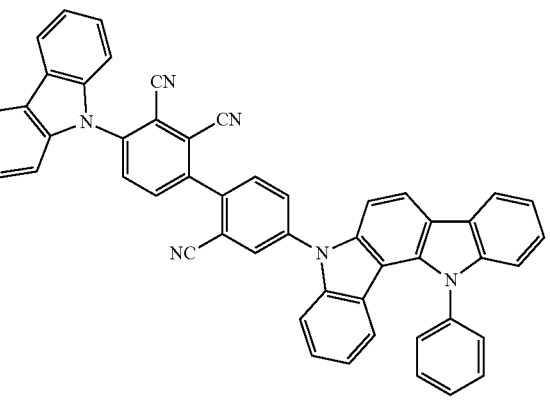
91
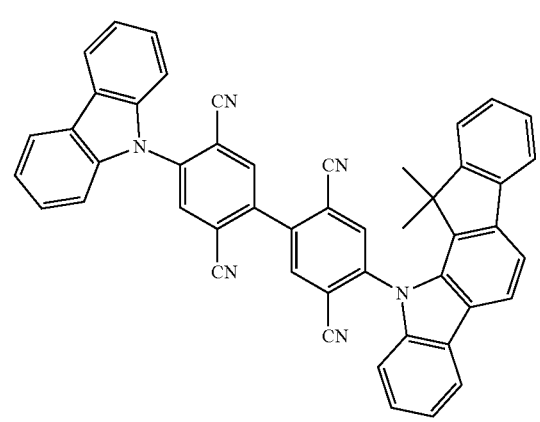

-continued
92
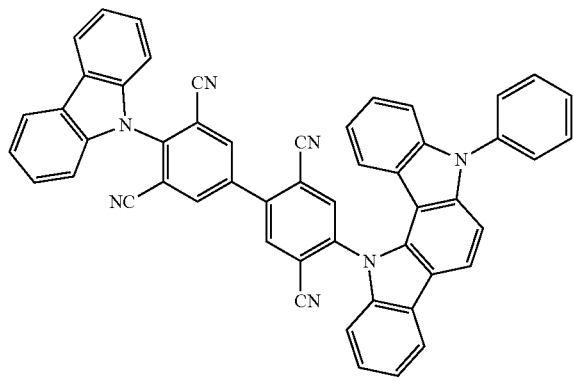
93
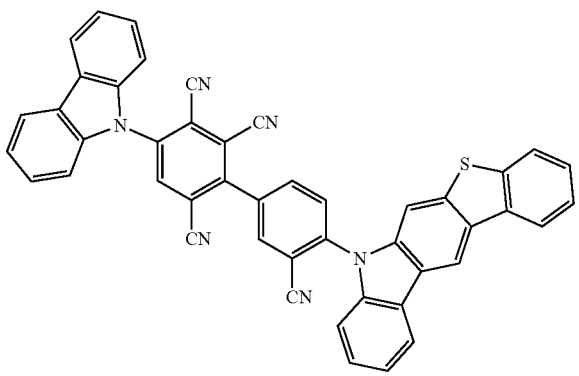
94
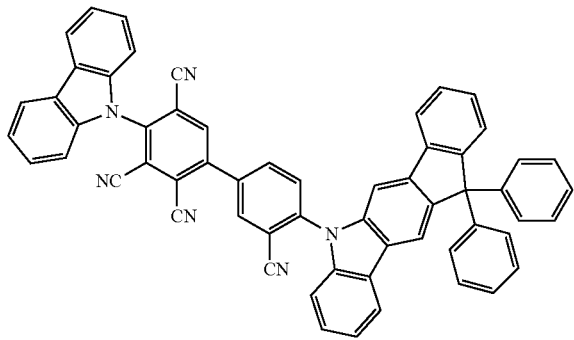
95
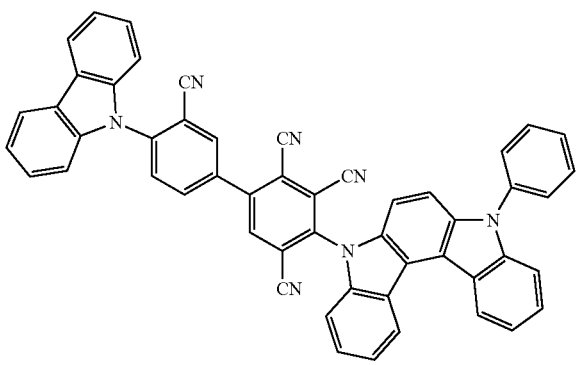
-continued
96
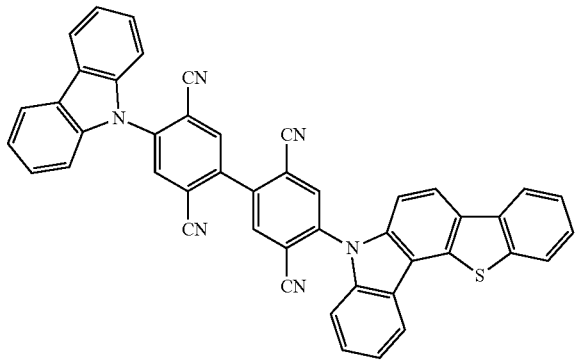
97
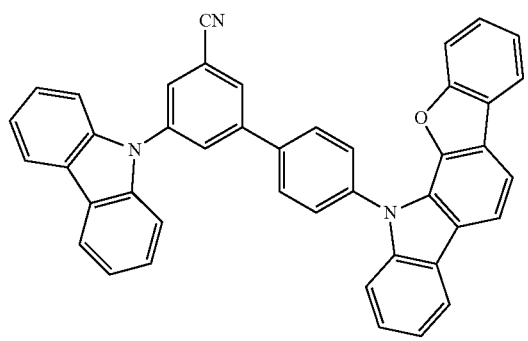
98
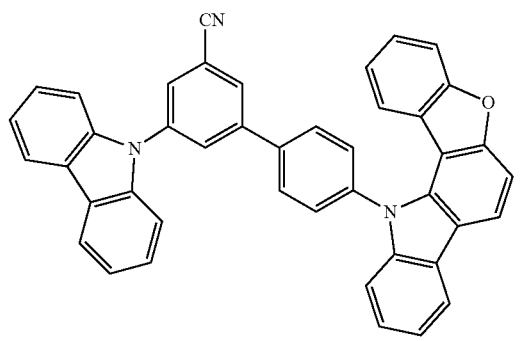
99
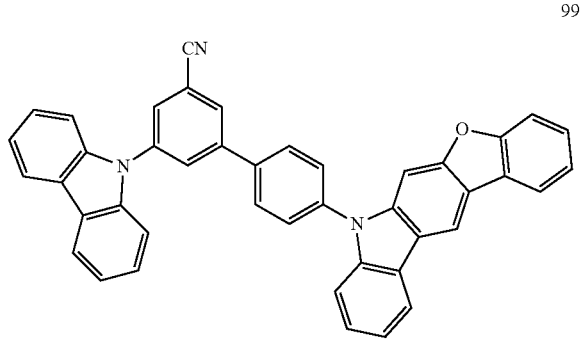

100
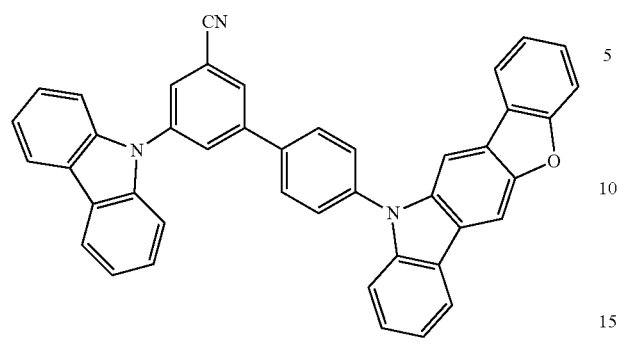
101
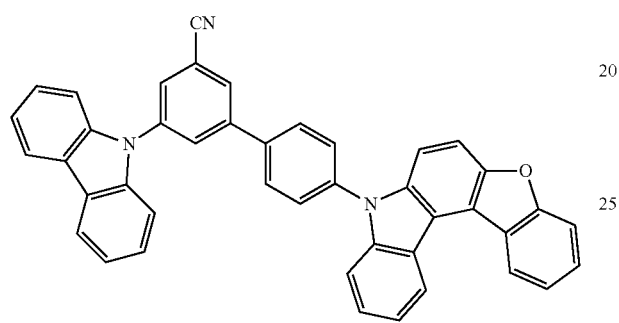
102
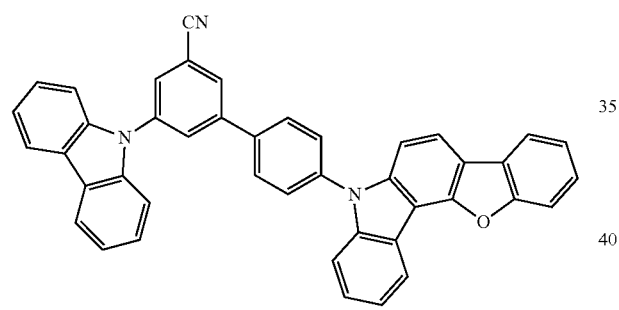
103
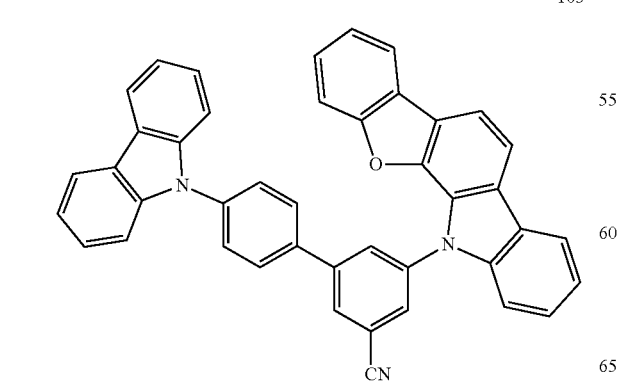
104
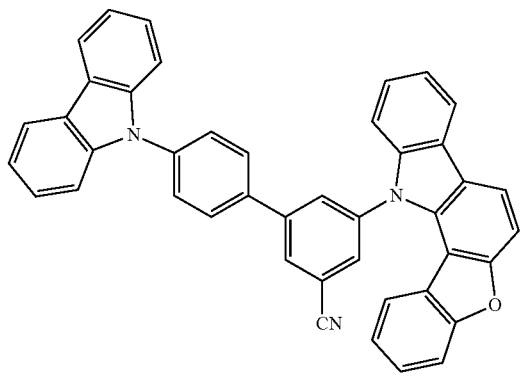
105
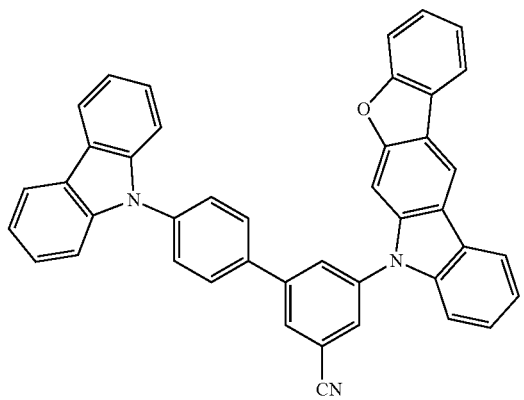
106
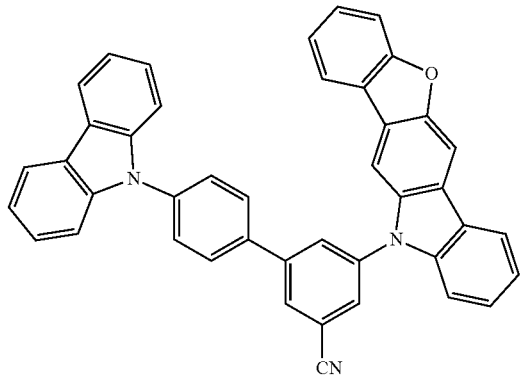
107
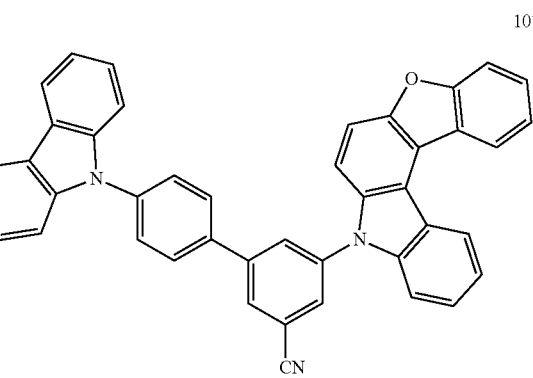

-continued
108
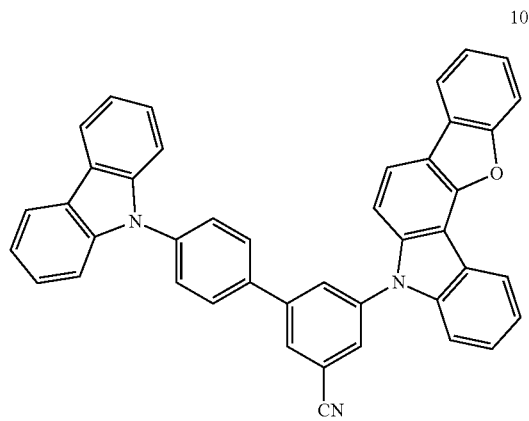
109
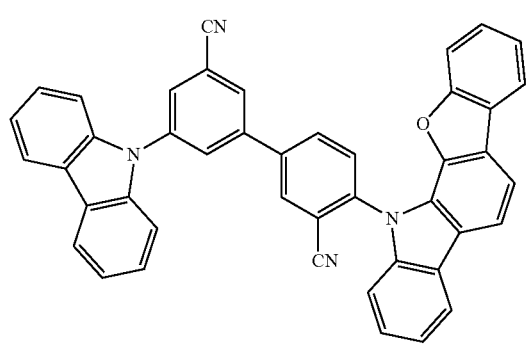
110
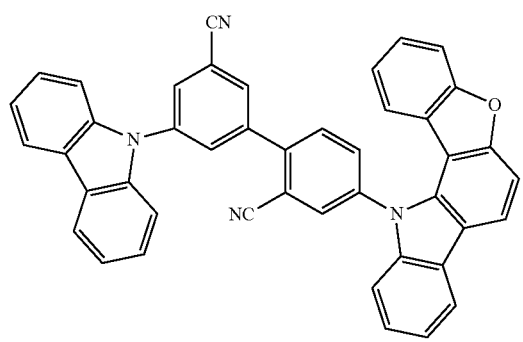
111
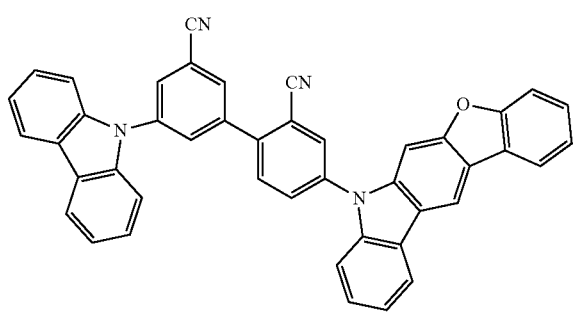
-continued
112
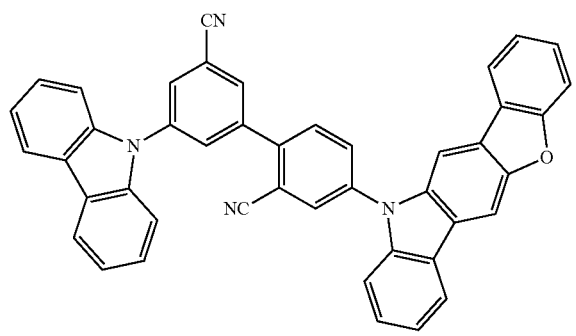
113
114
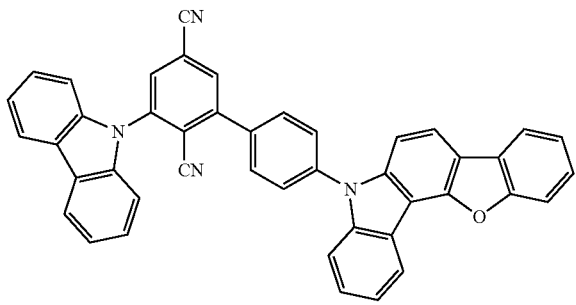
115
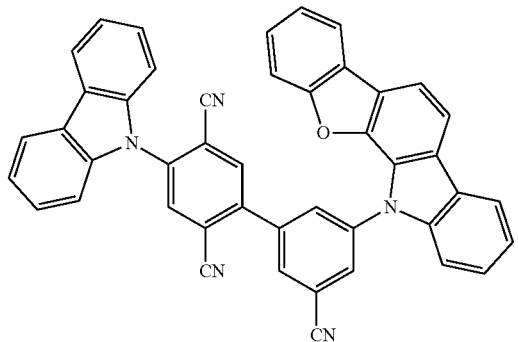

116
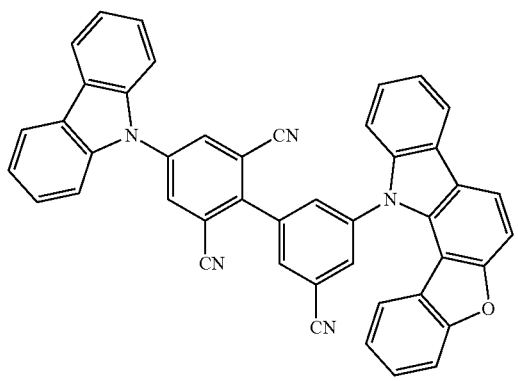
117
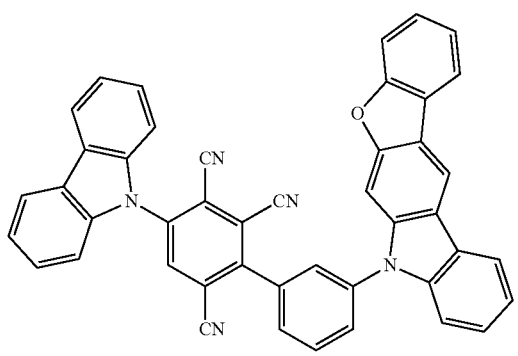
118
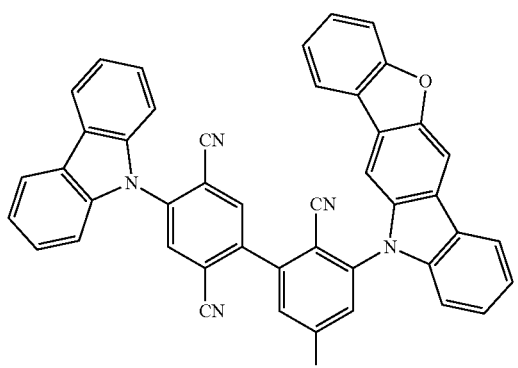
119
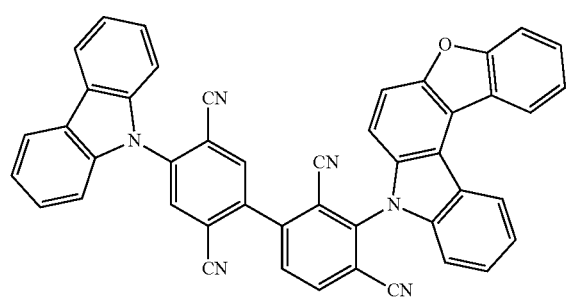
120
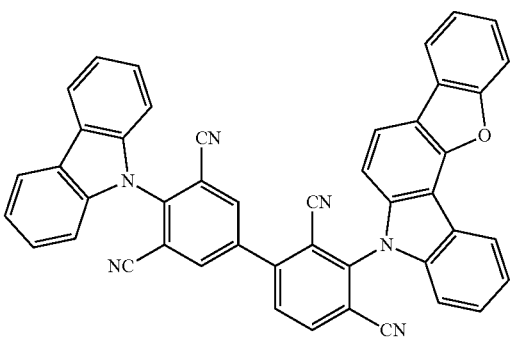
121
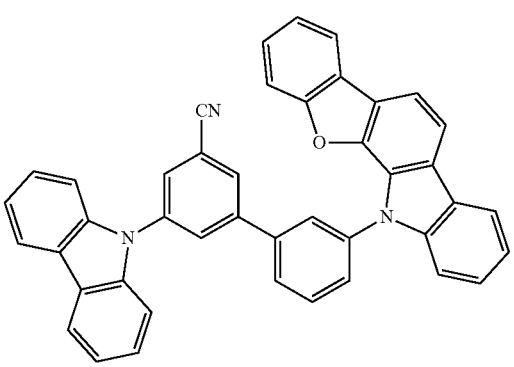
122
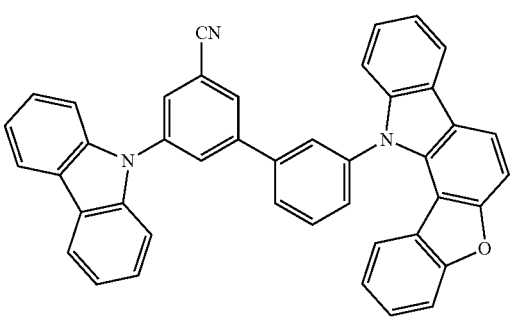
123
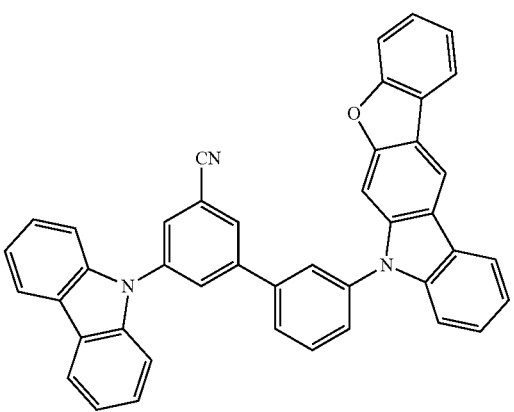

-continued
124
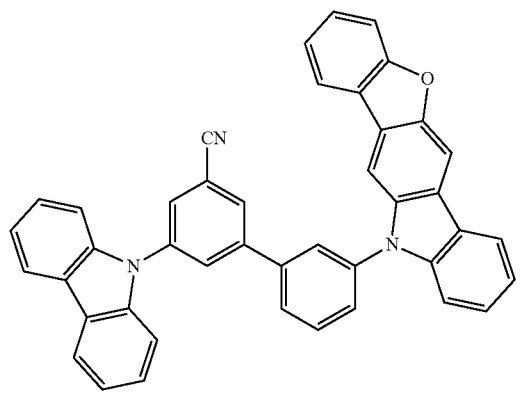
125
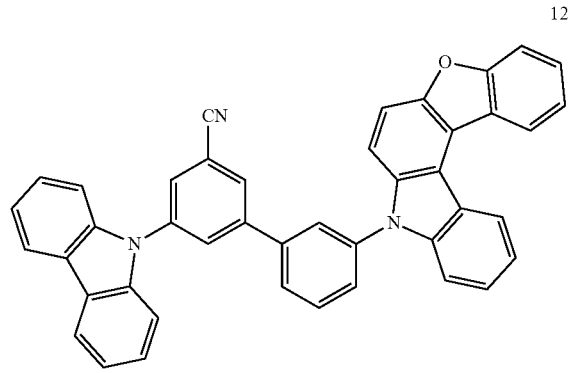
126
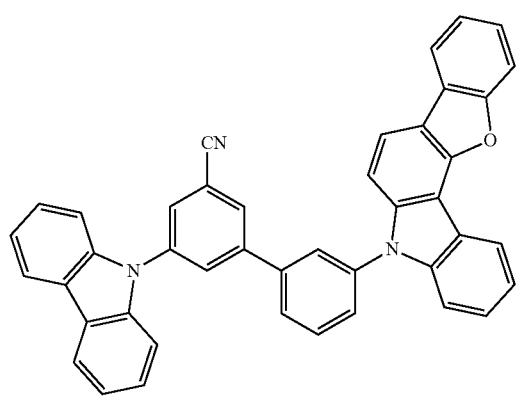
127
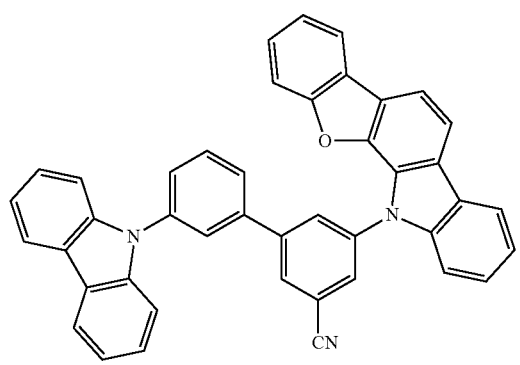
-continued
128
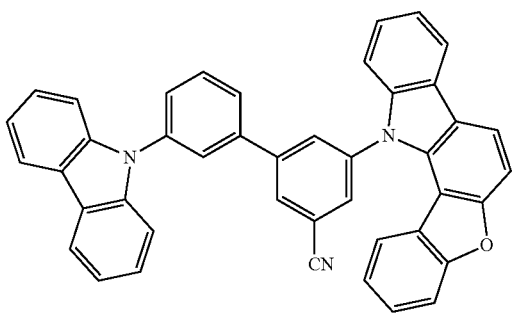
129
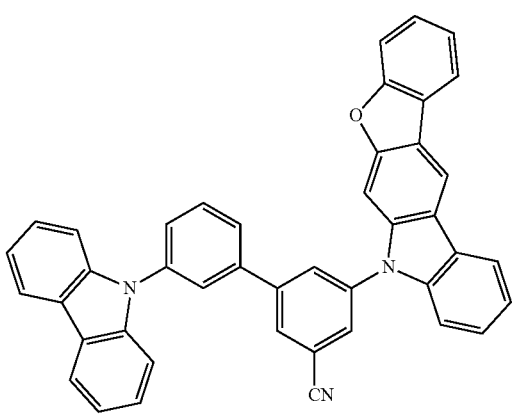
130
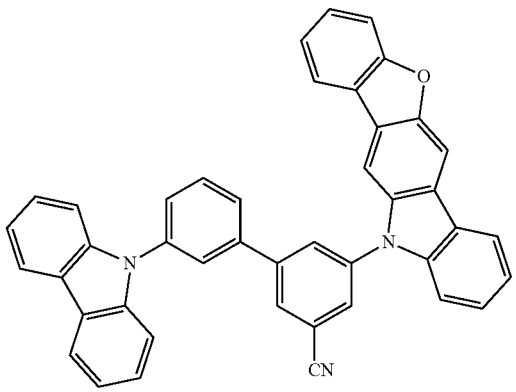
131
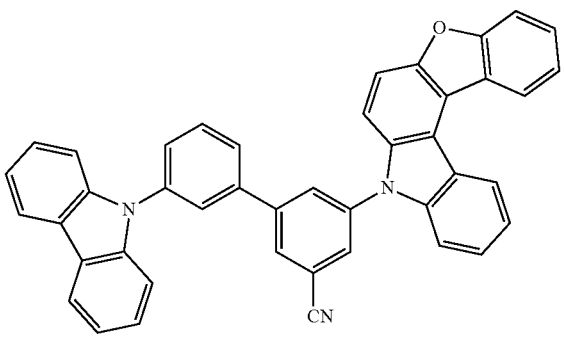

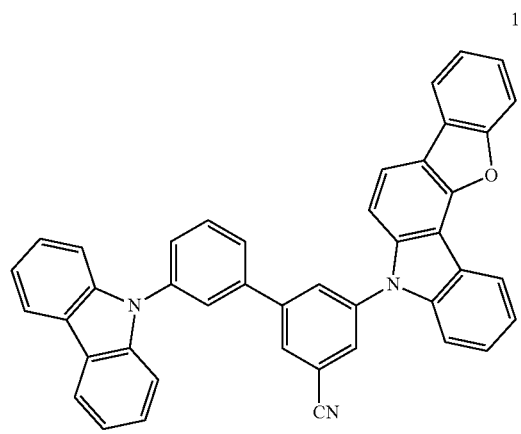
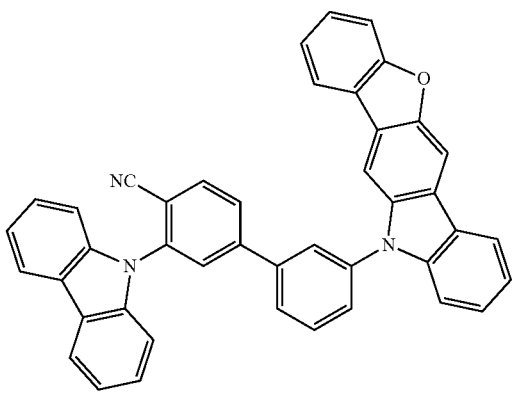

-continued
140
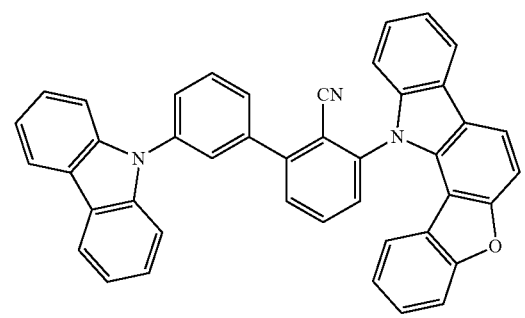
141
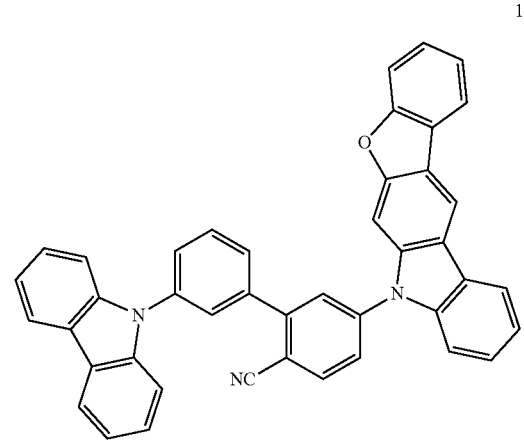
142

143
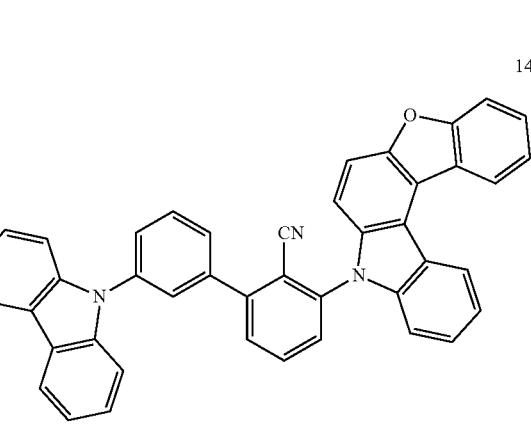
-continued
144
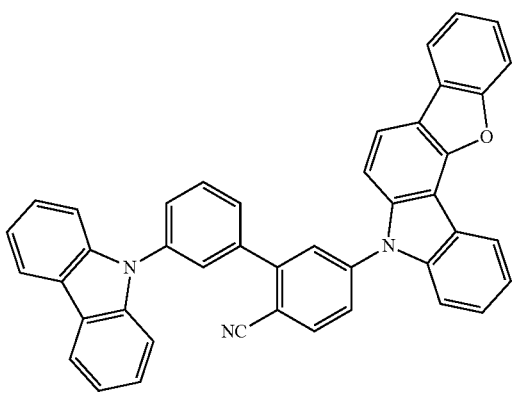
145
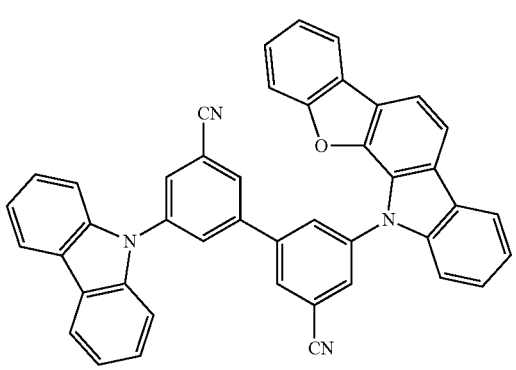
146
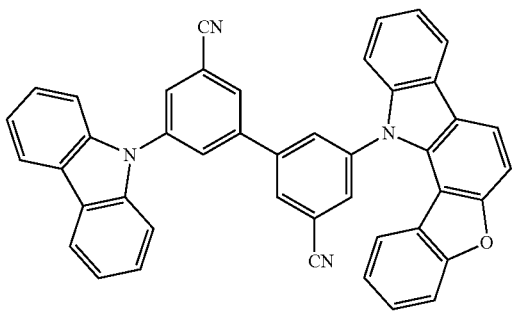
147
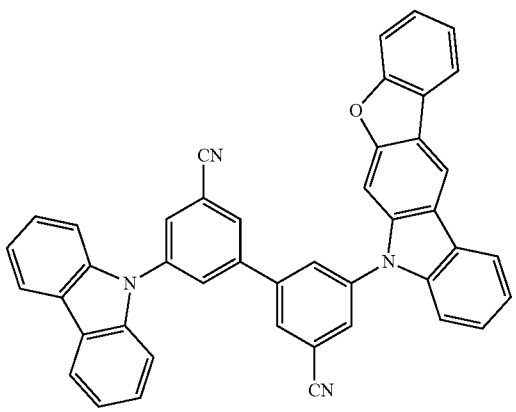

148
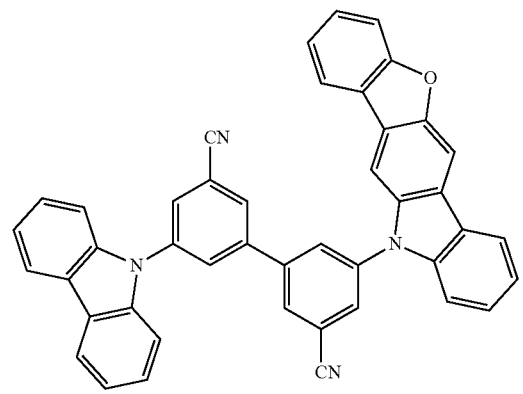
149
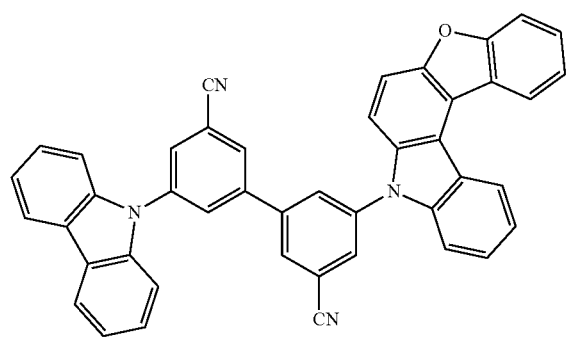
150
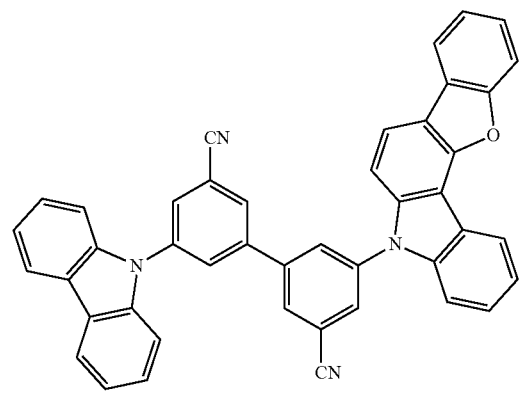
151
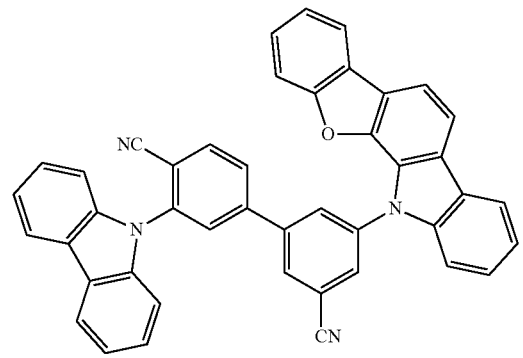
152
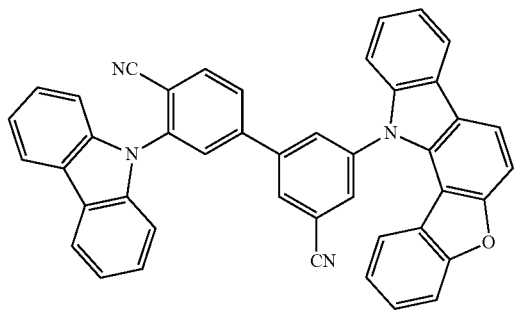
153
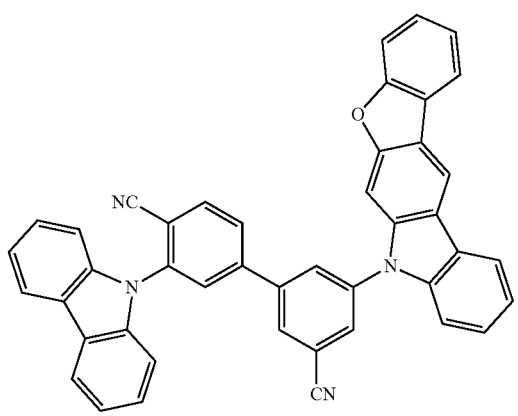
154
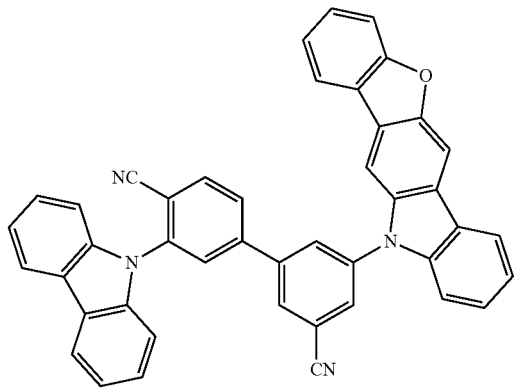
155
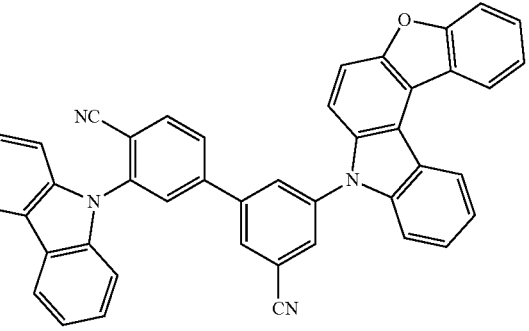

-continued

156

157

158

159

160

161

162

163

164
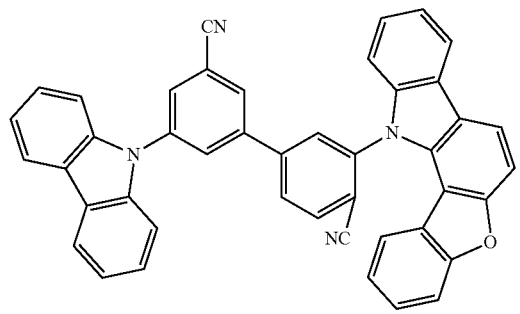
165
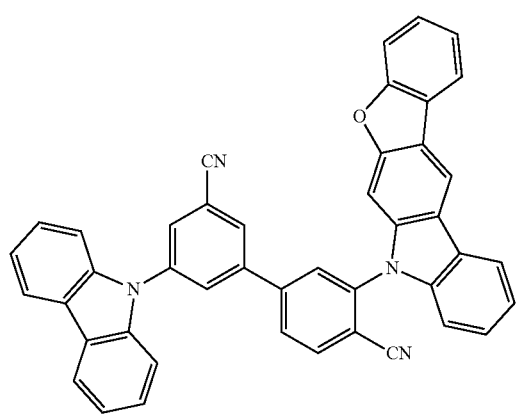
166
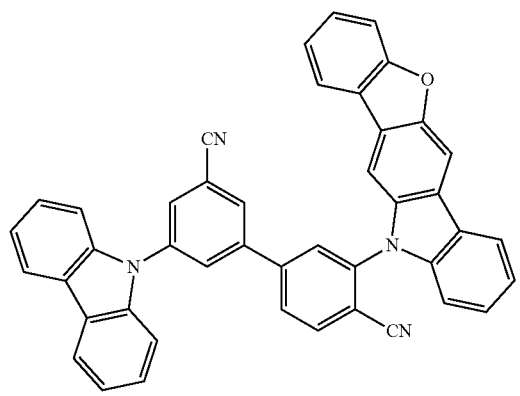
167
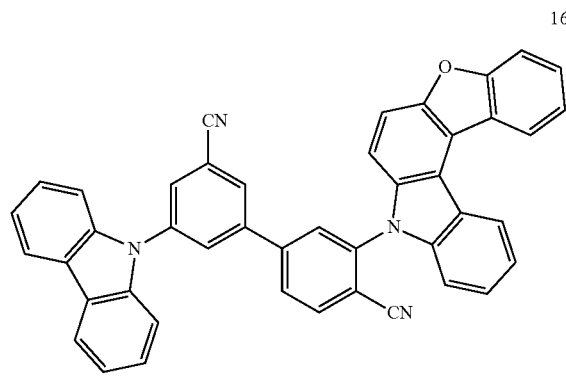
168
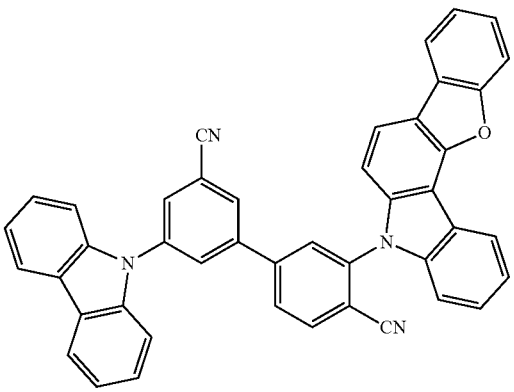
169
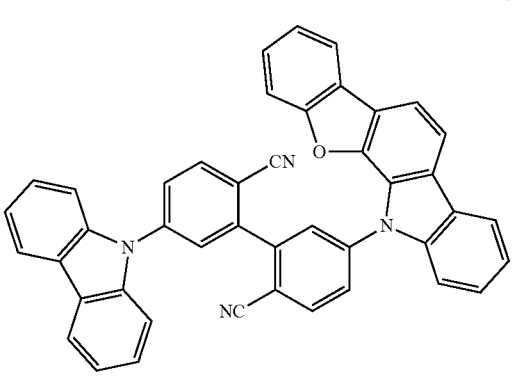
170
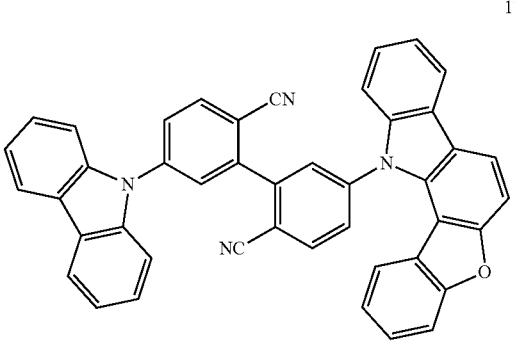
171
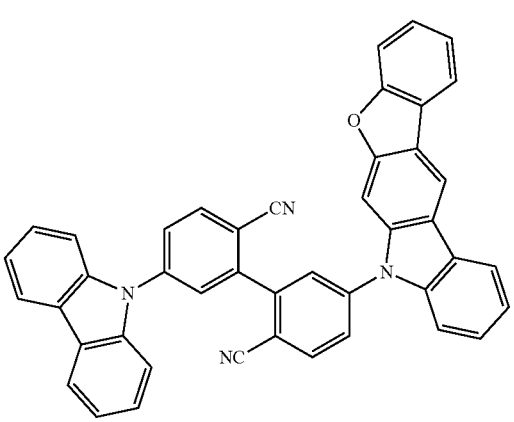

491
-continued
172
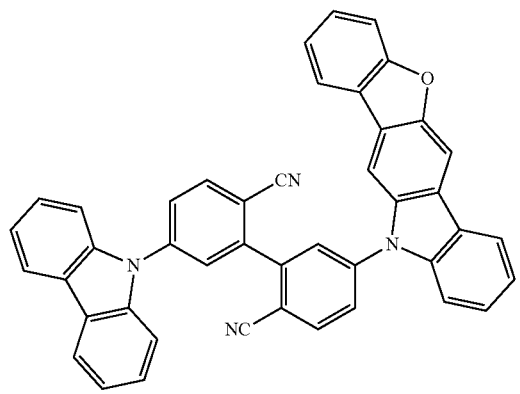
173
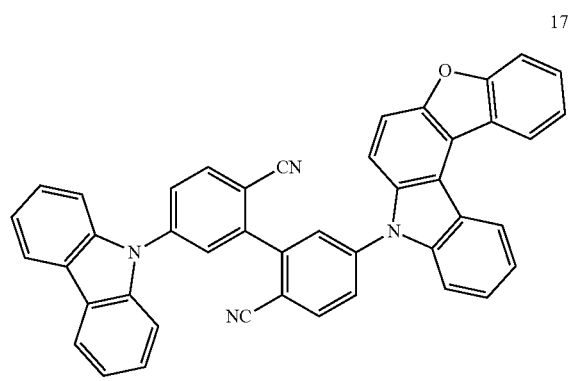
174
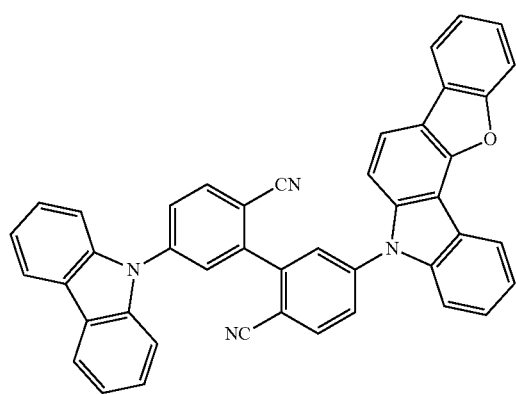
175
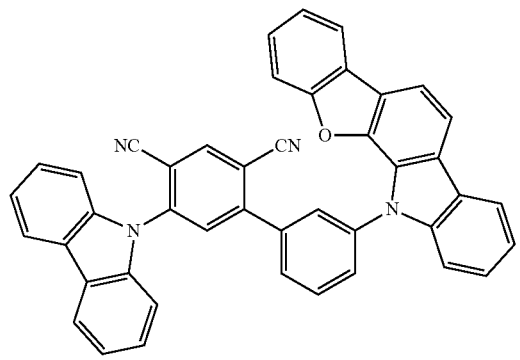
492
-continued
176
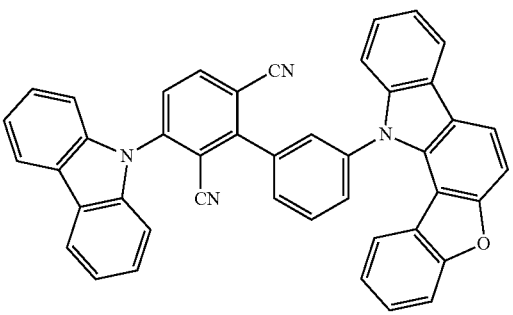
177
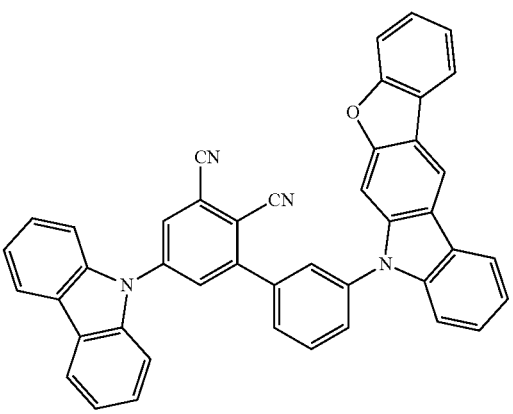
178
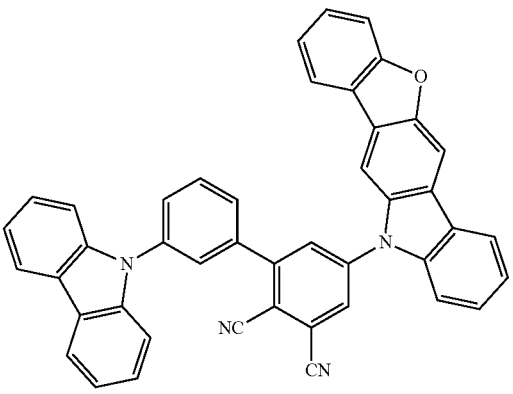
179
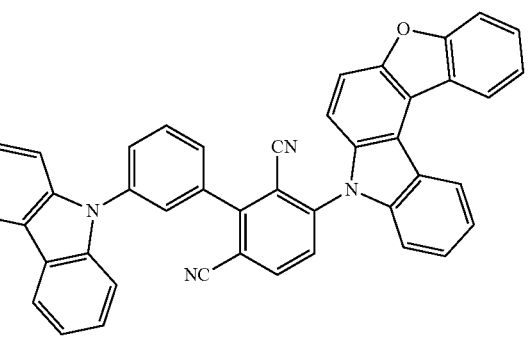

493
-continued
180
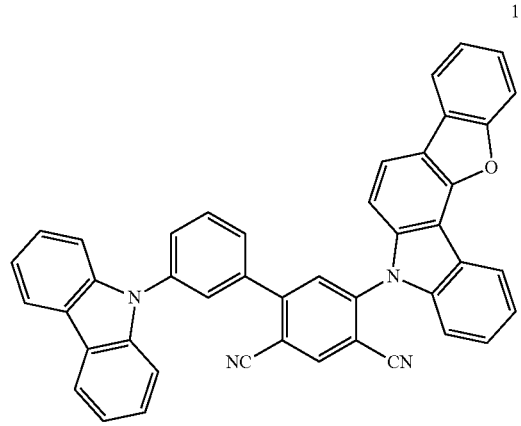
181
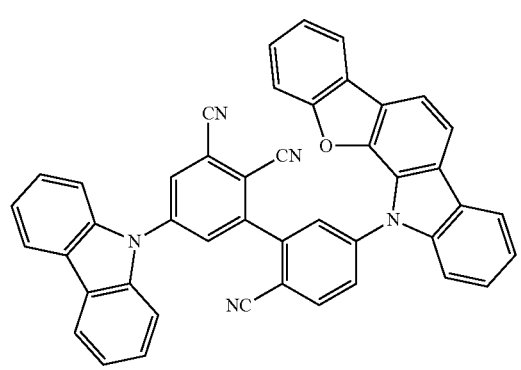
182
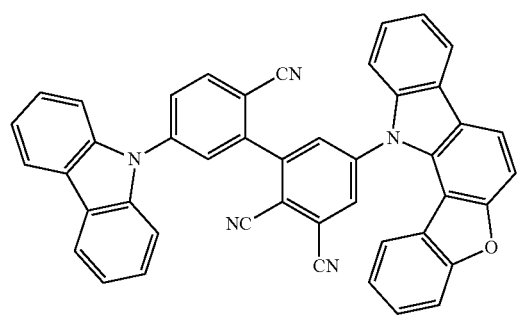
183
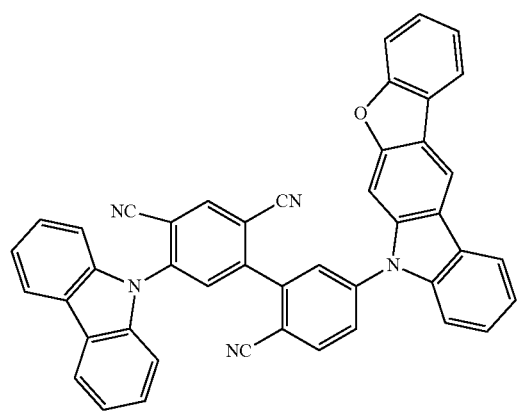
494
-continued
184
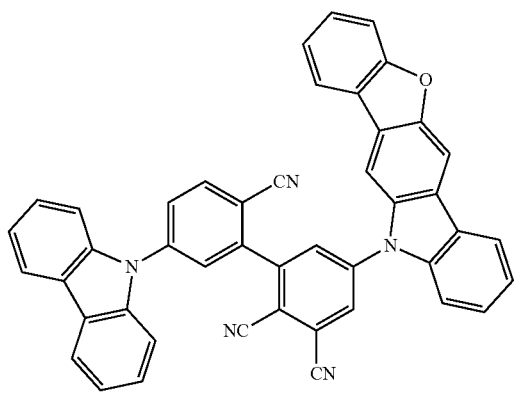
185
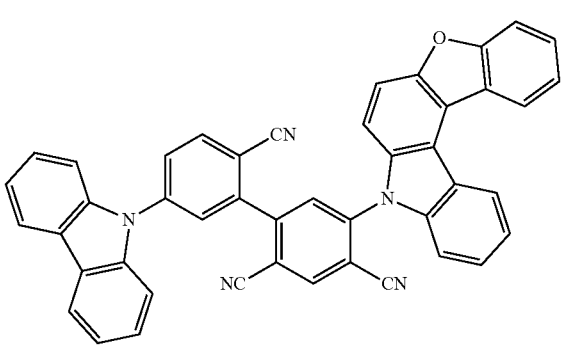
186
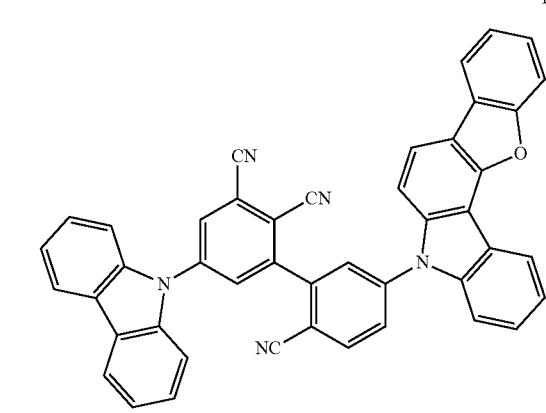
187
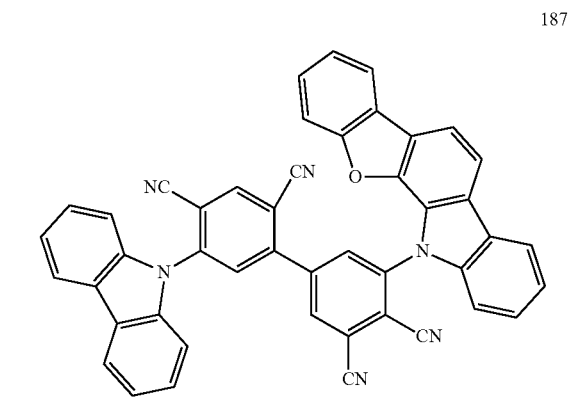

-continued
188
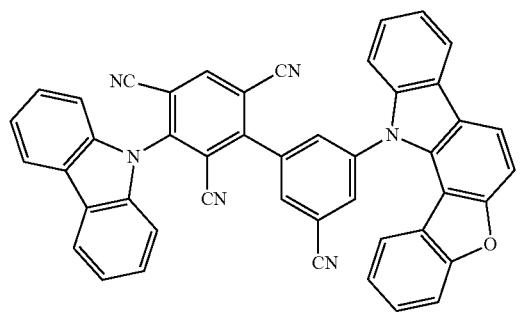
189
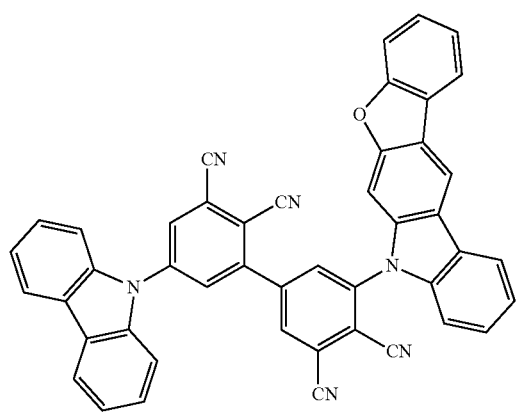
190
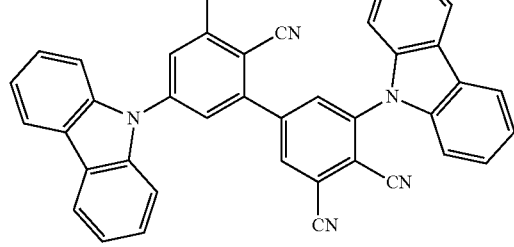
191
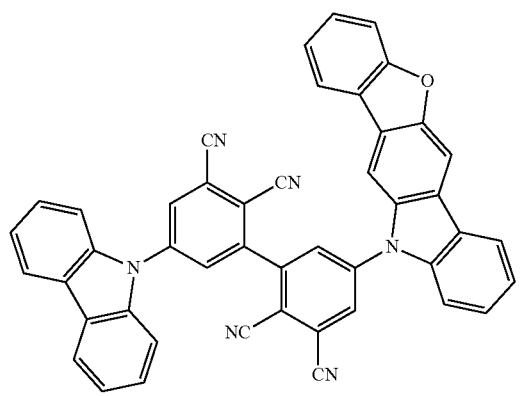
-continued
192
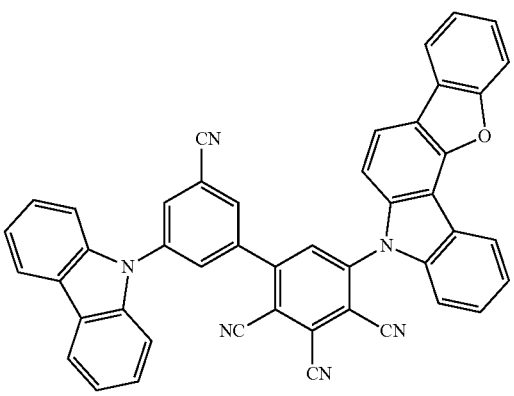
193
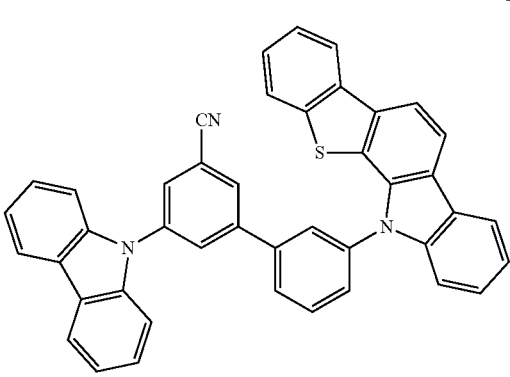
194
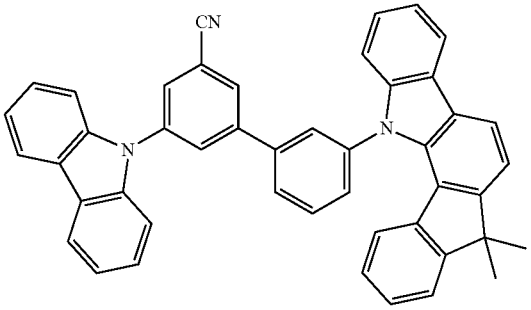
195
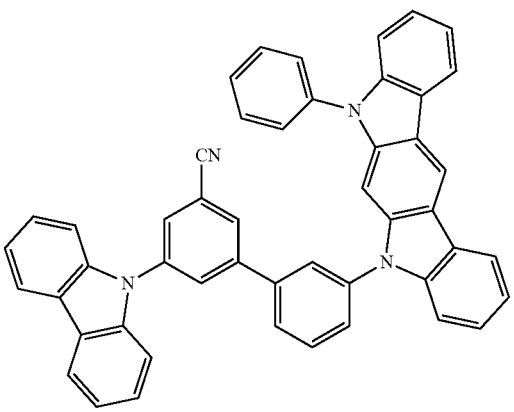

-continued
196
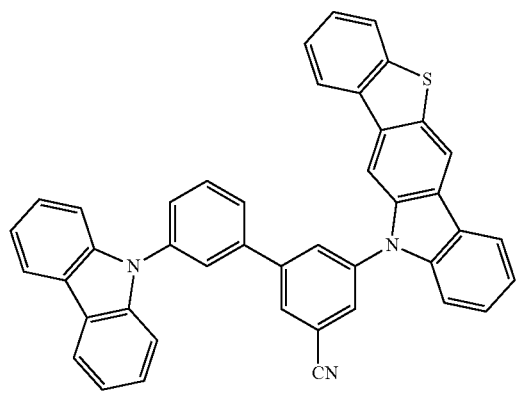
197
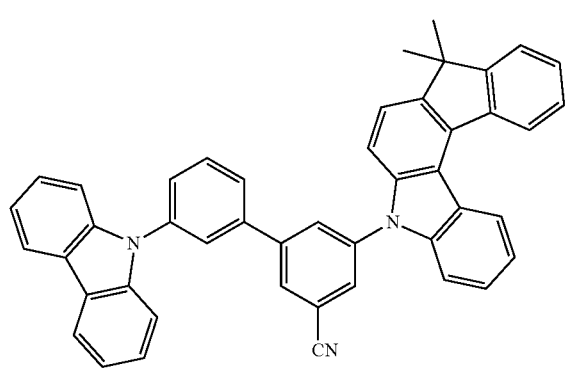
198
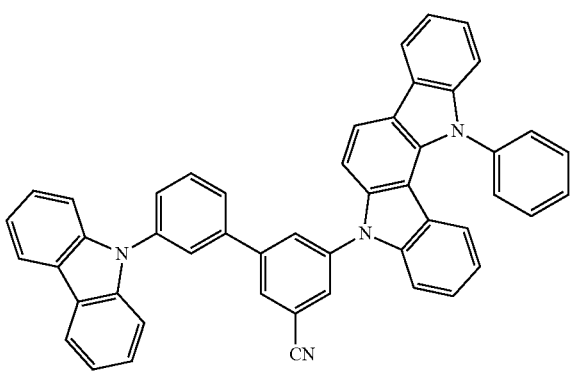
199
-continued
200
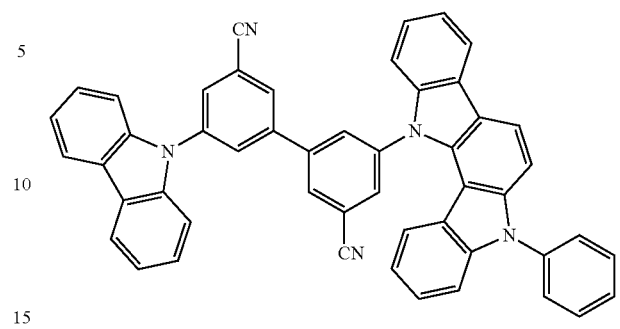
201
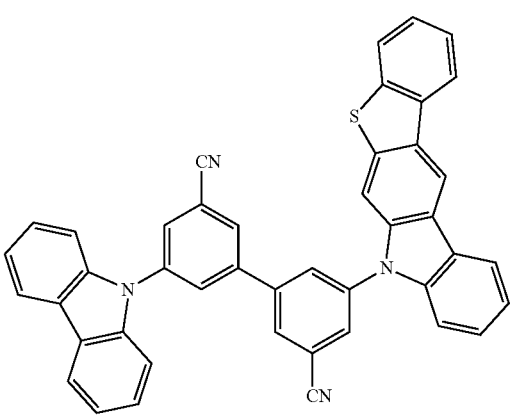
202
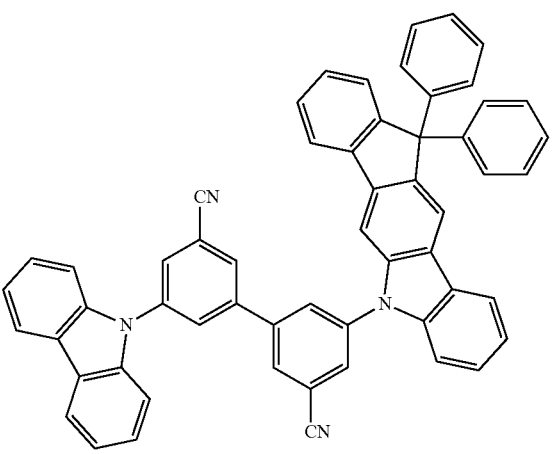

-continued
203
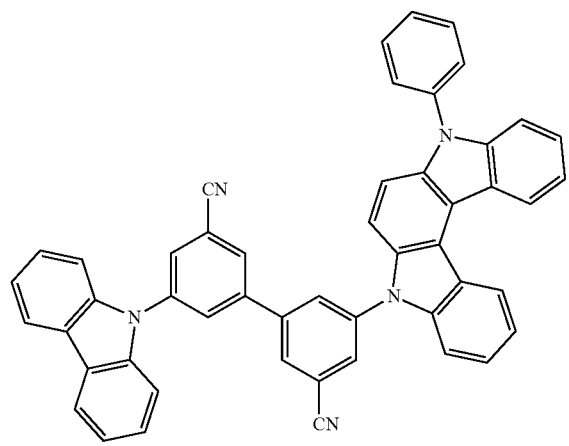
204
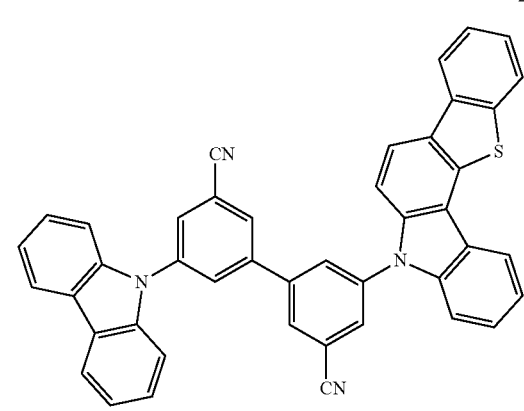
205
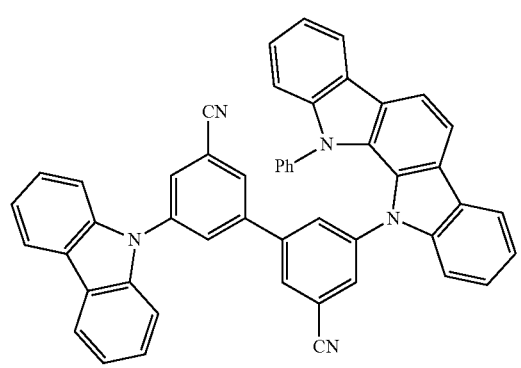
206
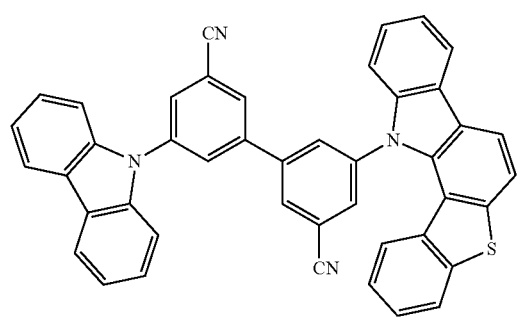
-continued
207
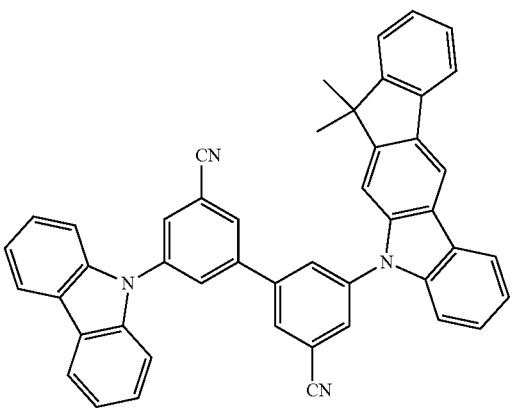
208
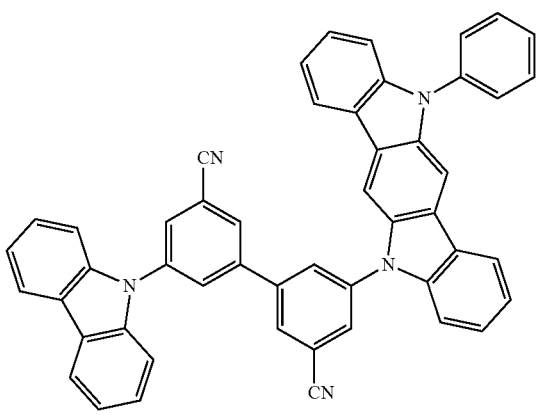
209
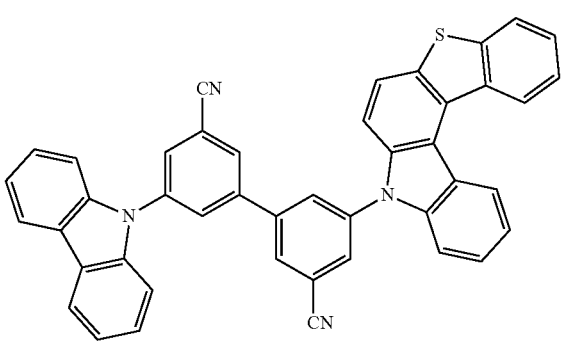
210
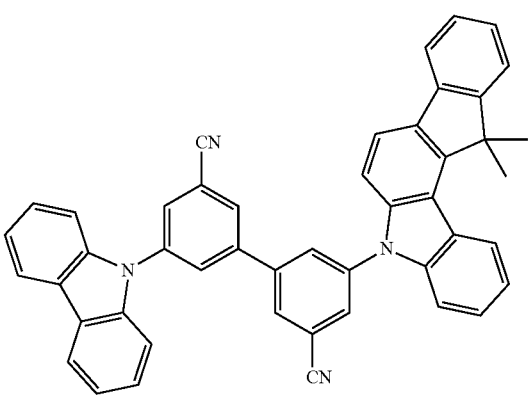

211
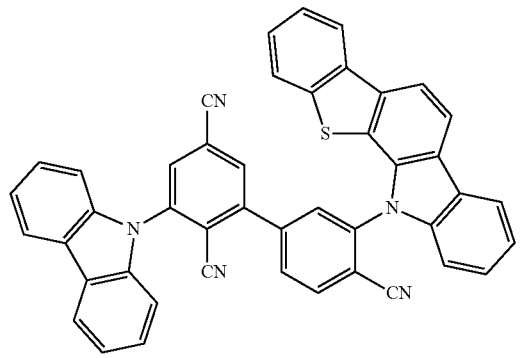
212
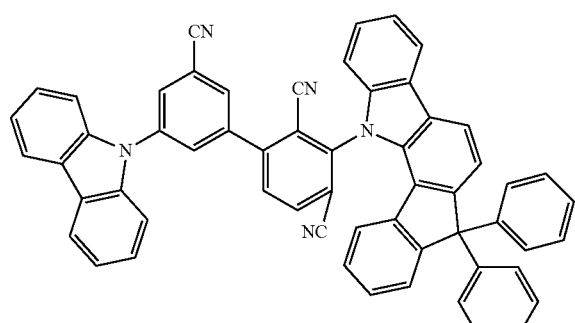
213
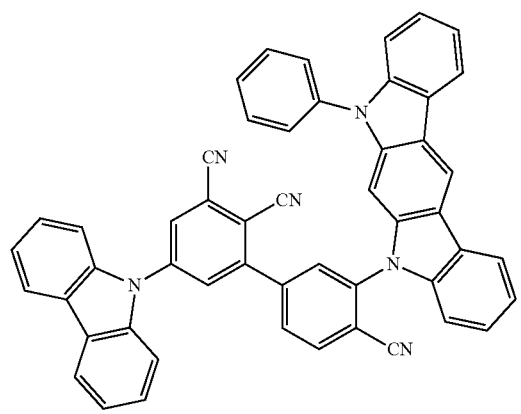
214
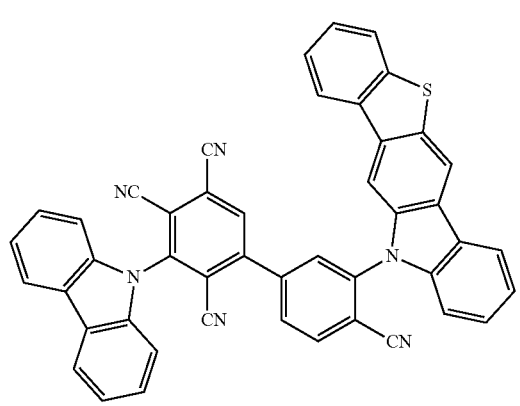
215
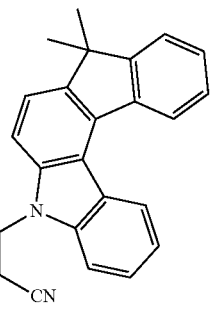
216
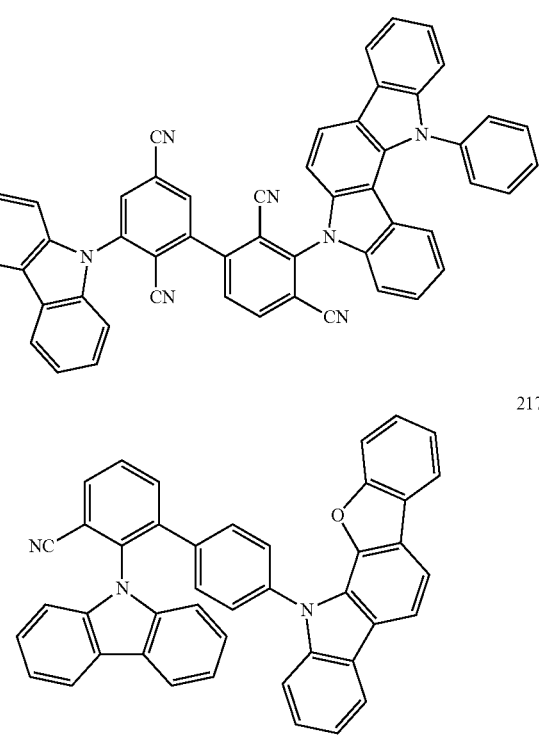
217
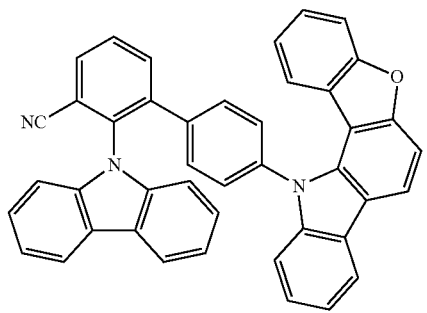
218

503
-continued
219
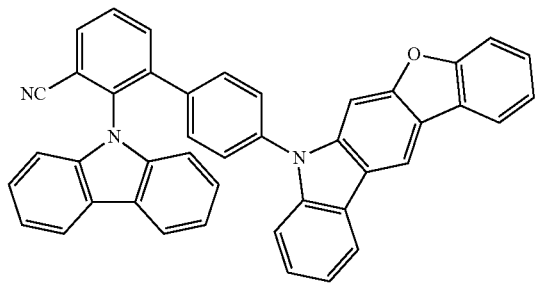
220
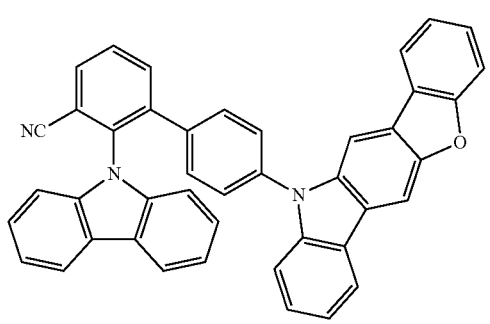
221
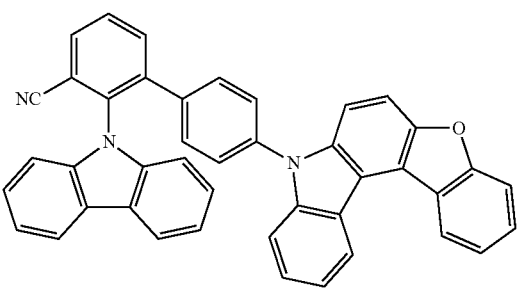
222
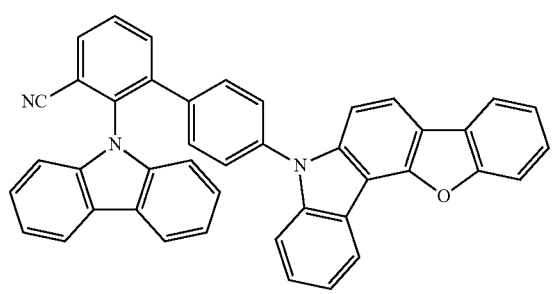
223
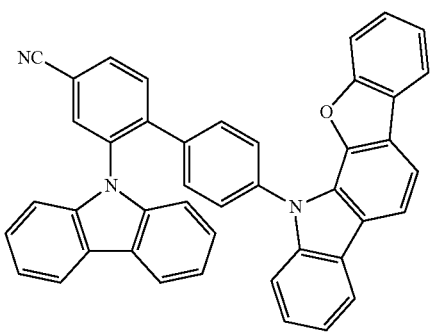
504
-continued
224
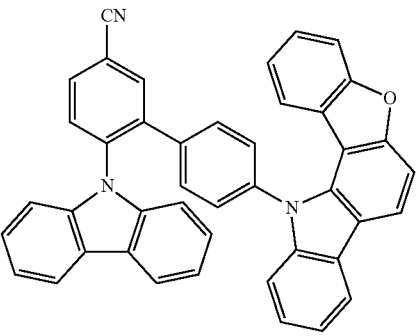
225
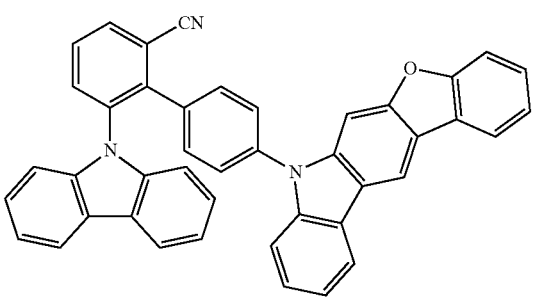
226
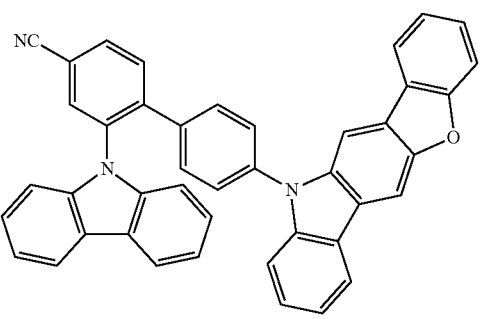
227
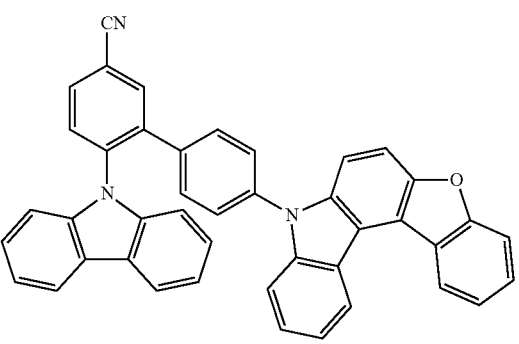

505
-continued
228
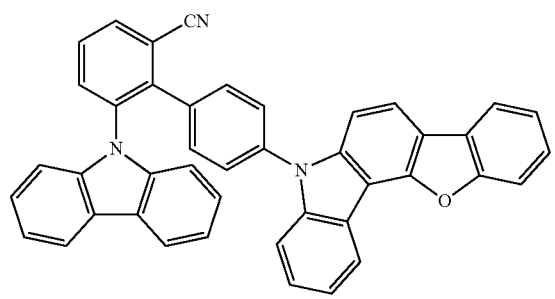
229
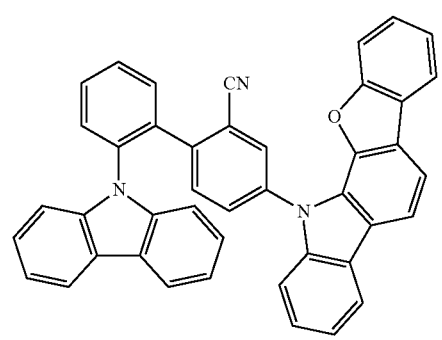
230
231
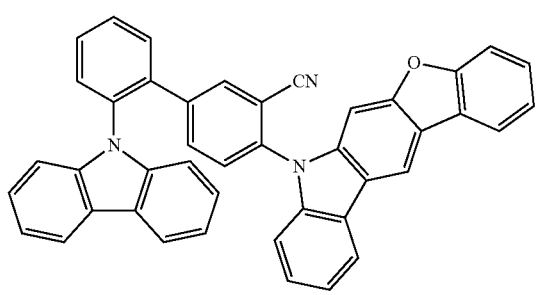
506
-continued
232
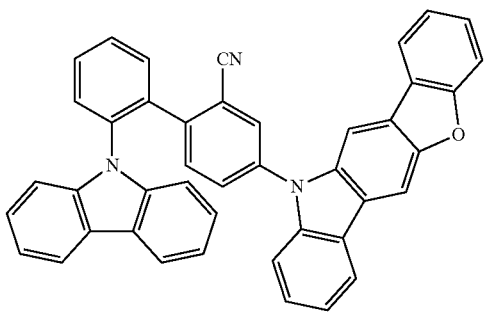
233
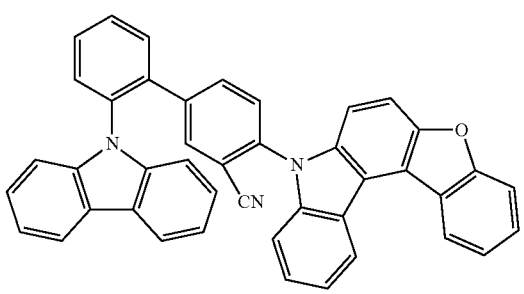
234
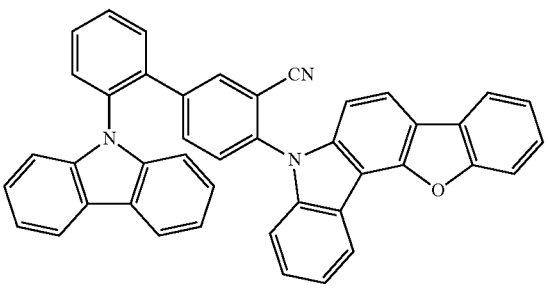
235
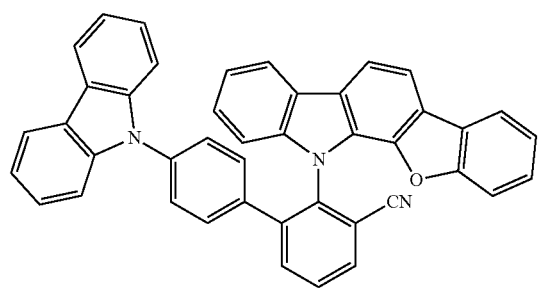
236
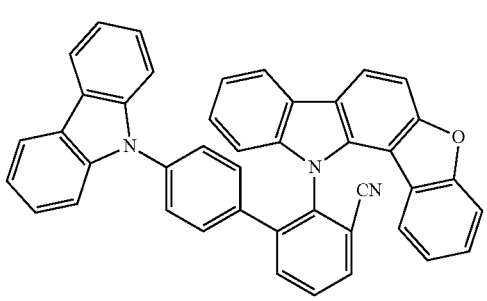

507
-continued
237
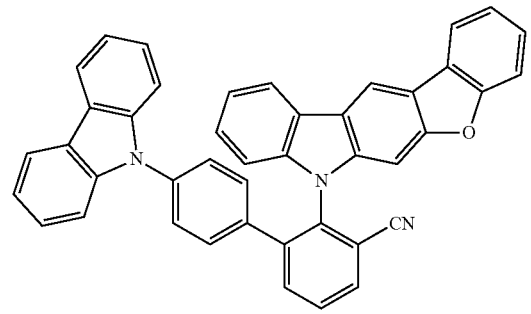
238
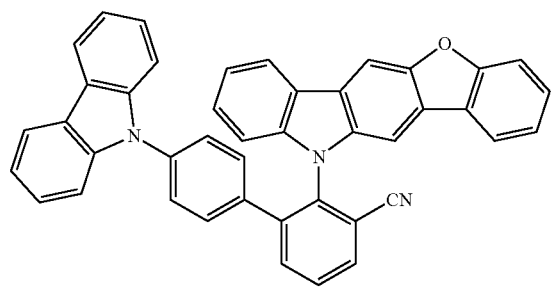
239
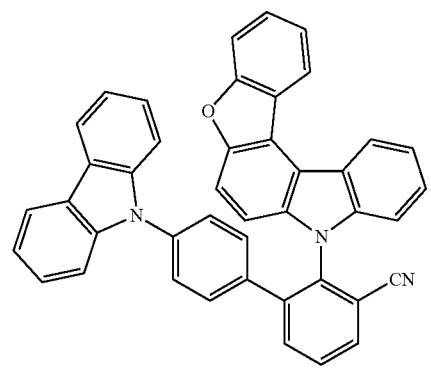
240
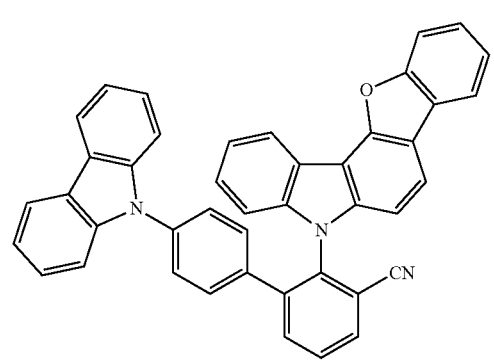
508
-continued
241
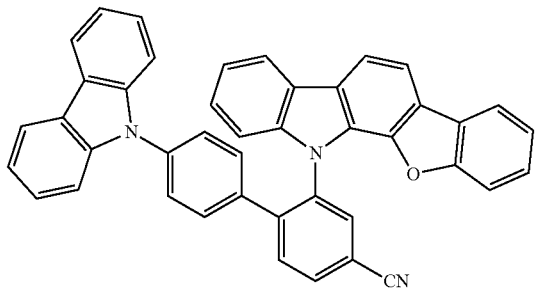
242
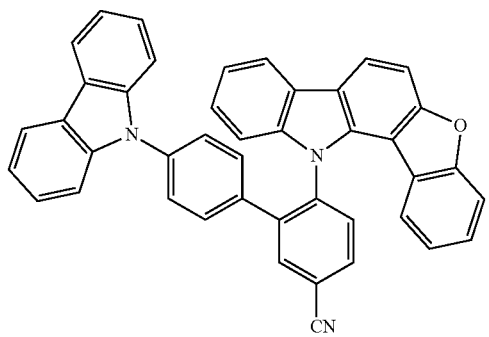
243
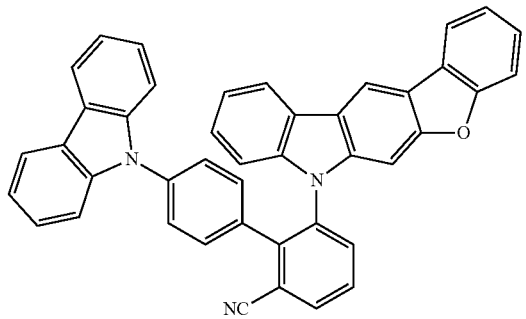
244
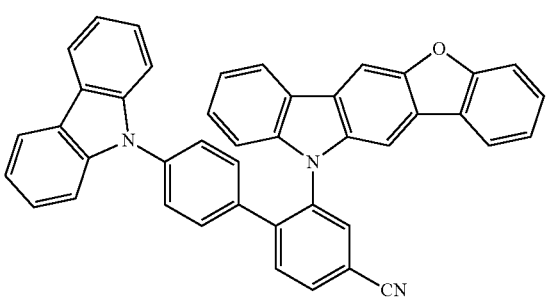

245
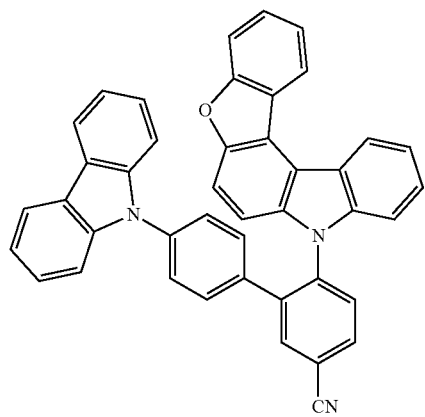
246
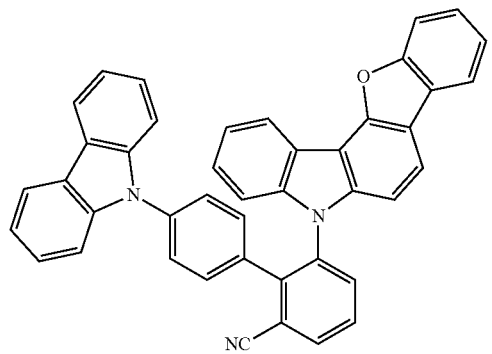
247
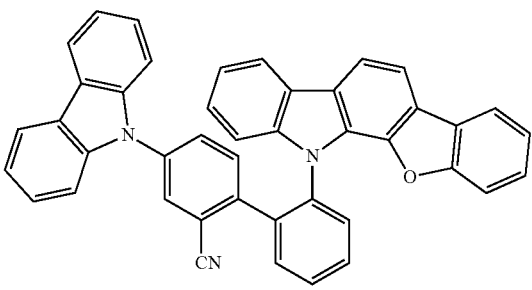
248
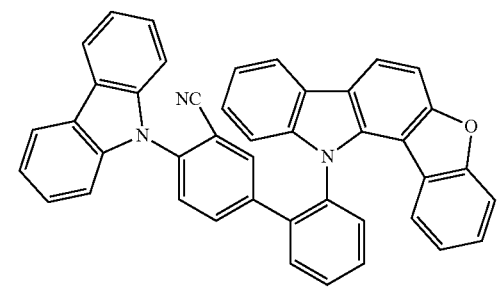
249
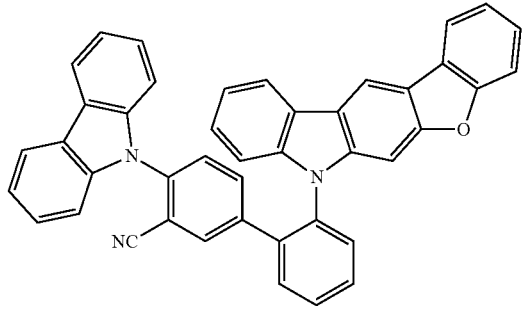
250
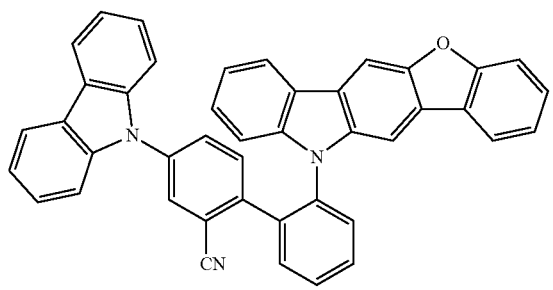
251
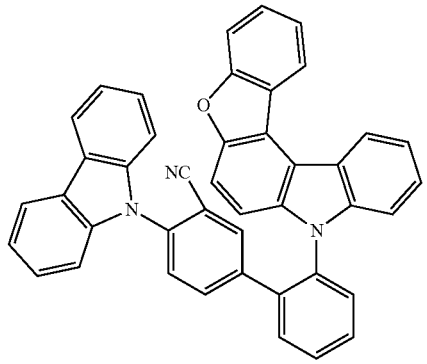
252
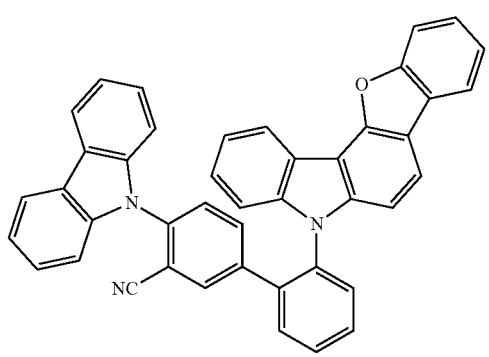

-continued
253
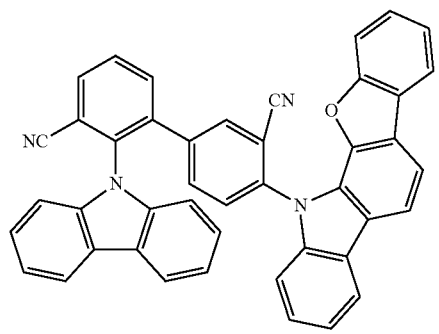
254
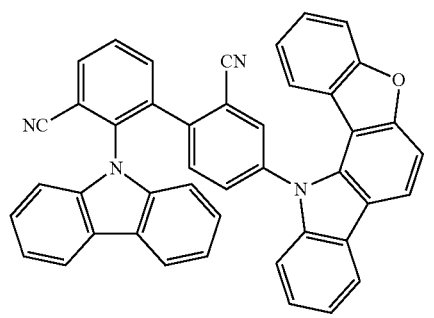
255
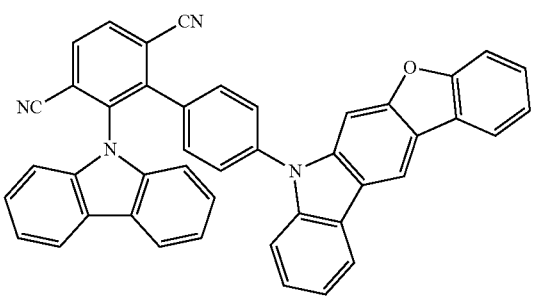
256
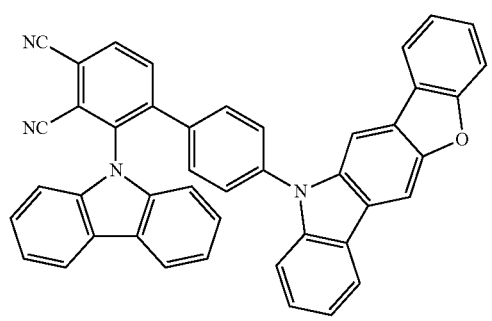
257
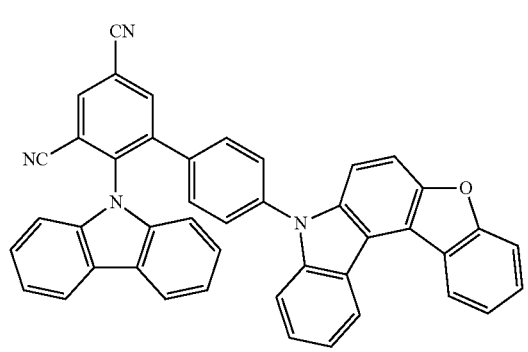
-continued
258
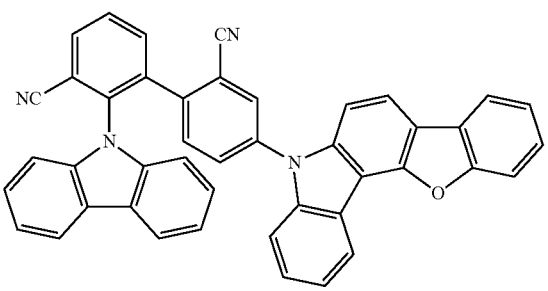
259
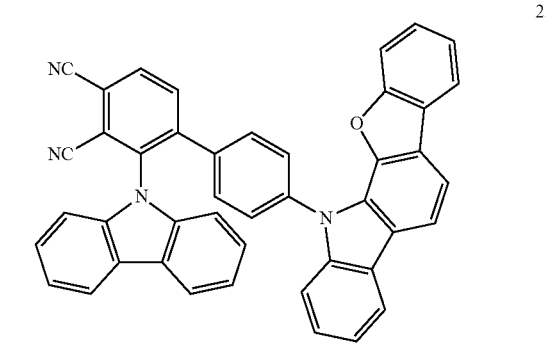
260
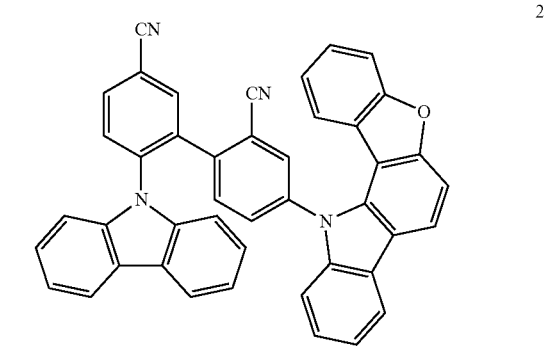
261
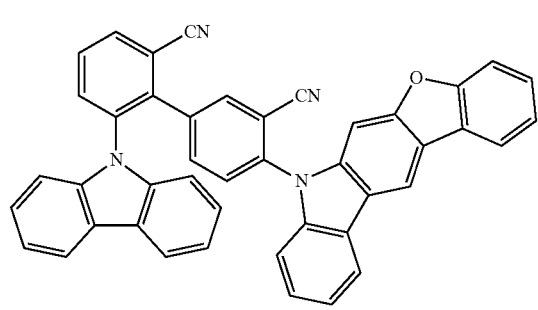
262
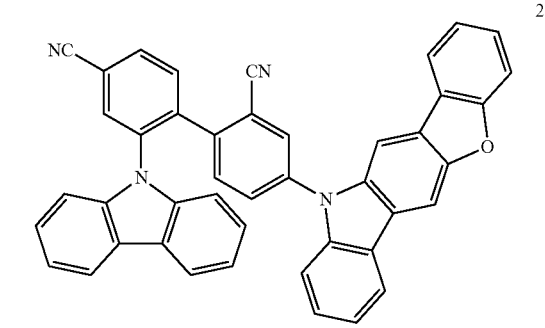

513
-continued

263

264

265

266

514
-continued

267

268

269

270

515
-continued
271
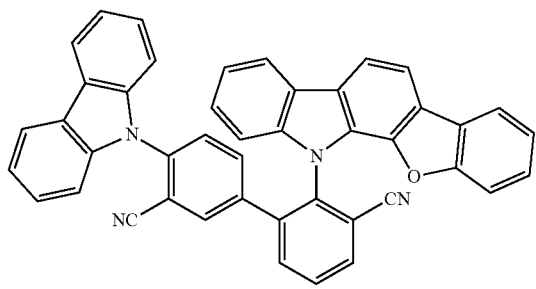
272
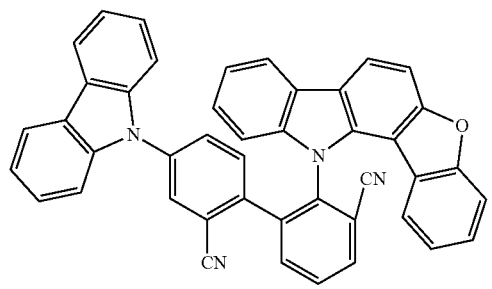
273
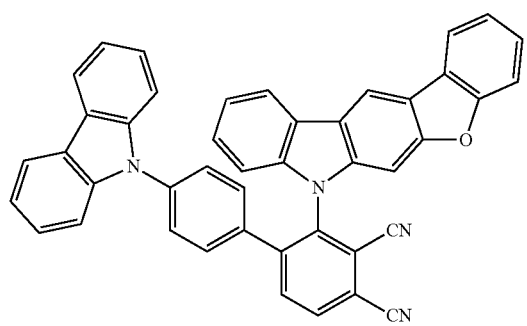
274
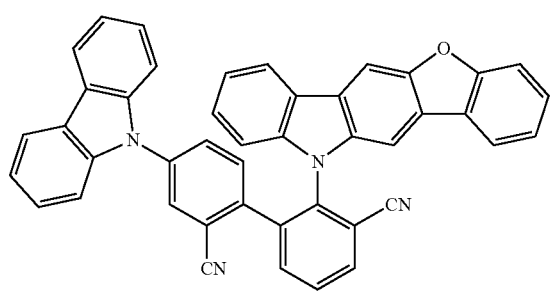
275
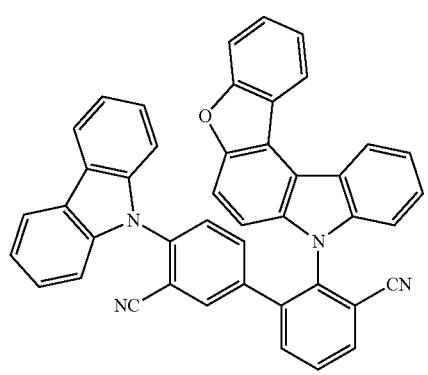
516
-continued
276
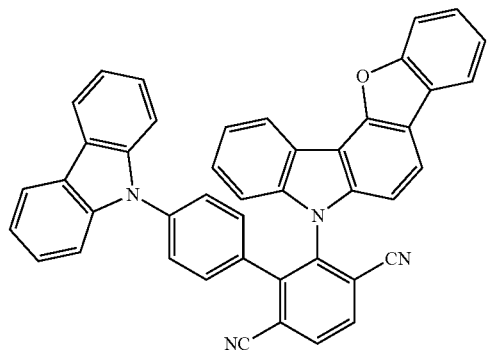
277
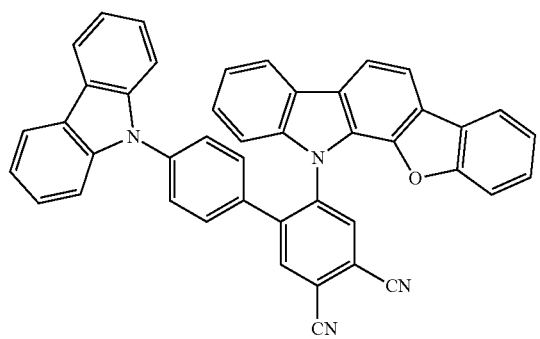
278
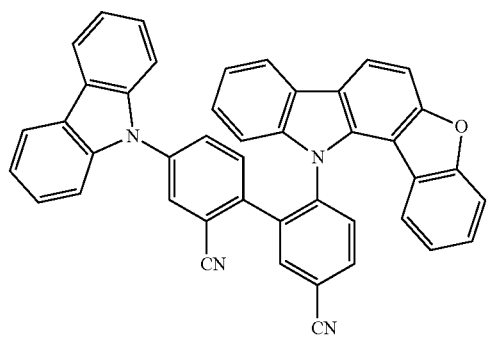
279
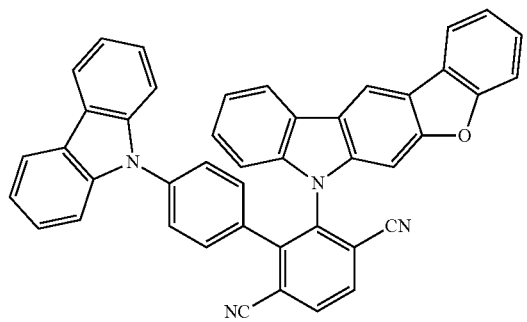

517
-continued
518
-continued
280
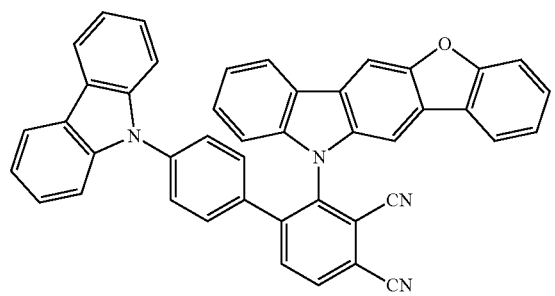
284
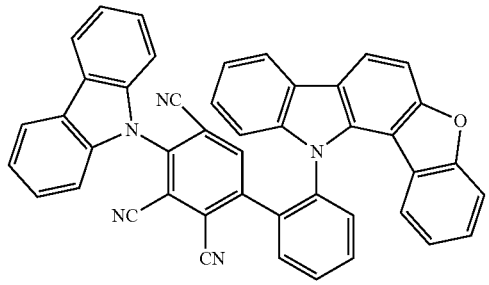
281
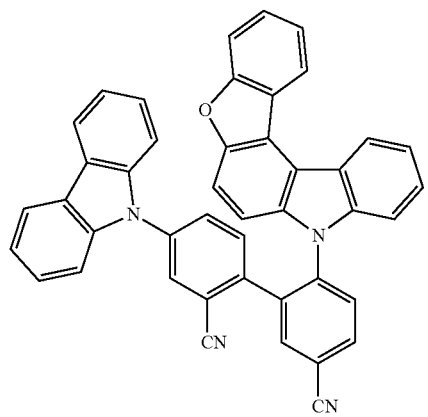
285
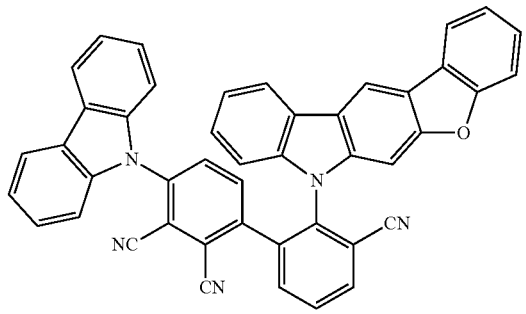
282
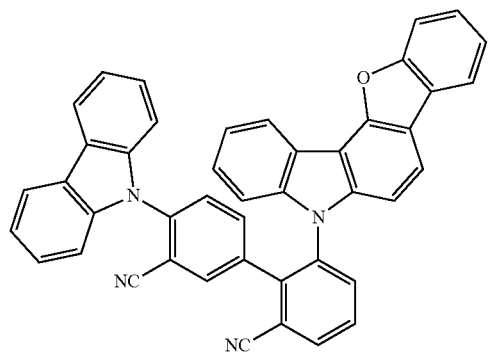
286
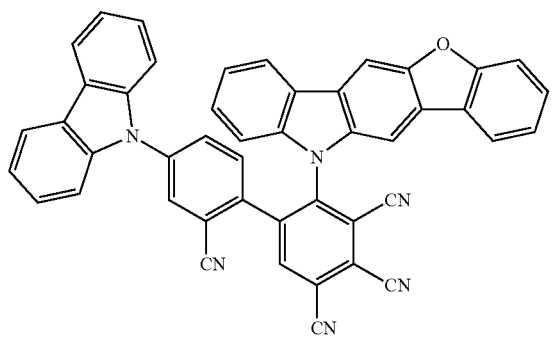
283
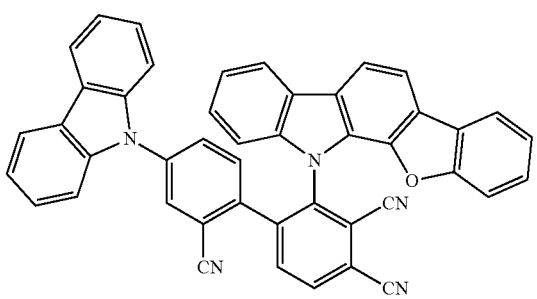
287
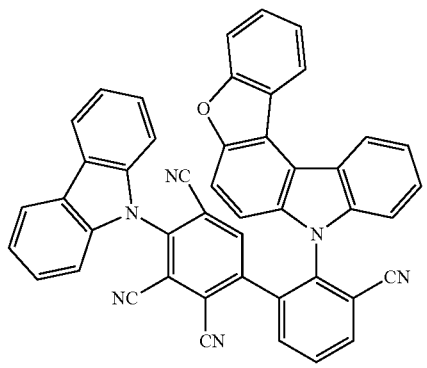

-continued
288
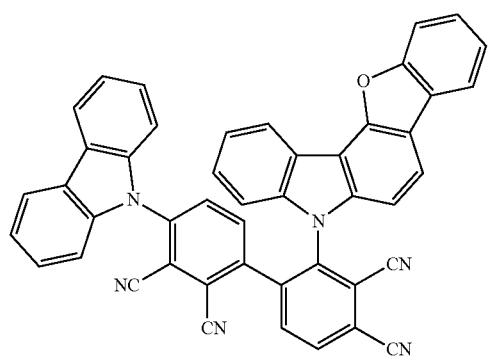
289
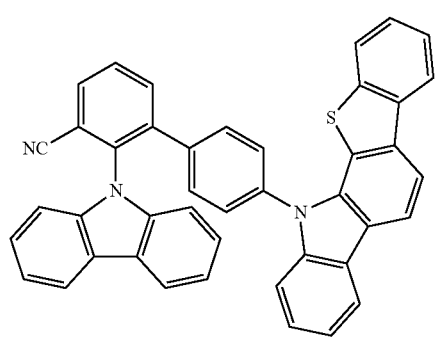
290
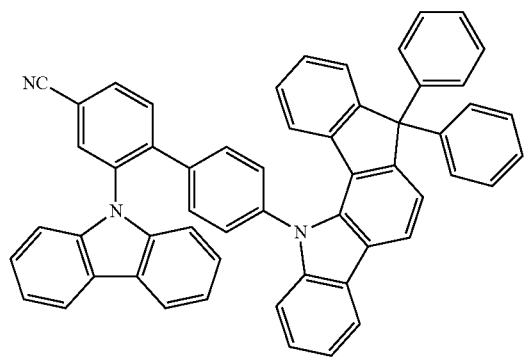
291
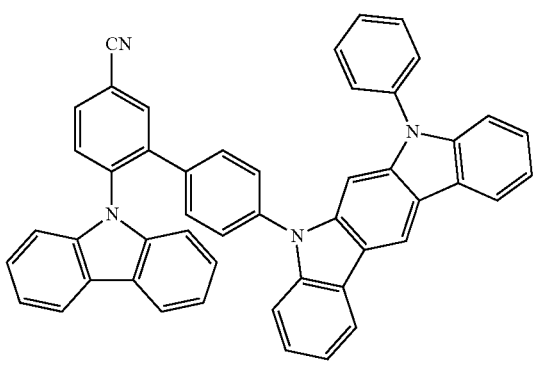
-continued
292
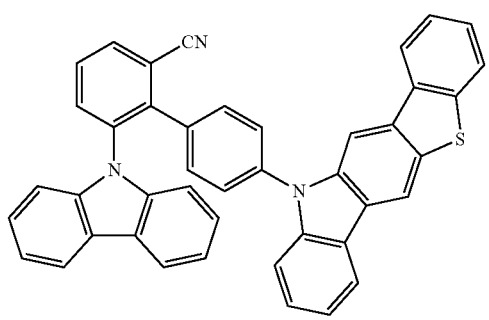
293
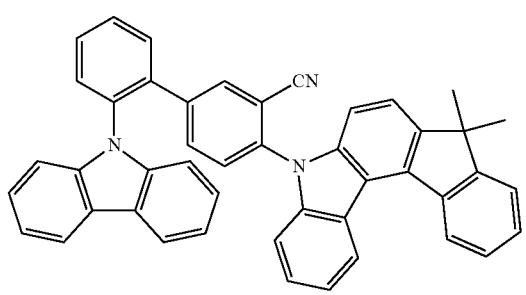
294
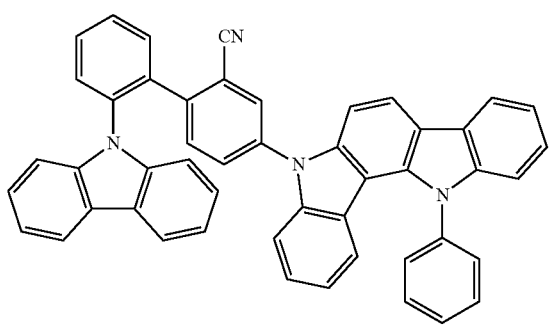
295
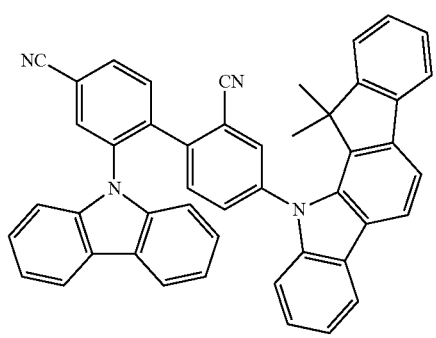

521
-continued
296
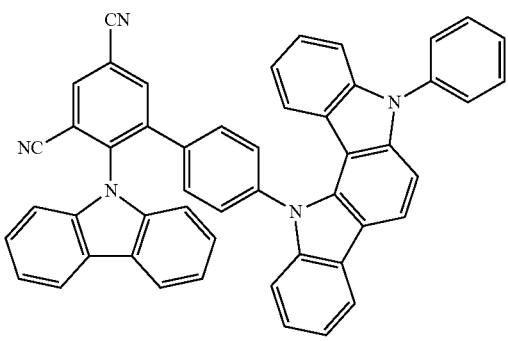
297
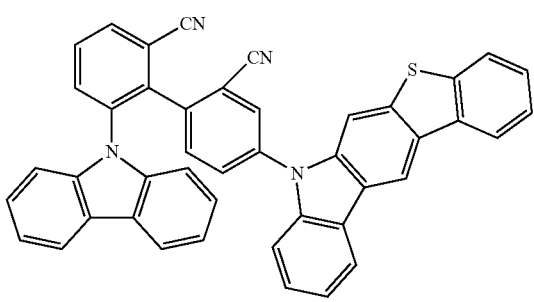
298
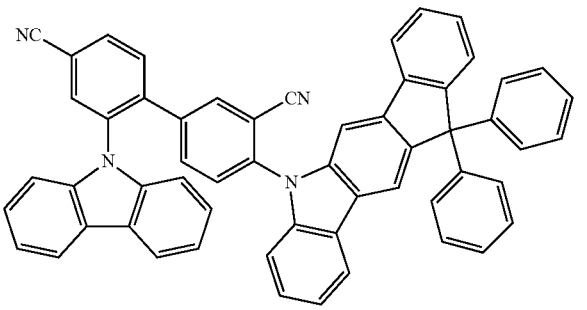
299
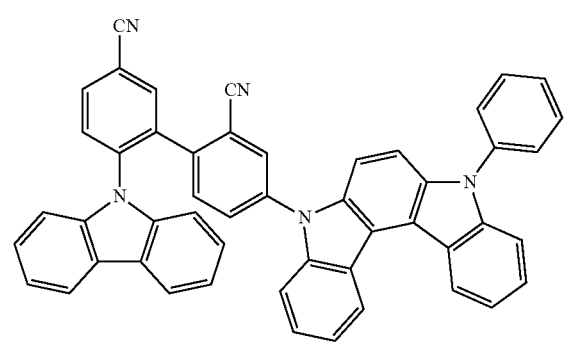
522
-continued
300
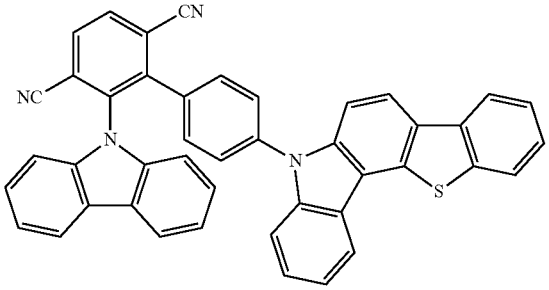
301
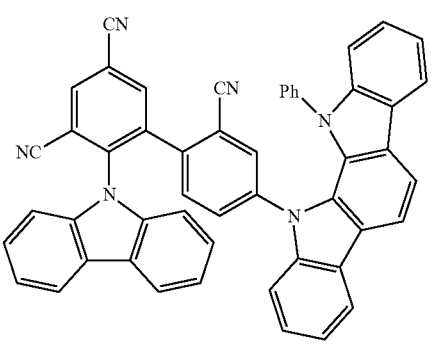
302
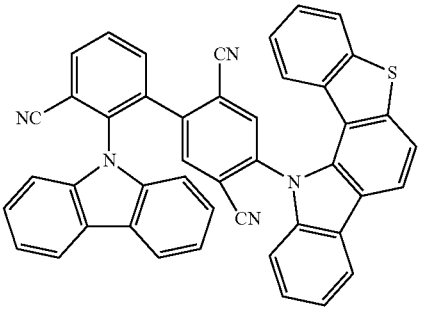
303
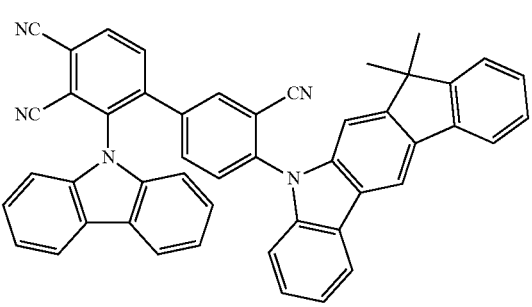
304
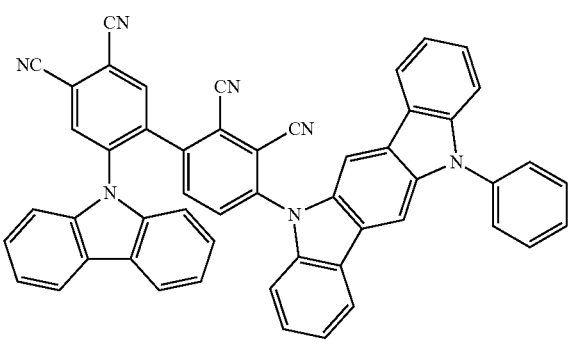

523
-continued
305
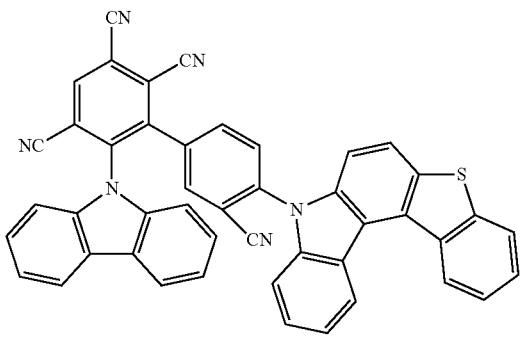
306
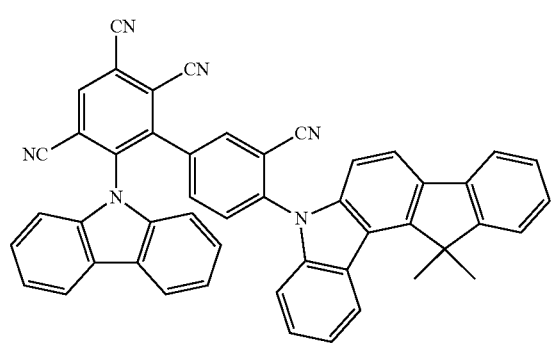
307
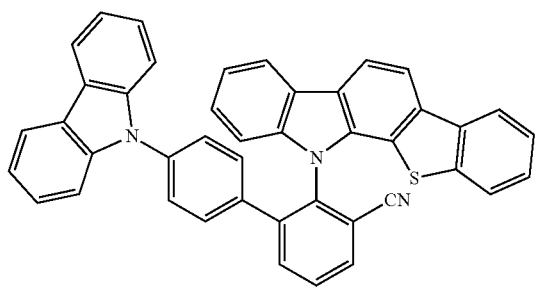
308
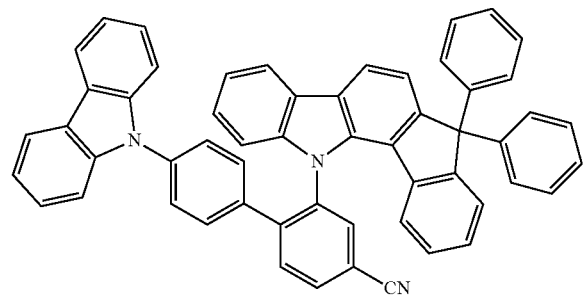
524
-continued
309
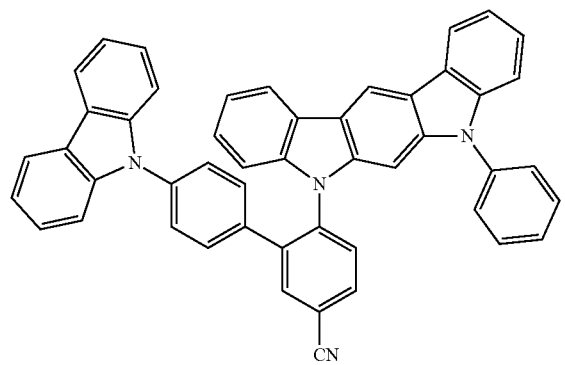
310
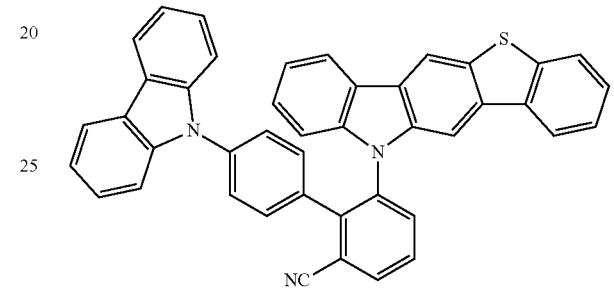
311
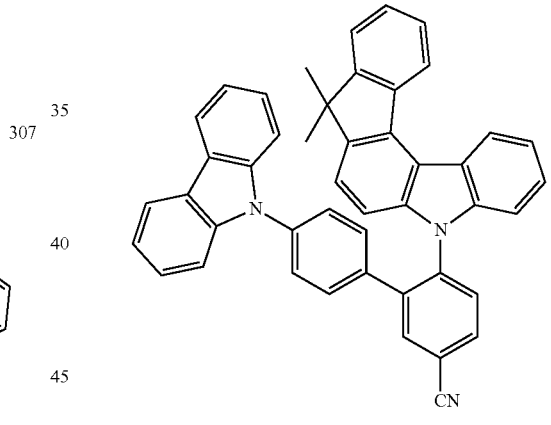
312
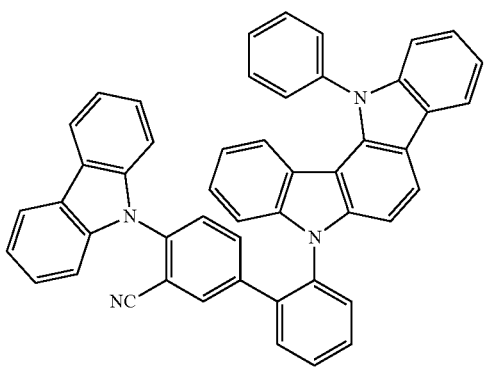

525
-continued
313
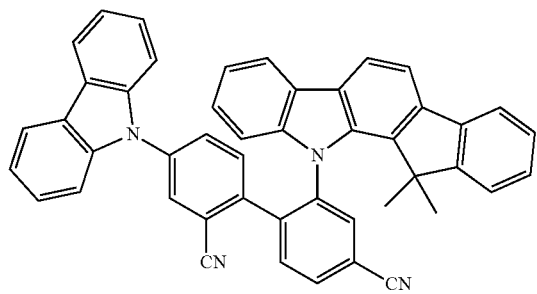
314
315
316
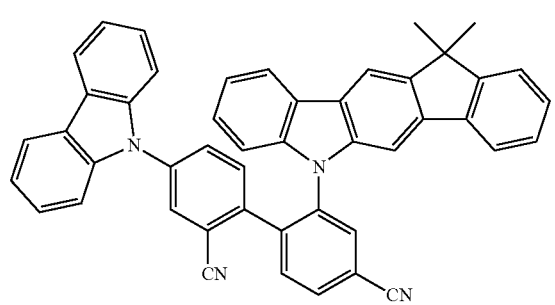
526
-continued
317
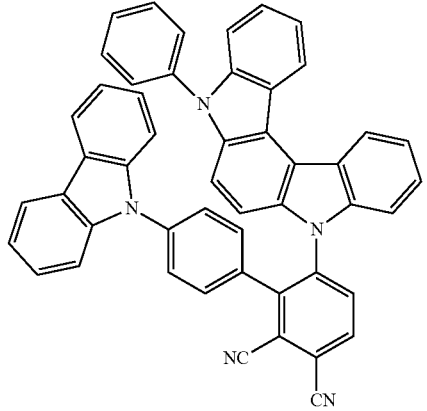
318
319
320
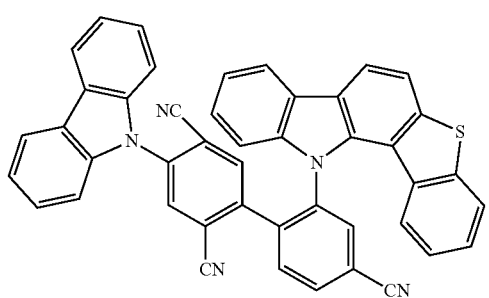

321
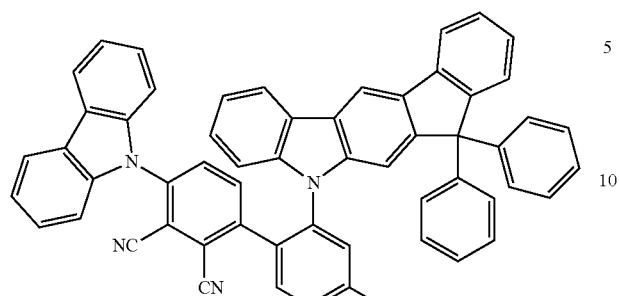
322
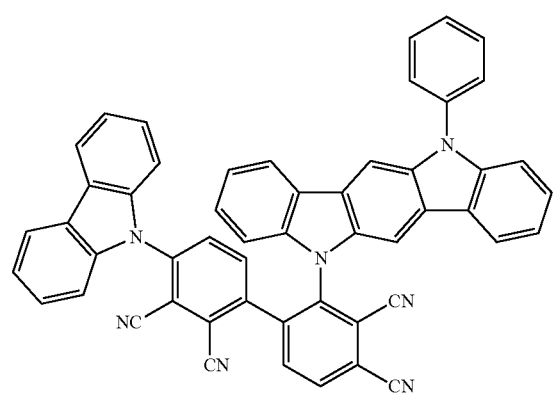
323
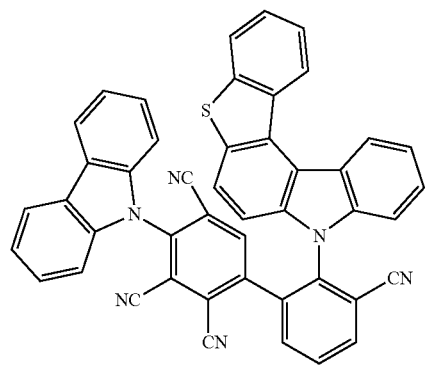
324
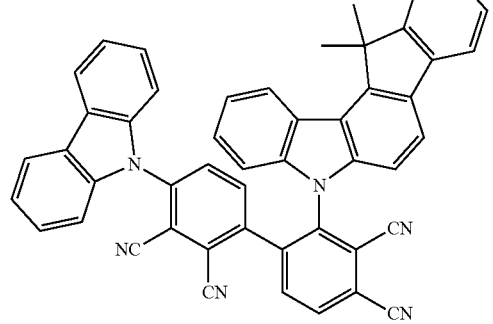
325
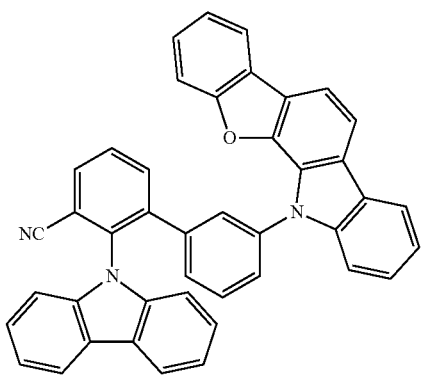
326
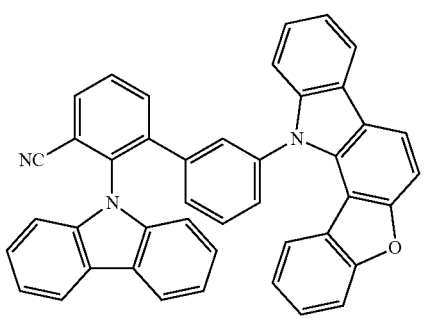
327
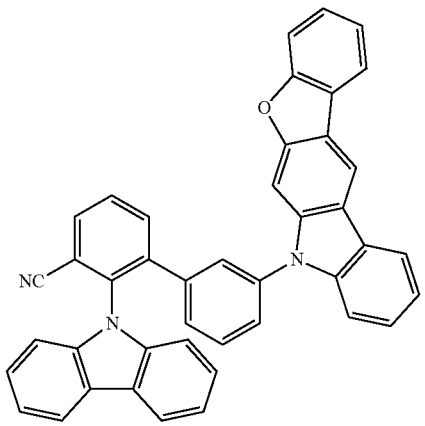
328
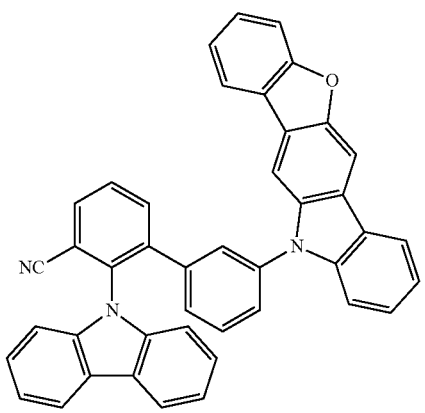

329
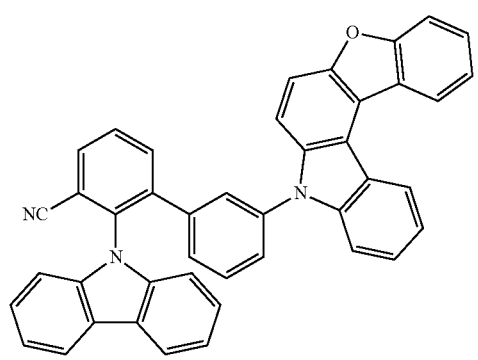
330
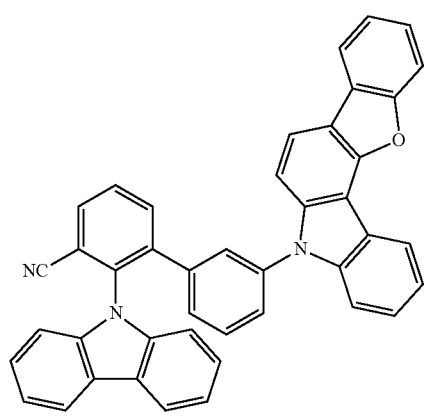
331
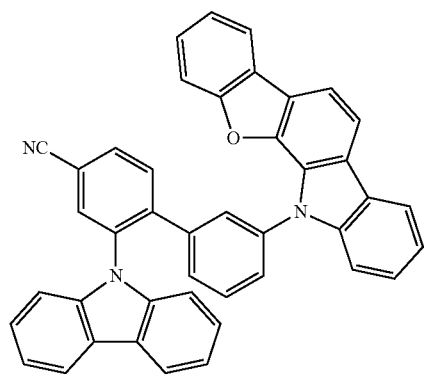
332
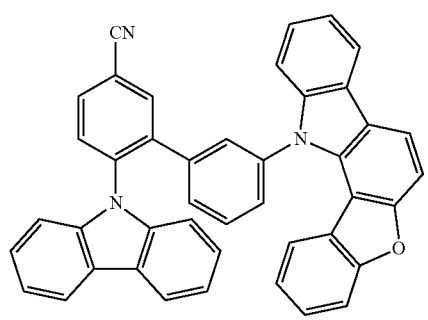
333
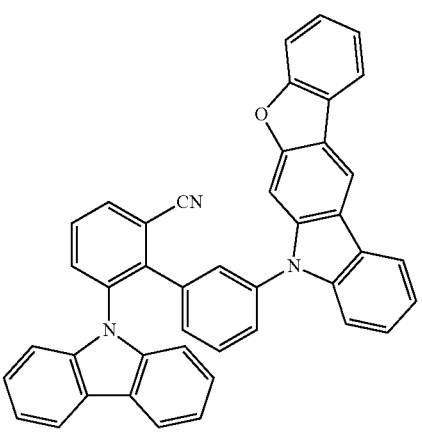
334
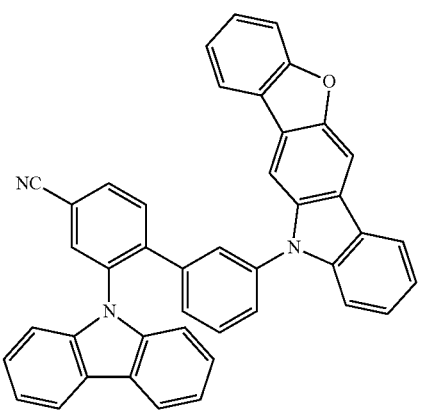
335
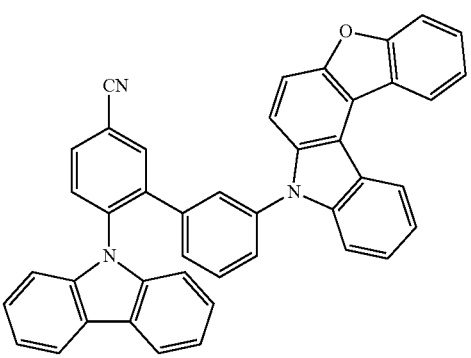
336
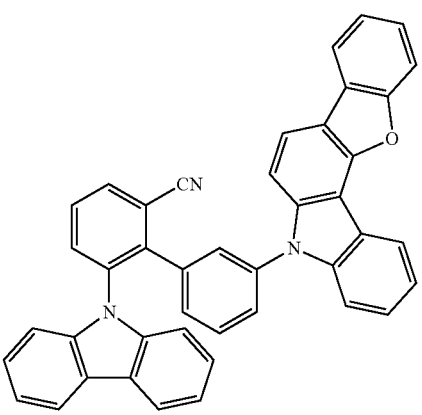

337
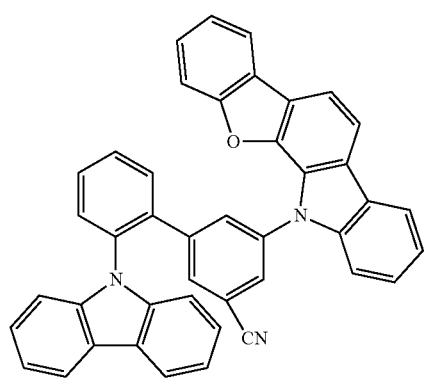
338
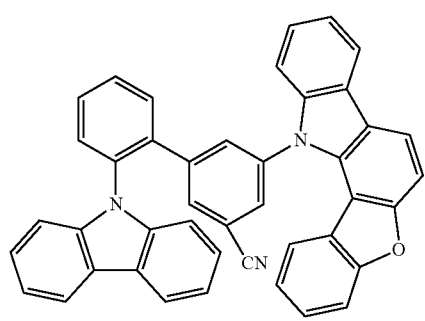
339
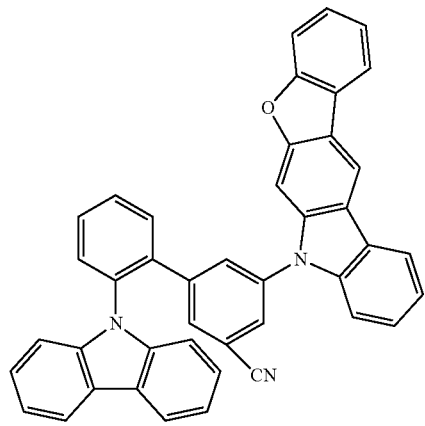
340
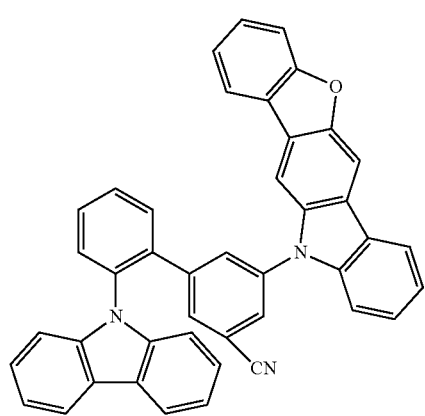
341
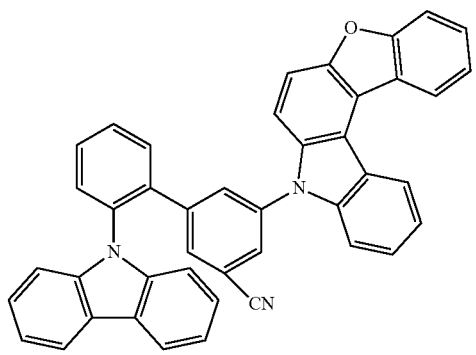
342
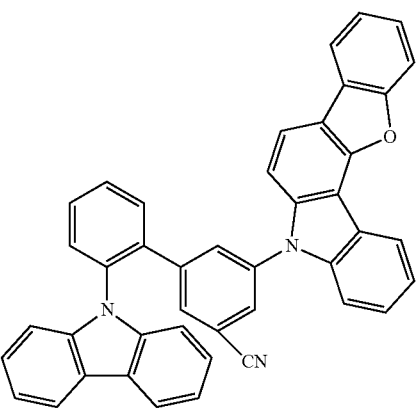
343
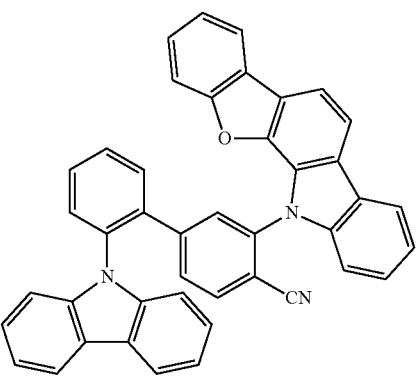
344
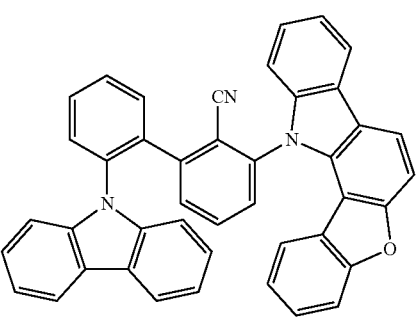

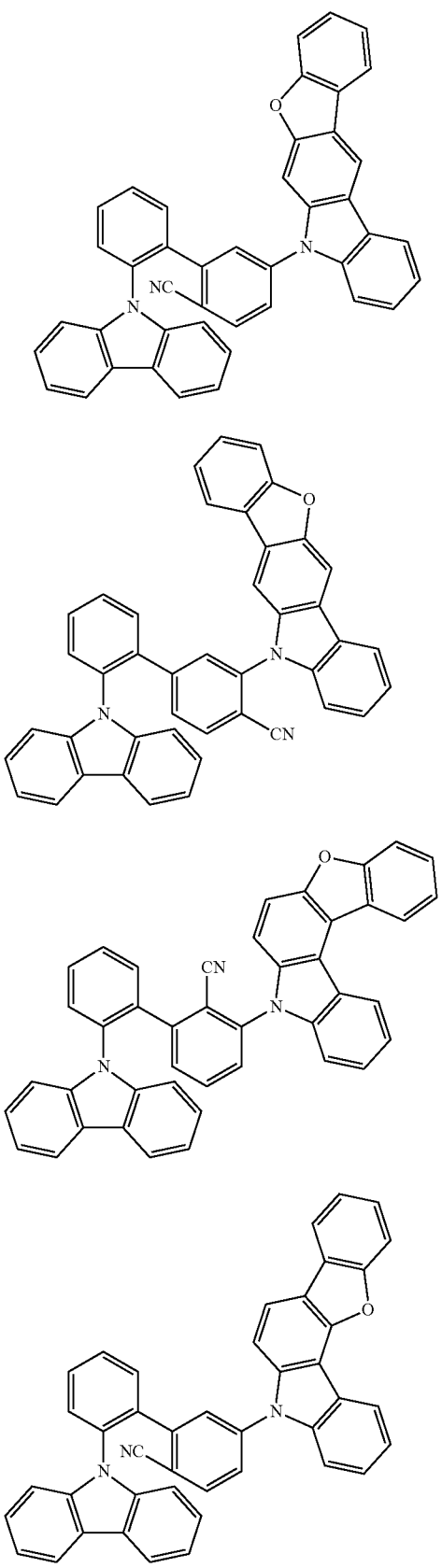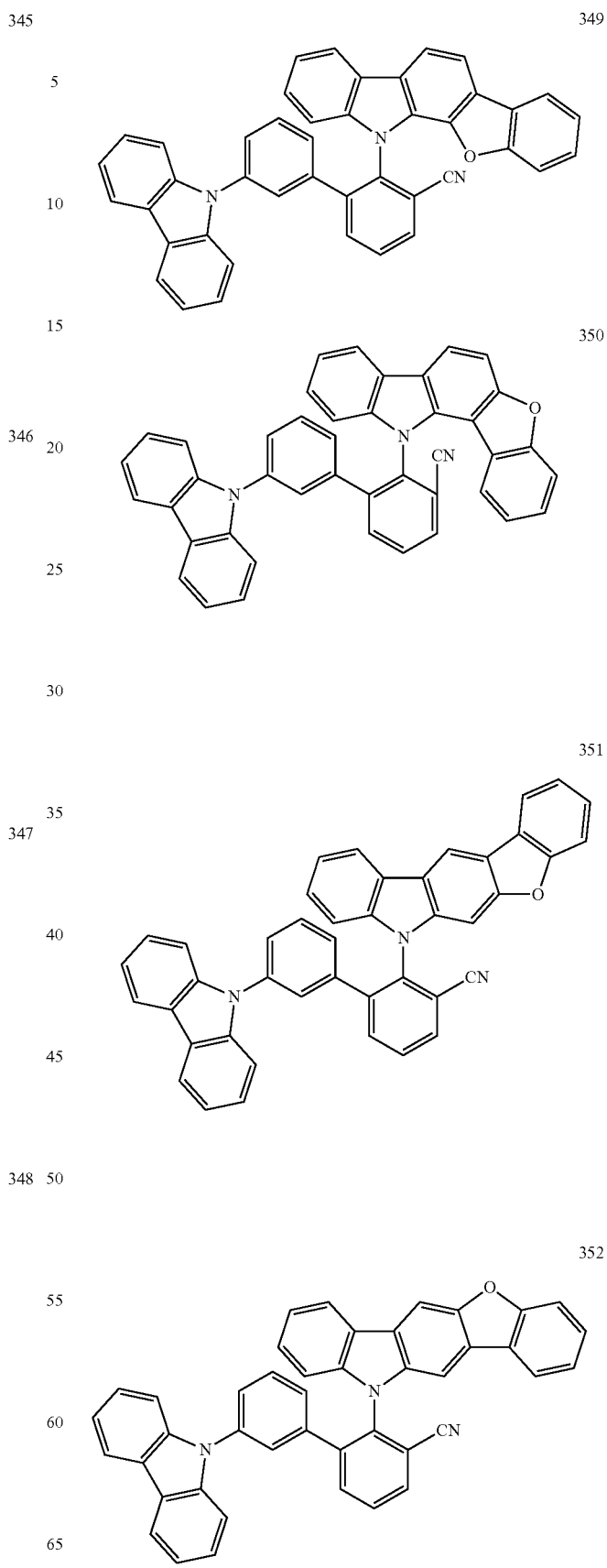

-continued
353
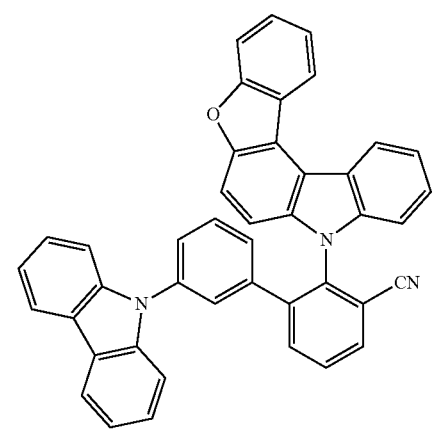
354
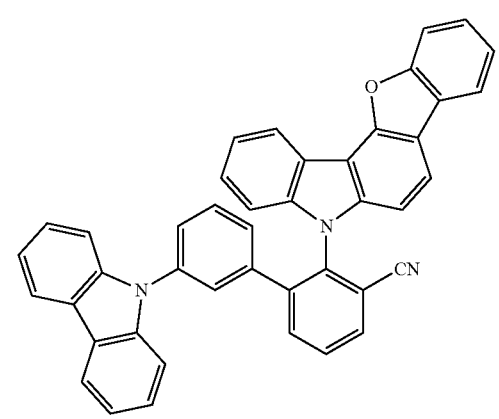
355
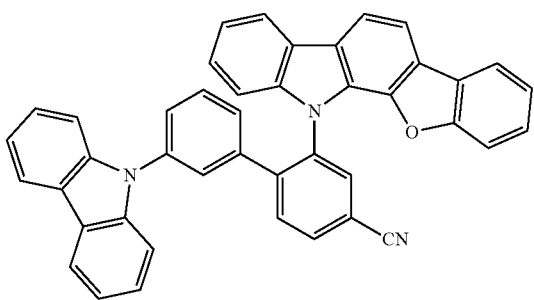
356
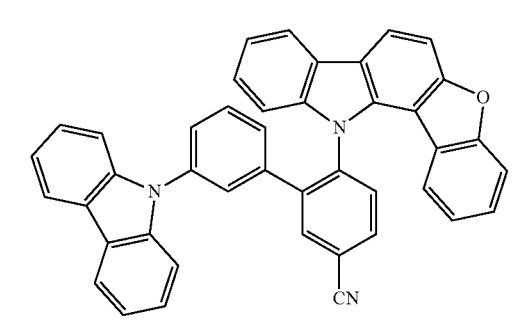
-continued
357
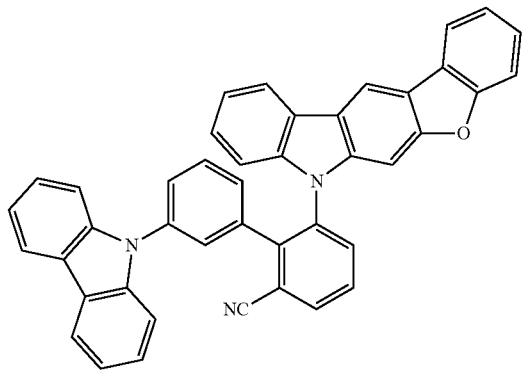
358
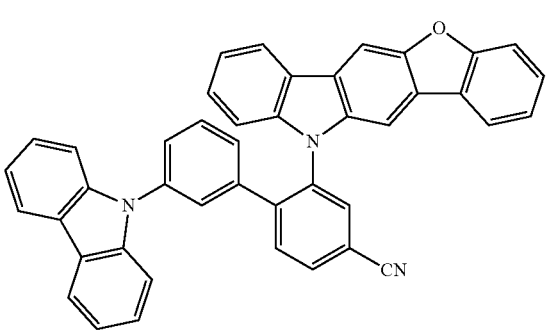
359
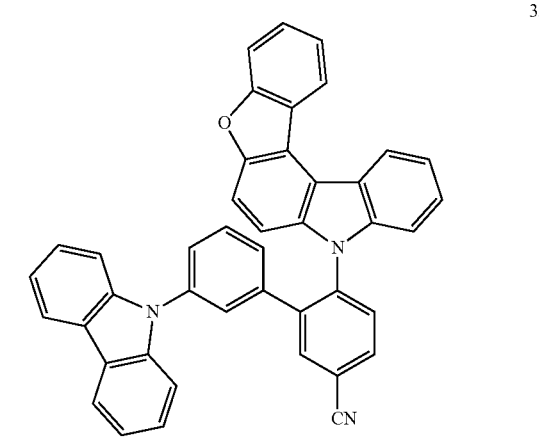
360
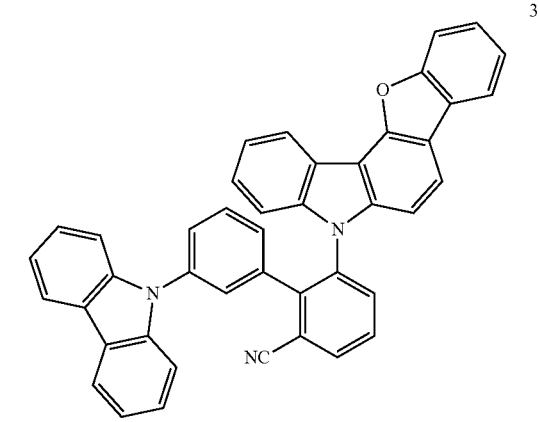

537
-continued
361
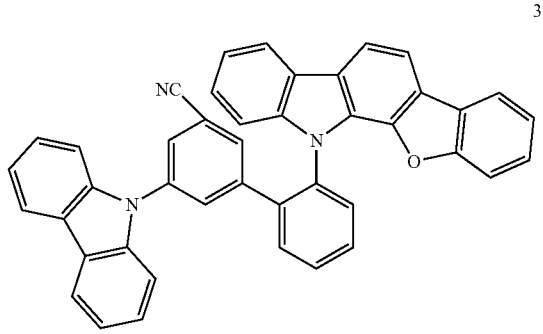
362
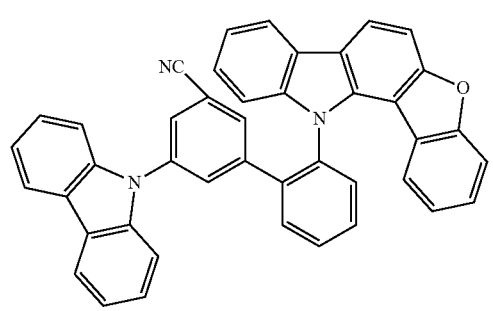
363
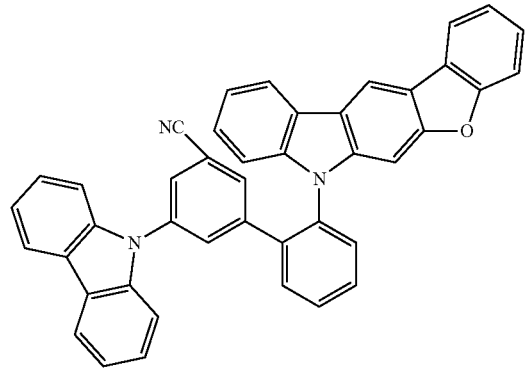
364
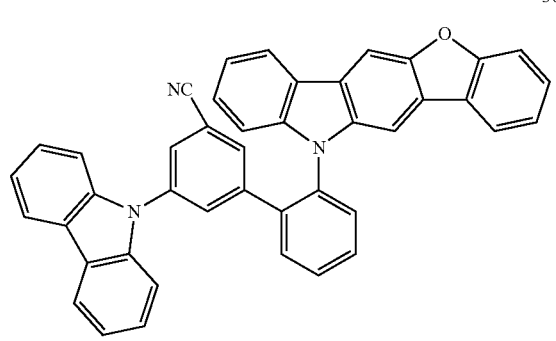
538
-continued
365
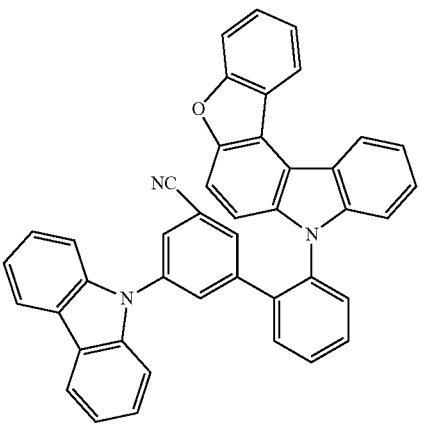
366
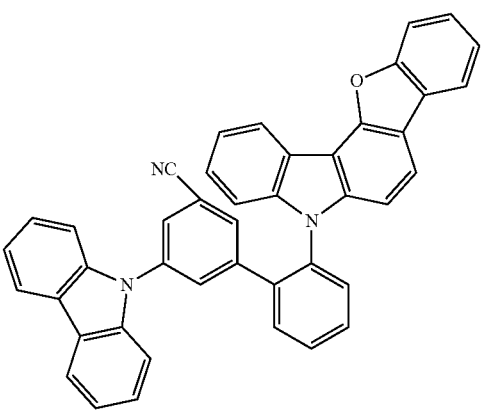
367
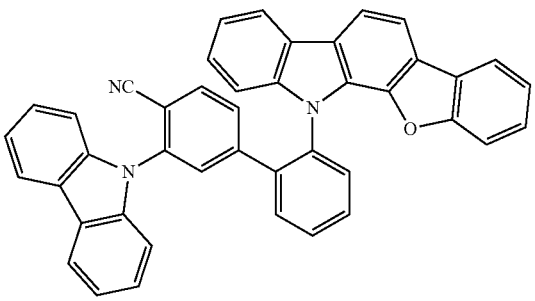
368
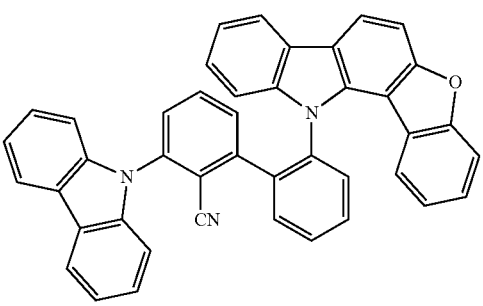

369
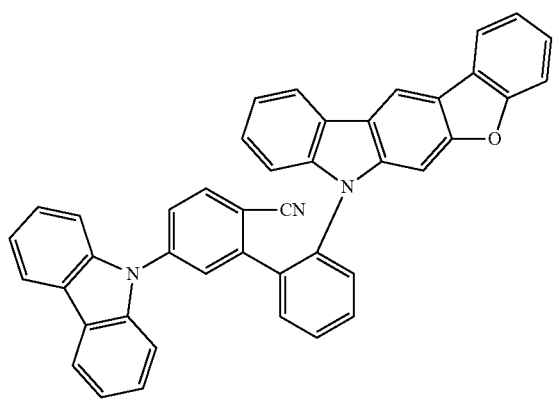
370
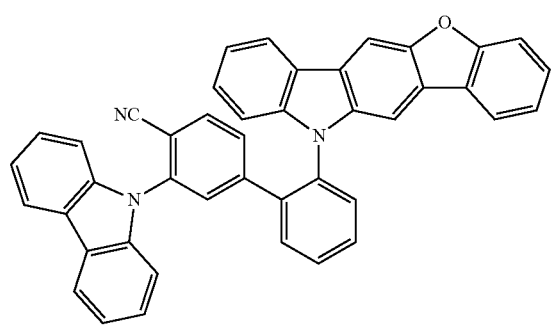
371
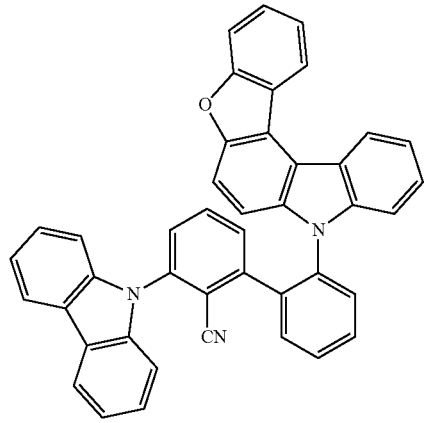
372
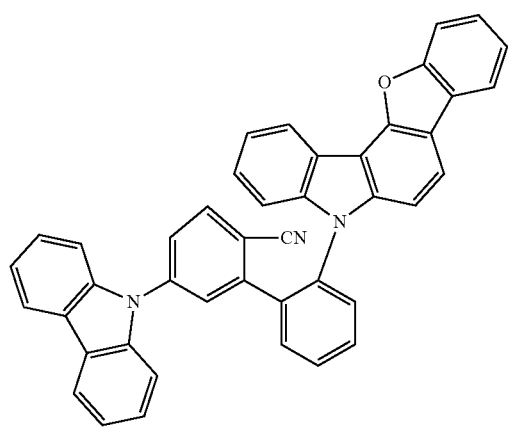
373
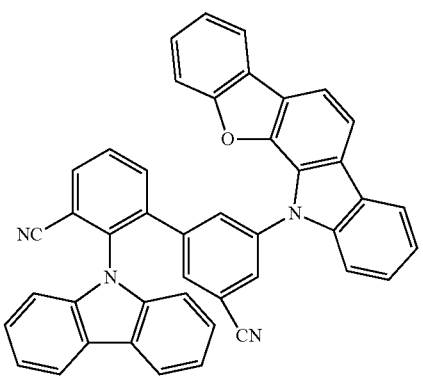
374
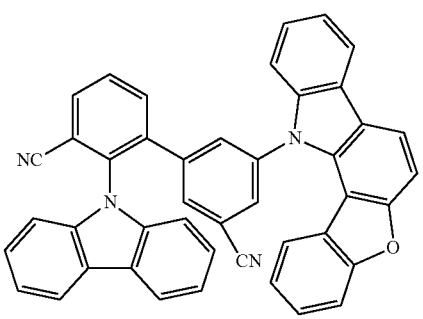
375
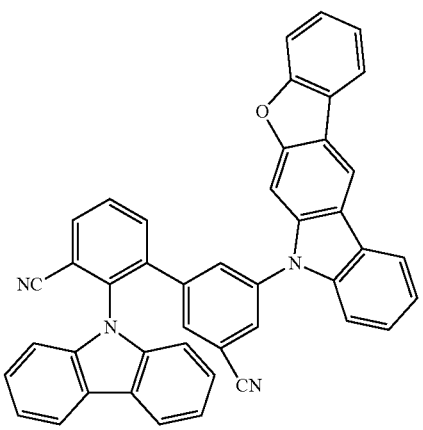
376
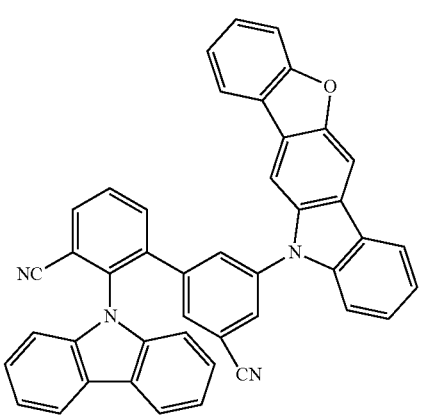

377
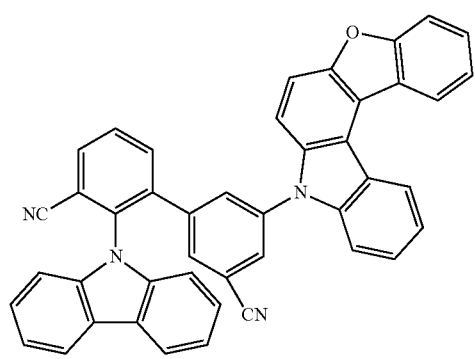
378
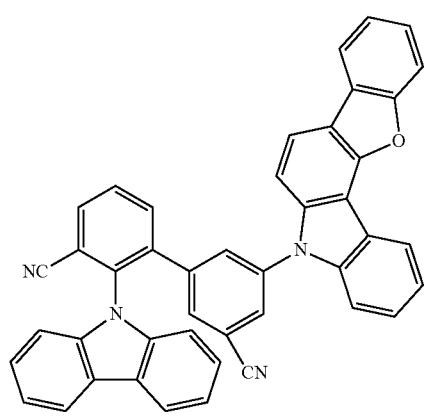
379
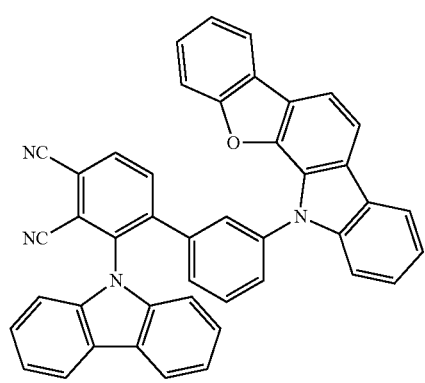
380
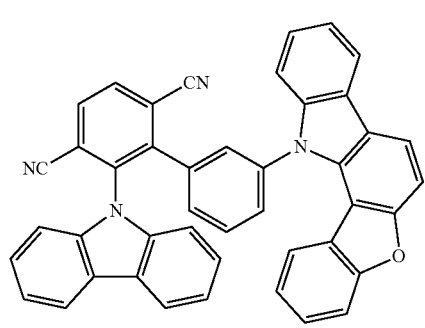
381
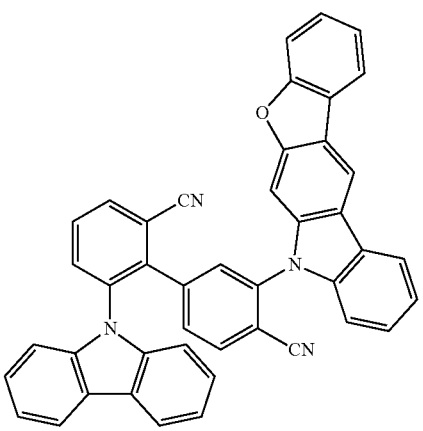
382
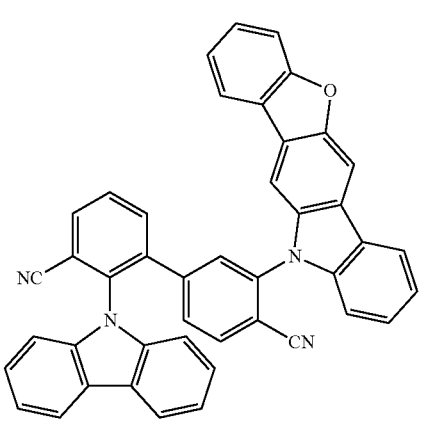
383
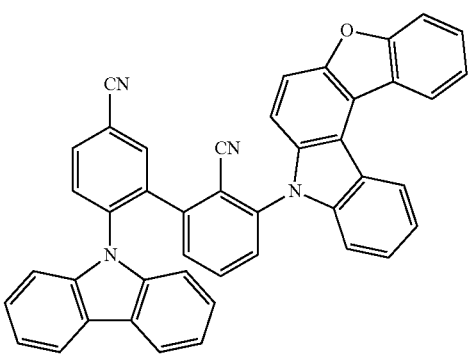
384
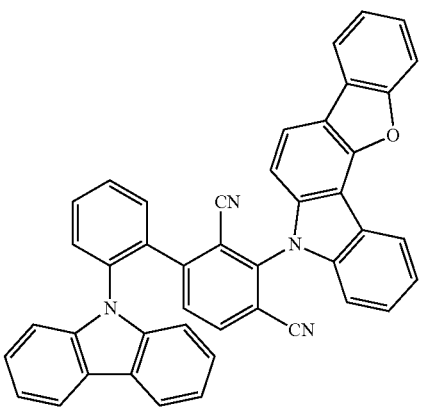

385
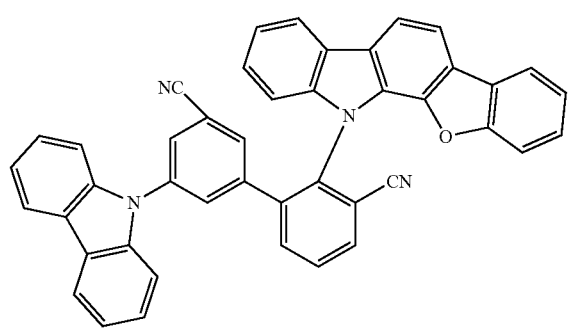
386
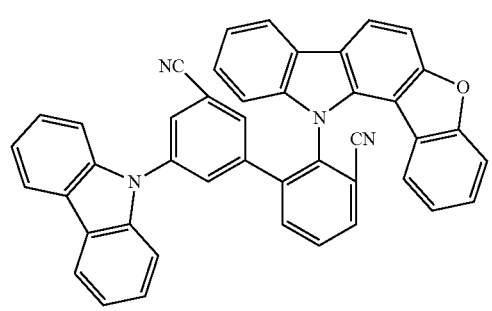
387
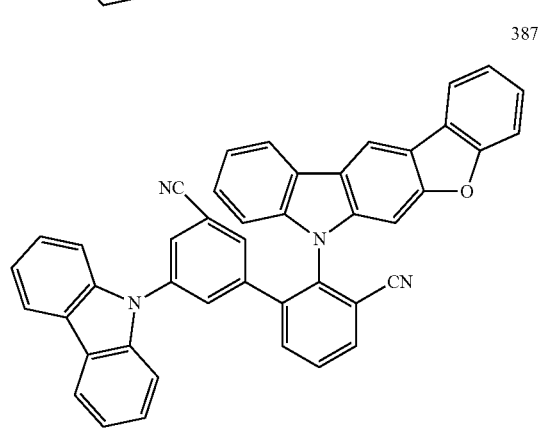
388
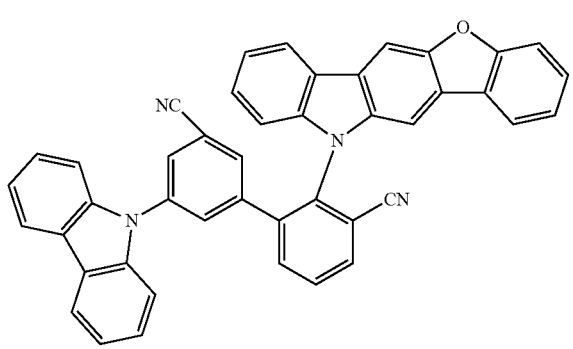
389
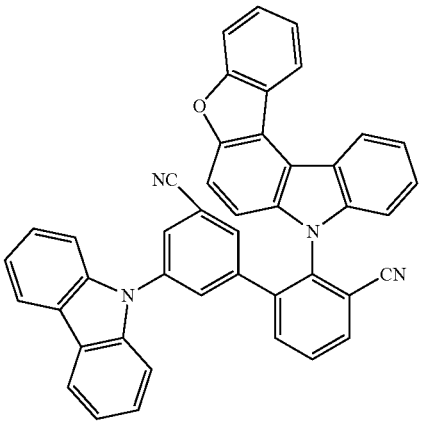
390
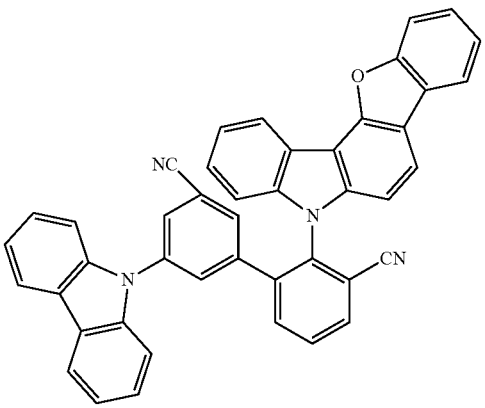
391
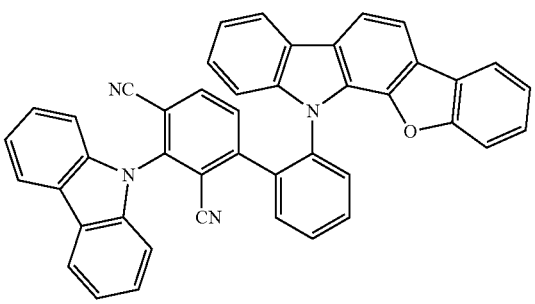
392
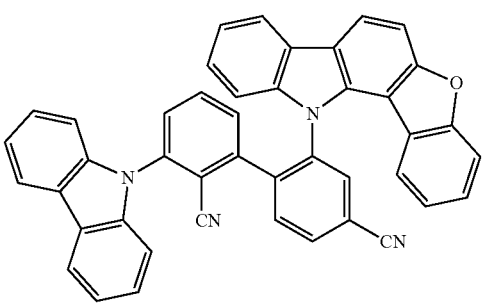

545
-continued
393
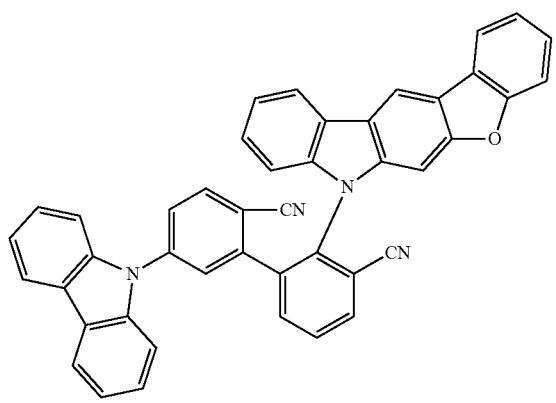
394

395

396

546
-continued
397
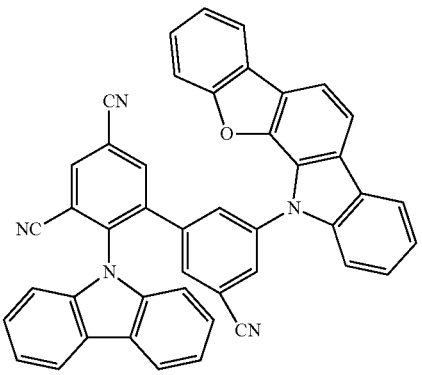
398
399

400

401
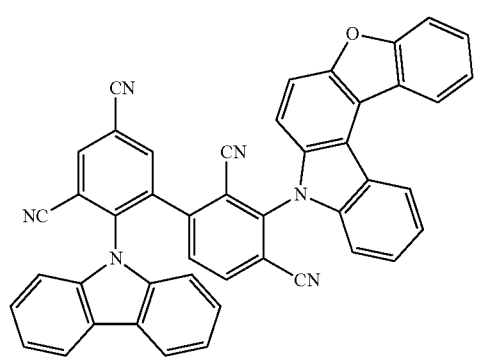
402
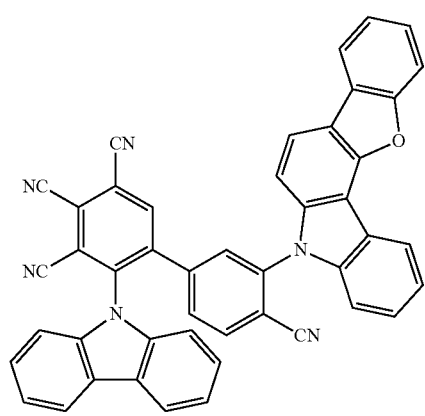
403
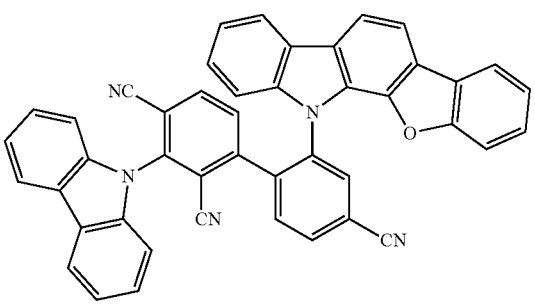
404
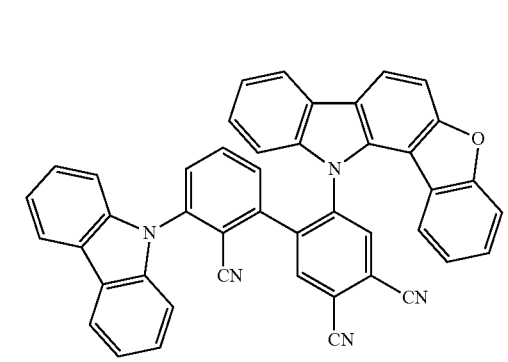
405
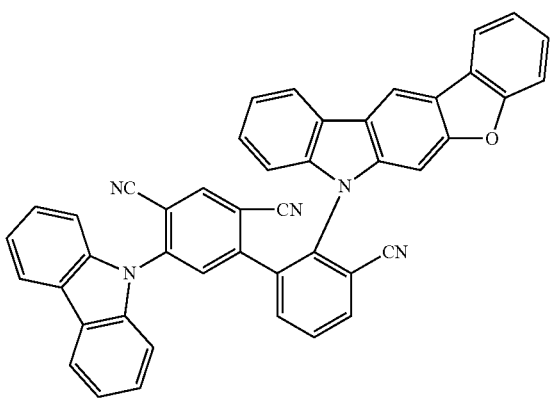
406
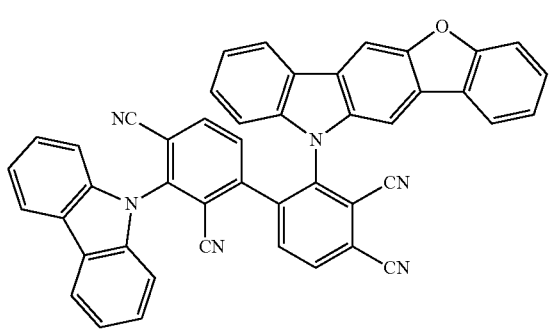
407
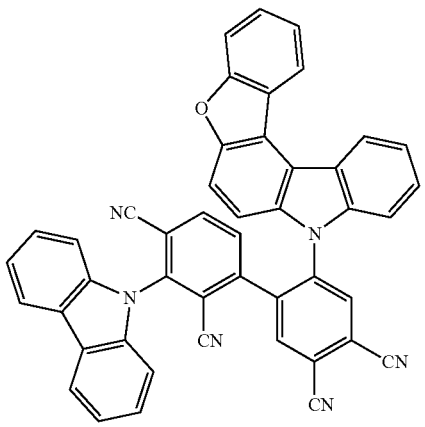
408
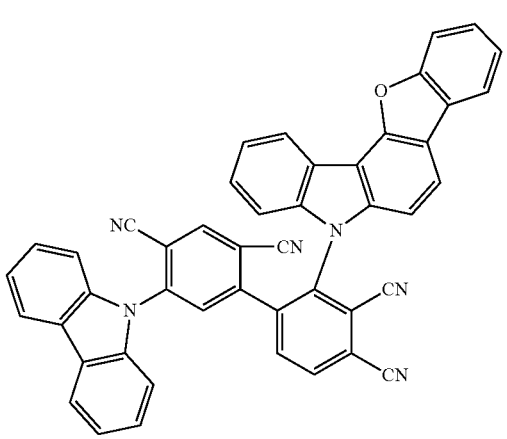

409
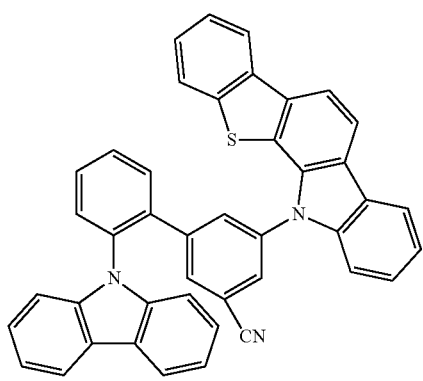
410
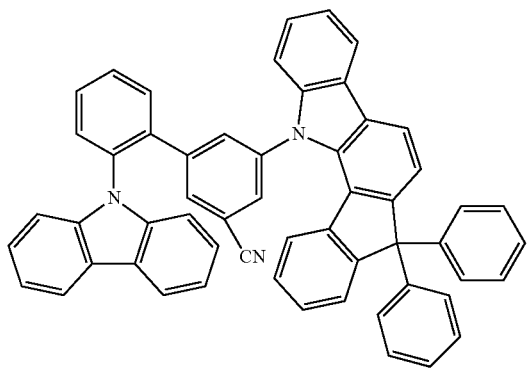
411
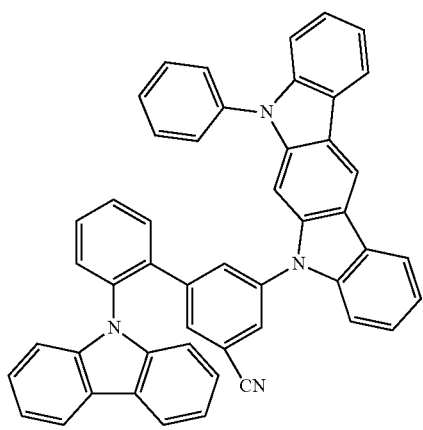
412
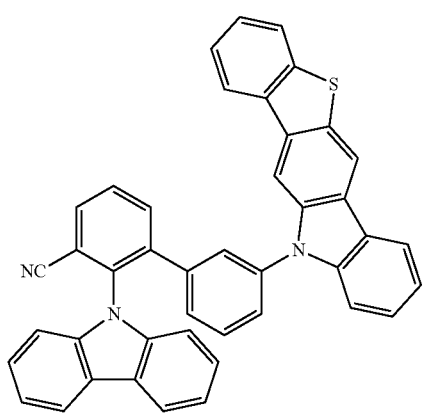
413
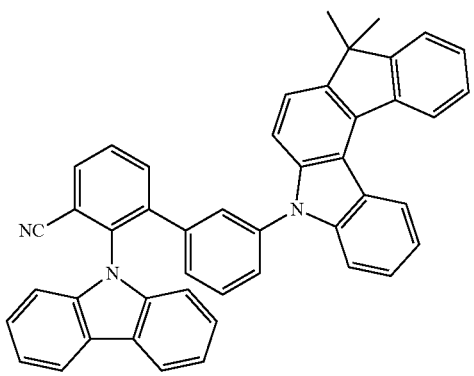
414

415

416
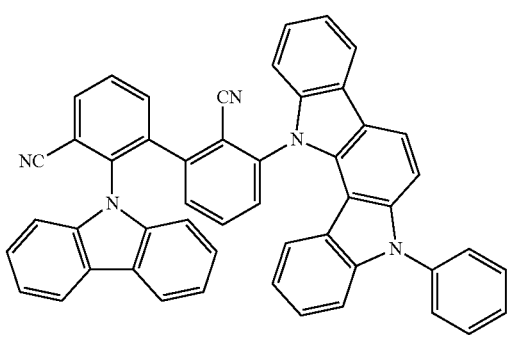

417
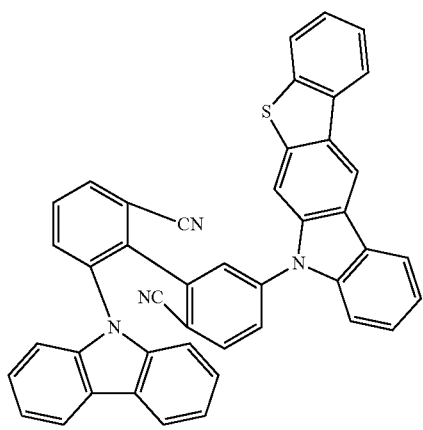
419
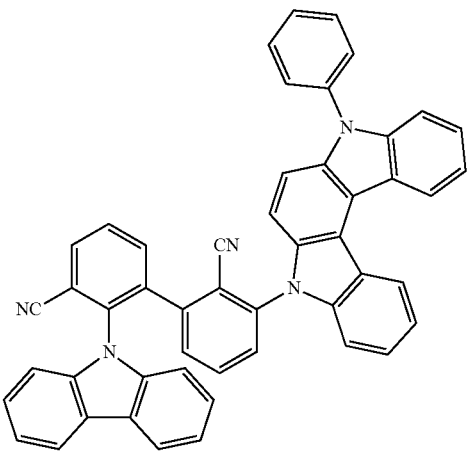
418
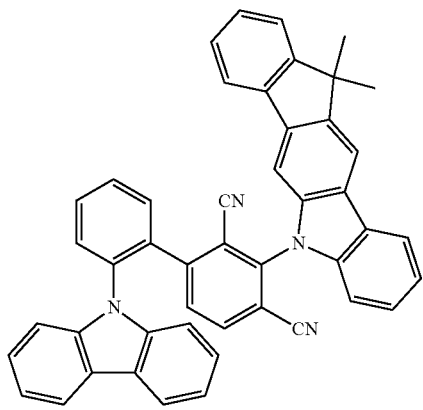
420
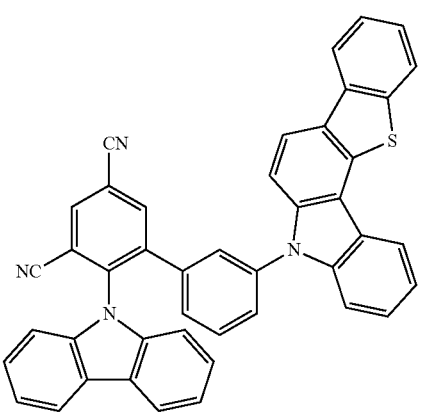
421
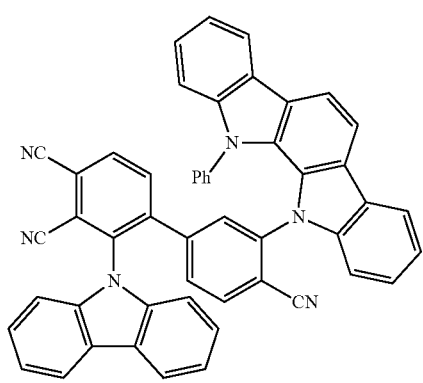
422
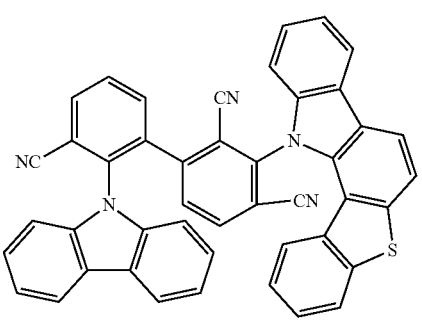

-continued
423
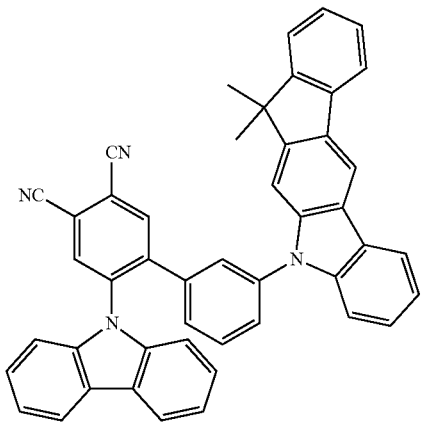
424
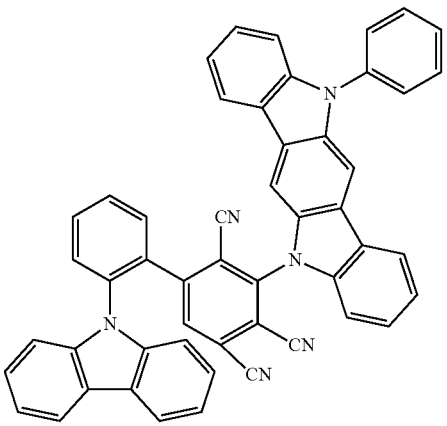
425
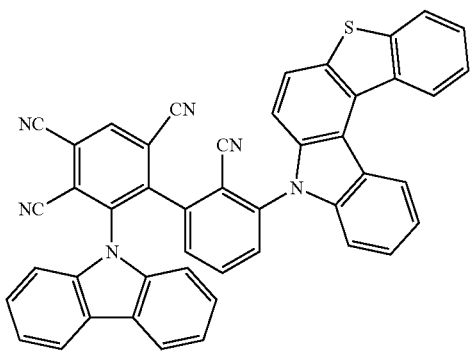
426
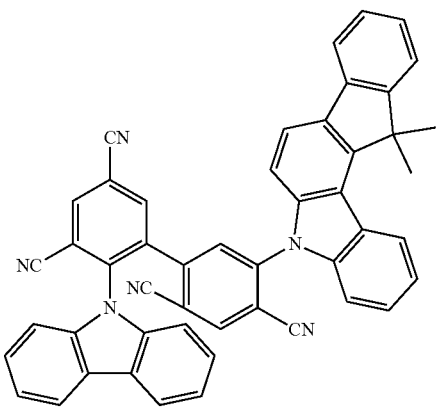
427
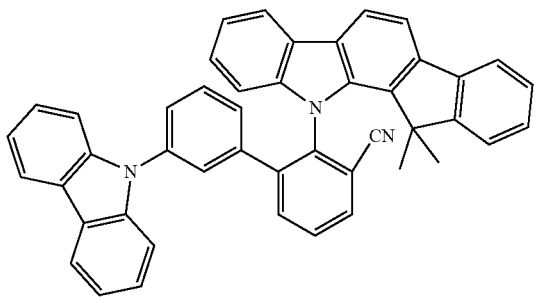
428
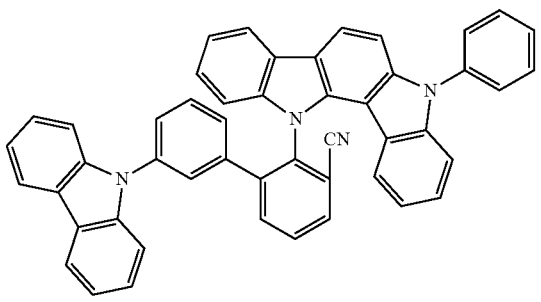
429
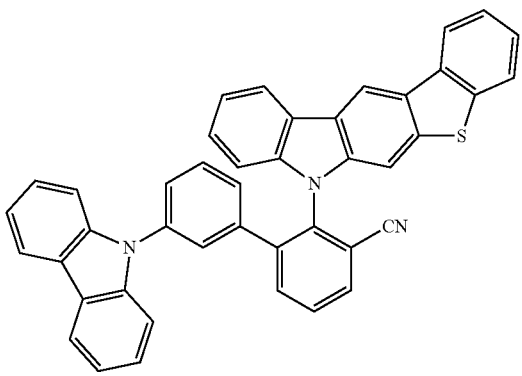
430
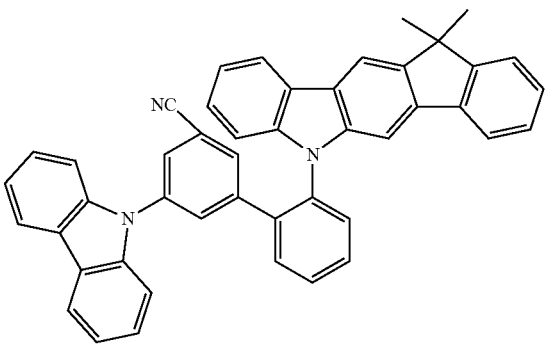

-continued
| 431 | 432 |
|---|---|
| 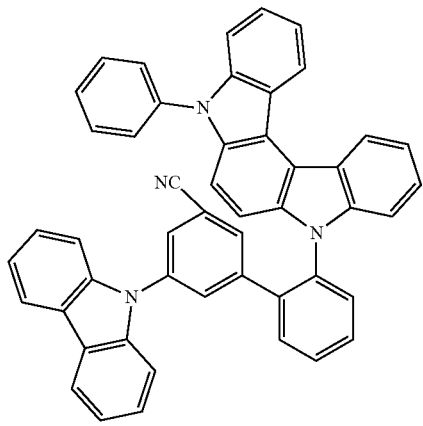 | 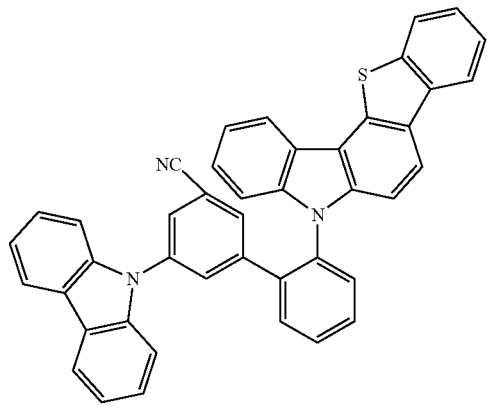 |
| 433 | 434 |
| 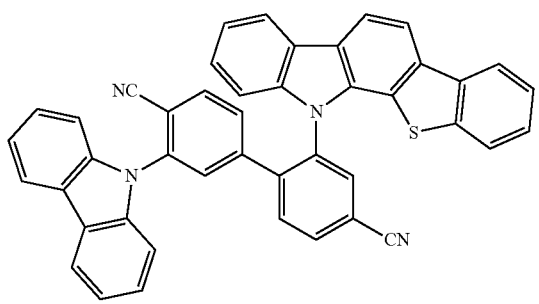 | 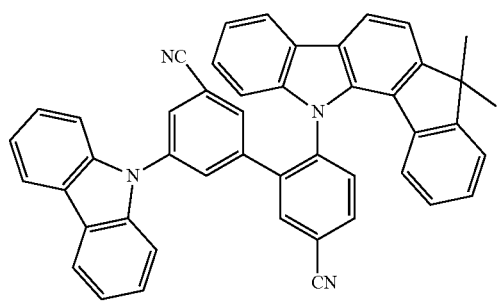 |
| 435 | 436 |
| 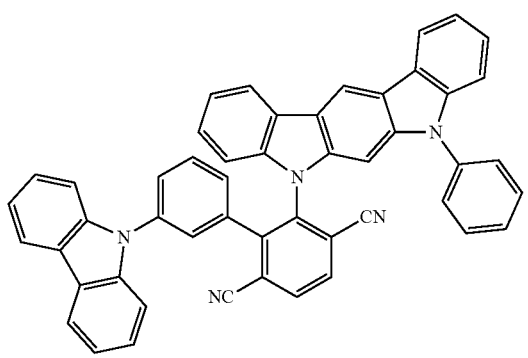 | 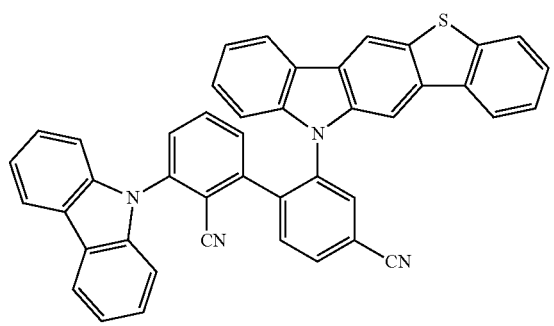 |
| 437 | 438 |
| 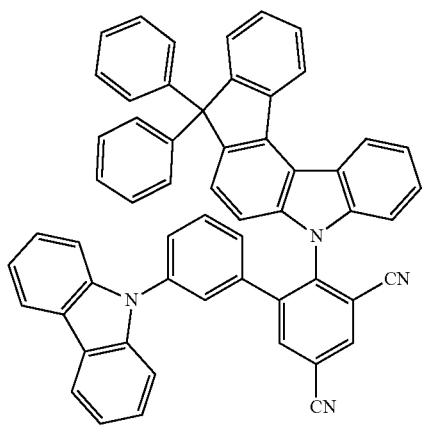 | 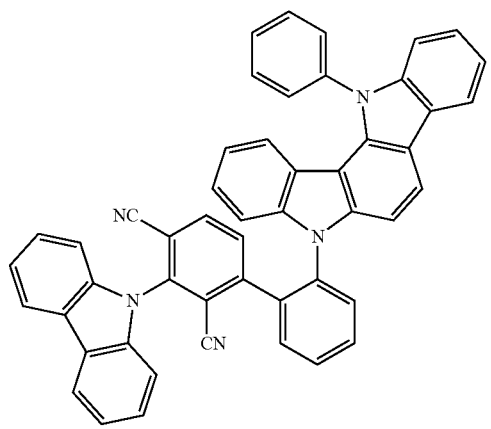 |

439
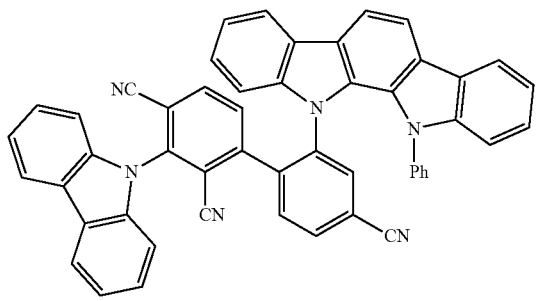
440
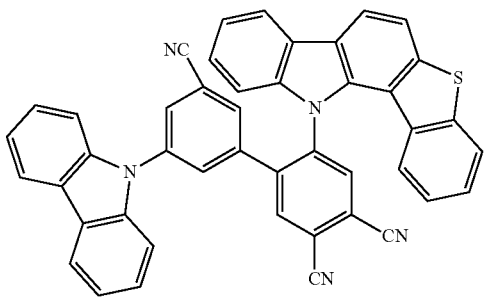
441
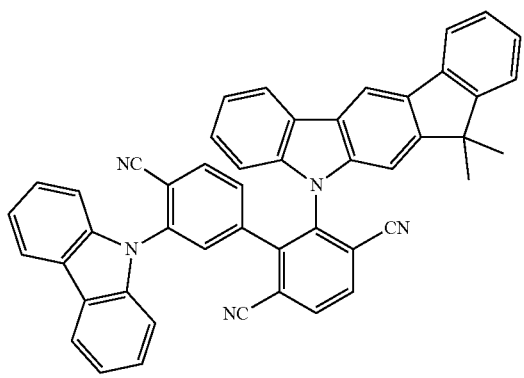
442
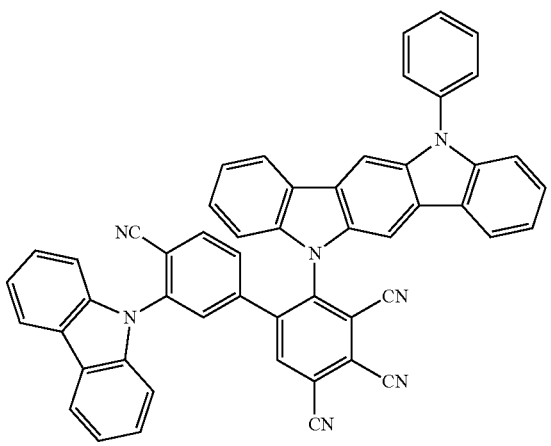
443
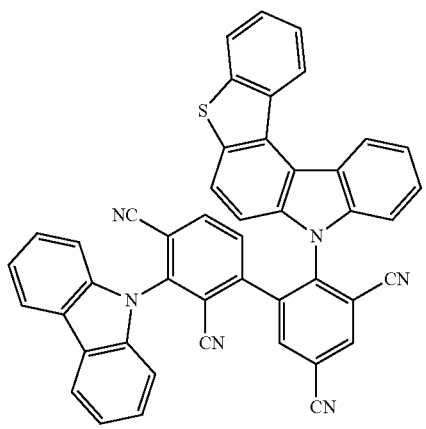
444
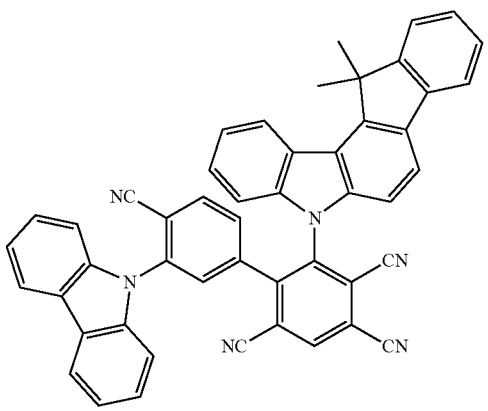
445
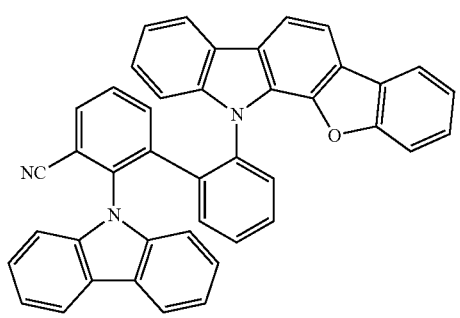
446
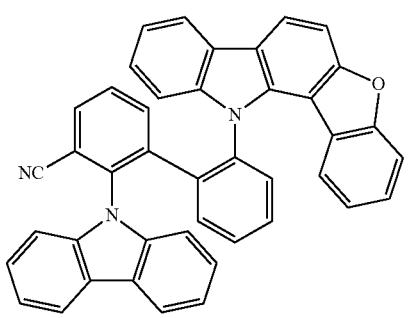

-continued
| 447 | 448 |
|---|---|
| 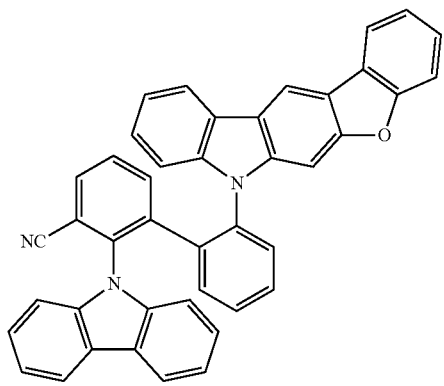 | 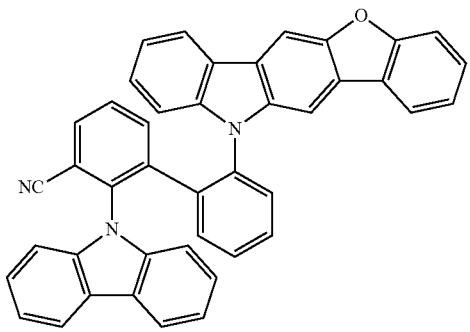 |
| 449 | 450 |
| 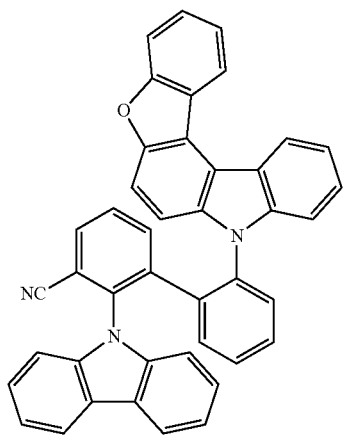 | 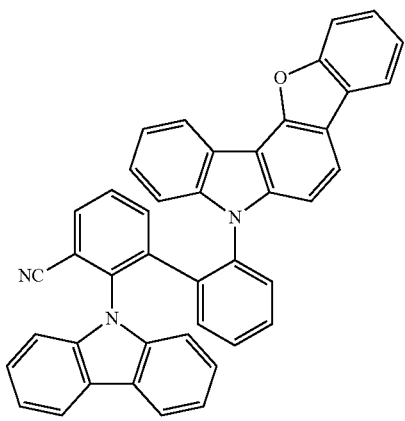 |
| 451 | 452 |
| 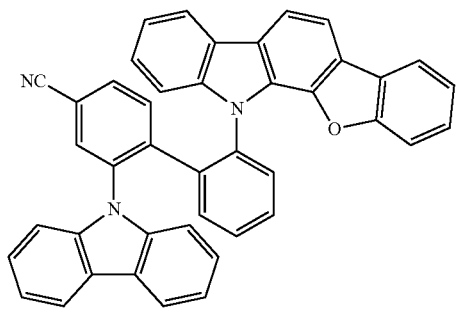 | 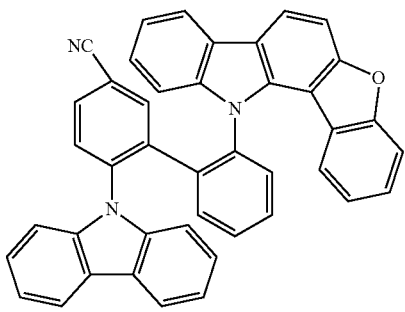 |
| 453 | 454 |
| 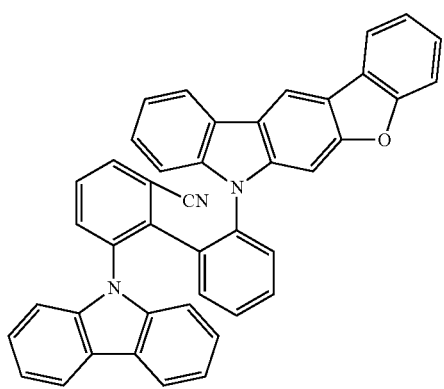 | 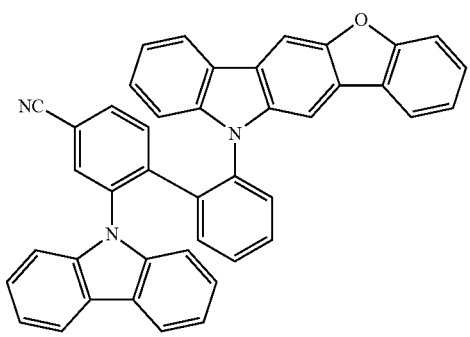 |

-continued
455
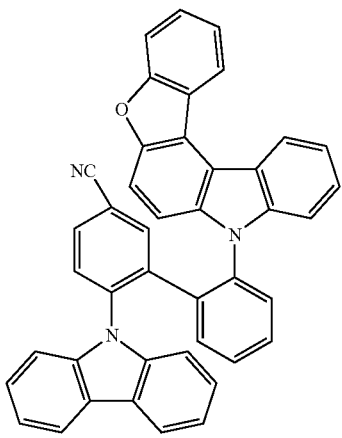
456
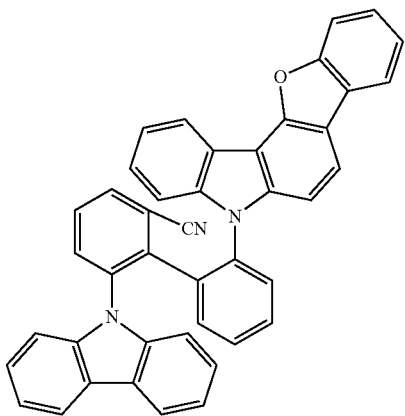
457
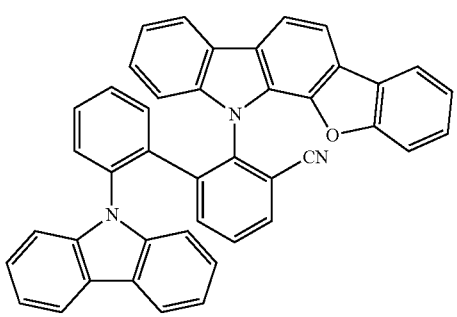
458
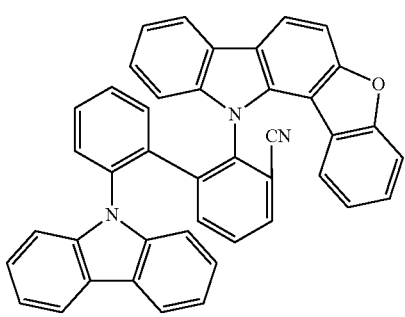
459
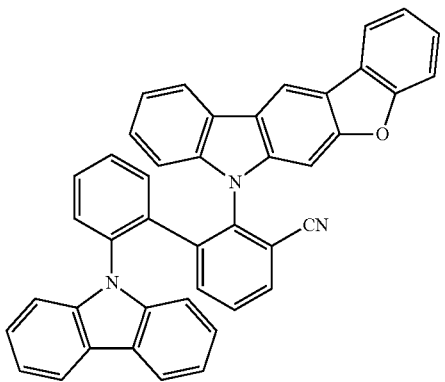
460
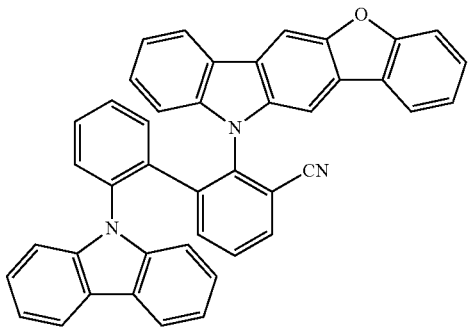
461
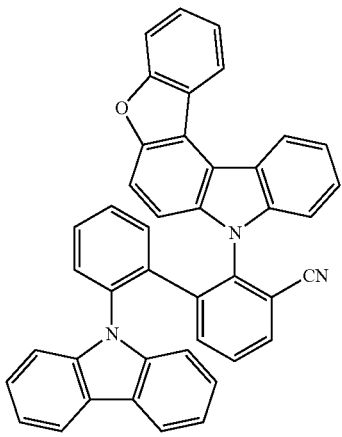
462
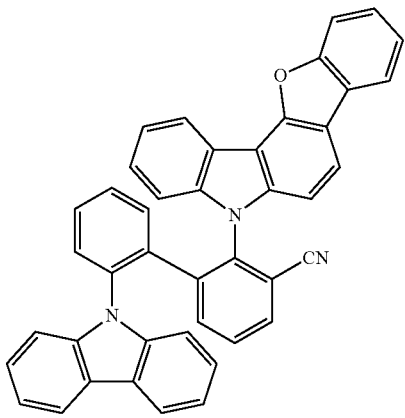

-continued
563
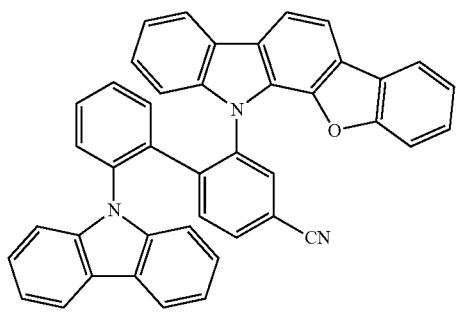
463
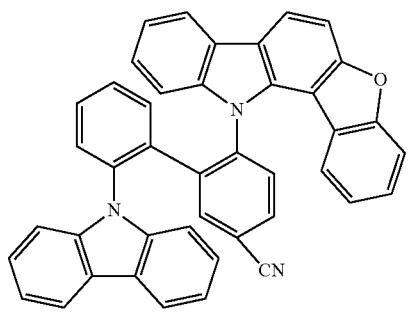
464
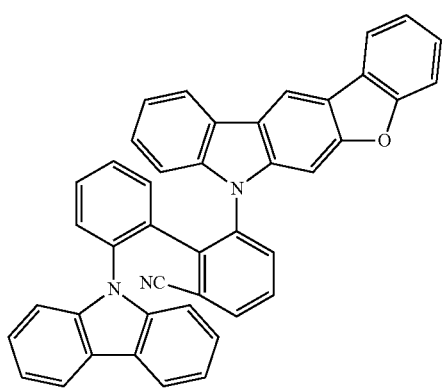
465
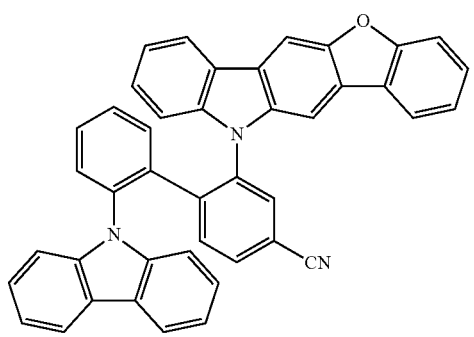
466
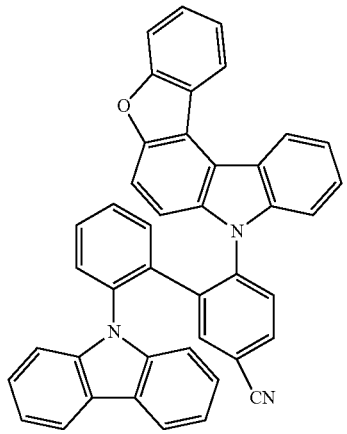
467
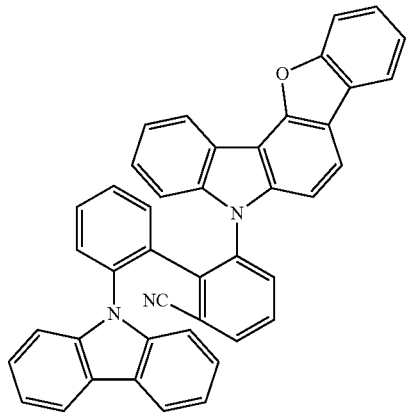
468
564
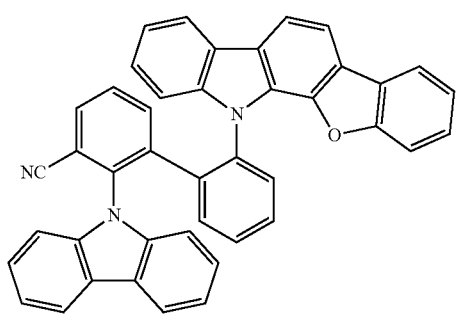
469
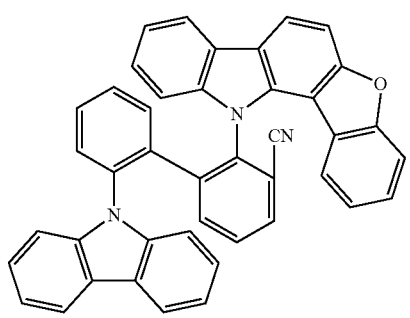
470

-continued
471 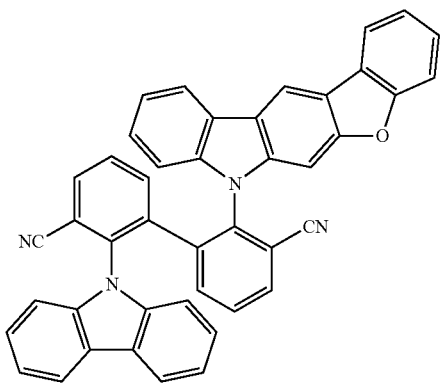
472 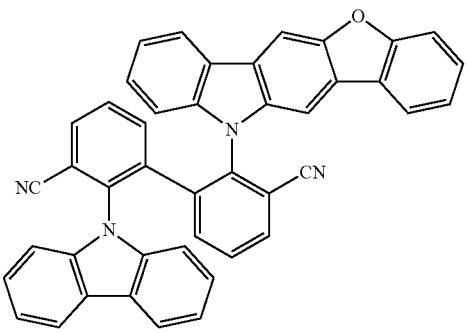
473 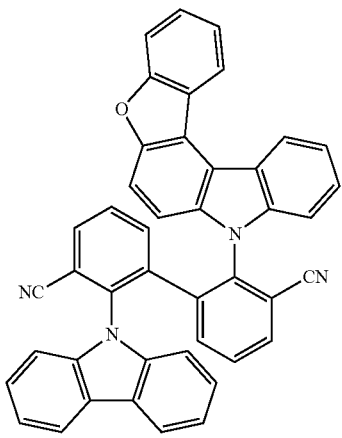
474 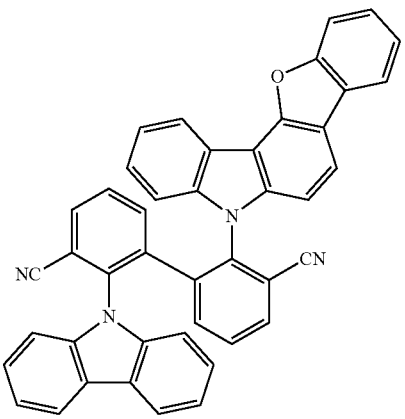
475 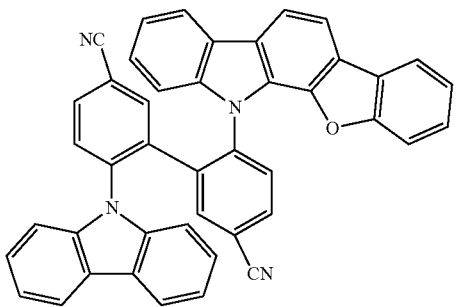
476 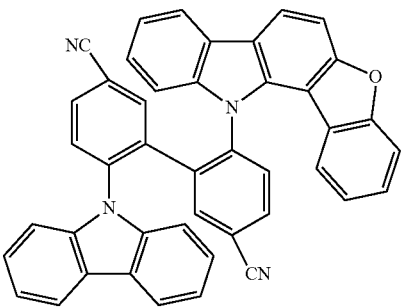
477 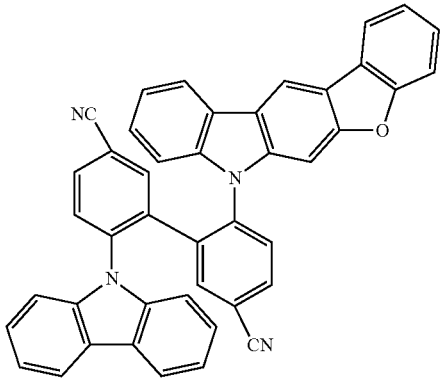
478 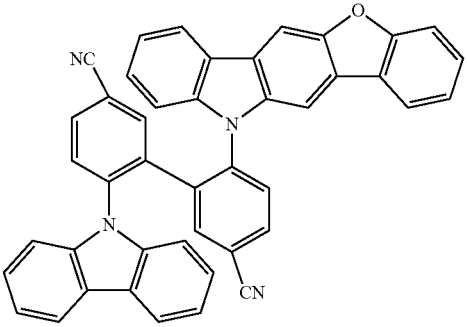

-continued
479
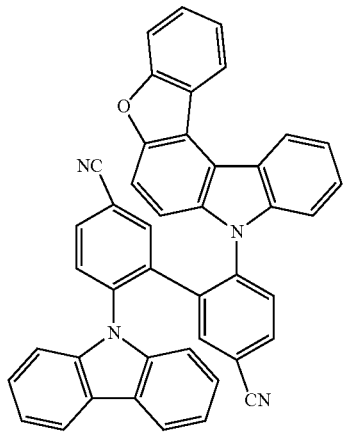
480
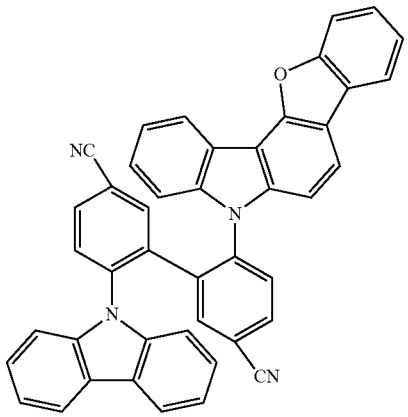
481
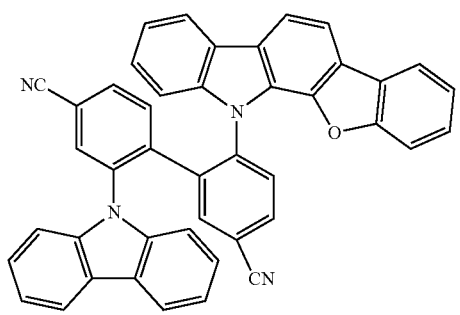
482
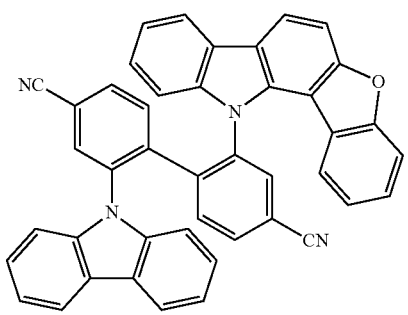
483
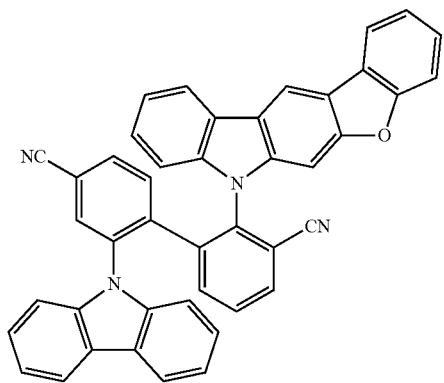
484
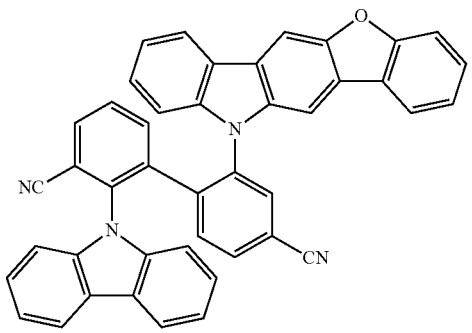
485
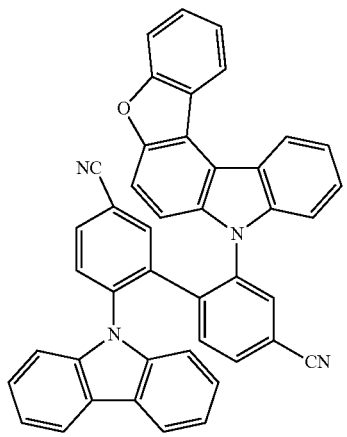
486
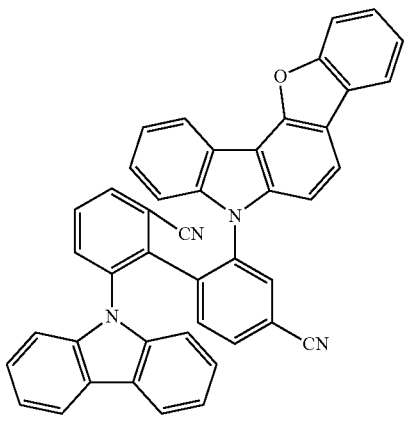

-continued
| 487 | 488 |
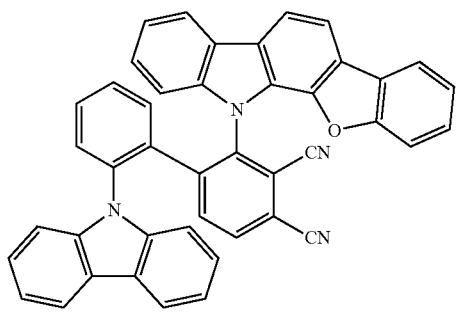
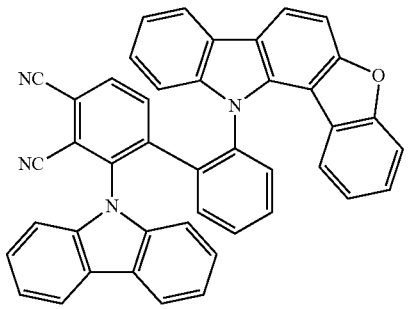
| 489 | 490 |
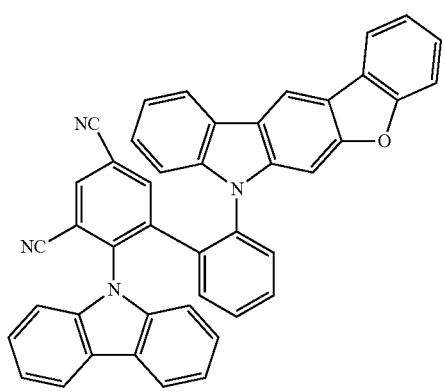
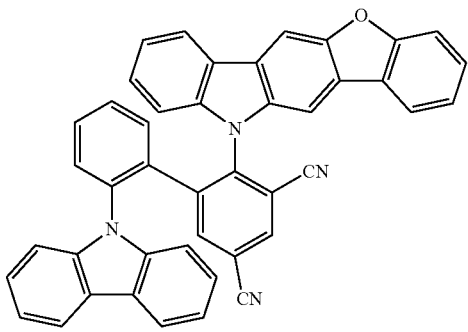
| 491 | 492 |
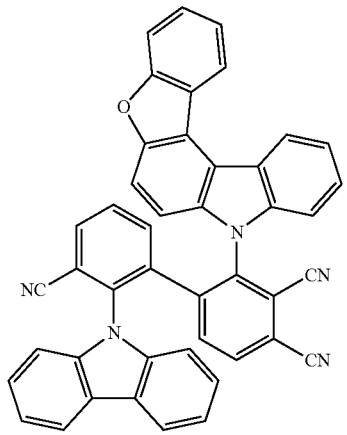
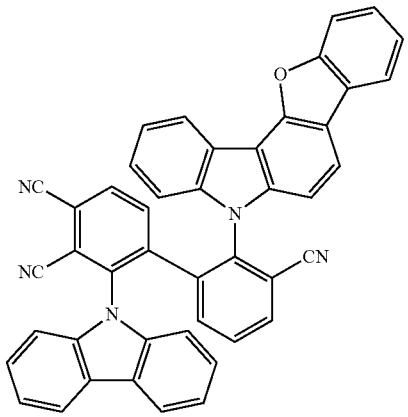
| 493 | 494 |
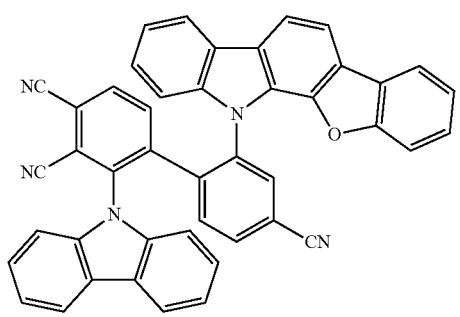
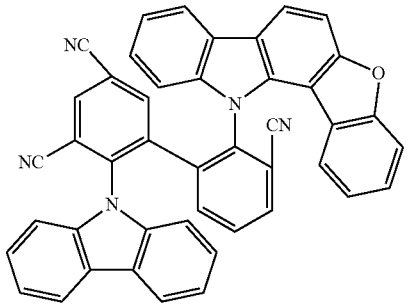

-continued
495
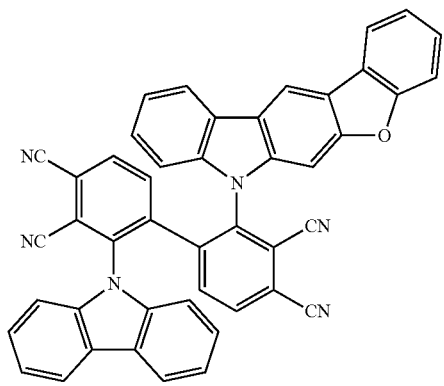
496
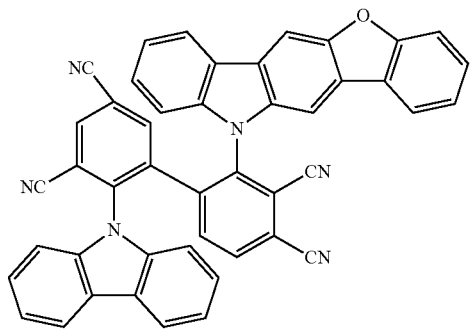
497
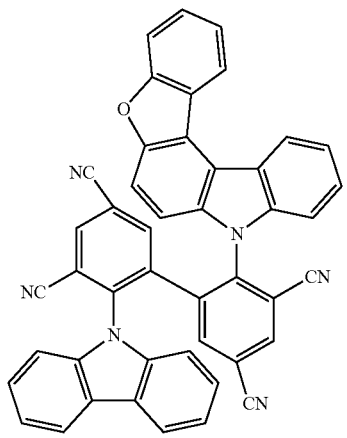
498
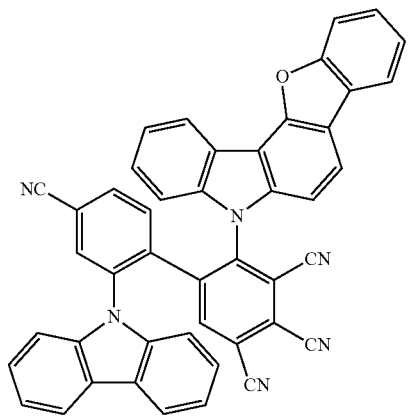
499
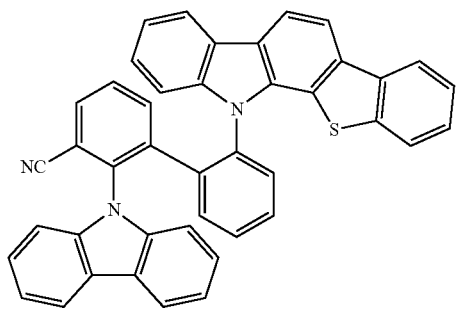
500
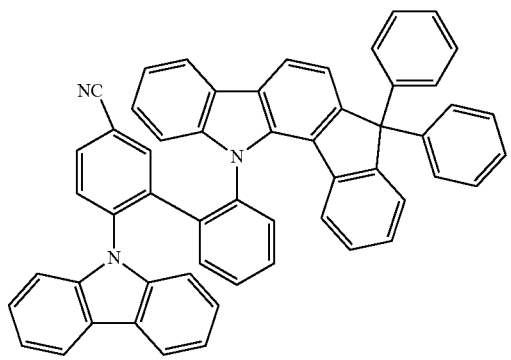
501
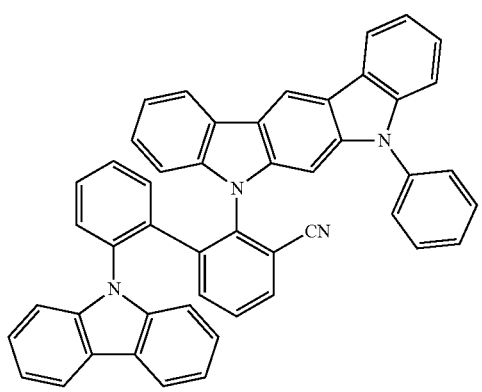
502
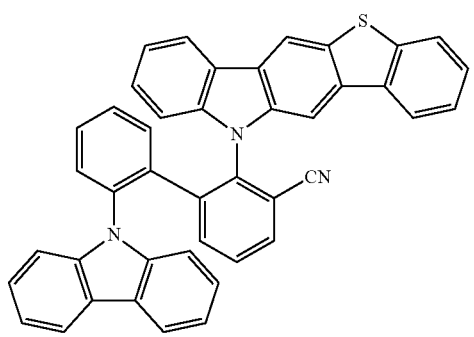

-continued
| 503 | 504 |
|---|---|
| 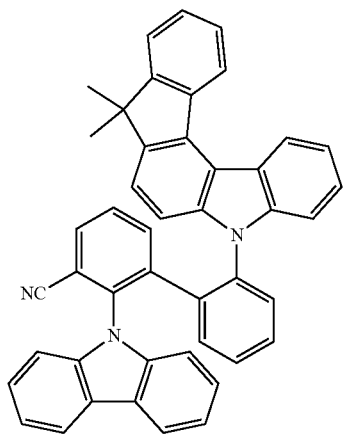 | 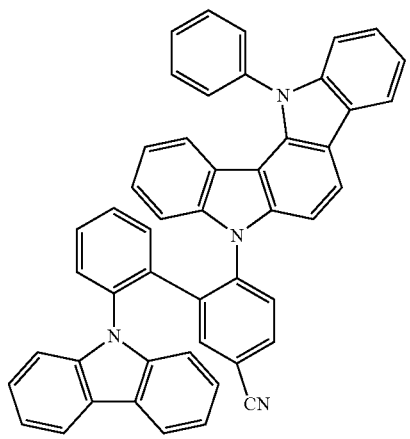 |
| 505 | 506 |
| 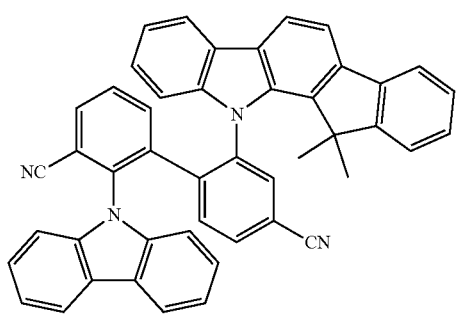 | 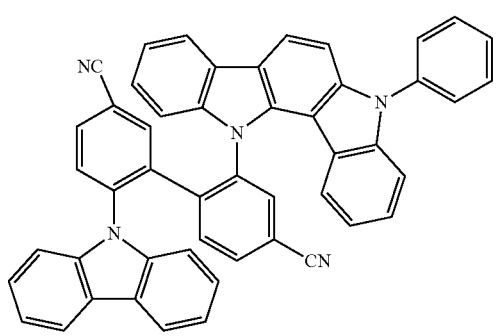 |
| 507 | 508 |
| 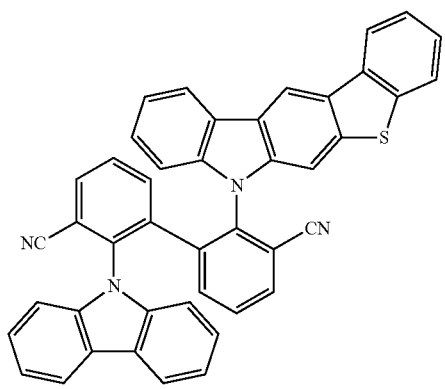 | 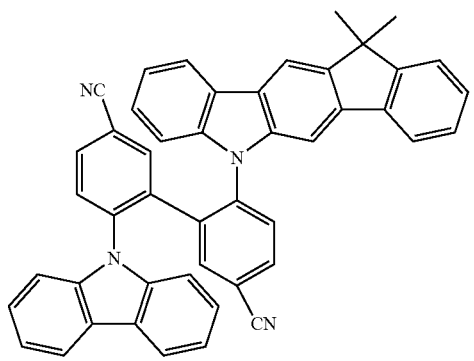 |
| 509 | 510 |
| 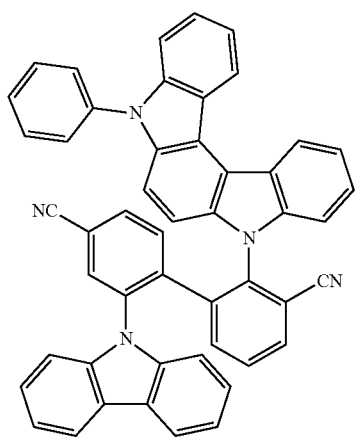 | 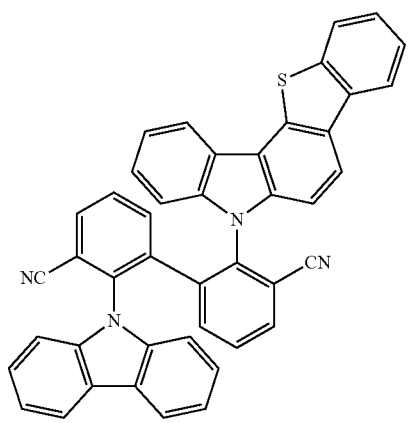 |

-continued
511
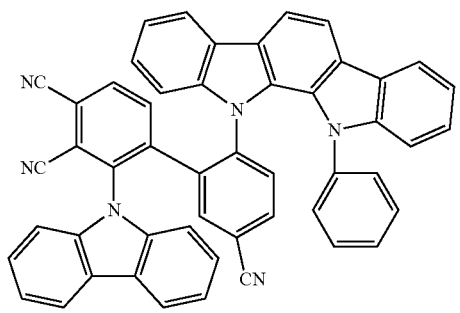
512
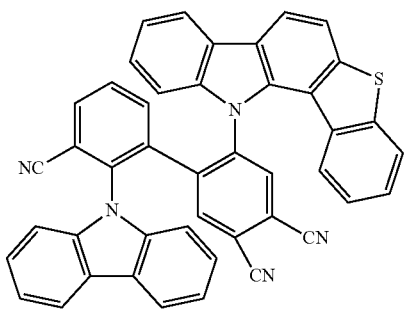
513
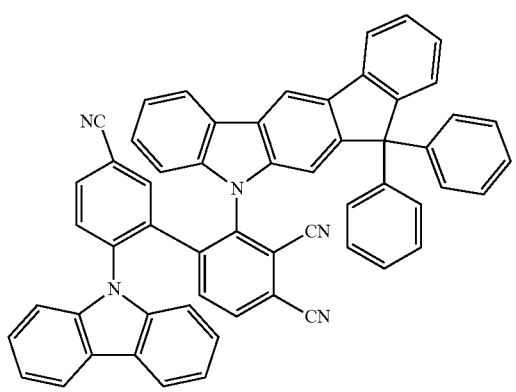
514
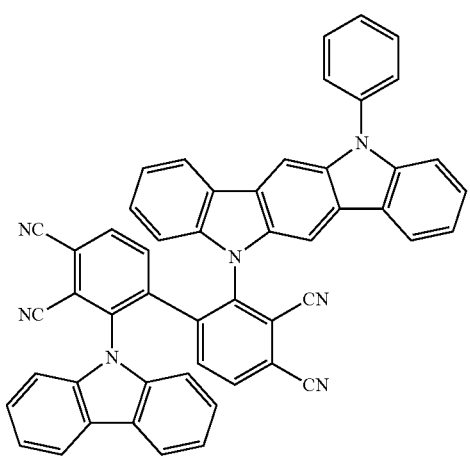
515
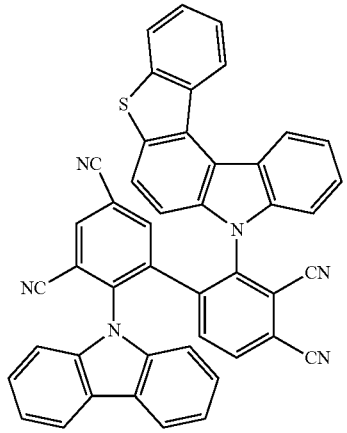
516
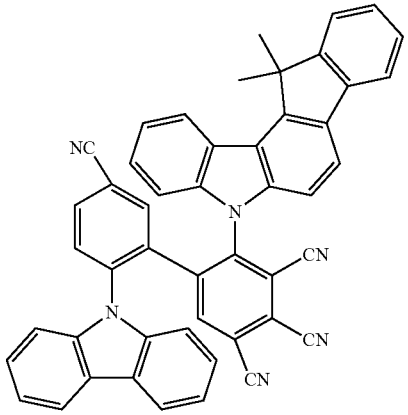
517
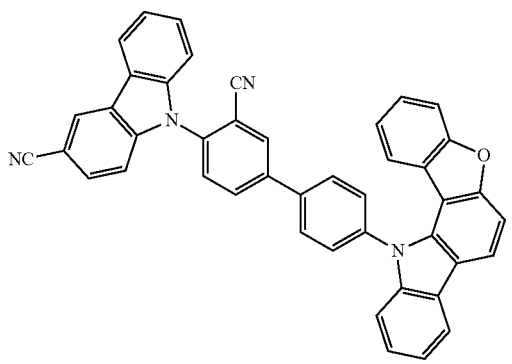
518
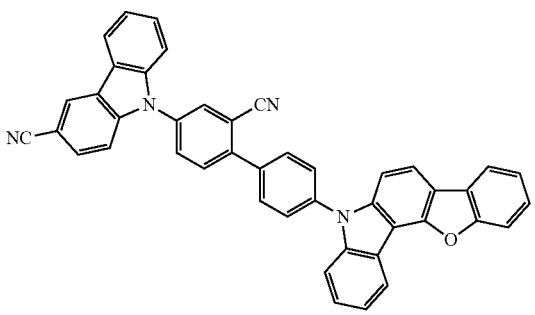

-continued
519
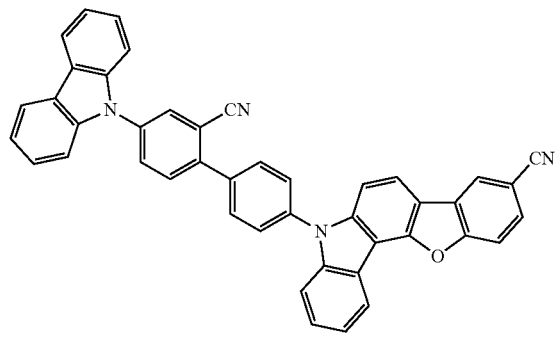
520
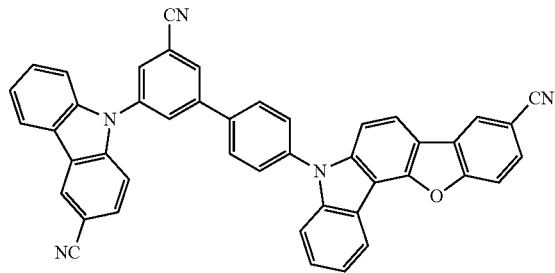
521
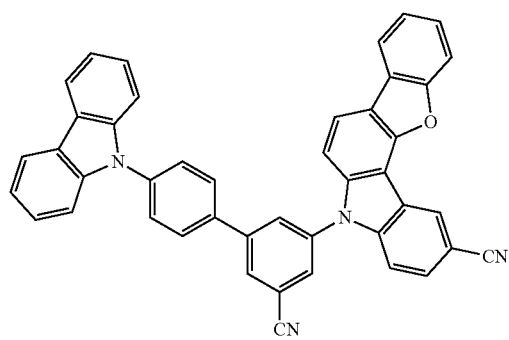
522
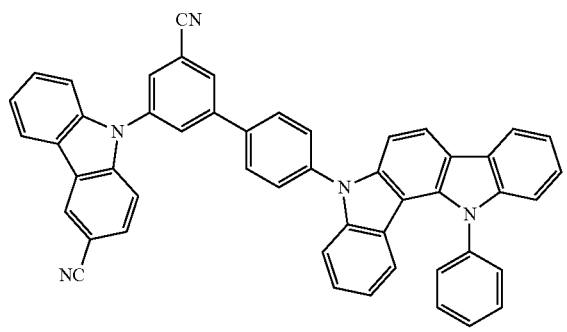
523
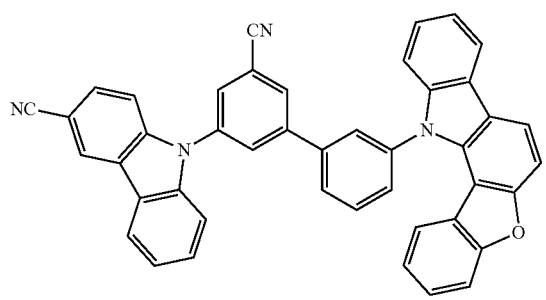
524
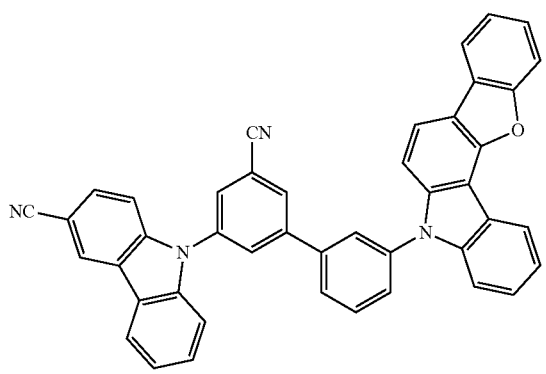
525
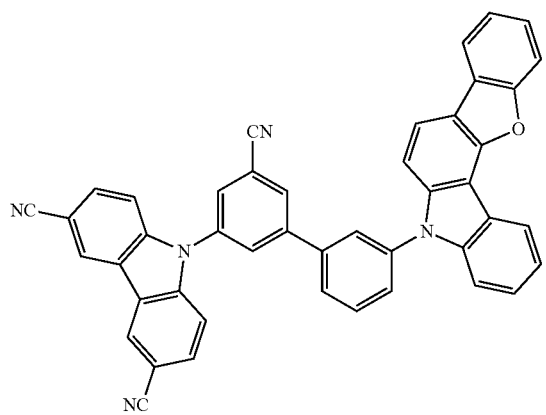
523
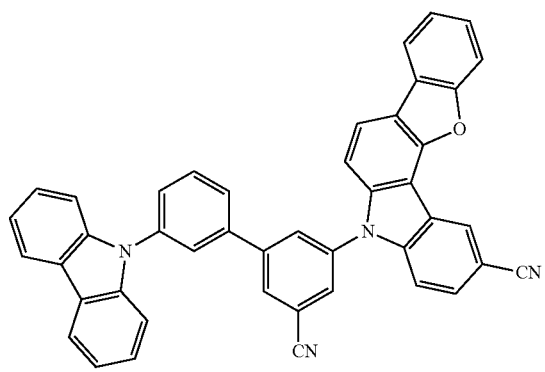

-continued
527
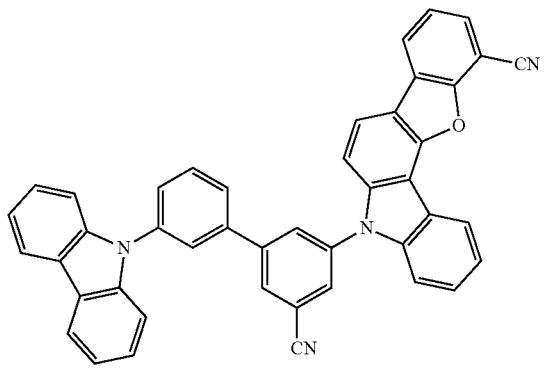
528
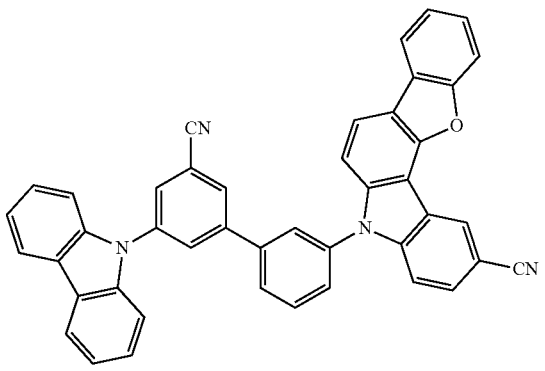
529
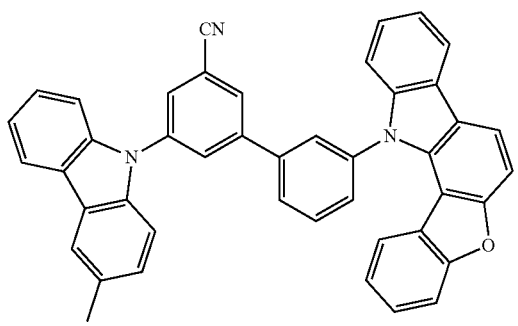
530
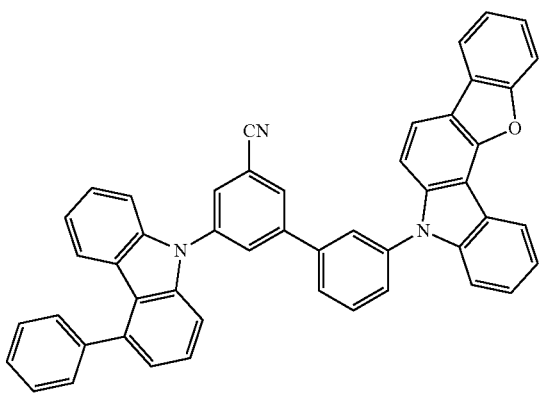
531
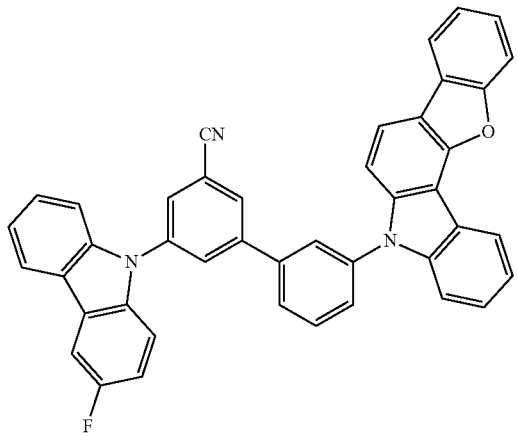
532
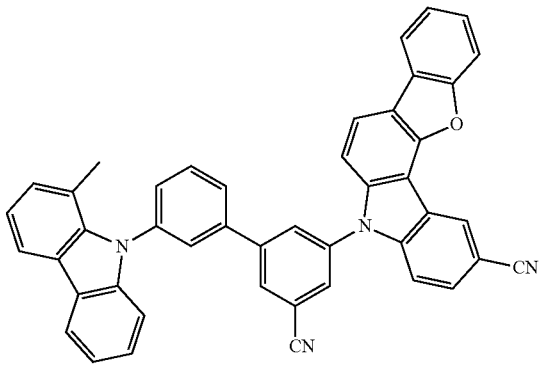
533
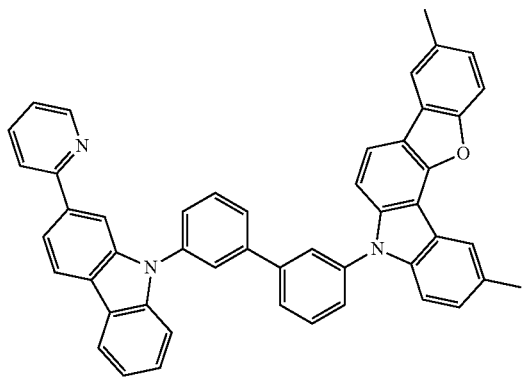
534
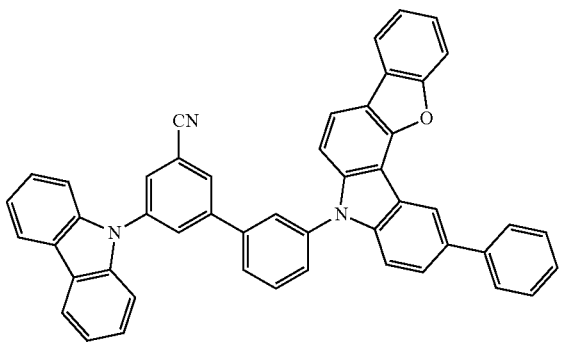

-continued
535 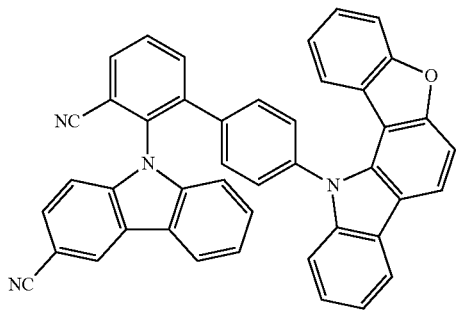
536 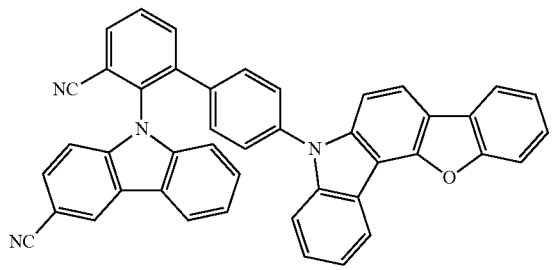
537 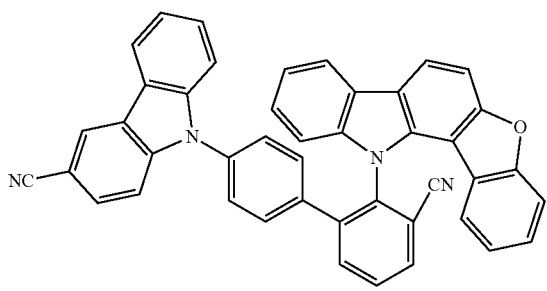
538 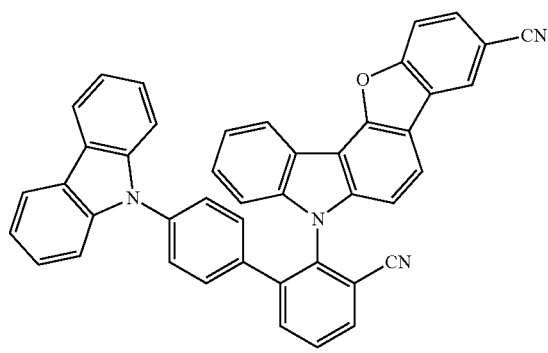
539 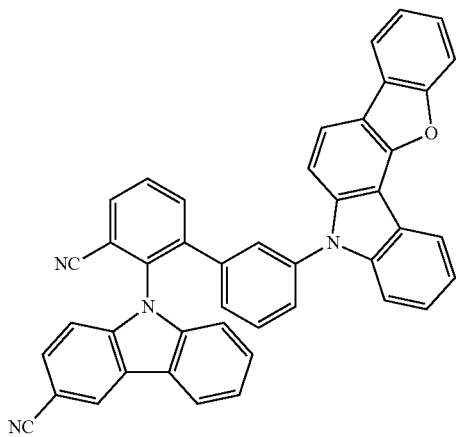
540 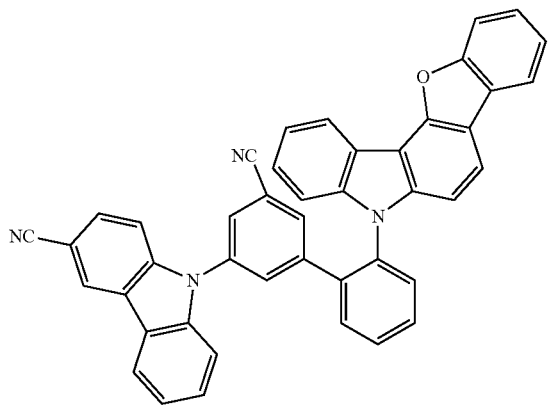
541 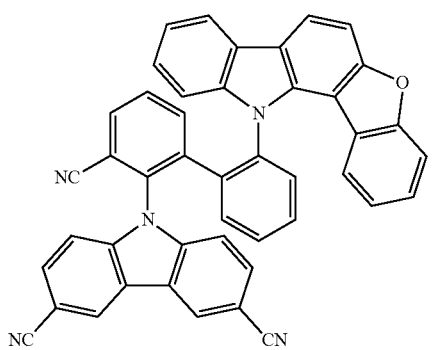
542 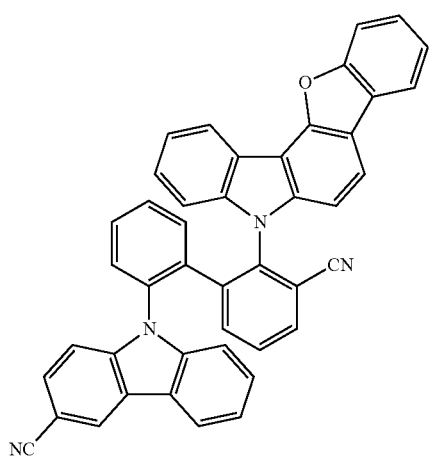

543
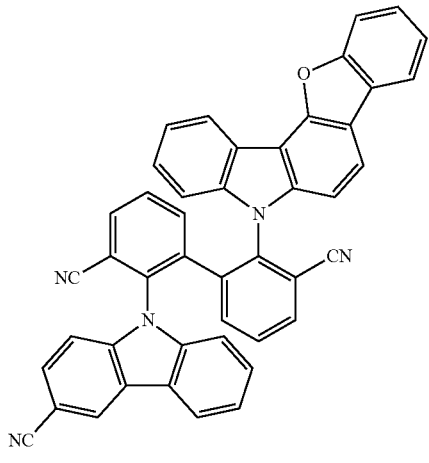
544
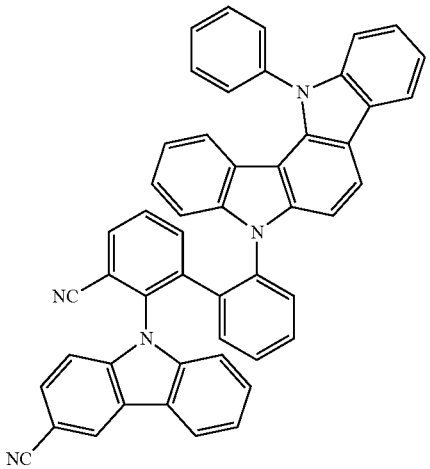
545
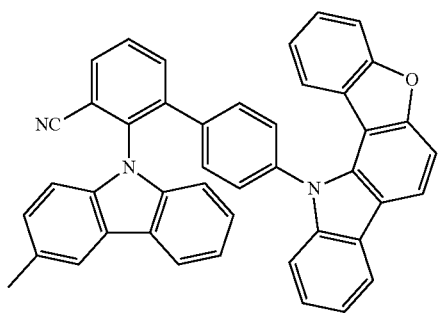
546
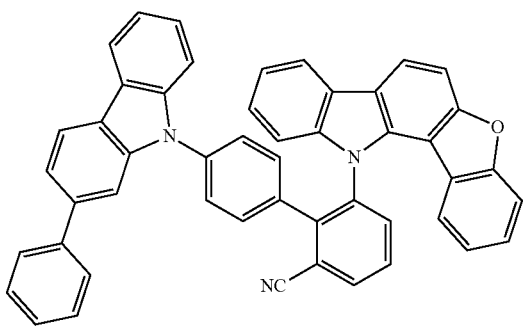
547
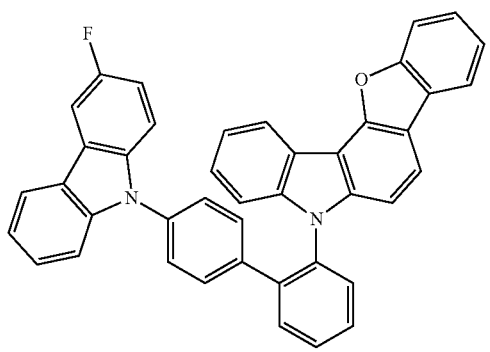
548
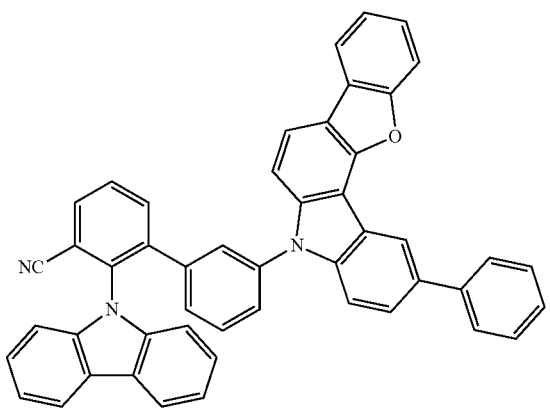

-continued
549
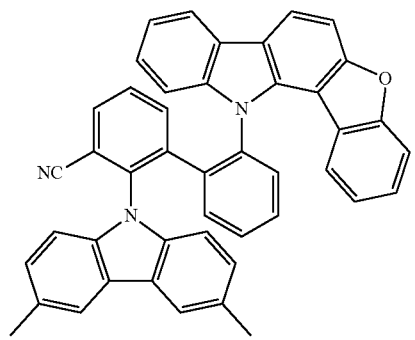
550
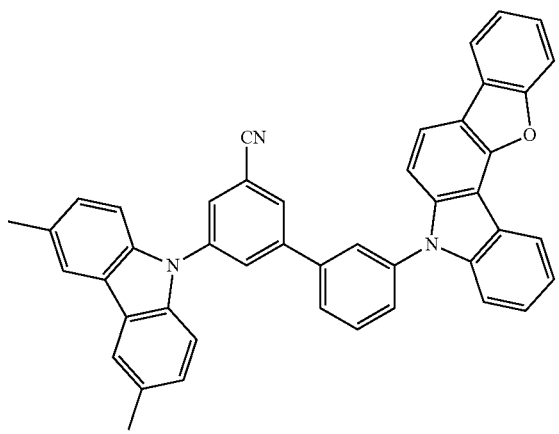
551
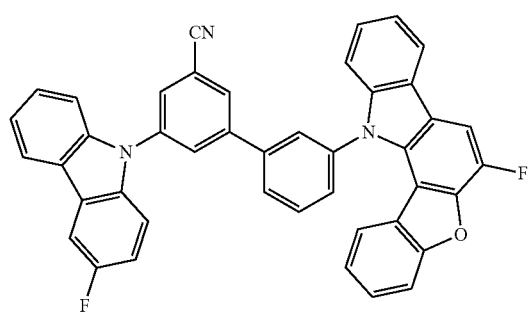
552
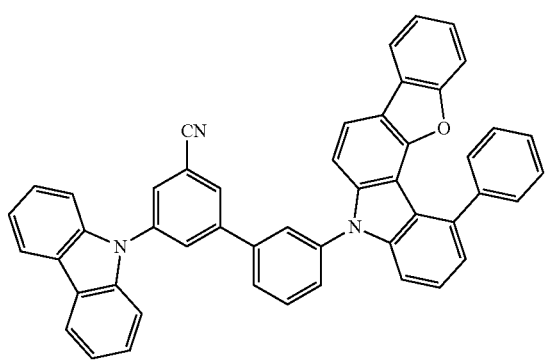
553
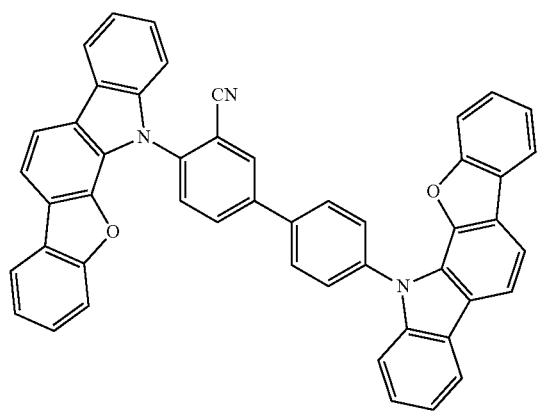
554
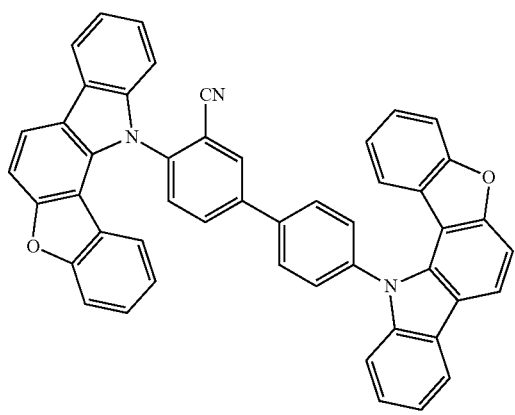
555
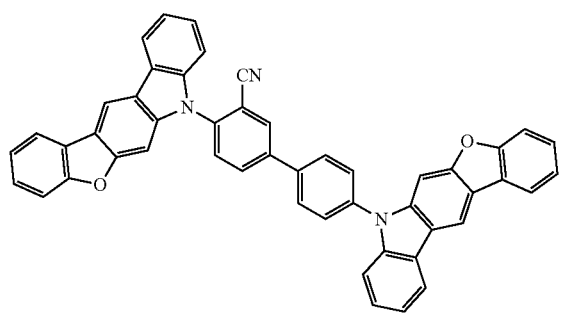
556
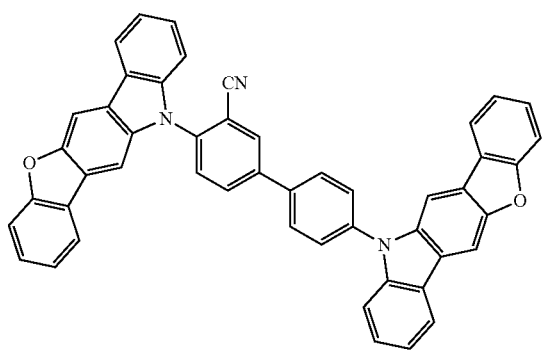

-continued
557
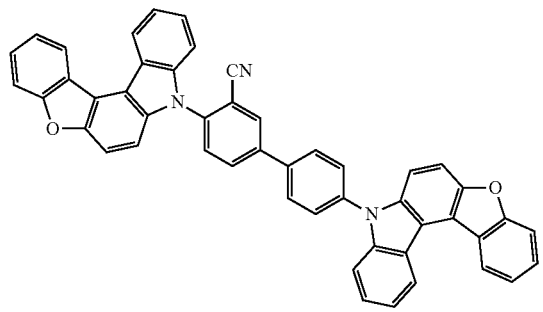
558
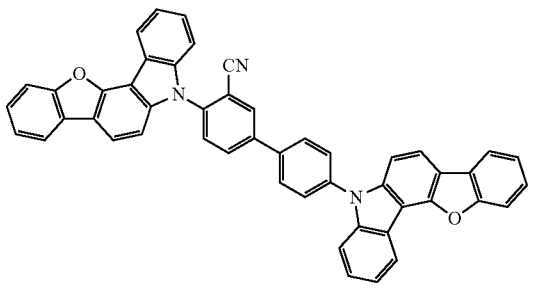
559
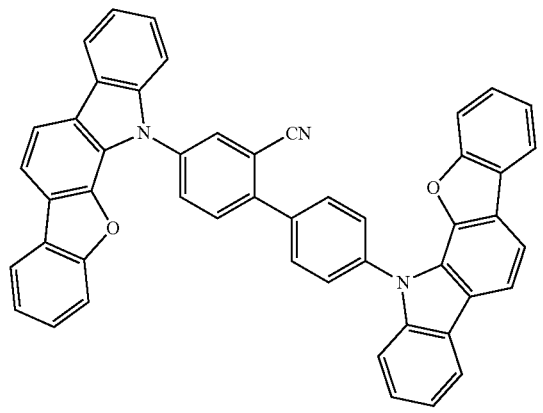
560
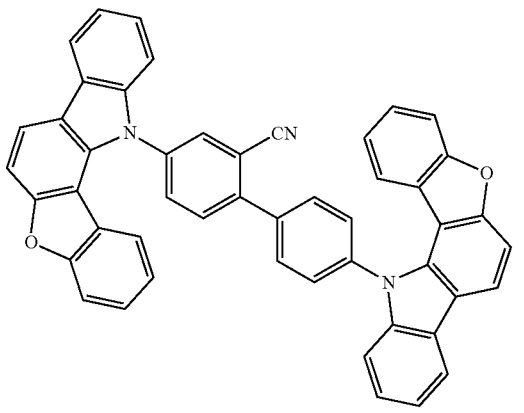
561
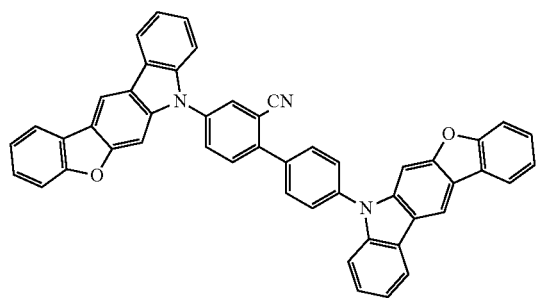
562
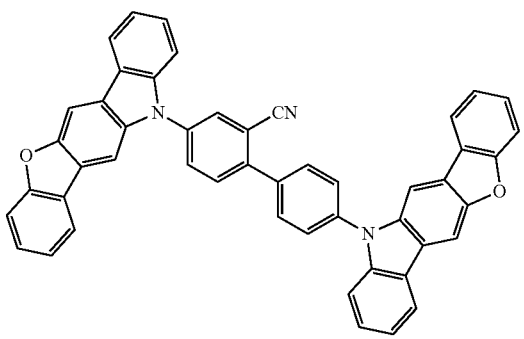
563
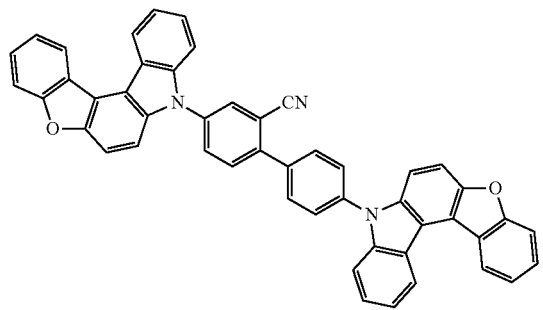
564
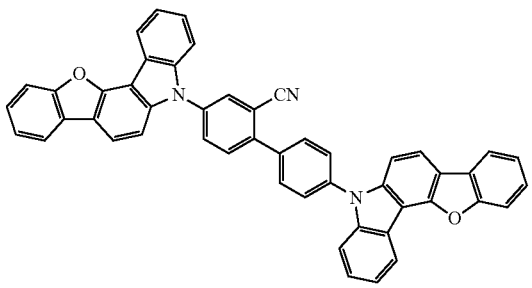

565
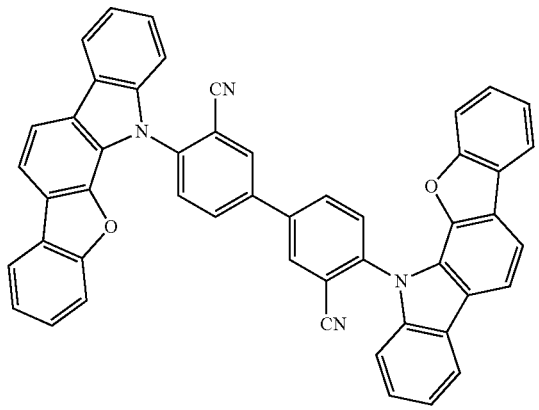
566
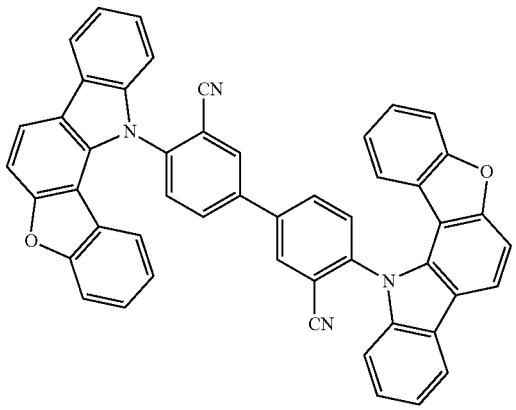
567
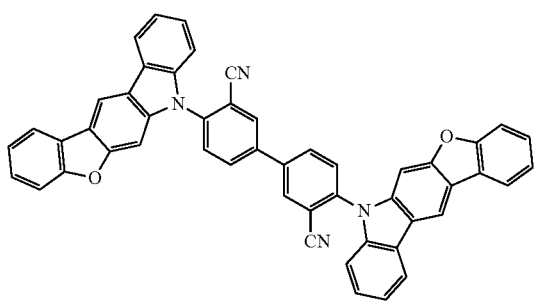
568
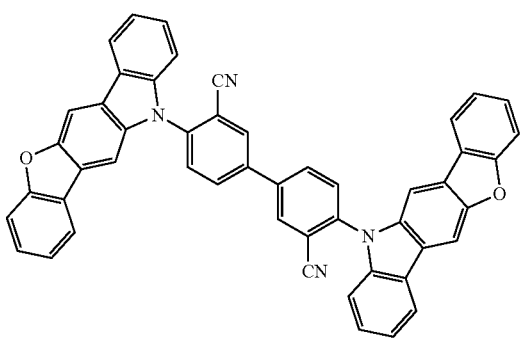
569
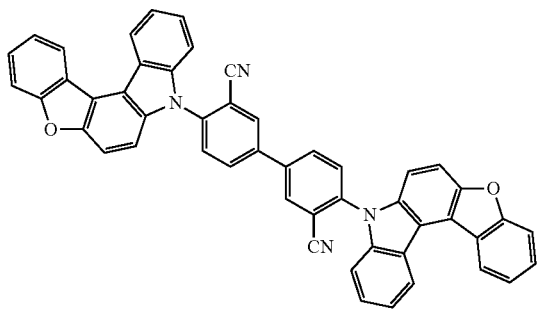
570
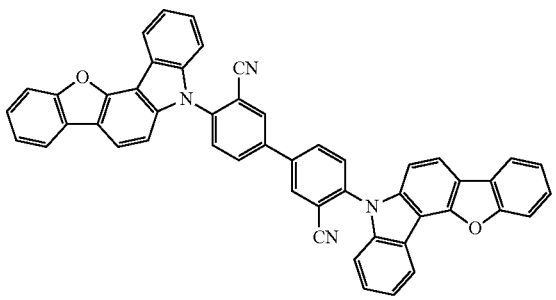
571
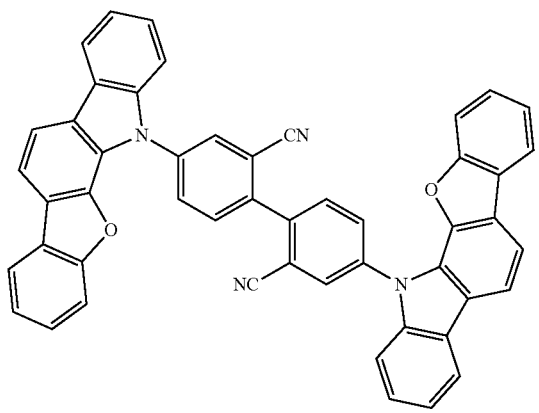
572
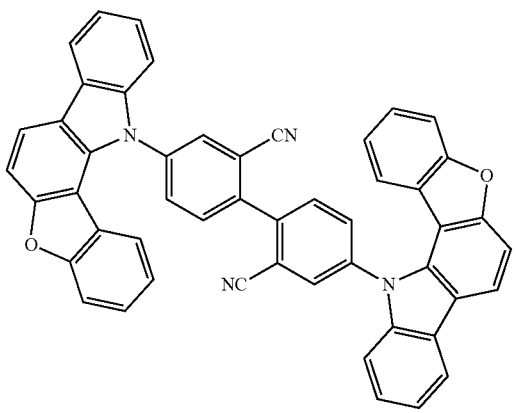

-continued
573
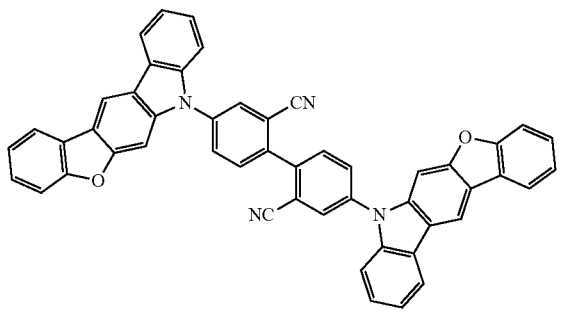
574
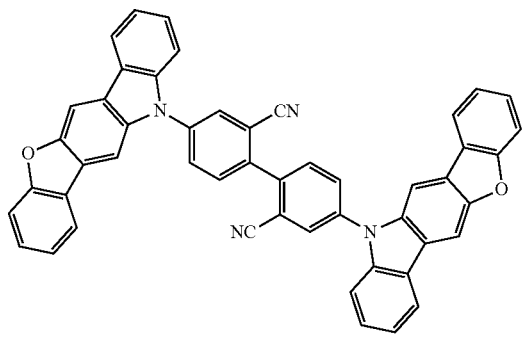
575
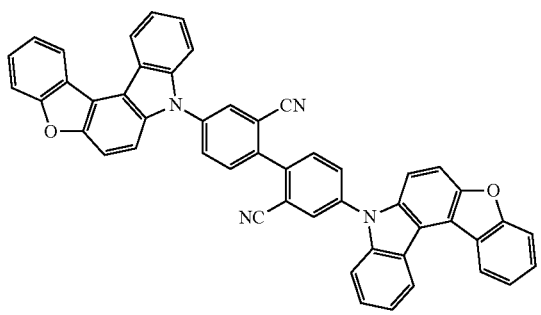
576
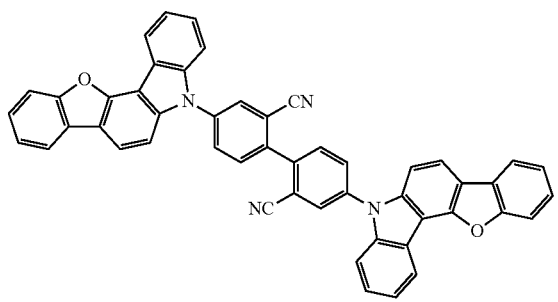
577
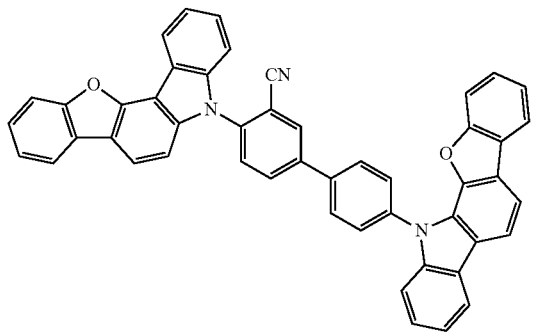
578
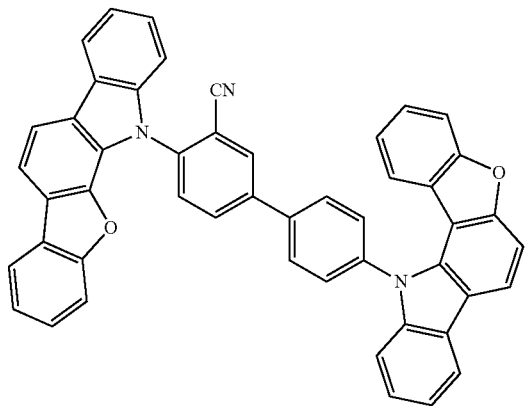
579
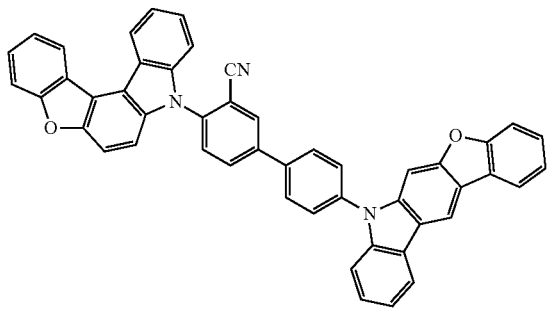
580
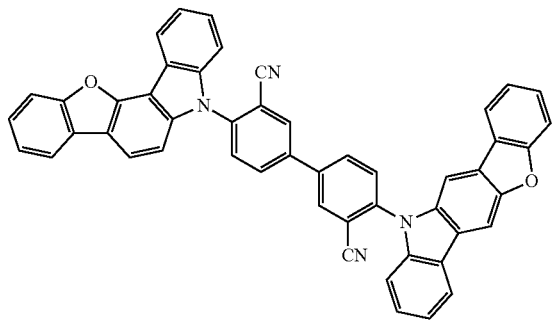

-continued
581
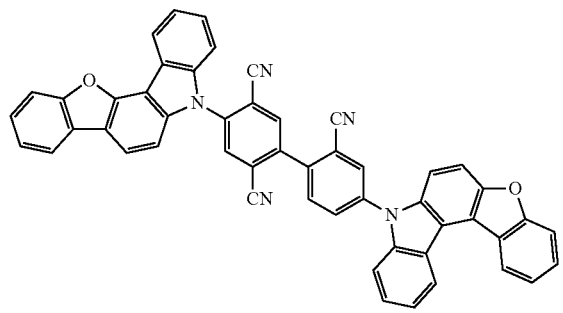
582
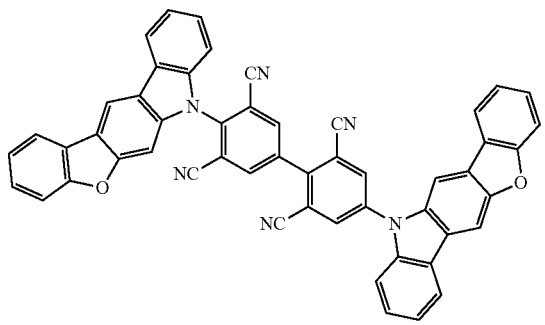
583
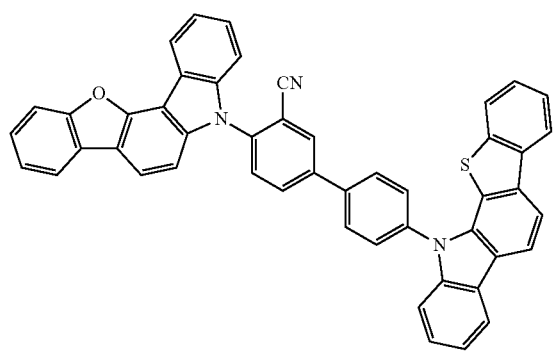
584
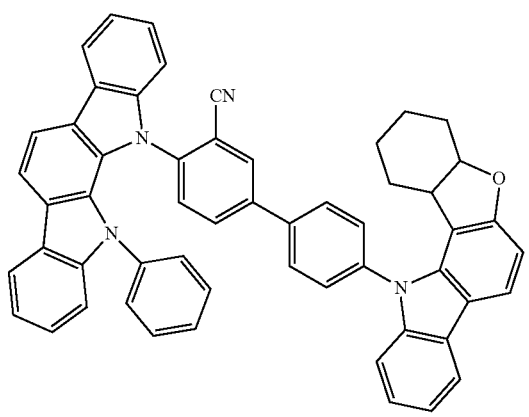
585
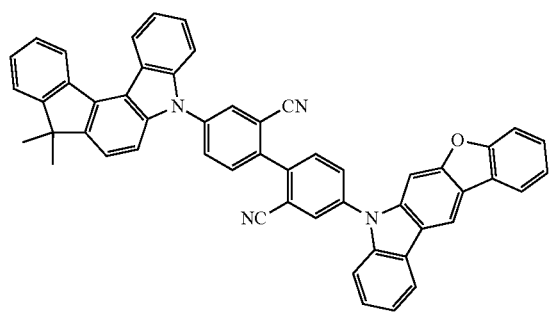
586
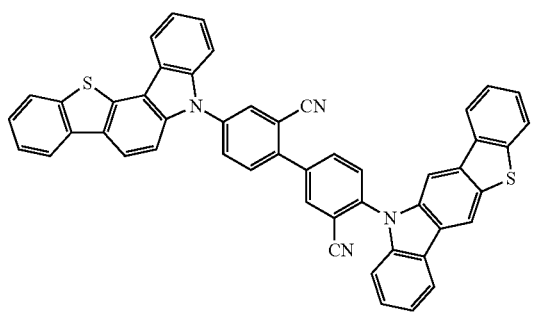
587
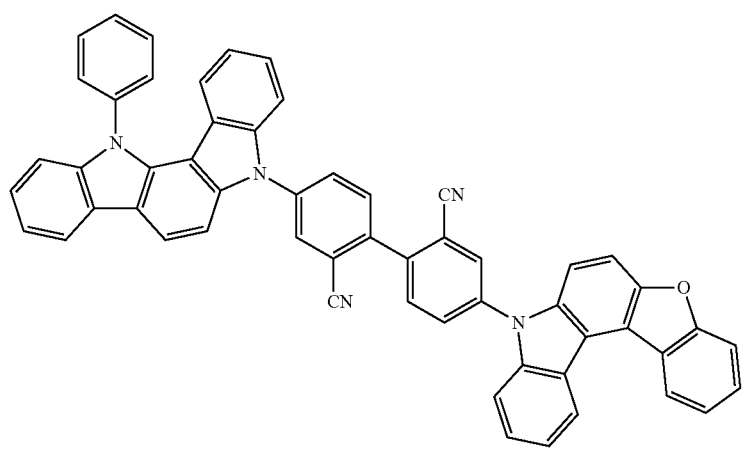

-continued
588
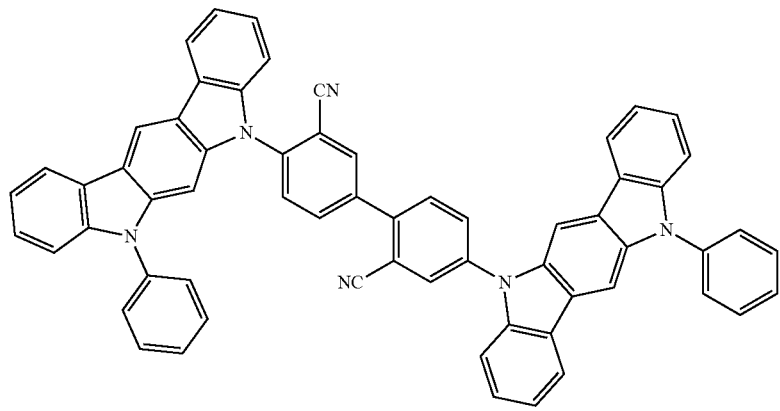
589
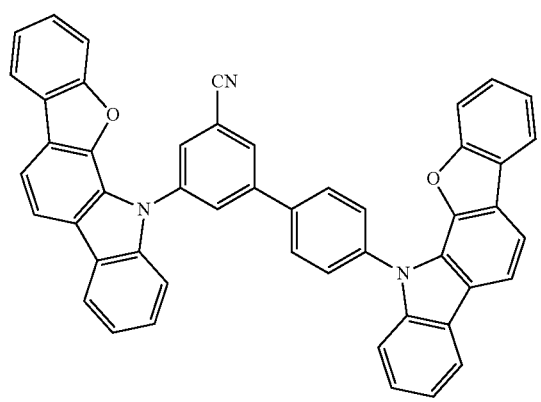
590
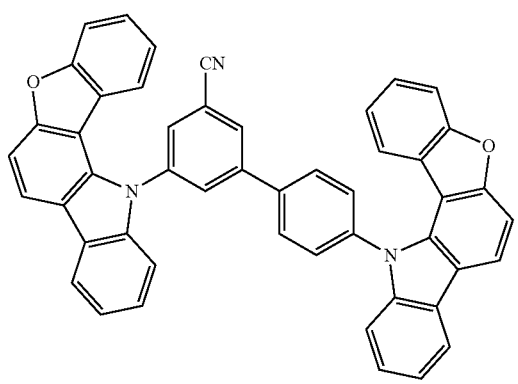
591
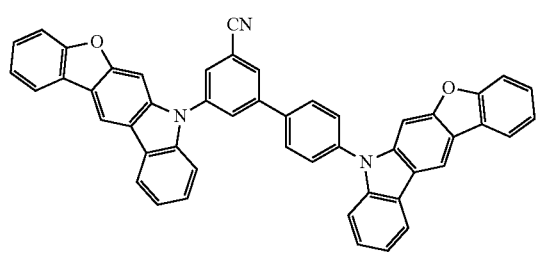
592
593
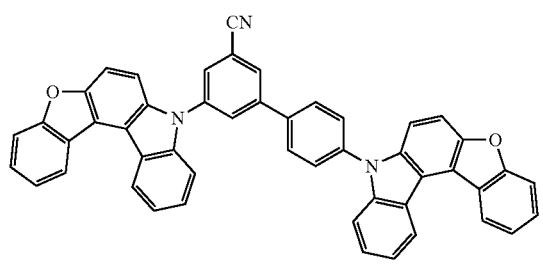
594
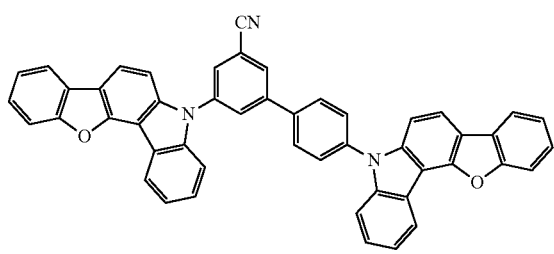

595
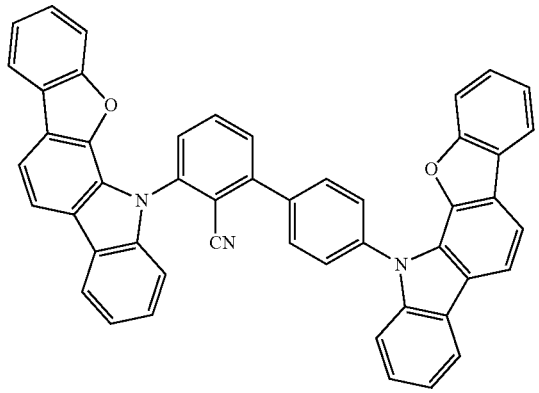
596
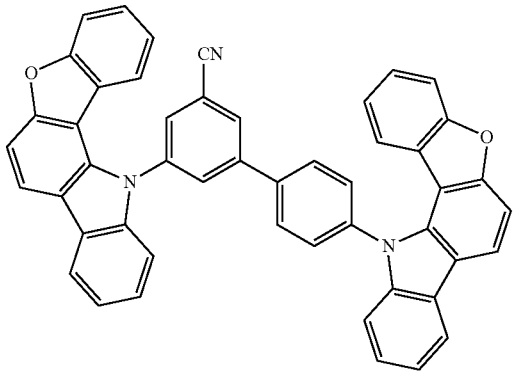
597
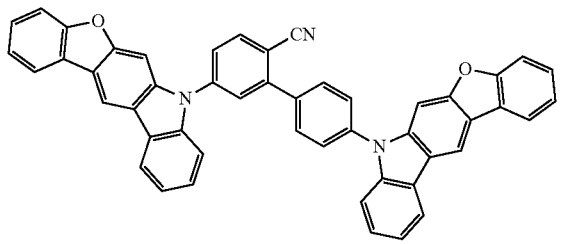
598
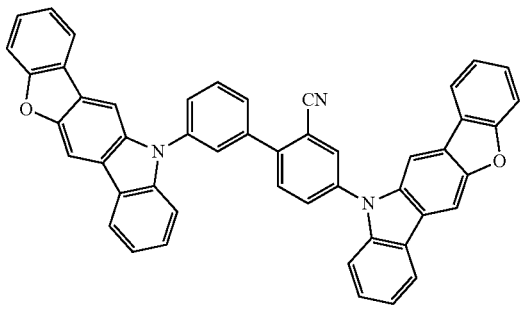
599
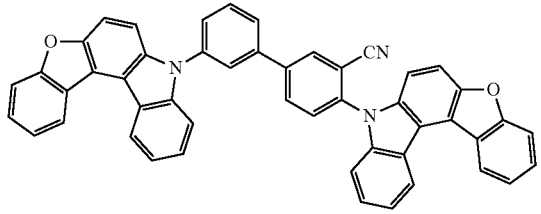
600
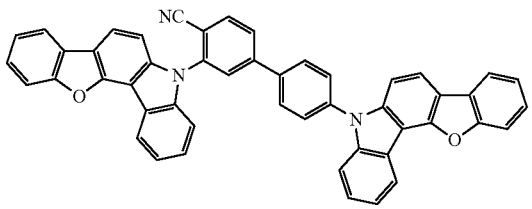
601
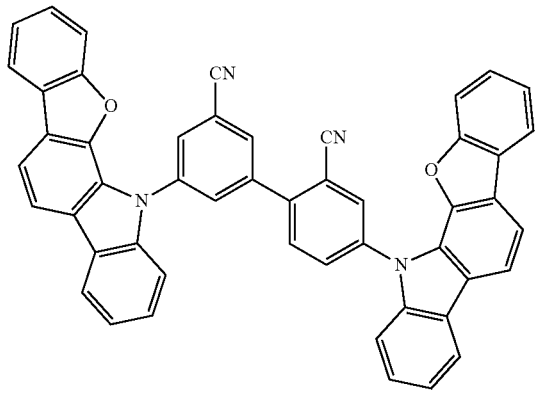
602
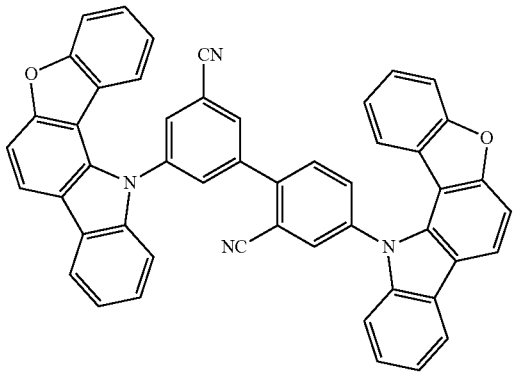

-continued
603
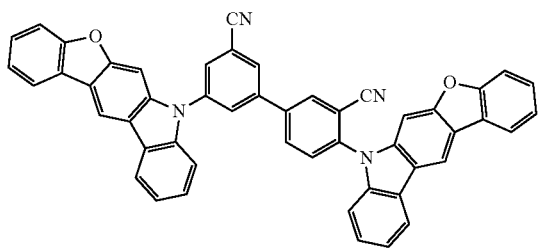
604
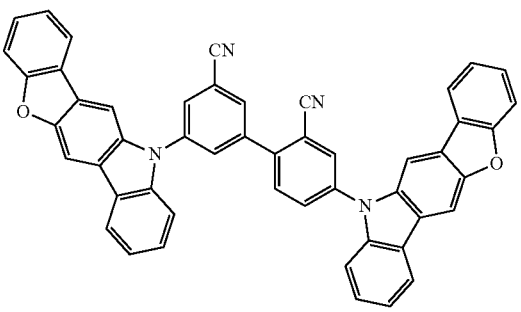
605
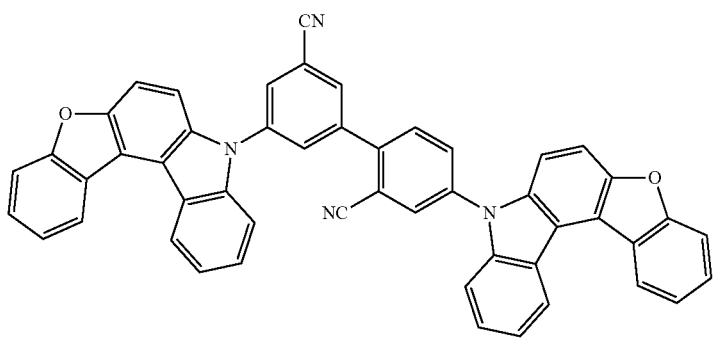
606
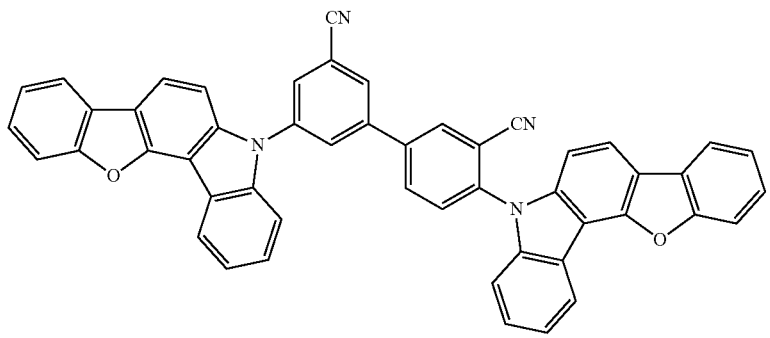
607
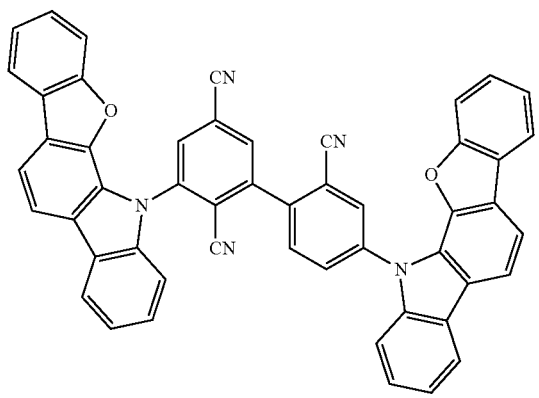
608
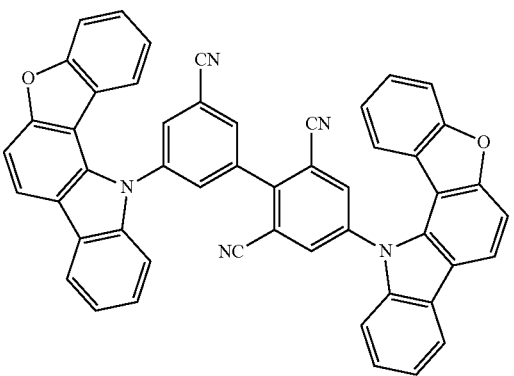

-continued
601
609
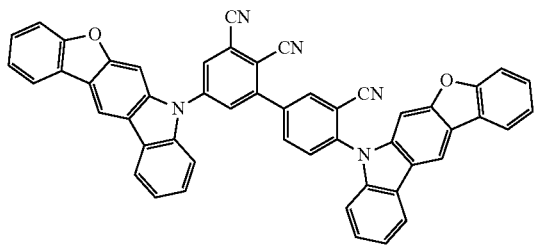
602
610
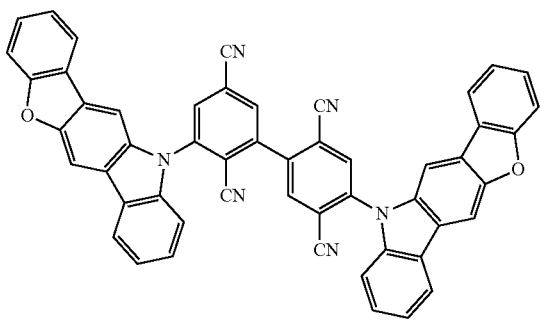
611
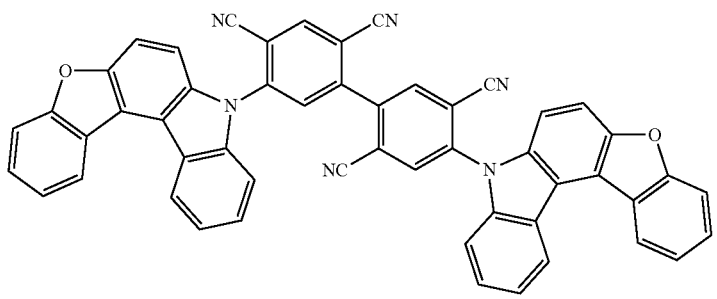
612
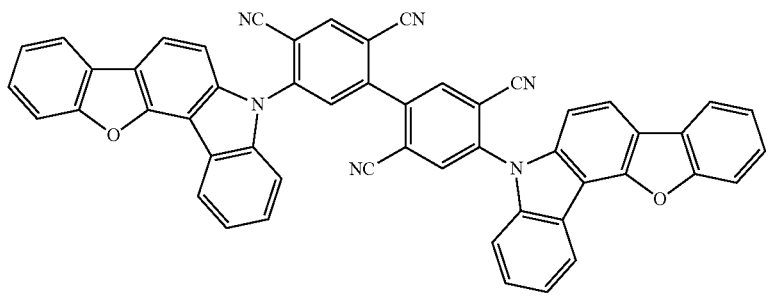
613
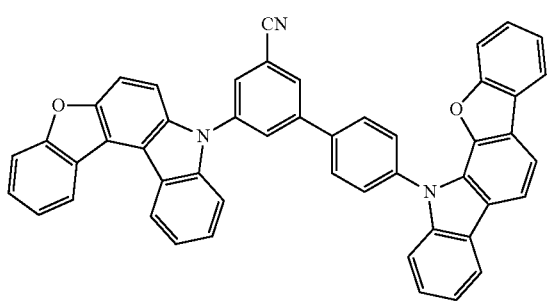
614
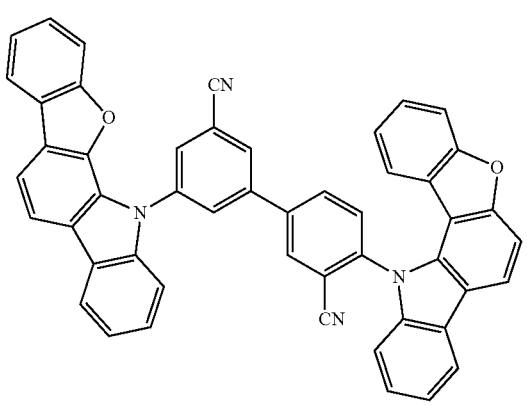

-continued
615
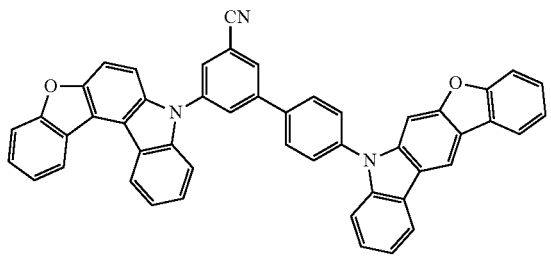
616
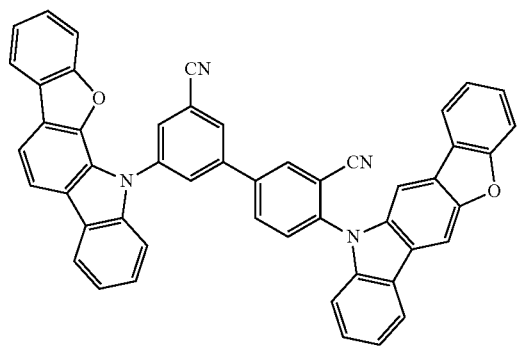
617
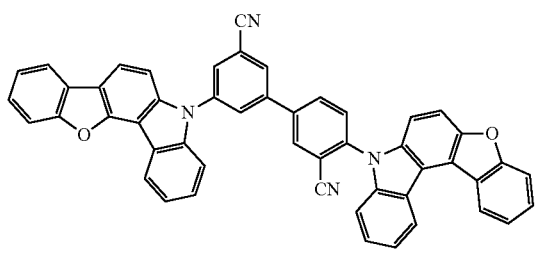
618
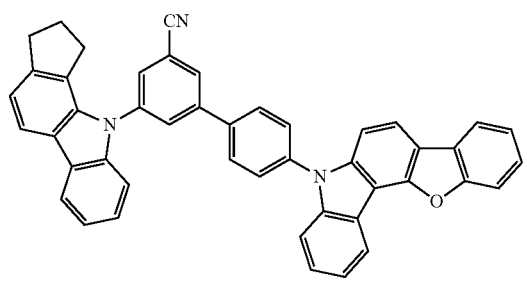
619
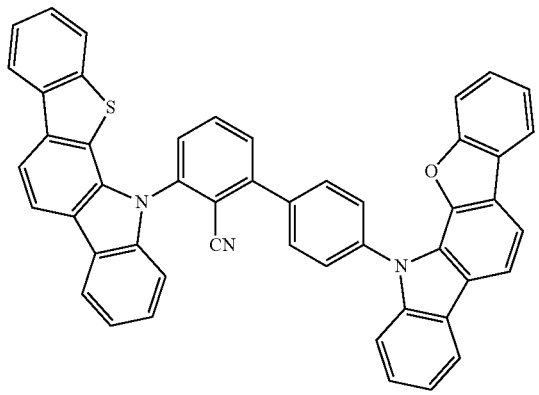
620
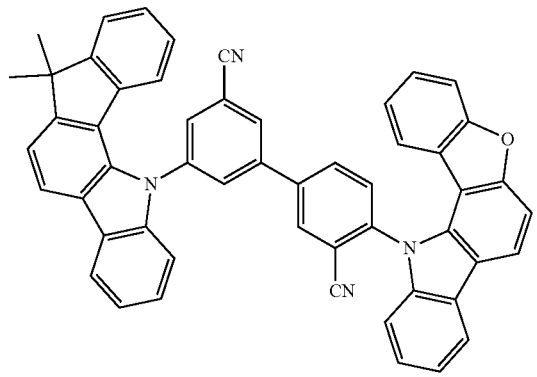
621
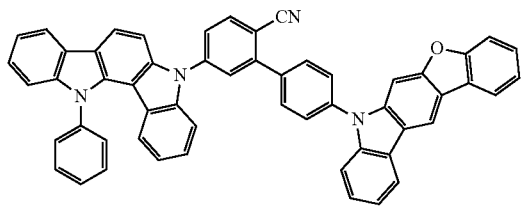
622
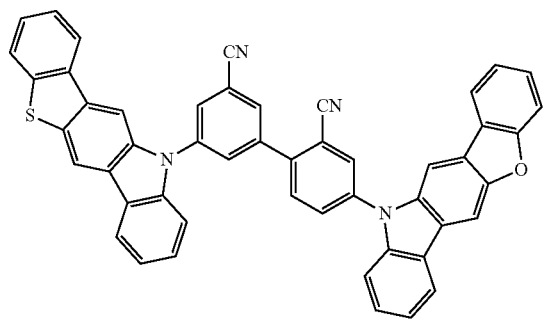

-continued
623
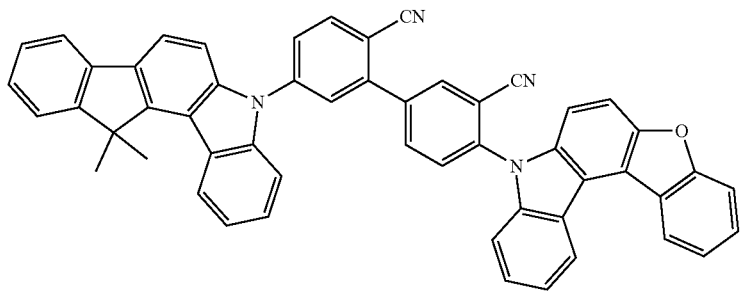
624
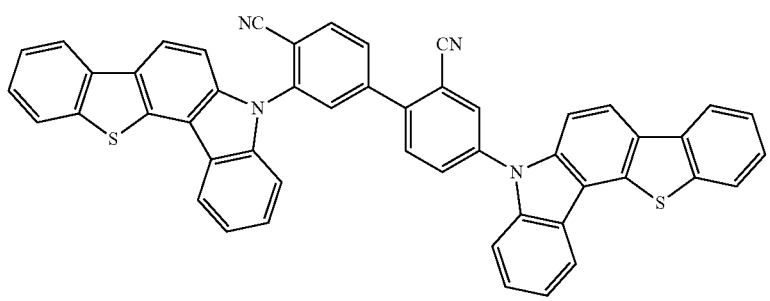
-continued
625
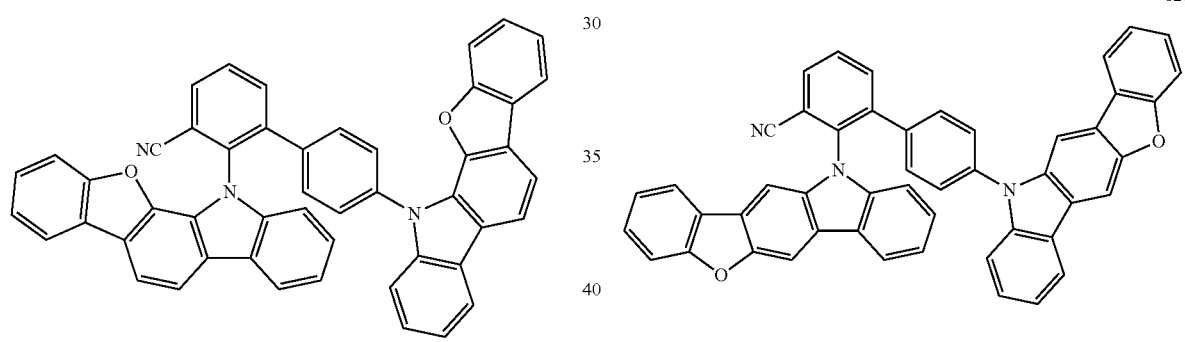
626
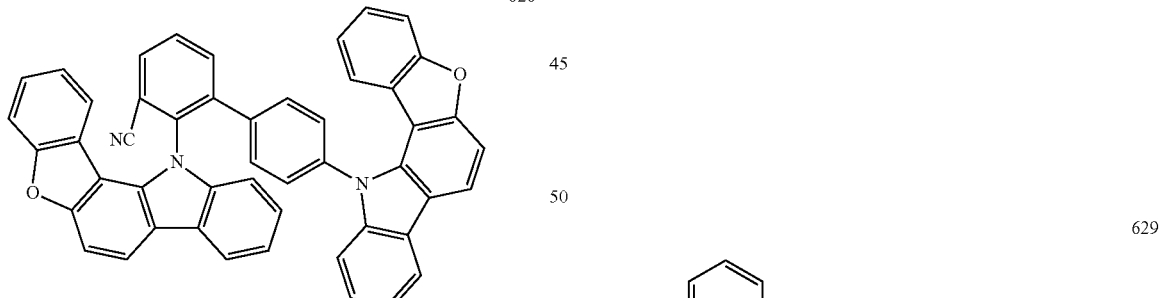
627
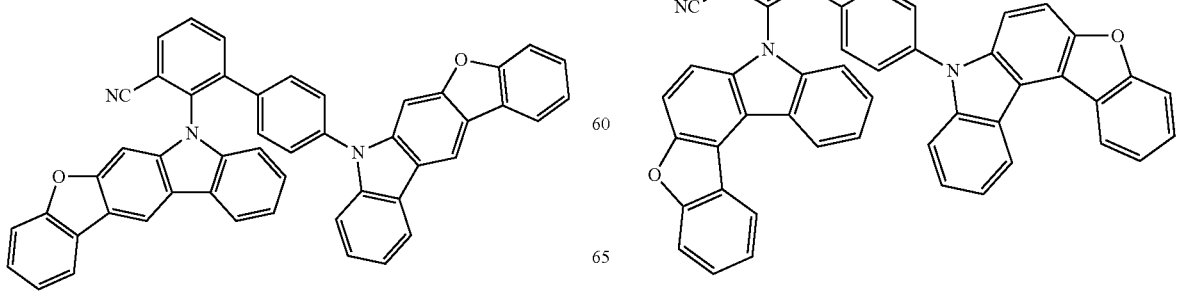
628
629

607
-continued
630
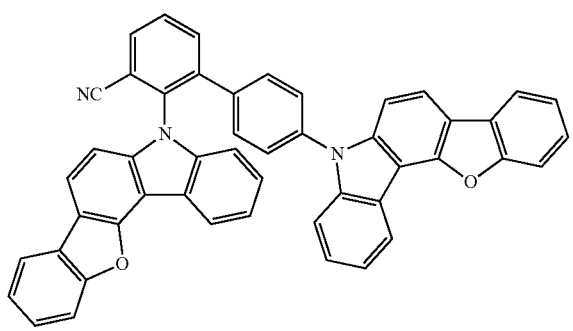
631
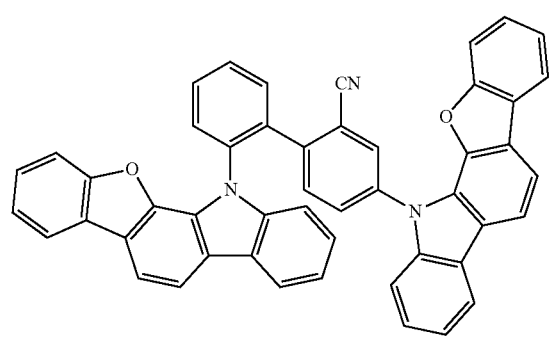
632
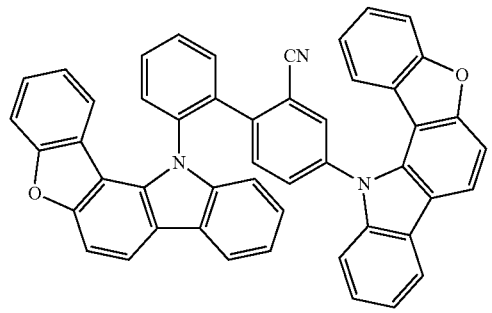
633
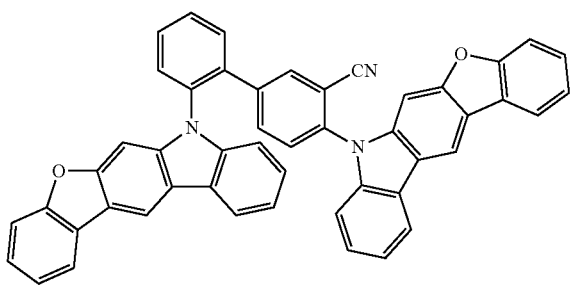
634
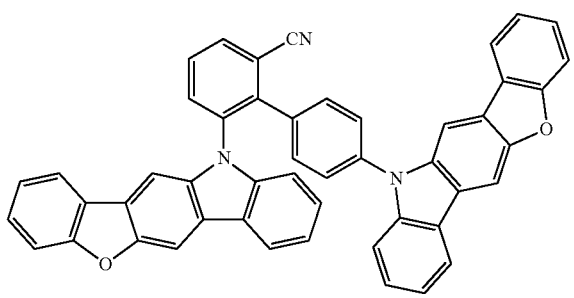
608
-continued
635
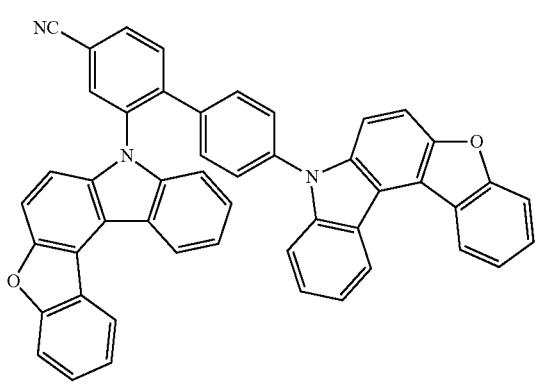
636
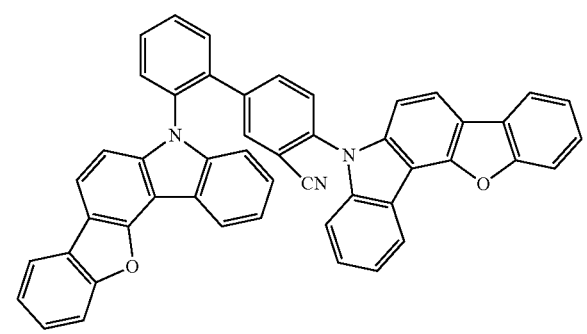
637
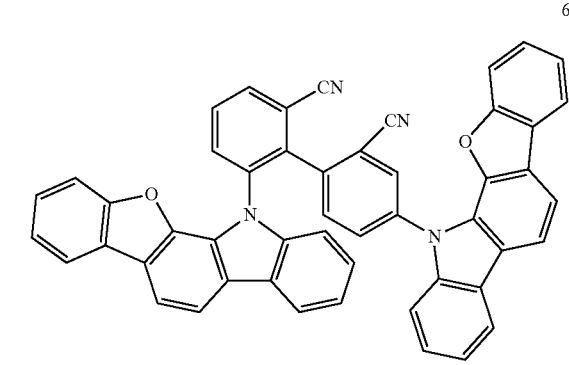
638
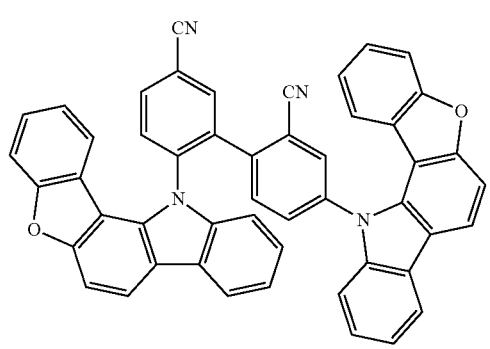

609
-continued
639
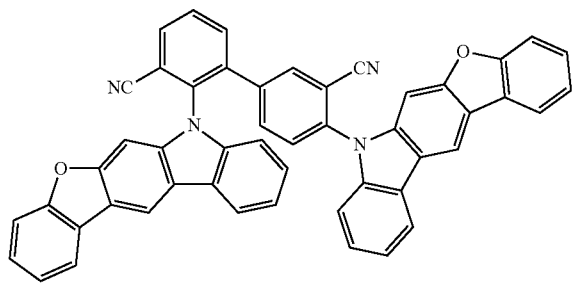
640
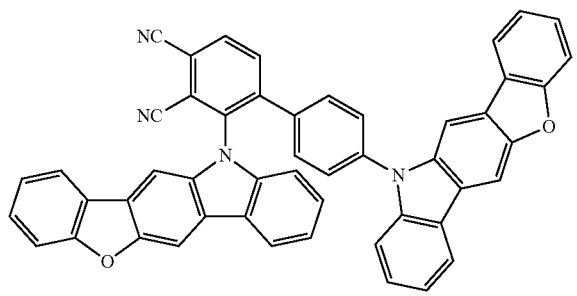
641
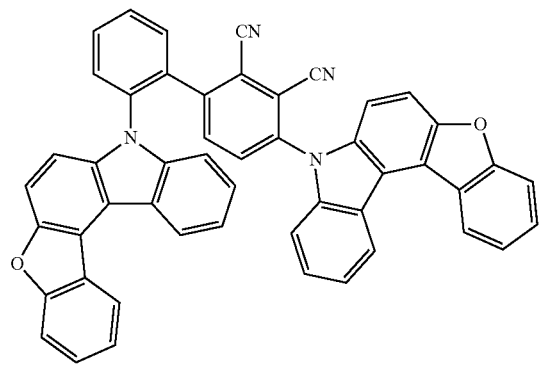
642
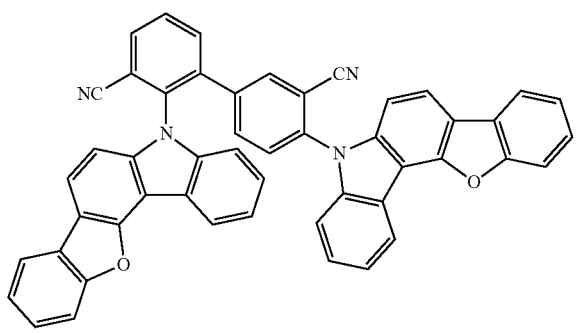
610
-continued
643
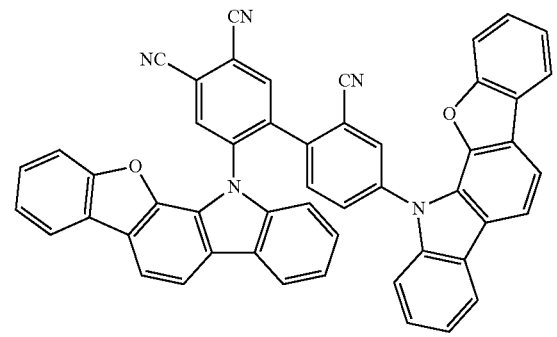
644
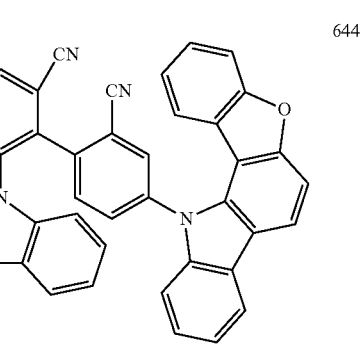
645
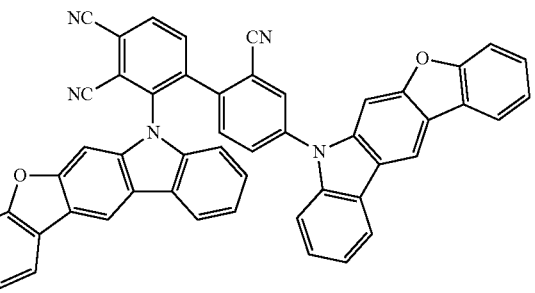
646
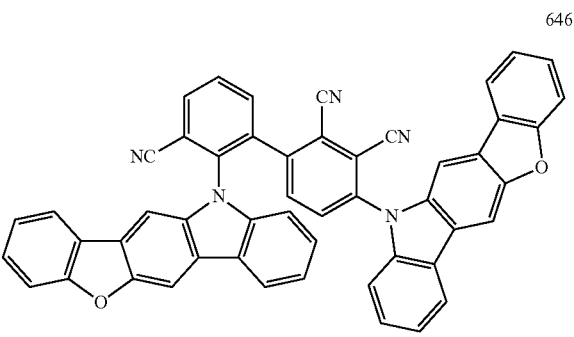

611
-continued
647
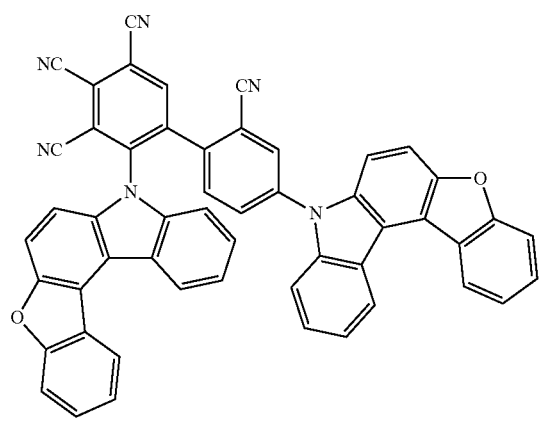
648
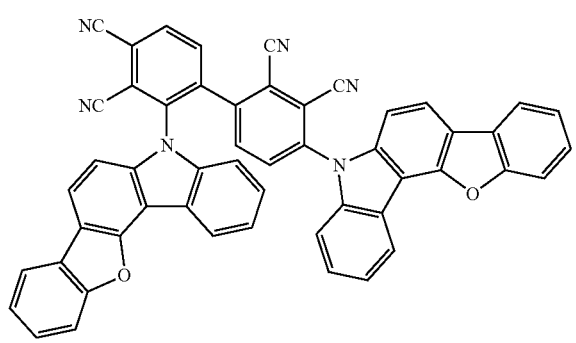
649
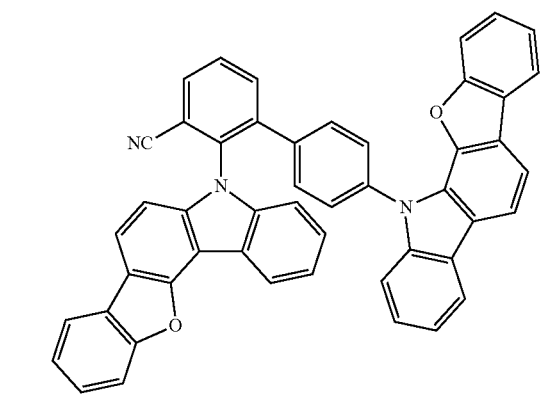
650
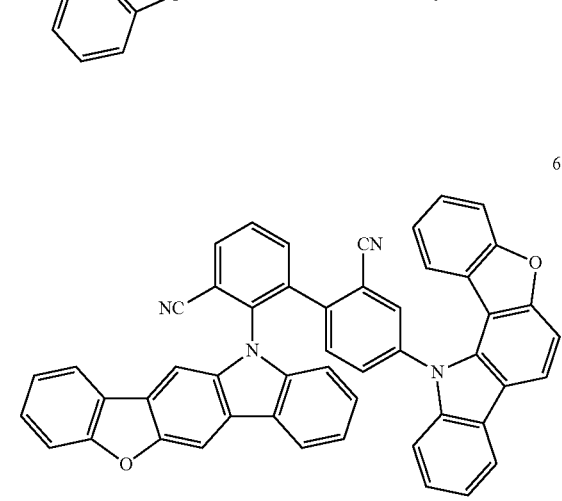
612
-continued
651
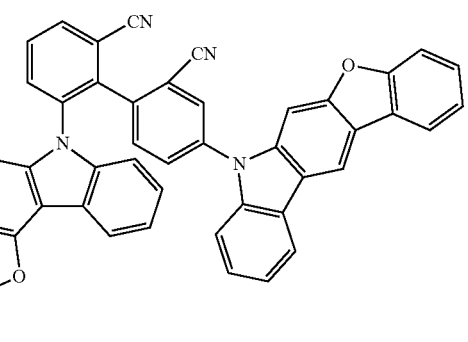
652
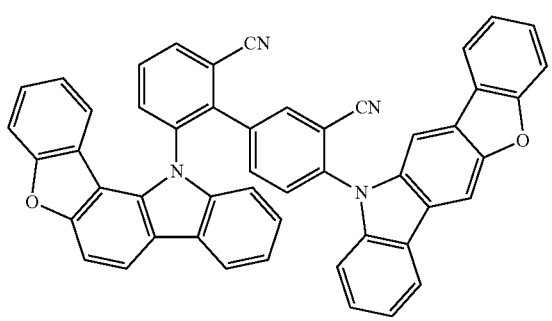
653
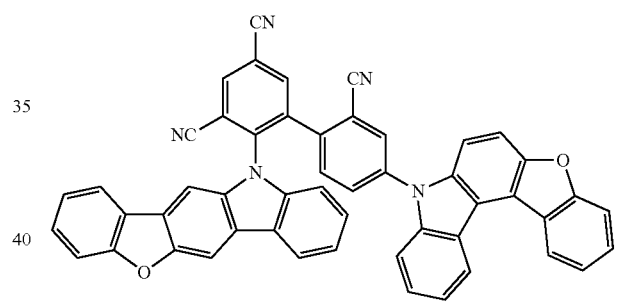
654
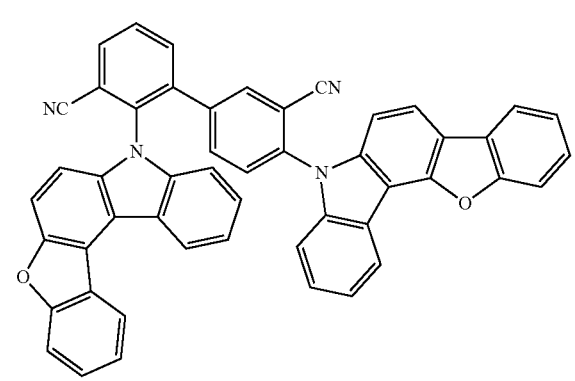

-continued
655
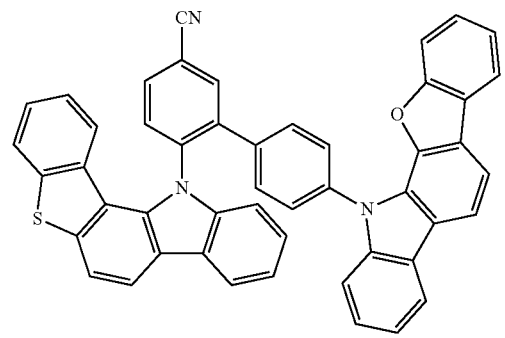
656
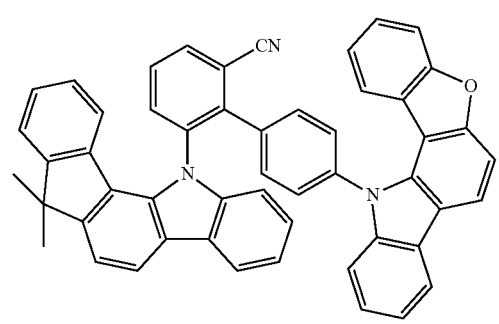
657
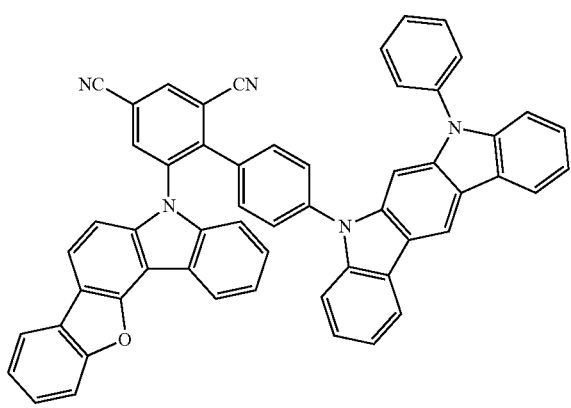
658
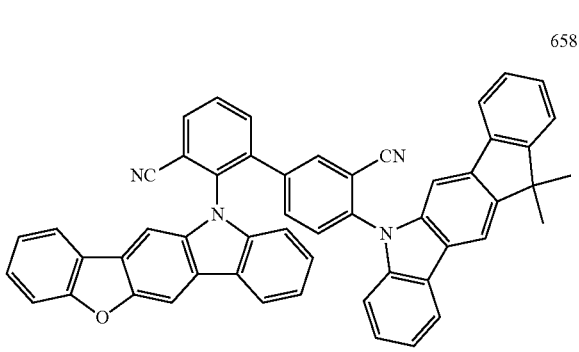
-continued
659
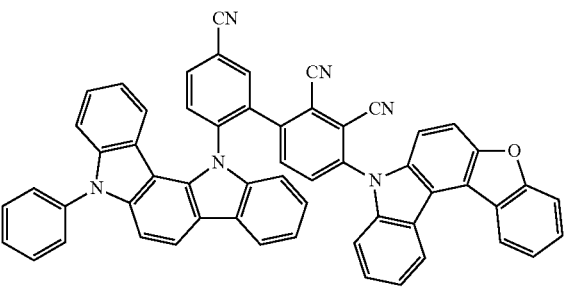
660
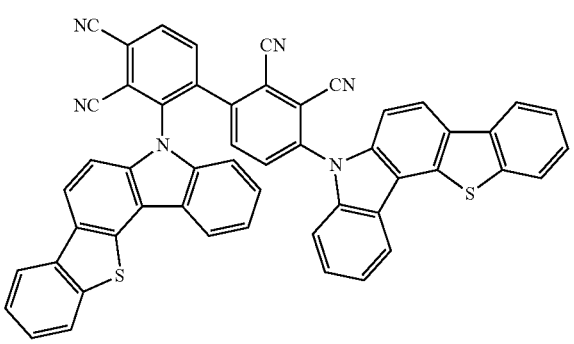
661
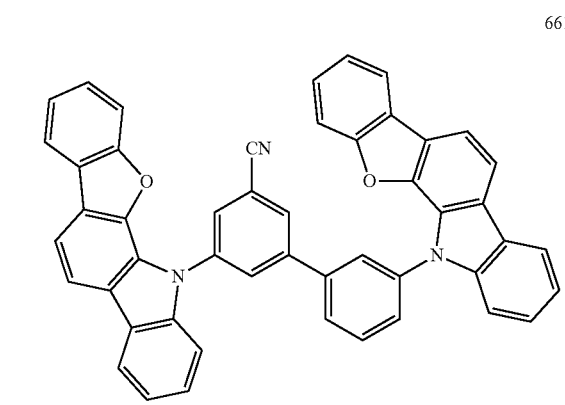
662
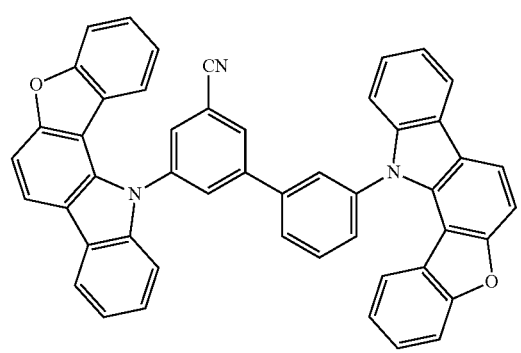

-continued
663
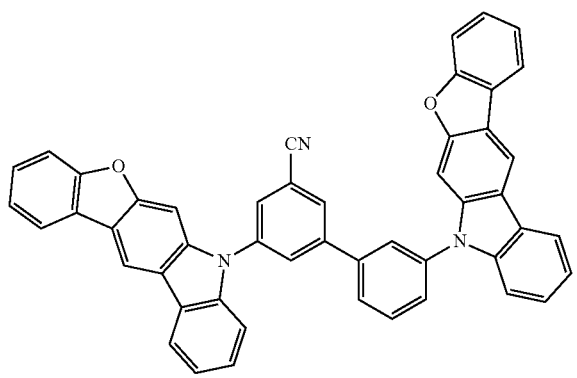
664
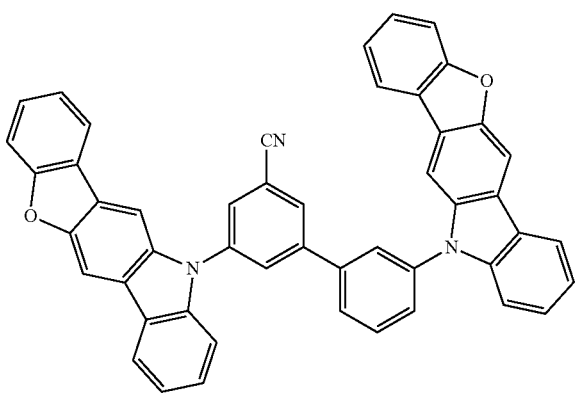
665
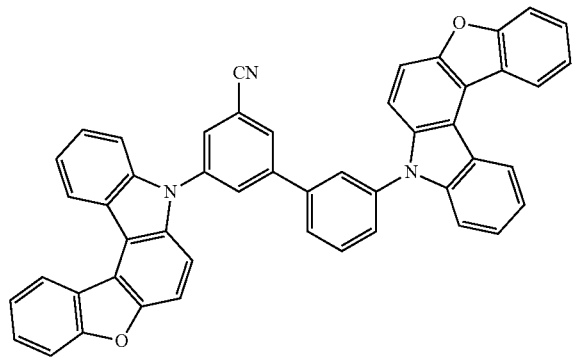
-continued
666
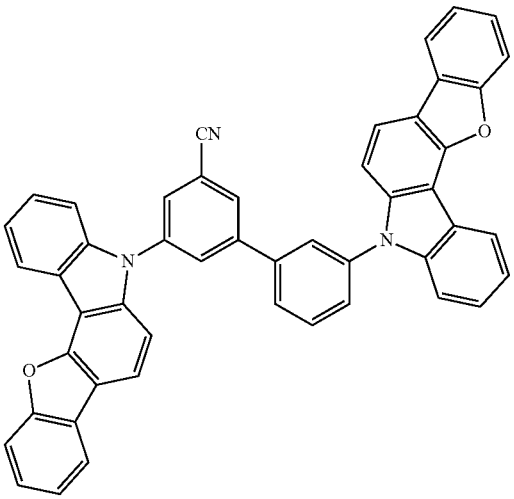
667
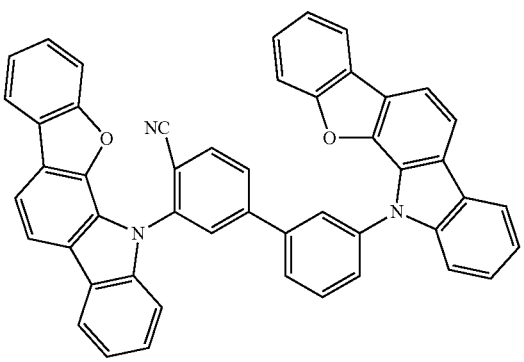
668
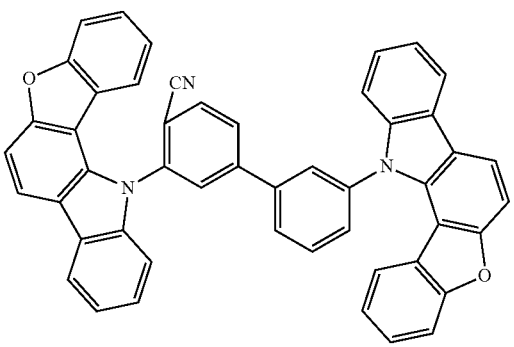
669
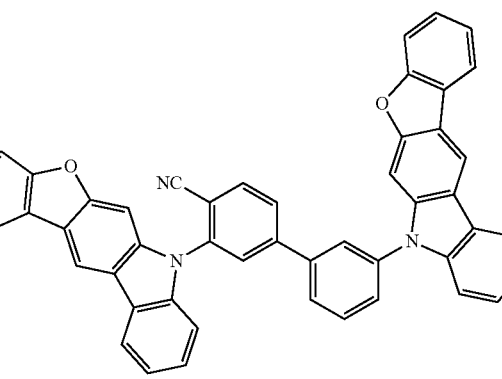

670
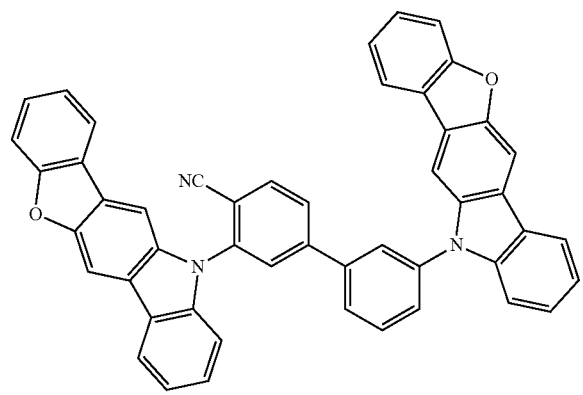
671
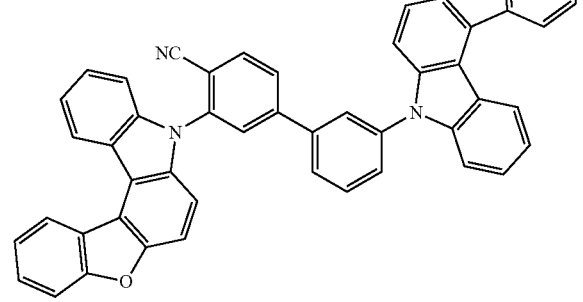
672
673
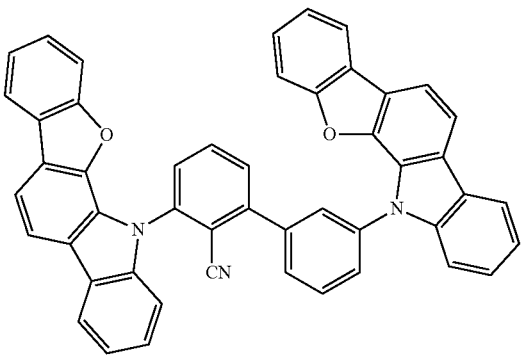
674
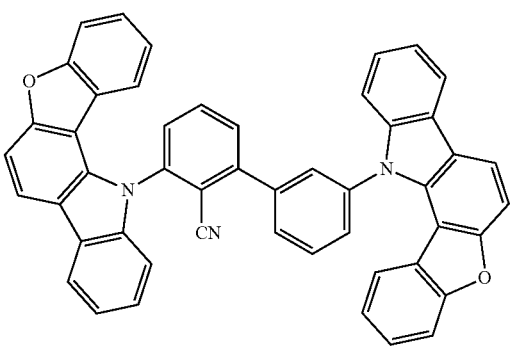
675
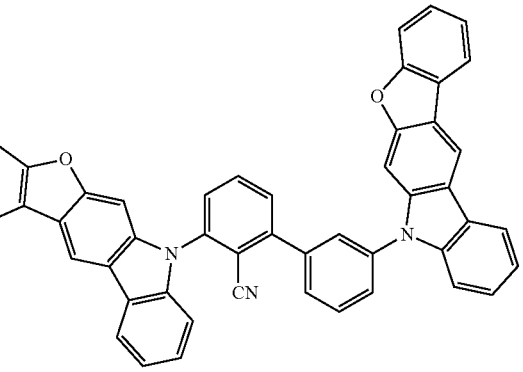
676
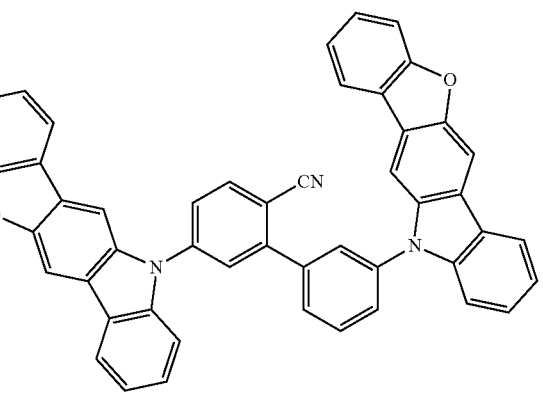

619
-continued
677
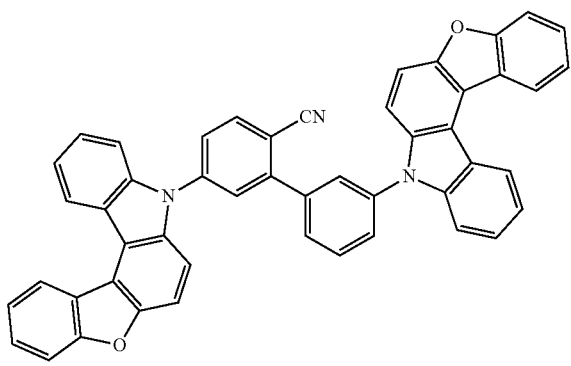
678
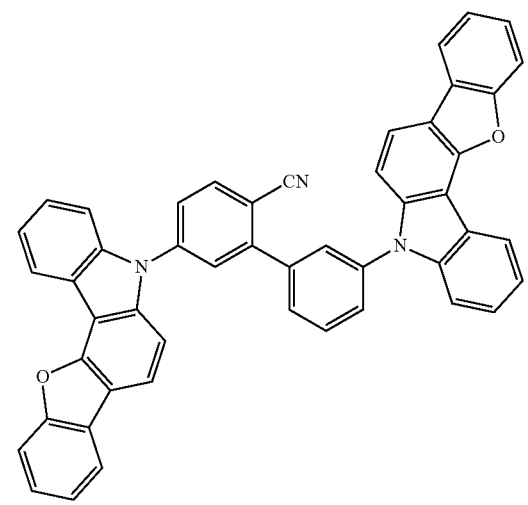
679
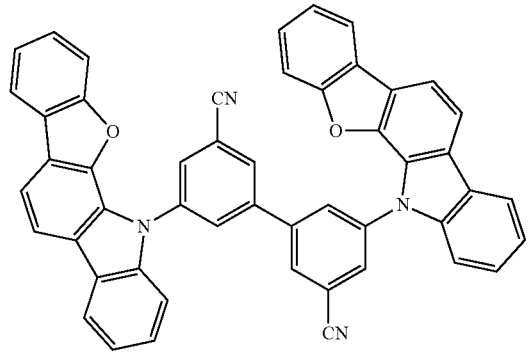
680
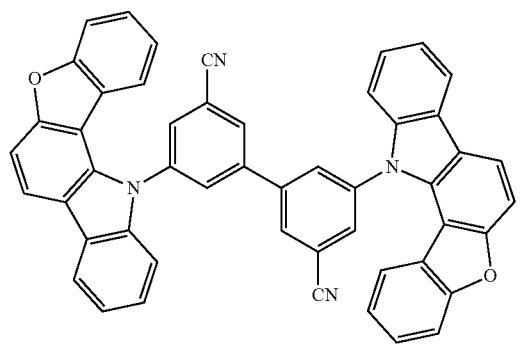
620
-continued
681
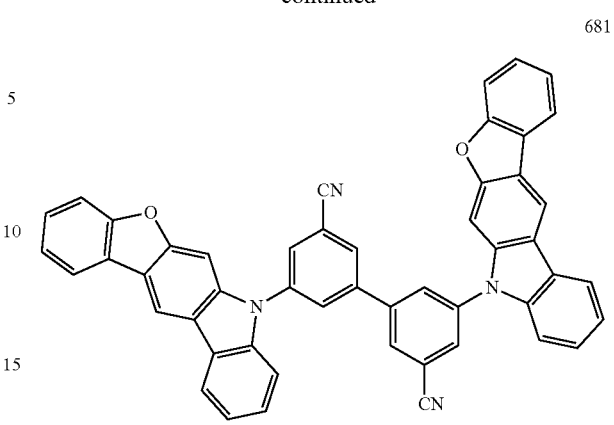
682
683
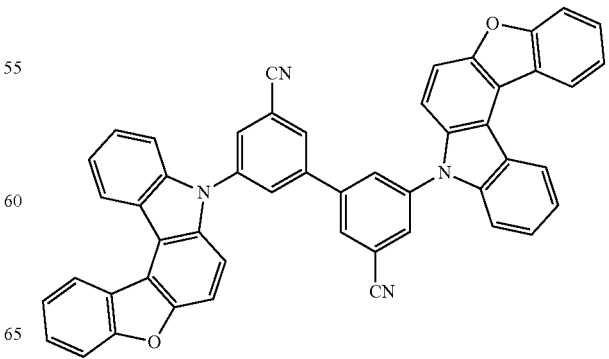

621
-continued
684
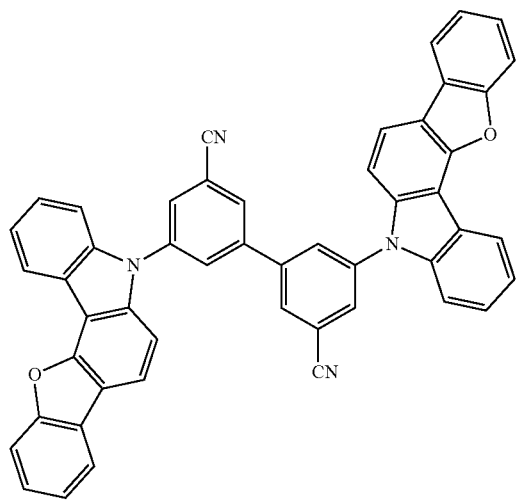
685
686
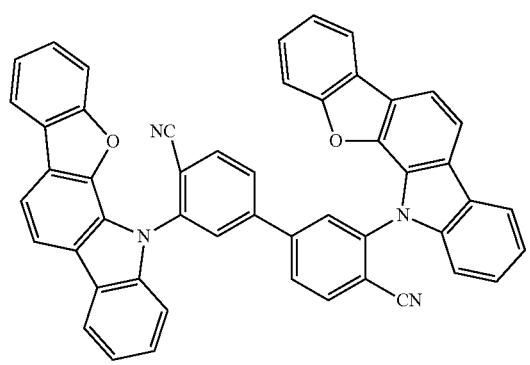
687
622
-continued
688
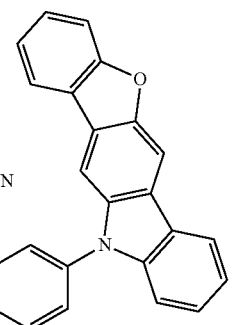
689
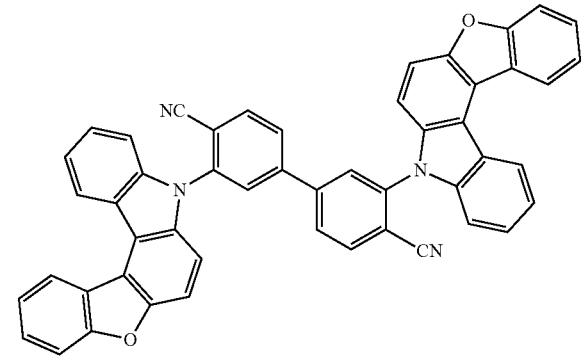
690
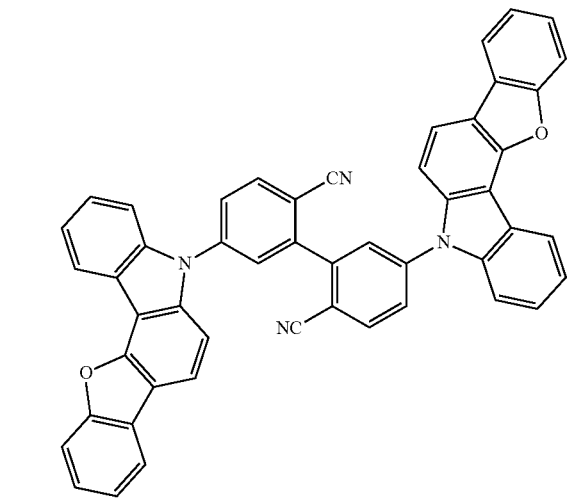

623
-continued
691
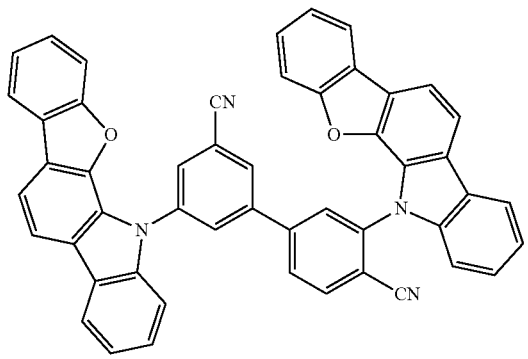
692
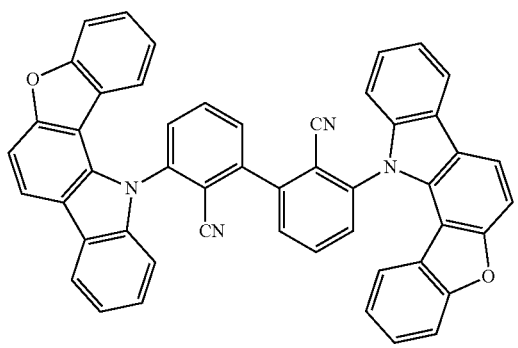
693
694
624
-continued
695
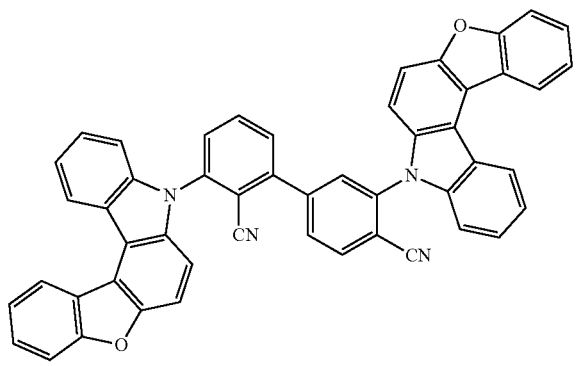
696
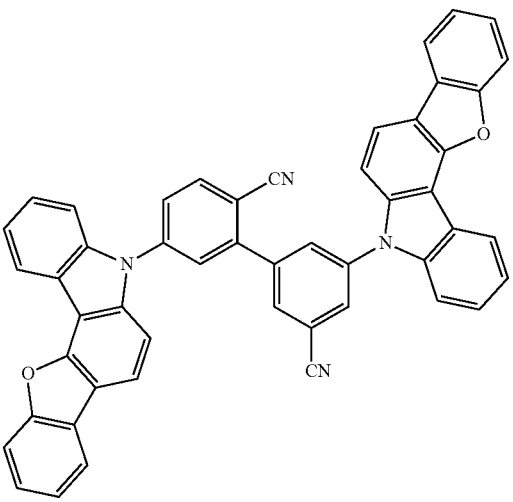
697
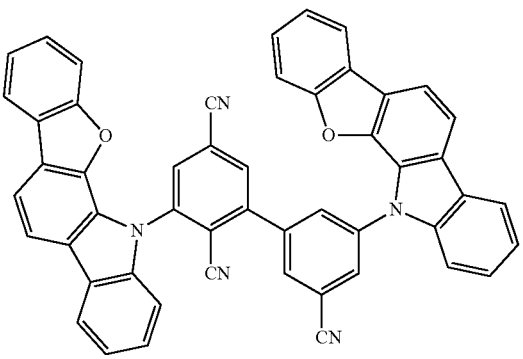
698
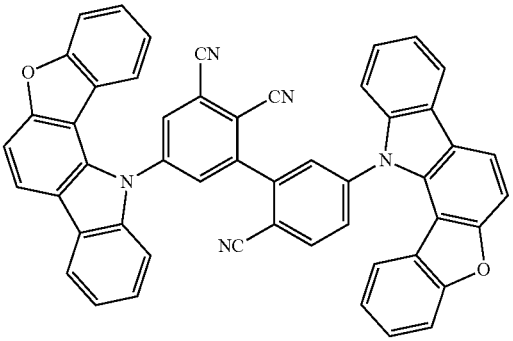

625
-continued
699
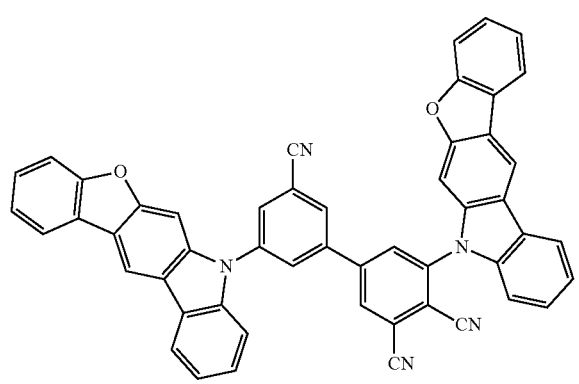
700
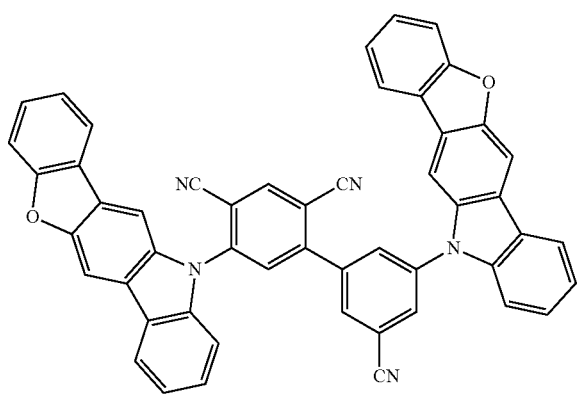
701
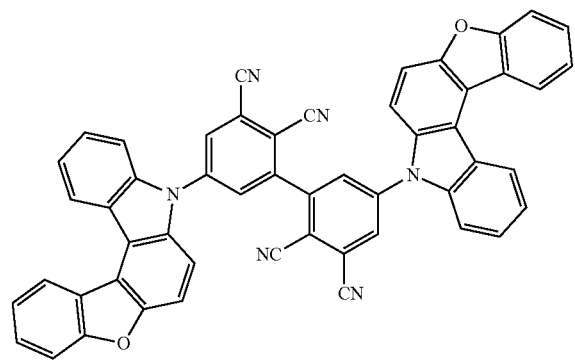
626
-continued
702
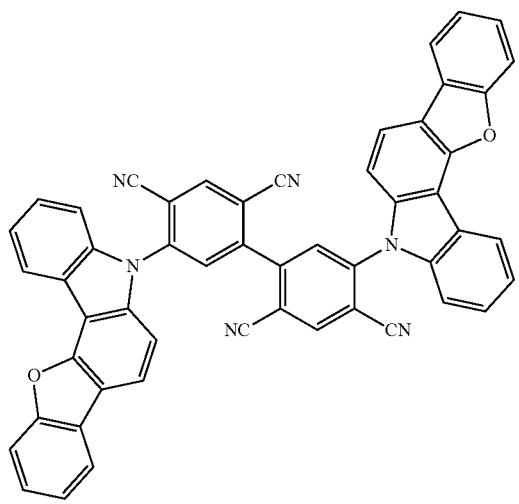
703
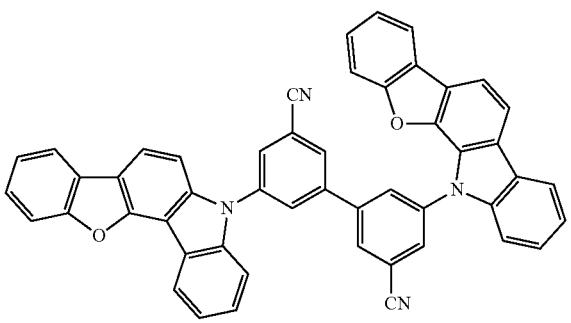
704
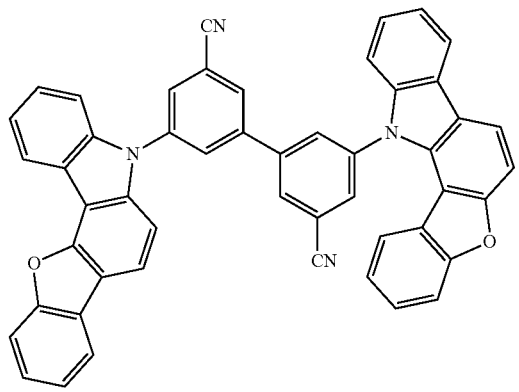

705
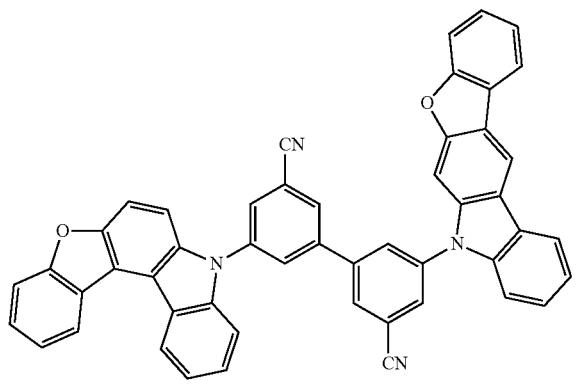
706
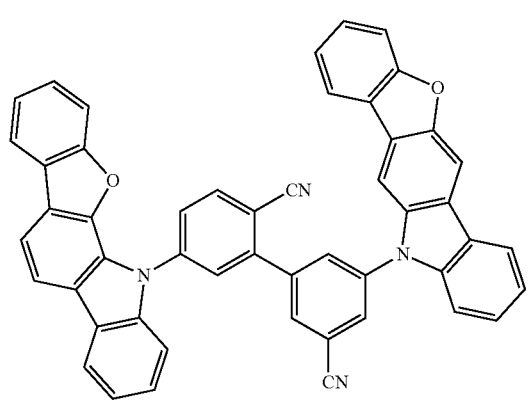
707
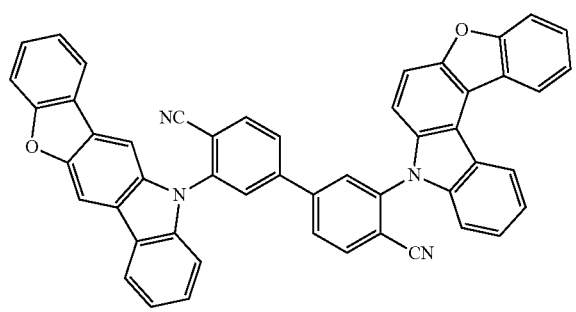
708
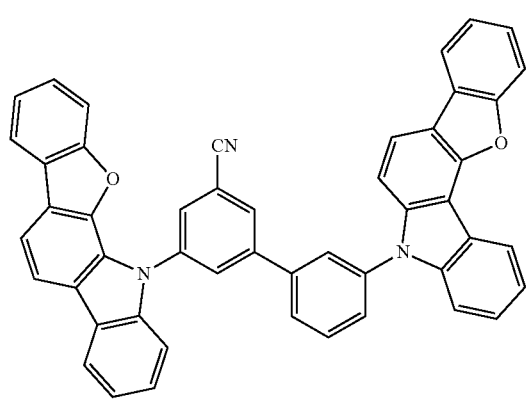
709
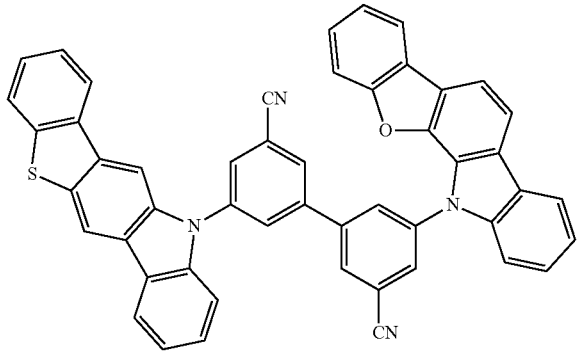
710
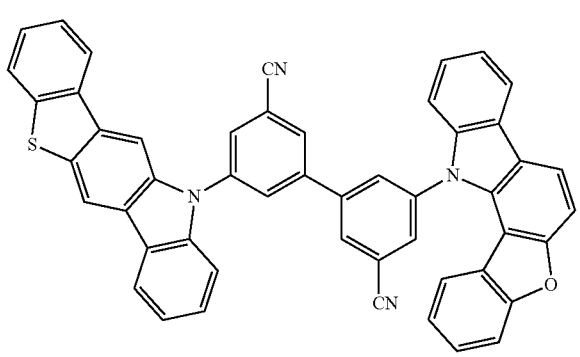
711
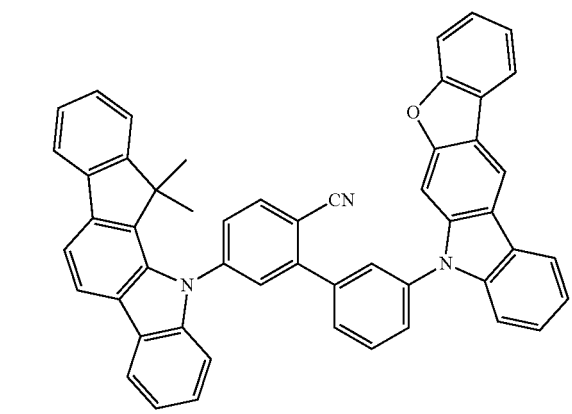
712
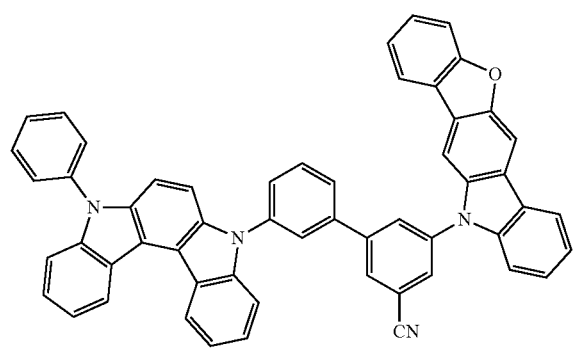

713
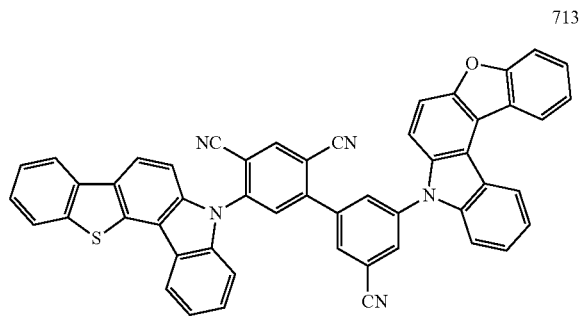
714
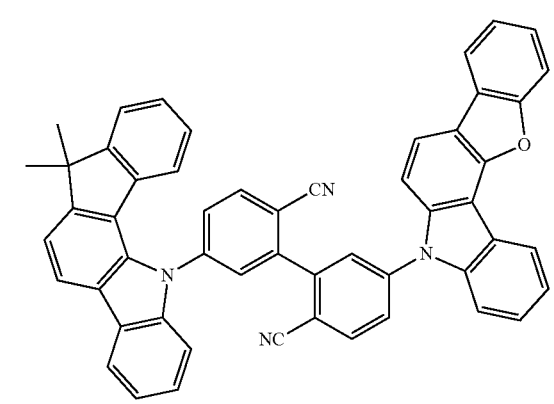
715
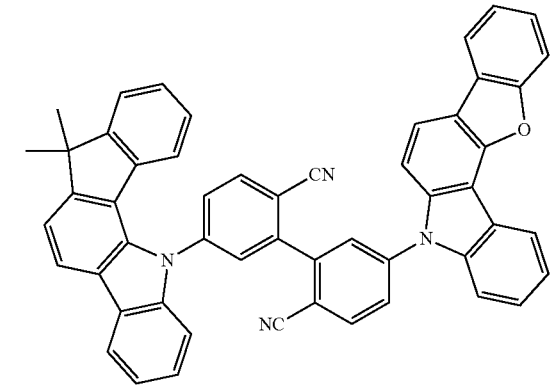
716
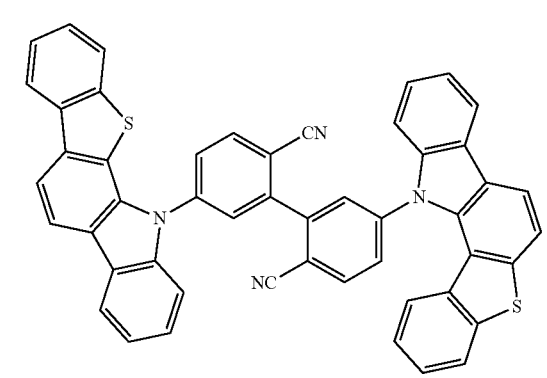
717
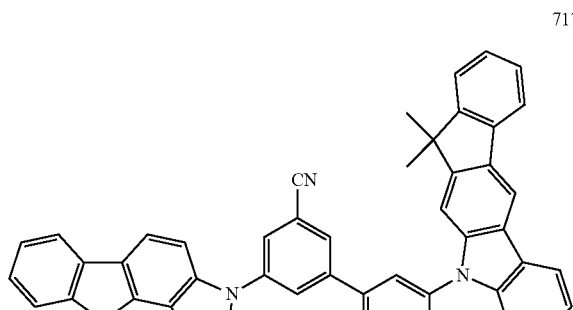
718
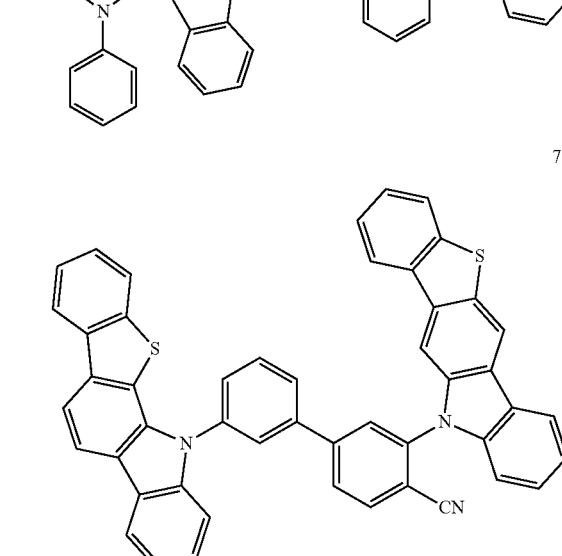
719
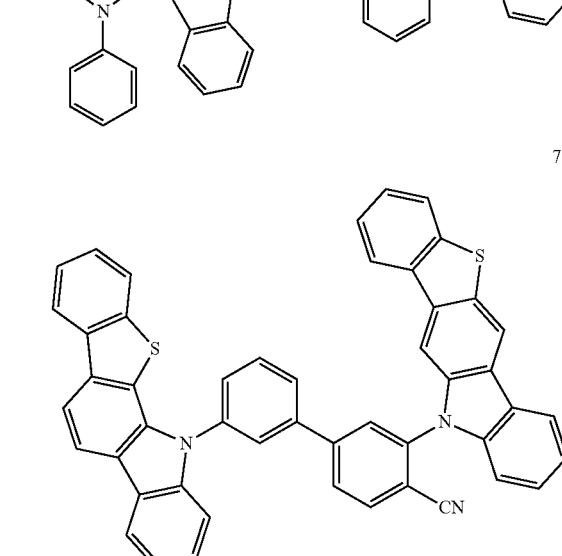
720
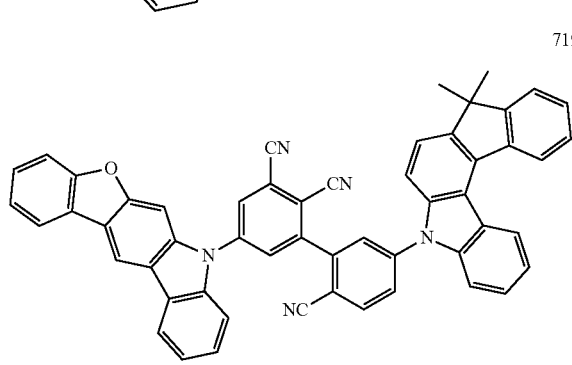

-continued
721
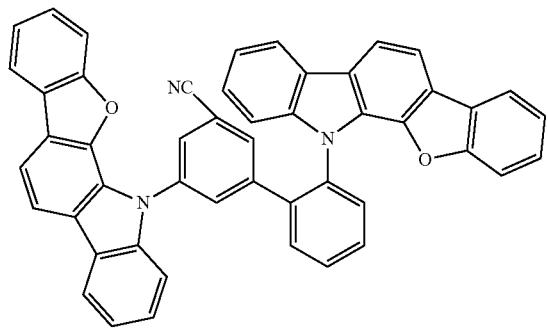
722
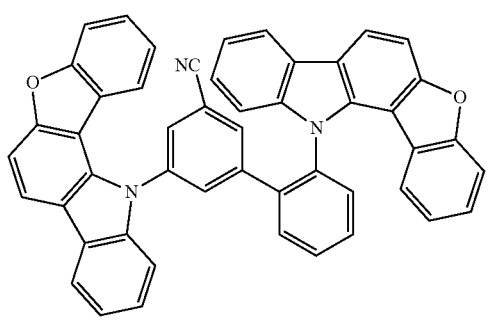
723
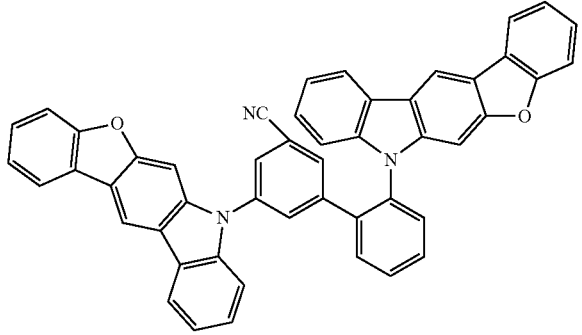
724
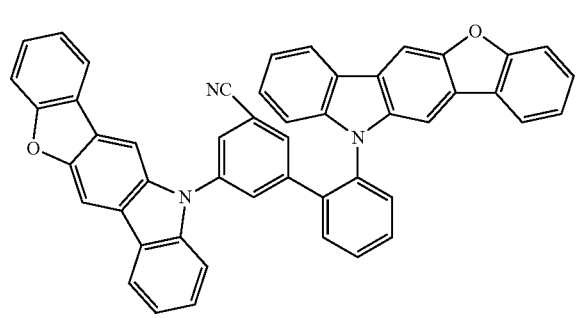
-continued
725
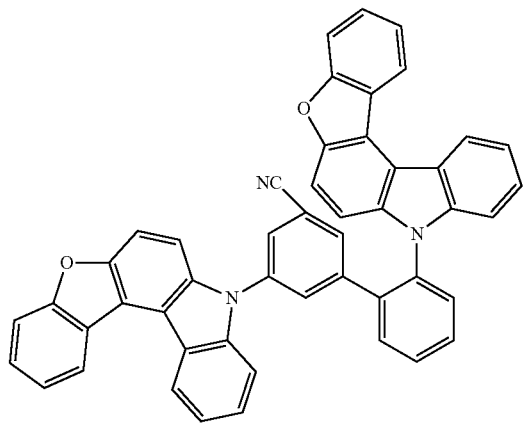
726
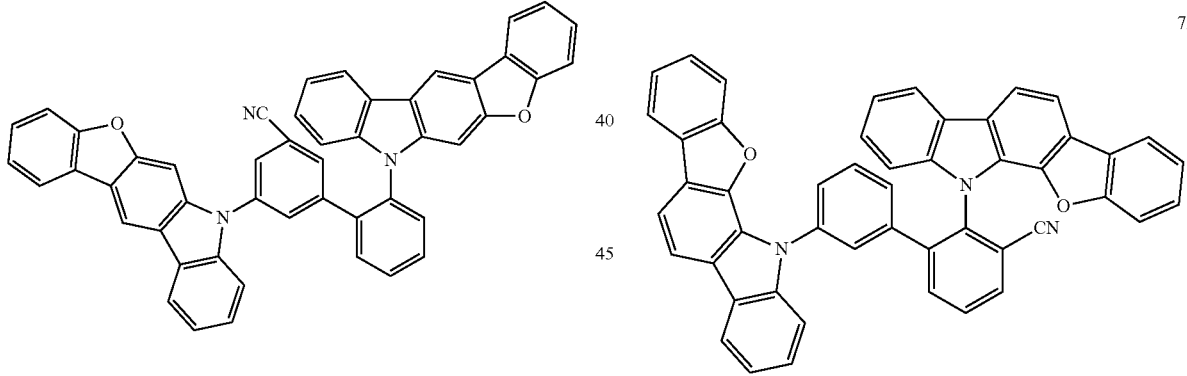
727
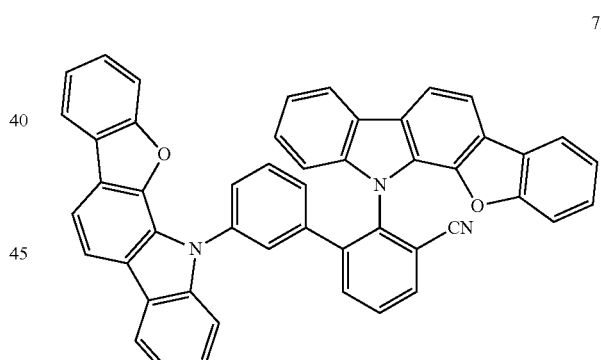
728
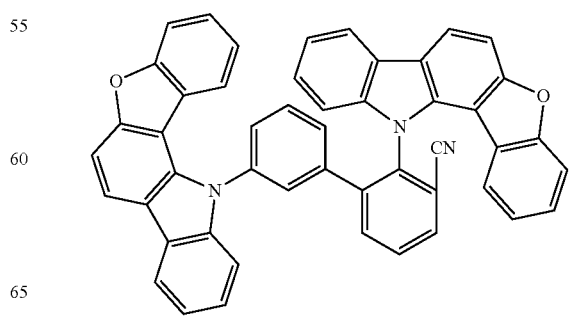

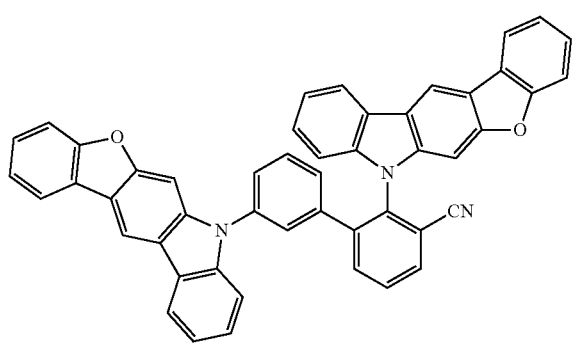
729
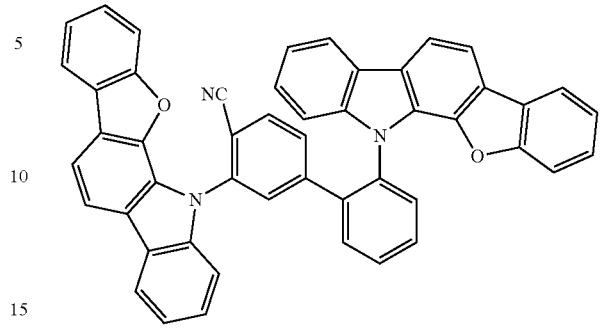
733
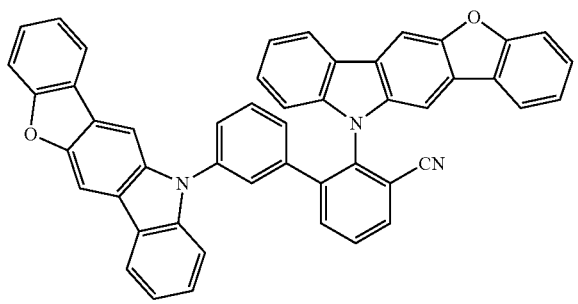
730
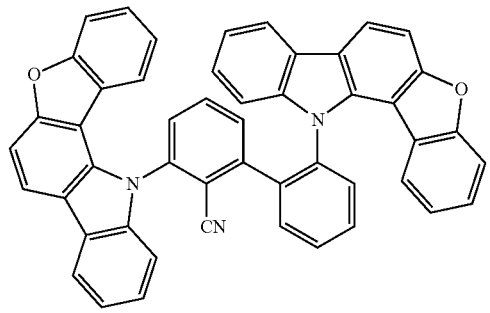
734
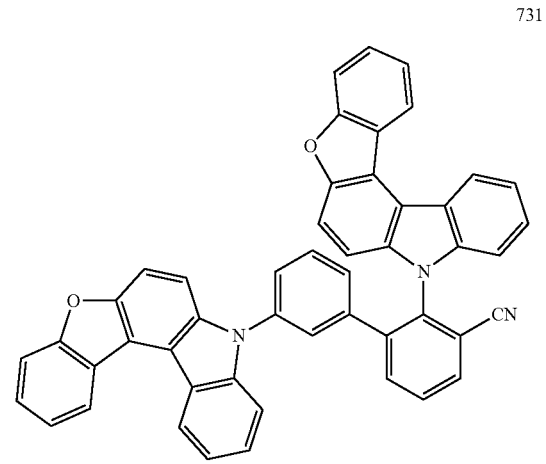
731
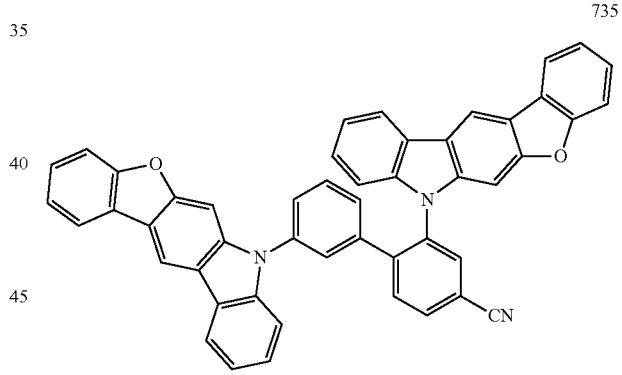
735
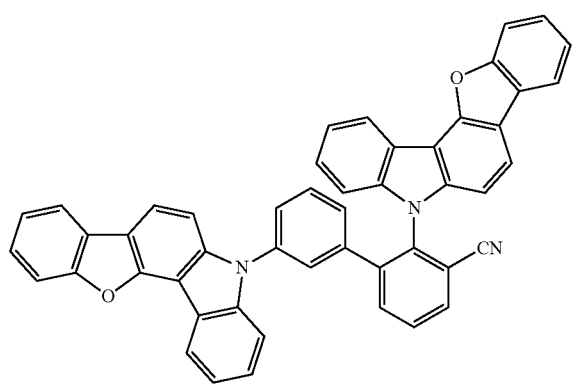
732
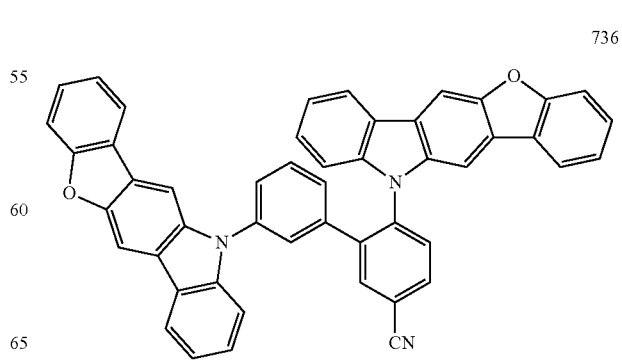
736

-continued
737
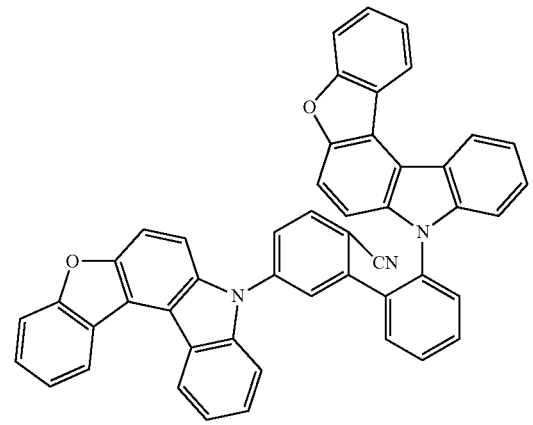
738
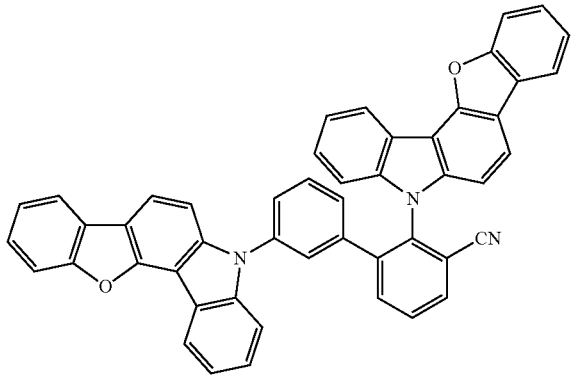
739
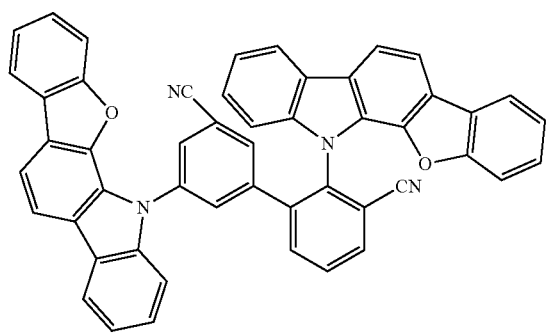
740
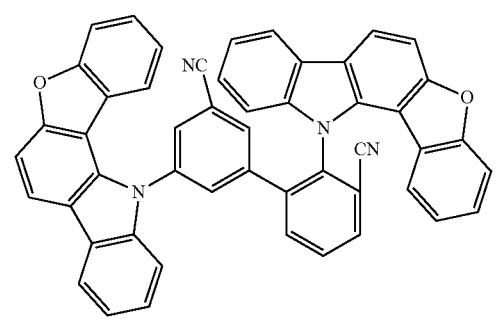
-continued
741
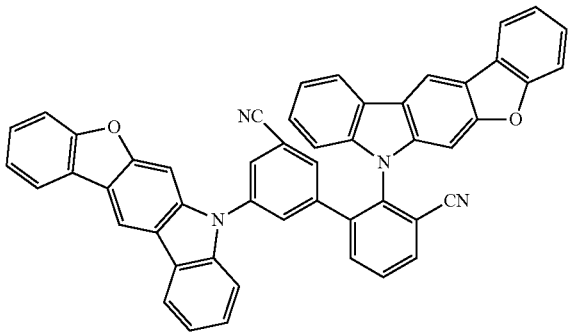
742
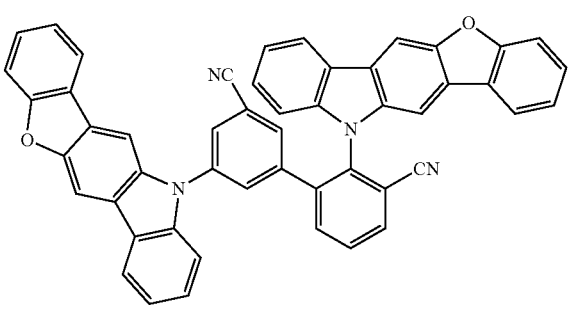
743
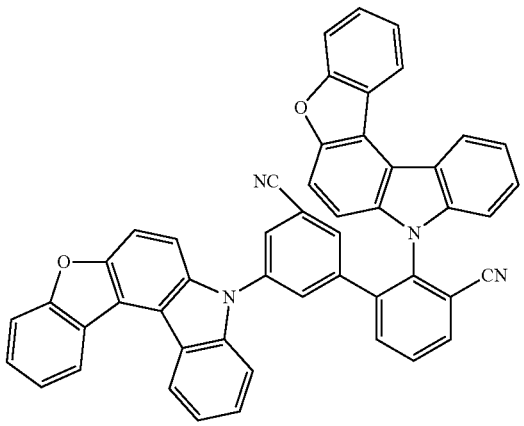
744
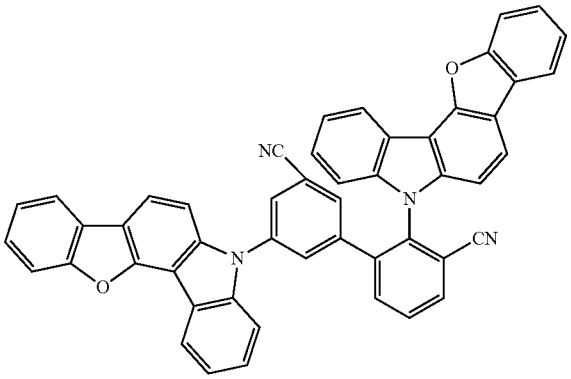

637
-continued
745
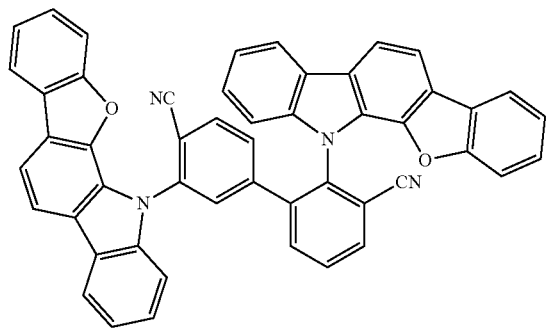
746
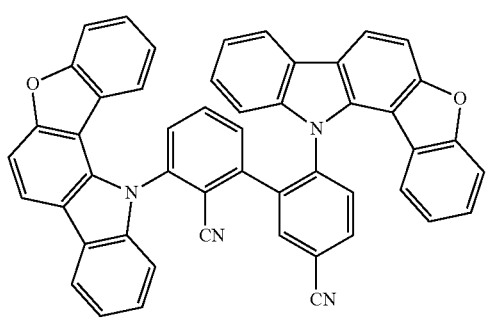
747
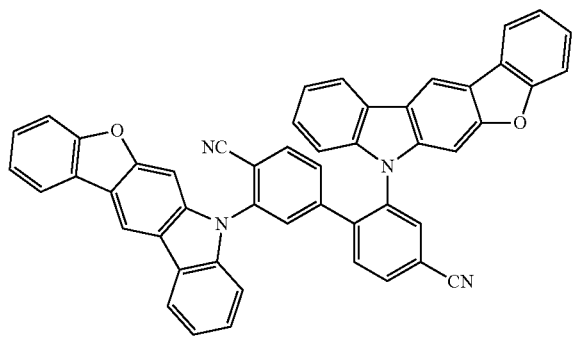
748
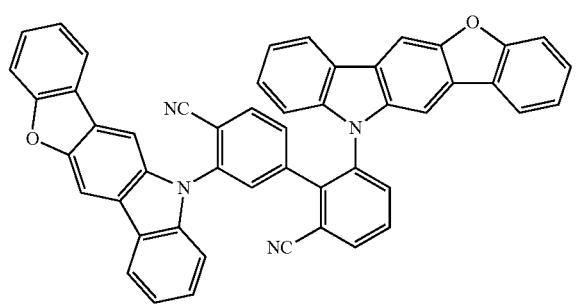
638
-continued
749
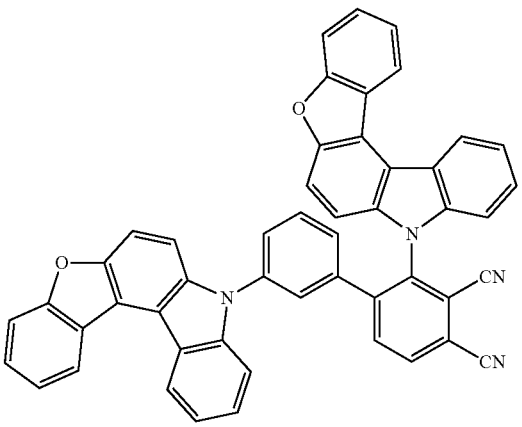
750
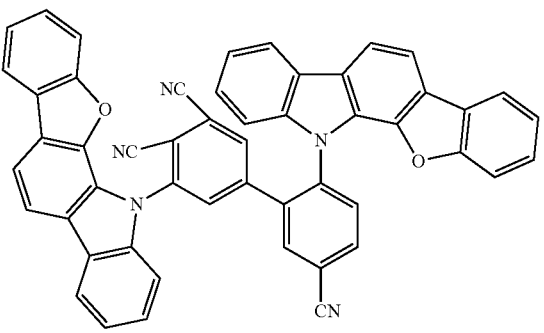
751
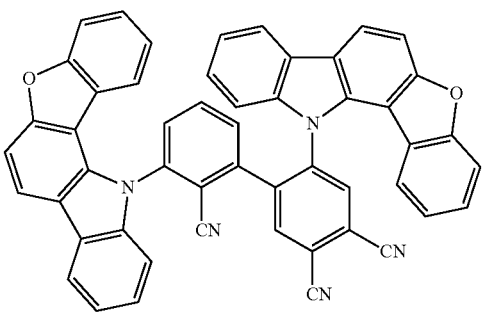
752

753
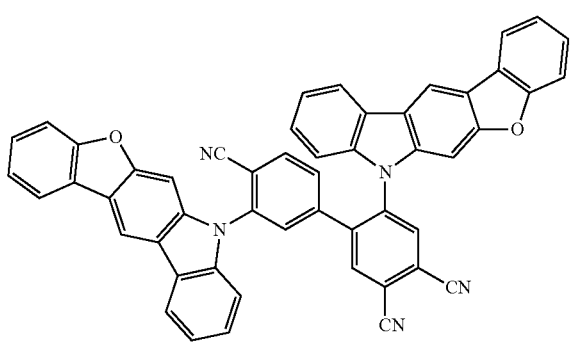
757
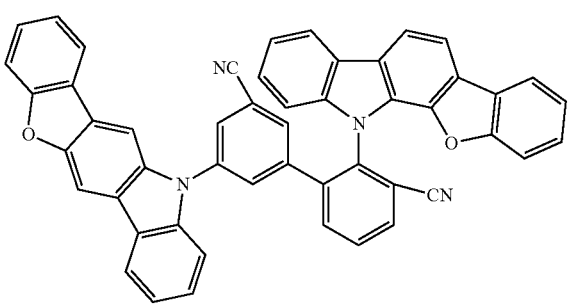
754
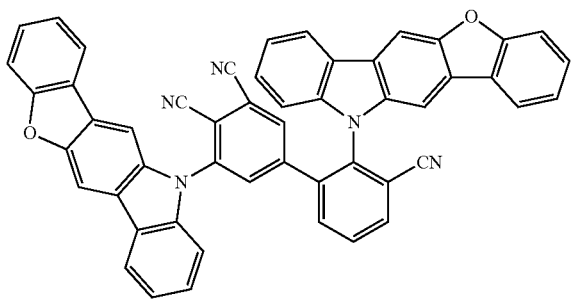
758
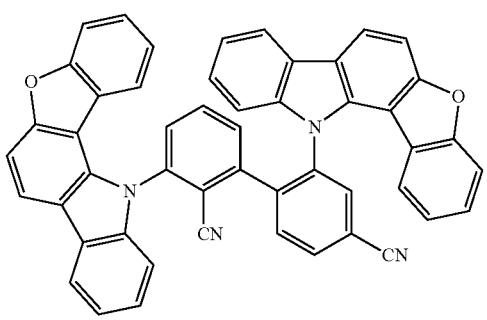
755
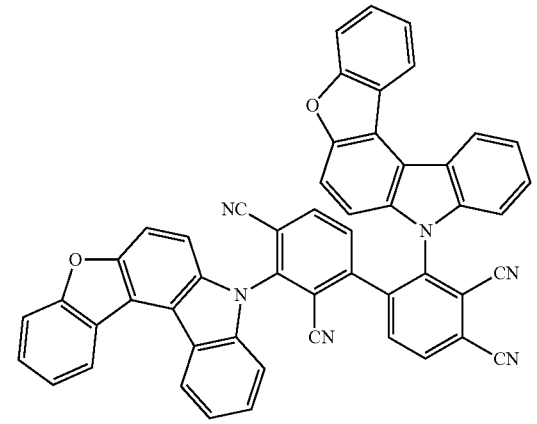
759
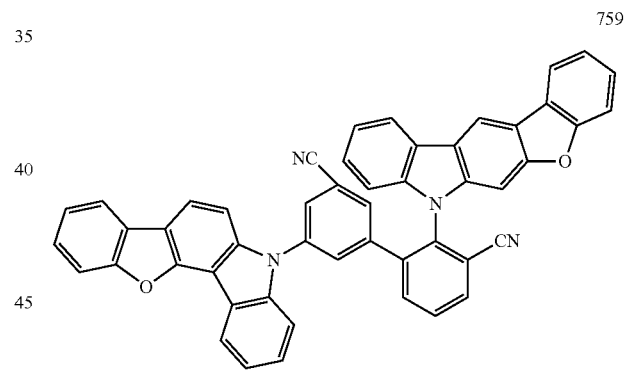
756
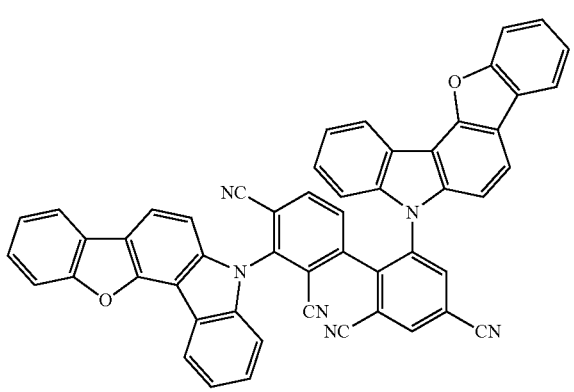
760
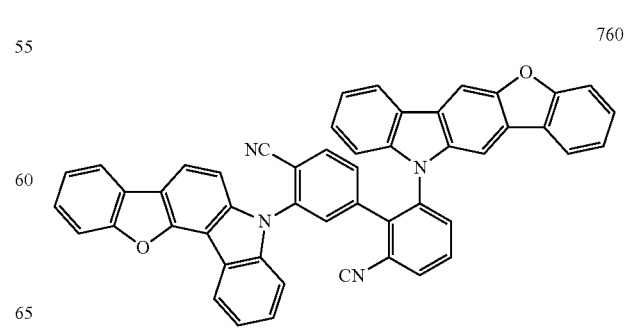

761
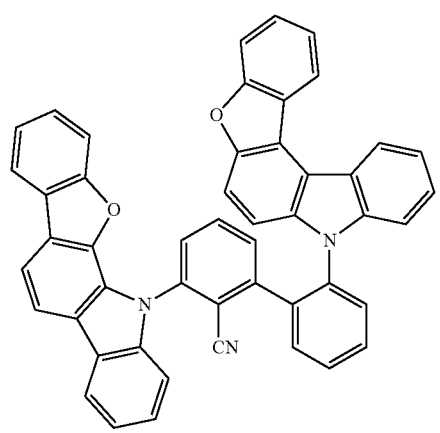
762
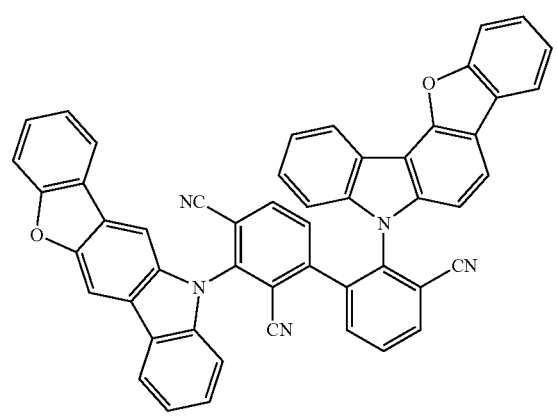
763
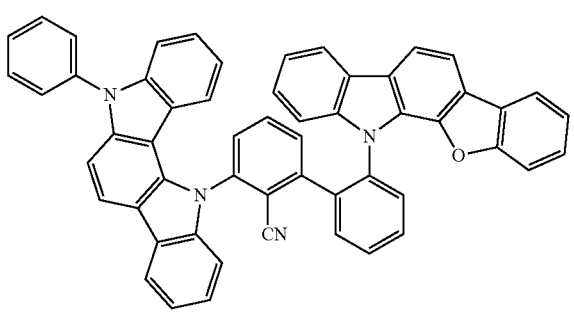
764
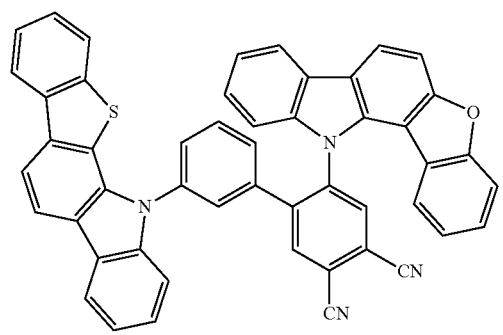
765
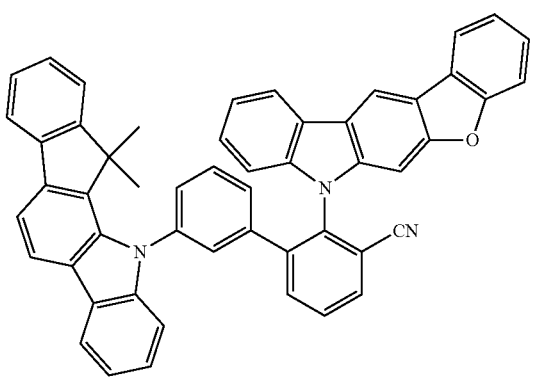
766
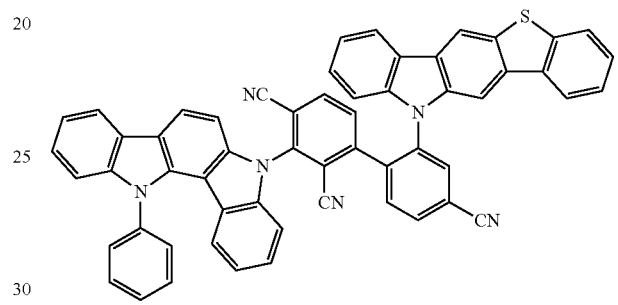
767
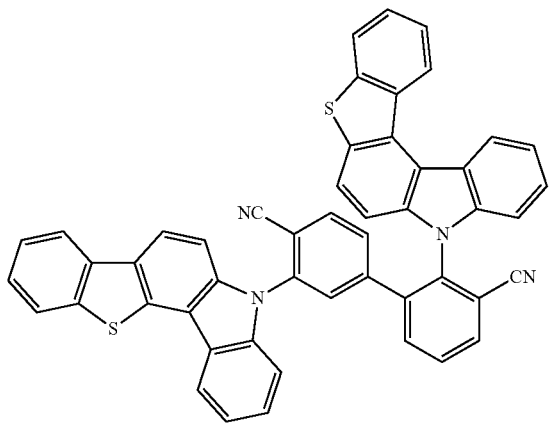
768
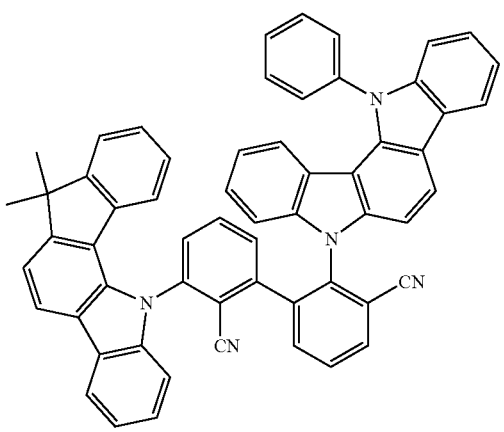

769
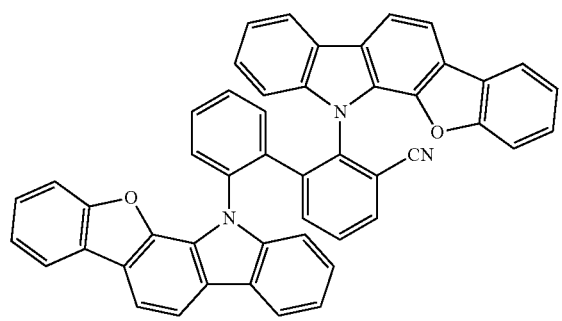
770
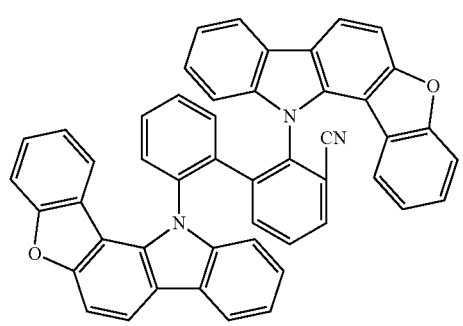
771
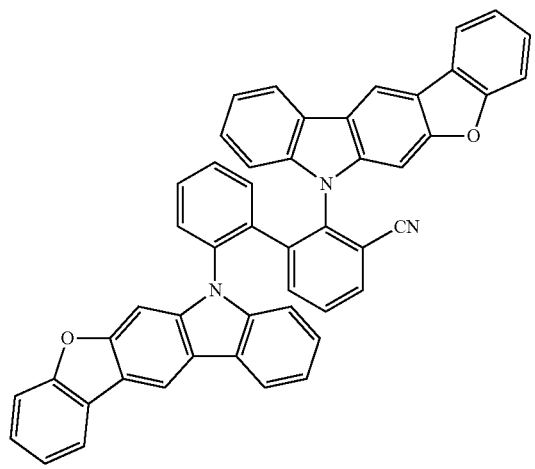
772
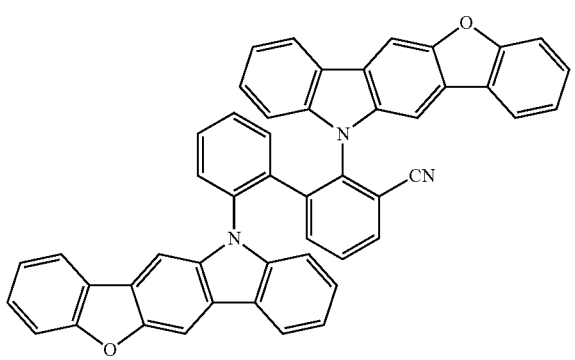
773
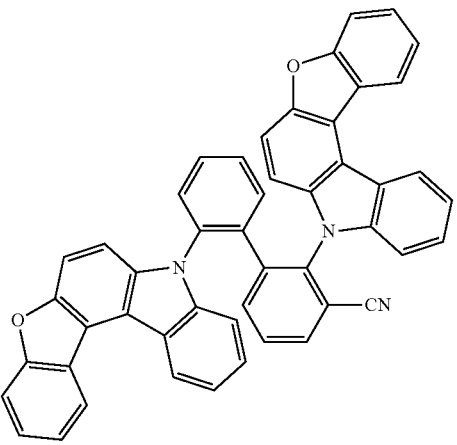
774
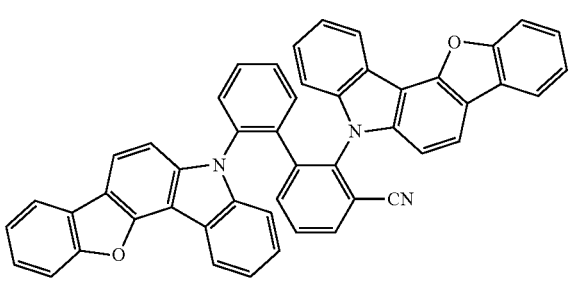
775
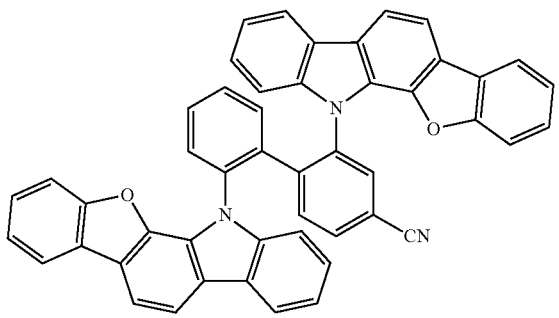
776
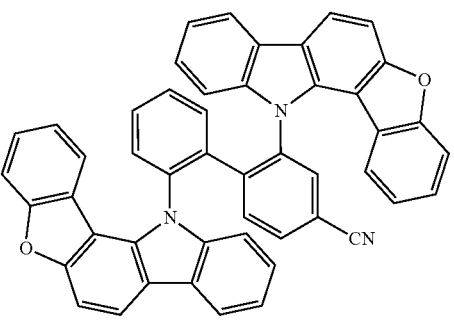

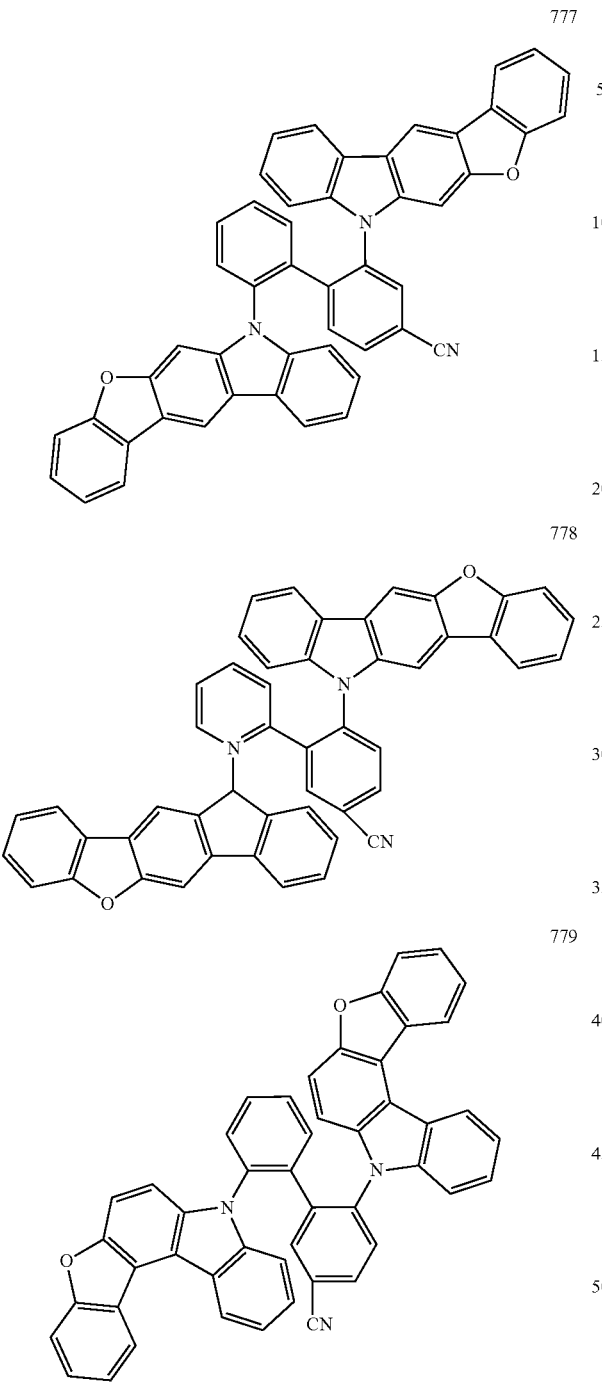
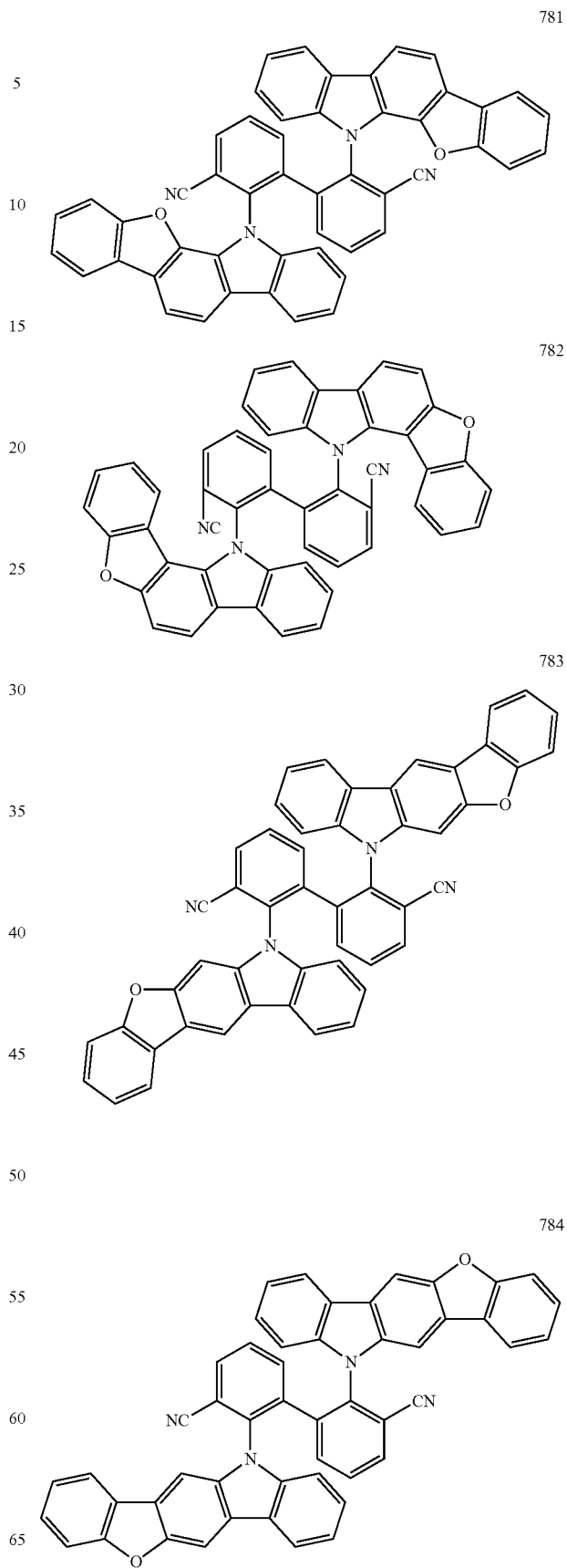

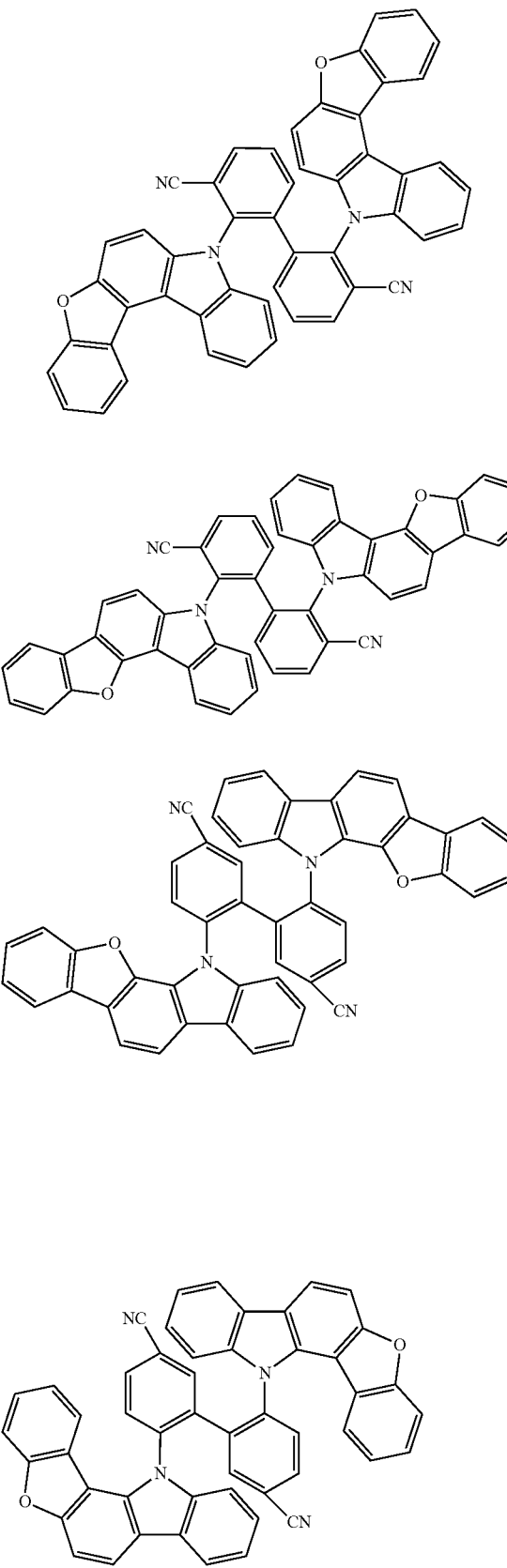
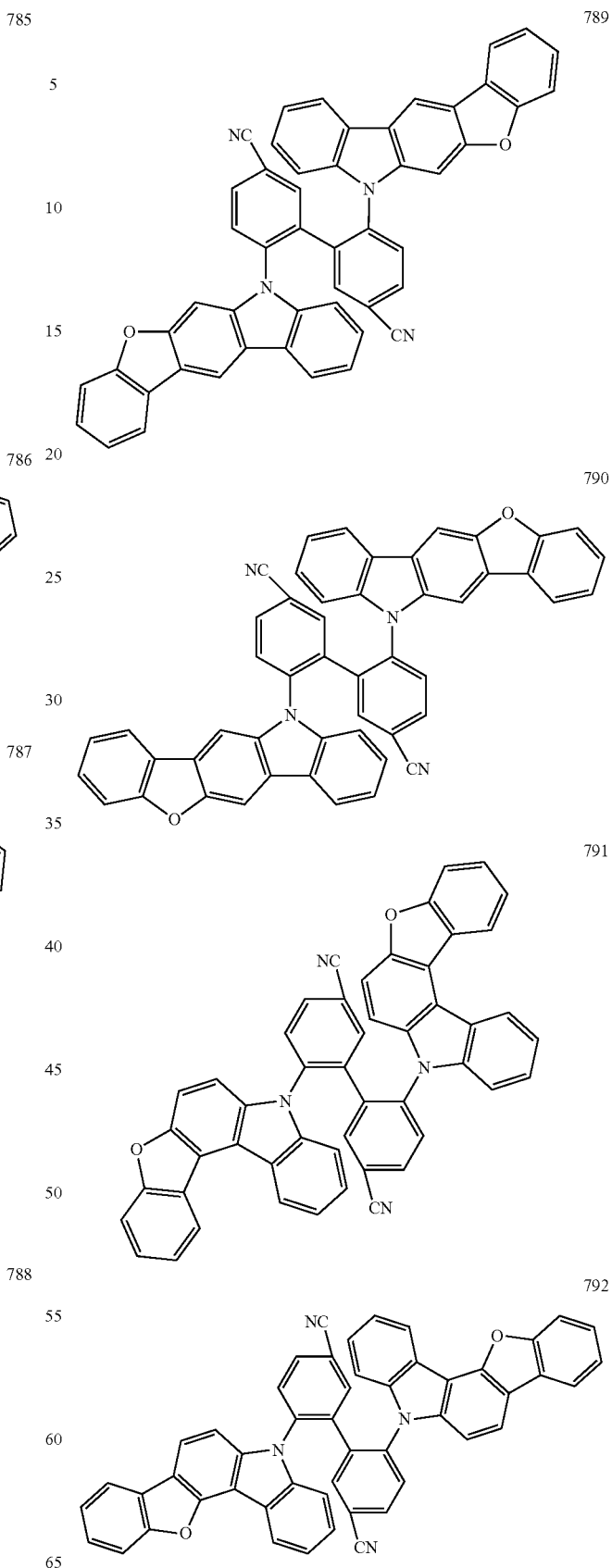

-continued
793
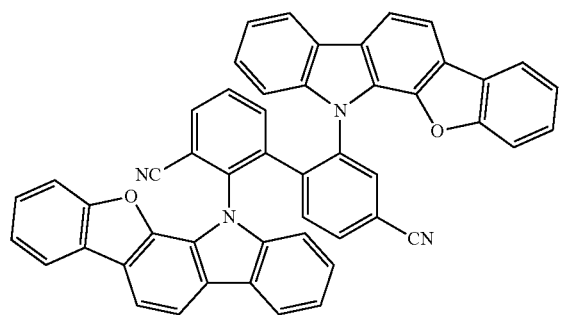
794
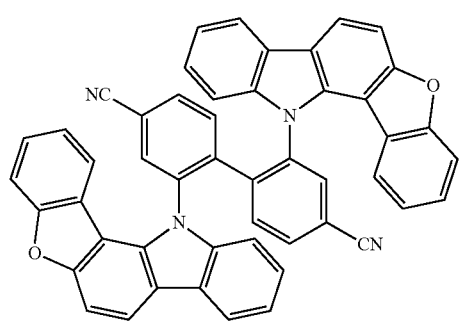
795
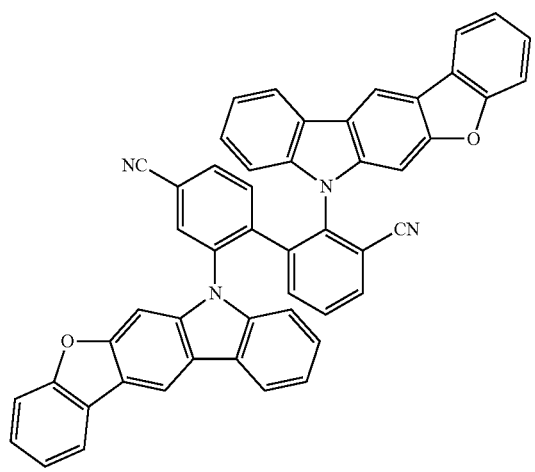
796
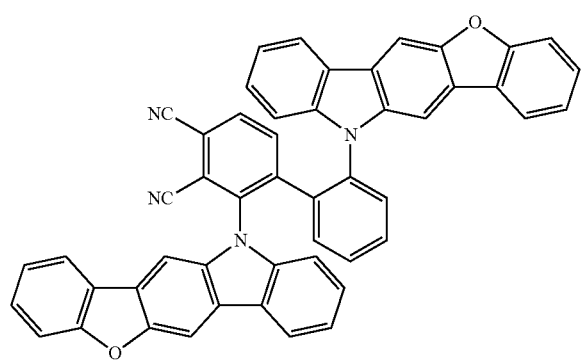
-continued
797
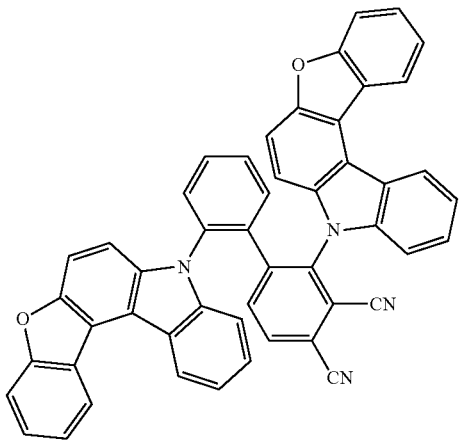
798
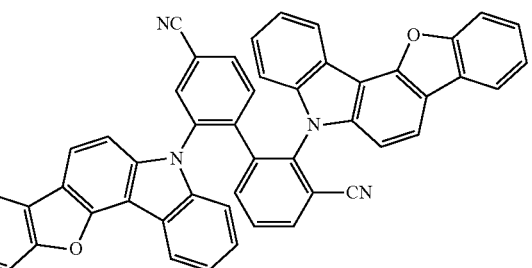
799
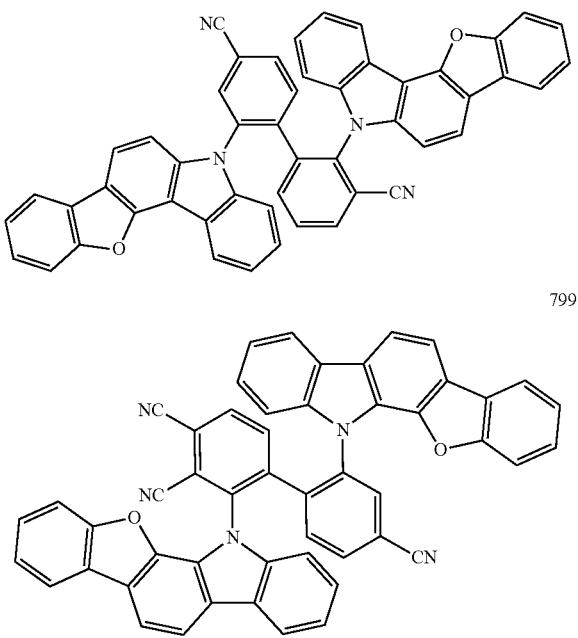
800
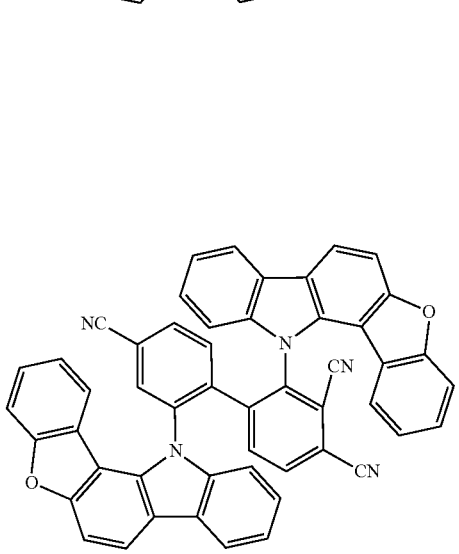

-continued
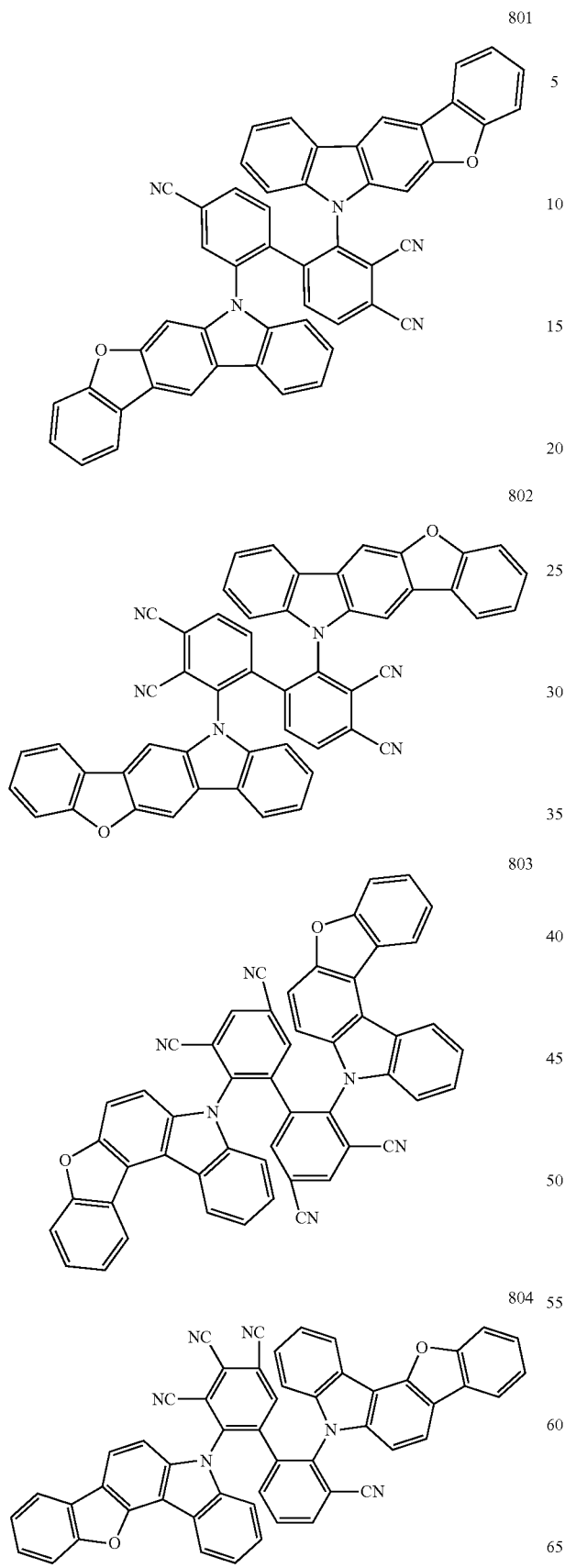
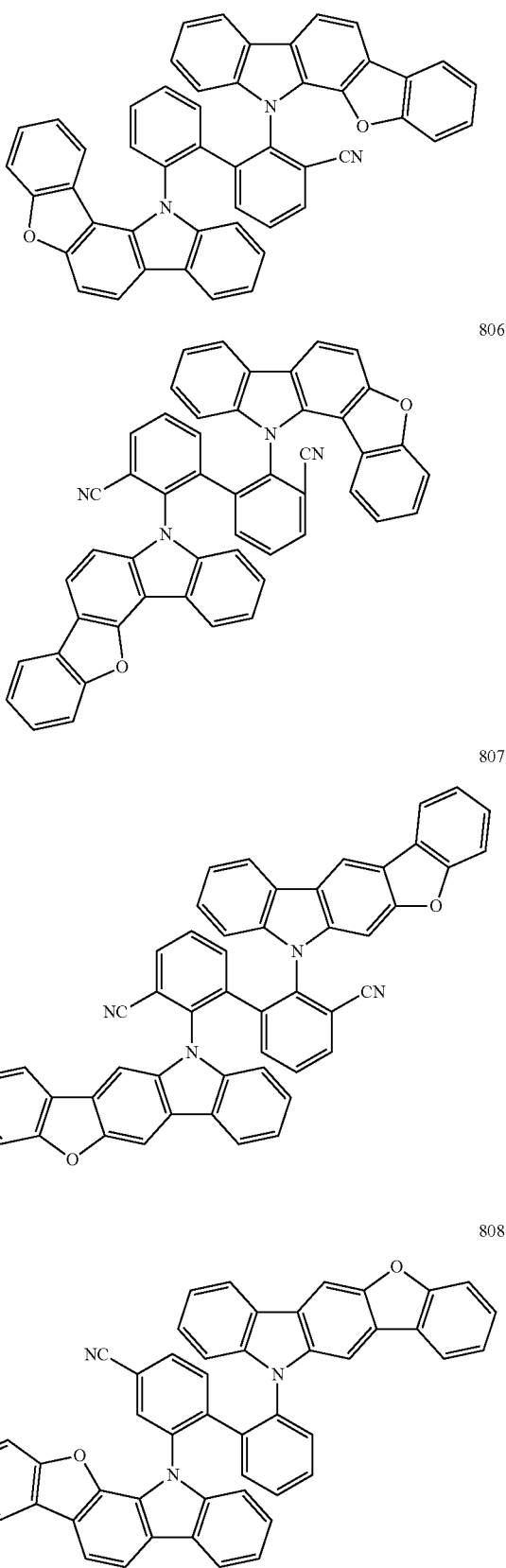

809
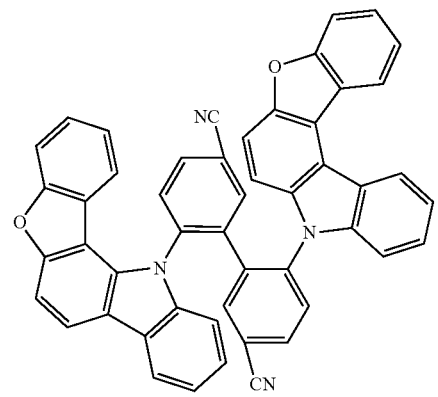
810
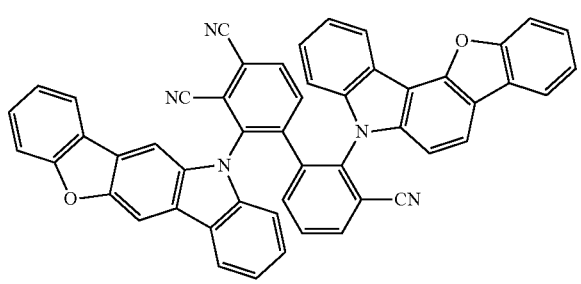
811
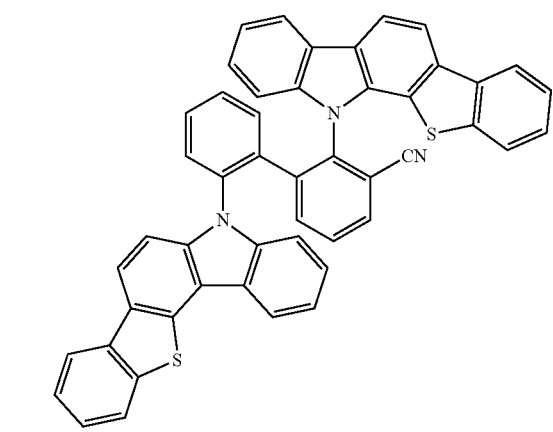
812
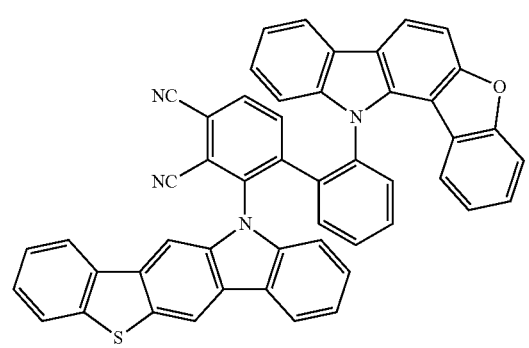
813
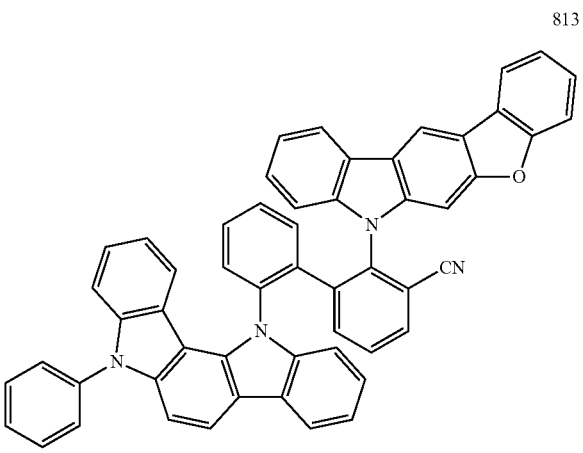
814
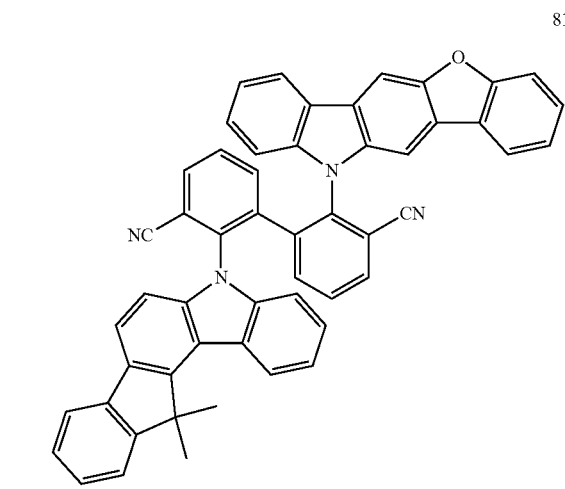
815
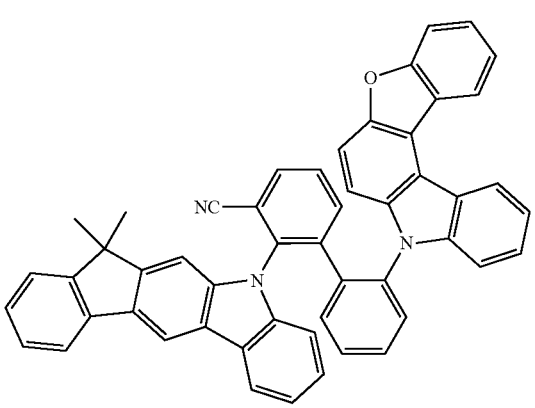
816
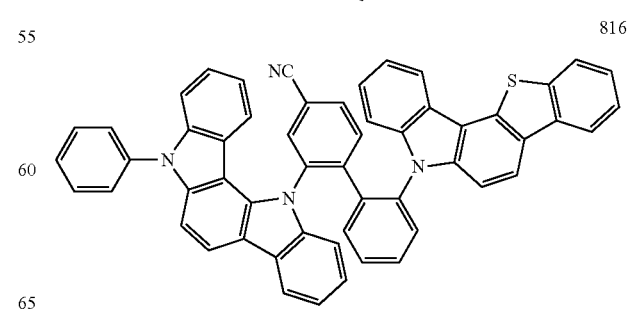

817
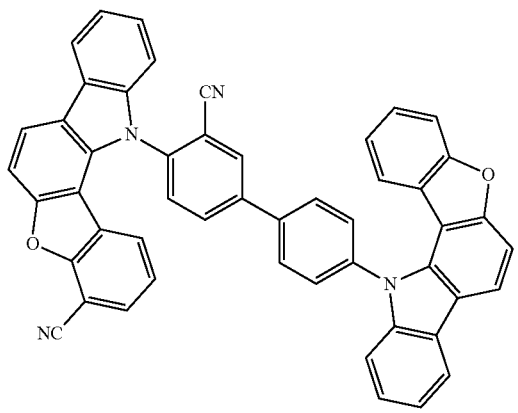
818
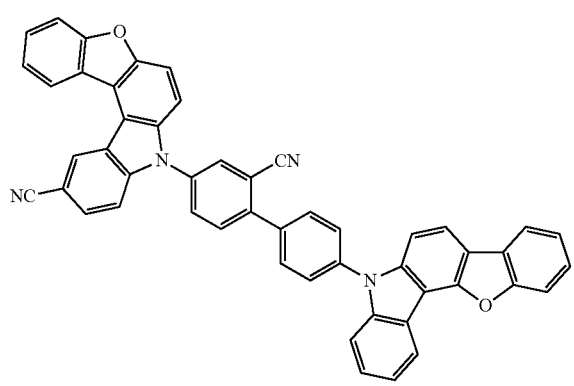
819
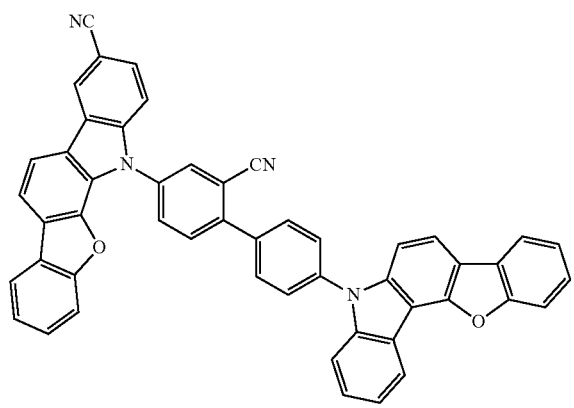
820
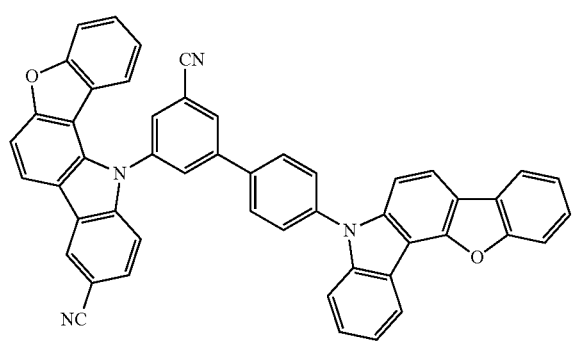
821
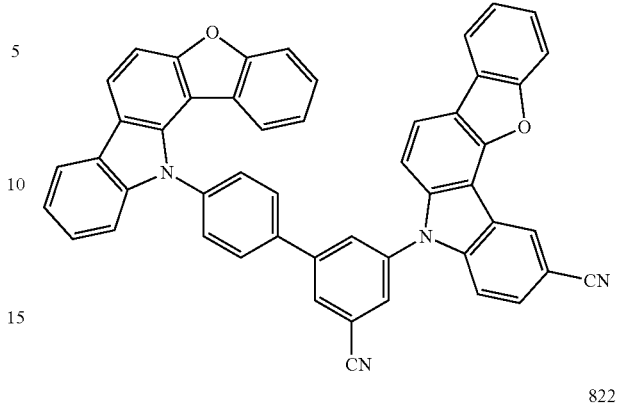
822
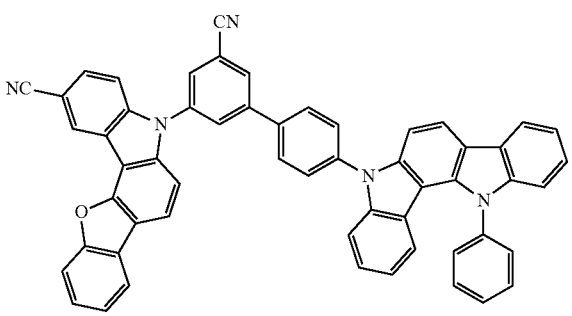
823
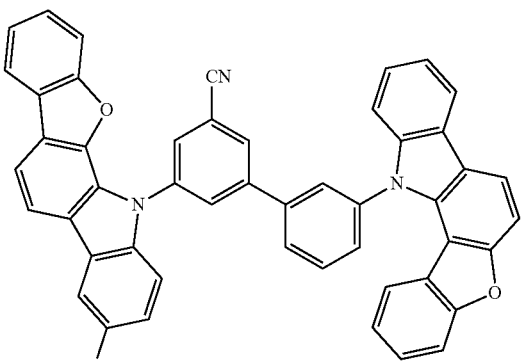
824
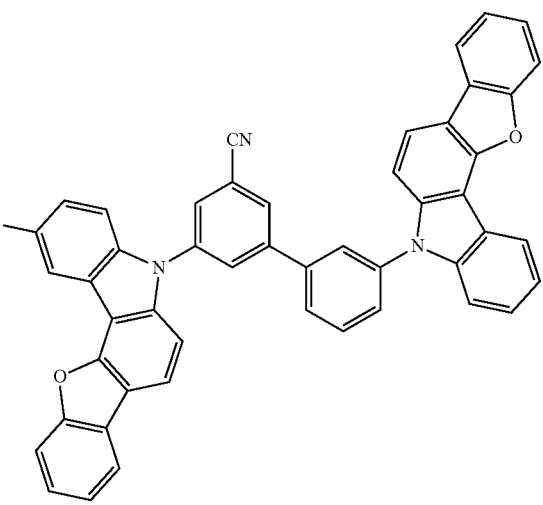

825
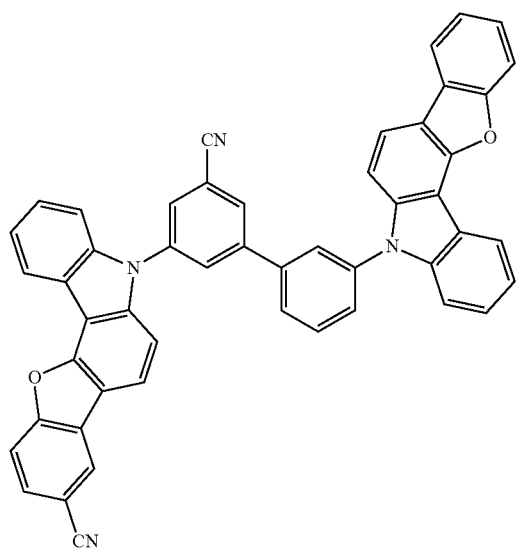
828
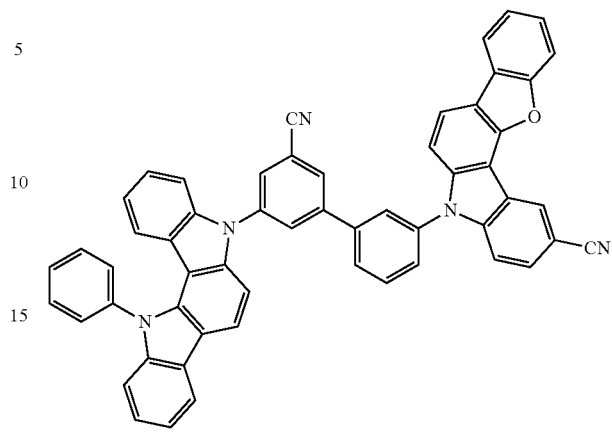
826
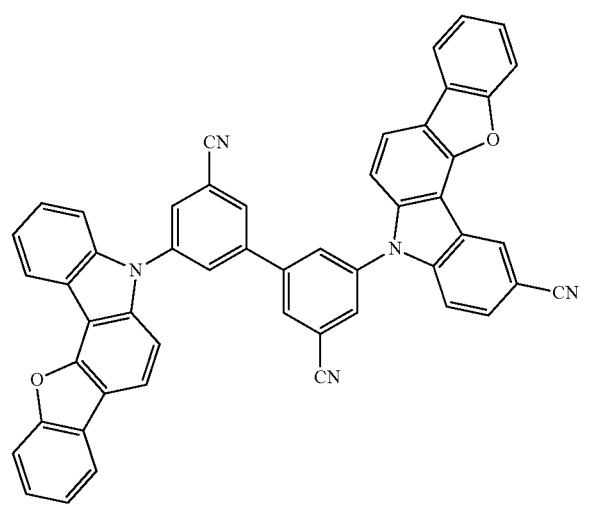
829
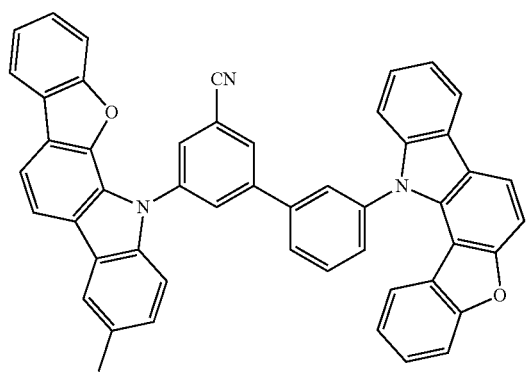
827
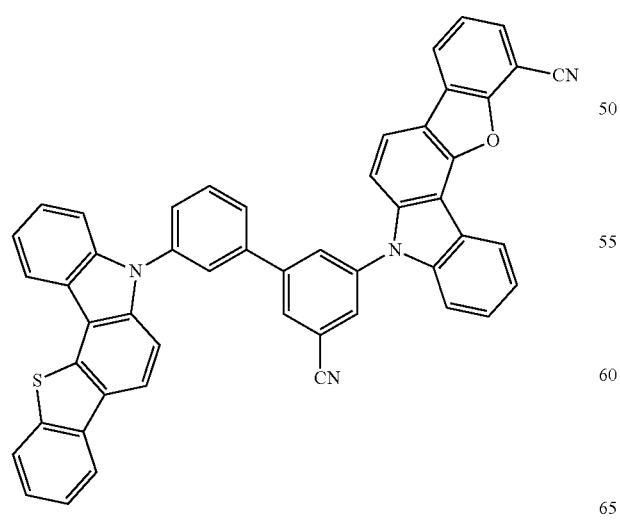
830
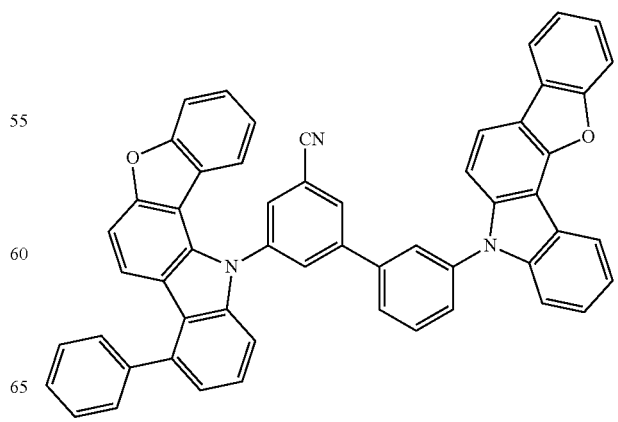

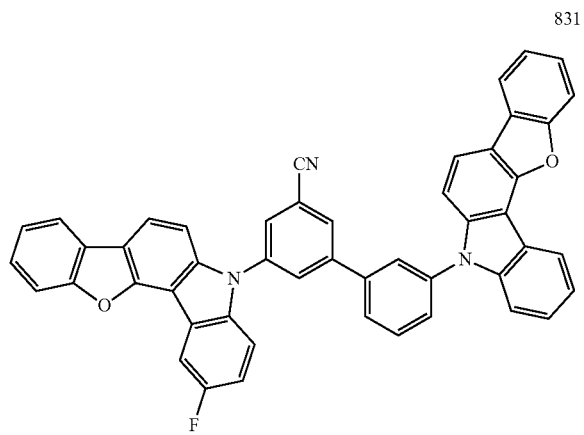
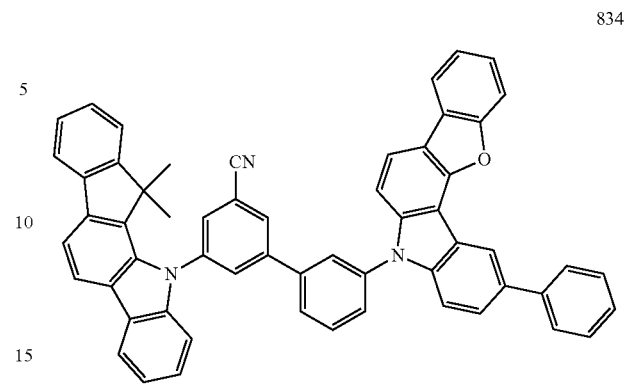
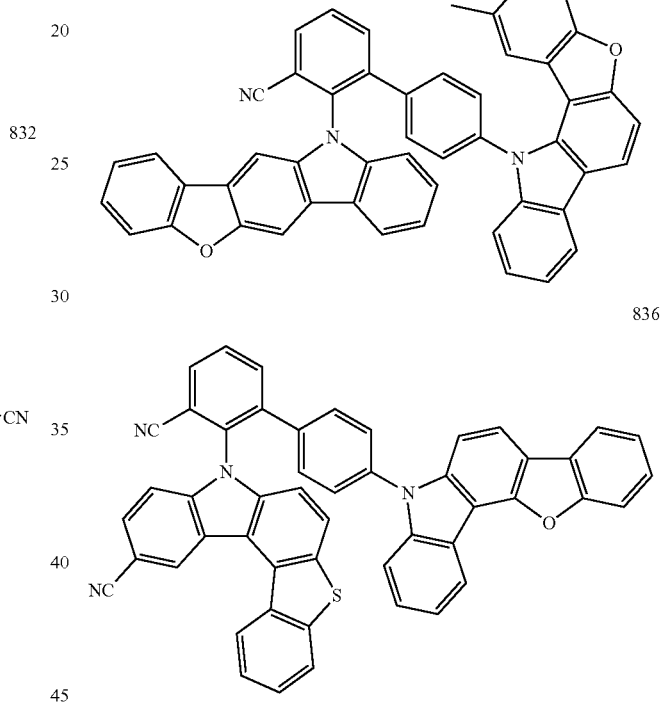
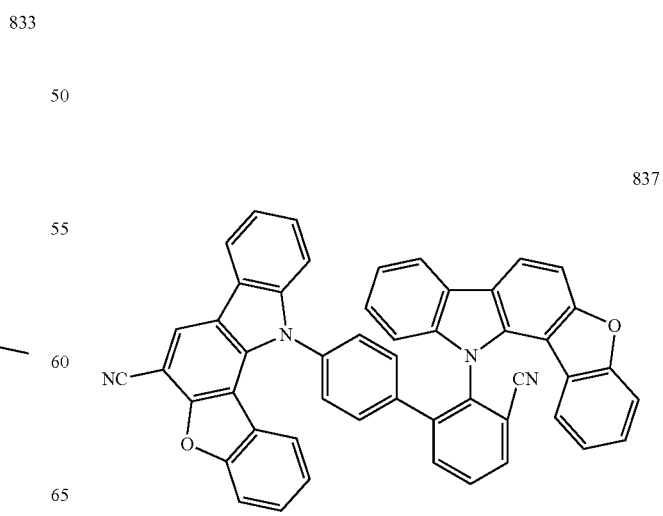

| 661 | 662 |
|---|---|
| -continued | -continued |
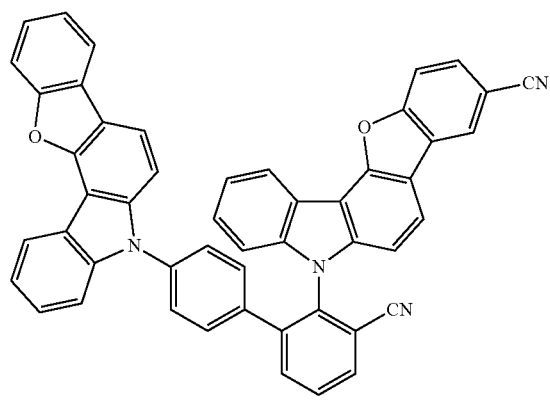
838
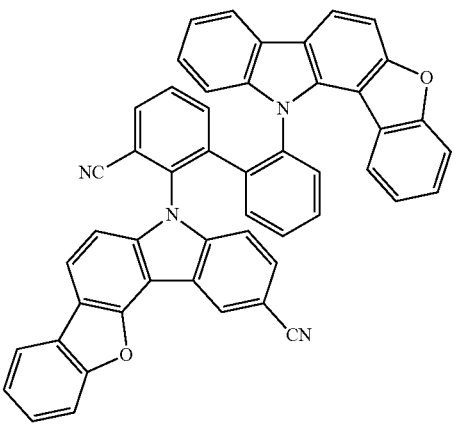
841
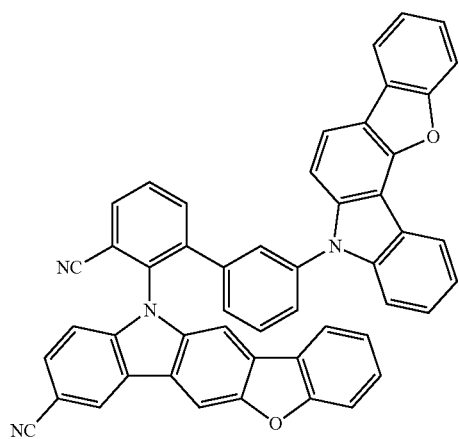
839
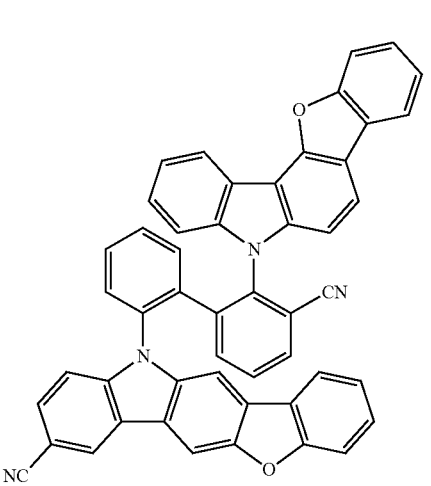
842
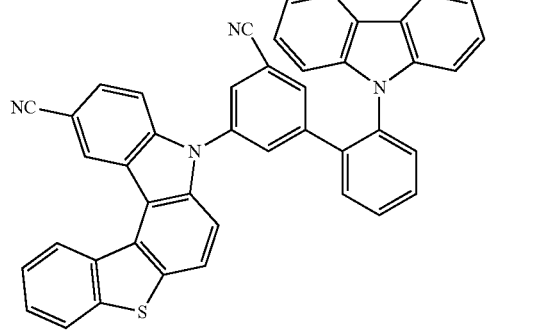
840
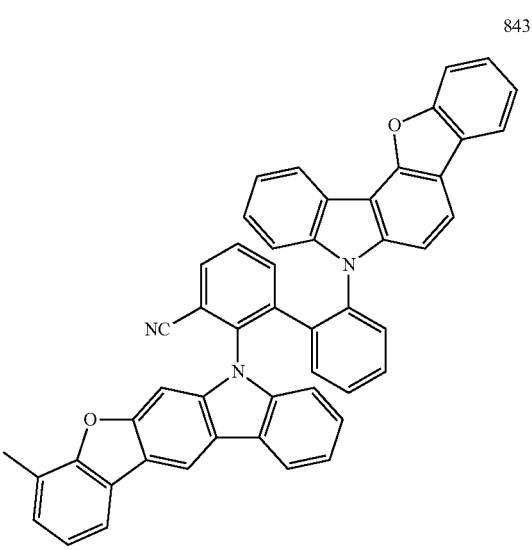
843

844
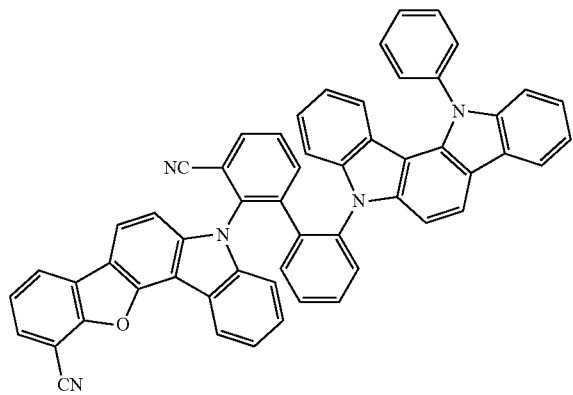
845
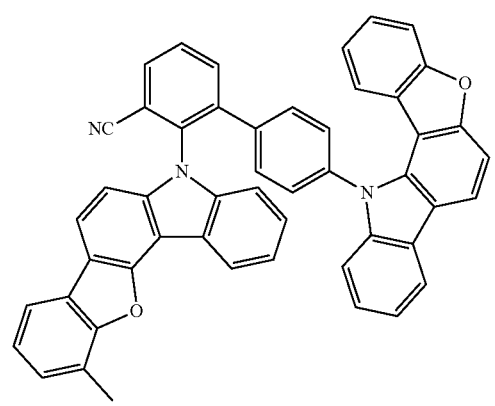
846
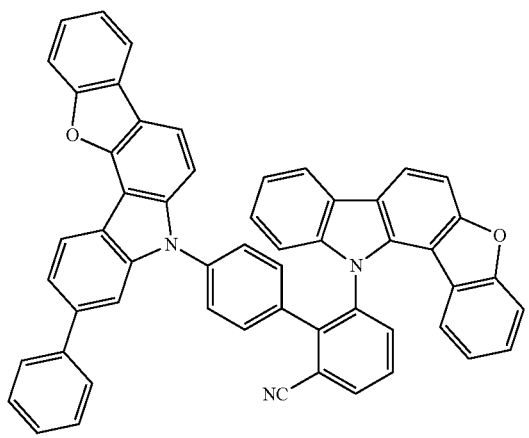
847
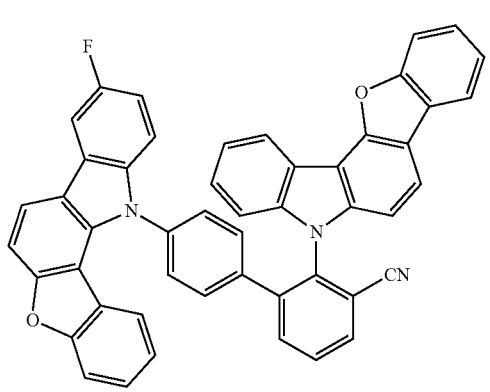
848
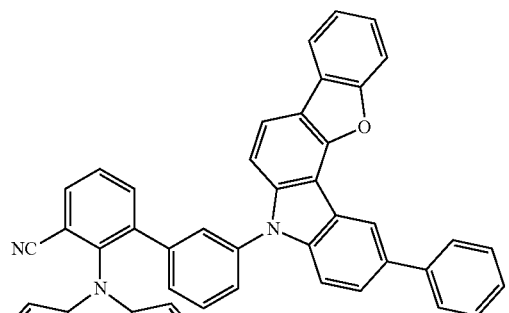
849
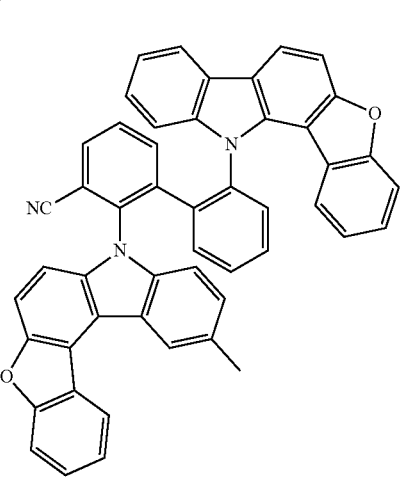
850
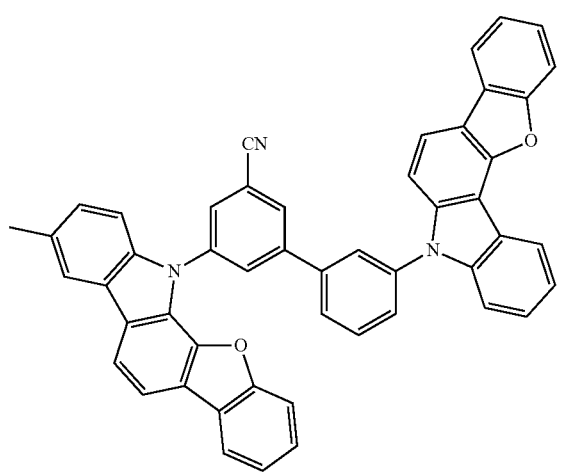

851
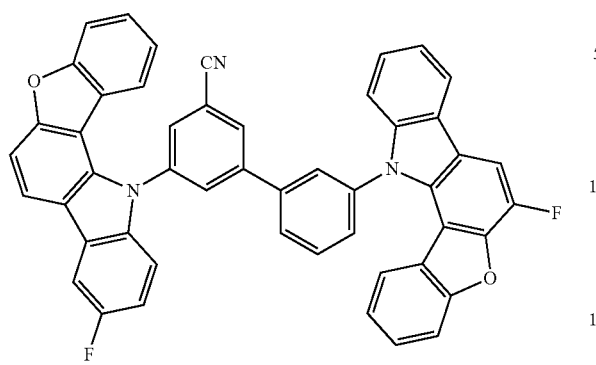
852
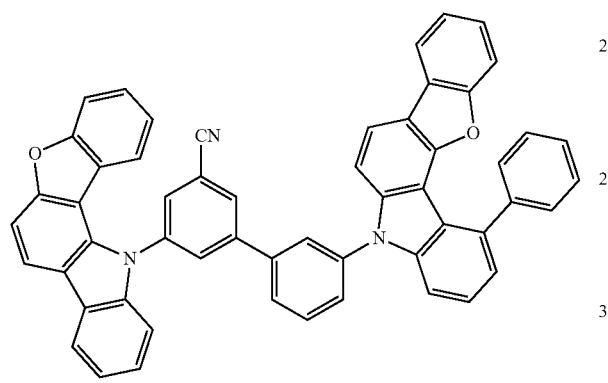
Group HE3
1
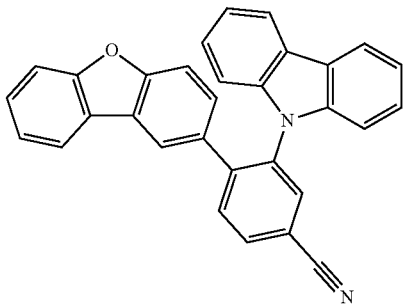
2
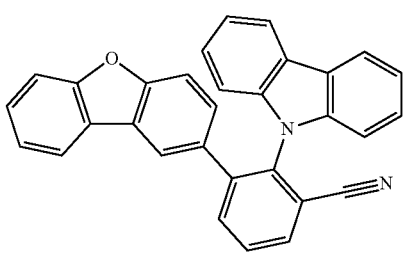
3
4
5
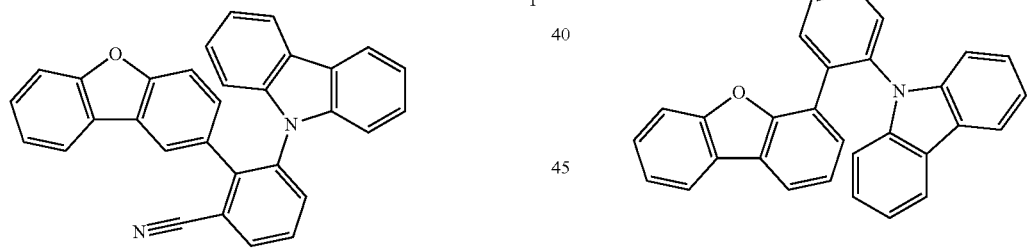
6
7
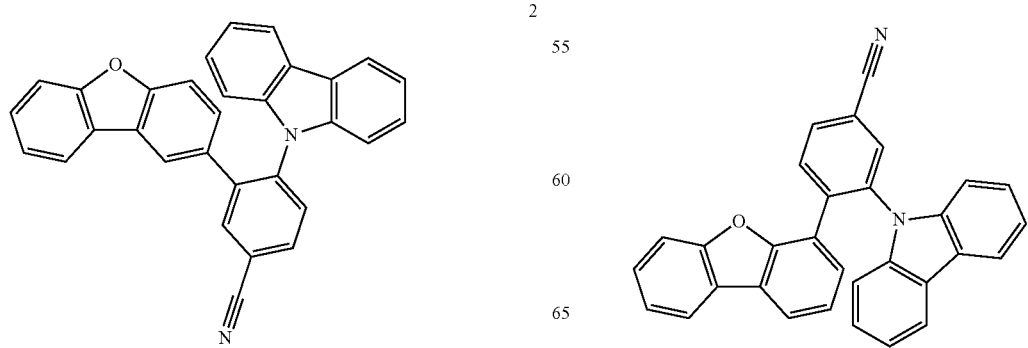

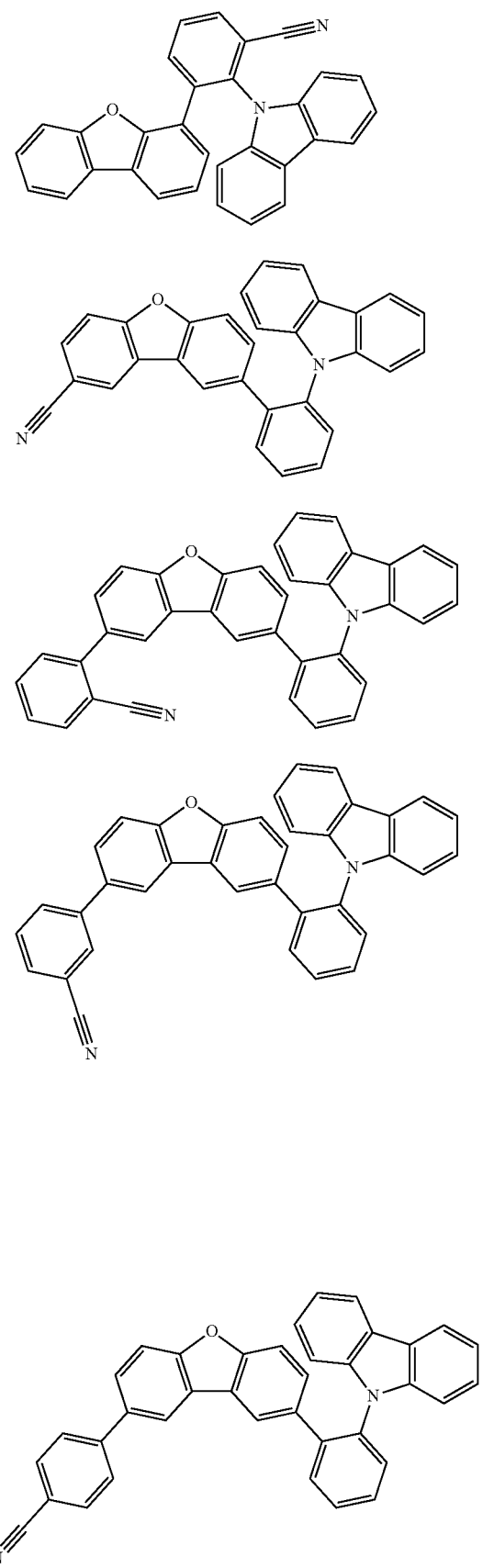
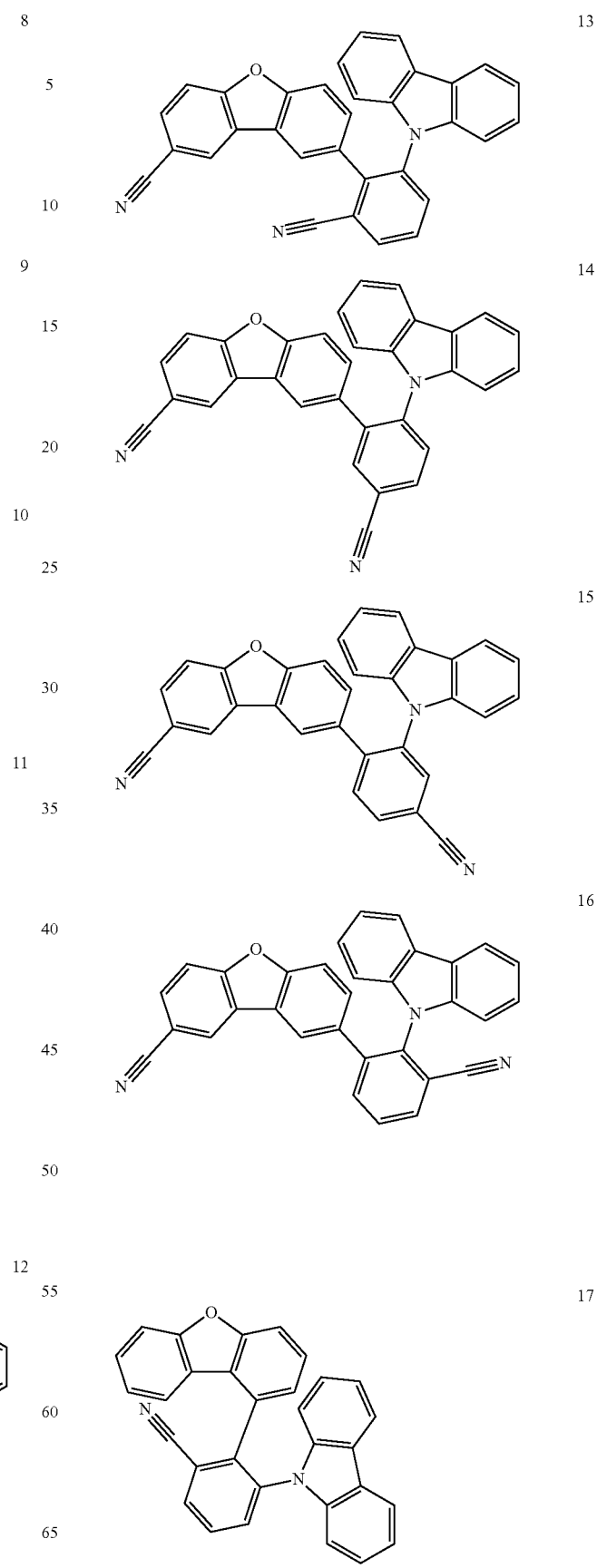

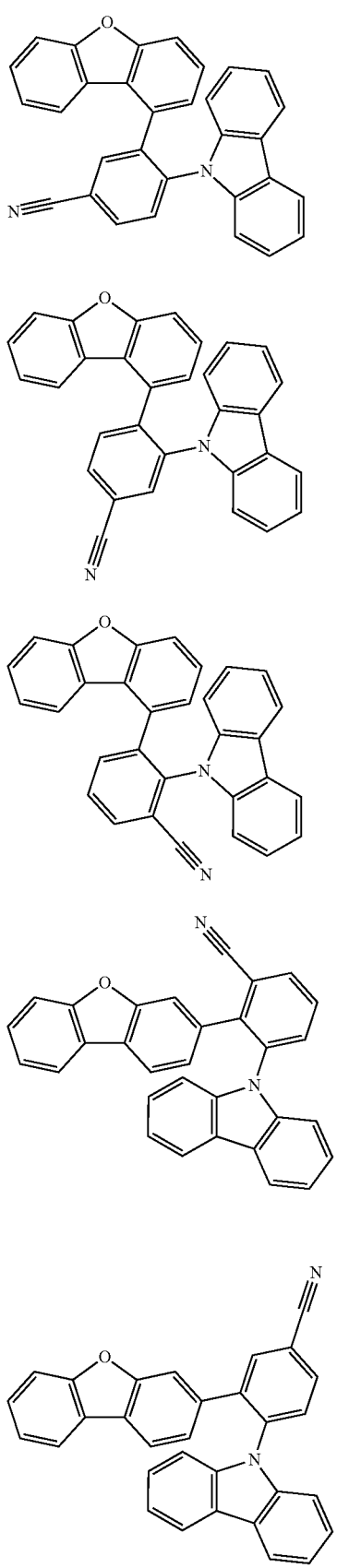
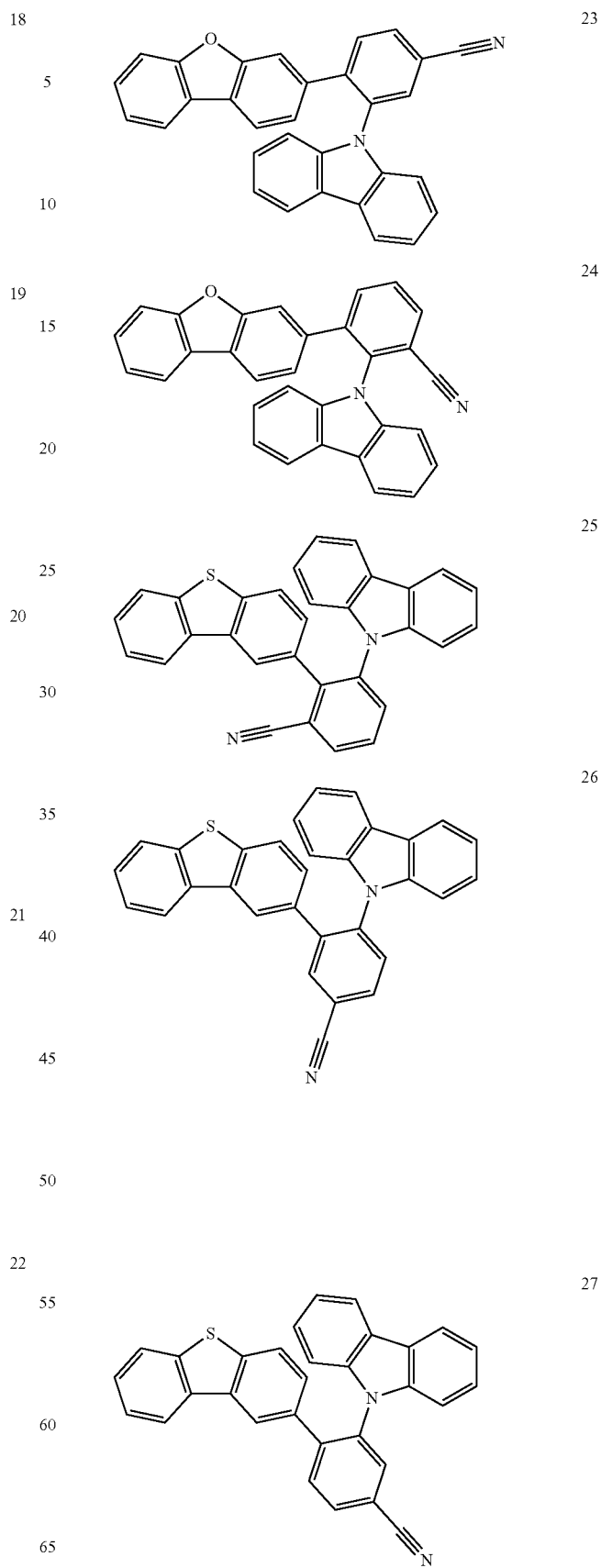

28
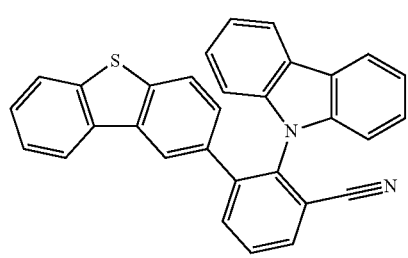
29
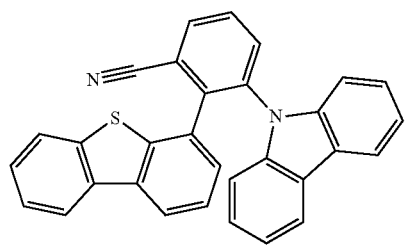
30
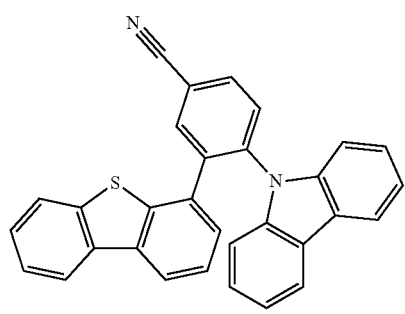
31
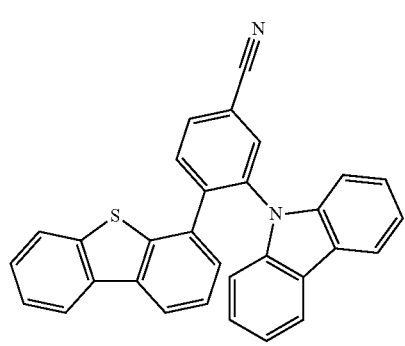
32
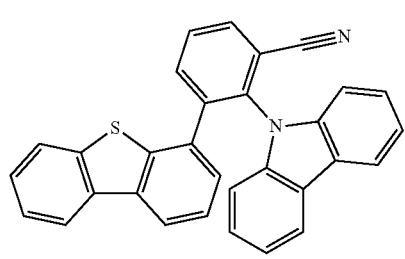
33
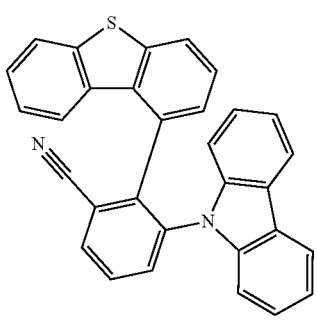
34
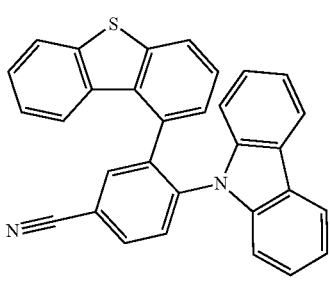
35
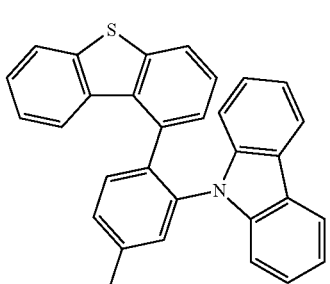
36
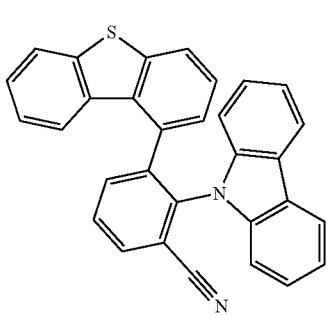
37
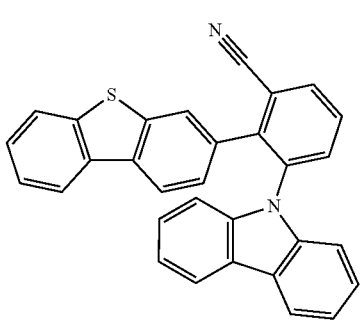

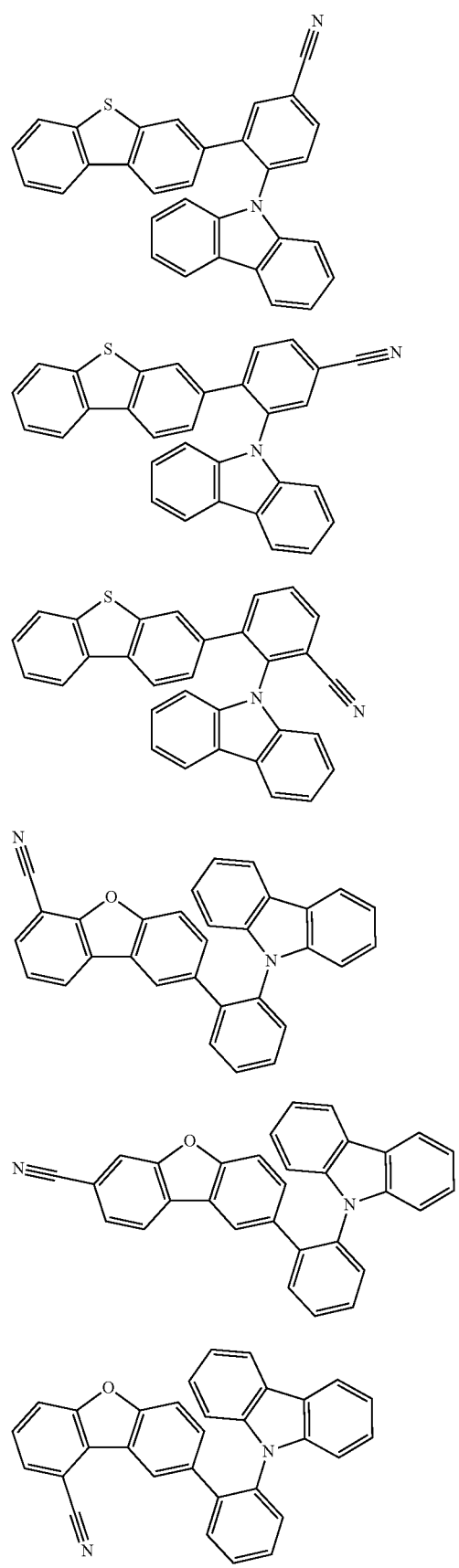
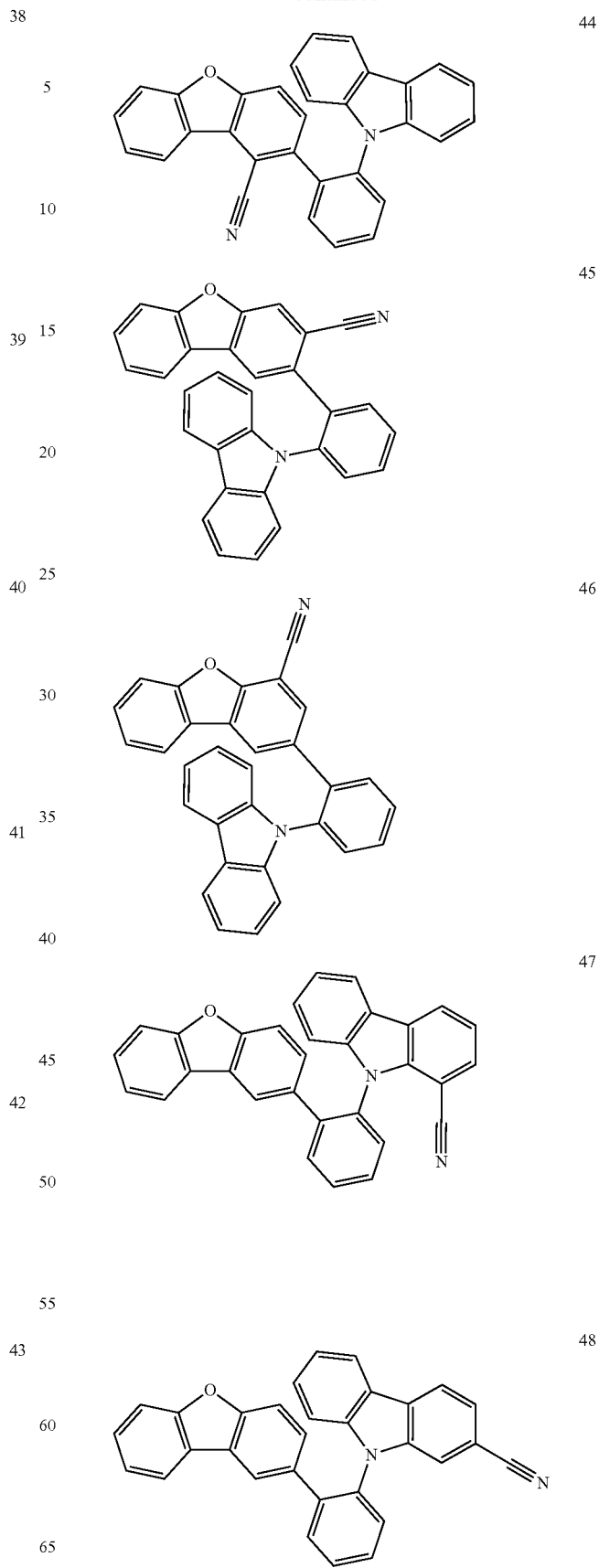

49
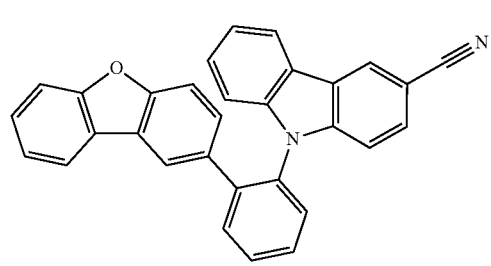
50
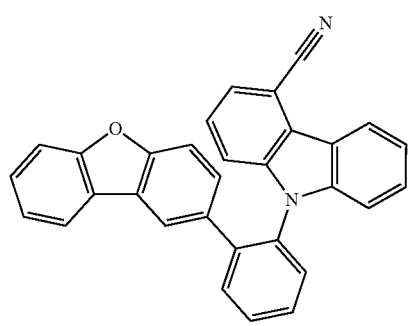
51
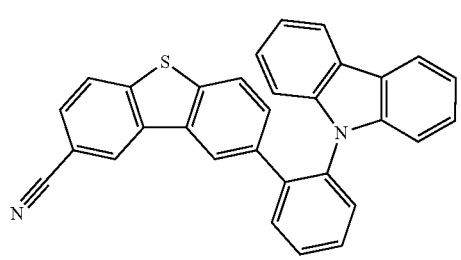
52
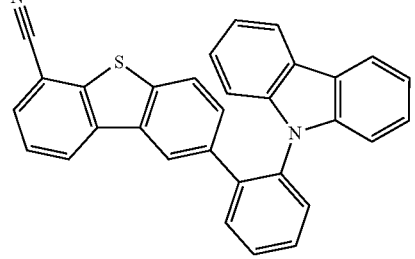
53
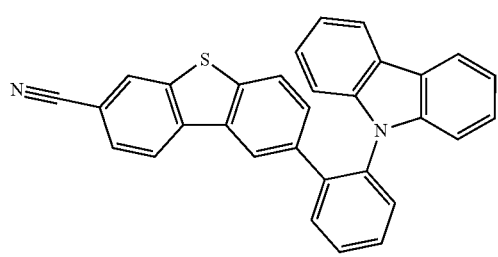
54
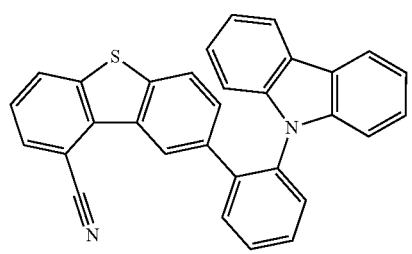
55
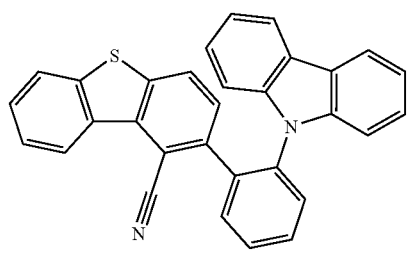
56
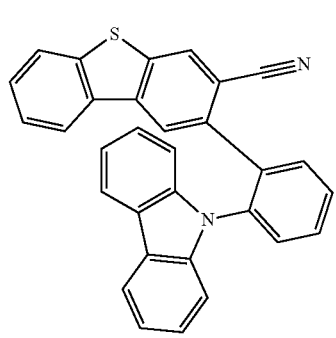
57
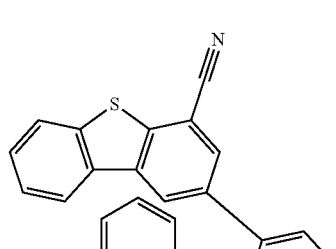
58
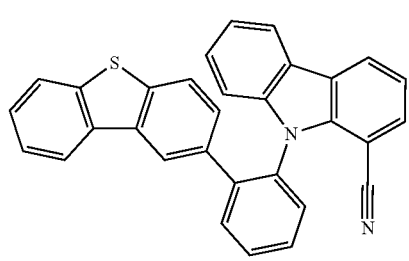
59
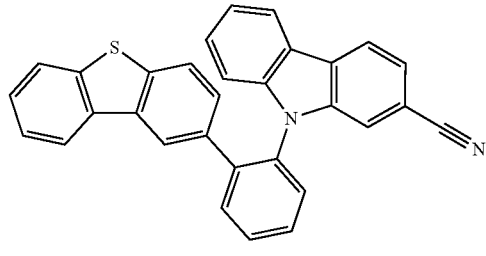

60
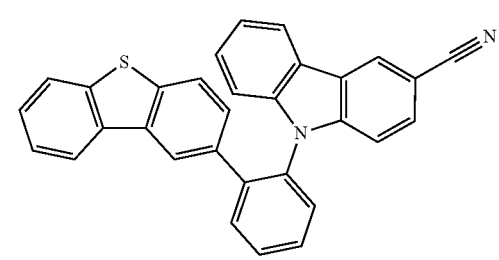
61
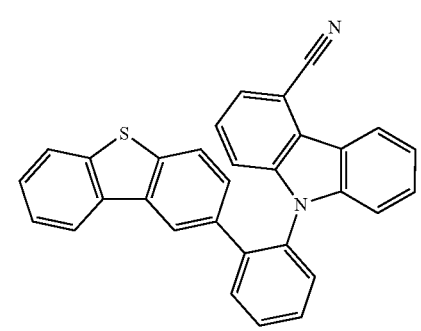
62
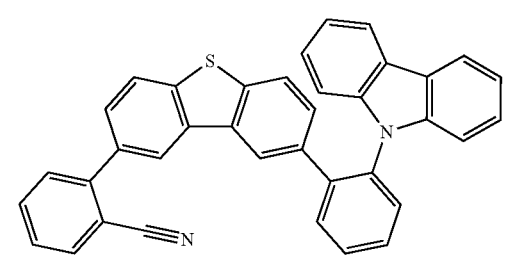
63
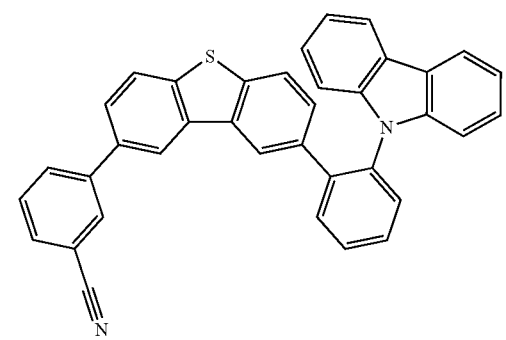
64
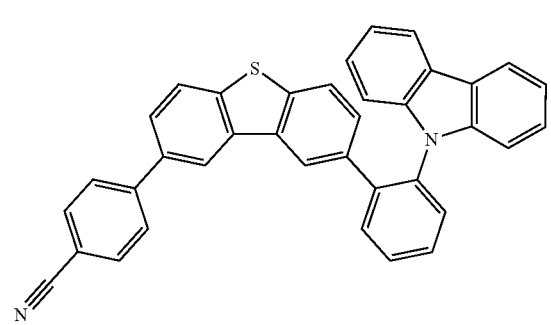
65
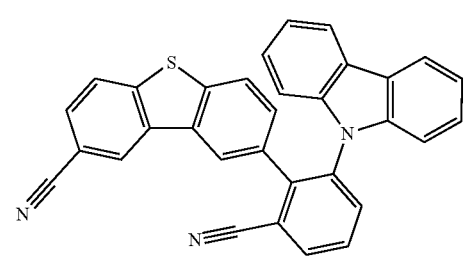
66
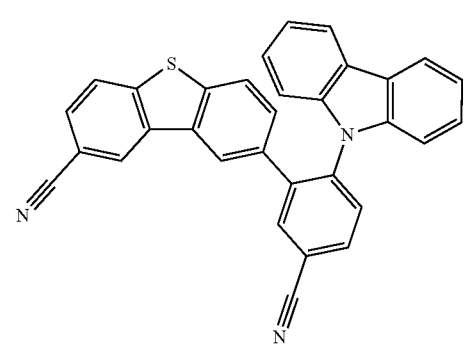
67
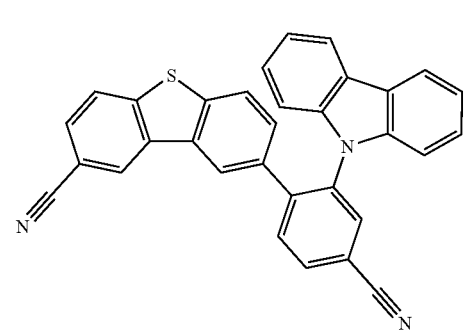
68
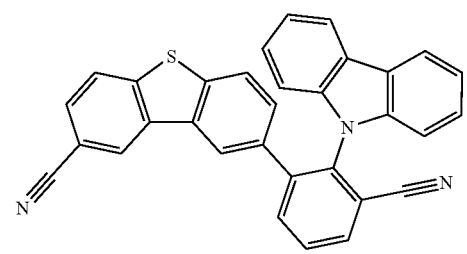
69
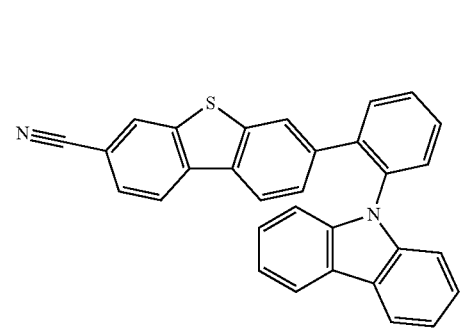

-continued
70
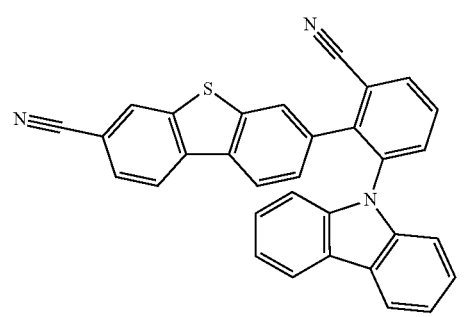
71
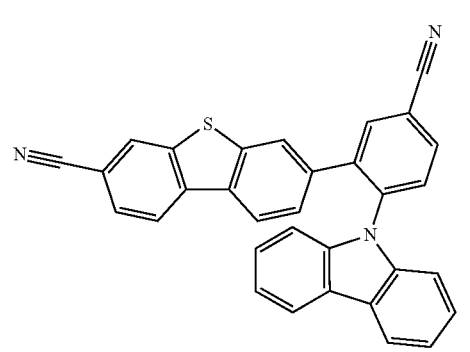
72
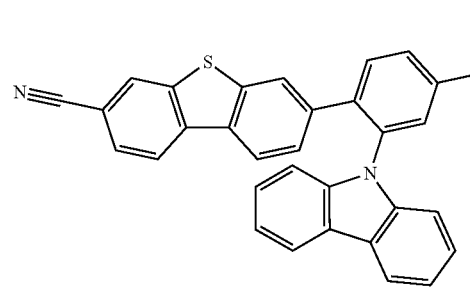
73
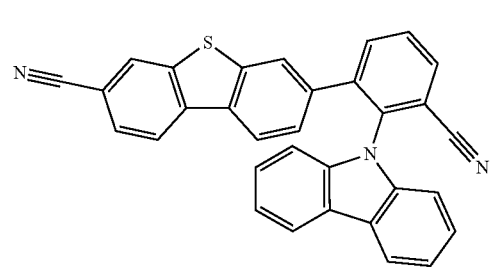
74
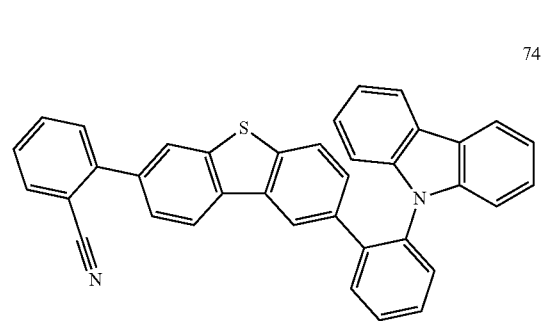
-continued
75
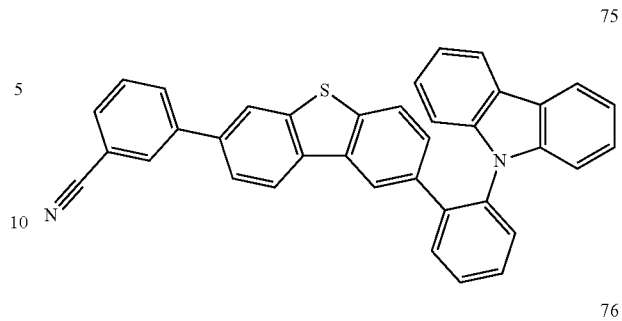
76
77
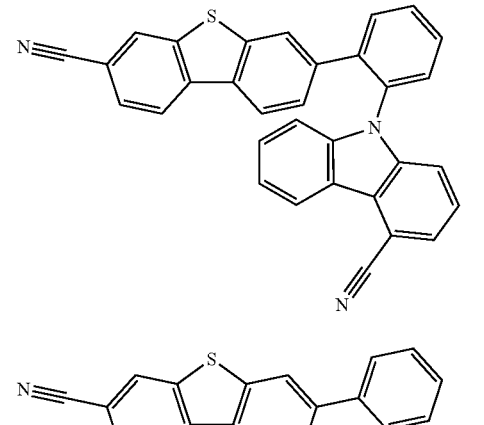
78
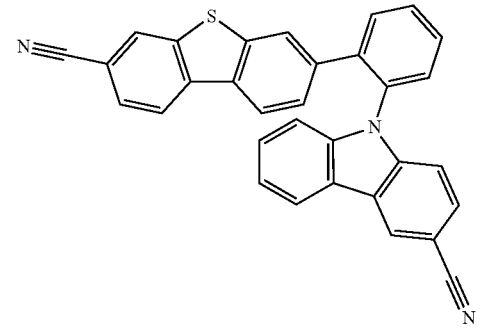
79
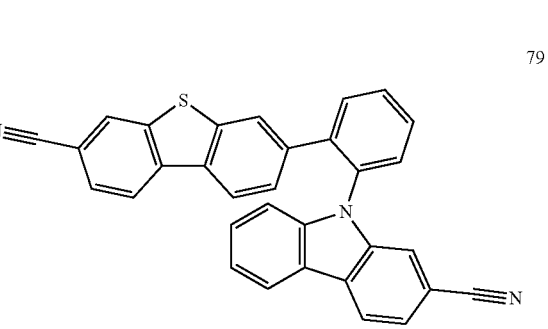

80
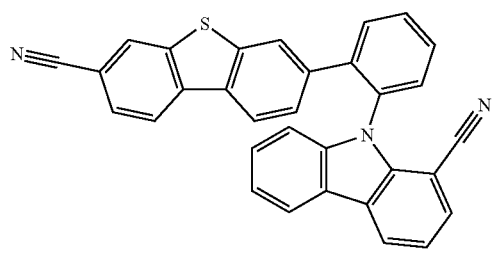
81
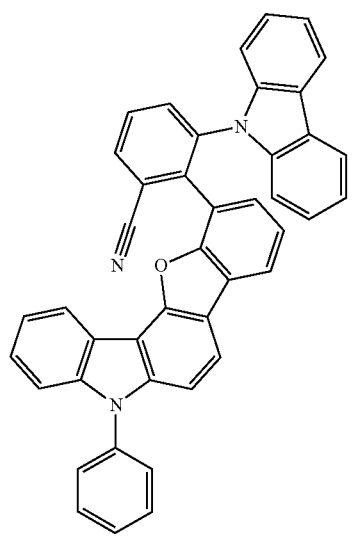
82
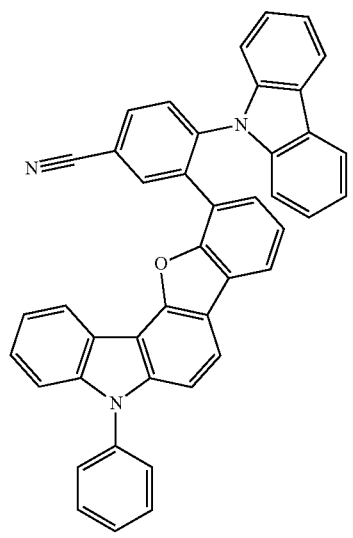
83
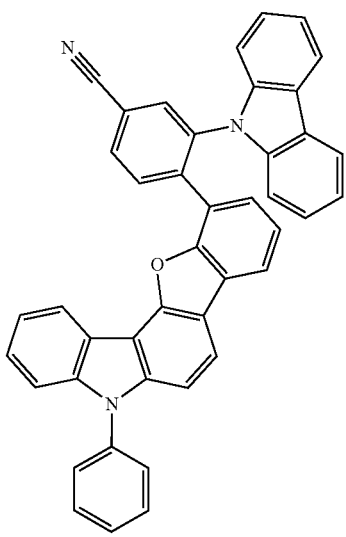
84
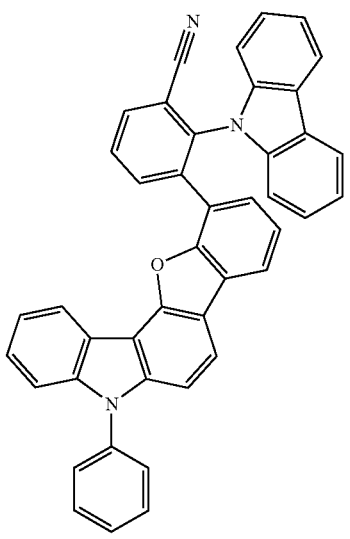
85
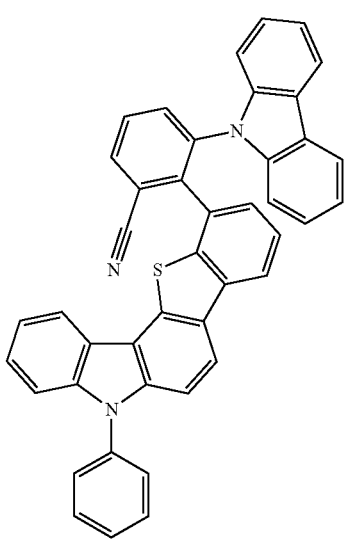

86
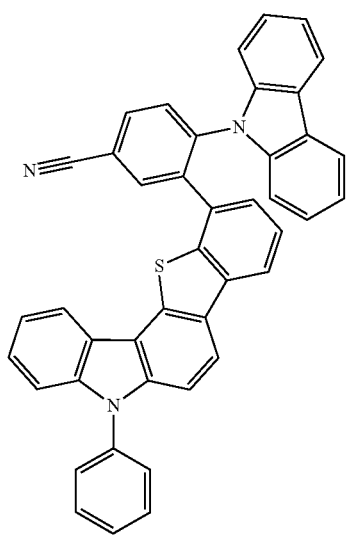
87
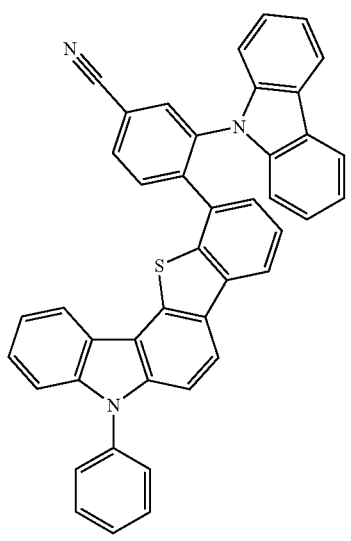
88
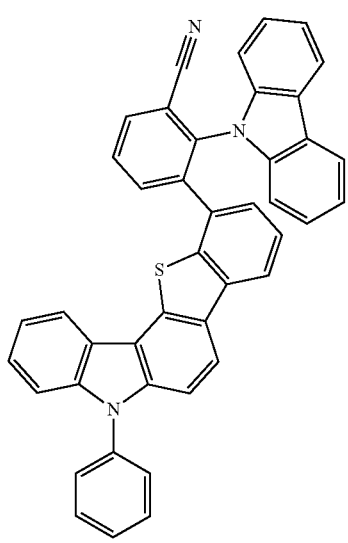
89
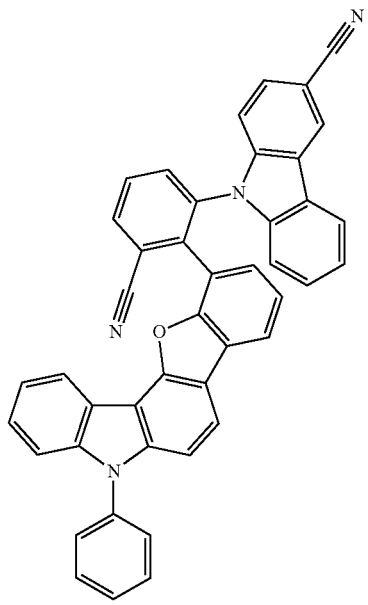
90
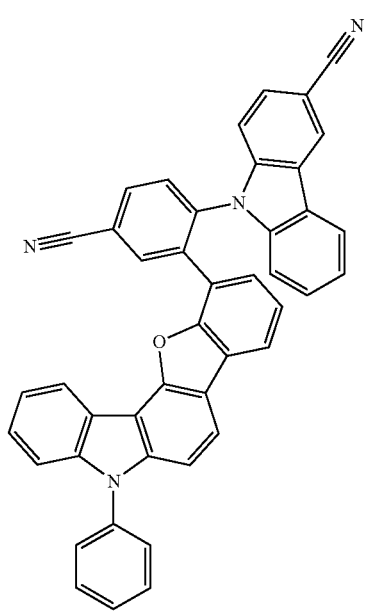

-continued
91
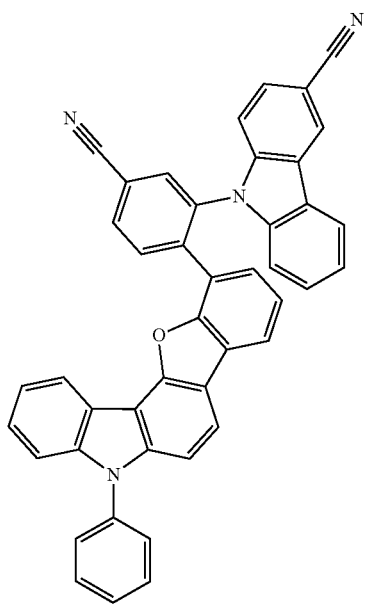
92
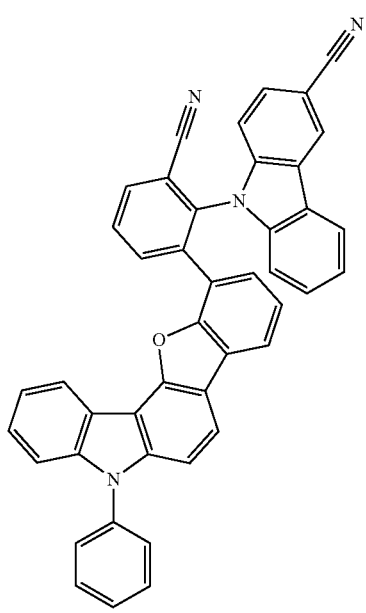
-continued
93
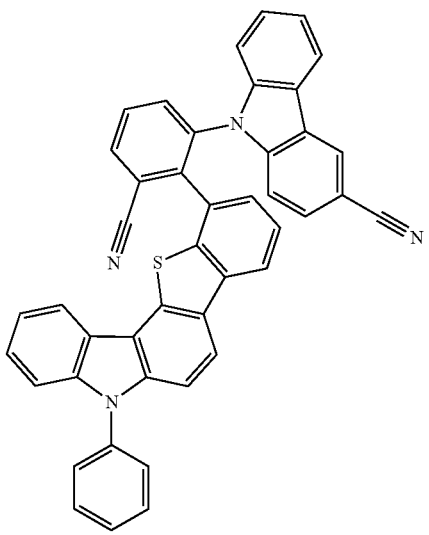
94
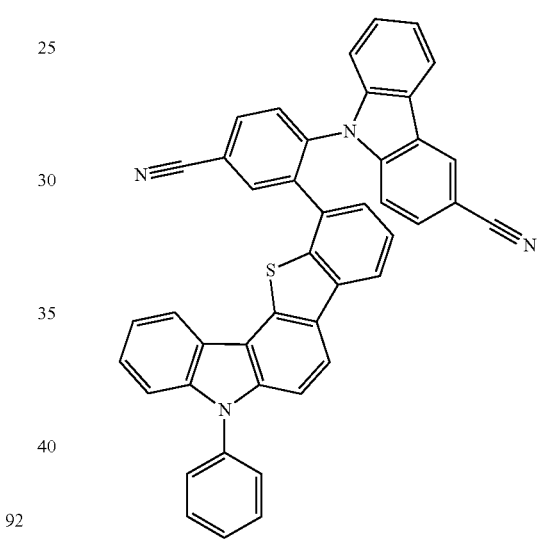
95
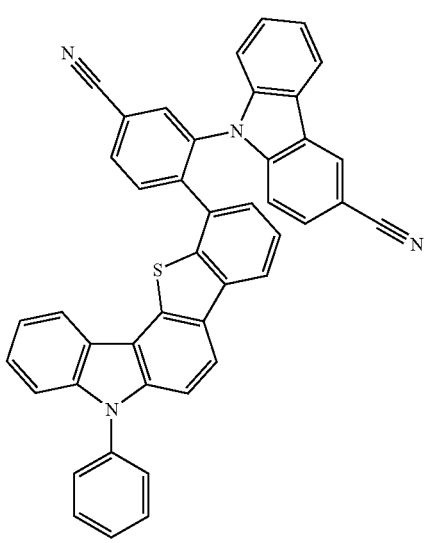

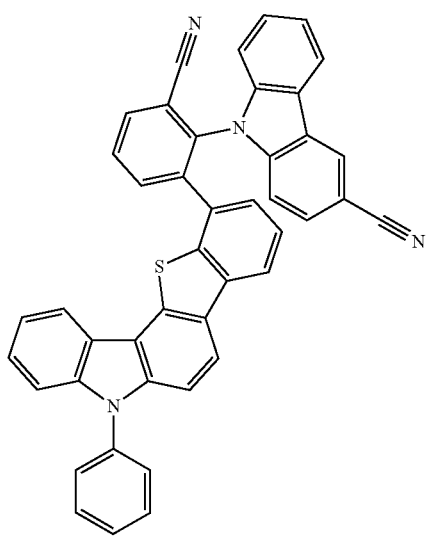
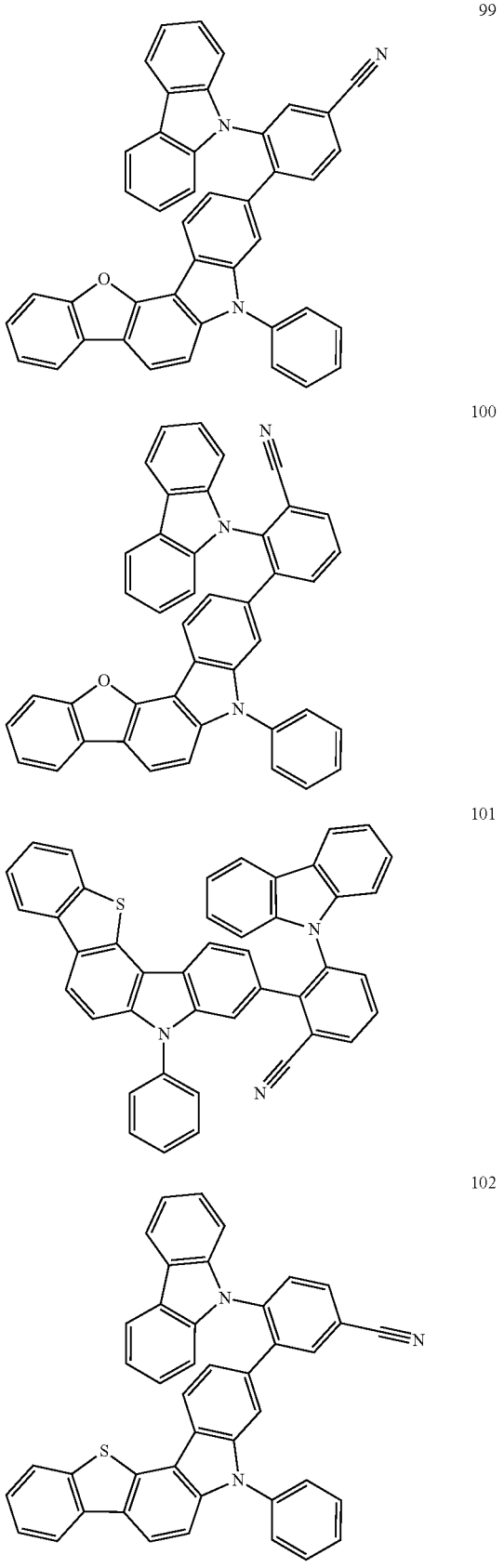

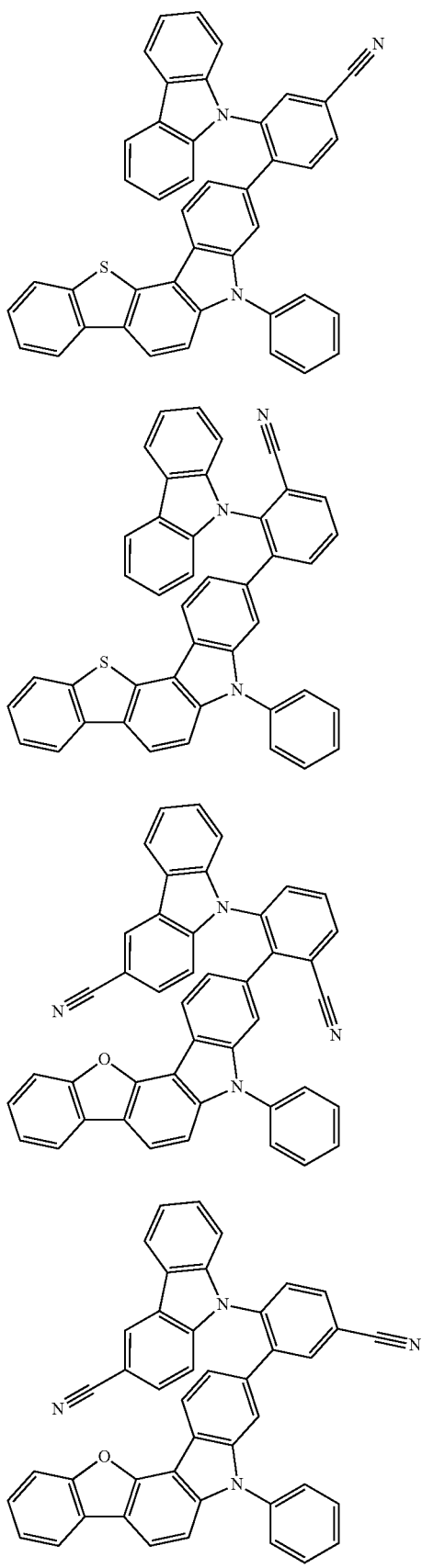
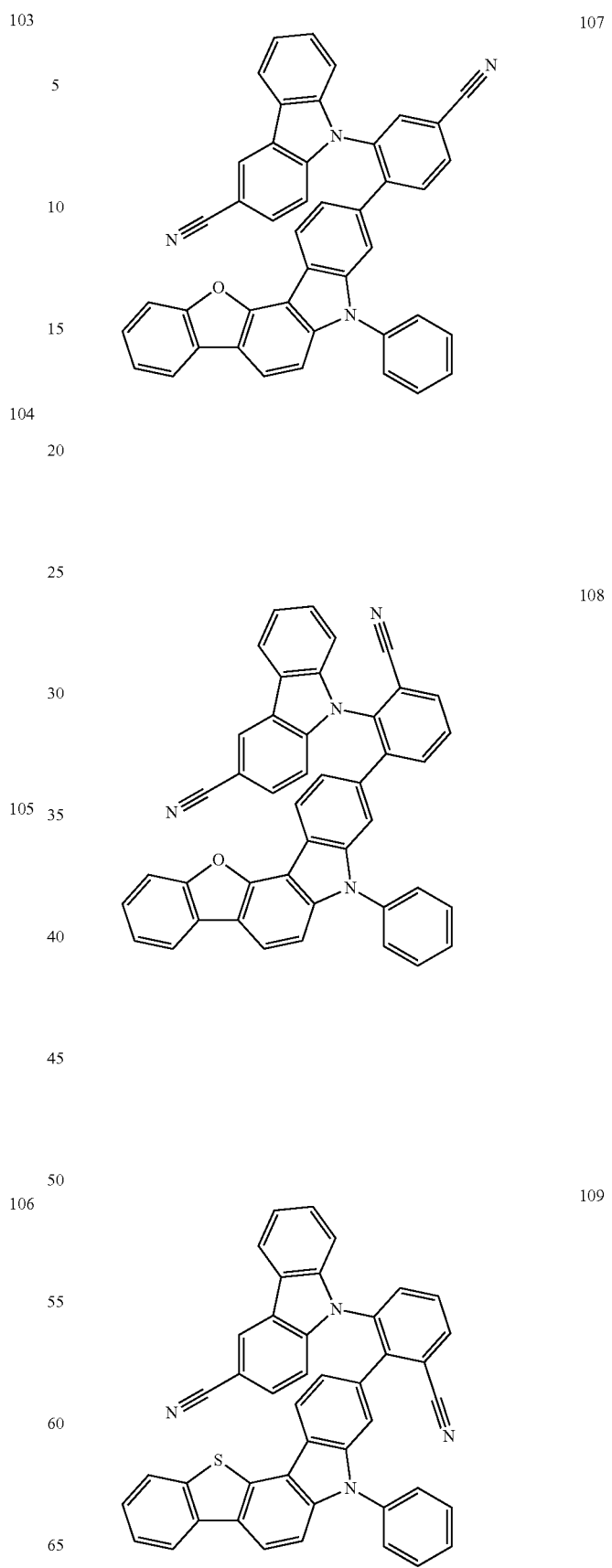

691
-continued
110
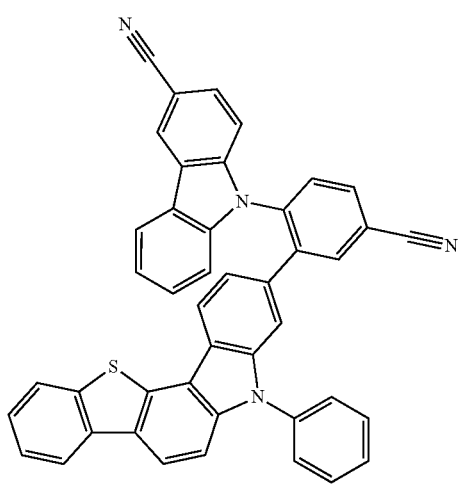
111
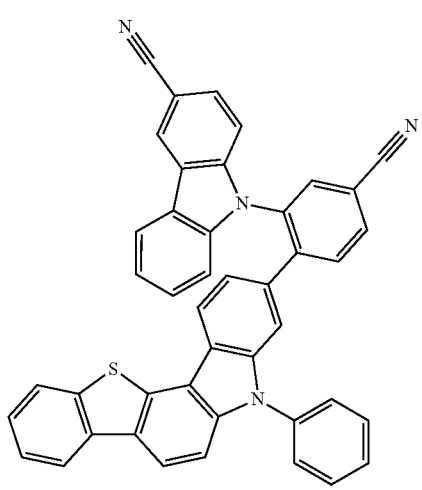
112
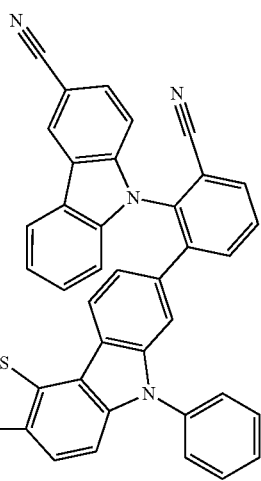
692
-continued
113
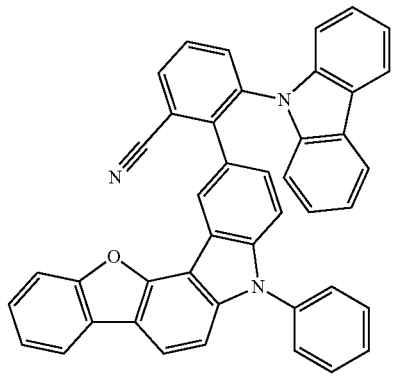
114
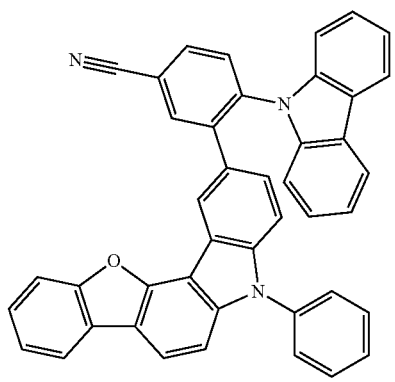
115
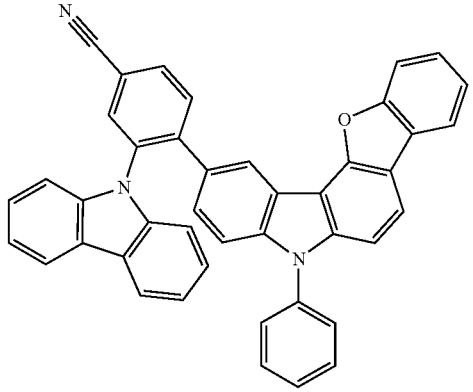
116
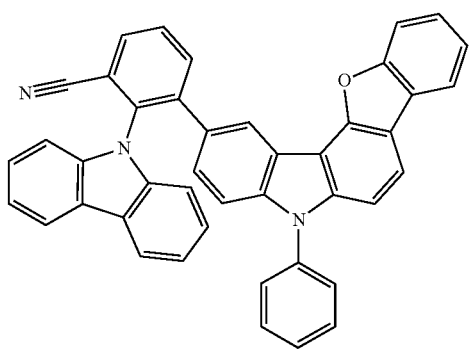

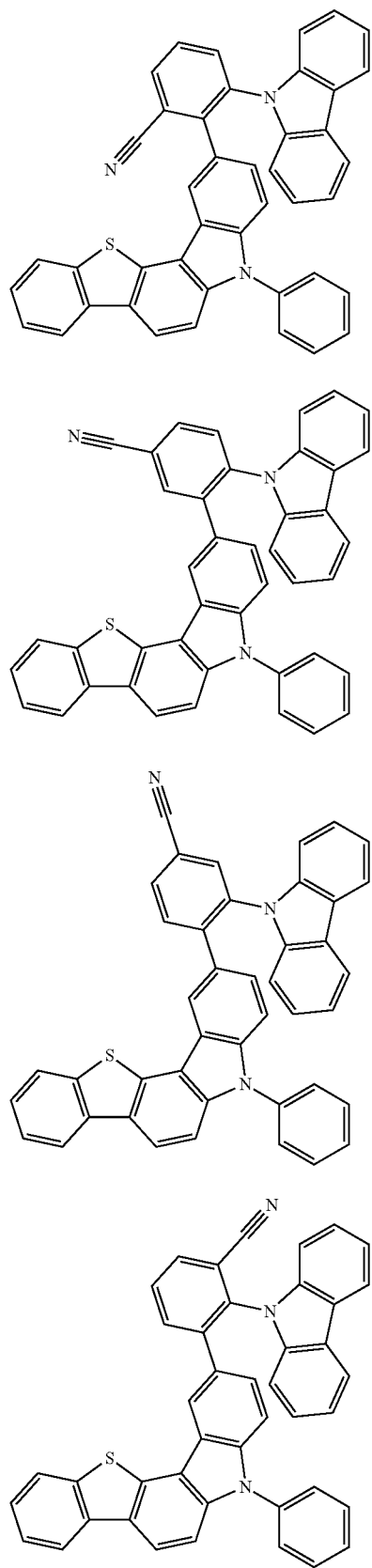
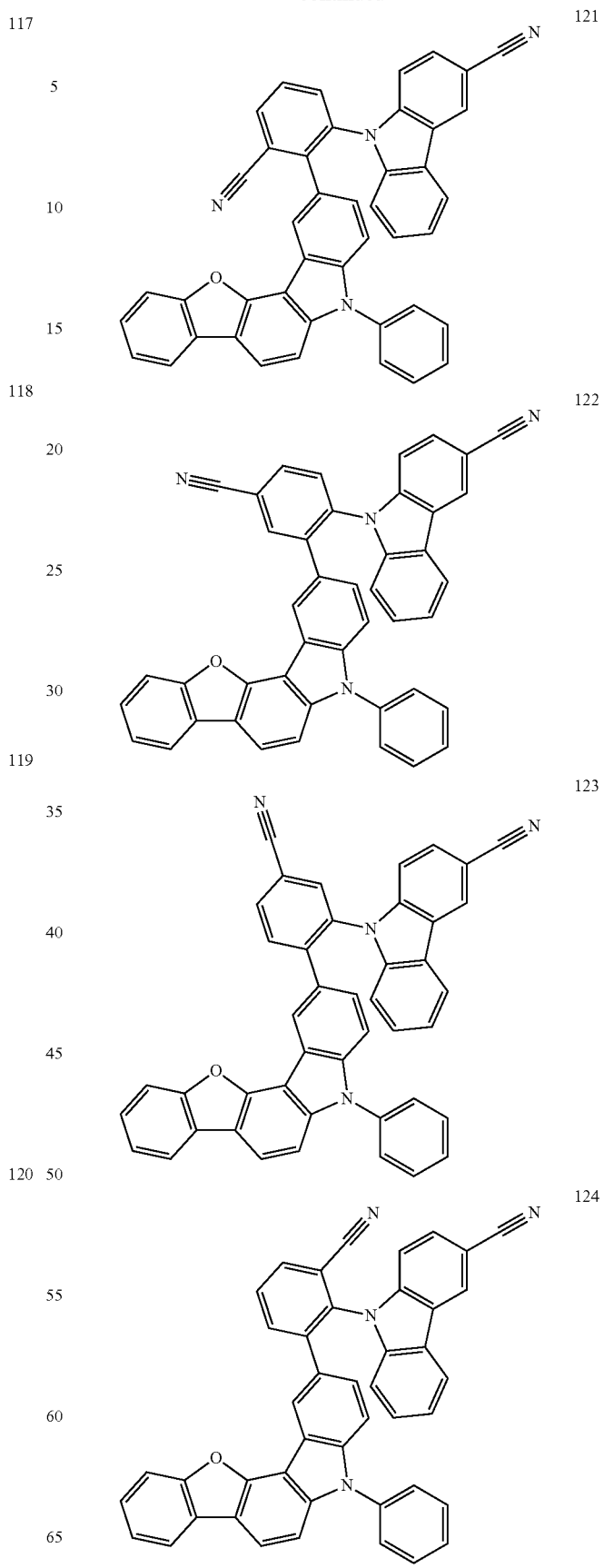

-continued
125
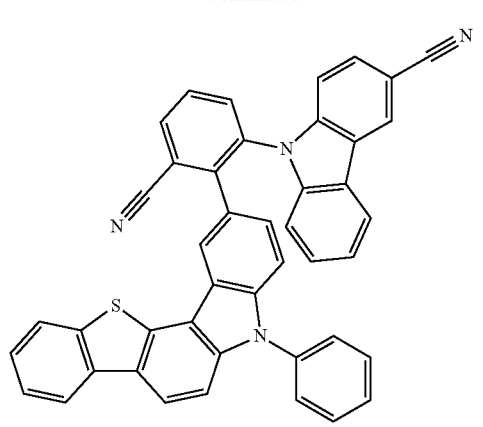
126
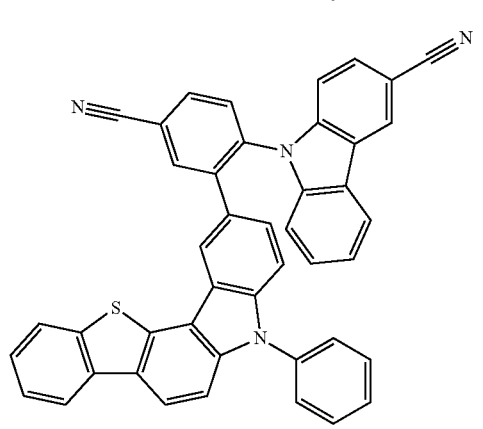
127
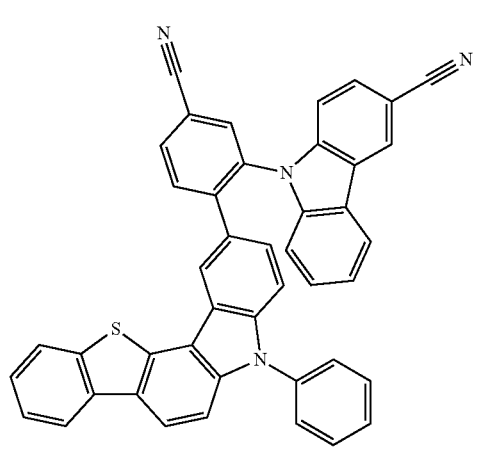
128
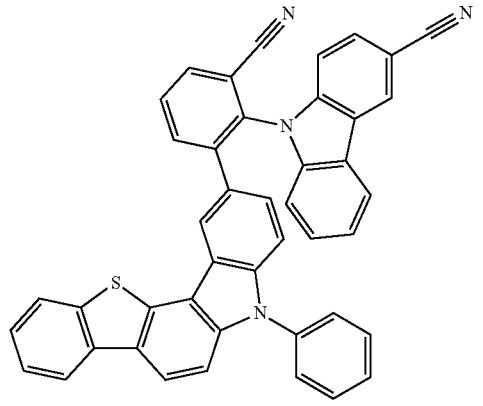
-continued
129
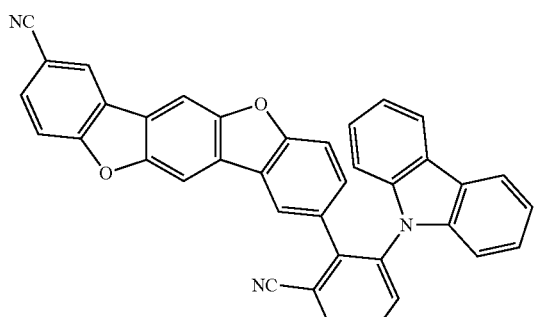
130
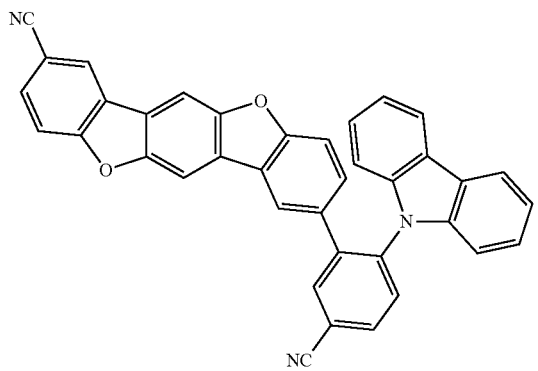
131
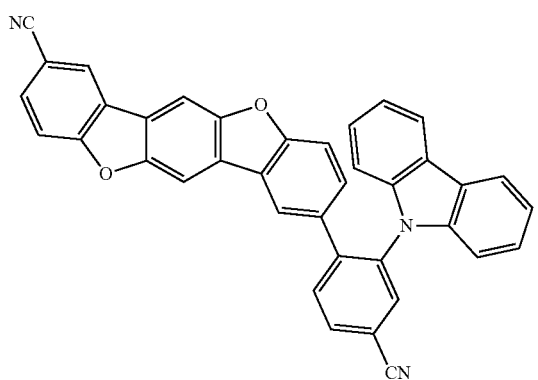
132
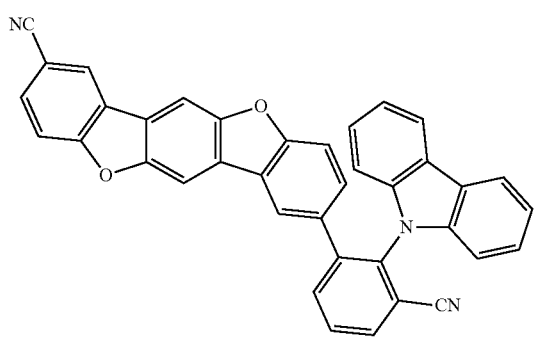

133
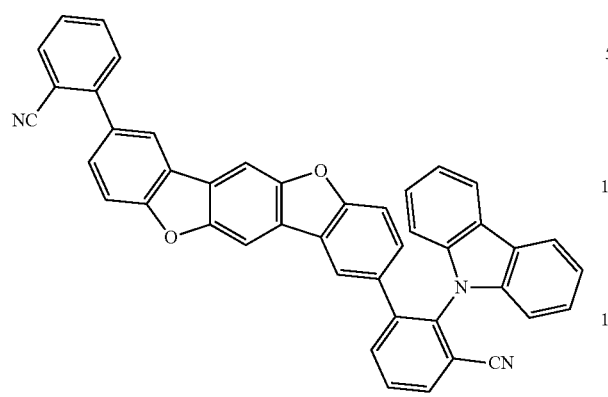
134
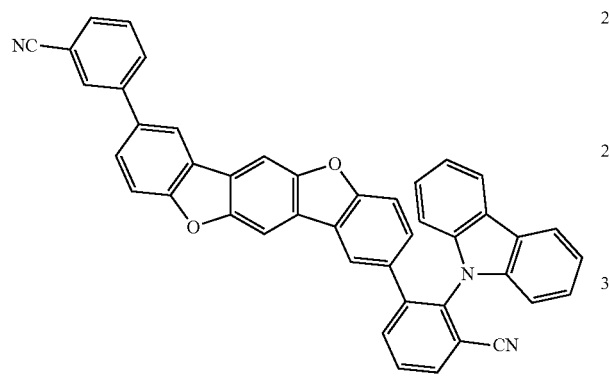
135
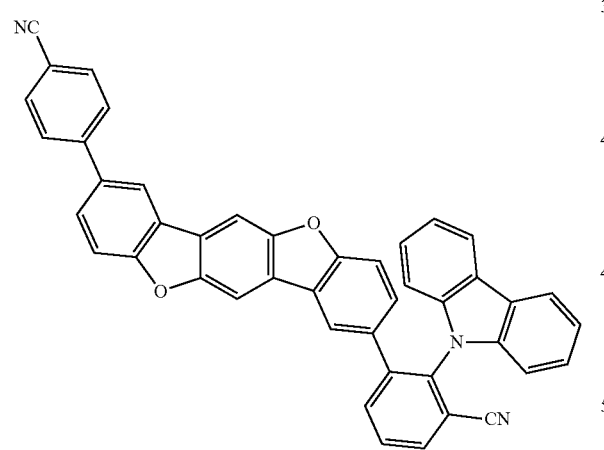
136
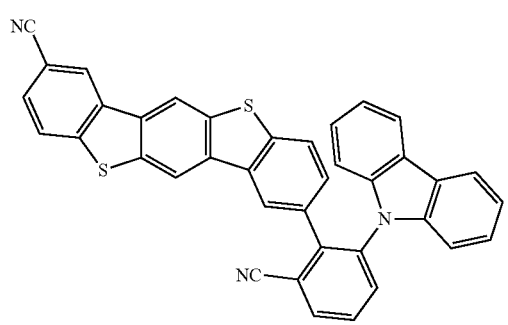
137
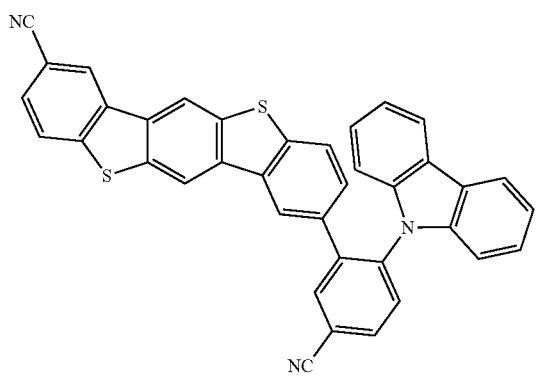
138
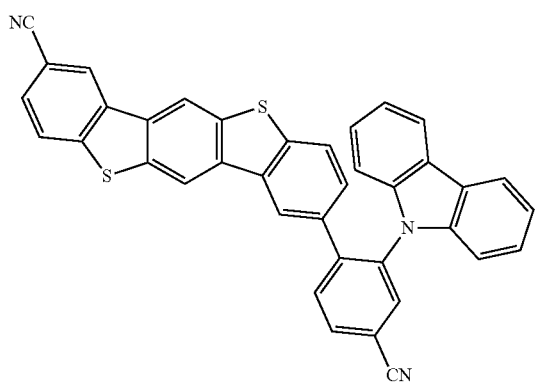
139
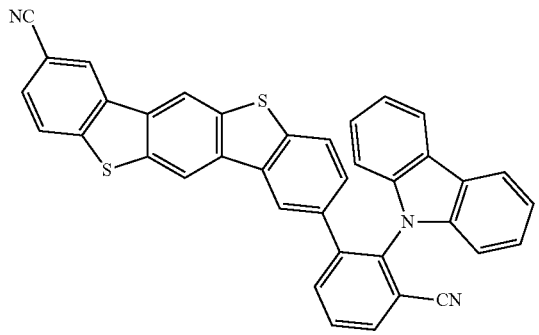
140
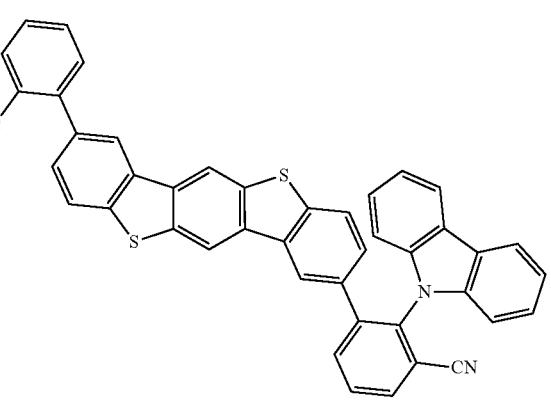

699
-continued
141
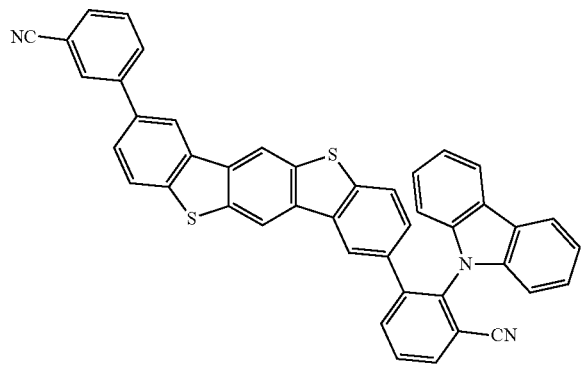
142
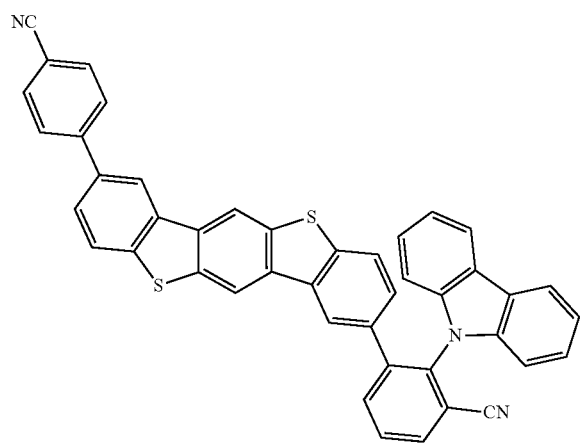
143
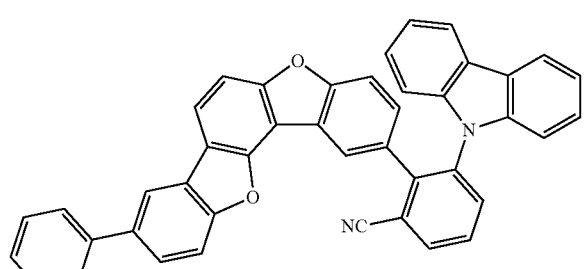
144
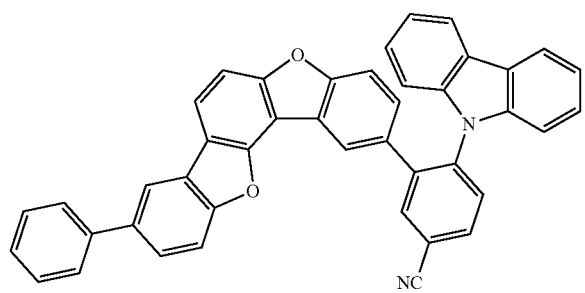
700
-continued
145
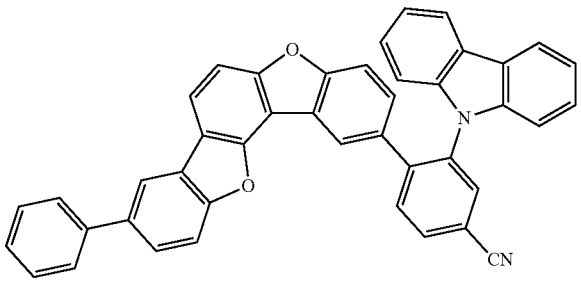
146
147
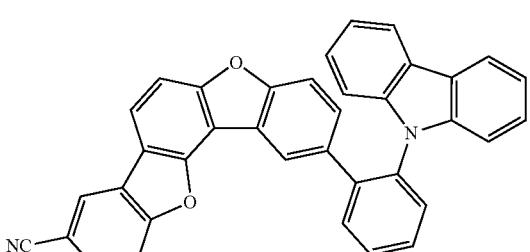
148
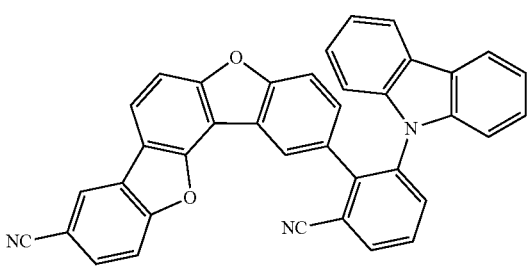
149
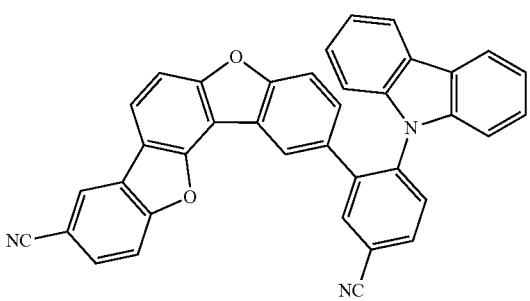

701
-continued
150
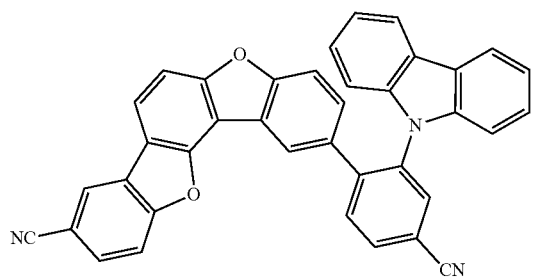
151
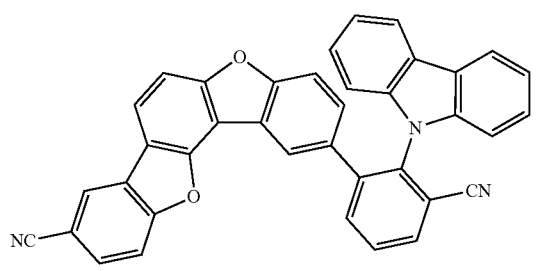
152
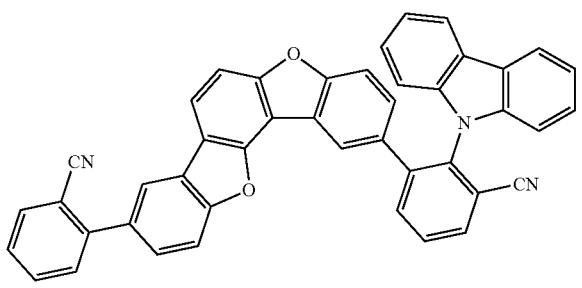
153
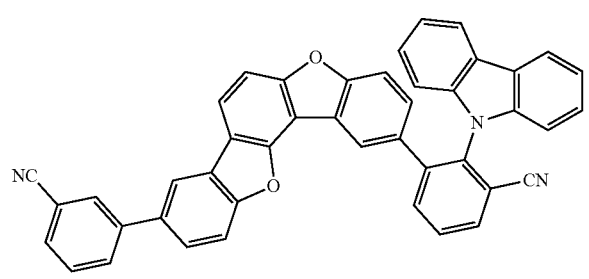
154
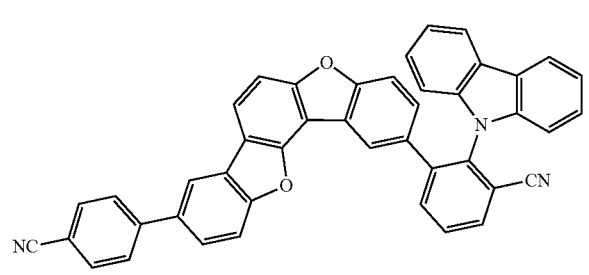
702
-continued
155
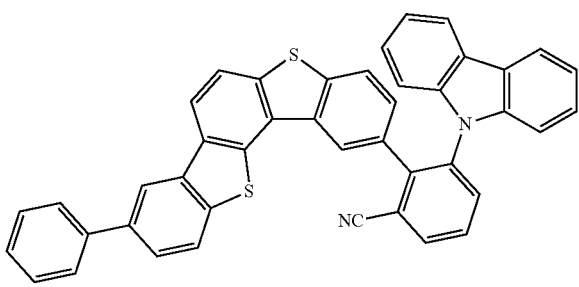
156
157
158
159
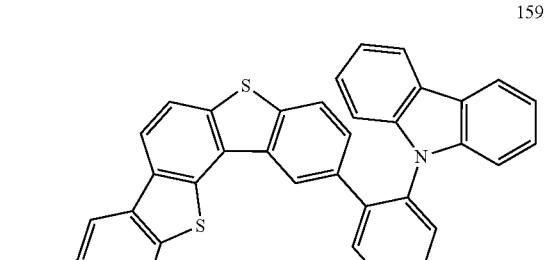

-continued
160
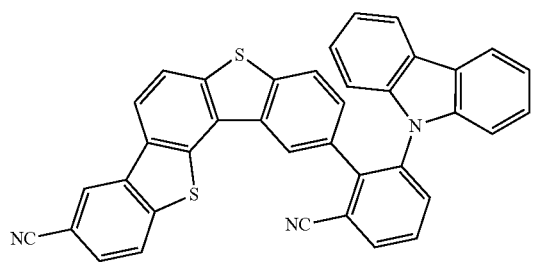
161
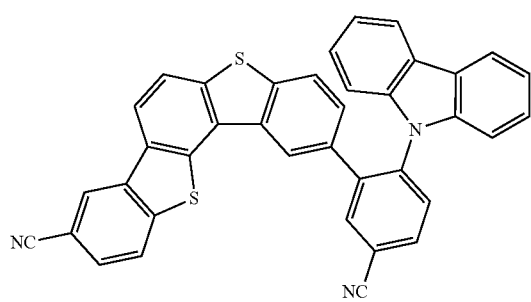
162
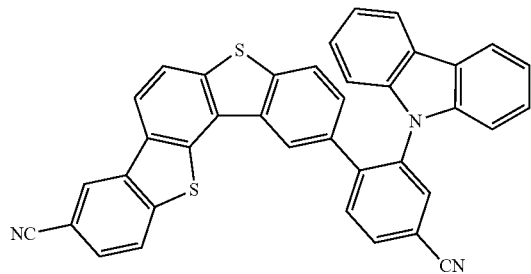
163
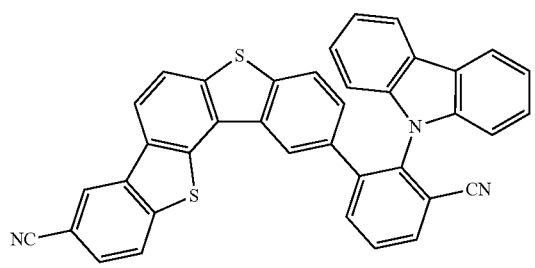
164
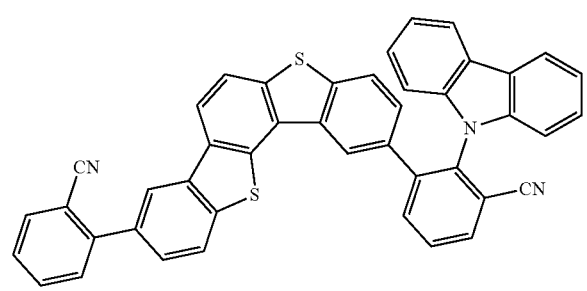
-continued
165
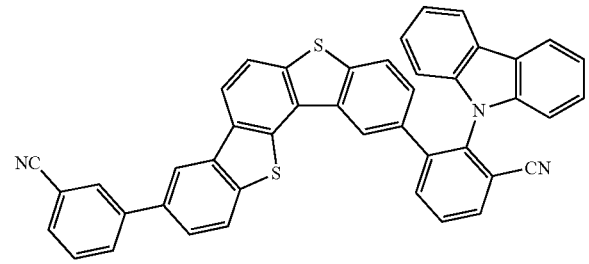
166
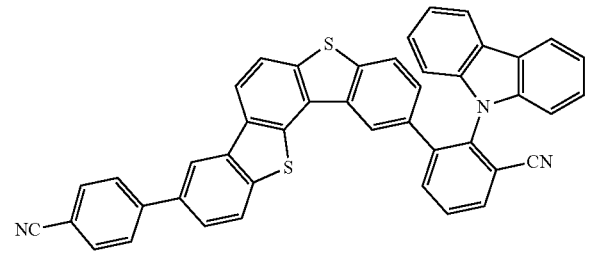
167
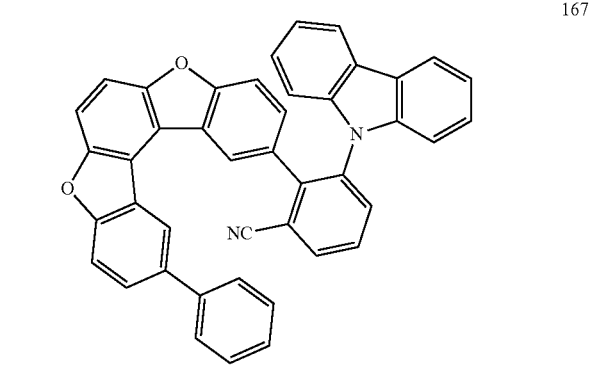
168
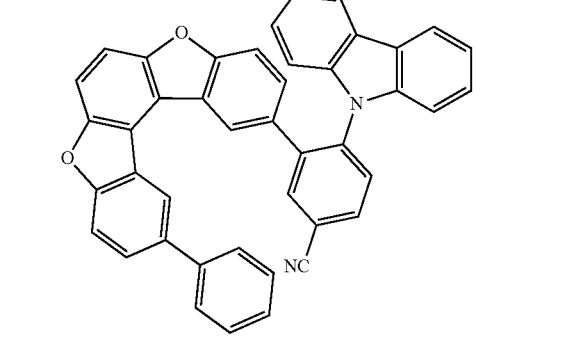
169
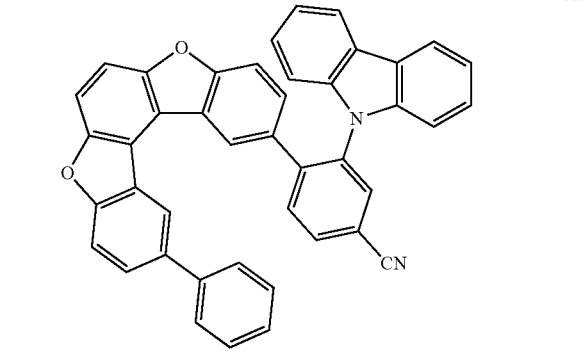

170
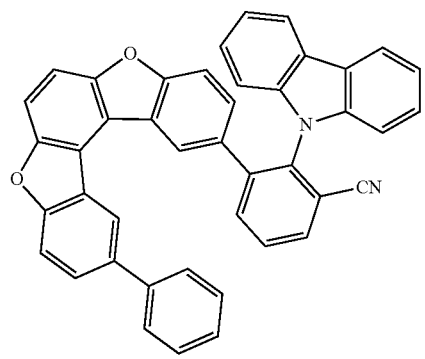
171
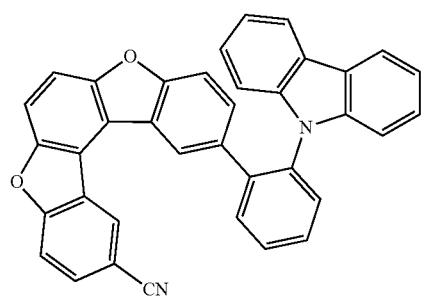
172
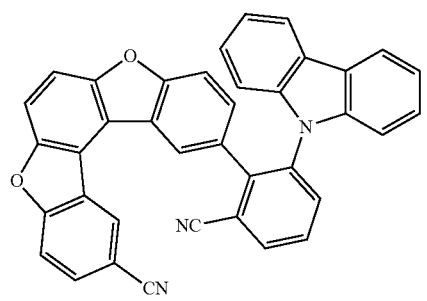
173
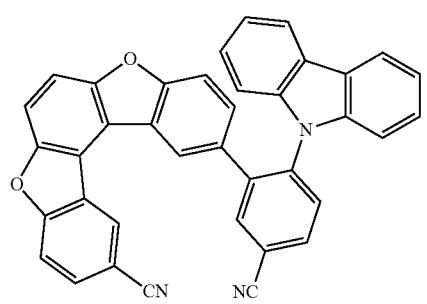
174
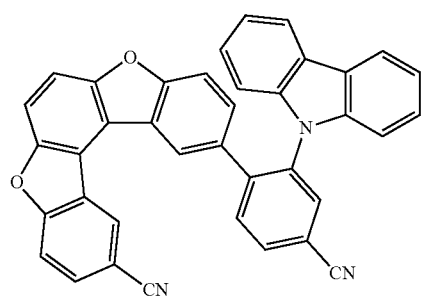
175
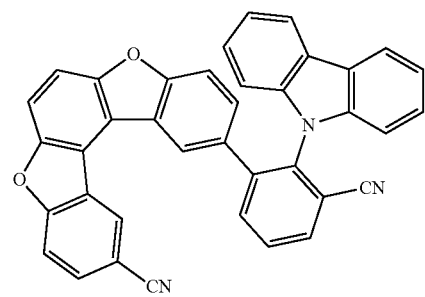
176
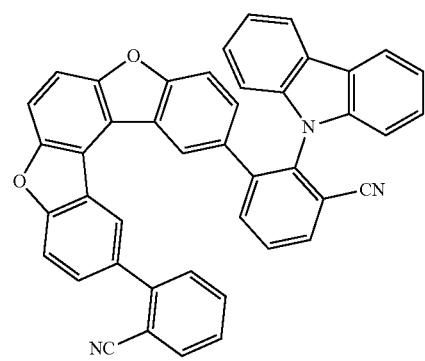
177
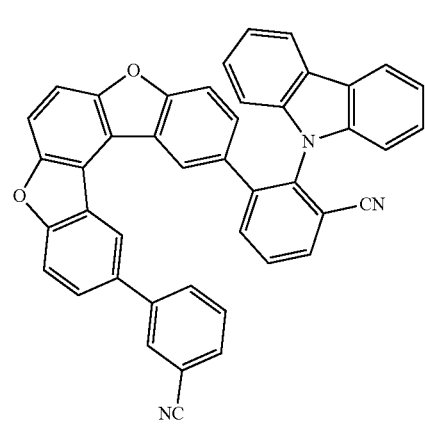
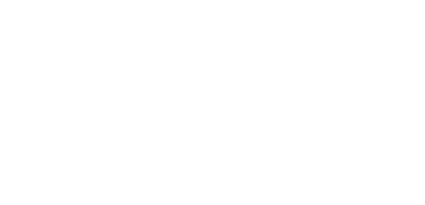
178
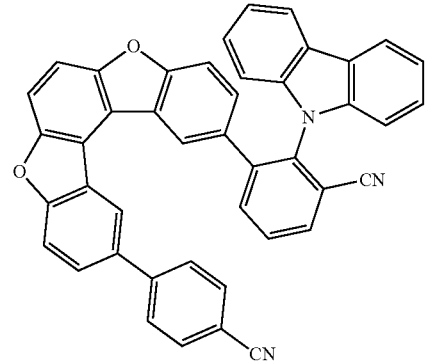

-continued
179
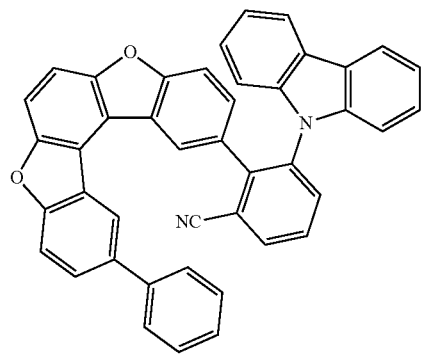
180
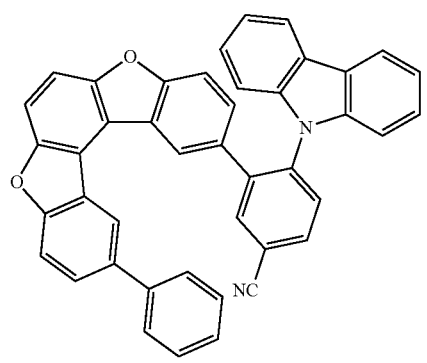
181
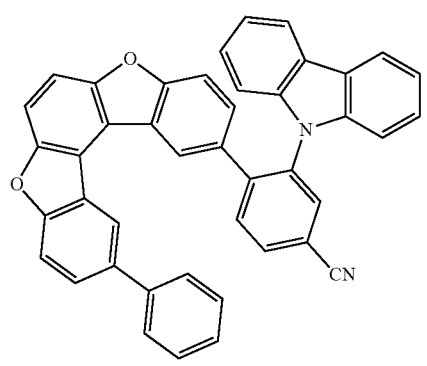
182
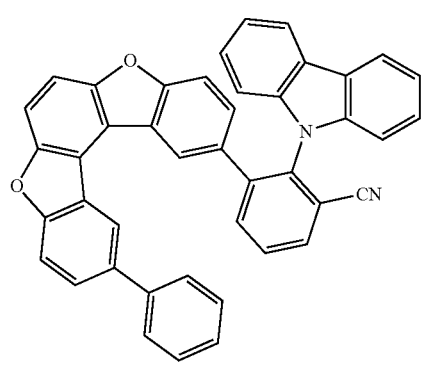
-continued
183
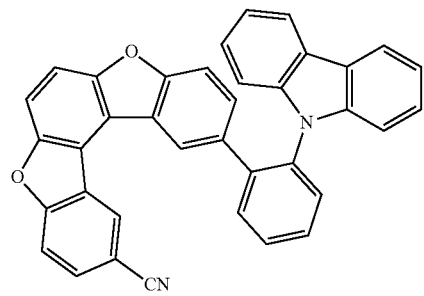
184
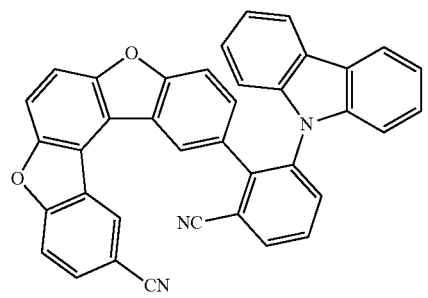
185
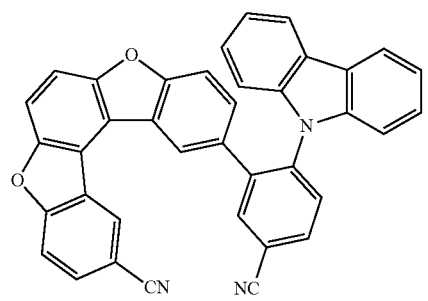
186
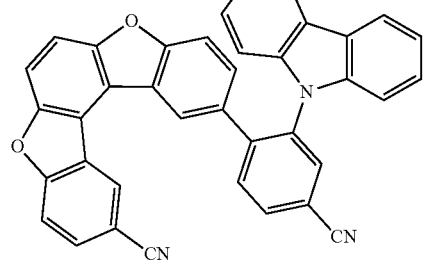
187
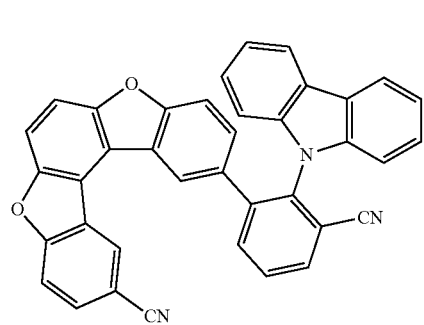

188
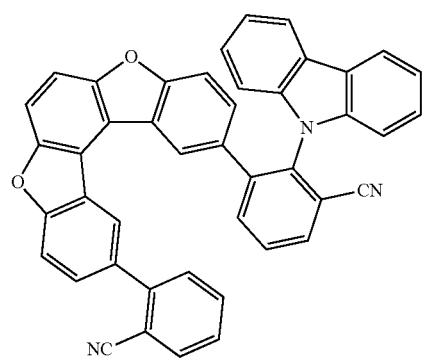
189
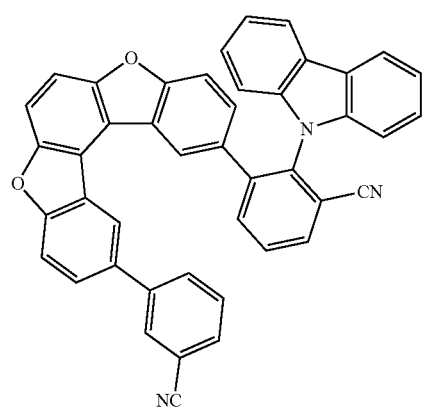
190
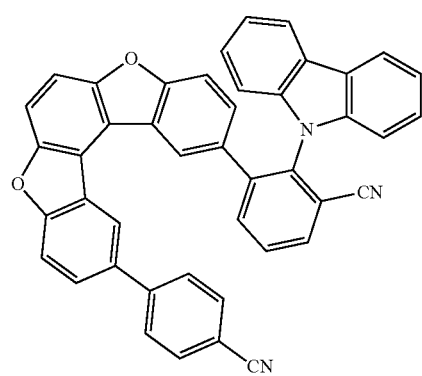
191
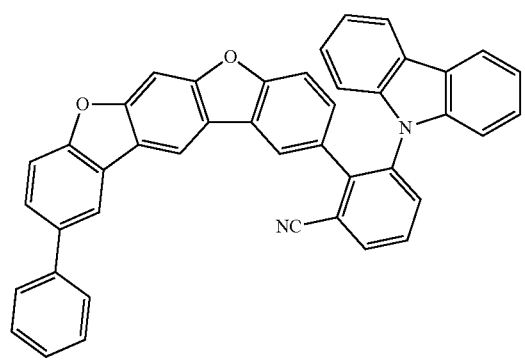
192
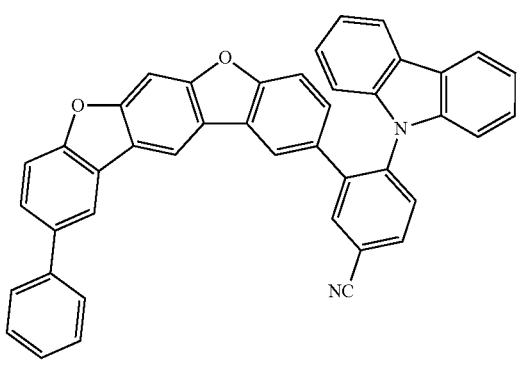
193
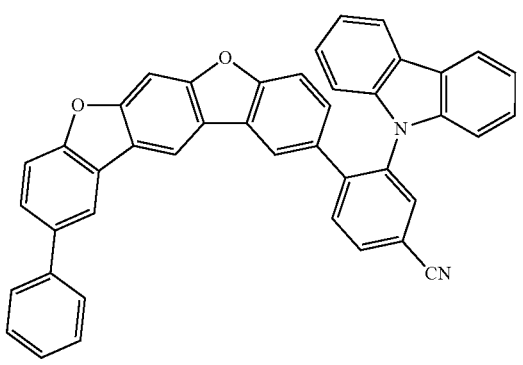
194
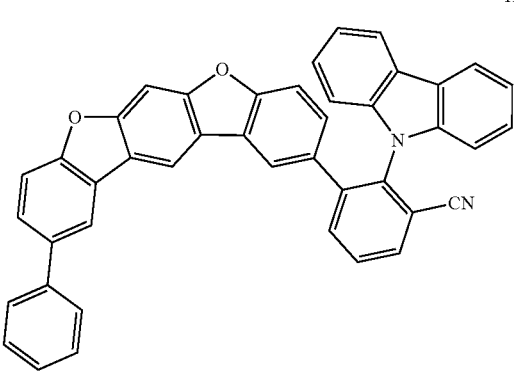
195
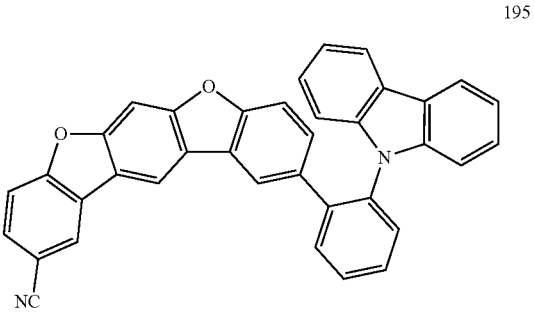

-continued
196
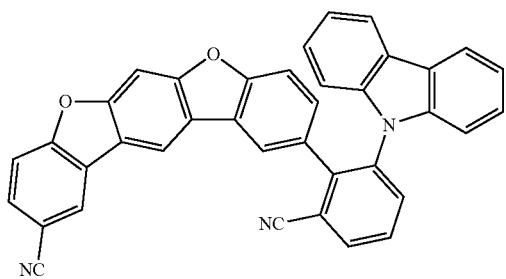
197
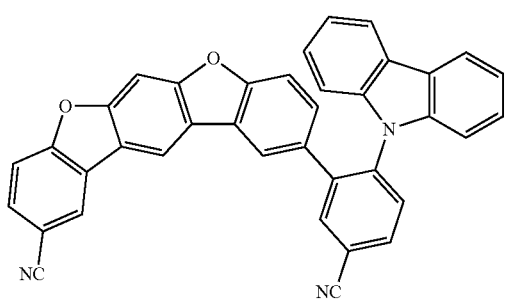
198
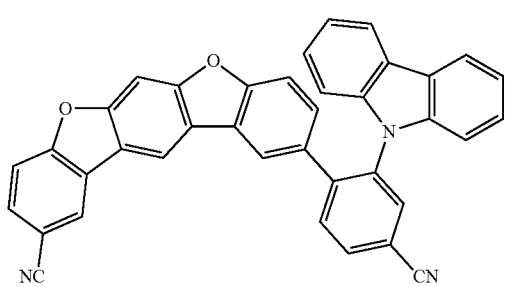
199
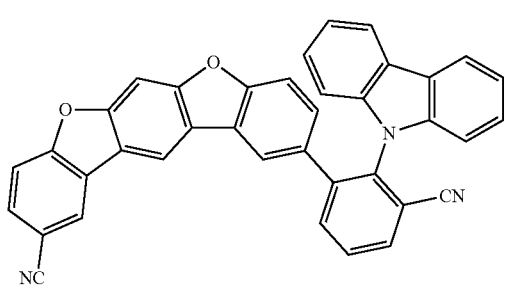
200
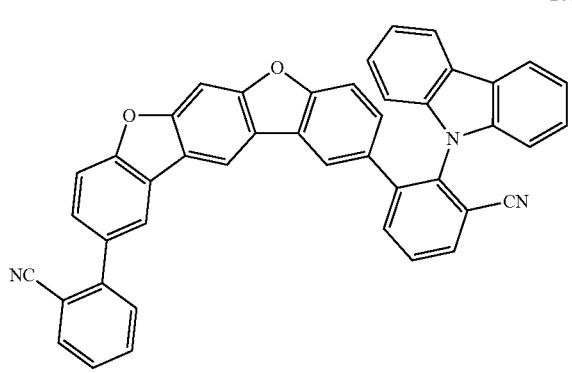
-continued
201
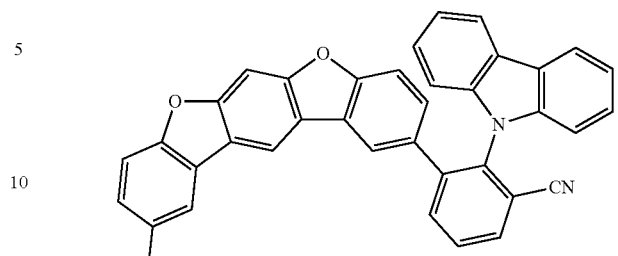
202
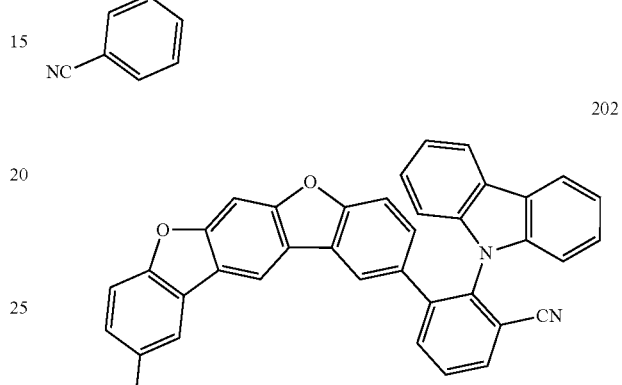
203
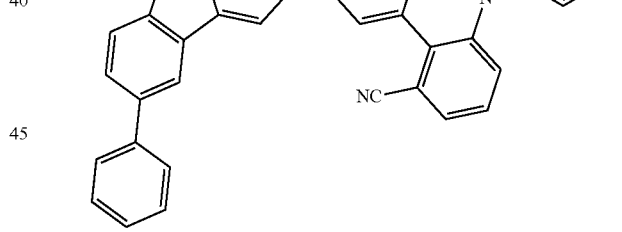
204
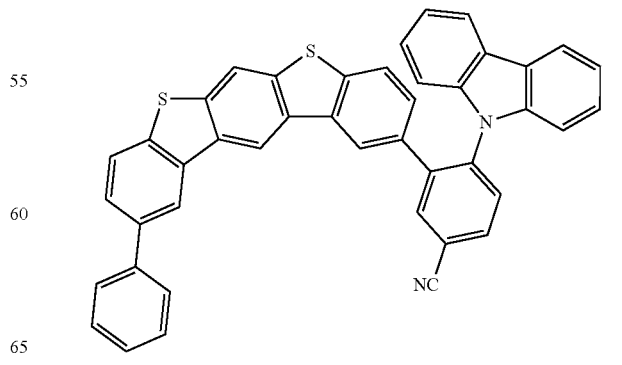

205
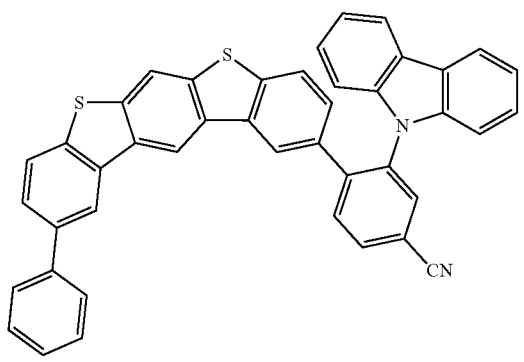
206
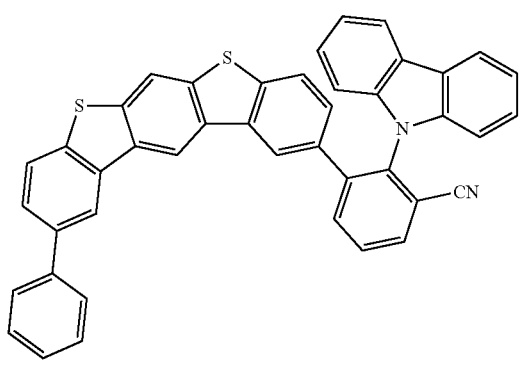
207
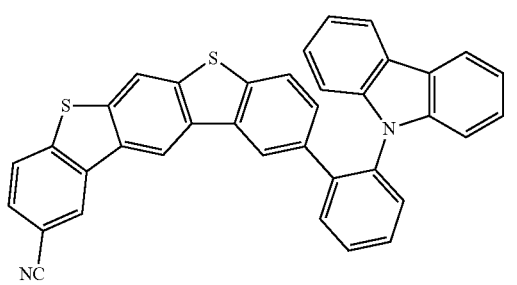
208
209
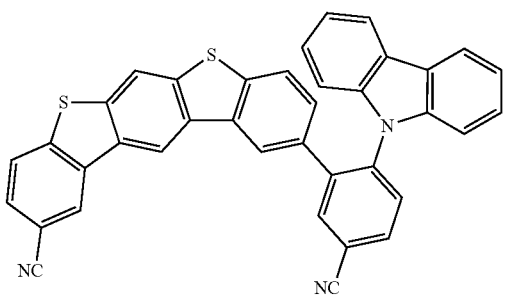
210
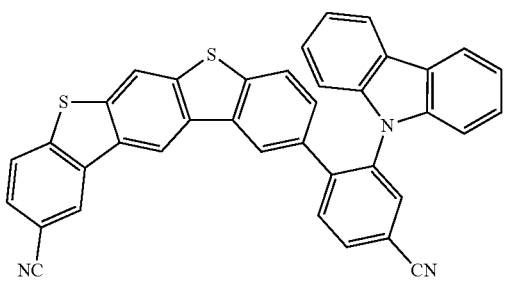
211
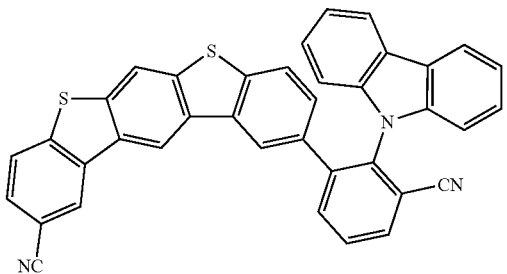
212
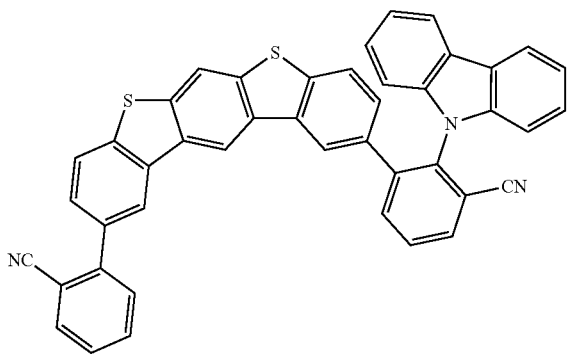

715
-continued
716
-continued
213
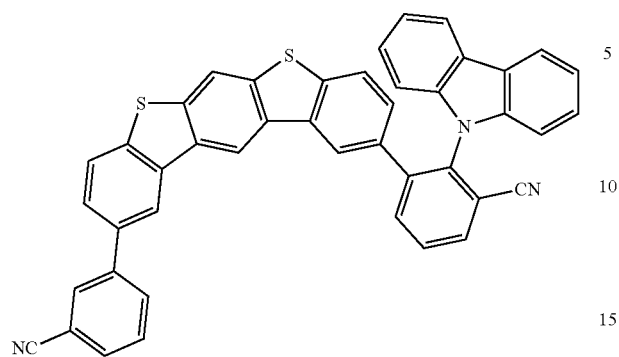
214
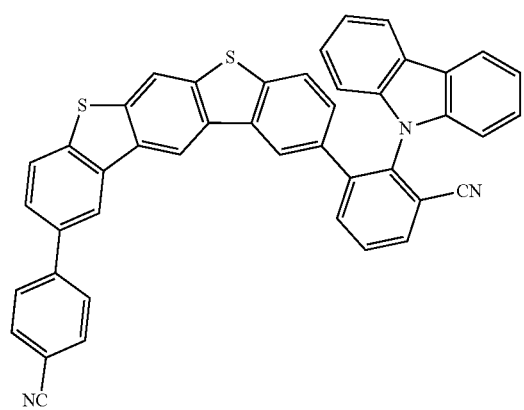
215
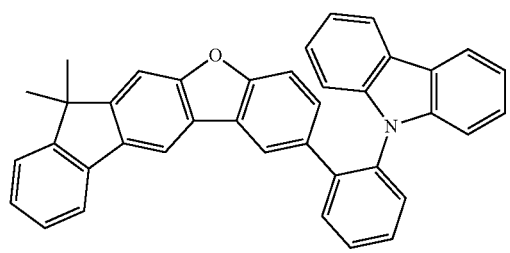
216
217
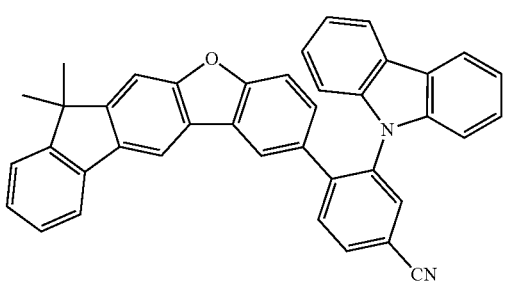
218
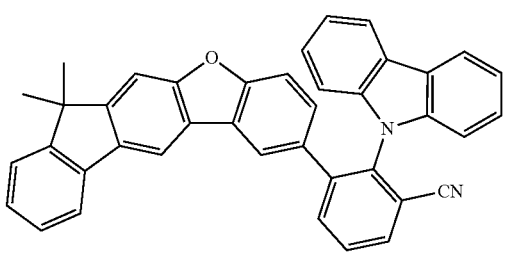
219
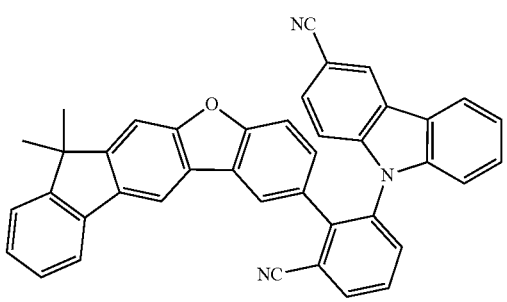
220
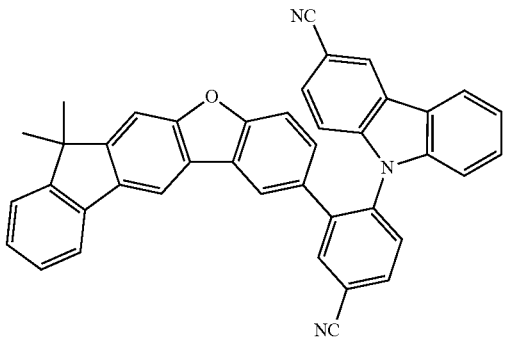
221
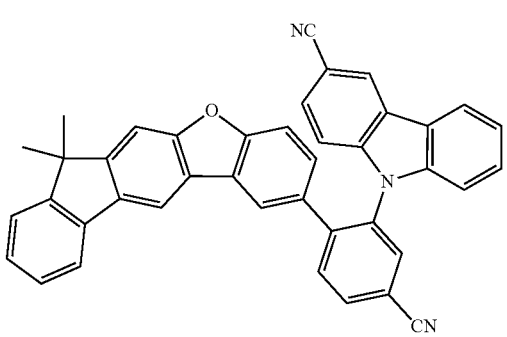

| 717 -continued | | 718 -continued | |
|---|---|---|---|
| 222 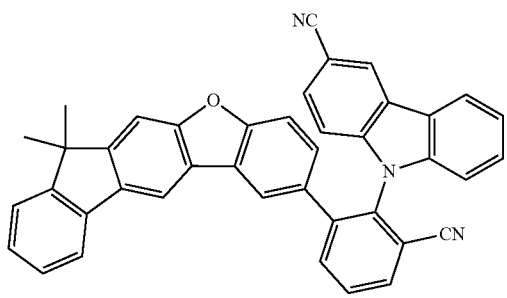 | | 227 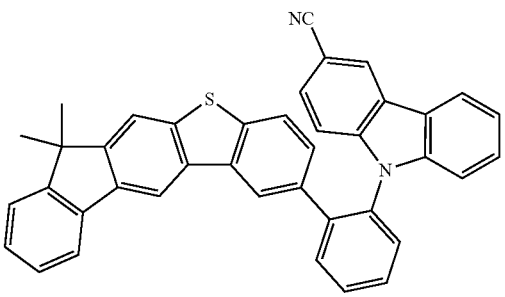 | |
| 223 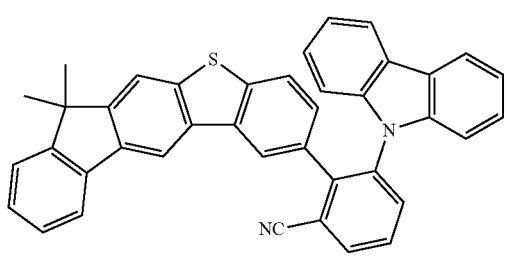 | | 228 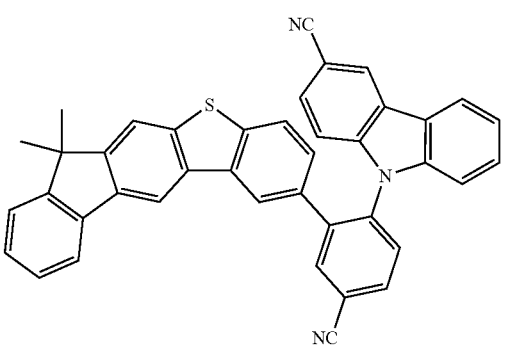 | |
| 224 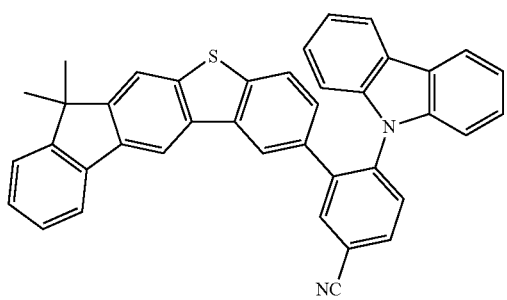 | | 229 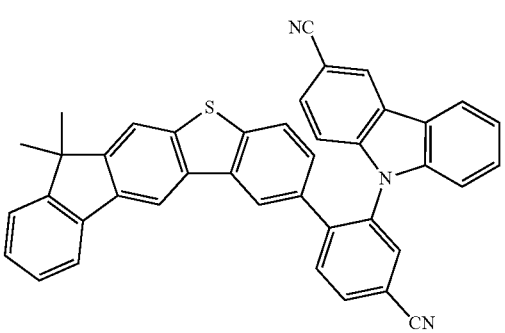 | |
| 225 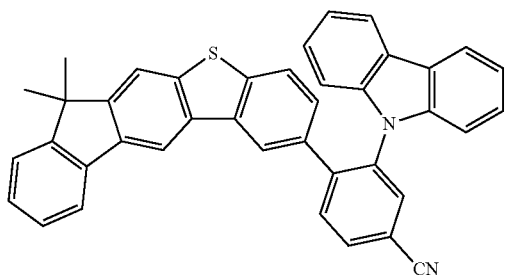 | | 230 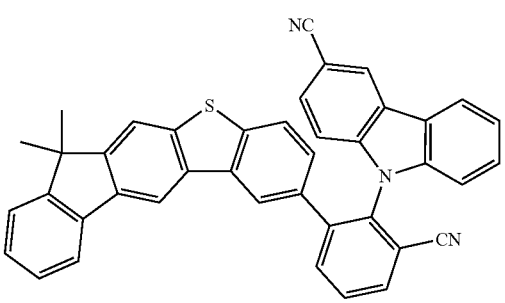 | |
| 226 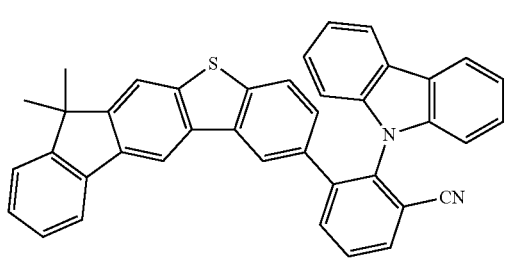 | | 231 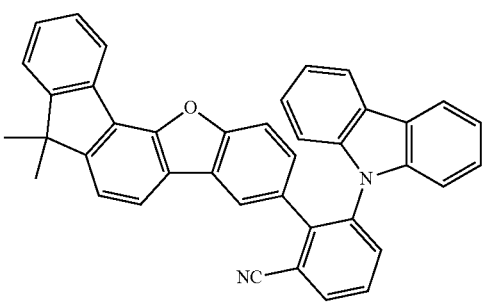 | |

232 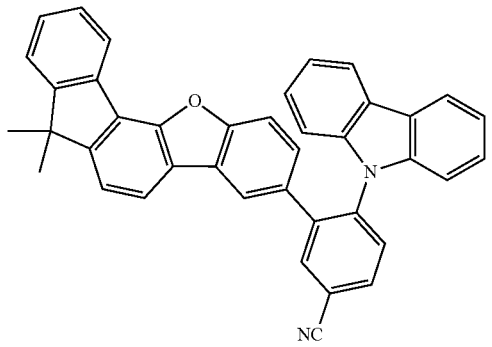
233 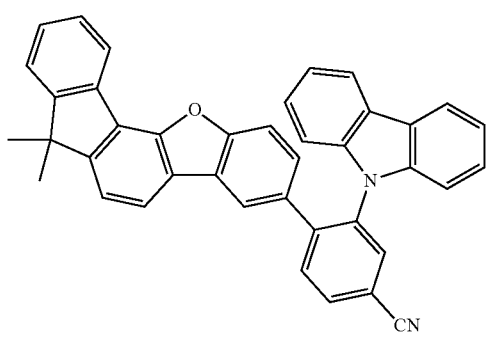
234 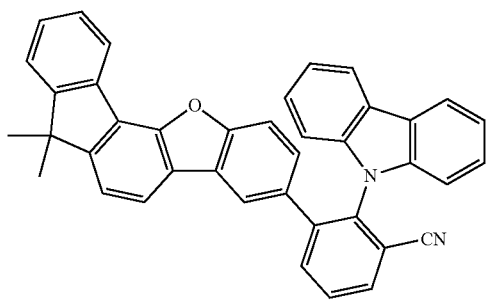
235
236 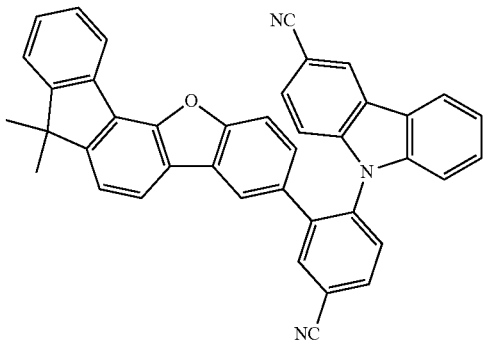
237 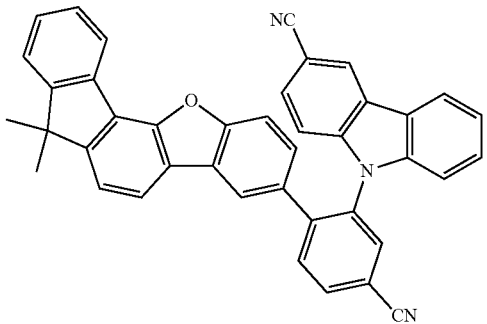
238 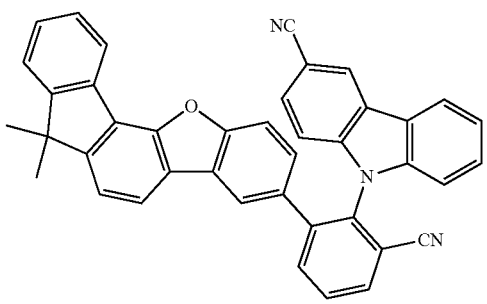
239 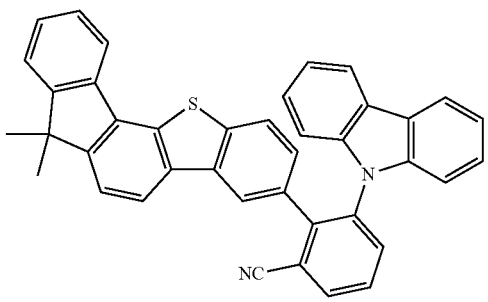
240 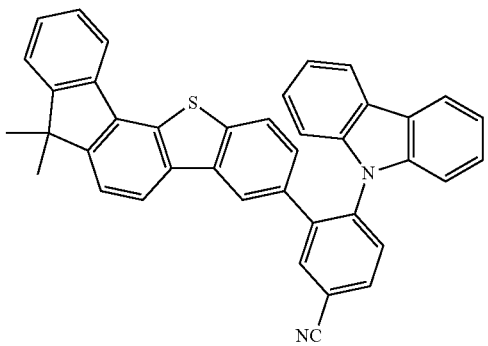

| 241 | 246 |
|---|---|
| 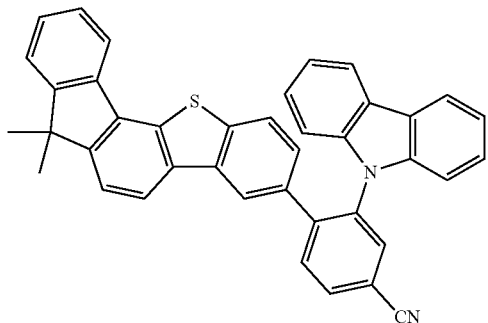 | 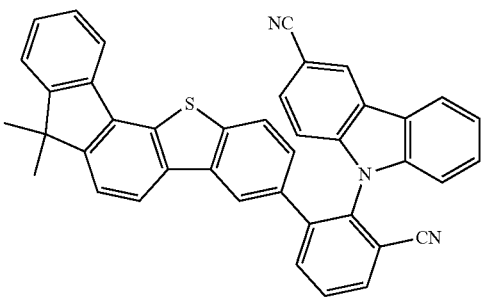 |
| 242 | 247 |
|---|---|
| 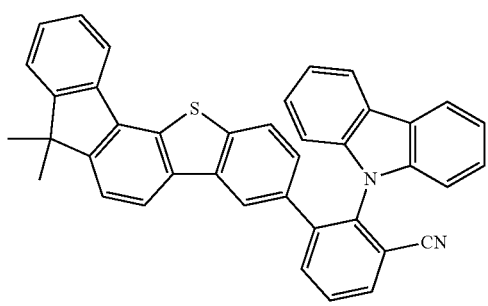 | 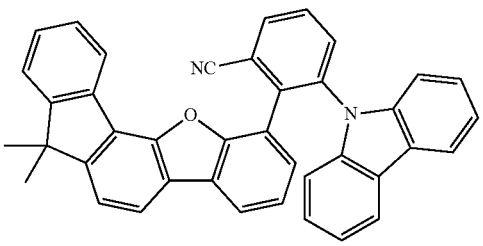 |
| 243 | 248 |
|---|---|
| 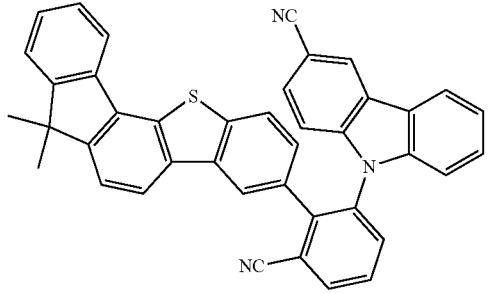 | 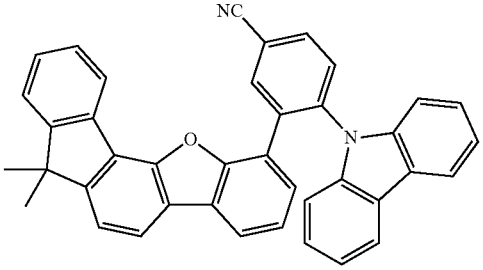 |
| 244 | 249 |
|---|---|
| 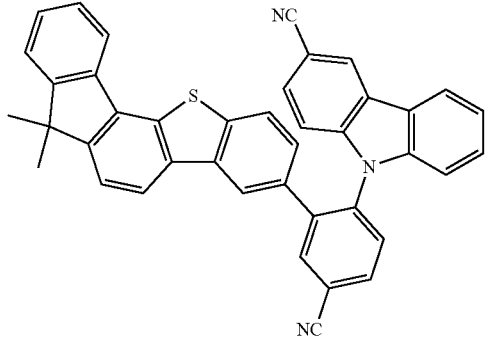 | 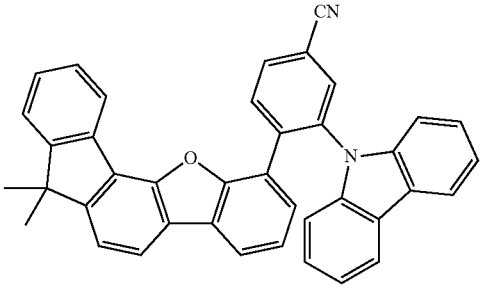 |
| 245 | 250 |
|---|---|
| 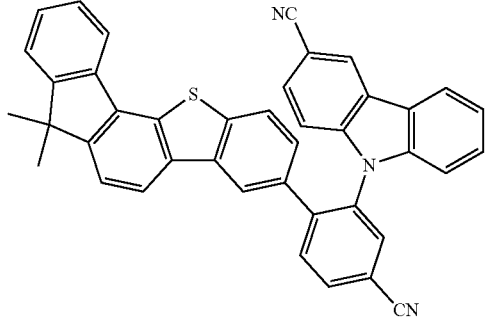 | 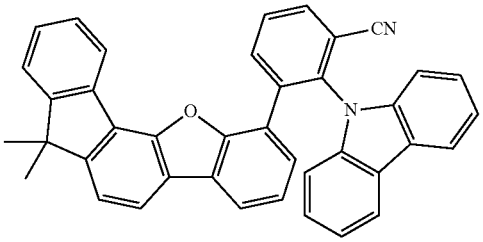 |

-continued
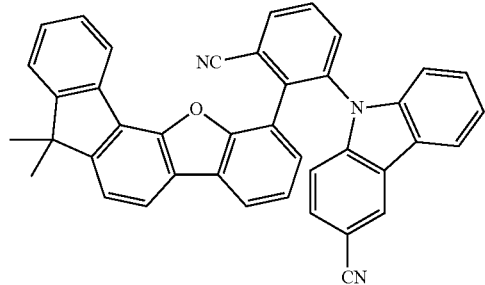 251
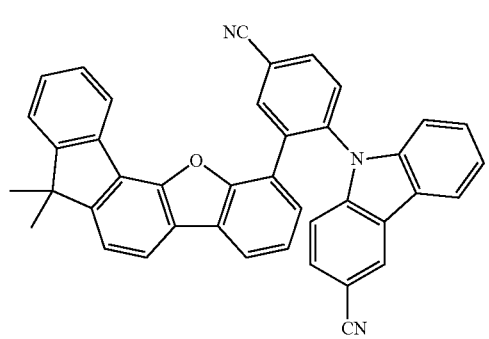 252
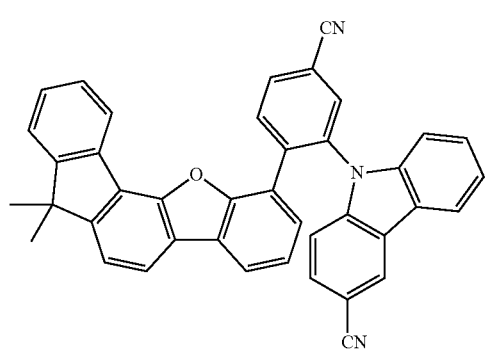 253
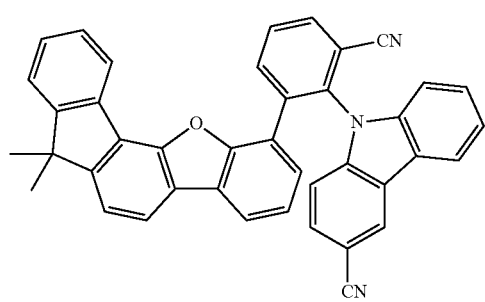 254
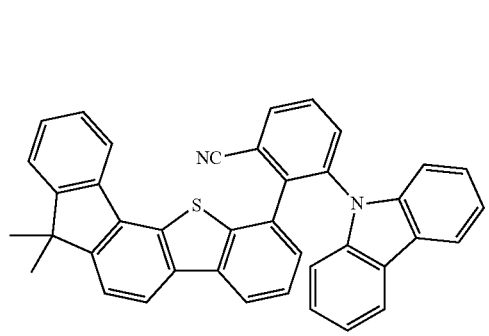 255
-continued
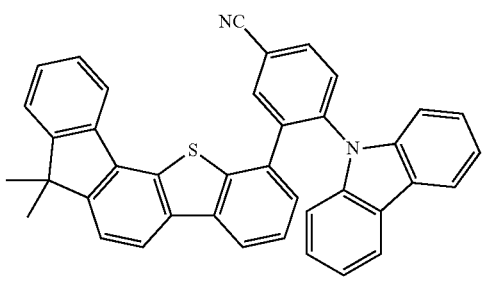 256
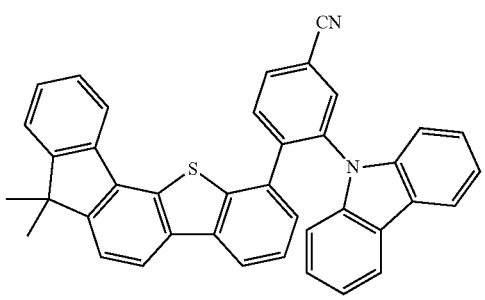 257
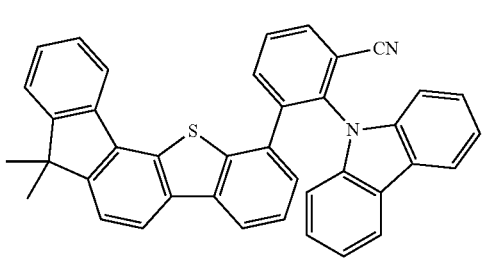 258
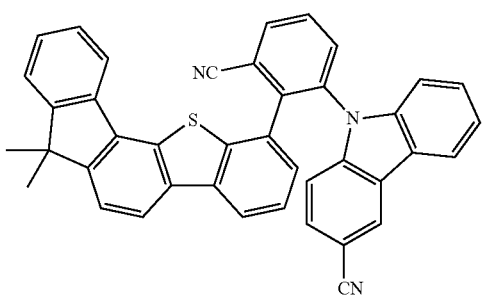 259
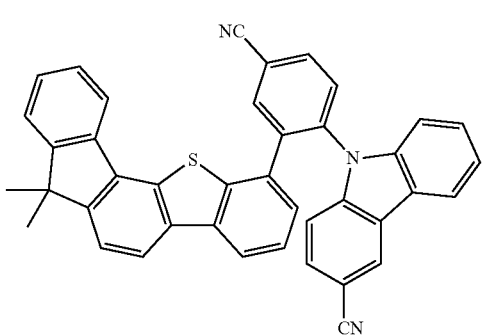 260

725
-continued
261
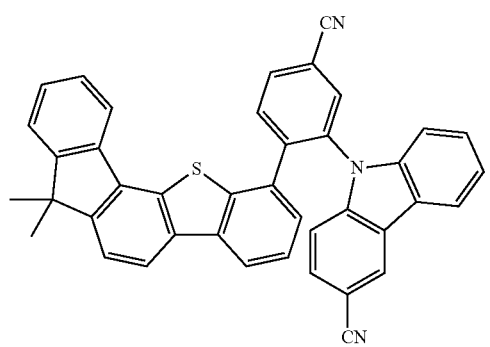
262
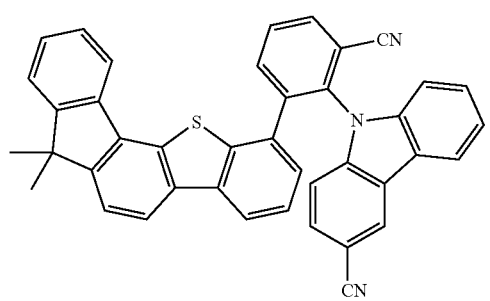
263
264
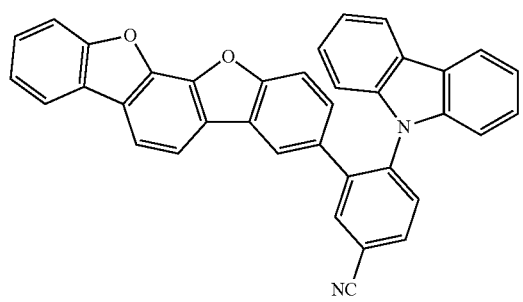
265
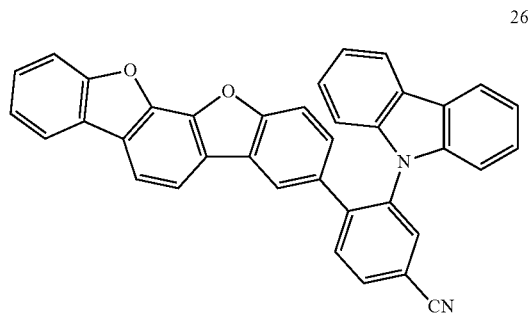
726
-continued
266
267
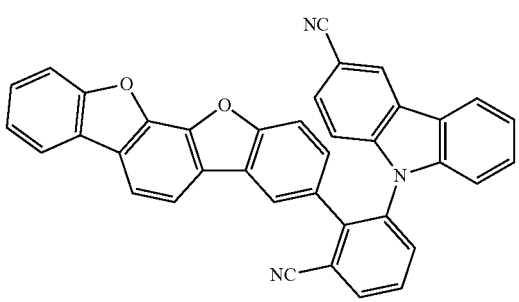
268
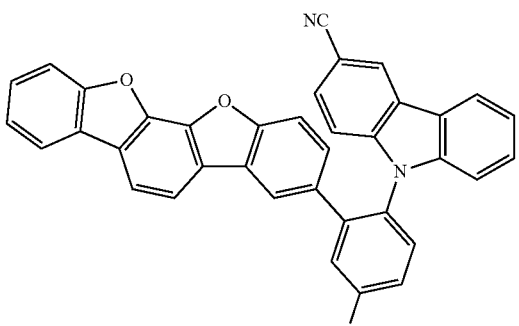
269
270
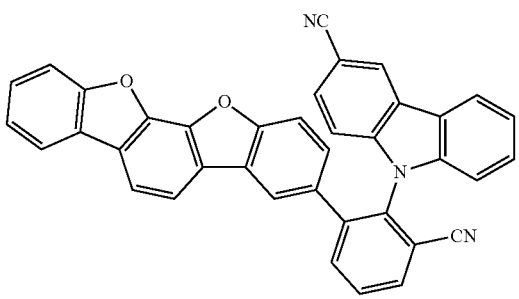

271
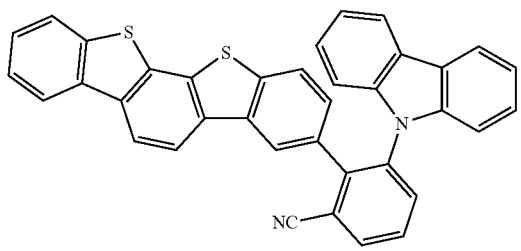
272
273
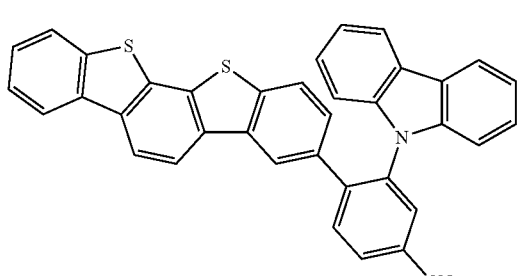
274
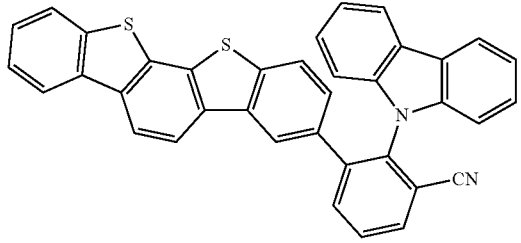
275
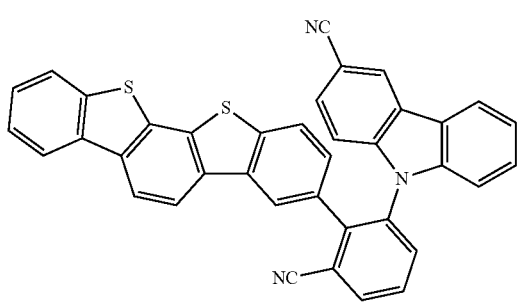
276
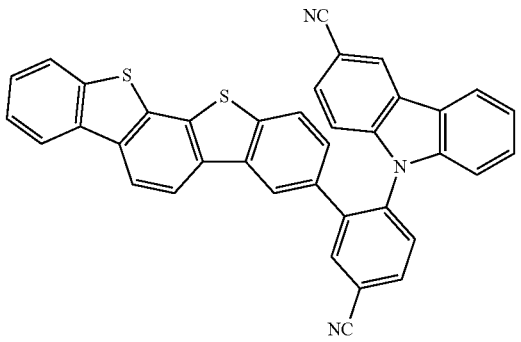
277
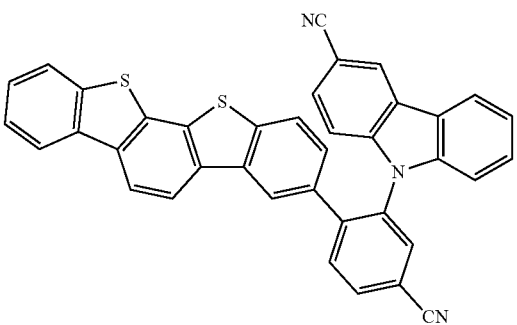
278
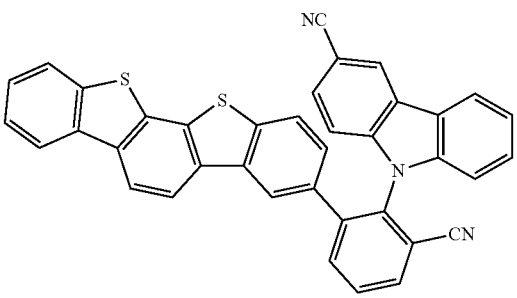
279
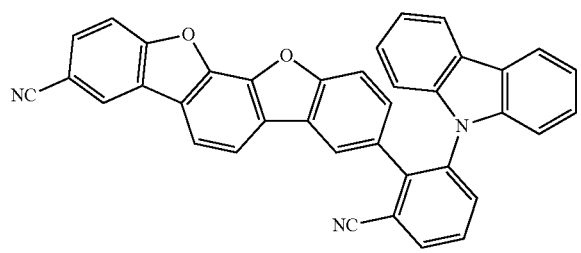
280
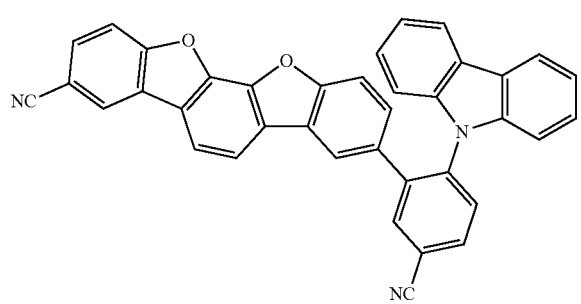

281
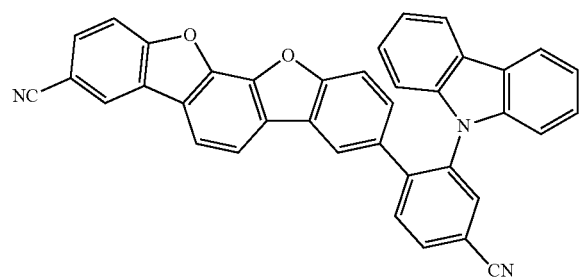
282
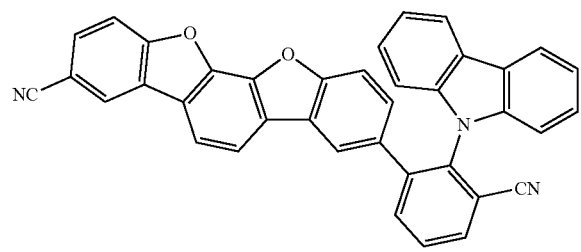
283
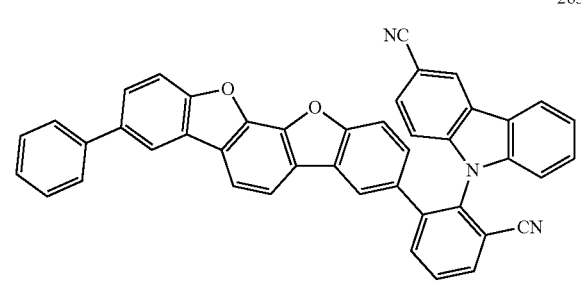
284
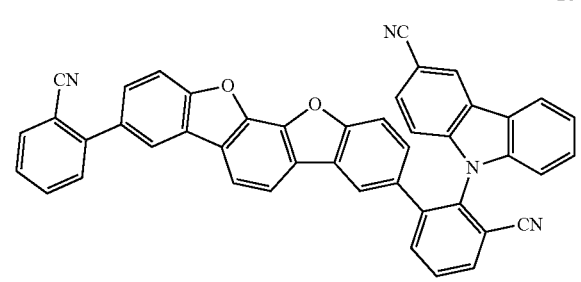
285
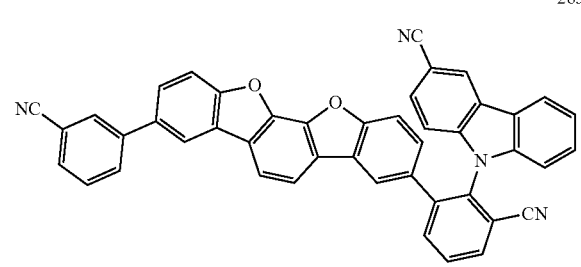
286
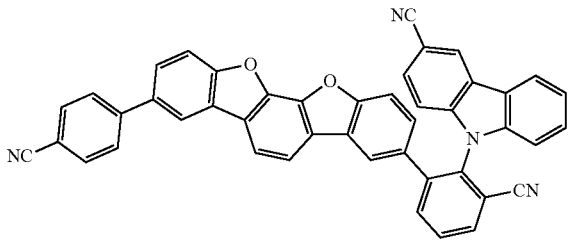
287
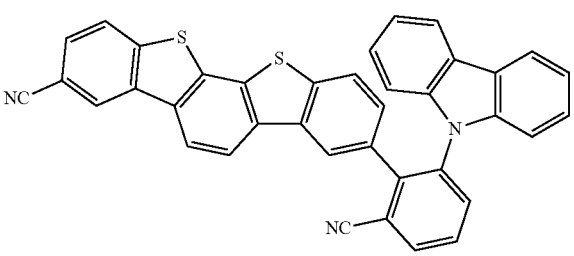
288
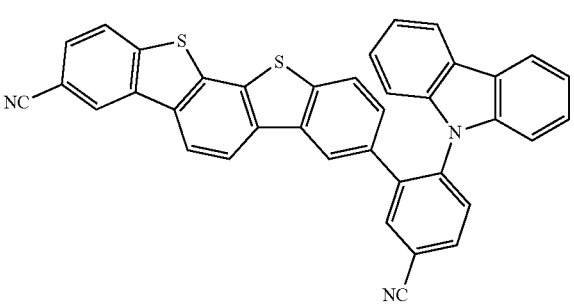
289
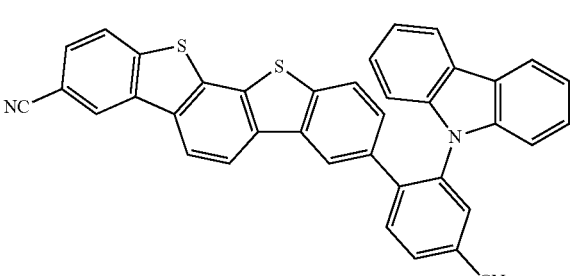
290
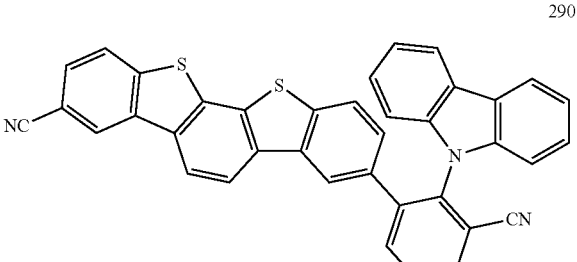

731
-continued
291
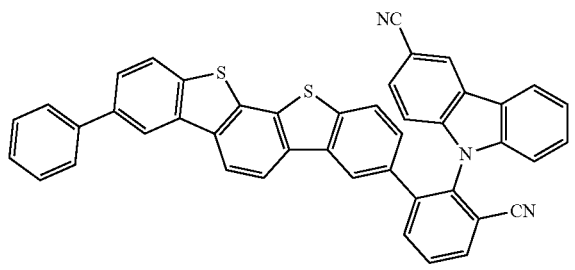
292
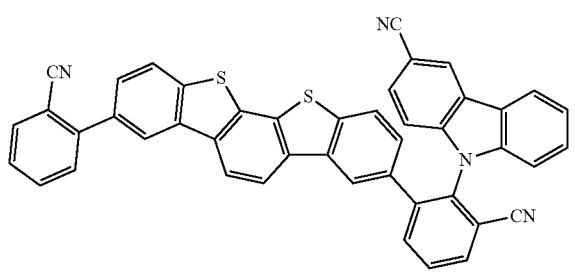
293
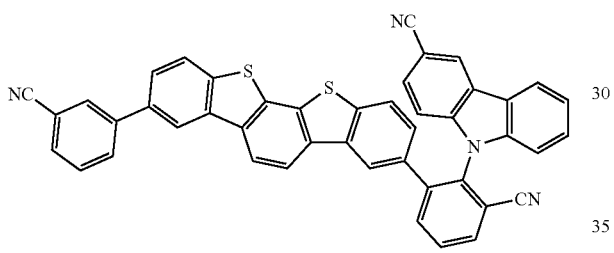
294
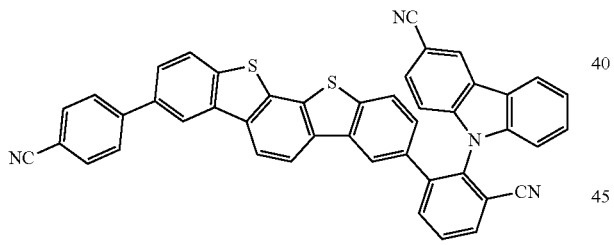
295
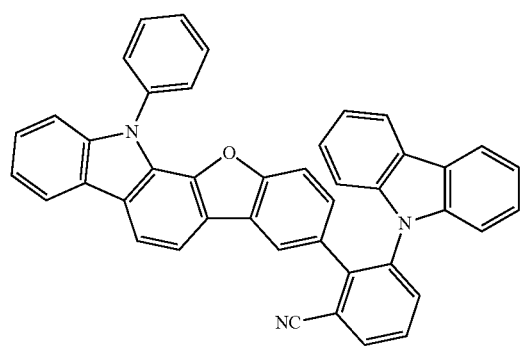
732
-continued
296
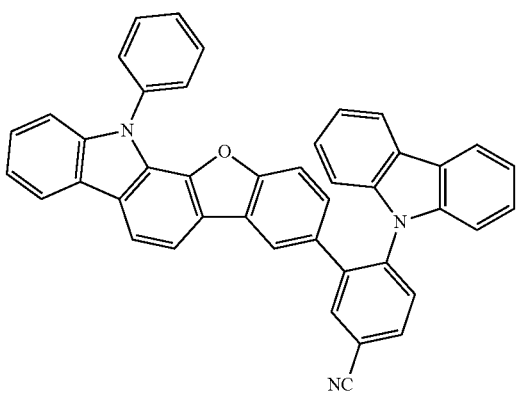
297
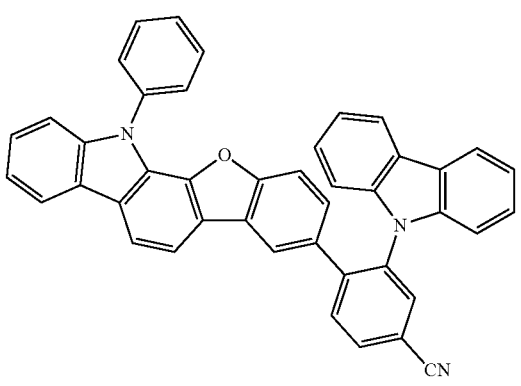
298
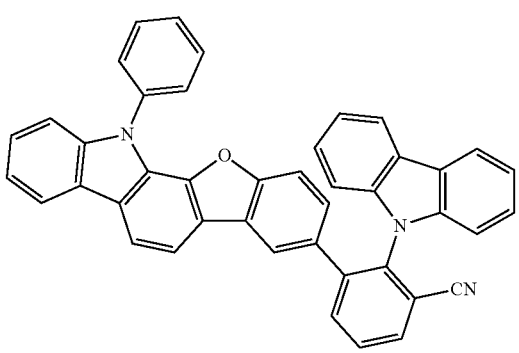
299
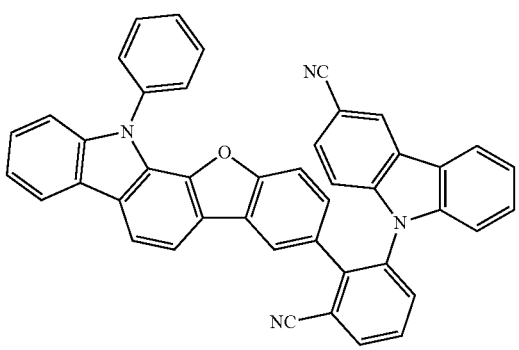

-continued
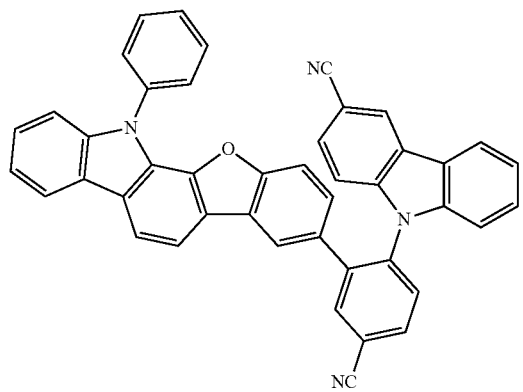
300
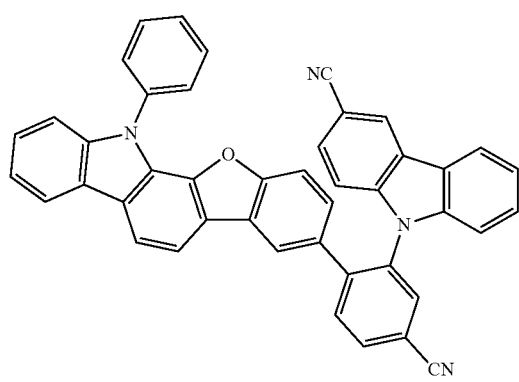
301
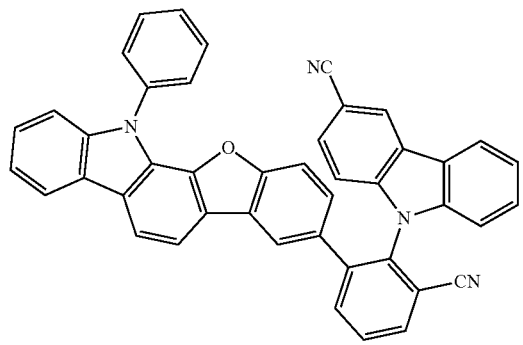
302
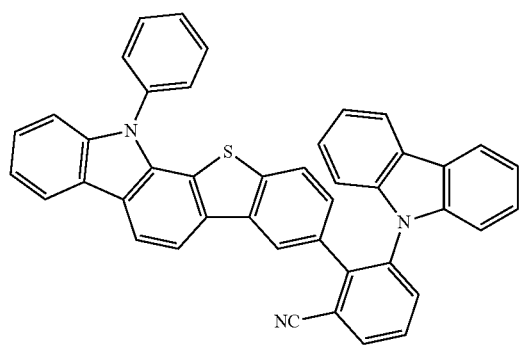
303
-continued
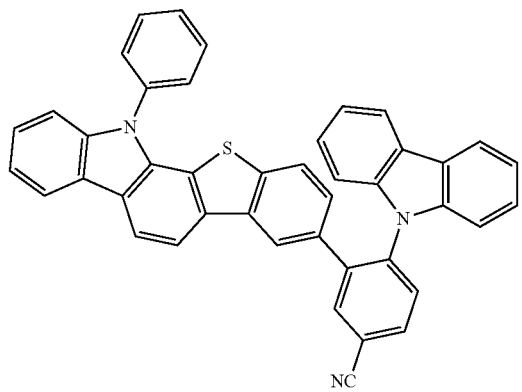
304
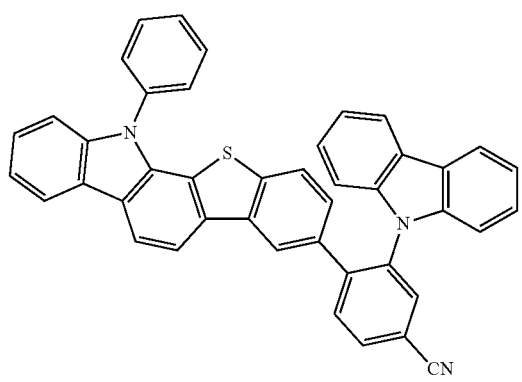
305
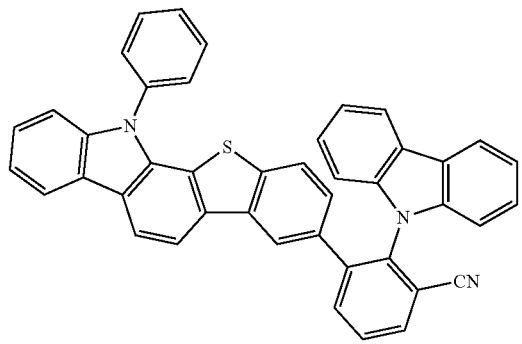
306
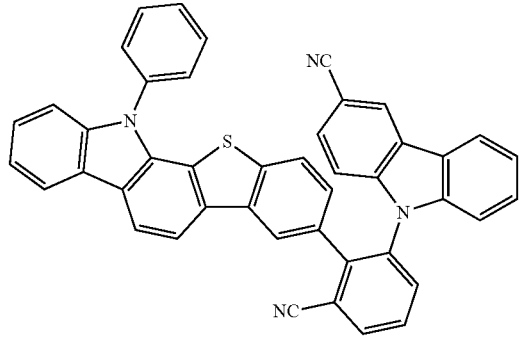
307

735
-continued
308
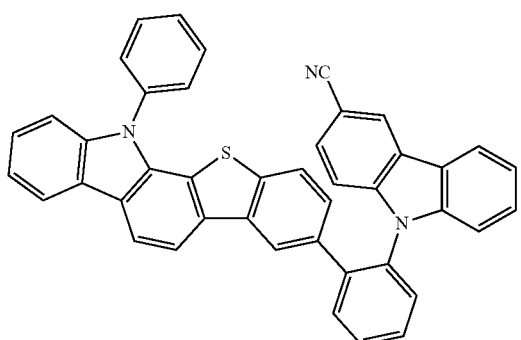
309
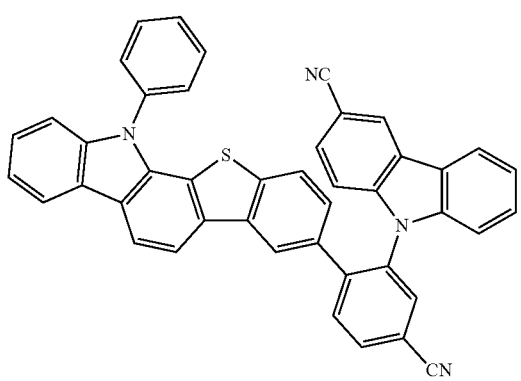
310
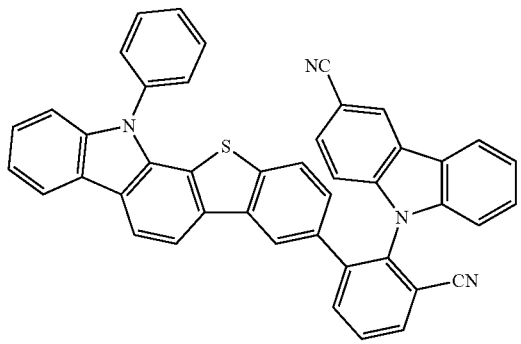
311
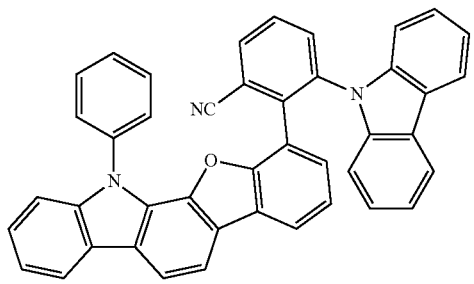
736
-continued
312
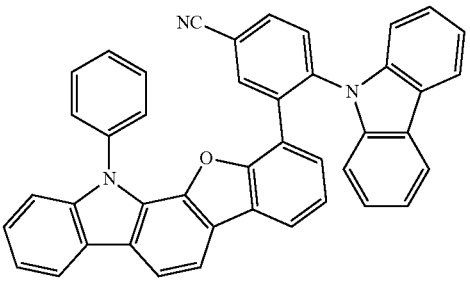
313
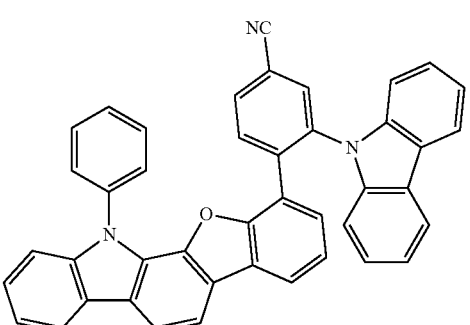
314
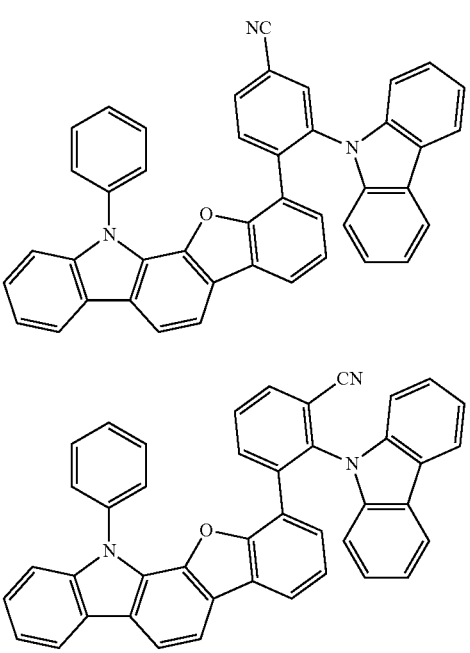
315
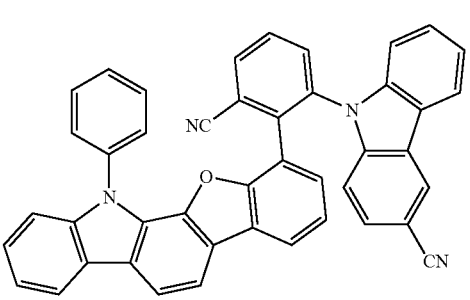
316
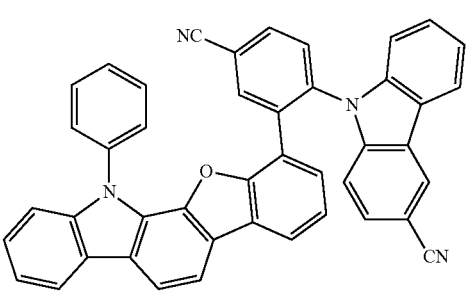

317
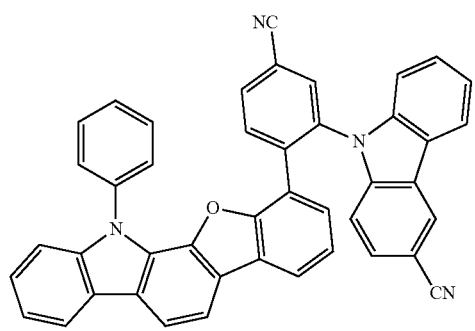
318
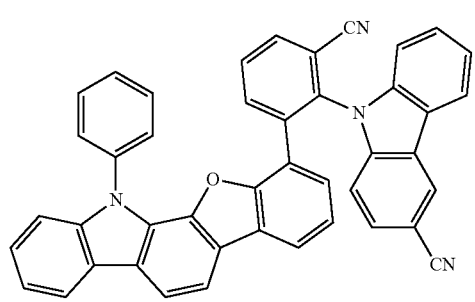
319
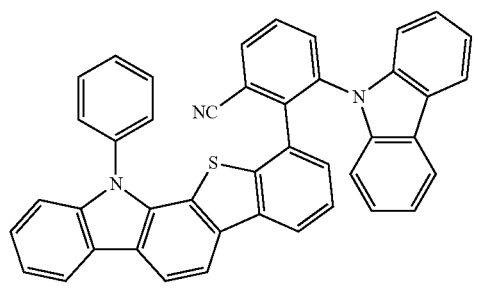
320
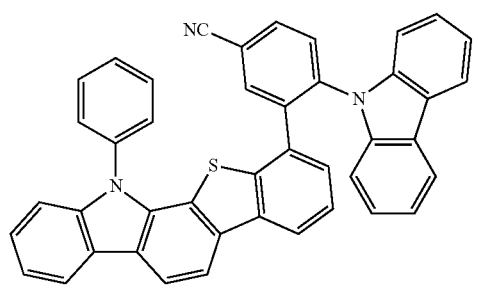
321
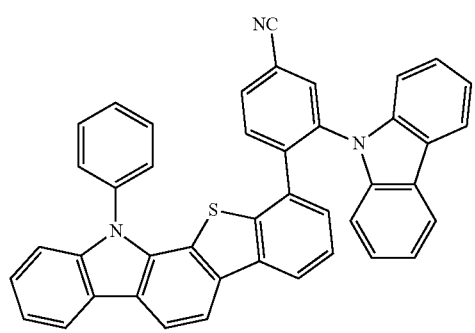
322
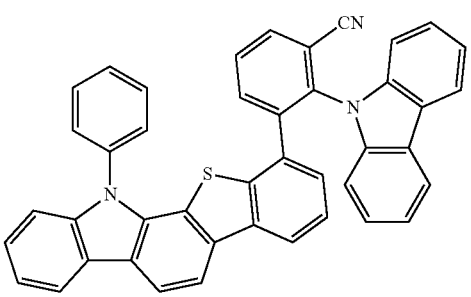
323
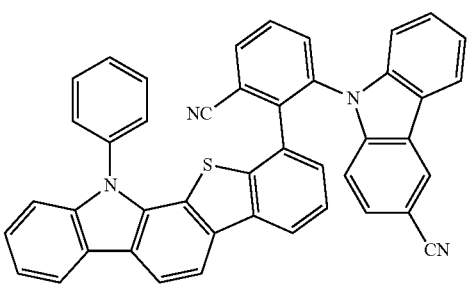
324
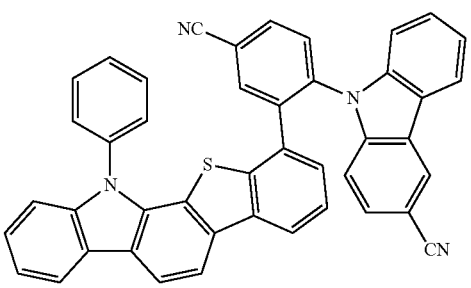
325
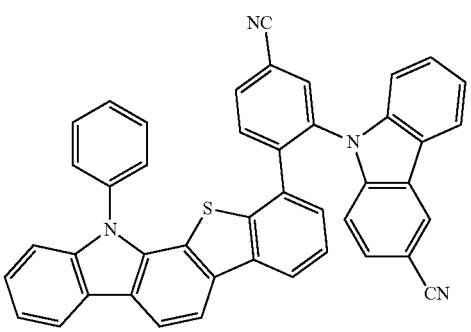
326
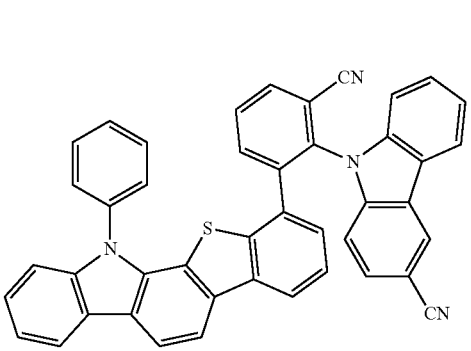

327
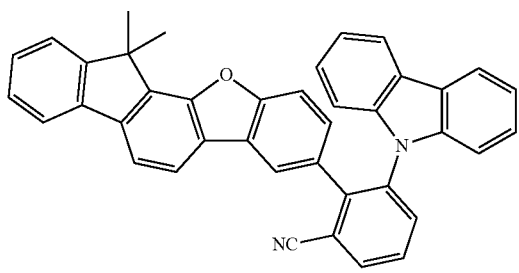
328
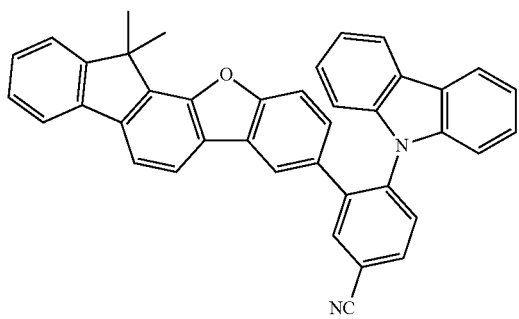
329
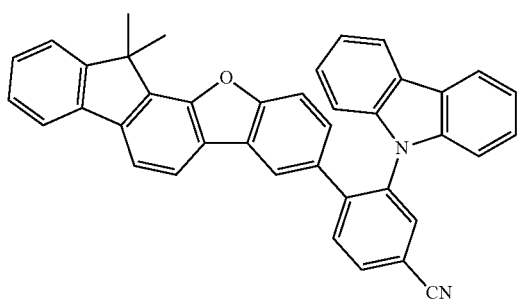
330
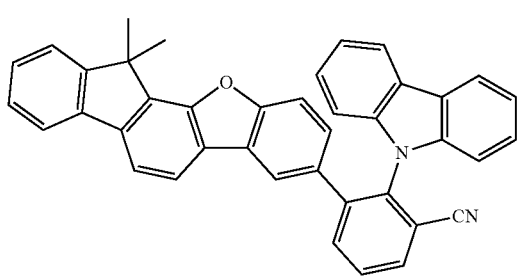
331
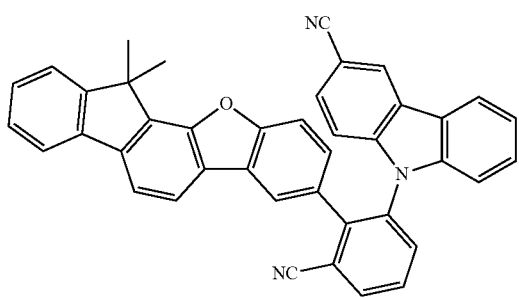
332
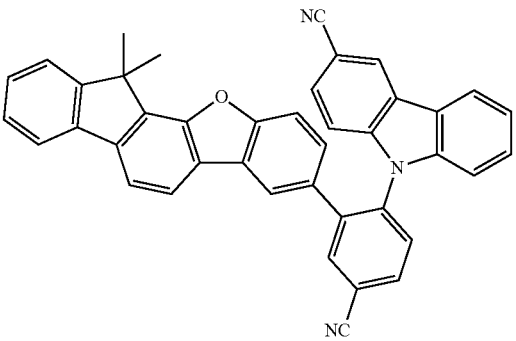
333
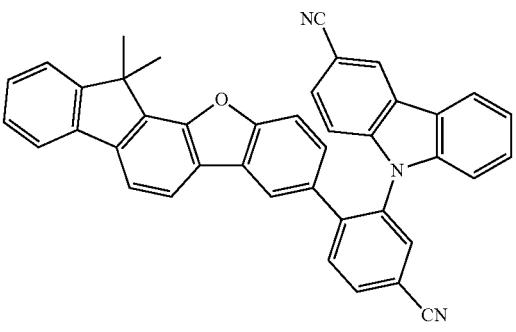
334
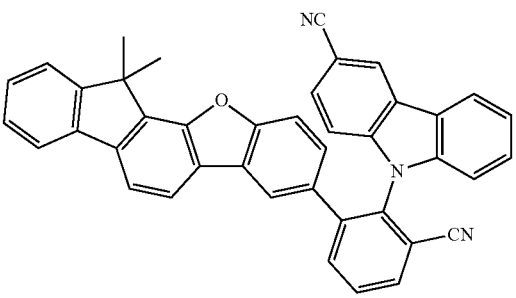
335
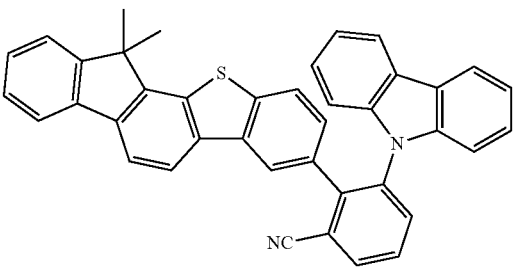
336
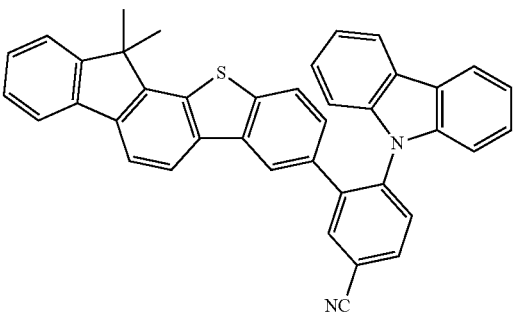

| 337 | 342 |
|---|---|
| 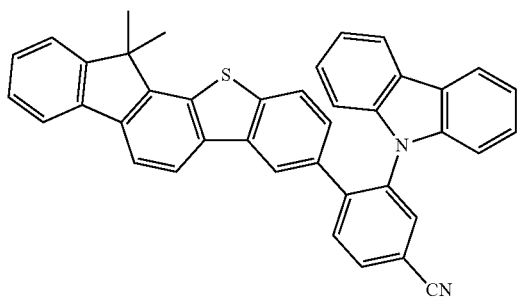 | 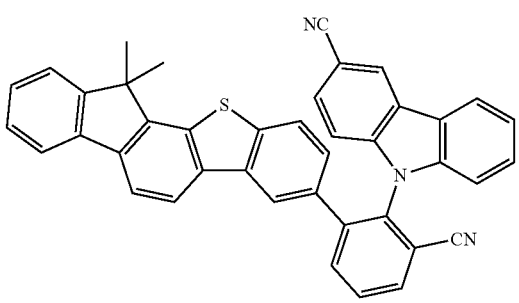 |
| 338 | 343 |
| 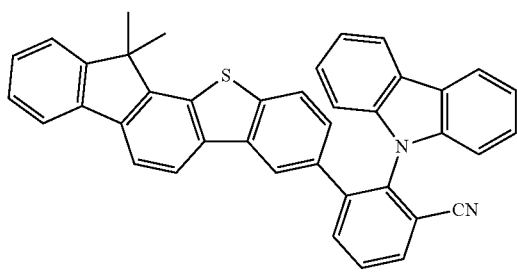 | 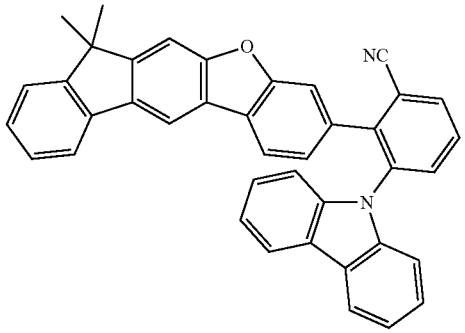 |
| 339 | |
| 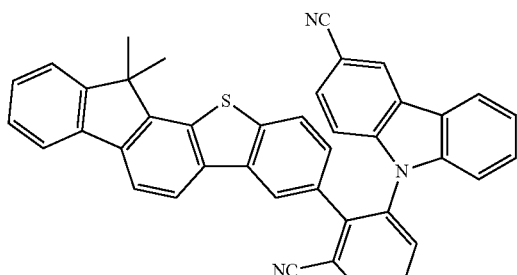 | |
| 340 | 344 |
| 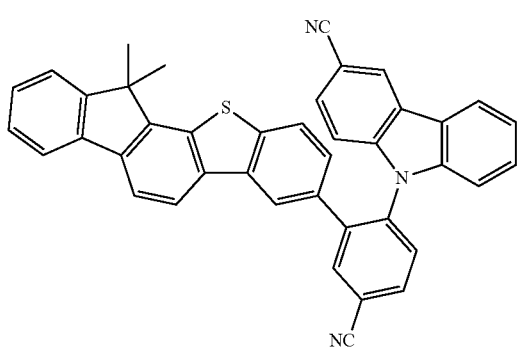 | 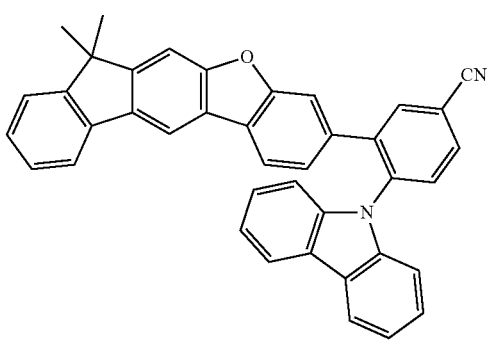 |
| 341 | 345 |
| 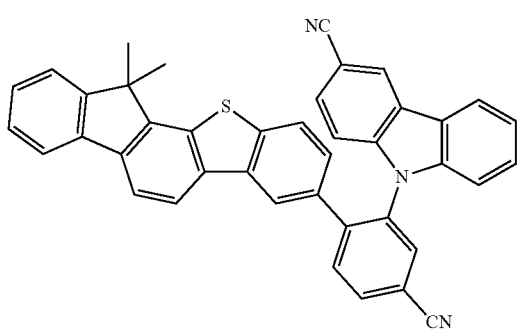 | 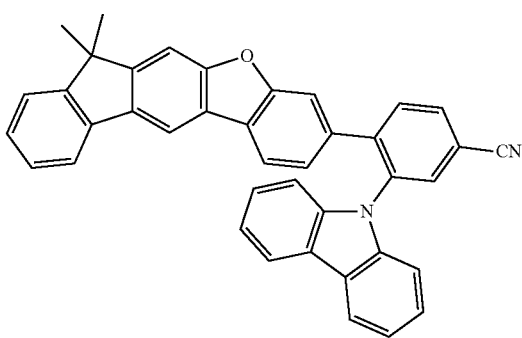 |

346
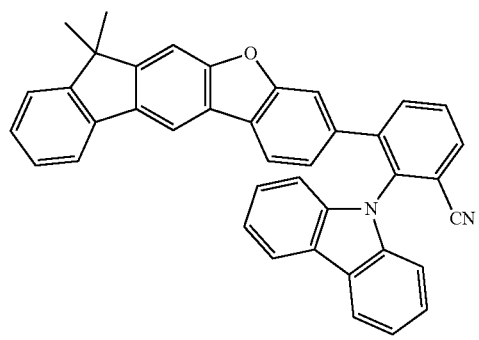
347
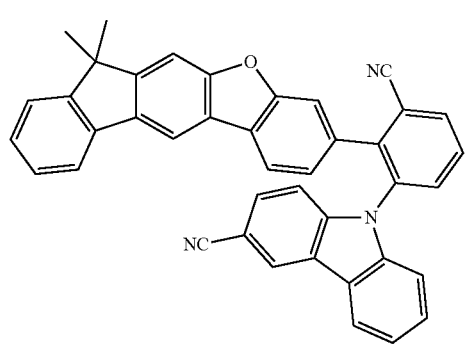
348
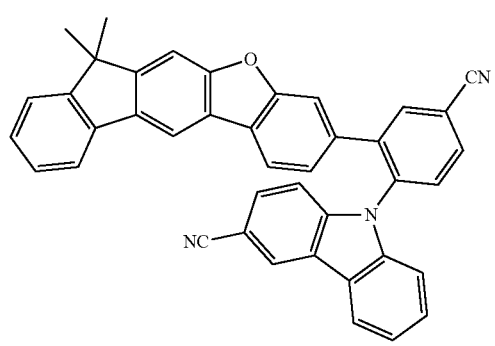
349
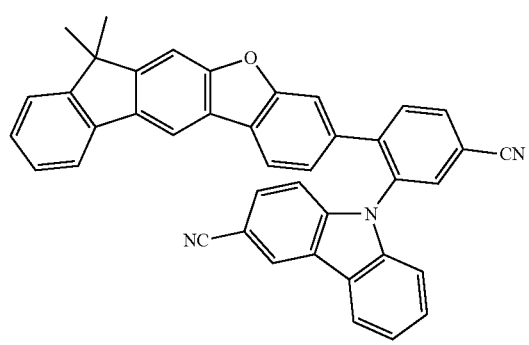
350
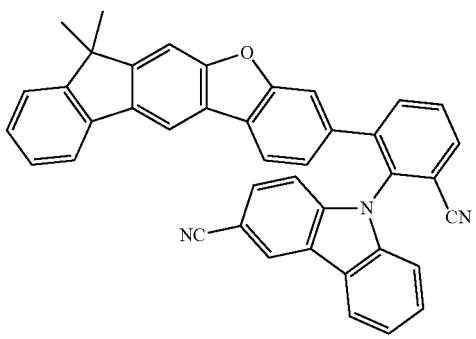
351
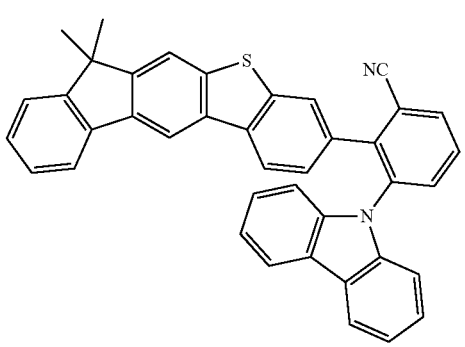
352
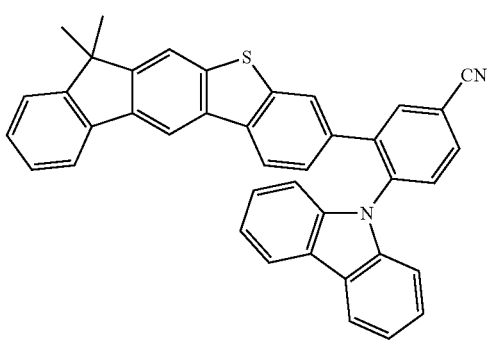
353
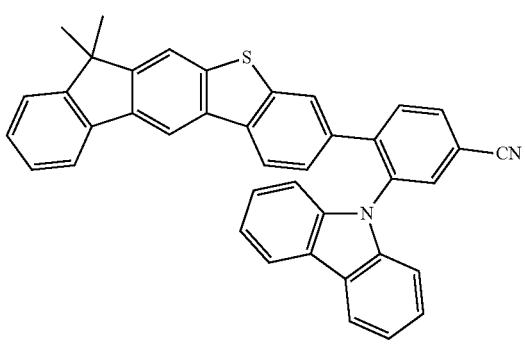

354
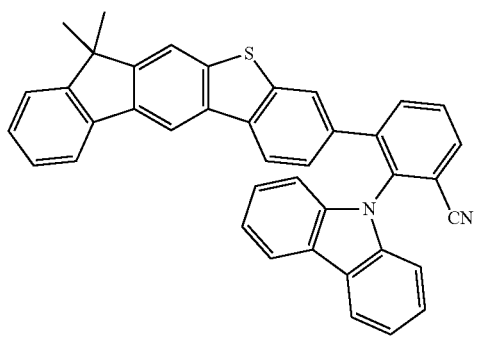
355
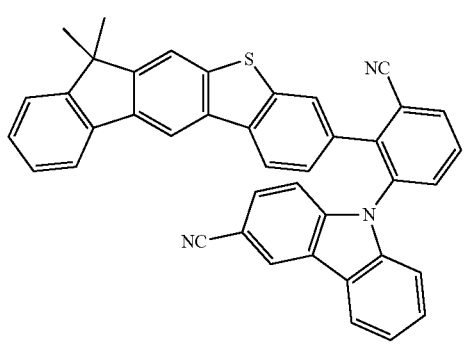
356
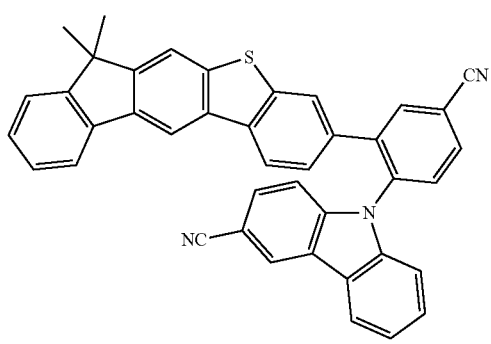
357
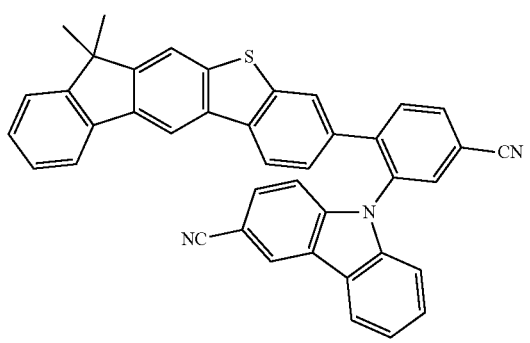
358
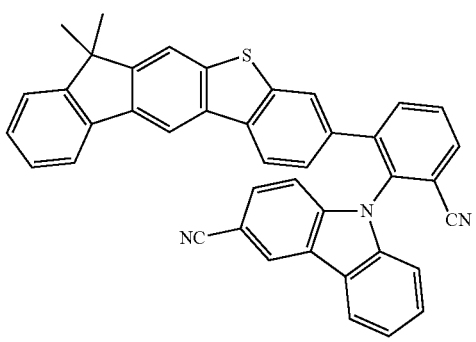
359
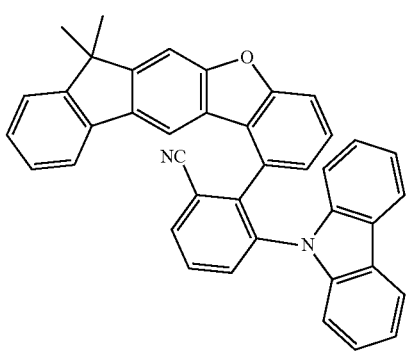
360
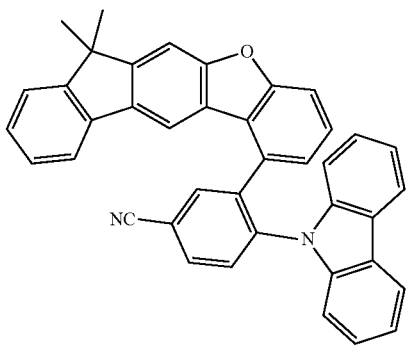
361
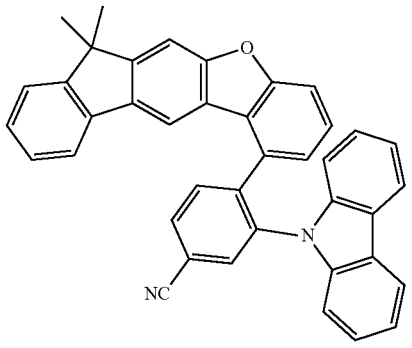

| 747 | 748 |
|---|---|
| -continued | -continued |
362

363
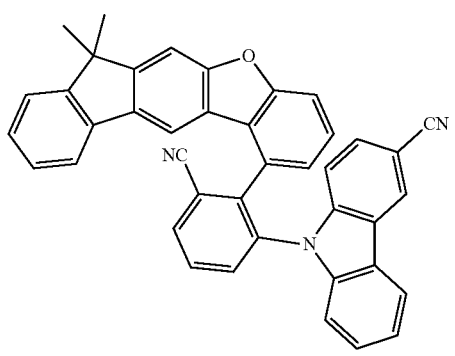
364
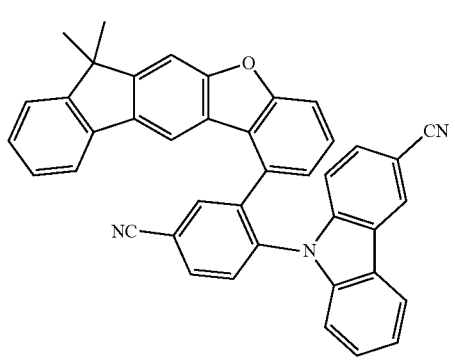
365
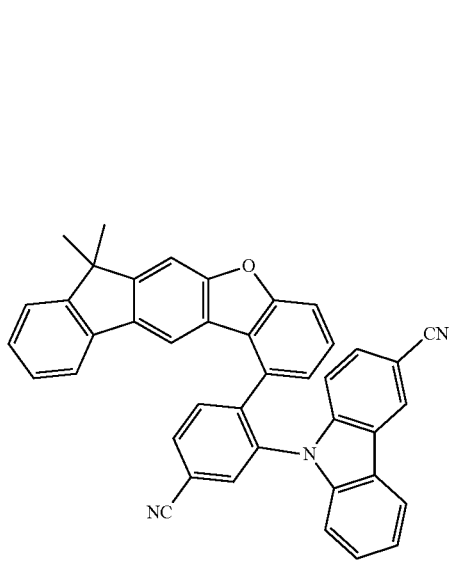
366
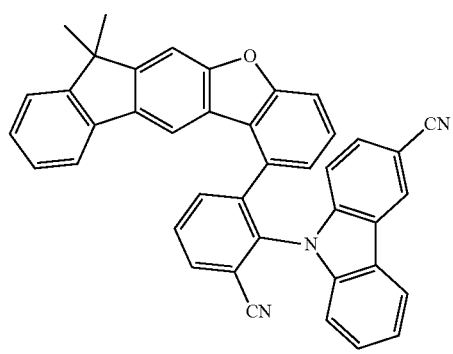
367
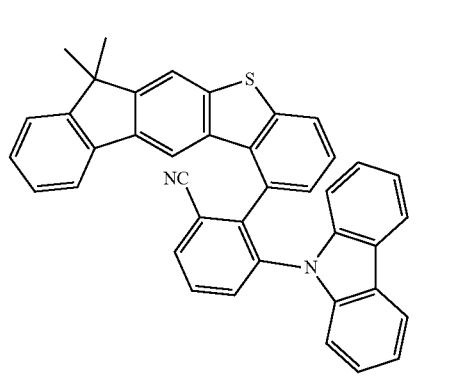
368
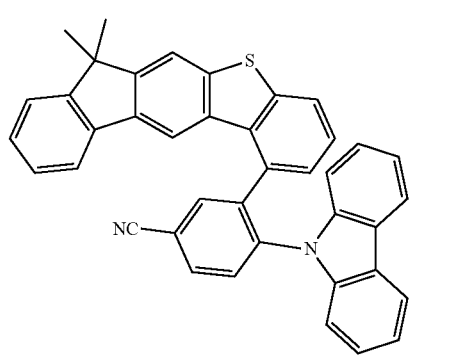
369
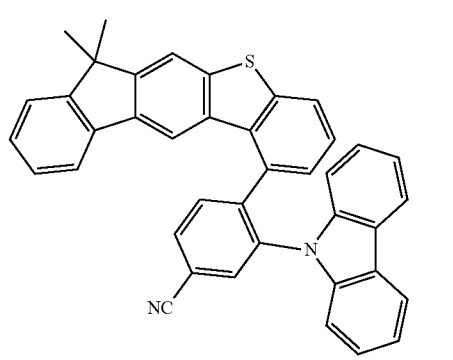

749
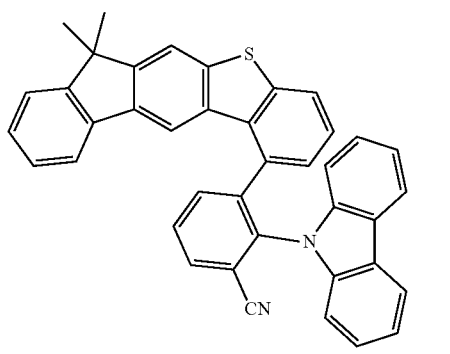
370

371
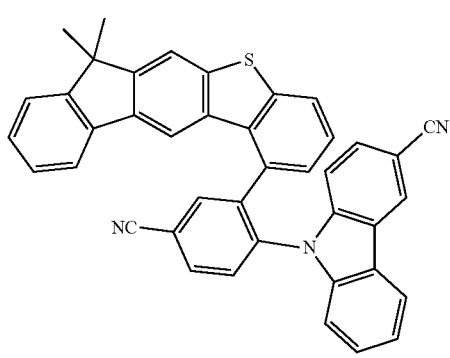
372

373
750
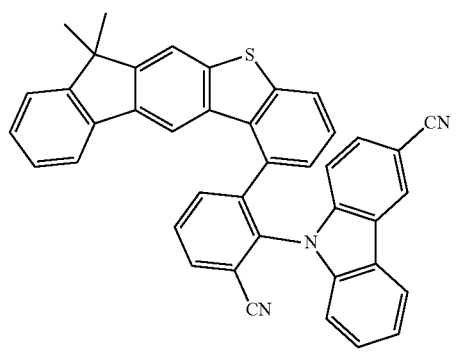
374

375
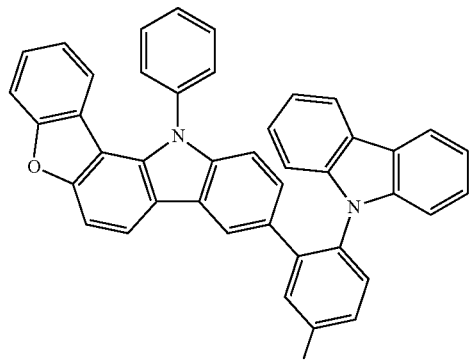
376
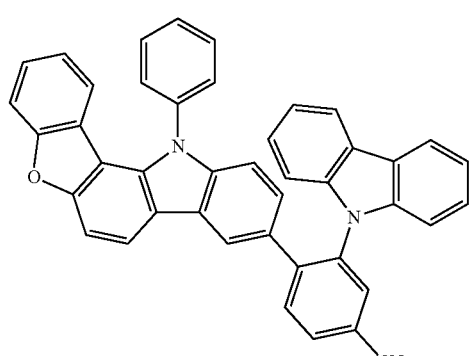
377

751 -continued
378
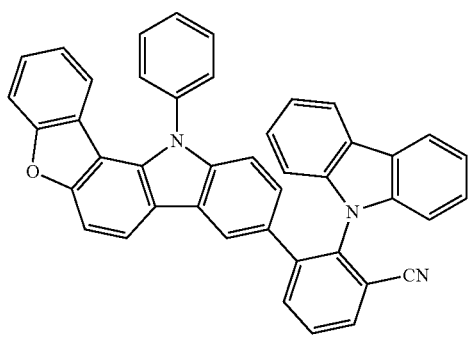
379
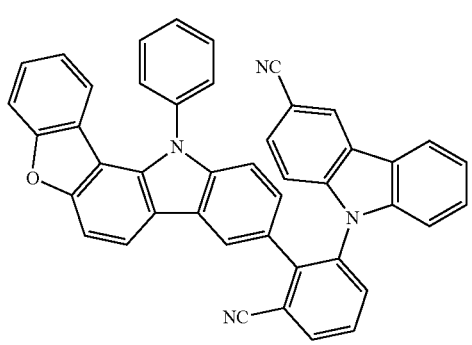
380
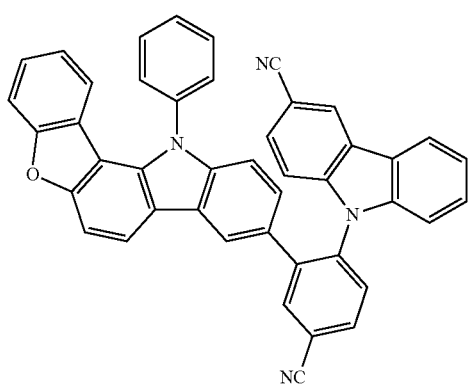
381
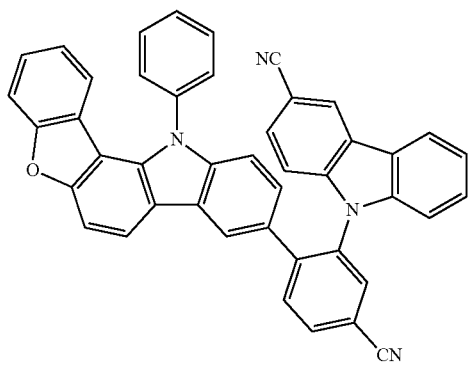
752 -continued
382
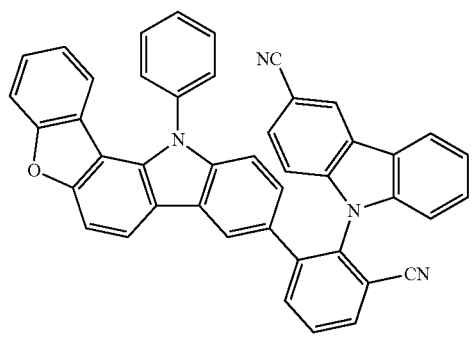
383
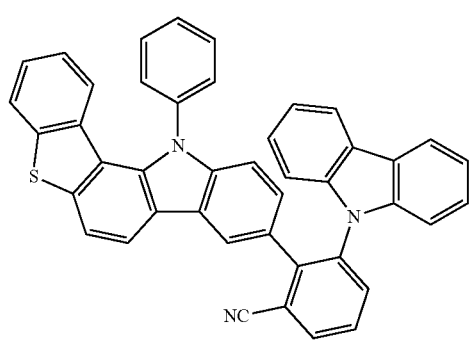
384
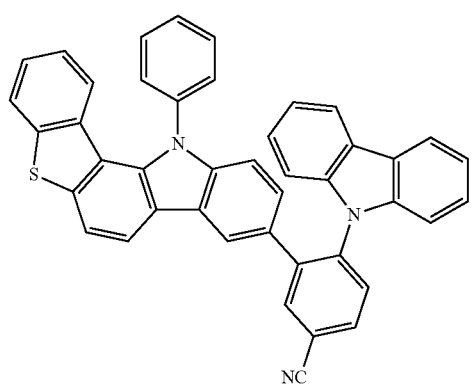
385
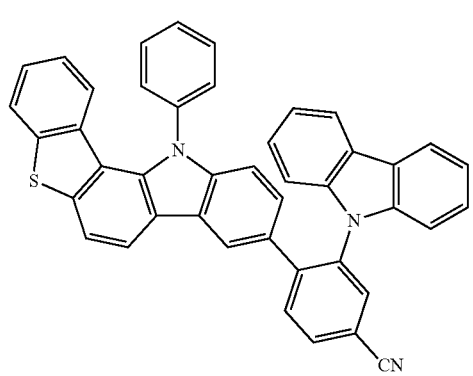

386
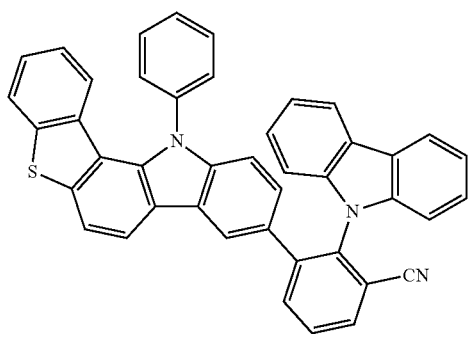
387
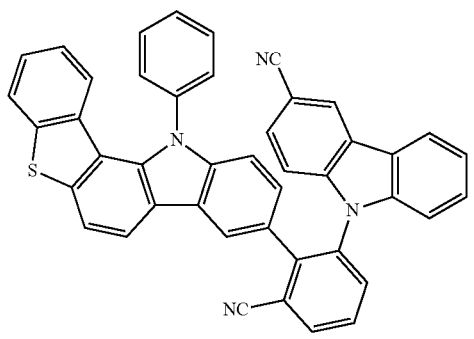
388
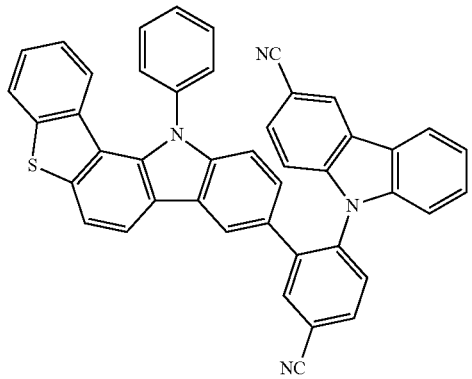
389
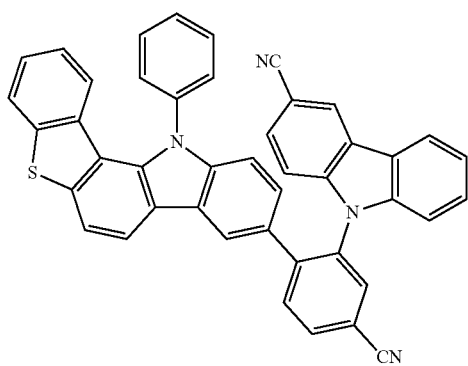
390
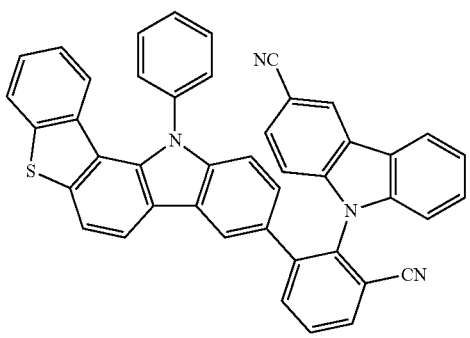
391
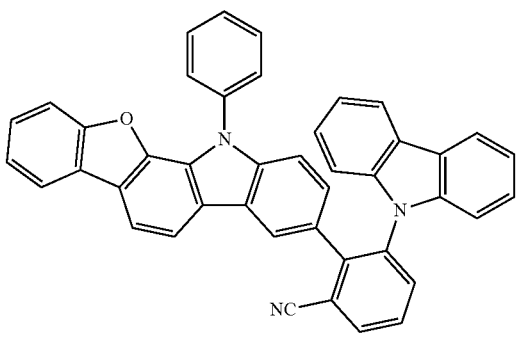
392
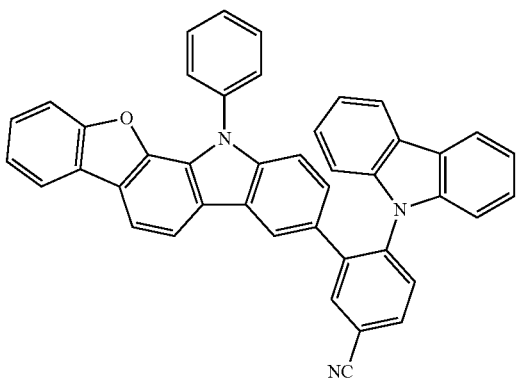
393
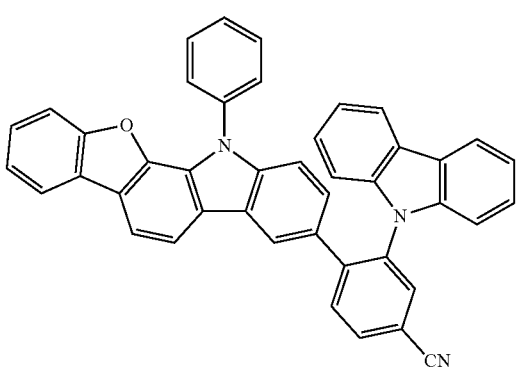

755
-continued
394
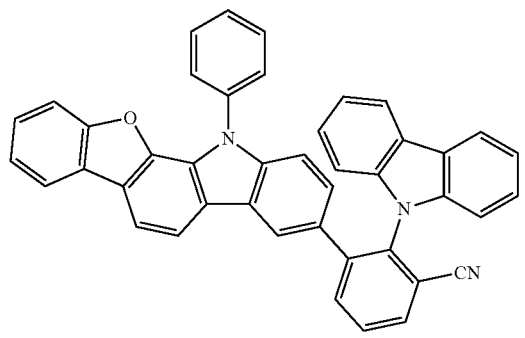
395
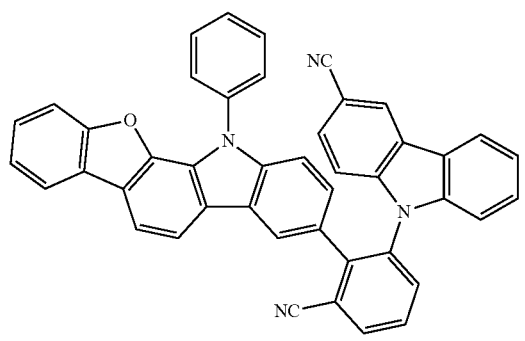
396
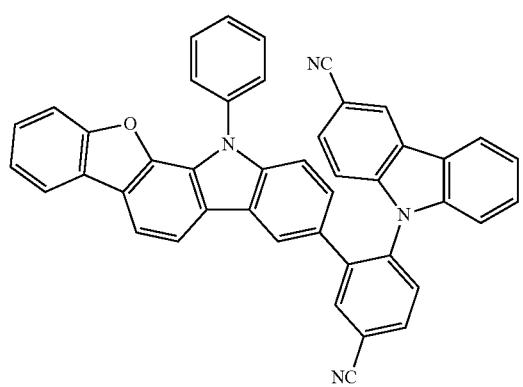
397
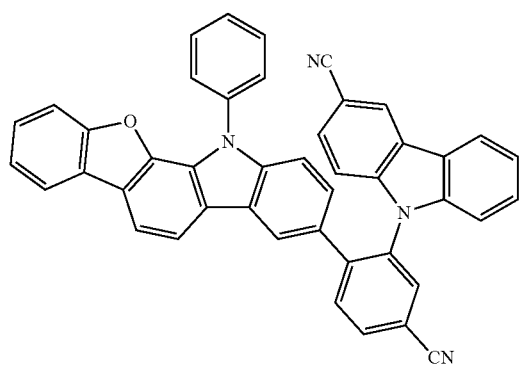
756
-continued
398
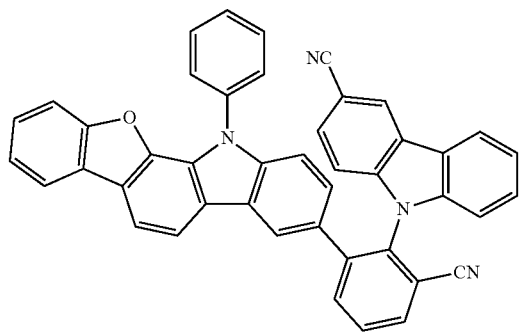
399
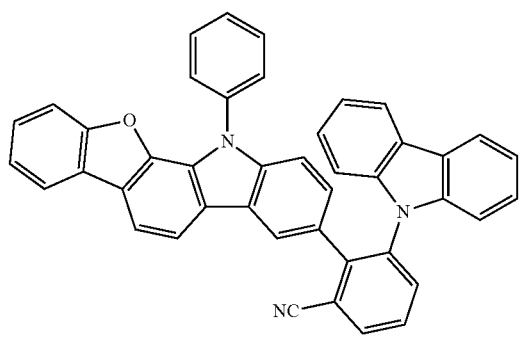
400
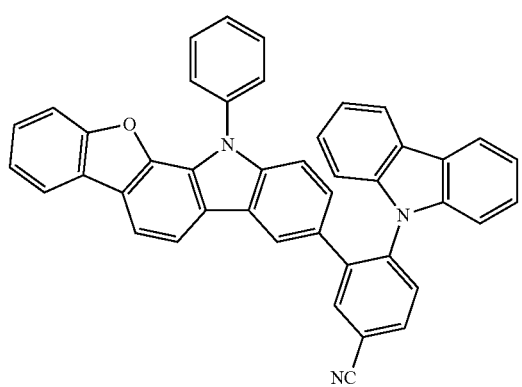
401
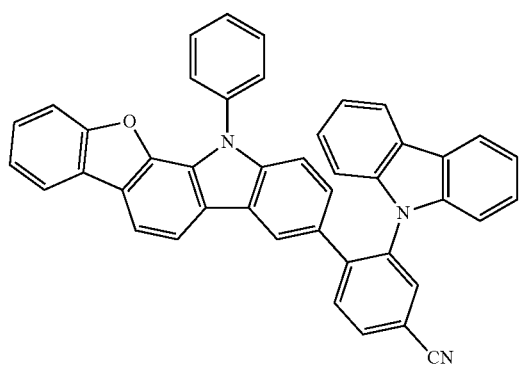

| 402 | 406 |
|---|---|
| 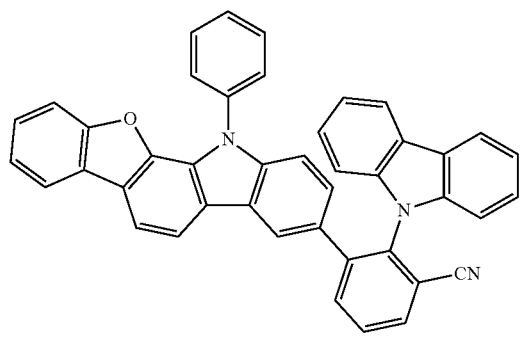 | 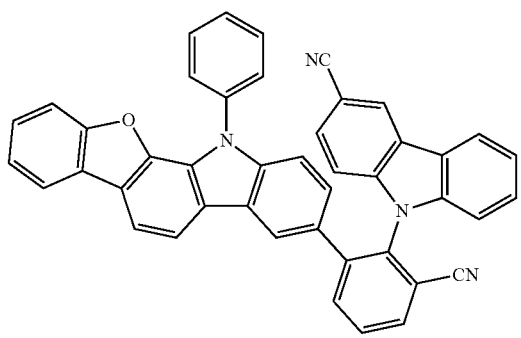 |
| 403 | 407 |
| 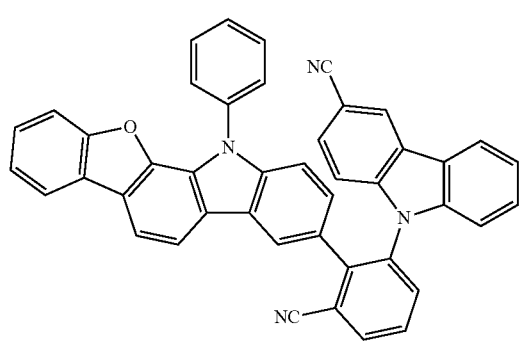 | 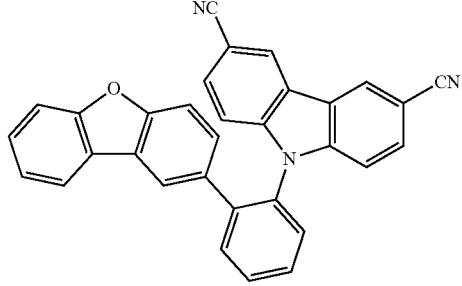 |
| 404 | 408 |
| 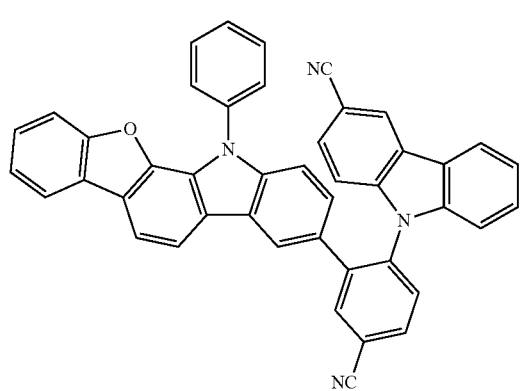 | 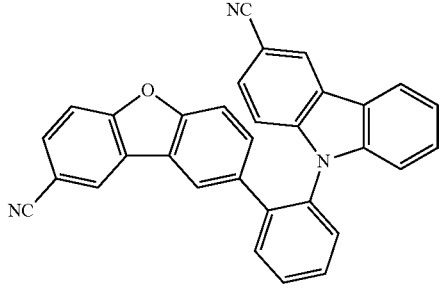 |
| | 409 |
| | 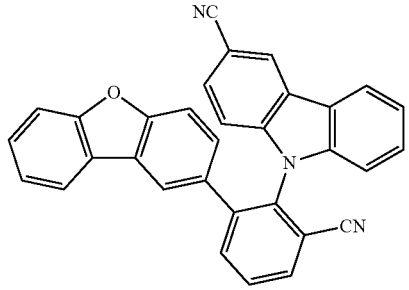 |
| 405 | 410 |
| 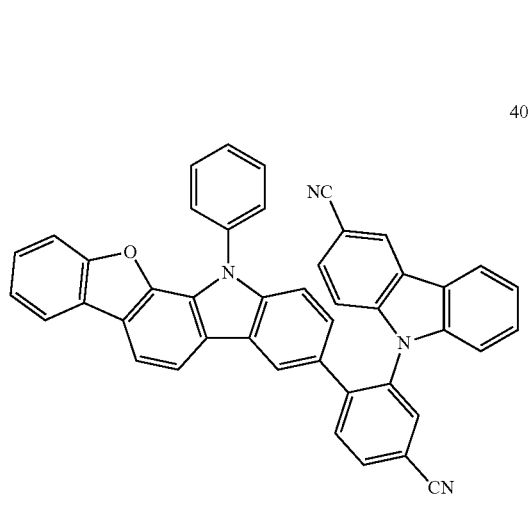 | 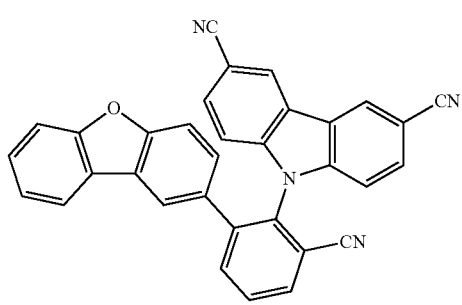 |

| 411 | 415 |
|---|---|
| 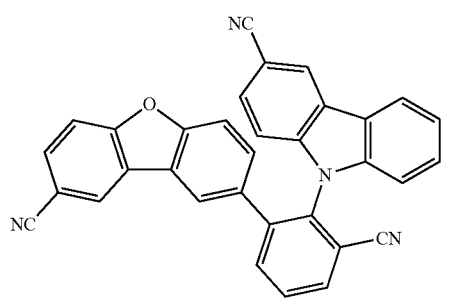 | 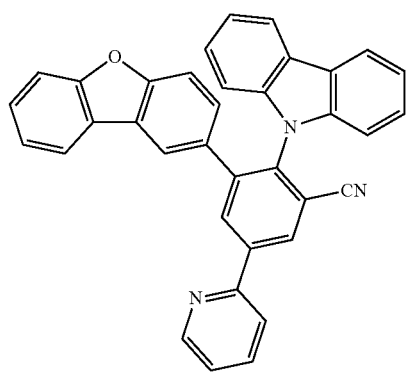 |
| 412 | 416 |
| 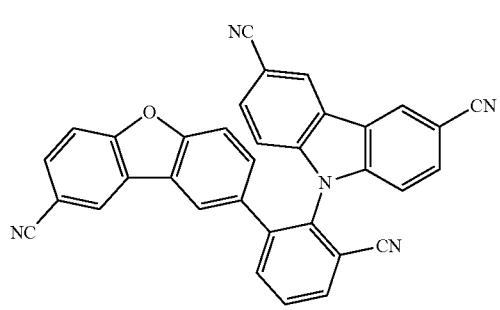 | 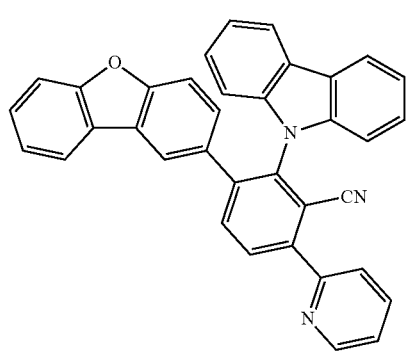 |
| 413 | 417 |
| 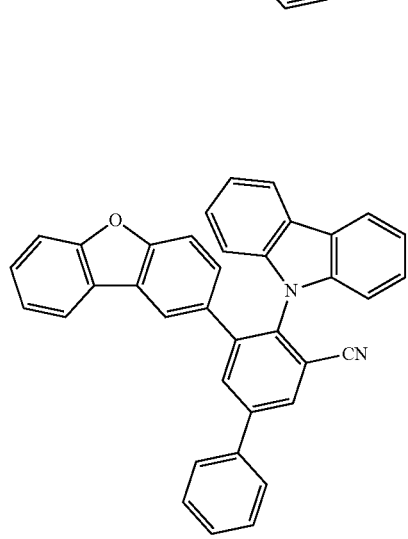 | 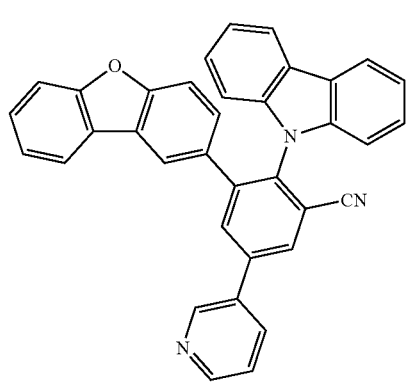 |
| 414 | 418 |
| | 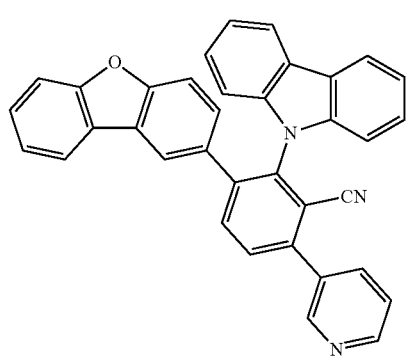 |

-continued
419
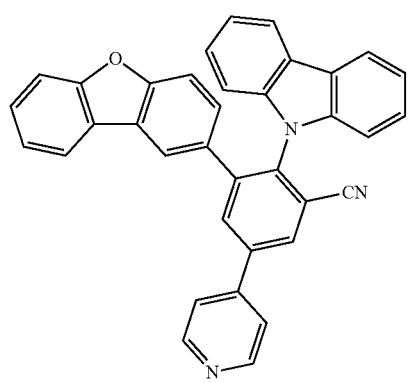
420
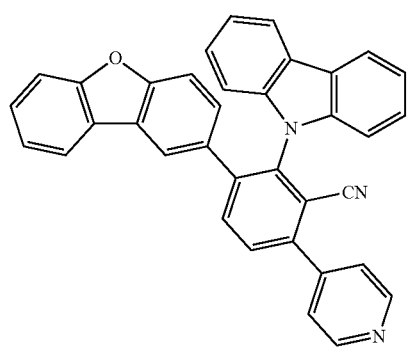
421
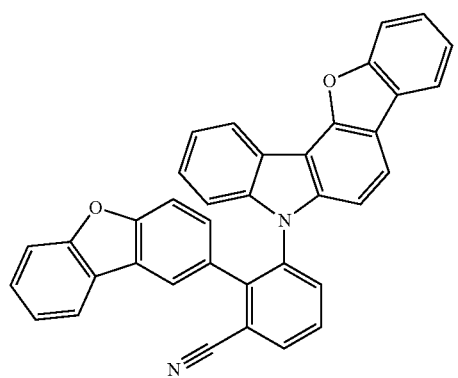
422
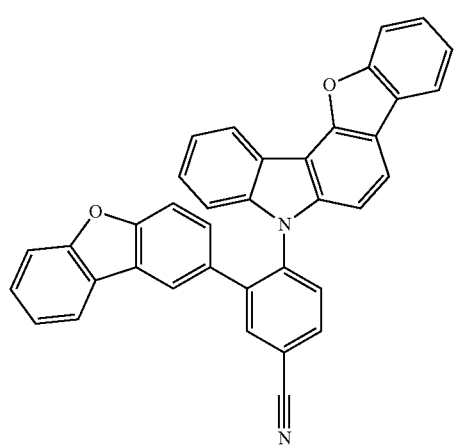
-continued
423
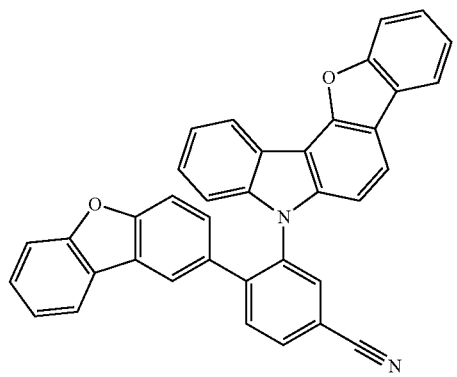
424
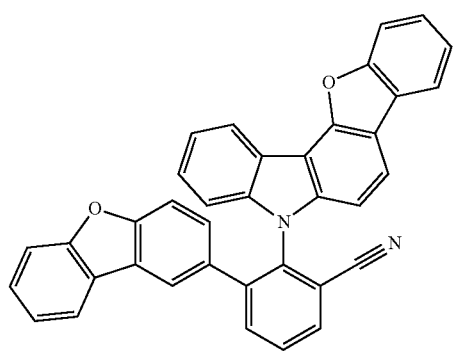
425
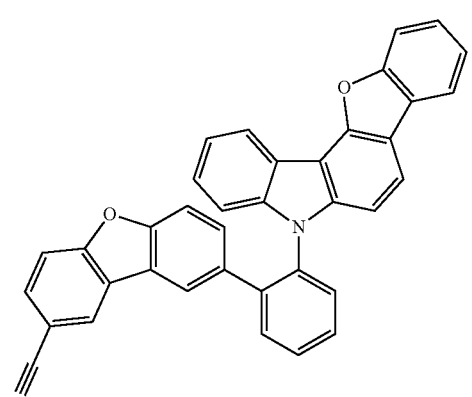
426
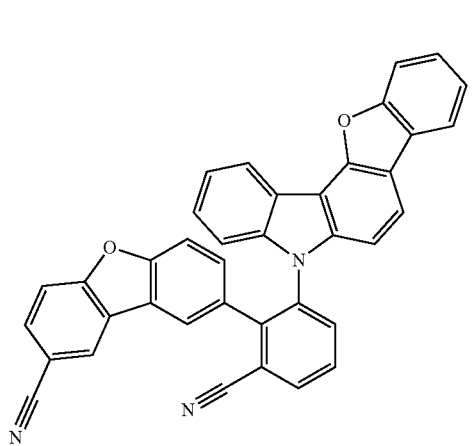

763
-continued
427
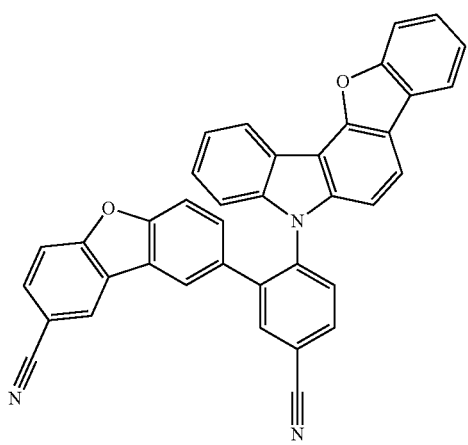
428
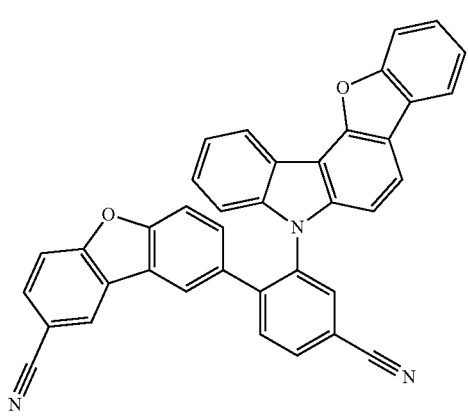
429
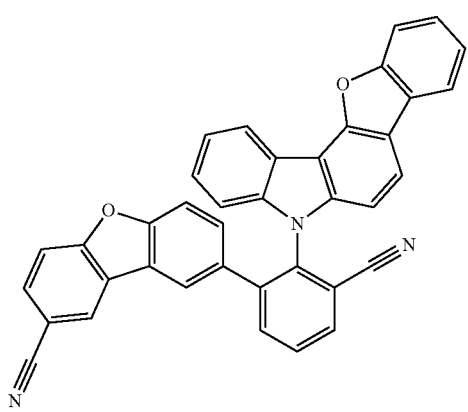
764
-continued
430
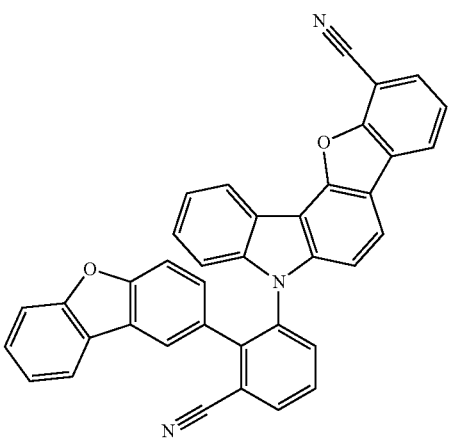
431
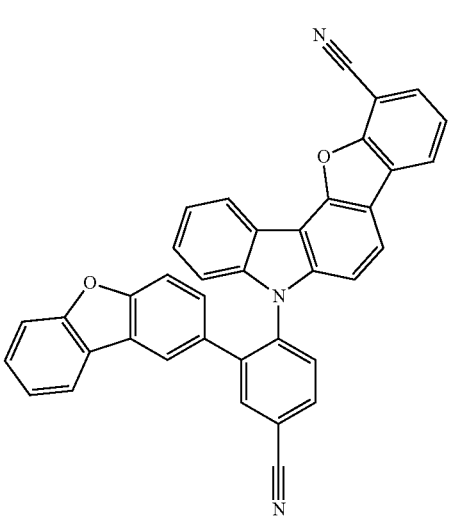
432
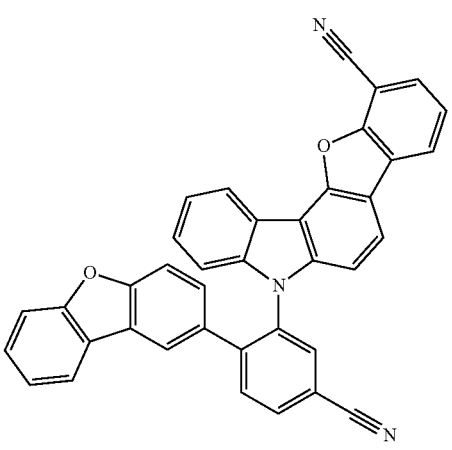

765
-continued
433
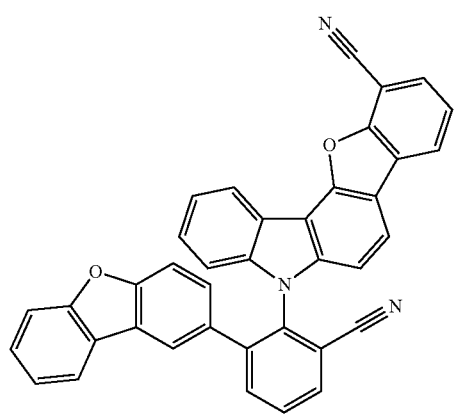
434
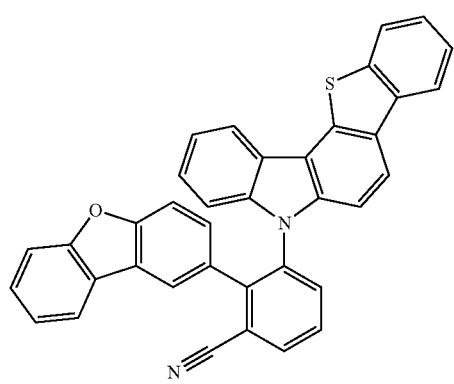
435
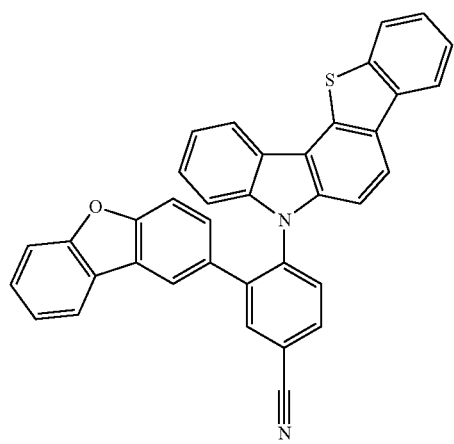
436
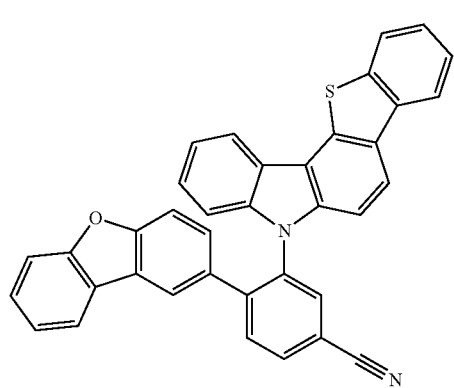
766
-continued
437
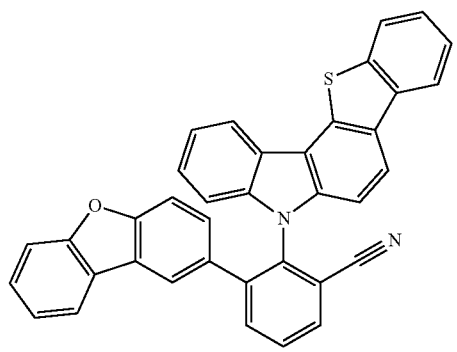
438
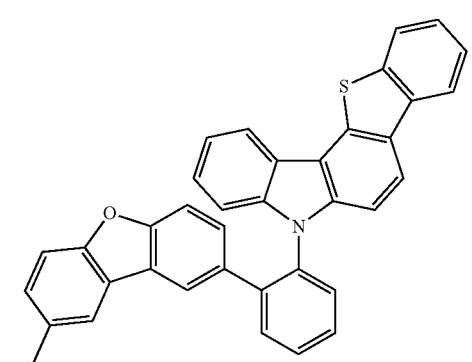
439
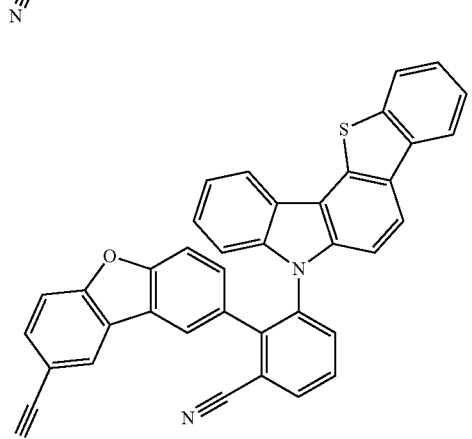
440
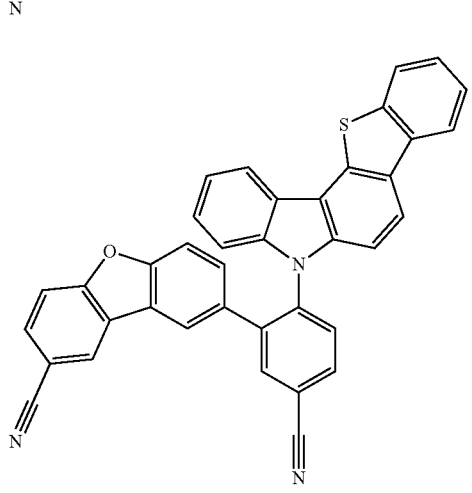

441
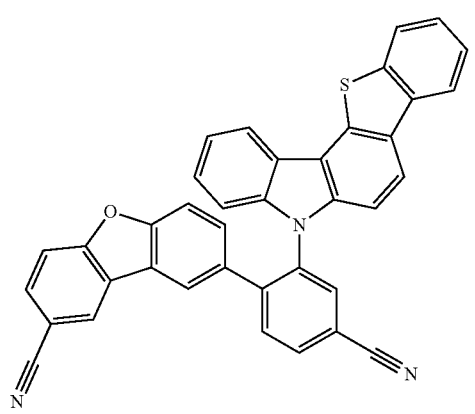
442
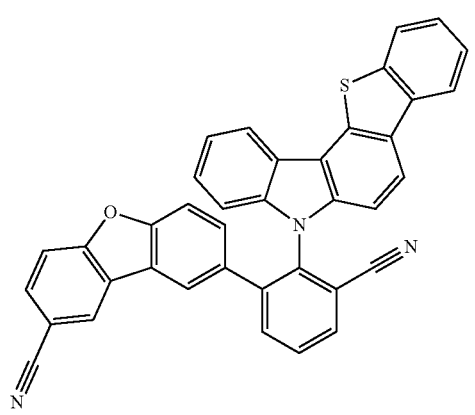
443
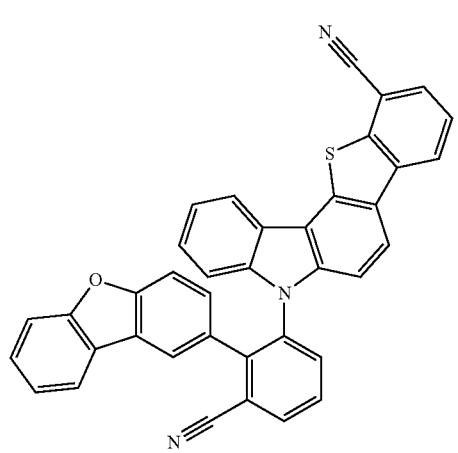
444
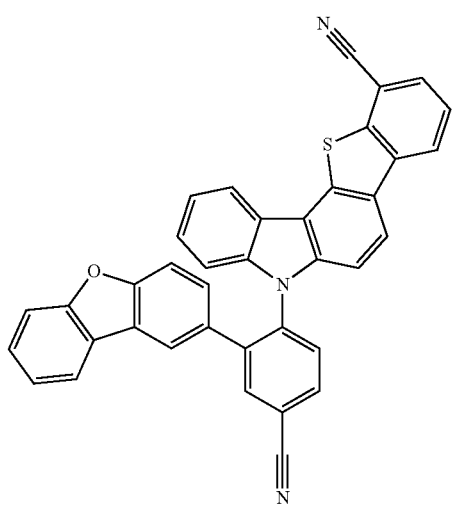
445
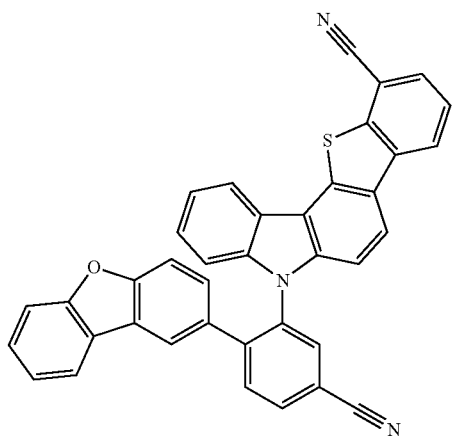
446

769
-continued
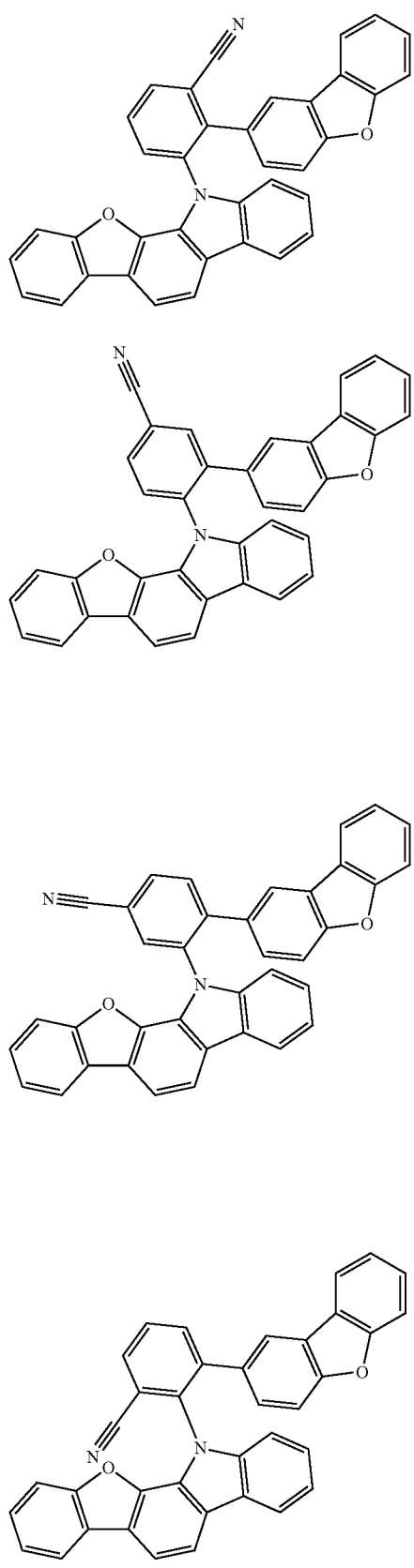
770
-continued
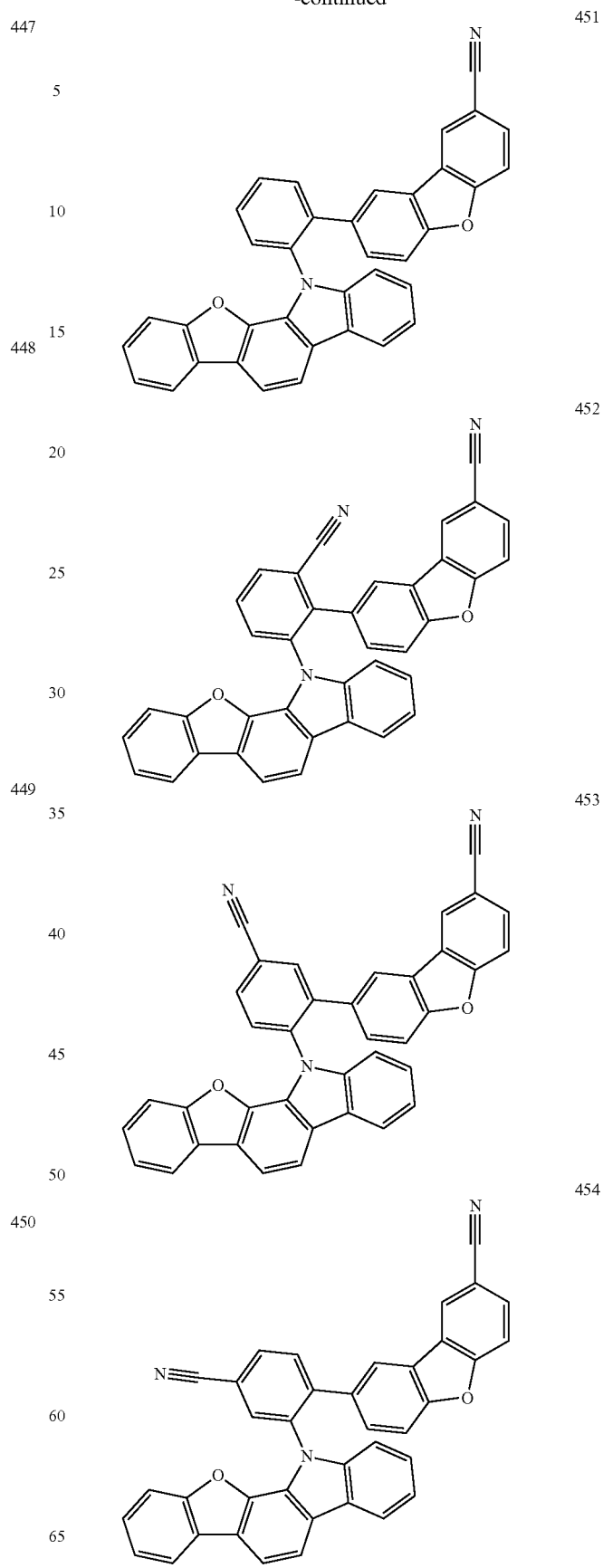

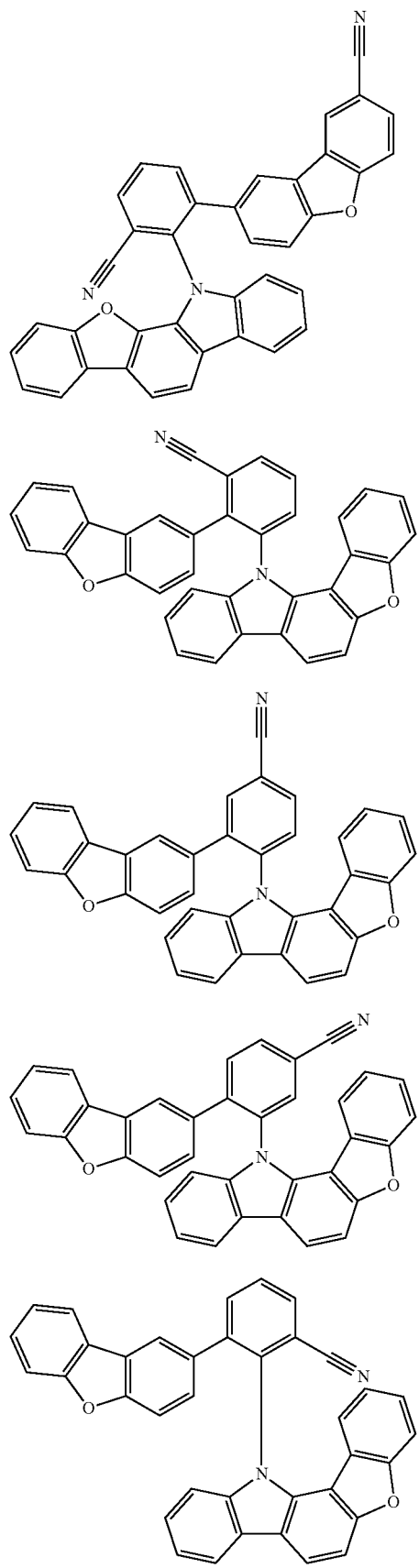
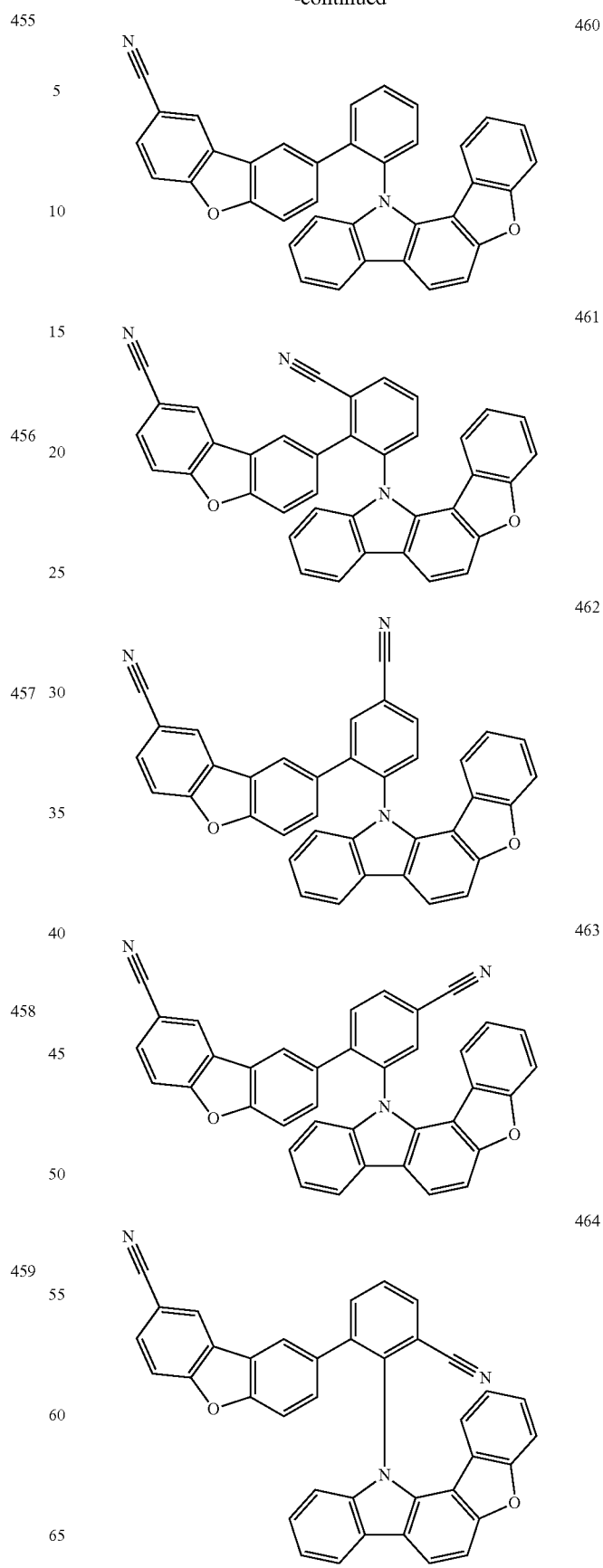

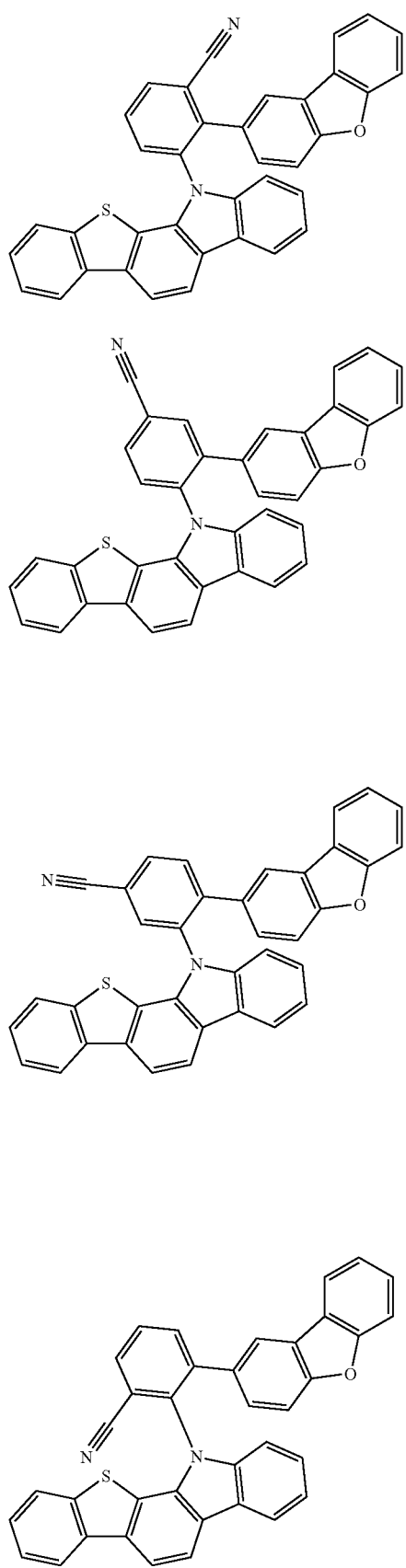
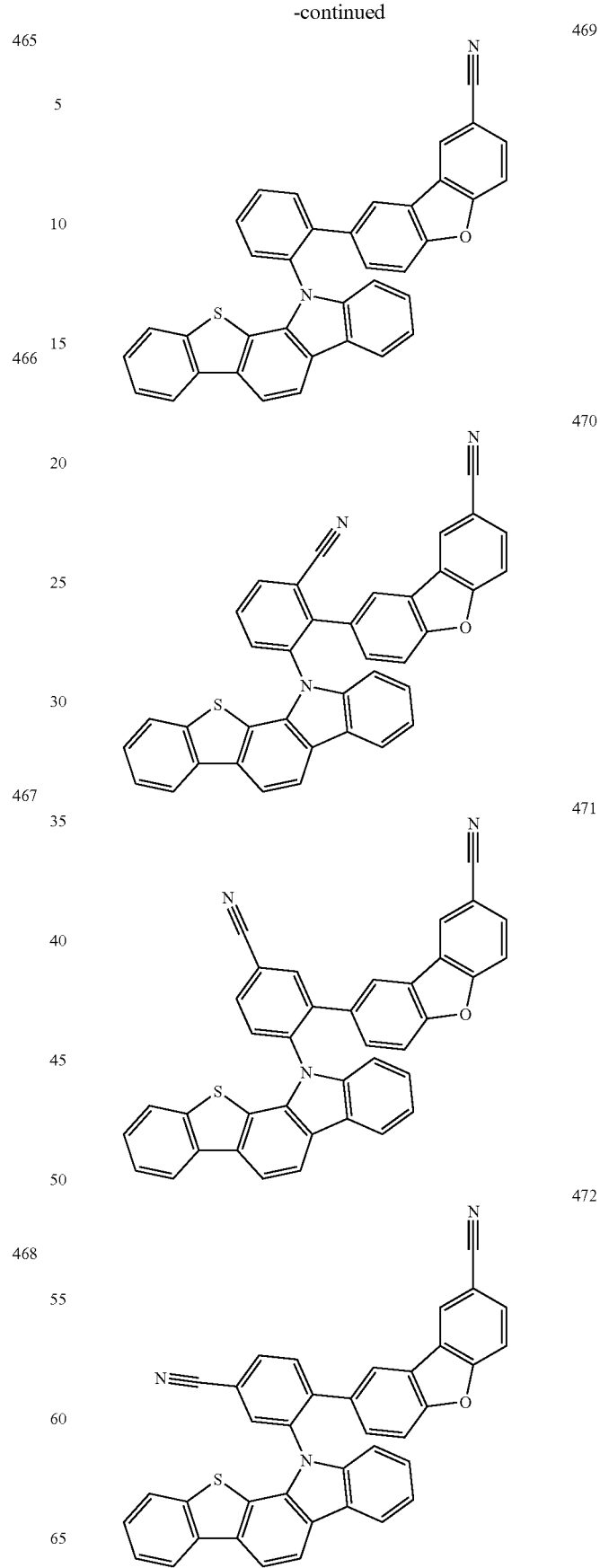

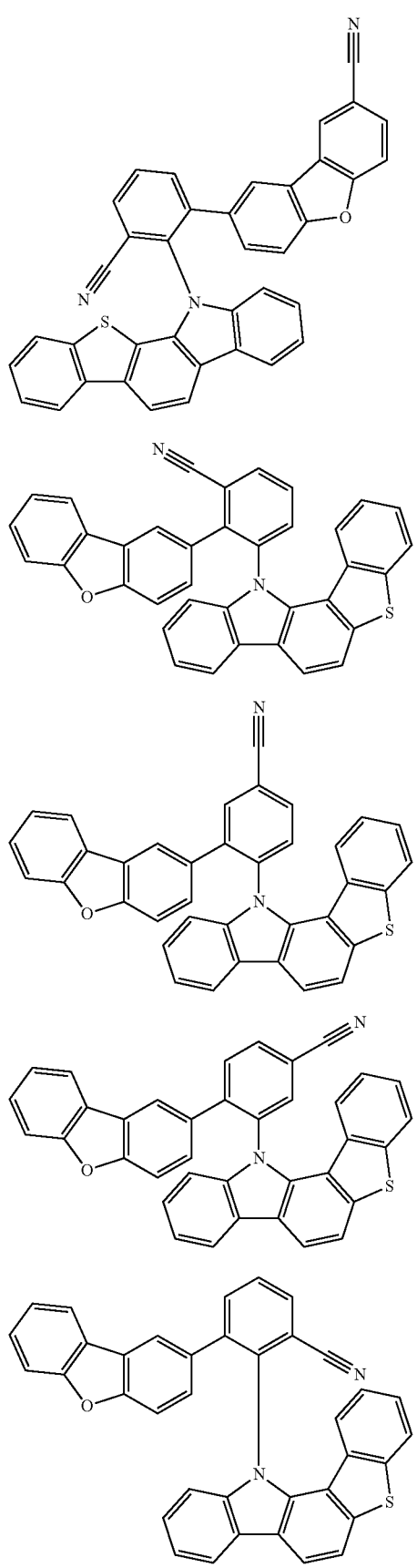
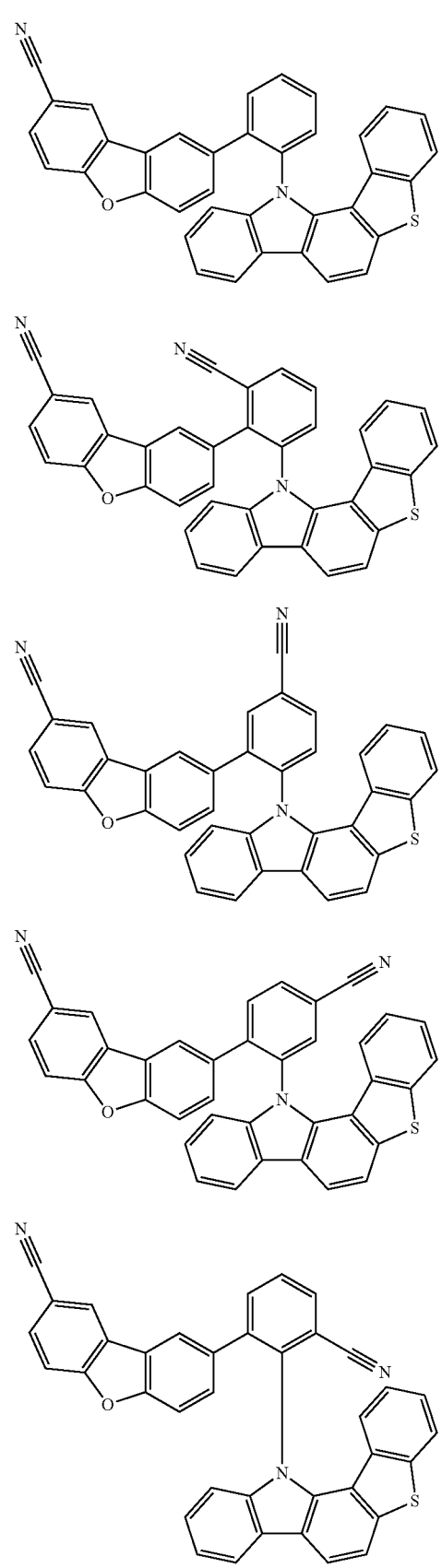

Group HE4
1
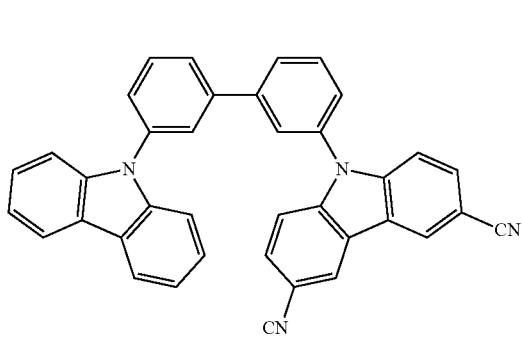
2
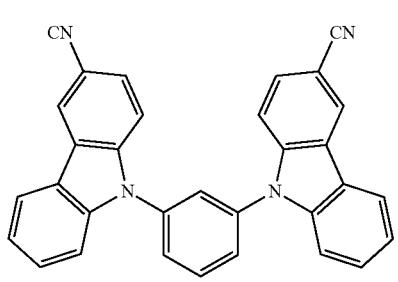
3
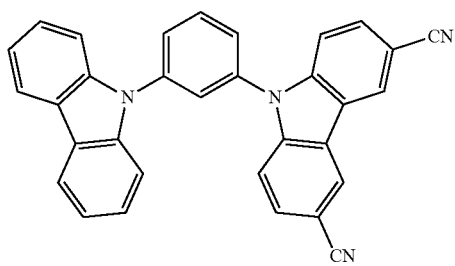
4
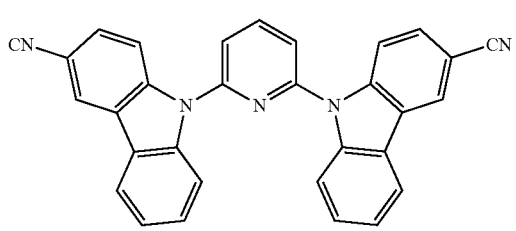
5
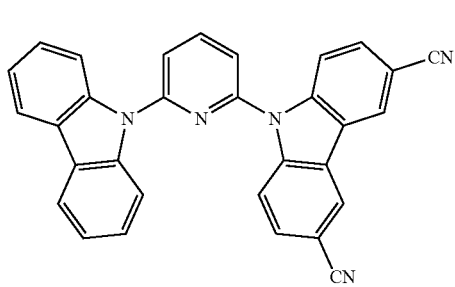
-continued
6
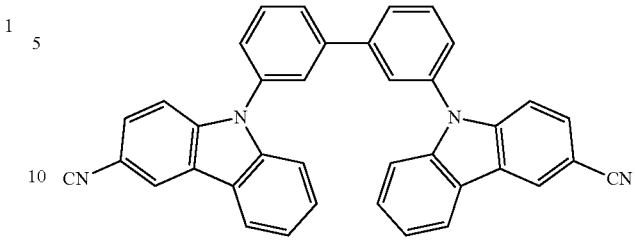
7
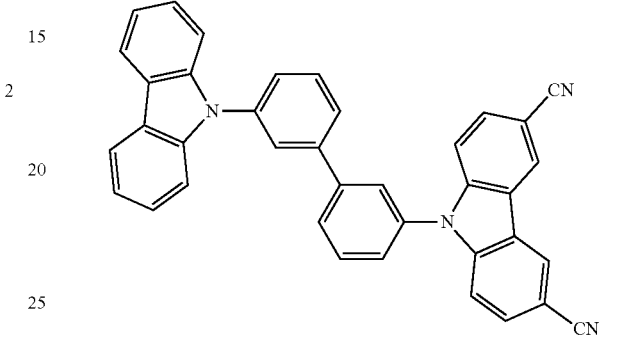
8
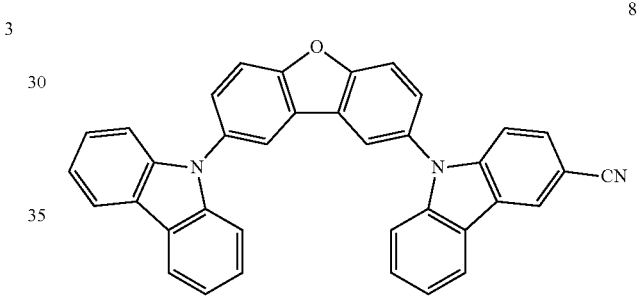
9
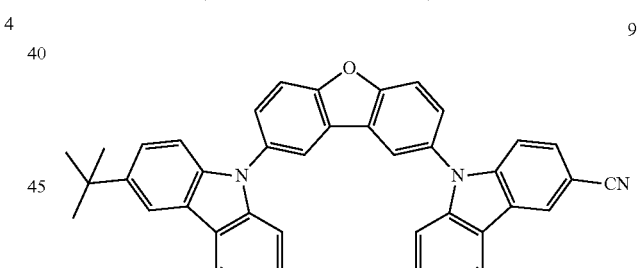
10
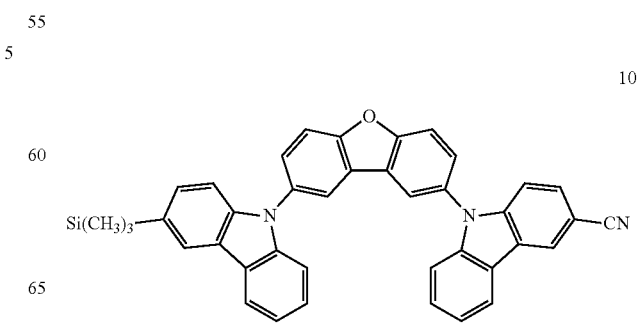

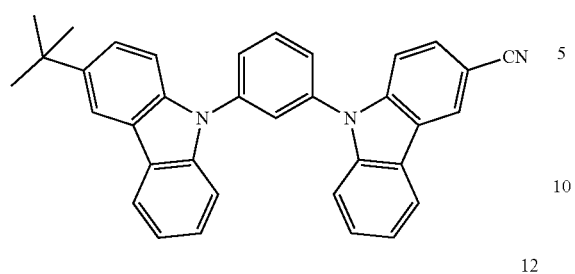
11
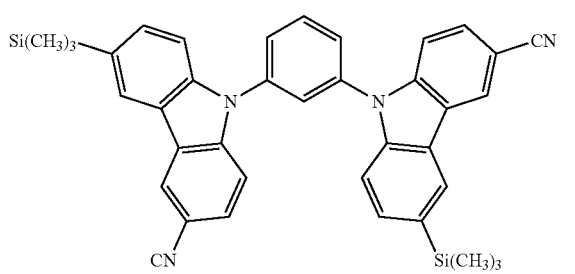
16
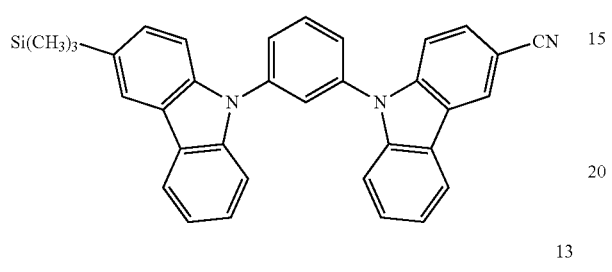
12
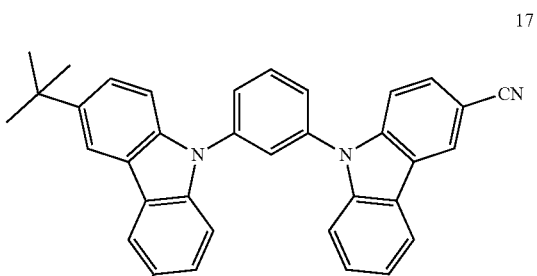
17
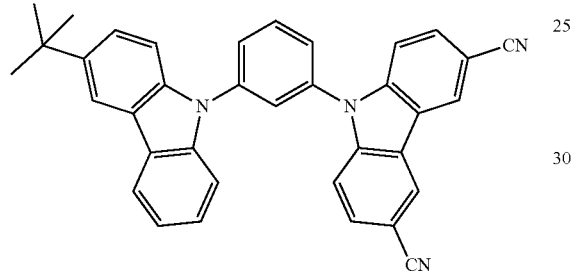
13
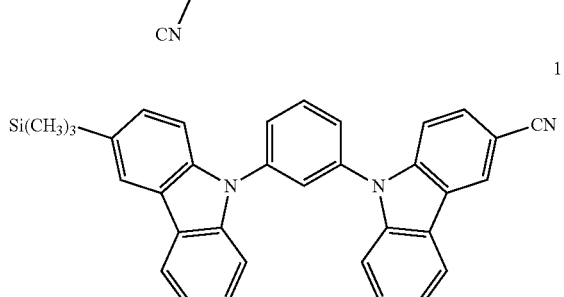
18
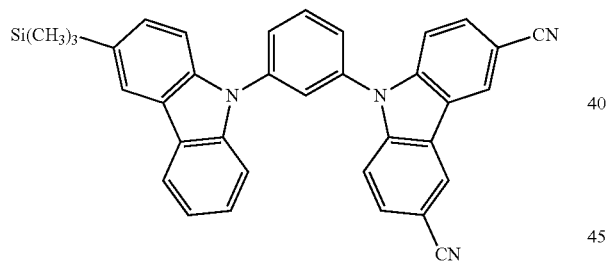
14
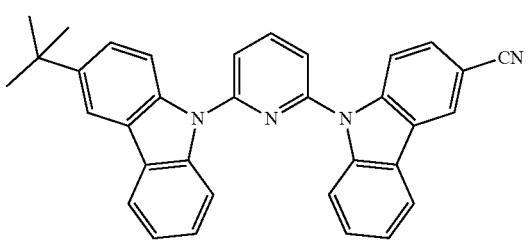
19
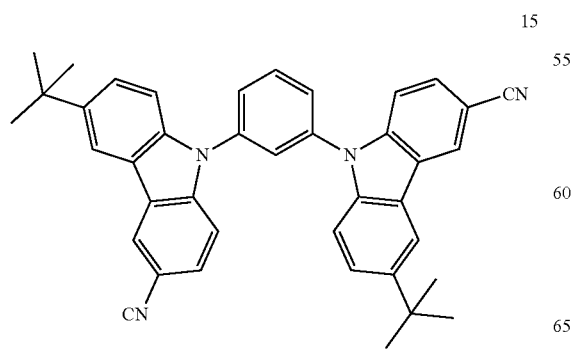
15
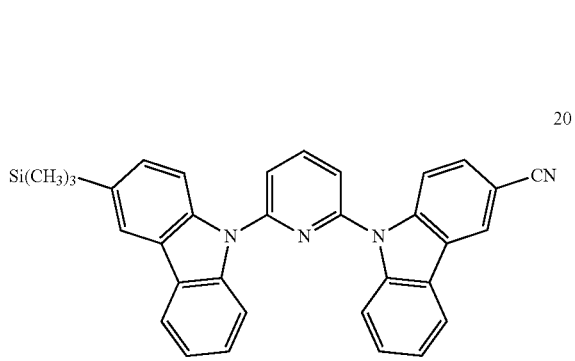
20

21
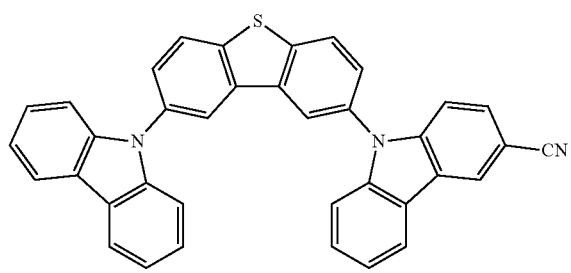
22
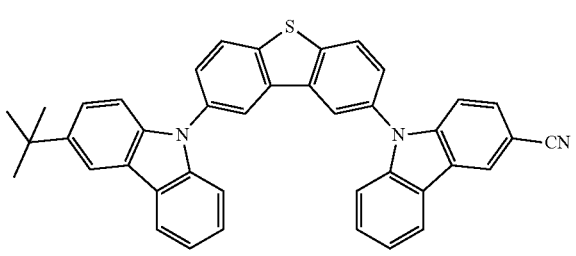
23

24
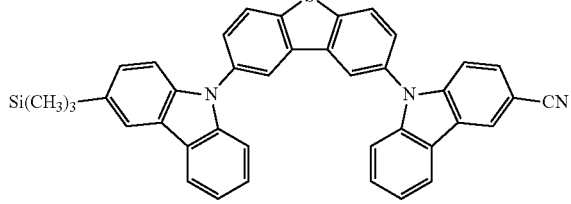
25
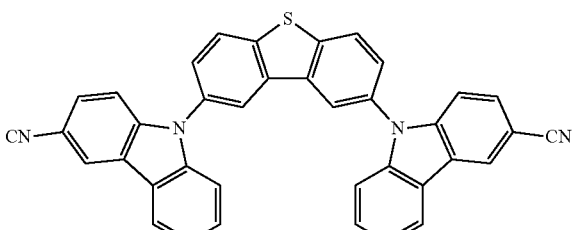
26
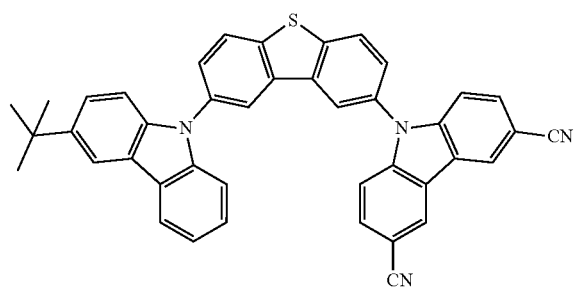
27
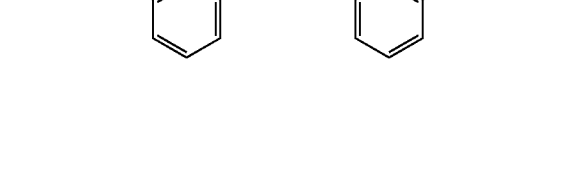
28
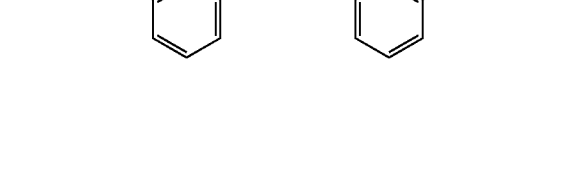
29
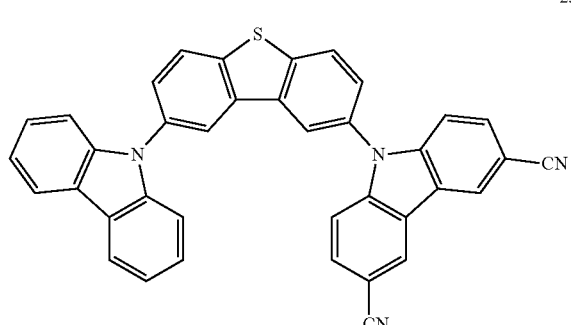
30
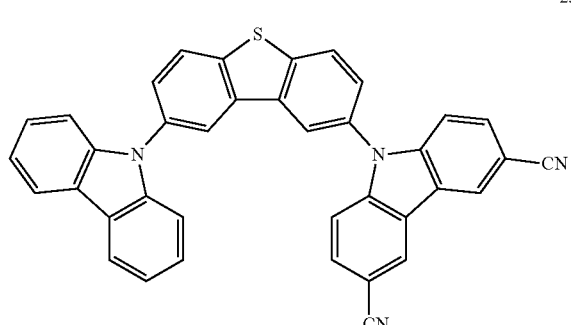

-continued
31
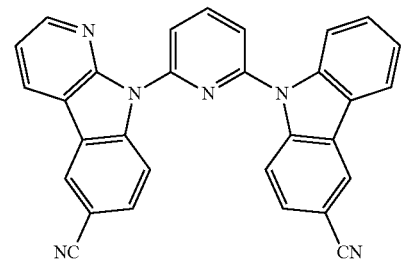
32
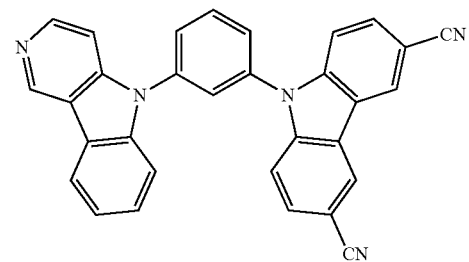
33
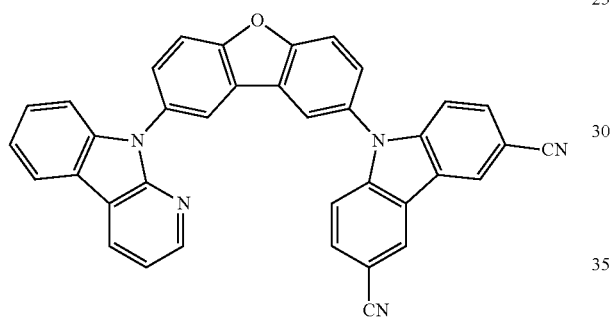
34
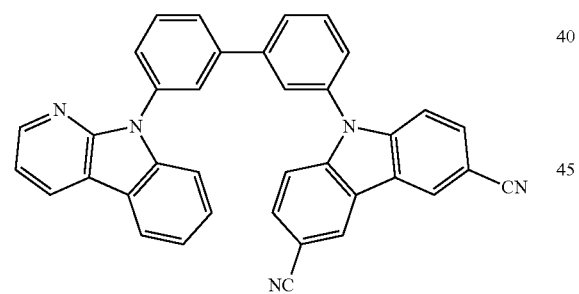
35
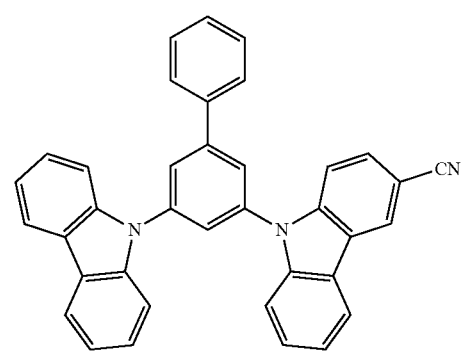
-continued
36
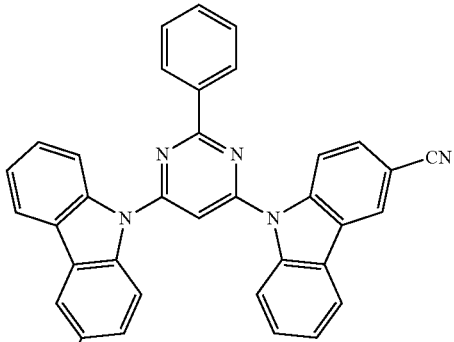
37
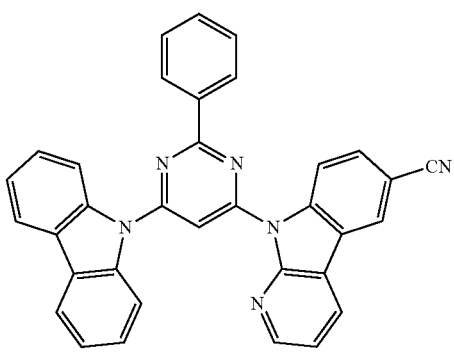
38
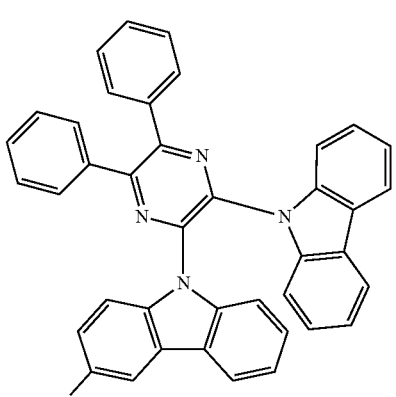
39
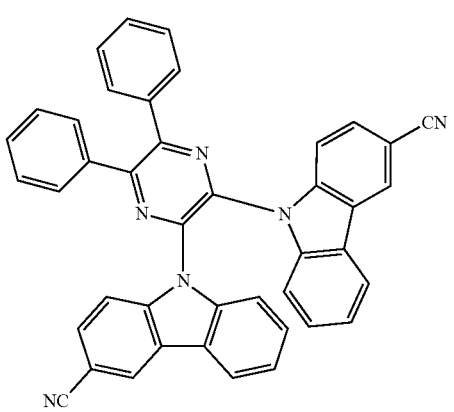

40
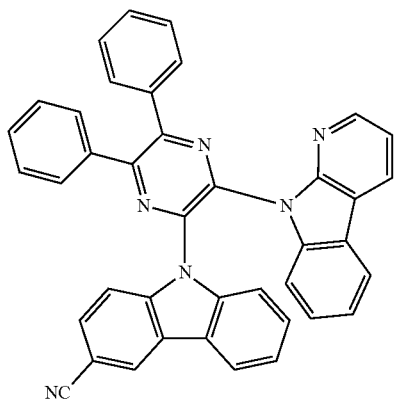
41
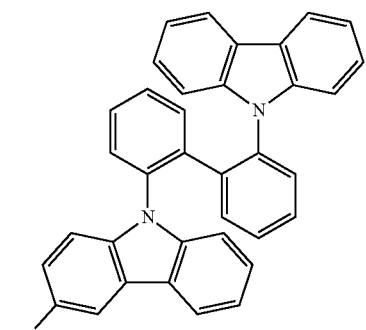
42
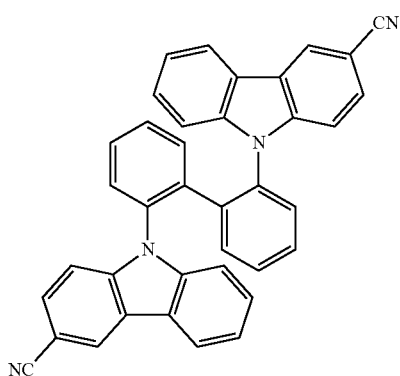
43
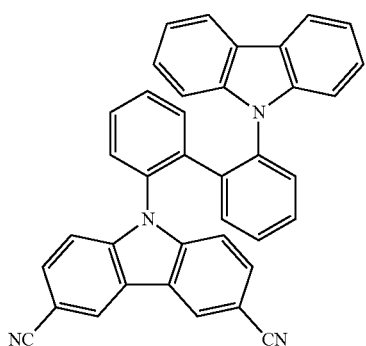
44
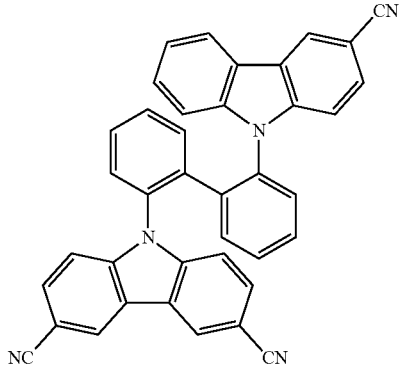
45
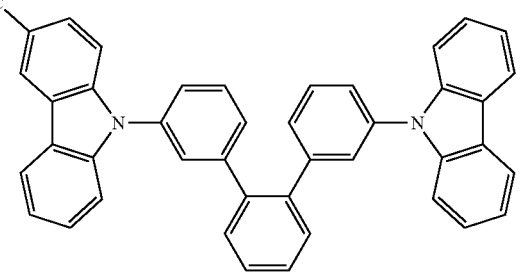
46
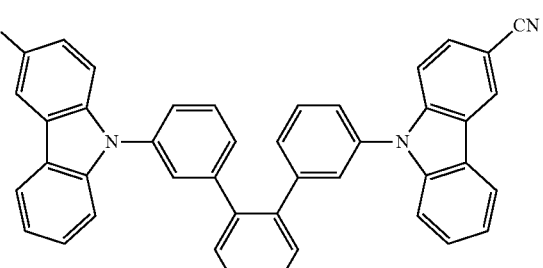
47
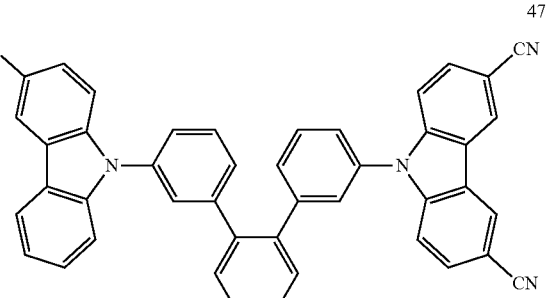
48
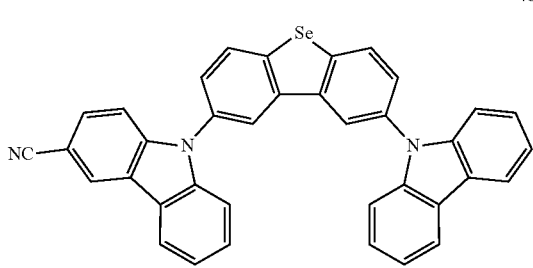

49
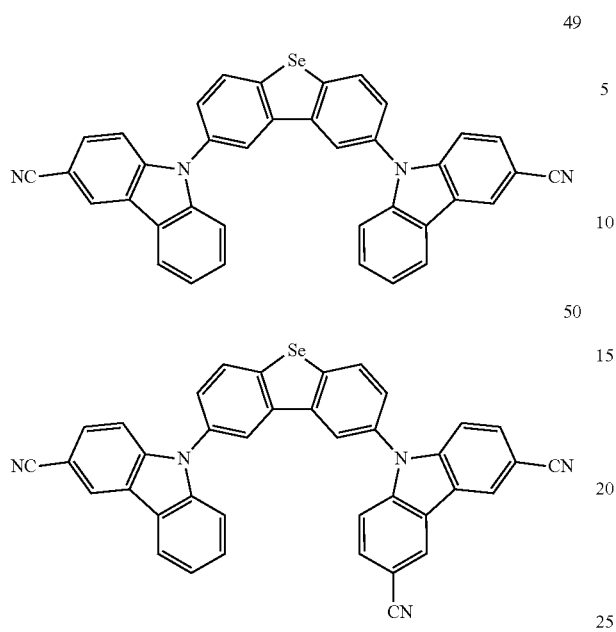
50
51
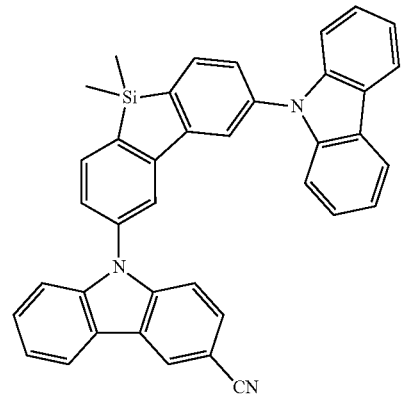
52
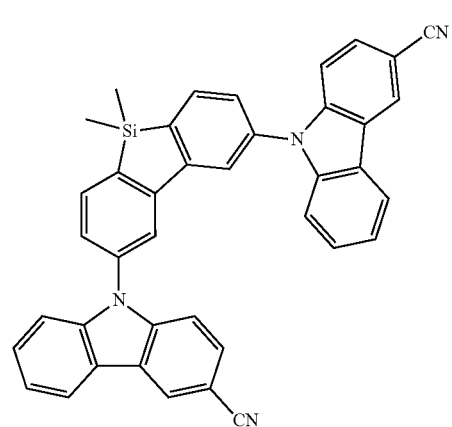
53
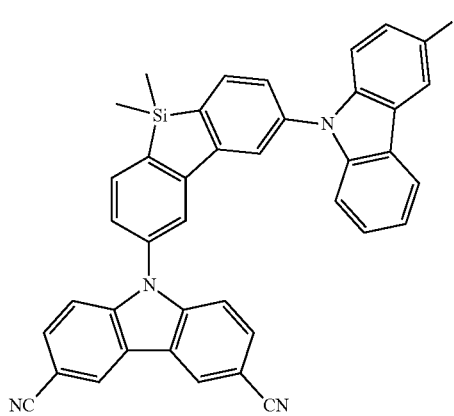
54
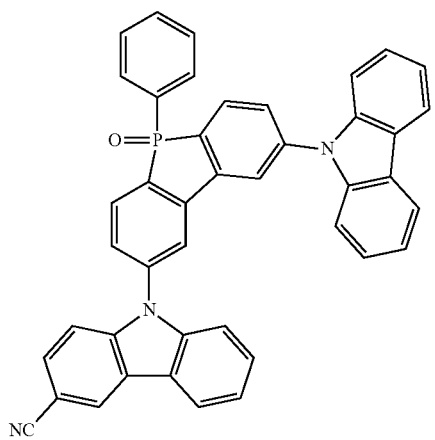
55
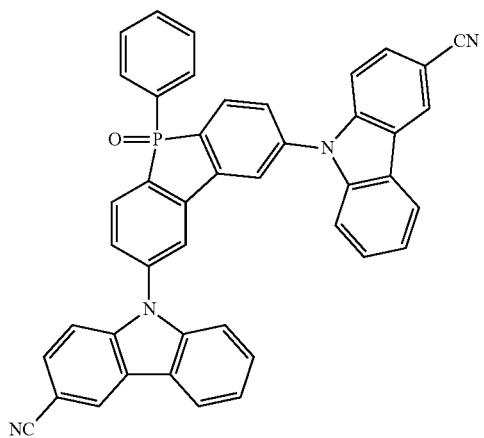

789
-continued
56
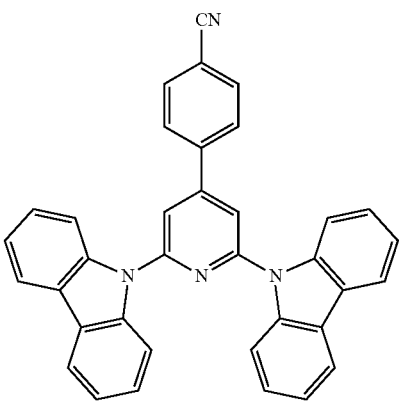
Group HE5
1
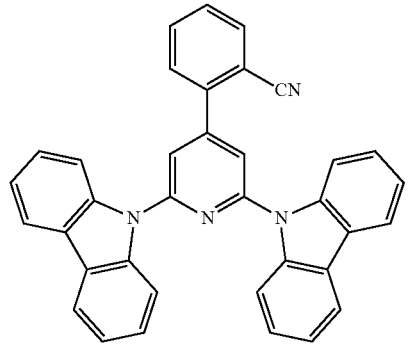
2
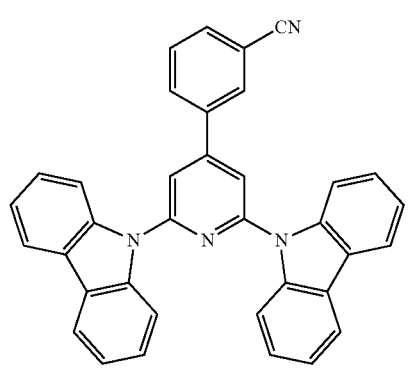
790
-continued
3
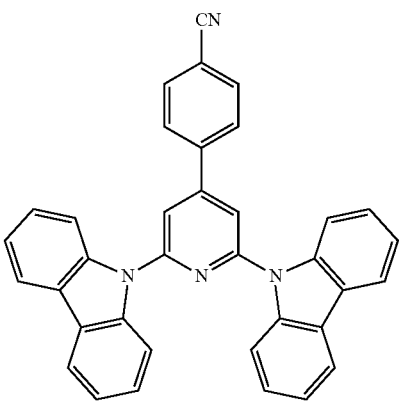
4
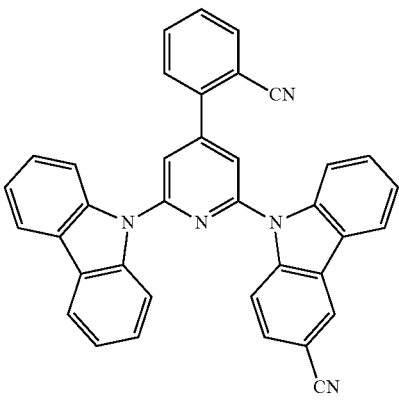
5
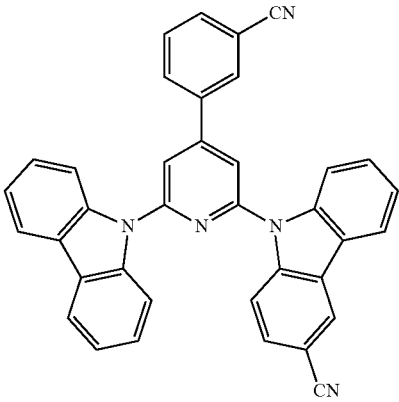
6
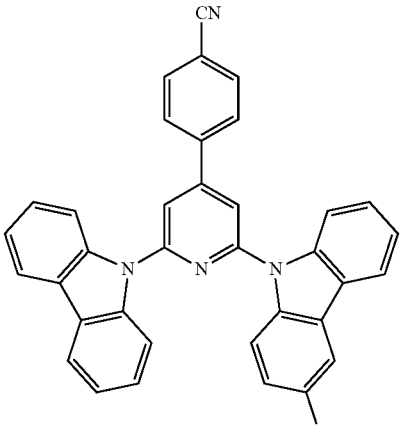

-continued
7
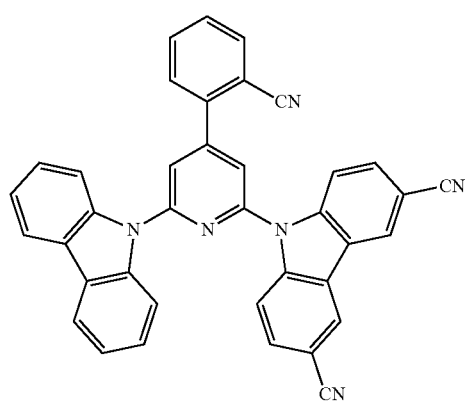
8
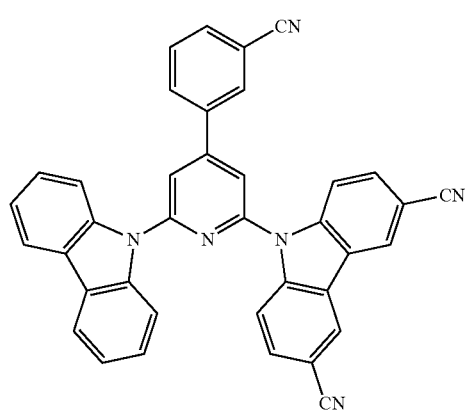
9
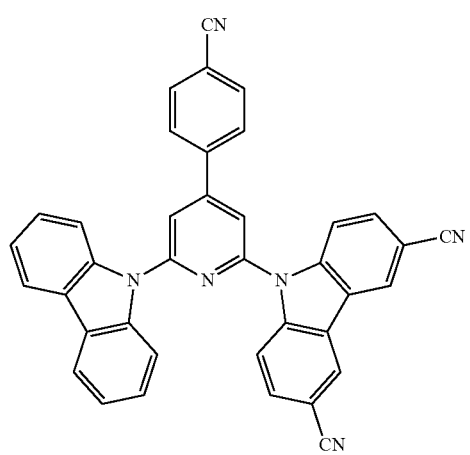
10
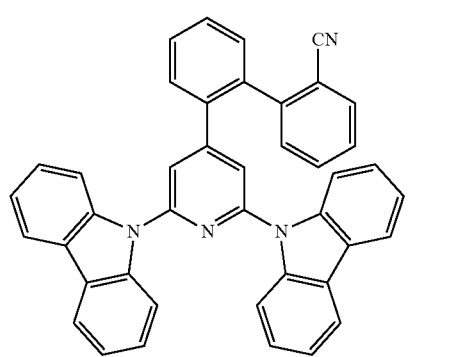
-continued
11
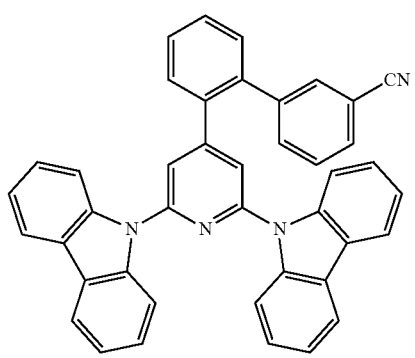
12
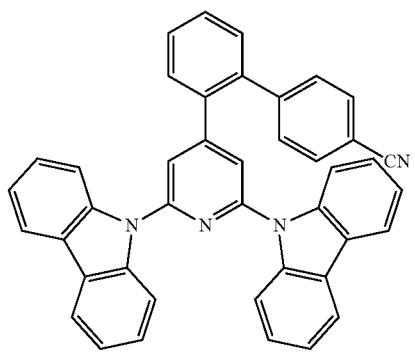
13
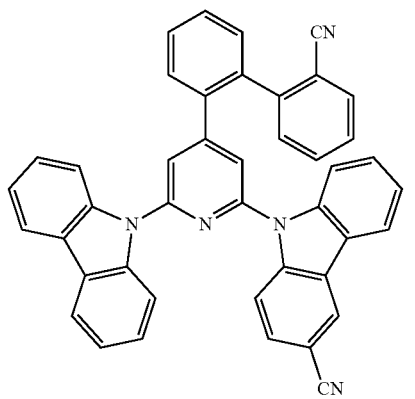
14
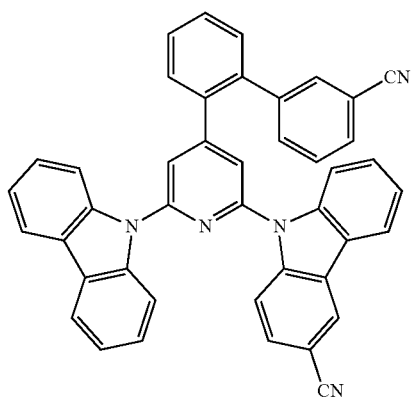

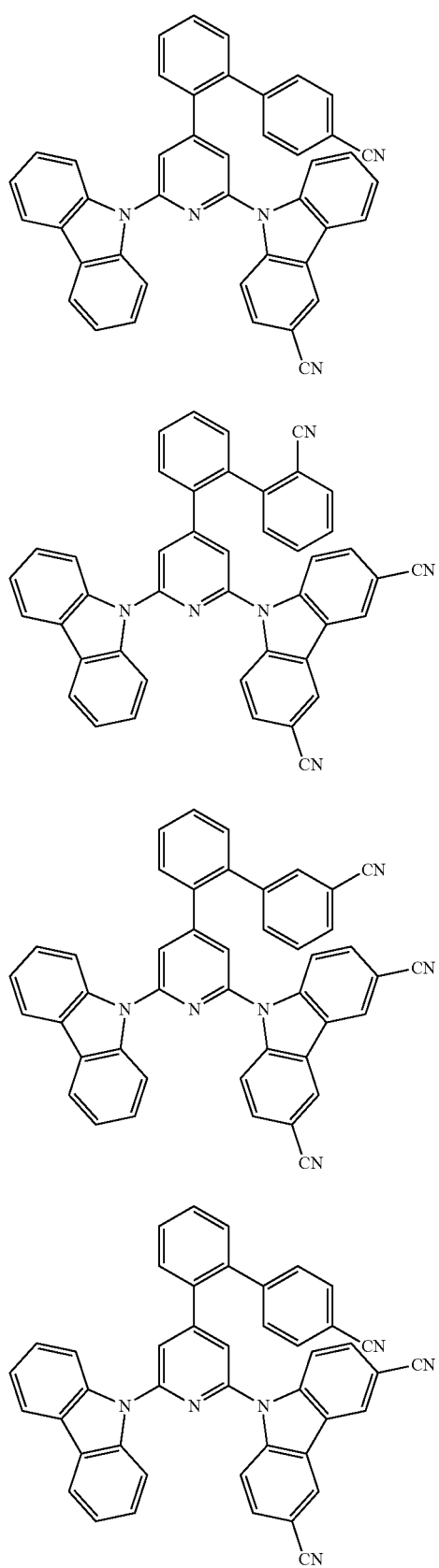
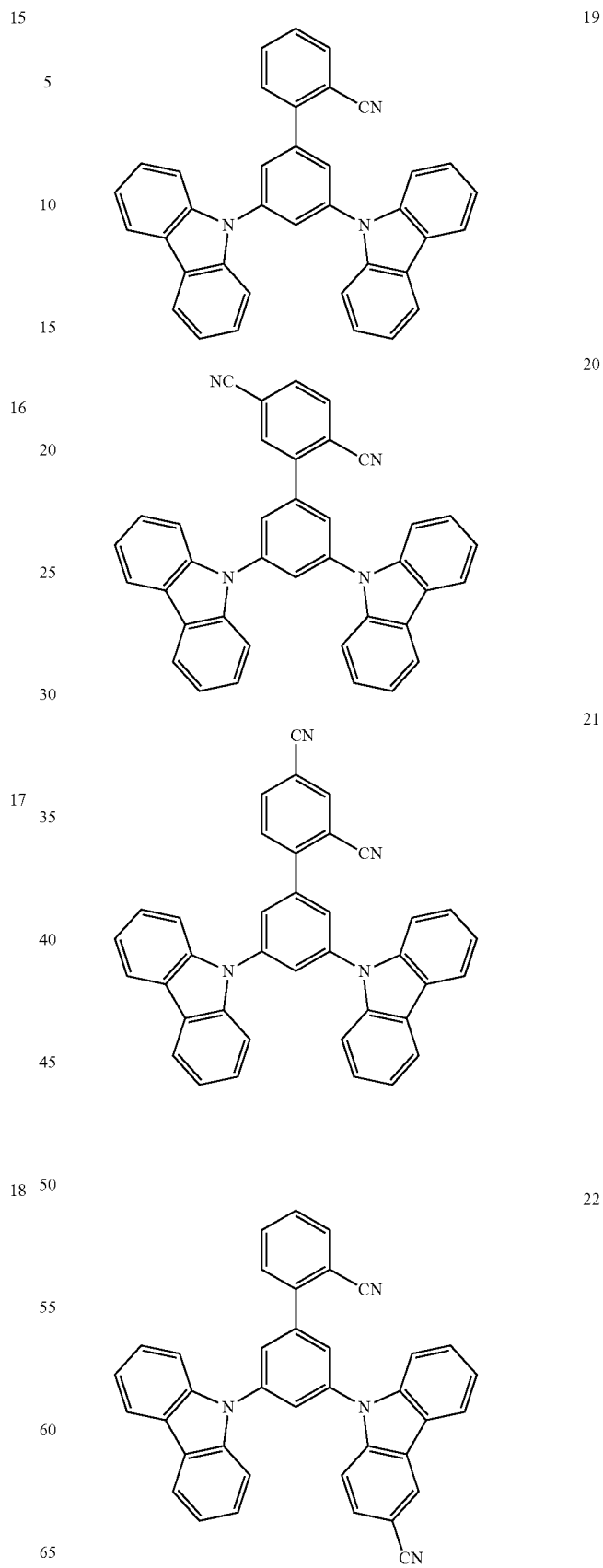

-continued
23
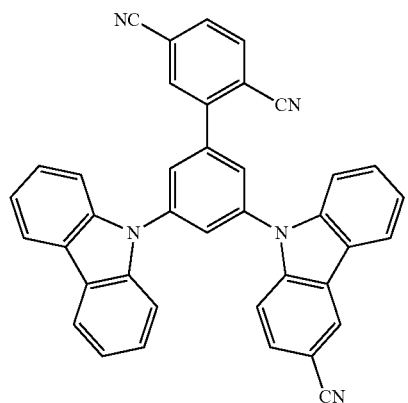
24
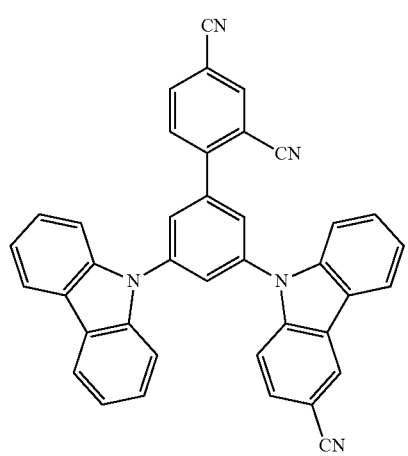
25
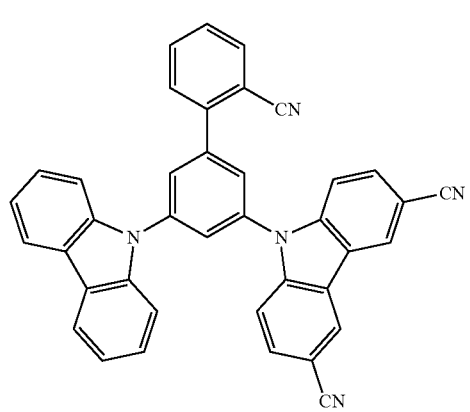
26
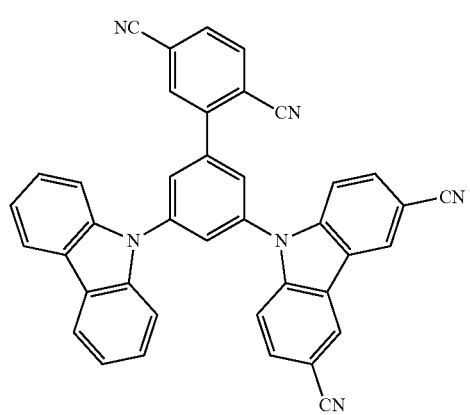
-continued
27
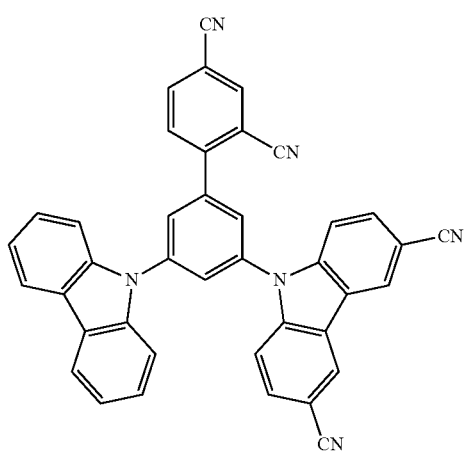
28
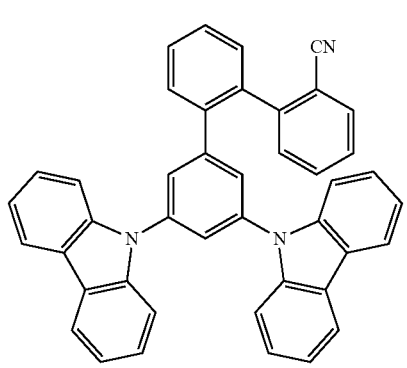
29
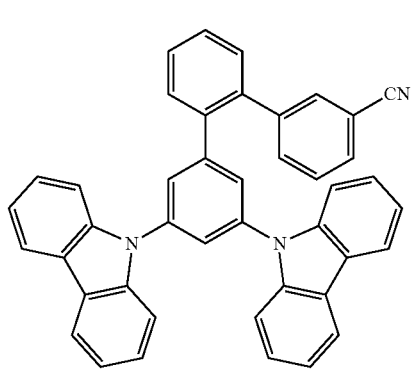
30
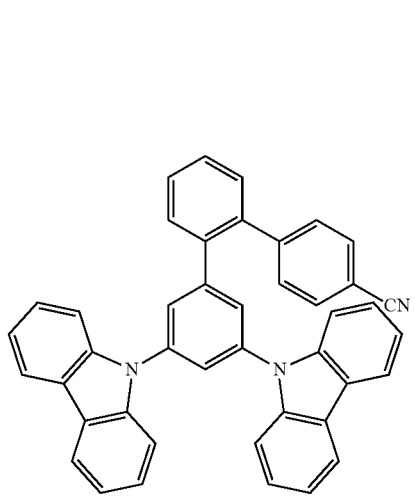

31
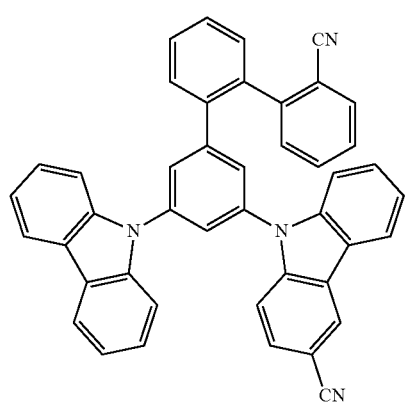
32
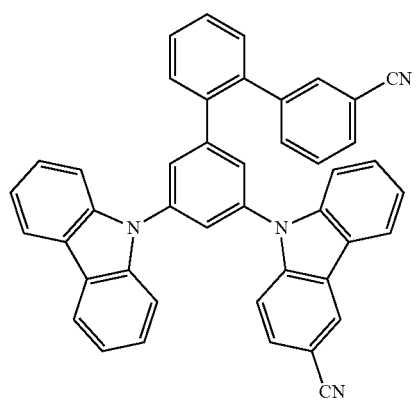
33
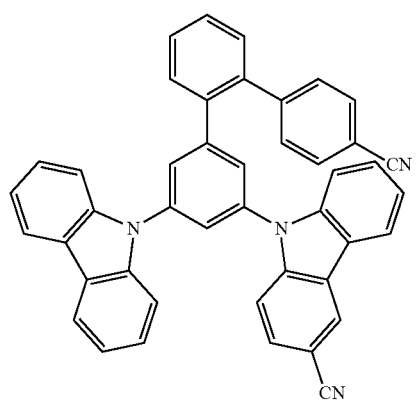
34
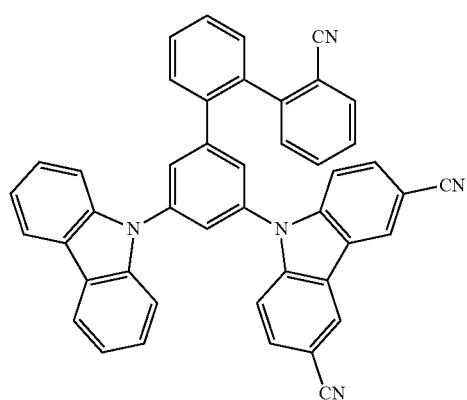
35
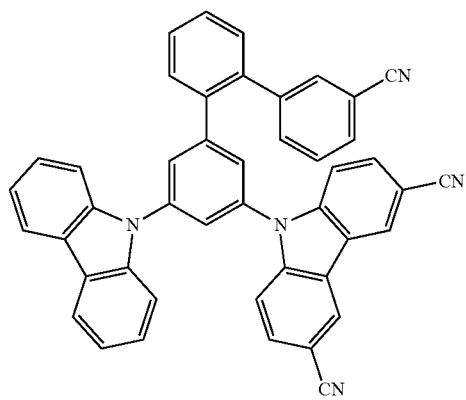
36
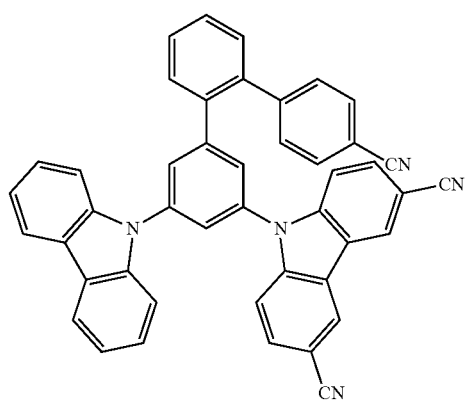
37
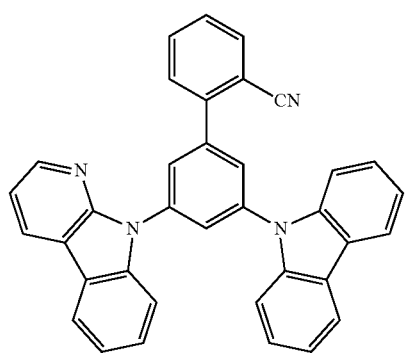
38
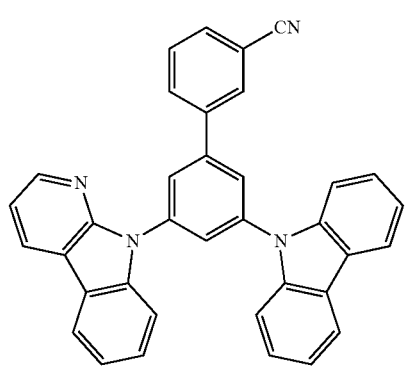

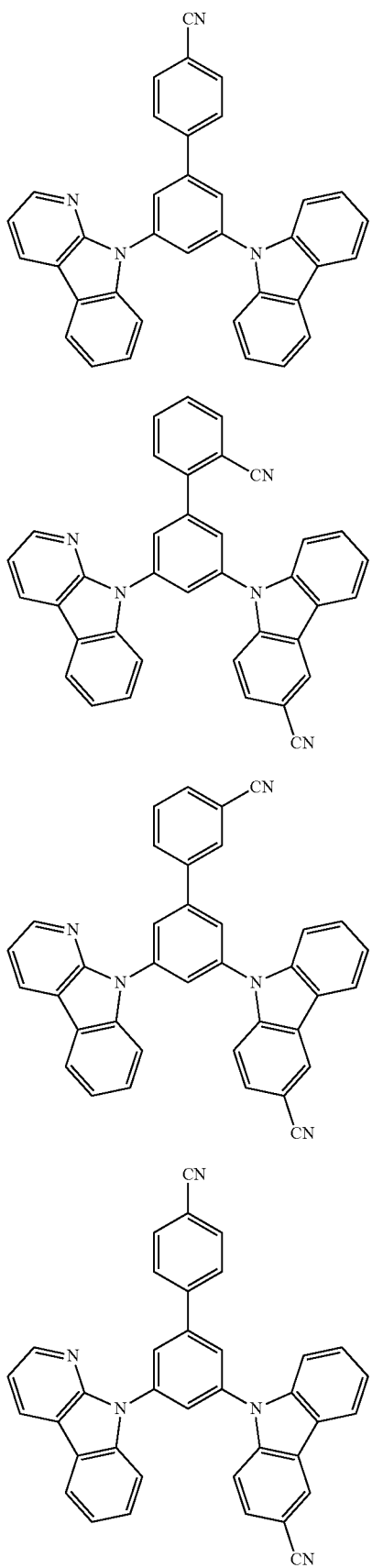
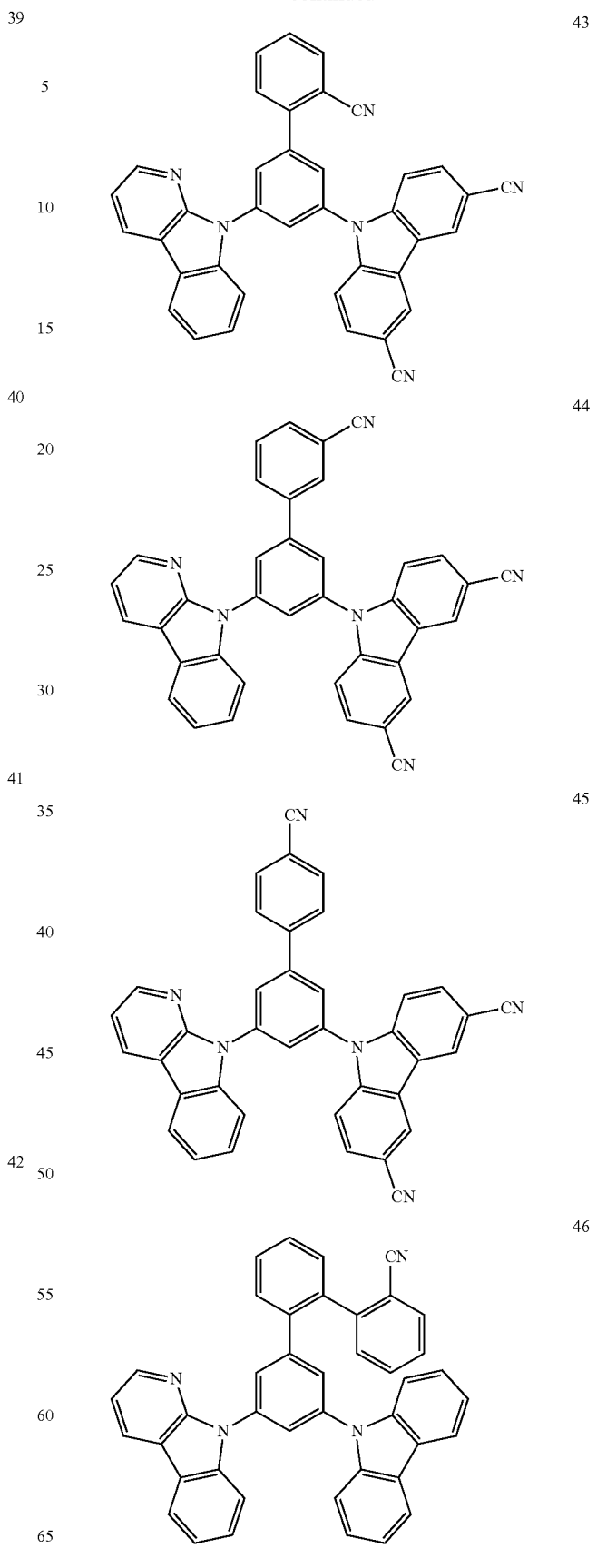

-continued
47
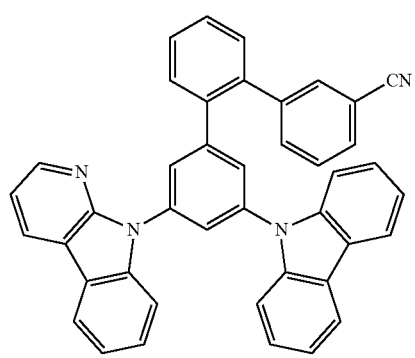
48
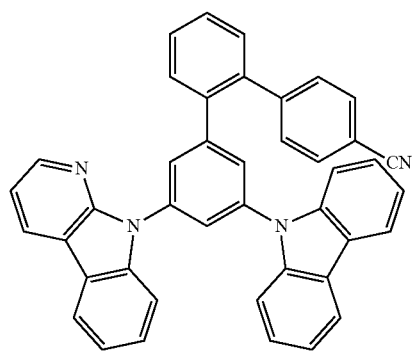
49
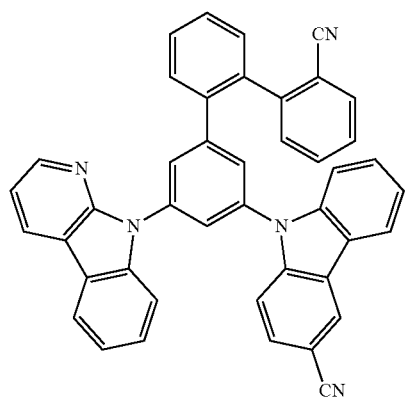
50
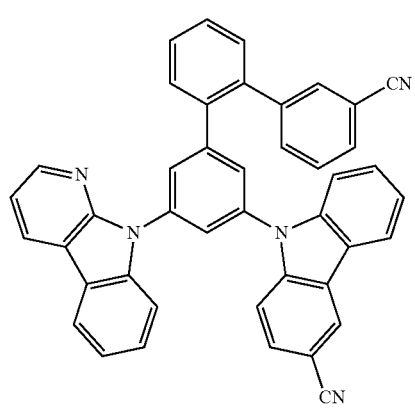
-continued
51
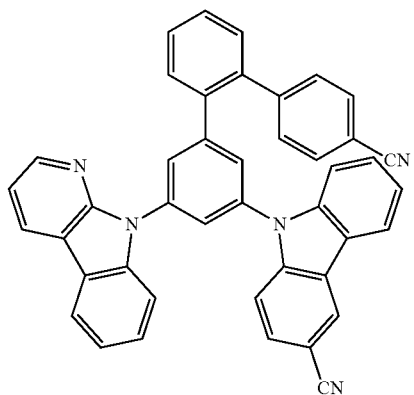
52
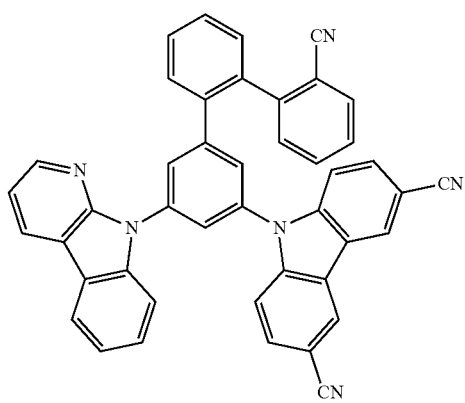
53
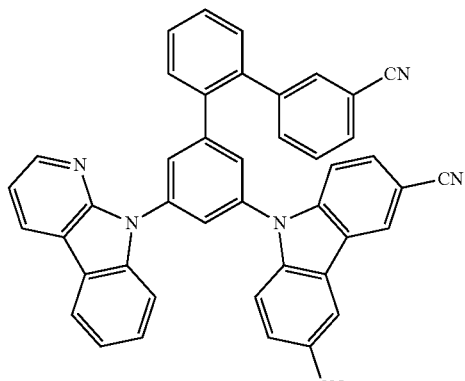
54
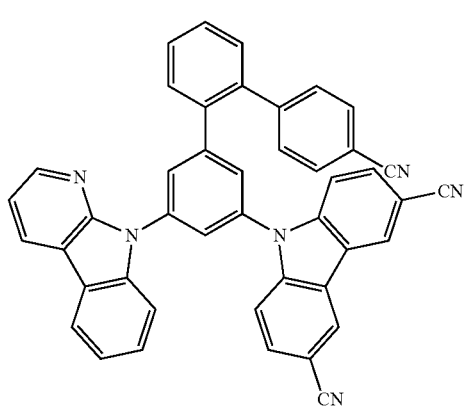

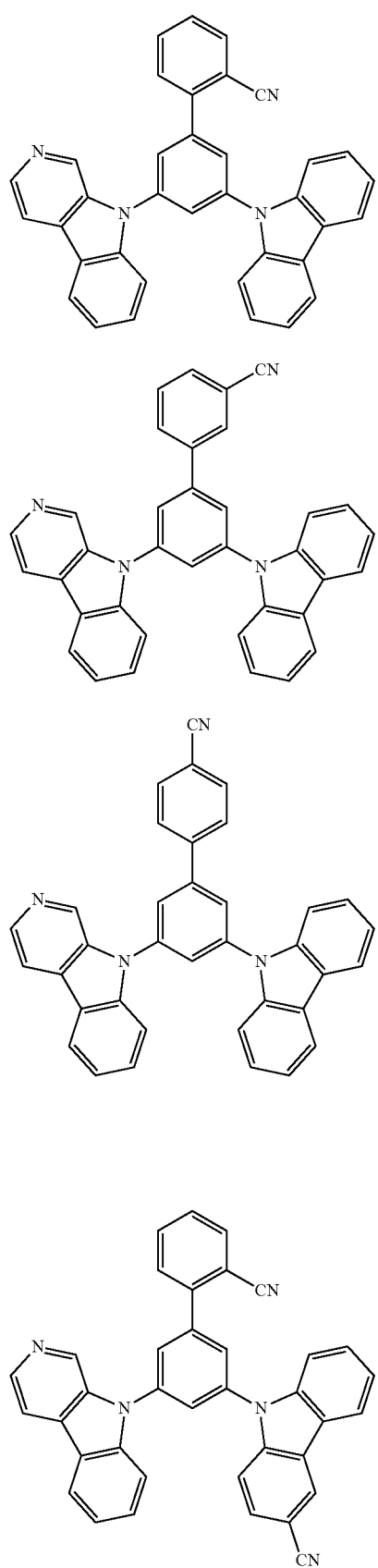
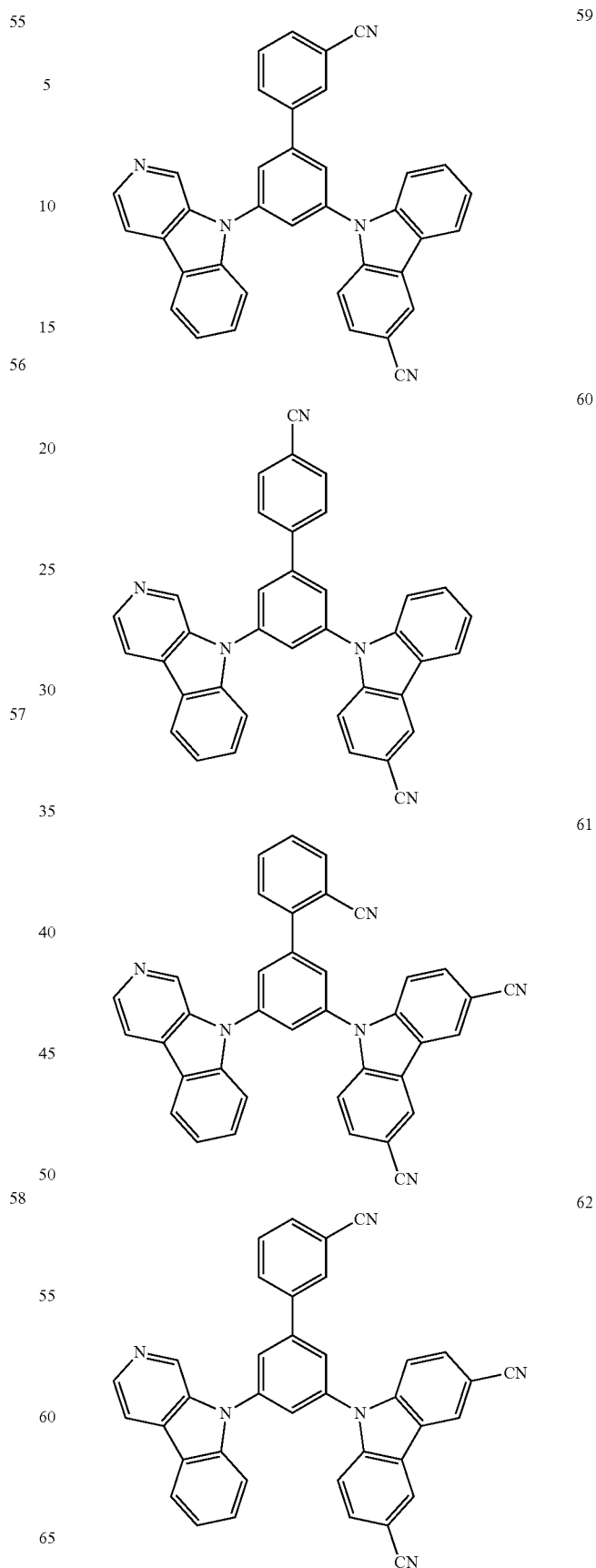

805
-continued
63
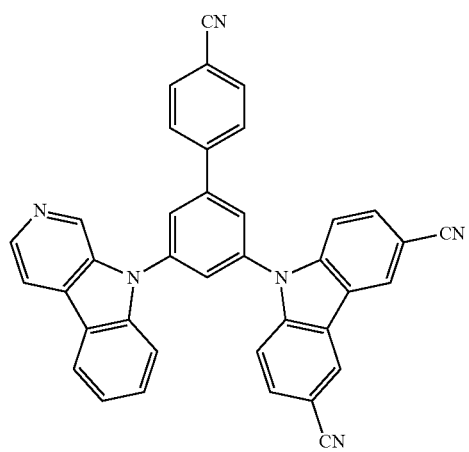
64
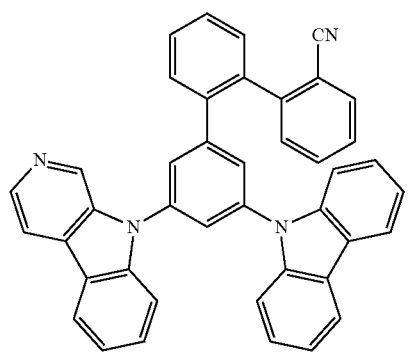
65
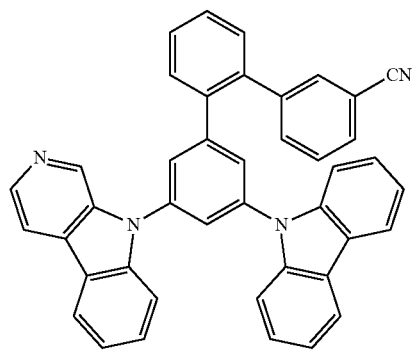
66
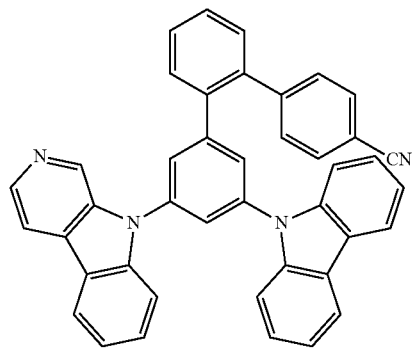
806
-continued
67
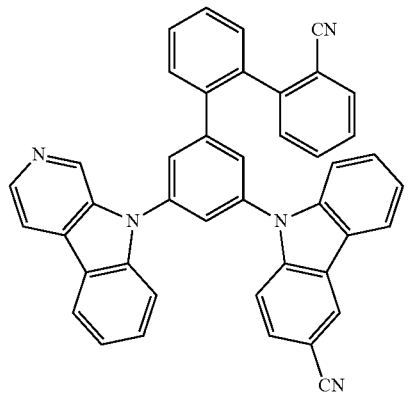
68
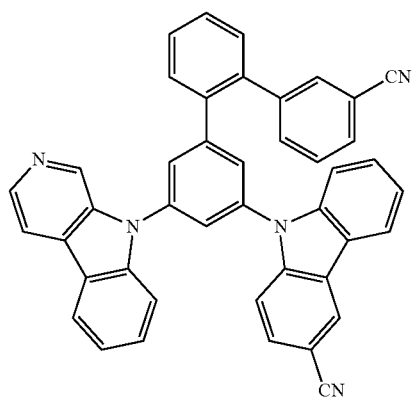
69
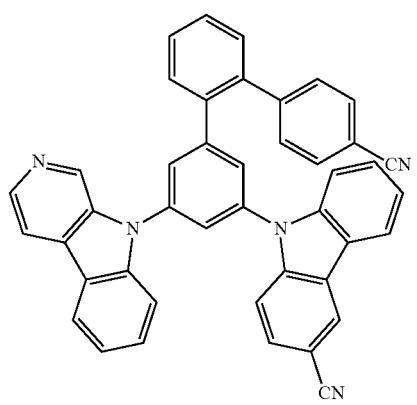
70
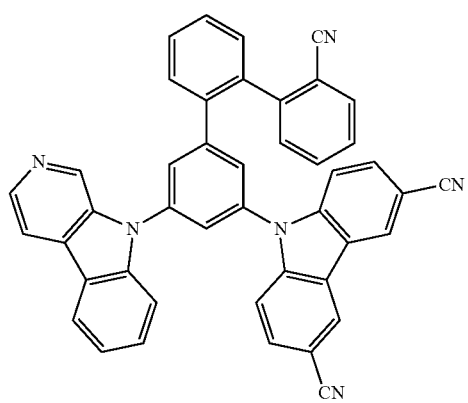

| 71 | 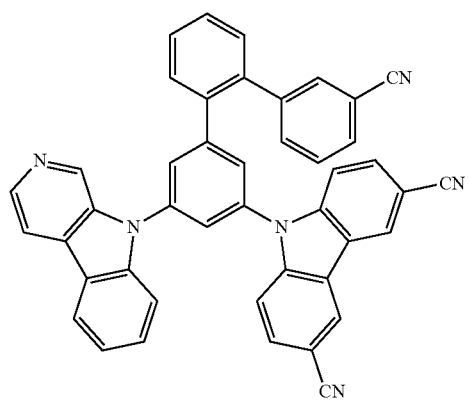 |
| --- | --- |
| 72 | 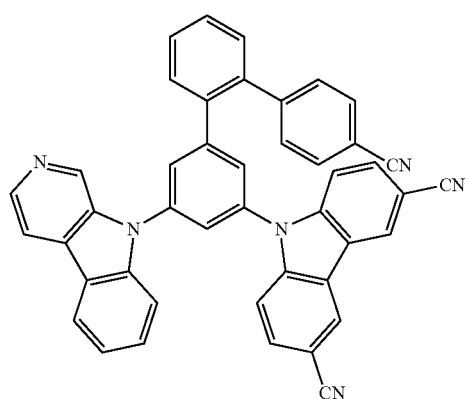 |
| 73 | 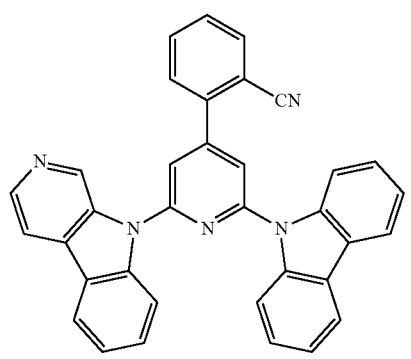 |
| 74 | 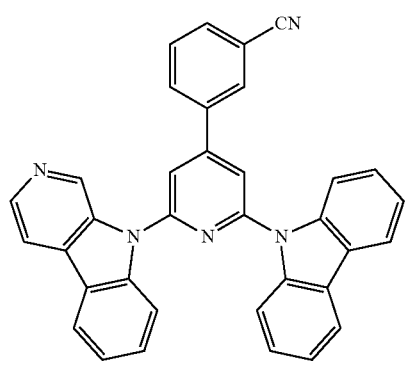 |
| 75 | 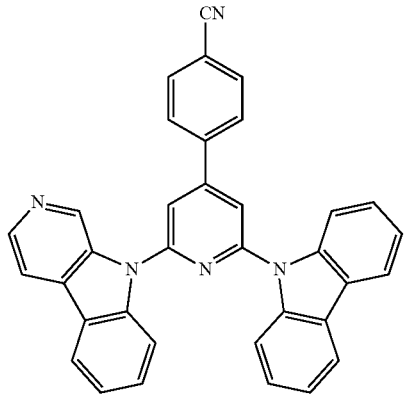 |
| 76 | 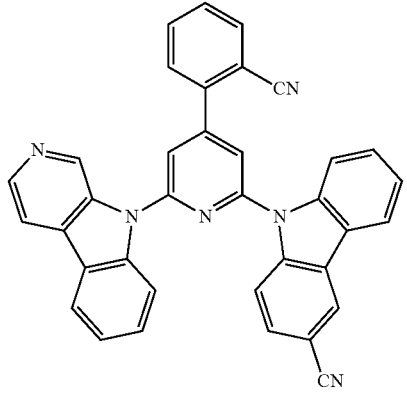 |
| 77 | 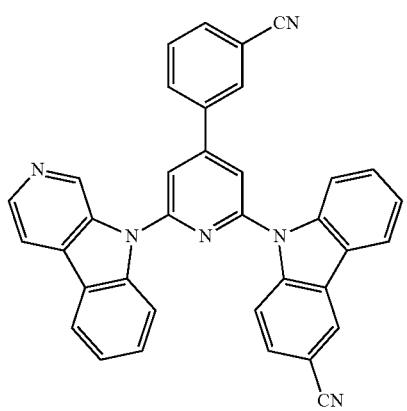 |
| 78 | 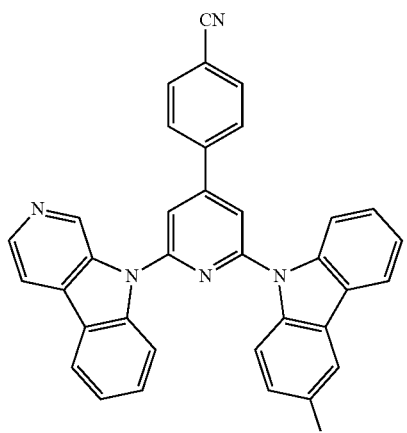 |

809
-continued
79
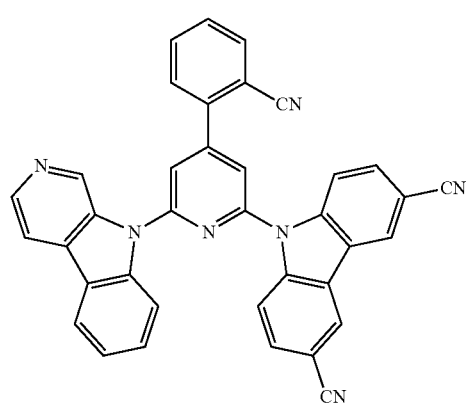
80
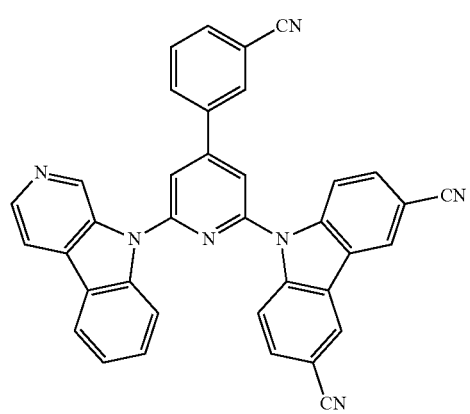
81
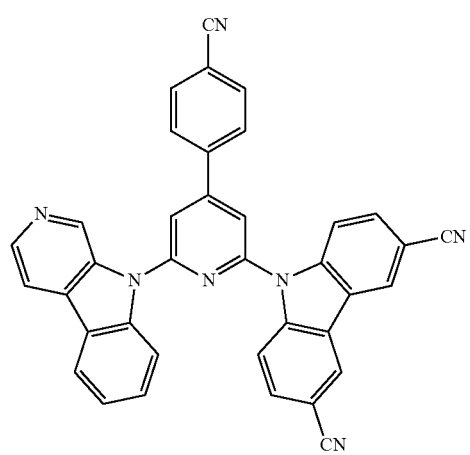
82
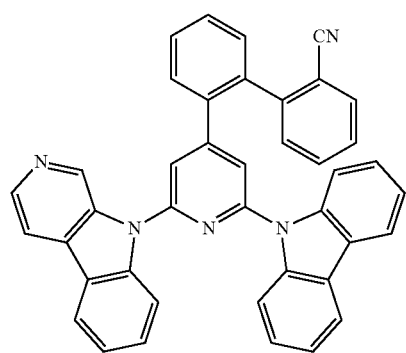
810
-continued
83
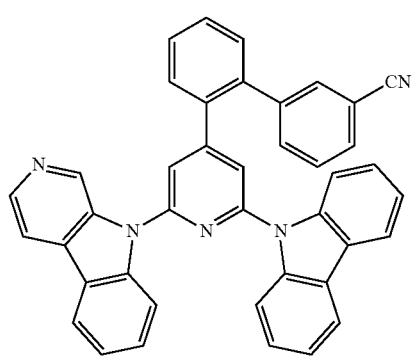
84

85
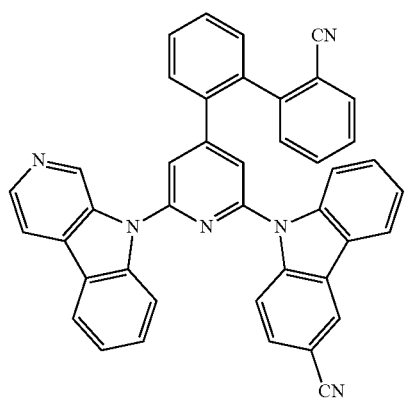
86
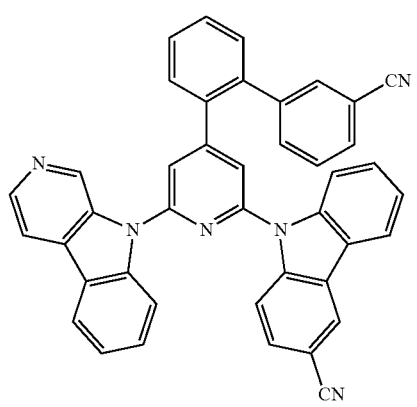

811
-continued
87
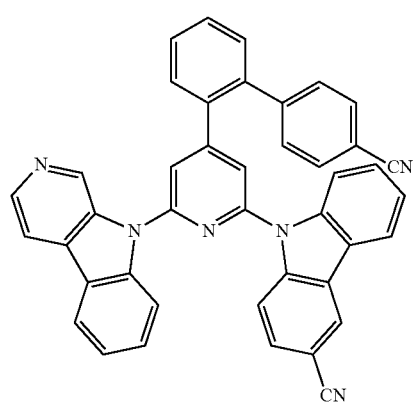
88
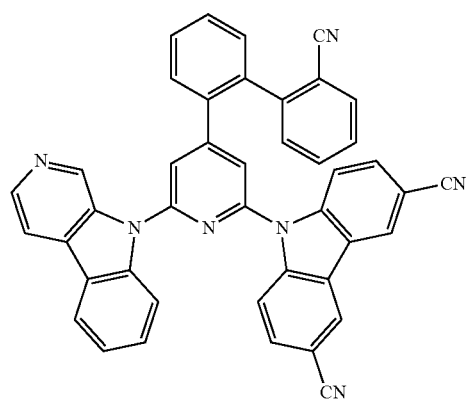
89
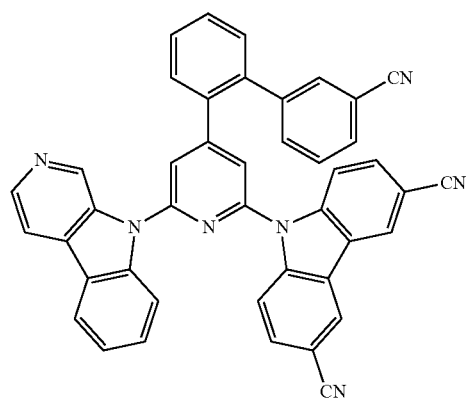
90
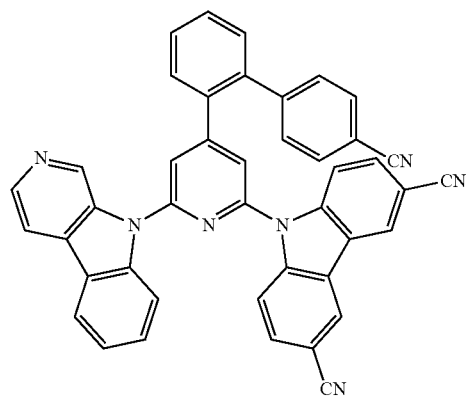
812
-continued
91
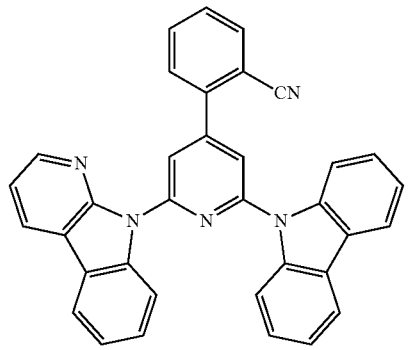
92
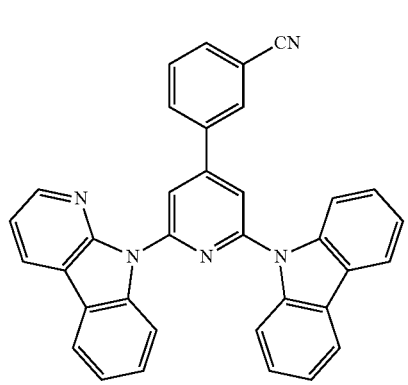
93
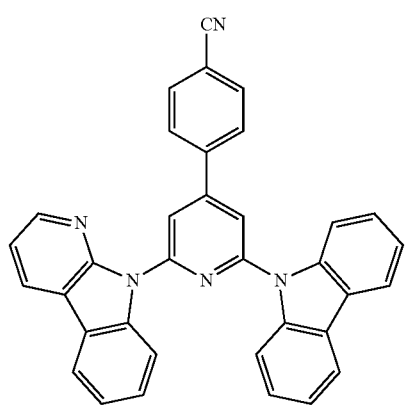
94
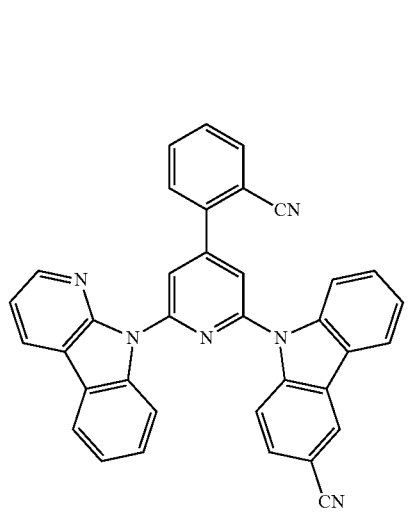

95
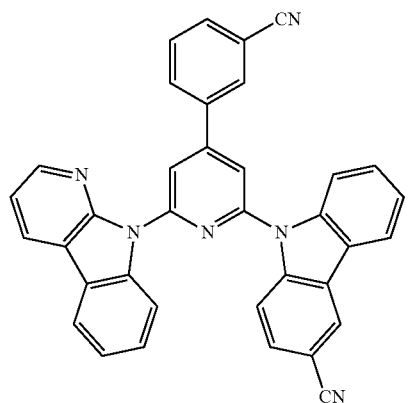
96
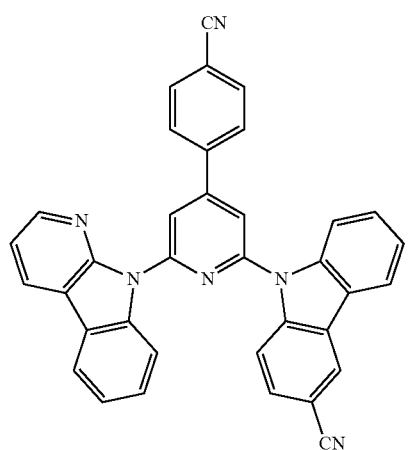
97
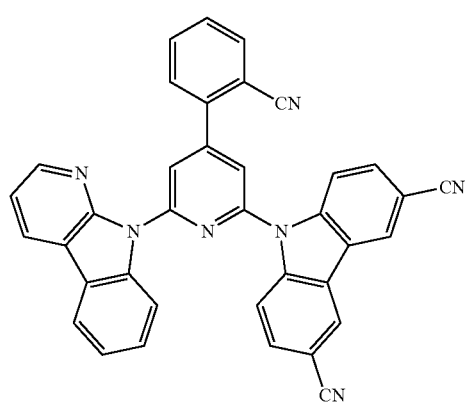
98
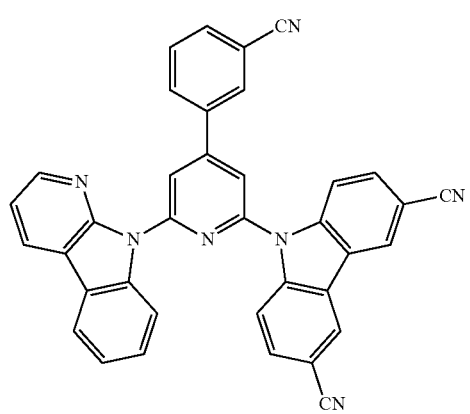
99
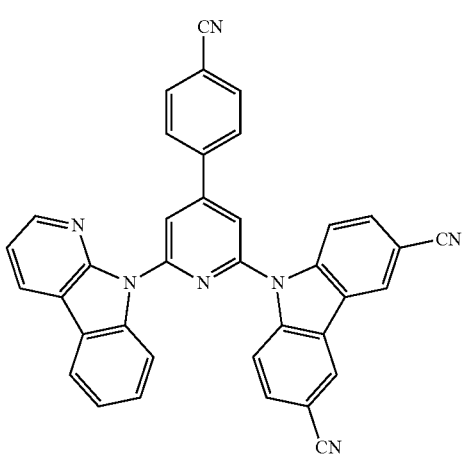
100
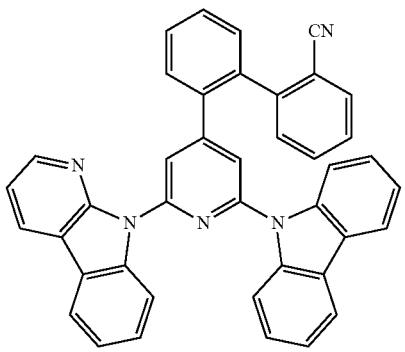
101
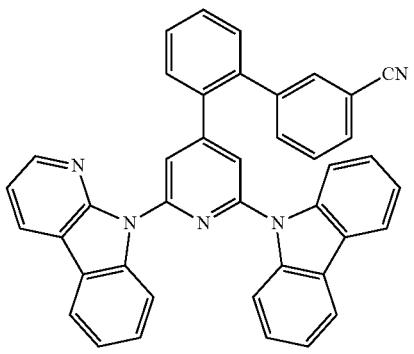
102
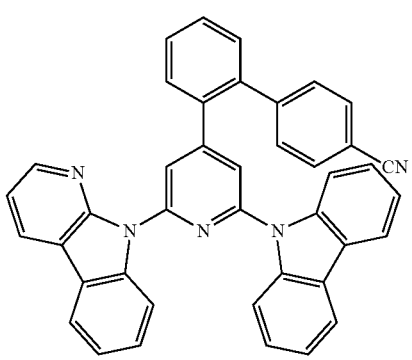

-continued
103
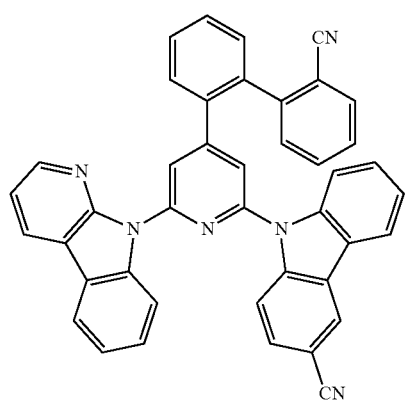
104
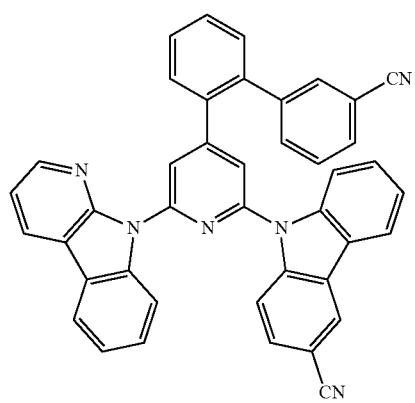
105
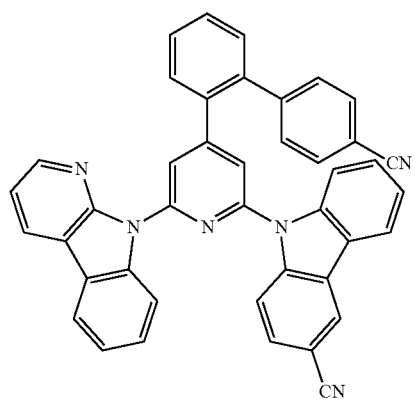
106
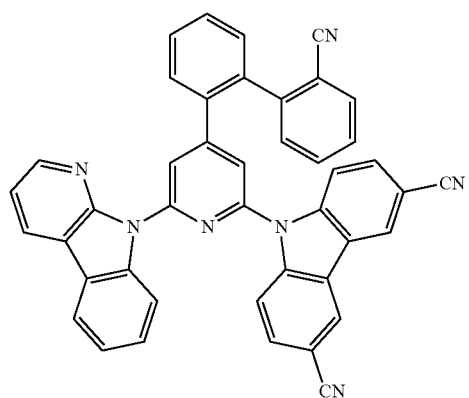
-continued
107
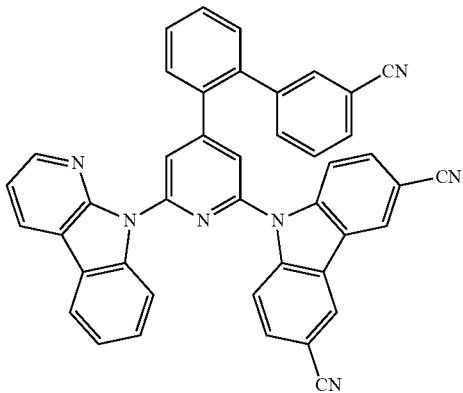
108
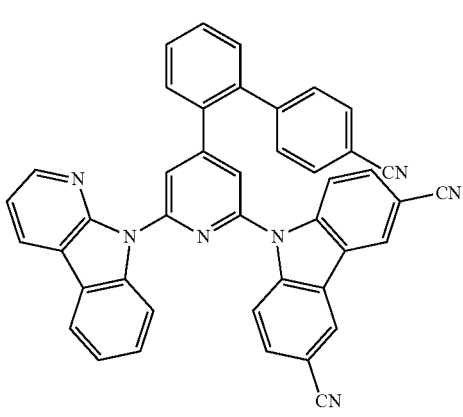
109
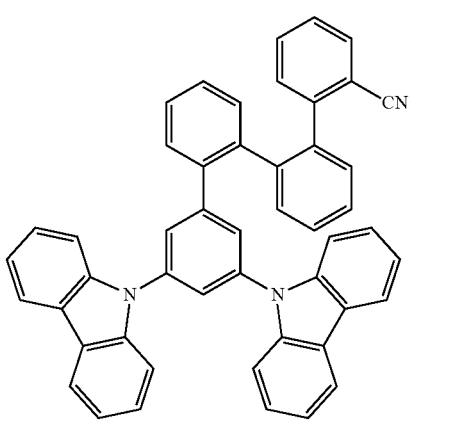
110
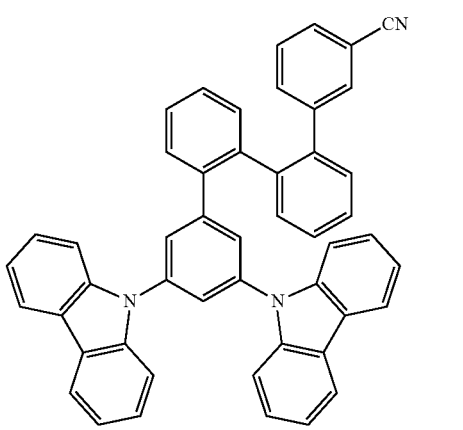

-continued
111
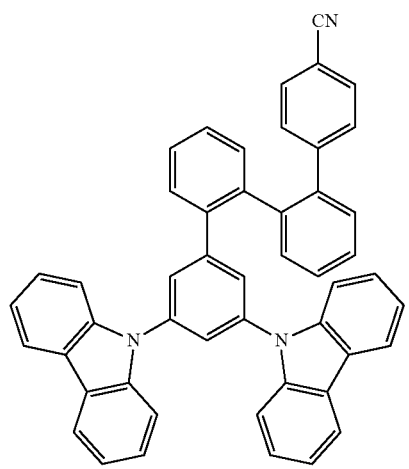
112
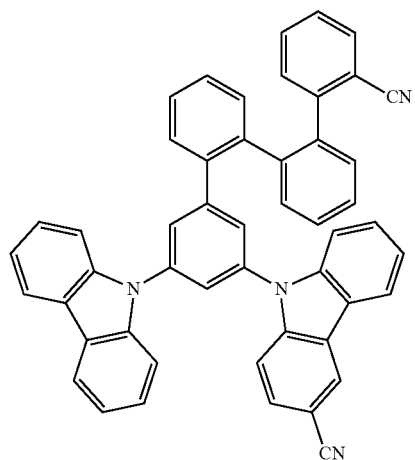
113
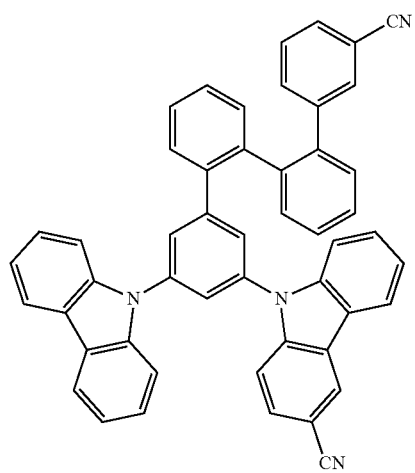
-continued
114
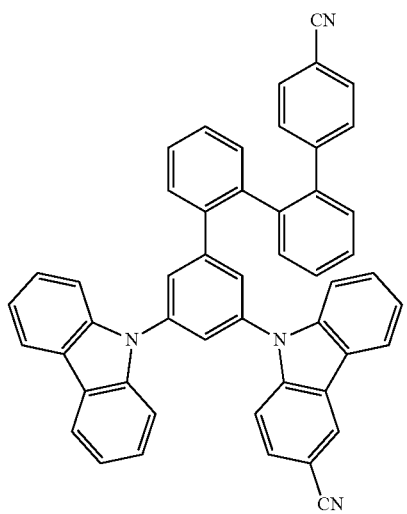
115
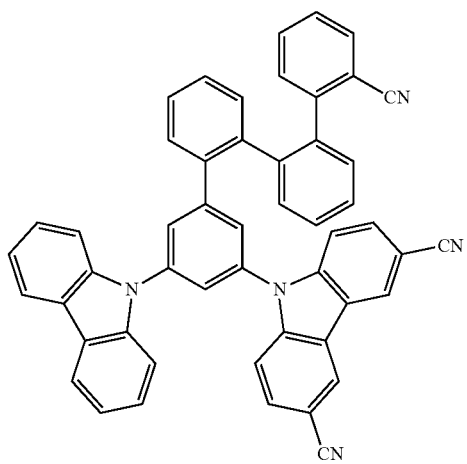
116
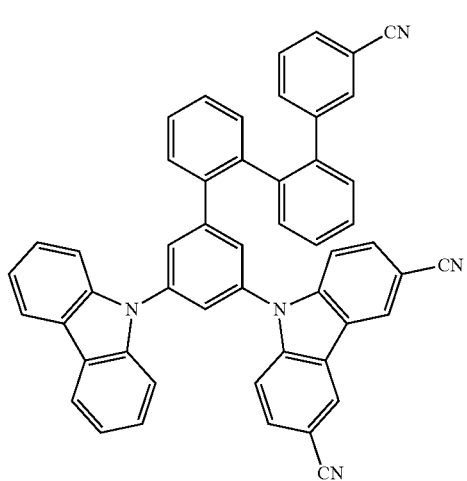

-continued
117
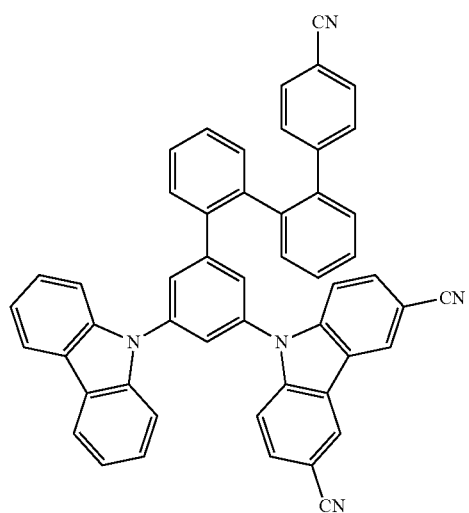
118
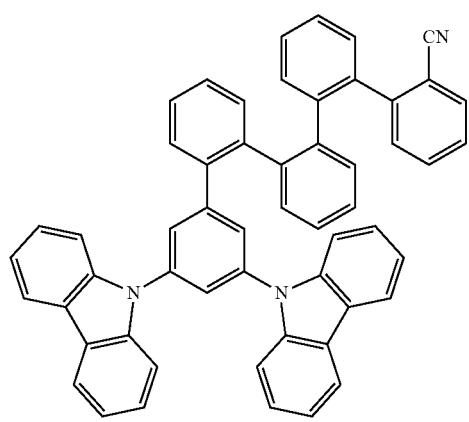
119
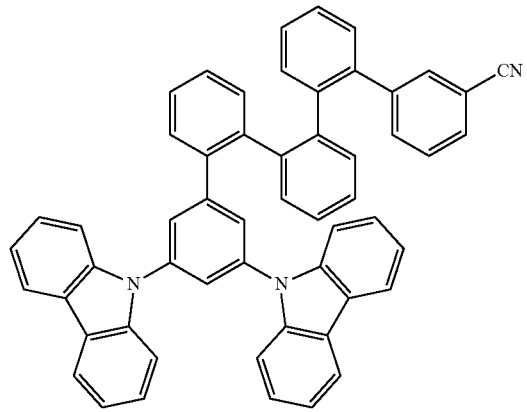
-continued
120
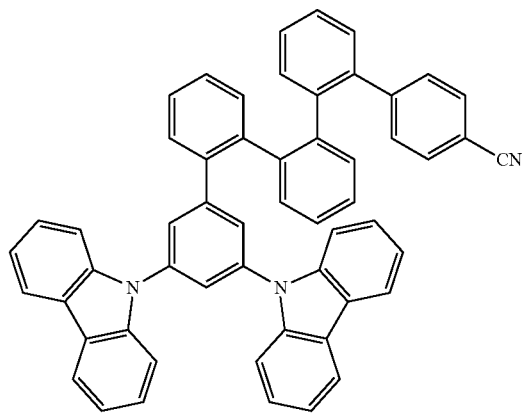
121
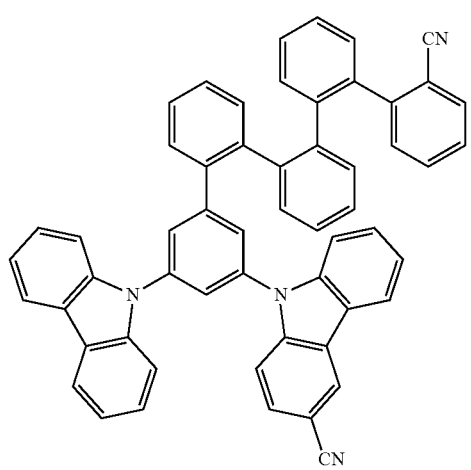
122
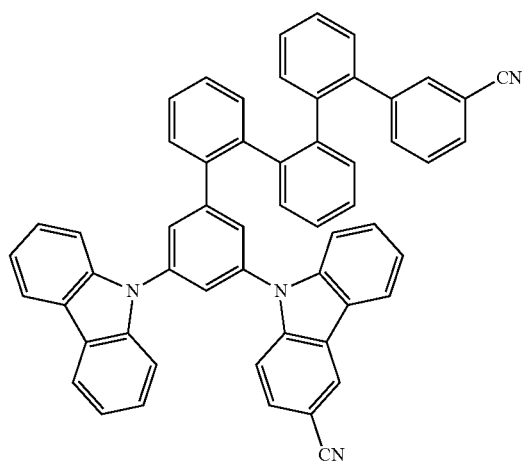

123
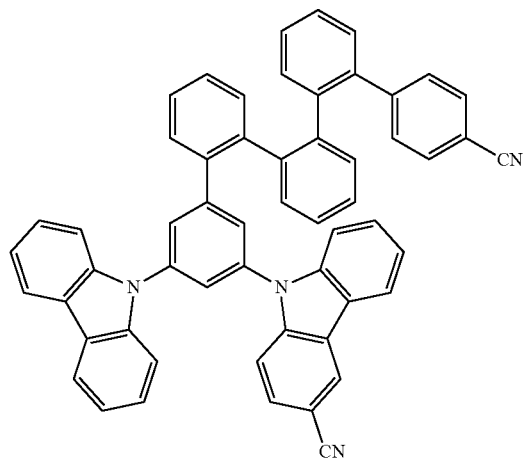
124
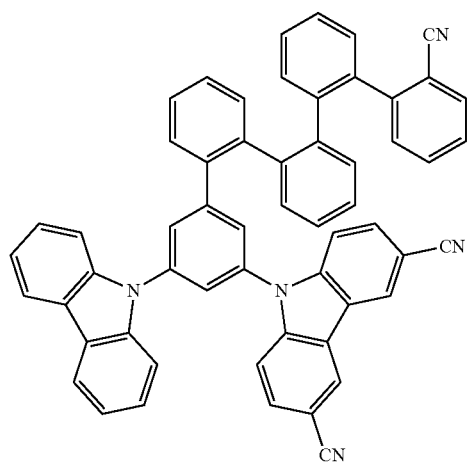
125
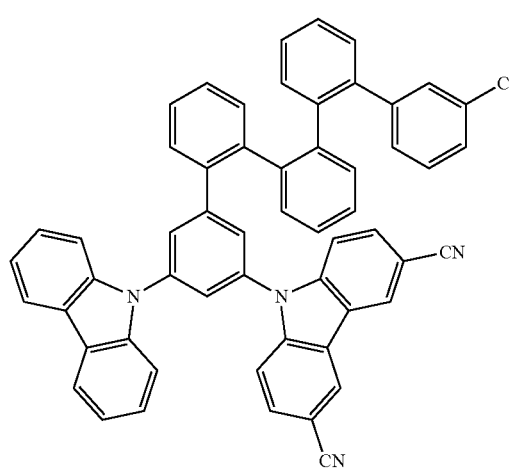
126
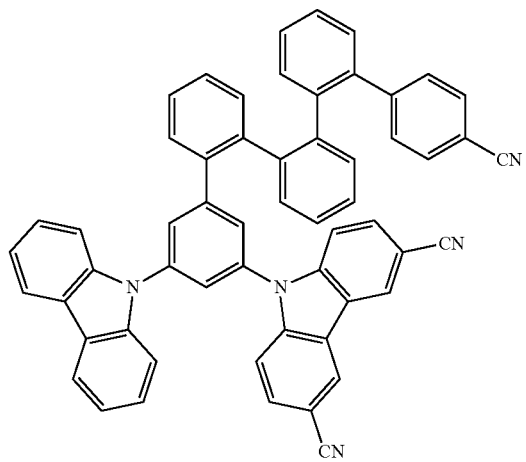
127
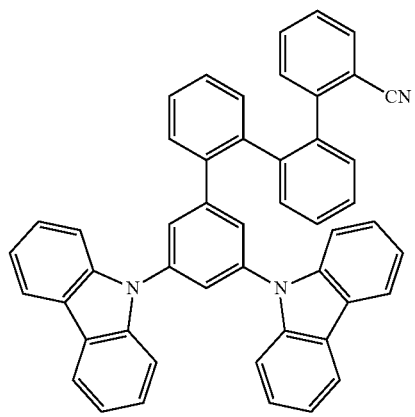
128
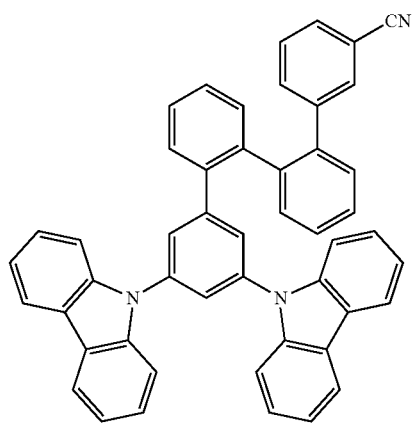

-continued
129
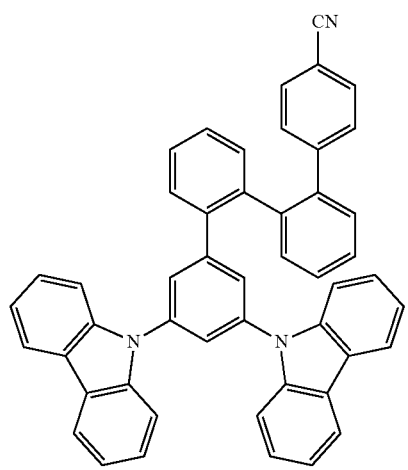
130
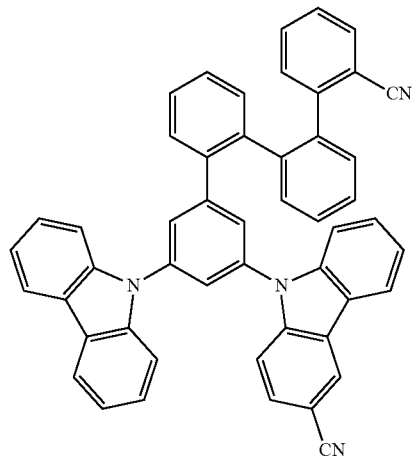
131
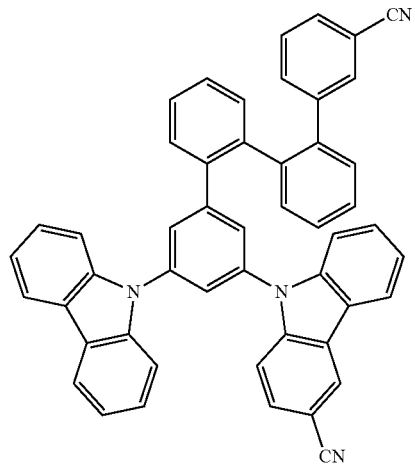
-continued
132
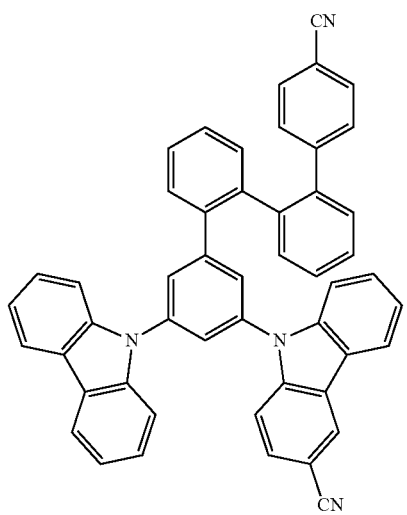
133
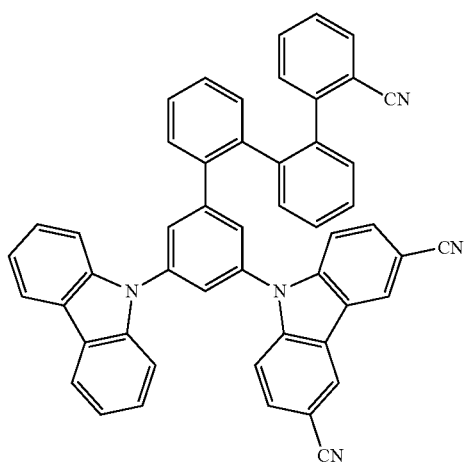
134
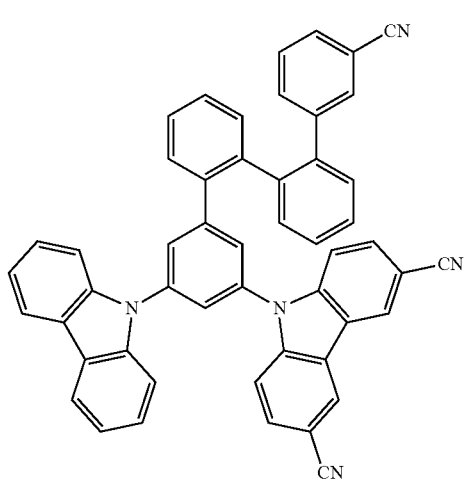

-continued
135
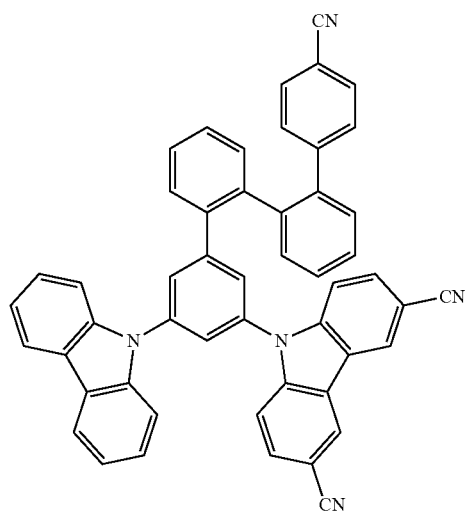
136
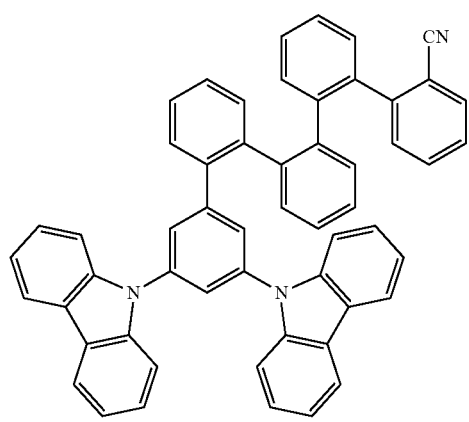
137
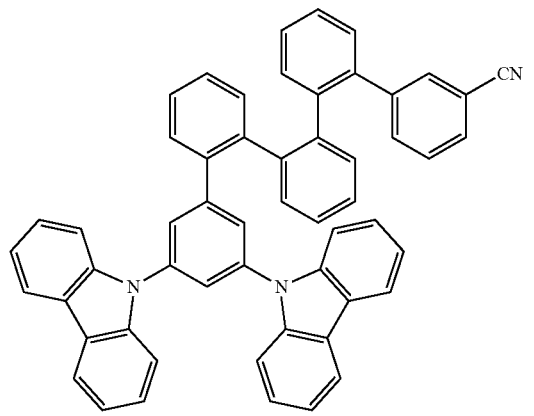
-continued
138
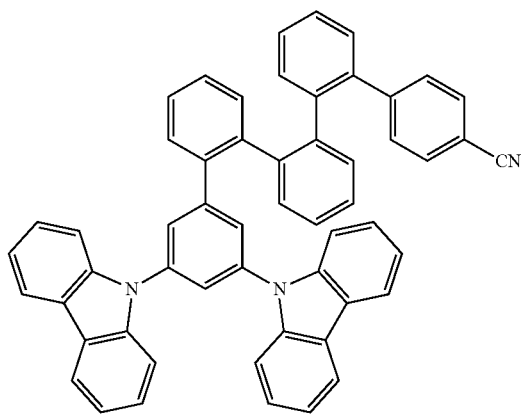
139
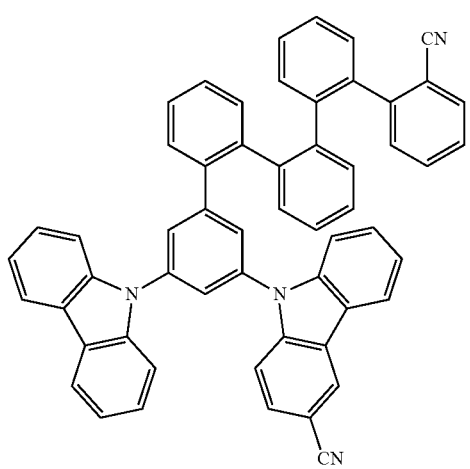
140
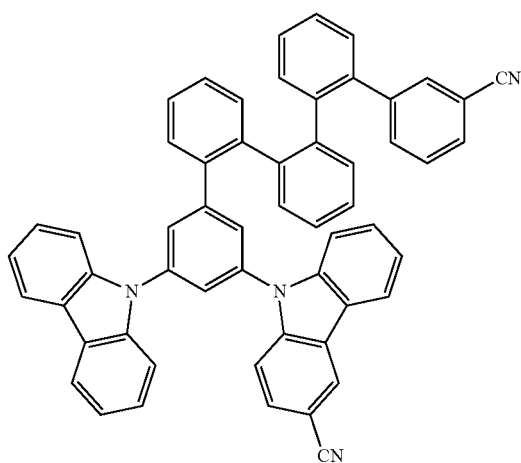

141
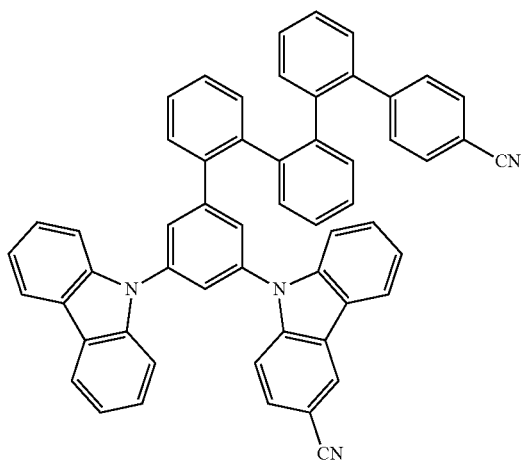
144
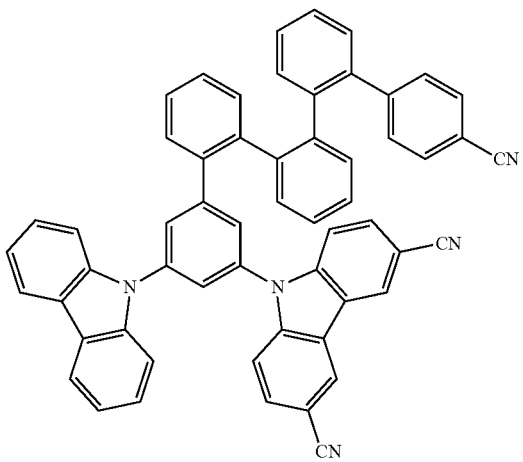
142
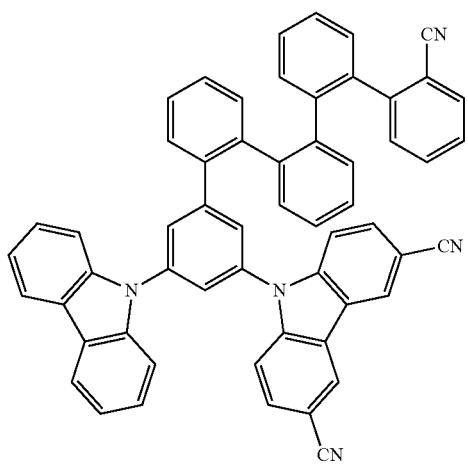
145
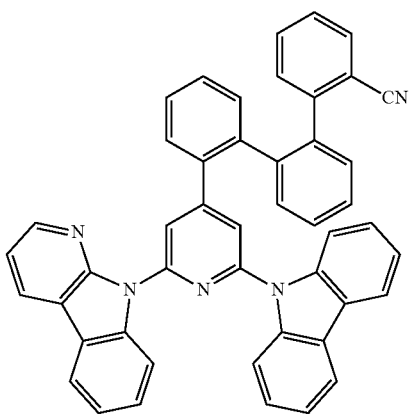
143
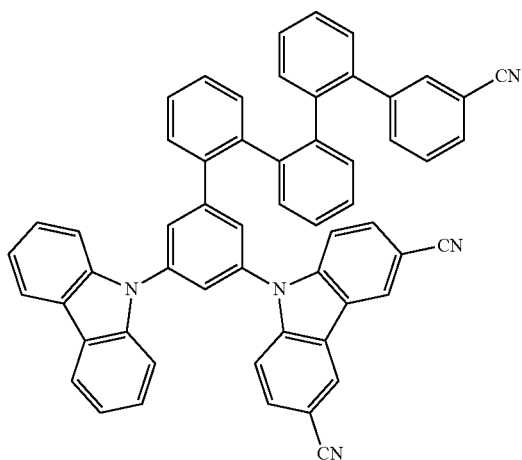
146
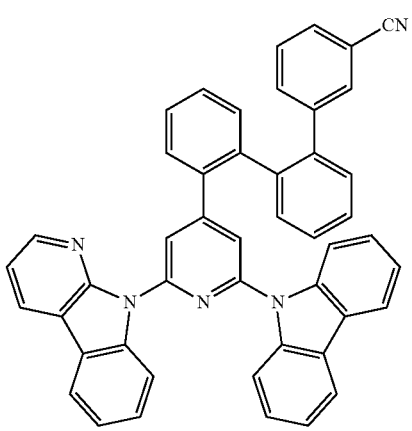

829
-continued
147
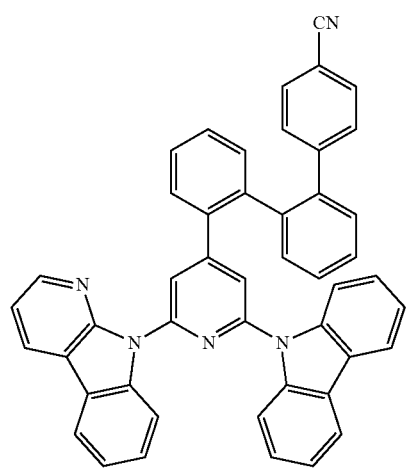
148
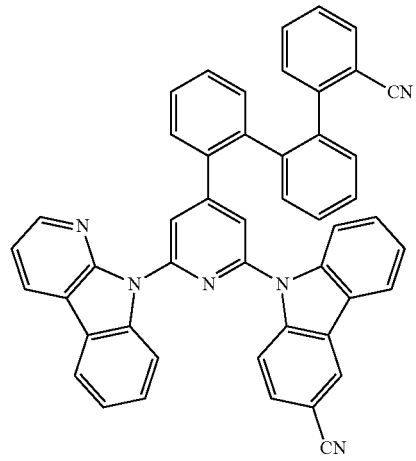
149
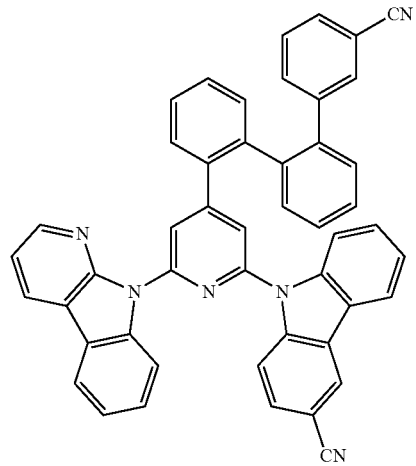
830
-continued
150
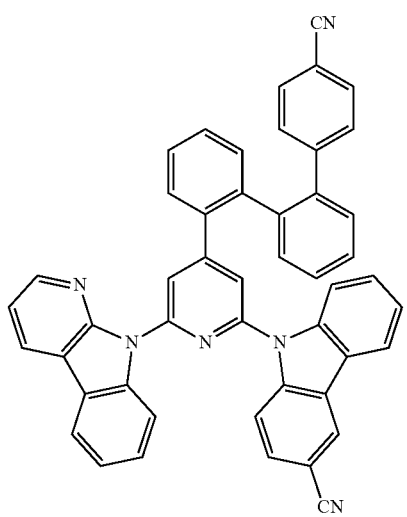
151
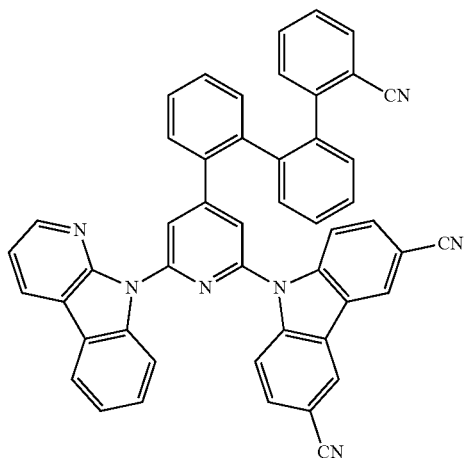
152
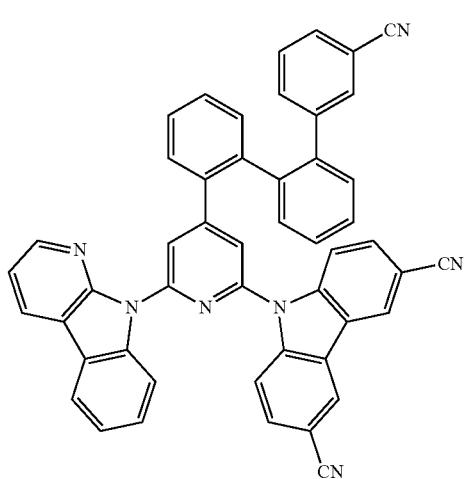

153
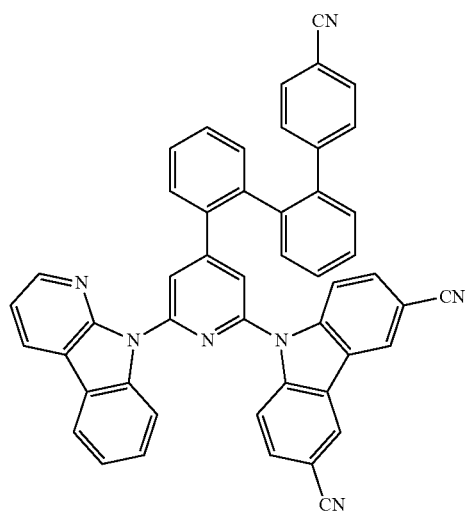
154
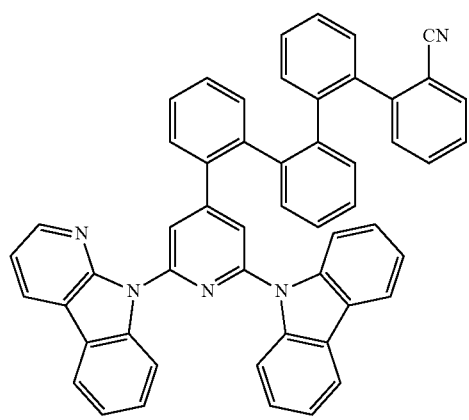
155
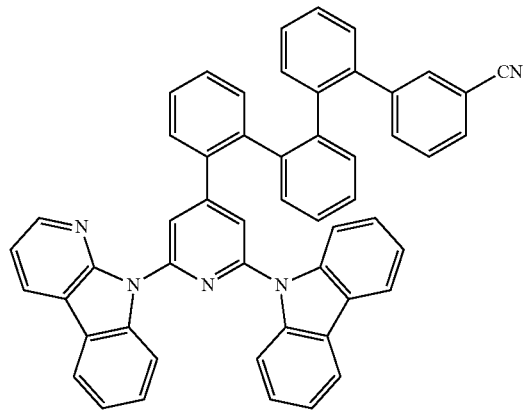
156
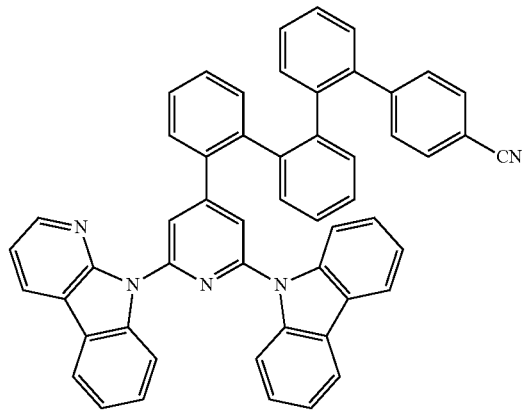
157
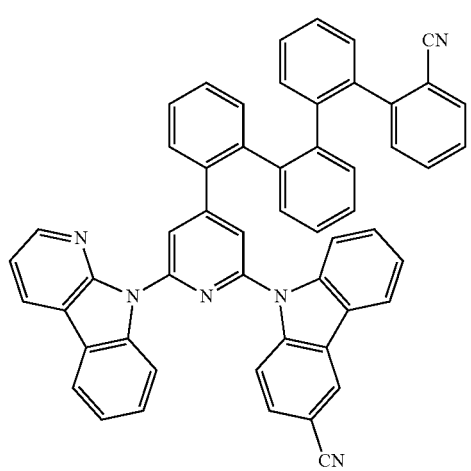
158
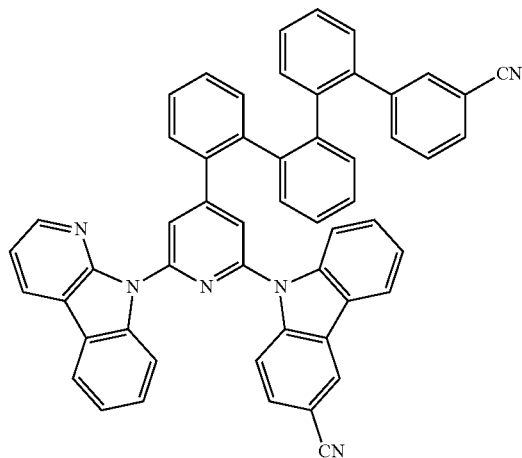

159
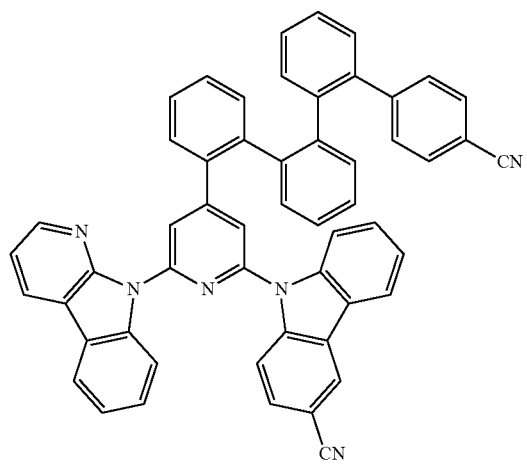
160
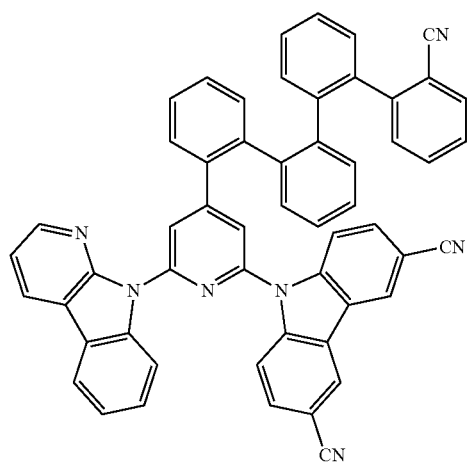
161
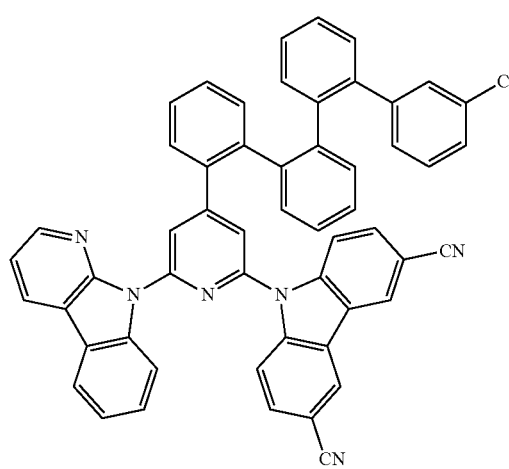
162
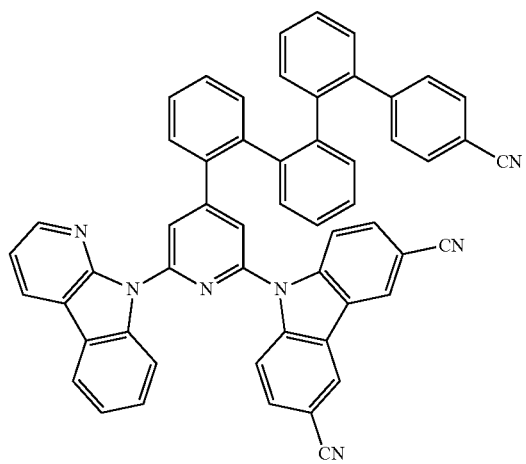
163
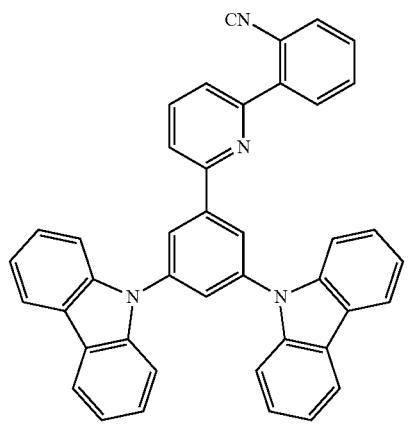
164
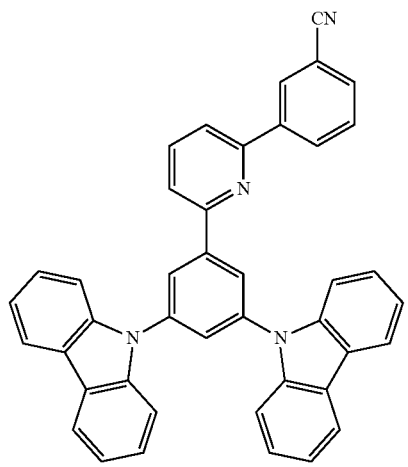

835
-continued
165
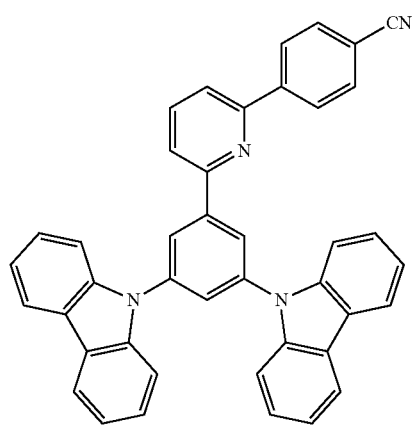
166
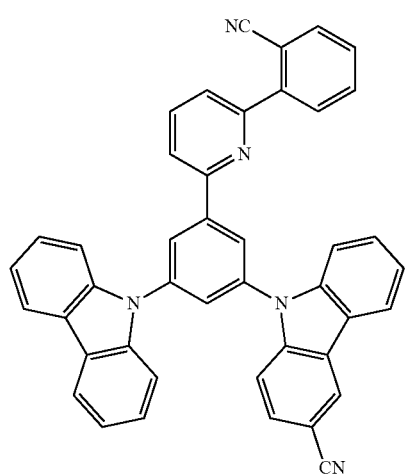
167
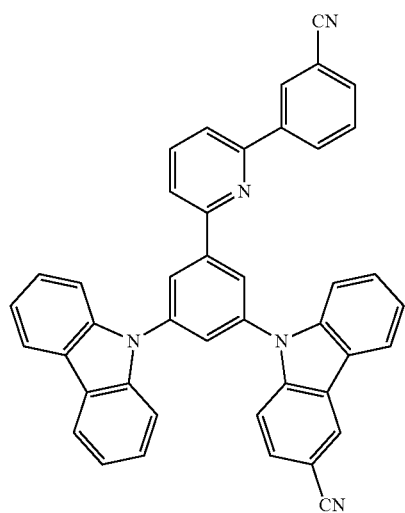
836
-continued
168
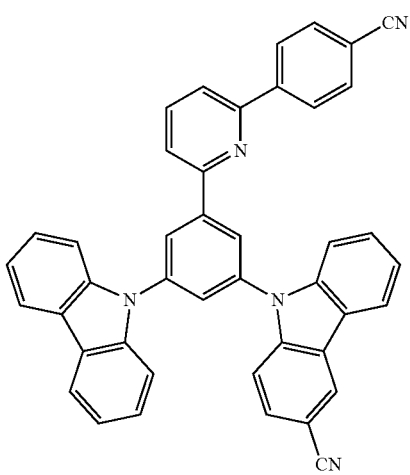
169
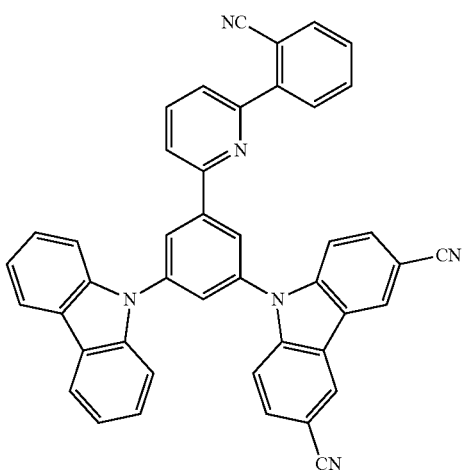
170
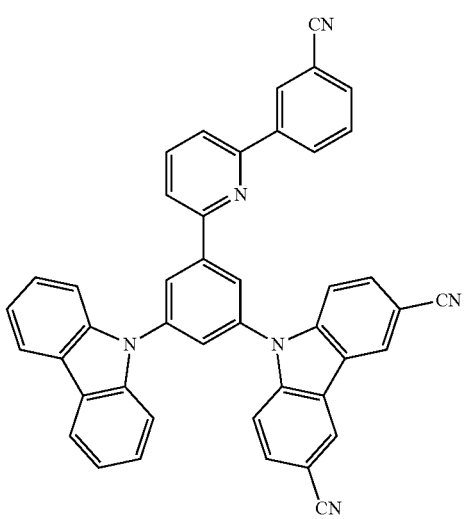

| 171 | 174 |
|---|---|
| 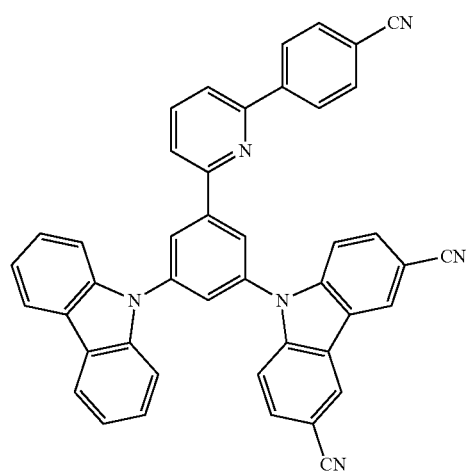 | 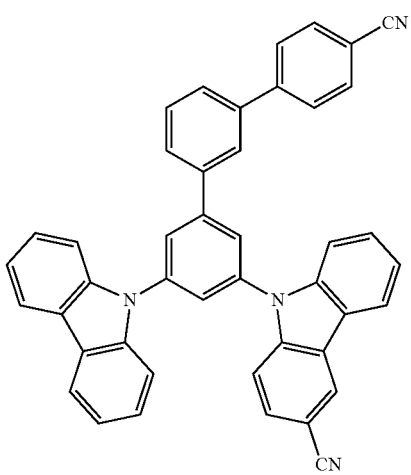 |
| 172 | 175 |
| 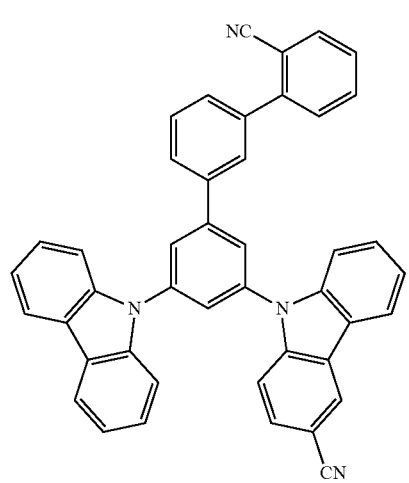 | 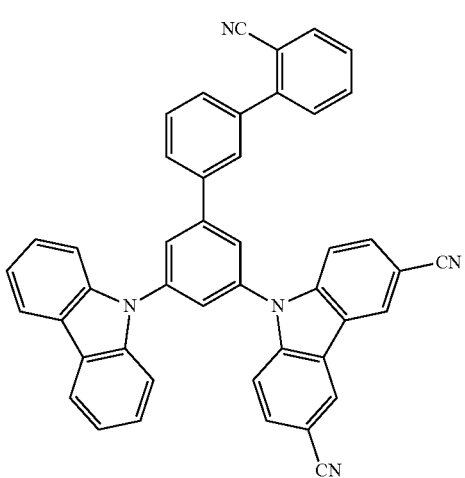 |
| 173 | 176 |
| 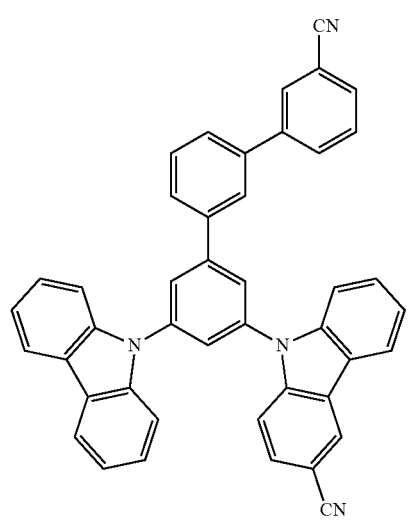 | 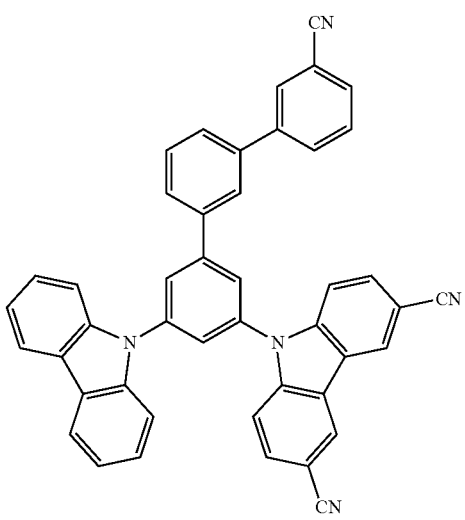 |

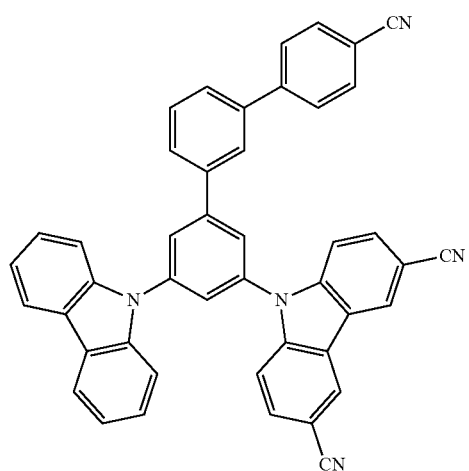
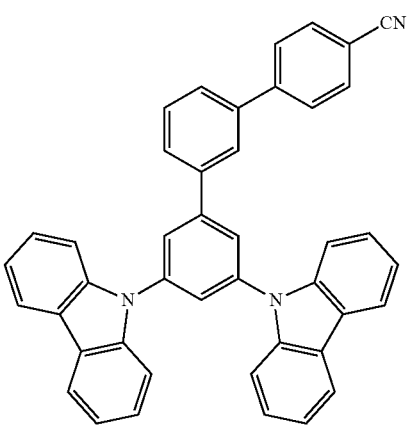

183 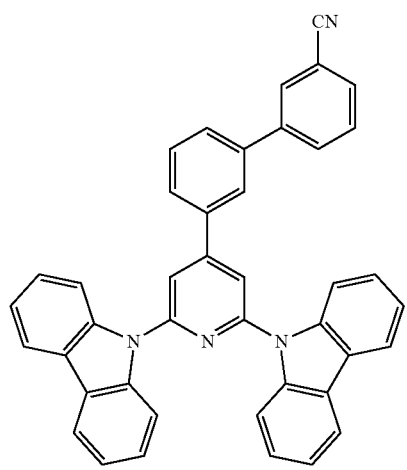
184 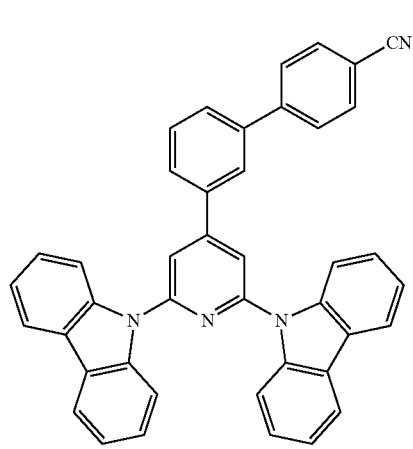
185 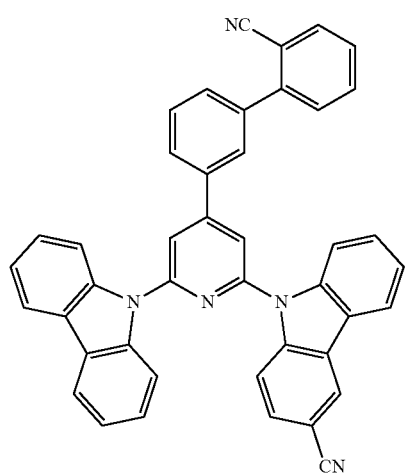
186 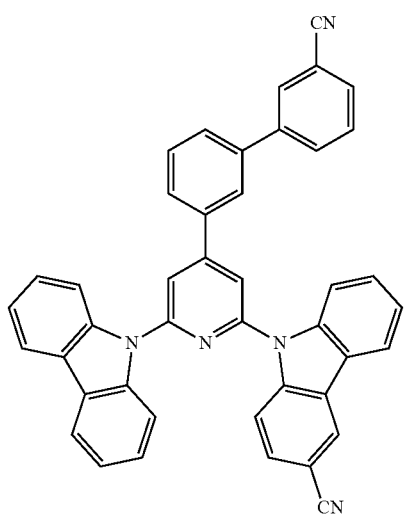
187 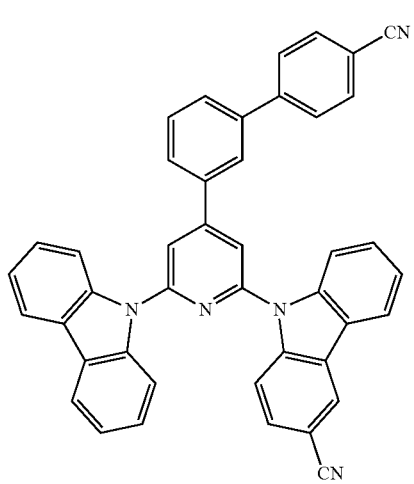
188 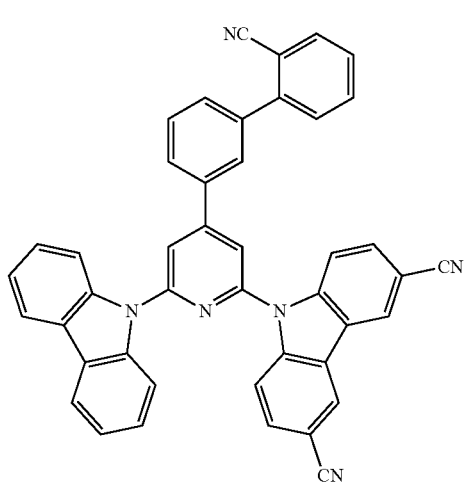

189
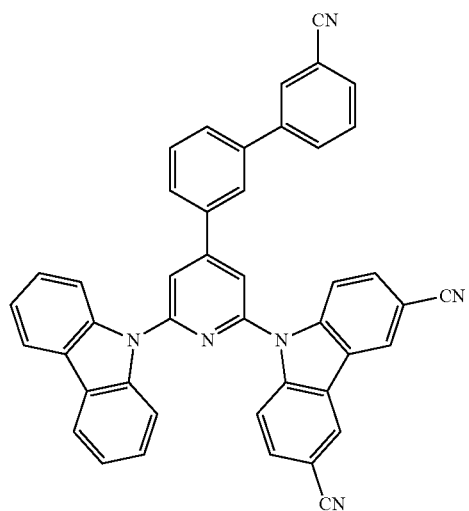
190
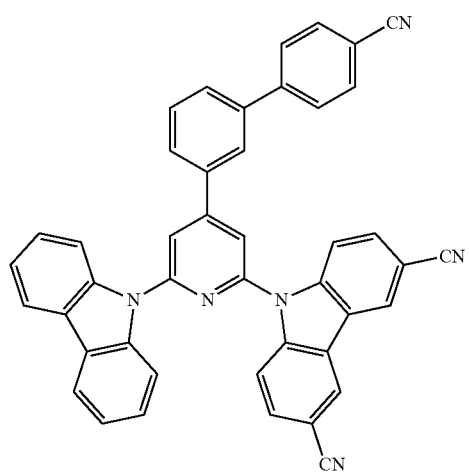
191
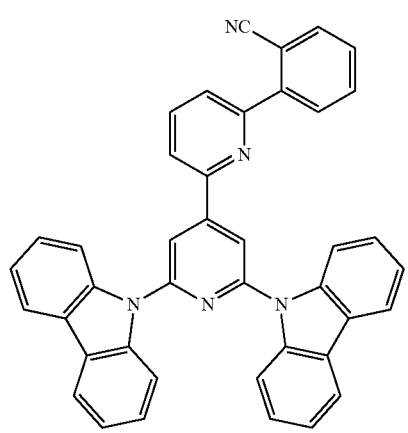
192
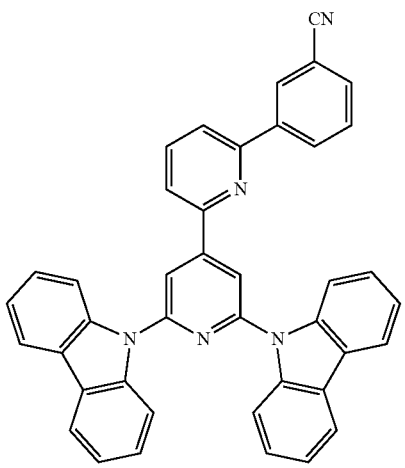
193
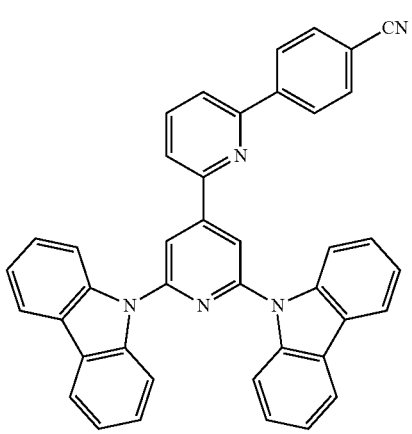
194
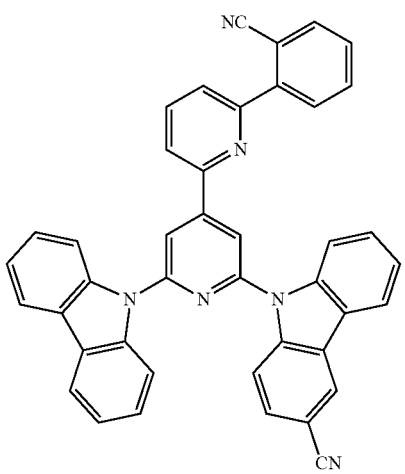

-continued
195
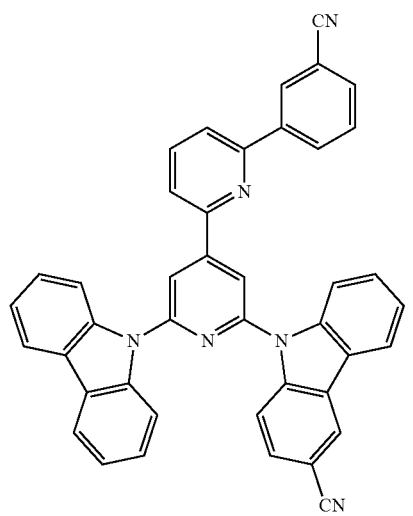
196
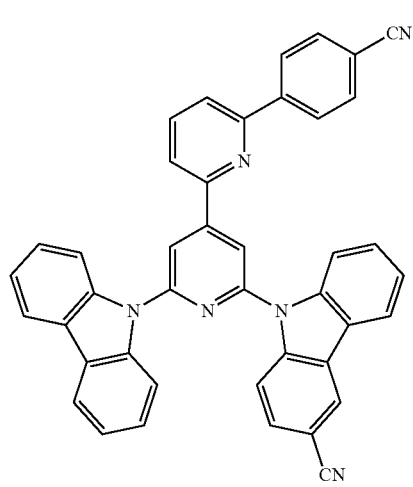
197
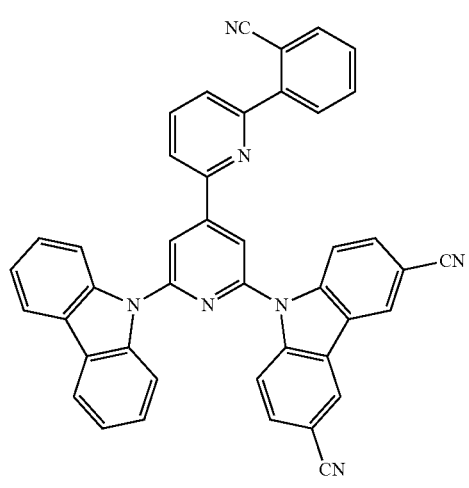
-continued
198
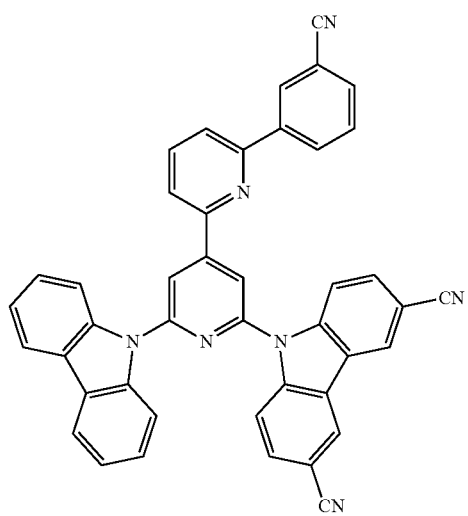
199
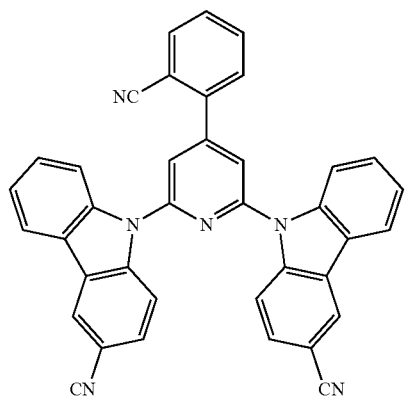
200
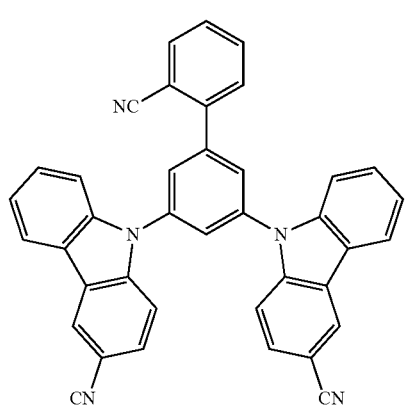

847
-continued
201
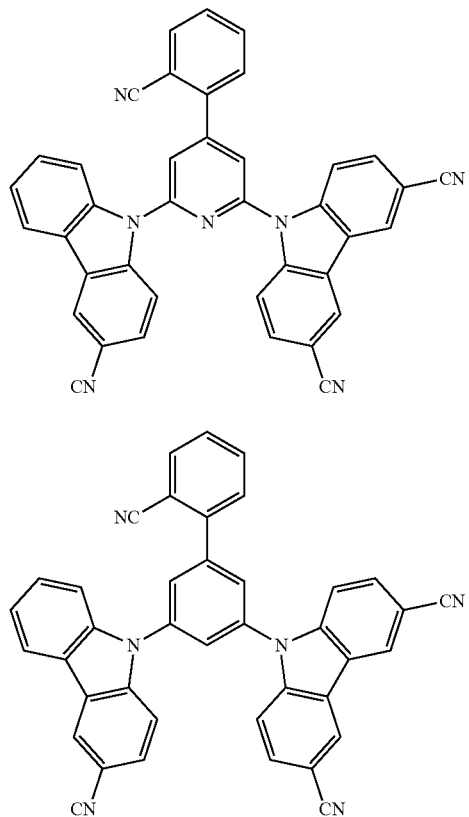
202
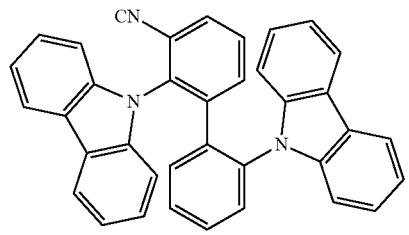
Group HE6
1
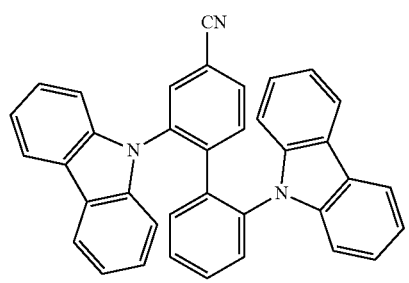
2
848
-continued
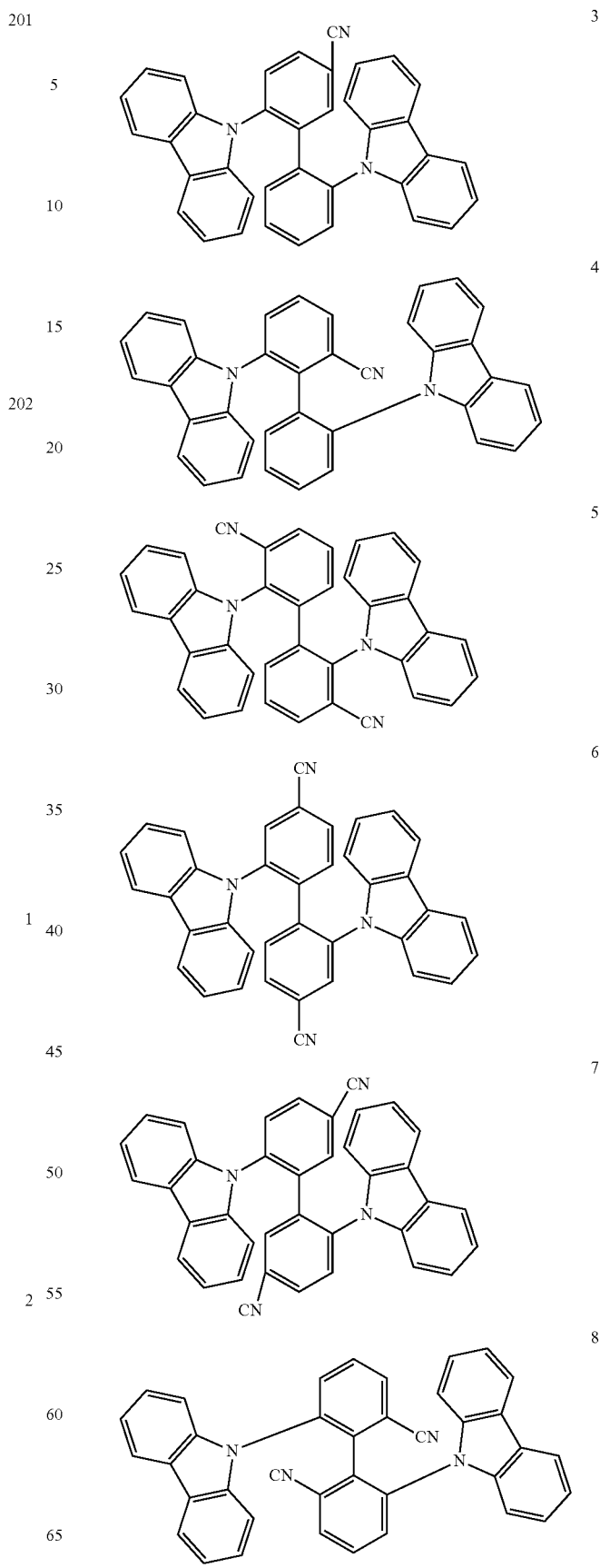

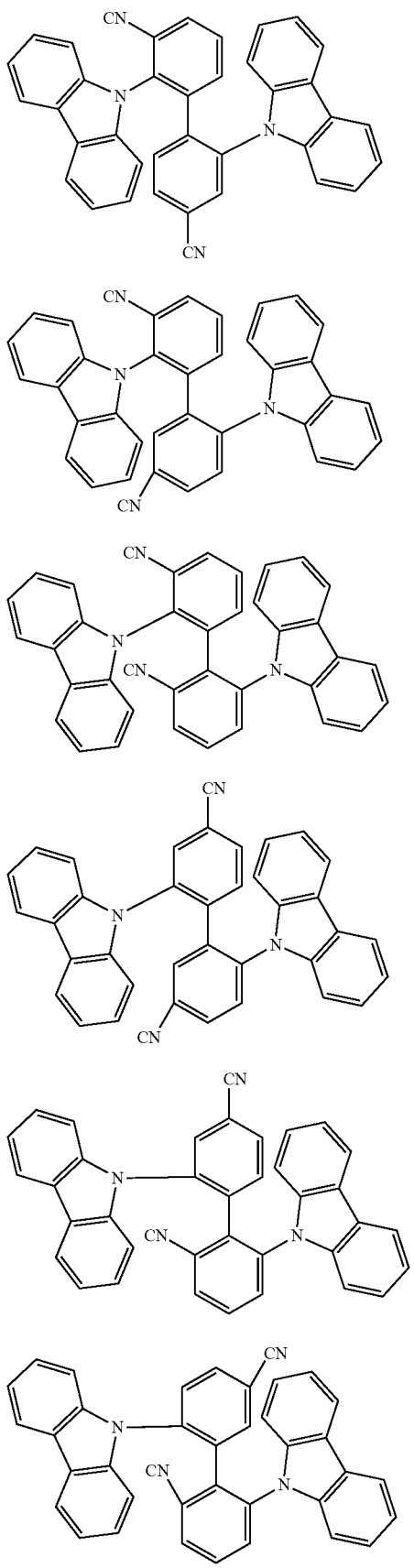
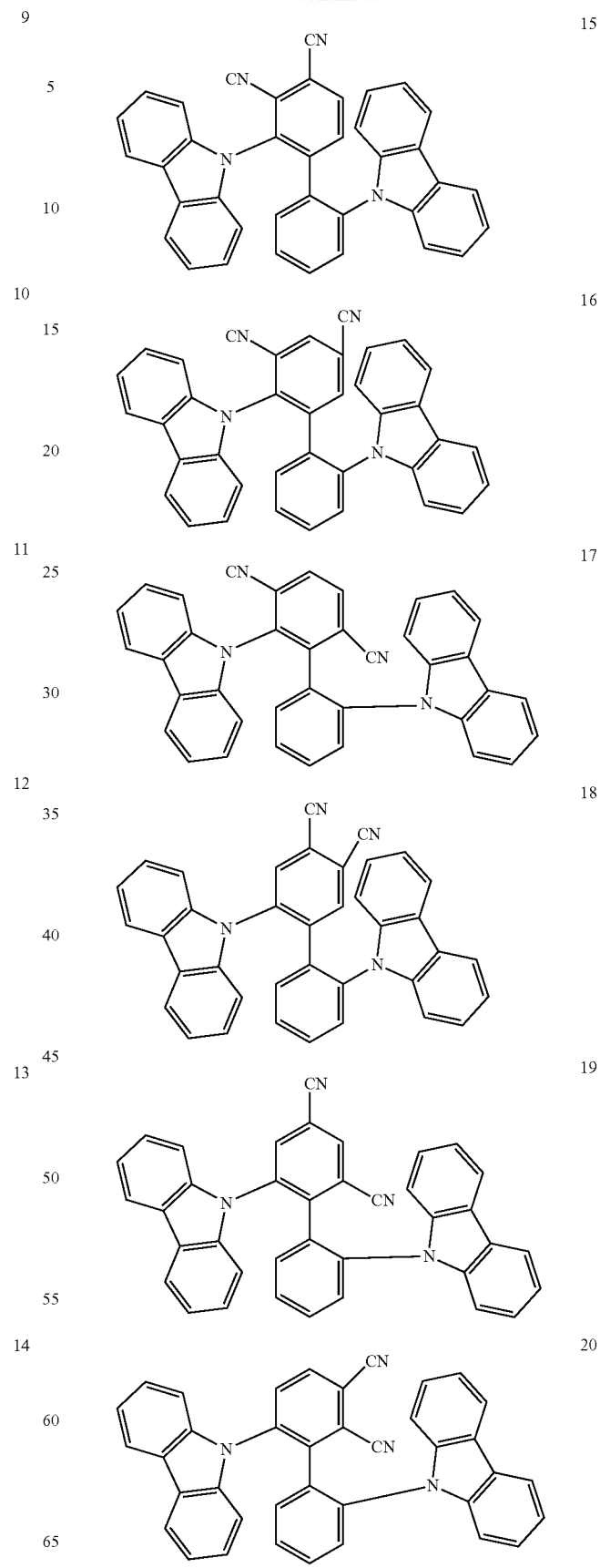

-continued
21
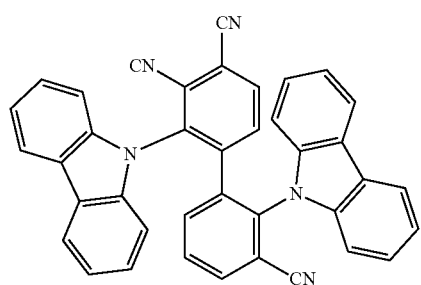
22
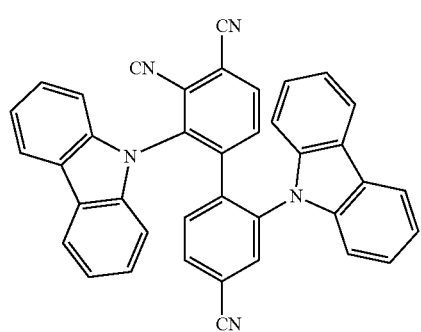
23
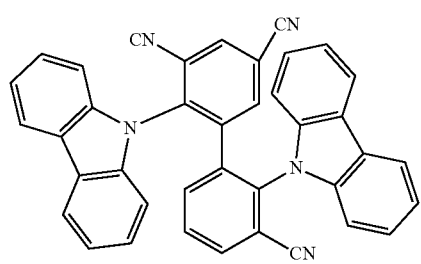
24
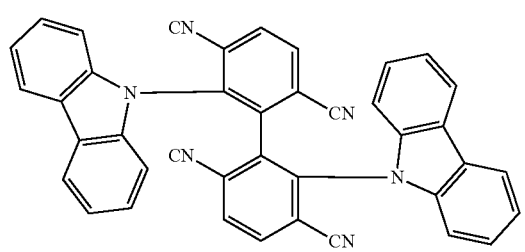
25
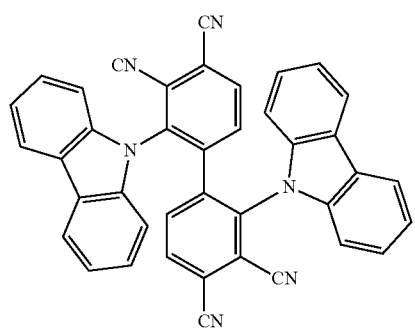
-continued
26
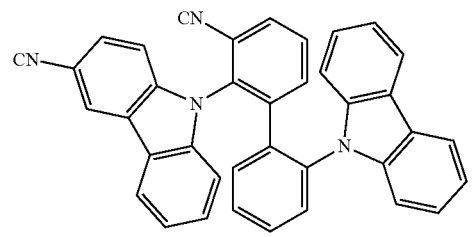
27
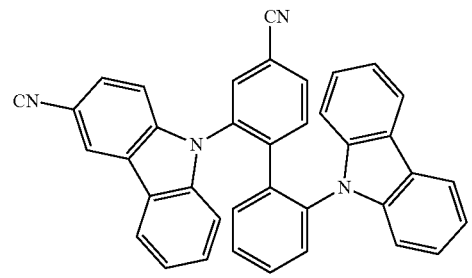
28
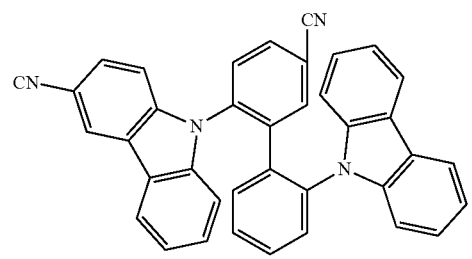
29
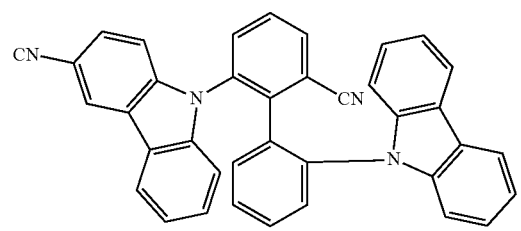
30
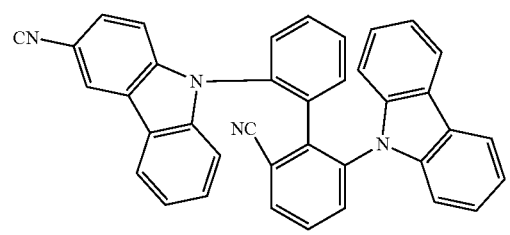
31
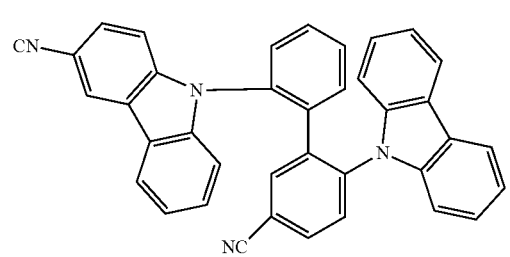

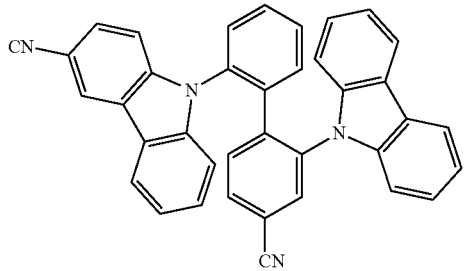
32
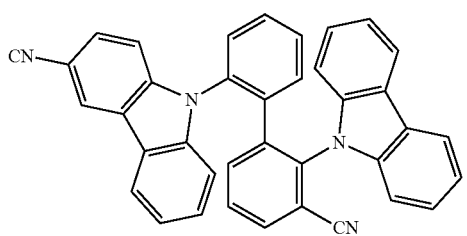
33
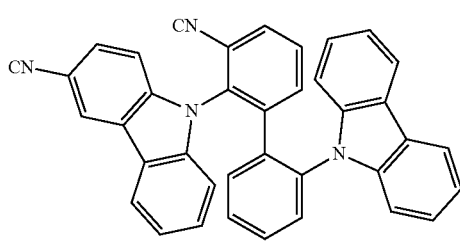
34
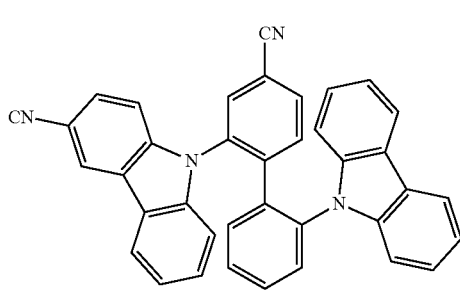
35
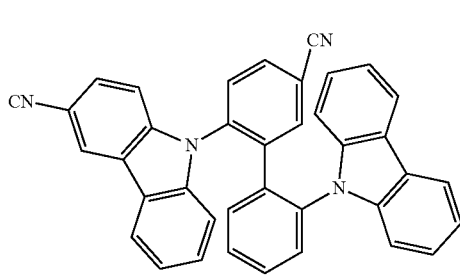
36
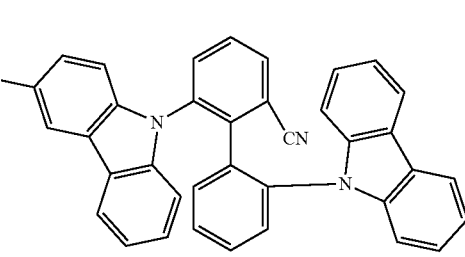
37
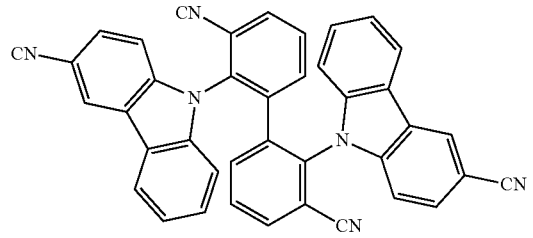
38

39
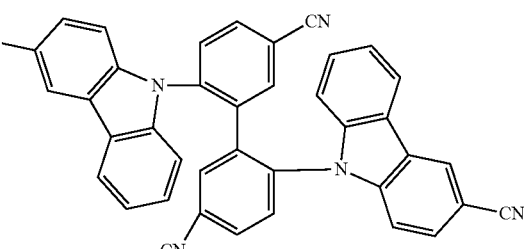
40
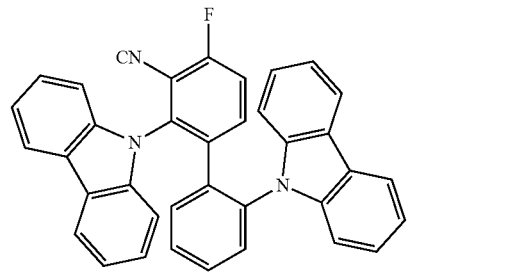
41
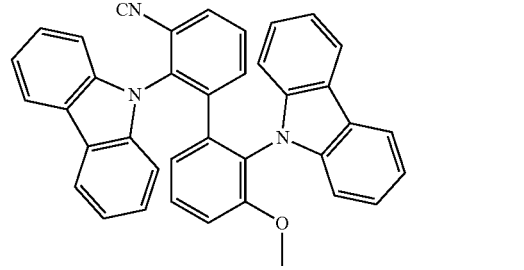
42

43
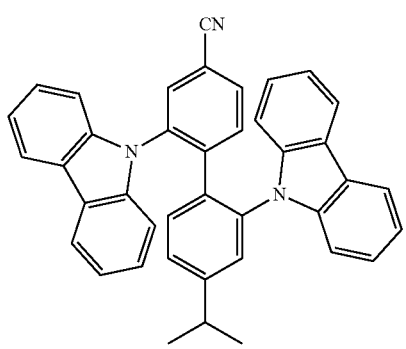
44
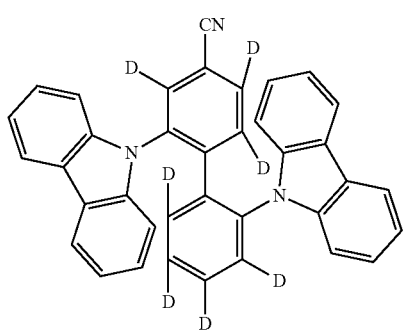
45
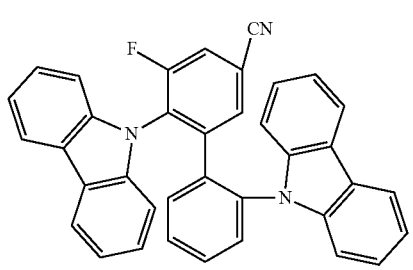
46
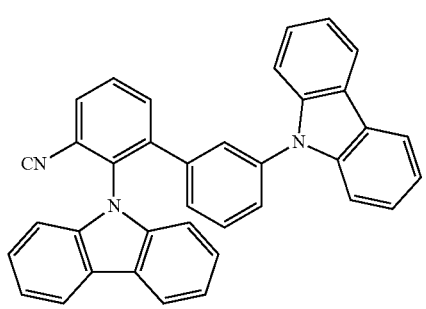
47
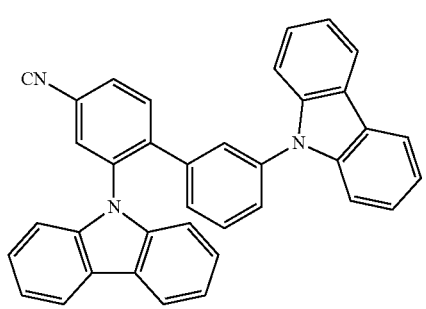
48

49
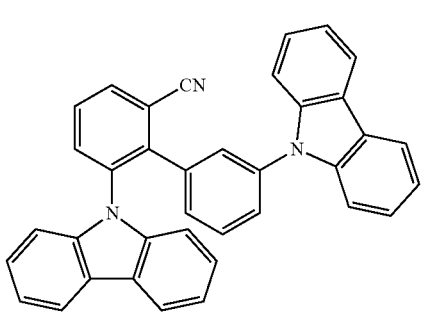
50

51

52
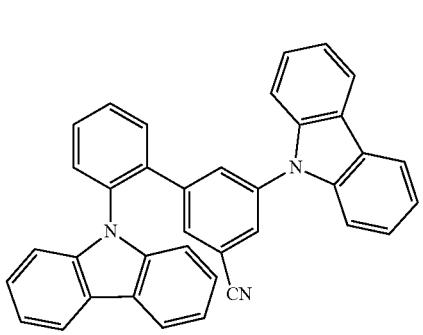

53
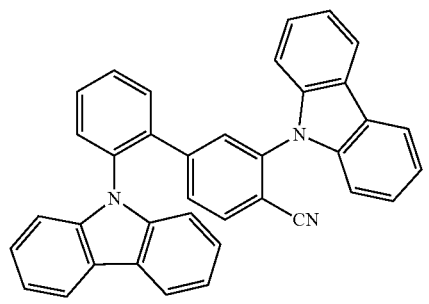
54
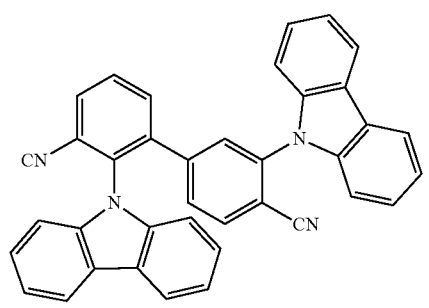
55
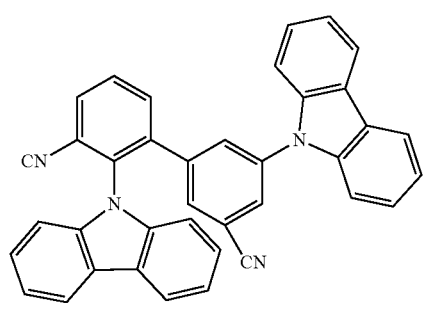
56
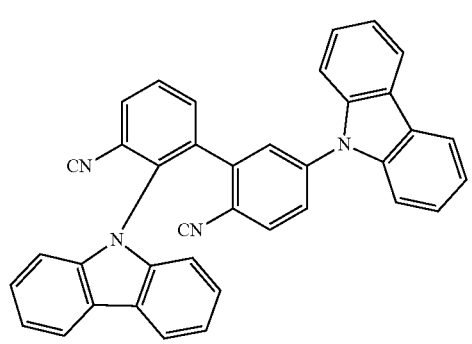
57
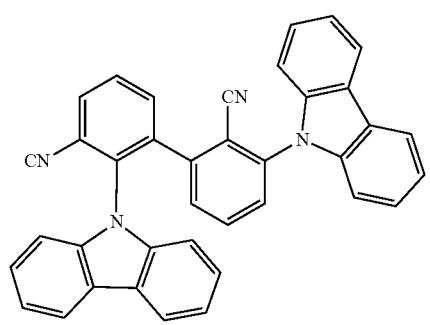
58
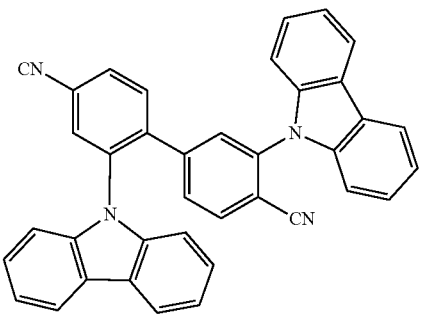
59
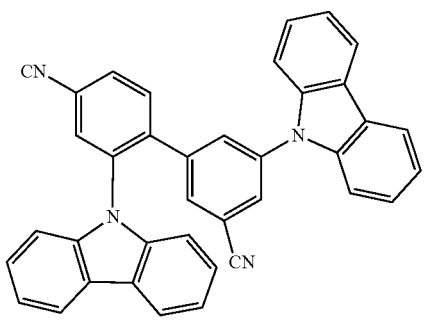
60
61
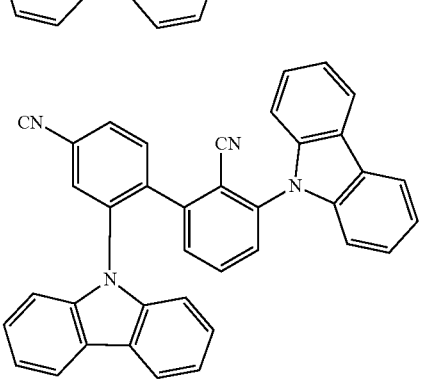
62
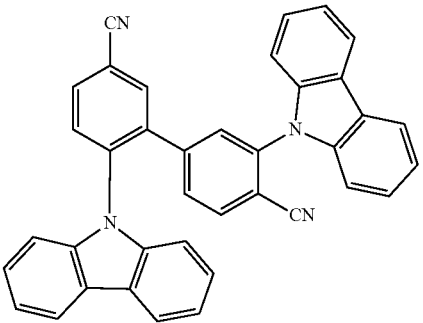

859
-continued
63
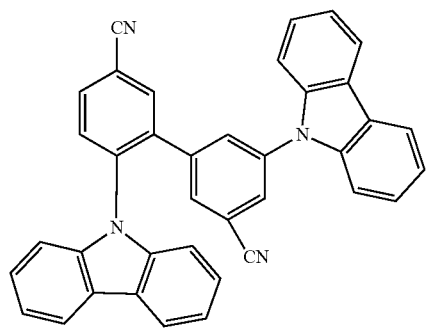
64
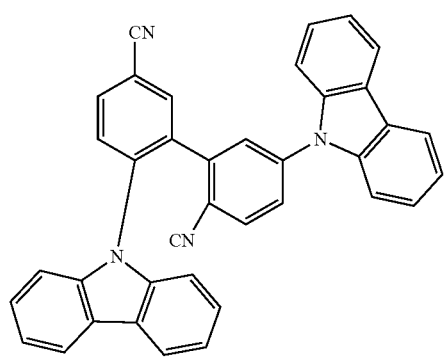
65
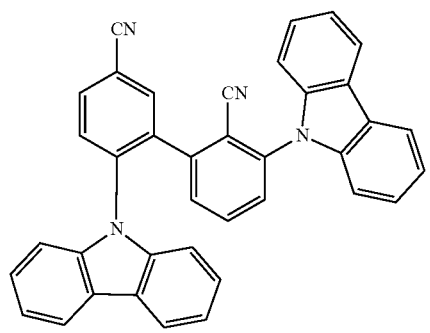
66
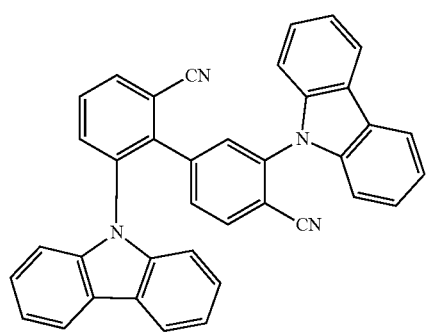
860
-continued
67
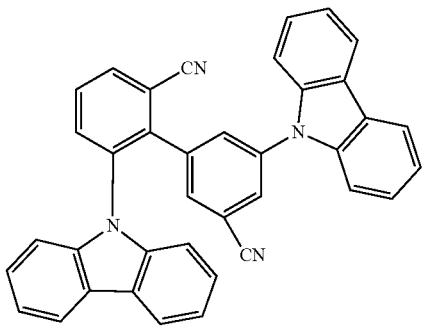
68
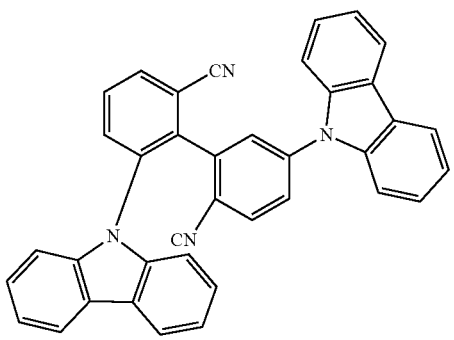
69
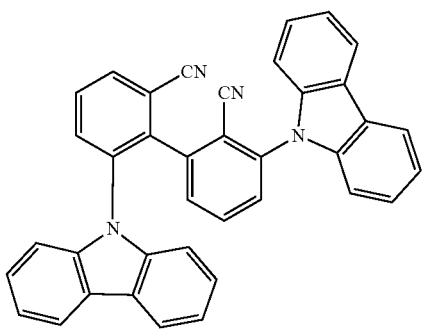
70
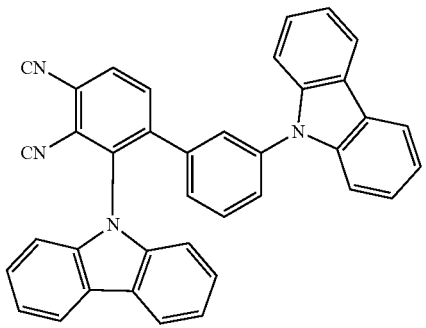

71
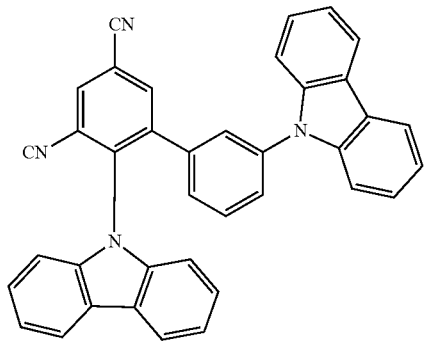
72
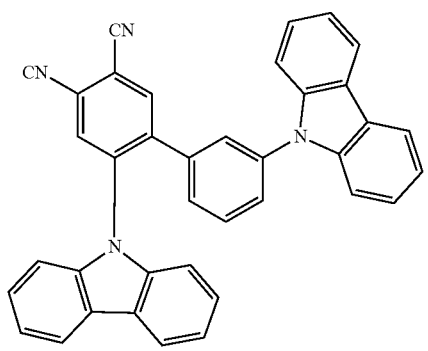
73
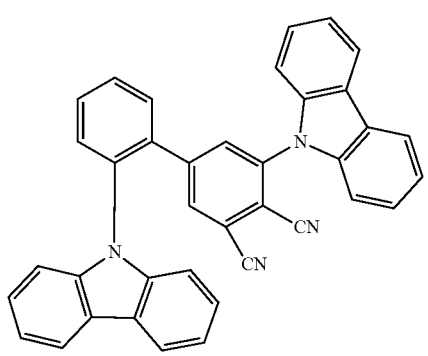
74

75
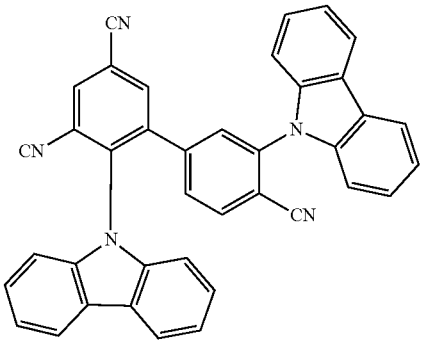
76
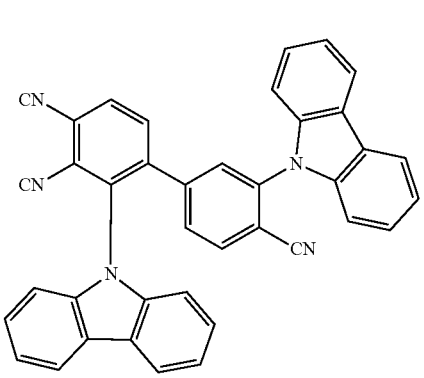
77
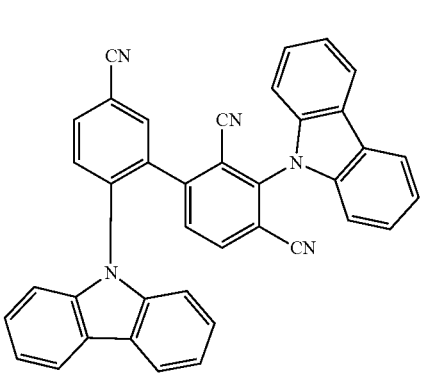
78
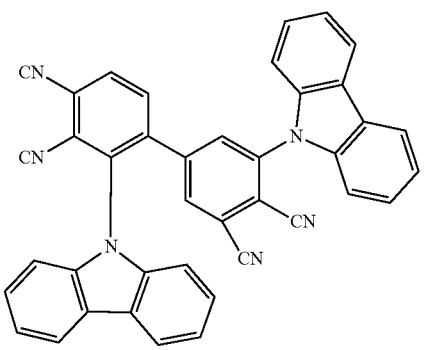

79
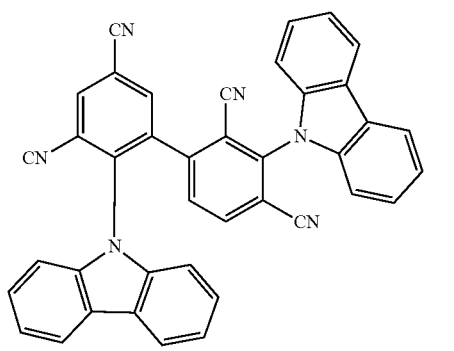
80
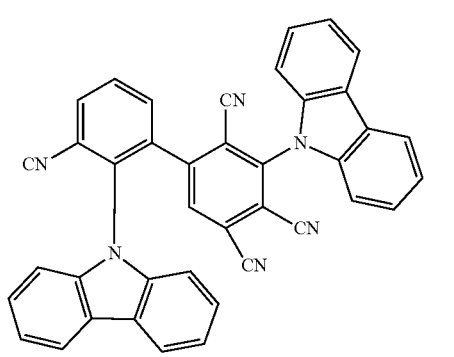
81
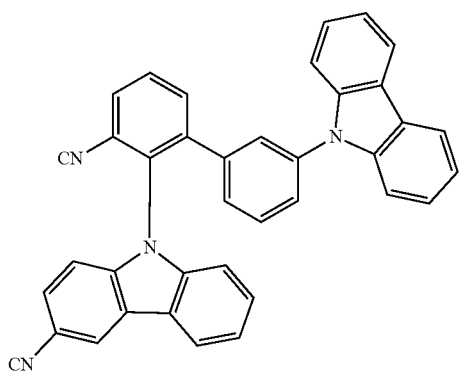
82
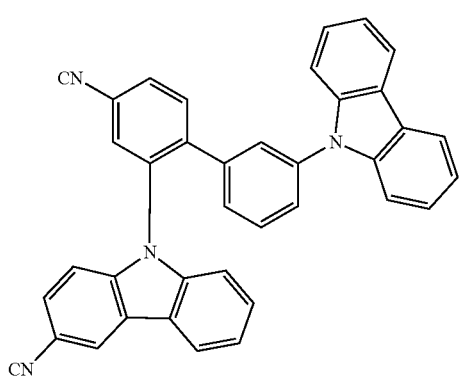
83
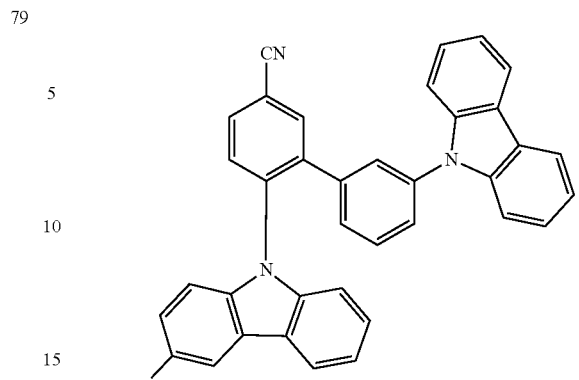
84
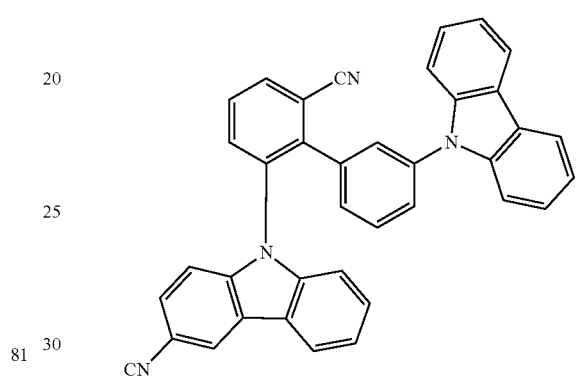
85
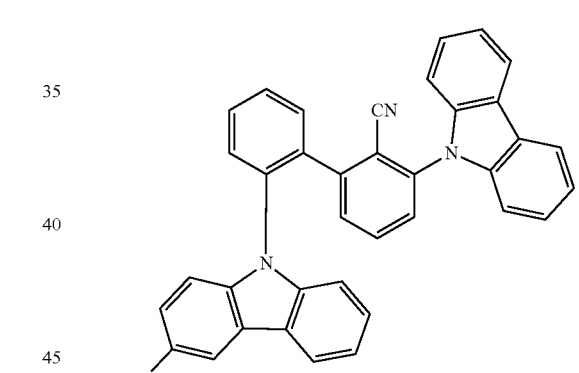
86
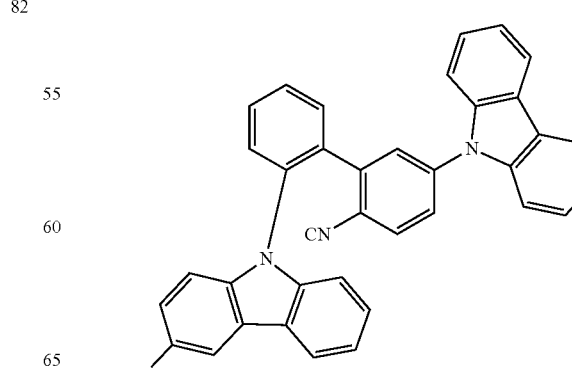

87
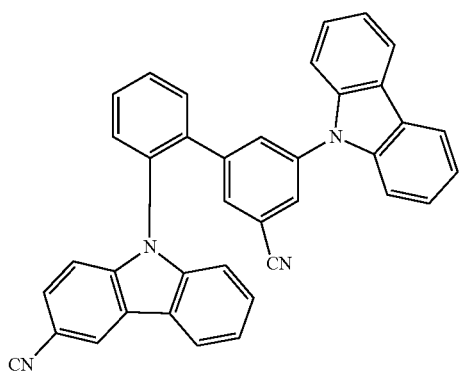
88
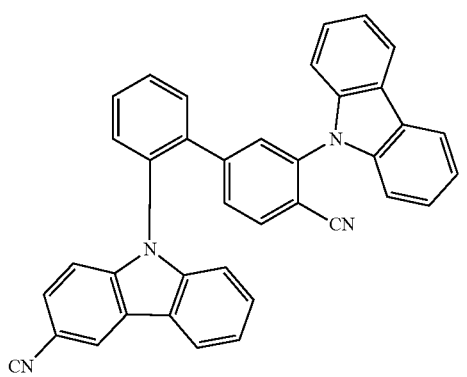
89
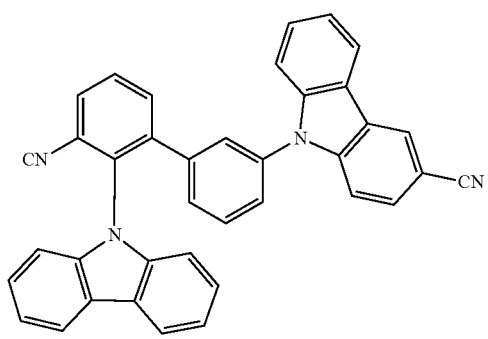
90

91
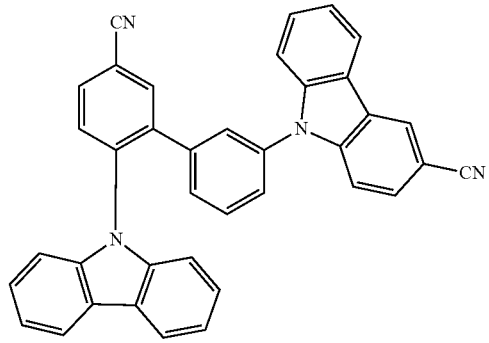
92
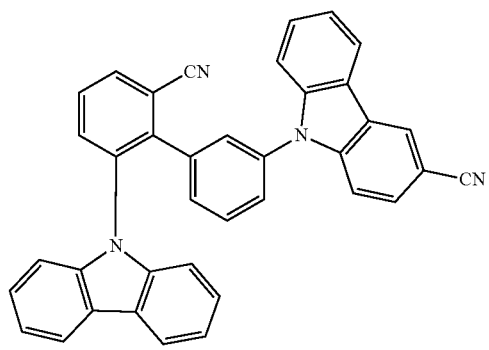
93
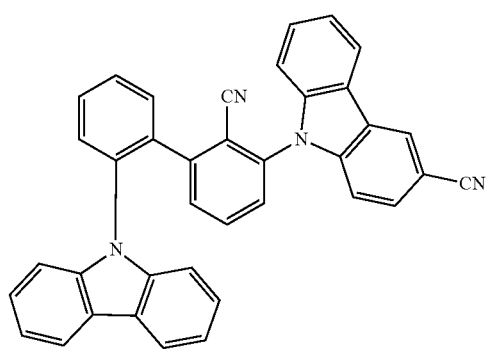
94
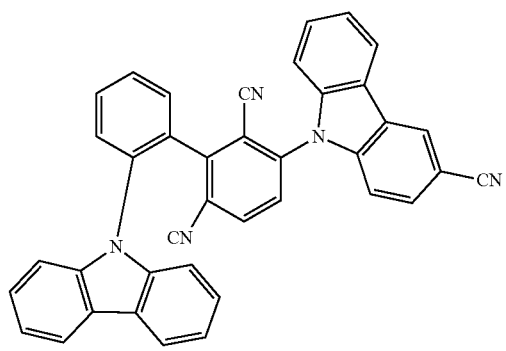

95
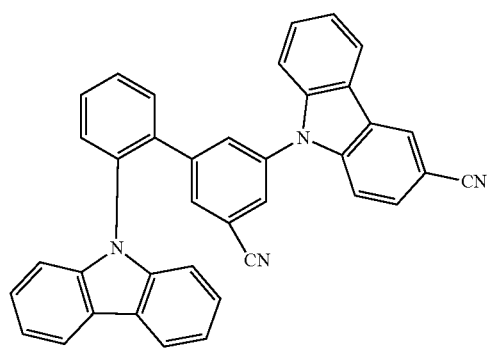
96
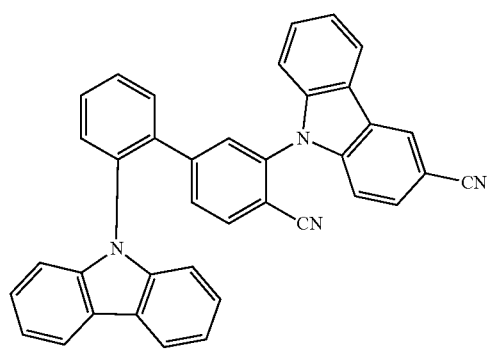
97
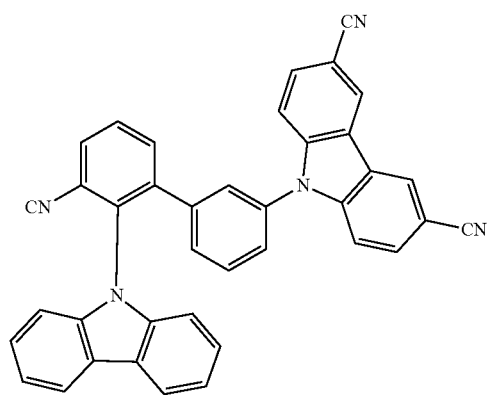
98

99
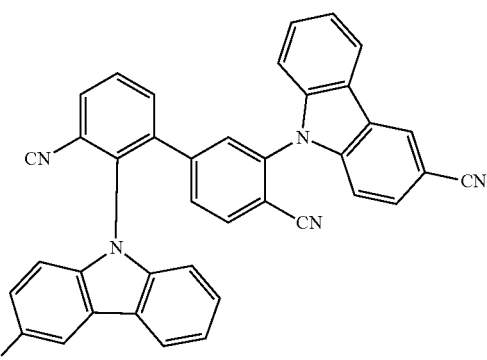
100
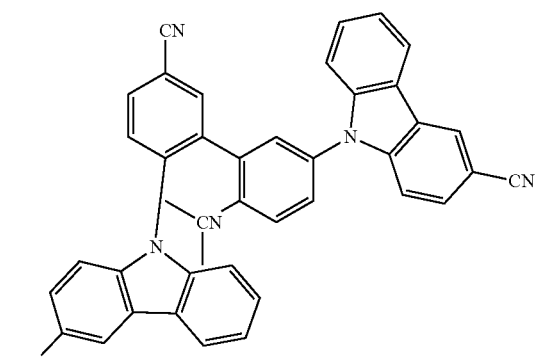
101
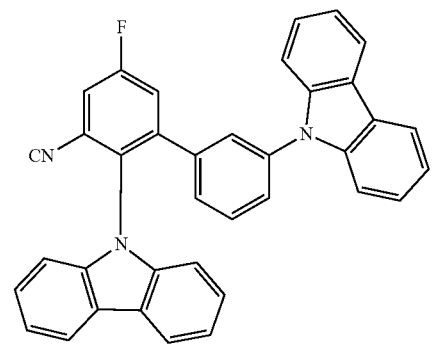
102
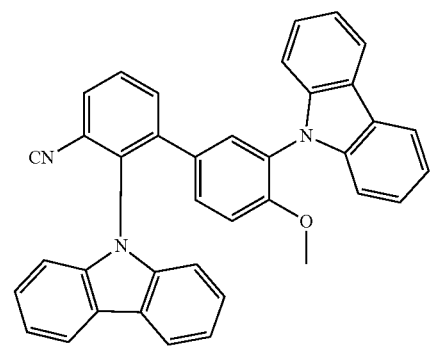

-continued
| 103 | 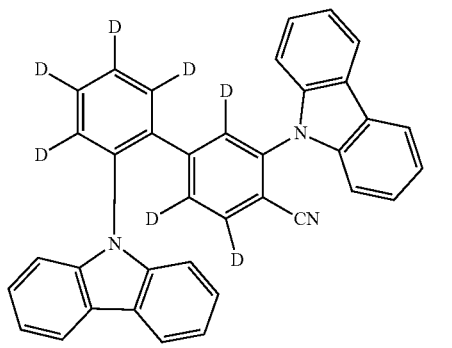 |
| 104 | 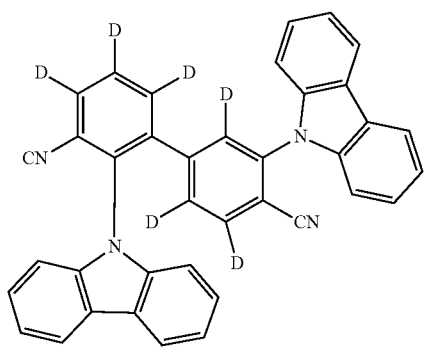 |
| 105 | 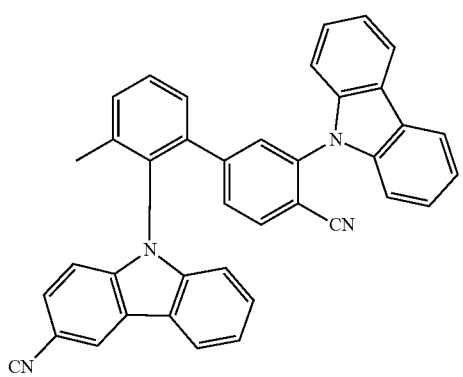 |
| 106 | 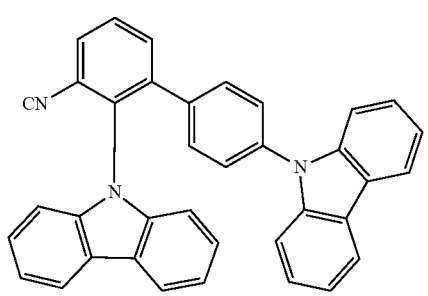 |
| 107 | 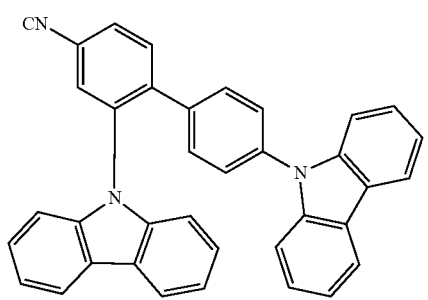 |
-continued
| 108 | 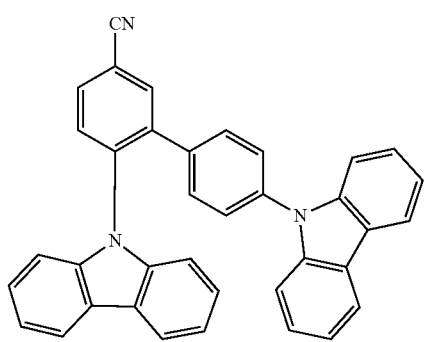 |
| 109 | 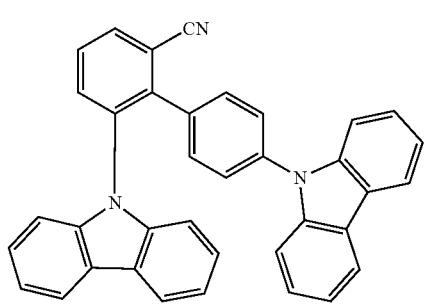 |
| 110 | 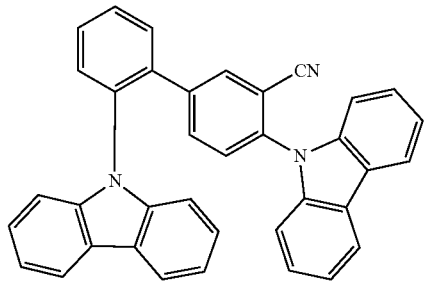 |
| 111 | 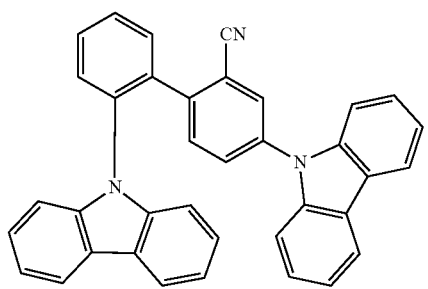 |
| 112 | 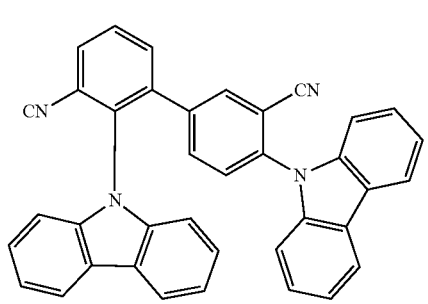 |

113 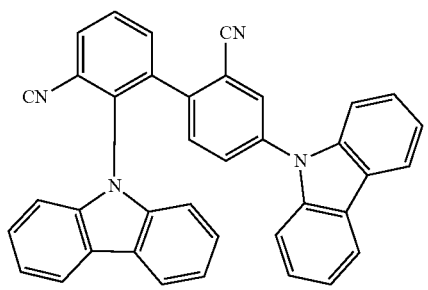
114 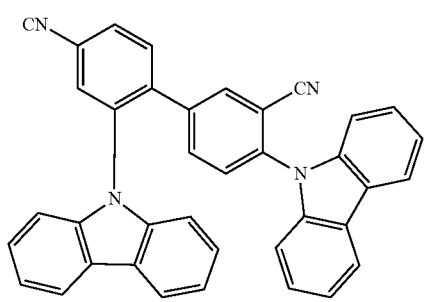
115 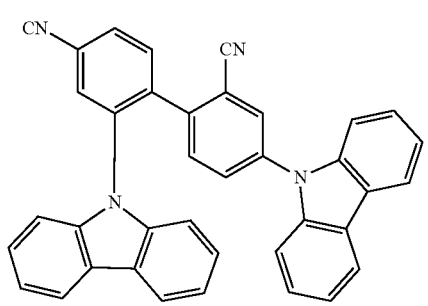
116 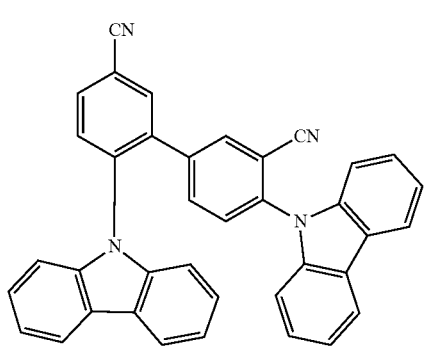
117 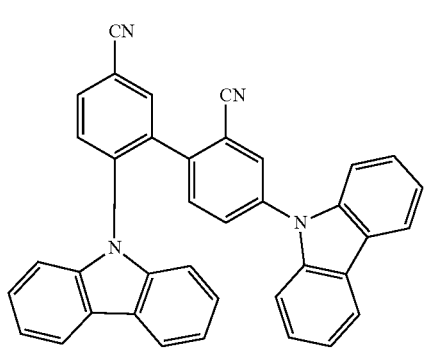
118 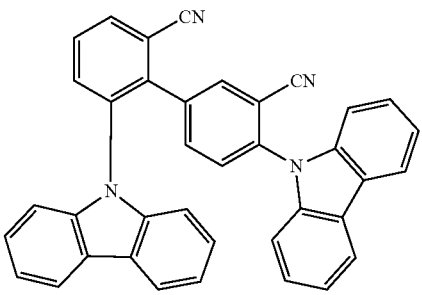
119 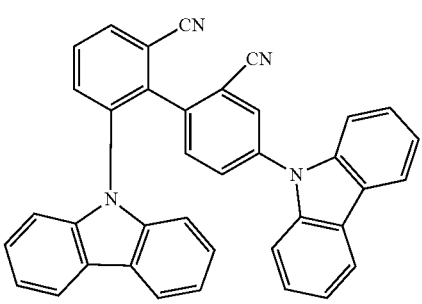
120 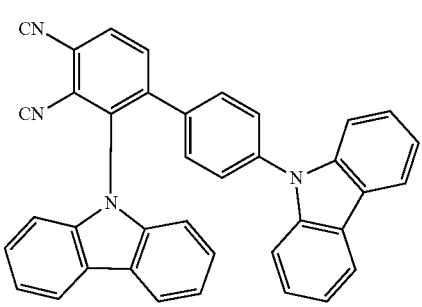
121 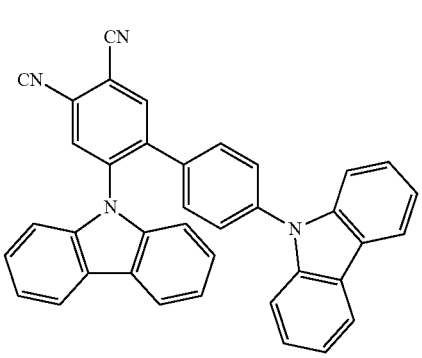
122 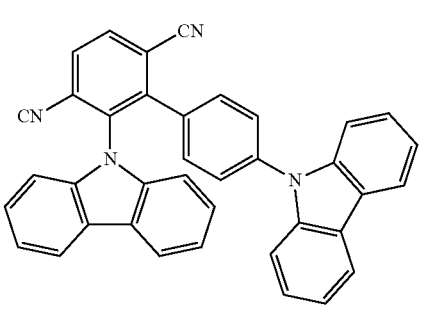

123
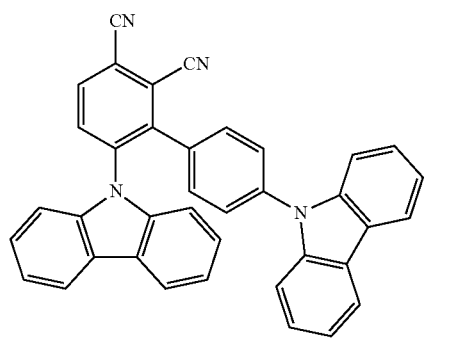
124
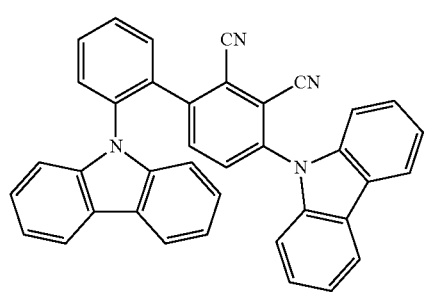
125
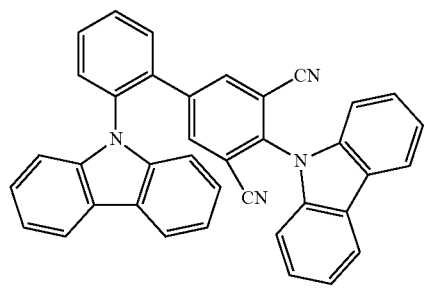
126
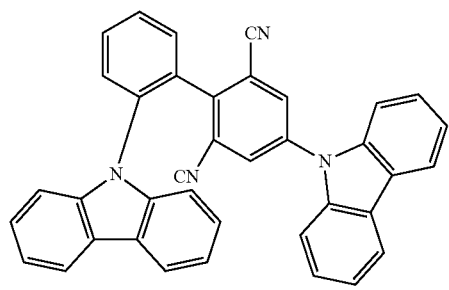
127
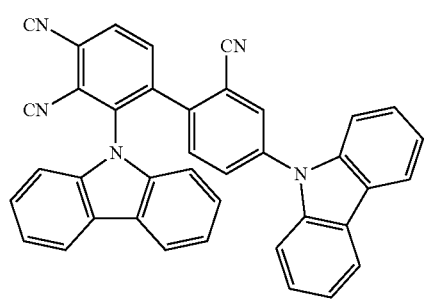
128
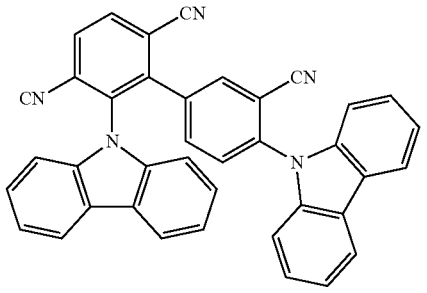
129
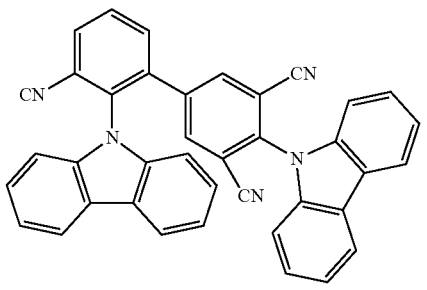
130
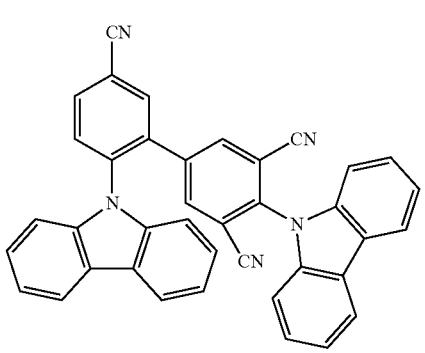
131
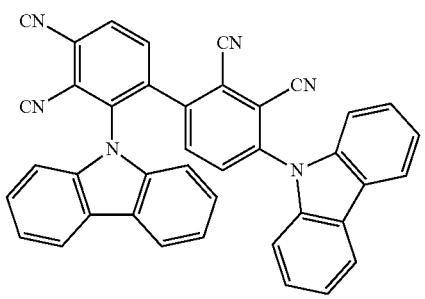
132
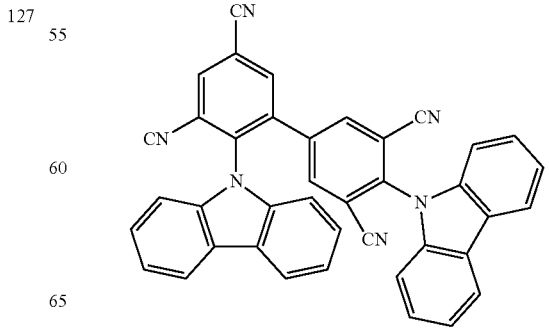

133
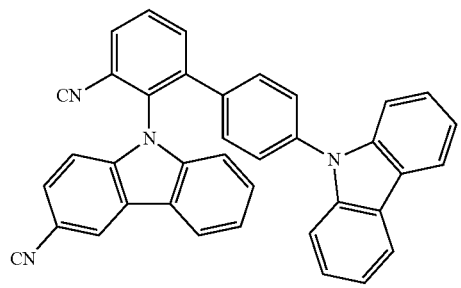
134
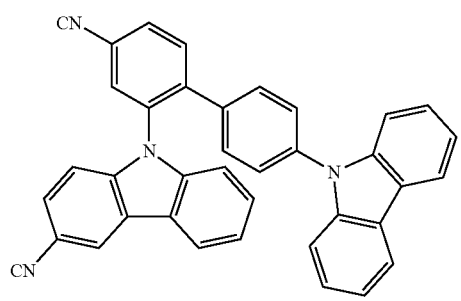
135
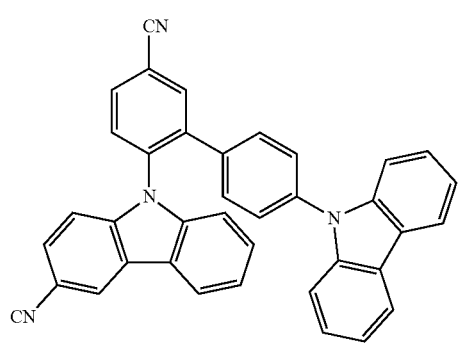
136
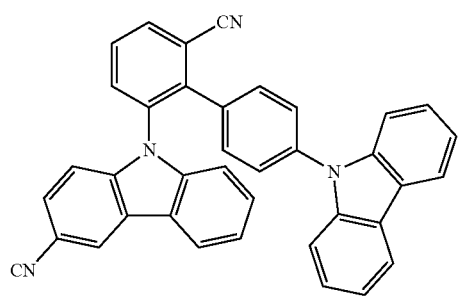
137
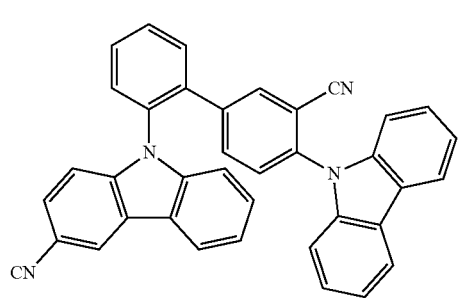
138
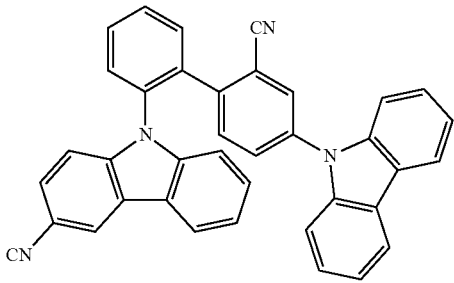
139
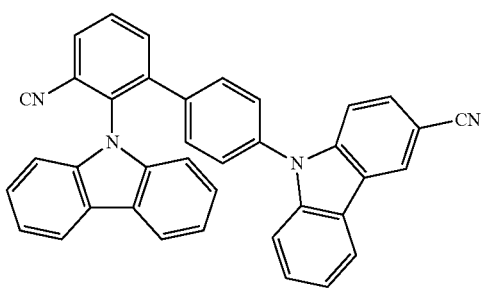
140
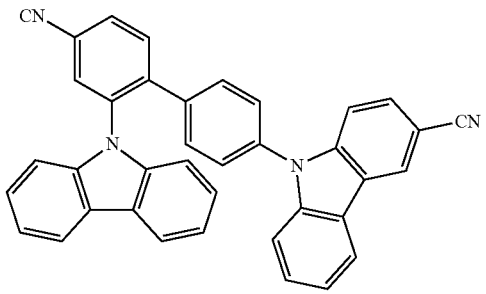
141
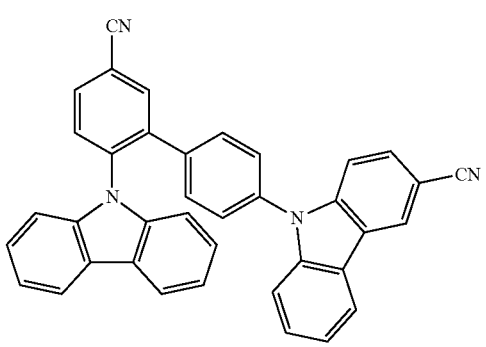
142
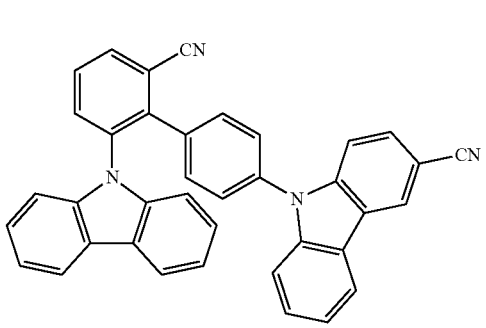

143
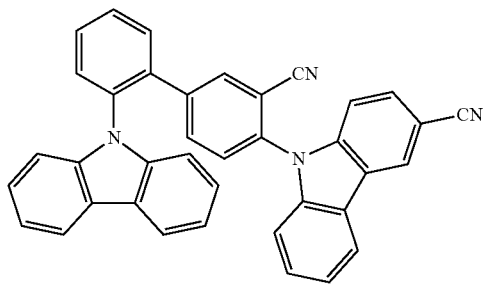
144
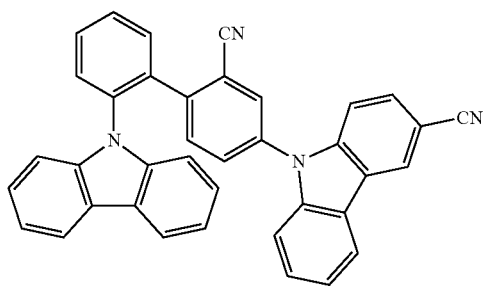
145
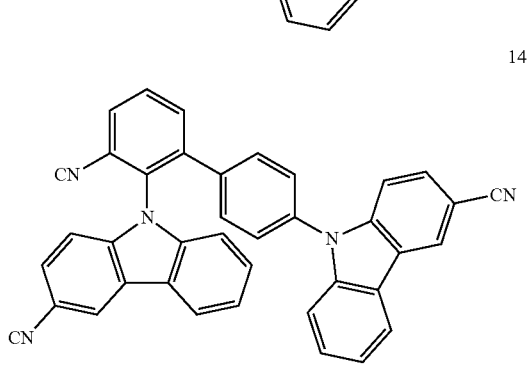
146
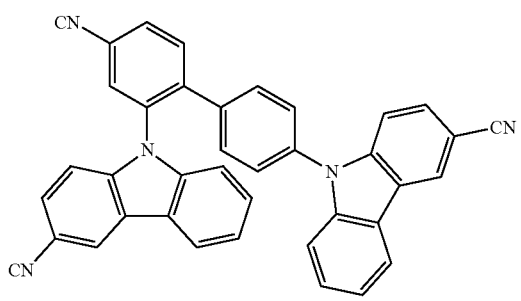
147
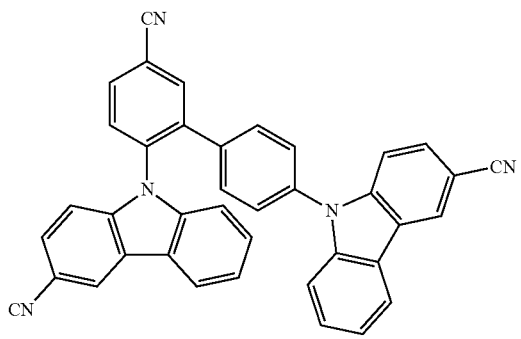
148
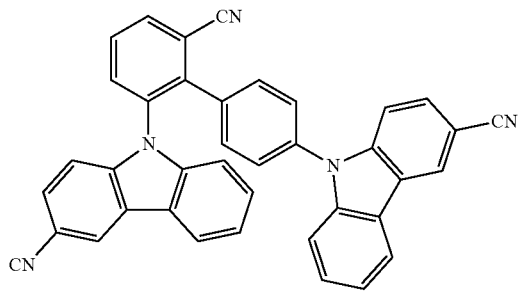
149
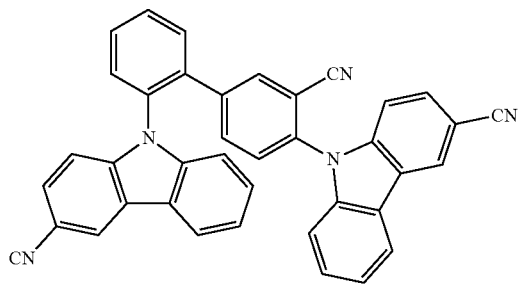
150
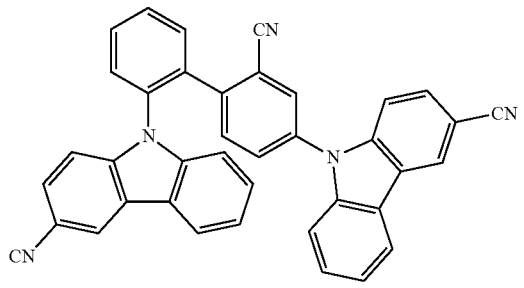
151
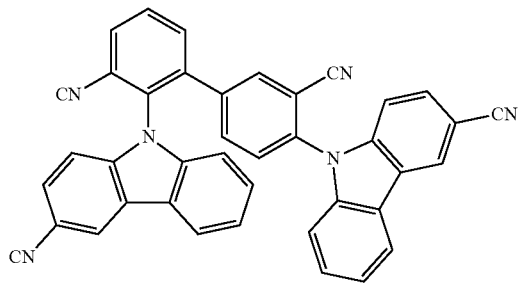
152
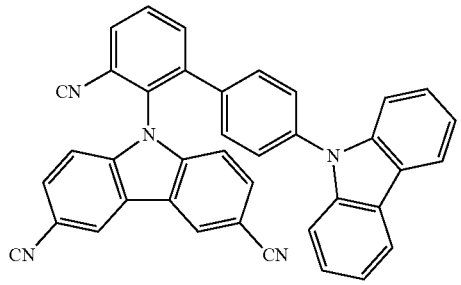

153
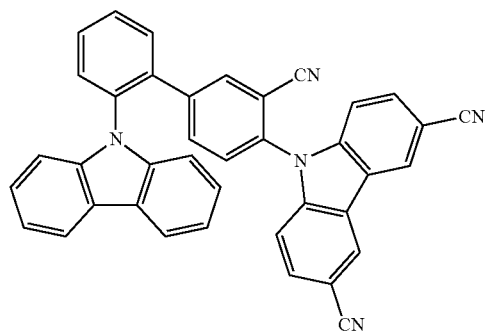
154
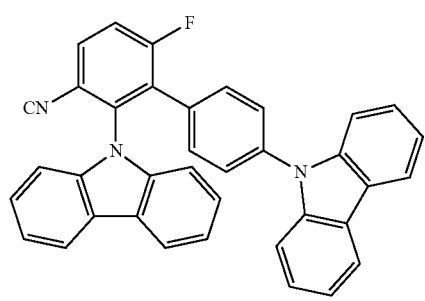
155
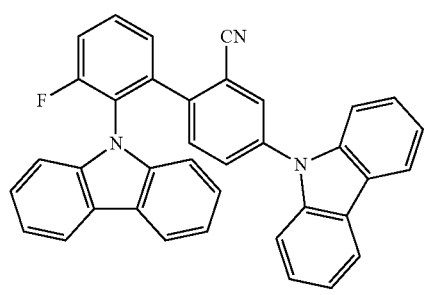
156
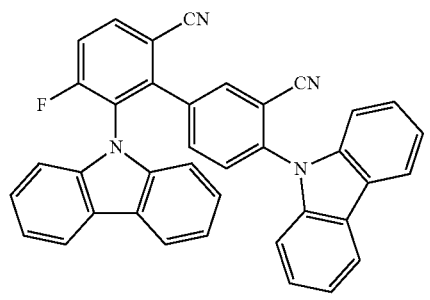
157
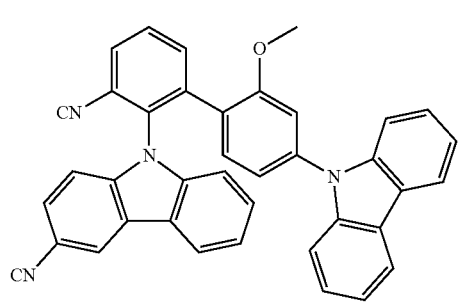
158
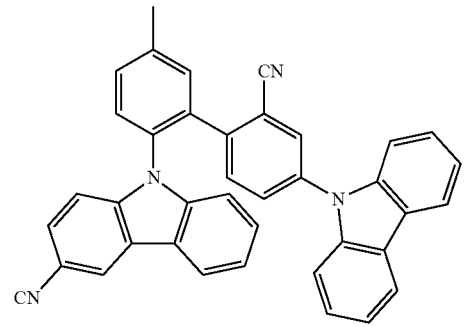
159
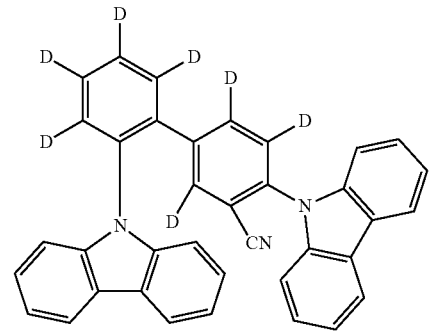
160
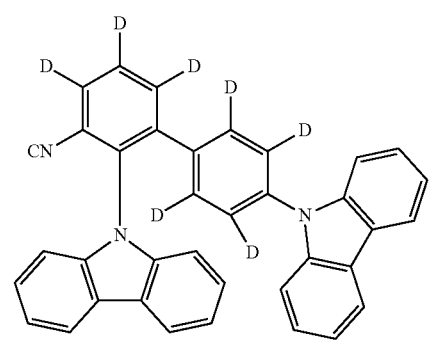
161
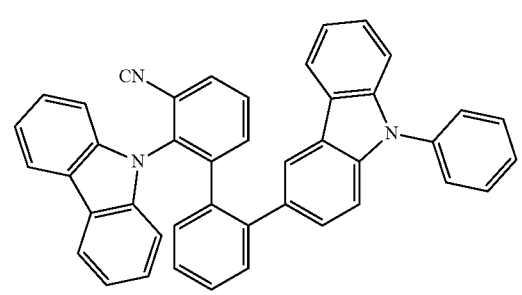

-continued
162
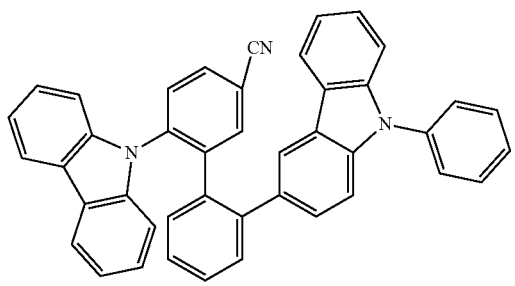
163
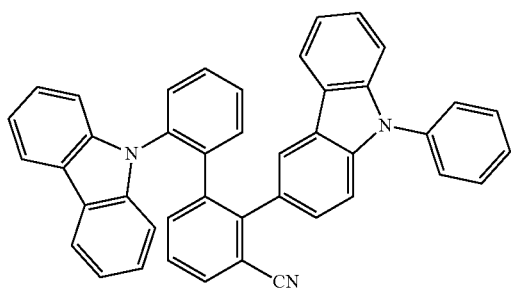
164
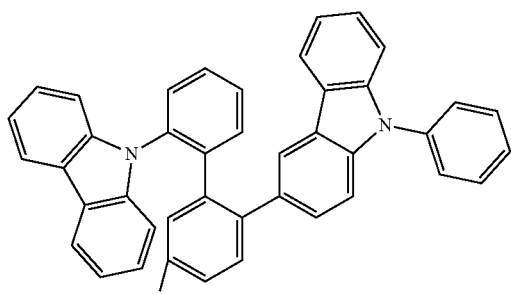
165
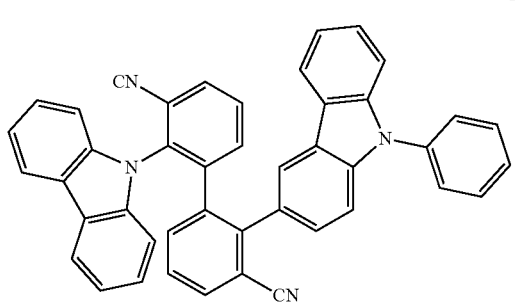
166
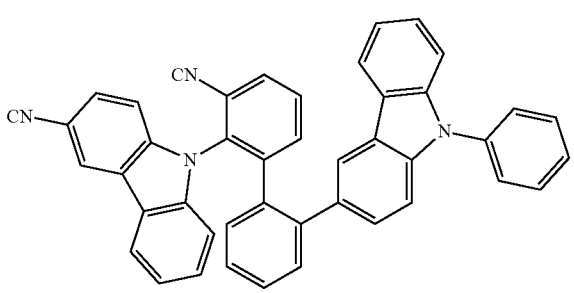
-continued
167
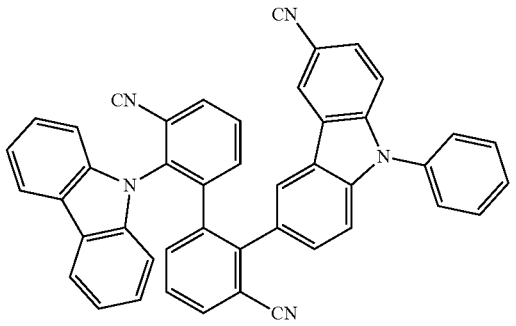
168
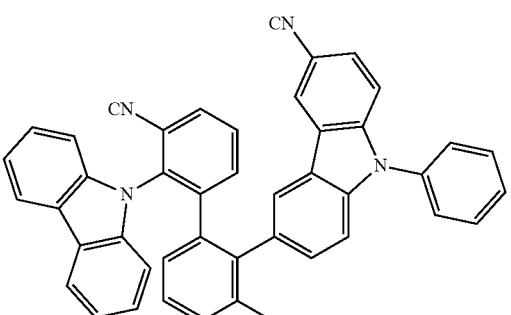
169
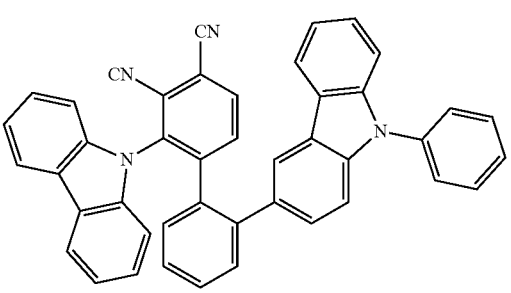
170
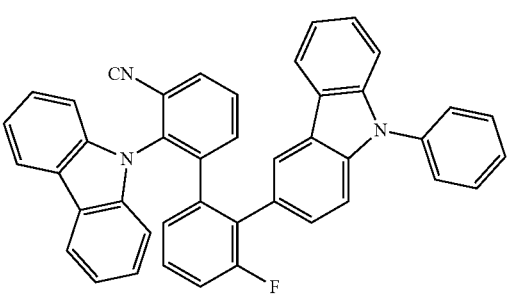
171
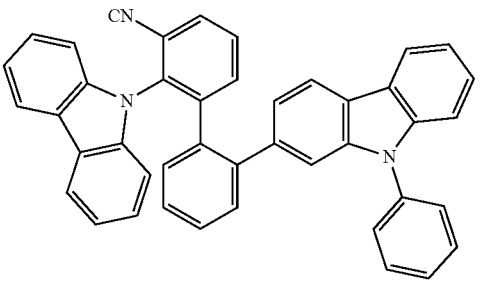

883
-continued
172
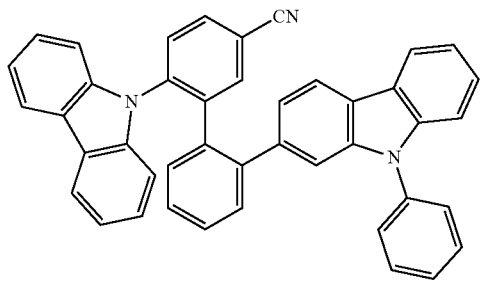
173
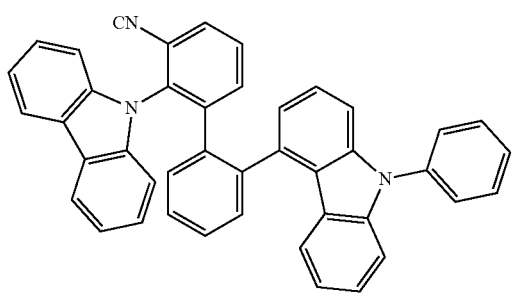
174
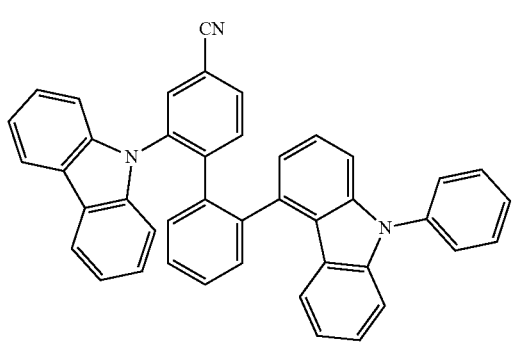
175
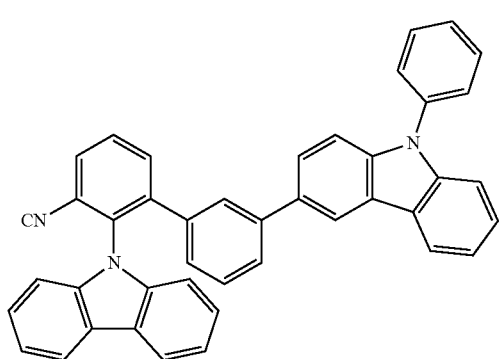
176
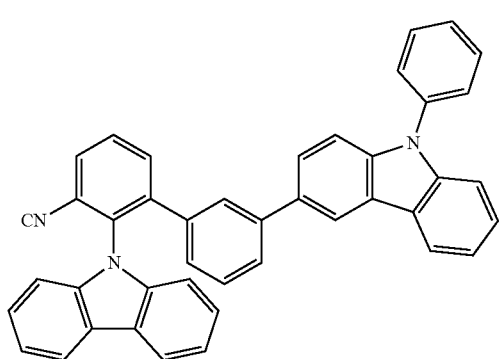
884
-continued
177
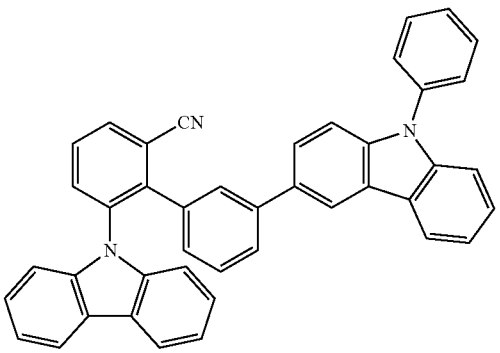
178
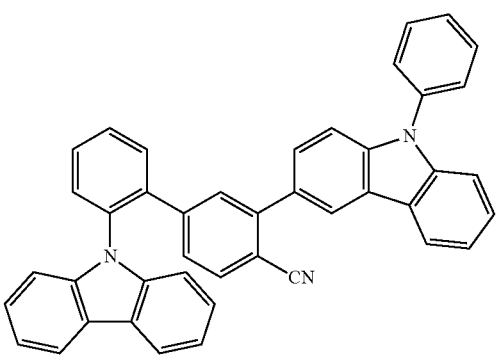
179
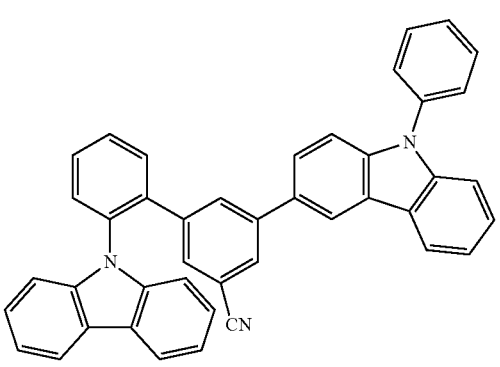
180
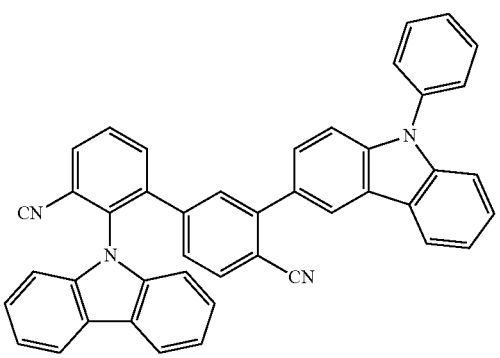

-continued
181
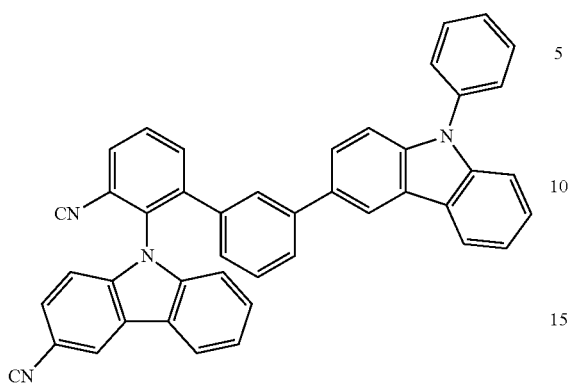
182
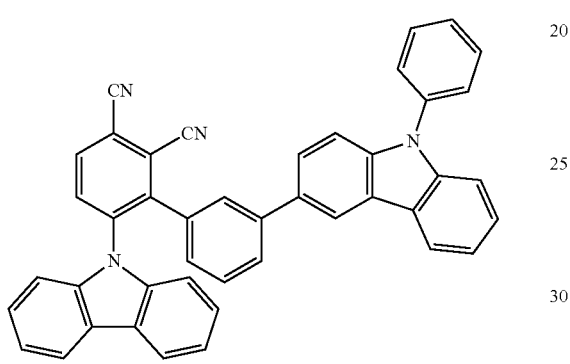
183
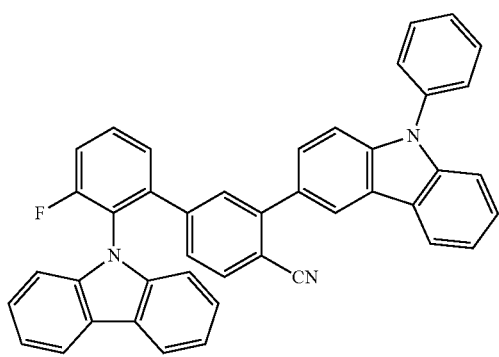
184
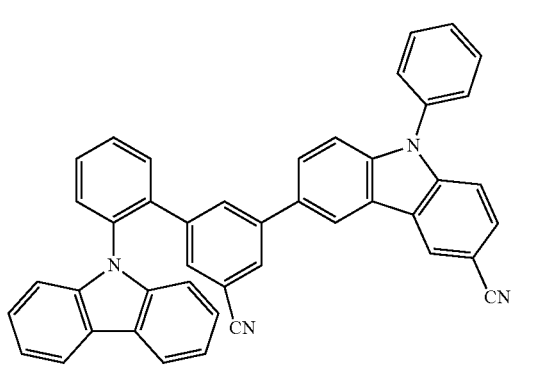
-continued
185
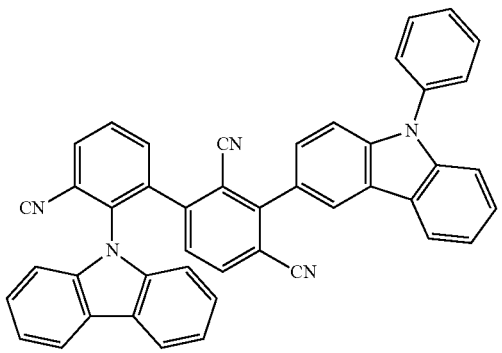
186
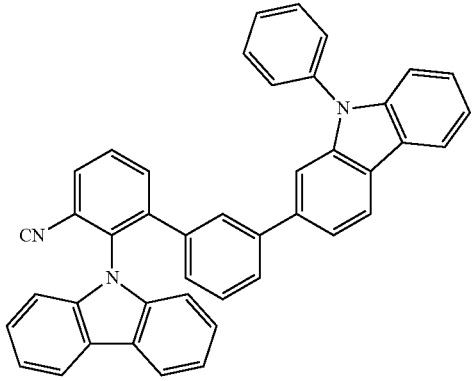
187
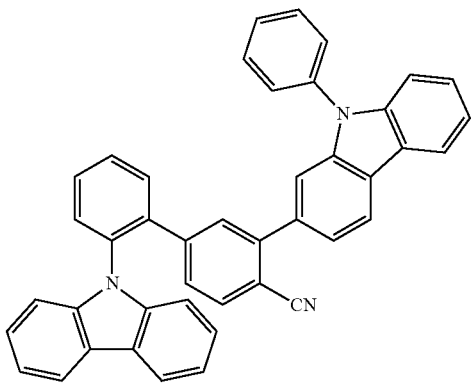
188
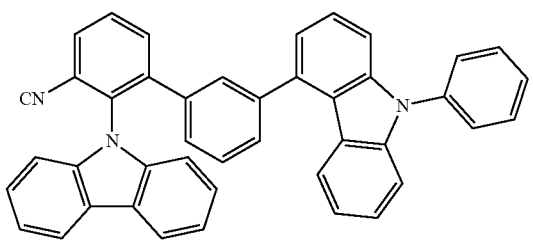

189
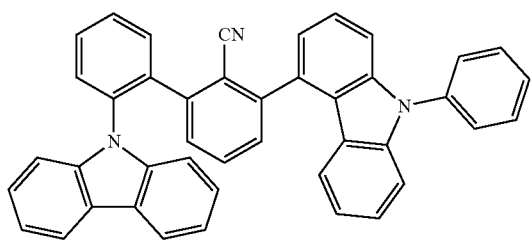
190
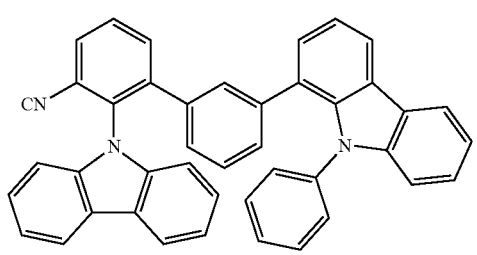
191
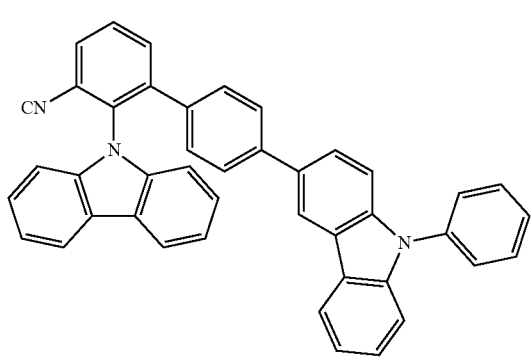
192
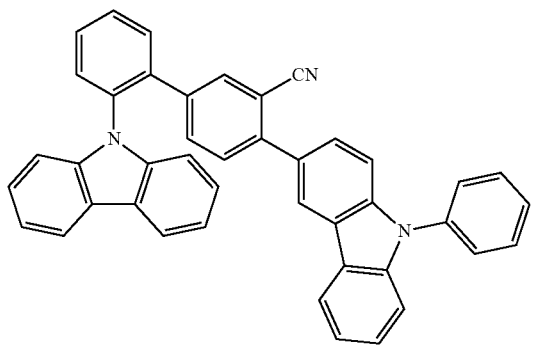
193
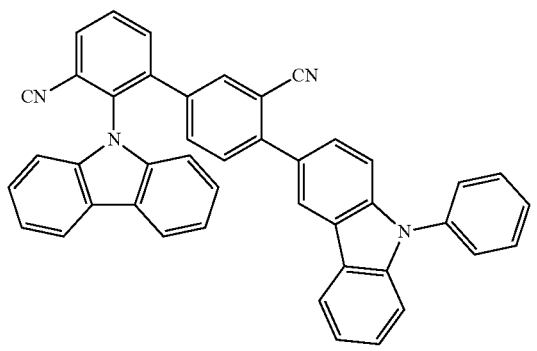
194
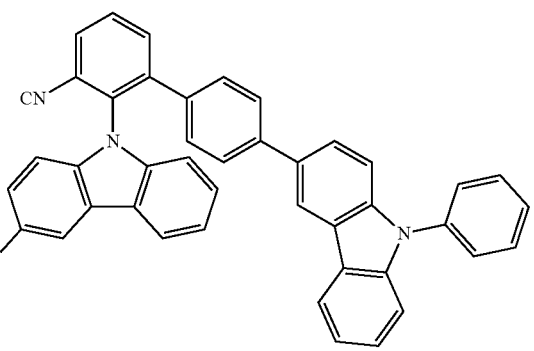
195
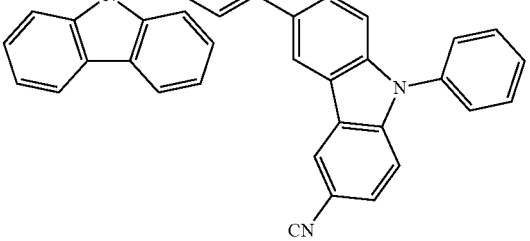
196
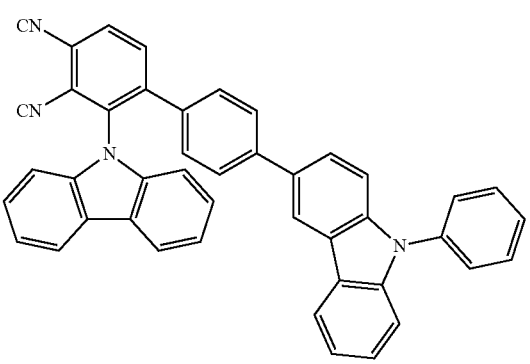
197
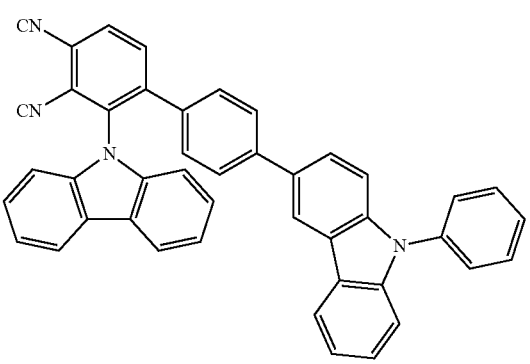

198
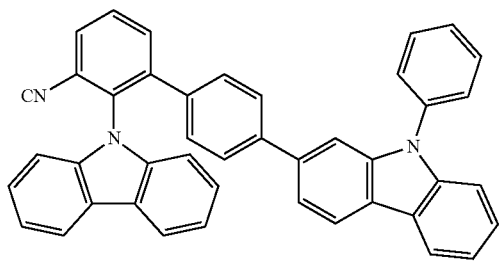
199
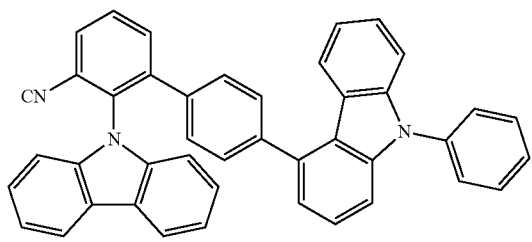
200
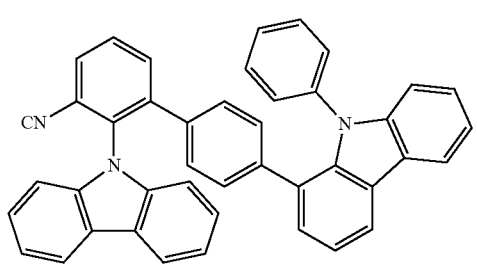
201
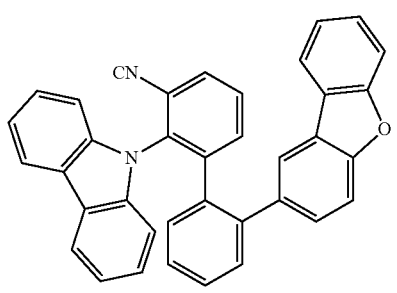
202
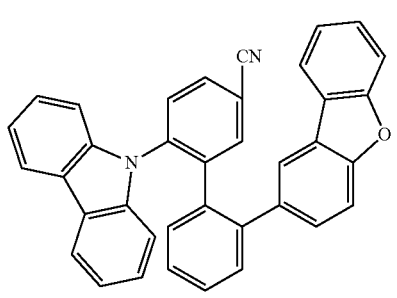
203
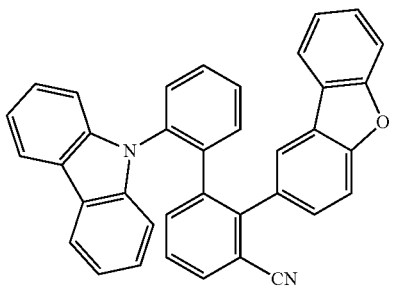
204
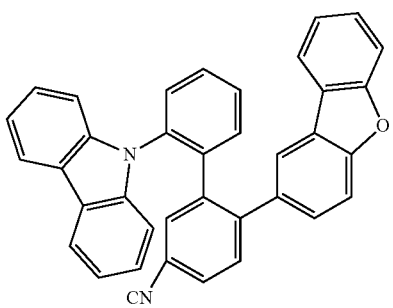
205
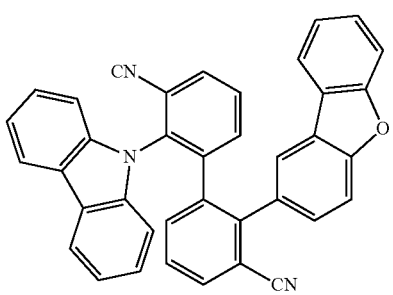
206
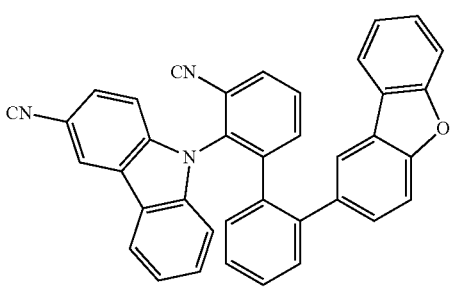
207
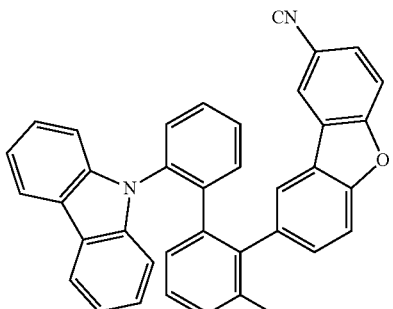

208
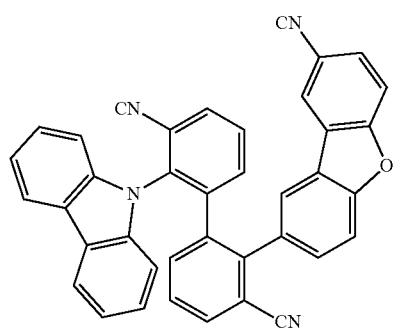
209
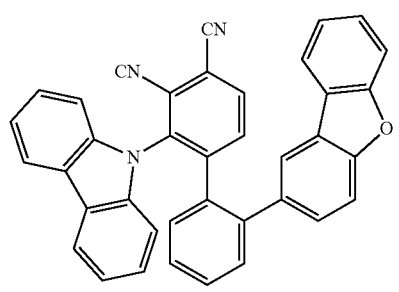
210
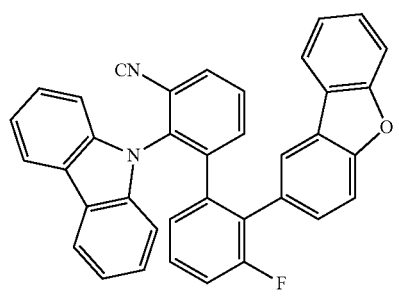
211
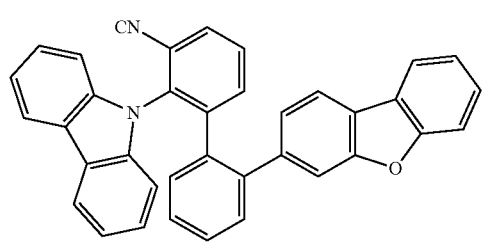
212
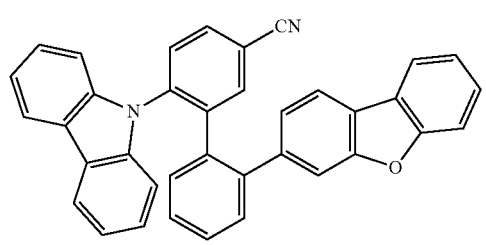
213
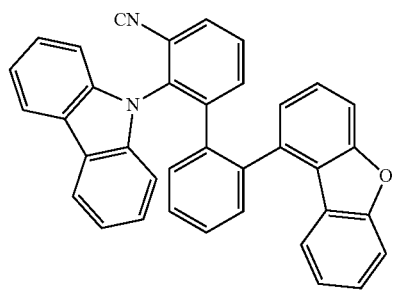
214
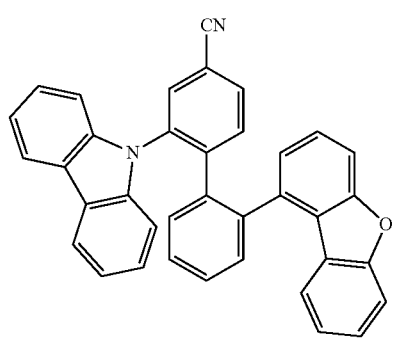
215
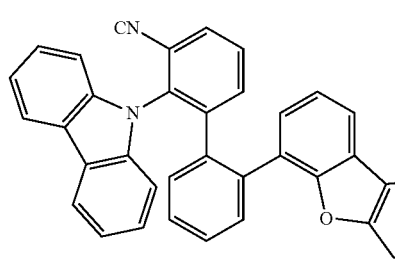
216
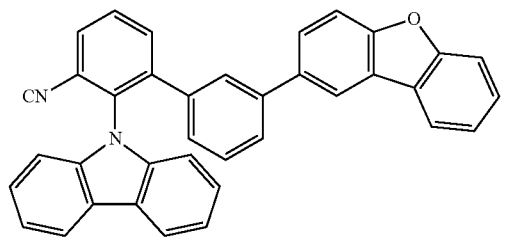
217
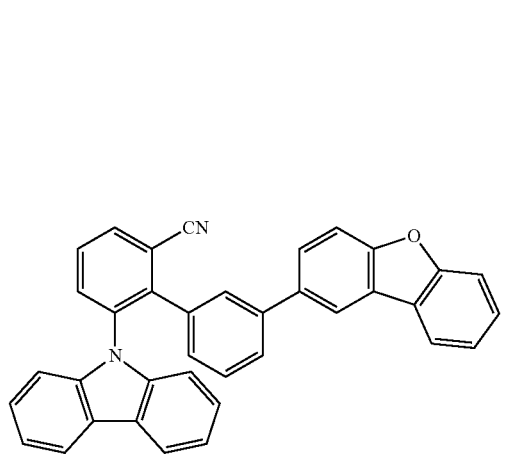

218
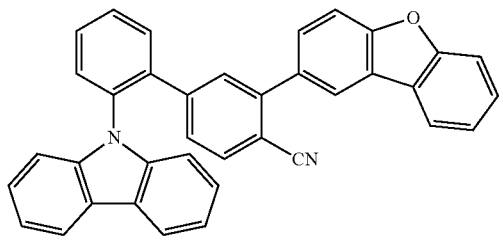
219
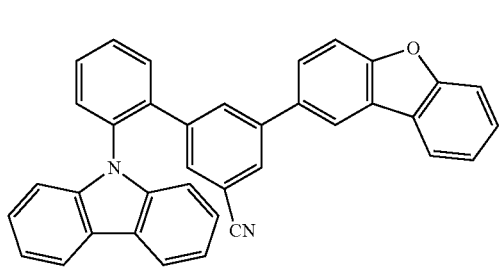
220
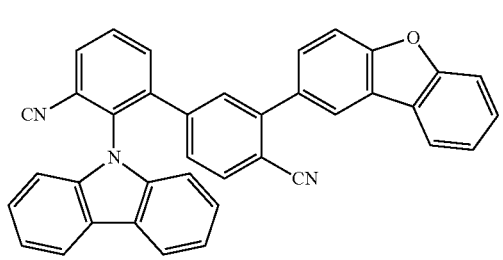
221
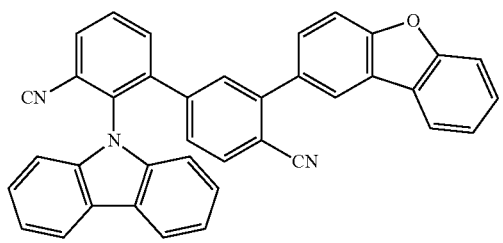
222
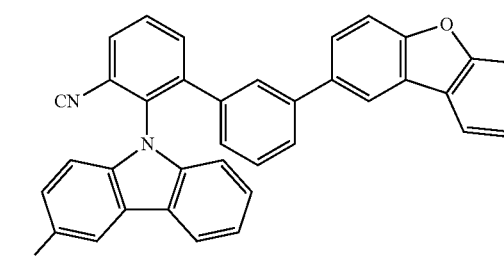
223
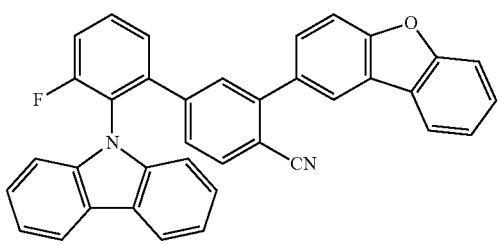
224
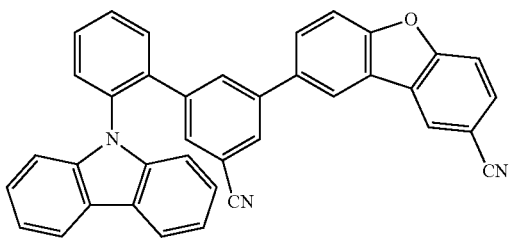
225
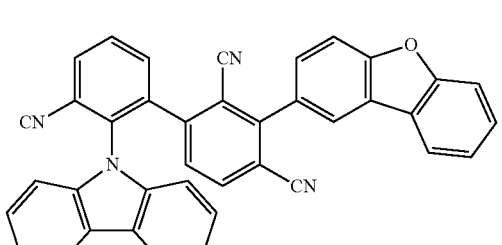
226
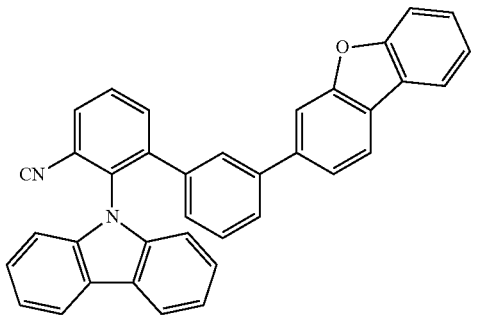
227
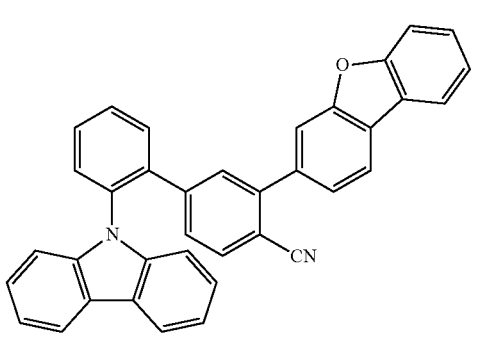

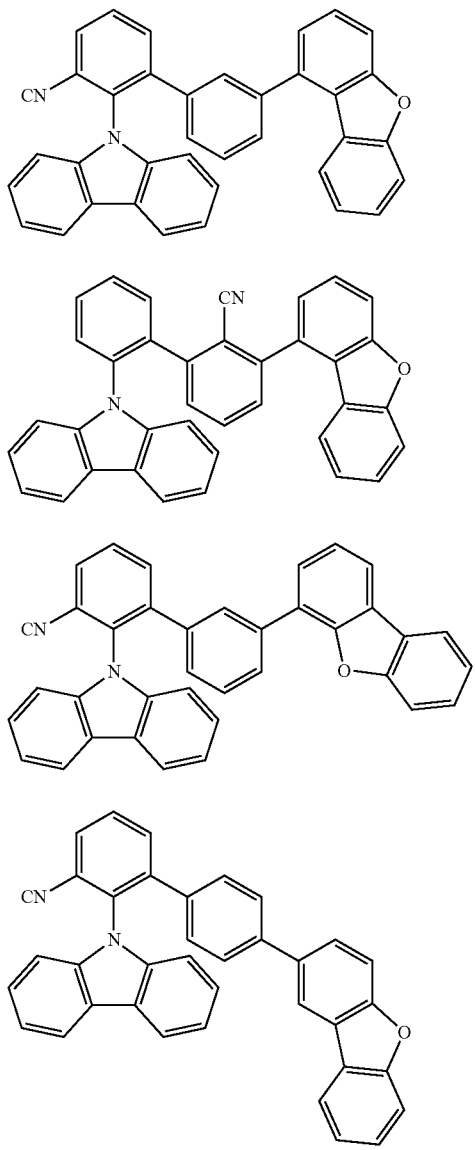
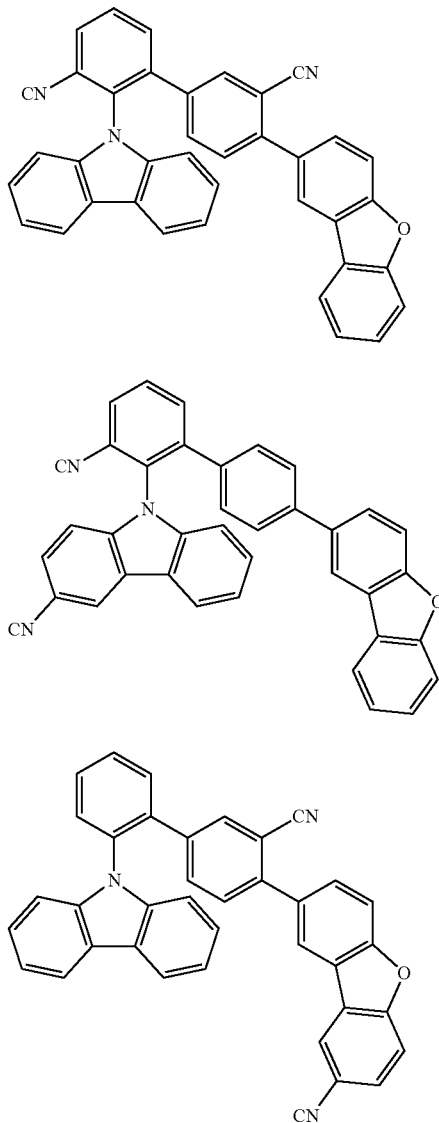
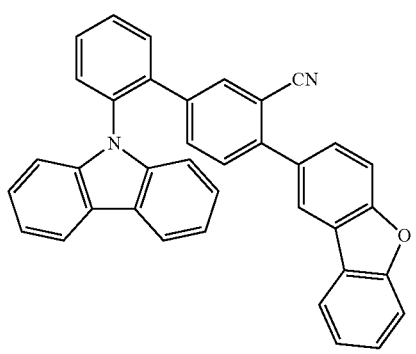

237
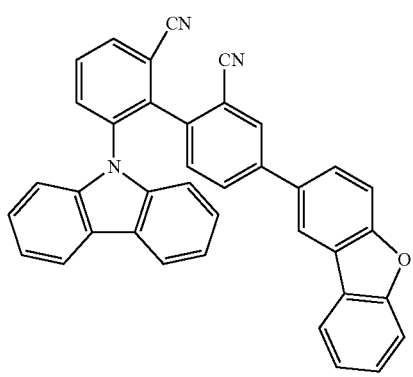
238
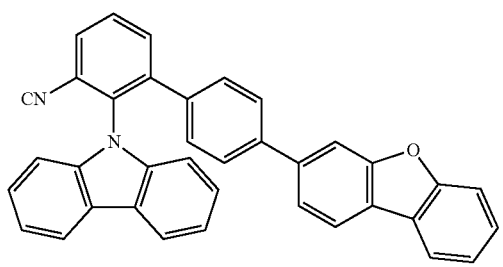
239
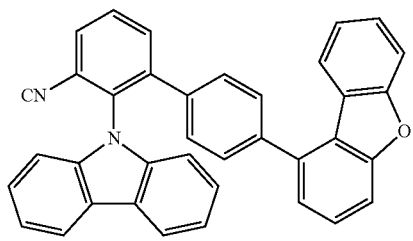
240
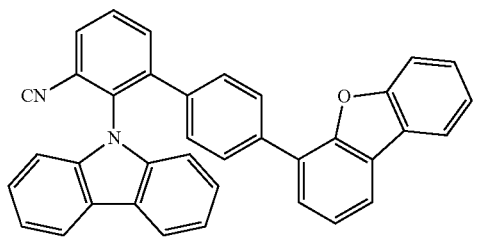
241
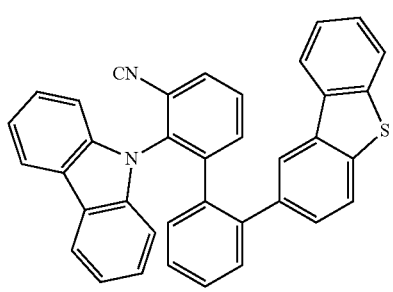
242
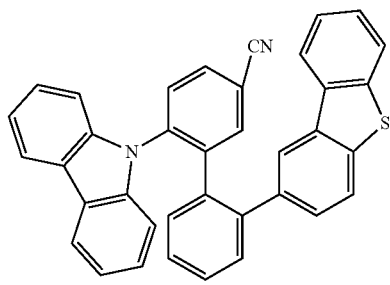
243
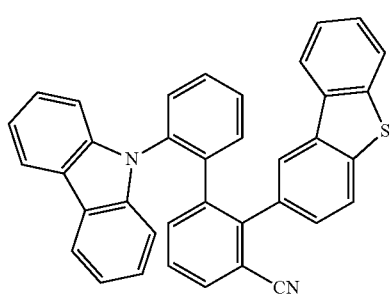
244
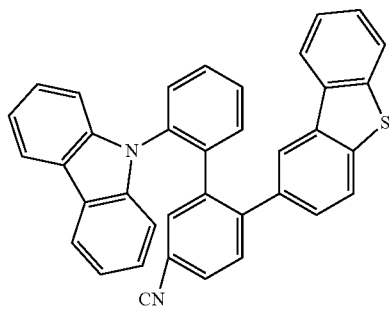
245
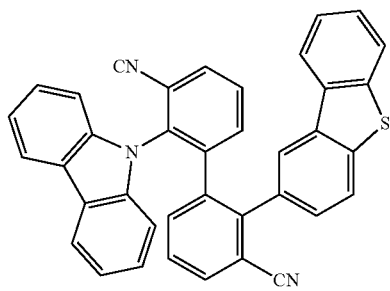
246
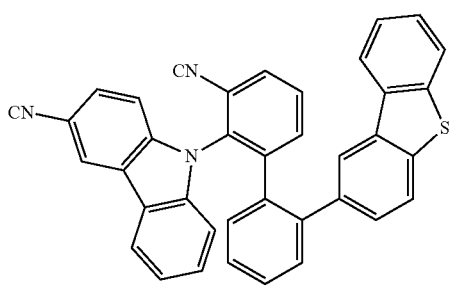

-continued
247
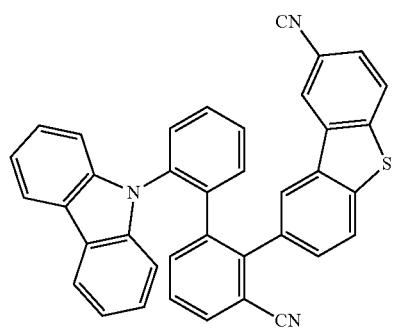
248
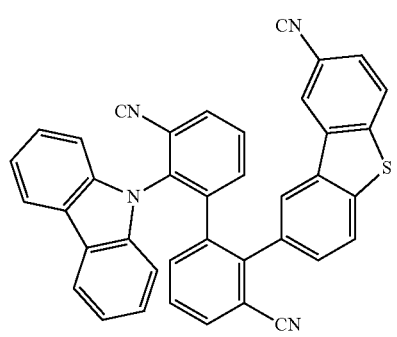
249
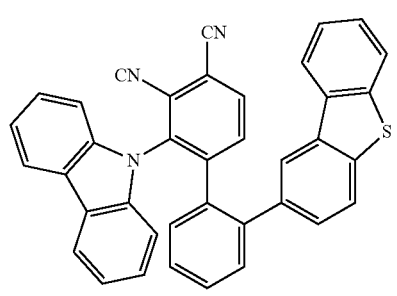
250
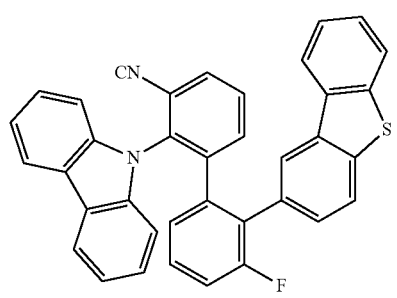
251
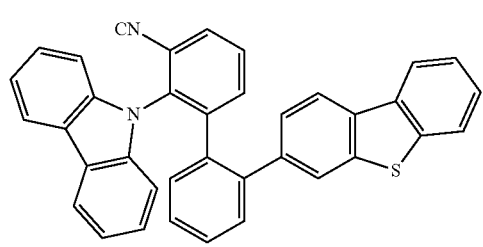
-continued
252
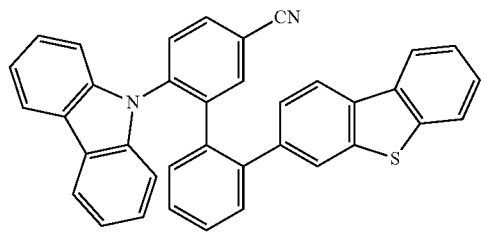
253
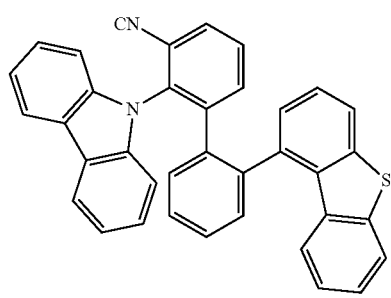
254
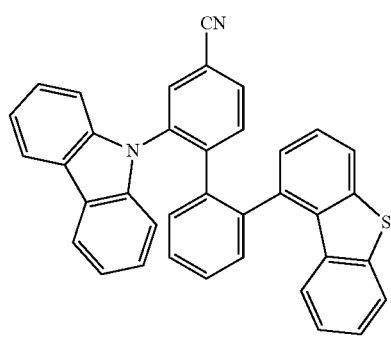
255
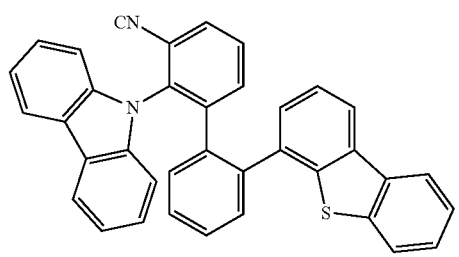
256
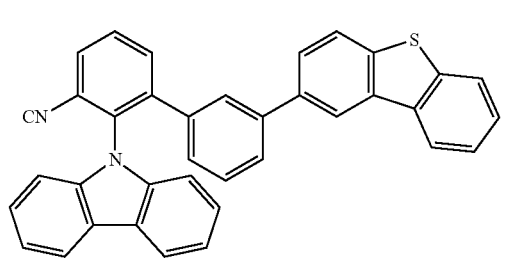

901
-continued
257
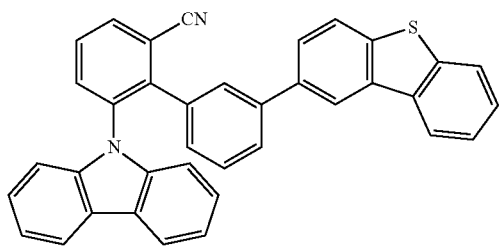
258
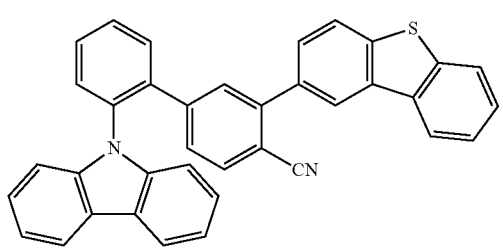
259
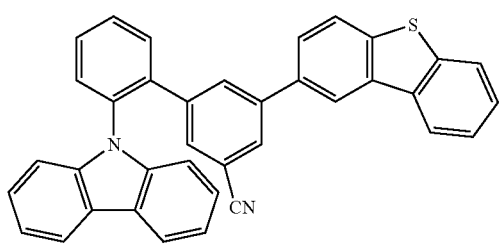
260
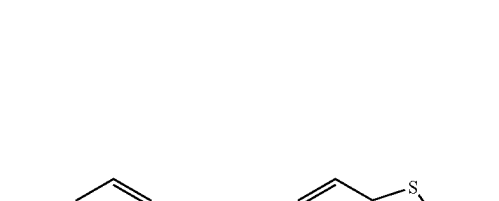
261
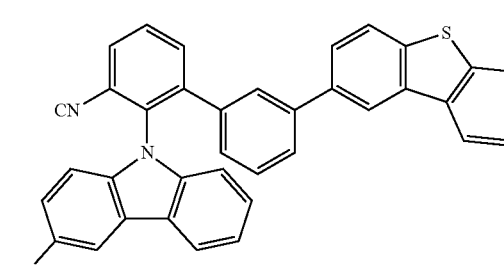
902
-continued
262
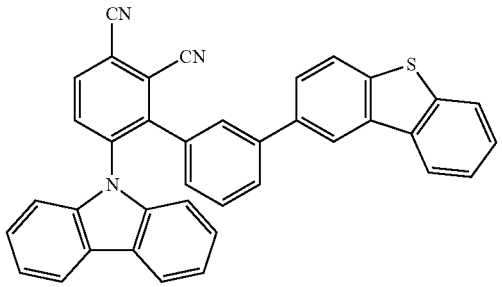
263
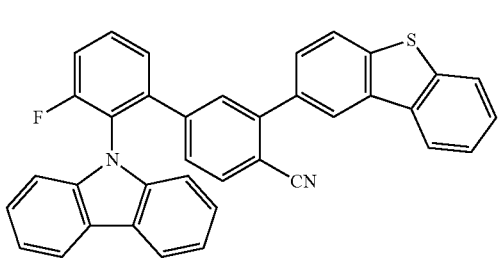
264
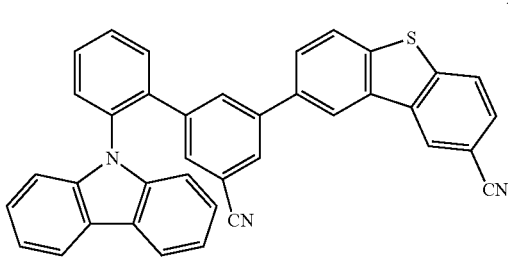
265
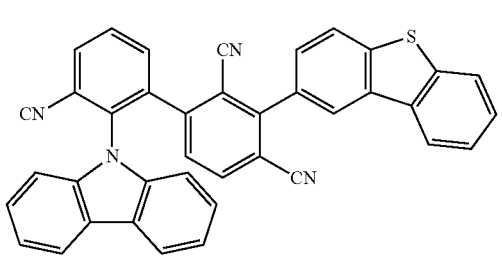
266
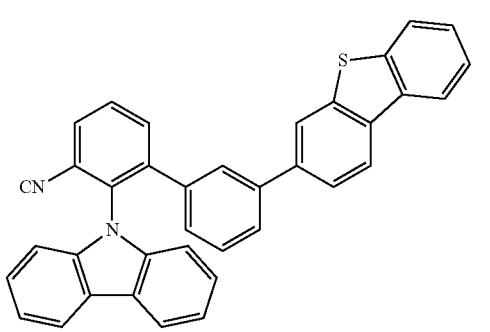

903
-continued
267
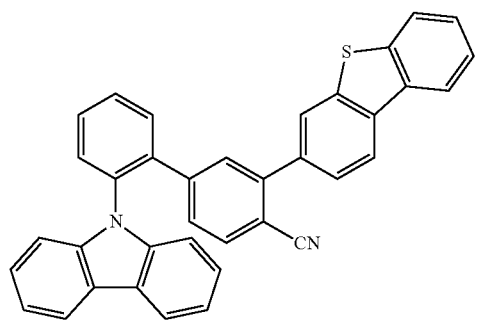
268
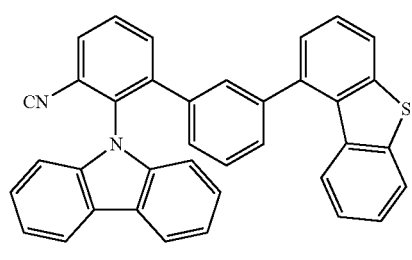
269
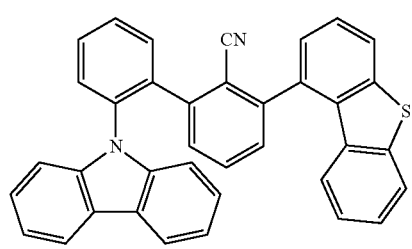
270
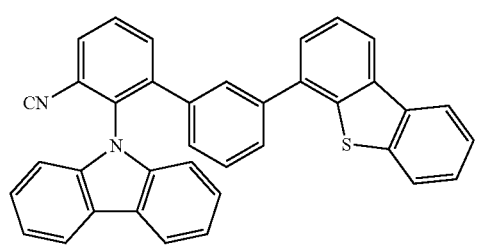
271
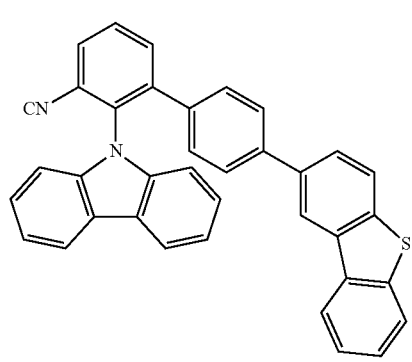
904
-continued
272
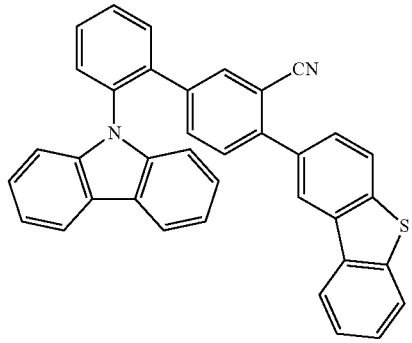
273
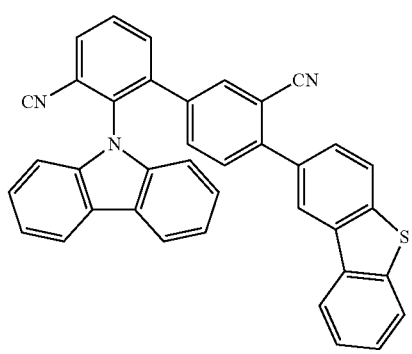
274
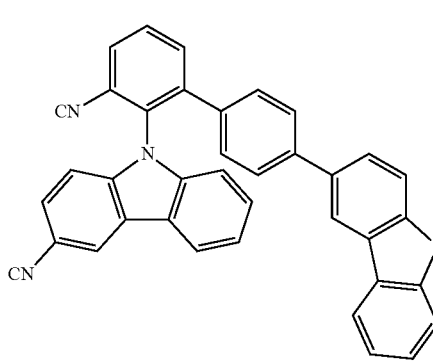
275
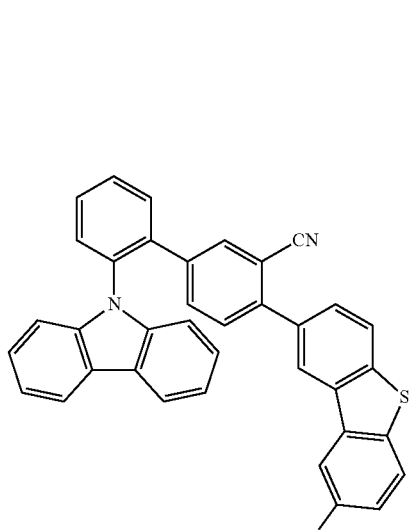

905
-continued
276
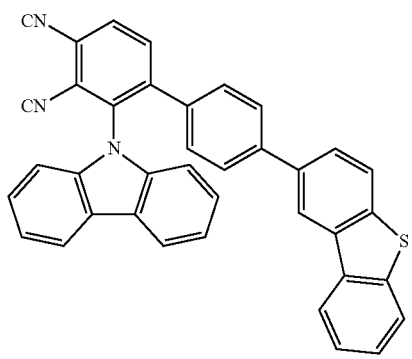
277
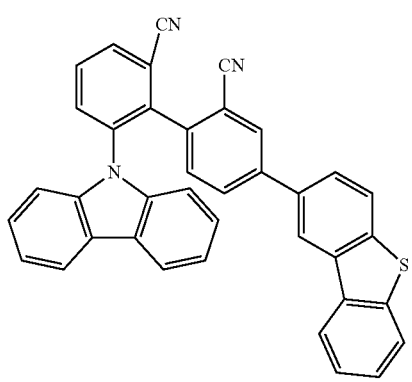
278
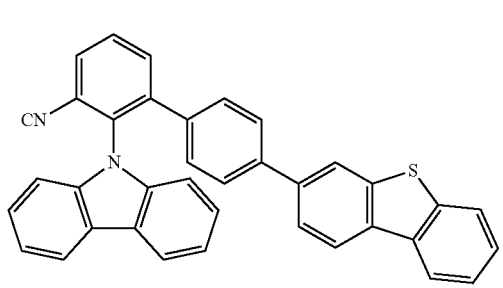
279
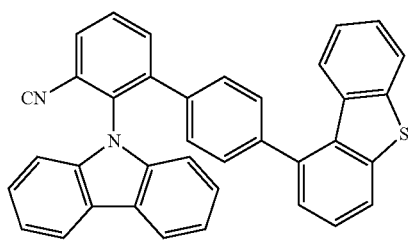
280
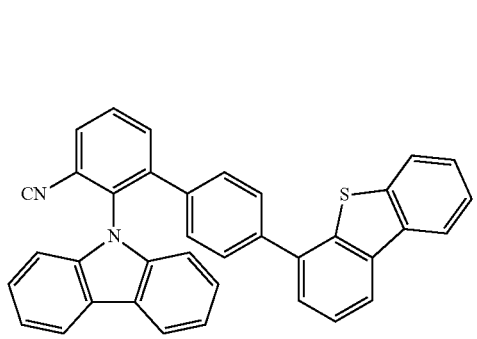
906
-continued
281
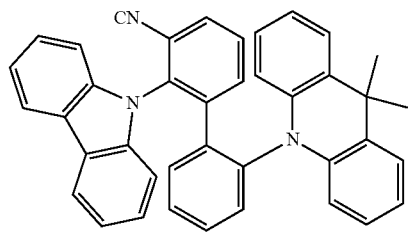
282
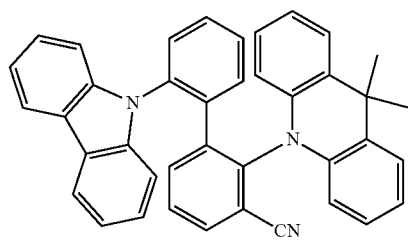
283
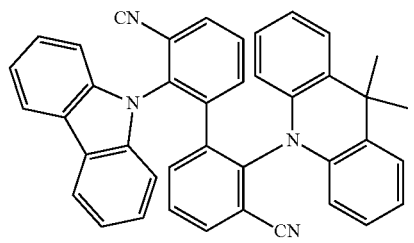
284
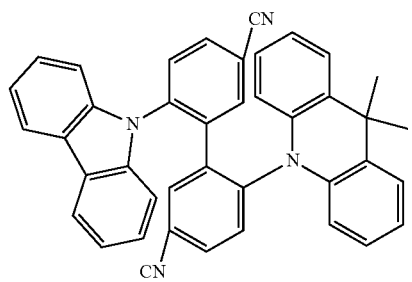
285
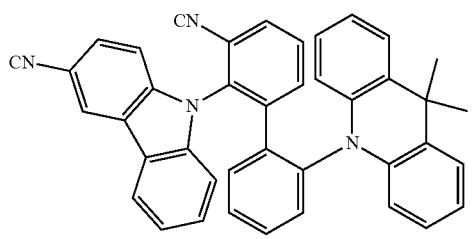
286
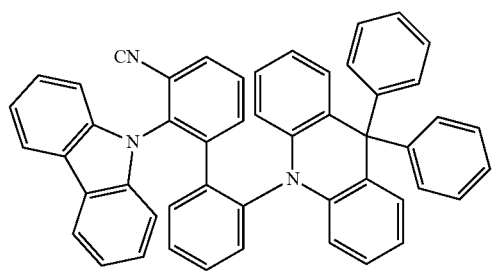

907 -continued
287
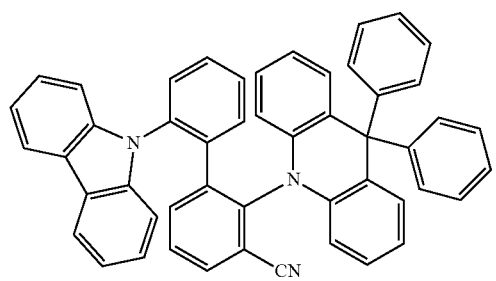
288
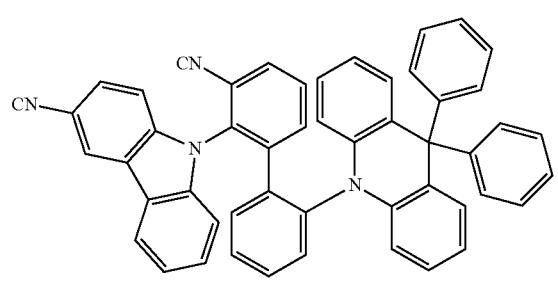
289
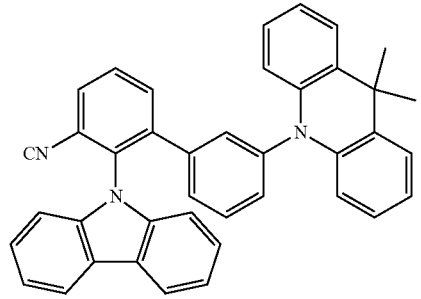
290
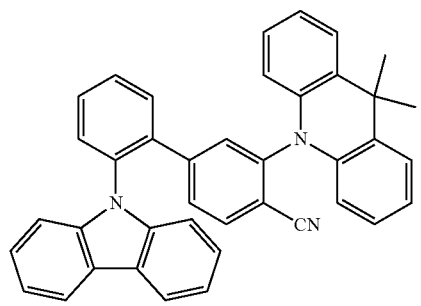
291
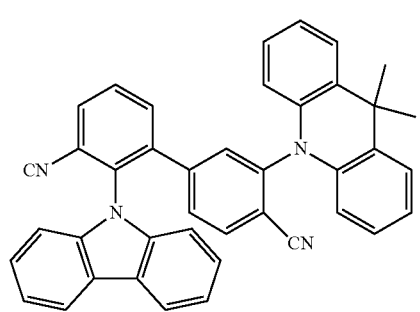
908 -continued
292
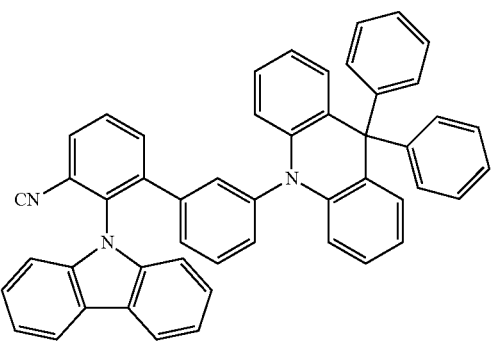
293
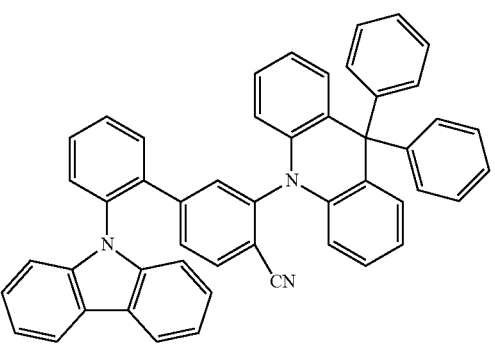
294
295
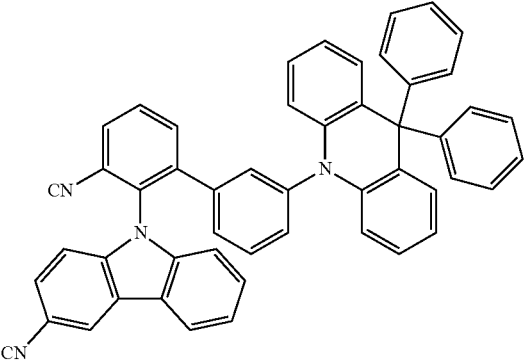

| 909 -continued | 910 -continued |
|---|---|
| 296 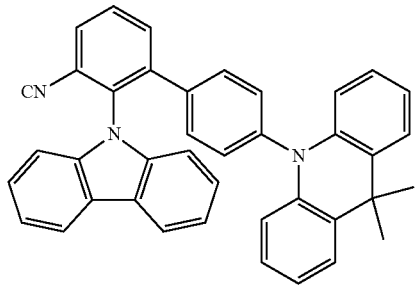 | 301 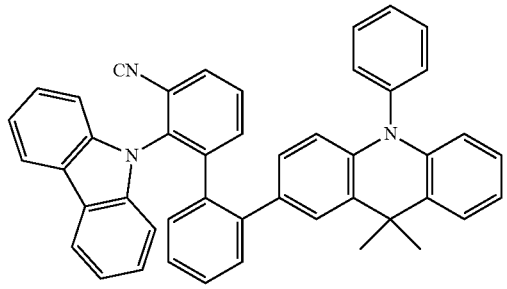 |
| 297 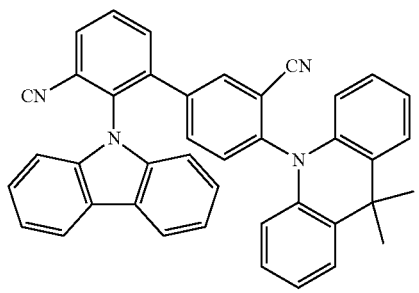 | 302 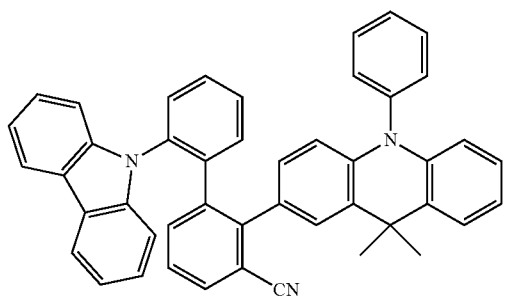 |
| 298 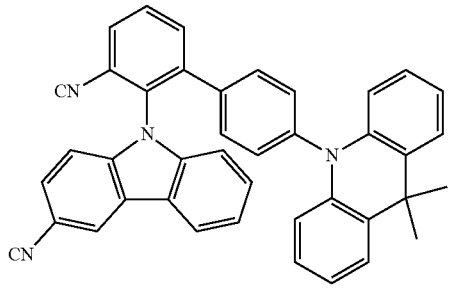 | 303 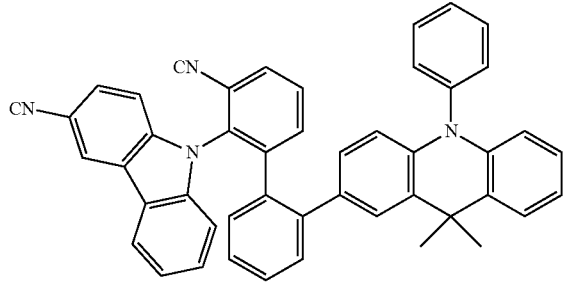 |
| 299 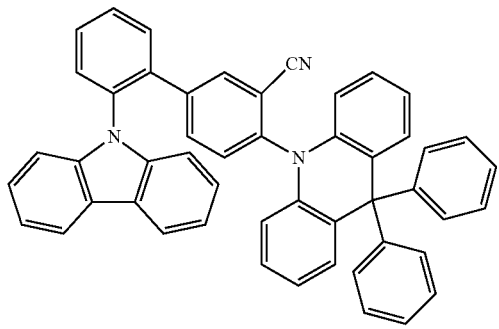 | 304 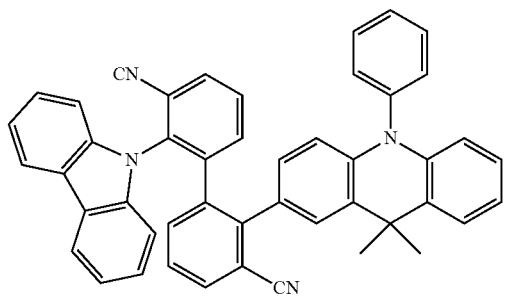 |
| 300 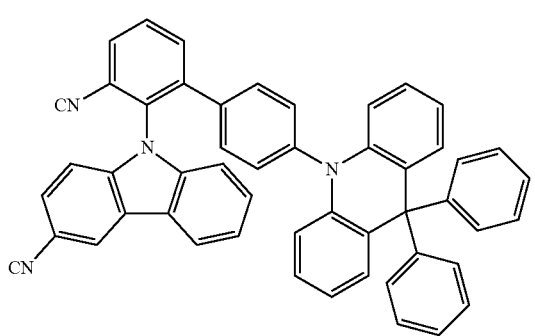 | 305 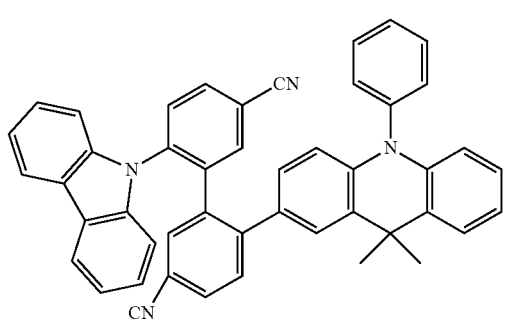 |

-continued
306
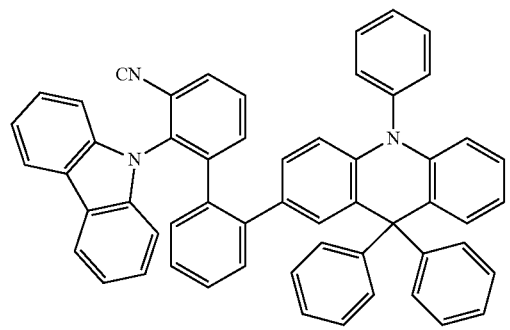
307
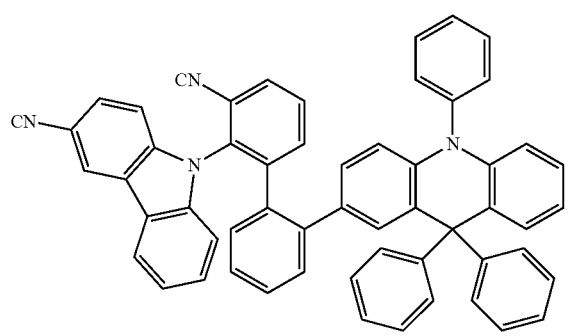
308
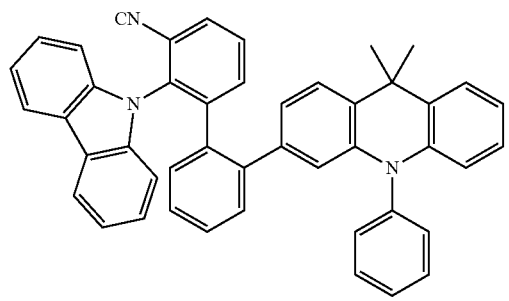
309
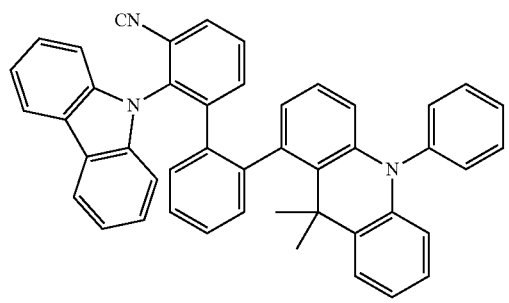
310
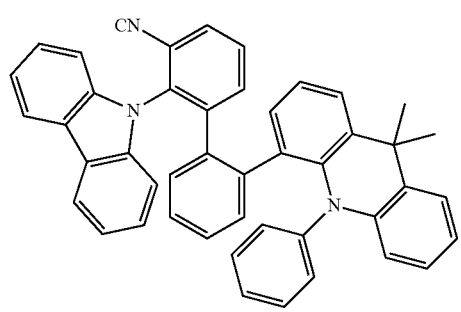
-continued
311
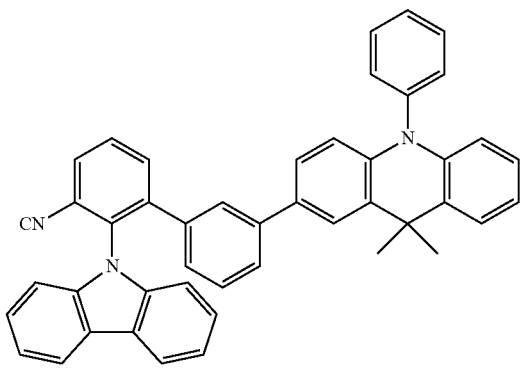
312
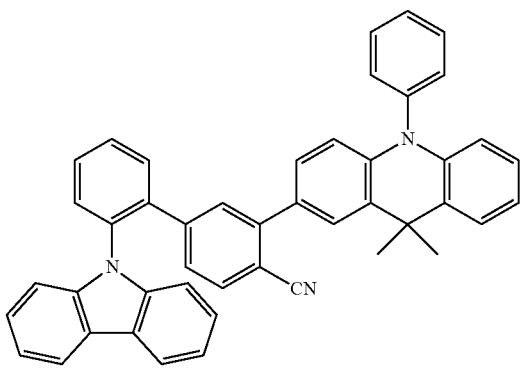
313
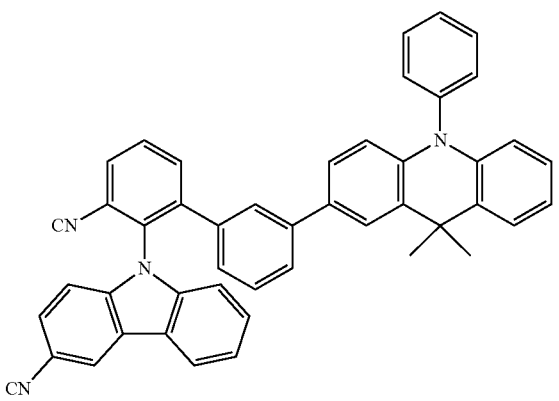
314
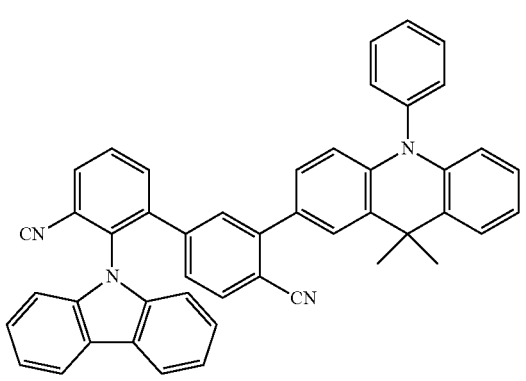

| 913 | 914 |
|---|---|
| -continued | -continued |
315
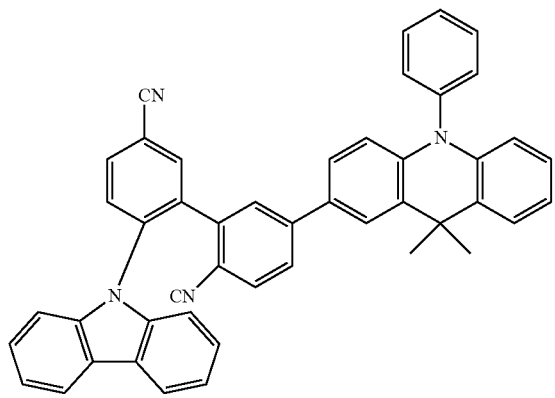
316
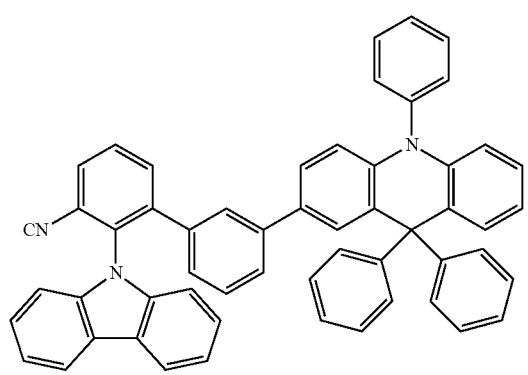
317
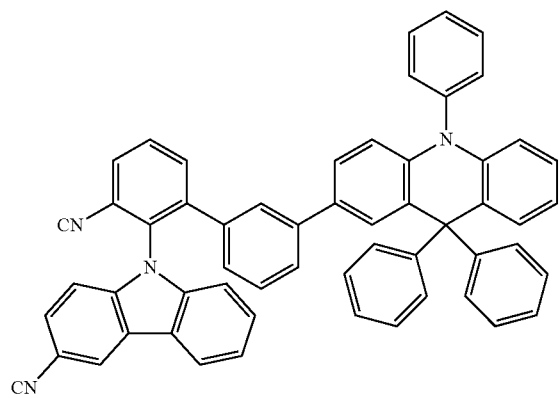
318
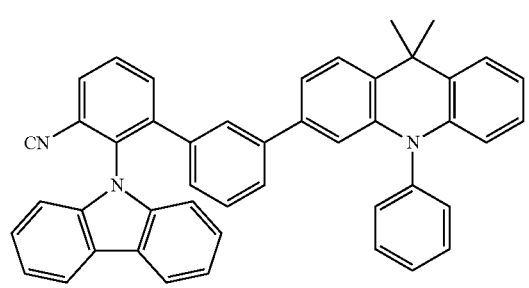
319
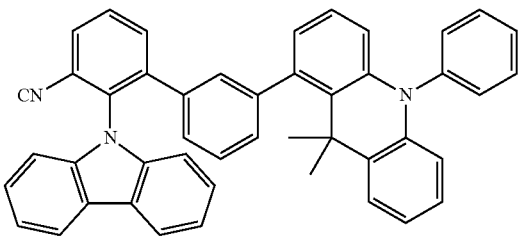
320
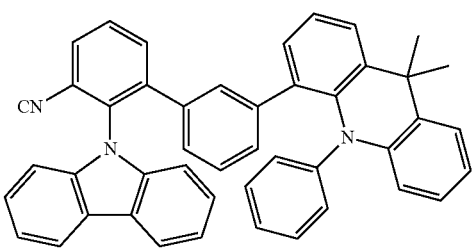
321
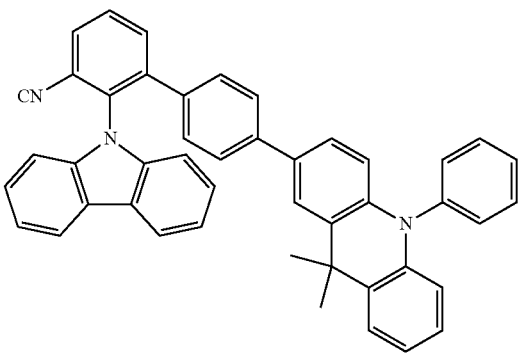
322
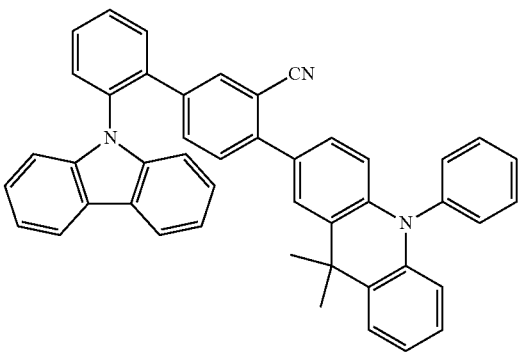
323
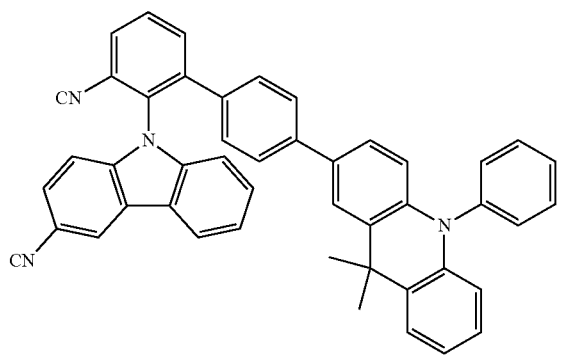

-continued
324
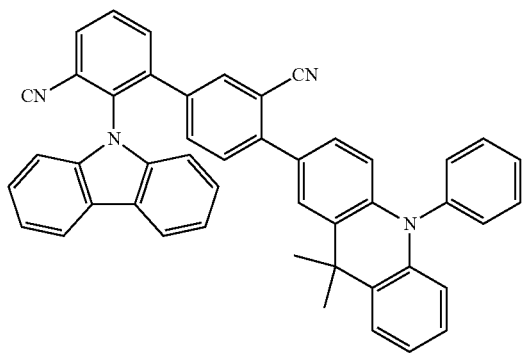
325
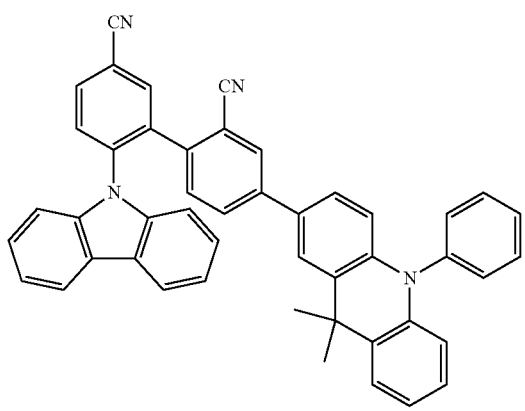
326
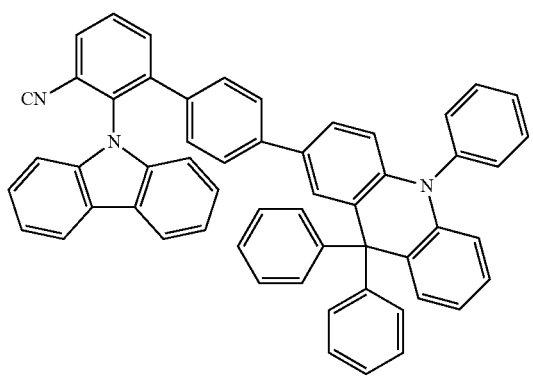
327
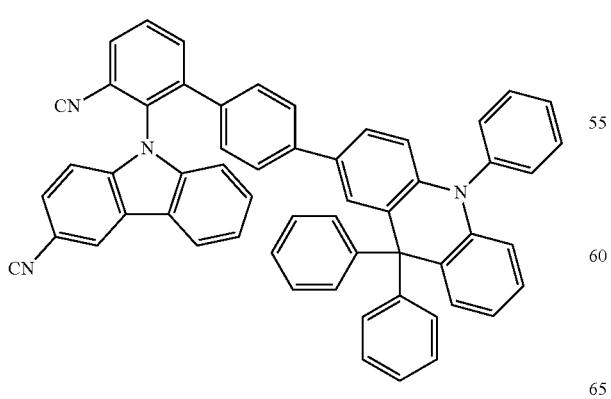
-continued
328
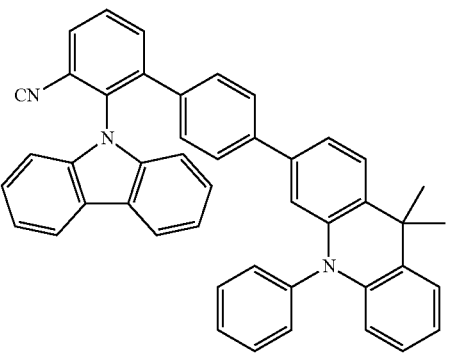
329
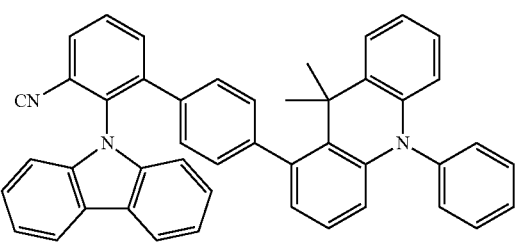
330
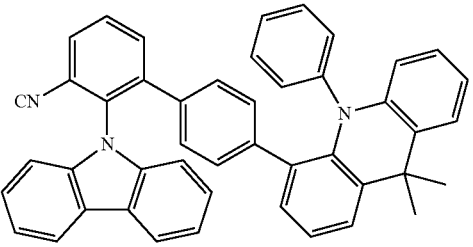
Group HE7
1
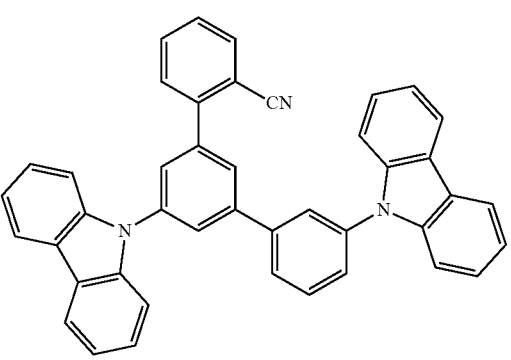

917
-continued
2
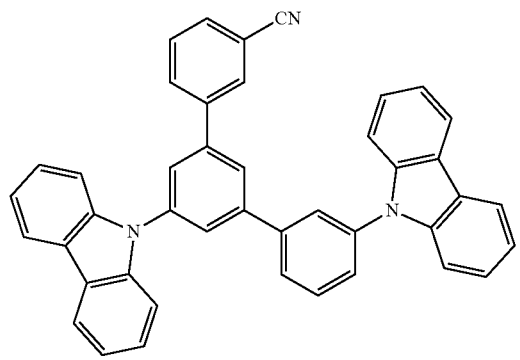
3
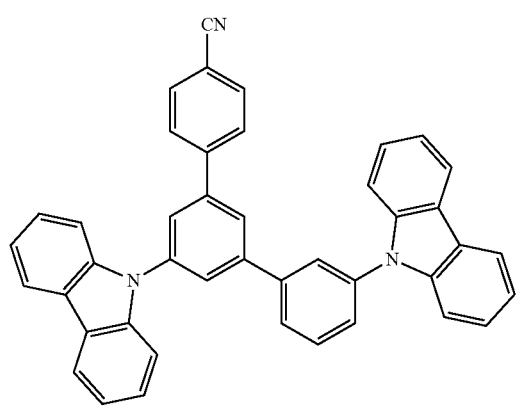
4
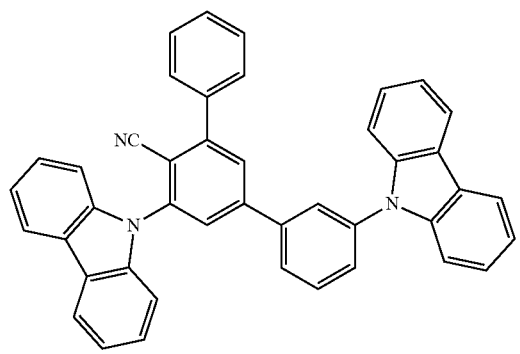
5
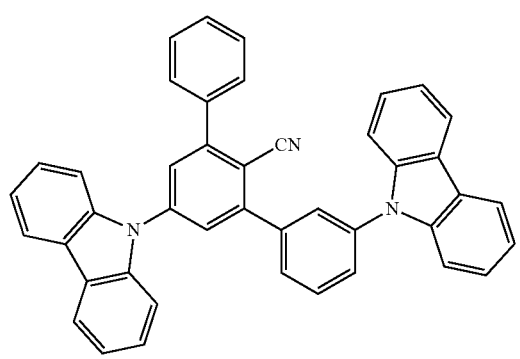
918
-continued
6
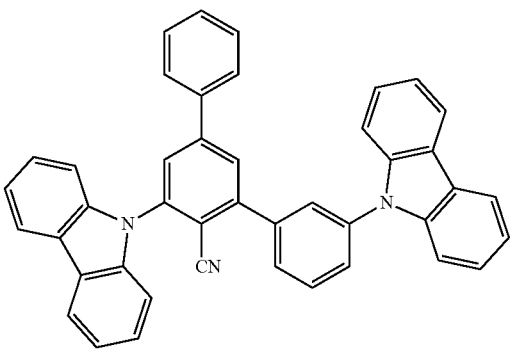
7
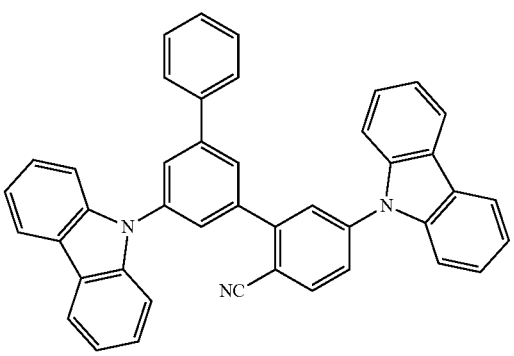
8
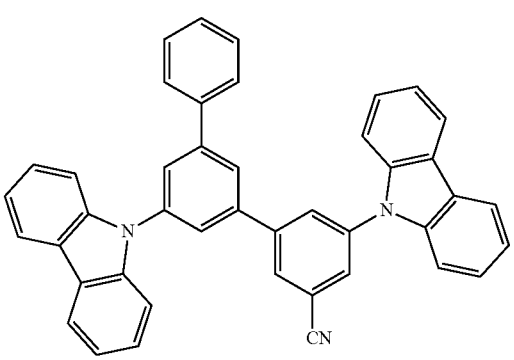
9
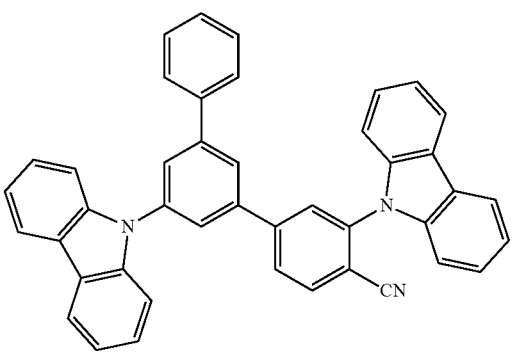

919
-continued
10
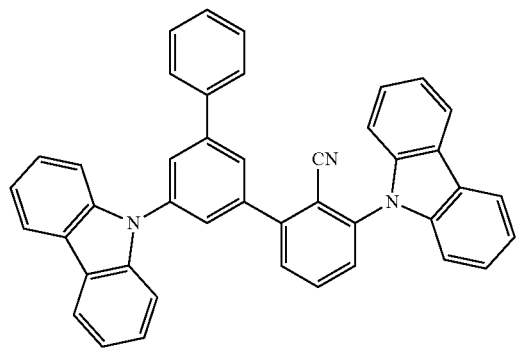
11
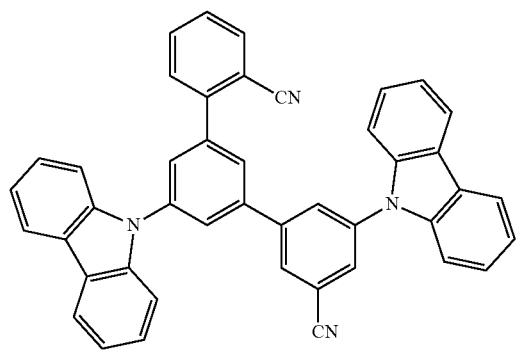
12
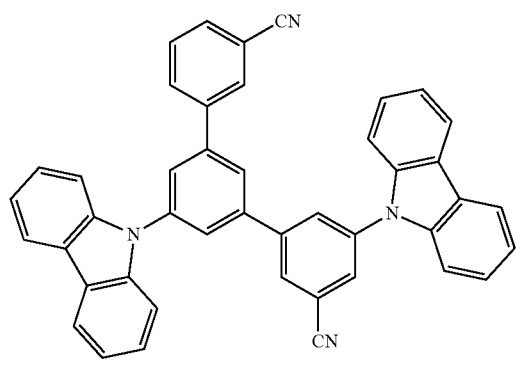
13
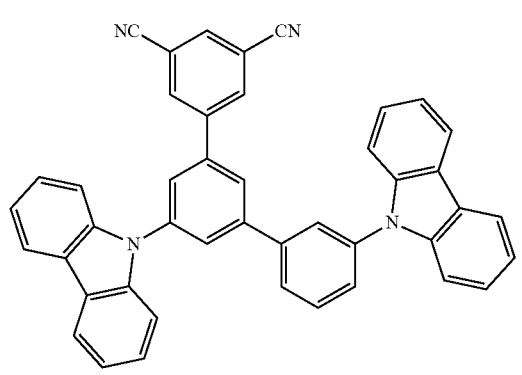
920
-continued
14
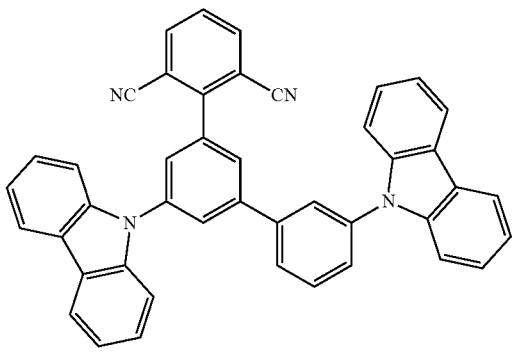
15
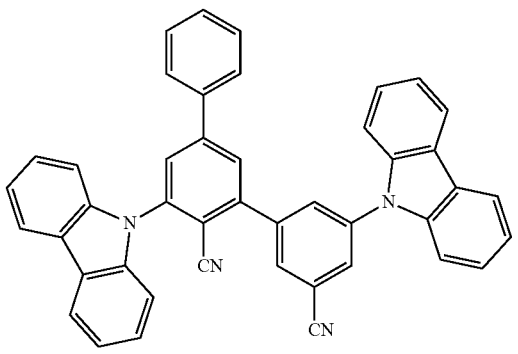
16
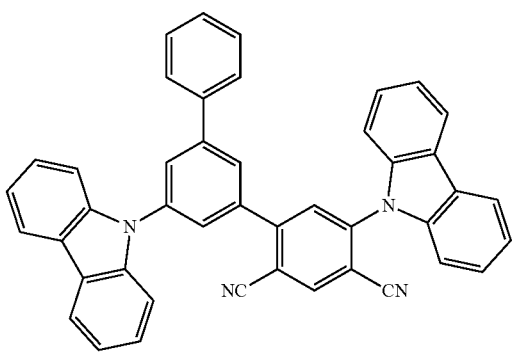
17
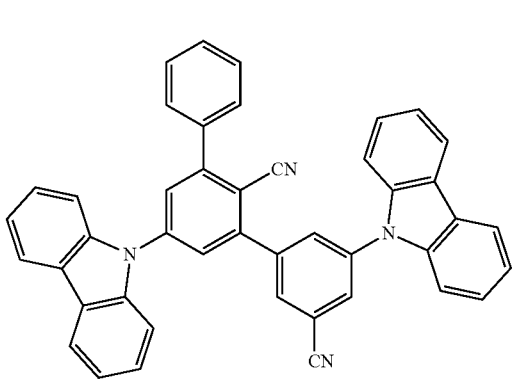

18
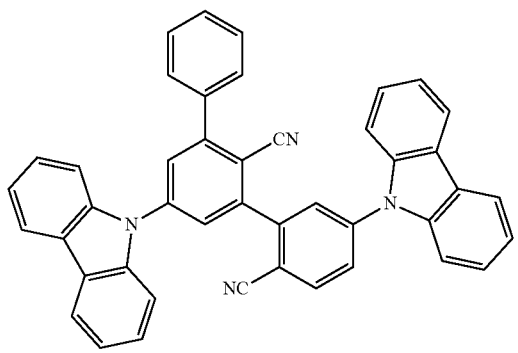
19
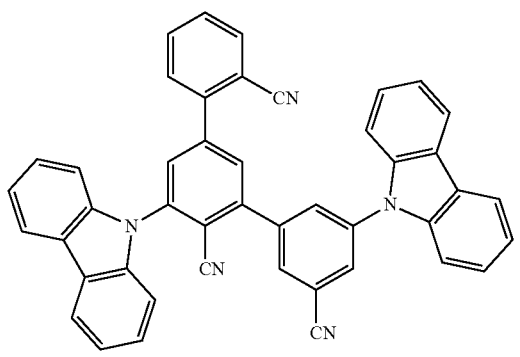
20
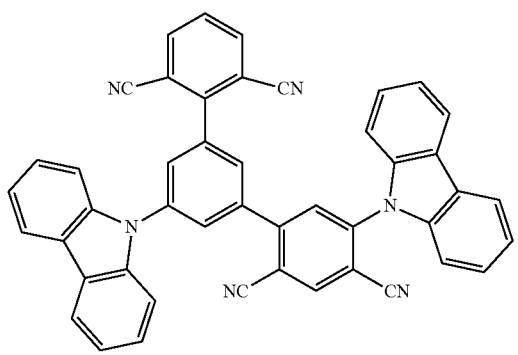
In some embodiments, the electron transporting host may include DPEPO and/or TSPO1:
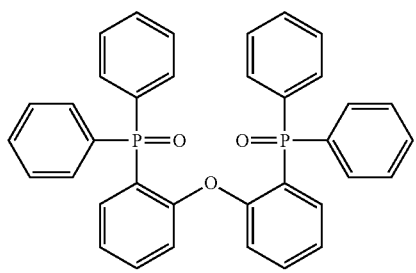
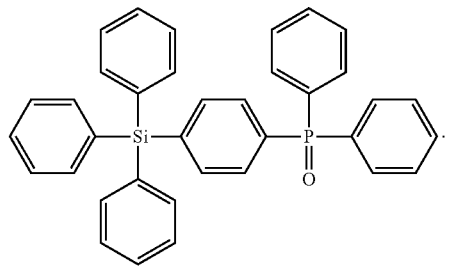
In some embodiments, the hole transporting host may be Group HH1, but embodiments are not limited thereto:
Group HH1
H-H1
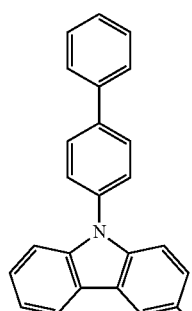
H-H2
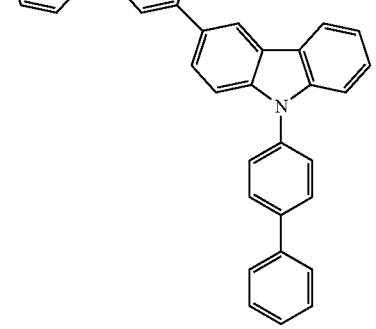

923
-continued
H-H3
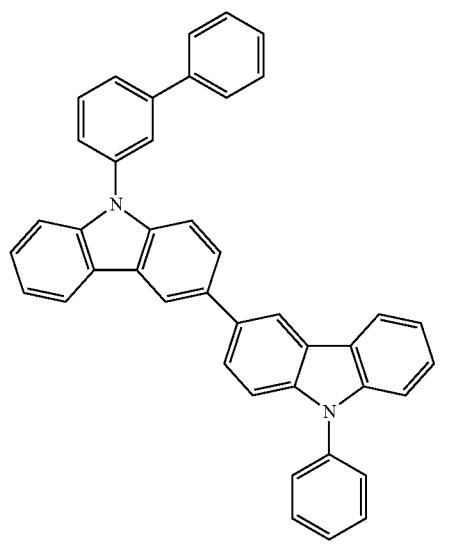
H-H4
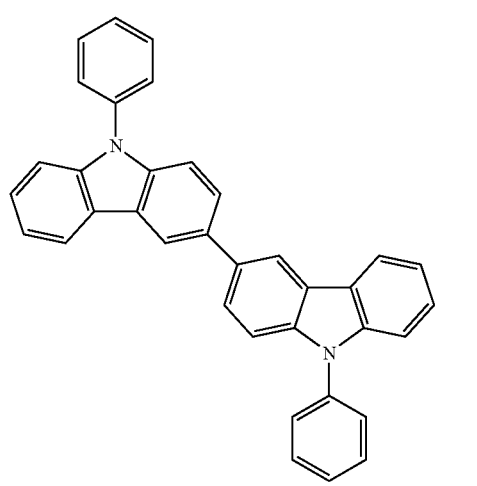
H-H5
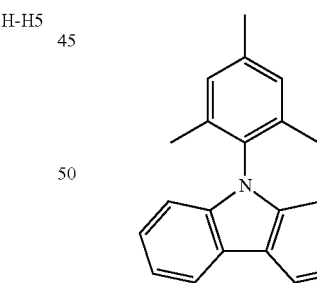
924
-continued
H-H6
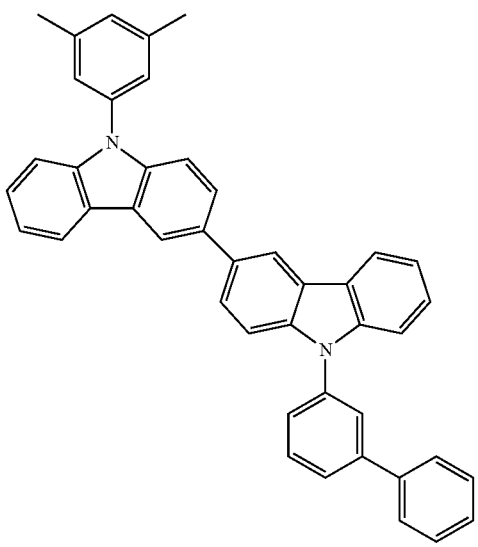
H-H7
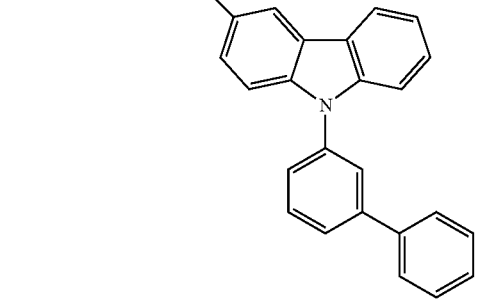

925
-continued
926
-continued
H-H8
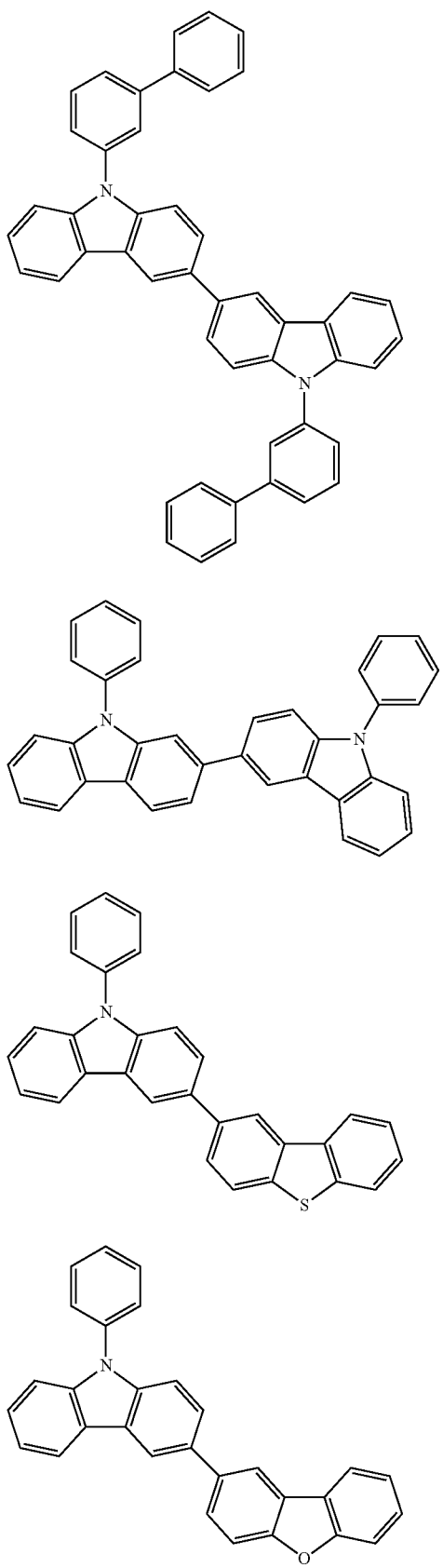
H-H9
H-H10
H-H11
H-H12
H-H13
H-H14
H-H15

927
-continued
H-H16
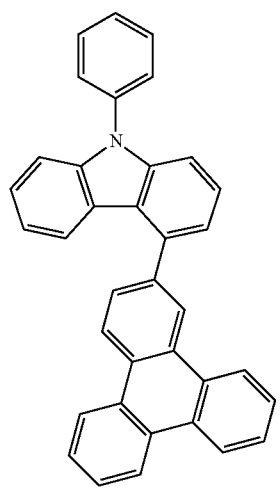
H-H17
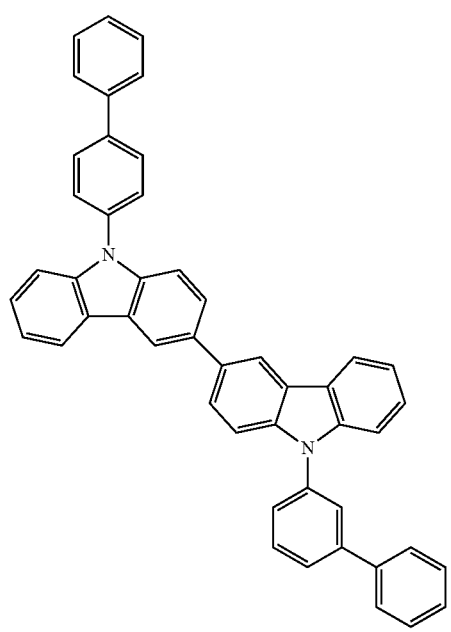
H-H18
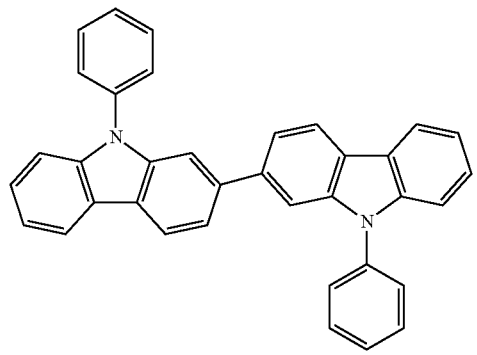
928
-continued
H-H19
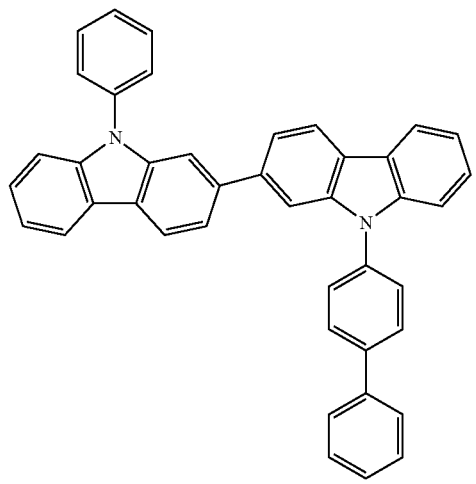
H-H20
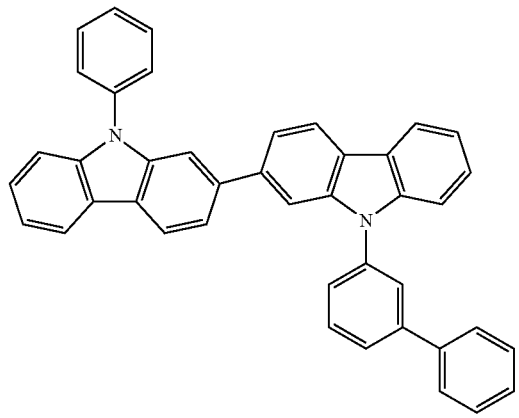
H-H21
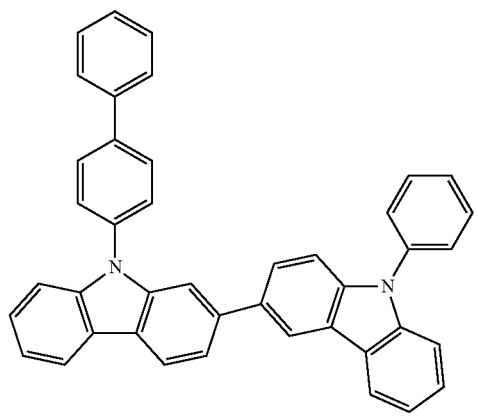

H-H22
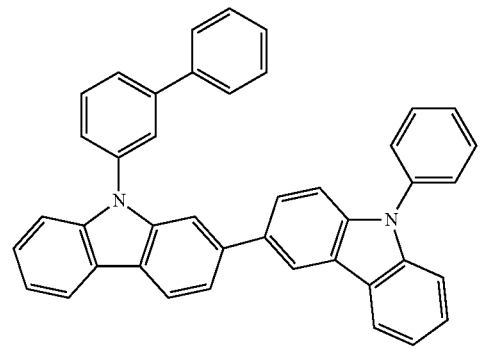
H-H23
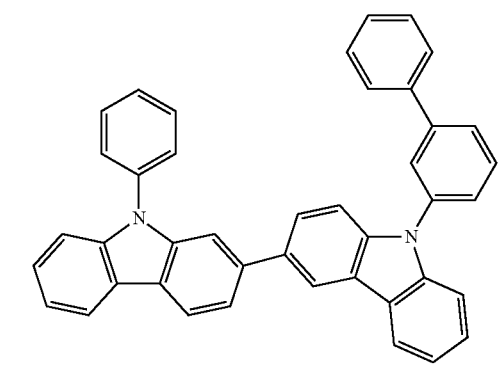
H-H24
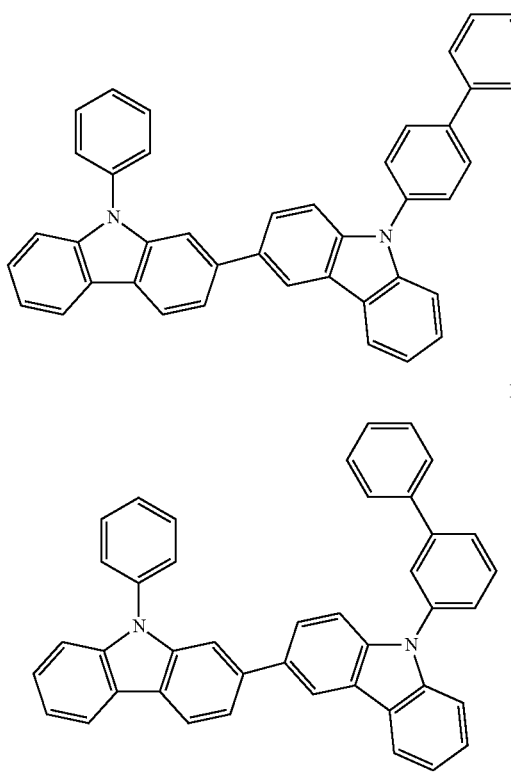
H-H25
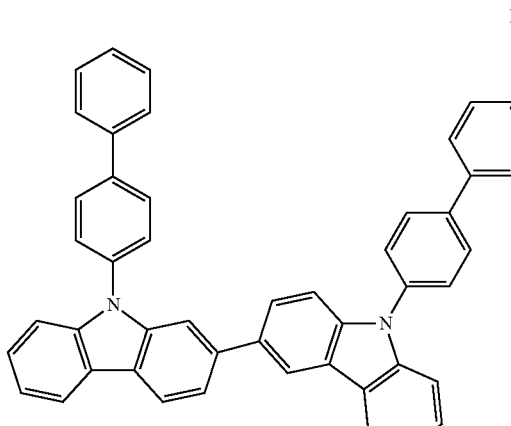
H-H26
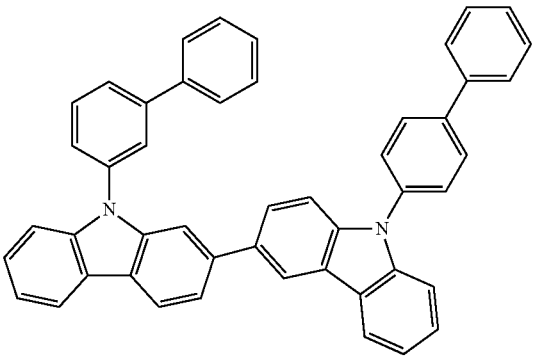
H-H27
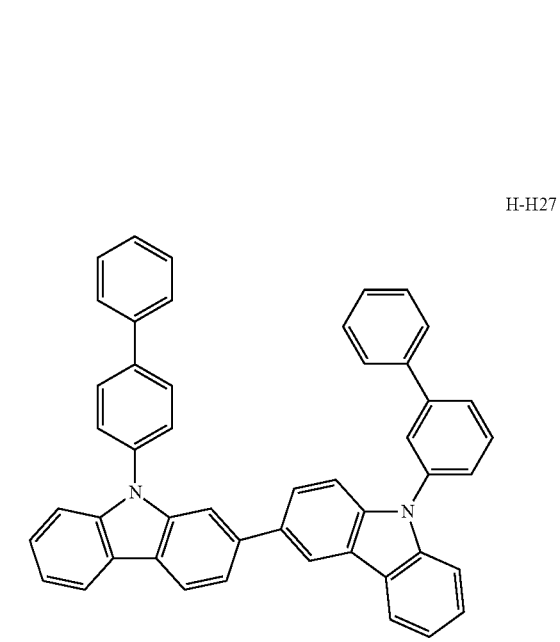
H-H28
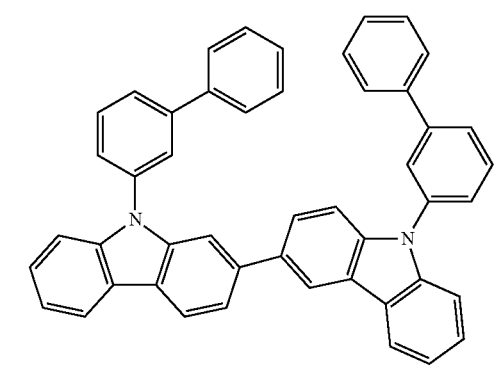

931
-continued
H-H29
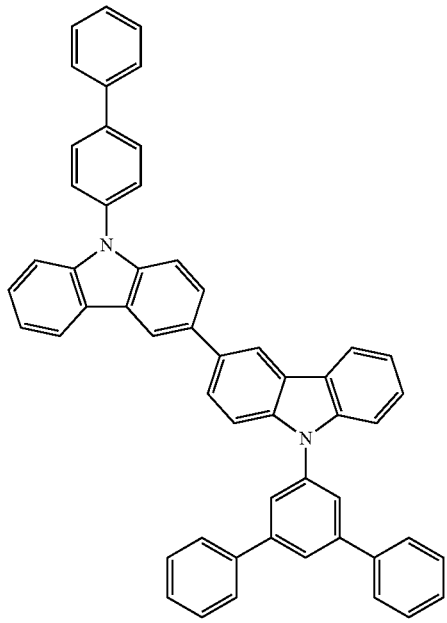
932
-continued
H-H31
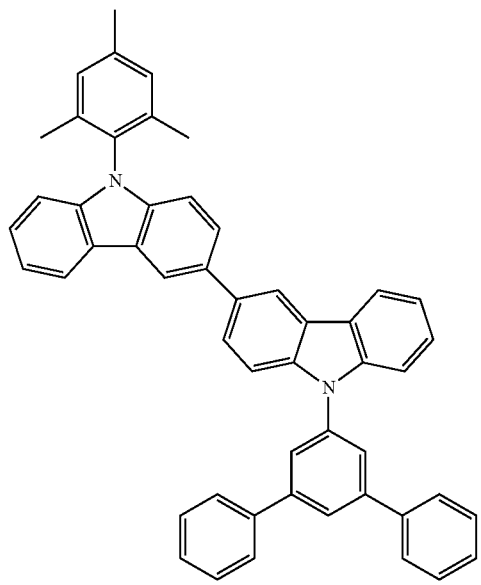
H-H30
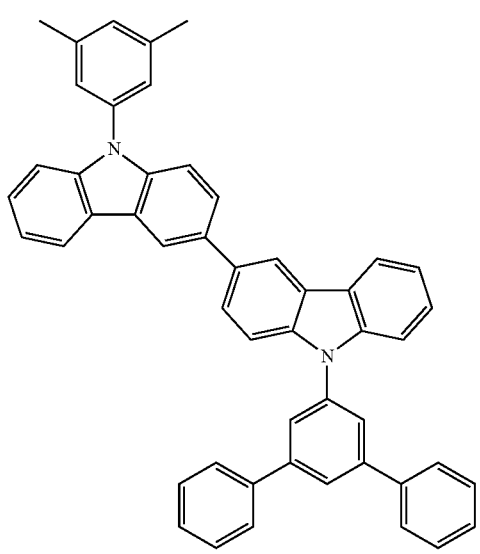
H-H32
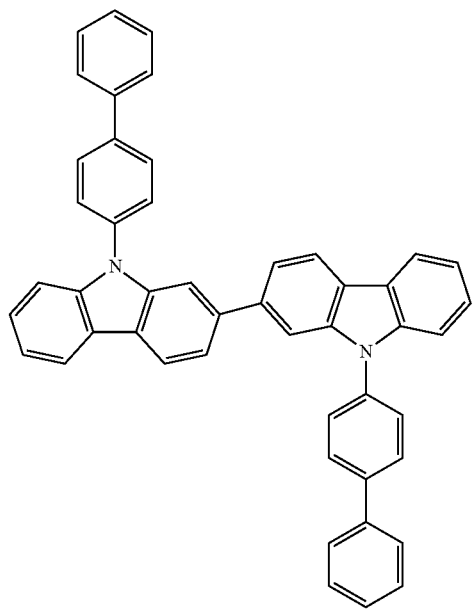

H-H33
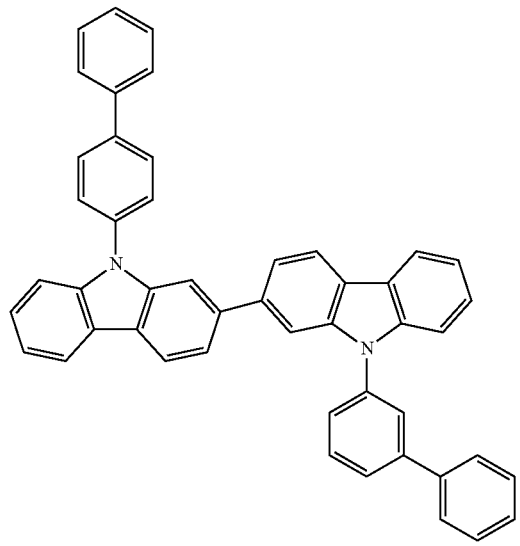
H-H34
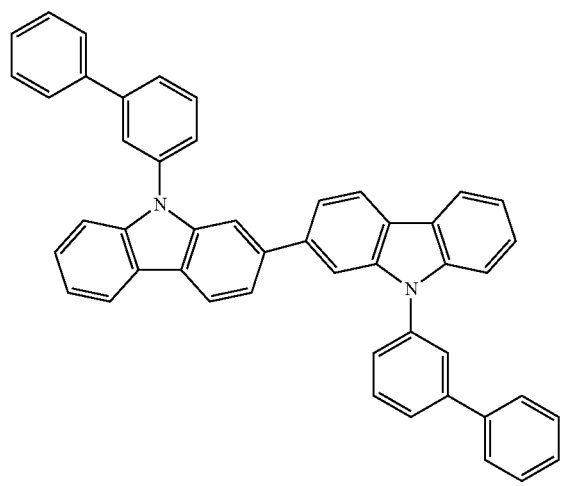
H-H35
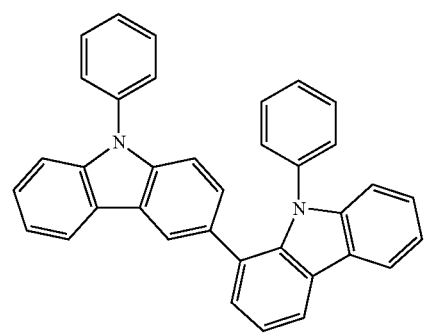
H-H36
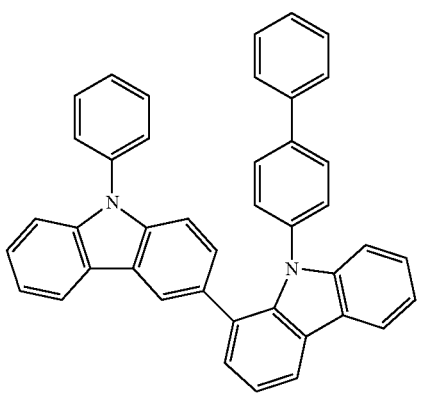
H-H37
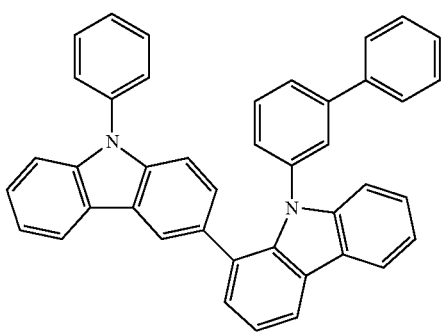
H-H38
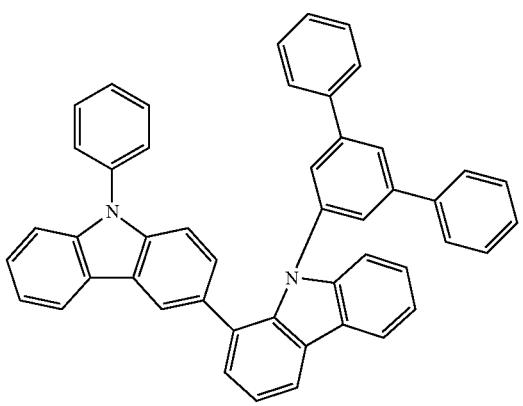
H-H39
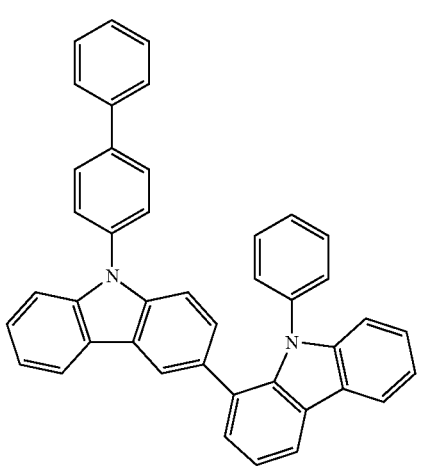

935
-continued
H-H40
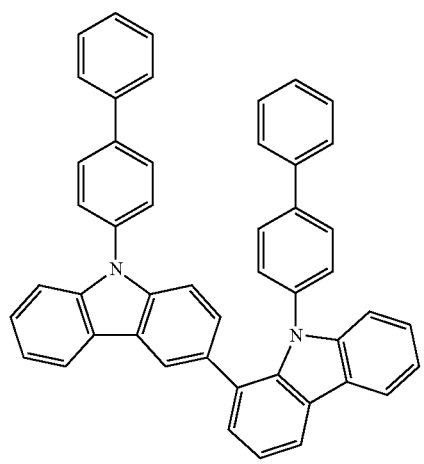
H-H41
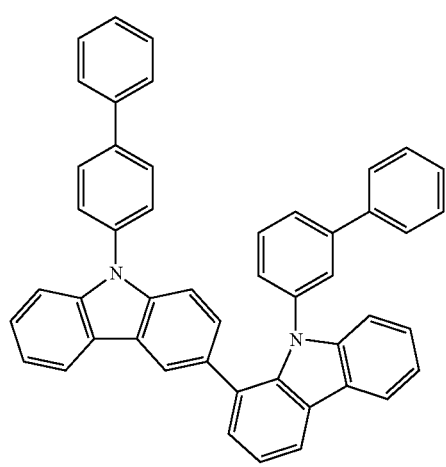
H-H42
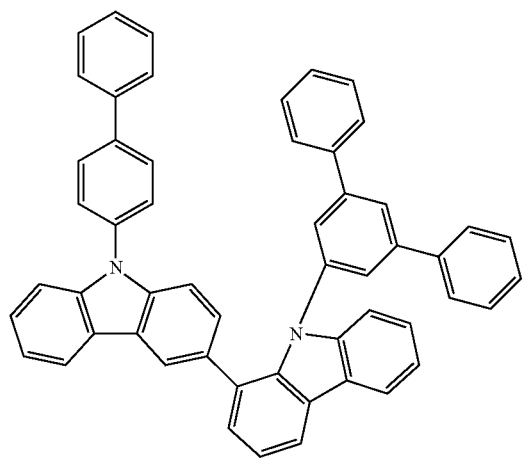
936
-continued
H-H43
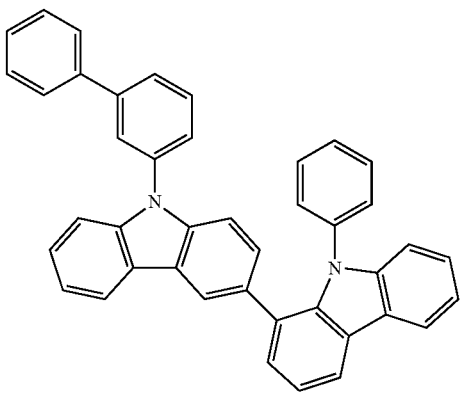
H-H44
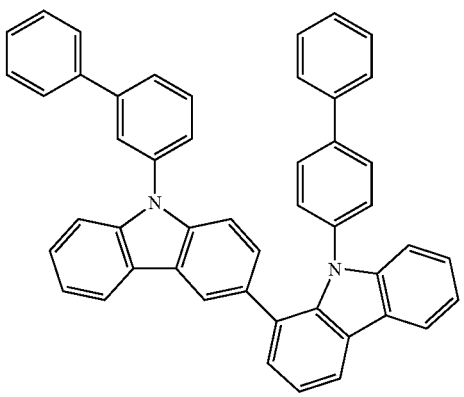
H-H45
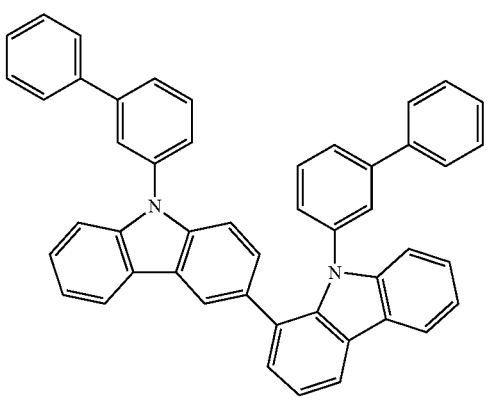
H-H46
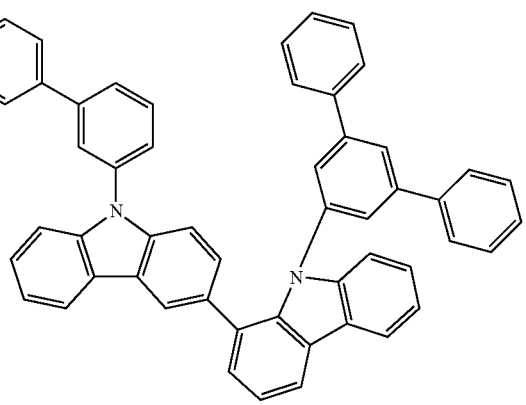

H-H47
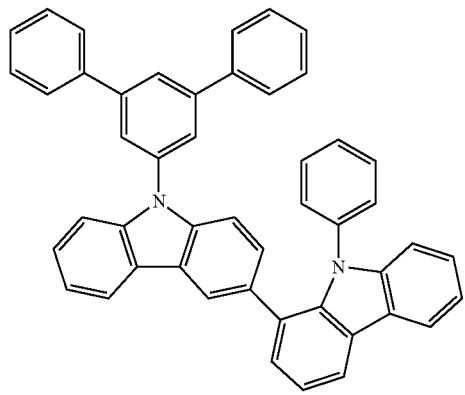
H-H48
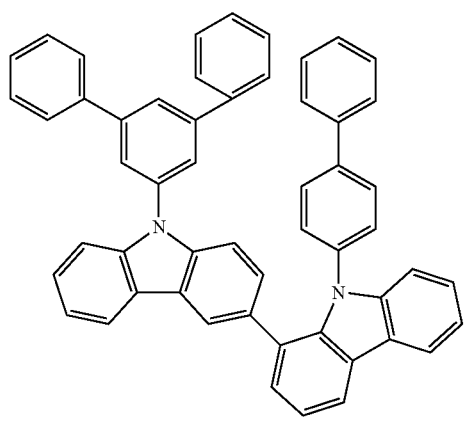
H-H49
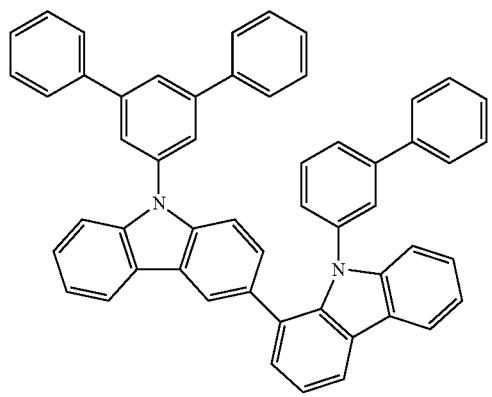
H-H50
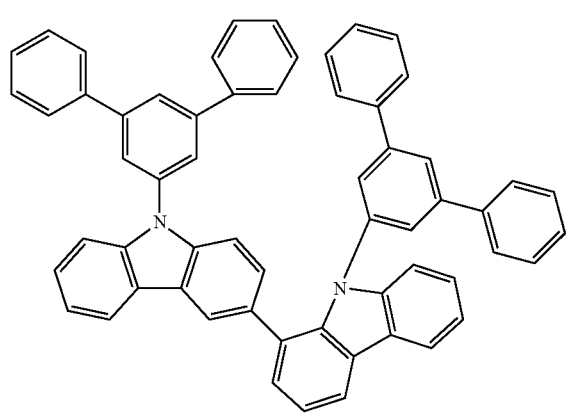
H-H51
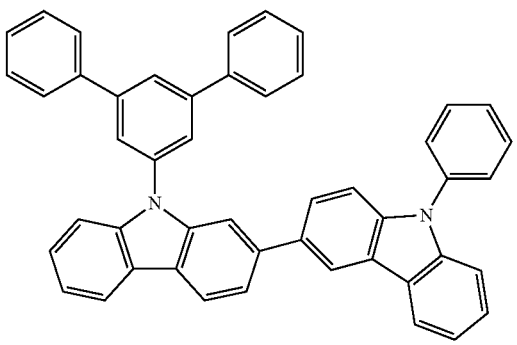
H-H52
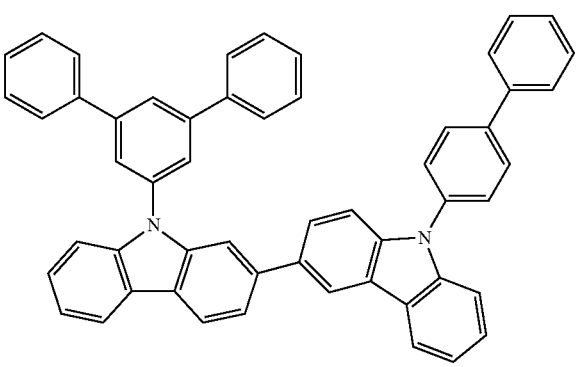
H-H53
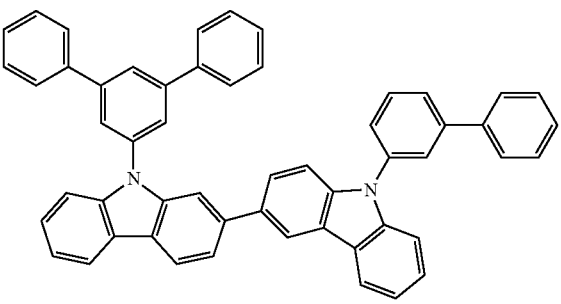
H-H54
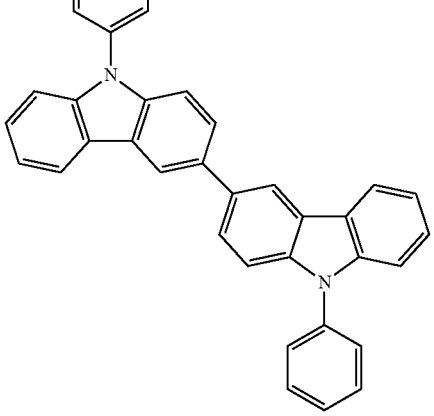

939
-continued
H-H55
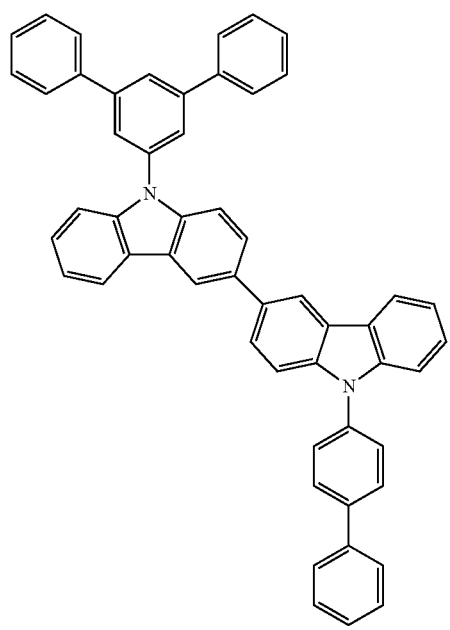
H-H56
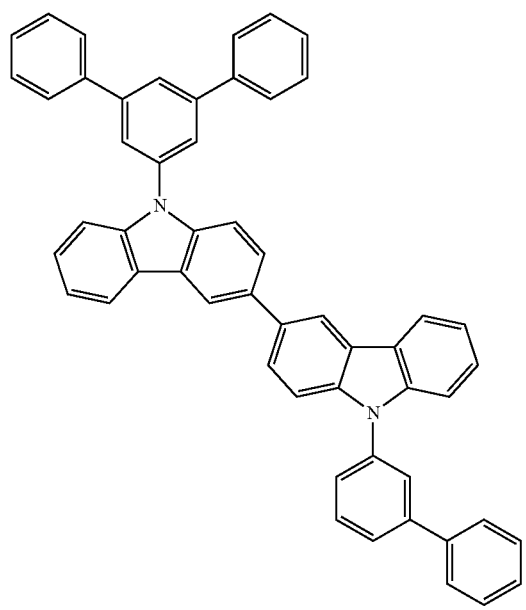
940
-continued
H-H57
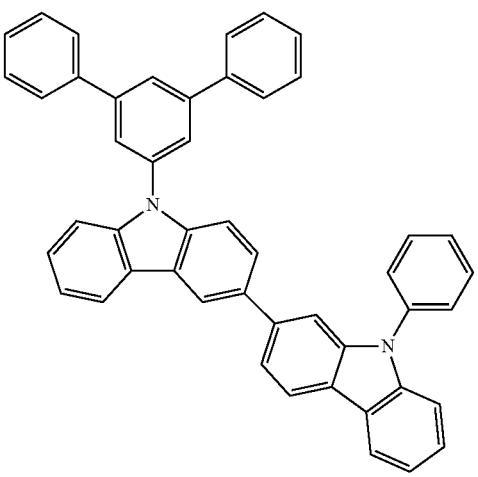
H-H58
H-H59
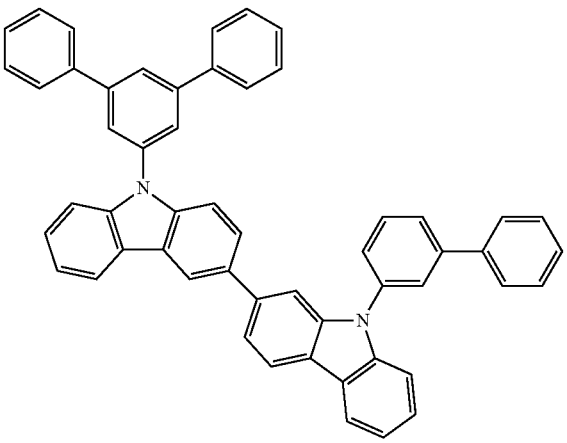

H-H60
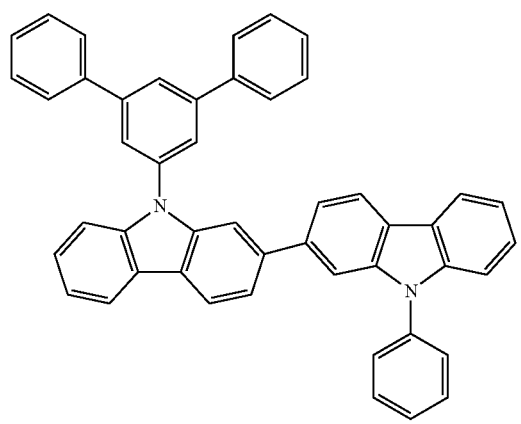
H-H61
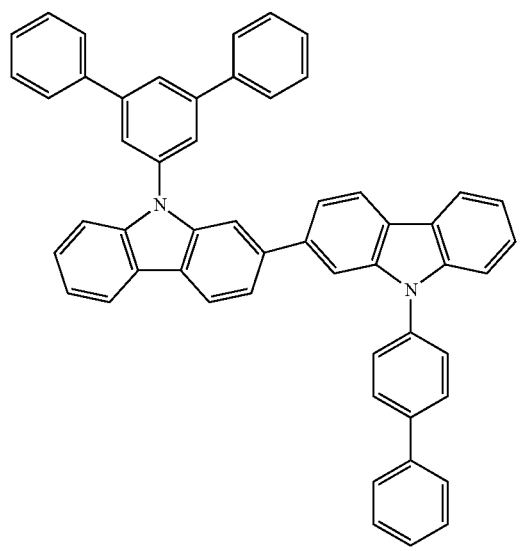
H-H62
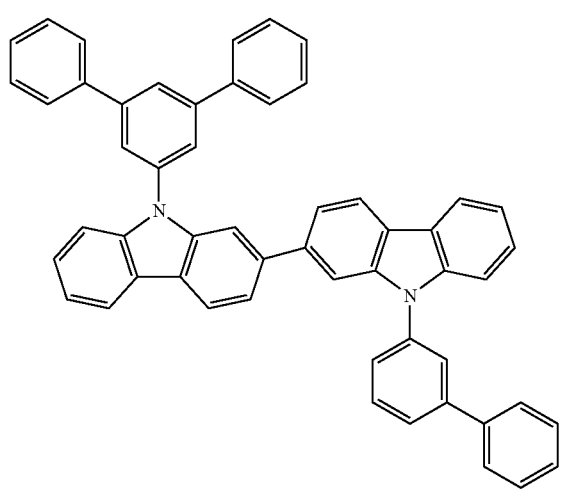
H-H63
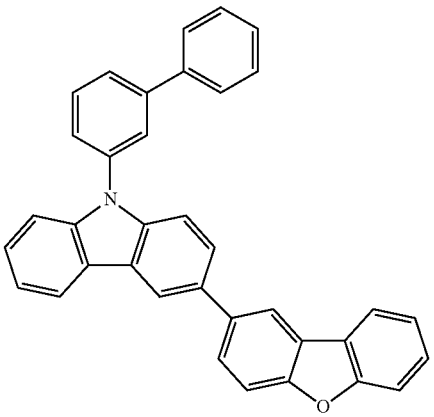
H-H64
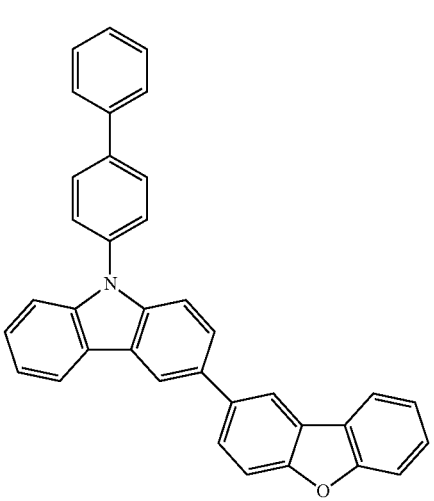
H-H65
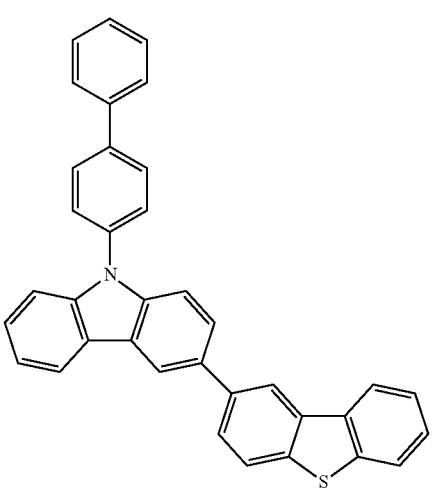

H-H66
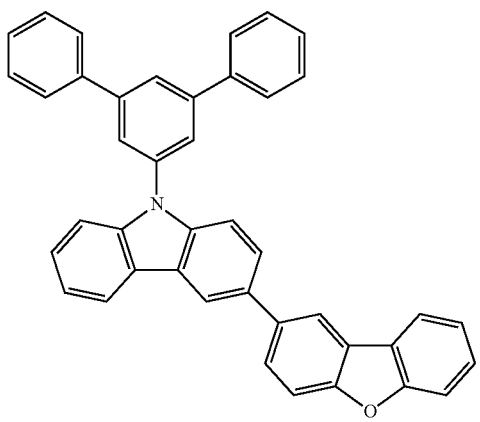
H-H67
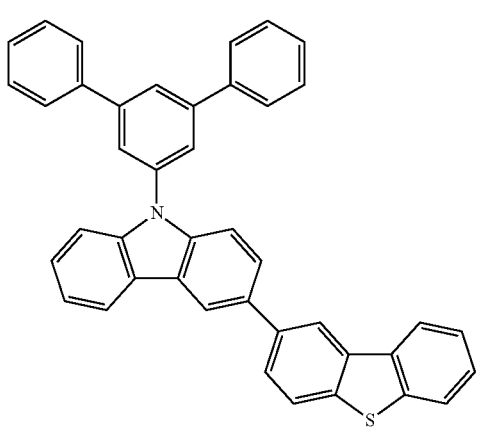
H-H68
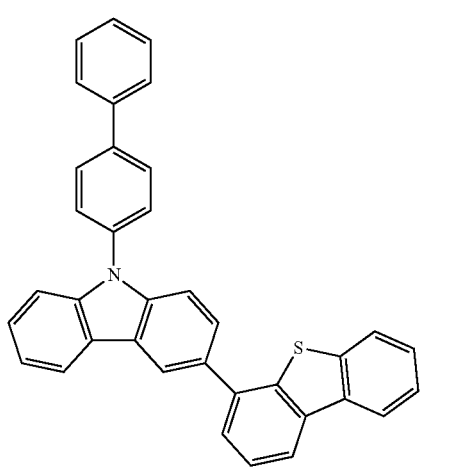
H-H69
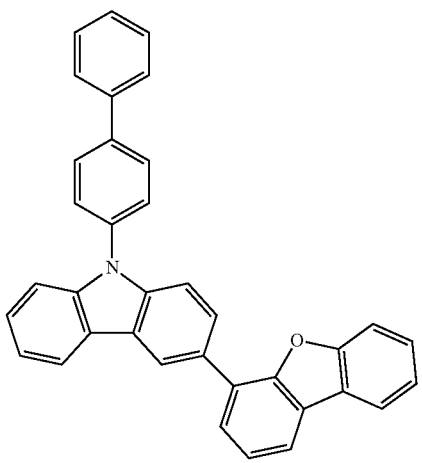
H-H70
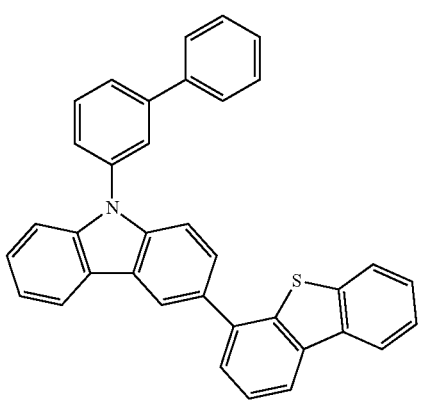
H-H71
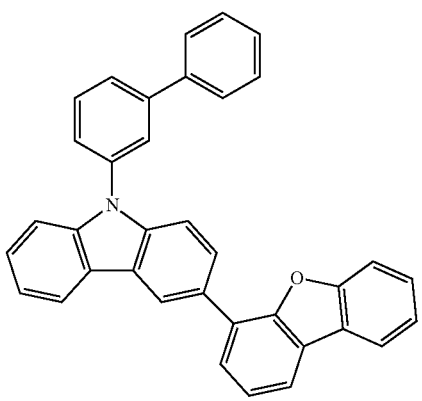
H-H72

945
-continued
946
-continued
H-H73
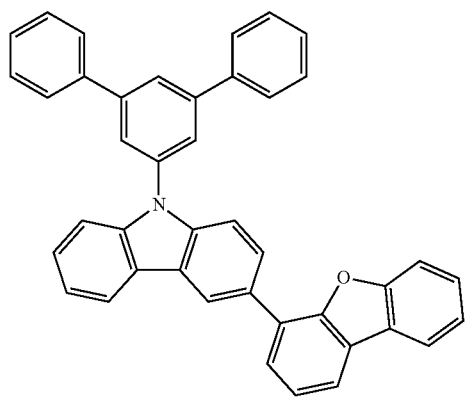
H-H76
H-H74
H-H77
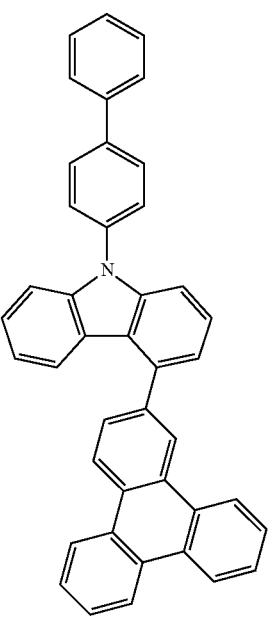
H-H75
H-H78
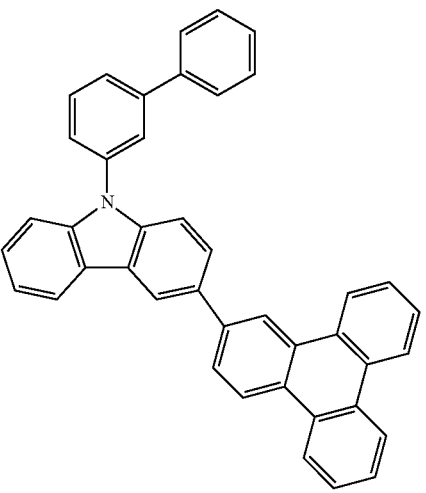

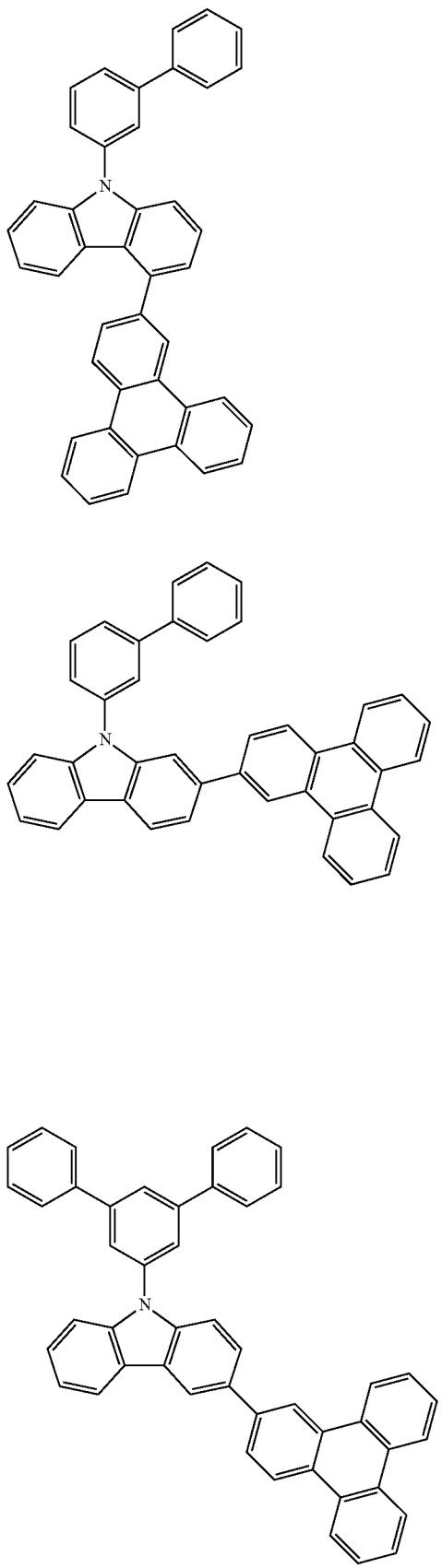
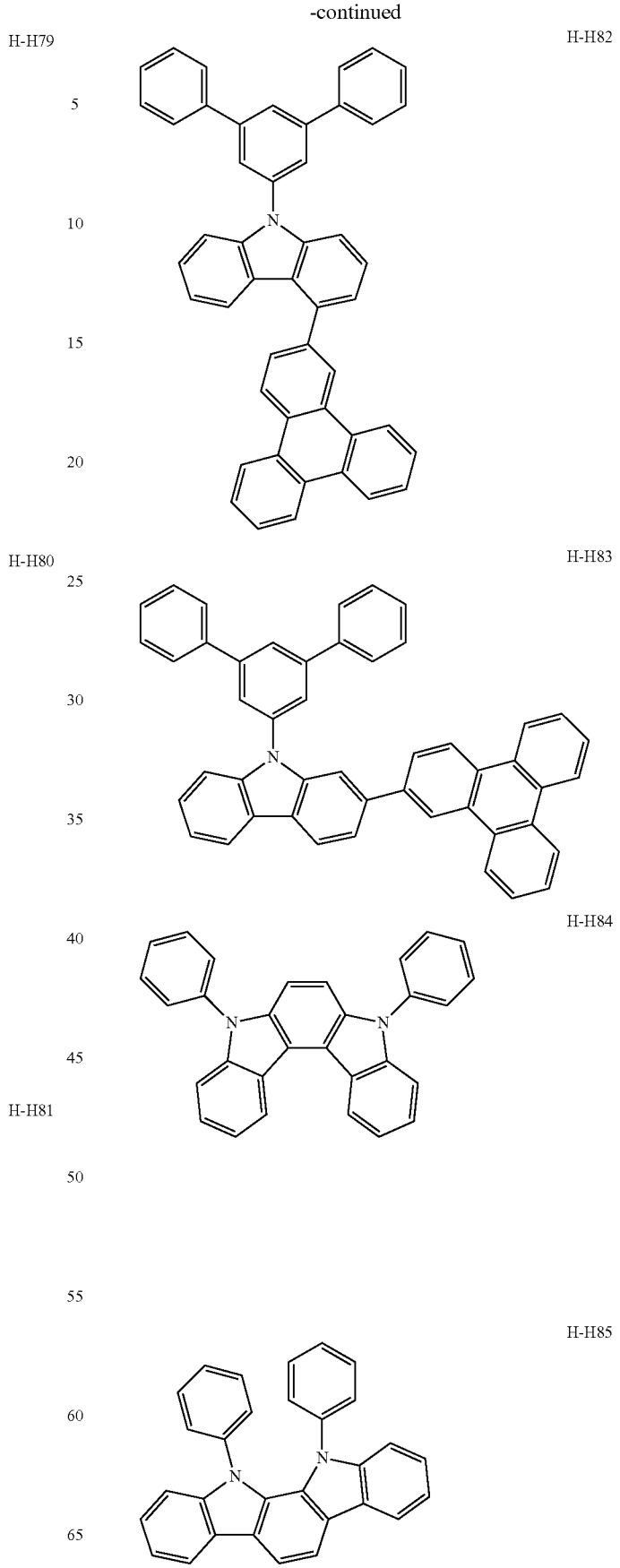

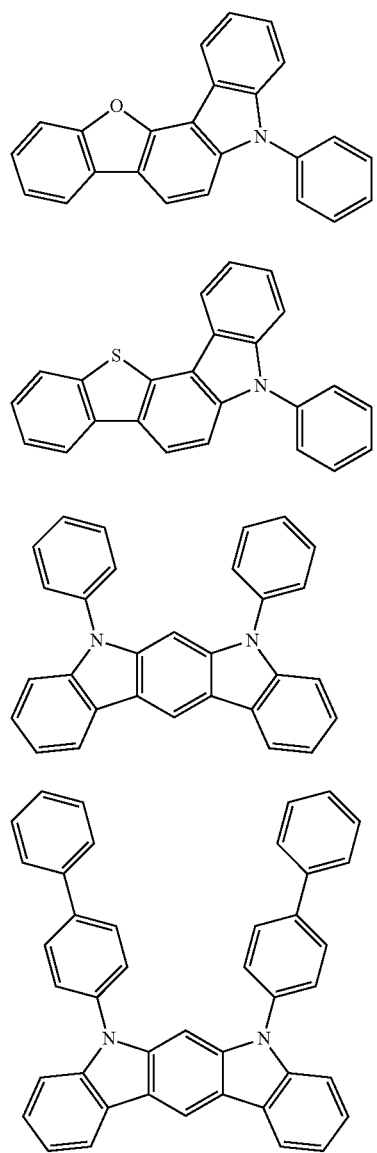
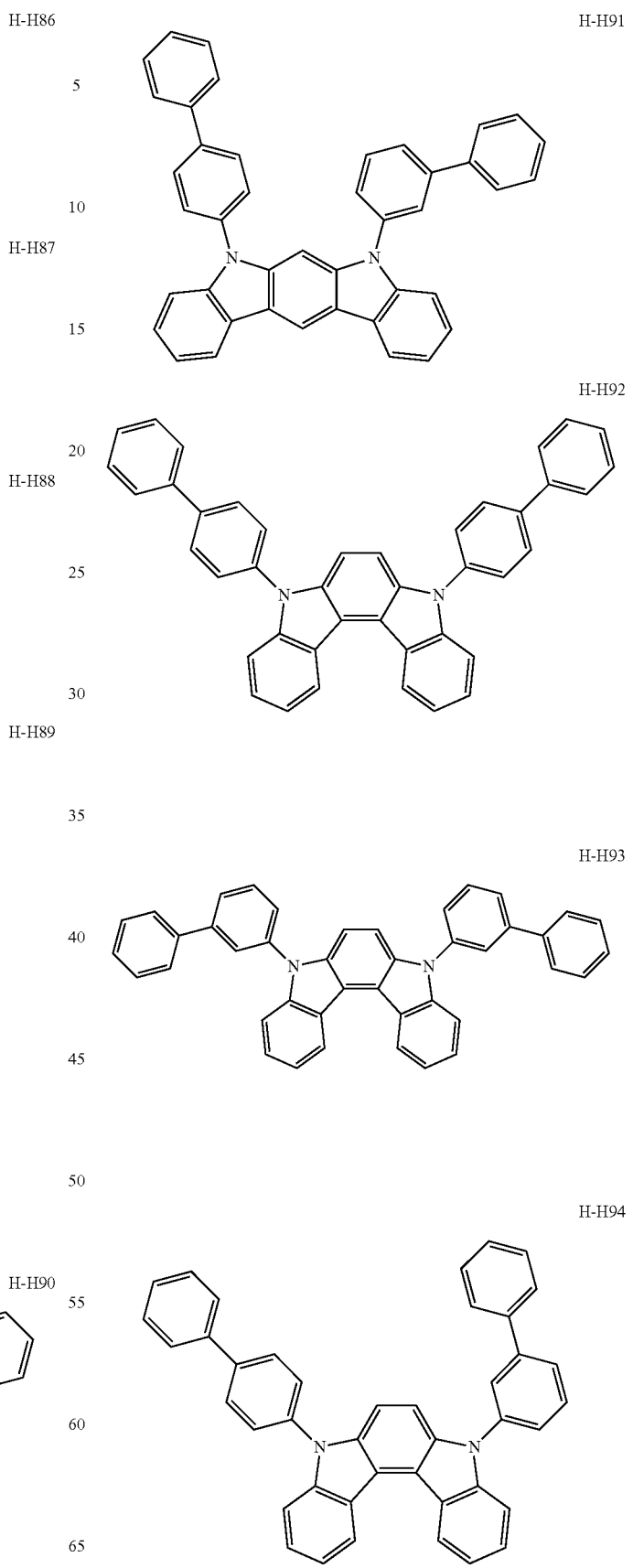

-continued
H-H95
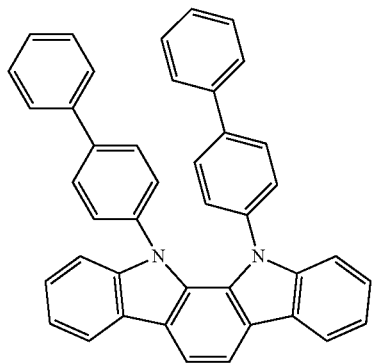
H-H96
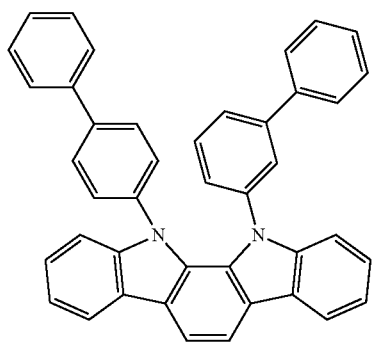
H-H97
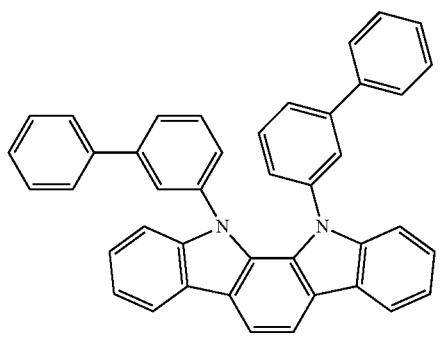
H-H98
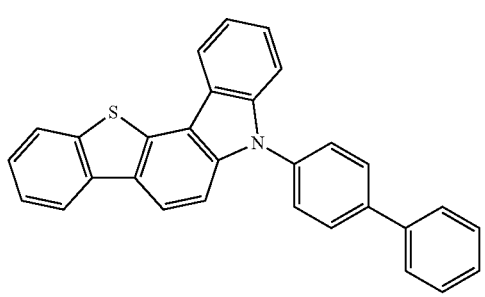
H-H99
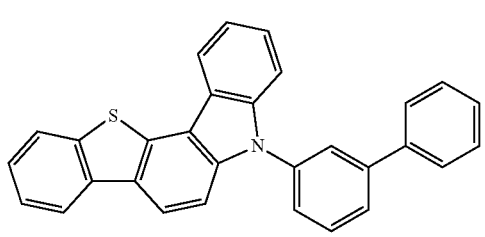
-continued
H-H100
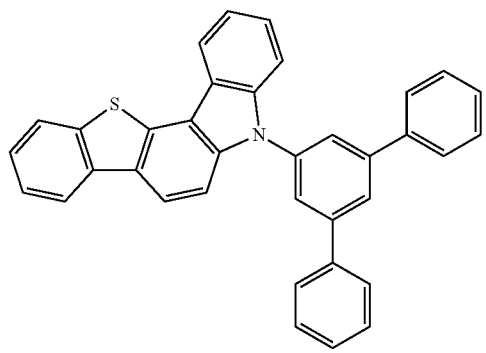
H-H101
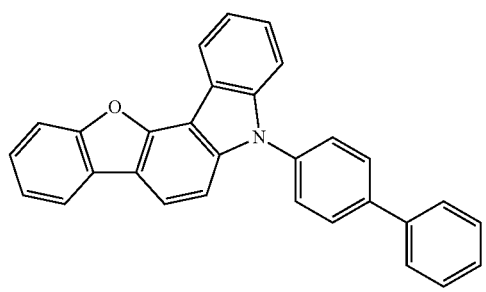
H-H102
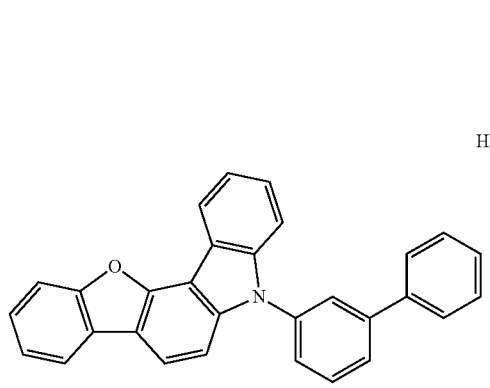
H-H103
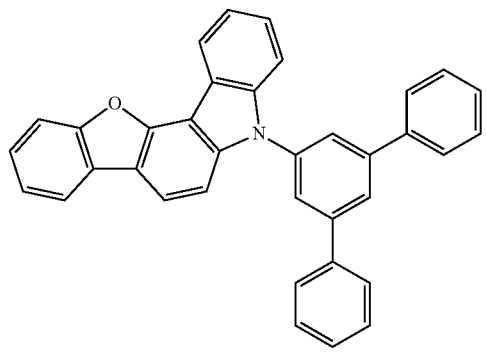

In some embodiments, the bipolar host may be Group HEH1, but embodiments are not limited thereto:
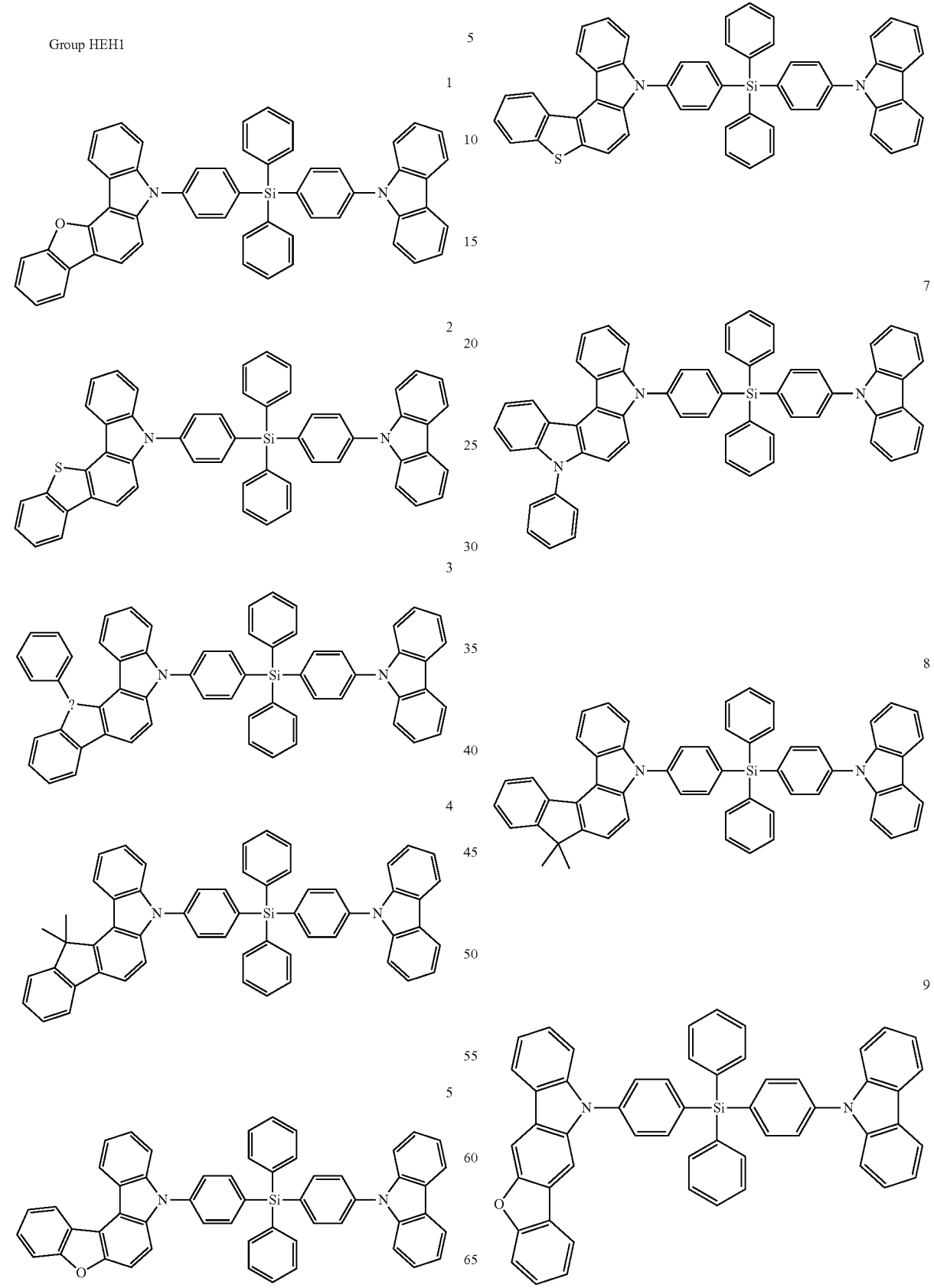

-continued
10
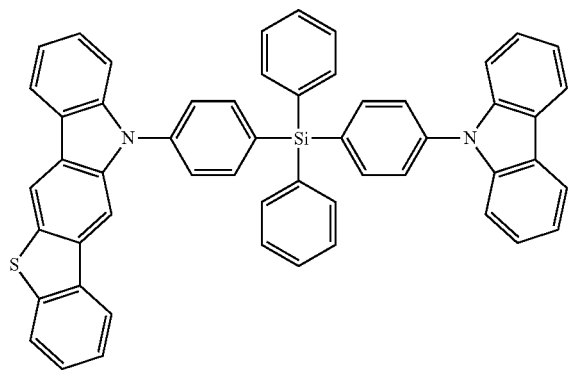
11
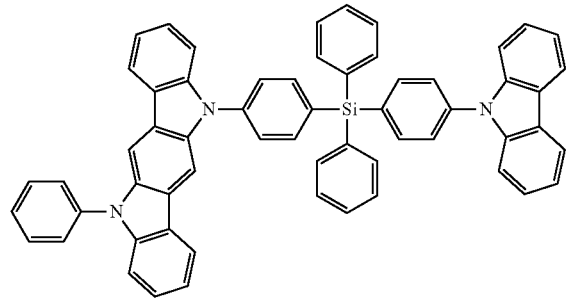
12
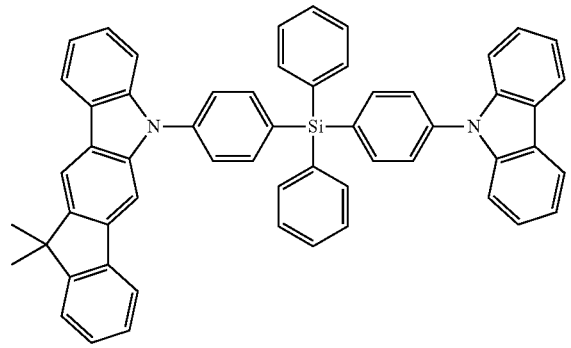
13
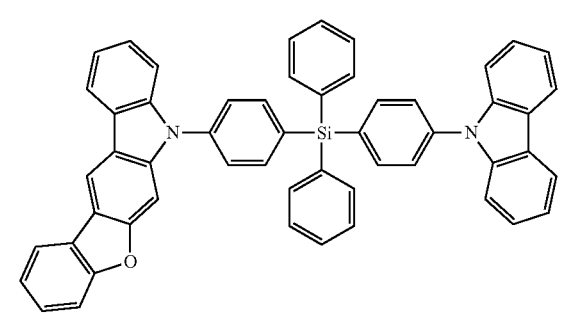
-continued
14
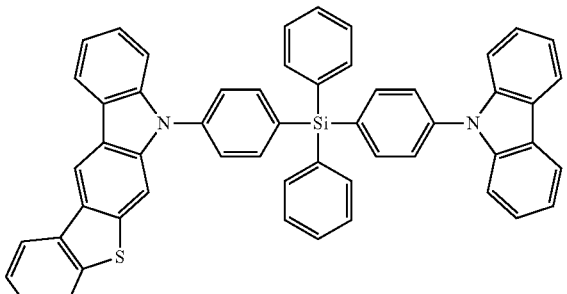
15
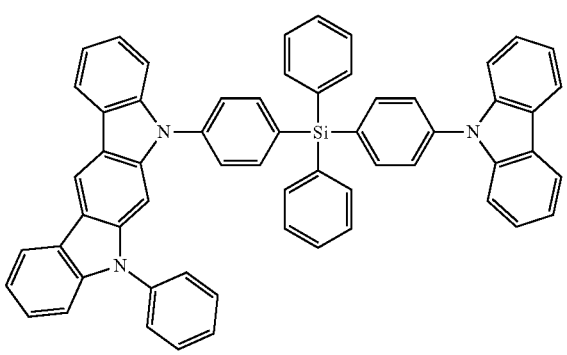
16
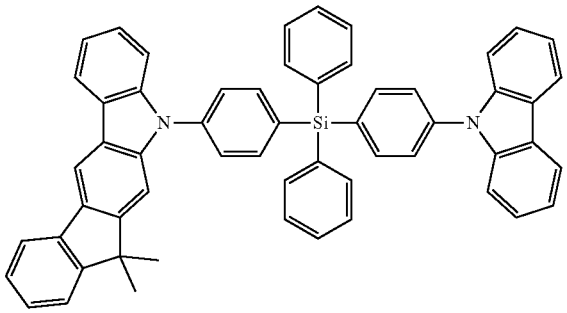
17
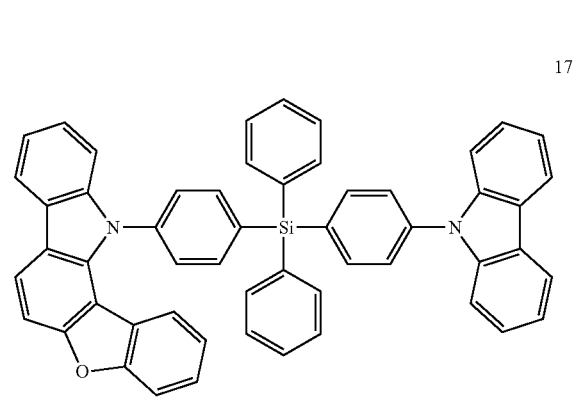

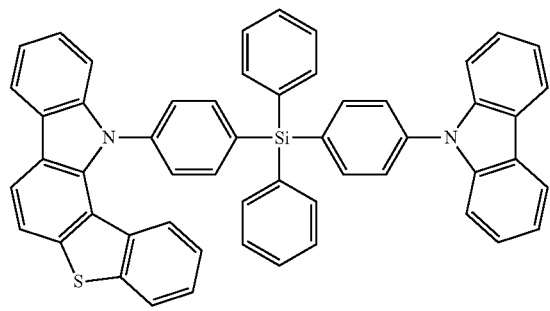
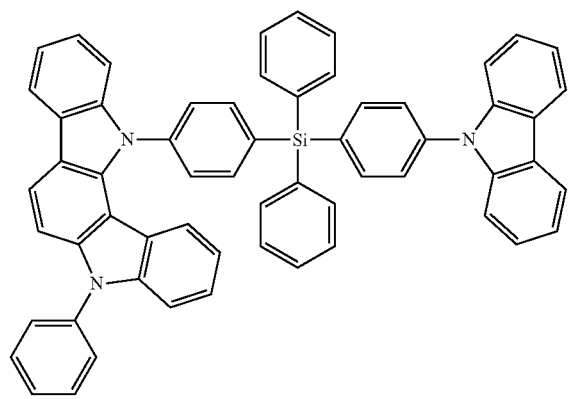
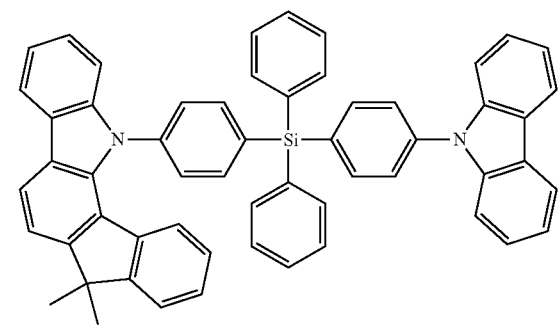
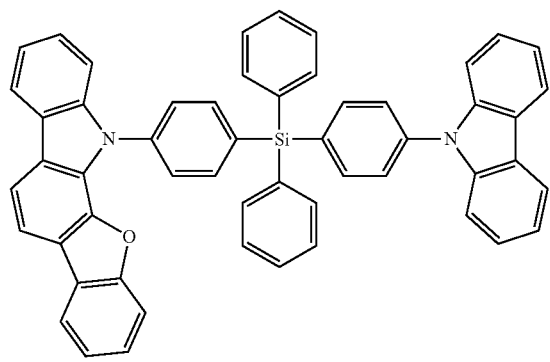
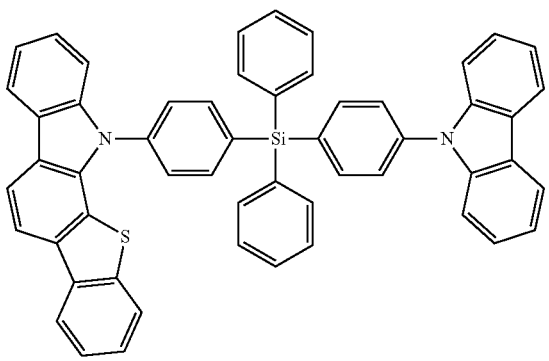
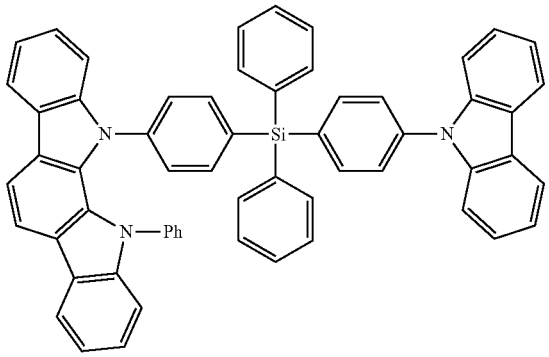
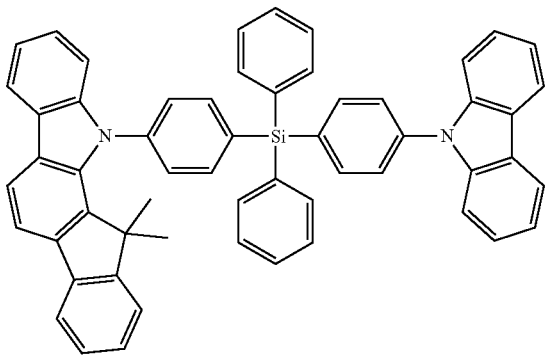
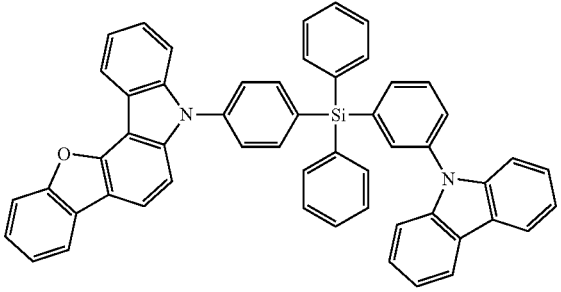

959
-continued
26
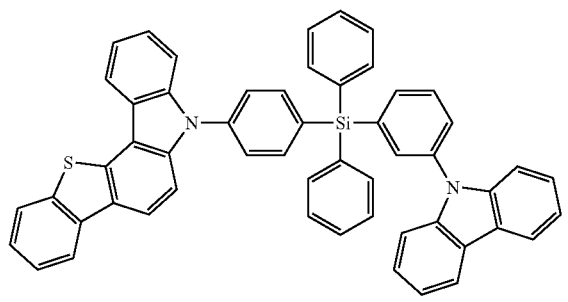
27
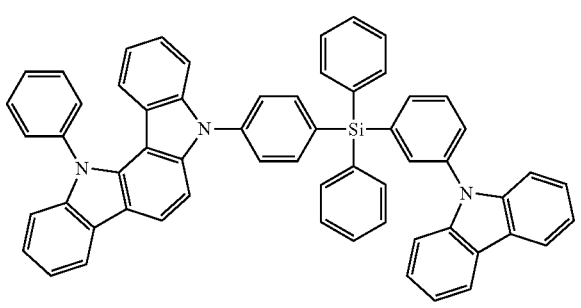
28
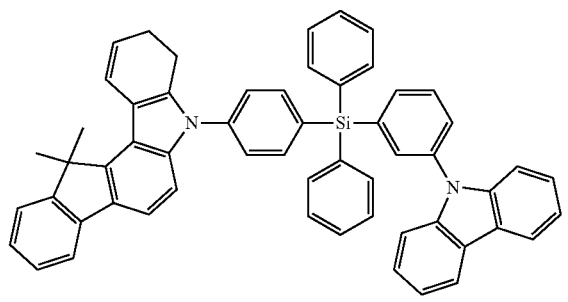
29
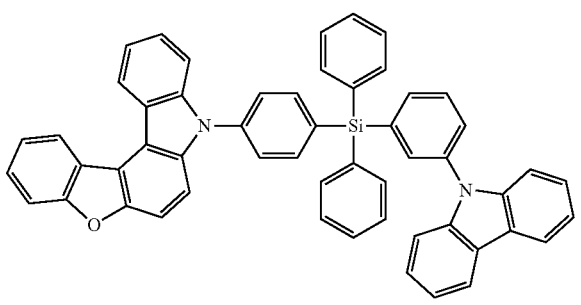
30
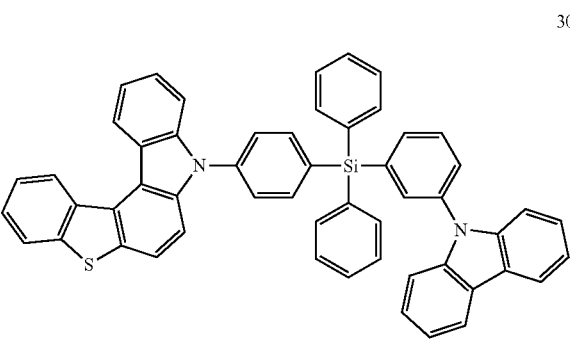
960
-continued
31
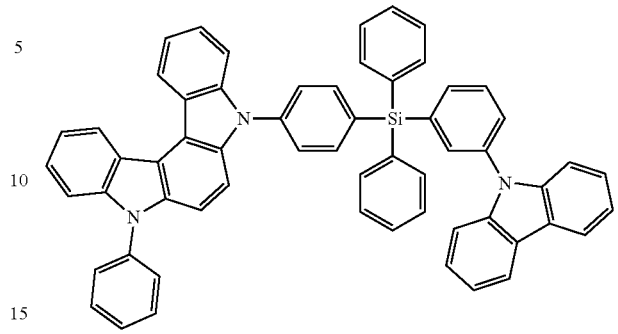
32
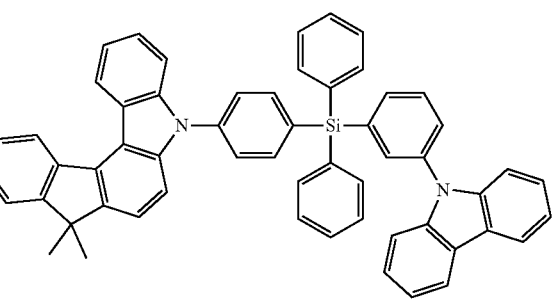
33
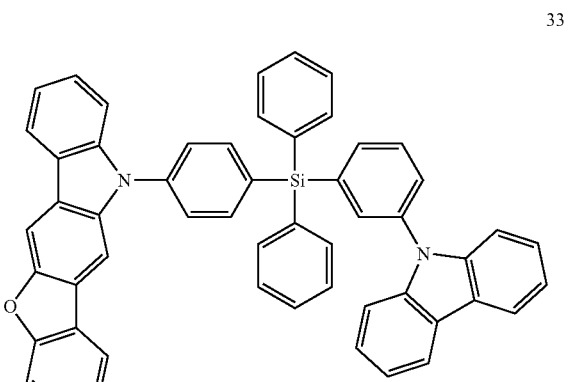
34
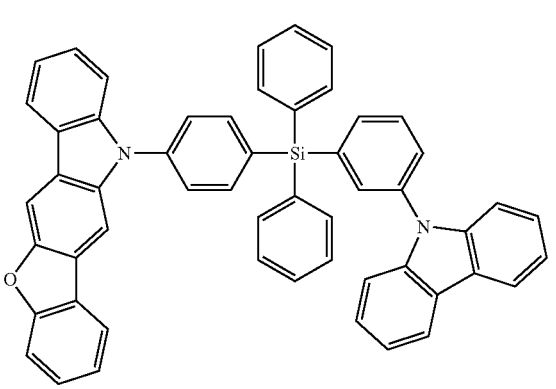

961
-continued
35
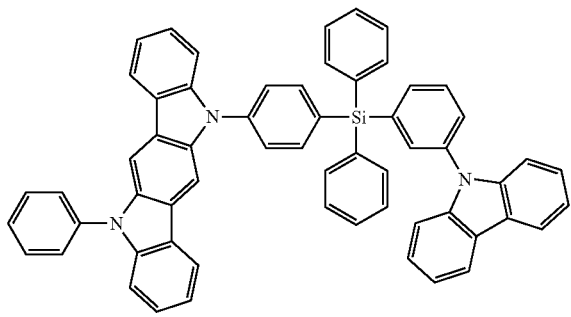
36
37
38
962
-continued
39
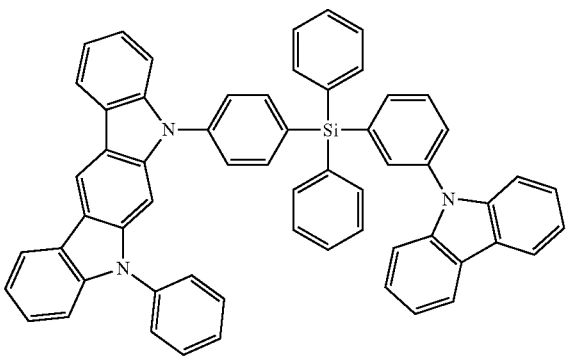
40
41
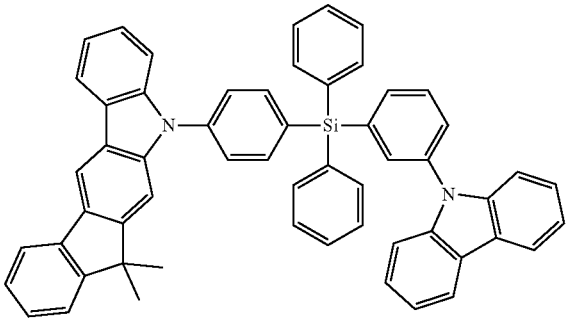
42
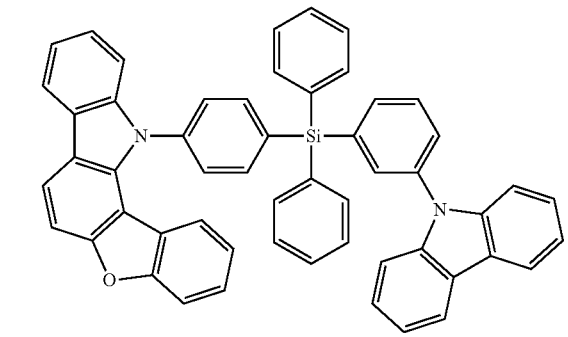
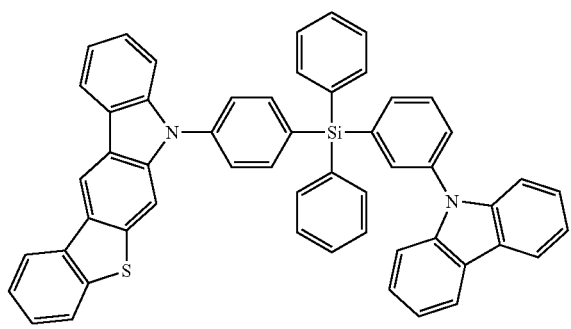

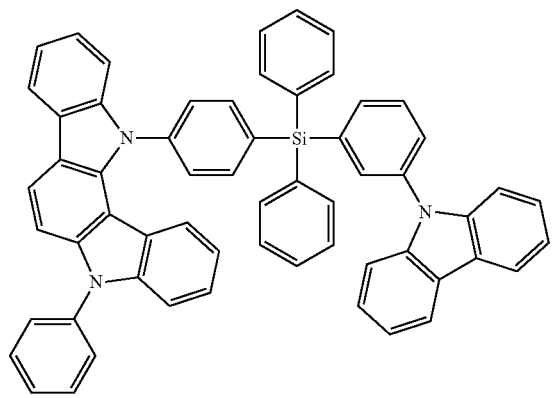
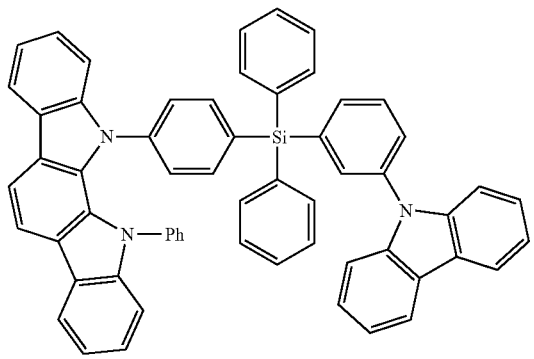
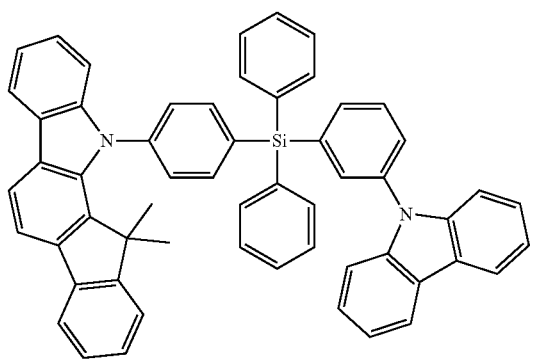
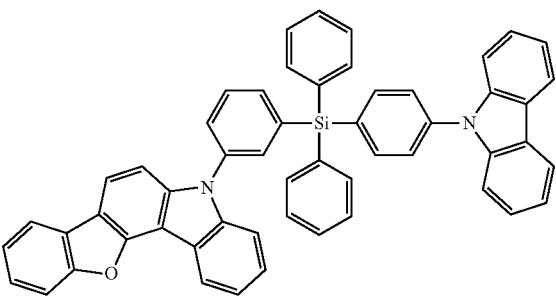
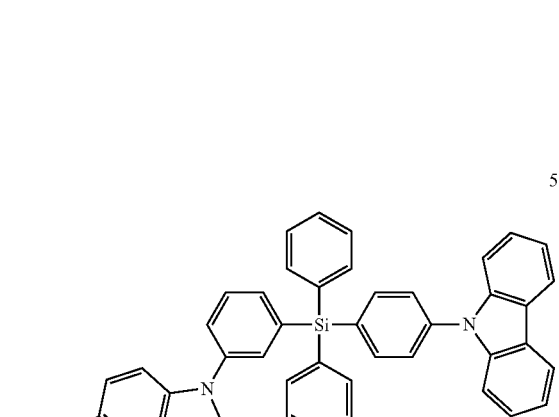

965
-continued
51
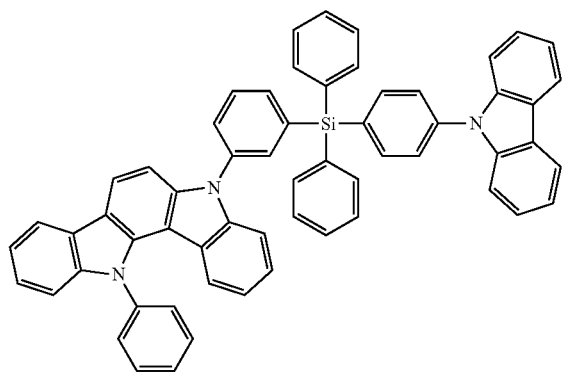
52
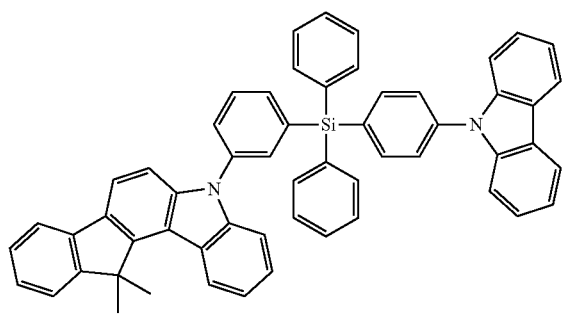
53
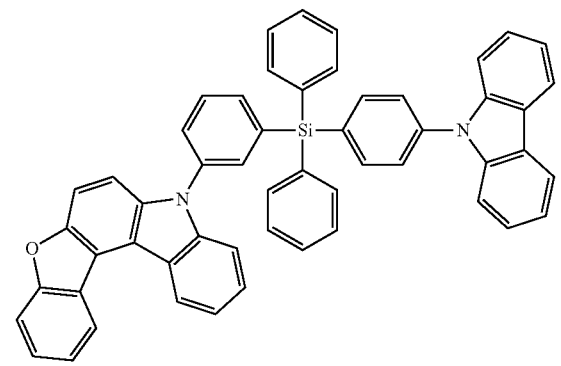
54
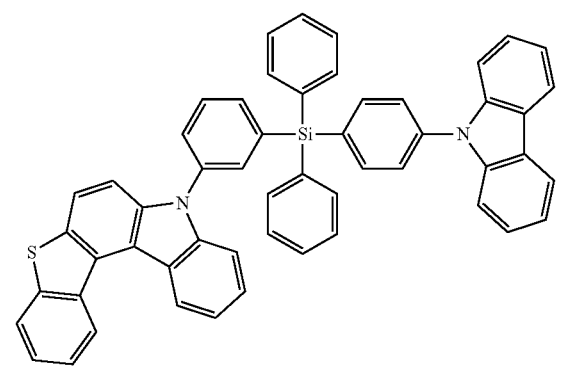
966
-continued
55
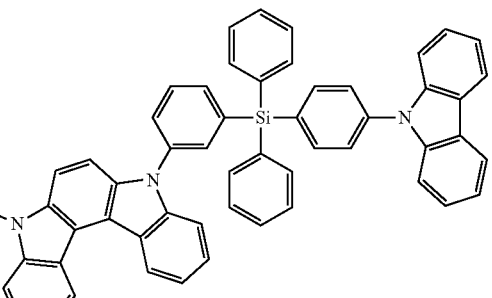
56
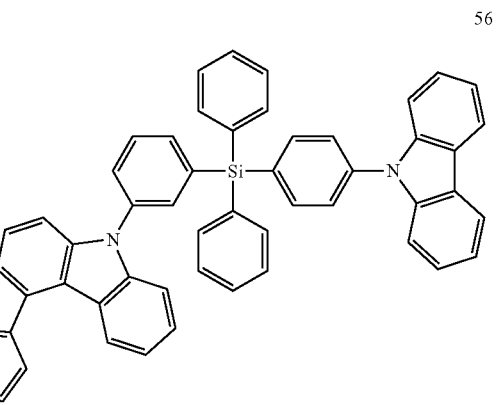
57
58
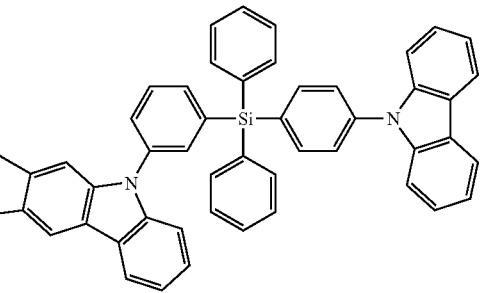

-continued
59
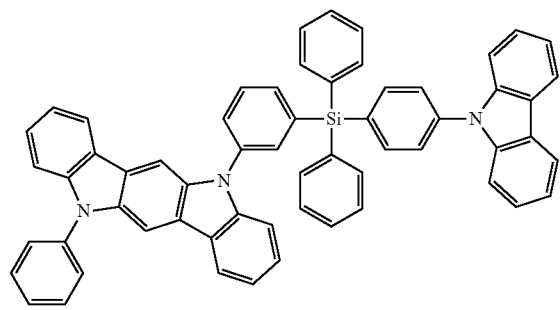
60
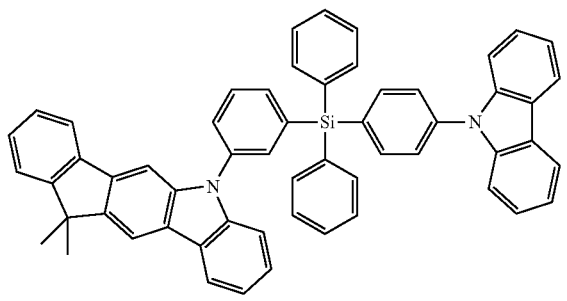
61
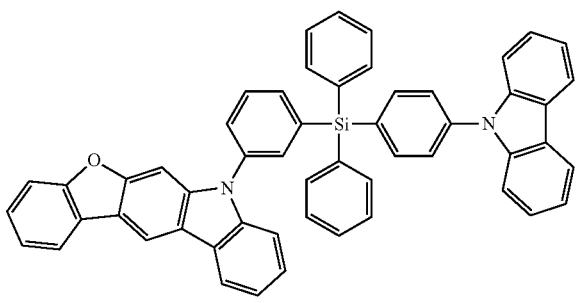
62
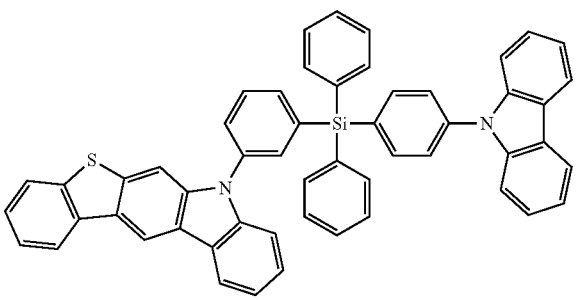
63
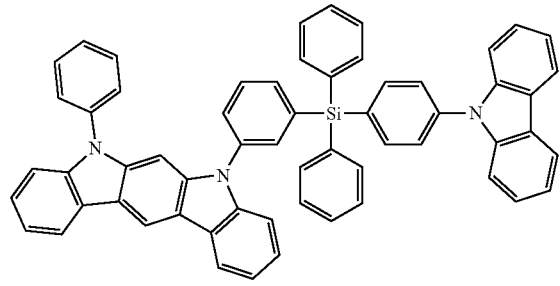
-continued
64
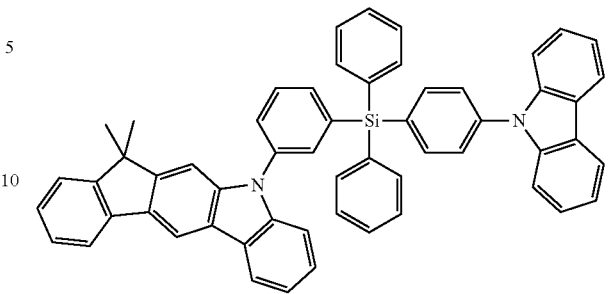
65
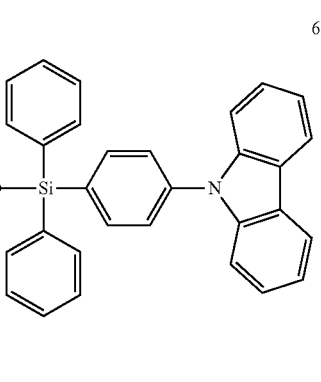
66
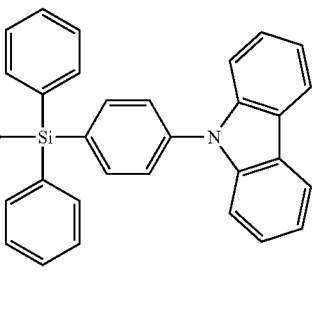
67
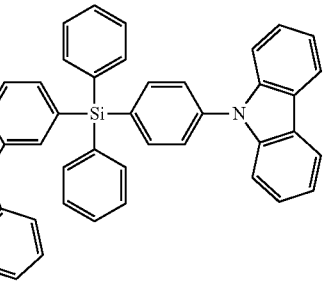

969
-continued
68
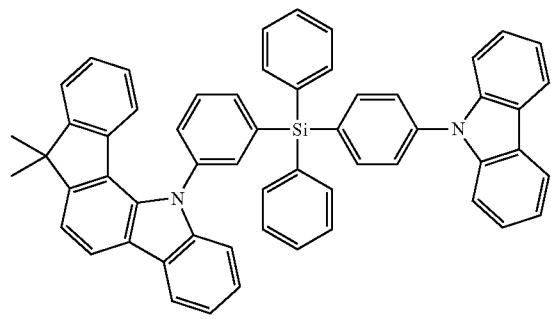
69
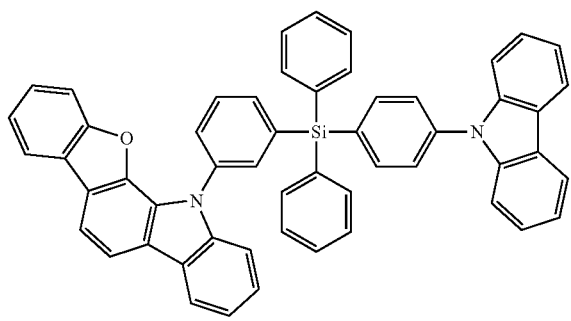
70
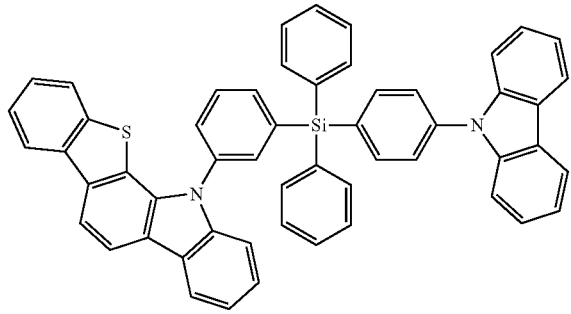
71
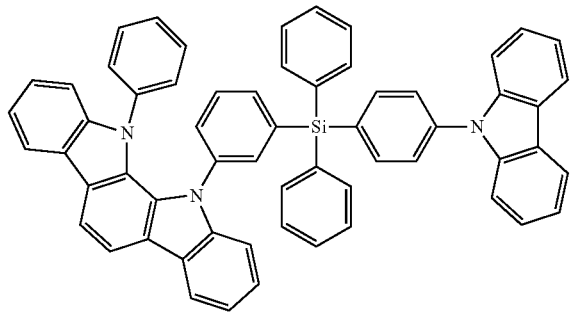
970
-continued
72
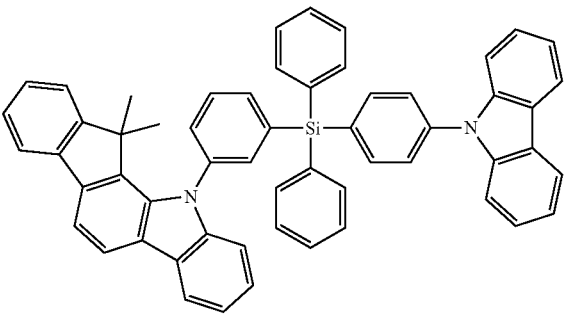
73
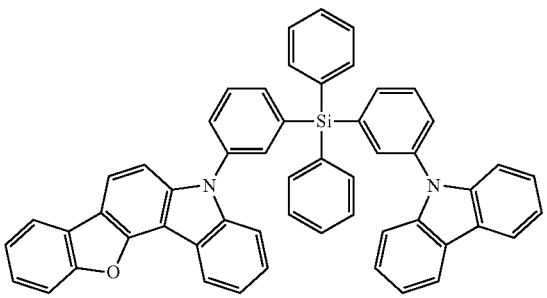
74
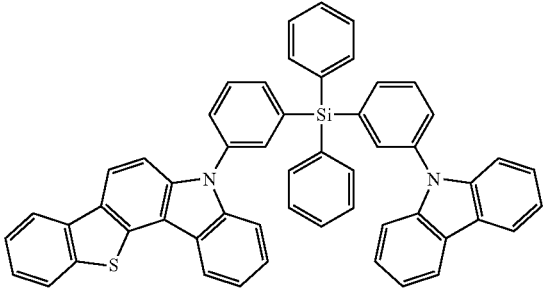
75
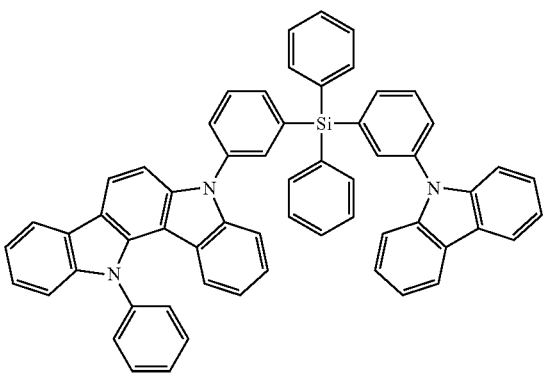

76
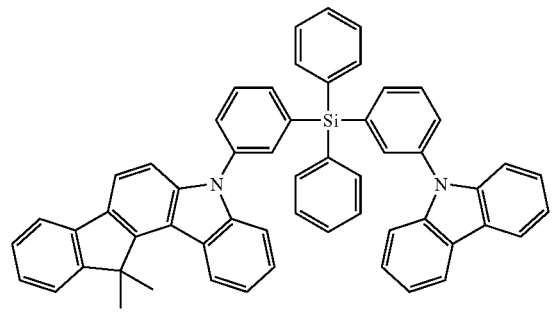
77

78
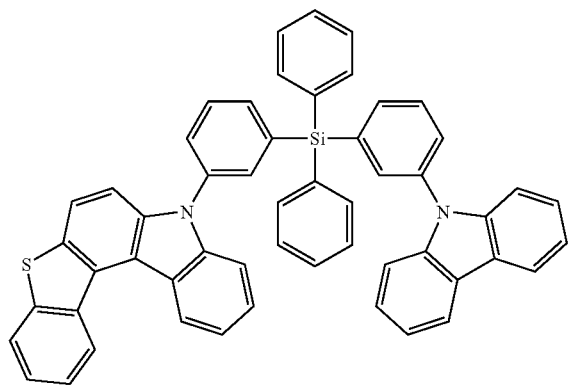
79
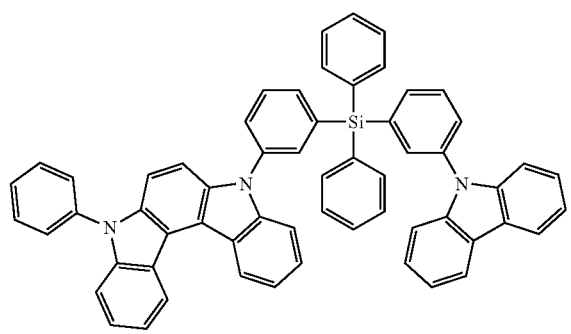
80
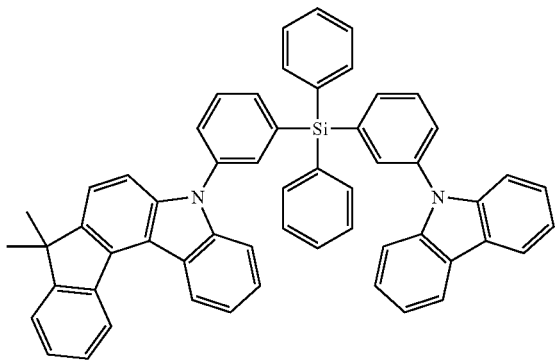
81
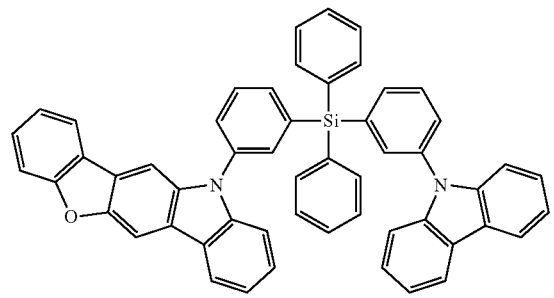
82
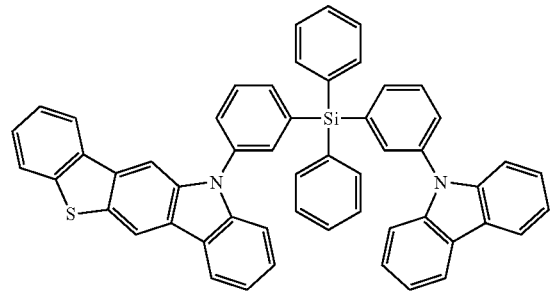
83
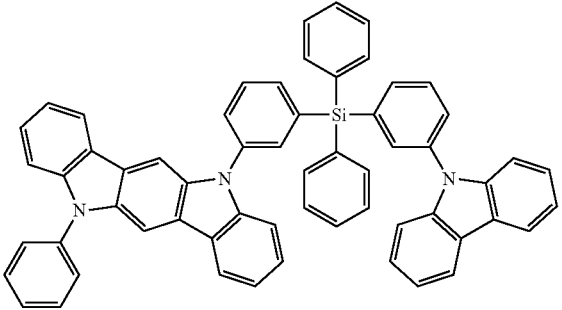

84
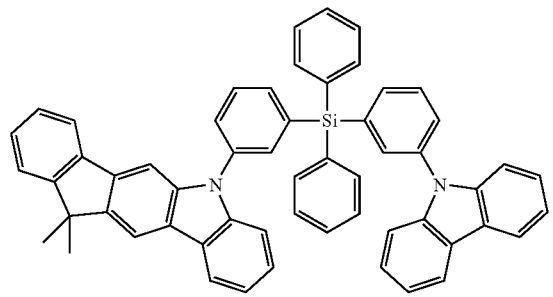
85
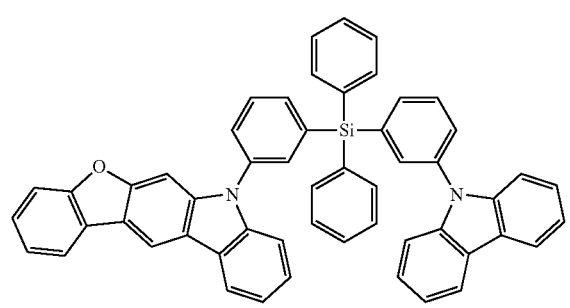
86
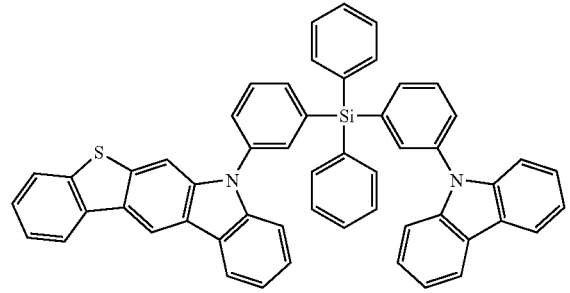
87
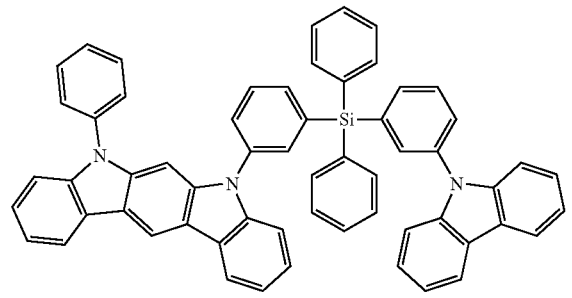
88
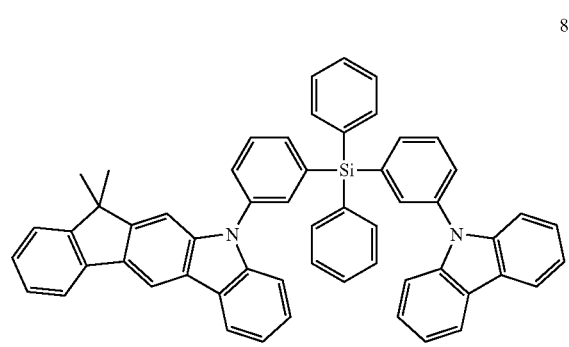
89
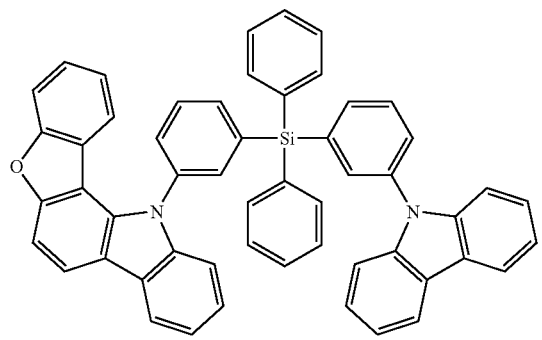
90
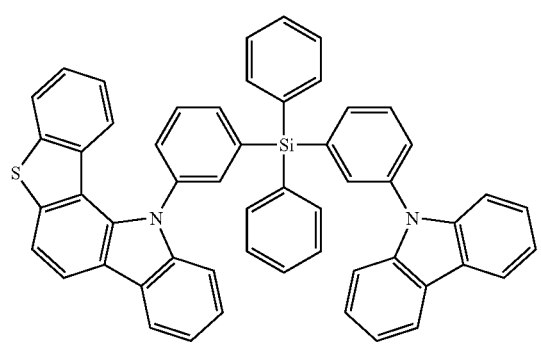
91
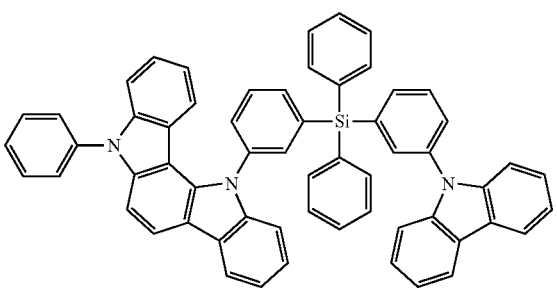
92
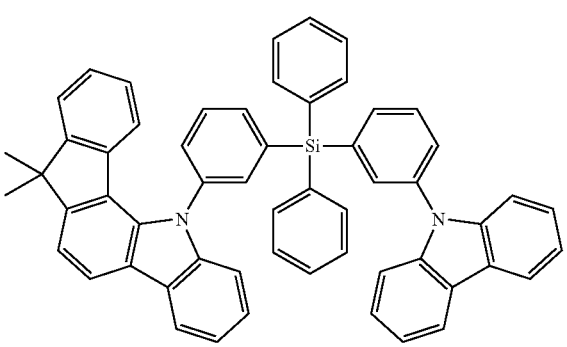

975
-continued
976
-continued
93
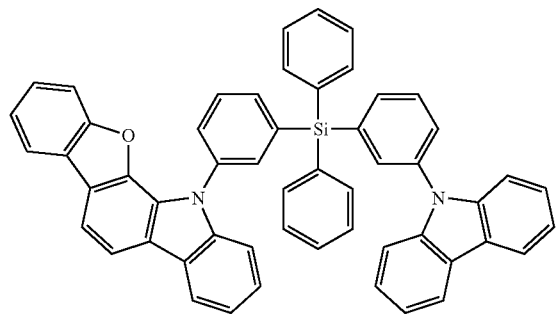
94
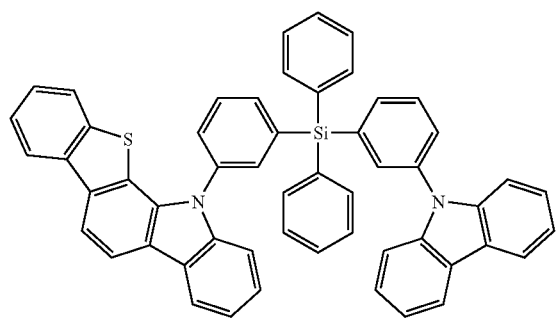
95
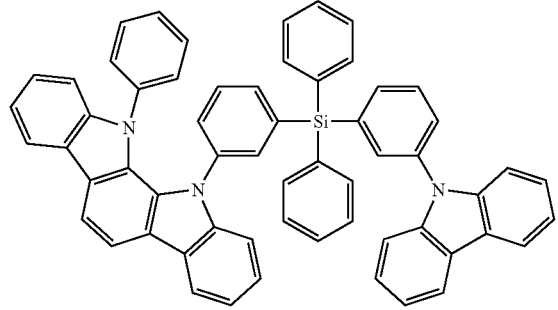
96
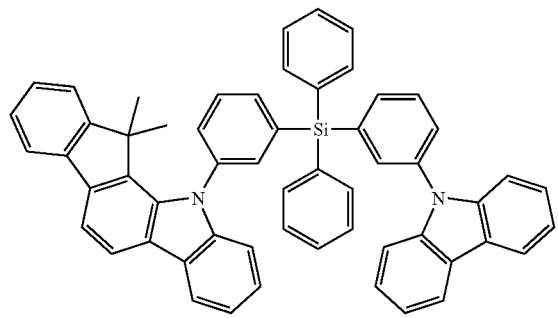
97
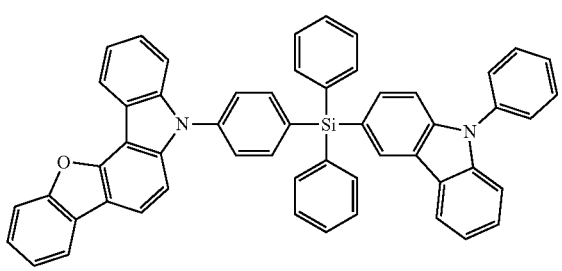
98
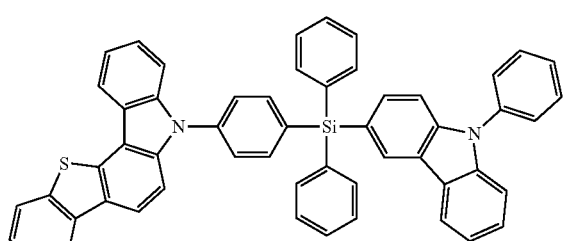
99
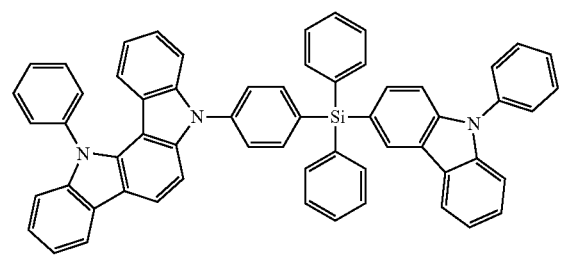
100
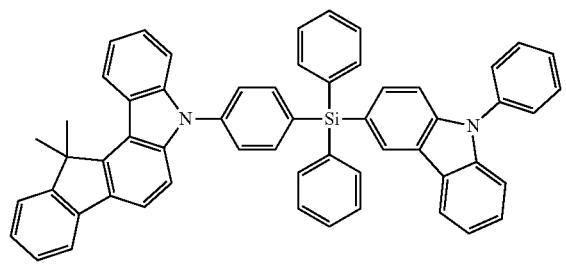
101
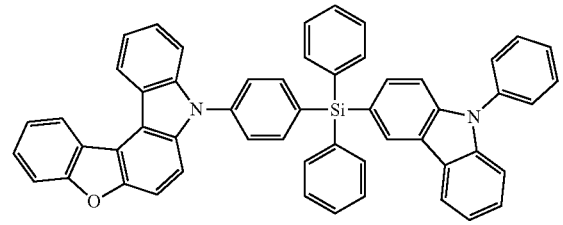
102
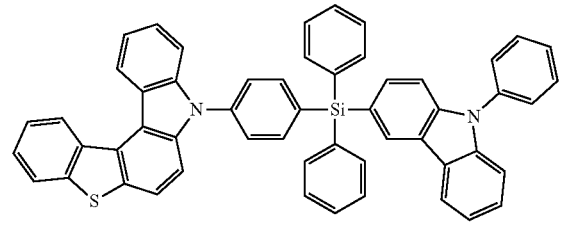

103
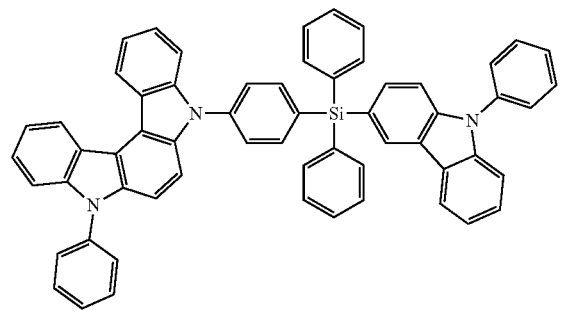
104
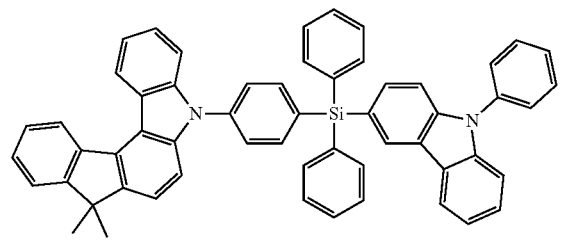
105
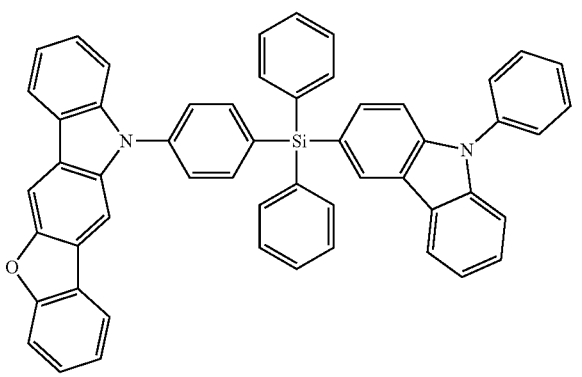
106
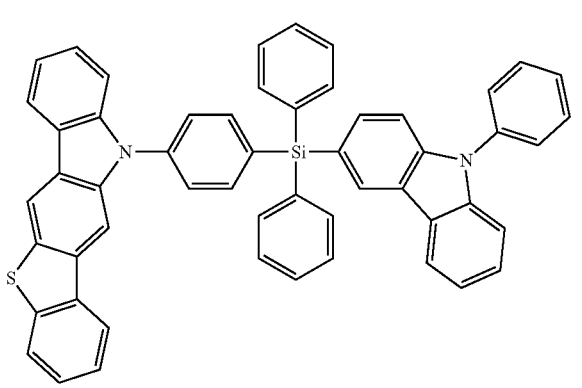
107
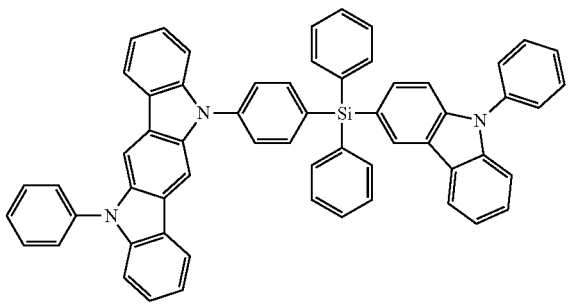
108
109
110

111
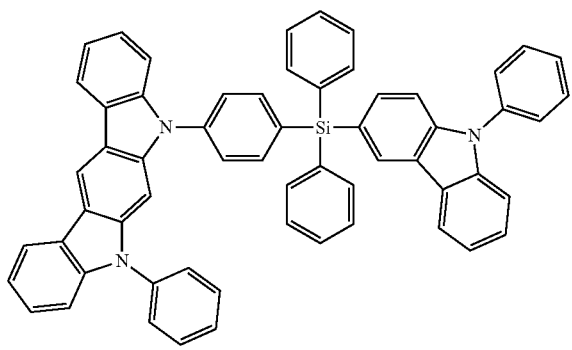
112
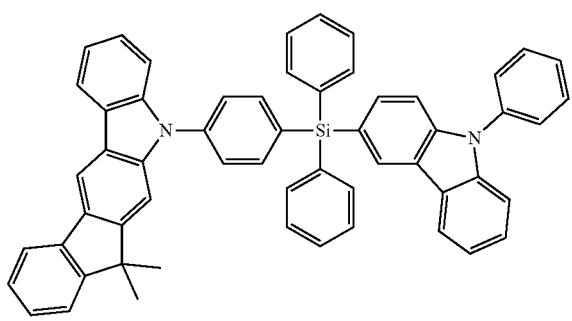
113
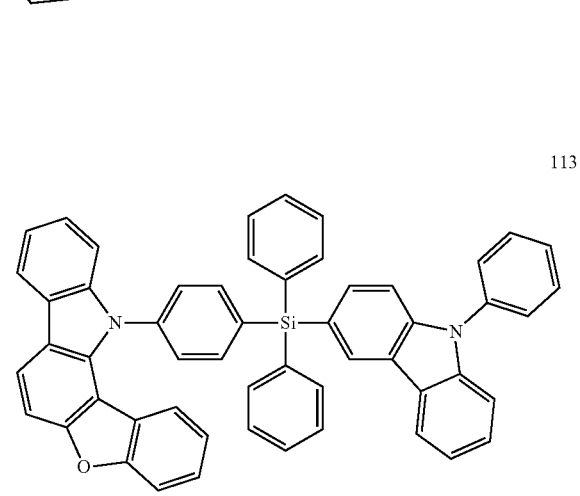
114
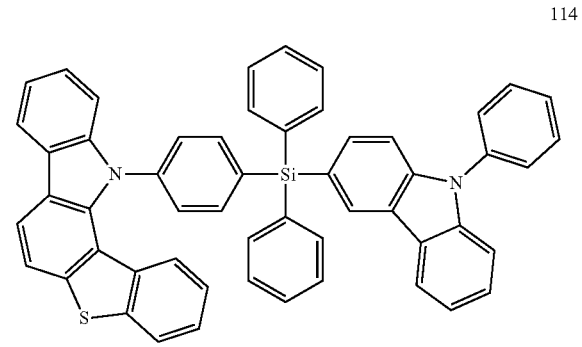
115
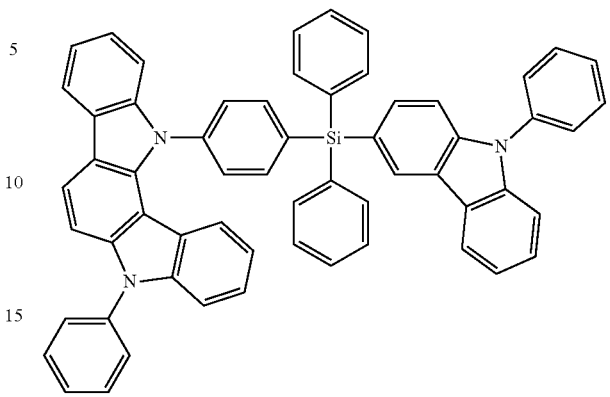
116

117

118

-continued
119
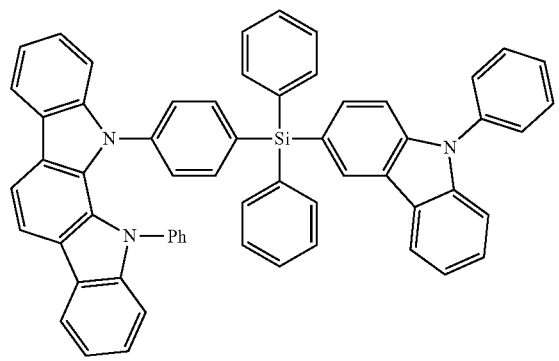
120
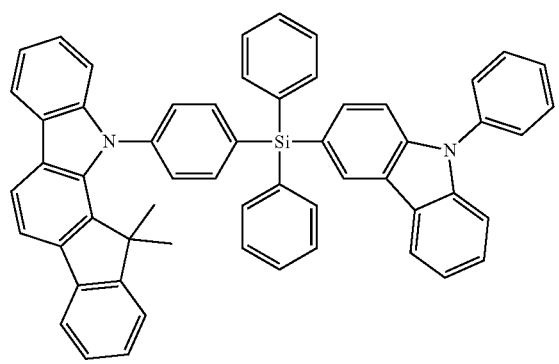
121
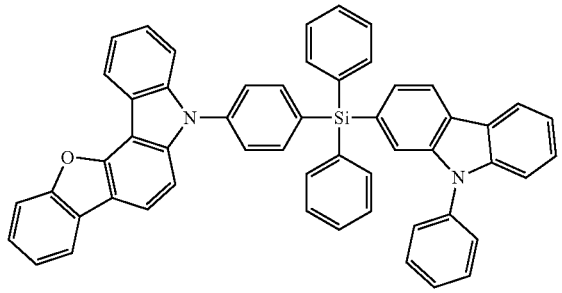
122
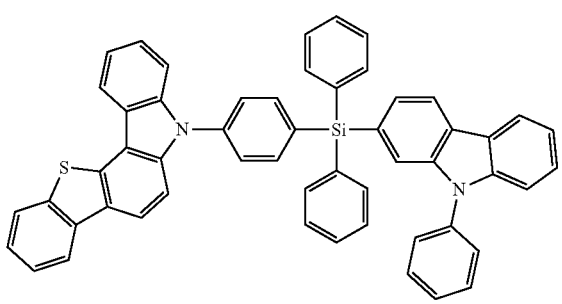
-continued
123
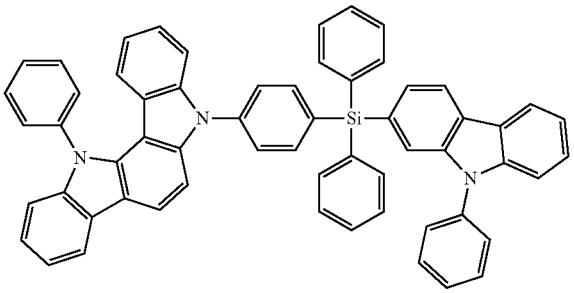
124
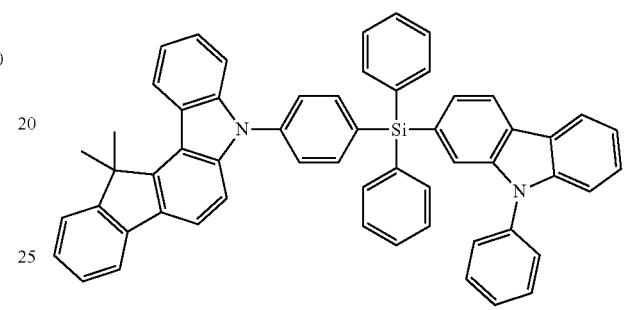
125
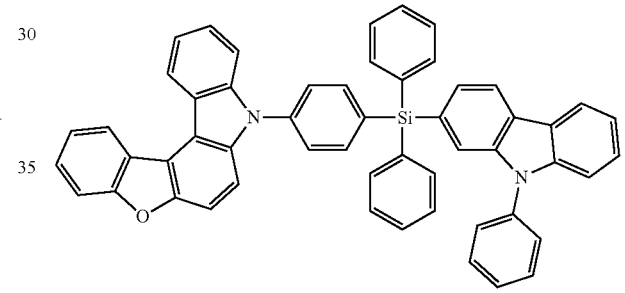
126
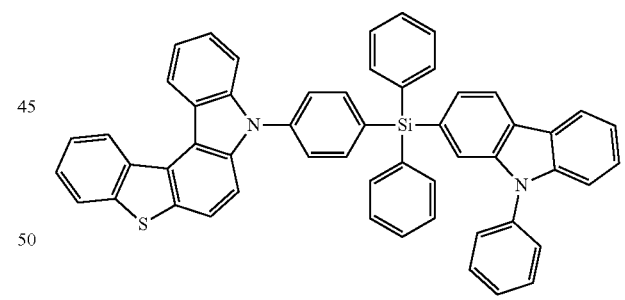
127
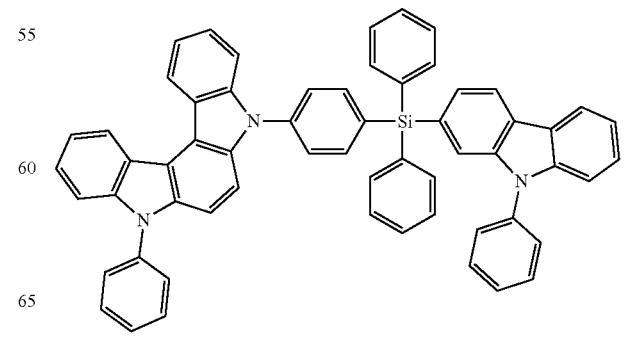

128
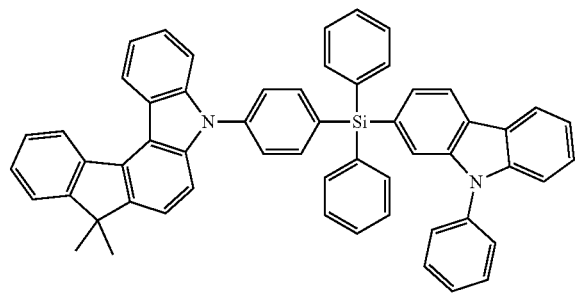
129
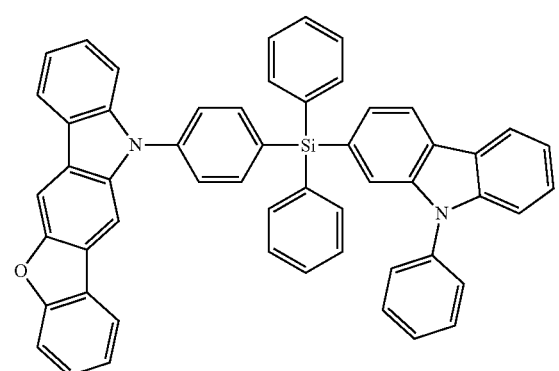
130
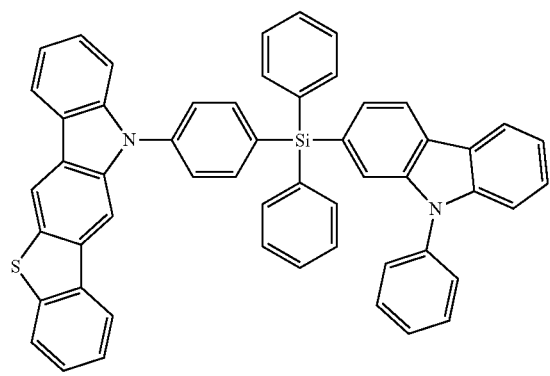
131
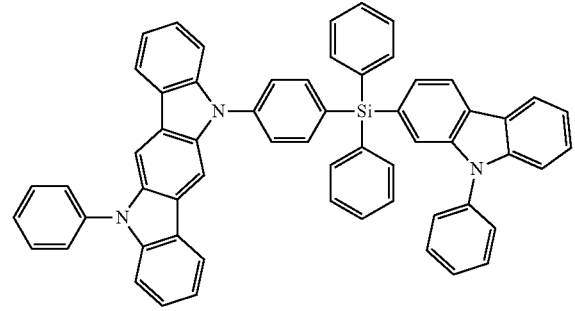
132
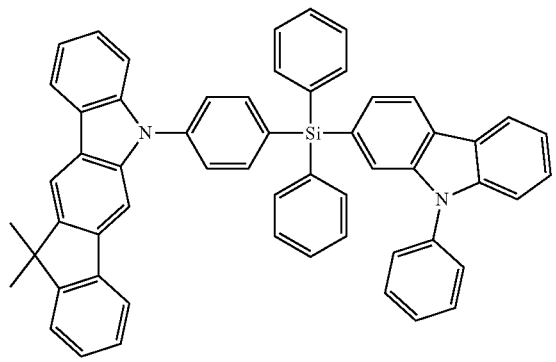
133
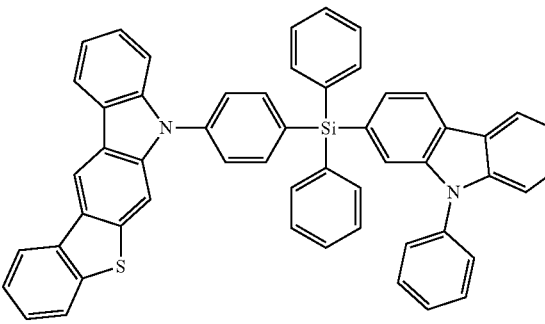
134
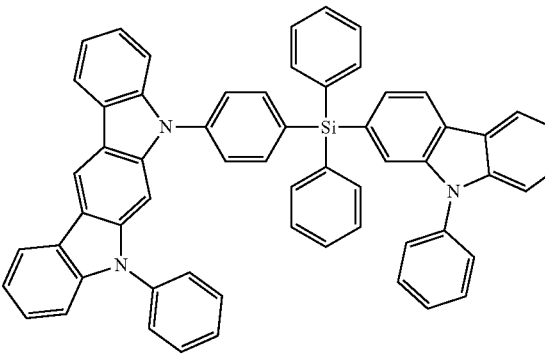
135

-continued
136
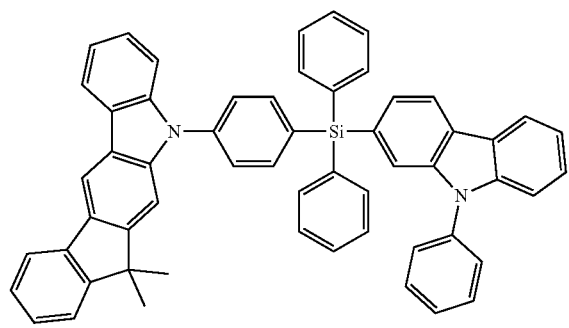
137
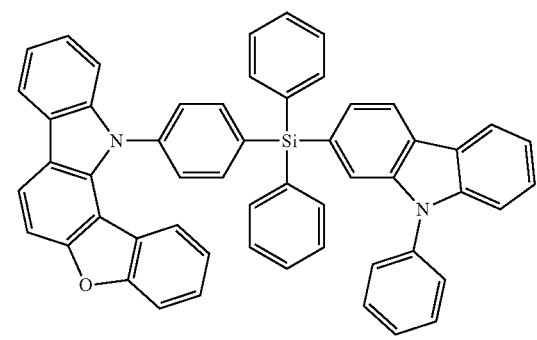
138
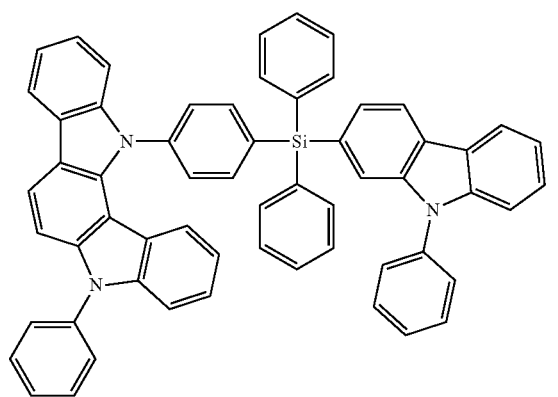
139
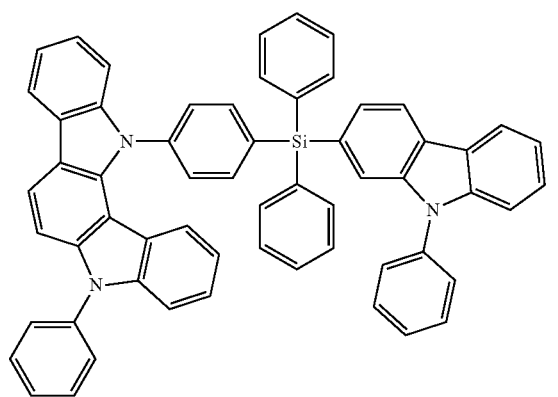
-continued
140
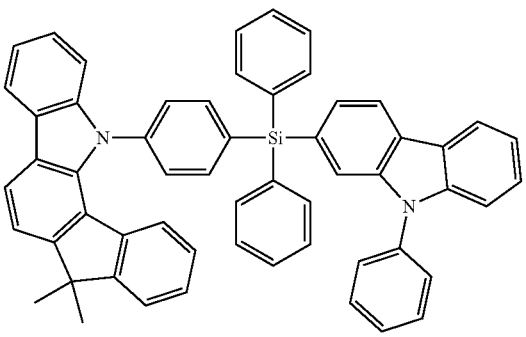
141
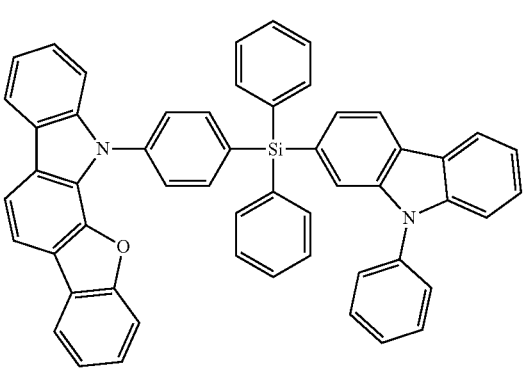
142
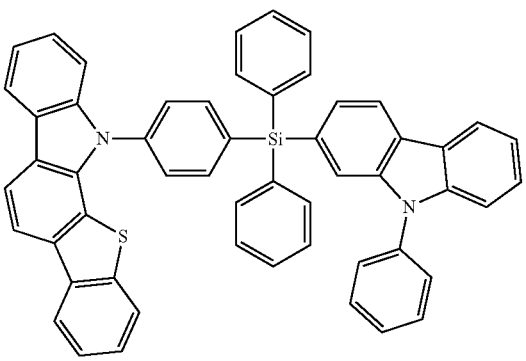
143
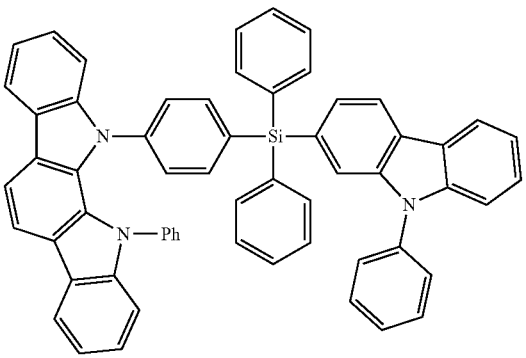

987 -continued
144
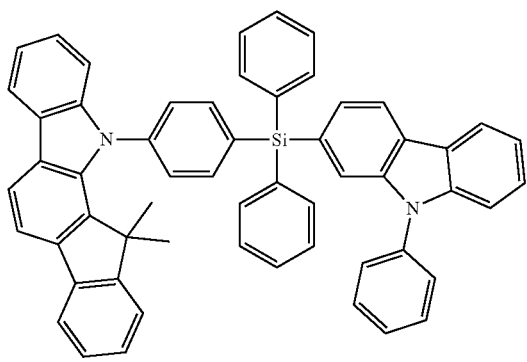
145
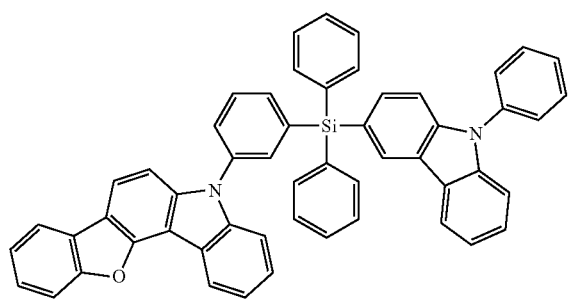
146
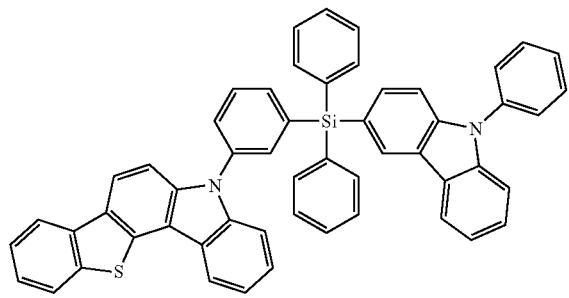
147
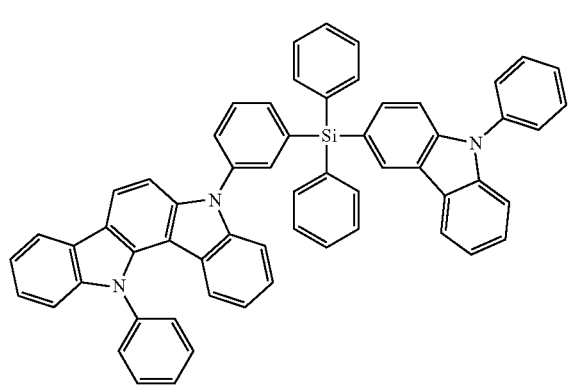
988 -continued
148
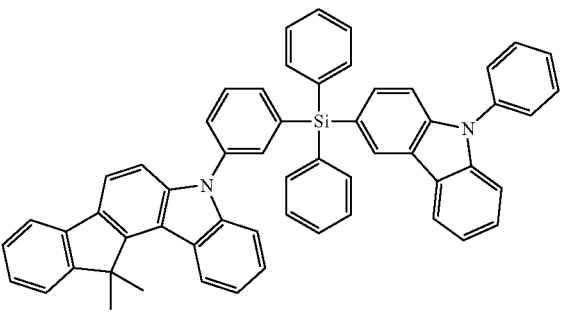
149
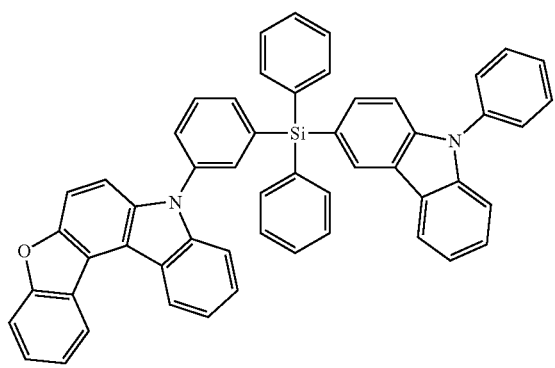
150
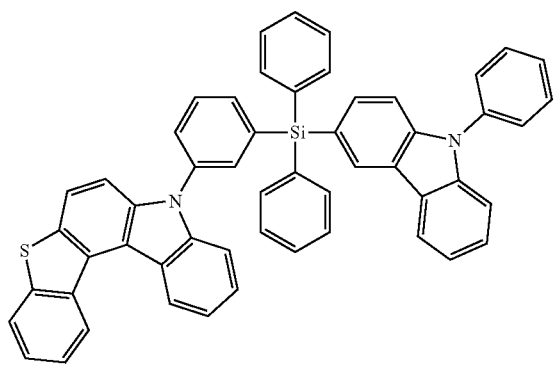
151
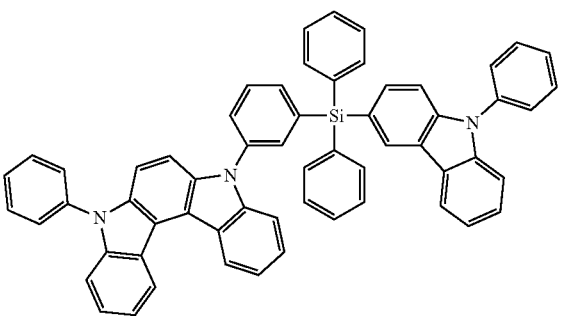

152
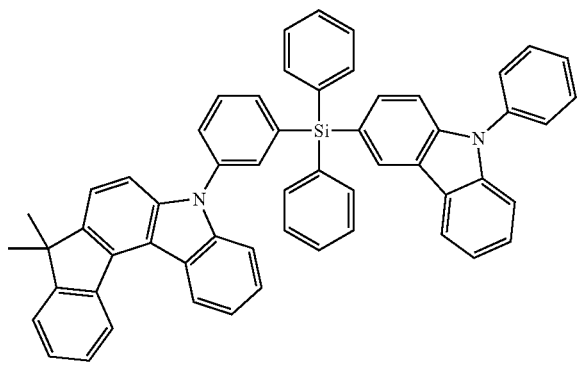
153
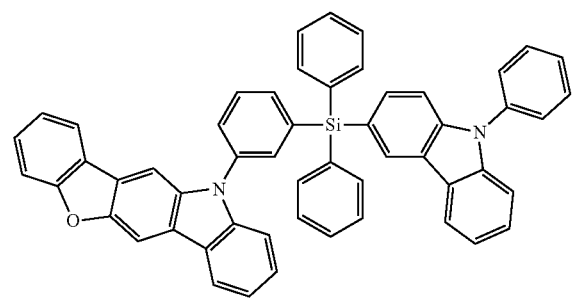
154
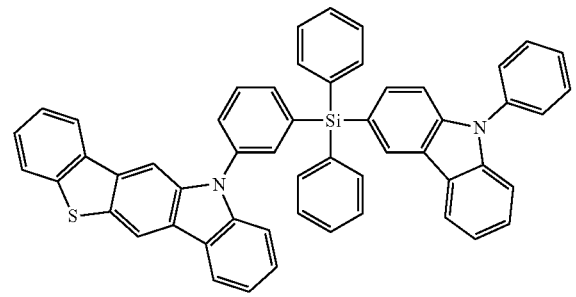
155
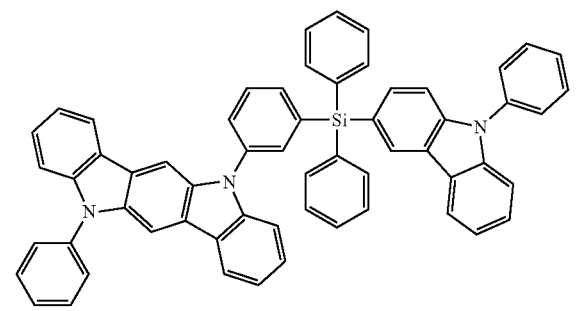
156
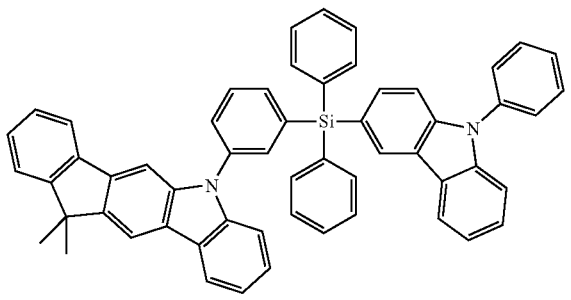
157
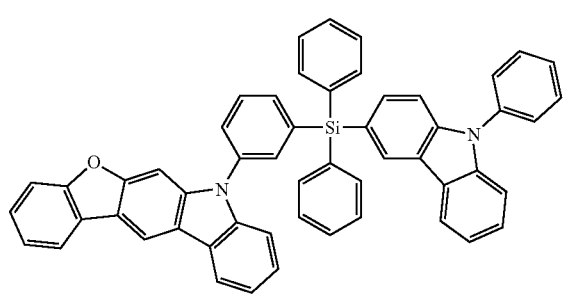
158
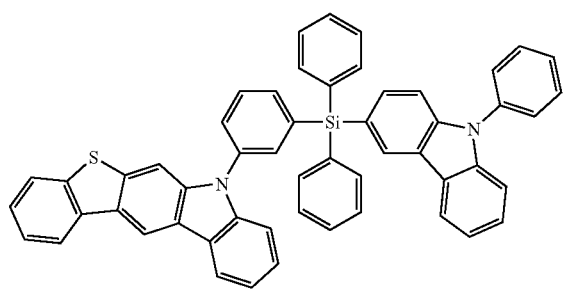
159
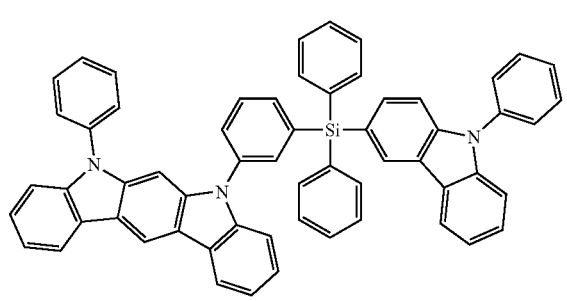
160
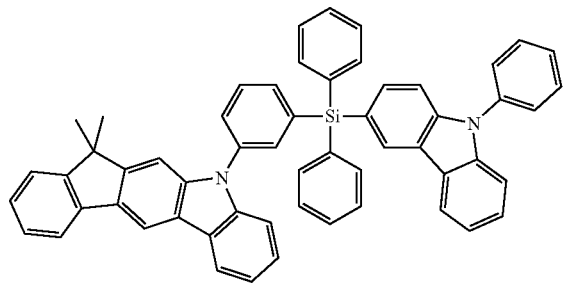

991
-continued
161
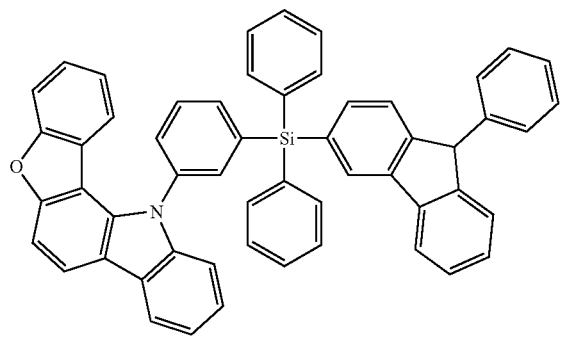
162
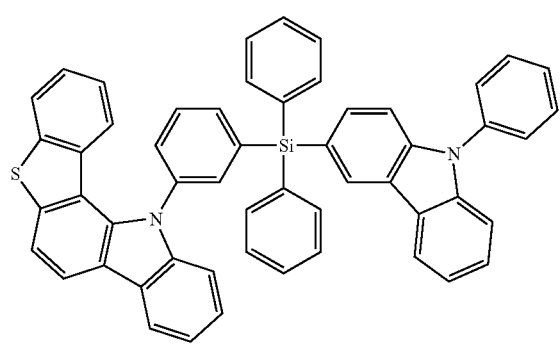
163
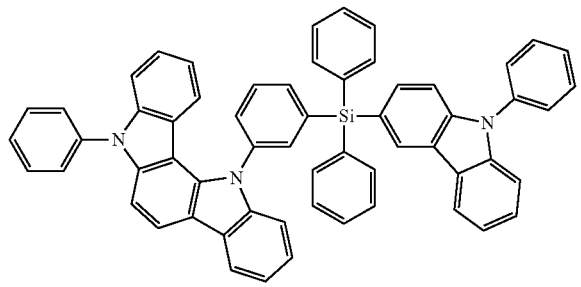
164
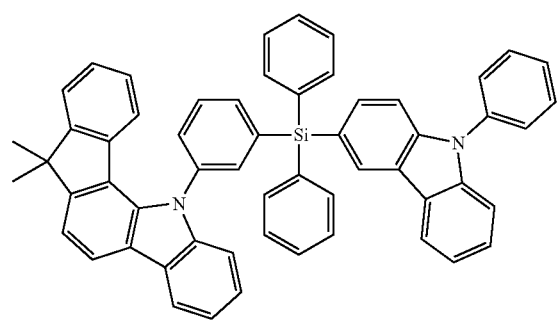
992
-continued
165
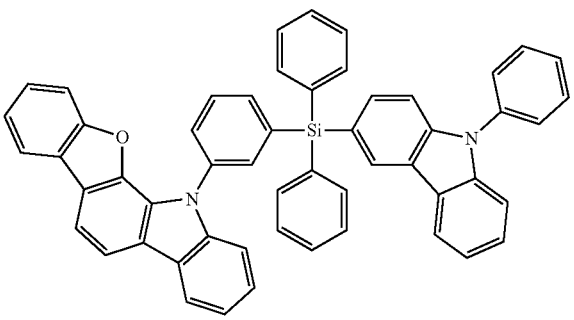
166
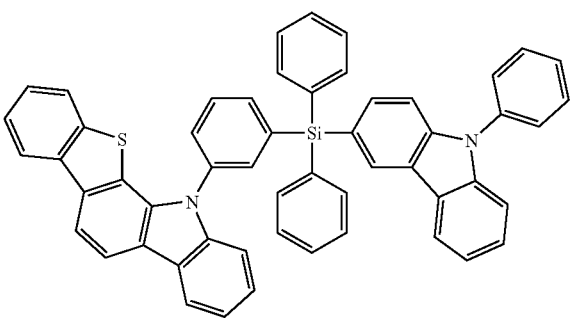
167
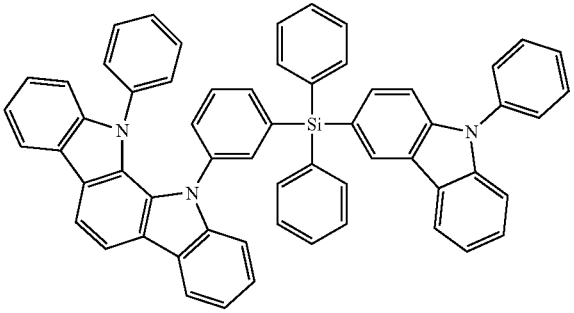
168
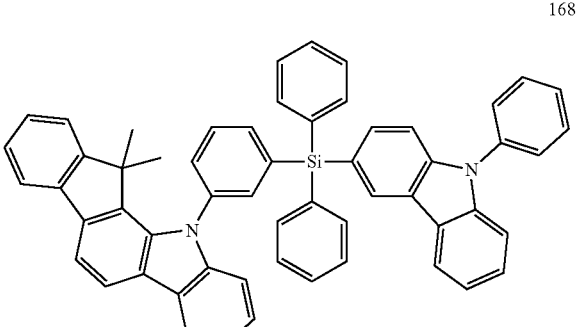

993
-continued
169
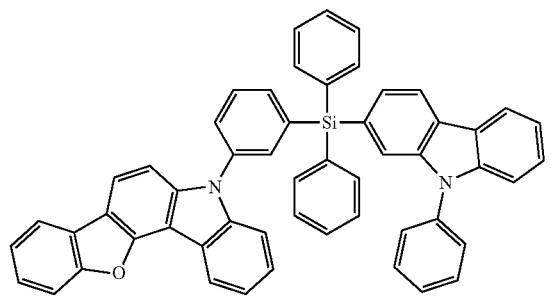
170
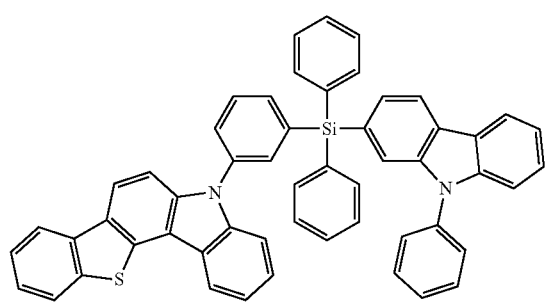
171
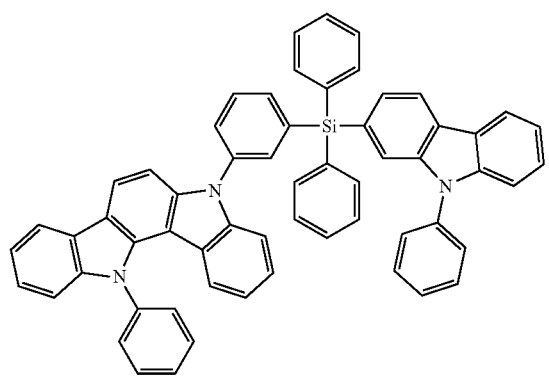
172
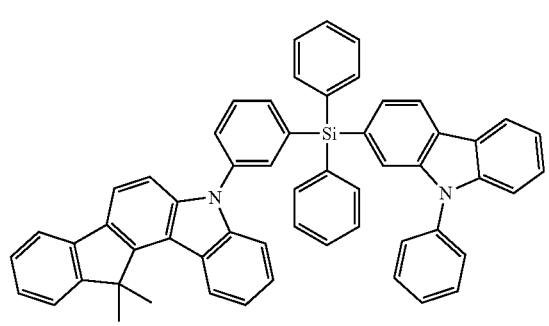
994
-continued
173
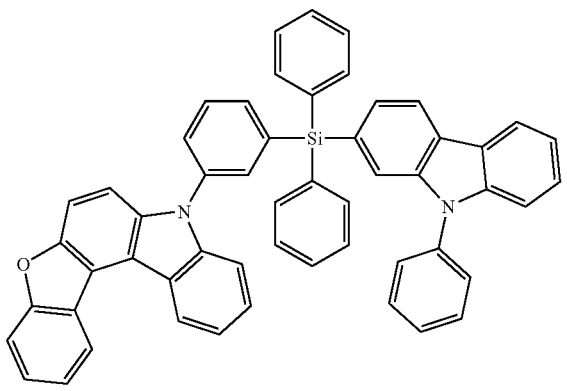
174
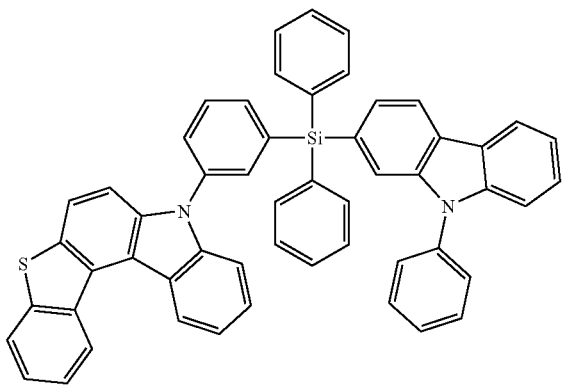
175
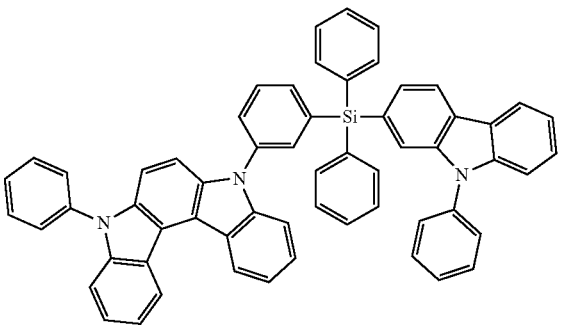
176
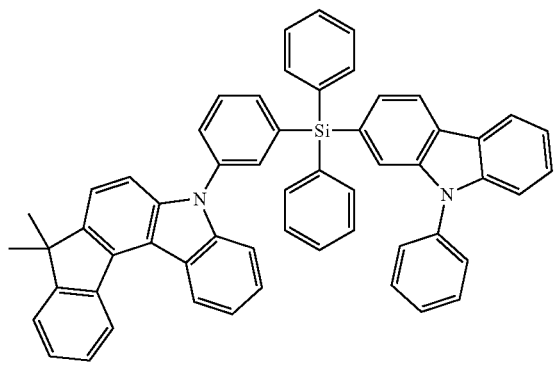

177
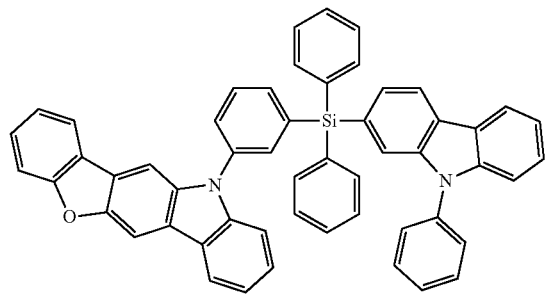
178
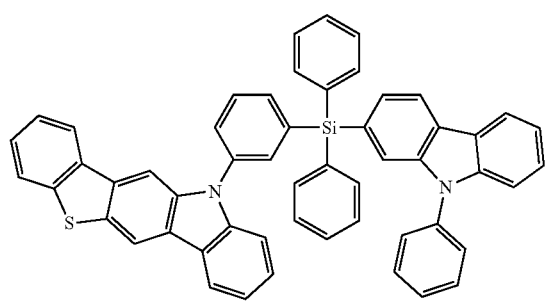
179
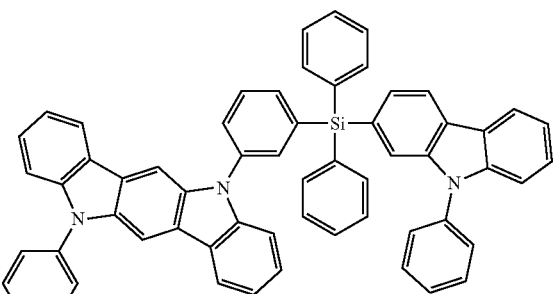
180
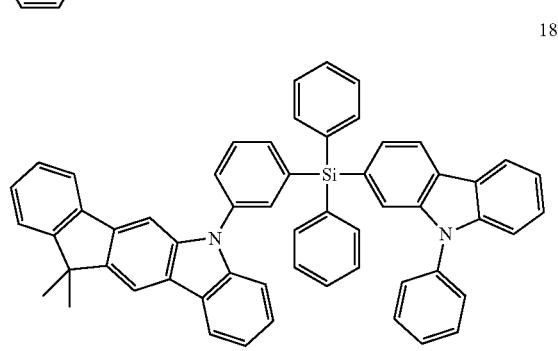
181
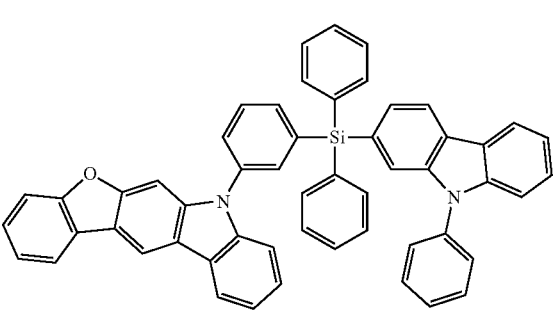
182
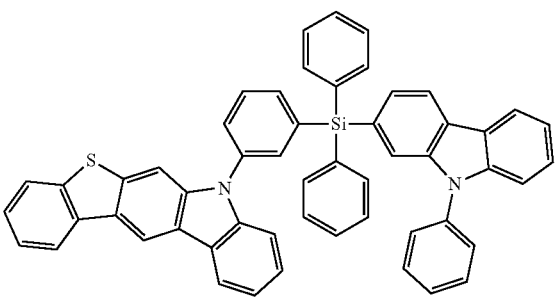
183
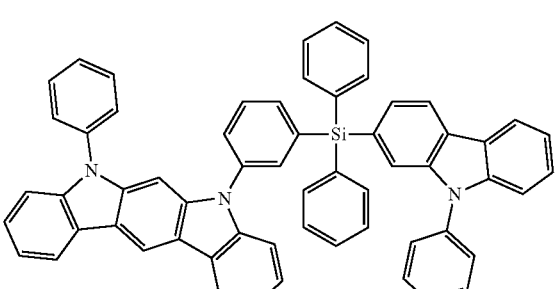
184
185
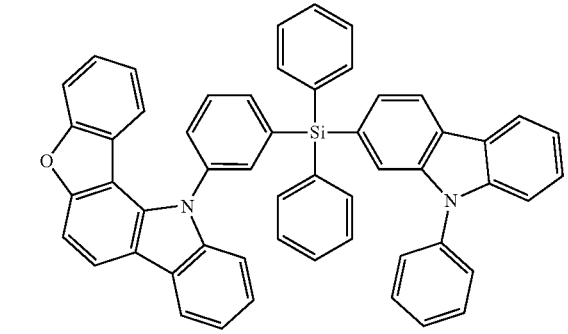

186
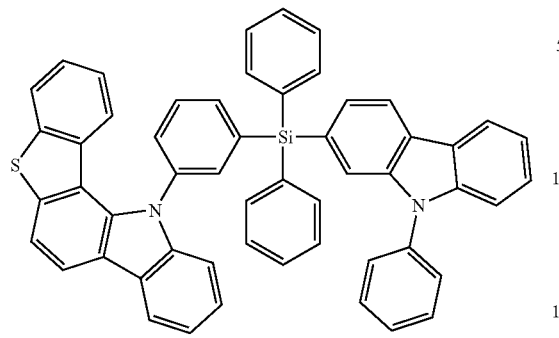
187
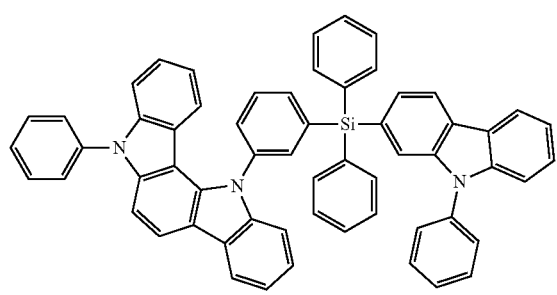
188
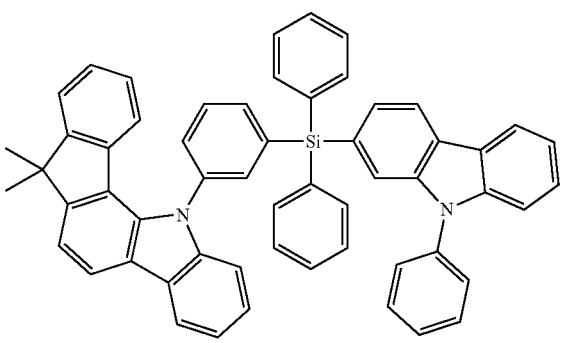
189
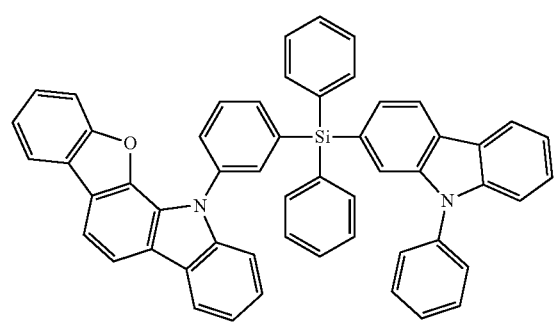
190
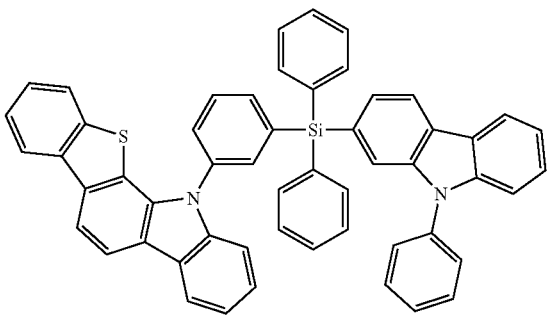
191
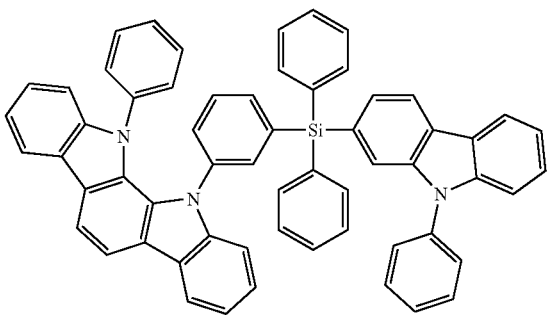
192
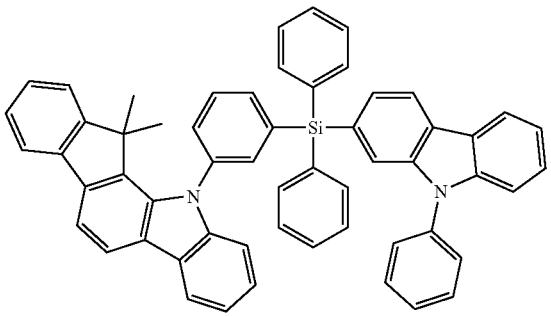
193
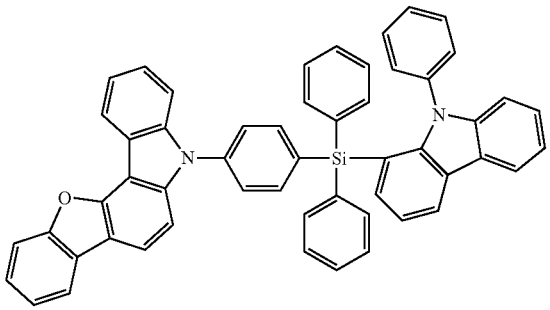

194
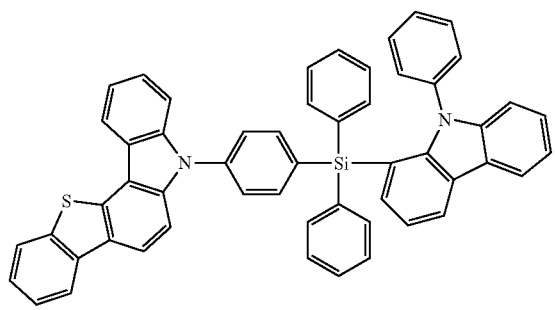
195
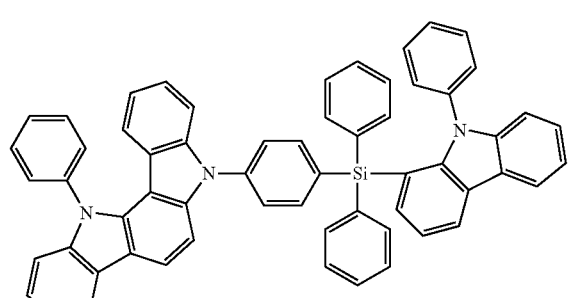
196
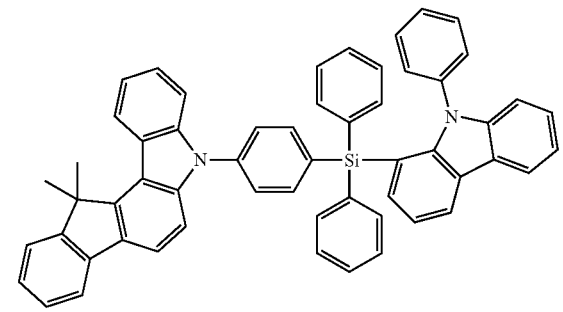
197
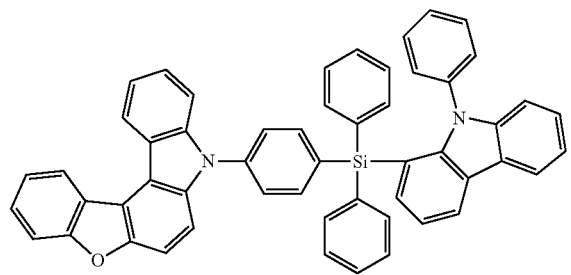
198
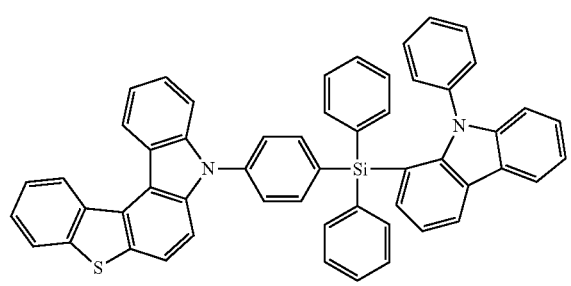
199
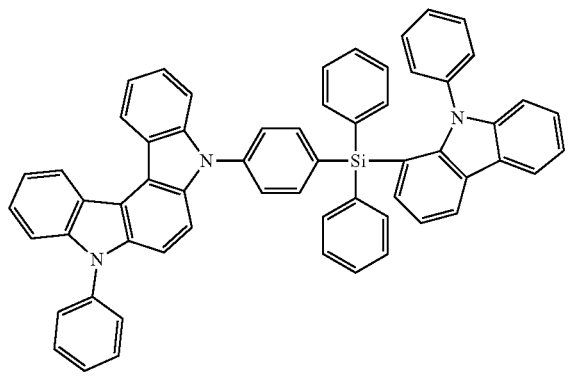
200
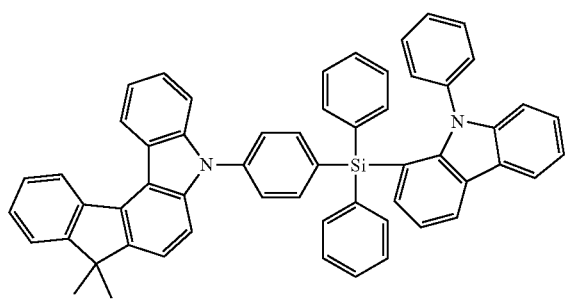
201
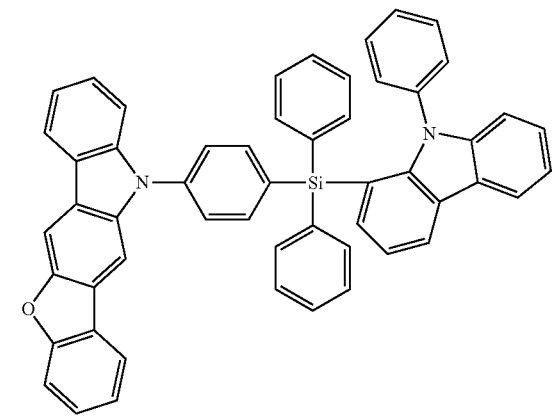
202
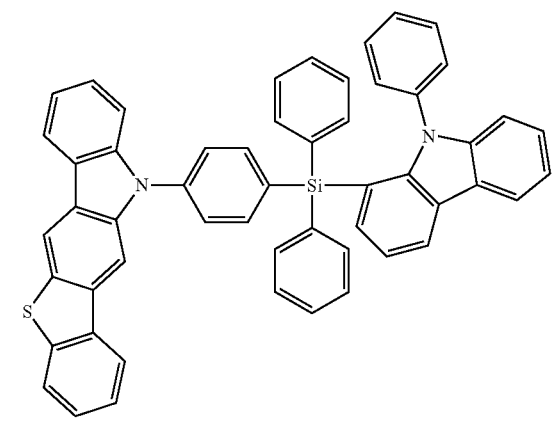

1001
-continued
203
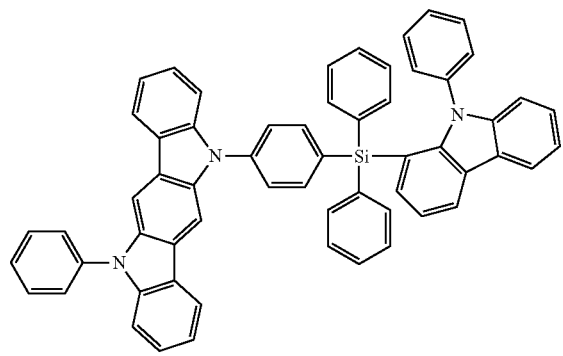
204
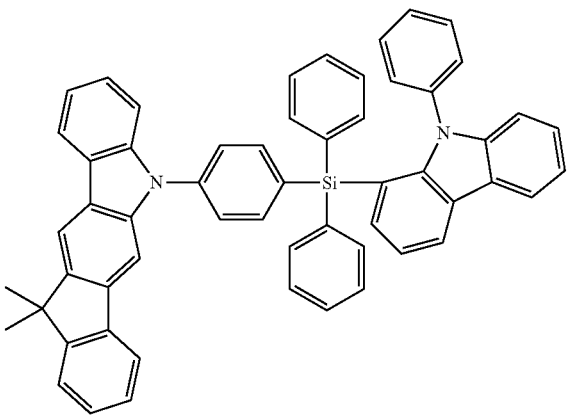
205
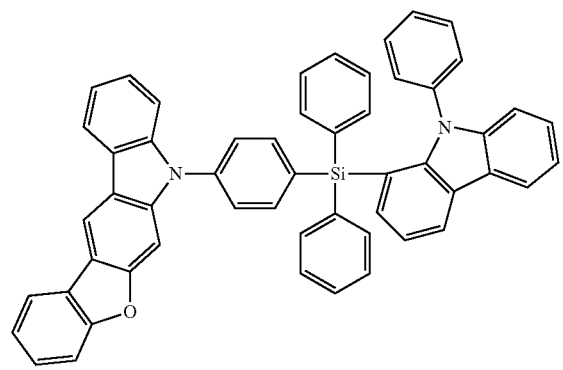
206
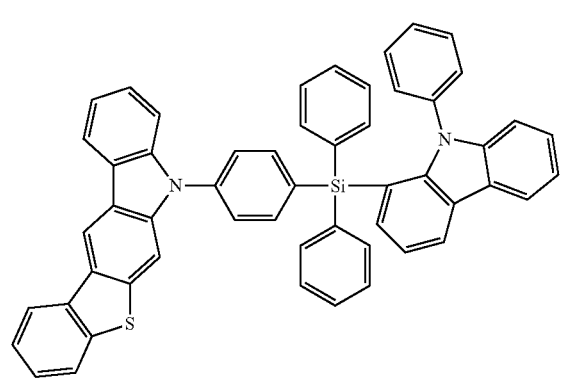
1002
-continued
207
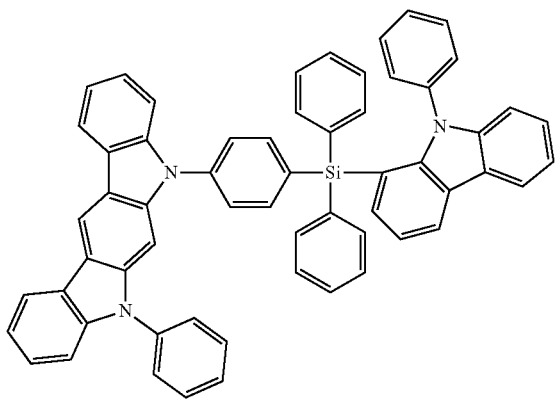
208
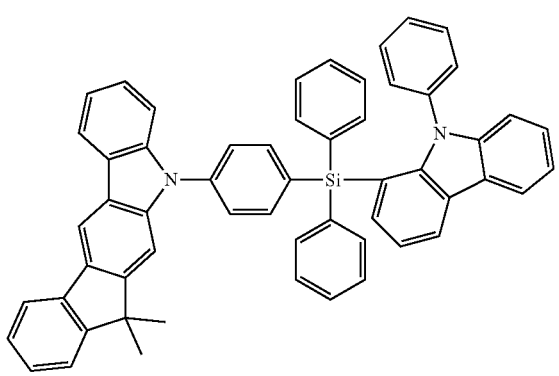
209
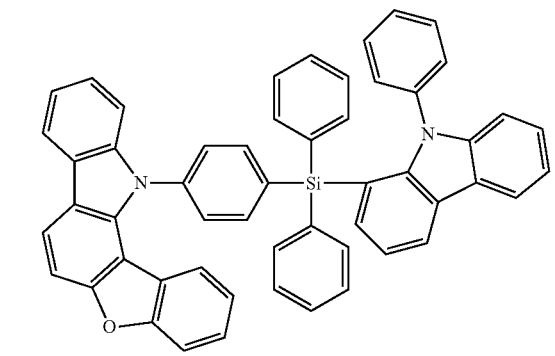
210
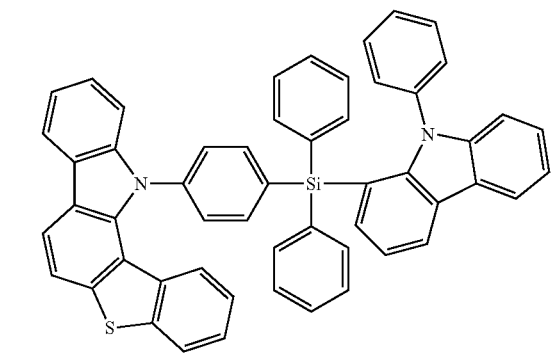

1003
-continued
211
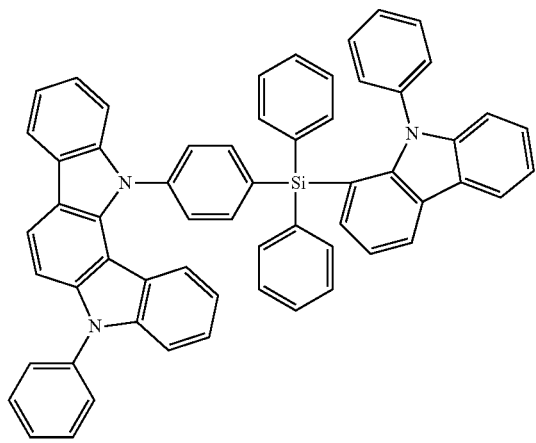
212
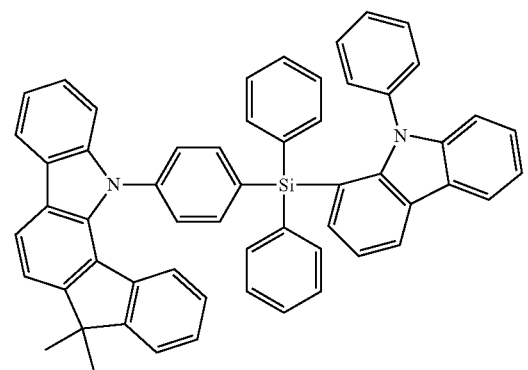
213
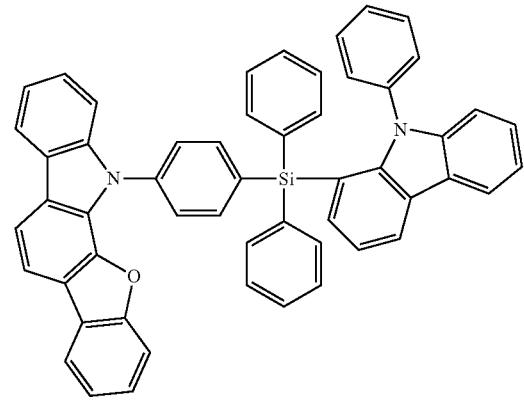
1004
-continued
214
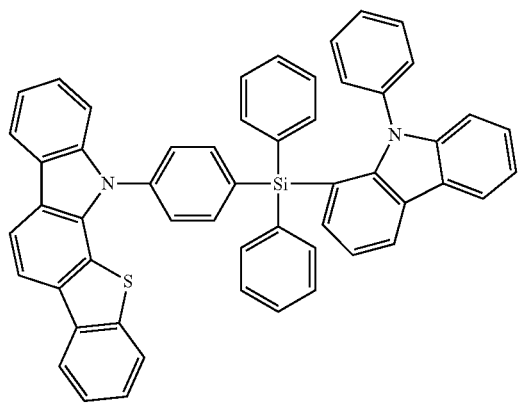
215
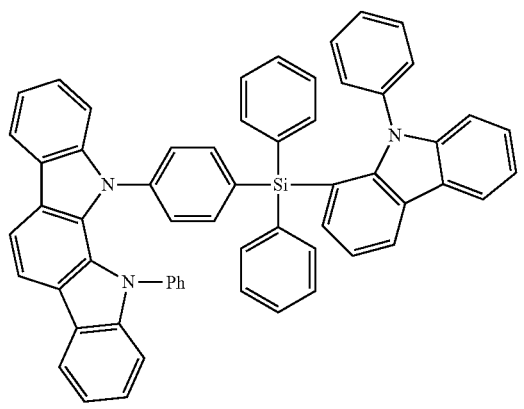
216
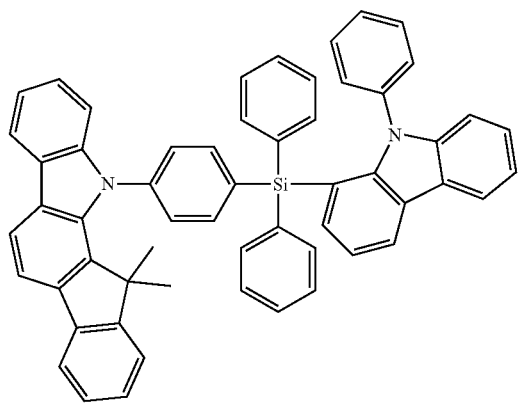
217
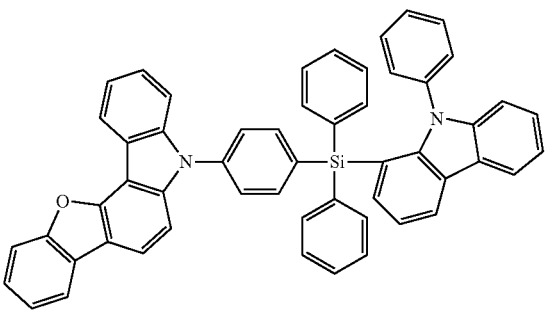

1005
-continued
218
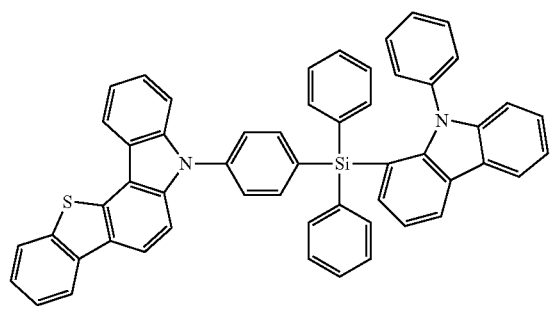
219
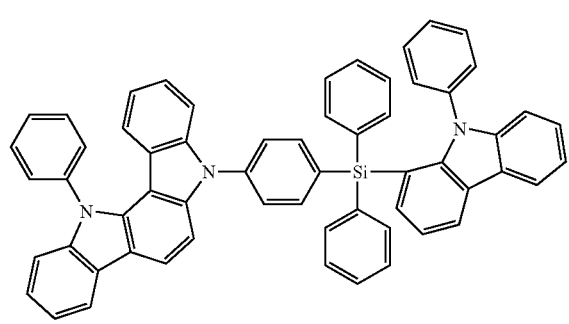
220
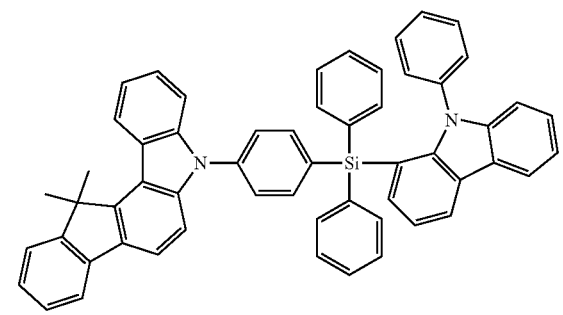
221
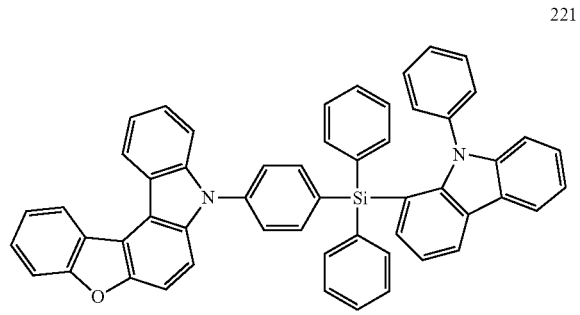
1006
-continued
222
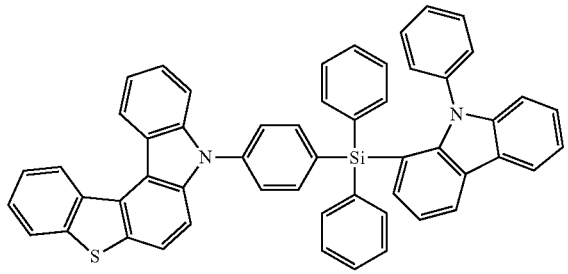
223
224
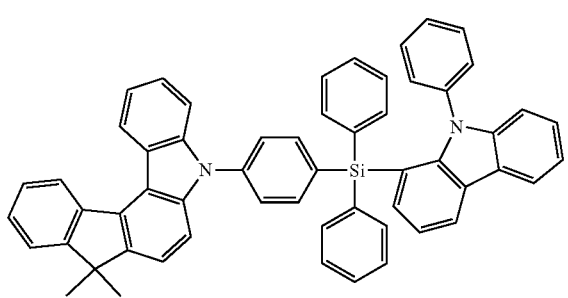

1007
225
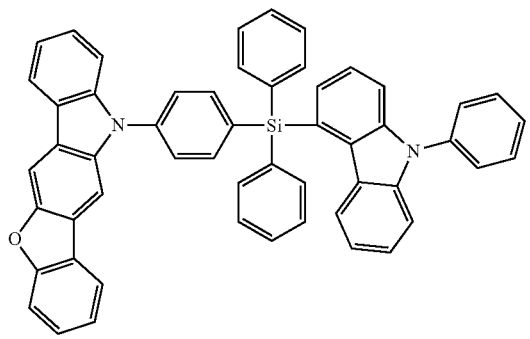
1008
226
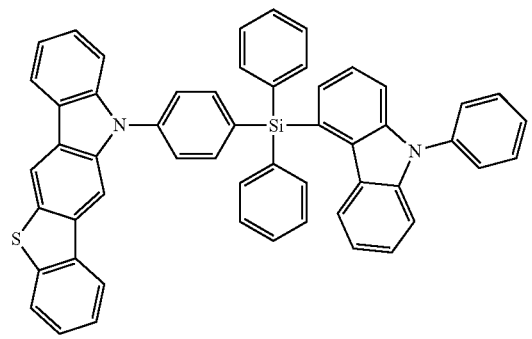
227
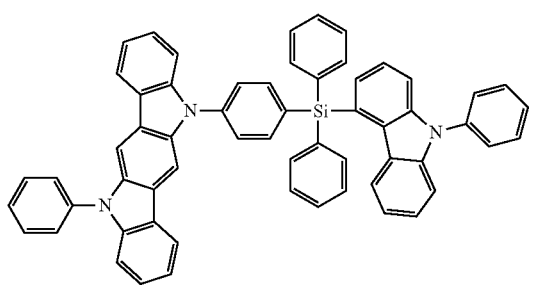
228
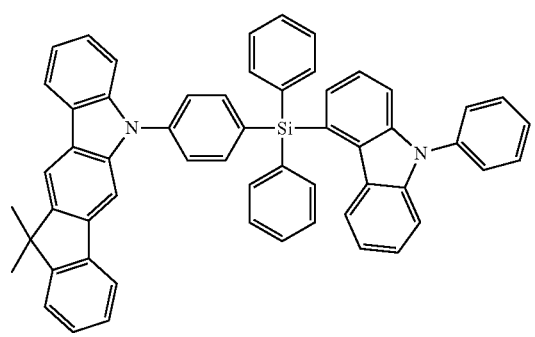
229
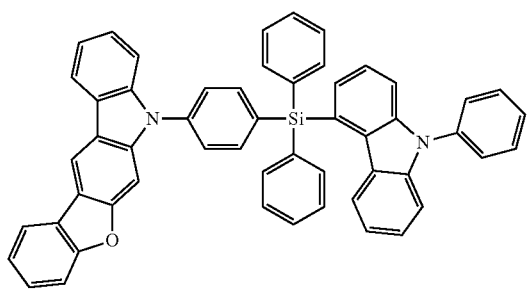
230
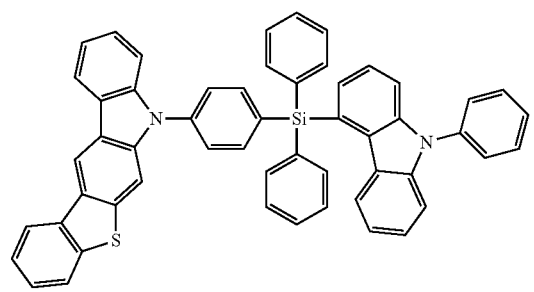
231
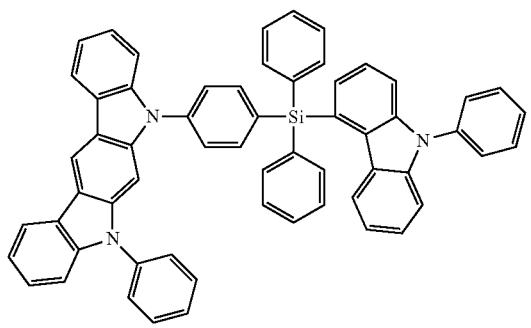
232
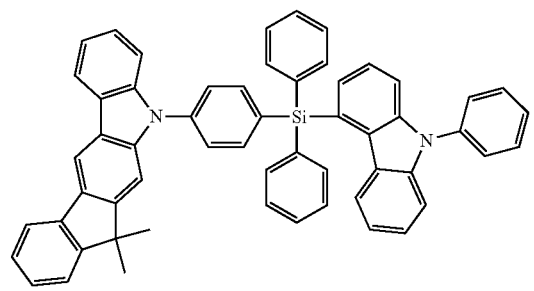

-continued
233
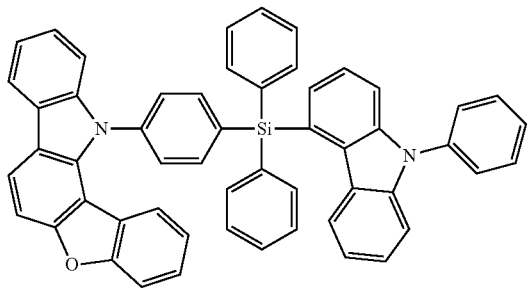
234
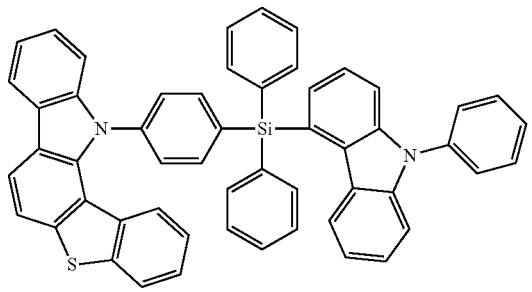
235
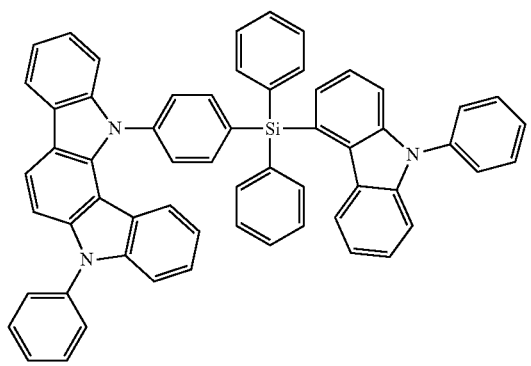
236
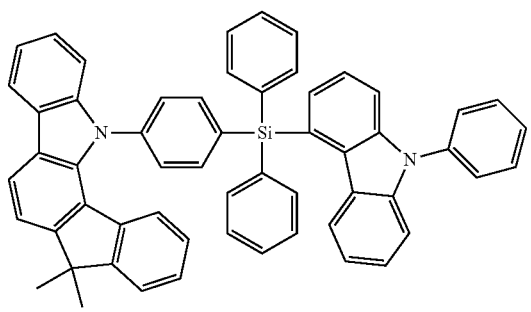
237
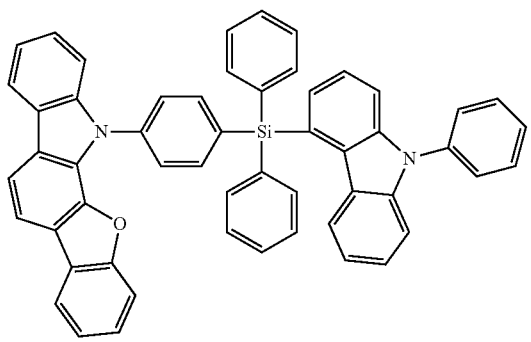
238
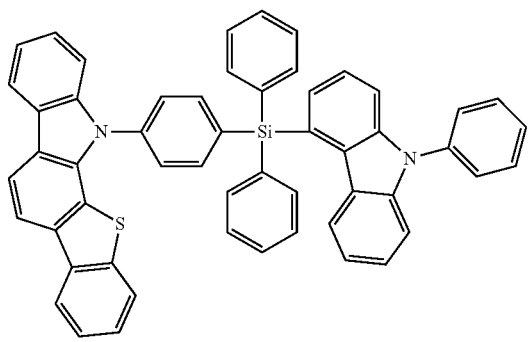
239
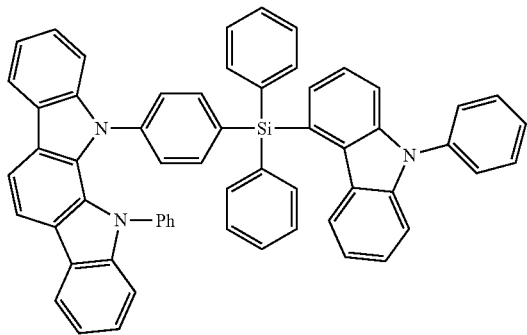
240
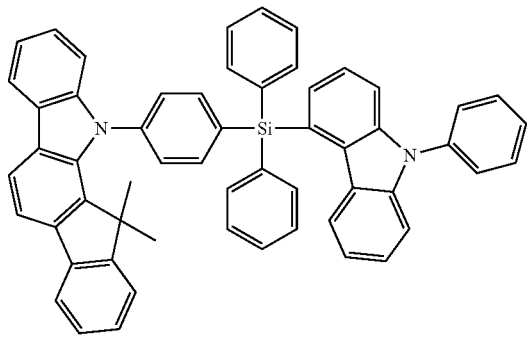

-continued
241
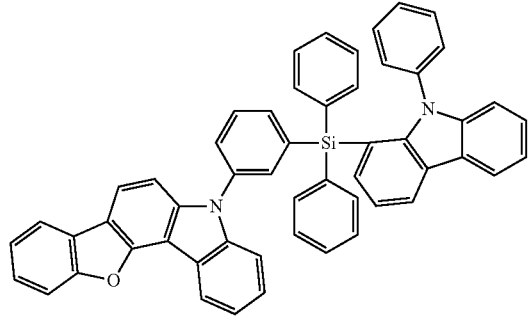
242
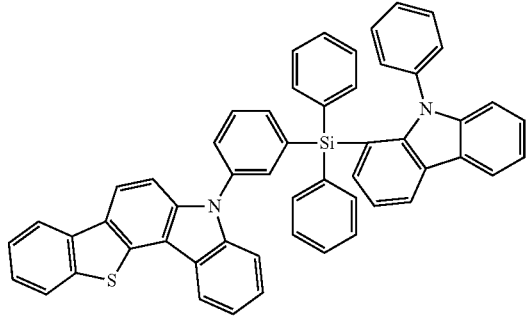
243
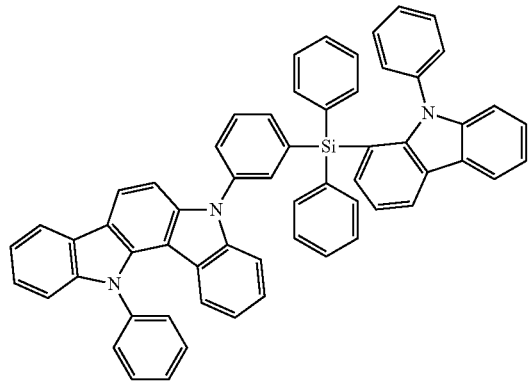
244
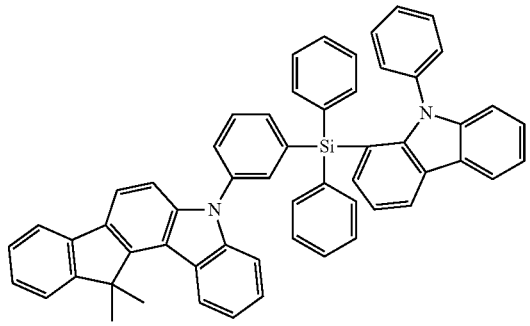
245
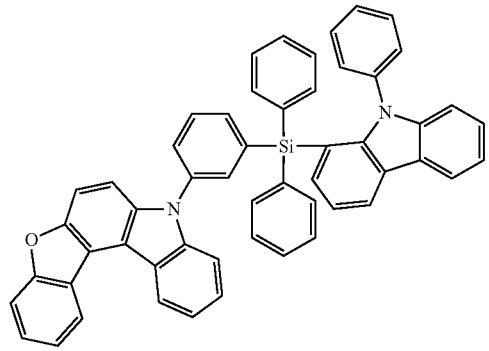
246
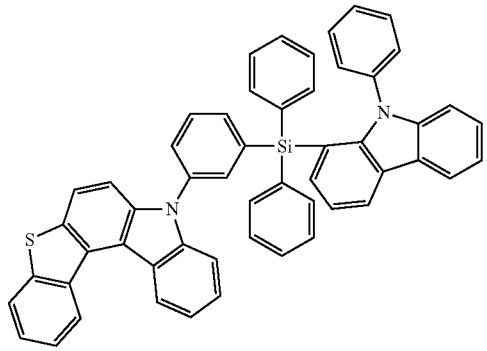
247
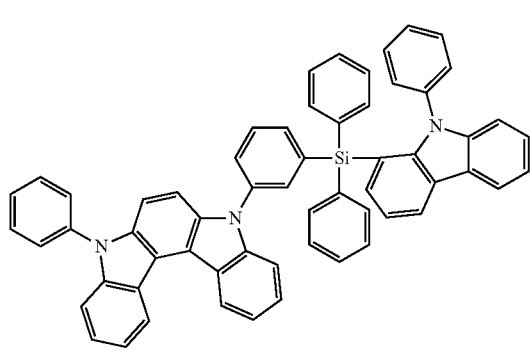
248
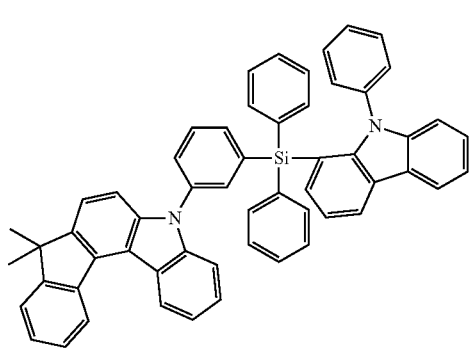

-continued
249
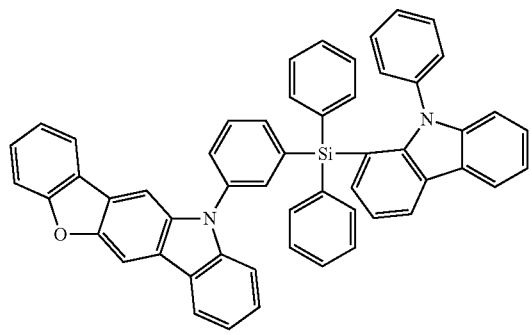
250
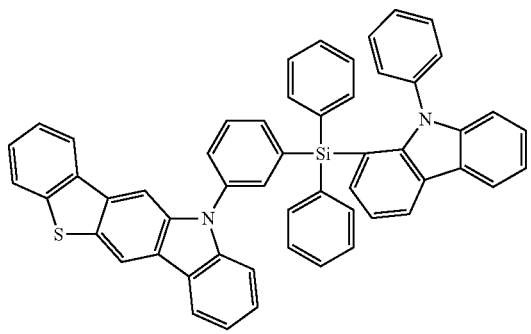
251
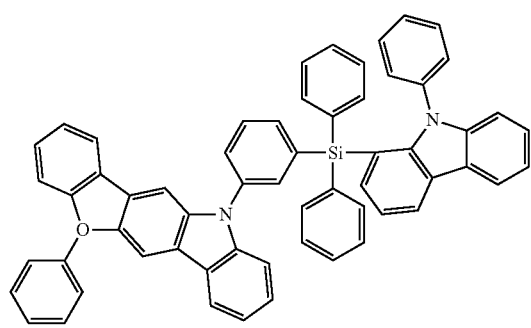
252
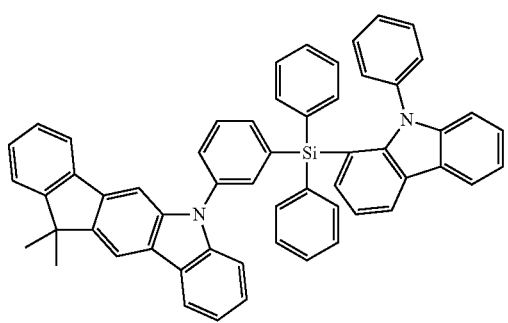
253
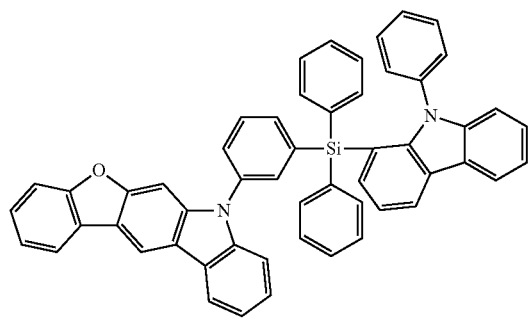
254
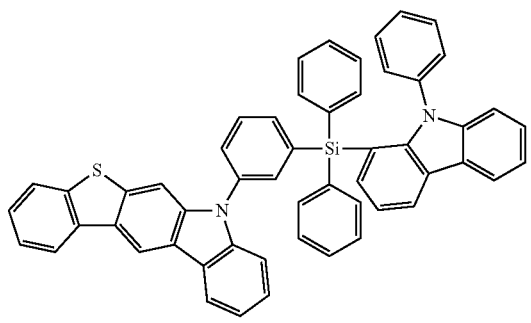
255
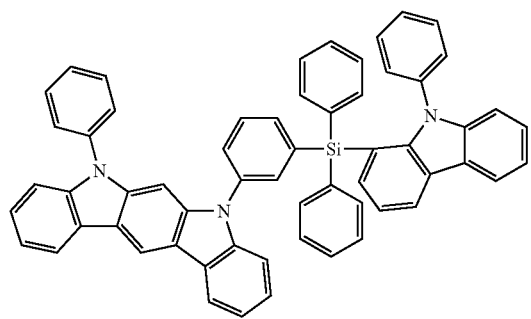
256
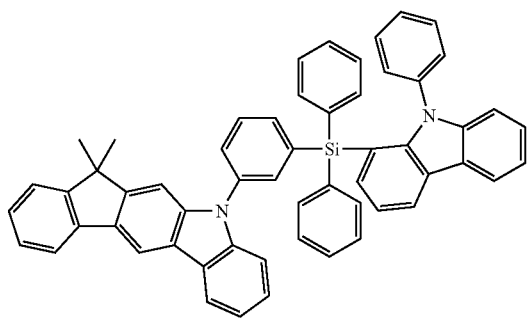

-continued
257
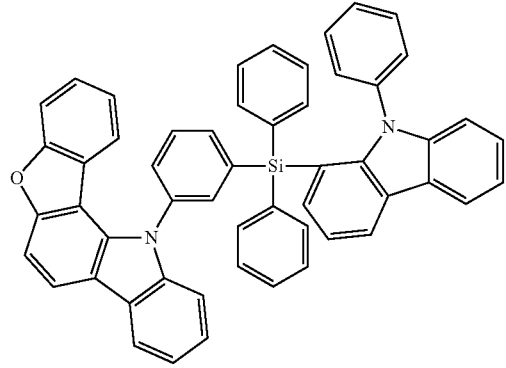
258
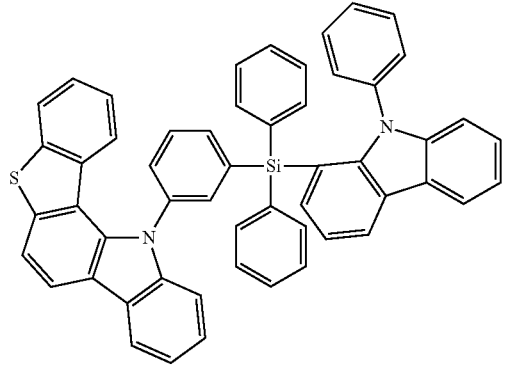
259
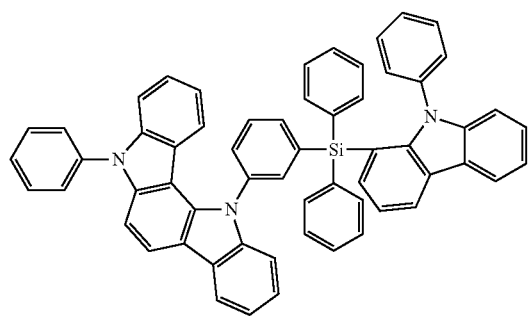
260
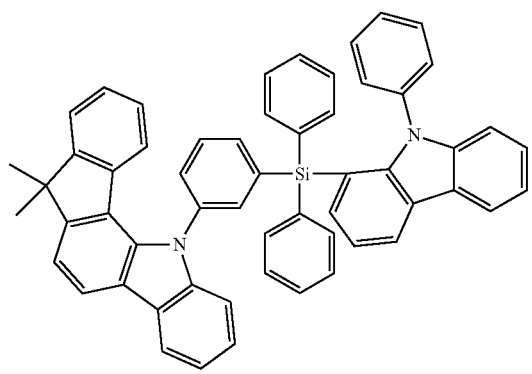
261
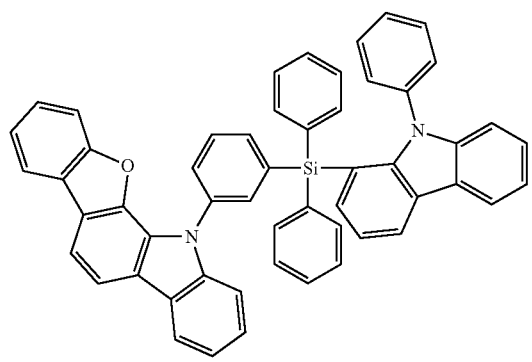
262
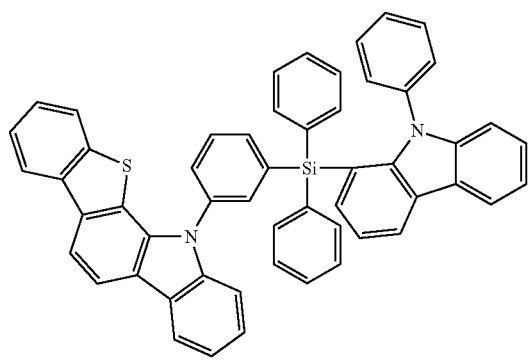
263
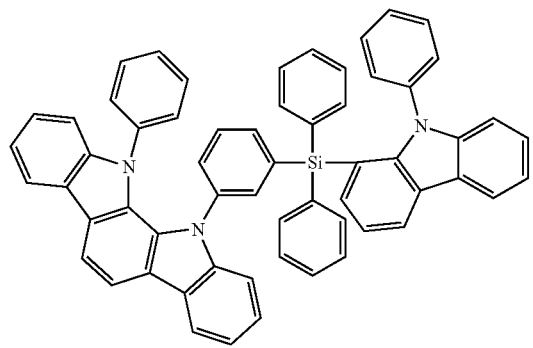
264
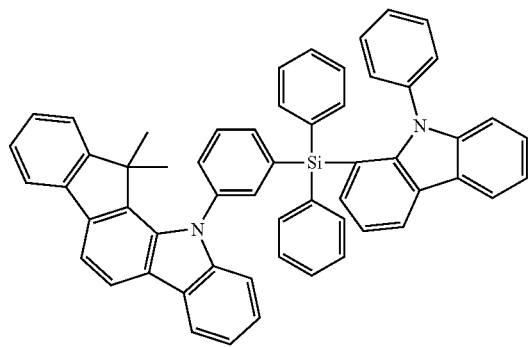

-continued
265
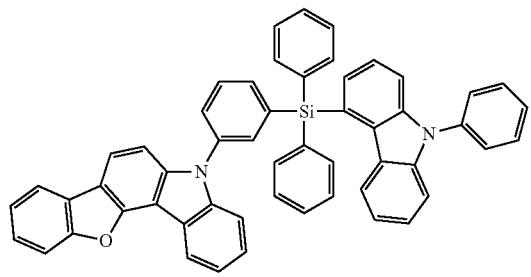
266
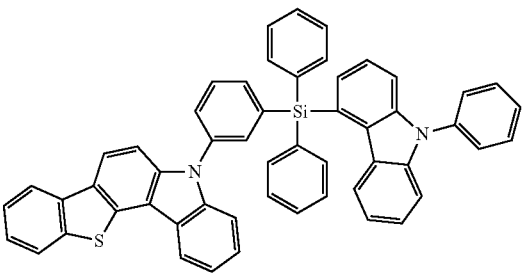
267
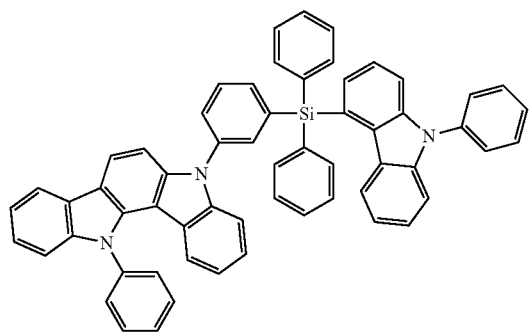
268
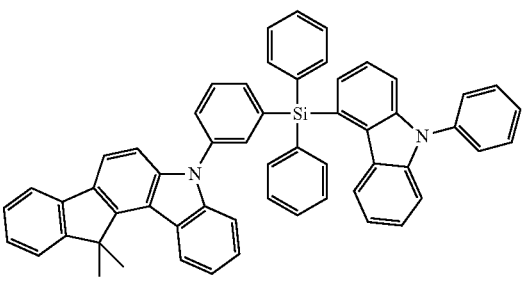
269
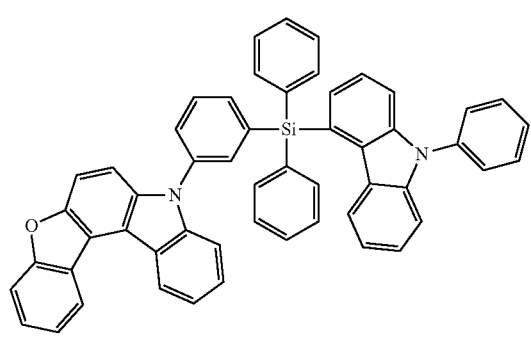
270
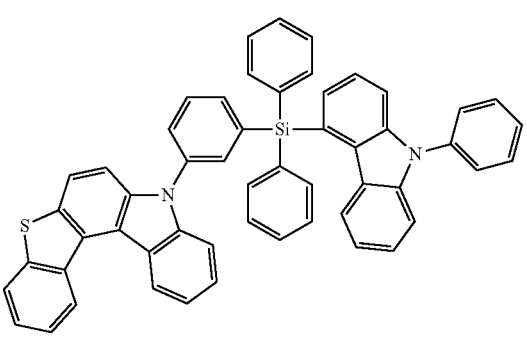
271
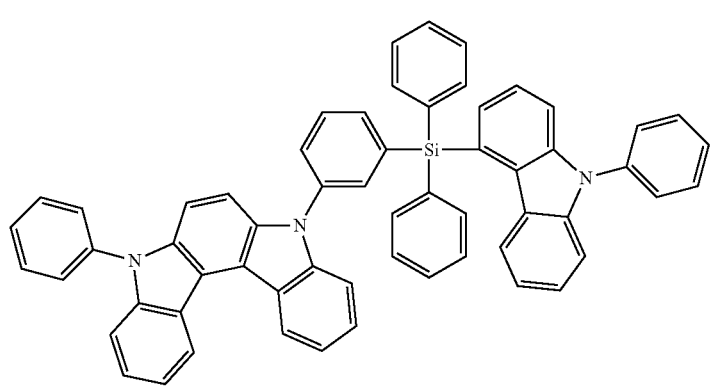

1019 1020
-continued
272 273
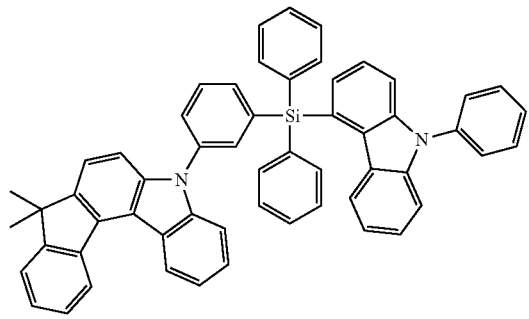 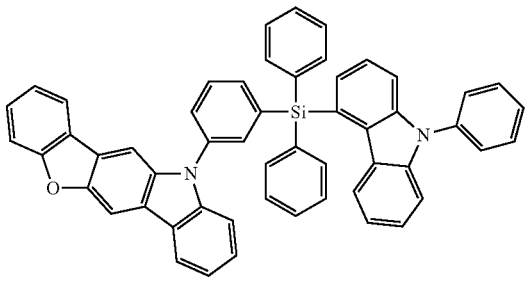
274 275
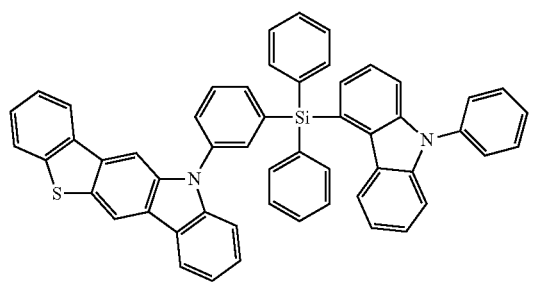 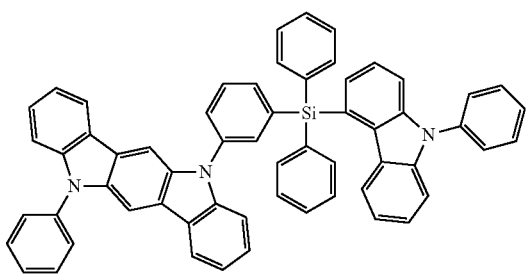
276 277
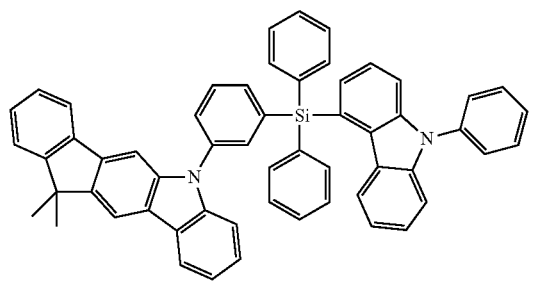 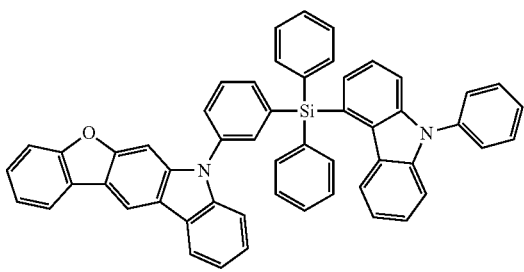
278 279
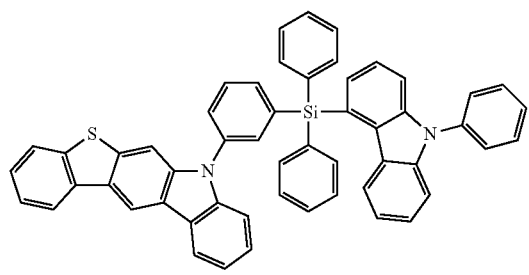 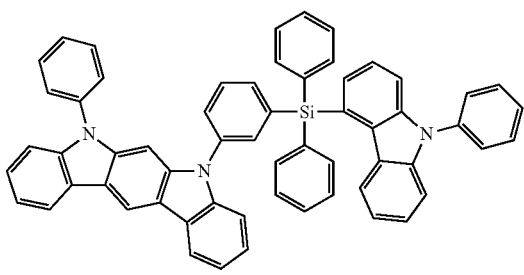
280 281
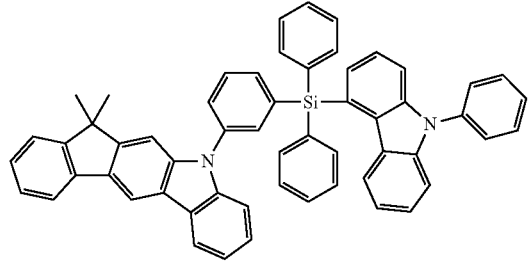 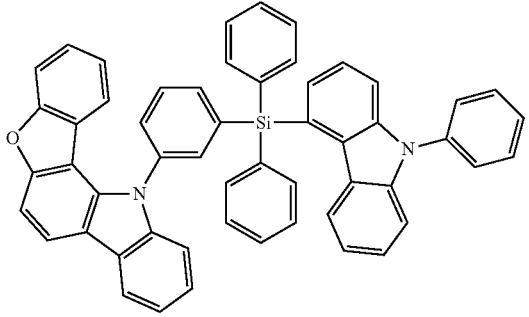

-continued
282
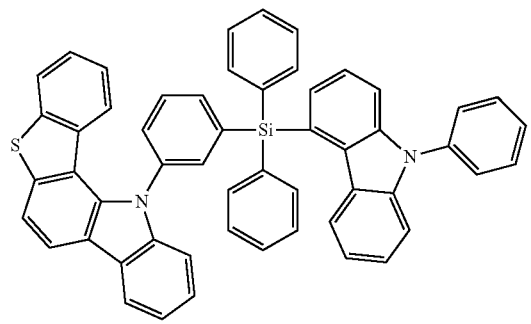
283
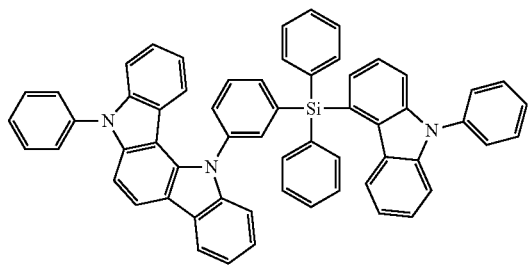
284
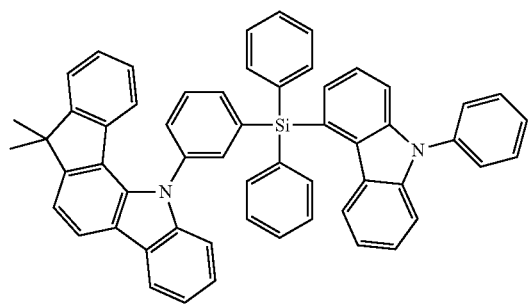
285
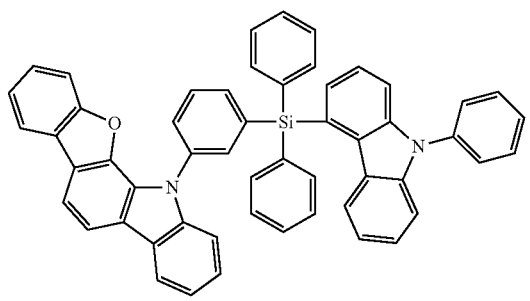
286
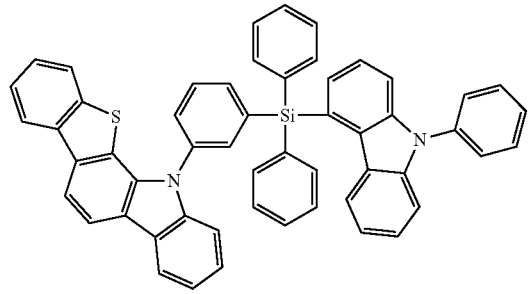
287
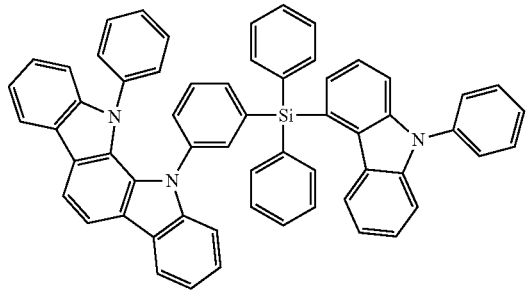
288
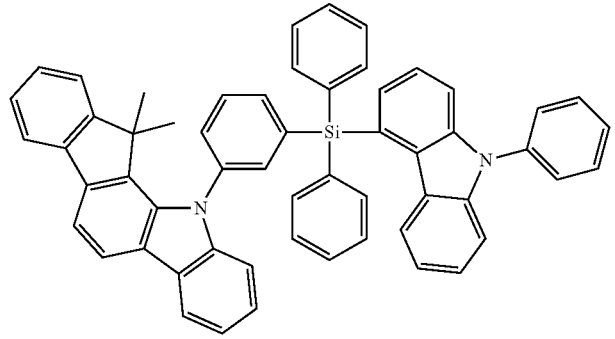
289
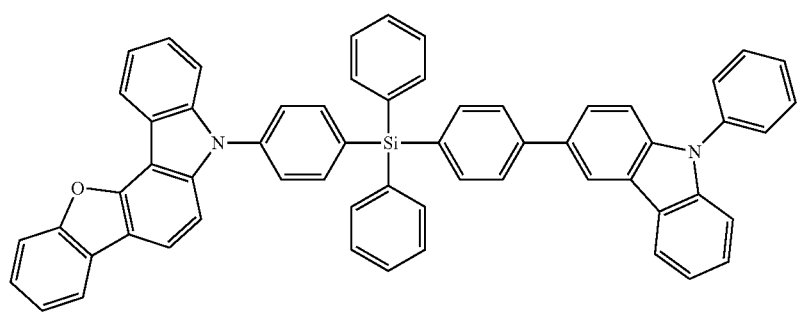

-continued
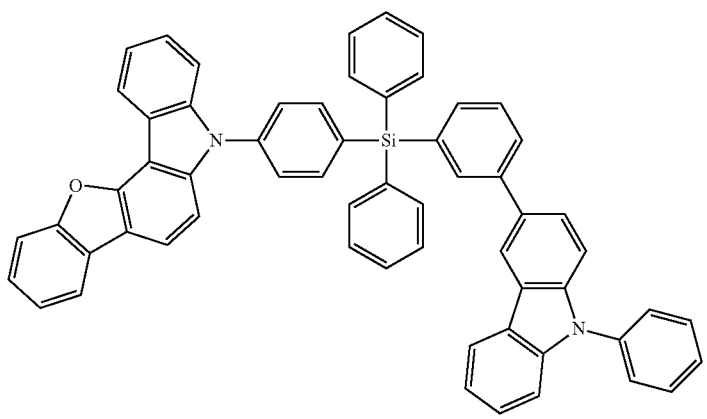
290
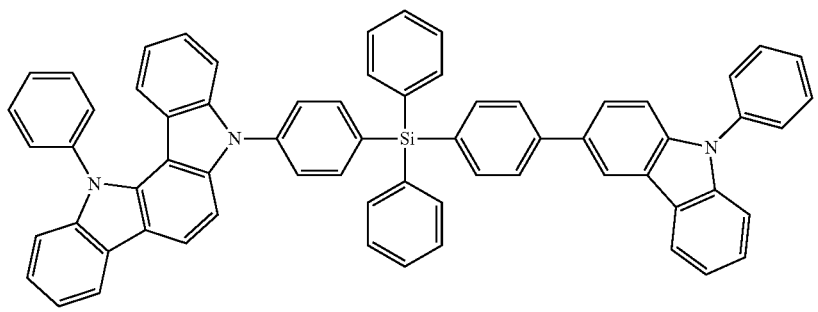
291
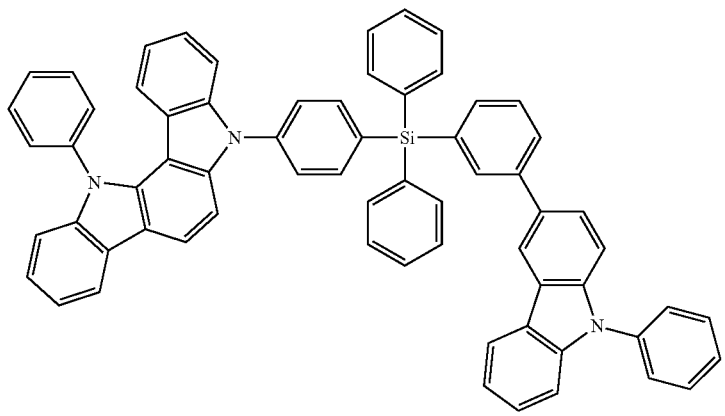
292
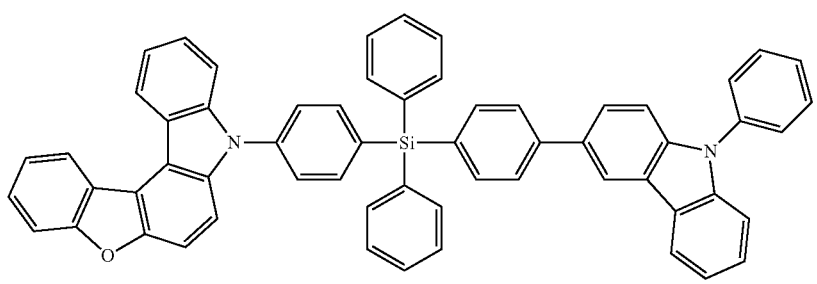
293

-continued
294
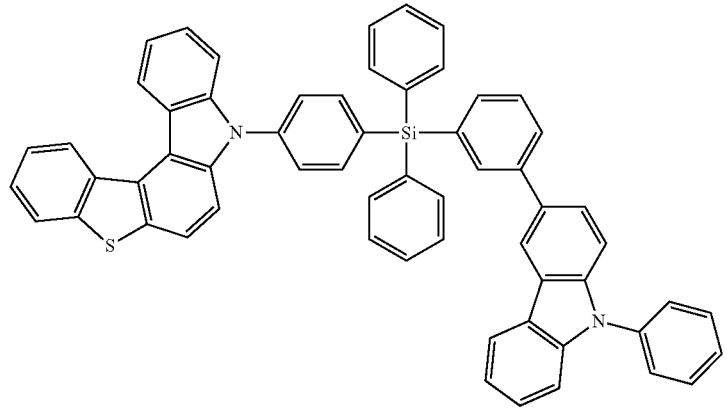
295
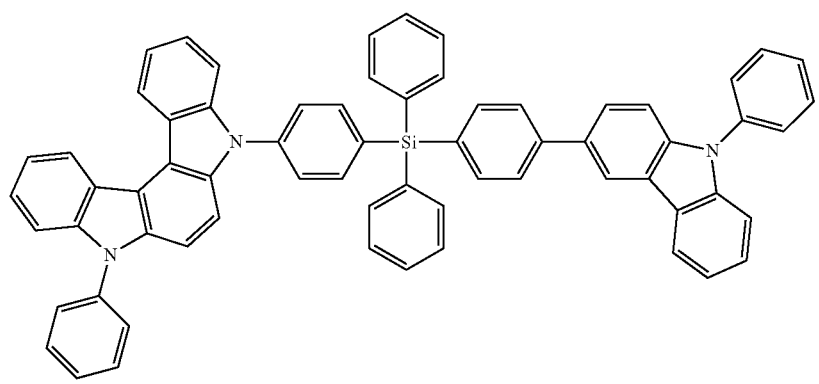
296
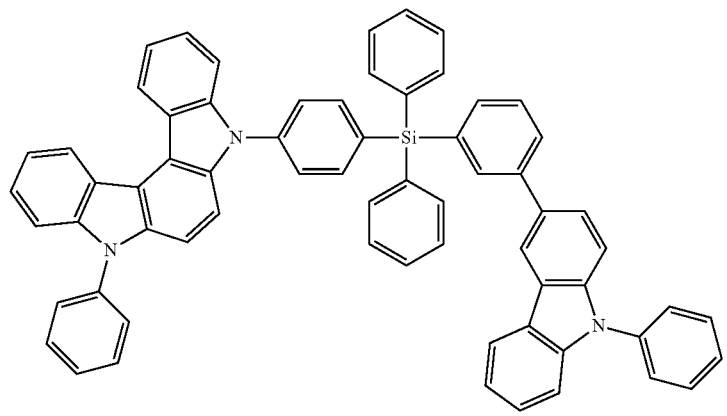
297
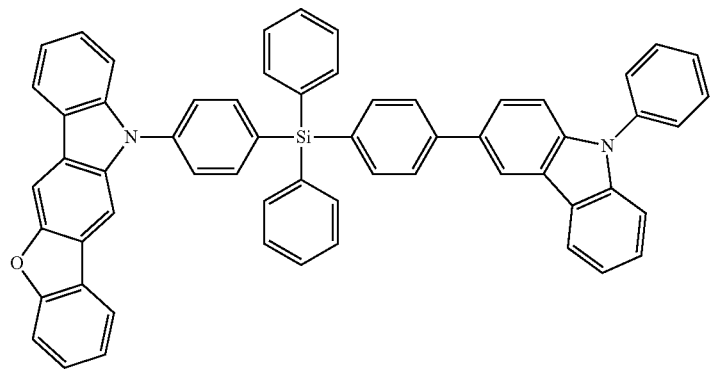

298
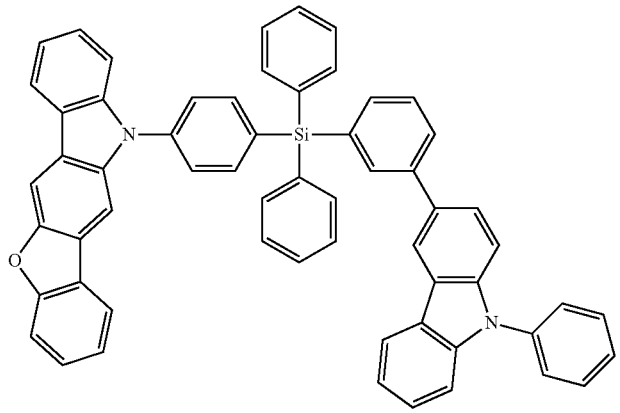
299
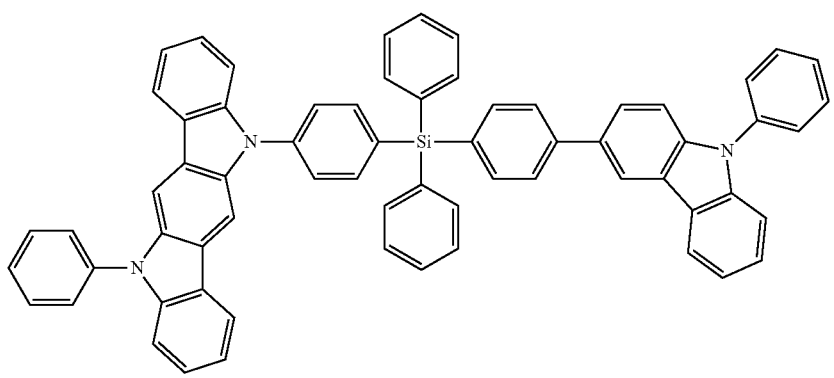
300
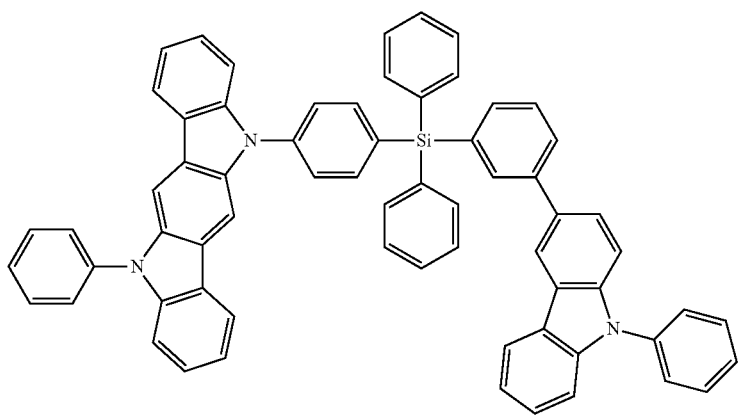
301
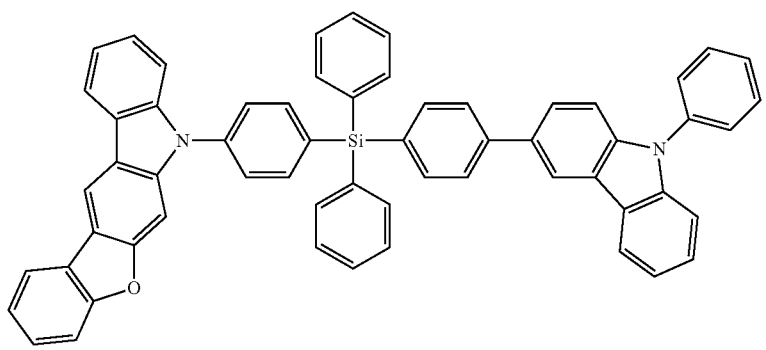

-continued
302
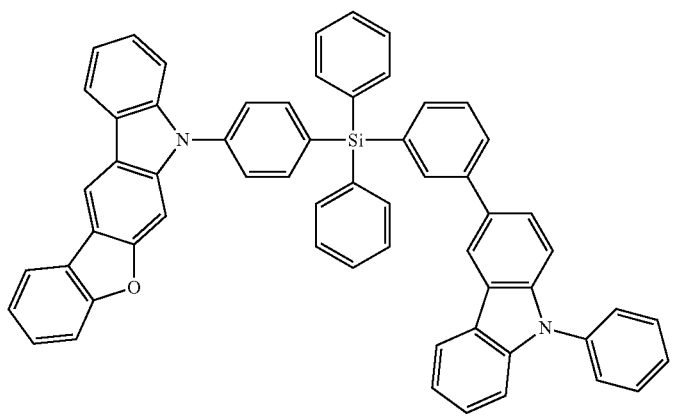
303
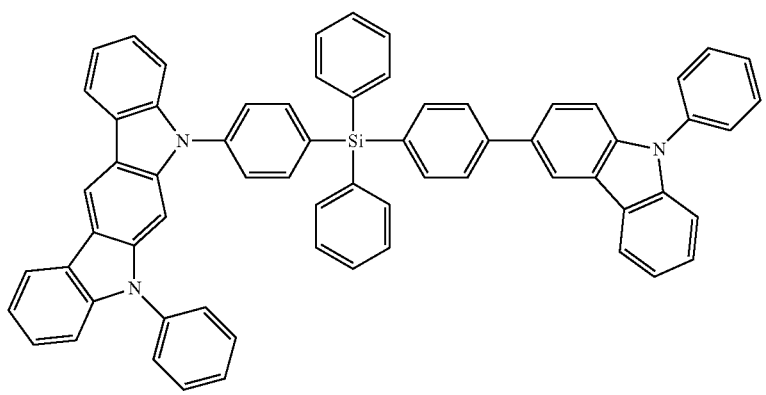
304
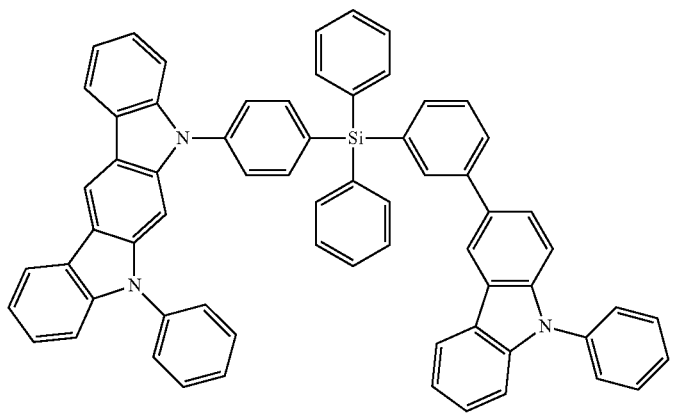
305
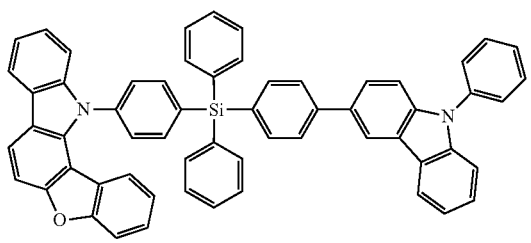
306
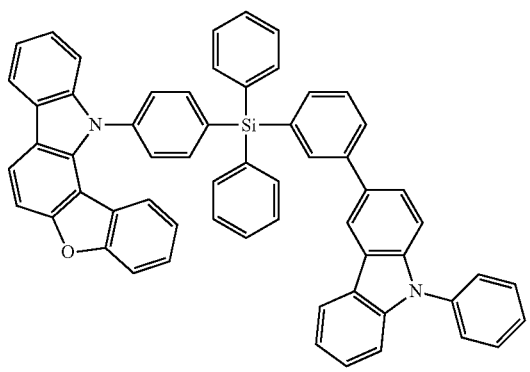

-continued
307
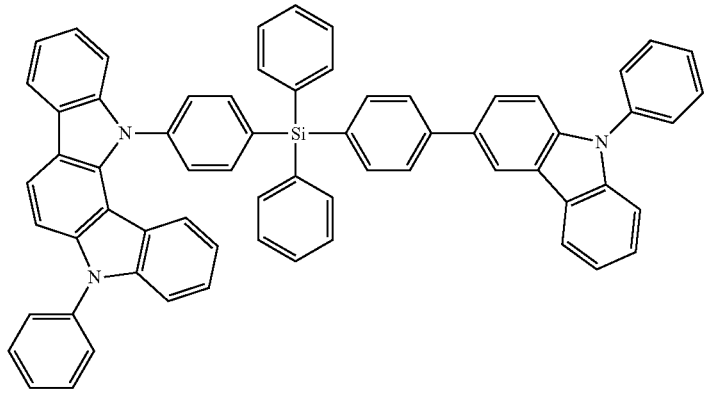
308
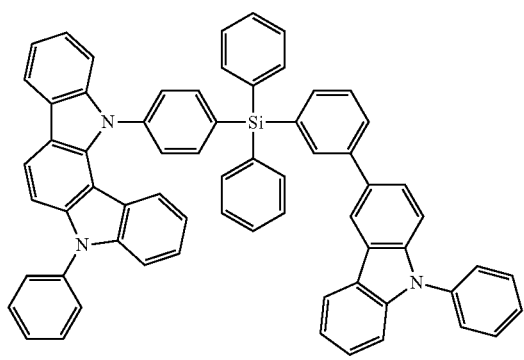
309
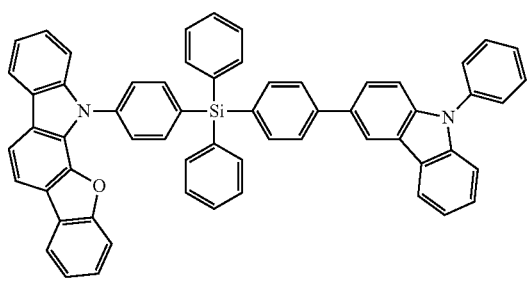
310
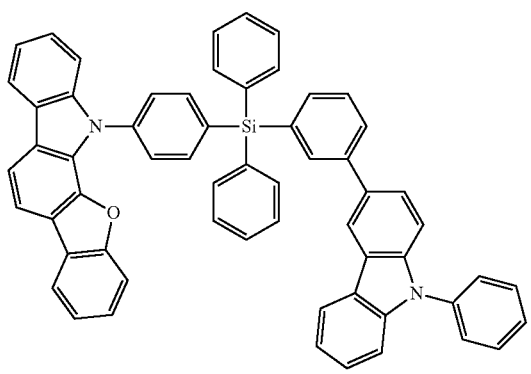
311
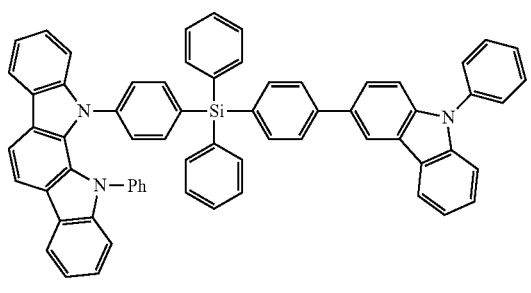
312
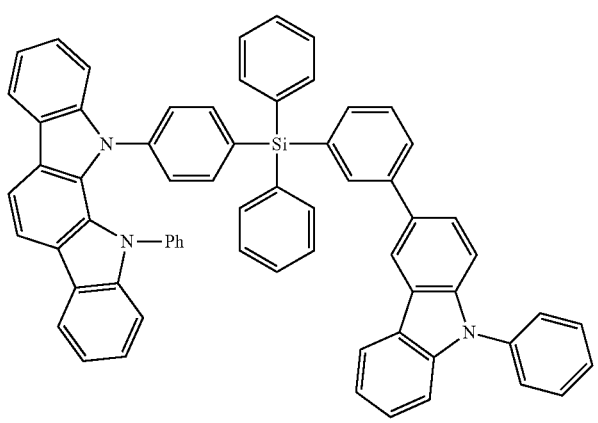

313
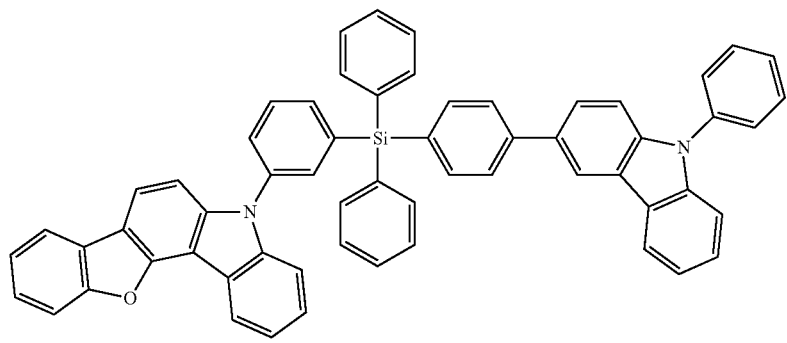
314
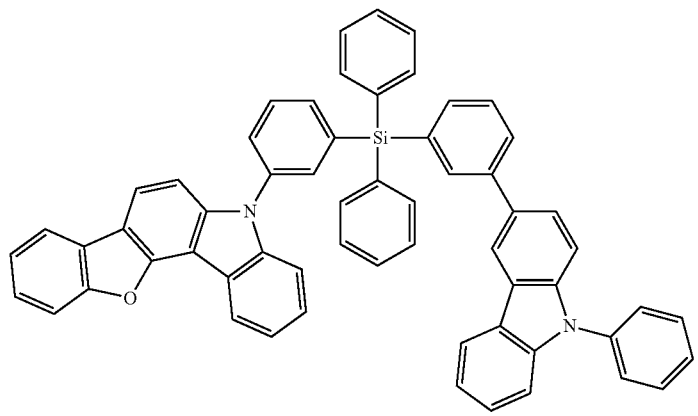
315
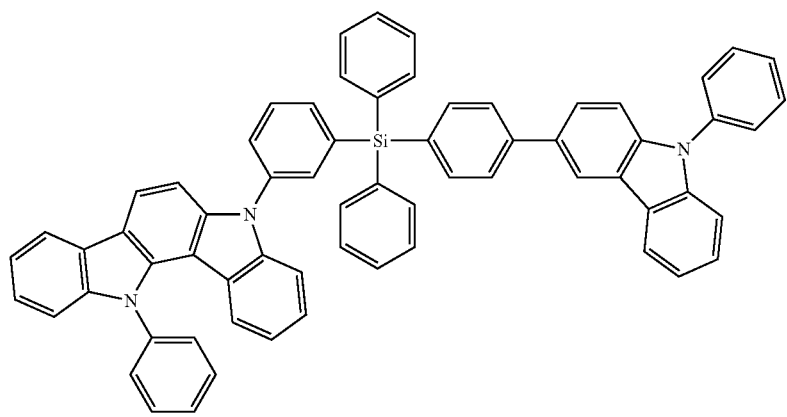
316
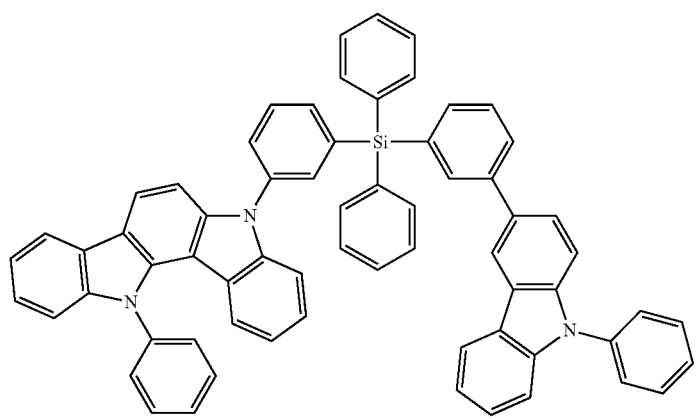

317
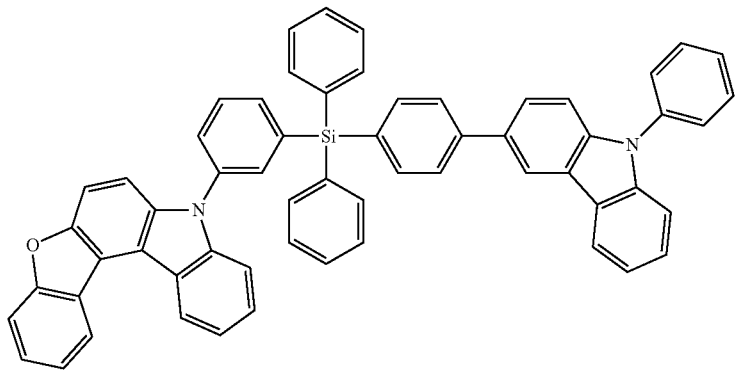
318
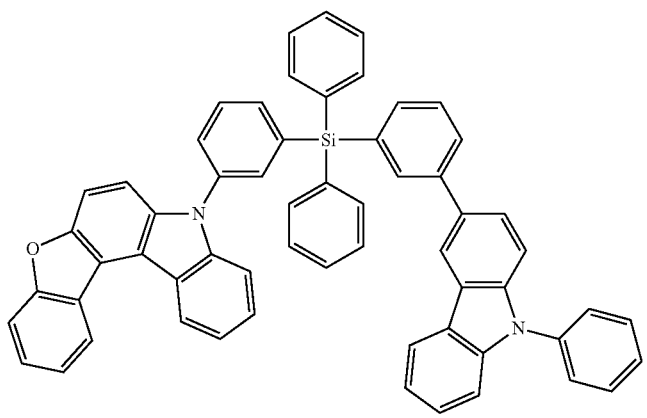
319
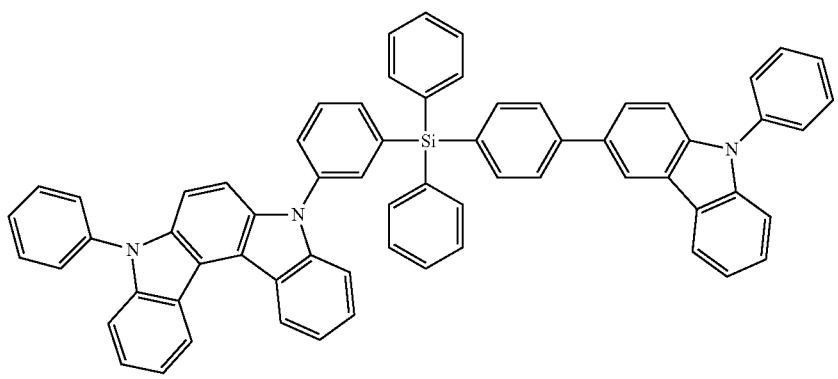
320
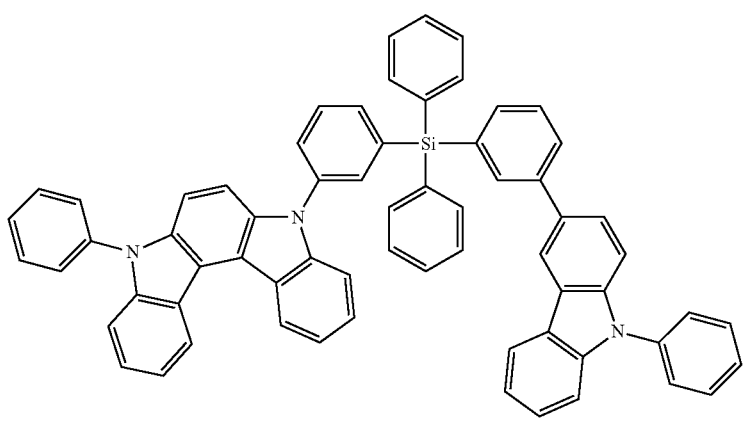

321
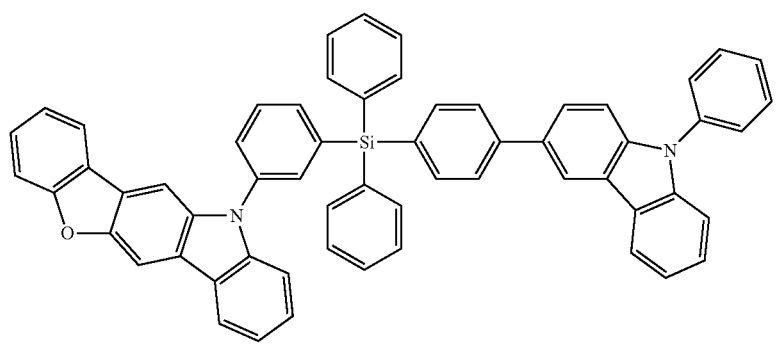
322
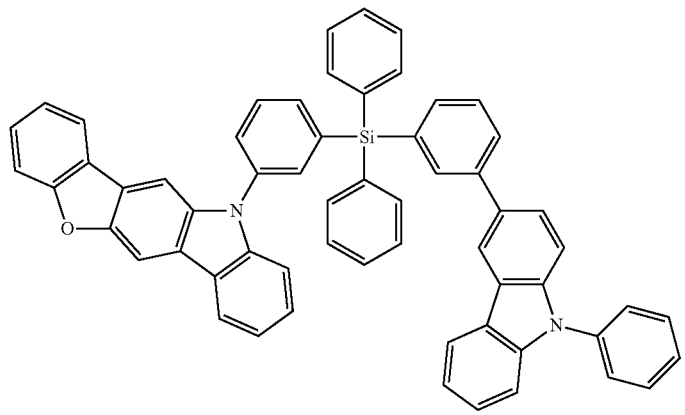
323
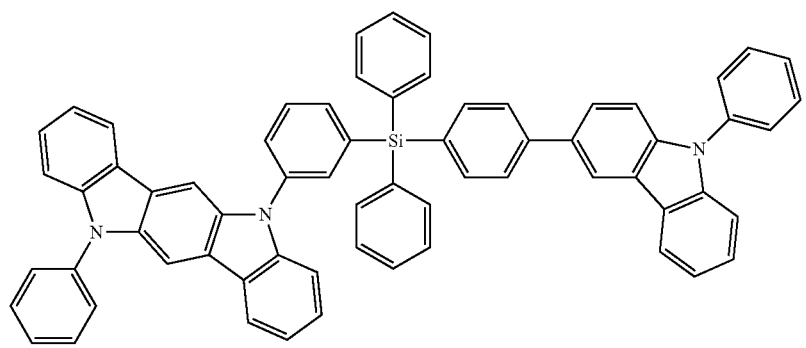
324
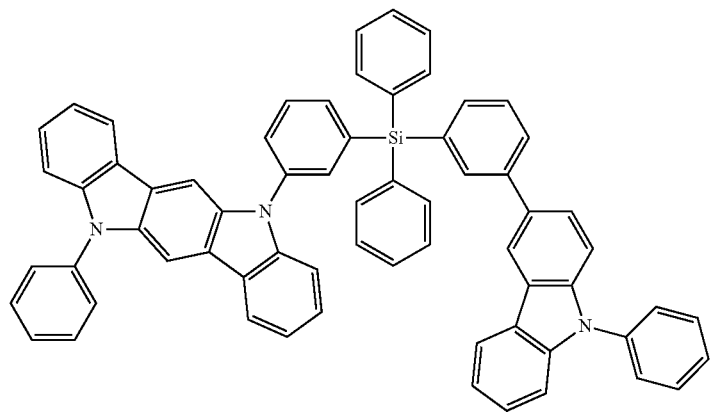

-continued
325
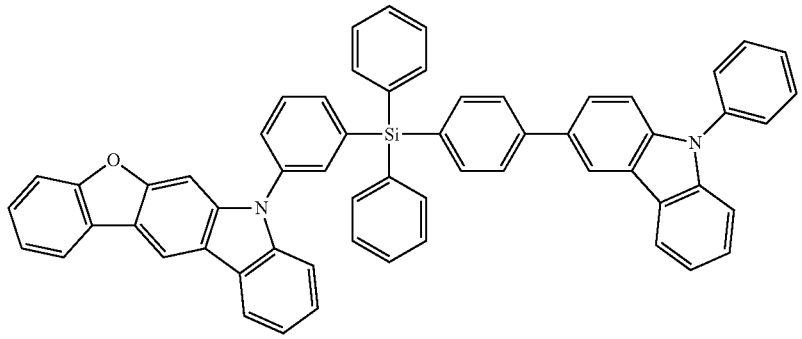
326
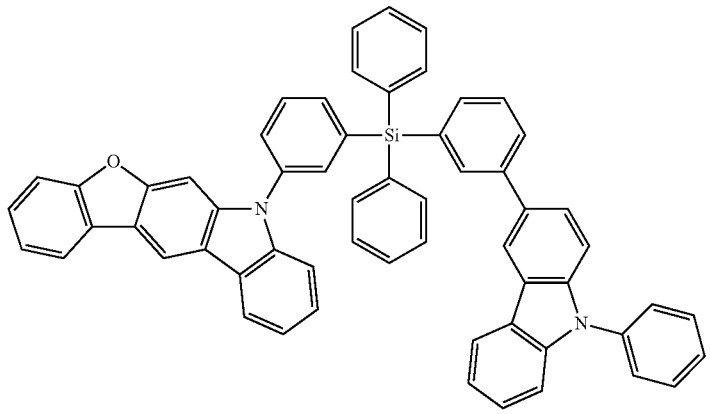
327
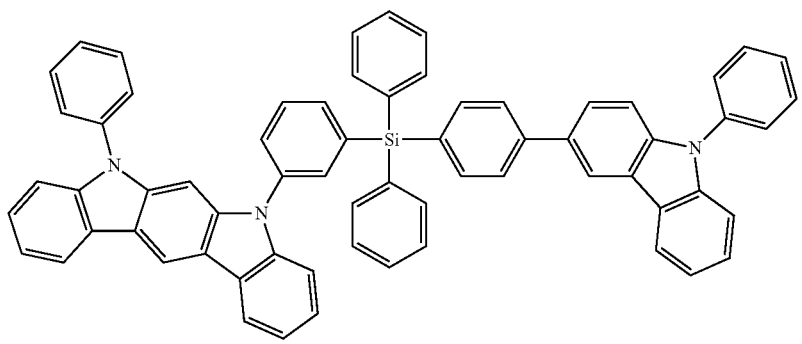
328
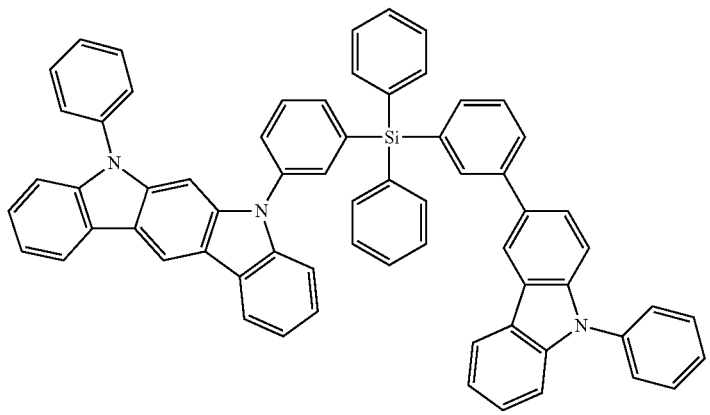

-continued
329
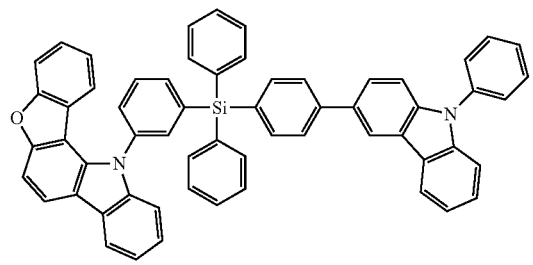
330
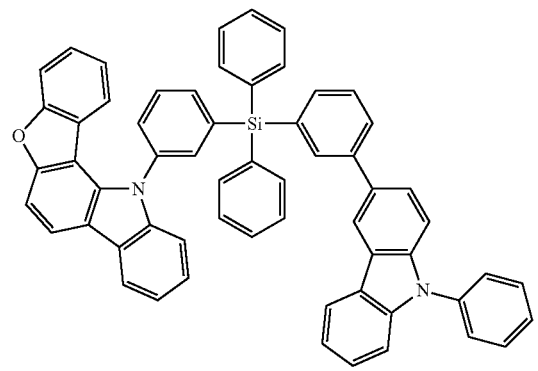
331
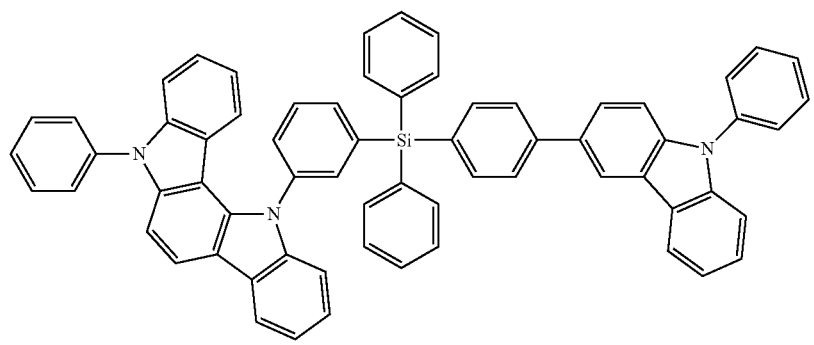
332
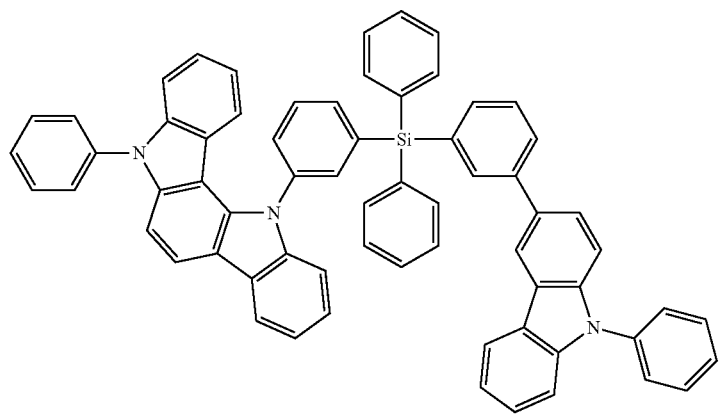
333
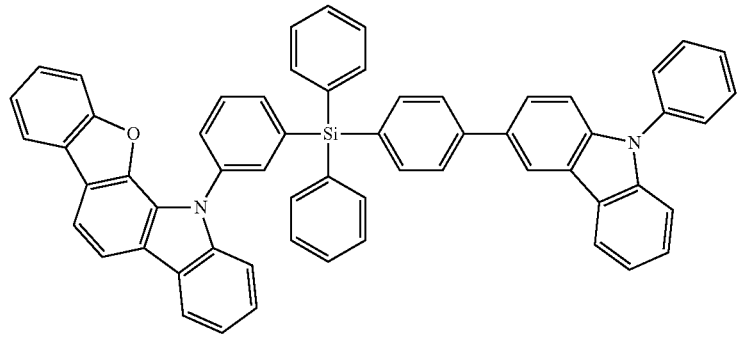

334
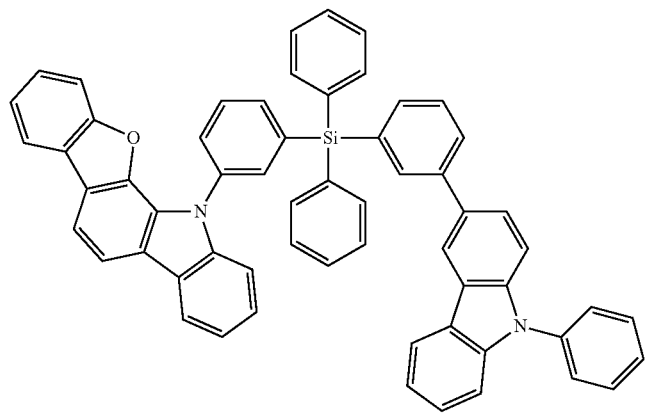
335
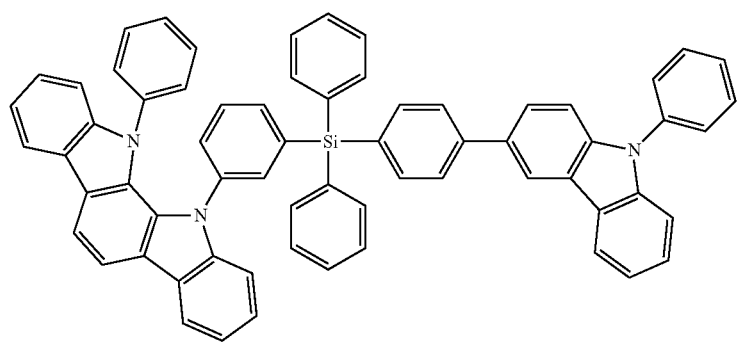
336
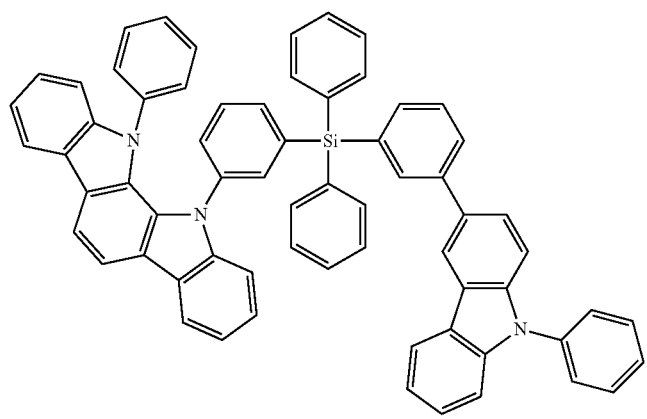
337
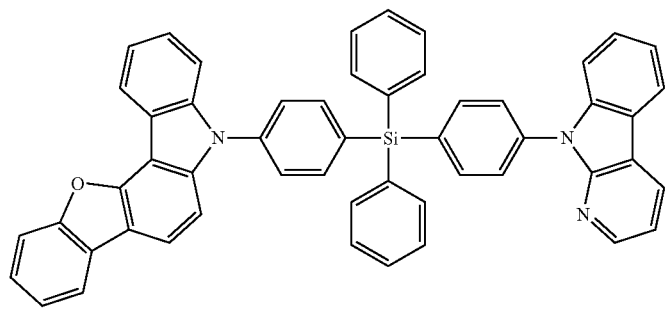

338
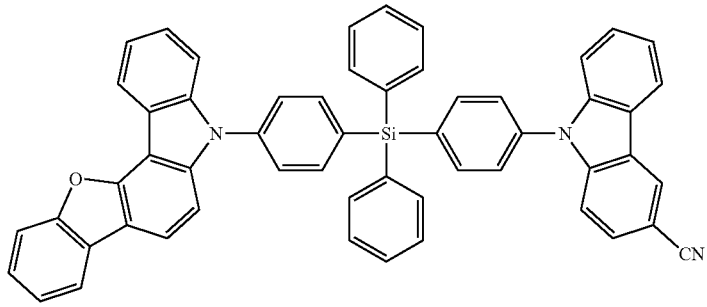
339
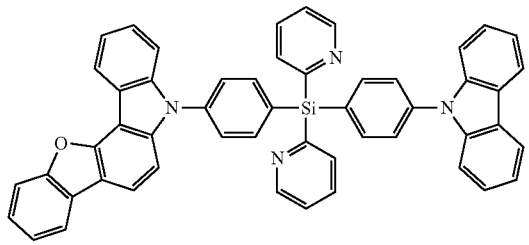
340
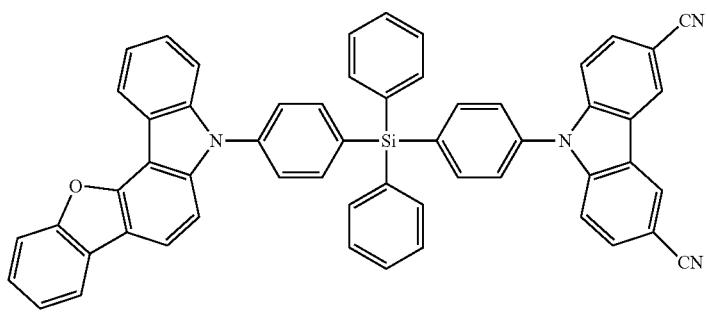
341
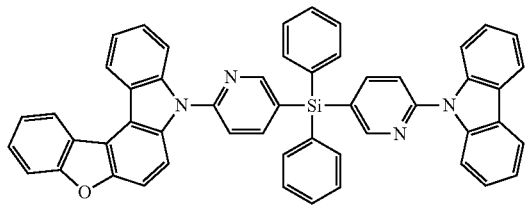
342
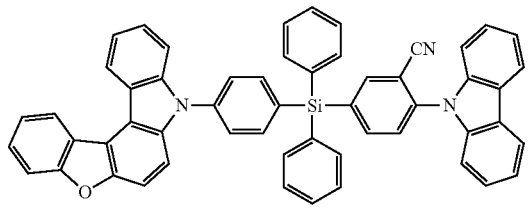
343
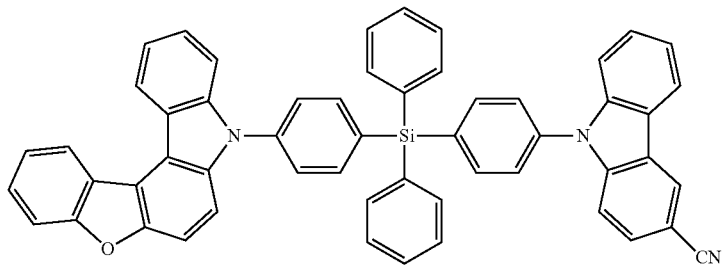

-continued
344
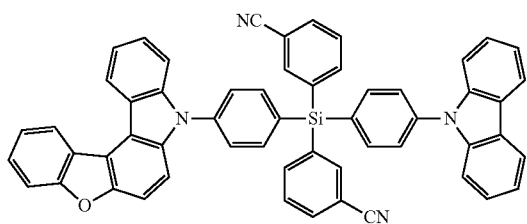
345
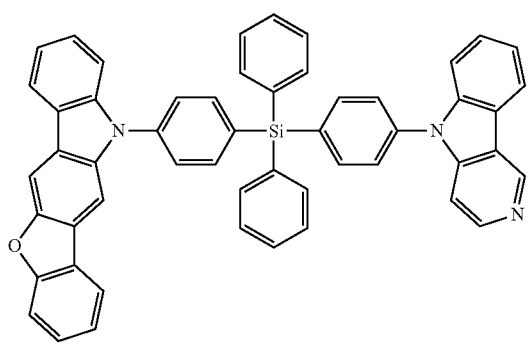
346
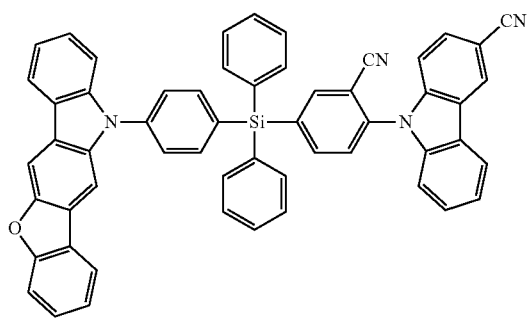
347
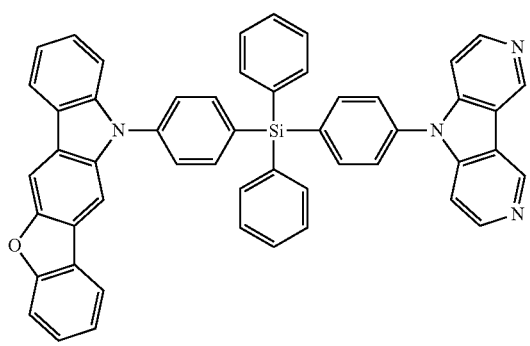
348
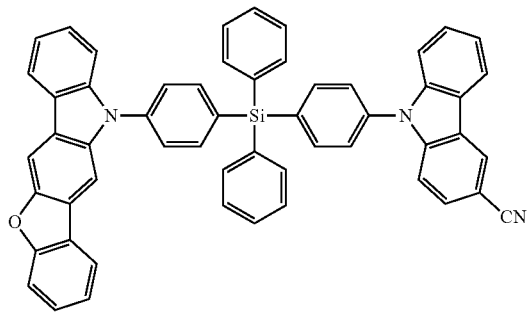
349
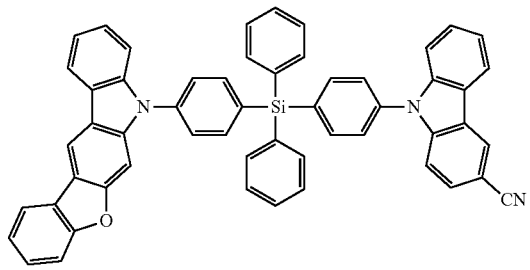
350
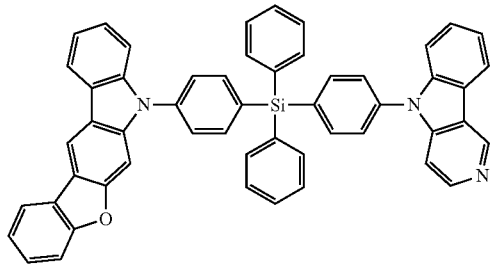
351
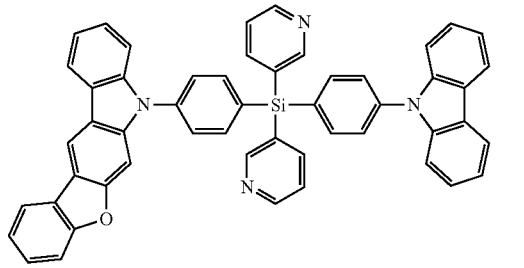
352
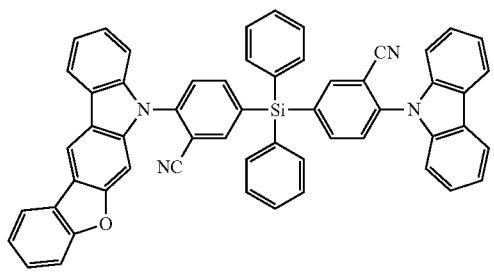
353
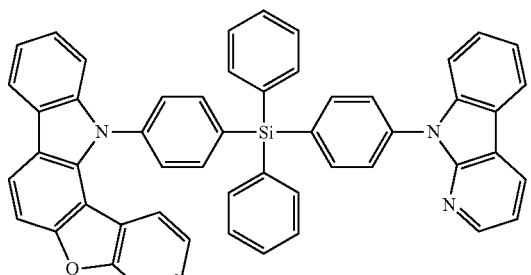

-continued
354
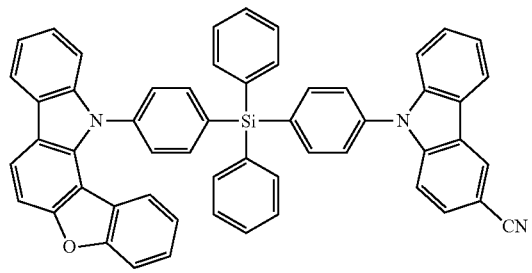
355
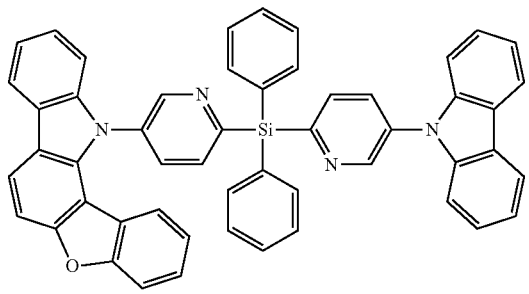
356
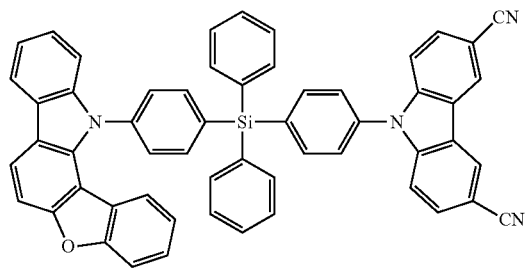
357
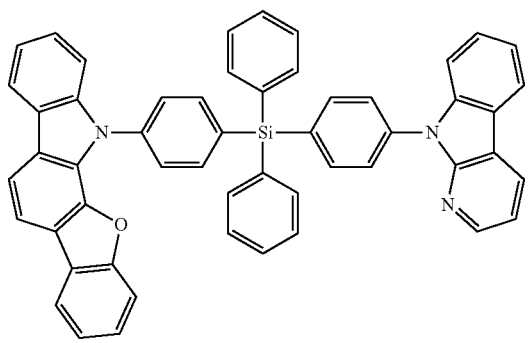
358
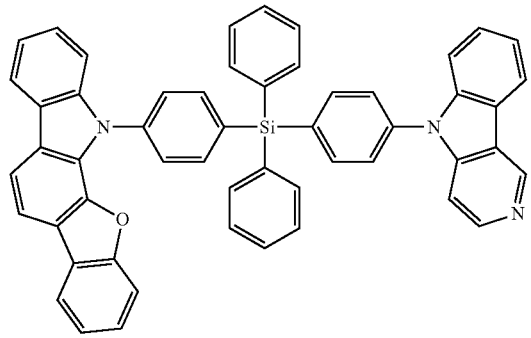
359
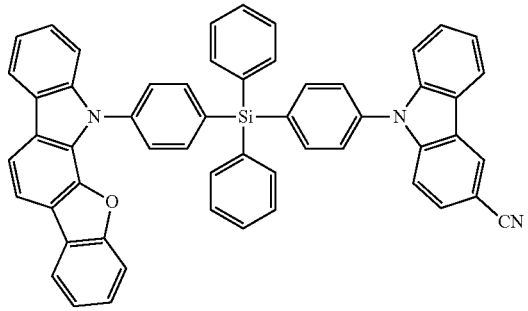
360
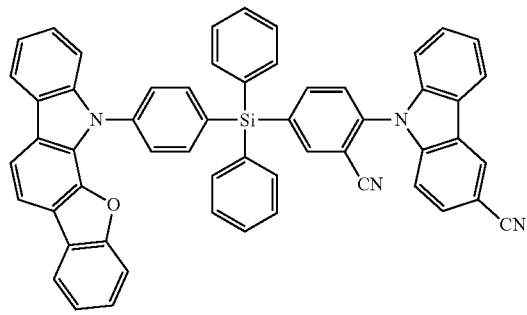
361
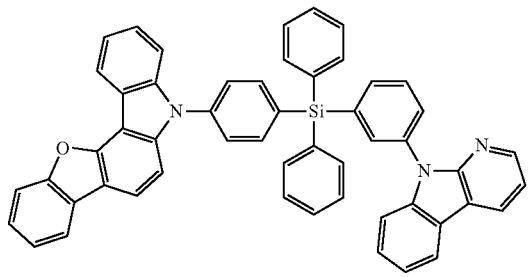

362
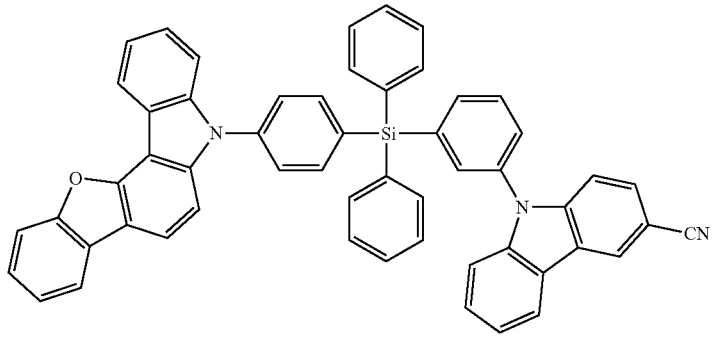
363
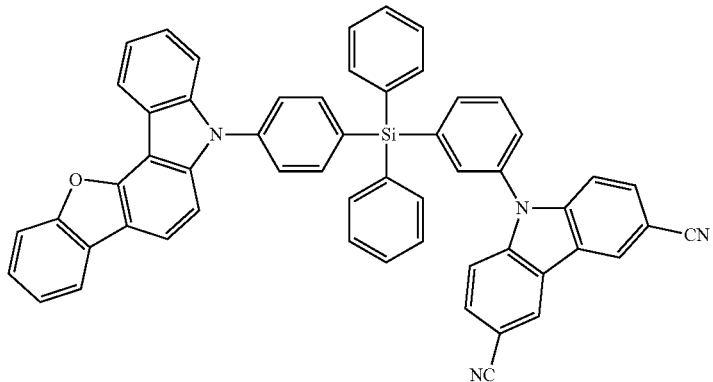
364
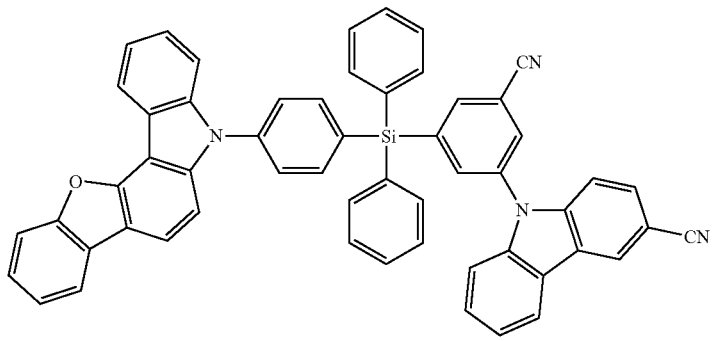
365
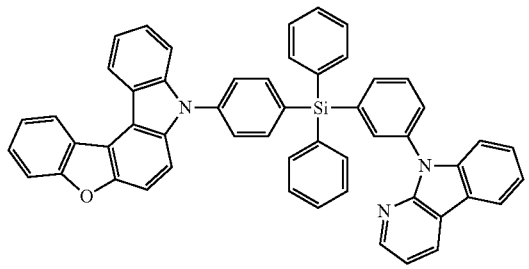
366
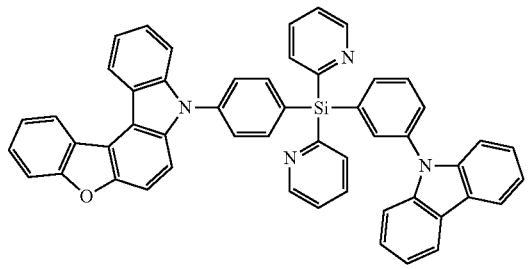

367
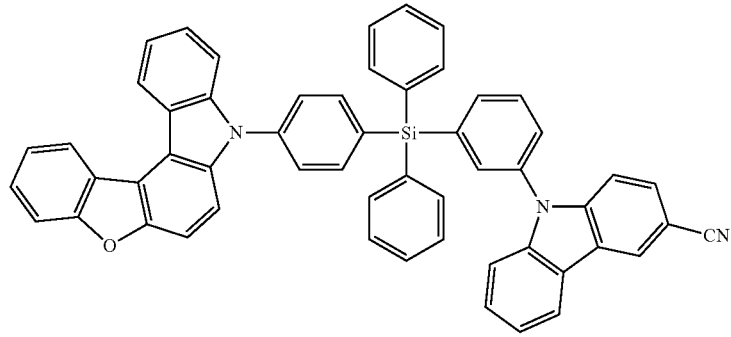
368
369
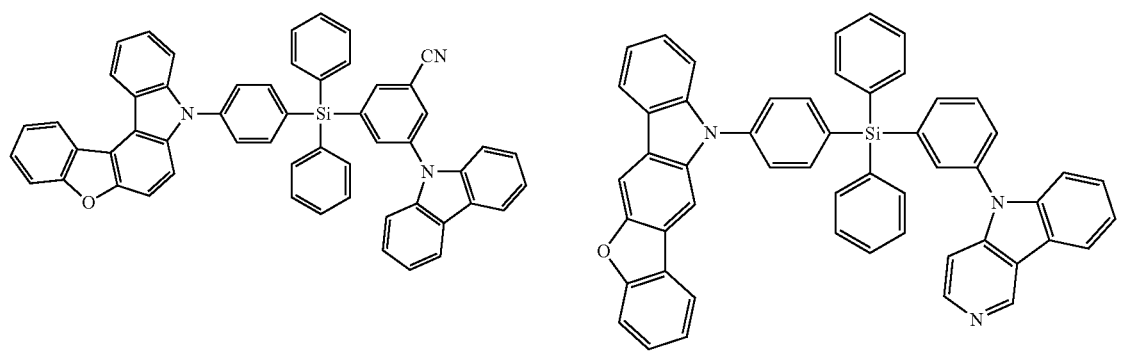
370
371
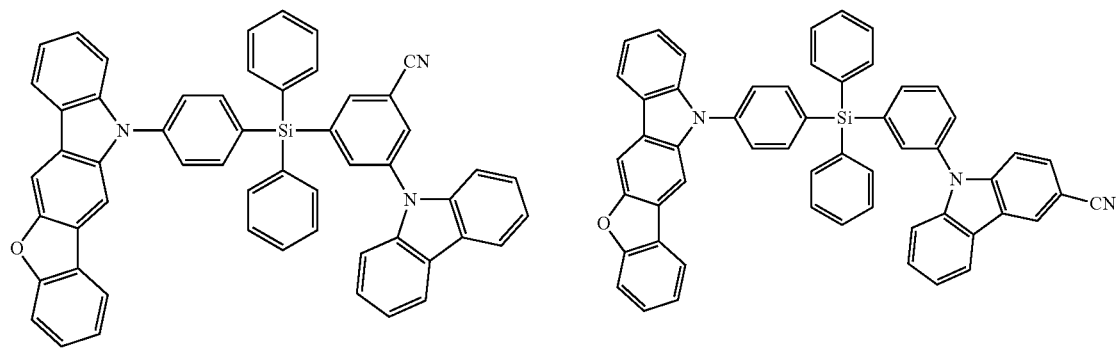
372
373
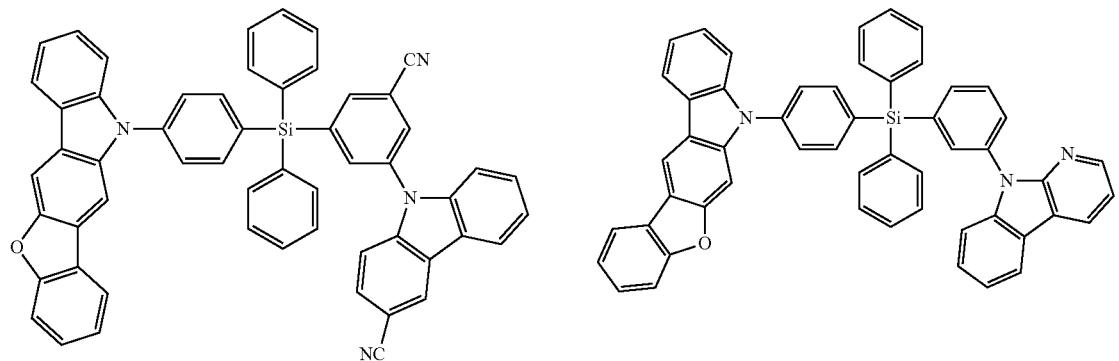

-continued
374
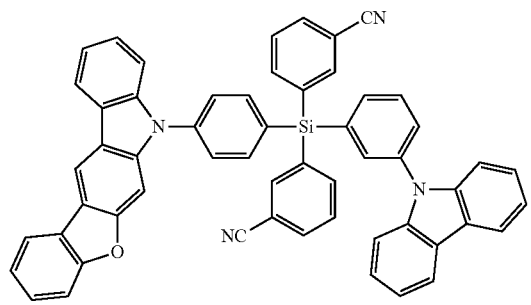
375
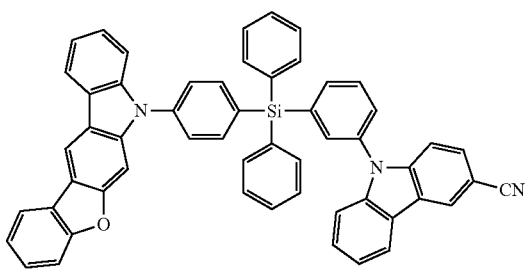
376
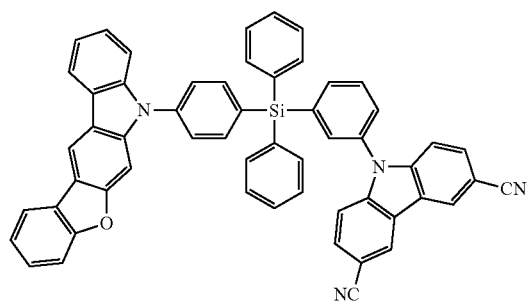
377
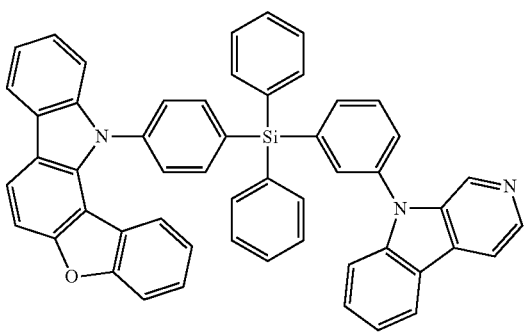
378
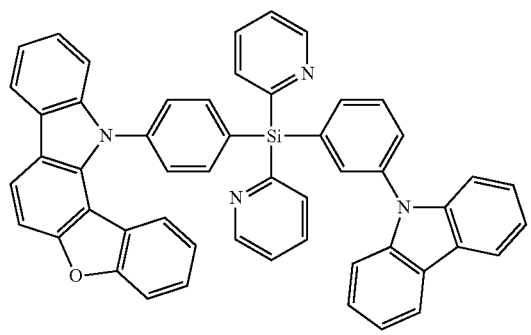
379
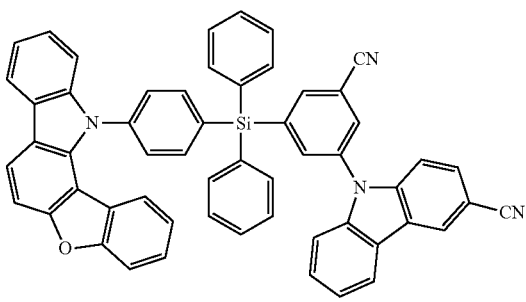
380
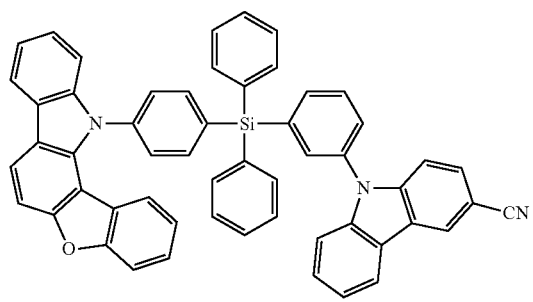
381
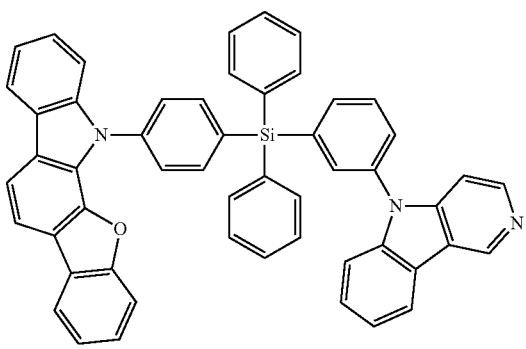

-continued
382
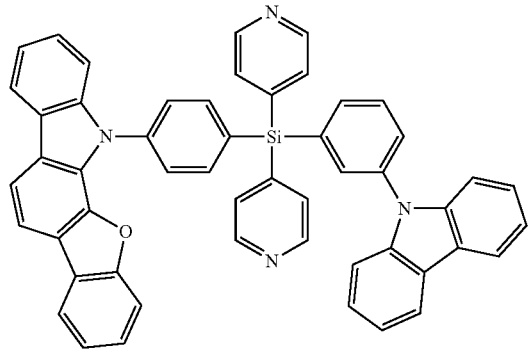
383
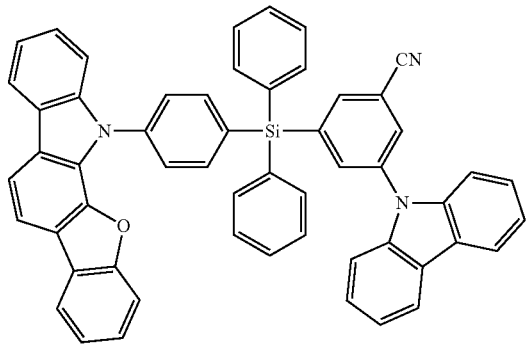
384
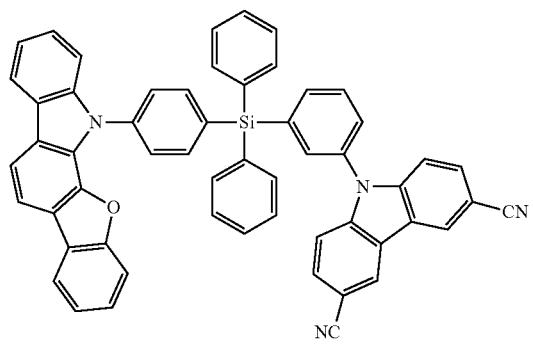
385
386
387
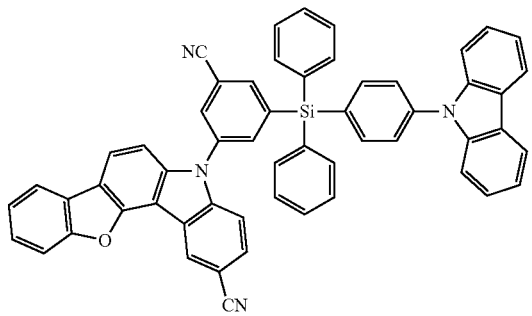
388
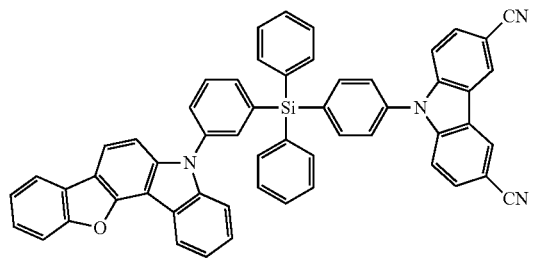
389
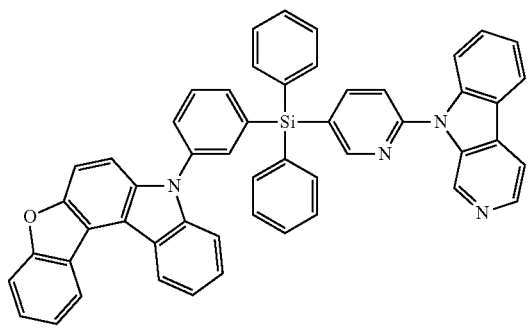

-continued
390
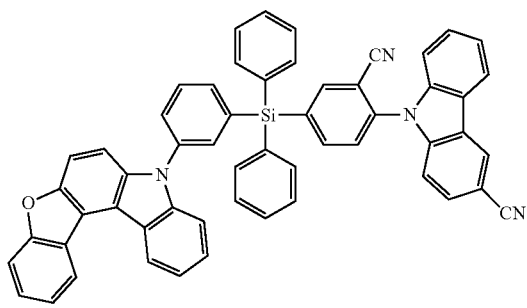
391
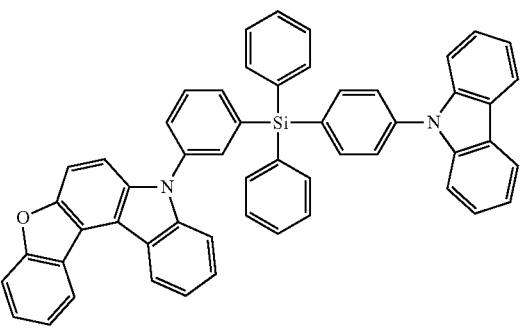
392
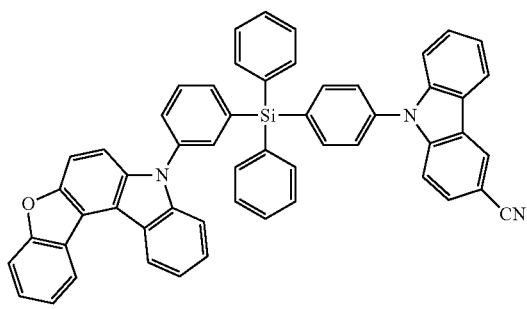
393
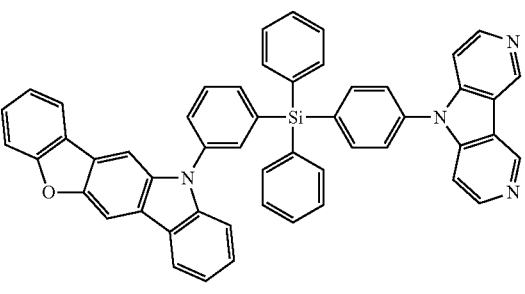
394
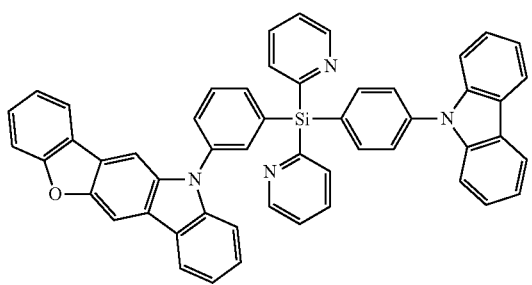
395
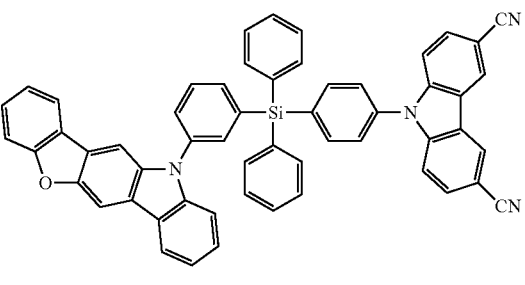
396
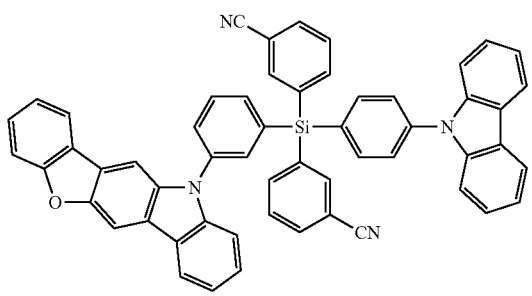
397
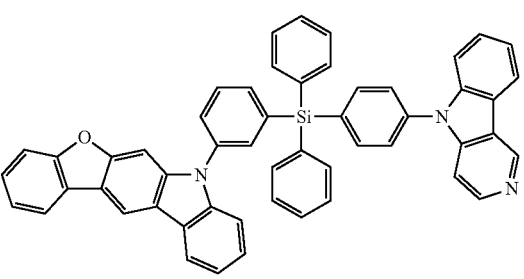
398
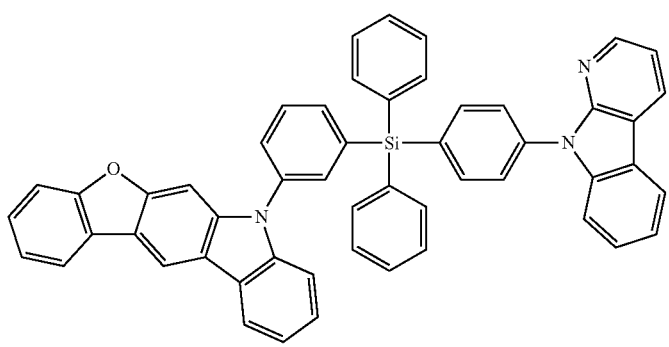

-continued
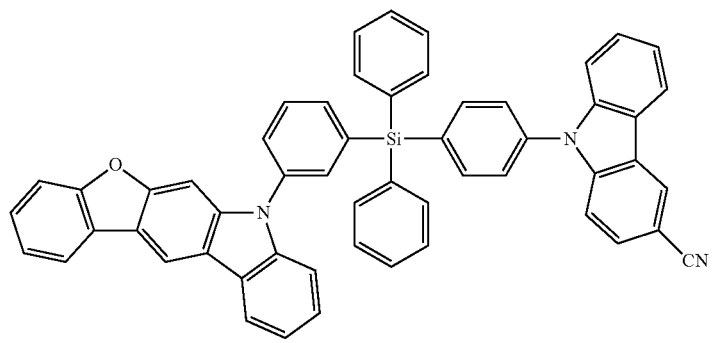
399
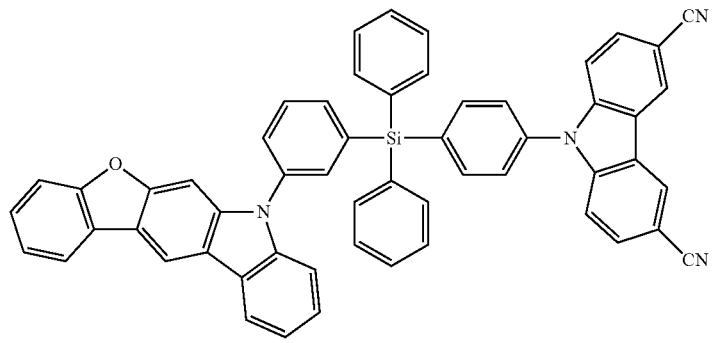
400
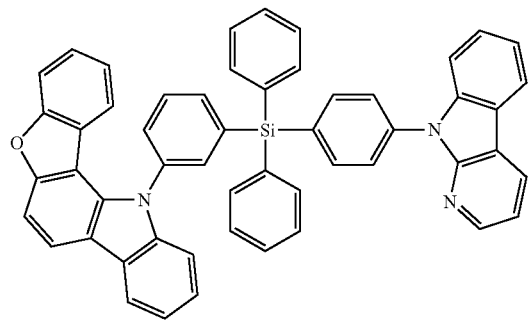
401
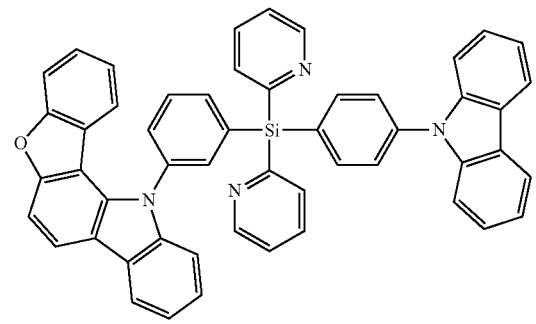
402
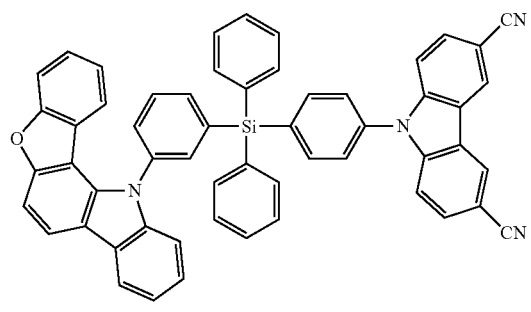
403
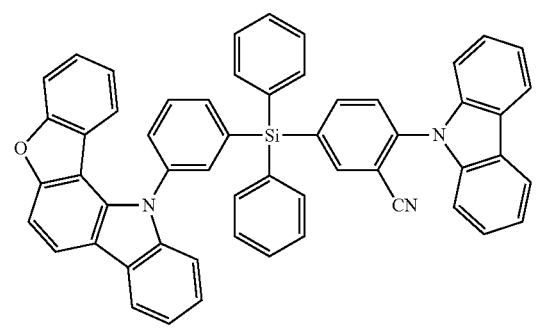
404

-continued
| 405 | 406 |
|---|---|
| 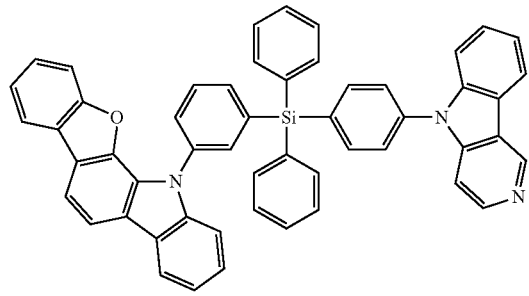 | 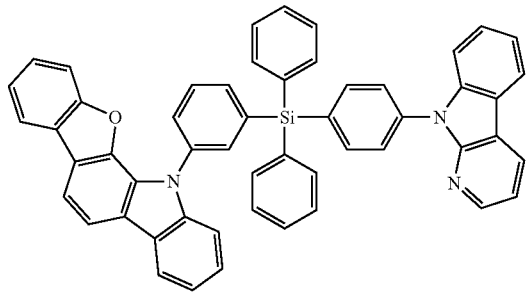 |
| 407 | 408 |
| 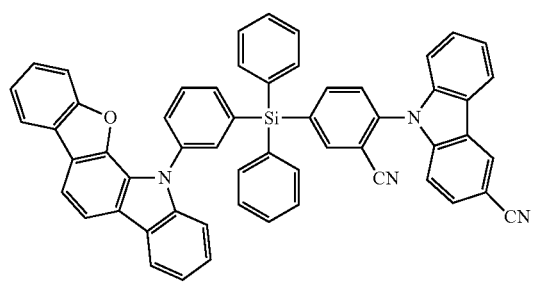 | 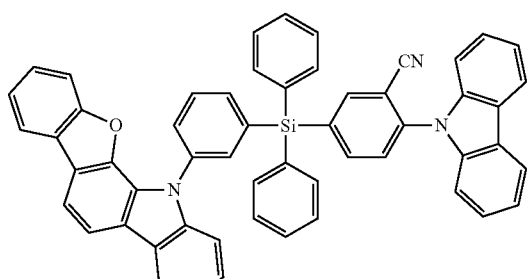 |
409
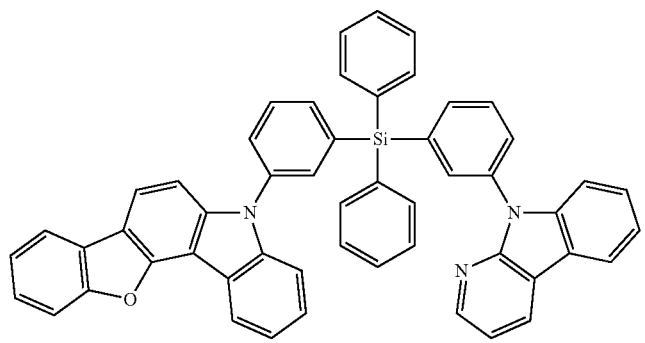
410
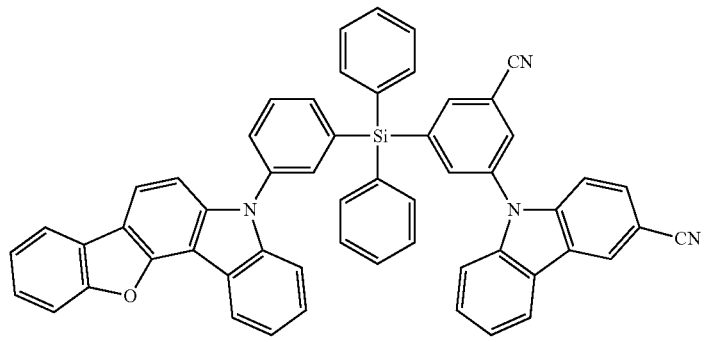
411
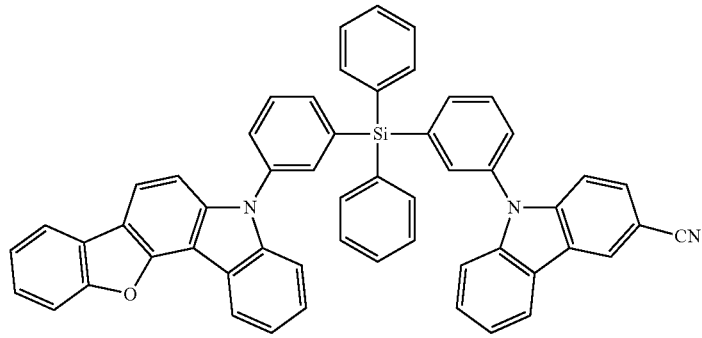

| 1065 | 1066 |
|---|---|
| -continued | |
412
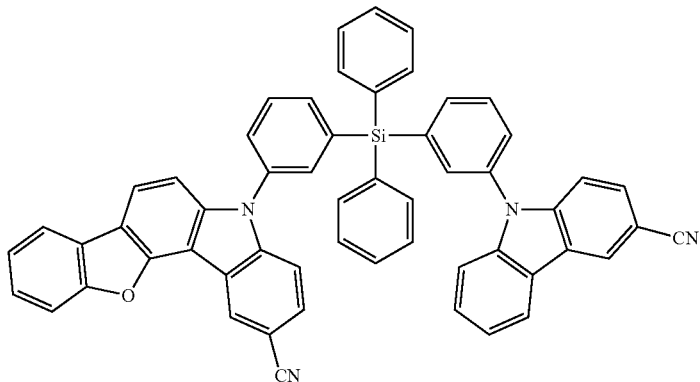
| 413 | 414 |
|---|---|
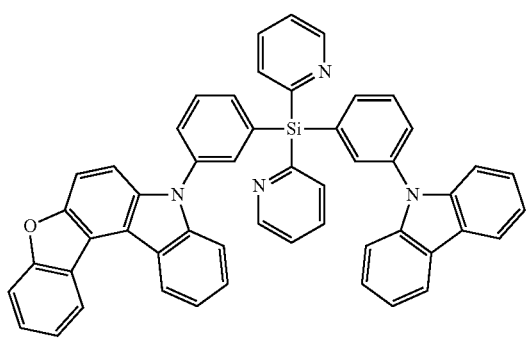 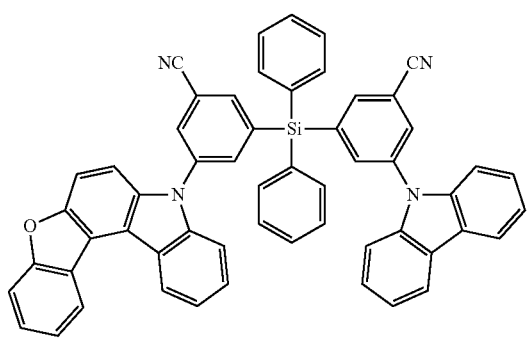
| 415 | 416 |
|---|---|
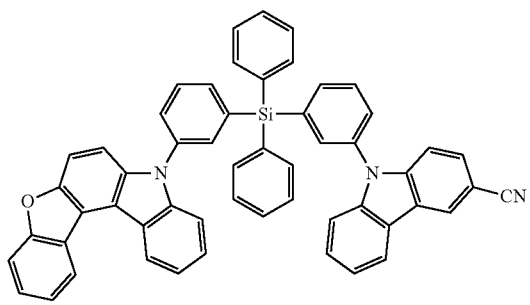 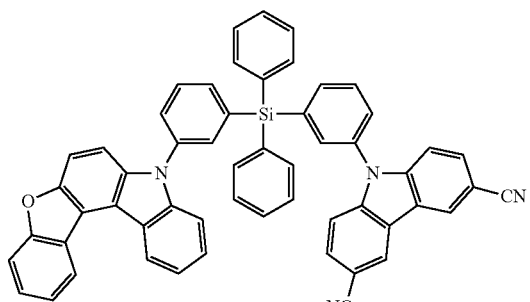
| 417 | 418 |
|---|---|
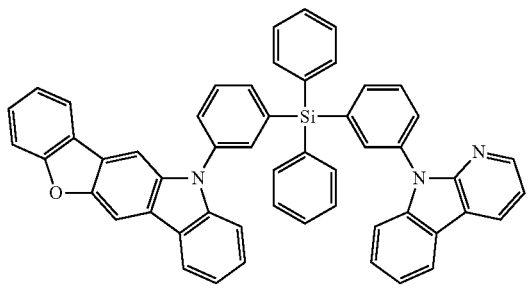 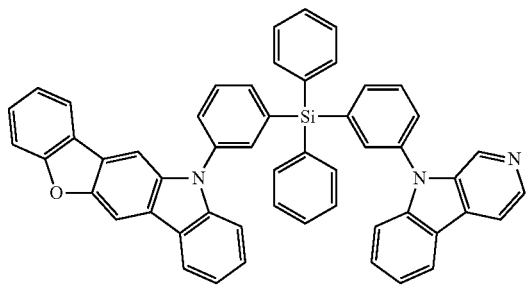

-continued
419
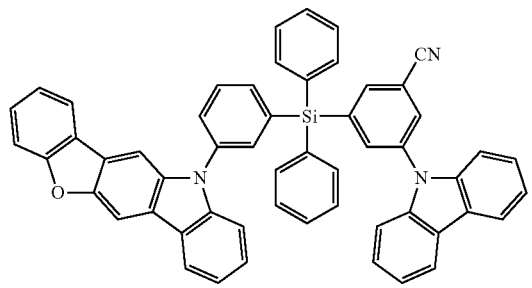
420
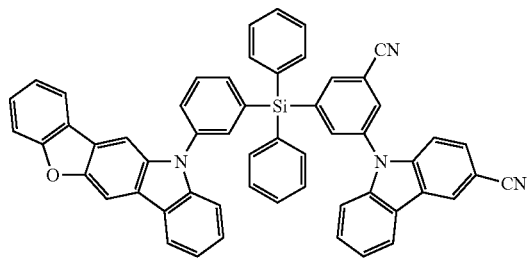
421
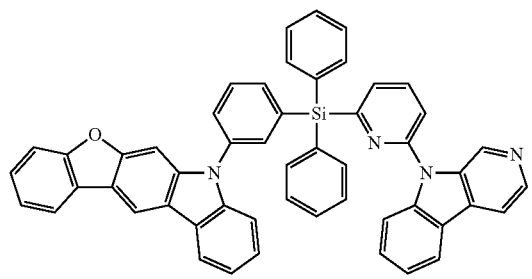
422
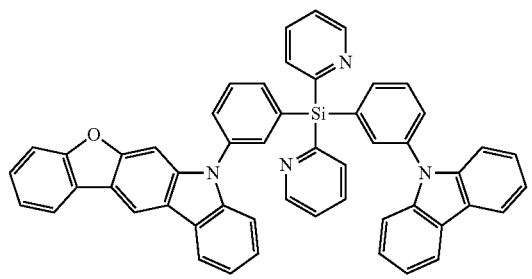
423
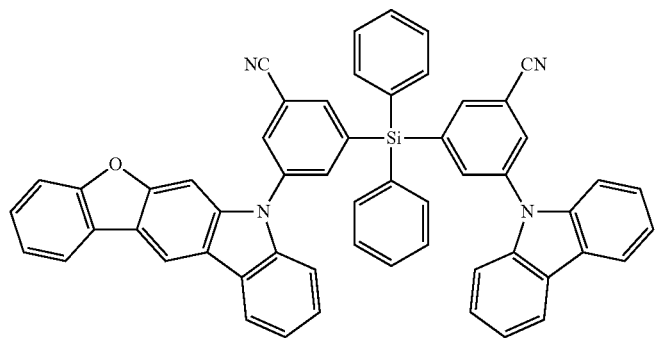
424
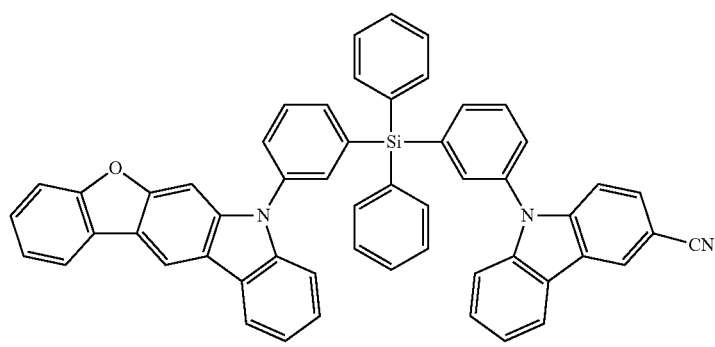
425
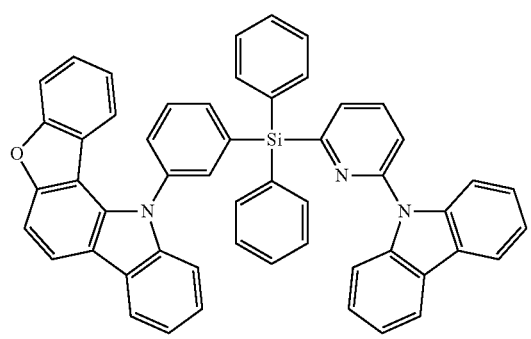
426
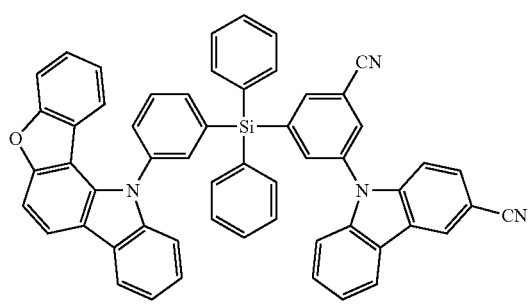

-continued
427
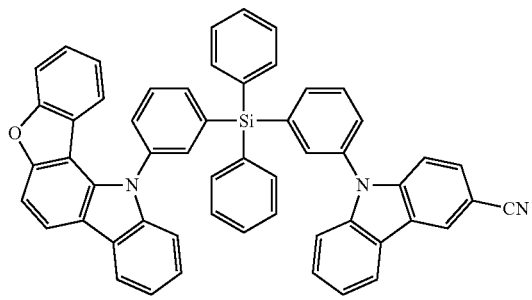
428
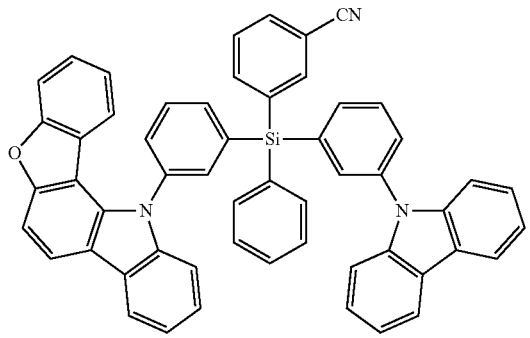
429
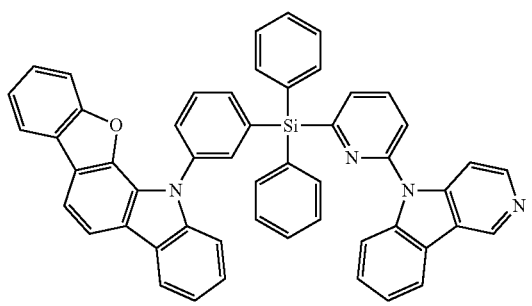
430
431
432
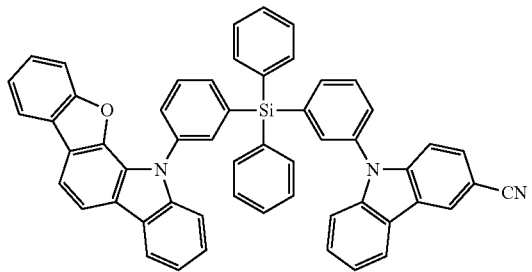
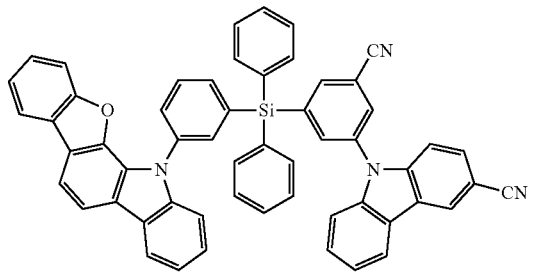
wherein in Compounds 1 to 432,
"Ph" represents a phenyl group.
In some embodiments, the hole transporting host may include o-CBP or mCP:
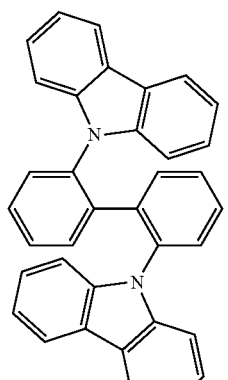
o-CBP
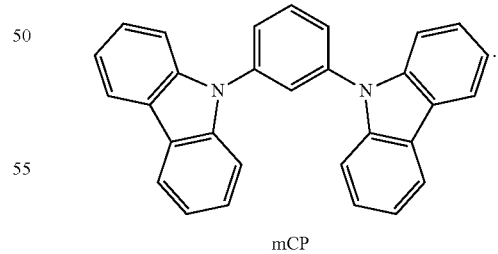
mCP
In some embodiments, the host may be a fluorescent host, and the fluorescent host may be represented by, for example, one of Formulae FH-1 to FH-4.

In some embodiments, the fluorescent host may be represented by Formula FH-1:

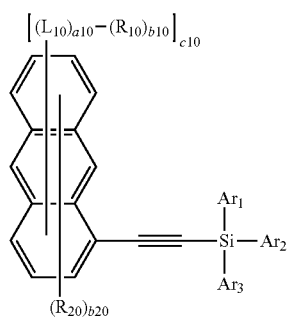

Formula FH-1 wherein, in Formula FH-1, $Ar_1$ to $Ar_3$ may each independently be a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_5)$, $-B(Q_6)(Q_7)$, or $-P(=O)(Q:)(Q_9)$, and at least one of $Ar_1$ to $Ar_3$ may be a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, $L_{10}$ may be a substituted or unsubstituted $C_5$-$C_{30}$ carbocyclic group or a substituted or unsubstituted $C_1$-$C_{30}$ heterocyclic group, a10 may be an integer from 0 to 3, and when a10 is 2 or greater, at least two $L_{10}(s)$ may be identical to or different from each other, $R_{10}$ and $R_{20}$ may each independently be hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_5)$, $-B(Q_6)(Q_7)$, or $-P(=O)(Q:)(Q_9)$, b10 and b20 may each independently be an integer from 1 to 8, when b10 is 2 or greater, at least two $R_{10}(s)$ may be identical to or different from each other, and when b20 is 2 or greater, at least two $R_{20}(s)$ may be identical to or different from each other, c10 may be an integer from 1 to 9, and when c10 is 2 or greater, at least two $-[(L_{10})_{a10}-(R_{10})_{b10}]$ (s) may be identical to or different from each other.

In some embodiments, the fluorescent host represented by Formula FH-1 may be Group FH1, but embodiments are not limited thereto:

Group FH1

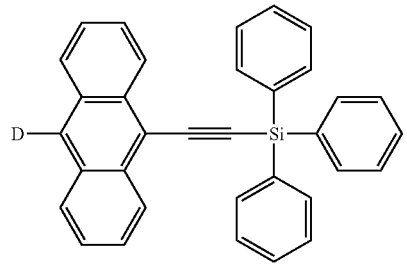

1

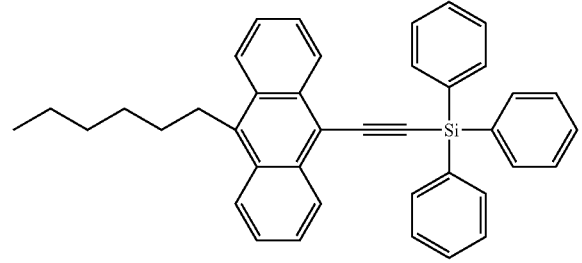

2

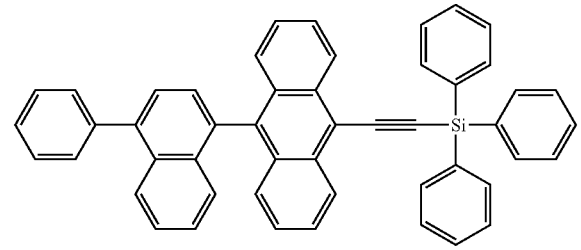

3

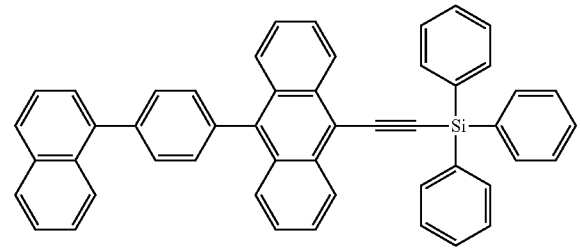

4

5
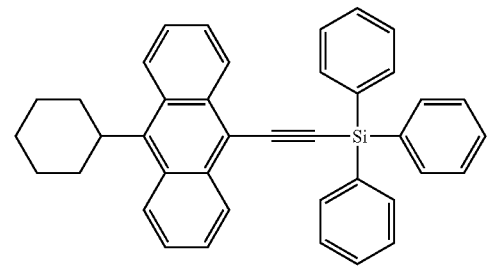
6
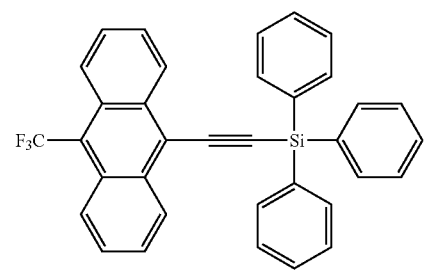
7
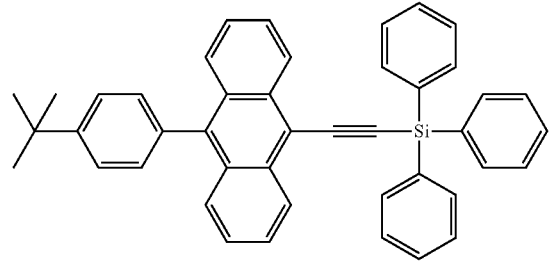
8
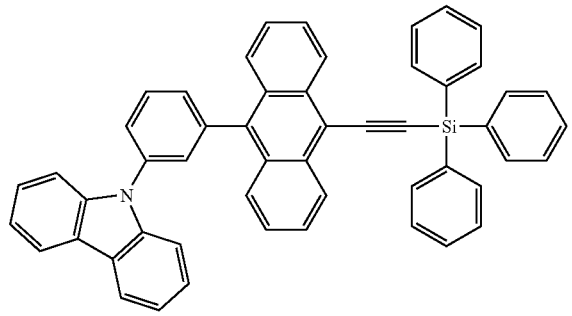
9
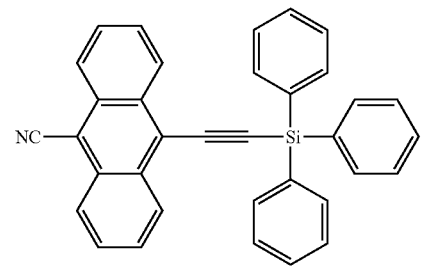
10
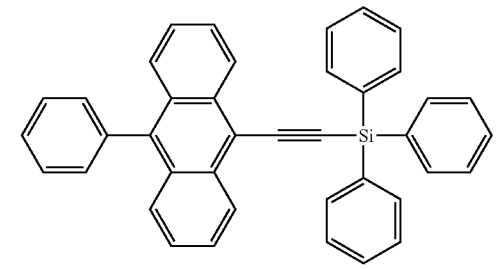
11
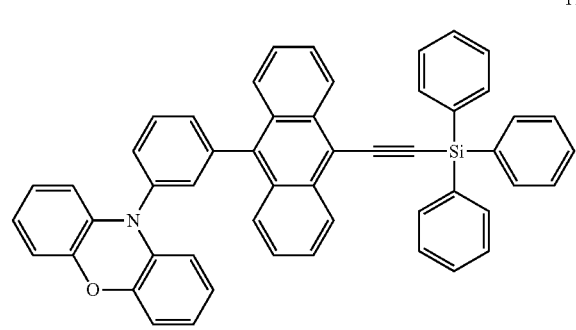
12
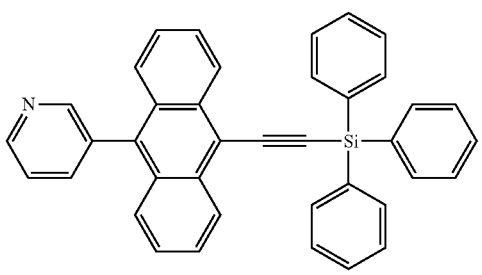
13
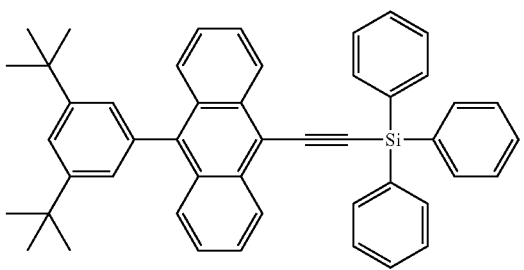
14
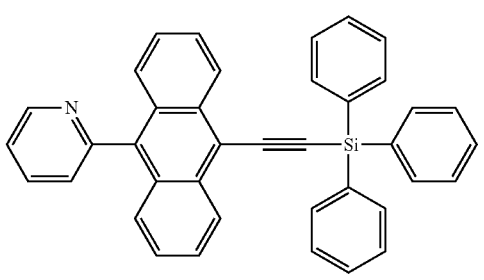

15

16
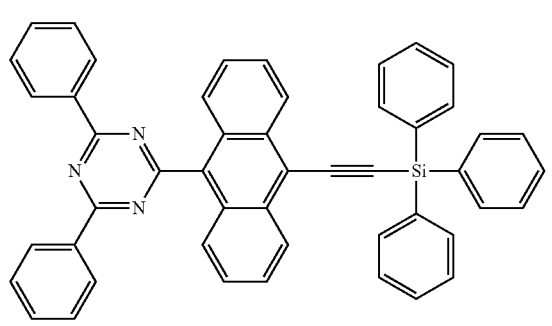
17
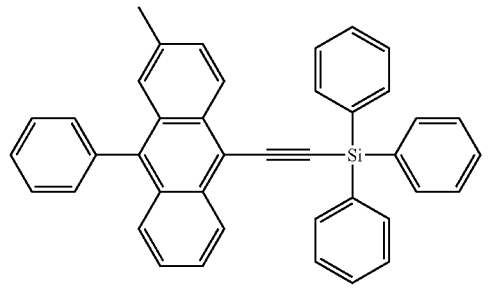
18

19
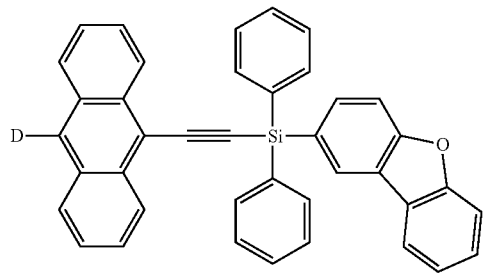
20

21
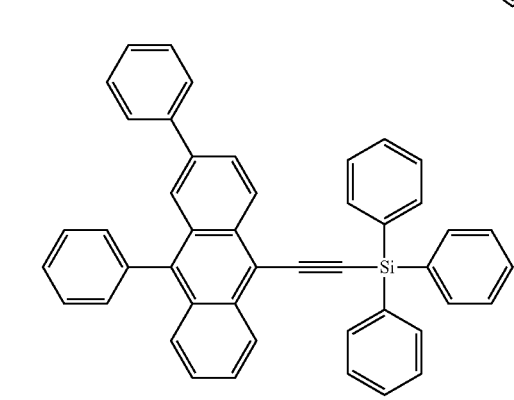
22
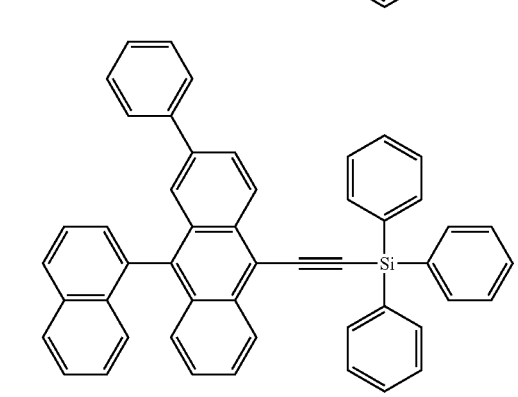
23

24

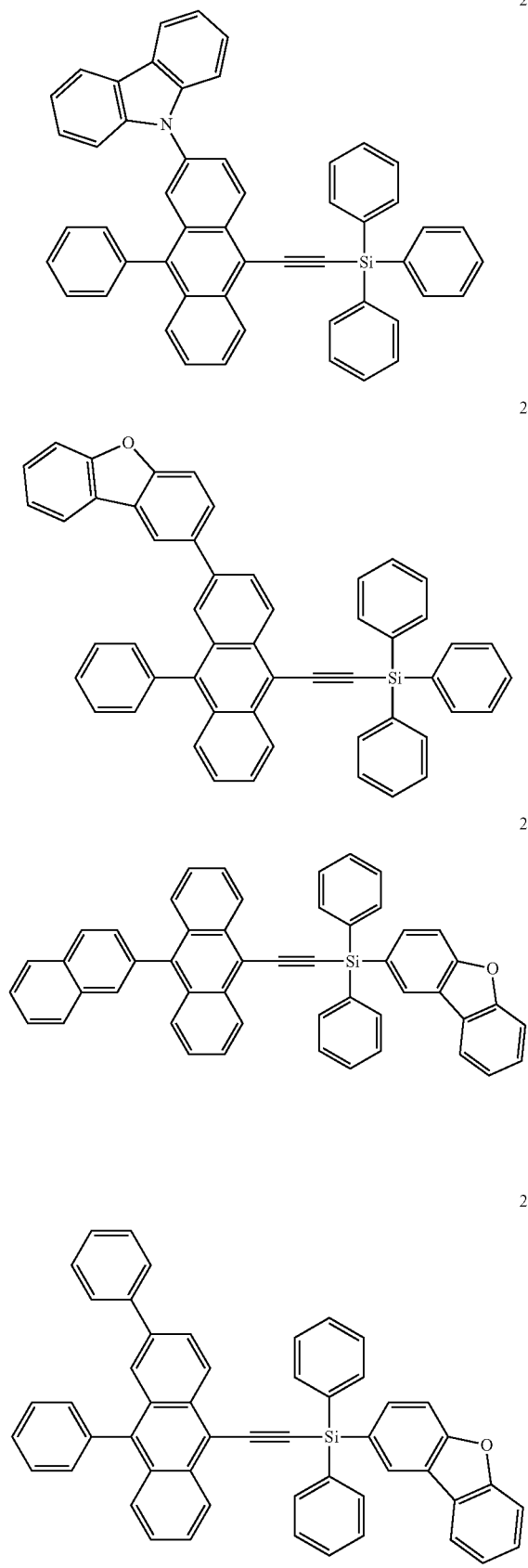
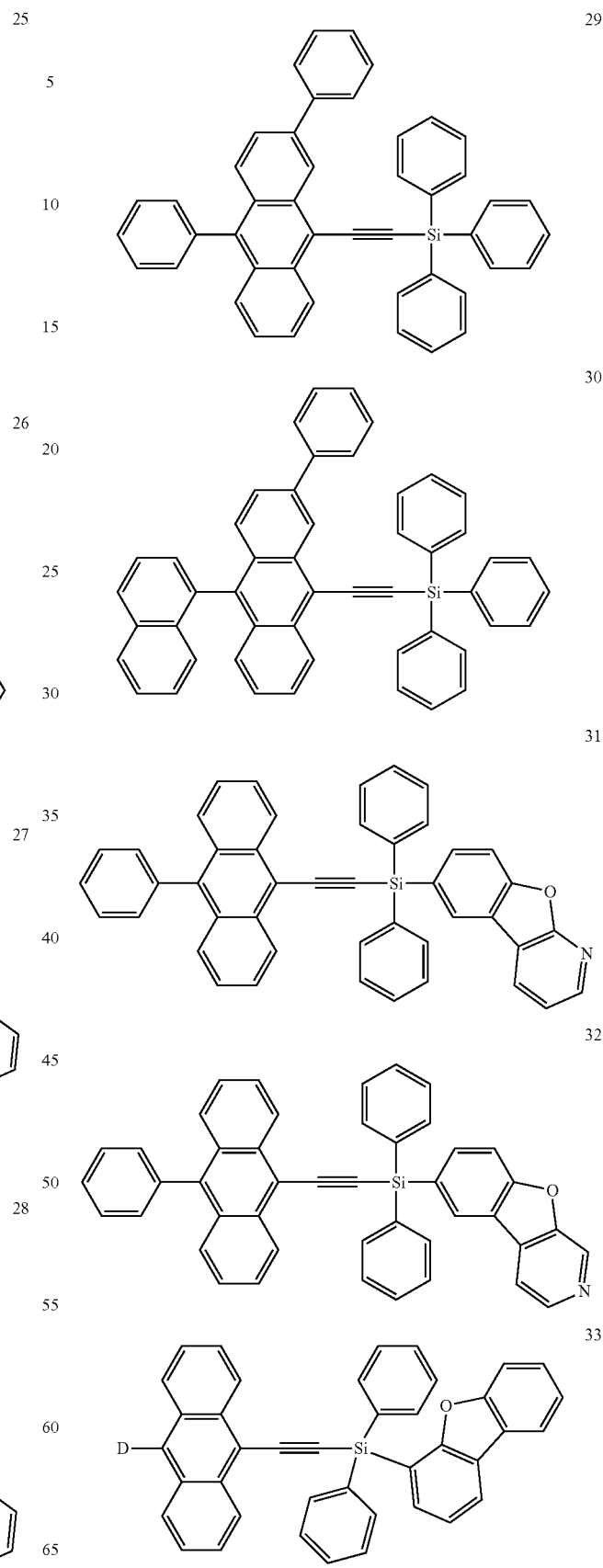

1079
-continued
34
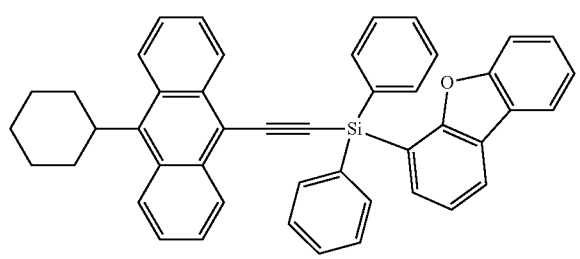
35
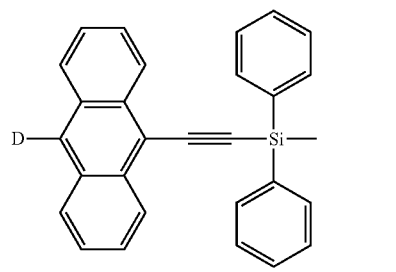
36
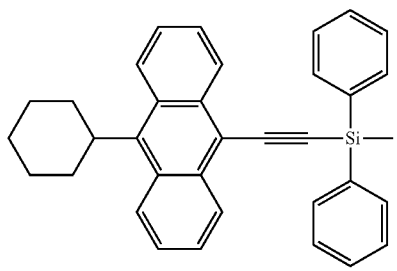
37
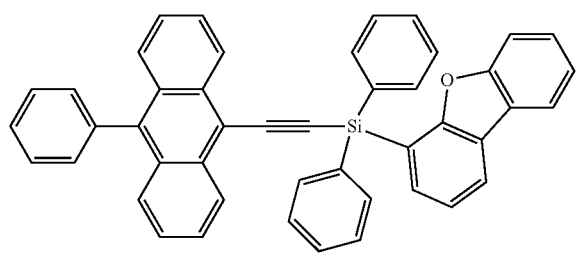
38
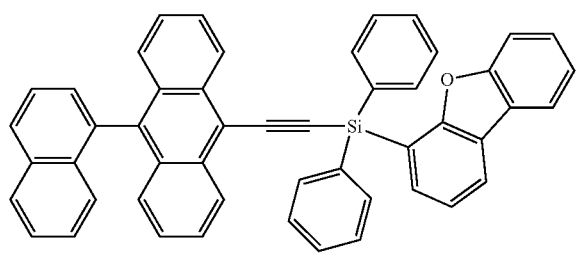
39
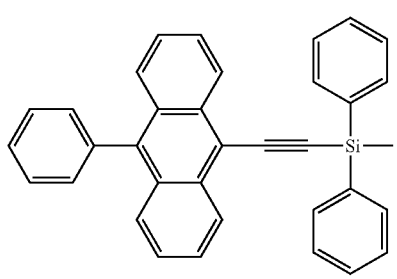
1080
-continued
40
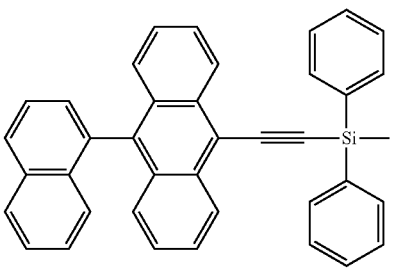
41
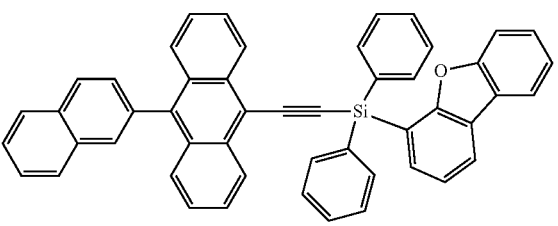
42
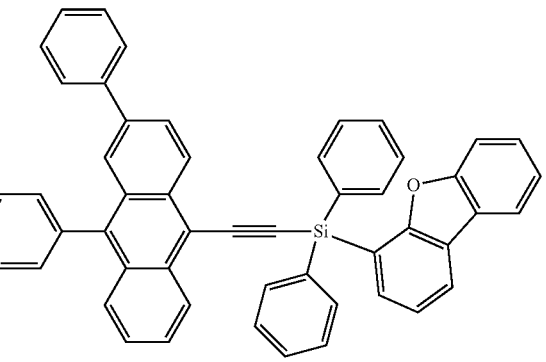
43
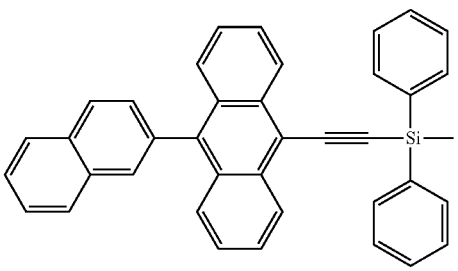
44
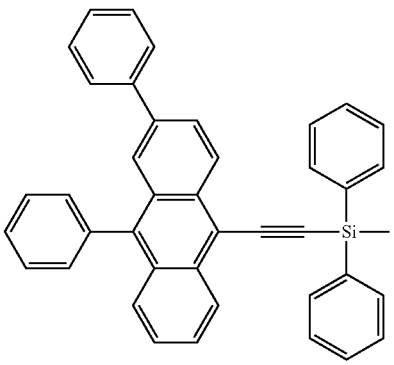

1081
-continued
45
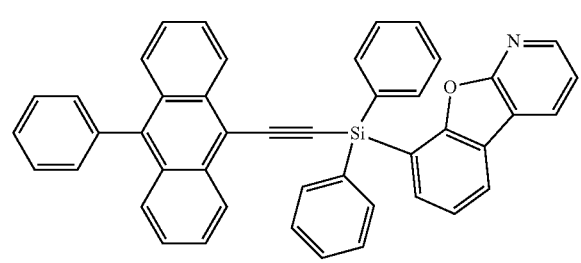
46
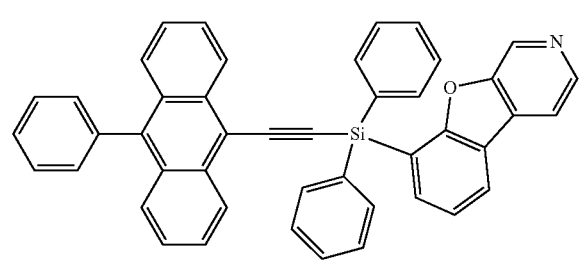
47
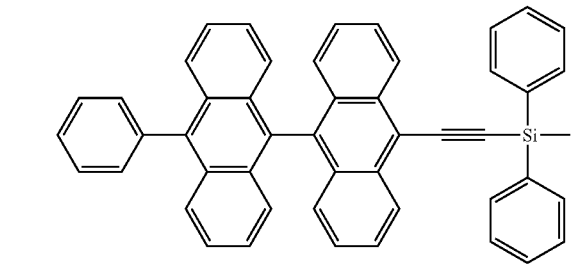
48
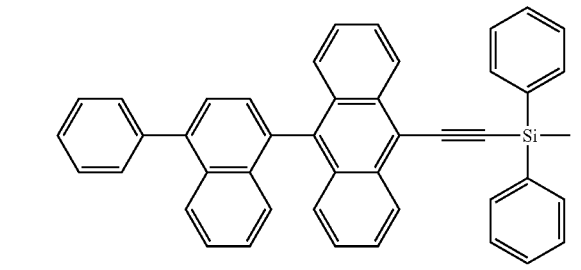
49
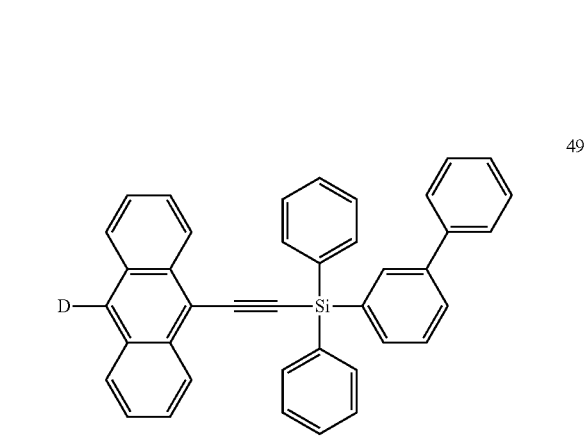
1082
-continued
50
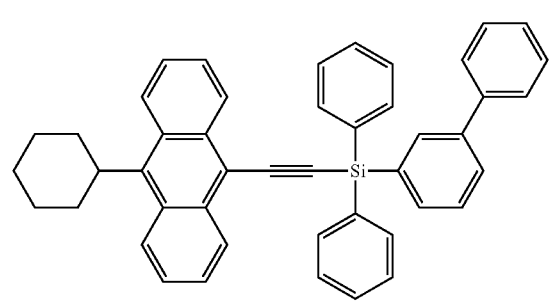
51
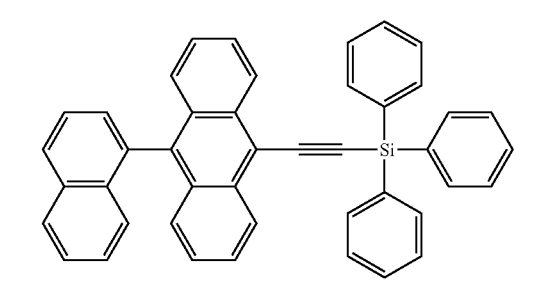
52
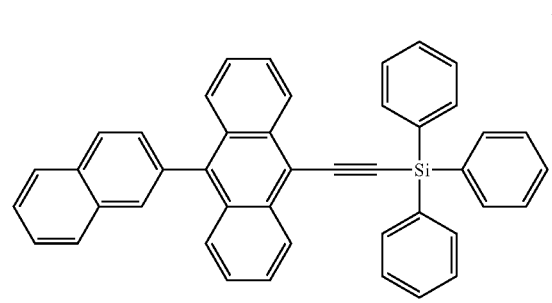
53
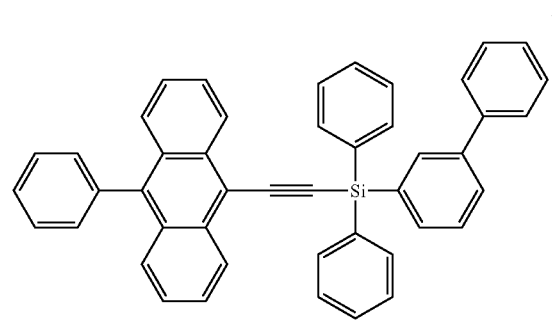
54
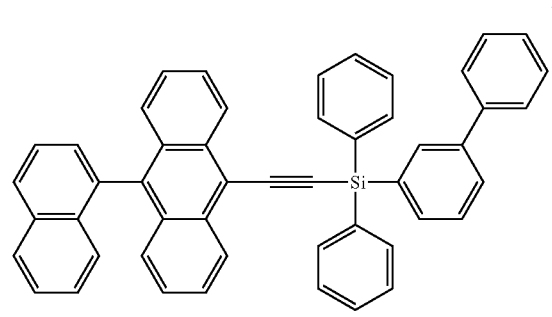

55
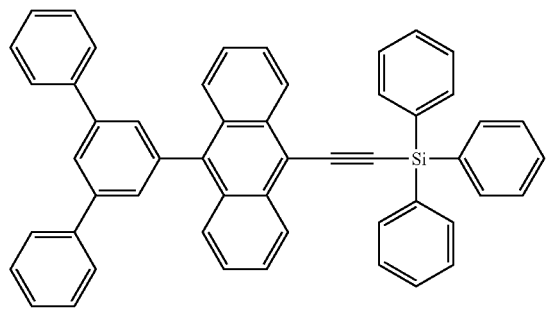
56
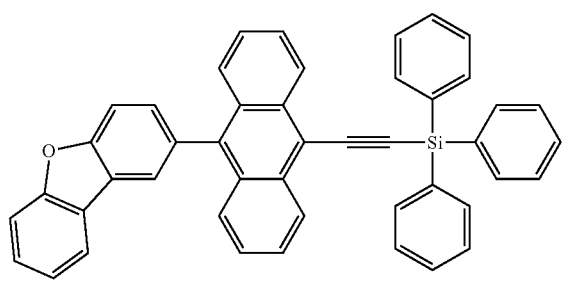
57
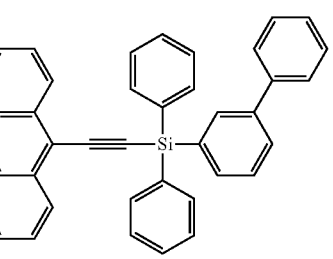
58
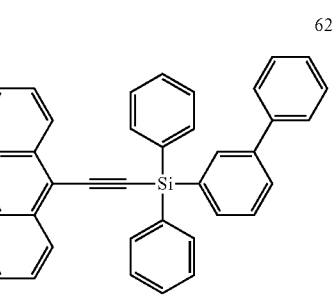
59
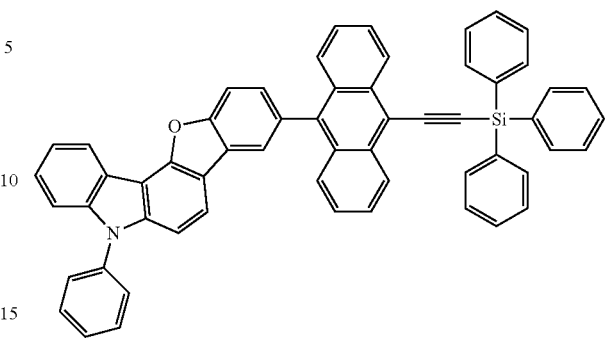
60
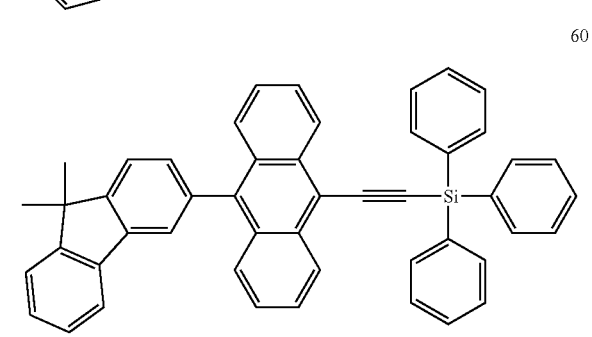
61

62
63

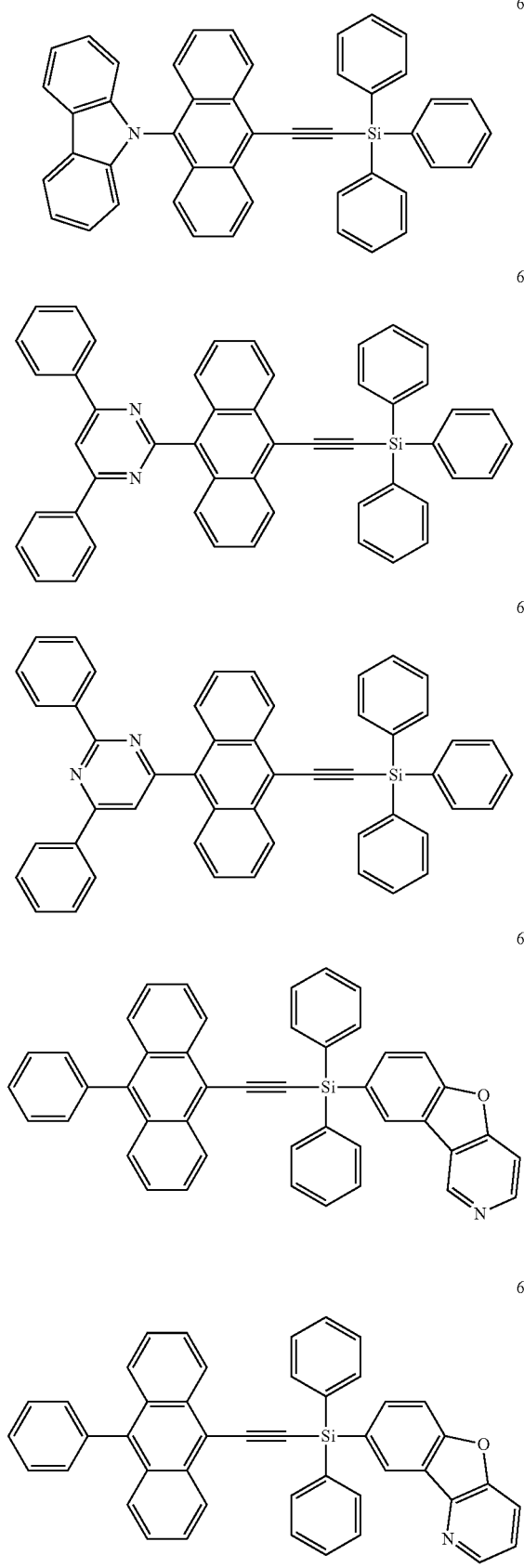
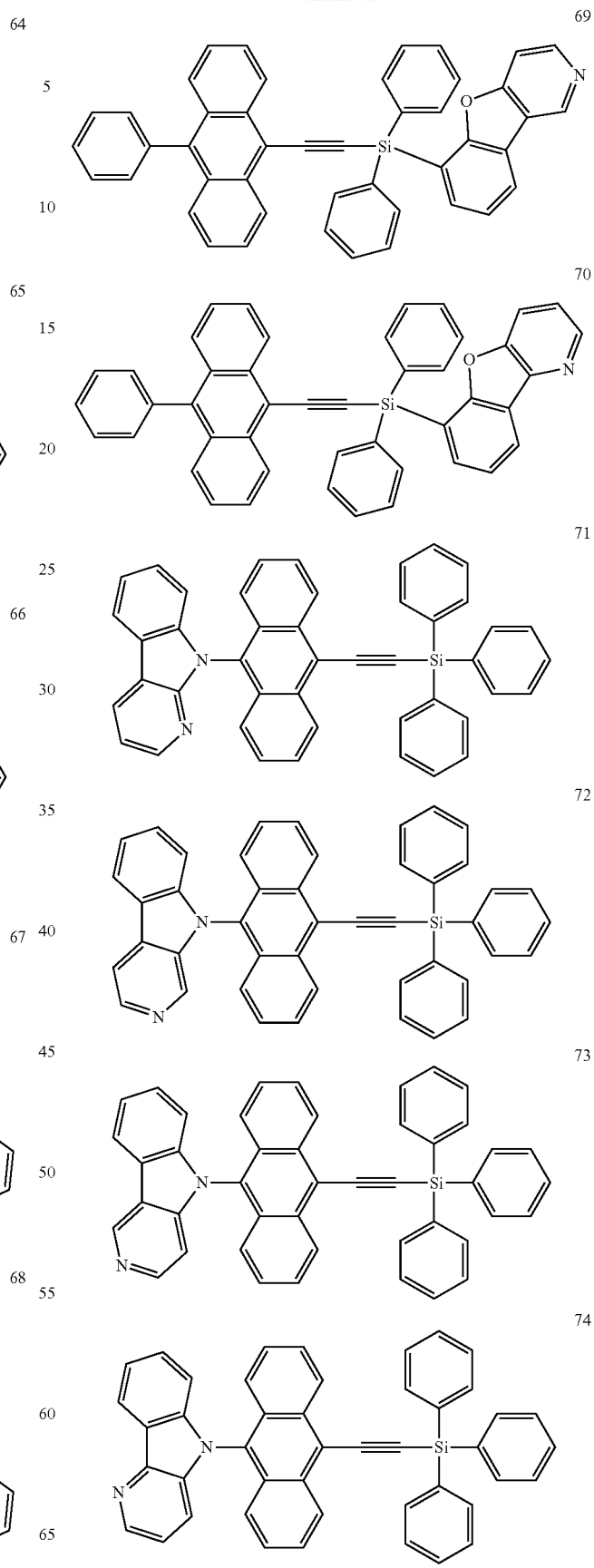

1087 -continued
75
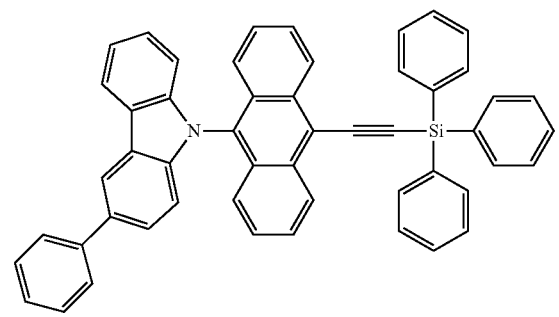
76
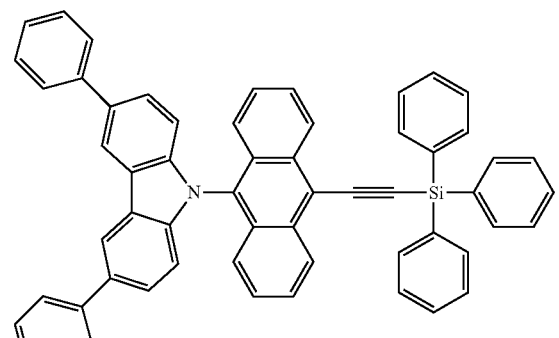
77
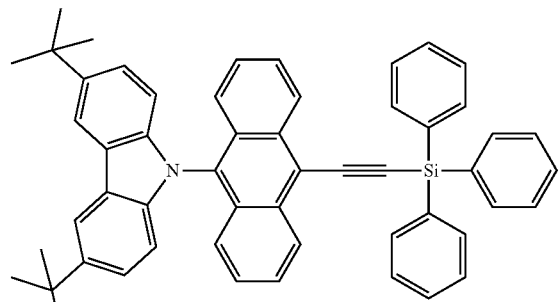
78
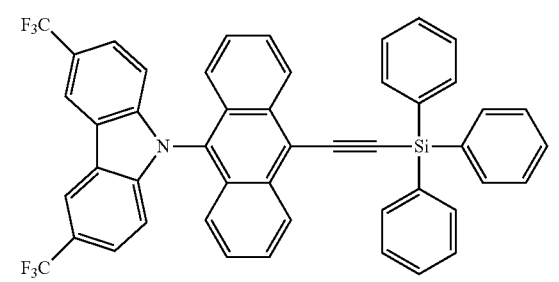
1088 -continued
79
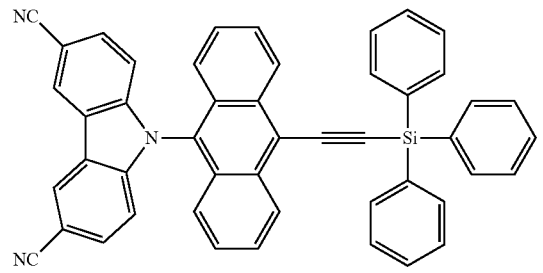
80
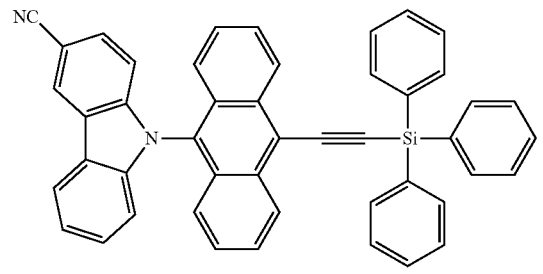
81
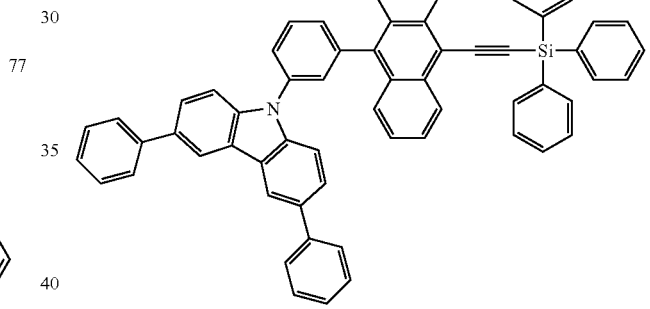
82
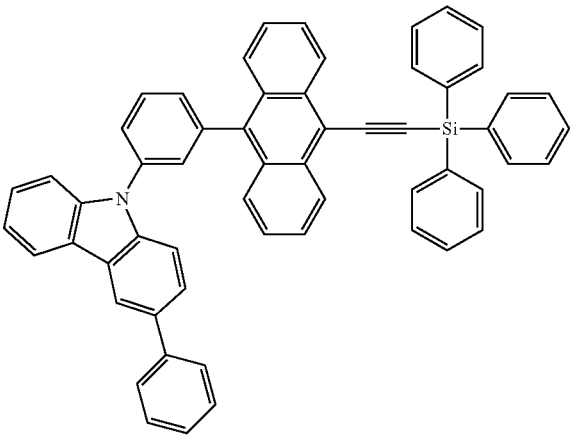

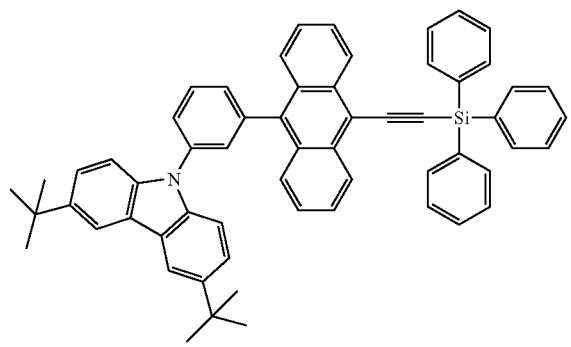
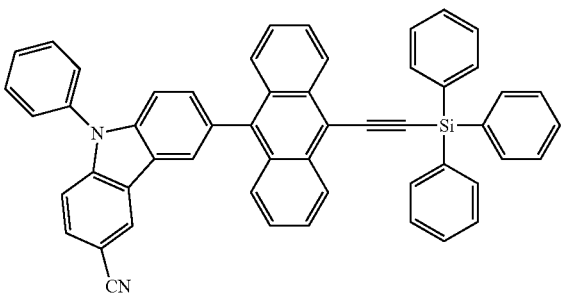
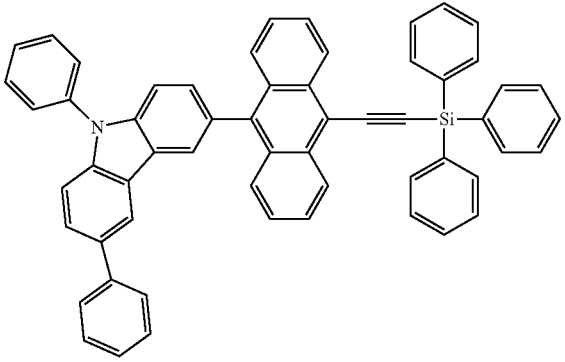
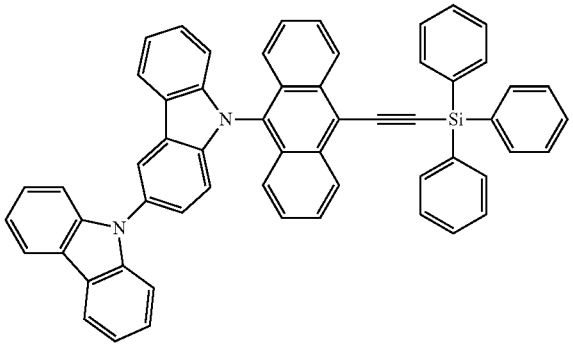
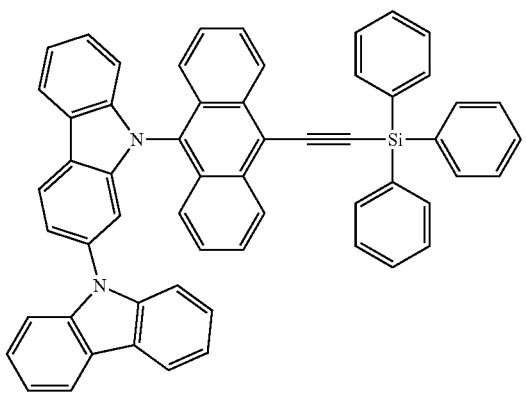

1091
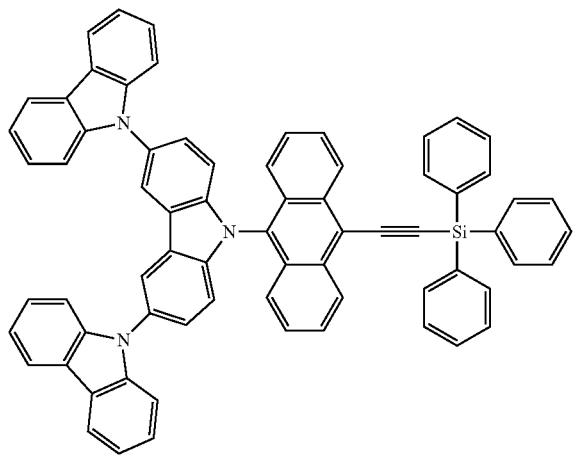
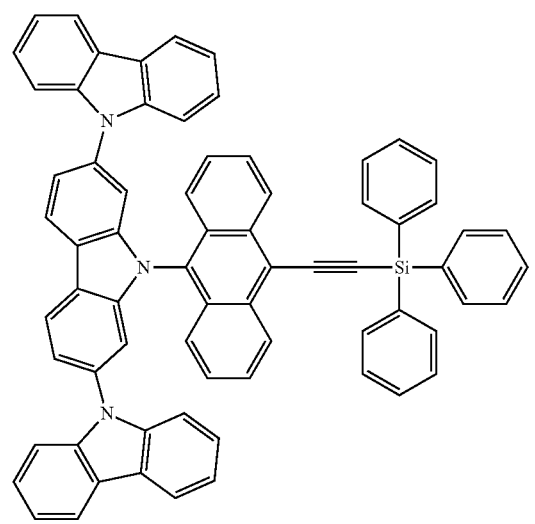
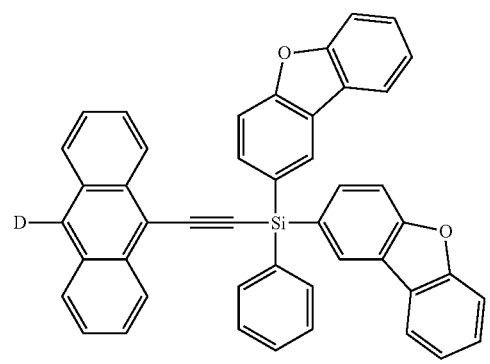
1092
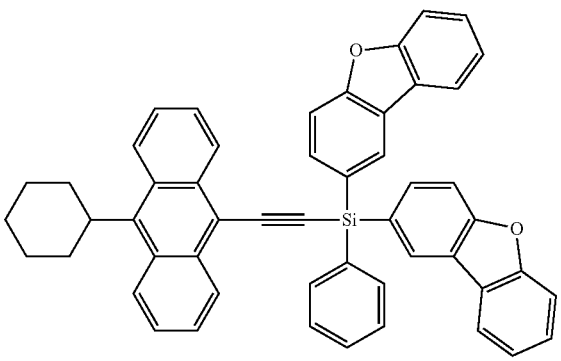
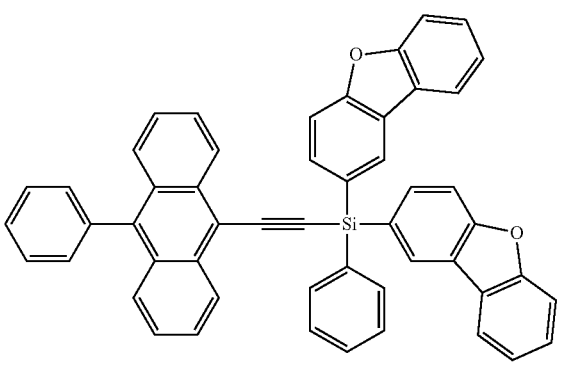
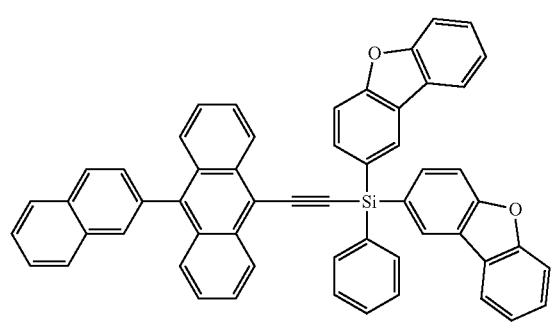

-continued
98
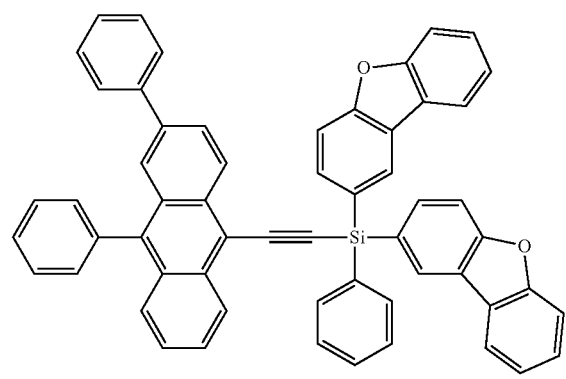
99
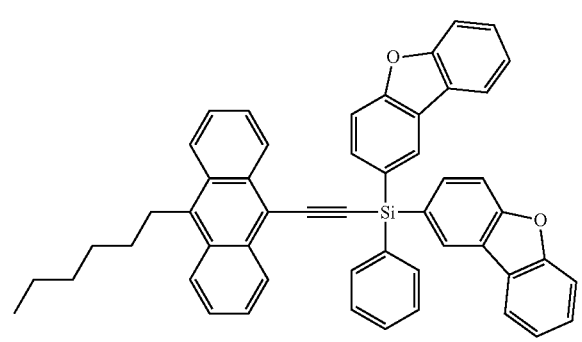
100
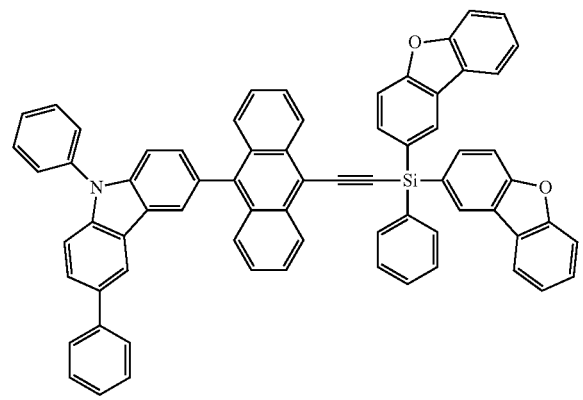
101
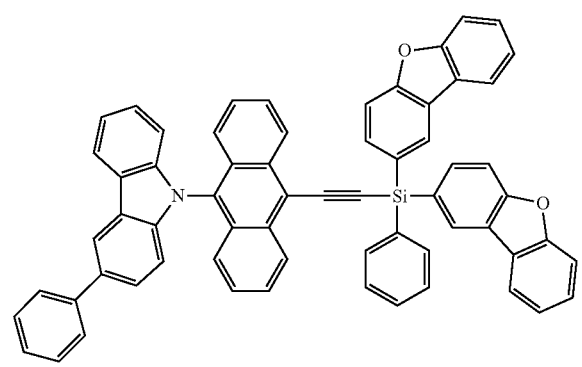
-continued
102
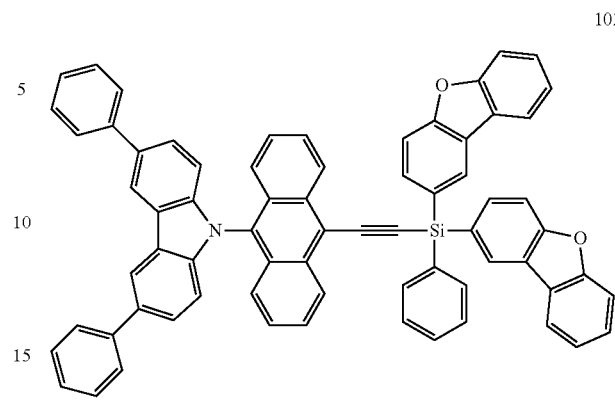
103
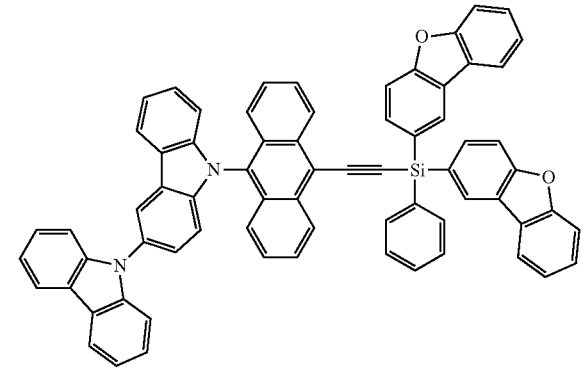
104
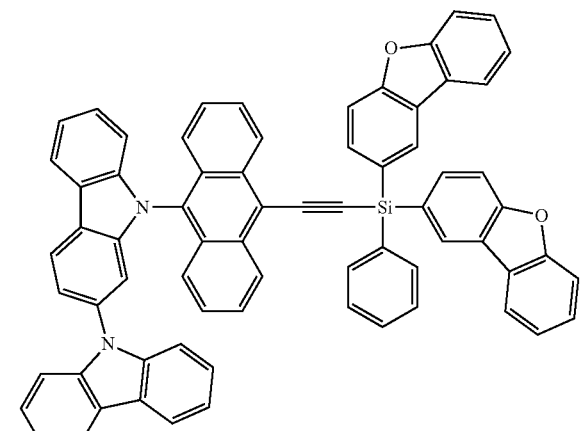
105
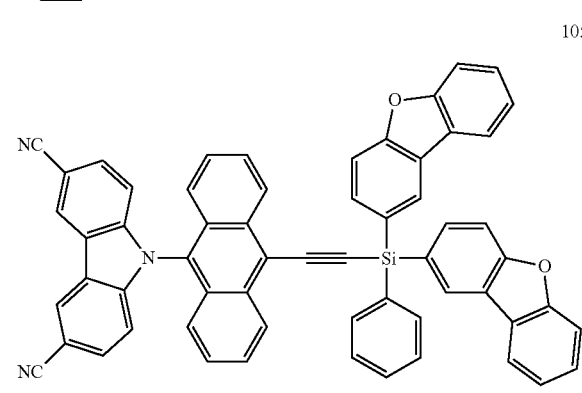

1095
-continued
106
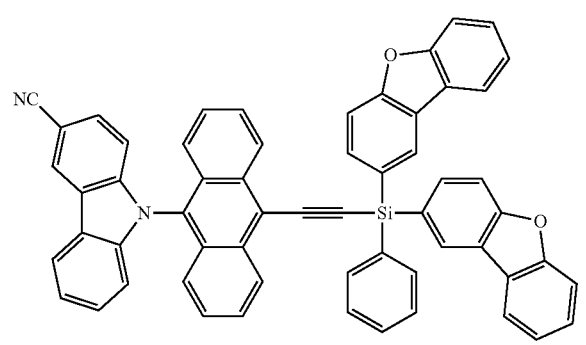
107
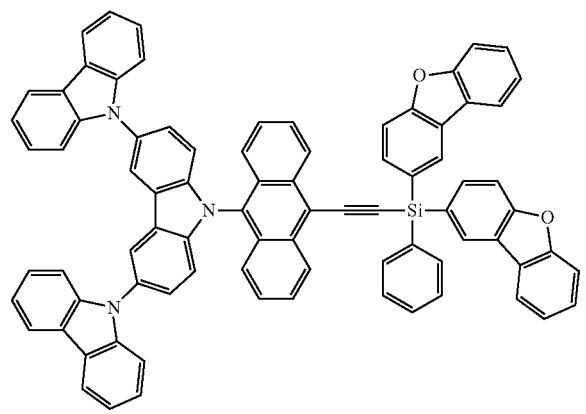
108
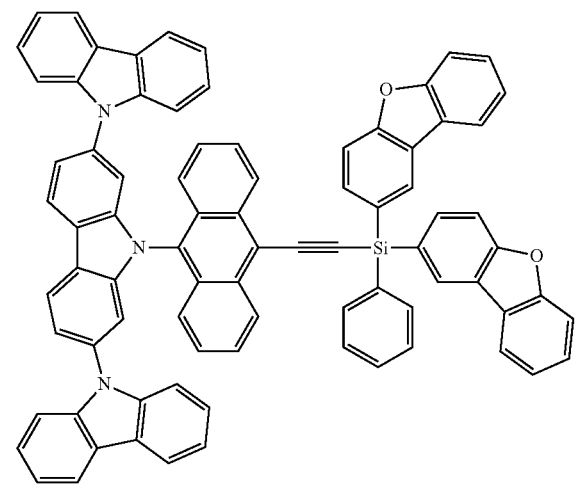
109
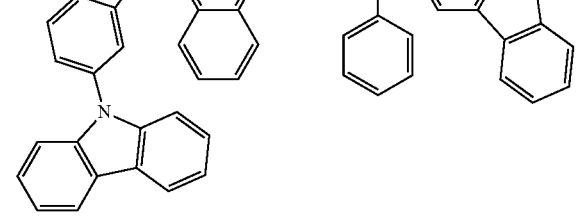
1096
-continued
110
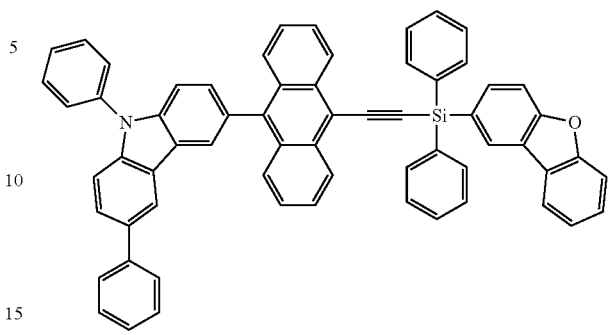
111
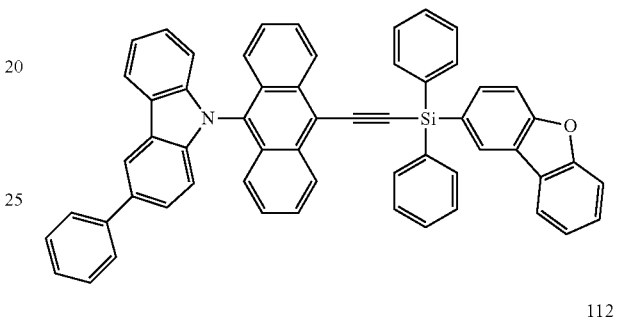
112
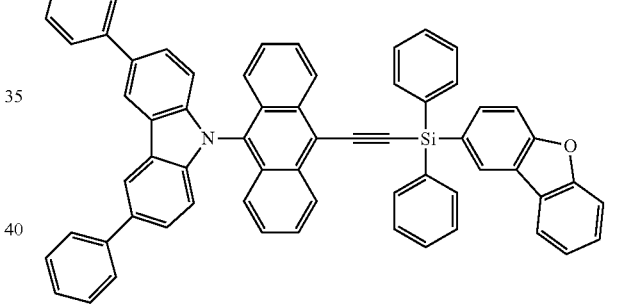
113
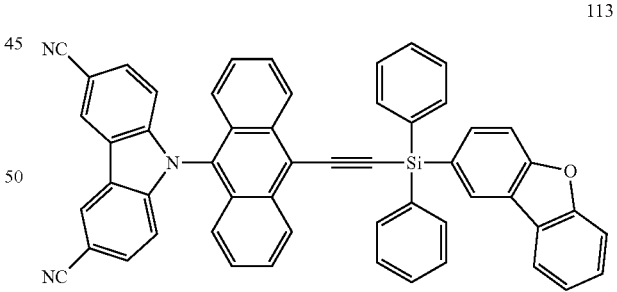
114
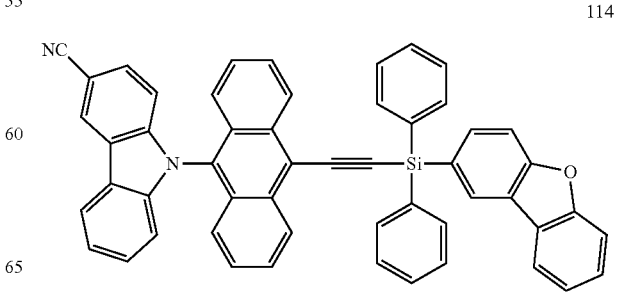

1097
-continued
115
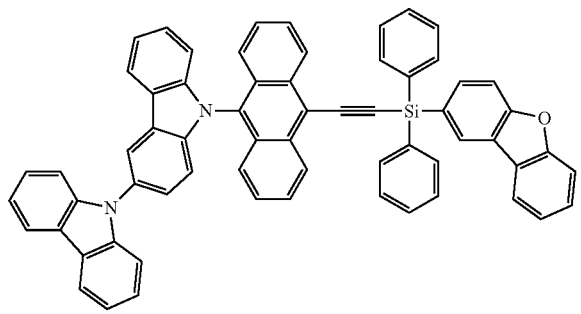
116
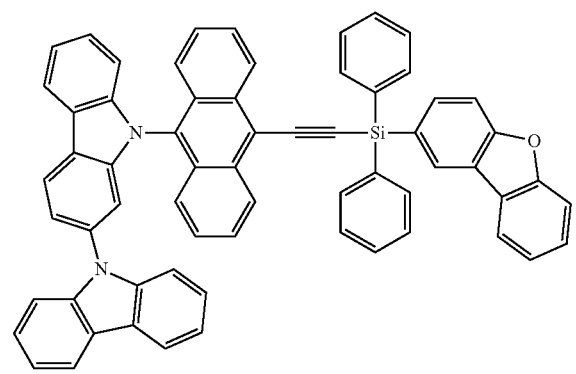
117
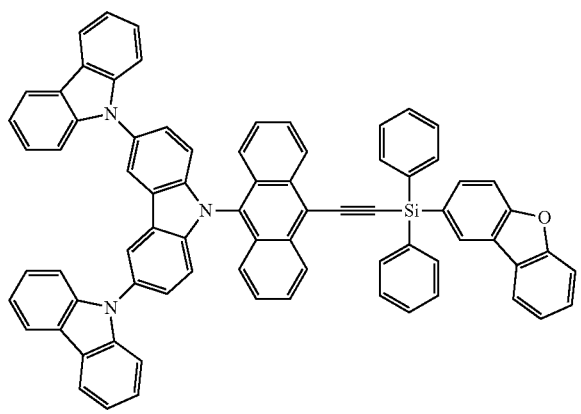
118
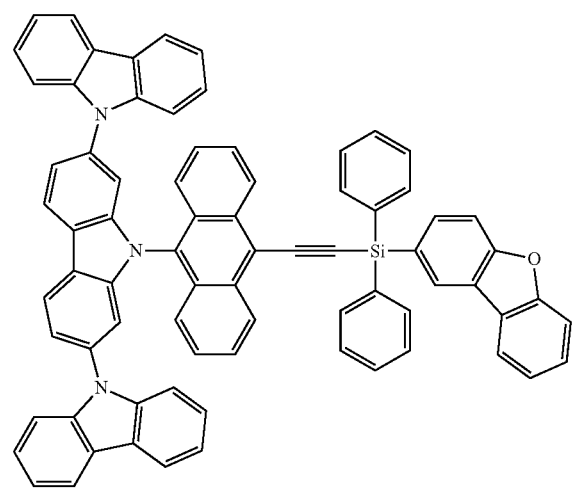
1098
-continued
119
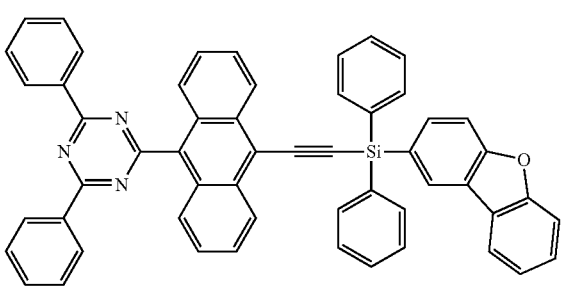
120
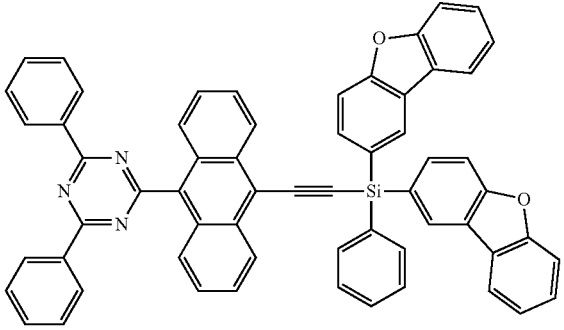
121
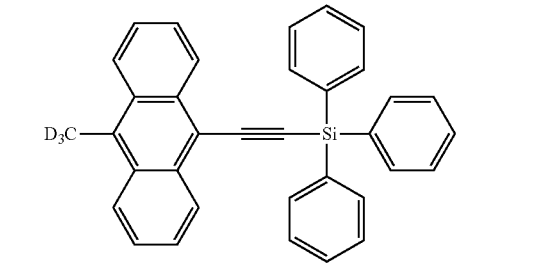
122
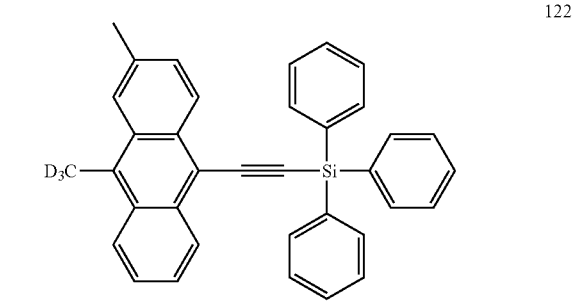
123
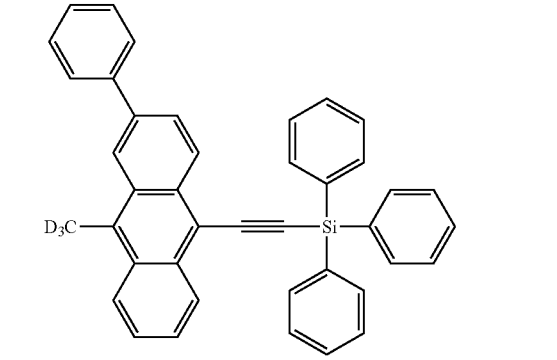

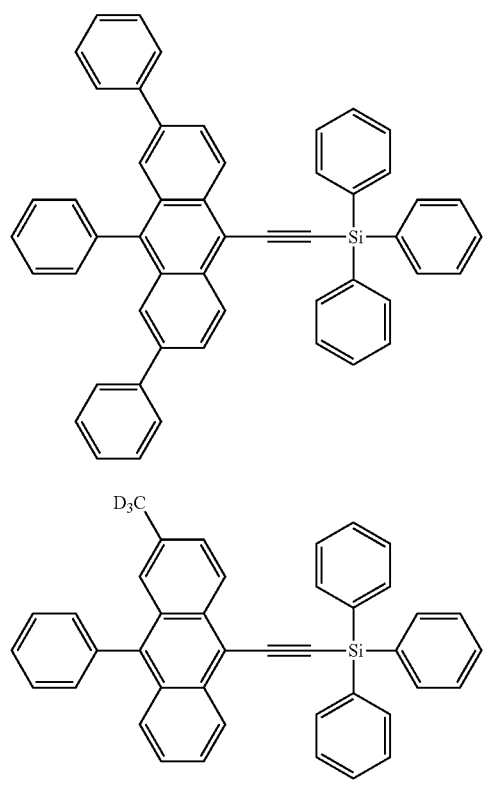
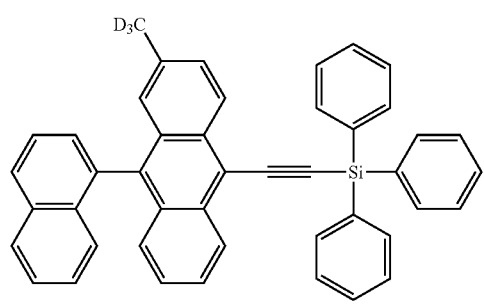
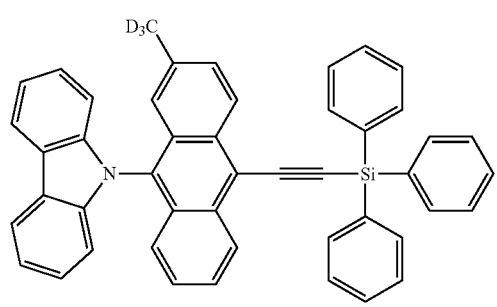
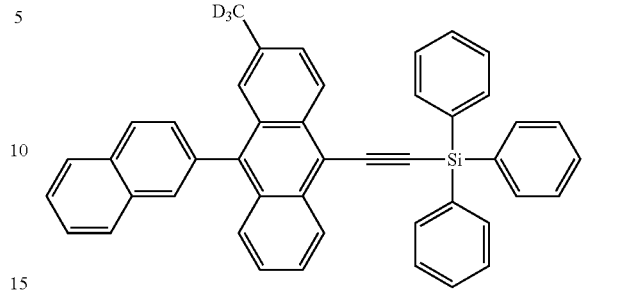
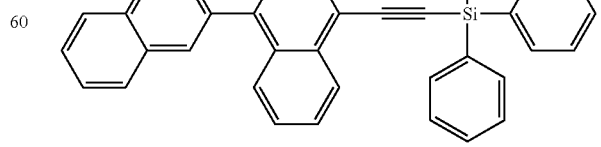

-continued
133
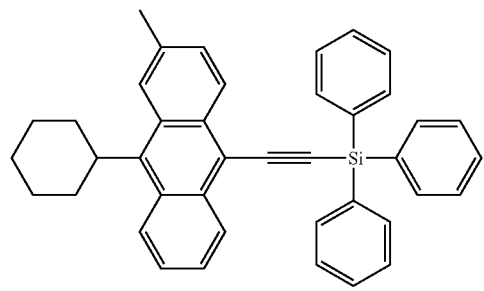
134
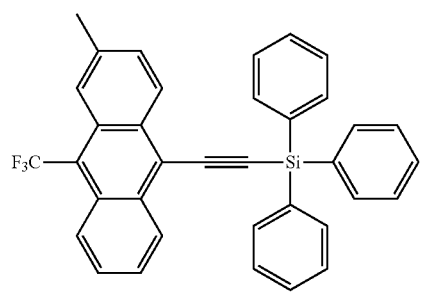
135
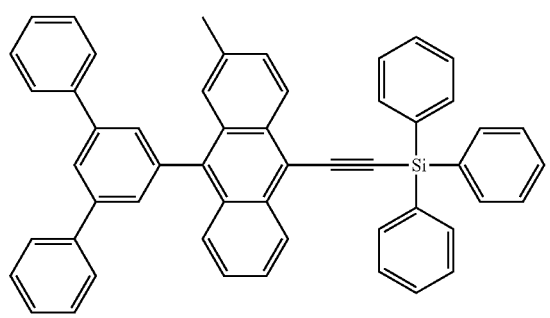
136
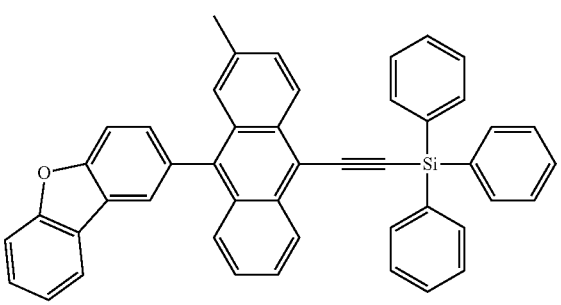
137
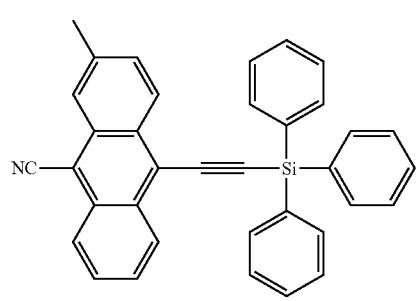
-continued
138
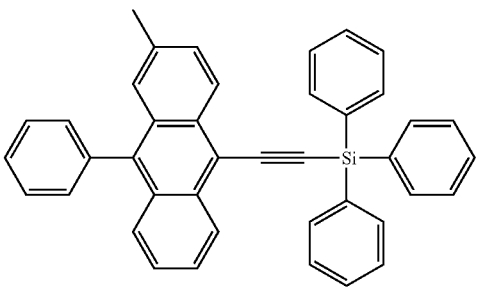
139
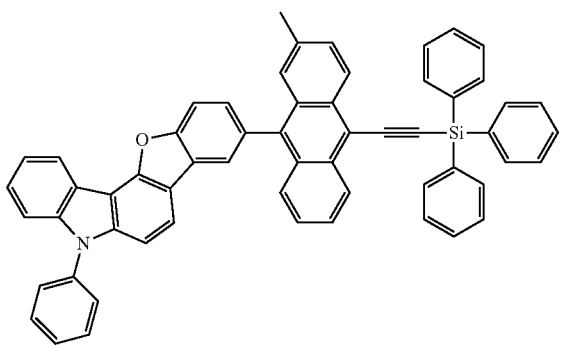
140
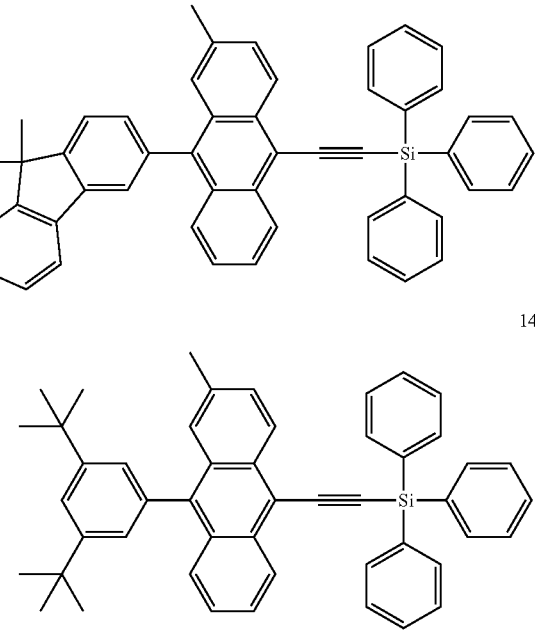
141
142
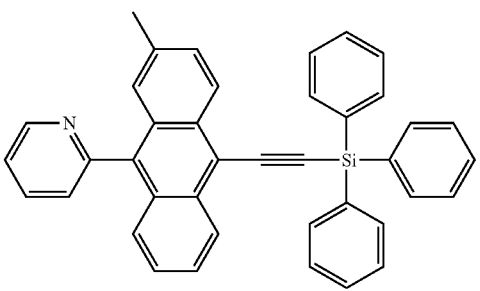

143
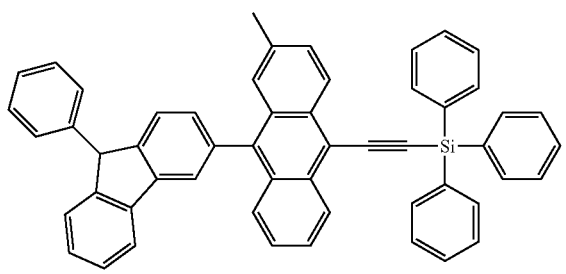
144
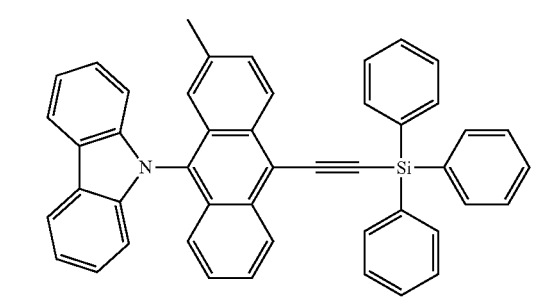
145
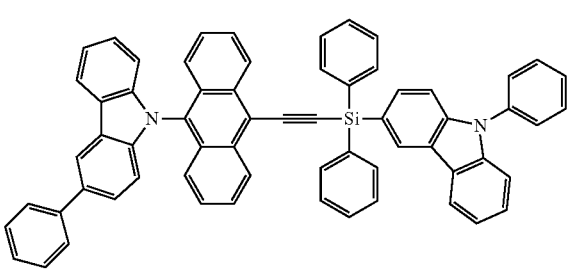
146
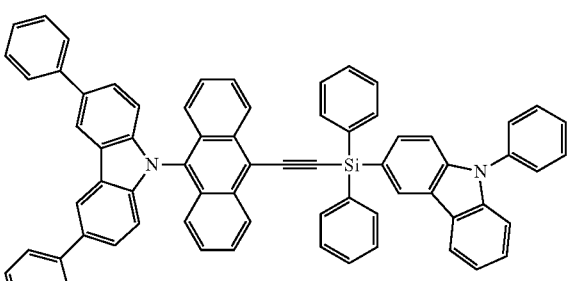
147
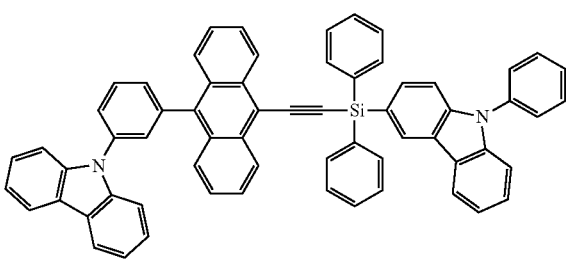
148
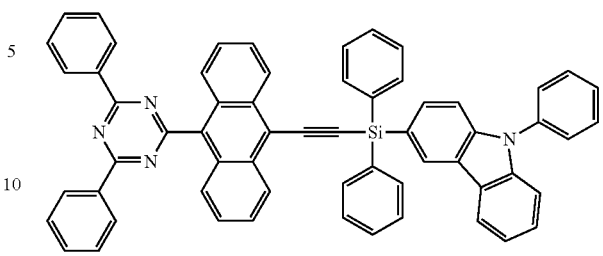
149
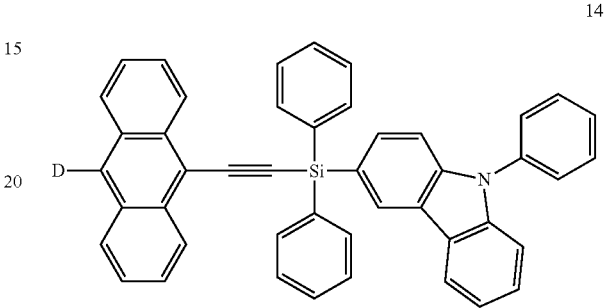
150
151
152
153

1105
-continued

154
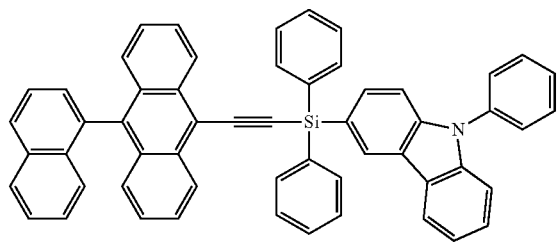

155
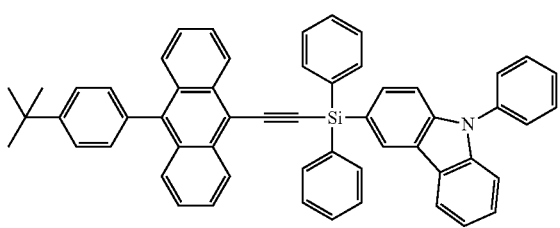

156
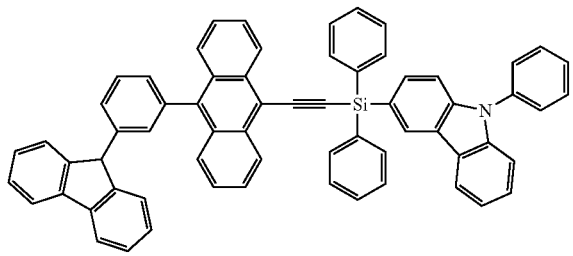

157
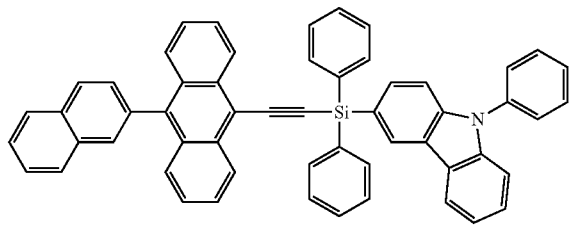

158
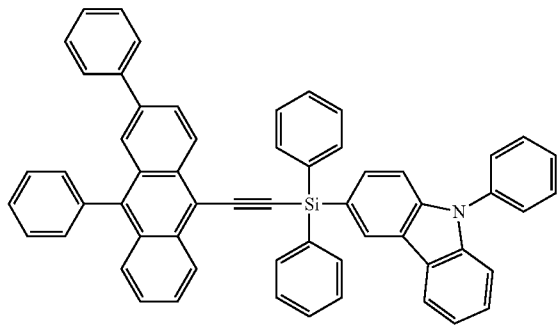

1106
-continued

159
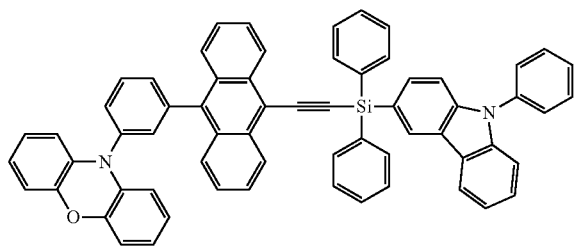

160
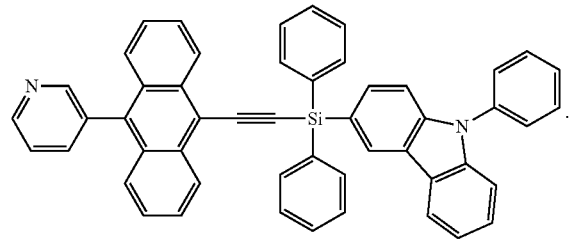

In some embodiments, the fluorescent host may be represented by Formula FH-2:

Formula FH-2

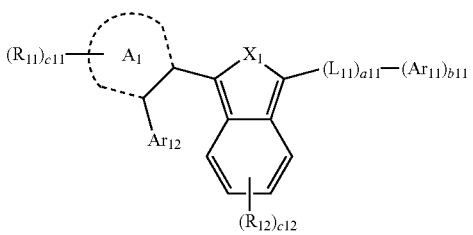

wherein, in Formula FH-2, $X_1$ may be O or S, $A_1$ may be a $C_5$-$C_{60}$ carbocyclic group or a $C_1$-$C_{60}$ heterocyclic group, $L_{11}$ may be a substituted or unsubstituted $C_5$-$C_{60}$ carbocyclic group or a substituted or unsubstituted $C_1$-$C_{60}$ heterocyclic group, a11 may be an integer from 0 to 3, $Ar_{11}$ and $Ar_{12}$ may each independently be a $C_6$-$C_{60}$ aryl group, a $C_1$-$C_{60}$ heteroaryl group, a monovalent non-aromatic condensed polycyclic group, or a monovalent non-aromatic condensed heteropolycyclic group, each unsubstituted or substituted with at least one $R_a$, b11 may be an integer from 1 to 5, $R_{11}$, $R_{12}$, and $R_a$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), c11 may be an integer from 1 to 20, c12 may be an integer from 1 to 4, when c11 is 2 or greater, two adjacent $R_{11}$(s) may optionally be bound to each other to form a substituted or unsubstituted $C_5$-$C_{30}$ carbocyclic group or a substituted or unsubstituted $C_1$-$C_{30}$ heterocyclic group, when c12 is 2 or greater, two adjacent $R_{12}$(s) may optionally be bound to each other to form a substituted or unsubstituted $C_5$-$C_{30}$ carbocyclic group or a substituted or unsubstituted $C_1$-$C_{30}$ heterocyclic group, $A_1$ and $Ar_{12}$ may optionally be bound to each other via a first linking group a single bond, *—$Ar_{31}$—*', *—O—*', *—S—*', *—[C($R_{31}$)($R_{32}$)]$_{k11}$—*', *—C($R_{31}$)=*', *=C($R_{31}$)—*', *—C($R_{31}$)=C($R_{32}$)—*', *—C(=O)—*', *—C(=S)—*', *—C≡C—*', *—N($R_{31}$)—*', *—P($R_{31}$)—*', *—[S$_1$($R_{31}$)($R_{32}$)]$_{k11}$—*', and *—P($R_{31}$)($R_{32}$)—*' to form a substituted or unsubstituted $C_5$-$C_{30}$ carbocyclic group or a substituted or unsubstituted $C_1$-$C_{30}$ heterocyclic group, $Ar_{31}$ may be a $C_5$-$C_{30}$ carbocyclic group, $R_{31}$ and $R_{32}$ may each be understood by referring to the description of $R_{11}$ provided herein, and k11 may be 1, 2, 3, or 4.

In some embodiments, the fluorescent host represented by Formula FH-2 may be Group FH2, but embodiments are not limited thereto:

Group FH2

1

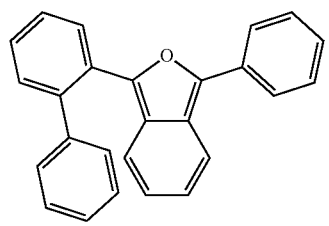

2

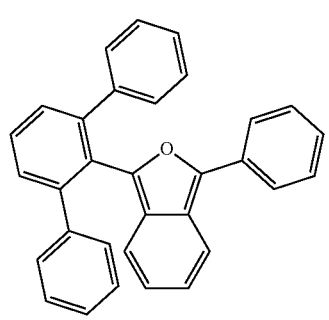

3

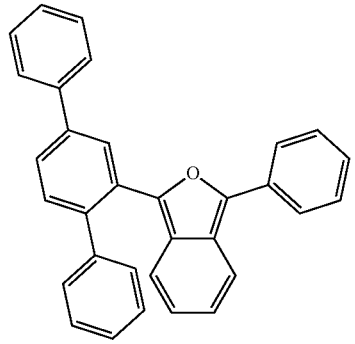

4

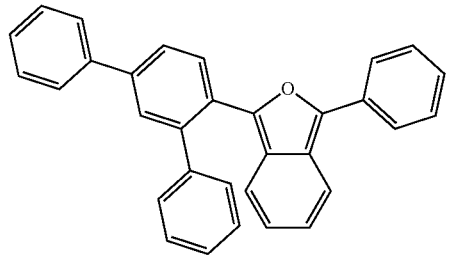

5

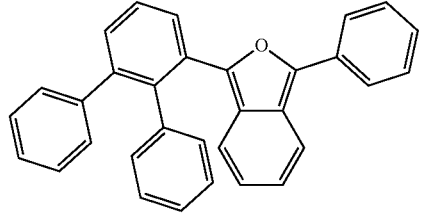

6

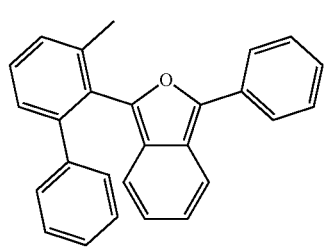

7

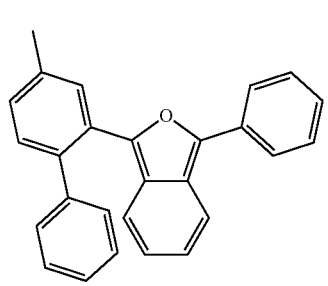

8

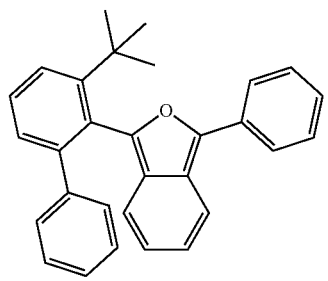

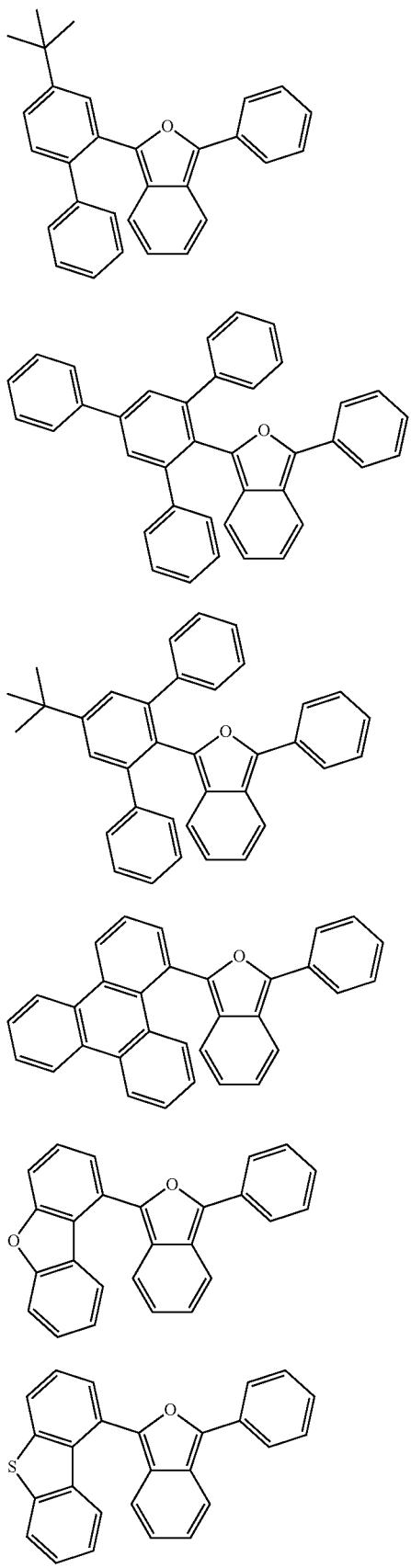
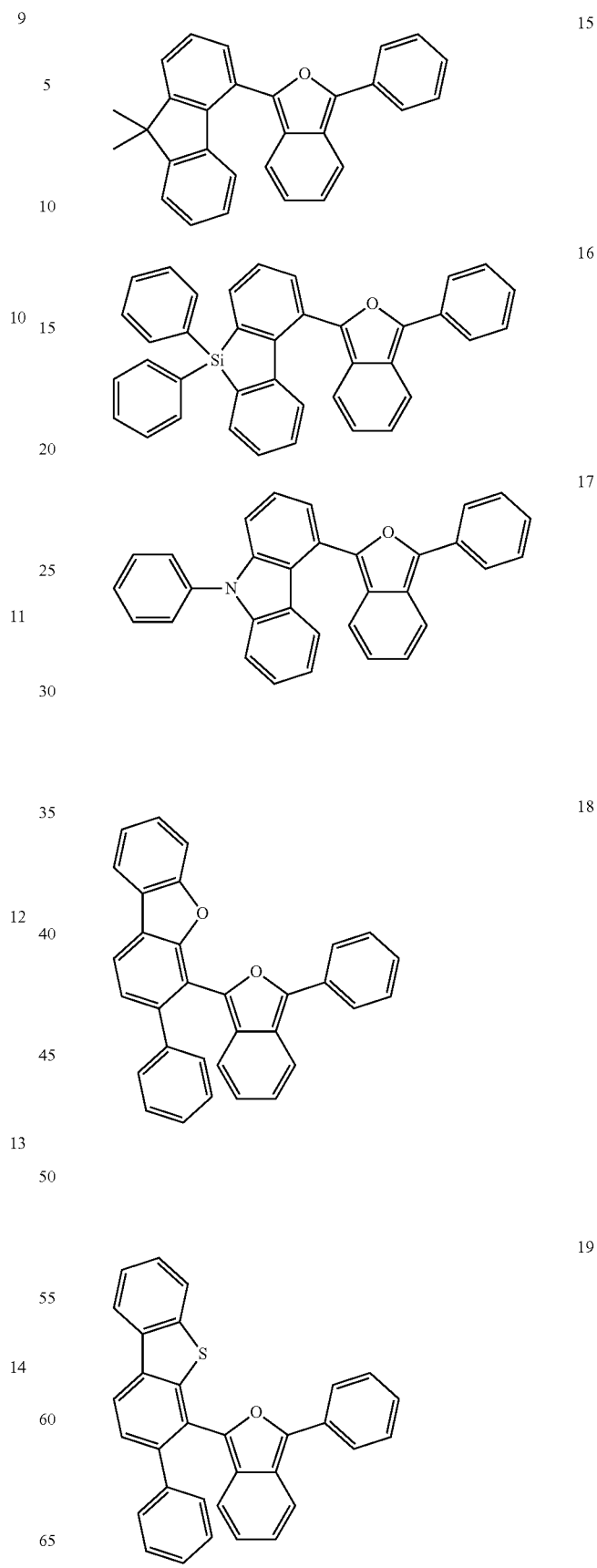

1111
-continued
20
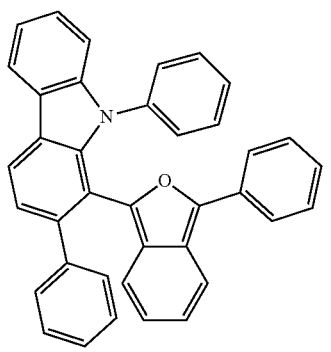
21
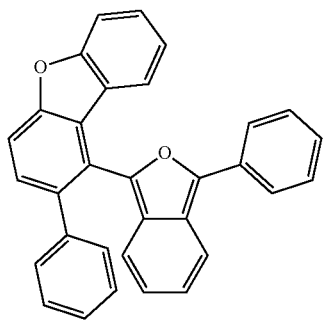
22
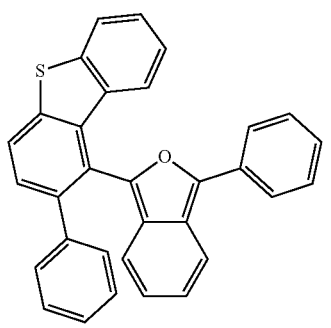
23
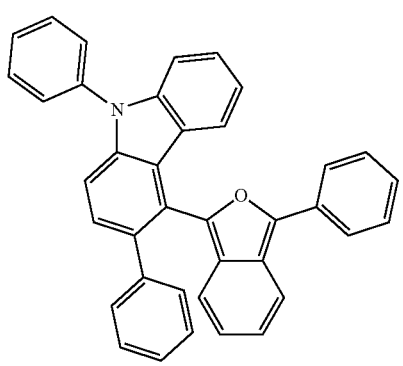
1112
-continued
24
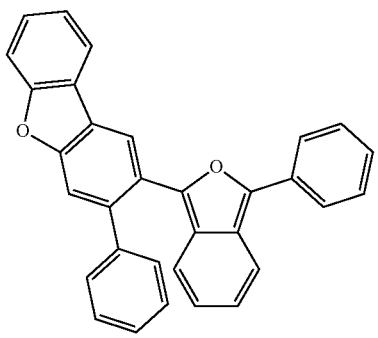
25
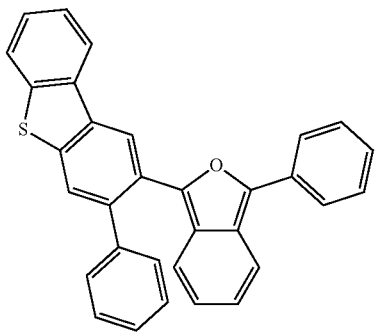
26
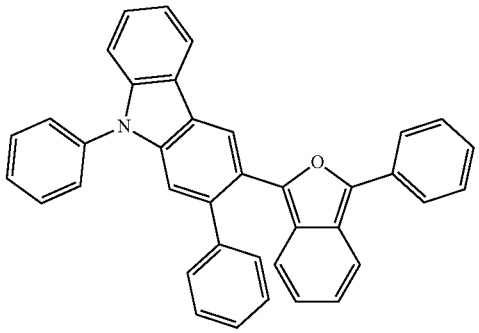
27
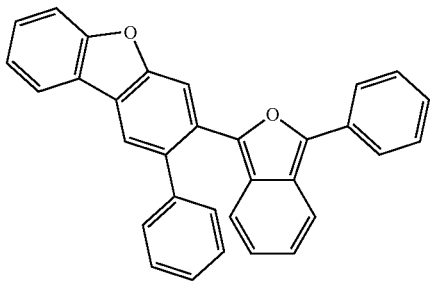
28
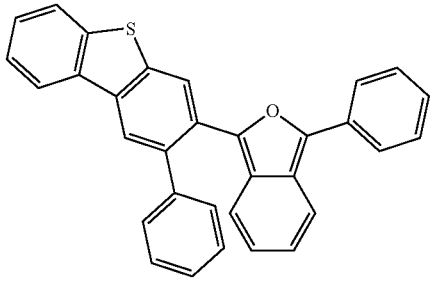

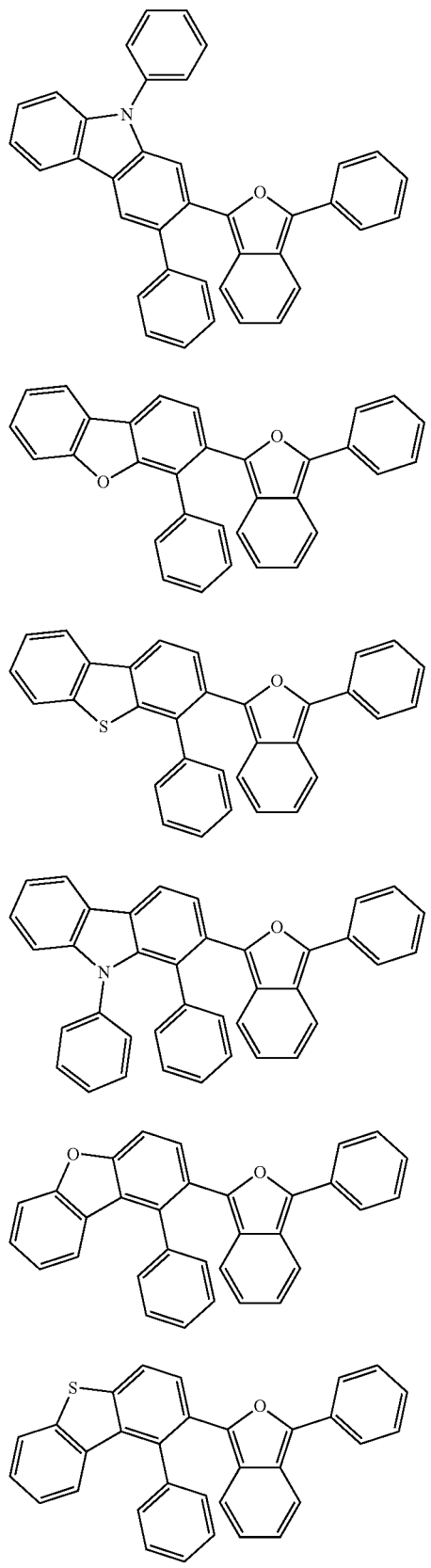

1117
-continued
48
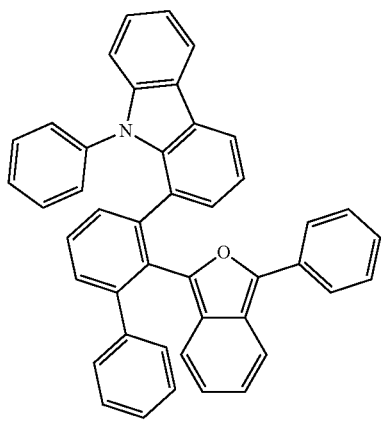
49
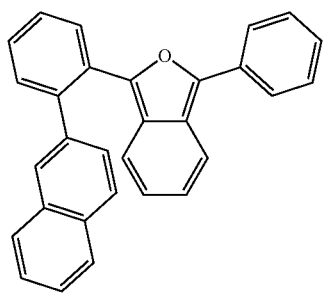
50
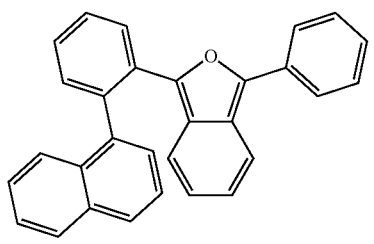
51
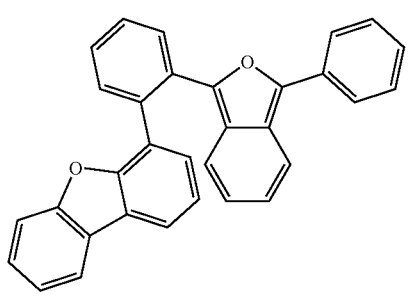
52
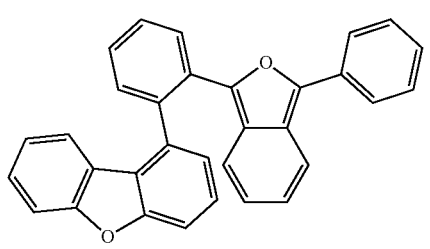
1118
-continued
53
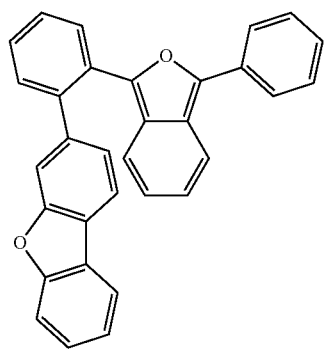
54
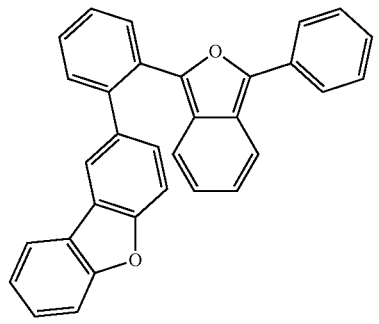
55
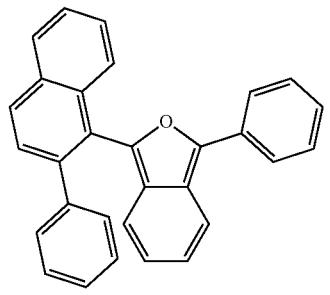
56
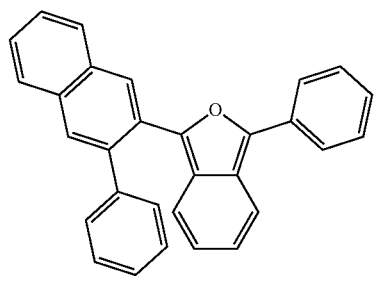
57

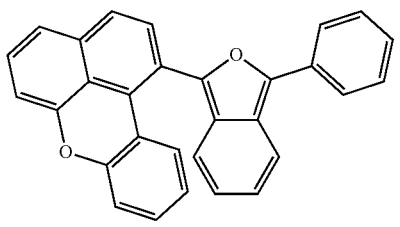
58

59

60

61

62

63

64

65

66

67

68

1121
-continued
69
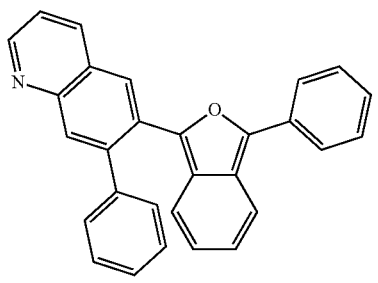
70
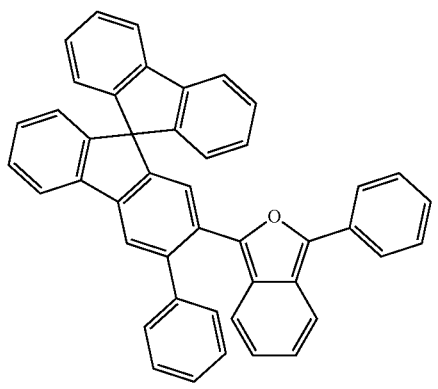
71
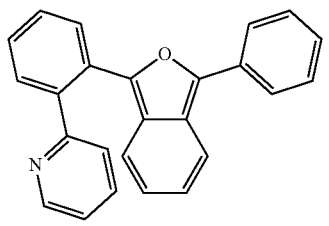
72
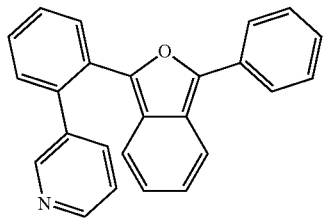
73
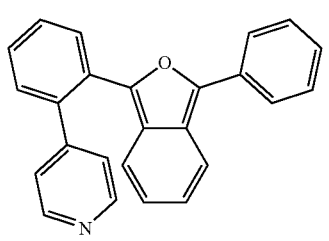
1122
-continued
74

75

76

77
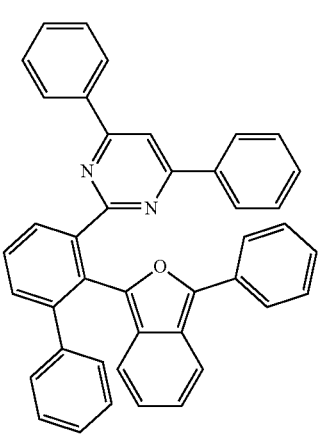

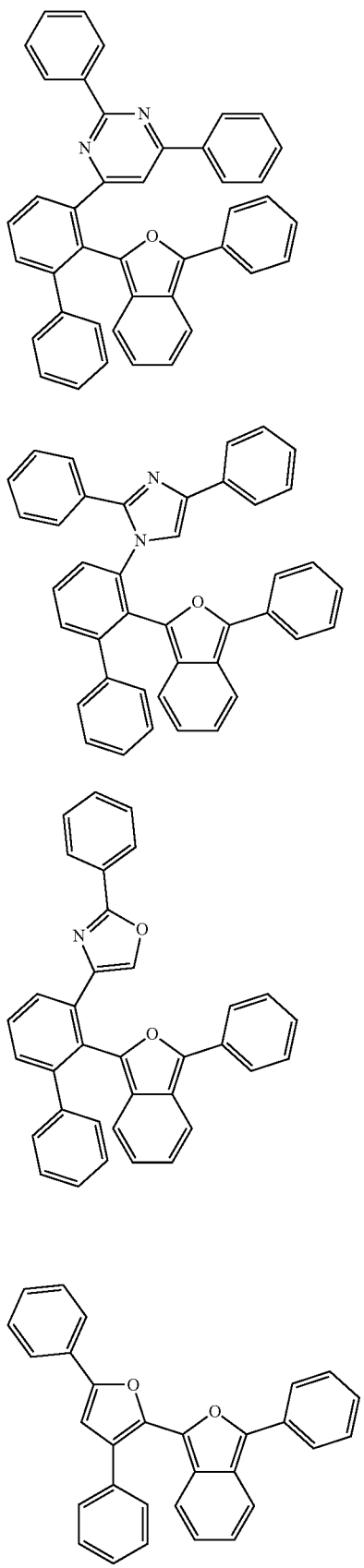
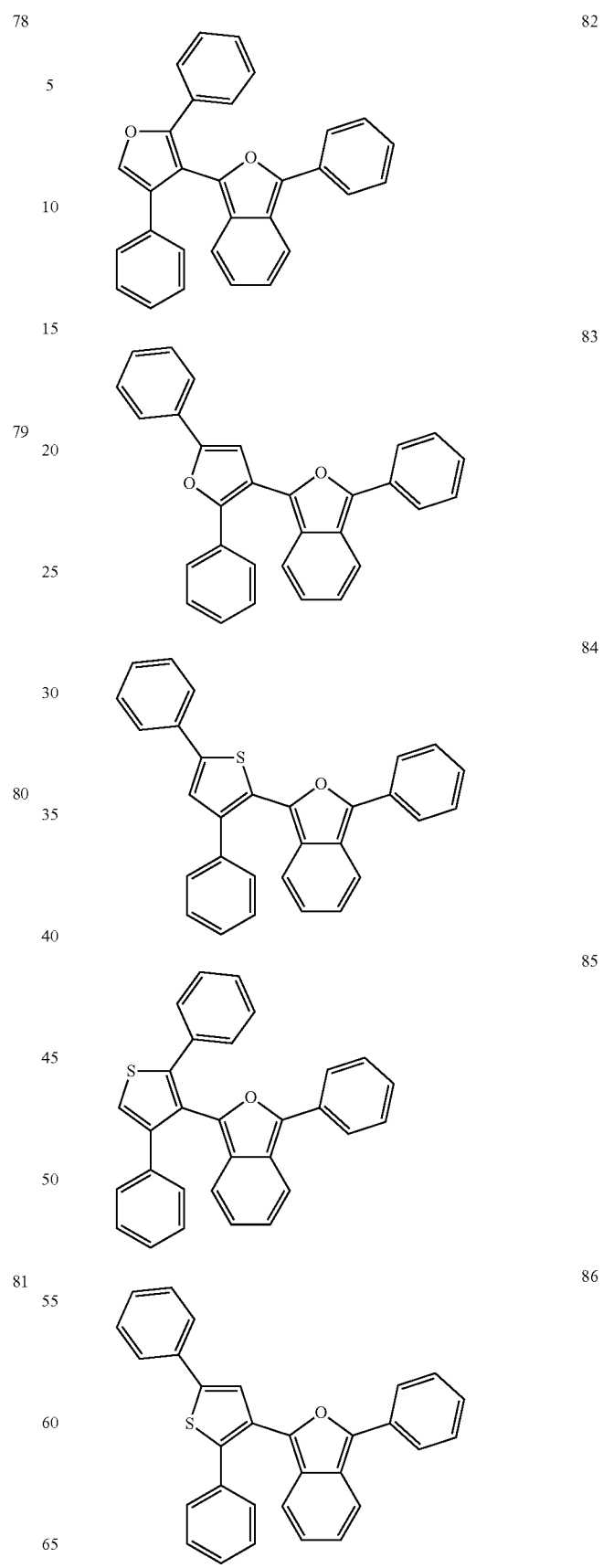

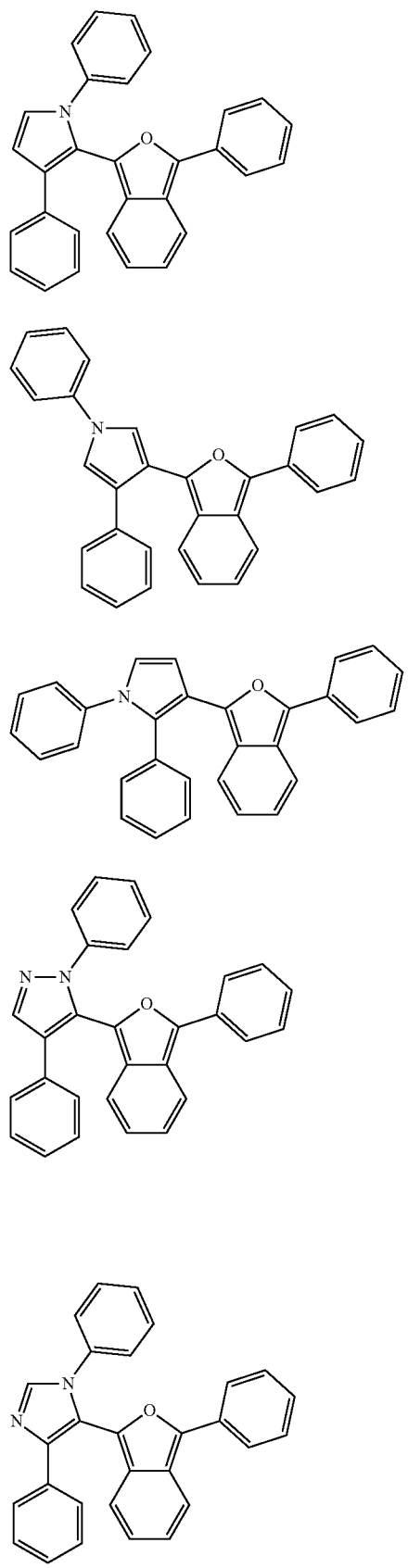
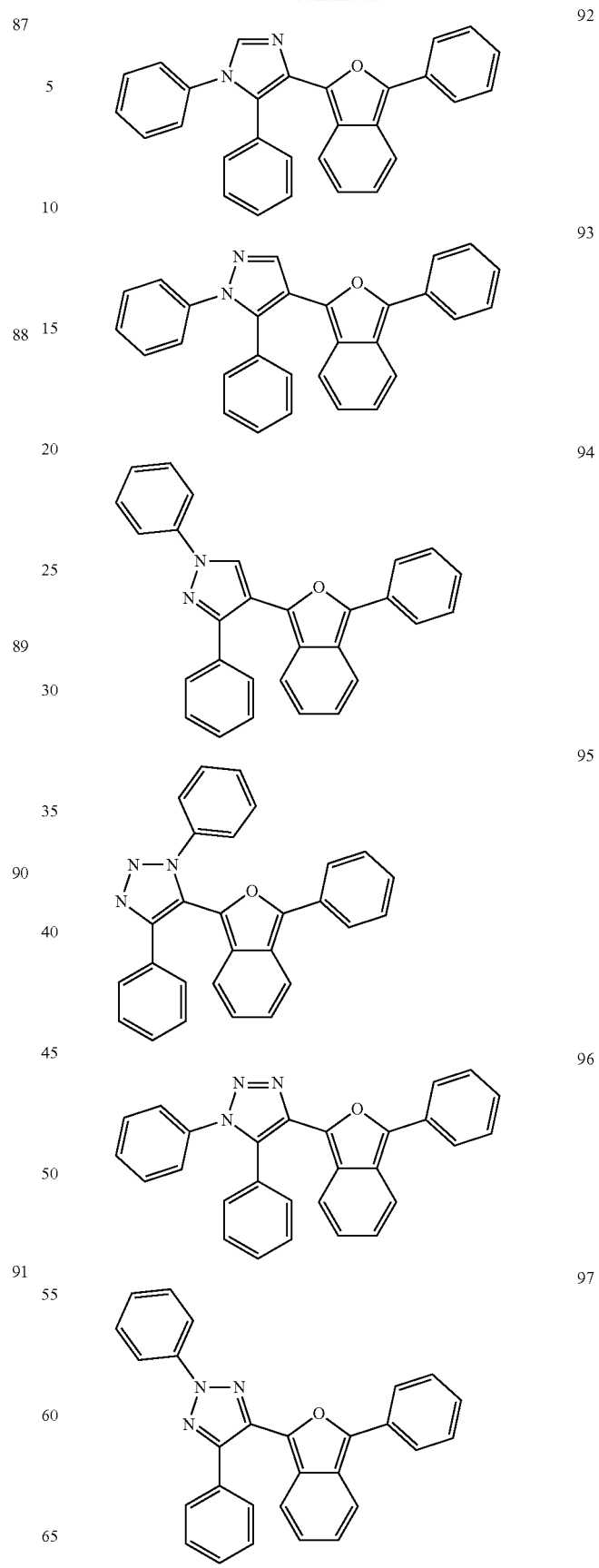

1127
-continued
98
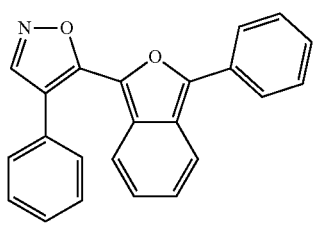
99
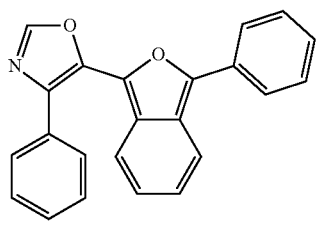
100
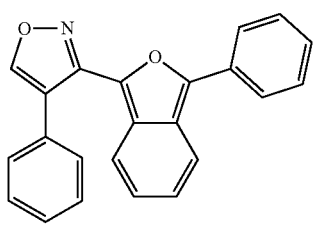
101
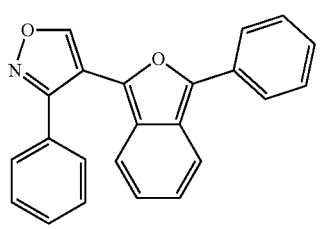
102
103
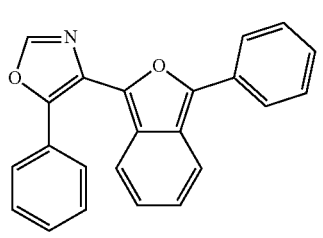
104
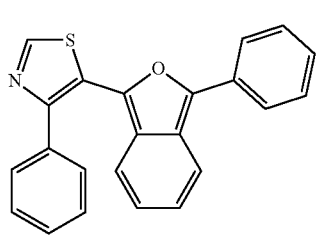
1128
-continued
105
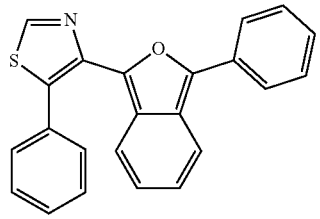
106
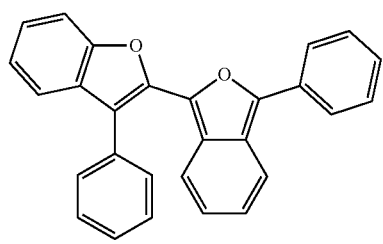
107
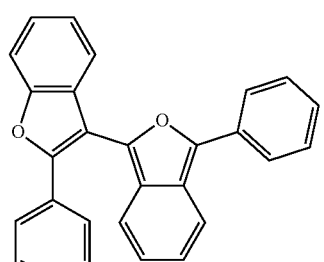
108
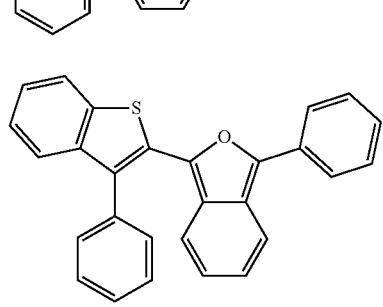
109
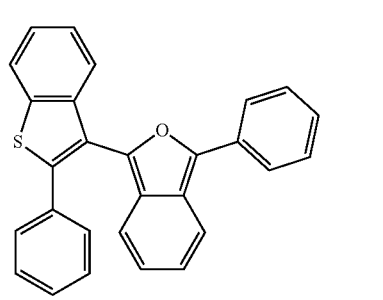
110
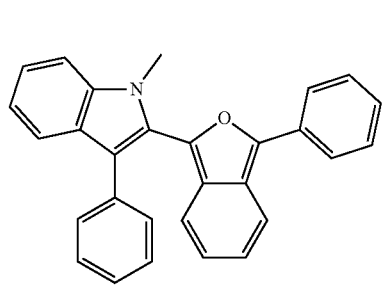

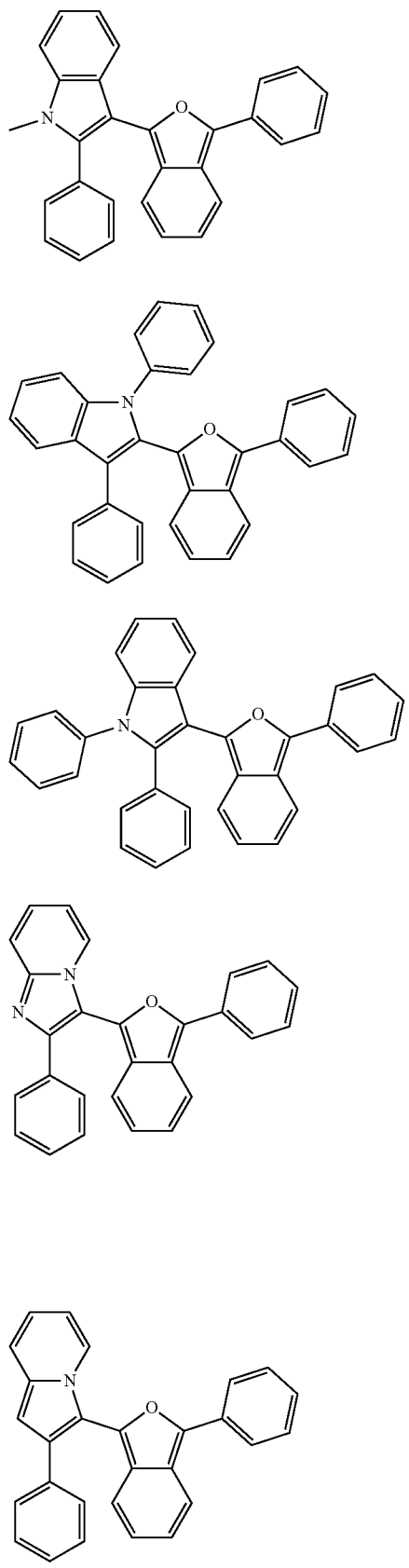
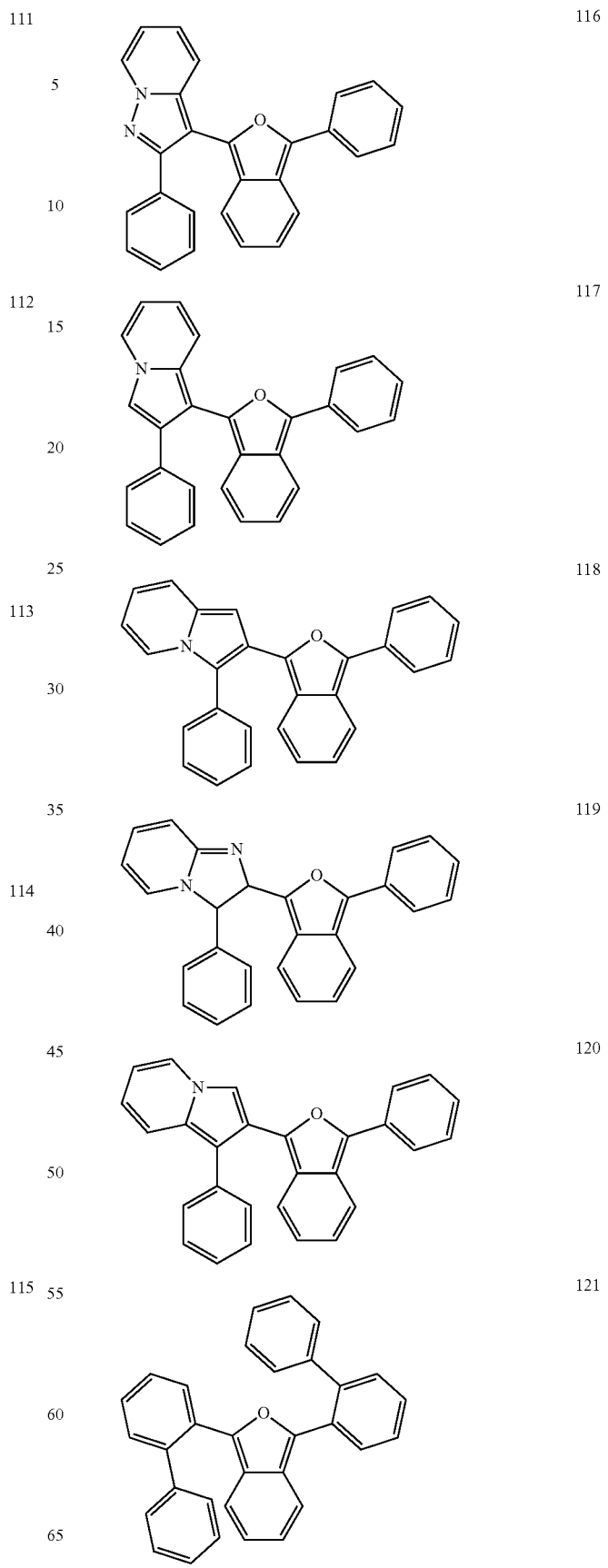

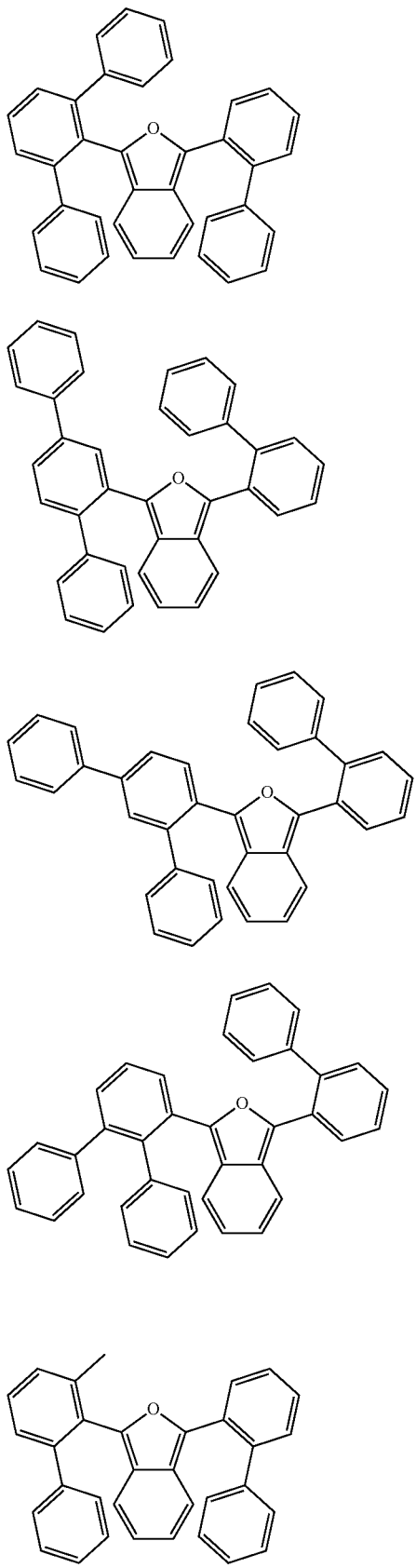
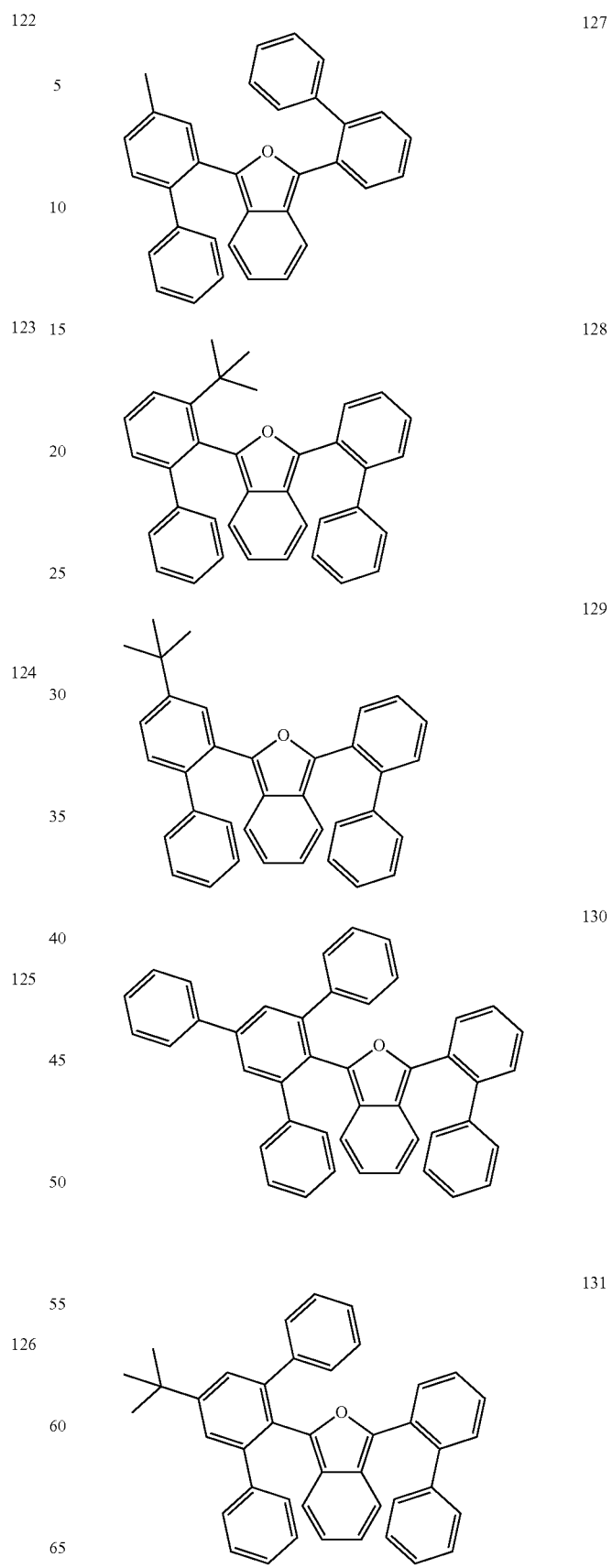

132
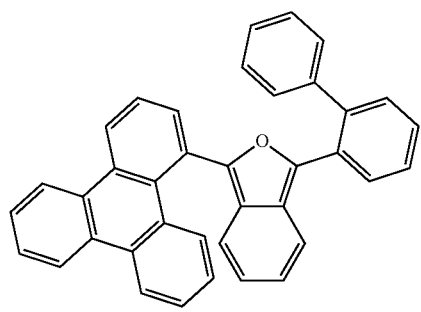
133
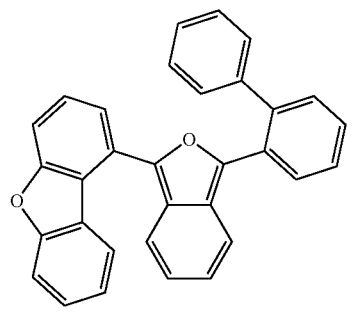
134
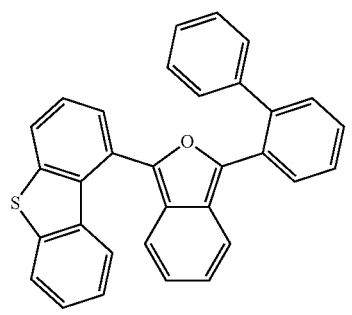
135
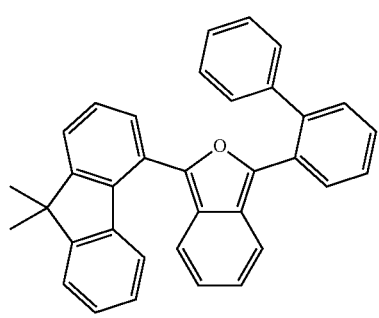
136
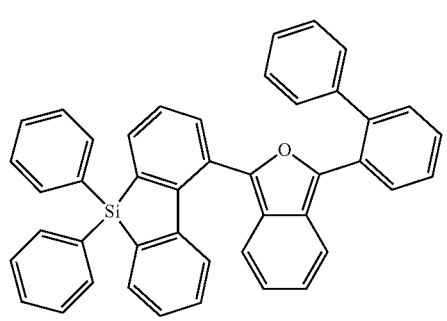
137
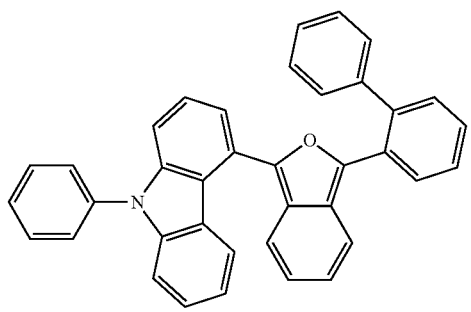
138
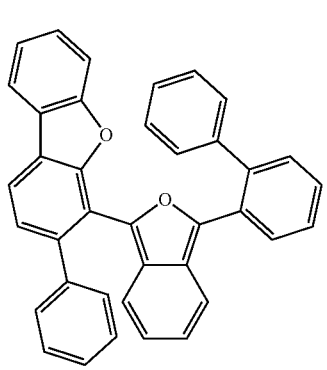
139
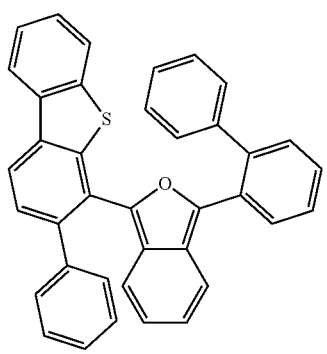
140
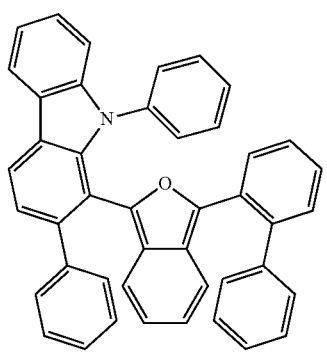

1135 -continued
141
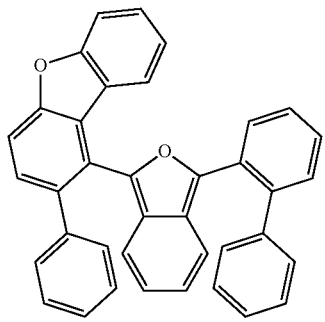
142
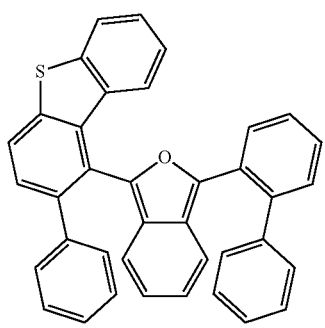
143
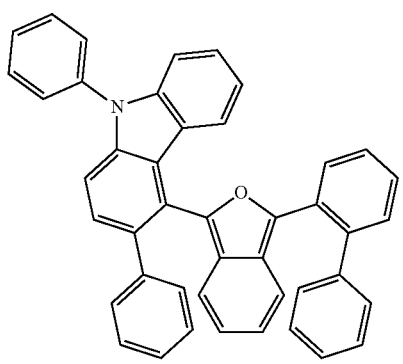
144
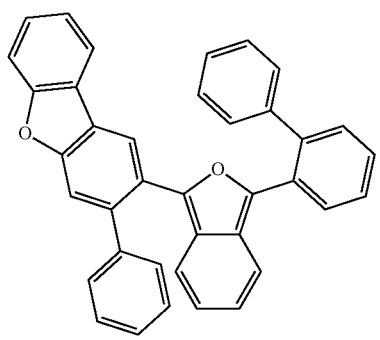
1136 -continued
145
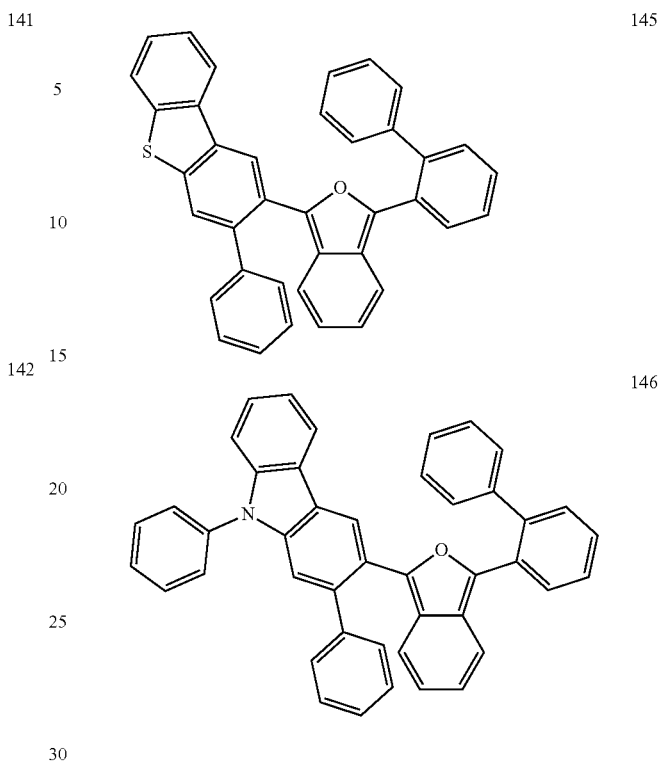
146
147
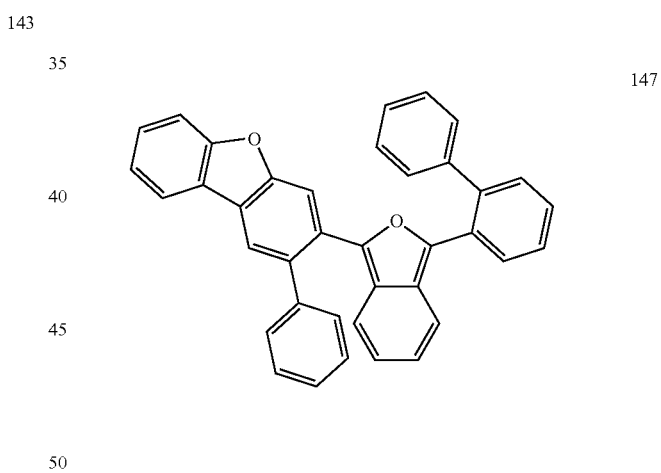
148
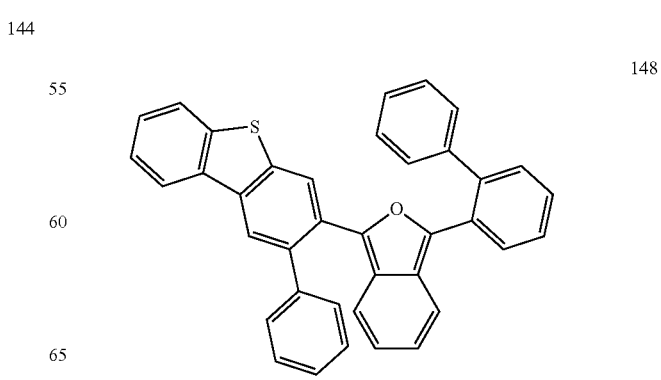

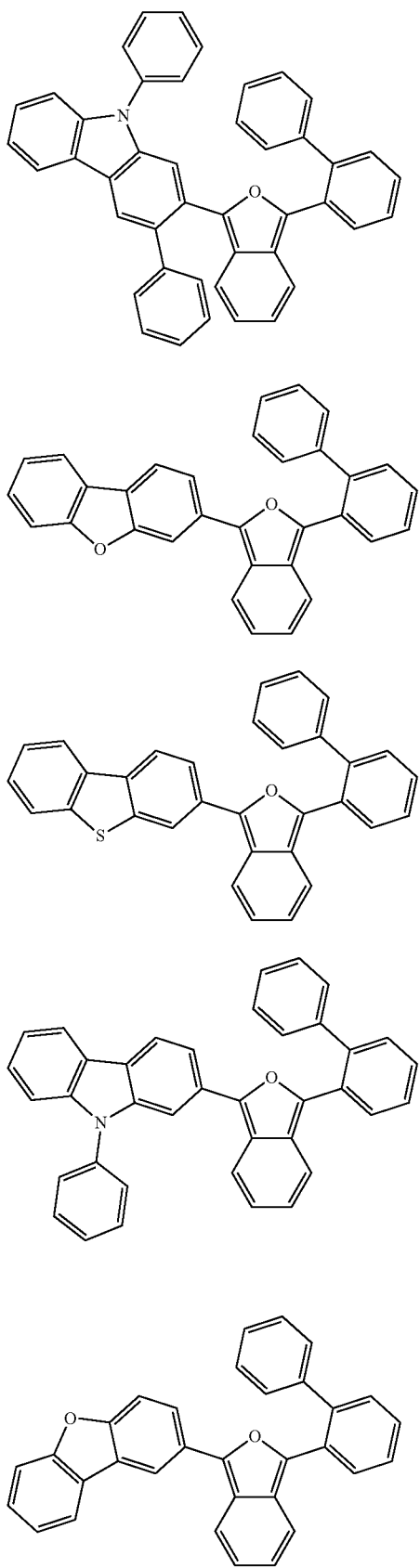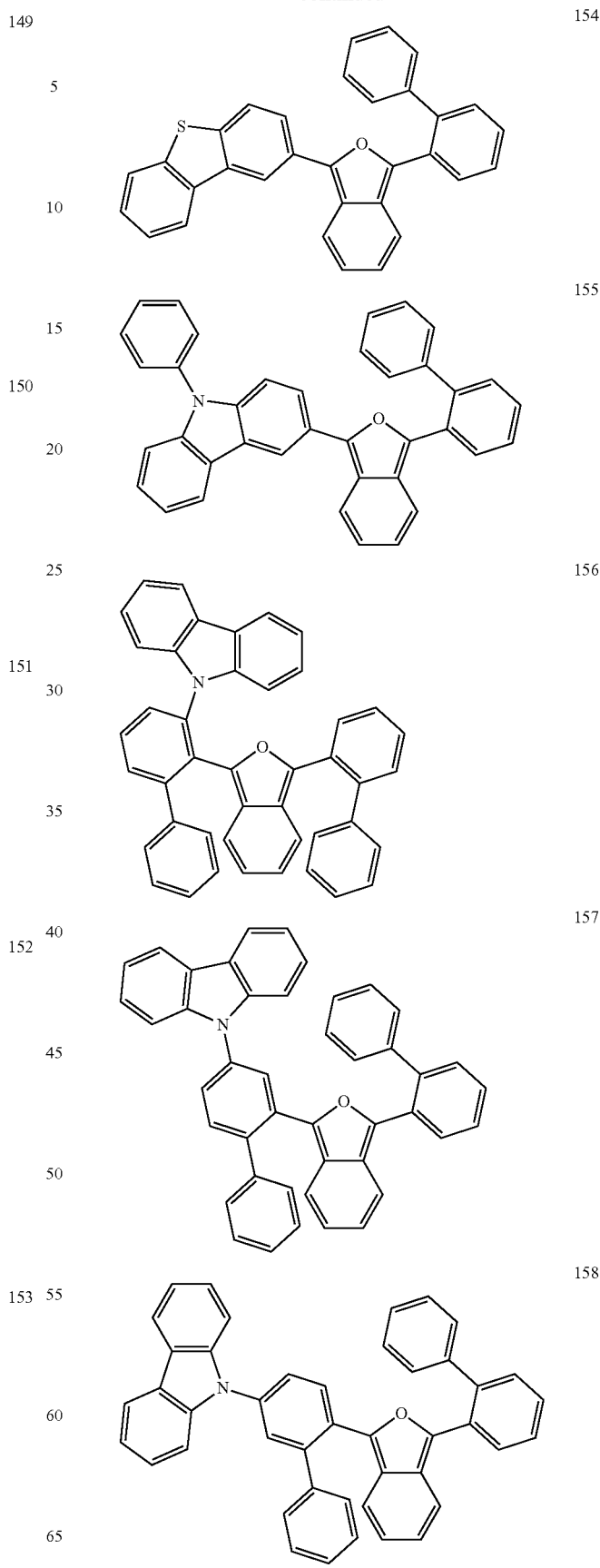

159
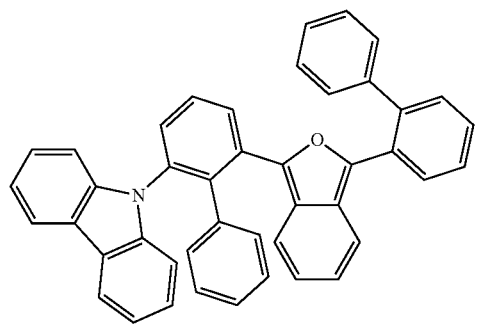
160
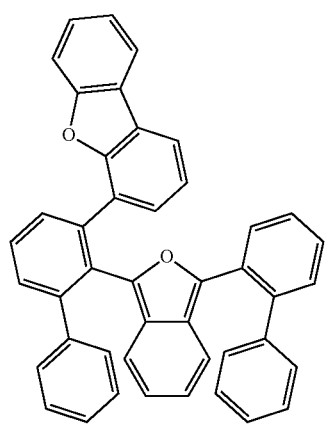
161
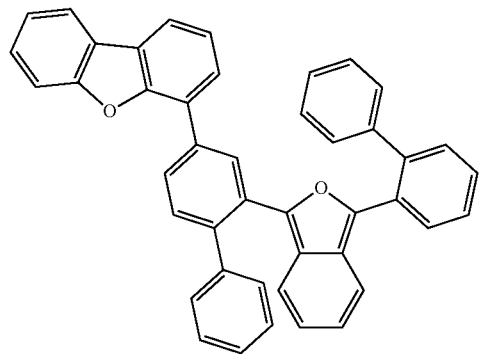
162
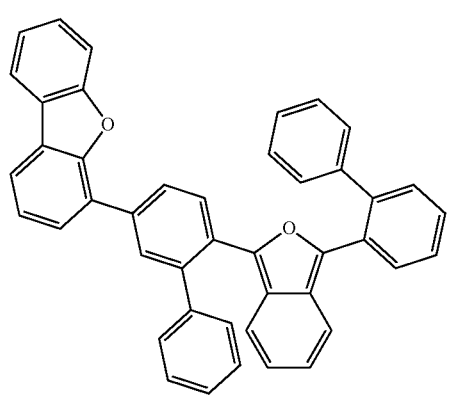
163
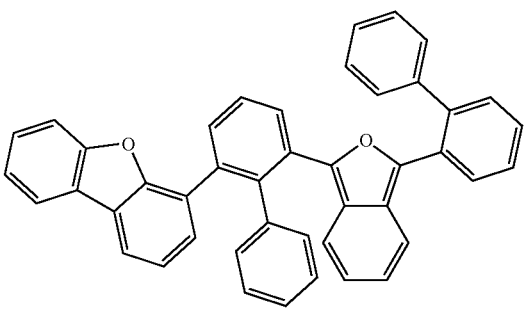
164
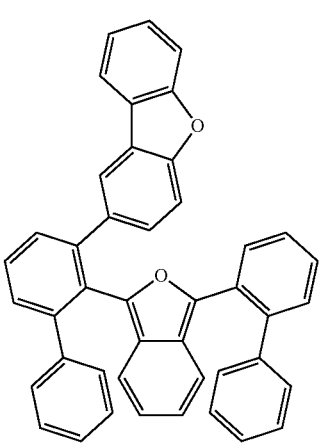
165
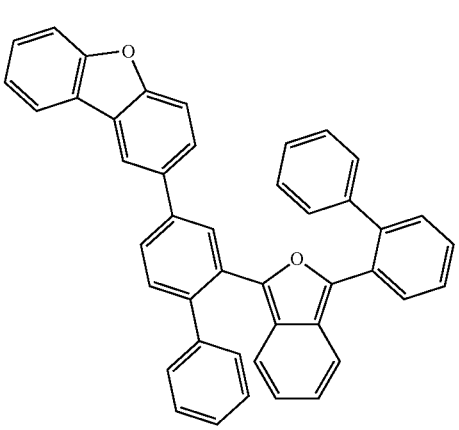
166
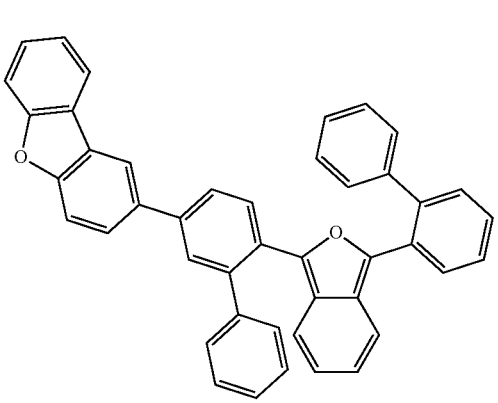

167
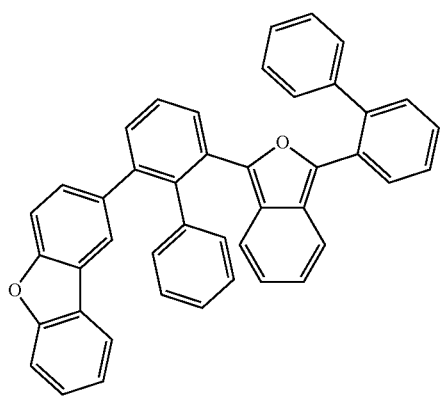
168
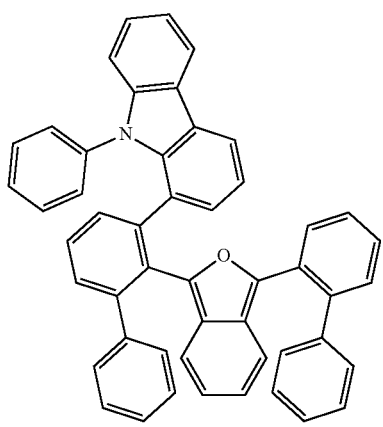
169
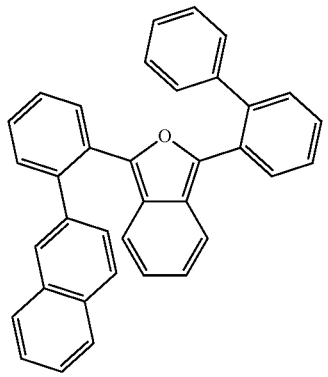
170
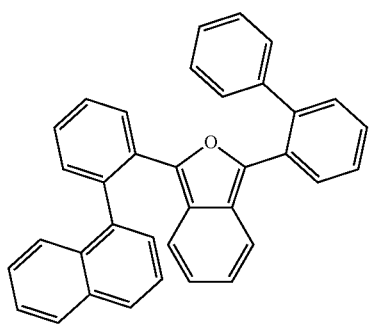
171
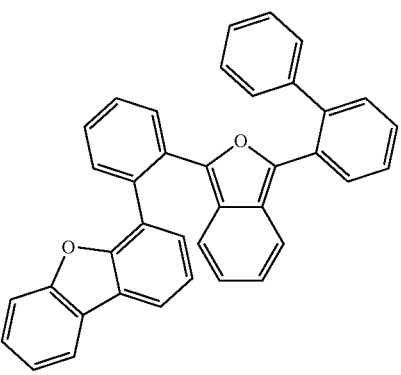
172
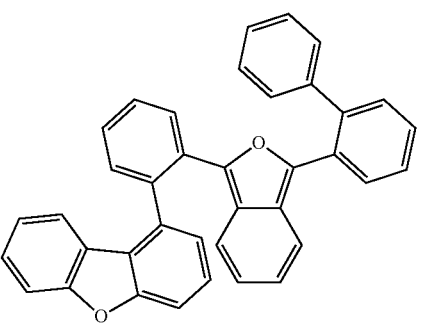
173
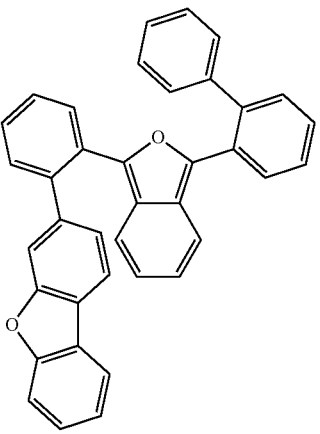
174
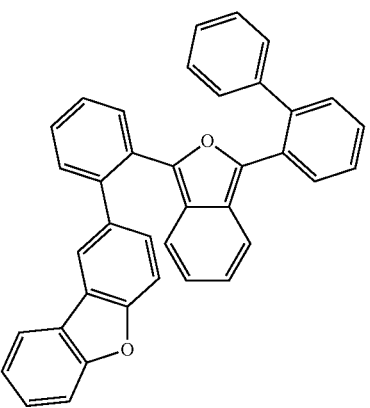

175
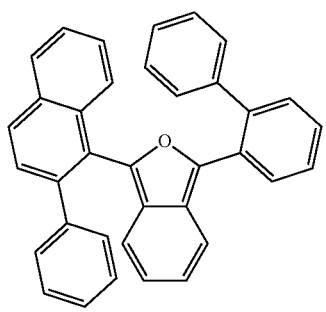
176
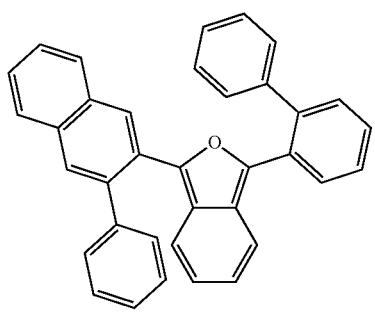
177
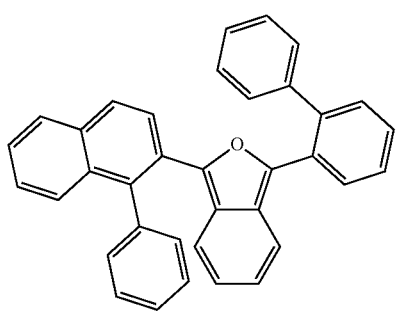
178
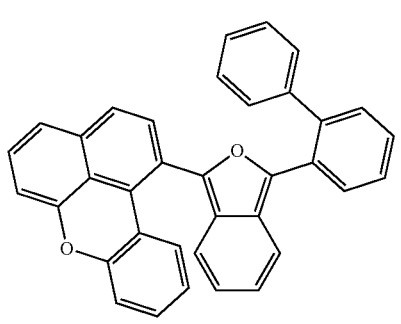
179
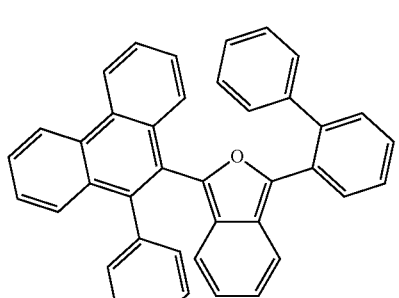
180
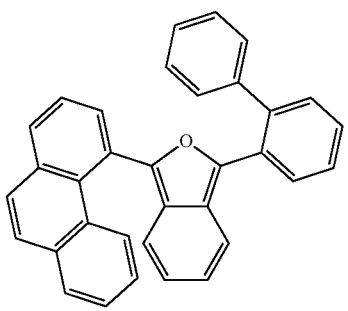
181
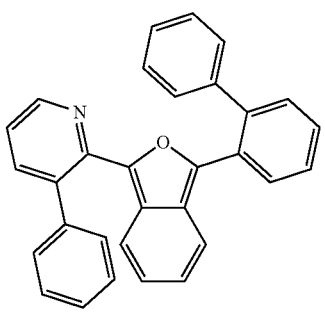
182
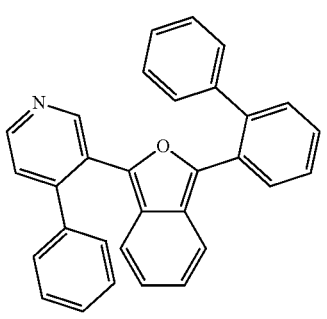
183
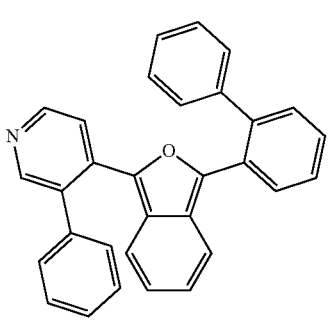
184
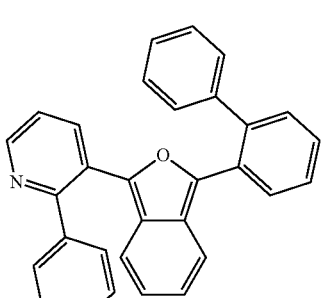

185
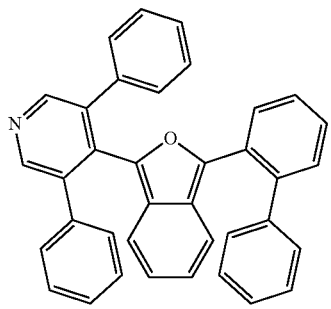
186
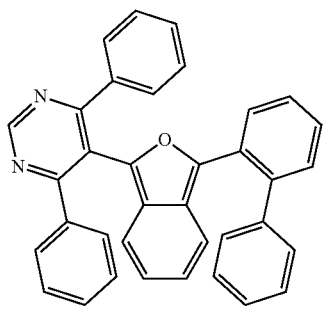
187
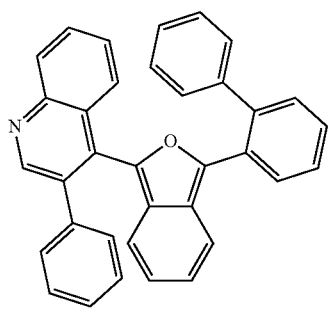
188
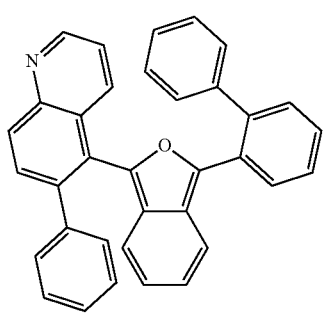
189
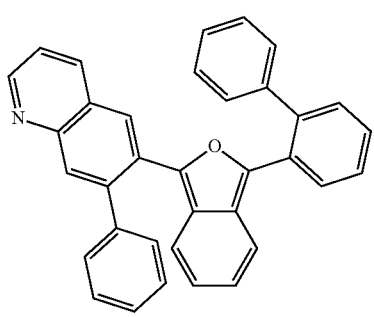
190
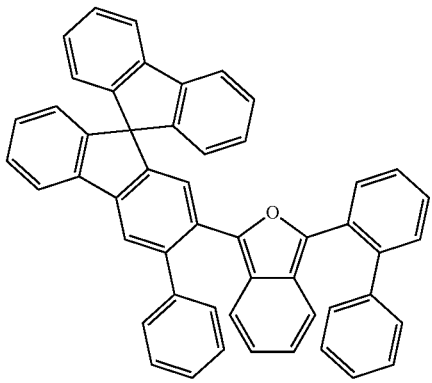
191
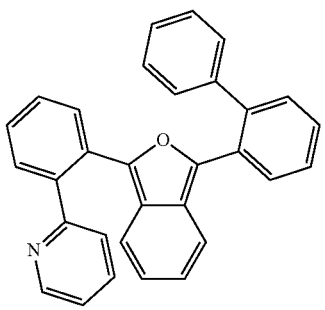
192
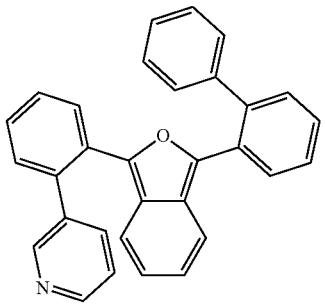
193
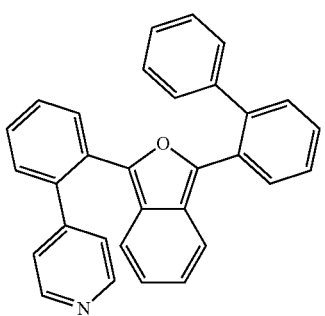

194
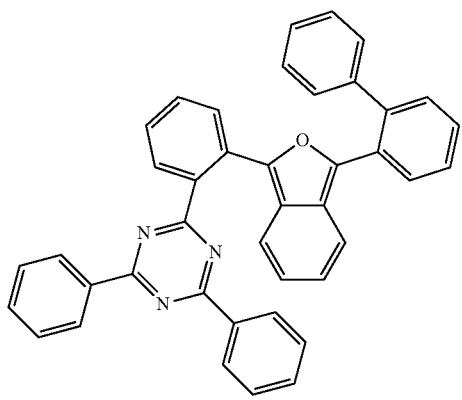
195
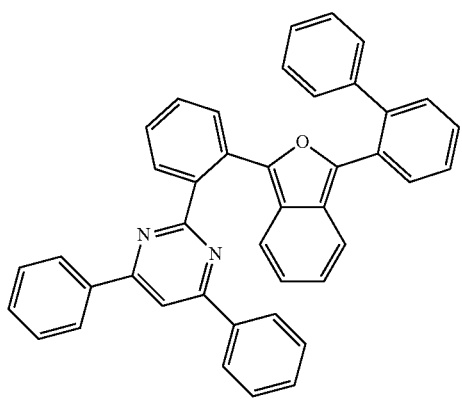
196
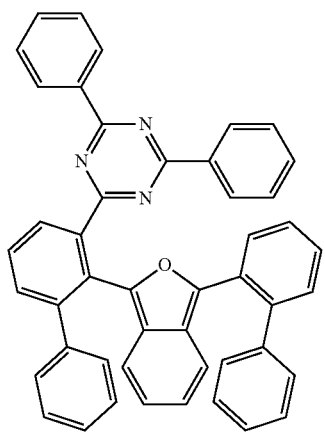
197
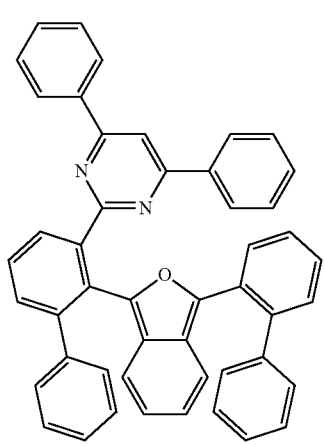
198
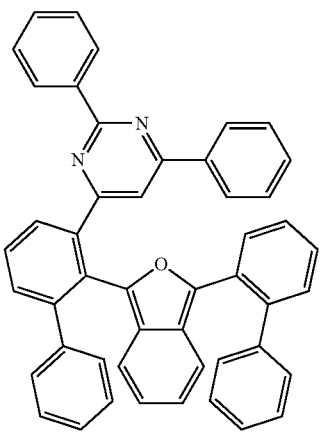
199
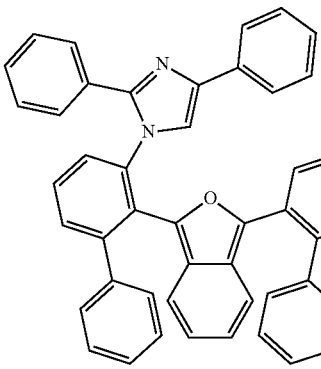
200
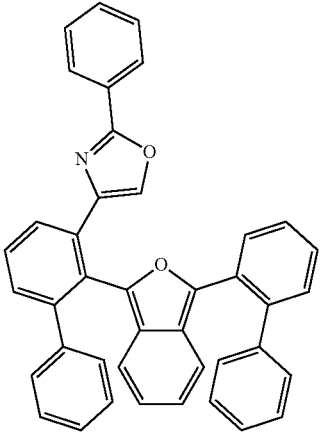
201
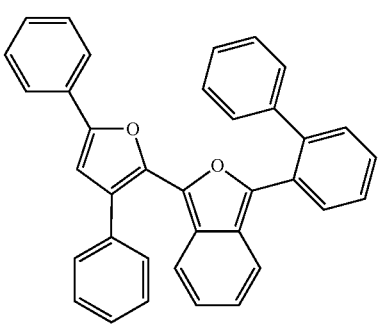

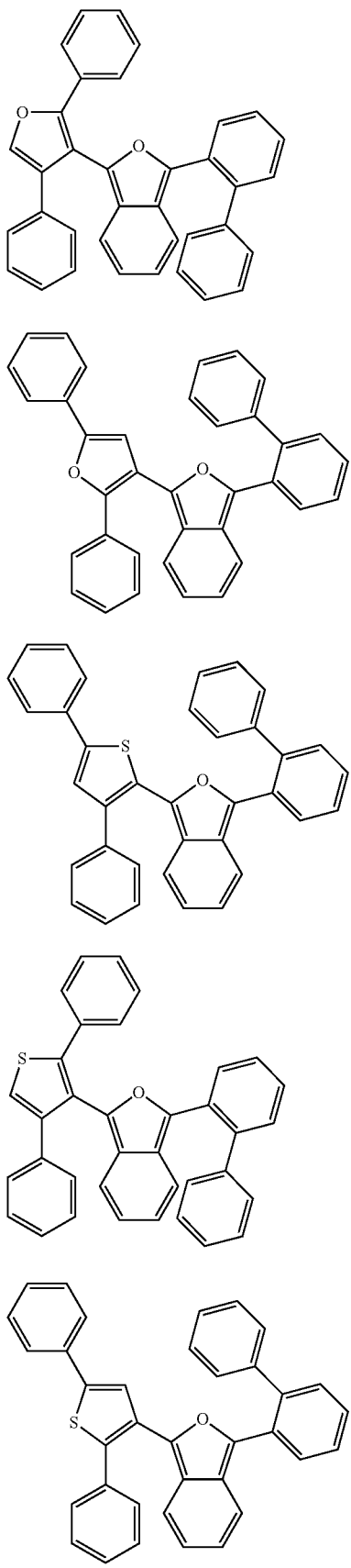
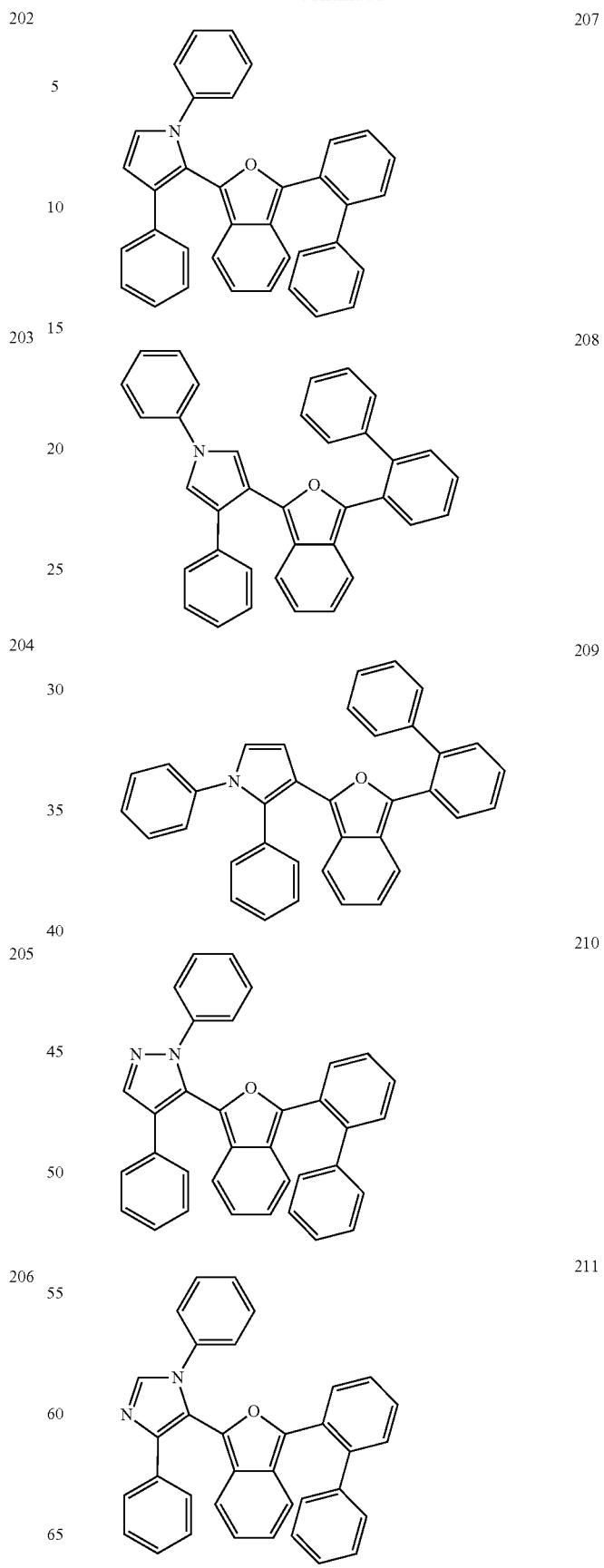

212
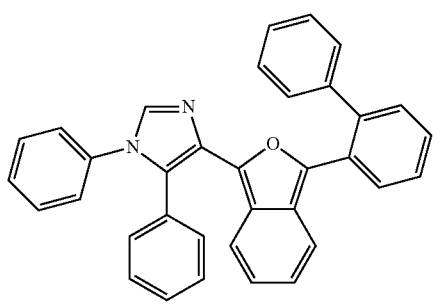
213
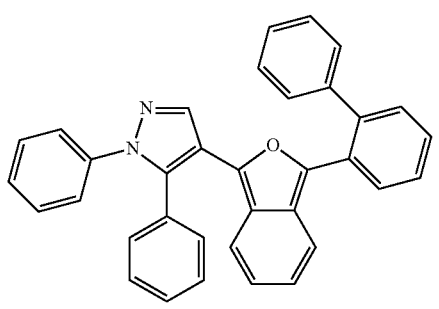
214
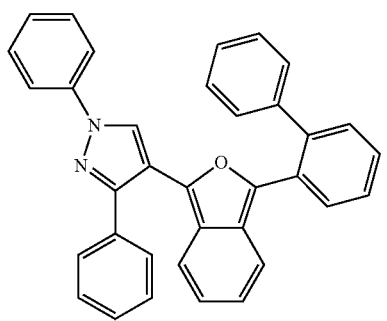
215
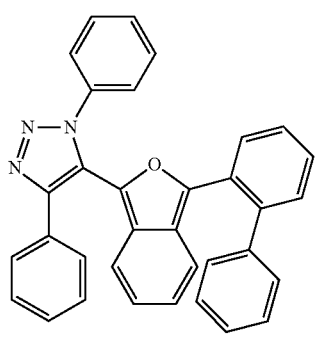
216
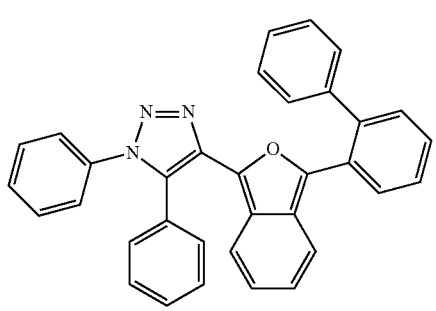
217
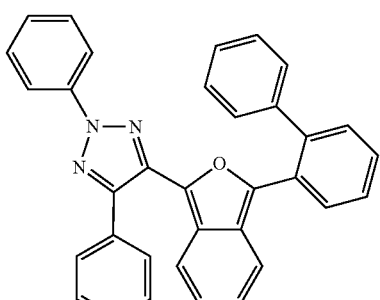
218
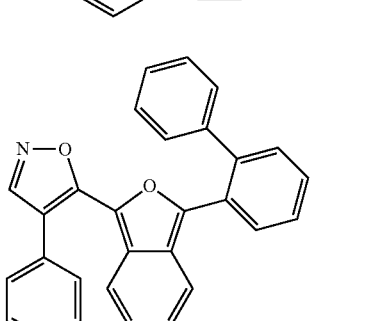
219
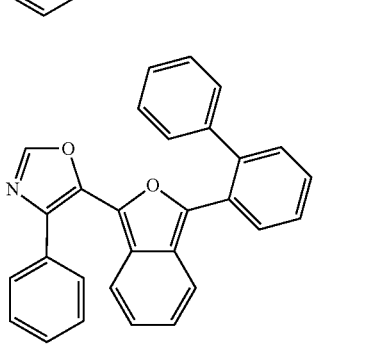
220
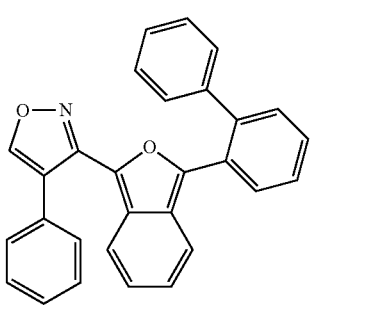
221
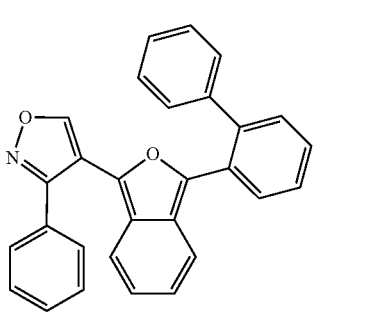

222
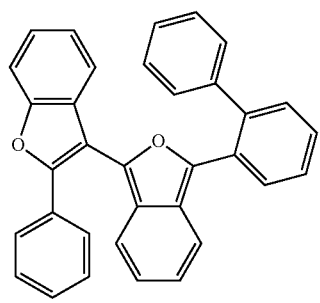
223
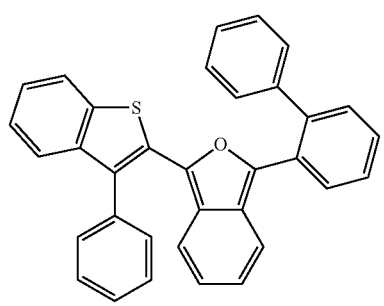
224
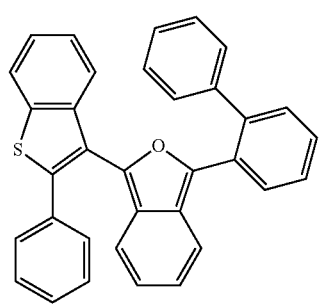
225
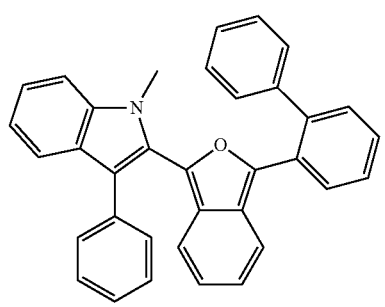
226
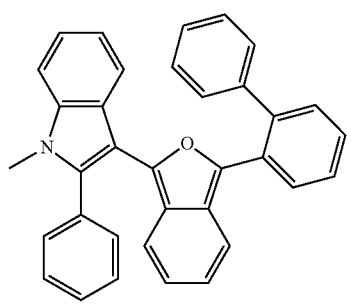
227

228

229

230
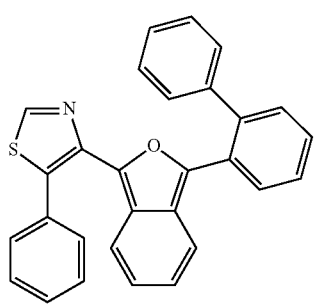
231
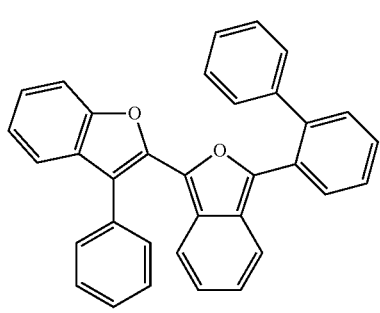

1155
-continued
232
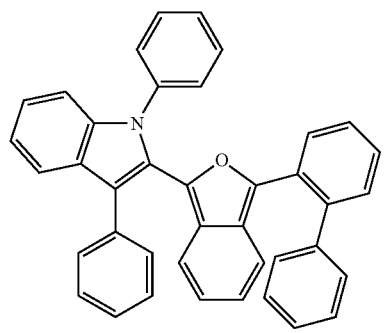
233
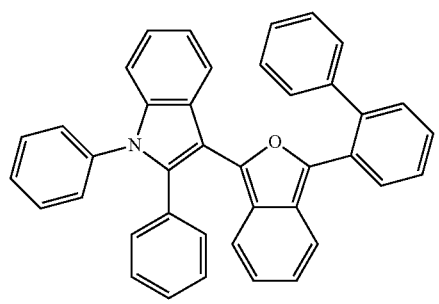
234
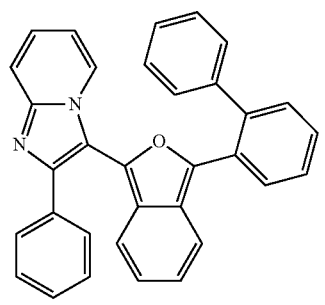
235
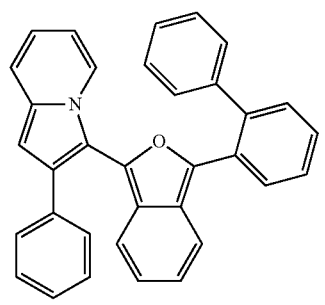
236
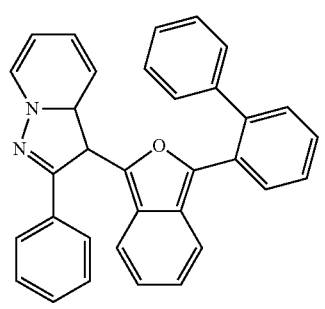
1156
-continued
237
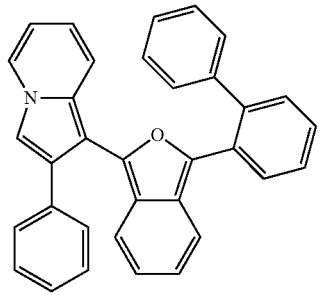
238
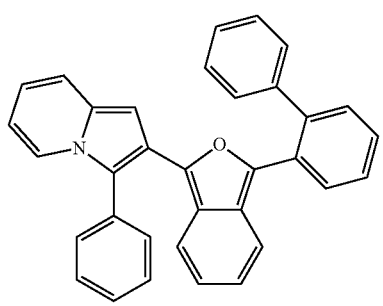
239
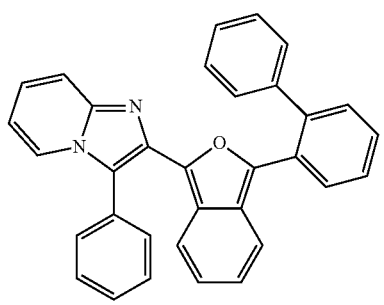
240
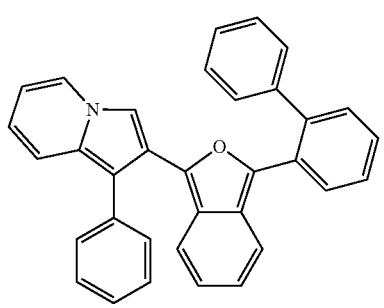
241
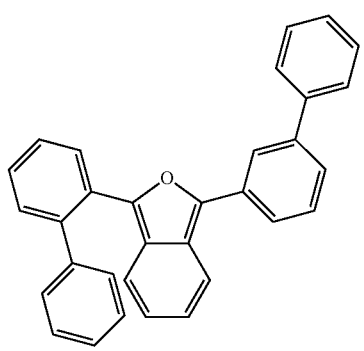

242
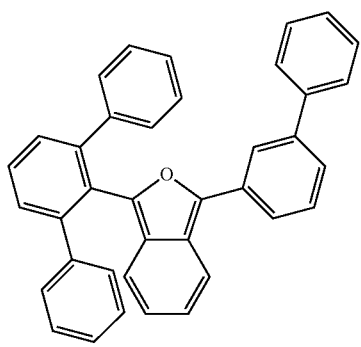
243
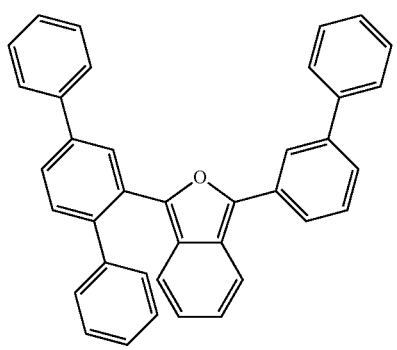
244
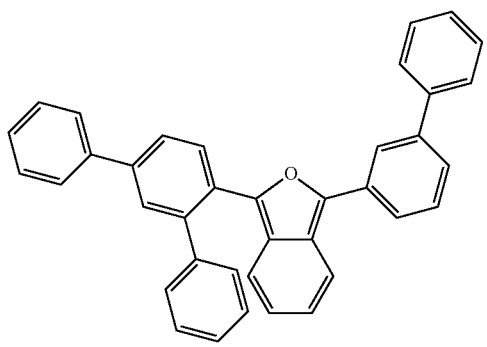
245
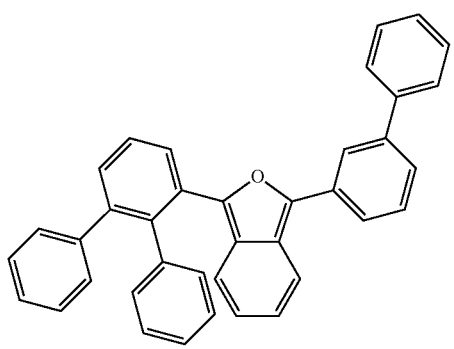
246
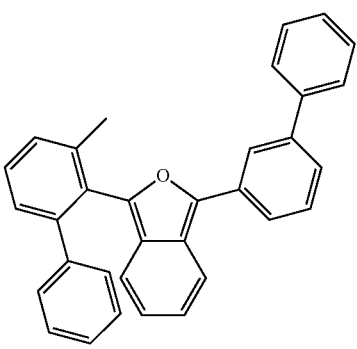
247
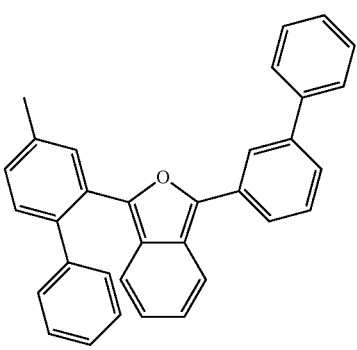
248
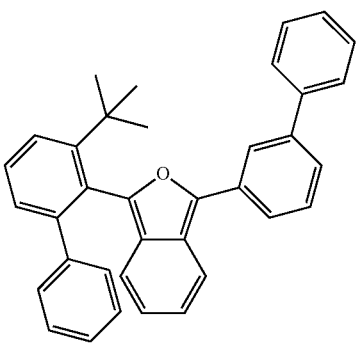
249
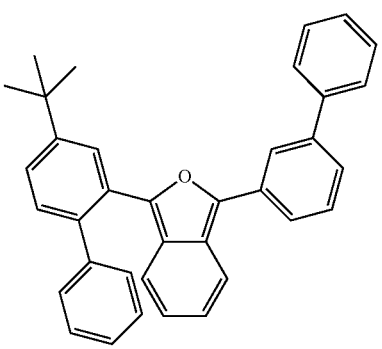

250
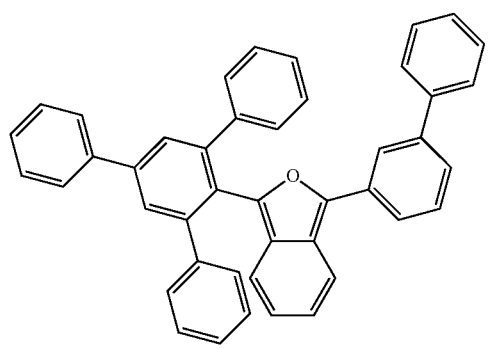
251
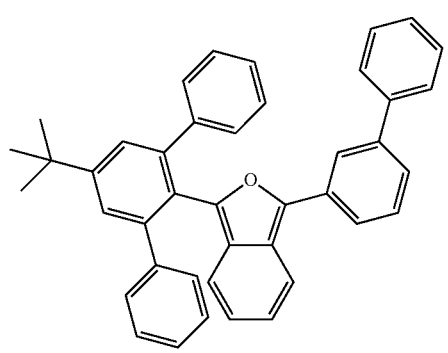
252
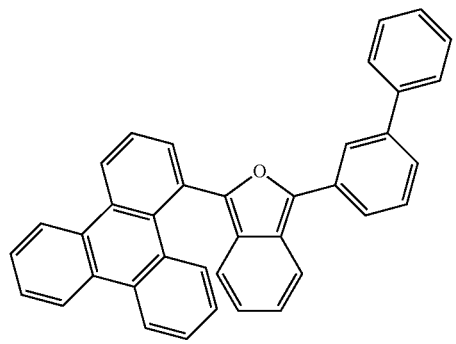
253
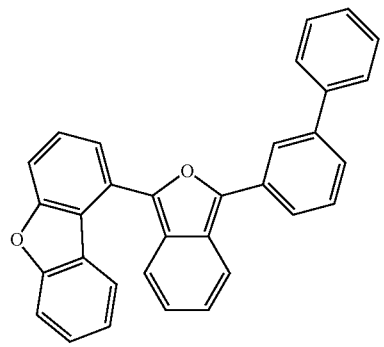
254
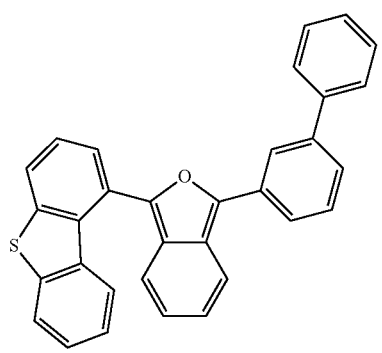
255
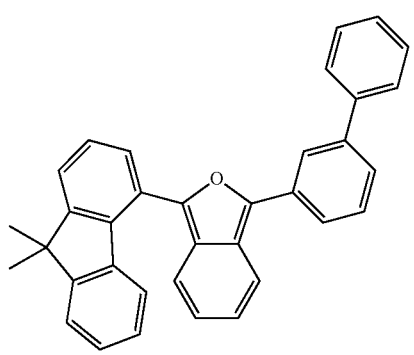
256
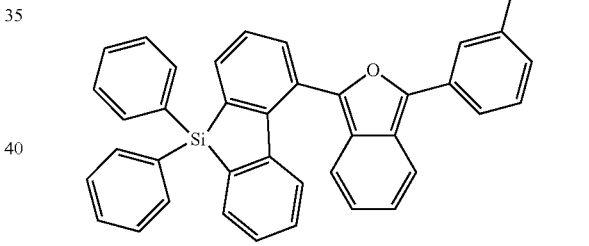
257
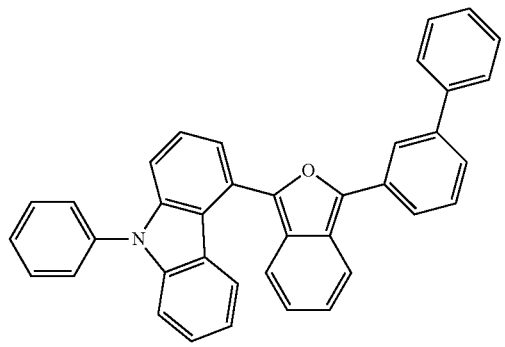

258
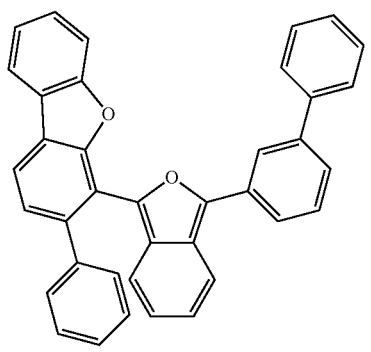
259
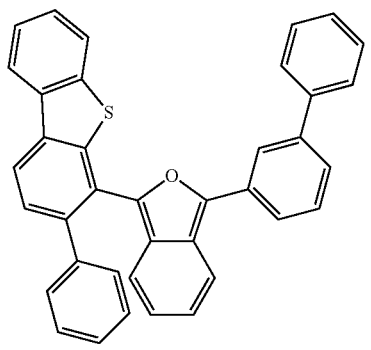
260
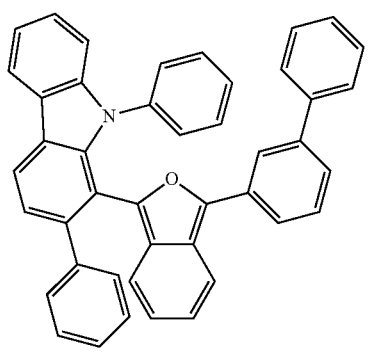
261
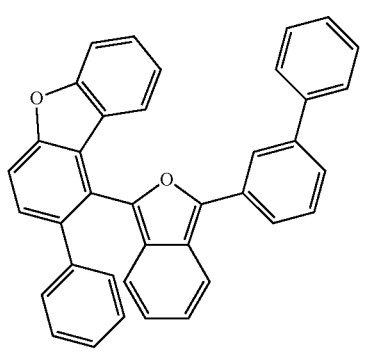
262
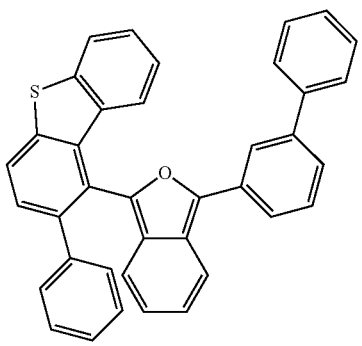
263
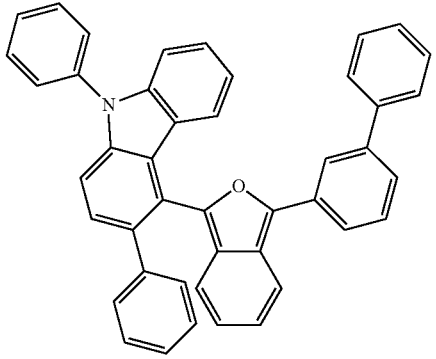
264
265

-continued
266
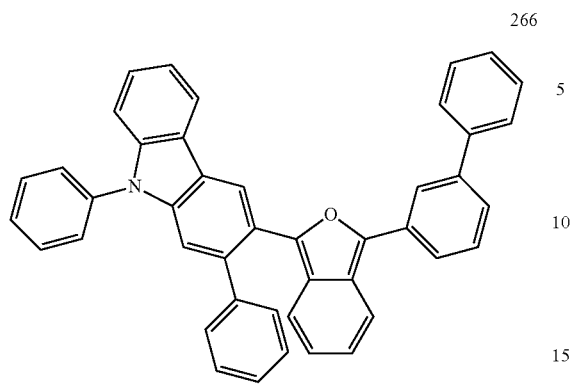
267
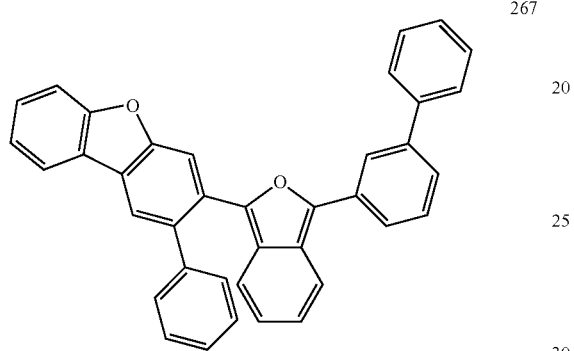
268
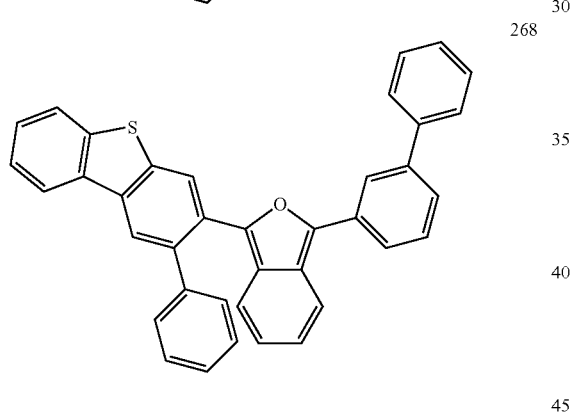
269
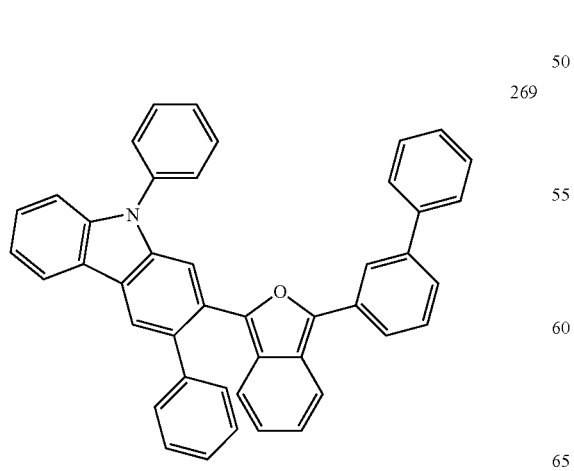
-continued
270
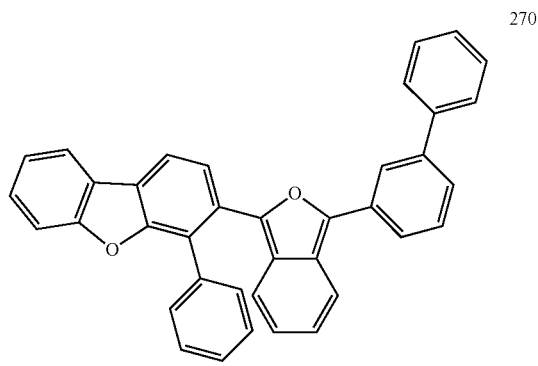
271
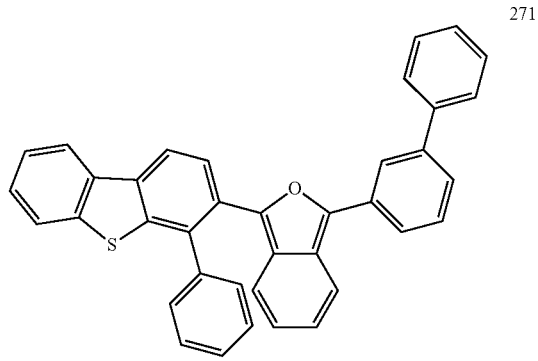
272
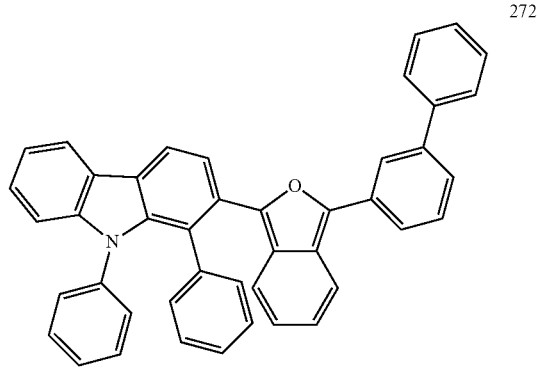
273
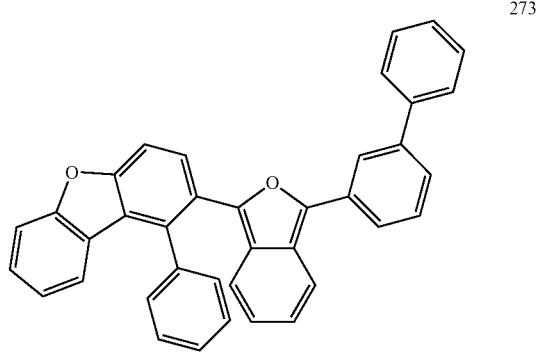

274
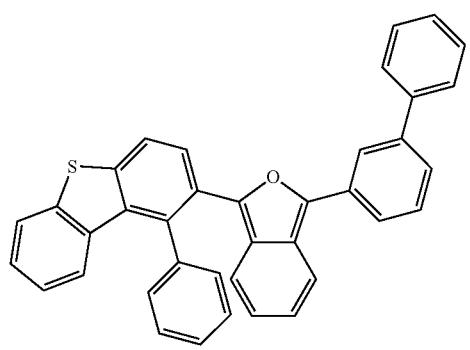
275
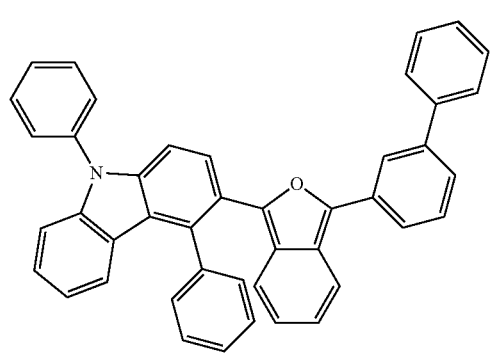
276
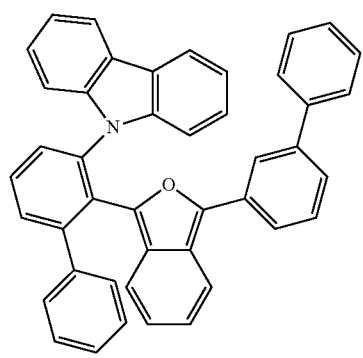
277
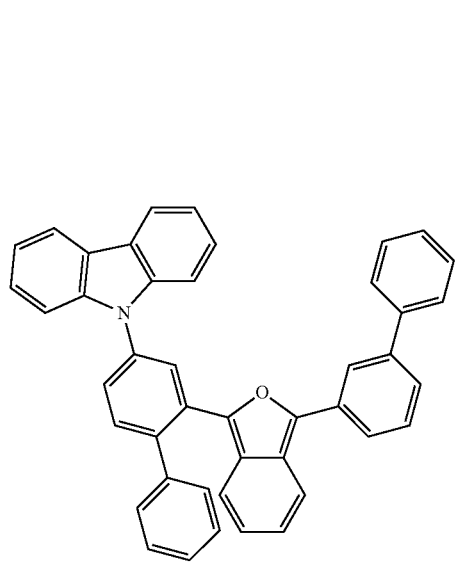
278
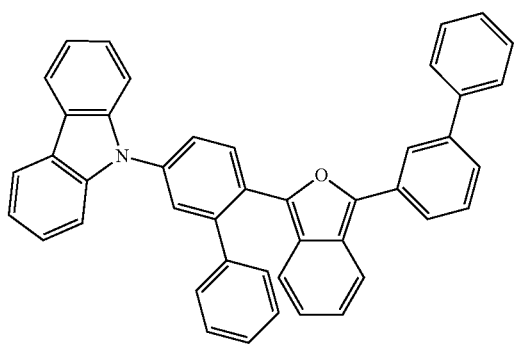
279
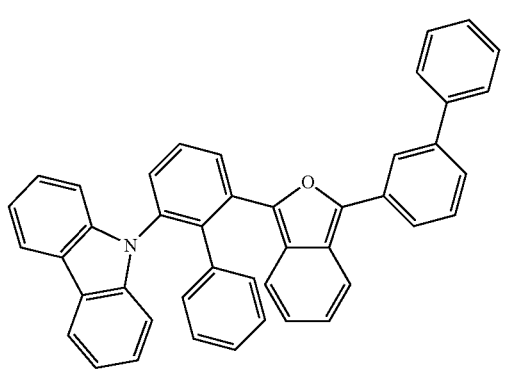
280
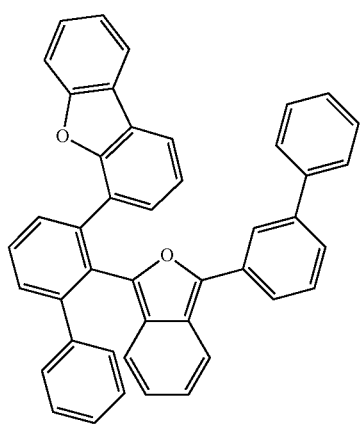
281
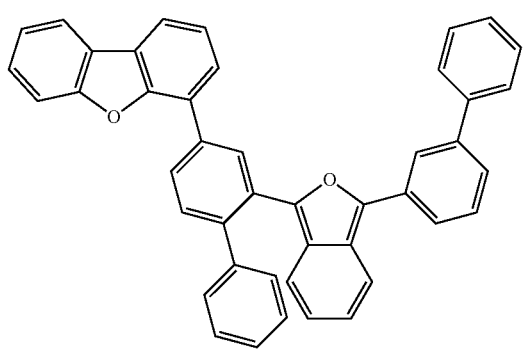

-continued
282
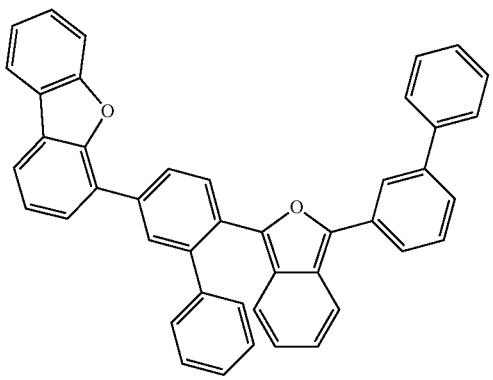
283
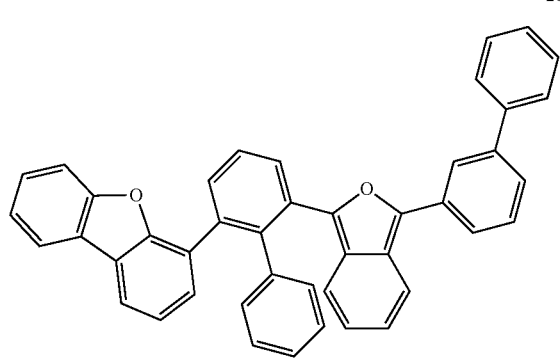
284
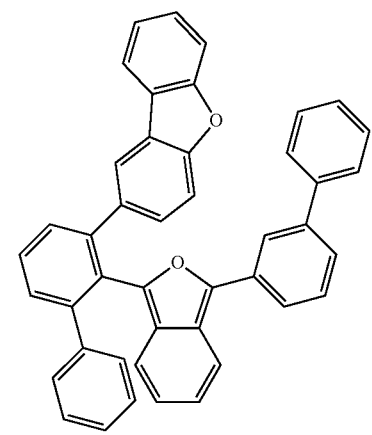
285
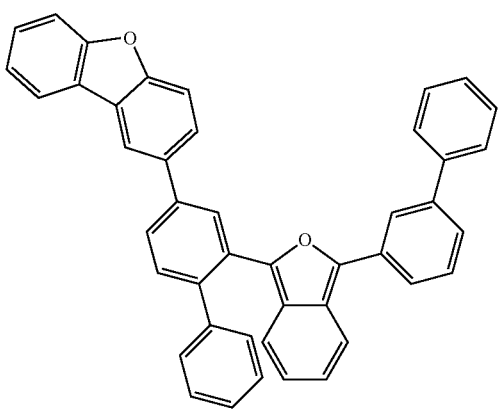
-continued
286
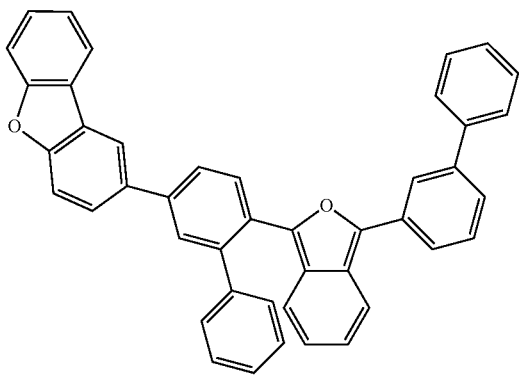
287
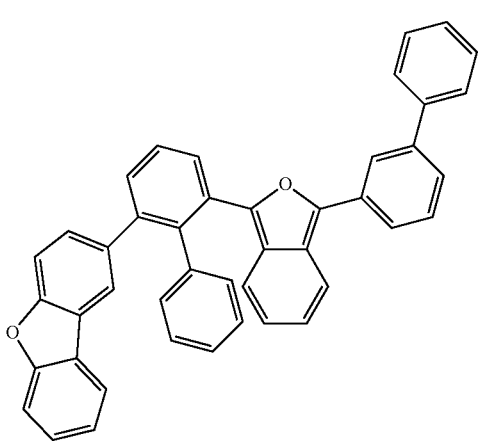
288
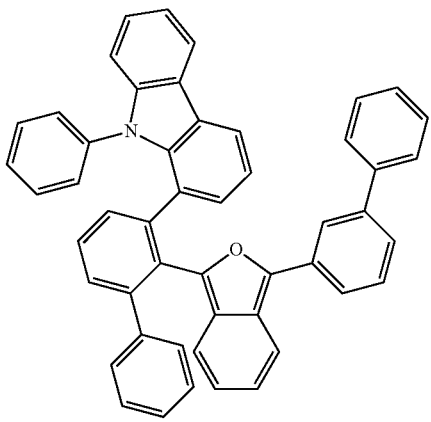
289
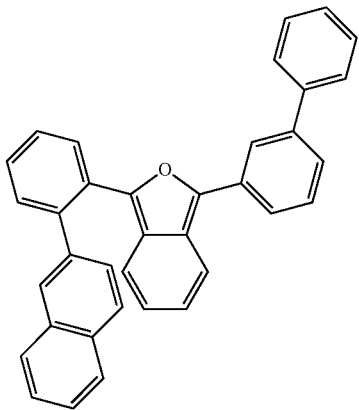

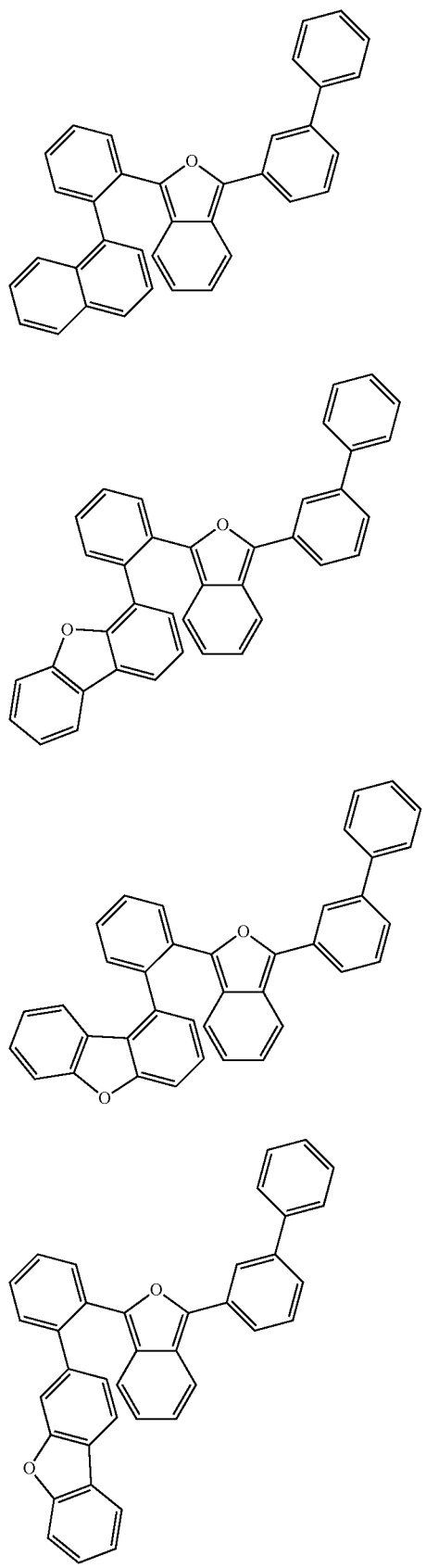
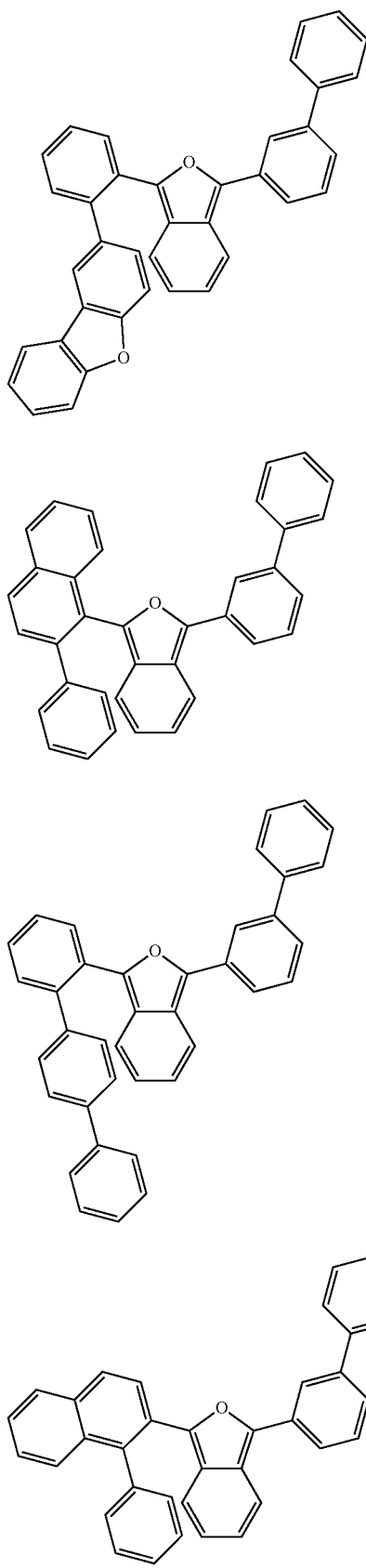

298
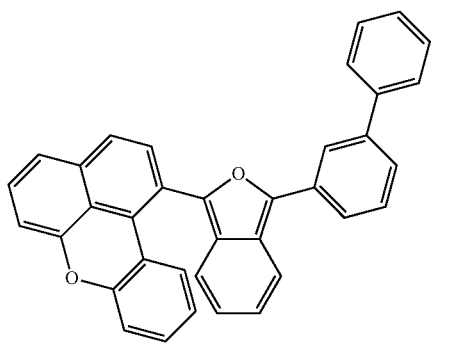
299
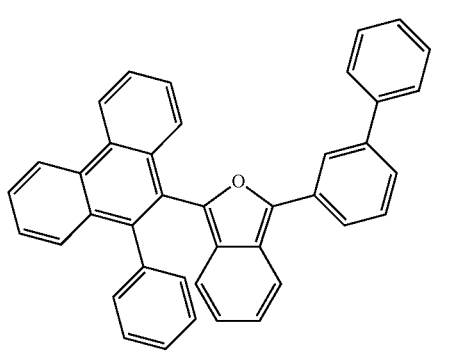
300
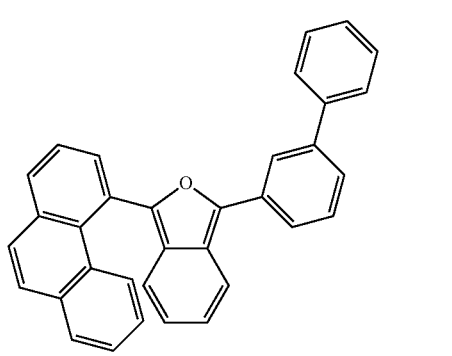
301
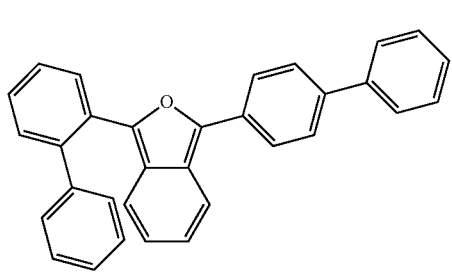
302
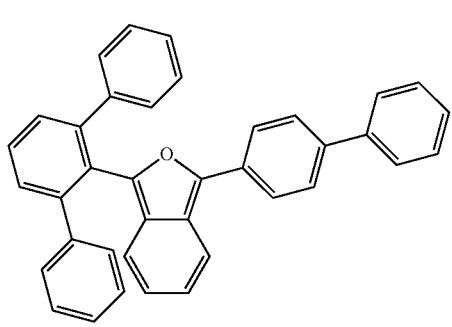
303
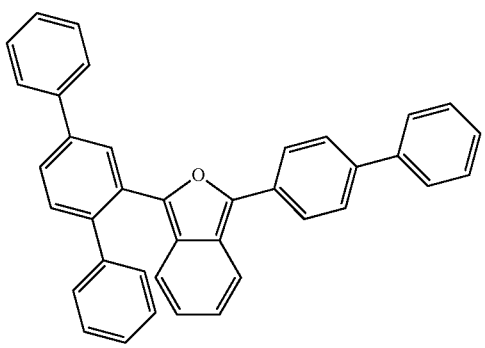
304
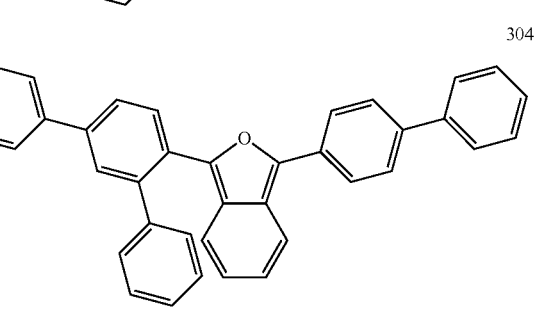
305
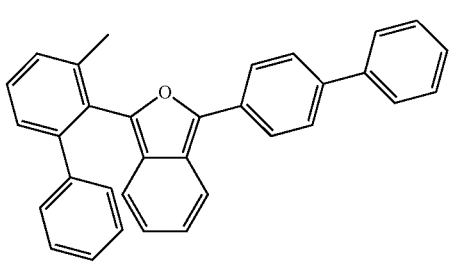
306
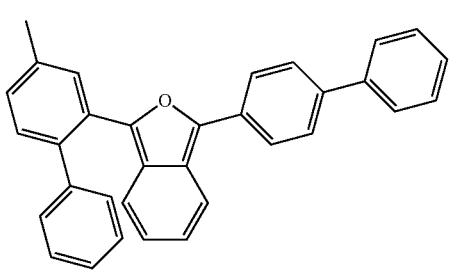
307

308
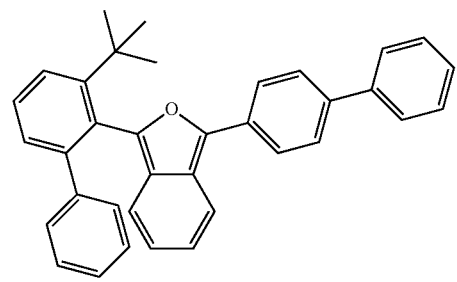
309
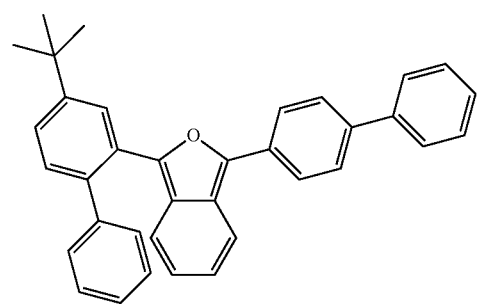
310
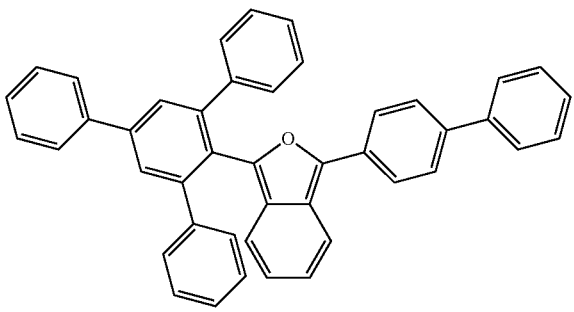
311
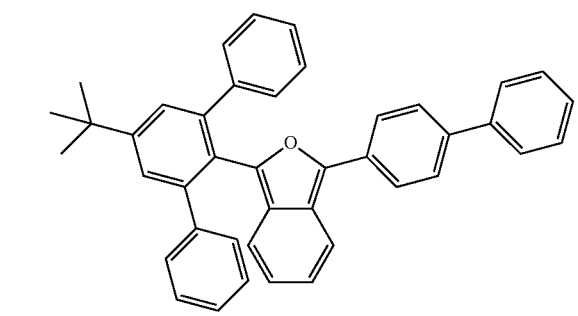
312
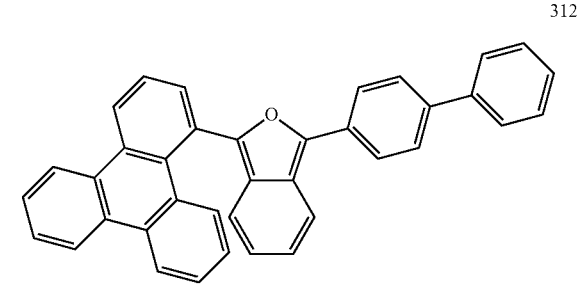
313
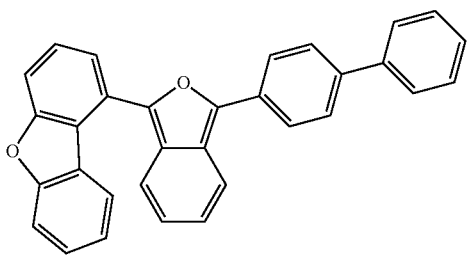
314
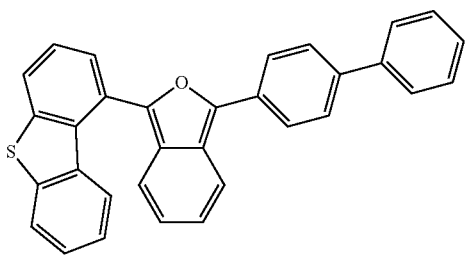
315
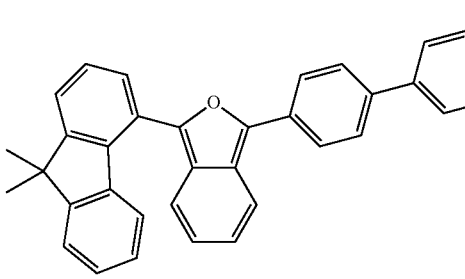
316
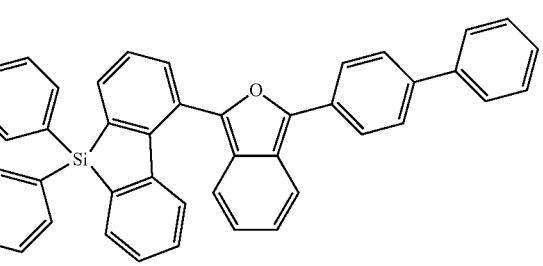
317
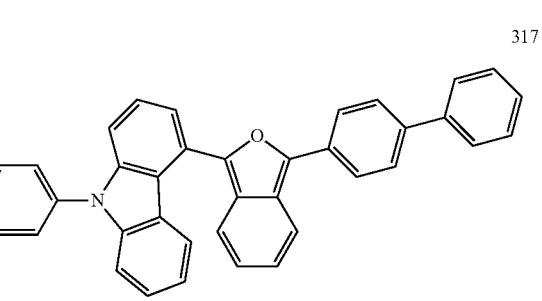

1175
-continued
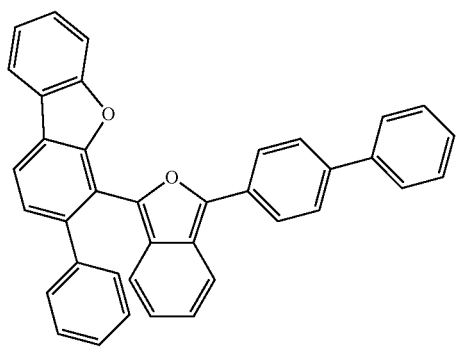
318
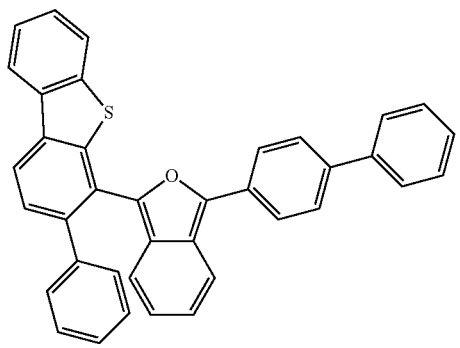
319
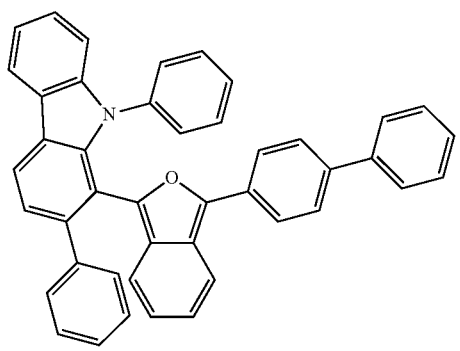
320
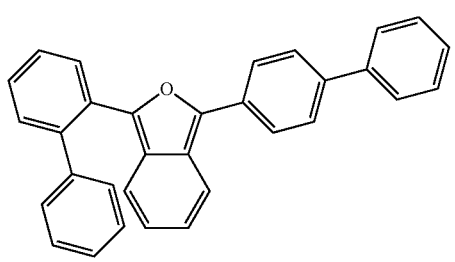
321
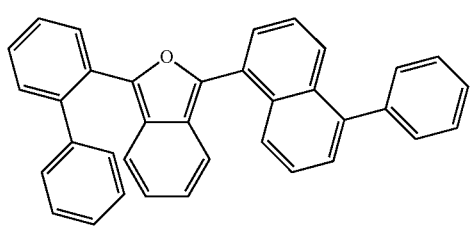
322
1176
-continued
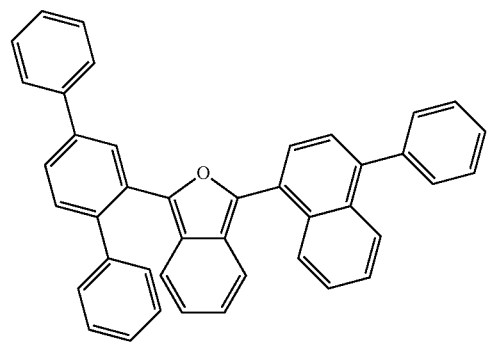
323
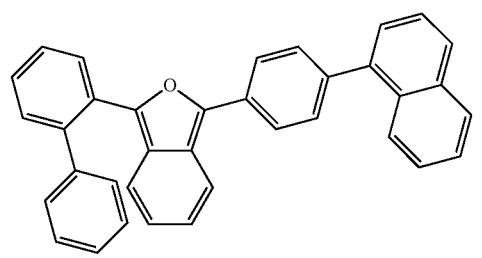
324
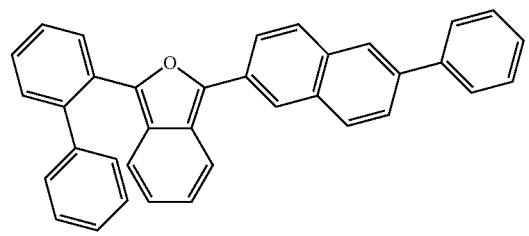
325
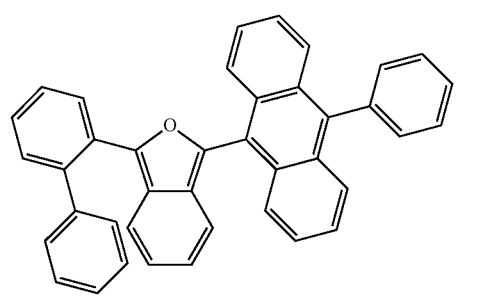
326
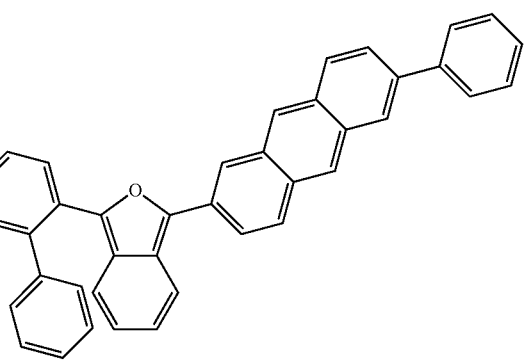
327

| 1177 -continued | 1178 -continued |
|---|---|
| 328 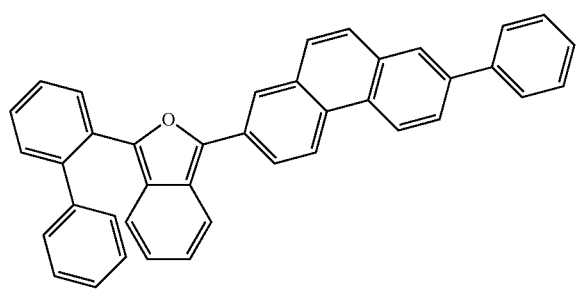 | 334 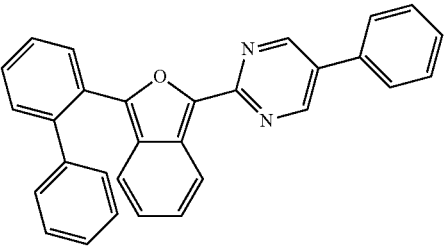 |
| 329 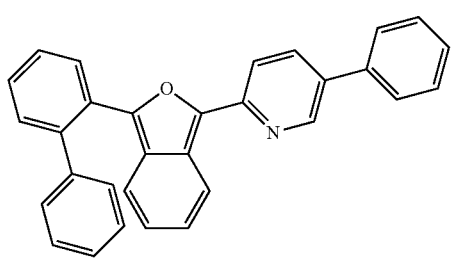 | 335 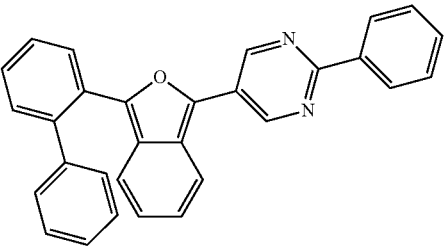 |
| 330 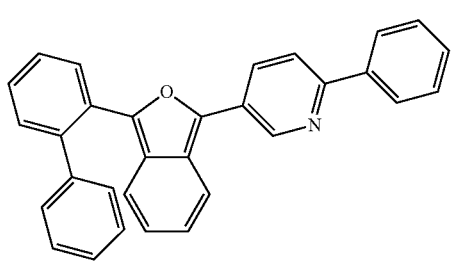 | 336 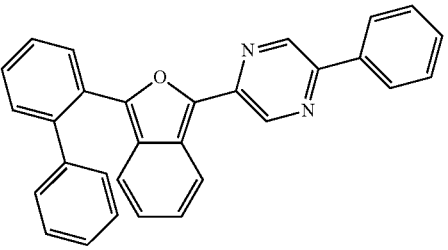 |
| 331 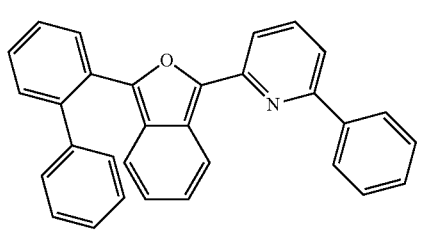 | 337 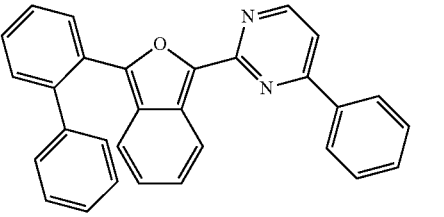 |
| 332 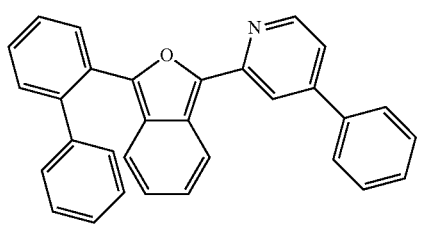 | 338 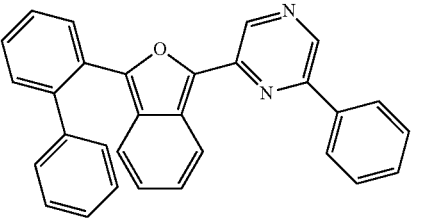 |
| 333 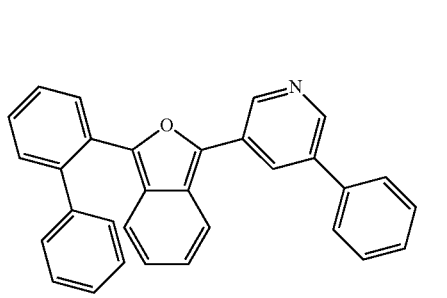 | 339 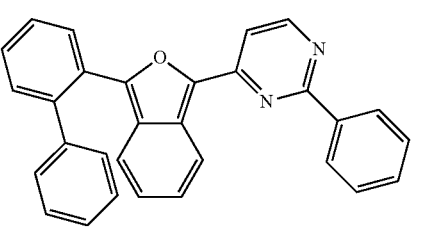 |

1179
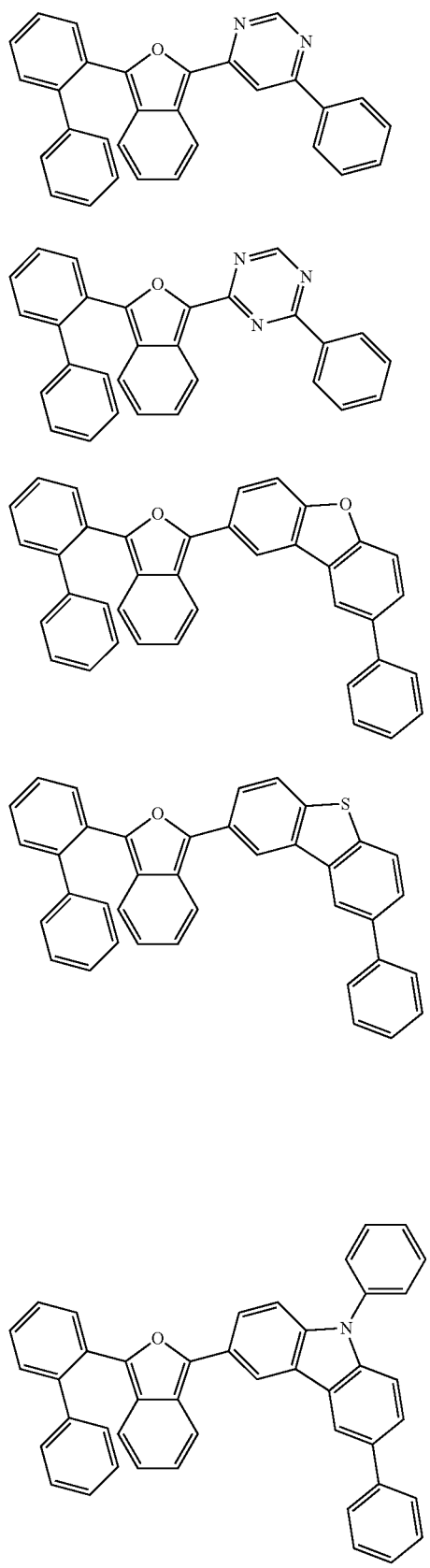
1180
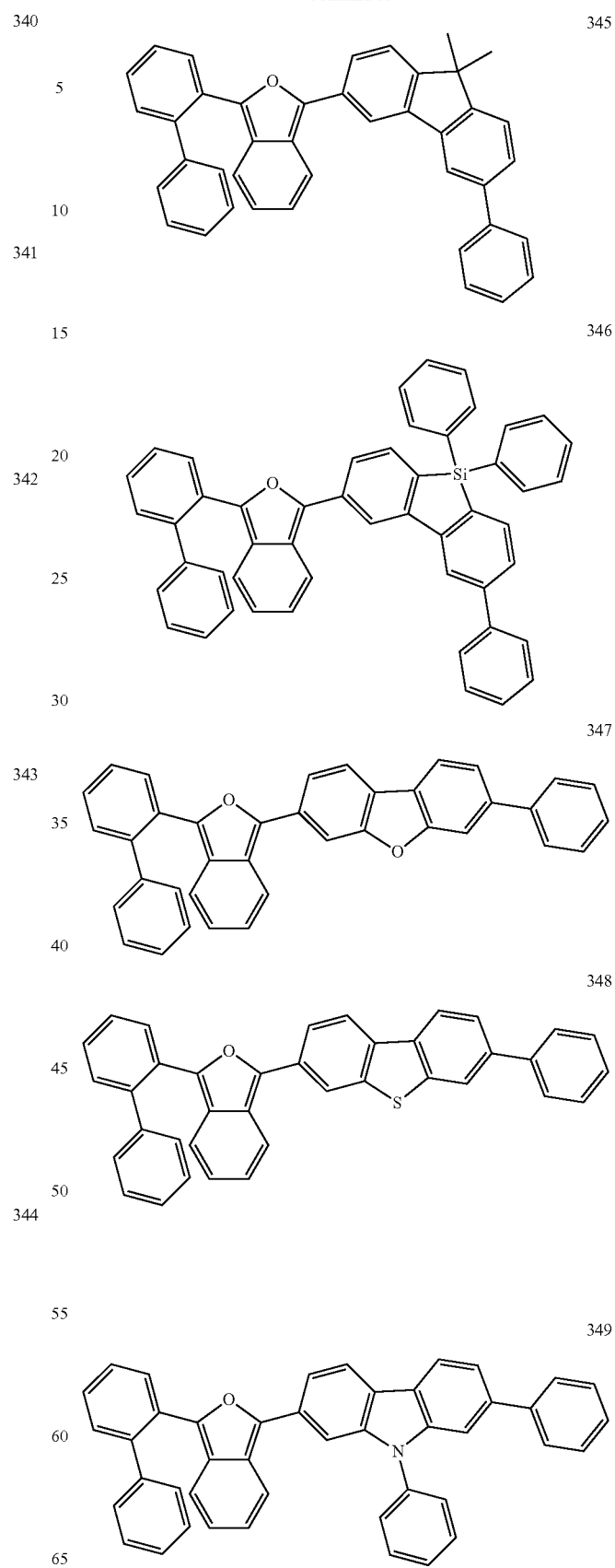

1181
-continued
350 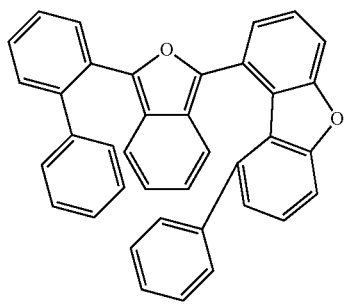
351 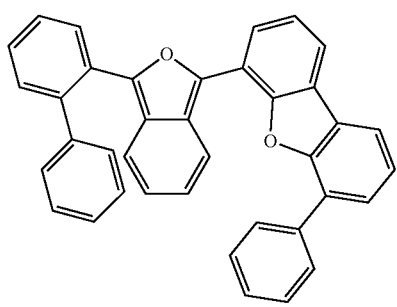
352 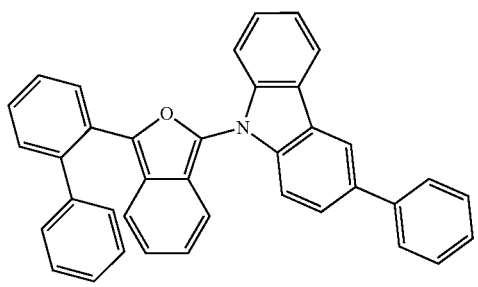
353 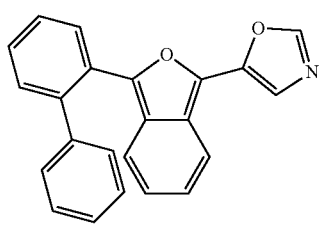
354 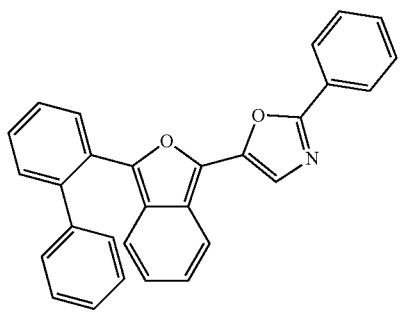
1182
-continued
355 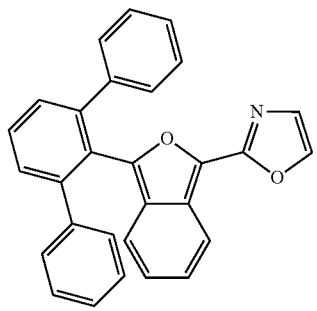
356 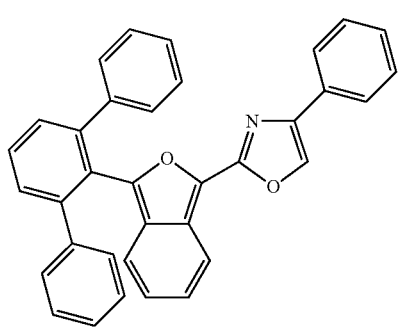
357 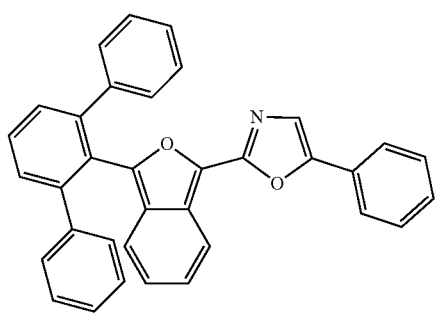
358 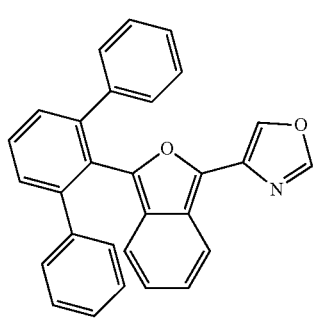
359 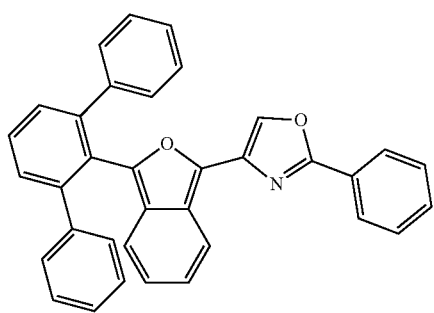

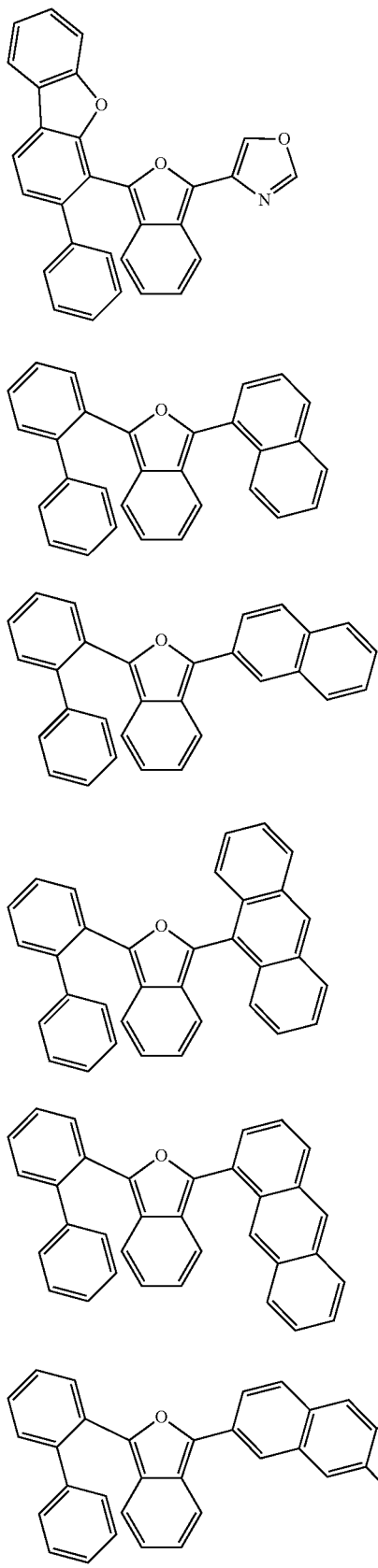
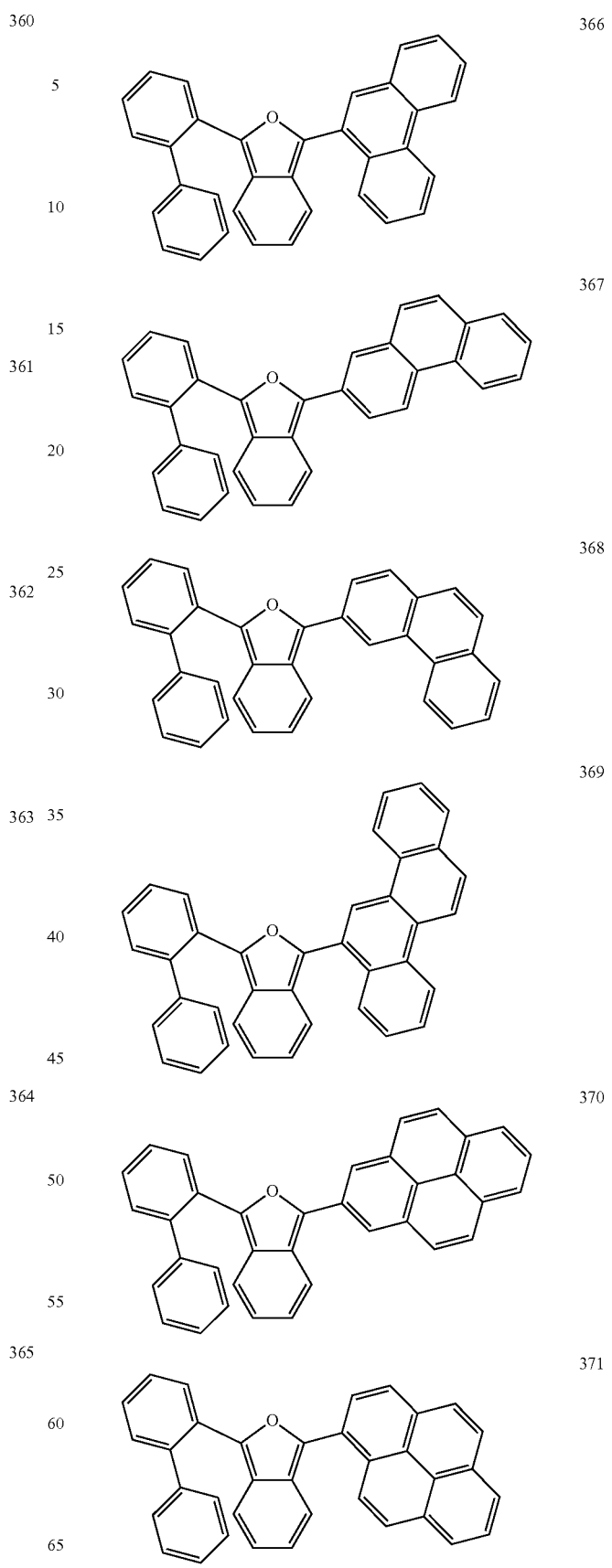

| 1185 -continued | | 1186 -continued | |
|---|---|---|---|
| 372 | 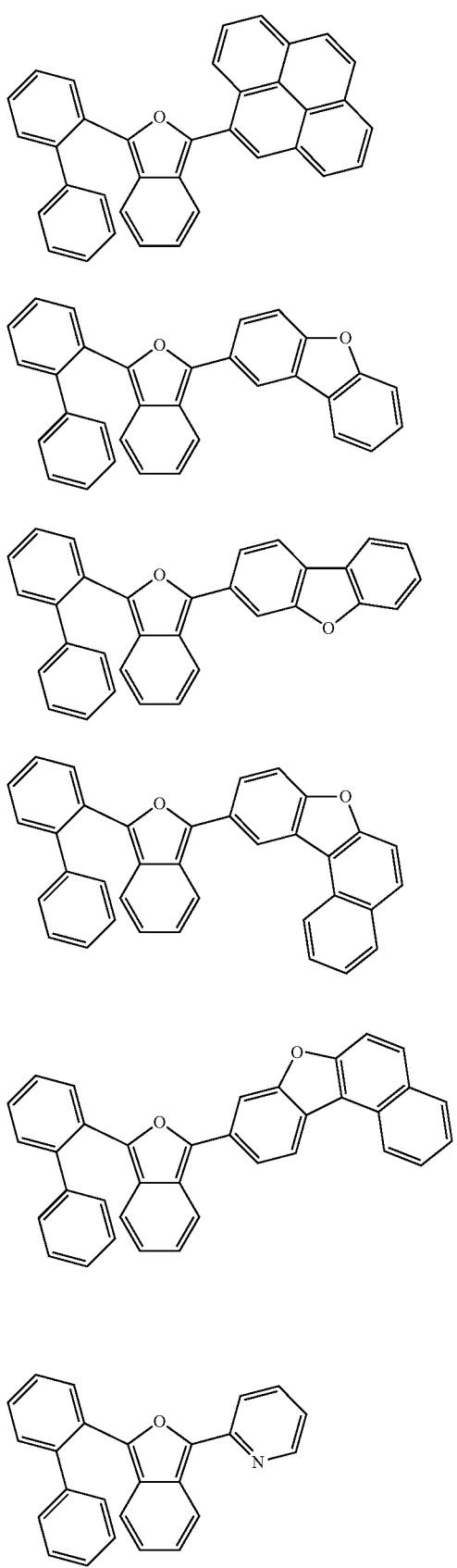 | 378 | 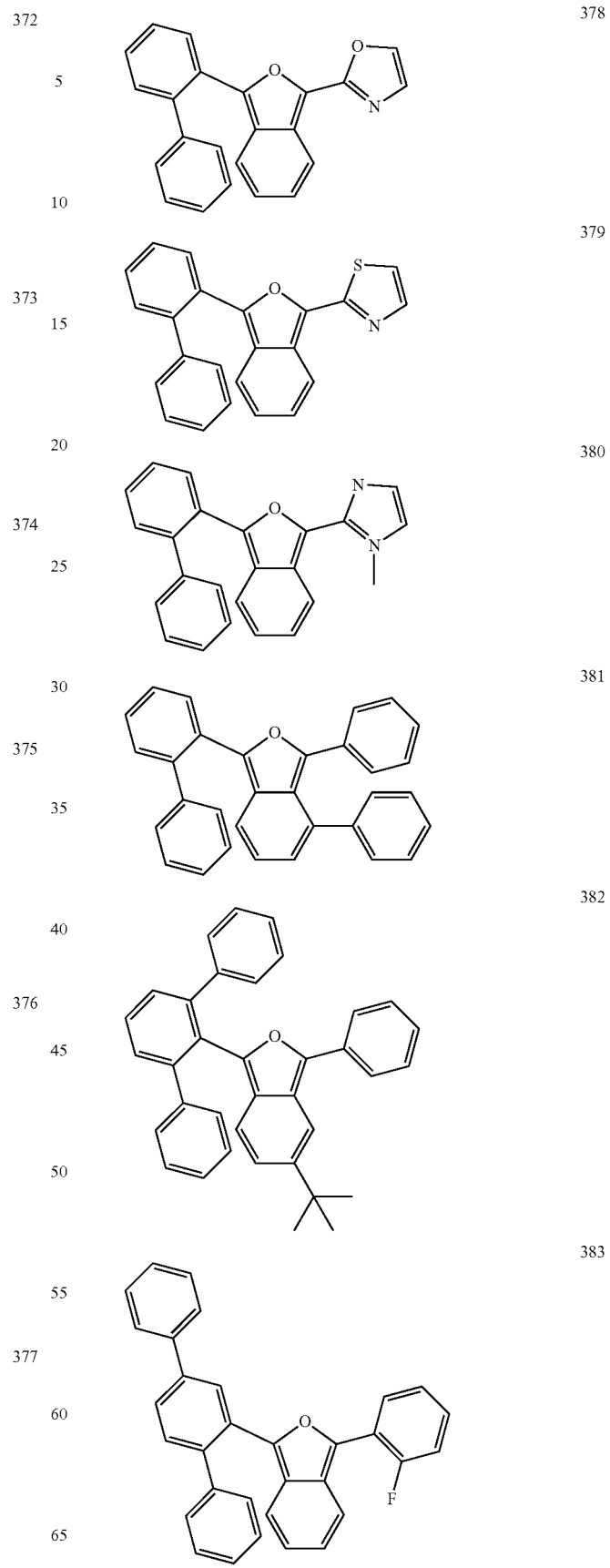 |
| 373 | | 379 | |
| 374 | | 380 | |
| 375 | | 381 | |
| 376 | | 382 | |
| 377 | | 383 | |

384 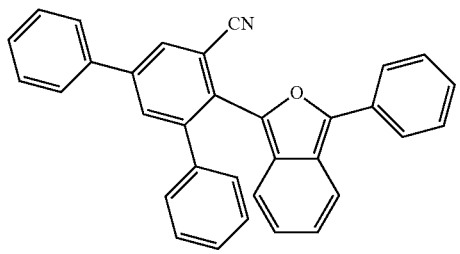
385 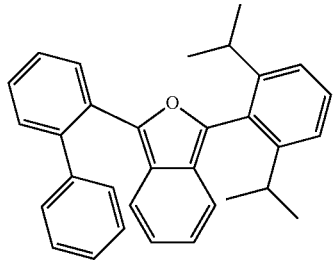
386 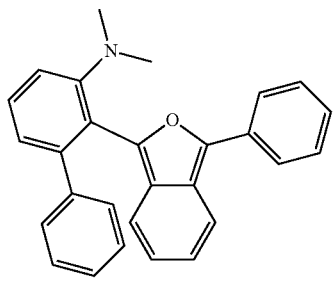
387 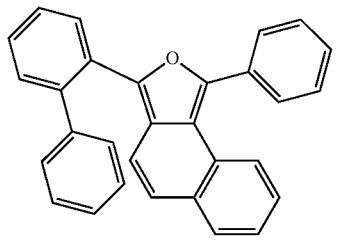
388 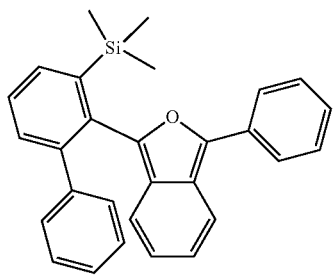
389 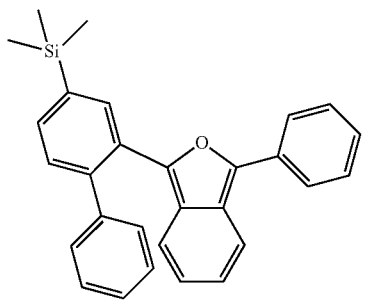
390 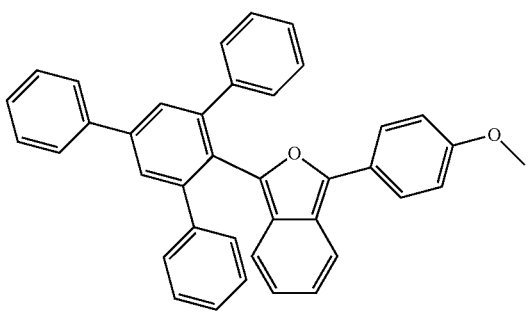
391 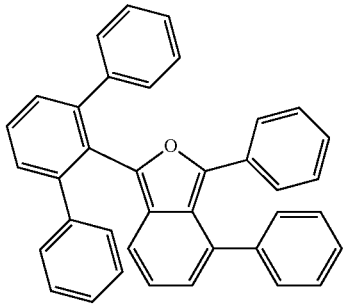
392 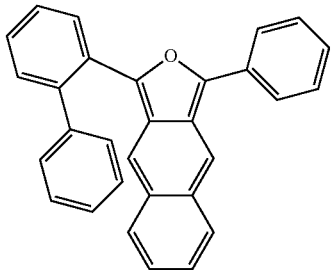
393 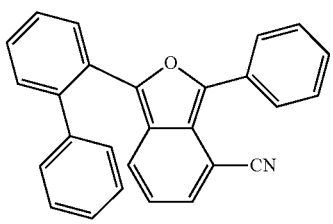
394 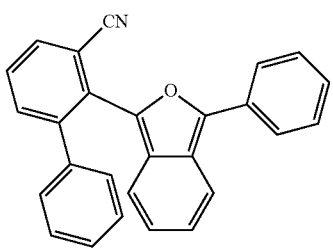

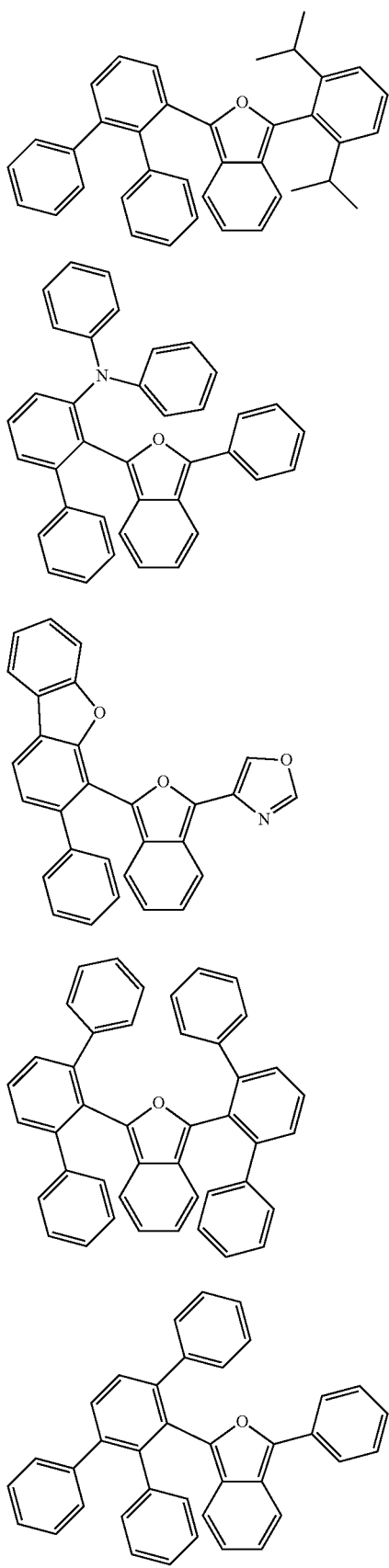
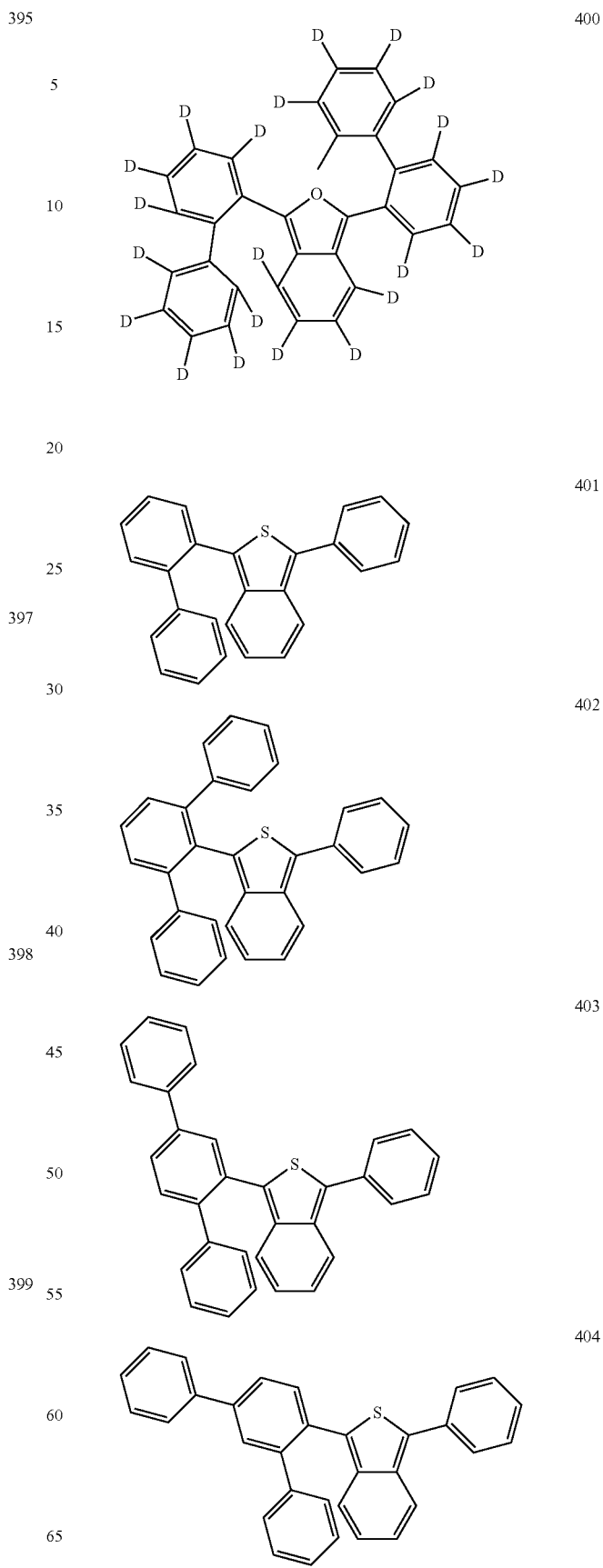

405
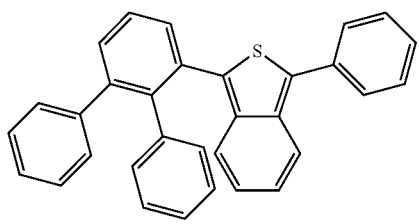
406
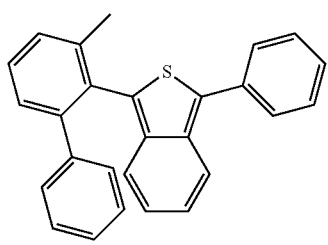
407
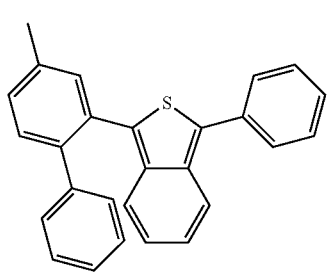
408
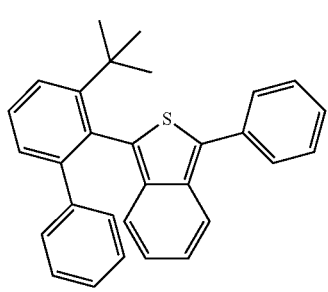
409
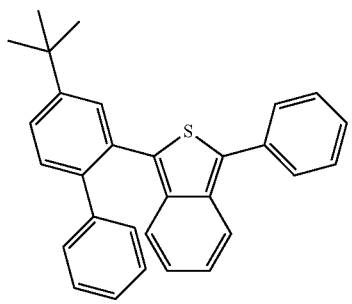
410
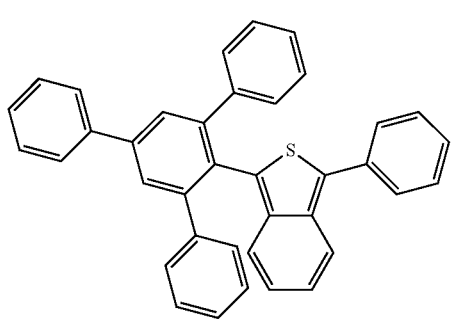
411
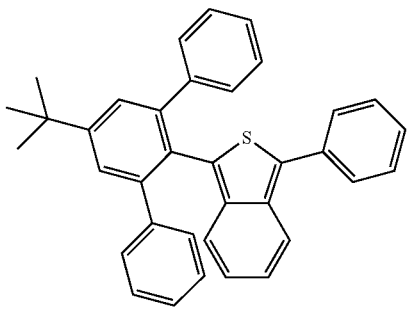
412
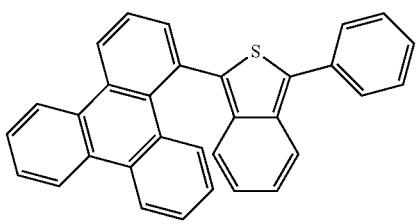
413
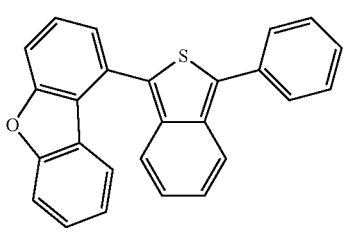
414
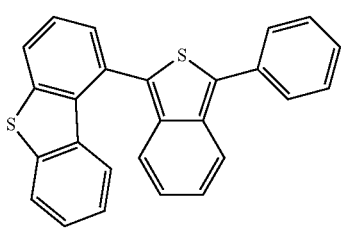
415
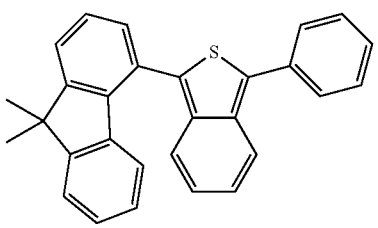
416
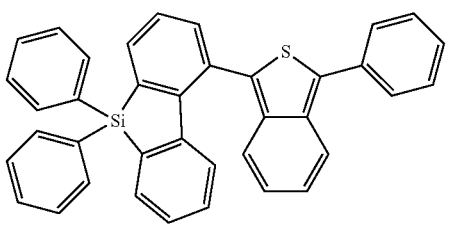

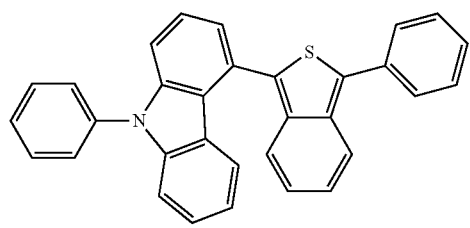
417
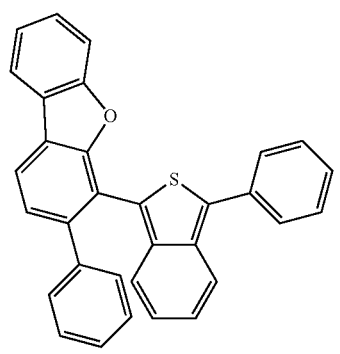
418

419
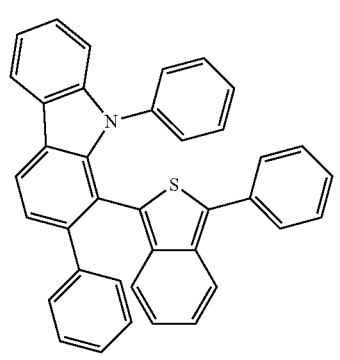
420
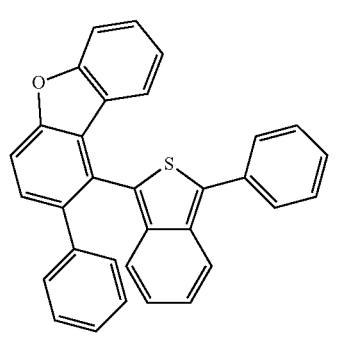
421
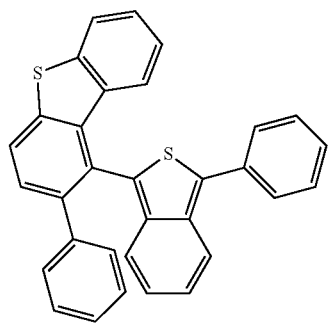
422
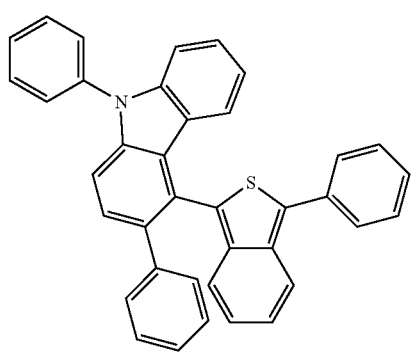
423
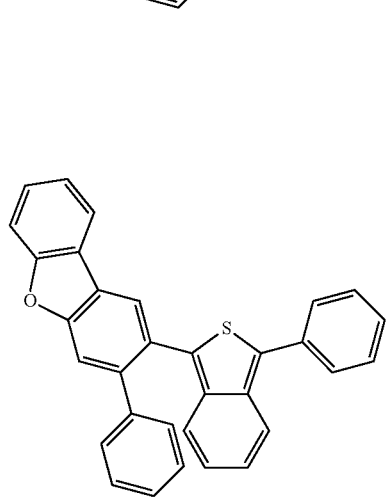
424
425

-continued
426
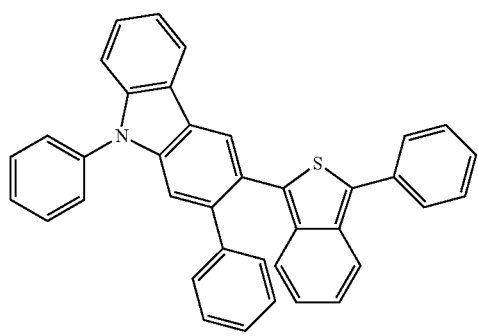
427
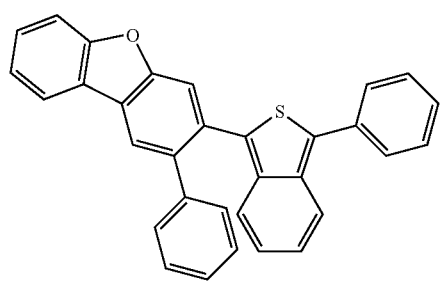
428
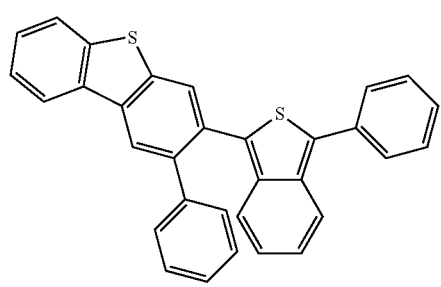
429
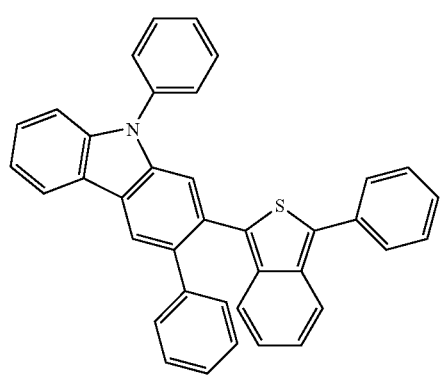
430
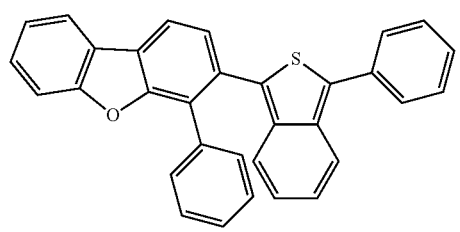
-continued
431
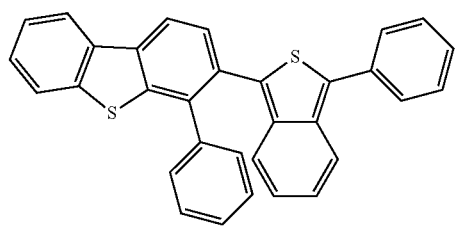
432
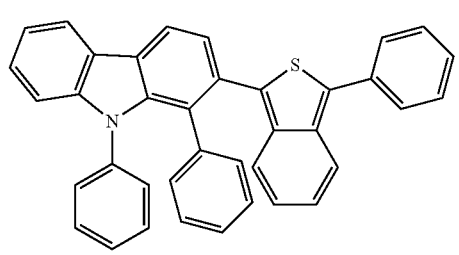
433
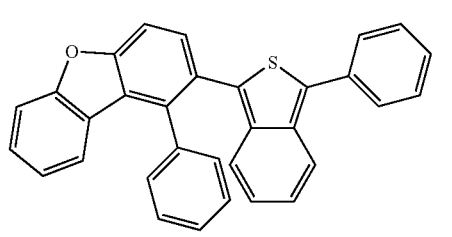
434
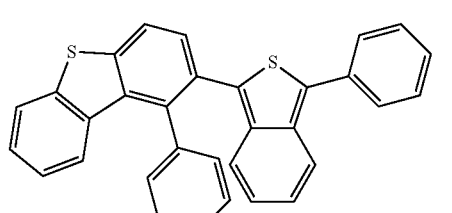
435
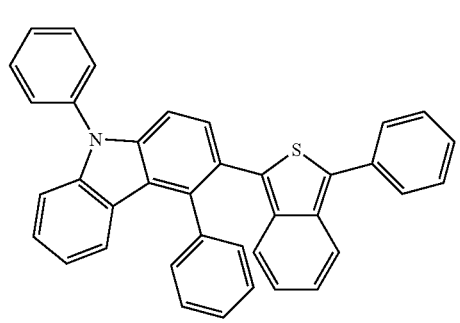
436
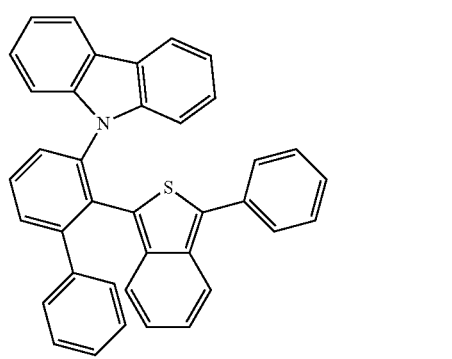

437
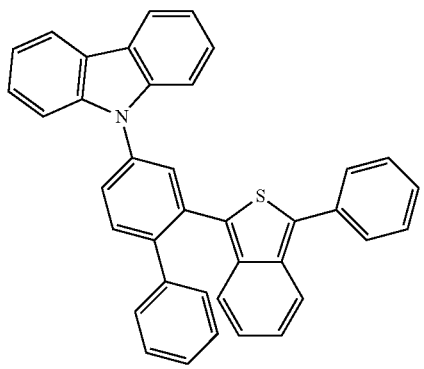
438
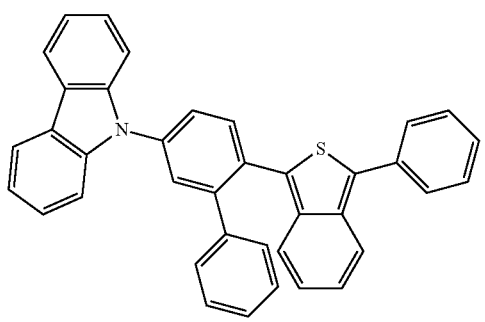
439
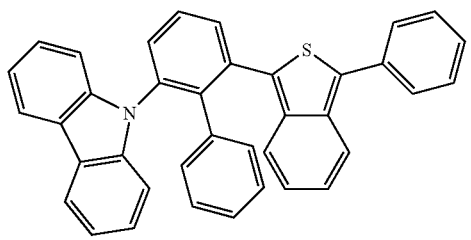
440
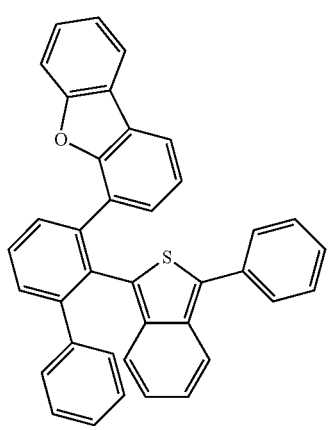
441
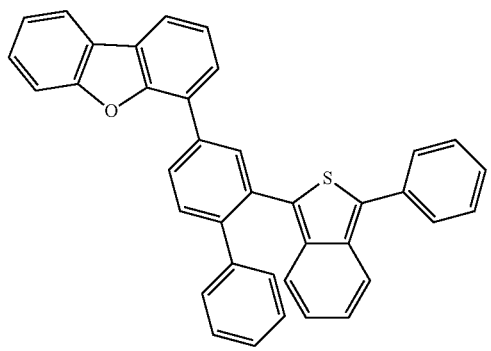
442
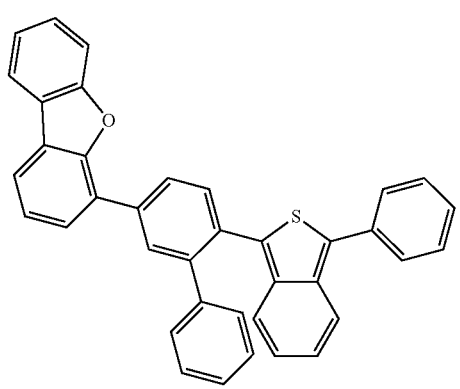
443
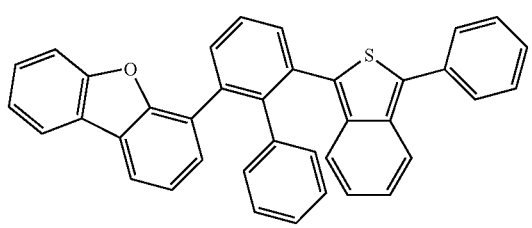
444
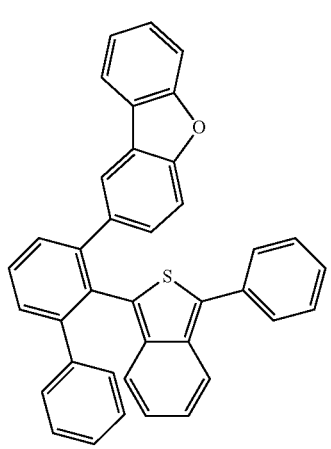

1199
-continued
445
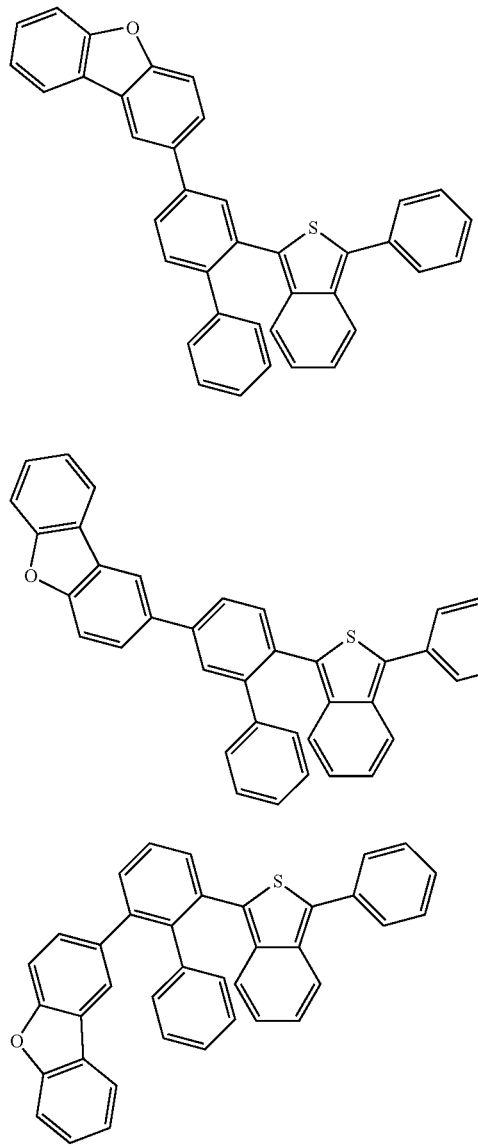
446

447

448
1200
-continued
449
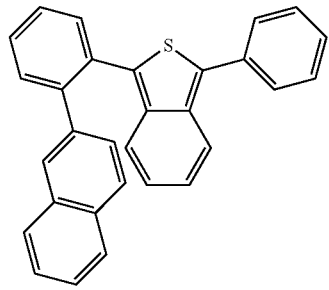
450
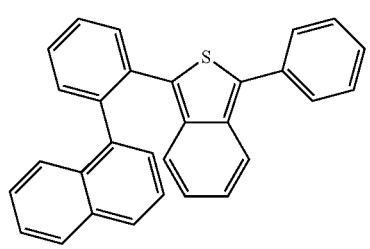
451
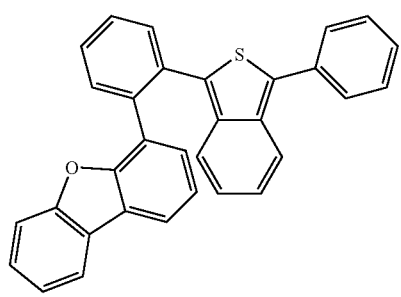
452
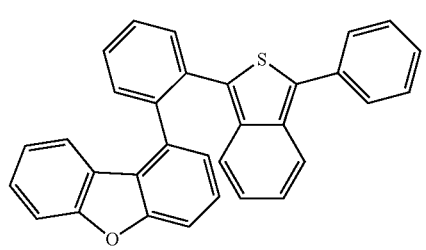
453
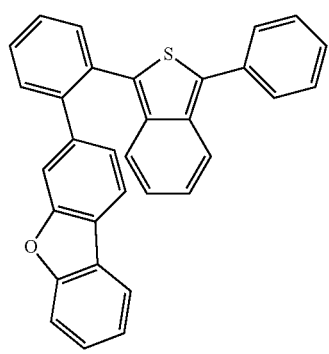

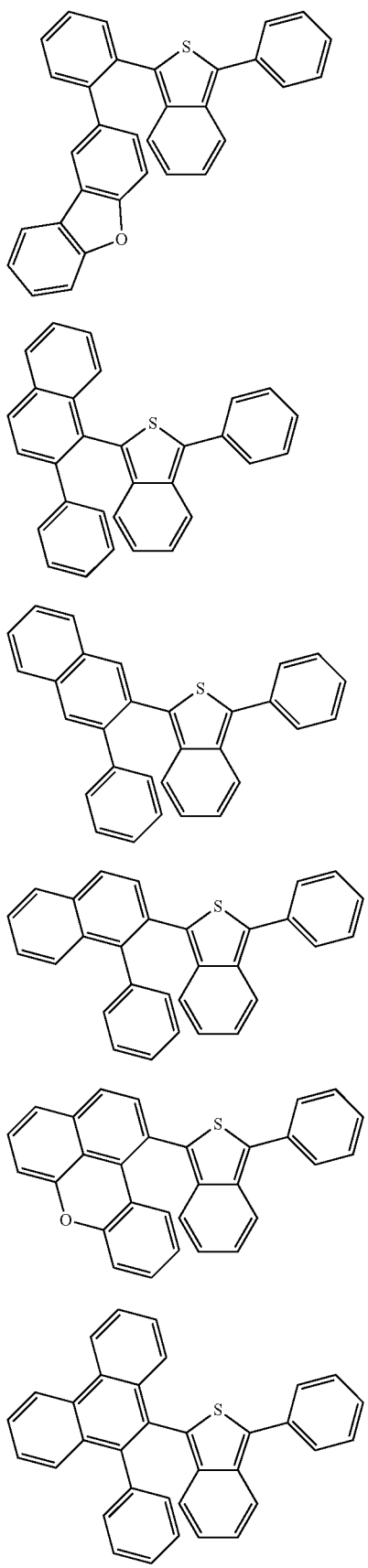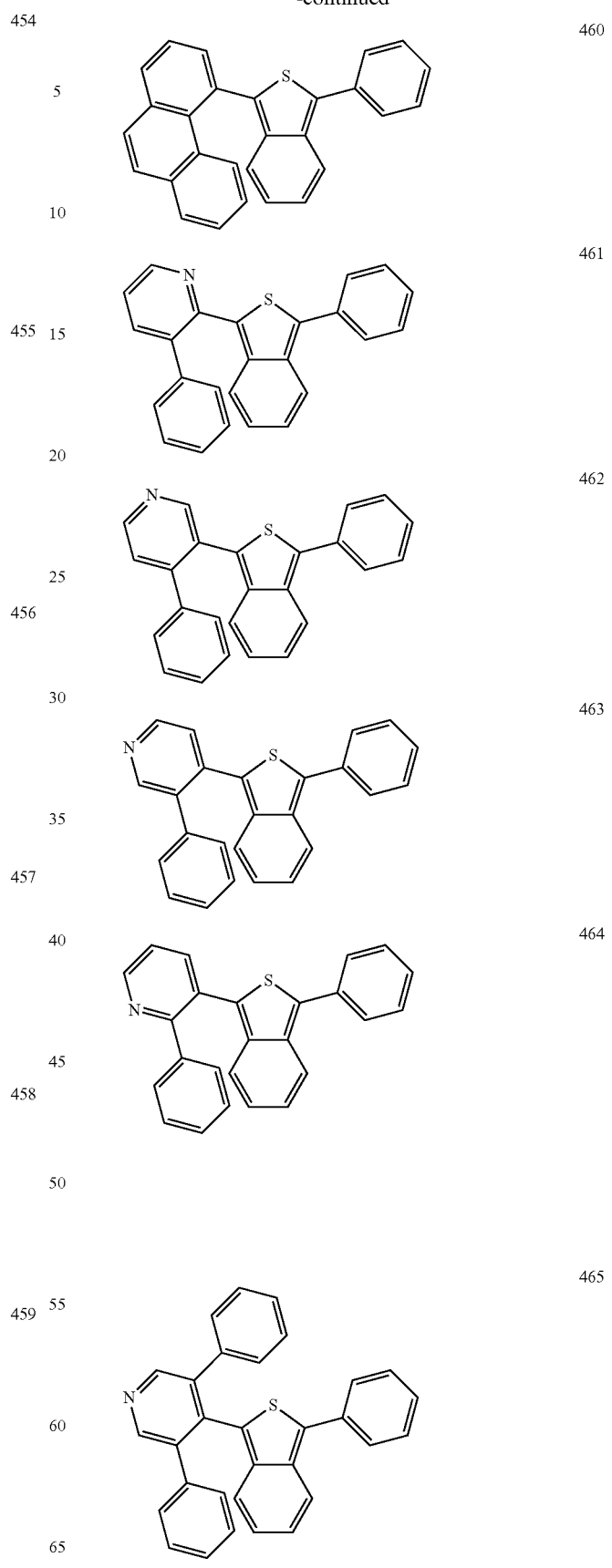

1203
-continued
466
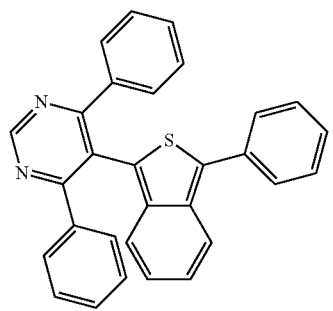
467
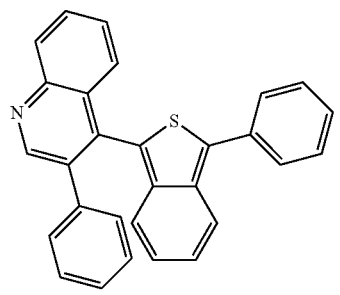
468
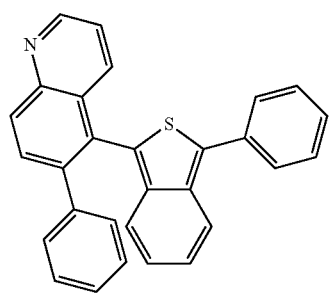
469
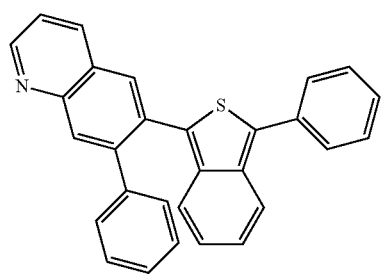
470
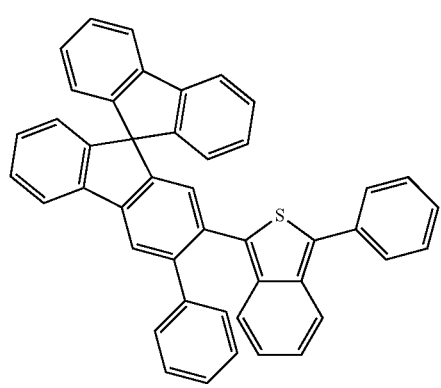
1204
-continued
471
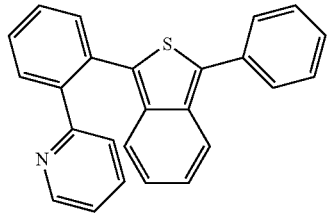
472
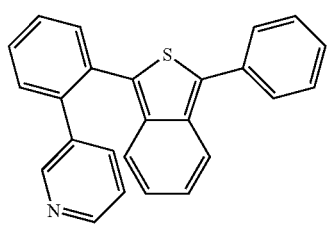
473
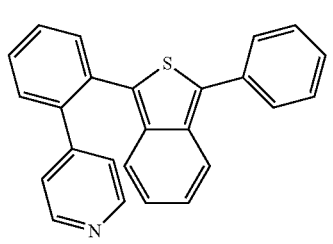
474
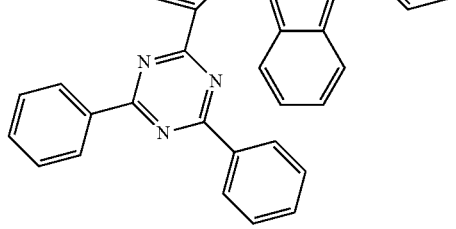
475
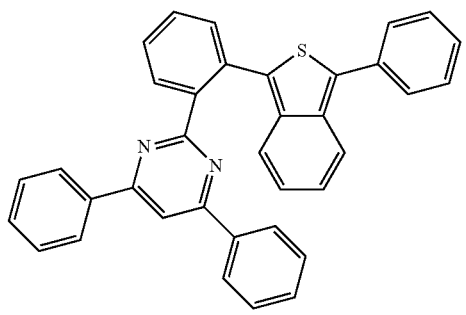

1205
-continued
476
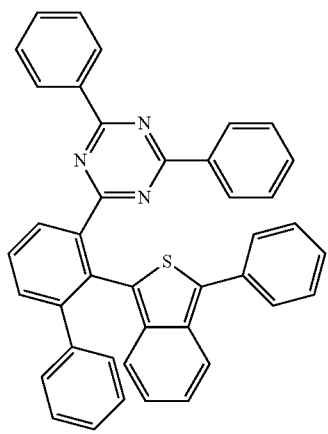
477
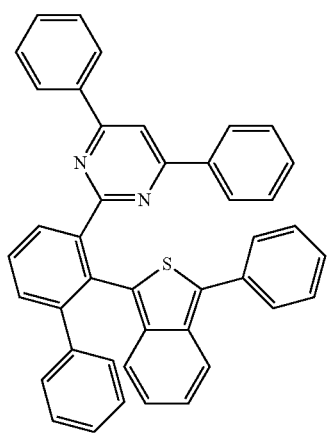
478
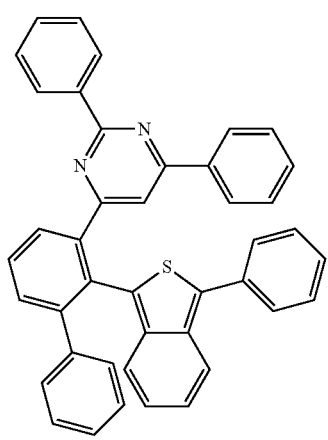
1206
-continued
479
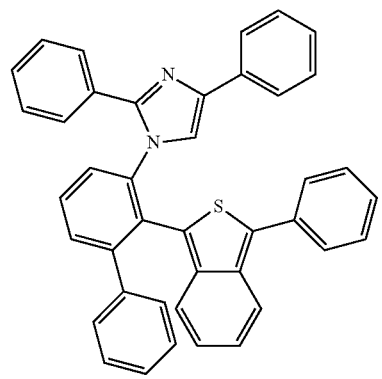
480
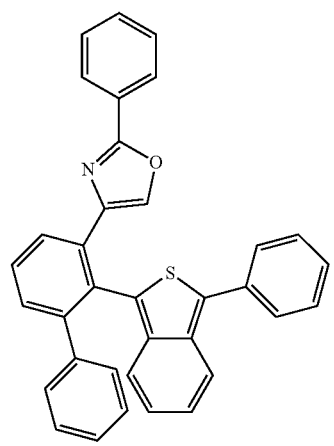
481
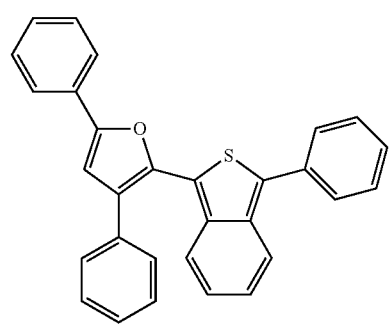
482
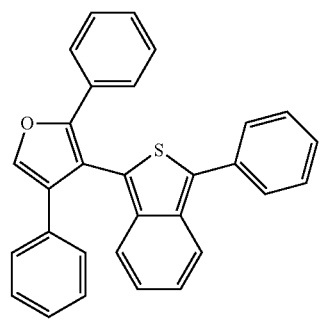

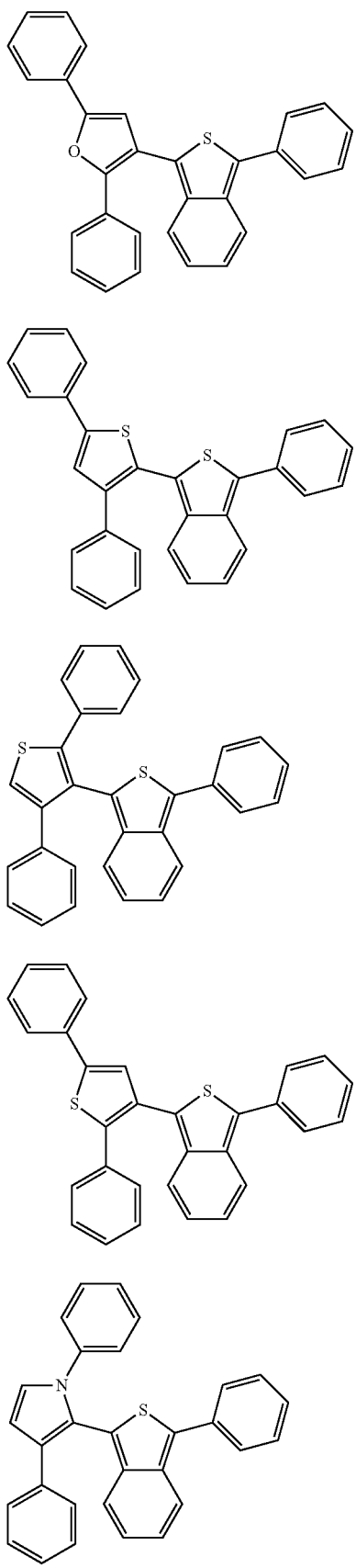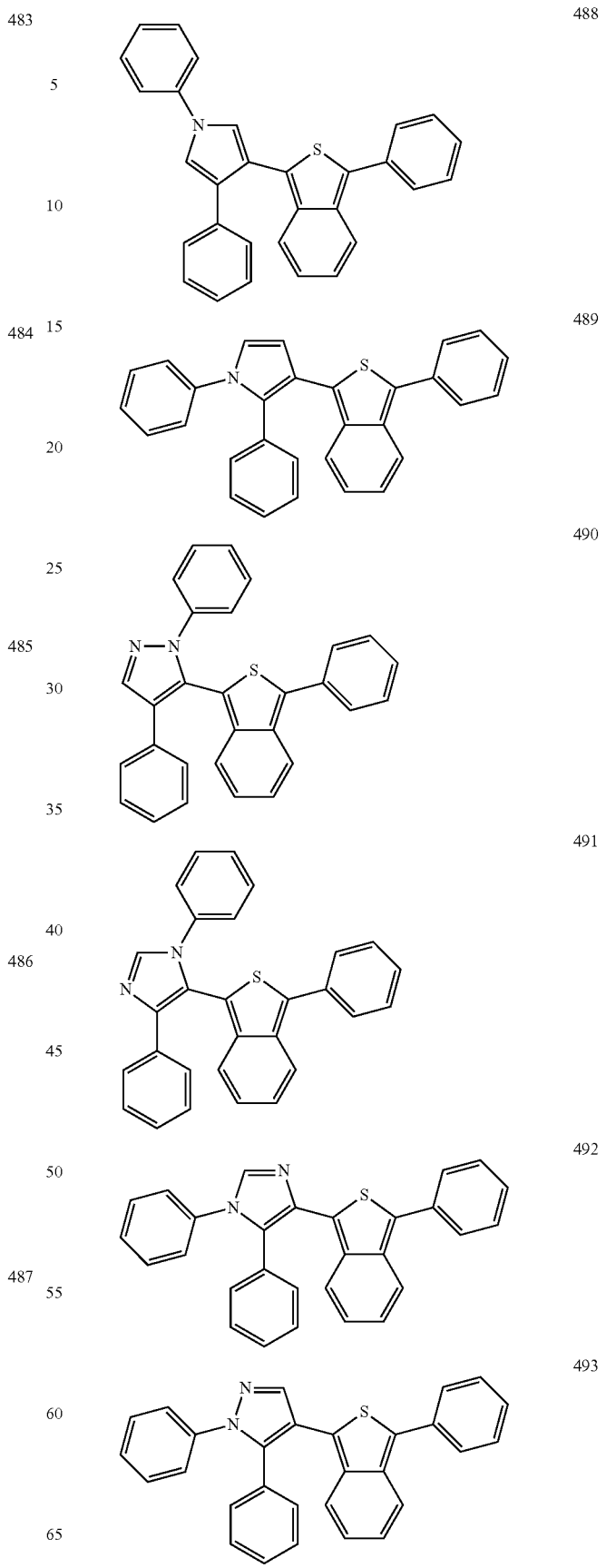

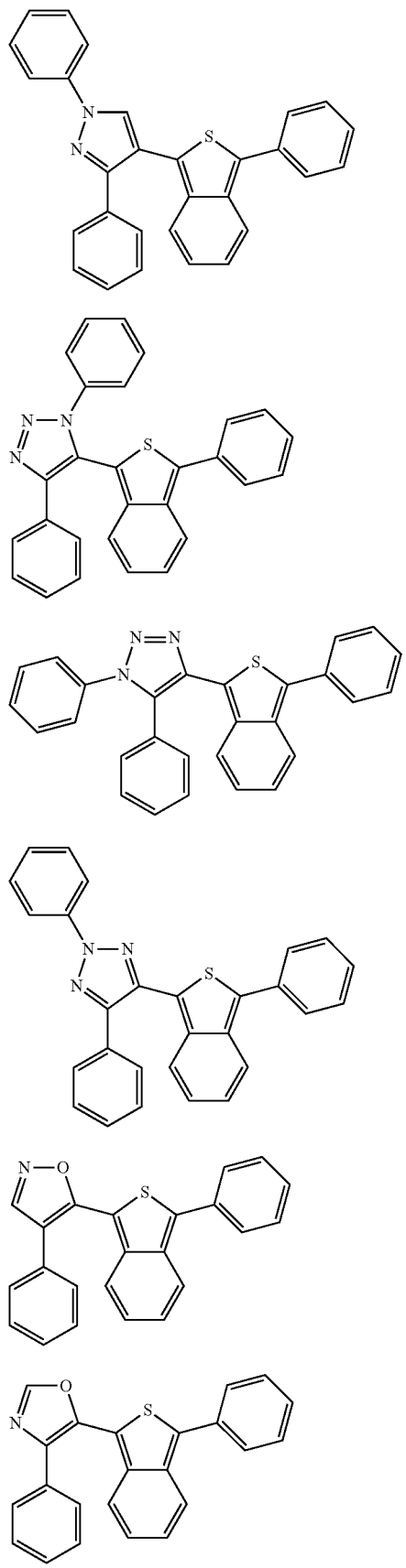
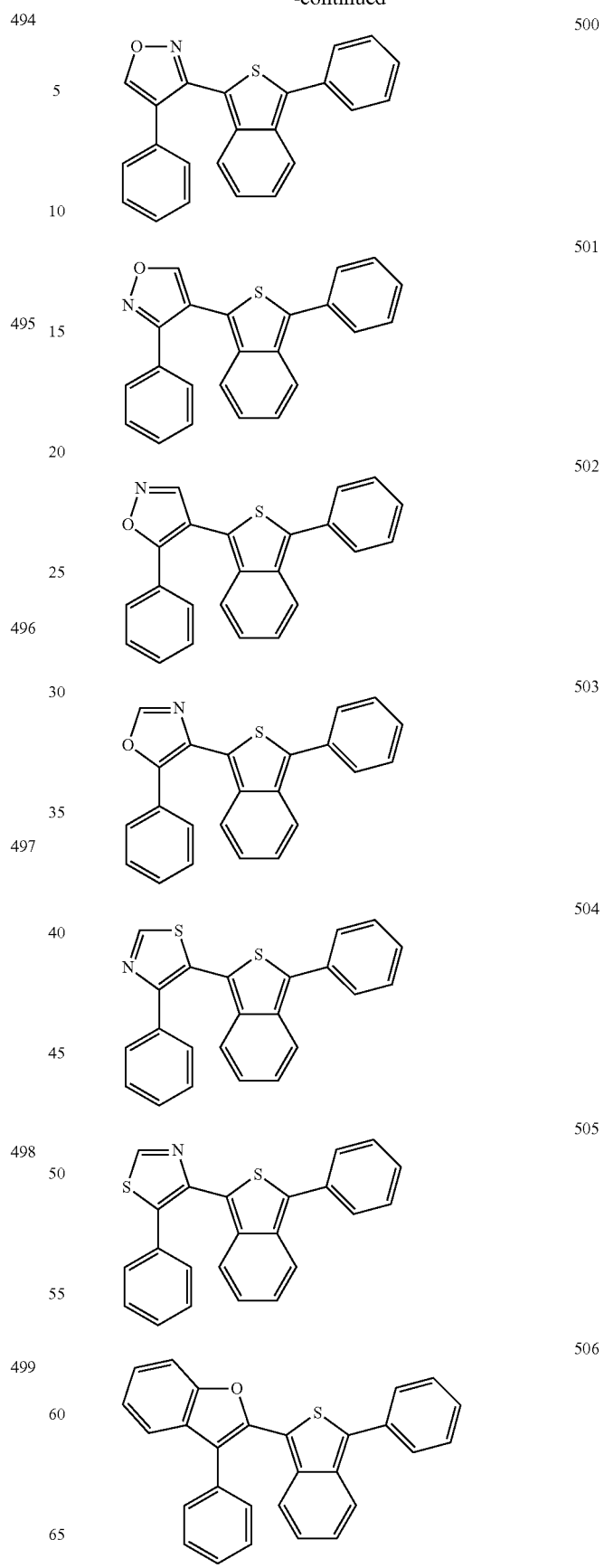

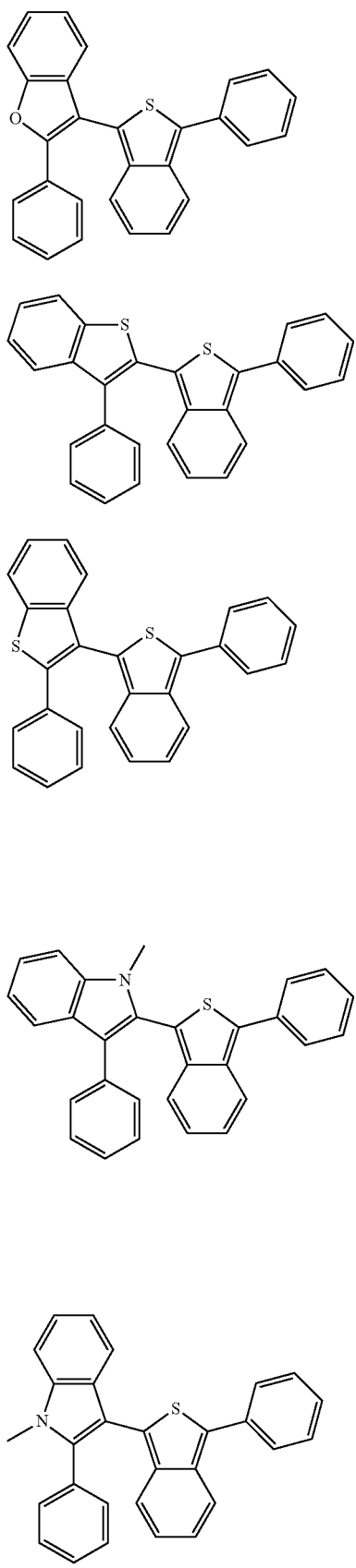
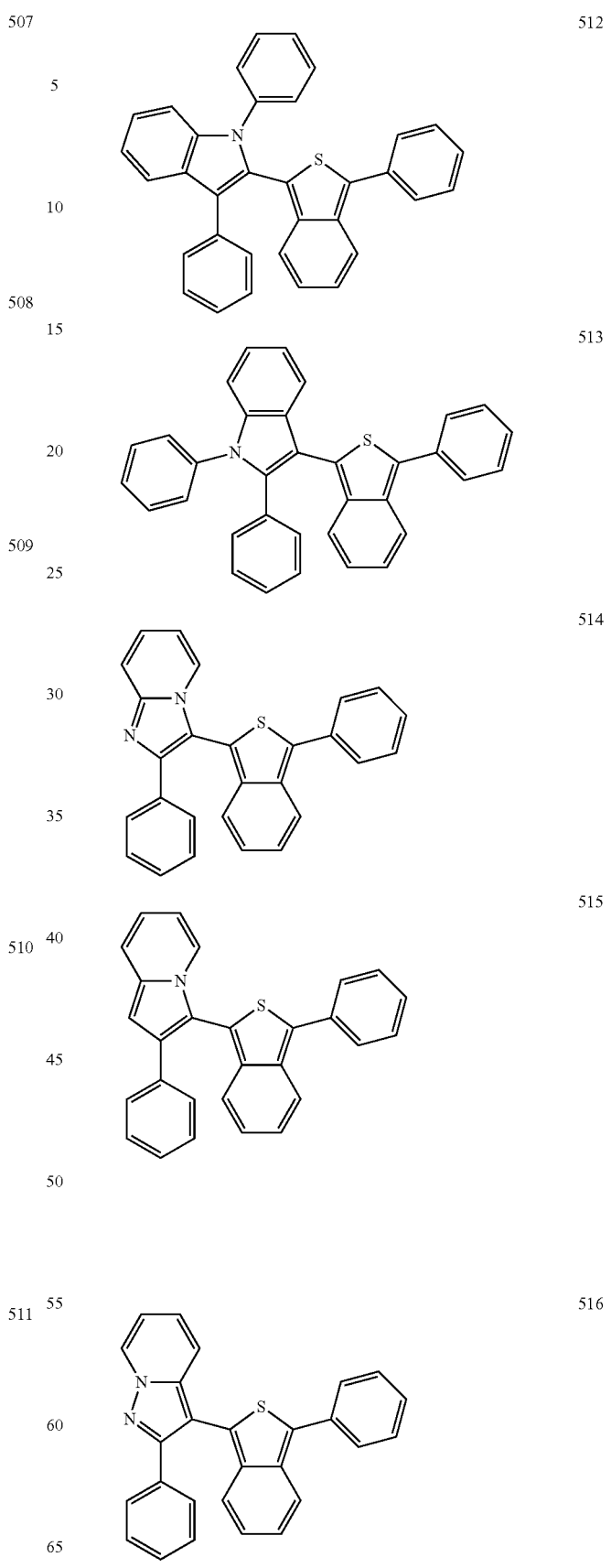

1213
-continued
517
518
519
520
521
522
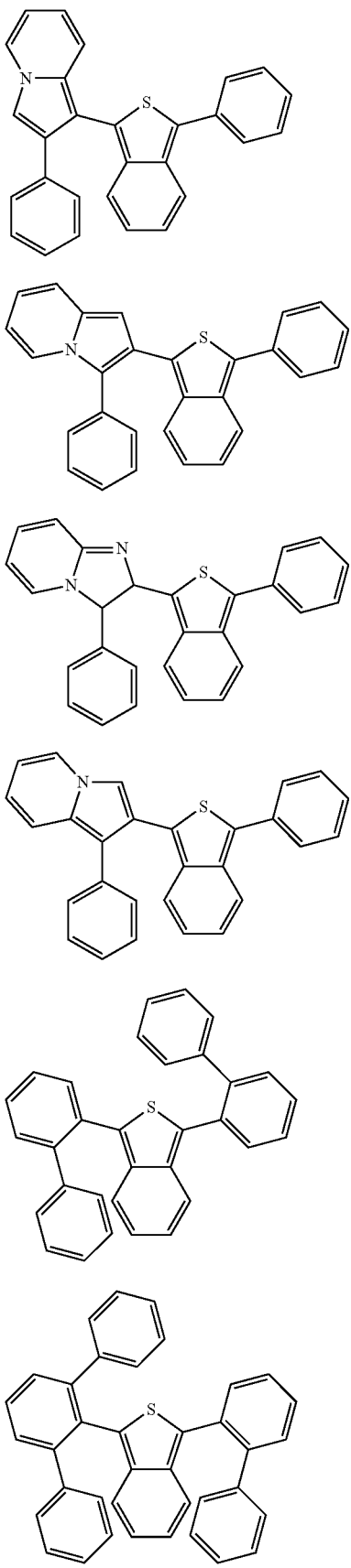
1214
-continued
523
524
525
526
527
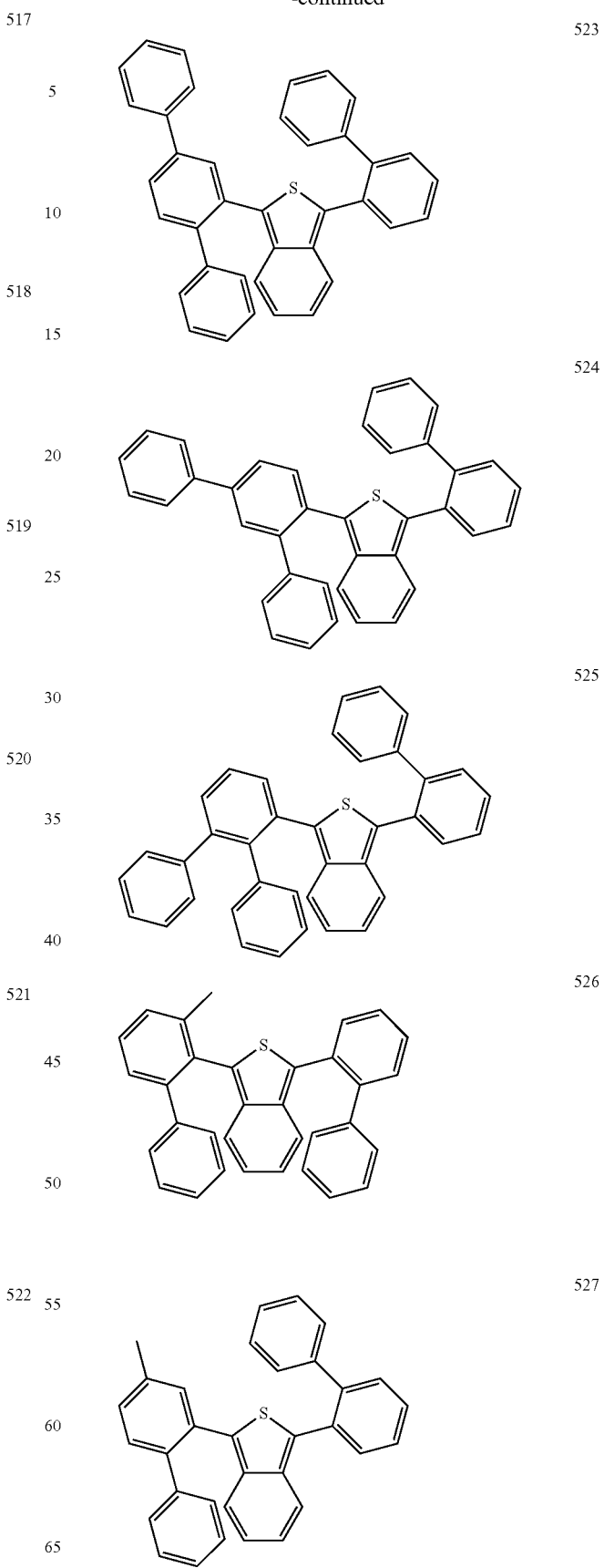

1215
-continued
528
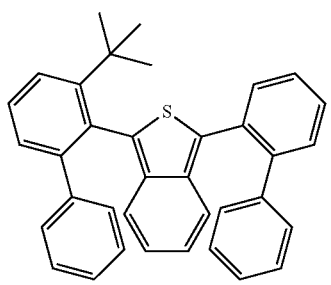
529
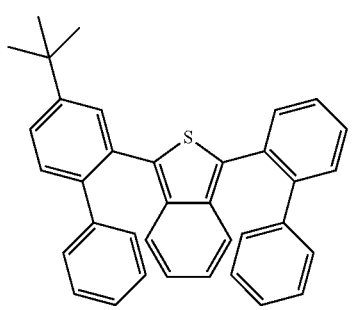
530
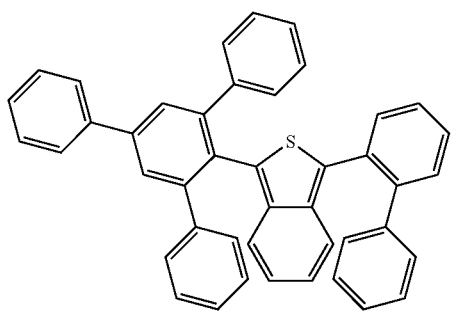
531
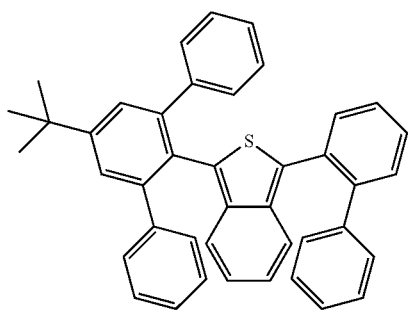
532
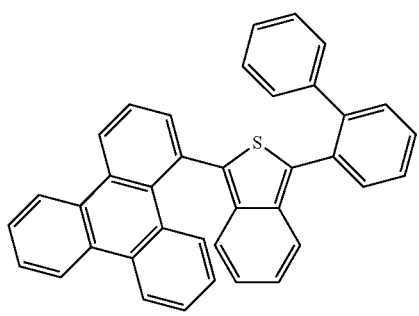
1216
-continued
533
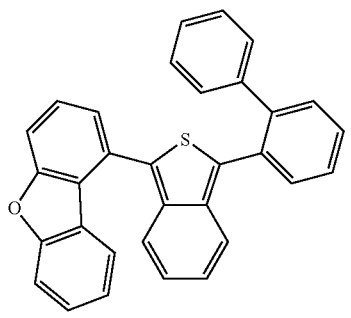
534
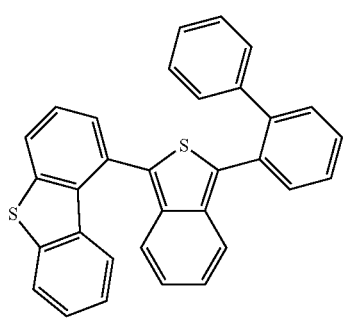
535
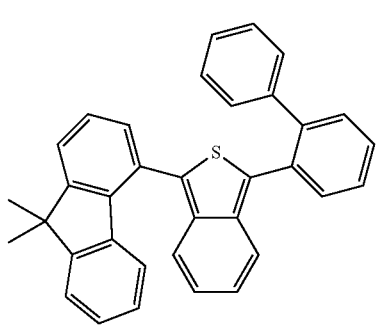
536
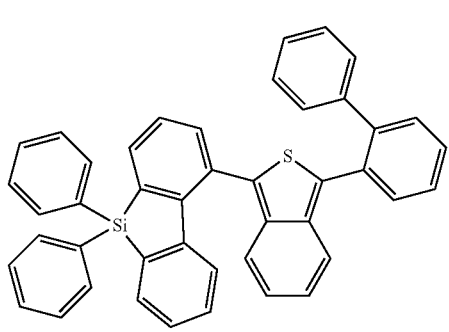
537
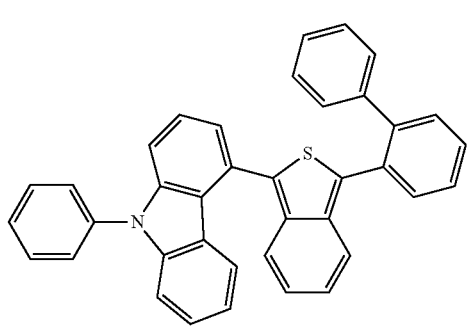

1217
-continued
538 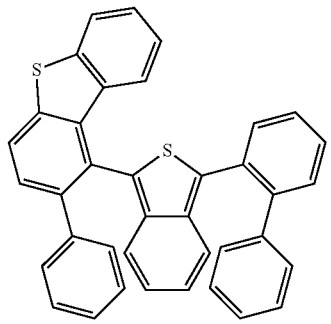
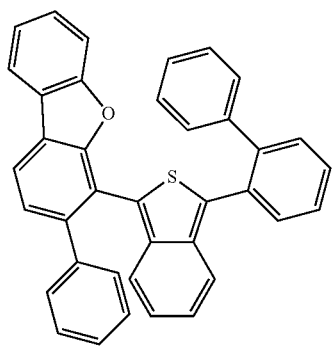
539
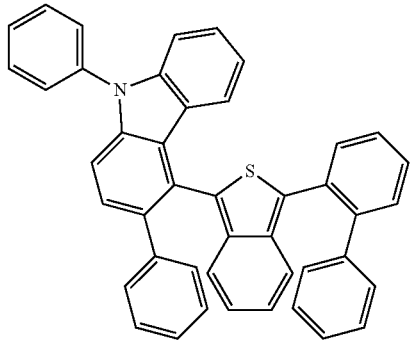

540
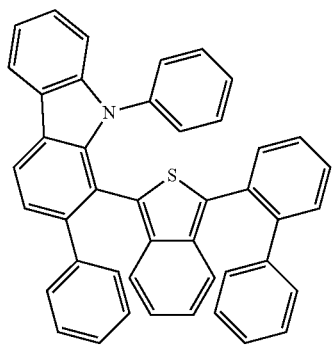

541
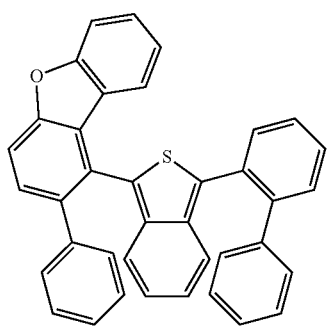
1218
-continued
542
543
544
545
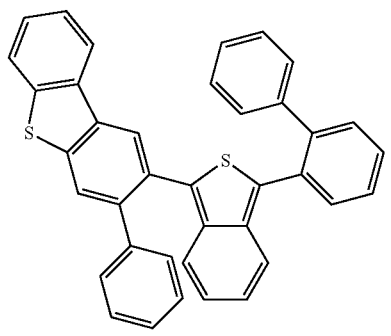

546
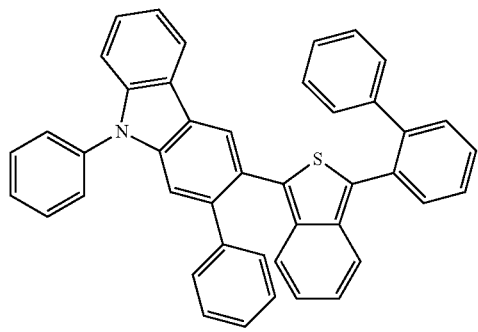
547
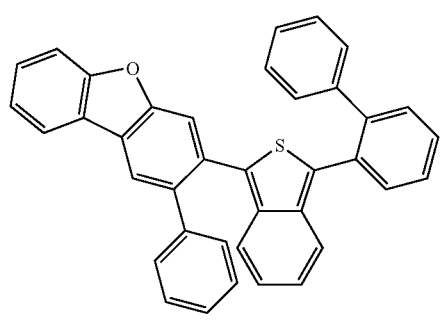
548
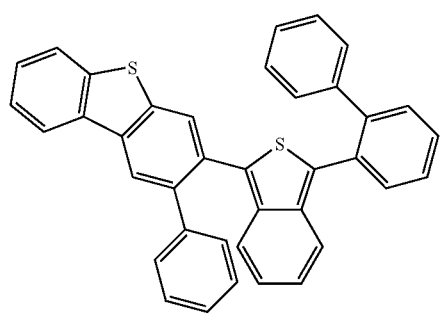
549
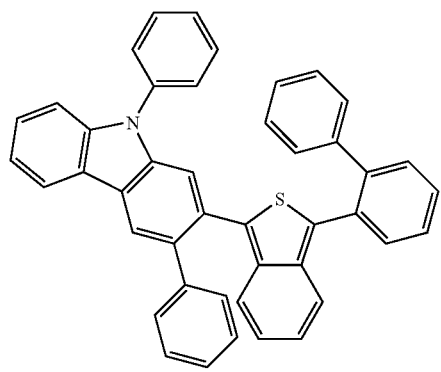
550
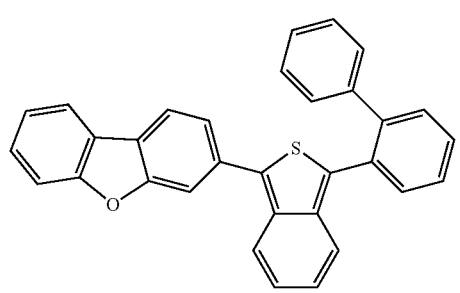
551
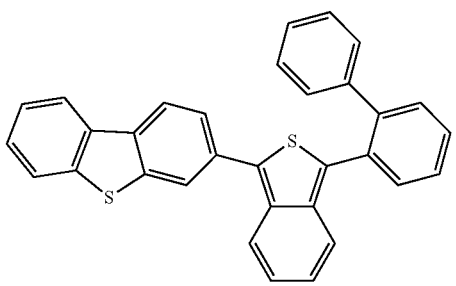
552
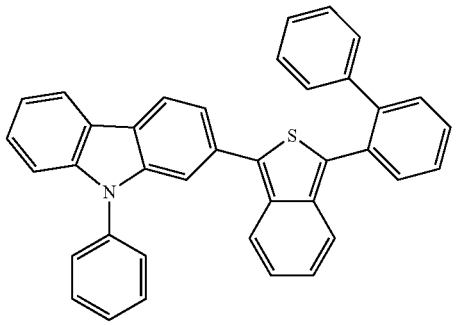
553
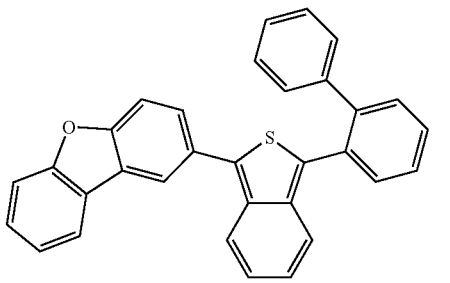
554
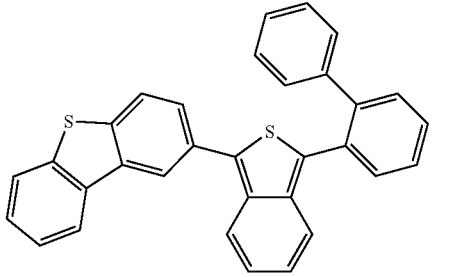
555
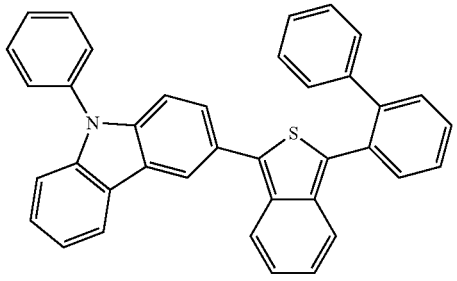

1221
-continued
556
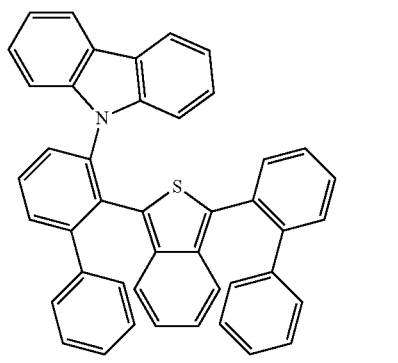
557
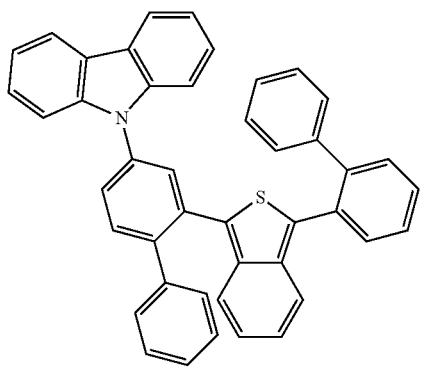
558
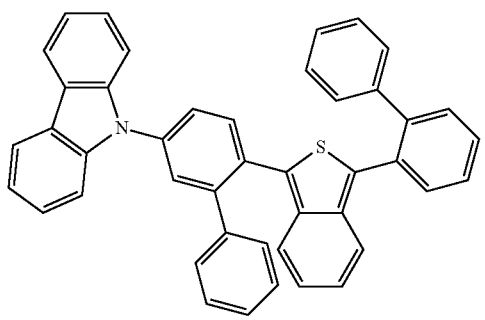
559
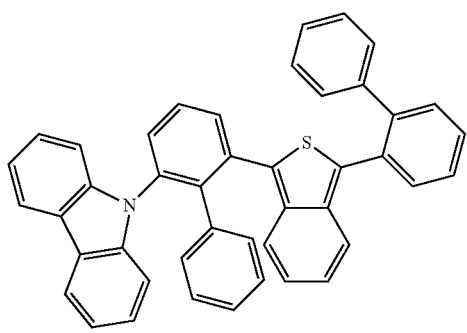
1222
-continued
560

561

562
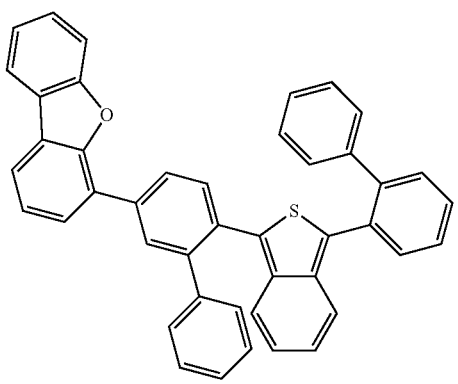
563
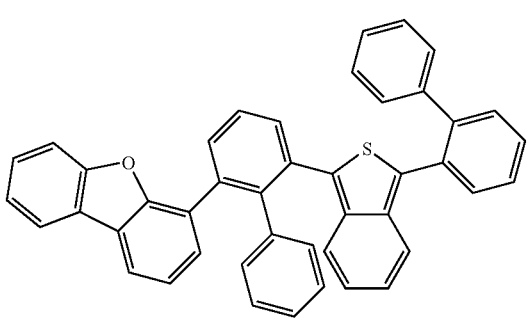

1223
-continued
564
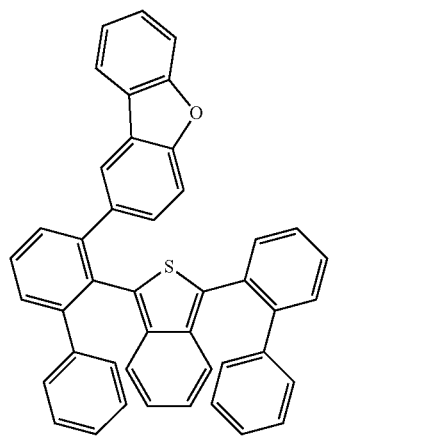
565
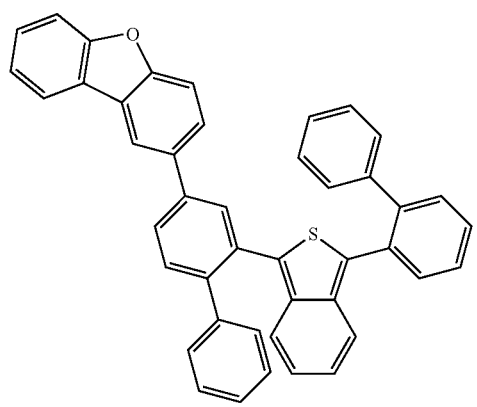
566
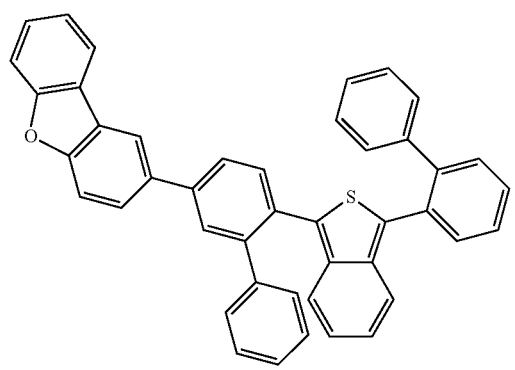
567
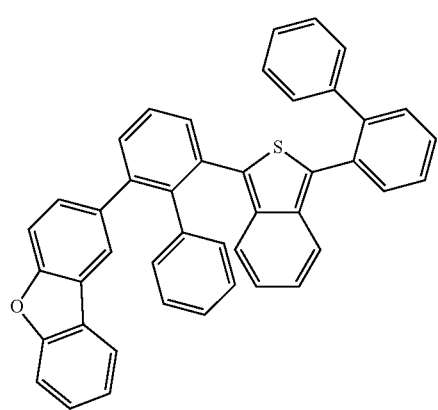
1224
-continued
568
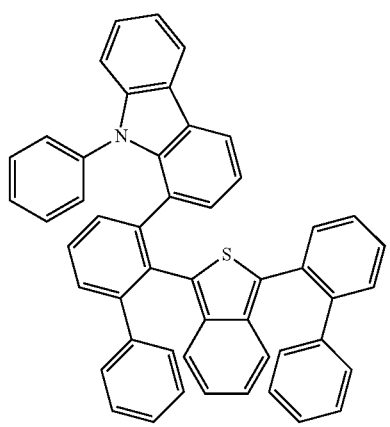
569
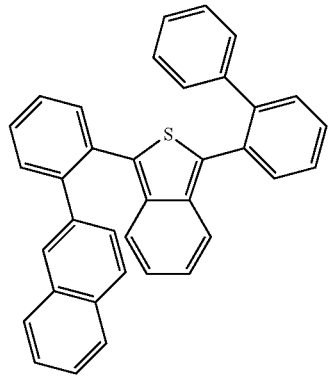
570
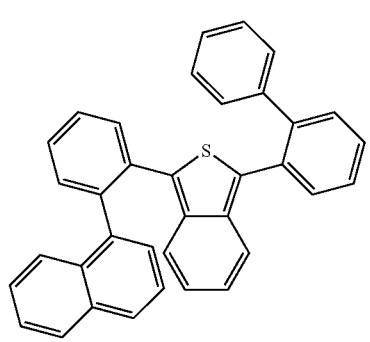
571
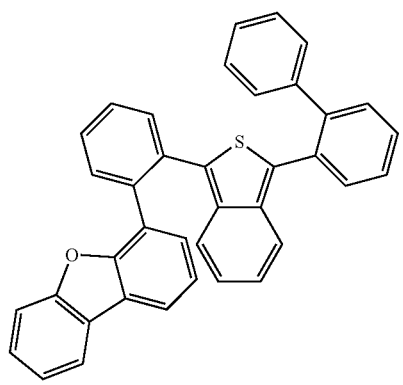

1225
-continued
572
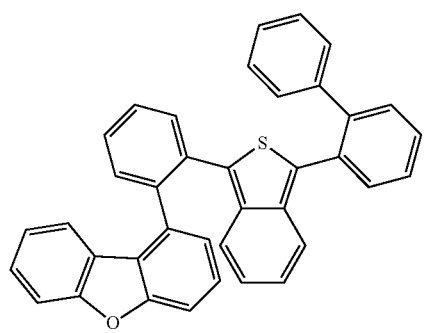
573
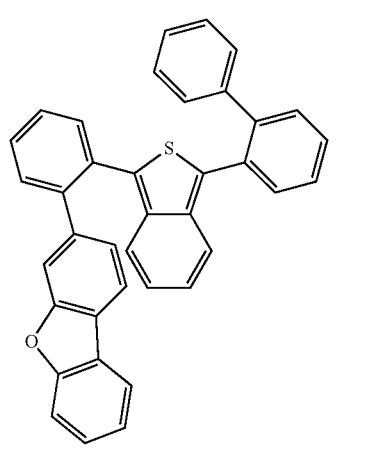
574
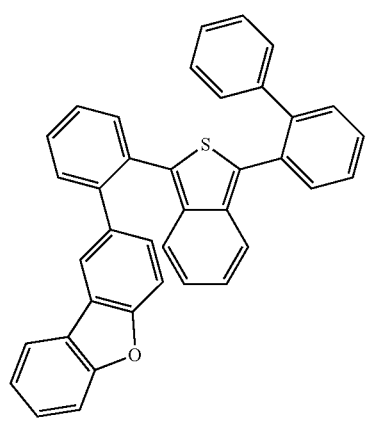
575
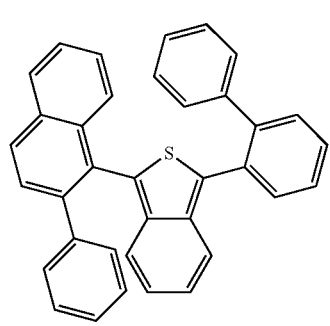
1226
-continued
576
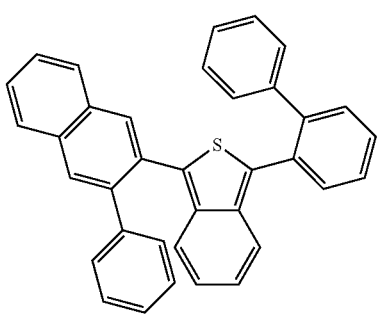
577
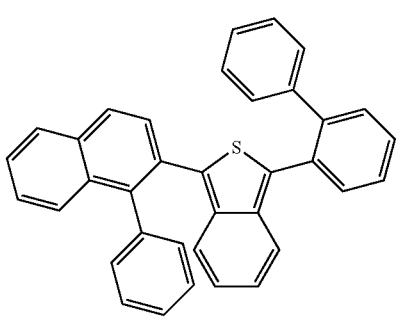
578
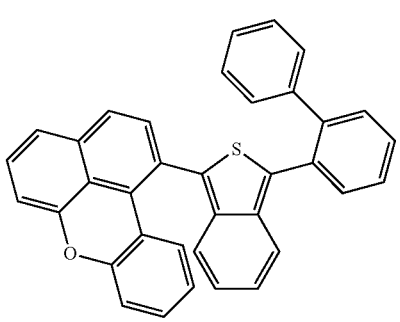
579
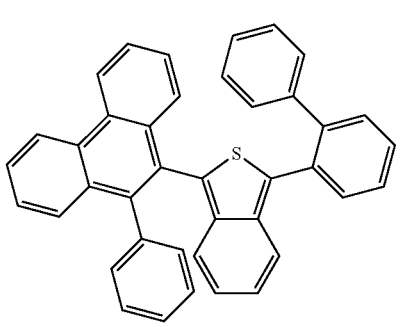
580
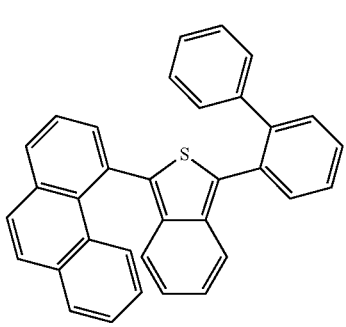

581 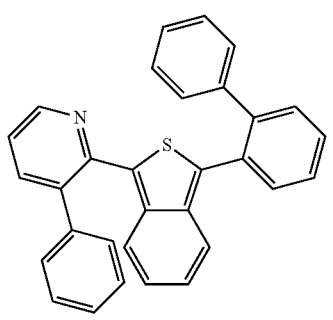
582 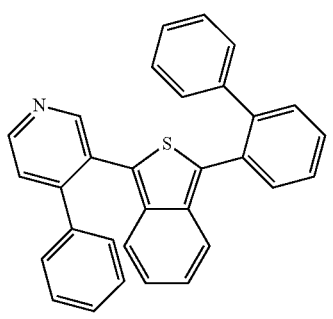
583 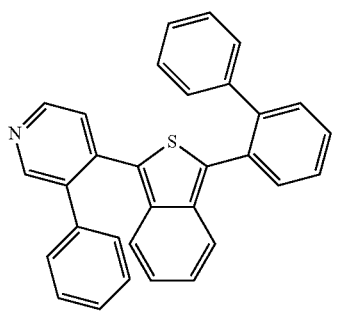
584 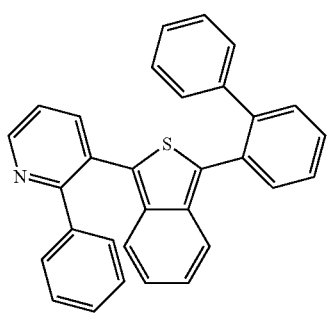
585 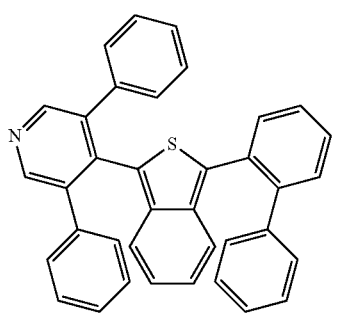
586 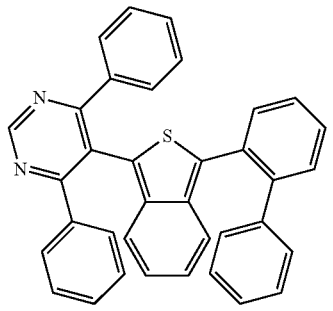
587 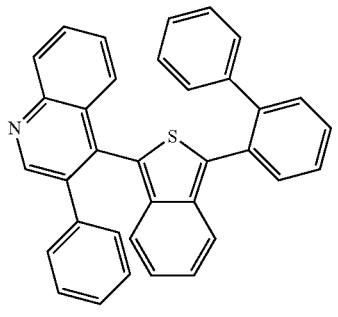
588 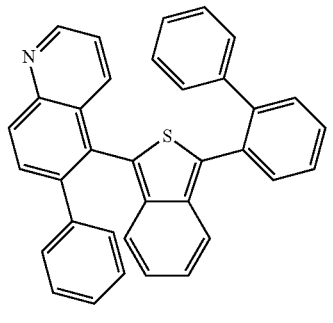
589 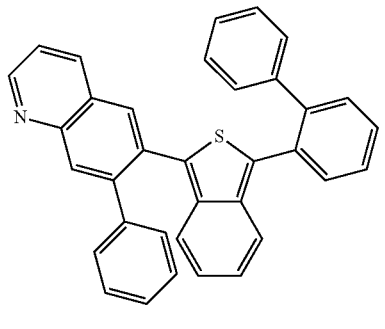
590 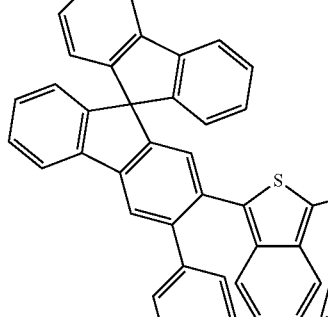

1229
-continued
591
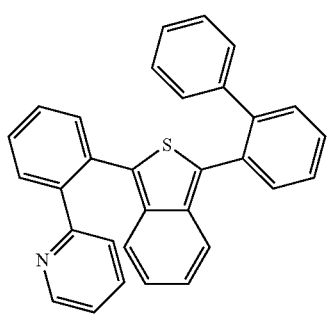
592
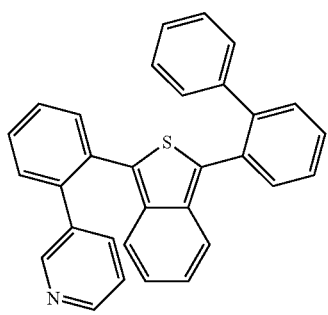
593
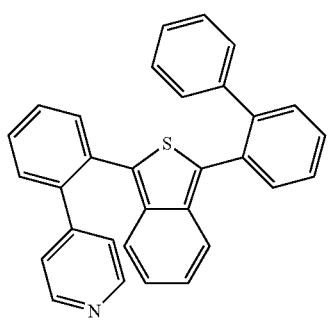
594
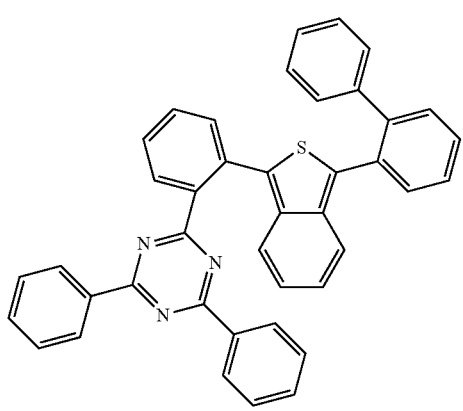
1230
-continued
595
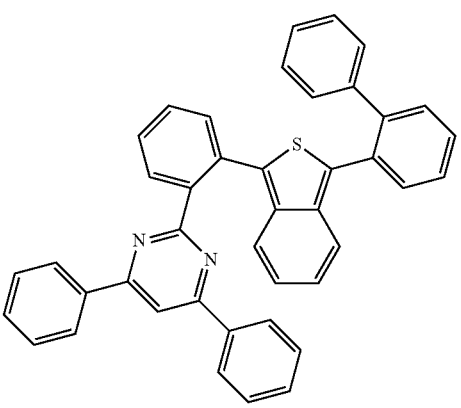
596
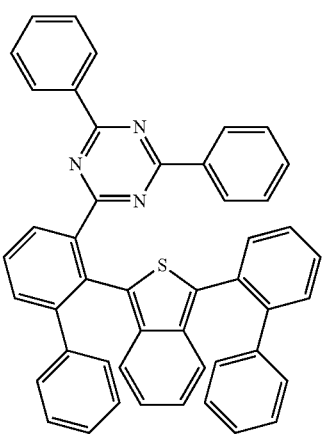
597
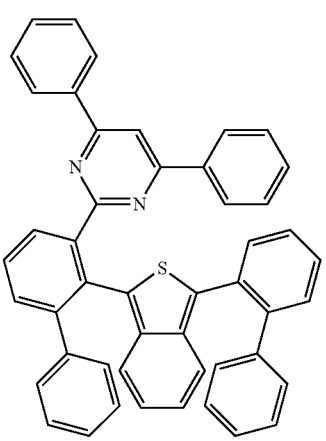

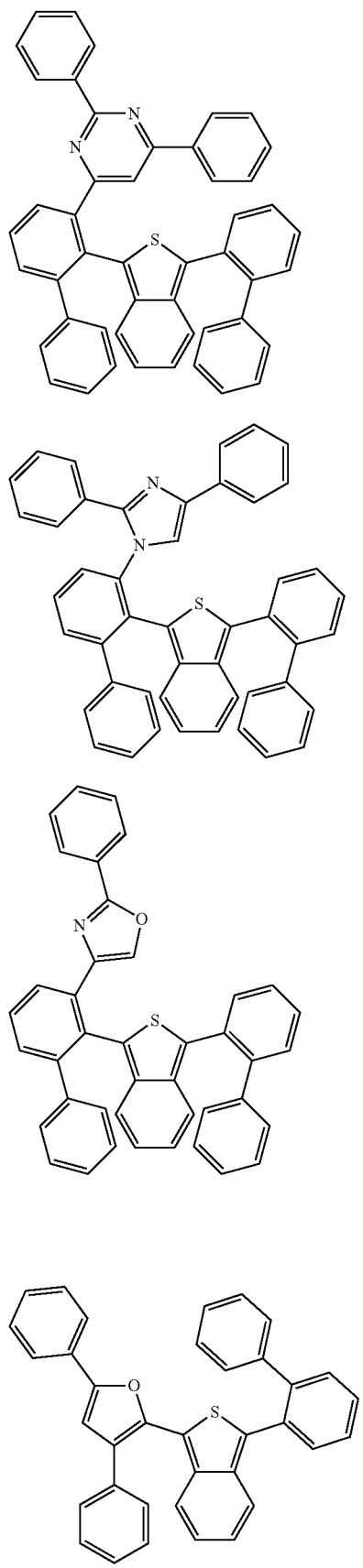
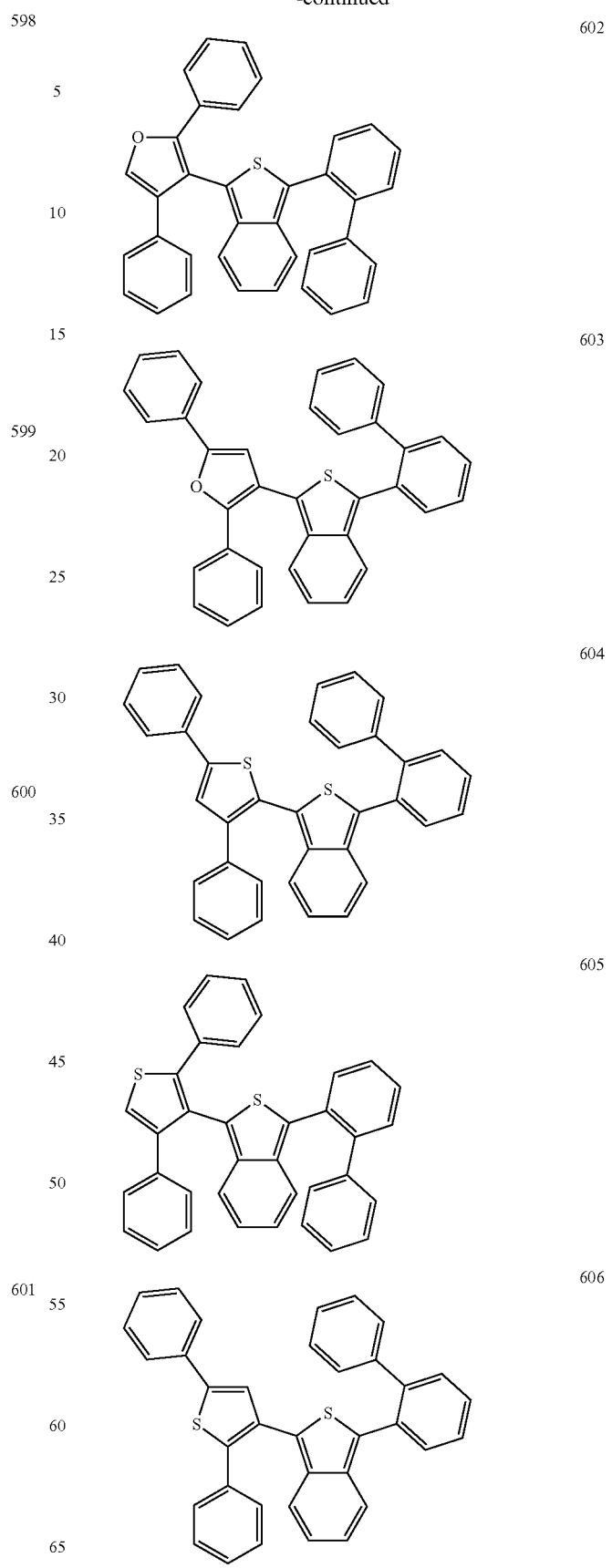

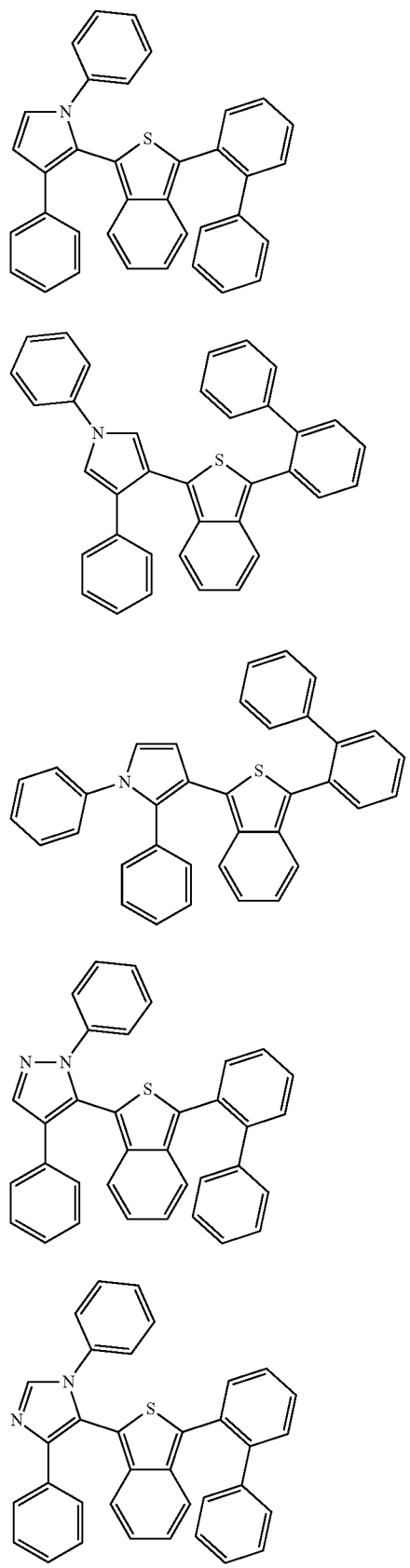
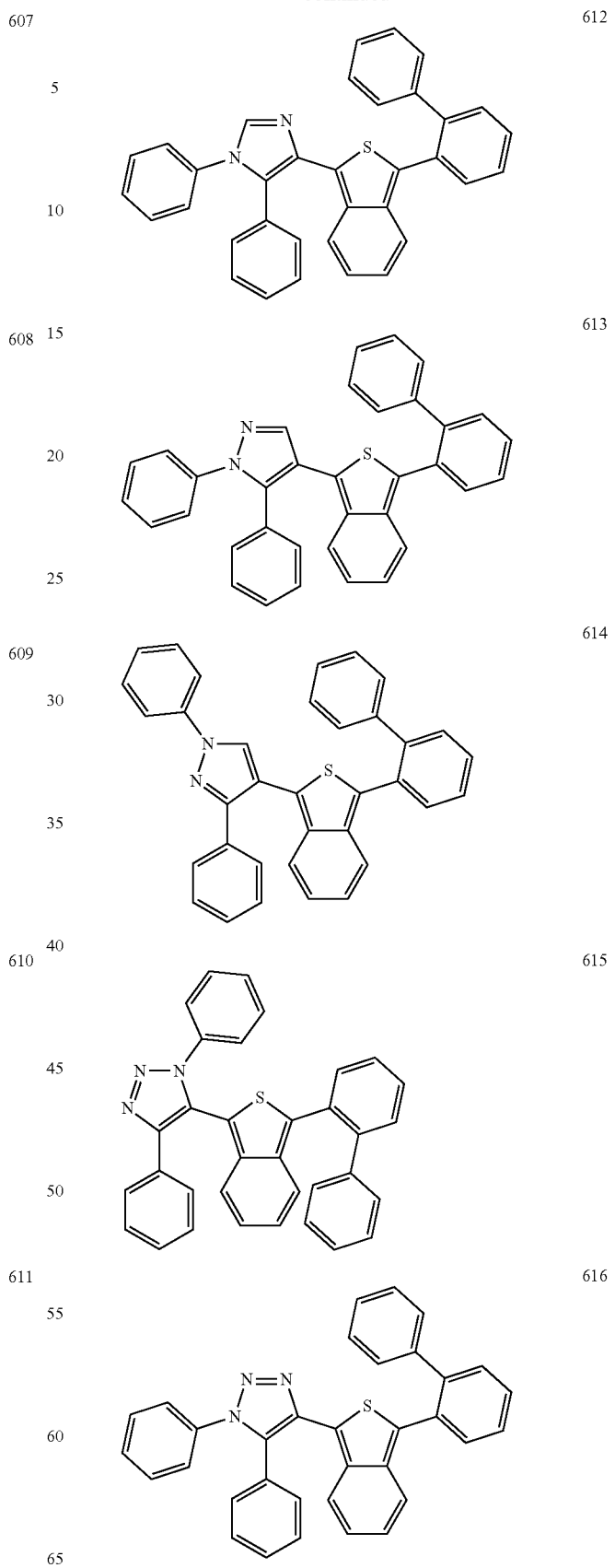

1235
-continued
617
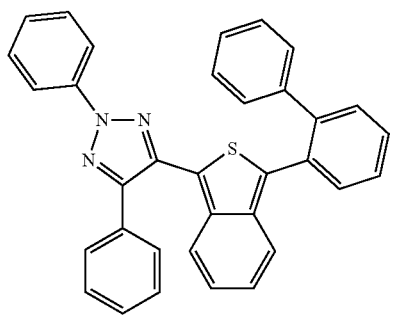
618
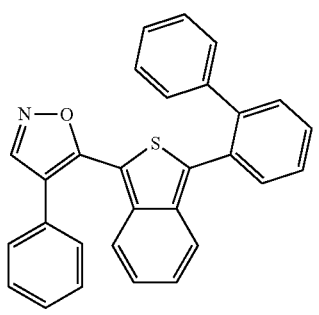
619
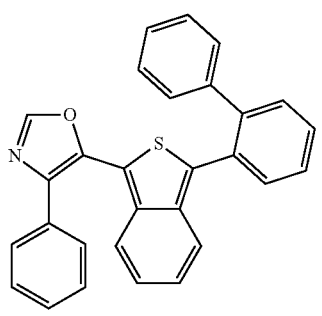
620
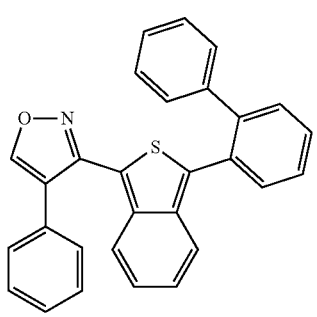
621
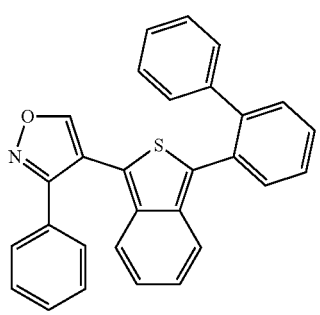
1236
-continued
622
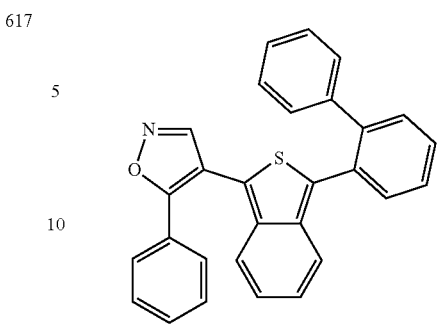
623
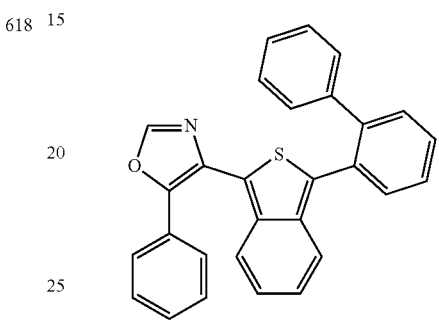
624
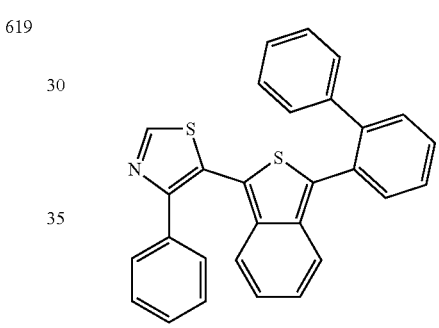
625
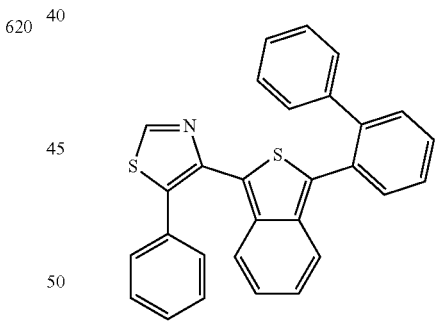
626
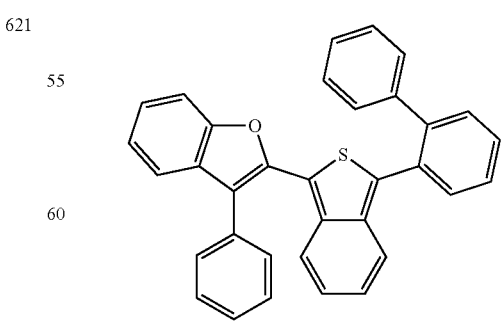

1237
-continued
627
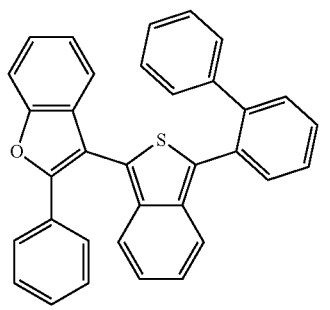
628
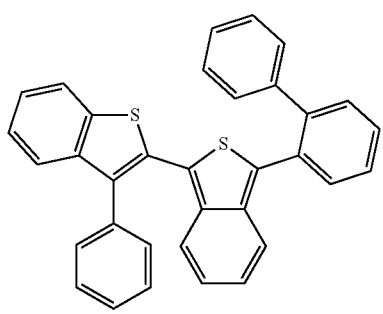
629
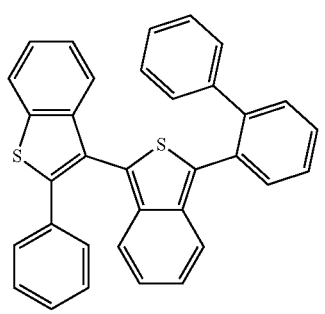
630
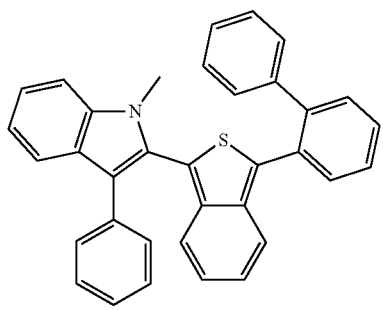
631
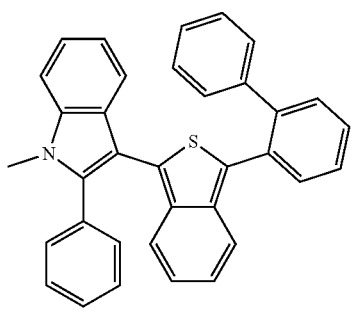
1238
-continued
632
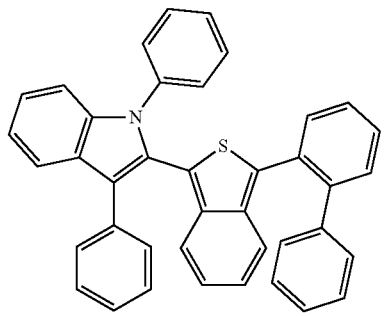
633
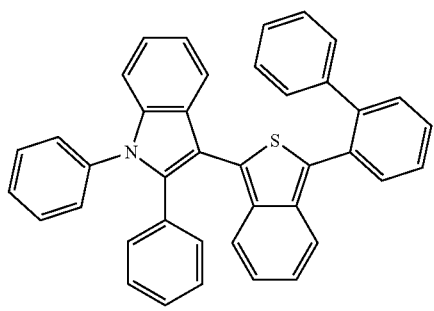
634
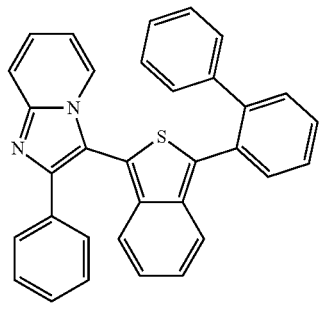
635
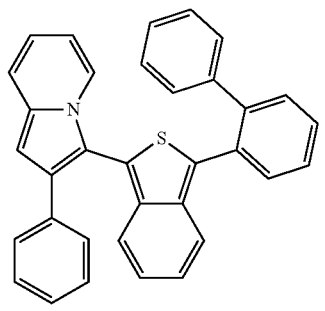
636
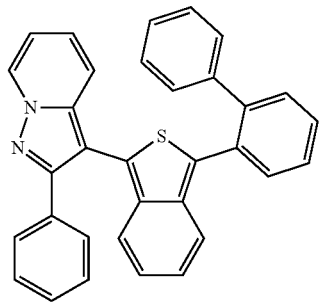

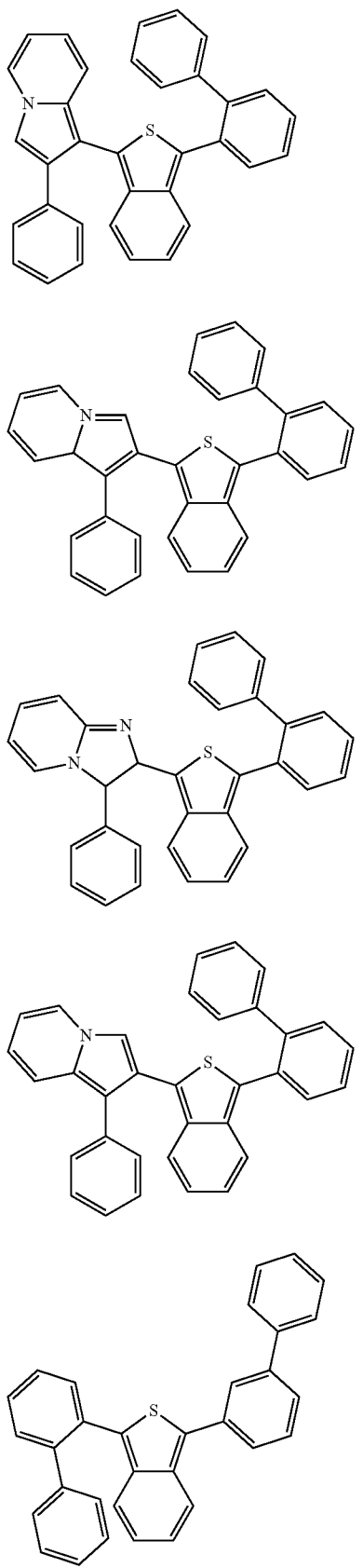
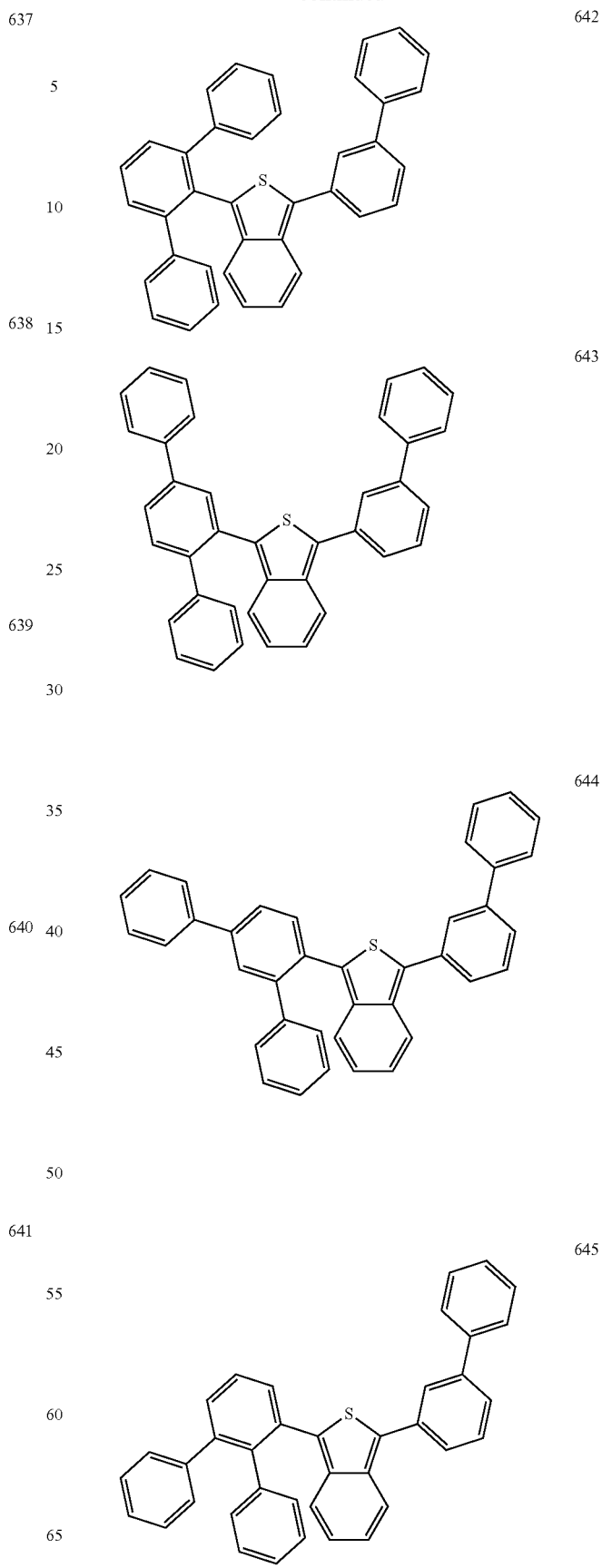

646
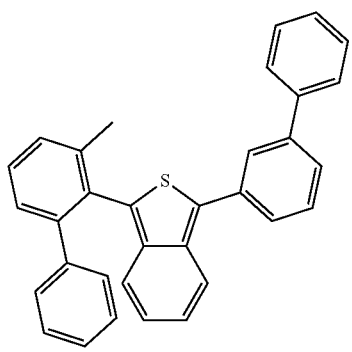
647
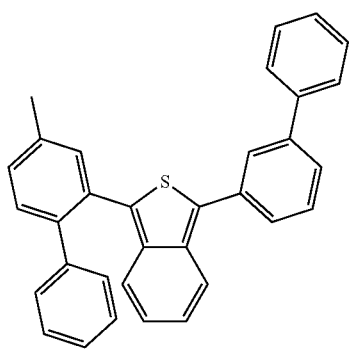
648
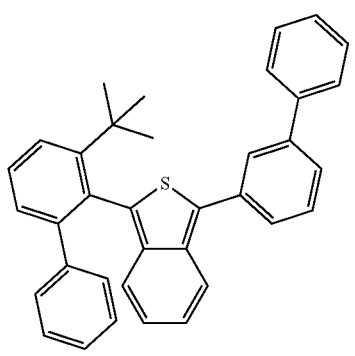
649
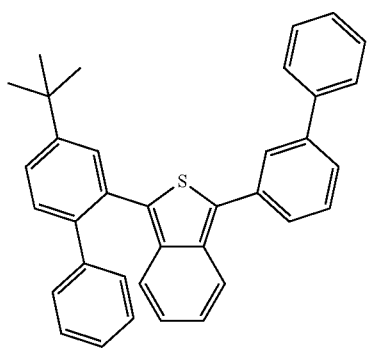
650
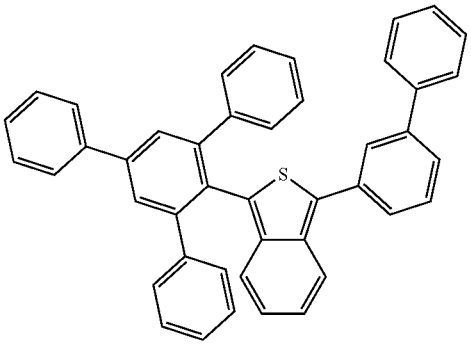
651
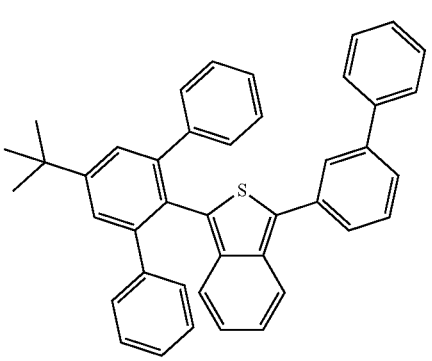
652
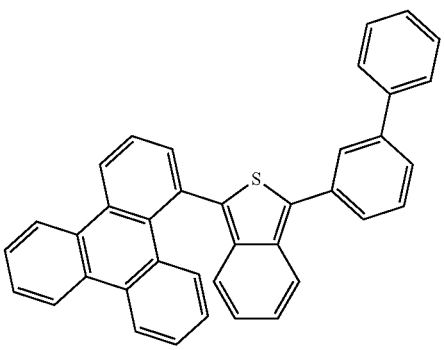
653
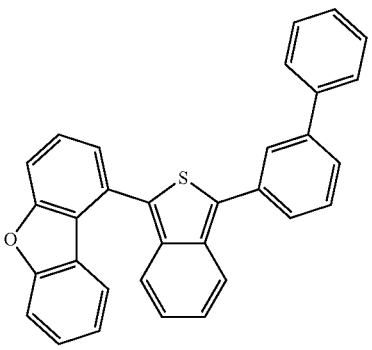

1243
-continued
654
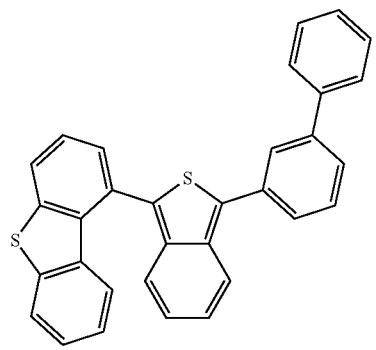
655
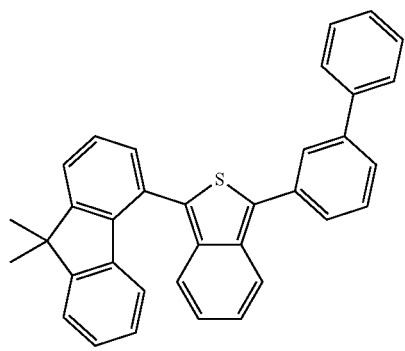
656
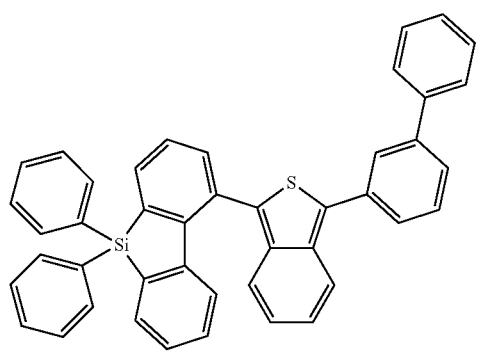
657
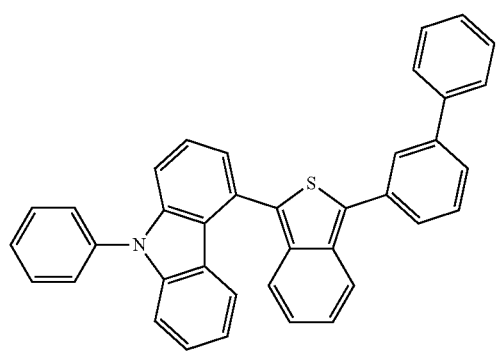
1244
-continued
658
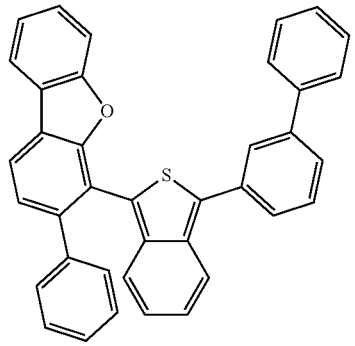
659
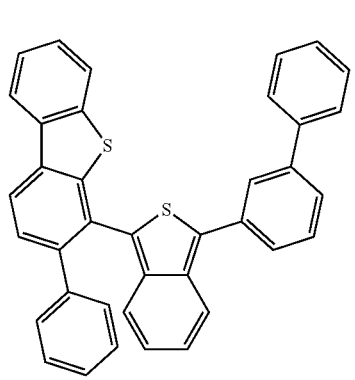
660
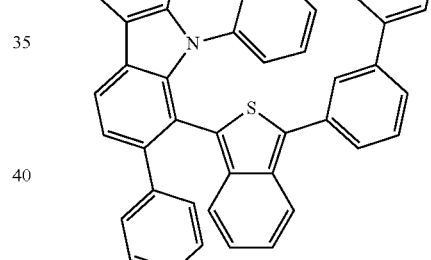
661
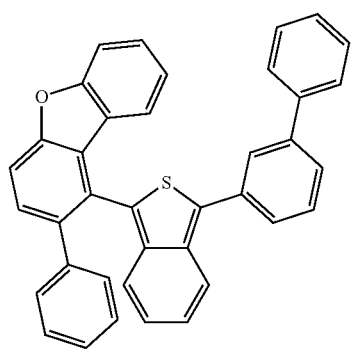

1245
-continued
662
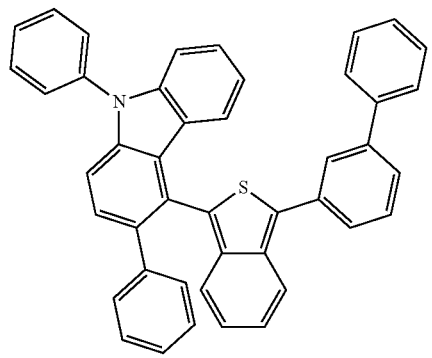
663
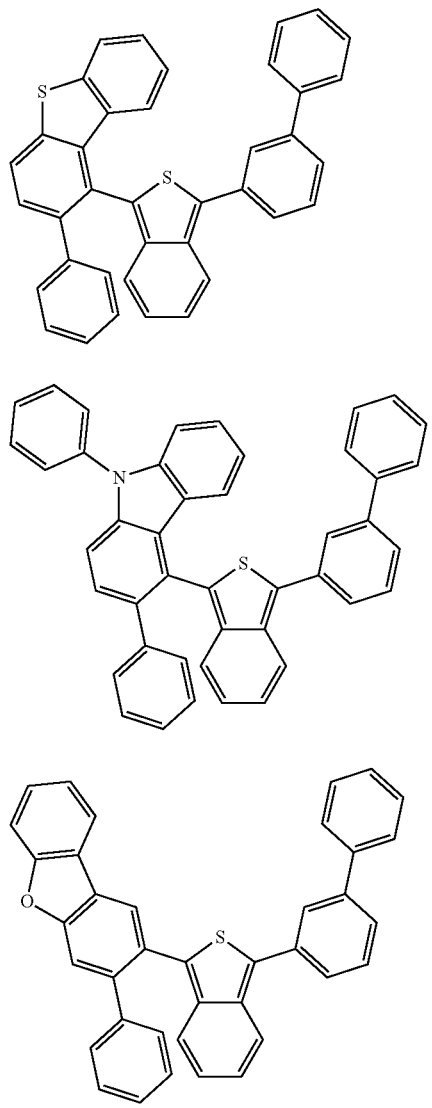
664
665
1246
-continued
666
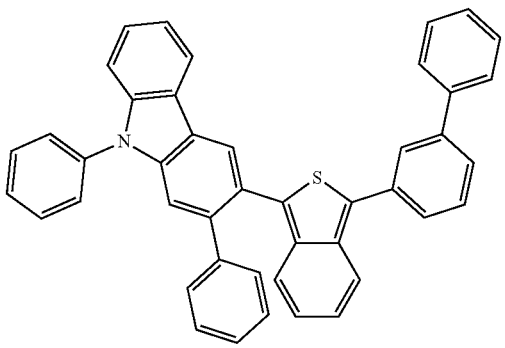
667
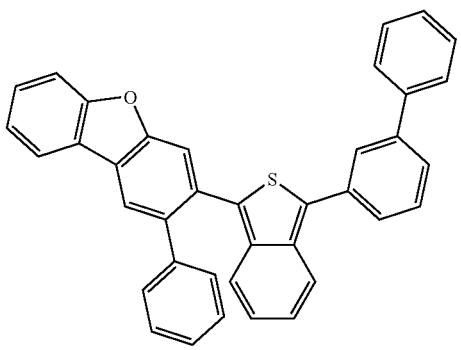
668
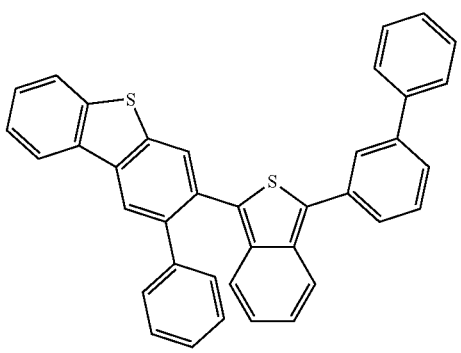
669
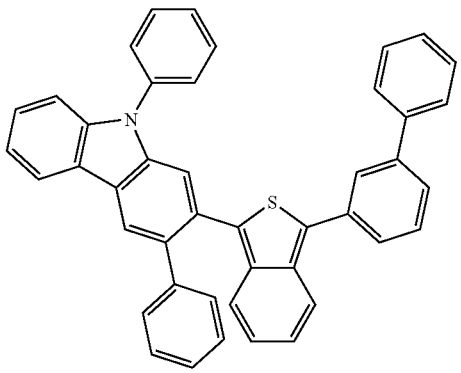

670
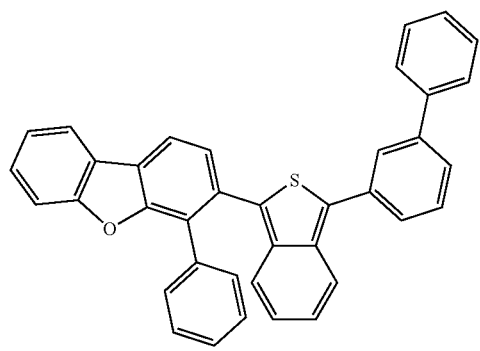
671
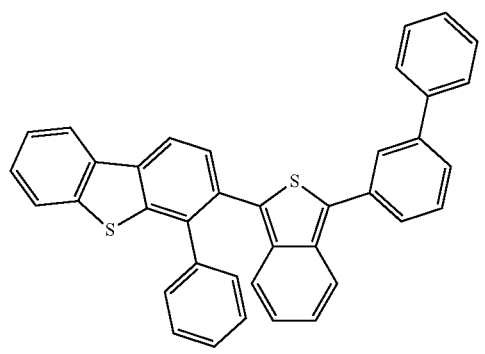
672
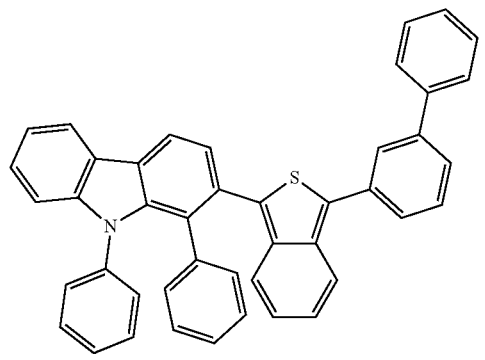
673
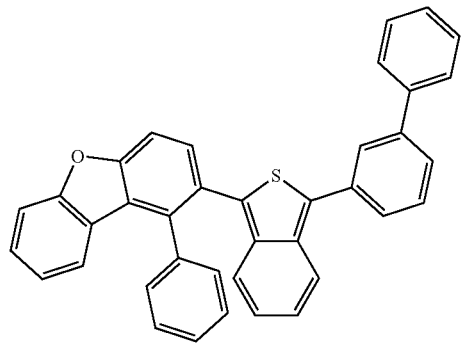
674
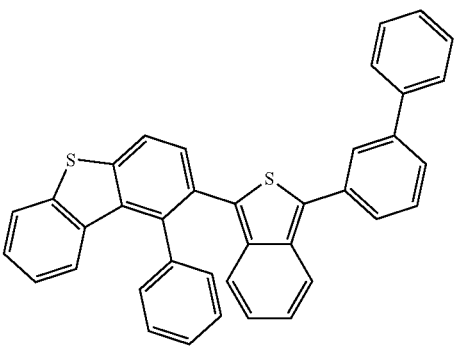
675
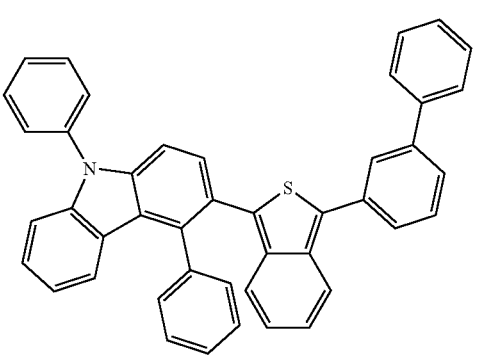
676
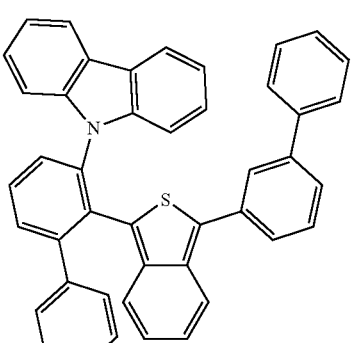
677
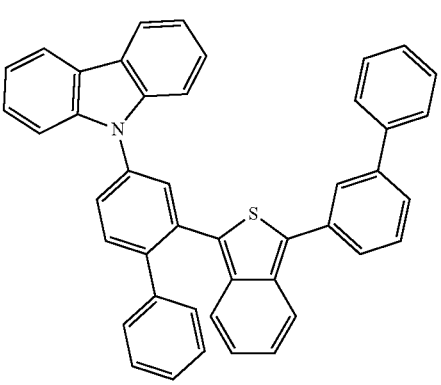

1249
-continued
678
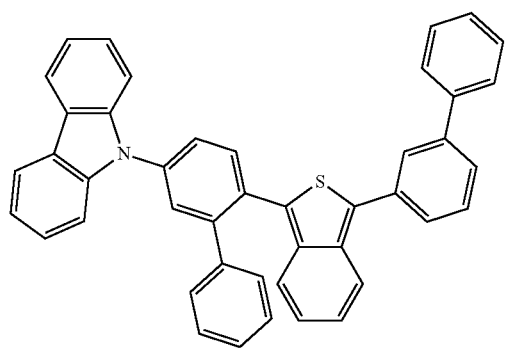
679
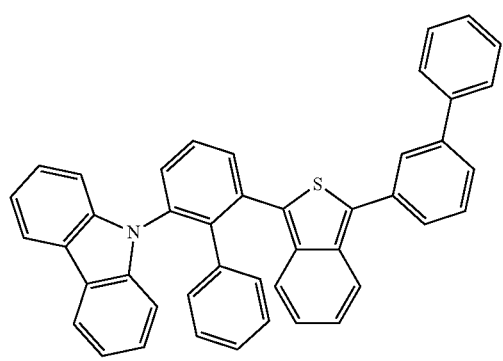
680
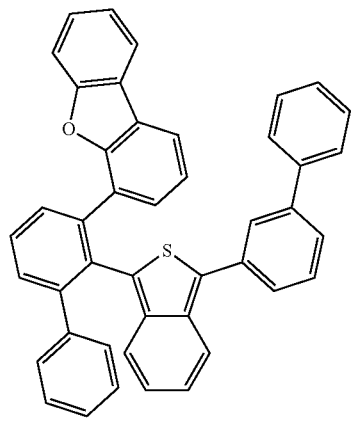
681
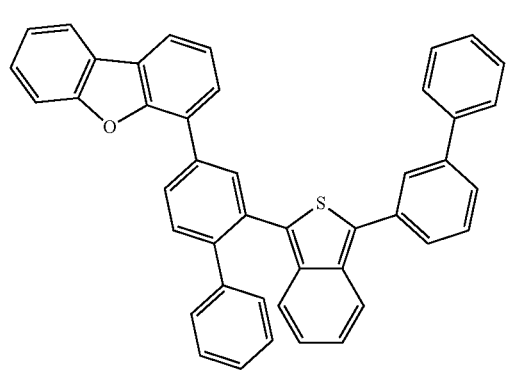
1250
-continued
682
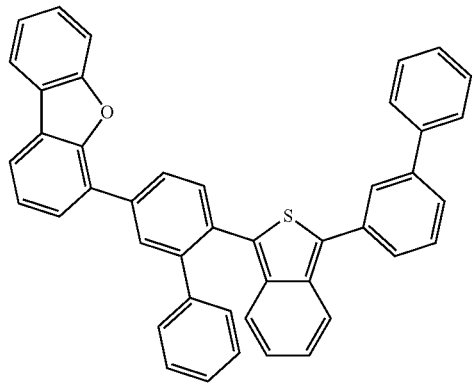
683
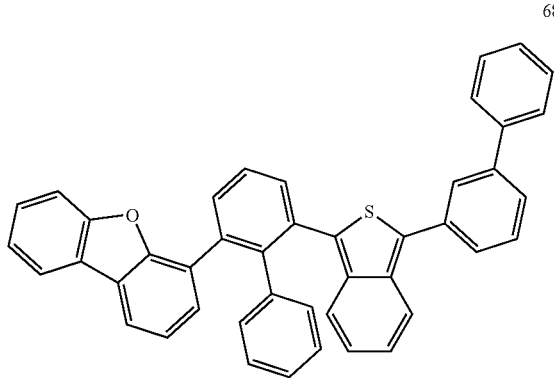
684
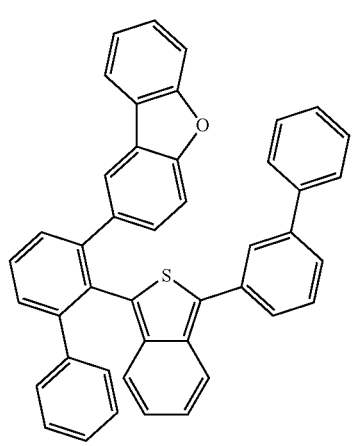
685
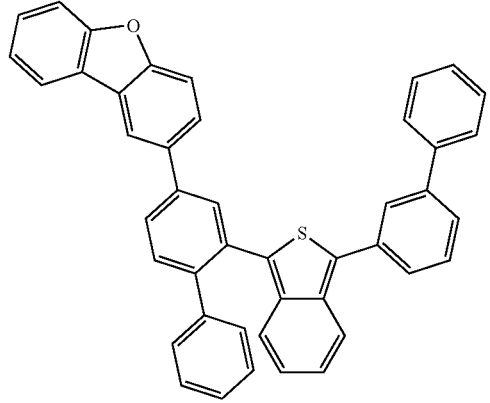

1251
-continued
686
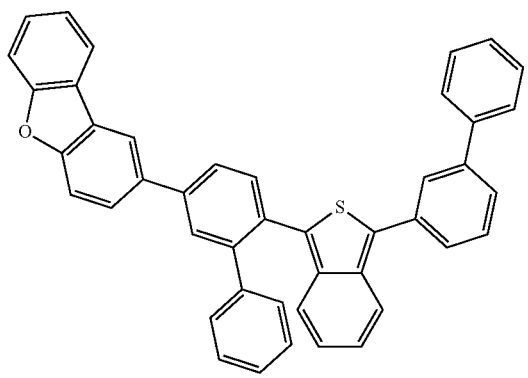
687
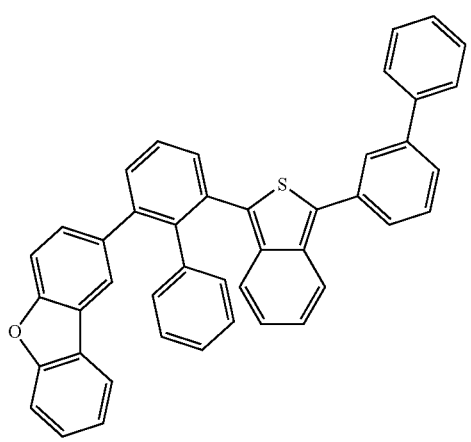
688
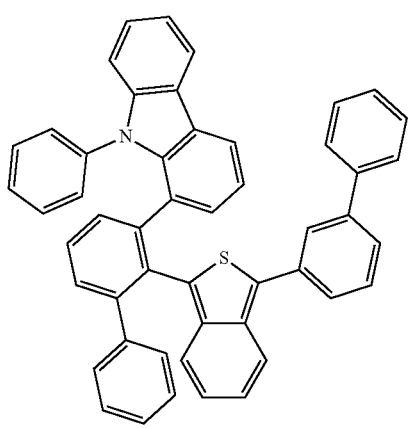
1252
-continued
689
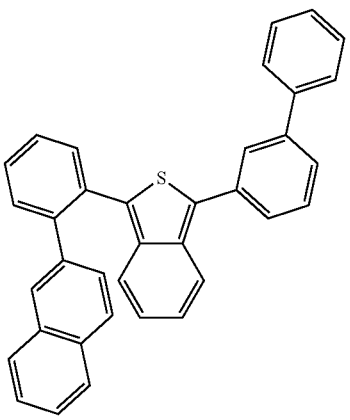
690
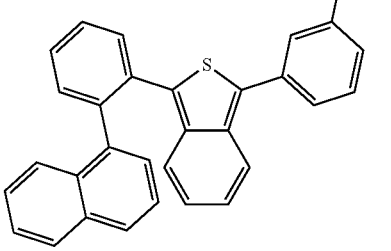
691
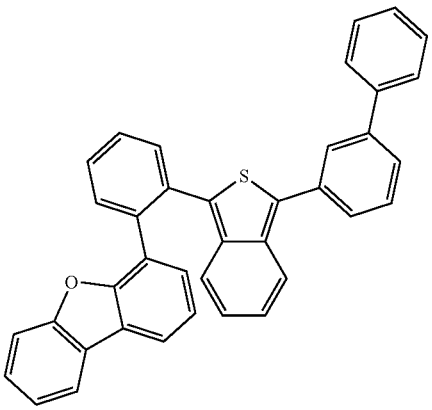
692
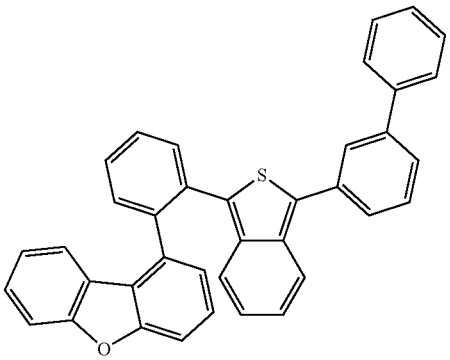

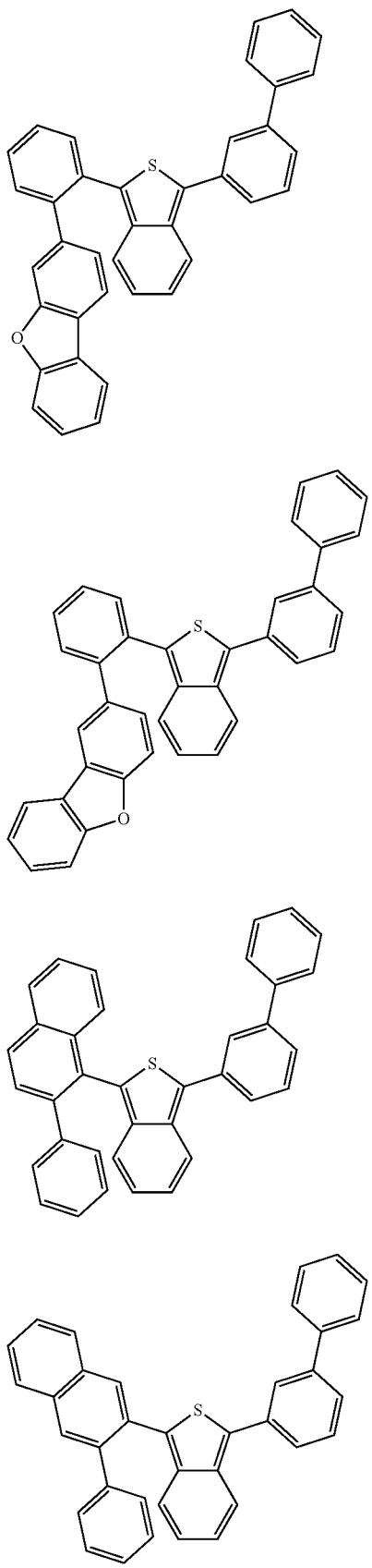
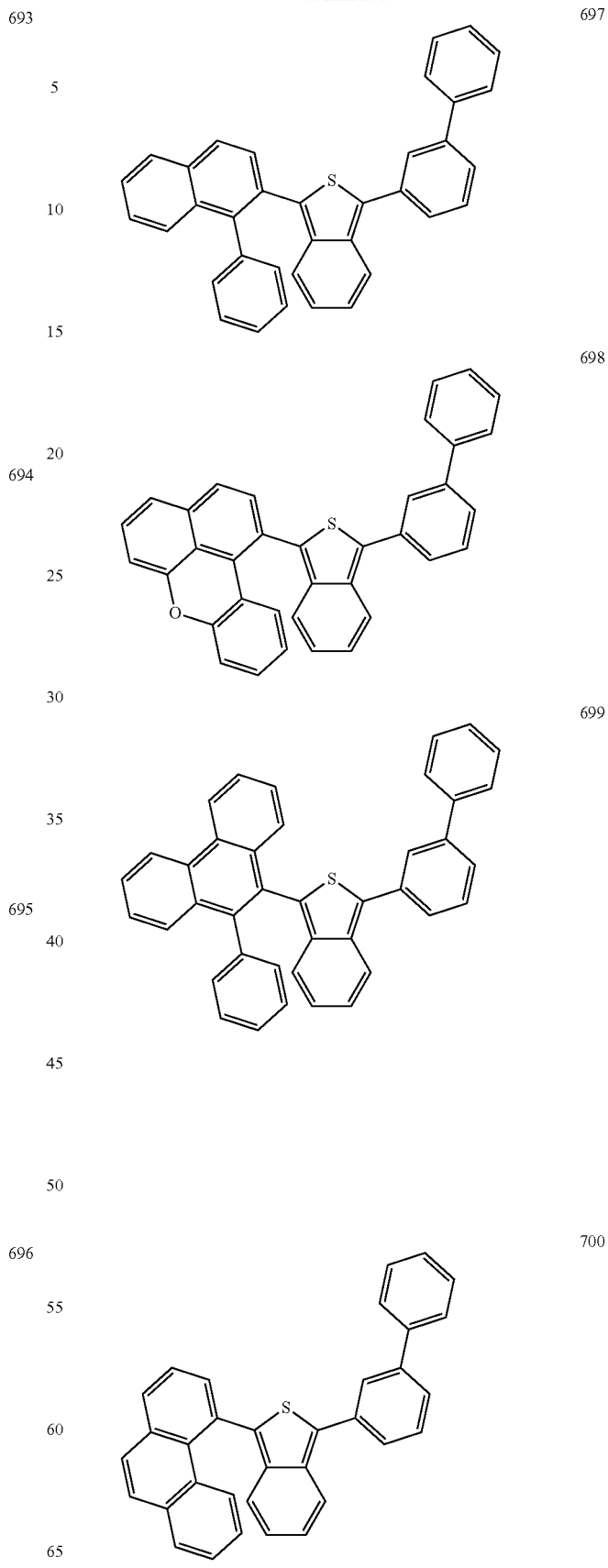

701
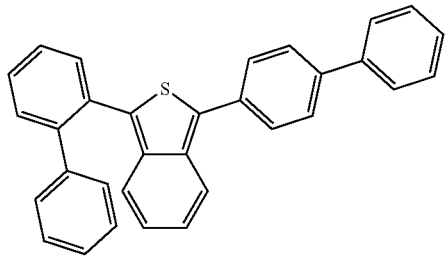
702
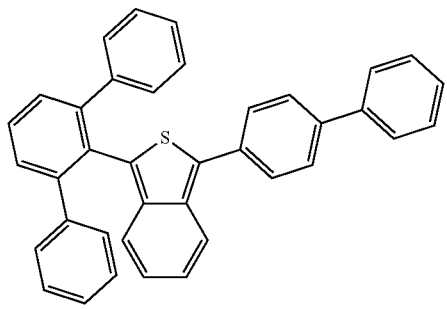
703
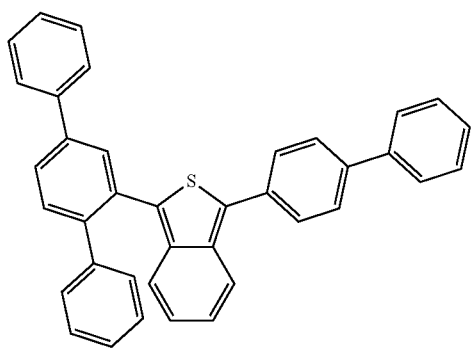
704
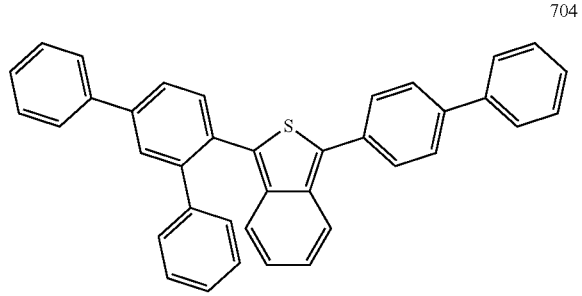
705
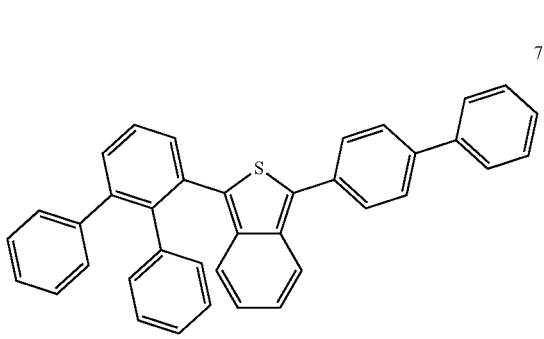
706
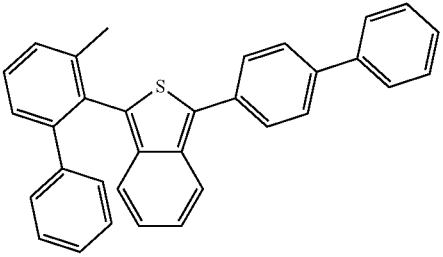
707
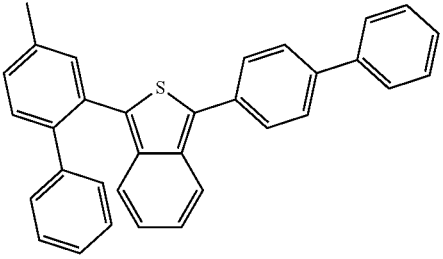
708
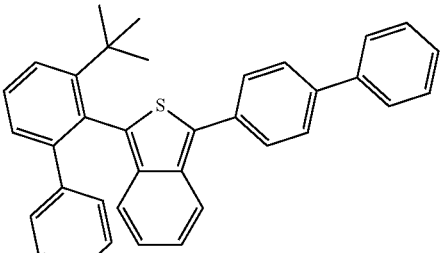
709
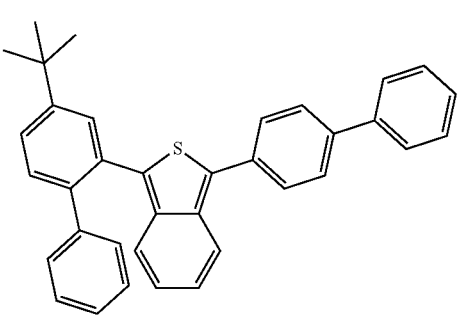
710
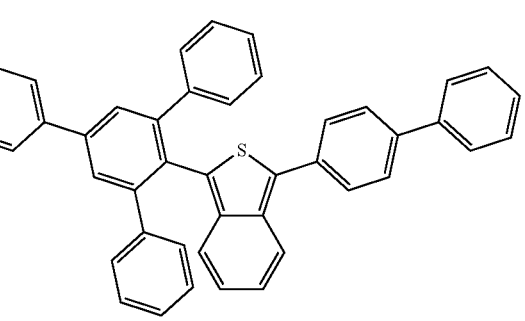

1257
-continued
711
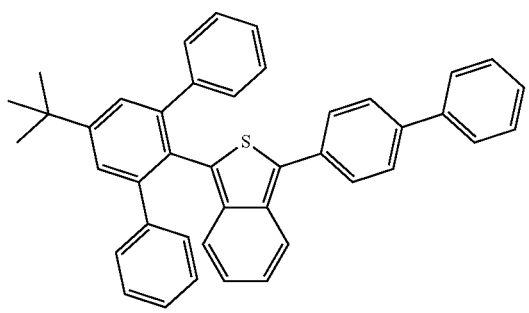
712
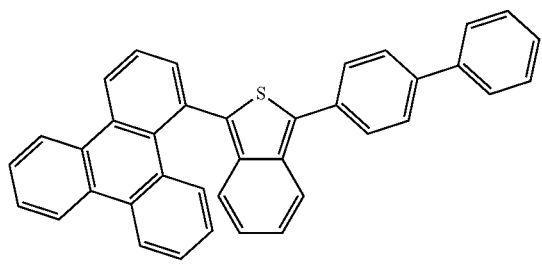
713
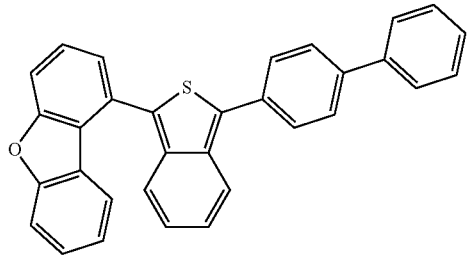
714
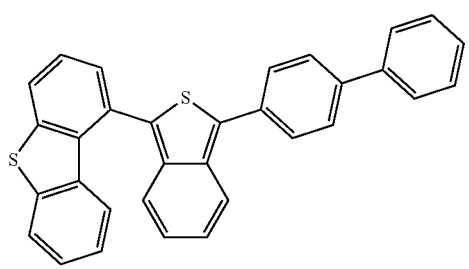
715

1258
-continued
716
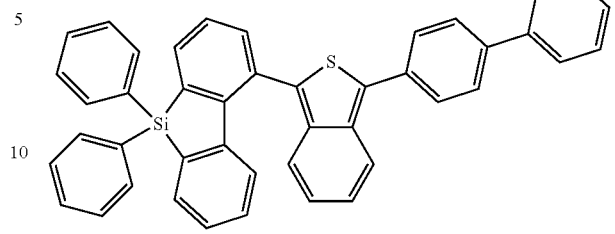
717
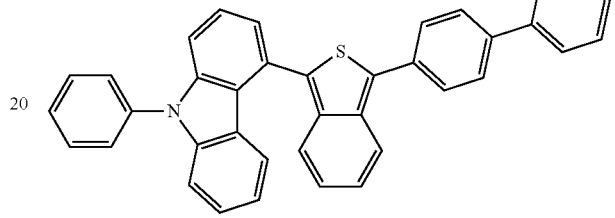
718
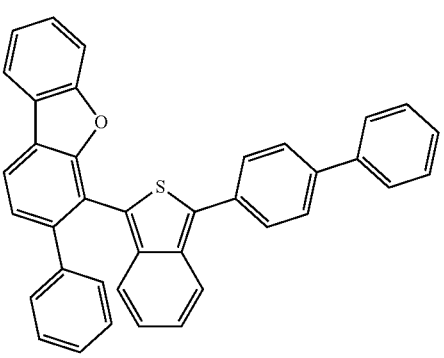
719
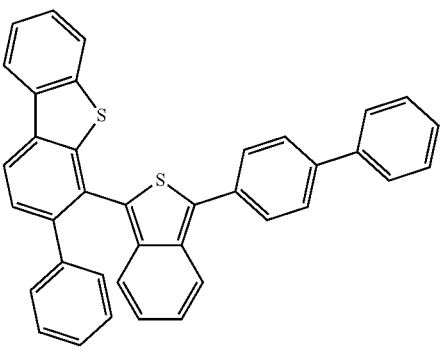
720
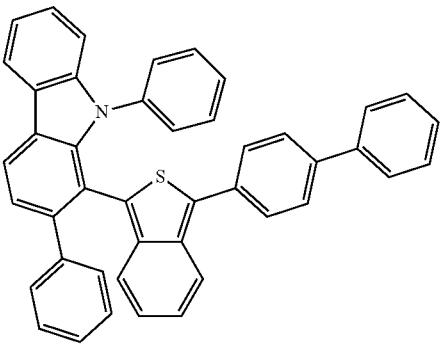

721
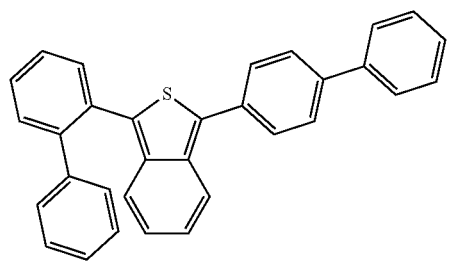
722
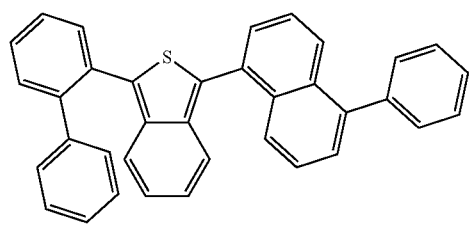
723
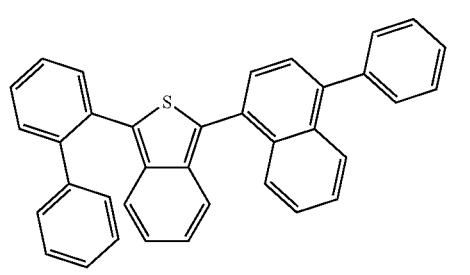
724
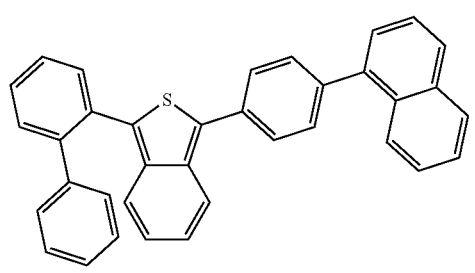
725
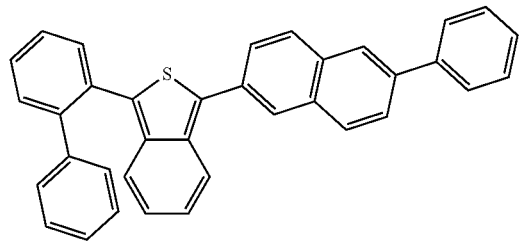
726
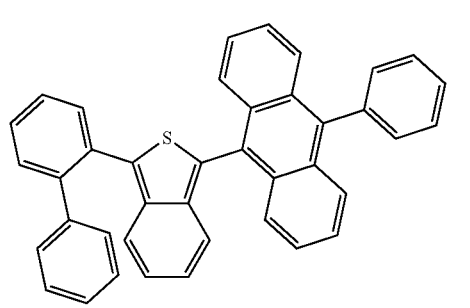
727
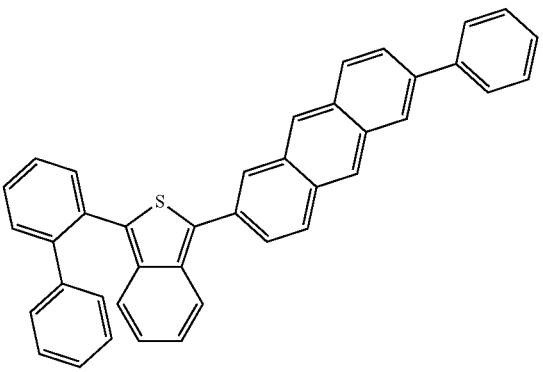
728
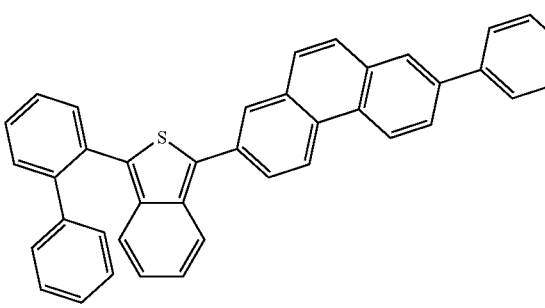
729
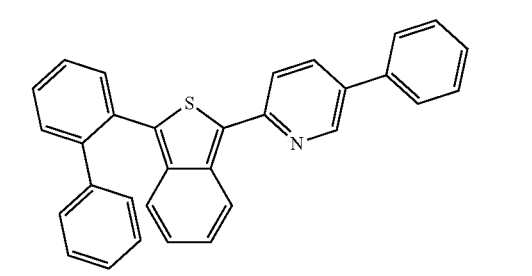
730
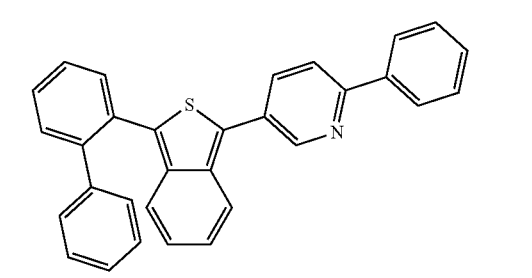
731
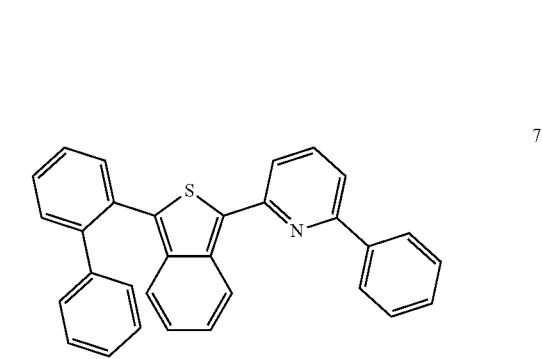

1261
-continued
732 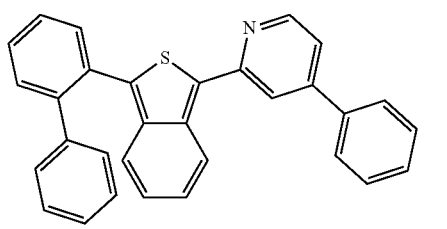
733 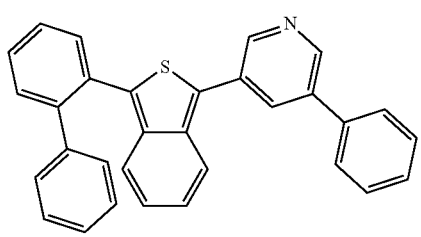
734 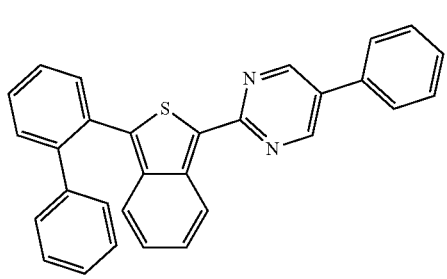
735 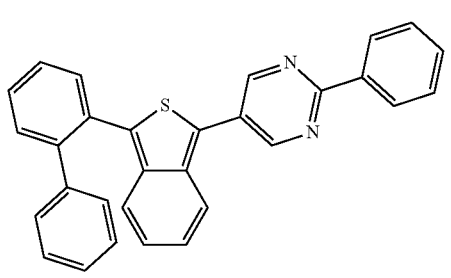
736 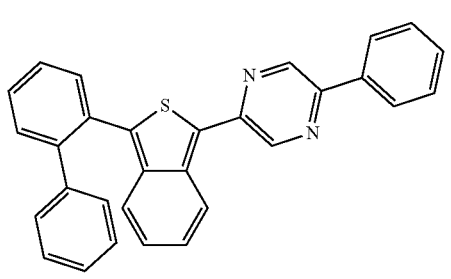
737 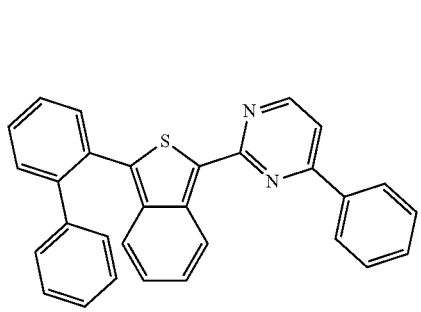
1262
-continued
738 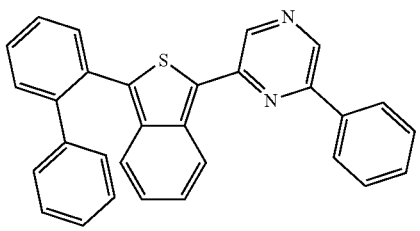
739 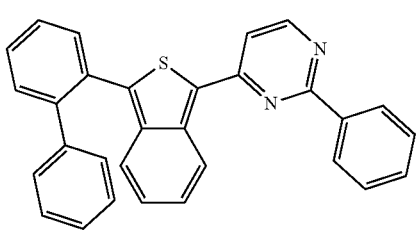
740 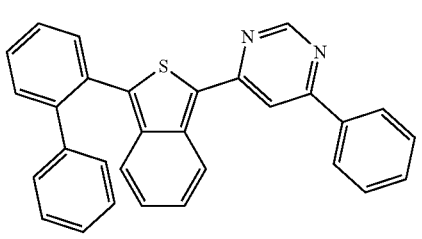
741 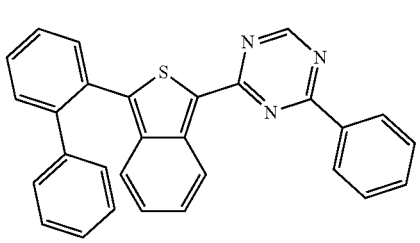
742 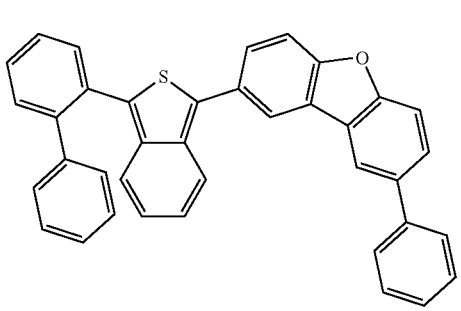
743 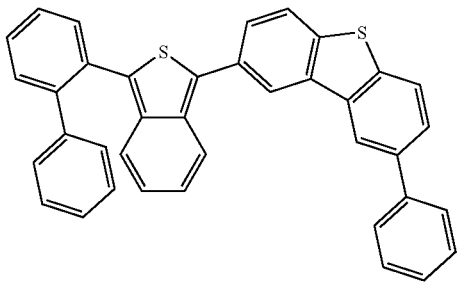

1263
-continued
1264
-continued
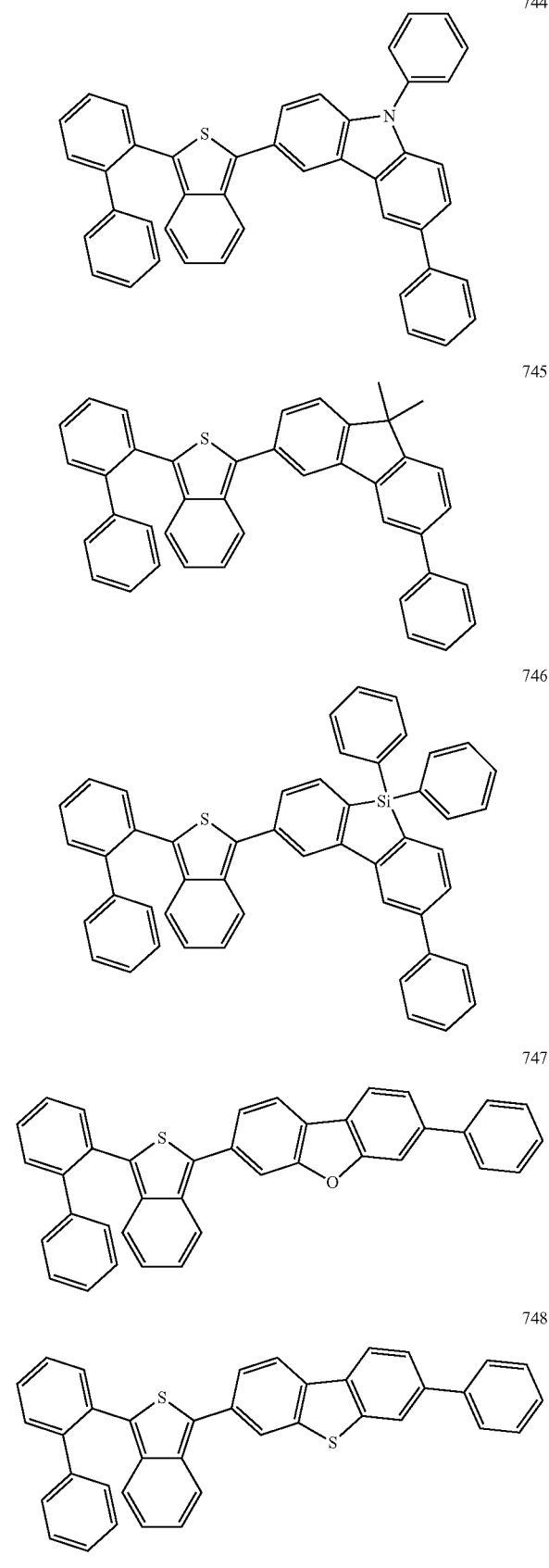
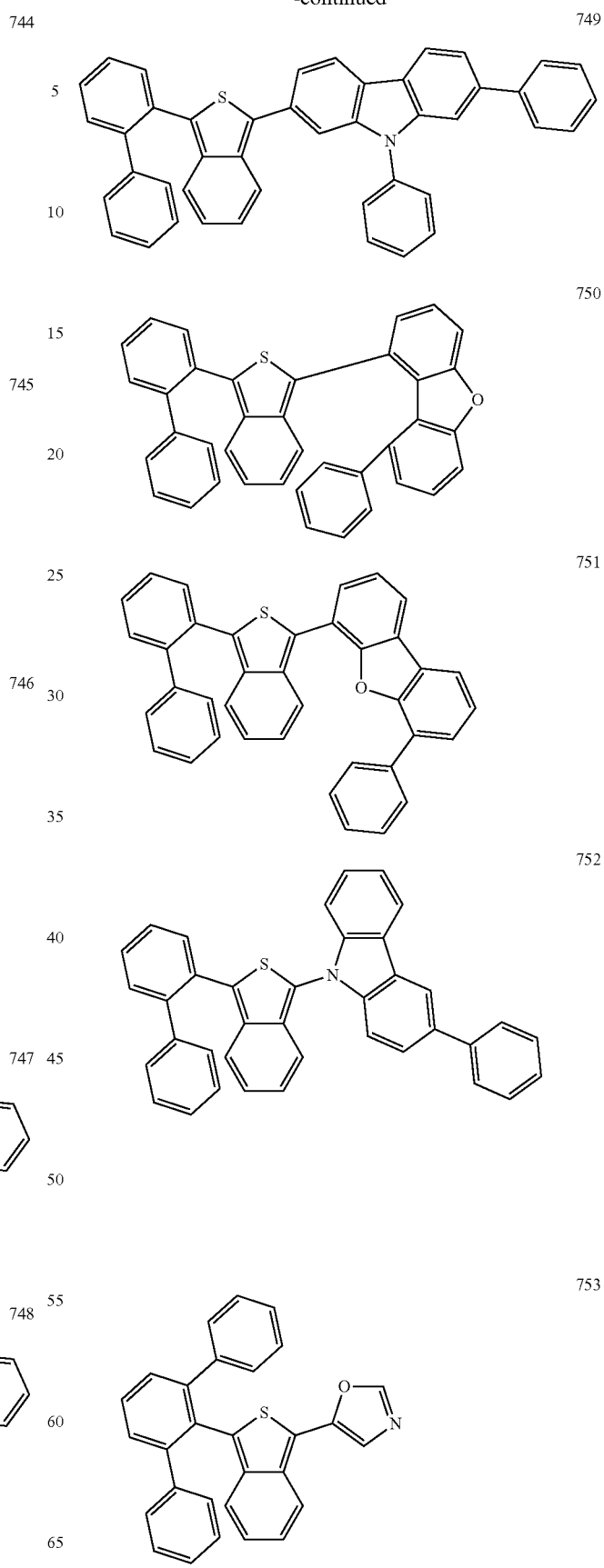

754
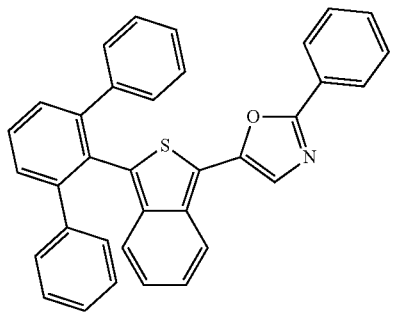
755
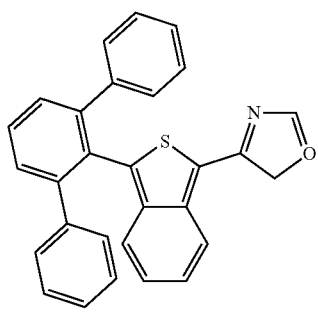
756
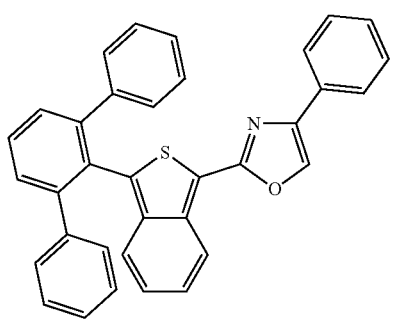
757
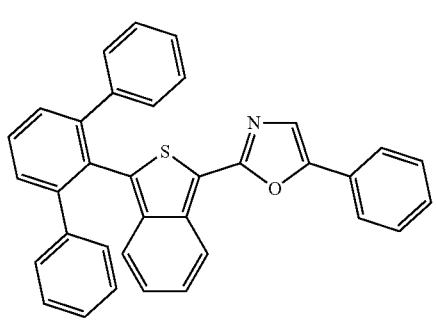
758
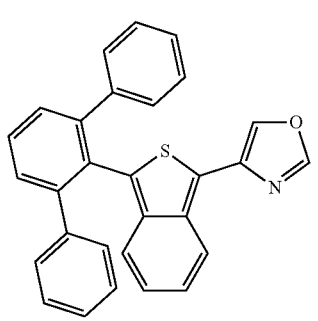
759
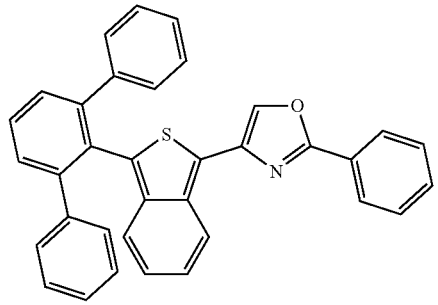
760
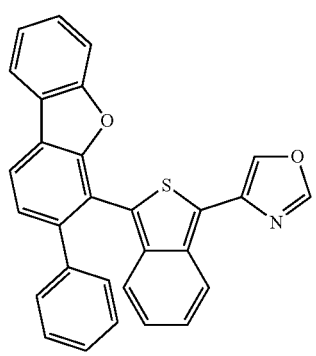
761
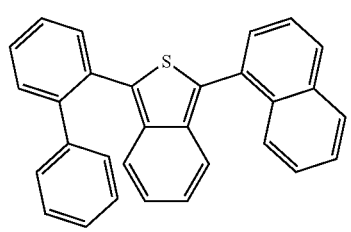
762
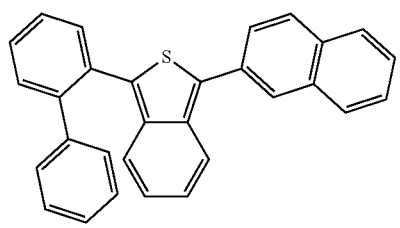
763
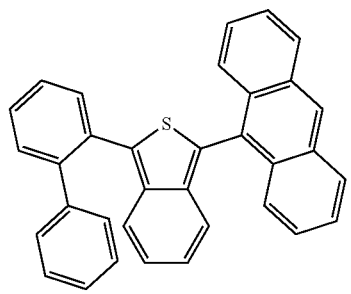

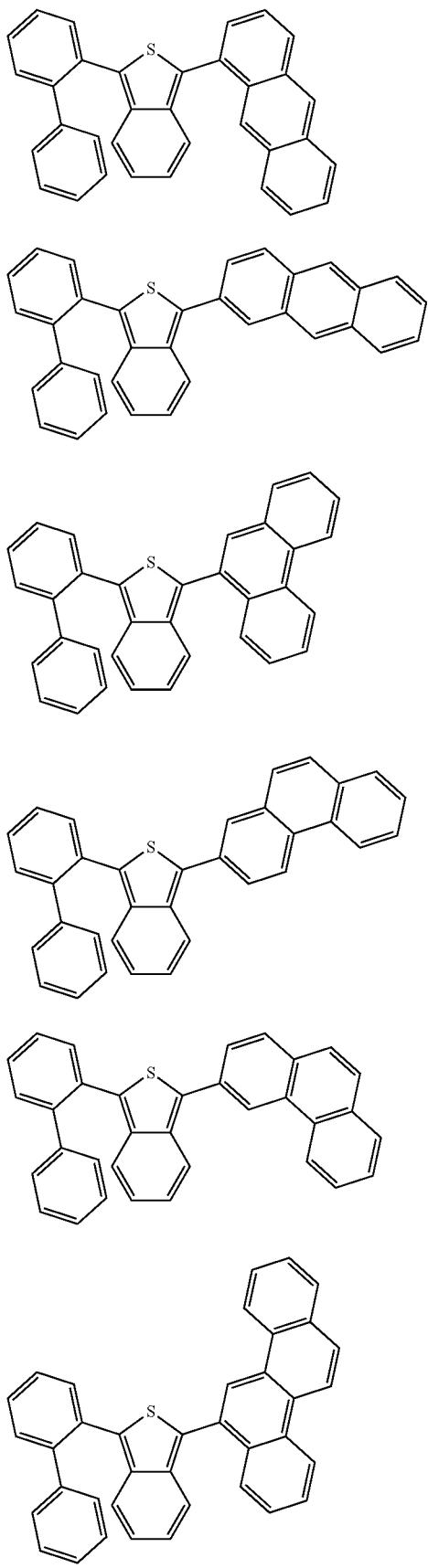
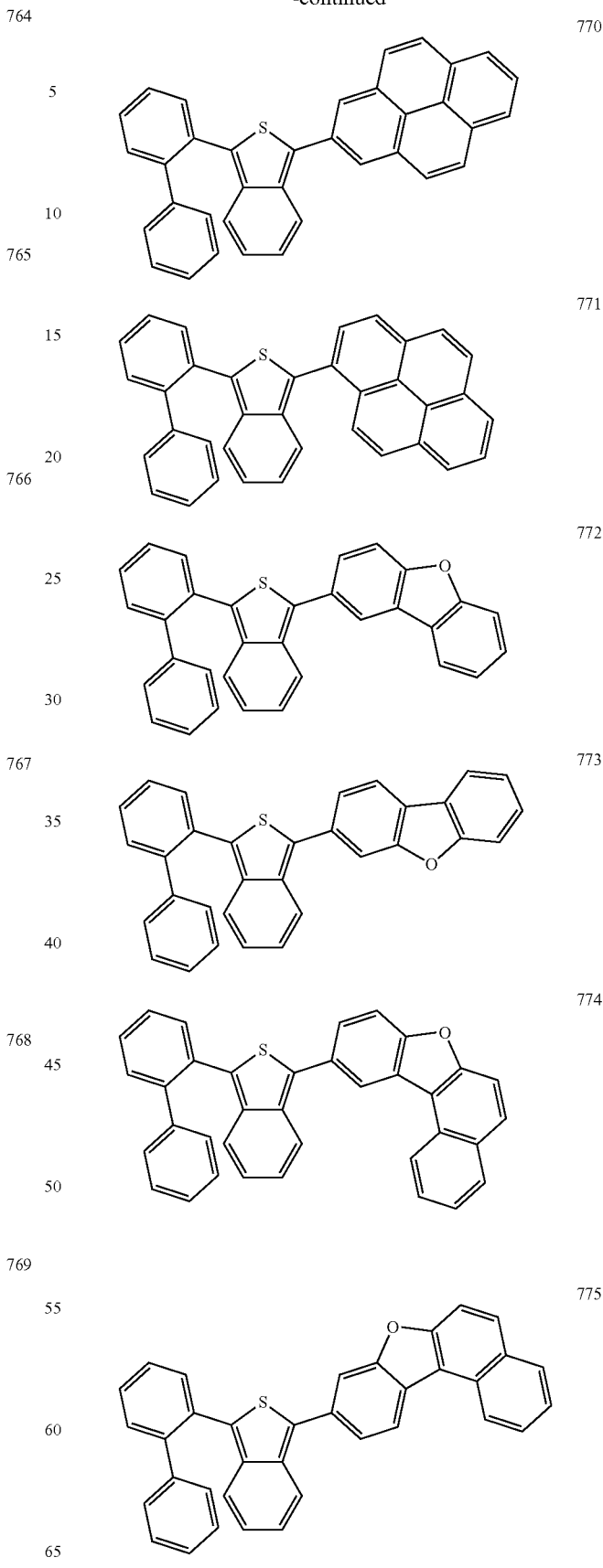

1269
-continued
776
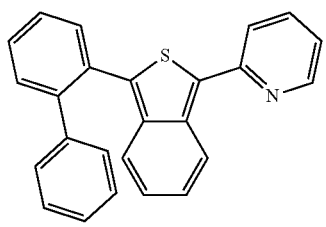
778
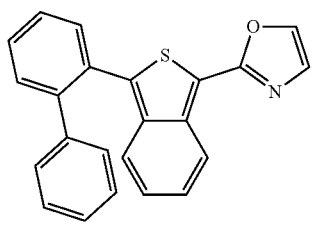
779
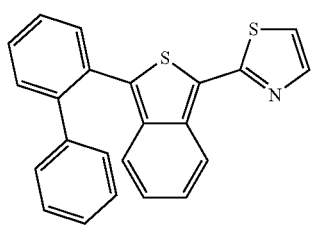
780
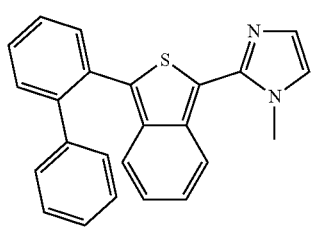
781
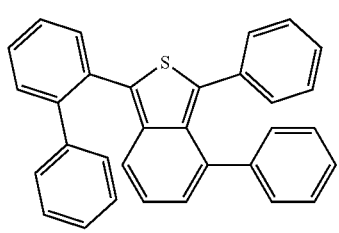
782
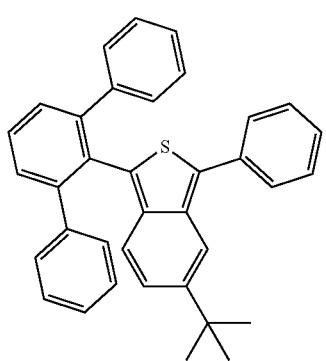
1270
-continued
783
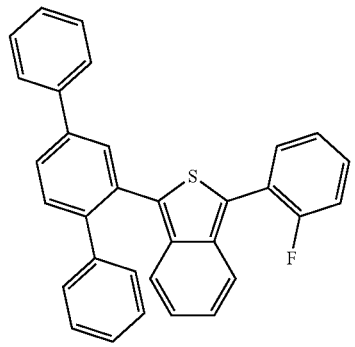
784
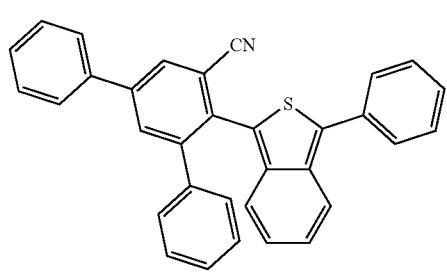
785
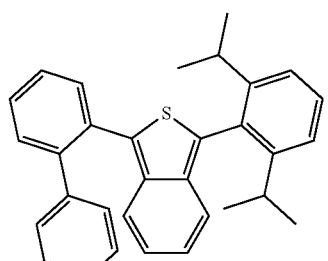
786
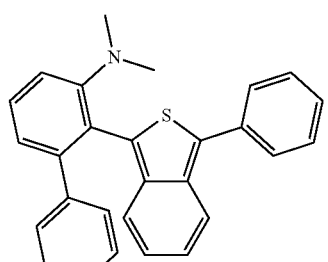
787
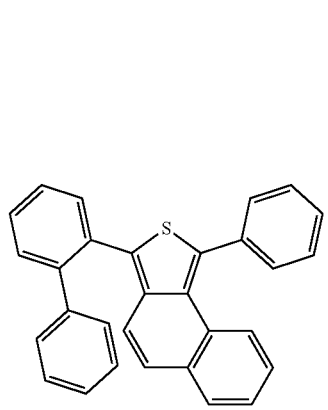

1271
-continued
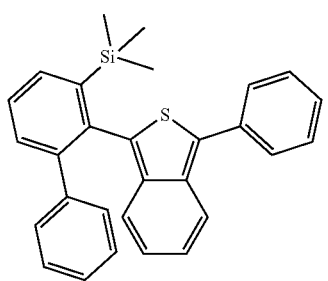
788
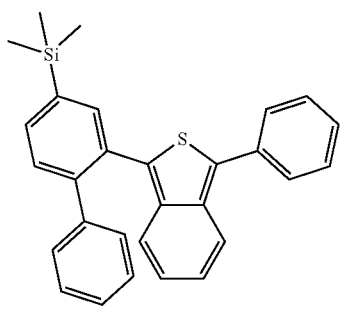
789
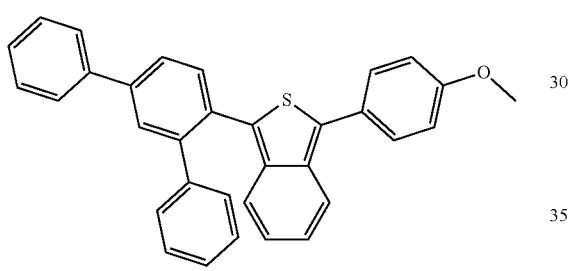
790
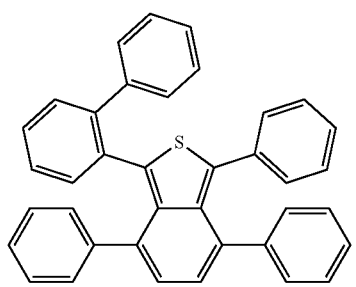
791
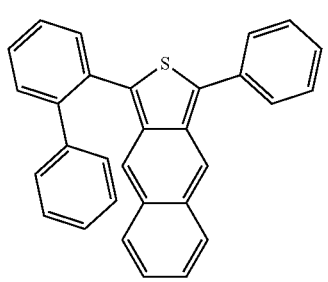
792
1272
-continued
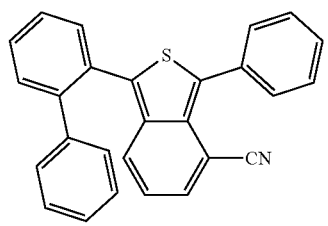
793
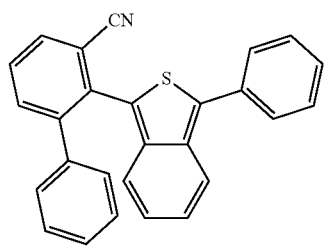
794
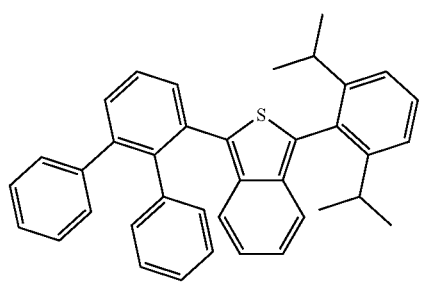
795
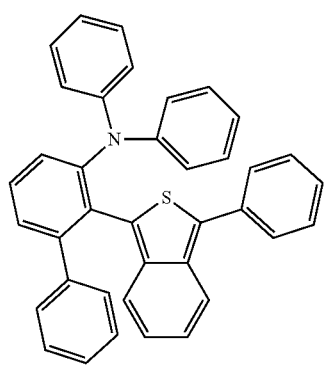
796
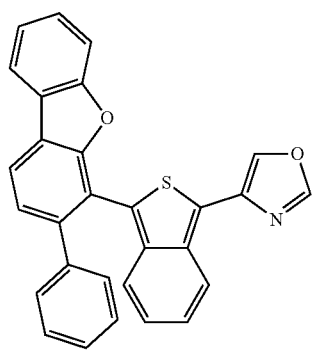
797

798

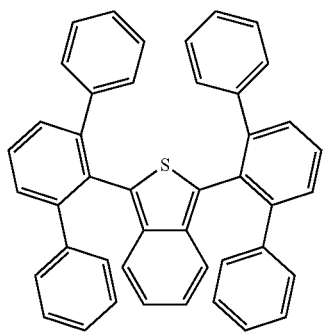

799

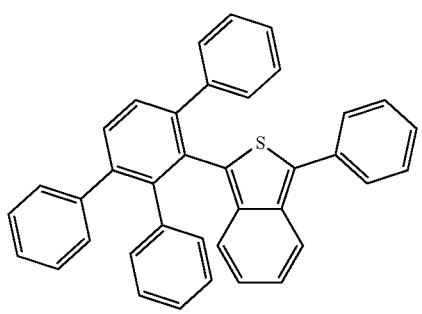

800

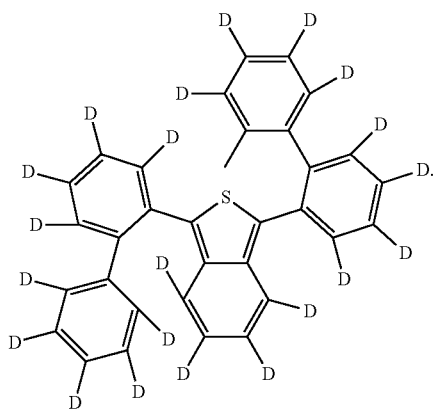

In some embodiments, the fluorescent host may be represented by Formula FH-3:

Formula FH-3

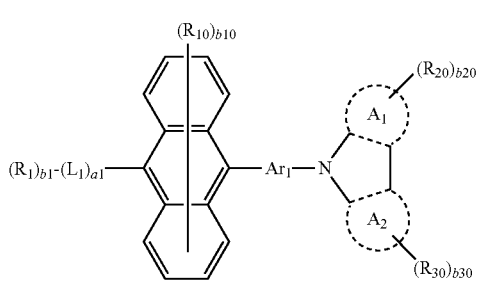

wherein, in Formula FH-3,
$Ar_1$ may be a group represented by Formula 2:

Formula 2

$$*—Ar_{11}\!-\!\!\left[Ar_{13}\right]_{m1}\!\!-\!Ar_{12}—*',$$

$Ar_1$ may include at least one cyano group,
$A_1$ and $A_2$ may each independently be a $C_5$-$C_{30}$ carbocyclic group or a $C_1$-$C_{30}$ heterocyclic group,
$L_1$ may be a substituted or unsubstituted $C_5$-$C_{30}$ carbocyclic group or a substituted or unsubstituted $C_1$-$C_{30}$ heterocyclic group,
a1 may be 0, 1, 2, or 3,
when a1 is 2 or greater, at least two $L_1$(s) may be identical to different from each other,
m1 may be 0, 1, 2, or 3, and
$Ar_{11}$ may be a group represented by Formula 4, $Ar_{12}$ may be a group represented by Formula 5, or $Ar_{13}$ may be a group represented by Formula 6:

Formula 4

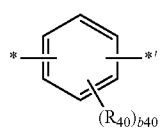

Formula 5

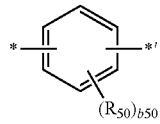

Formula 6

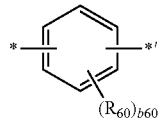

wherein, in Formulae 4 to 6,
$R_1$, $R_{10}$, $R_{20}$, $R_{30}$, $R_{40}$, $R_{50}$, and $R_{60}$ may each independently be hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), or —P(=O)($Q_8$)($Q_9$), b1 may be an integer from 1 to 5, when b1 is 2 or greater, at least two $R_1$(s) may be identical to or different from each other, b10 may be an integer from 1 to 8, when b10 is 2 or greater, at least two $R_{10}$(s) may be identical to or different from each other, b20 and b30 may each independently be an integer from 1 to 4, when b20 is 2 or greater, at least two $R_{20}$(s) may be identical to or different from each other, and when b30 is 2 or greater, at least two $R_{30}$(s) may be identical to or different from each other, b40, b50, and b60 may each independently be an integer from 1 to 4, when b40 is 2 or greater, at least two $R_{40}$(s) may be identical to or different from each other, when b50 is 2 or greater, at least two $R_{50}$(s) may be identical to or different from each other, and when b60 is 2 or greater, at least two $R_{60}$(s) may be identical to or different from each other, and

* and ** each indicate a binding site to an adjacent atom.

In some embodiments, the fluorescent host represented by Formula FH-3 may be Group FH3, but embodiments are not limited thereto:

Group FH3

1

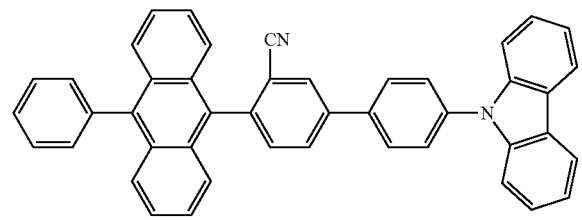

2

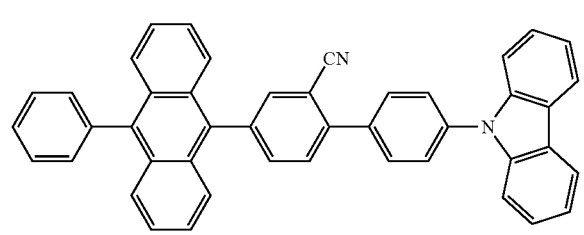

3

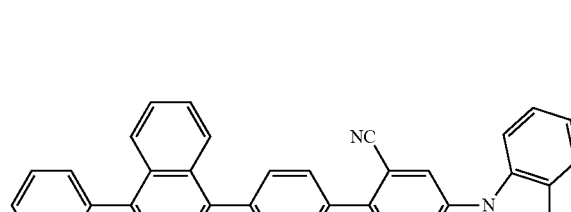

-continued

4

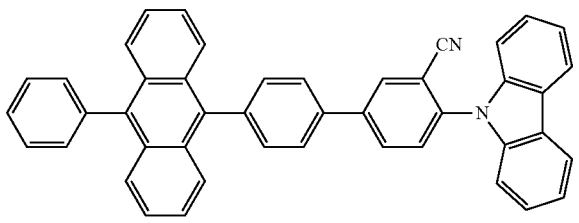

5

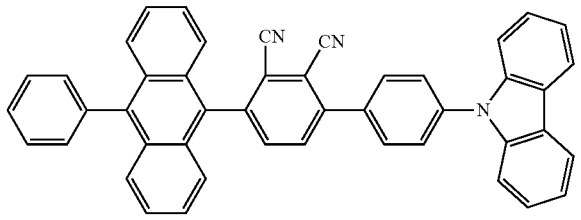

6

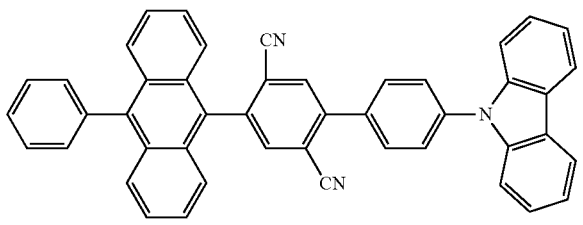

7

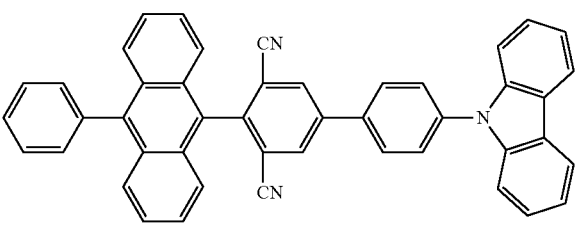

8

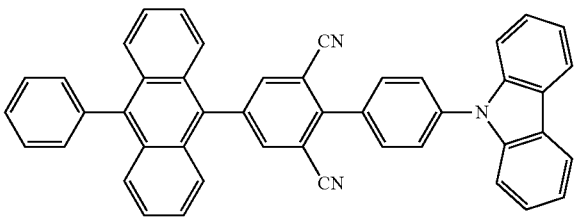

9

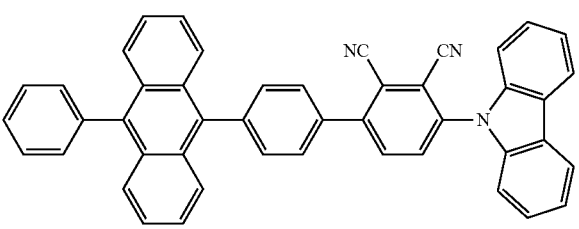

1277
-continued
10
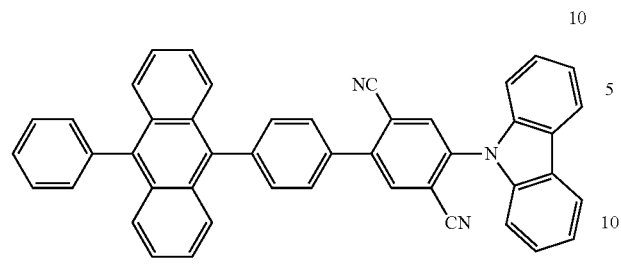
11
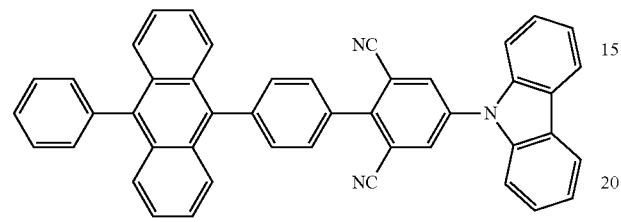
12

13

14

15

1278
-continued
16
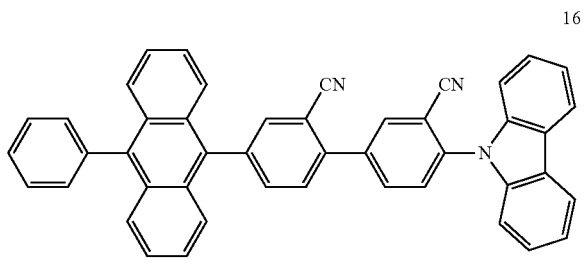
17
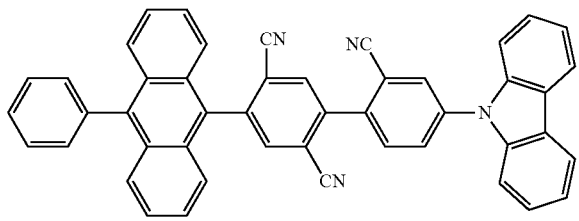
18
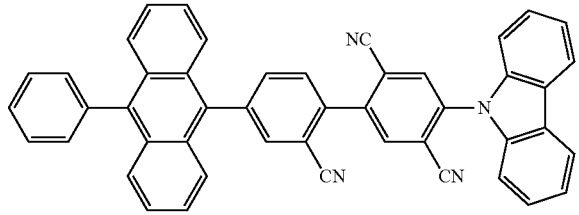
19
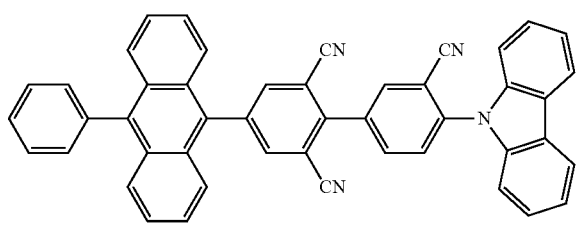
20
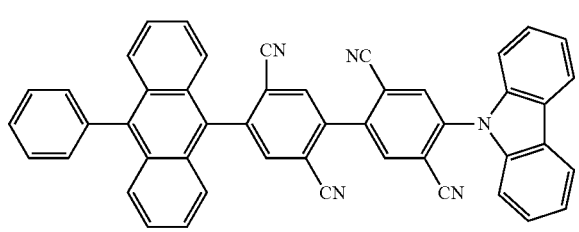
21
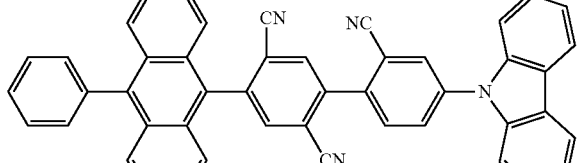

1279
-continued
22
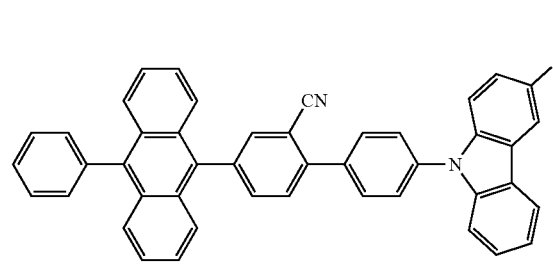
23
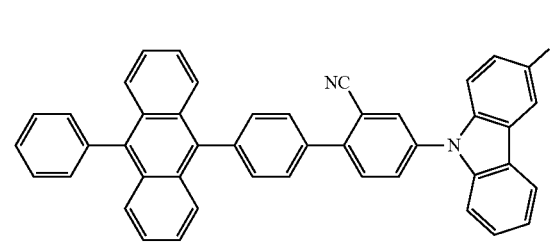
24
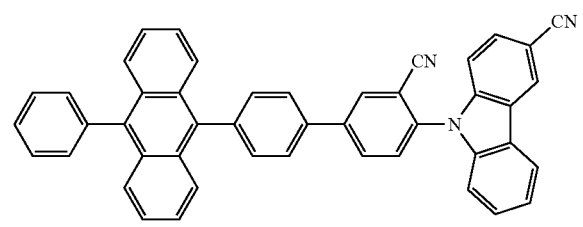
25
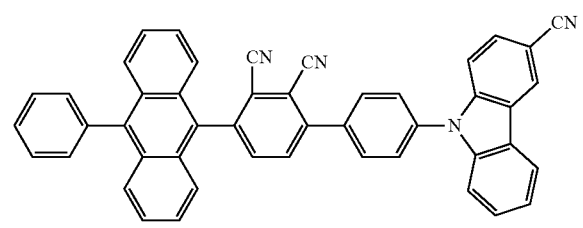
26
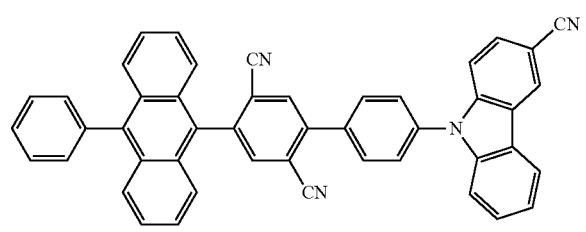
27
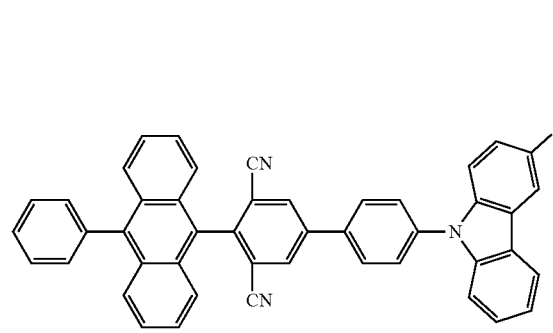
1280
-continued
28
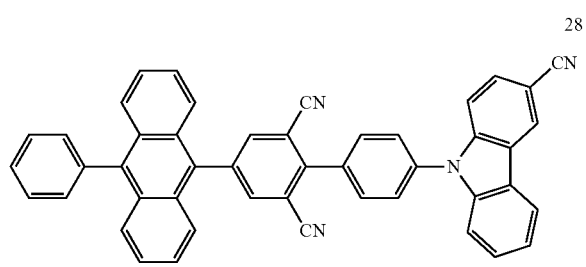
29
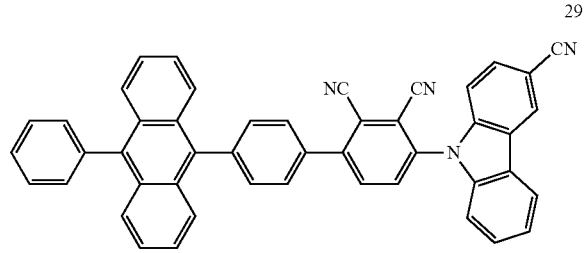
30
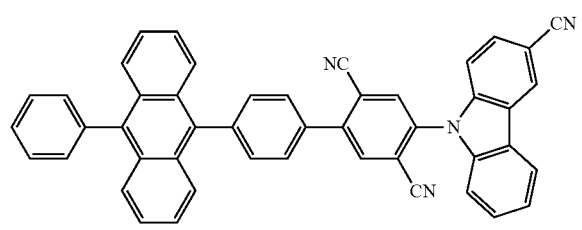
31
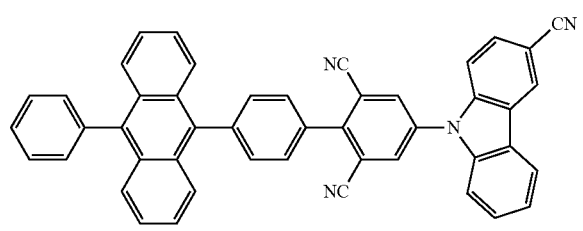
32
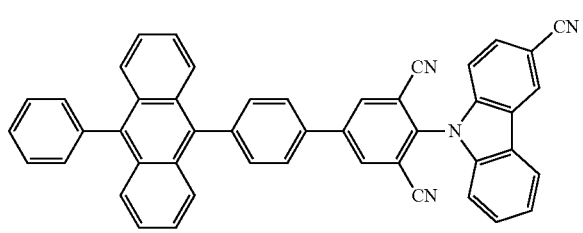
33
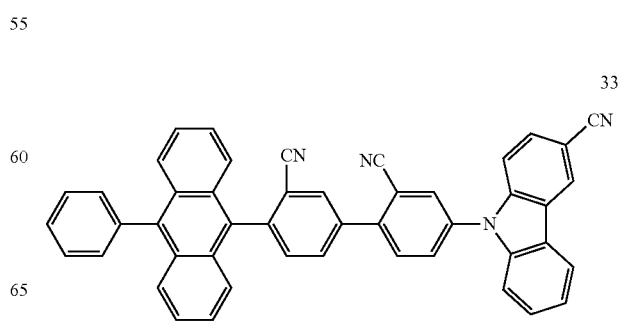

-continued

34

35

36

37

38

39

-continued

40

41

42

43

1283
44
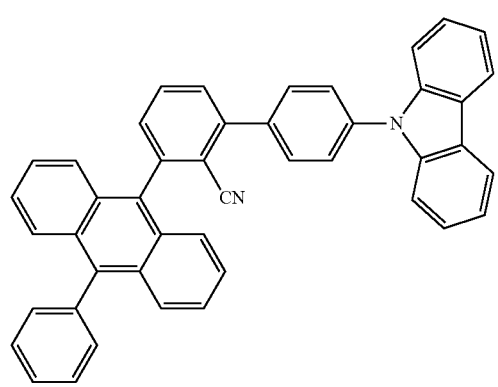
45
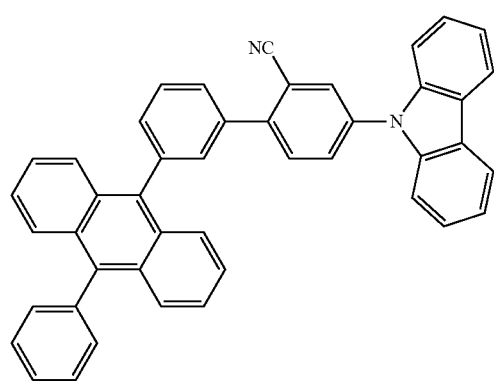
46
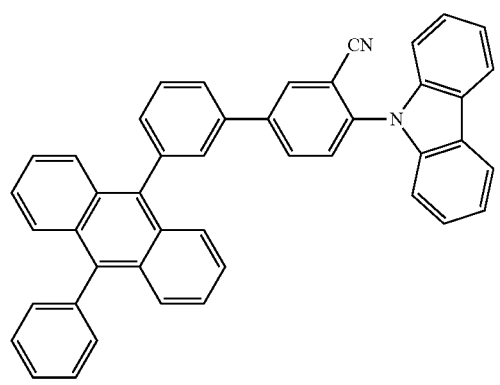
47
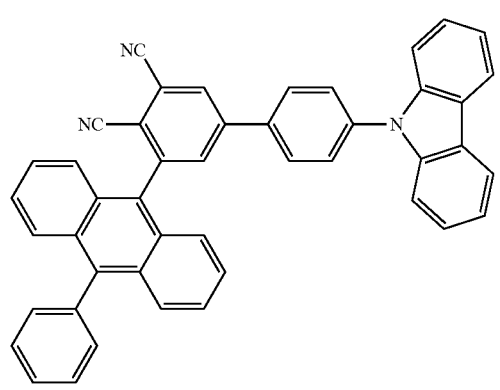
1284
48
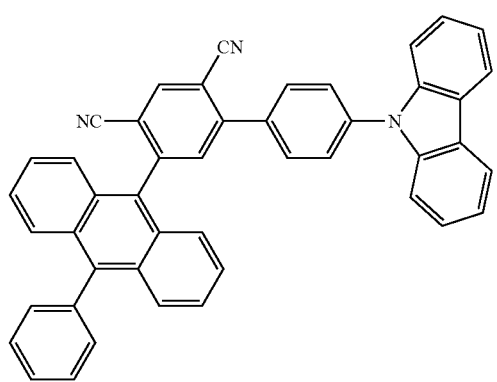
49
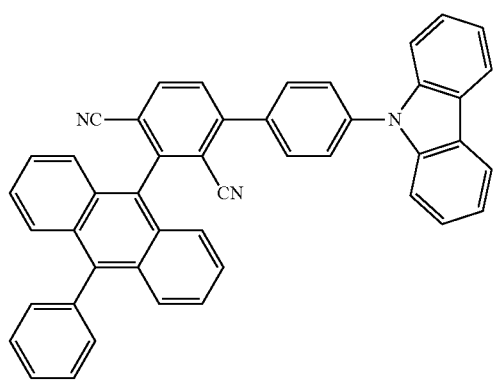
50
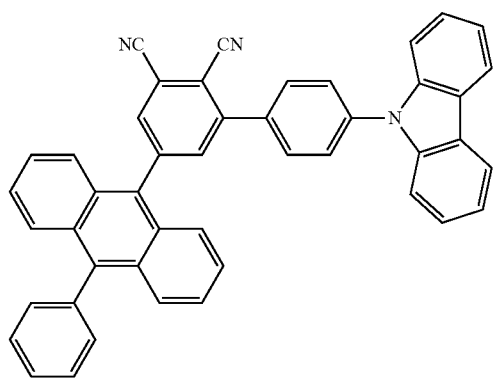
51
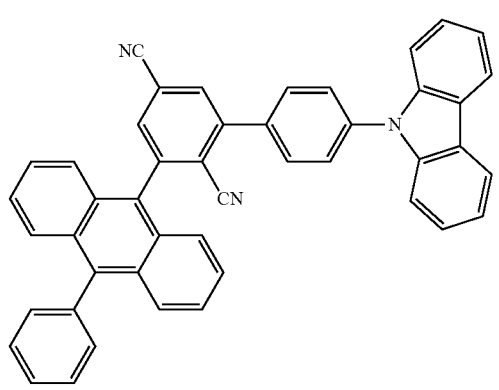

1285
-continued
52
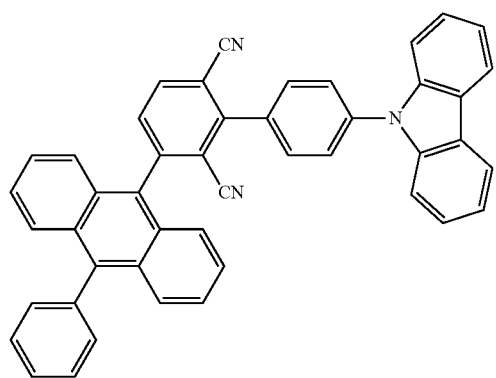
53
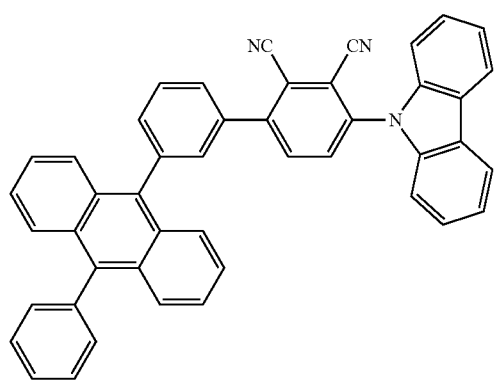
54

55

1286
-continued
56
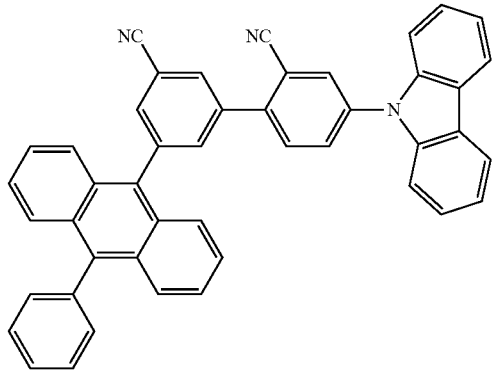
57
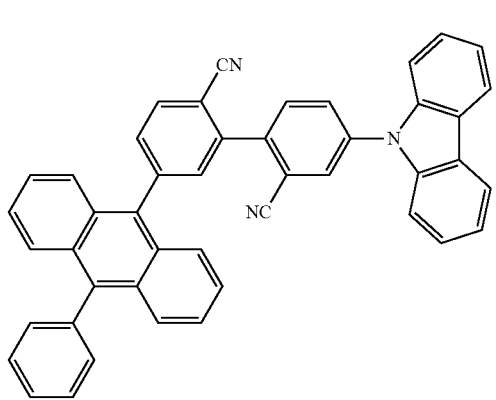
58
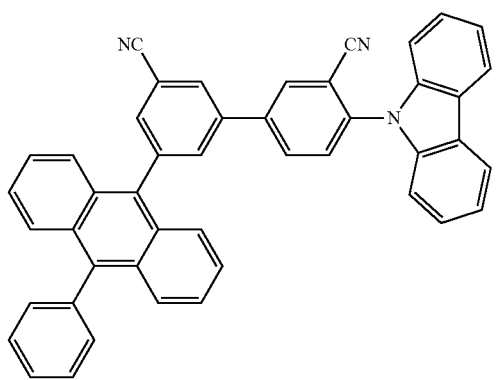
59
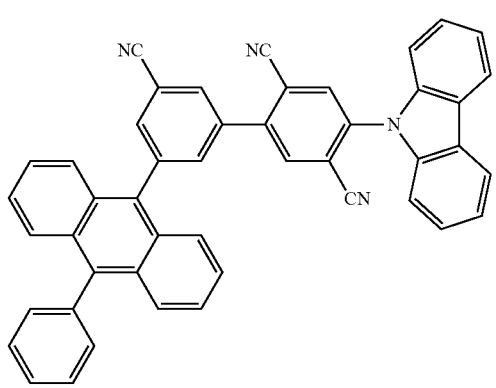

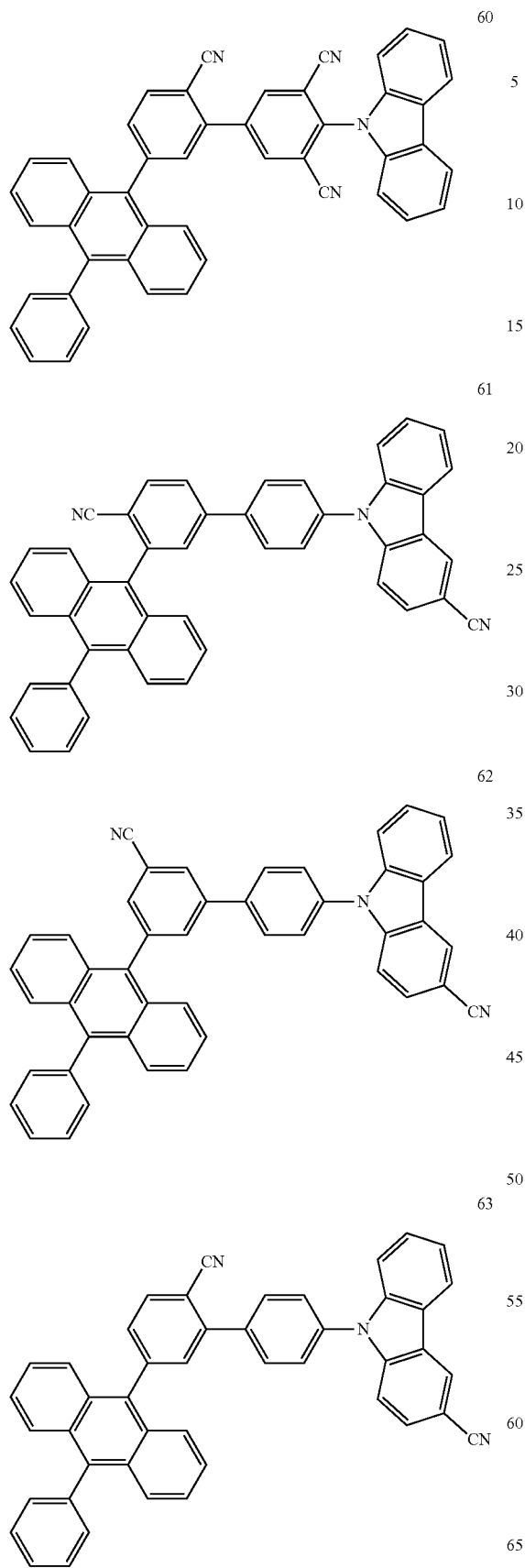

1289
-continued
68
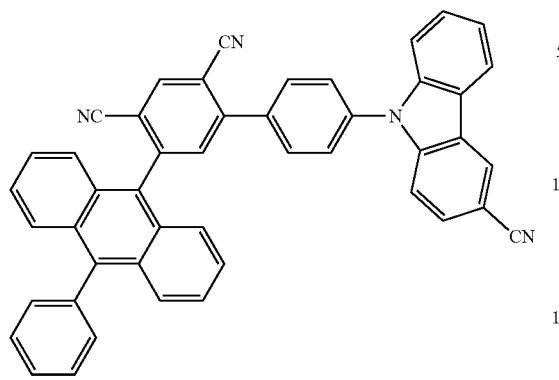
69
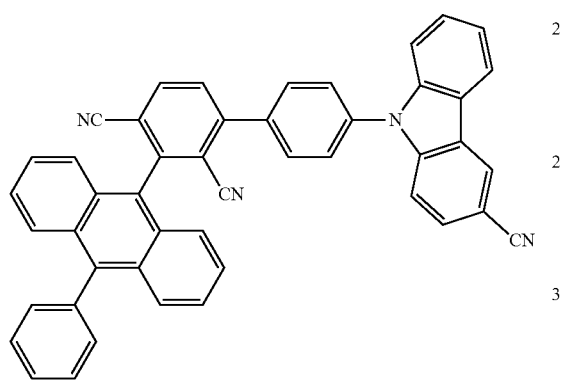
70
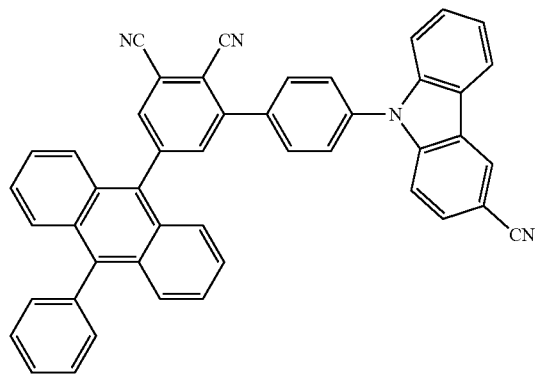
71
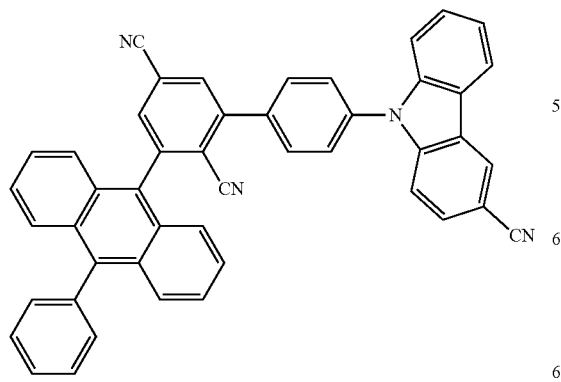
1290
-continued
72
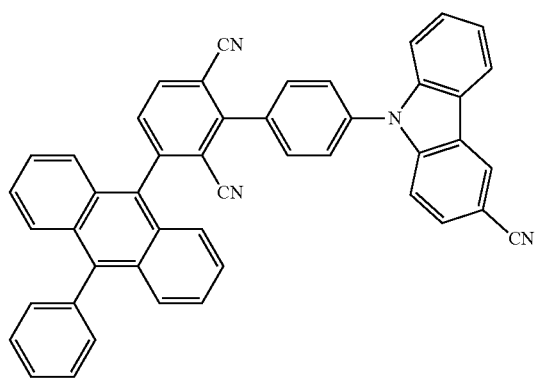
73
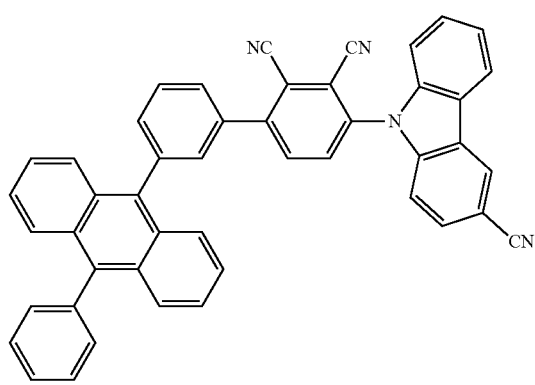
74
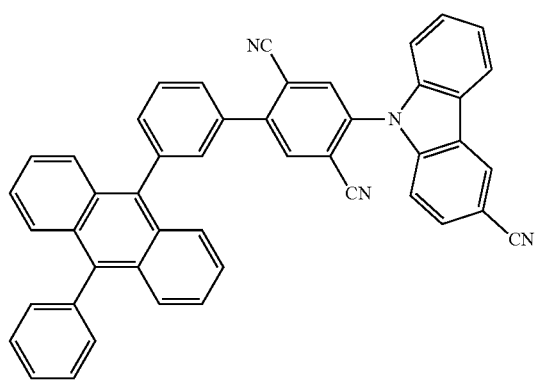
75
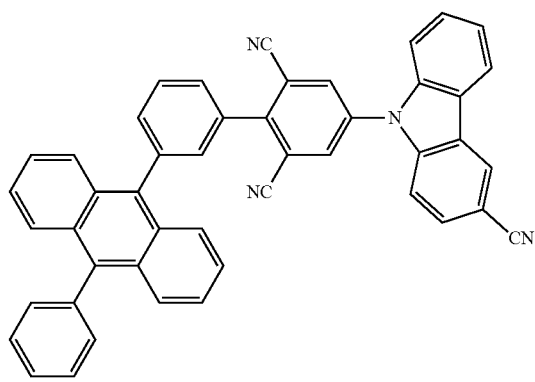

76
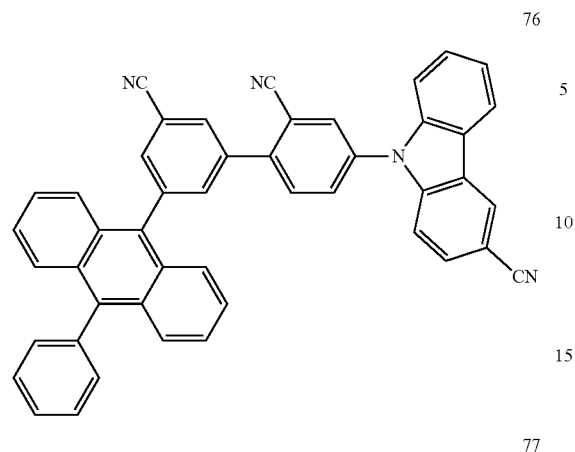
77
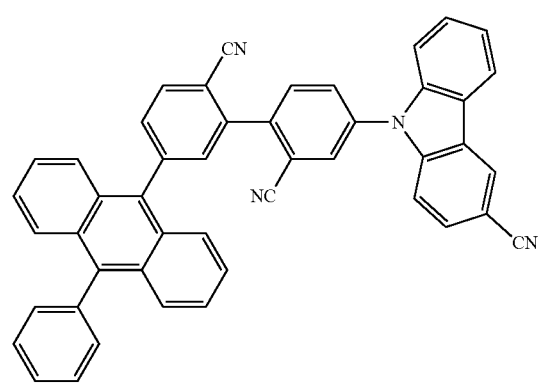
78
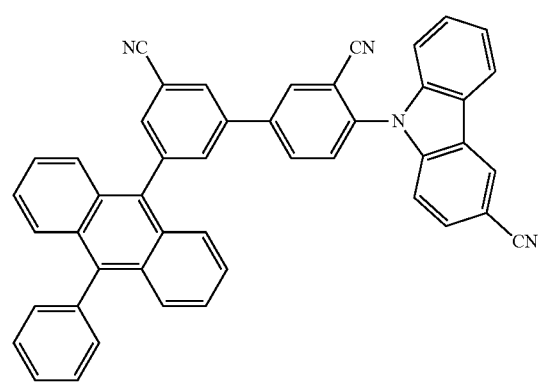
79
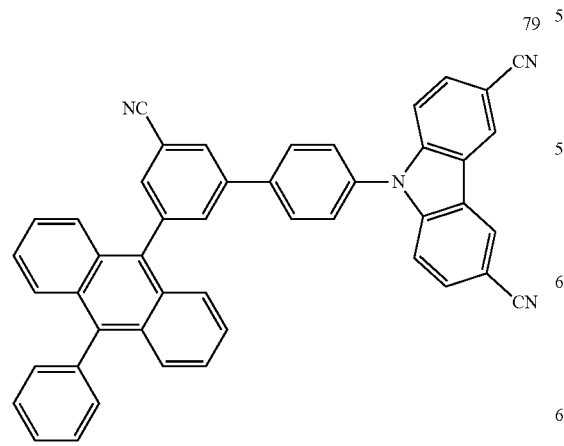
80
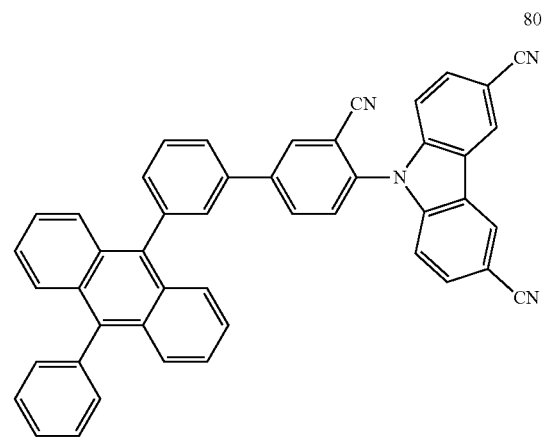
81
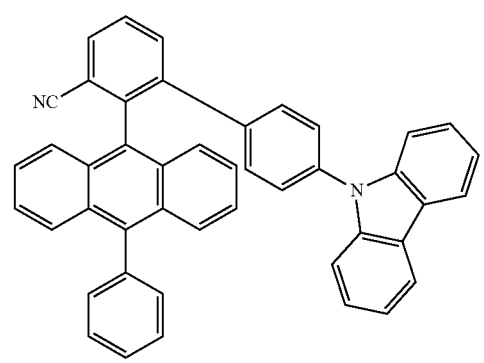
82
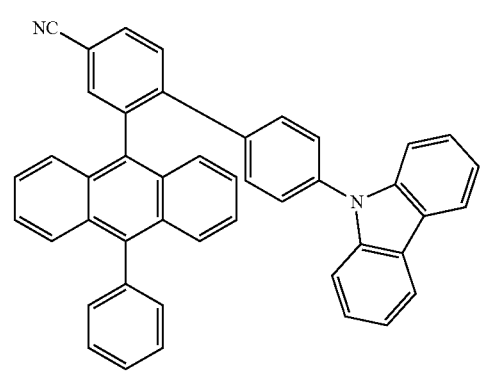
83
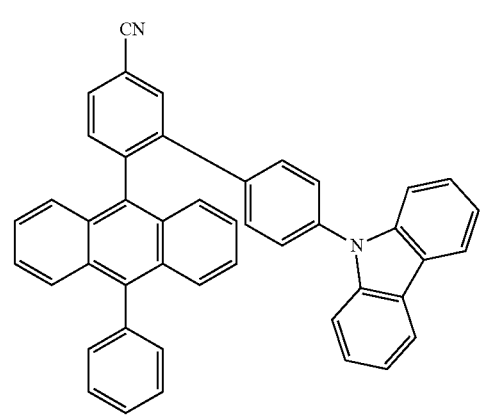

84
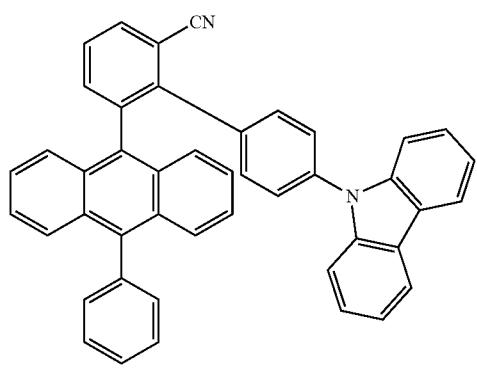
85
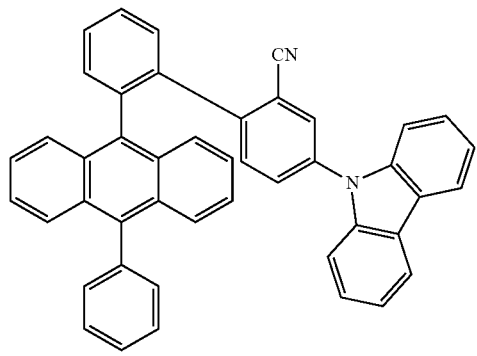
86
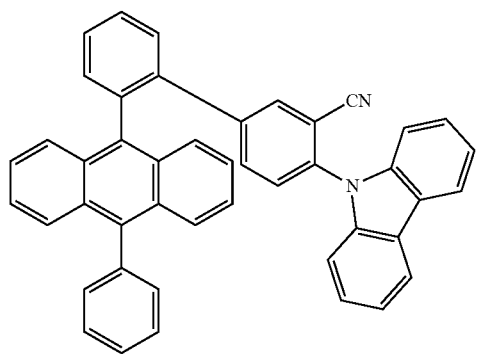
87
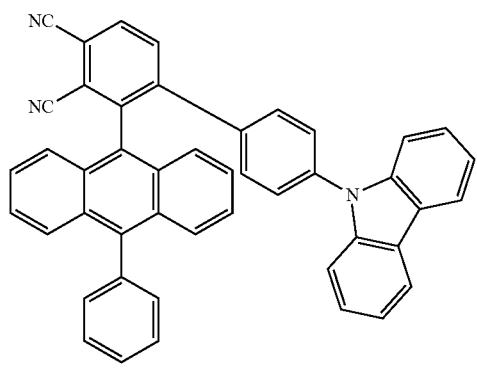
88
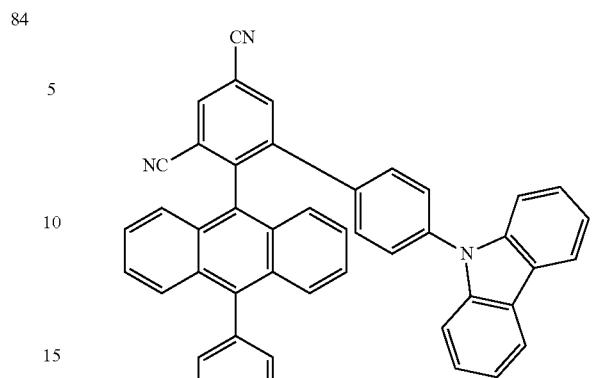
89
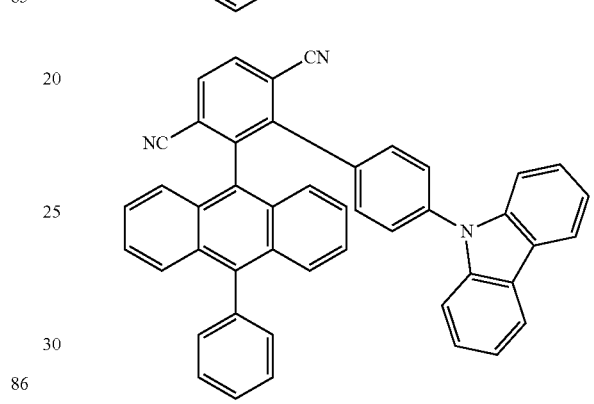
90
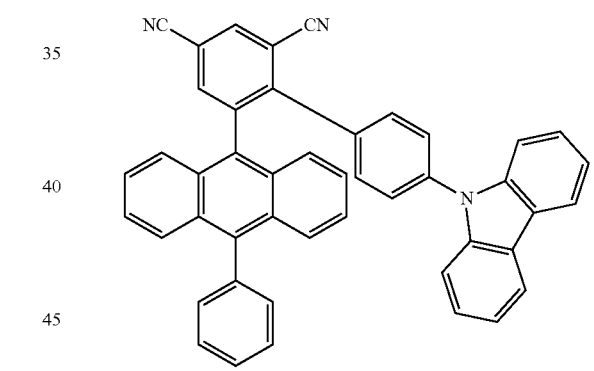
91
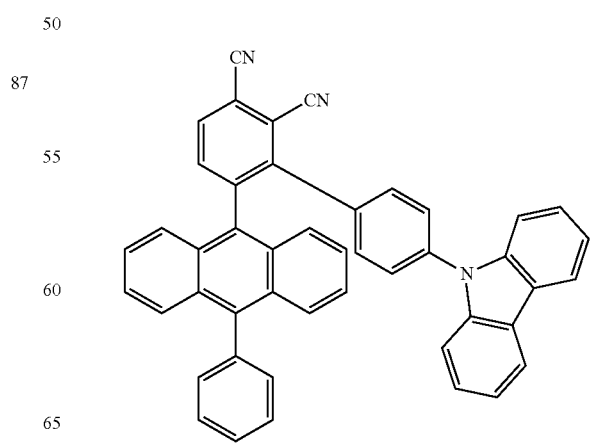

1295
-continued
92
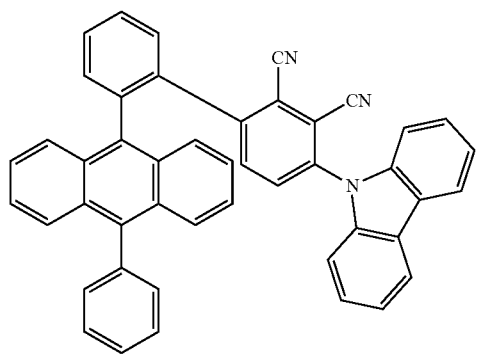
93
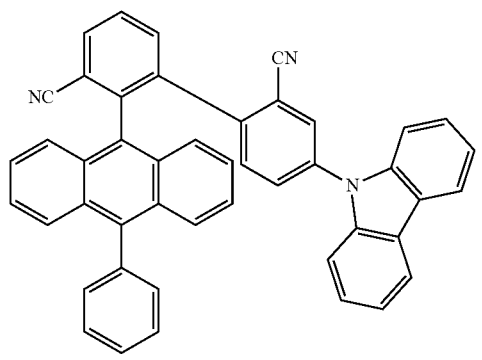
94
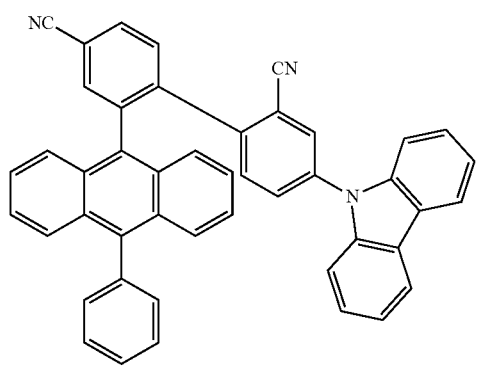
95
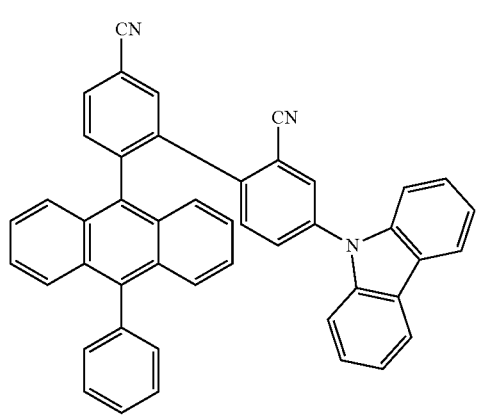
1296
-continued
96
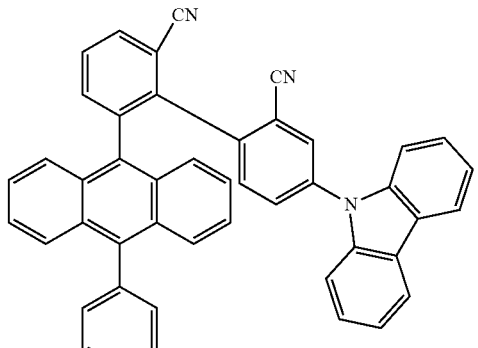
97
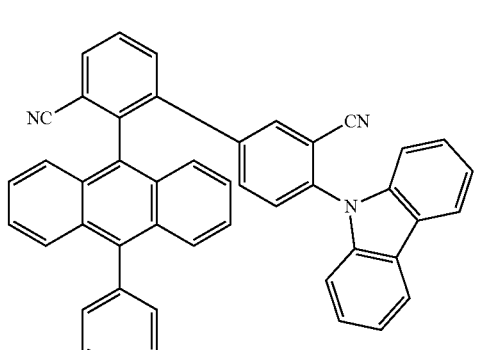
98
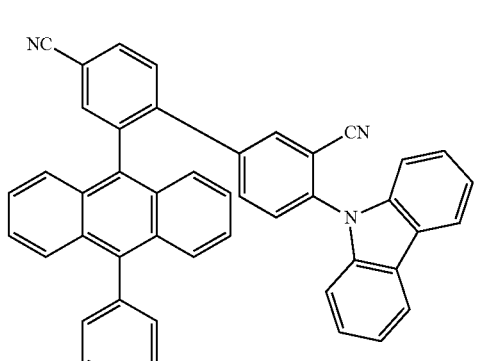
99

1297
-continued
100
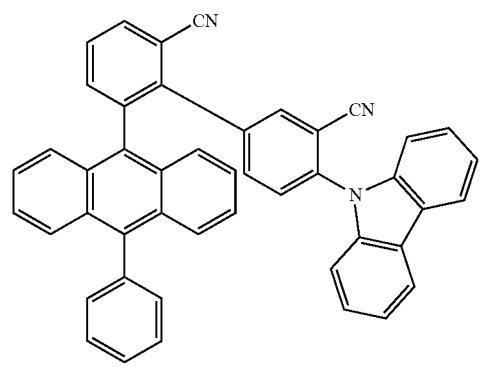
101
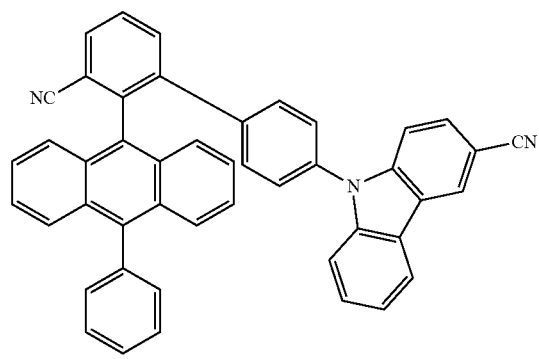
102
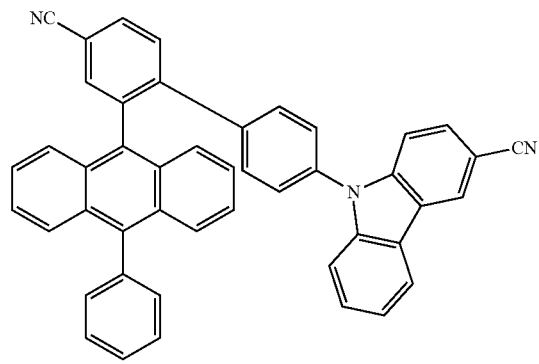
103
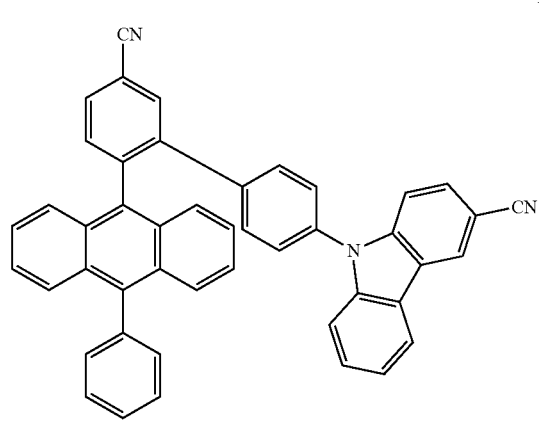
1298
-continued
104
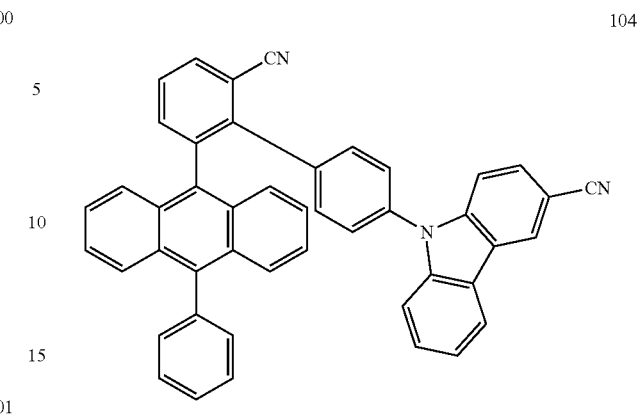
105
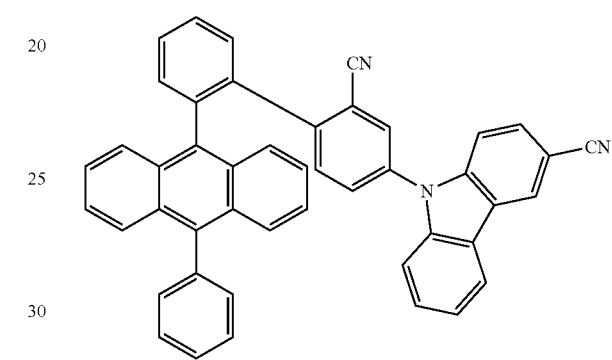
106
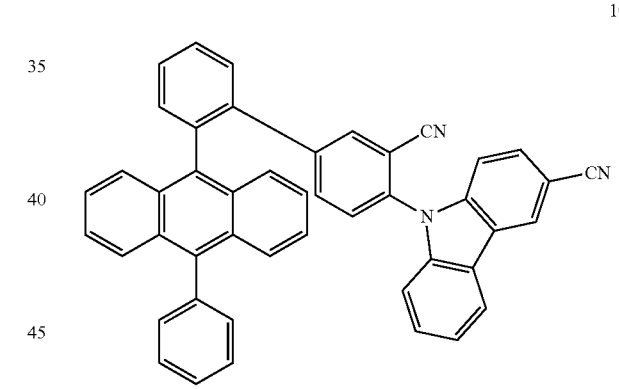
107
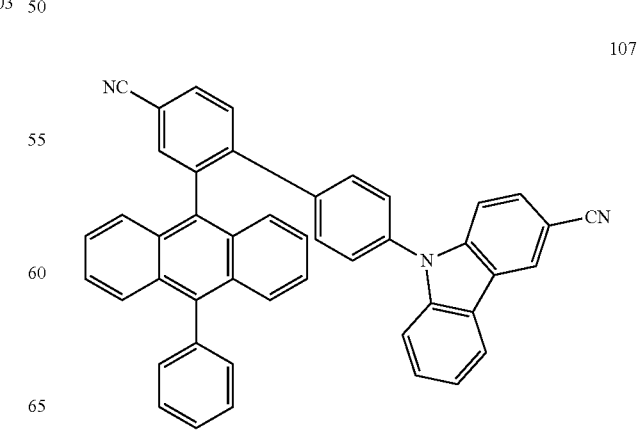

108
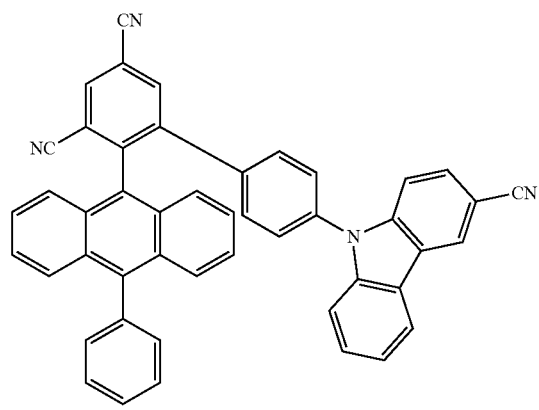
109
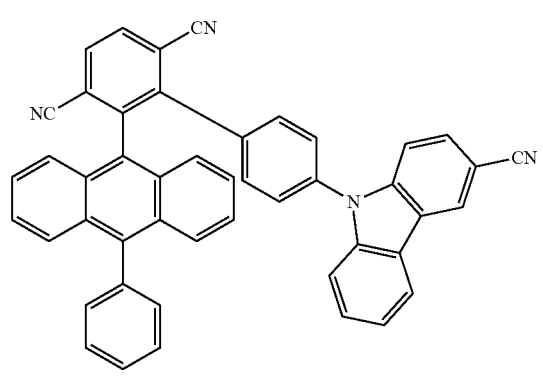
110
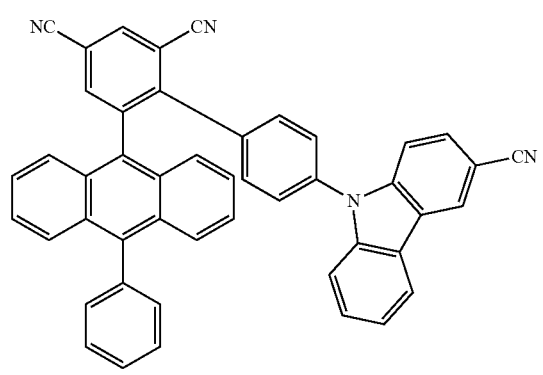
111
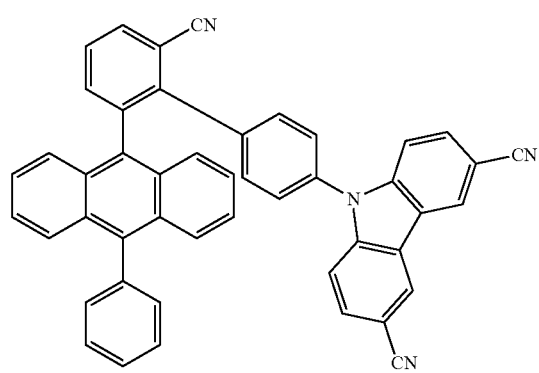
112
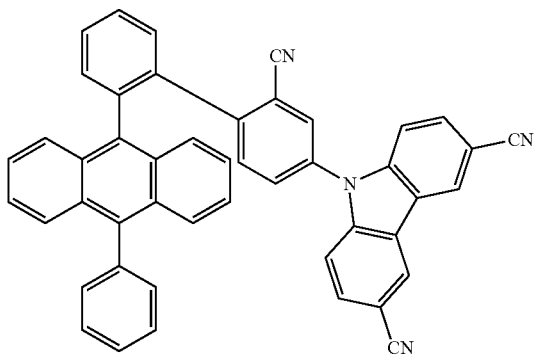
113
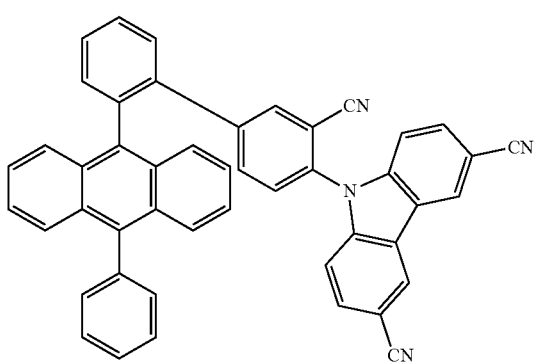
114
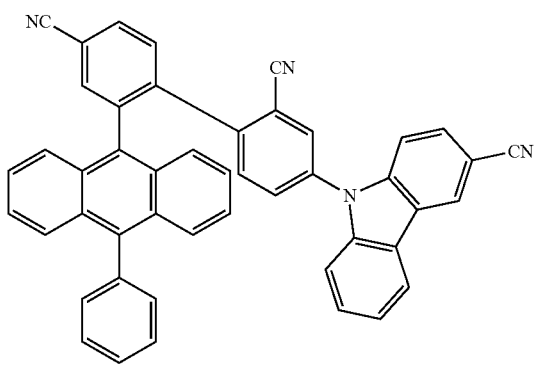
115
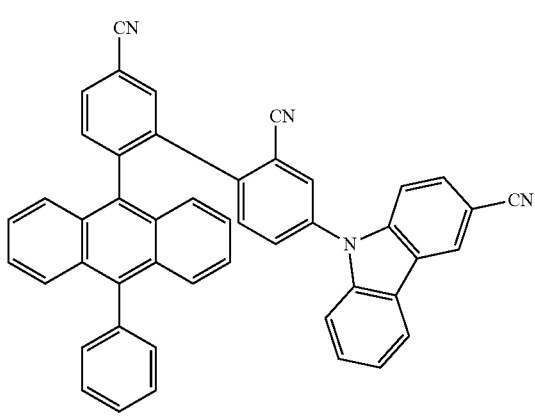

1301
-continued
116
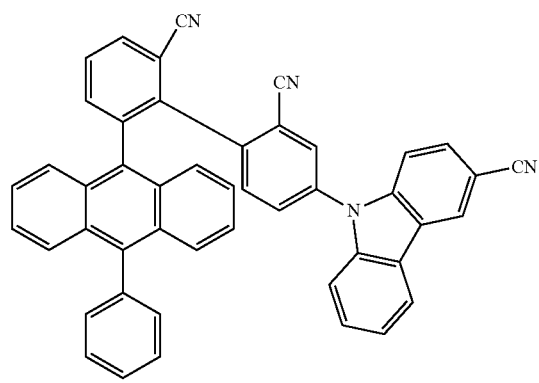
117
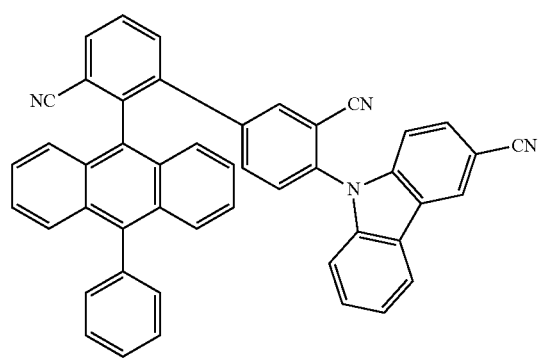
118
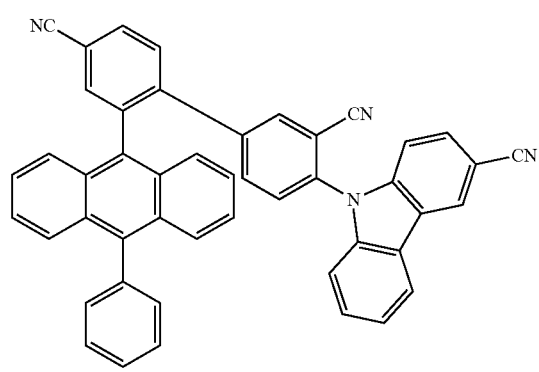
119
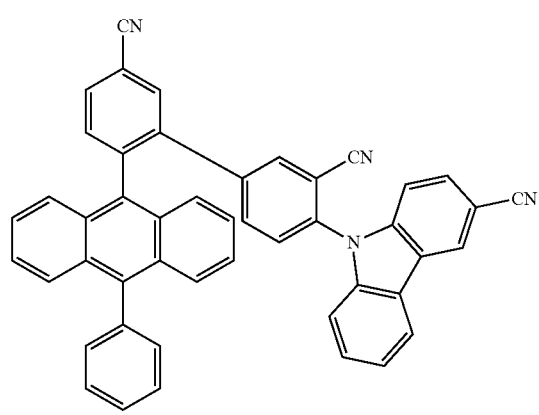
1302
-continued
120
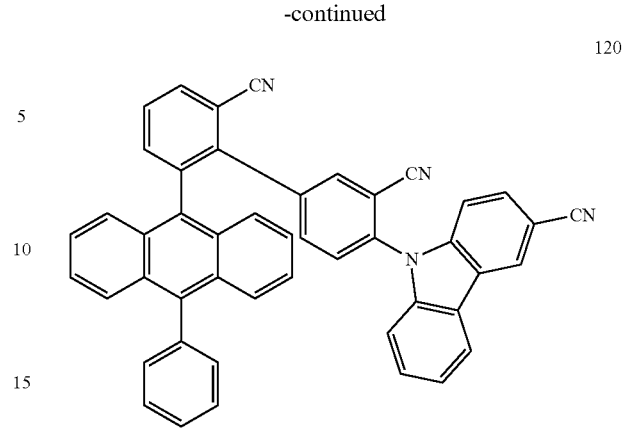
121
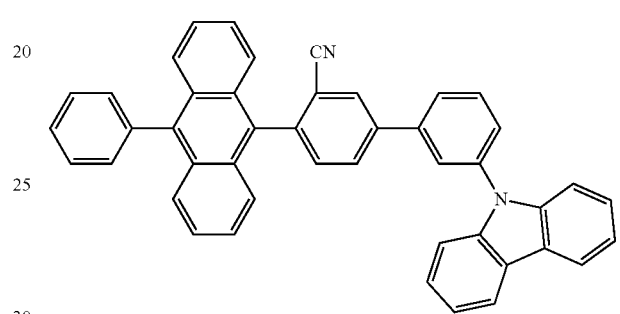
122
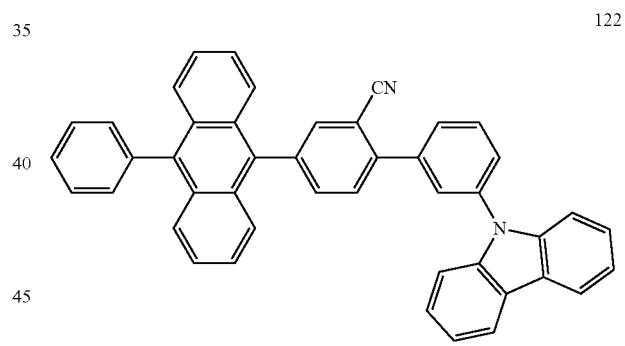
123
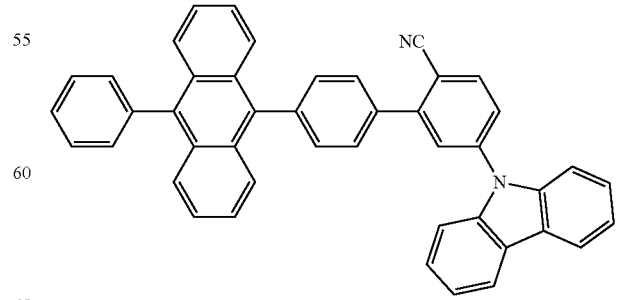

124
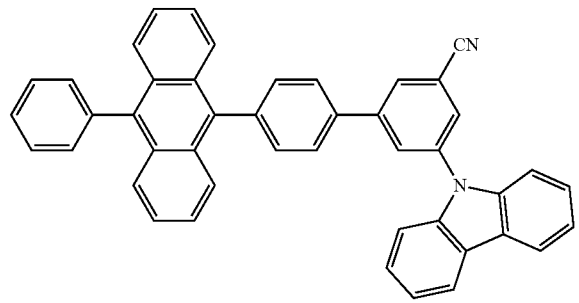
125
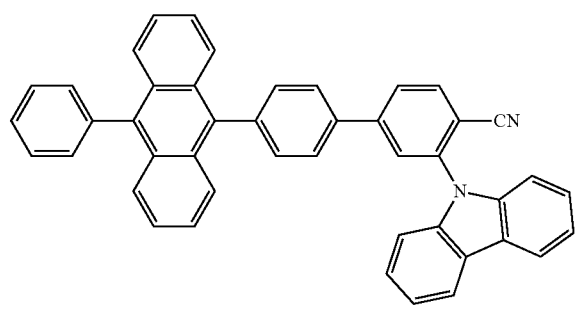
126
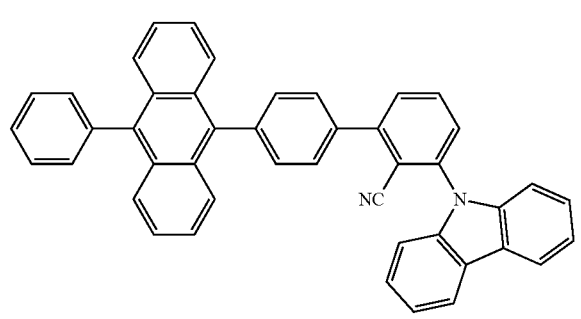
127
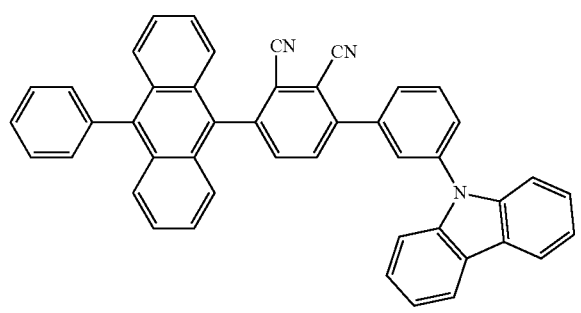
128
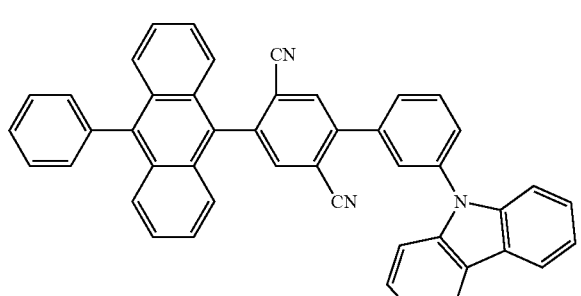
129
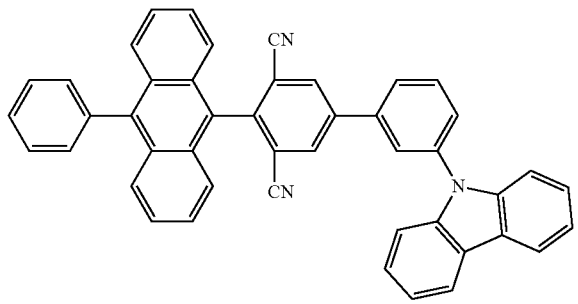
130
131
132
133

-continued
134
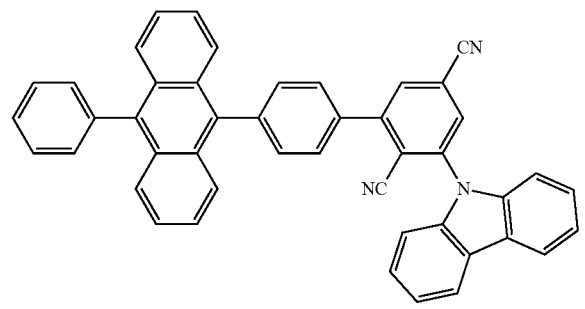
135
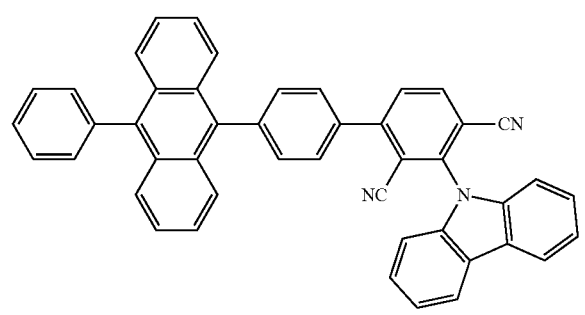
136
137
138
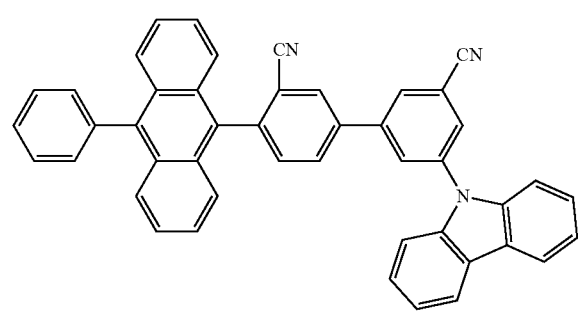
-continued
139
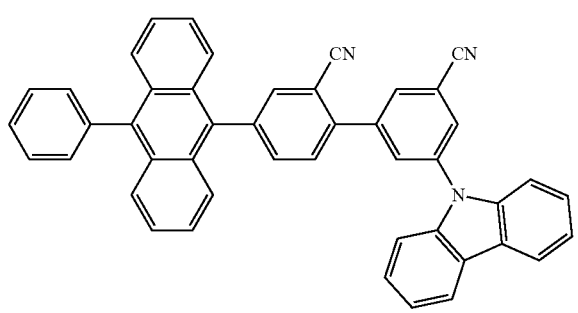
140
141
142
143

144
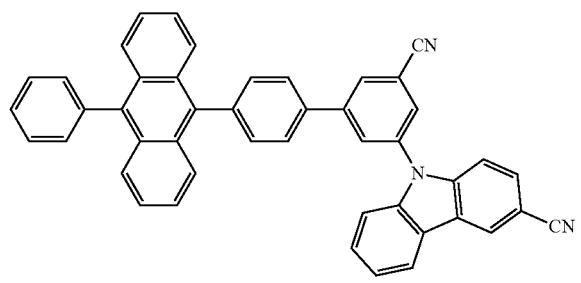
145
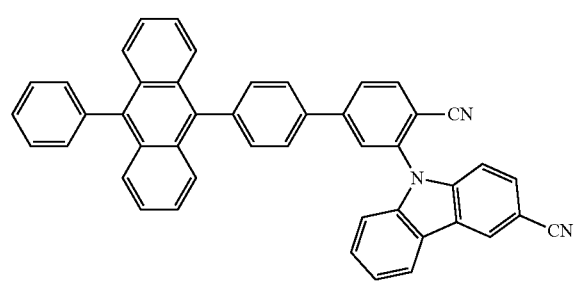
146
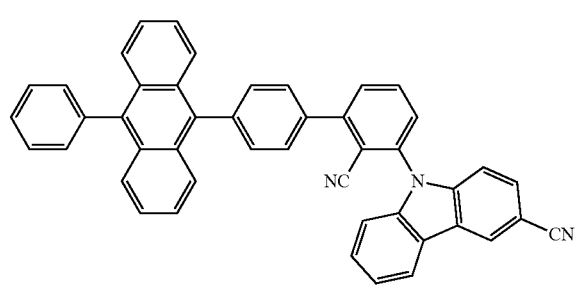
147
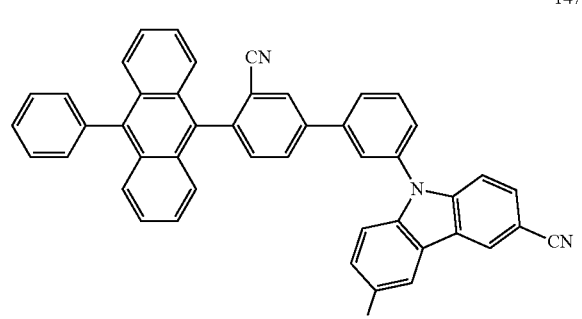
148
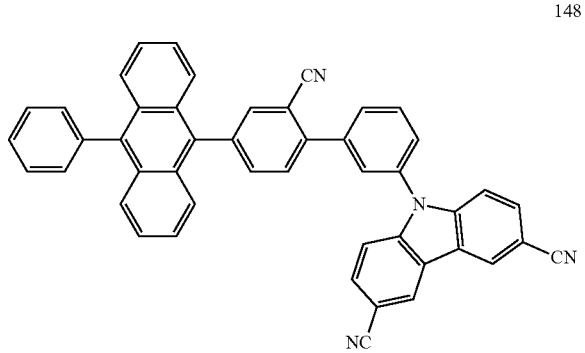
149
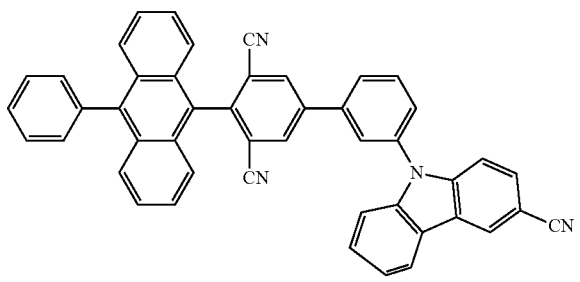
150
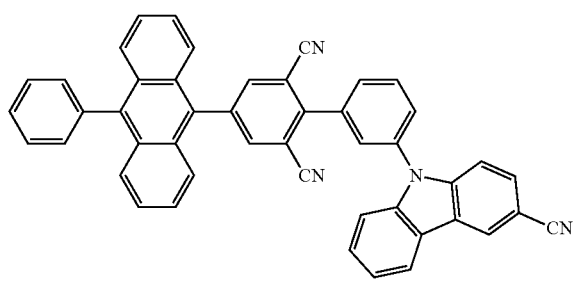
151
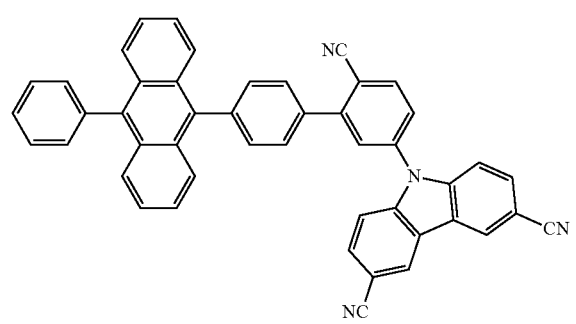
152
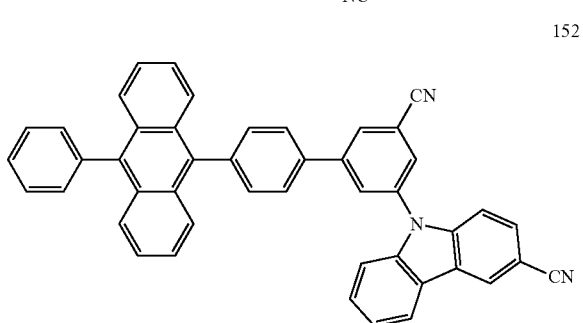
153
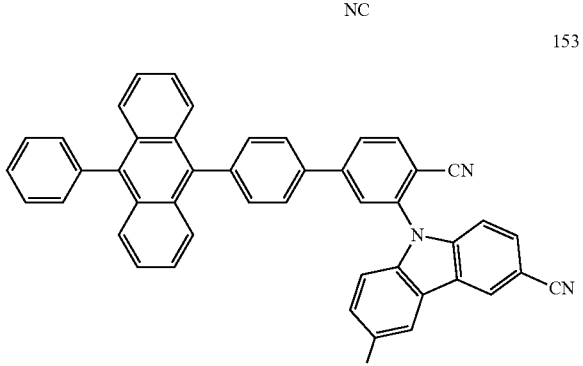

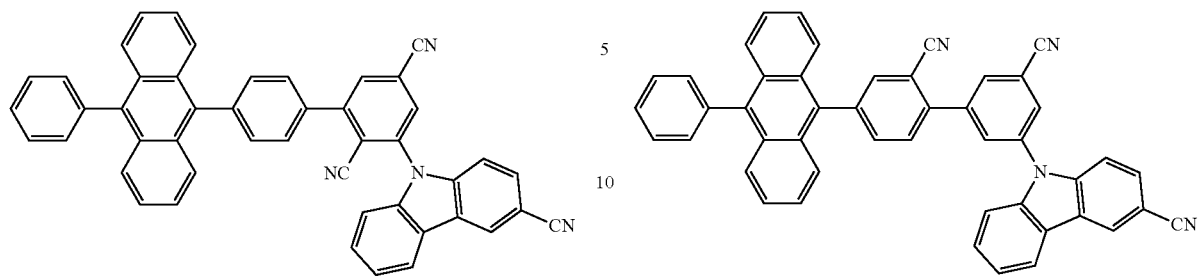

164
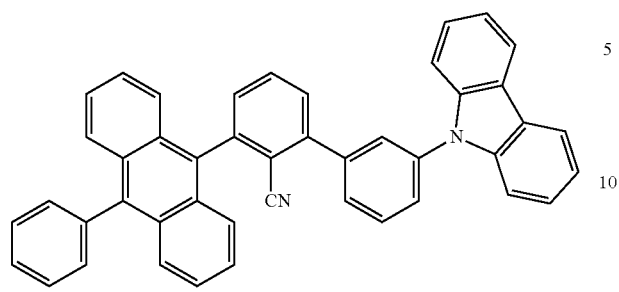
165
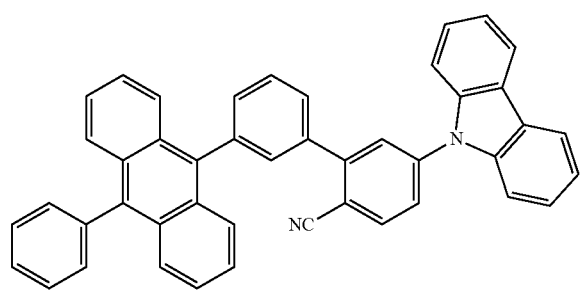
166
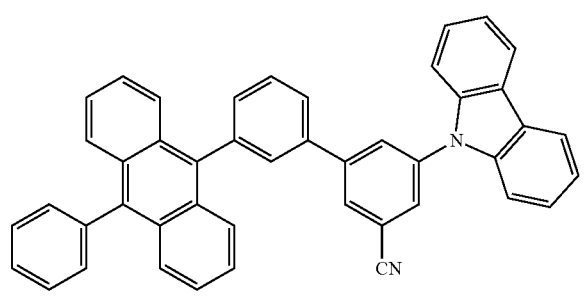
167
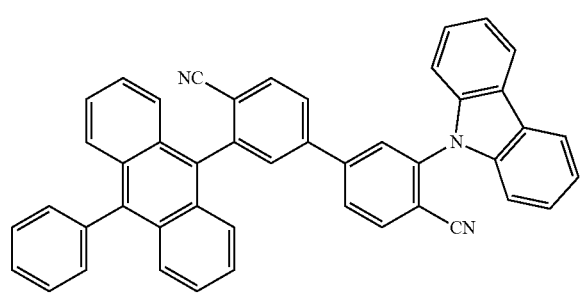
168
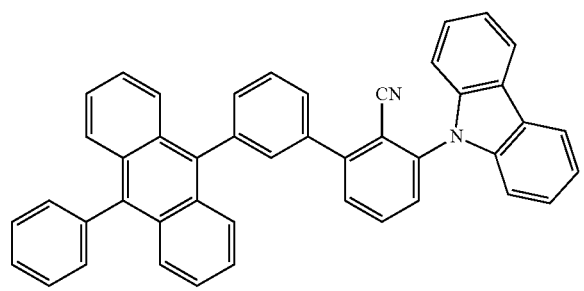
169
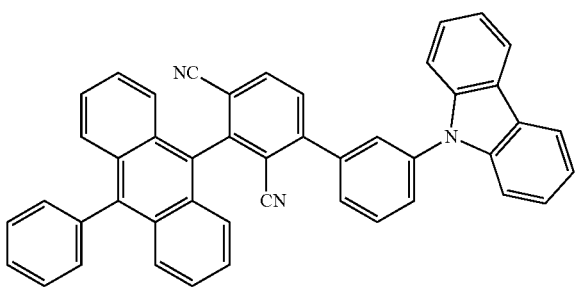
170
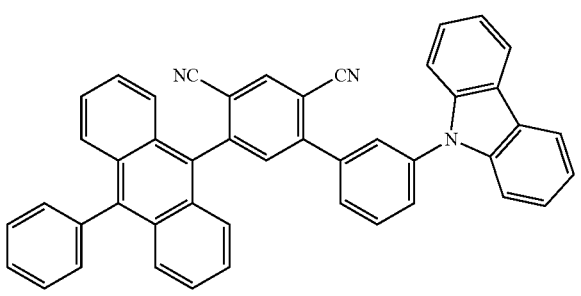
171
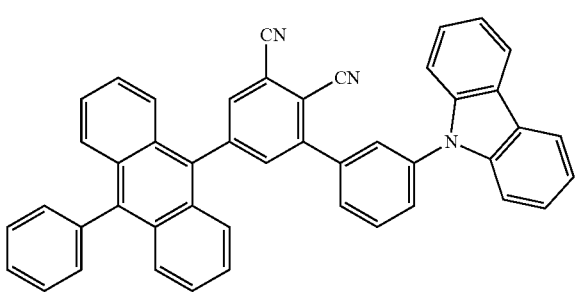
172
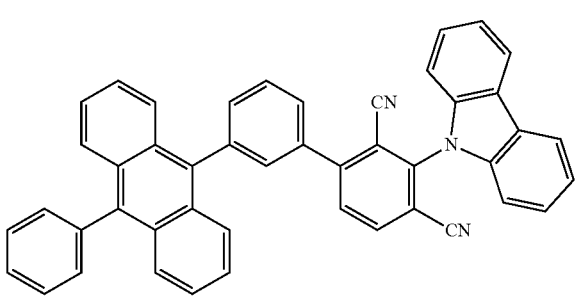
173
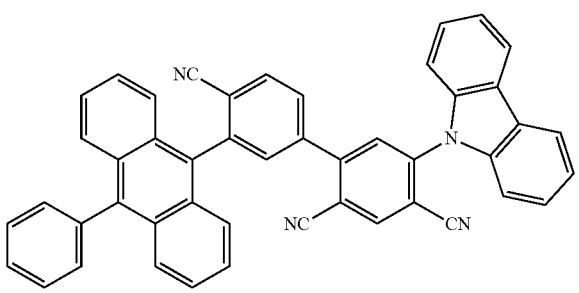

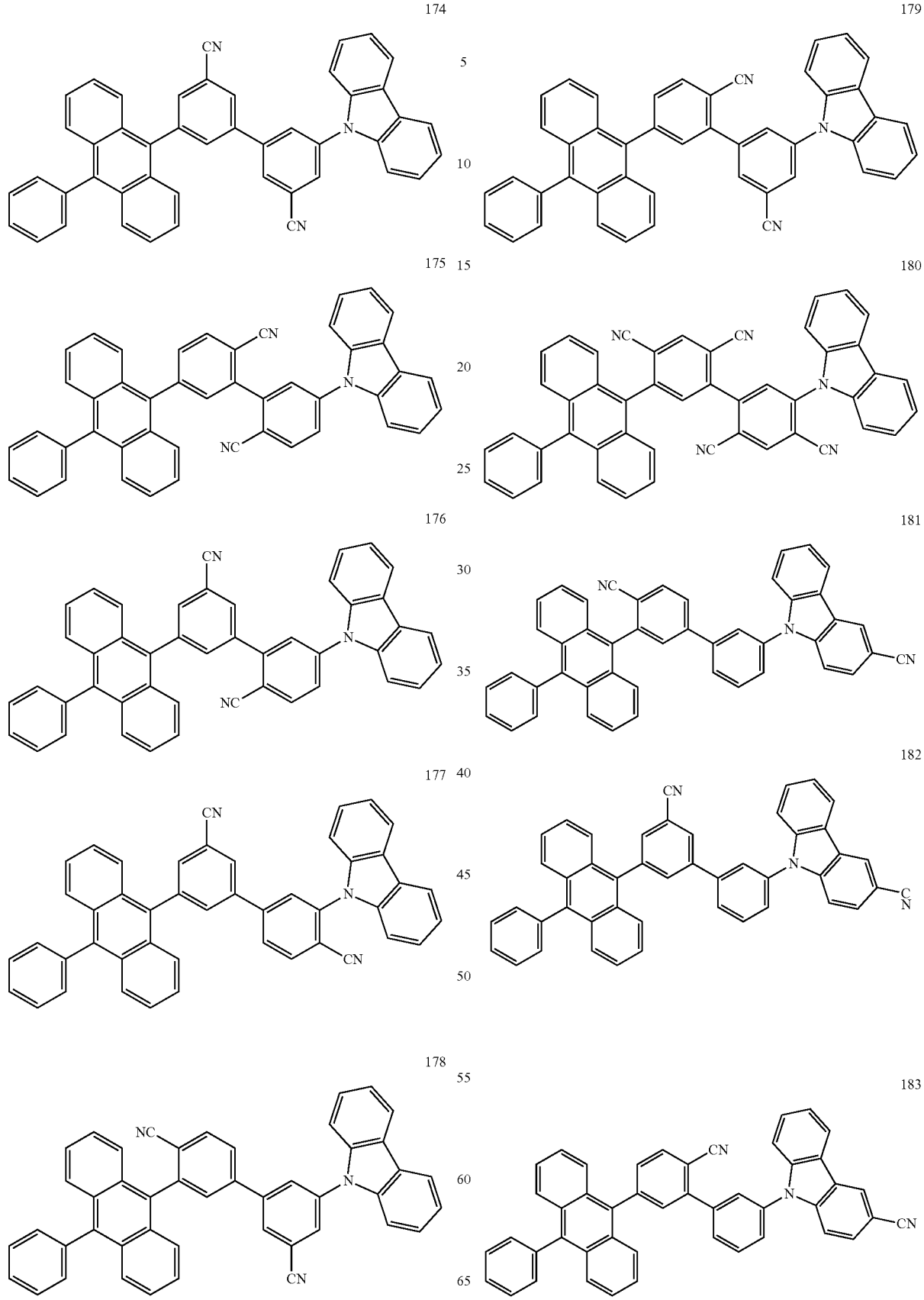

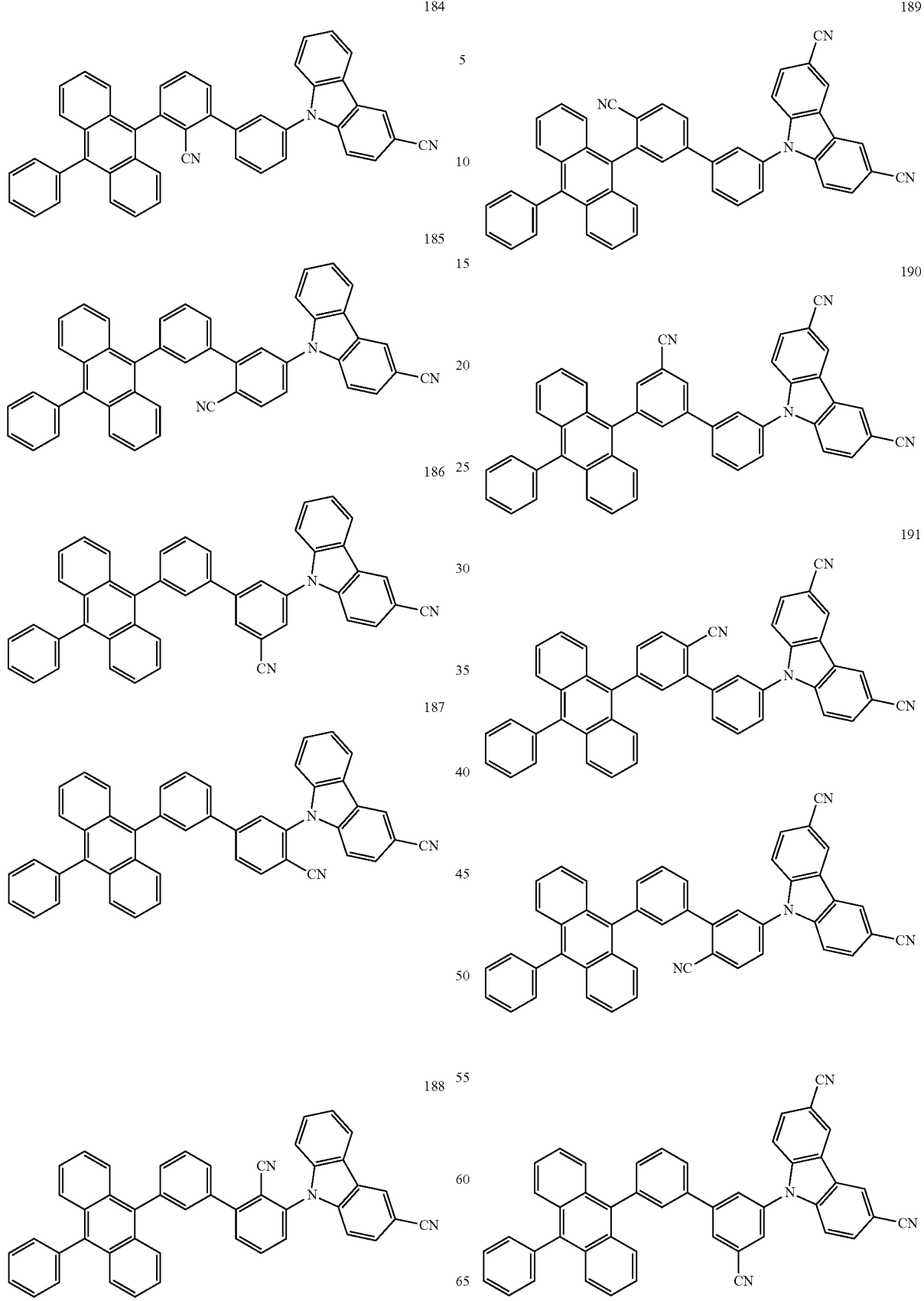

1317 -continued
1318 -continued
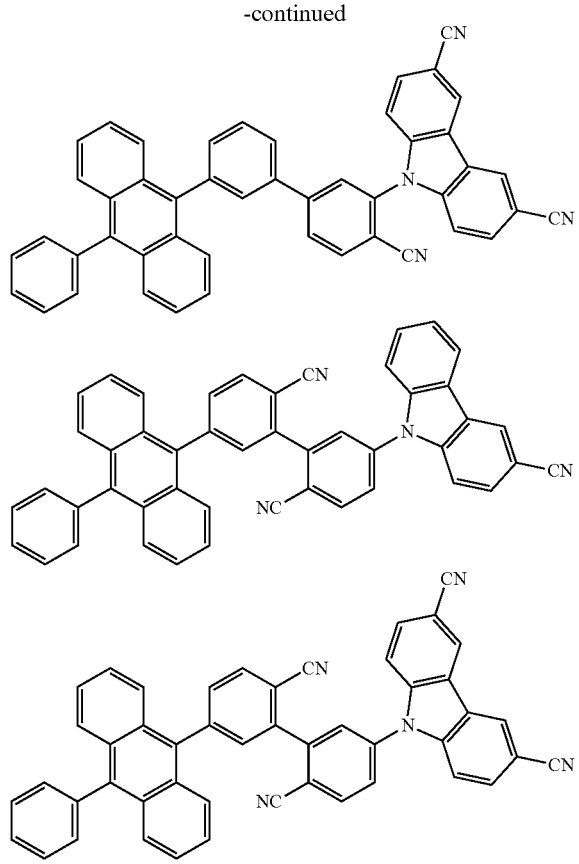
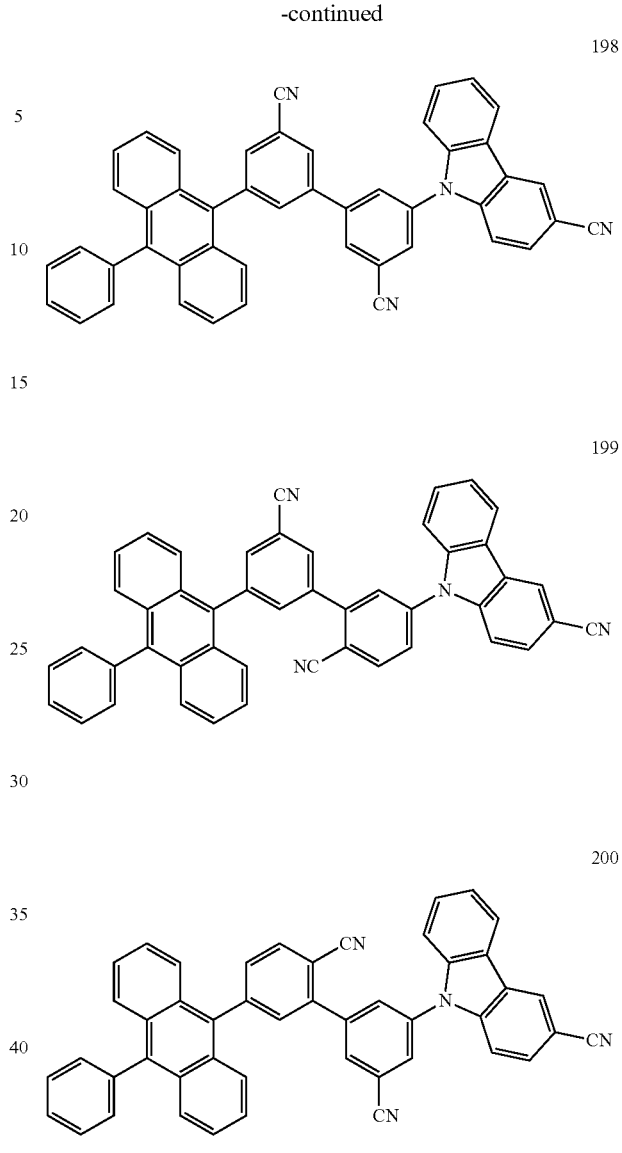
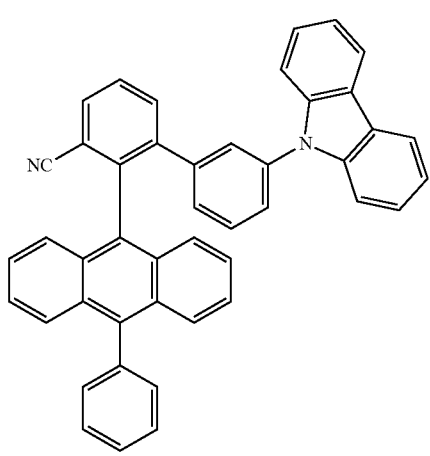

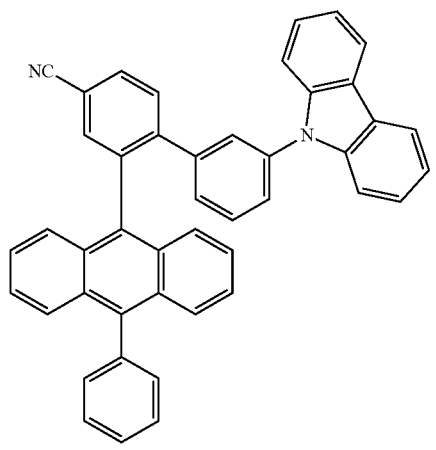
202

203
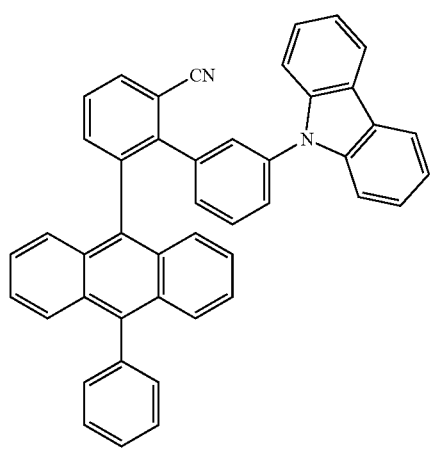
204

-continued
205
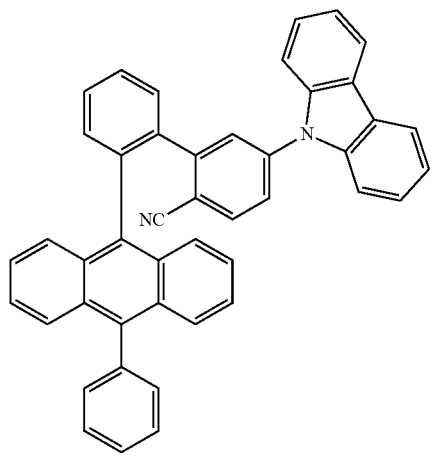
206
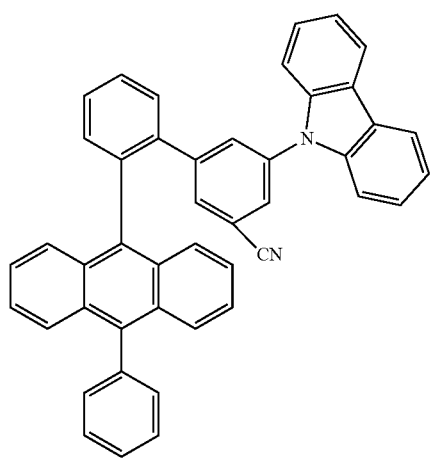
207
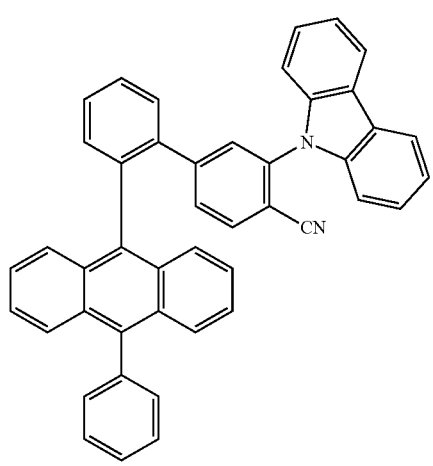

-continued
208
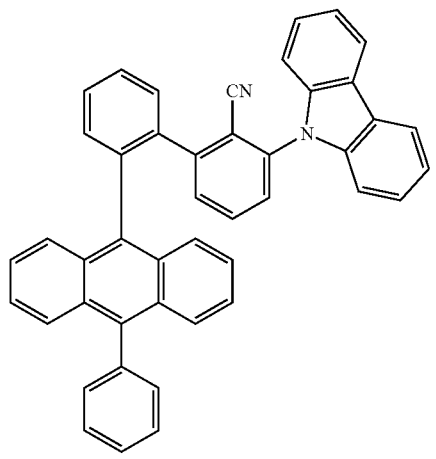
209
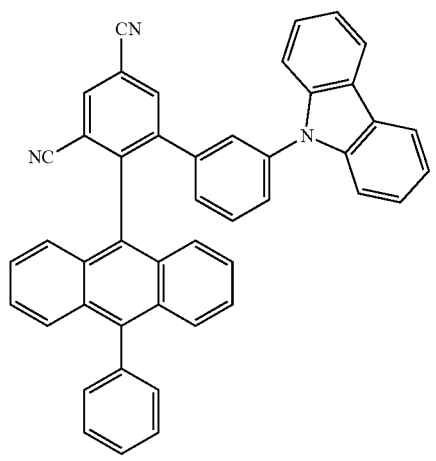
210
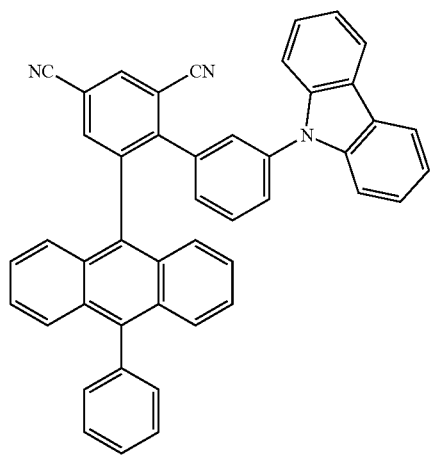

-continued
211
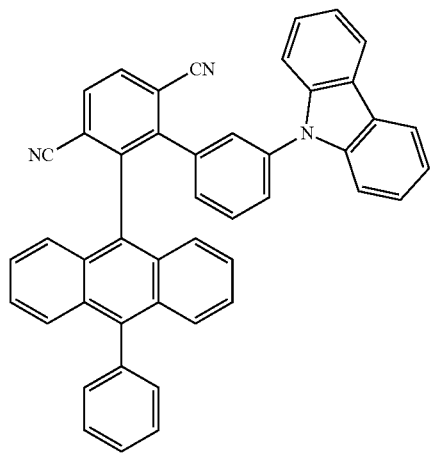
212
213
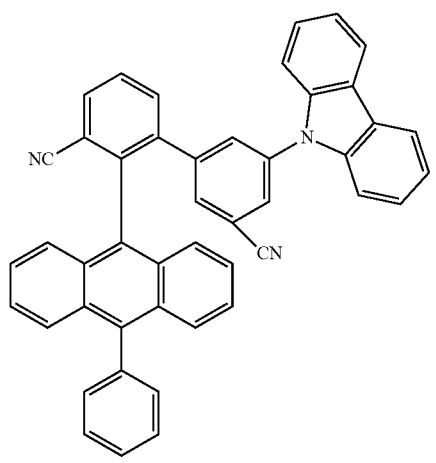

-continued
214
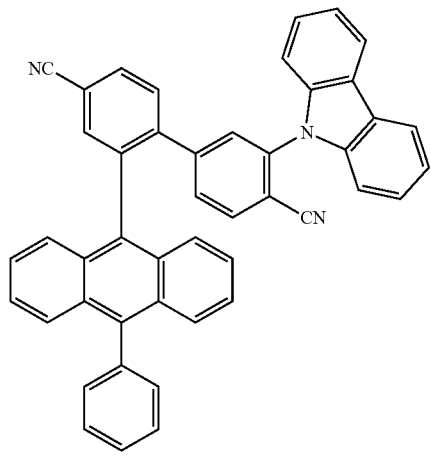
215
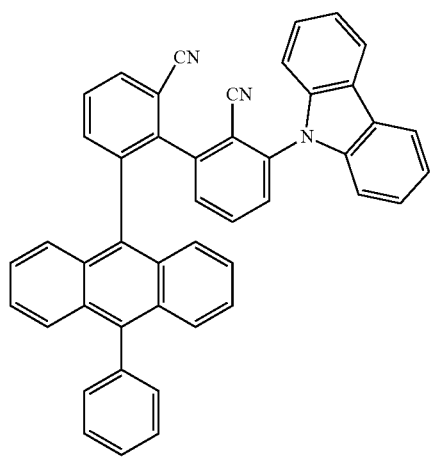
216
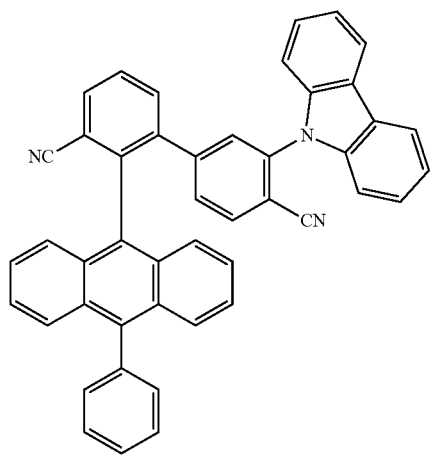

-continued
217
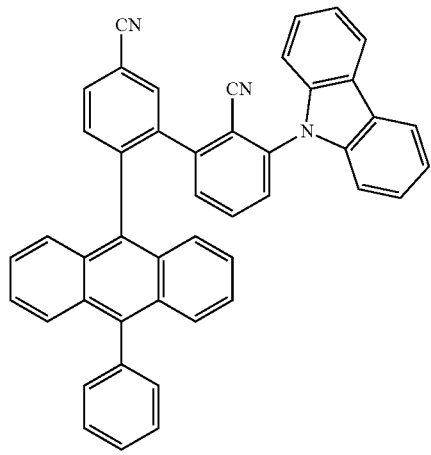
218
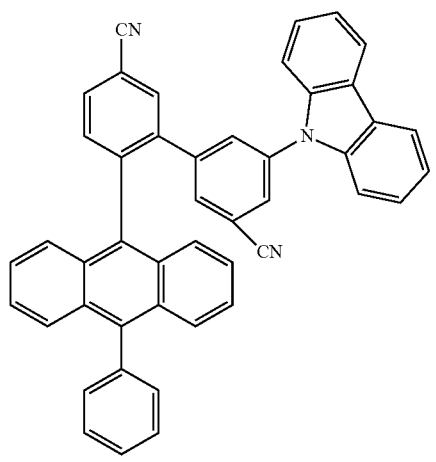
219
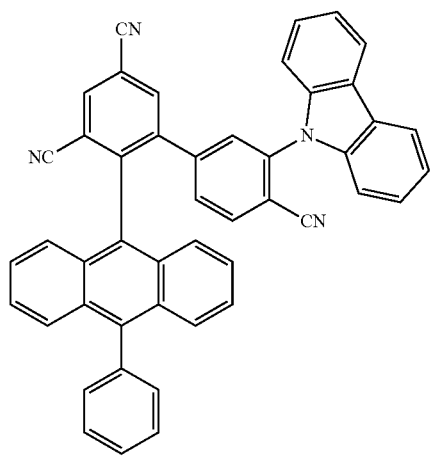

-continued
220
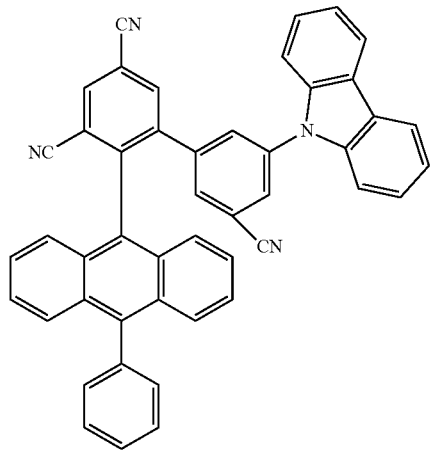
221
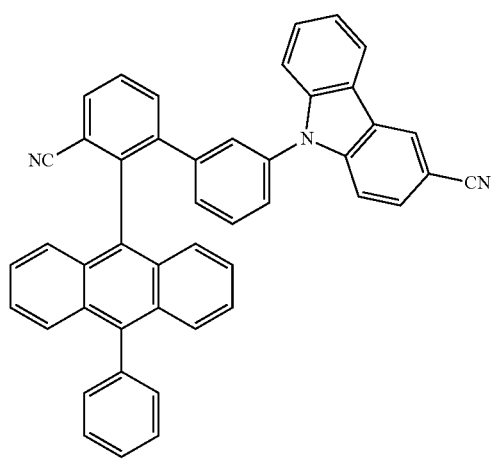
222
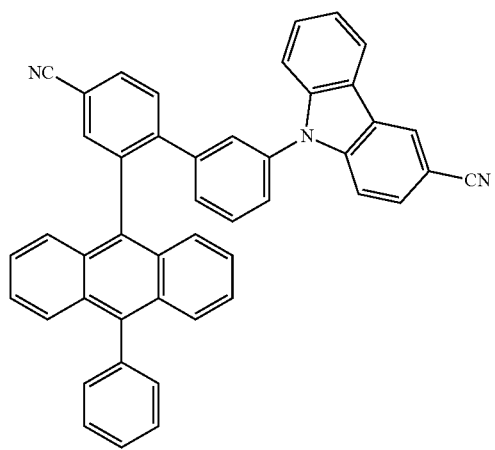

-continued
223
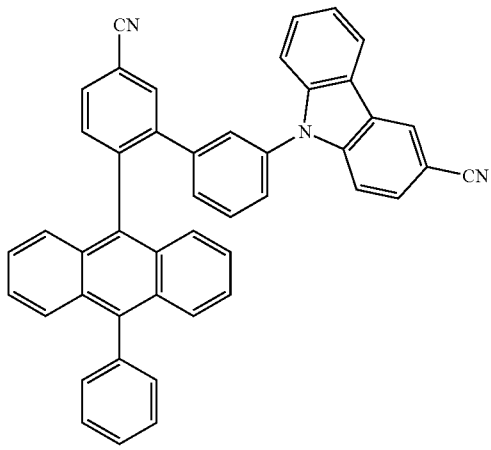
224
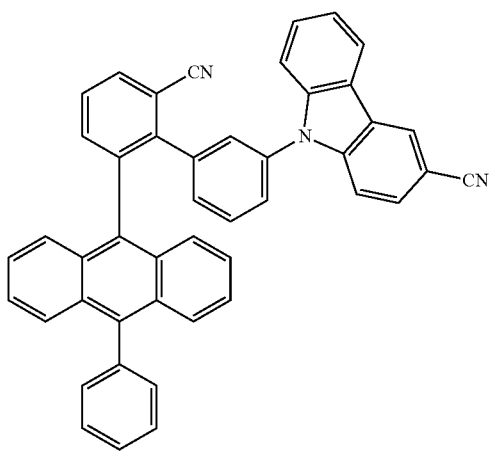
225
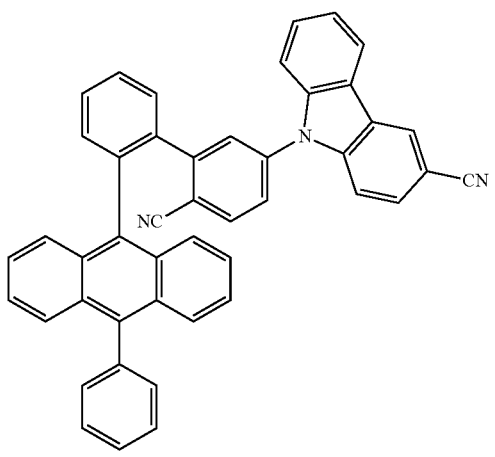

226
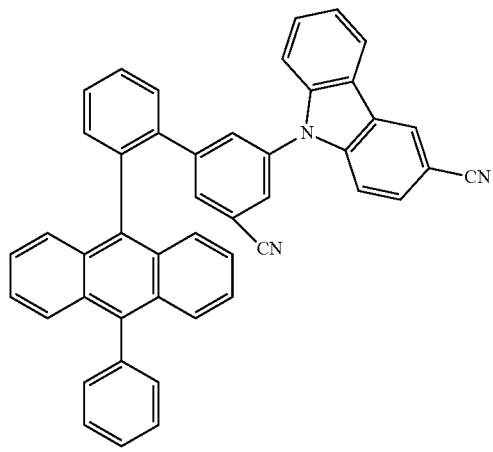
227
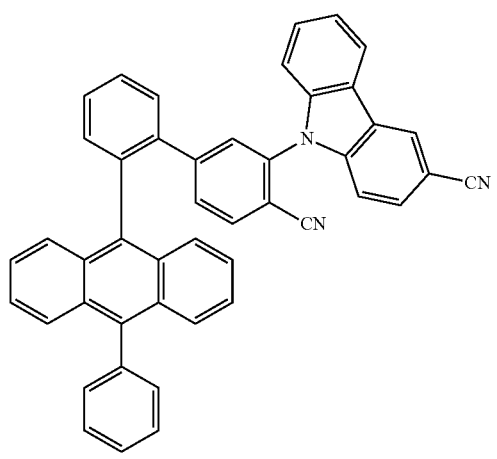
228
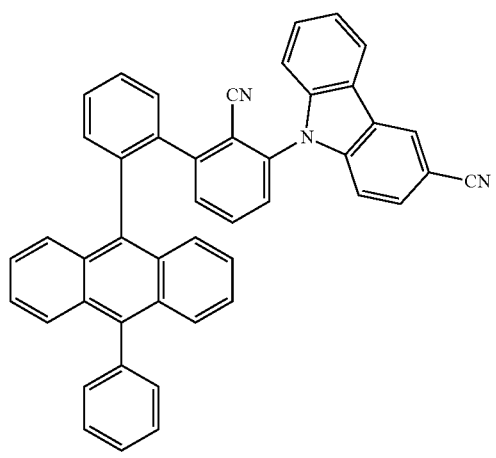

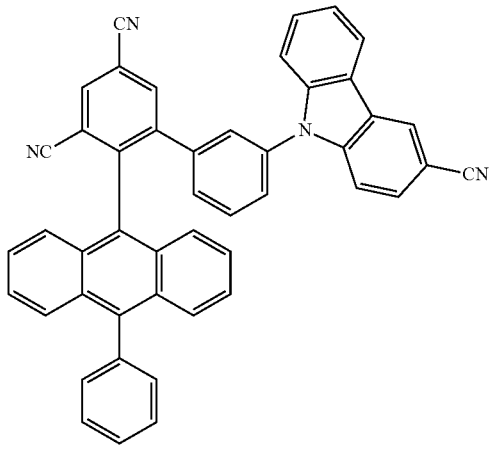
229
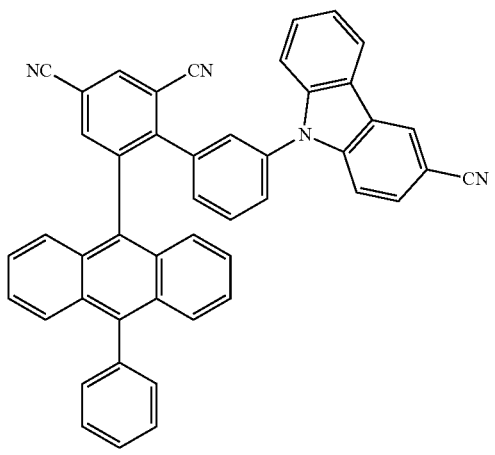
230

231

-continued
232
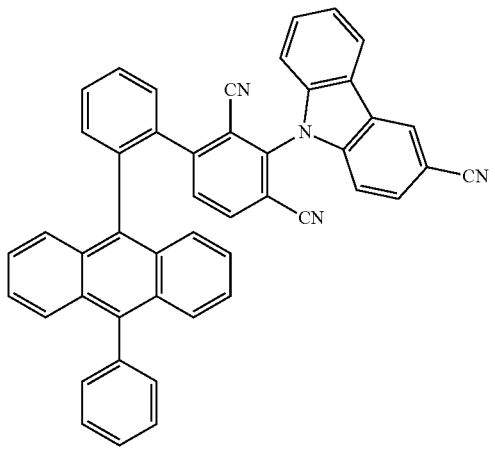
233
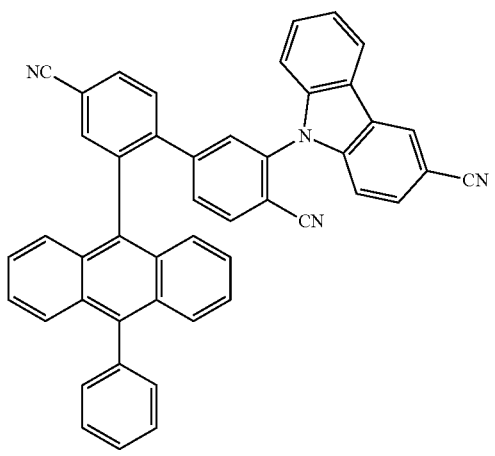
234
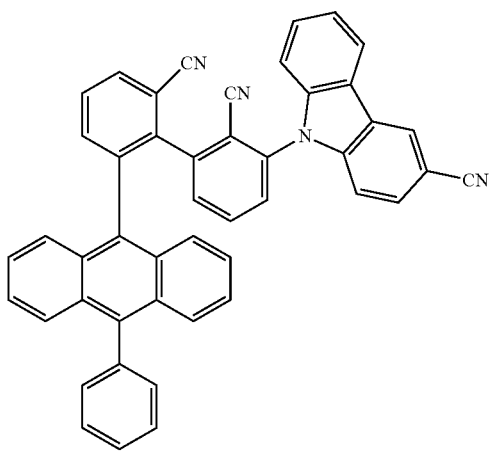

-continued
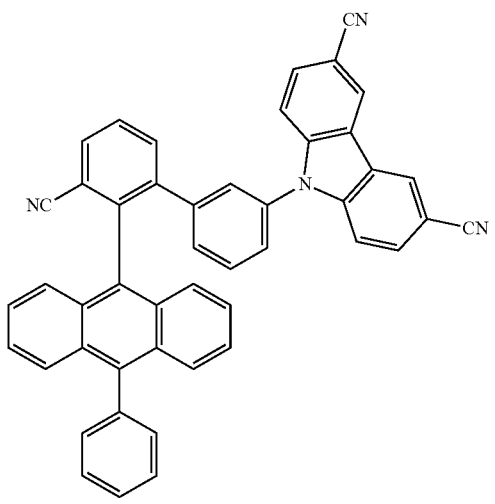
235

236
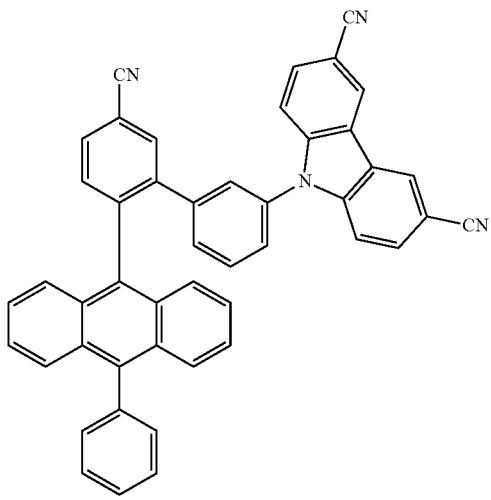
237

-continued
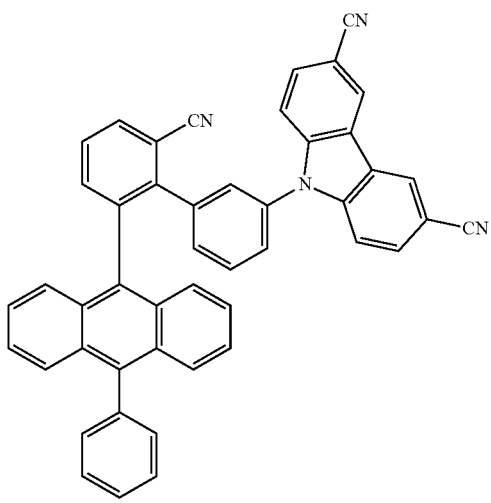
238
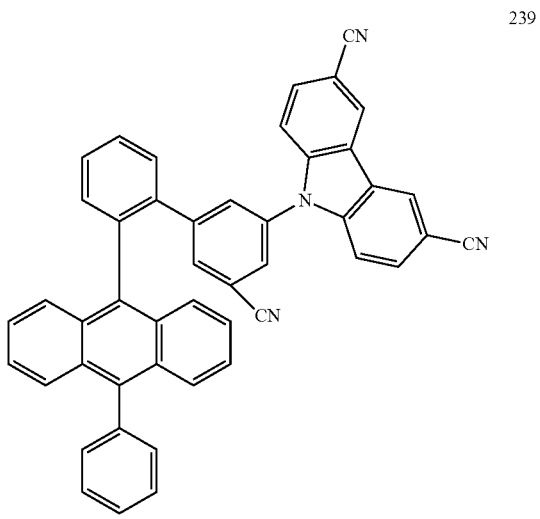
239
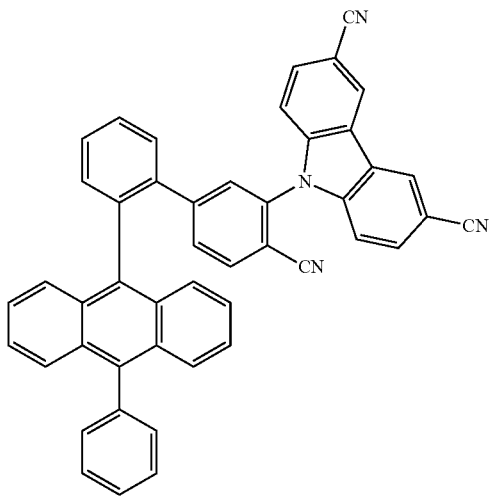
240

-continued
241
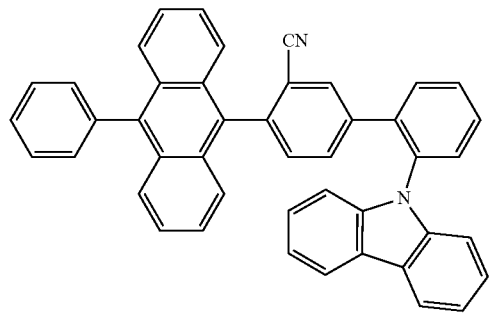
242
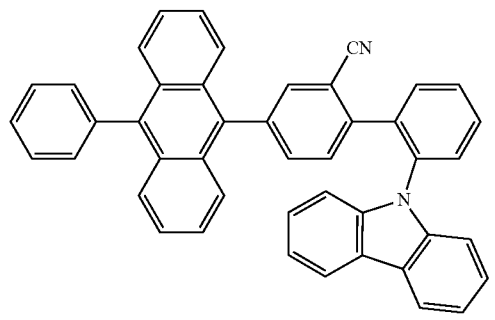
243
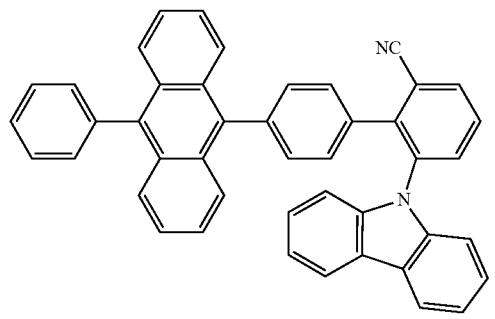
244
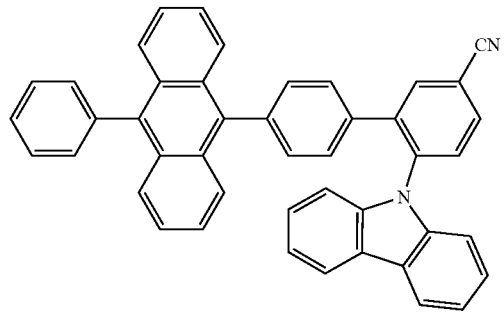
245
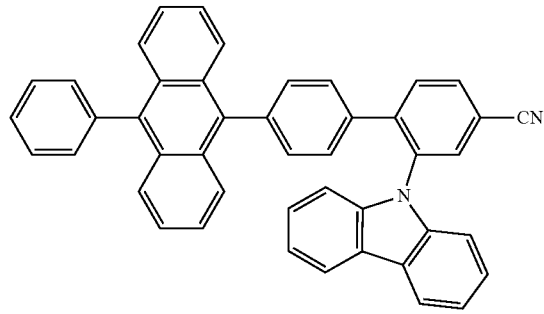

-continued
246
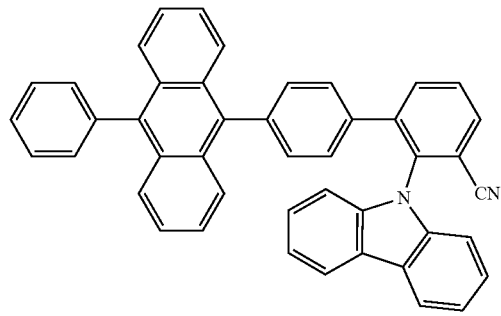
247
248
249
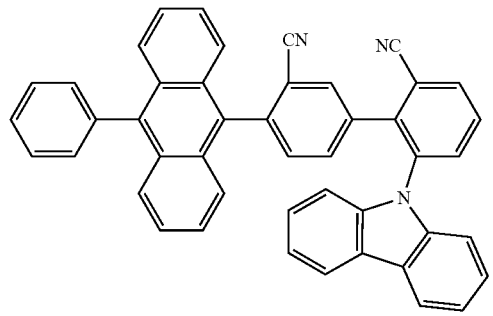
250
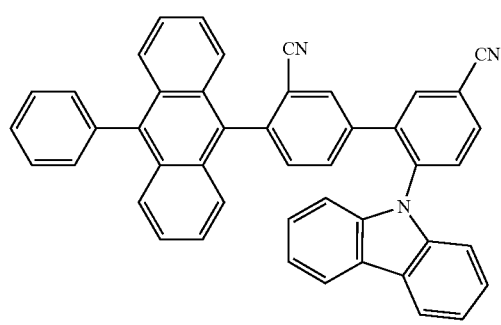

-continued
251
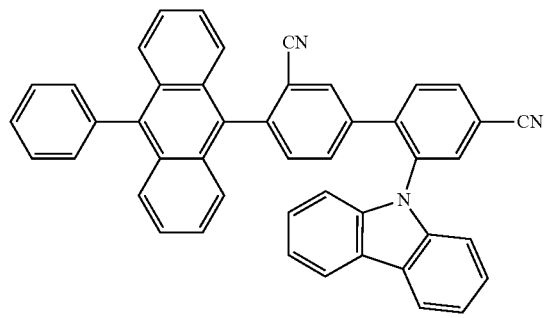
252
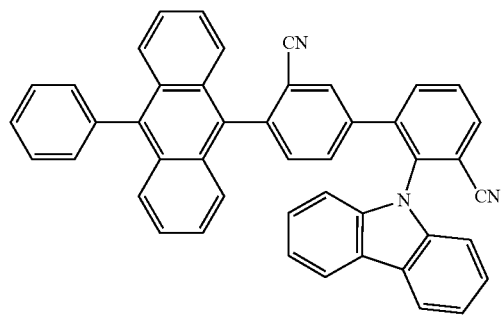
253
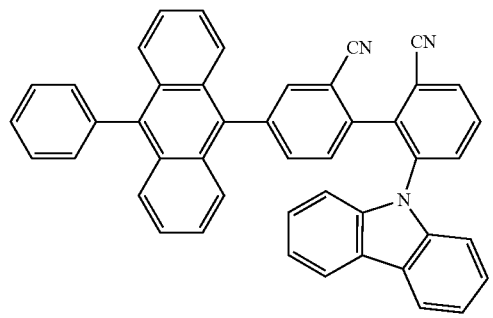
254
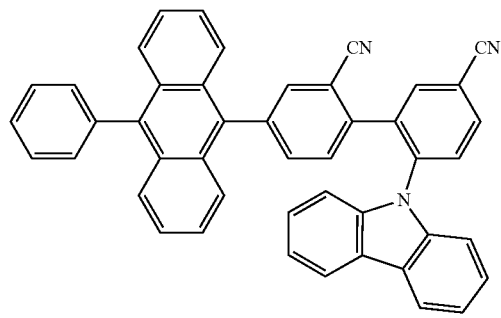
255
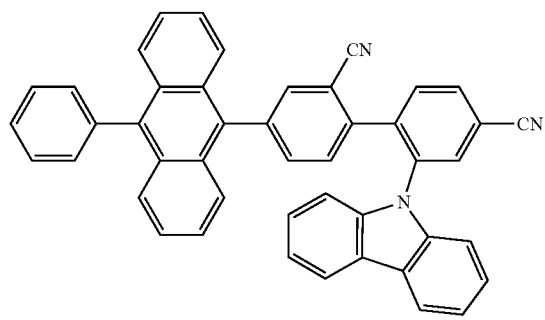

256
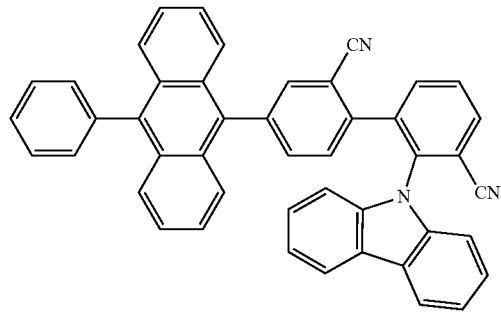
257
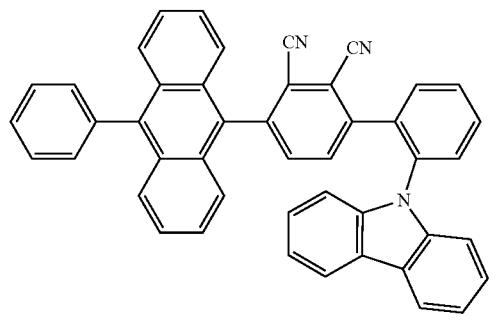
258
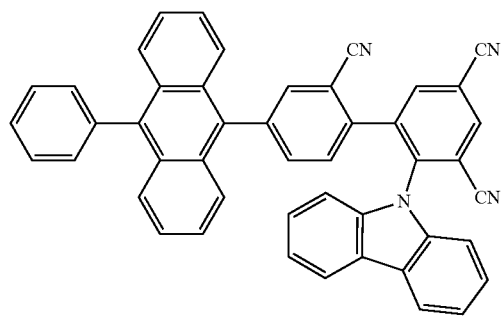
259
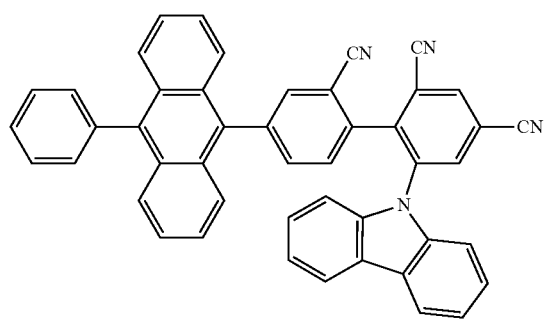
260
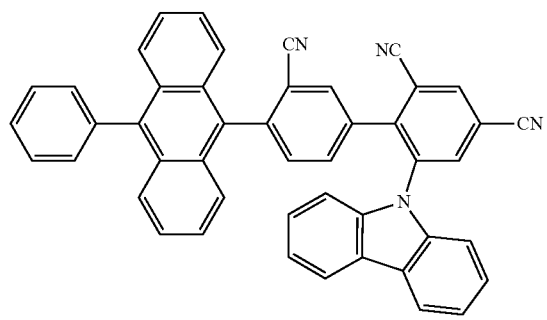

-continued
261
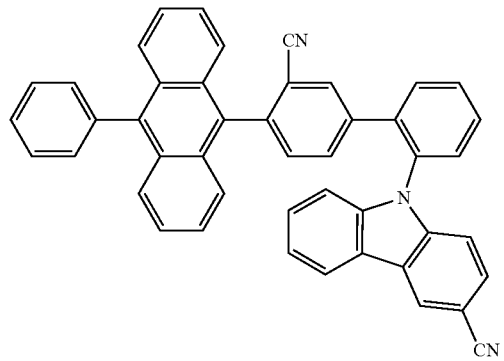
262
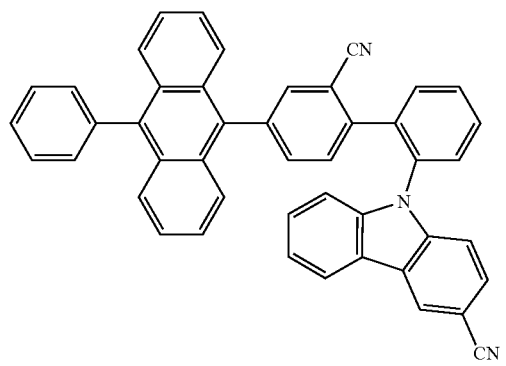
263
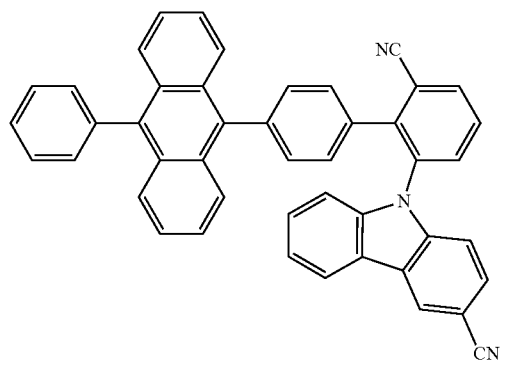
264
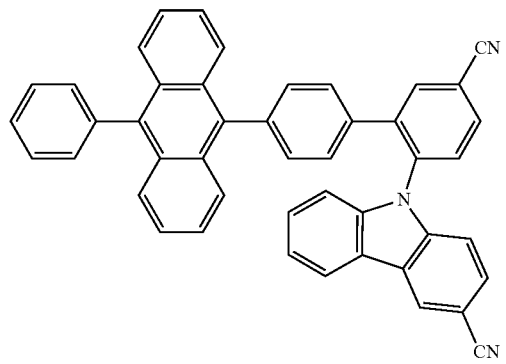

265
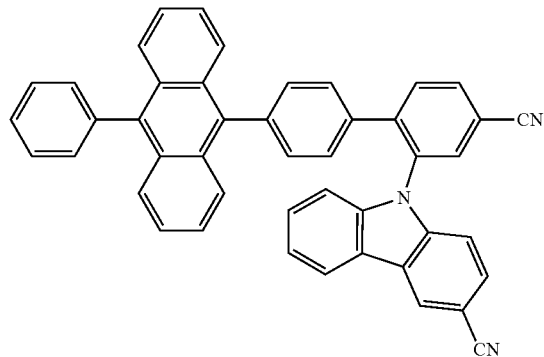
266
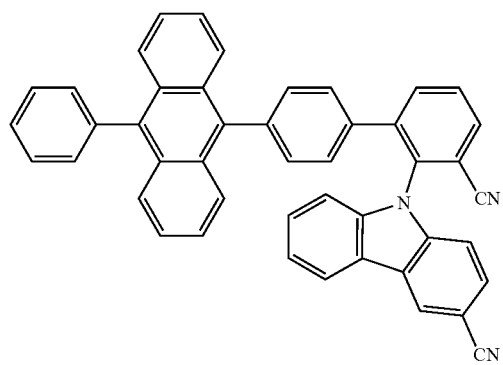
267
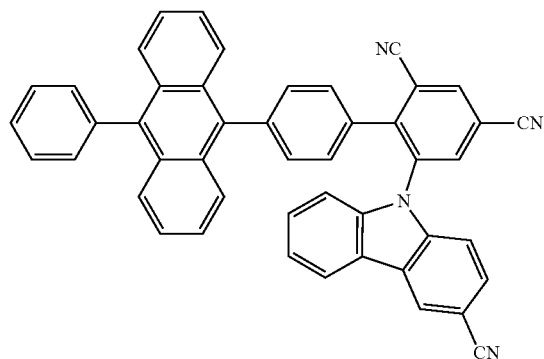
268
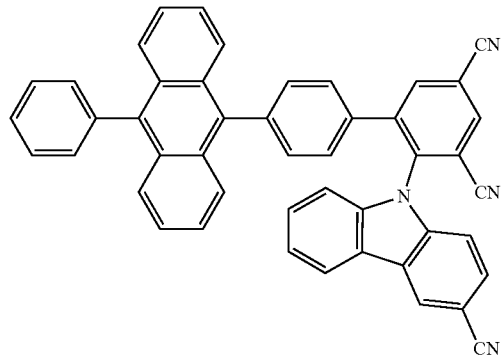

-continued
269
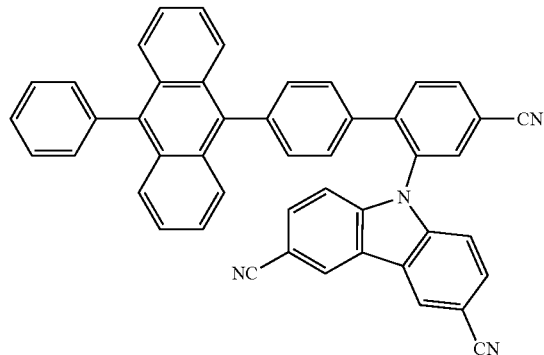
270
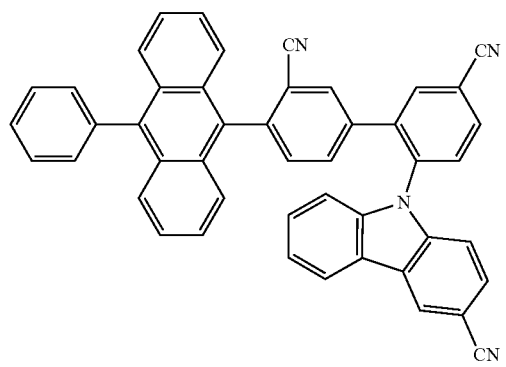
271
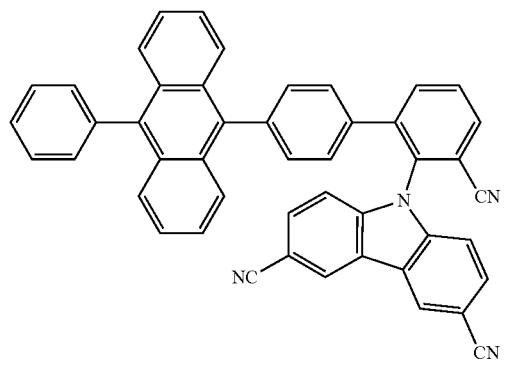
272
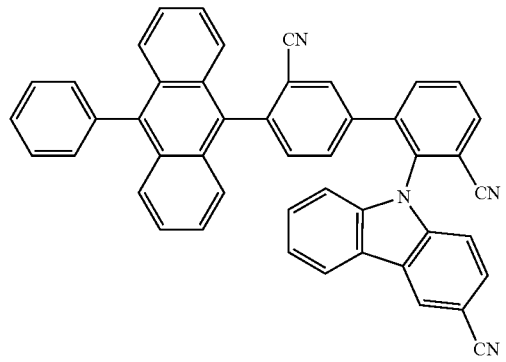

273
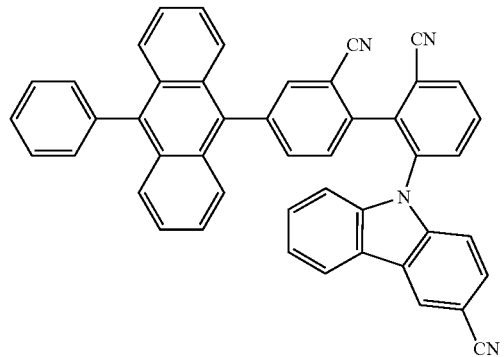
274
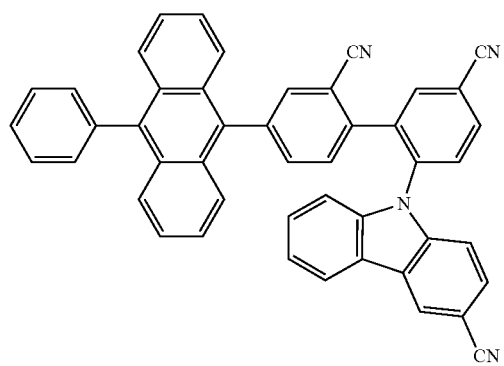
275
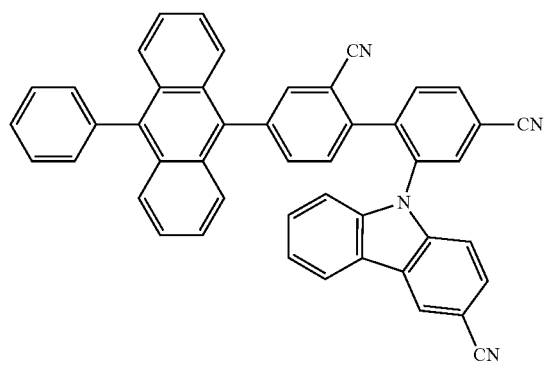
276
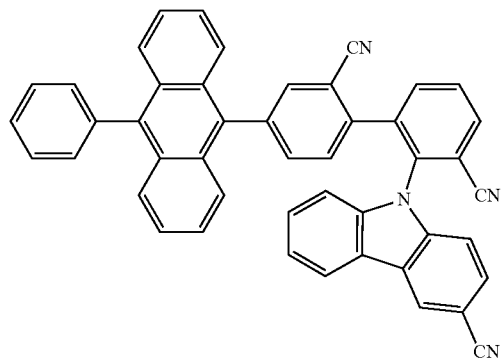

-continued
277
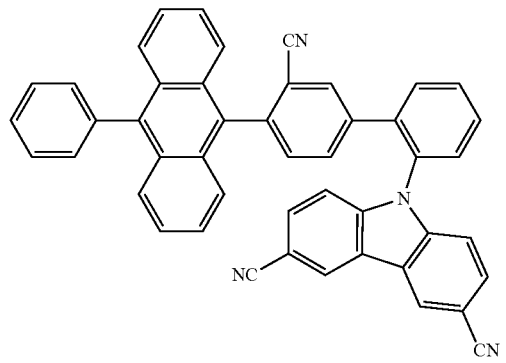
278
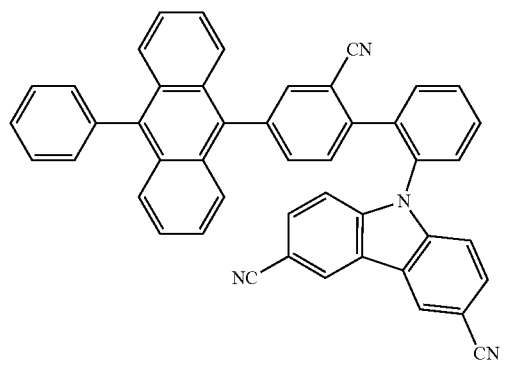
279
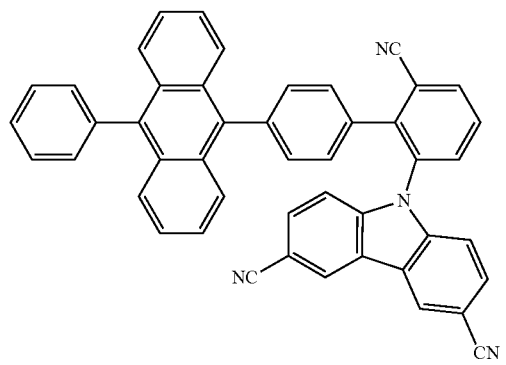
280
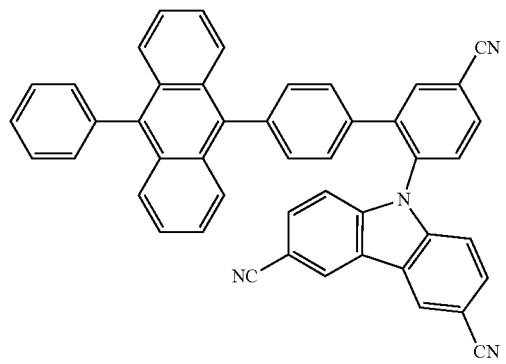

281
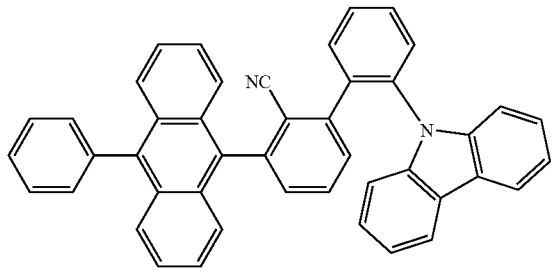
282
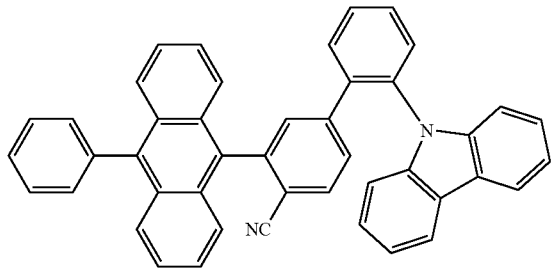
283
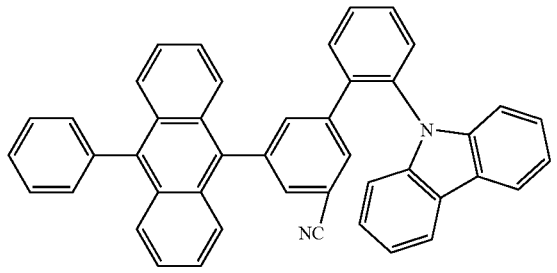
284
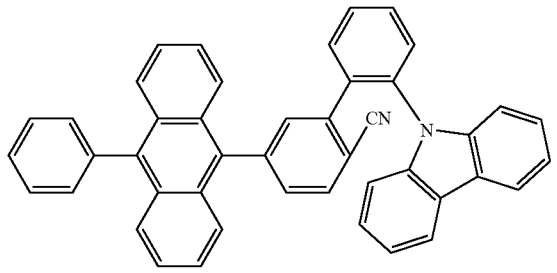
285
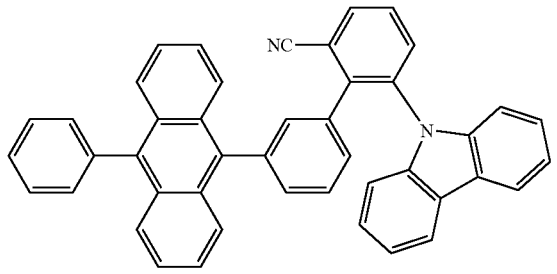

-continued
286
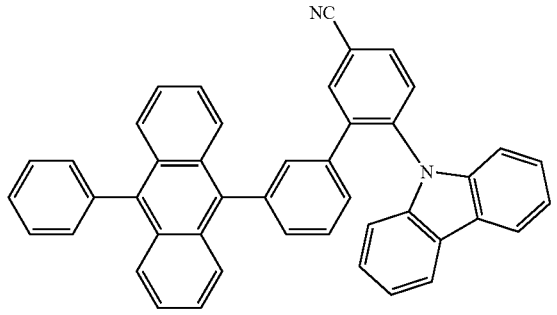
287
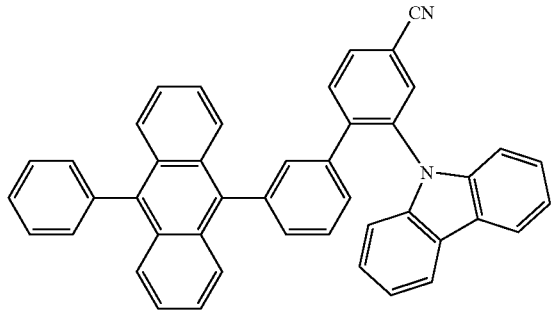
288
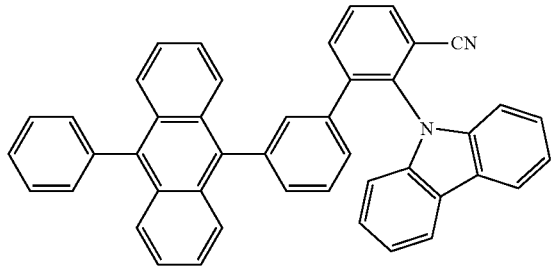
289
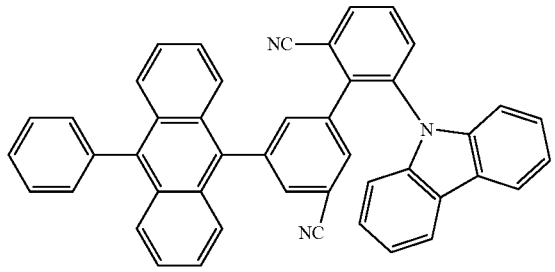
290
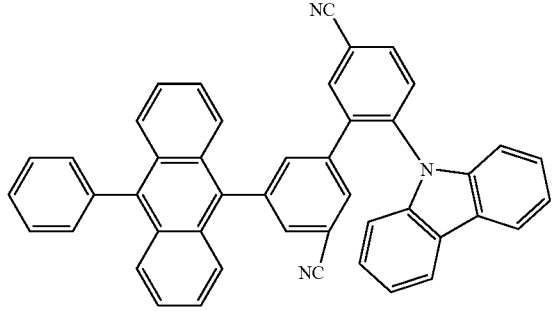

-continued
291
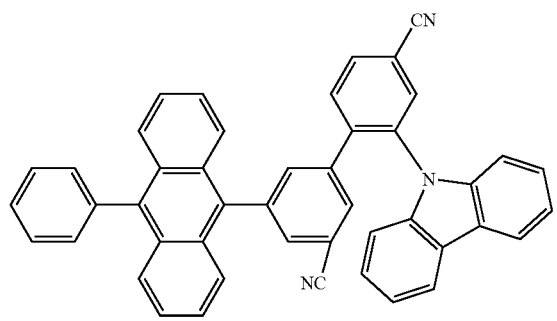
292
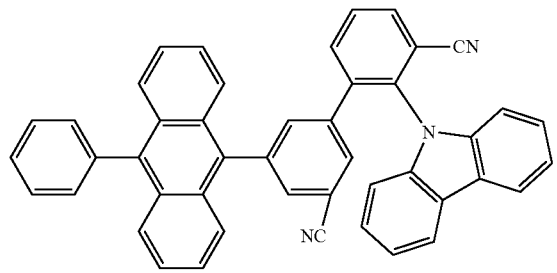
293
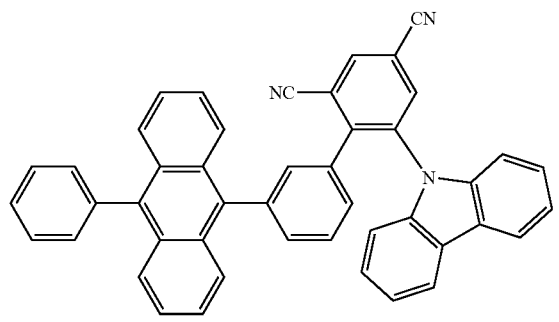
294
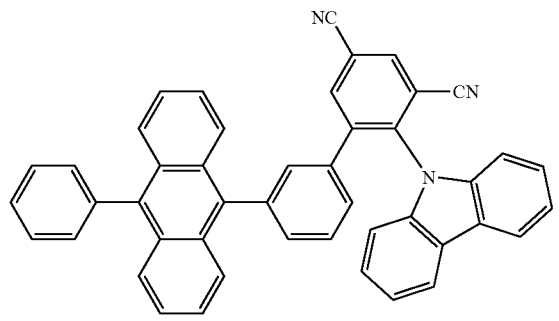
295
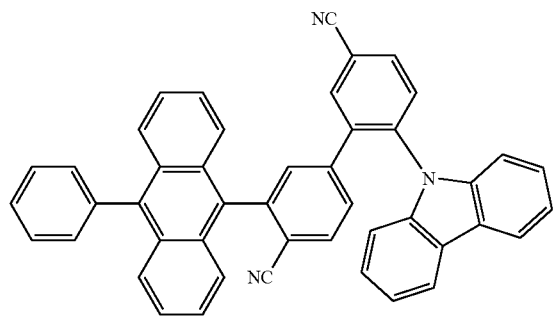

-continued
296
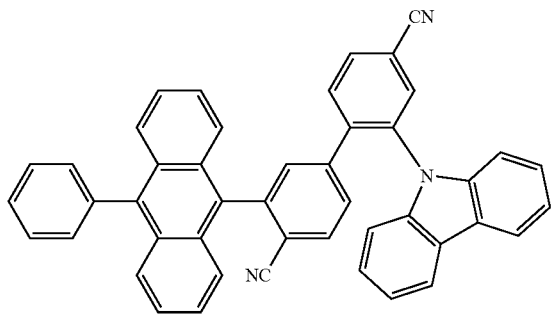
297
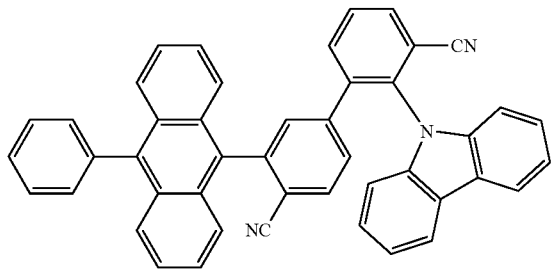
298
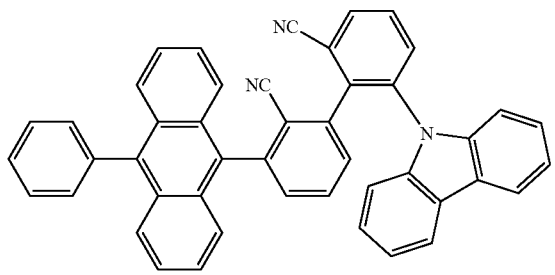
299
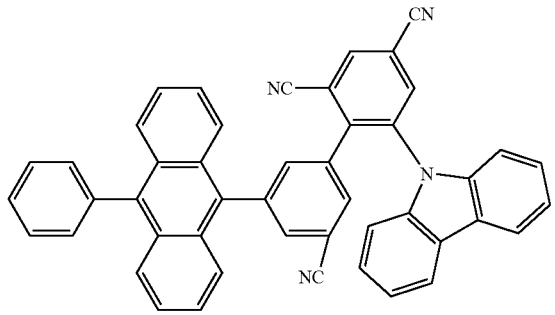
300
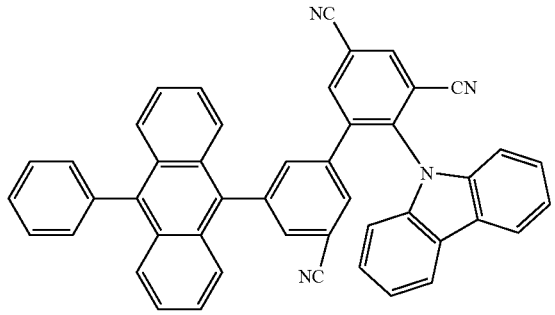

301
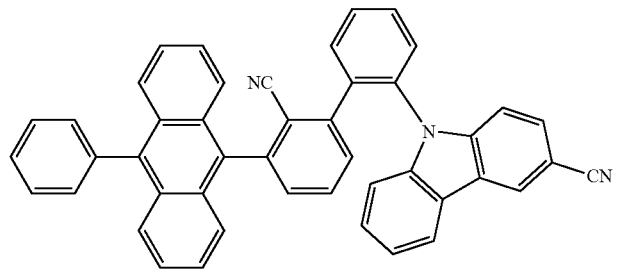
302
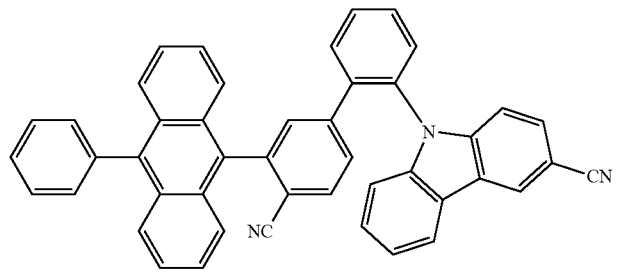
303
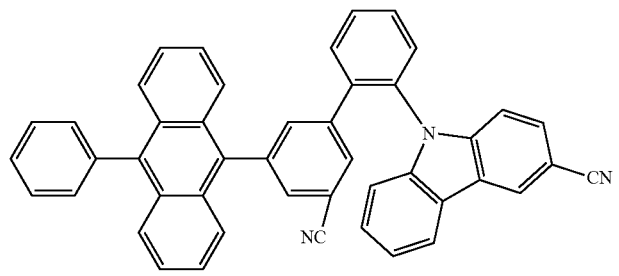
304
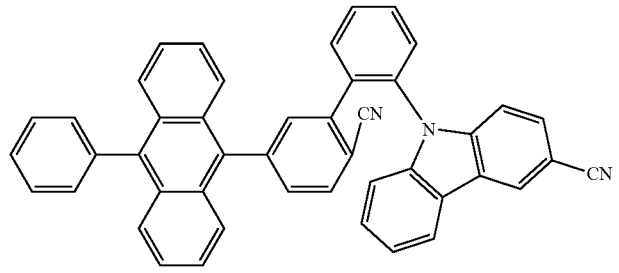
305
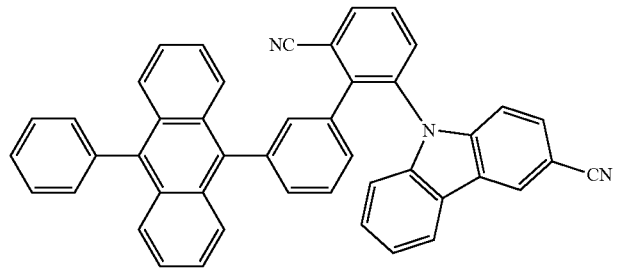

-continued
306
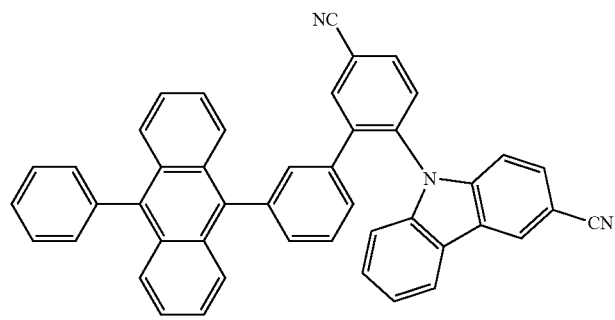
307
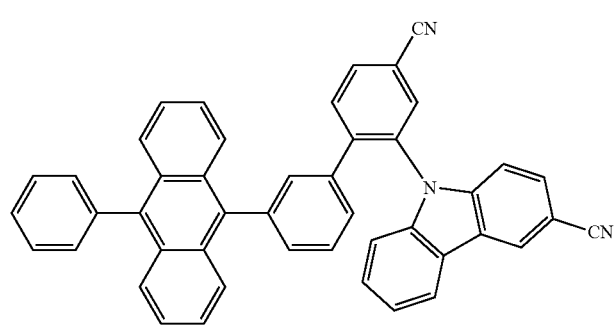
308
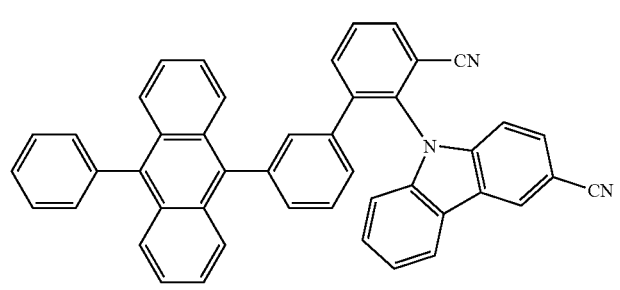
309
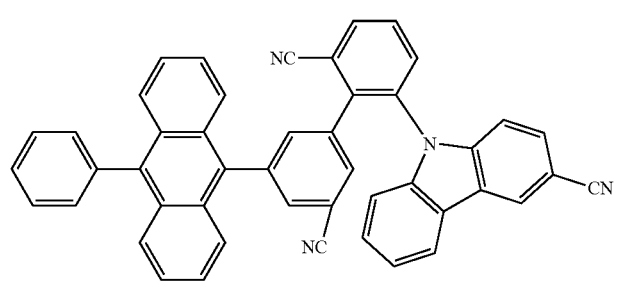
310
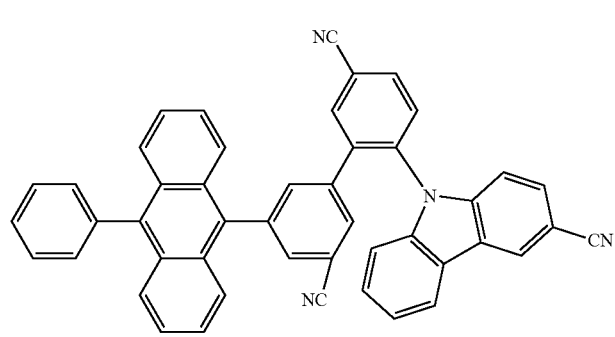

-continued
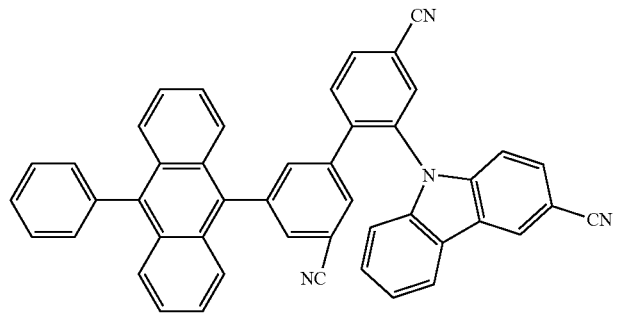
311
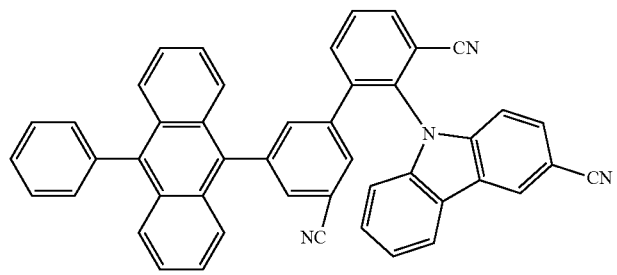
312
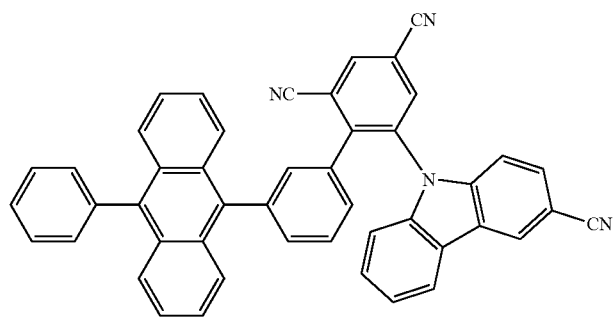
313
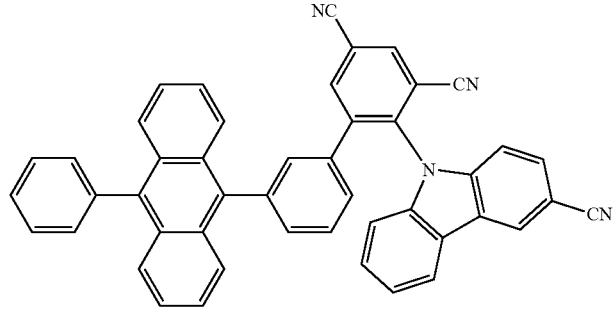
314
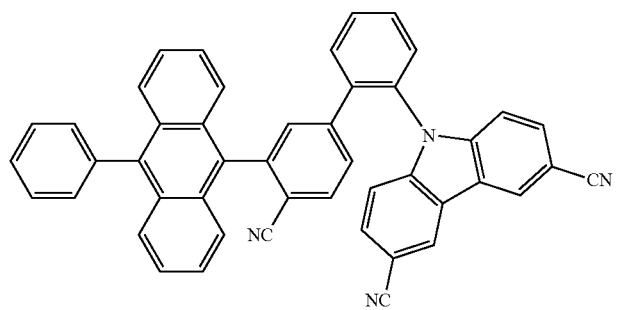
315

316
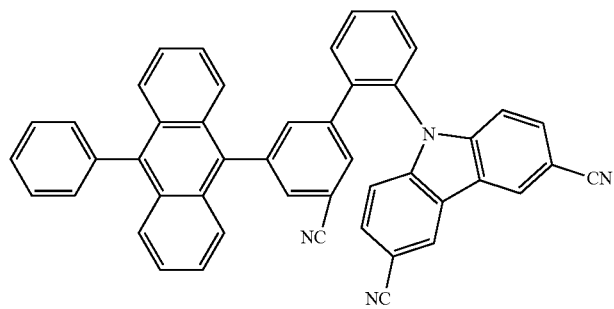
317
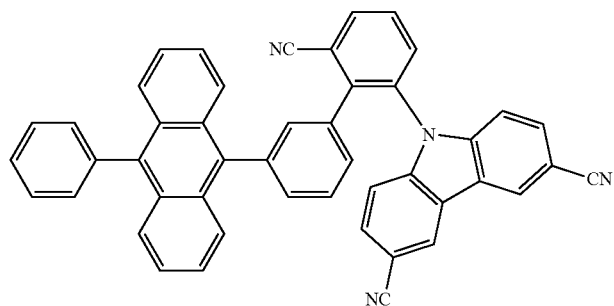
318
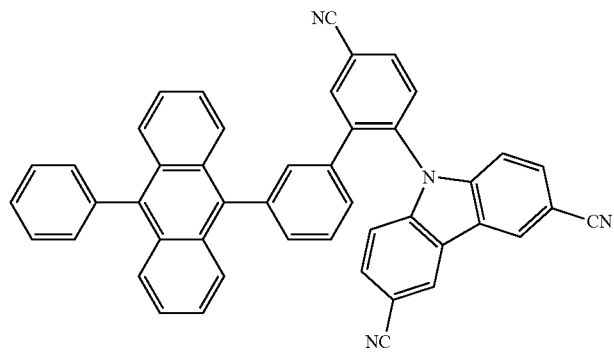
319
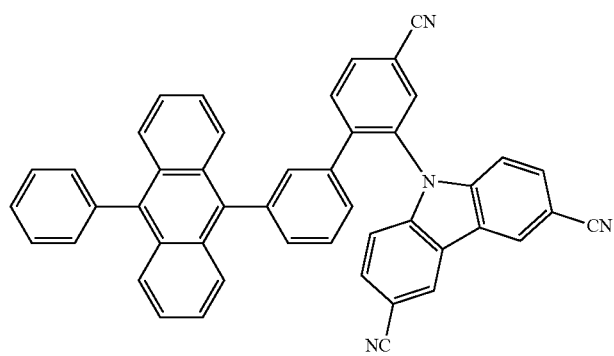
320
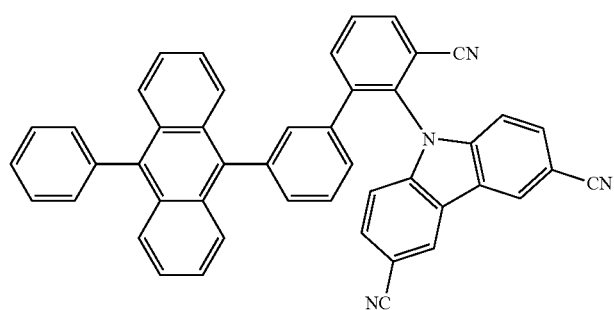

-continued
321
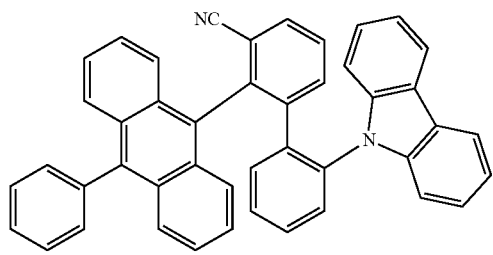
322
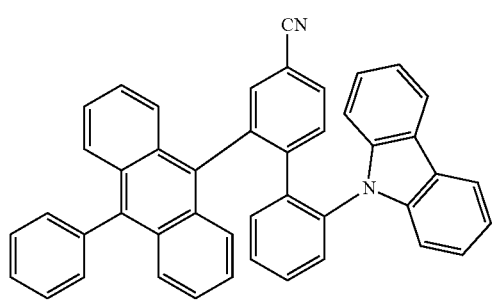
323
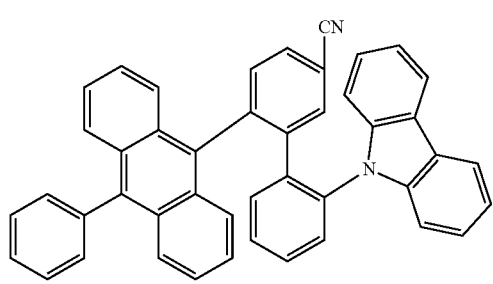
324

325
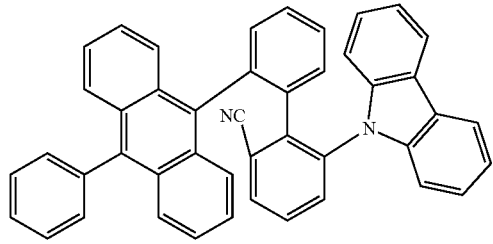
326
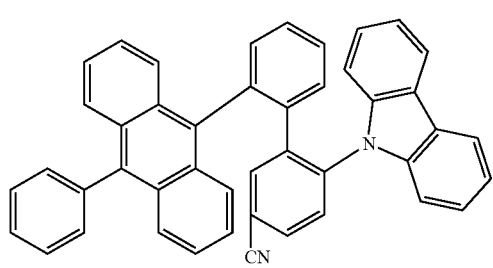

-continued
327
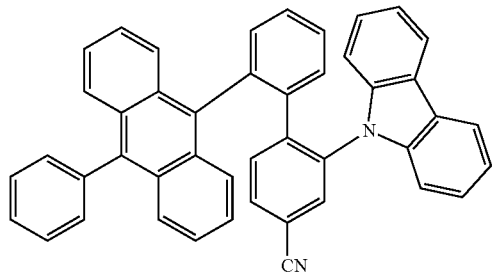
328
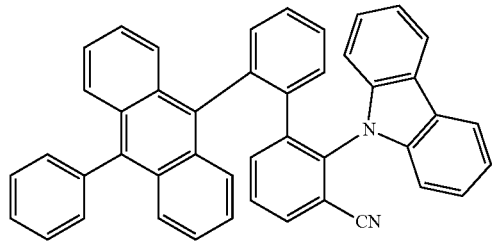
329
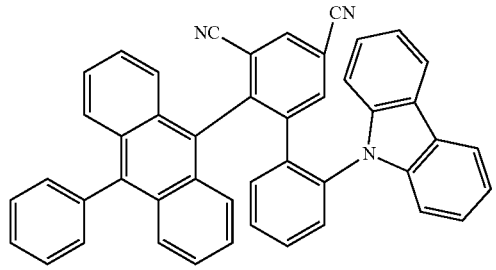
330
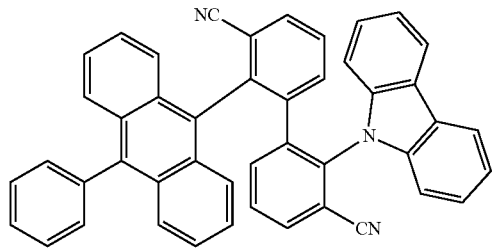
331
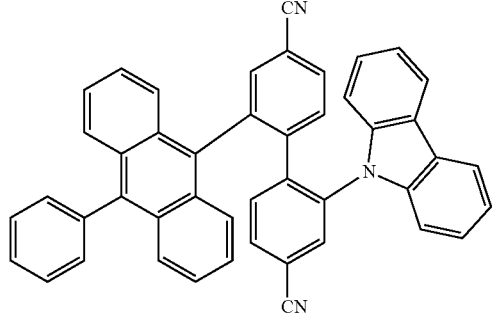

332
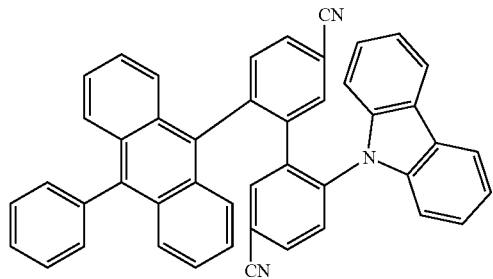
333
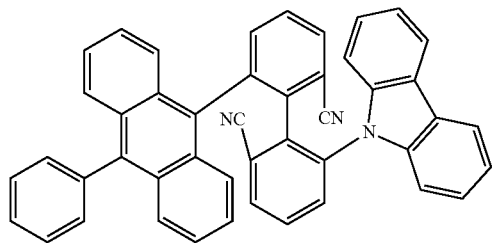
334
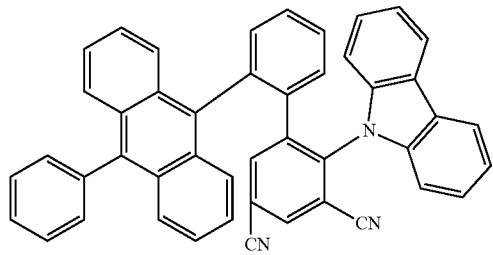
335
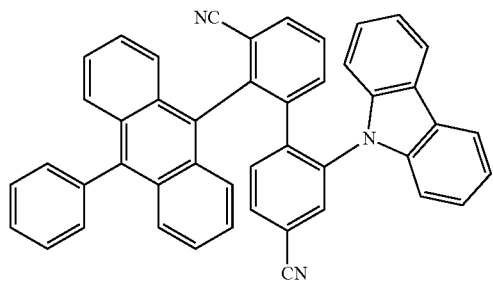
336
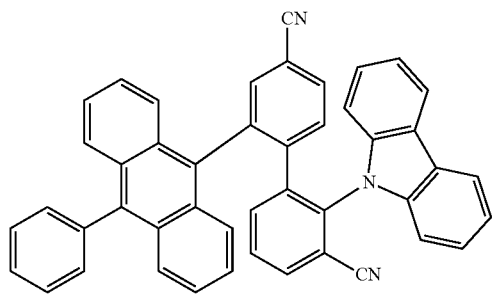

-continued
337
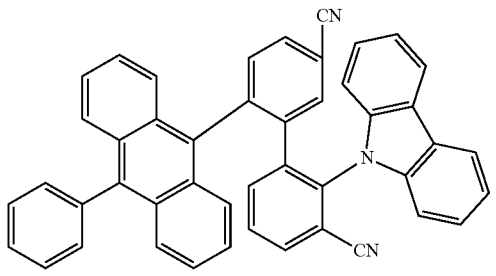
338
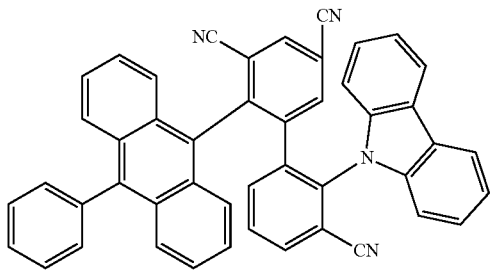
339
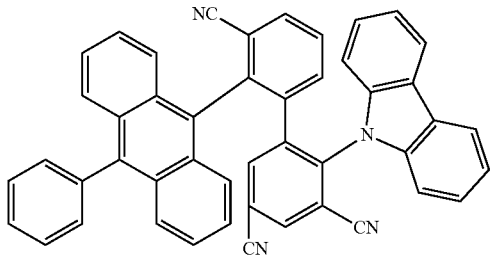
340
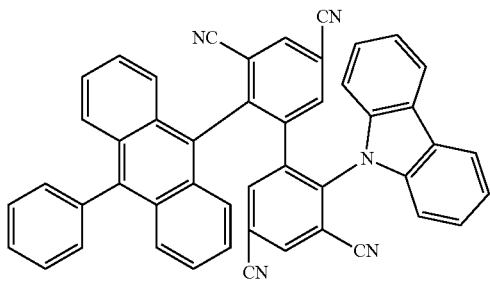
341
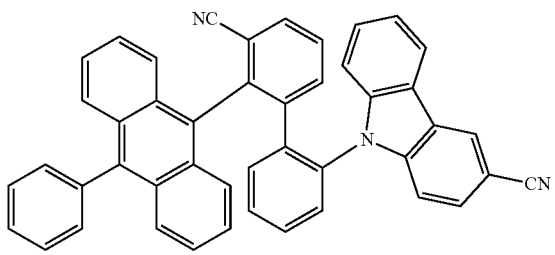

-continued
342
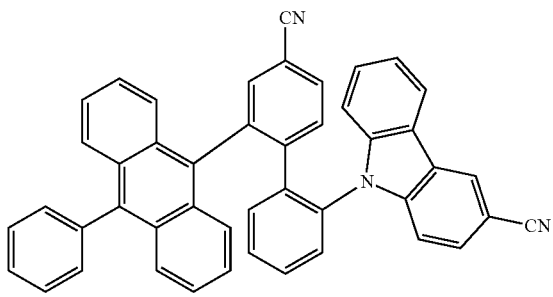
343
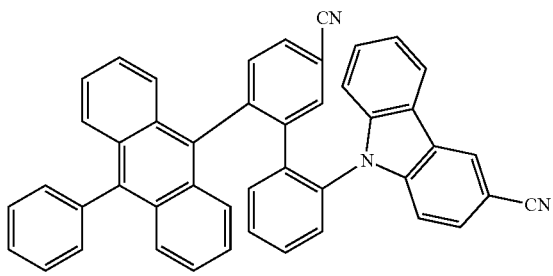
344
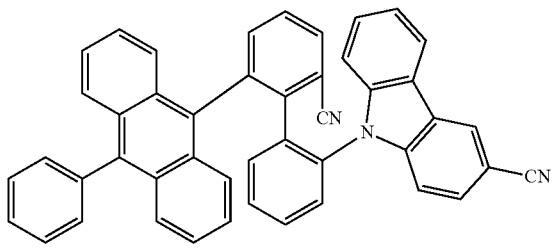
345
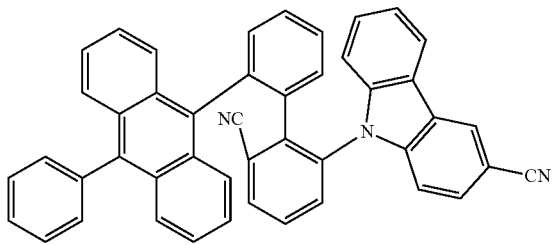
346
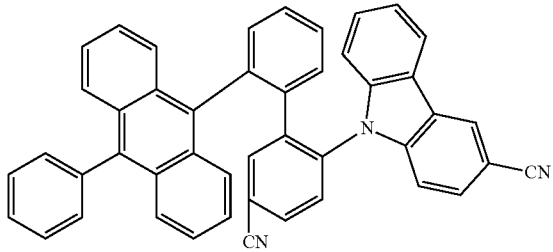
347
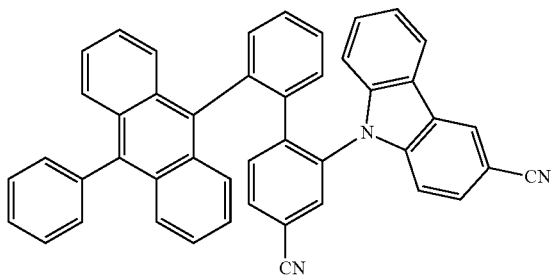

-continued
348
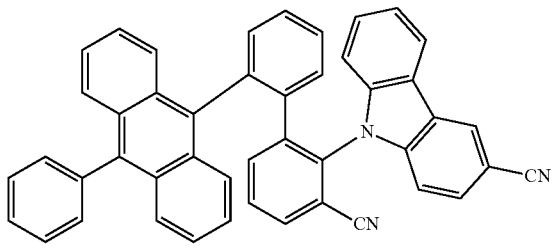
349
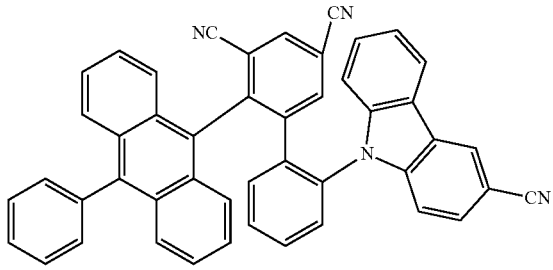
350
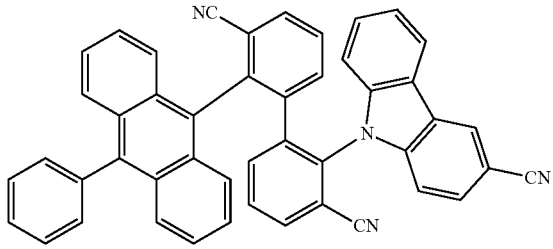
351
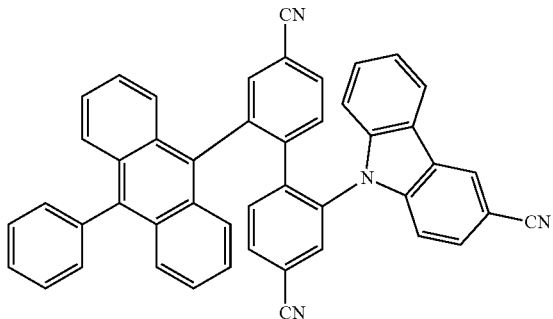
352
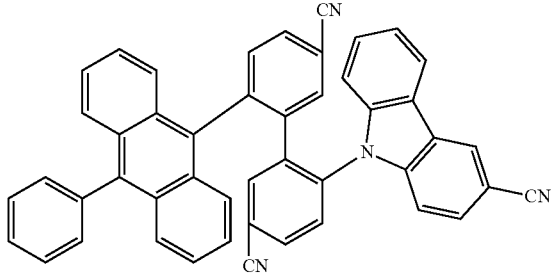
353
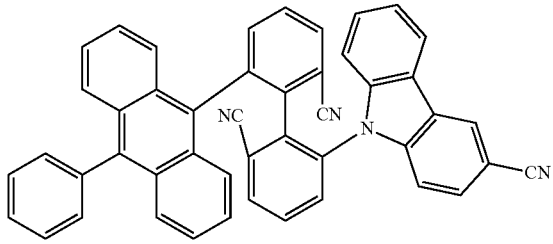

-continued
354
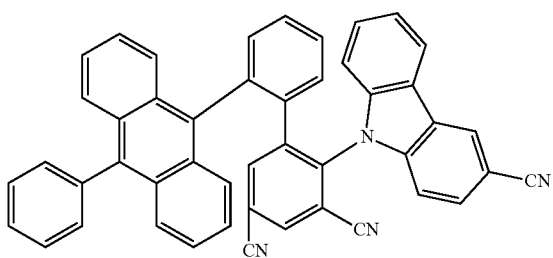
355
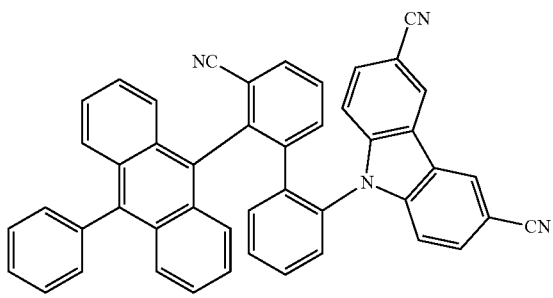
356
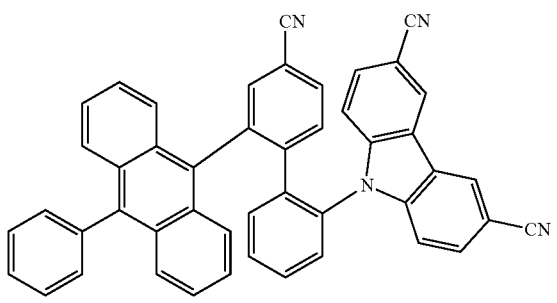
357
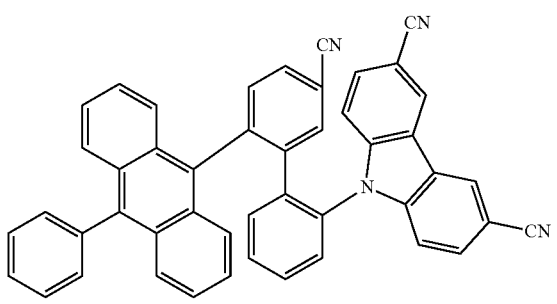
358
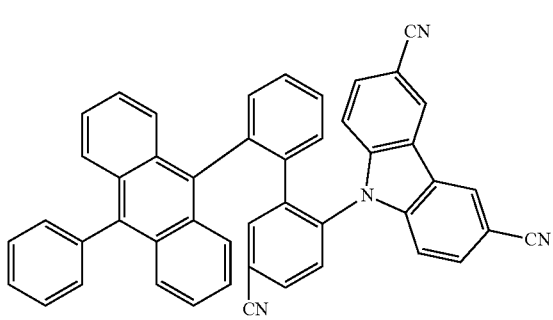

-continued
359
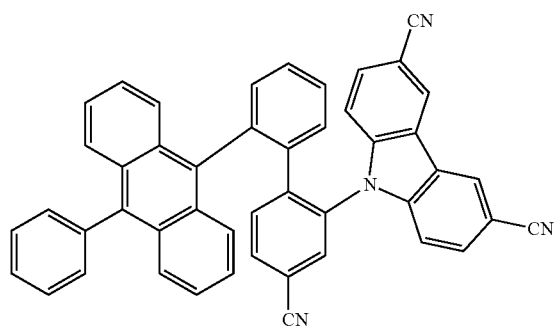
360
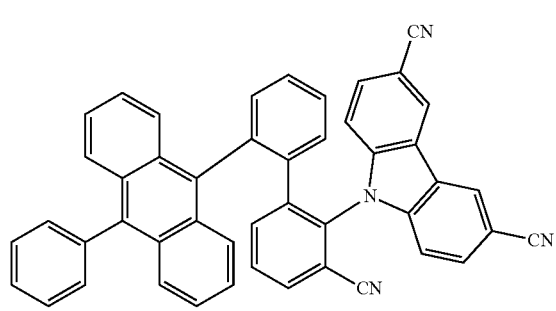
361
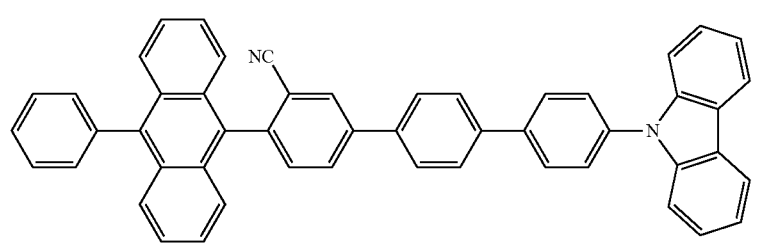
362
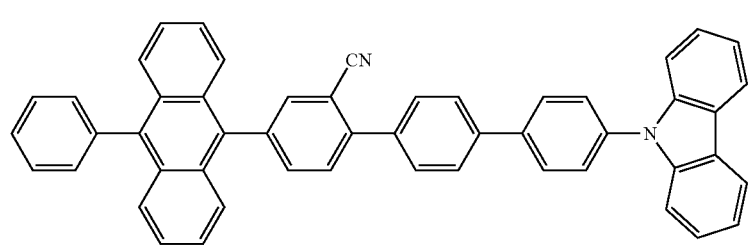
363
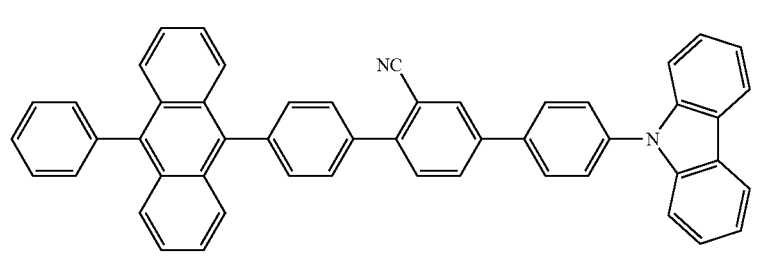
364
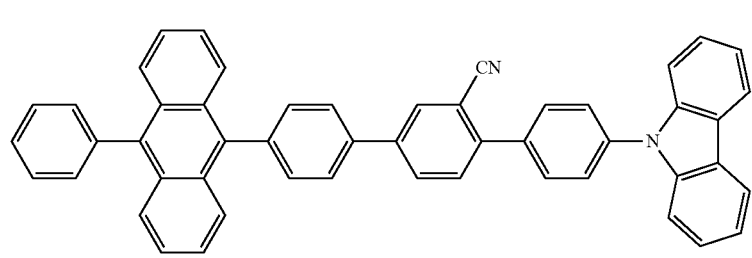

365
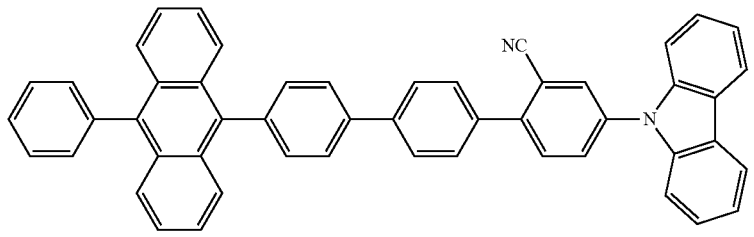
366
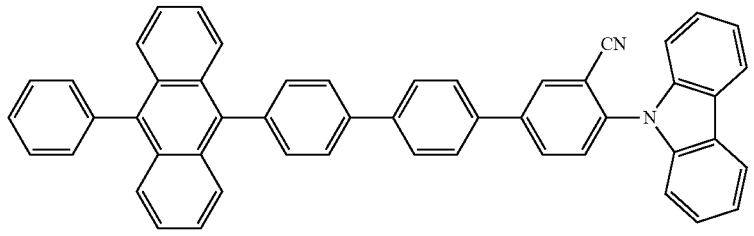
367
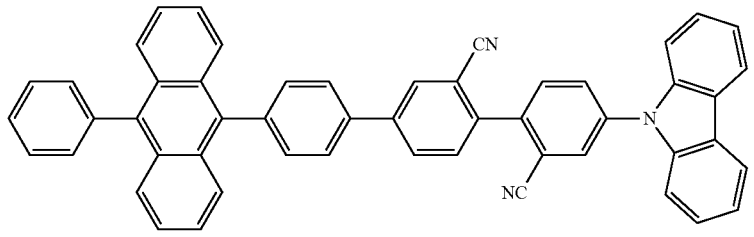
368
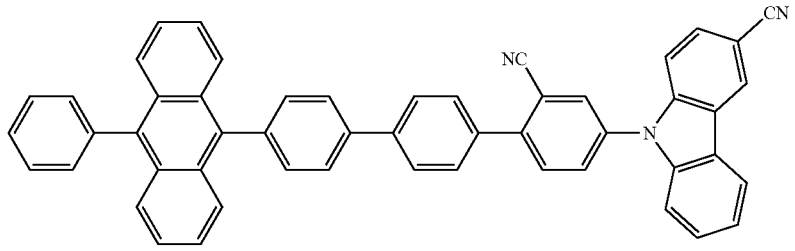
369
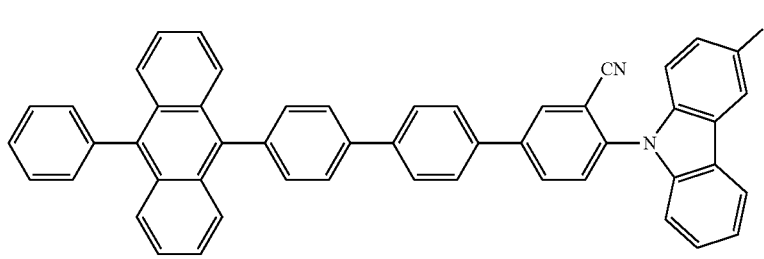
370
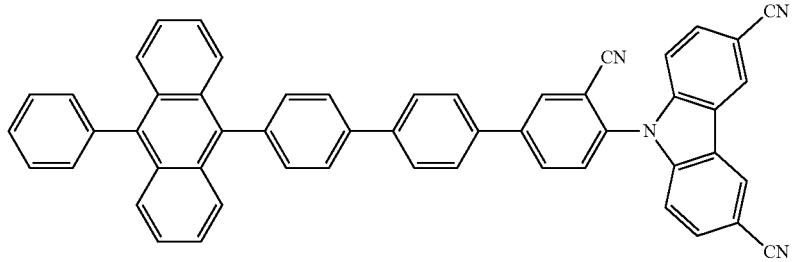

371
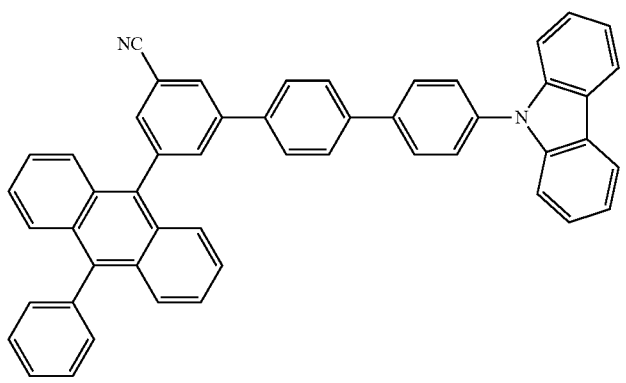
372
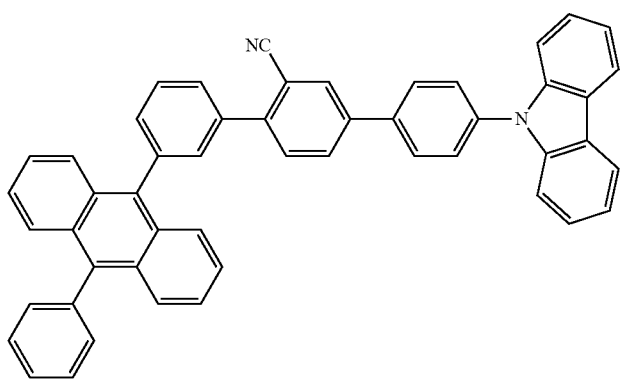
373
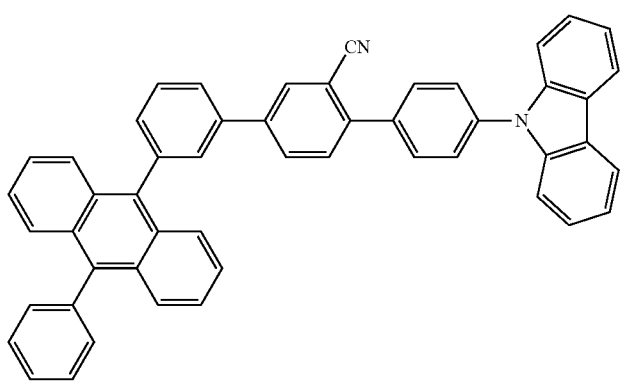
374
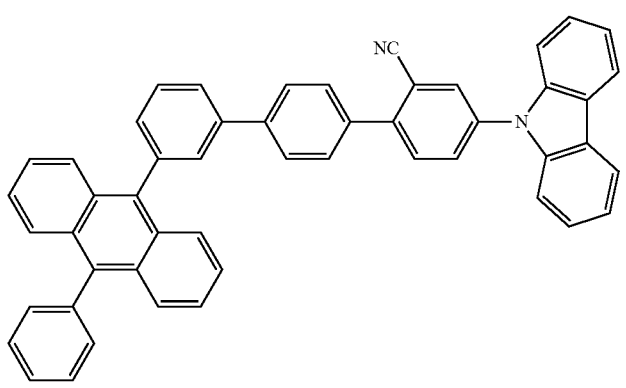

-continued
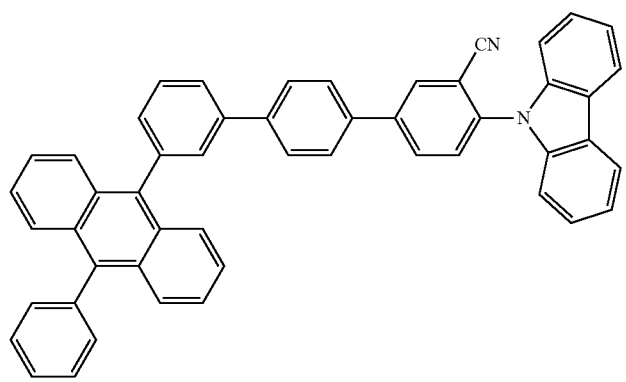
375
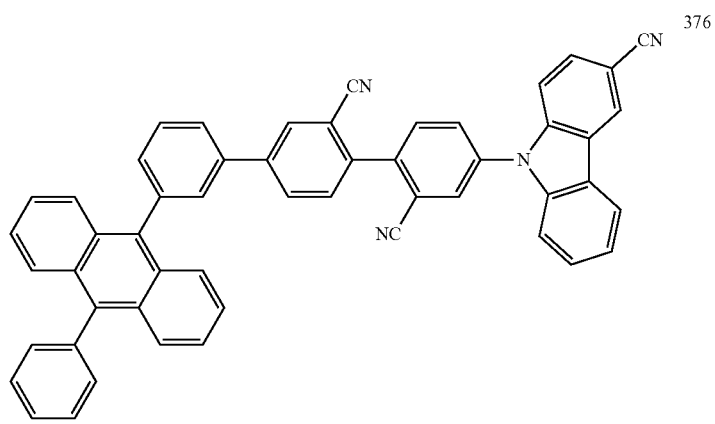
376
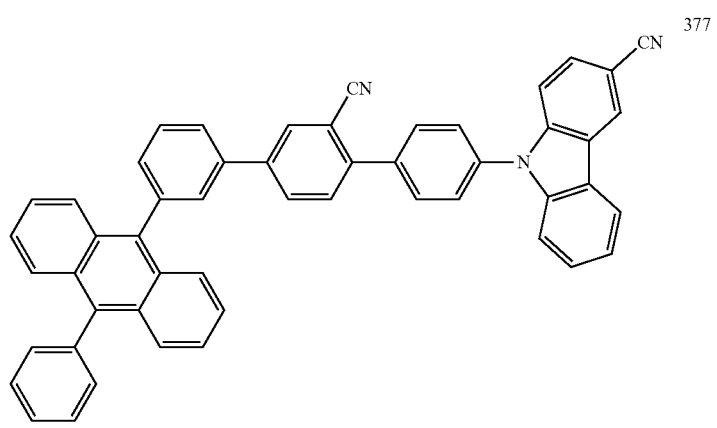
377
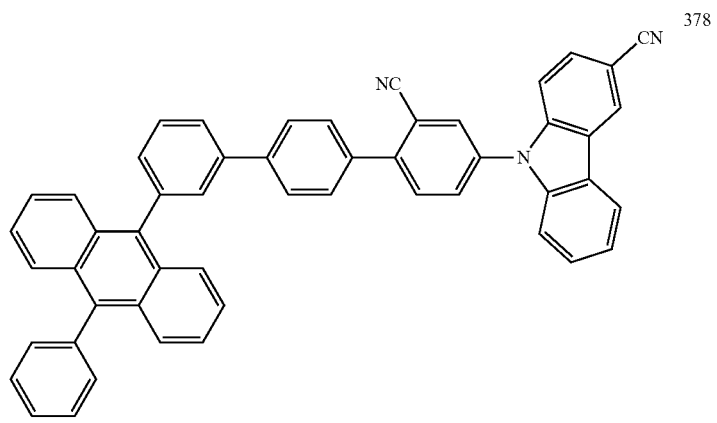
378

-continued
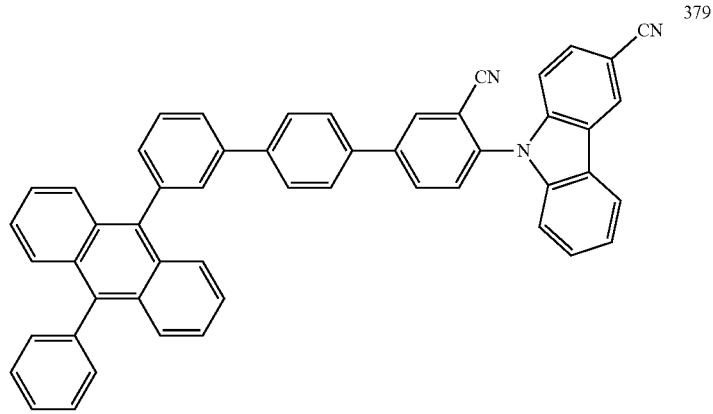
379
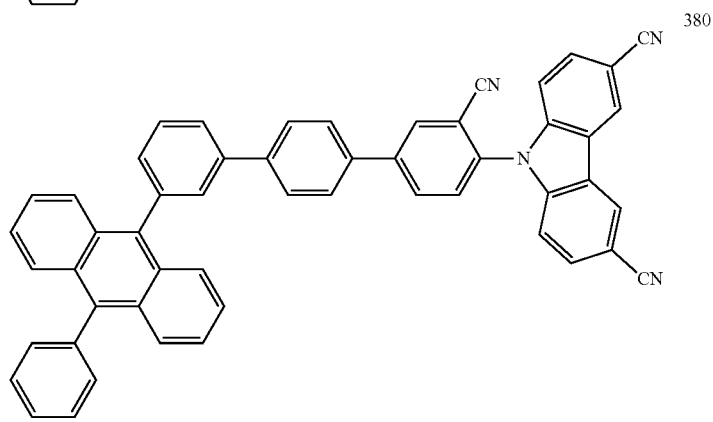
380
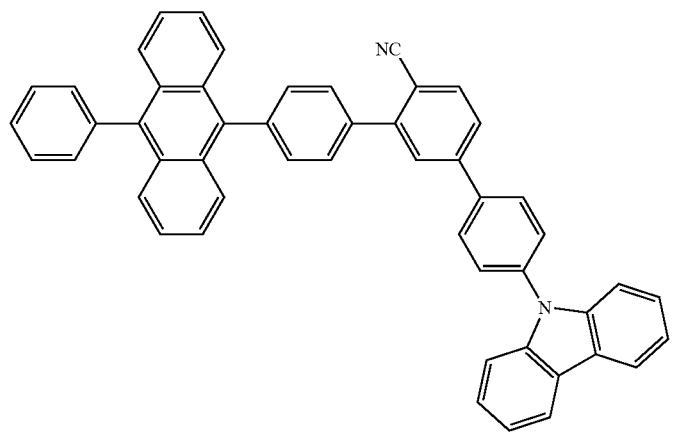
381
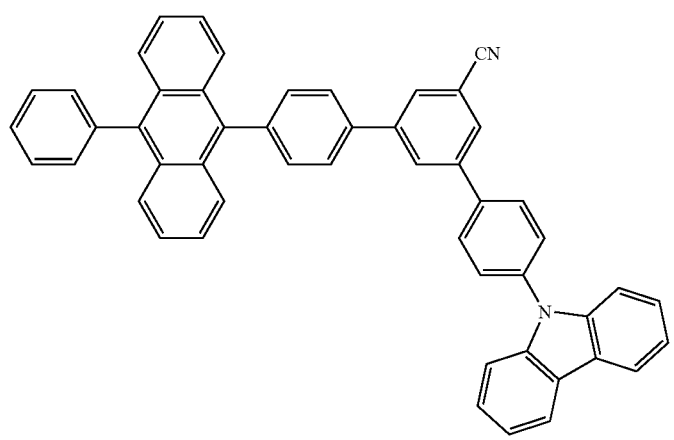
382

383
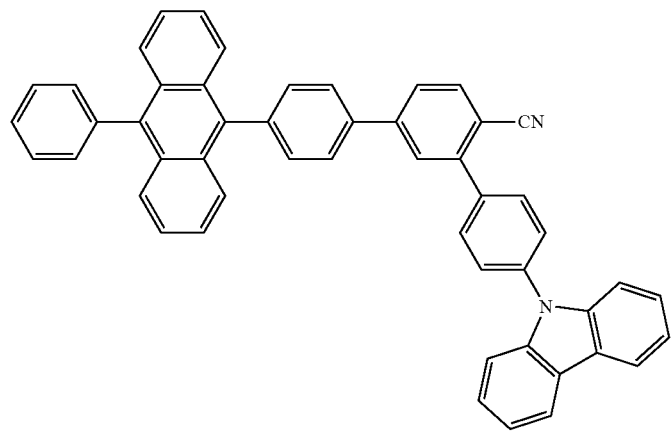
384
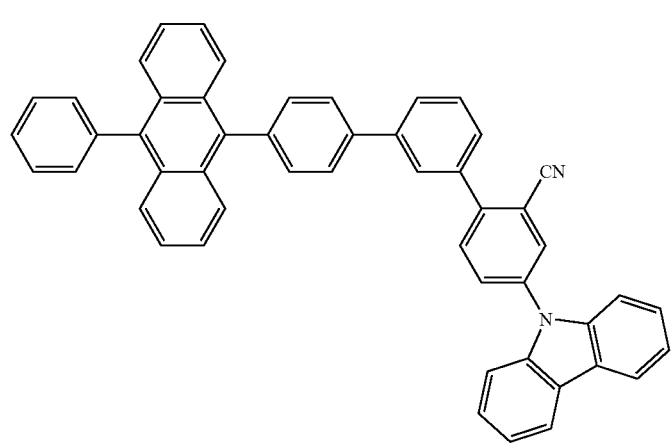
385
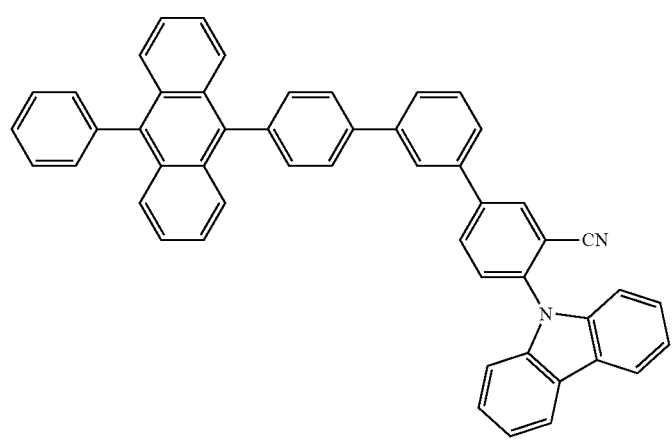

389
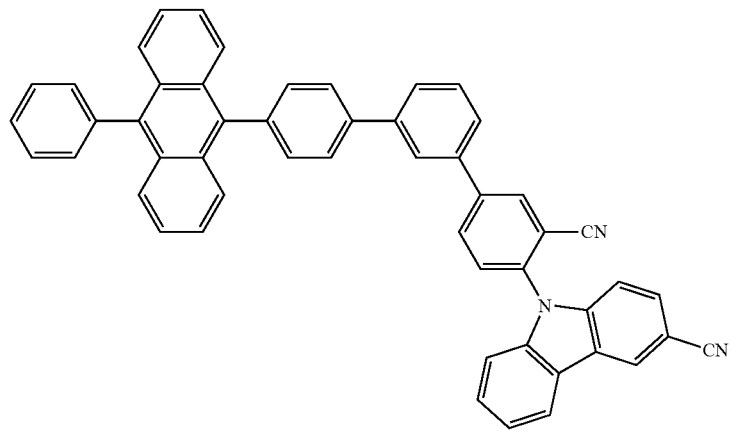
386
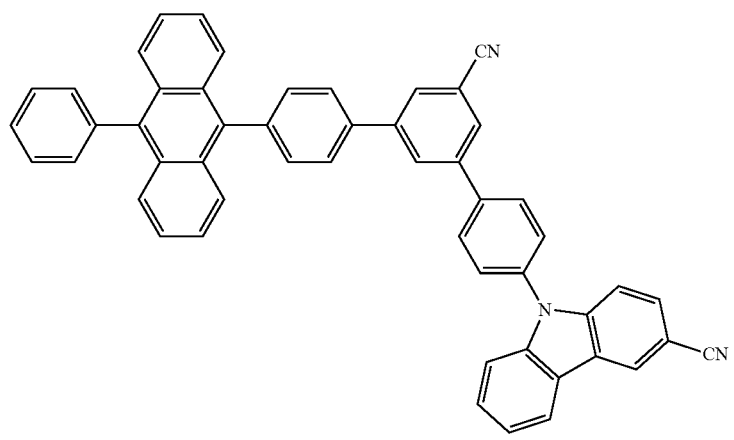
387
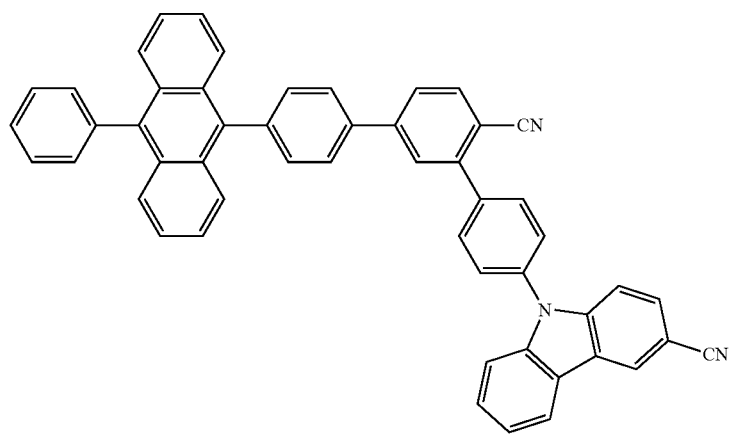

388
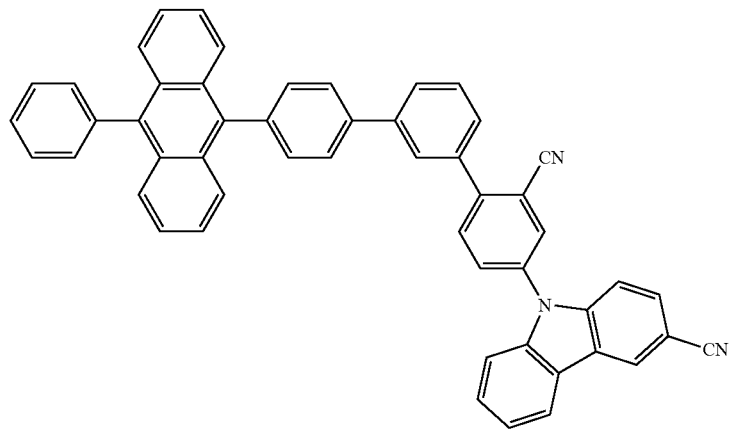
390
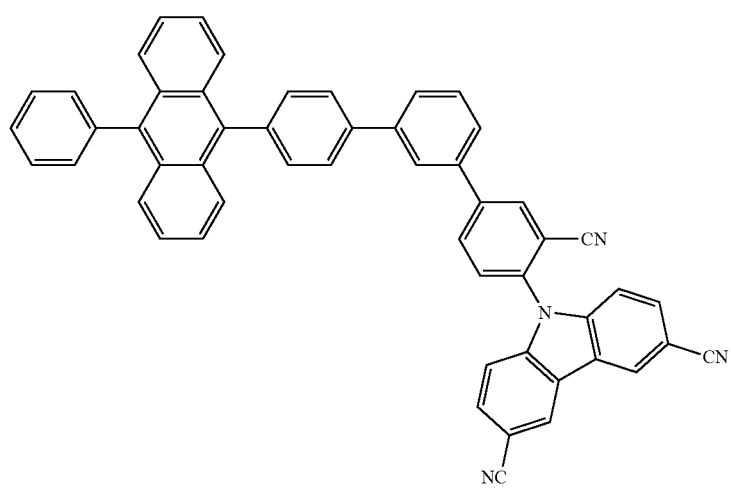
391
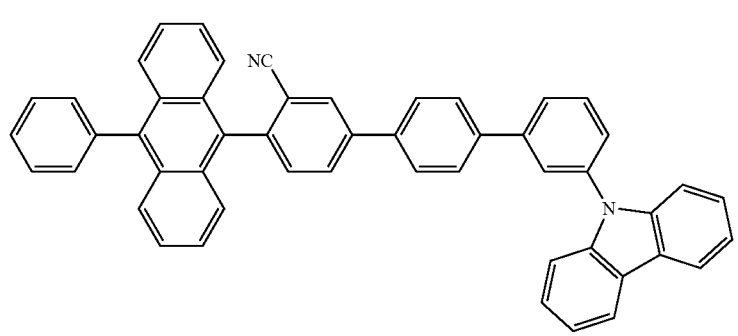
392
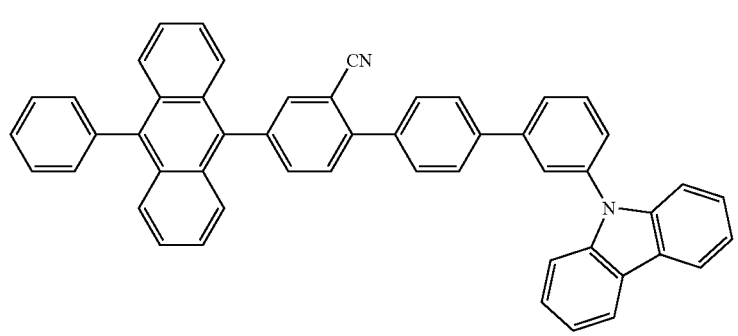

-continued
393
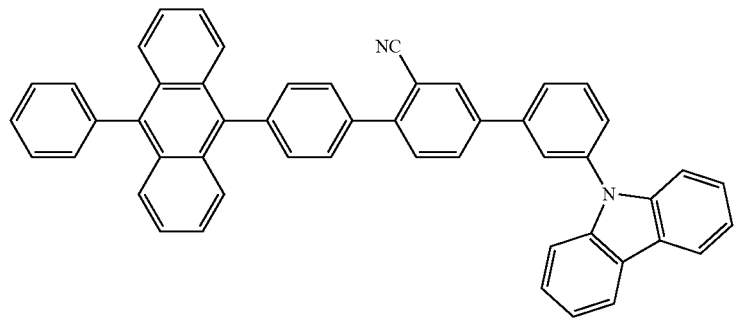
394
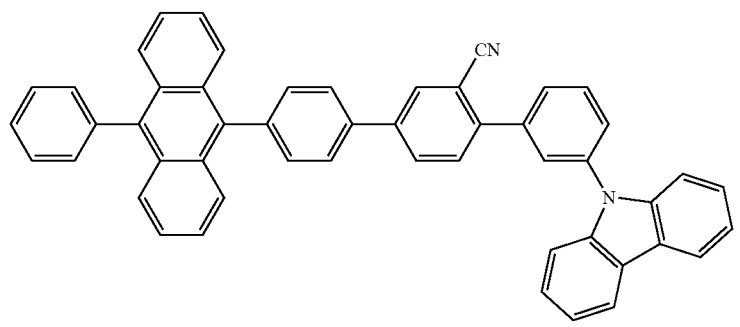
395
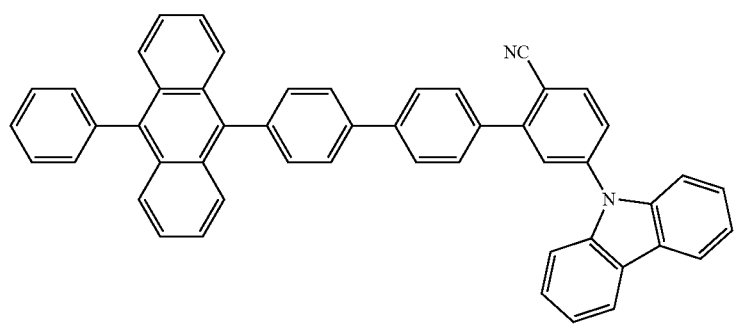
396
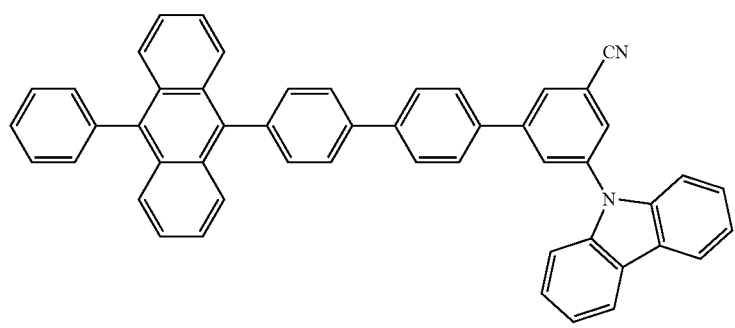
397
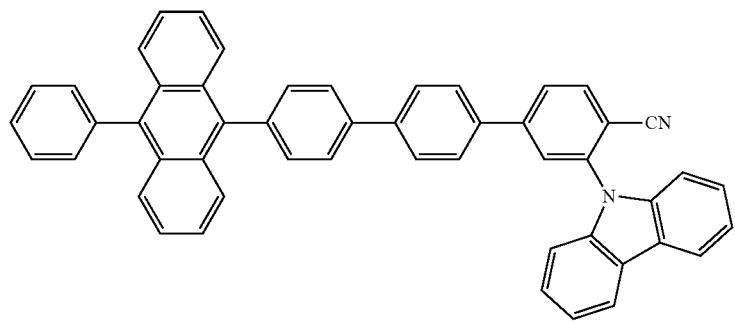

-continued
398
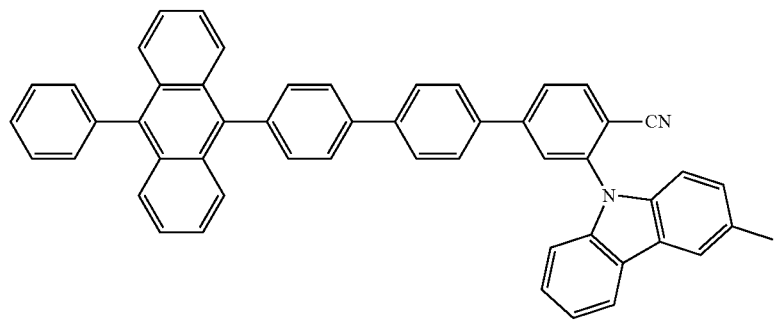
399
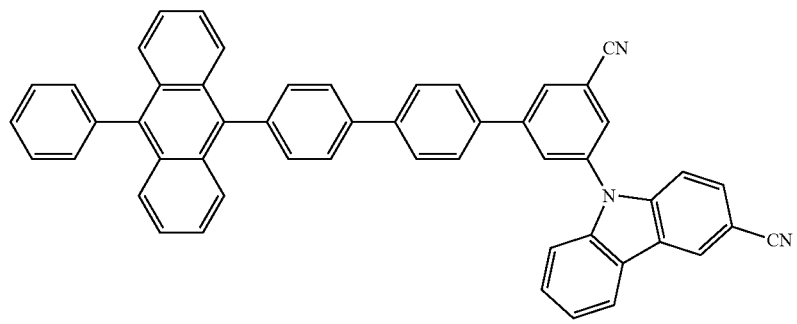
400
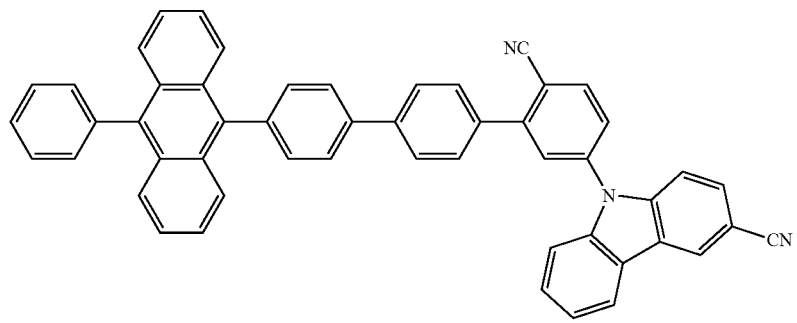
401
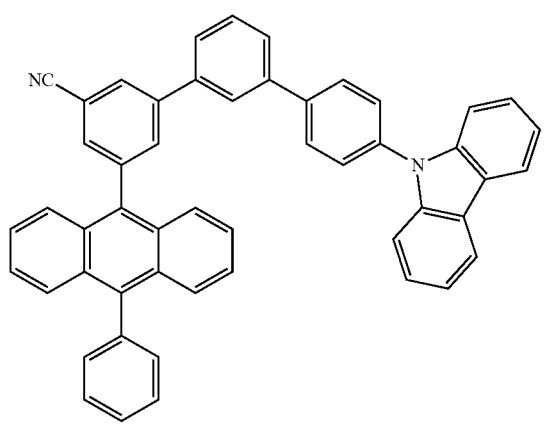
402
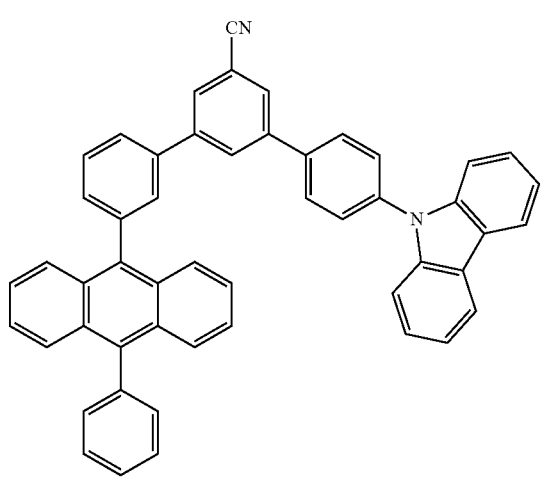

-continued
403
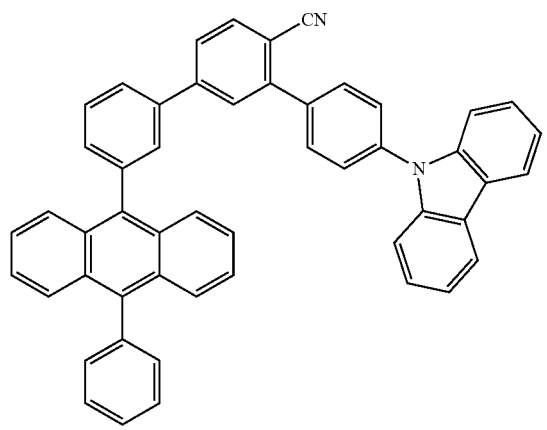
404
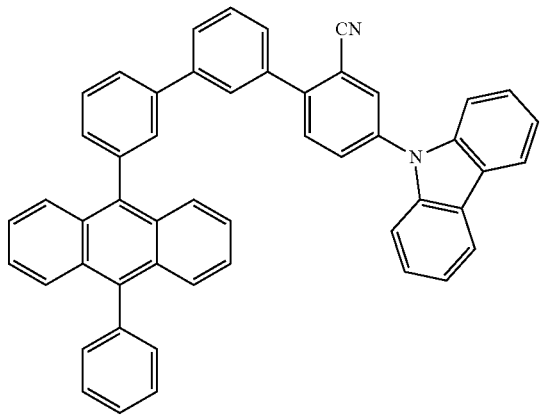
405
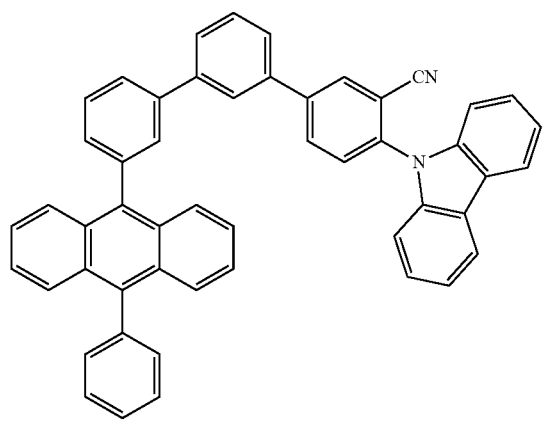
406
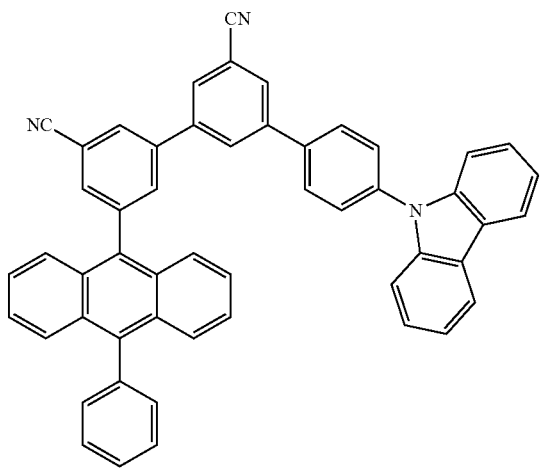
407
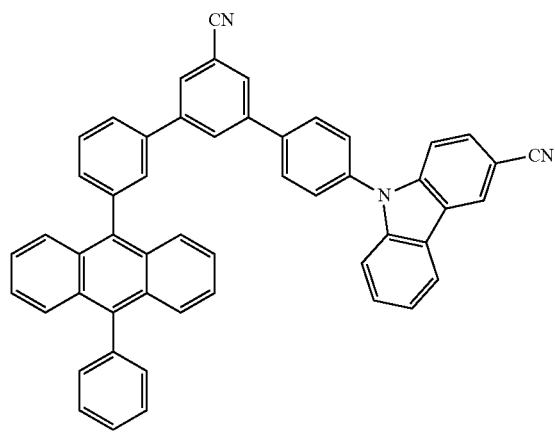
408
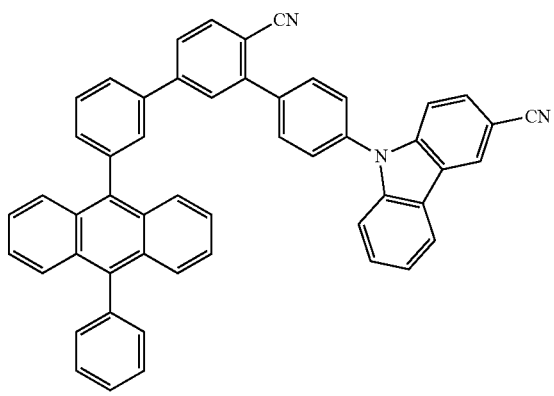

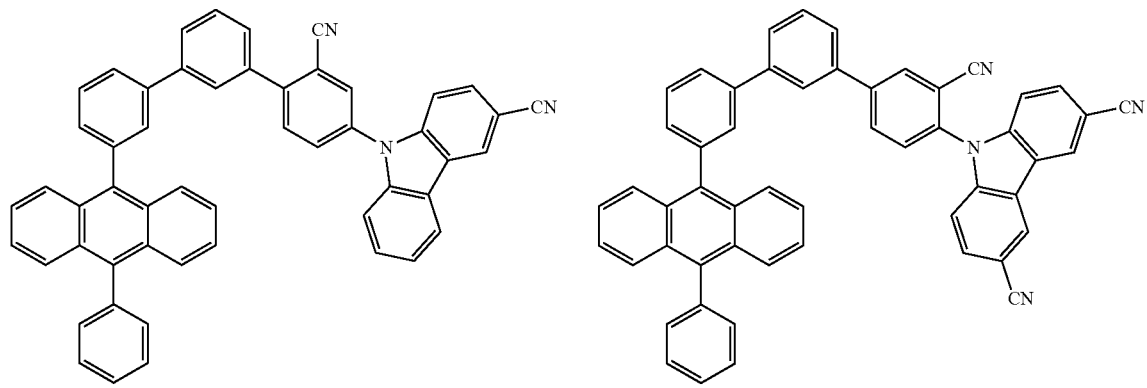
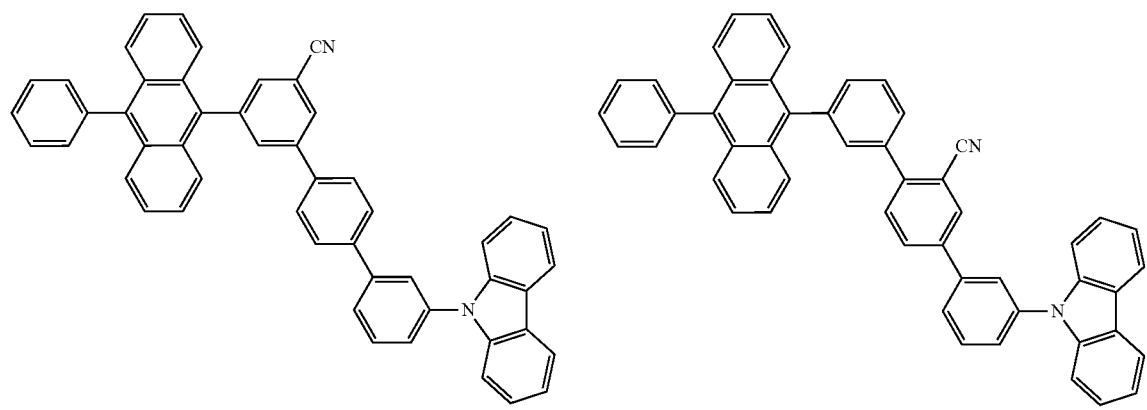
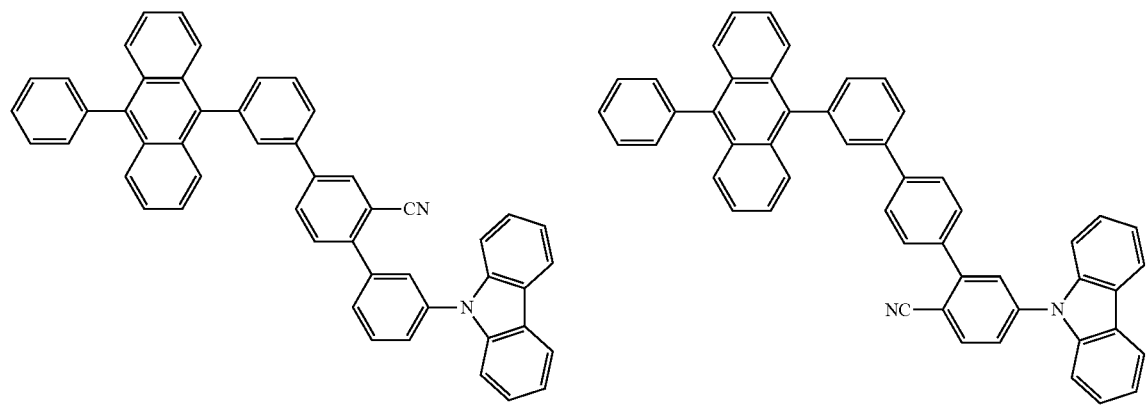

-continued
415
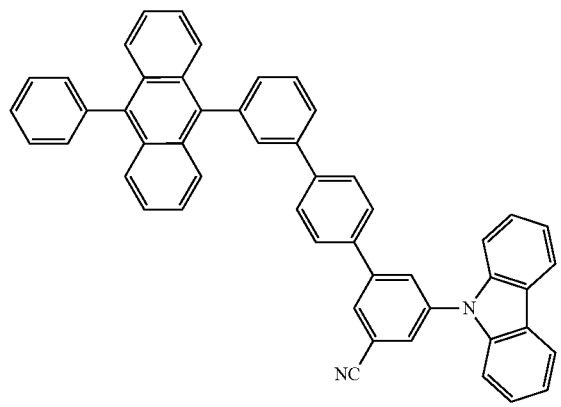
416
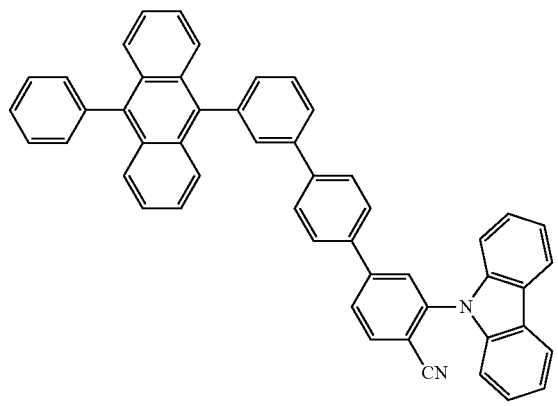
417
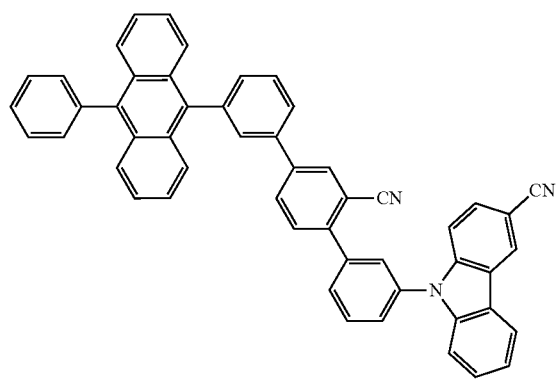
418
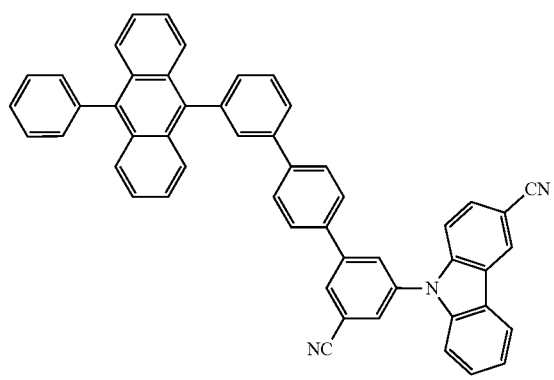
419
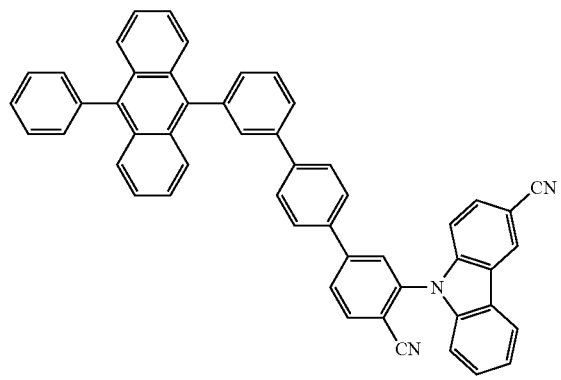
420
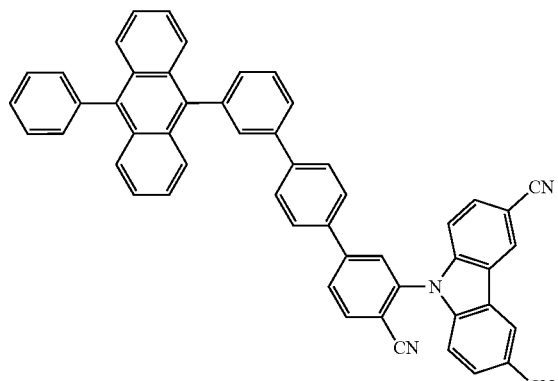

-continued
421
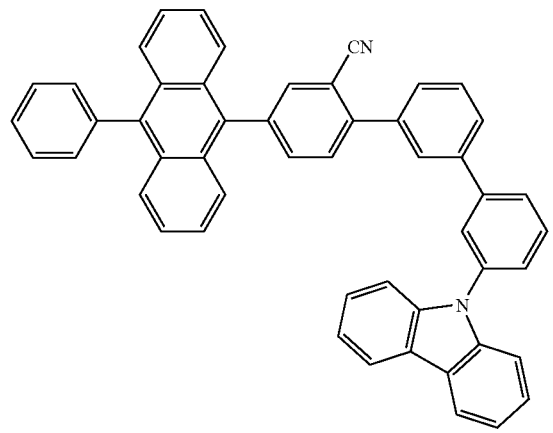
422
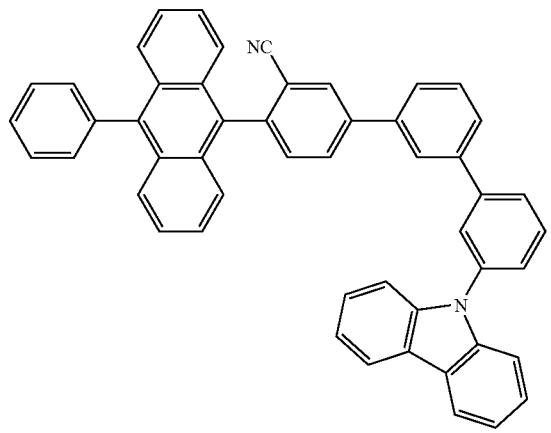
423
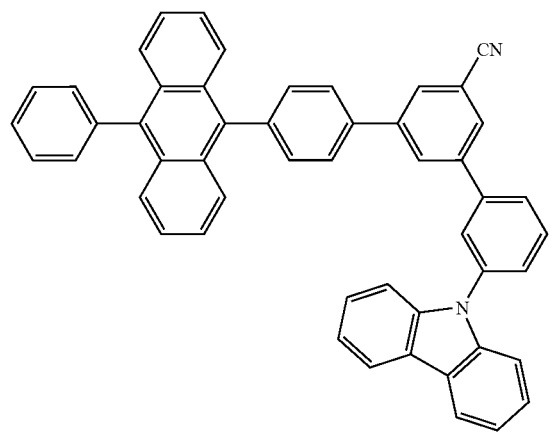
424
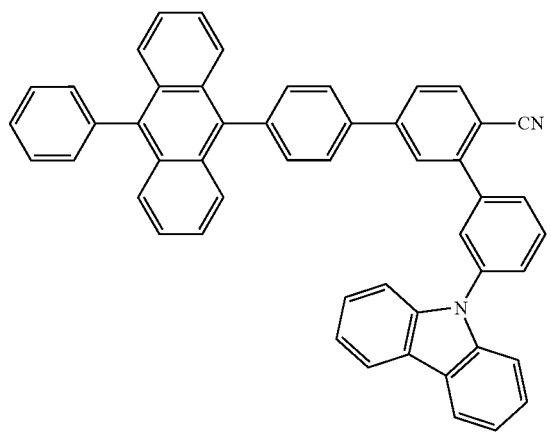
425
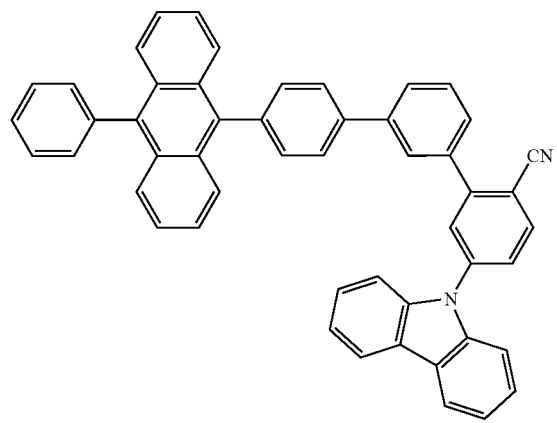
426
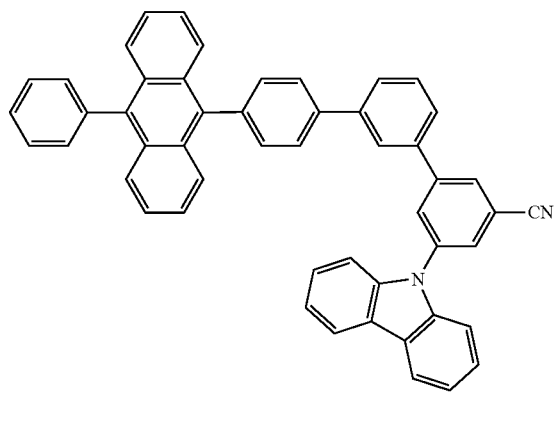

1421
427
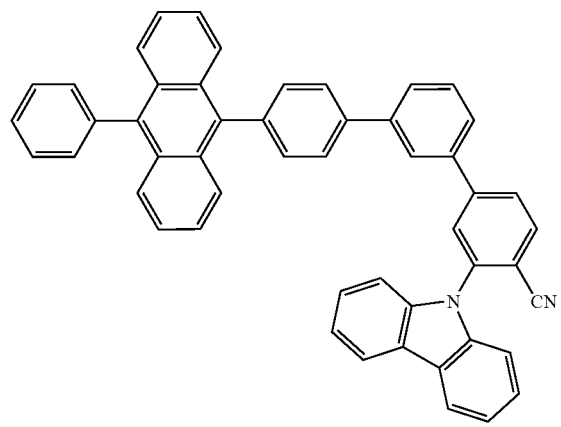
1422
428
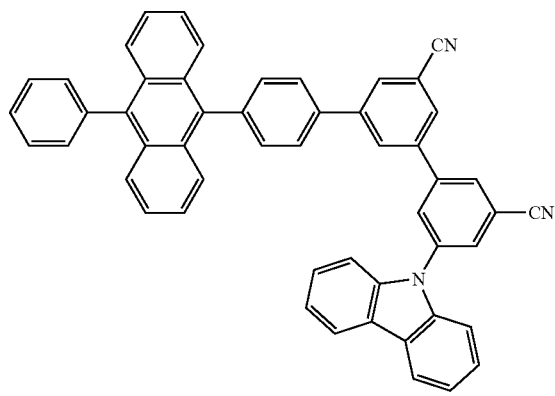
429
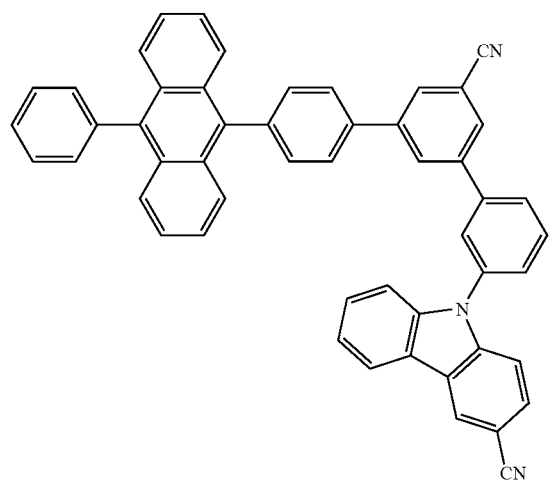
430
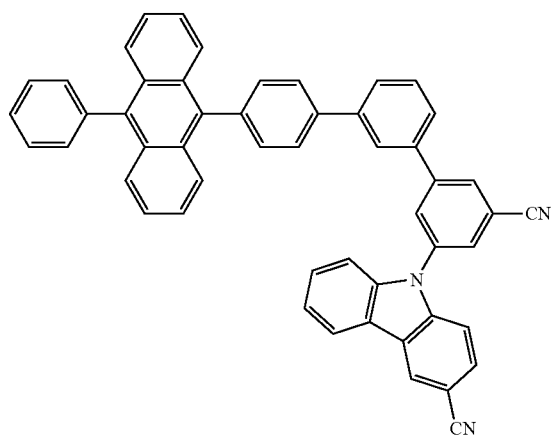
431
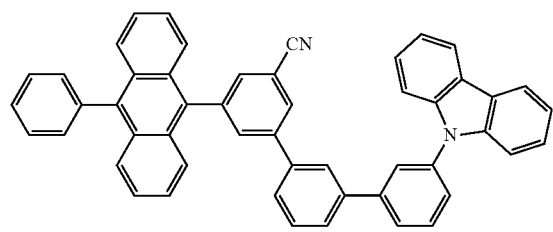
432
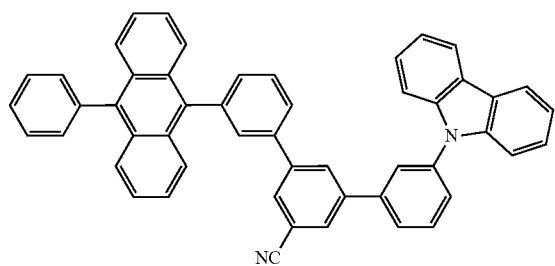
433
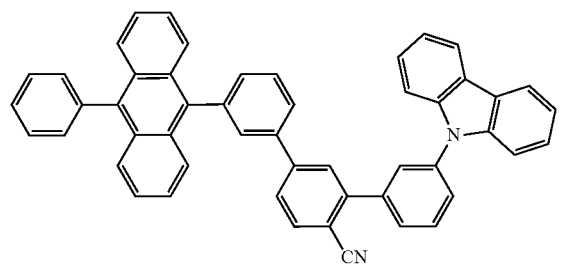
434
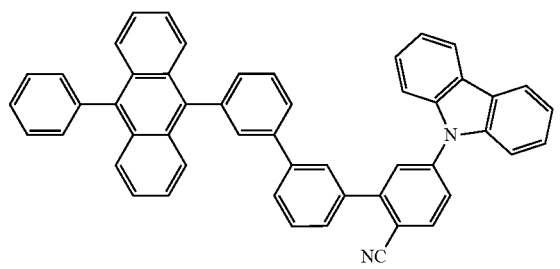

-continued
435
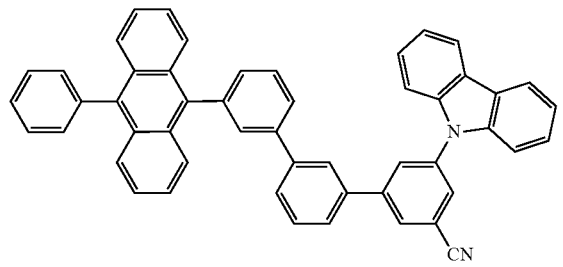
436
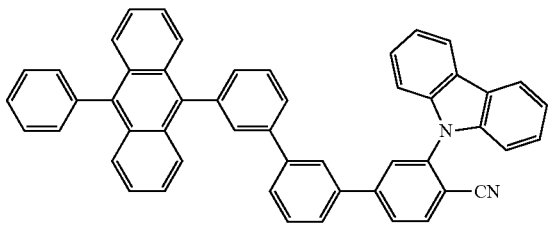
437
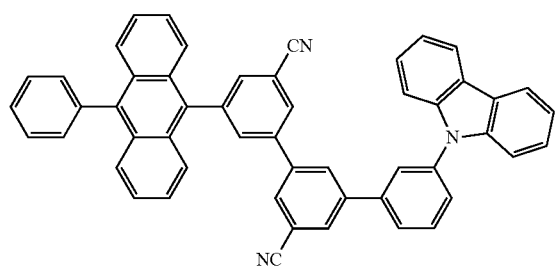
438
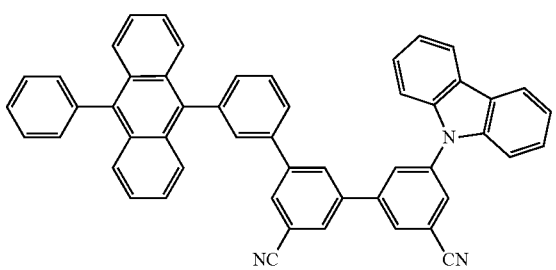
439
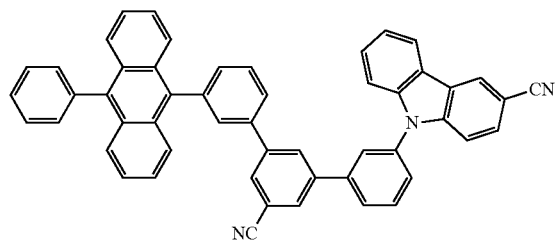
440
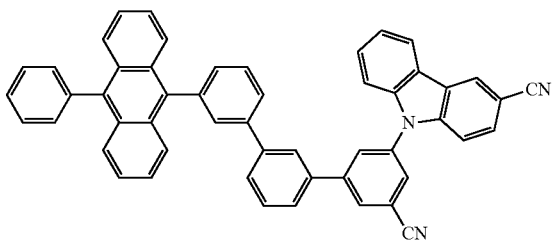
441
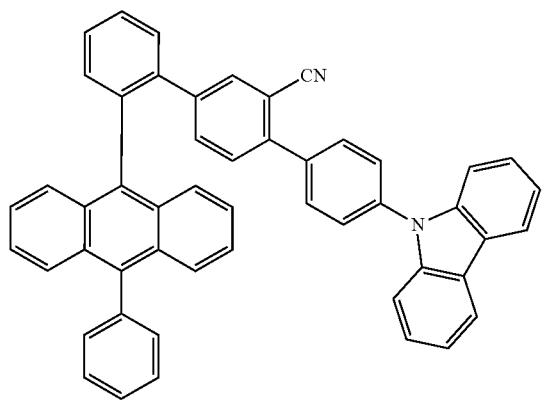
442
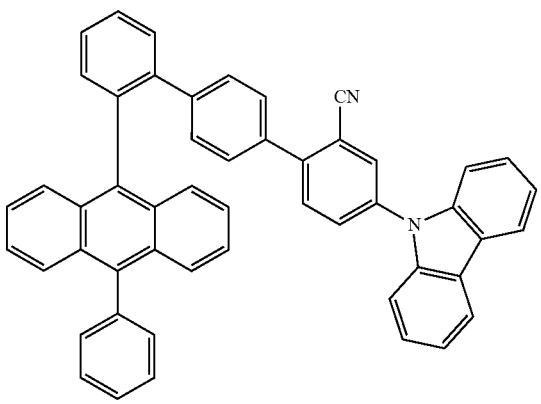

1425 1426
-continued
443
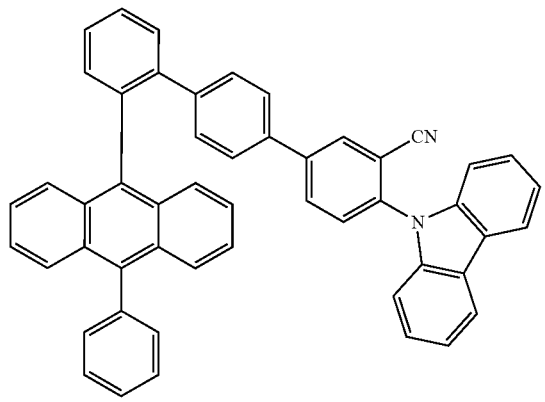
444
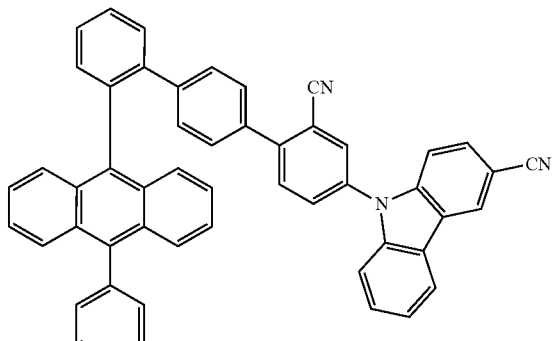
445
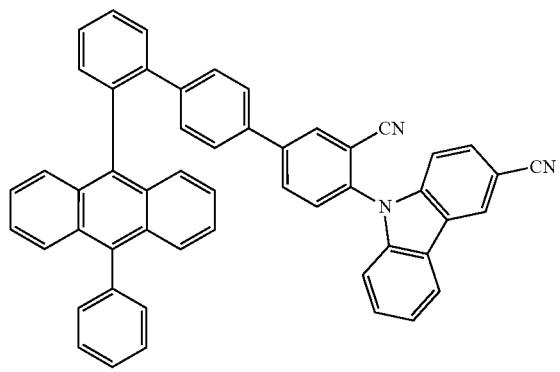
446
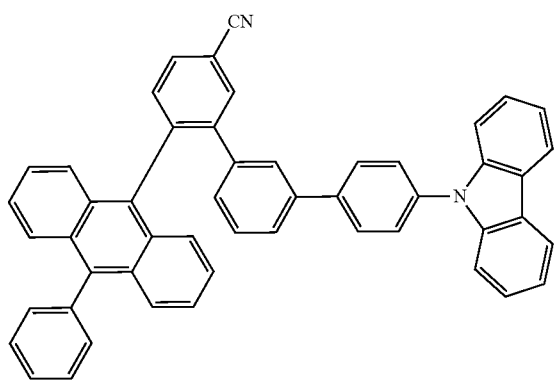
447
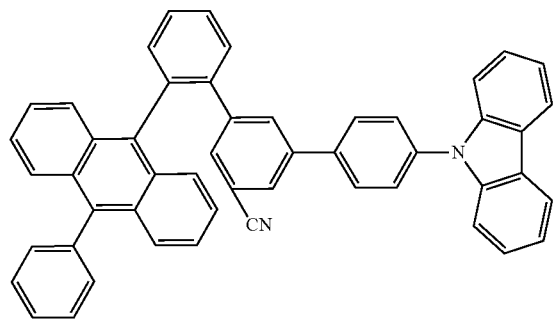
448
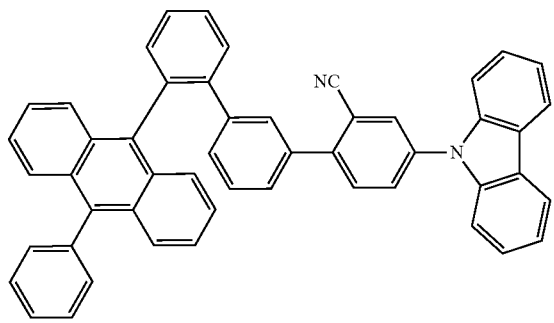
449
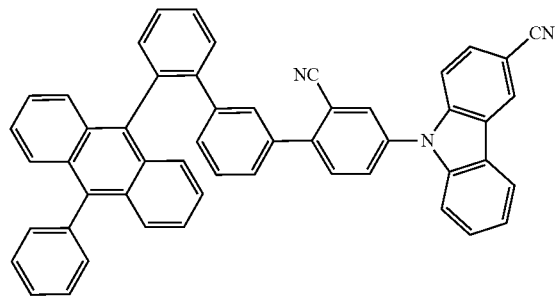
450
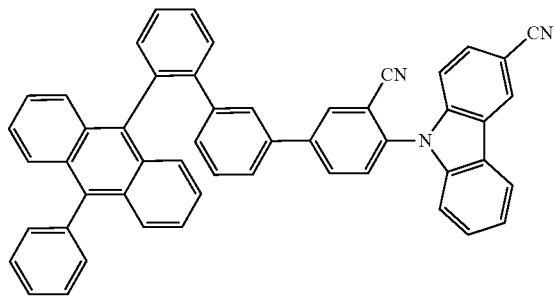

-continued
451
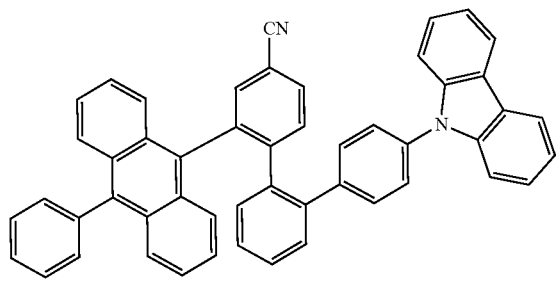
452
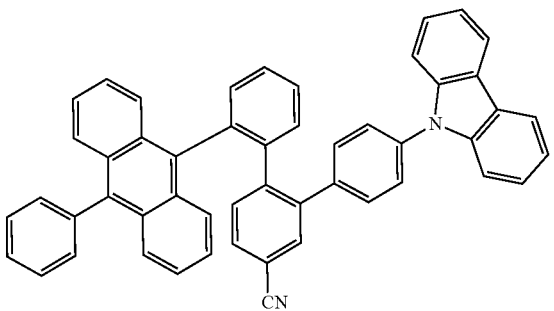
453
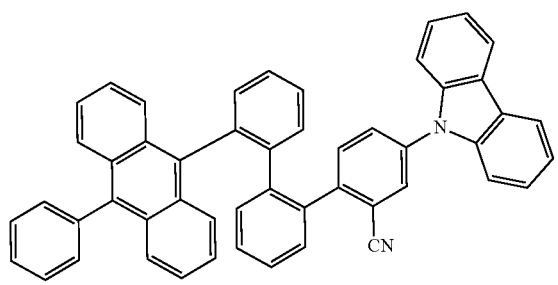
454
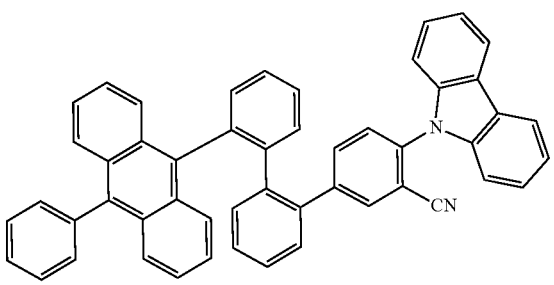
455
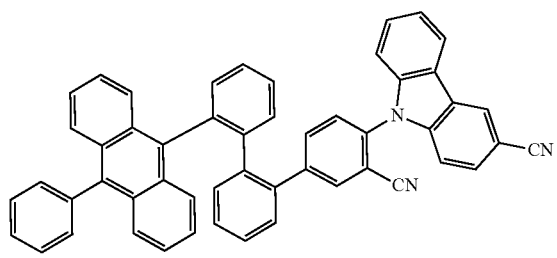
456
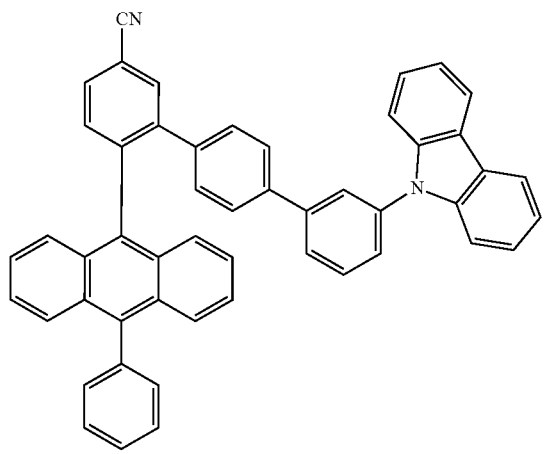
457
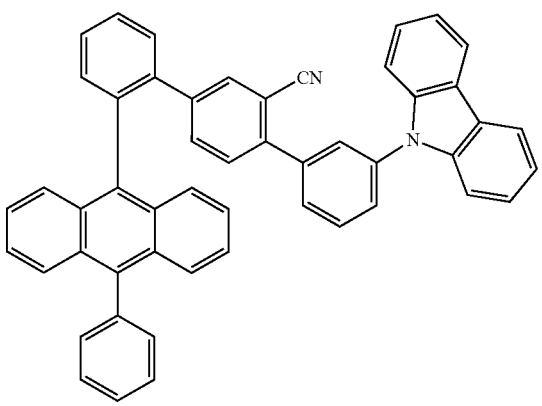

-continued
458
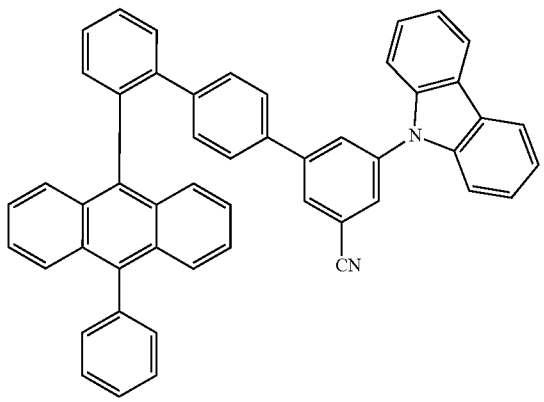
459
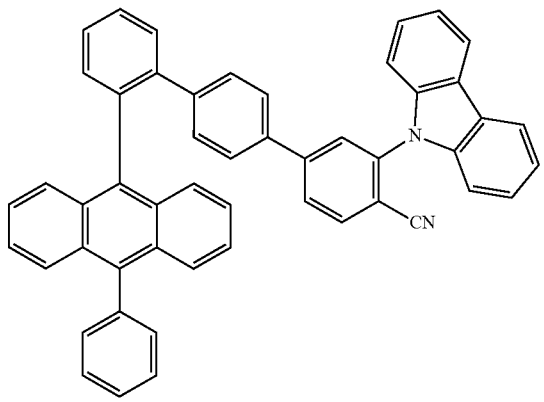
460
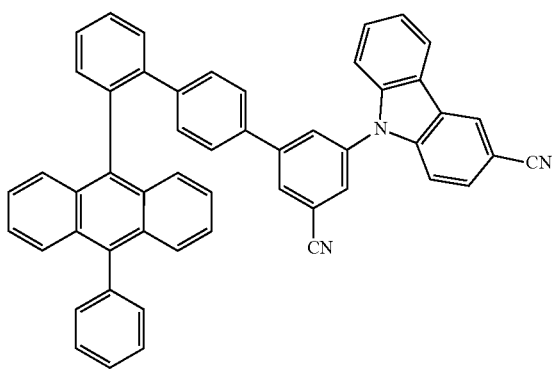
461
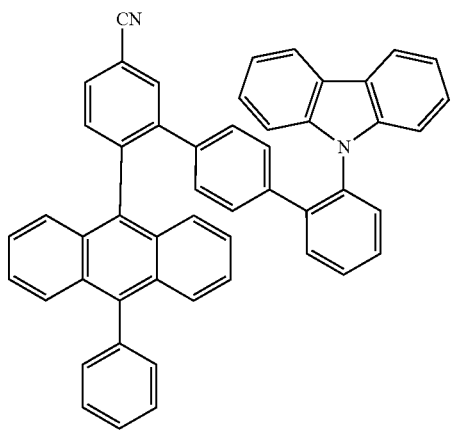
462
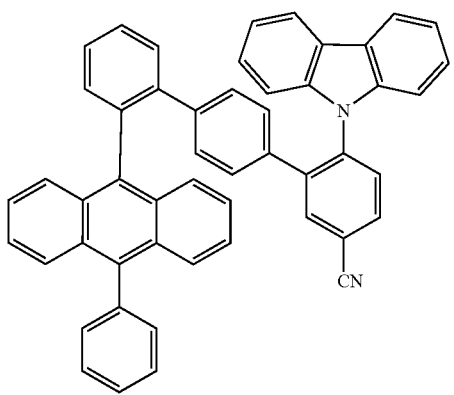
463
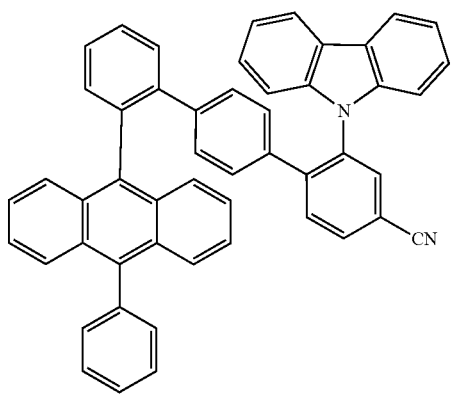

1431 1432
-continued
464
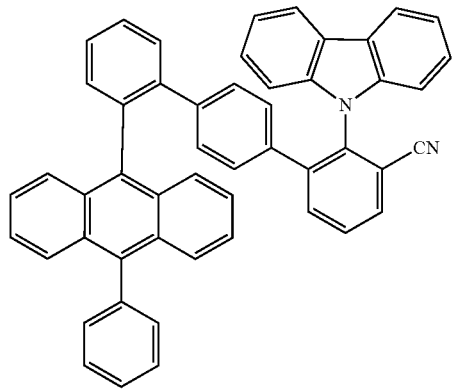
465
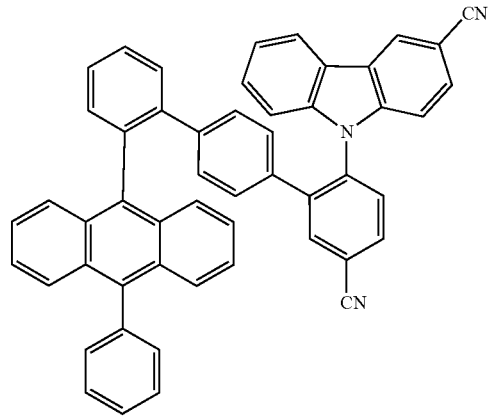
466
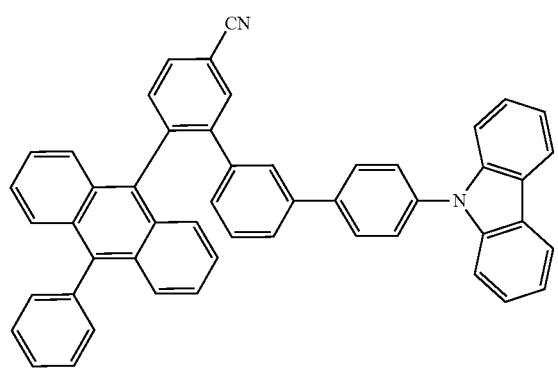
467
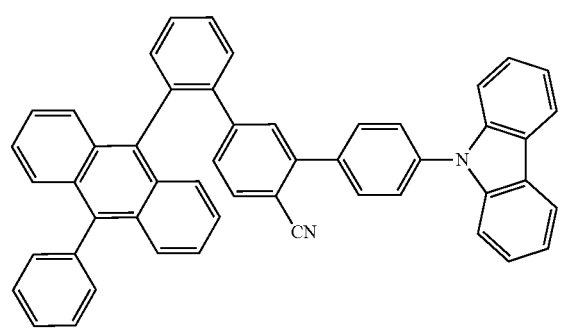
468
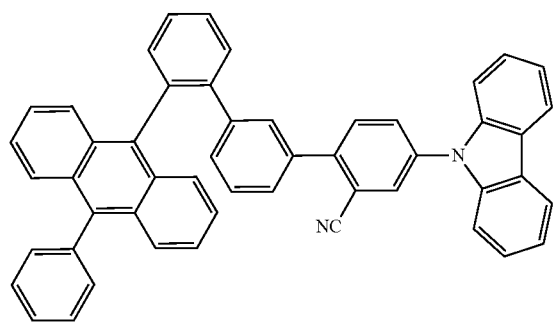
469
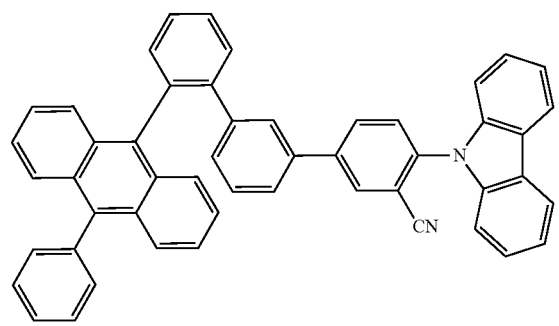
470
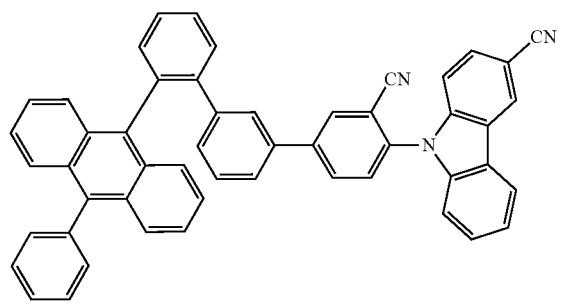
471
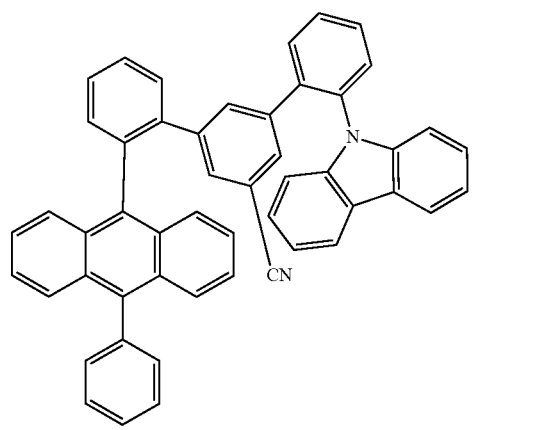

-continued
472
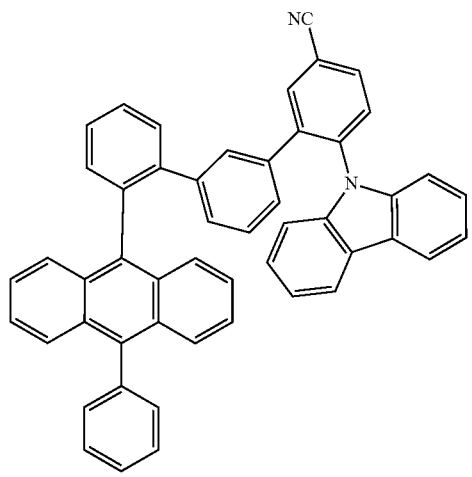
473
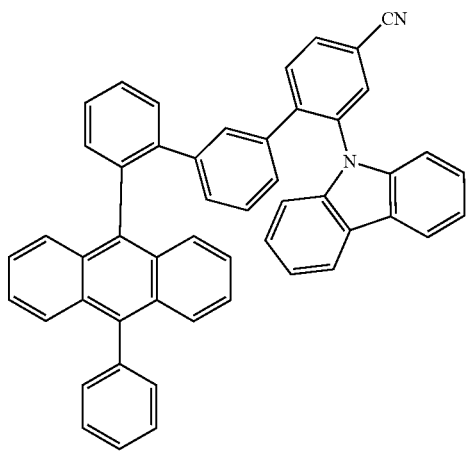
474
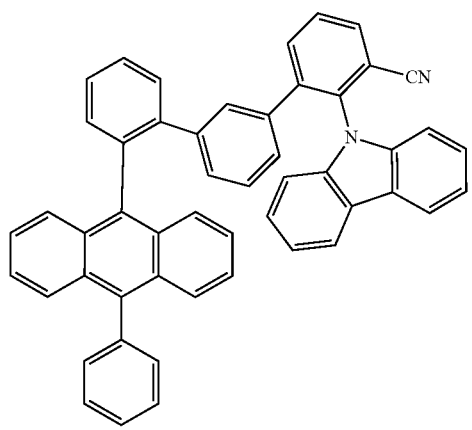
475
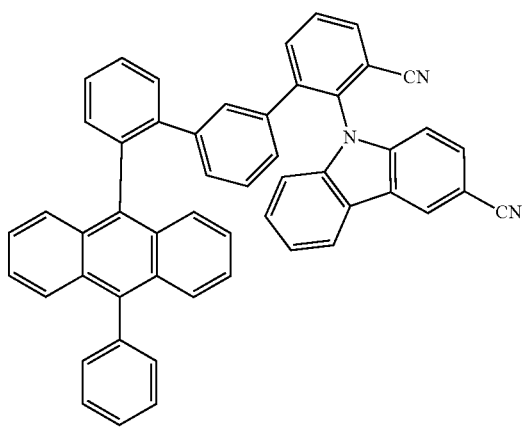
476
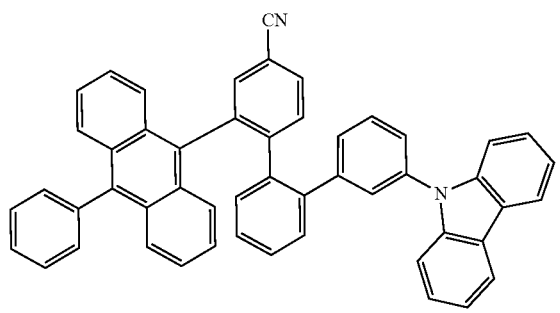
477
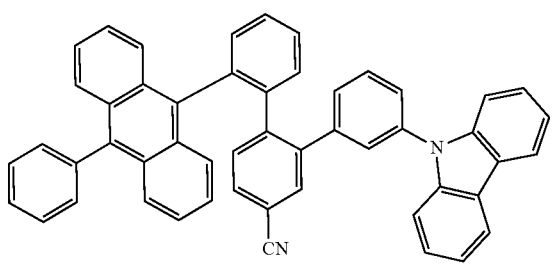
478
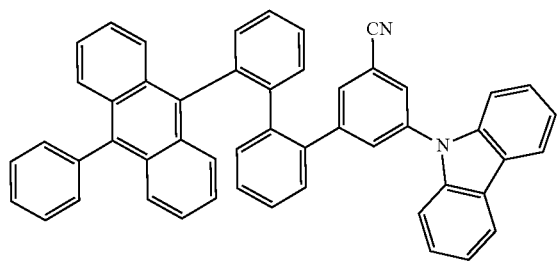
479
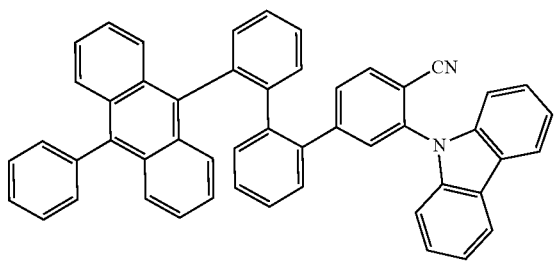

-continued
480
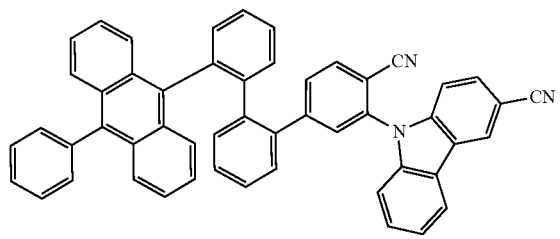
481
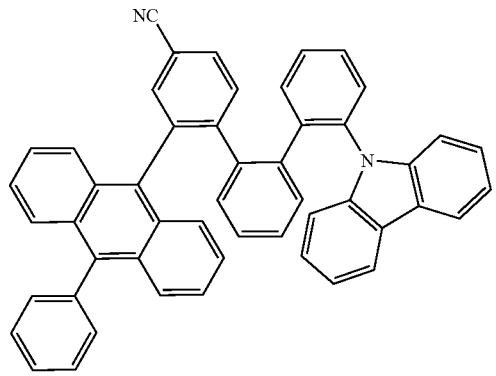
482
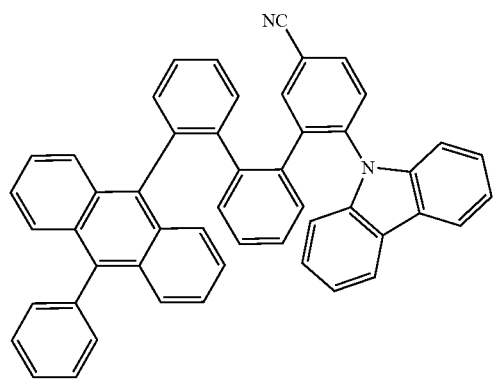
483
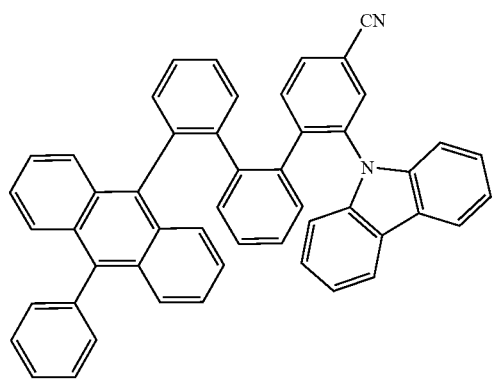
484
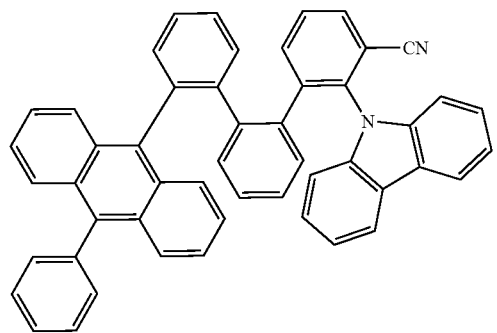
485
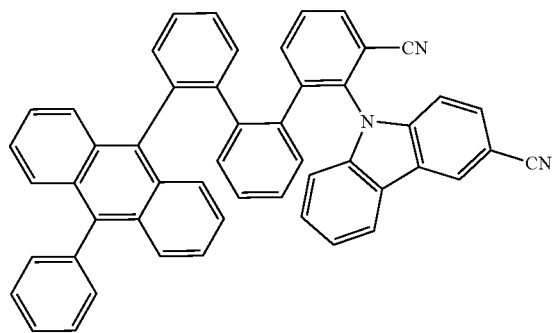
486
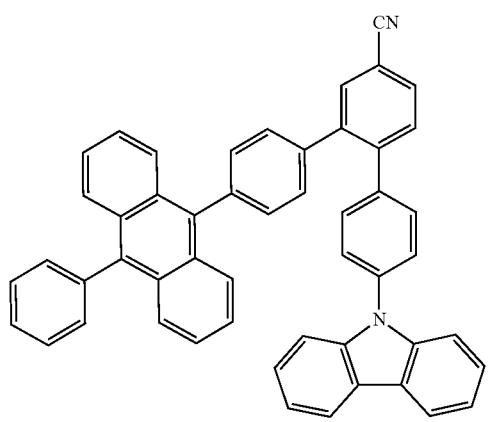
487
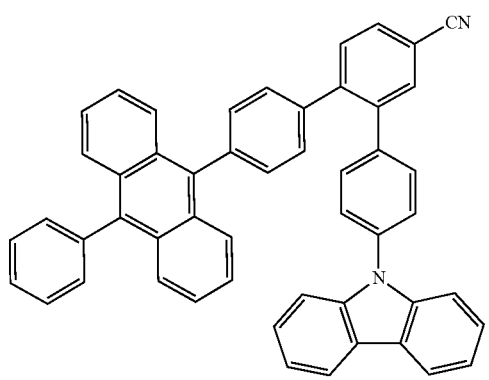

-continued
488
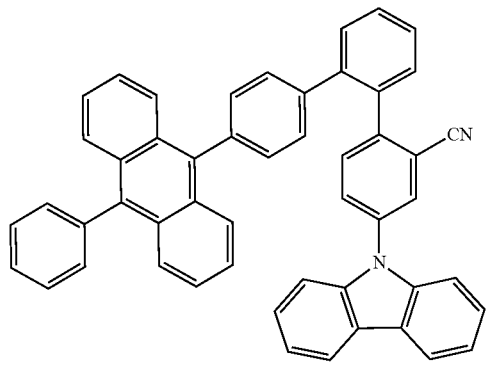
489
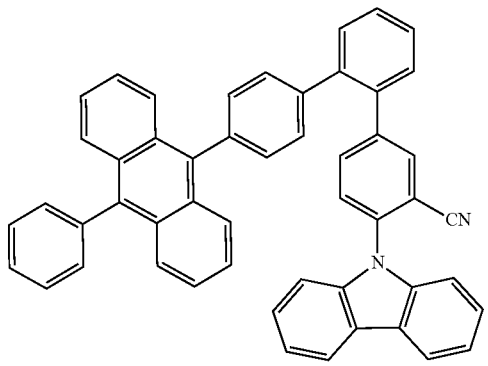
490
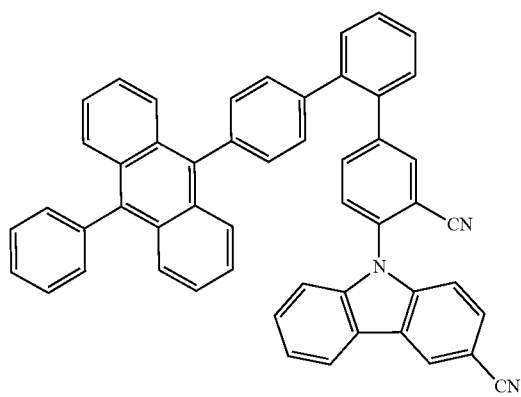
491
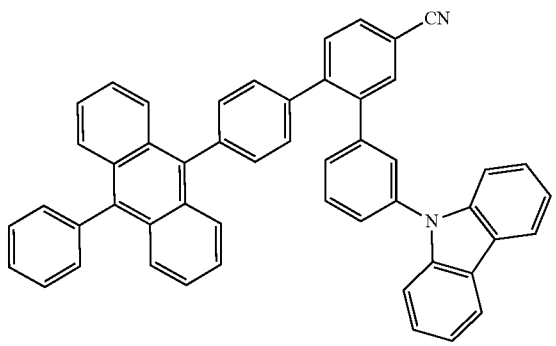
492
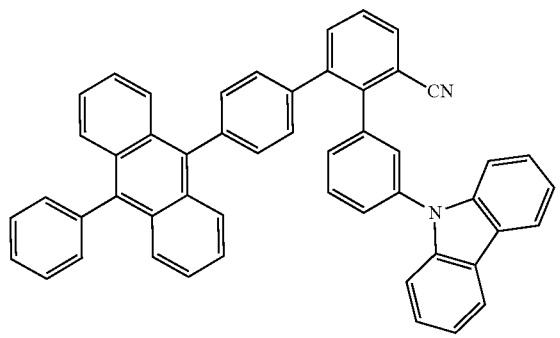
493
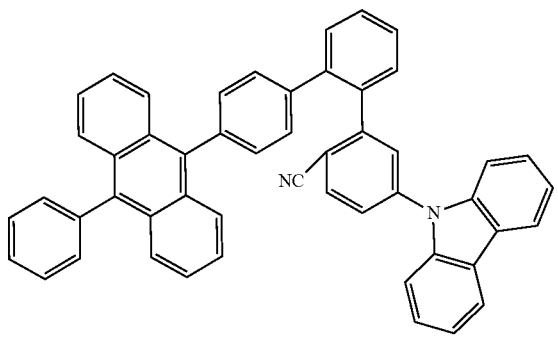
494
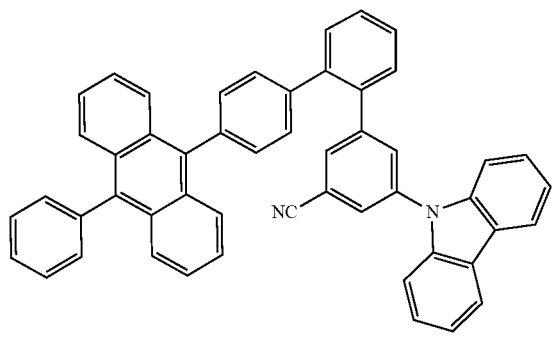
495
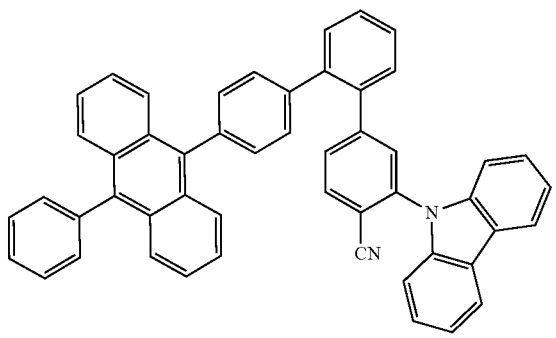

-continued
| 496 | 497 |
|---|---|
| 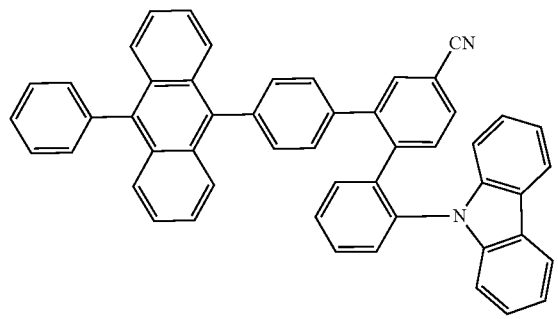 | 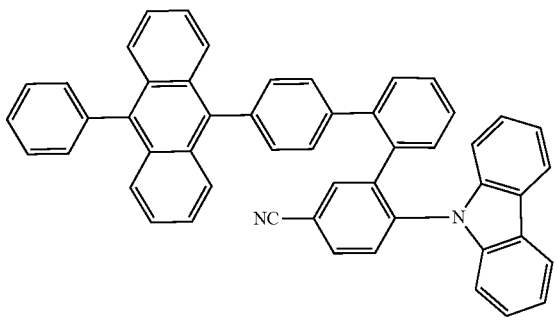 |
| 498 | 499 |
| 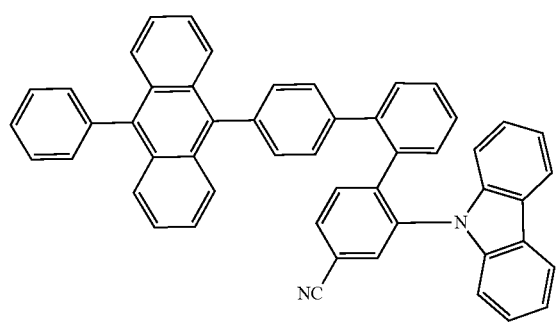 | 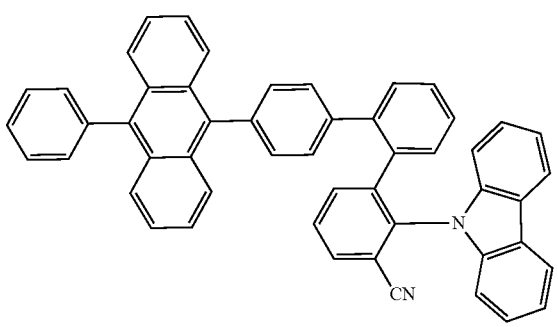 |
| 500 | 501 |
| 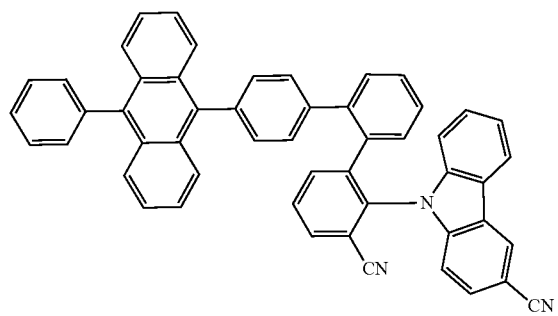 | 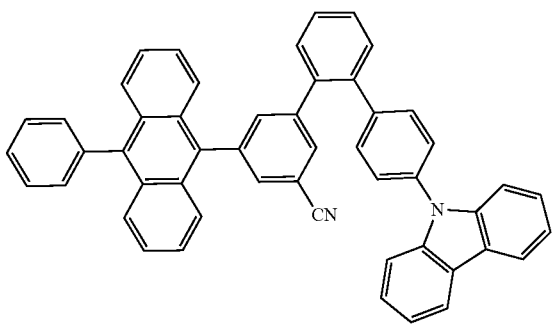 |
| 502 | 503 |
| 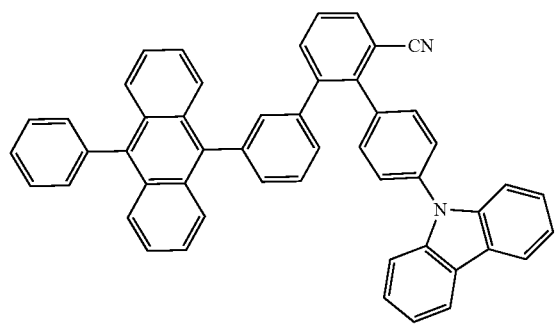 | 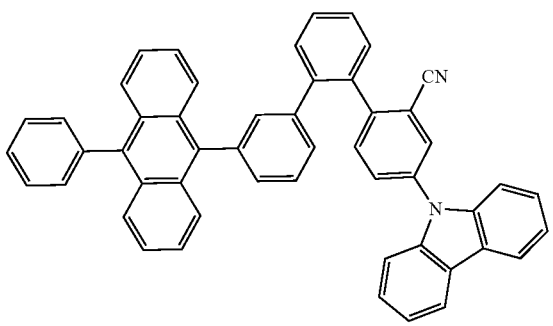 |

-continued
| 504 | 505 |
|---|---|
| 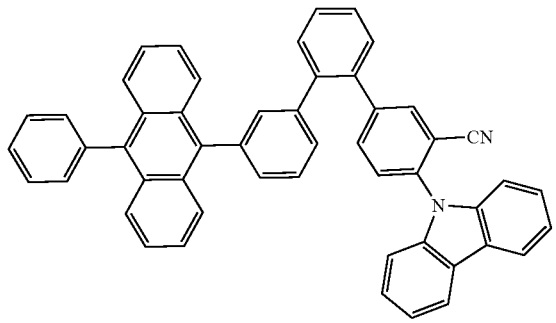 | 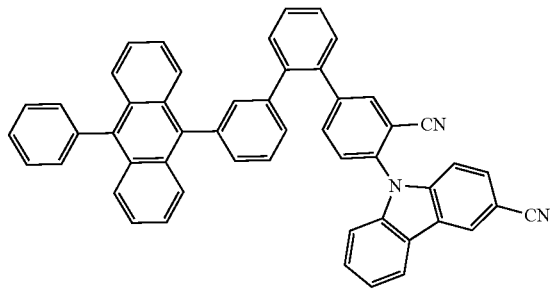 |
| 506 | 507 |
| 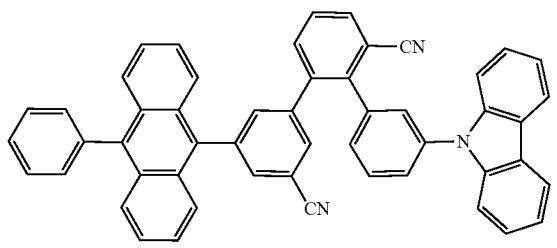 | 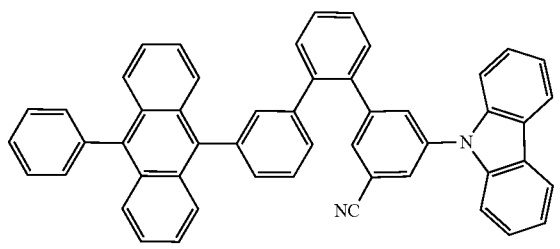 |
| 508 | 509 |
| 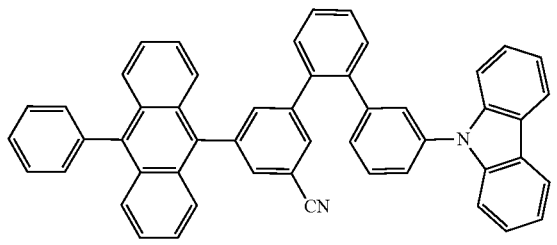 | 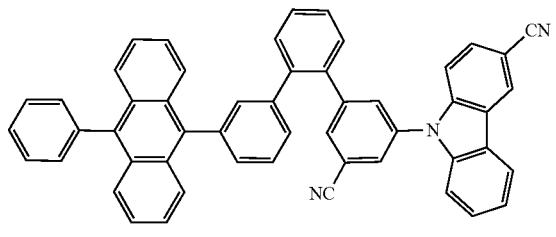 |
| 510 | 511 |
| 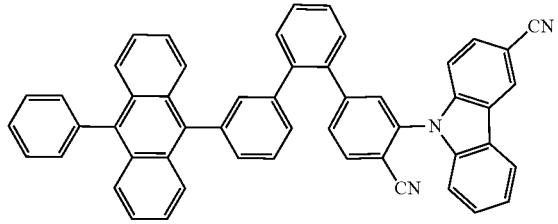 | 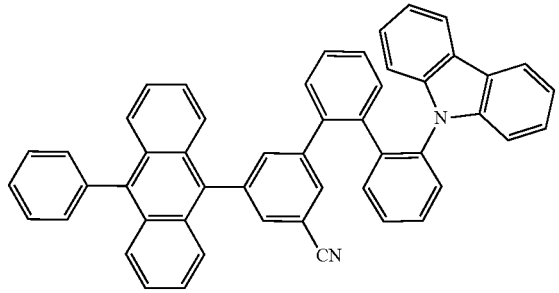 |
| 512 | 513 |
| 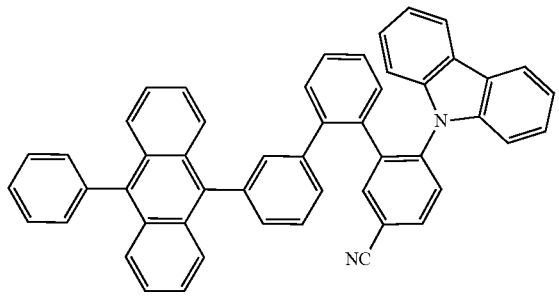 | 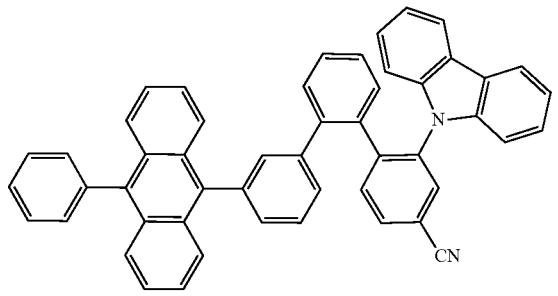 |

-continued
514
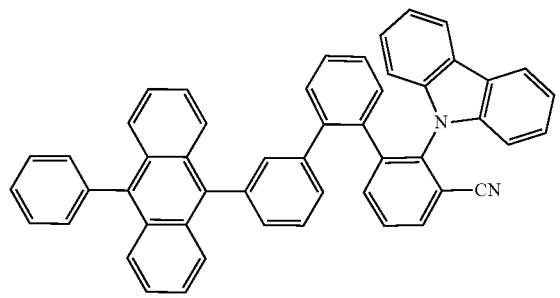
515
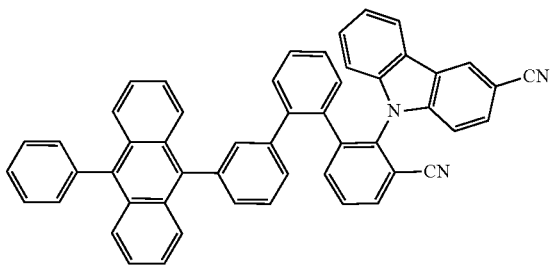
516
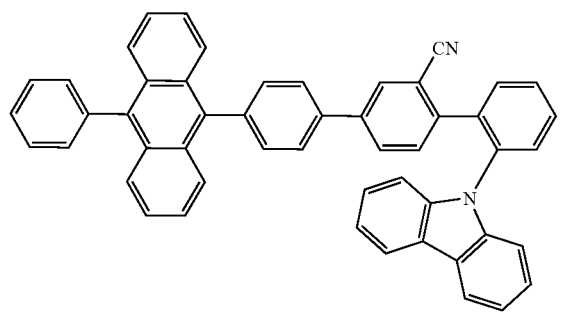
517
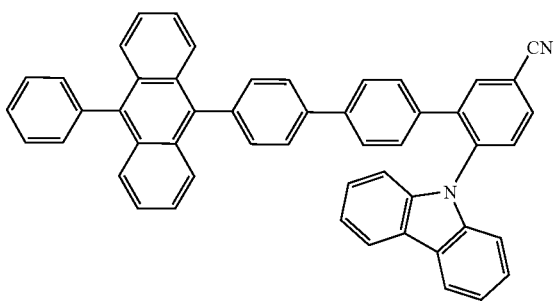
518
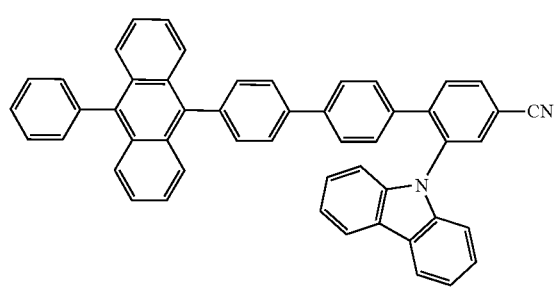
519
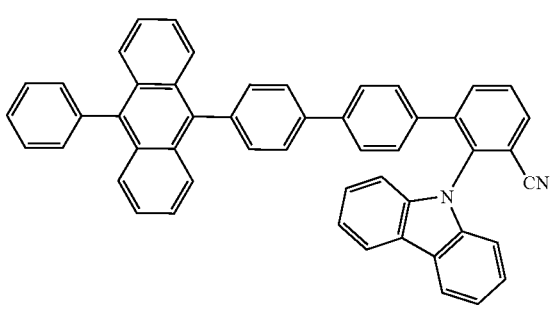
520
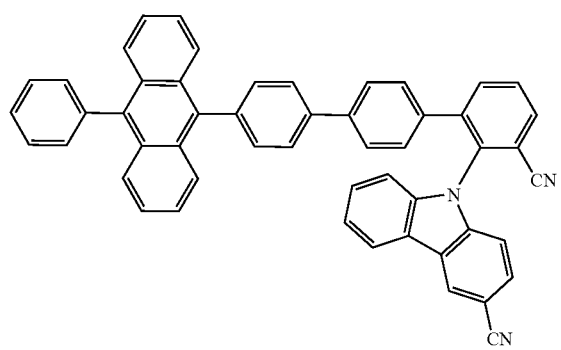
521
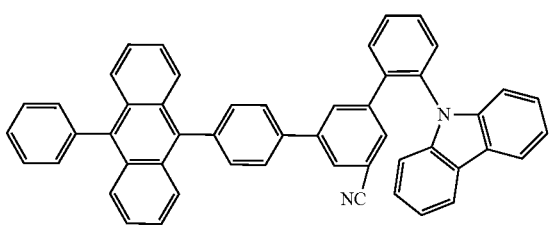
522
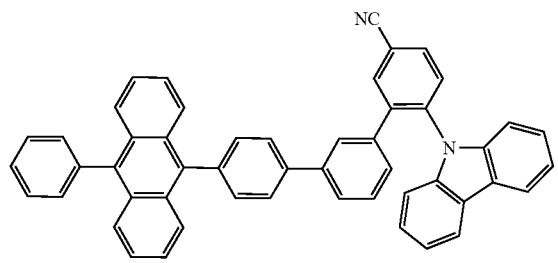
523
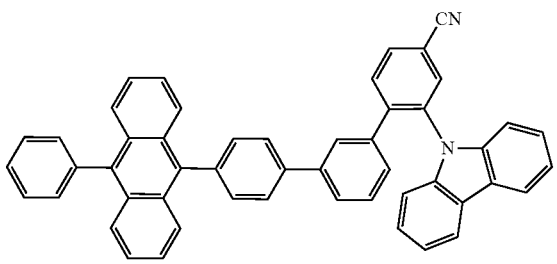

-continued
524
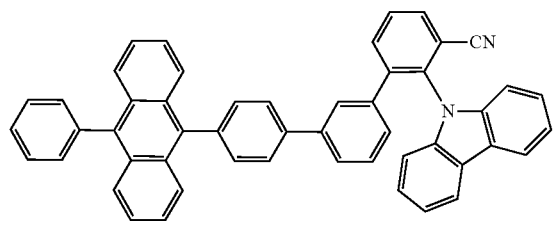
525
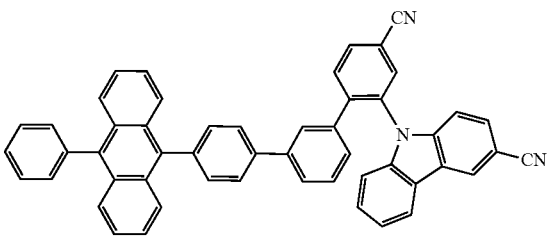
526
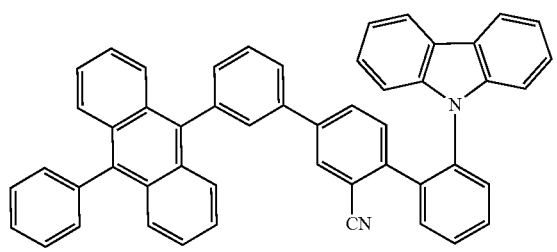
527
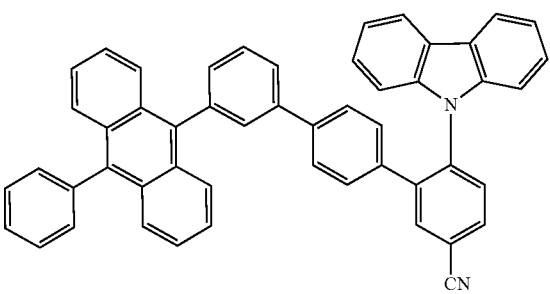
528
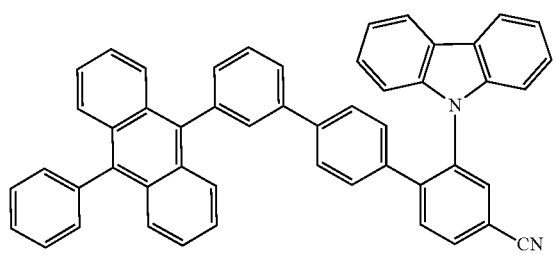
529
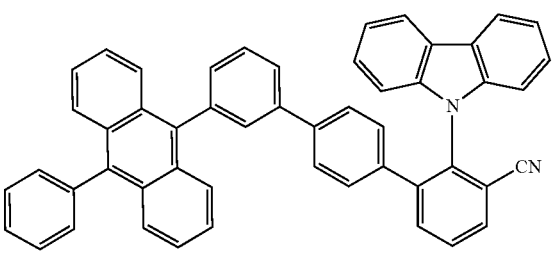
530
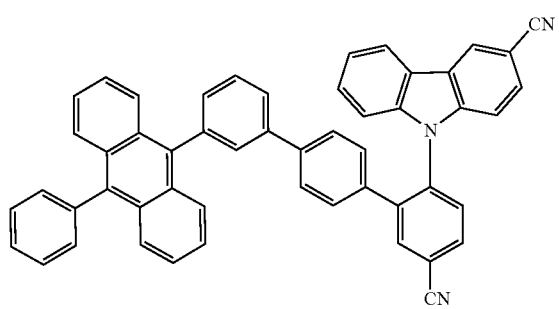
531
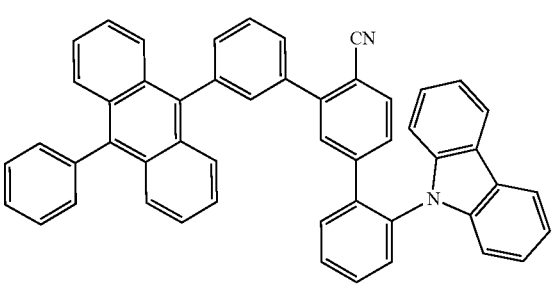
532
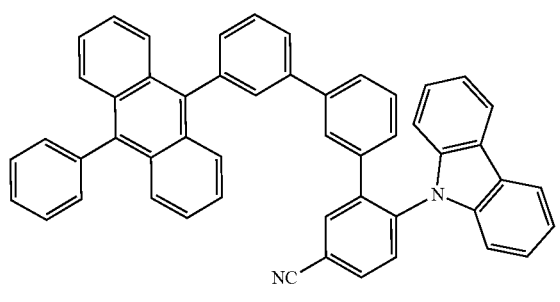
533
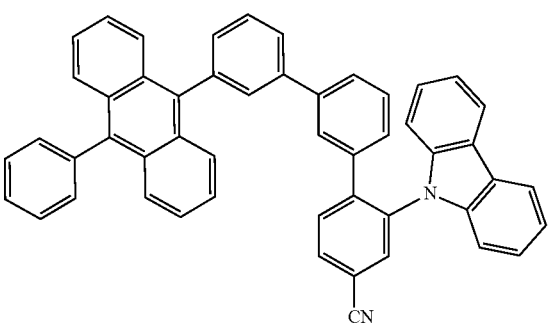

-continued
534
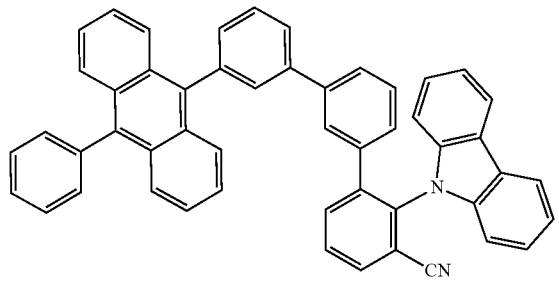
535
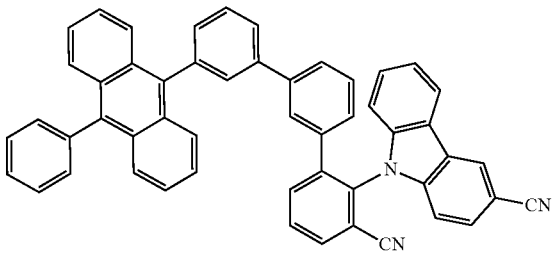
536
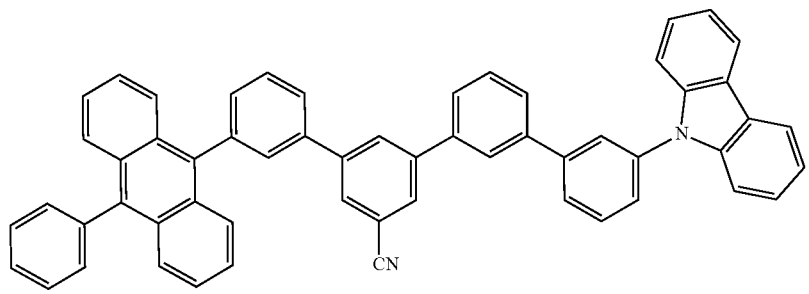
537
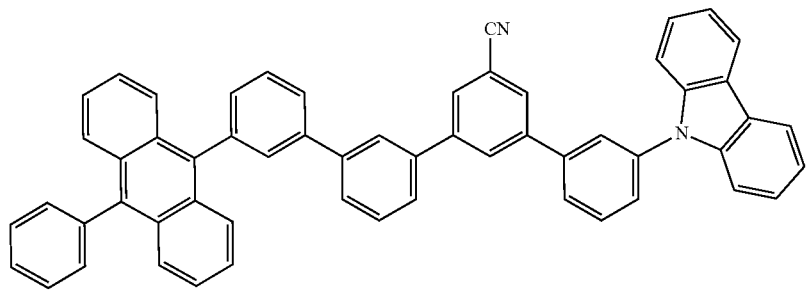
538
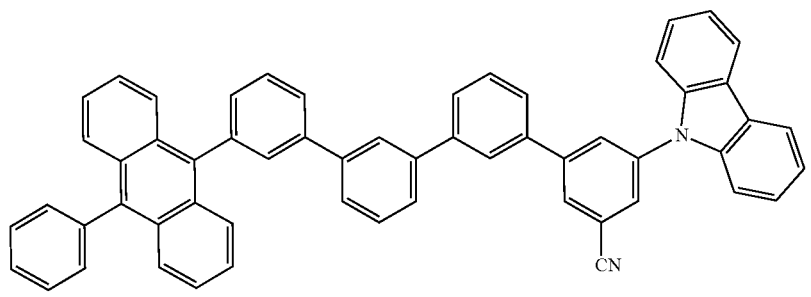
539
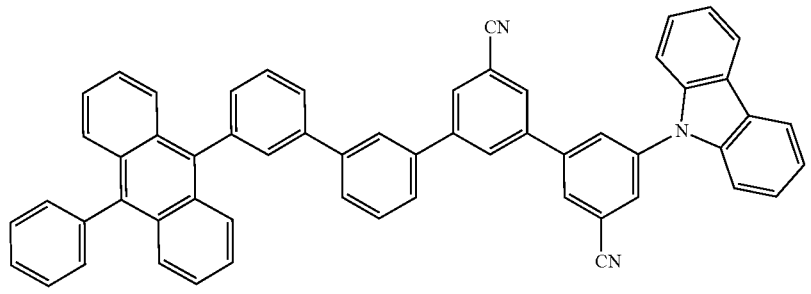

540
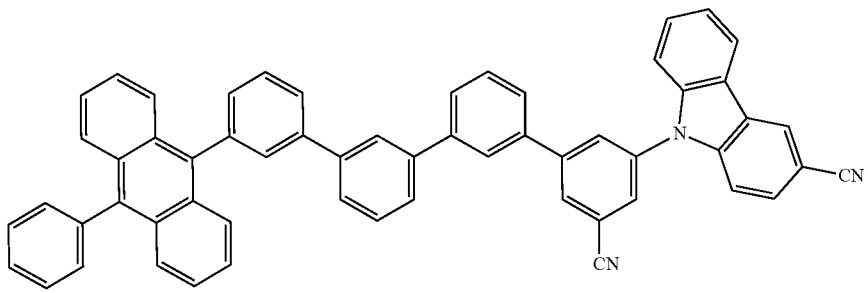
541
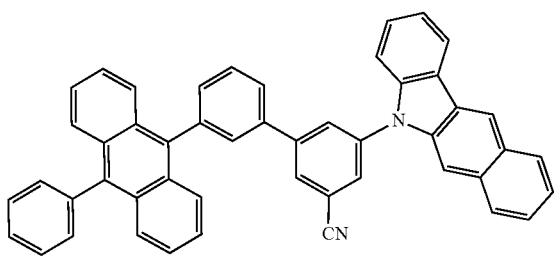
542
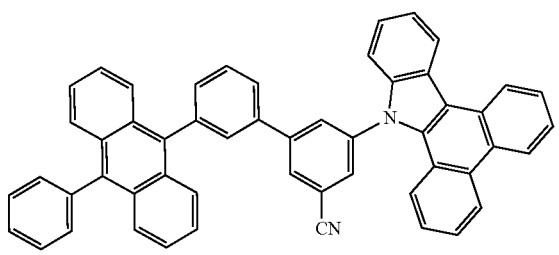
543
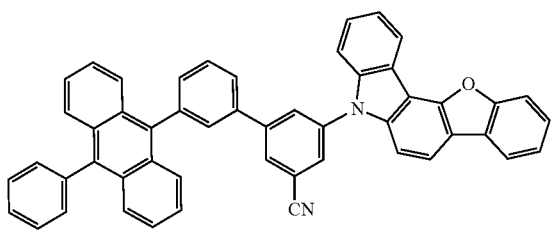
544
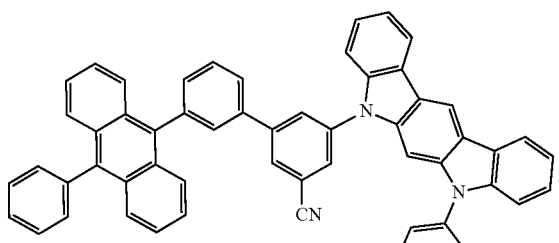
545
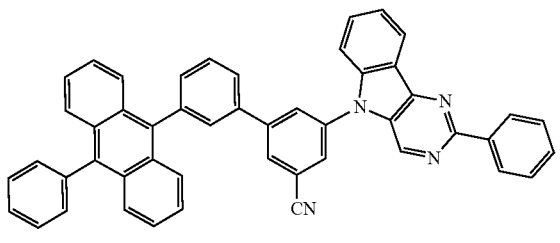
546
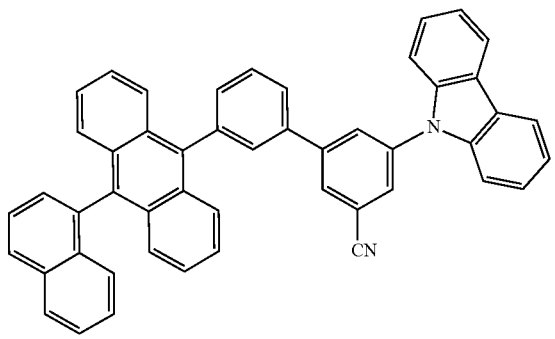
547
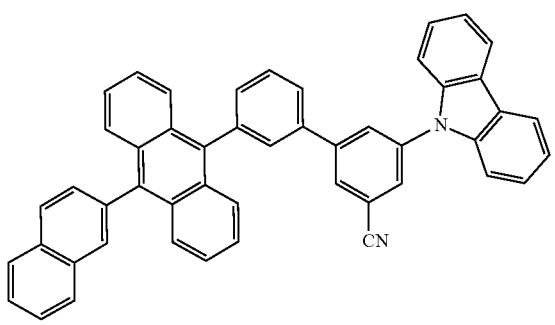
548
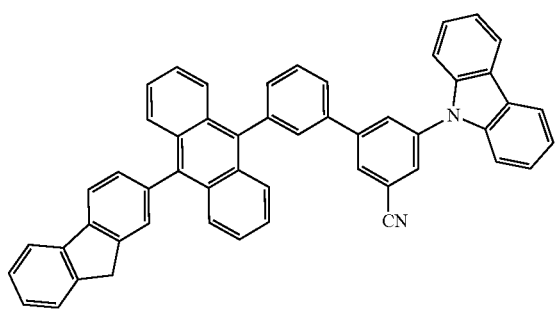

-continued
549
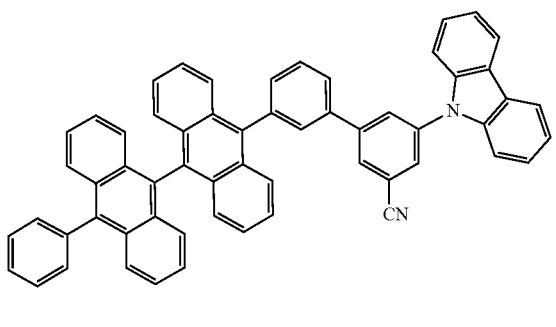
550
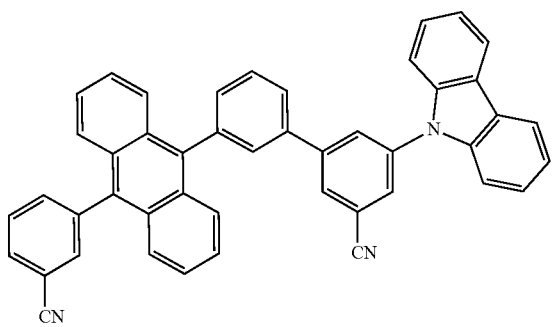
551
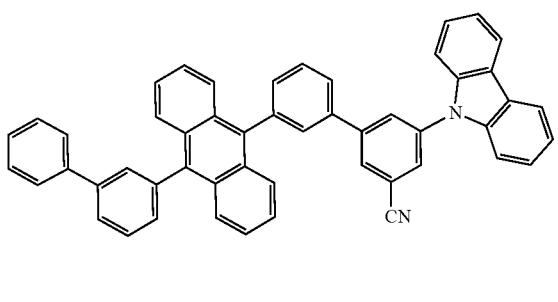
552
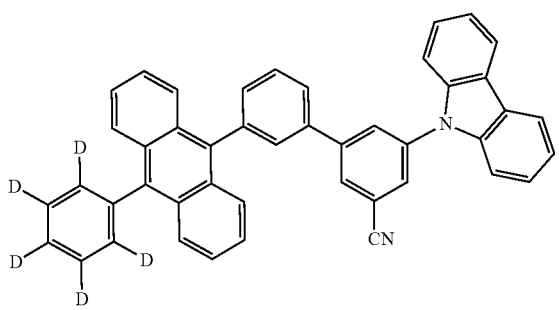
553
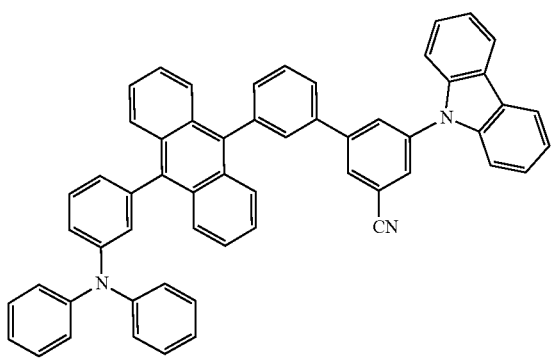
554
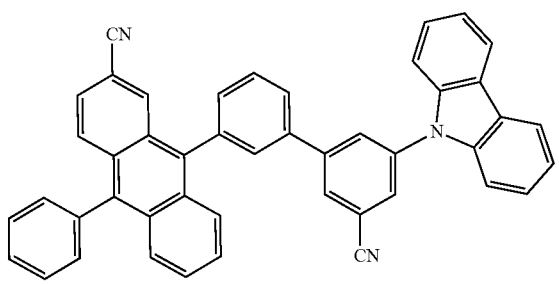
555
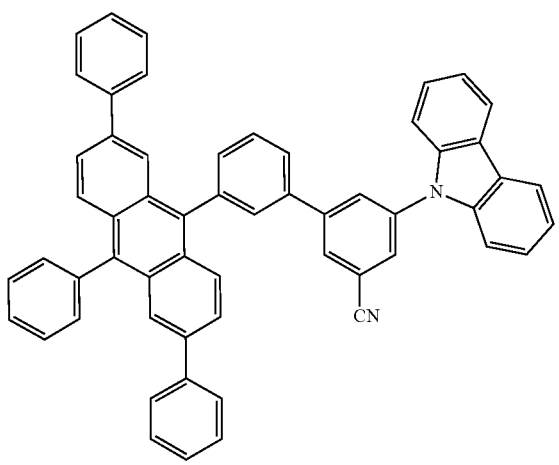
556
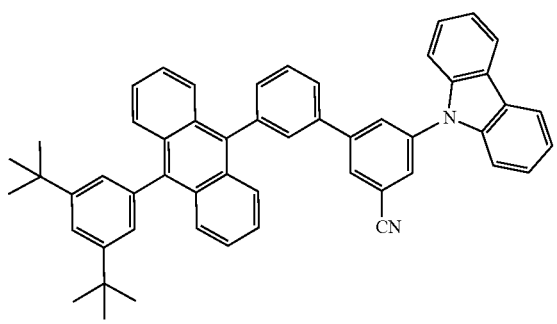

557

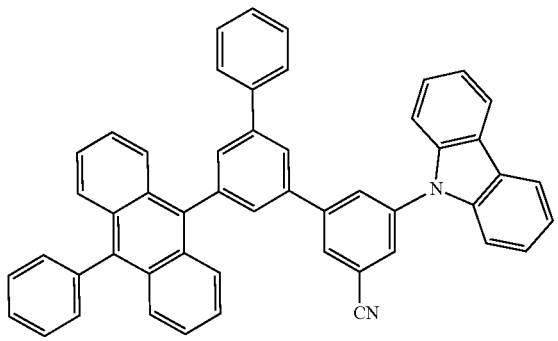

558

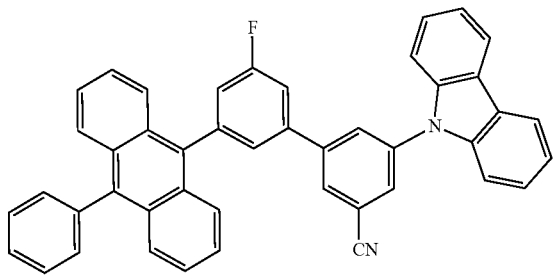

559

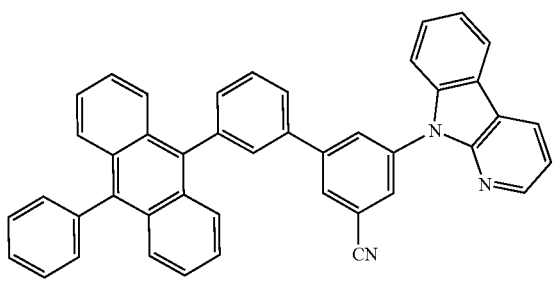

560

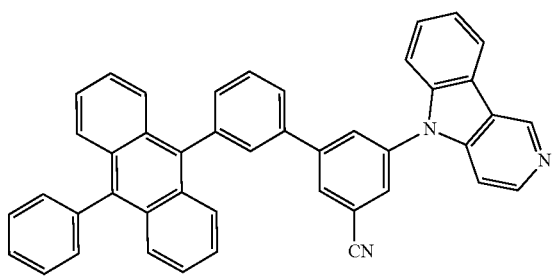

In some embodiments, the fluorescent host may be represented by Formula FH-4:

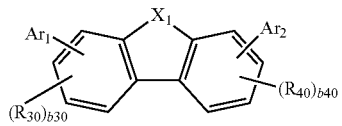

Formula FH-4 wherein, in Formula FH-4, $X_1$ may be O or Se, and $Ar_1$ may be a group represented by Formula 1A, and $Ar_2$ may be a group represented by Formula 1B:

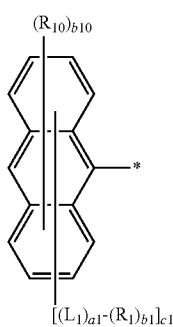

Formula 1A

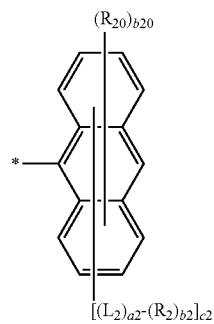

Formula 1B wherein, in Formulae 4 to 6, $L_1$ and $L_2$ may each independently be a substituted or unsubstituted $C_5$-$C_{30}$ carbocyclic group or a substituted or unsubstituted $C_1$-$C_{30}$ heterocyclic group, a1 and a2 may be each independently an integer from 0 to 3, when a1 is 2 or greater, at least two $L_1$(s) may be identical to or different from each other, and when a2 is 2 or greater, at least two $L_2$(s) may be identical to or different from each other, $R_1$, $R_2$, $R_{10}$, $R_{20}$, $R_{30}$, and $R_{40}$ may each independently be hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted C₁-C₆₀ alkyl group, a substituted or unsubstituted C₂-C₆₀ alkenyl group, a substituted or unsubstituted C₂-C₆₀ alkynyl group, a substituted or unsubstituted C₁-C₆₀ alkoxy group, a substituted or unsubstituted C₃-C₁₀ cycloalkyl group, a substituted or unsubstituted C₁-C₁₀ heterocycloalkyl group, a substituted or unsubstituted C₃-C₁₀ cycloalkenyl group, a substituted or unsubstituted C₁-C₁₀ heterocycloalkenyl group, a substituted or unsubstituted C₆-C₆₀ aryl group, a substituted or unsubstituted C₆-C₆₀ aryloxy group, a substituted or unsubstituted C₆-C₆₀ arylthio group, a substituted or unsubstituted C₁-C₆₀ heteroaryl group, a substituted or unsubstituted monovalent non-aromatic condensed polycyclic group, a substituted or unsubstituted monovalent non-aromatic condensed heteropolycyclic group, —N(Q₁)(Q₂), —Si(Q₃)(Q₄)(Q₅), —B(Q₆)(Q₇), or —P(=O)(Q₈)(Q₉), b1 and b2 may each independently be an integer from 1 to 5, when b1 is 2 or greater, at least two R₁(s) may be identical to or different from each other, and when b2 is 2 or greater, at least two R₂(s) may be identical to or different from each other, b10 and b20 may each independently be an integer from 1 to 8, b30 and b40 may each independently be an integer from 1 to 3, c1 and c2 may each independently be an integer from 1 to 8, and a sum of b10 and c1 may be 9, and a sum of b20 and c2 may be 9.

In some embodiments, the fluorescent host represented by Formula FH-4 may be Group FH4, but embodiments are not limited thereto:

Group FH4

1

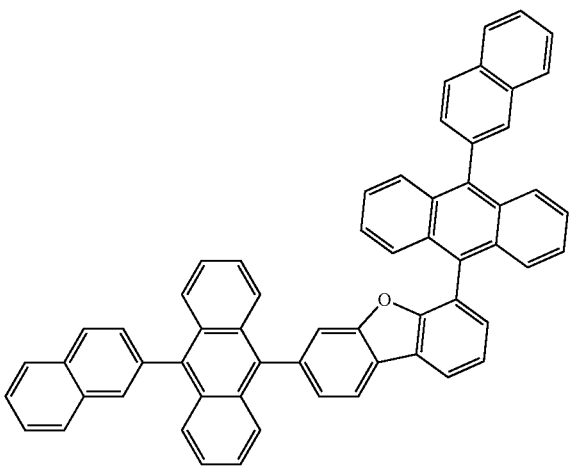

2

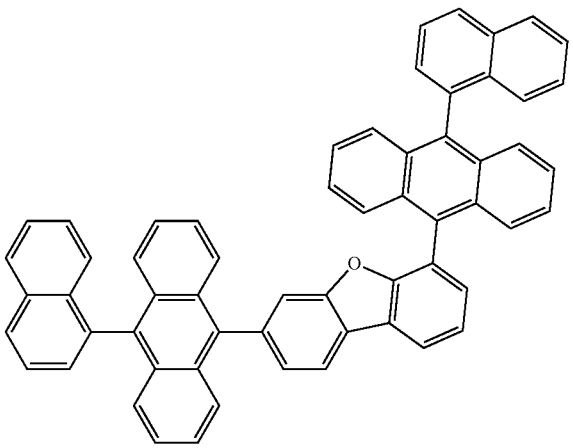

3

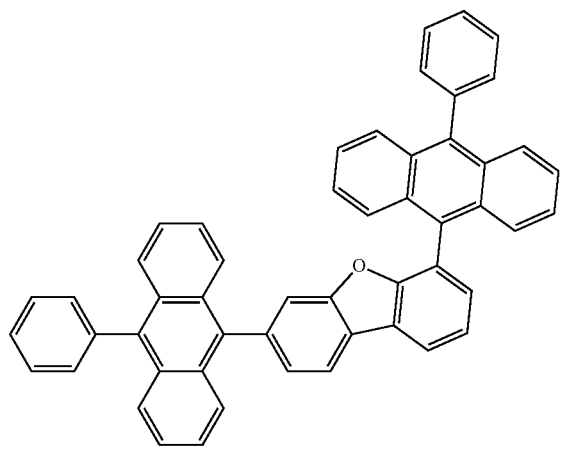

4

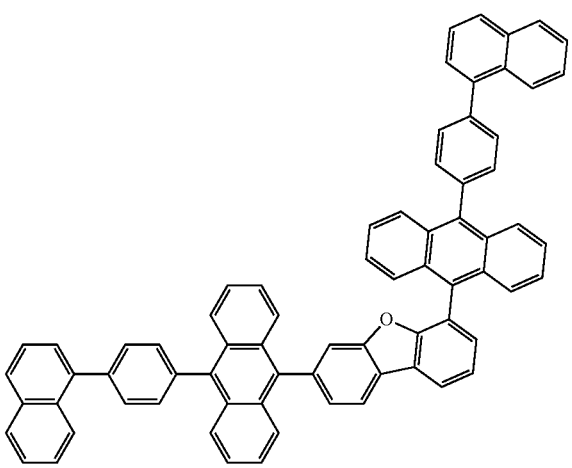

5
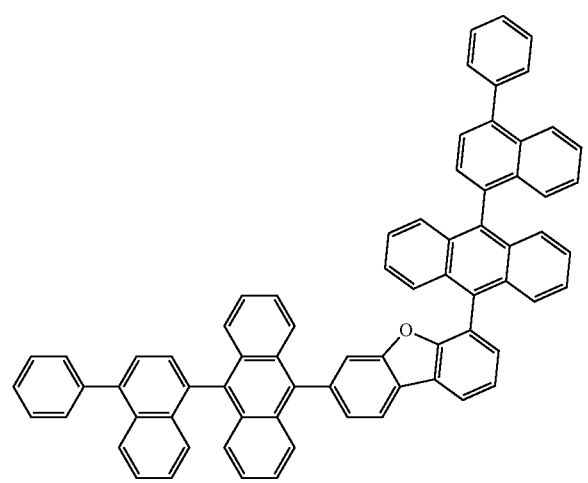
6
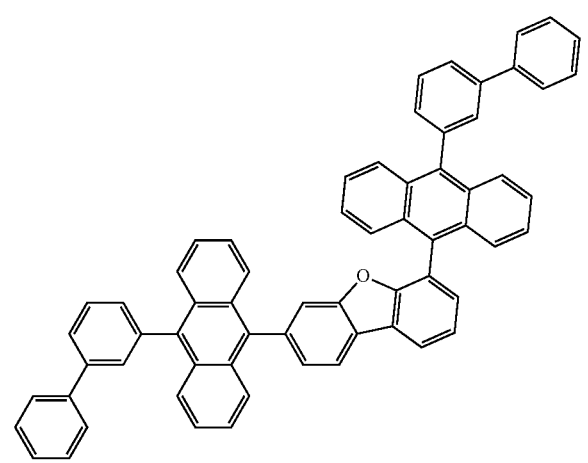
7
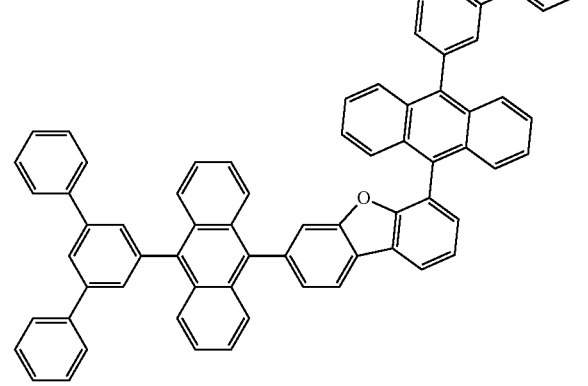
8
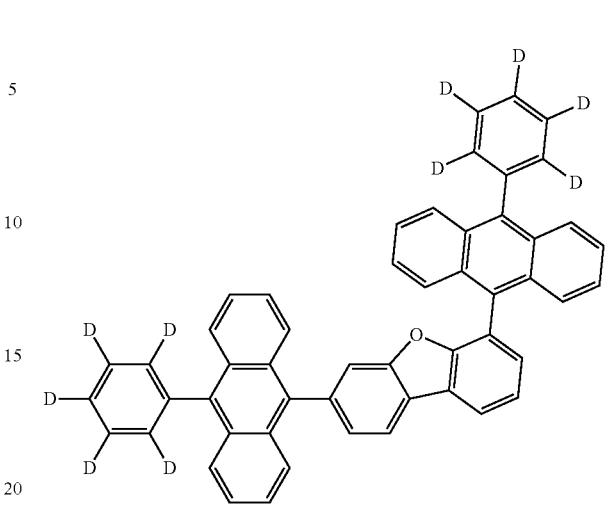
9
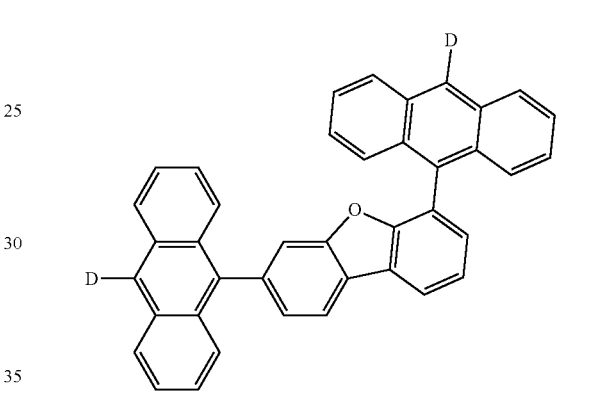
10
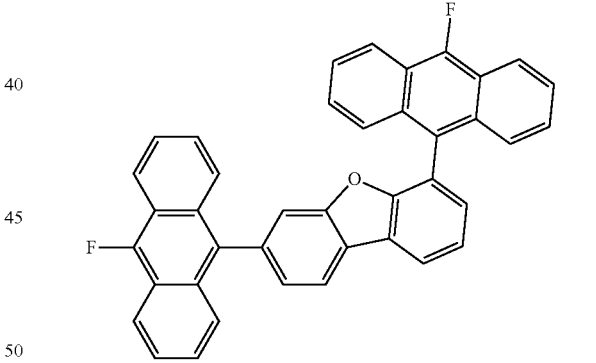
11
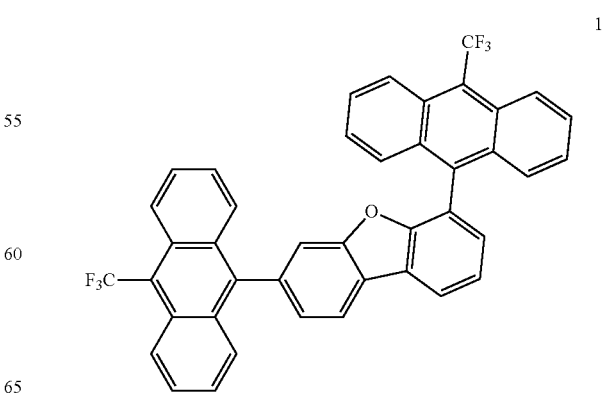

-continued
12
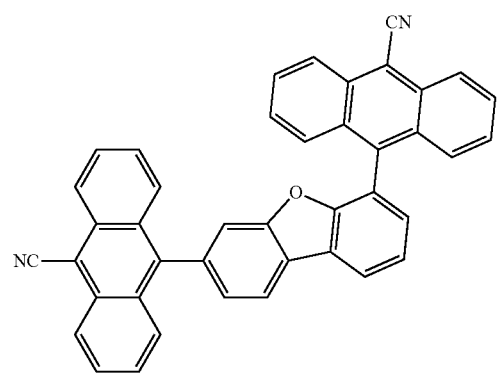
13
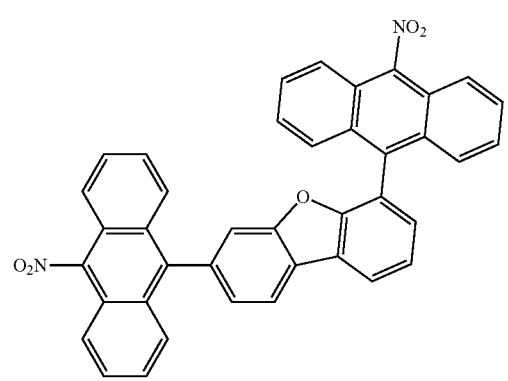
14
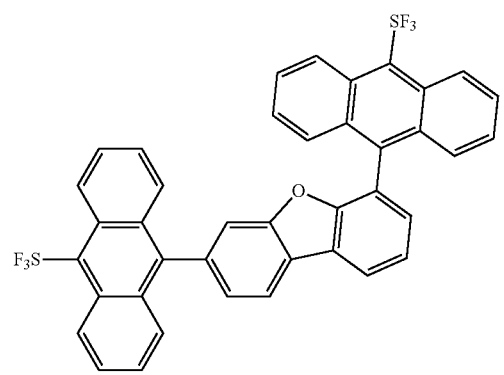
15
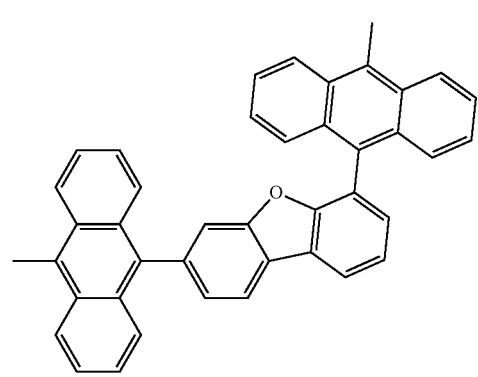
-continued
16
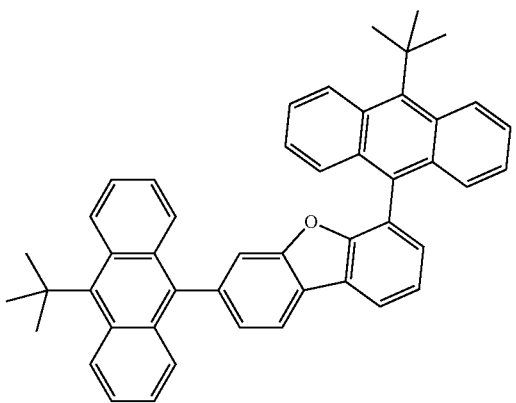
17
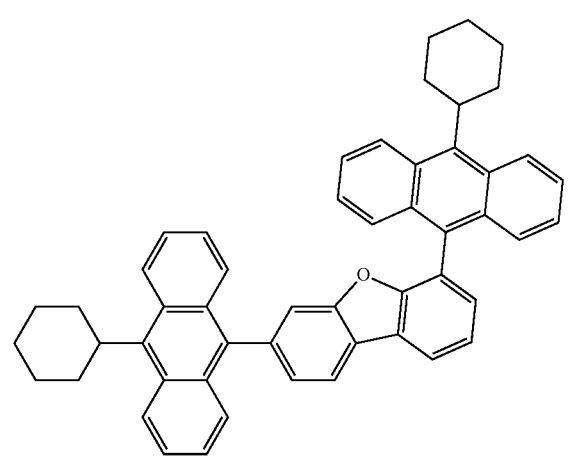
18
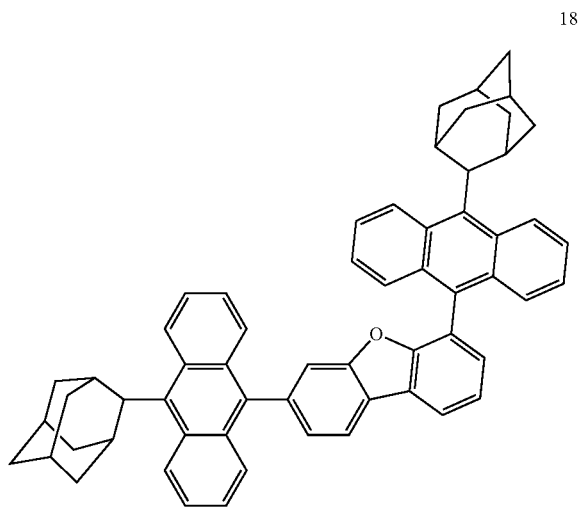

19
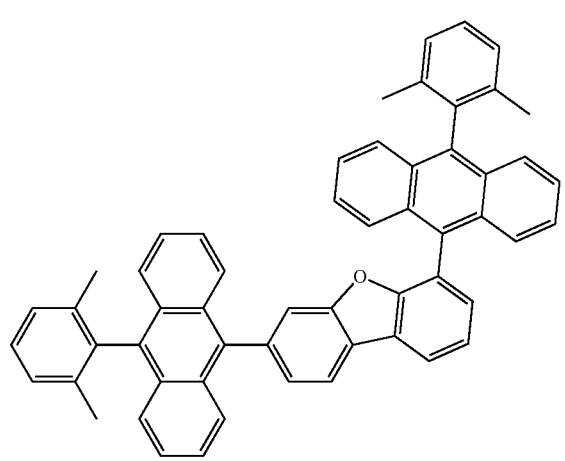
20
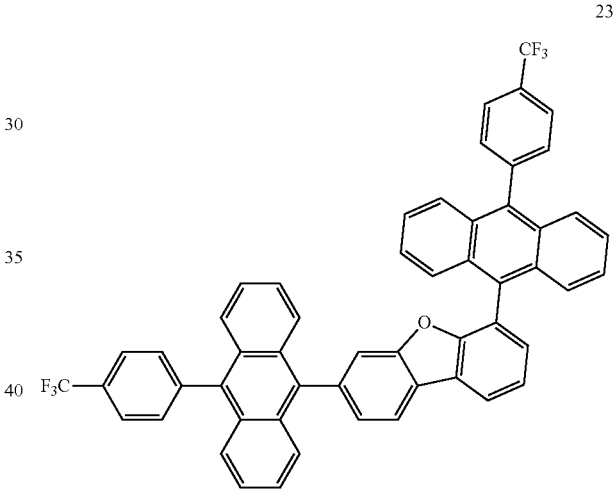
21
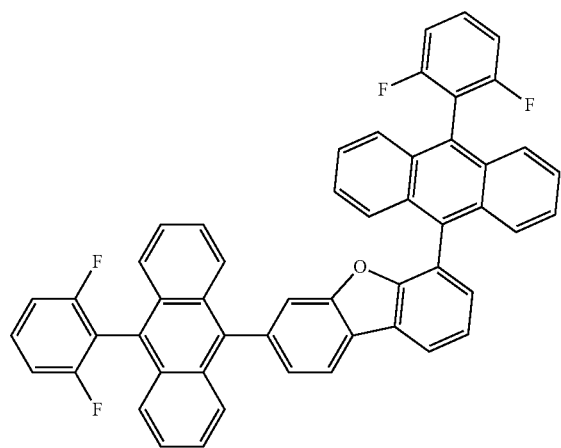
22
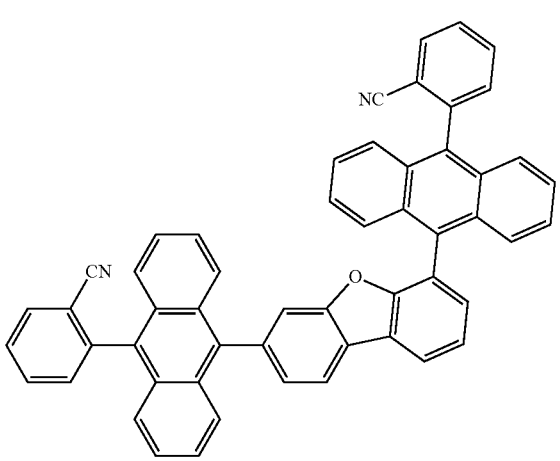
23
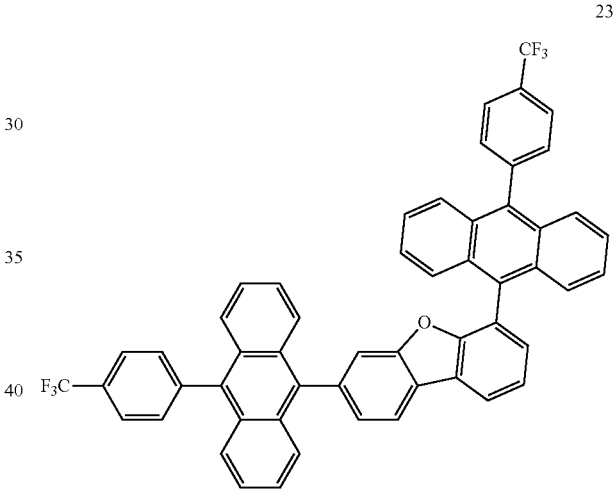
24
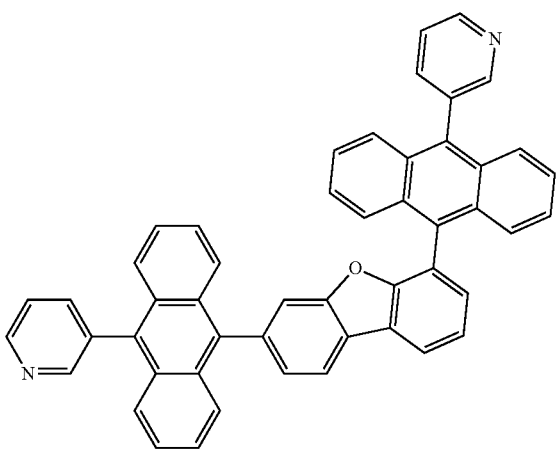

25
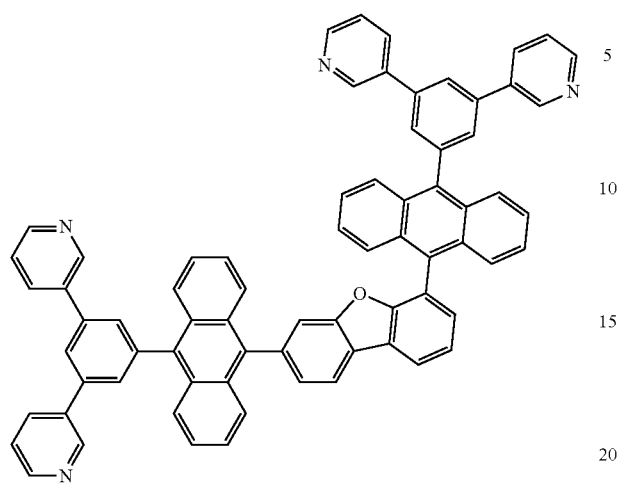
26
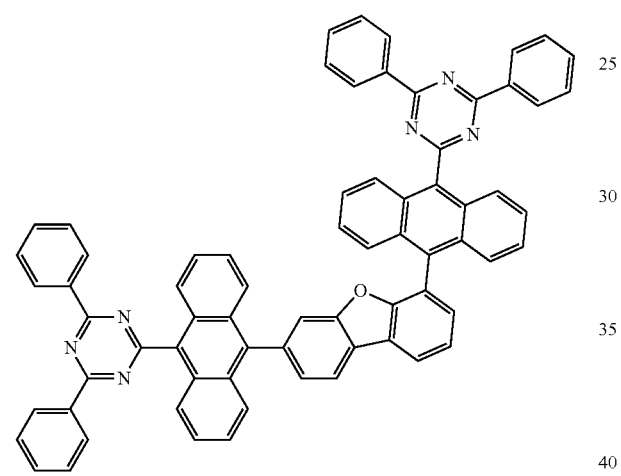
27
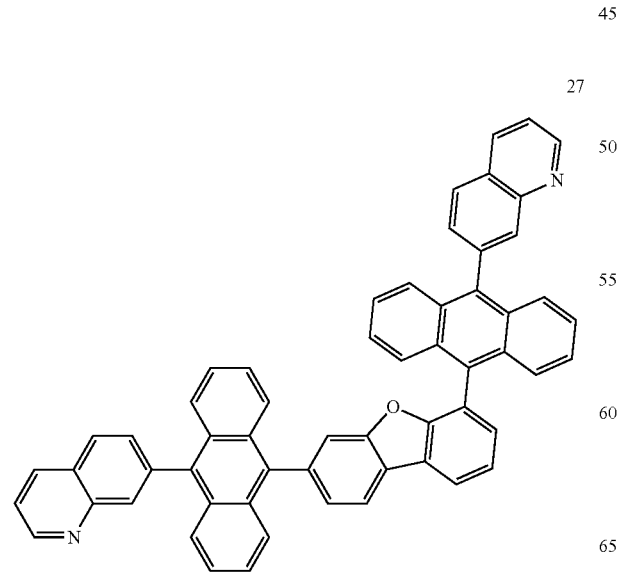
28
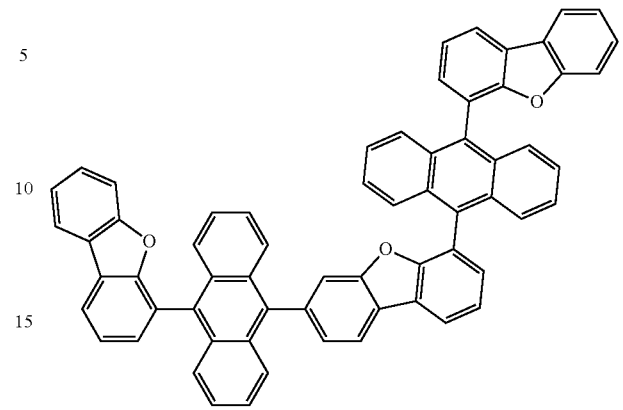
29
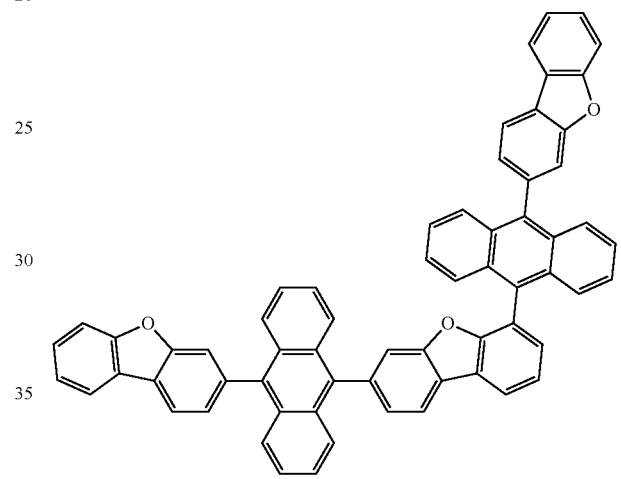
30
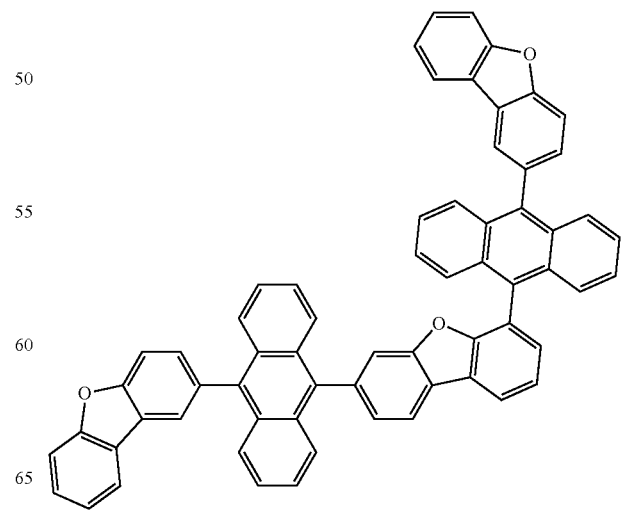

1465
-continued
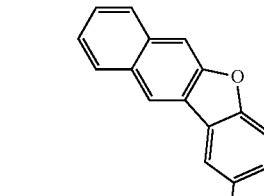
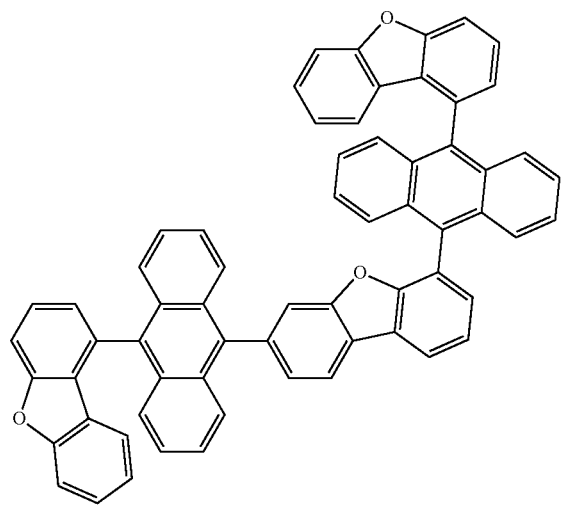
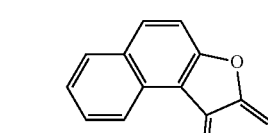
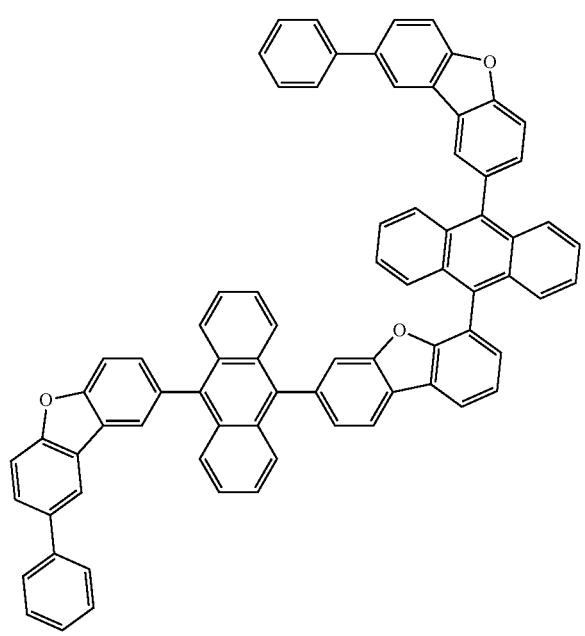
1466
-continued
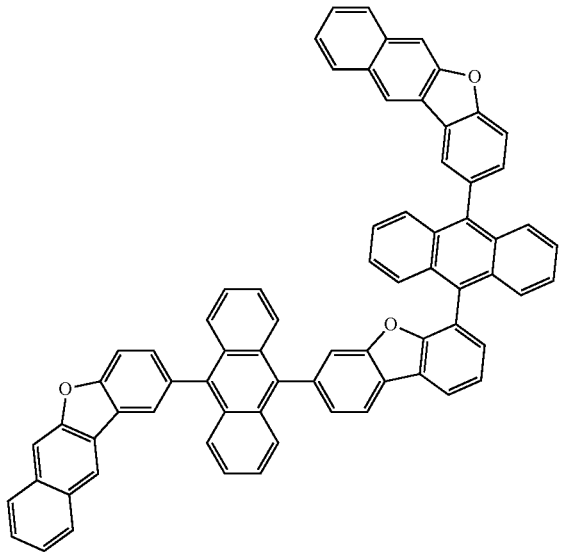
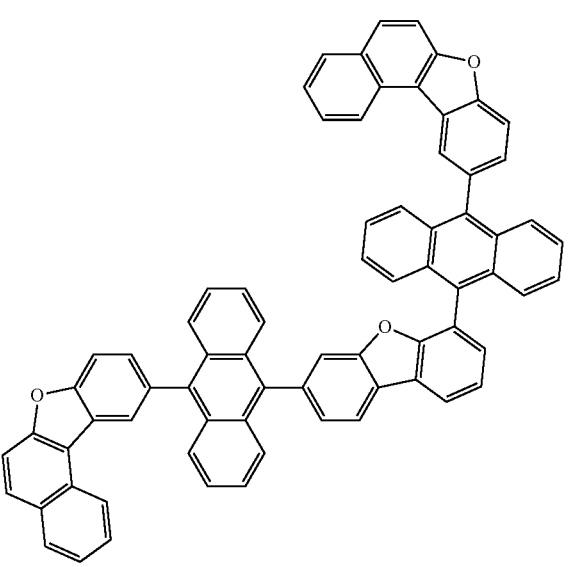

35
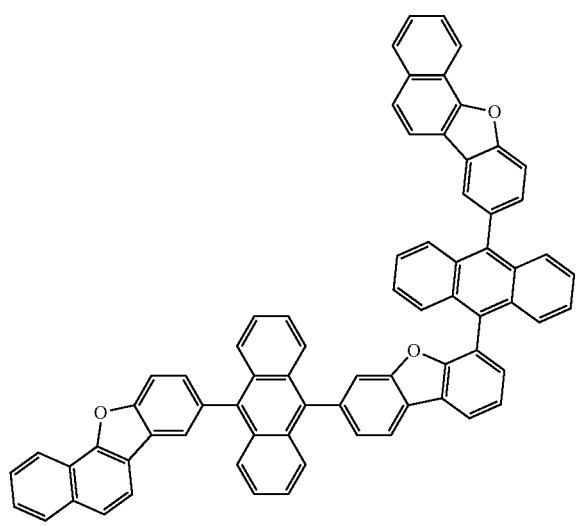
36
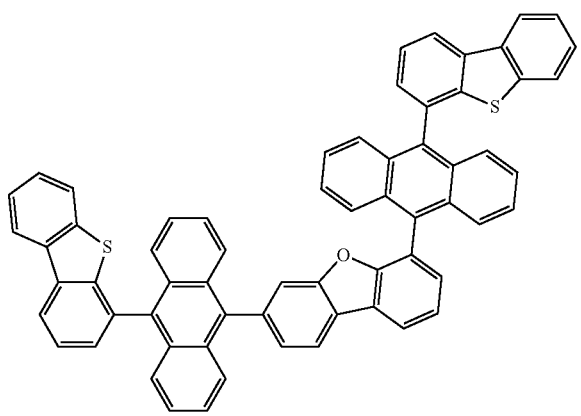
37
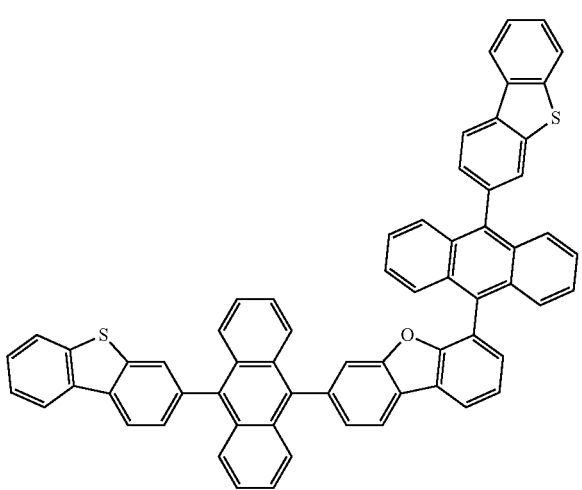
38
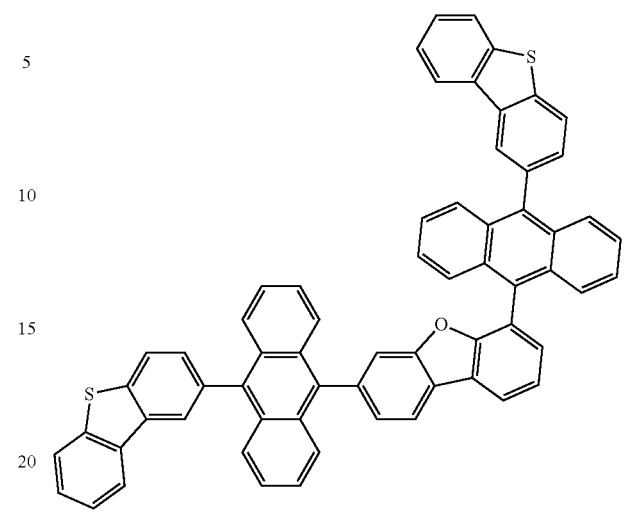
39
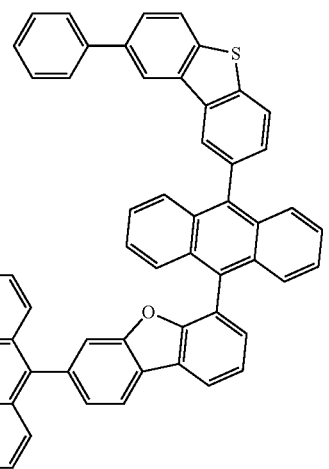
40

1469
-continued
41
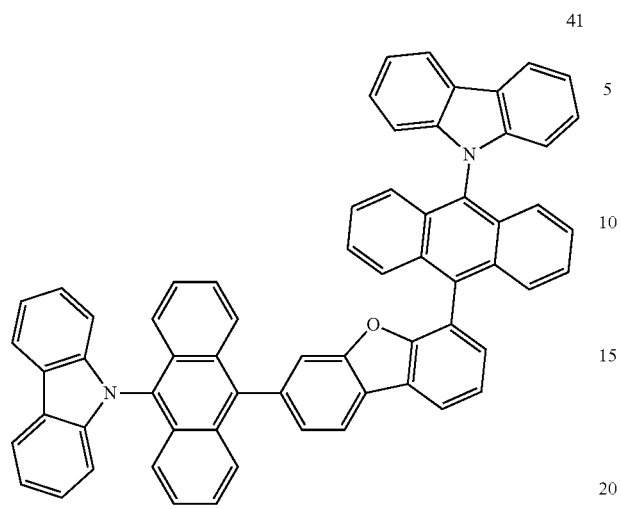
42
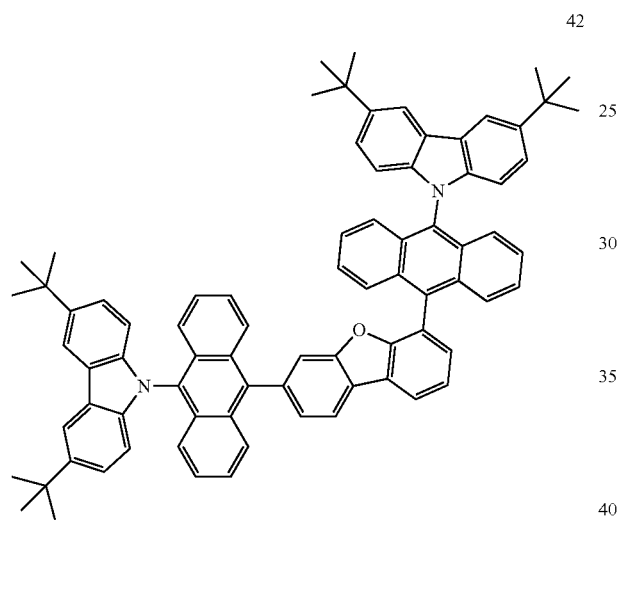
43
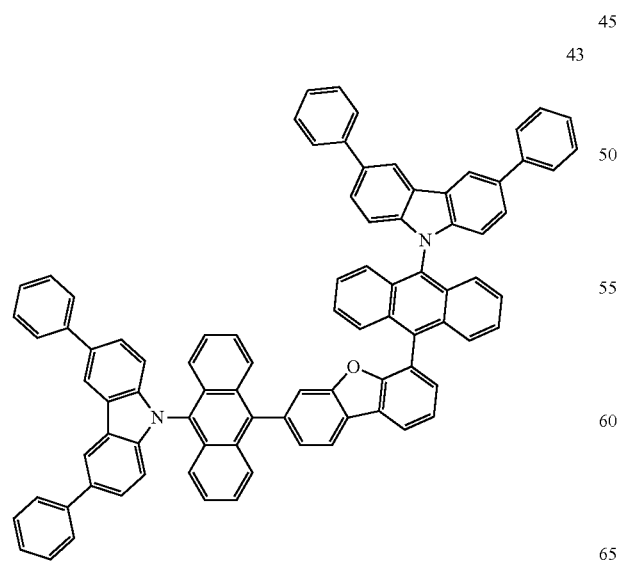
1470
-continued
44
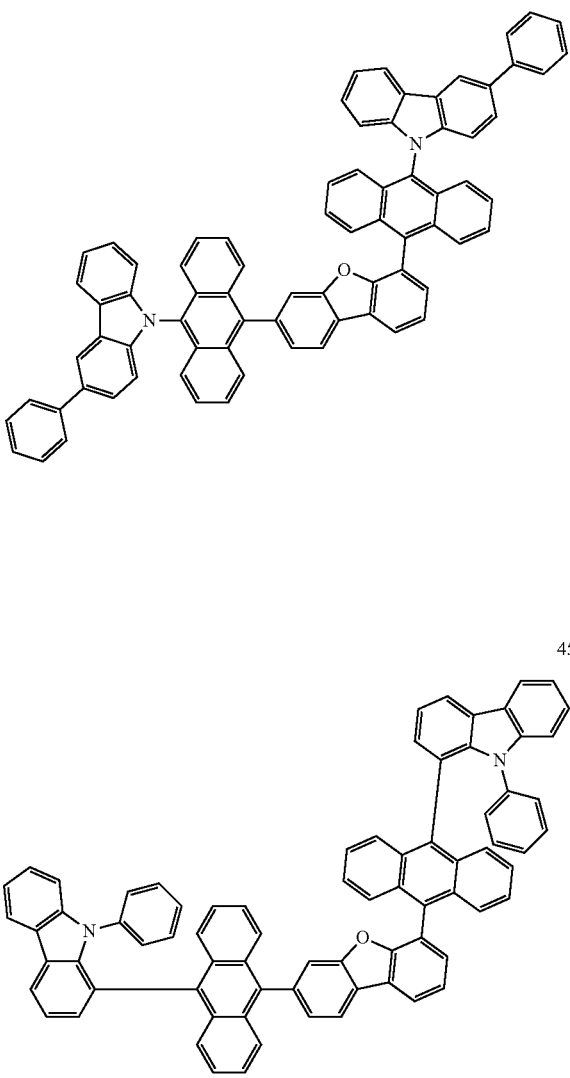
45
46

1471
-continued
47
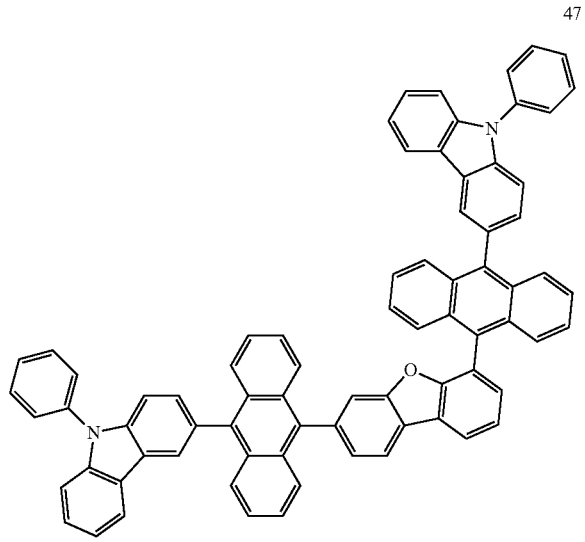
48
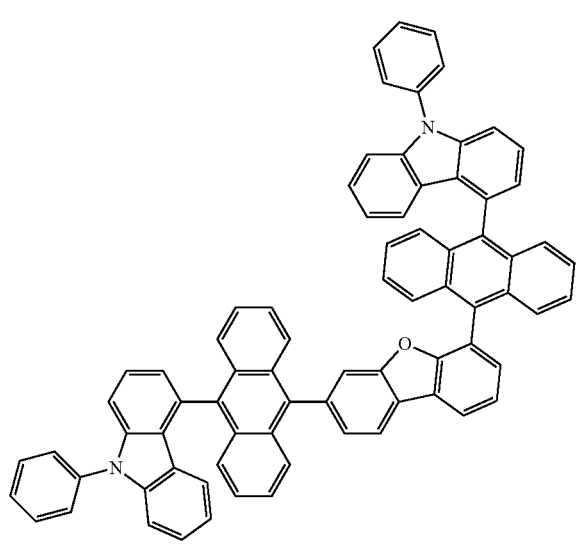
49
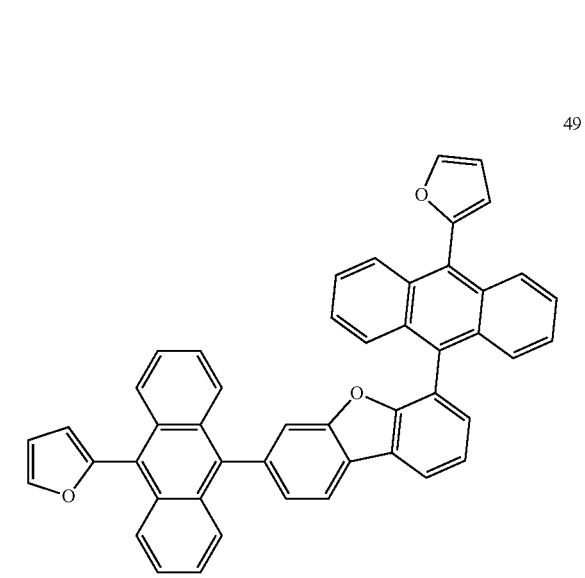
1472
-continued
50
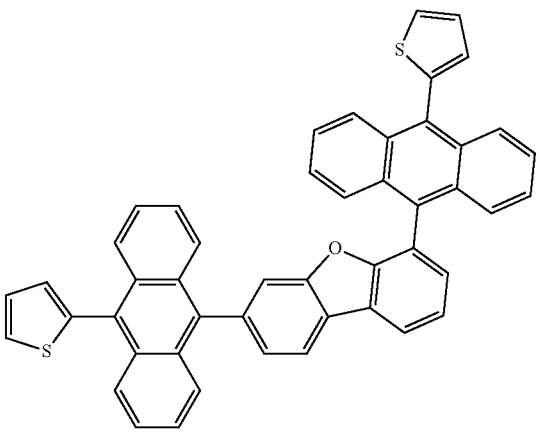
51
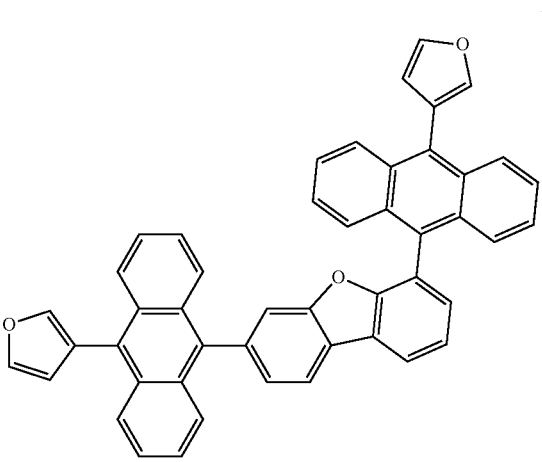
52
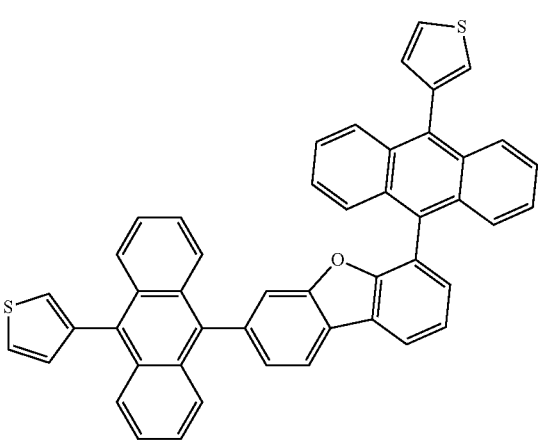

1473
-continued
1474
-continued
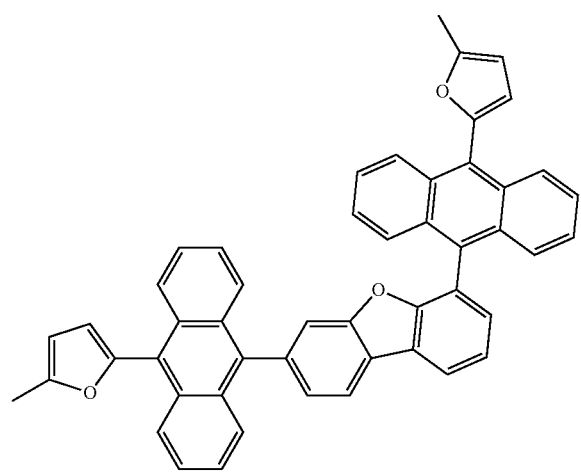
53
54
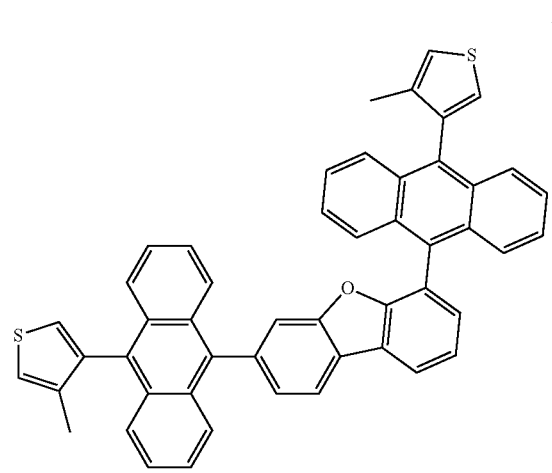
56
57
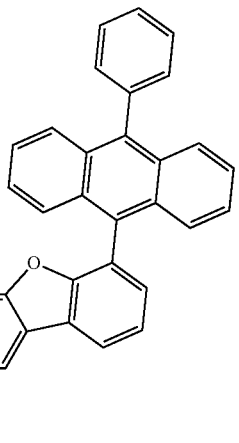
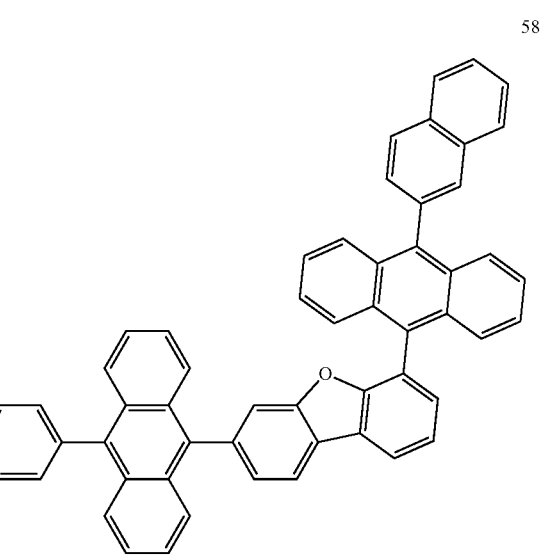
55
58

1475
-continued
59
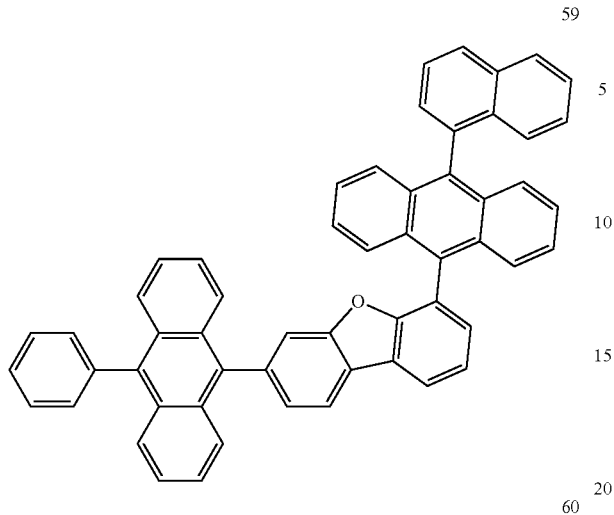
60
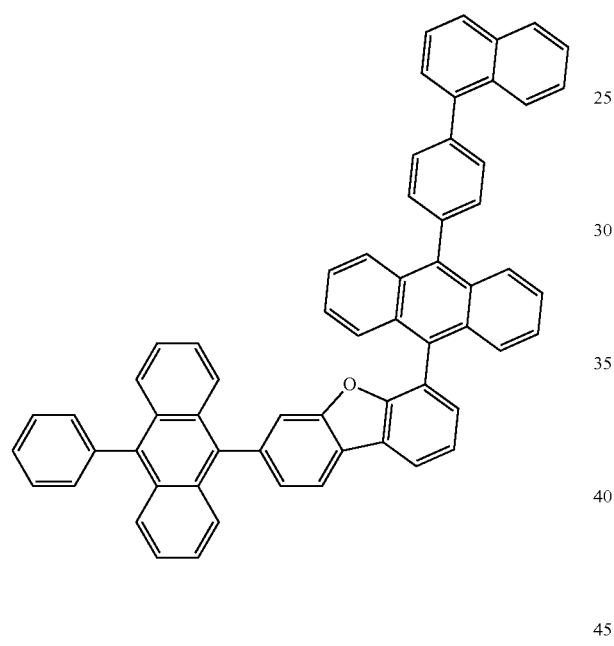
61
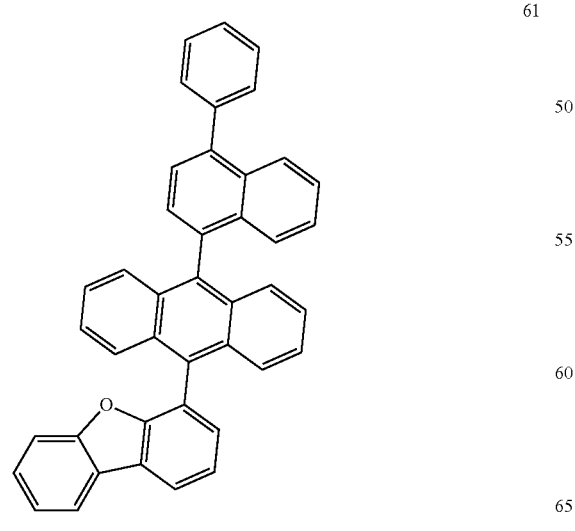
1476
-continued
62
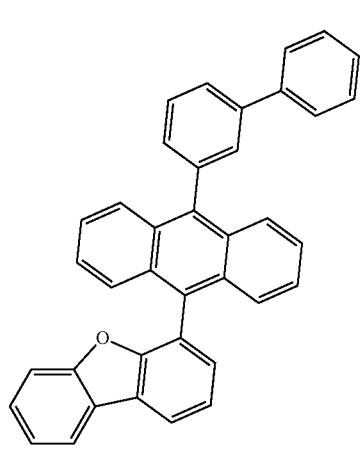
63
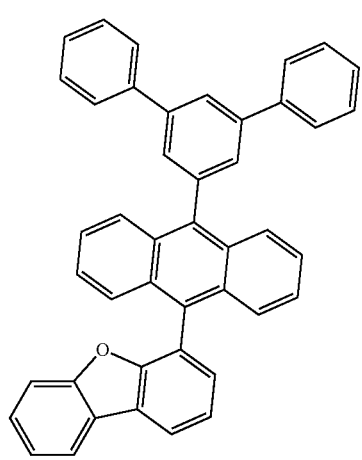
64
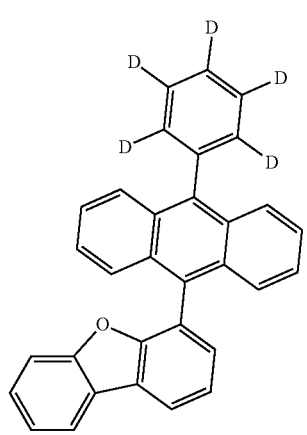

1477
-continued
65
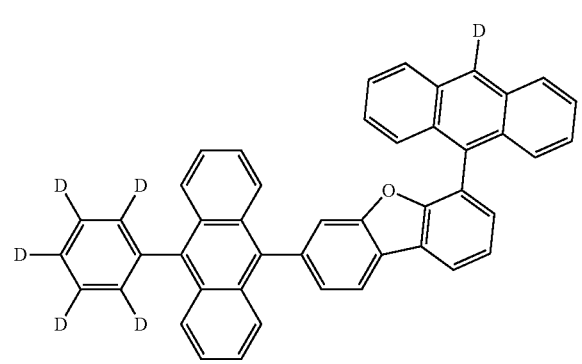
66
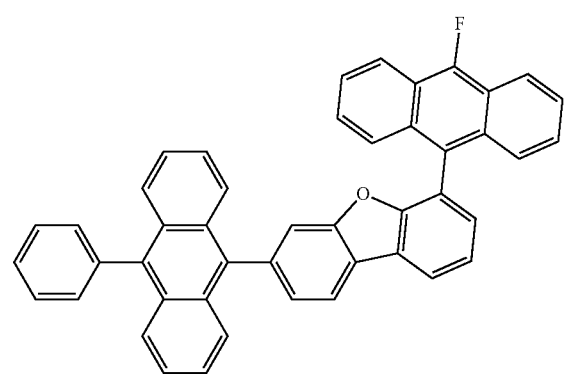
67
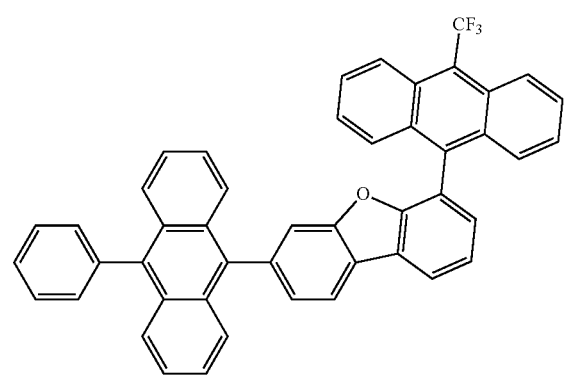
68
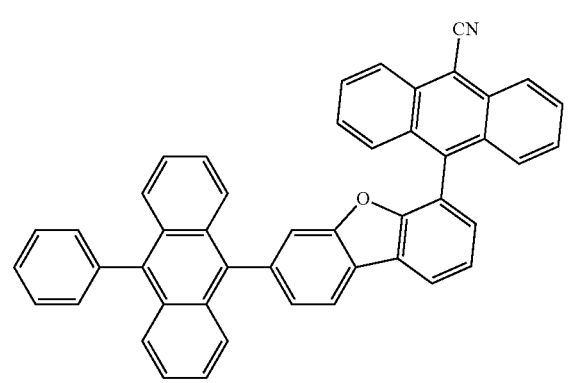
1478
-continued
69
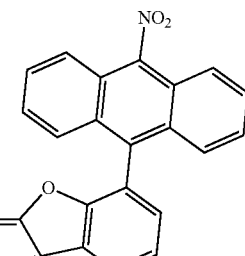
70
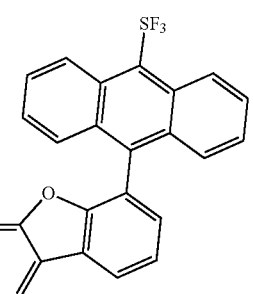
71
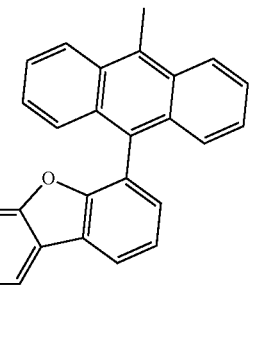
72
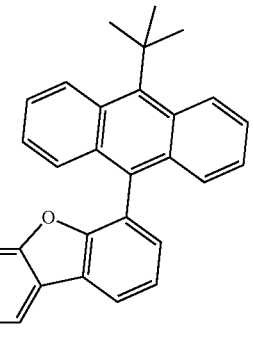

1479
-continued
73
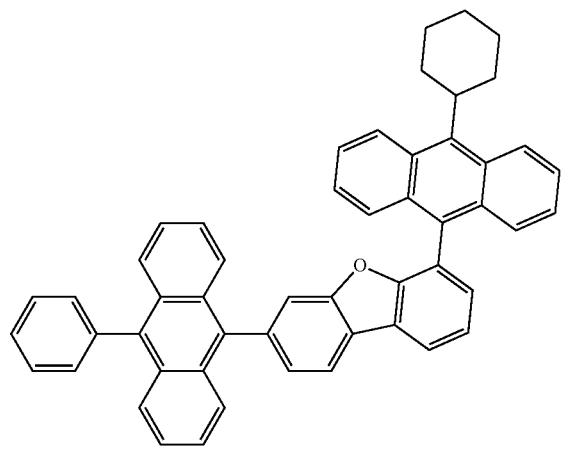
74
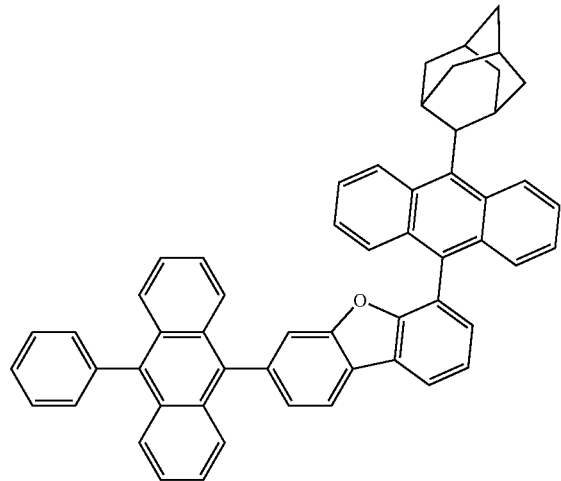
75
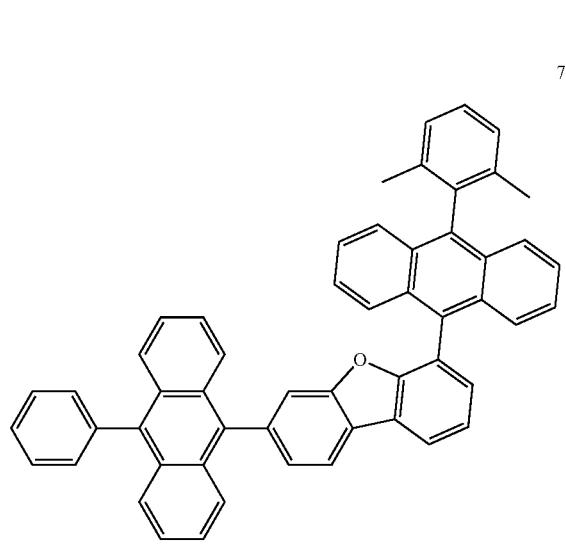
1480
-continued
76
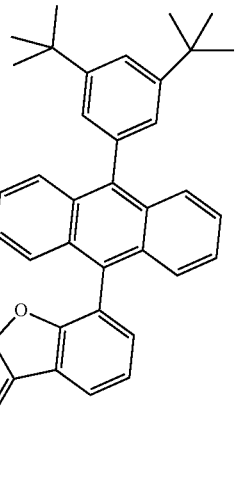
77
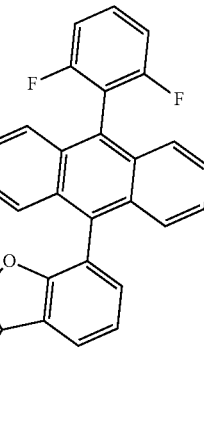
78
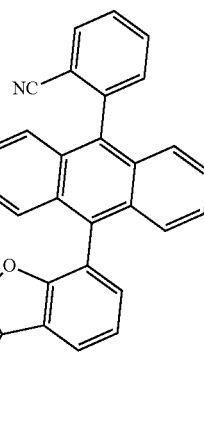

1481 -continued
79
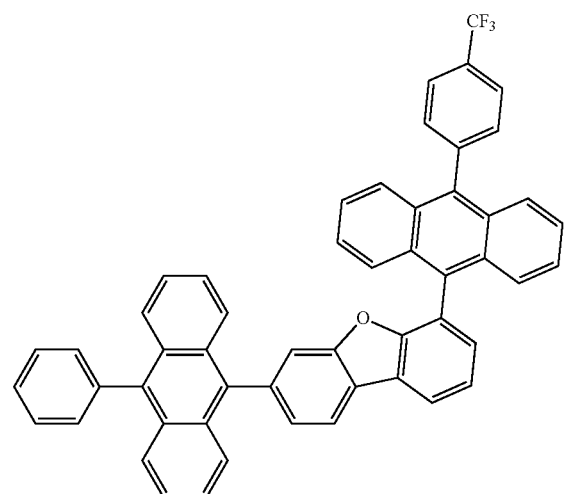
80
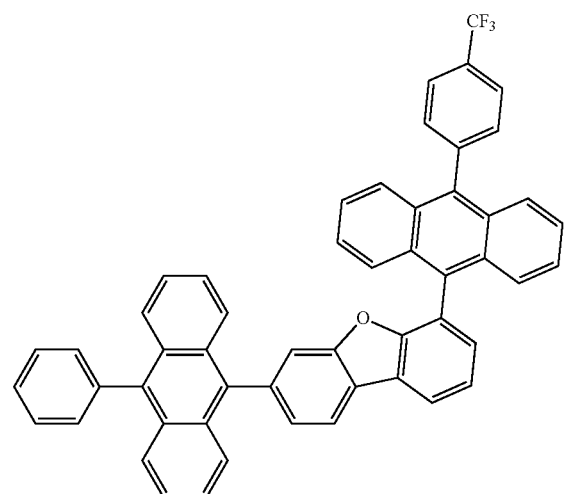
81
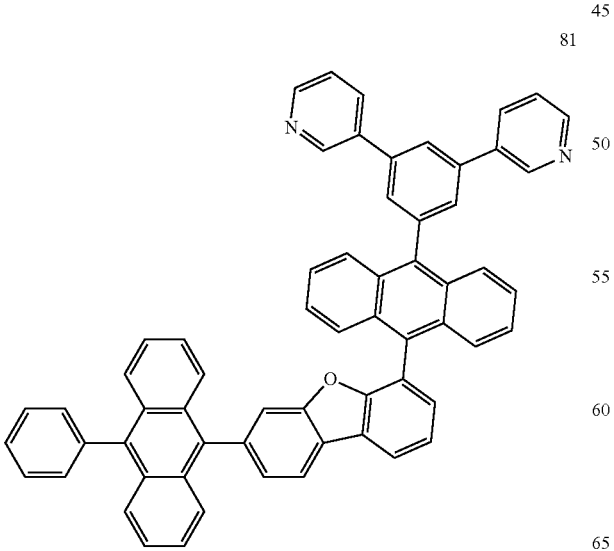
1482 -continued
82
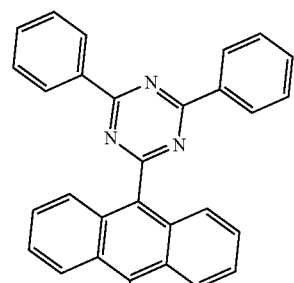
83
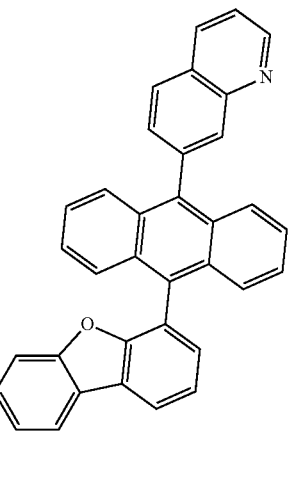
84
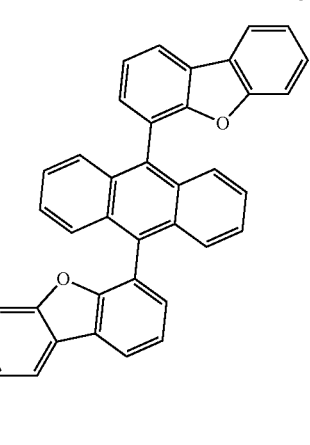

1483
-continued
85
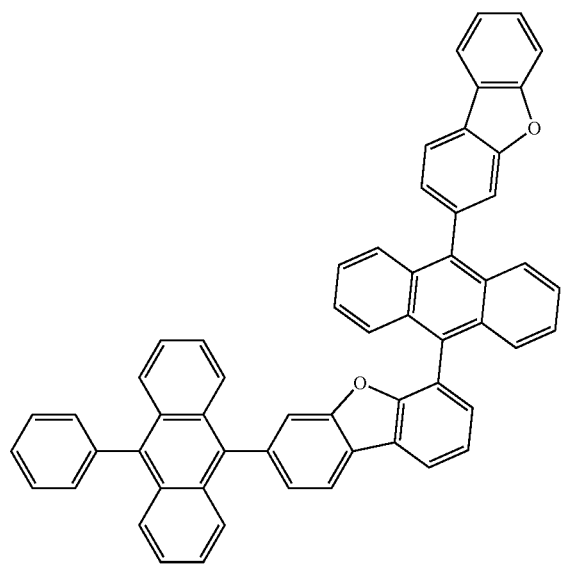
86
87
1484
-continued
88
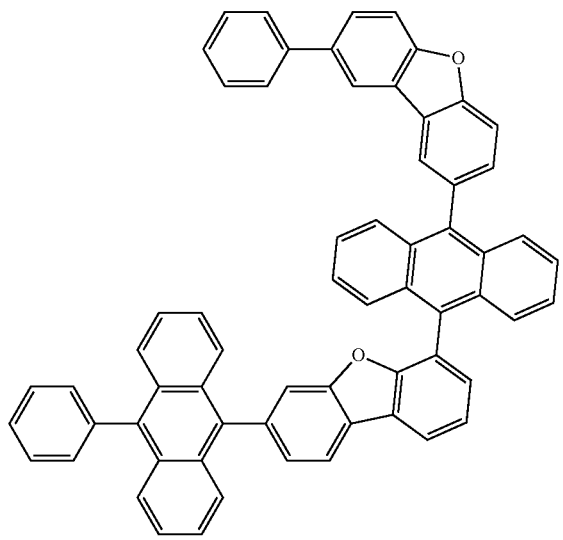
89

1485
-continued
90
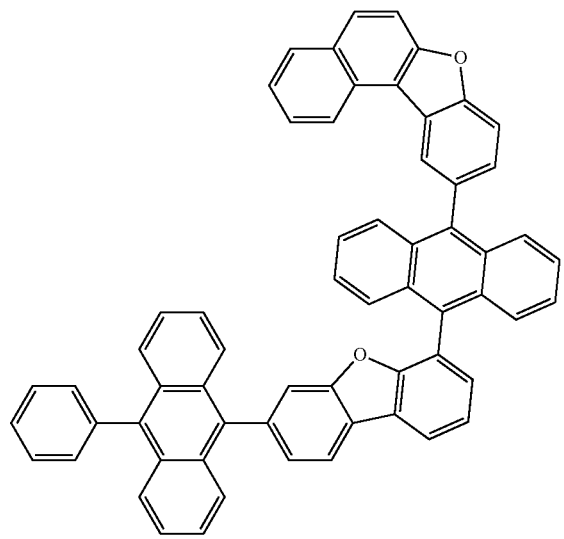
91
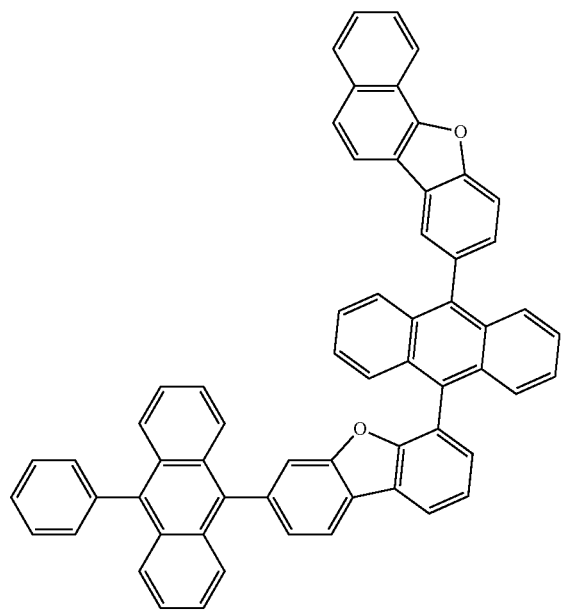
92
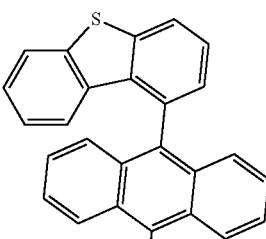
1486
-continued
93
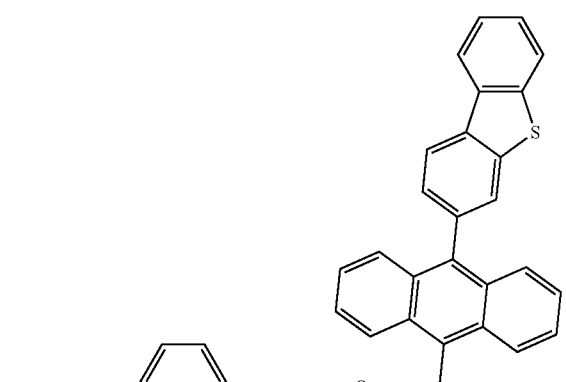
94
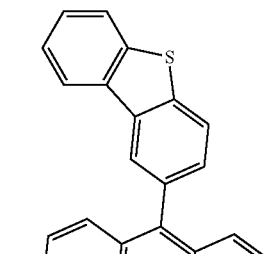
95
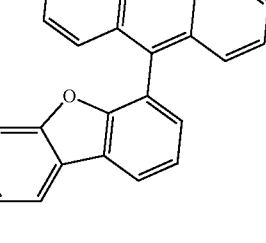

1487
-continued
96
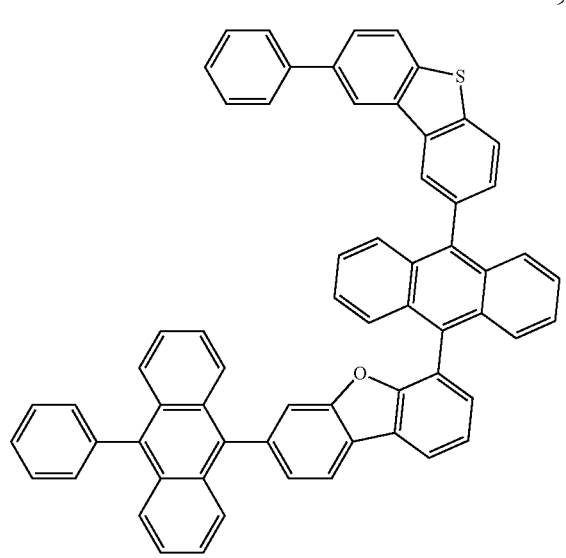
97
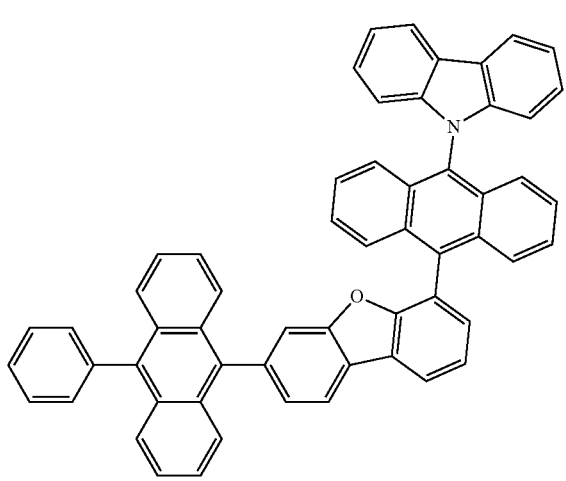
98
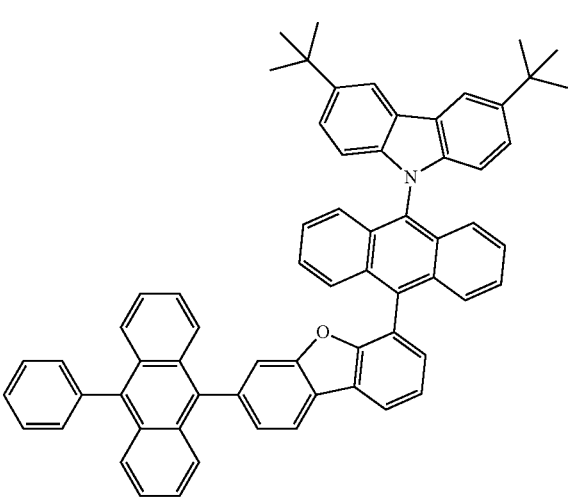
1488
-continued
99
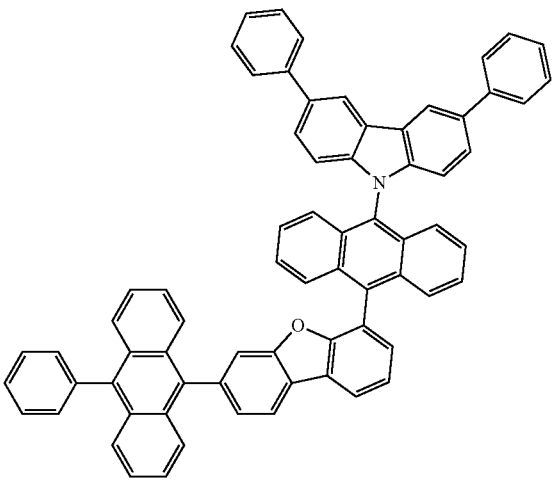
100
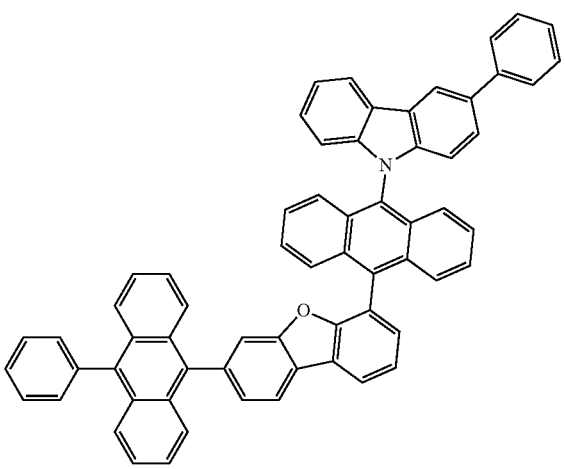
101
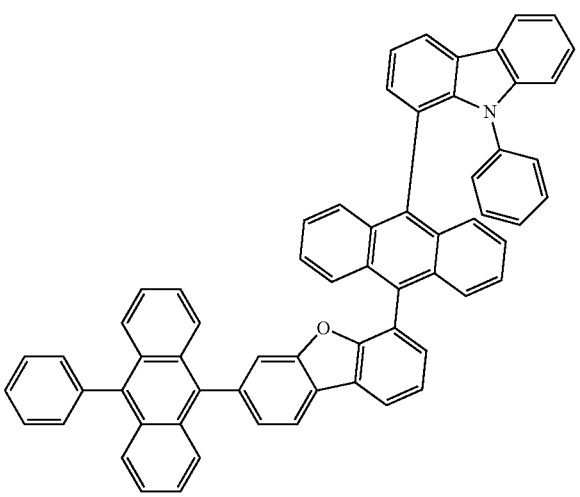

1489
-continued
102
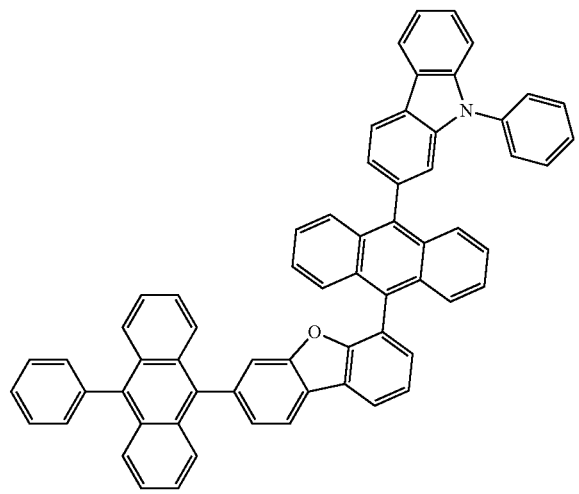
103
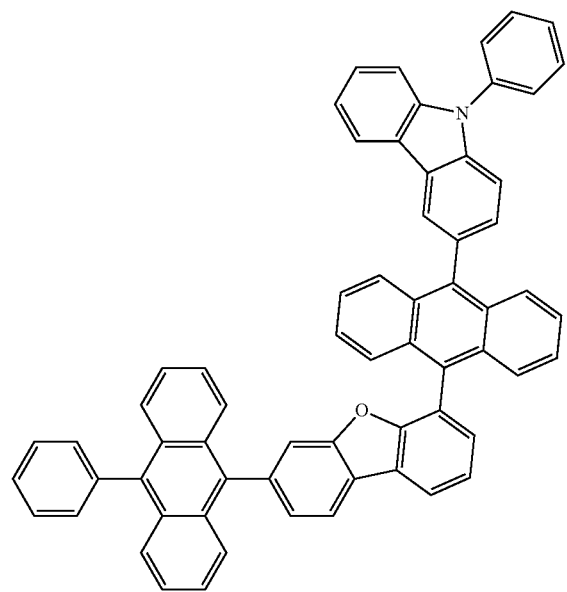
1490
-continued
104
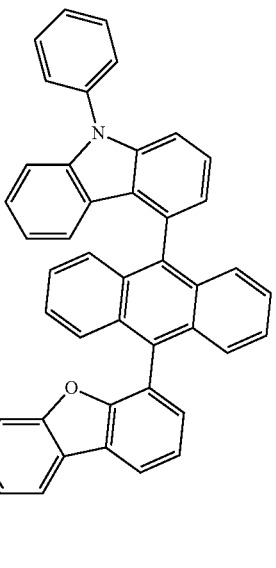
105
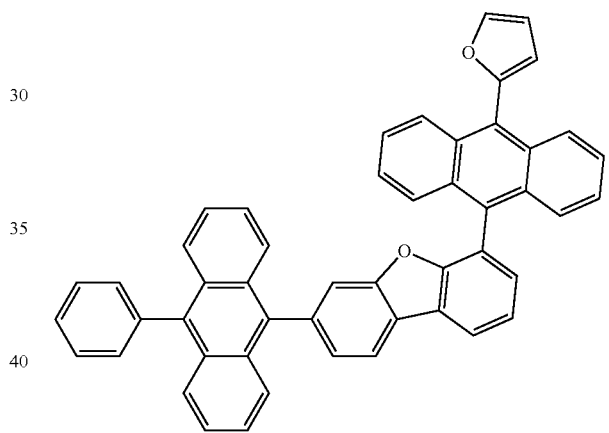
106
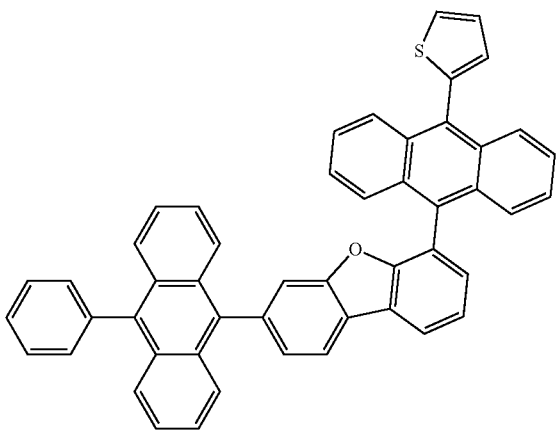

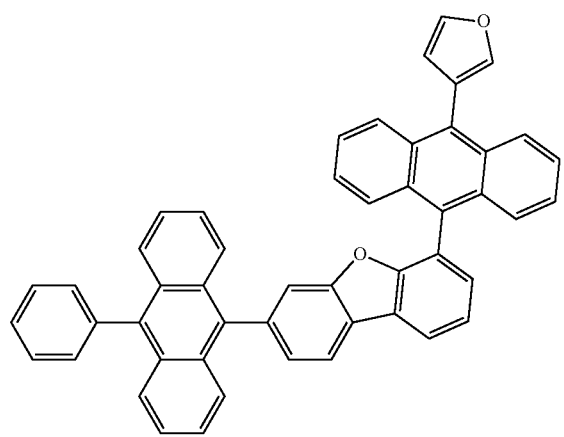
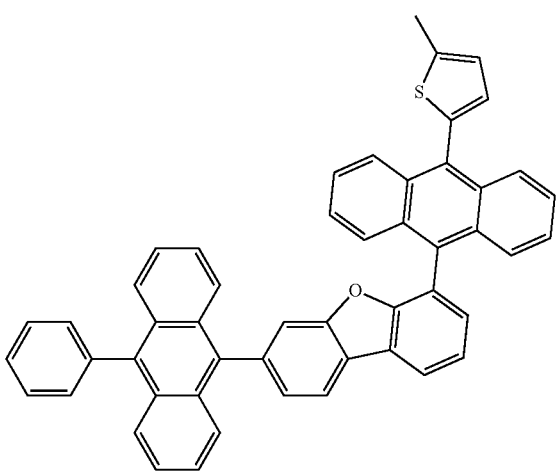

-continued

113

114

-continued

115

116

1495
-continued
117
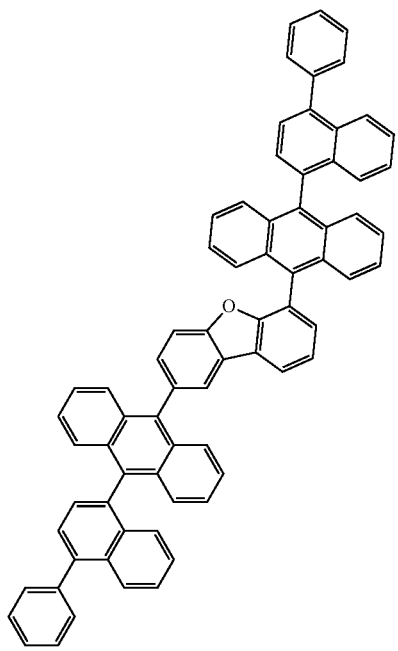
118
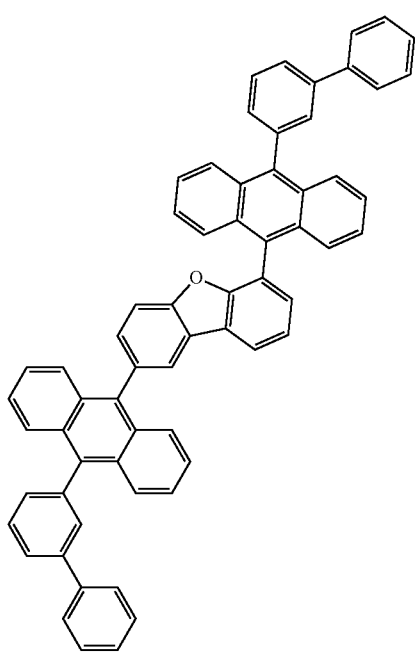
1496
-continued
119
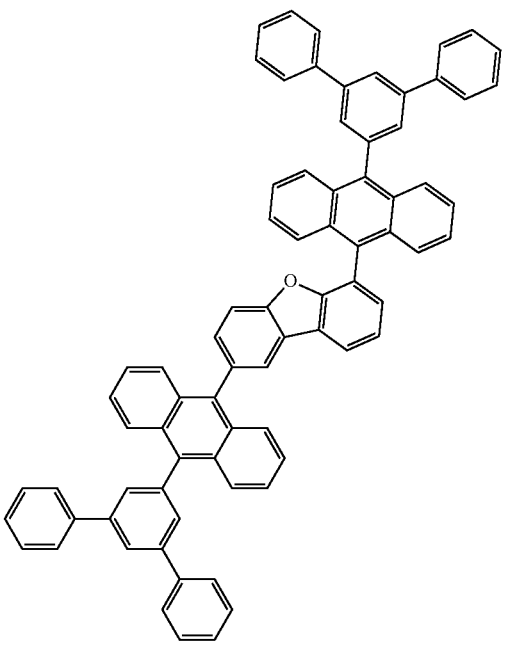
120
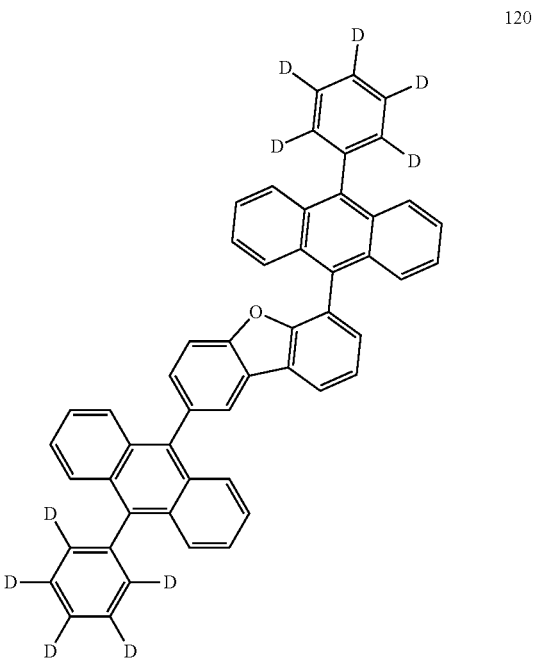

121
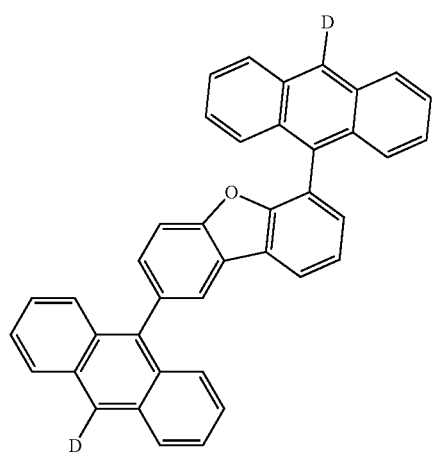
124
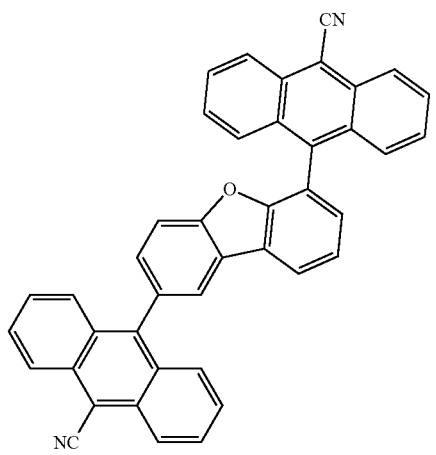
122
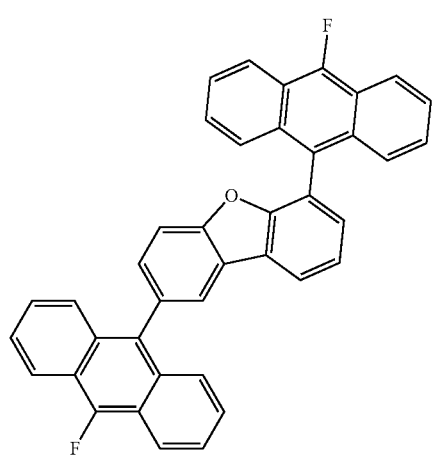
125
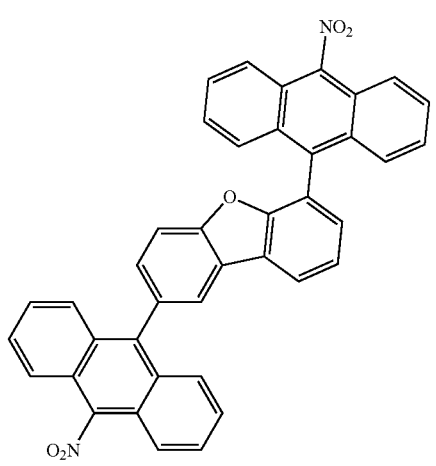
123
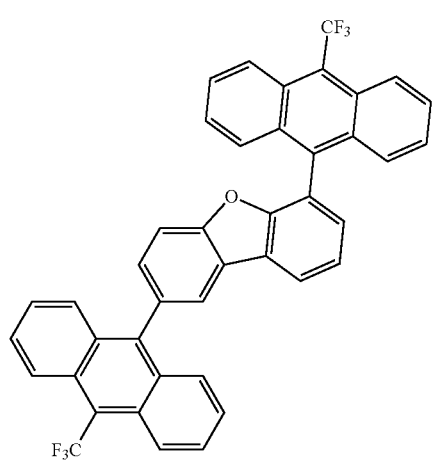
126
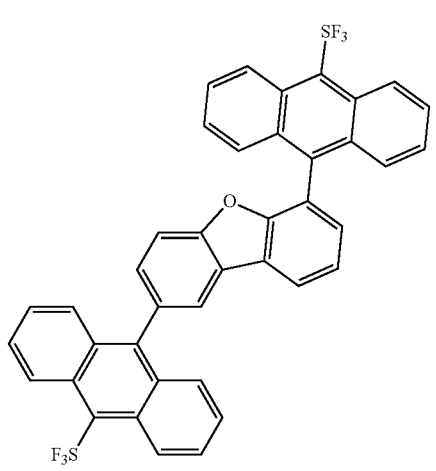

1499
-continued
1500
-continued
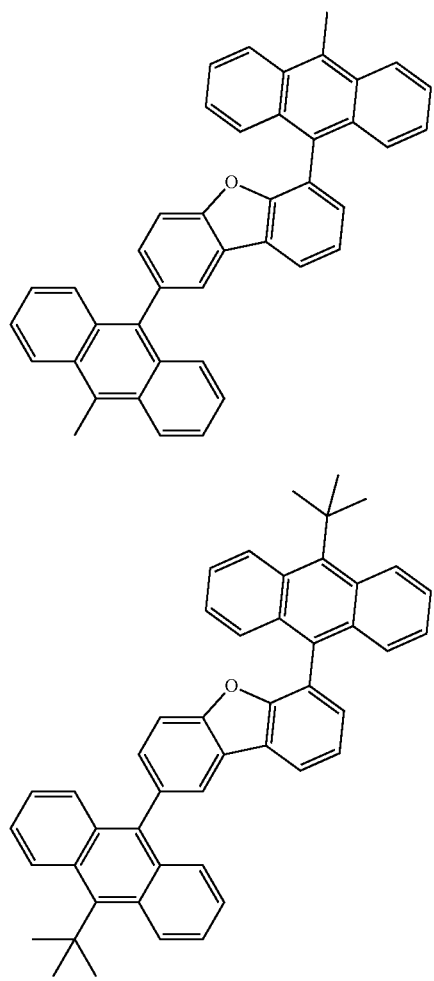
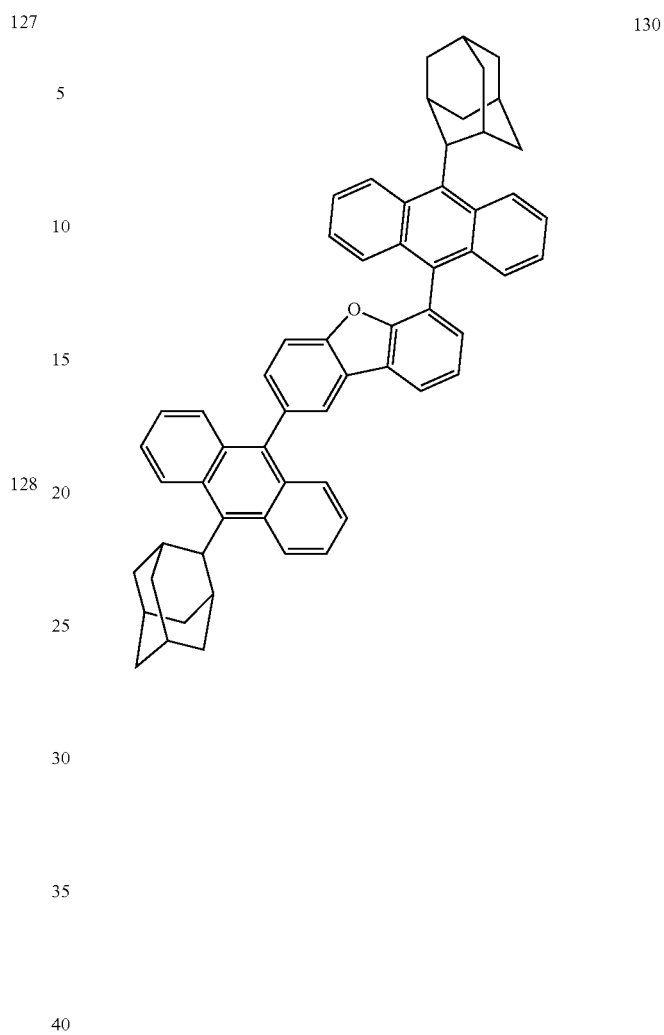
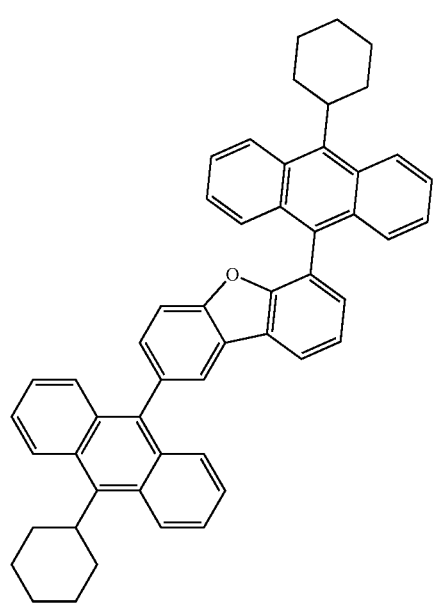
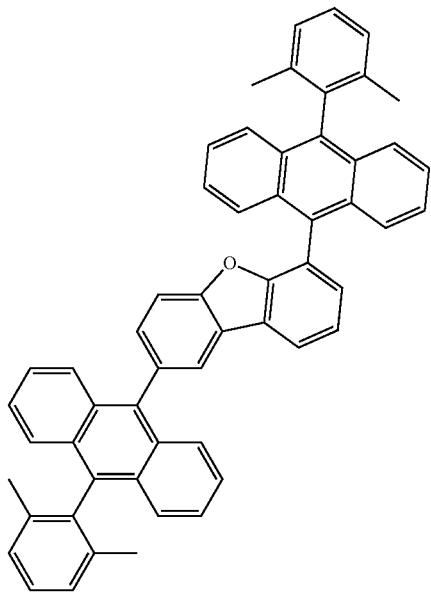

1501
-continued
132
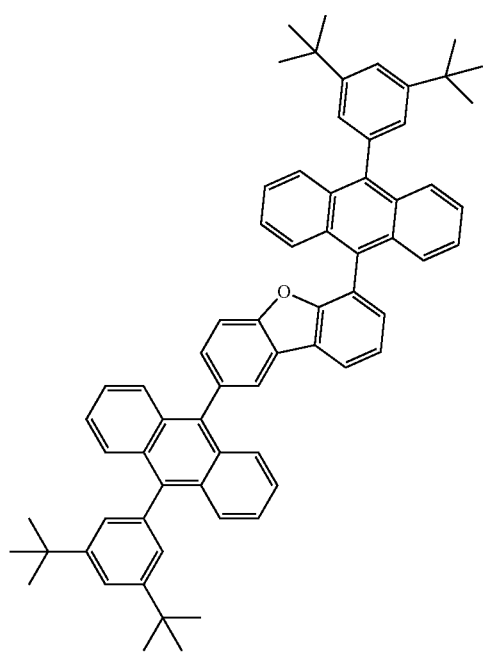
133
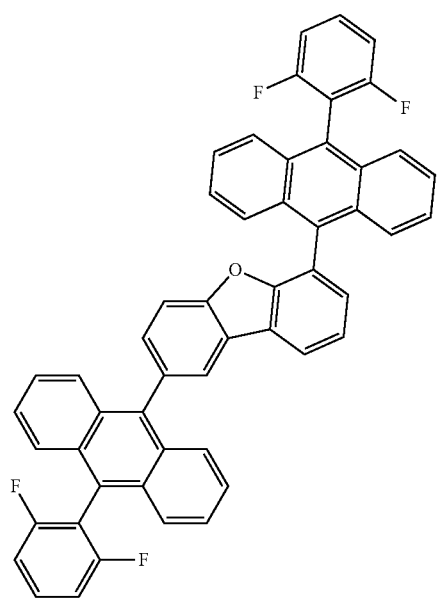
1502
-continued
134
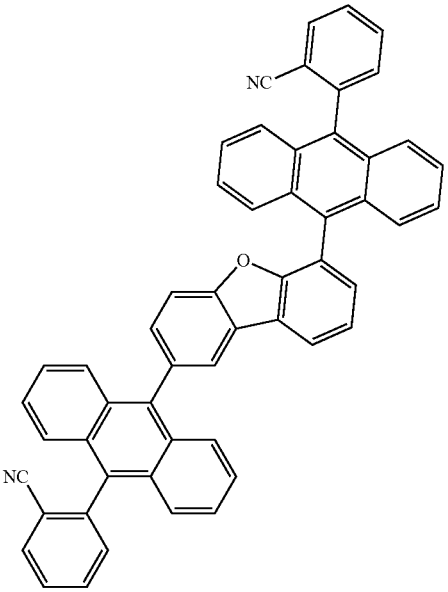
135
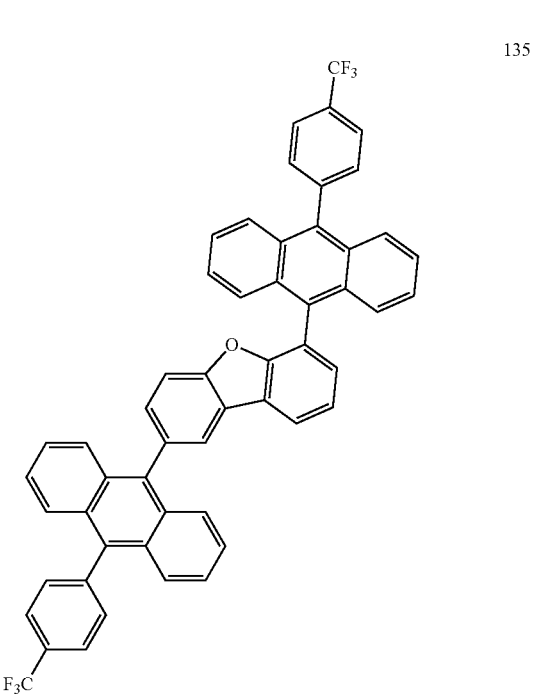

1503
-continued
136
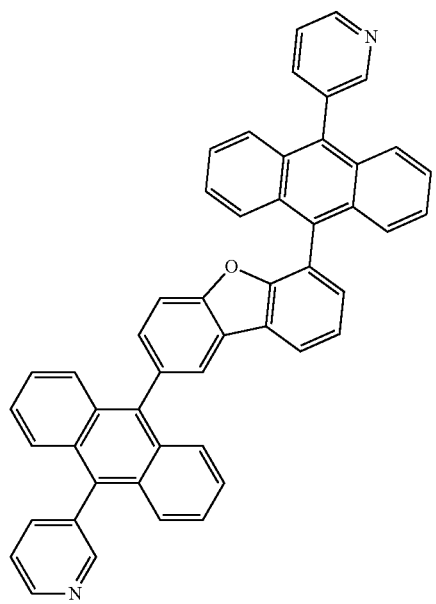
137
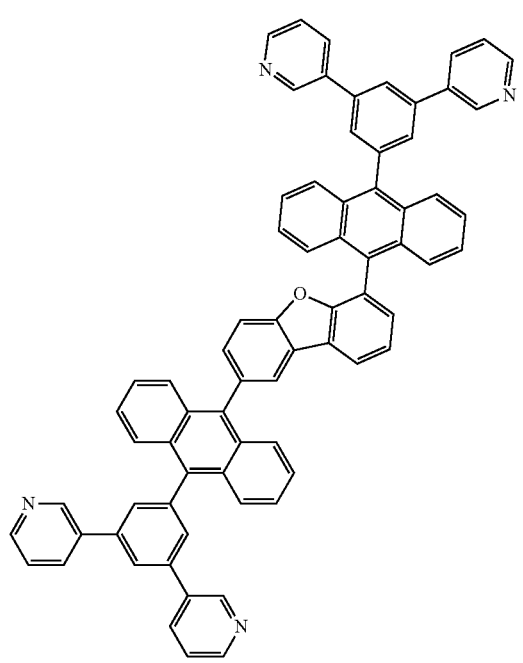
1504
-continued
138
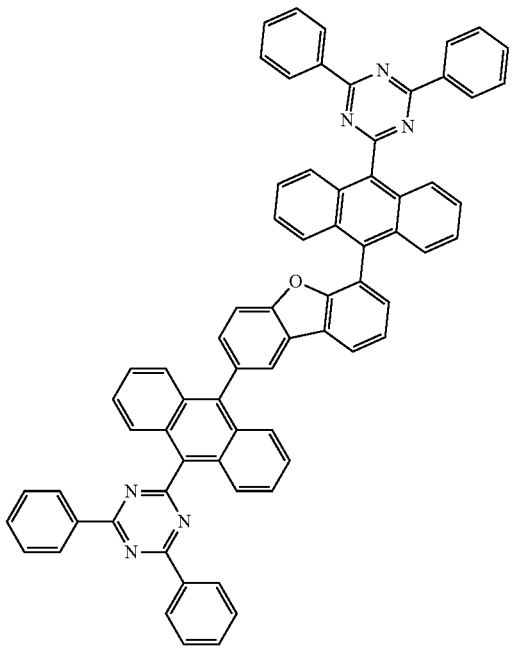
139
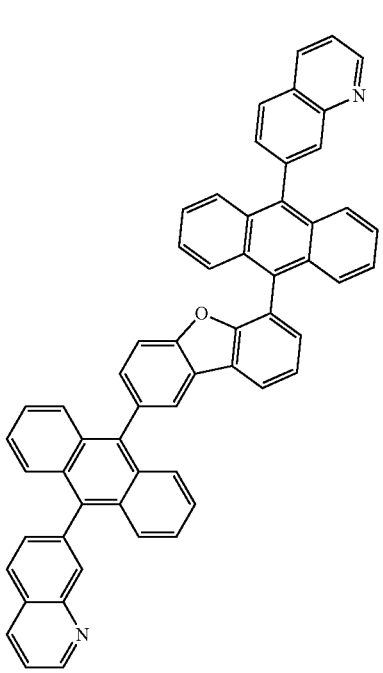

-continued
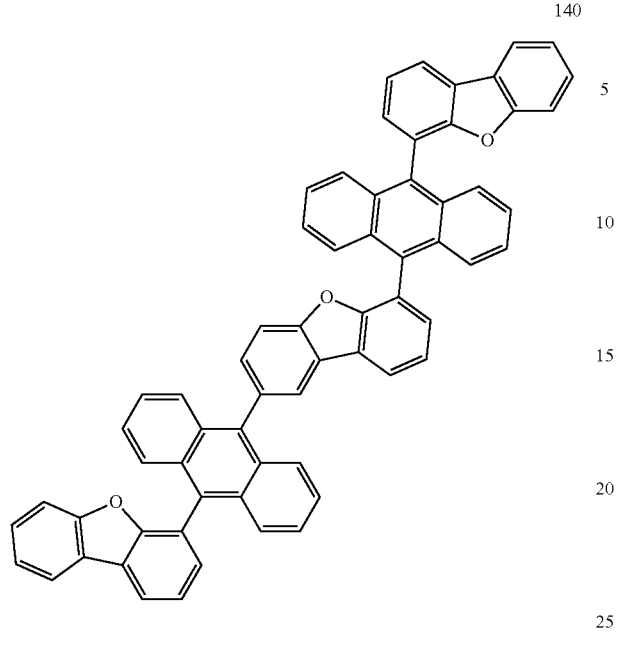
140
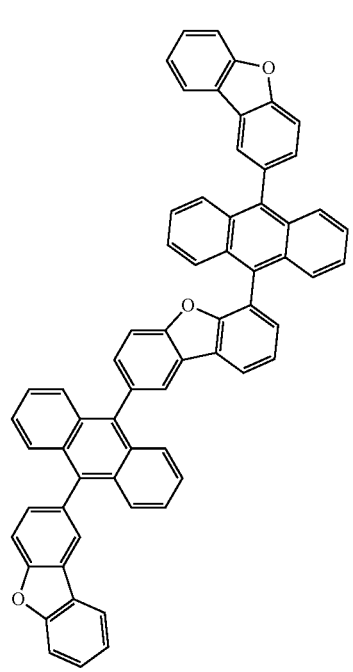
142
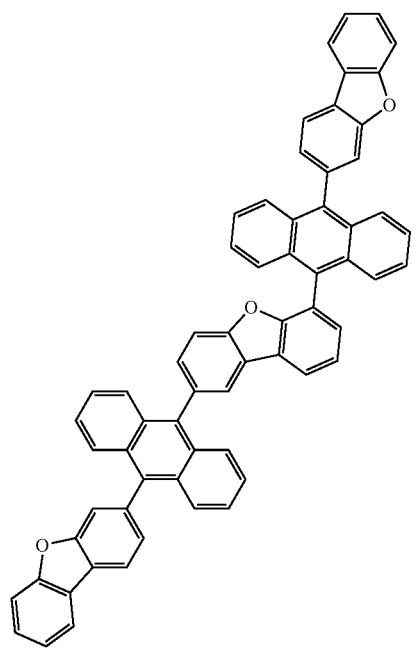
141
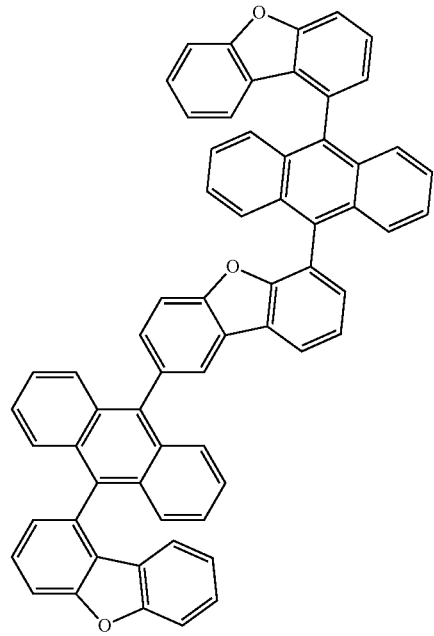
143

1507
-continued
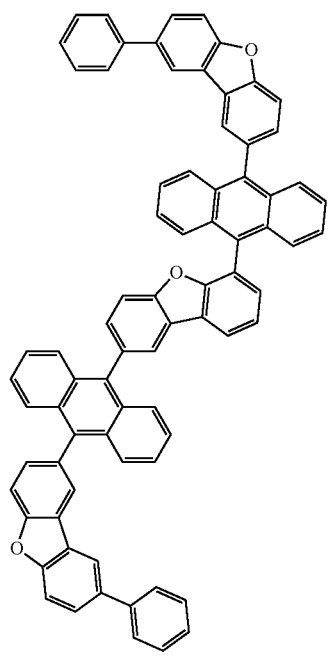
144
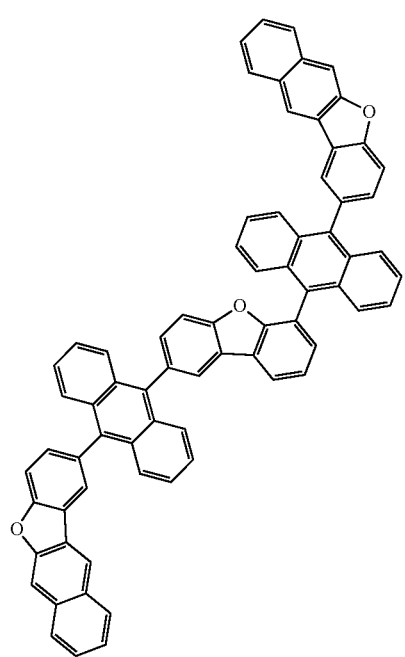
145
1508
-continued
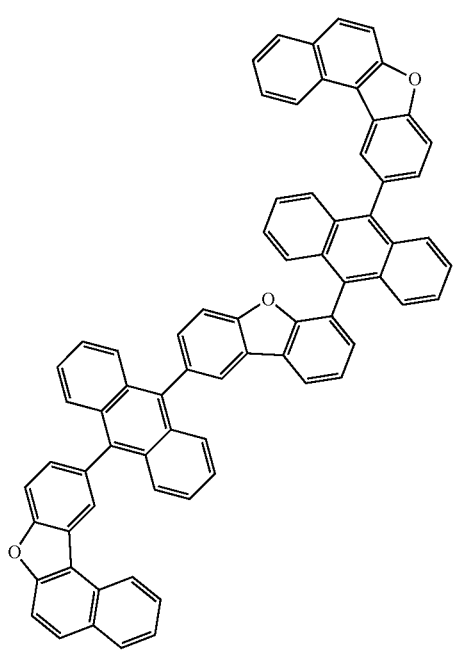
146
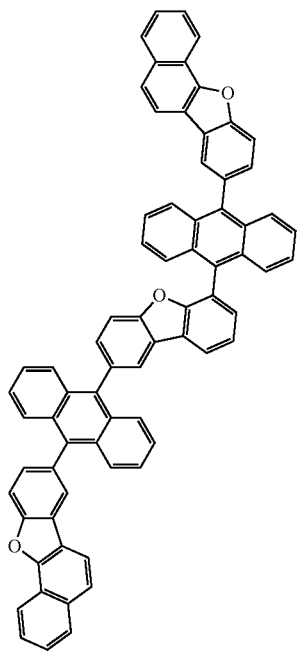
147

148
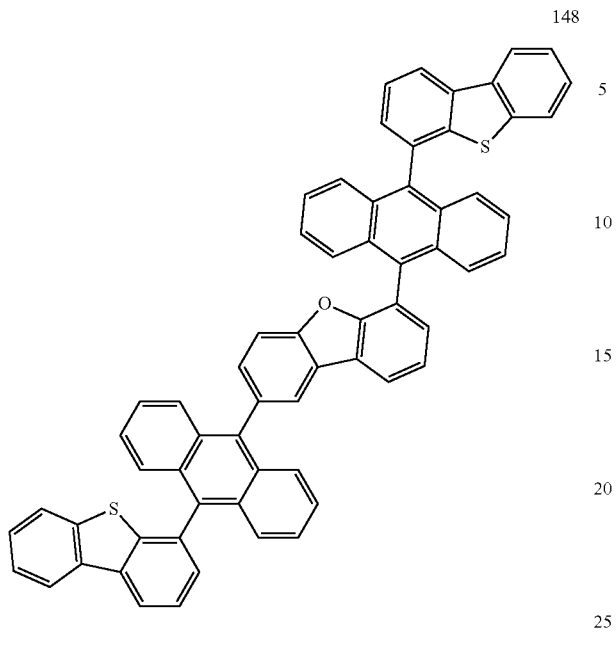
150
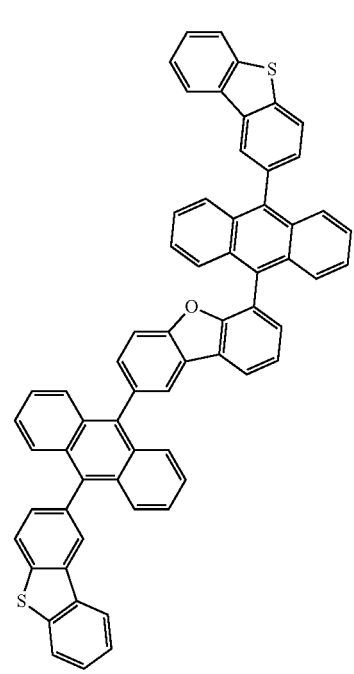
149
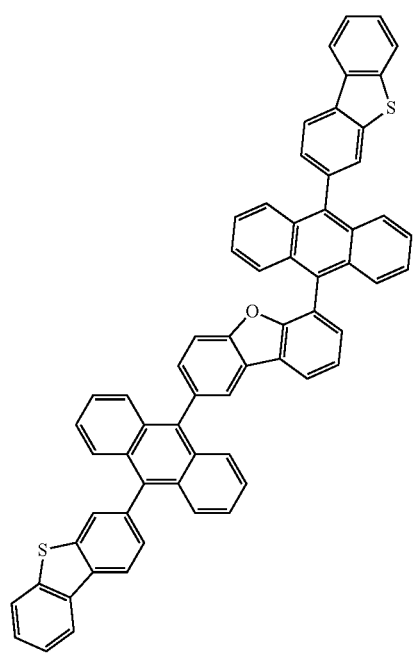
151
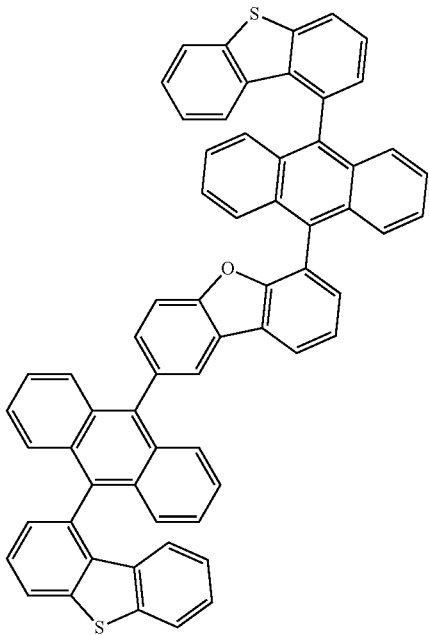

1511
-continued
152
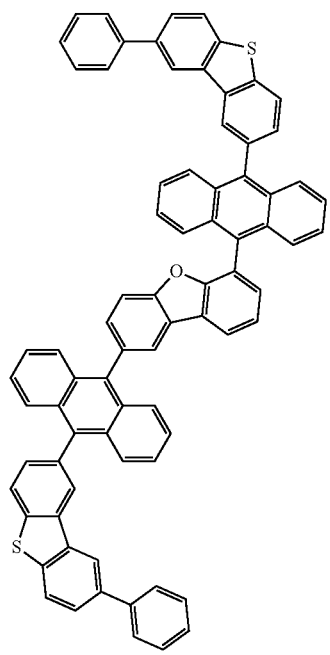
153
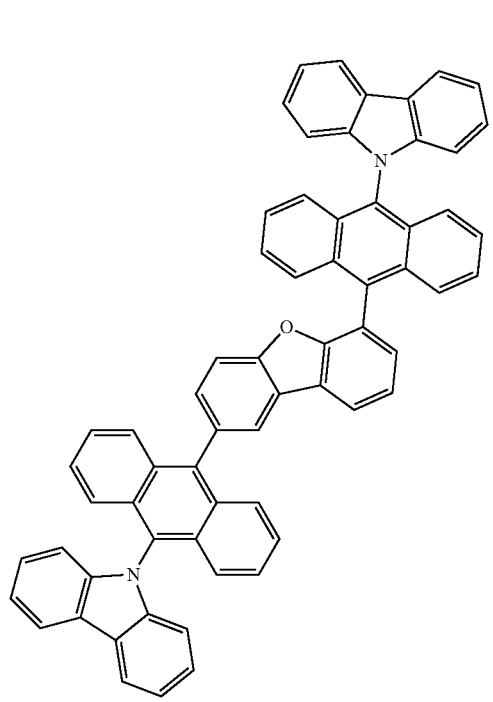
1512
-continued
154
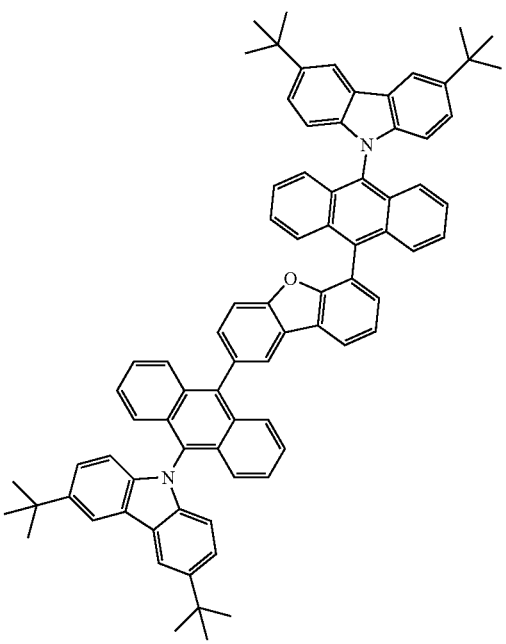
155
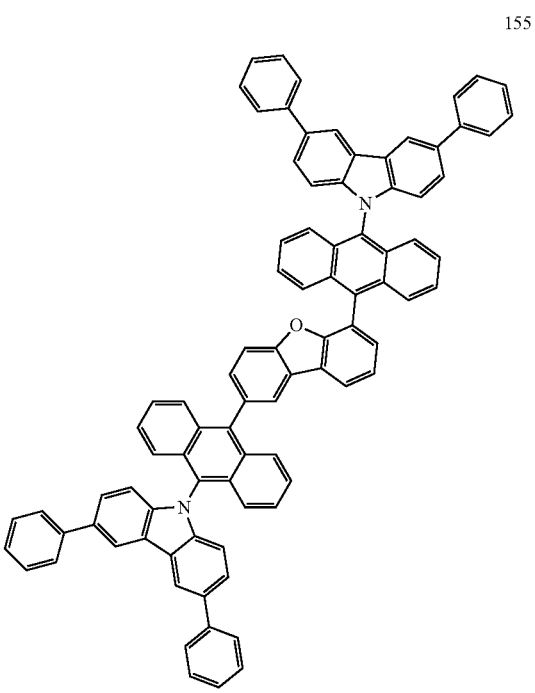

156
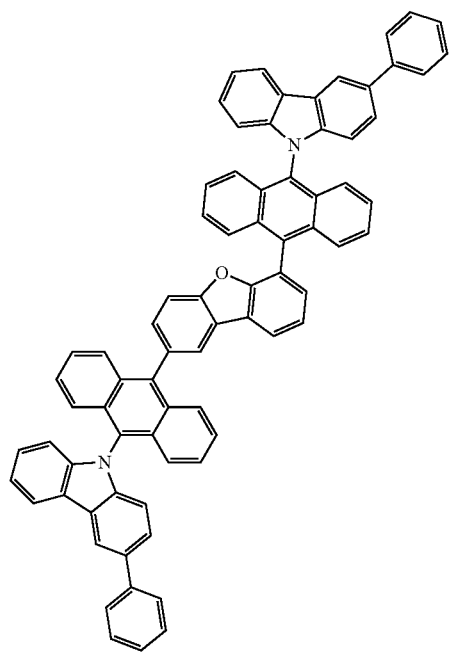
157
158
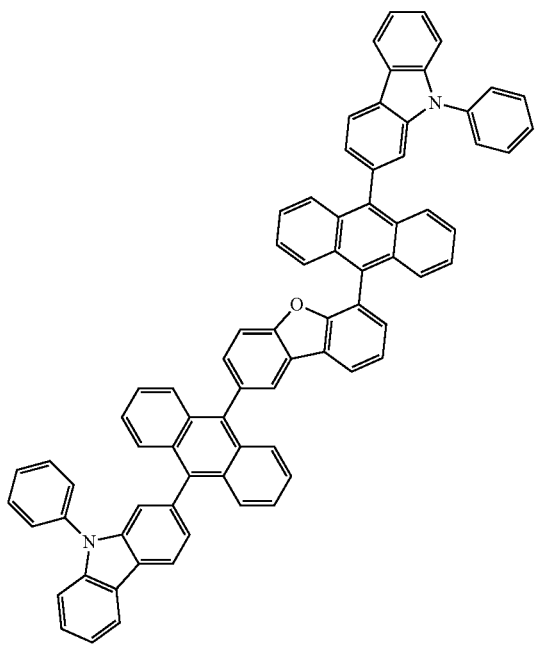
159
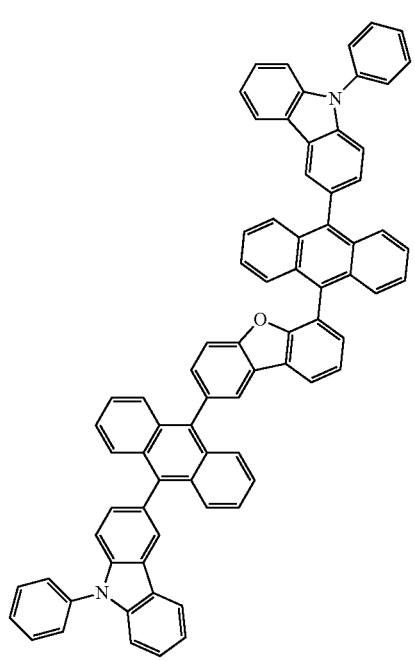

1515
-continued
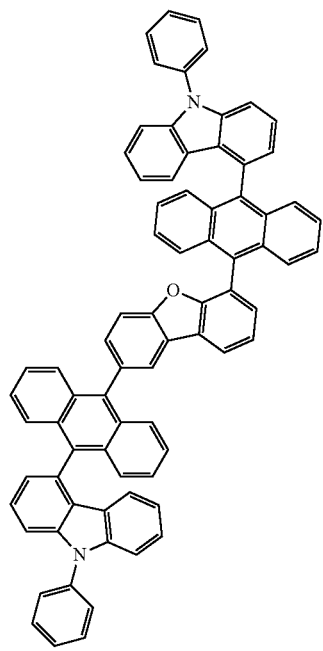
160
1516
-continued
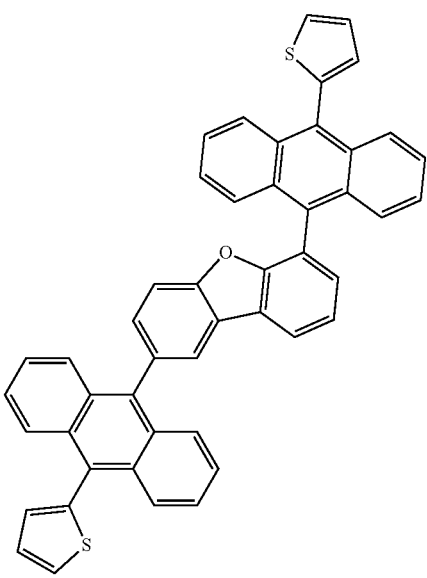
162
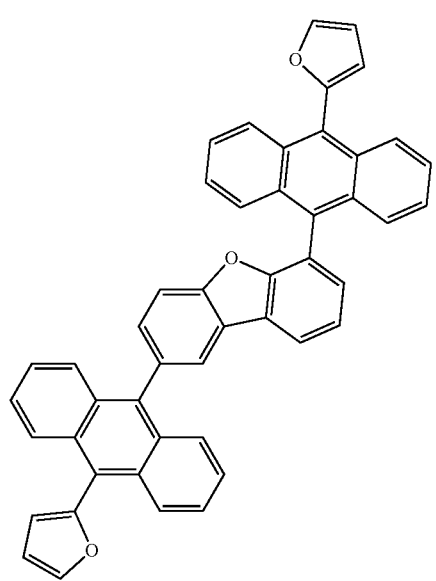
161
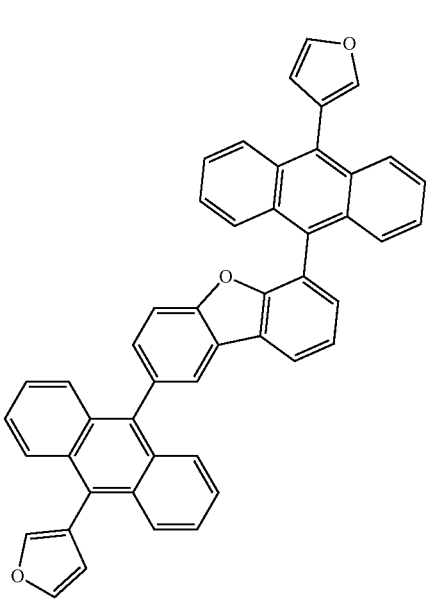
163

1517
-continued
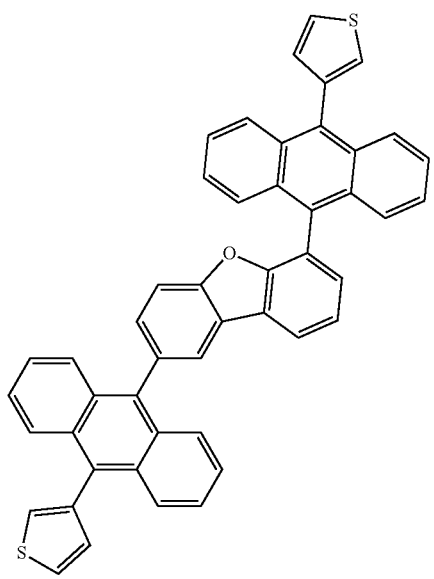
164
1518
-continued
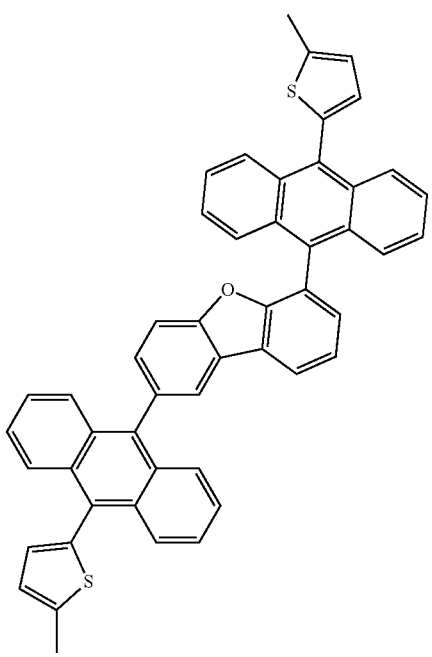
166
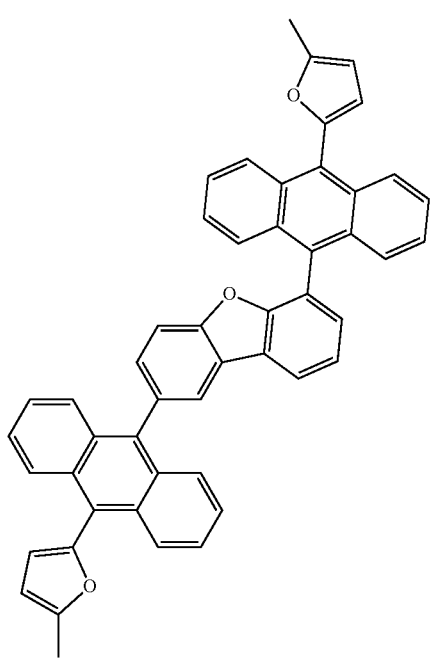
165
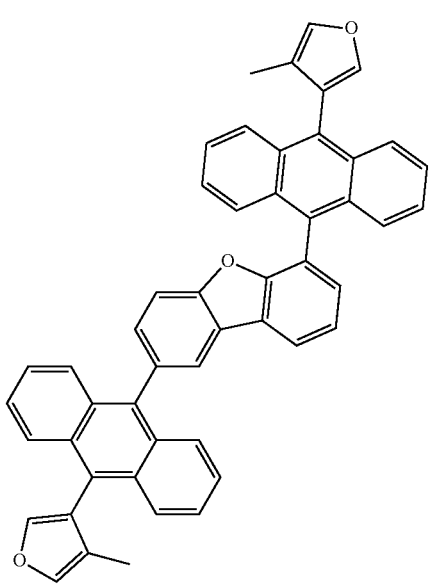
167

1519
-continued
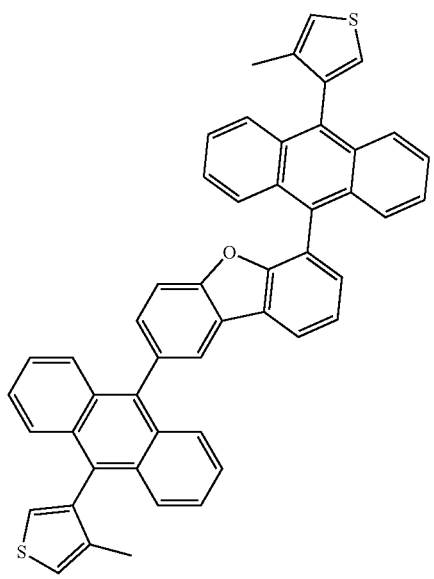
168
1520
-continued
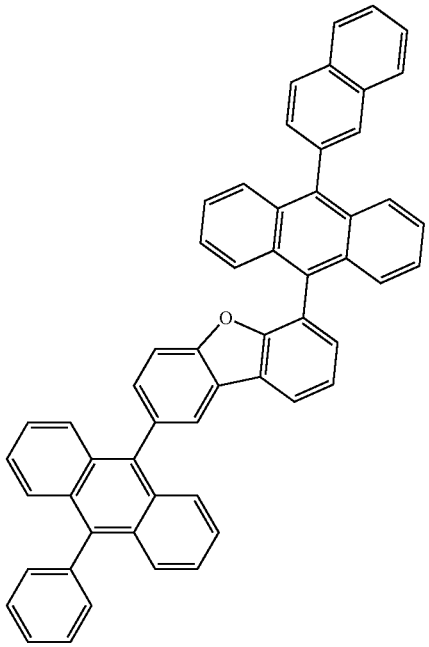
170
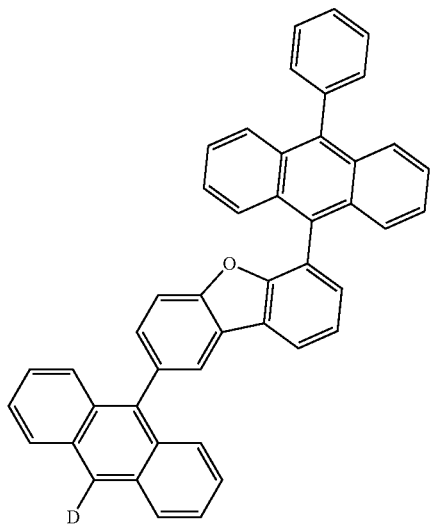
169
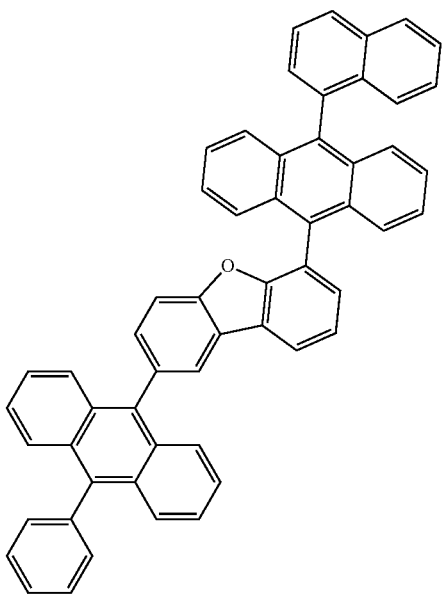
171

1521
-continued
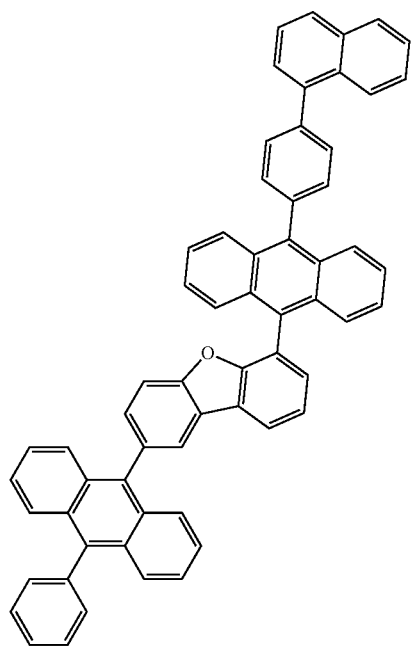
172
1522
-continued
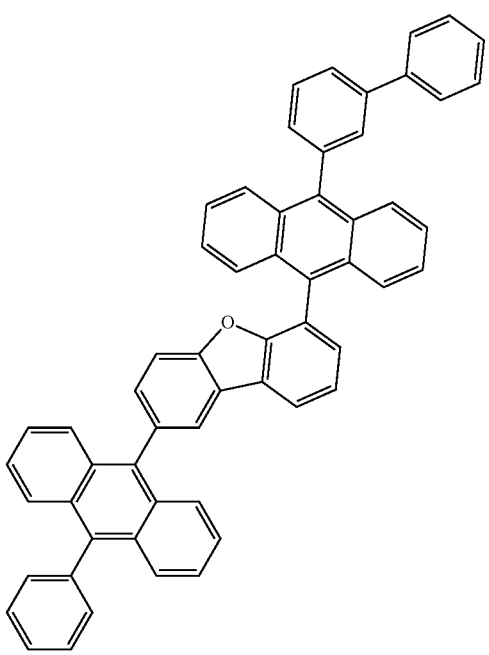
174
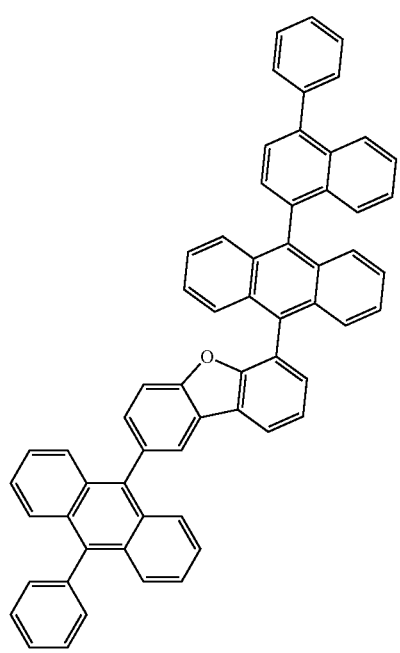
173
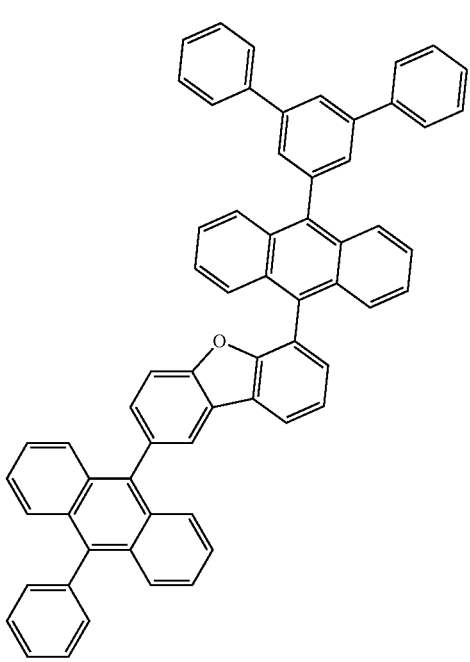
175

1523
-continued
176
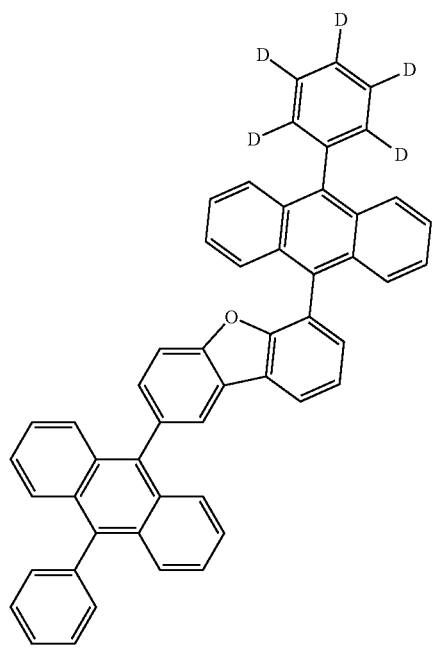
177
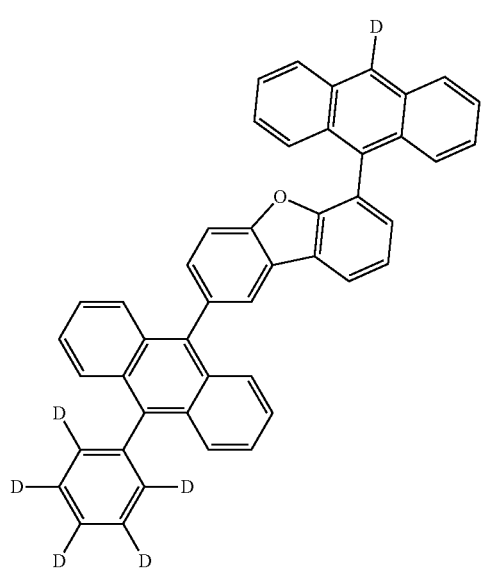
1524
-continued
178
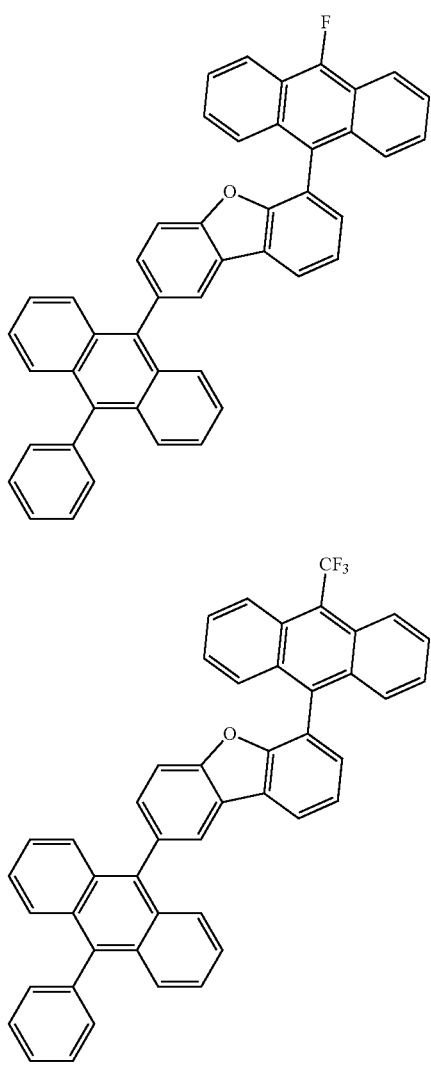
179
180
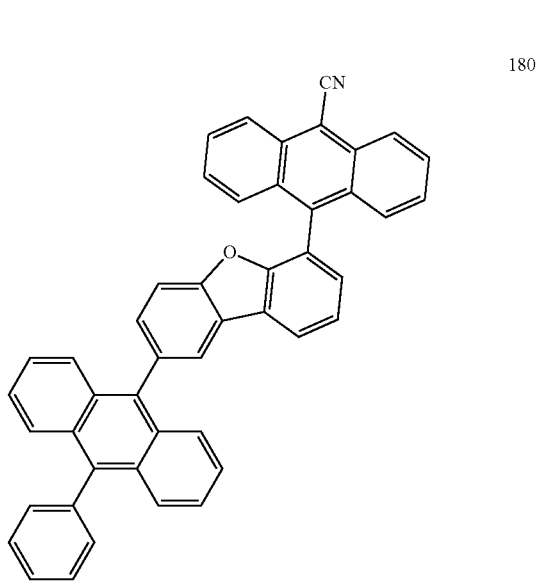

1525
-continued
1526
-continued
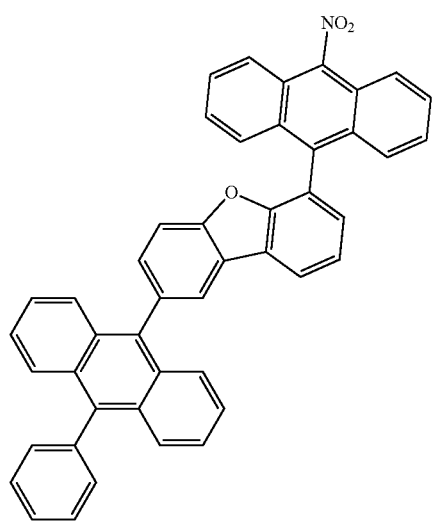
181
183
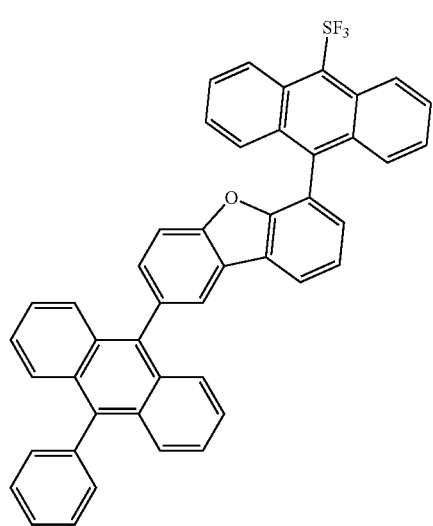
182
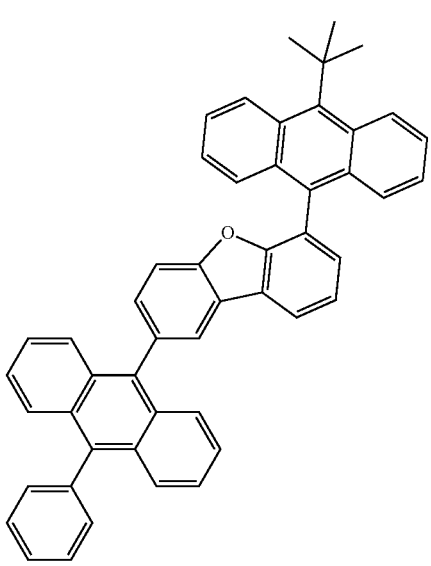
184

1527
-continued
185
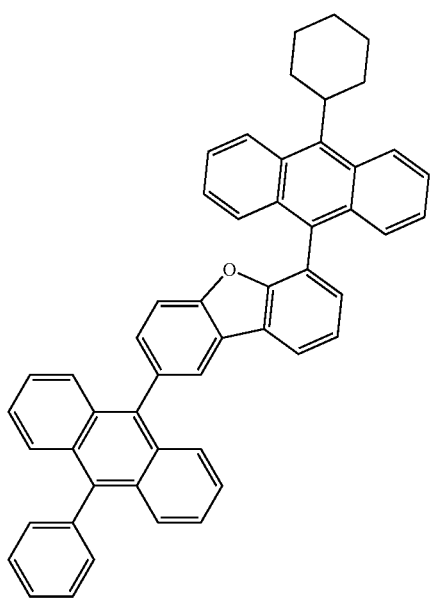
1528
-continued
187
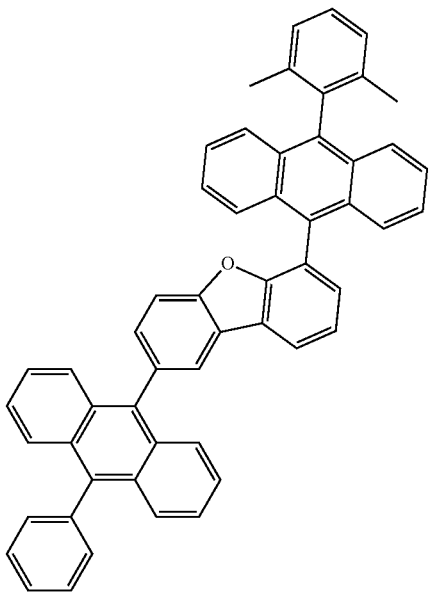
186
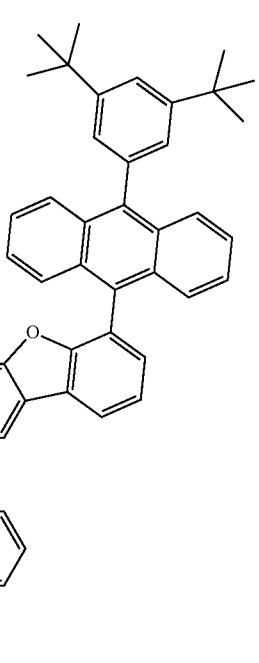
188

1529
-continued
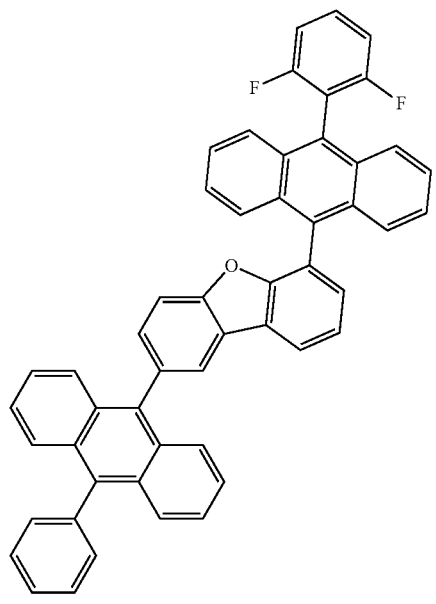
1530
-continued
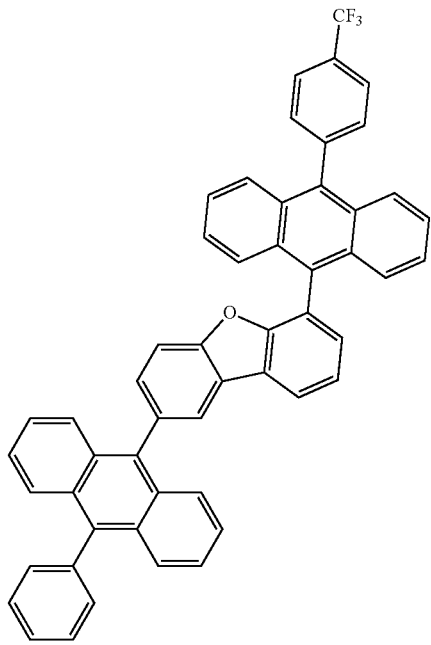
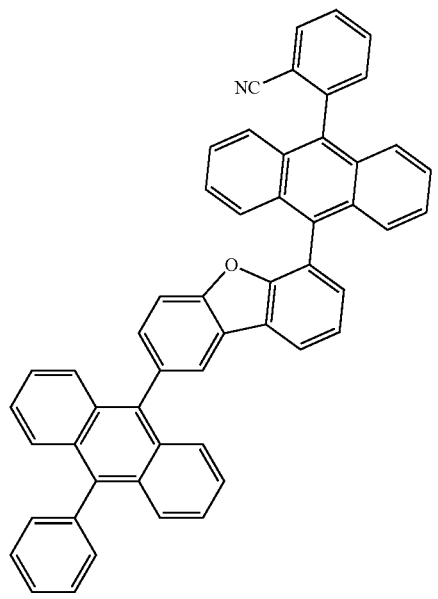
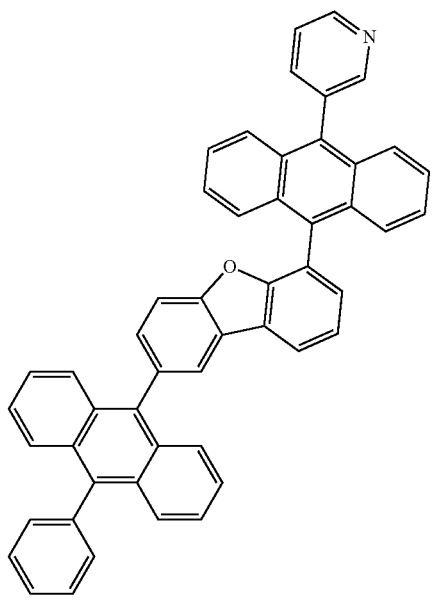

1531
-continued
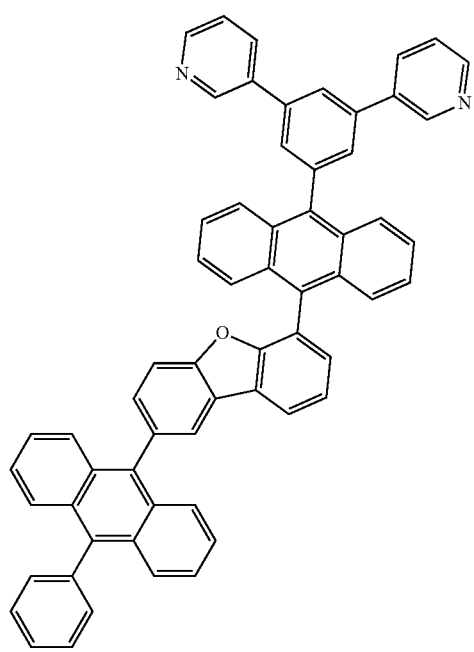
193
1532
-continued
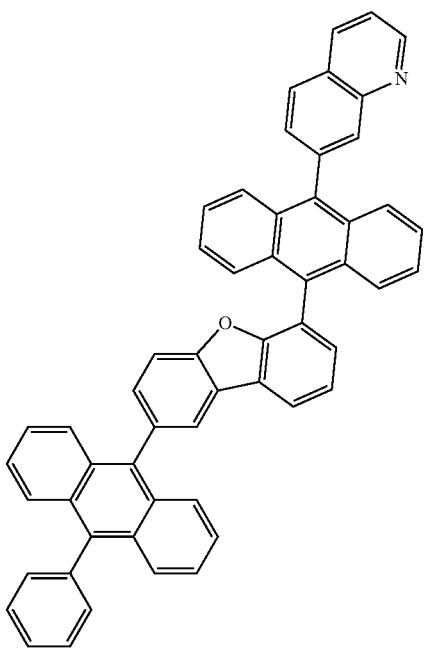
195
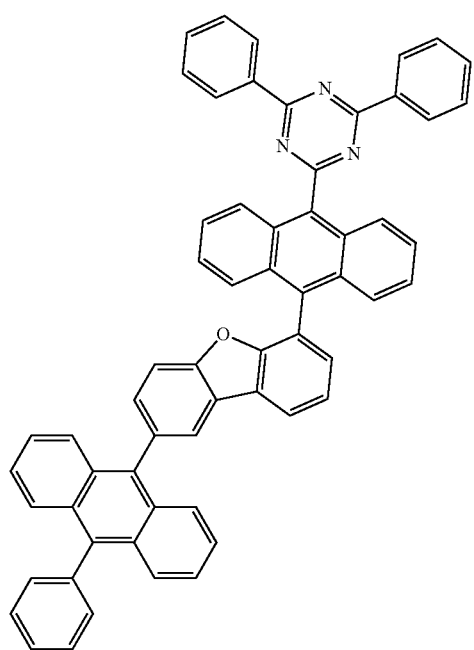
194
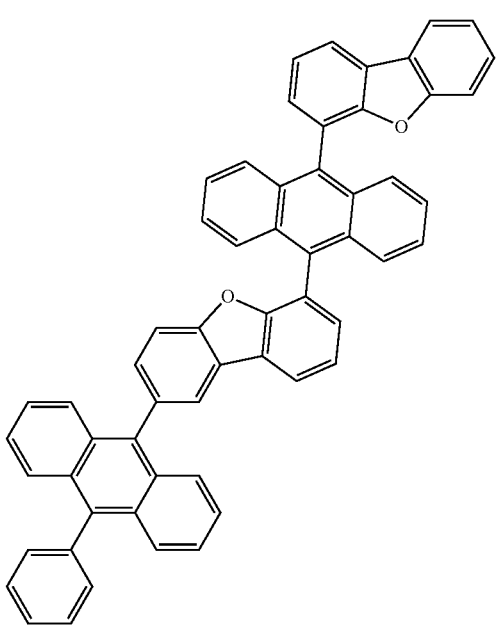
196

1533
-continued
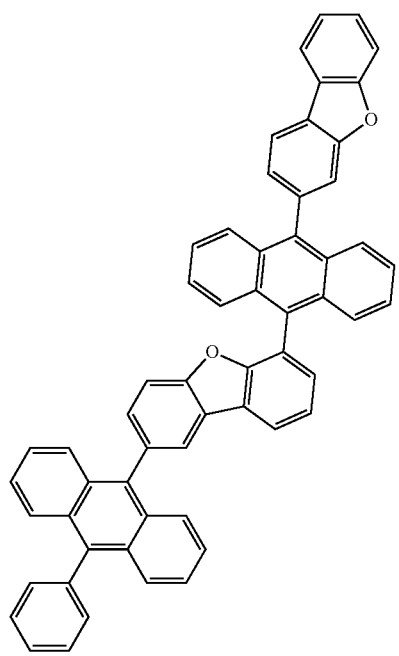
197
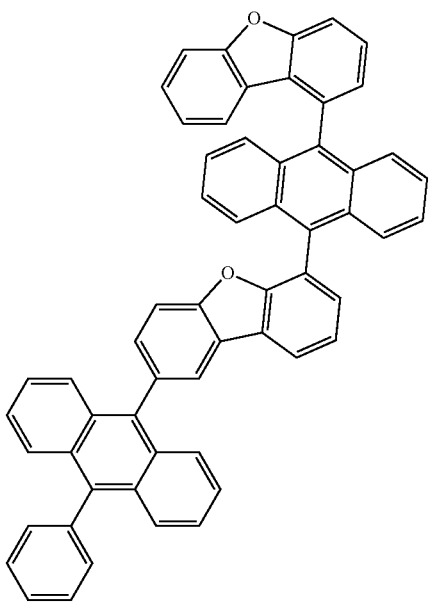
199
1534
-continued
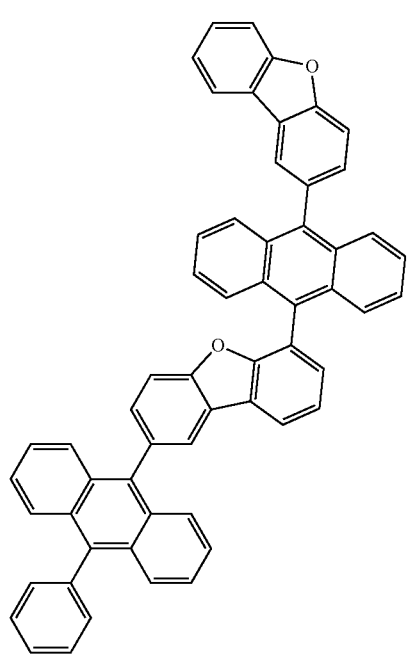
198
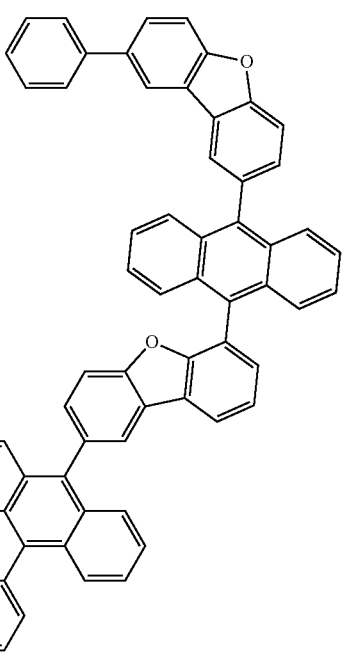
200

1535                      1536
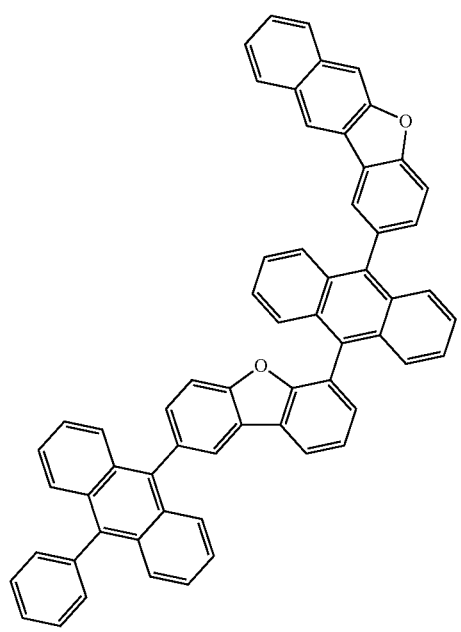
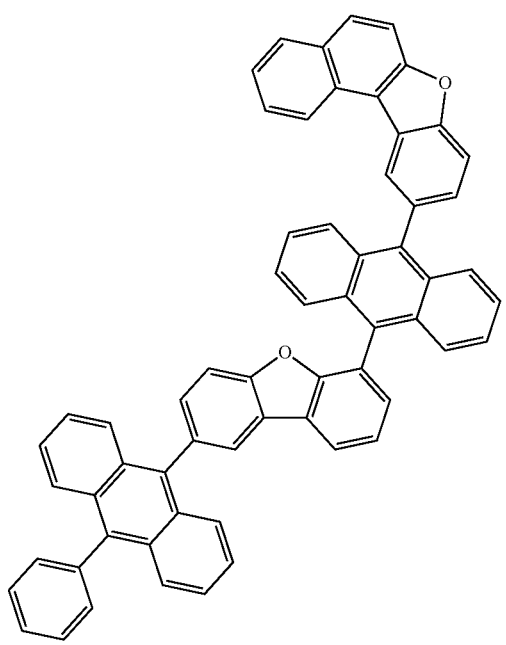
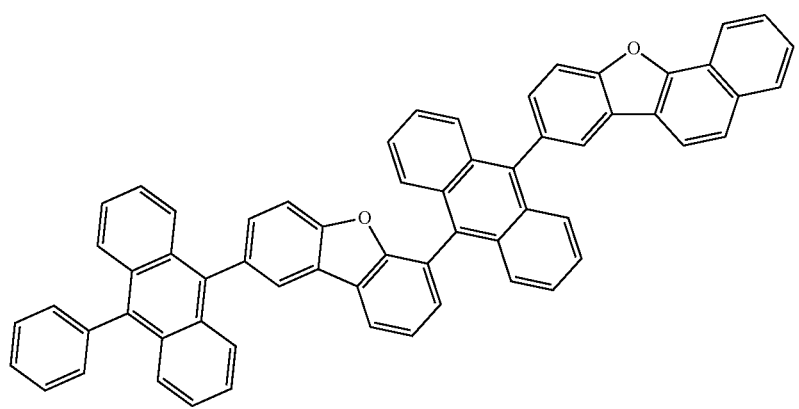

-continued
204
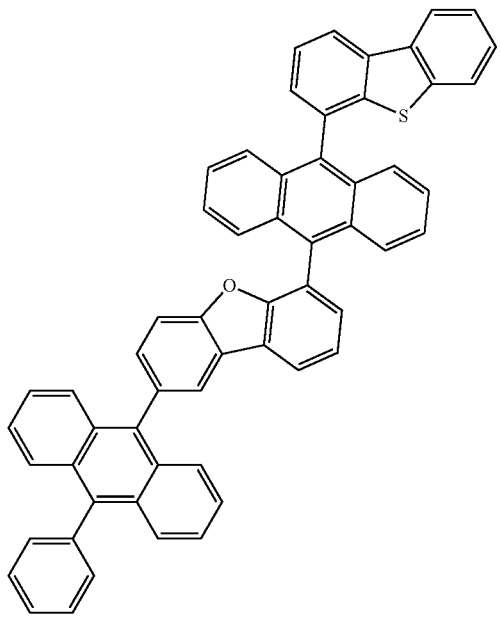
205
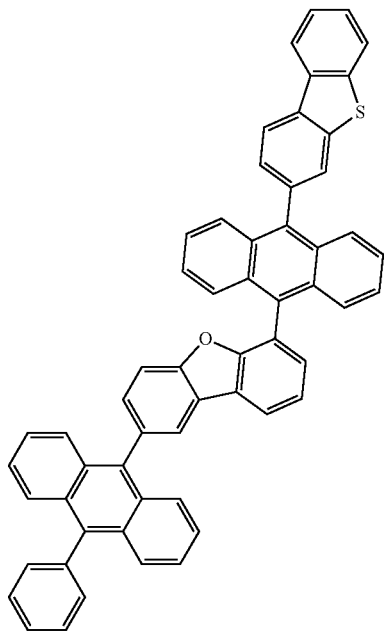
206
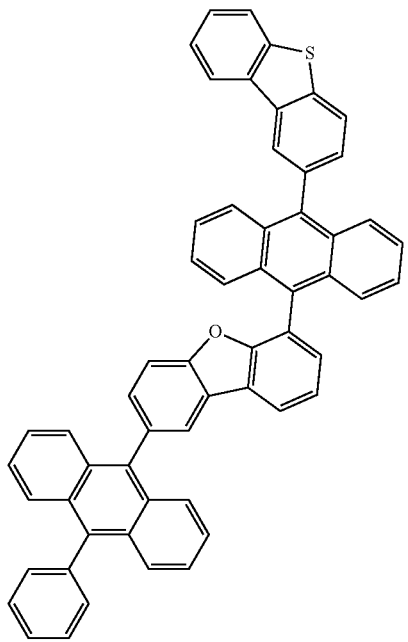
207
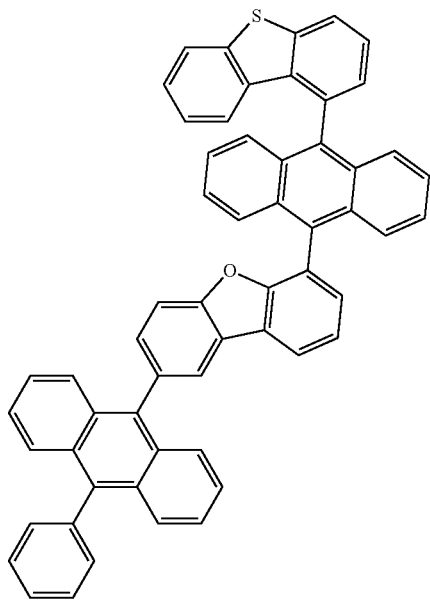

1539
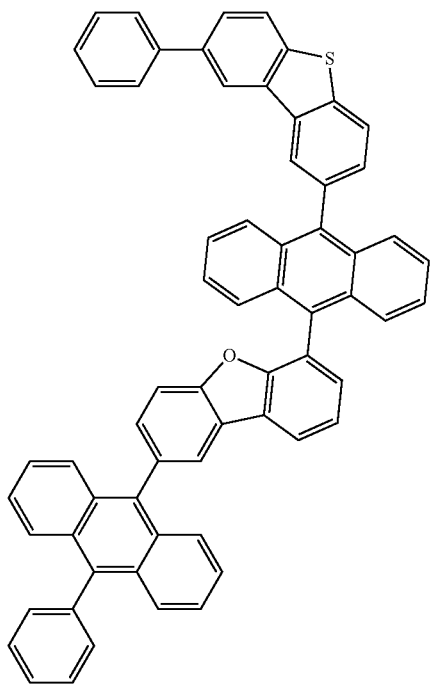
208
1540
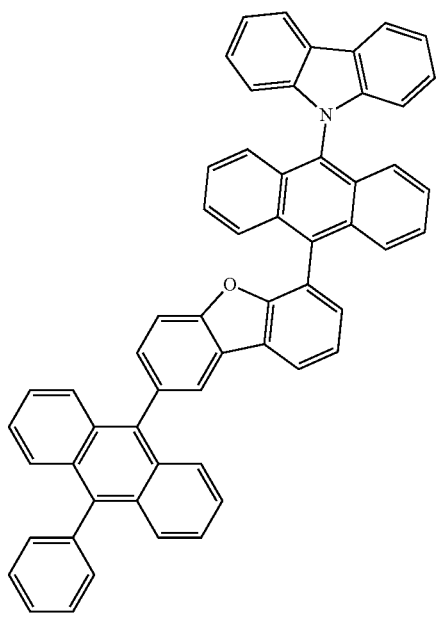
209
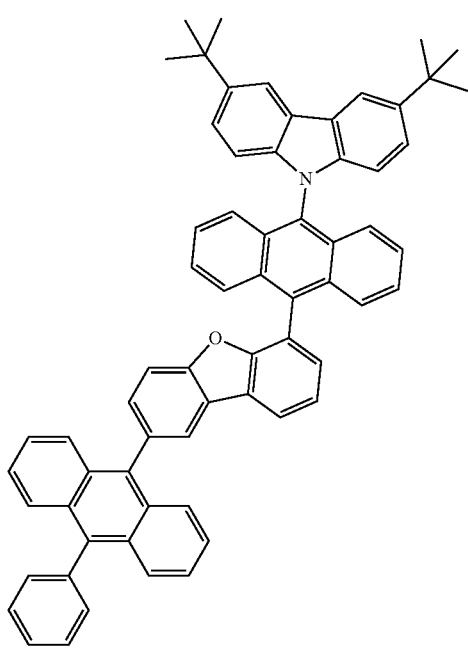
210
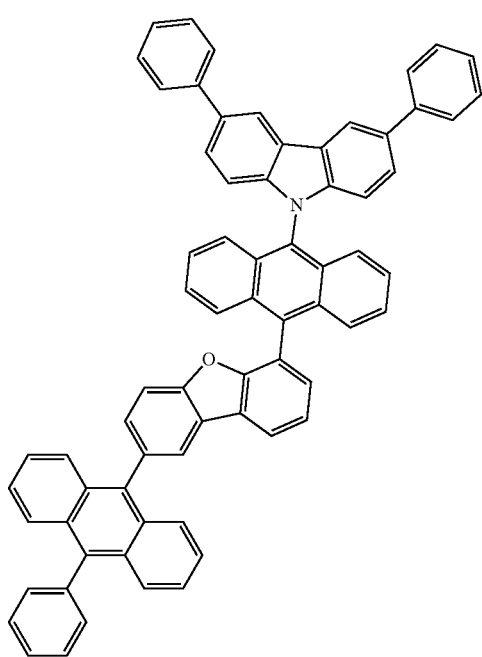
211

1541
-continued
212
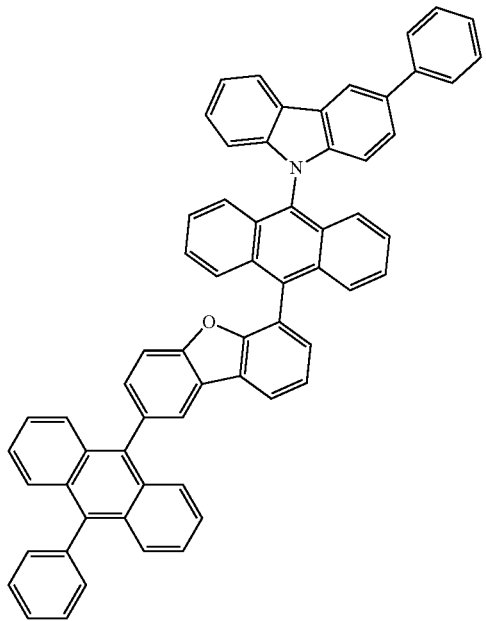
1542
213
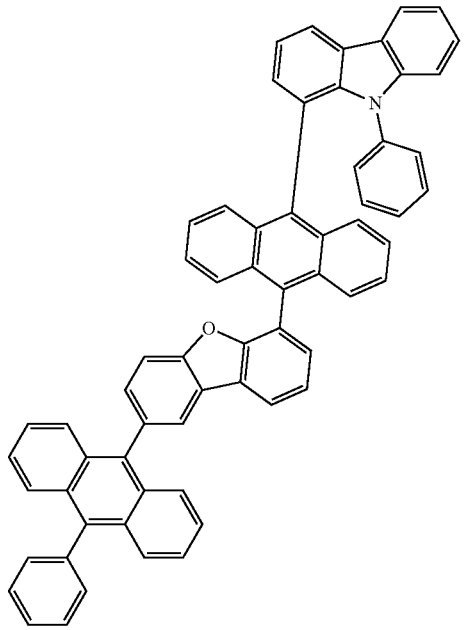
214
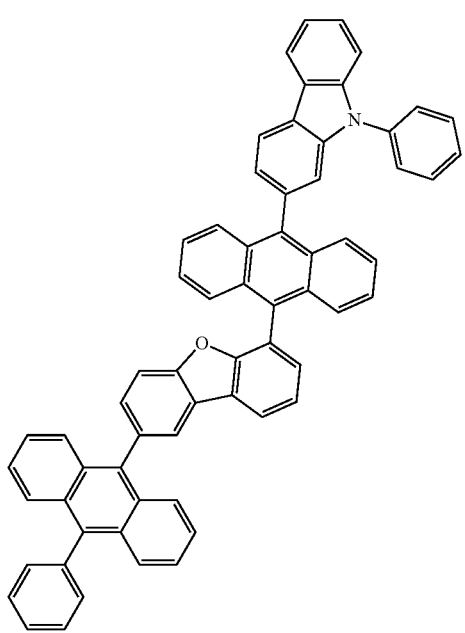
215
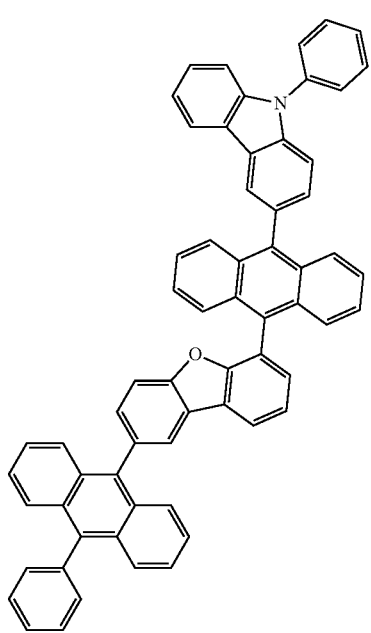

216
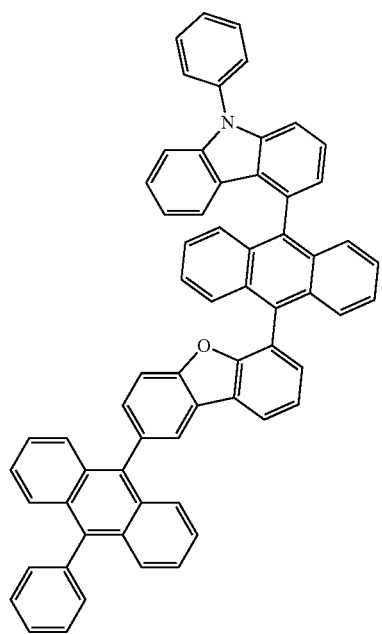
217
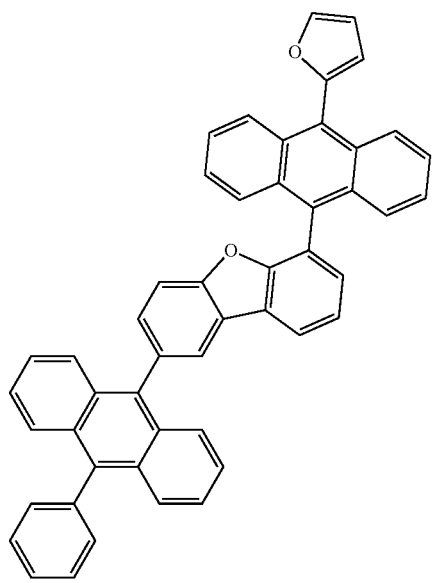
218
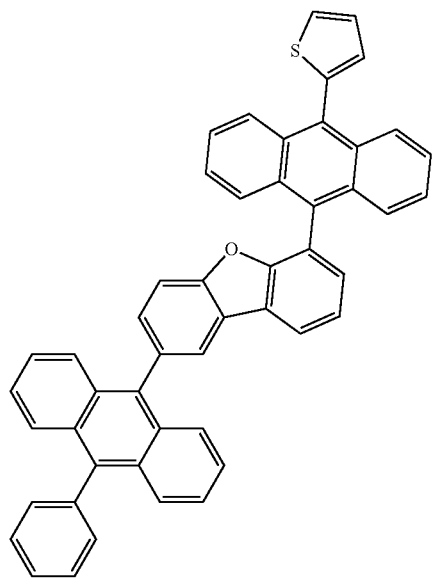
219
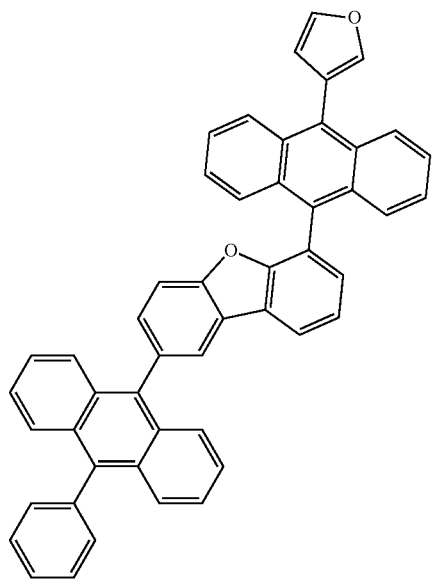

-continued
220
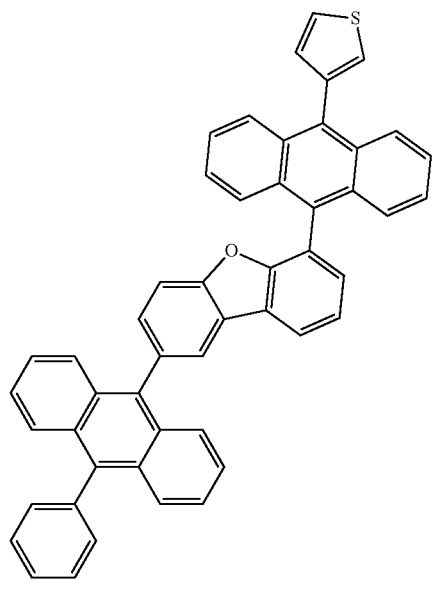
221
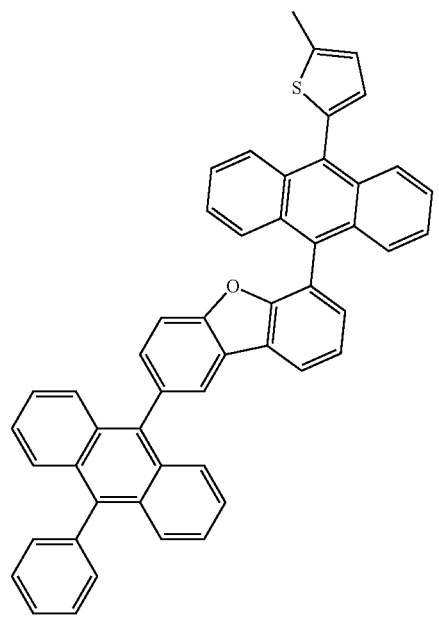
222
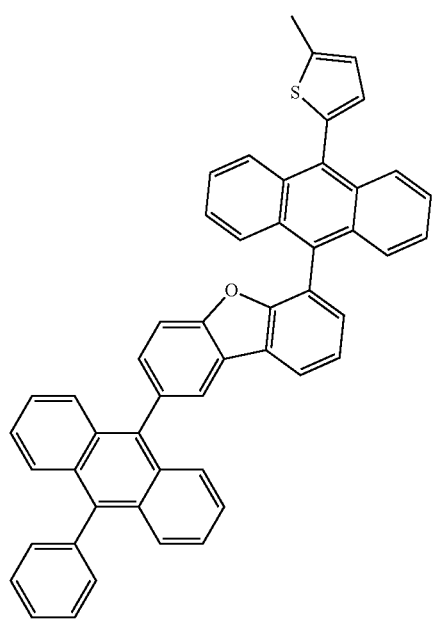
223
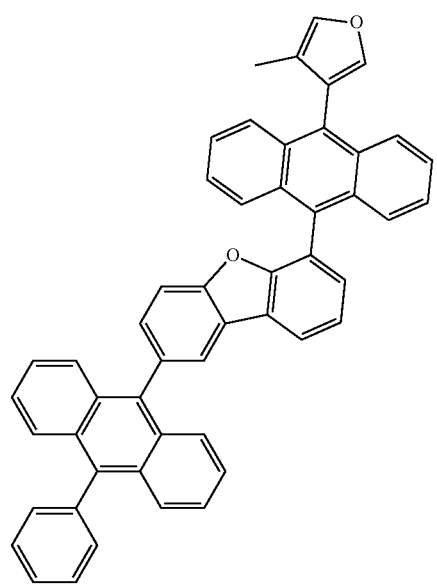

-continued
224
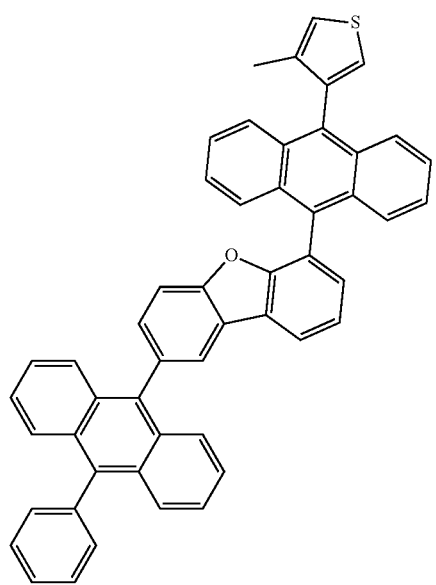
225
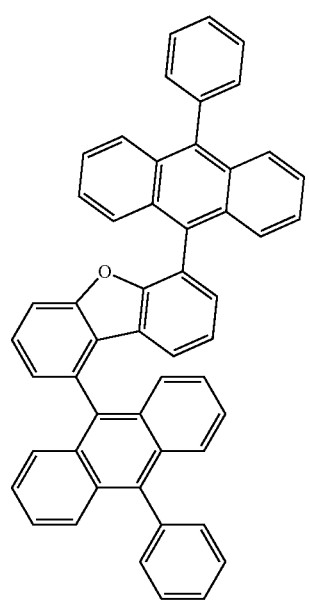
226
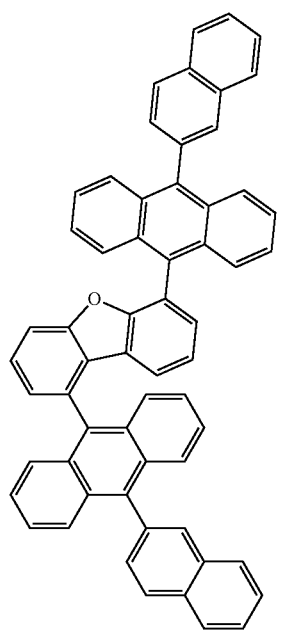
227
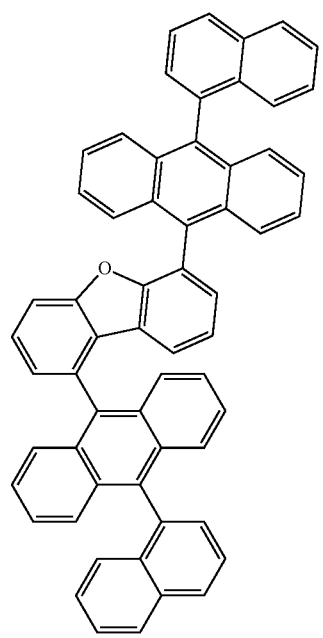

1549
-continued
228
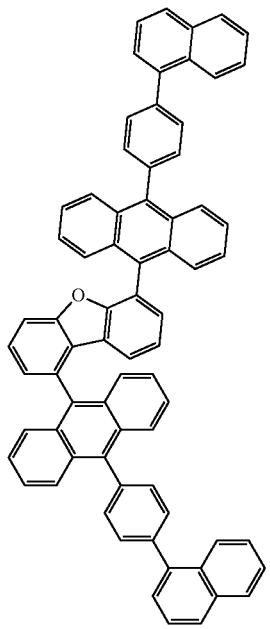
229
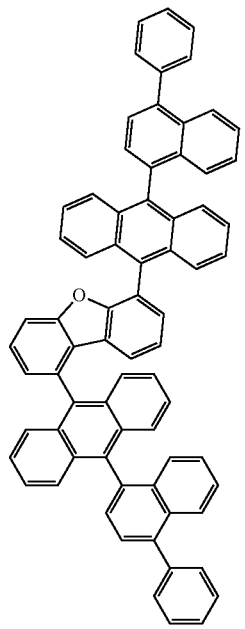
230
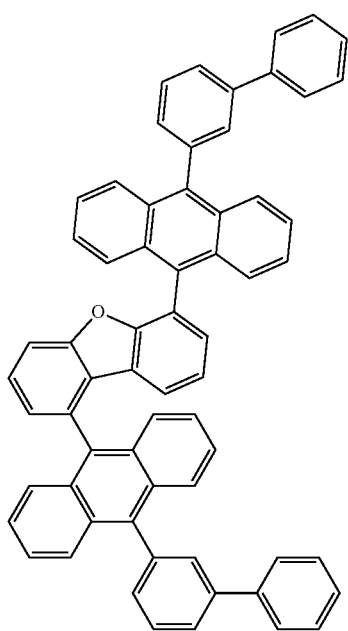
231
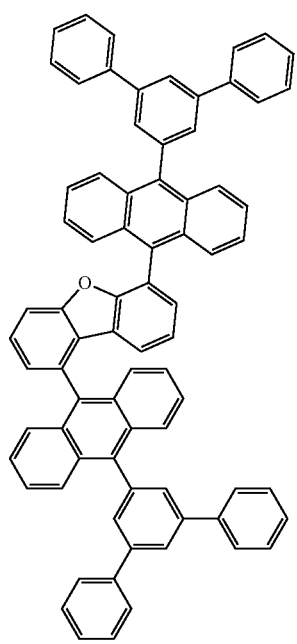

-continued
232
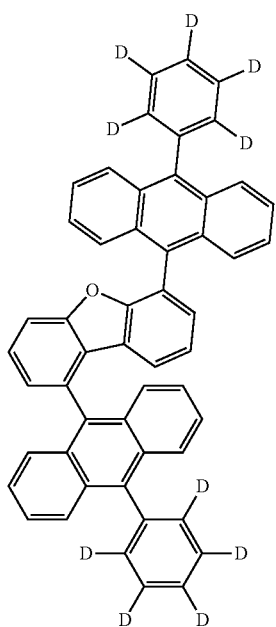
233
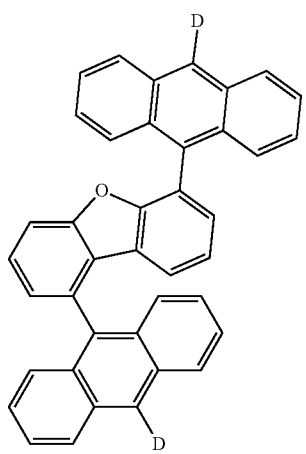
234
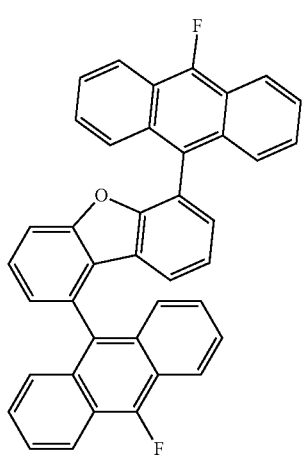
235
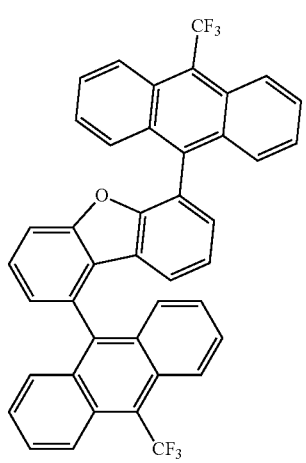
236
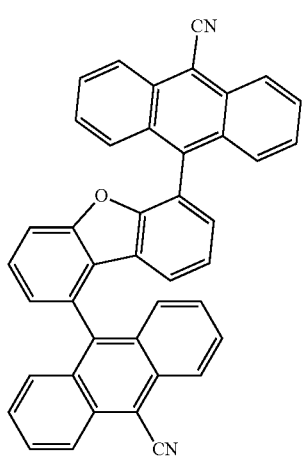
237
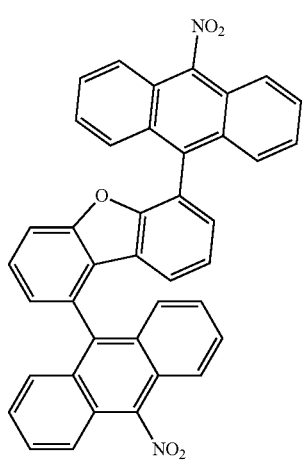

-continued
1553
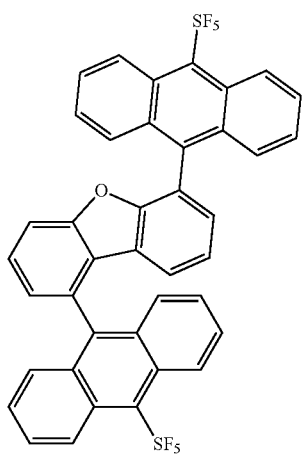
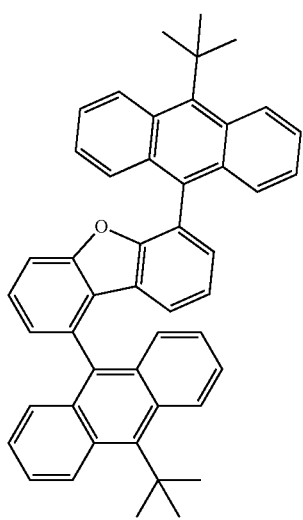
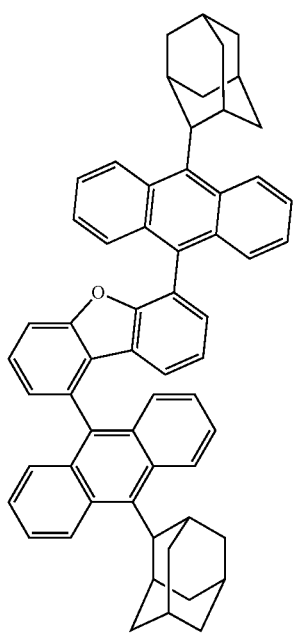
1554
238
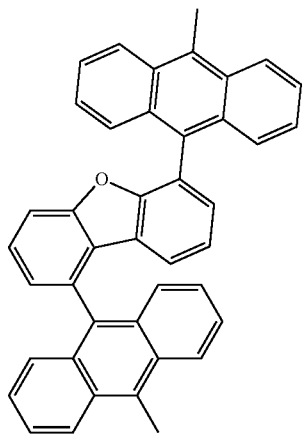
239
240
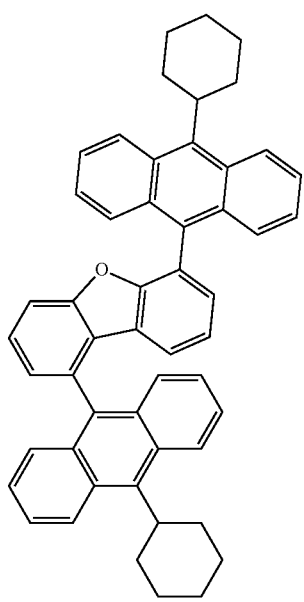
241
242
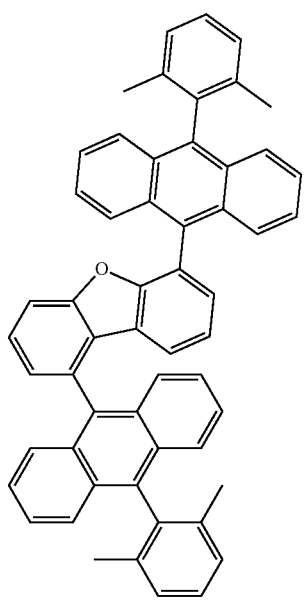
243

-continued
1555
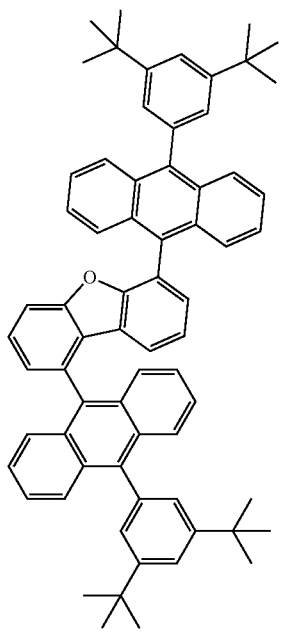
244
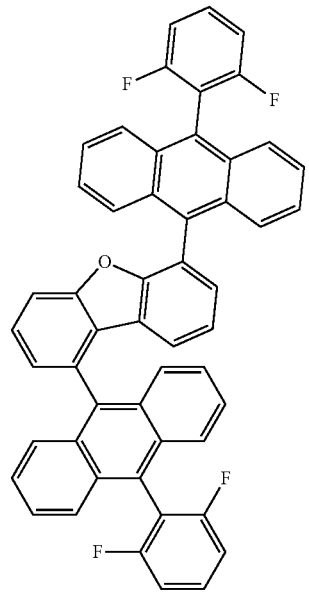
245
1556
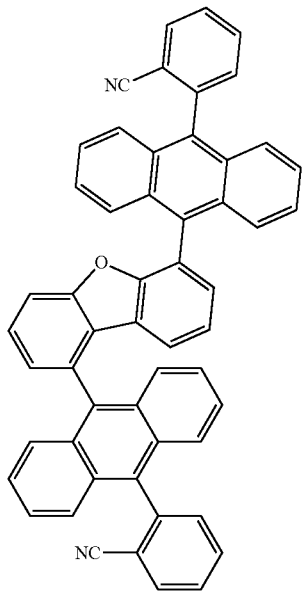
246
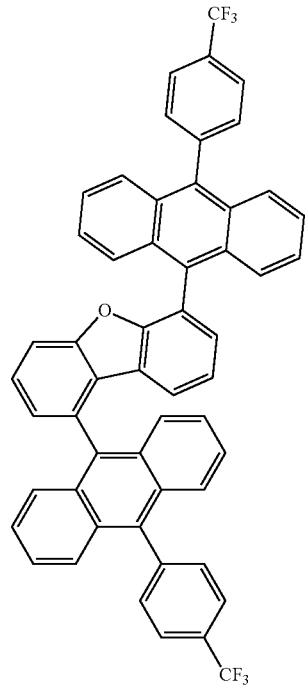
247

-continued
248
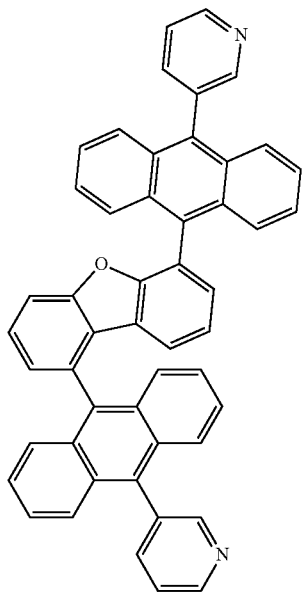
249
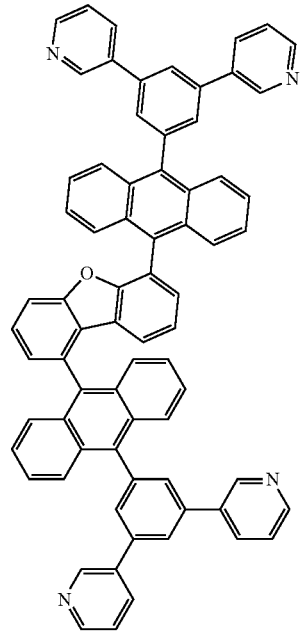
250
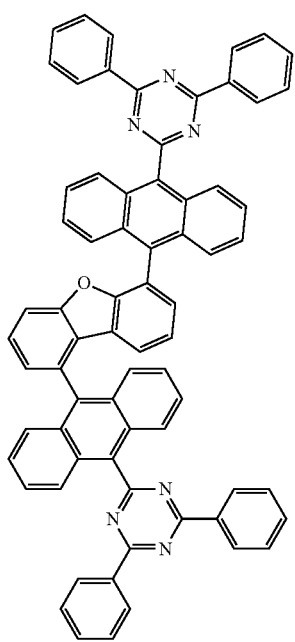
251
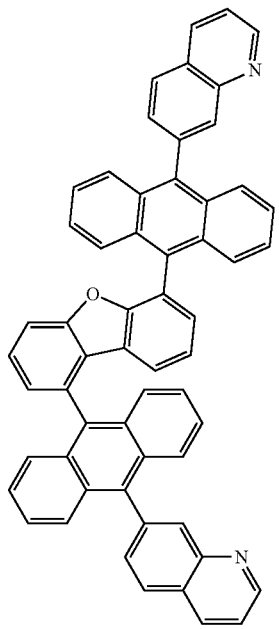

-continued
252
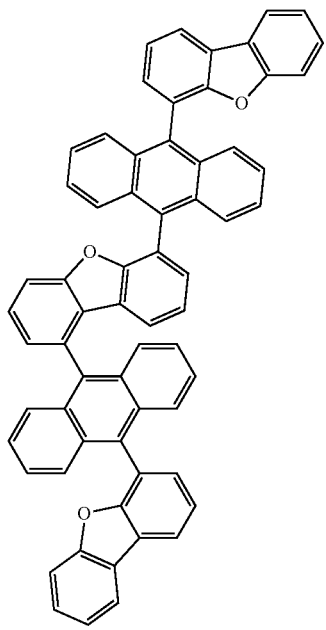
253
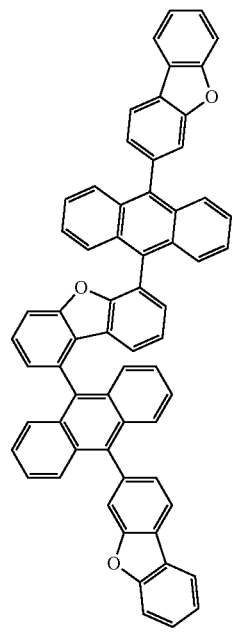
254
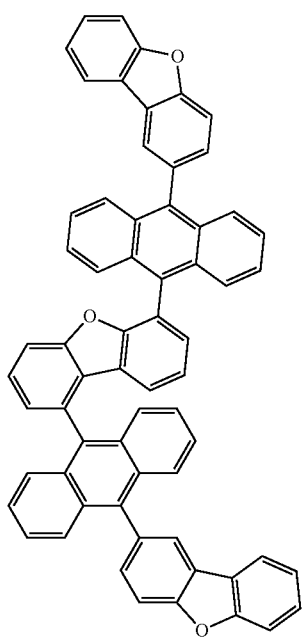
255
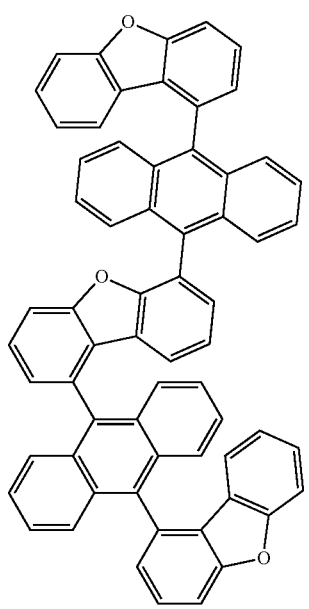

1561                                    1562
-continued
256                                    257
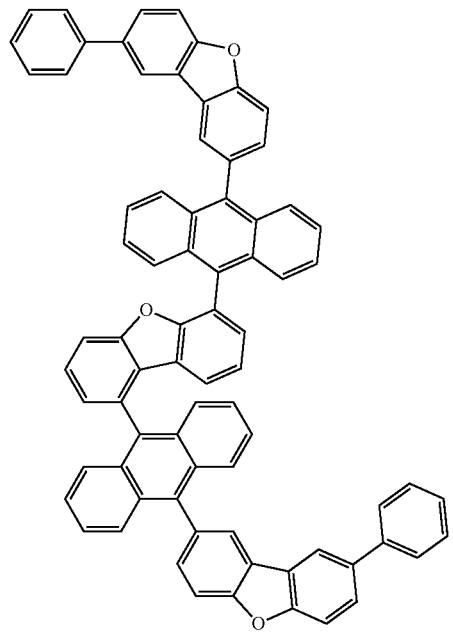
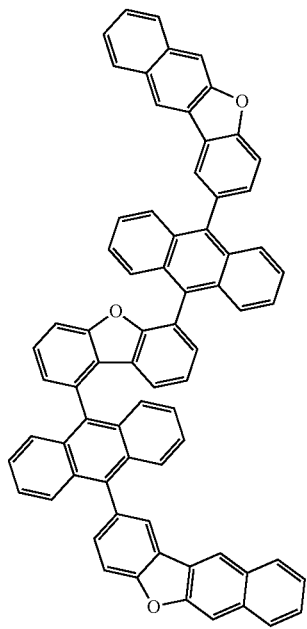
258                                    259
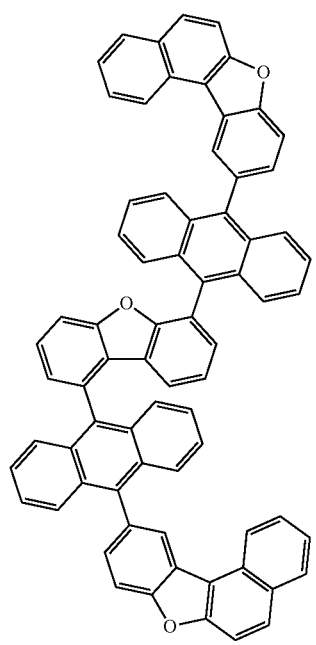
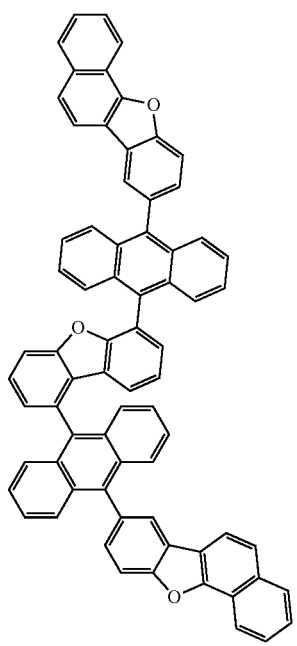

1563 1564
-continued
260 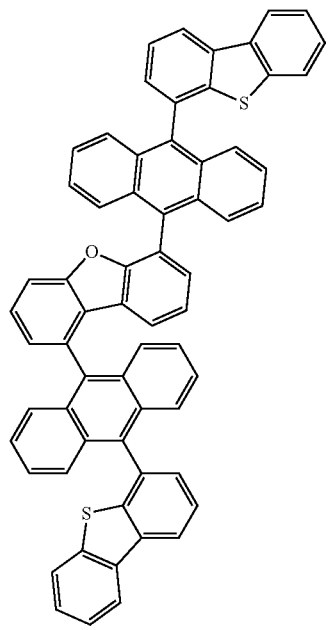 261 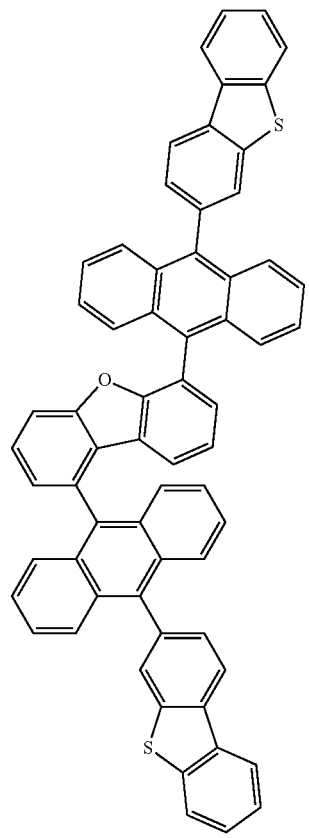
262 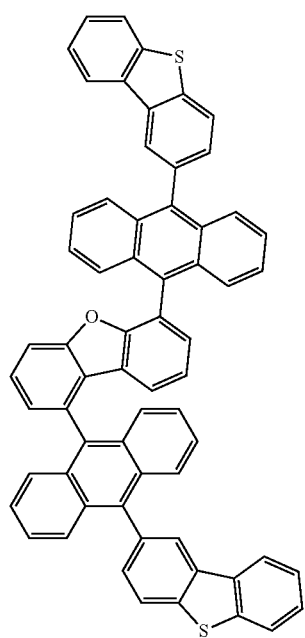 263 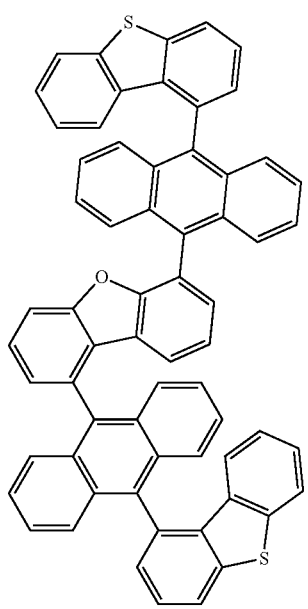

1565
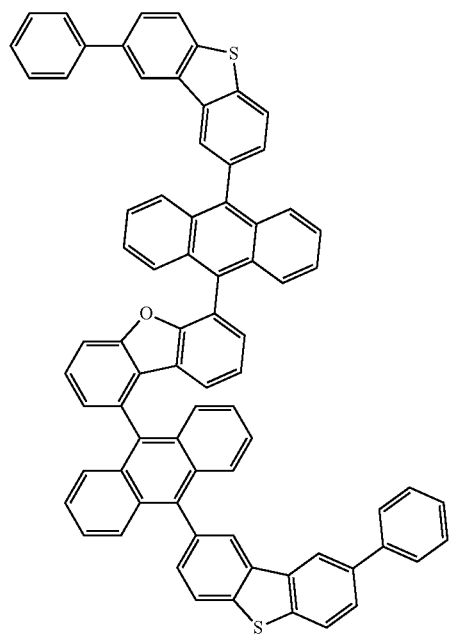
264
1566
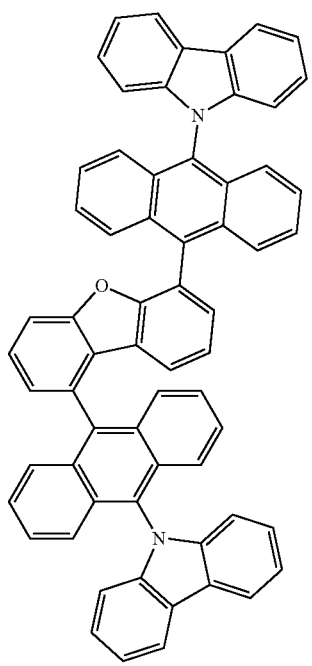
265
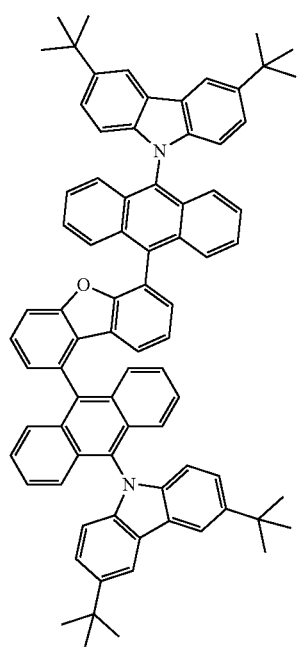
266
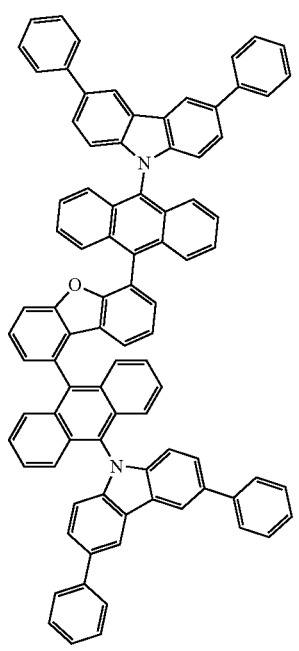
267

268
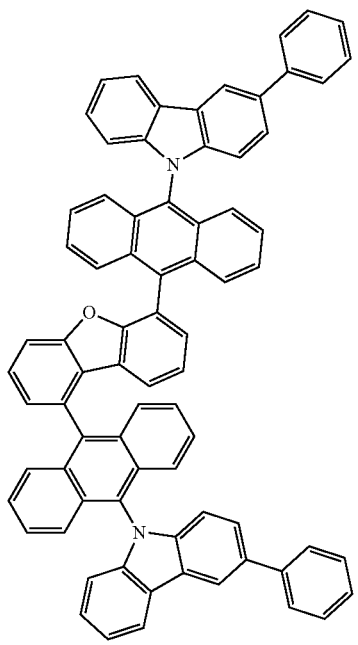
269
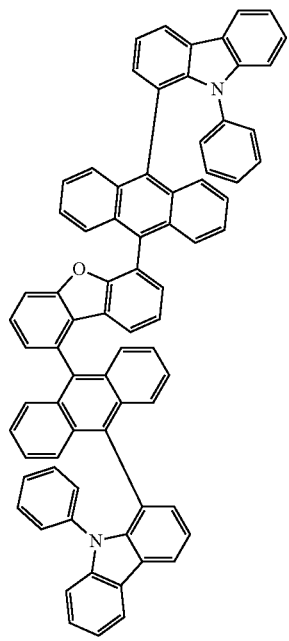
270
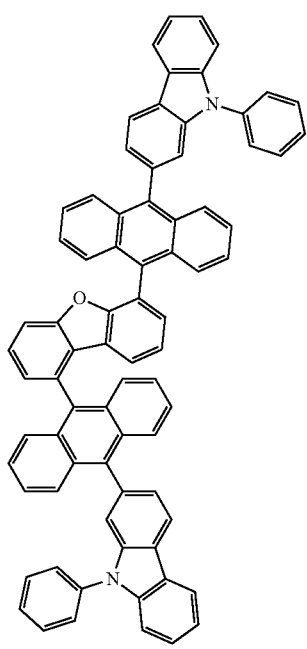
271
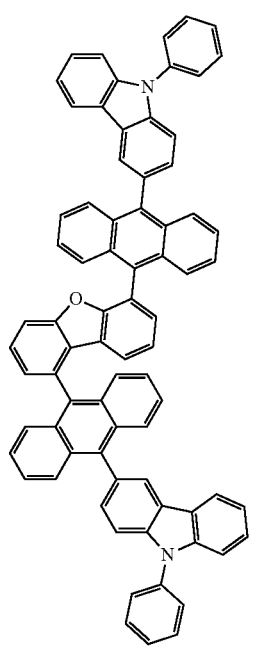

-continued
272 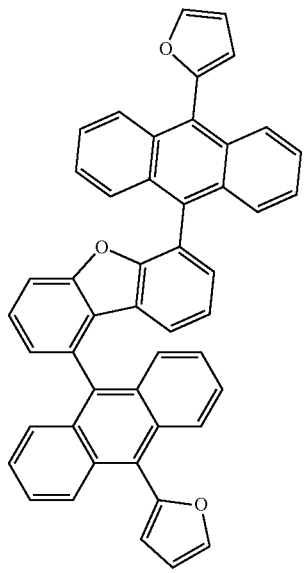
273 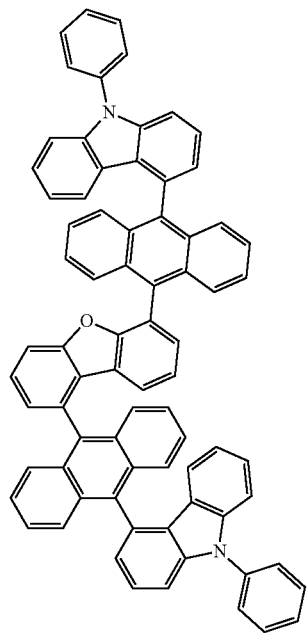
274 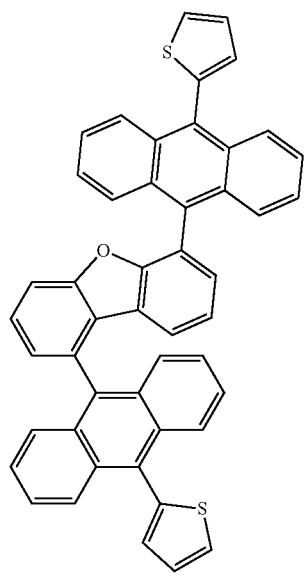
275 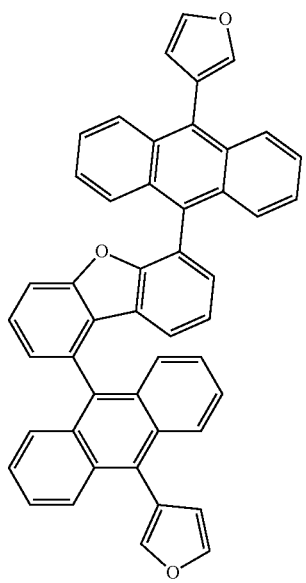

1571
276
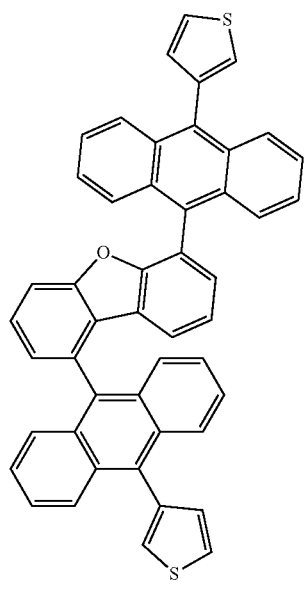
1572
277
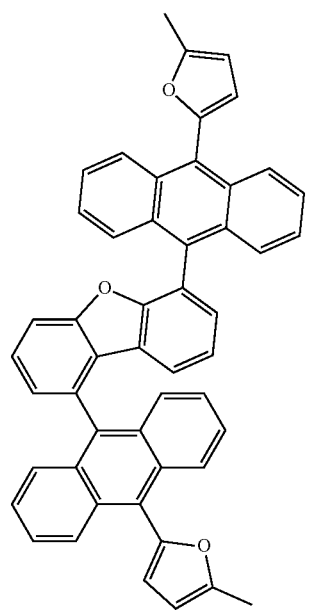
278
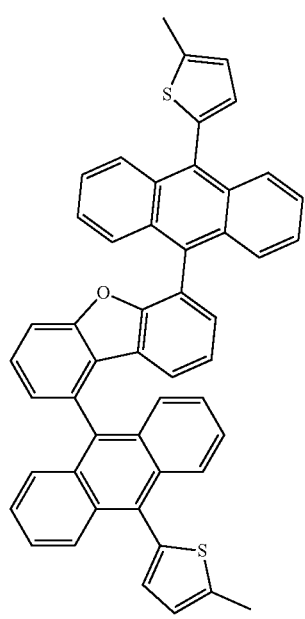
279
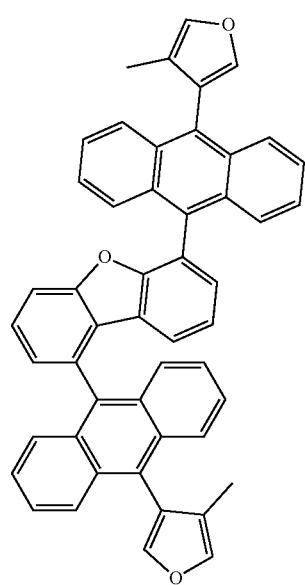

-continued
280
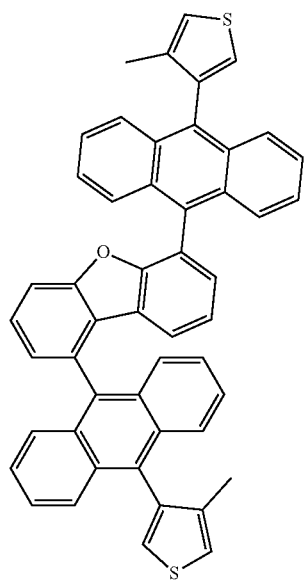
281
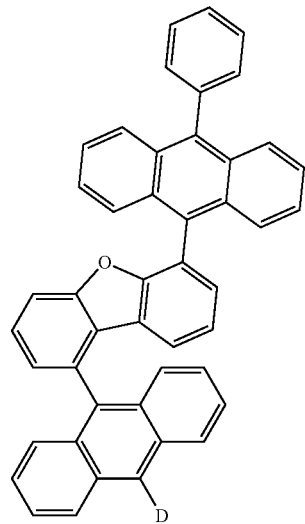
282
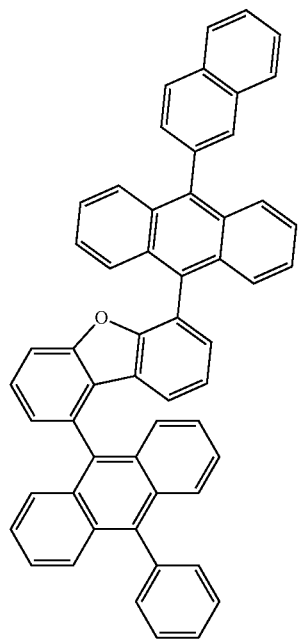
283
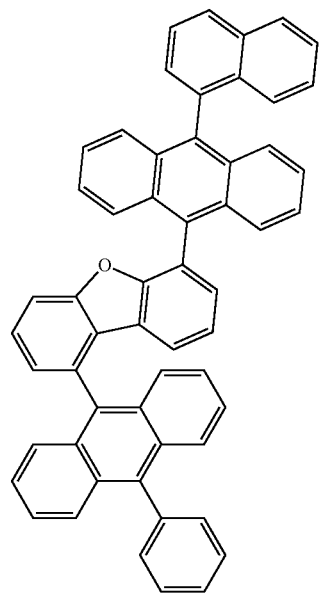

-continued
284
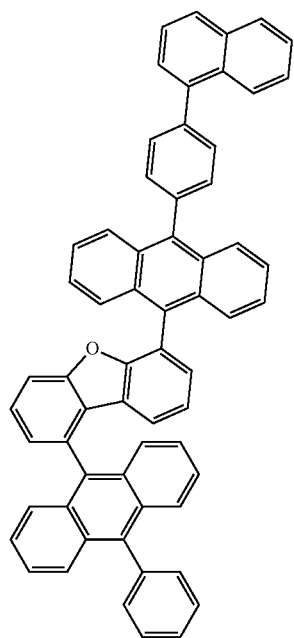
285
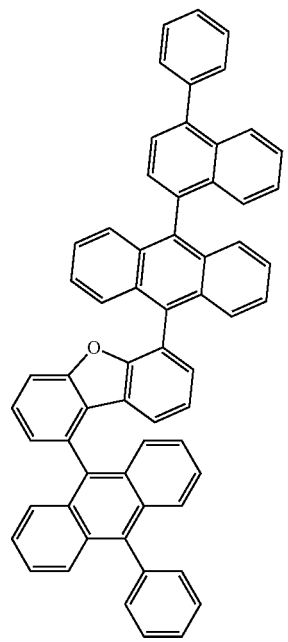
286
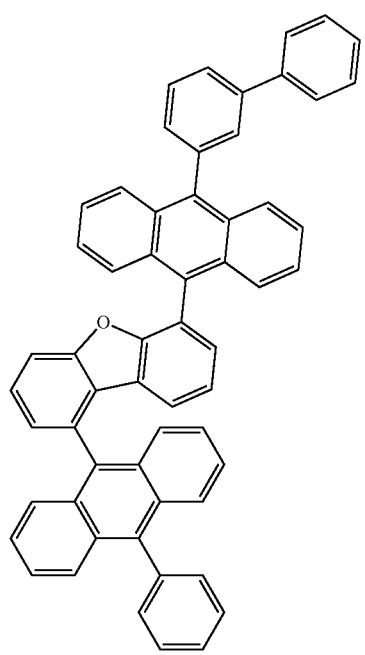
287
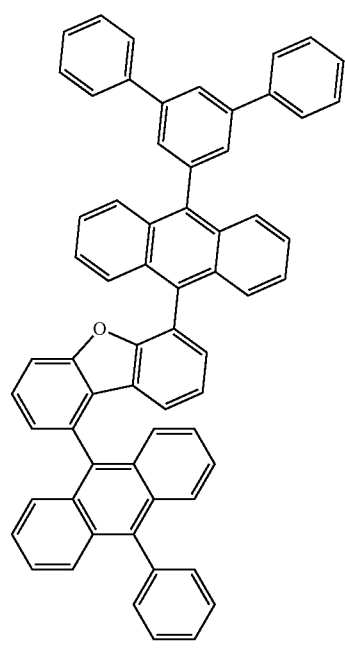

288
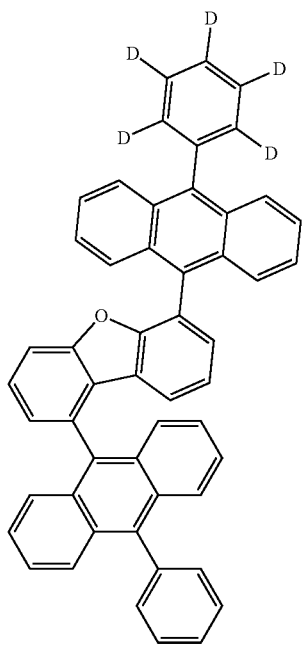
289
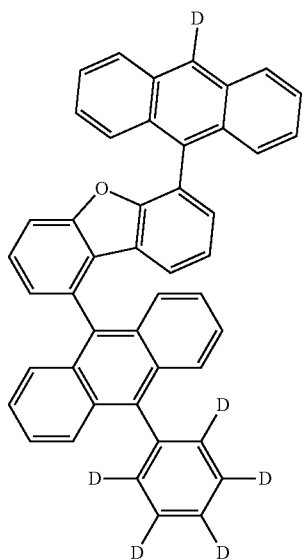
290
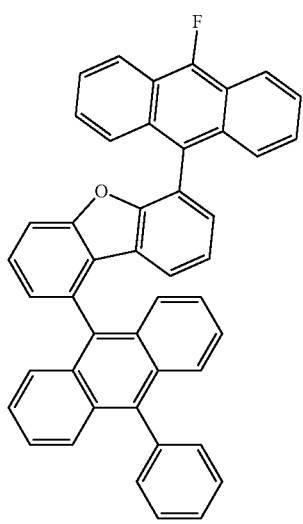
291
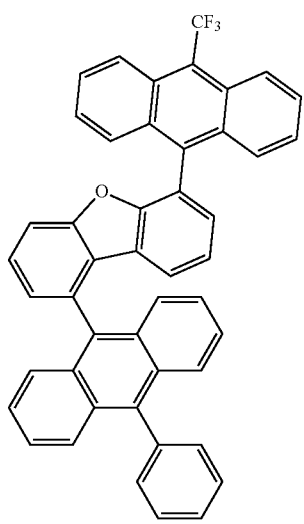
292
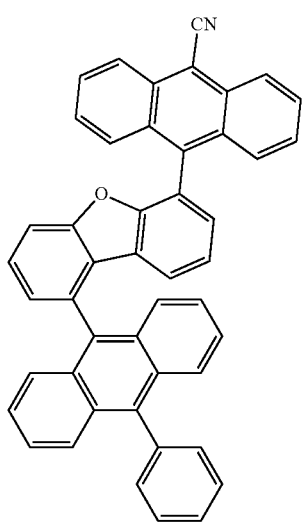
293
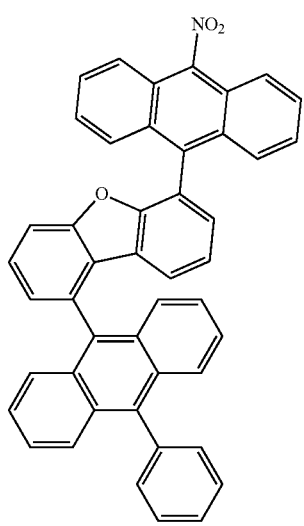

-continued
294
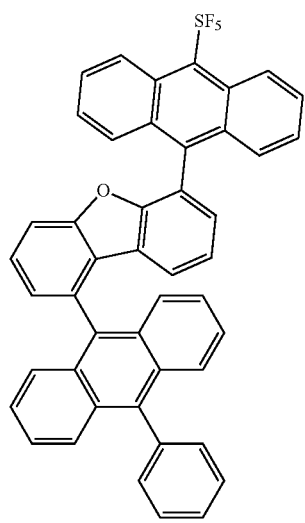
295
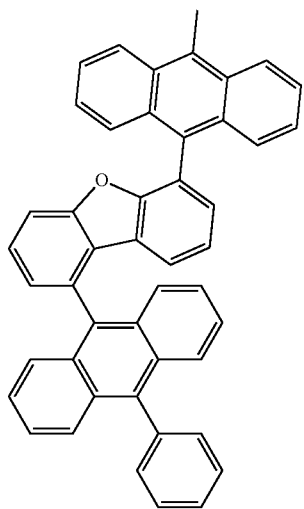
296
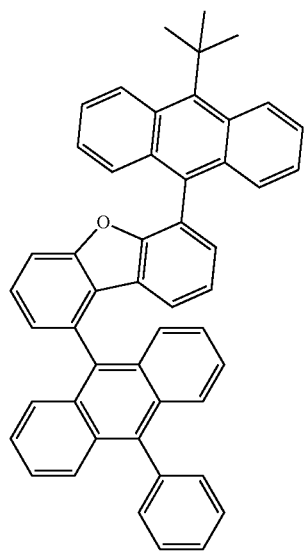
297
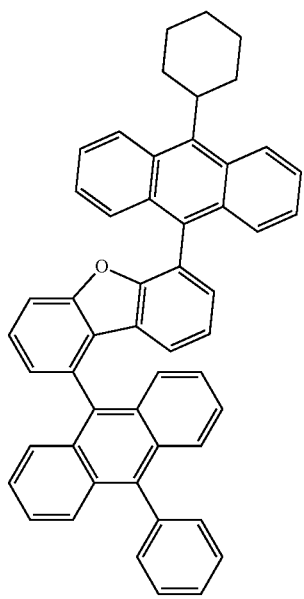

1581
-continued
298
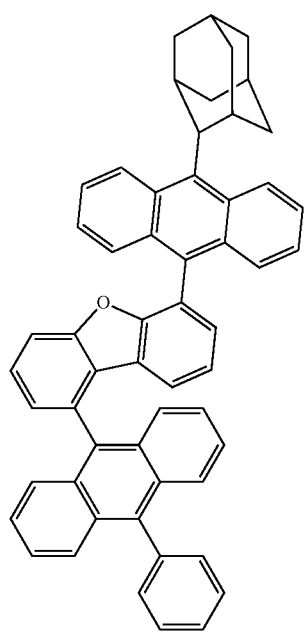
1582
299
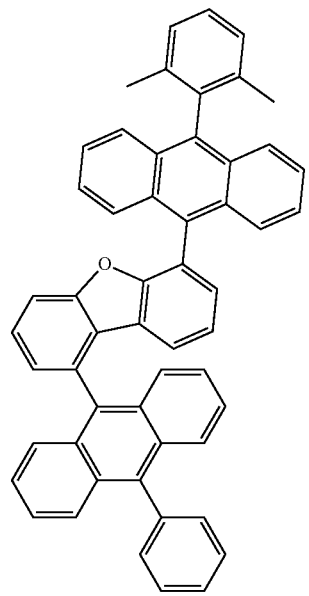
300
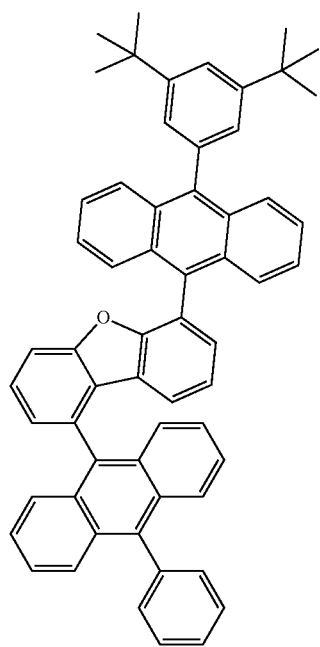
301
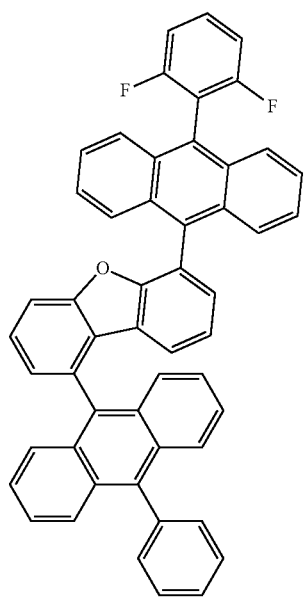

-continued
302
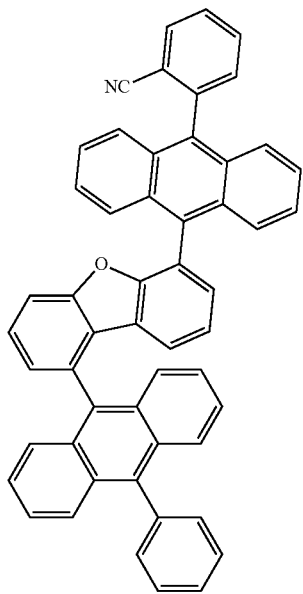
303
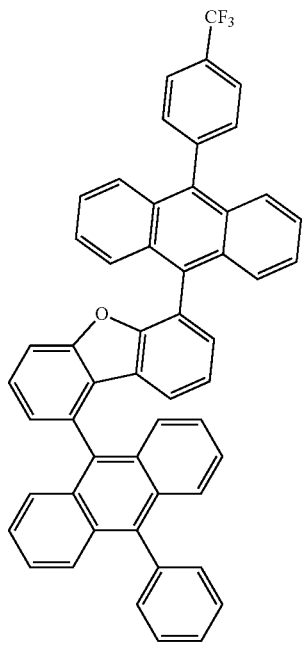
304
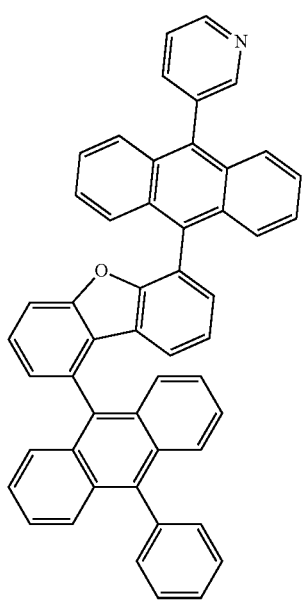
305
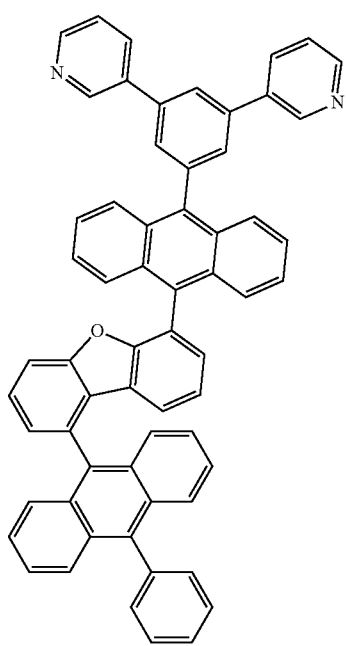

1585
-continued
306
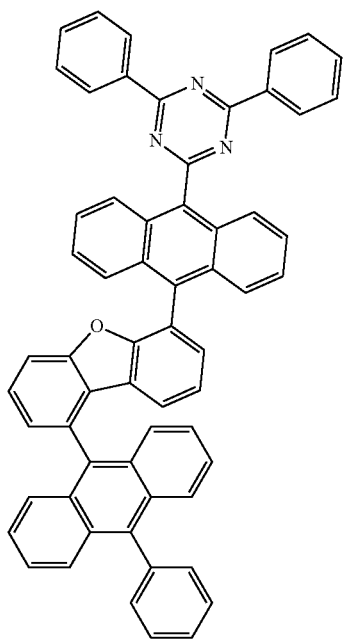
1586
307
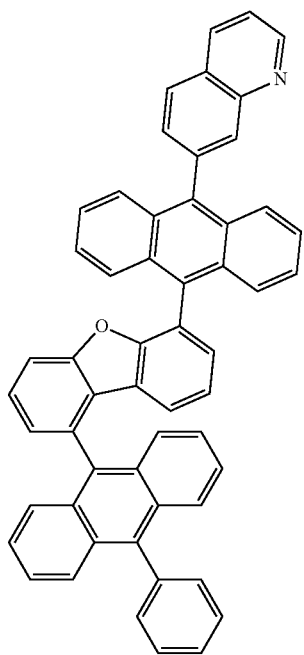
308
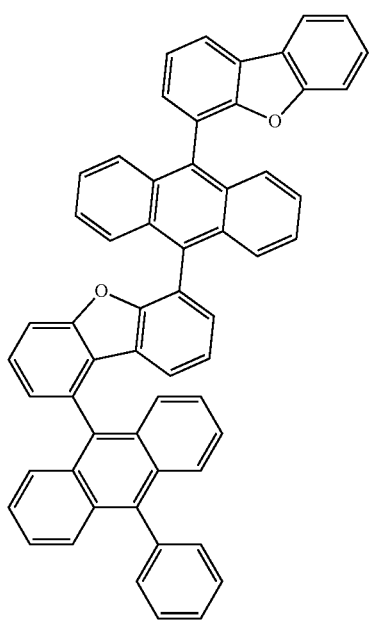
309
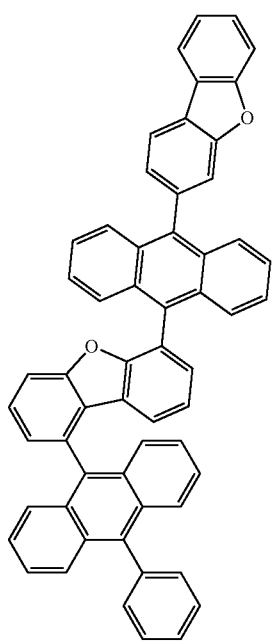

-continued
1587
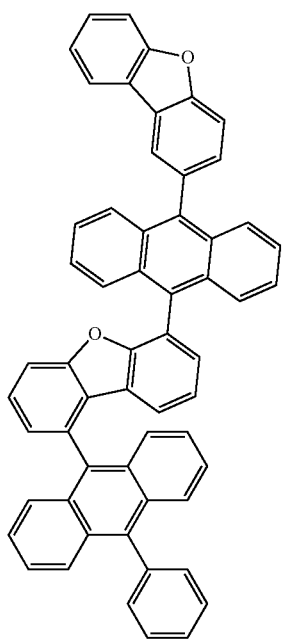
310
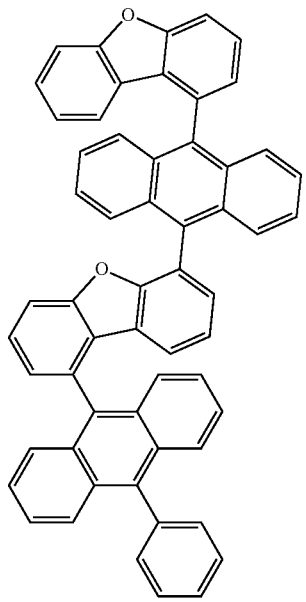
311
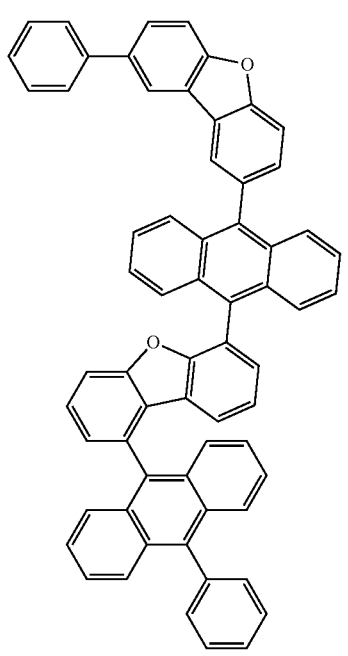
312
1588
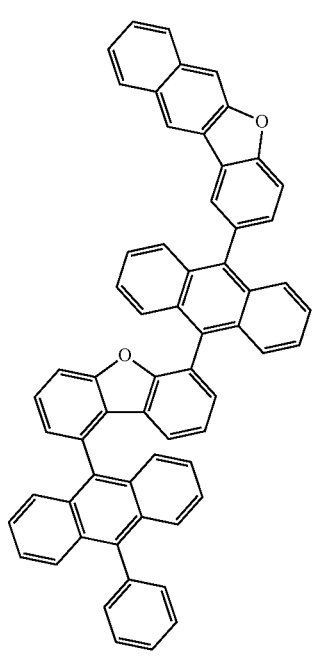
313

1589
-continued
314
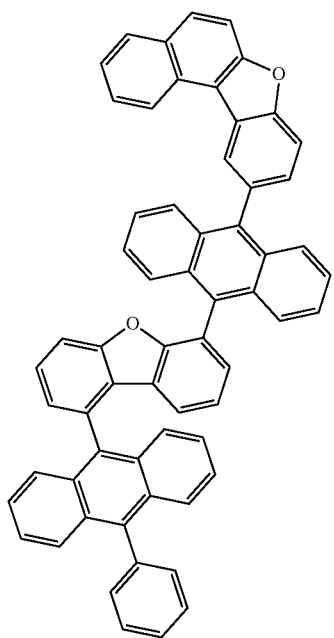
315
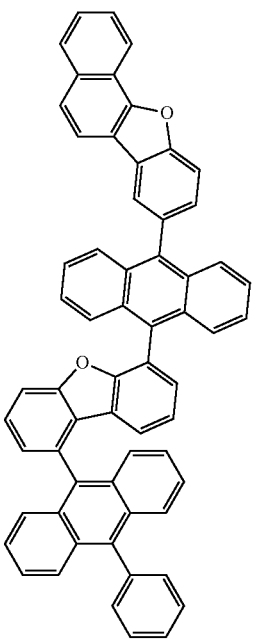
316
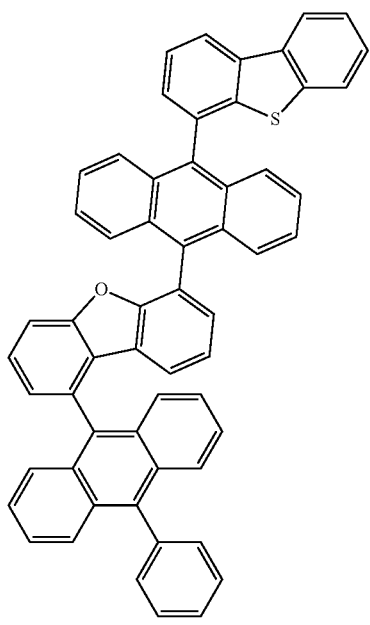
317
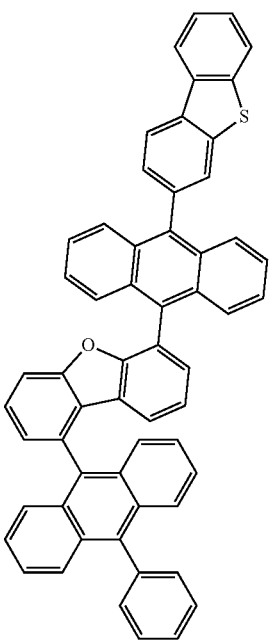

-continued
1591
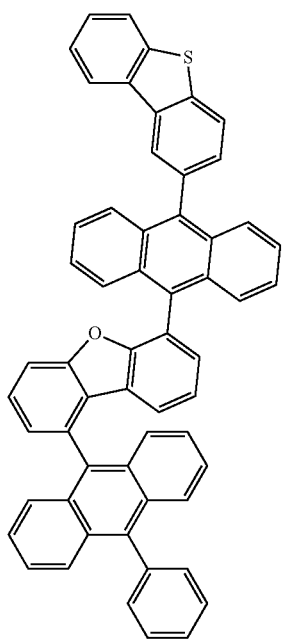
318
1592
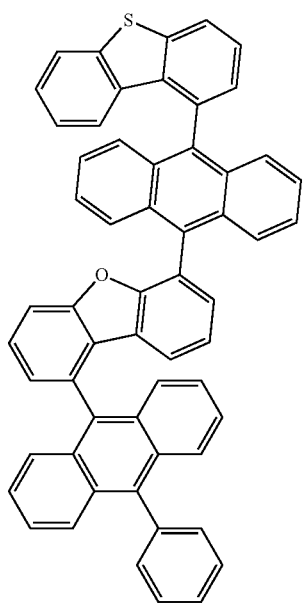
319
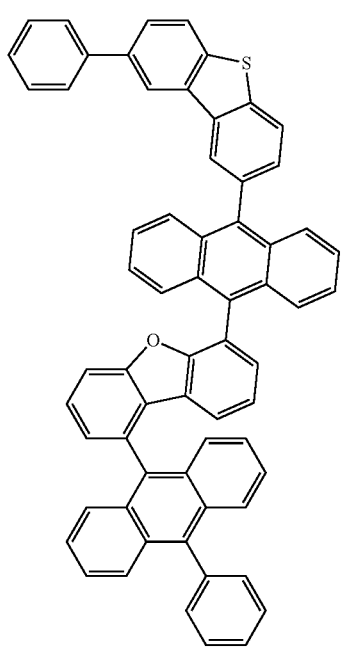
320
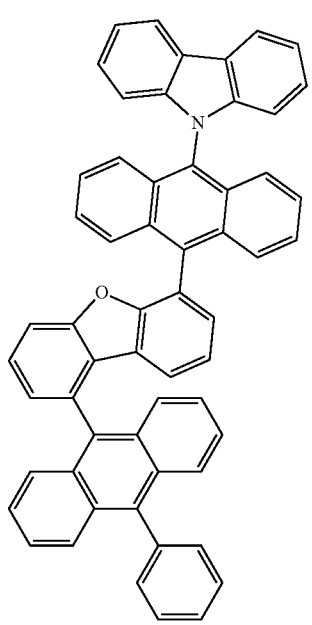
321

1593  1594
-continued
322  323
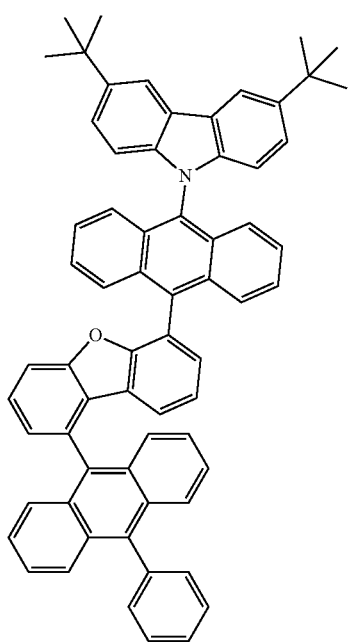
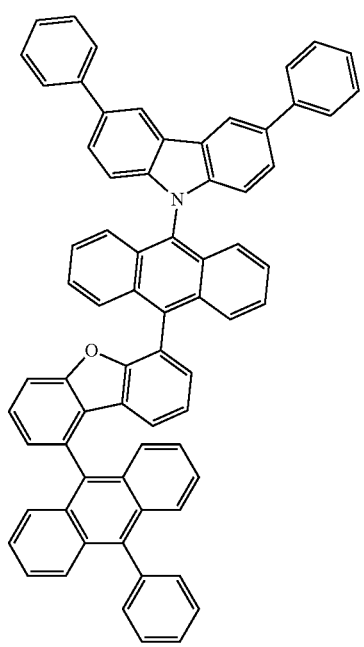
324  325
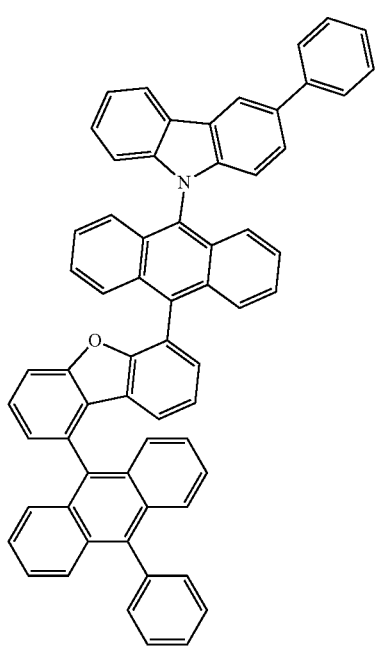
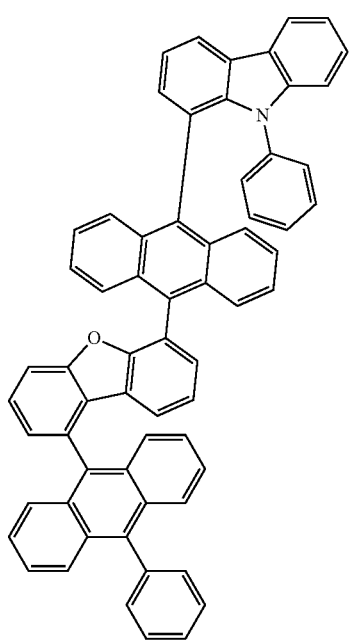

-continued
326
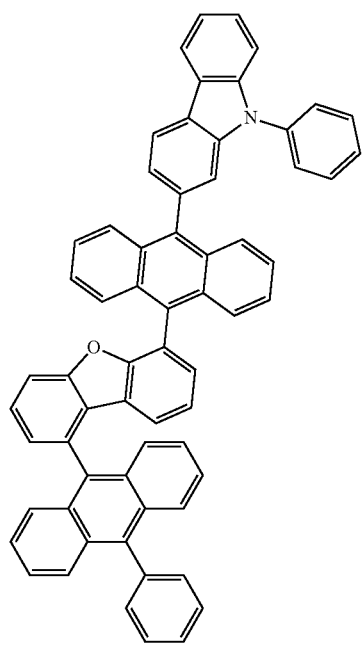
327
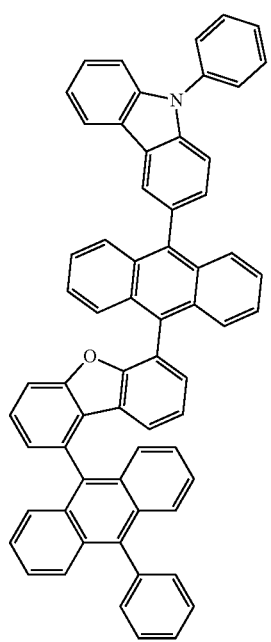
328
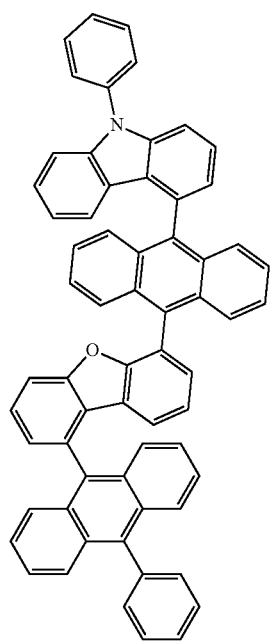
329
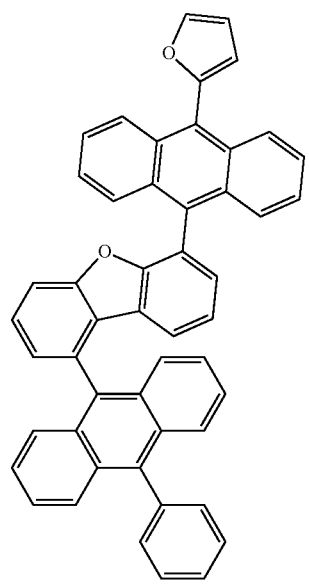

-continued
1597
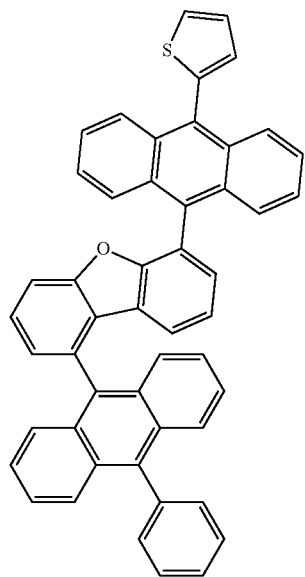
330
1598
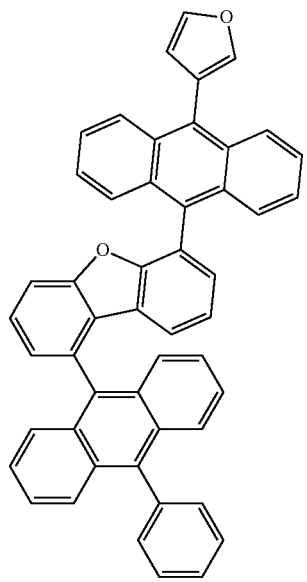
331
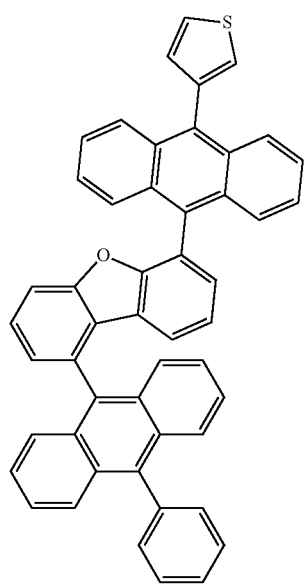
332
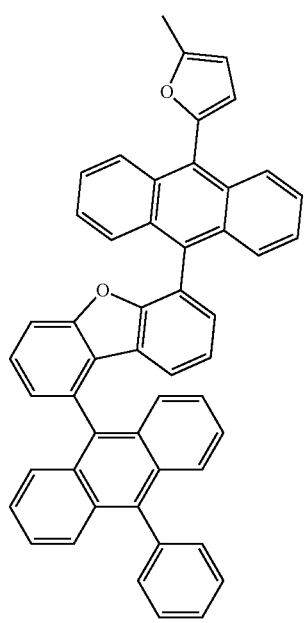
333

-continued
334
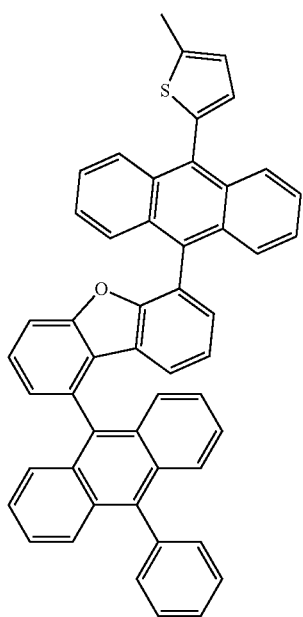
335
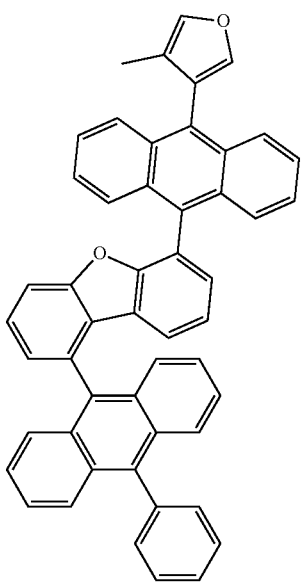
336
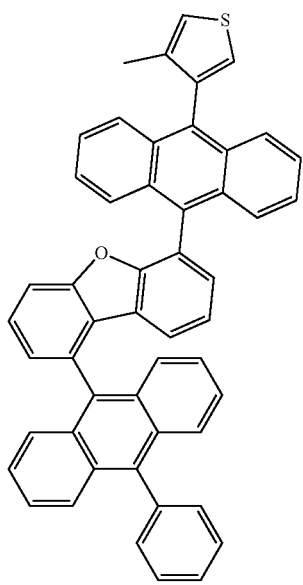
337
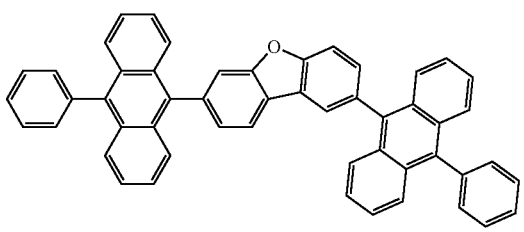
338
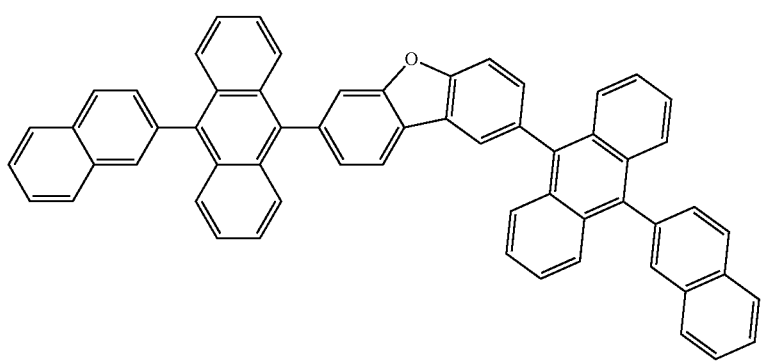

-continued
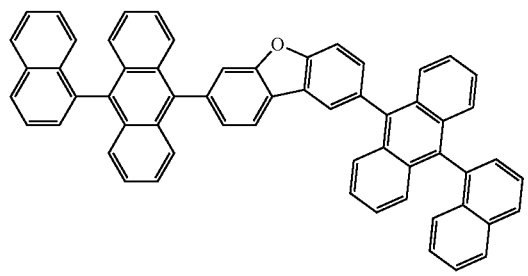
339
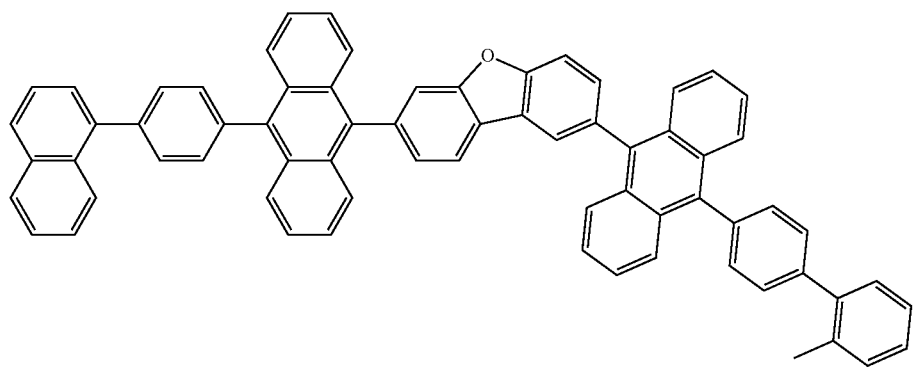
340
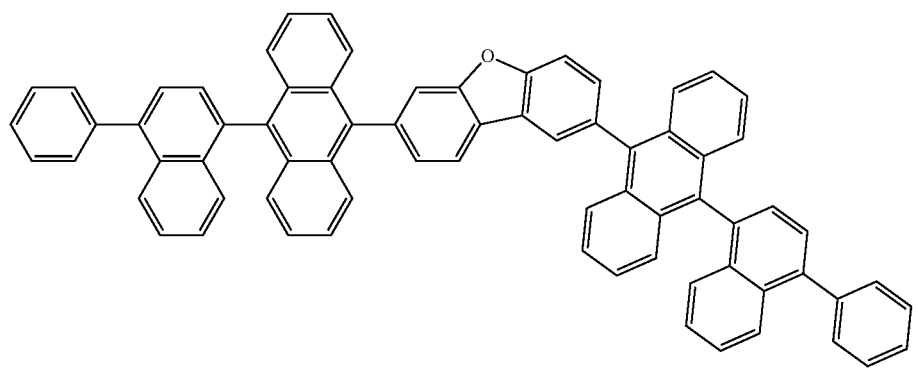
341
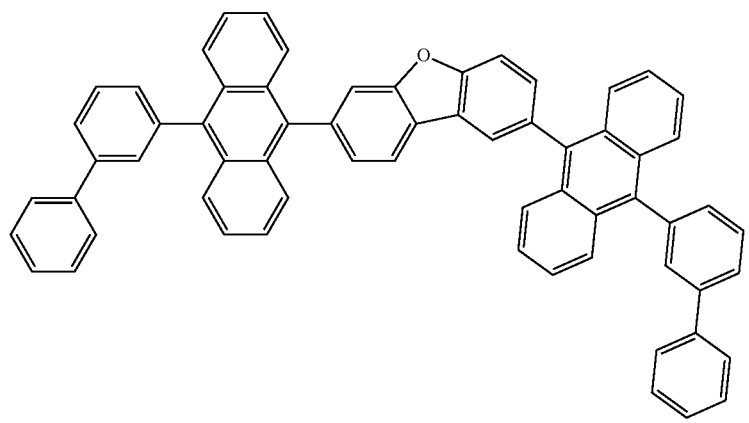
342

343
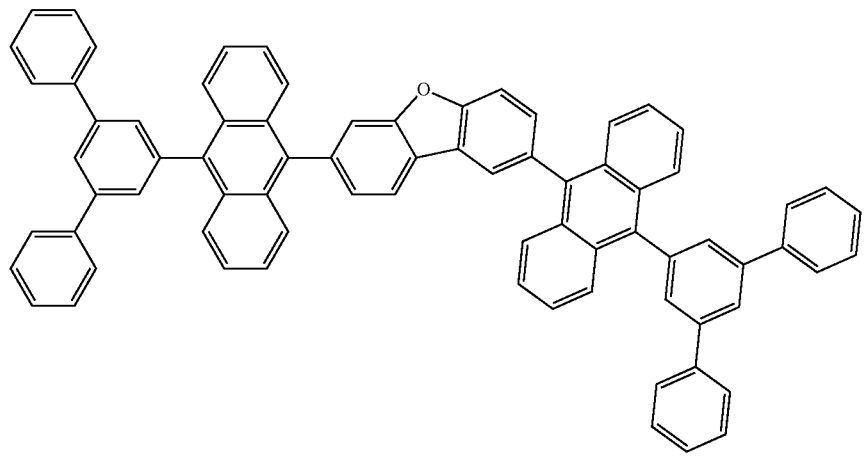
344
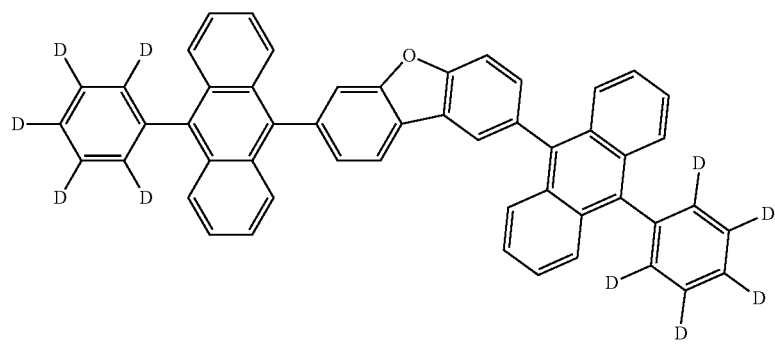
345 346
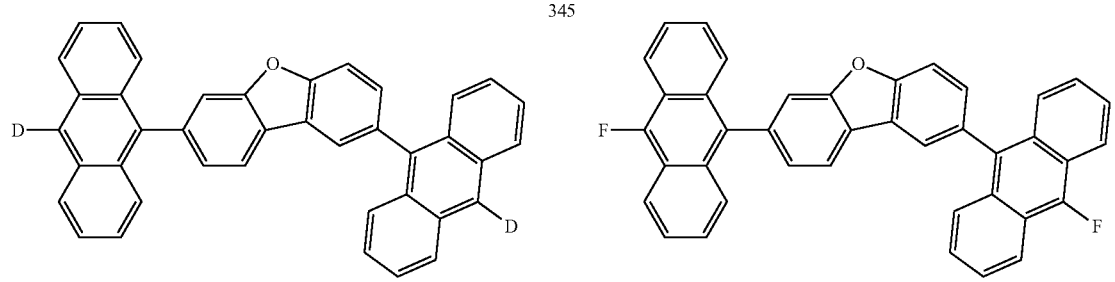
347 348
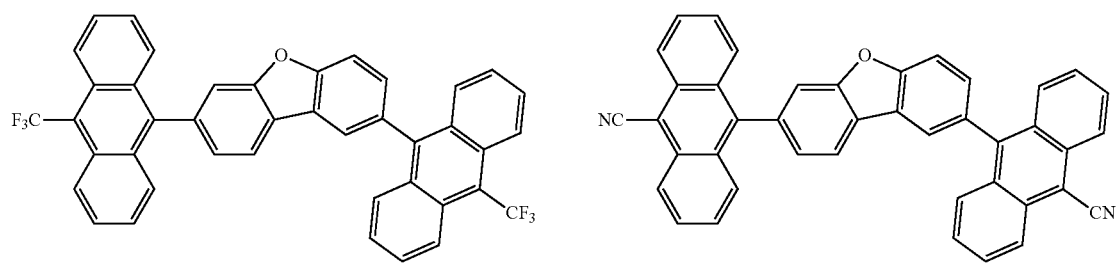
349 350
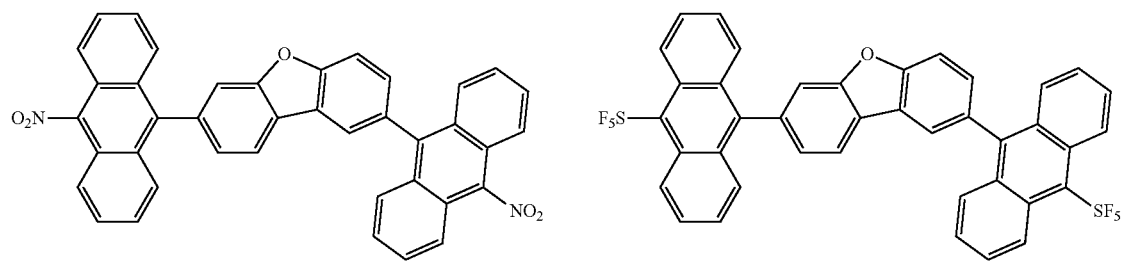

-continued
351
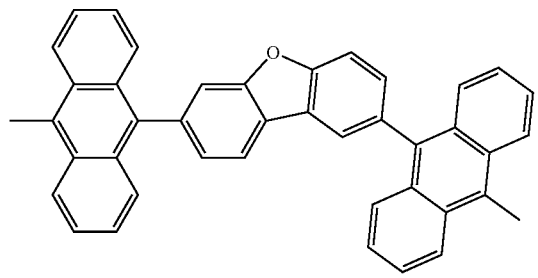
352
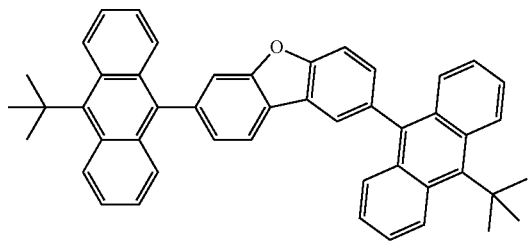
353
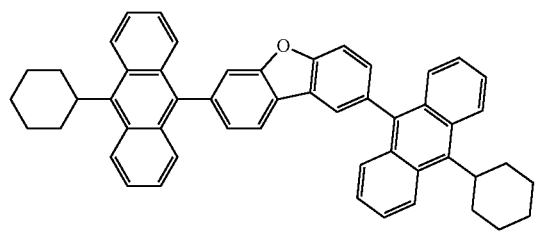
354
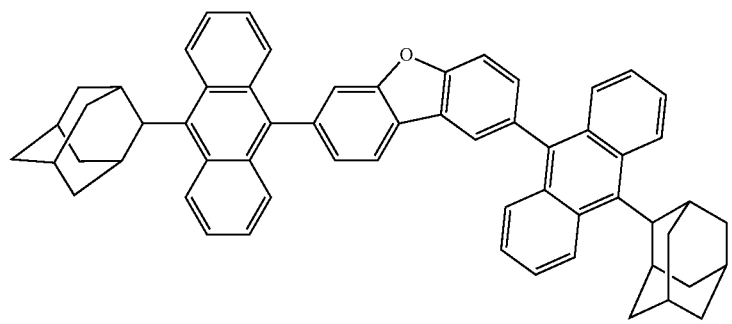
355
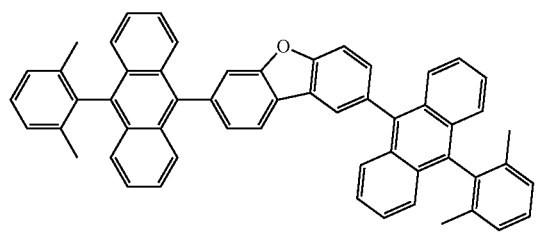
356
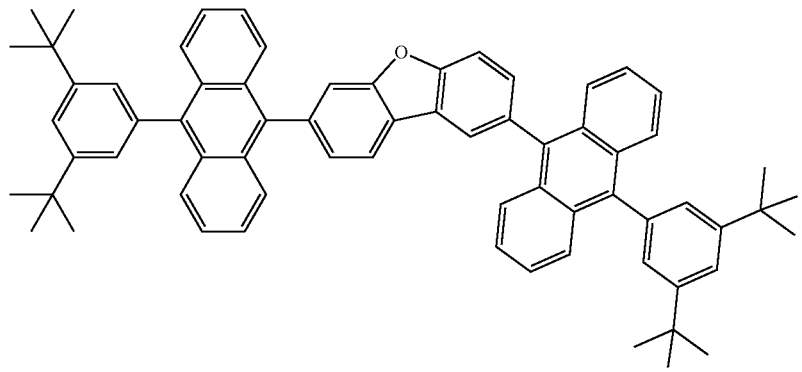

-continued
357
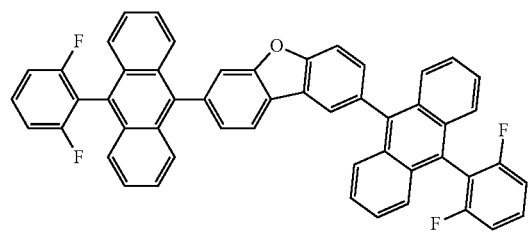
358
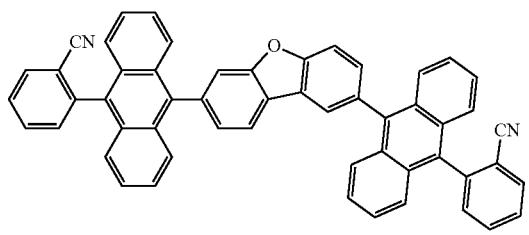
359
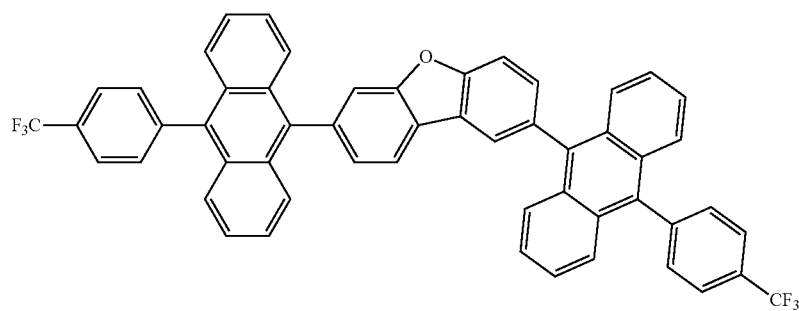
360
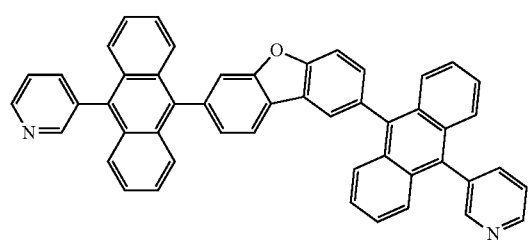
361
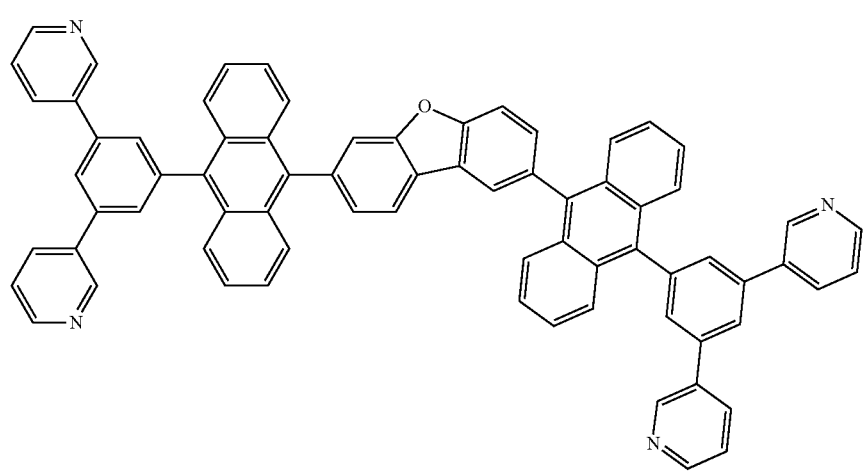

362
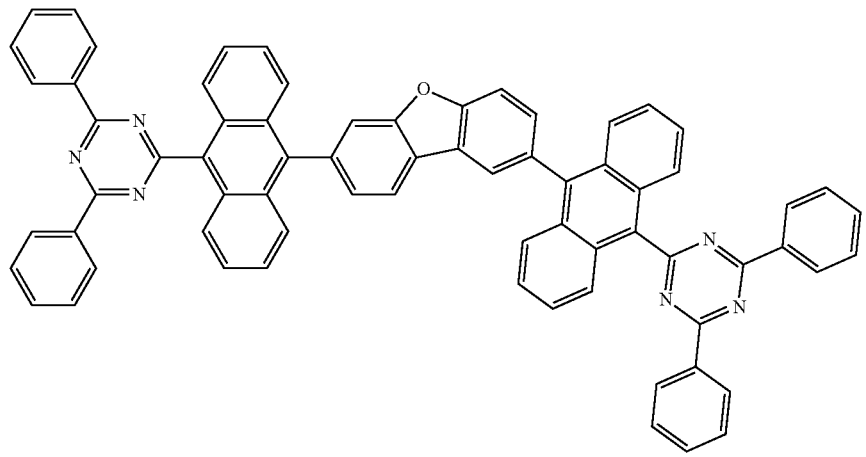
363
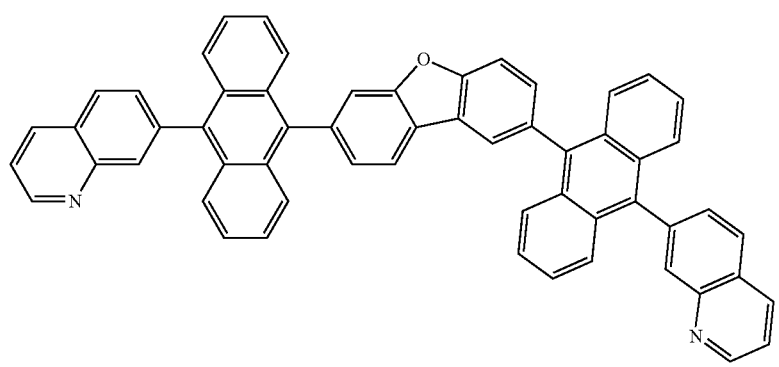
364
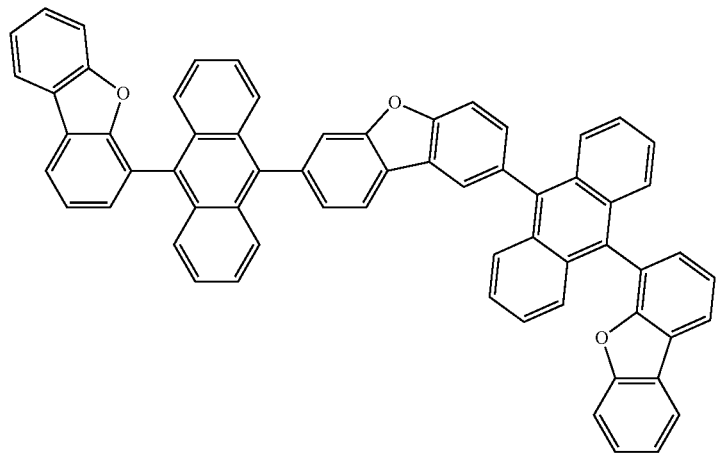
365
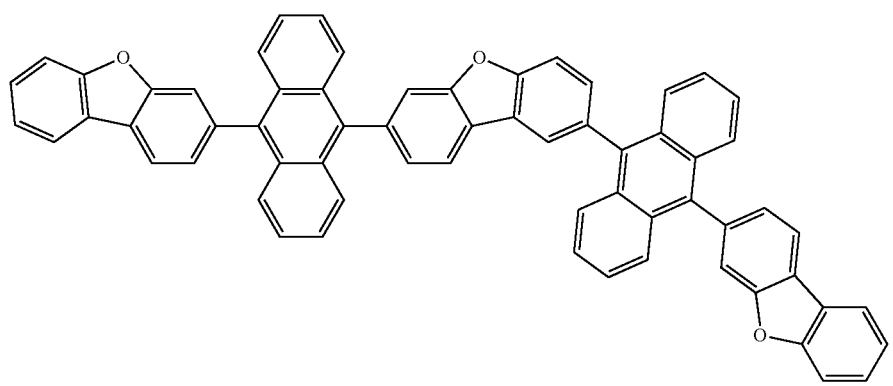

366
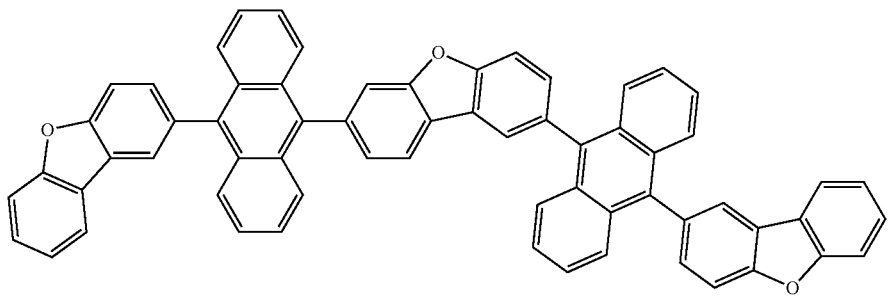
367
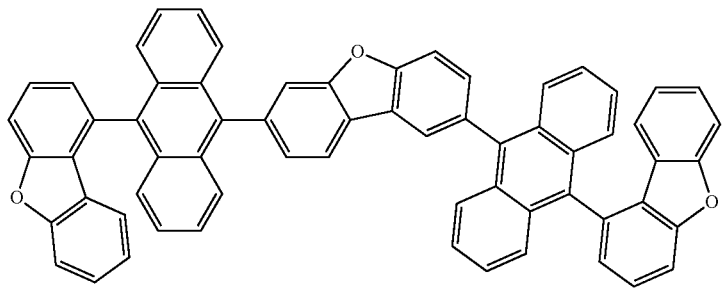
368
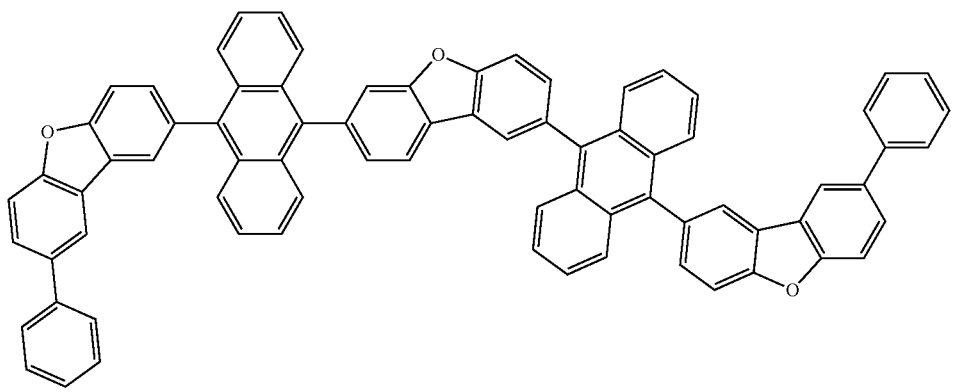
369
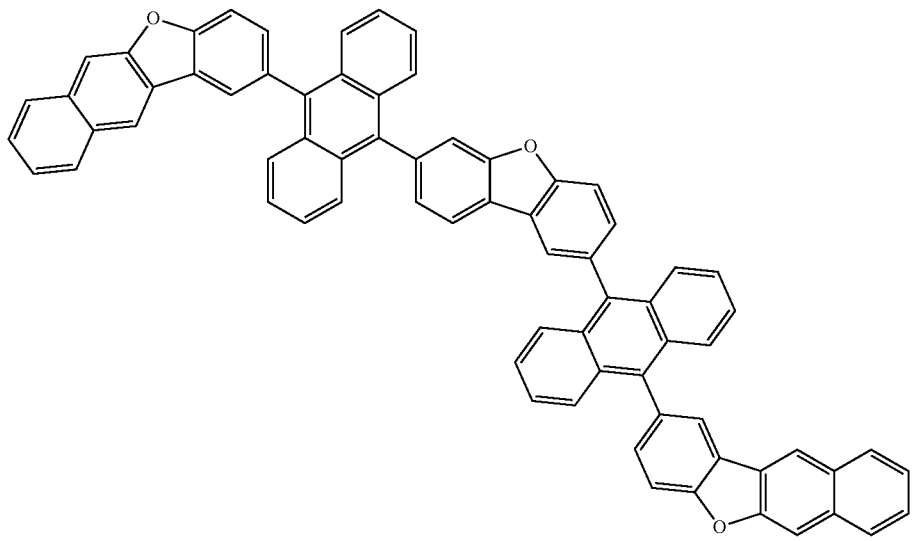

-continued
370
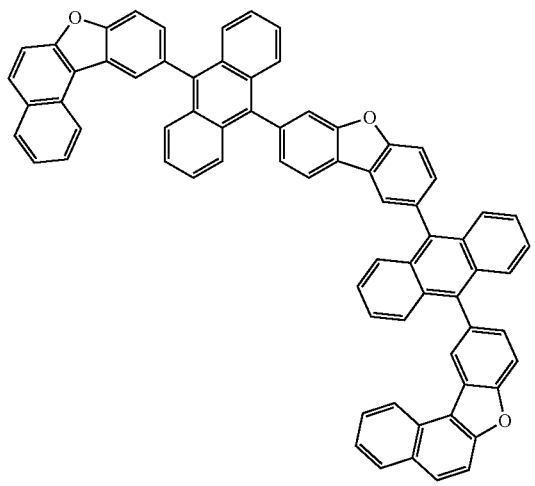
371
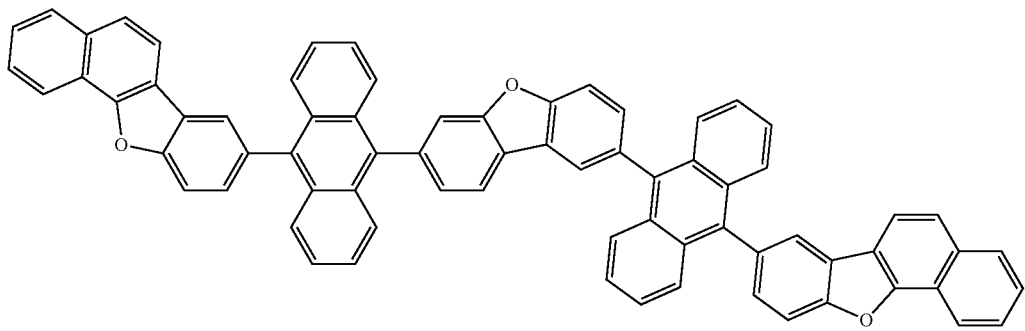
372
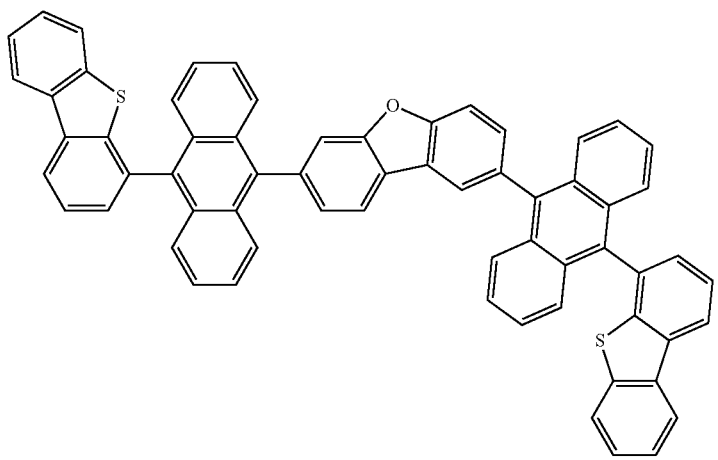
373
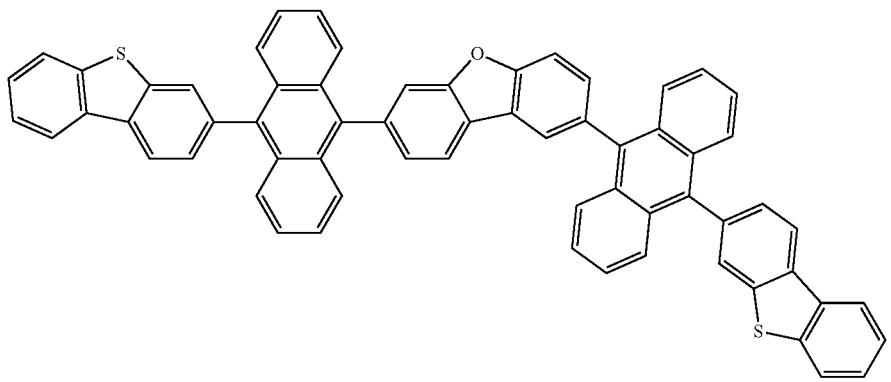

-continued
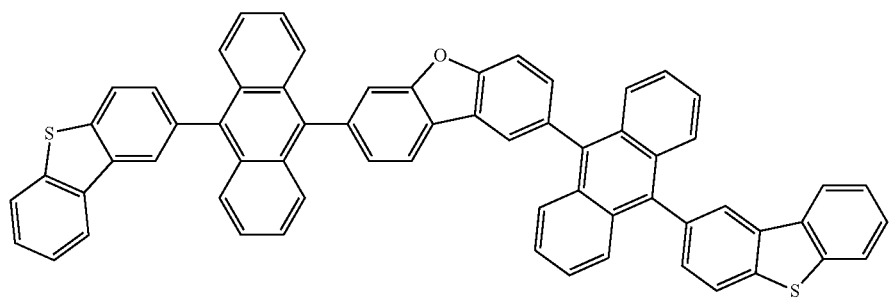
374
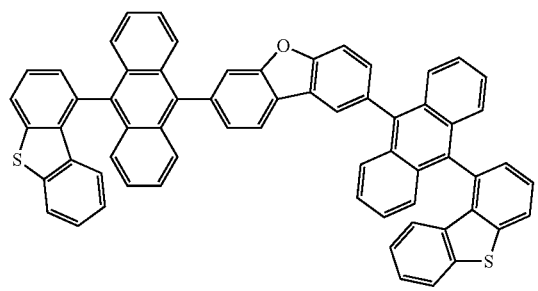
375
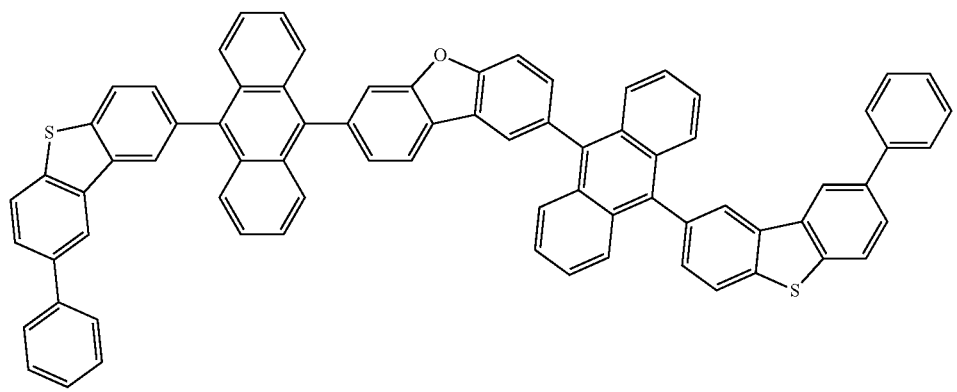
376
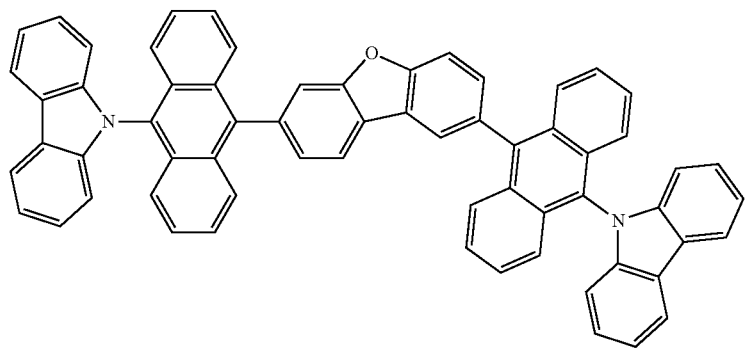
377

-continued
378
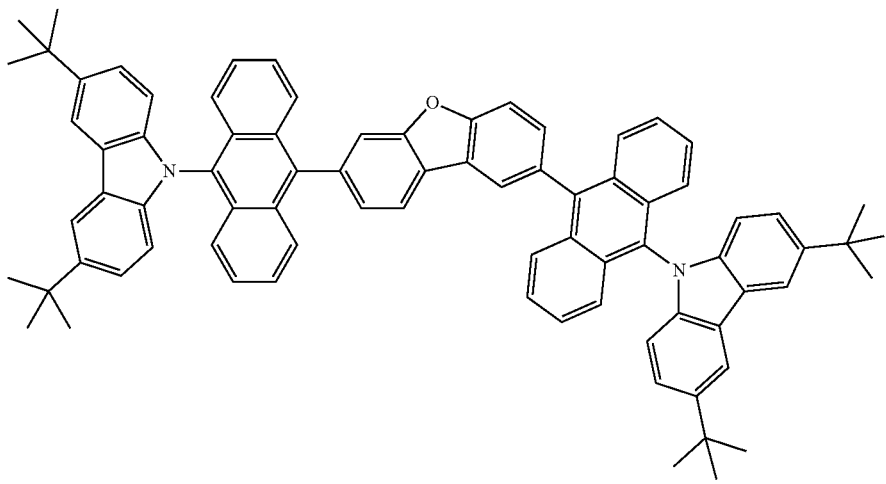
379
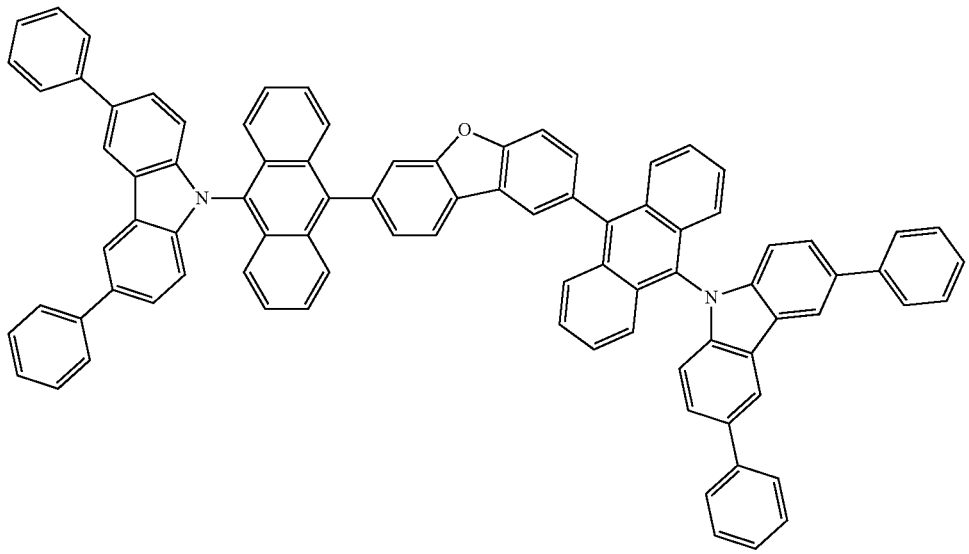
380
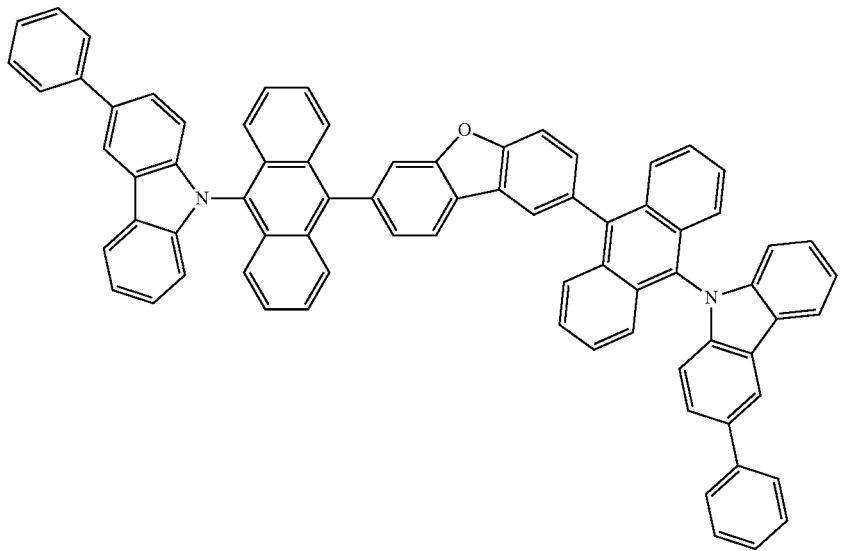

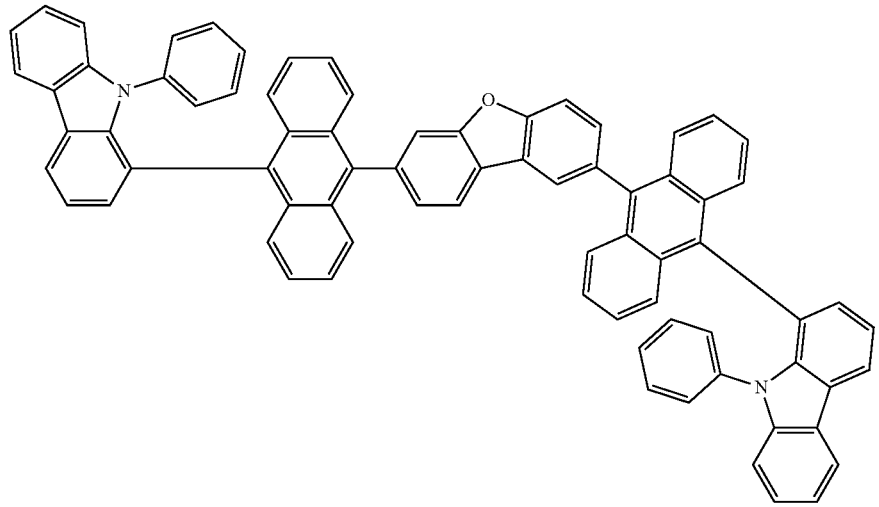
381
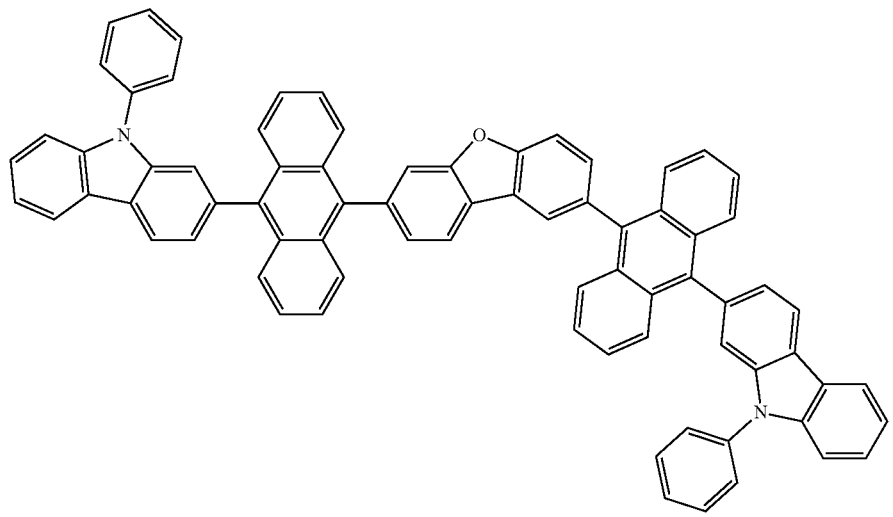
382
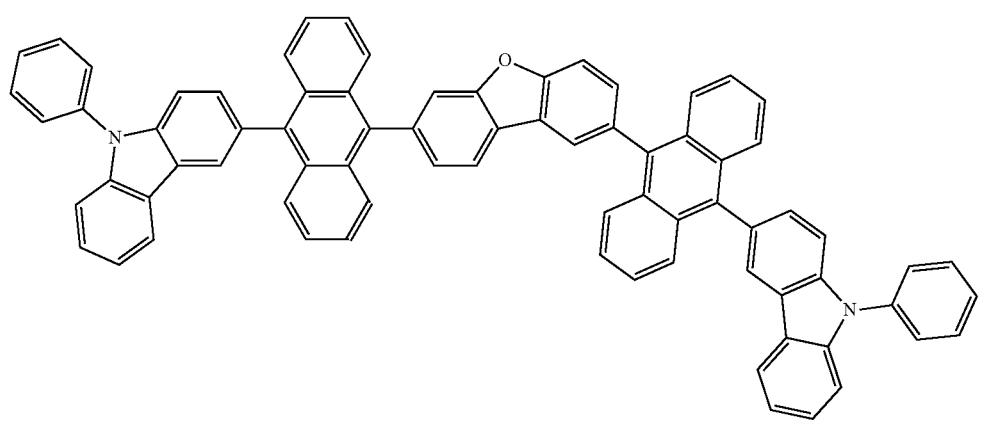
383

384
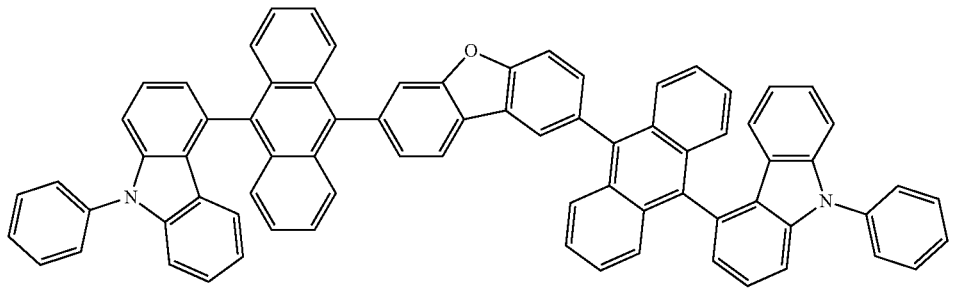
385
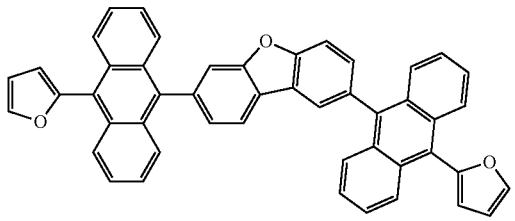
386
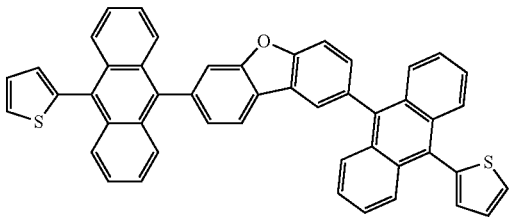
387
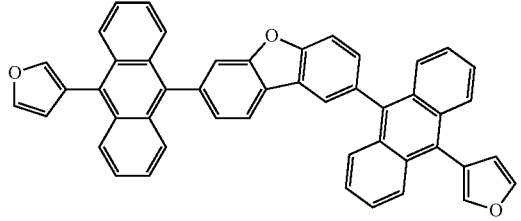
388
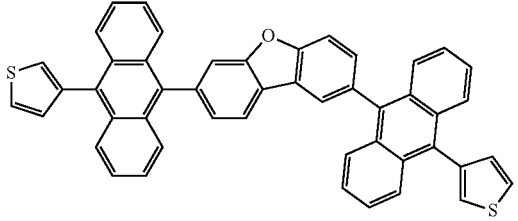
389
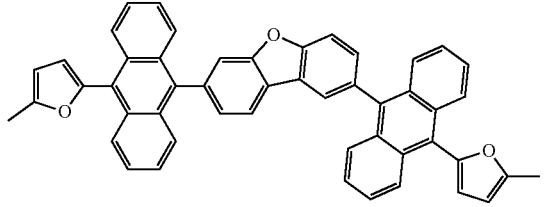
390
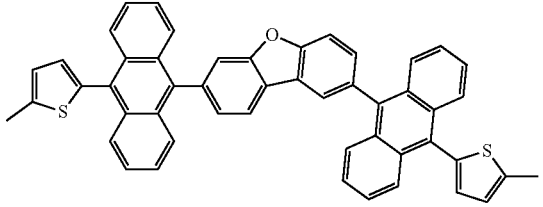
391
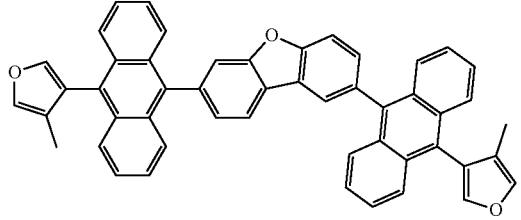
392
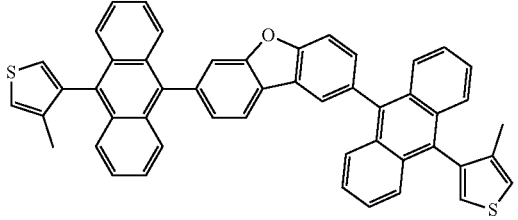
393
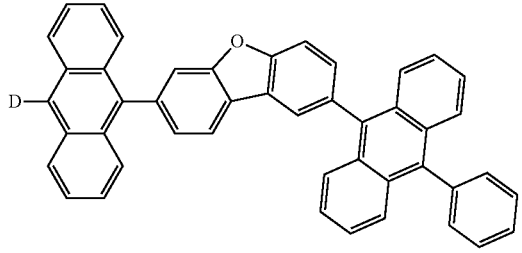
394
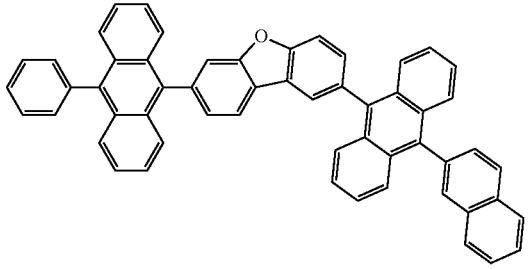

-continued
395
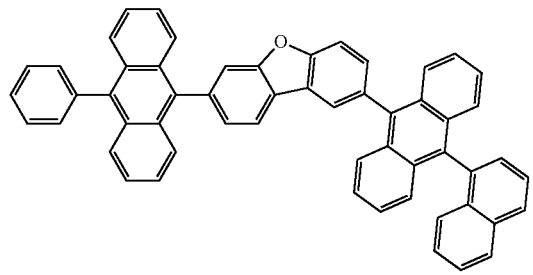
396
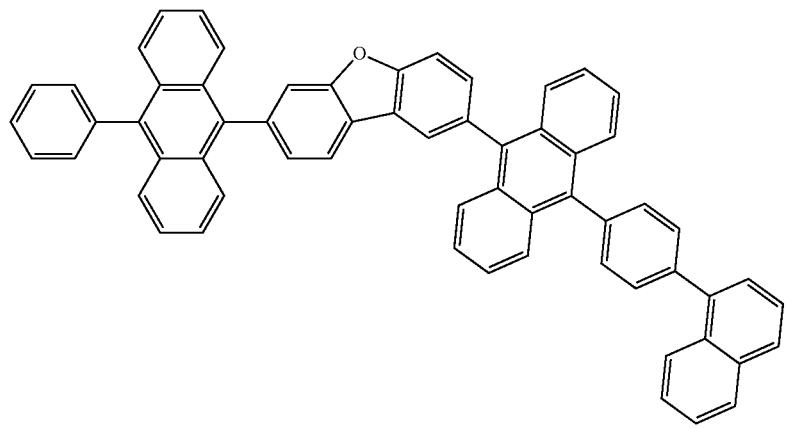
397
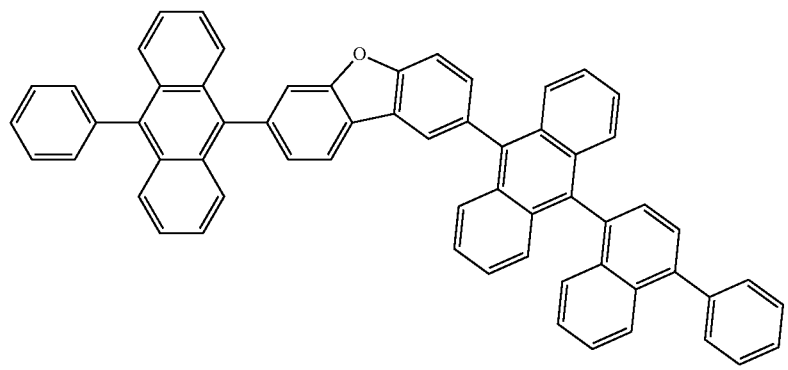
398
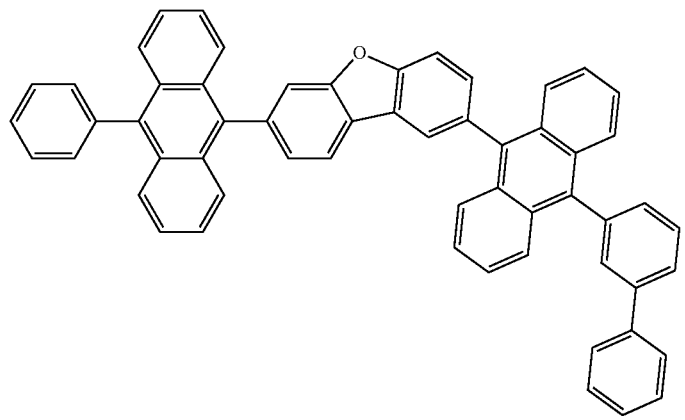

1625     1626
-continued
399
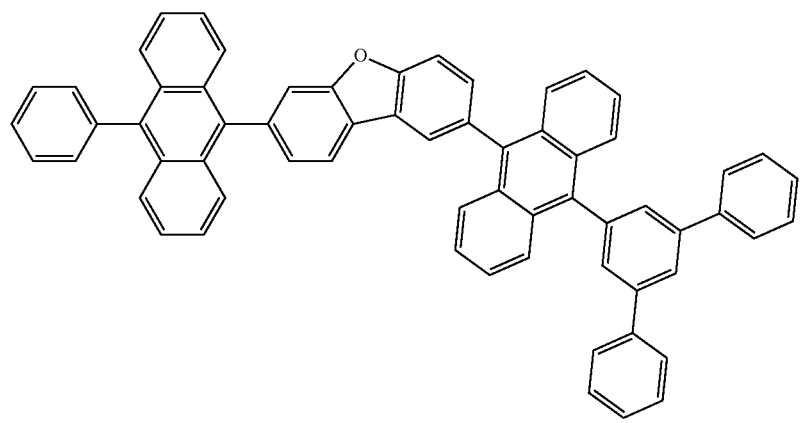
400
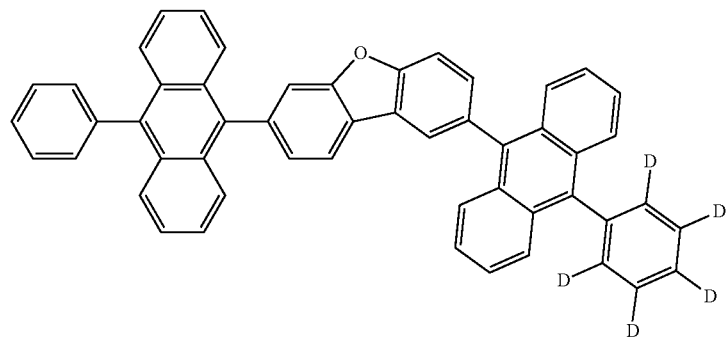
401     402
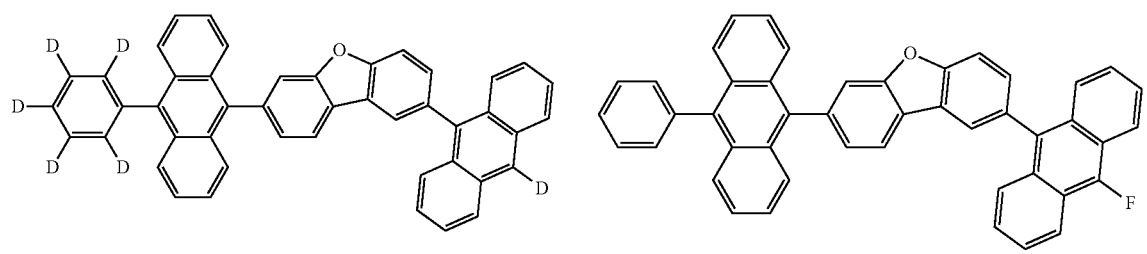
403     404
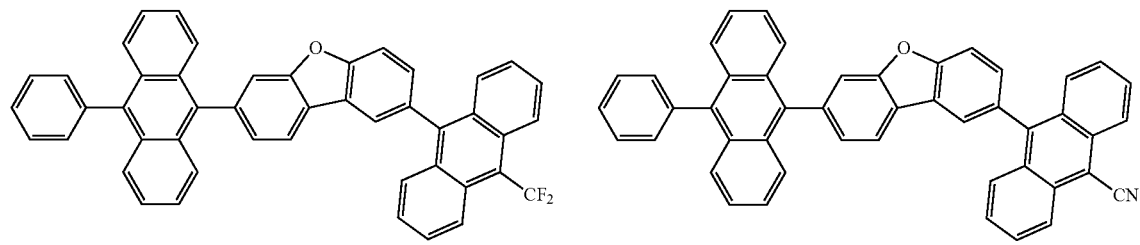

-continued
405
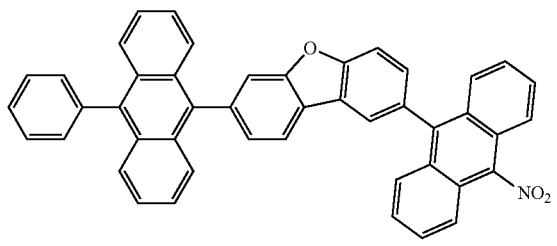
406
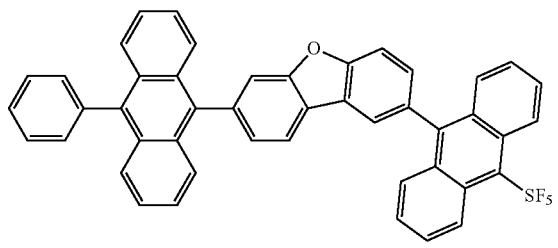
407
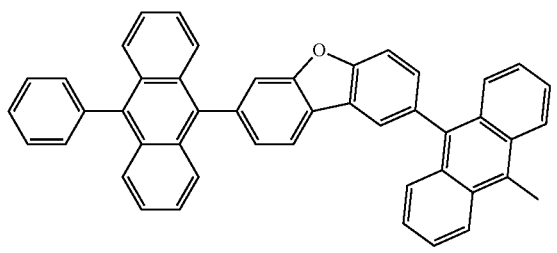
408
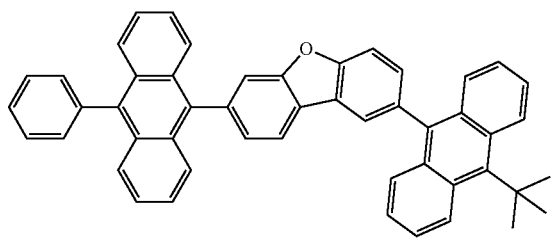
409
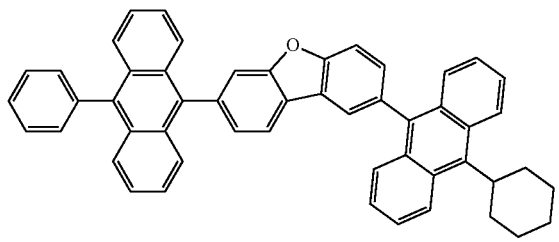
410
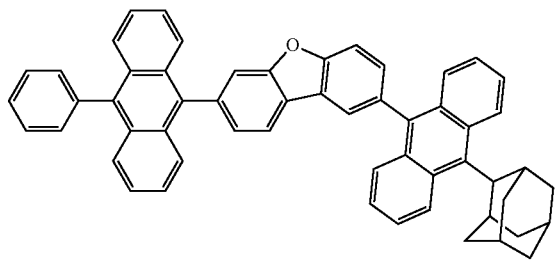
411
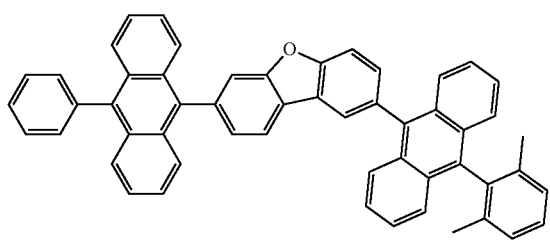
412
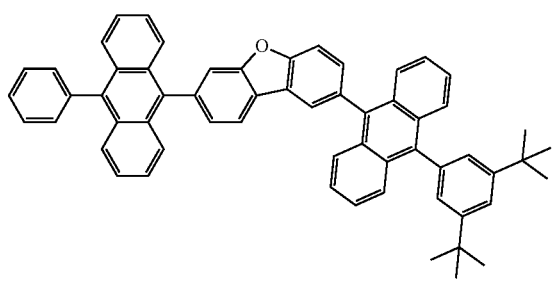
413
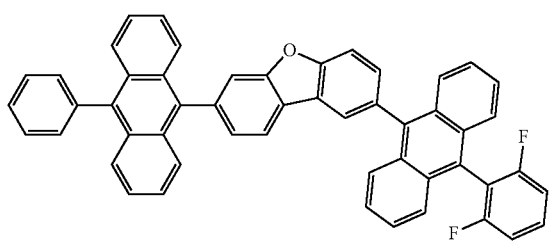
414
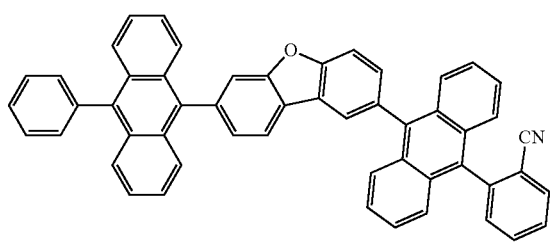

-continued
415
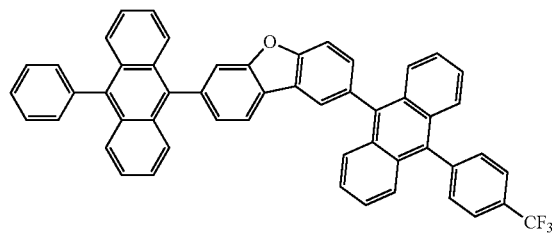
416
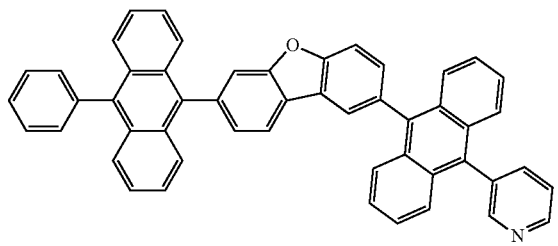
417
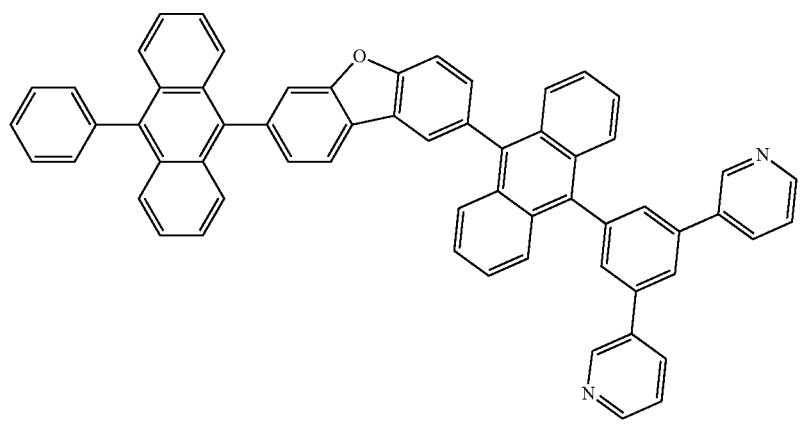
418
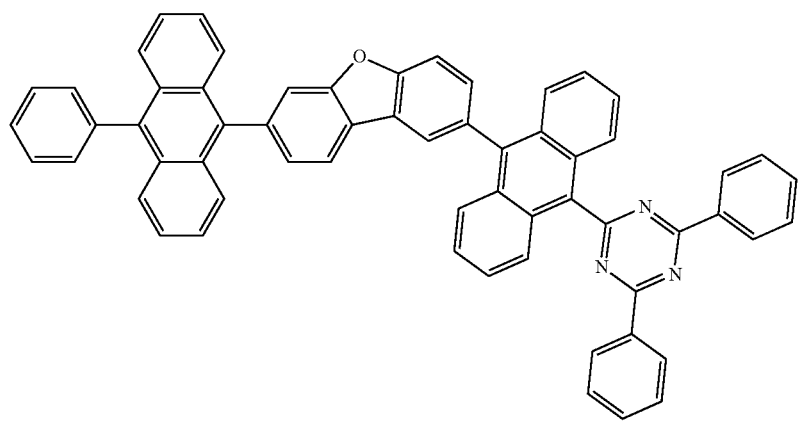
419
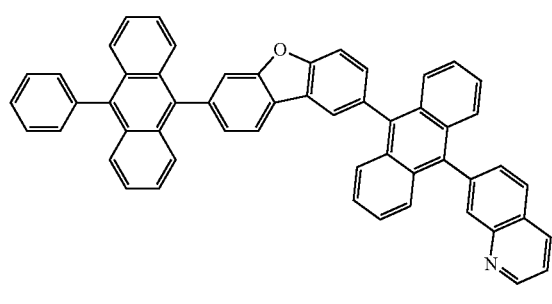
420
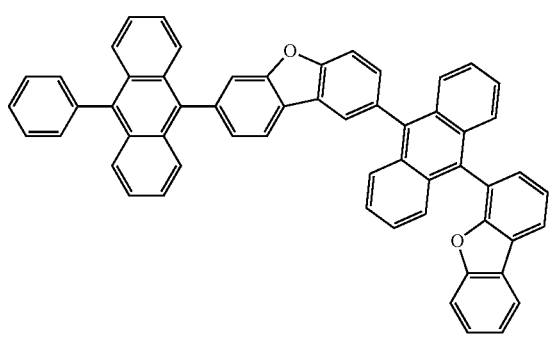

1631
1632
-continued
421
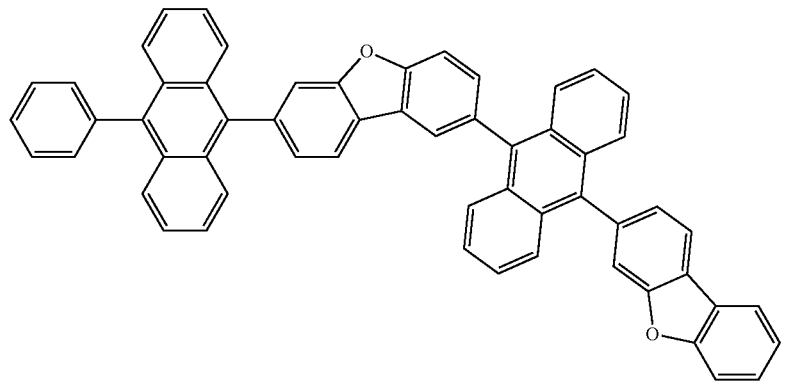
422
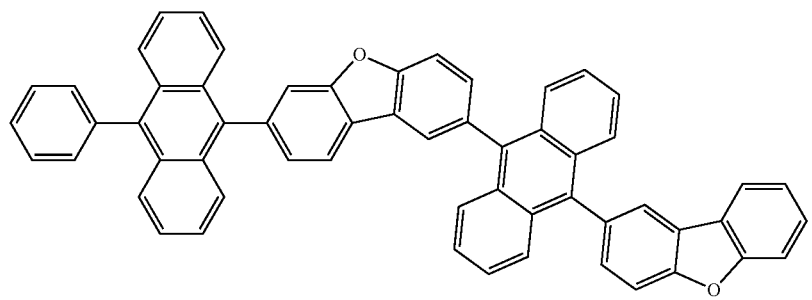
423
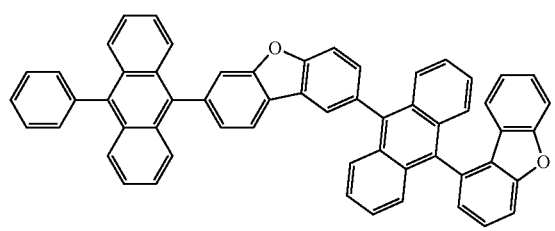
424
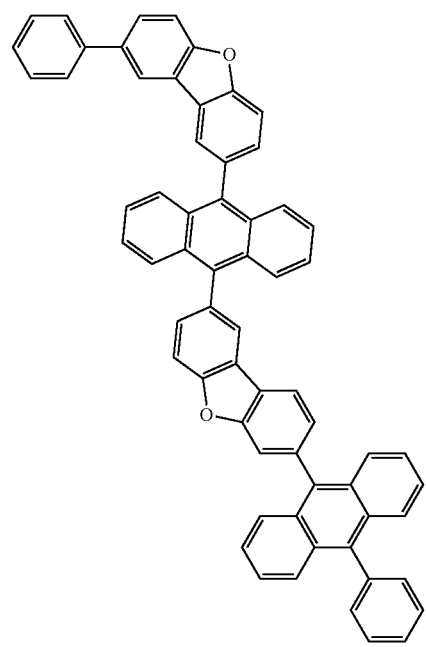

425
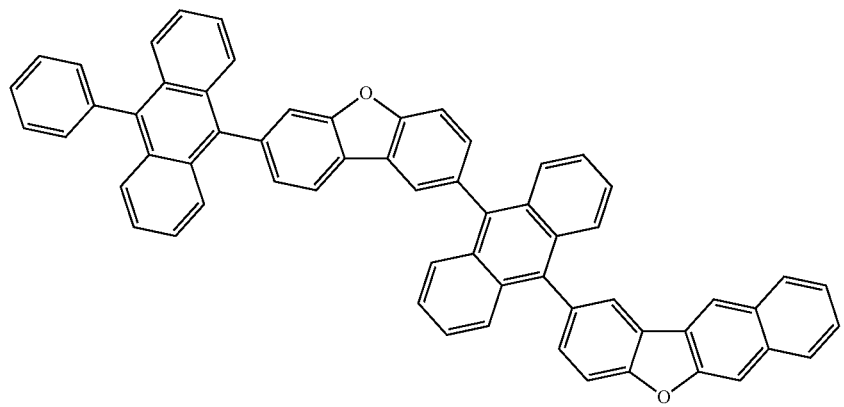
426
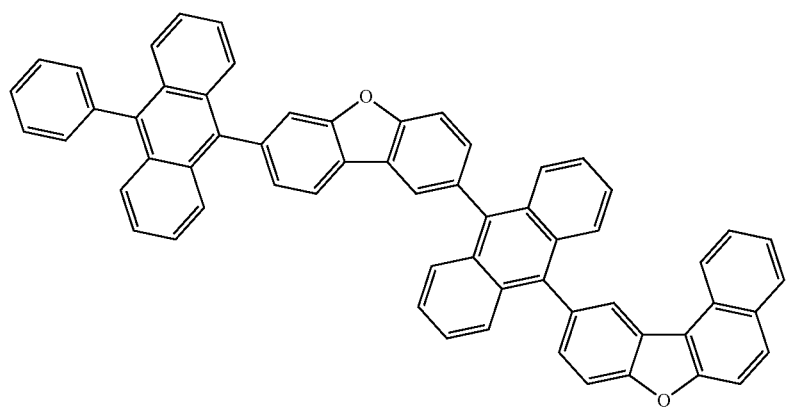
427
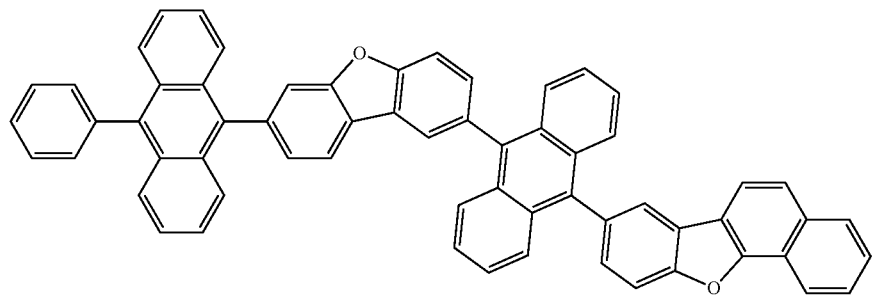
428
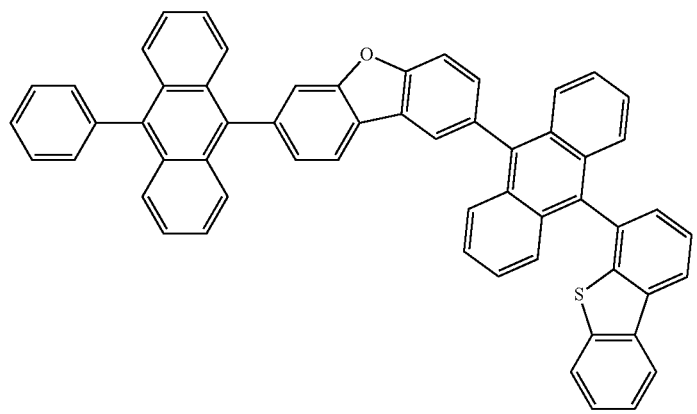

1635
-continued
429
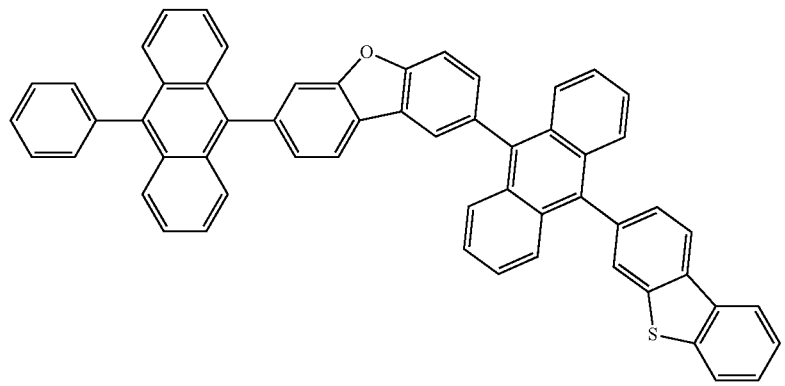
430
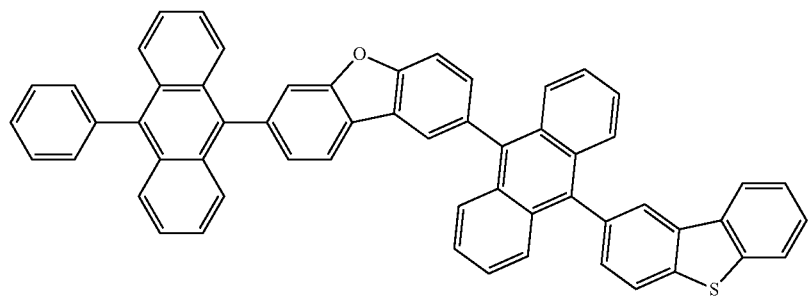
431
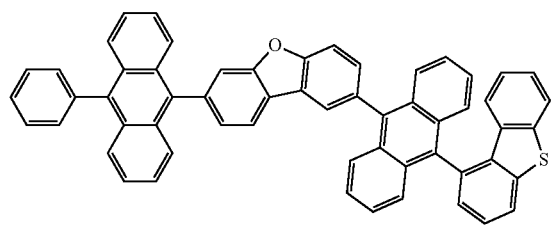
1636
432
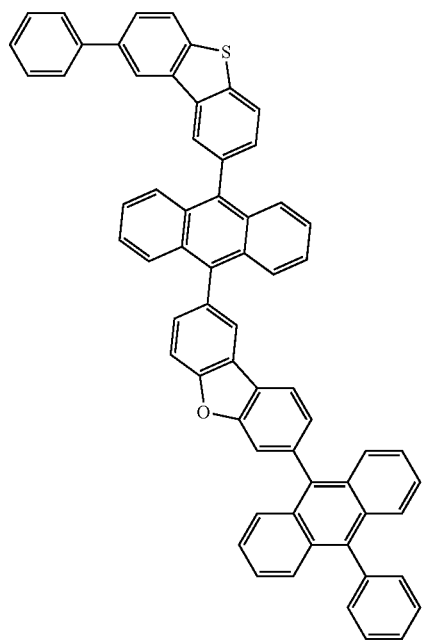

-continued
433
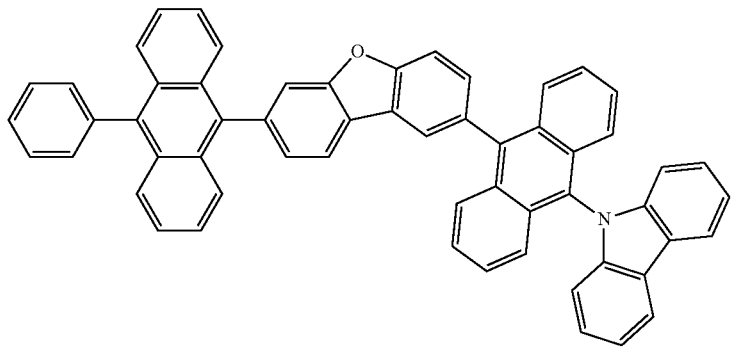
434
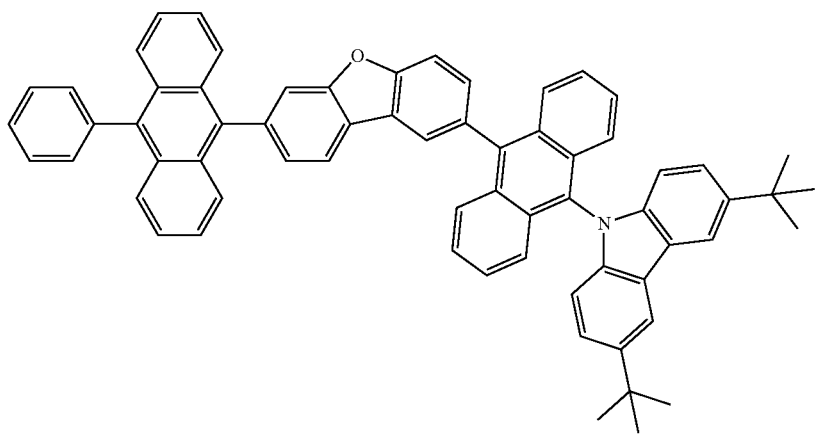
435
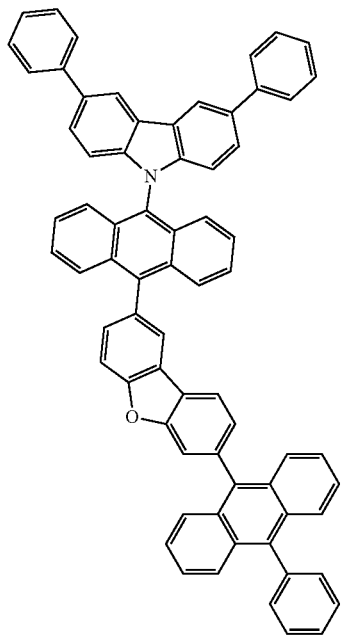
436
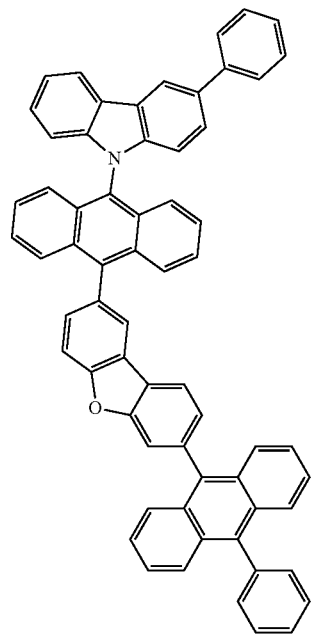

-continued
437
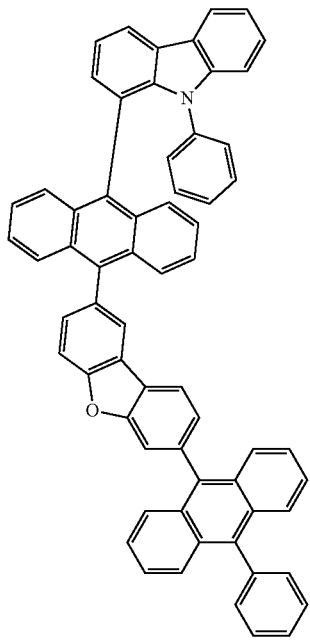
438
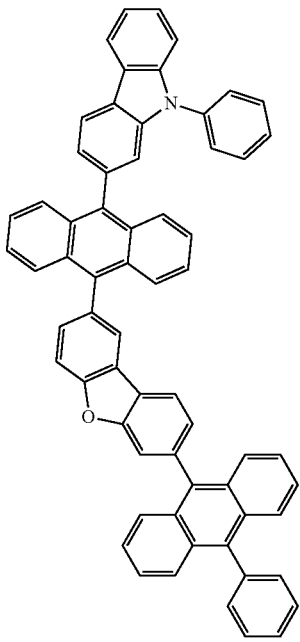
439
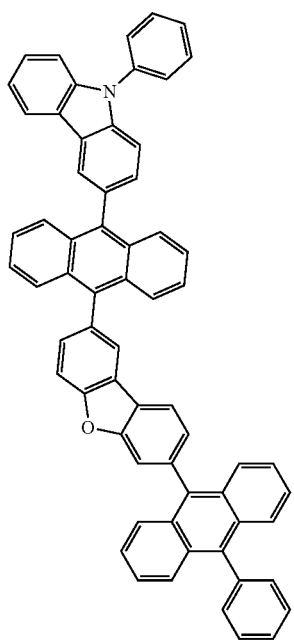
440
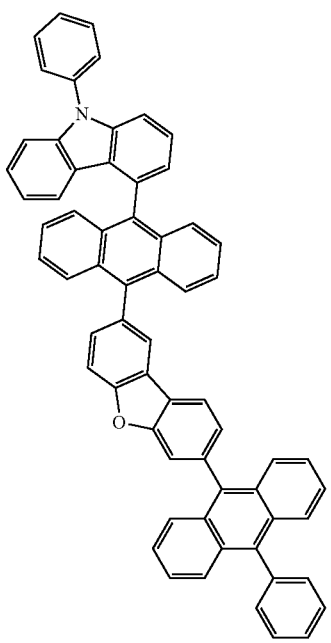
441
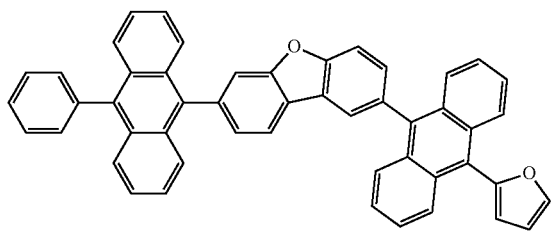
442
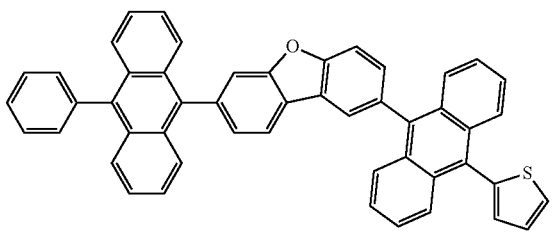

-continued
443
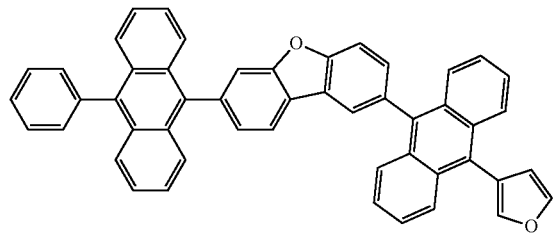
444
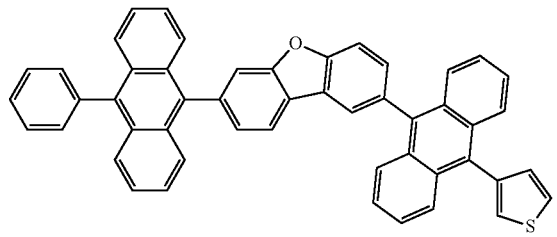
445
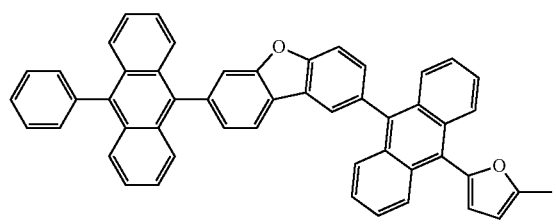
446
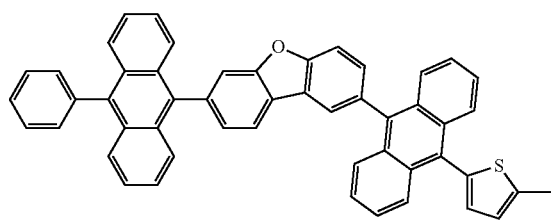
447
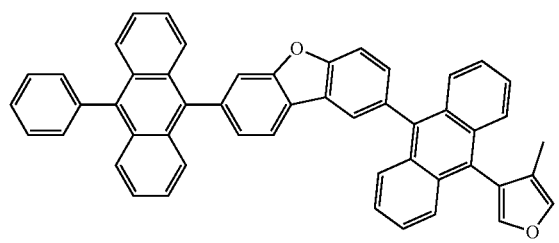
448
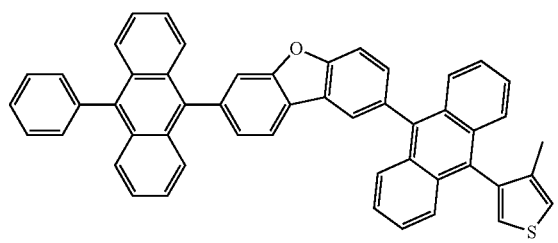
449
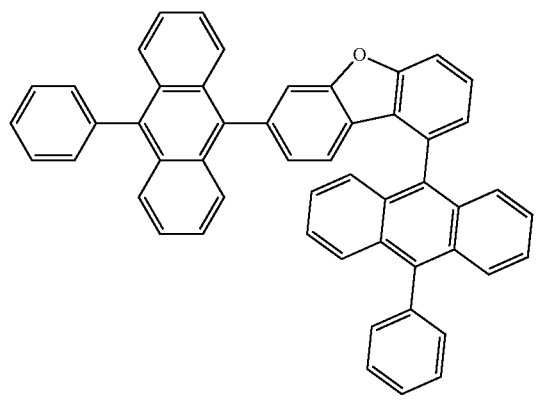
450
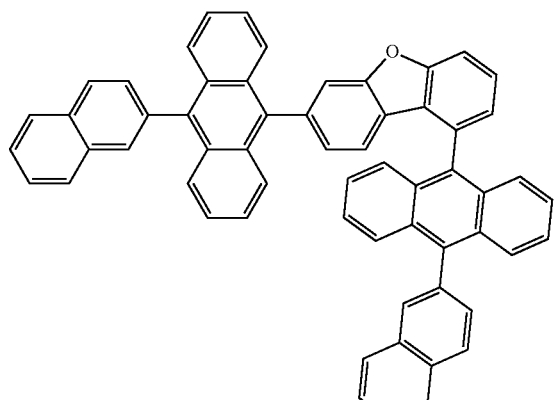

-continued
451
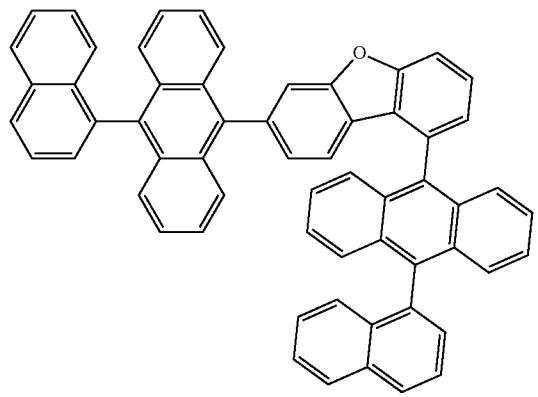
452
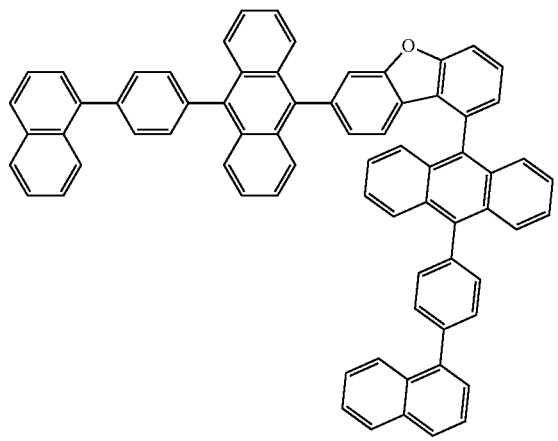
453
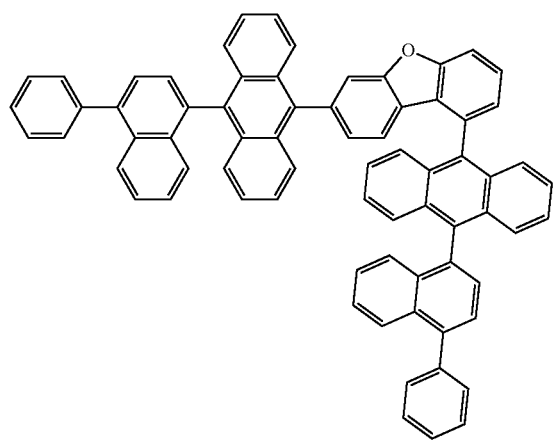
454
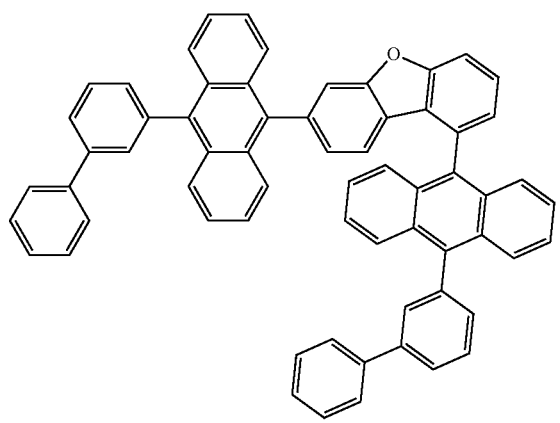
455
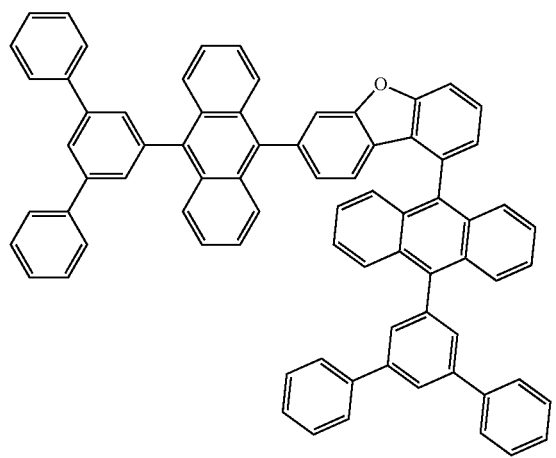
456
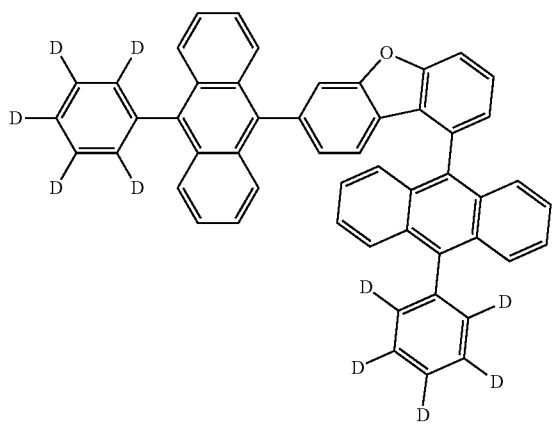

-continued
457
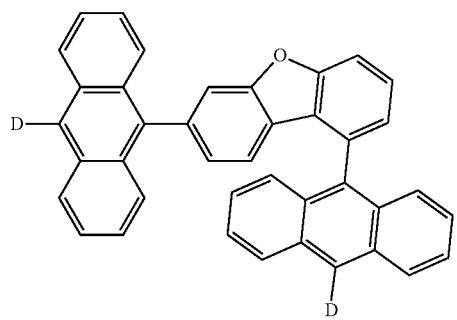
458
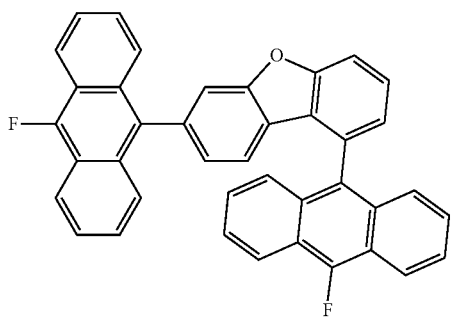
459
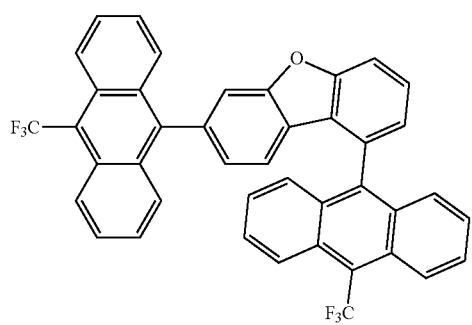
460
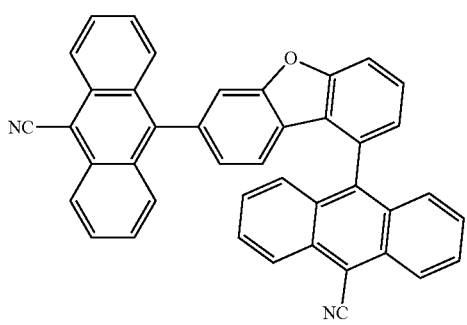
461
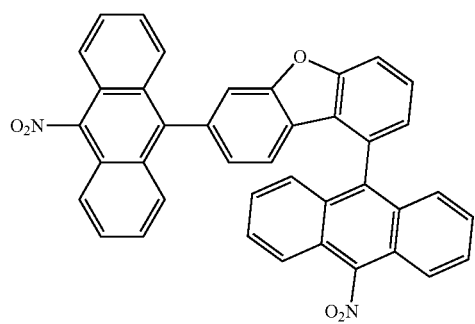
462
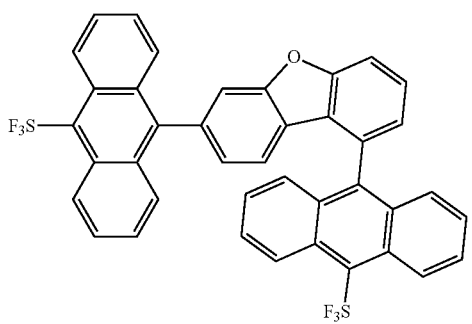
463
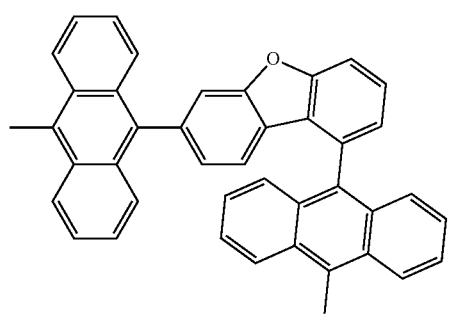
464
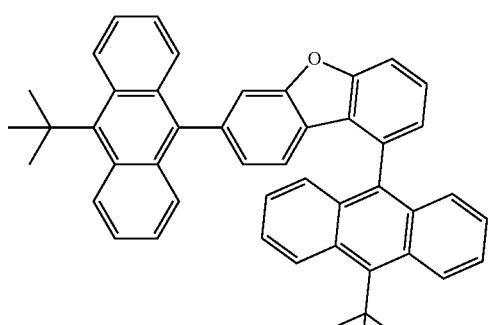

-continued
465
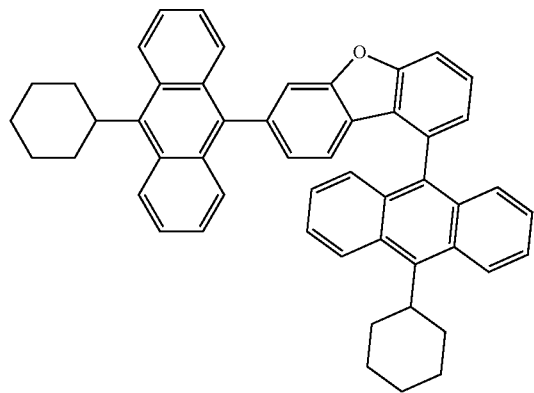
466
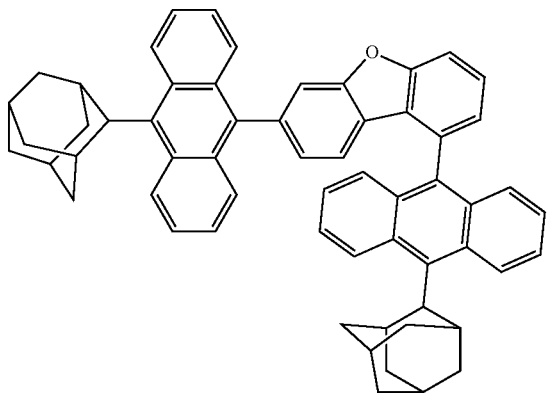
467
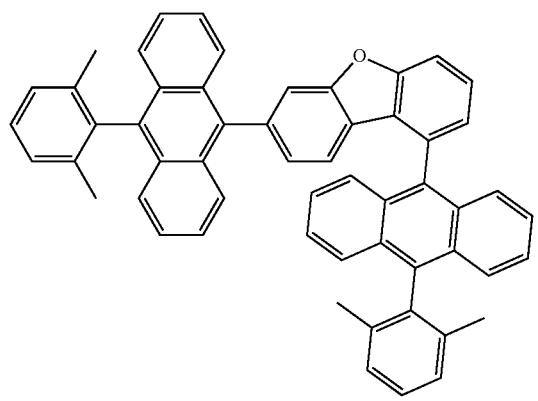
468
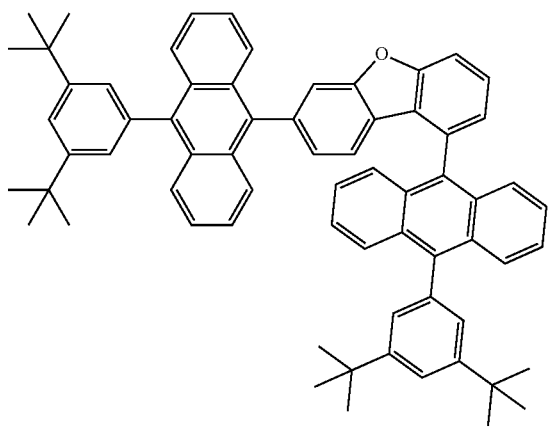
469
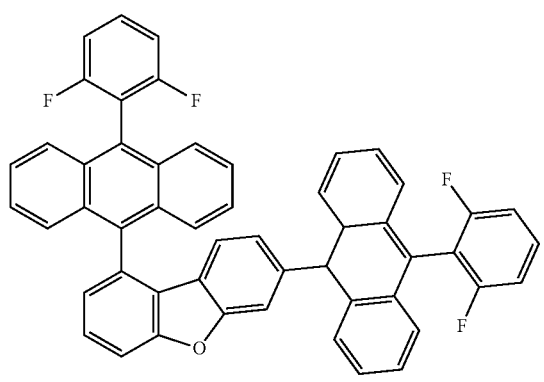
470
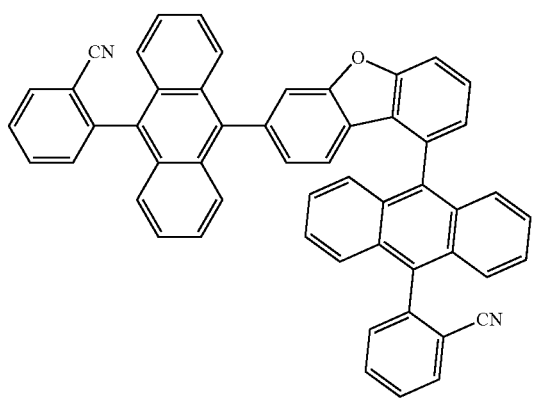

471
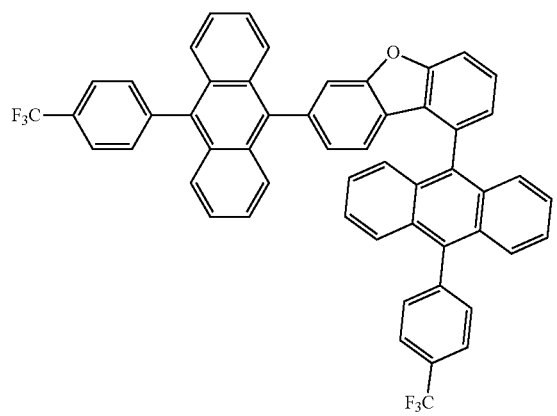
472
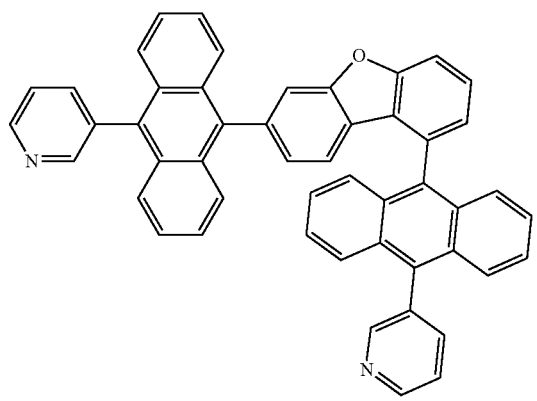
473
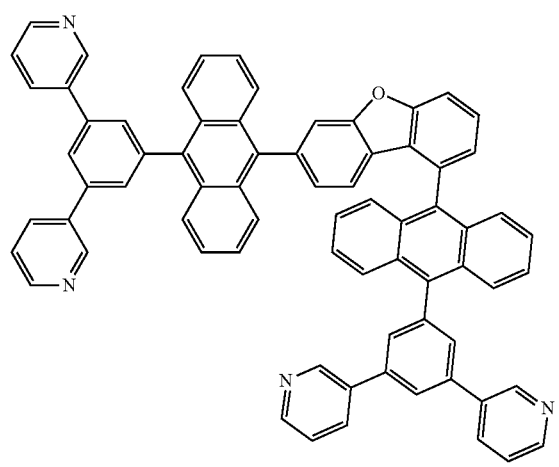
474
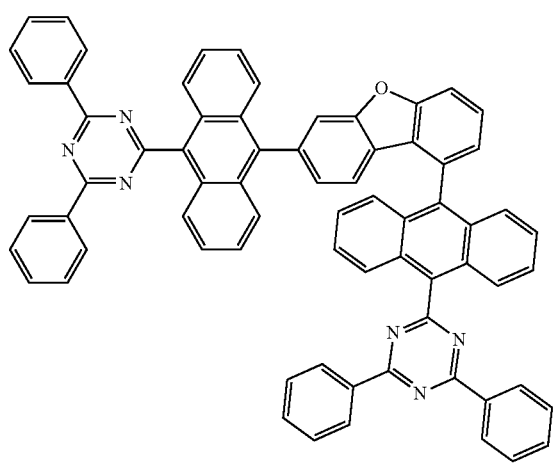
475
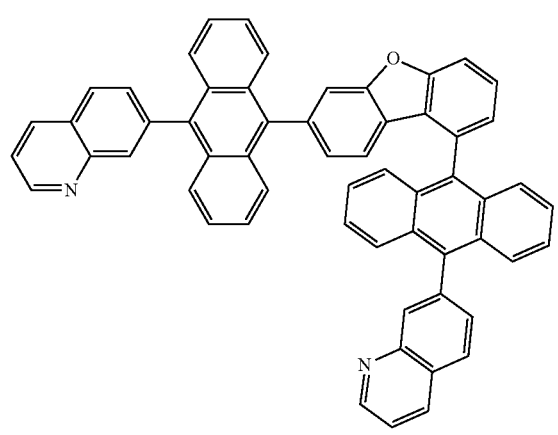
476
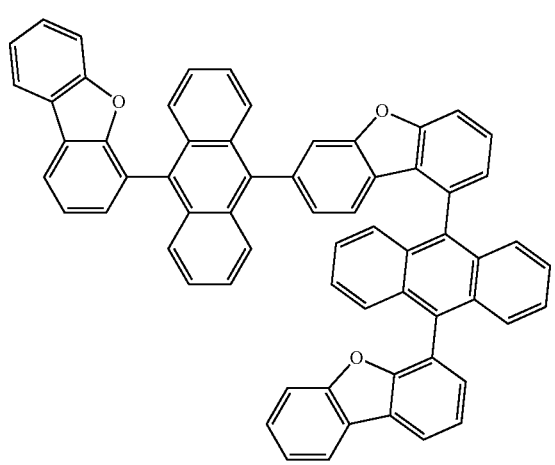

-continued
477
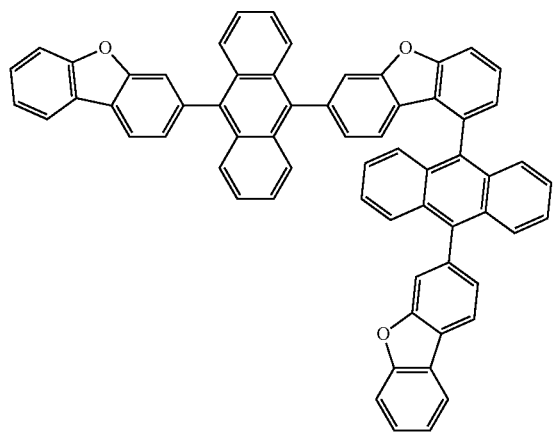
478
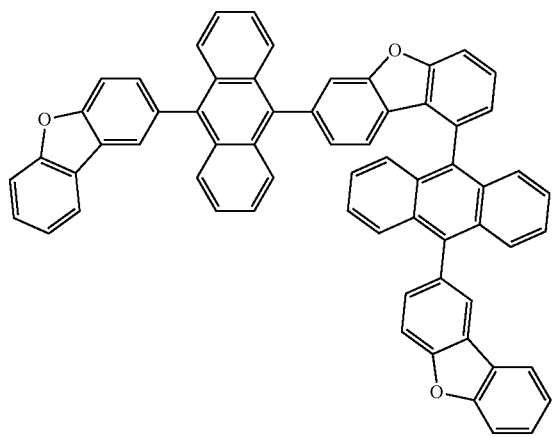
479
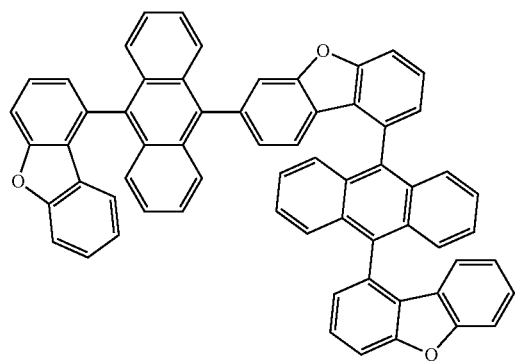
480
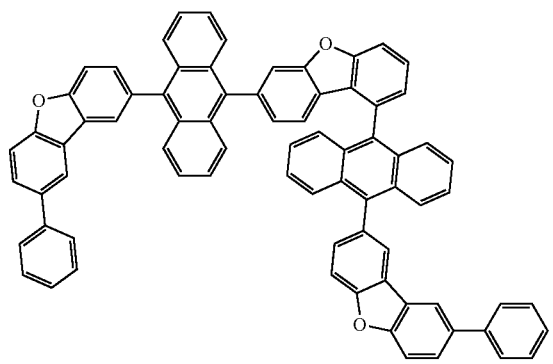
481
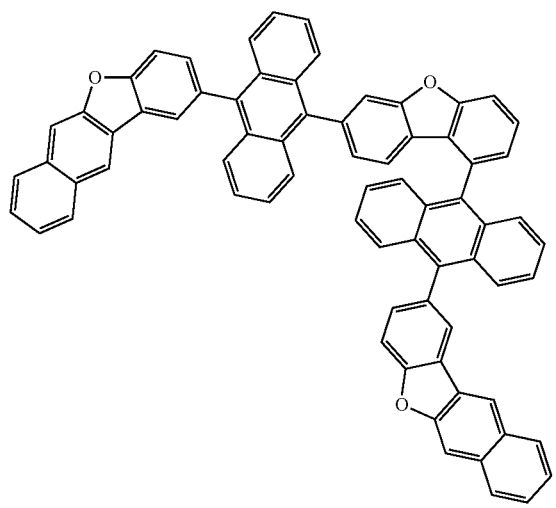
482
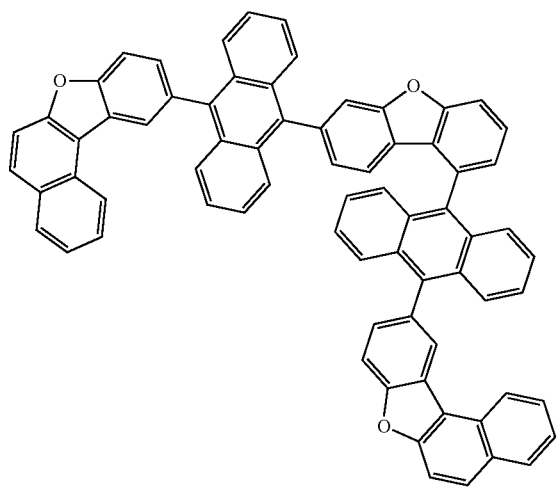

-continued
483
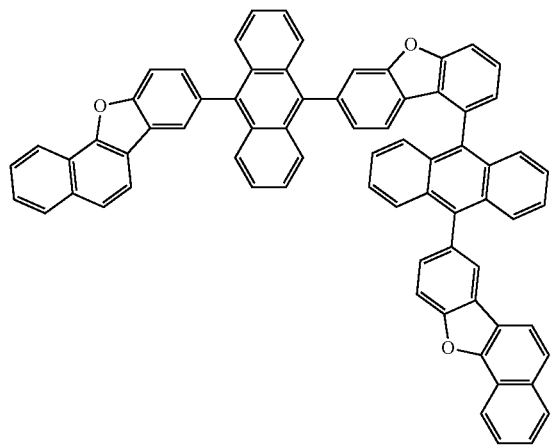
484
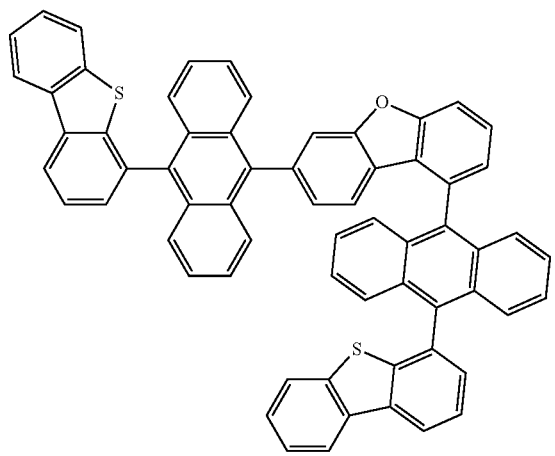
485
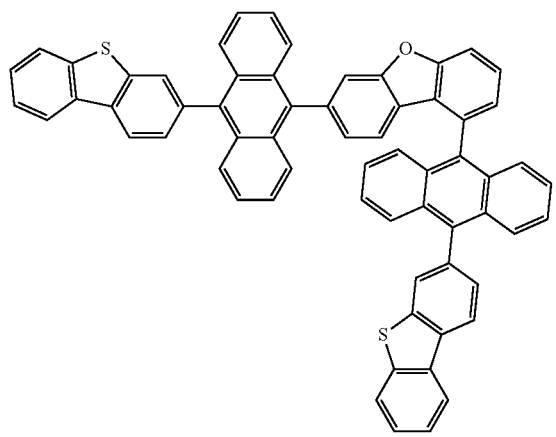
486
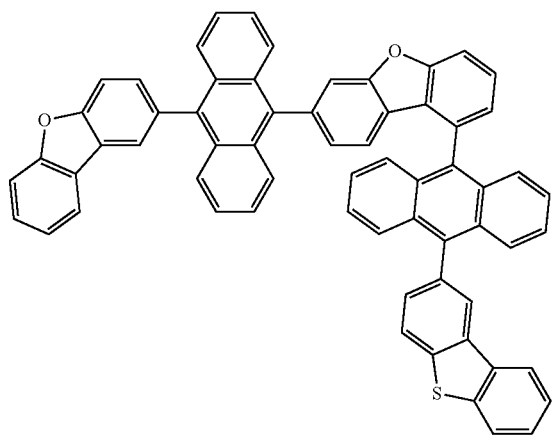
487
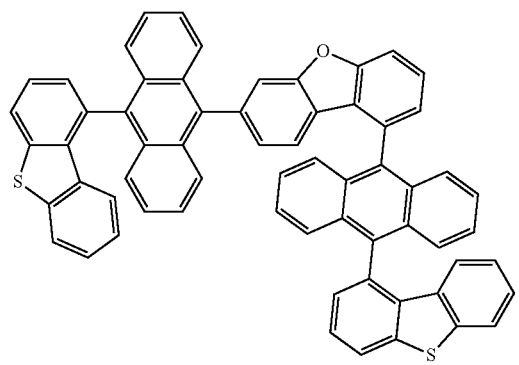
488
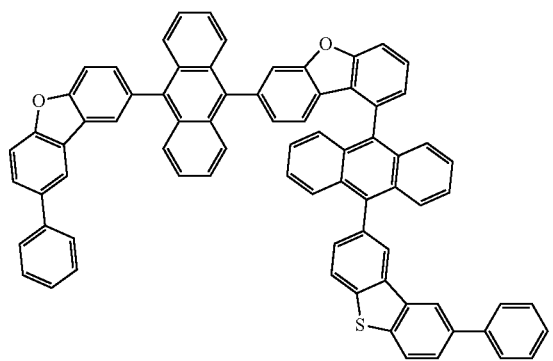

-continued
489
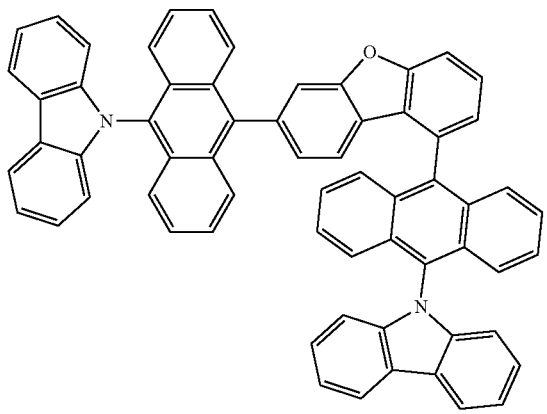
490
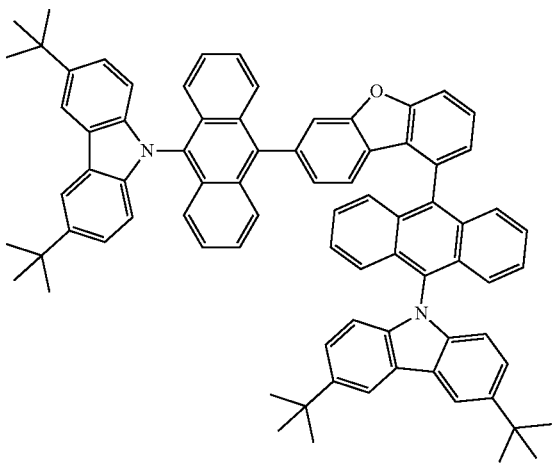
491
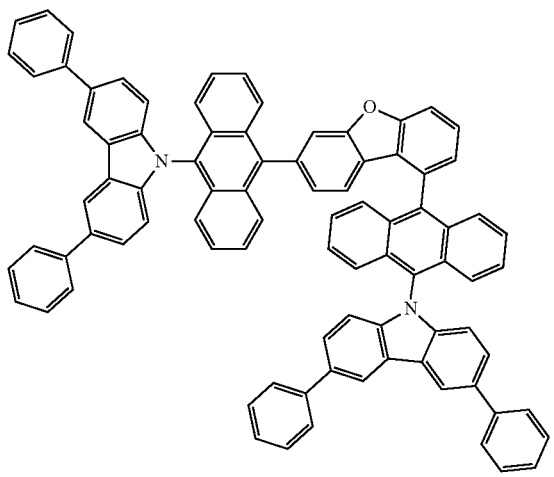
492
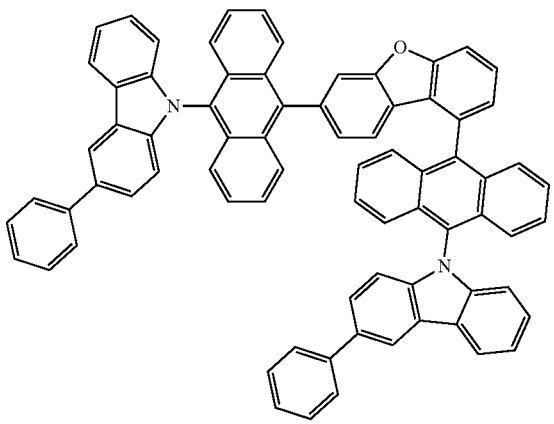
493
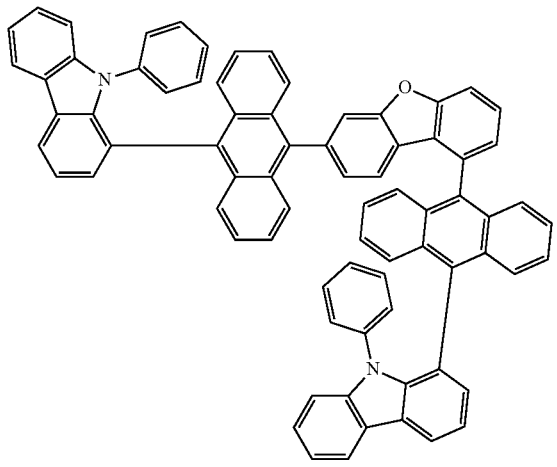
494
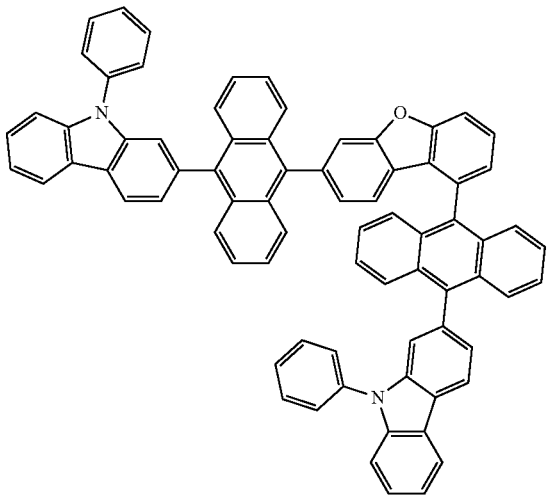

-continued
495
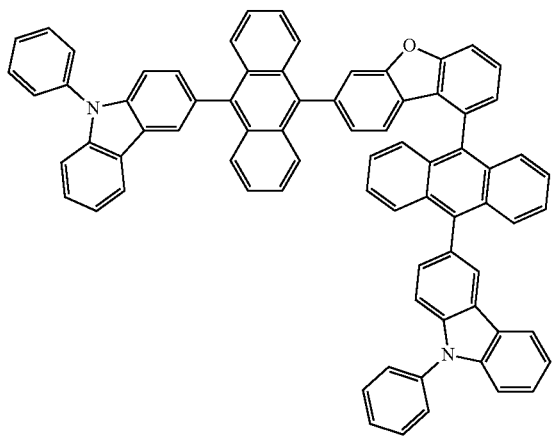
496
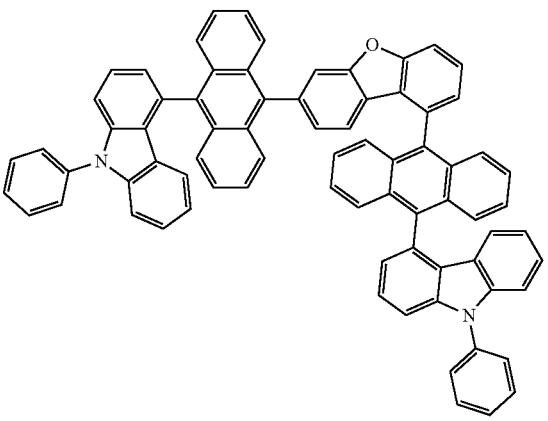
497
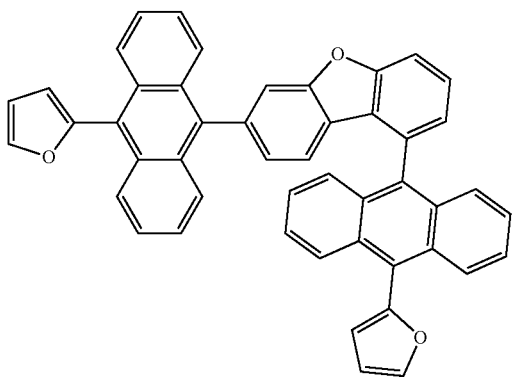
498
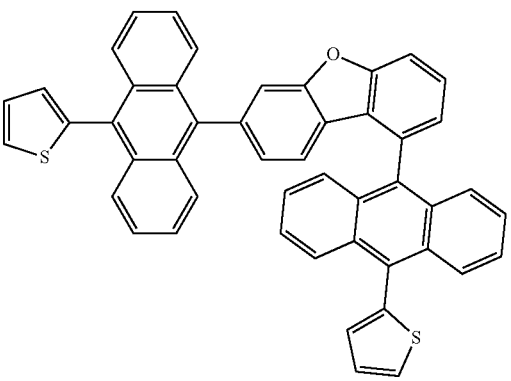
499
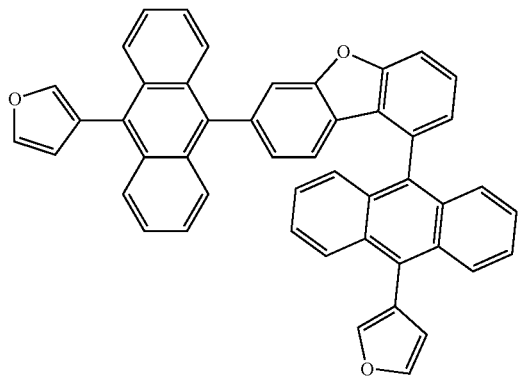
500
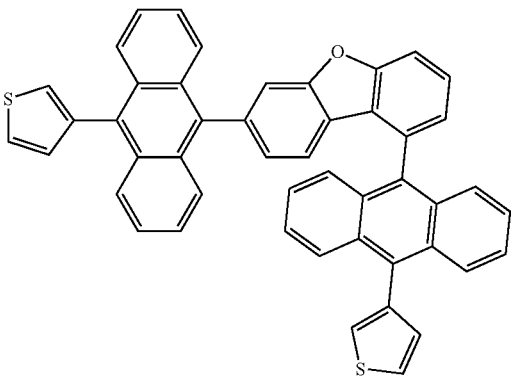
501
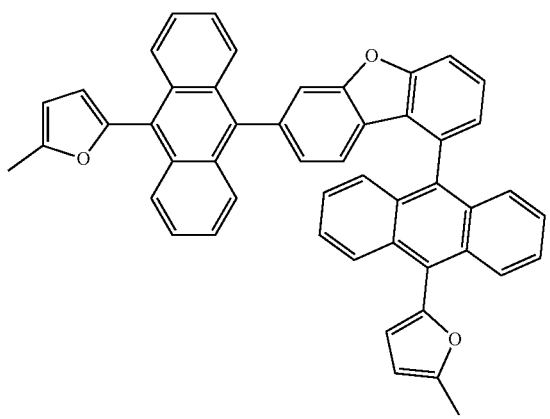
502
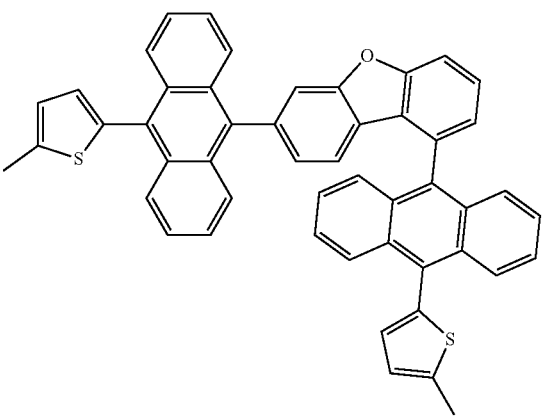

-continued
503
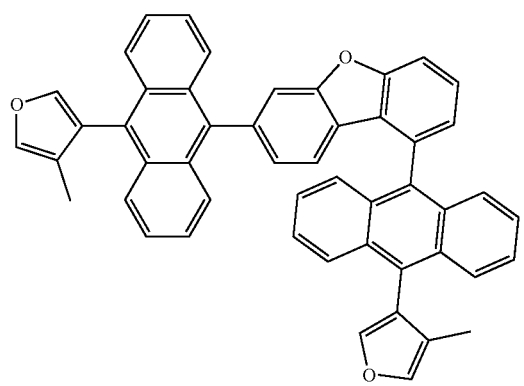
504
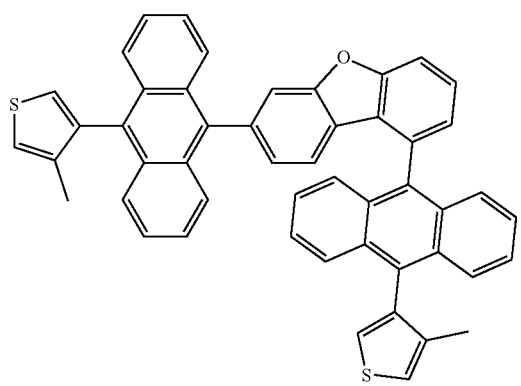
505
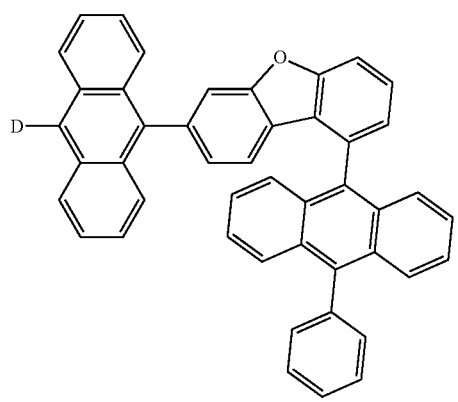
506
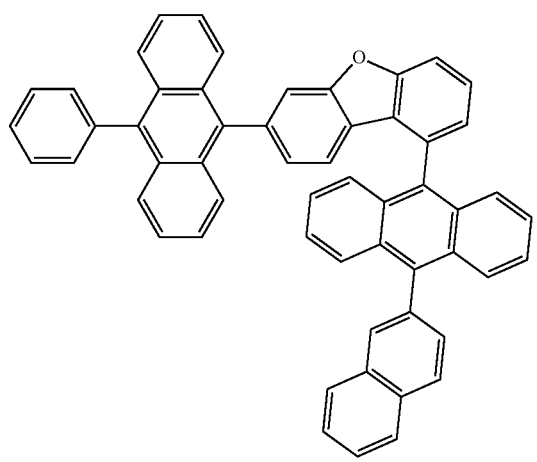
507
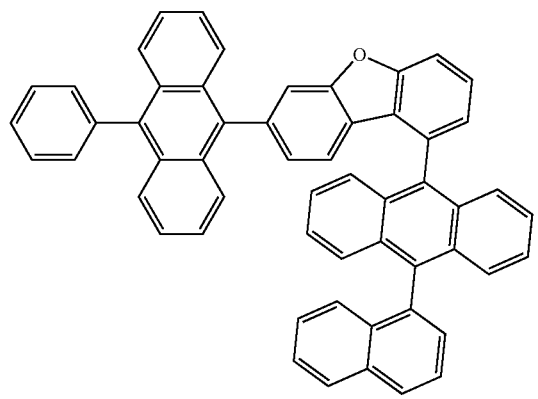
508
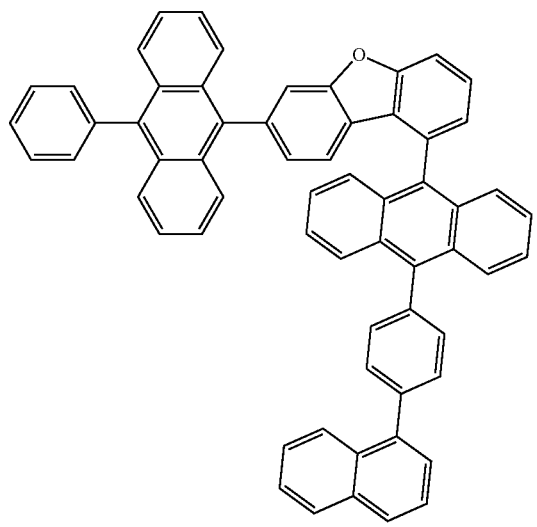

509
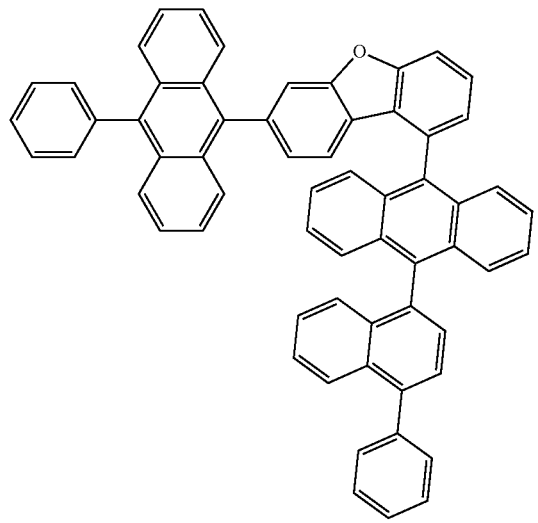
510
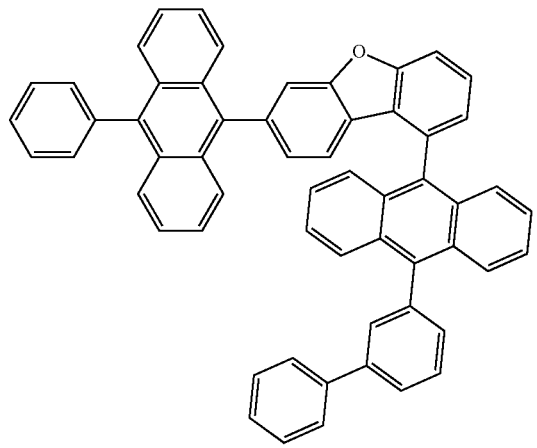
511
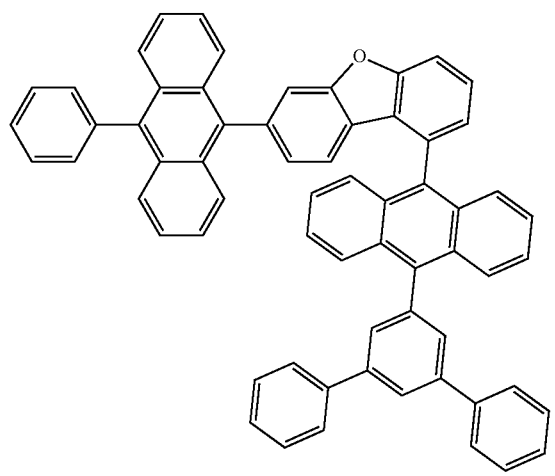
512
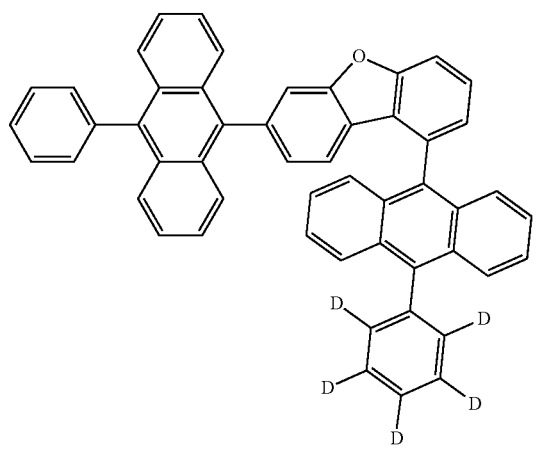
513
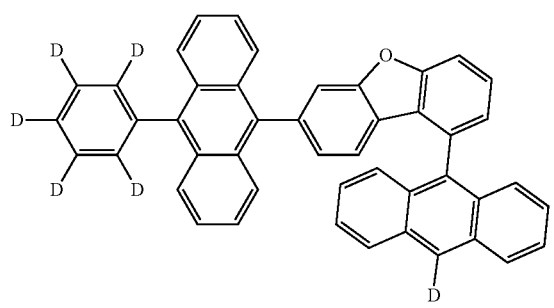
514
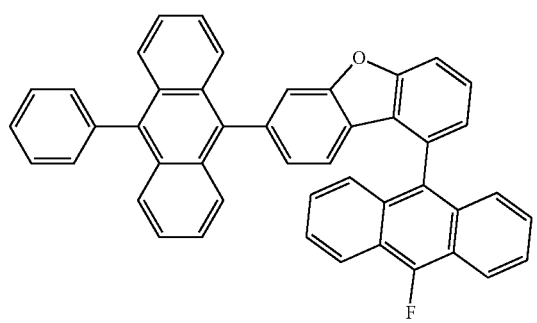

-continued
| 515 | 516 |
|---|---|
| 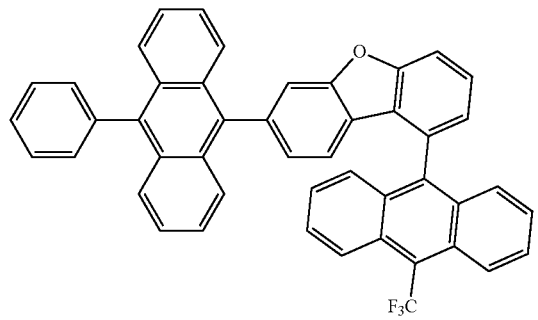 | 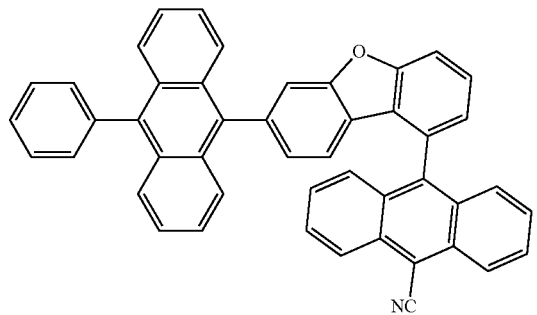 |
| 517 | 518 |
| 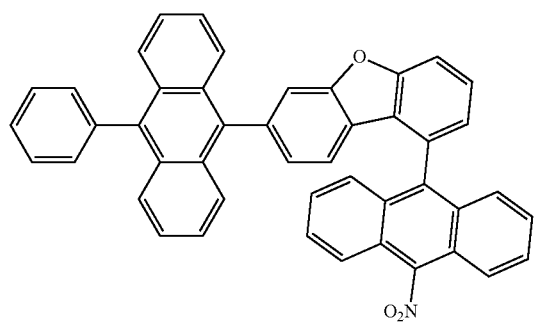 | 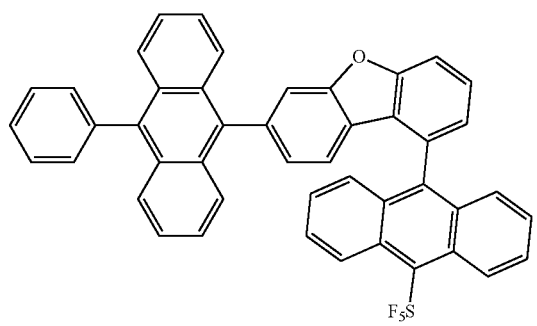 |
| 519 | 520 |
| 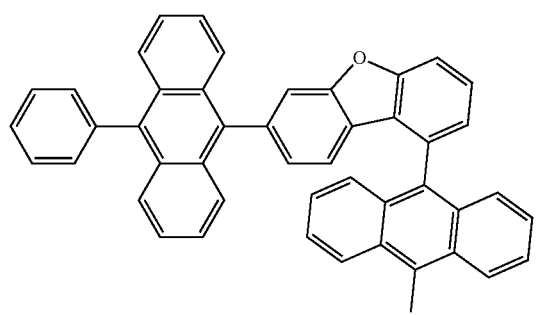 | 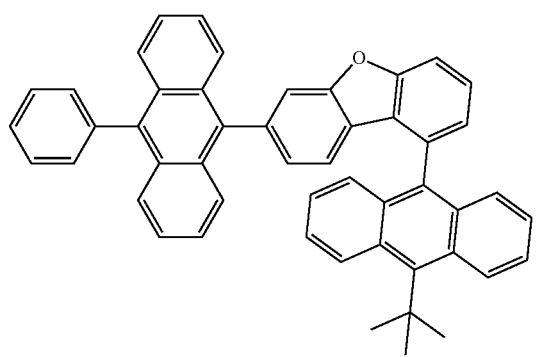 |
| 521 | 522 |
| 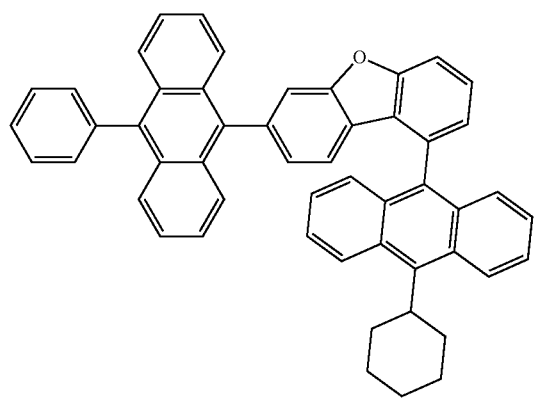 | 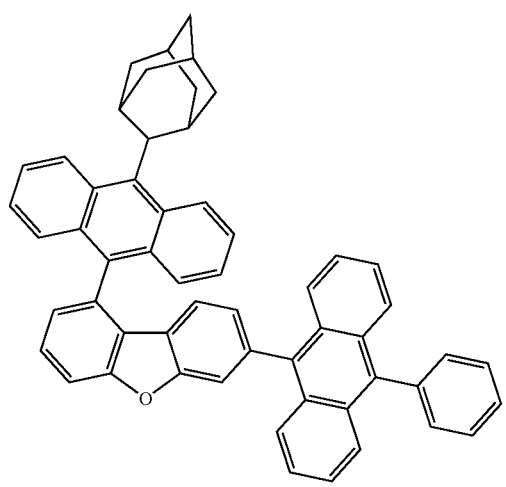 |

-continued
523
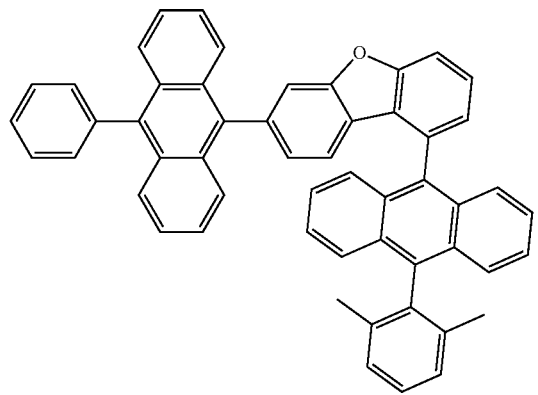
524
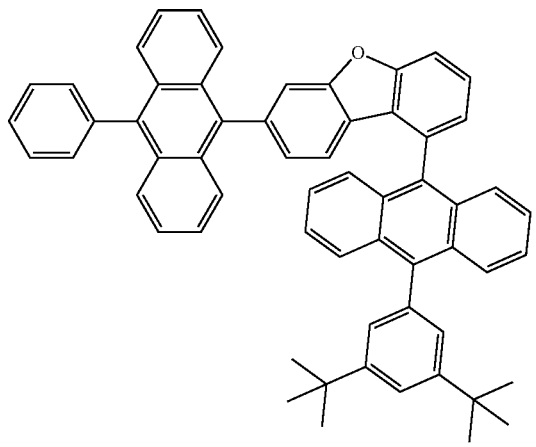
525
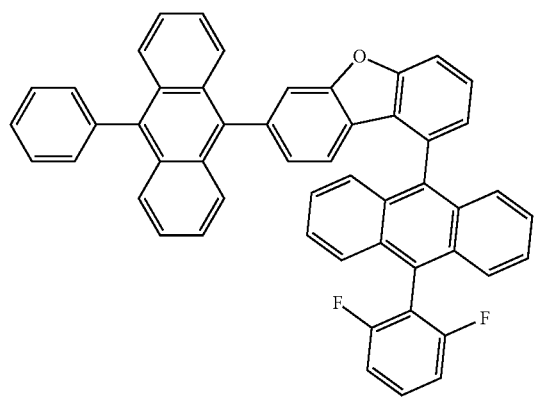
526
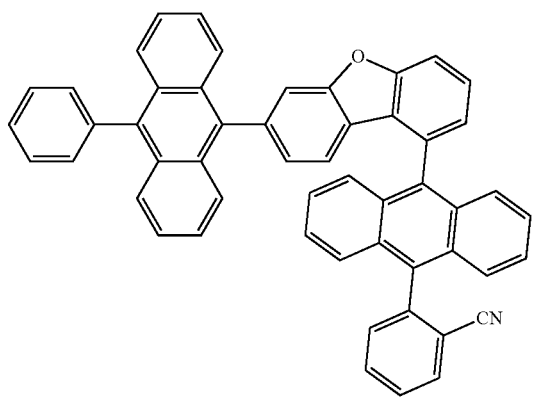
527
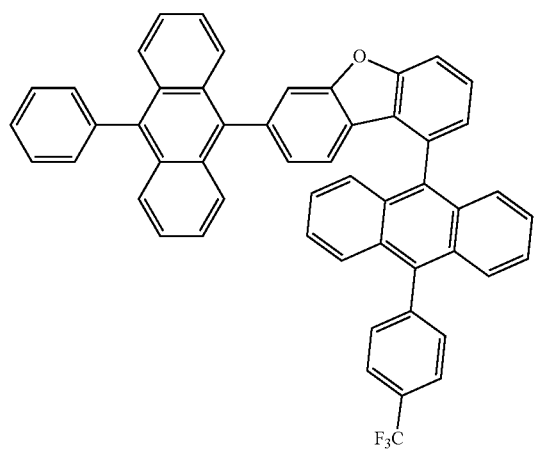
528
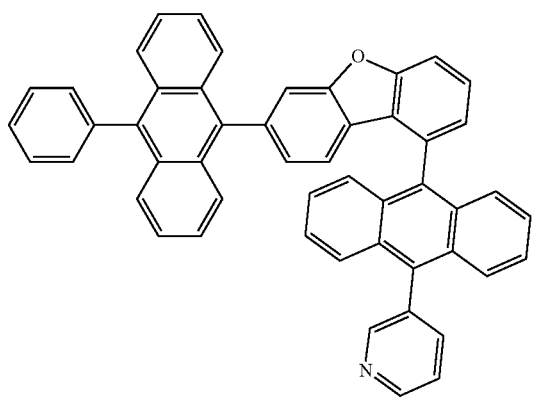

-continued
529
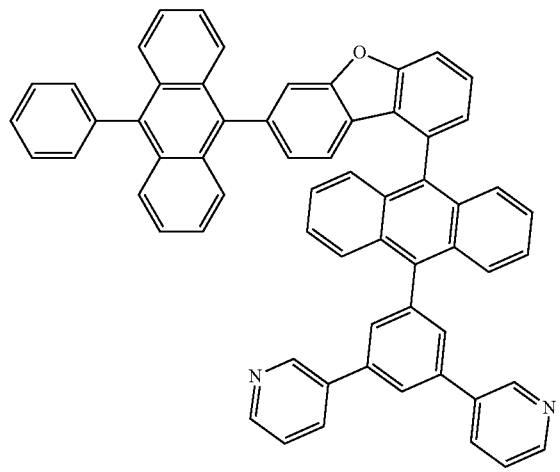
530
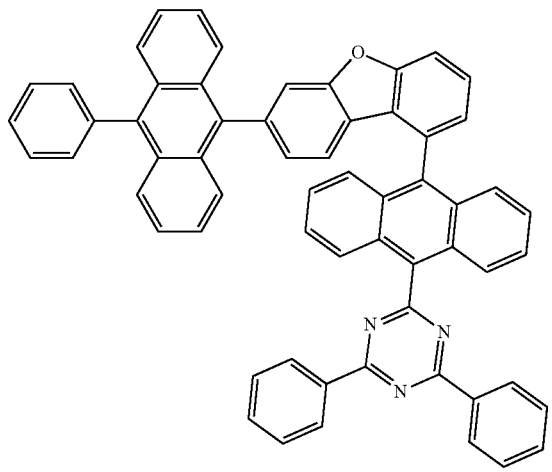
531
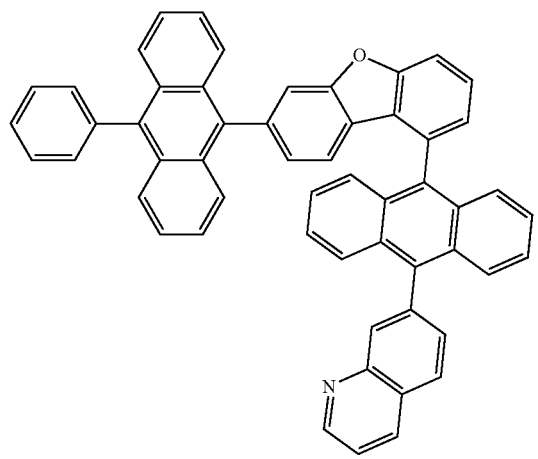
532
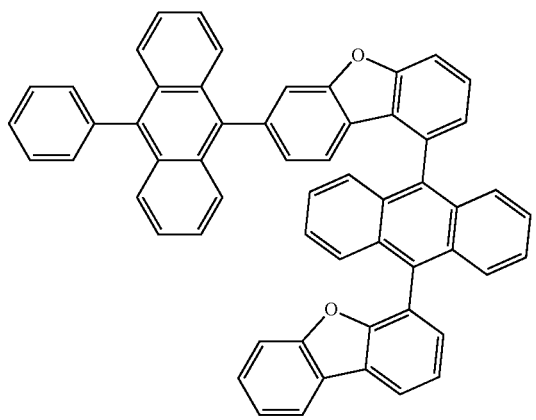
533
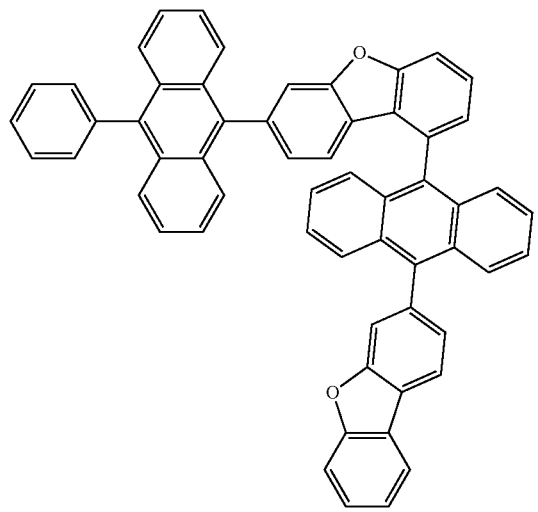
534
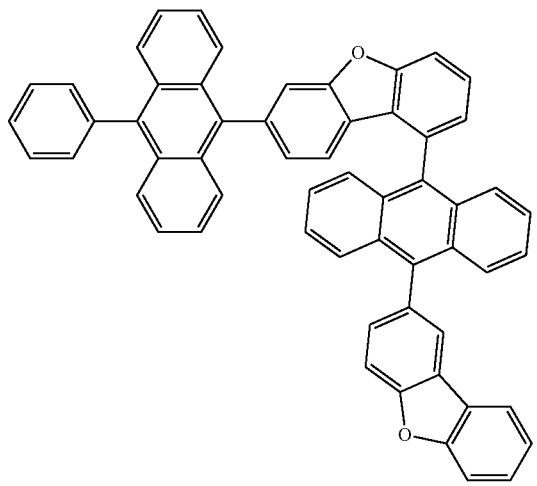

-continued
535
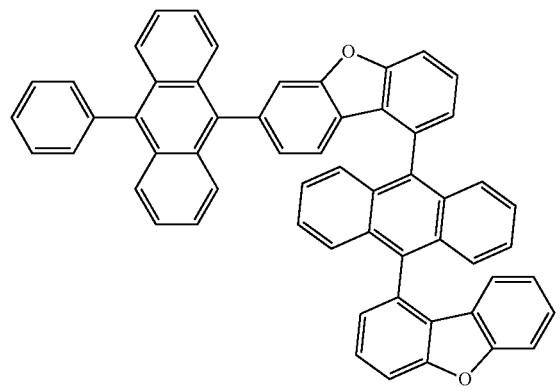
536
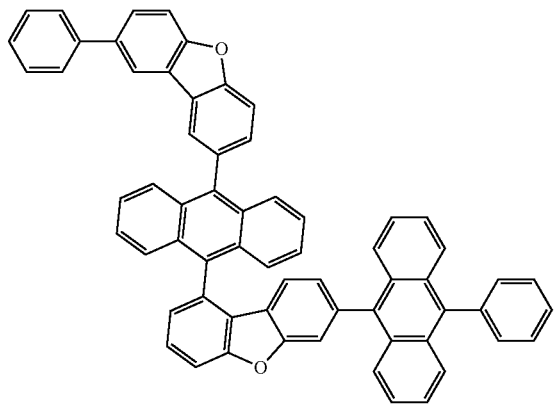
537
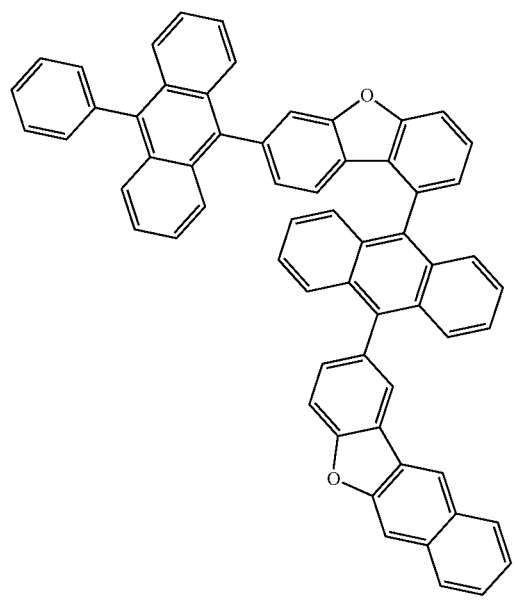
538
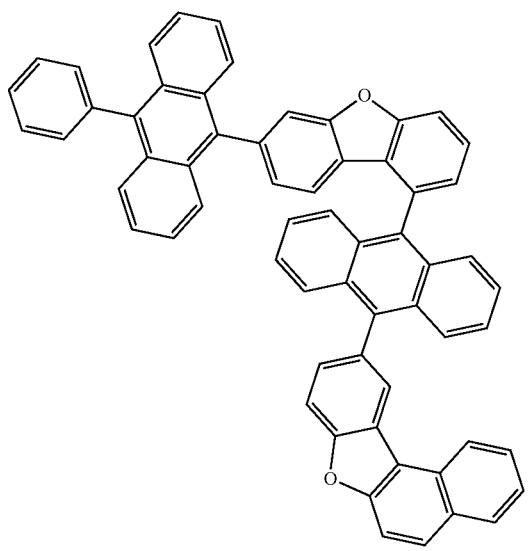
539
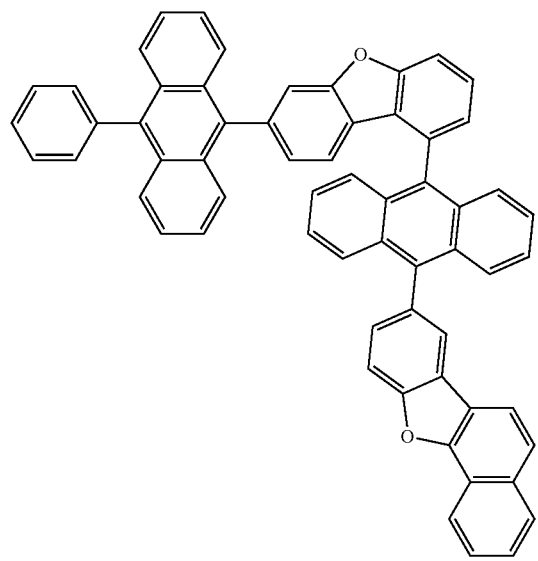
540
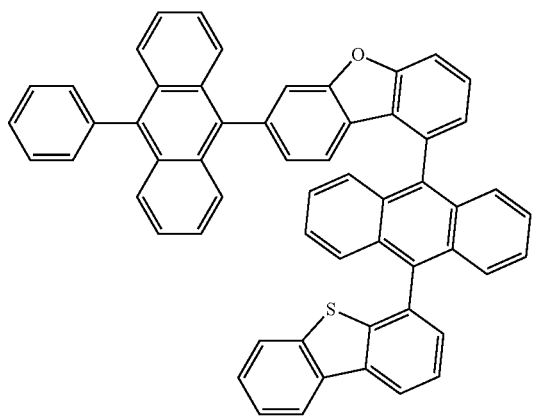

-continued
541
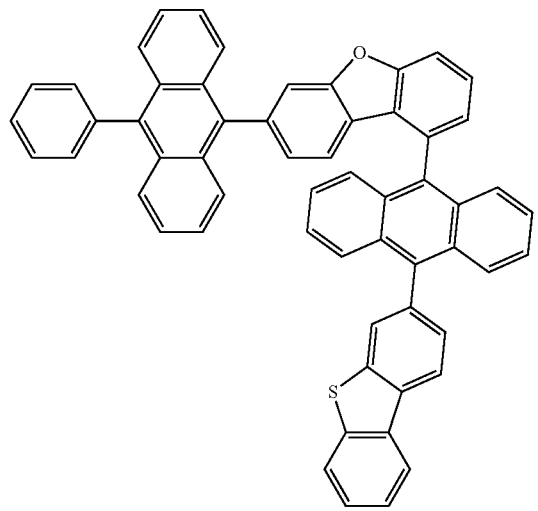
542
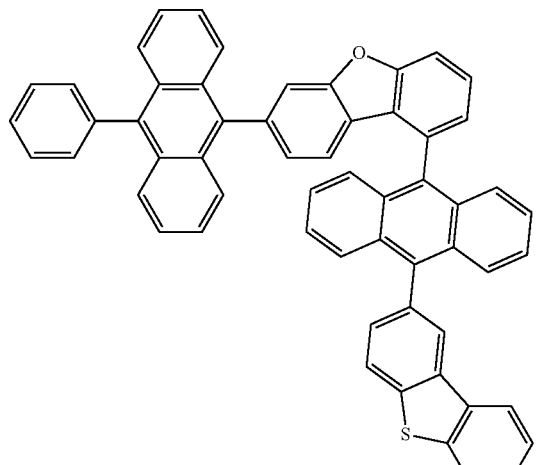
543
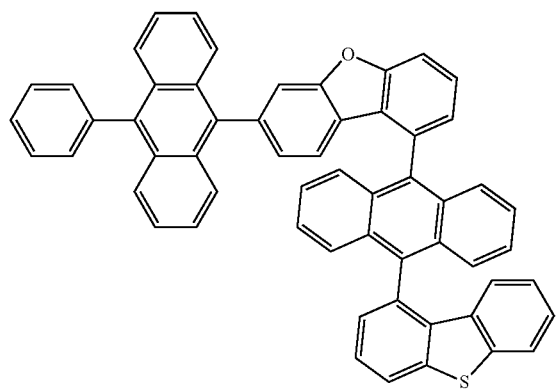
544
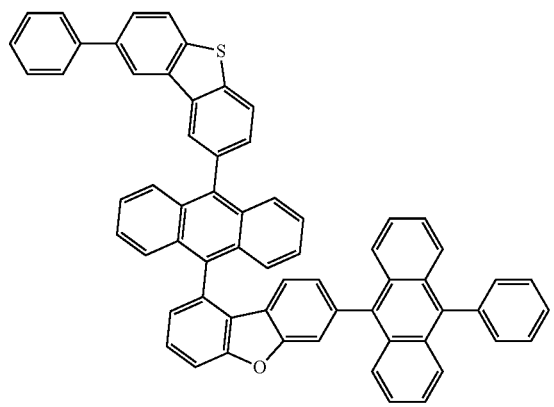
545
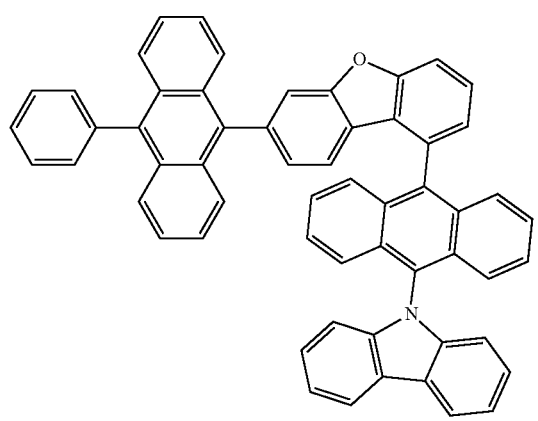
546
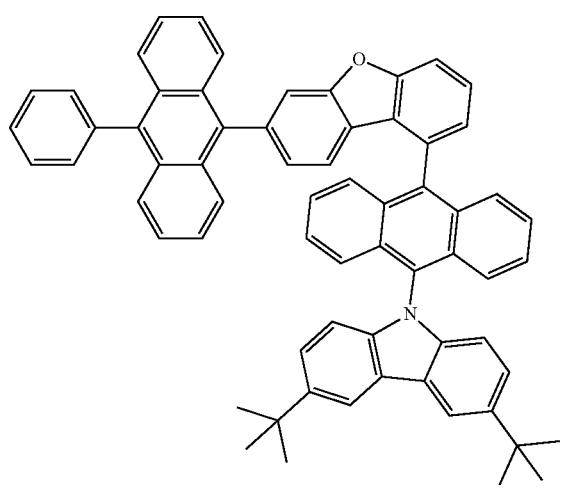

-continued
547
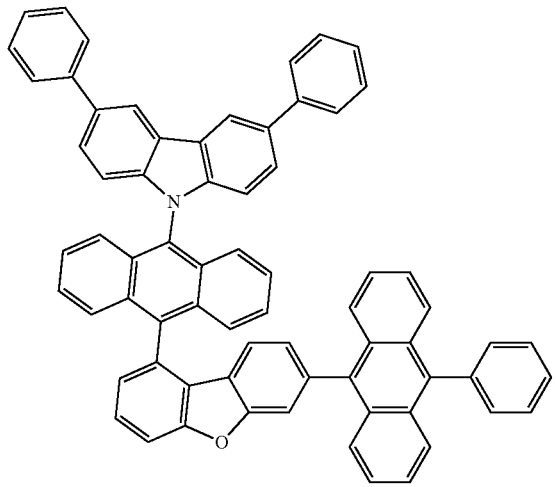
548
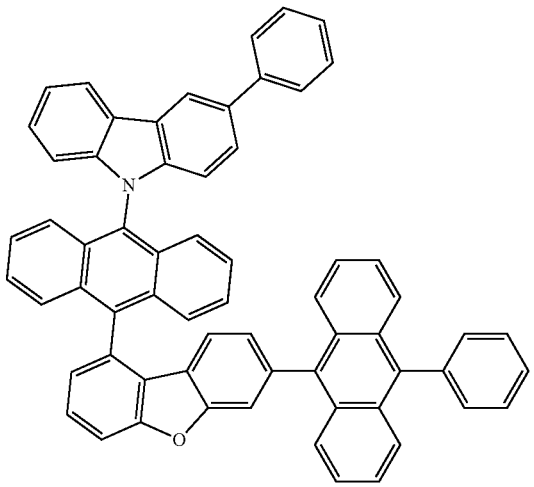
549
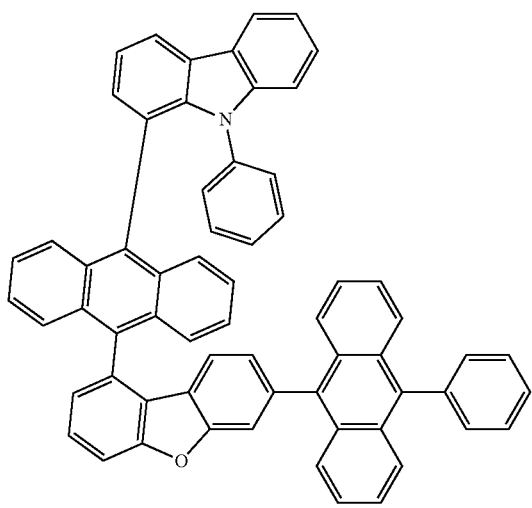
550
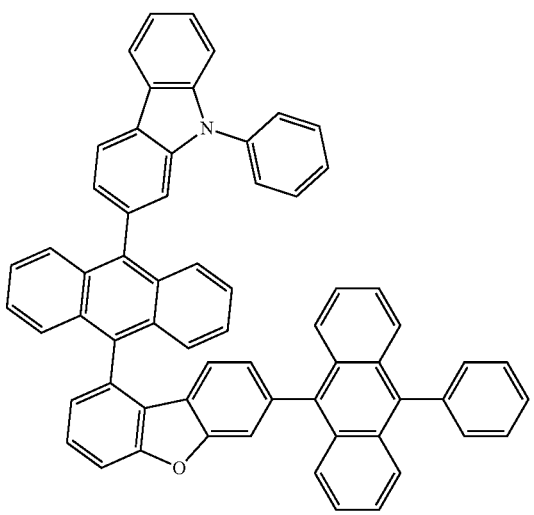
551
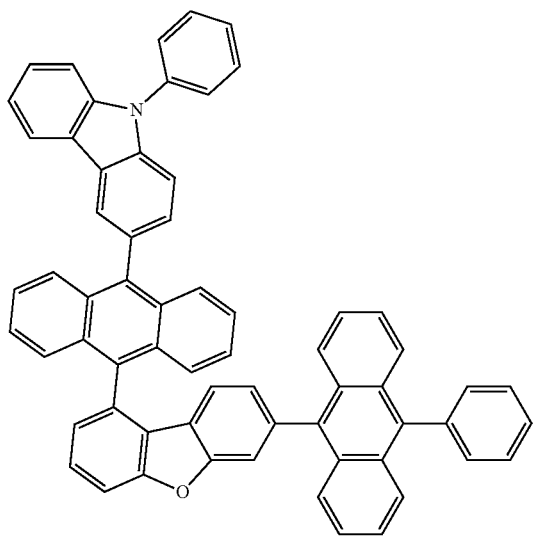
552
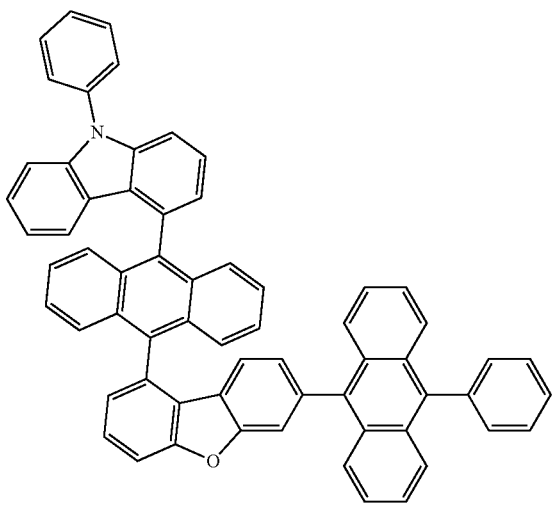

553
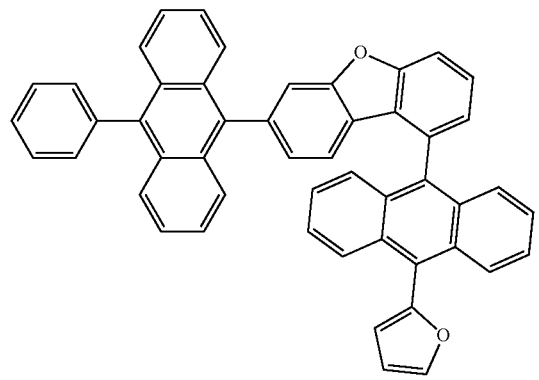
554
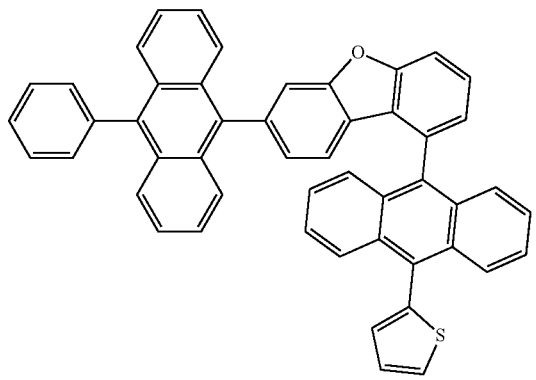
555
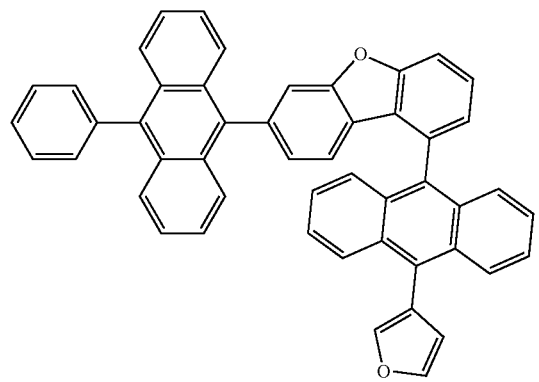
556
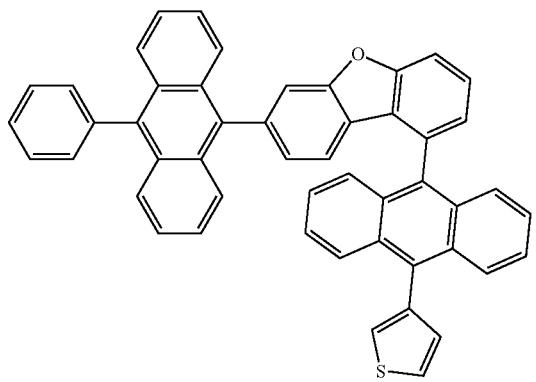
557
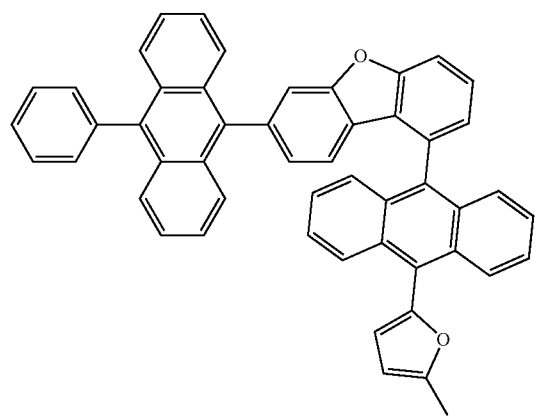
558
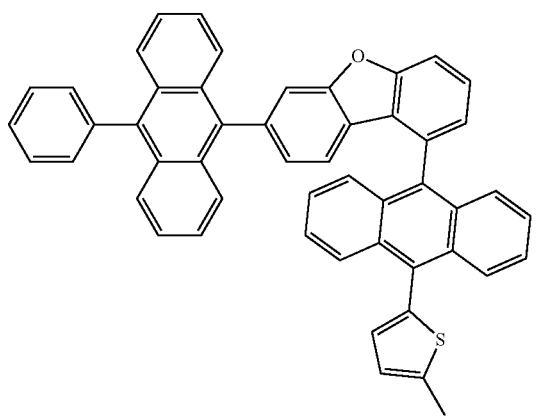
559
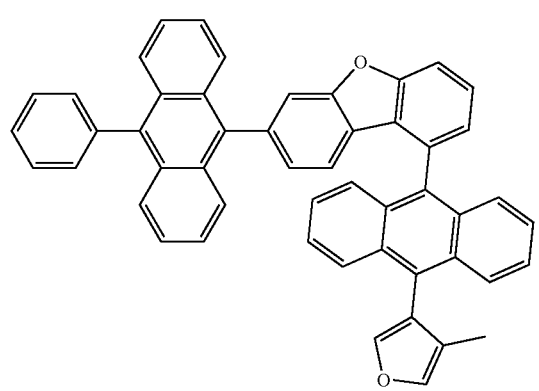
560
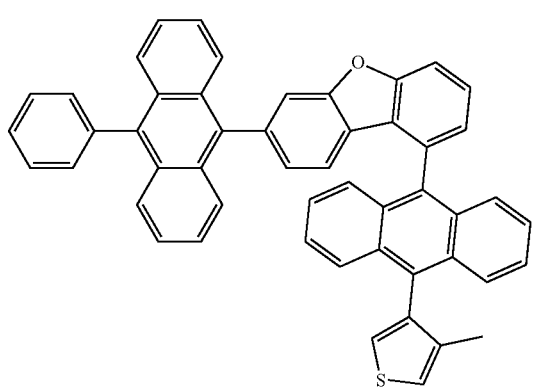

-continued
561
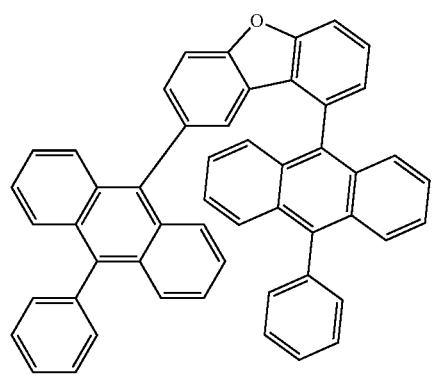
562
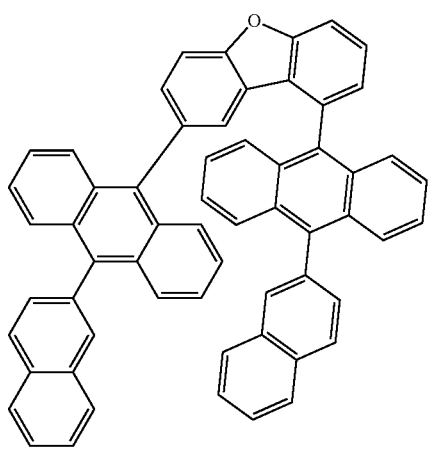
563
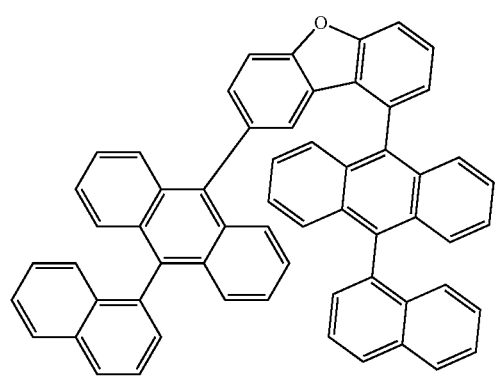
564
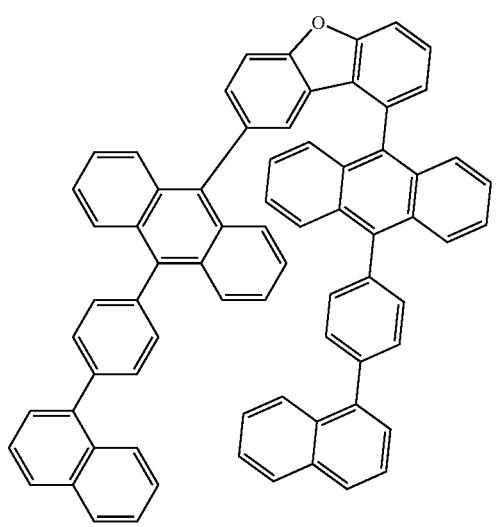
565
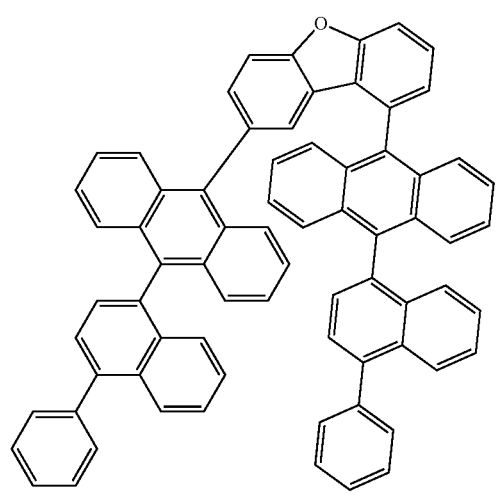
566
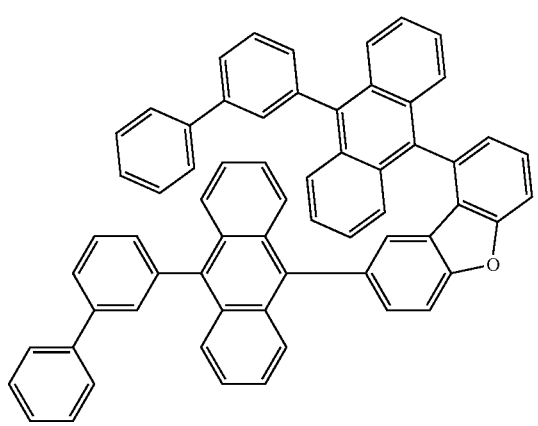

-continued
567
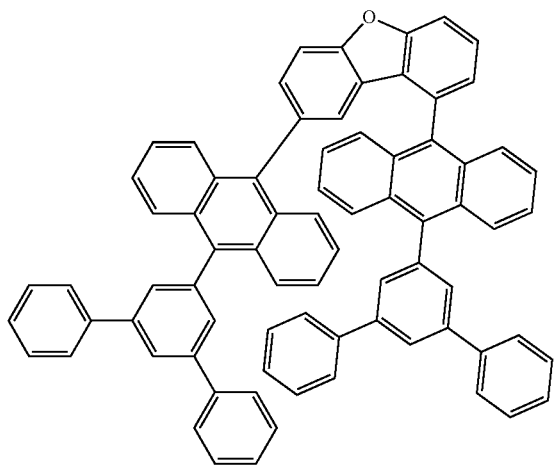
568
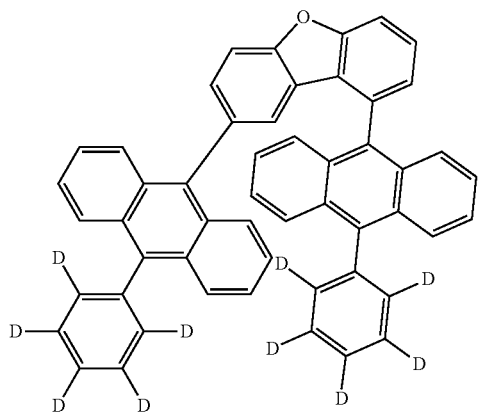
569
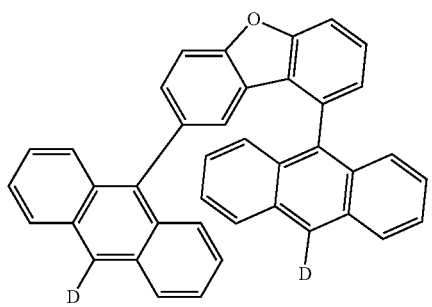
570
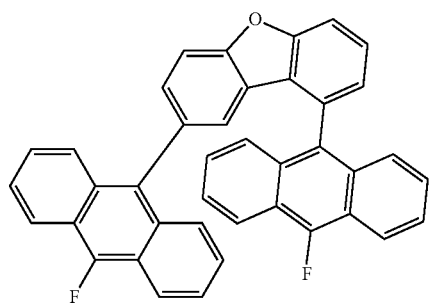
571
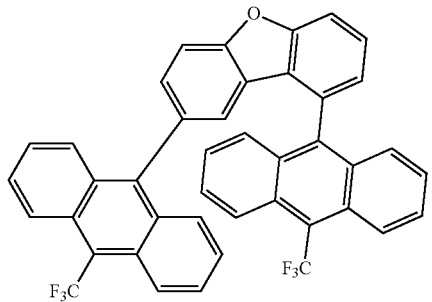
572
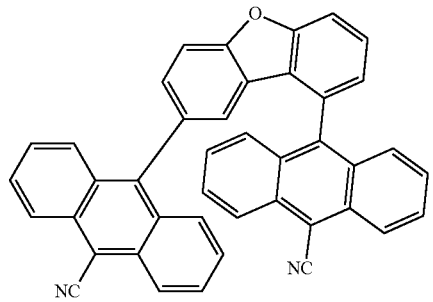
573
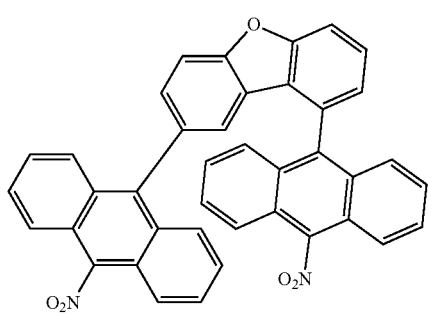
574
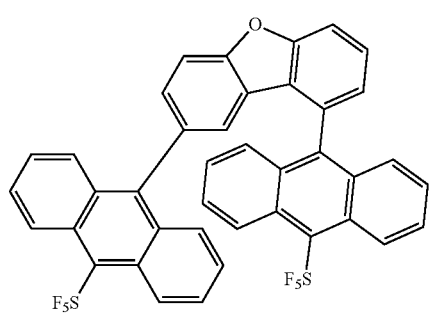

-continued
| 1681 | 1682 |
|---|---|
| 575 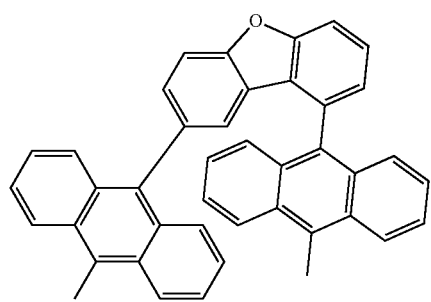 | 576 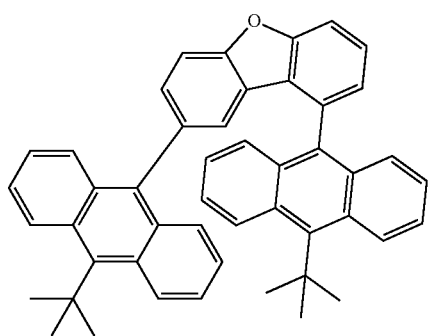 |
| 577 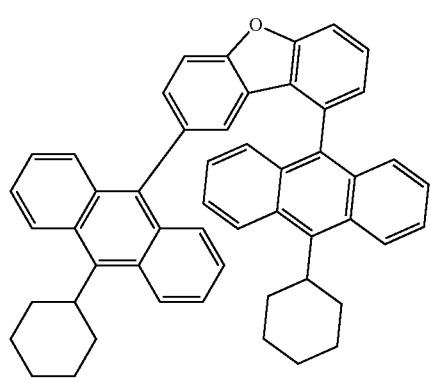 | 578 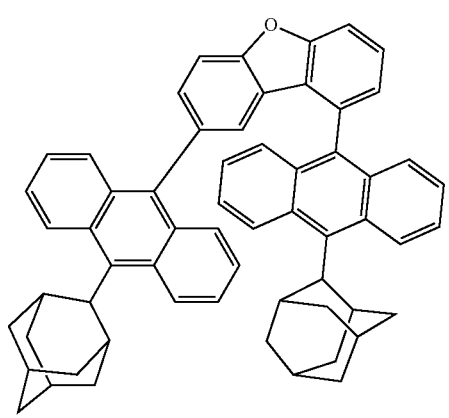 |
| 579 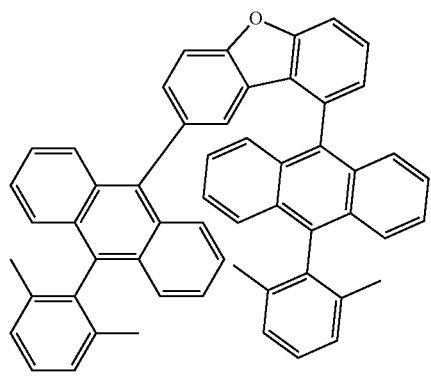 | 580 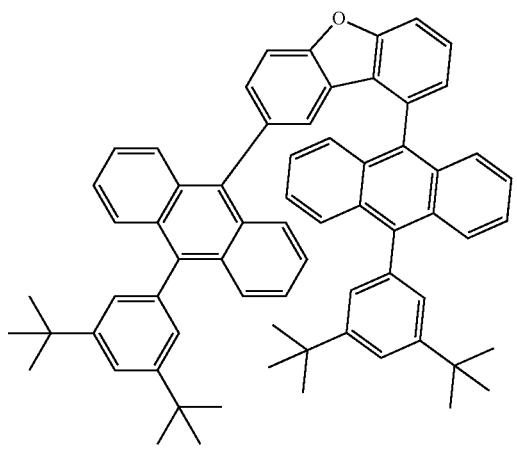 |
| 581 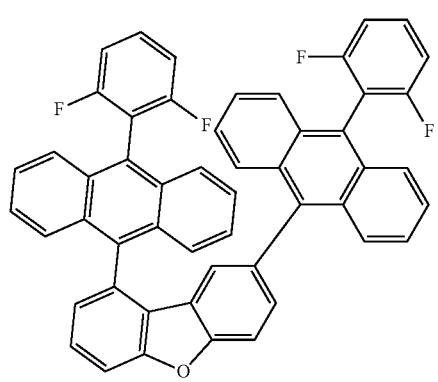 | 582 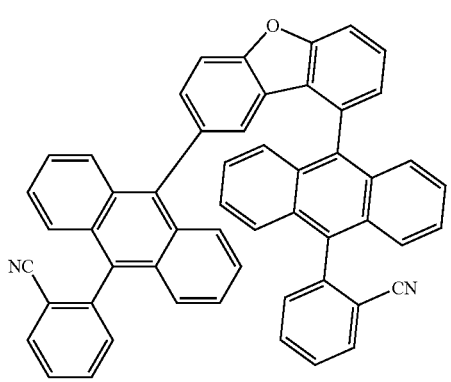 |

-continued
583
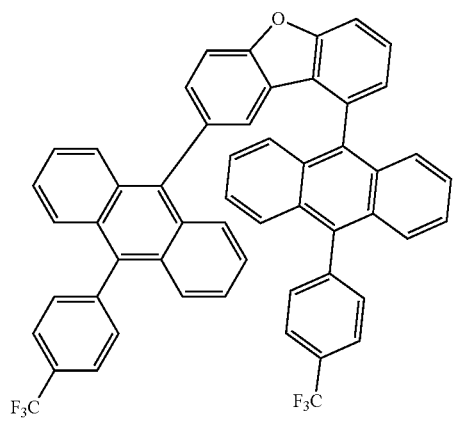
584
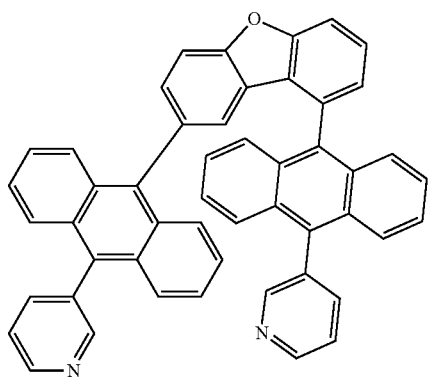
585
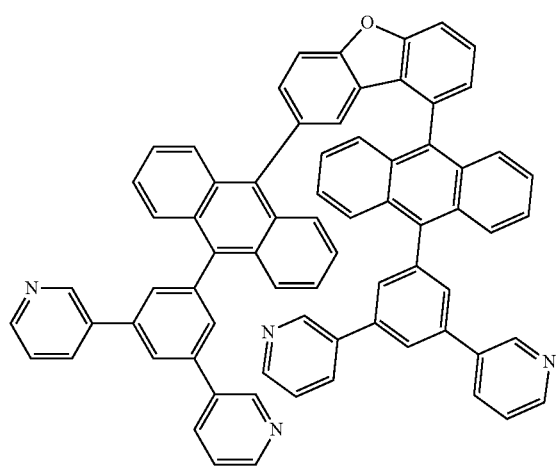
586
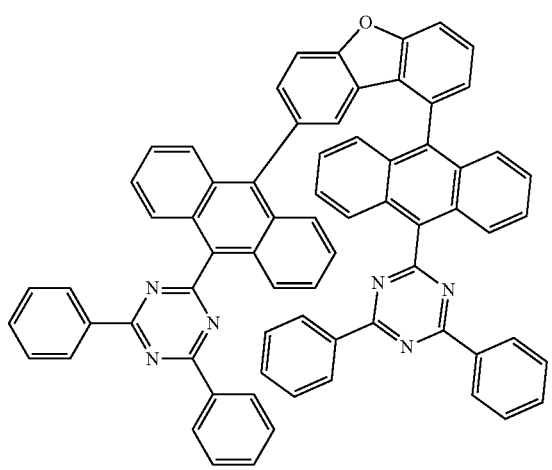
587
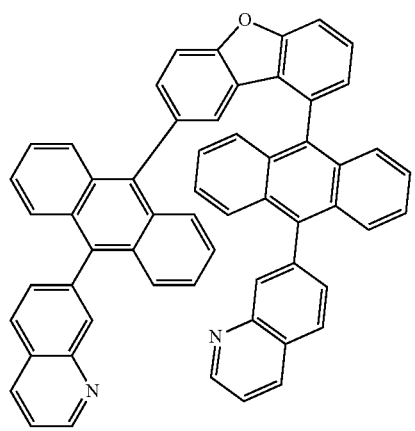
588
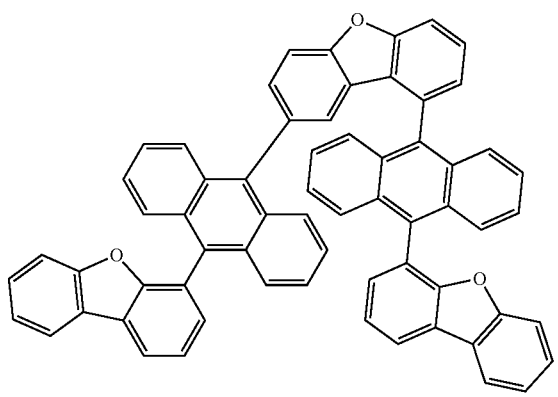

-continued
589
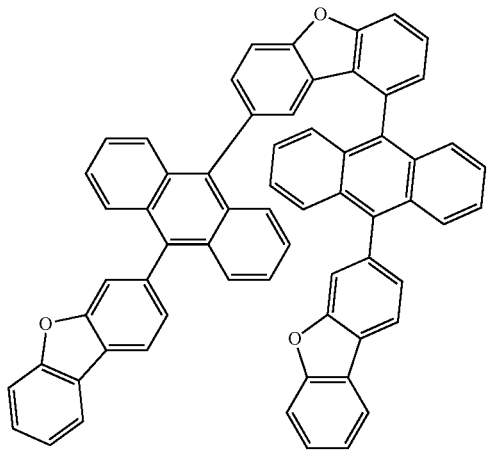
590
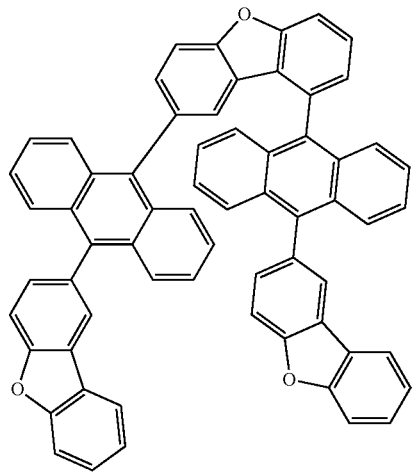
591
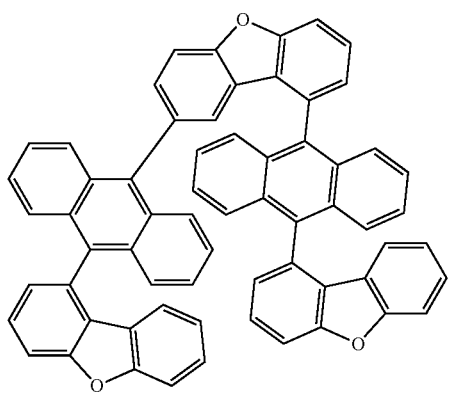
592
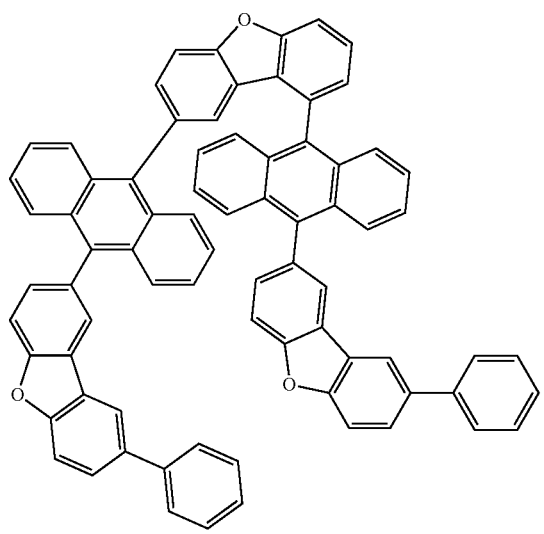
593
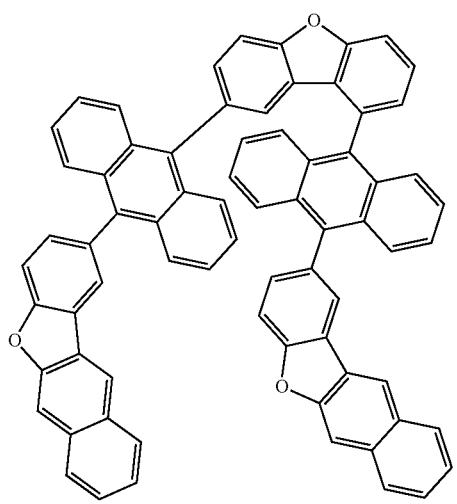
594
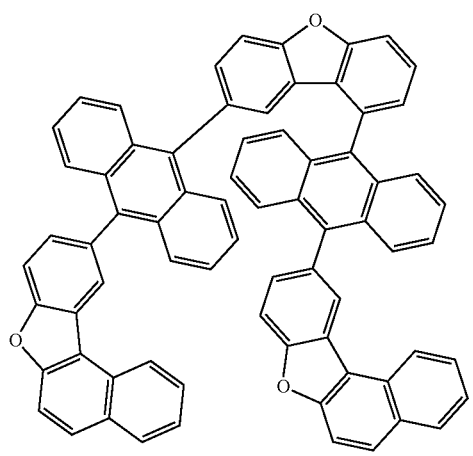

-continued
595
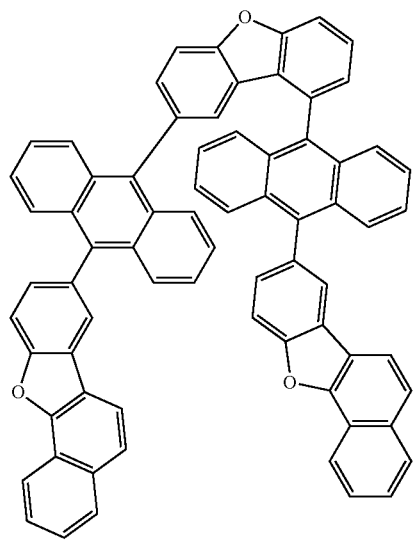
596
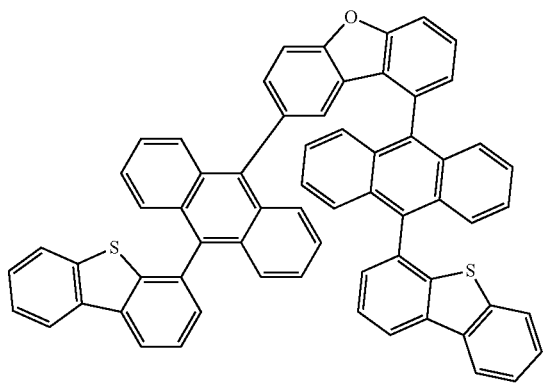
597
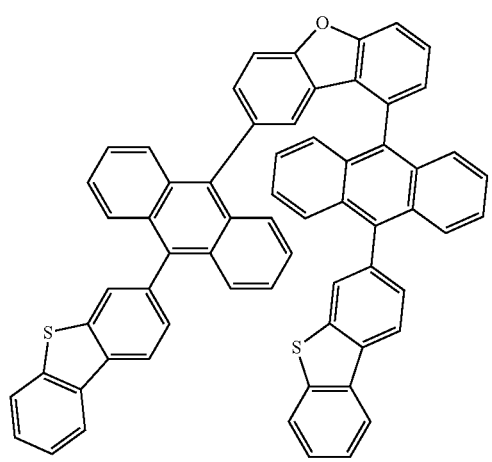
598
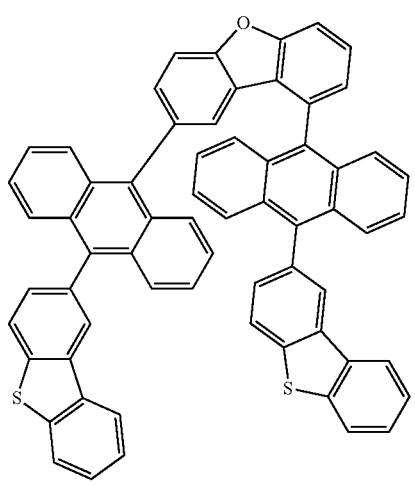
599
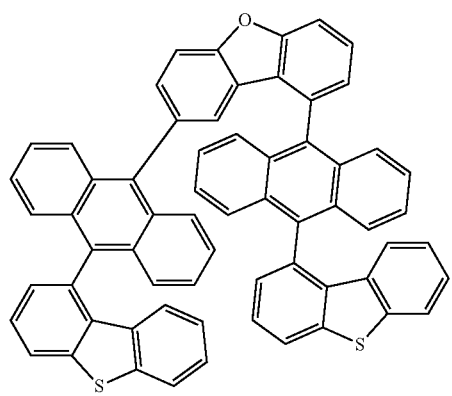
600
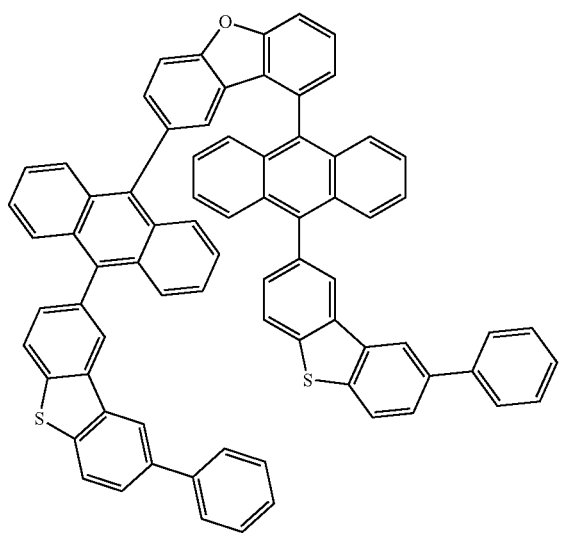

601
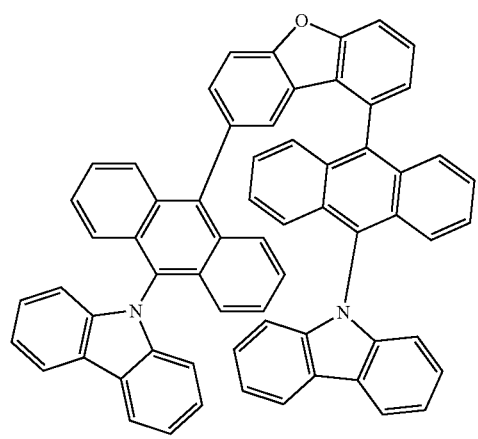
602
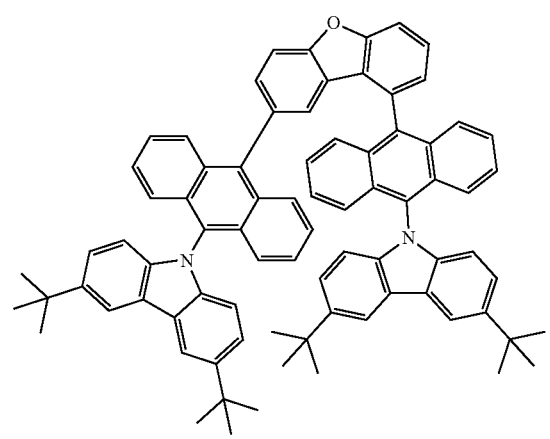
603
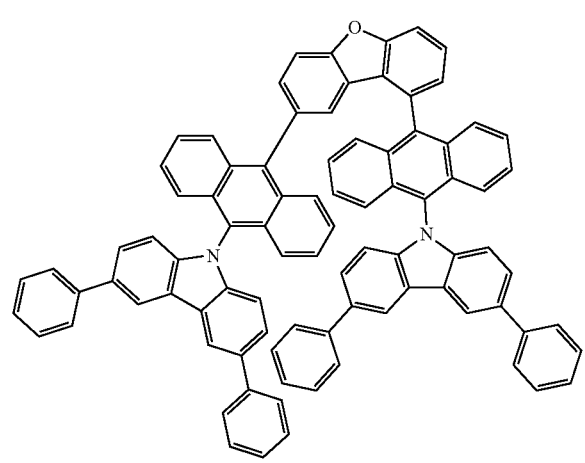
-continued
604
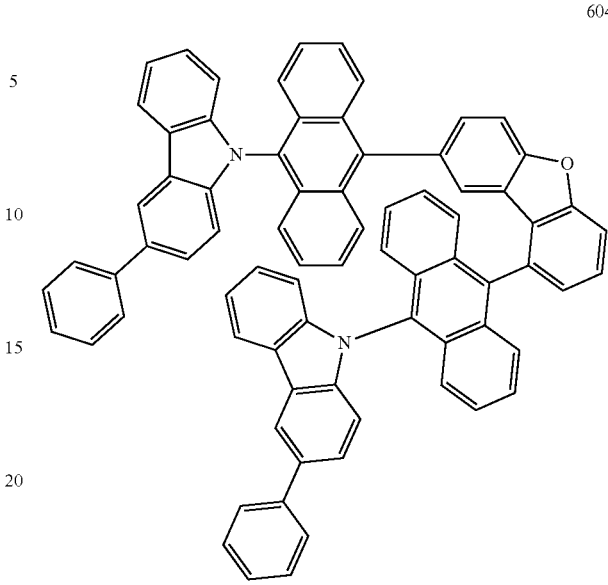
605
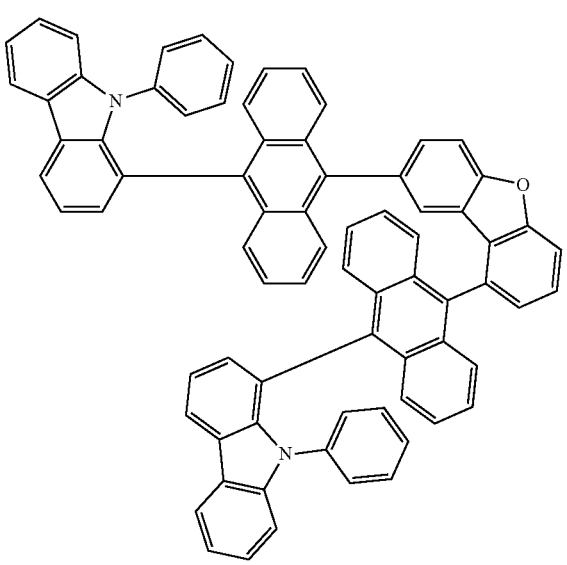

1691
-continued
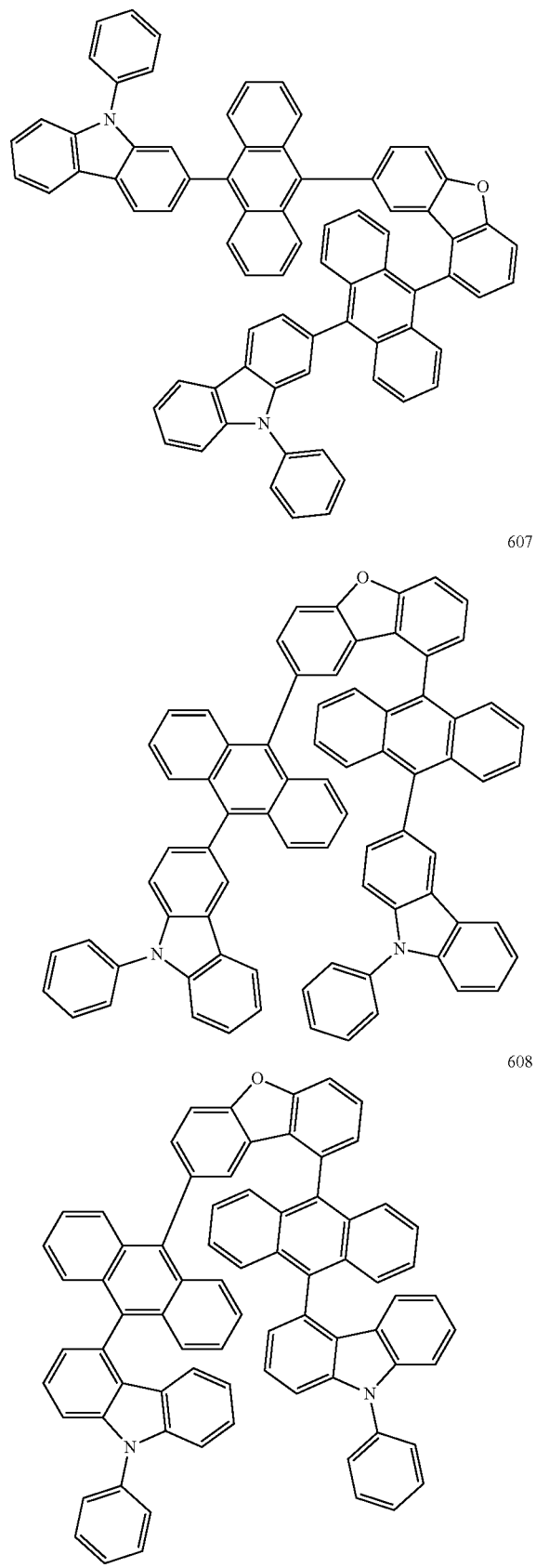
1692
-continued
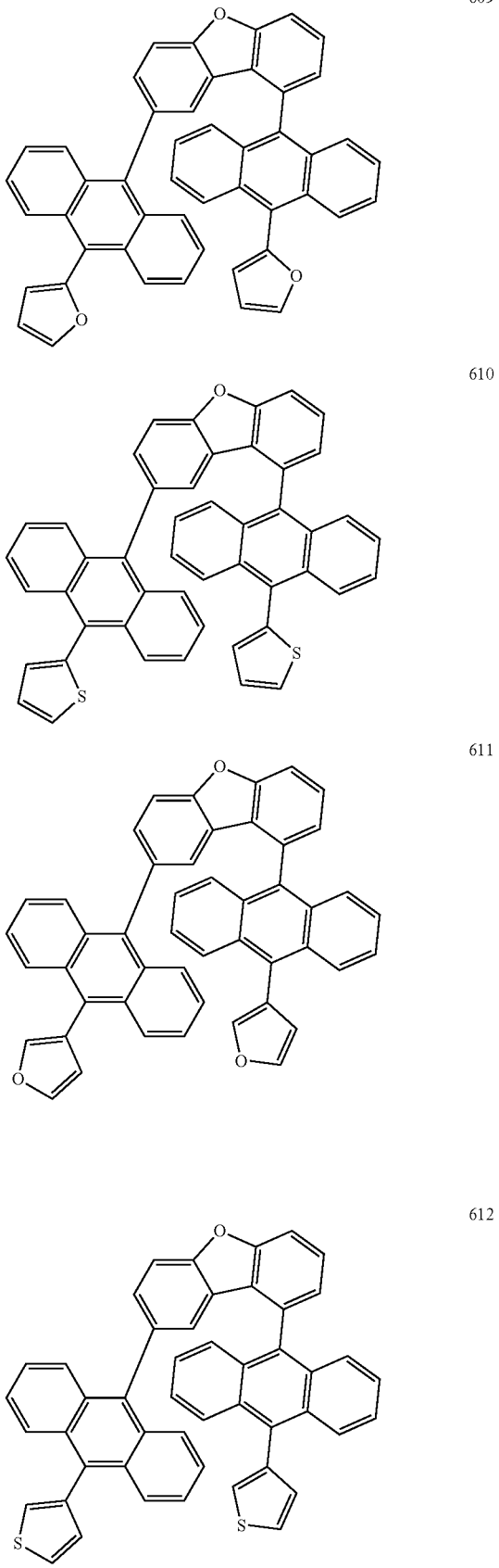

613 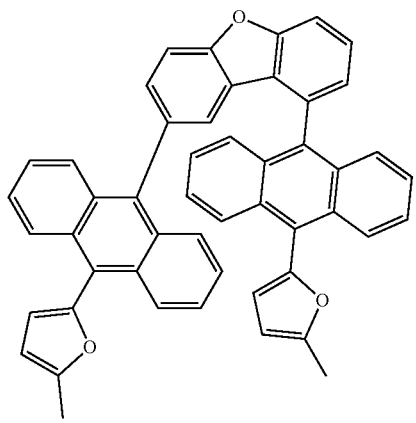
614 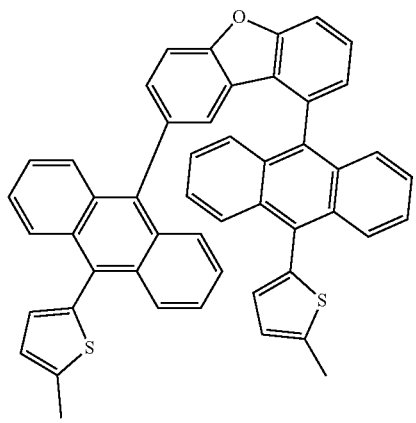
615 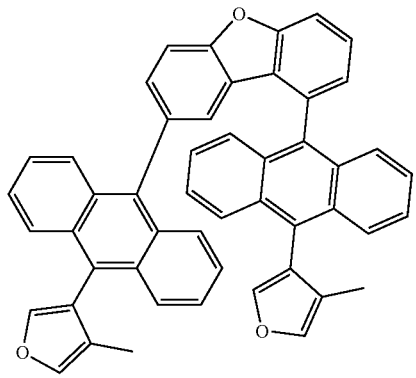
616 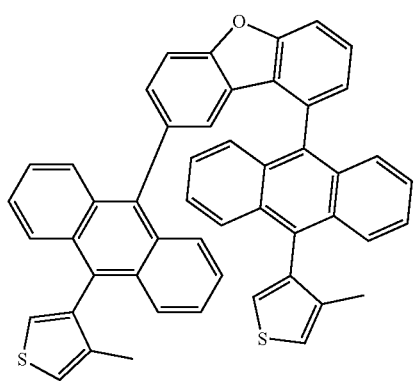
617 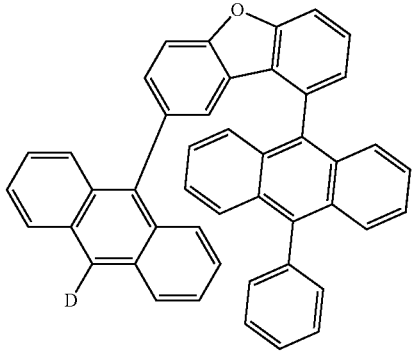
618 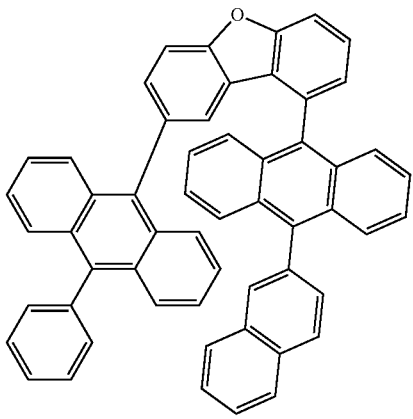
619 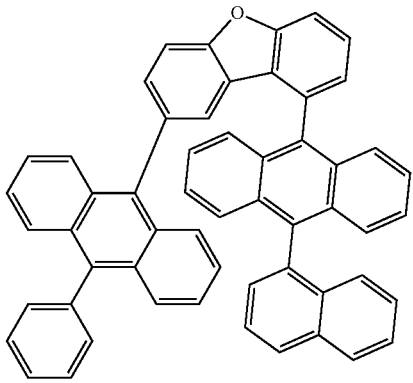
620 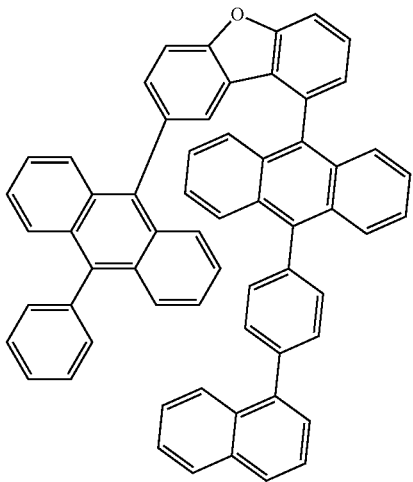

1695
-continued
621
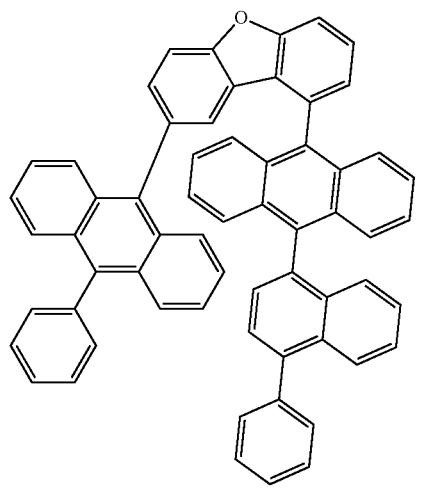
622
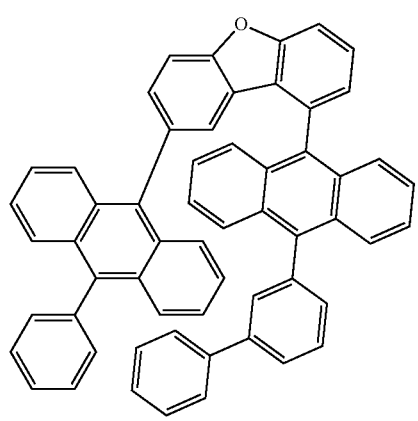
623
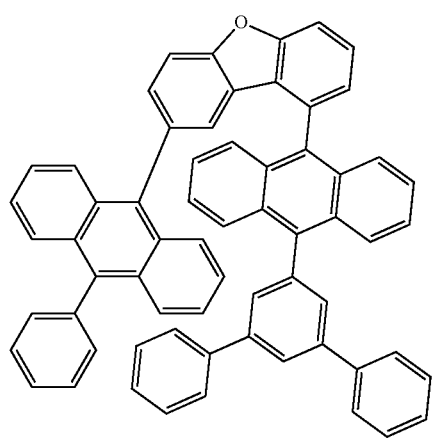
1696
-continued
624
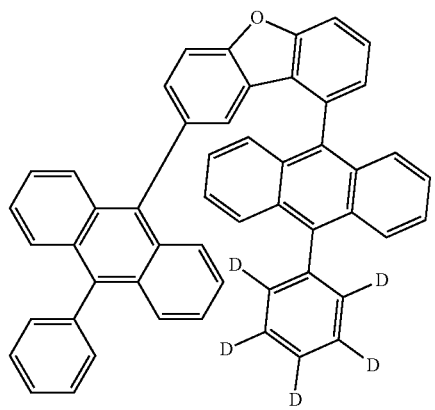
625
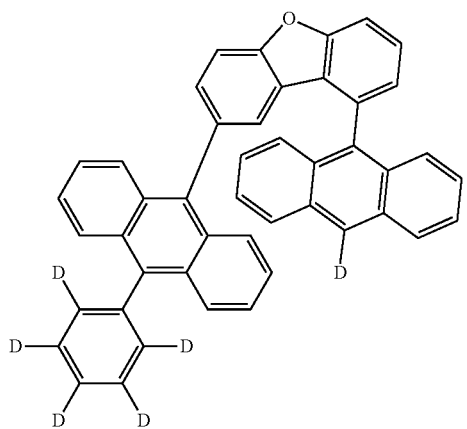
626
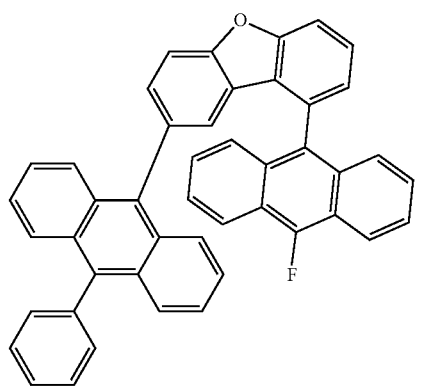
627
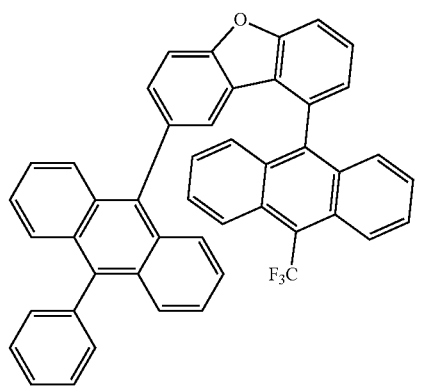

-continued
628
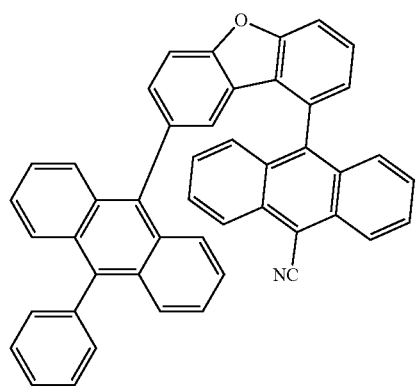
629
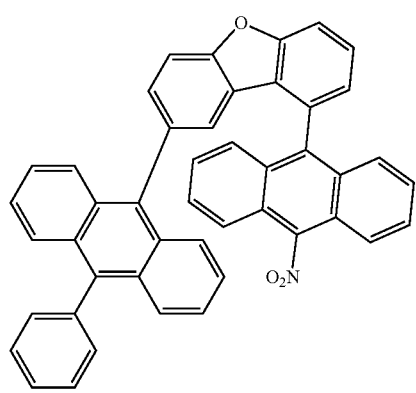
630
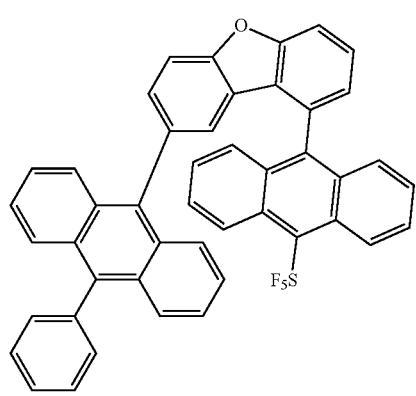
631
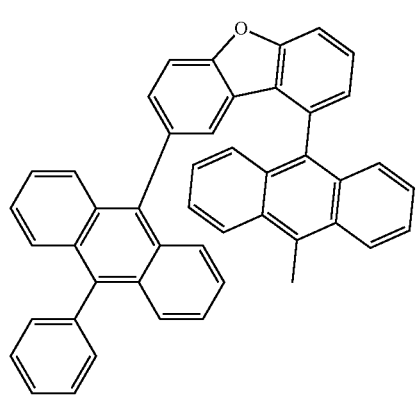
-continued
632
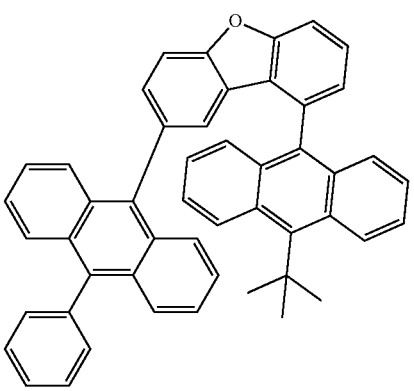
633
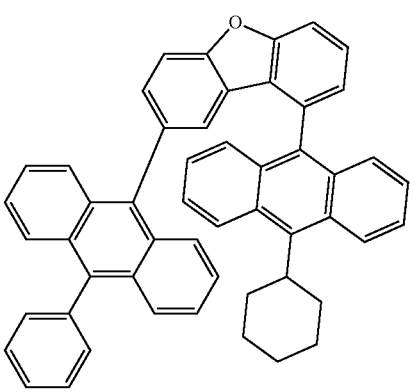
634
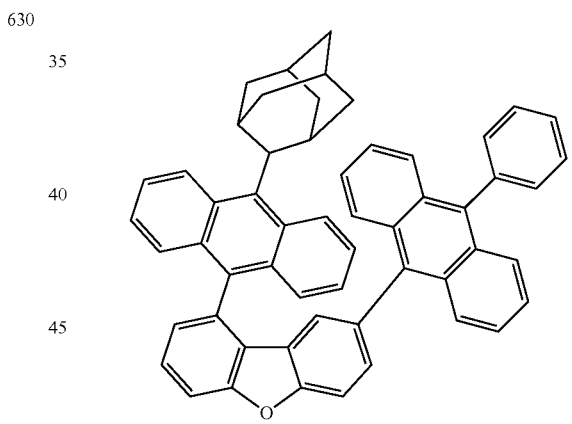
635
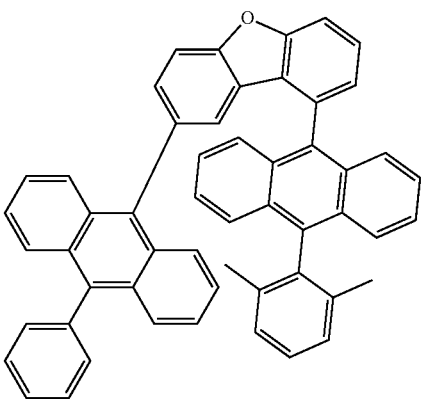

1699
-continued
636
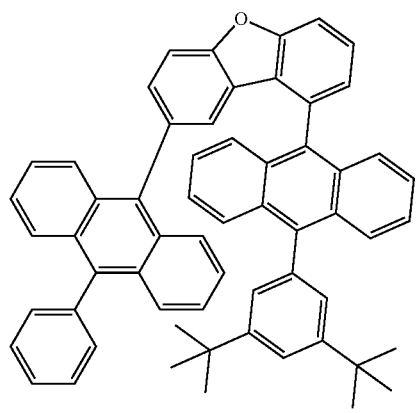
637
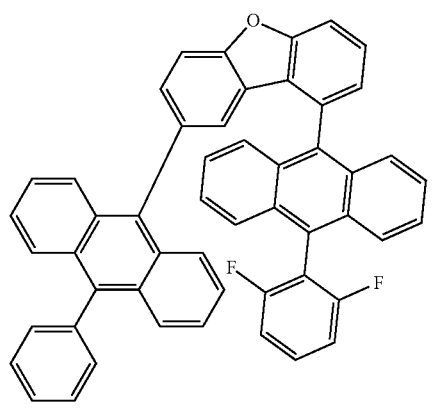
638
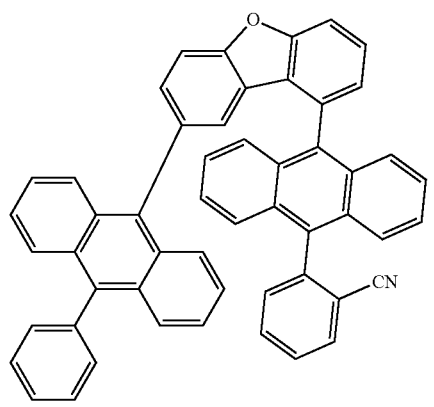
639
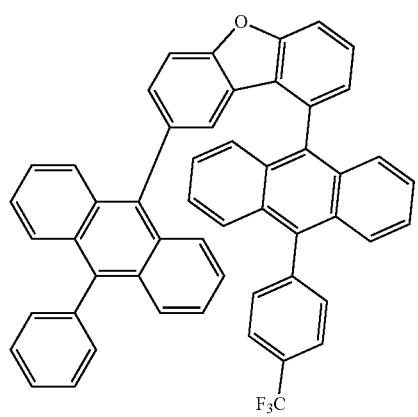
1700
-continued
640
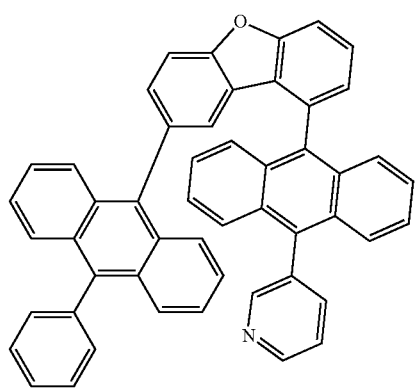
641
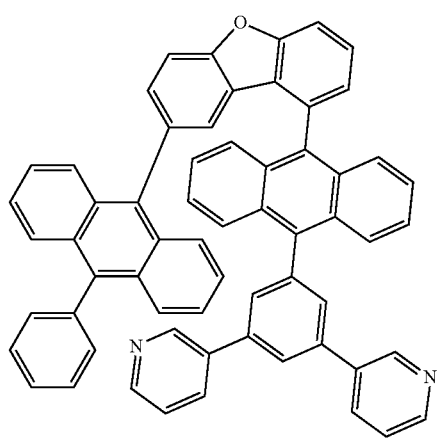
642
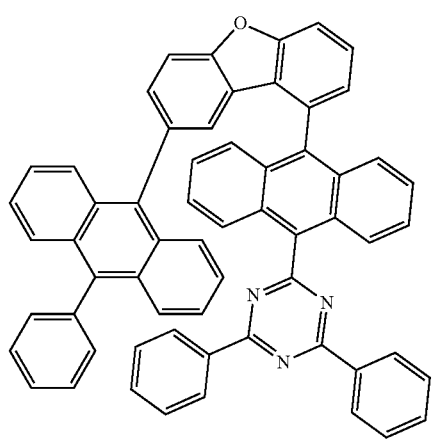

643
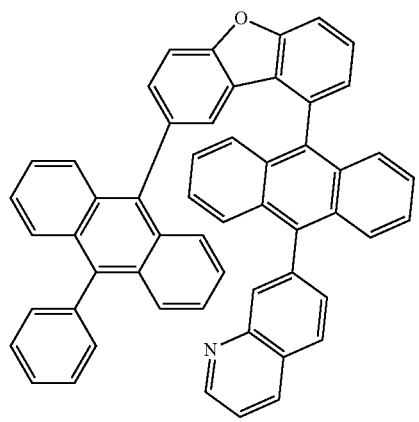
644
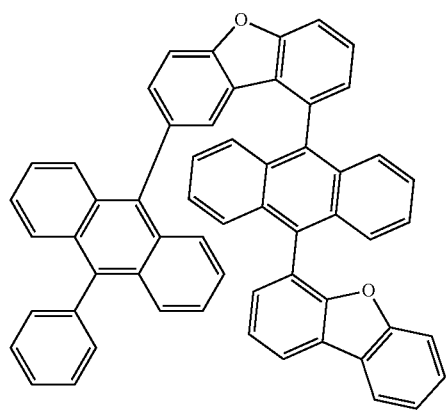
645
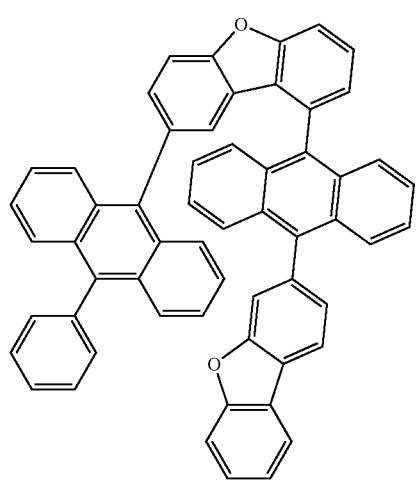
646
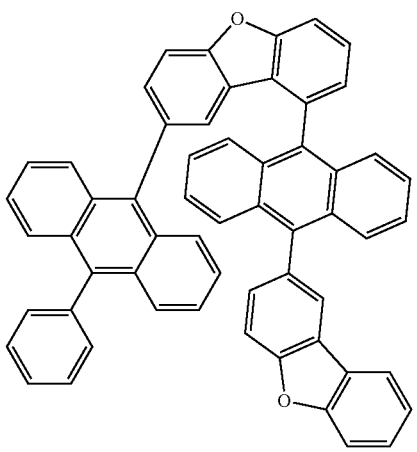
647
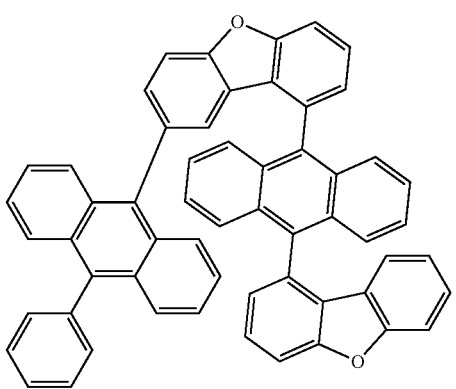
648
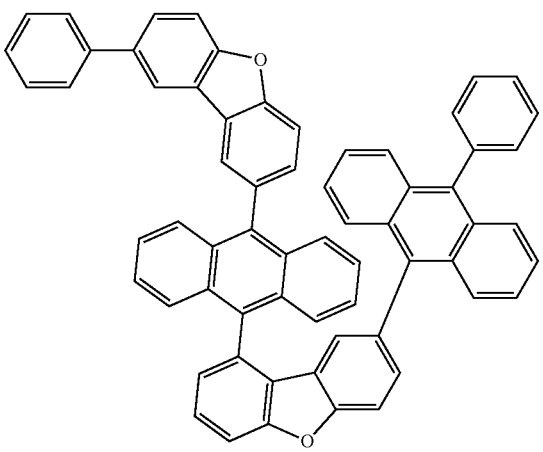

1703
-continued
649
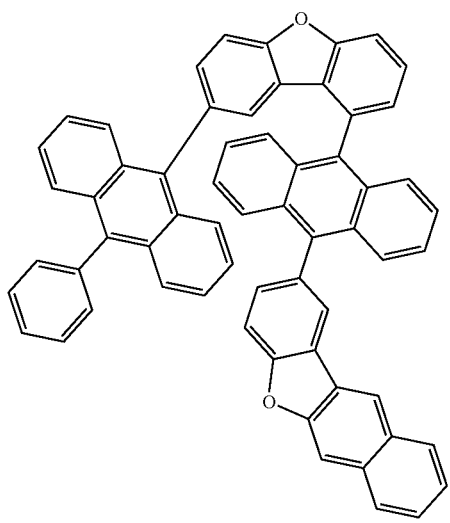
650
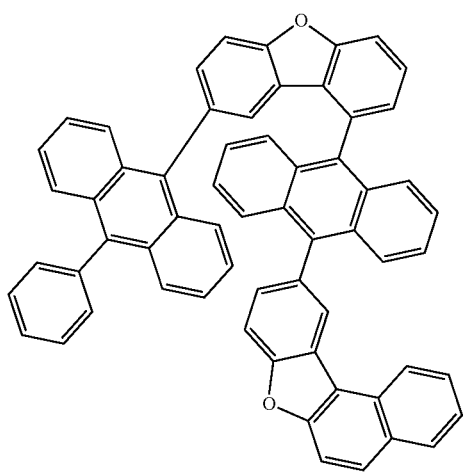
651
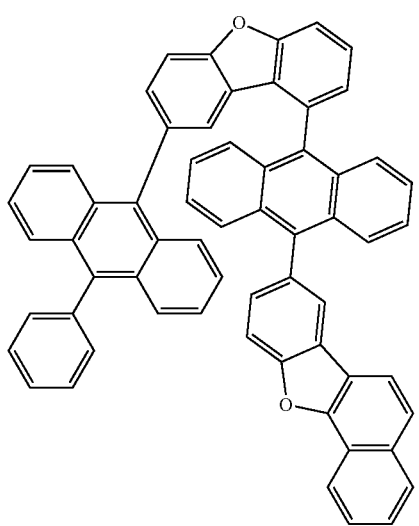
1704
-continued
652
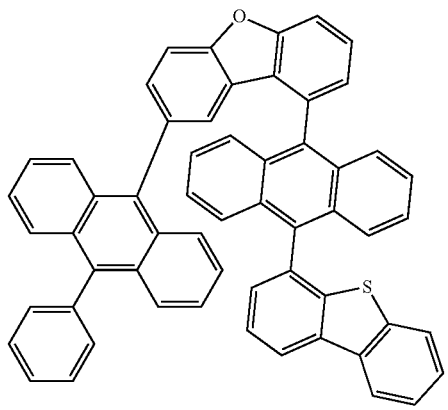
653
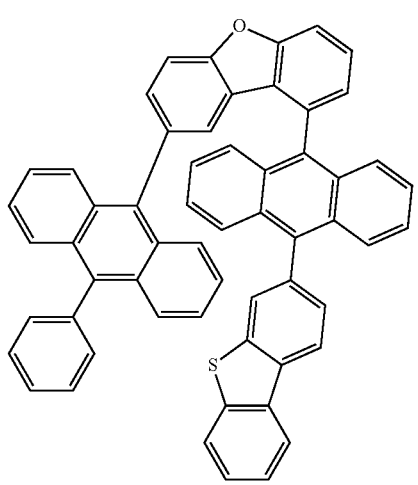
654
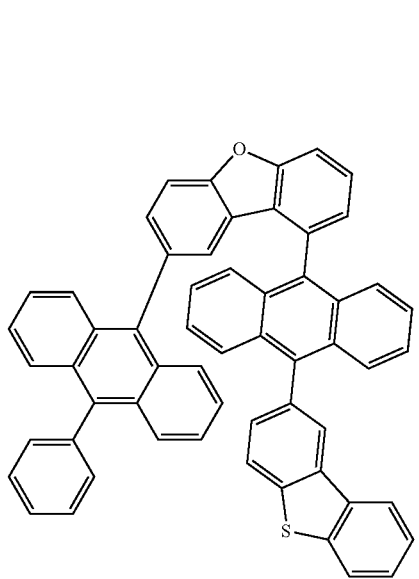

655
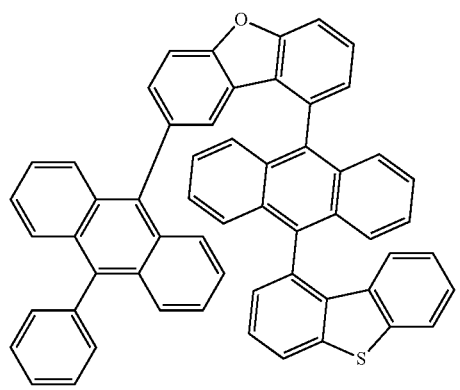
656
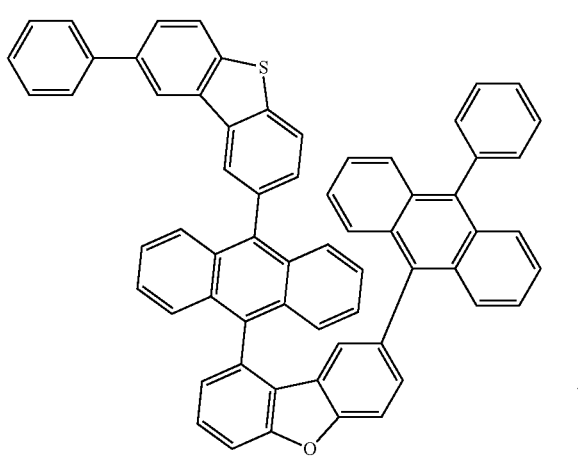
657
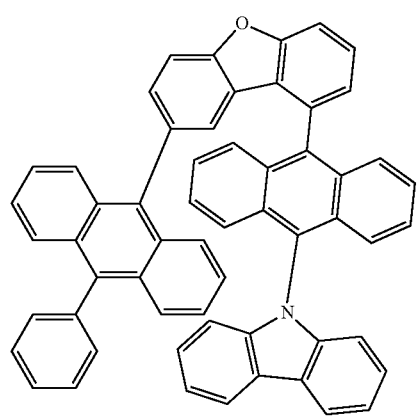
658
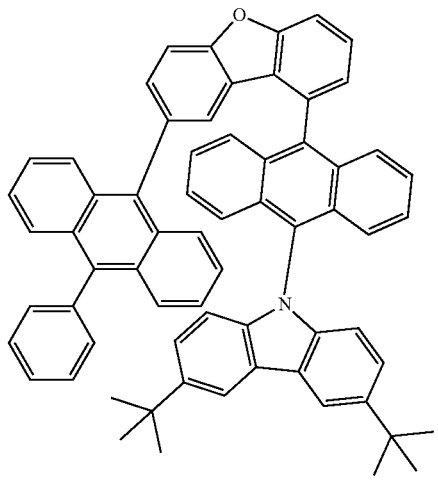
659
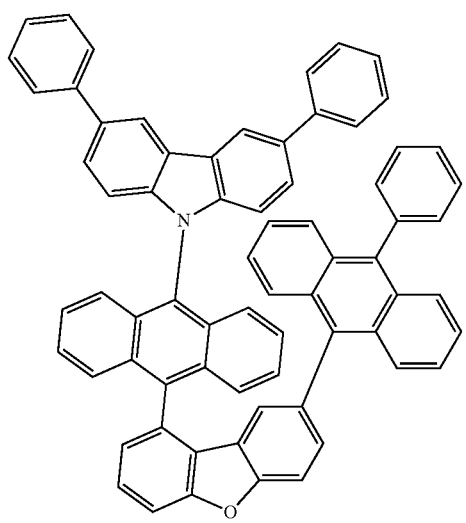
660
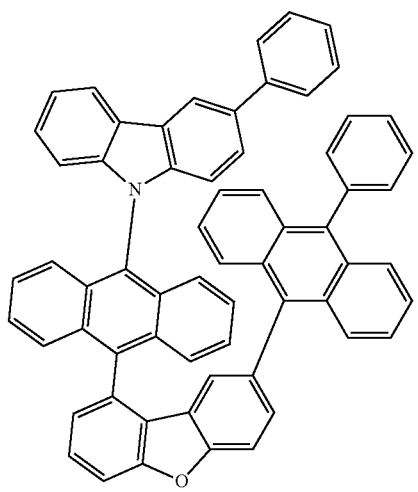

1707
-continued
661
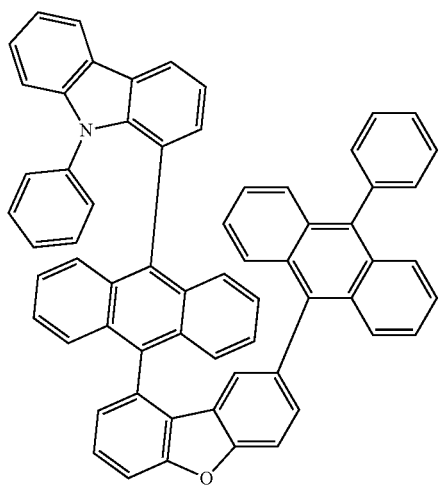
662
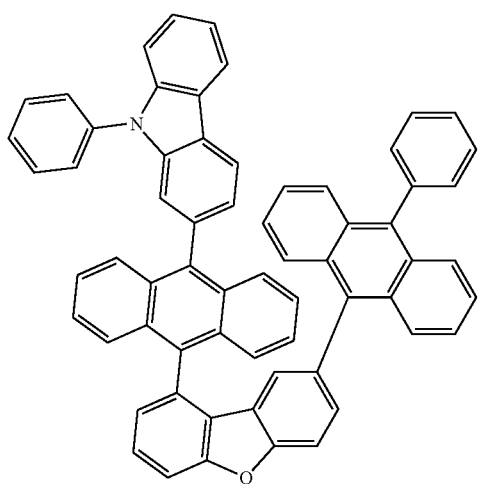
663
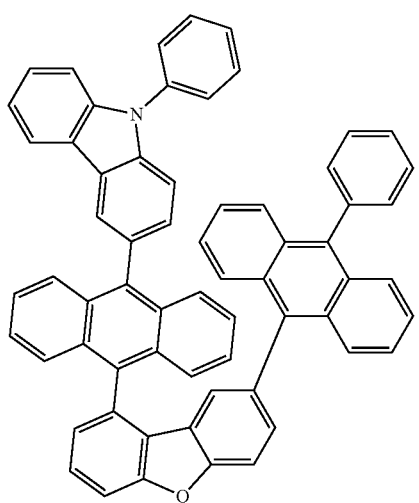
1708
-continued
664
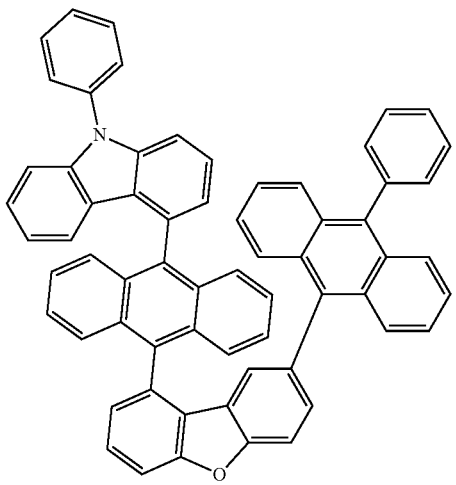
665
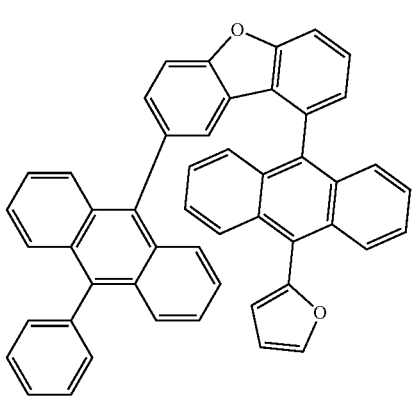
666
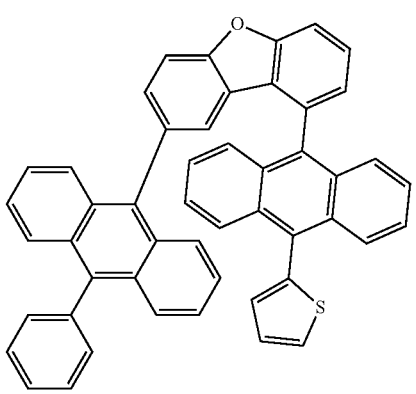
667
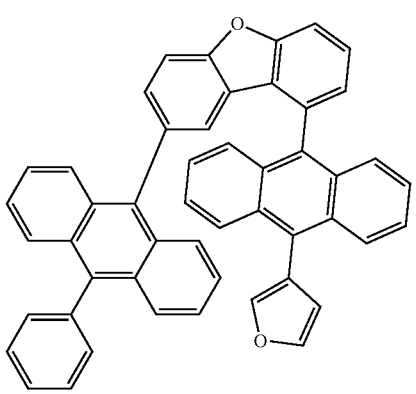

1709
-continued
668
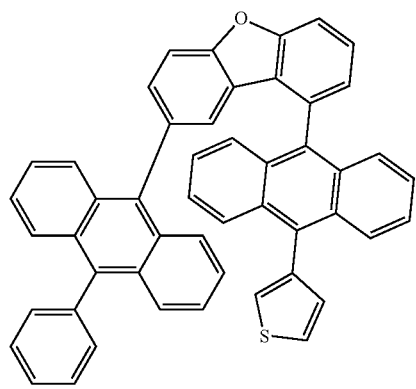
669
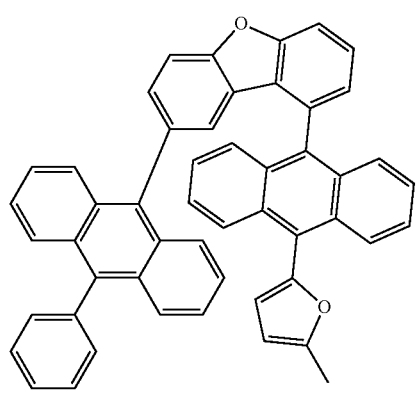
670
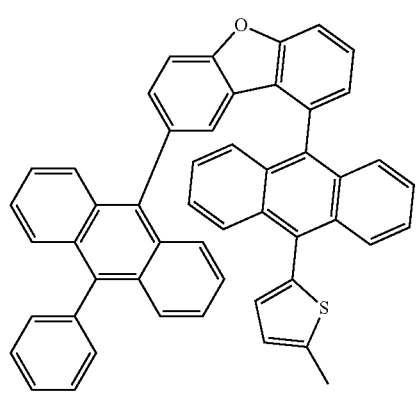
671
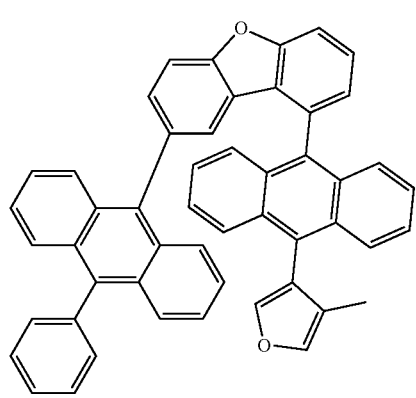
1710
-continued
672
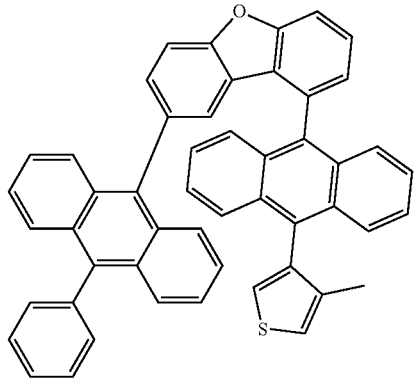
673
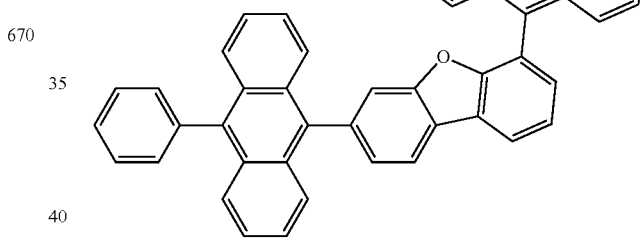
674
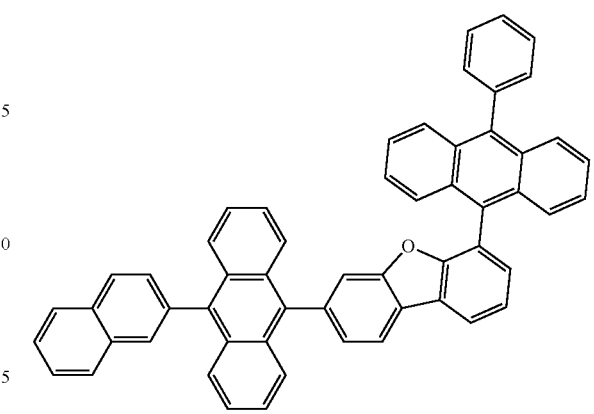

1711
-continued
675
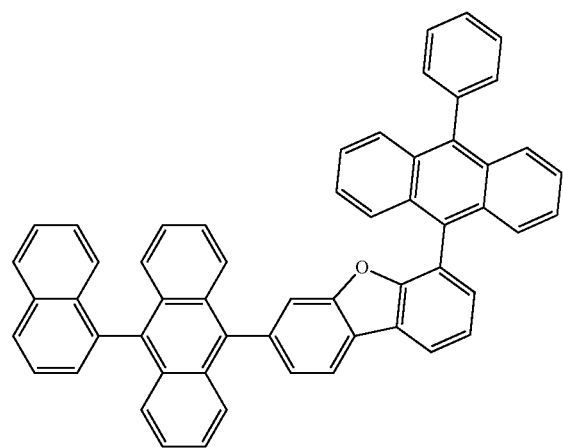
676
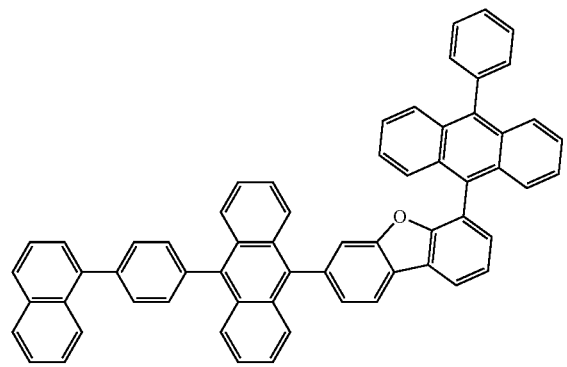
677
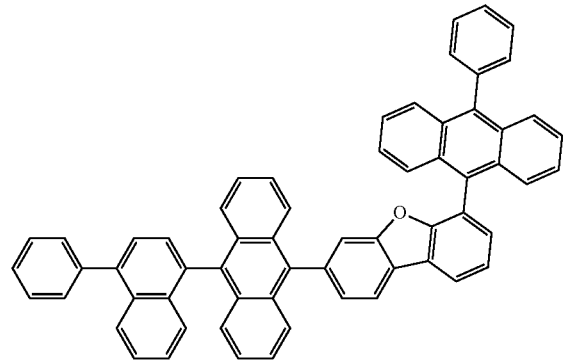
1712
-continued
678
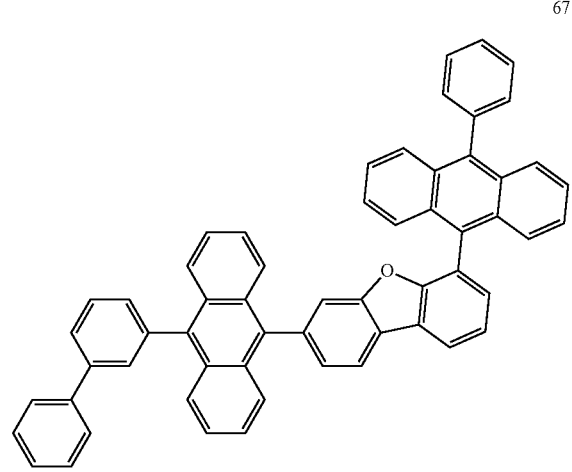
679
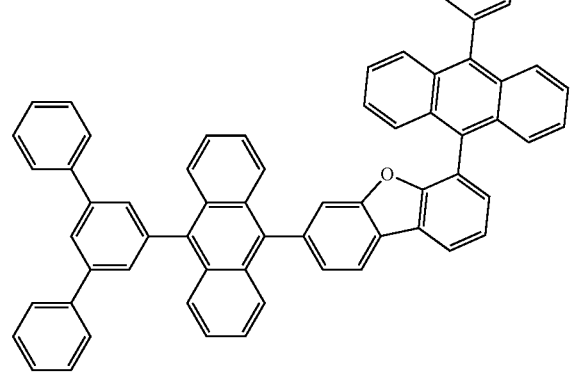
680
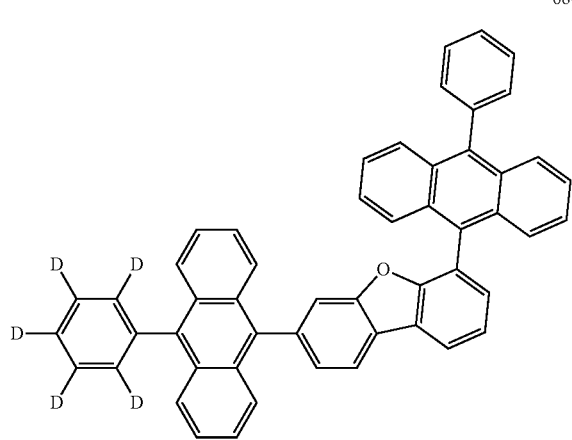

681
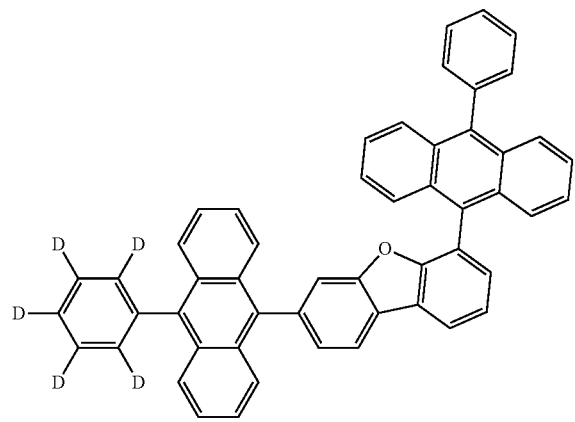
684
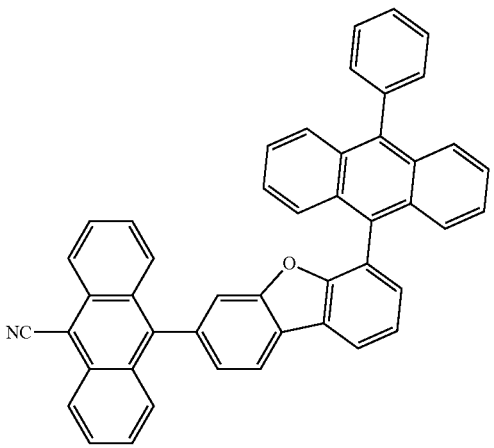
682
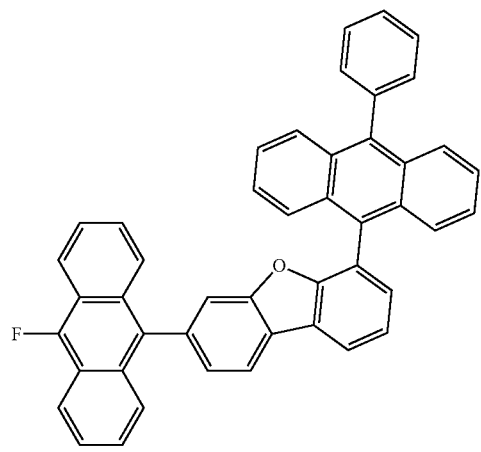
685
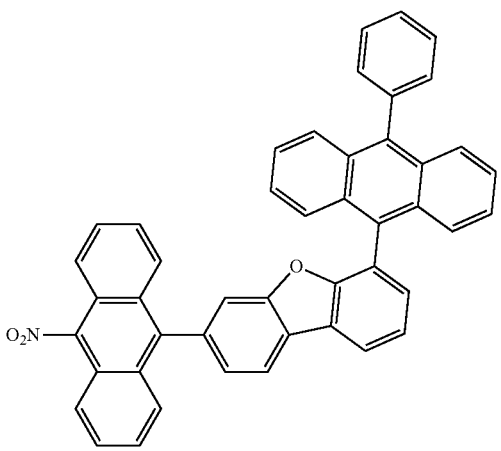
683
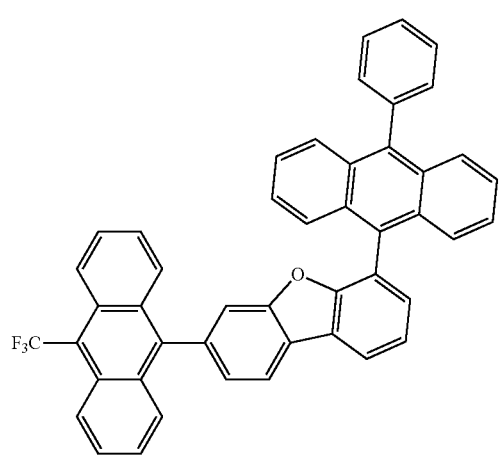
686
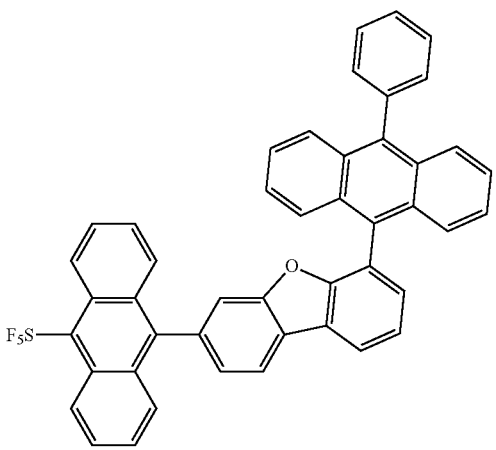

-continued
687
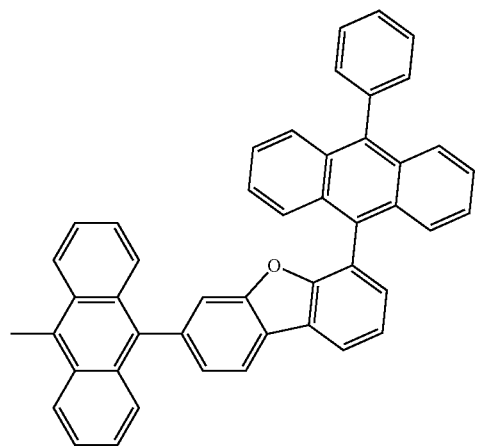
688
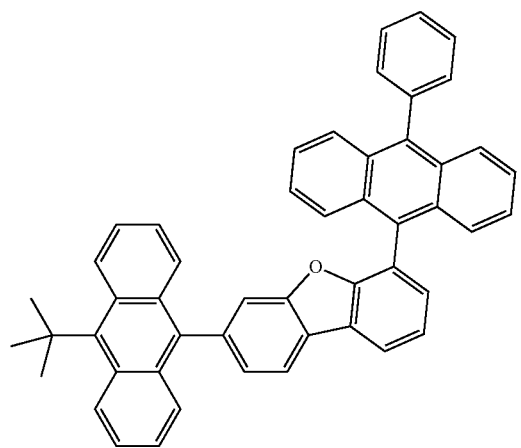
689
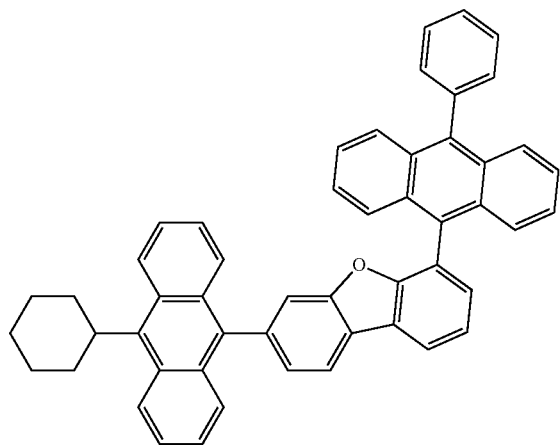
-continued
690
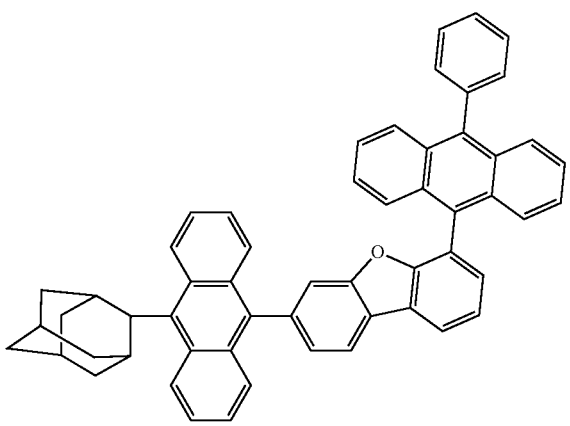
691
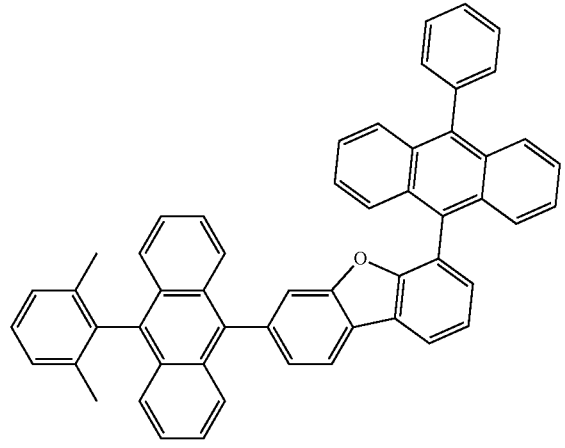
692
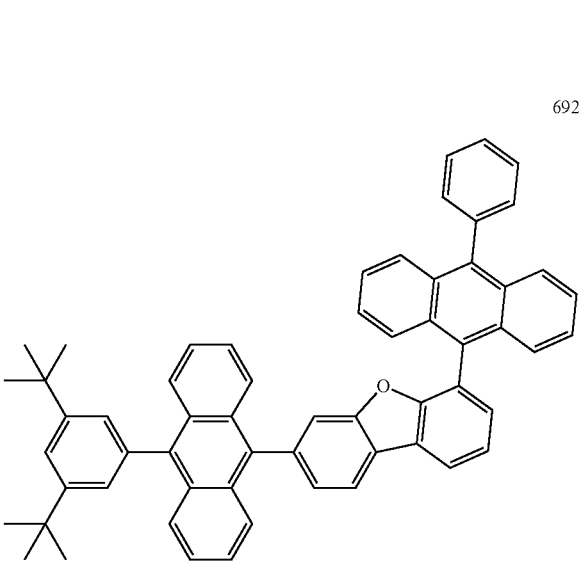

693
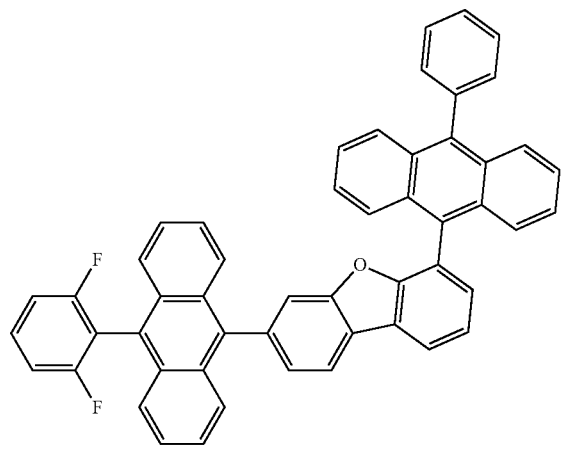
694
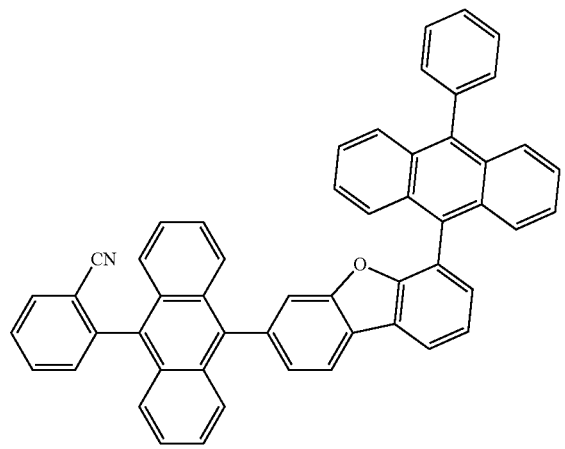
695
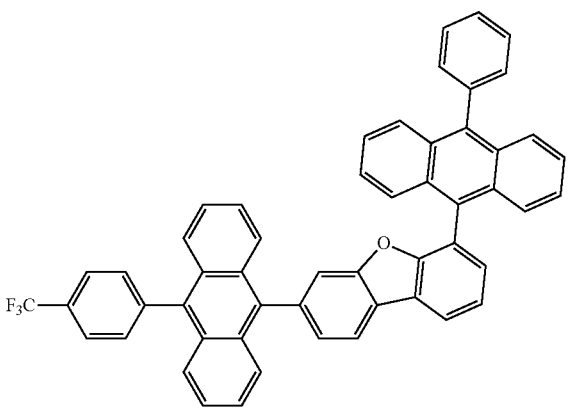
696
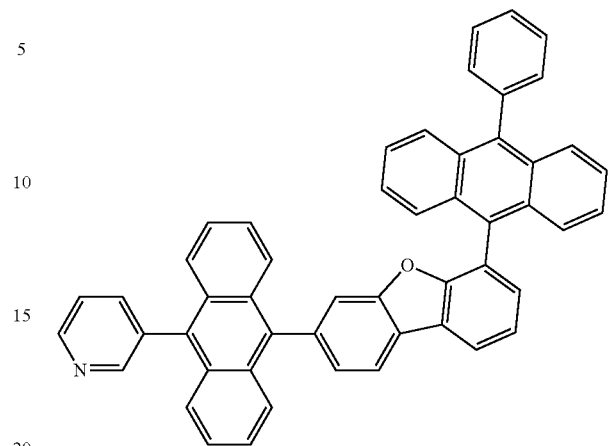
697
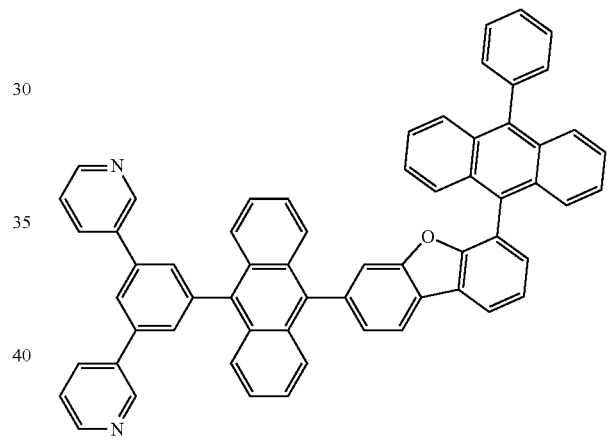
698
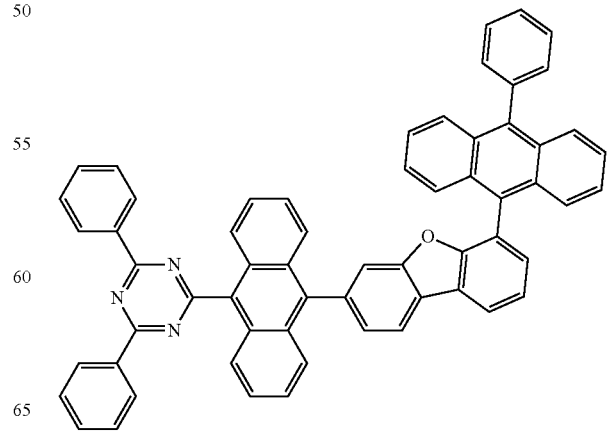

1719
-continued
699
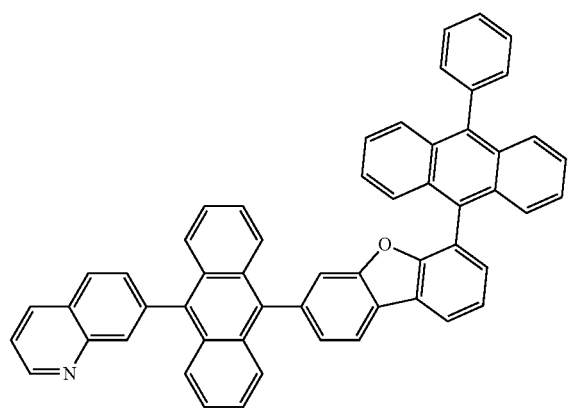
700
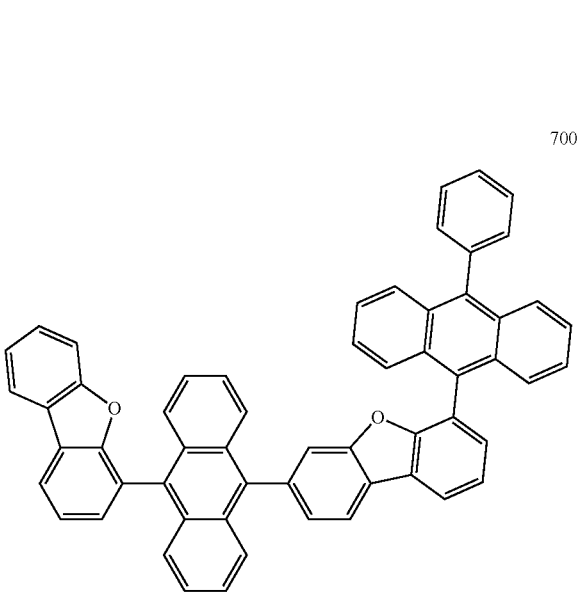
701
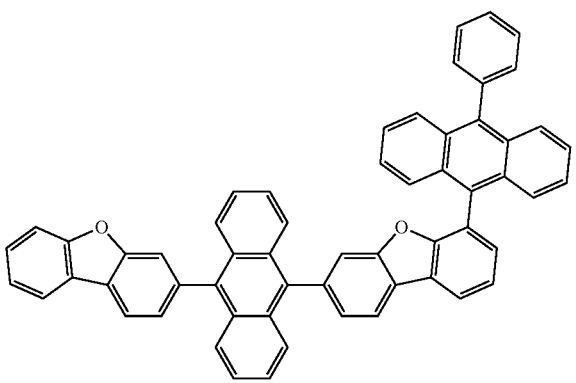
1720
-continued
702
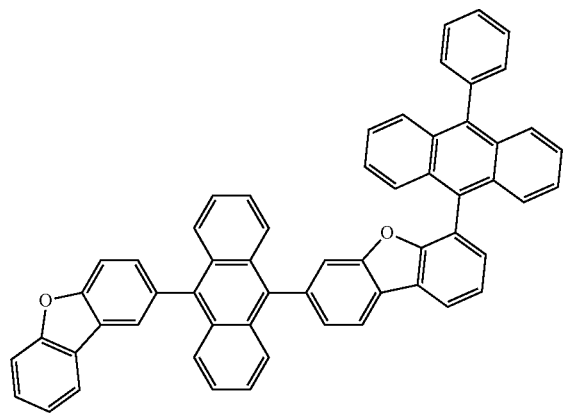
703
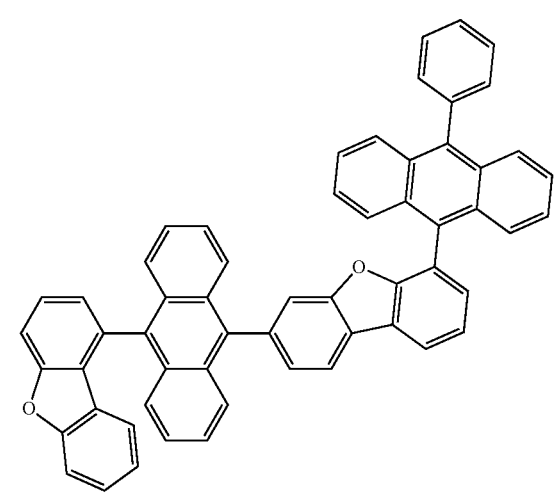
704
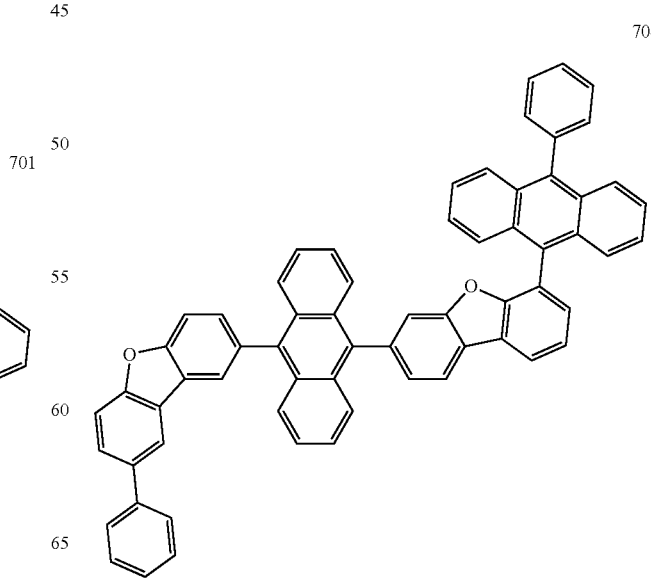

-continued
705
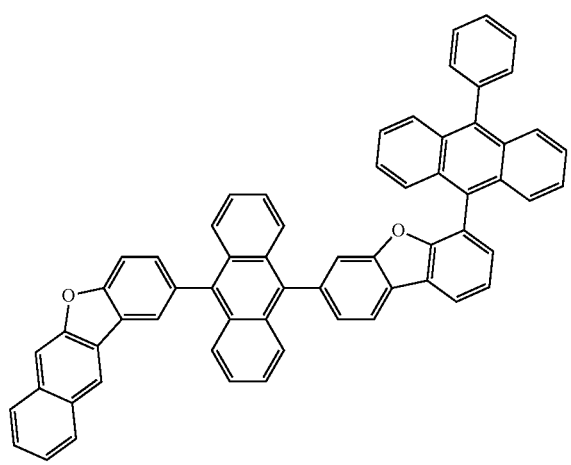
706
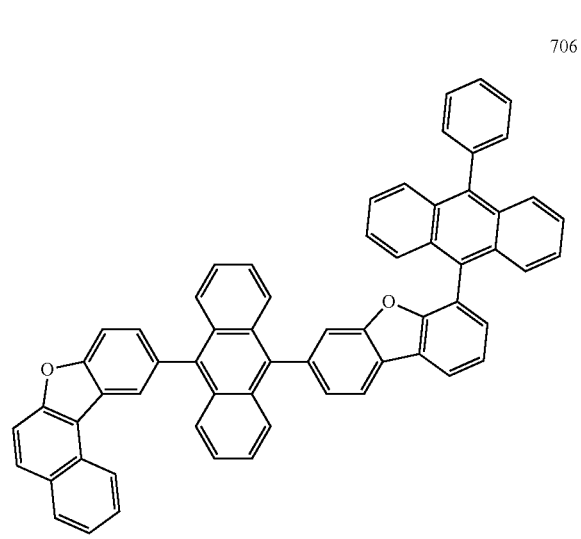
707
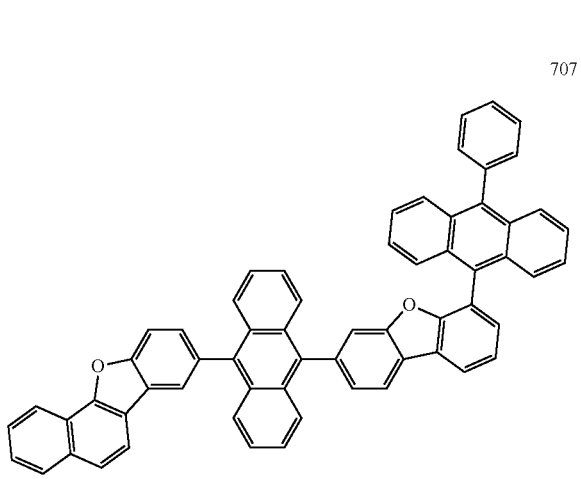
-continued
708
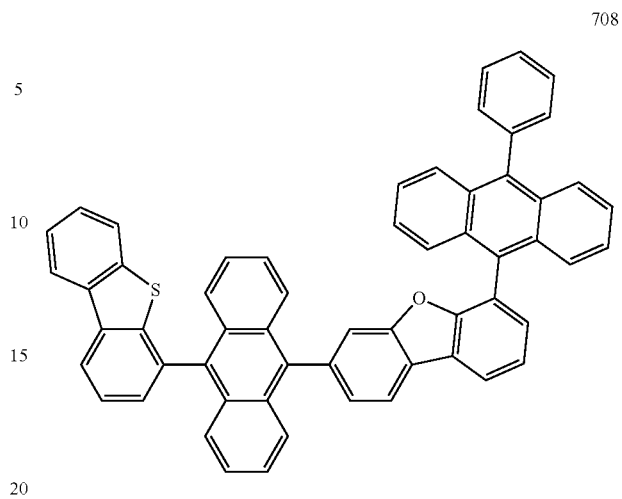
709
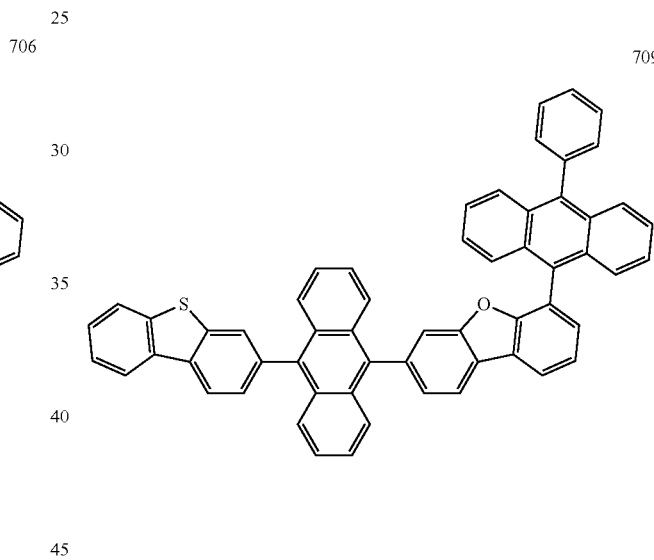
710
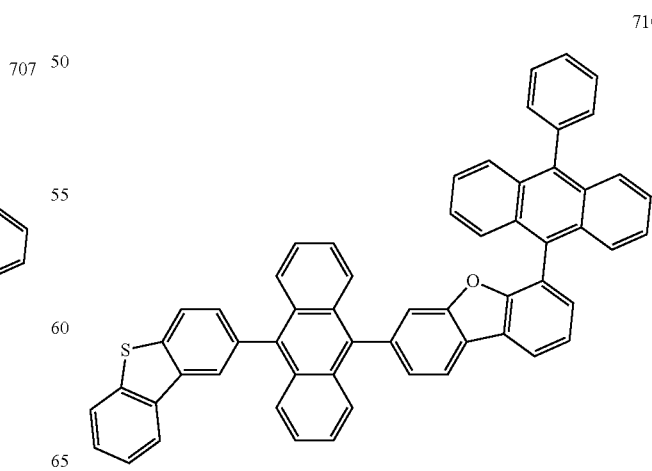

1723
-continued
711
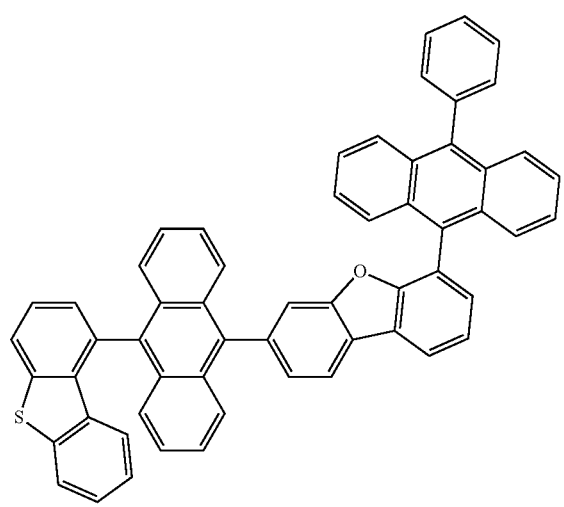
712
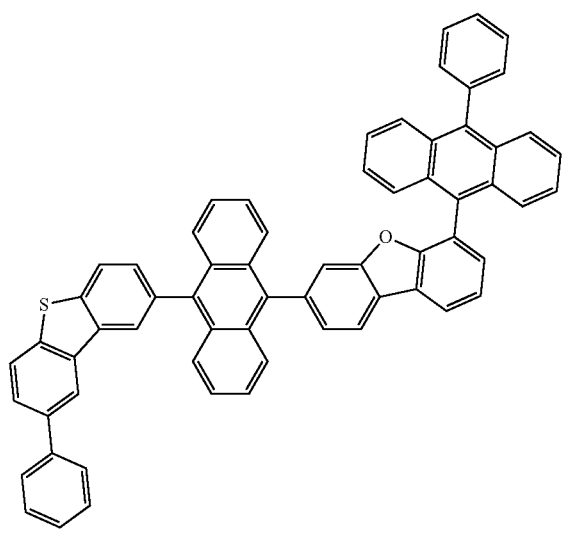
713
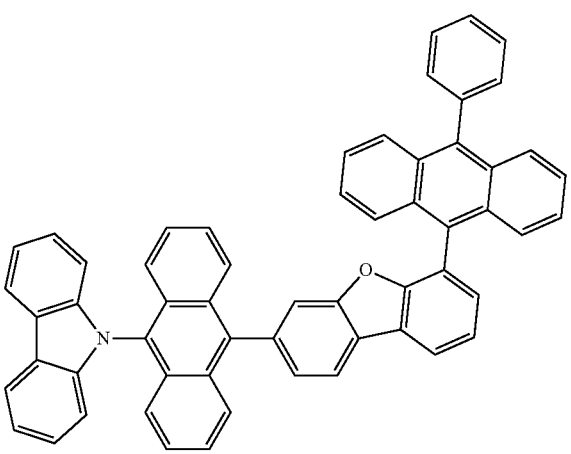
1724
-continued
714
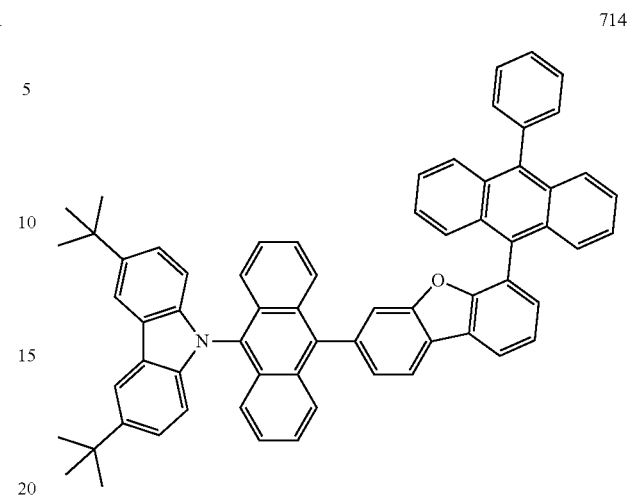
715
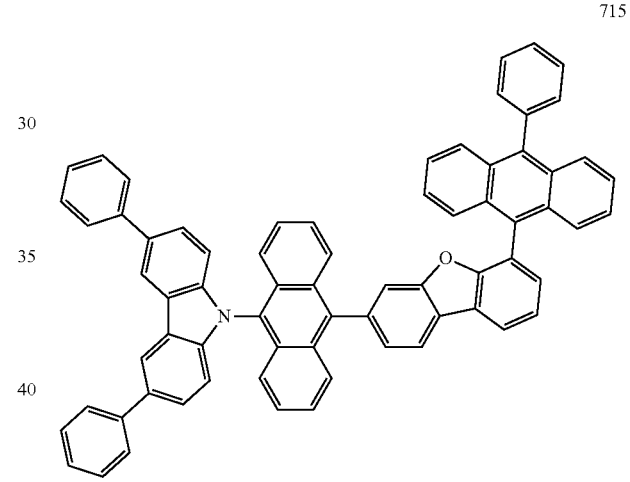
716
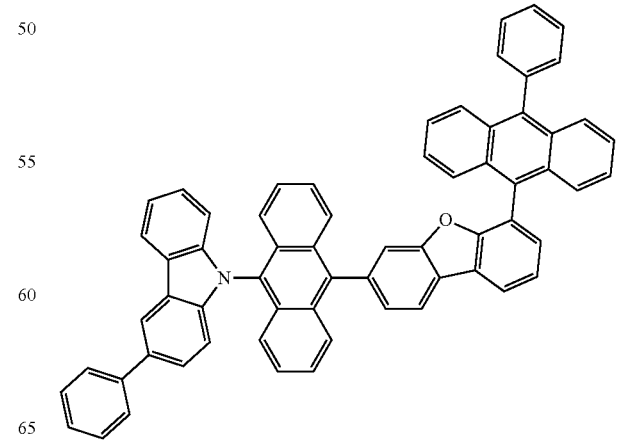

1725
-continued
717
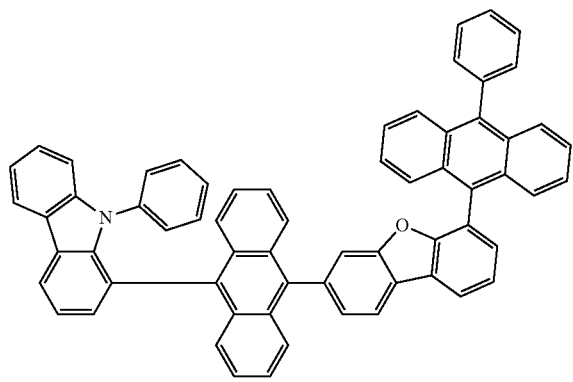
718
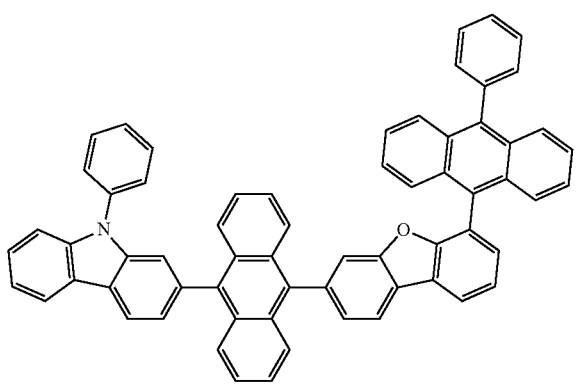
719
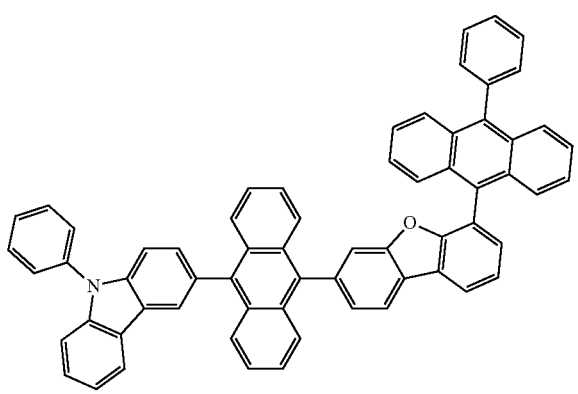
720
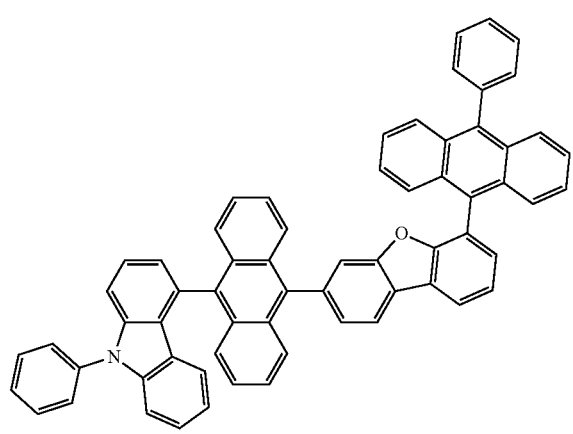
1726
-continued
721
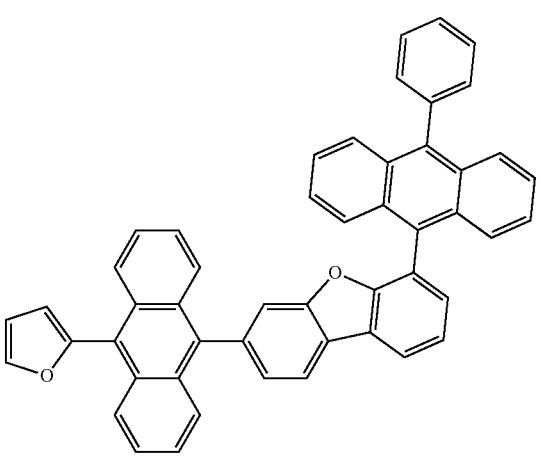
722
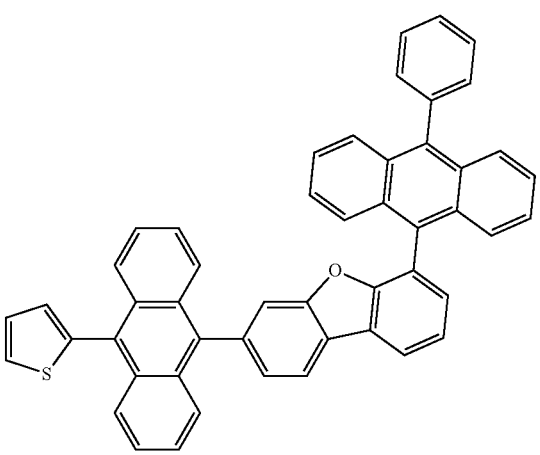
723
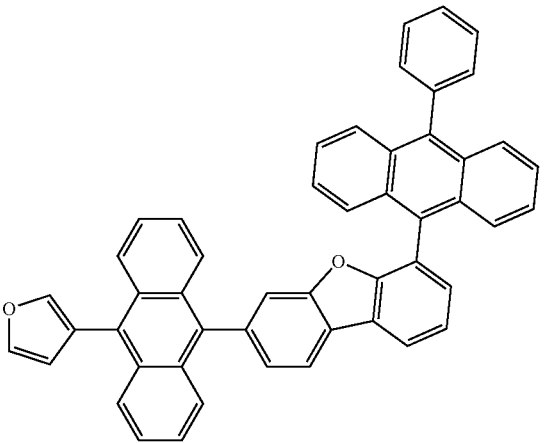

1727
-continued
724
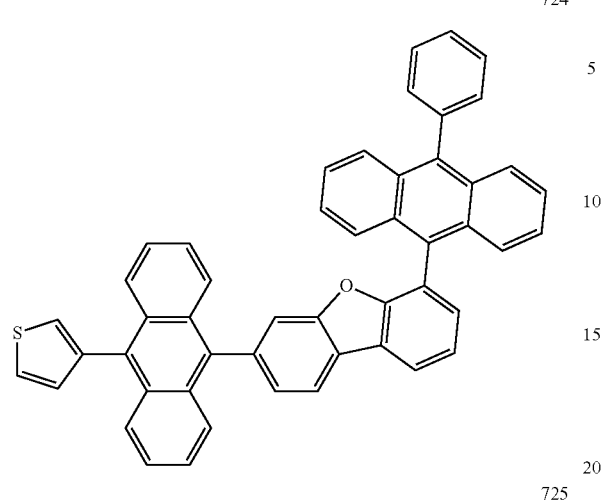
725
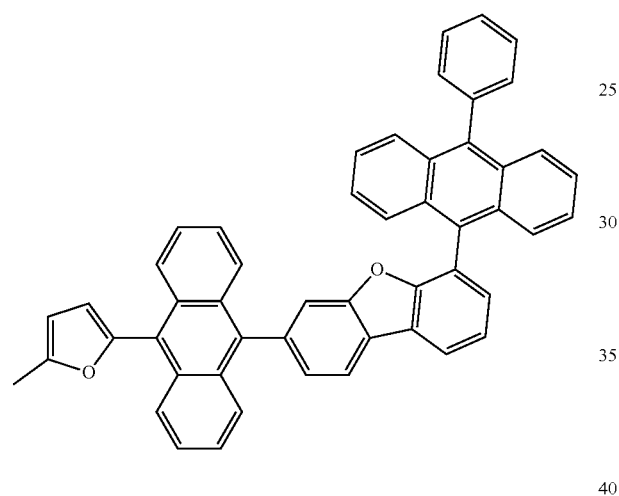
726
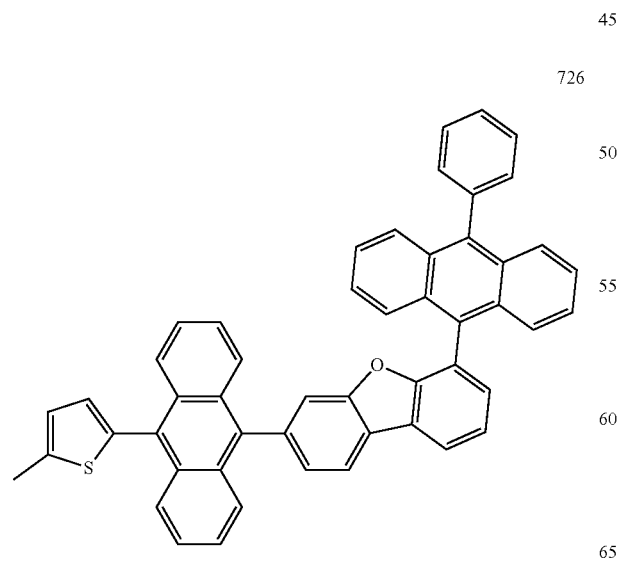
1728
-continued
727
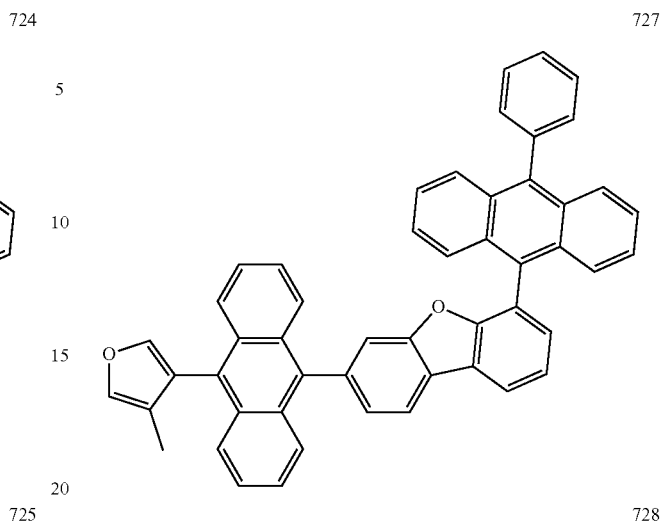
728
729
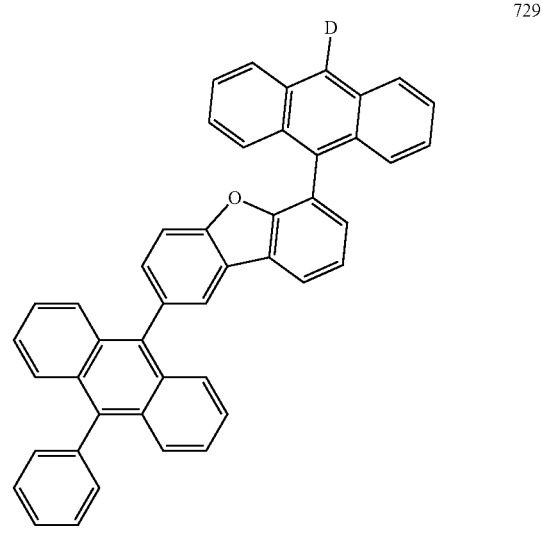

1729
-continued
730
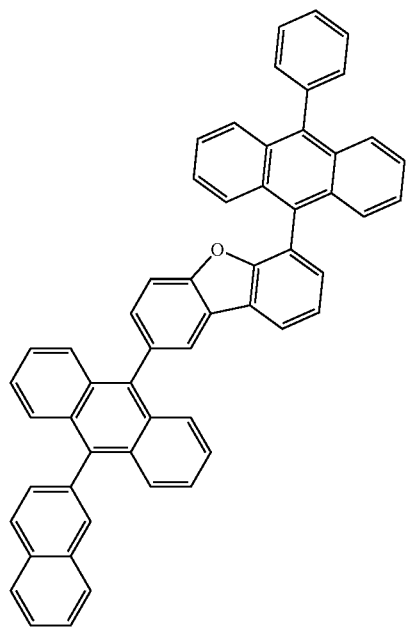
731
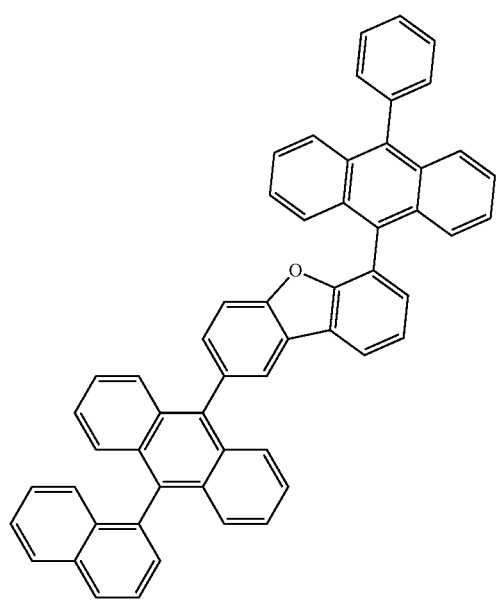
1730
-continued
732
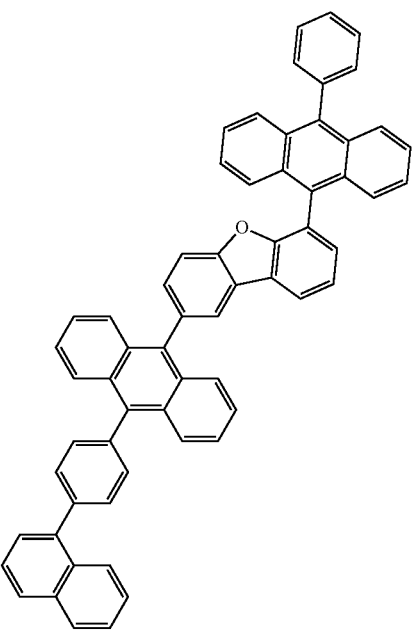
733
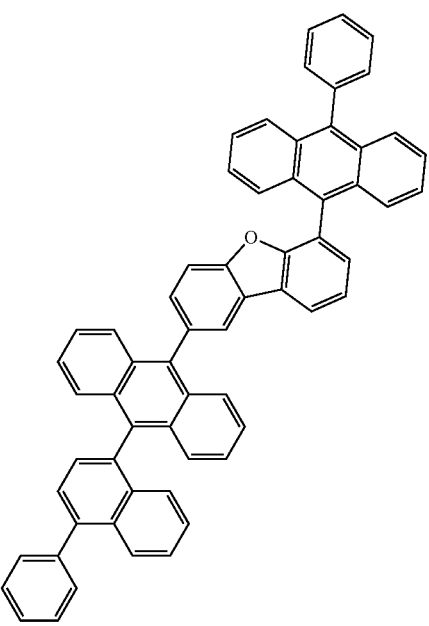

734
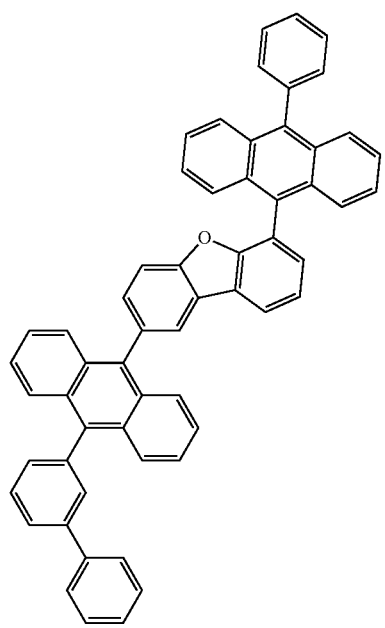
735
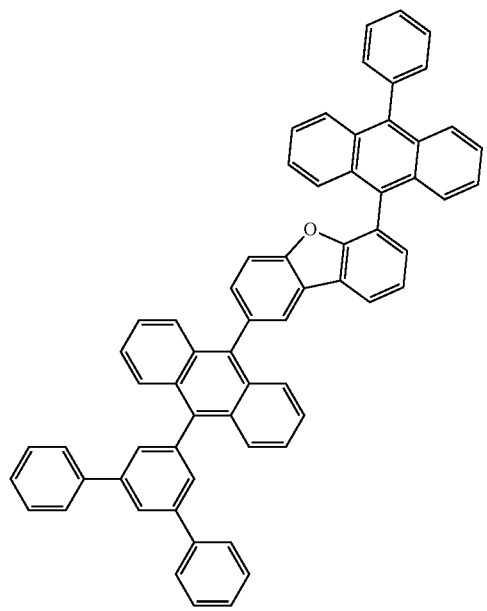
736
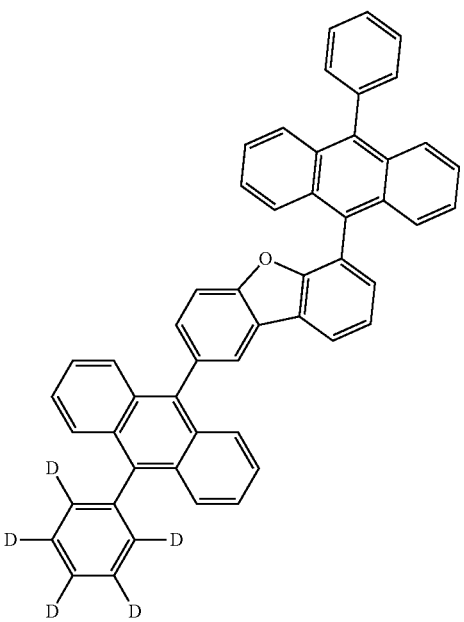
737
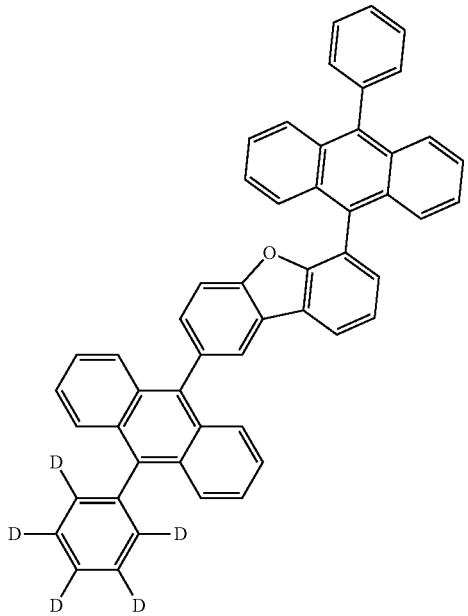

| 738 | 741 |
|---|---|
| 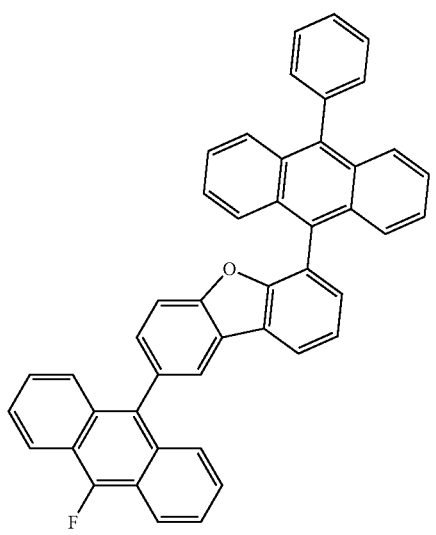 | 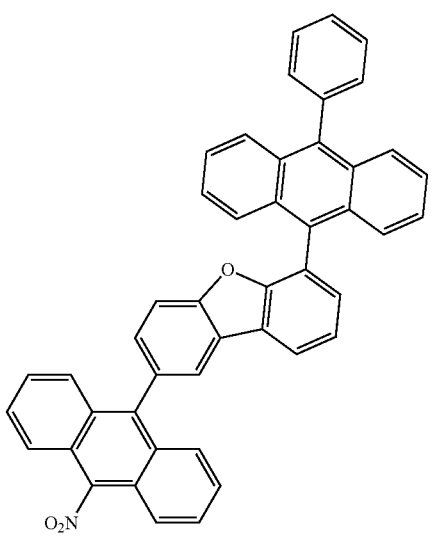 |
| 739 | 742 |
|---|---|
| 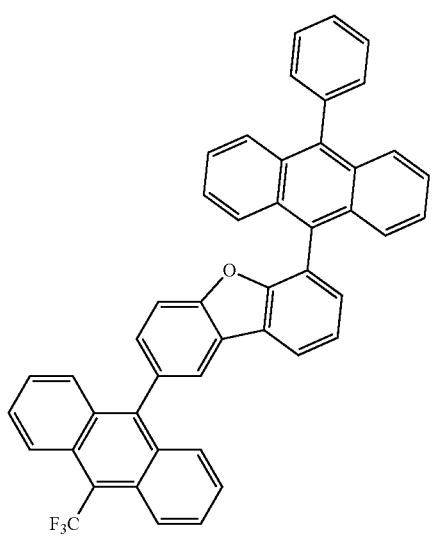 | 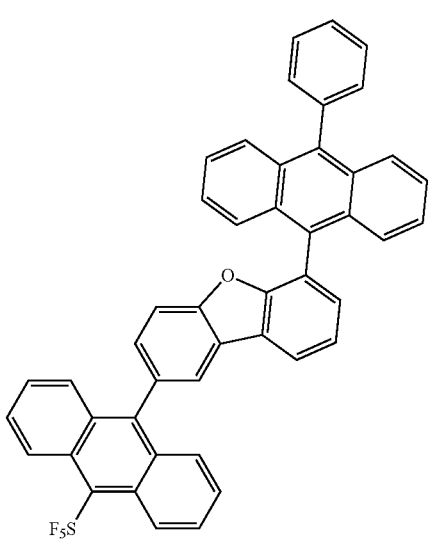 |
| 740 | 743 |
|---|---|
| 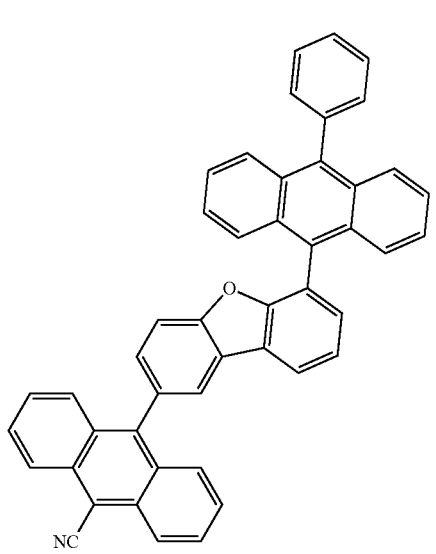 | 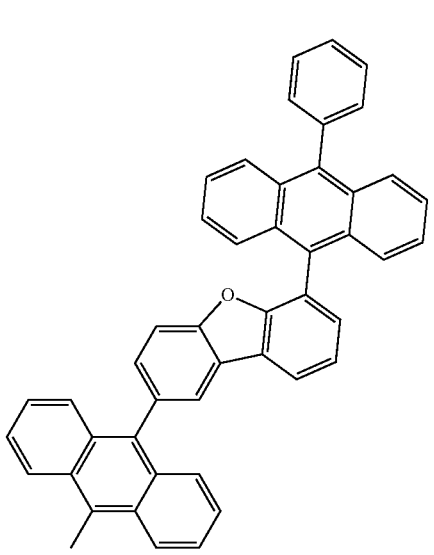 |

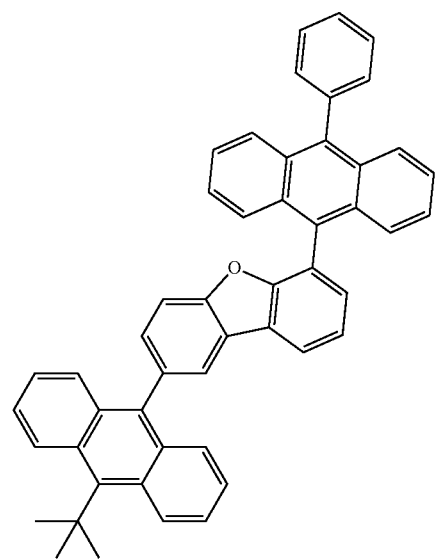
744
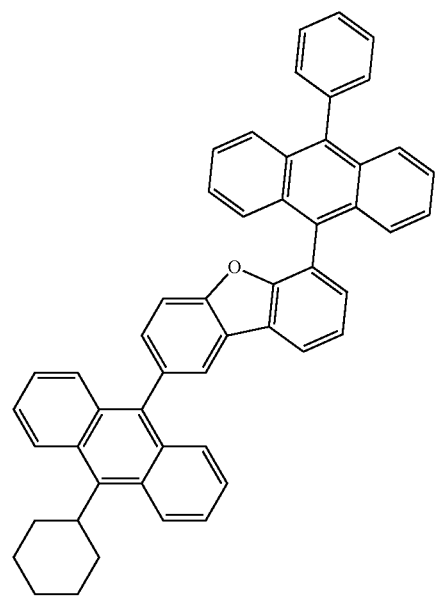
745
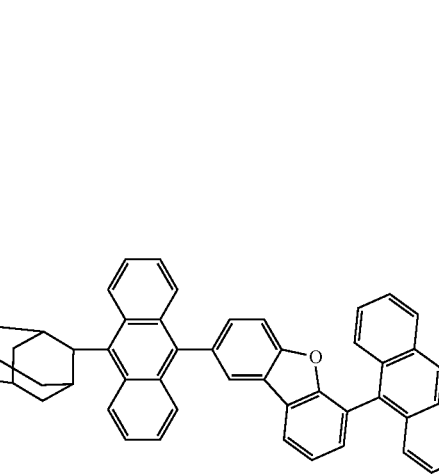
746
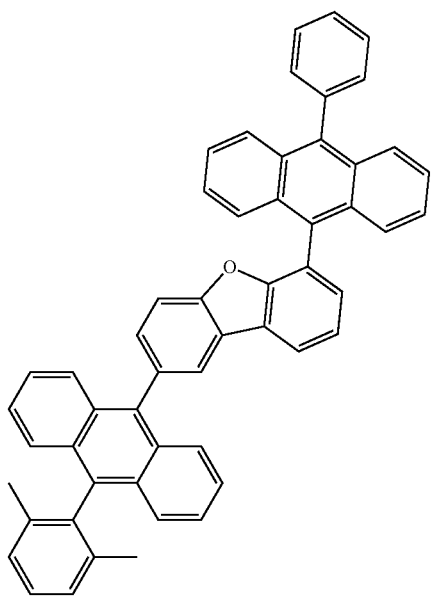
747
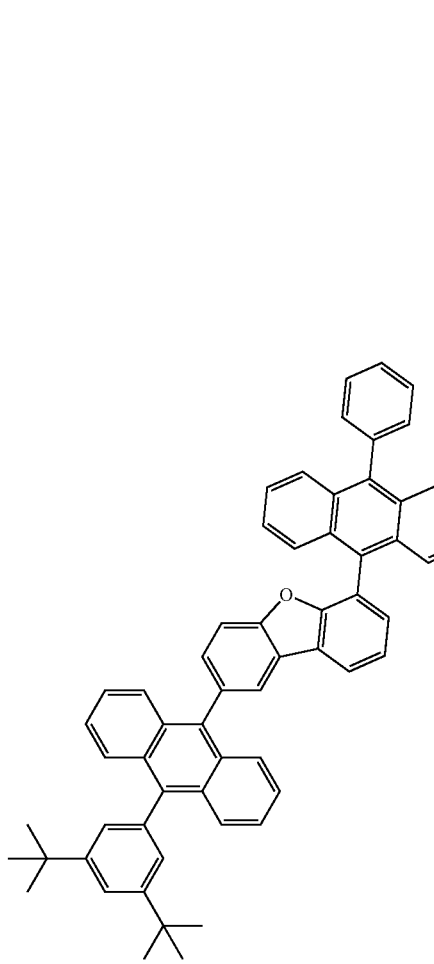
748

1737
-continued
749
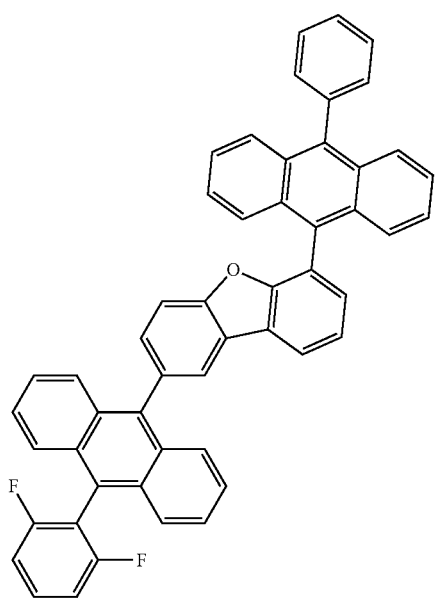
1738
-continued
751
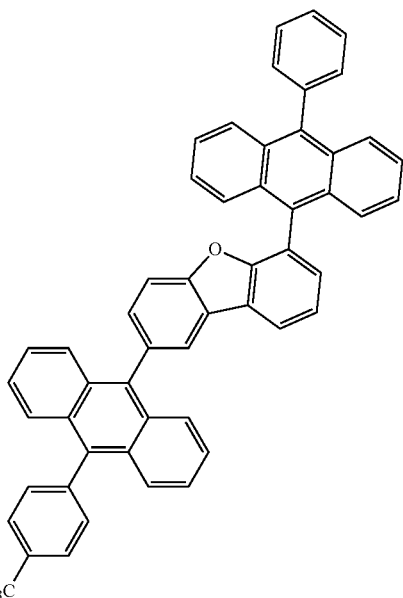
750
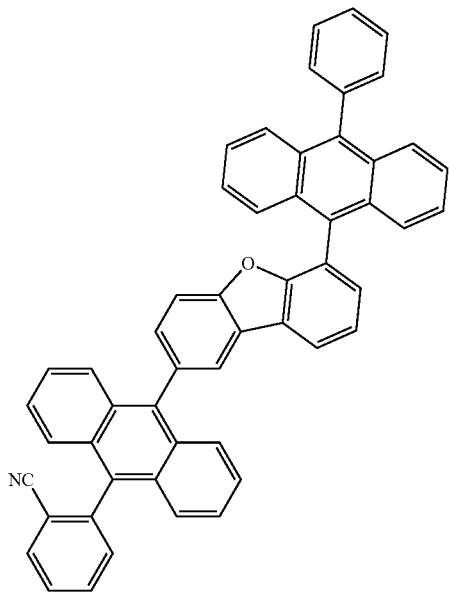
752
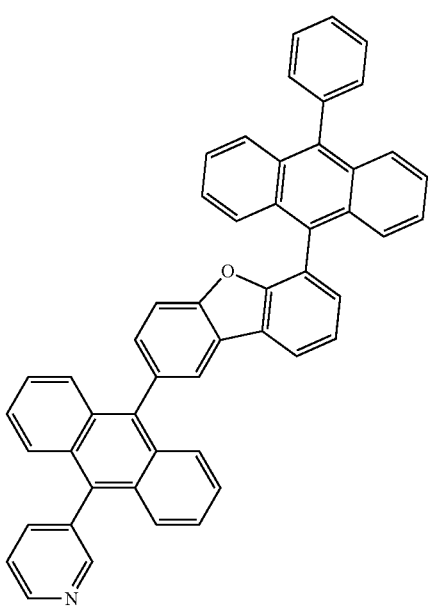

1739
-continued
753
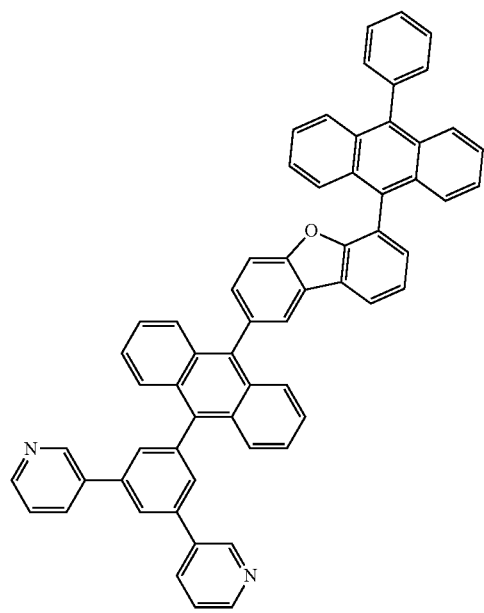
754
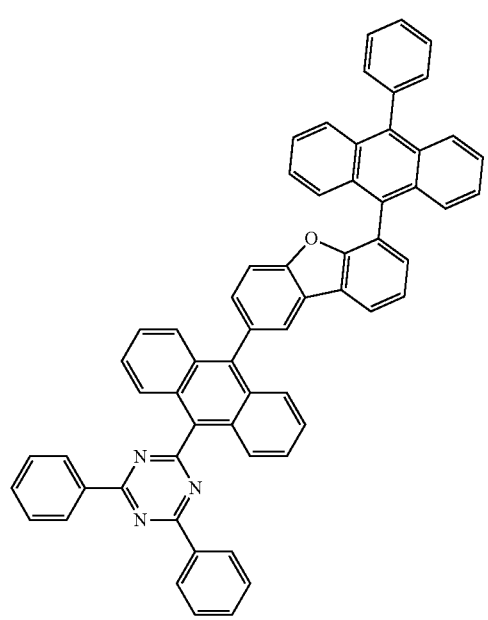
1740
-continued
755
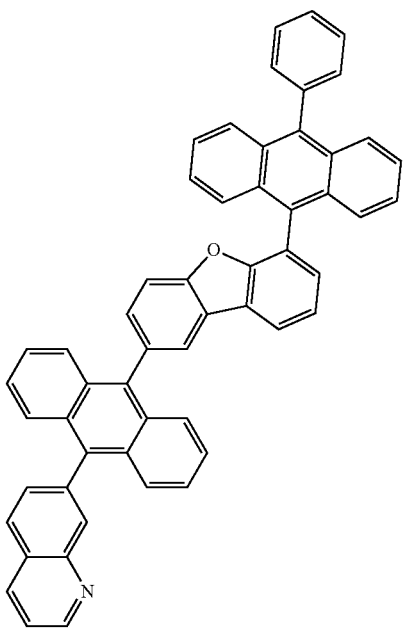
756

757
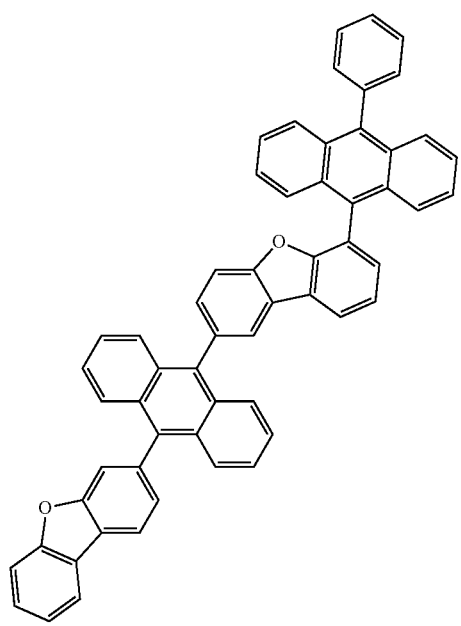
758
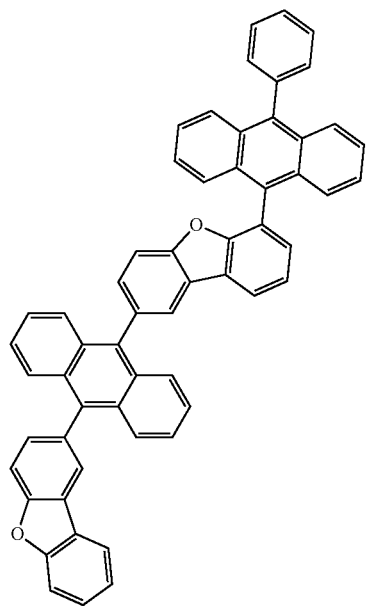
759
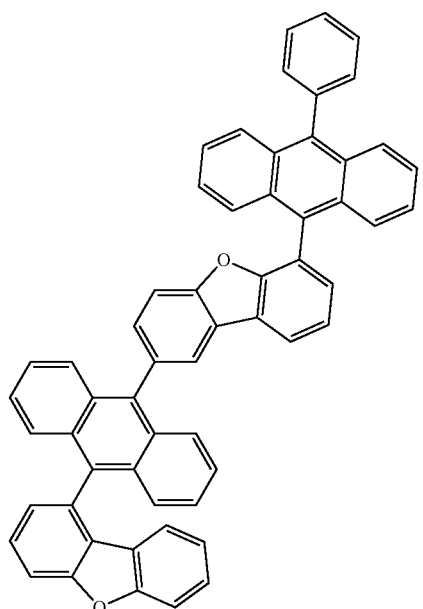
760
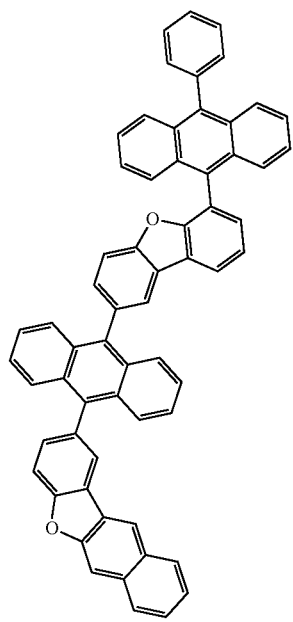
761

762
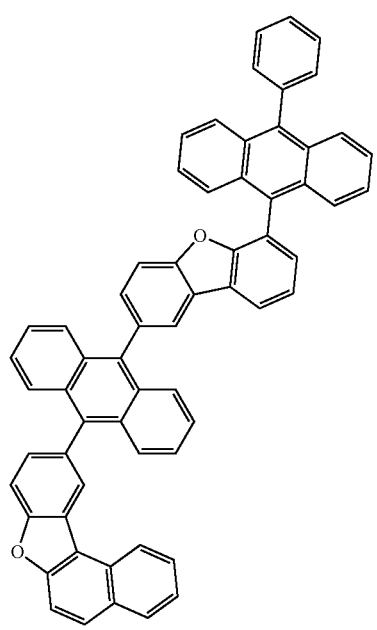
764
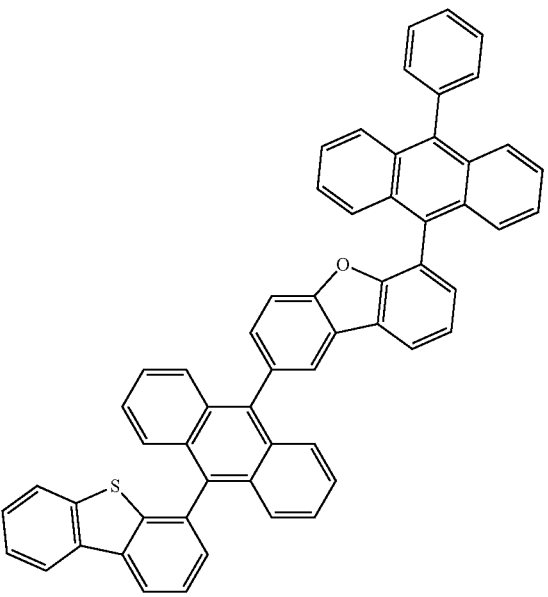
763
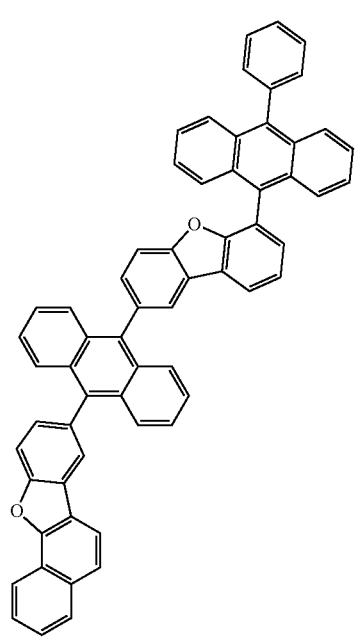
765
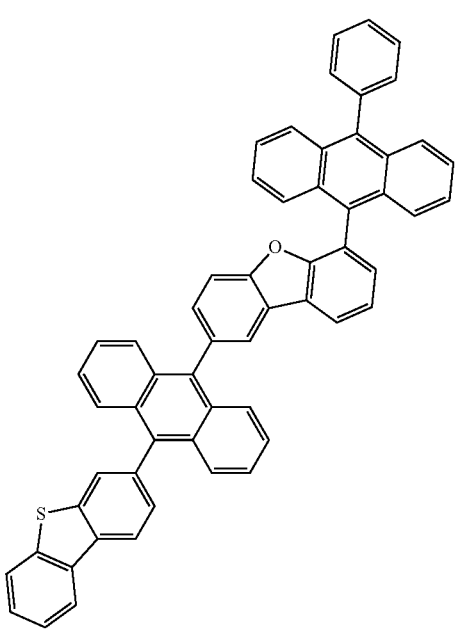

1745
-continued
766
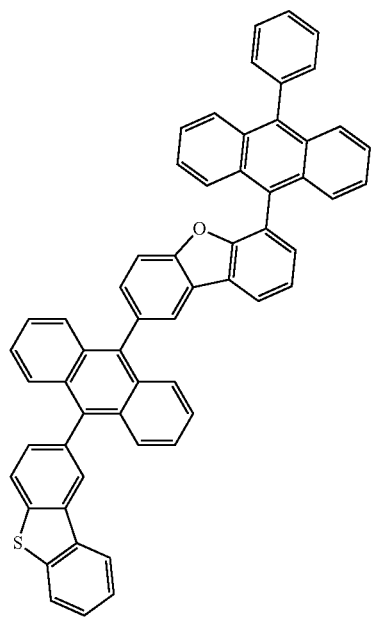
767
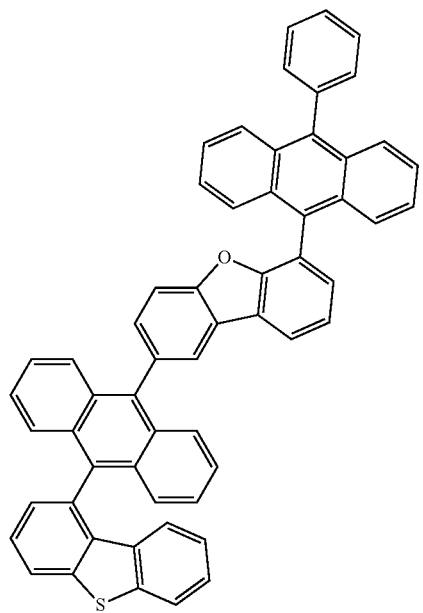
768
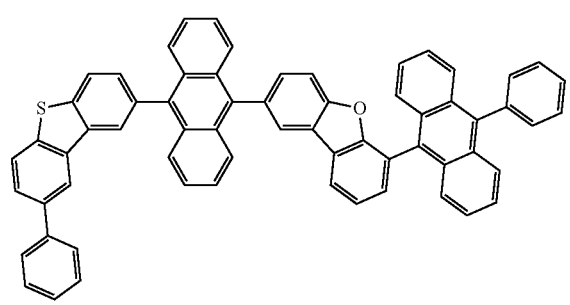
1746
-continued
769
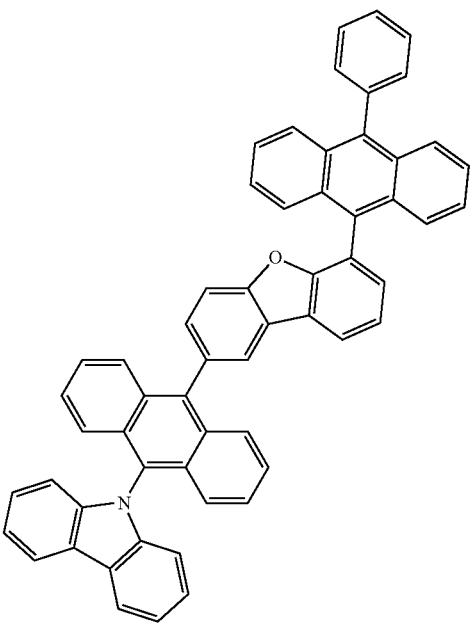
770
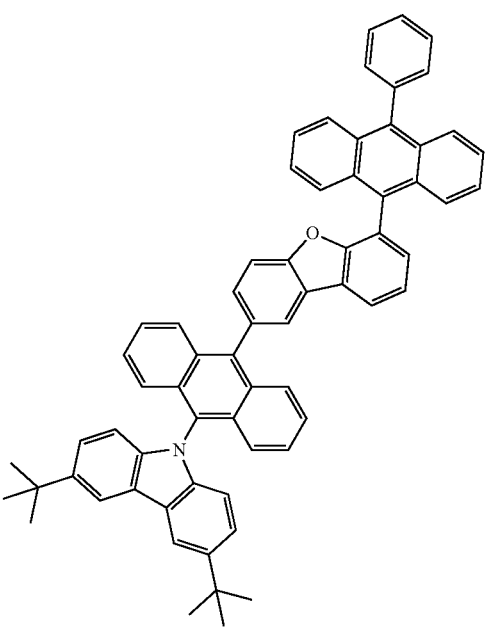
771
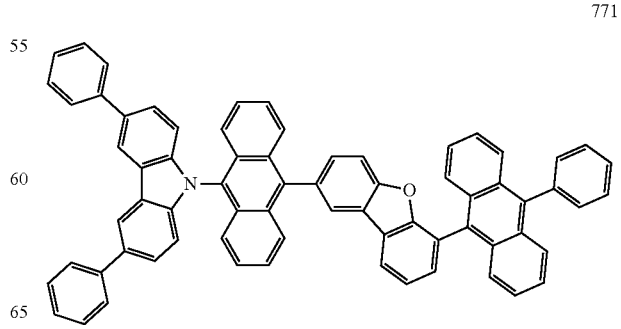

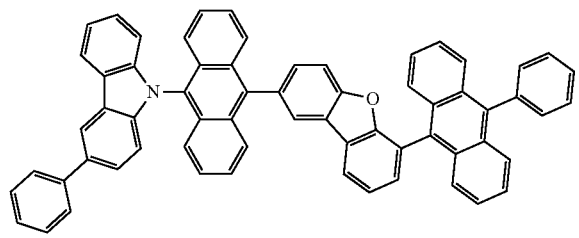
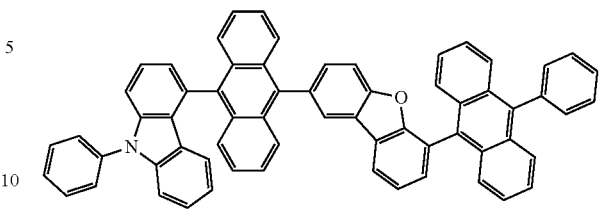
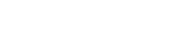
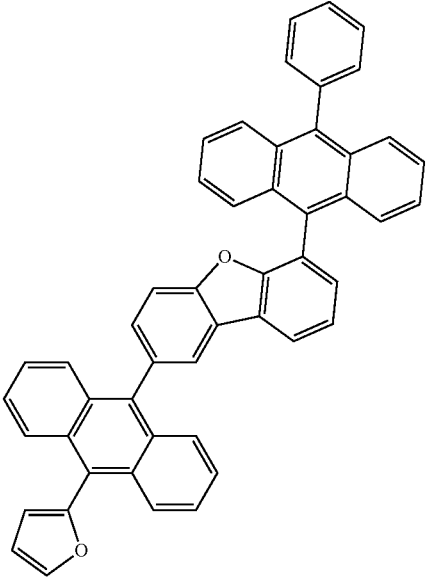
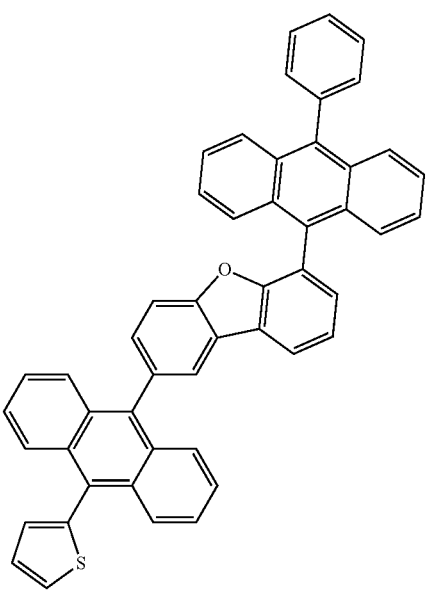

1749
-continued
779
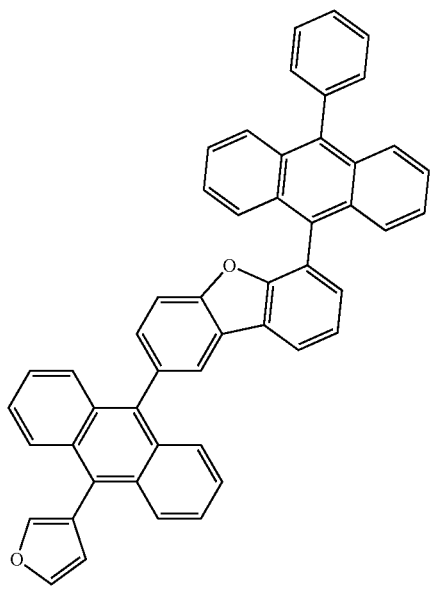
780
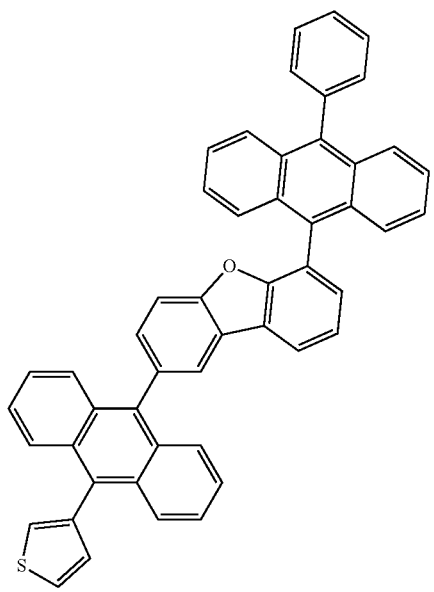
1750
-continued
781
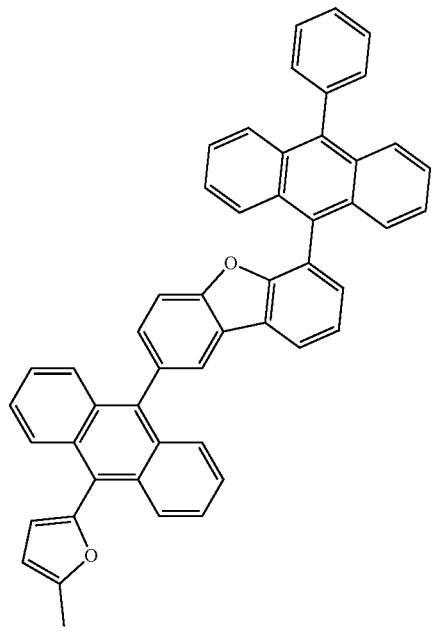
782
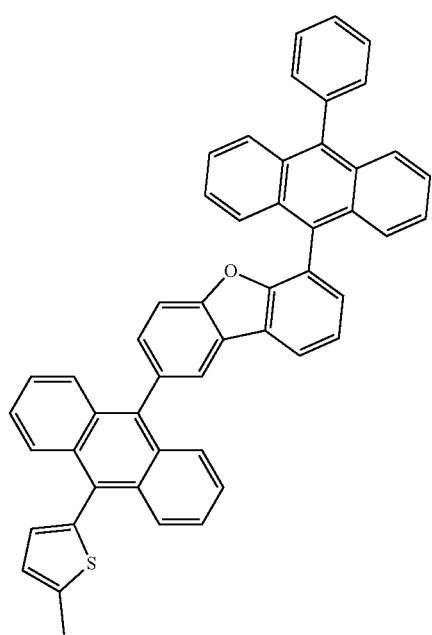

1751
-continued
783
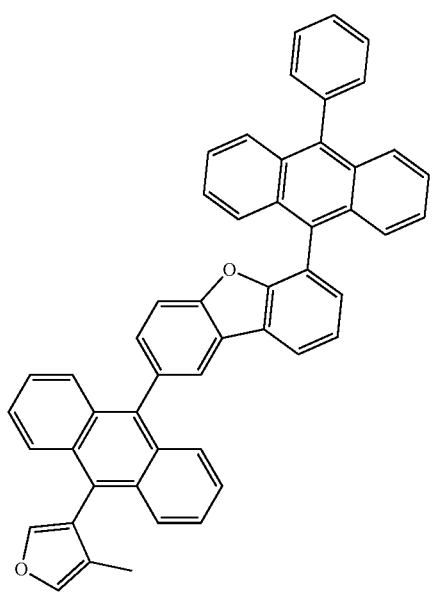
784
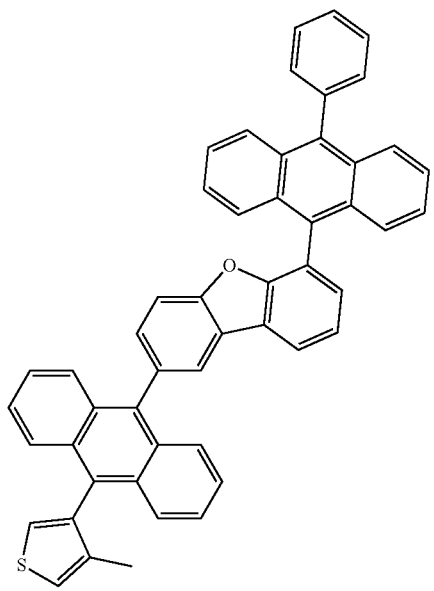
1752
-continued
785
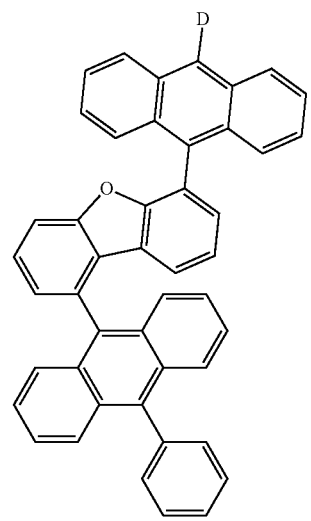
786
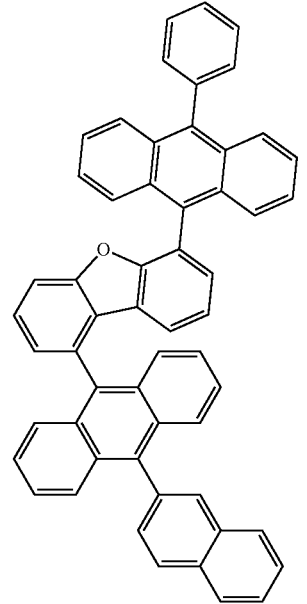

787
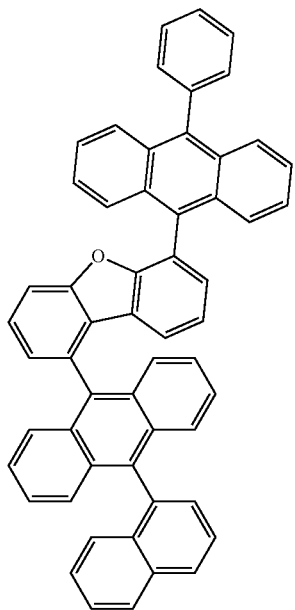
789
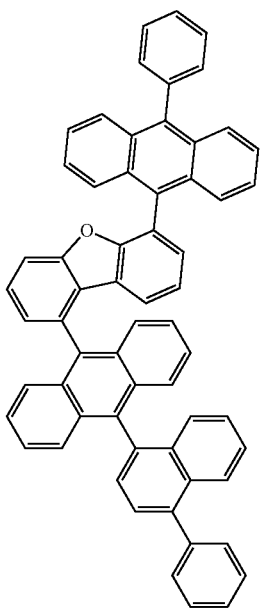
788
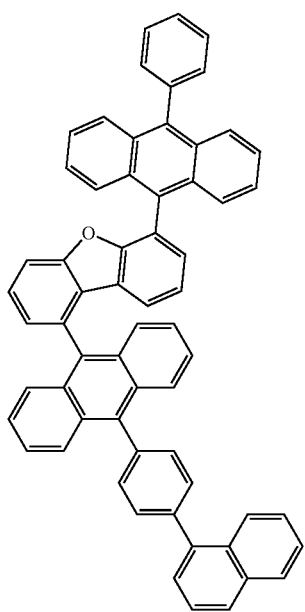
790
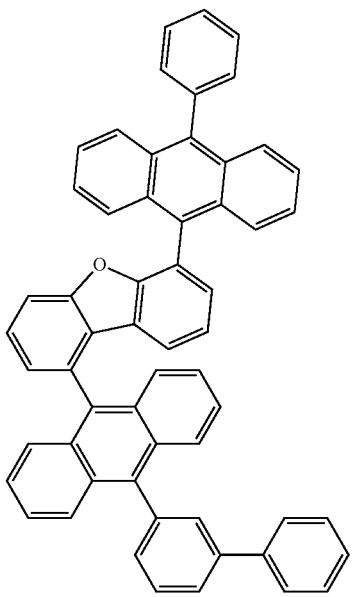

1755
-continued
791
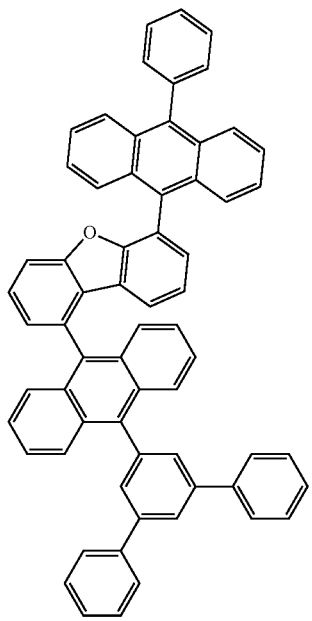
792
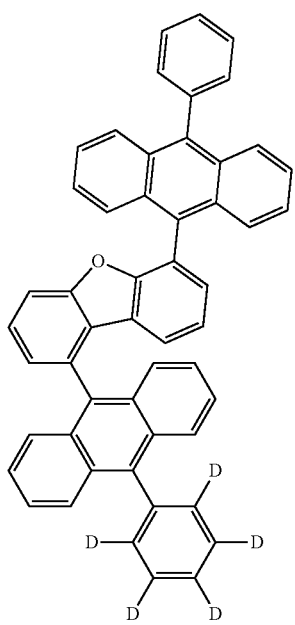
1756
-continued
793
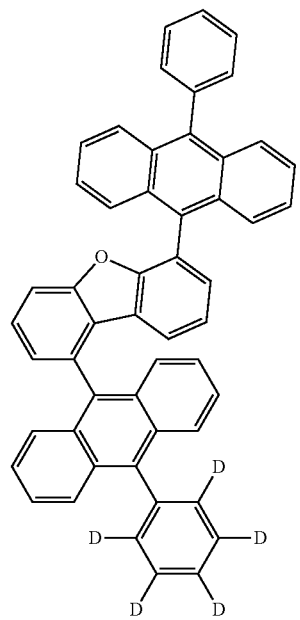
794
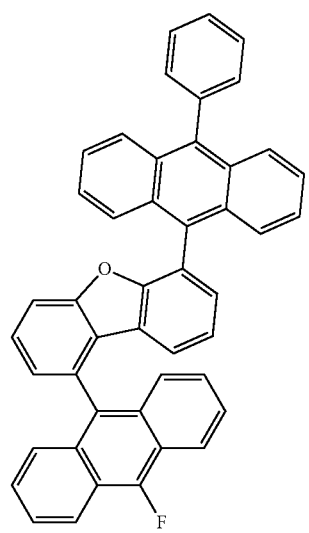

1757
-continued
795
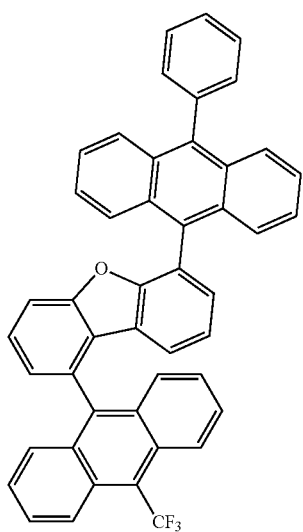
796
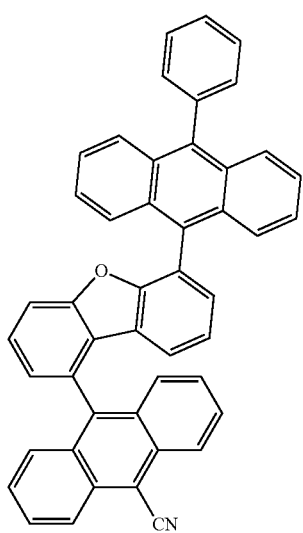
797
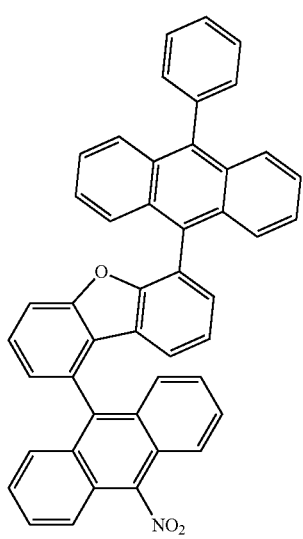
1758
-continued
798
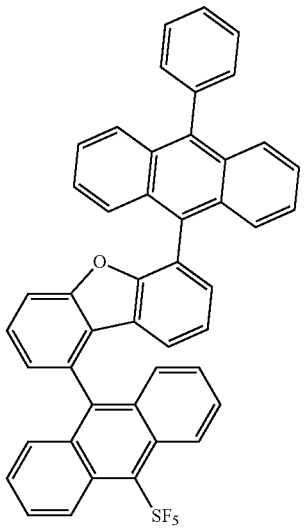
799
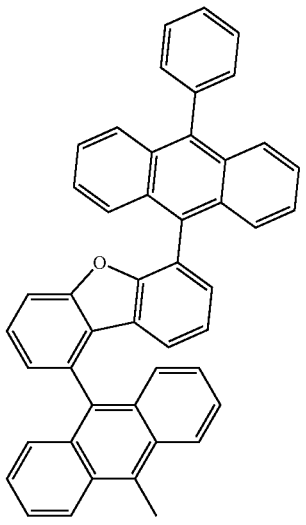
800
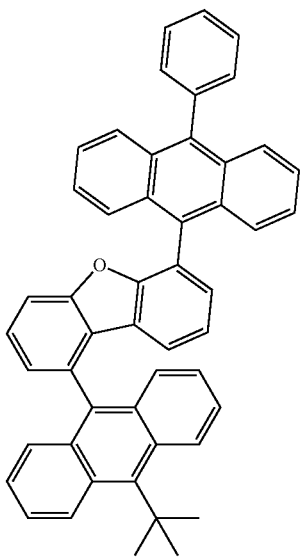

1759
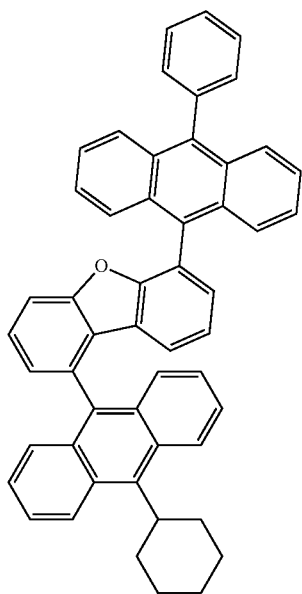
1760
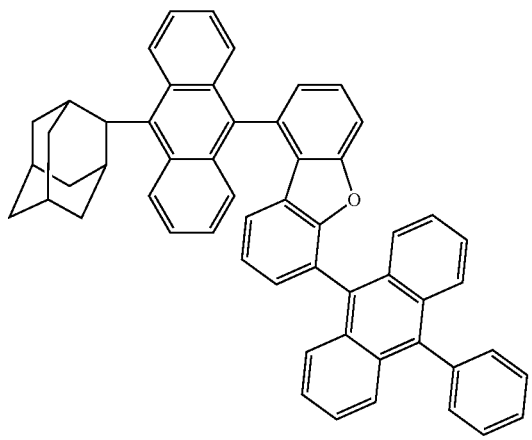
801  802
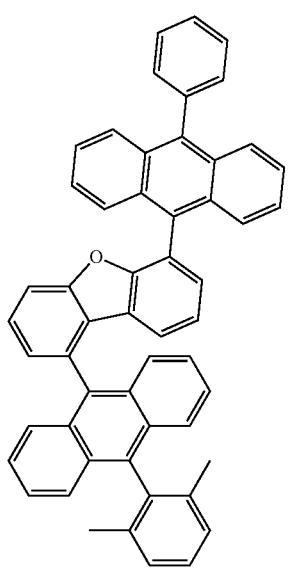  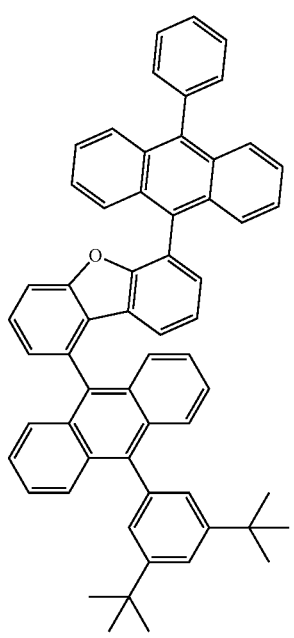
803  804

-continued
1761
805
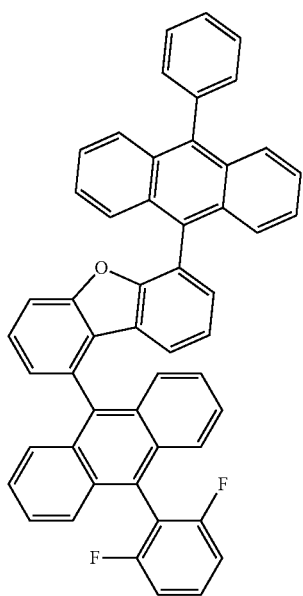
1762
806
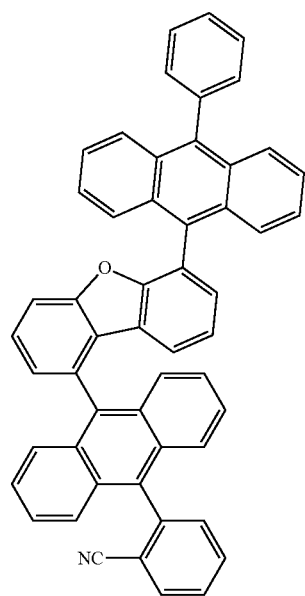
807
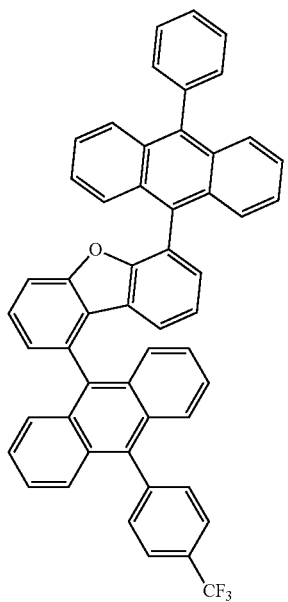
808
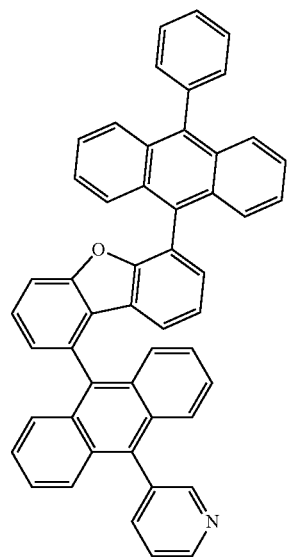

809
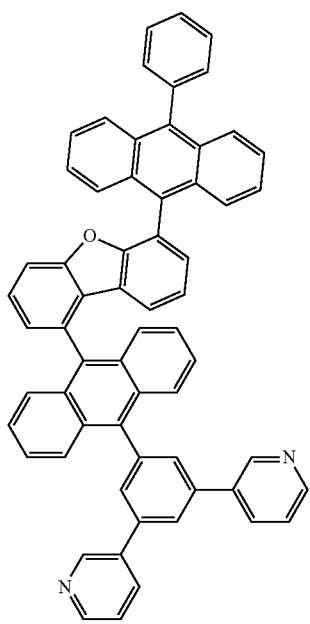
810
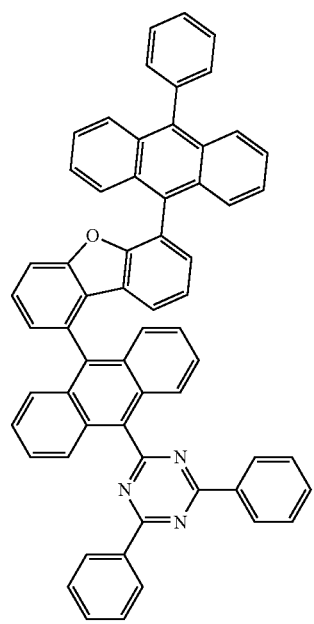
811
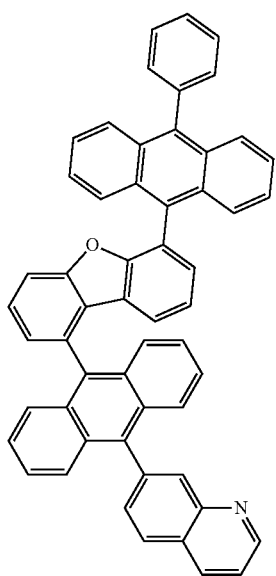
812
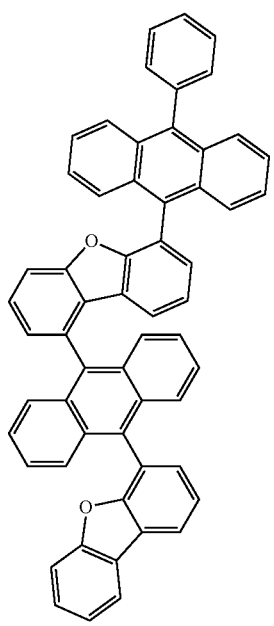

-continued
813
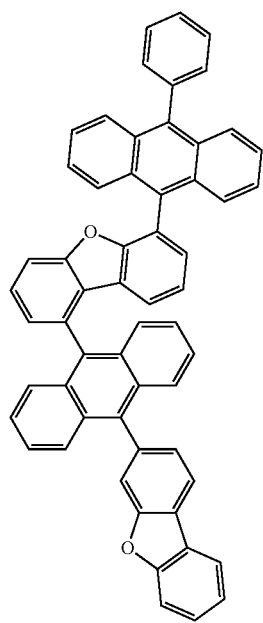
814
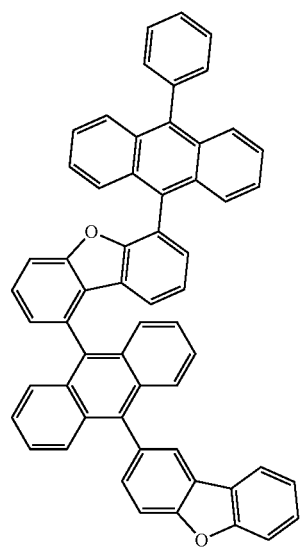
815
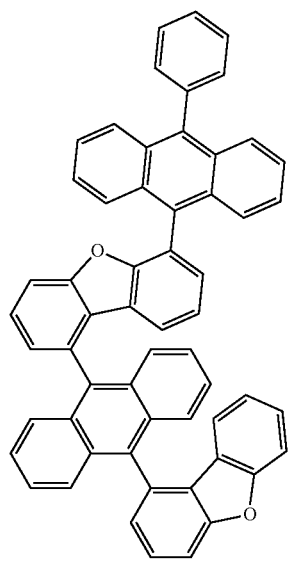
816
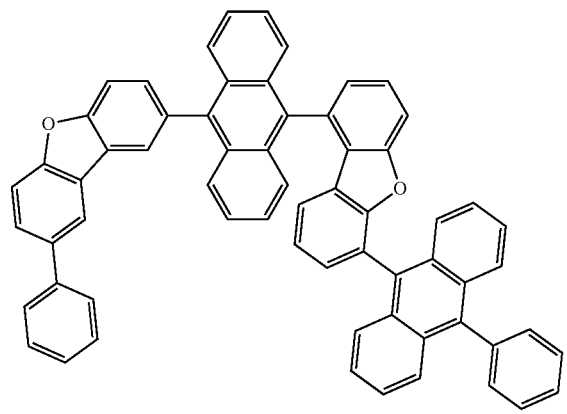

1767 1768
-continued
817
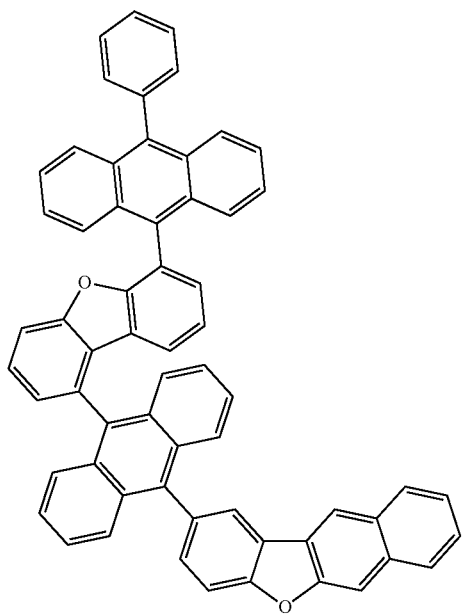
818
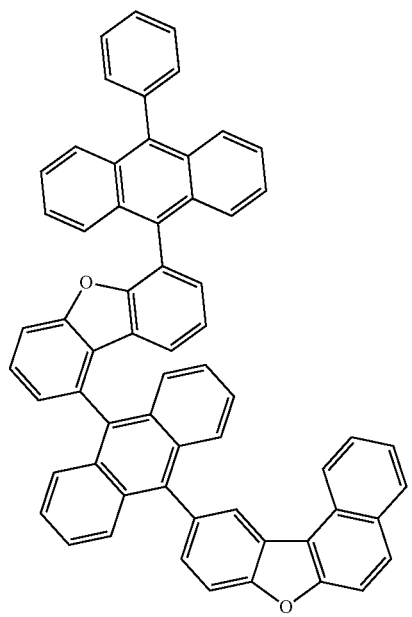
819
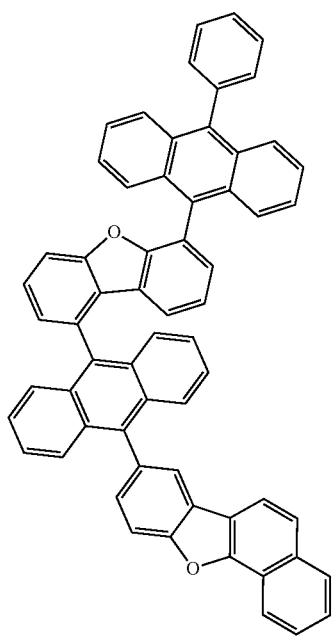
820
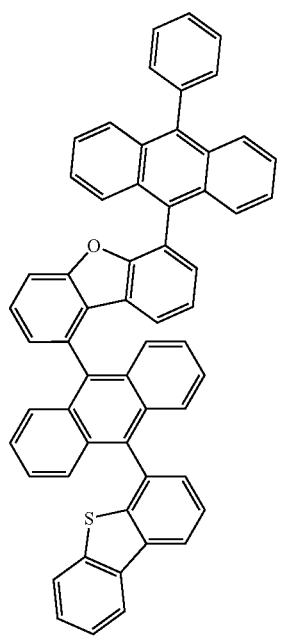

-continued
821 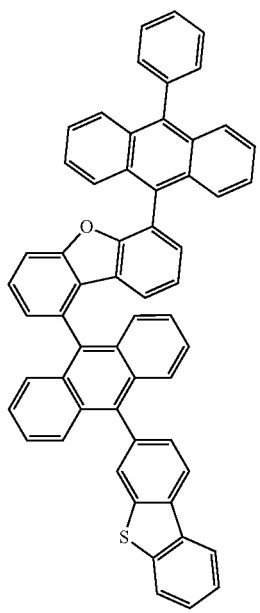
822 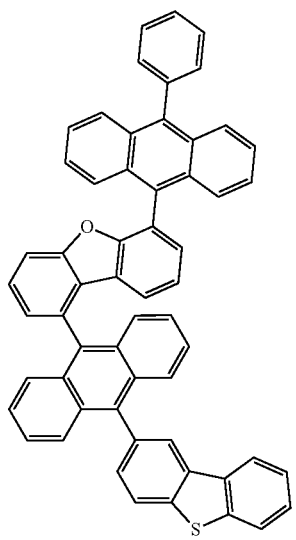
823 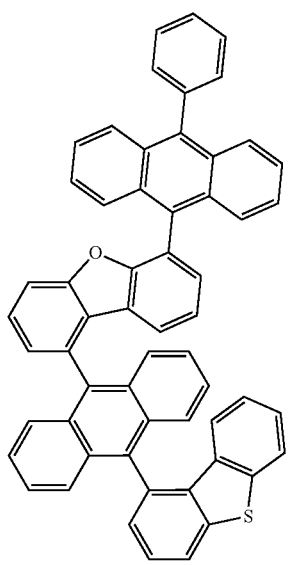
824 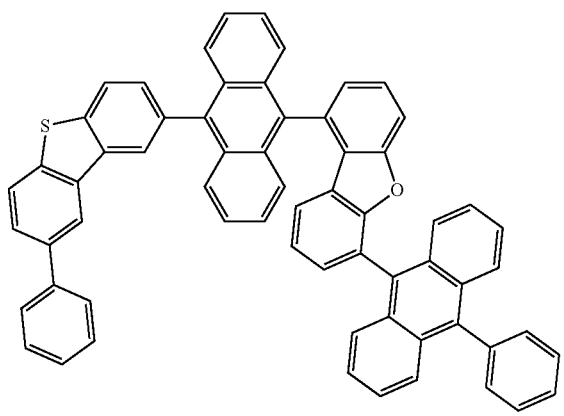

-continued
825
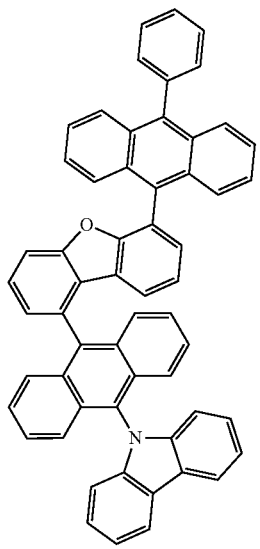
826
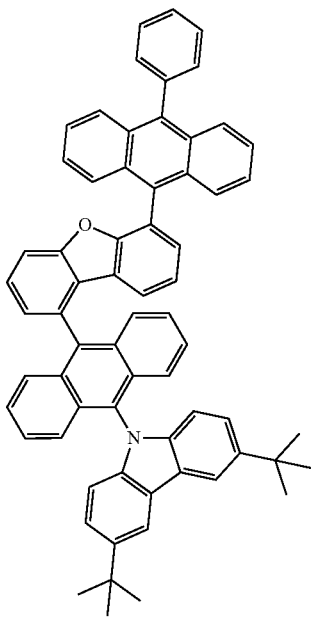
827
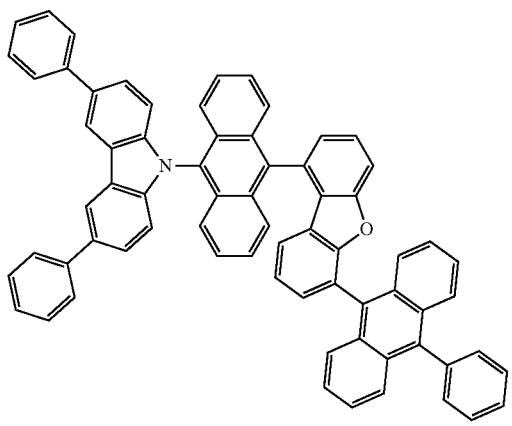
828
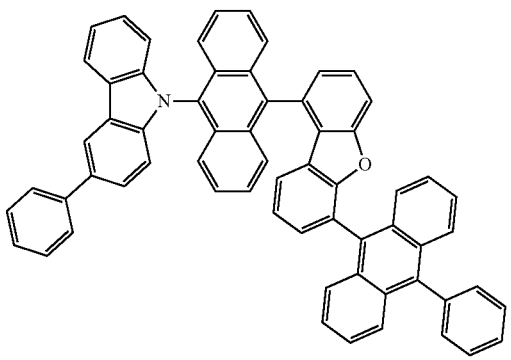
829
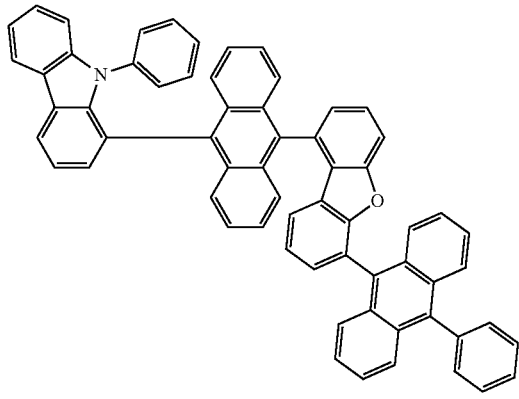
830
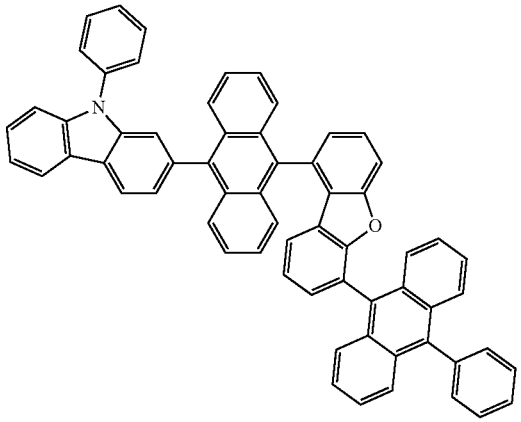

-continued
831
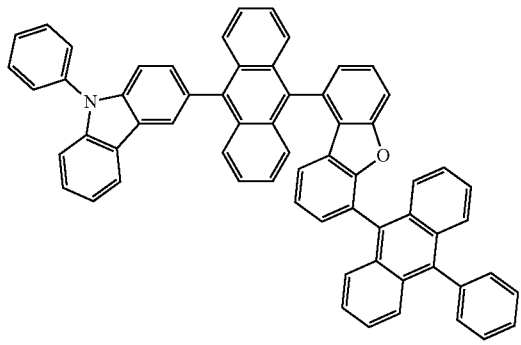
832
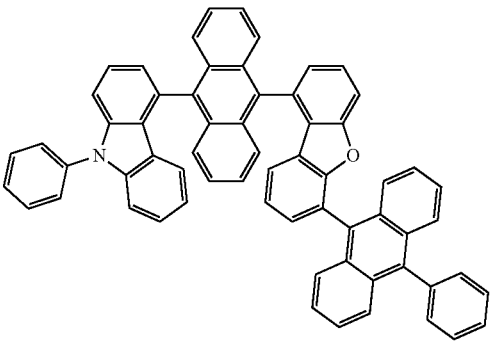
833
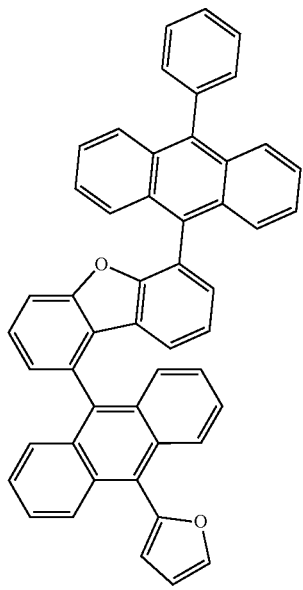
834
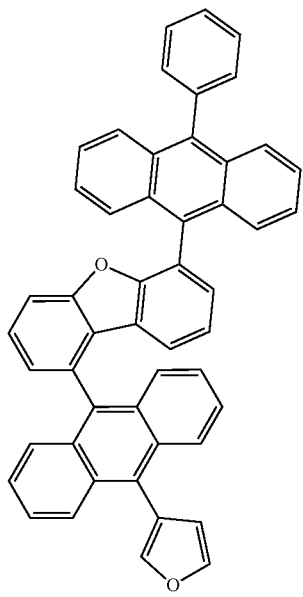
835
836

-continued
| 837 | 838 |
|---|---|
| 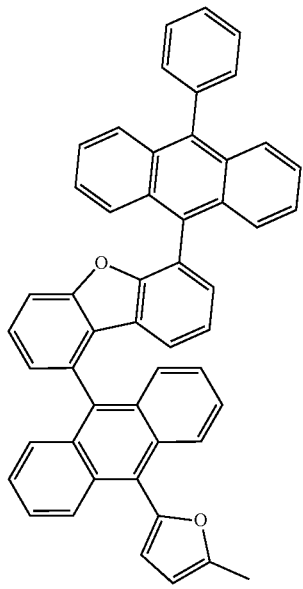 | 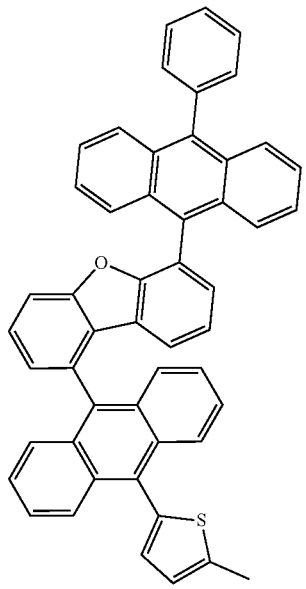 |
| 839 | 840 |
| 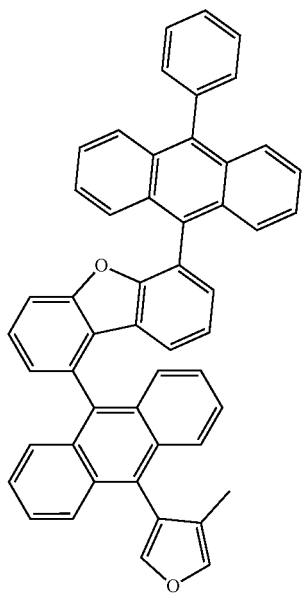 | 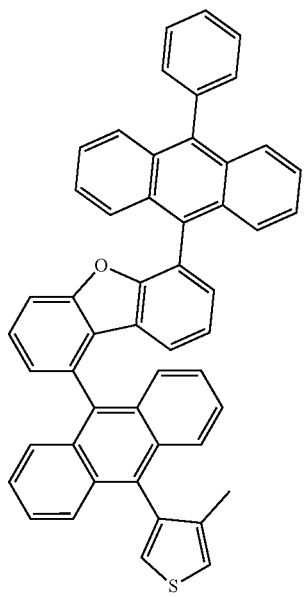 |
| 841 | 842 |
| 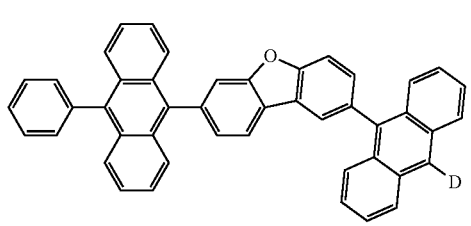 | 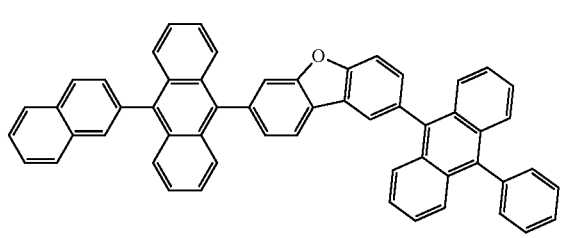 |
| 843 | 844 |
| 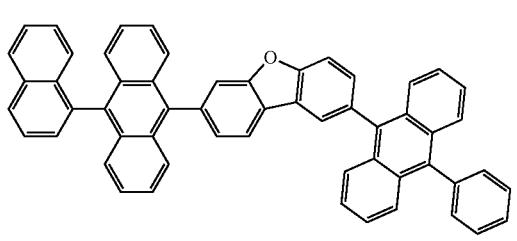 | 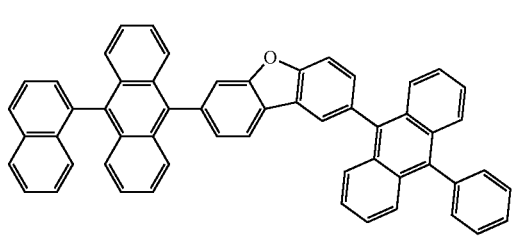 |

-continued
845
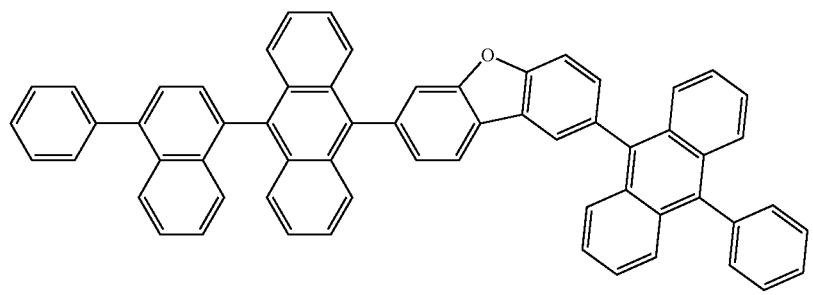
846
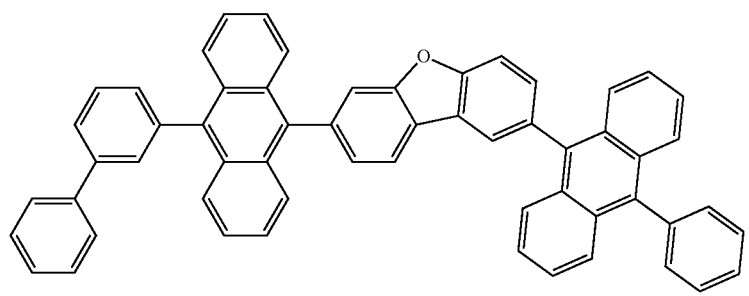
847
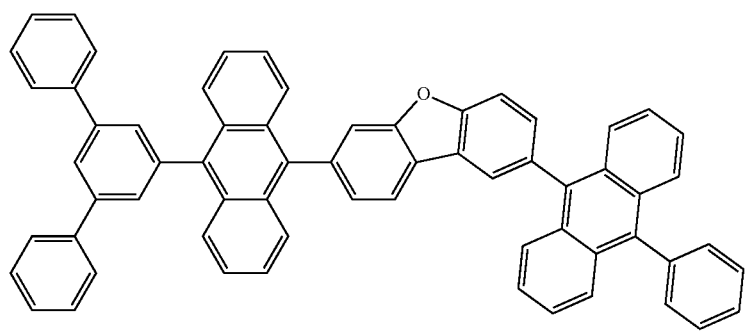
848
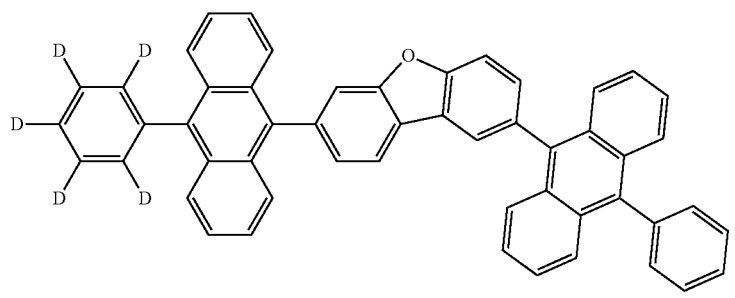
849
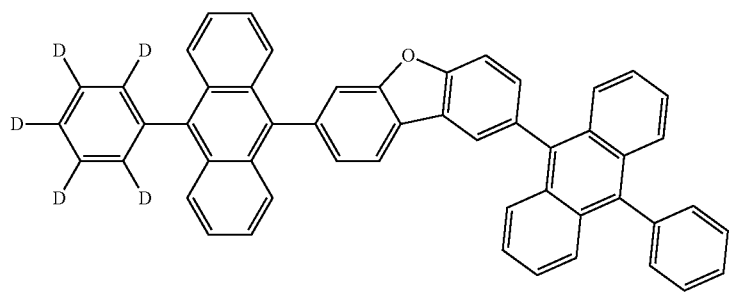

-continued
| | |
|---|---|
| 850 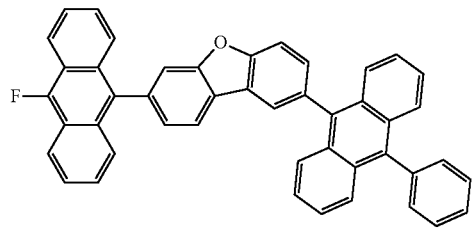 | 851 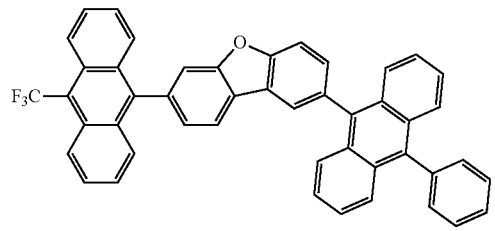 |
| 852 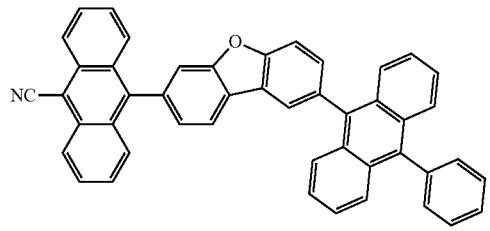 | 853 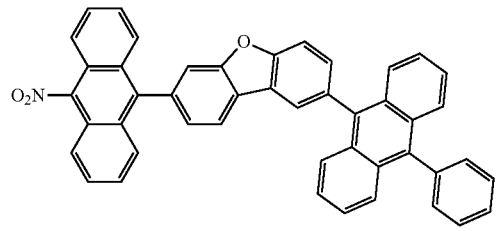 |
| 854 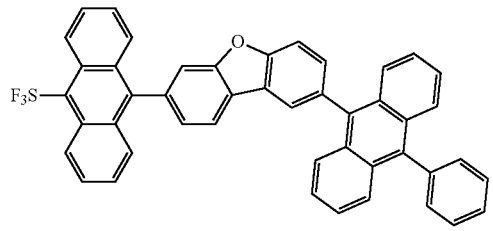 | 855 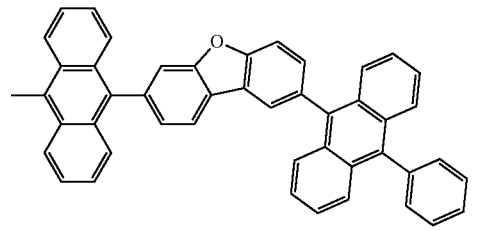 |
| 856 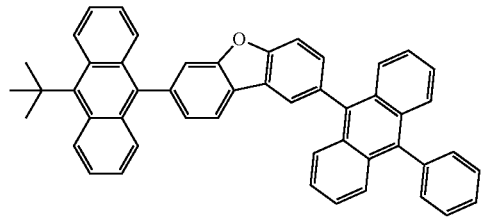 | 857 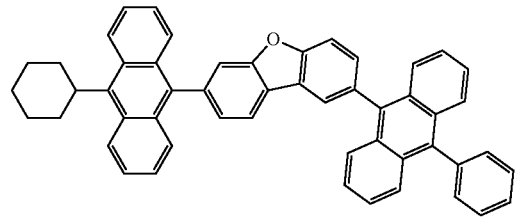 |
| 858 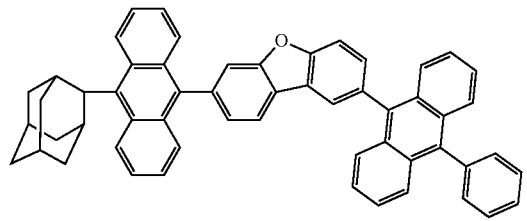 | 859 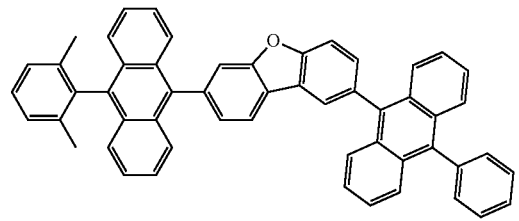 |
860
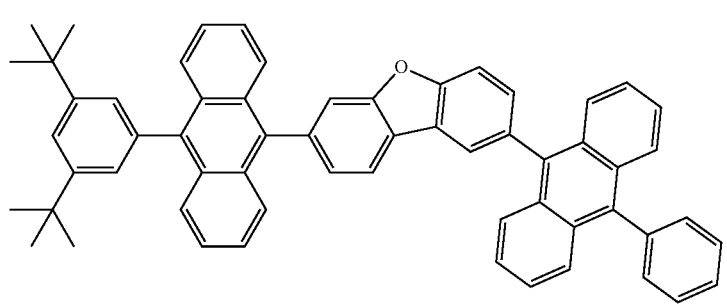

-continued
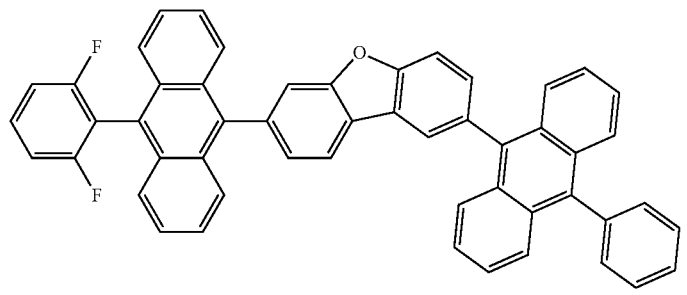
861

862
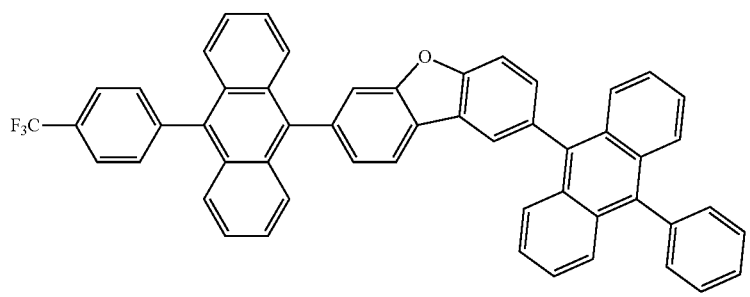
863
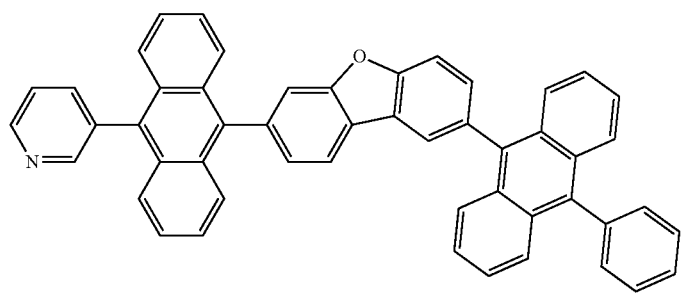
864
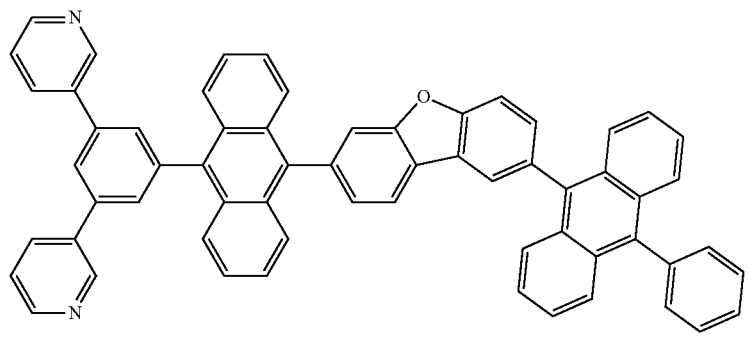
865

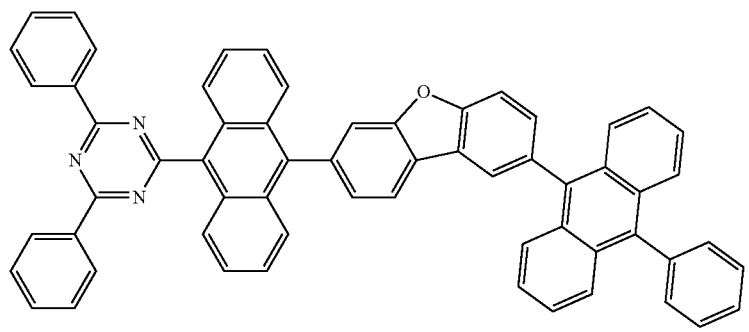
866
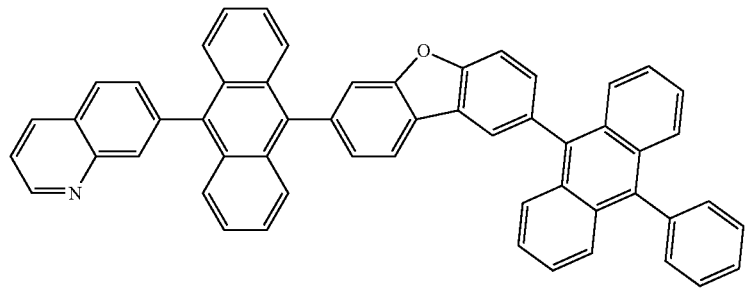
867
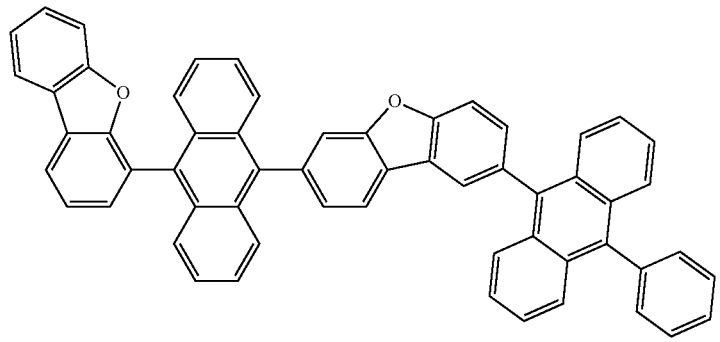
868
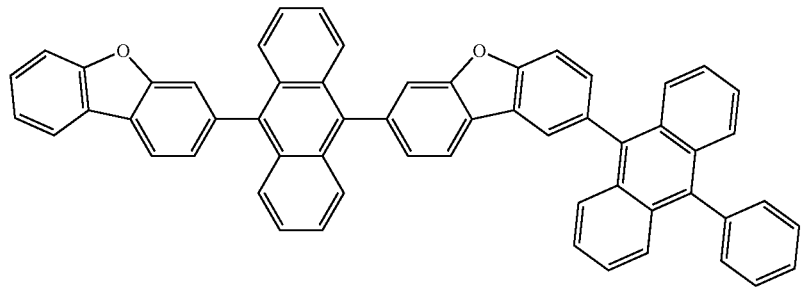
869
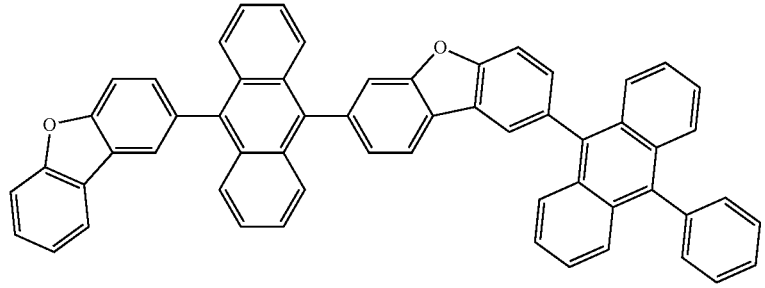
870

-continued
871
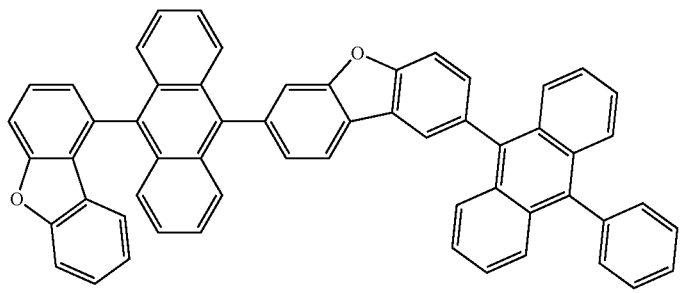
872
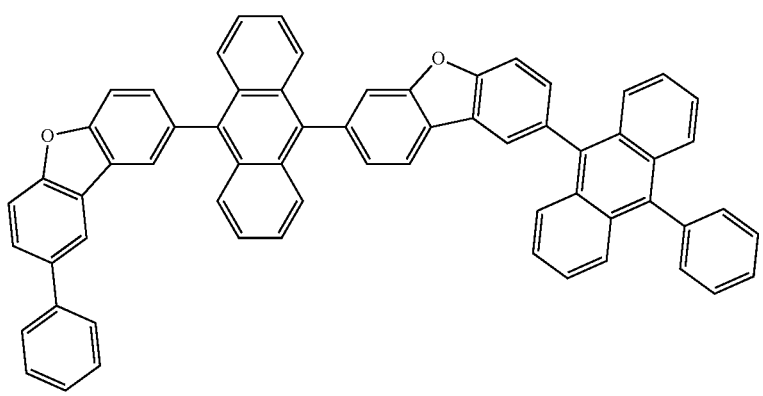
873
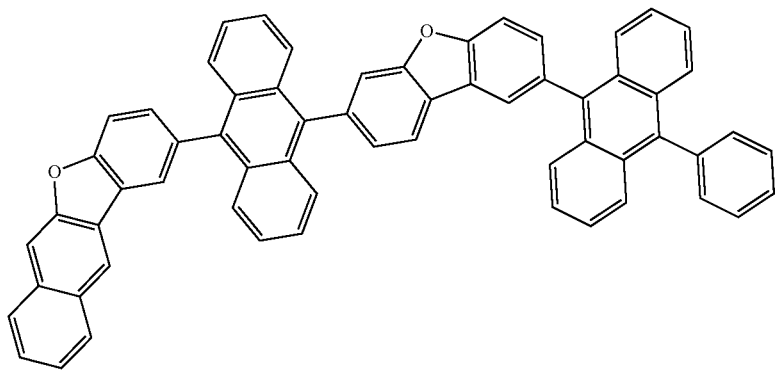
874
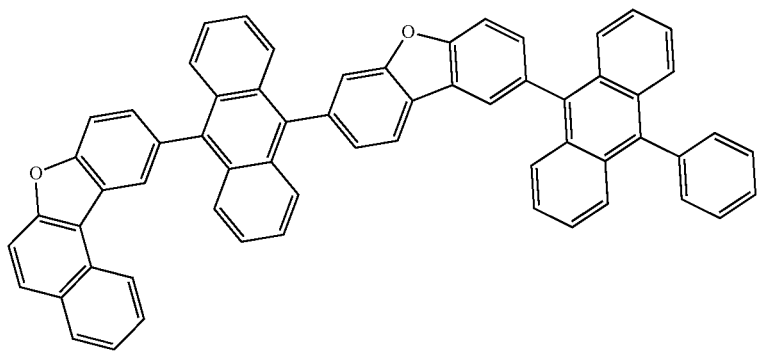

-continued
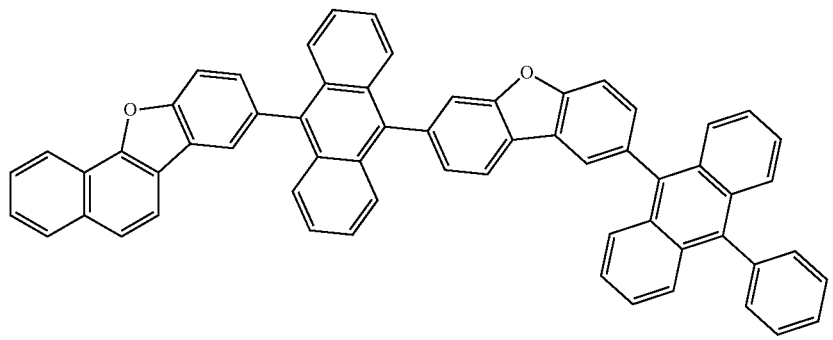
875
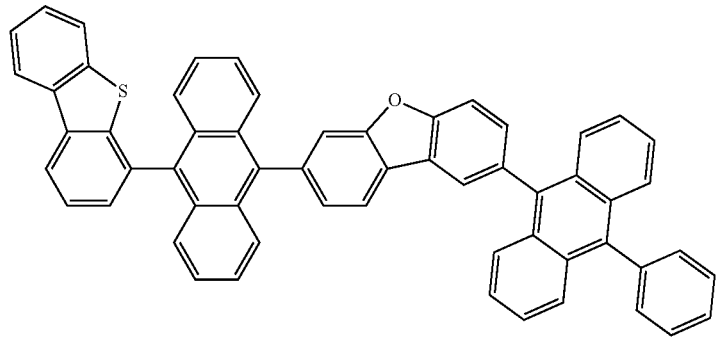
876
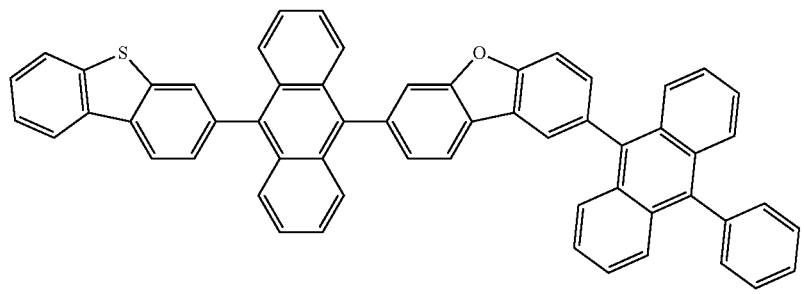
877
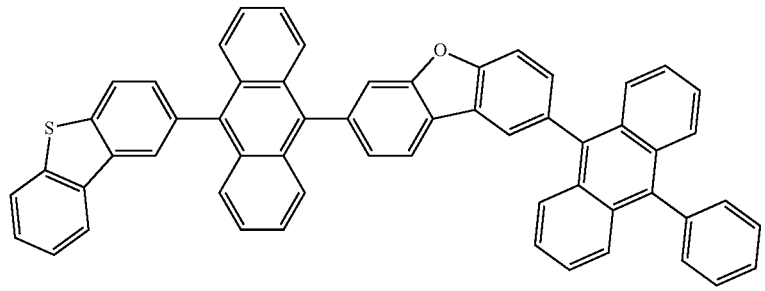
878
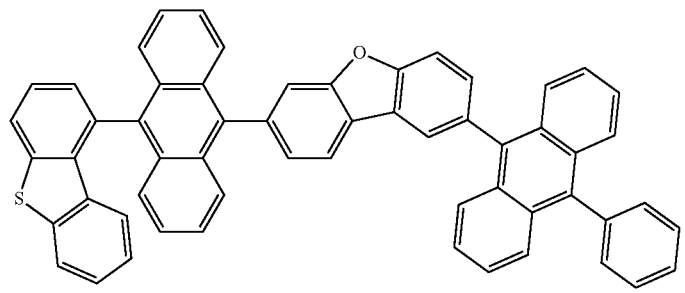
879

-continued
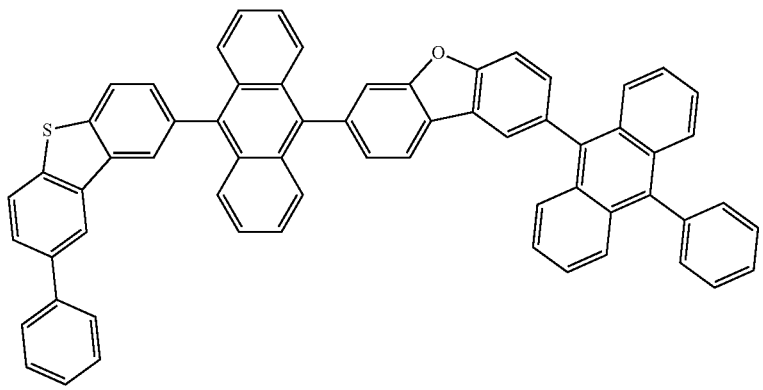
880
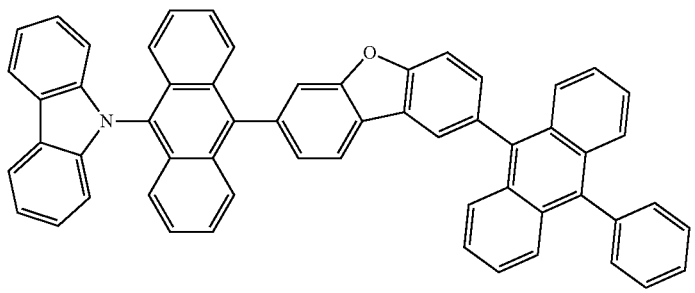
881
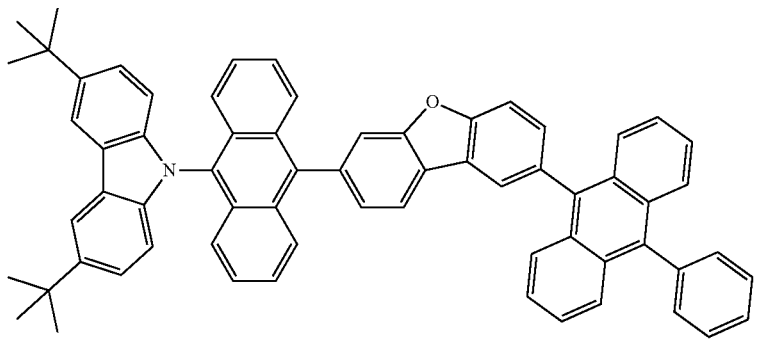
882
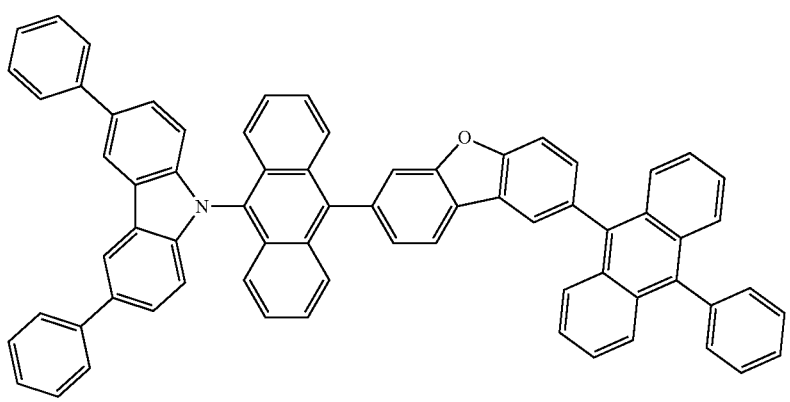
883

-continued
884
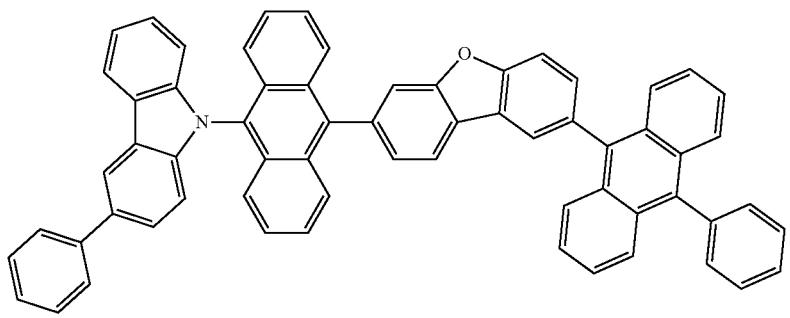
885
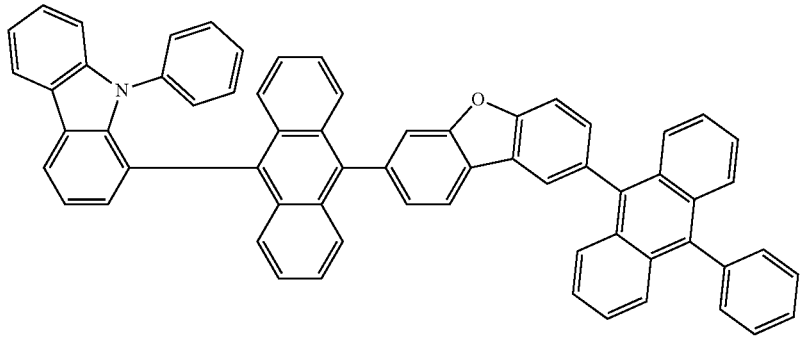
886
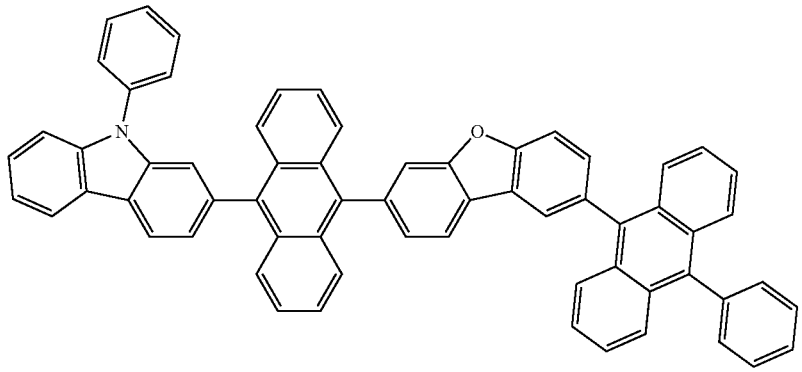
887
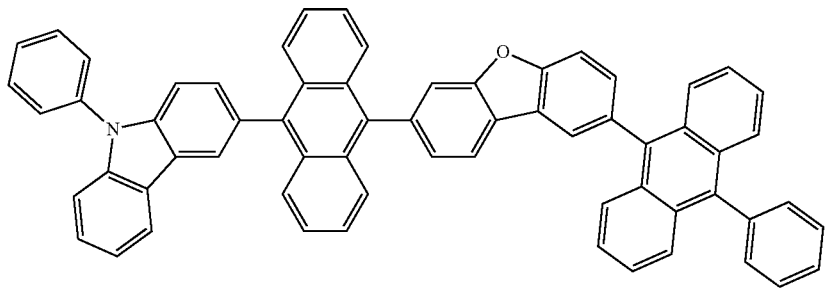
888
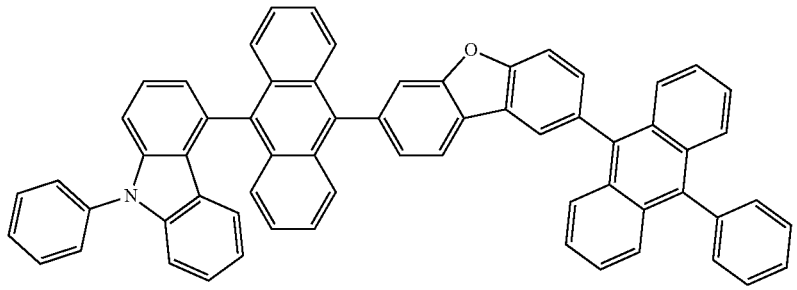

-continued
889
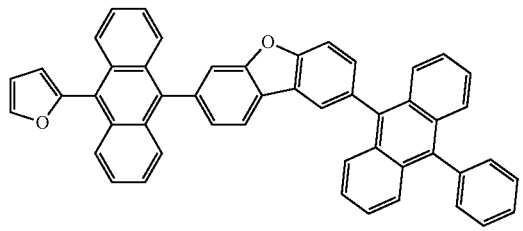
890
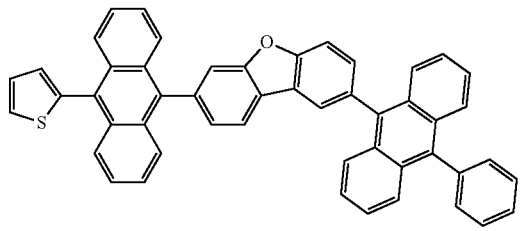
891
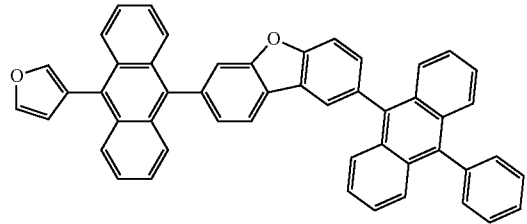
892
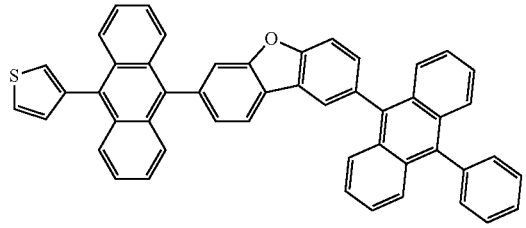
893
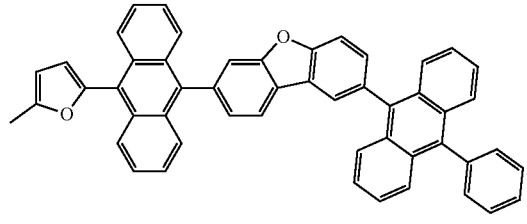
894
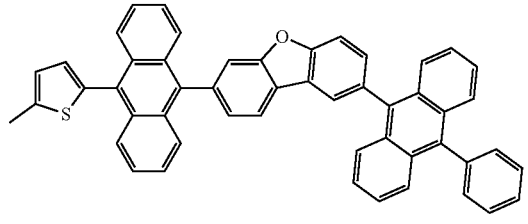
895
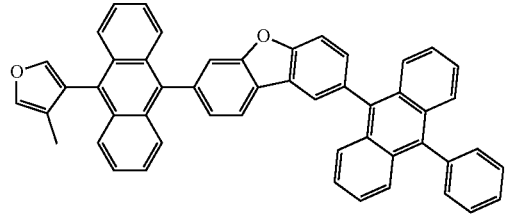
896
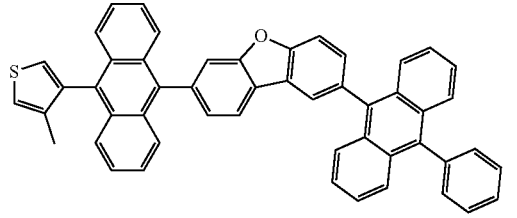
897
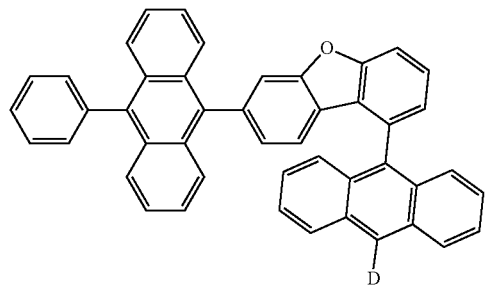
898
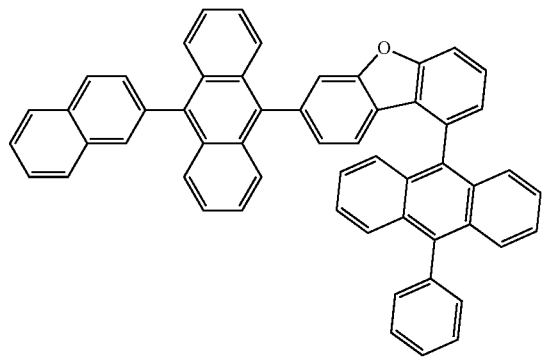
899
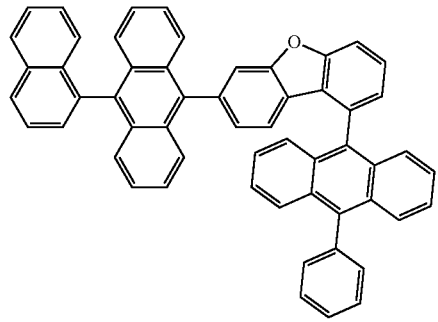
900
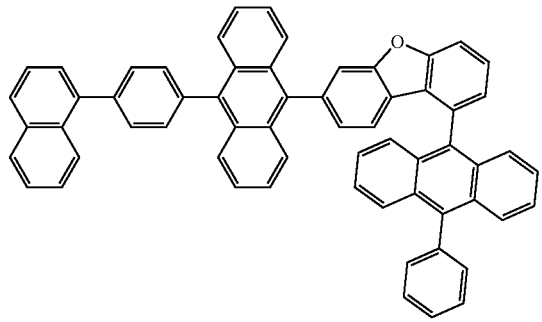

-continued
901
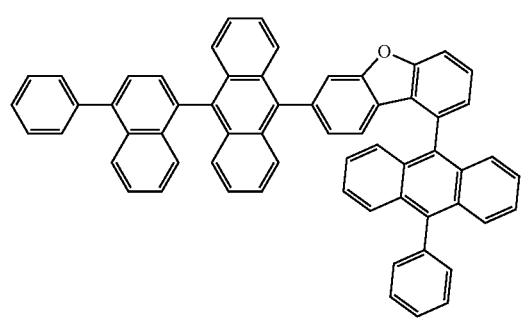
902
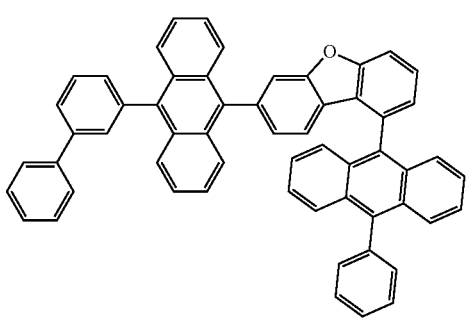
903
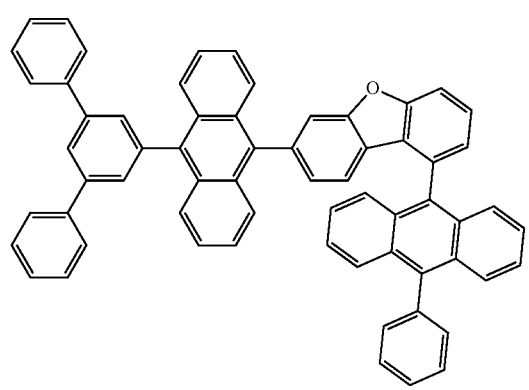
904
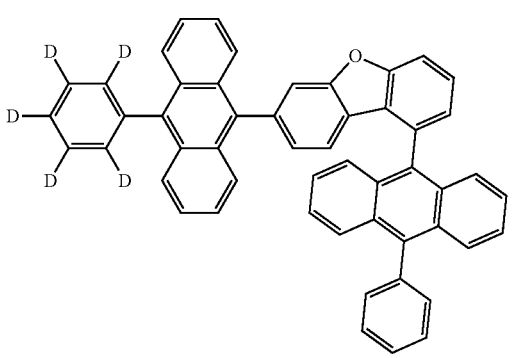
905
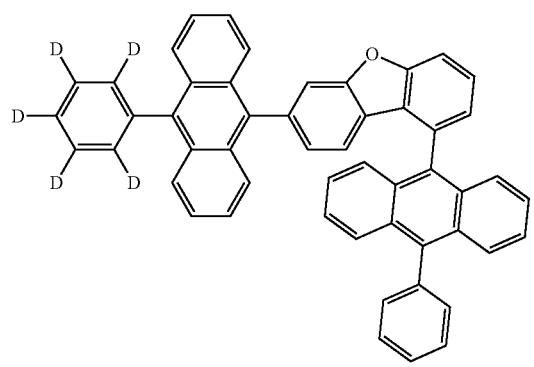
906
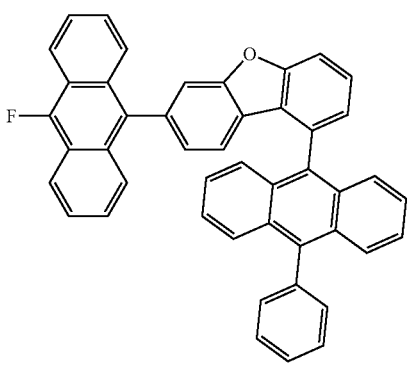
907
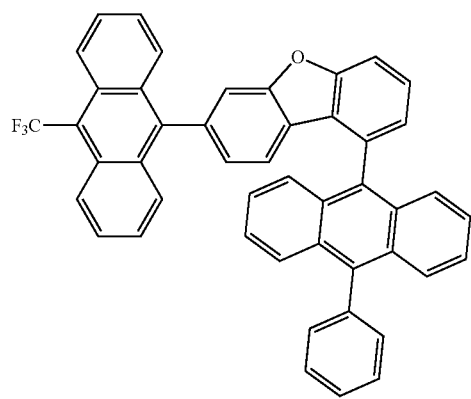
908
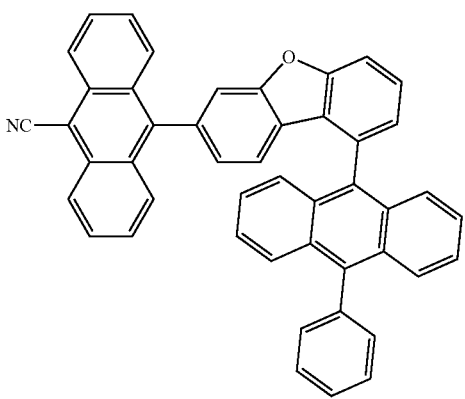

909
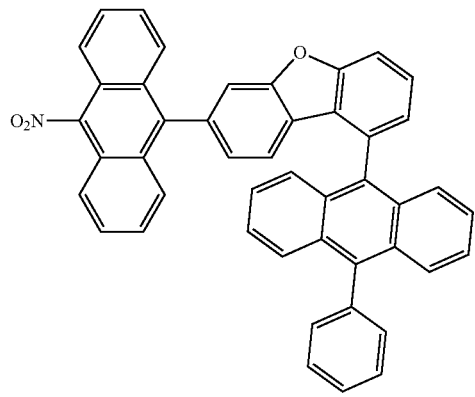
910
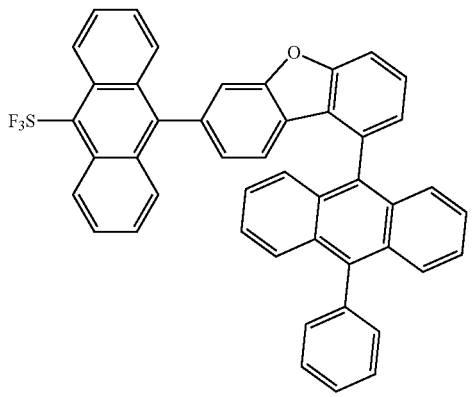
911
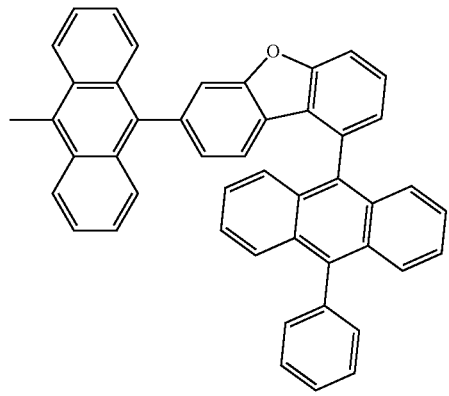
912
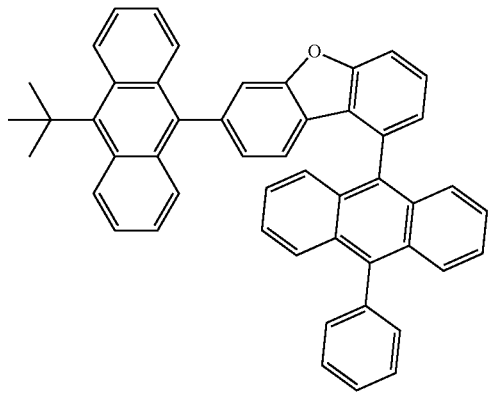
913
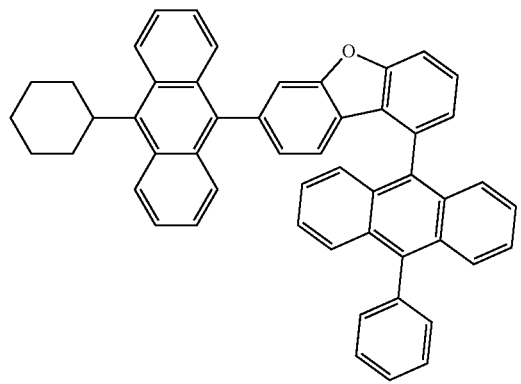
914
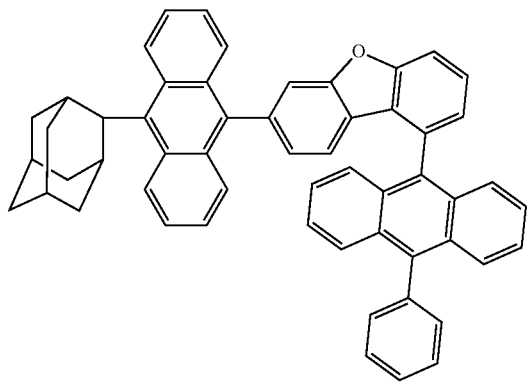
915
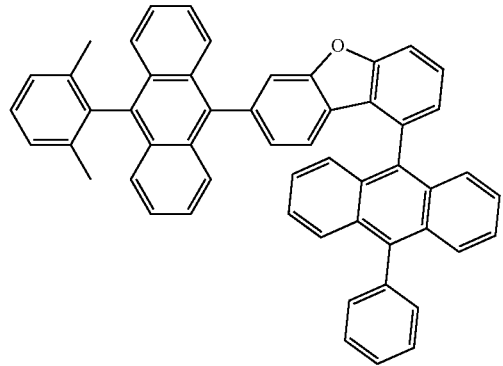
916
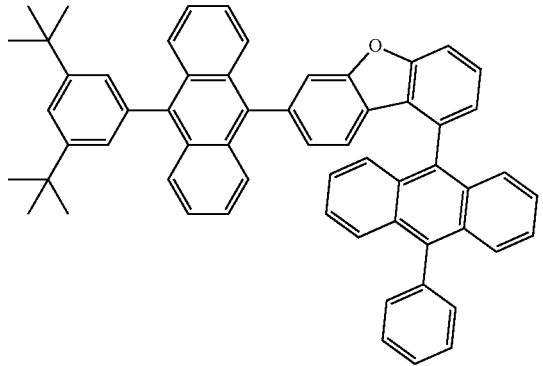

-continued
917
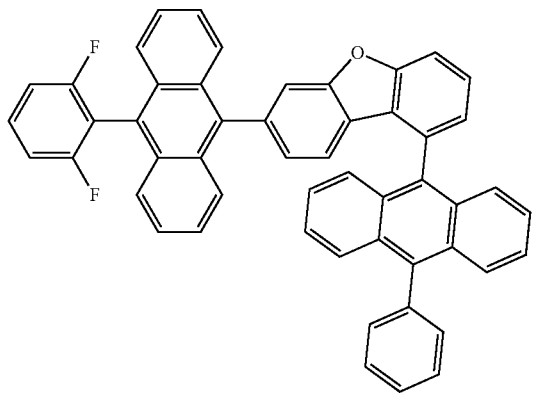
918
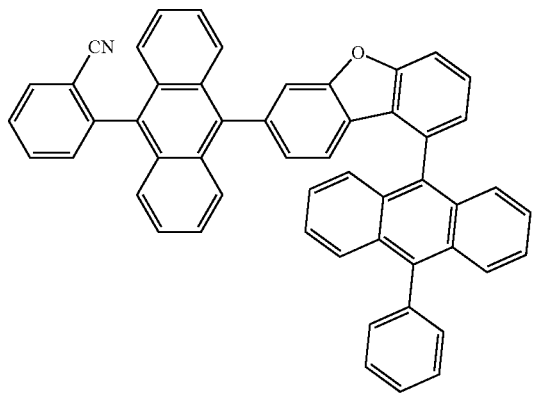
919
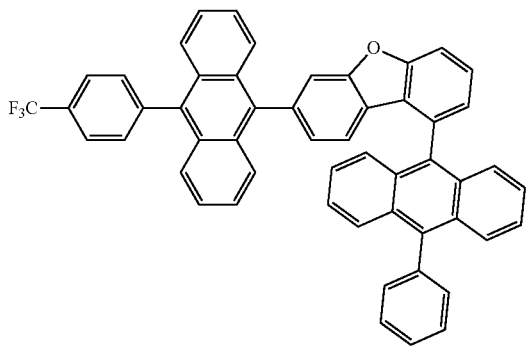
920
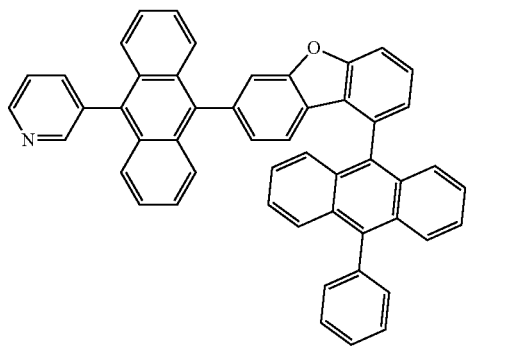
921
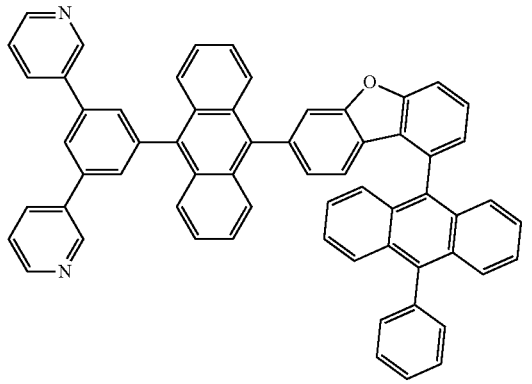
922
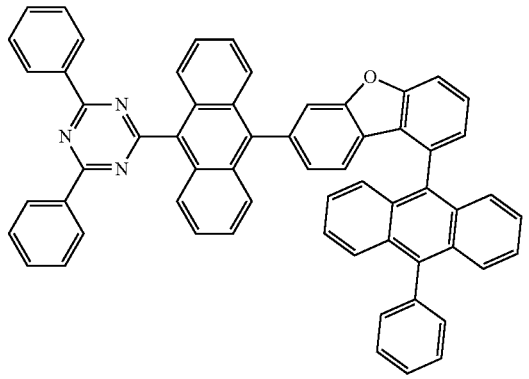
923
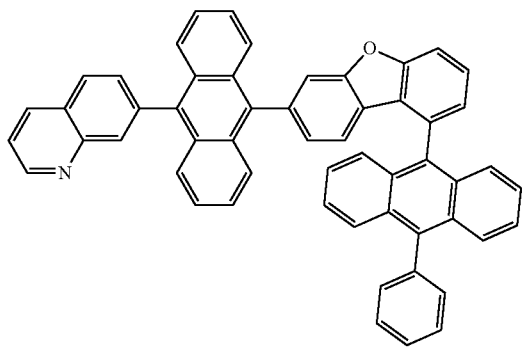
924
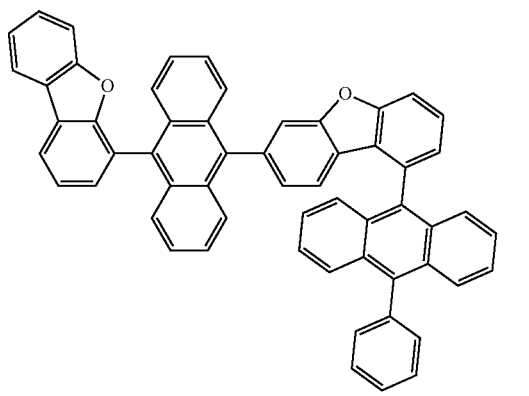

-continued
925
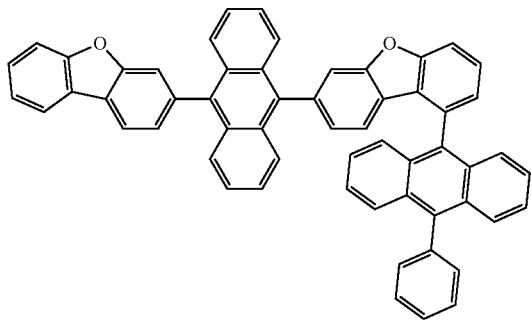
926
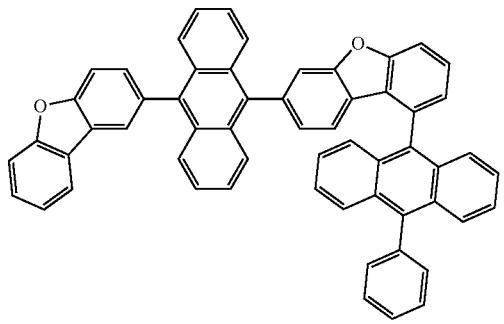
927
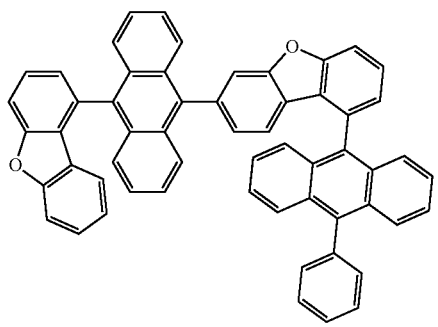
928
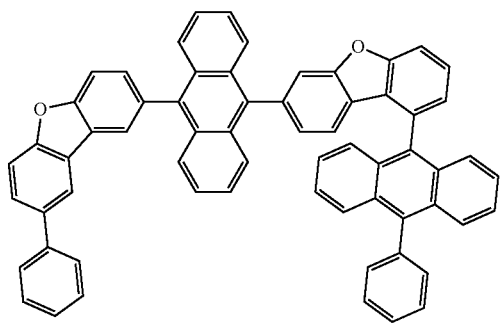
929
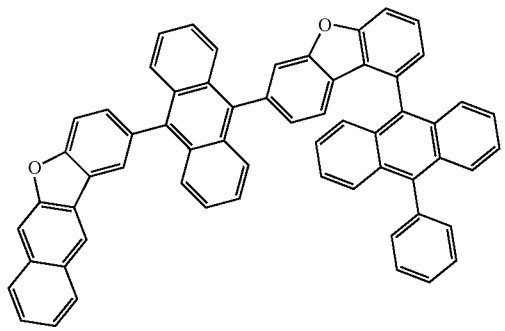
930
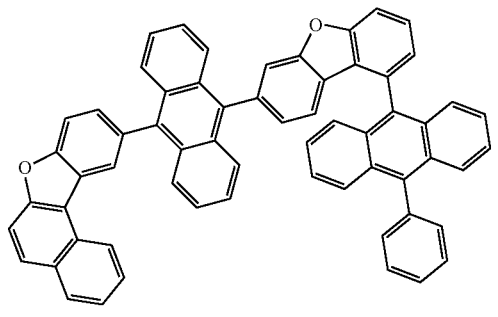
931
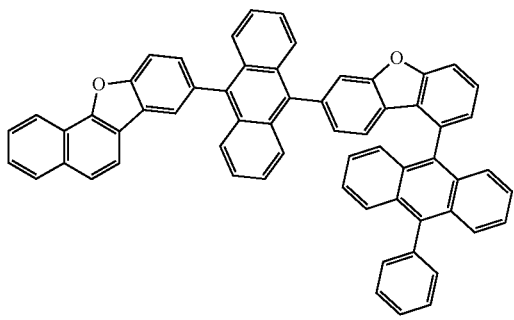
932
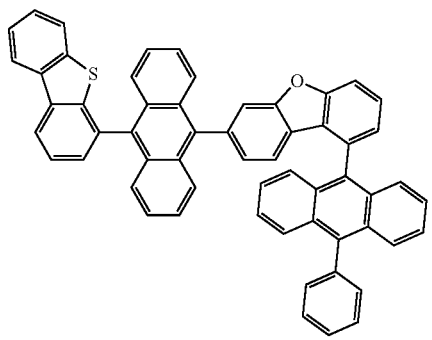
933
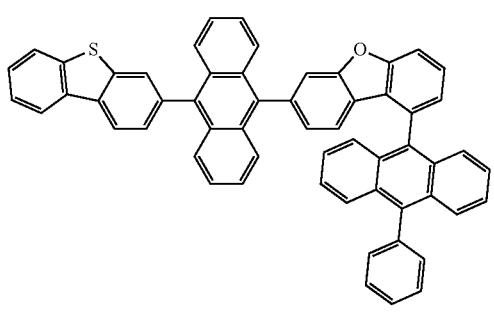
934
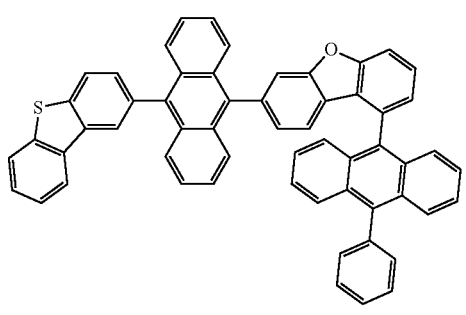

-continued
935
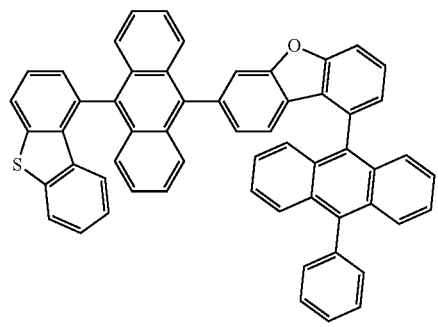
936
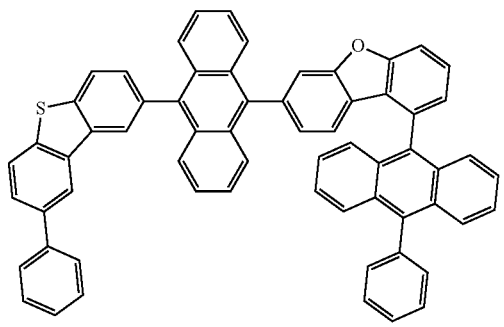
937
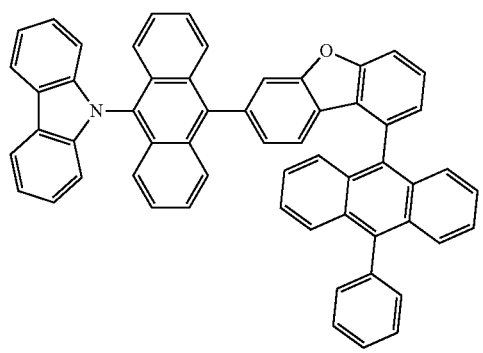
938
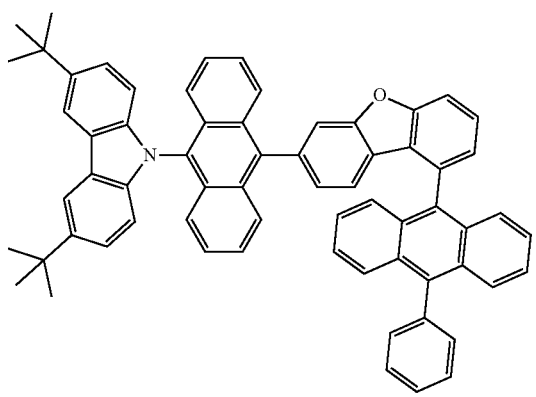
939
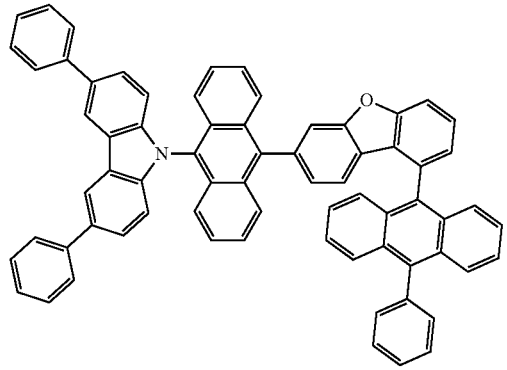
940
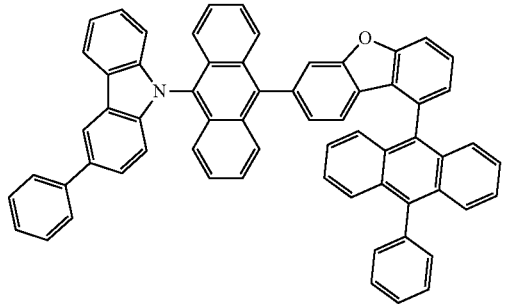
941
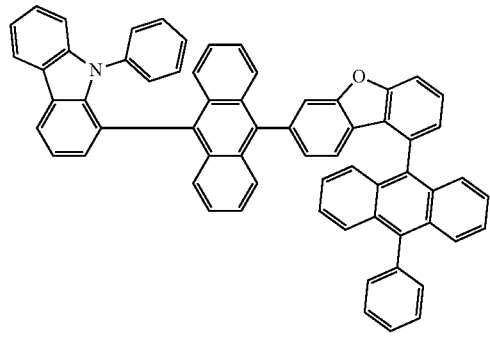
942
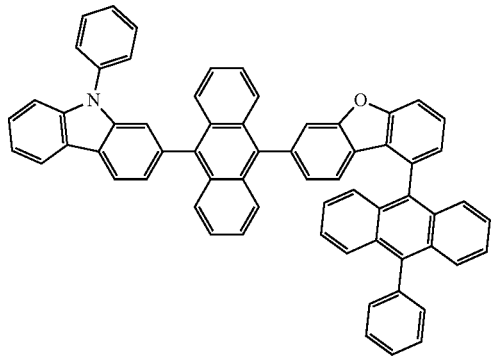

-continued
1805
943
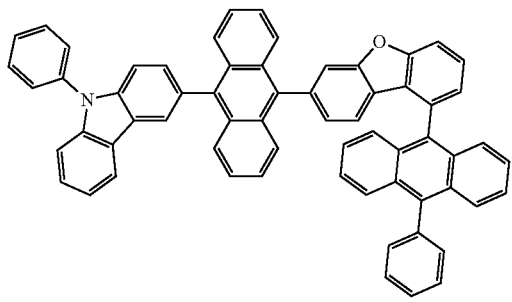
945
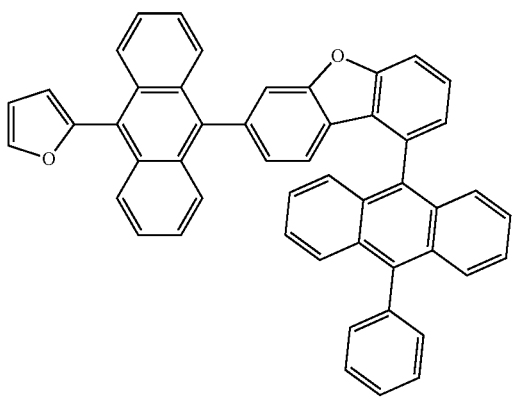
947
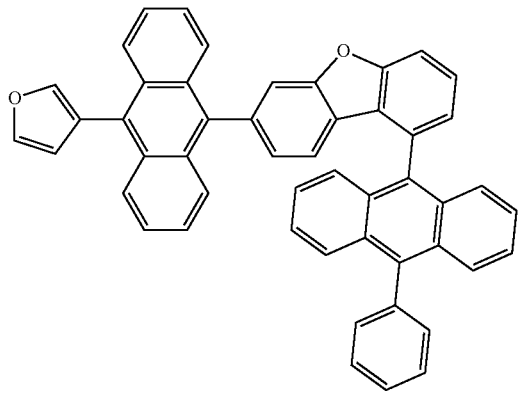
949
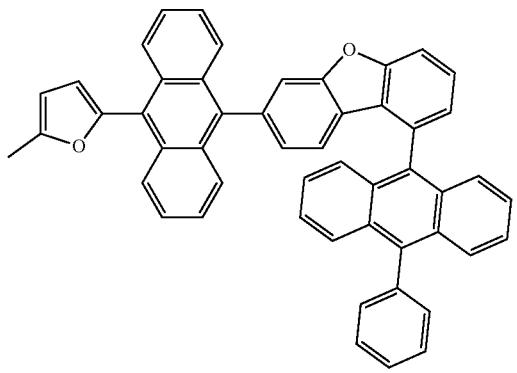
1806
944
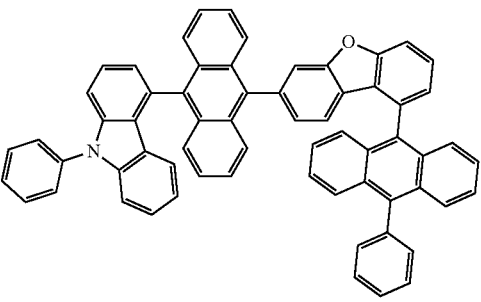
946
948
950
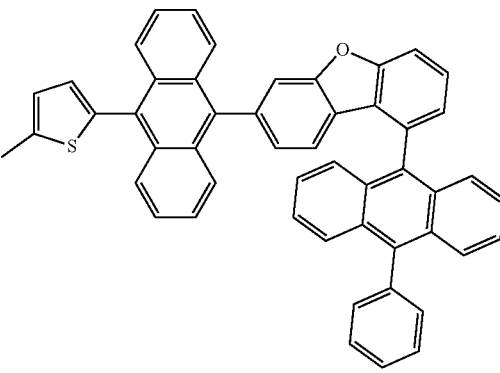

-continued
951 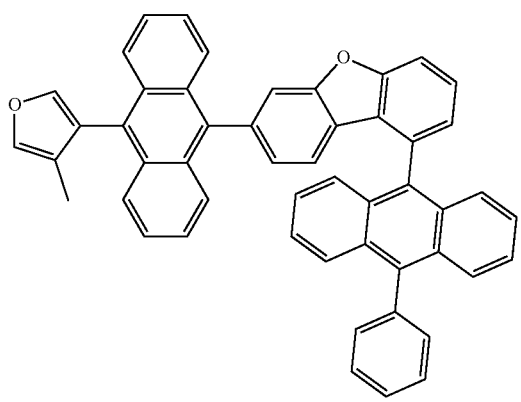
952 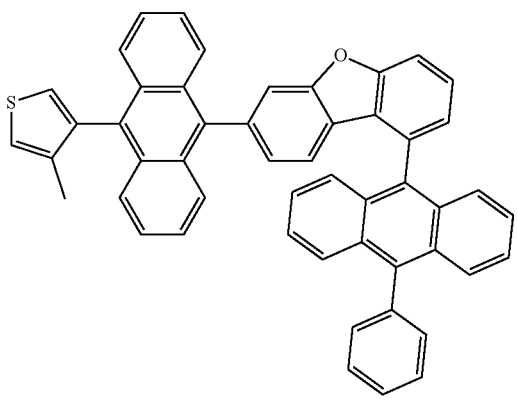
953 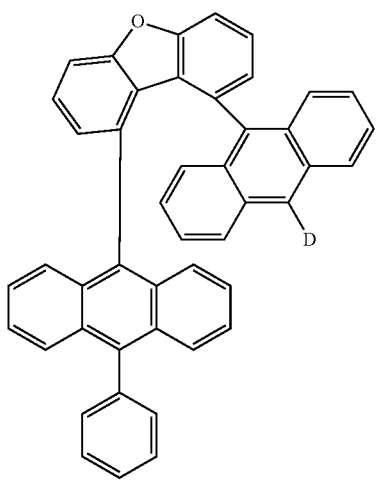
954 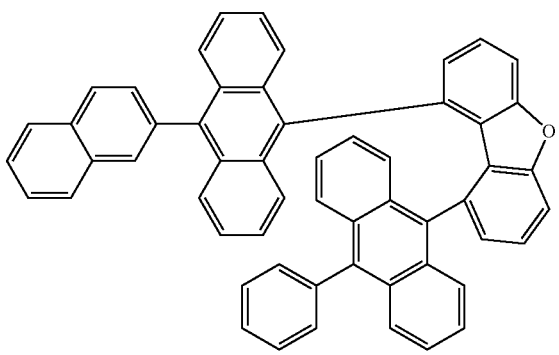
955 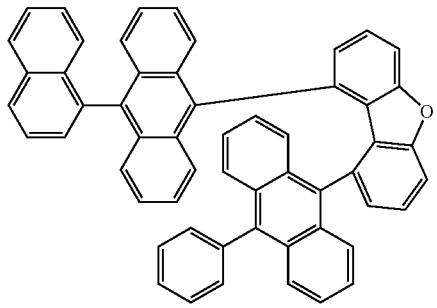
956 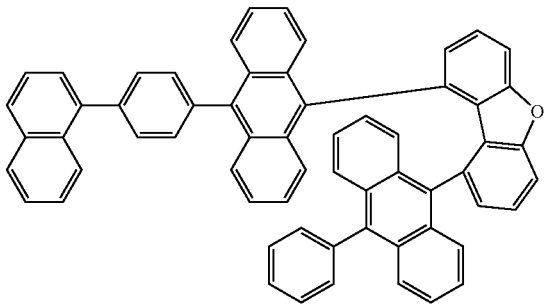
957 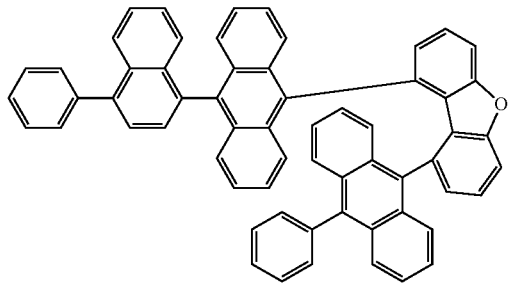
958 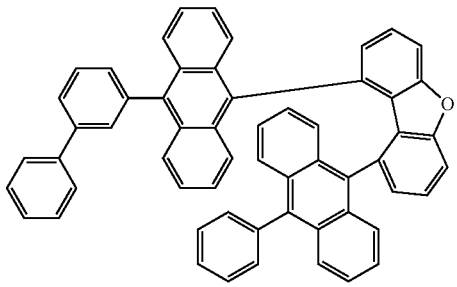

-continued
959
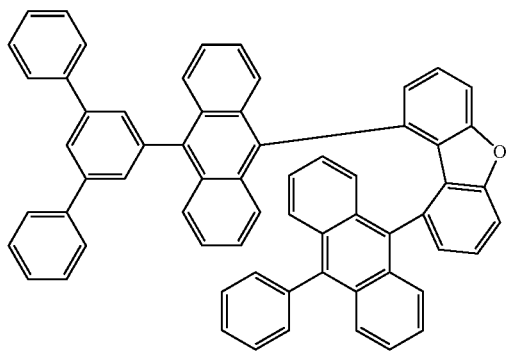
960
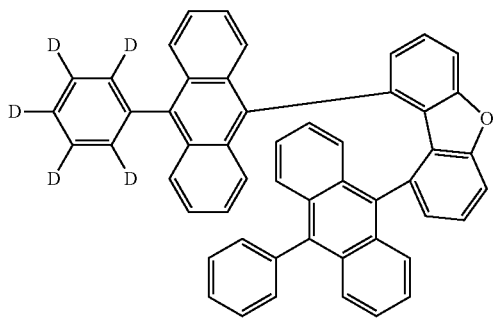
961
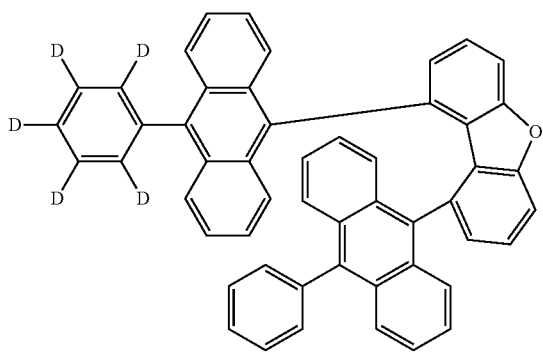
962
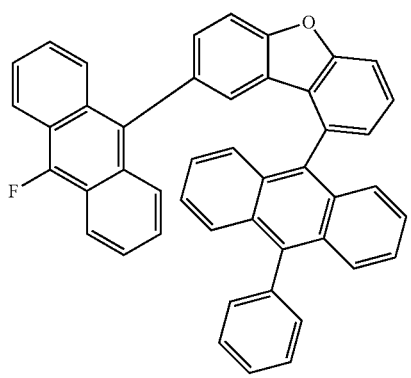
963
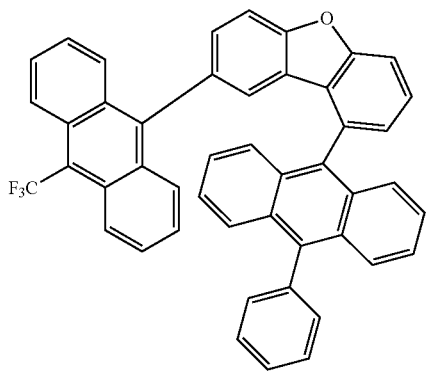
964
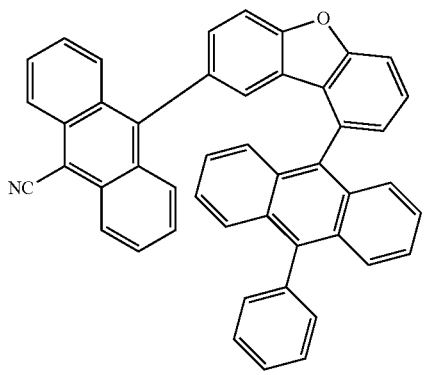
965
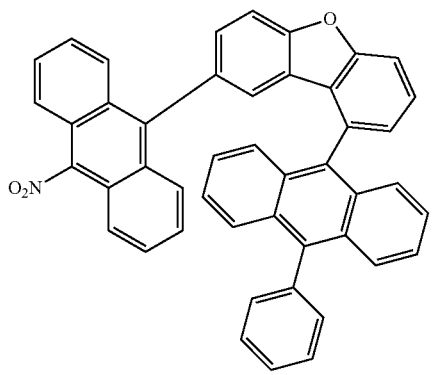
966
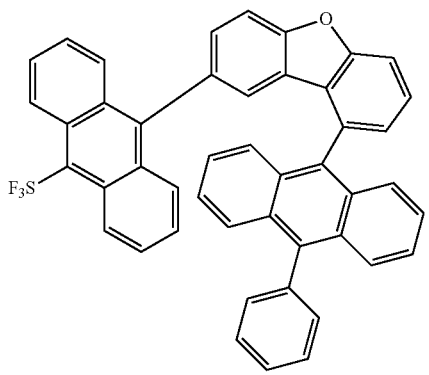

-continued
967
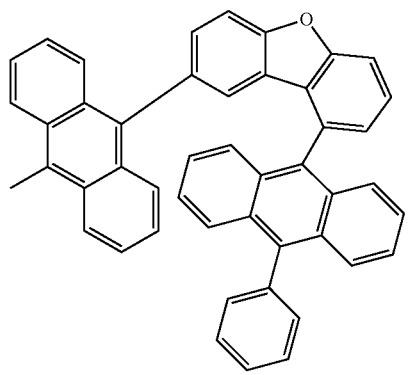
968
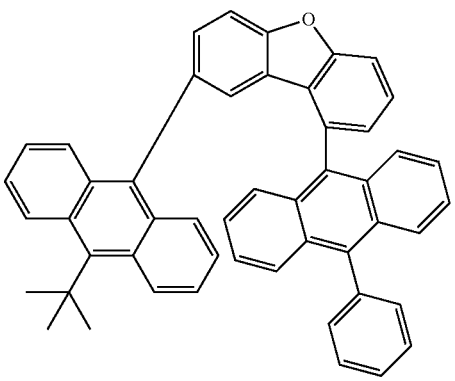
969
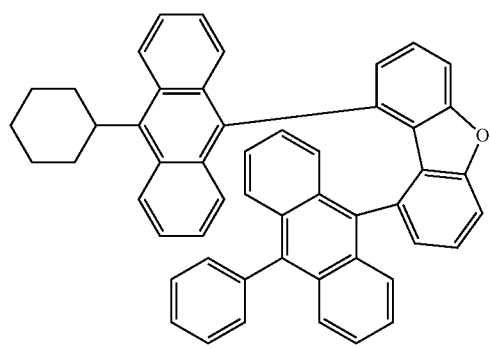
970
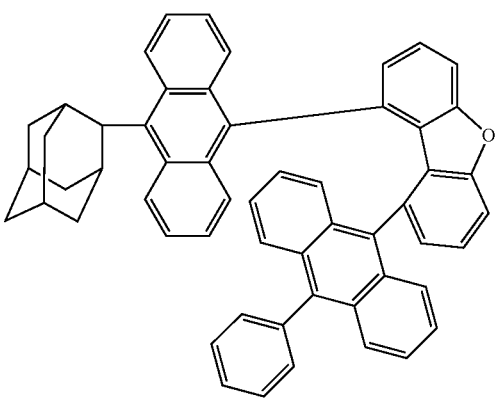
971
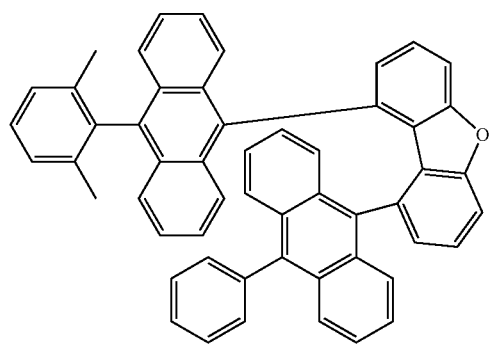
972
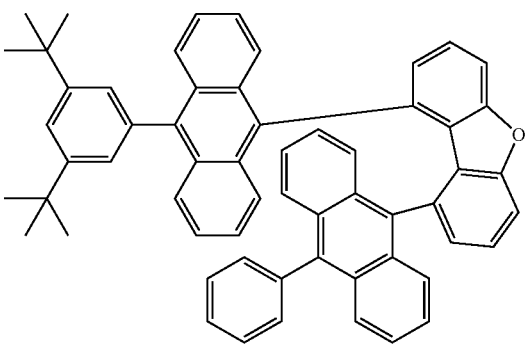
973
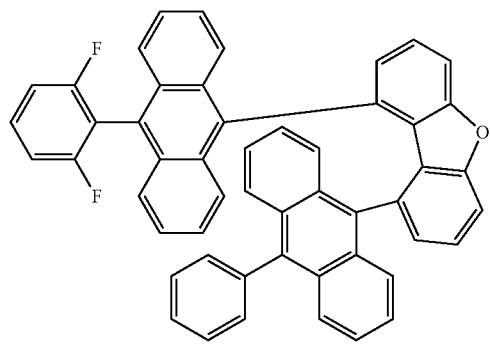
974
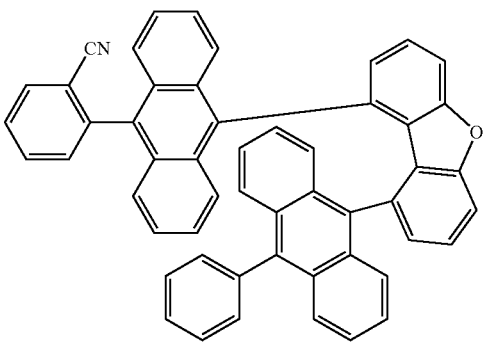

-continued
975 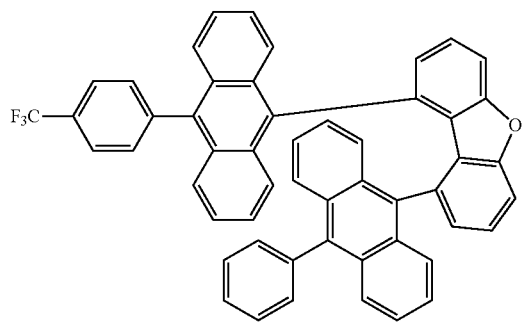
976 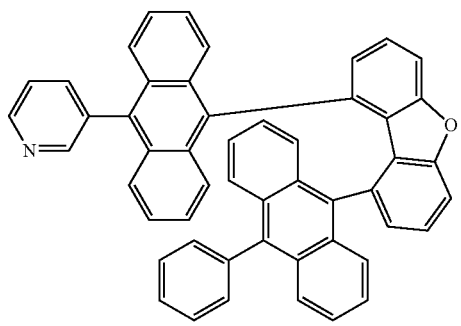
977 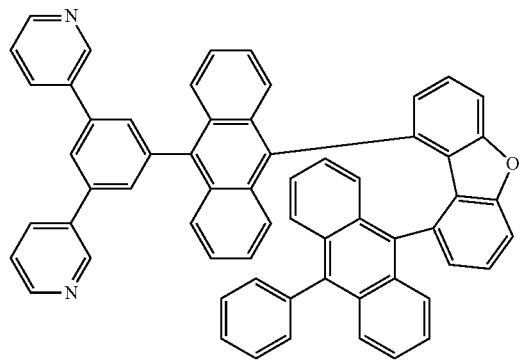
978 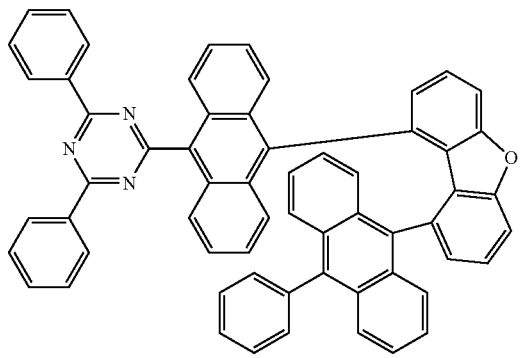
979 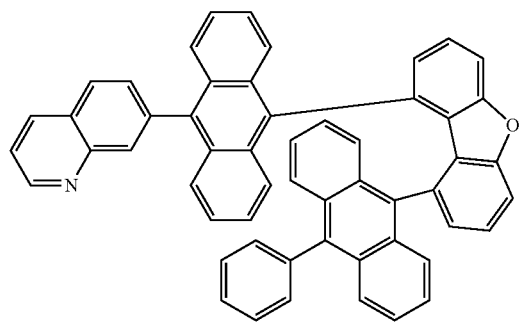
980 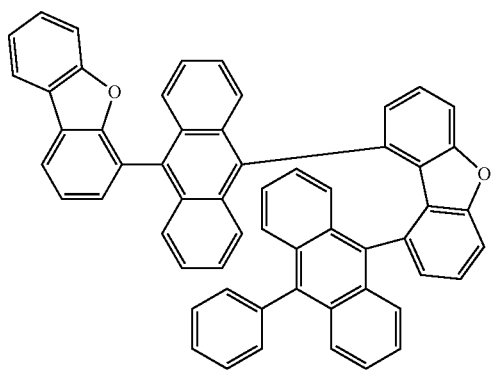
981 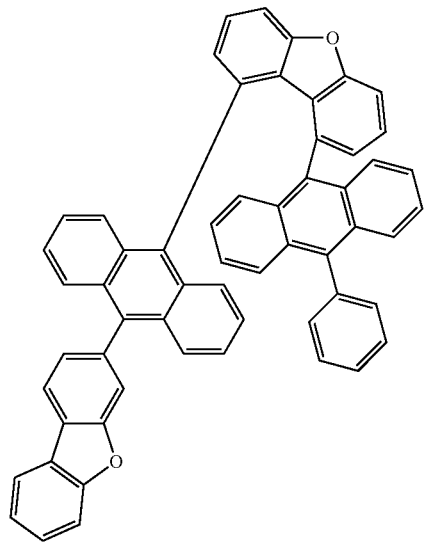
982 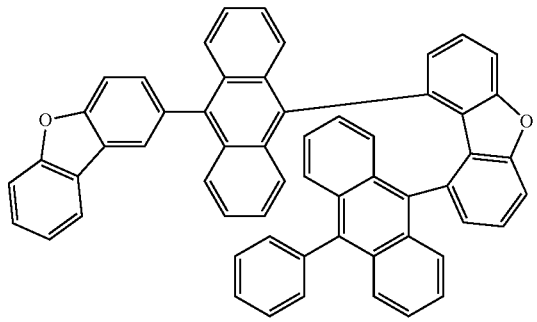

-continued
983
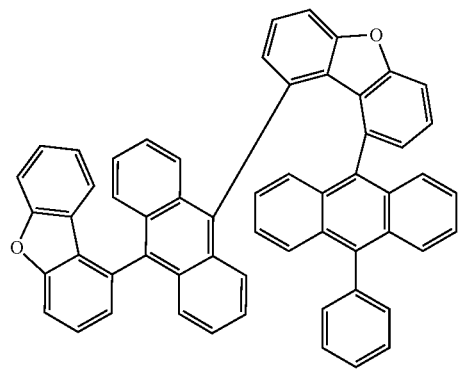
984
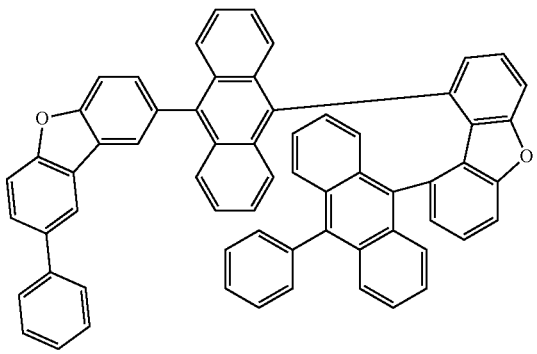
985
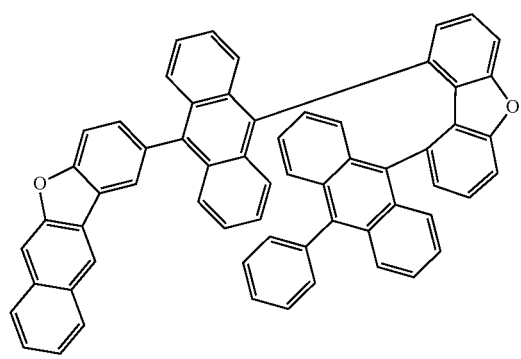
986
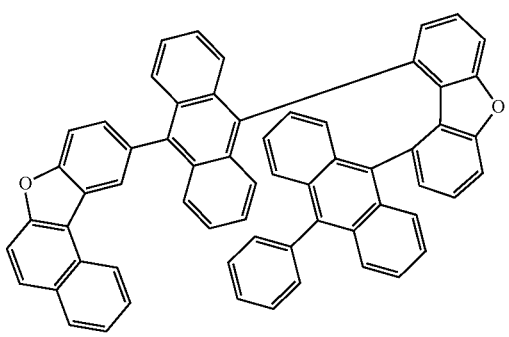
987
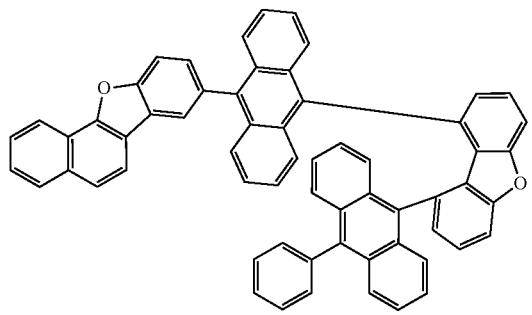
988
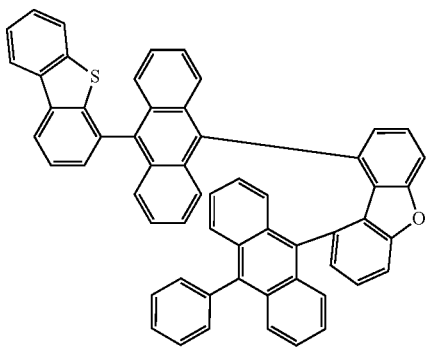
989
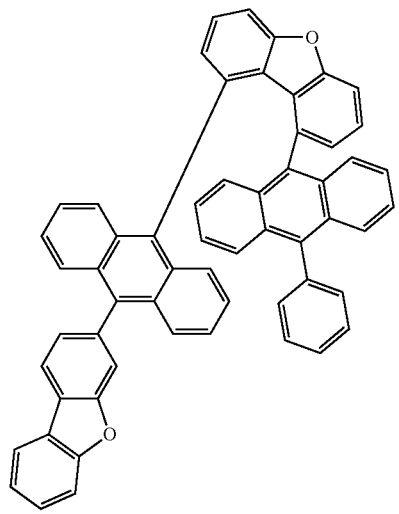
990
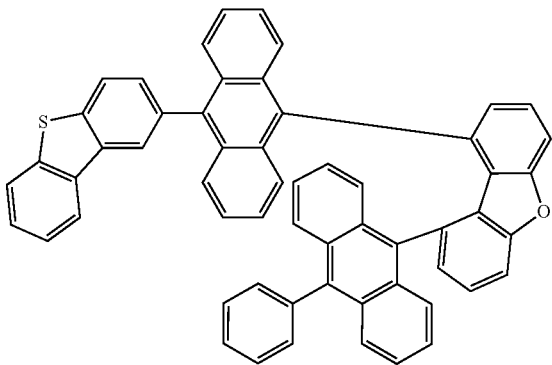

-continued
991
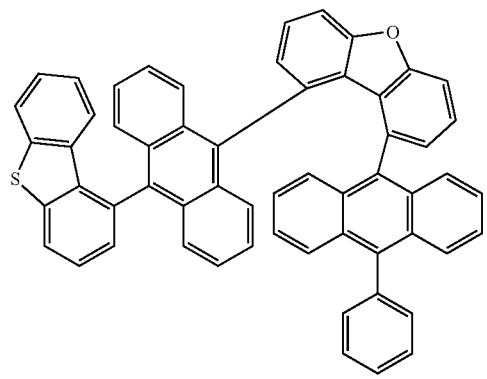
992
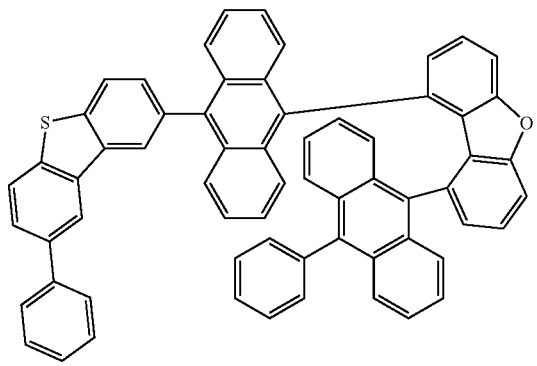
993
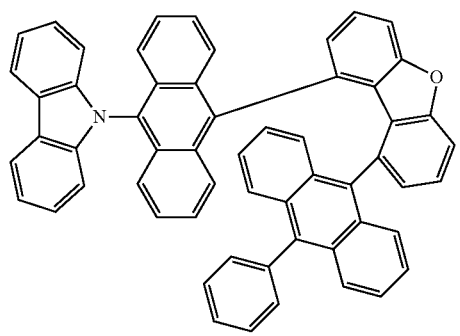
994
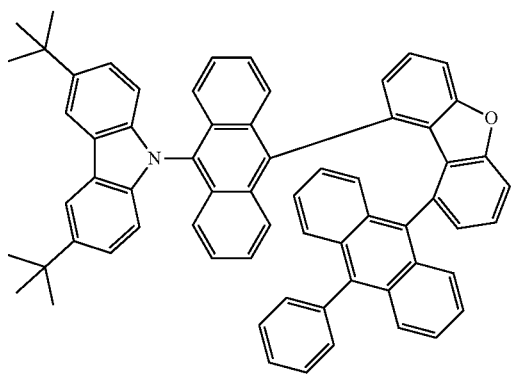
995
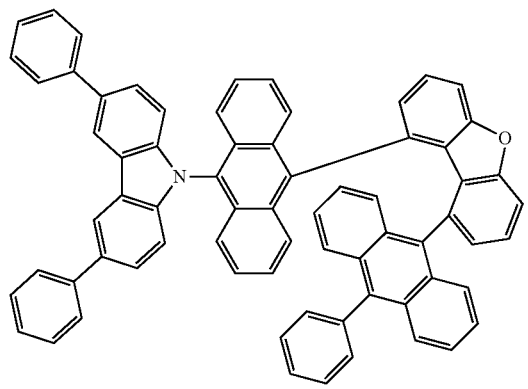
996
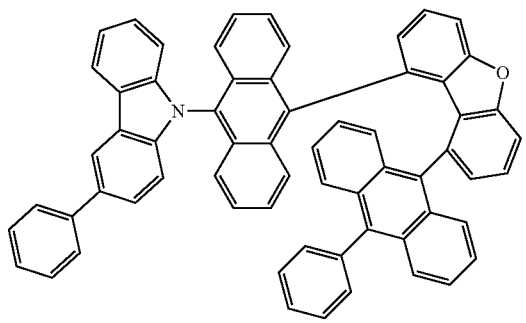
997
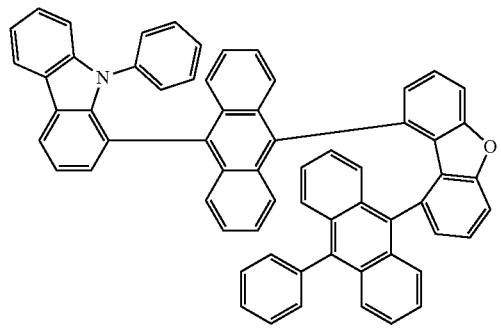
998
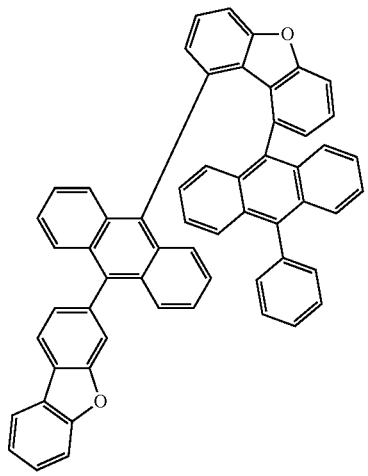

-continued
999 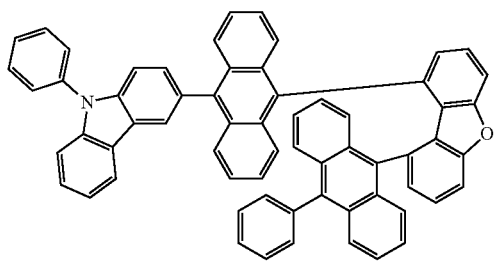
1000 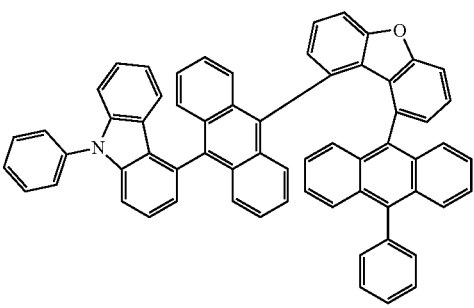
1001 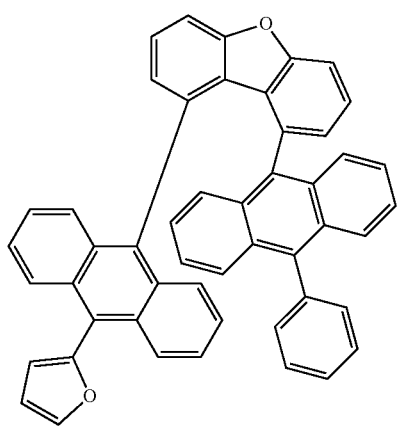
-continued
1003 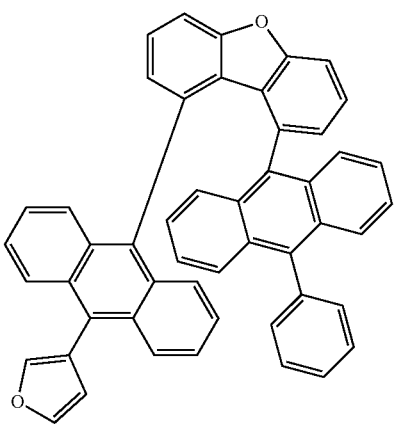
1002 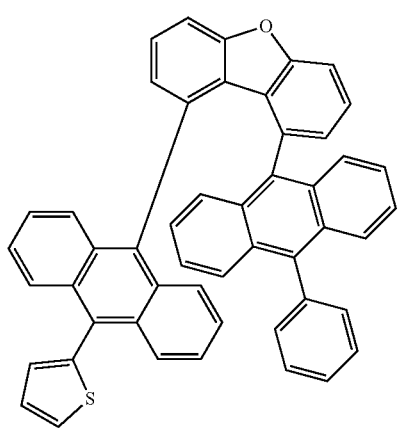
1004 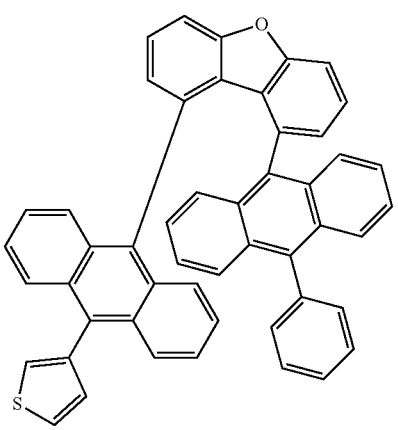

1821
-continued
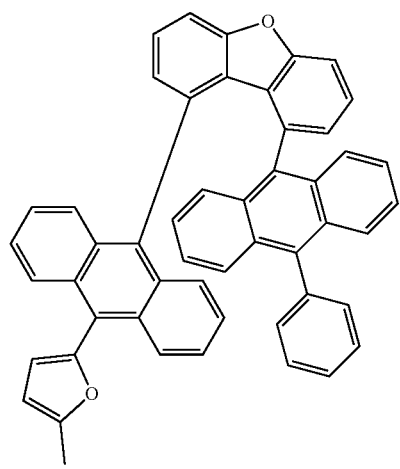
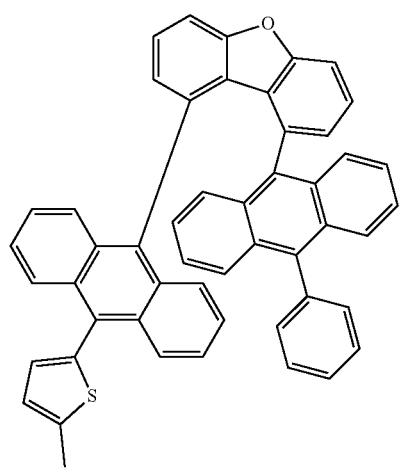
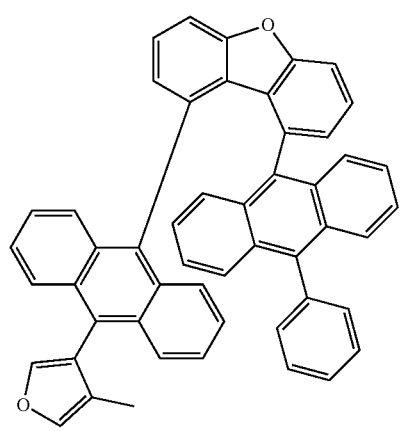
1822
-continued
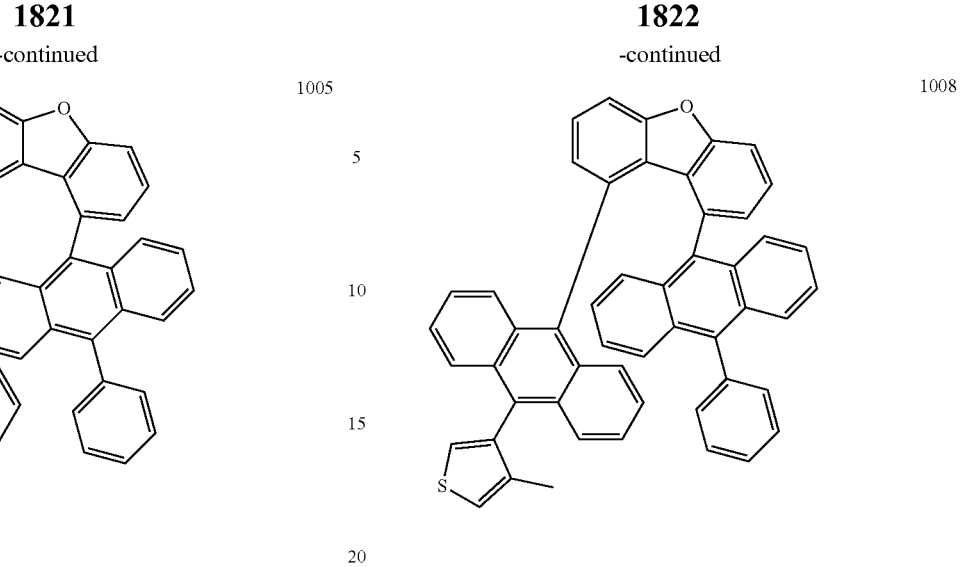
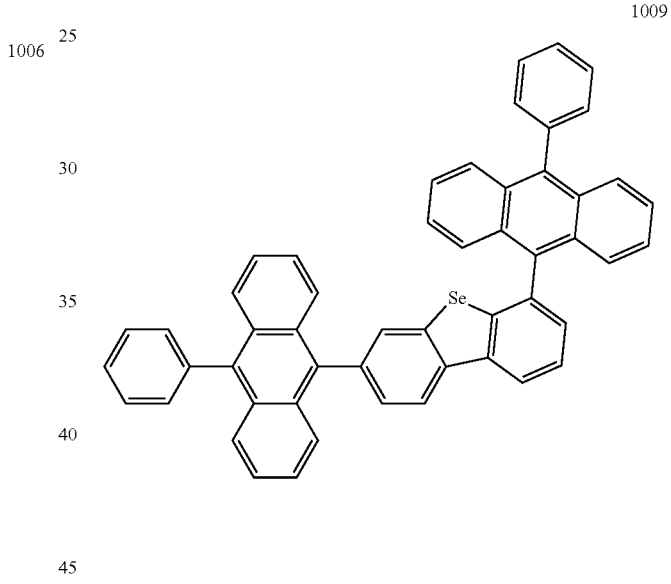
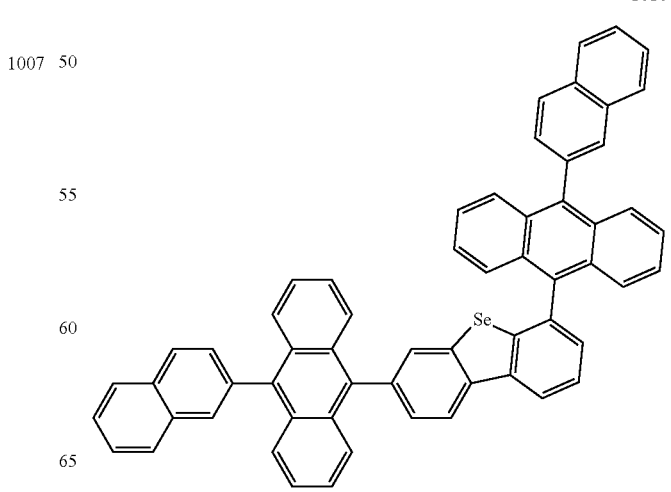

1823
-continued
1824
-continued
1011
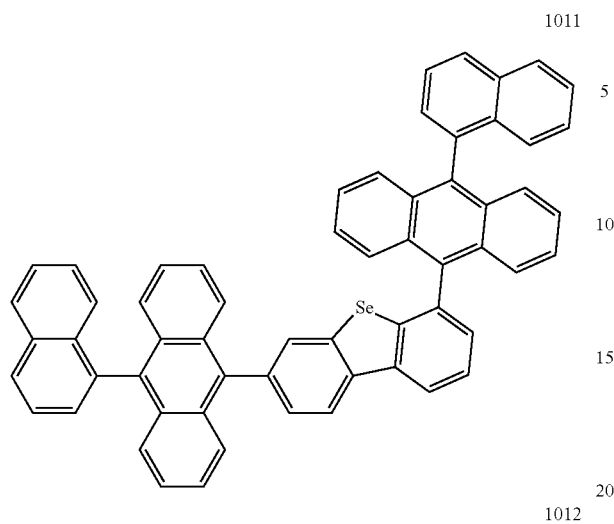
1014
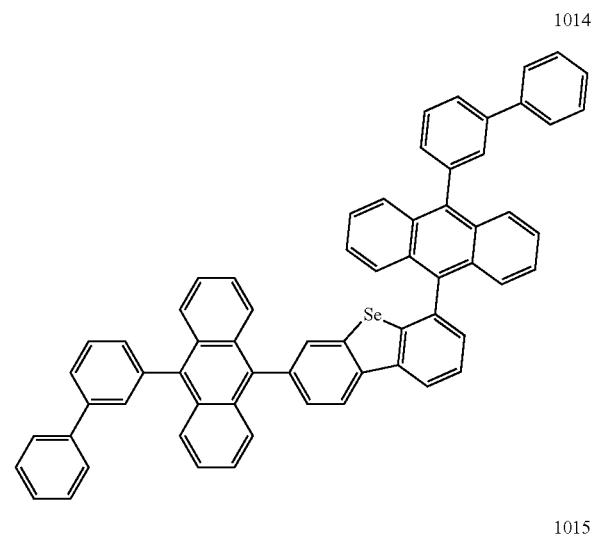
1012
1015
1013
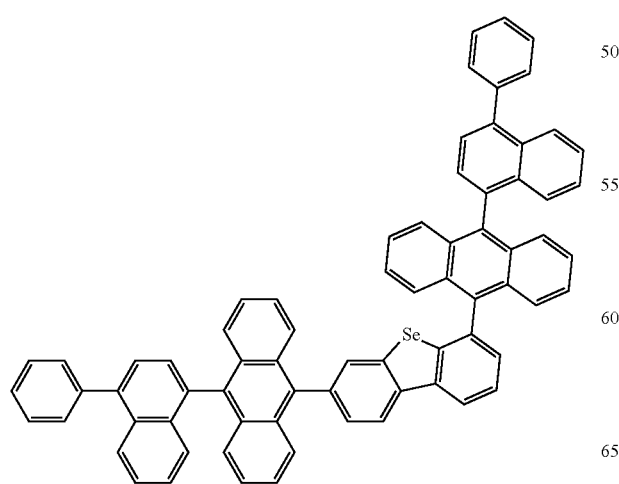
1016
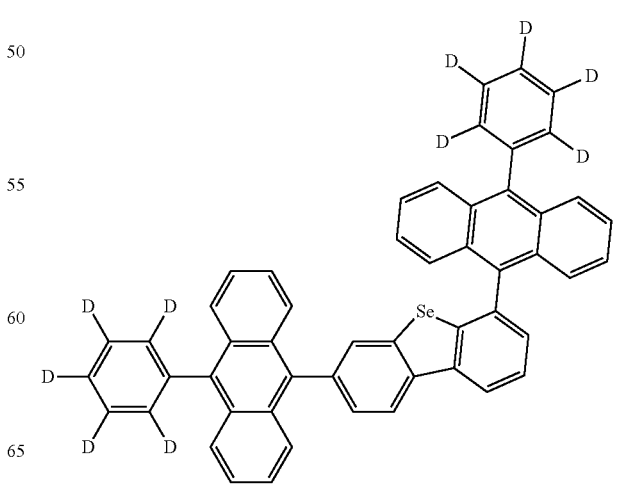

1825
-continued
1017
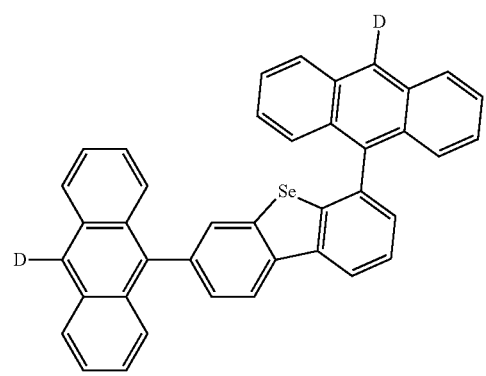
1018
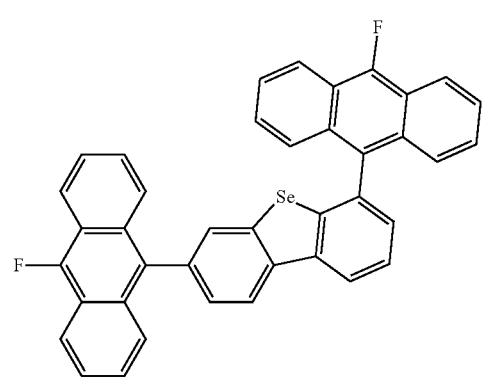
1019
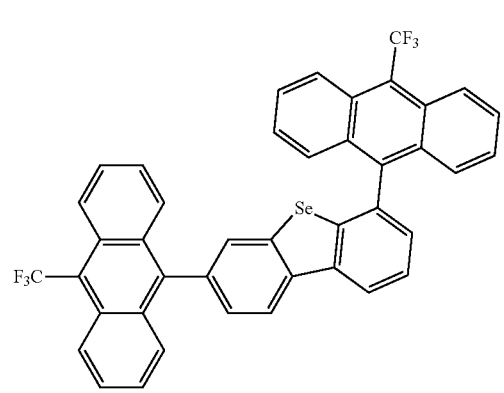
1020
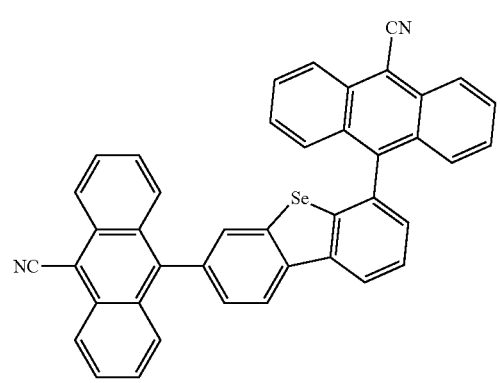
1826
-continued
1021
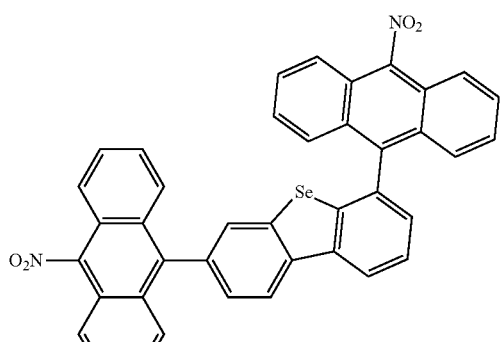
1022
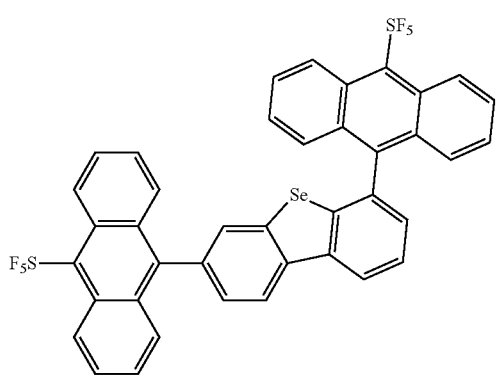
1023
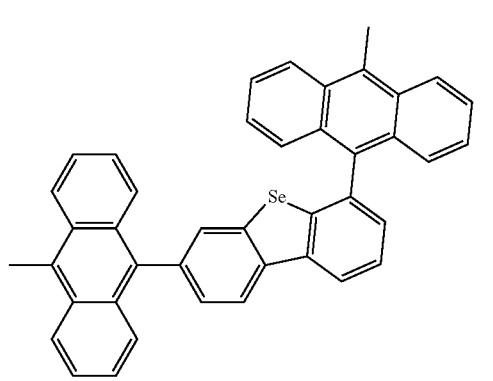
1024
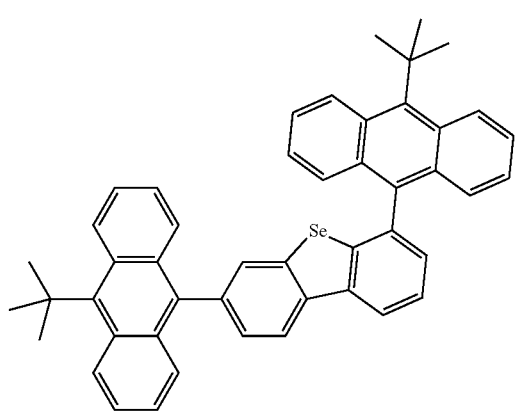

-continued
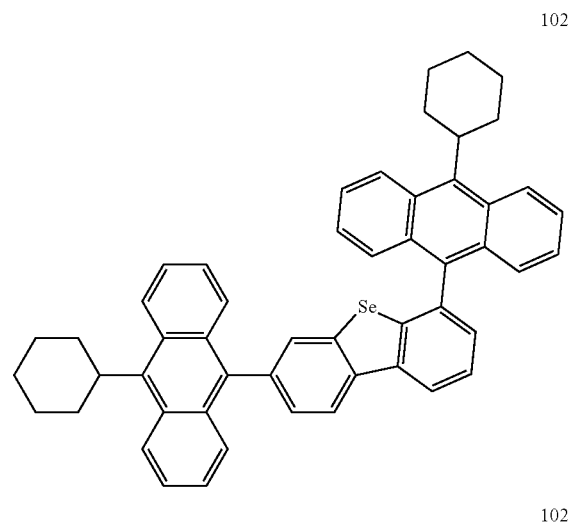
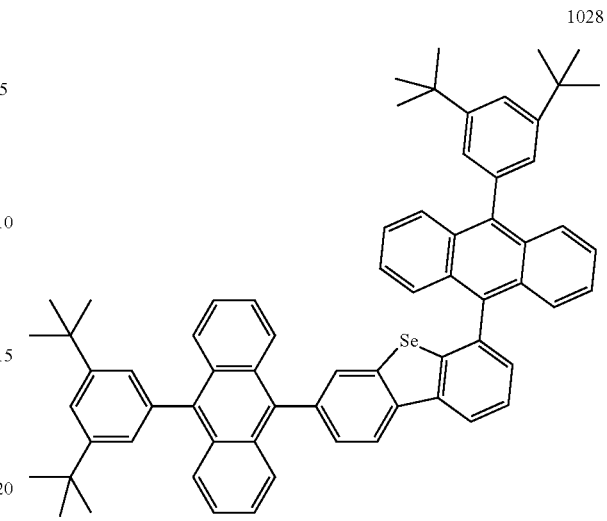
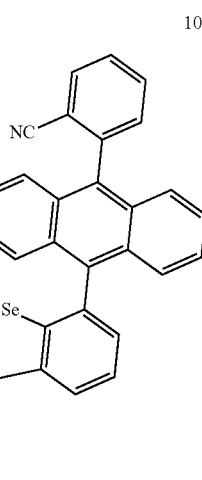

1829
-continued
1031
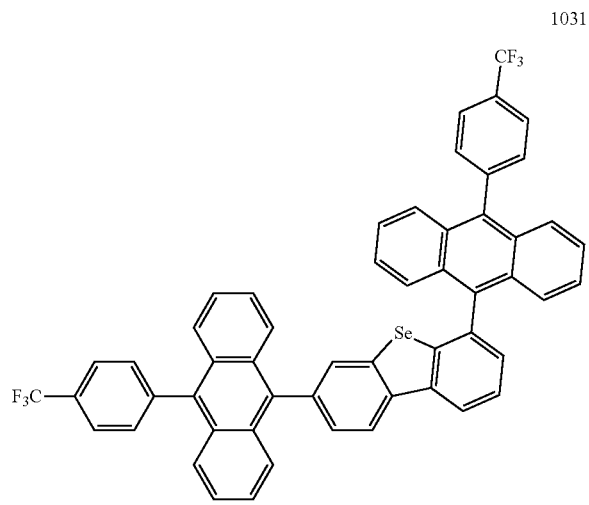
1032
1033
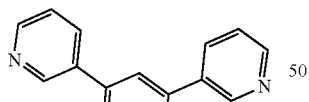
1830
-continued
1034
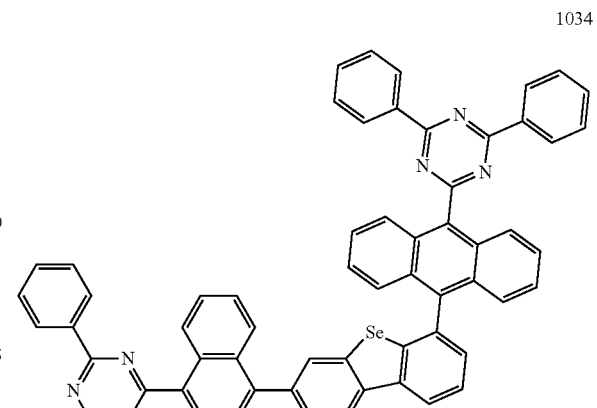
1035
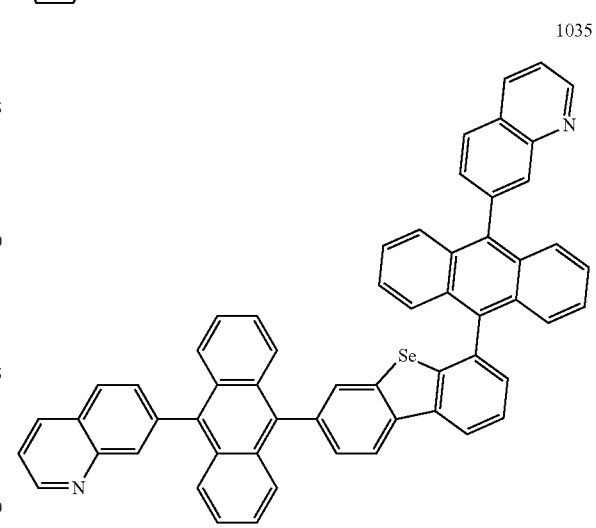
1036
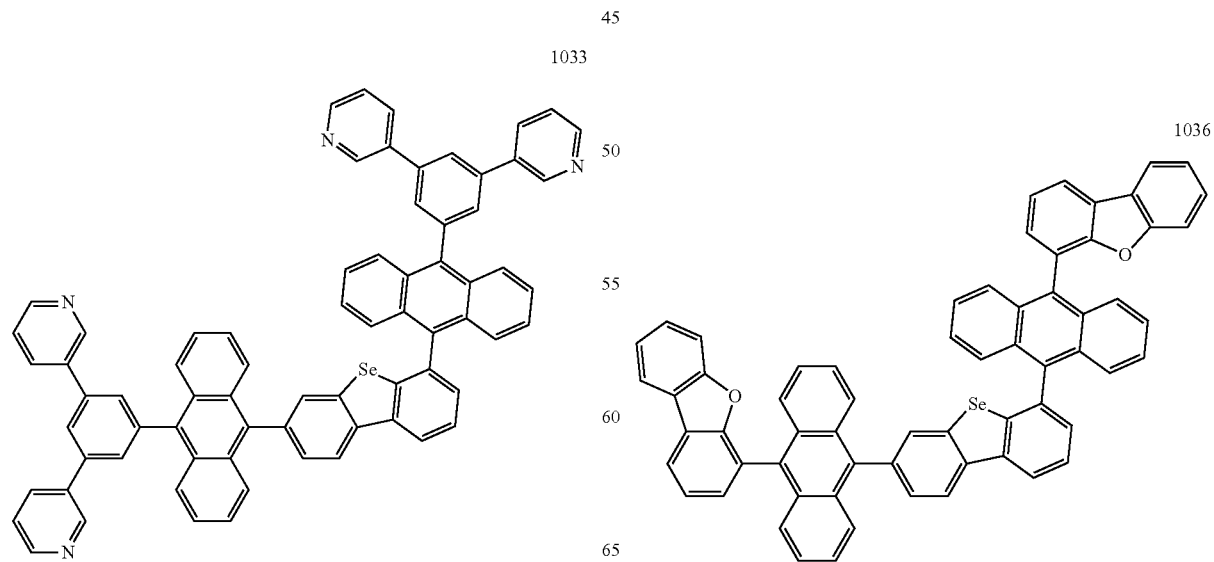

1831
-continued
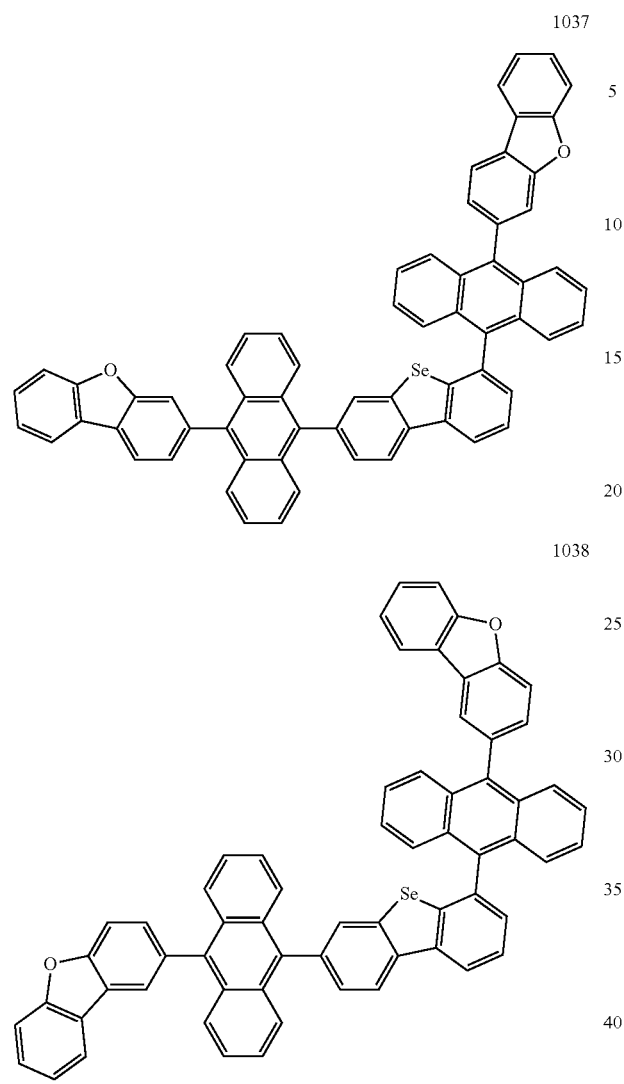
1832
-continued
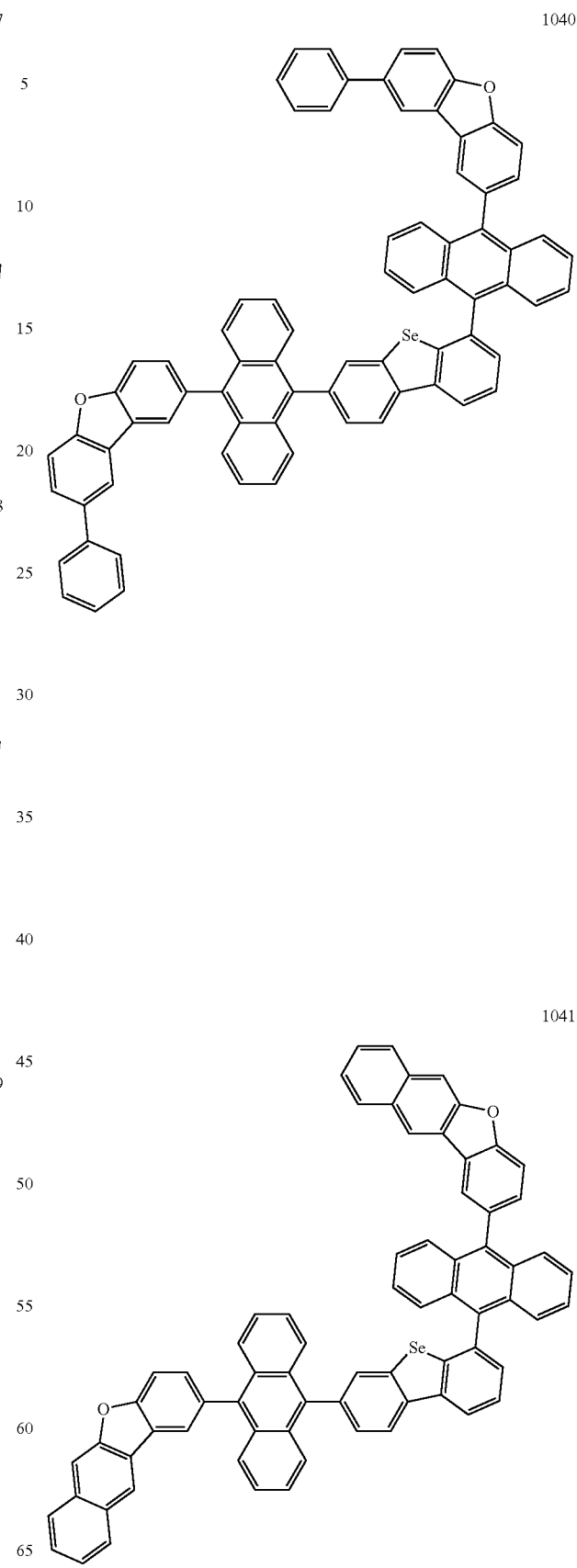

1833
-continued
1042
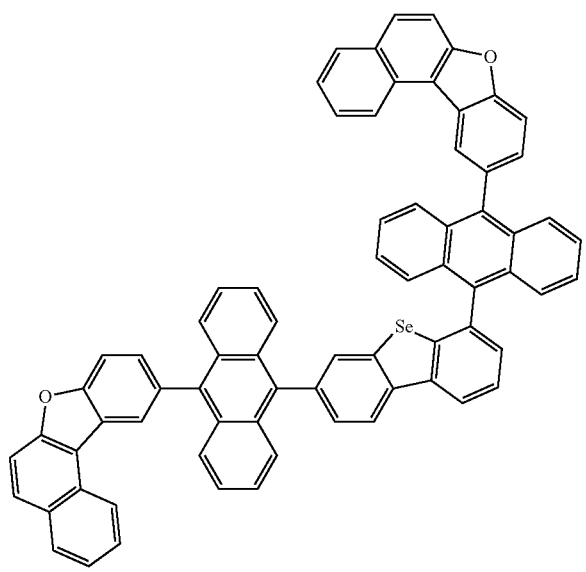
1043
1044
1834
-continued
1045
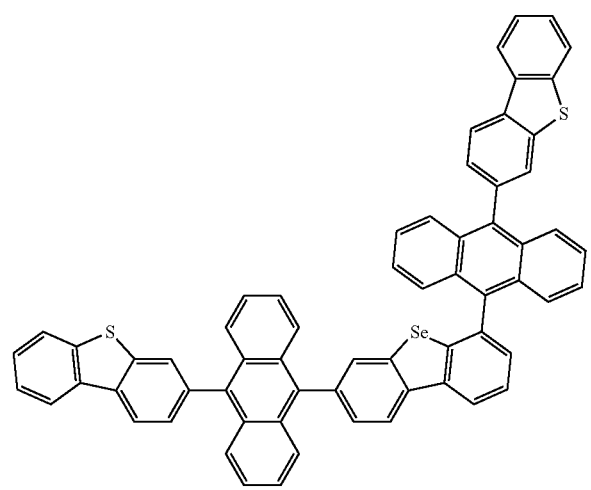
1046
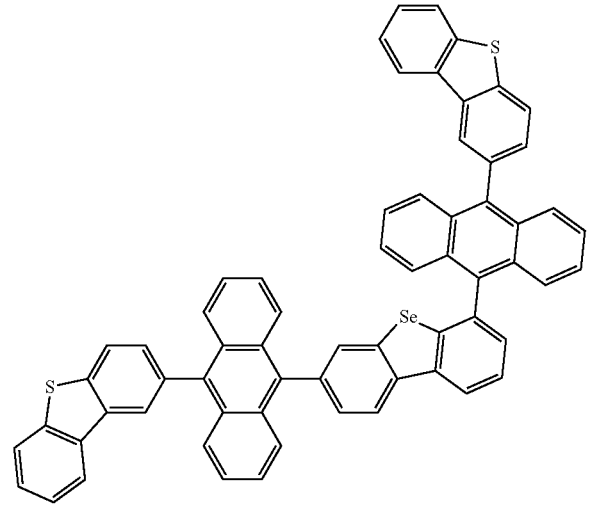
1047
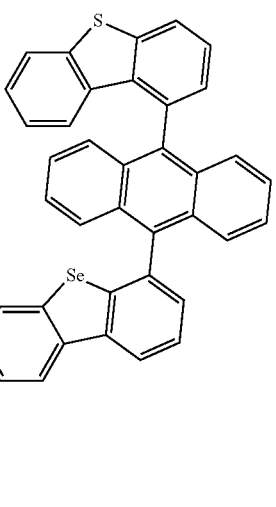

1835
-continued
1048
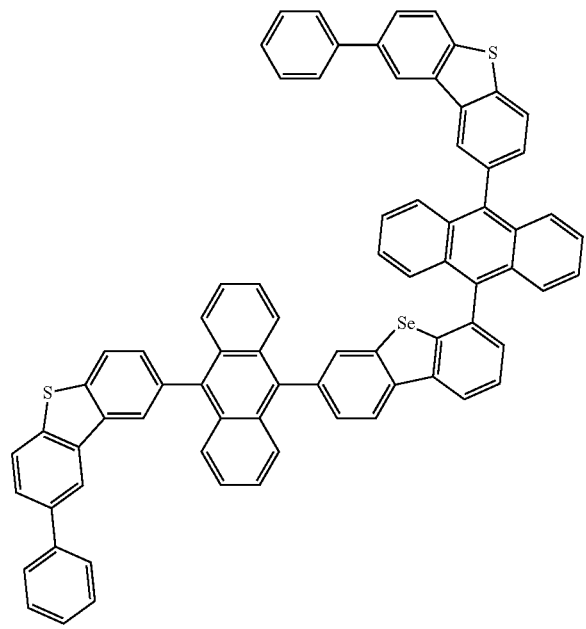
1049
1050
1836
-continued
1051
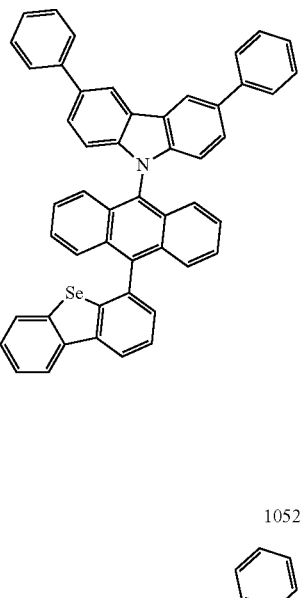
1052
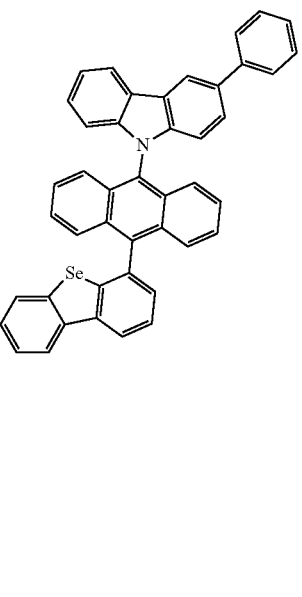
1053
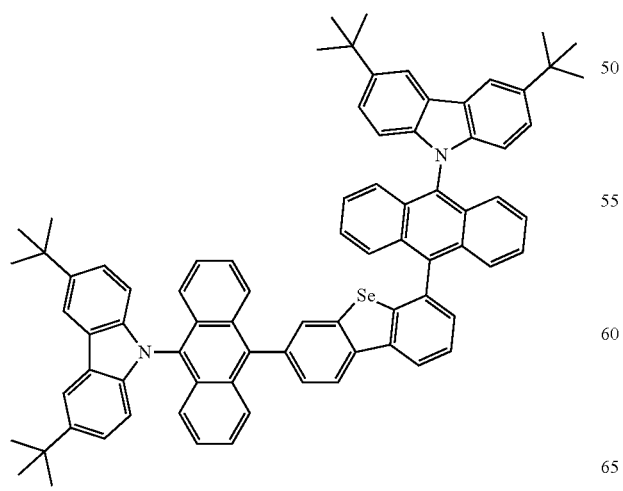

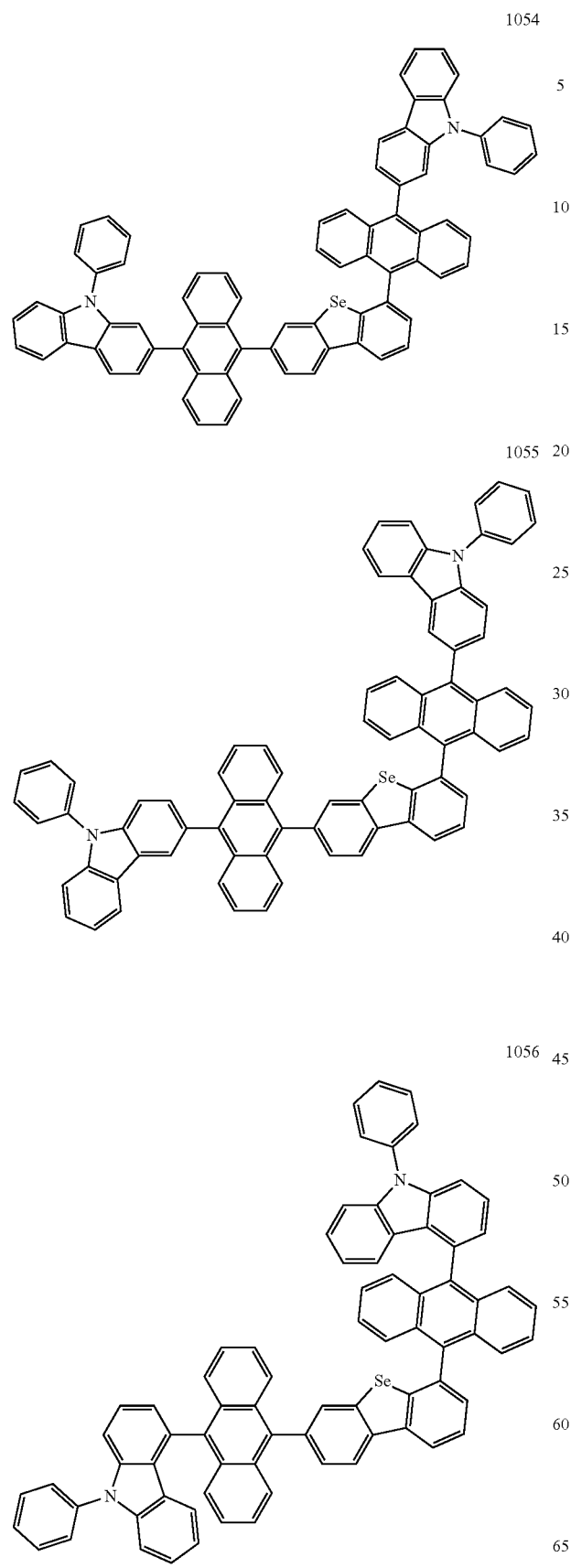
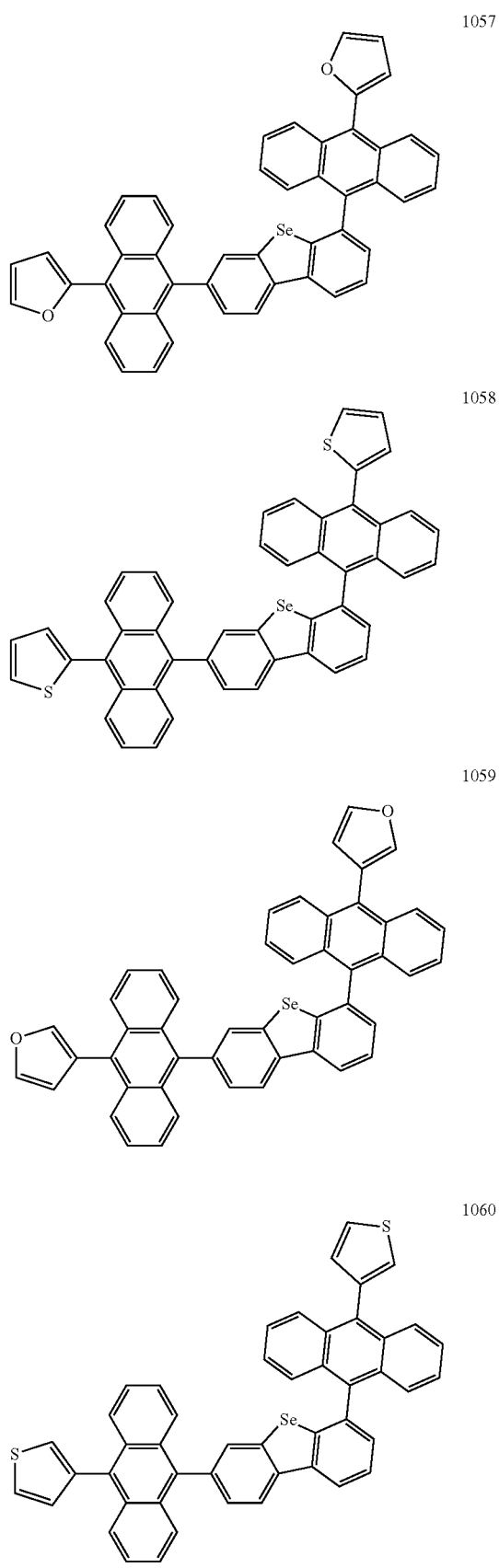

1839
-continued
1061
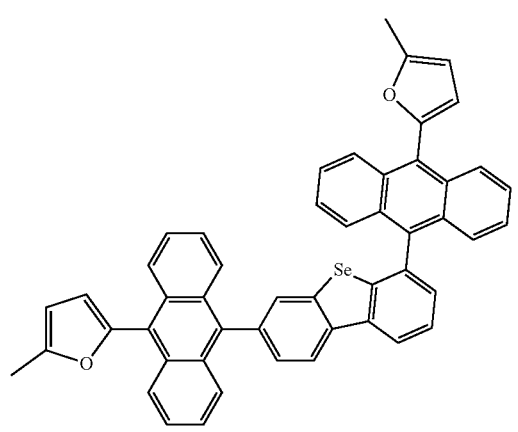
1062
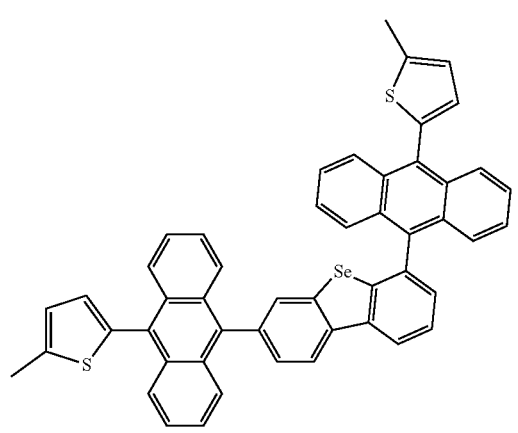
1063
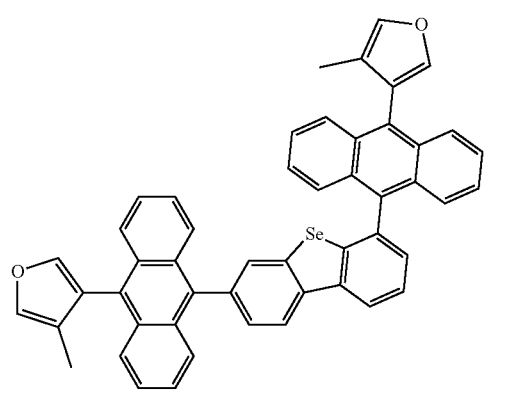
1064
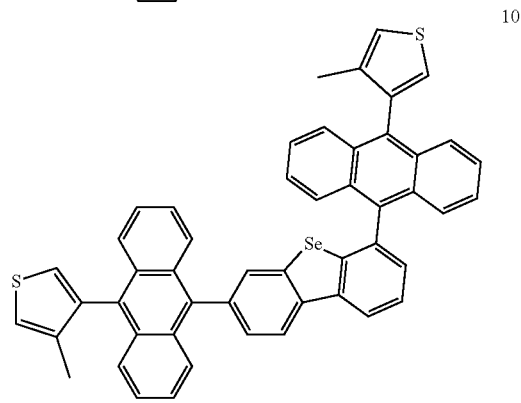
1840
-continued
1065
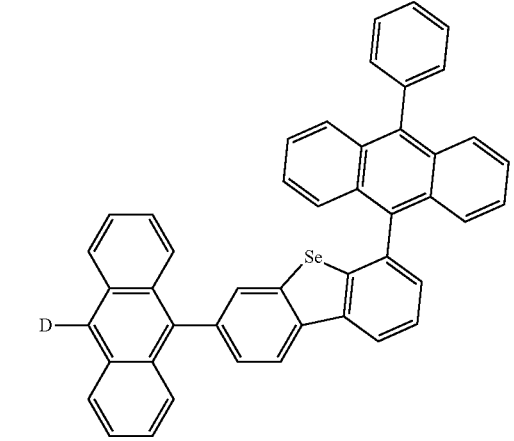
1066
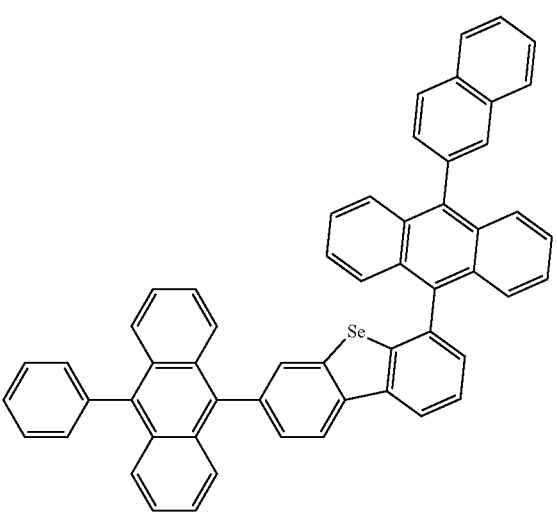
1067
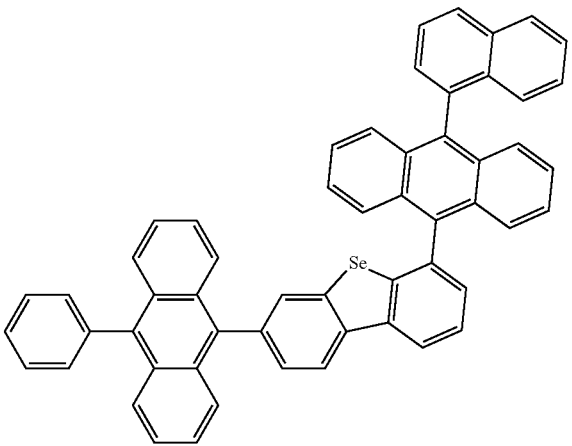

1841
-continued
1068
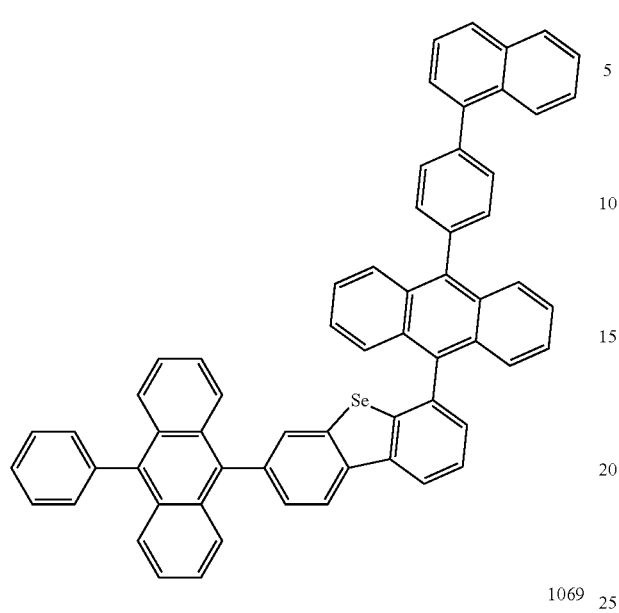
1069
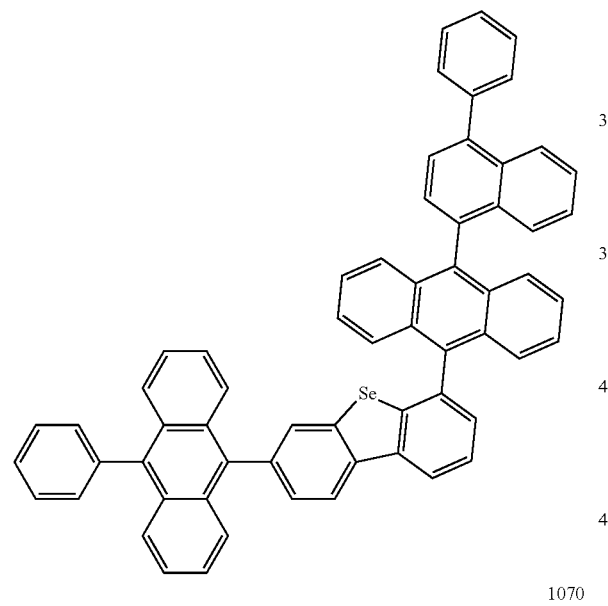
1070
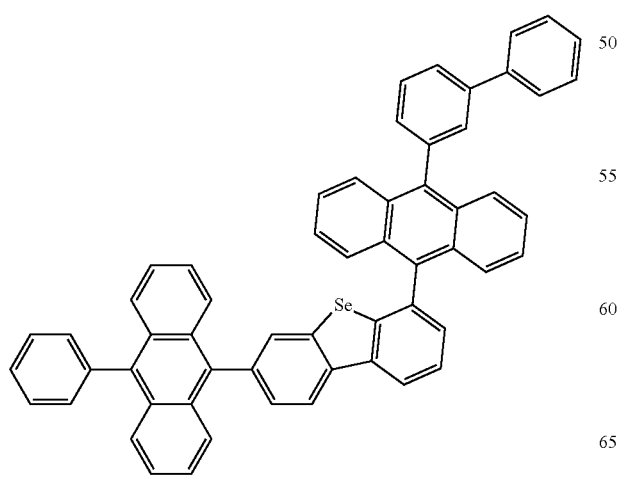
1842
-continued
1071
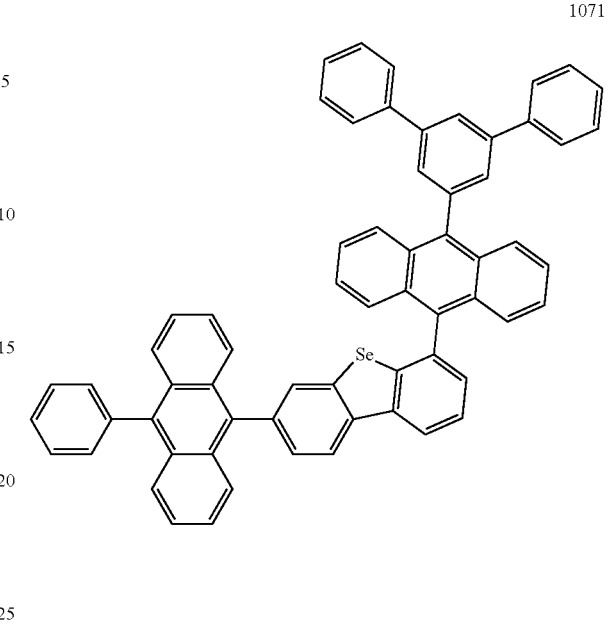
1072
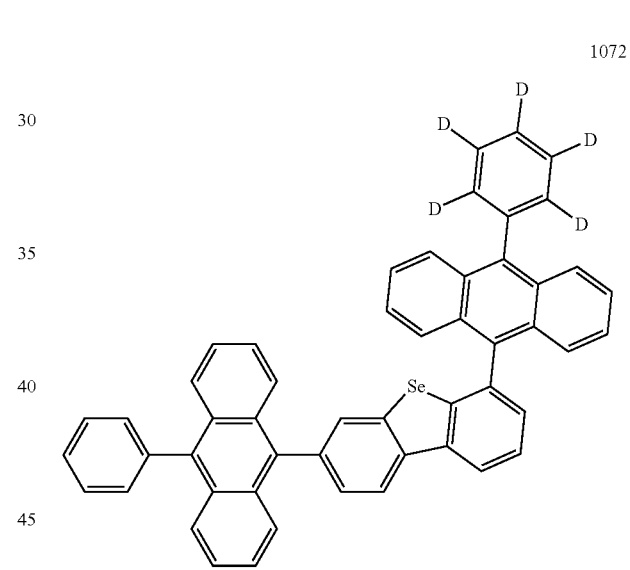
1073
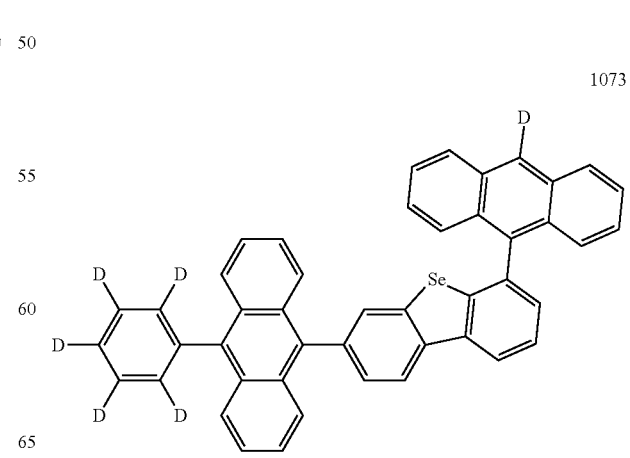

1843
-continued
1074
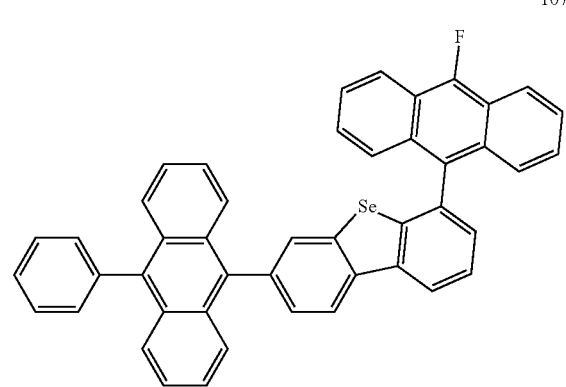
1075
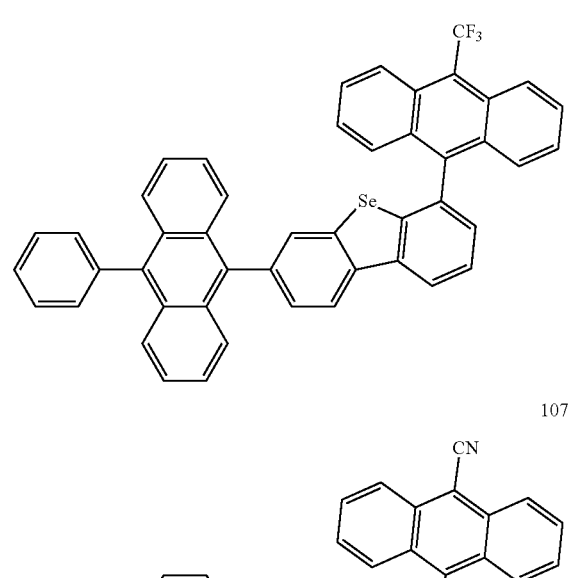
1076
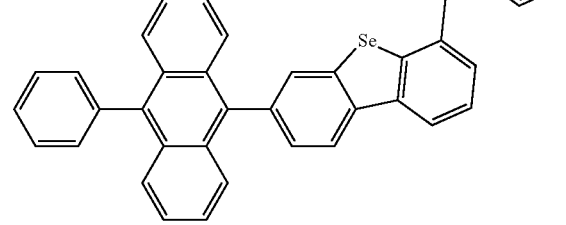
1077
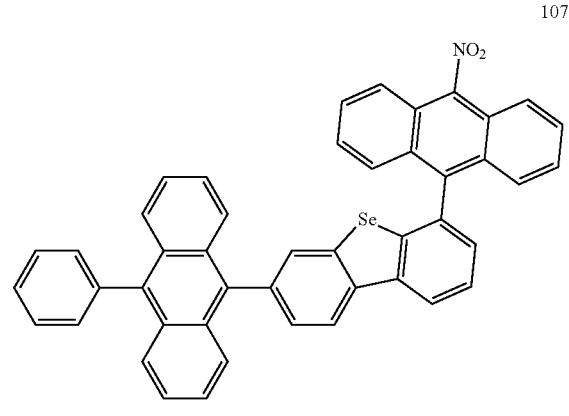
1844
-continued
1078
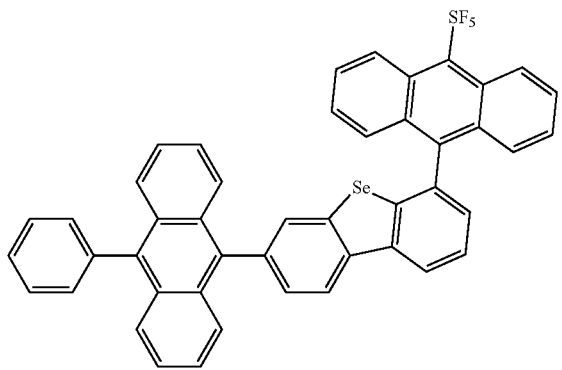
1079
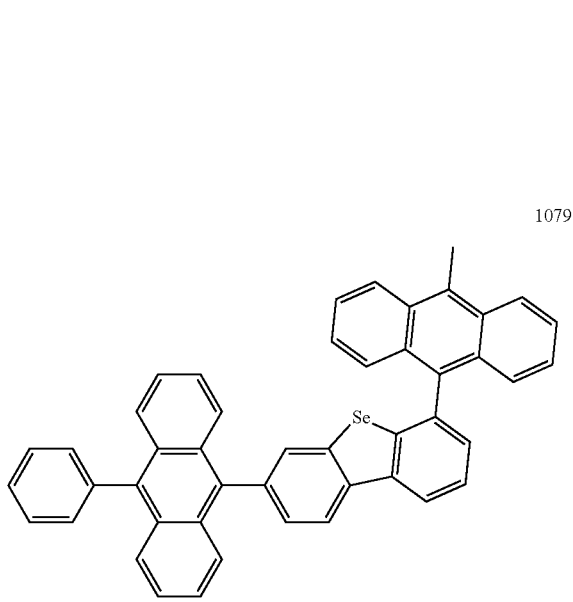
1080
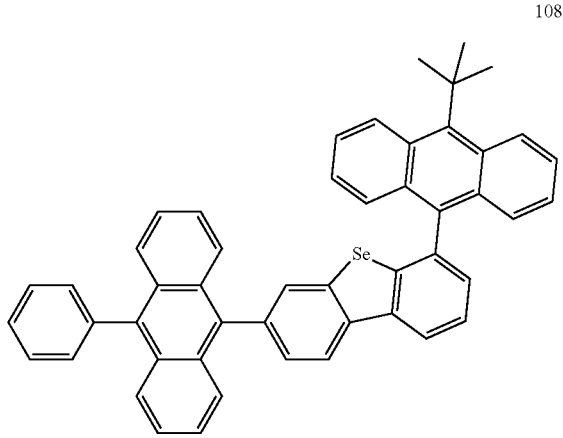

1845  1846
1081
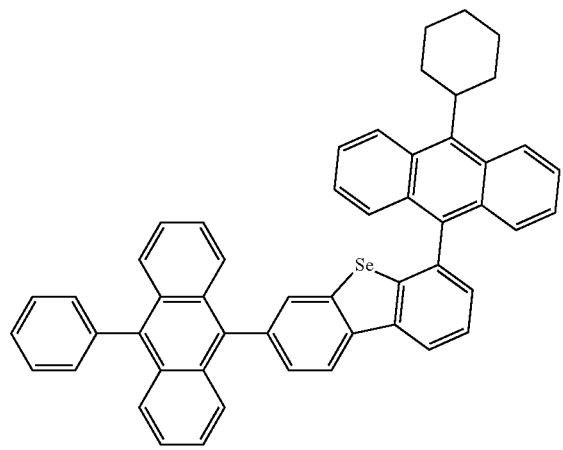
1082
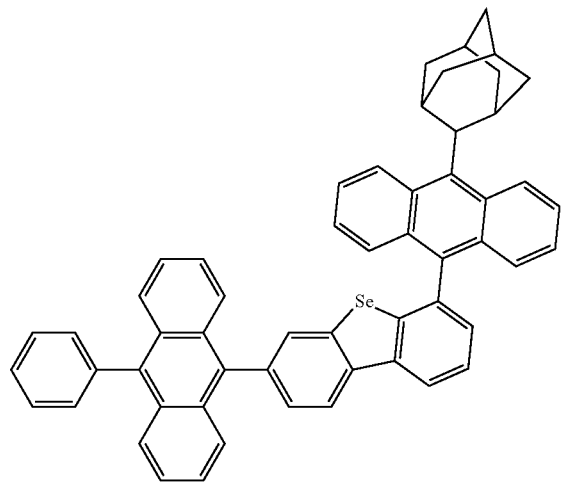
1083
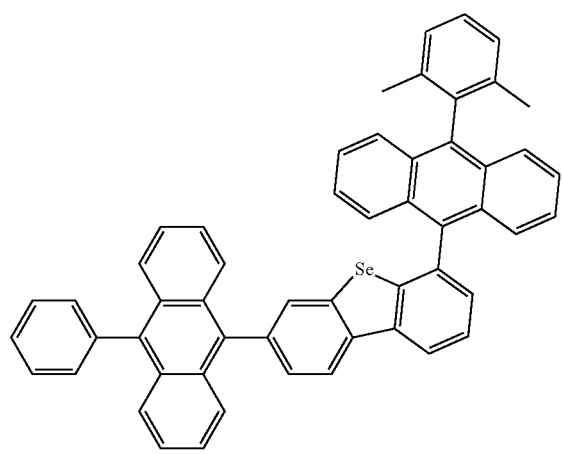
1084
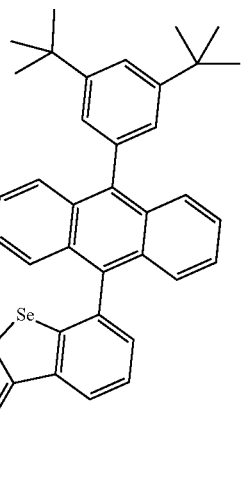
1085
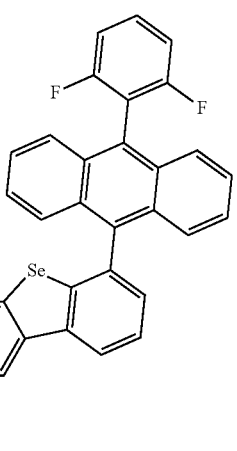
1086
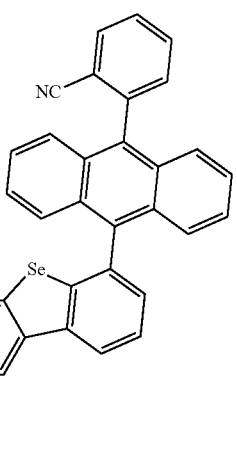

-continued
1087
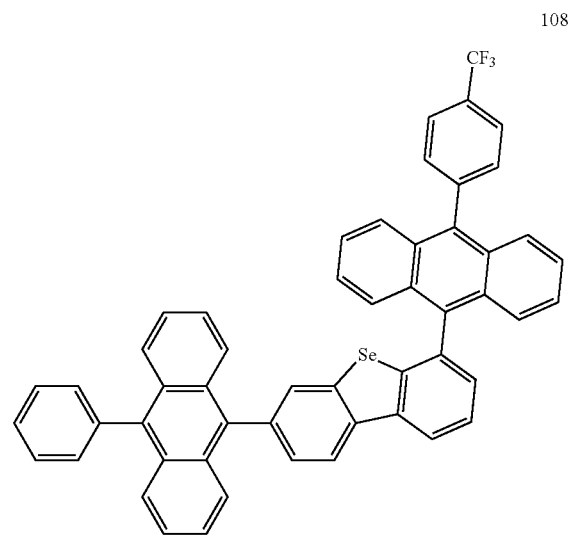
1088
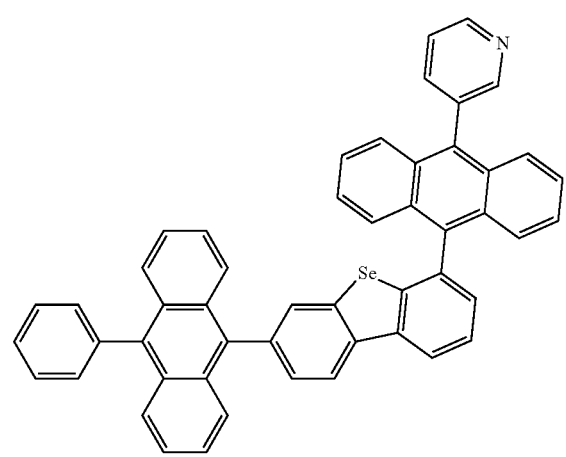
1089
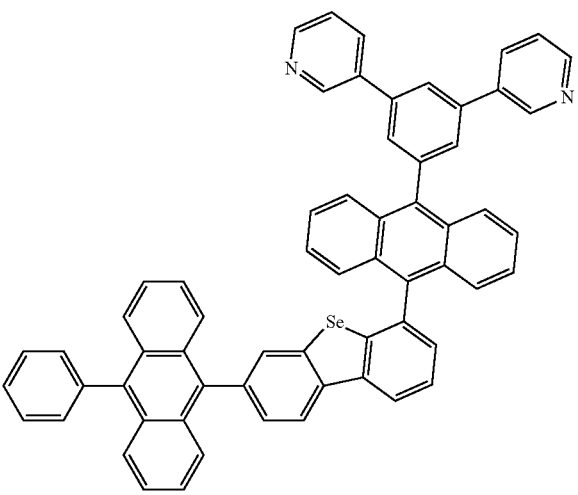
-continued
1090
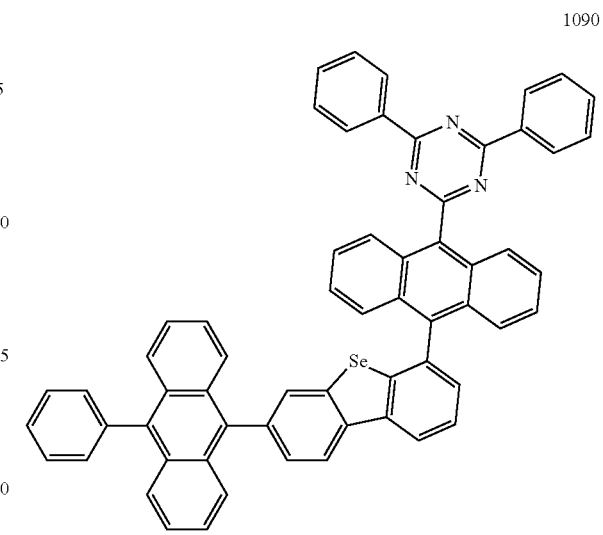
1091
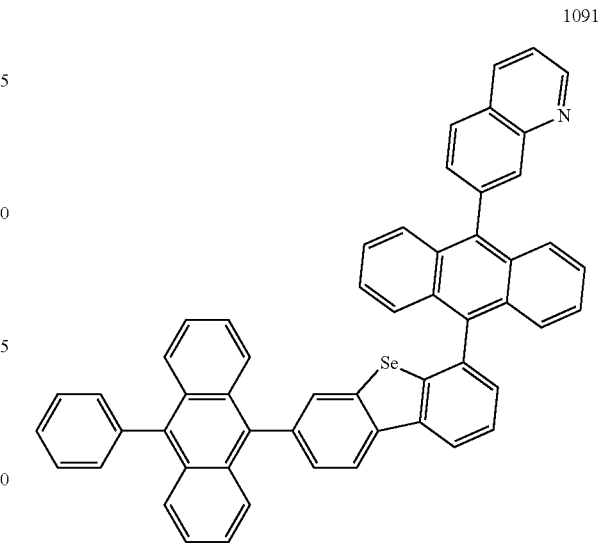
1092
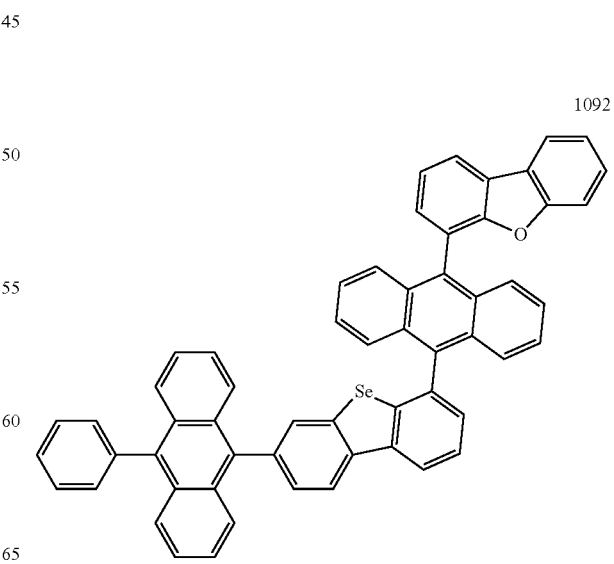

1849
-continued
1093
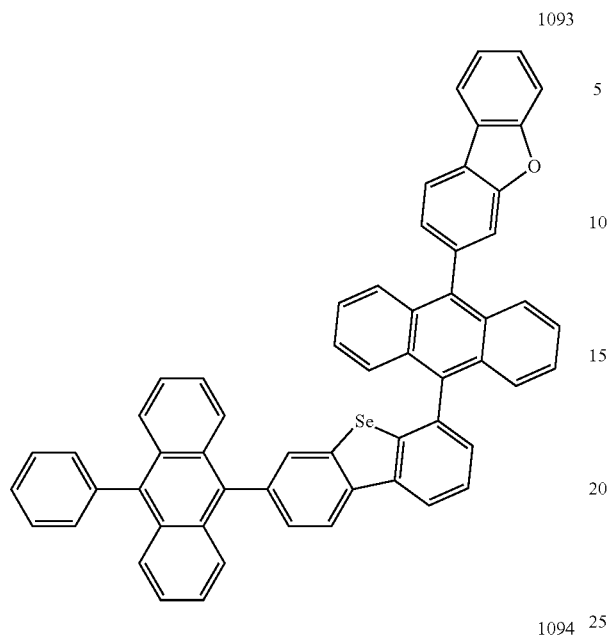
1094
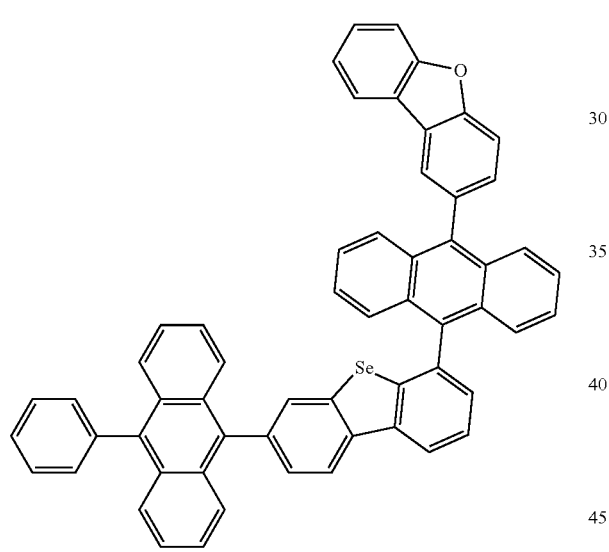
1095
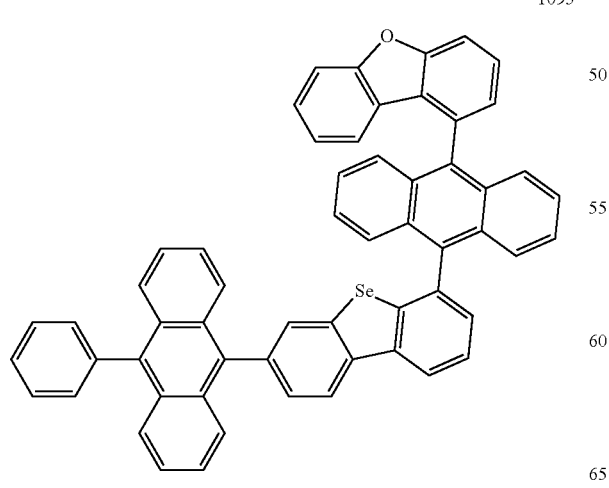
1850
-continued
1096
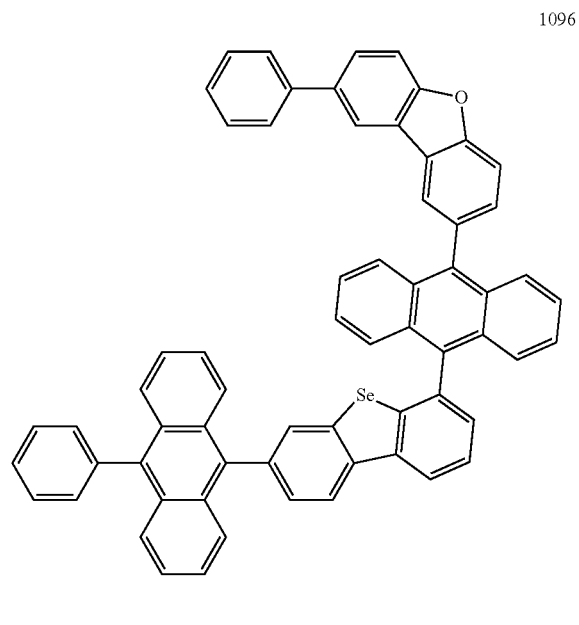
1097
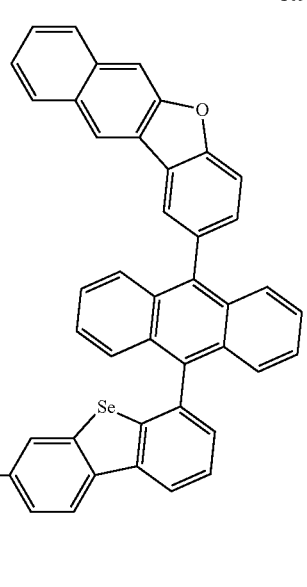

1098
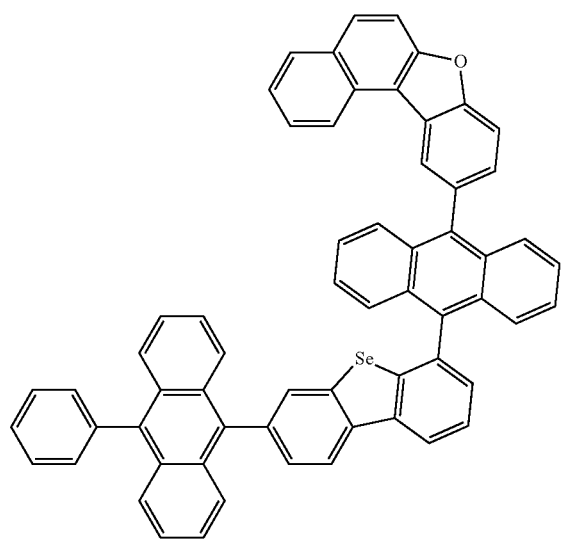
1099
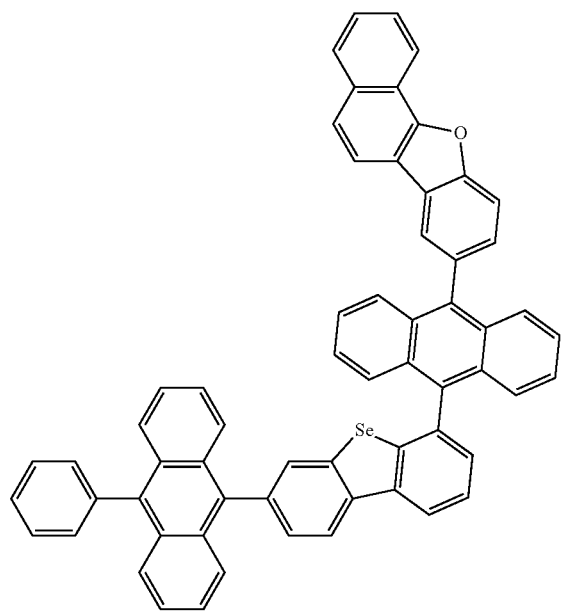
1100
1101
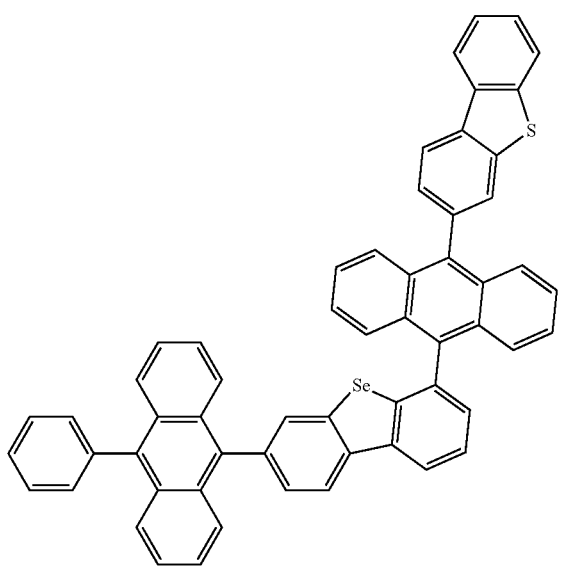
1102
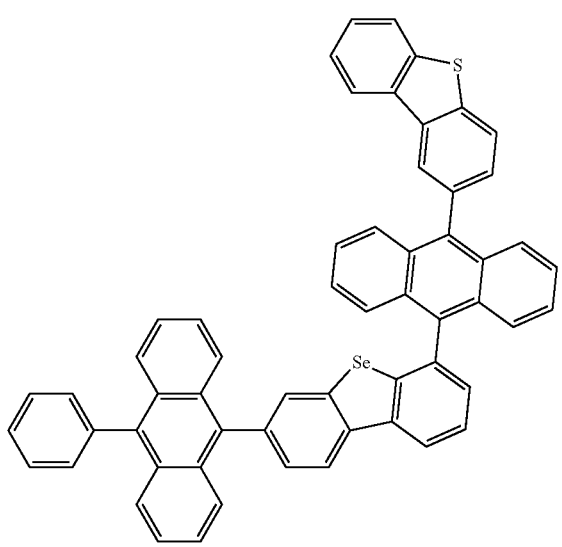
1103
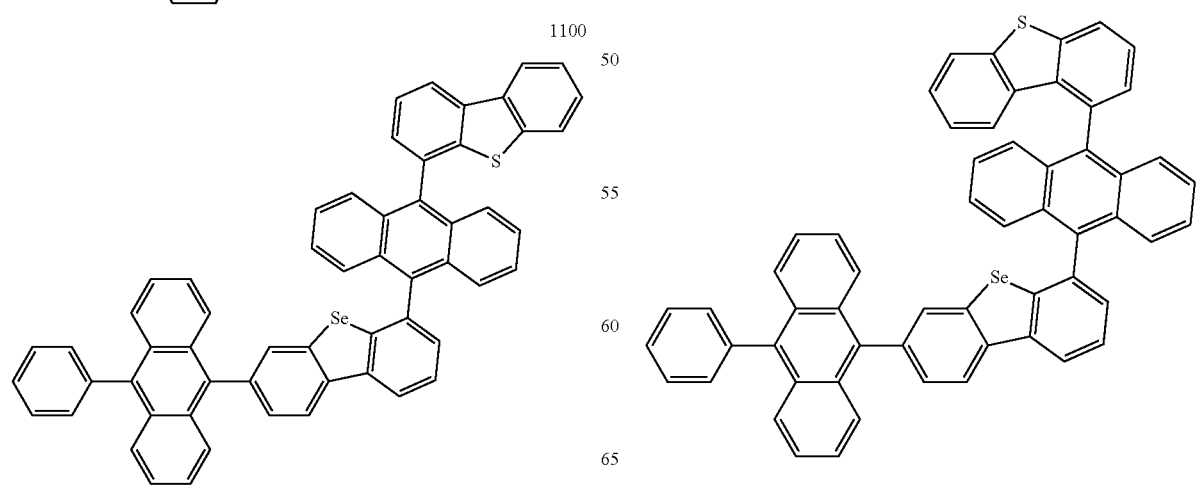

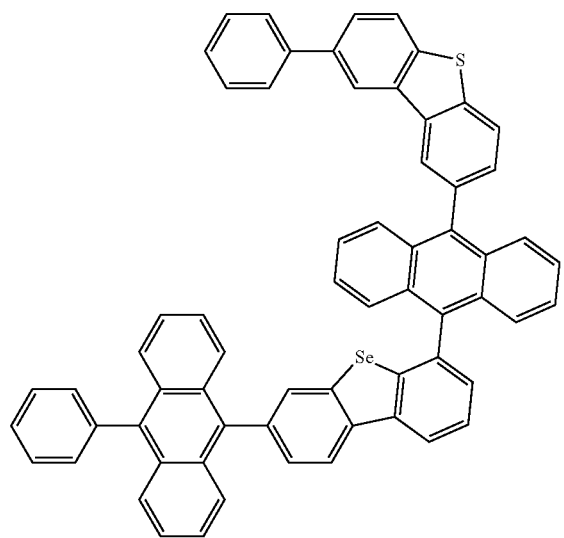
1104
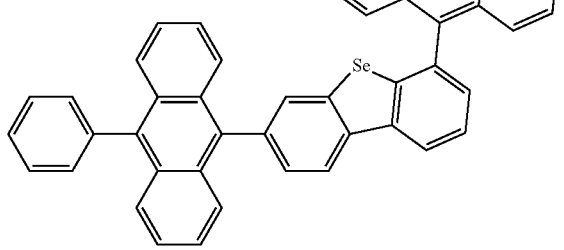
1105
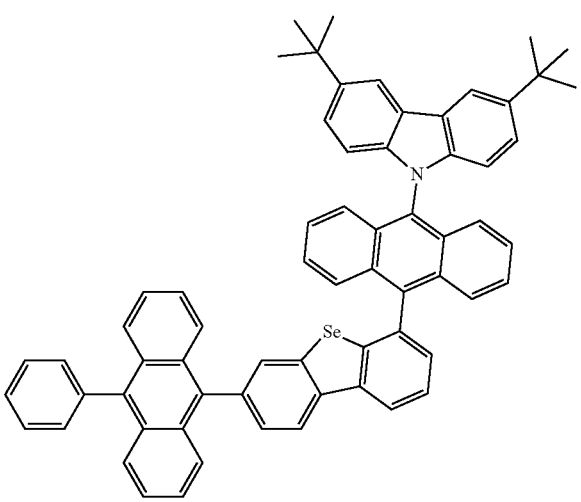
1106
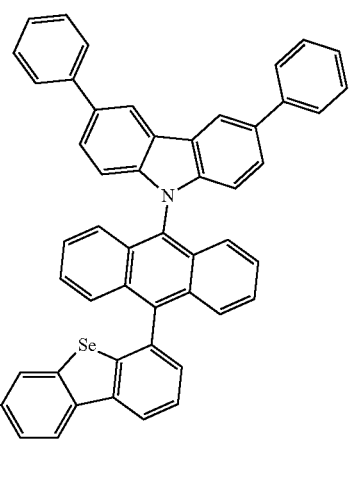
1107
1108
1109

1855
-continued
1110
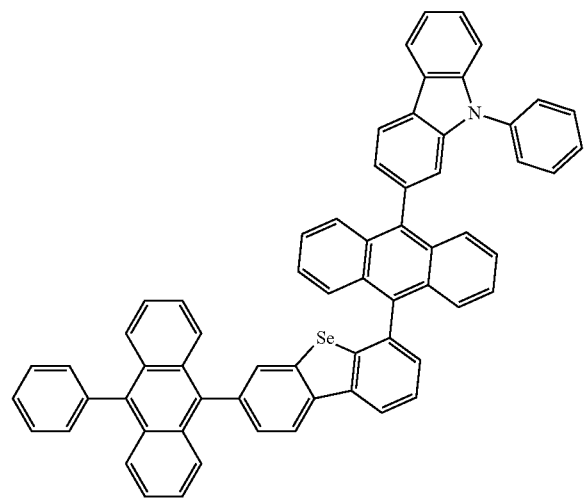
1111
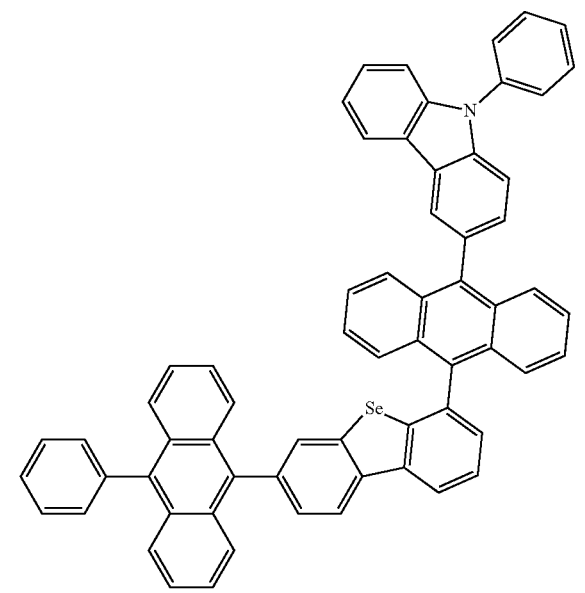
1856
-continued
1112
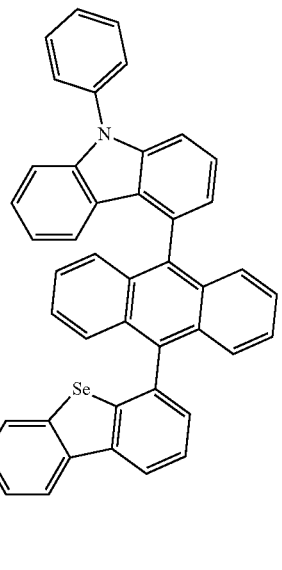
1113
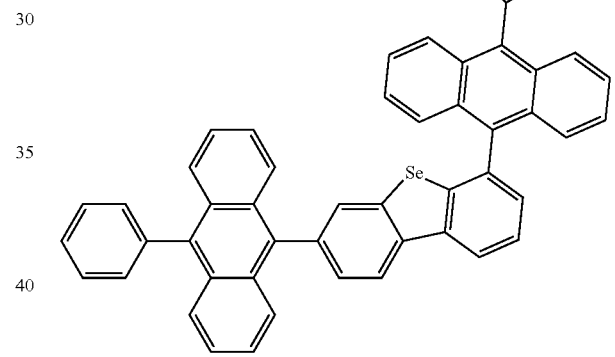
1114
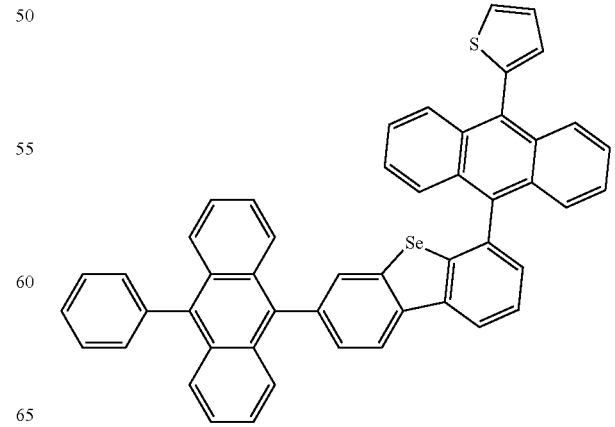

1857
-continued
1115
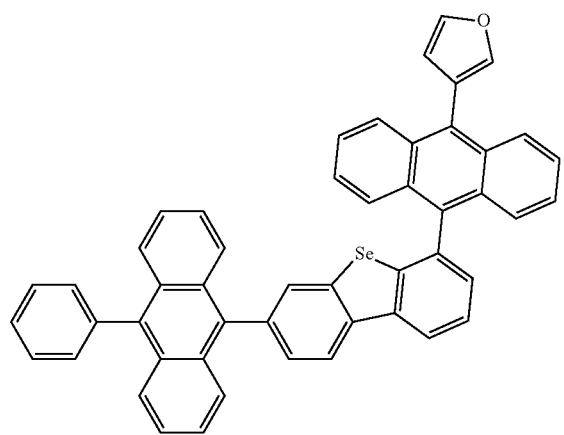
1116
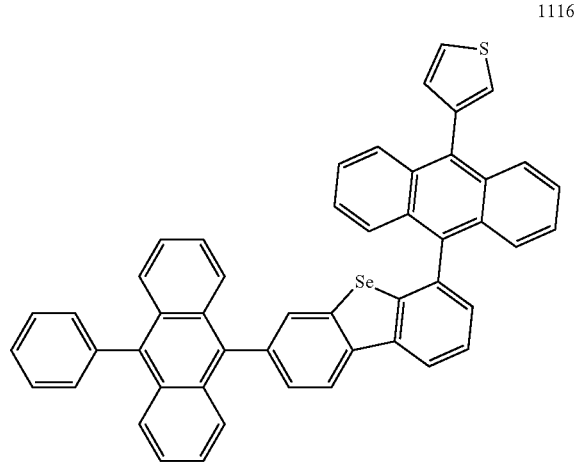
1117
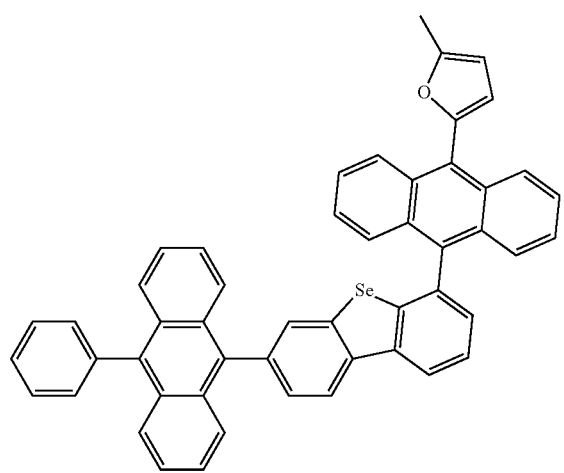
1858
-continued
1118
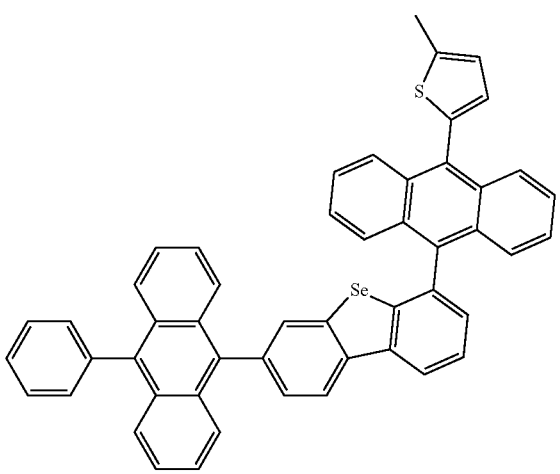
1119
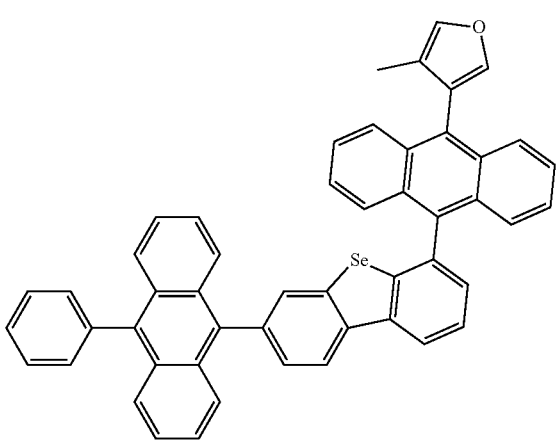
1120

1859
-continued
1121
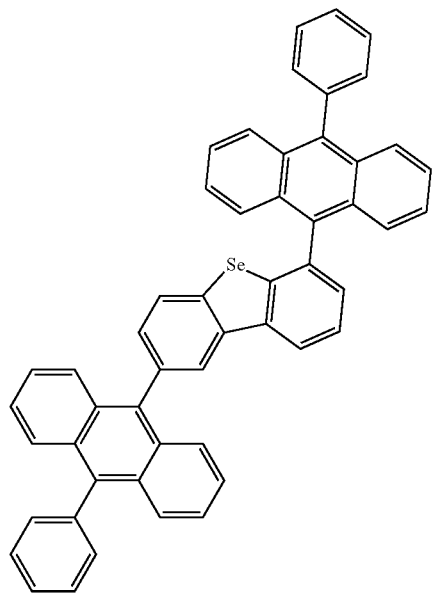
1122
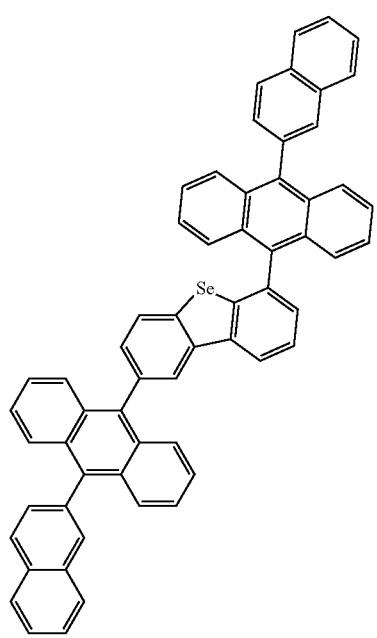
1860
-continued
1123
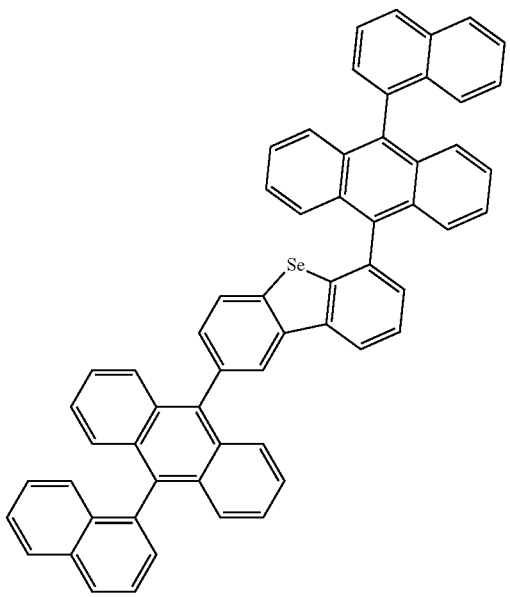
1124
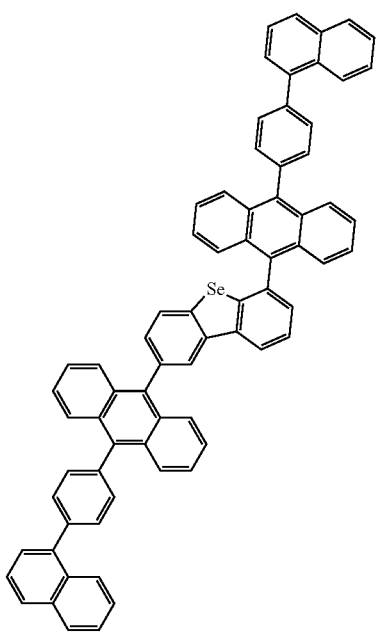

1861
-continued
1125
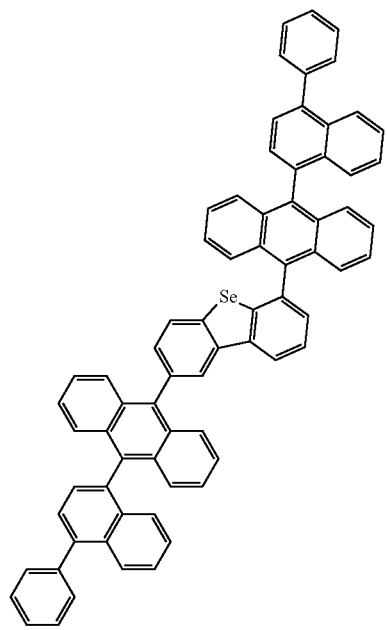
1126
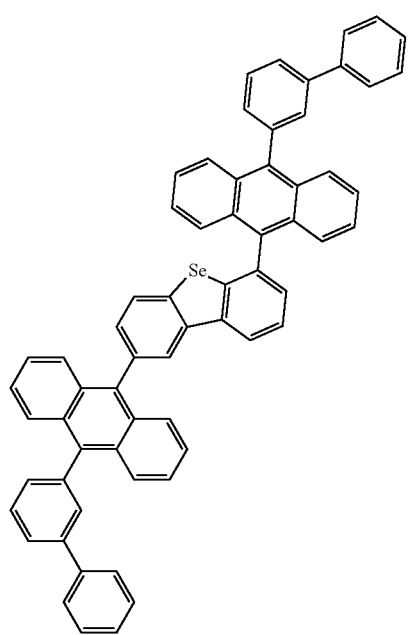
1862
-continued
1127
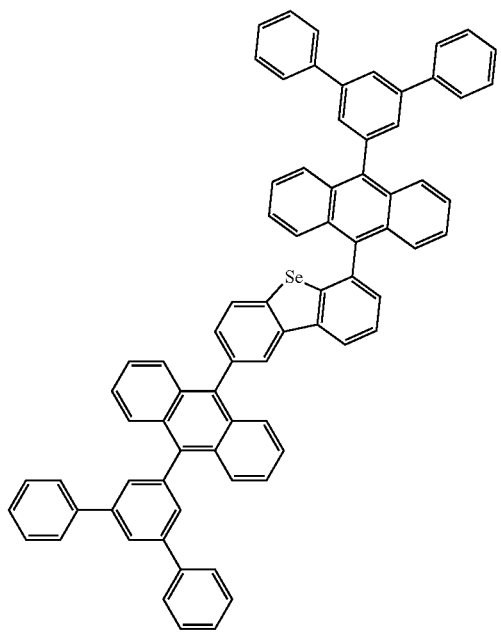
1128
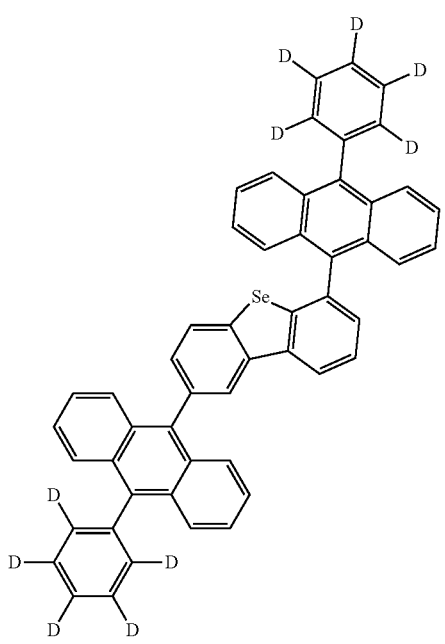

-continued
1129
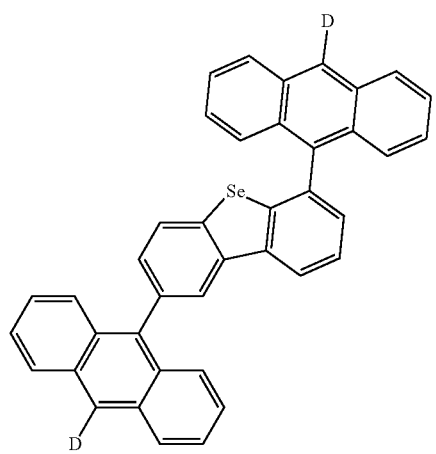
1130
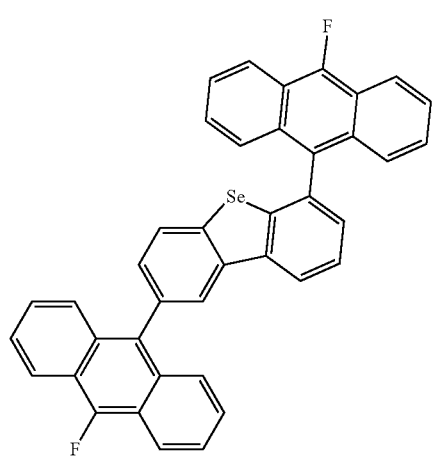
1131
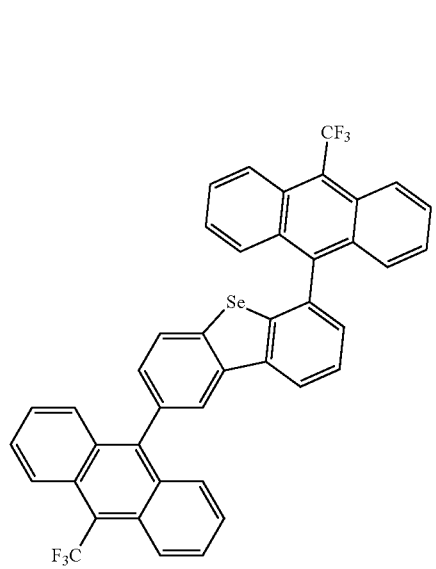
-continued
1132
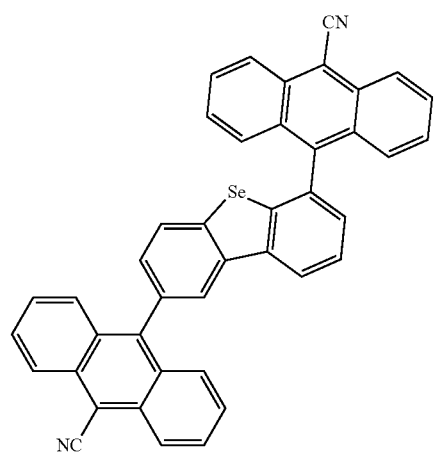
1133
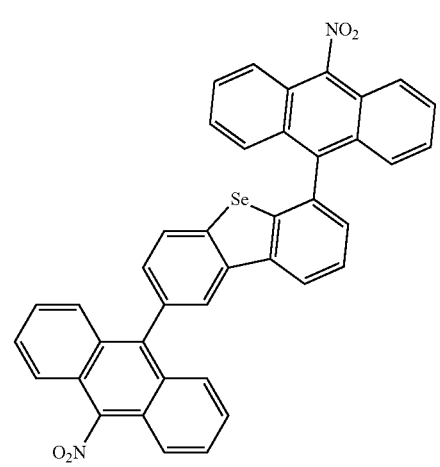
1134
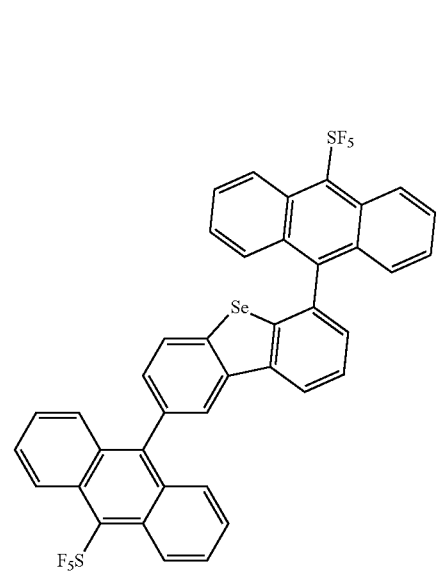

1865
-continued
1135
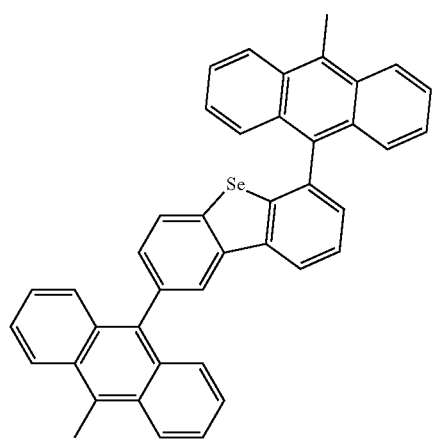
1136
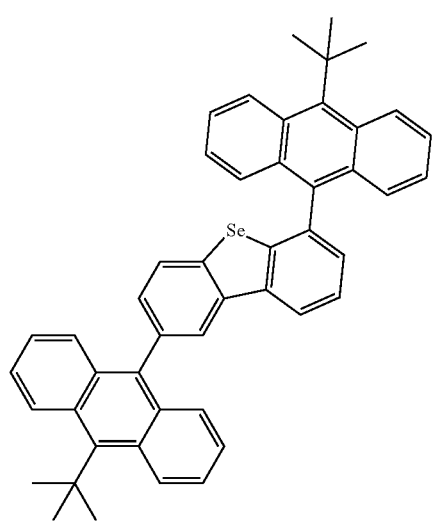
1137
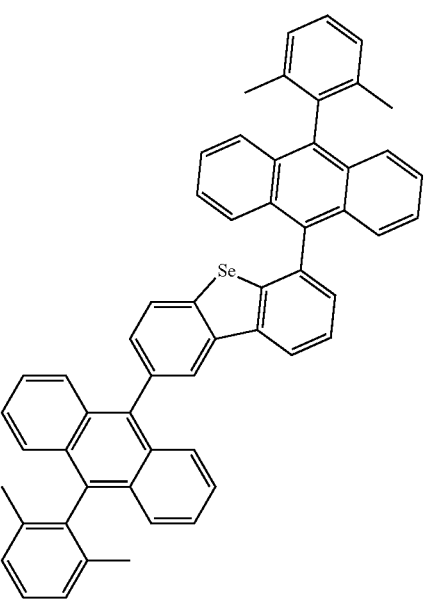
1866
-continued
1138
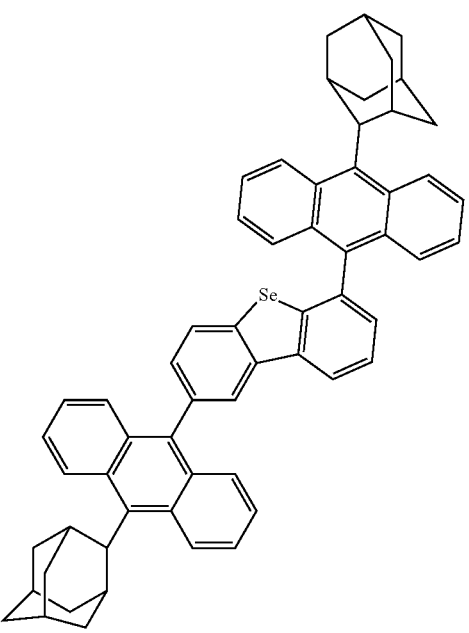
1139

1867
-continued
1140
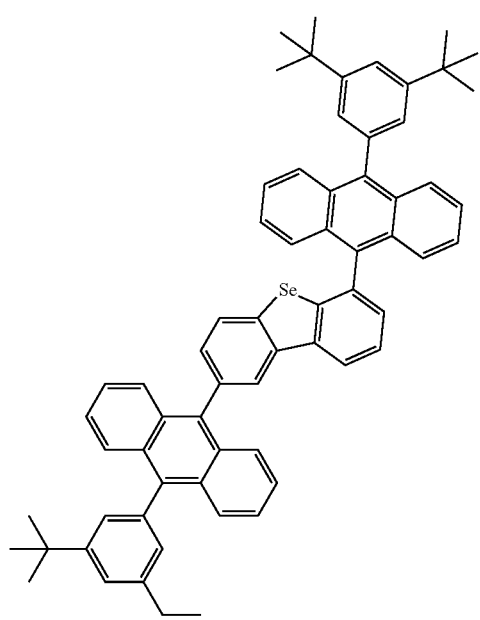
1141
1868
-continued
1142
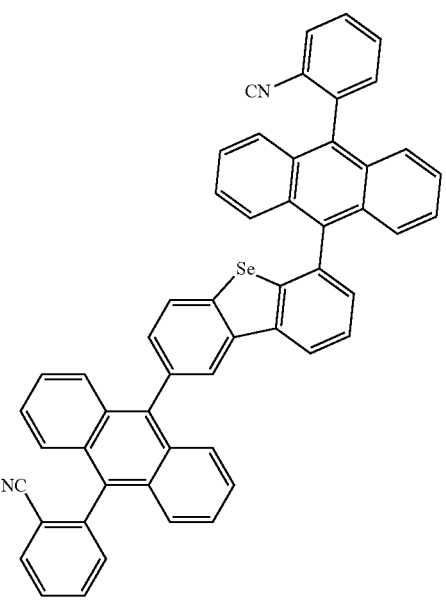
1143
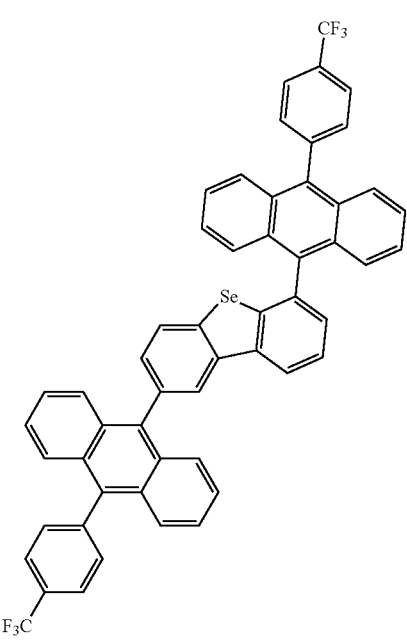

1144
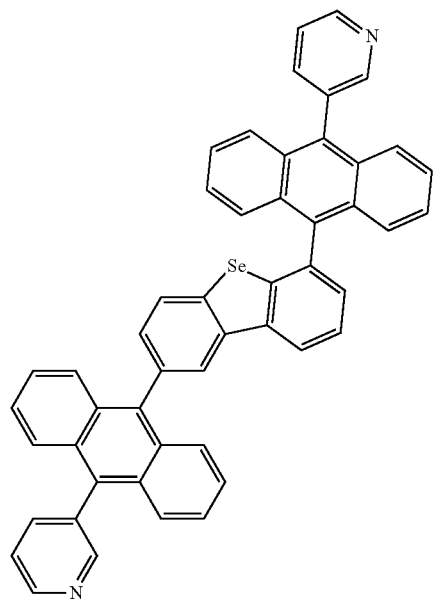
1146
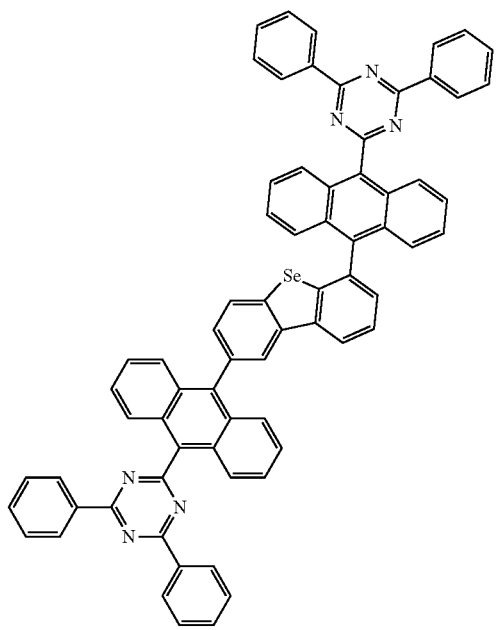
1145
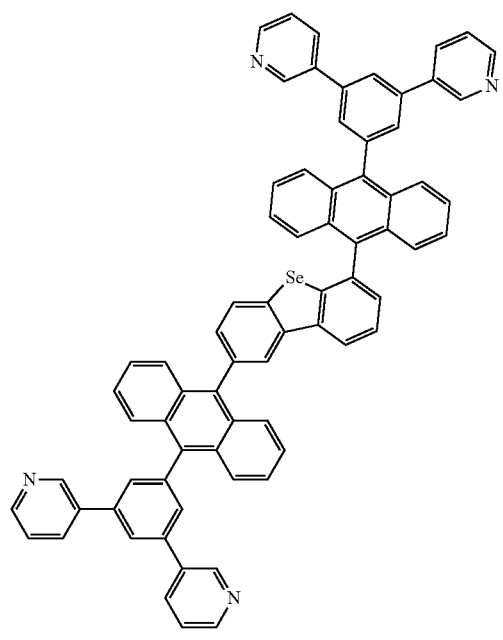
1147
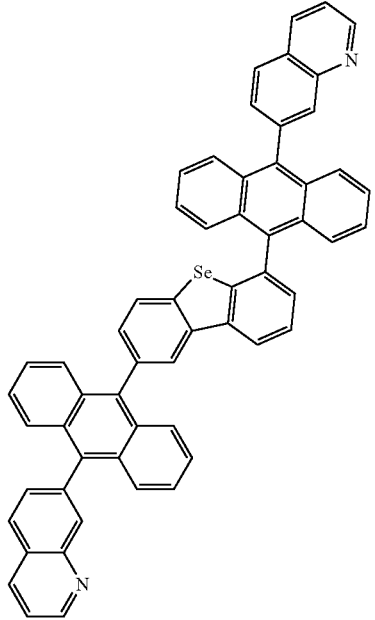

1871
-continued
1148
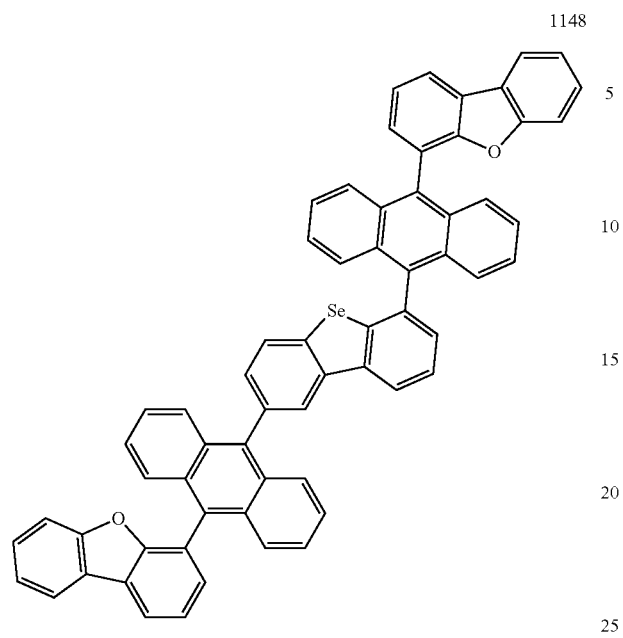
1149
1872
-continued
1150
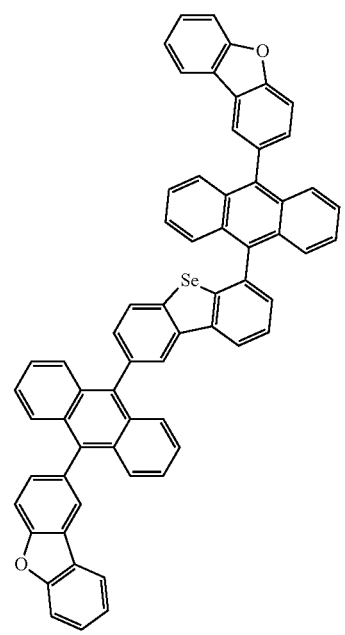
1151
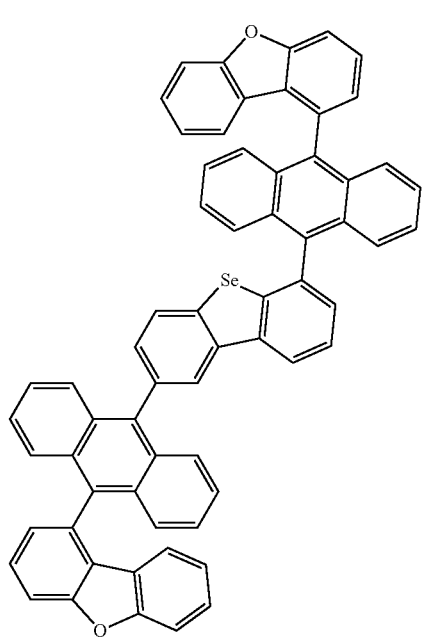

1873
-continued
1874
-continued
1152
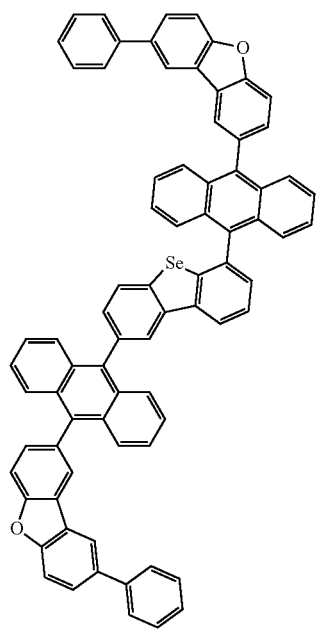
1154
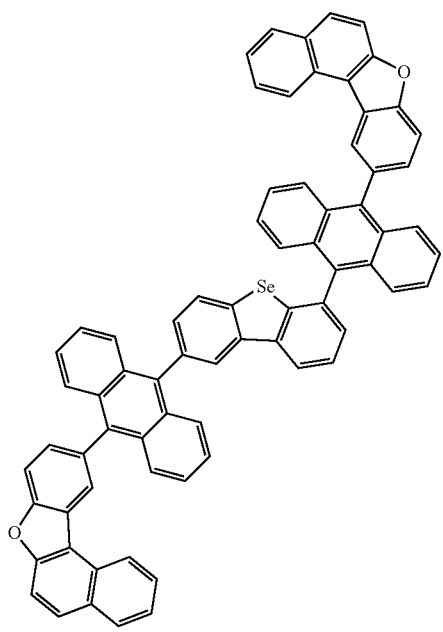
1153
1155

1875
-continued
1156
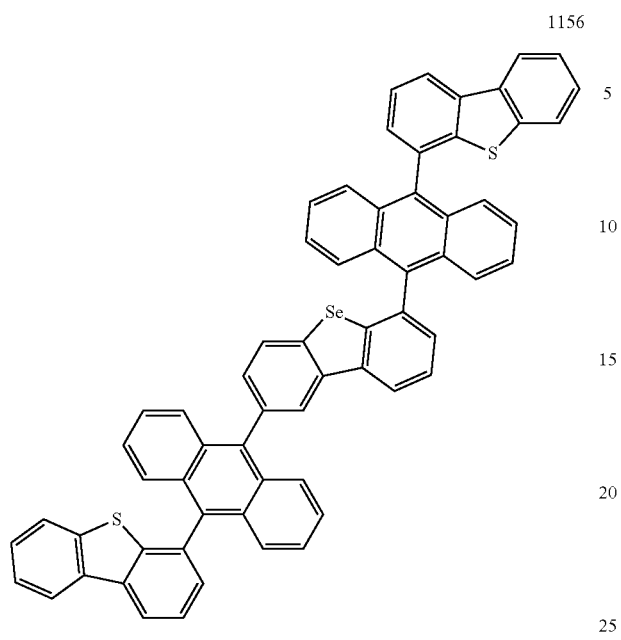
1876
-continued
1158
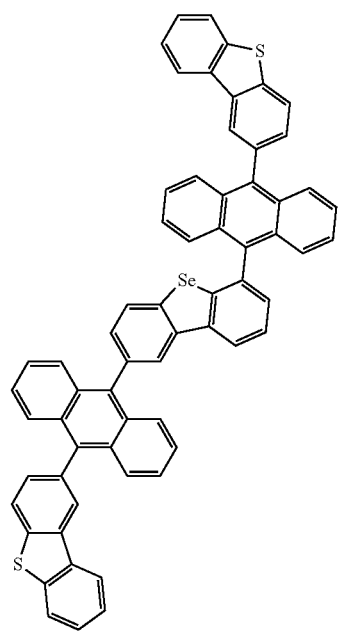
1157
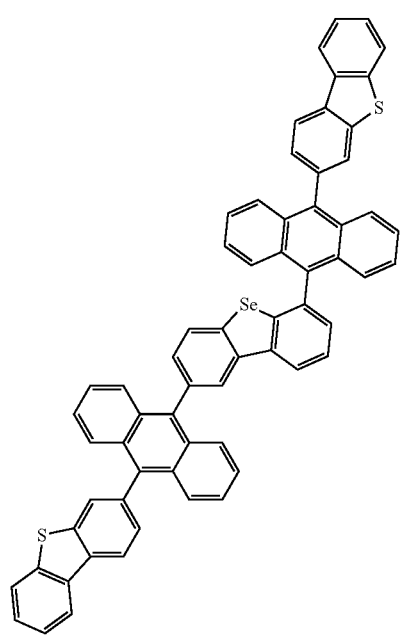
1159
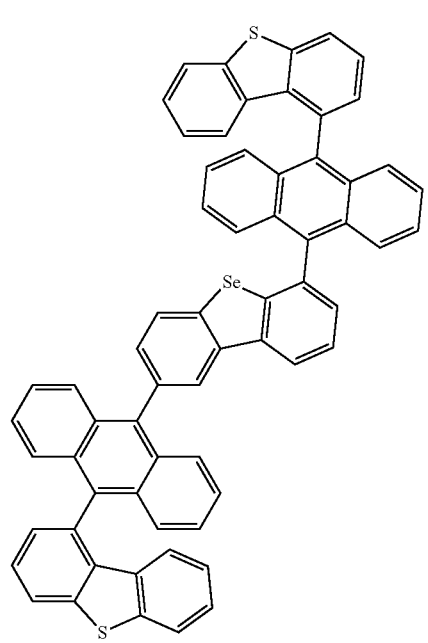

1877
-continued
1160
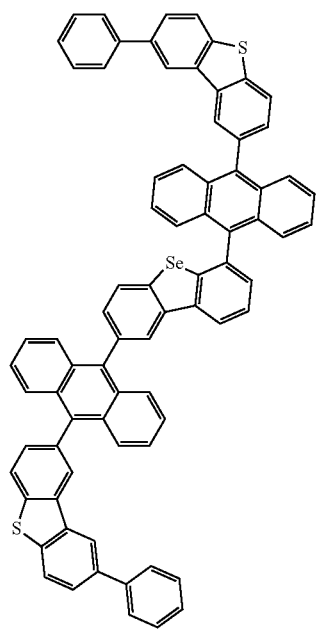
1161
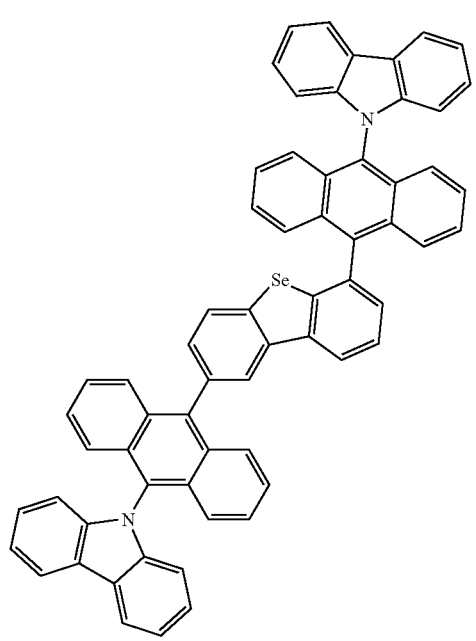
1878
-continued
1162
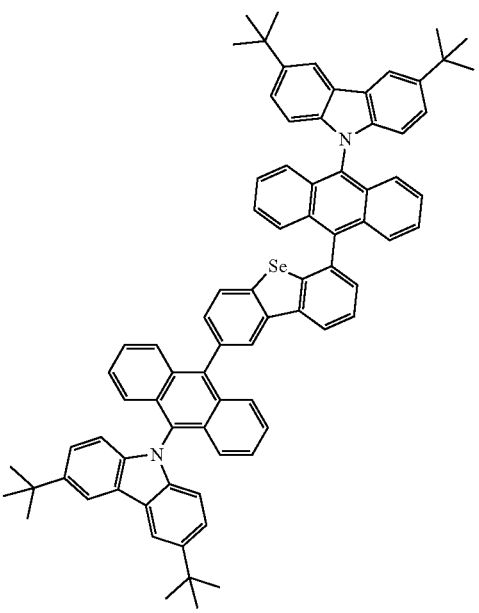
1163
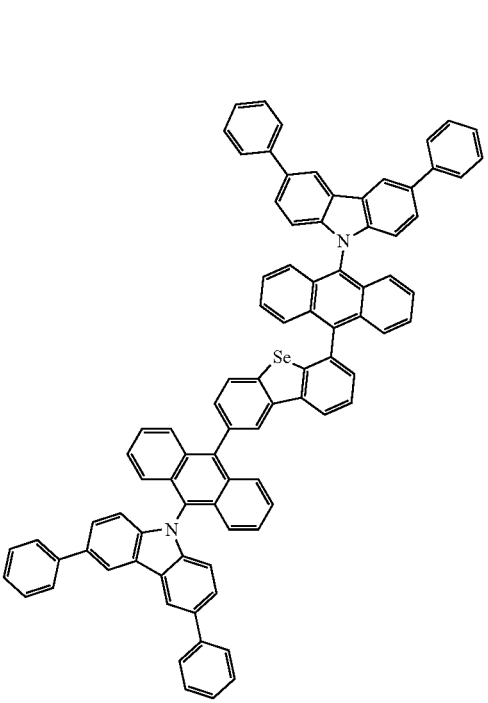

1879
-continued
1164
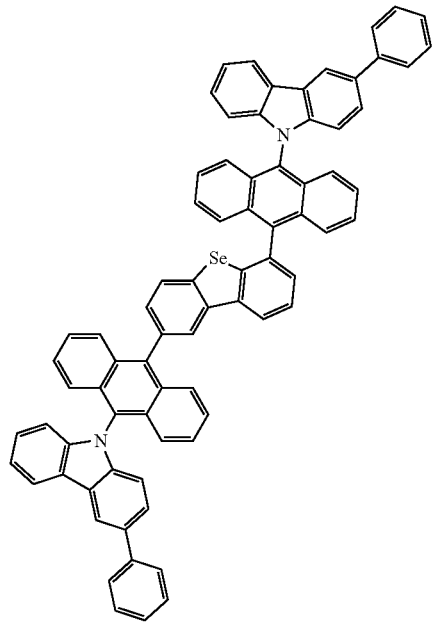
1165
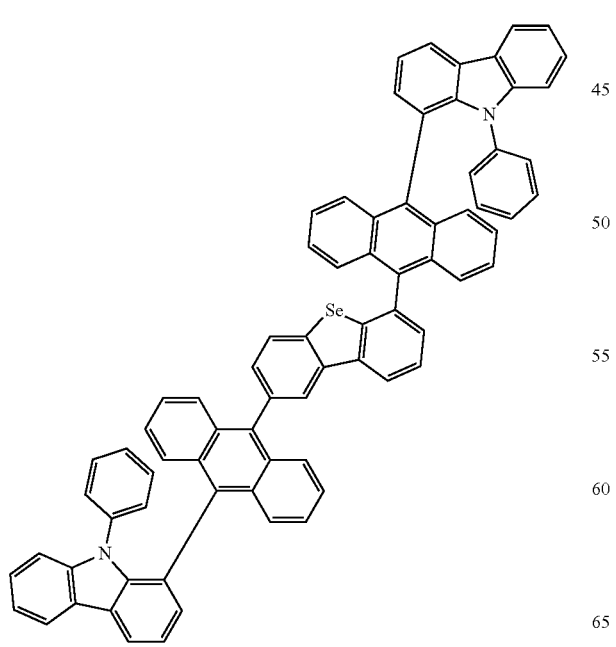
1880
-continued
1166
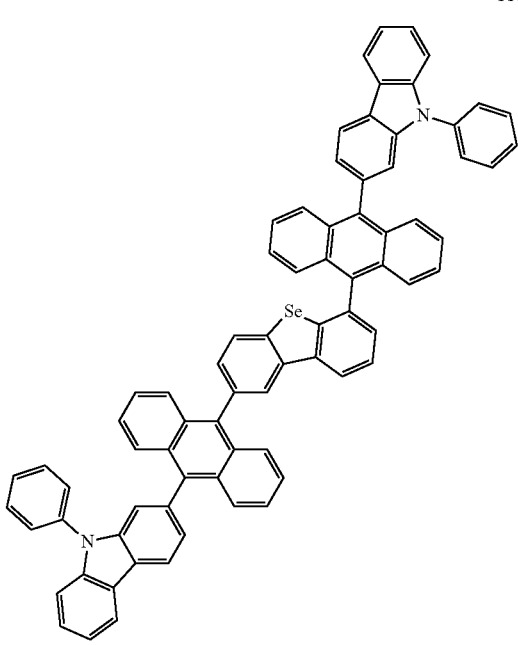
1167
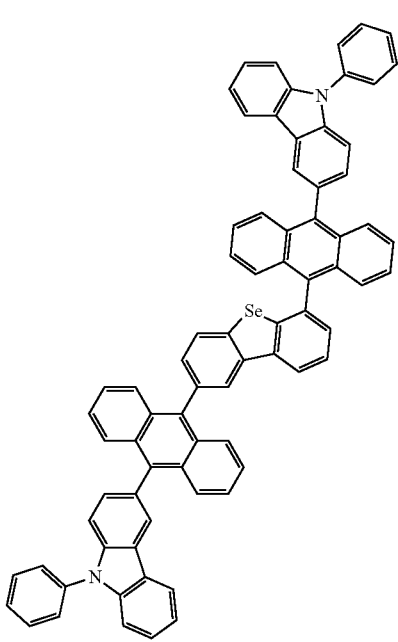

1881
-continued
1882
-continued
1168
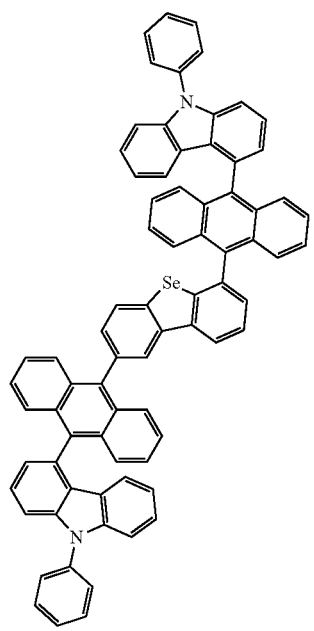
1170
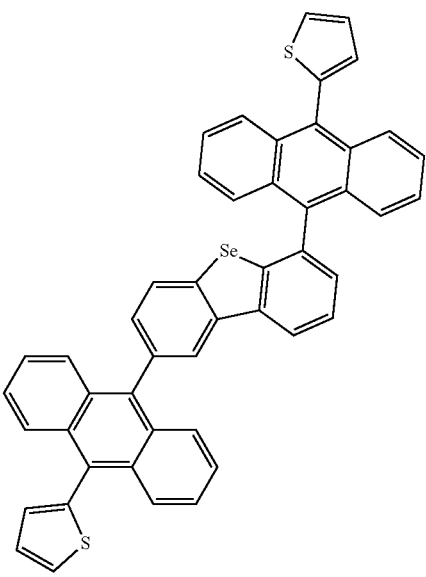
1169
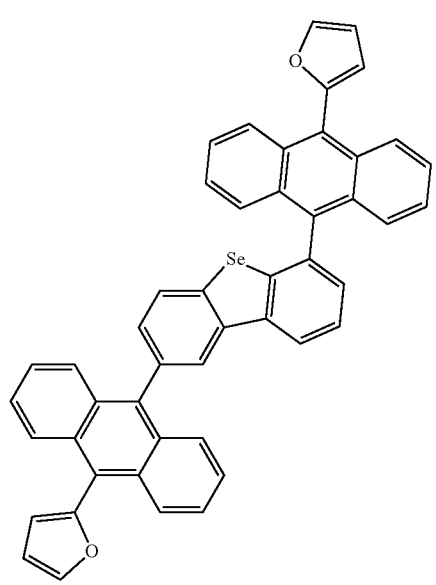
1171
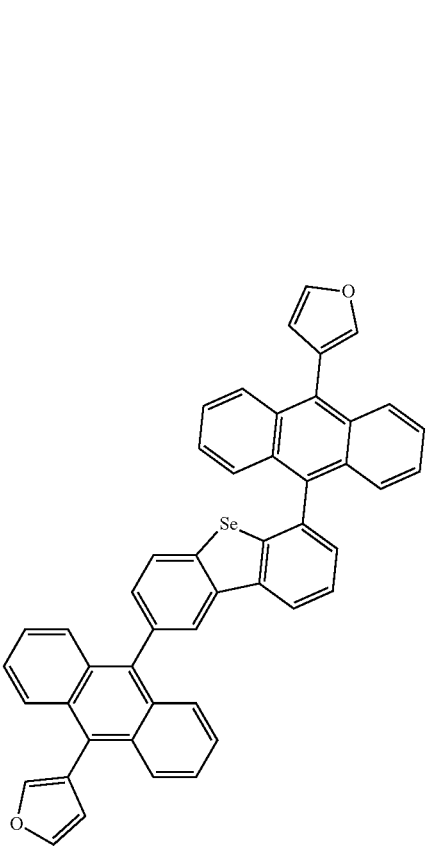

1883
-continued
1172
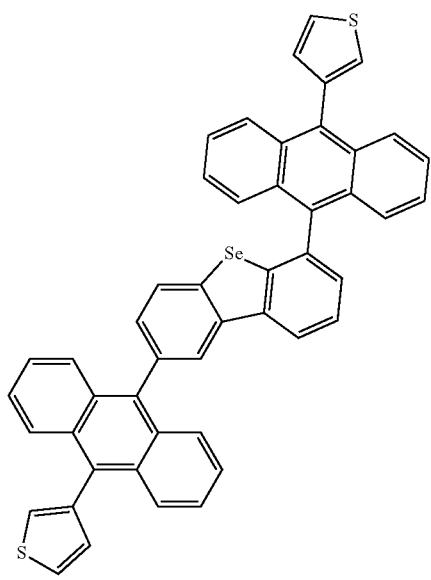
1173
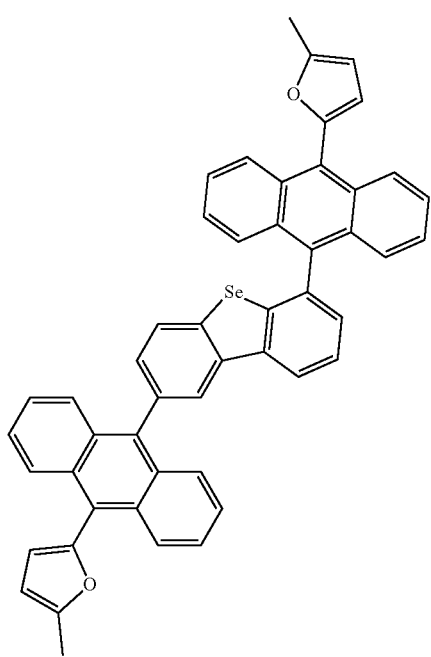
1884
-continued
1174
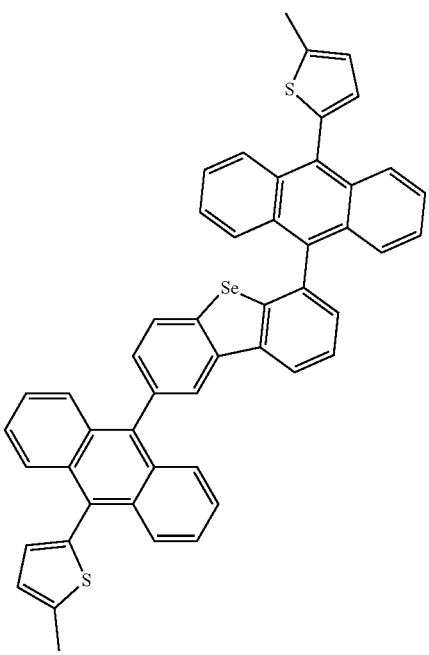
1175
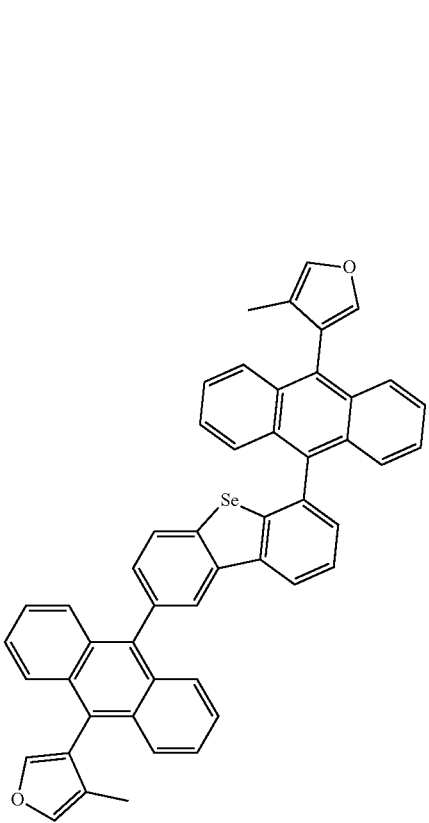

1885
-continued
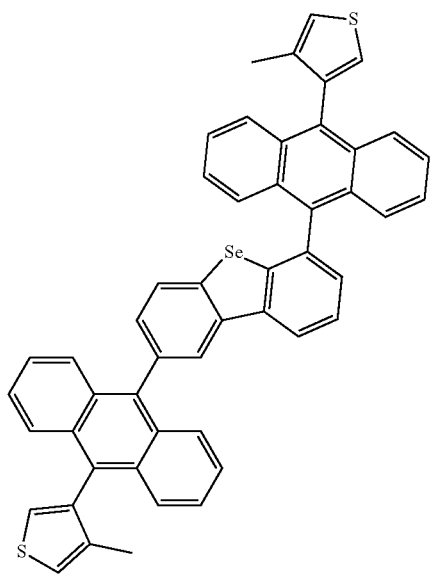
1176
1886
-continued
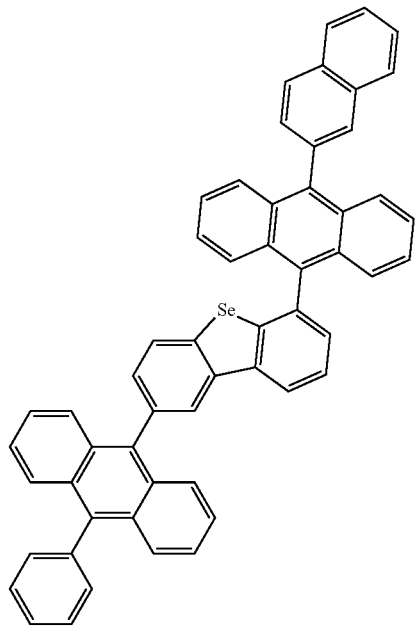
1178
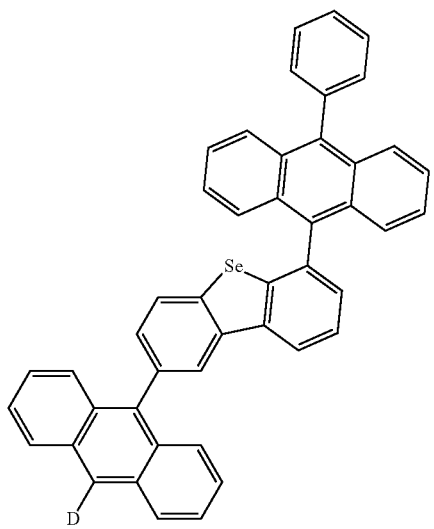
1177
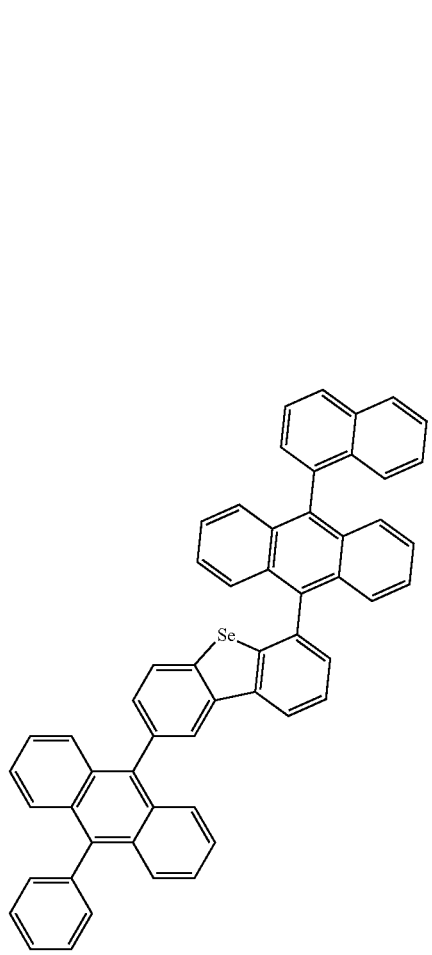
1179

1887
-continued
1180
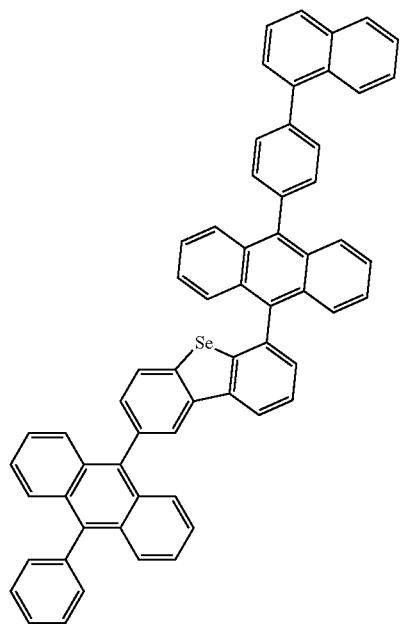
1888
-continued
1182
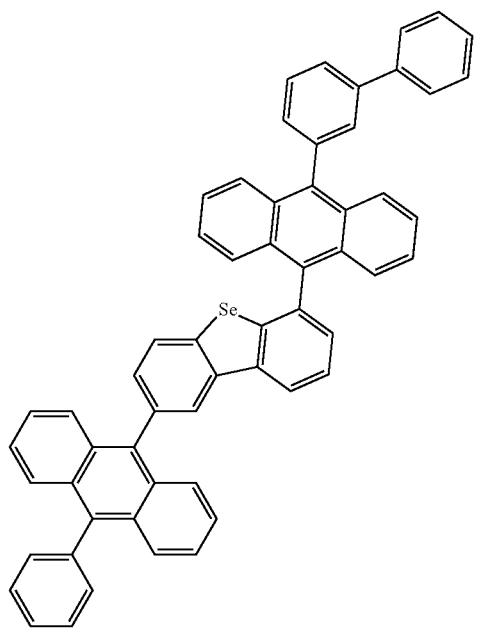
1181
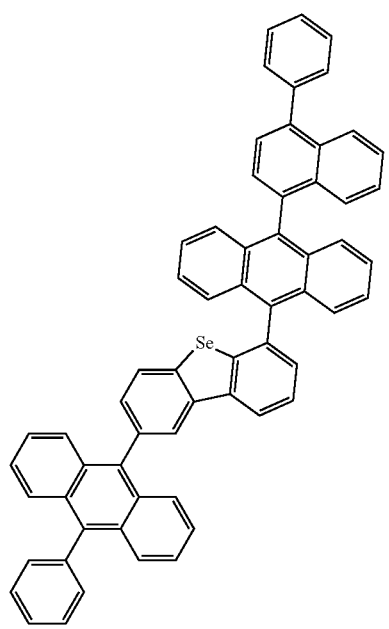
1183

1889
-continued
1184
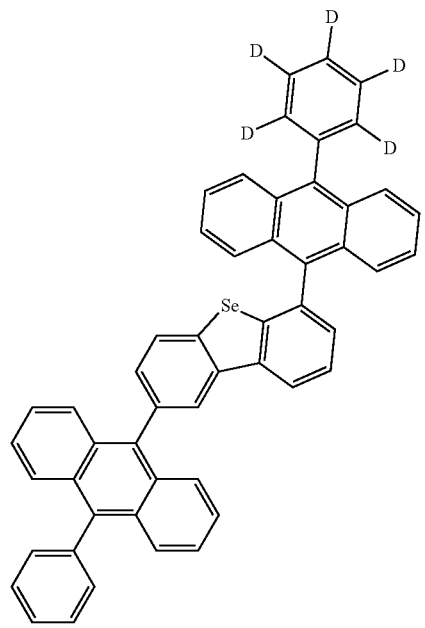
1185
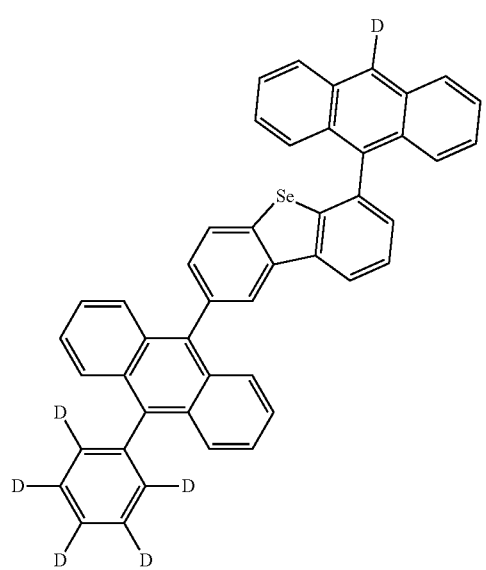
1890
-continued
1186
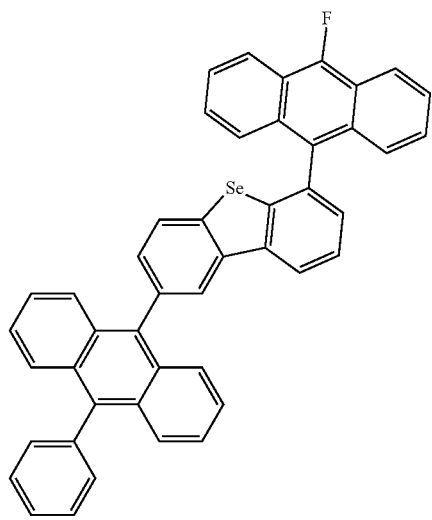
1187
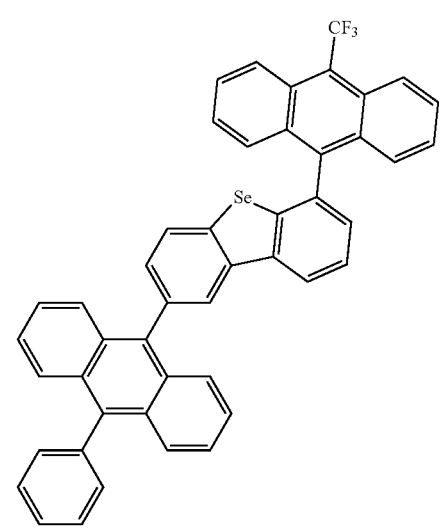
1188
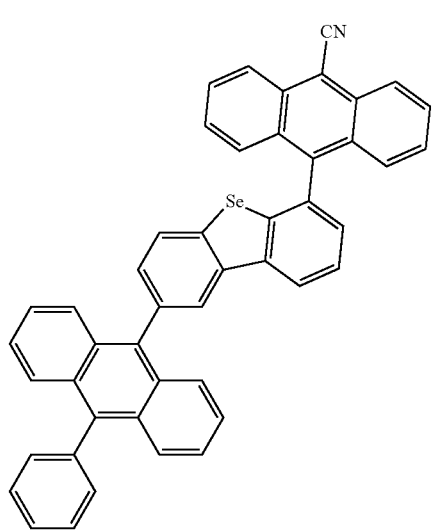

1891
-continued
1189
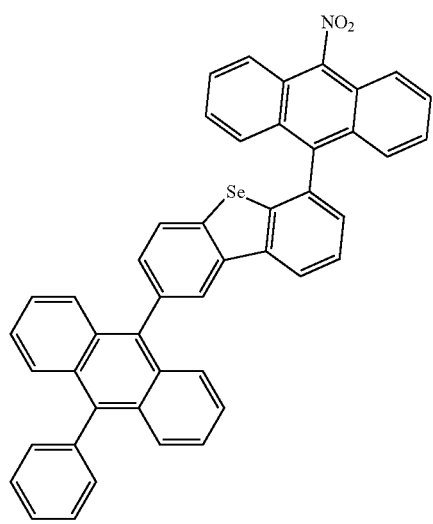
1892
-continued
1191
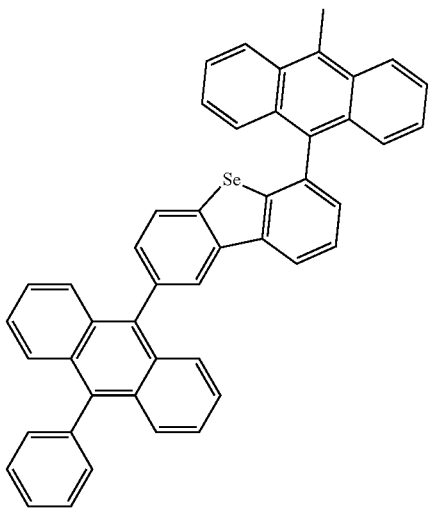
1190
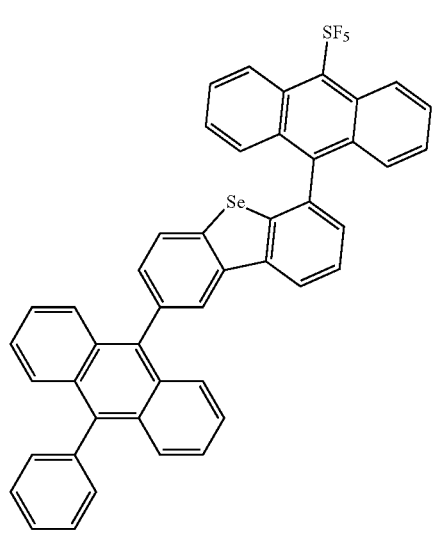
1192
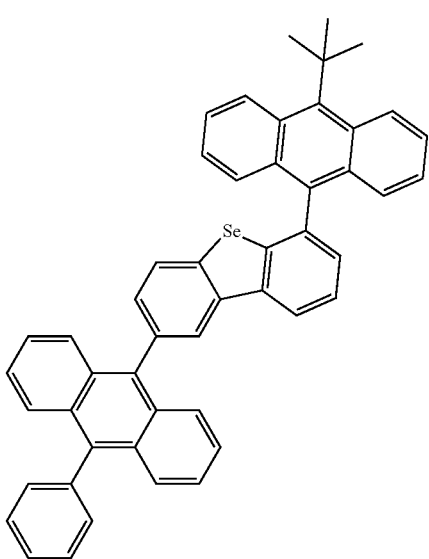

1893
-continued
1193
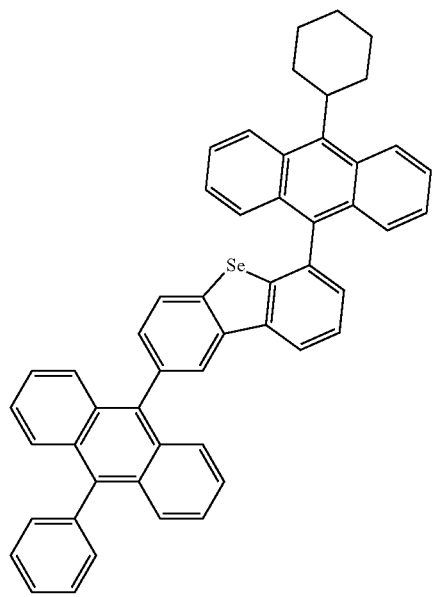
1194
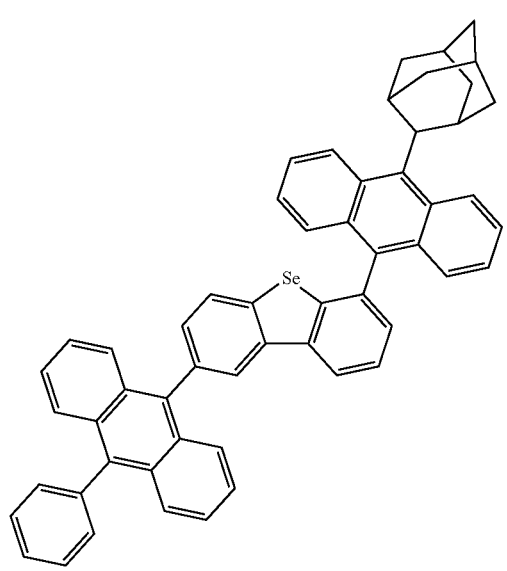
1894
-continued
1195
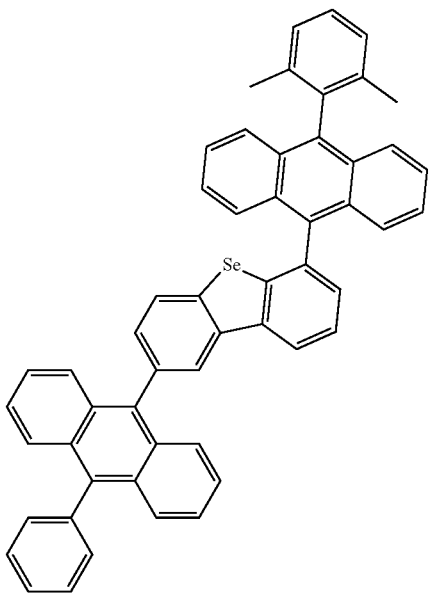
1196
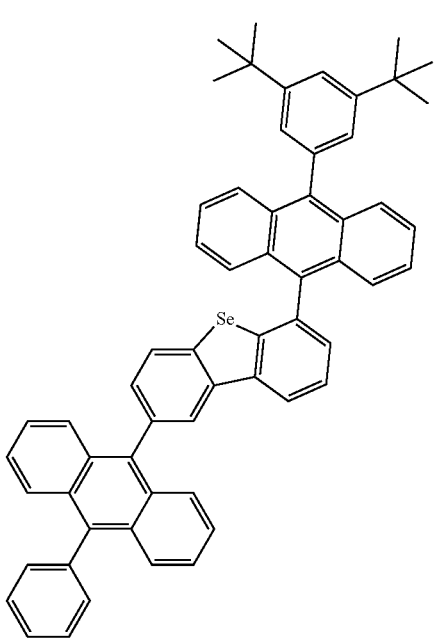

1895
-continued
1896
-continued
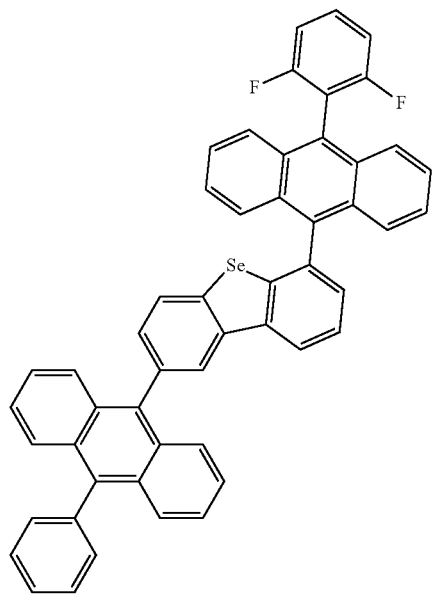
1197
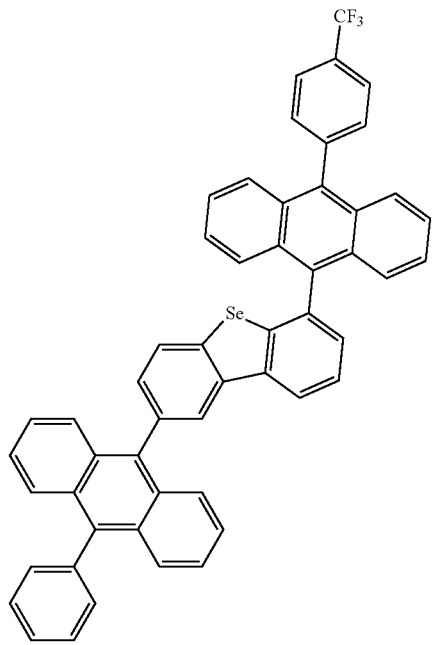
1199
1198
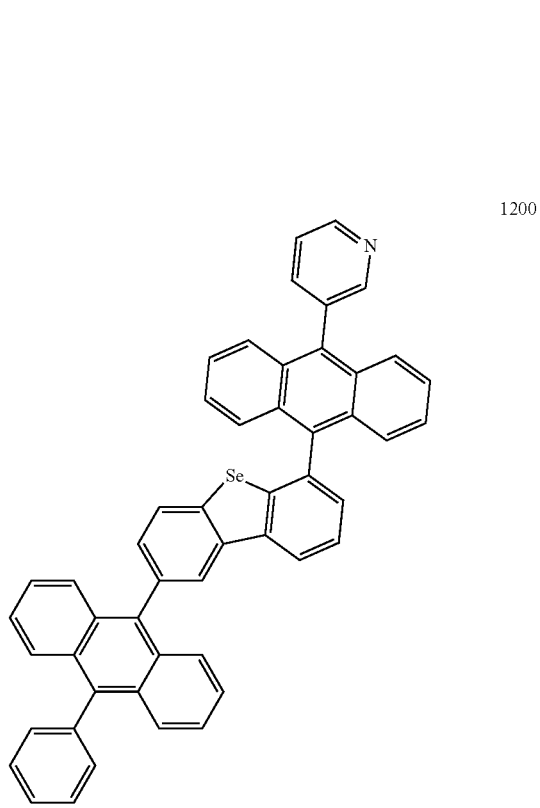
1200

1897
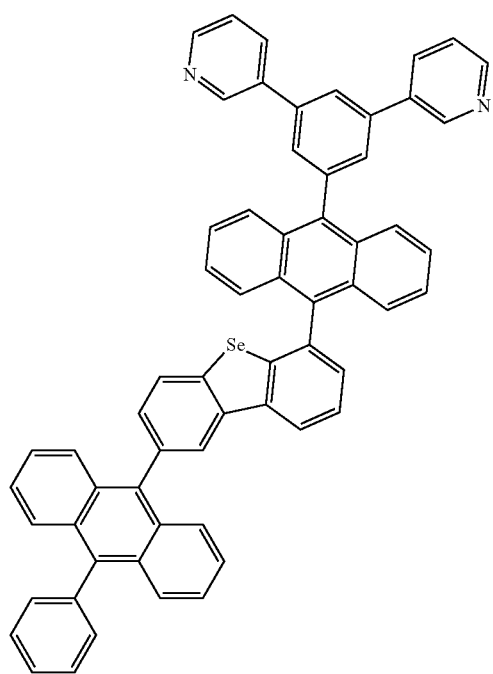
1898
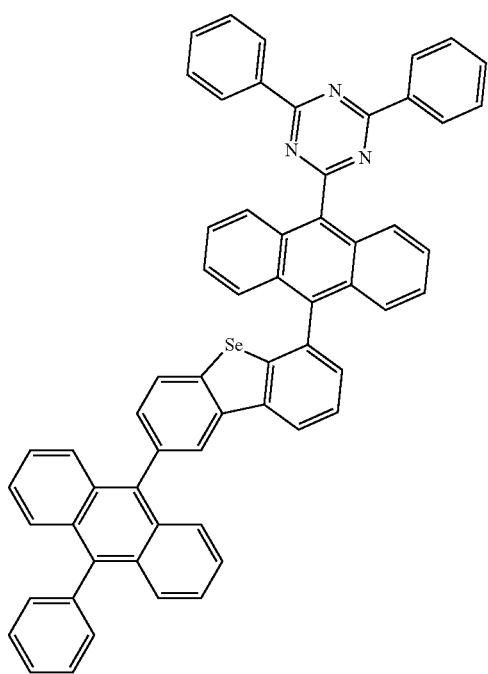
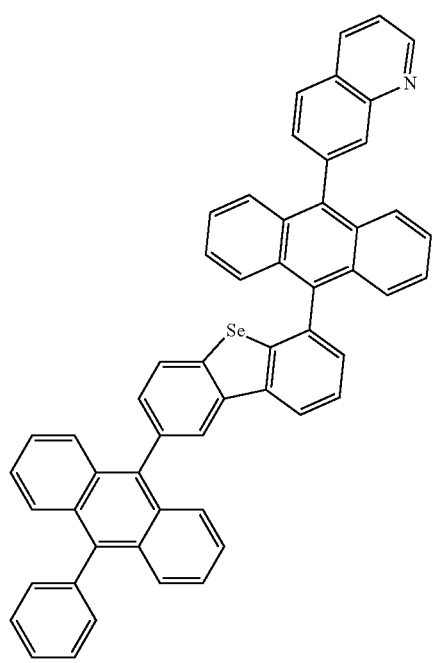
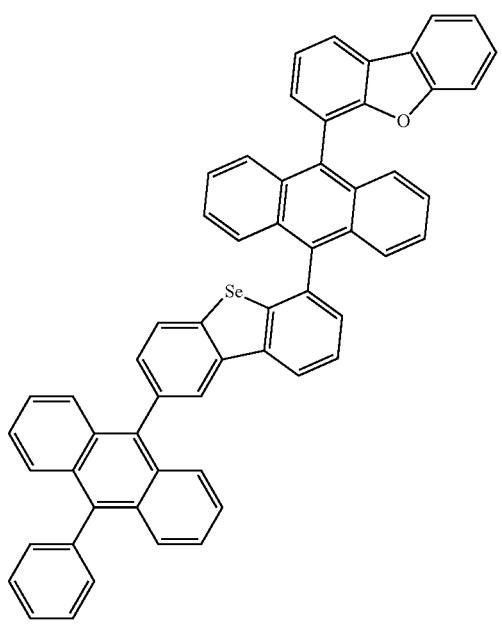

-continued
1205 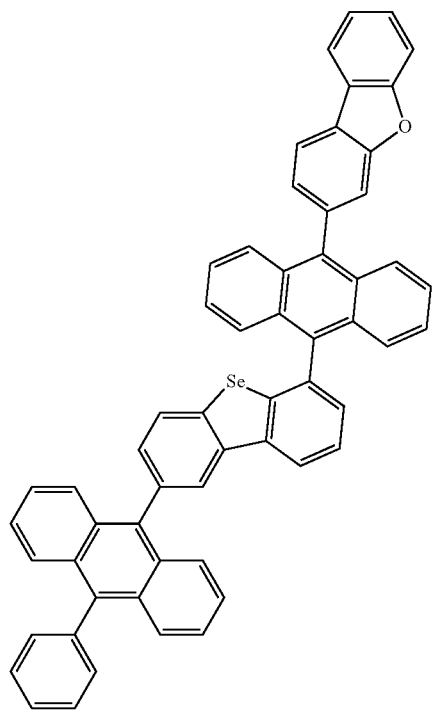
1206 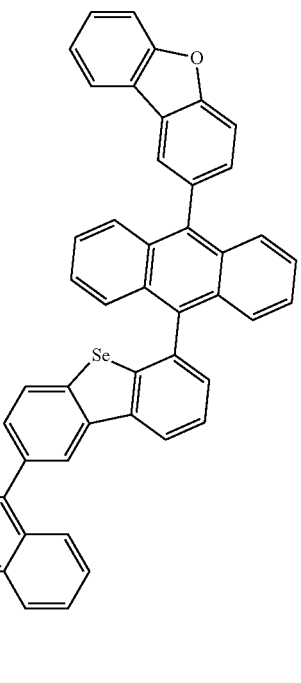
1207 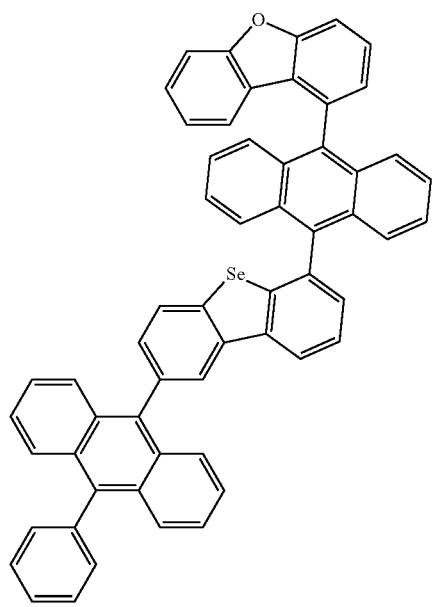
1208 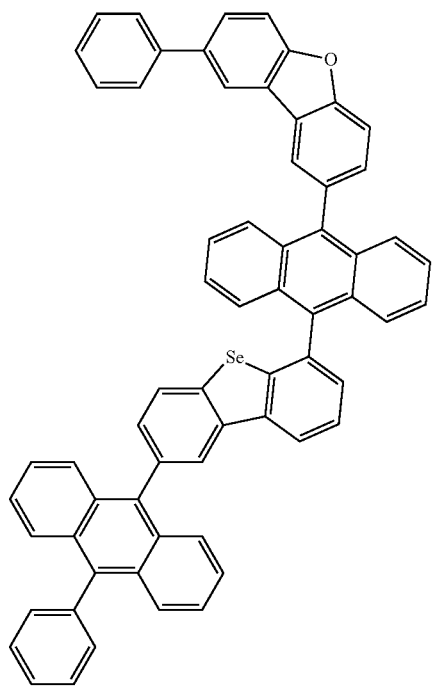

-continued
1901
1209
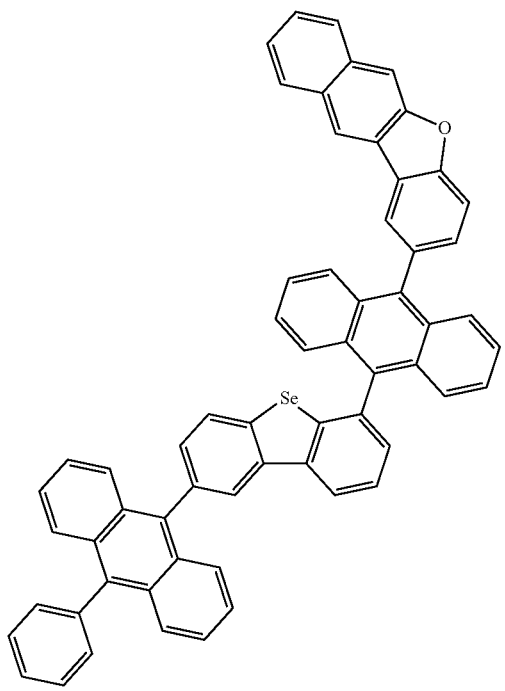
1902
1210
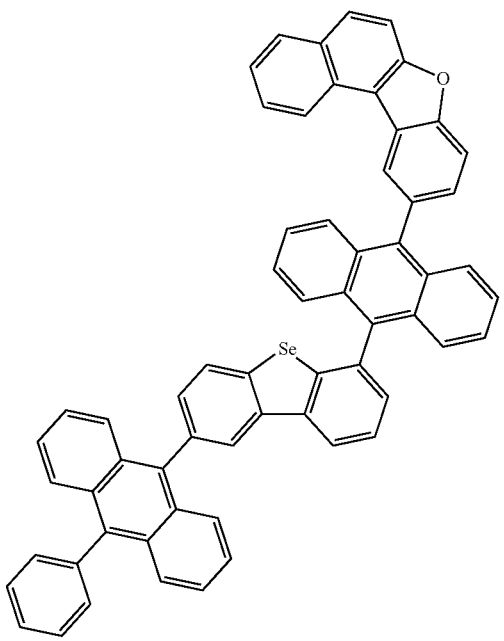
1211
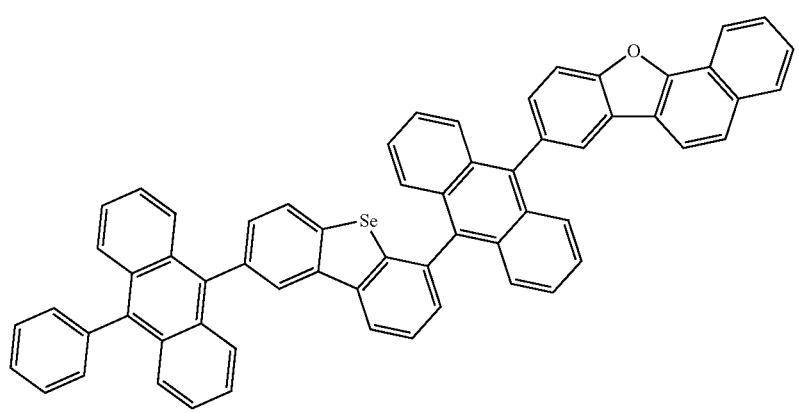

-continued
1212
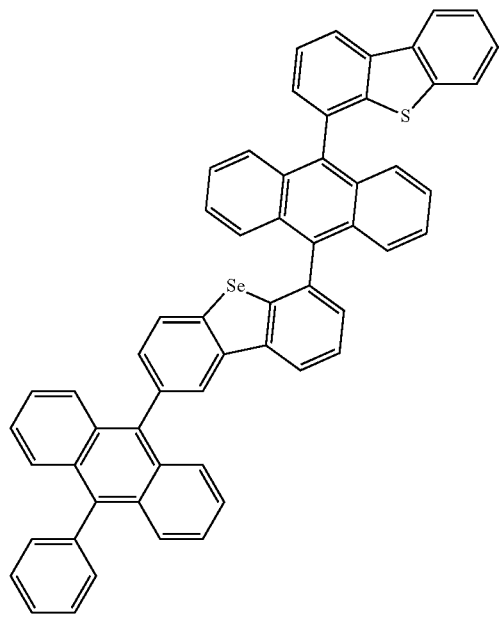
1213
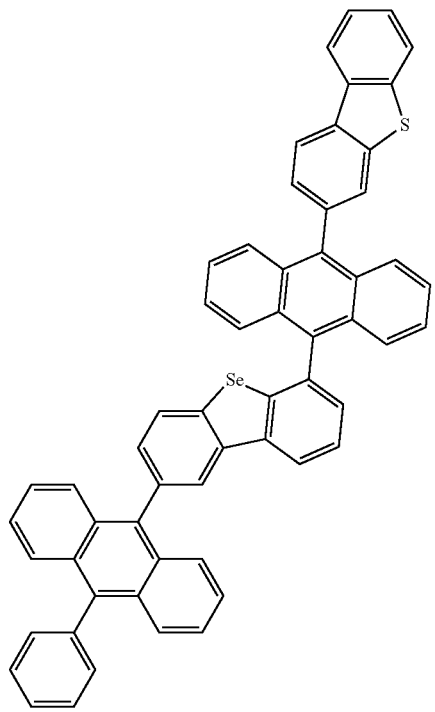
1214
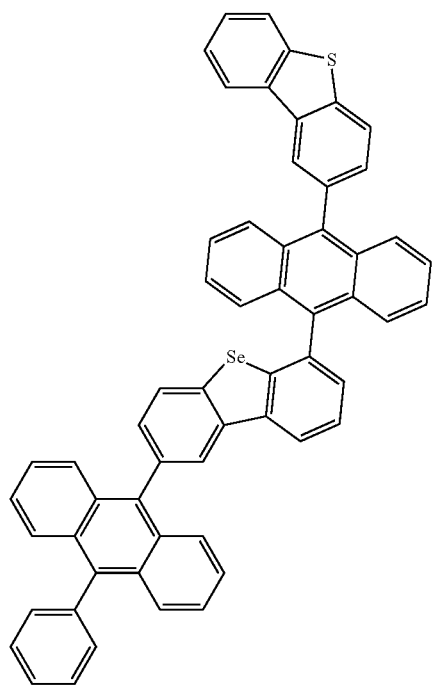
1215
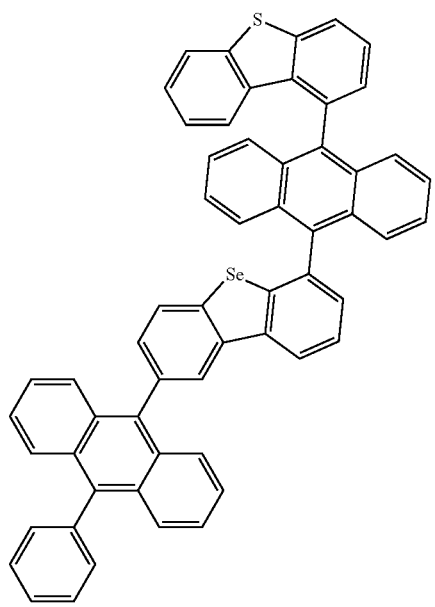

-continued
1216
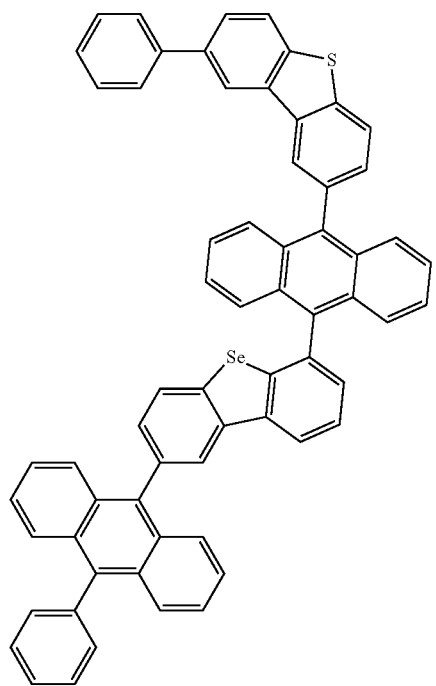
1217
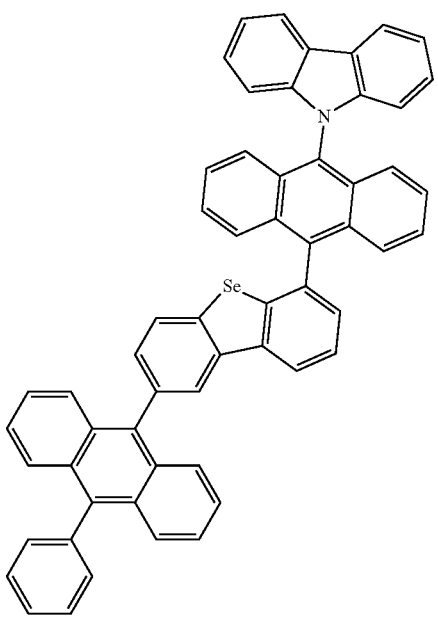
1218
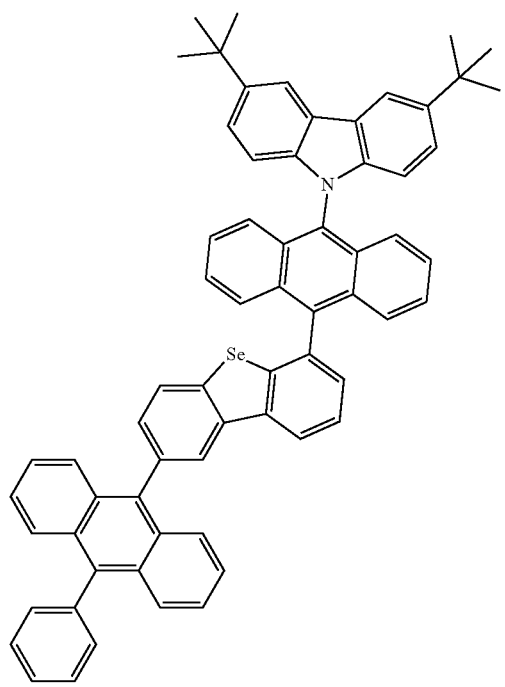
1219
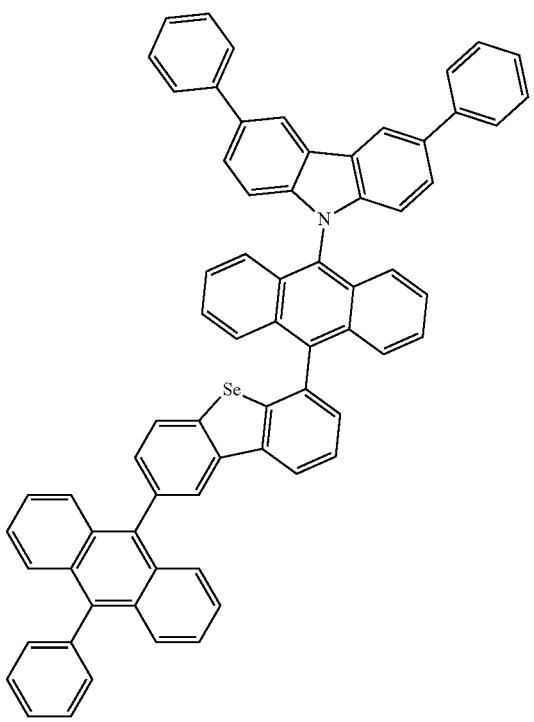

-continued
1220
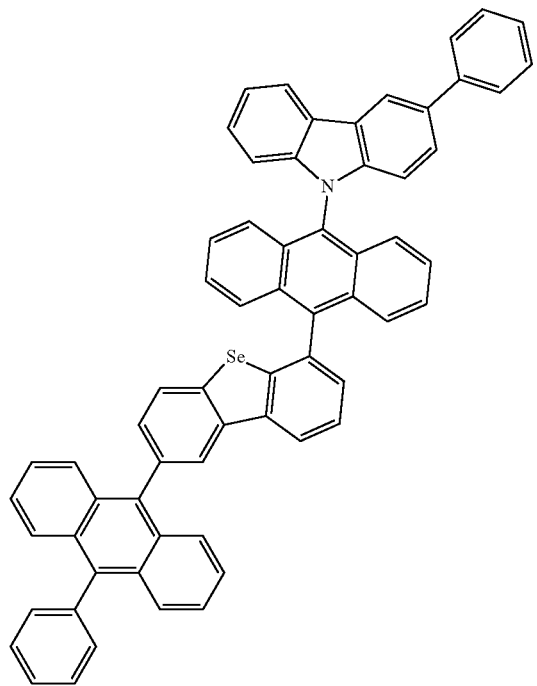
1221
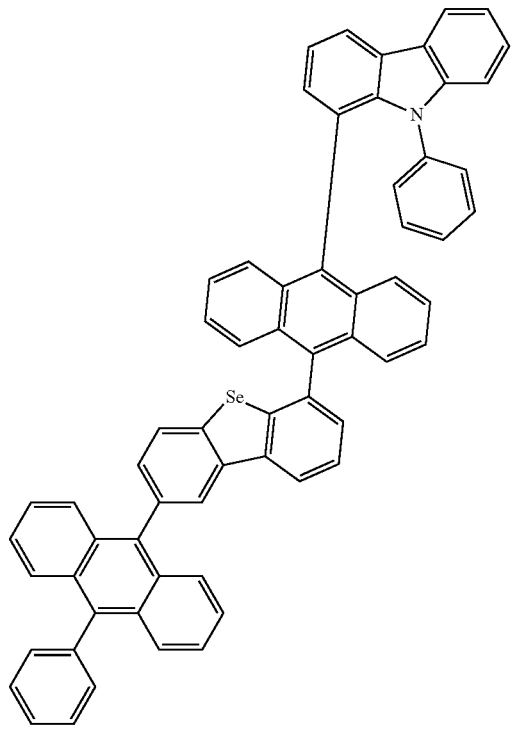
1222
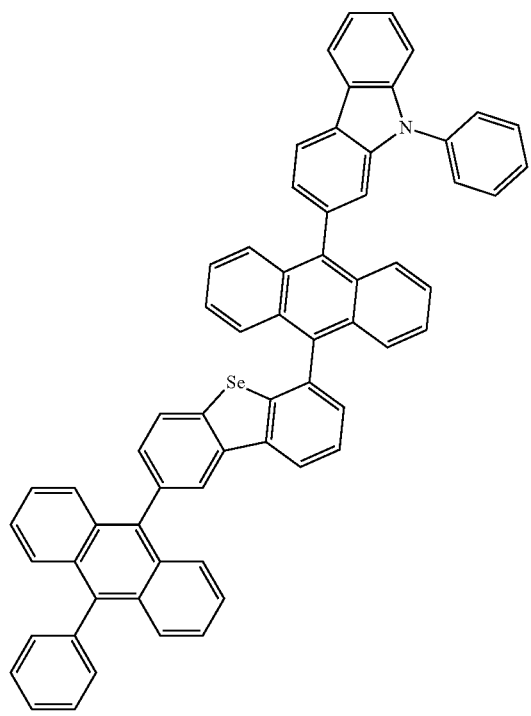
1223
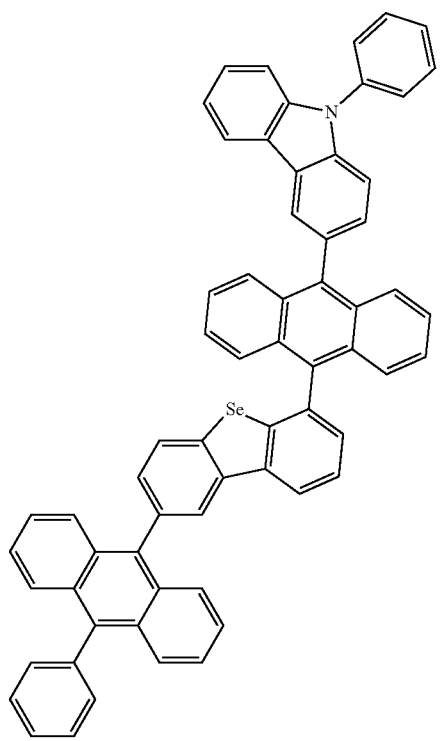

1909 1910
-continued
1224
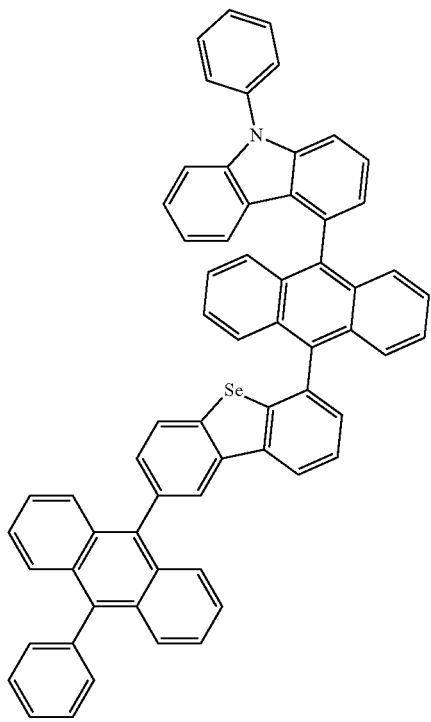
1225
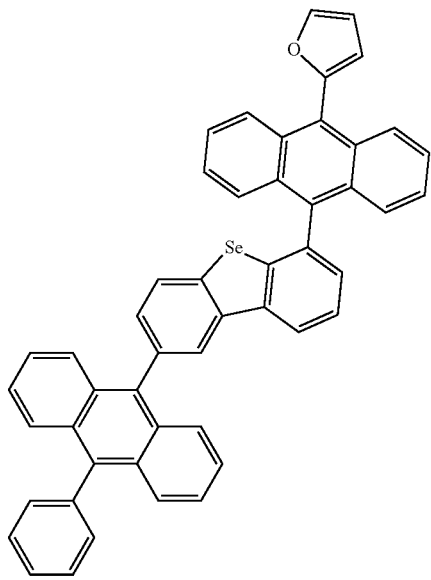
1226
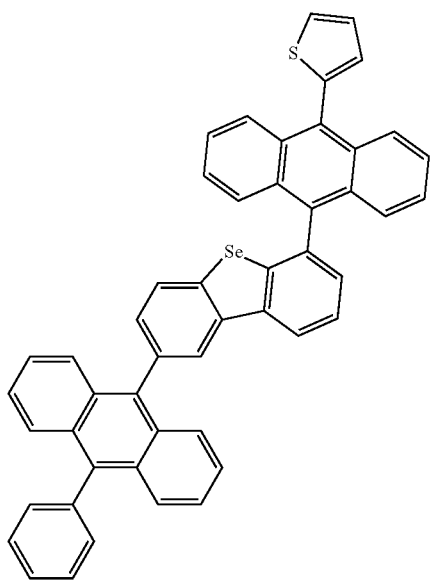
1227
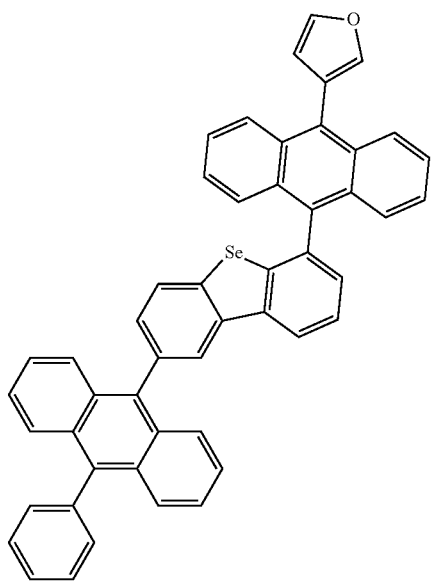

-continued
1228
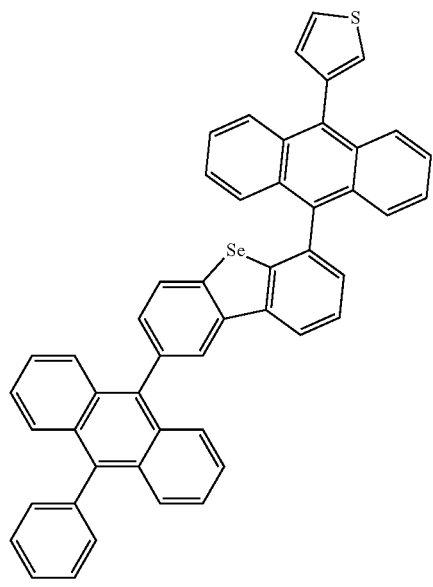
1229
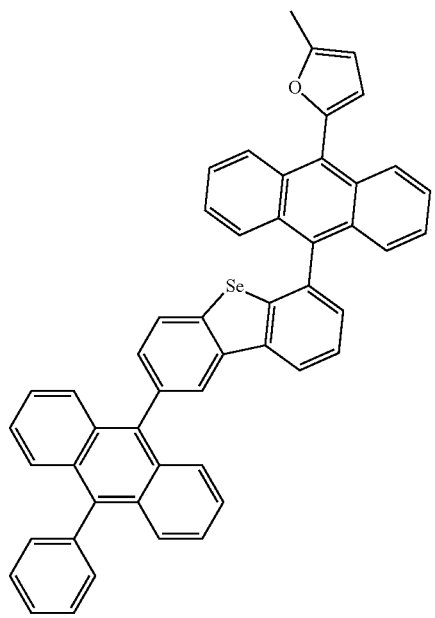
1230
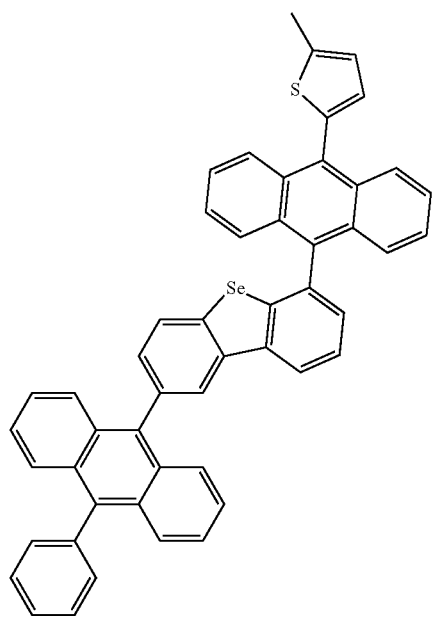
1231

-continued
1232
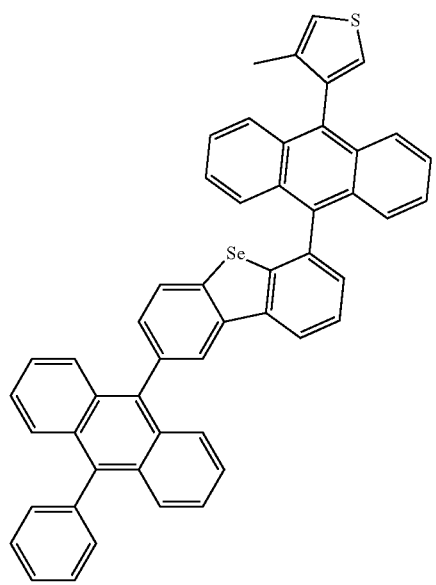
1233
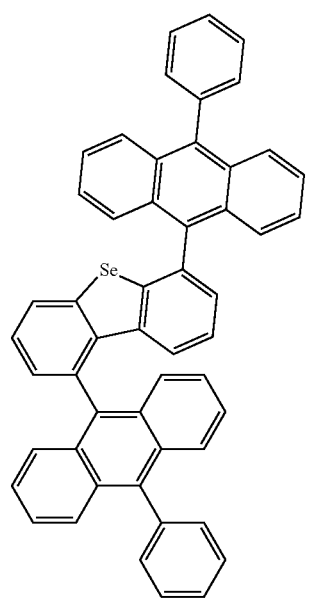
1234
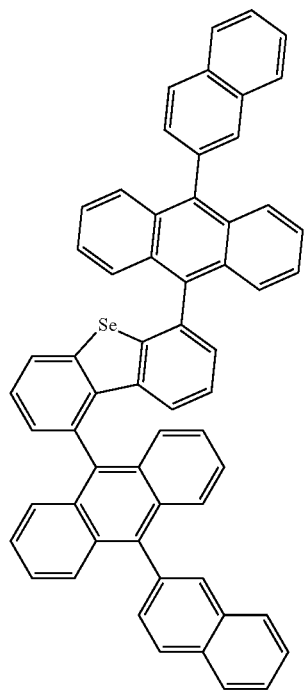
1235
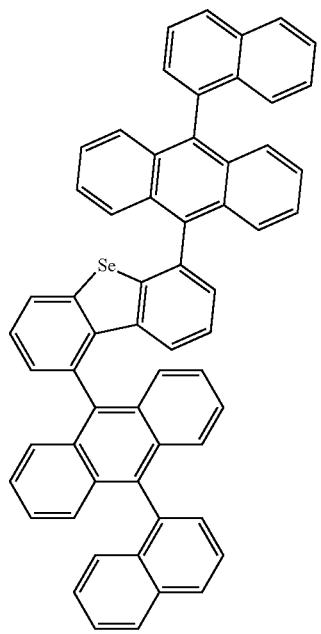

-continued
1236
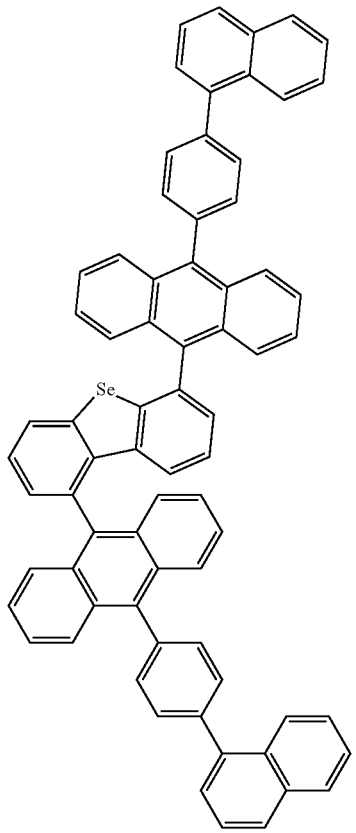
1237
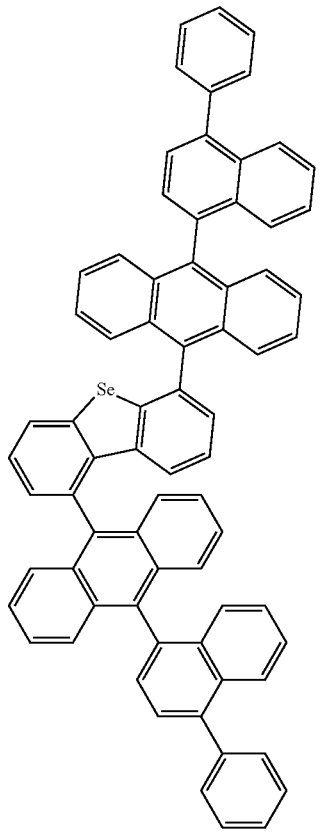
1238
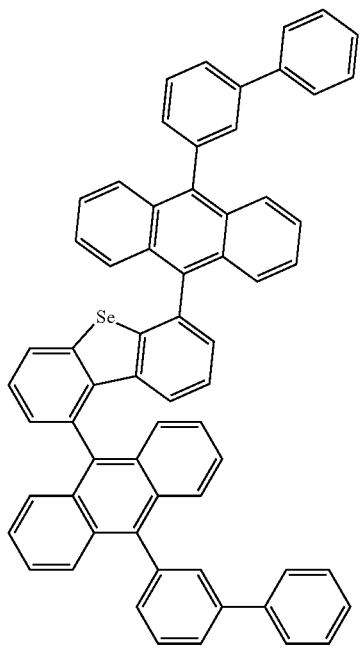
1239
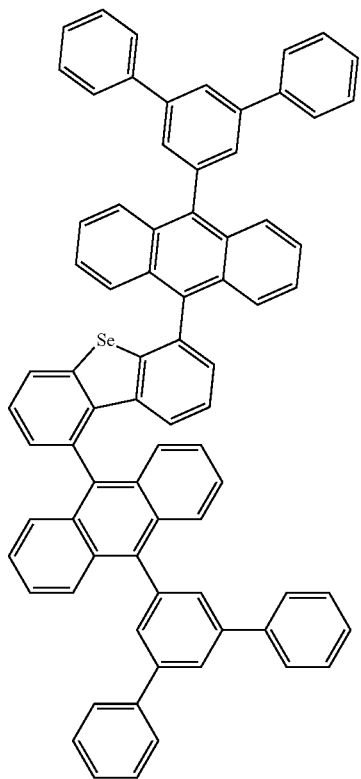

1917 | 1918
-continued
1240
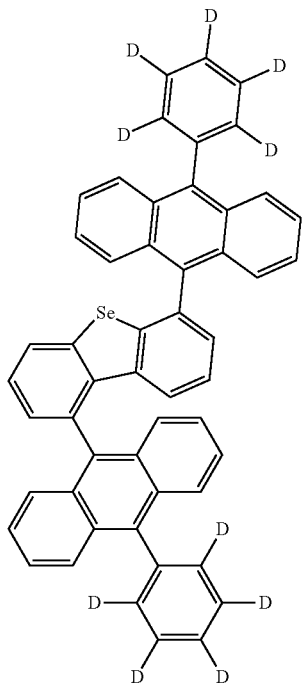
1241
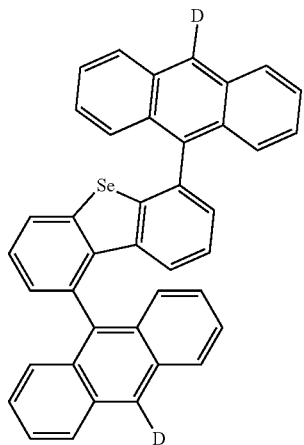
1242
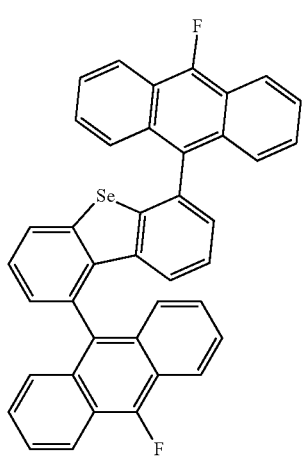
1243
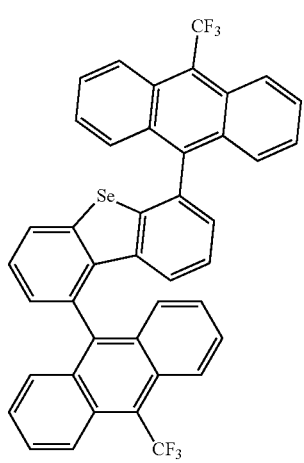
1244
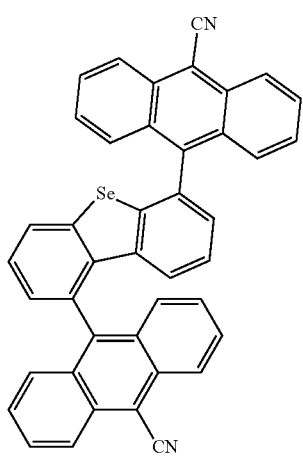
1245
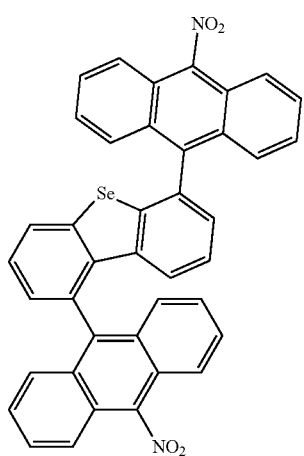

-continued
1246
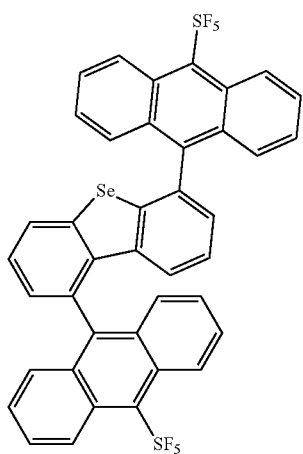
1247
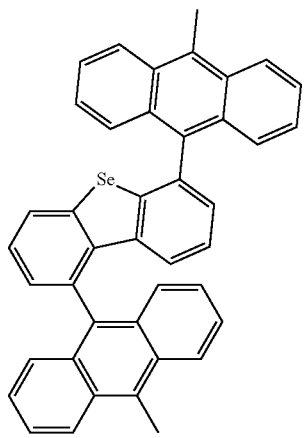
1248
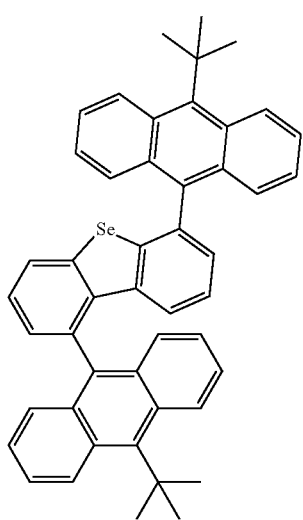
1249
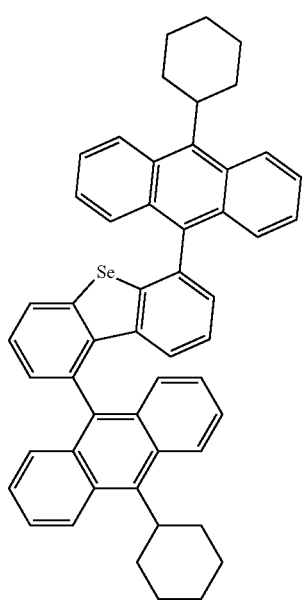
1250
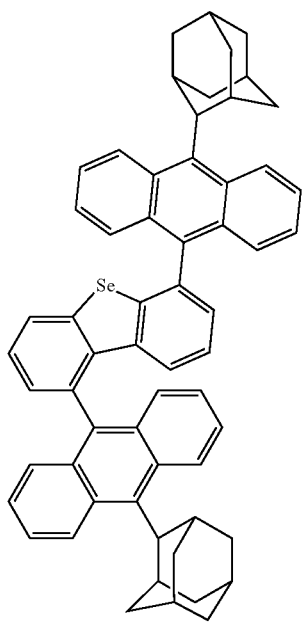
1251
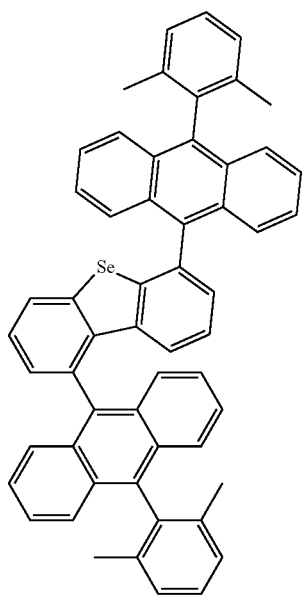

-continued
1252
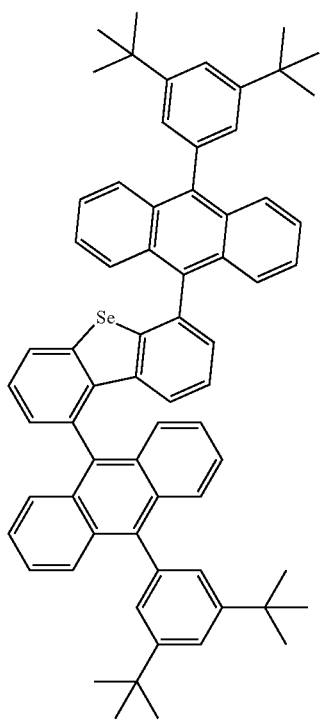
1253
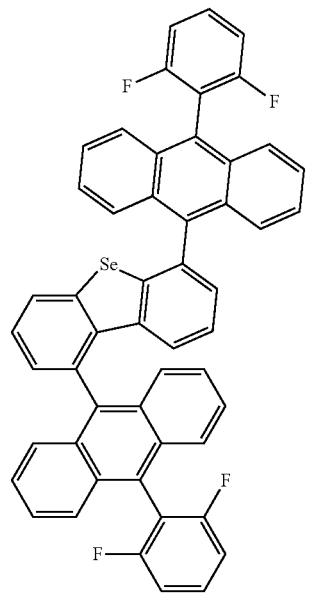
1254
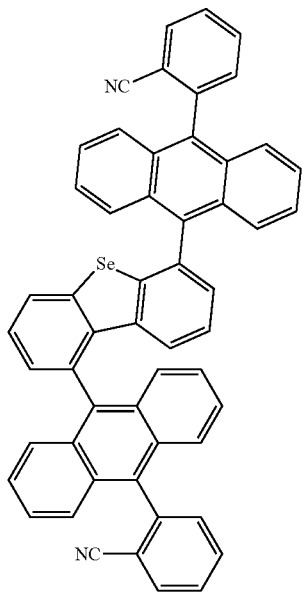
1255
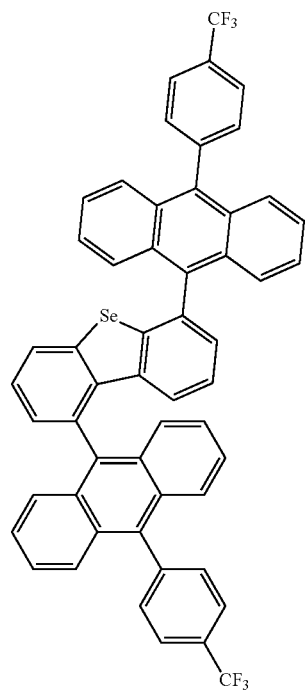

1923 1924
-continued
1256 1257
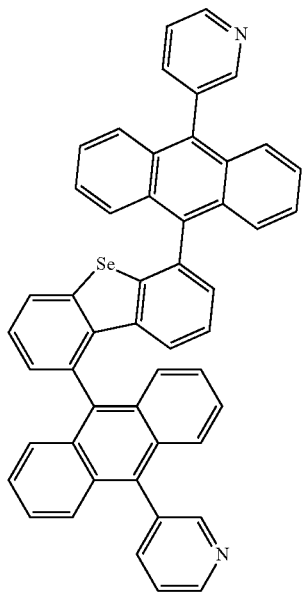
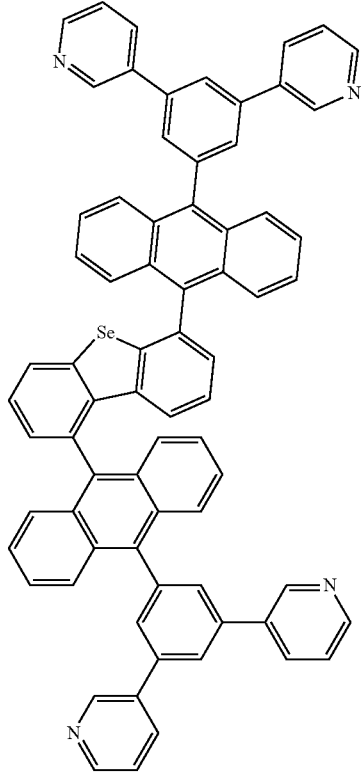
1258 1259
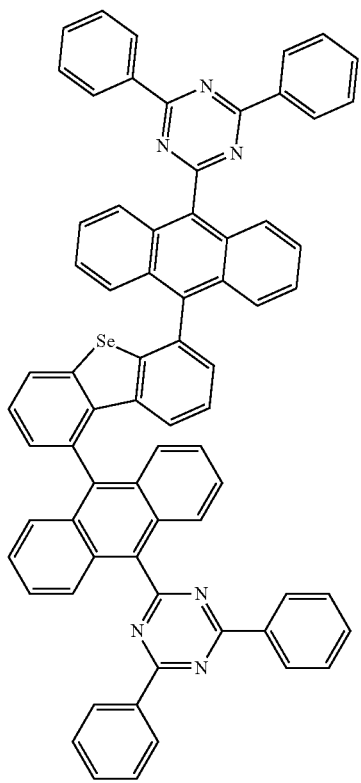

-continued
1260
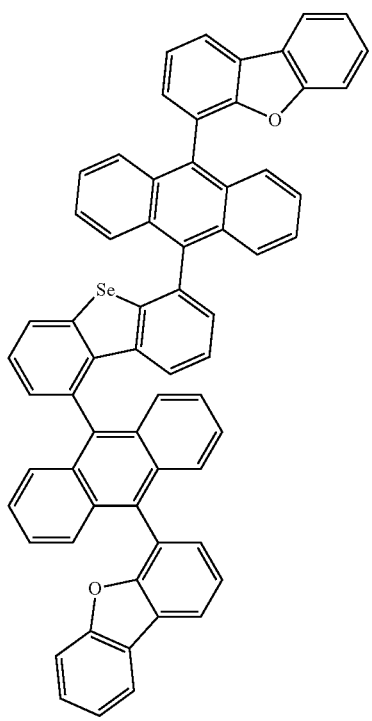
1261
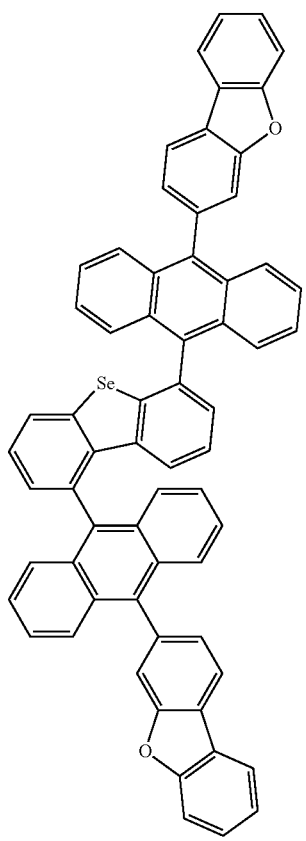
1262
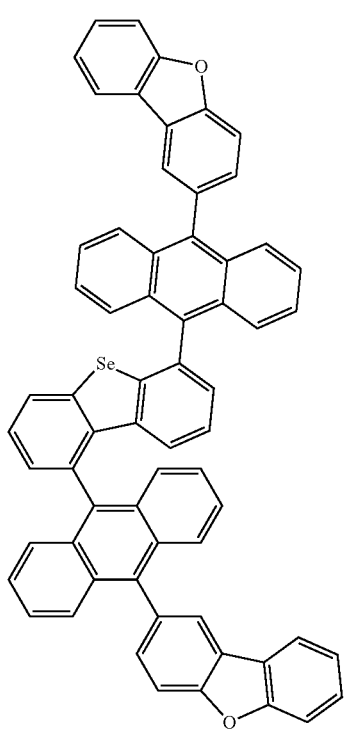
1263
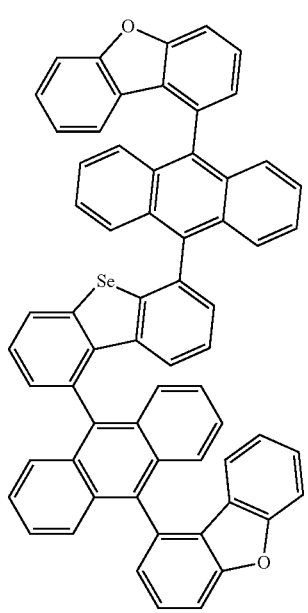

-continued
1264
1265
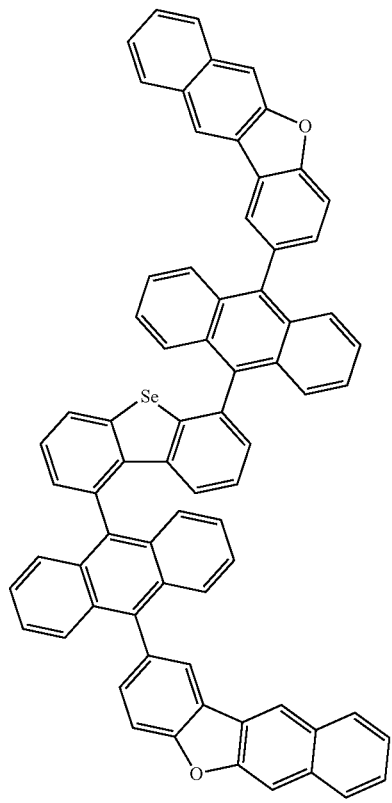
1266
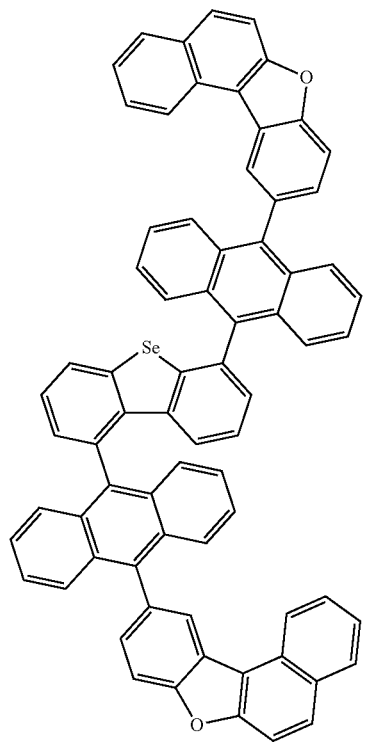
1267
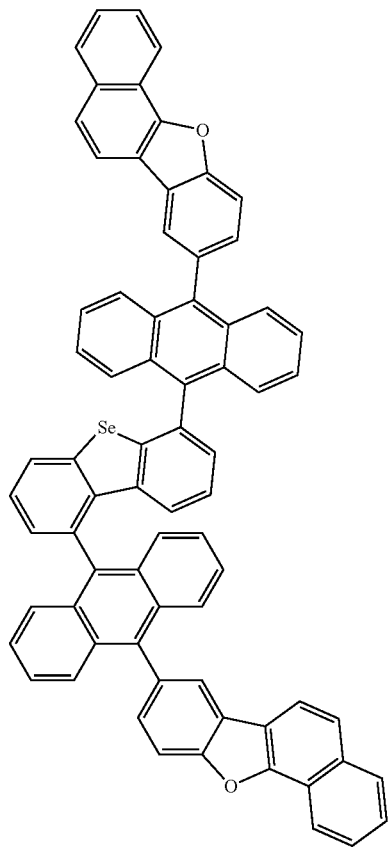

-continued
1268
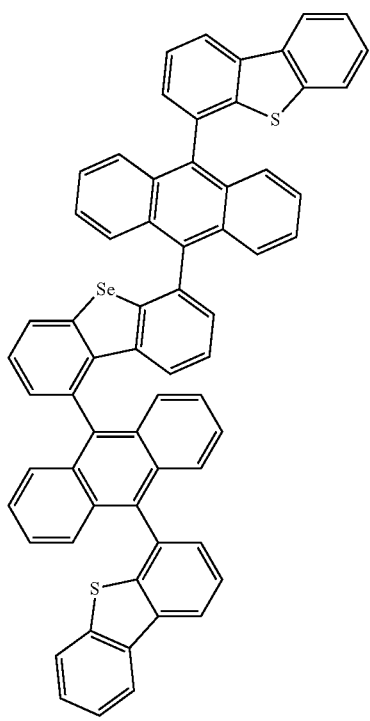
1269
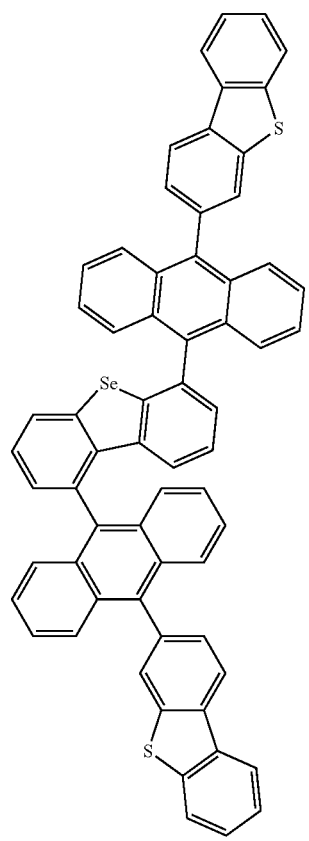
1270
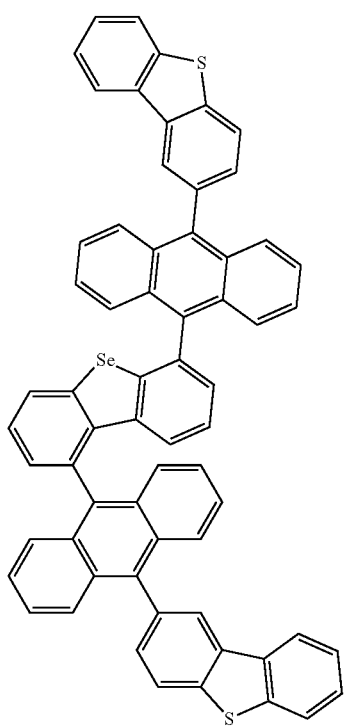
1271
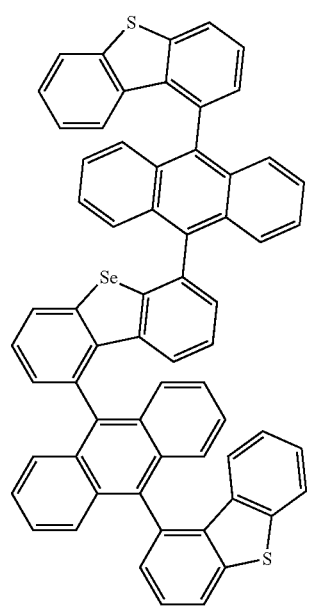

-continued
1272
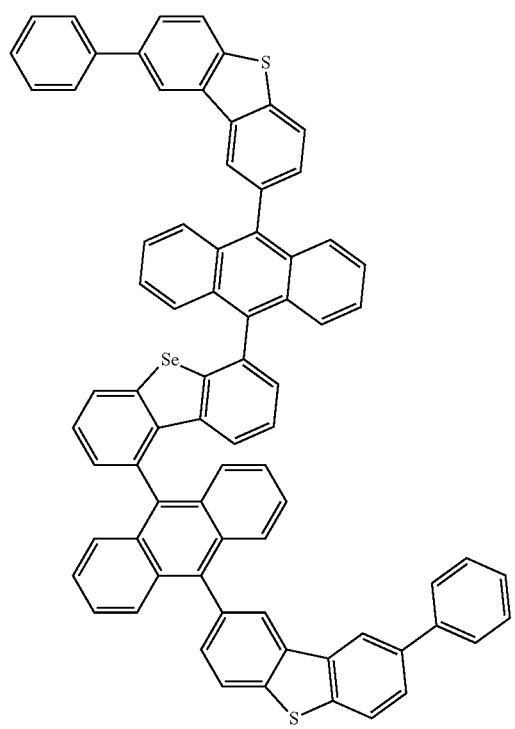
1273
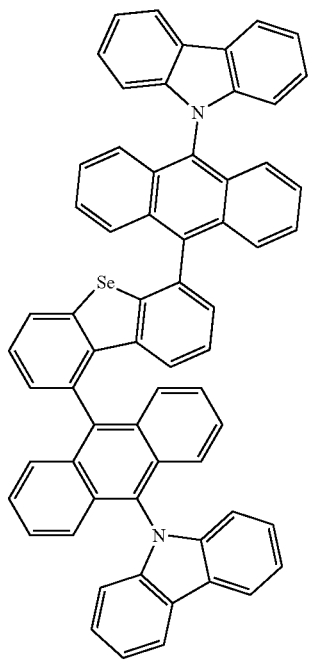
1274
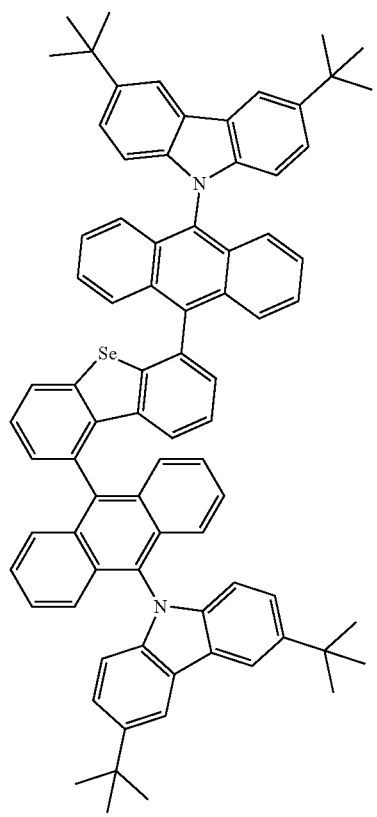
1275
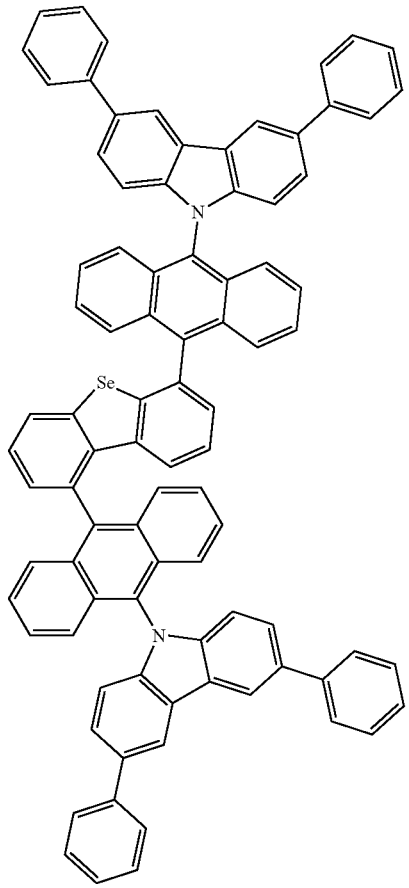

-continued
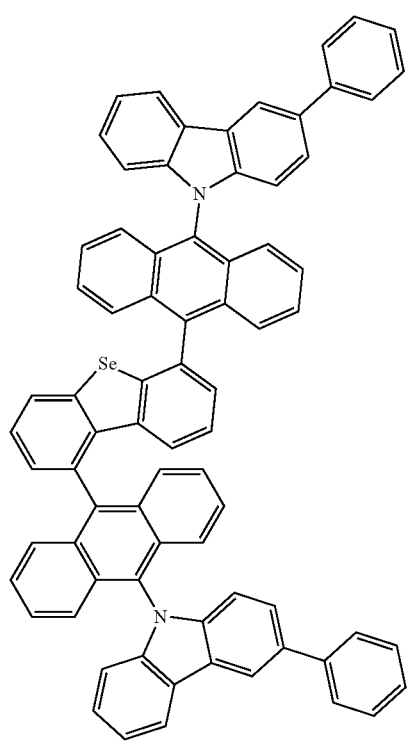
1276
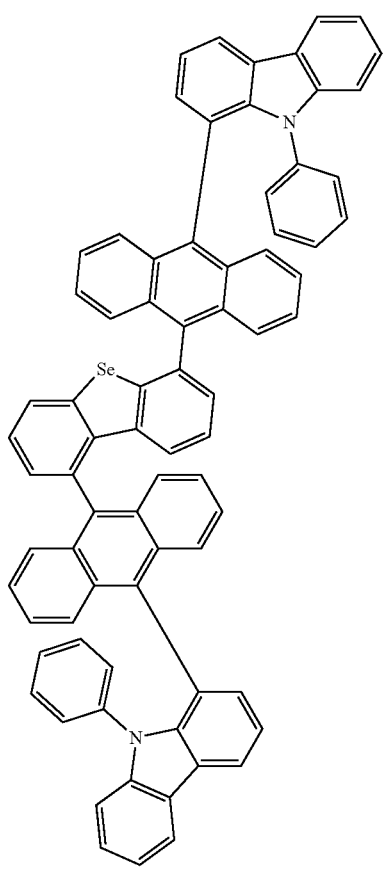
1277

1935 1936
-continued
1278
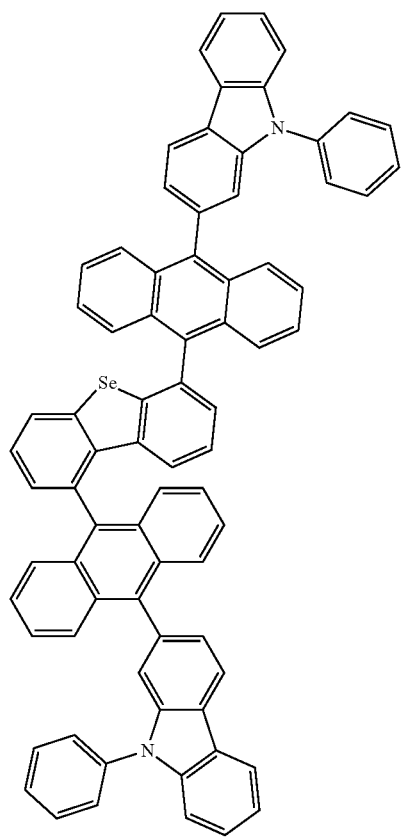
1279
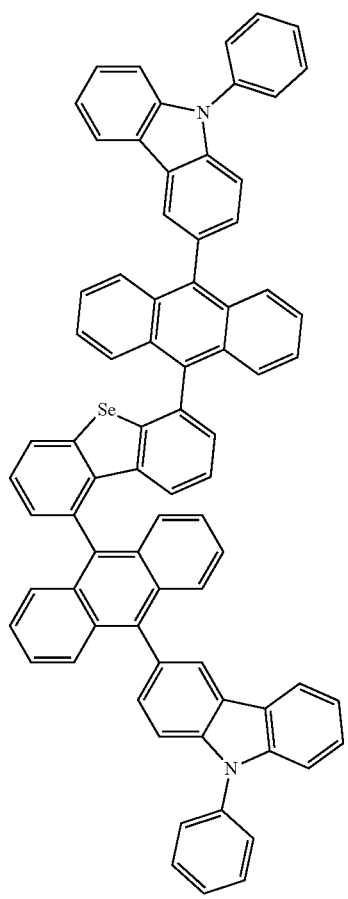
1280
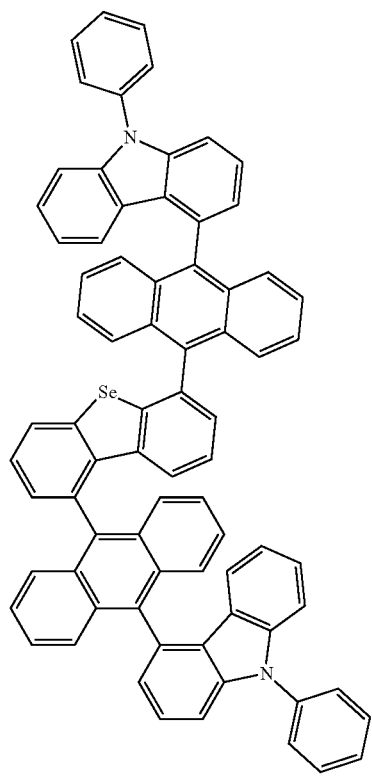
1281
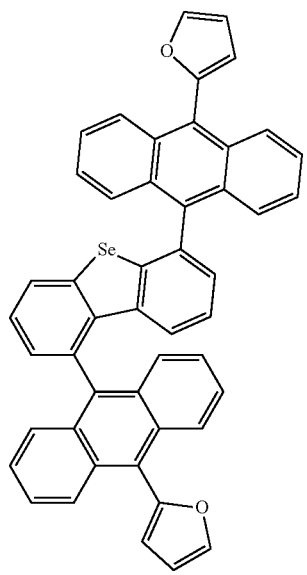

-continued
1282
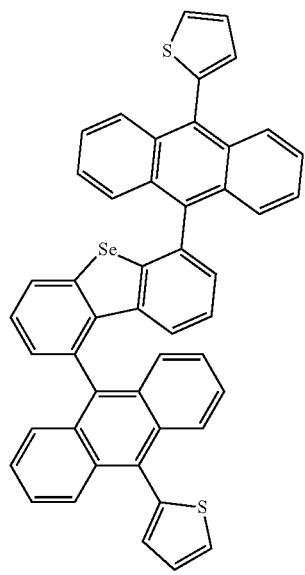
1283
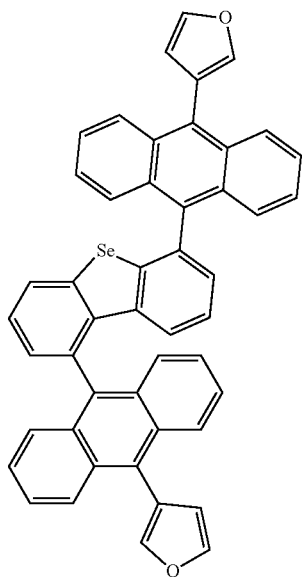
1284
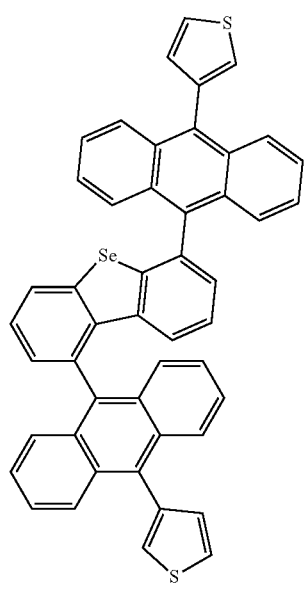
1285
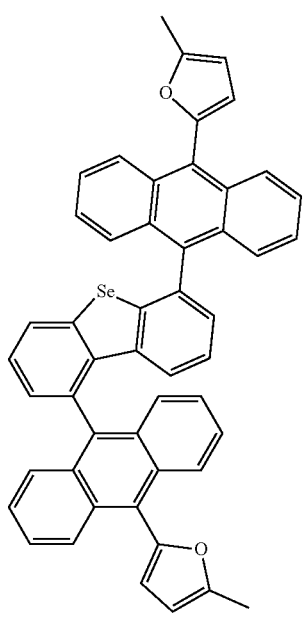

-continued
1286
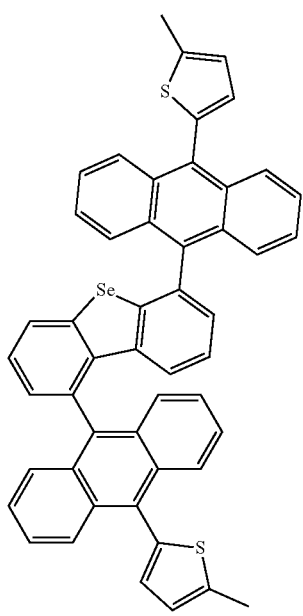
1287
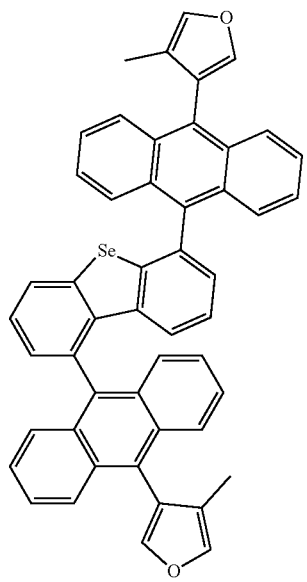
1288
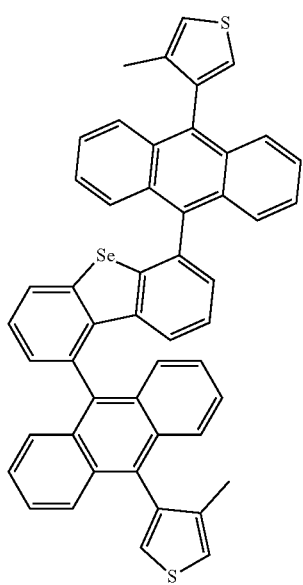
1289
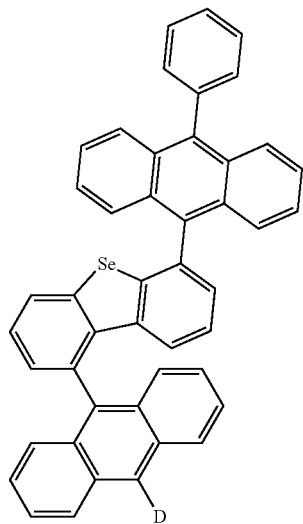

-continued
1290
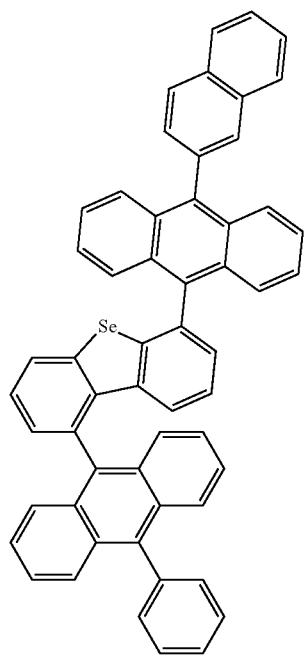
1291
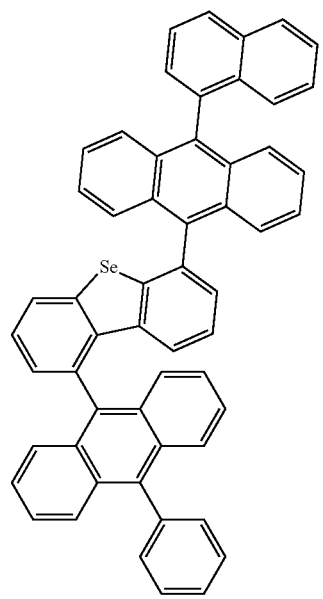
1292
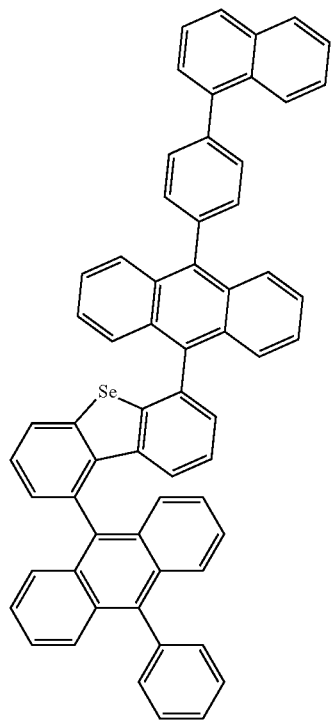
1293
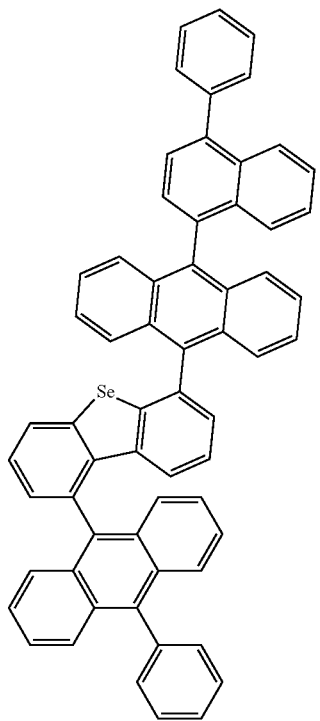

1943
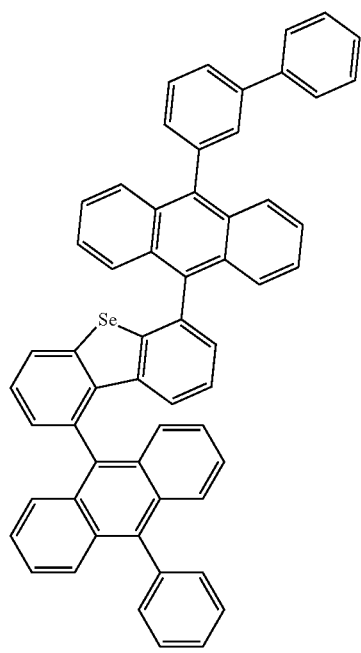
1294
-continued
1944
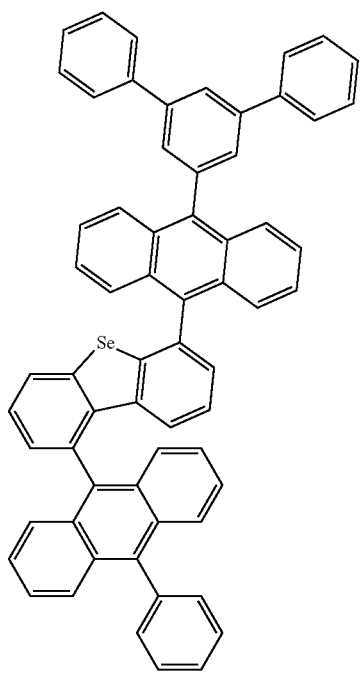
1295
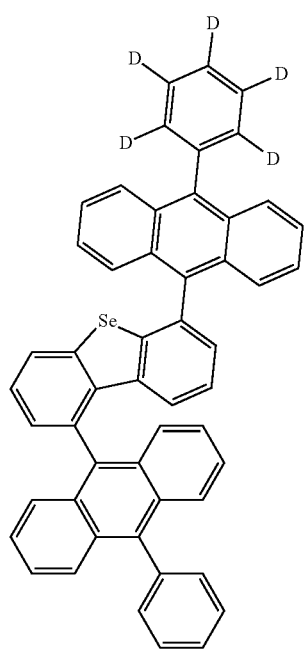
1296
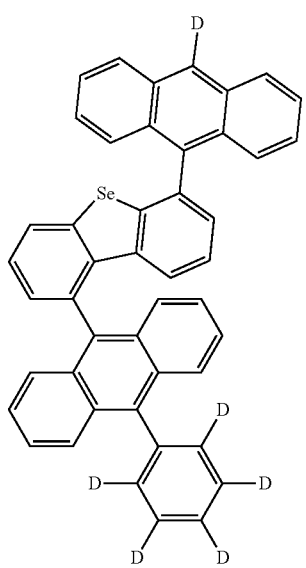
1297

-continued
1298 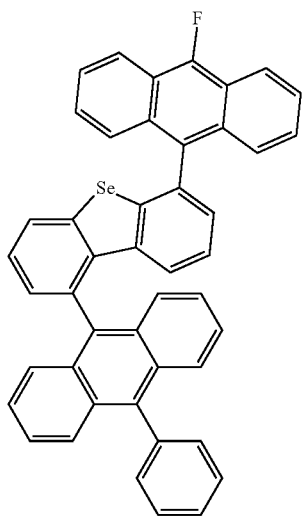 1299 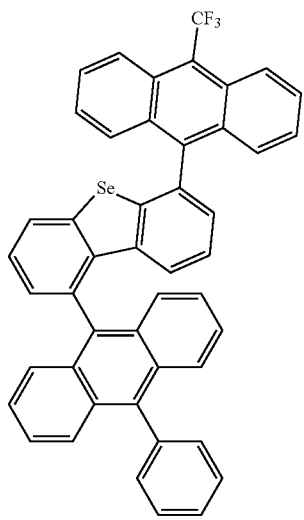
1300 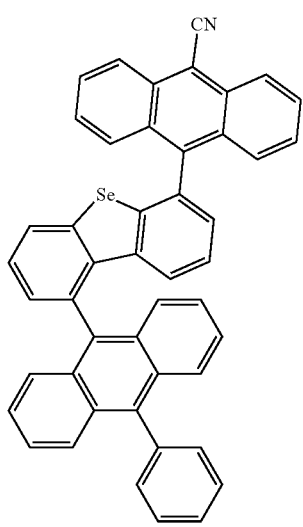 1301 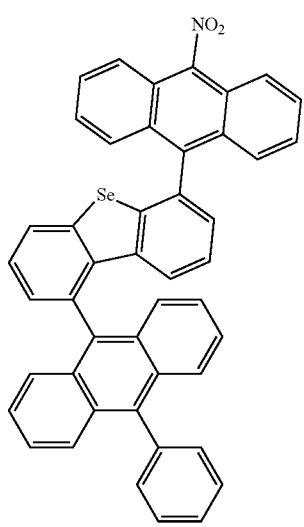
1302 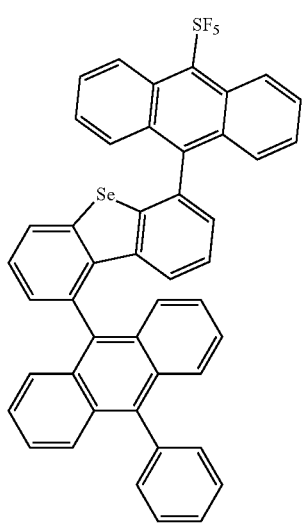 1303 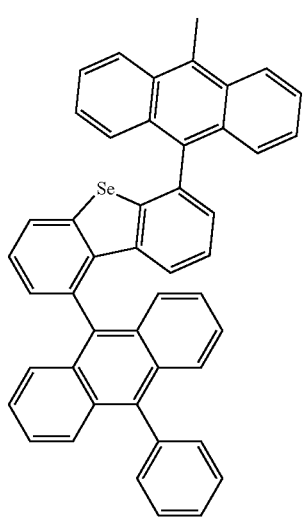

-continued
1947
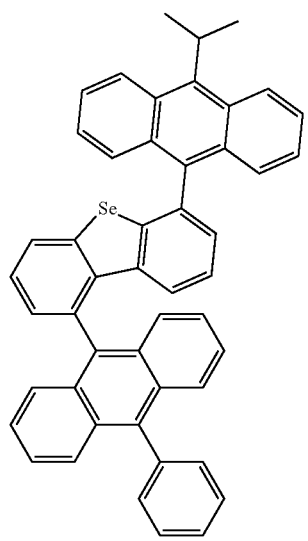
1948
1304
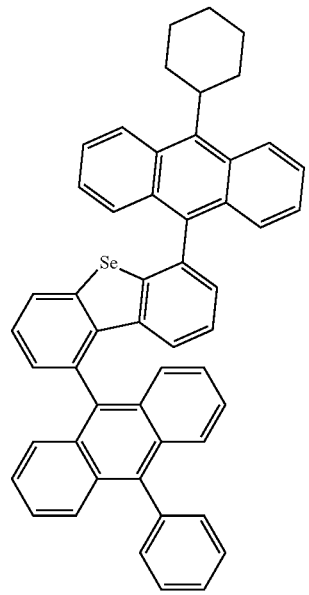
1305
1306
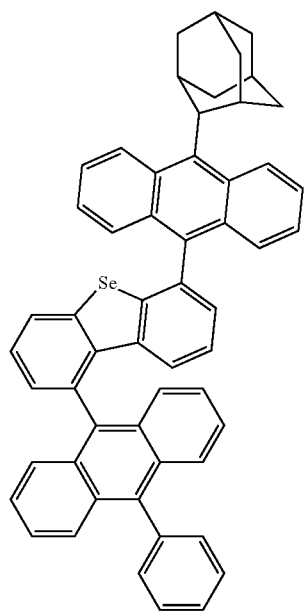
1307
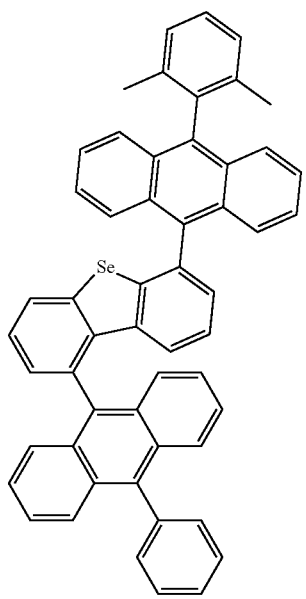

-continued
1308
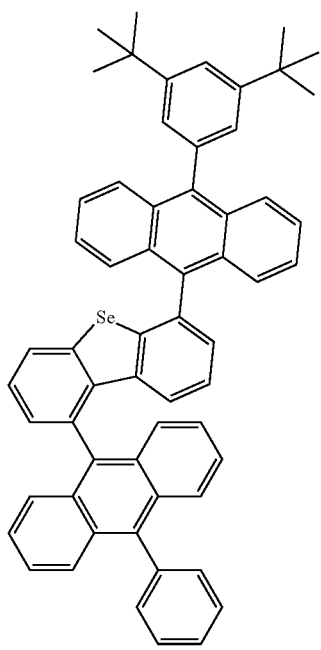
1309
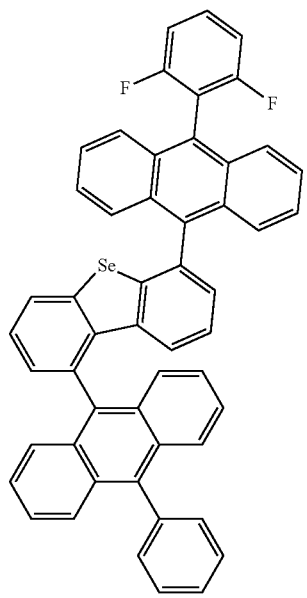
1310
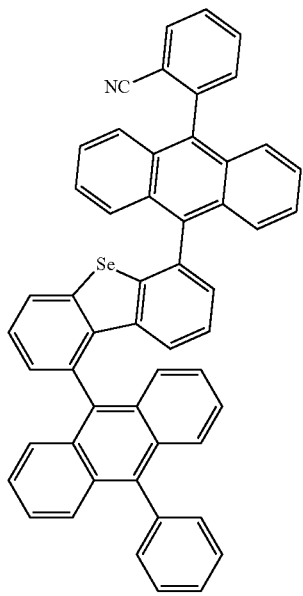
1311
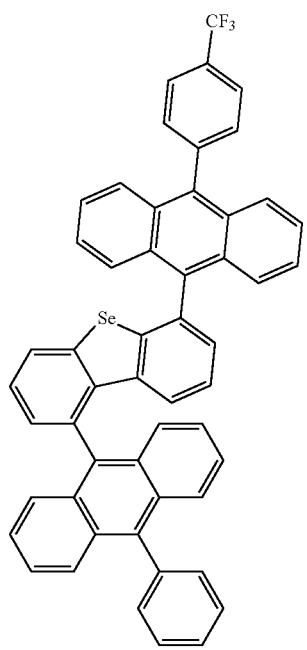

1951
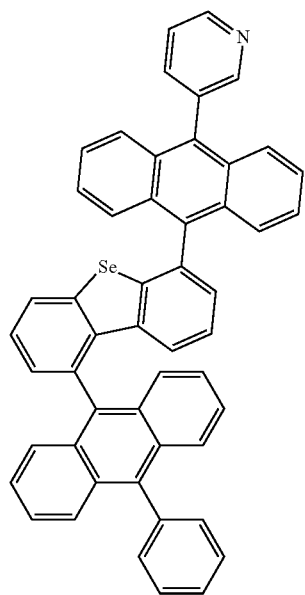
1952
-continued
1312
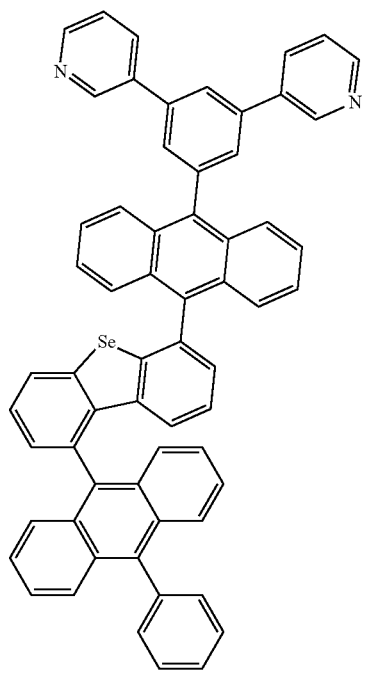
1313
1314
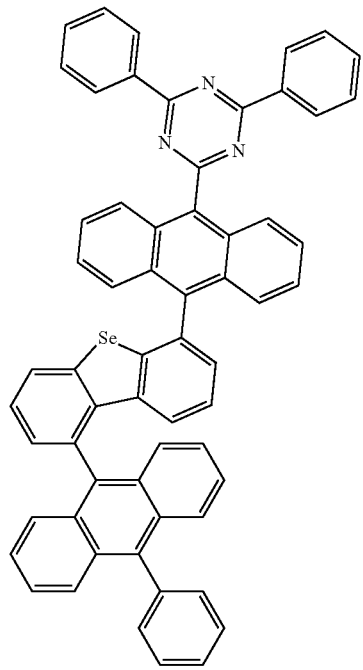
1315
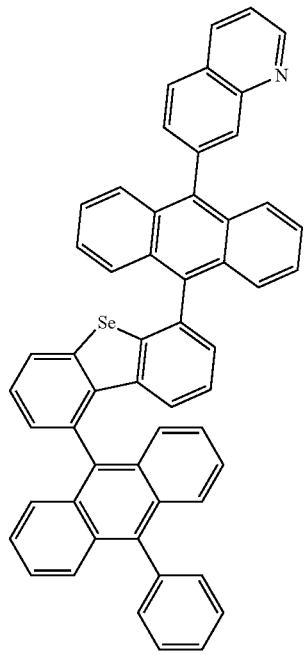

-continued
1316
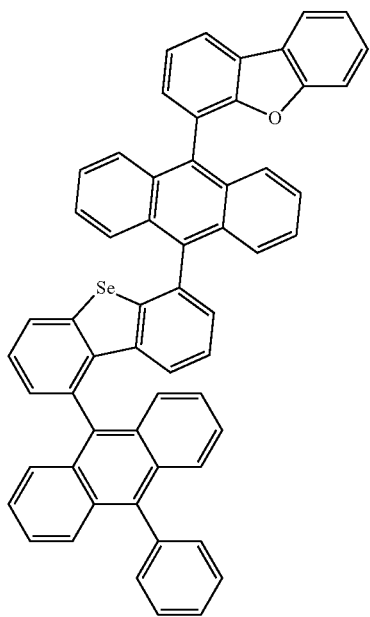
1317
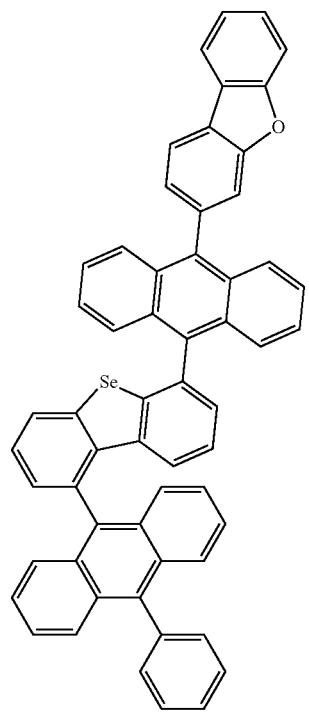
1318
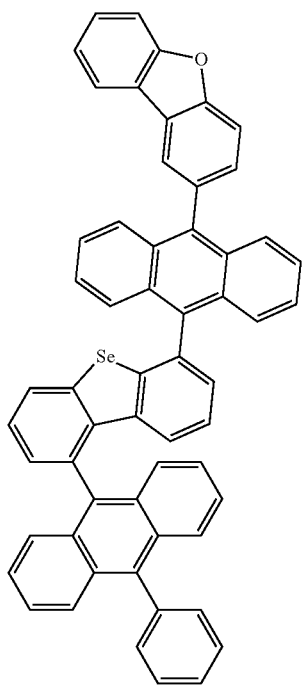
1319
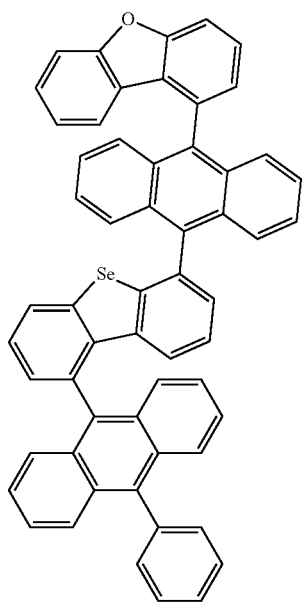

-continued
1955
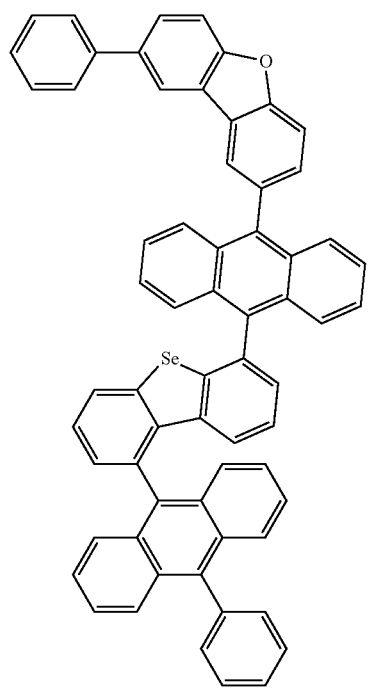
1956
1320
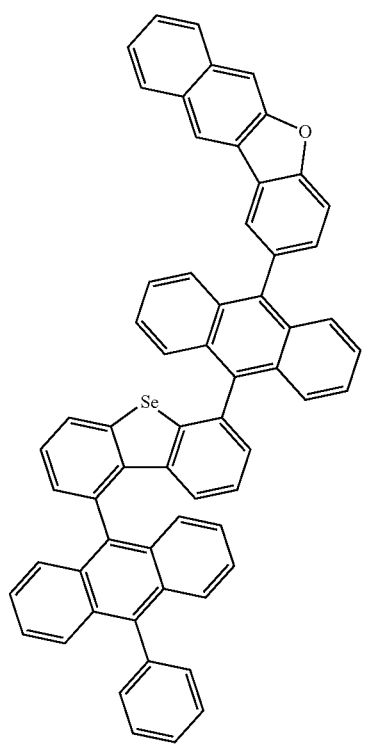
1321
1322
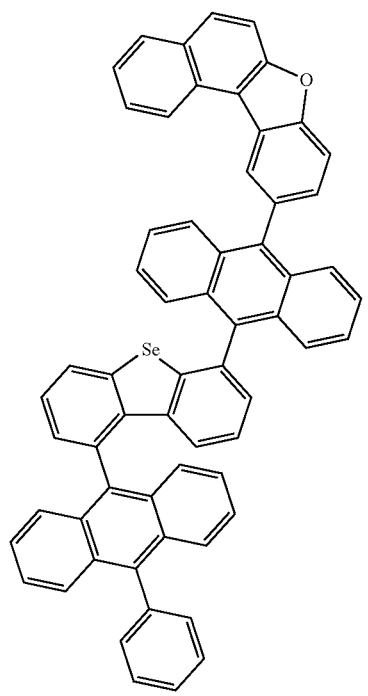
1323
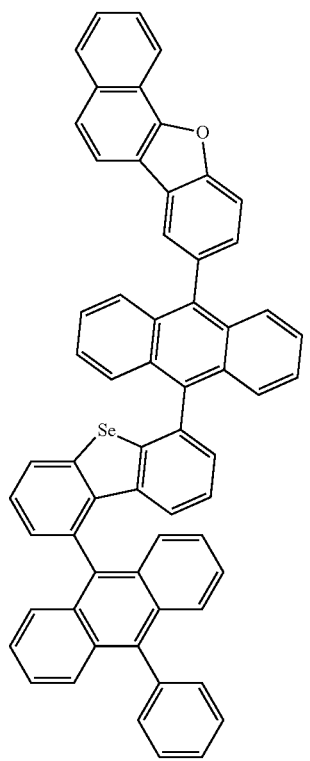

-continued
1324
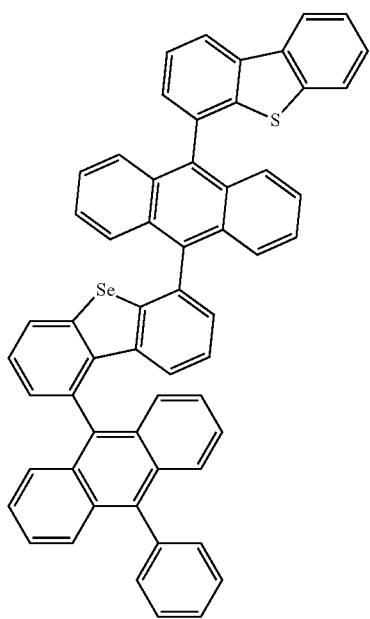
1325
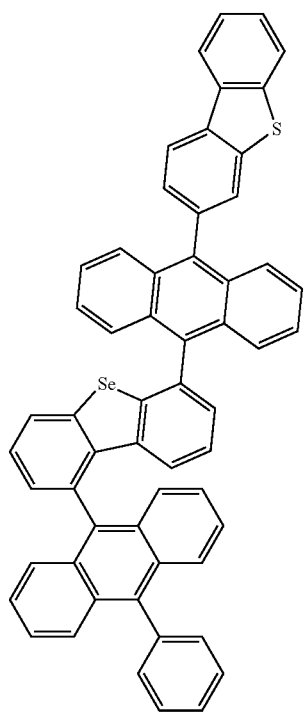
1326
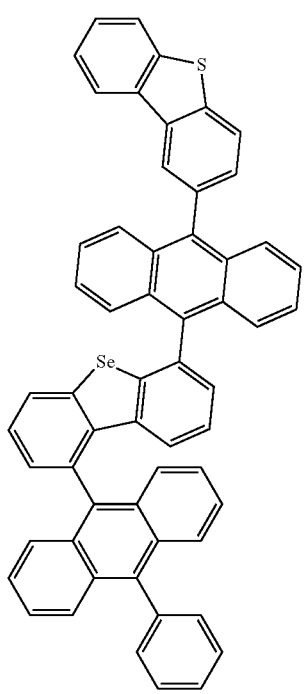
1327
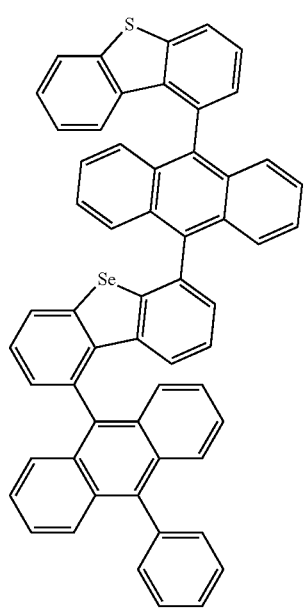

-continued
1959
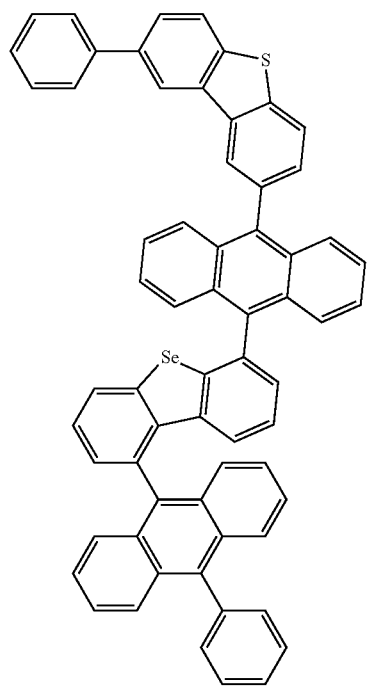
1328
1960
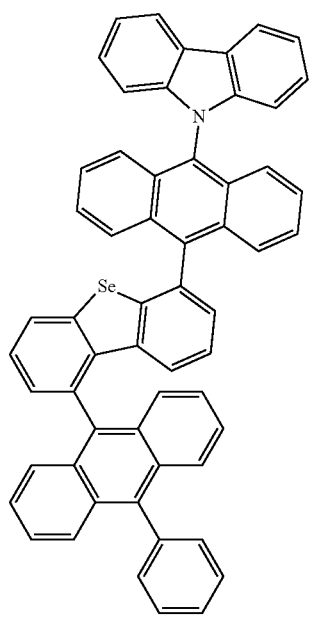
1329
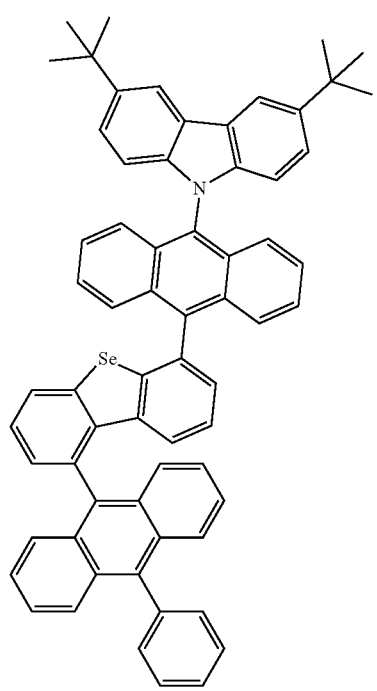
1330
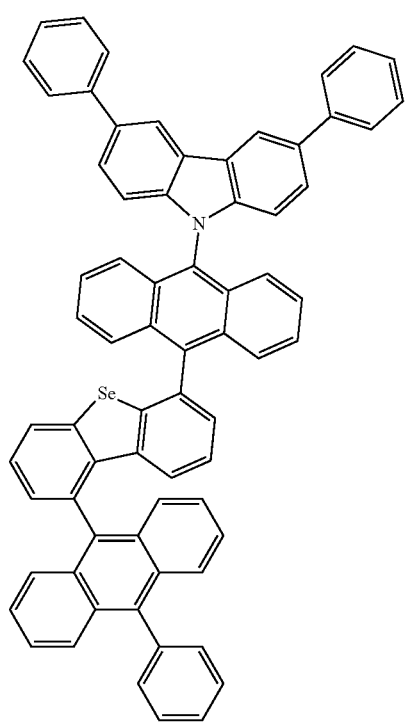
1331

-continued
1961
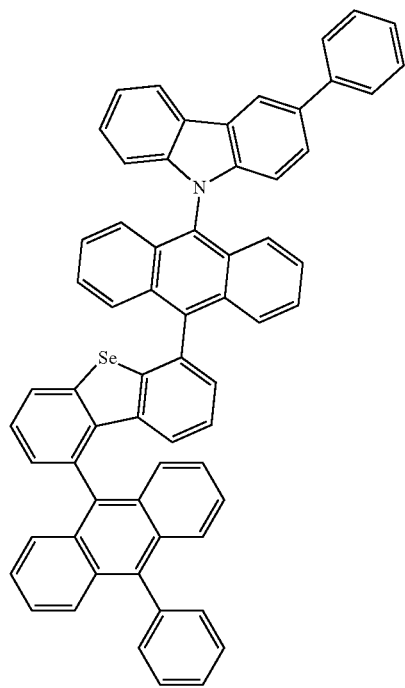
1962
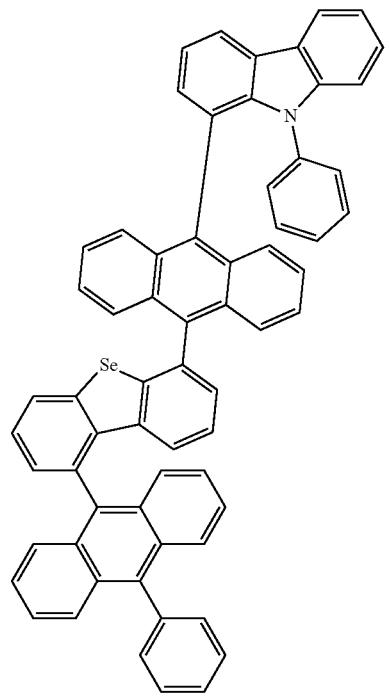
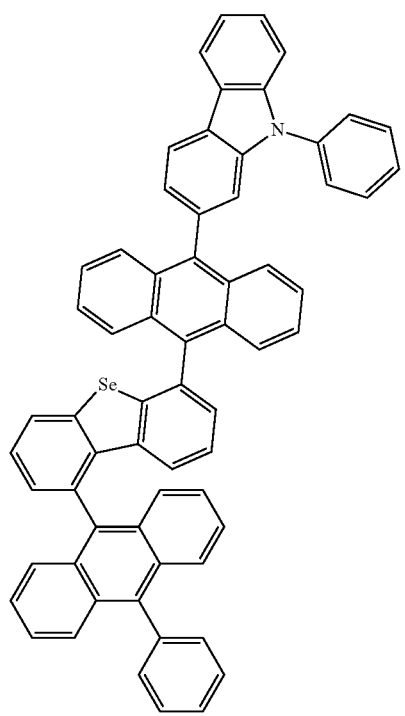
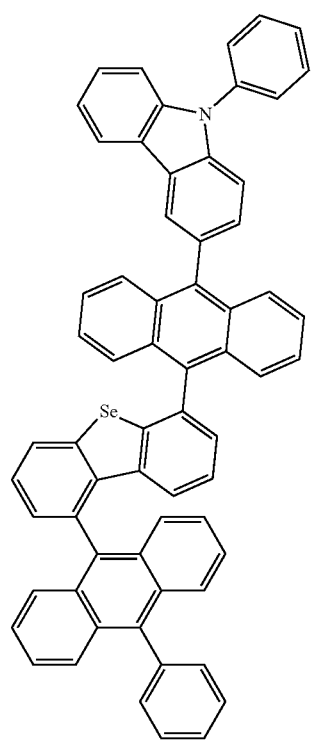

-continued
1336
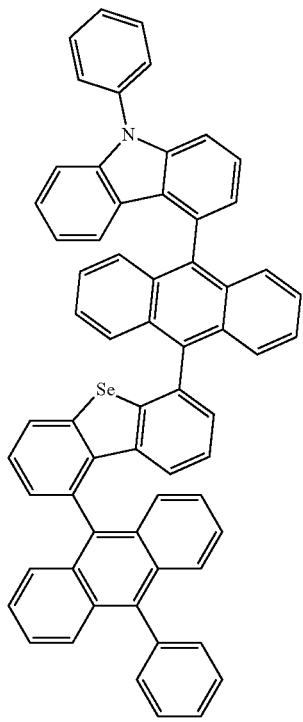
1963
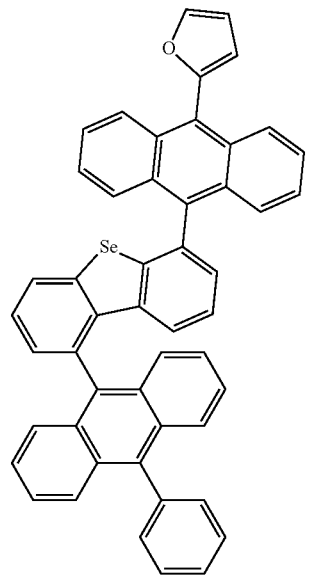
1337
1338
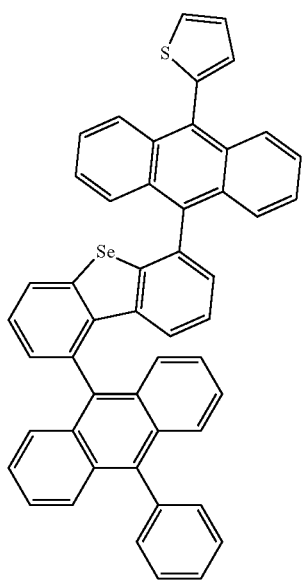
1339
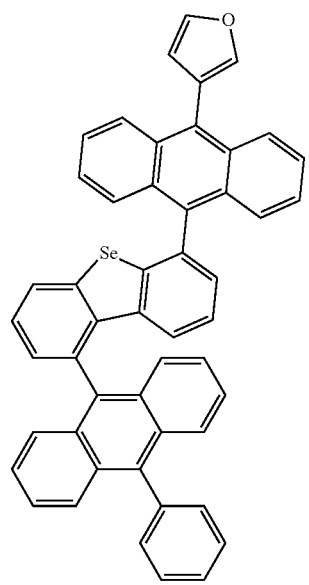
1964

-continued
1965
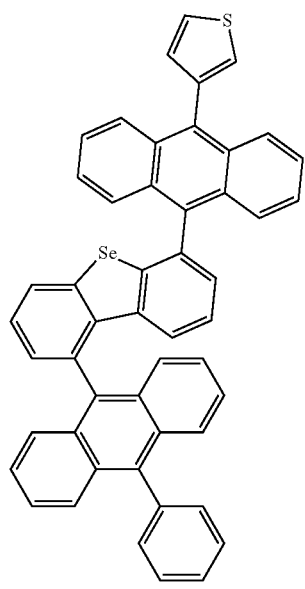
1966
1340
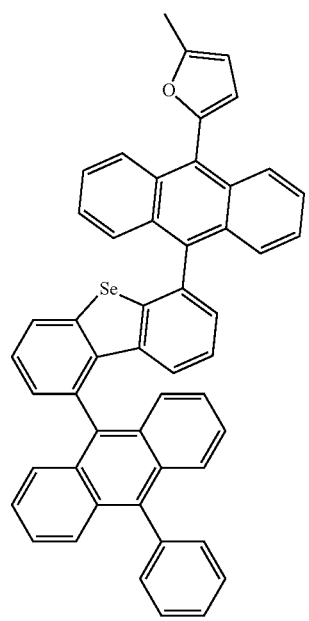
1341
1342
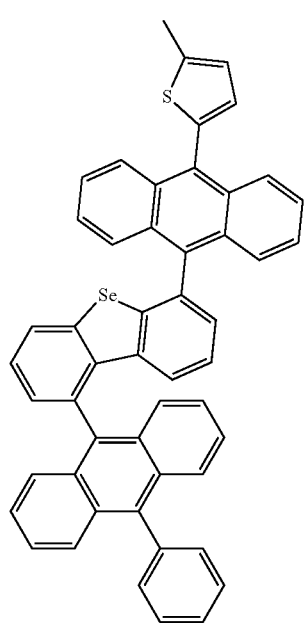
1343
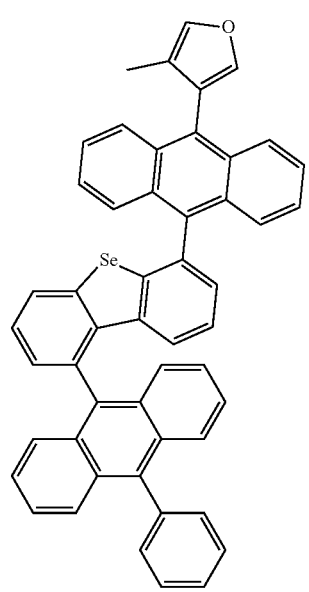

-continued
1344
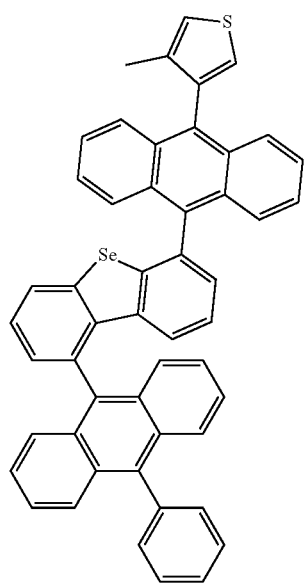
1345
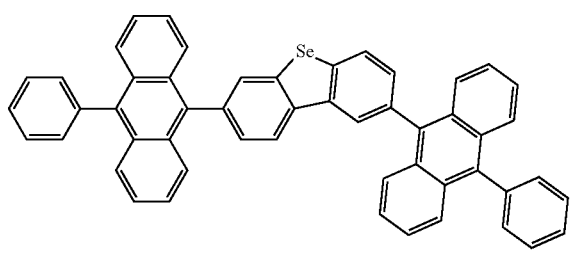
1346
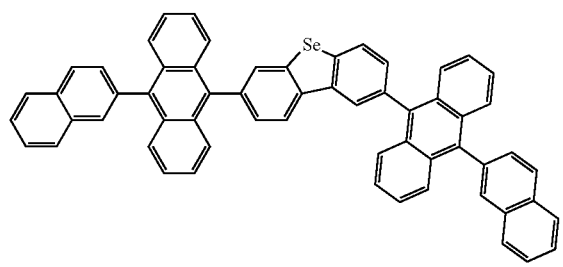
1347
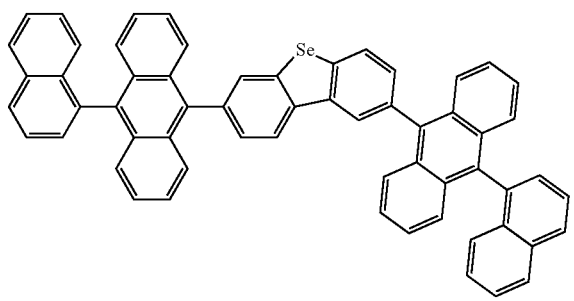
1348
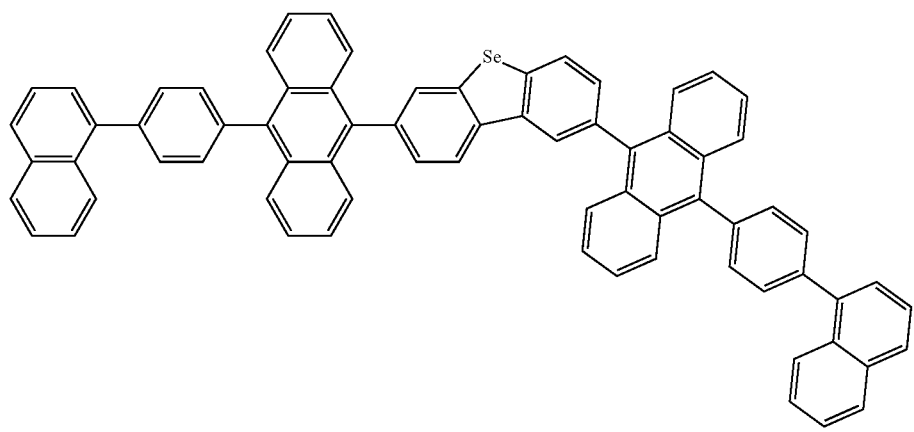

-continued
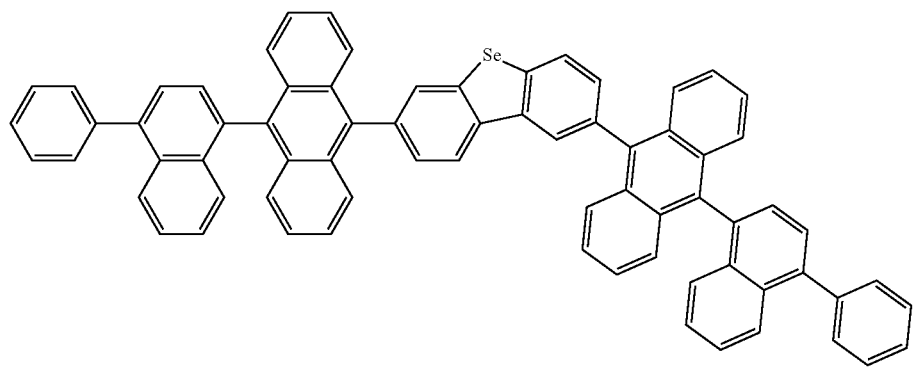
1349
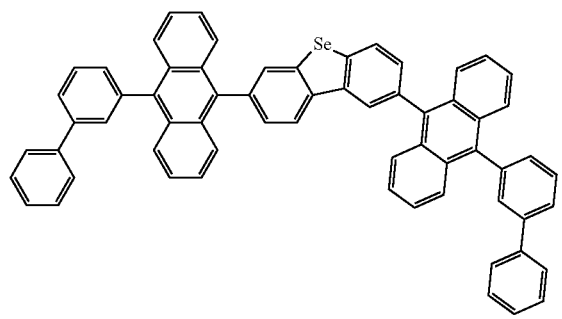
1350
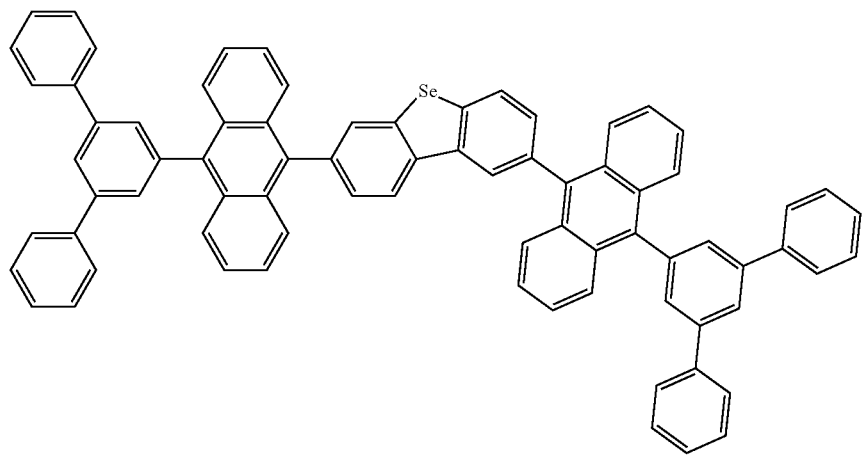
1351
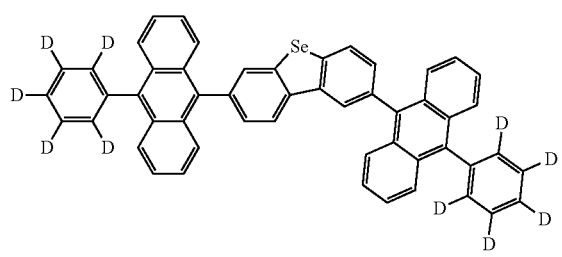
1352
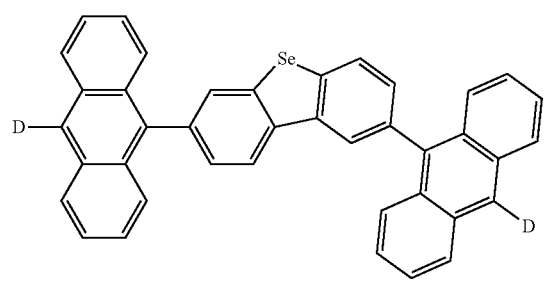
1353

1971                                           1972
-continued
1354
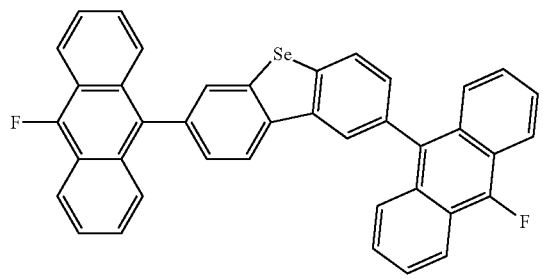
1355
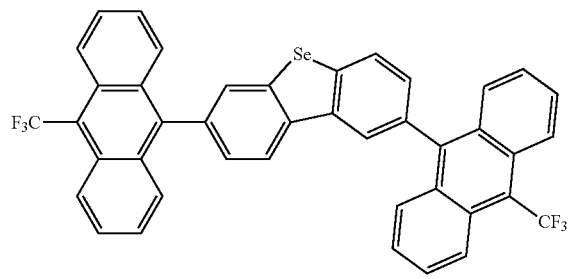
1356
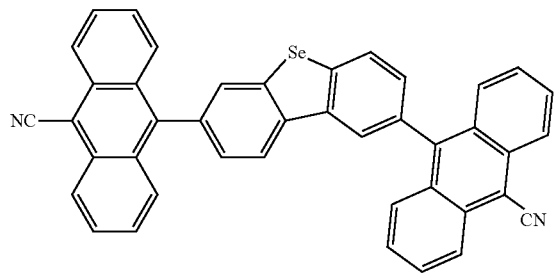
1357
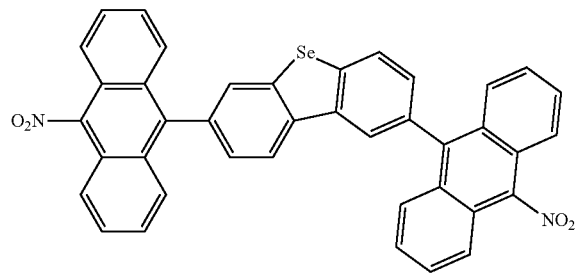
1358
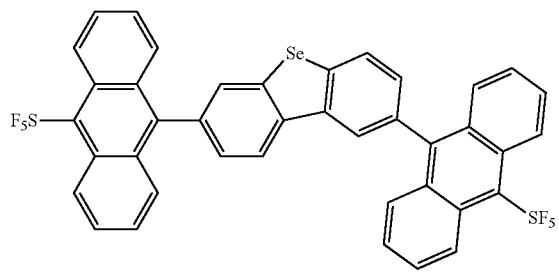
1359
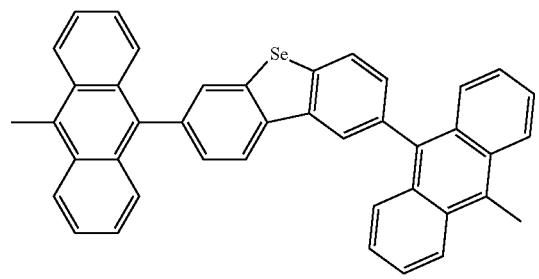
1360
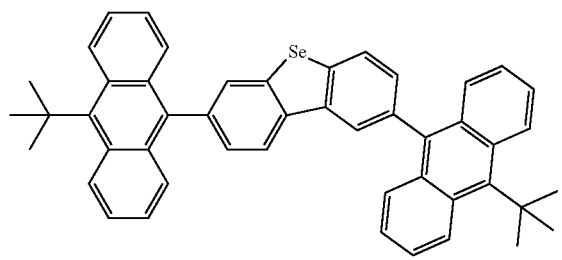
1361
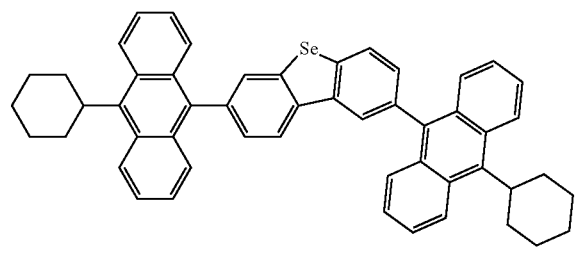
1362
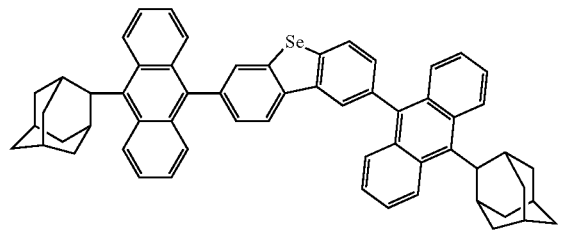
1363
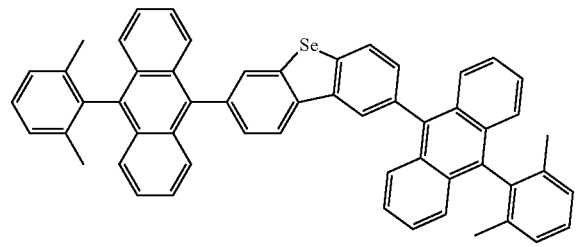

1973 1974
-continued
1364
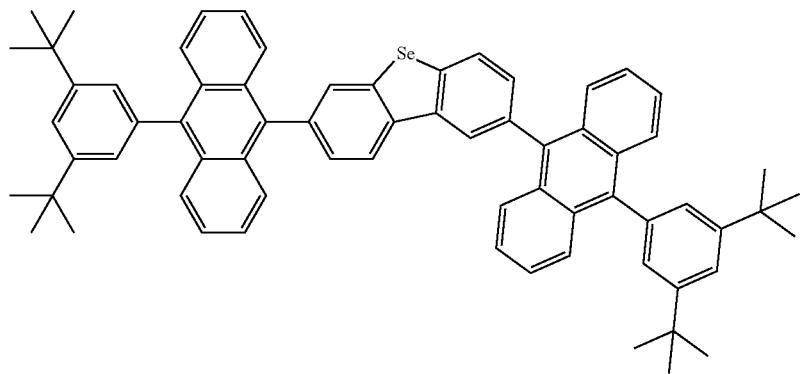
1365 1366
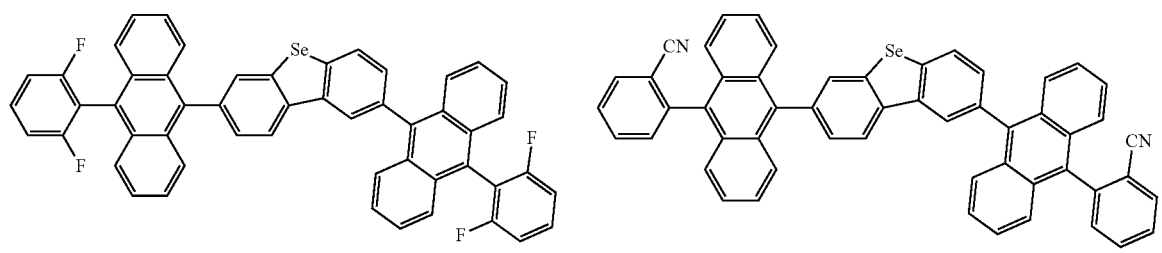
1367
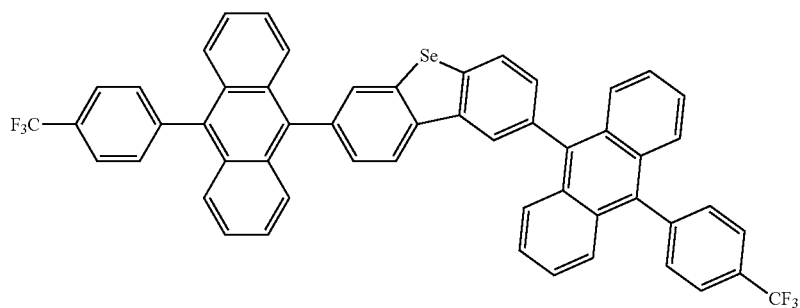
1368
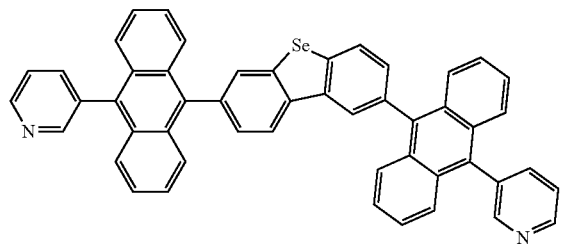

1975 1976
1369
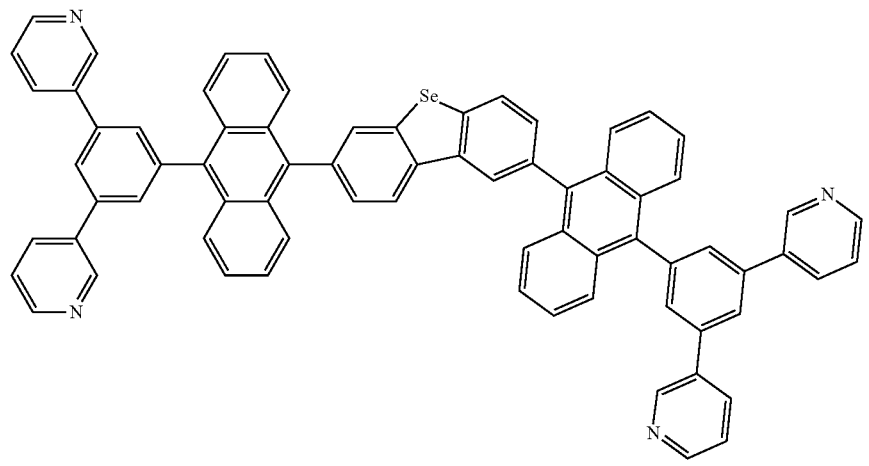
1370
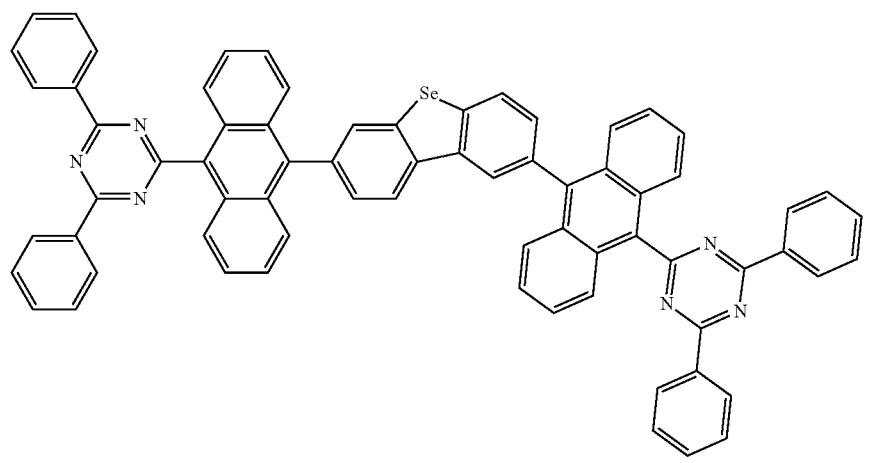
1371
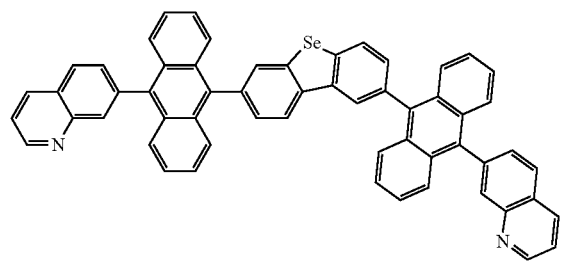
1372
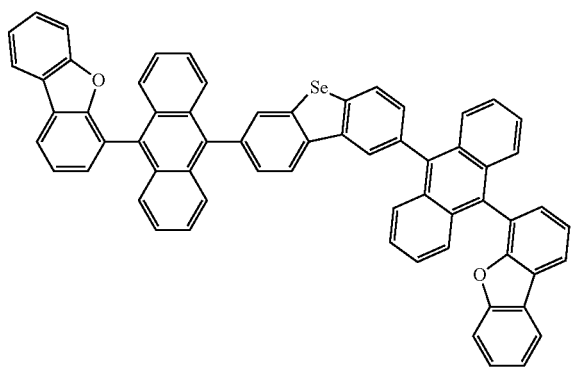

-continued
1373
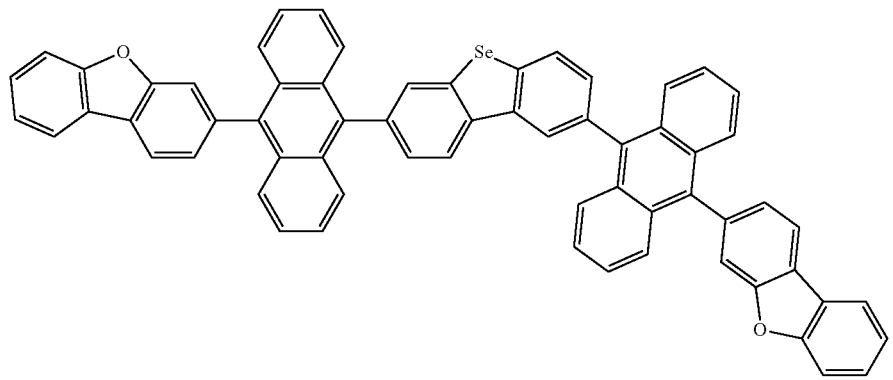
1374
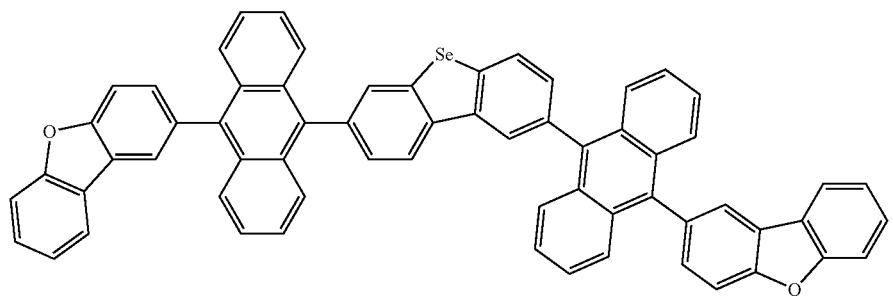
1375
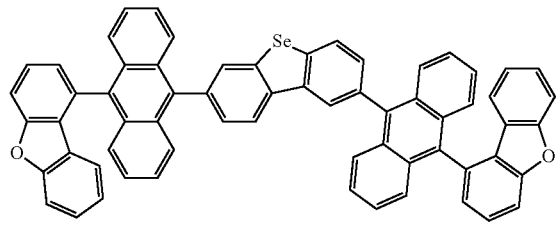
1376
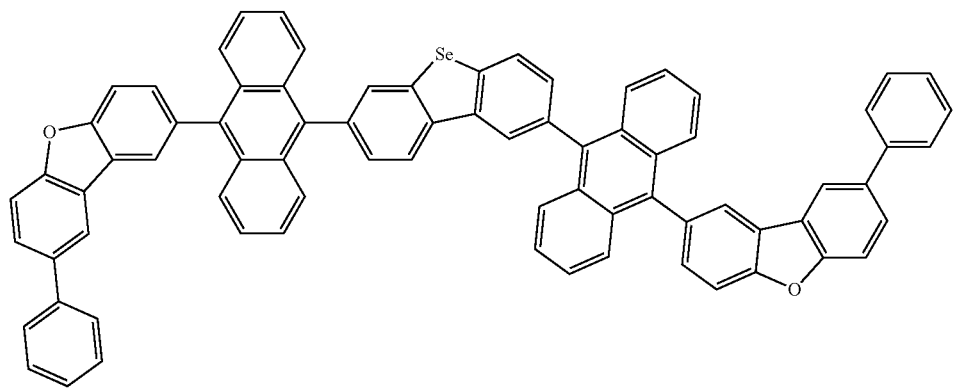

-continued
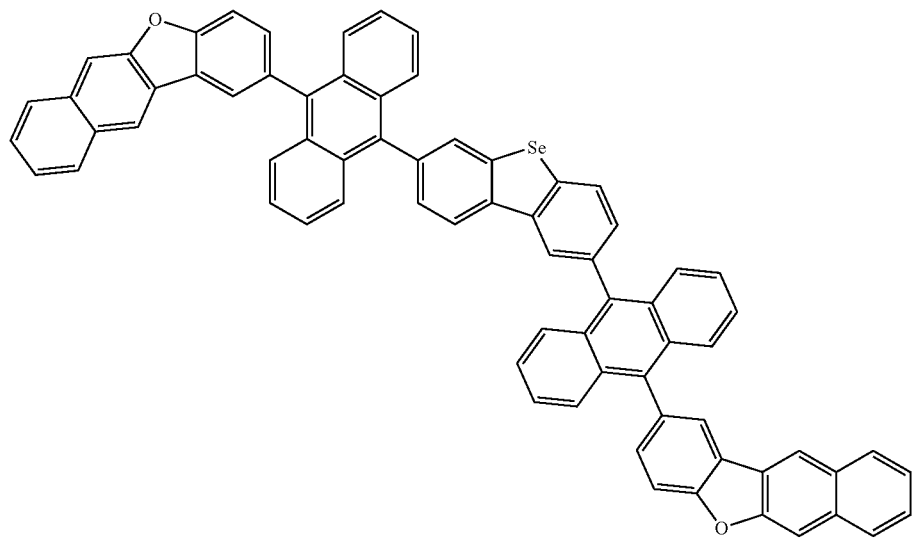

-continued
1380
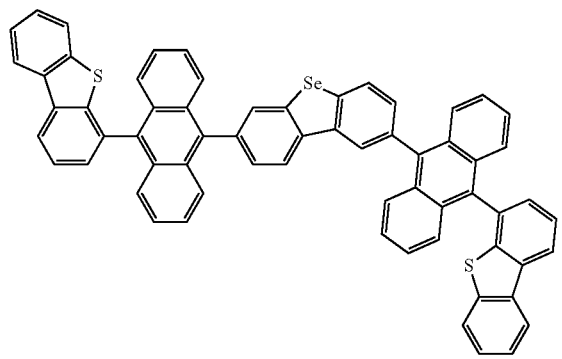
1381
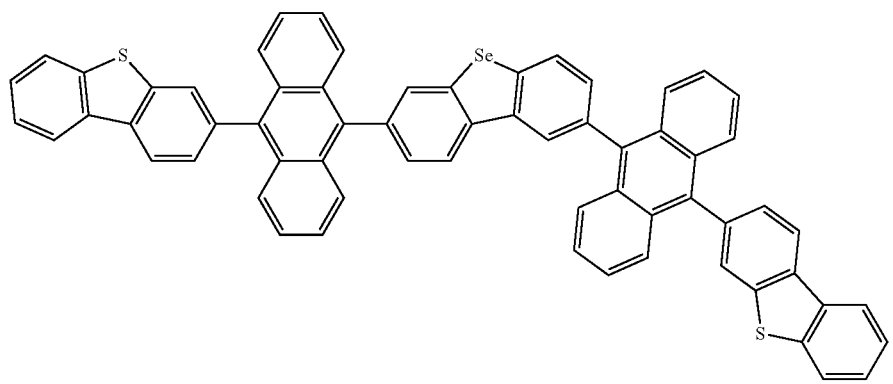
1382
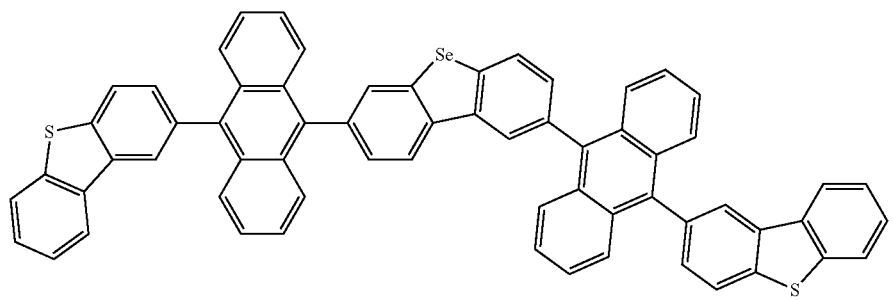
1383
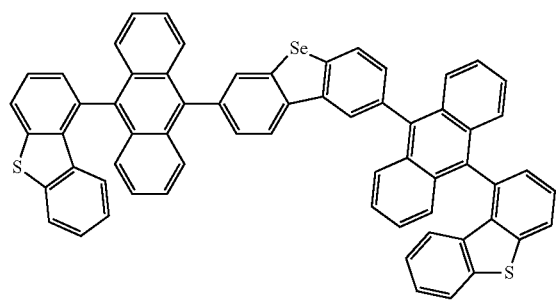

1983      1984
1384
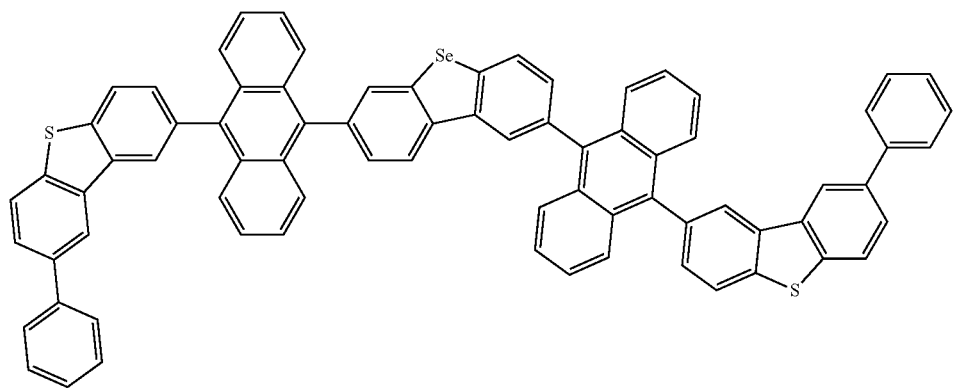
1385
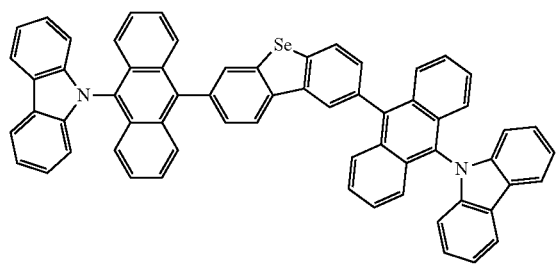
1386
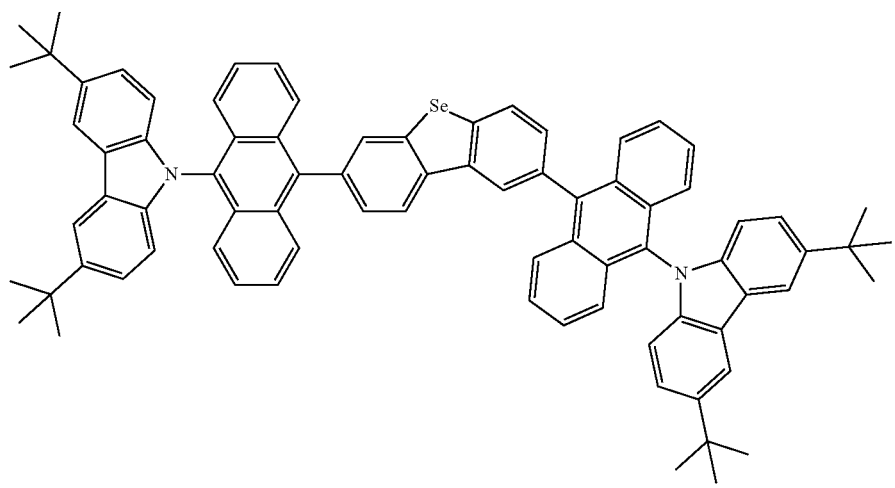

-continued
1985
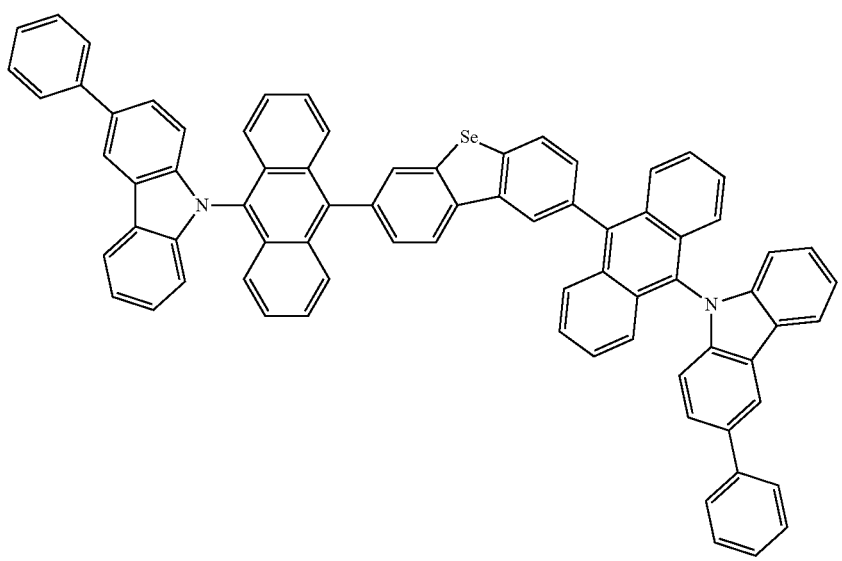
1388
1986
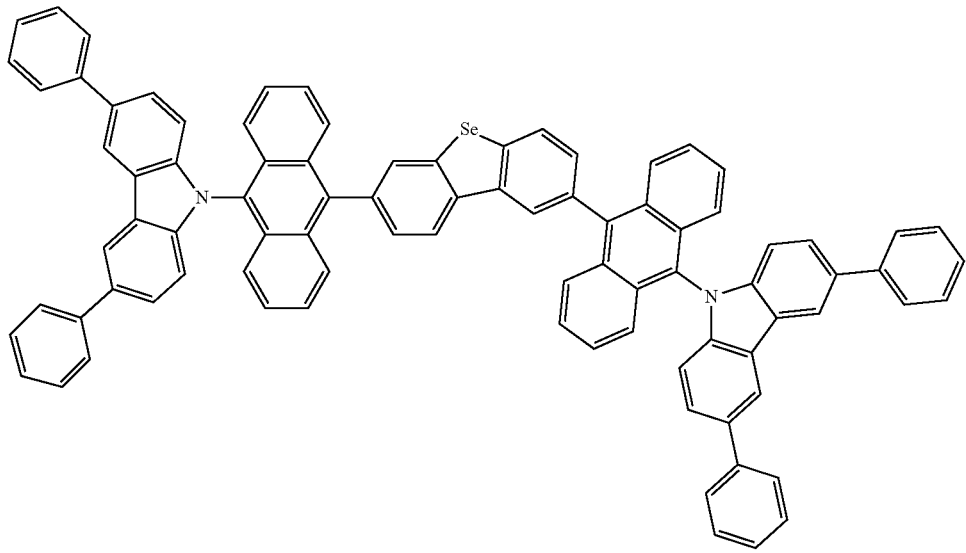
1387
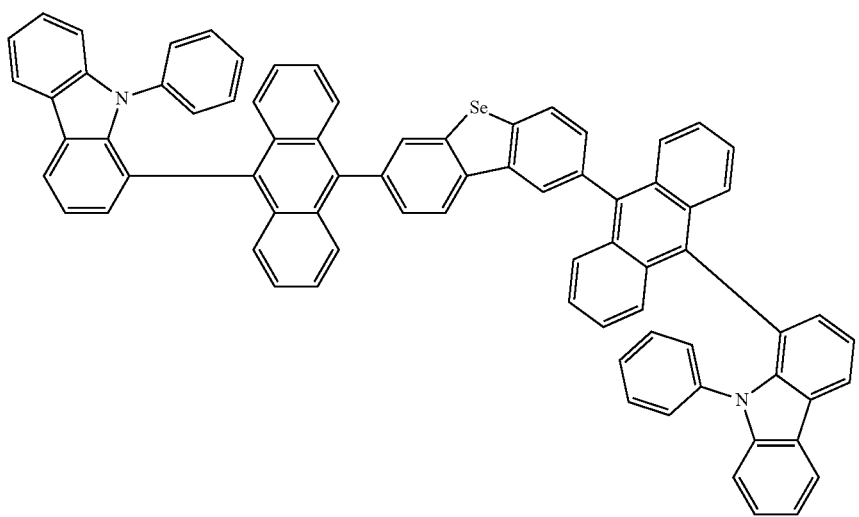
1389

1987
1988
-continued
1390
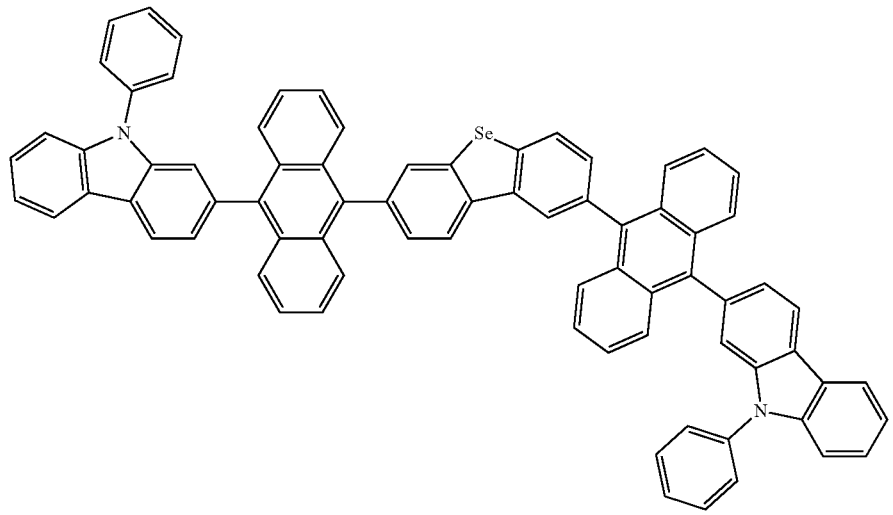
1391
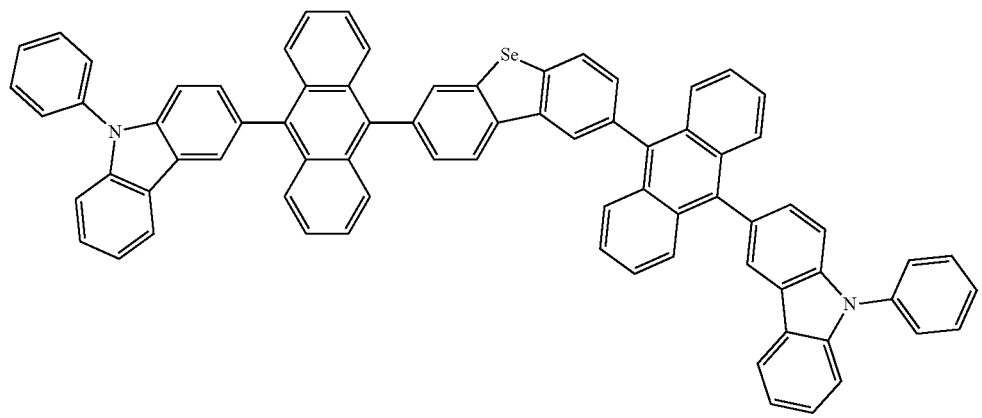
1392
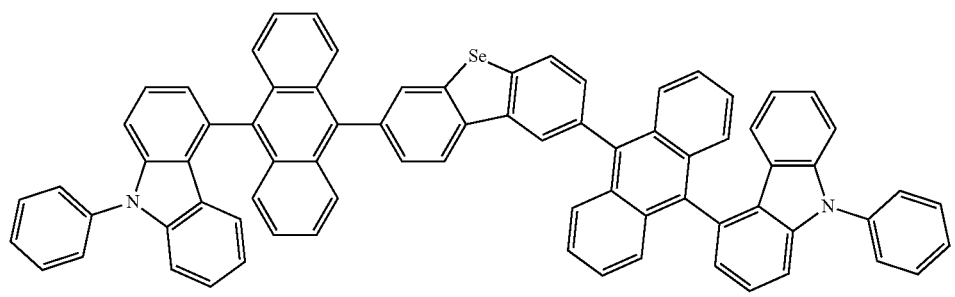
1393 1394
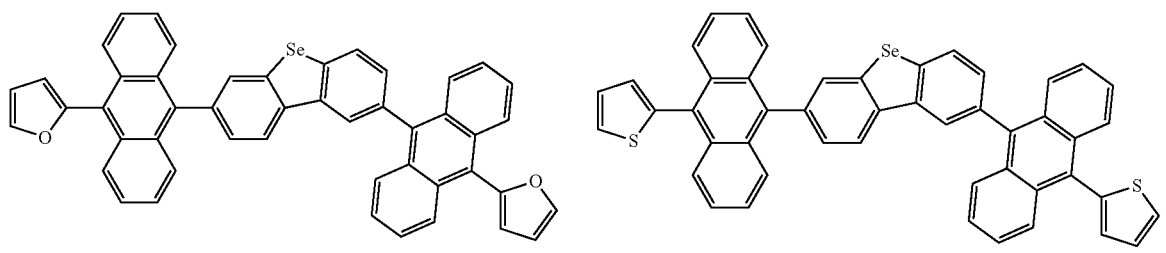

| 1989 | 1990 |
|---|---|
| 1395 | 1396 |
| 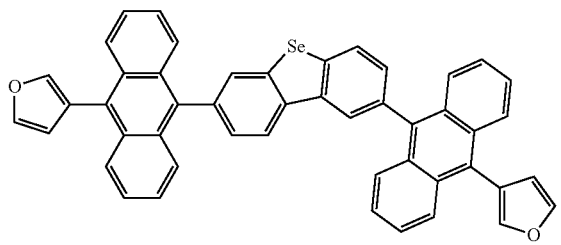 | 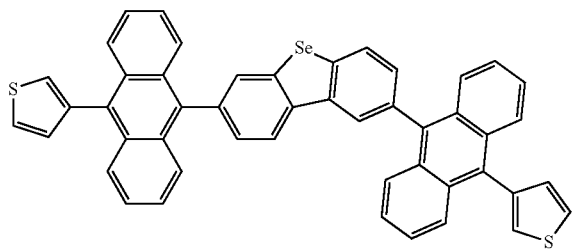 |
| 1397 | 1398 |
| 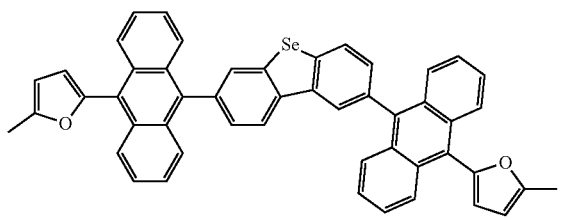 | 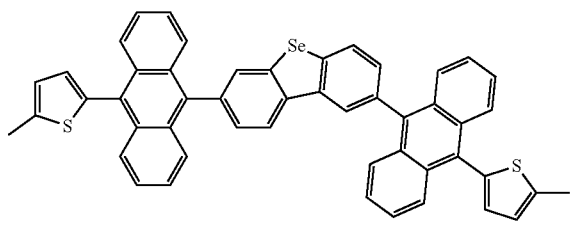 |
| 1399 | 1400 |
| 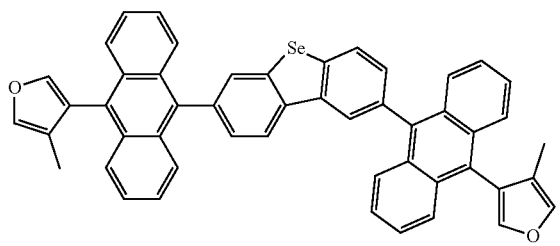 | 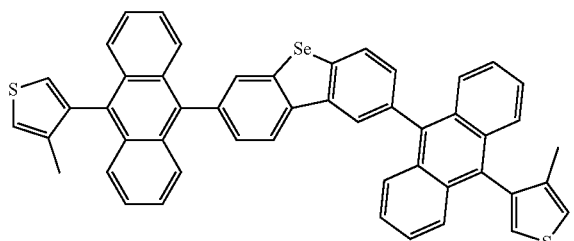 |
| 1401 | 1402 |
| 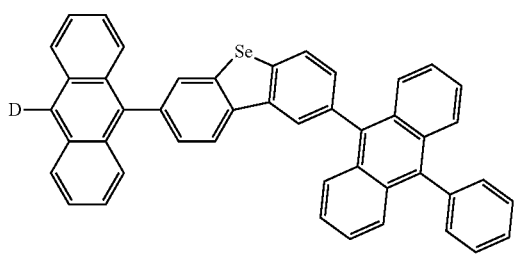 | 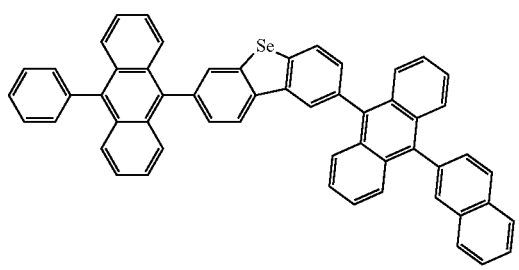 |
| 1403 | |
| 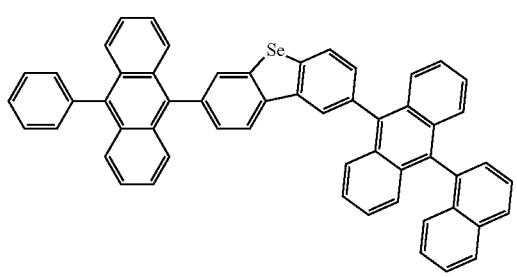 | |

1991 -continued 1992
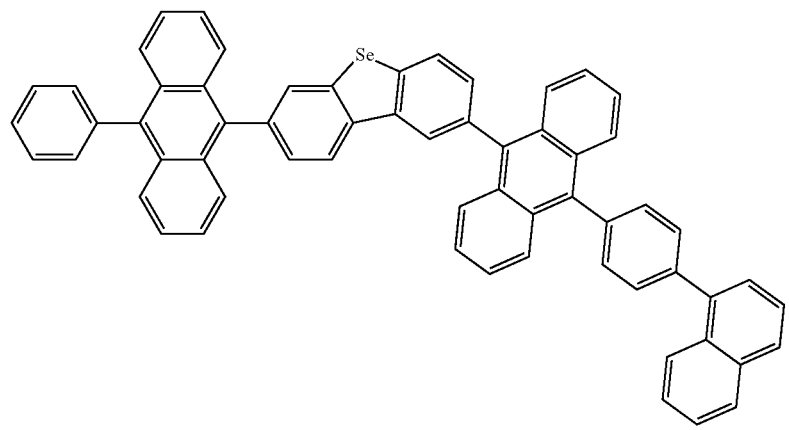
1404
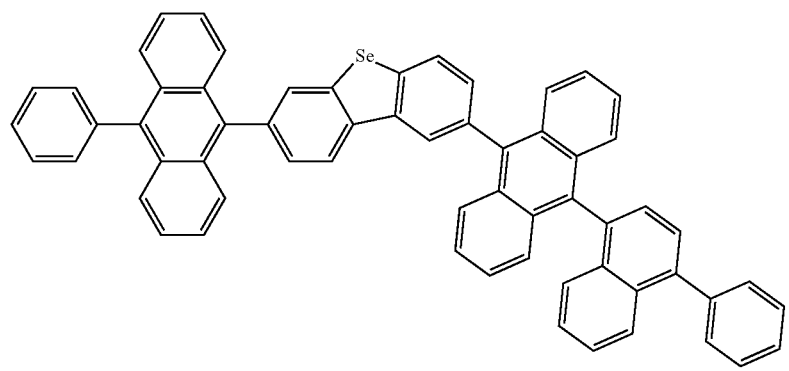
1405
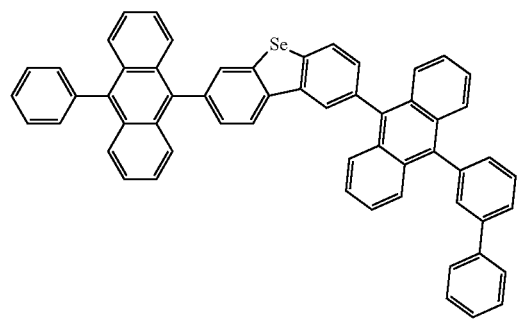
1406
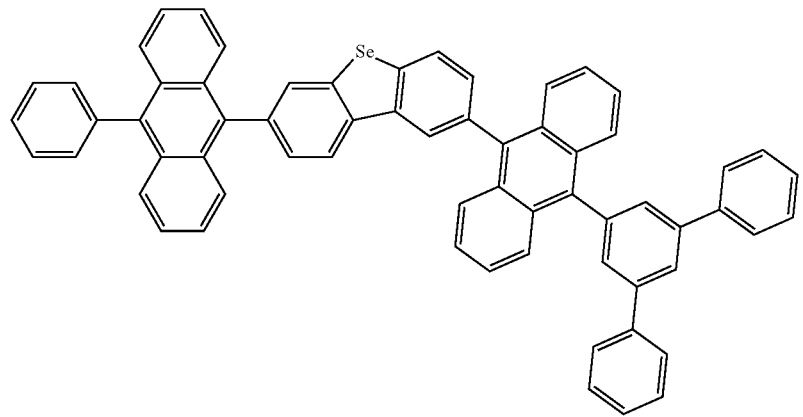
1407

1993    1994
-continued
1408
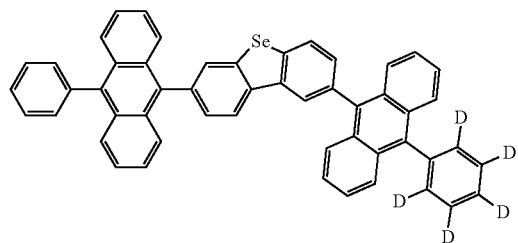
1409
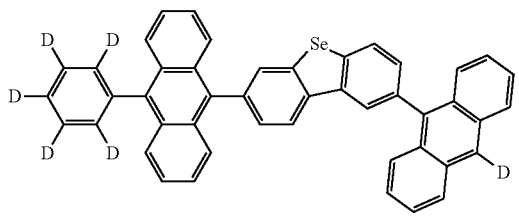
1410
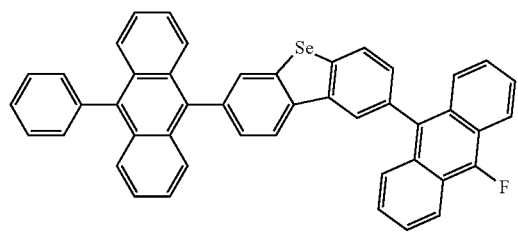
1411
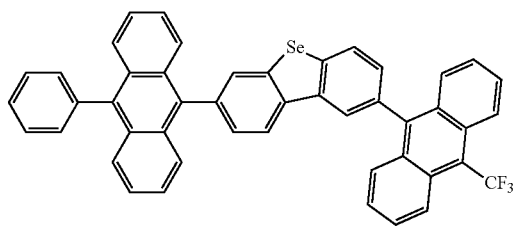
1412
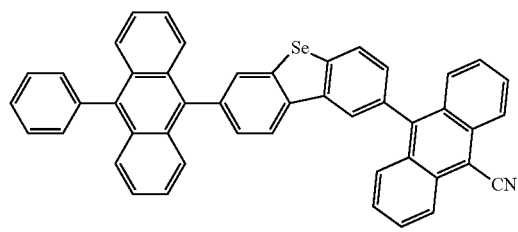
1413
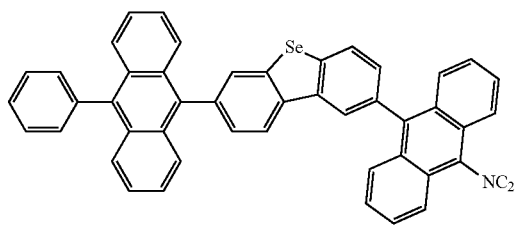
1414
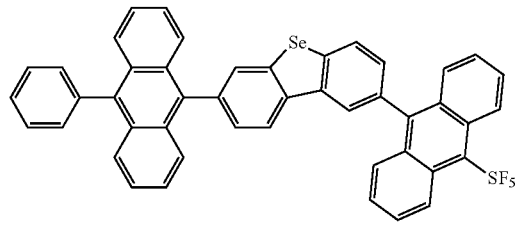
1415
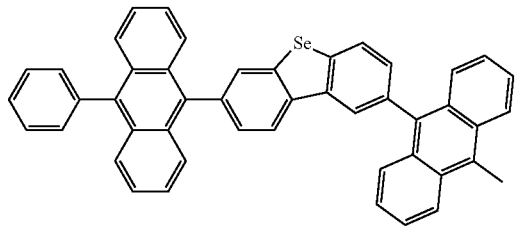
1416
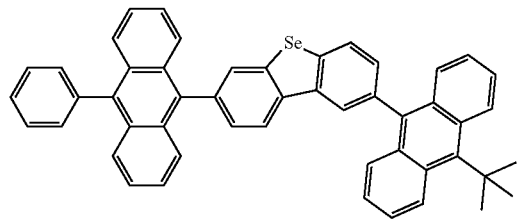
1417
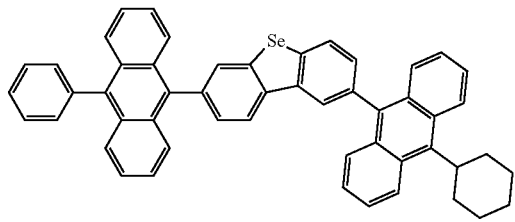
1418
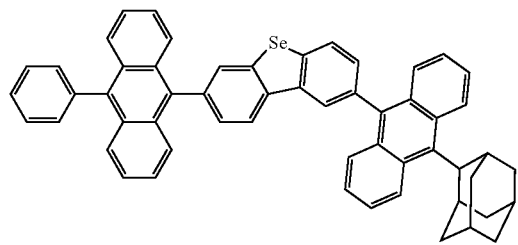
1419
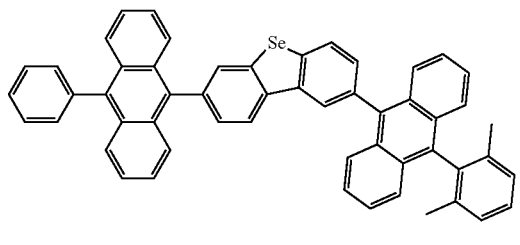

1995                              1996
-continued
1420
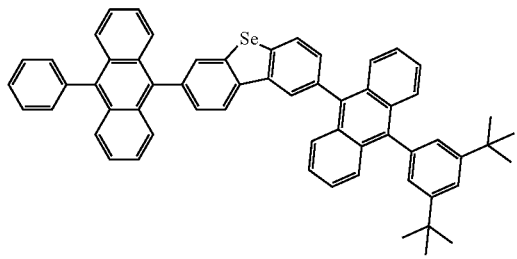
1421
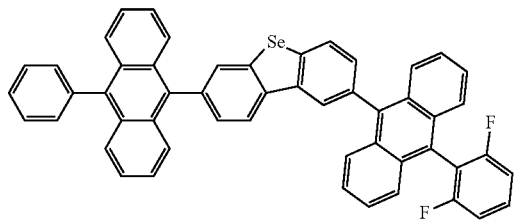
1422
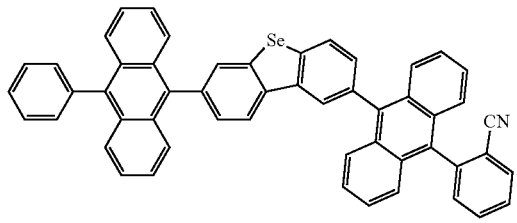
1423
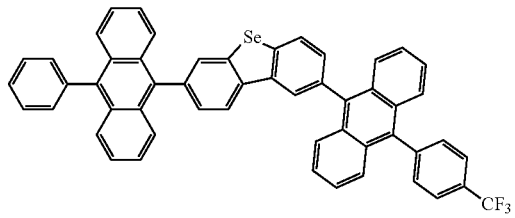
1424
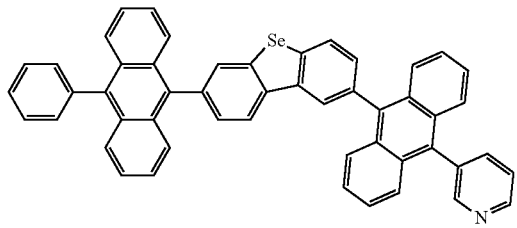
1425
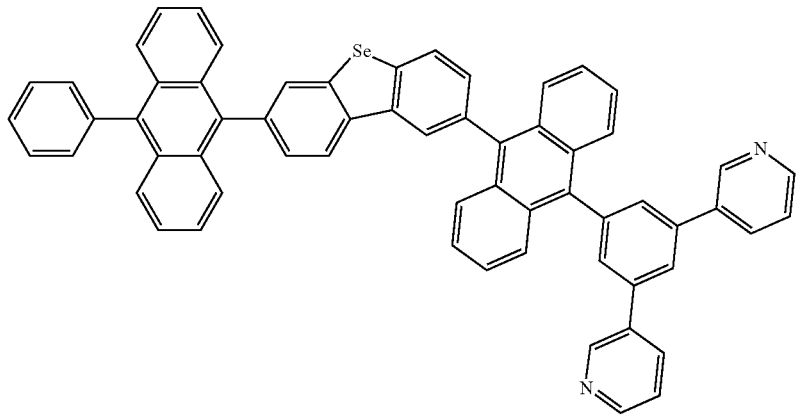
1426
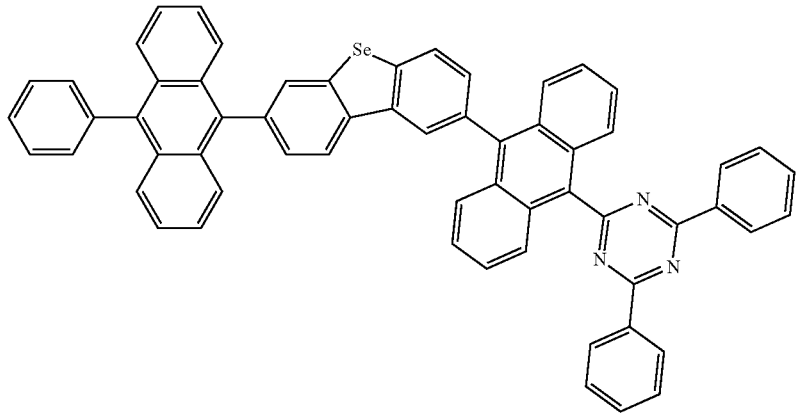

-continued
1427
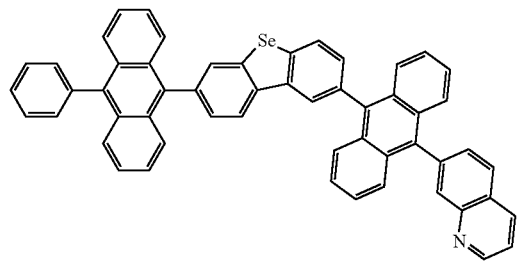
1428
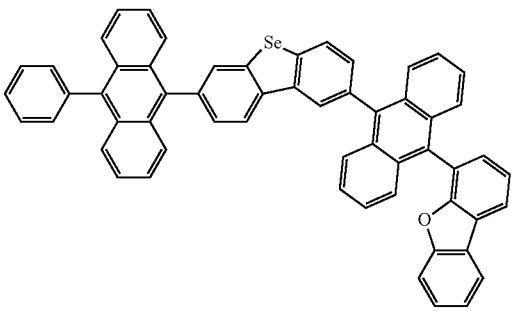
1429
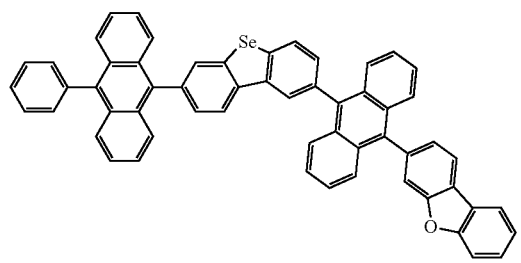
1430
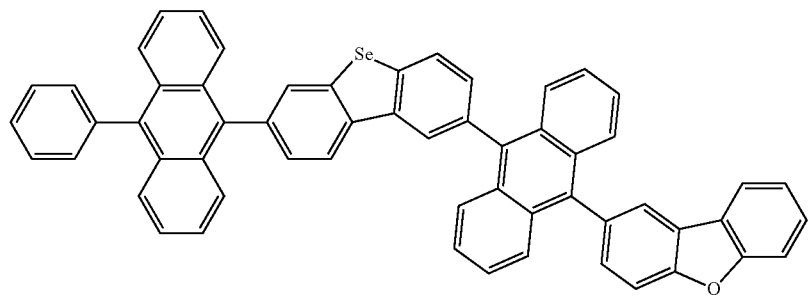
1431
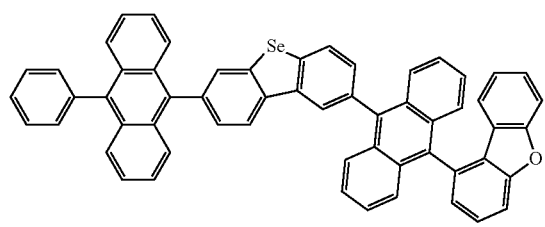

1999 2000
-continued
1432
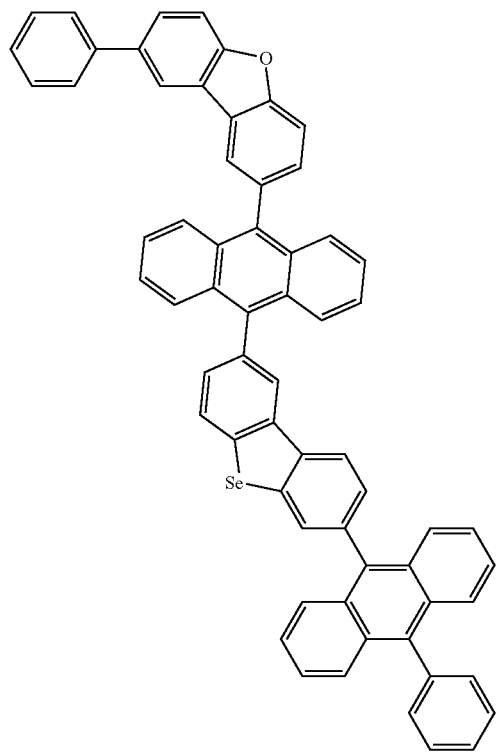
1433
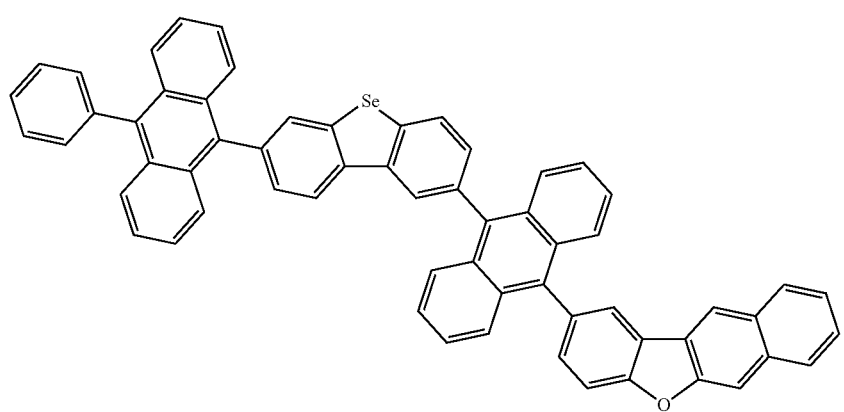
1434
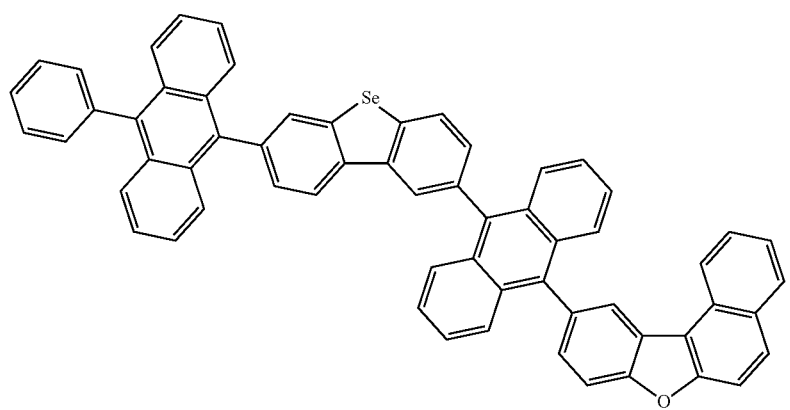

-continued
| 1435 |
|---|
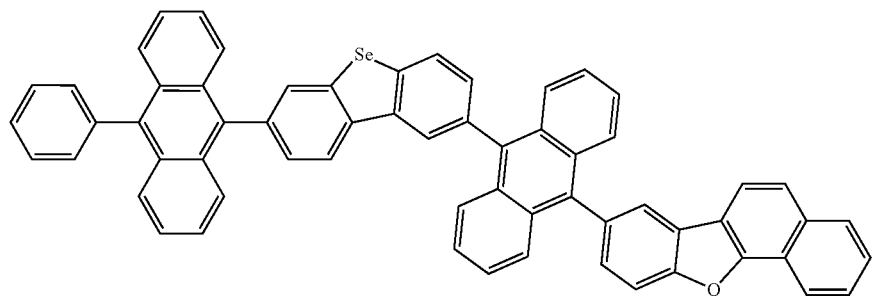
| 1436 | 1437 |
|---|---|
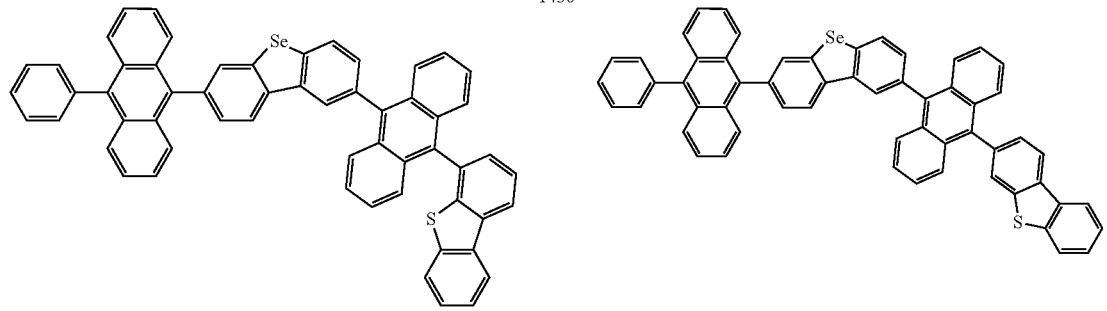
| 1438 |
|---|
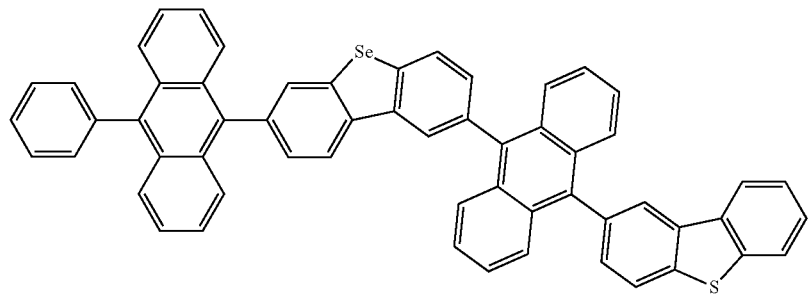
| 1439 | 1440 |
|---|---|
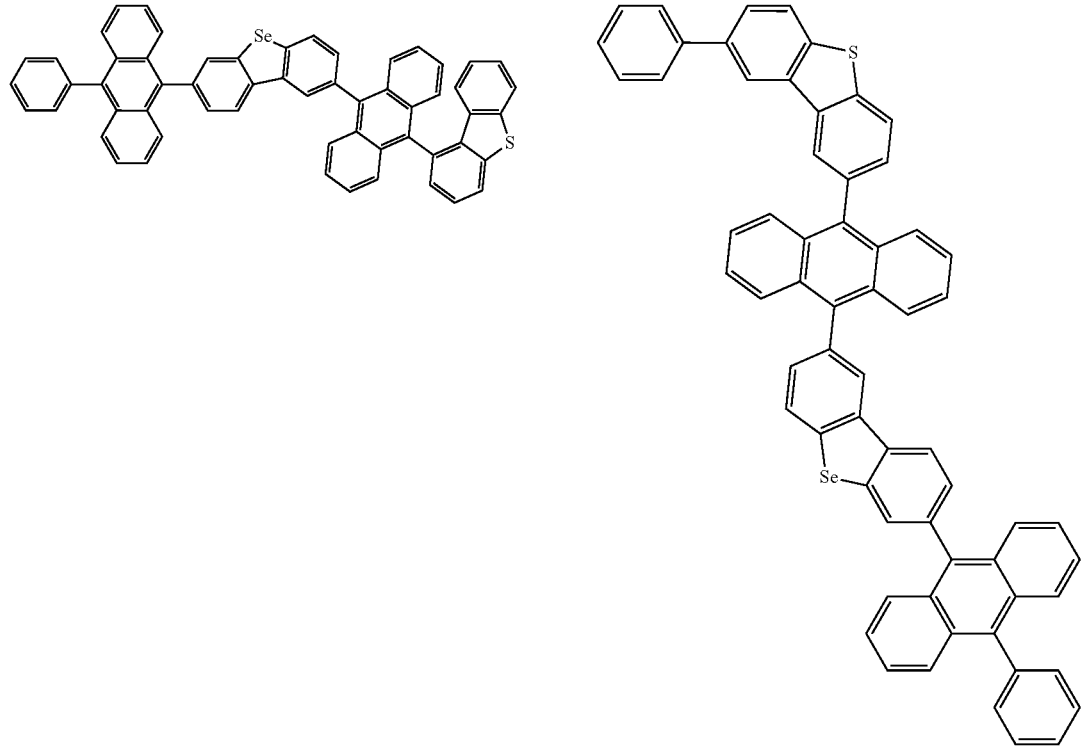

-continued
| 2003 | 2004 |
|---|---|
| 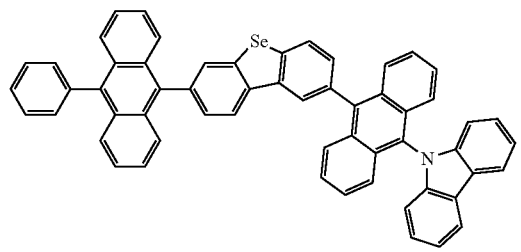 | 1441 |
| 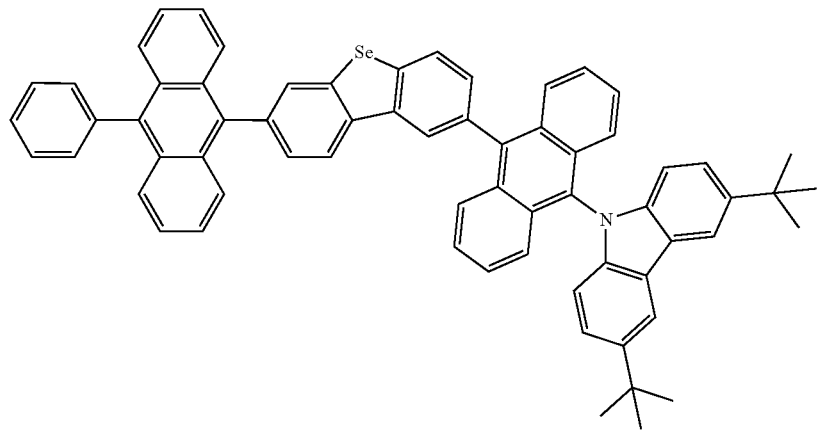 | 1442 |
| 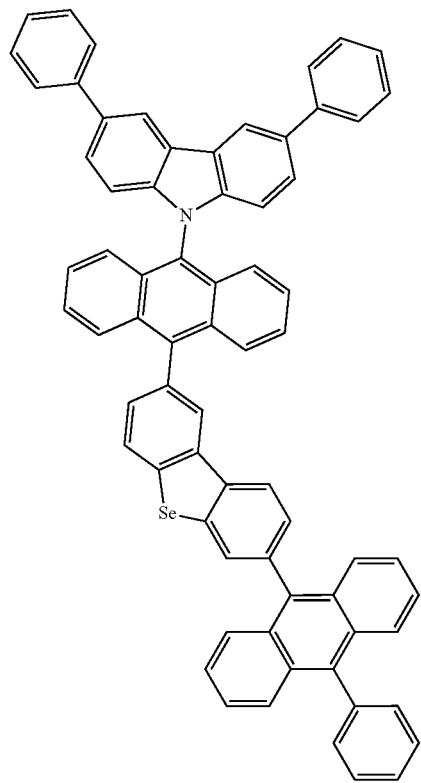  1443 | 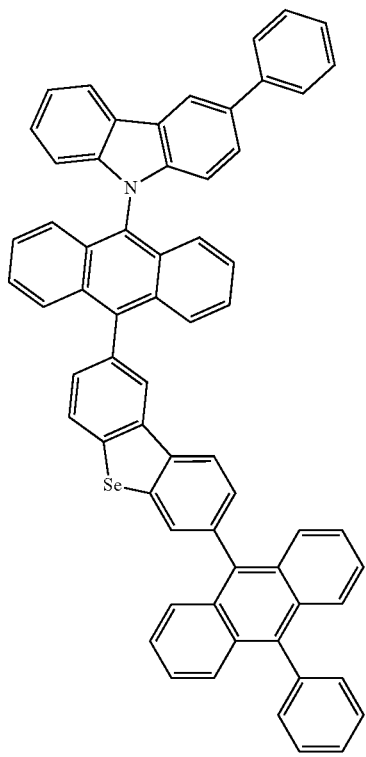  1444 |

-continued
1445
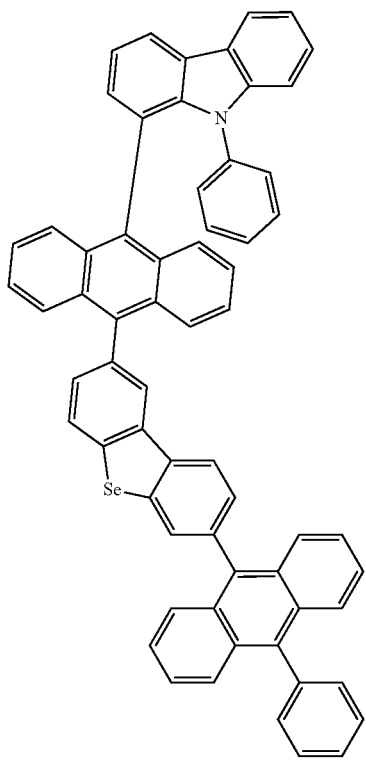
1446
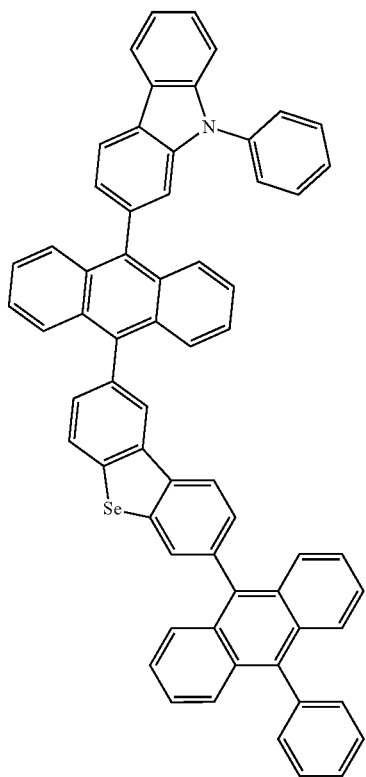
1447
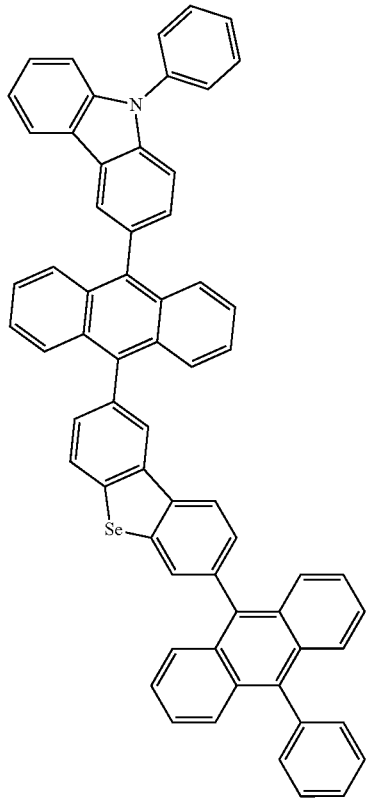
1448
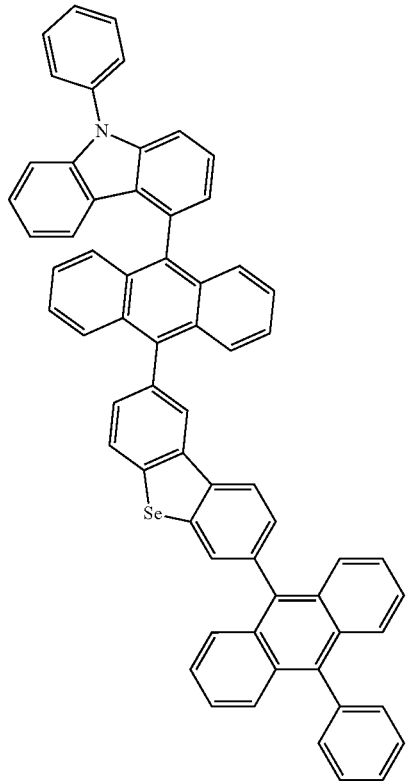

-continued
1449
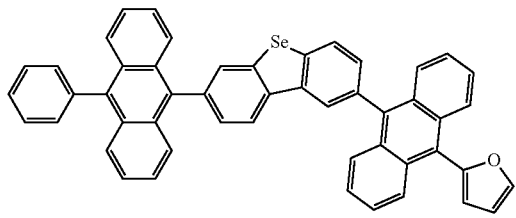
1450
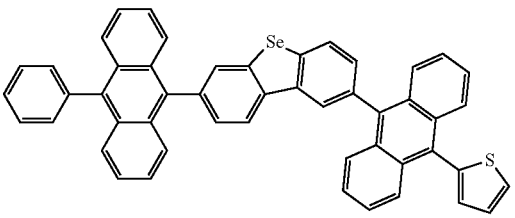
1451
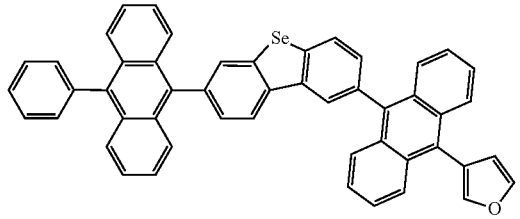
1452
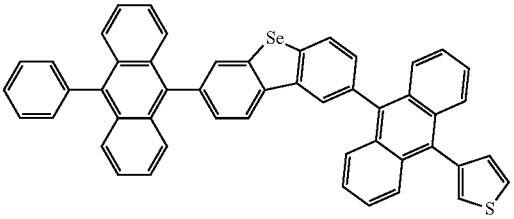
1453
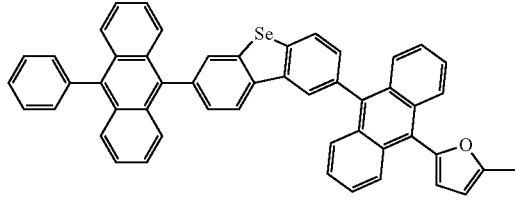
1454
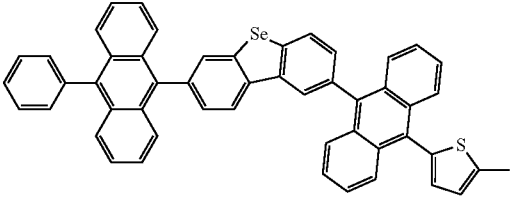
1455
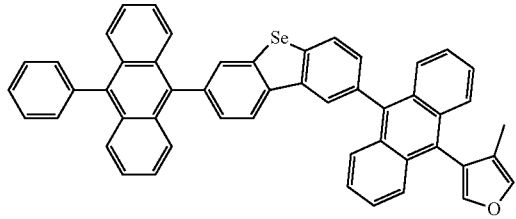
1456
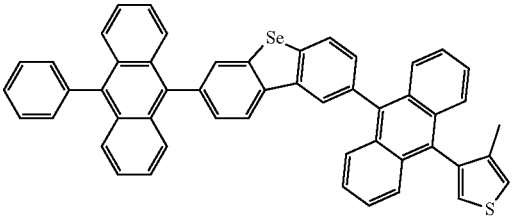
1457
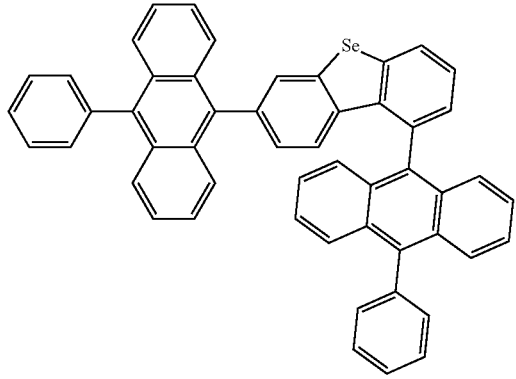
1458
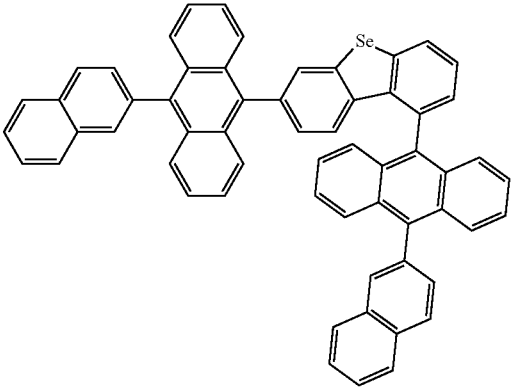

-continued
1459
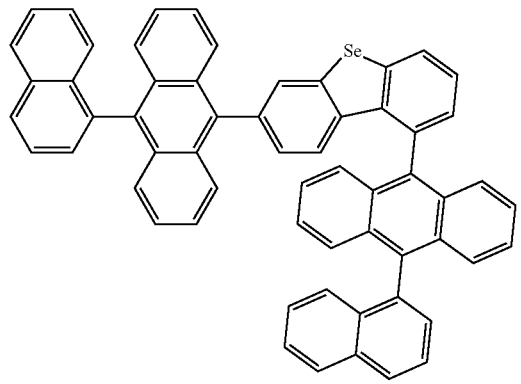
1460
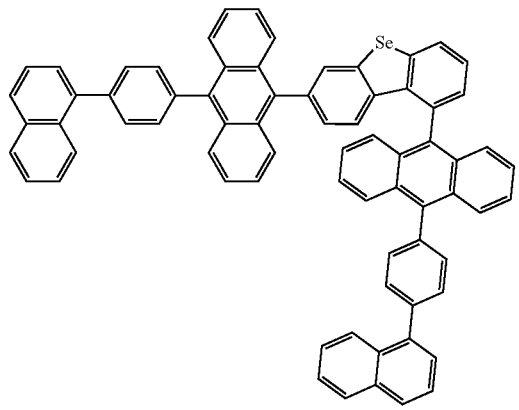
1461
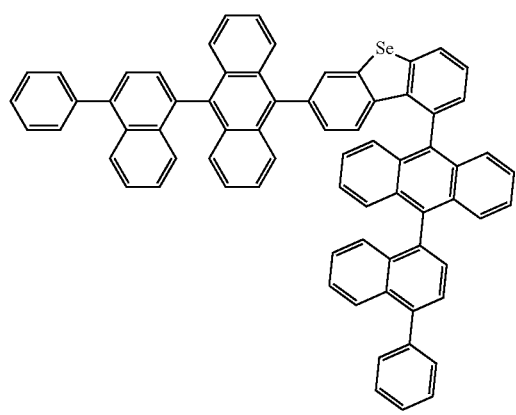
1462
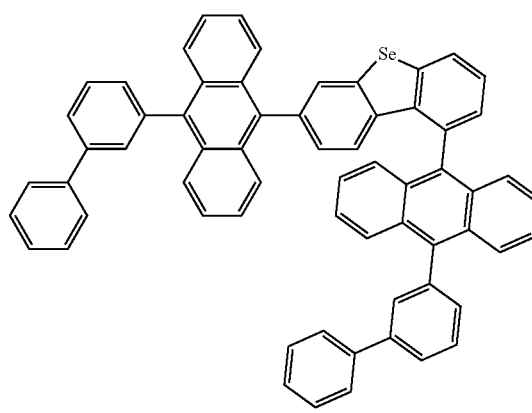
1463
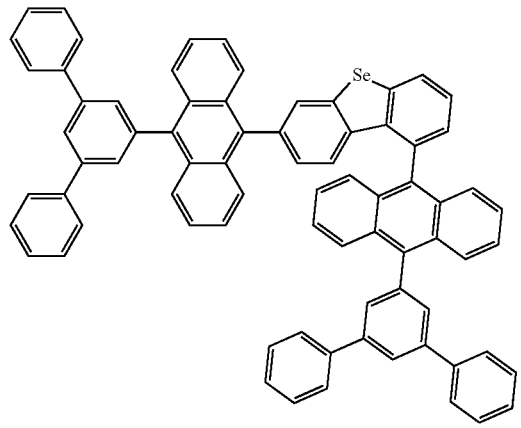
1464
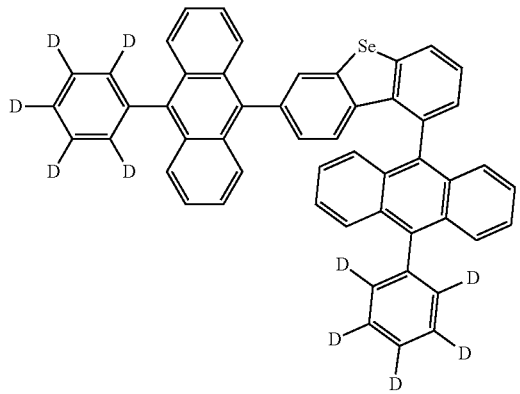
1465
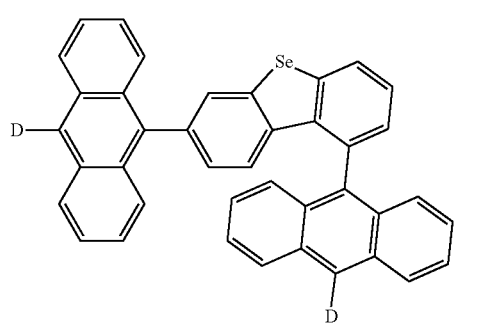
1466
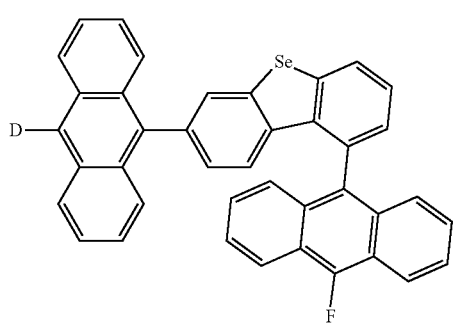

-continued
| 1467 | 1468 |
|---|---|
| 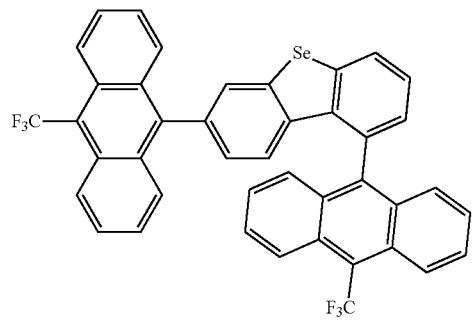 | 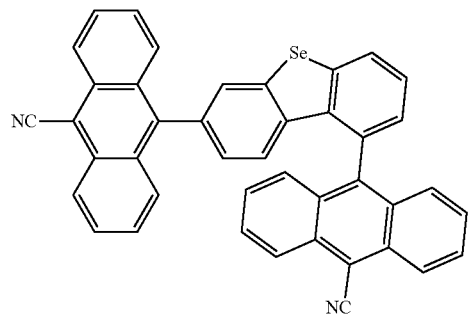 |
| 1469 | 1470 |
| 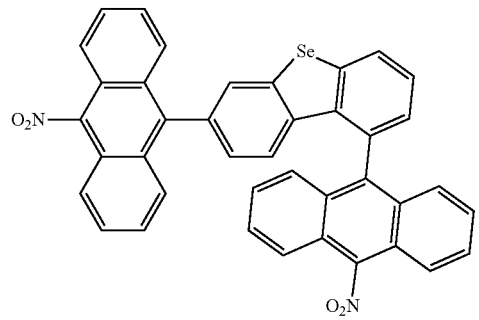 | 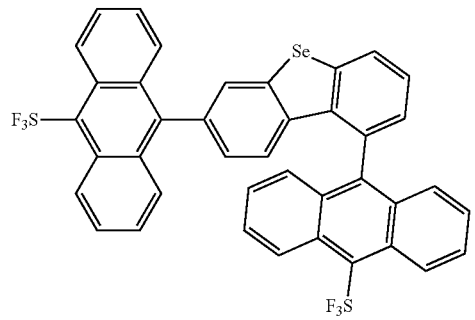 |
| 1471 | 1472 |
| 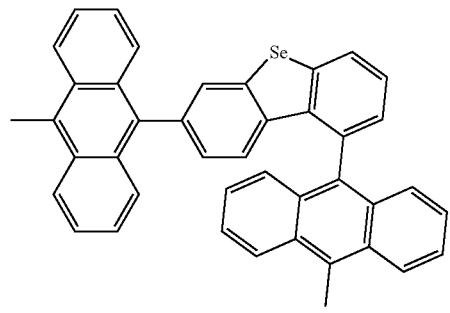 | 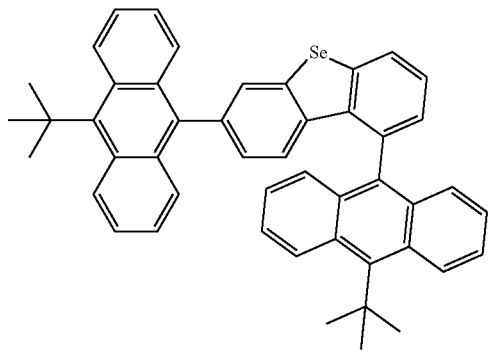 |
| 1473 | 1474 |
| 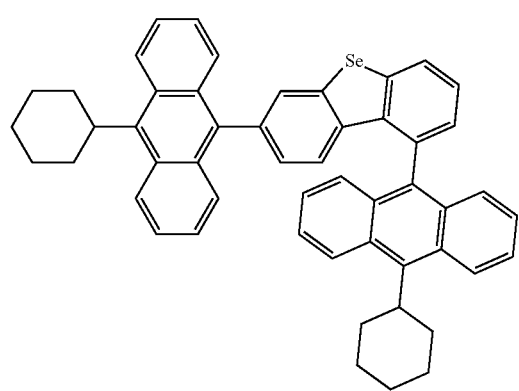 | 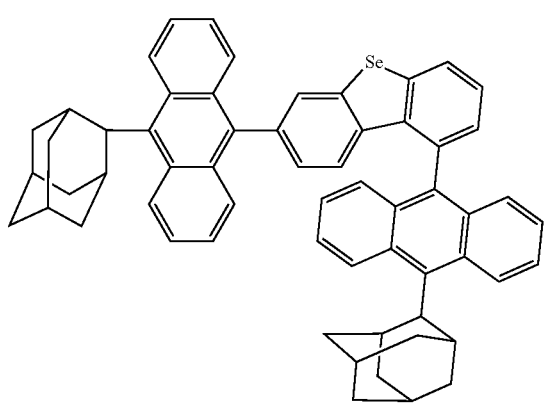 |

-continued
1475
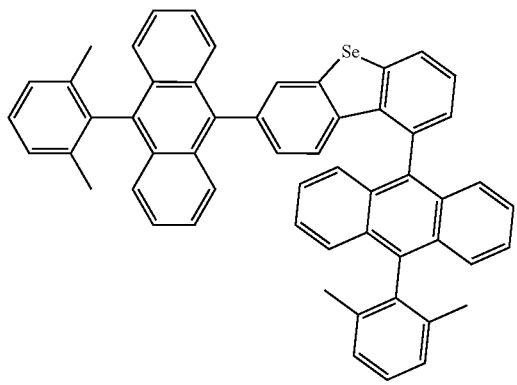
1476
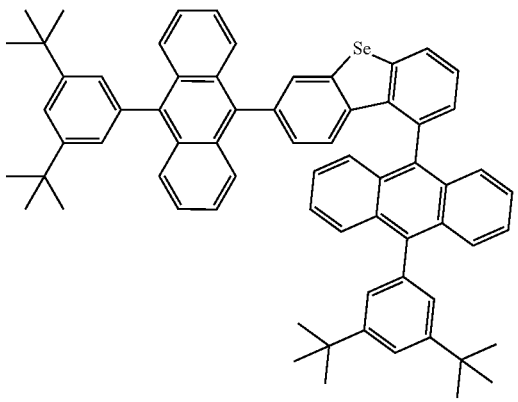
1477
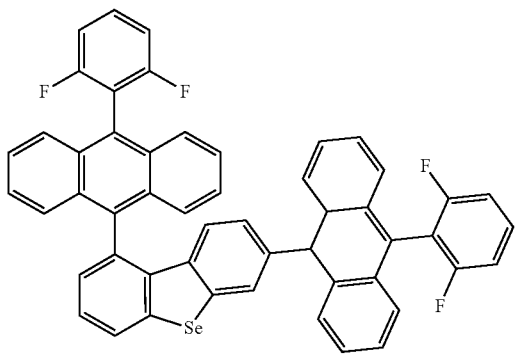
1478
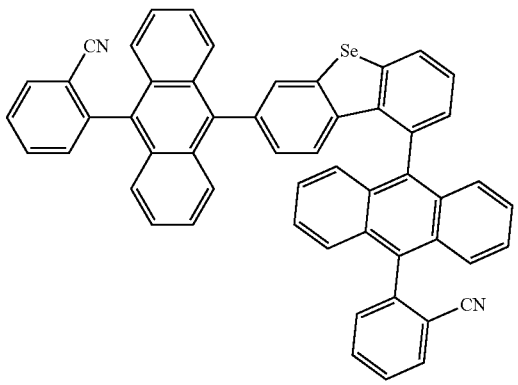
1479
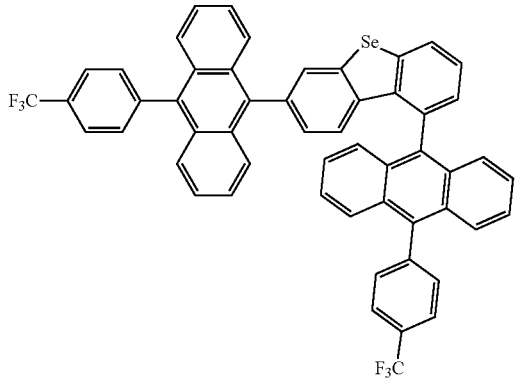
1480
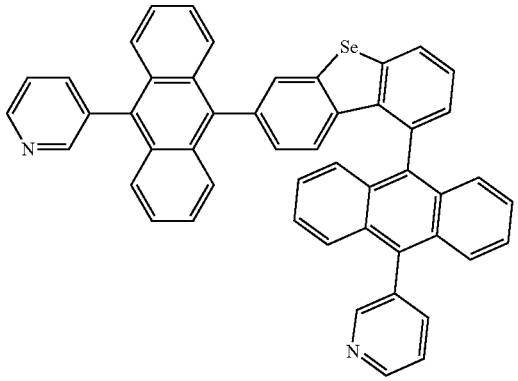
1481
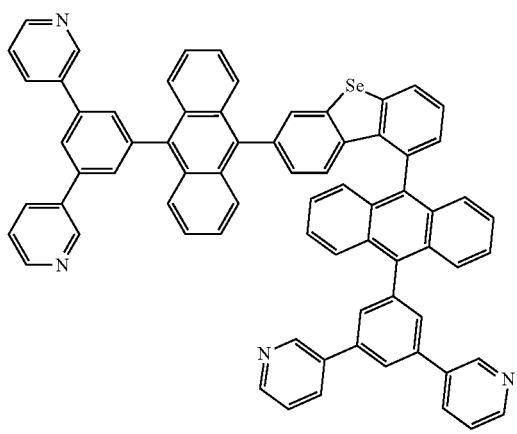
1482
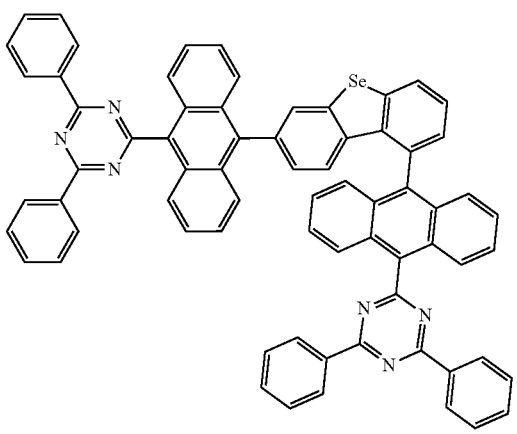

-continued
1483
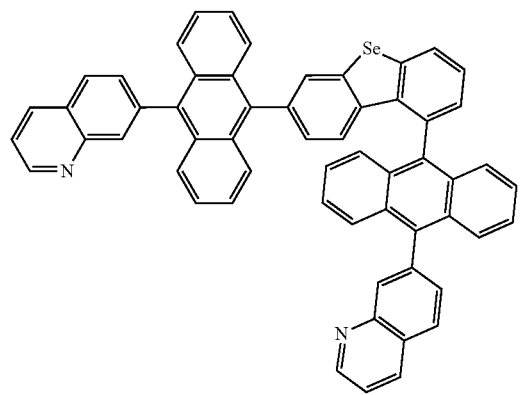
1484
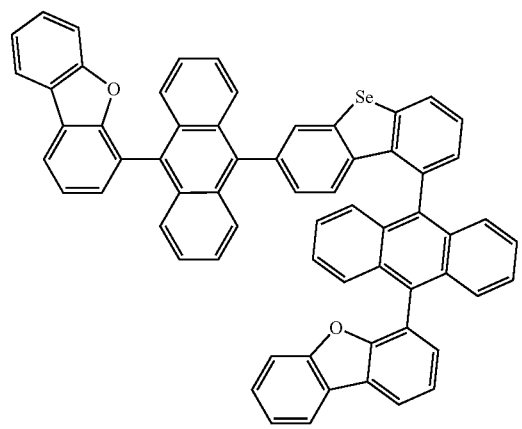
1485
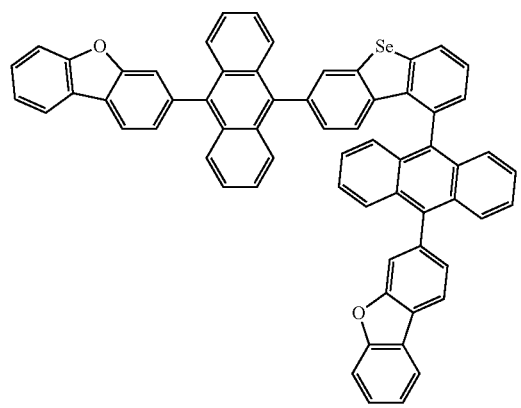
1486
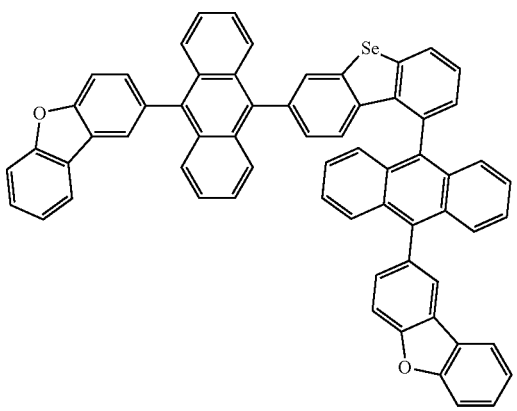
1487
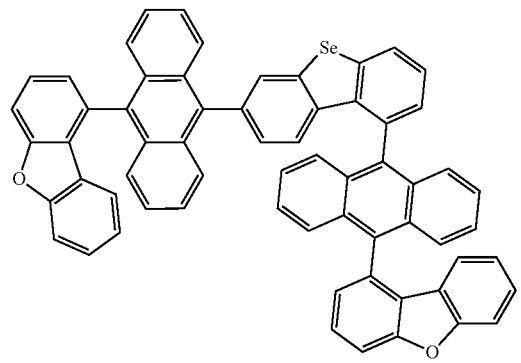
1488
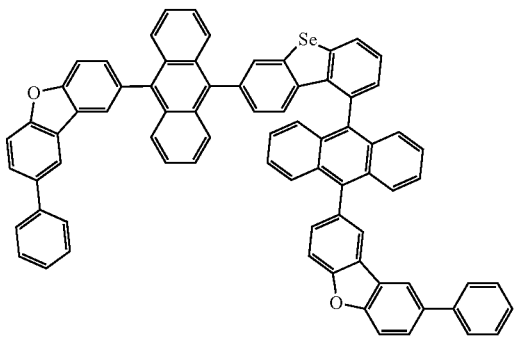

-continued
1489
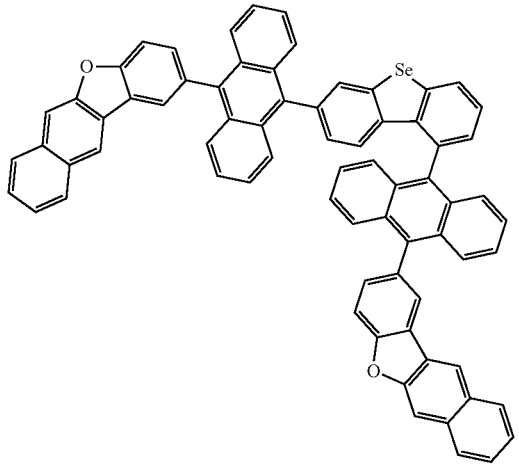
1490
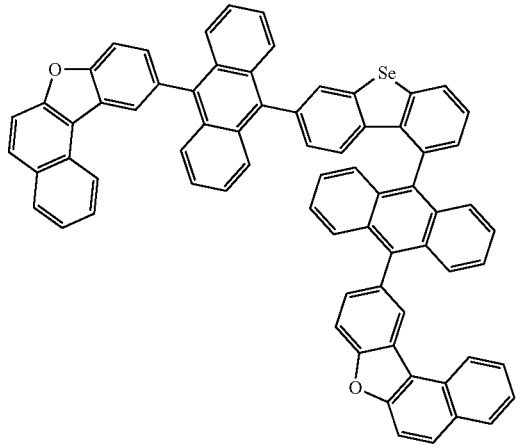
1491
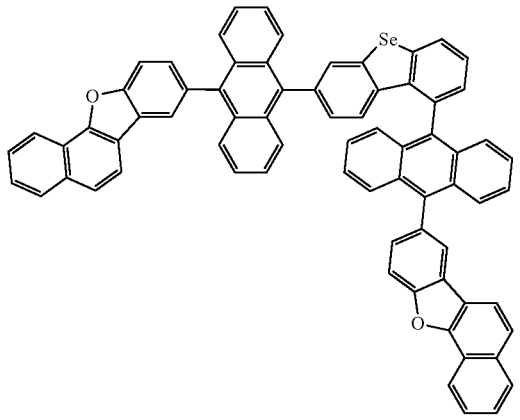
1492
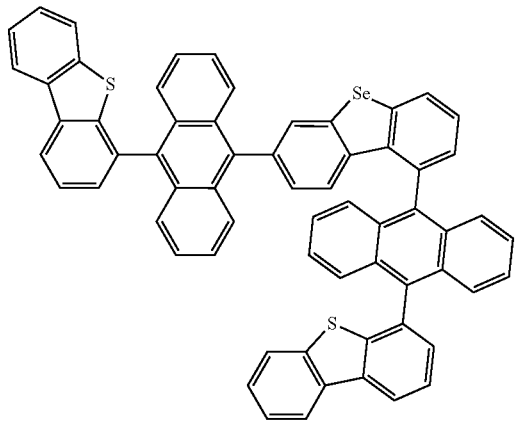
1493
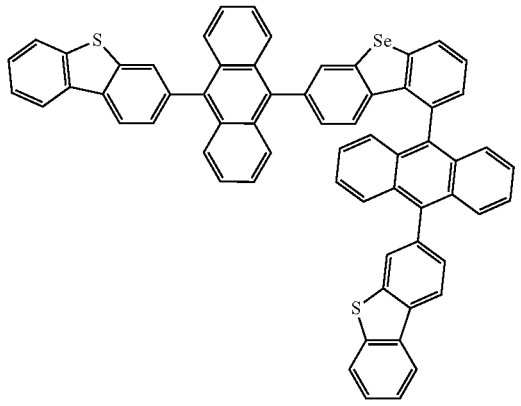
1494
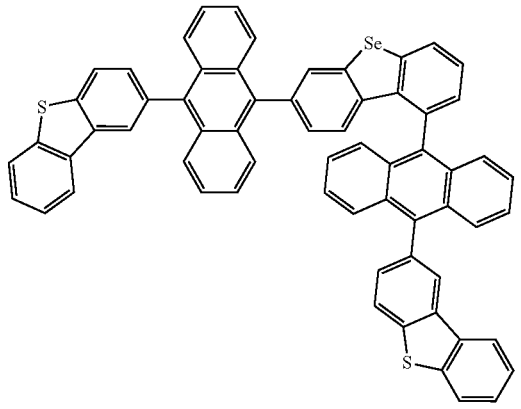

-continued
1495
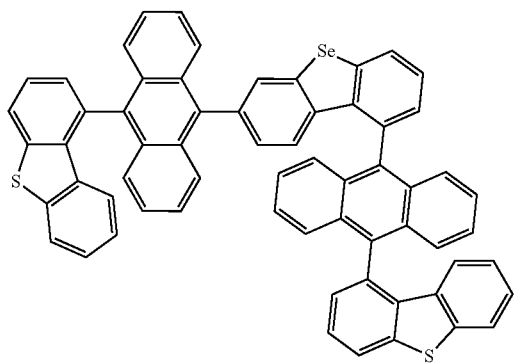
1496
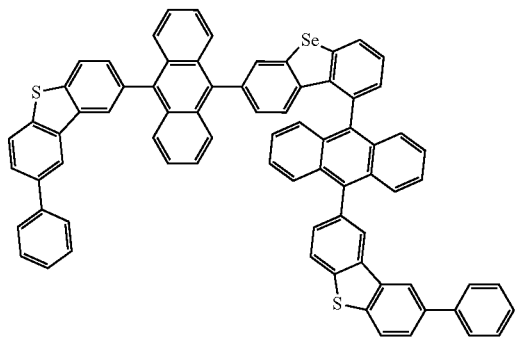
1497
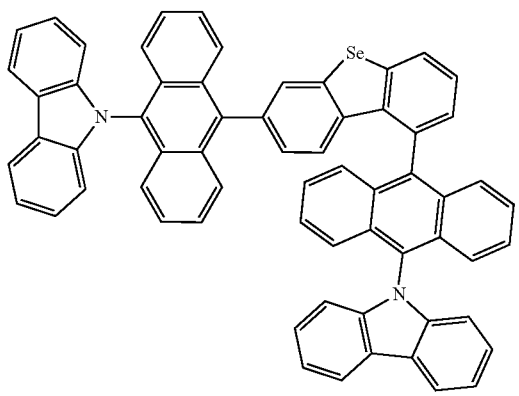
1498
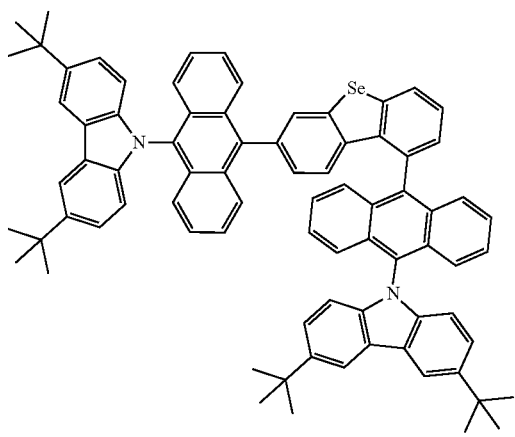
1499
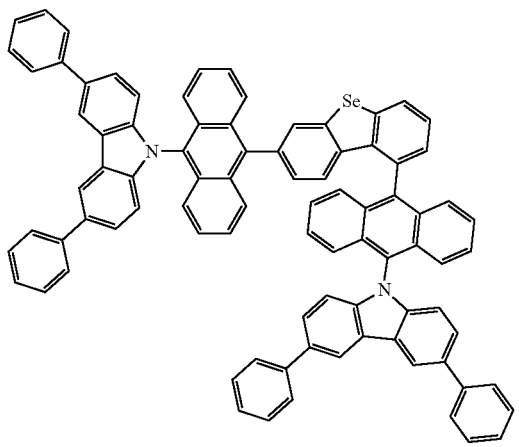
1500
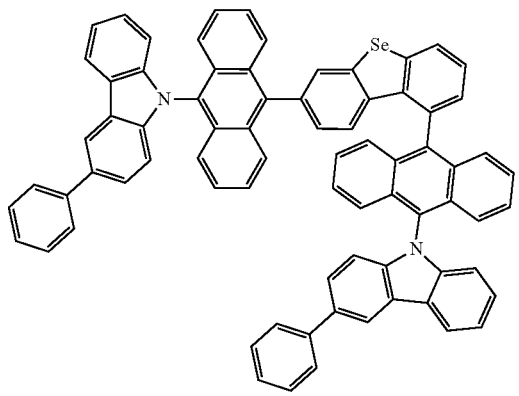

-continued
1501
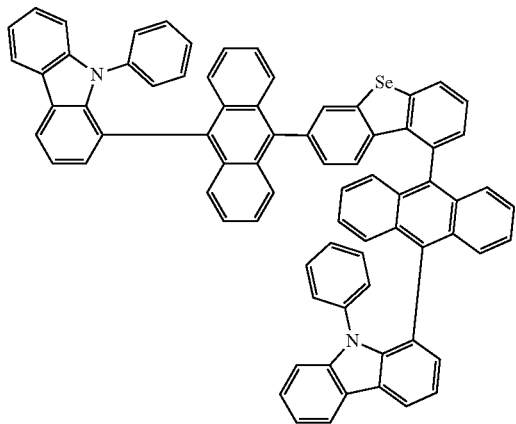
1502
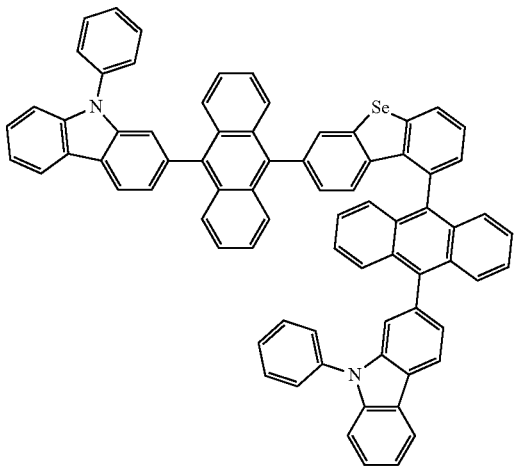
1503
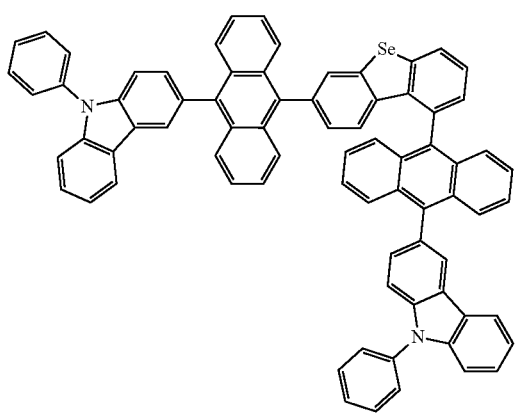
1504
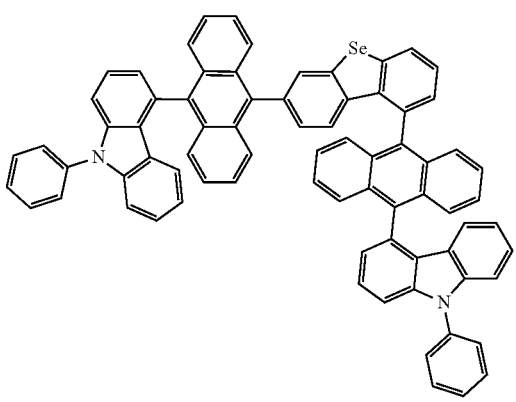
1505
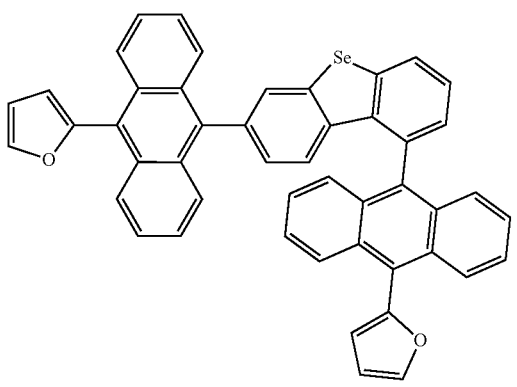
1506
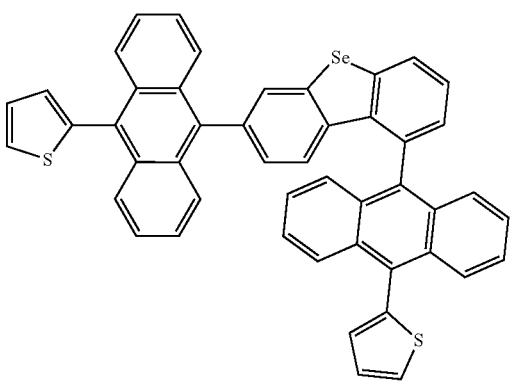
1507
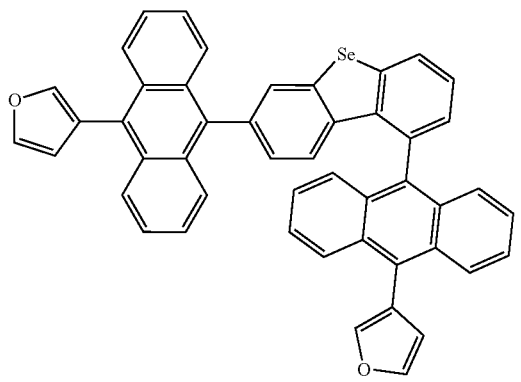
1508
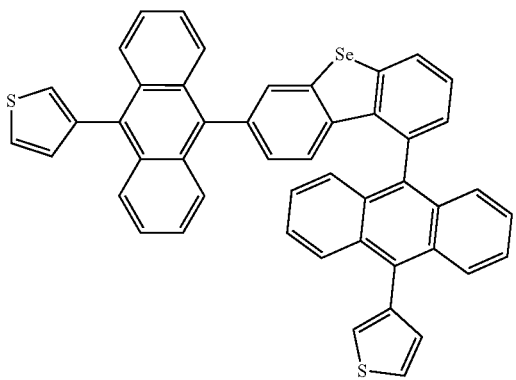

-continued
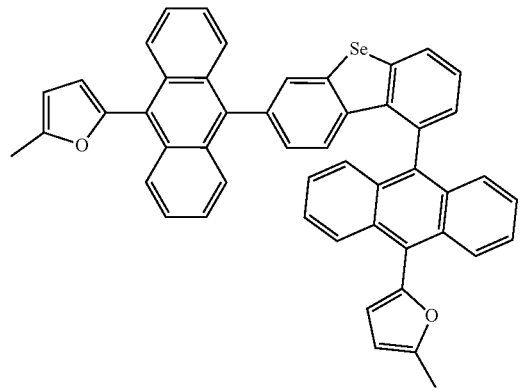
1509
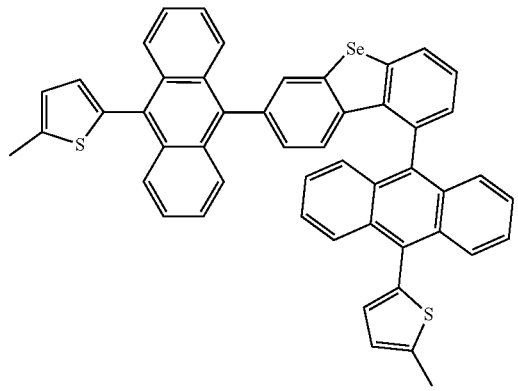
1510
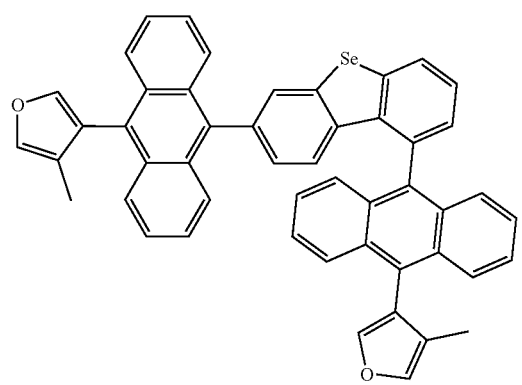
1511
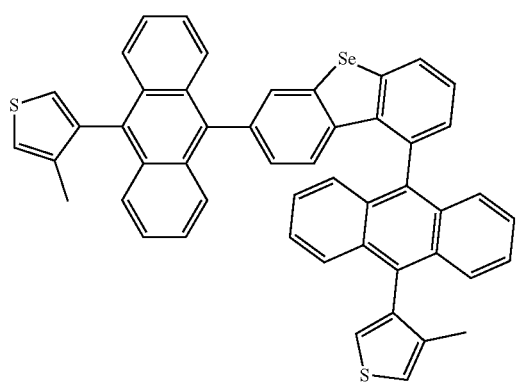
1512
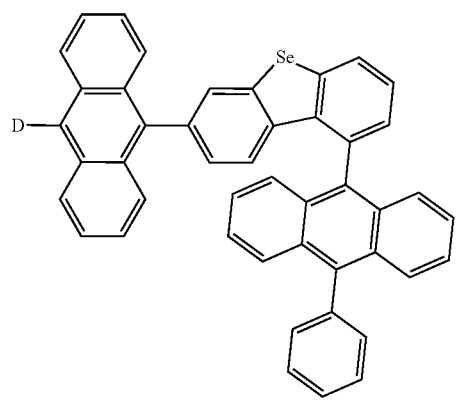
1513
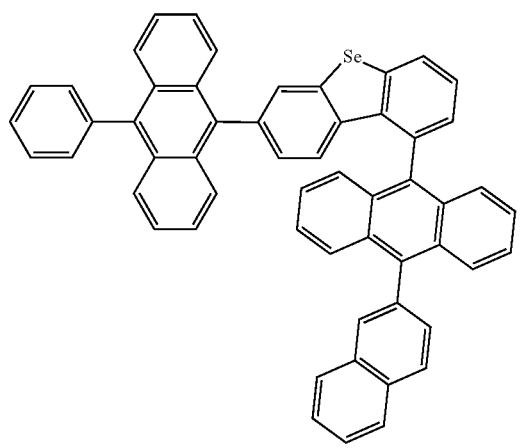
1514

-continued
1515
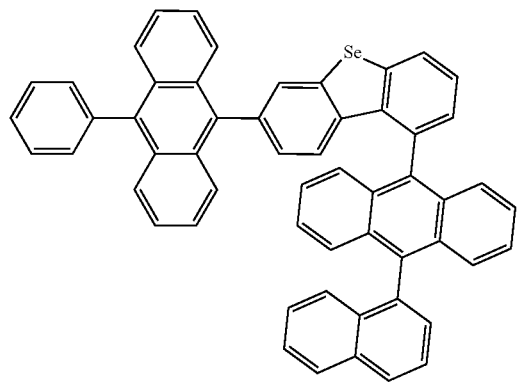
1516
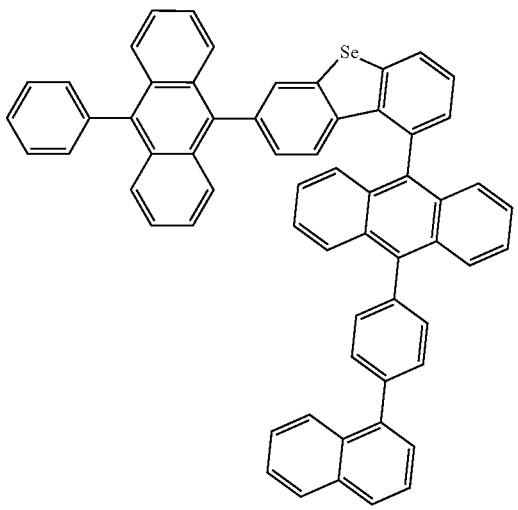
1517
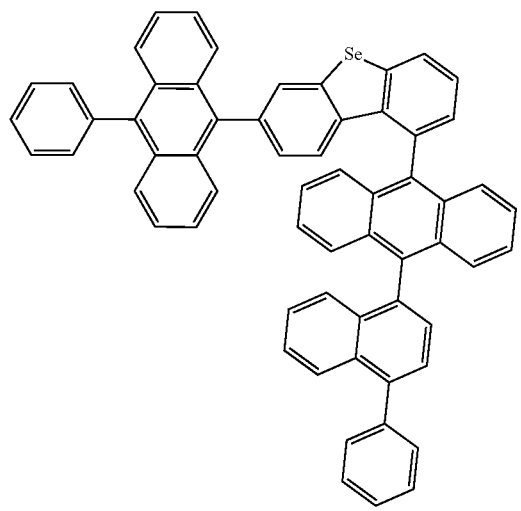
1518
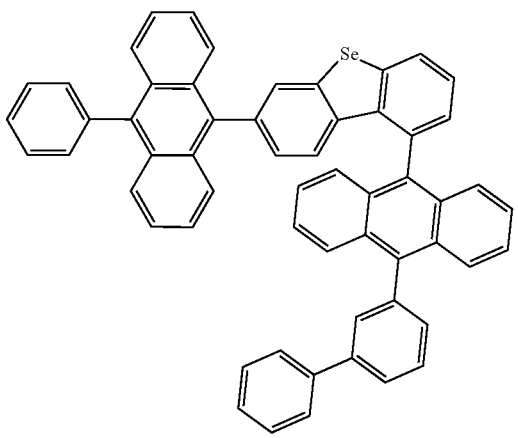
1519
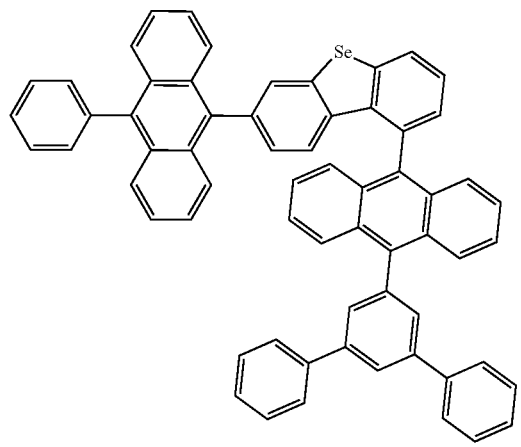
1520
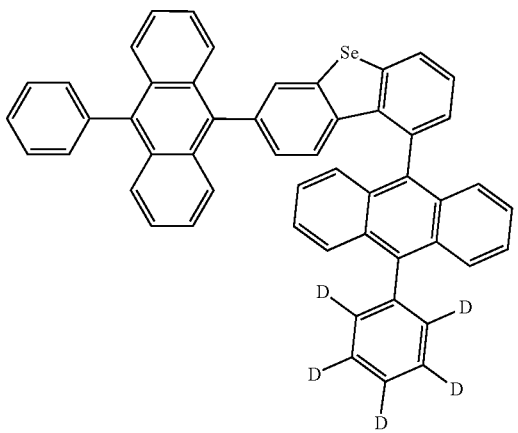

-continued
1521
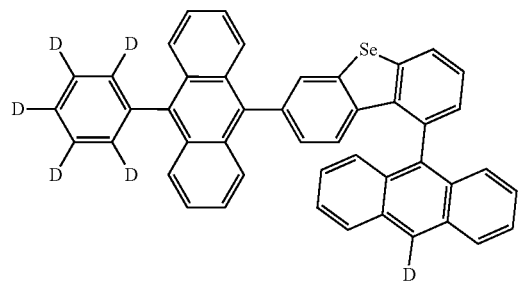
1522
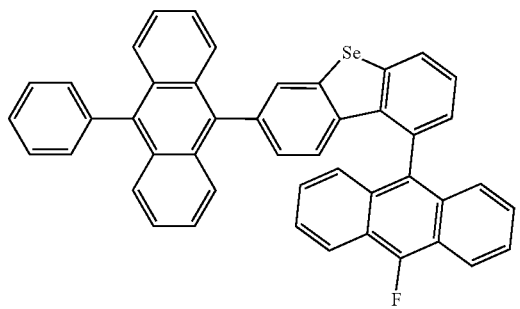
1523
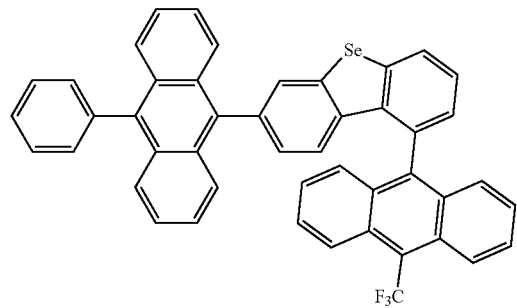
1524
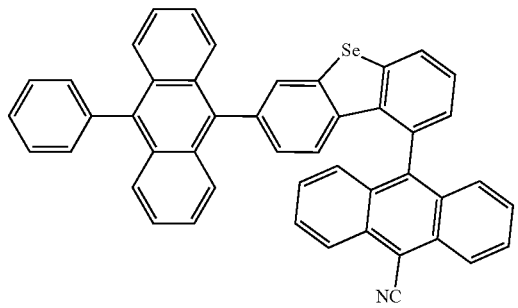
1525
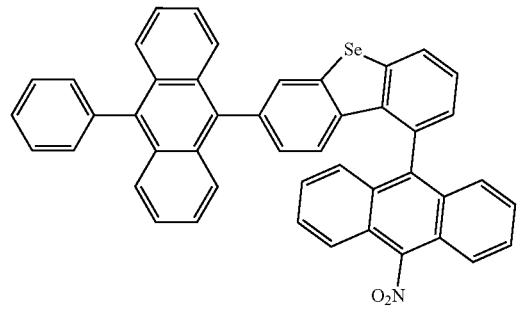
1526
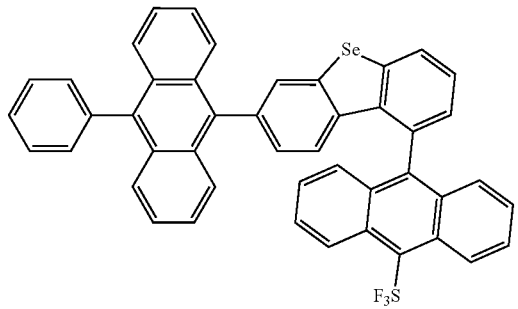
1527
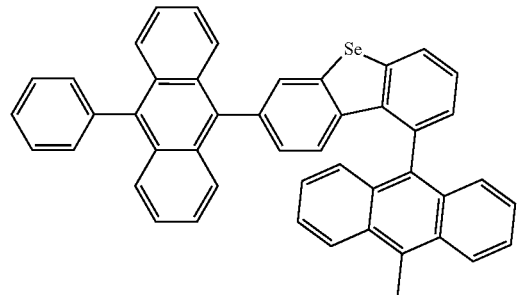
1528
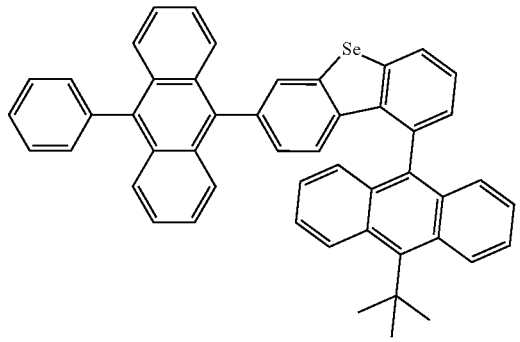

-continued
1529
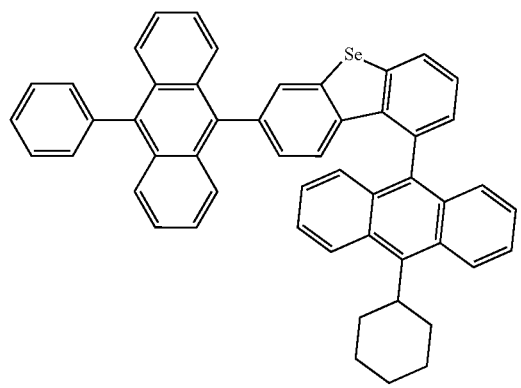
1530
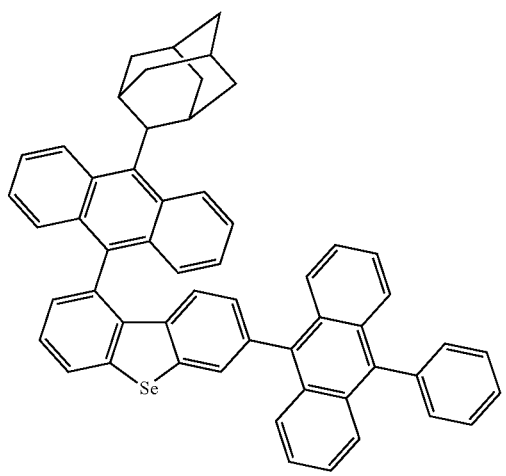
1531
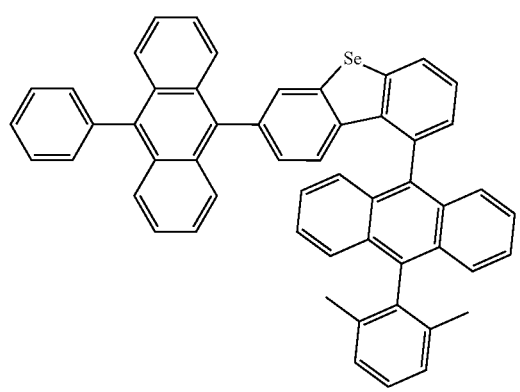
1532
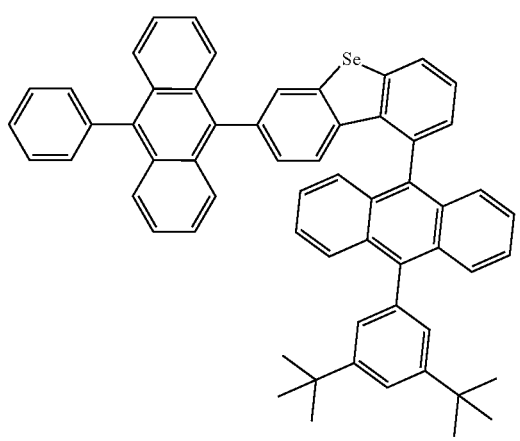
1533
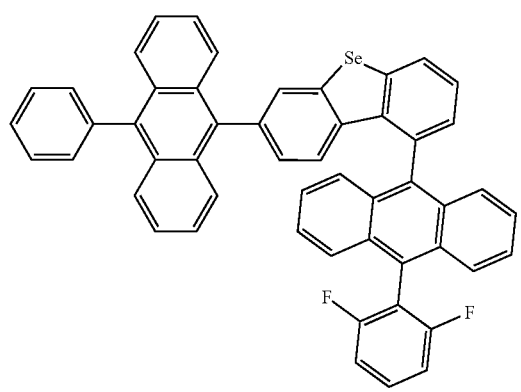
1534
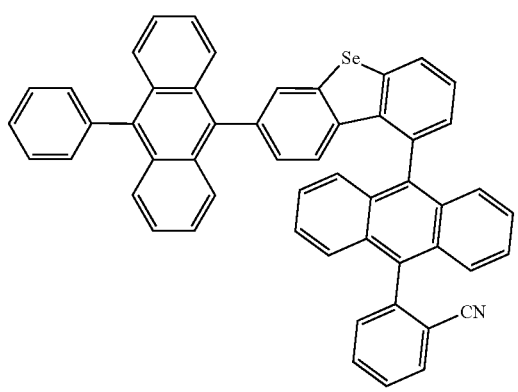

-continued
2031
1535
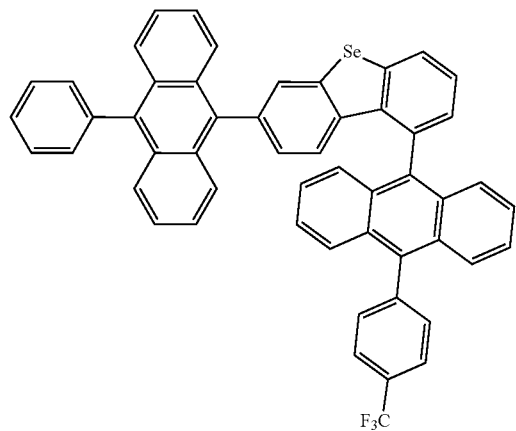
1537
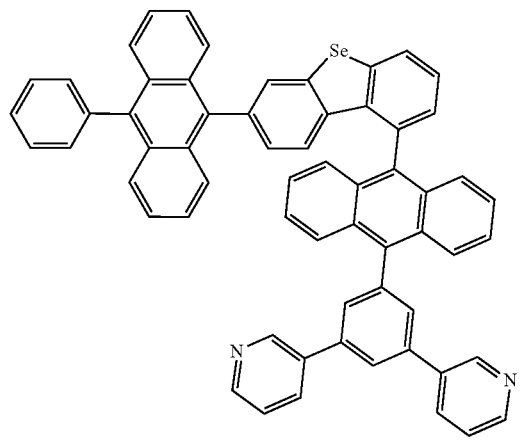
1539
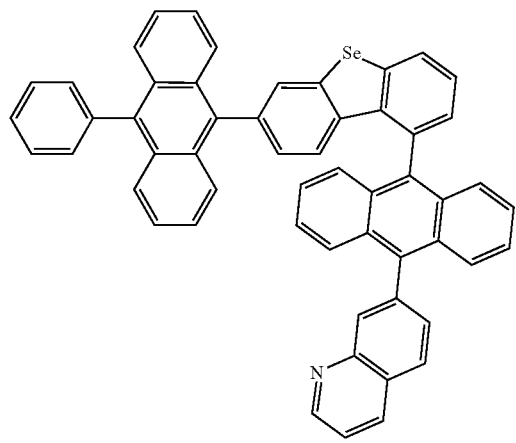
2032
1536
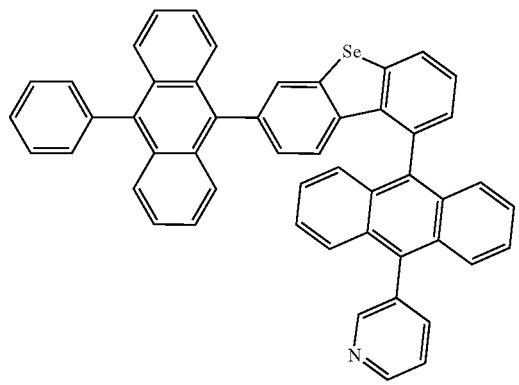
1538
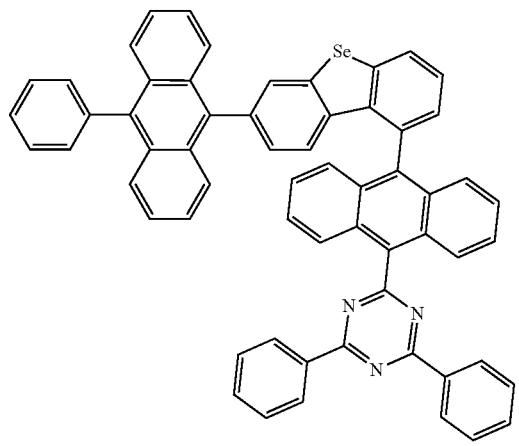
1540
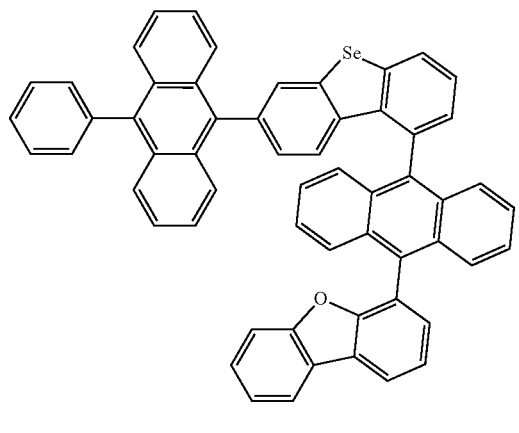

-continued
1541
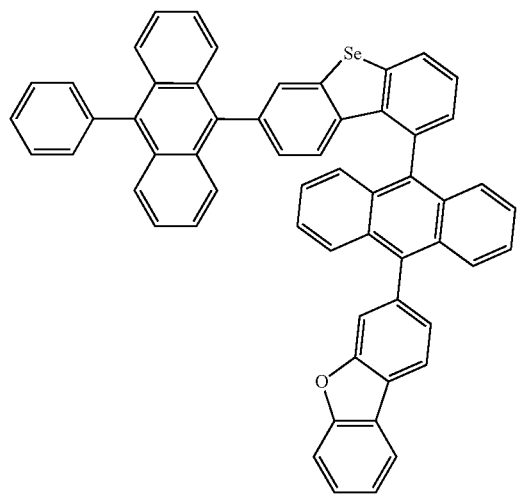
1542
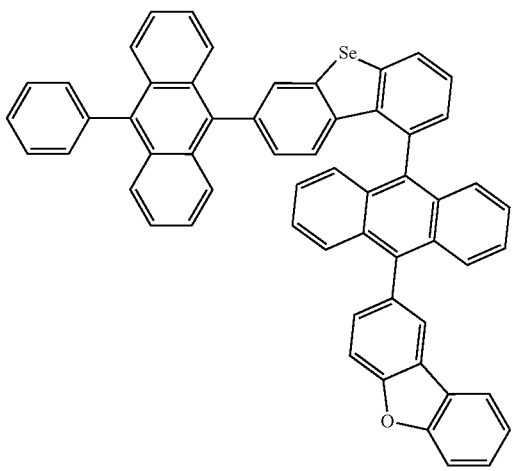
1543
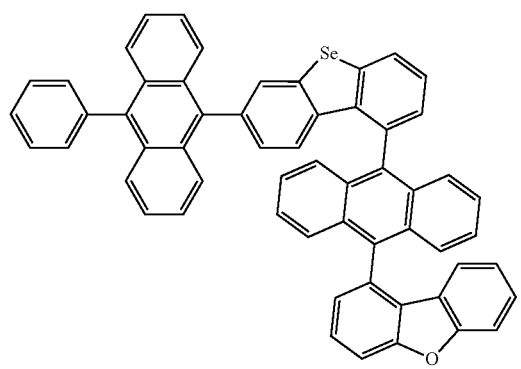
1544
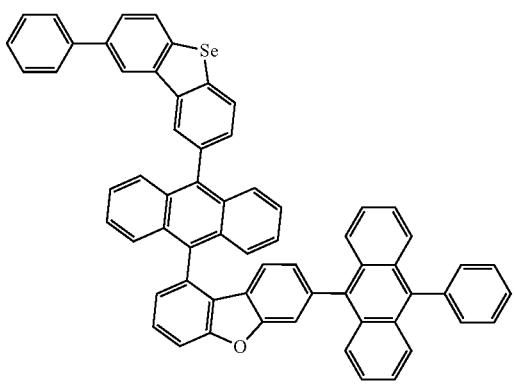
1545
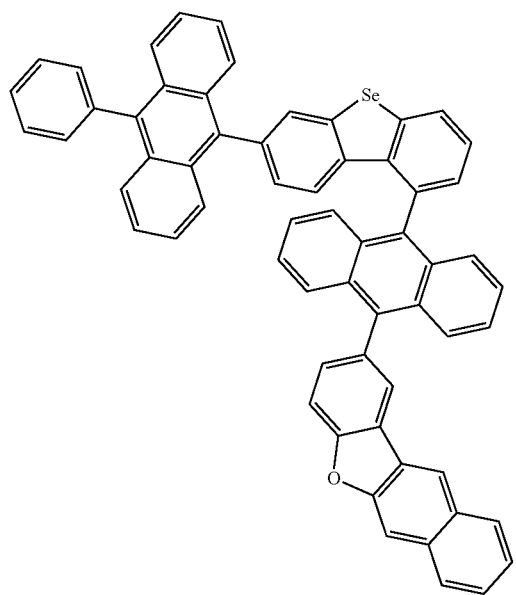
1546
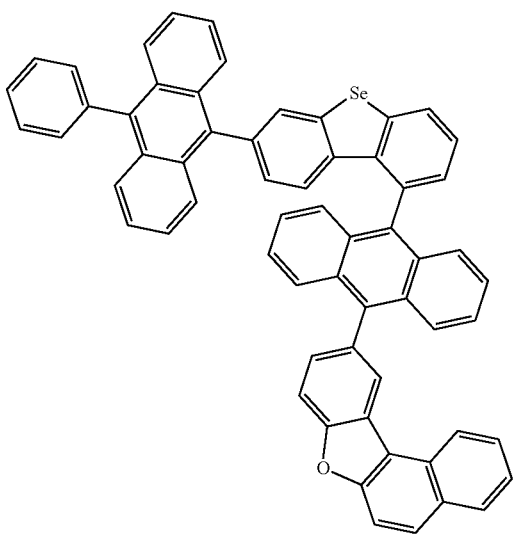

-continued
1547
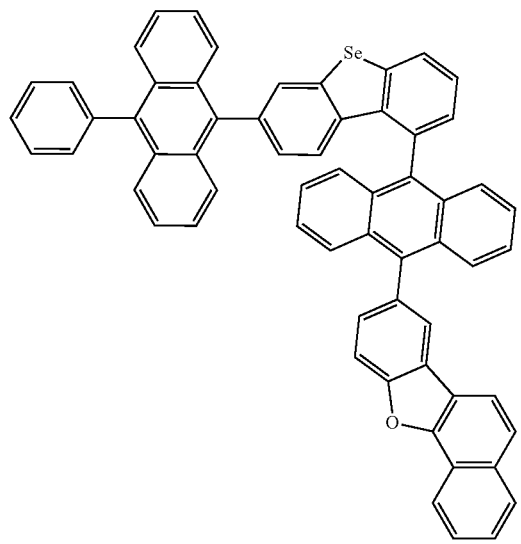
1548
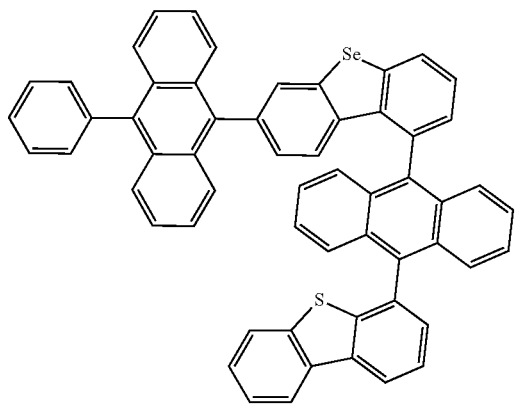
1549
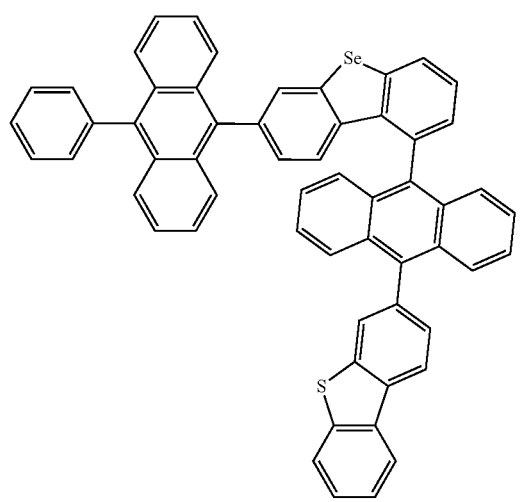
1550
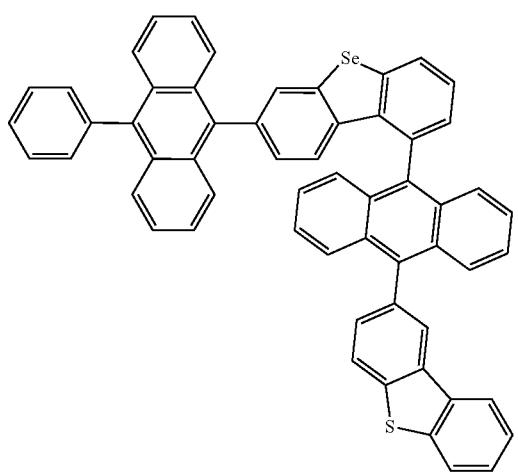
1551
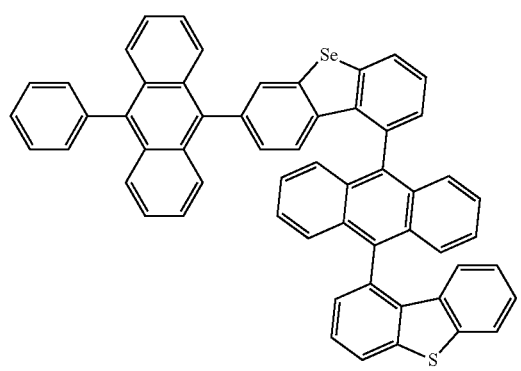
1552
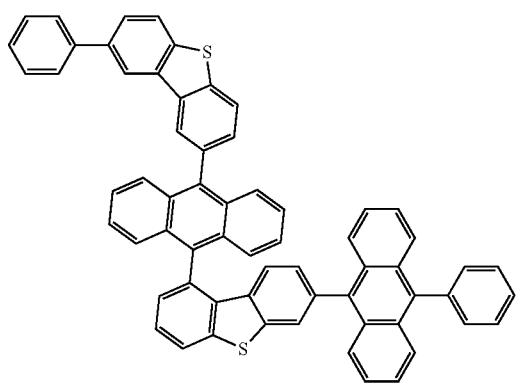

-continued
2037
1553
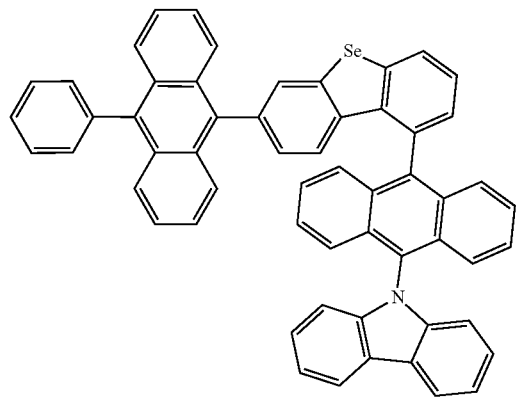
1555
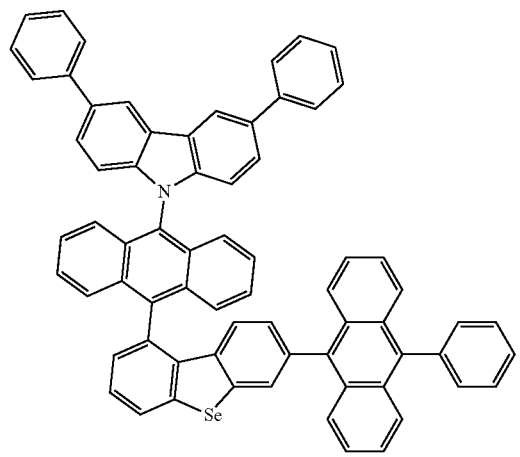
1557
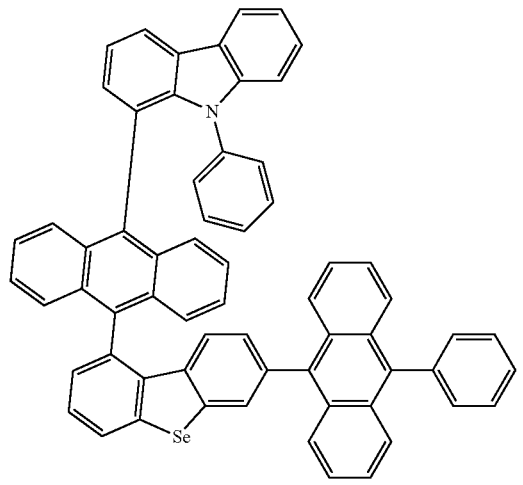
2038
1554
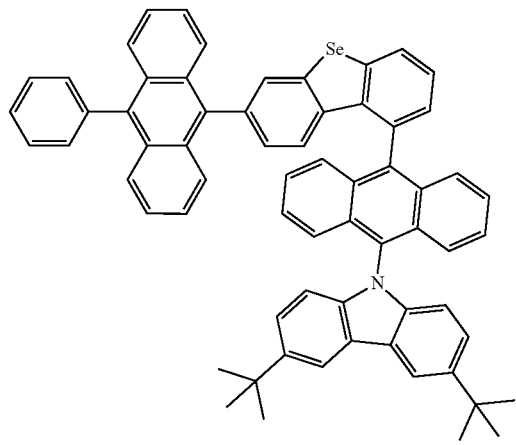
1556
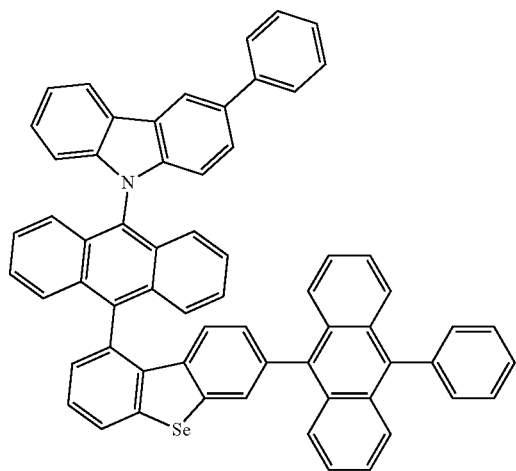
1558
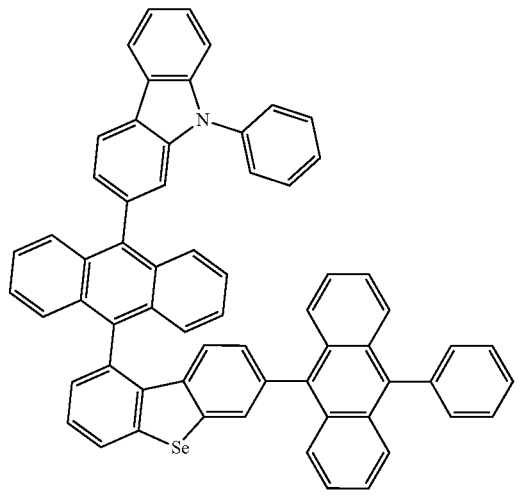

-continued
1559
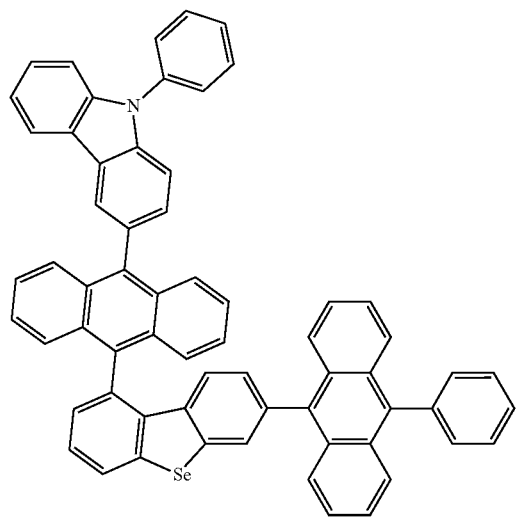
1560
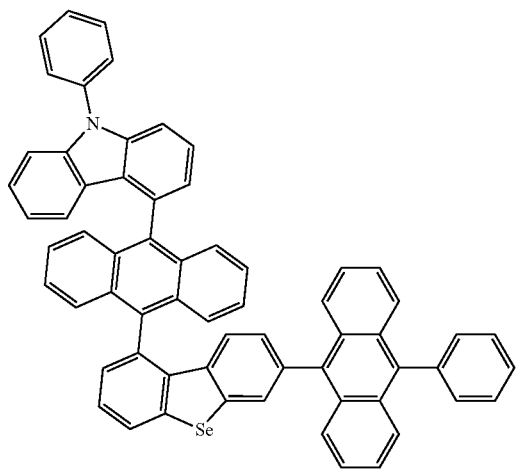
1561
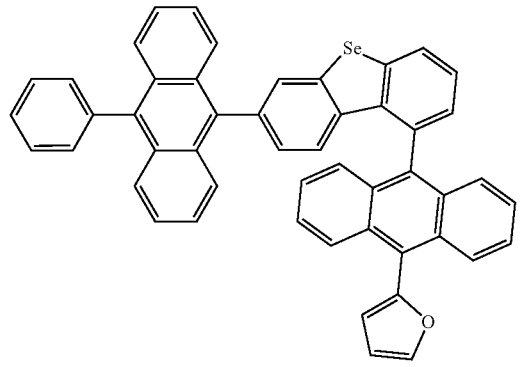
1562
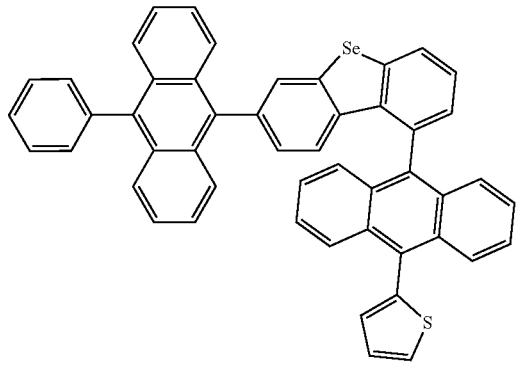
1563
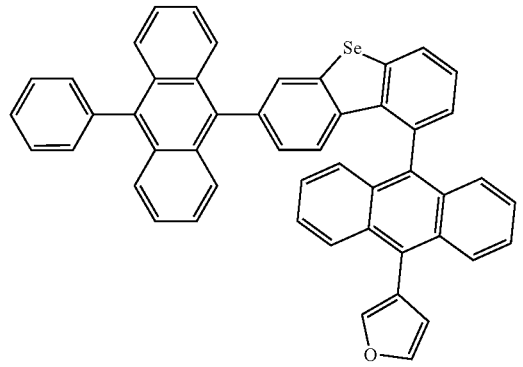
1564
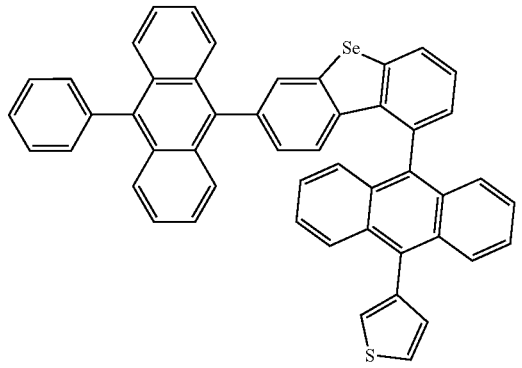

2041 2042
1565 1566
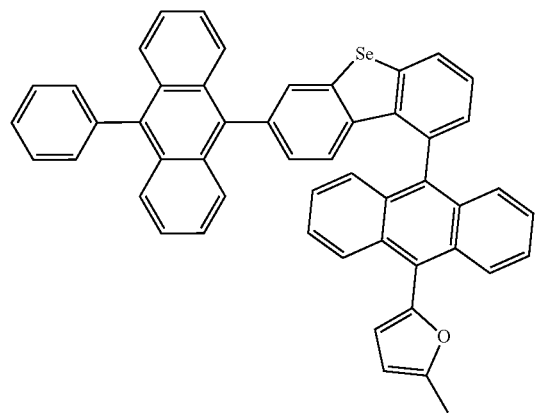 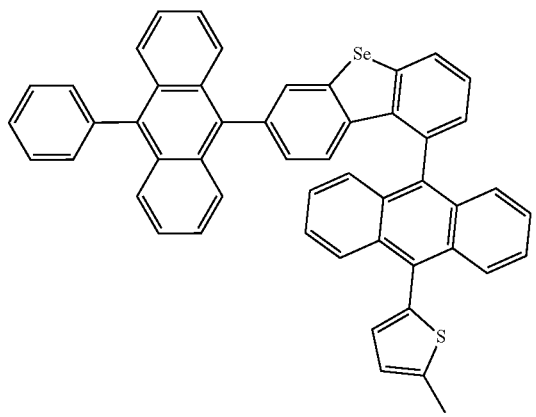
1567 1568
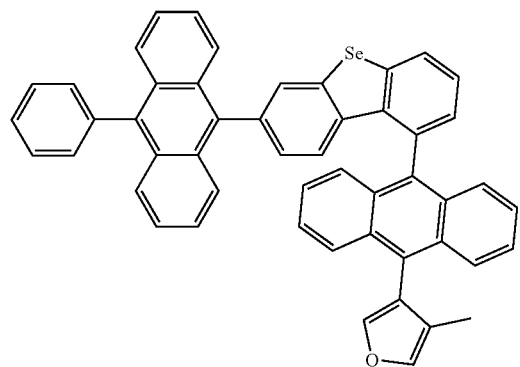 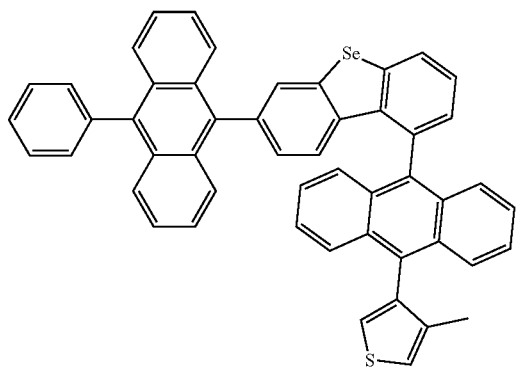
1569 1570
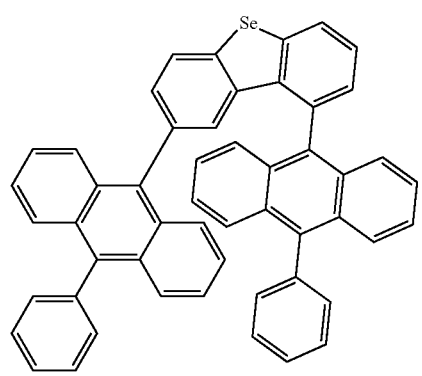 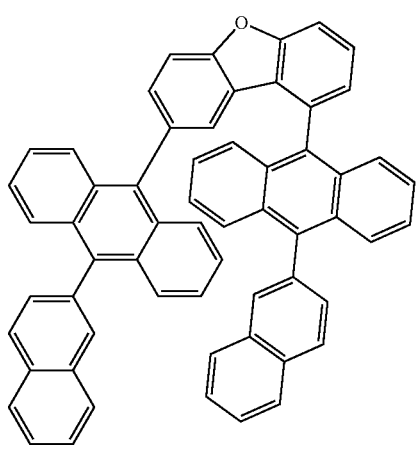

-continued
1571
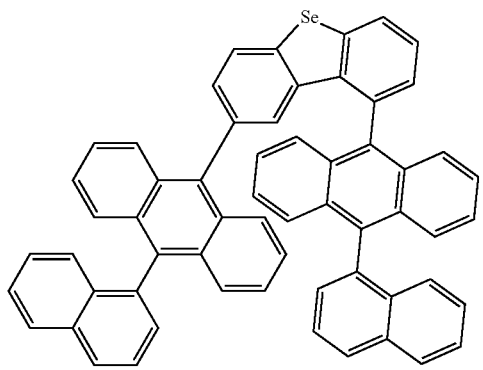
1572
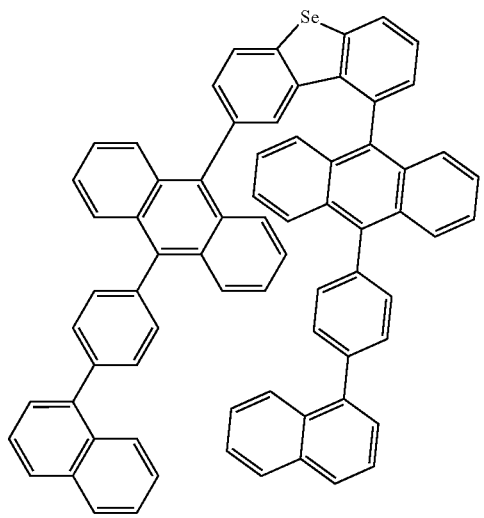
1573
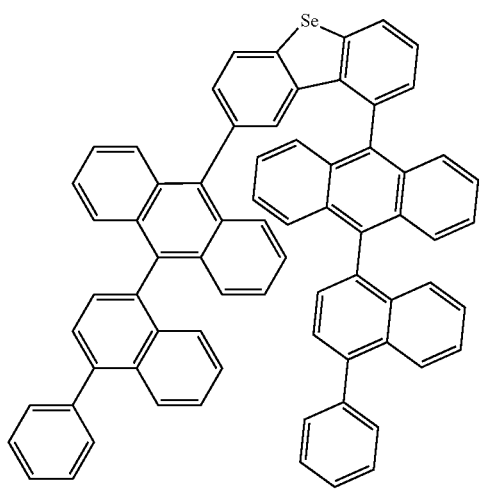
1574
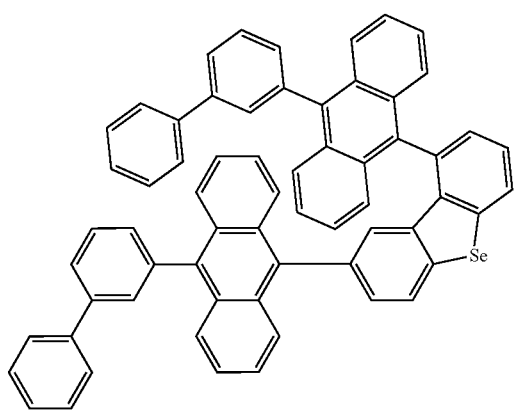
1575
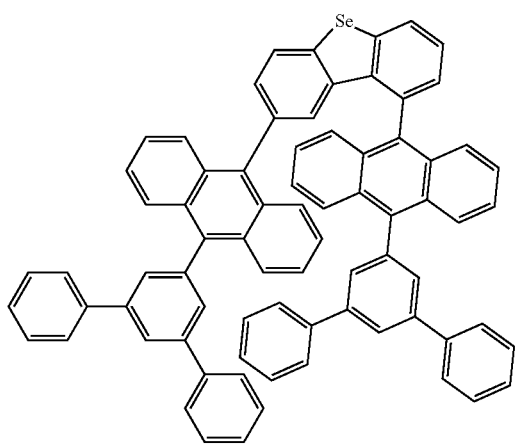
1576
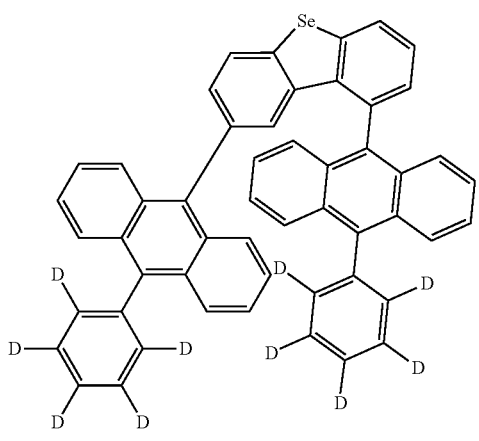

-continued
2045
1577
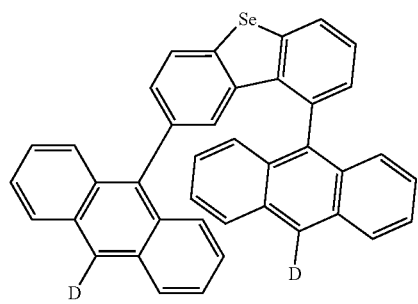
1579
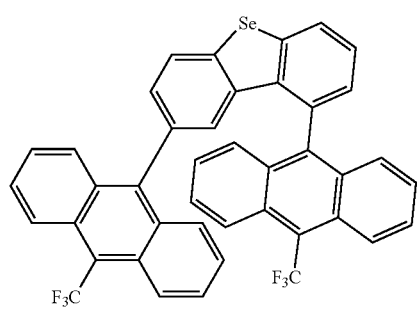
1581
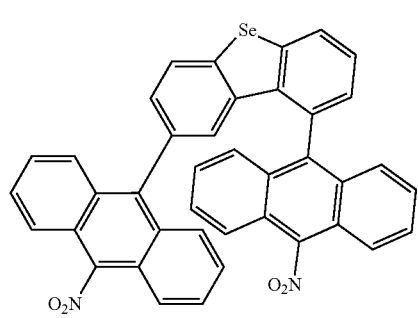
1583
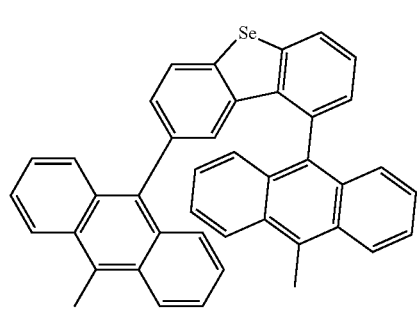
1585
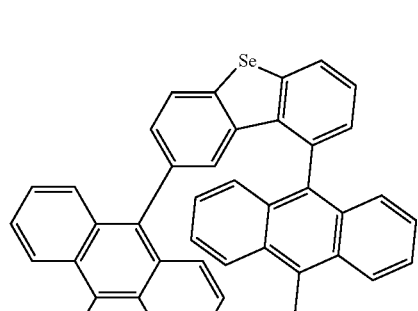
2046
1578
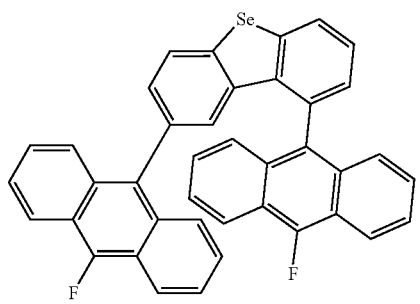
1580
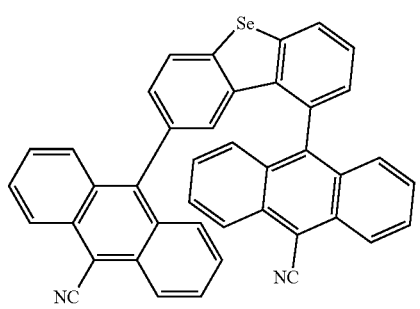
1582
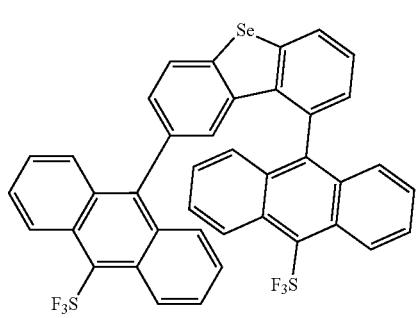
1584
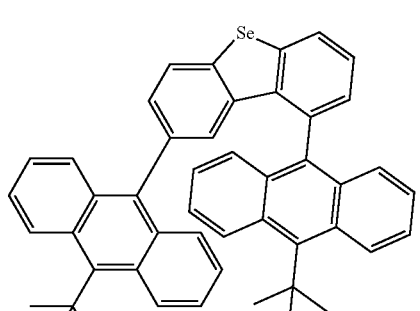
1586
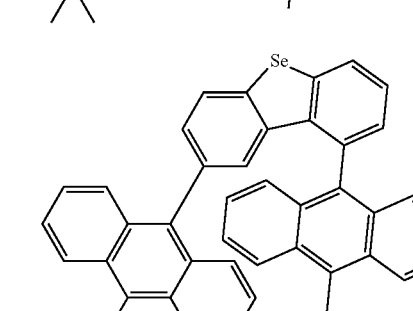

-continued
1587
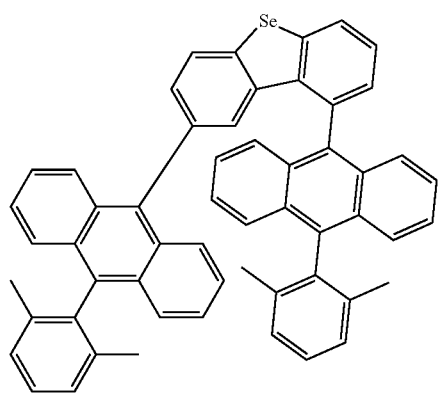
1588
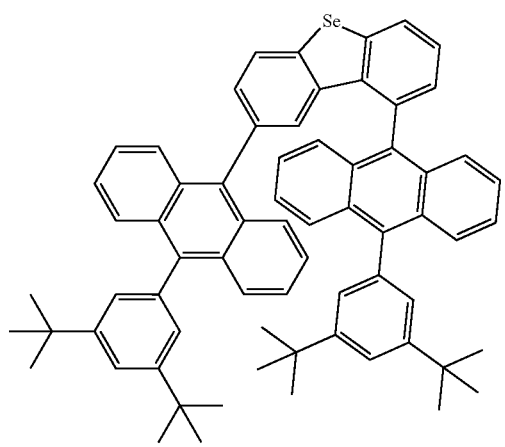
1590
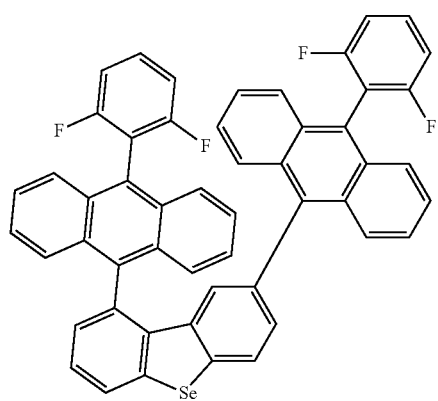
1589
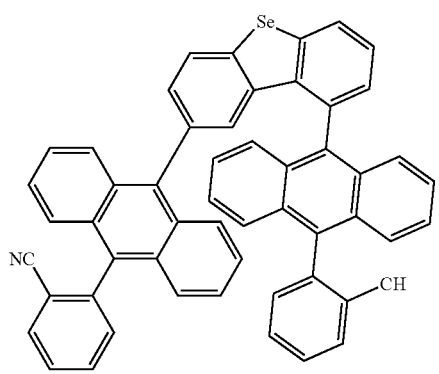
1591
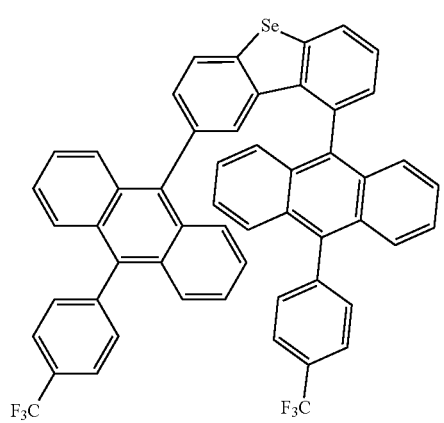
1592
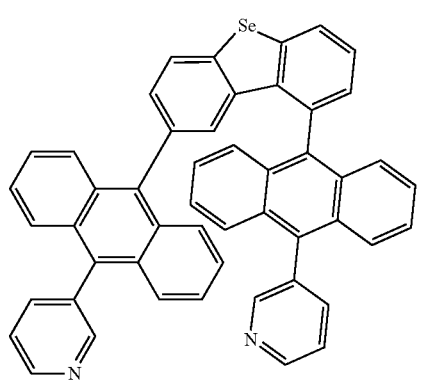

-continued
1593
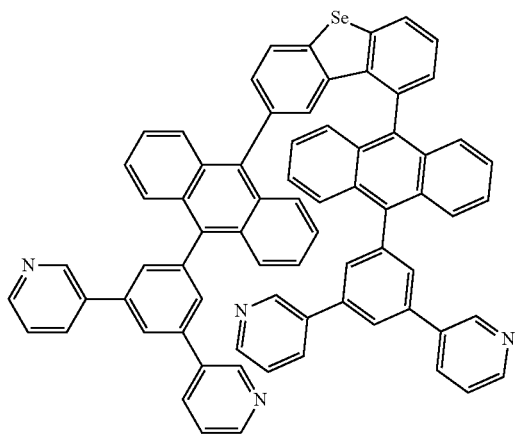
1594
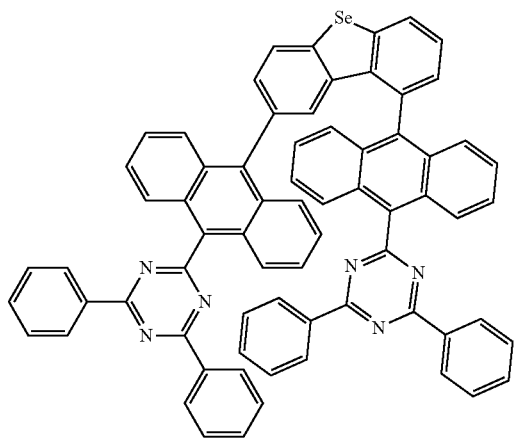
1595
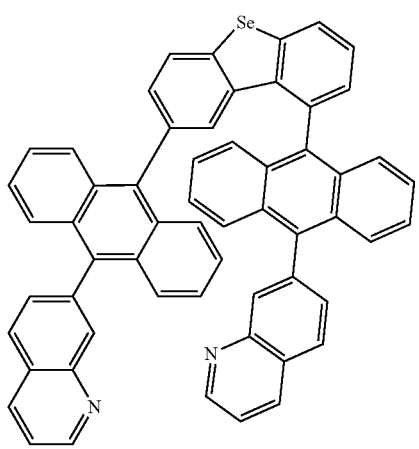
1596
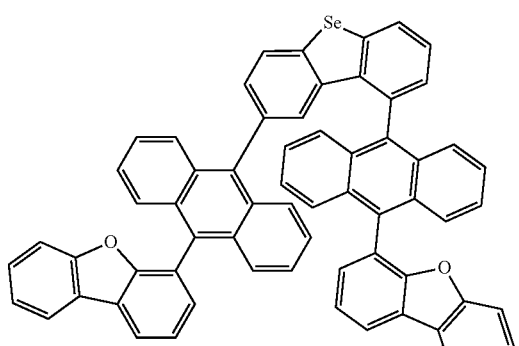
1597
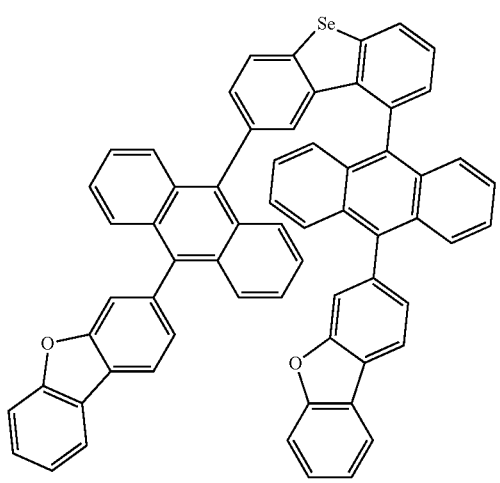
1598
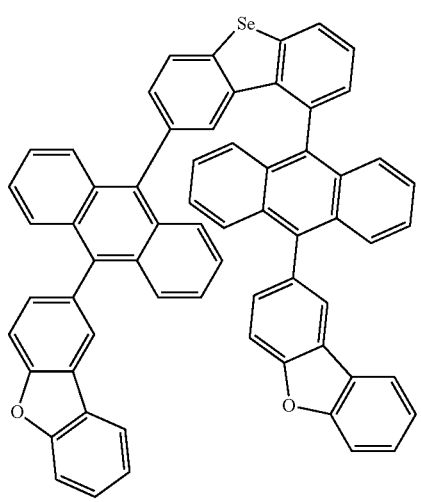

-continued
2051 1599 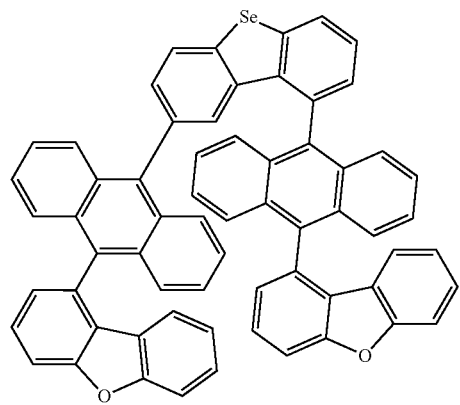
2052 1600 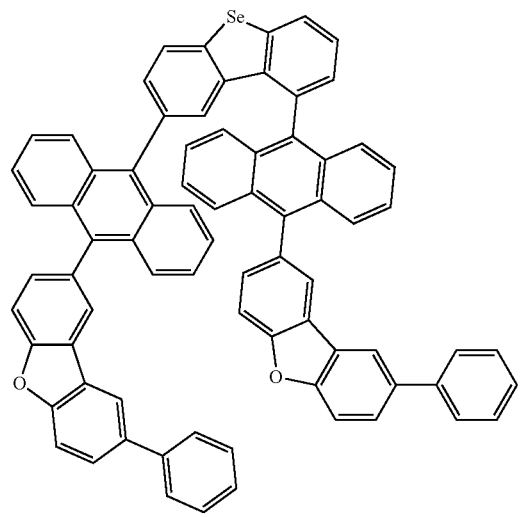
2051 1601 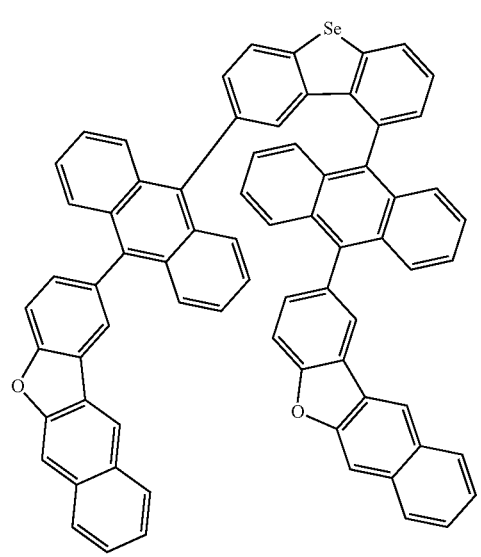
2052 1602 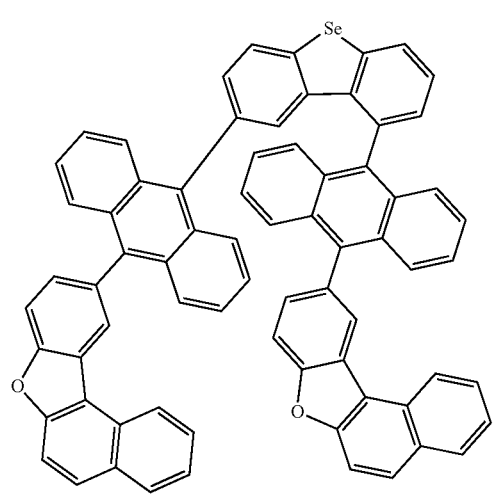

-continued
1603
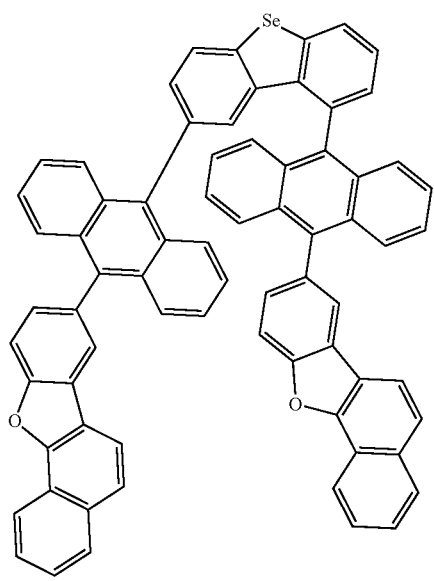
1604
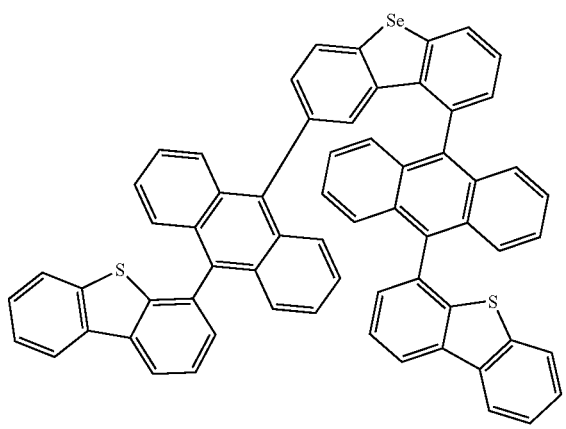
1605
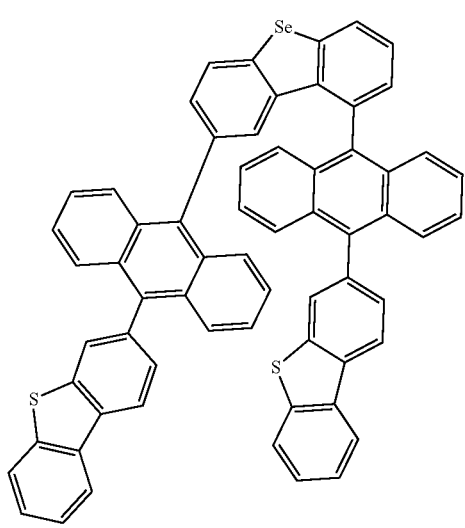
1606

-continued
1607
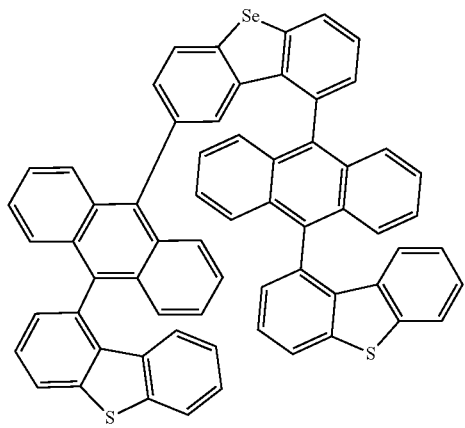
1608
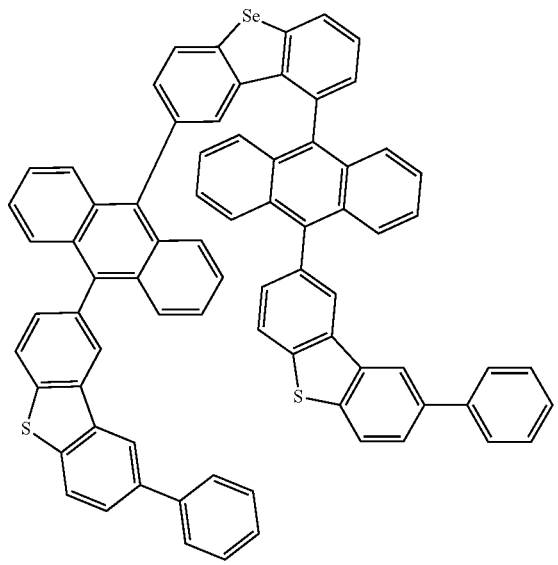
1609
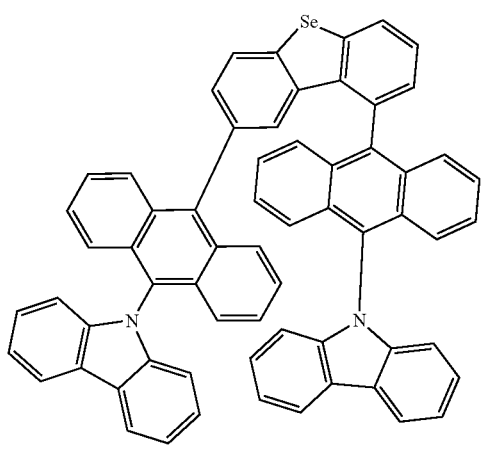
1610
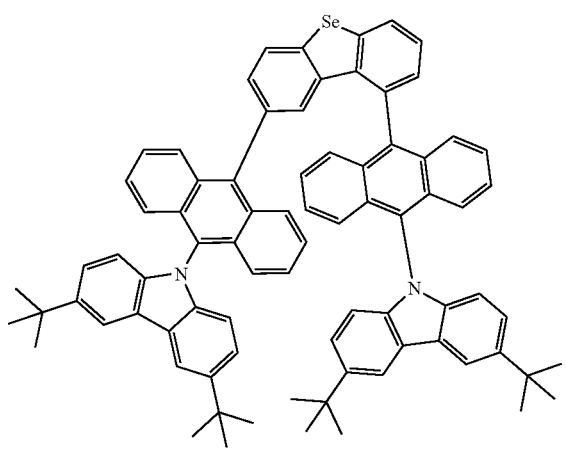
1611
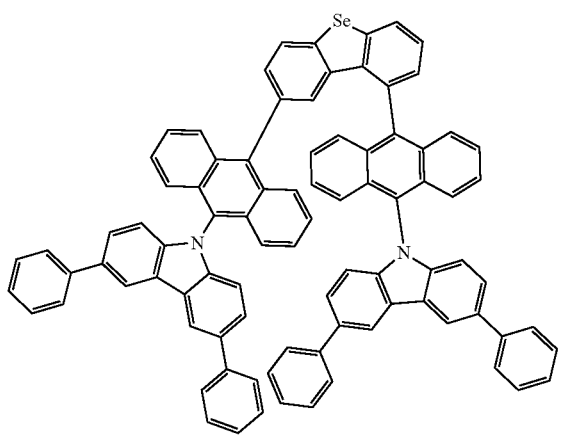
1612
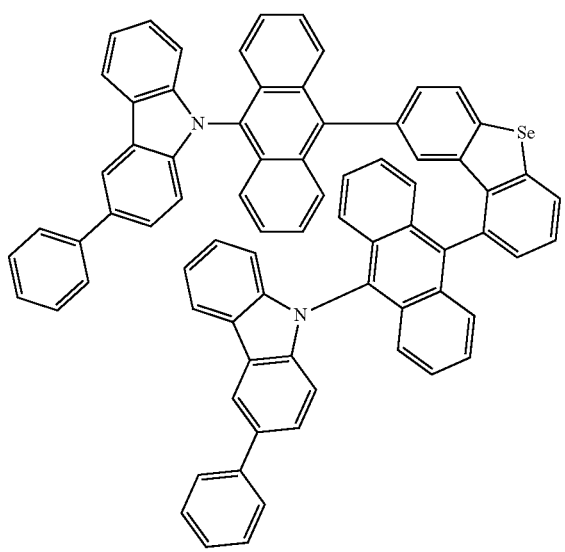

-continued
1613
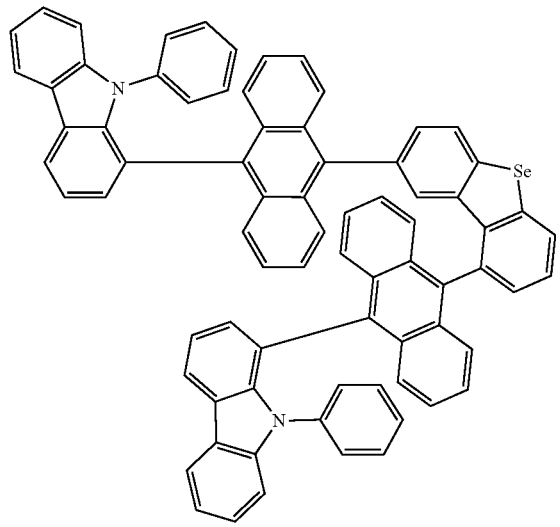
1614
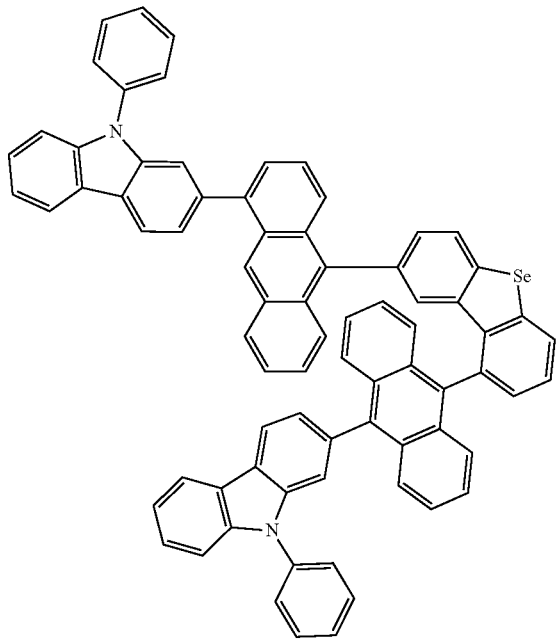
1615
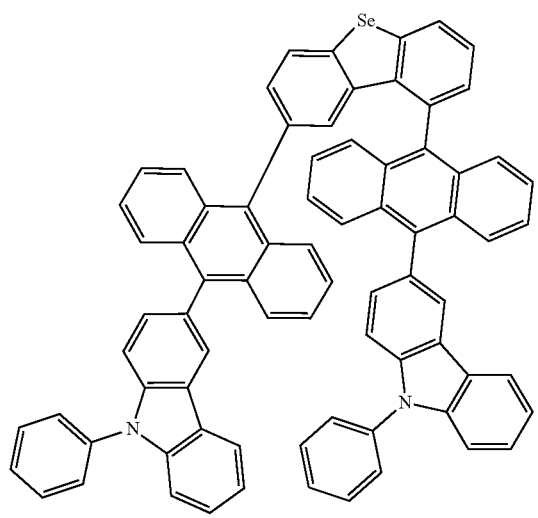
1616
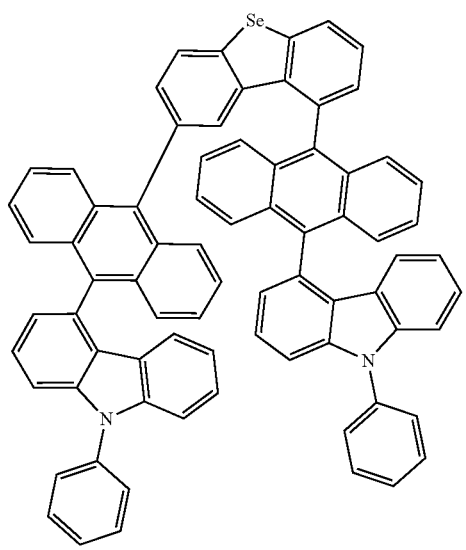
1617
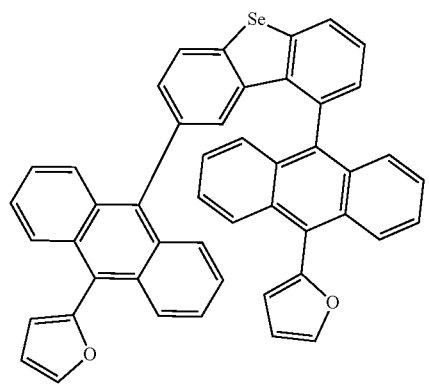
1618
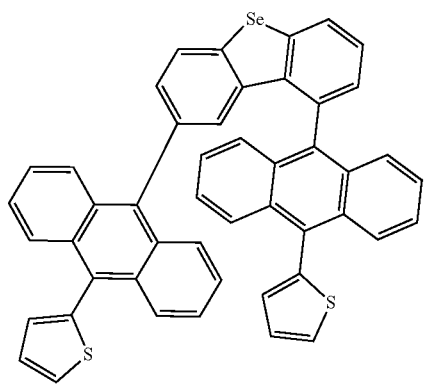

-continued
| 1619 | 1620 |
|---|---|
| 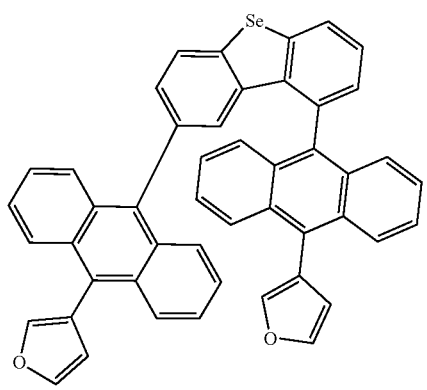 | 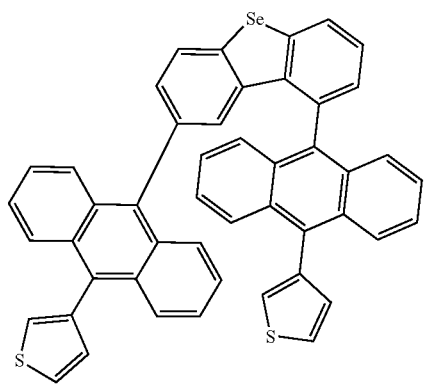 |
| 1621 | 1622 |
| 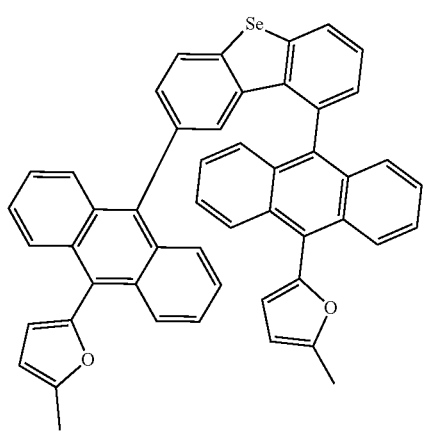 | 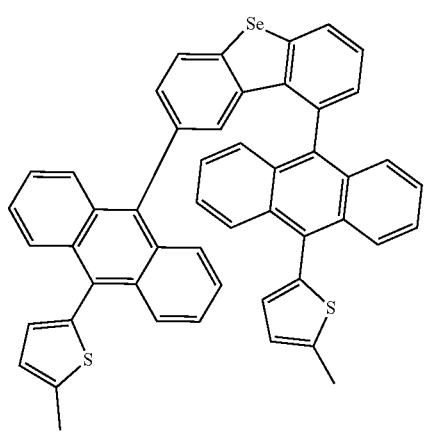 |
| 1623 | 1624 |
| 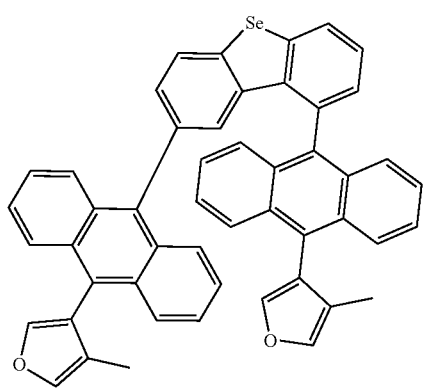 | 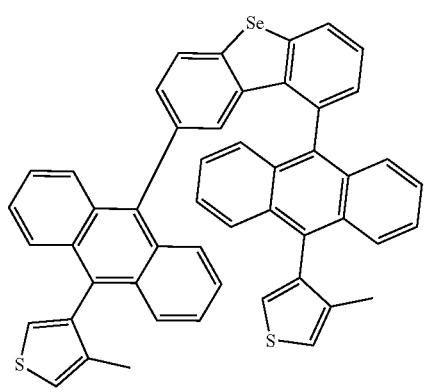 |
| 1625 | 1626 |
| 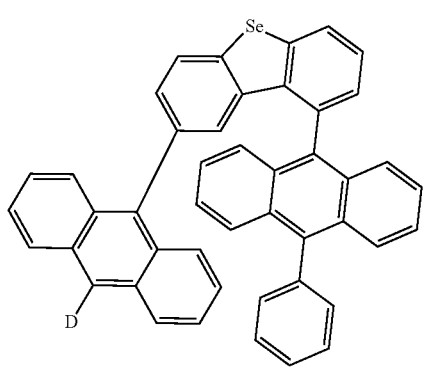 | 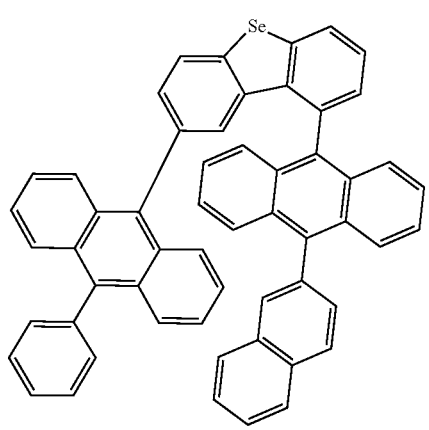 |

-continued
1627
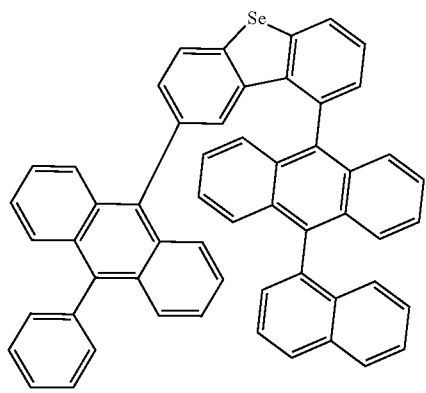
1628
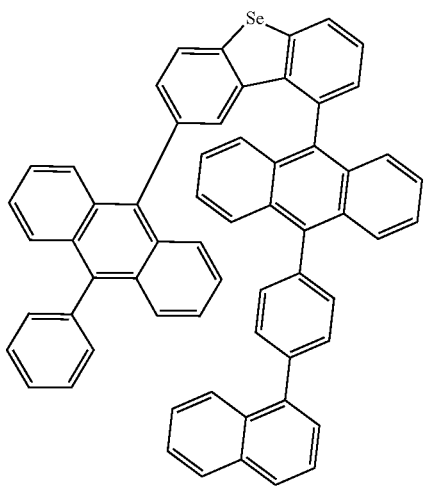
1629
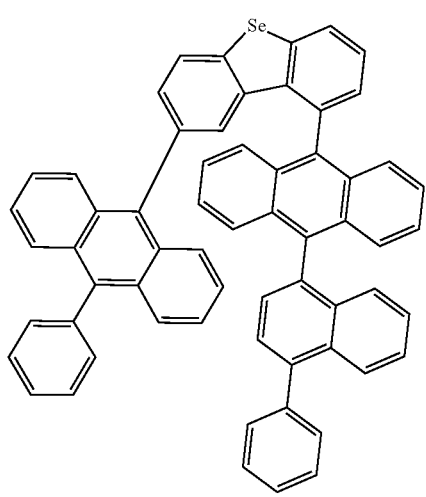
1630
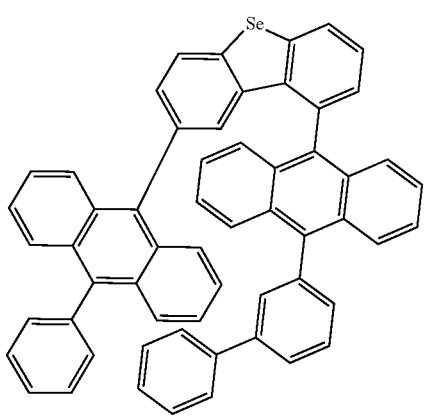
1631
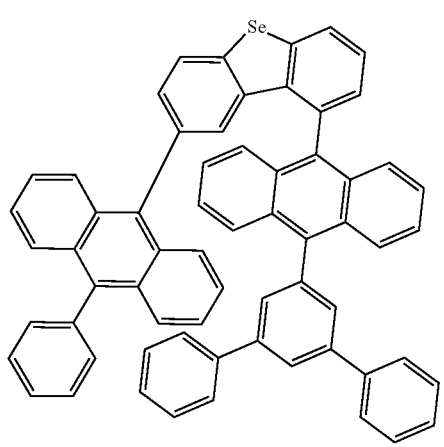
1632
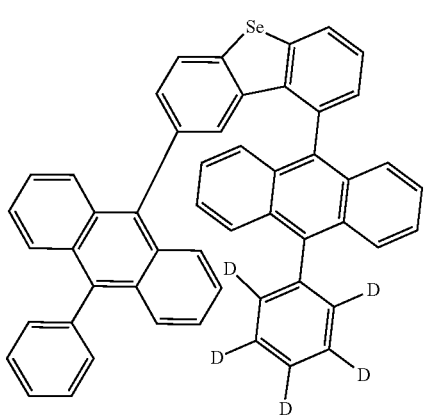

2063 / 2064
-continued
| 1633 | 1634 |
|---|---|
| 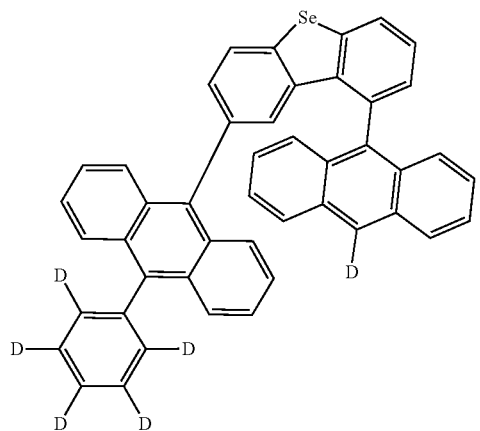 | 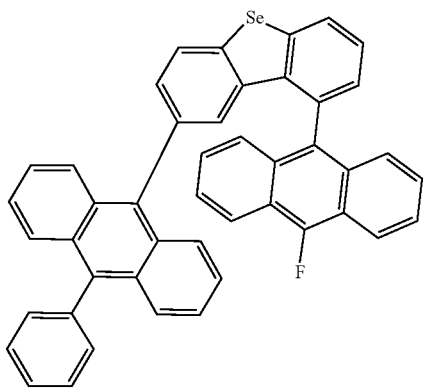 |
| 1635 | 1636 |
| 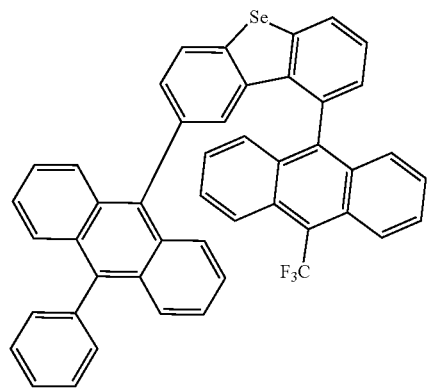 | 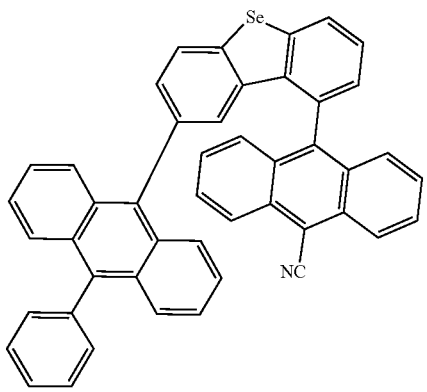 |
| 1637 | 1638 |
| 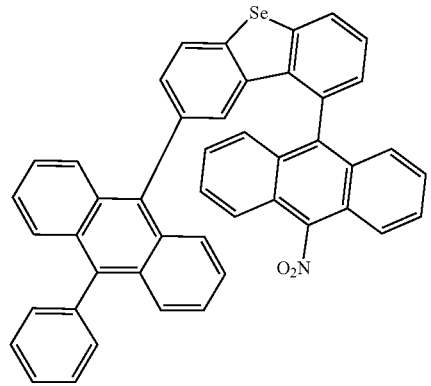 | 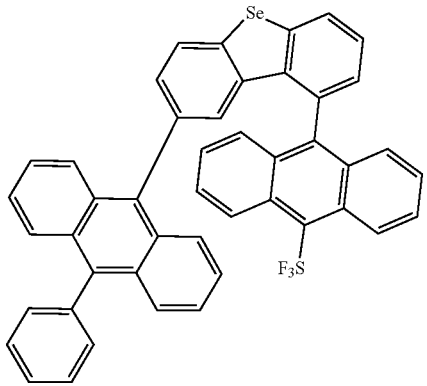 |
| 1639 | 1640 |
| 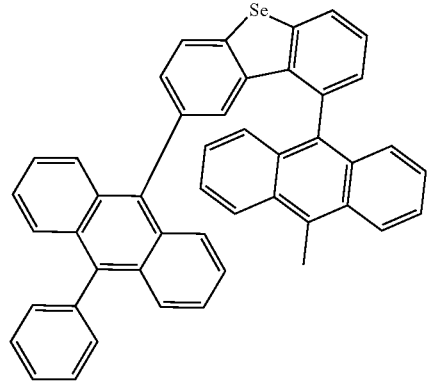 | 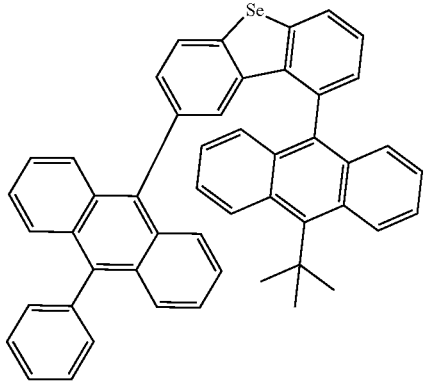 |

-continued
1641
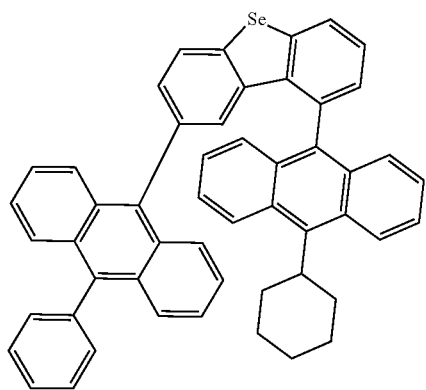
1642
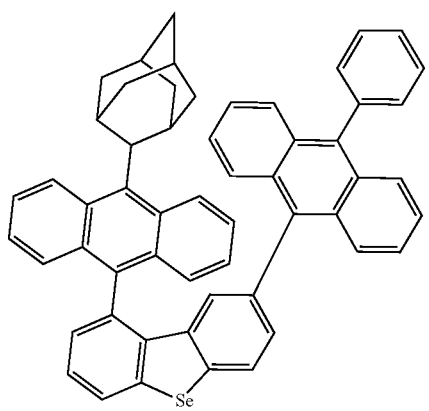
1643
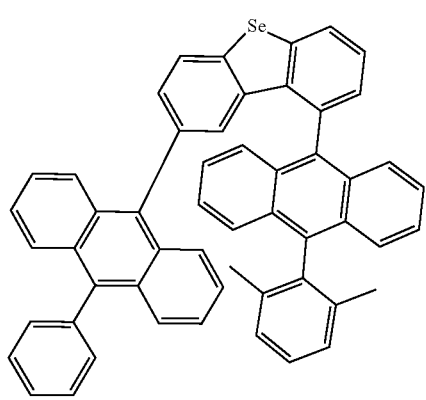
1644
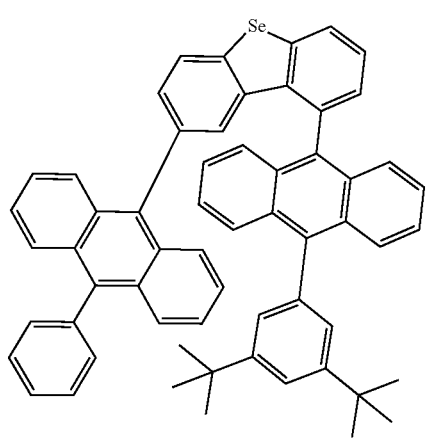
1645
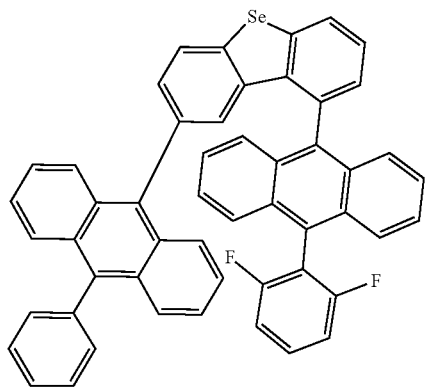
1646
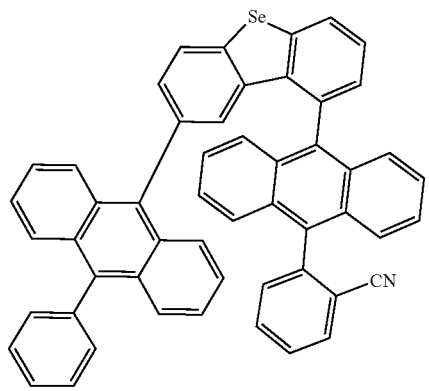
1647
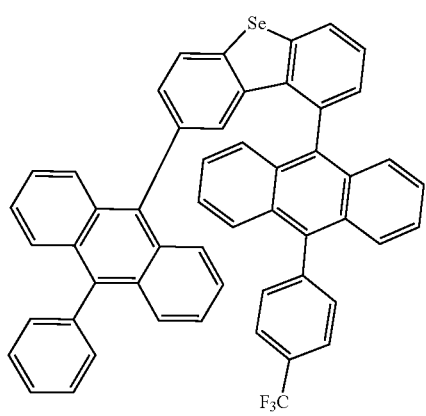
1648
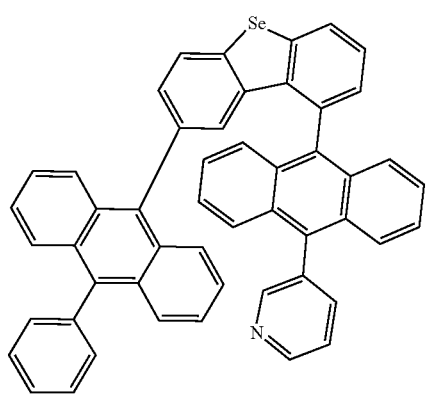

-continued
1649
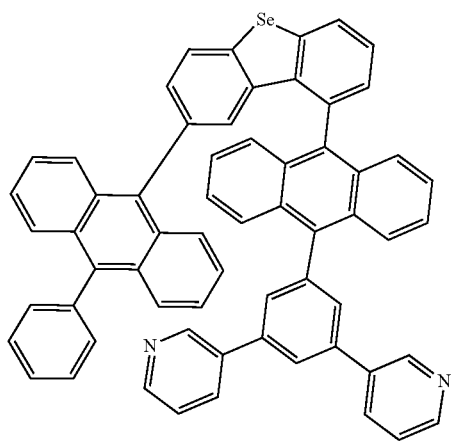
1650
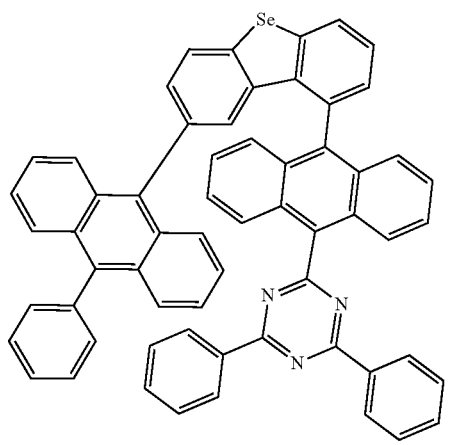
1651
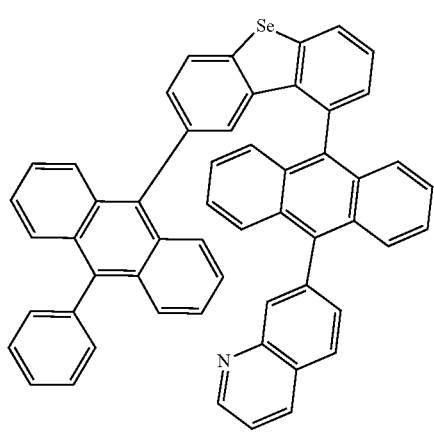
1652
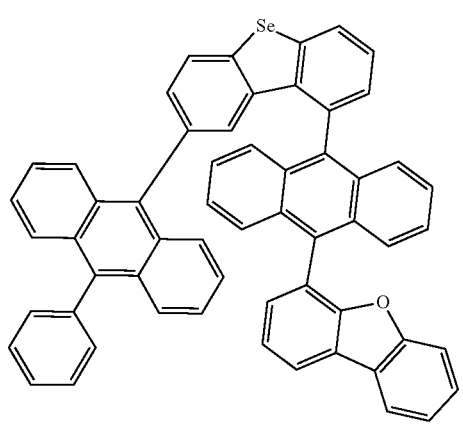
1653
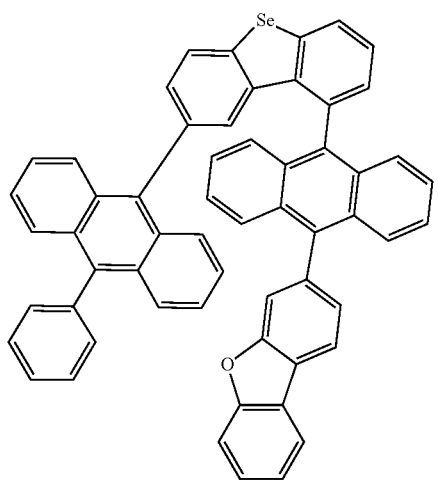
1654
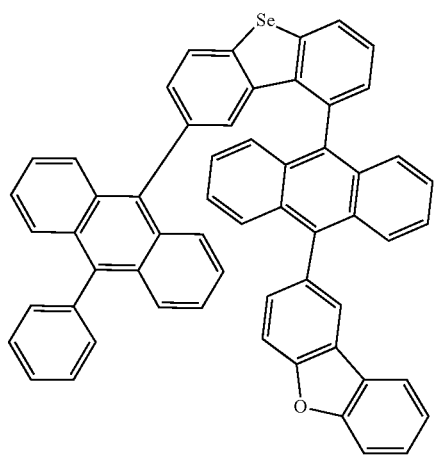

-continued
1655
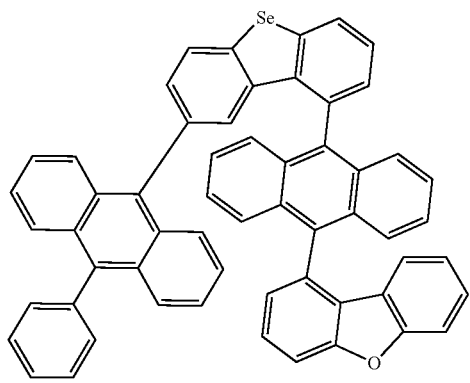
1656
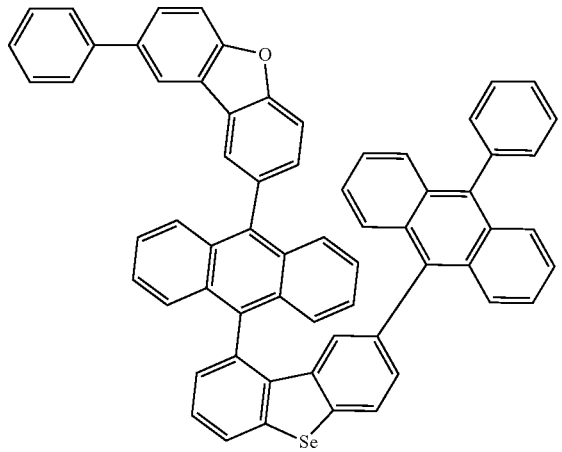
1657
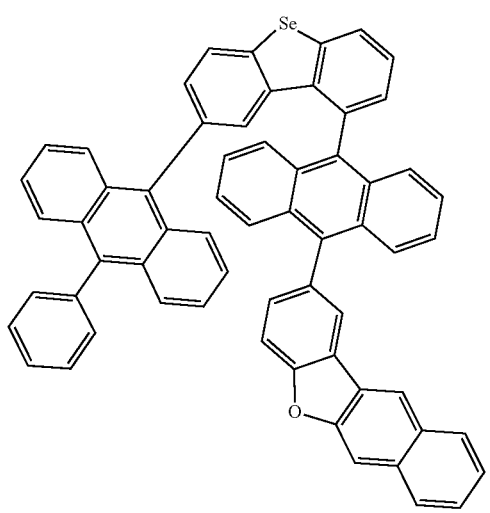
1658
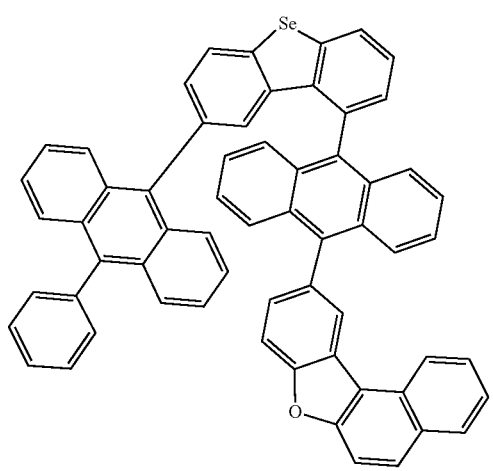
1659
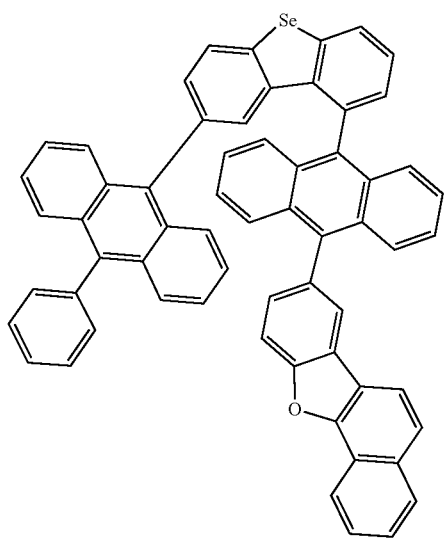
1660
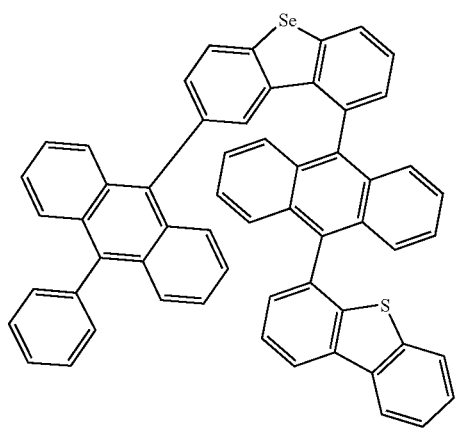

-continued
1661
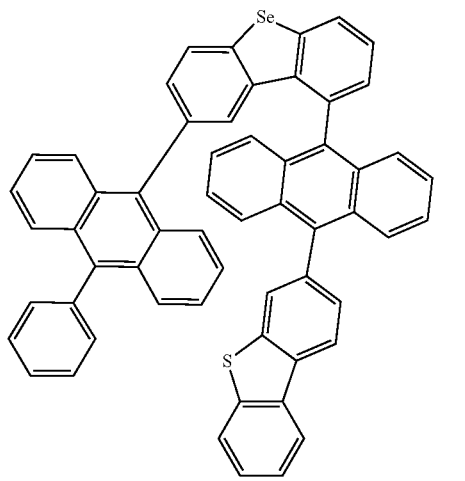
1662
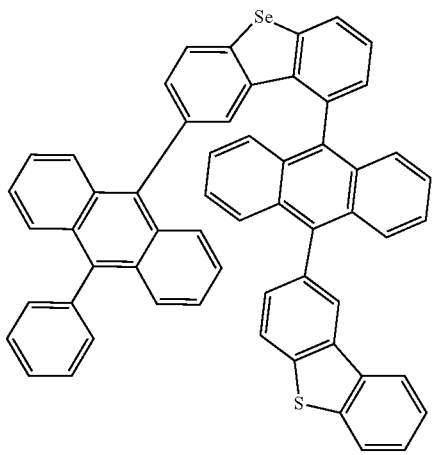
1663
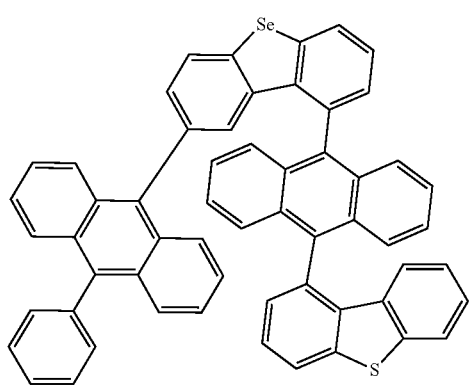
1664
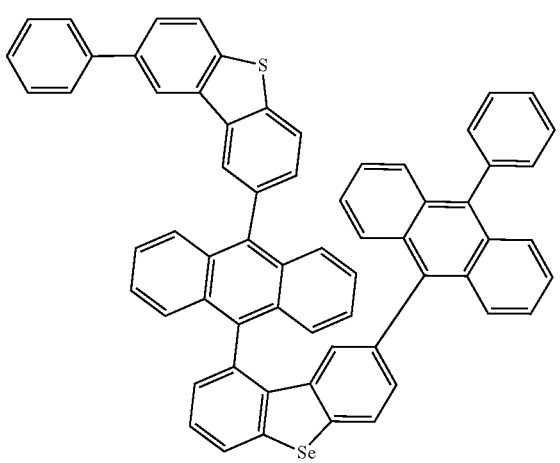
1665
1666
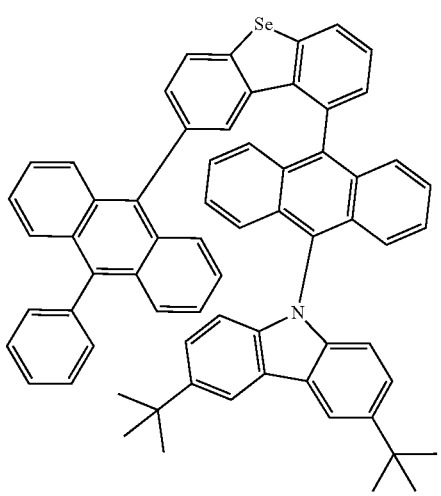

-continued
1667
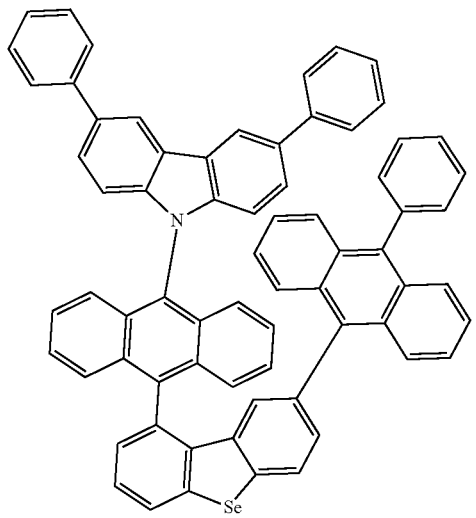
1668
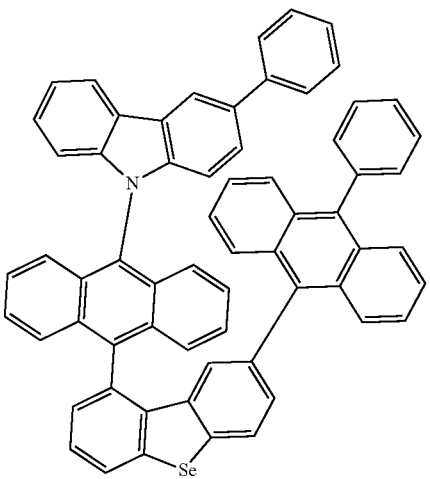
1669
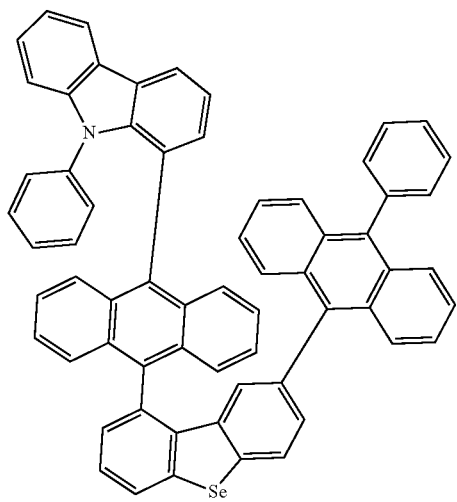
1670
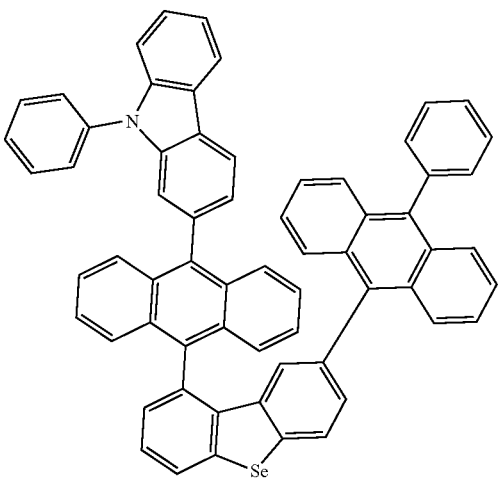
1671
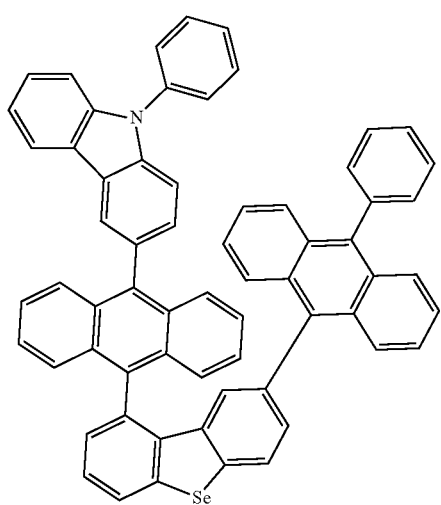
1672
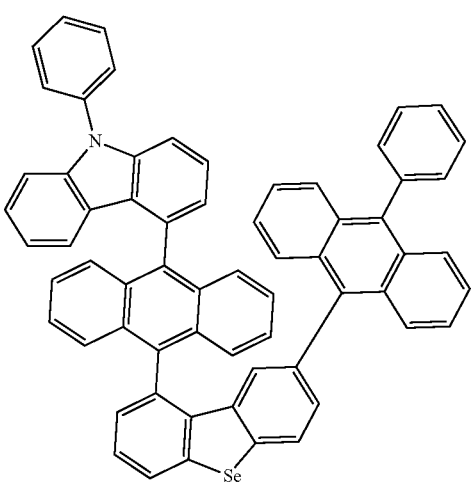

2075 2076
-continued
1673
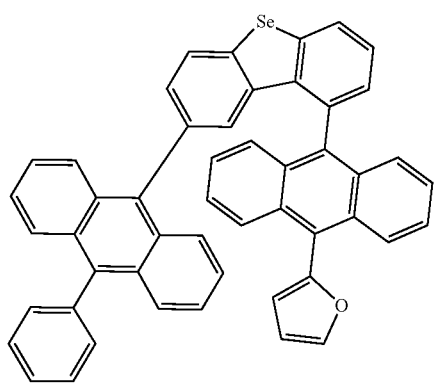
1674
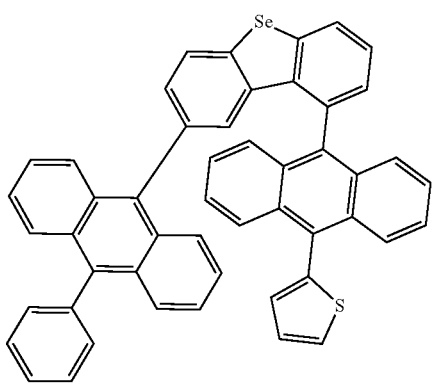
1675
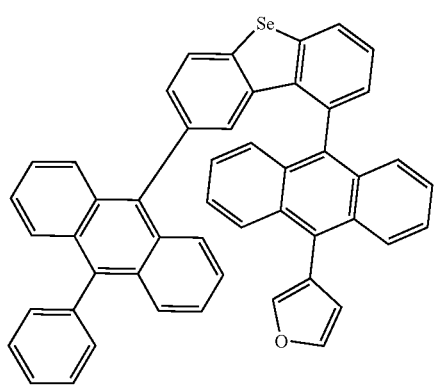
1676
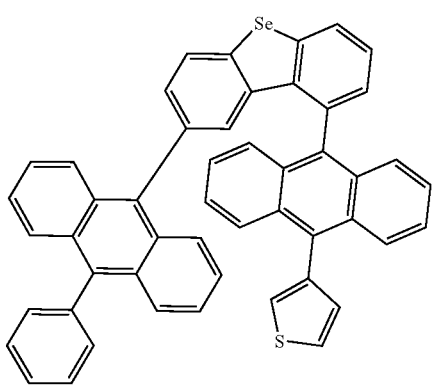
1677
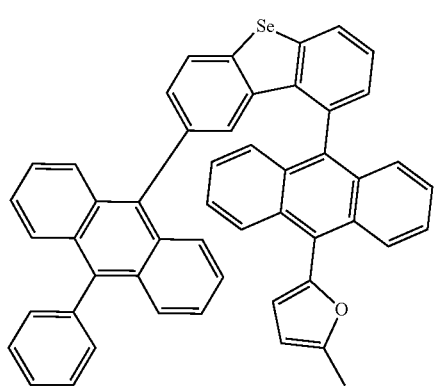
1678
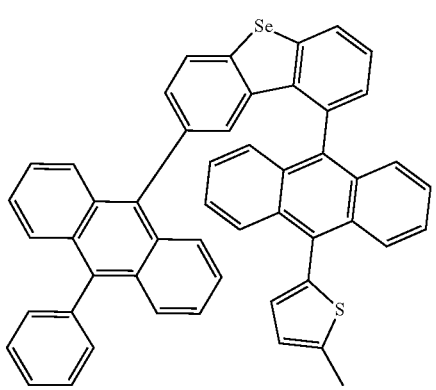
1679
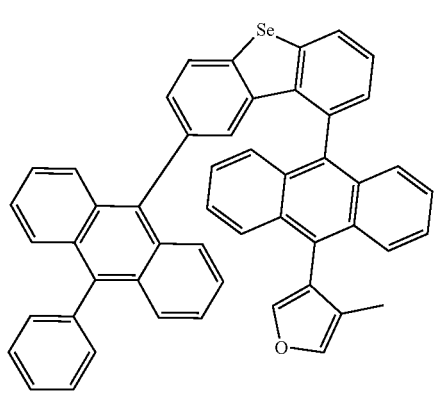
1680
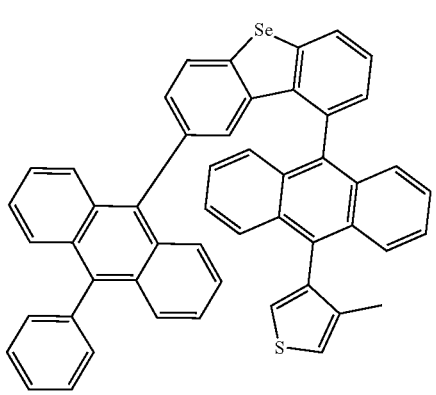

-continued
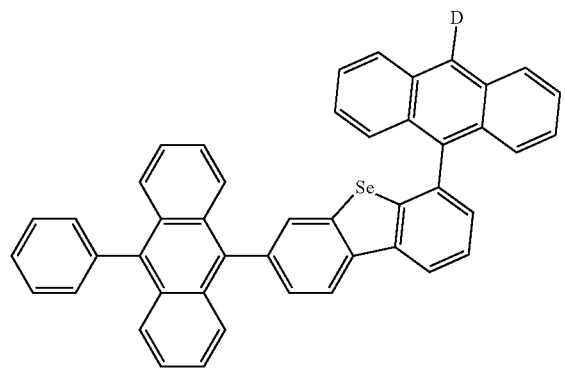

-continued
1687
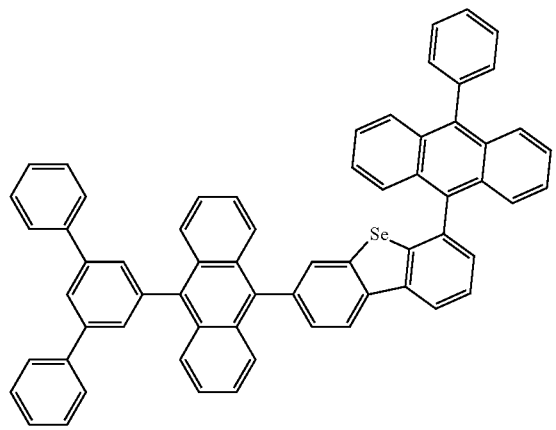
1688
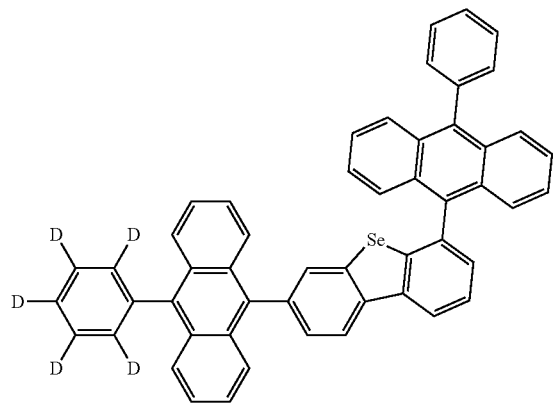
1689
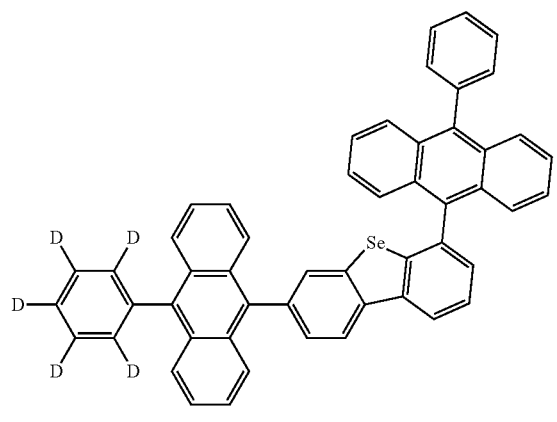
1690
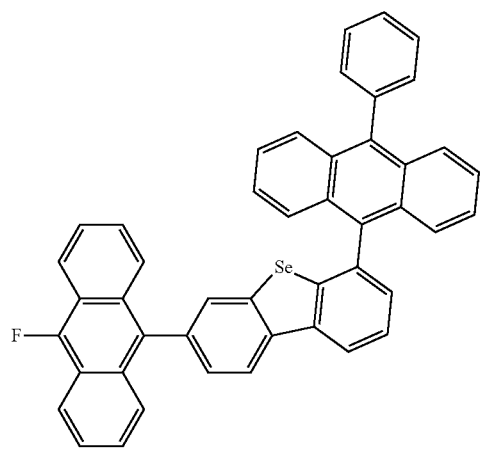
1691
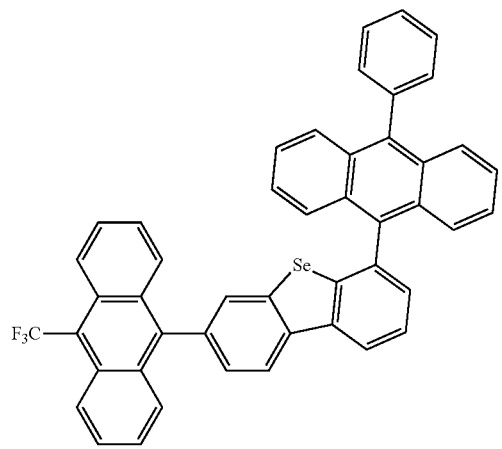
1692
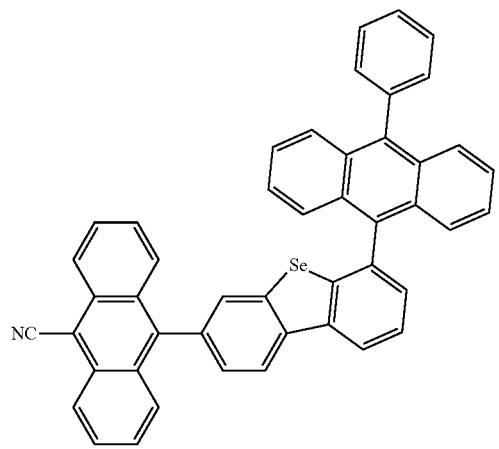

-continued
1693
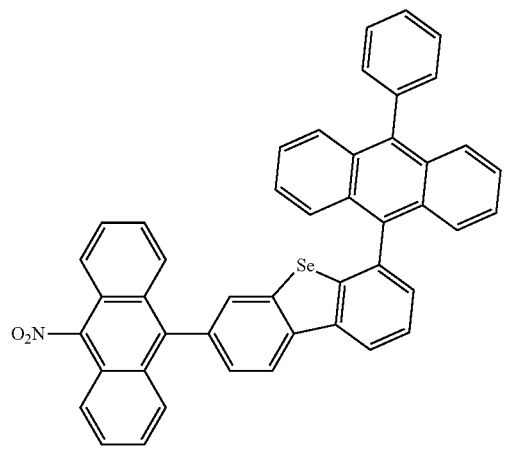
1694
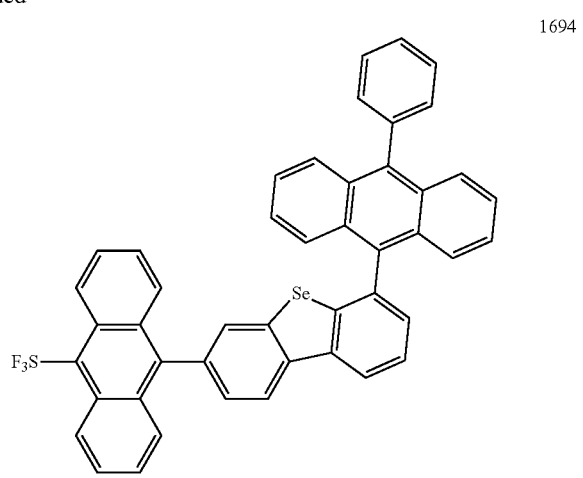
1695
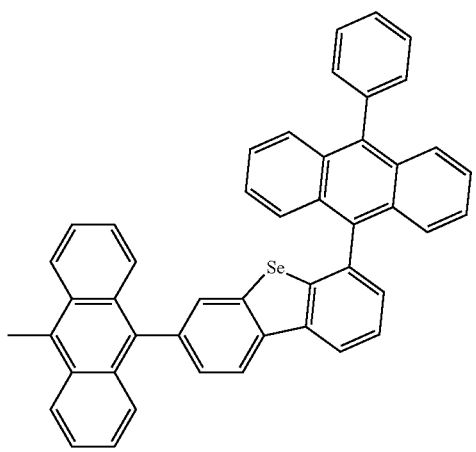
1696
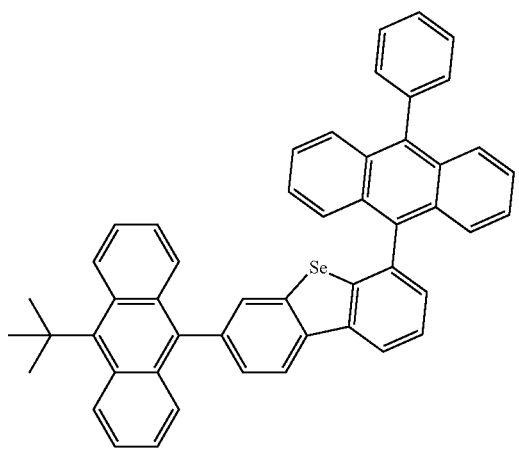
1697
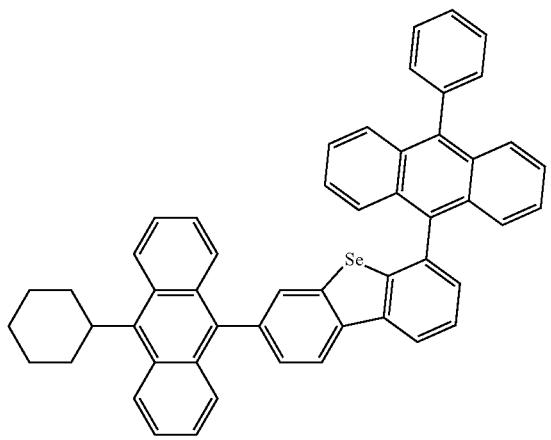
1698
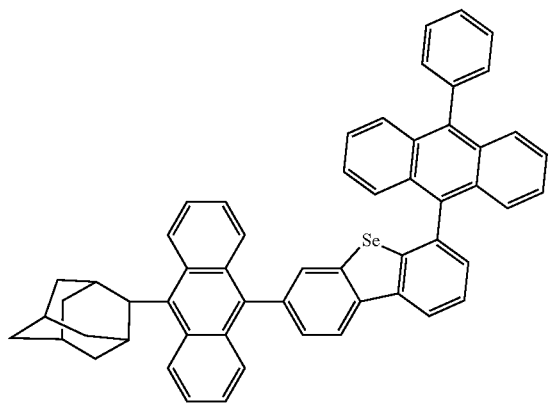

1699
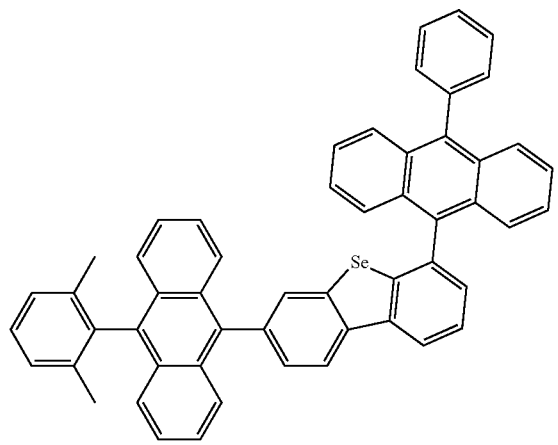
1700
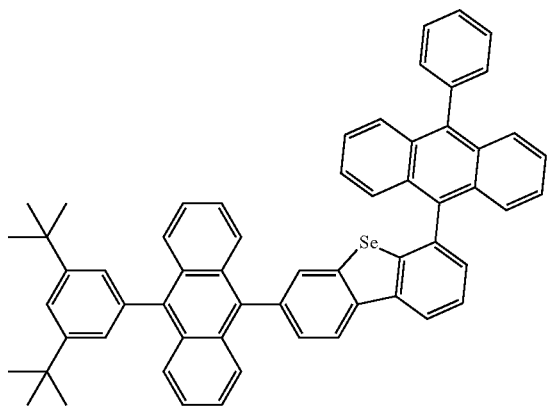
1701
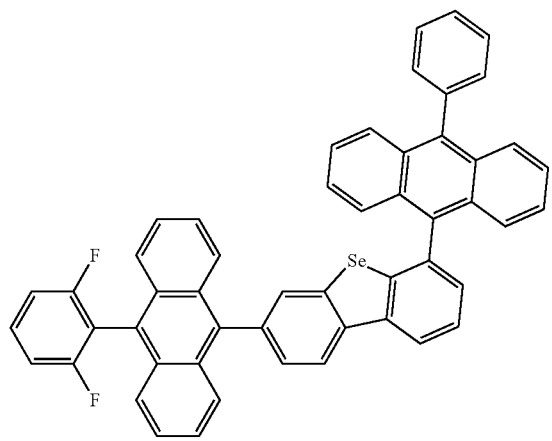
1702
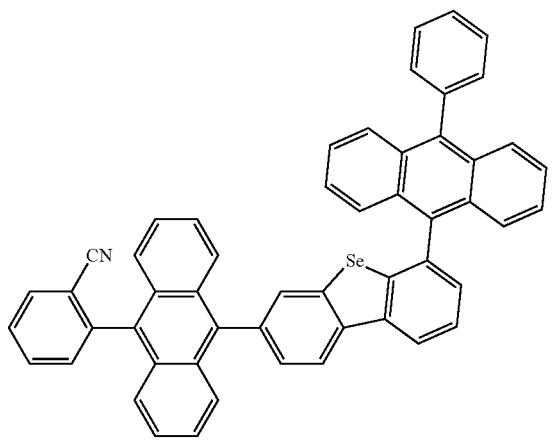
1703
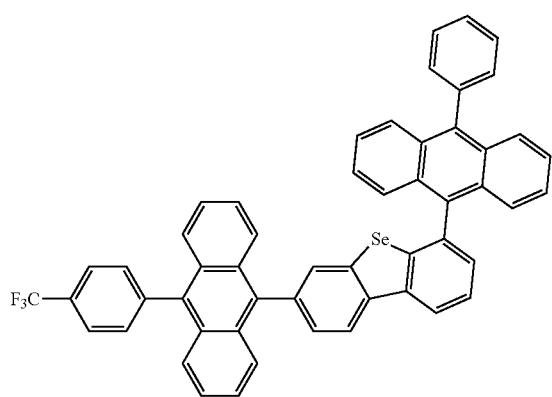
1704
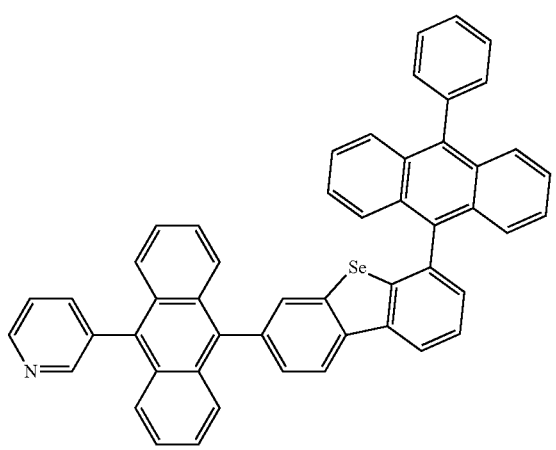

-continued
1705
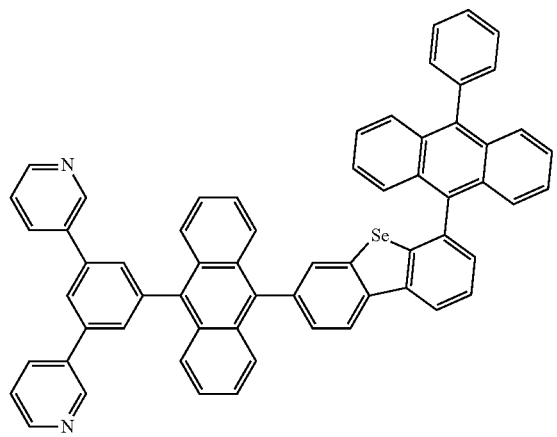
1706
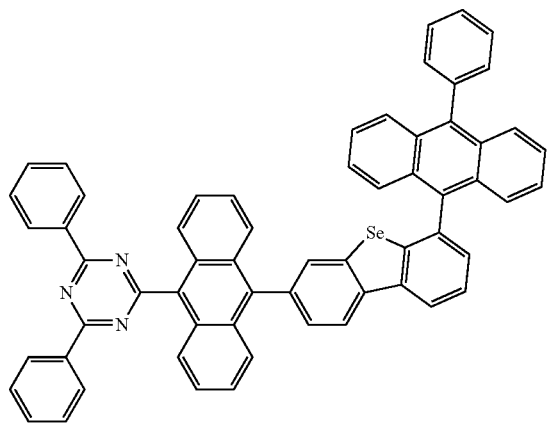
1707
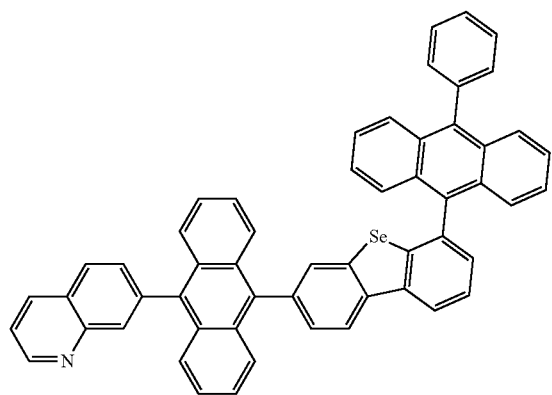
1708
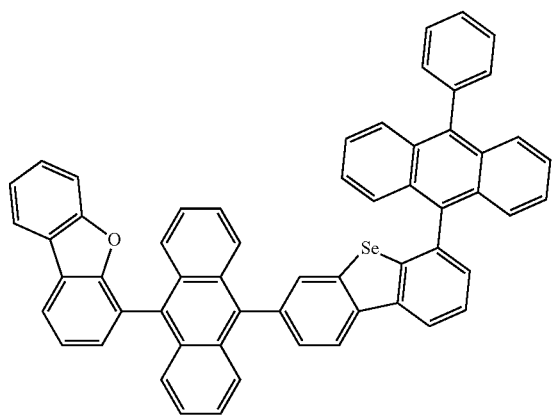
1709
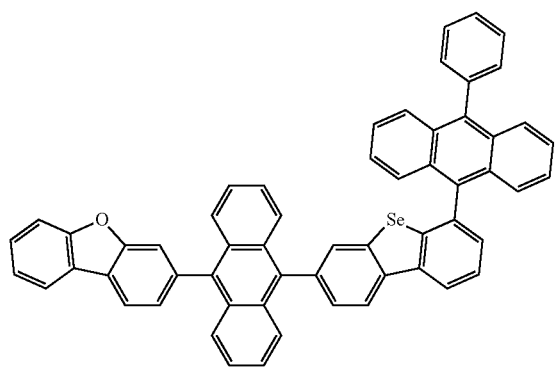
1710
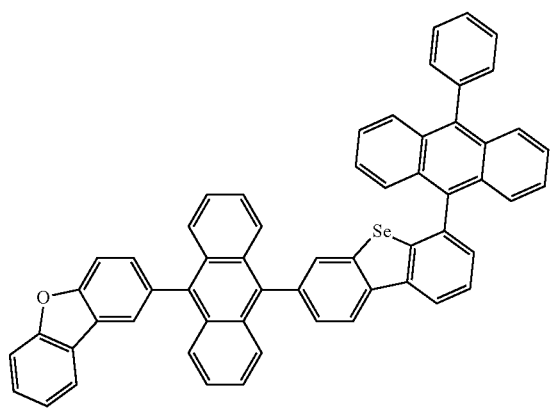

-continued
1711
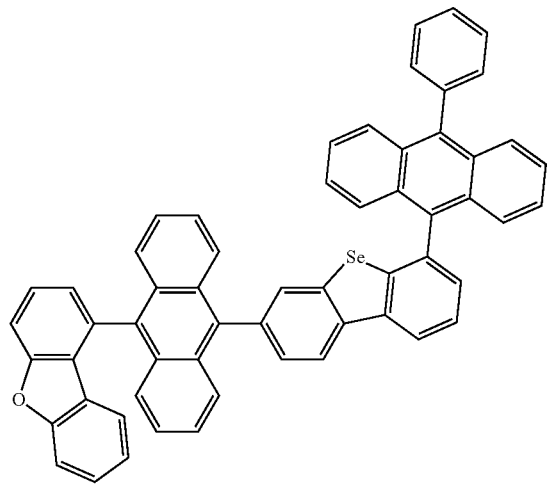
1712
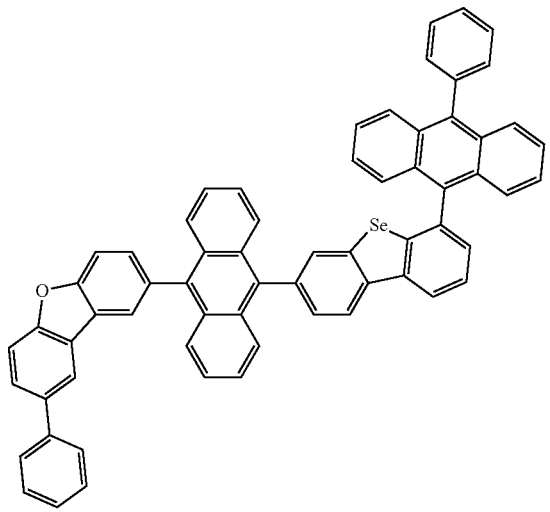
1713
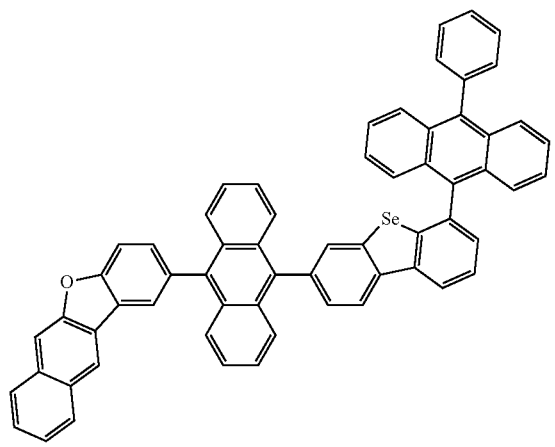
1714
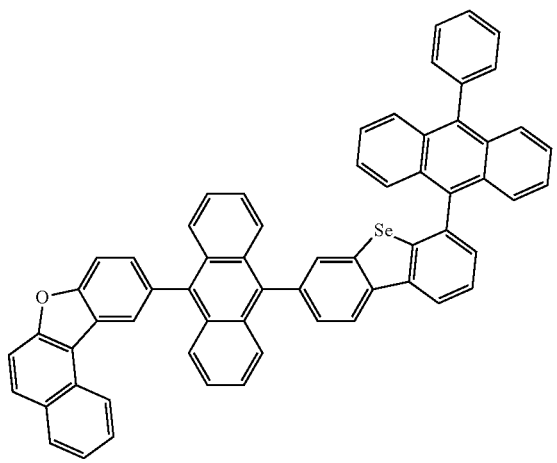
1715
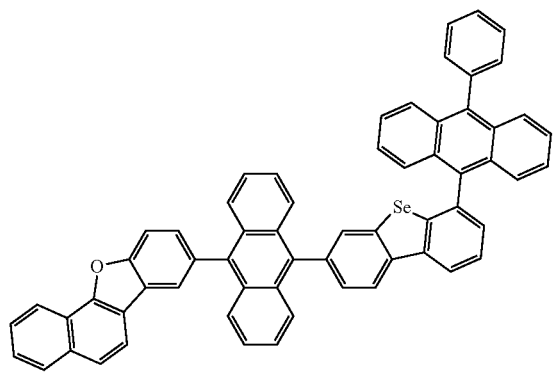
1716
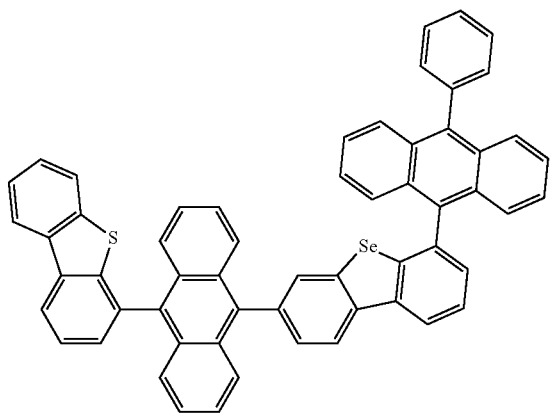

-continued
| 1717 | 1718 |
|---|---|
| 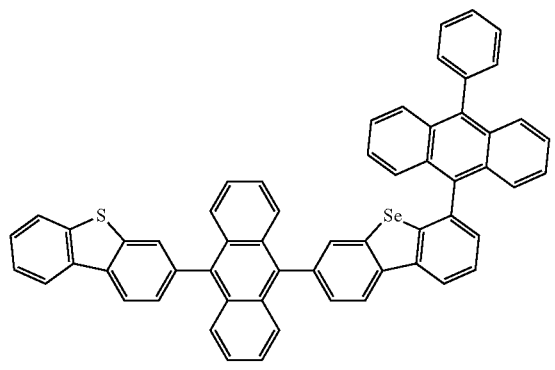 | 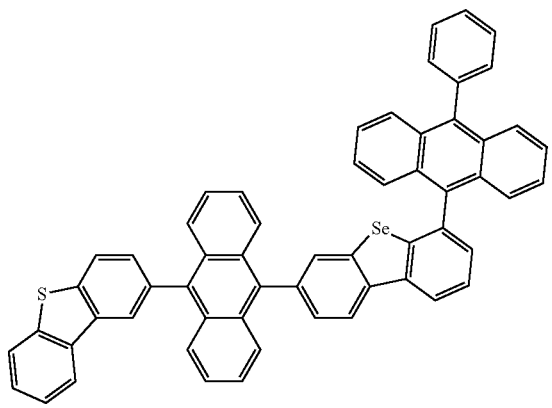 |
| 1719 | 1720 |
| 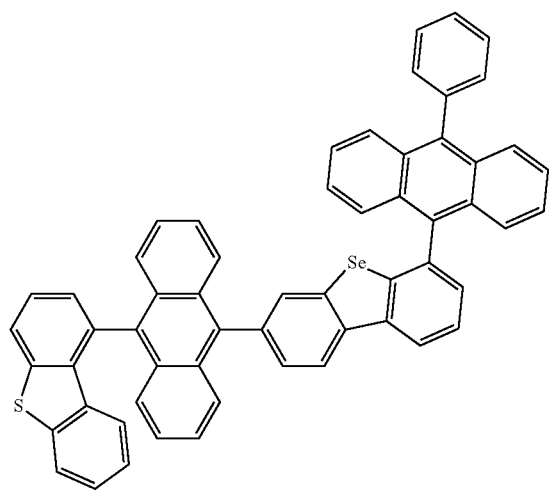 | 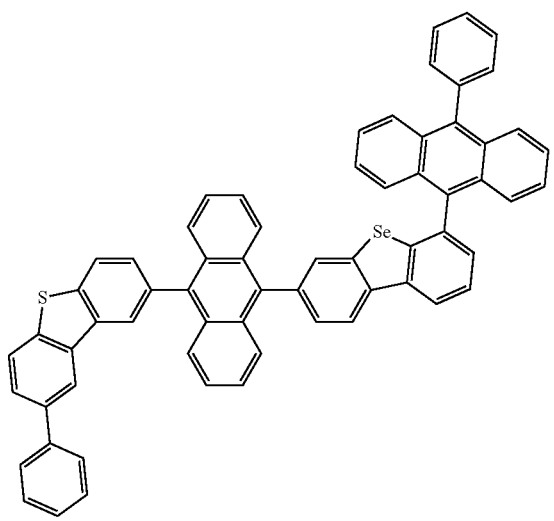 |
| 1721 | 1722 |
| 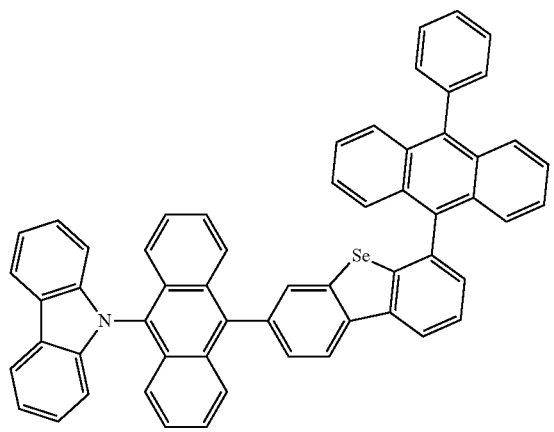 | 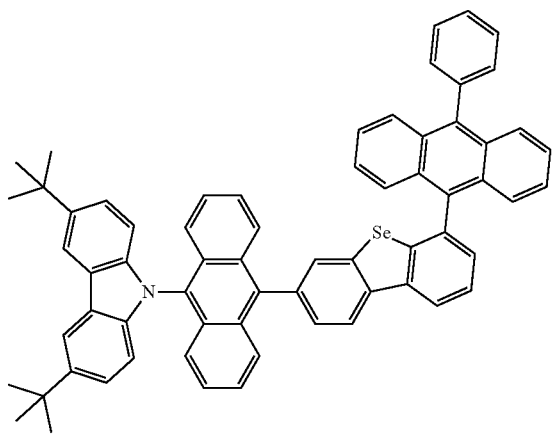 |

1723
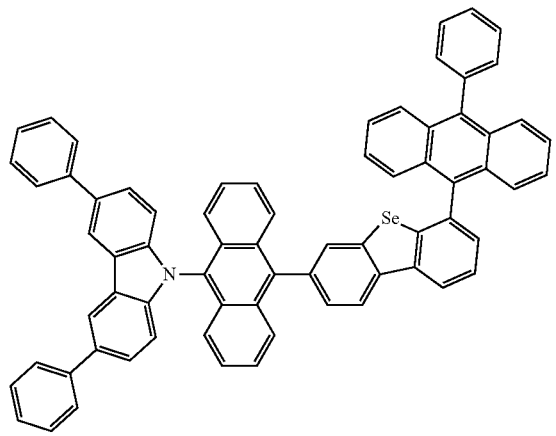
1724
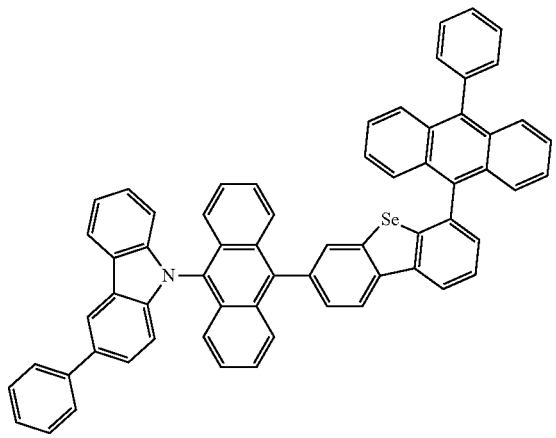
1725
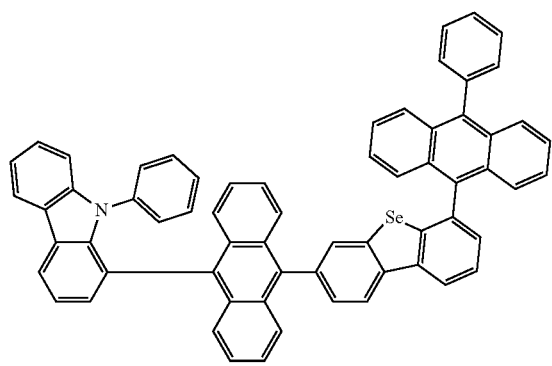
1726
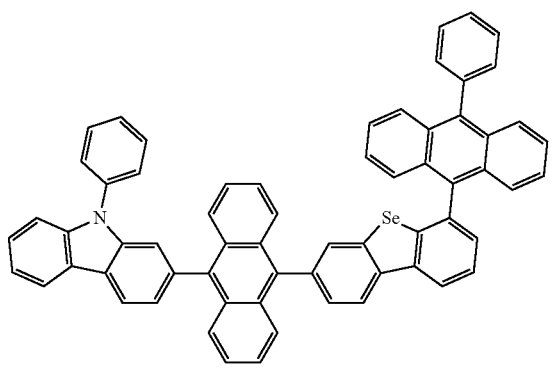
1727
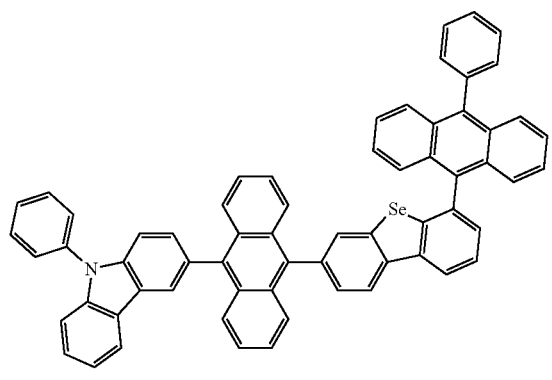
1728
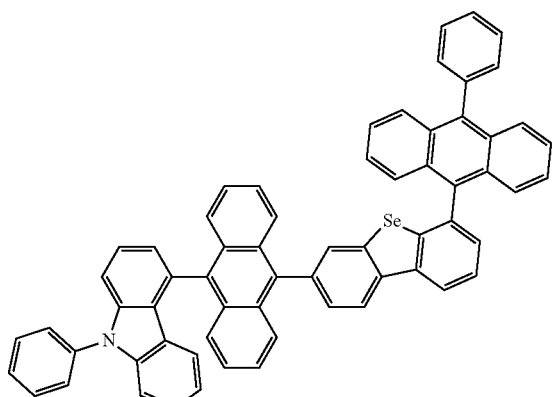

-continued
1729
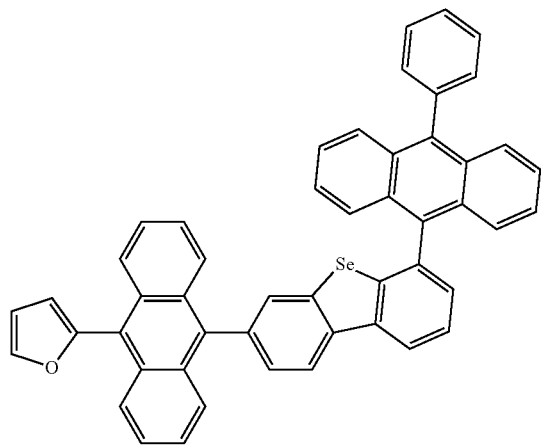
1730
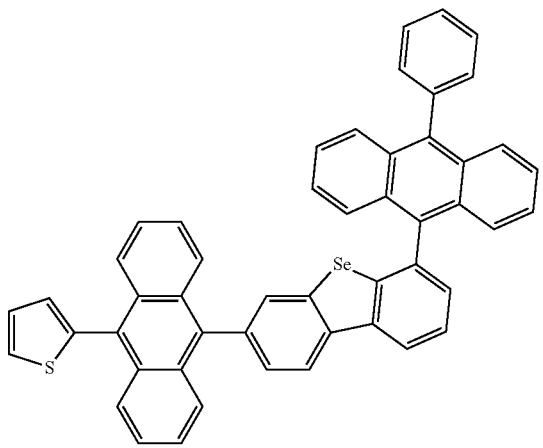
1731
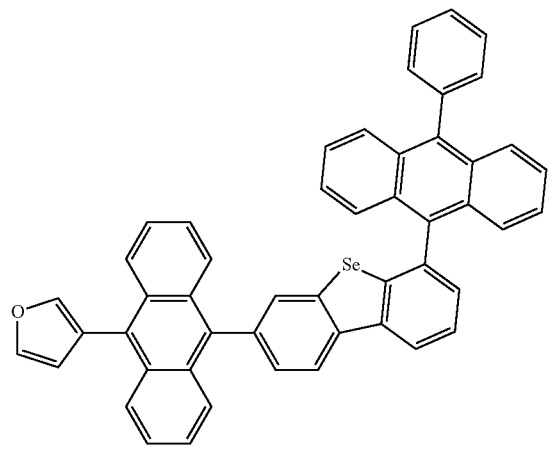
1732
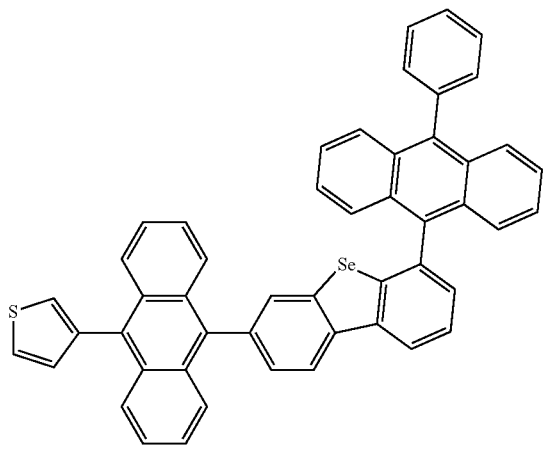
1733
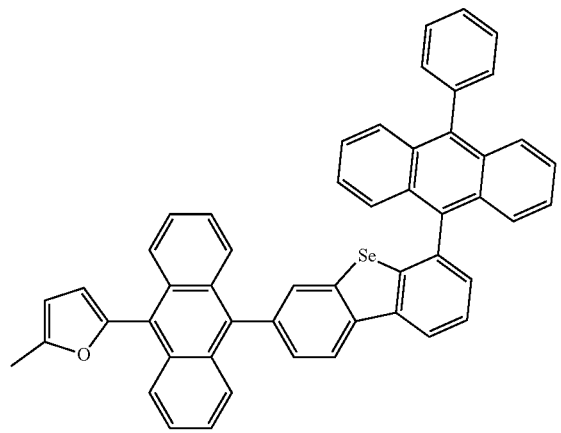
1734
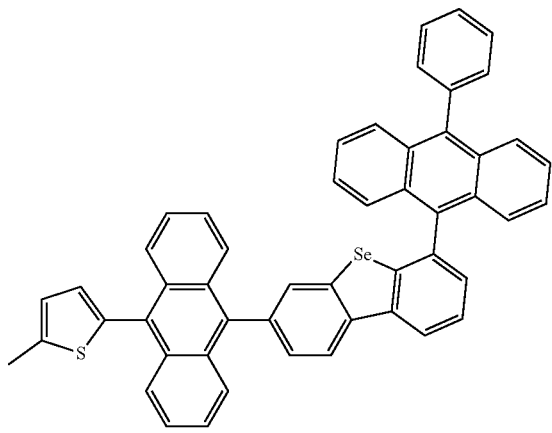

2095 2096
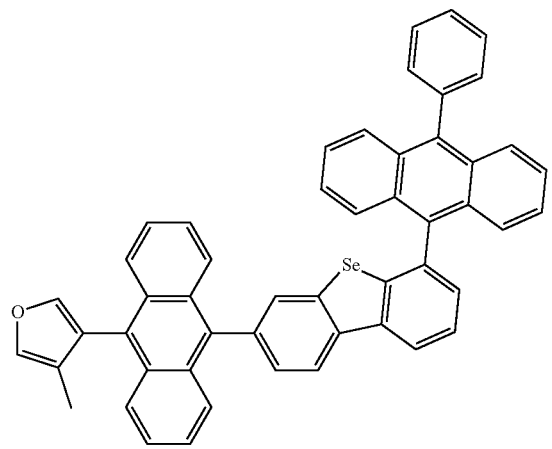
1735
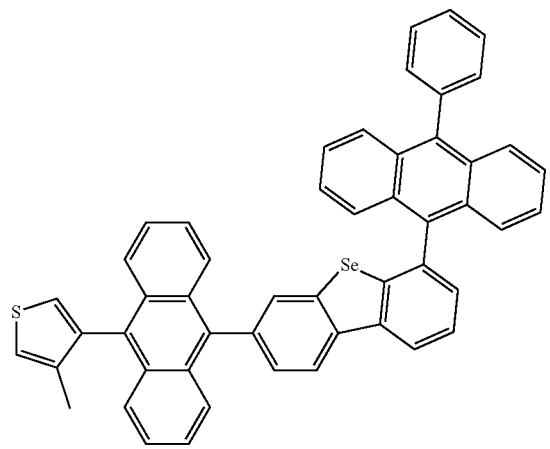
1736
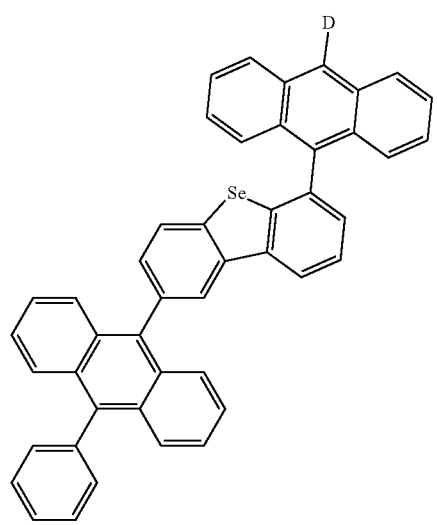
1737
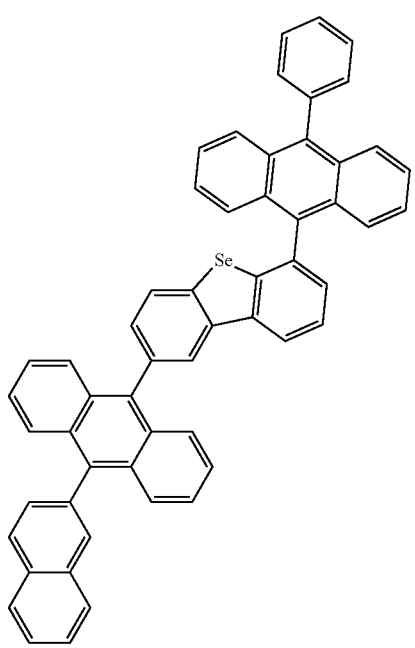
1738

2097 2098
-continued
1739
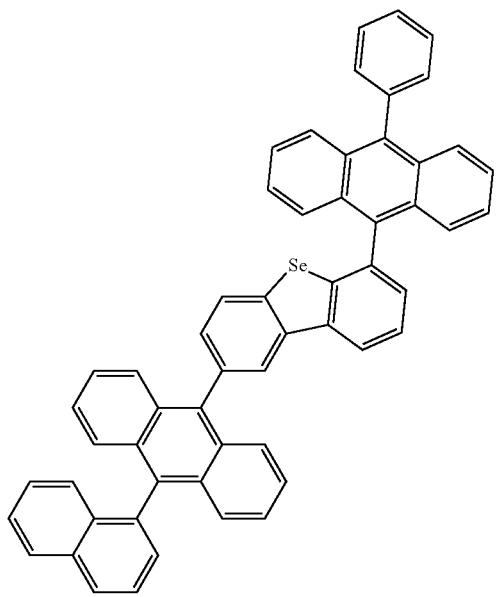
1740
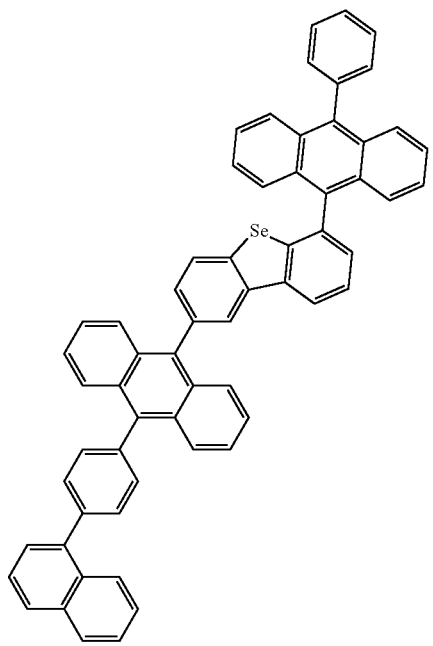
1741
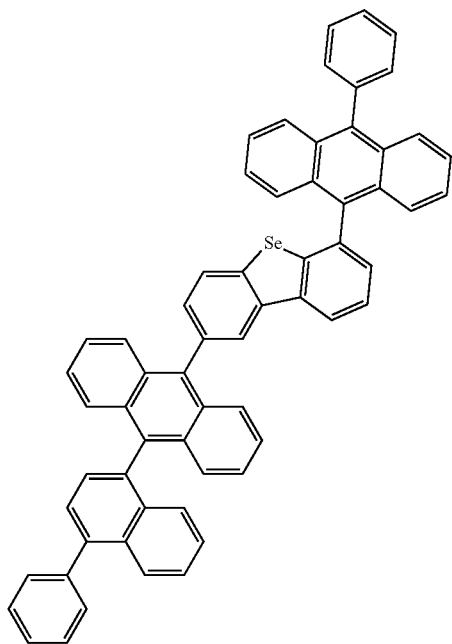
1742
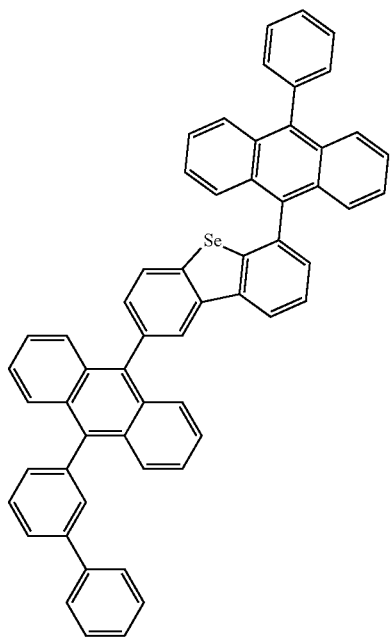

-continued
1743
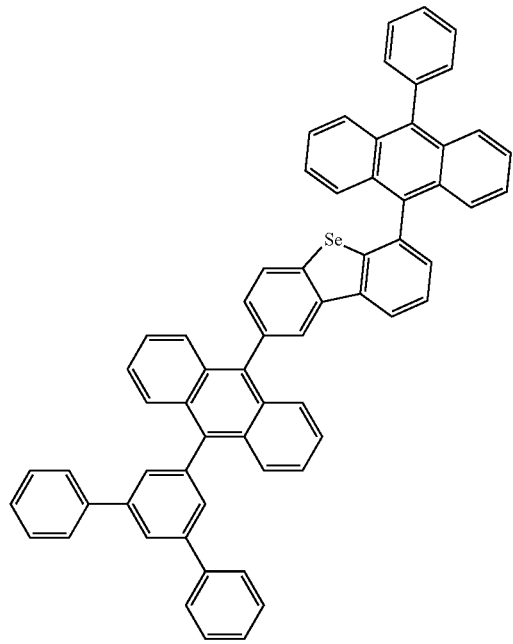
1744
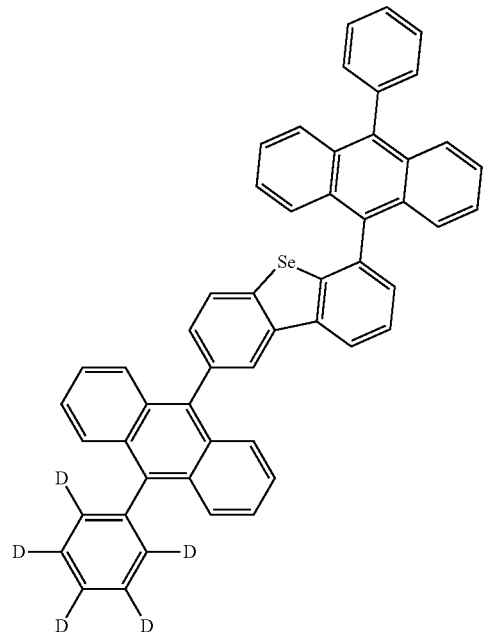
1745
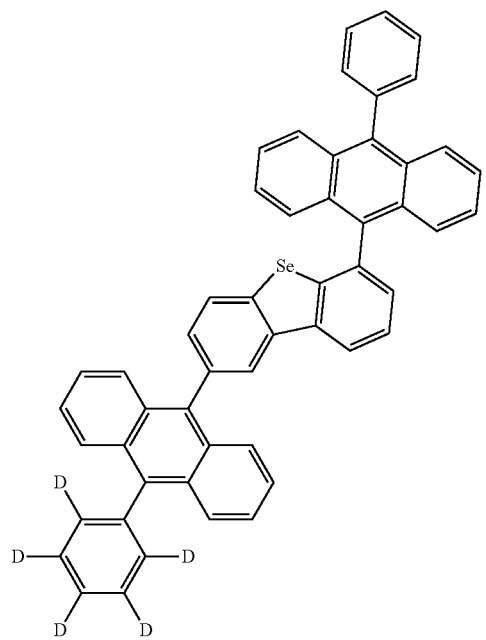
1746
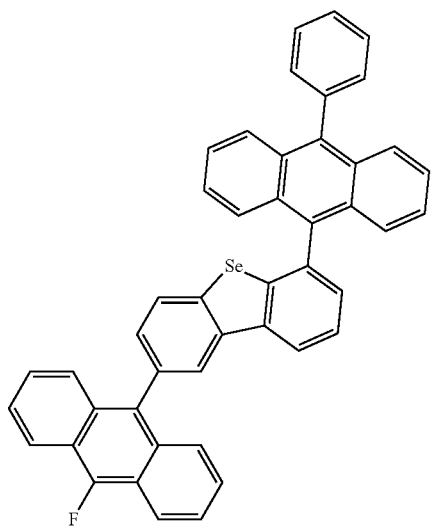

-continued
| 1747 | 1748 |
|---|---|
| 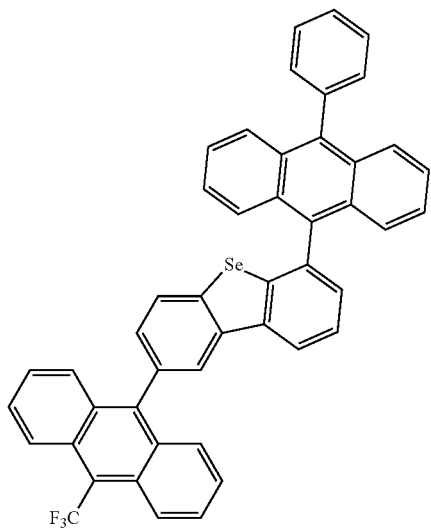 | 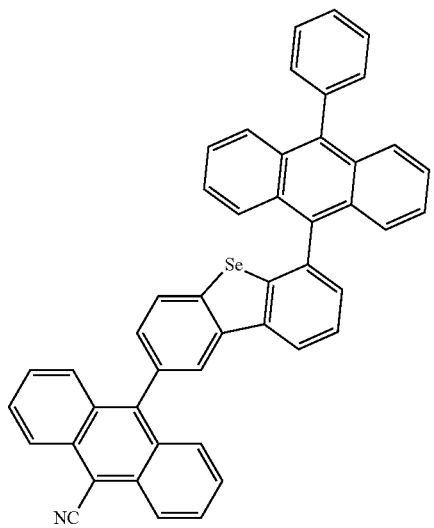 |
| 1749 | 1750 |
| 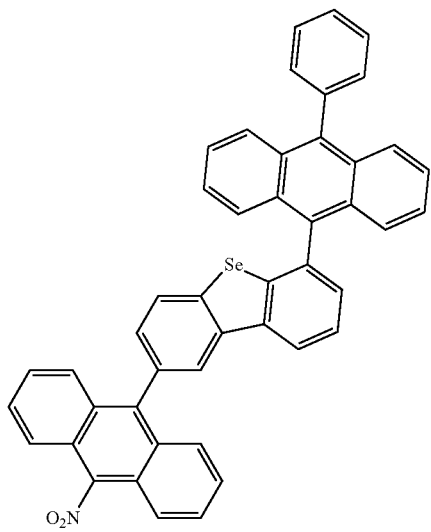 | 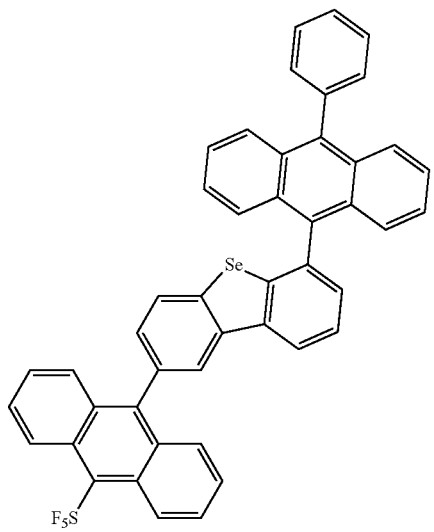 |
| 1751 | 1752 |
| 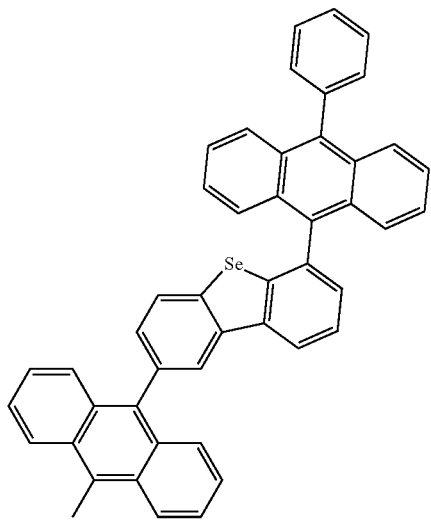 | 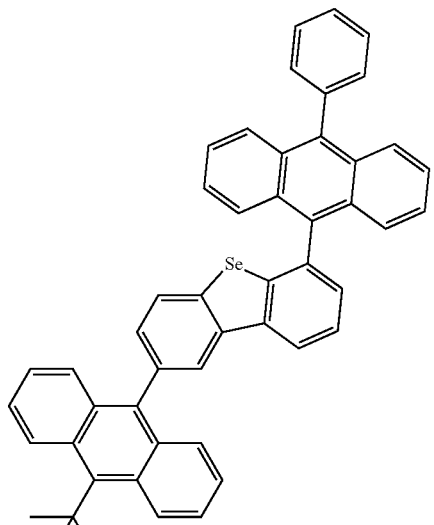 |

2103 2104
-continued
1753
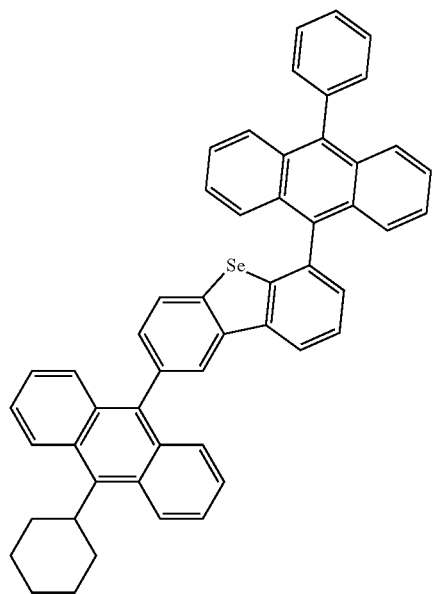
1754
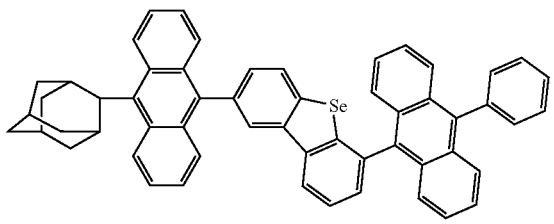
1755
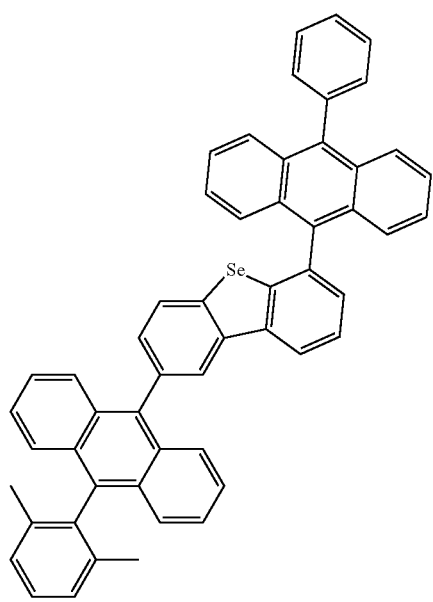
1756
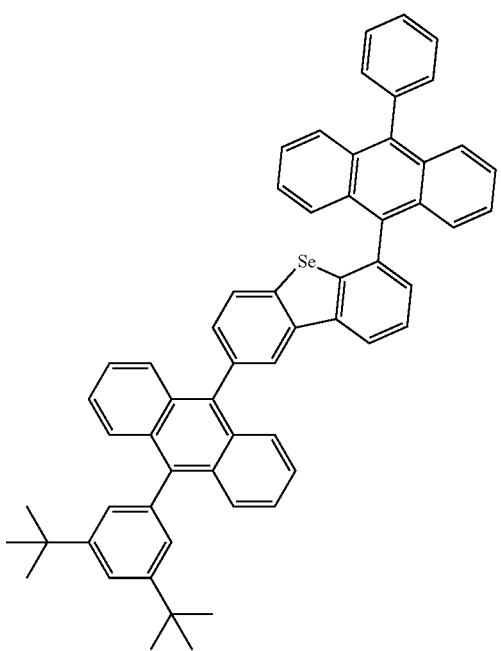

-continued
| 1757 | 1758 |
|---|---|
| 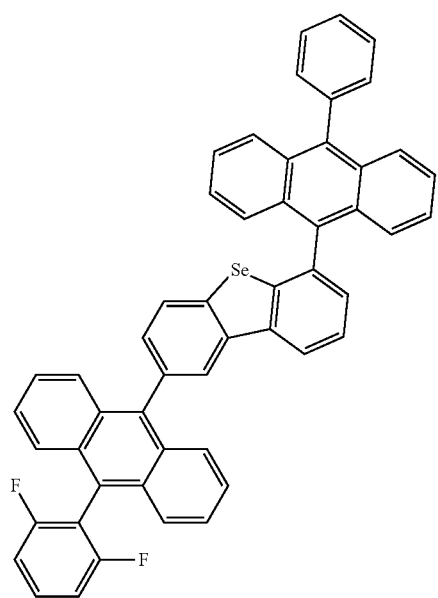 | 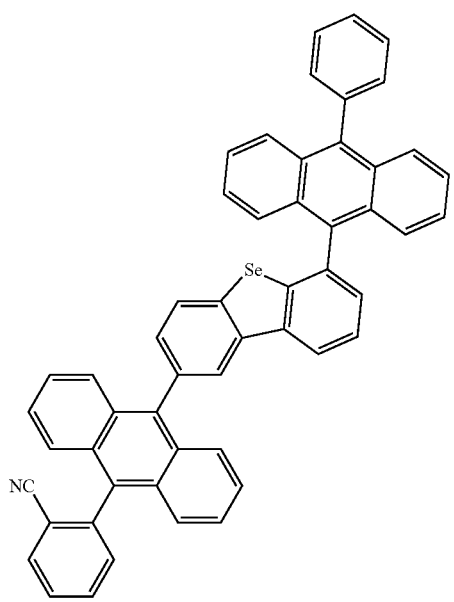 |
| 1759 | 1760 |
| 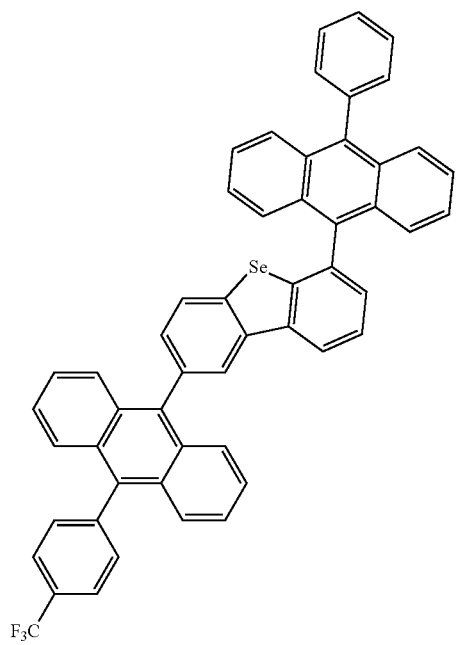 | 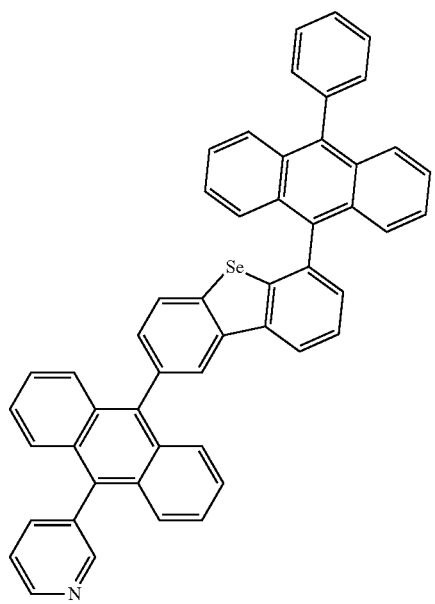 |

-continued
1761
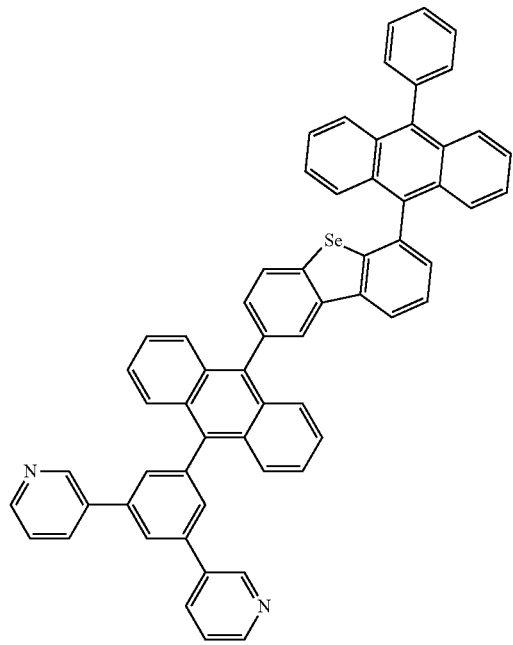
1762
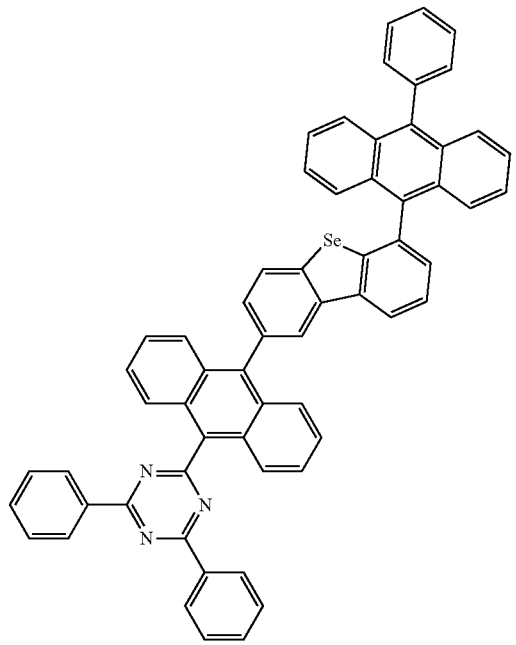
1763
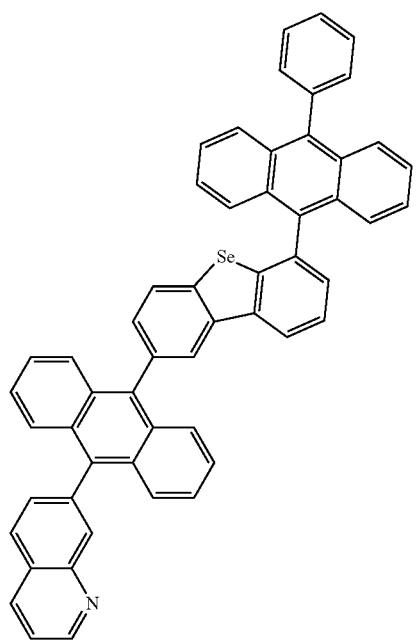
1764
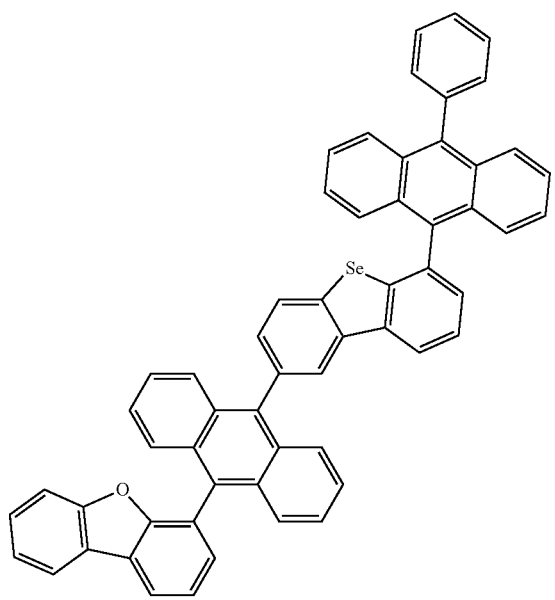

-continued
2109
1765
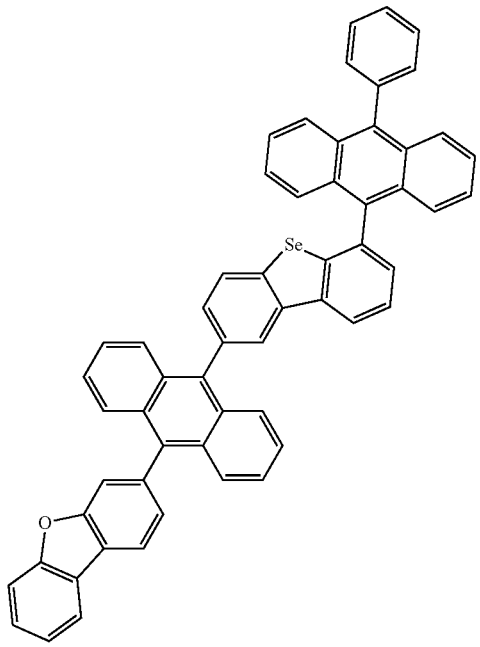
2110
1766
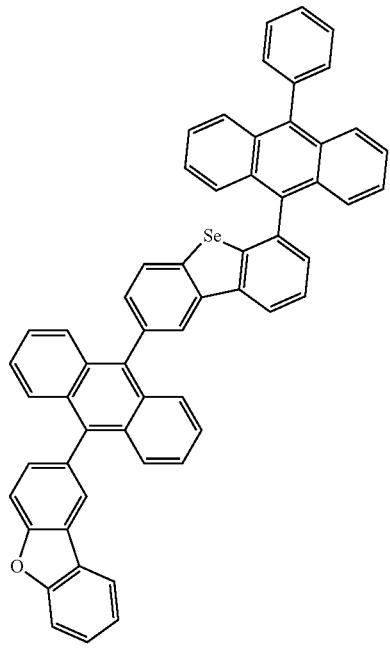
1767
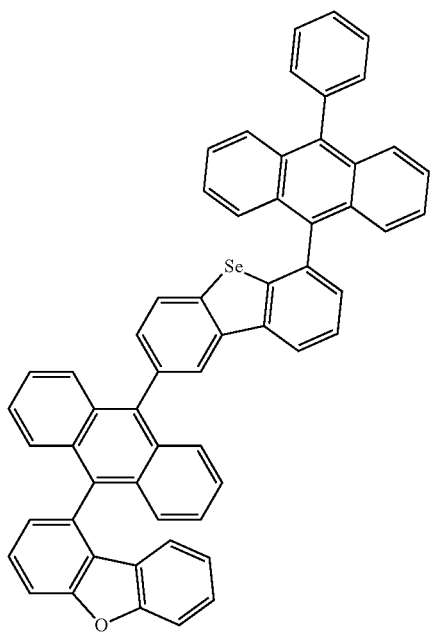
1768
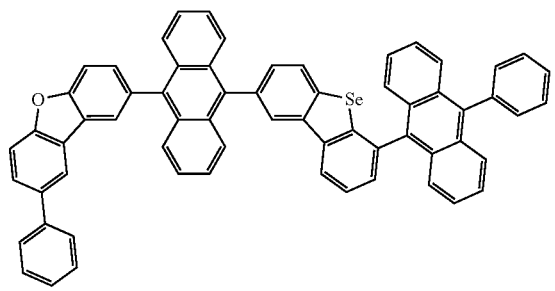

-continued
1769
2111
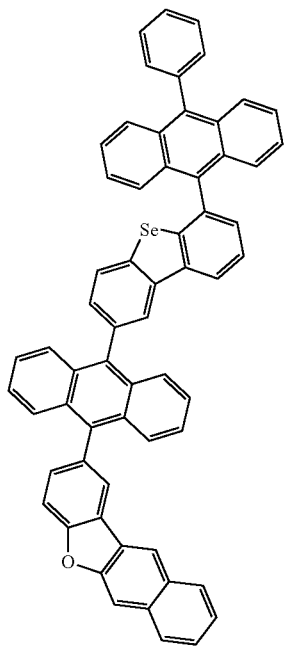
1770
2112
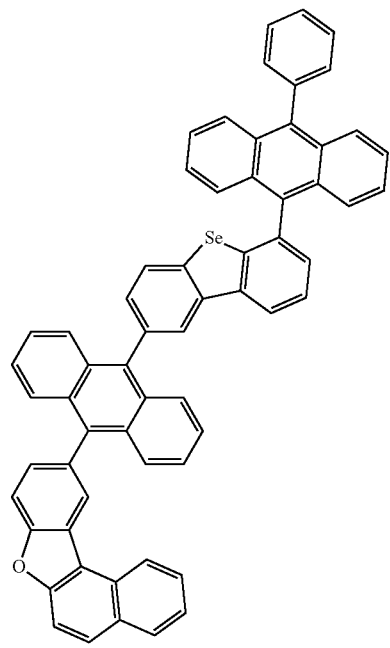
1771
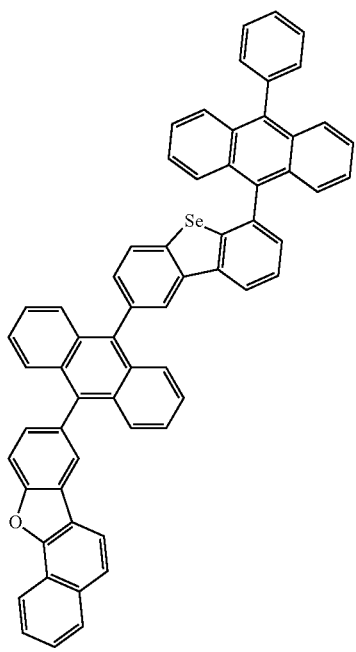
1772
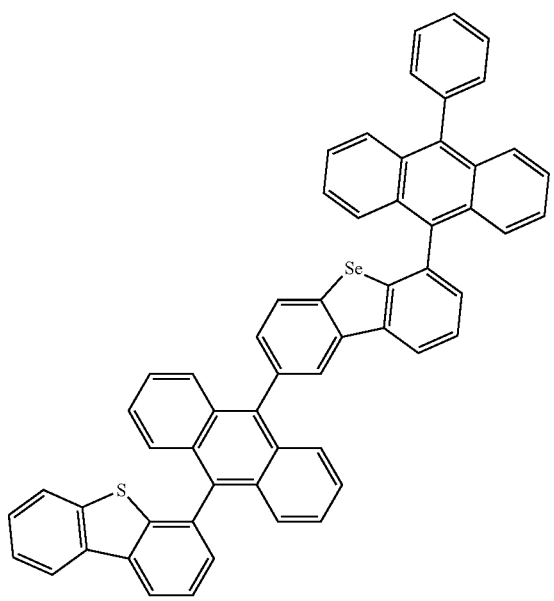

-continued
1773
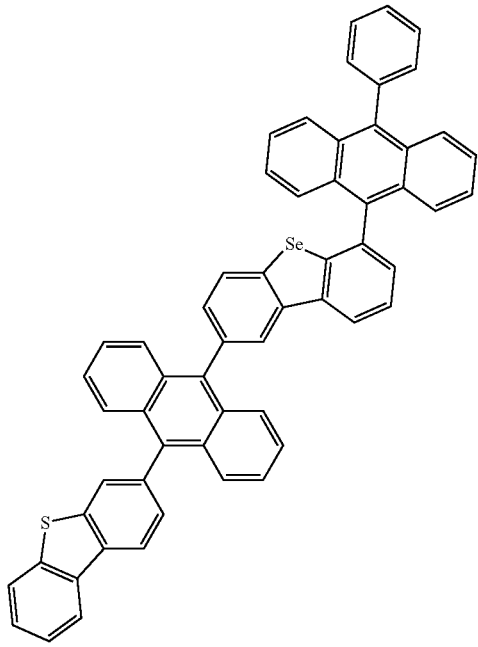
1774
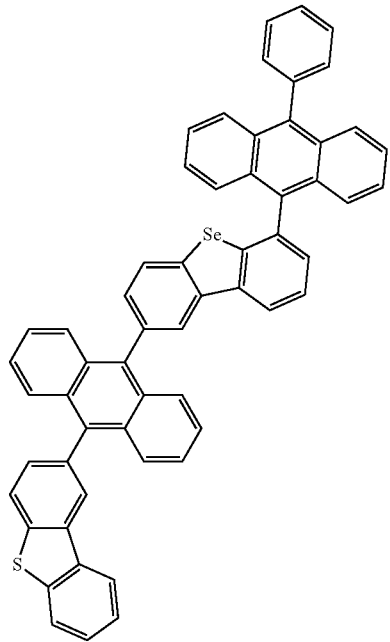
1775
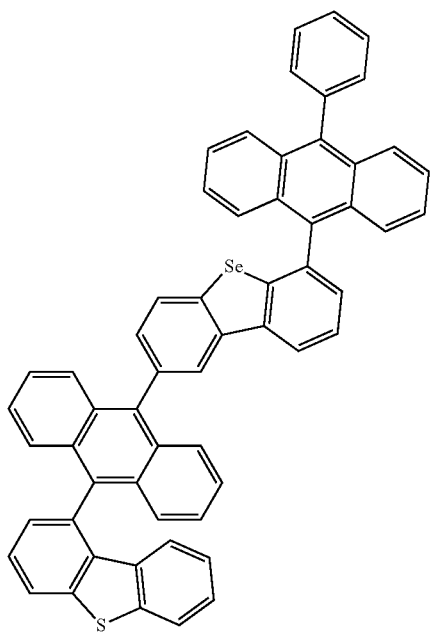
1776
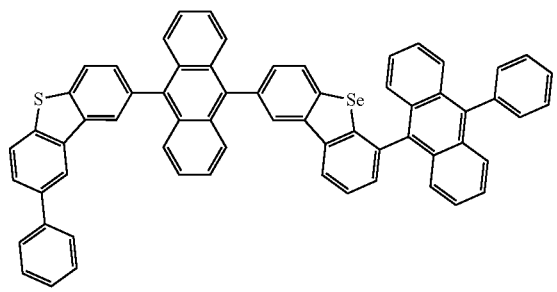

-continued
1777
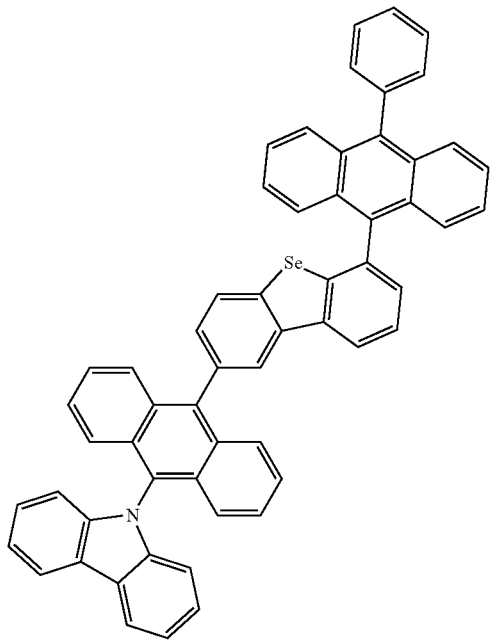
1778
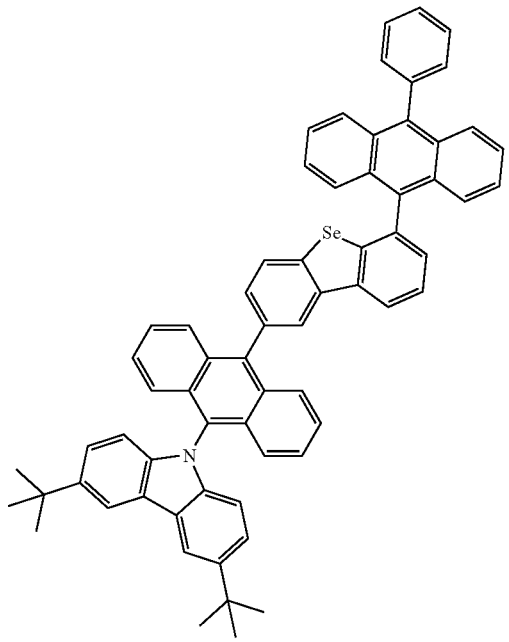
1779
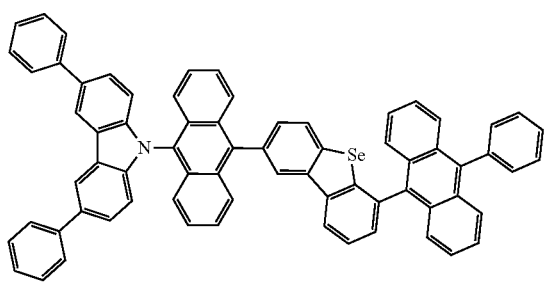
1780
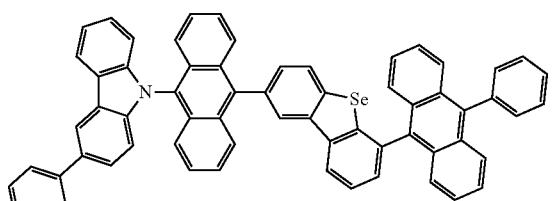
1781
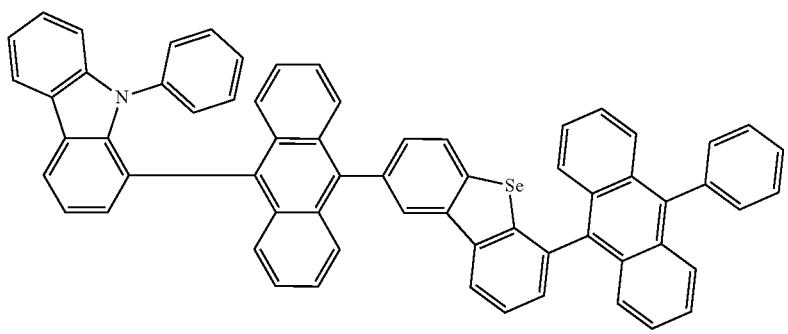
1782
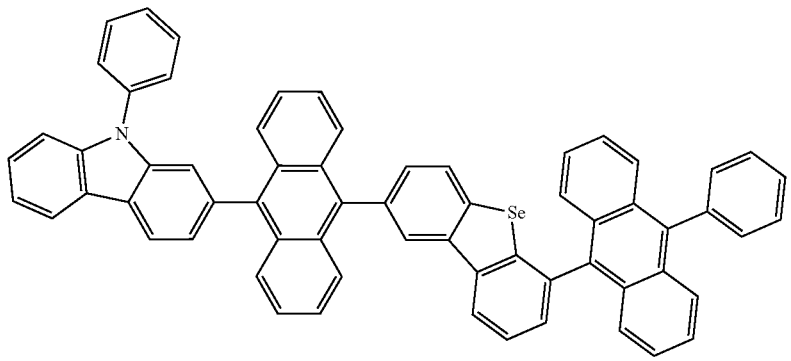

1783
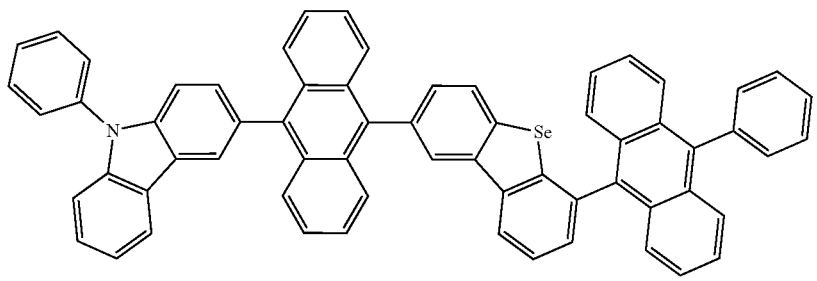
1784
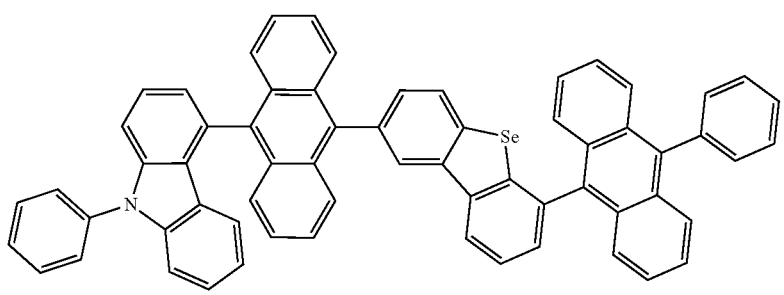
1785
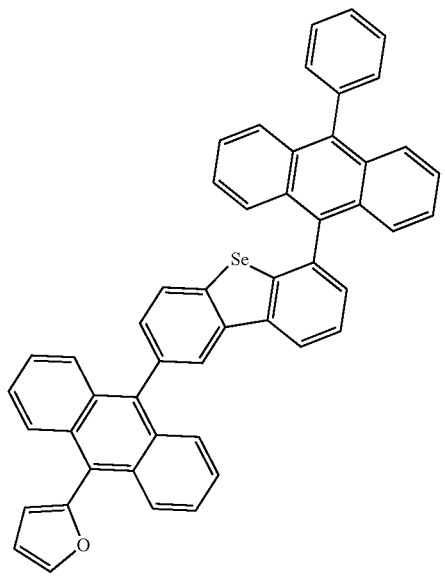
1786
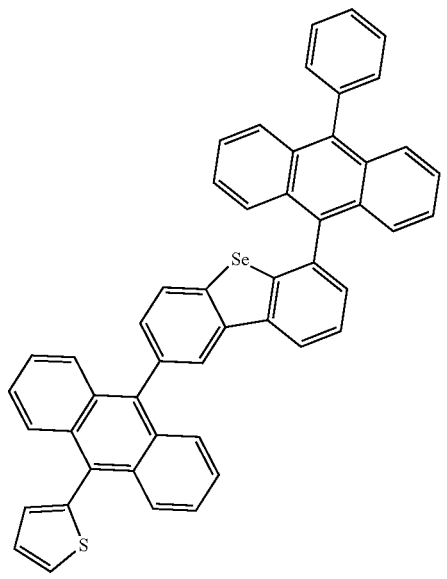

2119 2120
-continued
1787 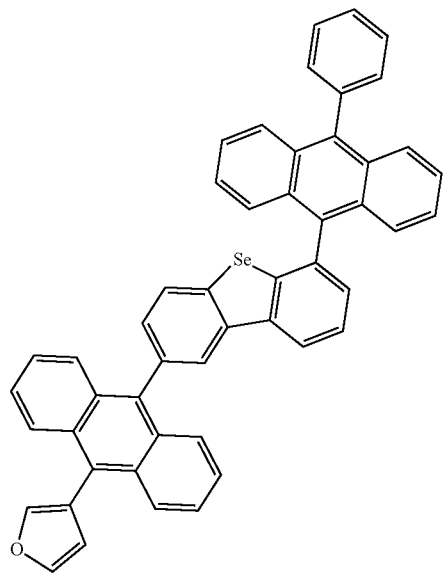 1788 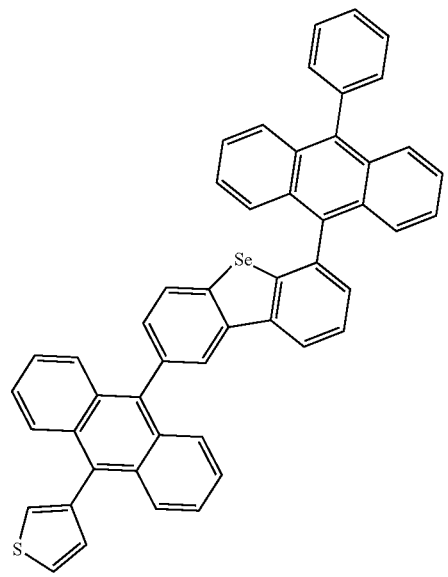
1789 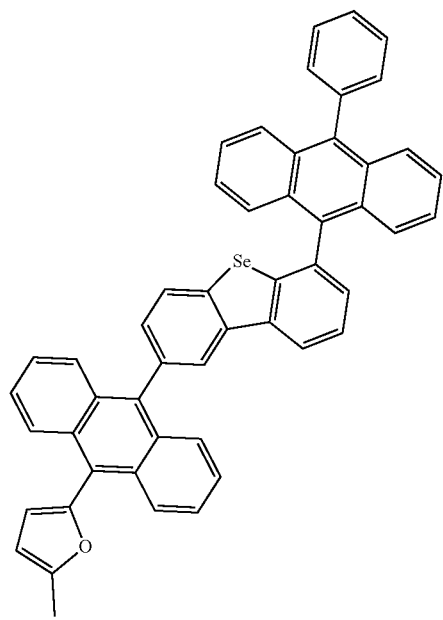 1790 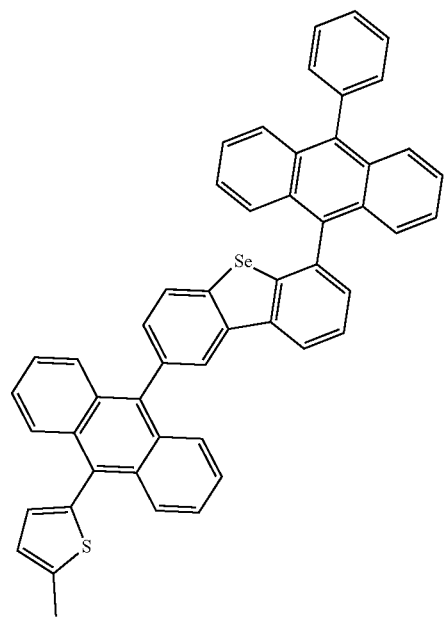

-continued
1791
2121
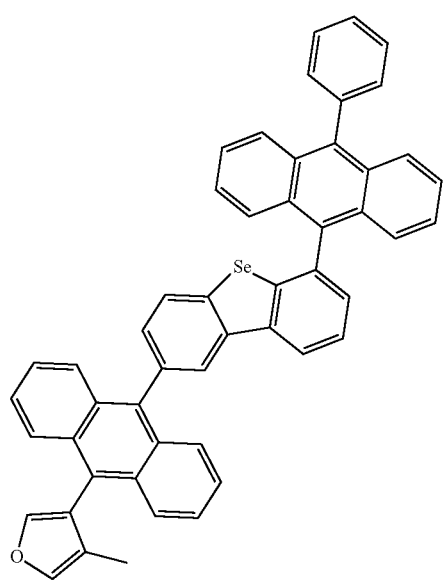
1792
2122
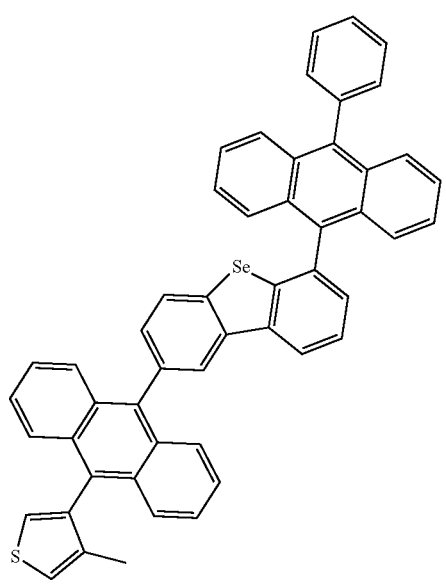
1793
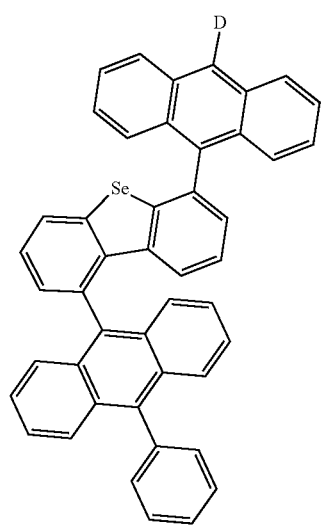
1794
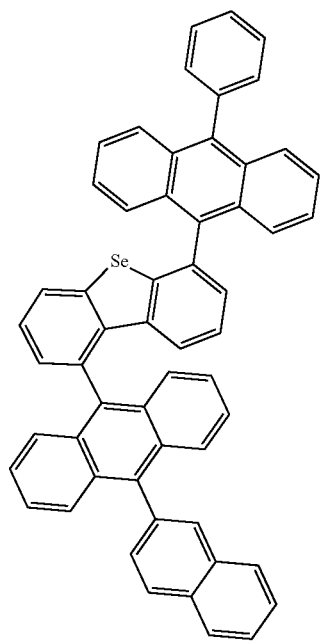

-continued
1795
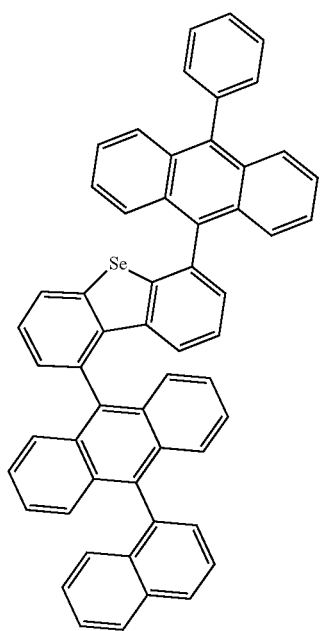
1796
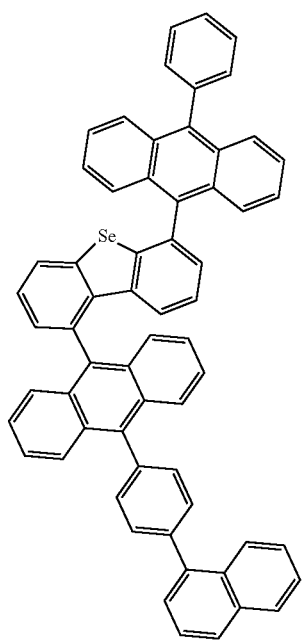
1797
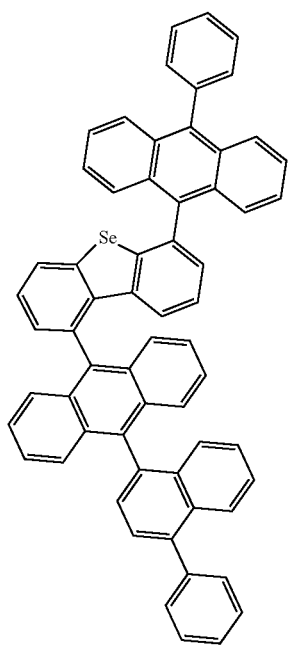
1798
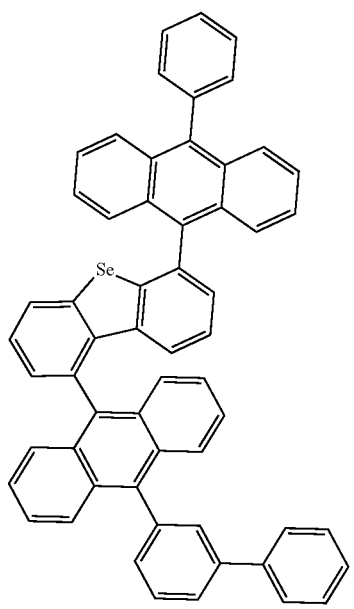

-continued
2125
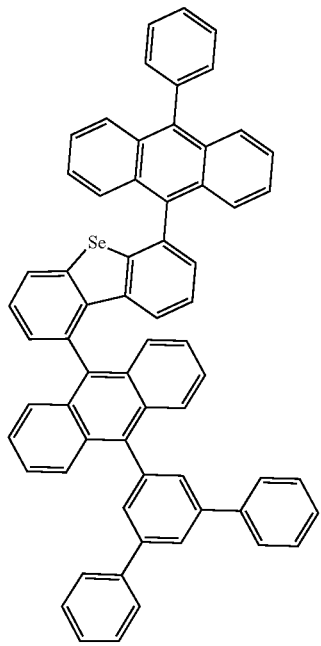
2126
1799
1800
1801
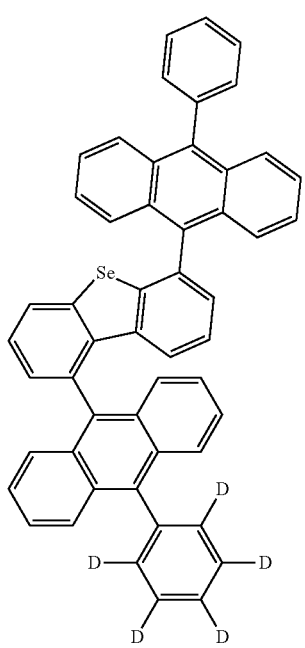
1802
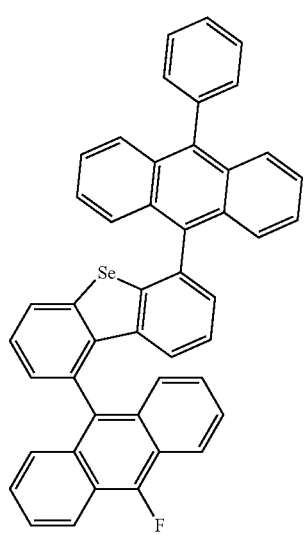

1803
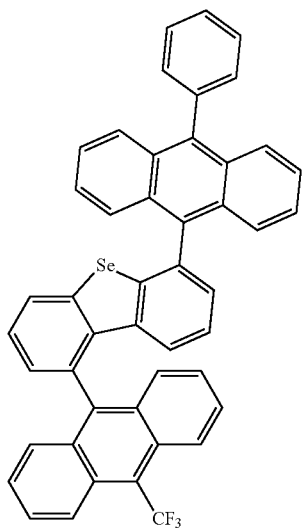
1804
1805
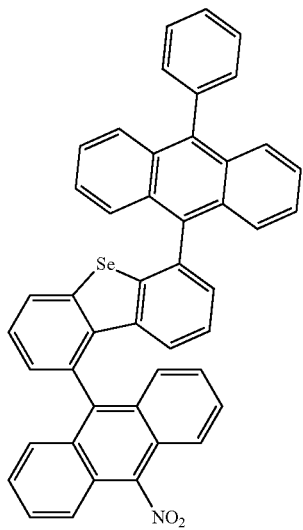
1806
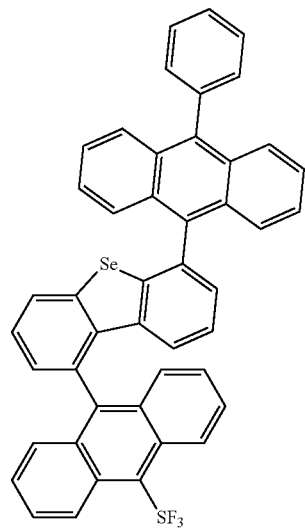
1807
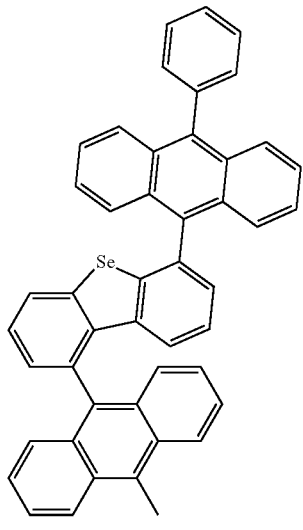
1808
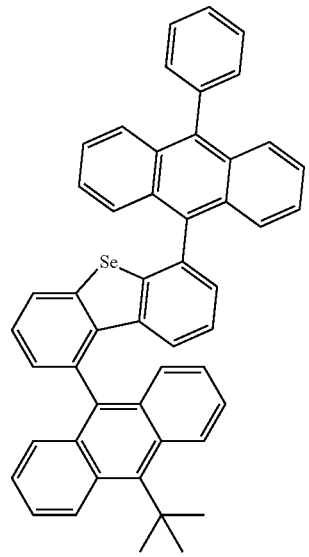

-continued
1809
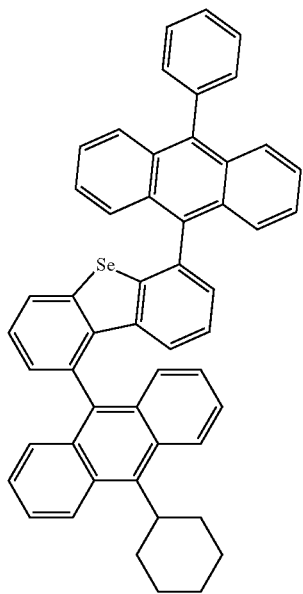
1810
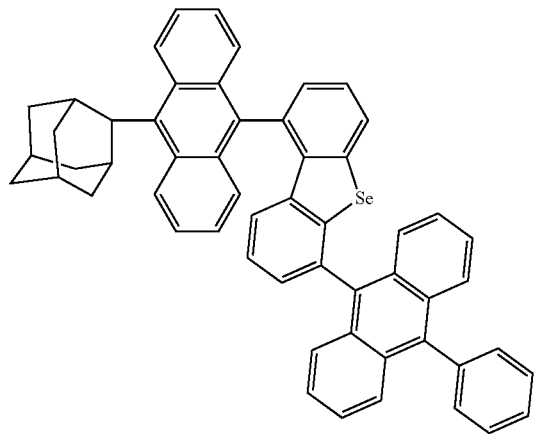
1811
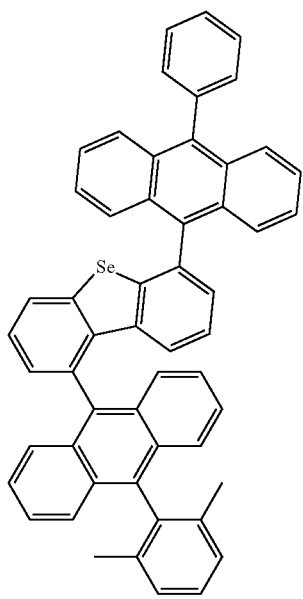
1812
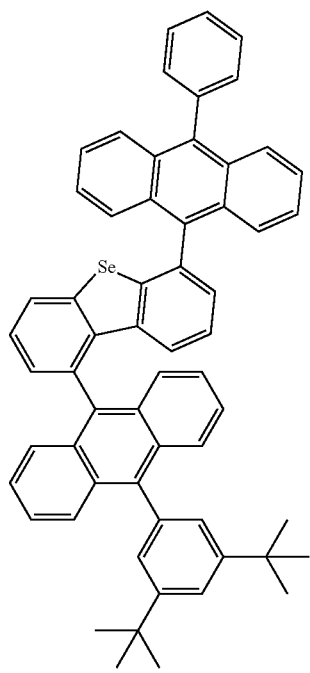

-continued
1813
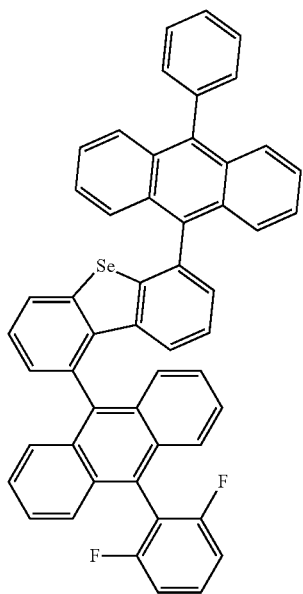
1814
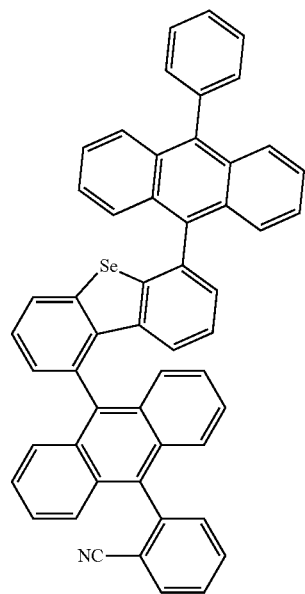
1815
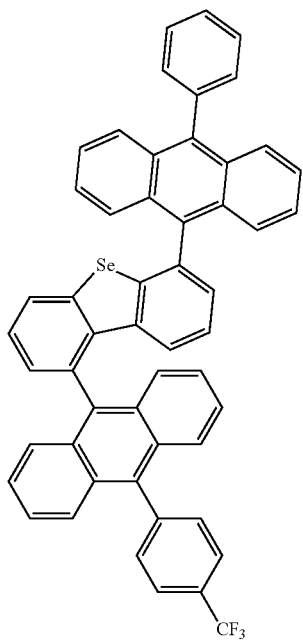
1816
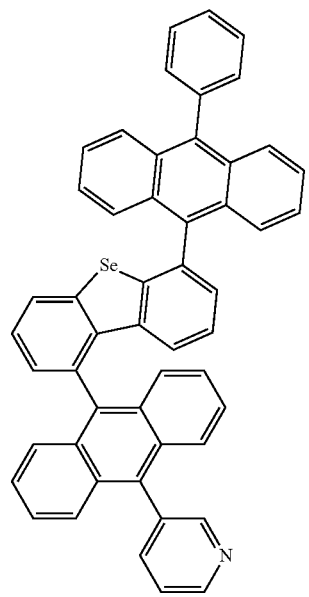

-continued
1817
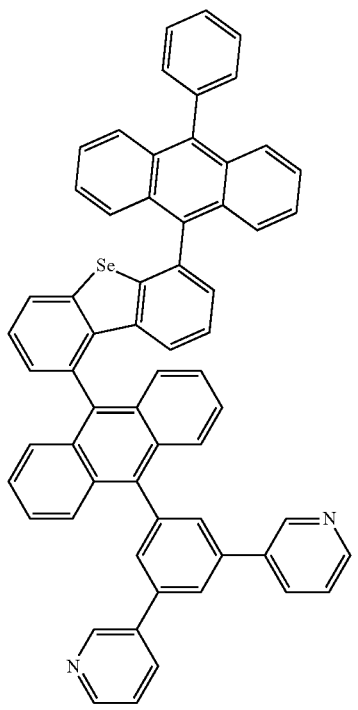
1818
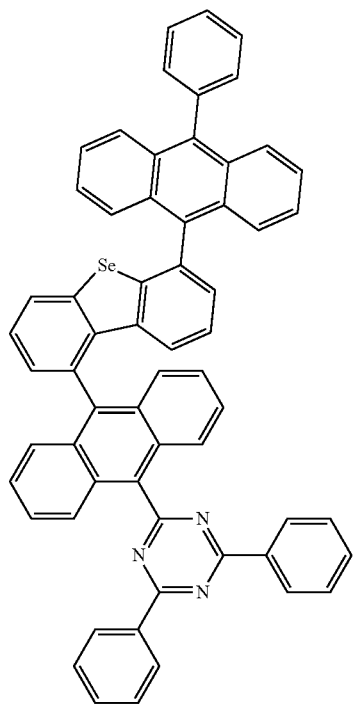
1819
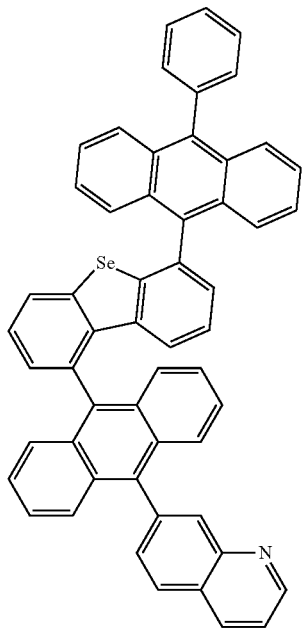
1820
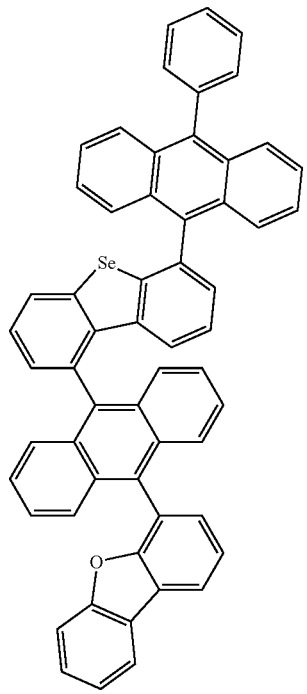

1821
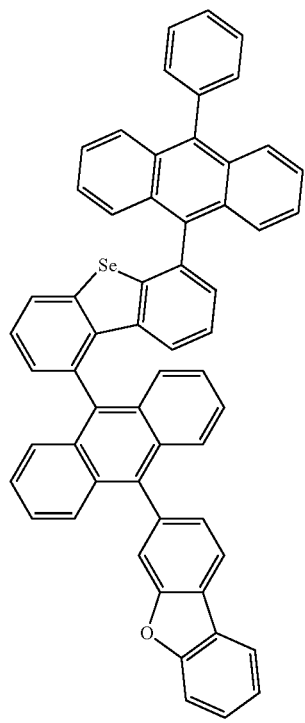
1822
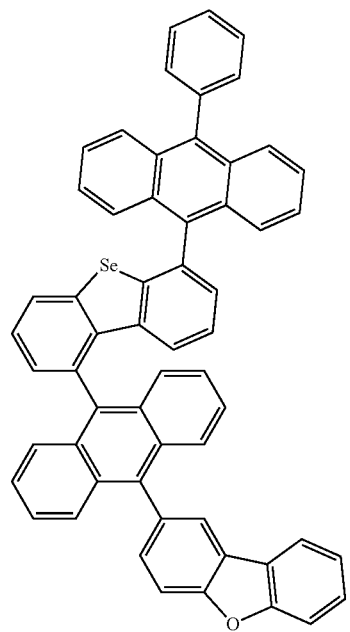
1823
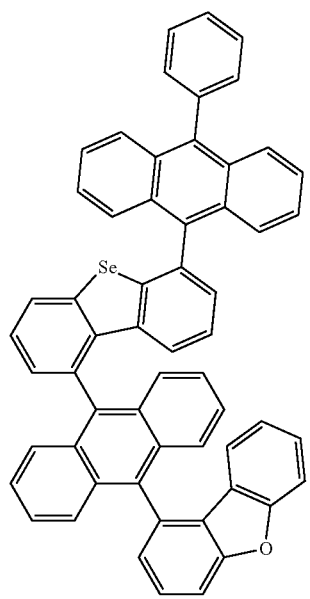
1824
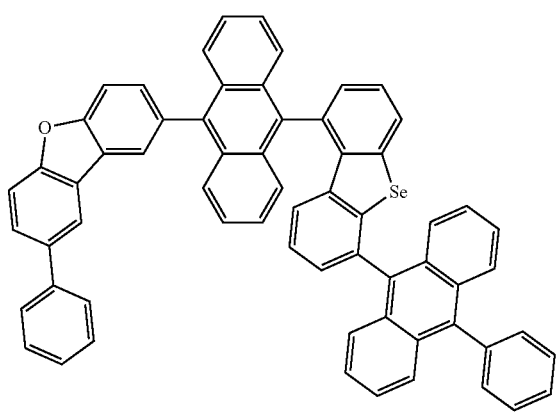

2137 2138
-continued
1825 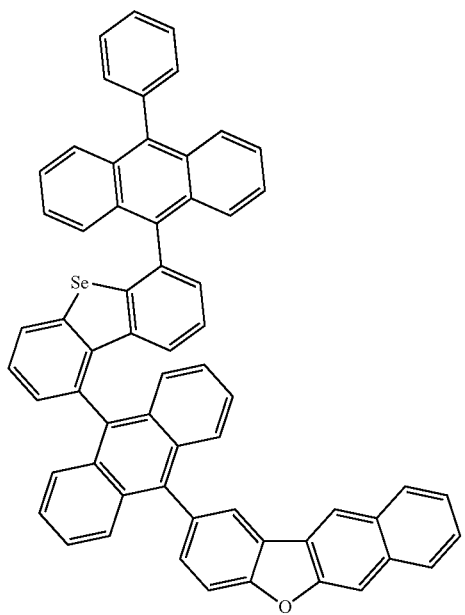 1826 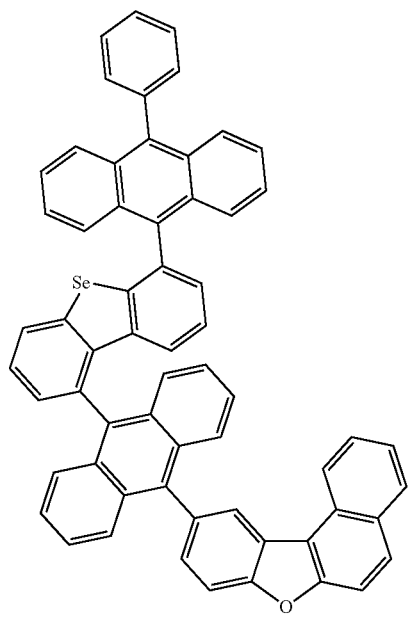
1827 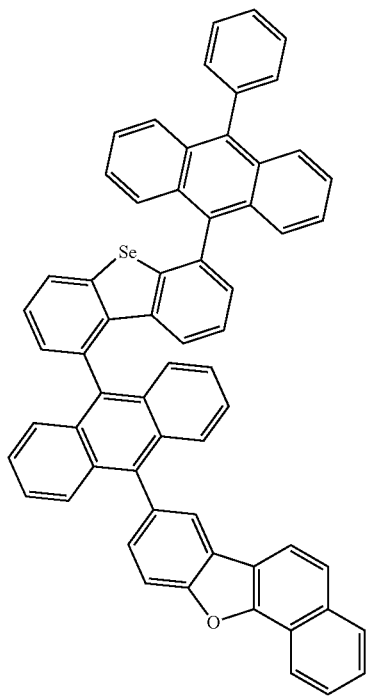 1828 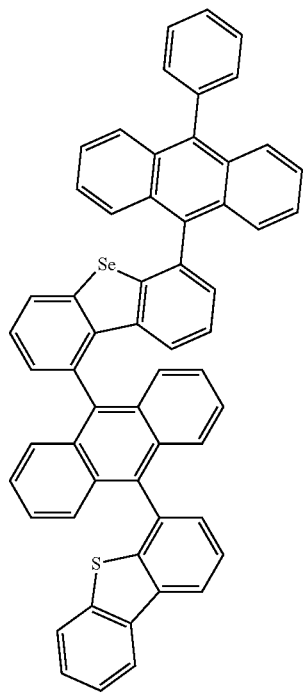

2139
1829
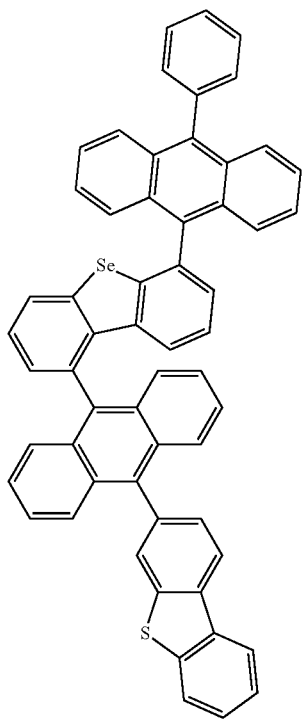
2140
1830
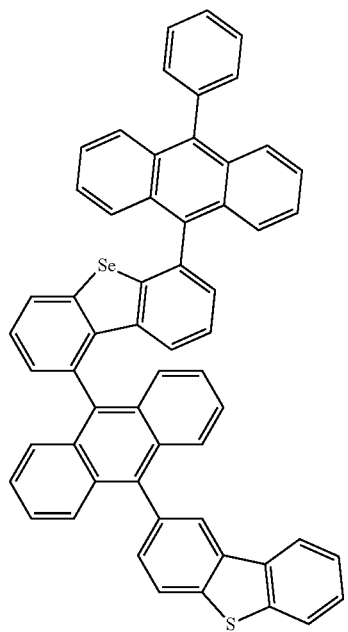
1831
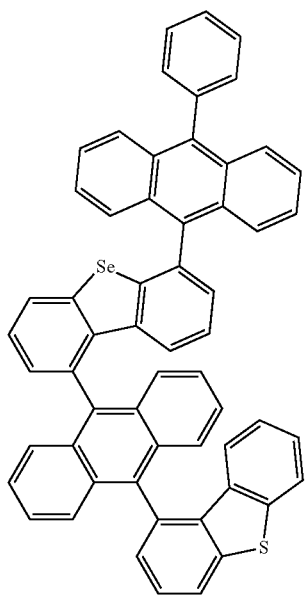
1832
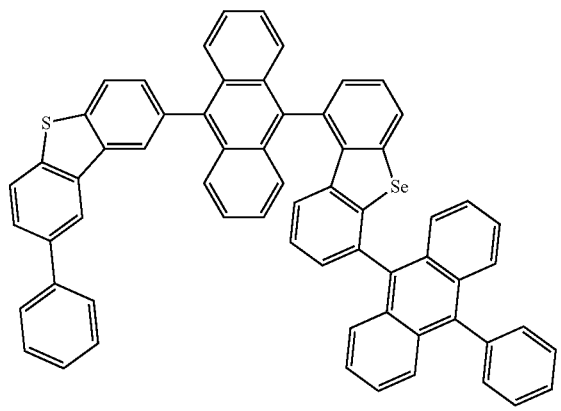

1833
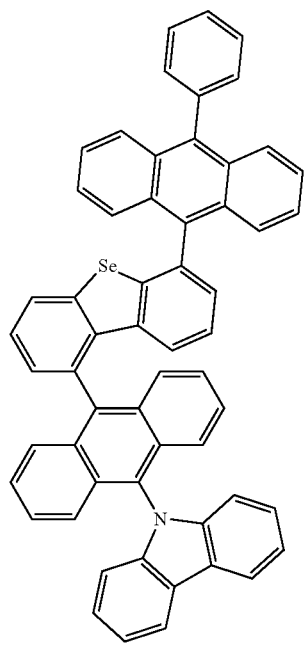
1834
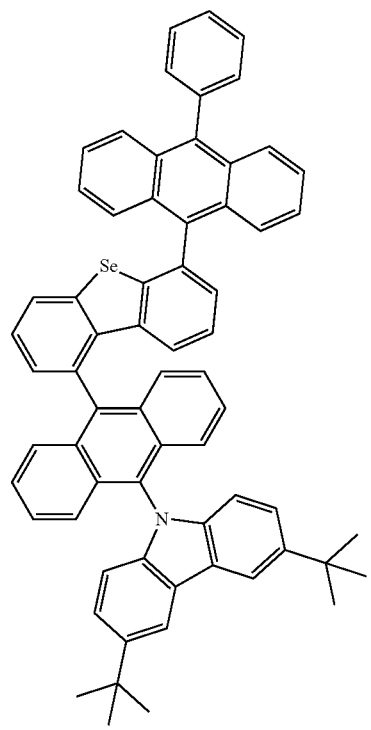
1835
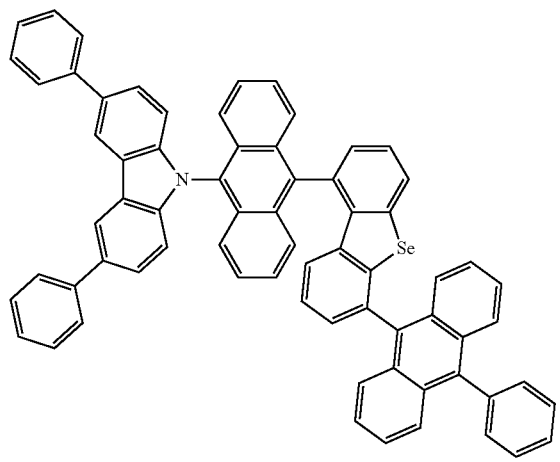
1836
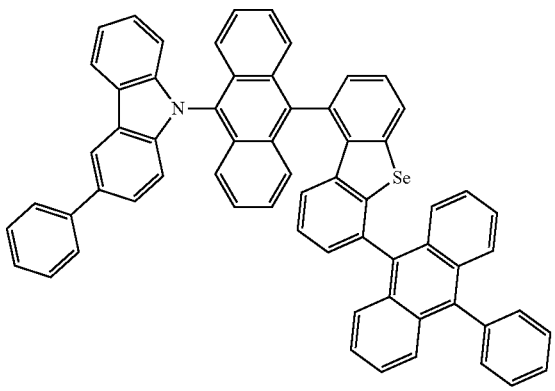

-continued
1837
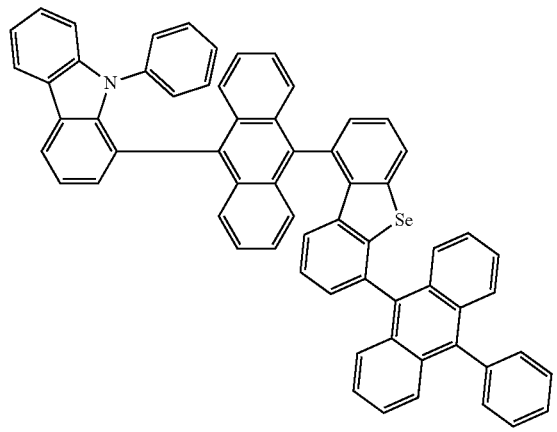
1838
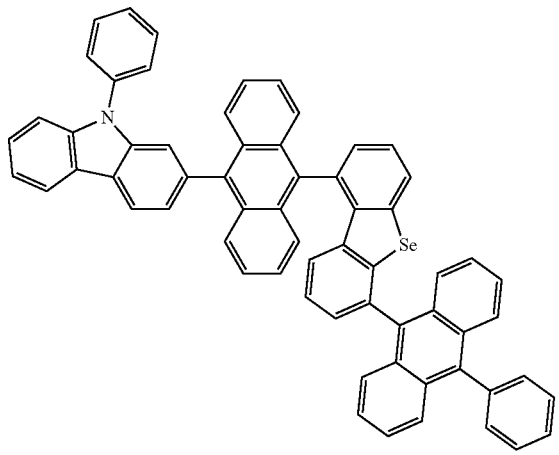
1839
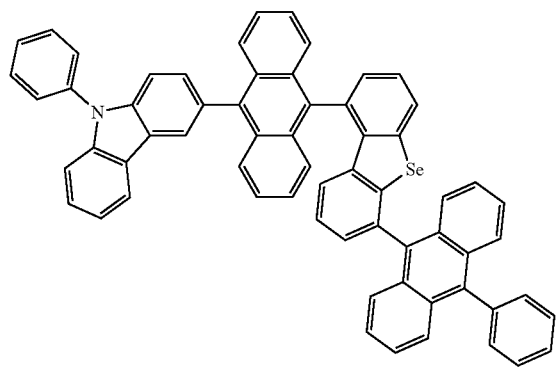
1840
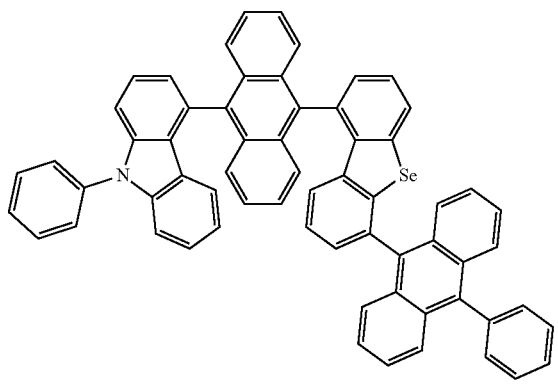
1841
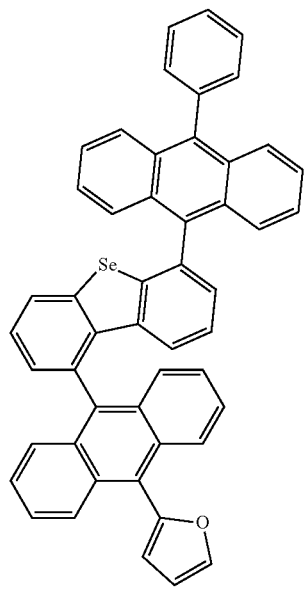
1842
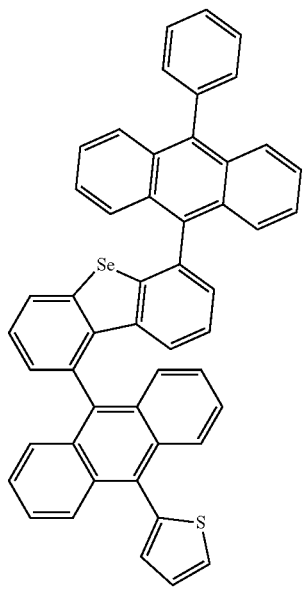

-continued
| 2145 | 2146 |
|---|---|
| 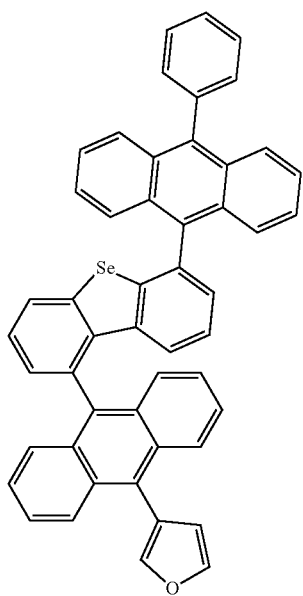 1843 | 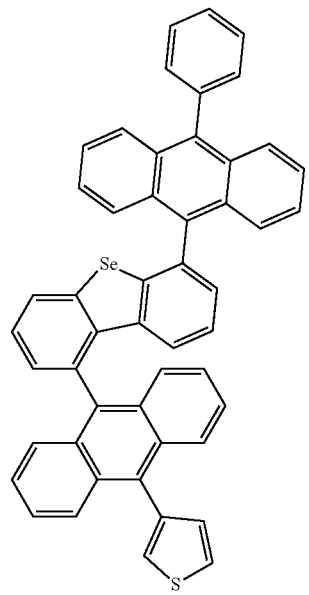 1844 |
| 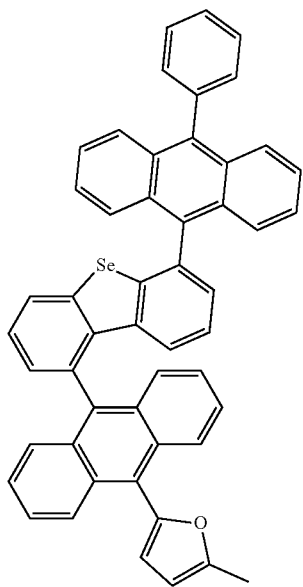 1845 | 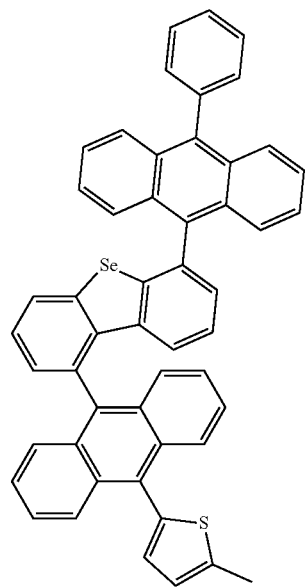 1846 |

1847
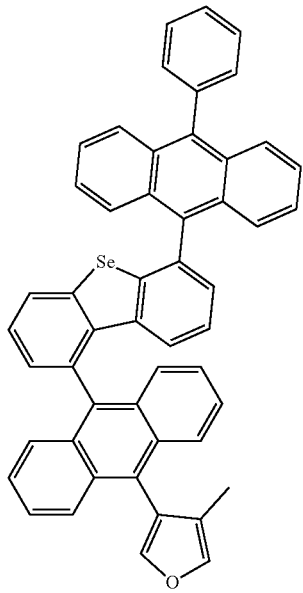
1848
1849
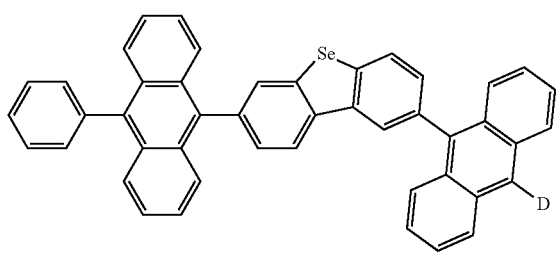
1850
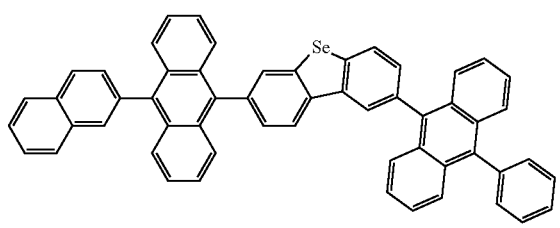
1851
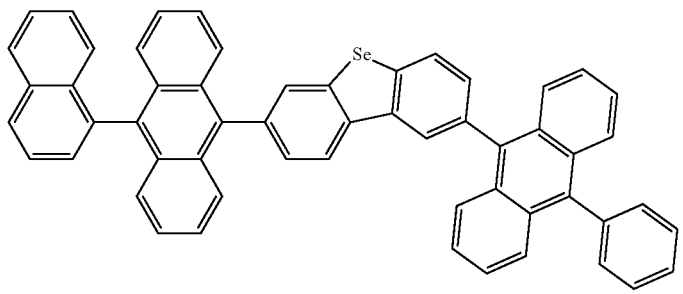
1852
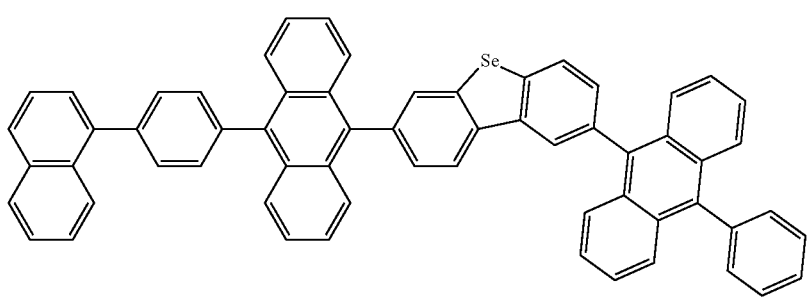

-continued
1853
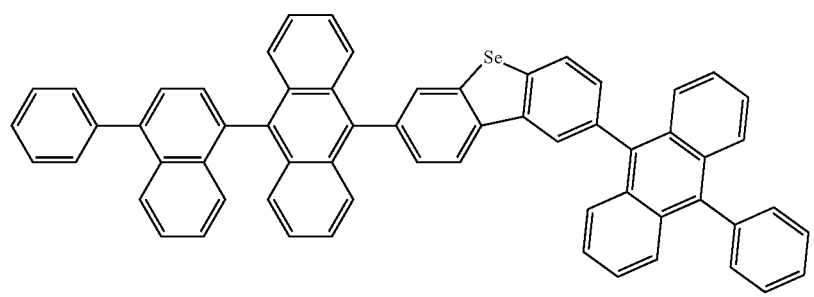
1854
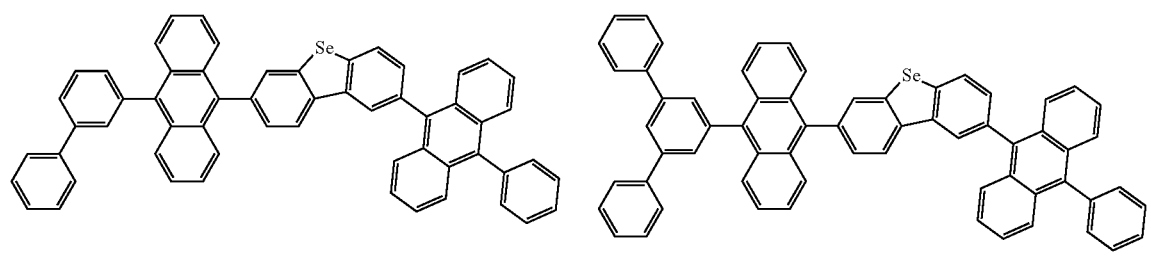
1855
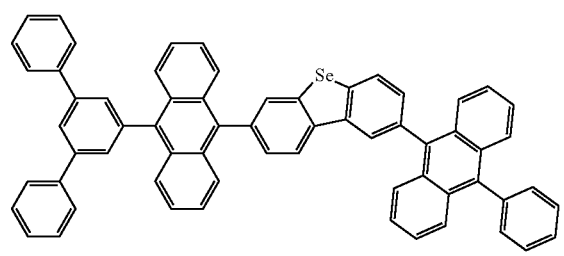
1856 1857
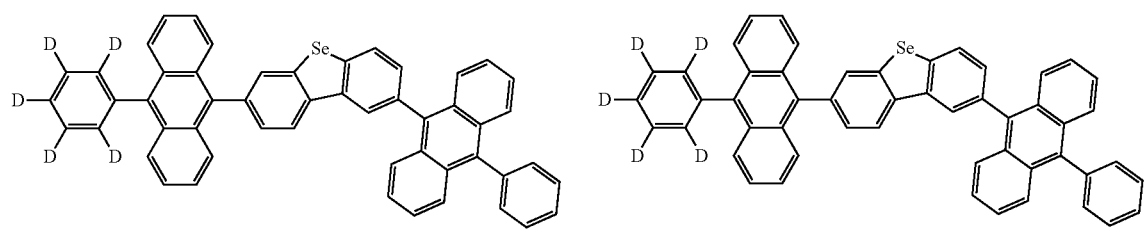
1858
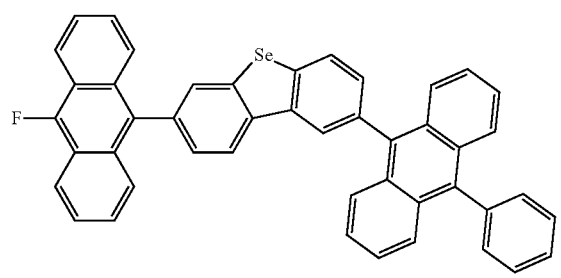
1859
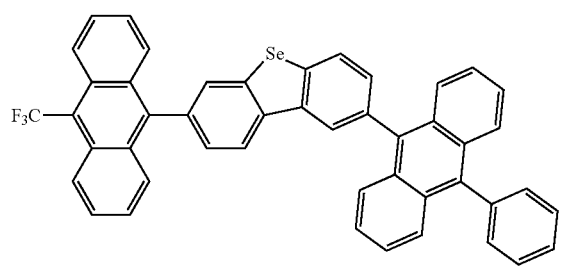
1860
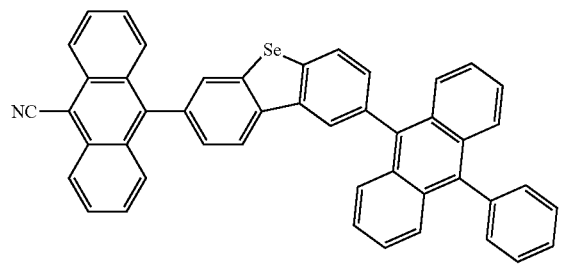
1861
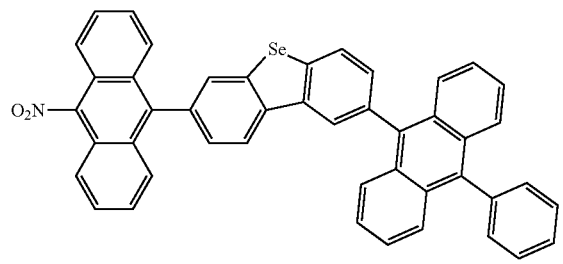

1862
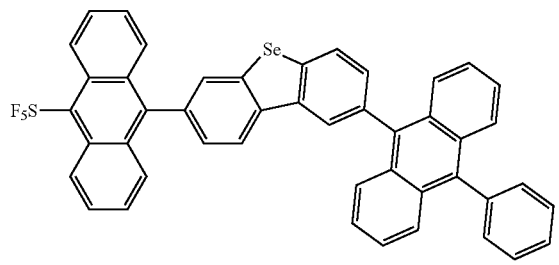
1863
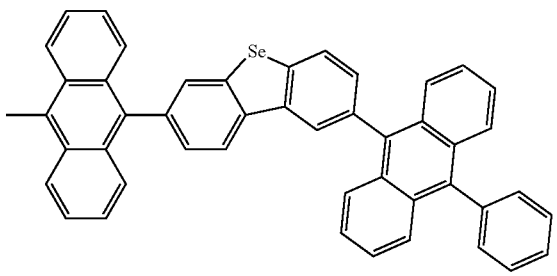
1864
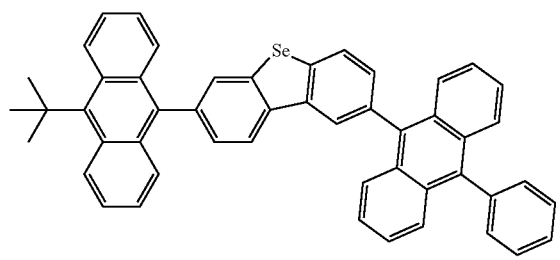
1865
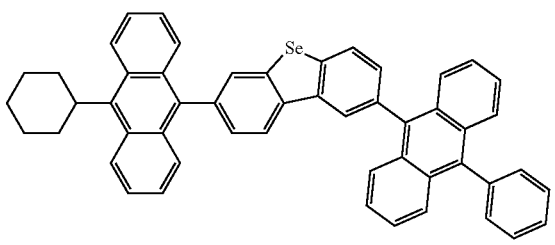
1866
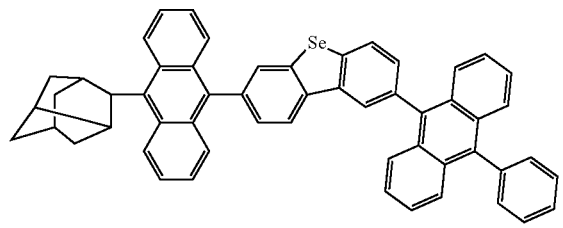
1867
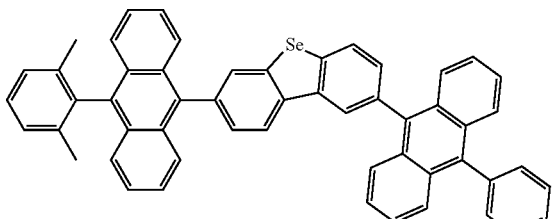
1868
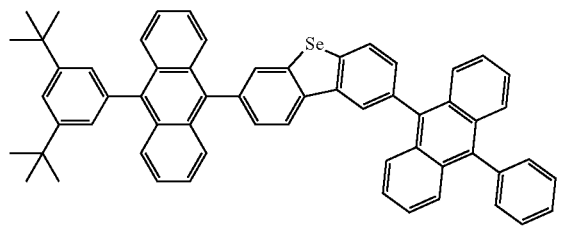
1869
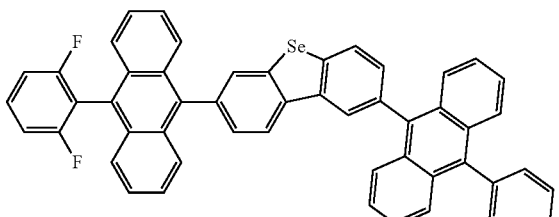
1870
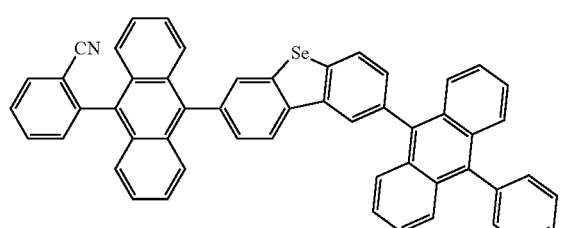
1871
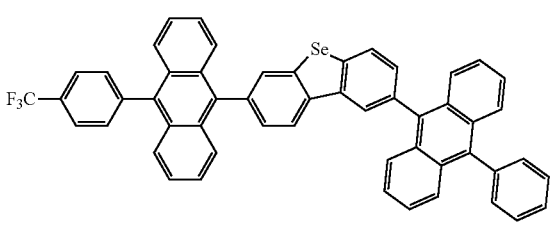
1872
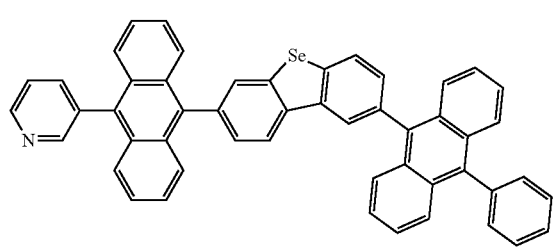
1873
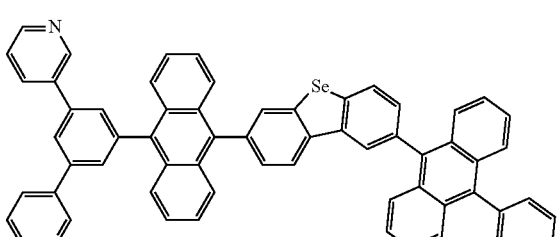

-continued
1874
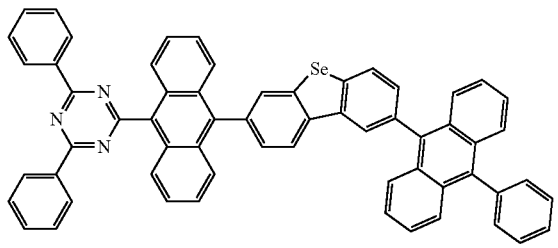
1875
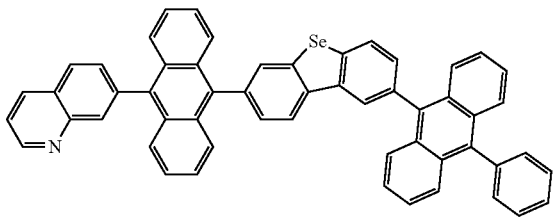
1876
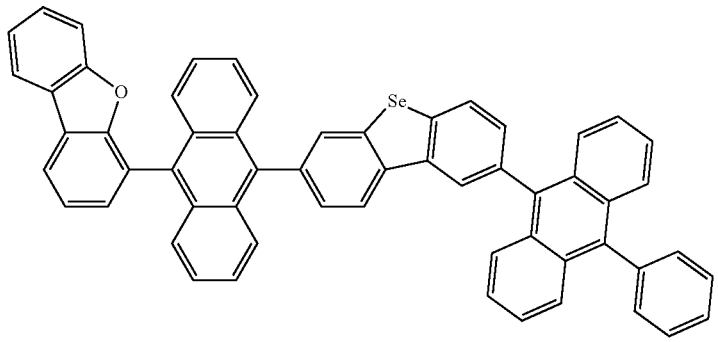
1877
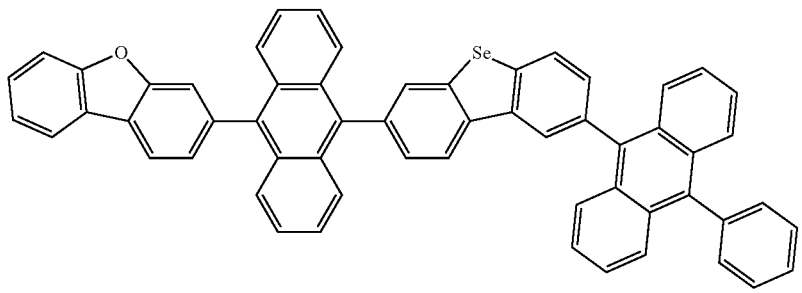
1878
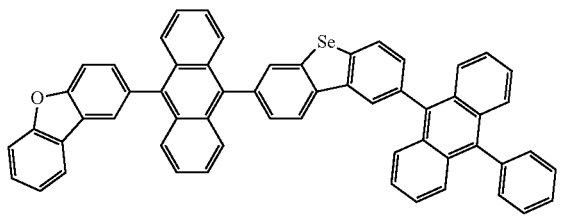
1879
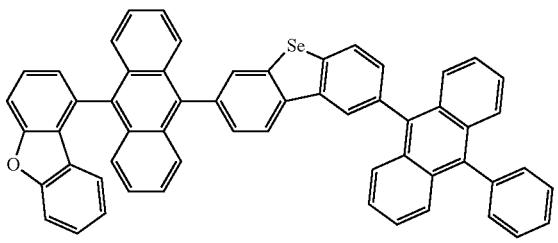
1880
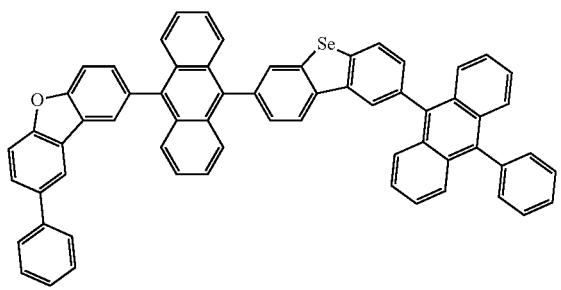
1881
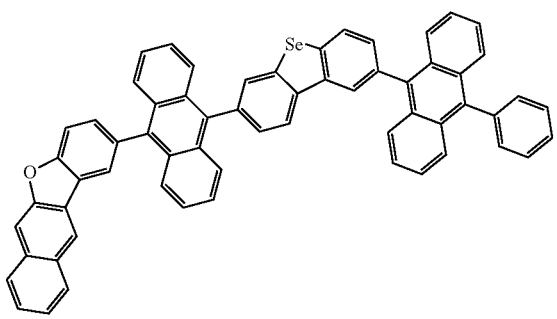

1882
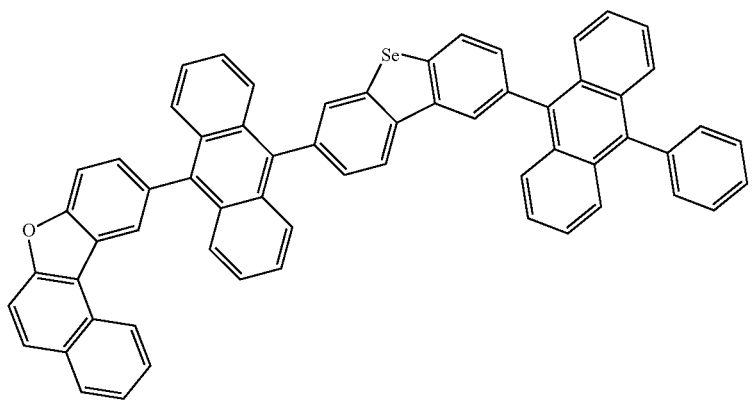
1883
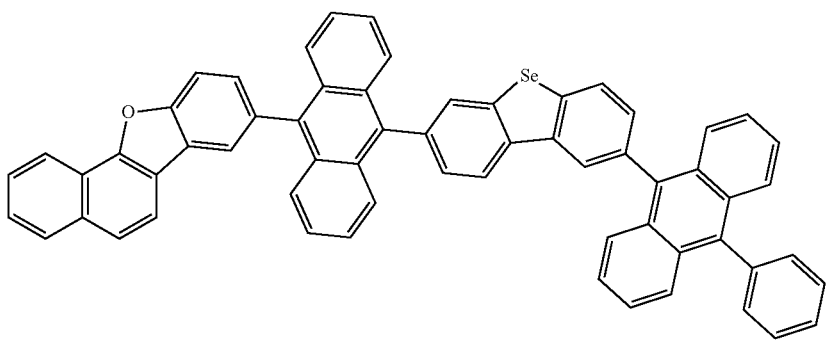
1884
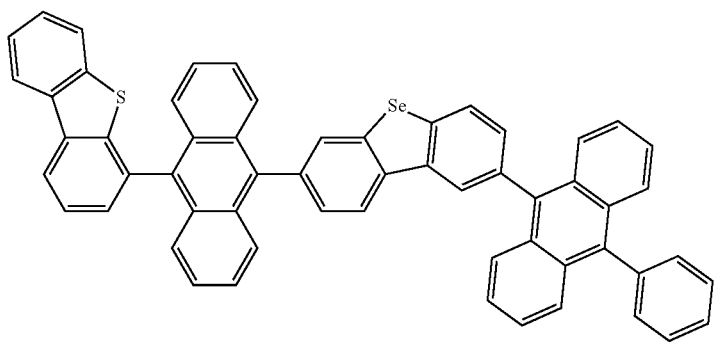
1885
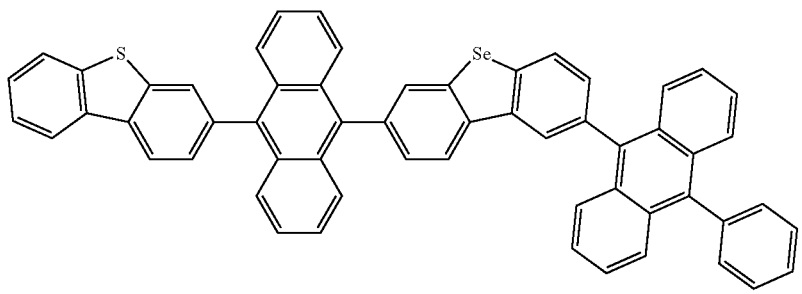
1886 1887
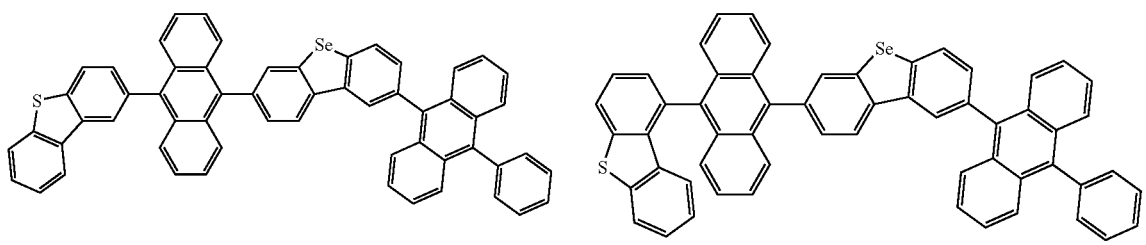

2157 2158
-continued
1888
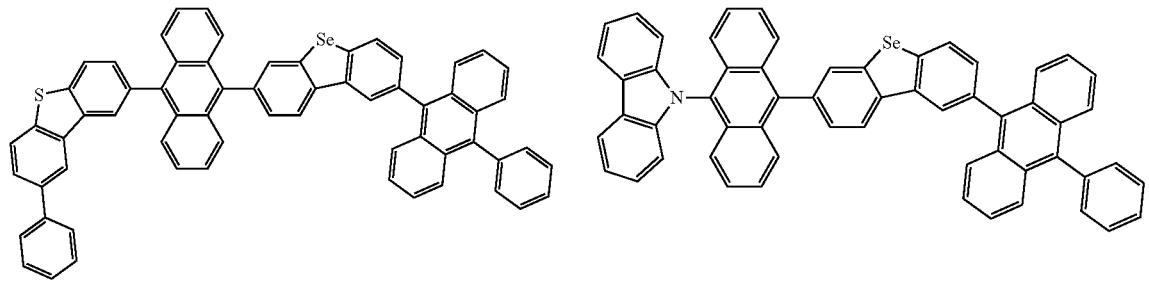
1889
1890
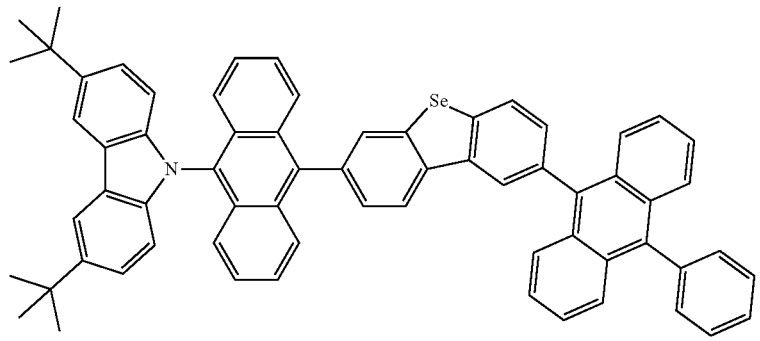
1891
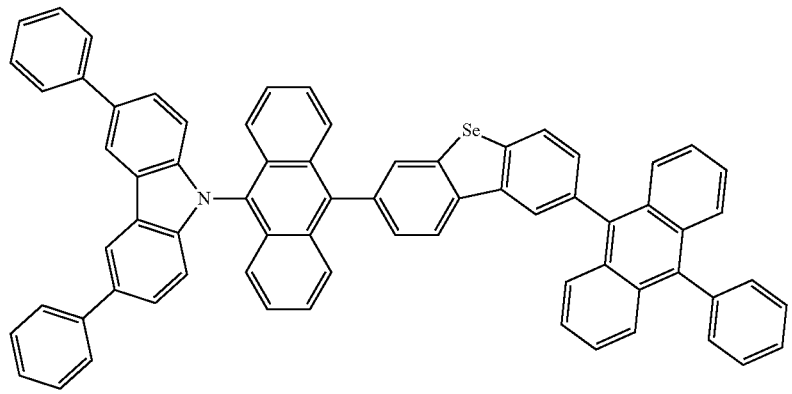
1892
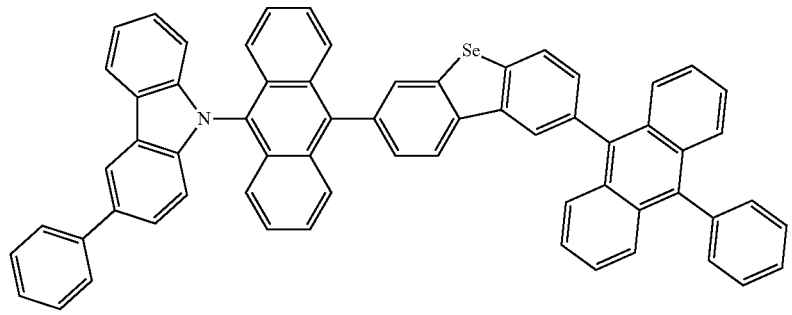

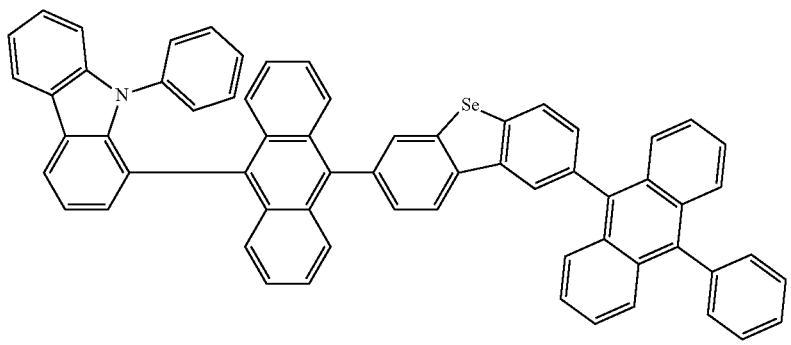
1893
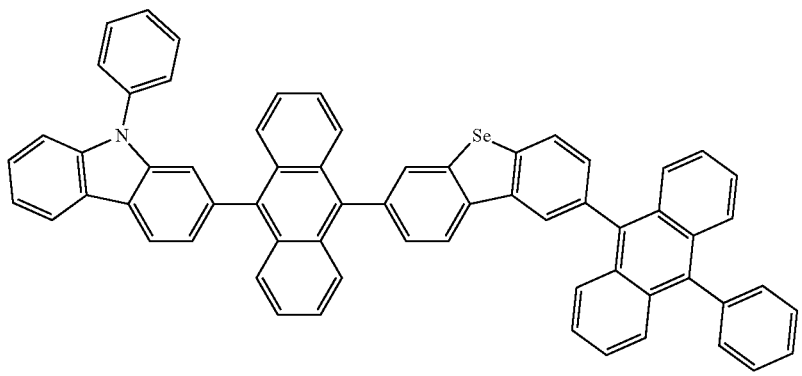
1894
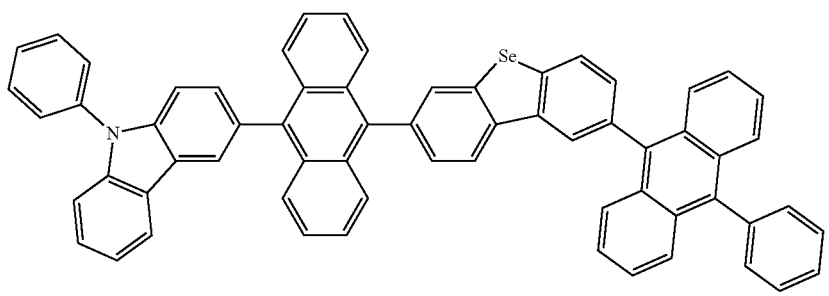
1895
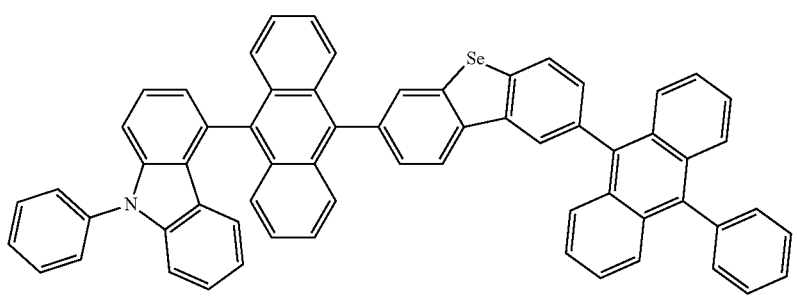
1896
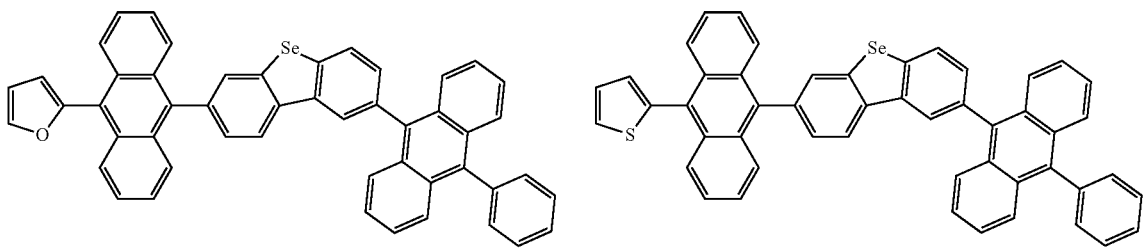
1897 1898

-continued
| 1899 | 1900 |
|---|---|
| 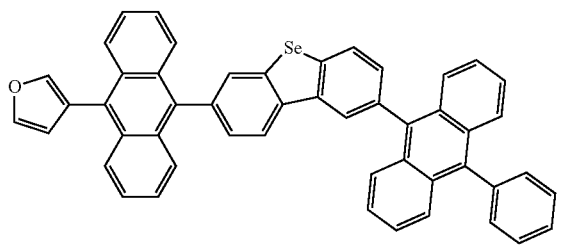 | 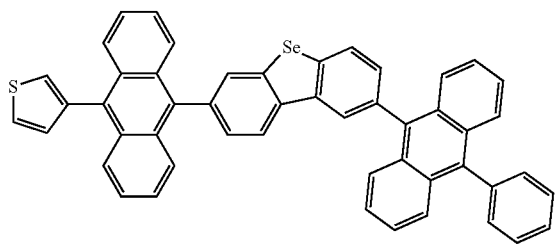 |
| 1901 | 1902 |
| 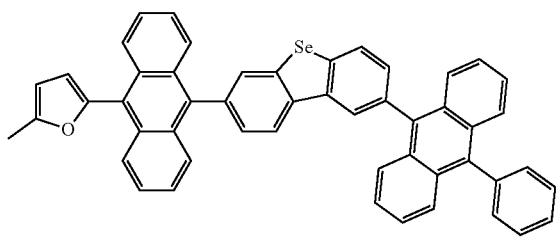 | 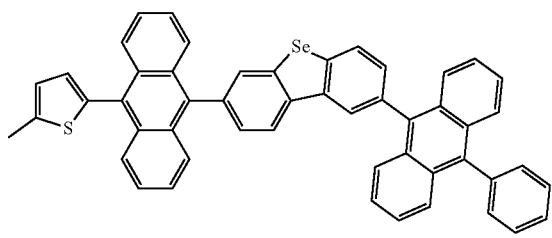 |
| 1903 | 1904 |
| 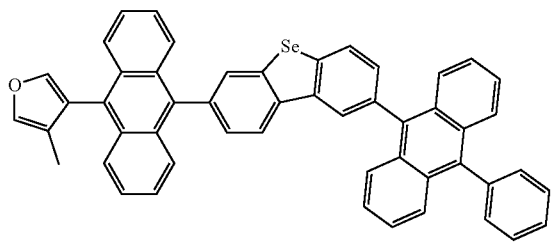 | 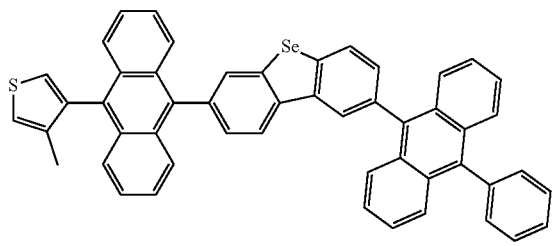 |
| 1905 | 1906 |
| 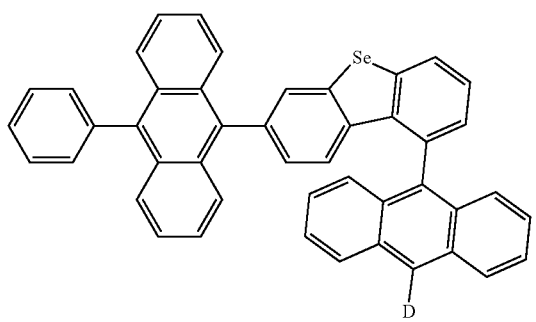 | 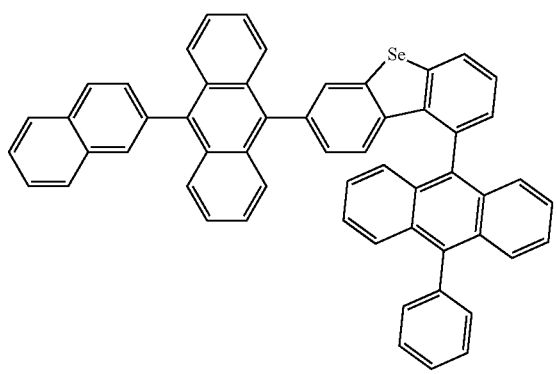 |
| 1907 | 1908 |
| 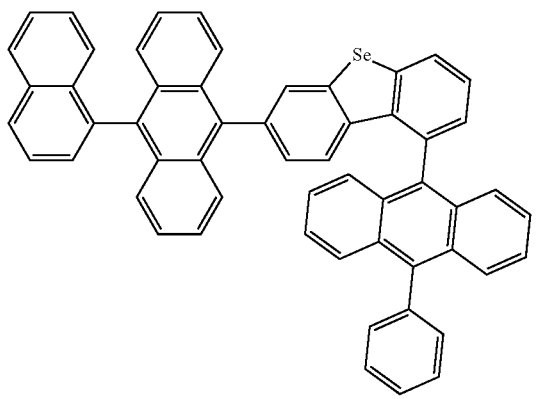 | 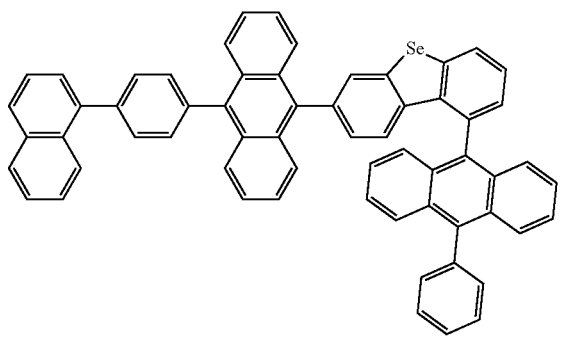 |

-continued
1909
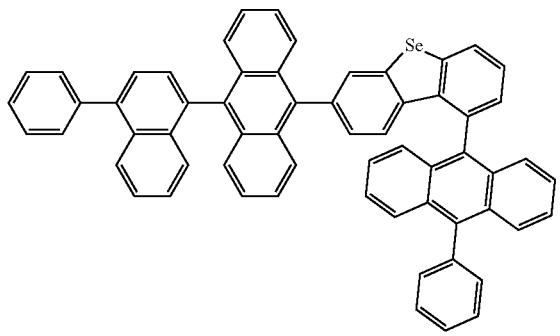
1910
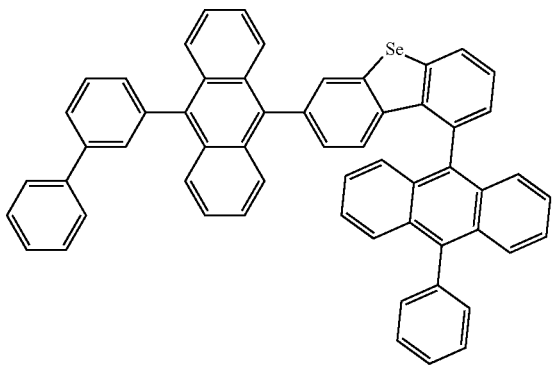
1911
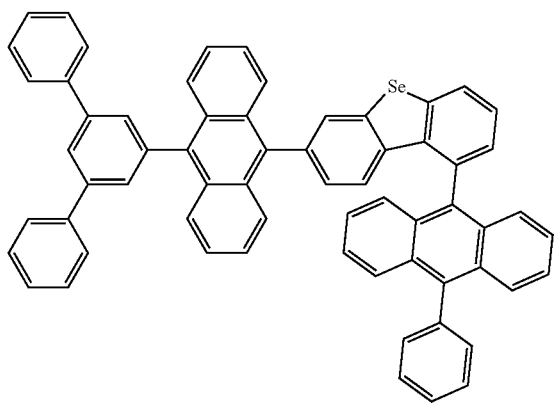
1912
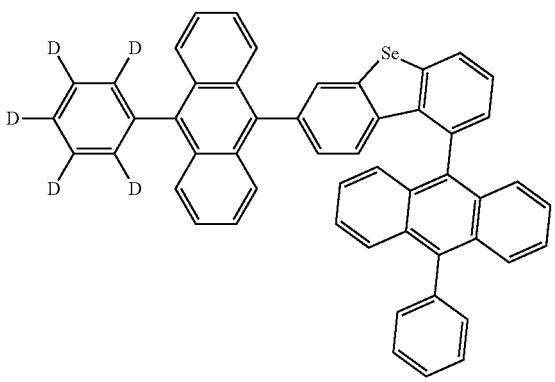
1913
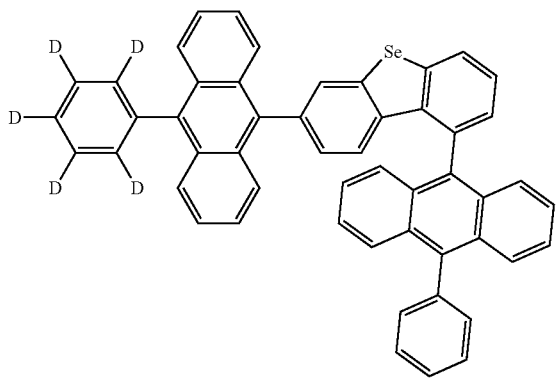
1914
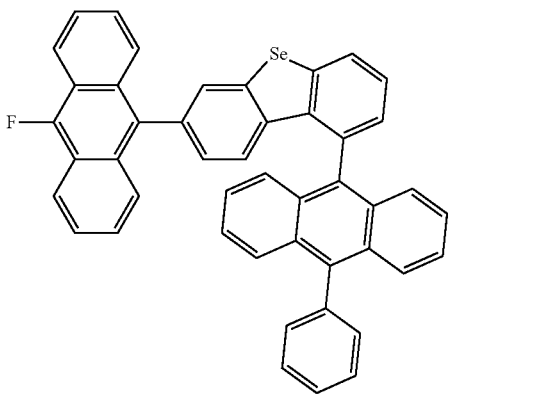
1915
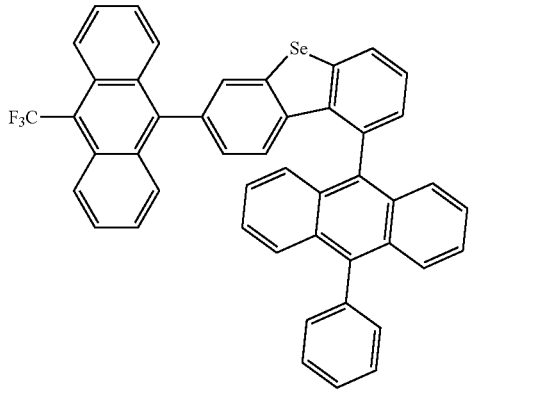
1916
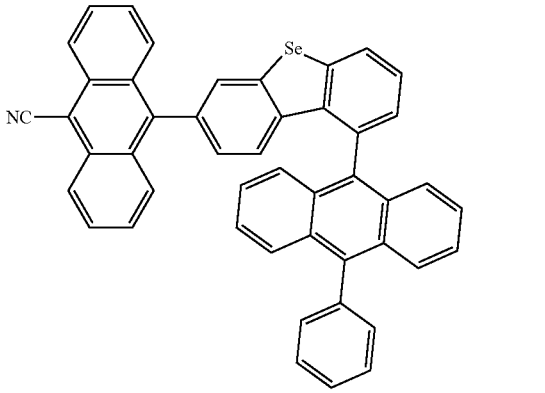

-continued
1917
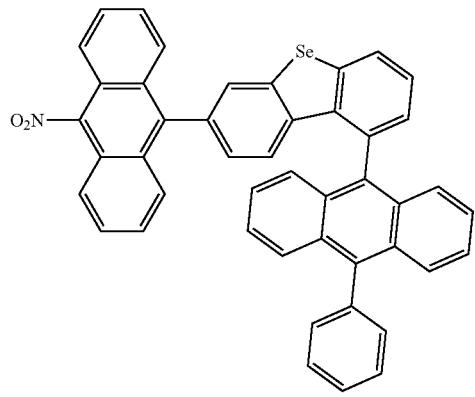
1918
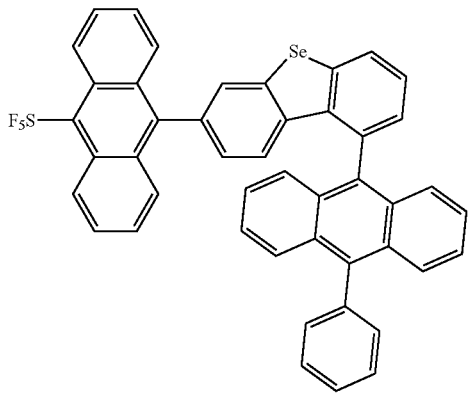
1919
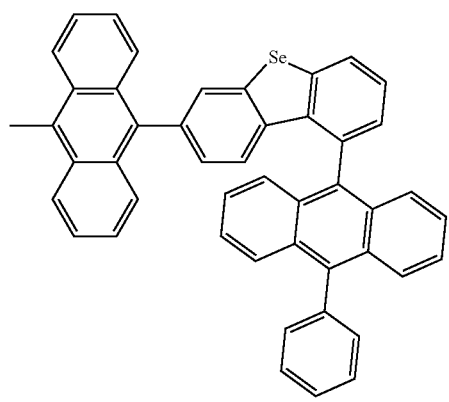
1920
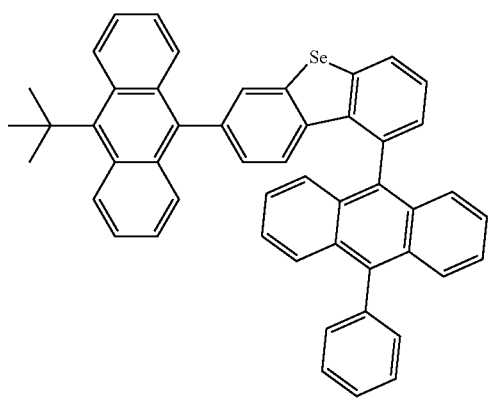
1921
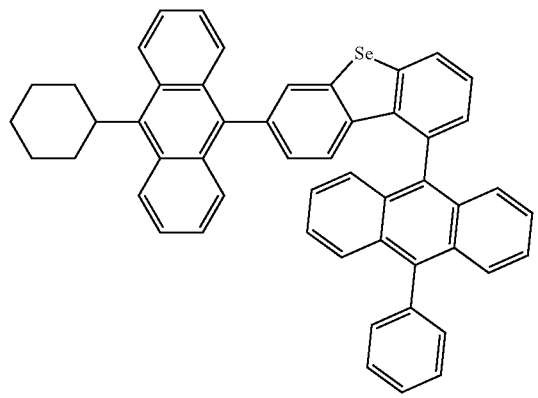
1922
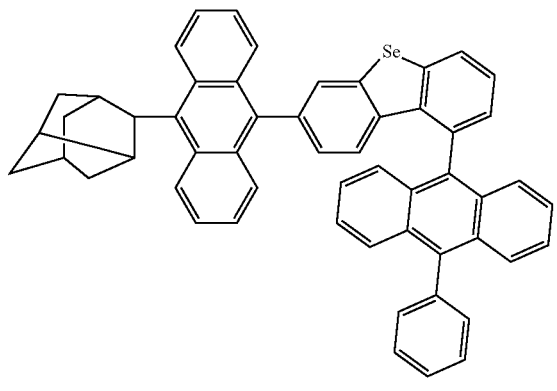
1923
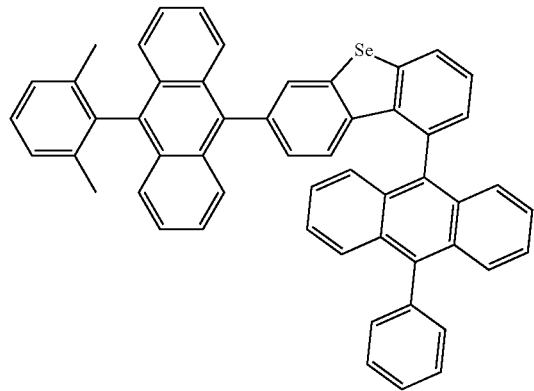
1924
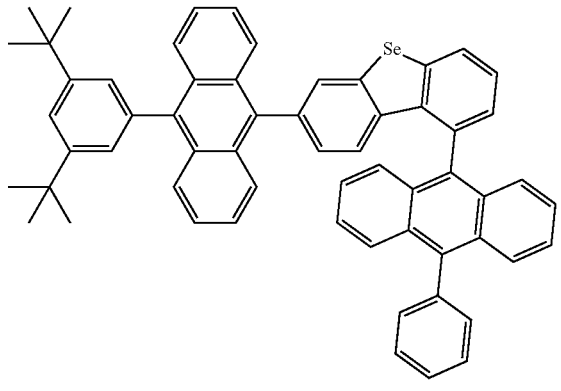

-continued
1925
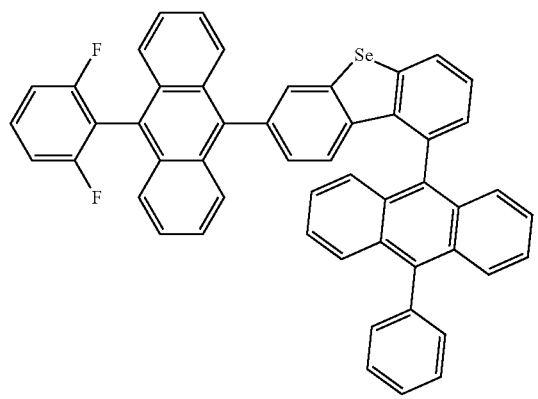
1926
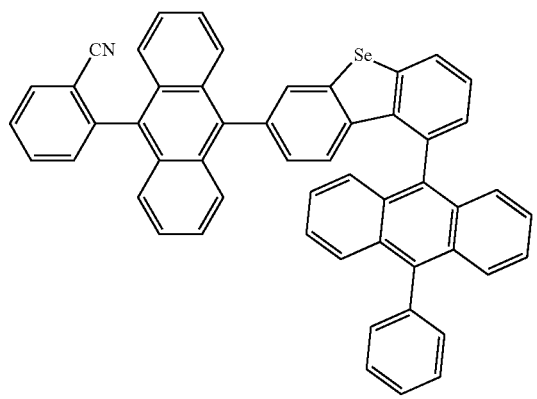
1927
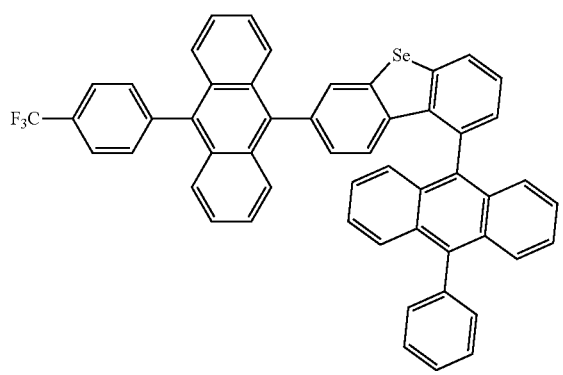
1928
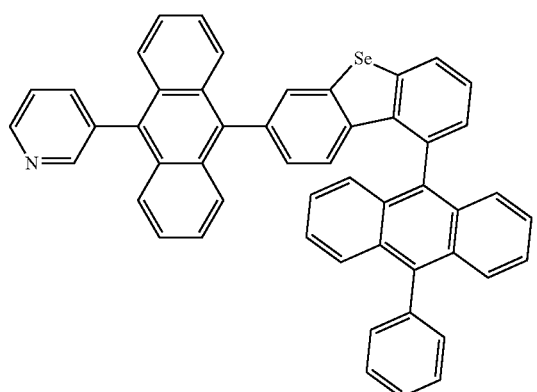
1929
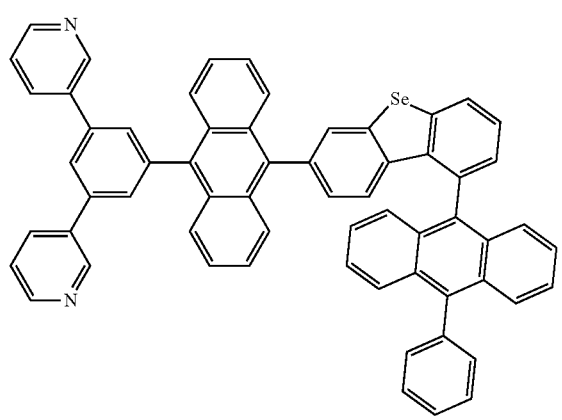
1930
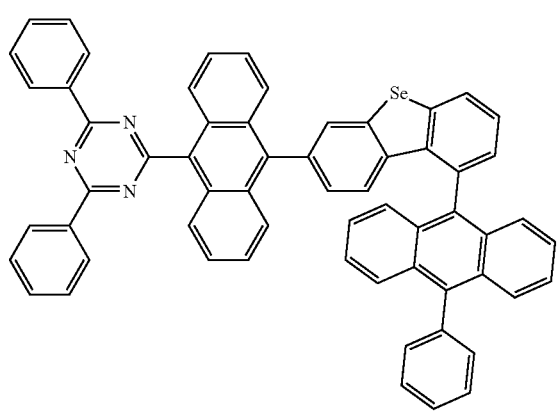

-continued
1931
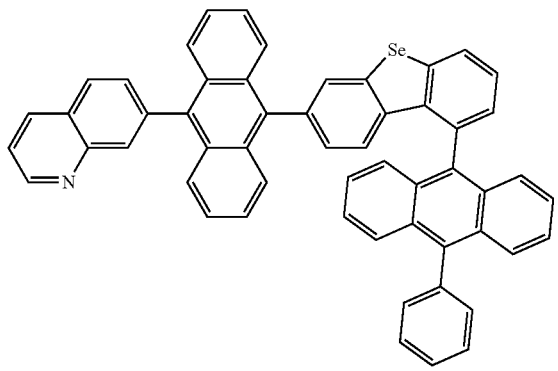
1932
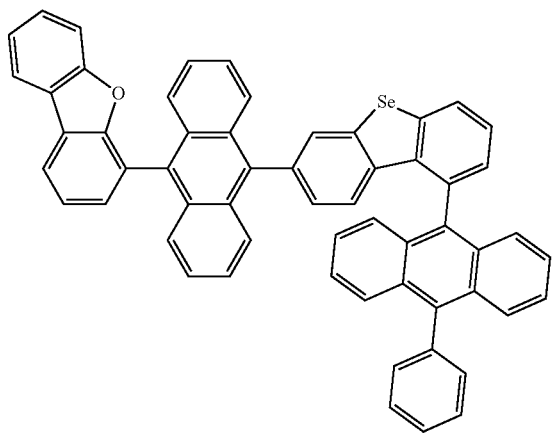
1933
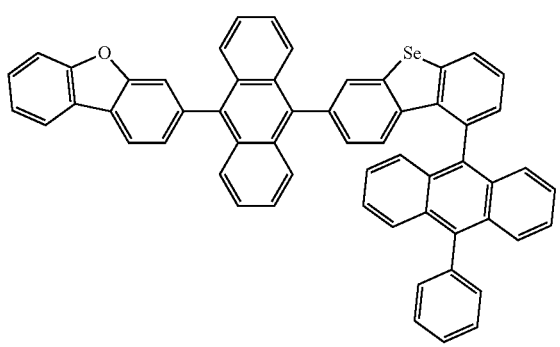
1934
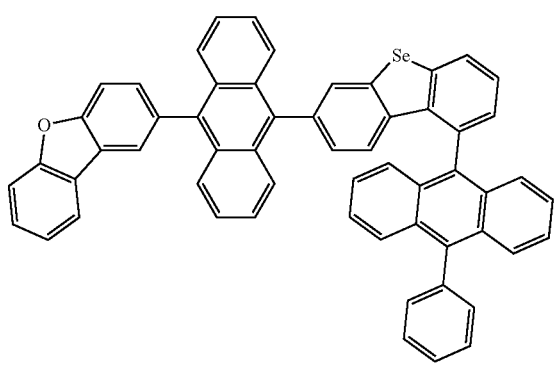
1935
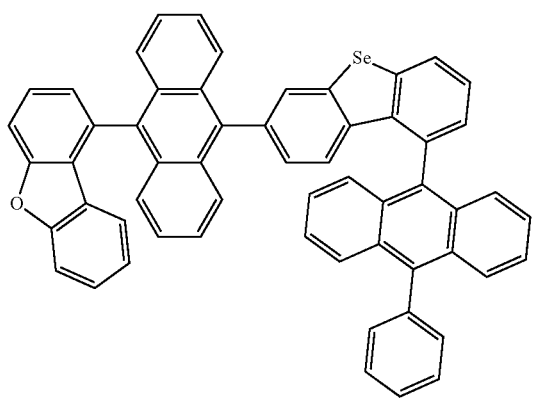
1936
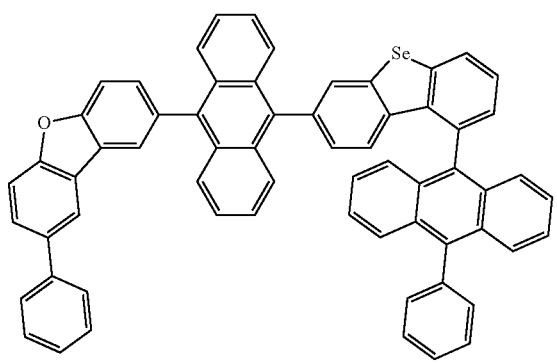
1937
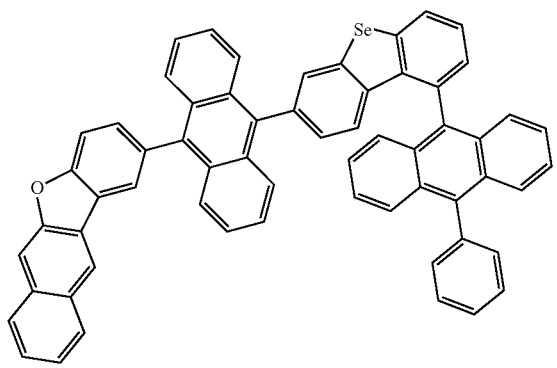
1938
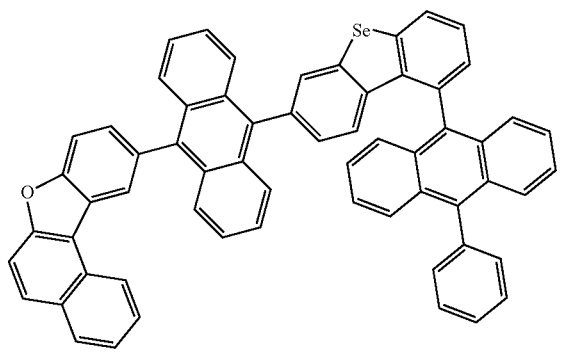

-continued
1939
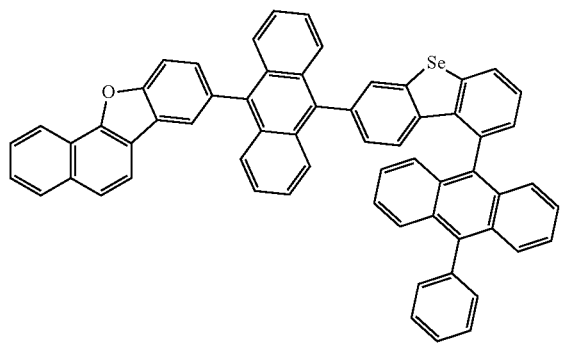
1940
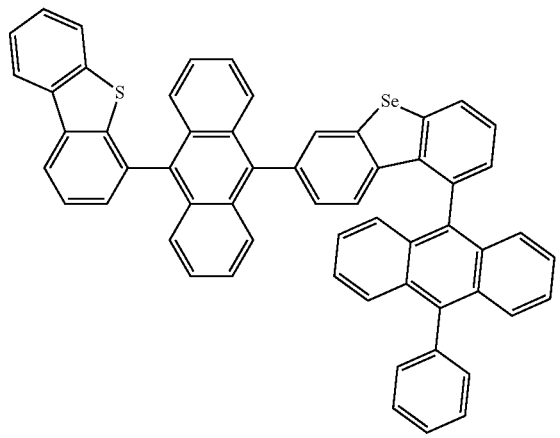
1941
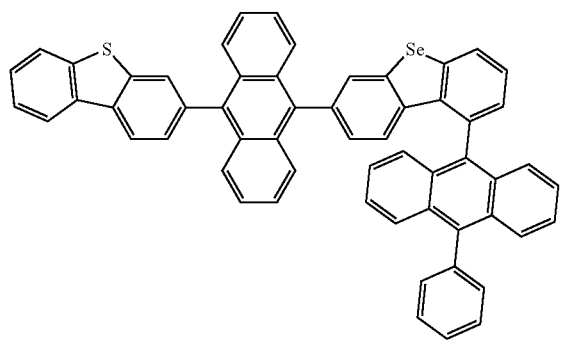
1942
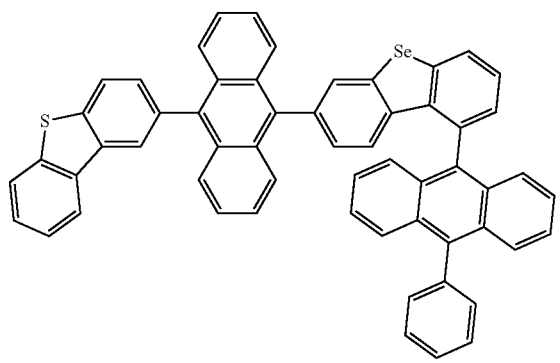
1943
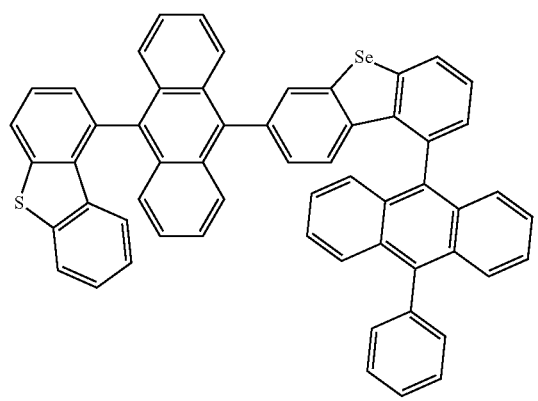
1944
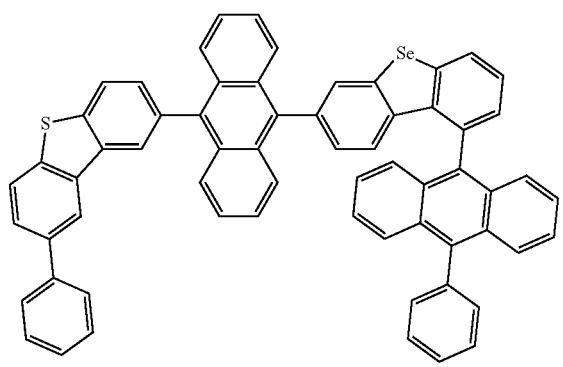

-continued
1945
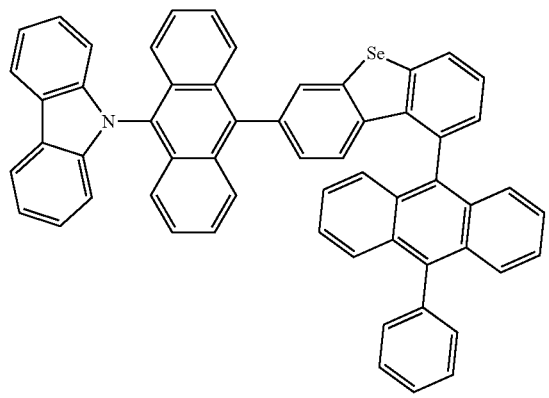
1946
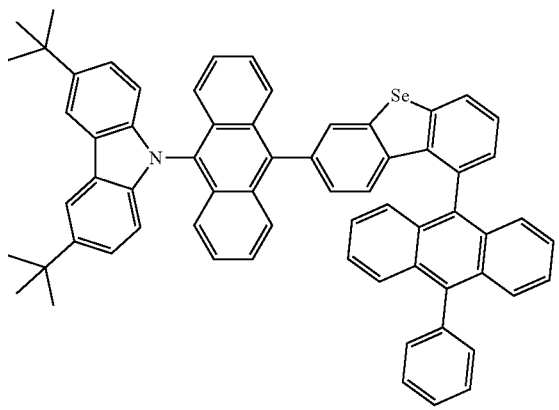
1947
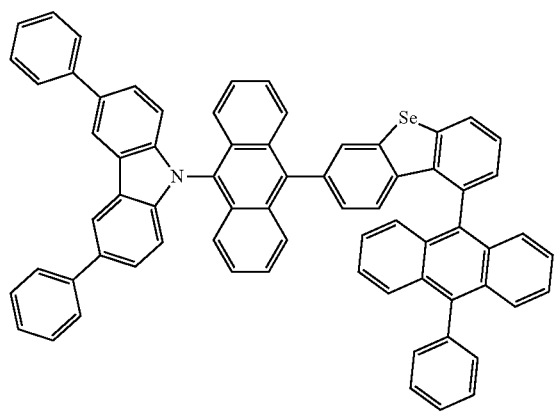
1948
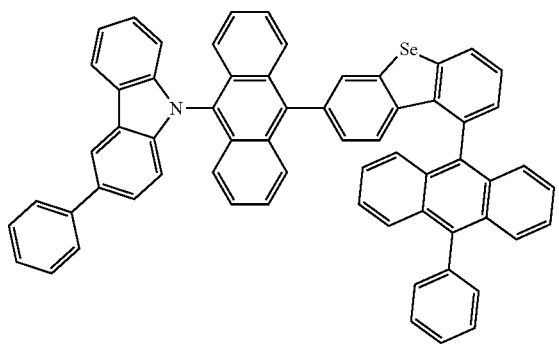
1949
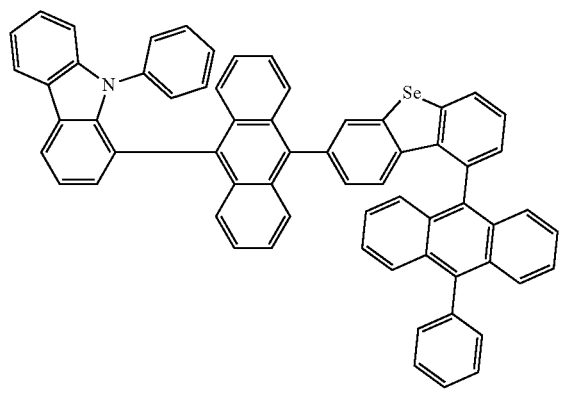
1950
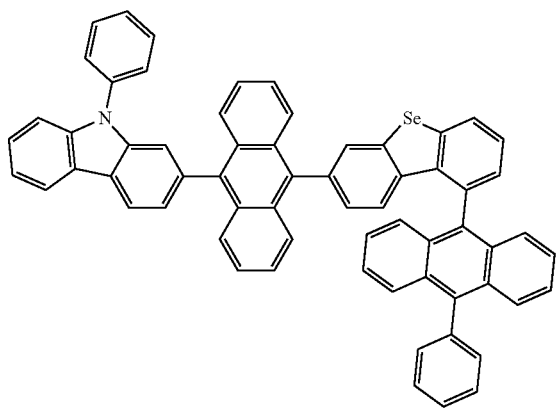
1951
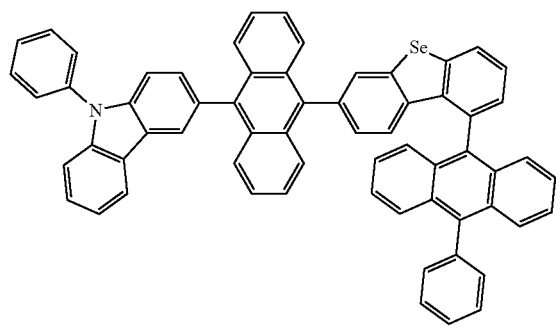
1952
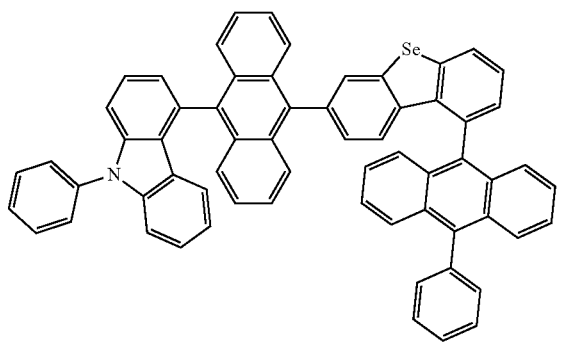

-continued
2175
1953
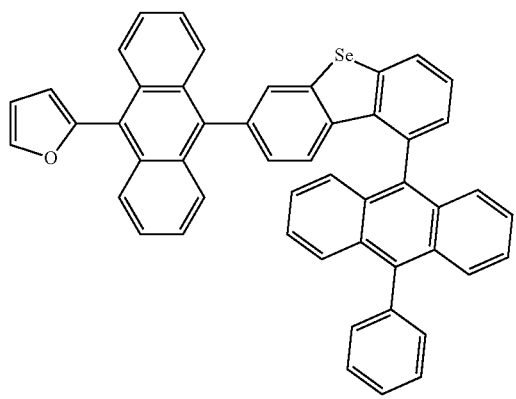
1955
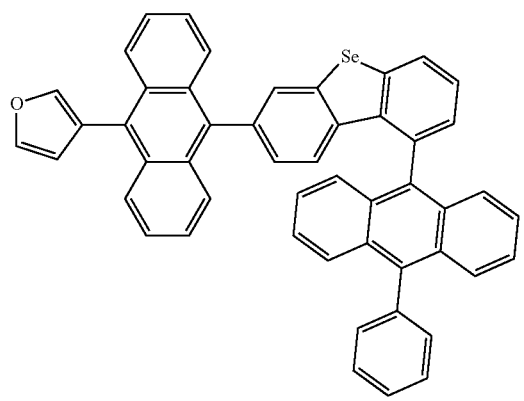
1957
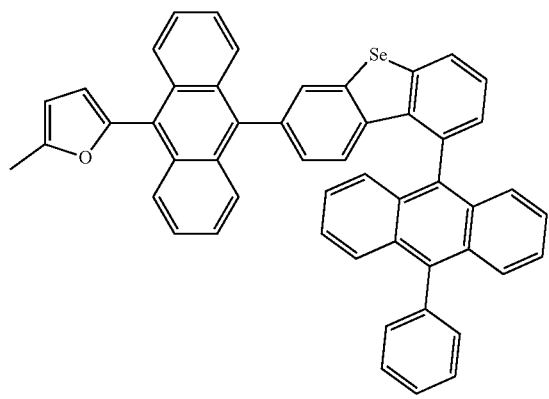
1958
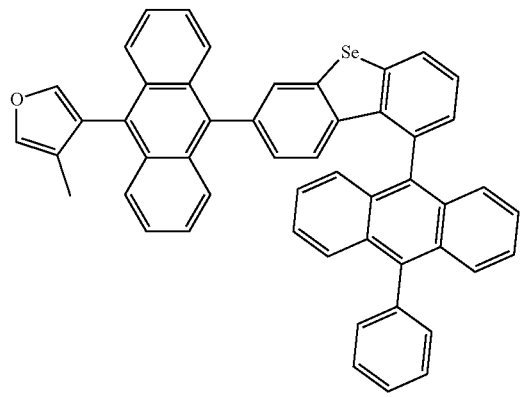
2176
1954
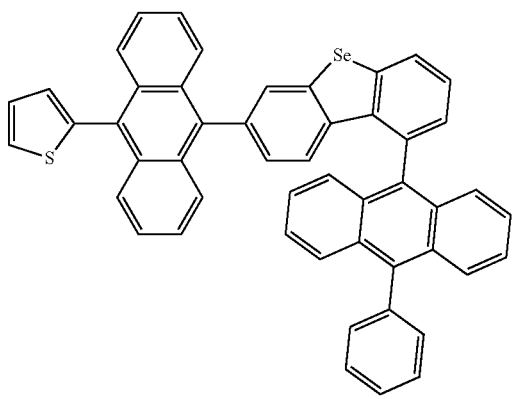
1956
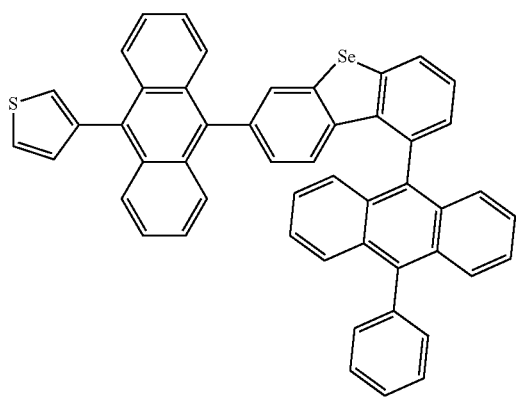
1958
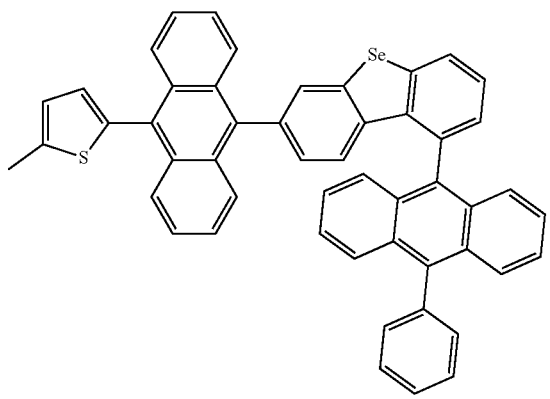
1960
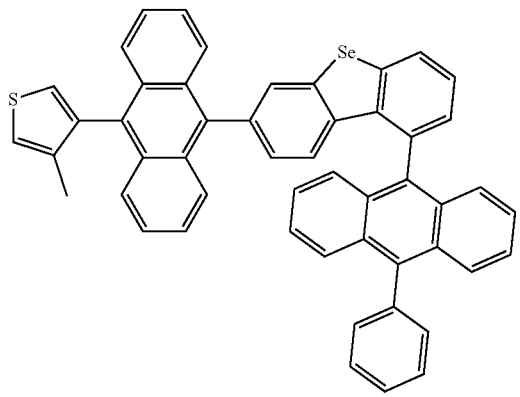

-continued
1961
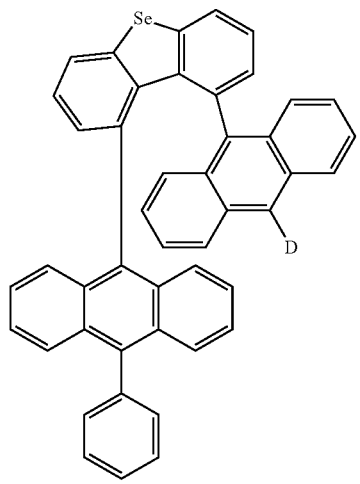
1962
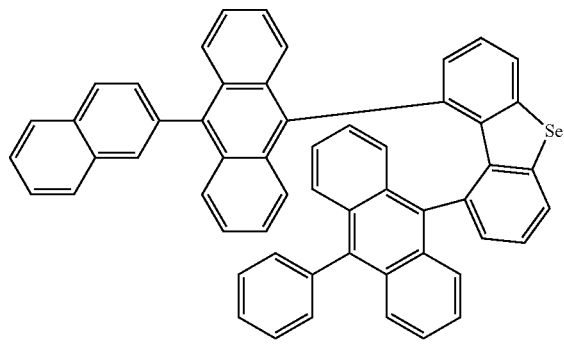
1963
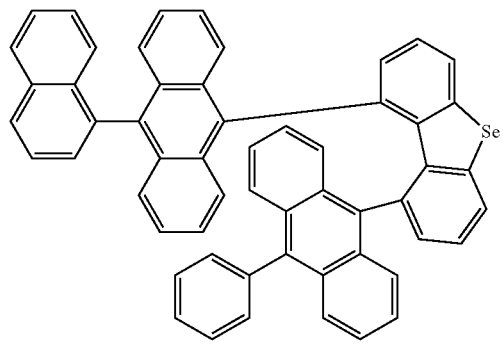
1964
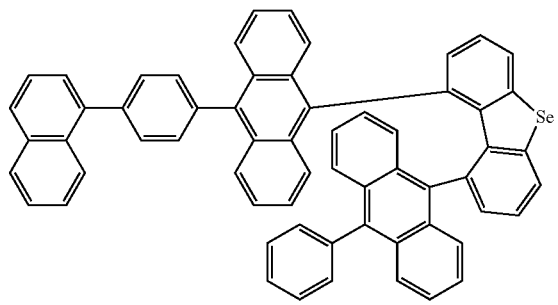
1965
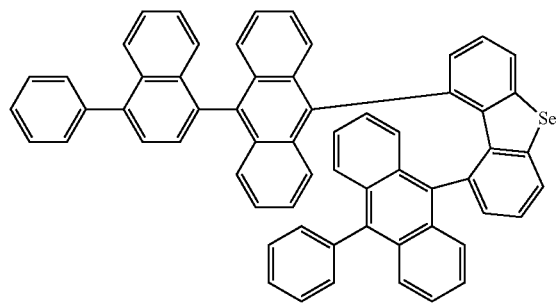
1966
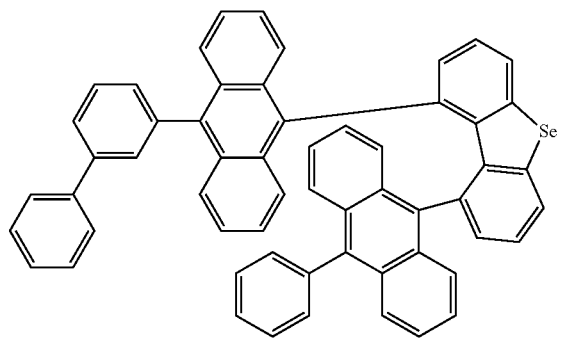
1967
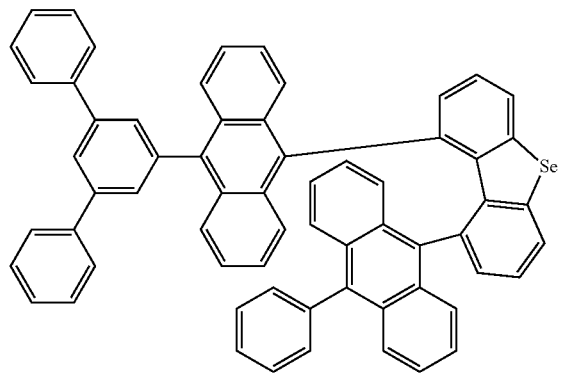
1968
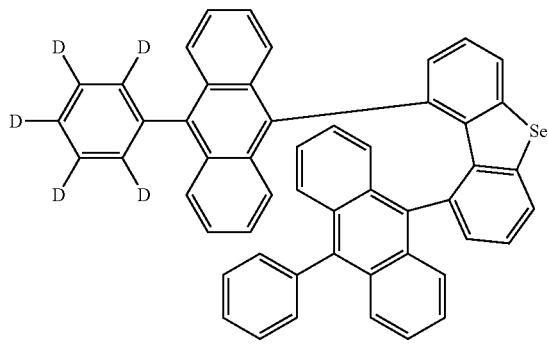

1969
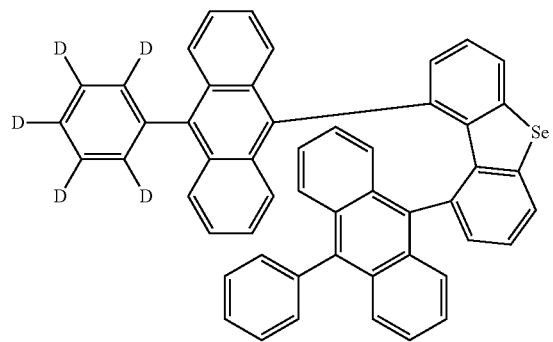
1970
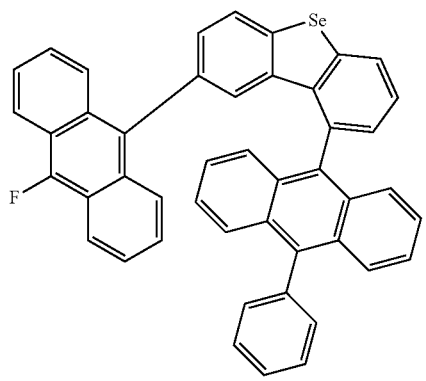
1971
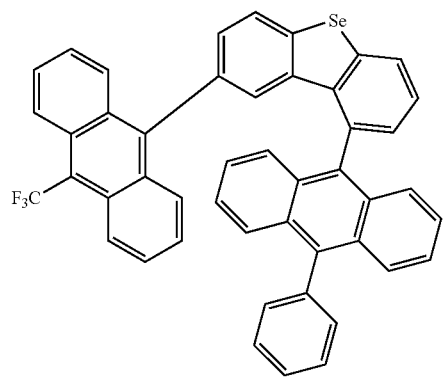
1972
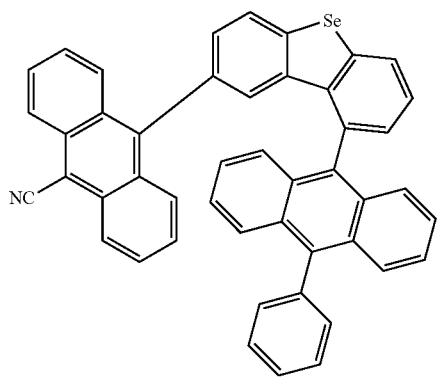
1973
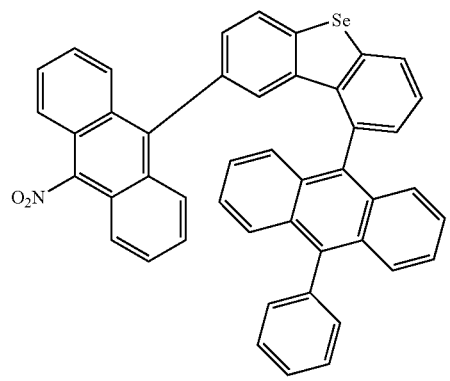
1974
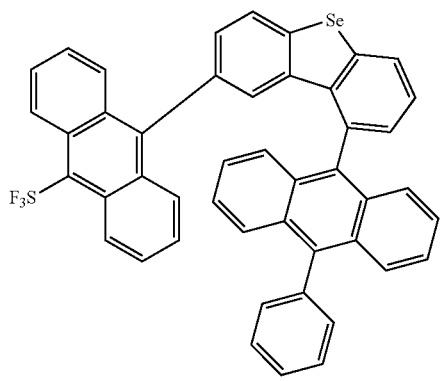
1975
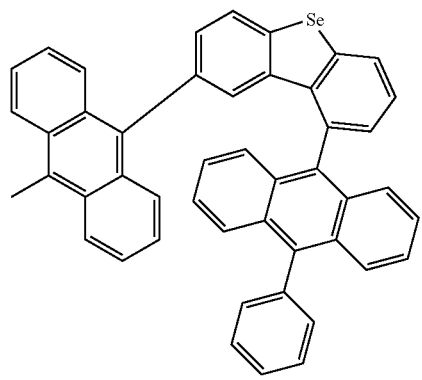
1976
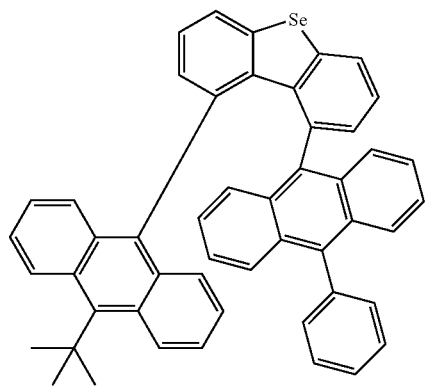

-continued
1977
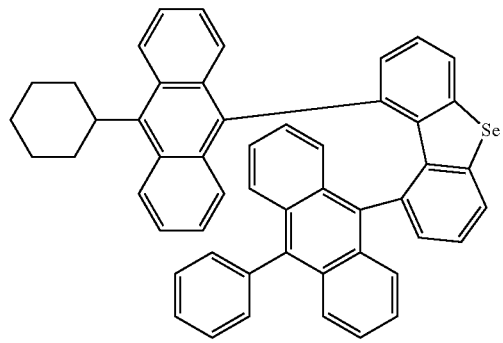
1978
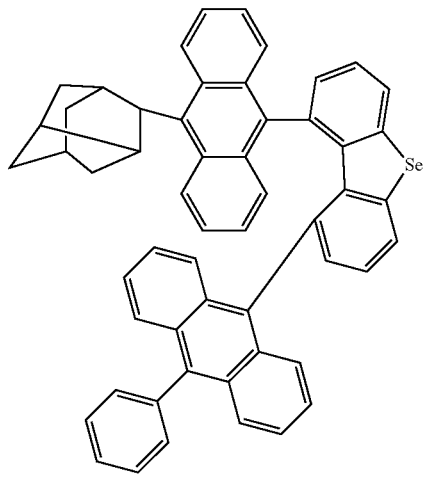
1979
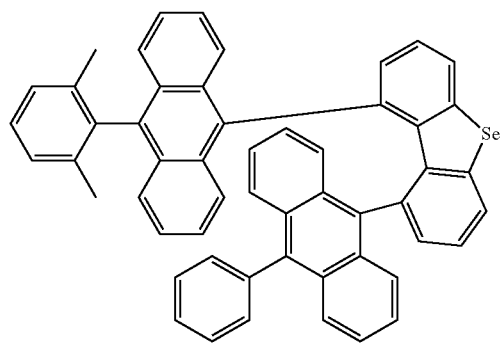
1980
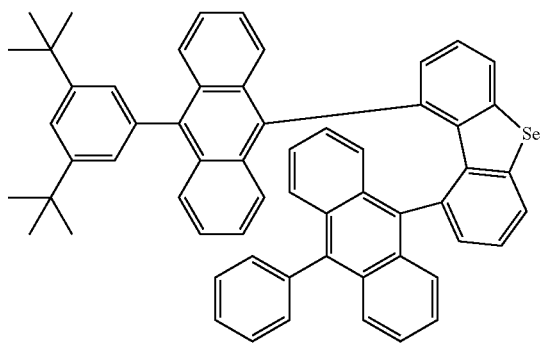
1981
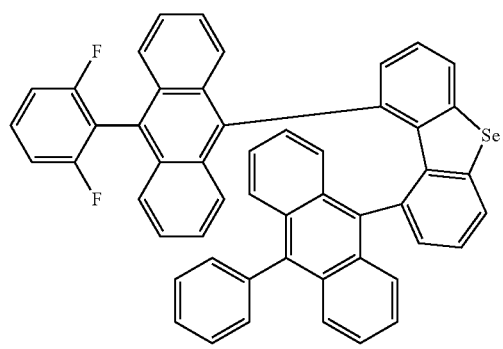
1982
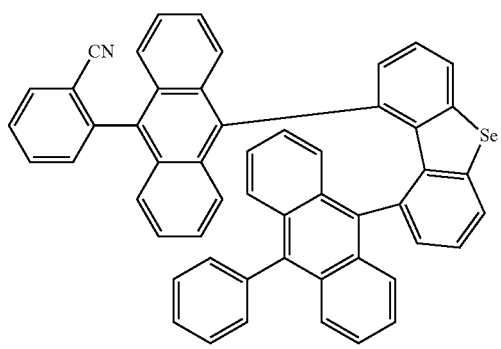
1983
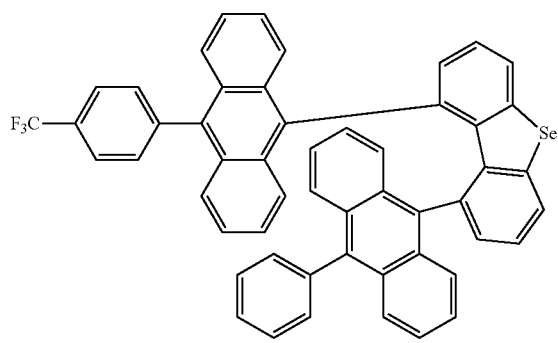
1984
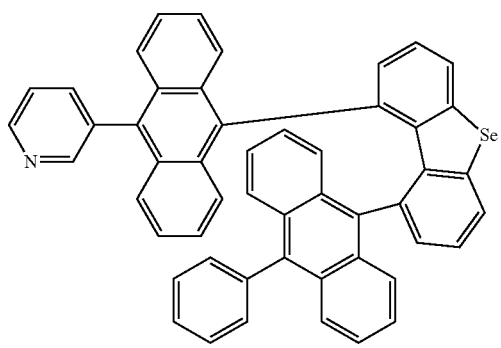

-continued
1985
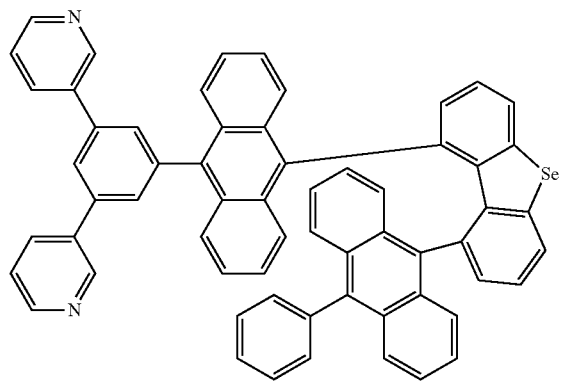
1986
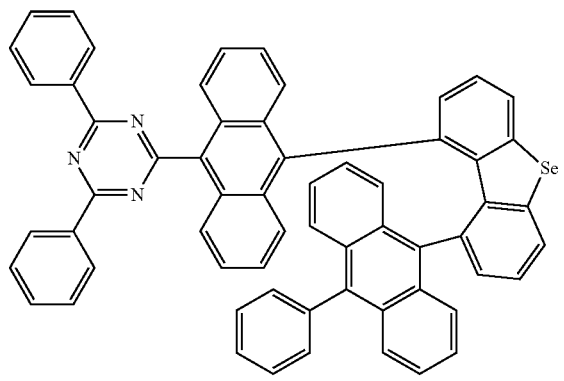
1987
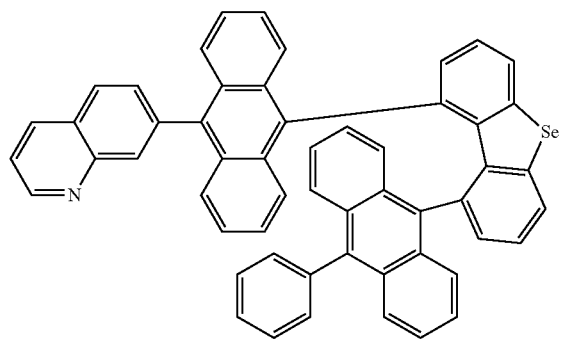
1988
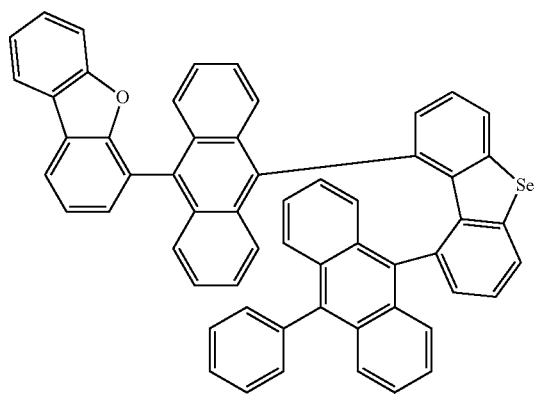
1989
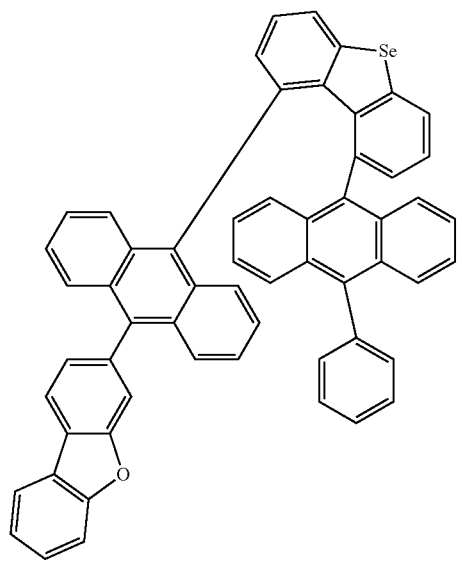
1990
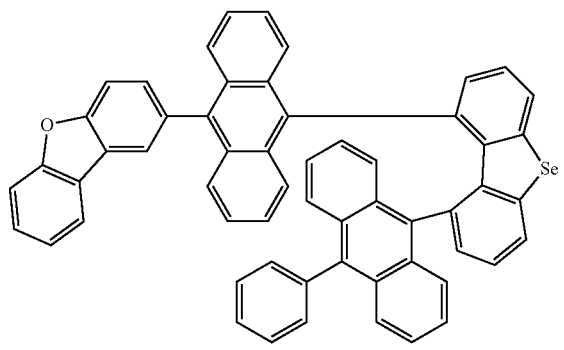

-continued
1991
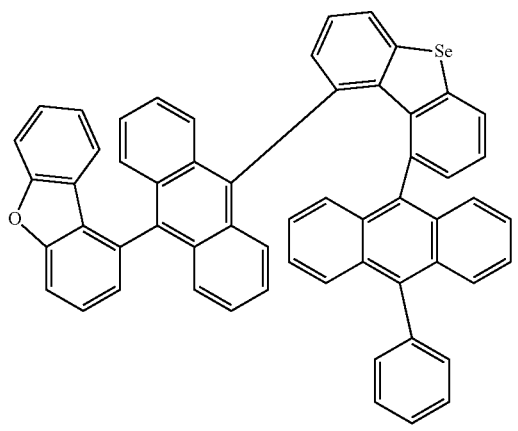
1992
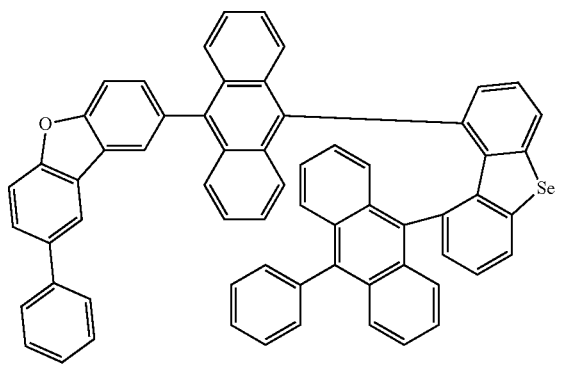
1993
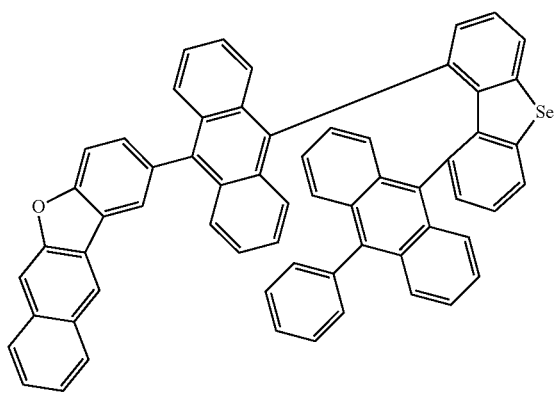
1994
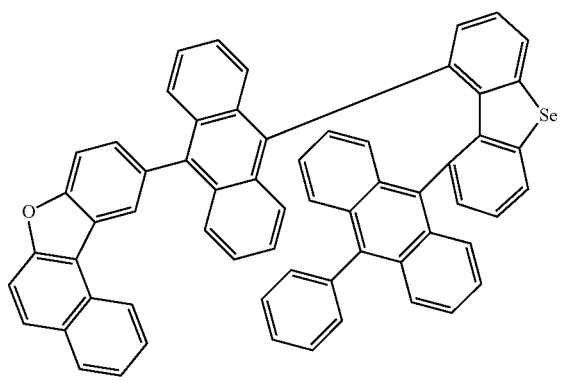
1995
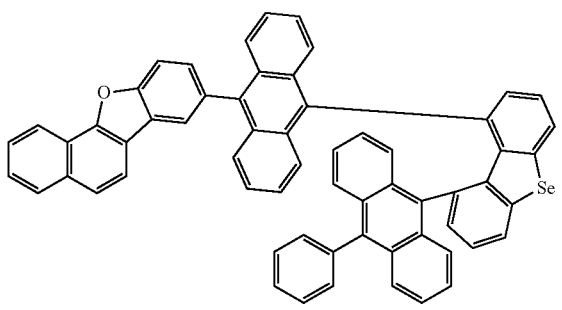
1996
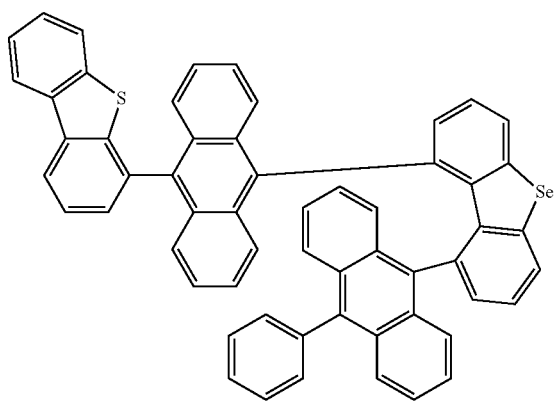

-continued
| 1997 | 1998 |
|---|---|
| 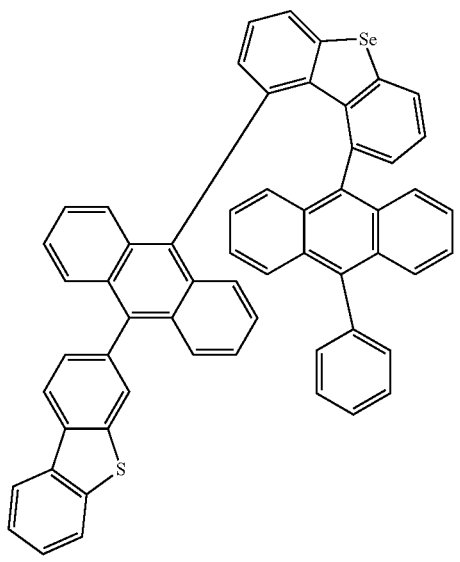 | 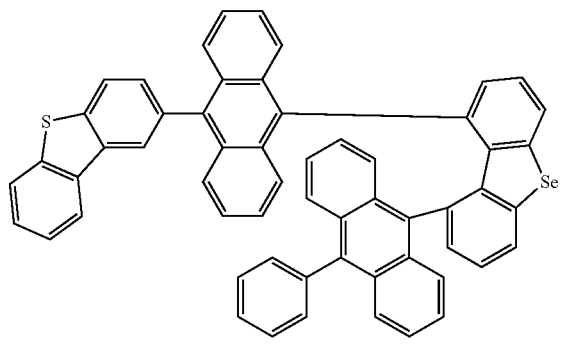 |
| 1999 | 2000 |
| 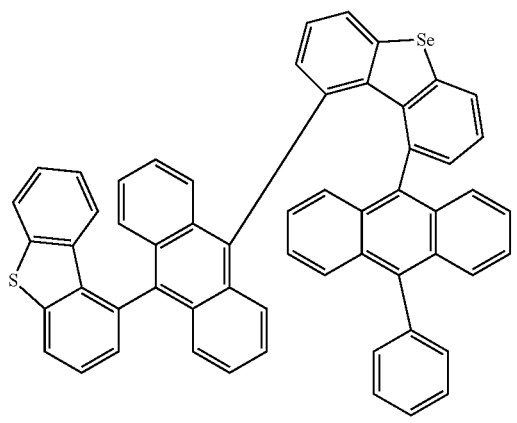 | 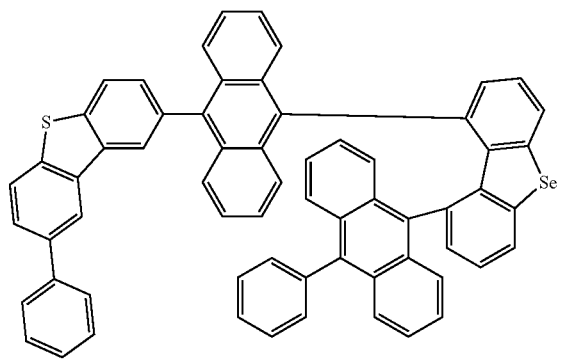 |
| 2001 | 2002 |
| 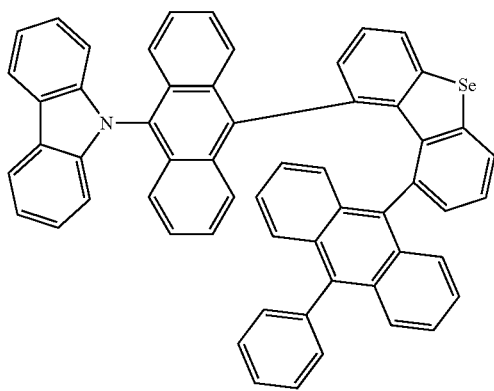 | 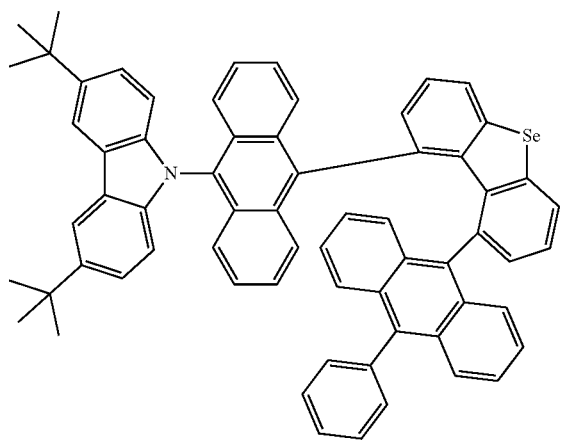 |

-continued
2003
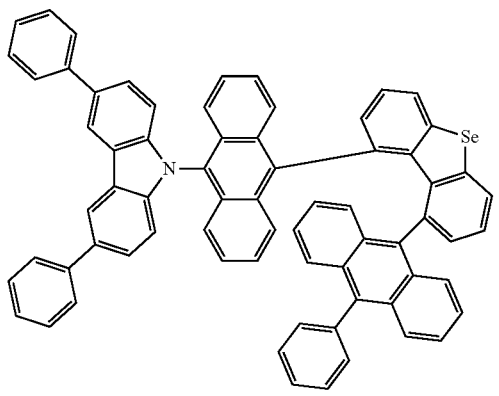
2004
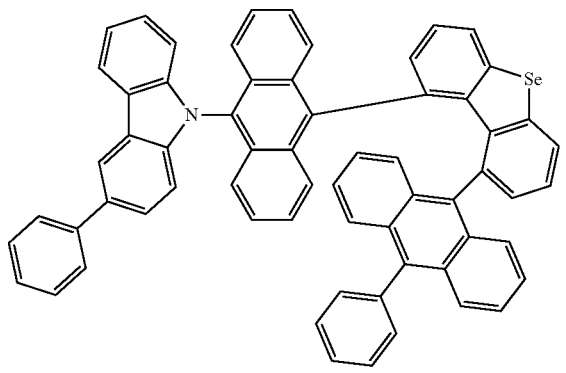
2005
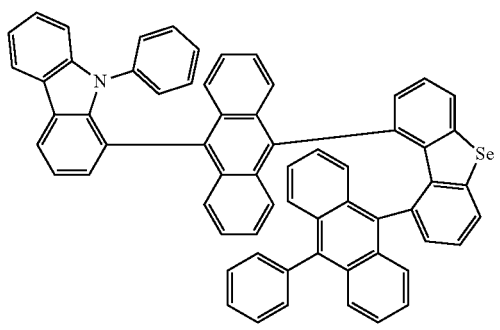
2006
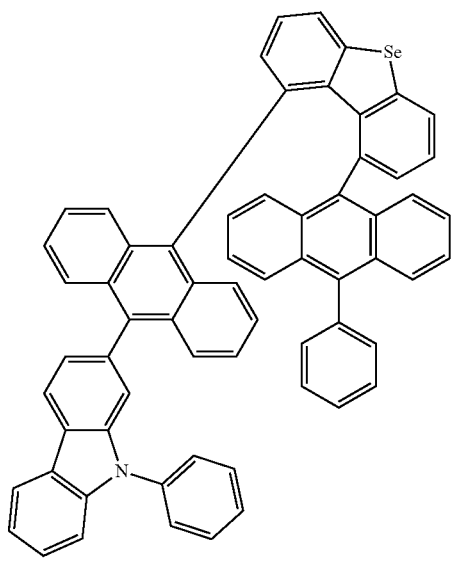
2007
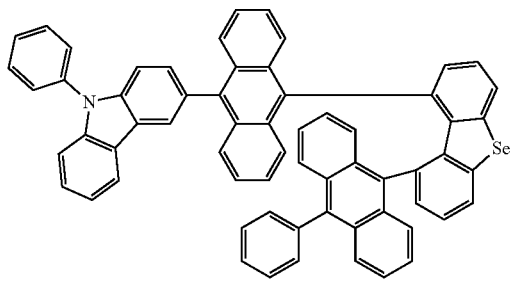
2008
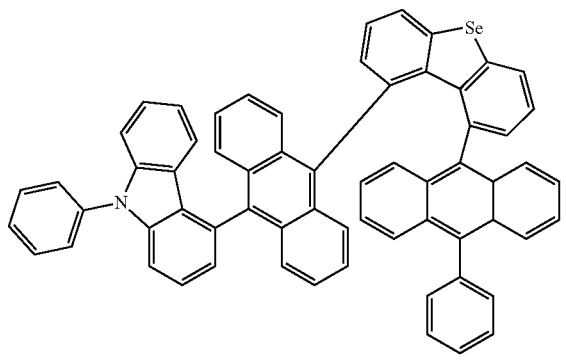

-continued
2191
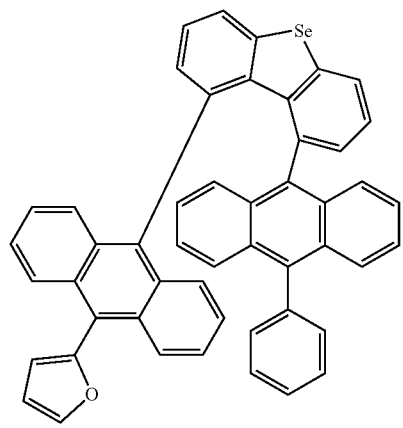
2009
2192
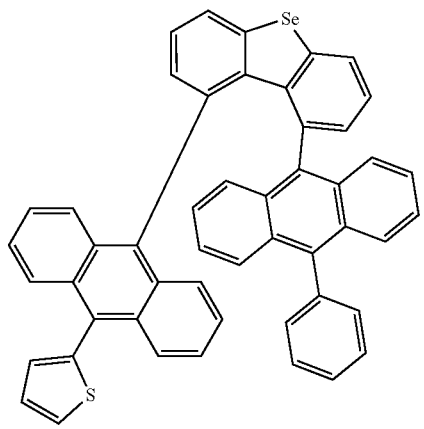
2010
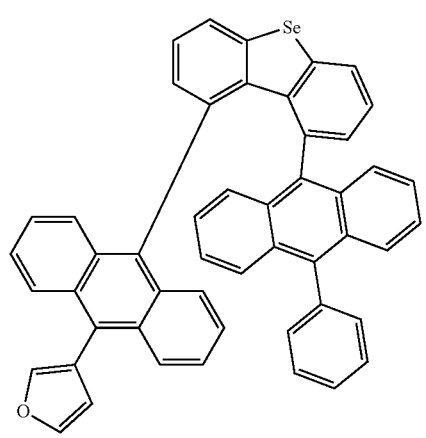
2011
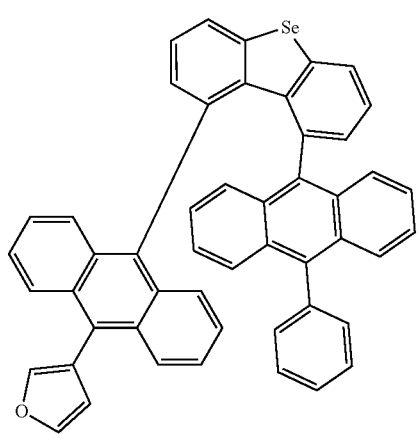
2012
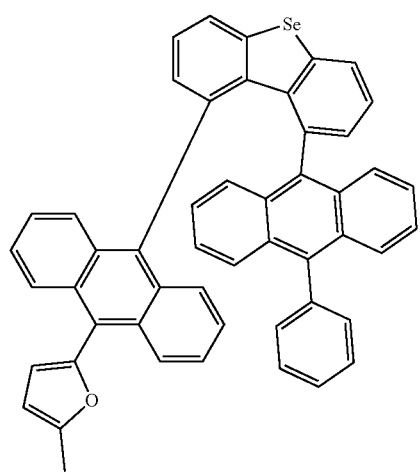
2013
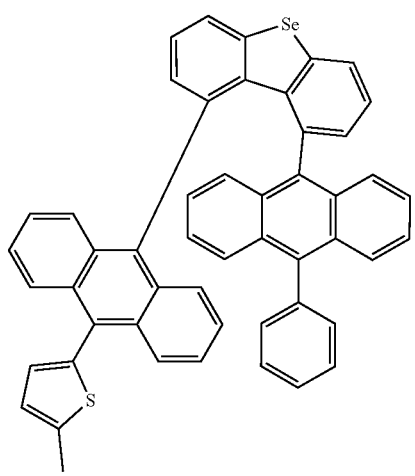
2014

-continued
2015
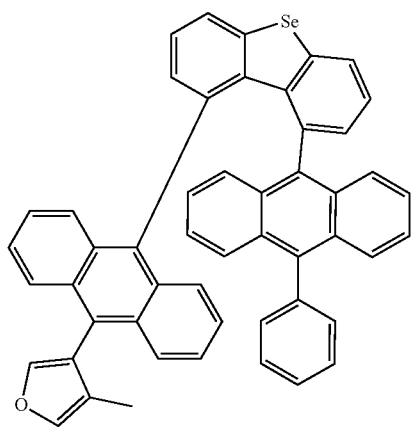
2016
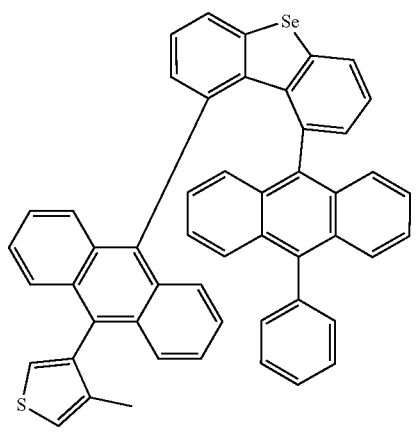
2017
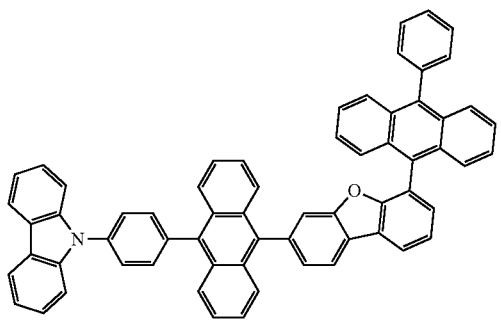
2018
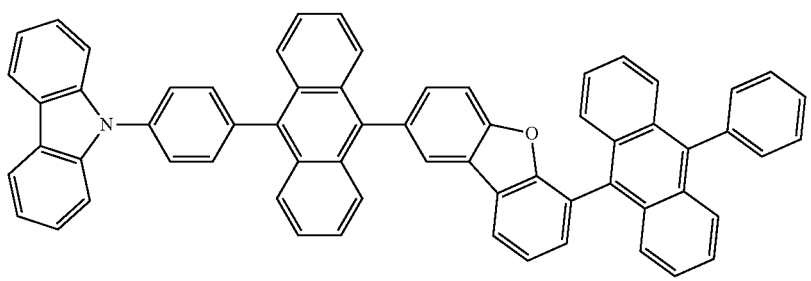
2019
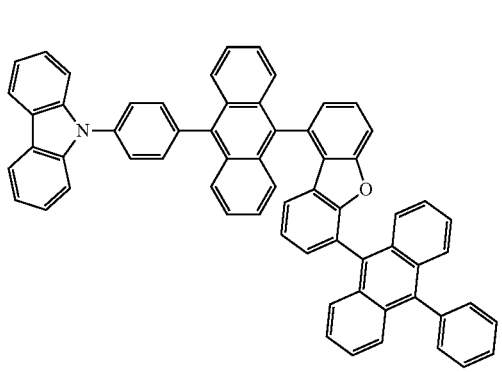
2020
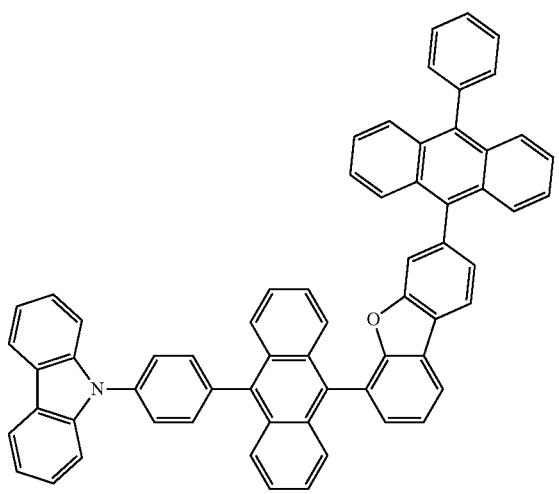

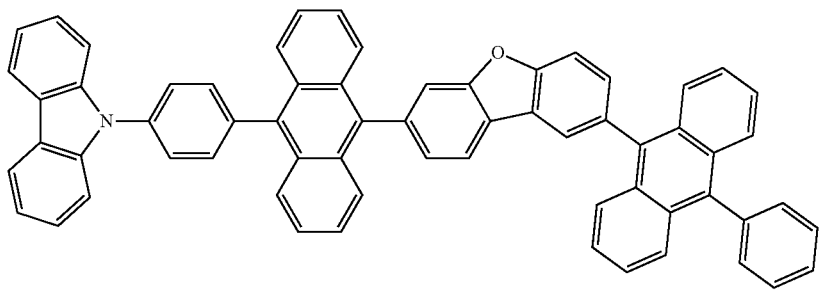
2021
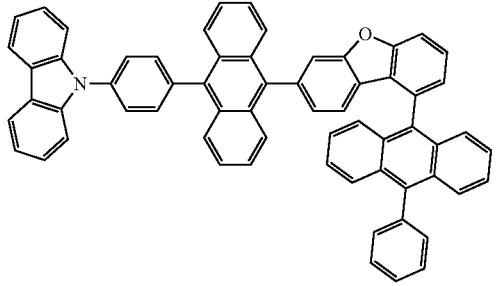
2022
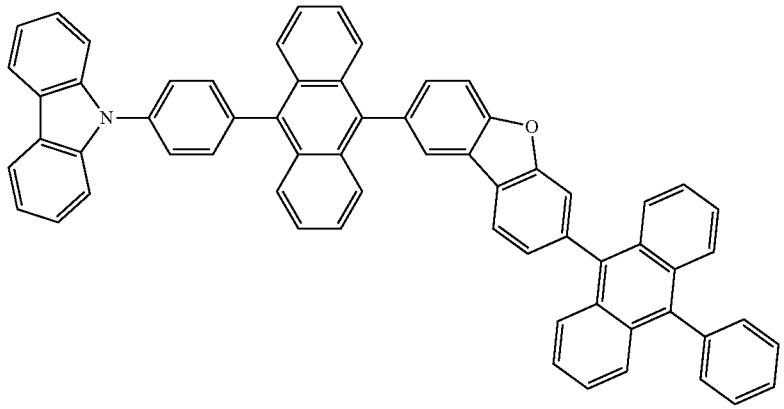
2023
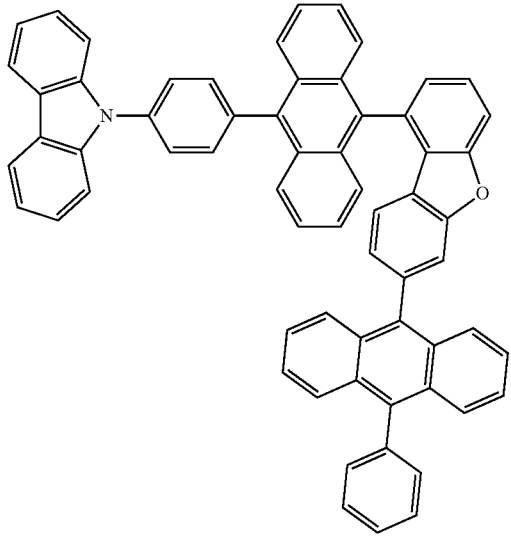
2024

-continued
2025
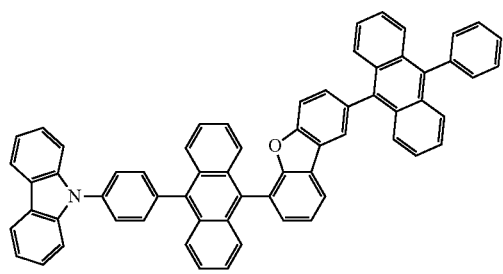
2026
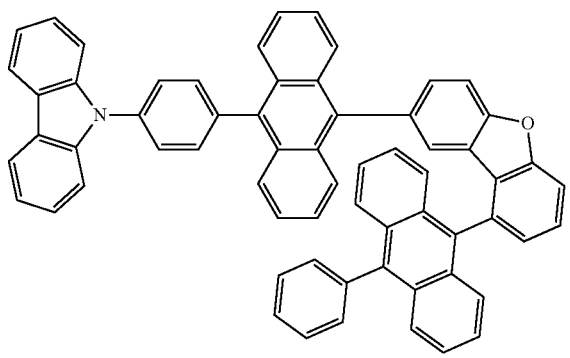
2027
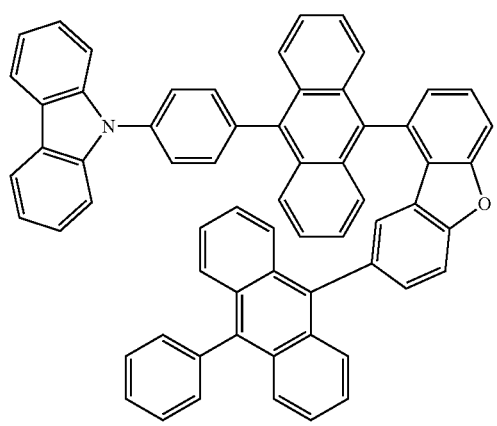
2028
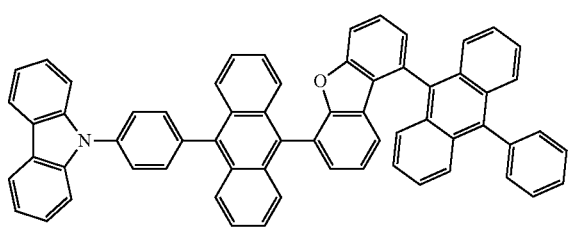
2029
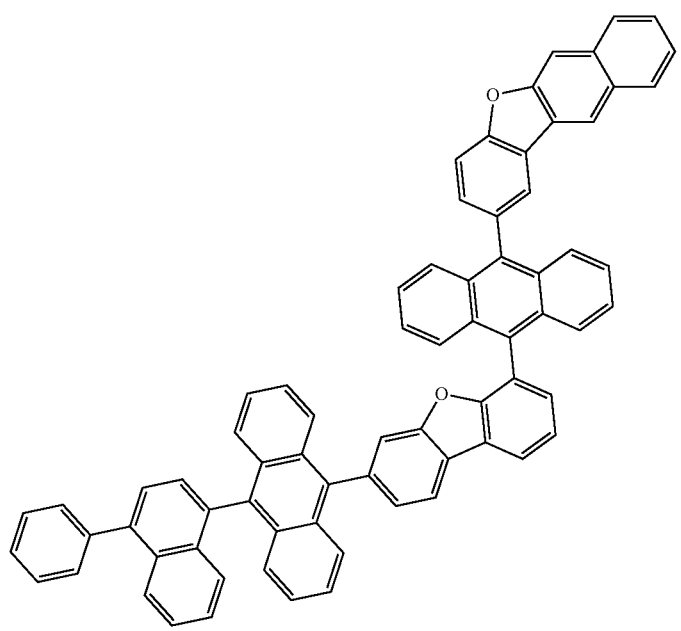

-continued
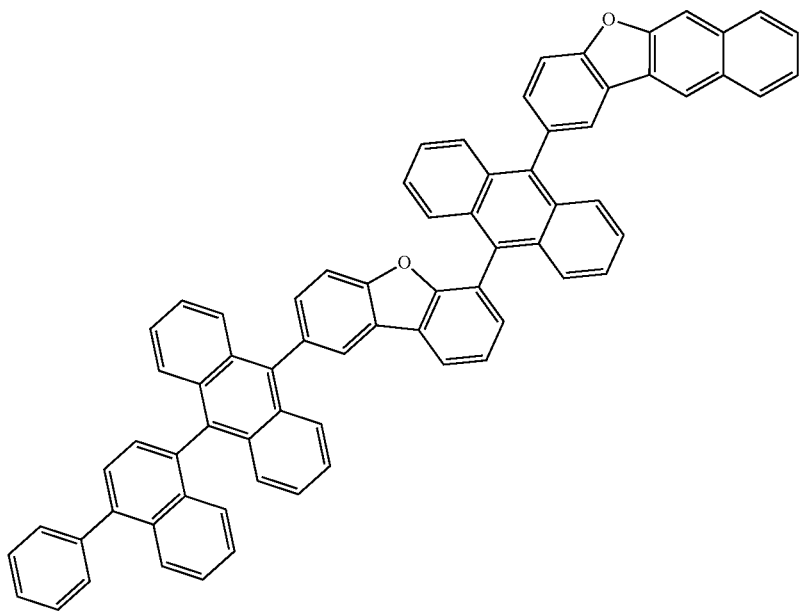
2030
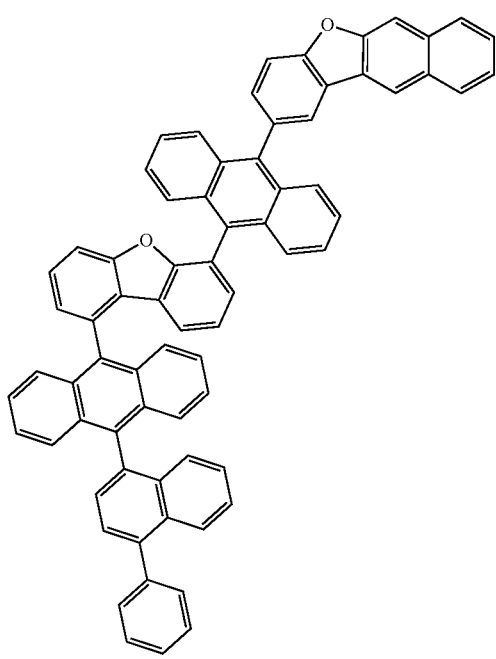
2031

2201
-continued
2202
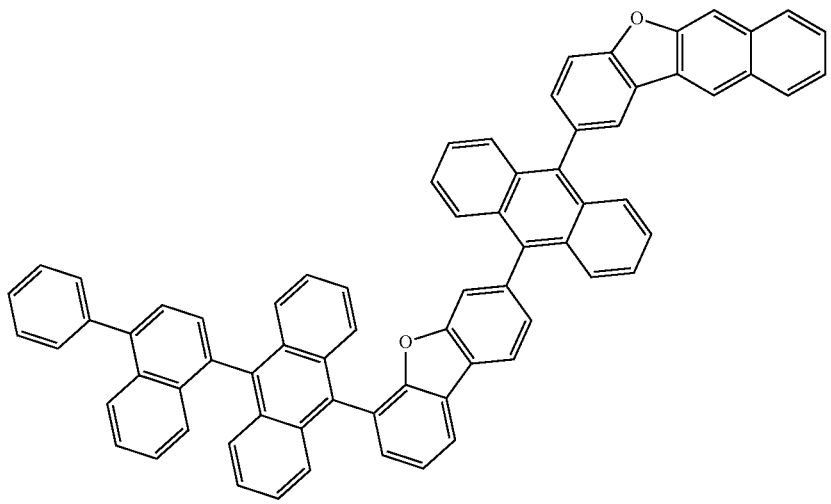
2032
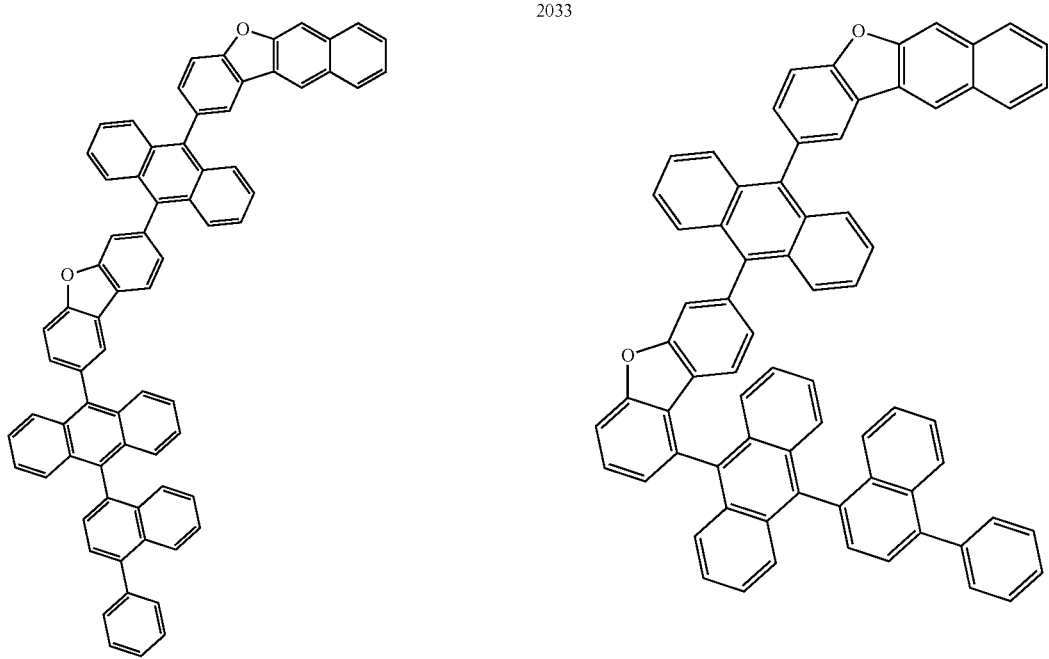
2033 2034

-continued
2035
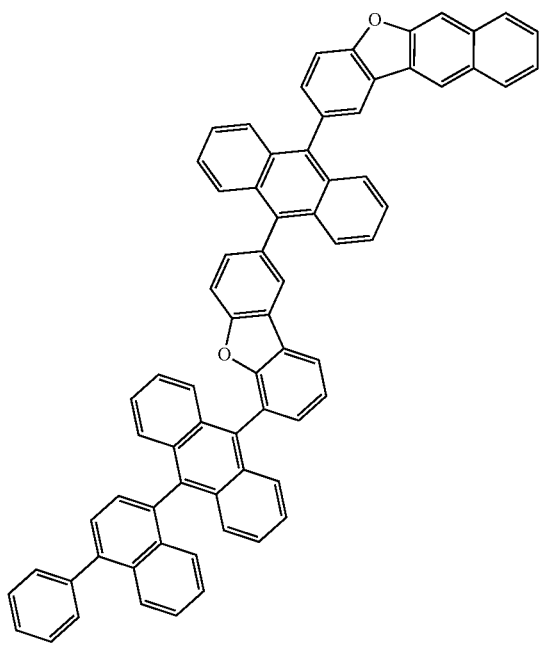
2036
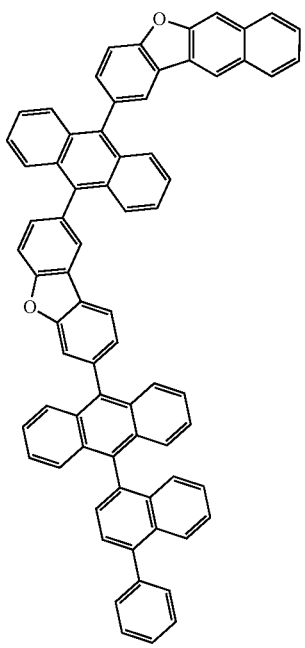
2037
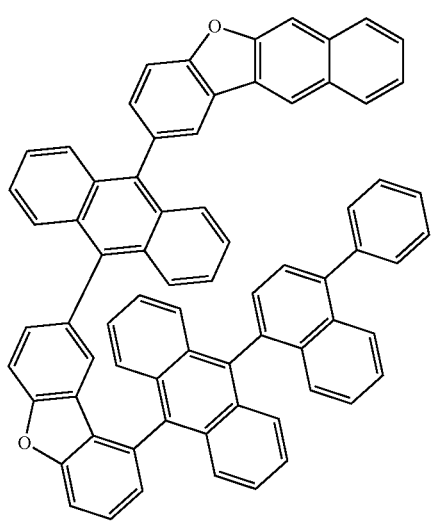
2038
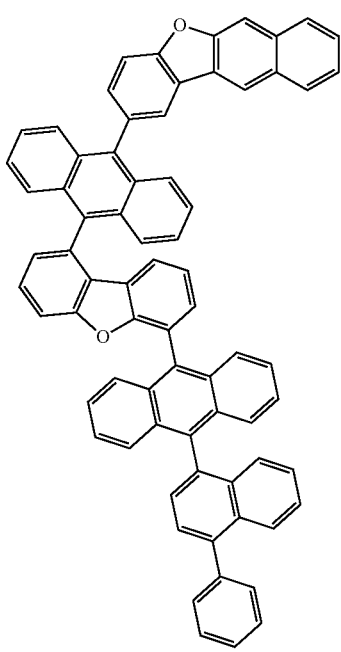

-continued
2039
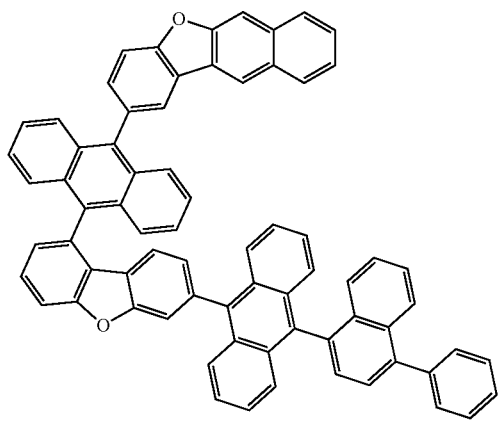
2040
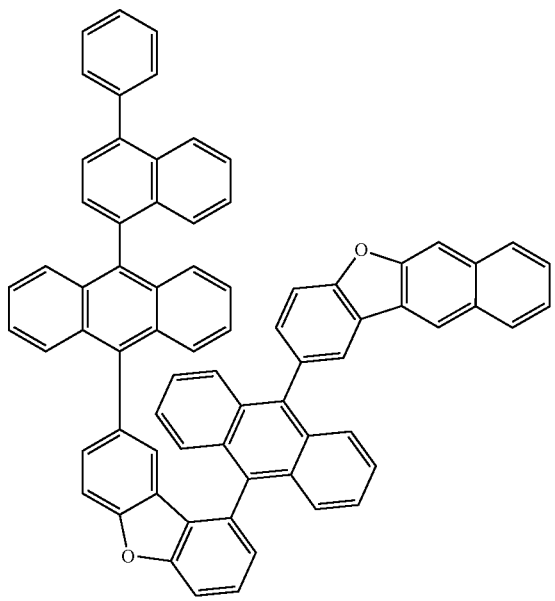
2041
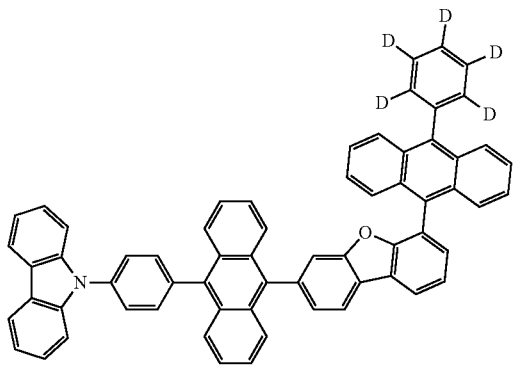
2042
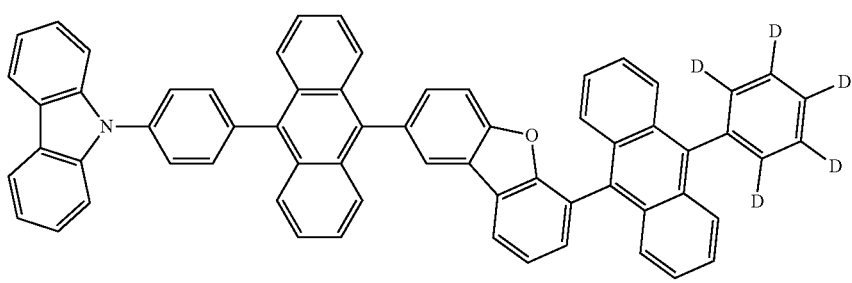

-continued
2043
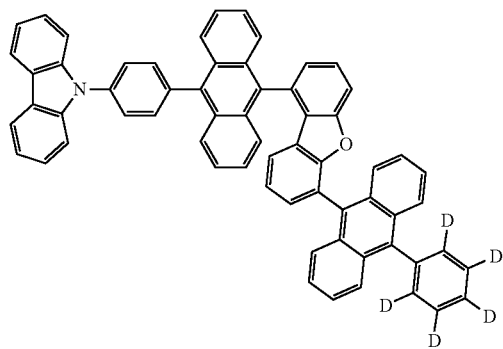
2044
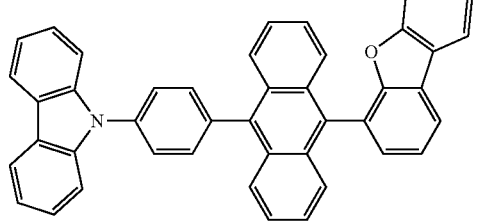
2045
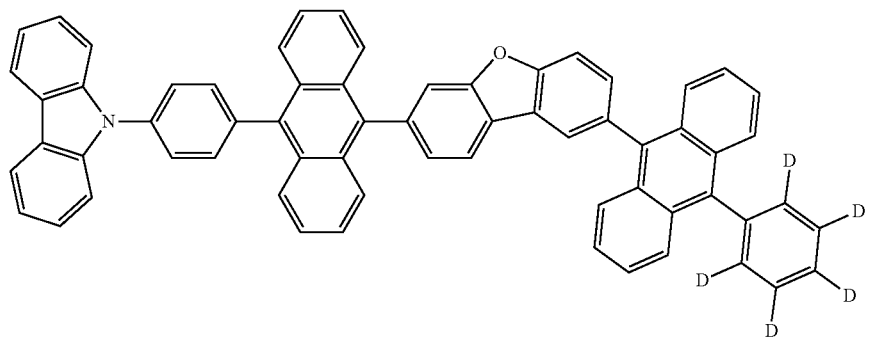
2046
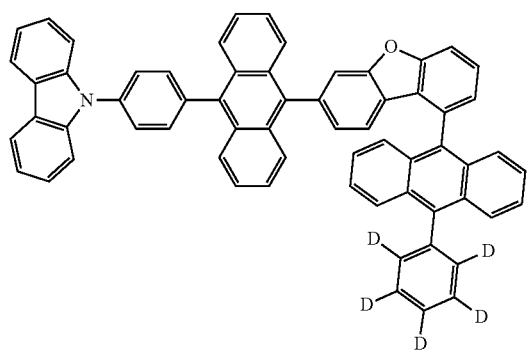

-continued
2047
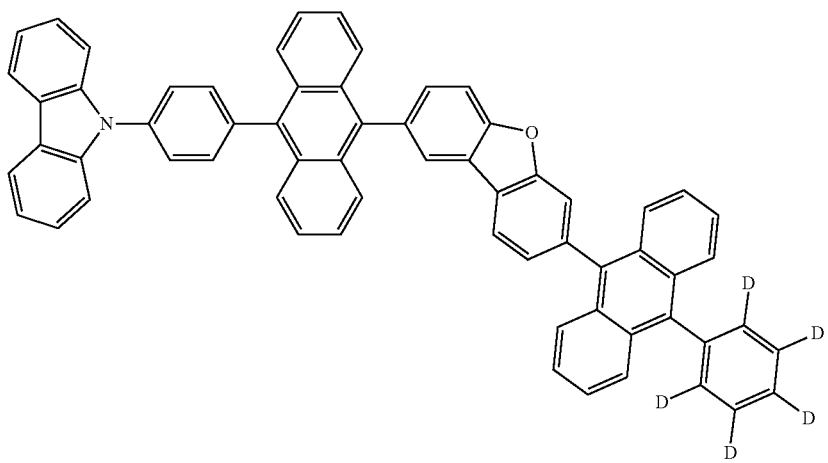
2048
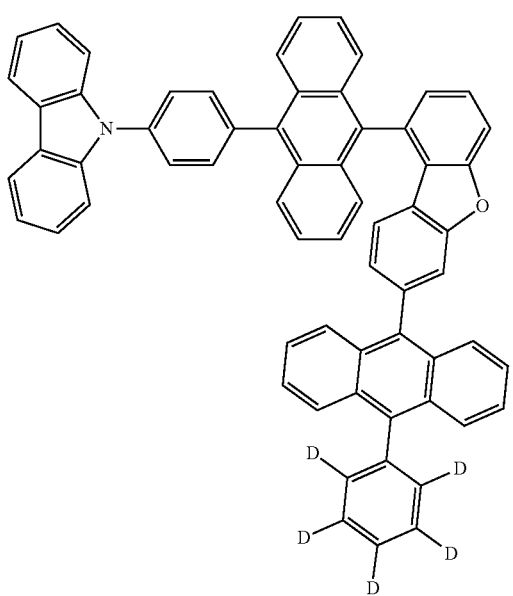
2049
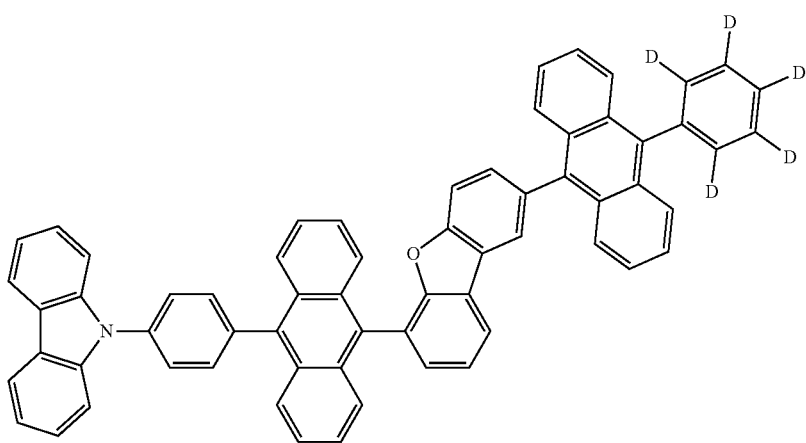

-continued
2050
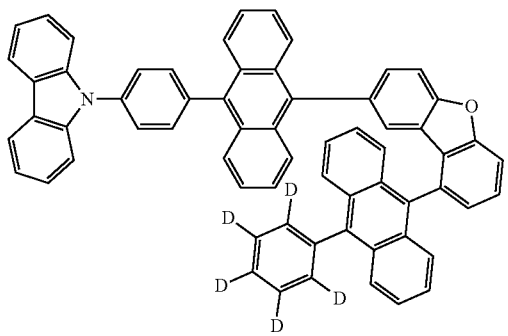
2051
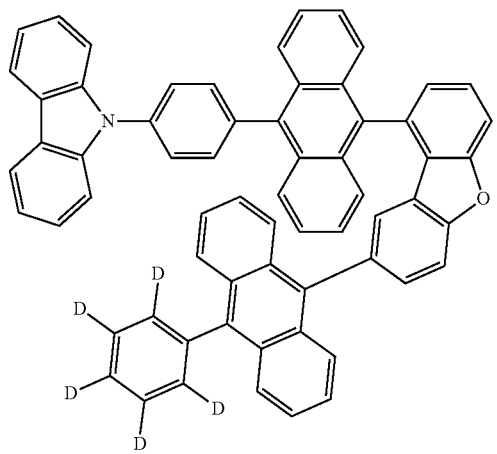
2052
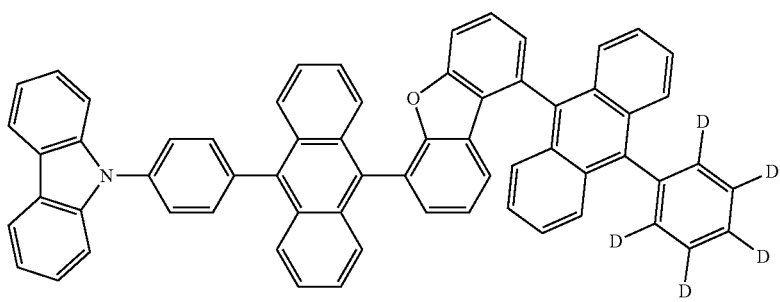
2053
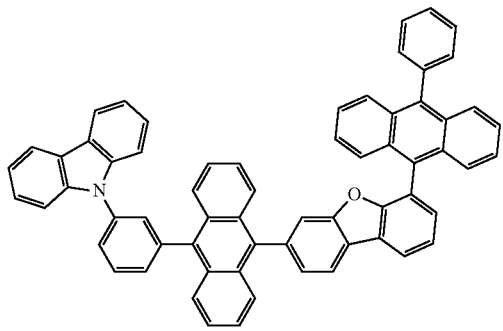
2054
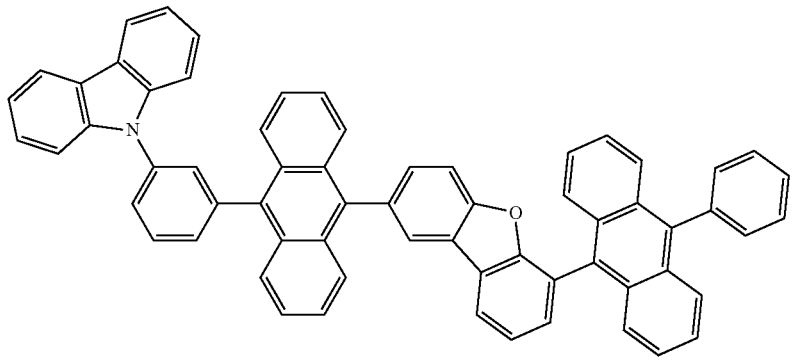

-continued
2055
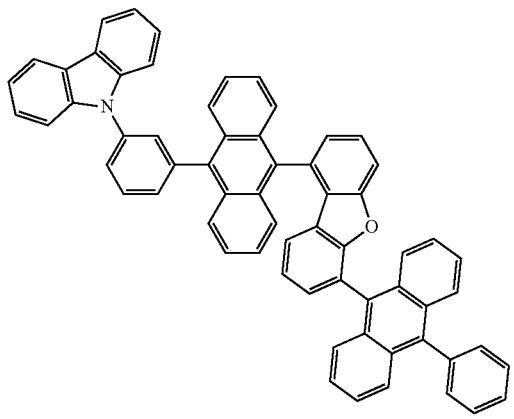
2056
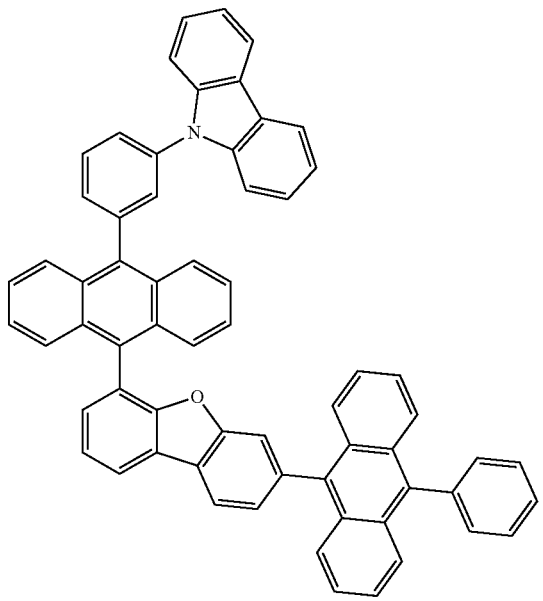
2057
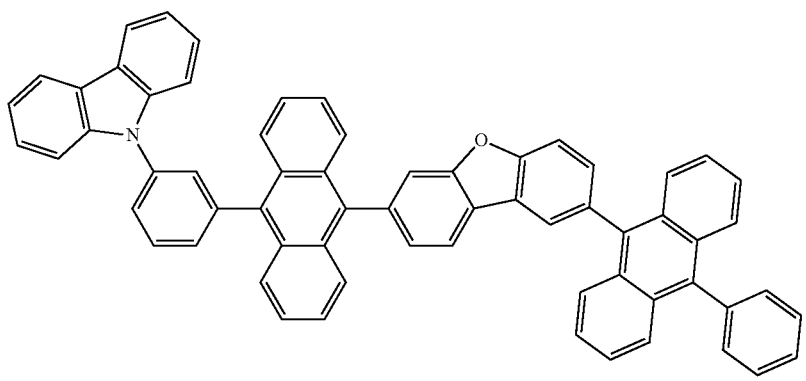
2058
2059
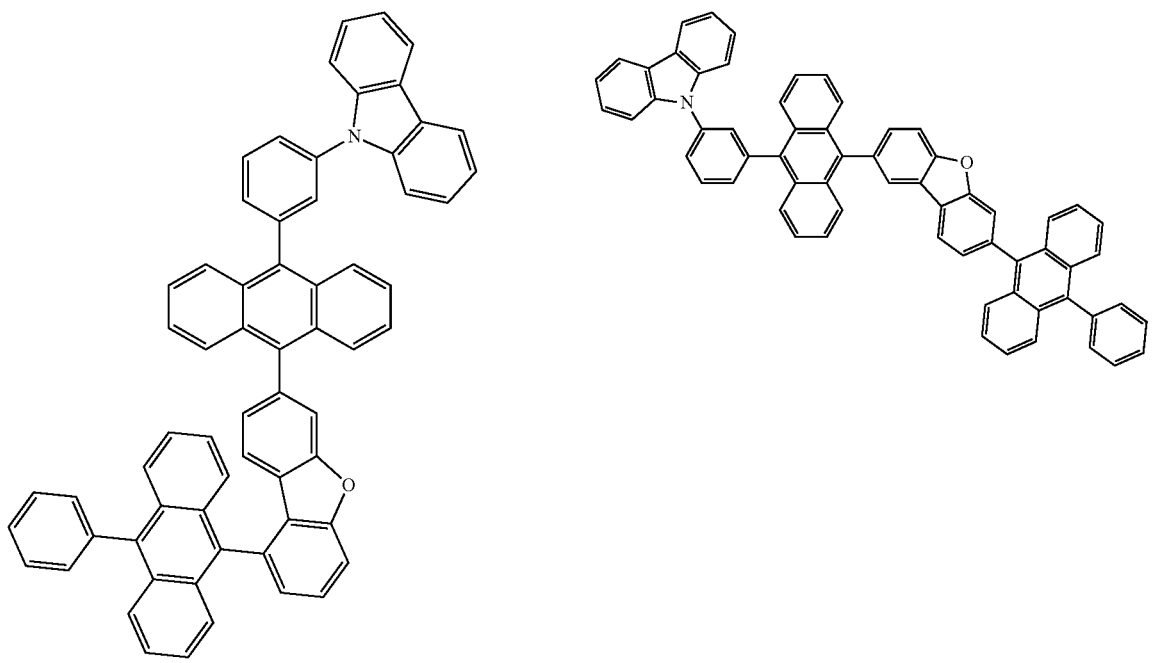

2060
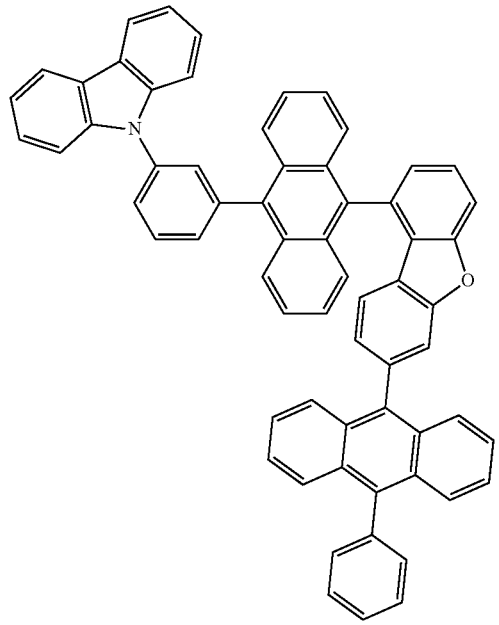
2061
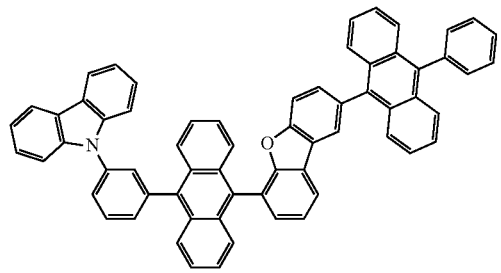
2062
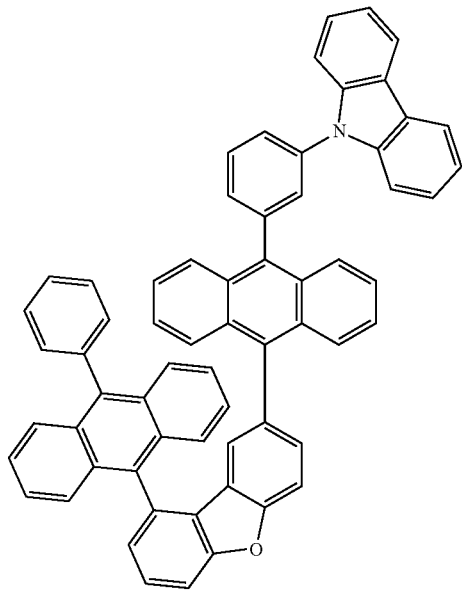

2063
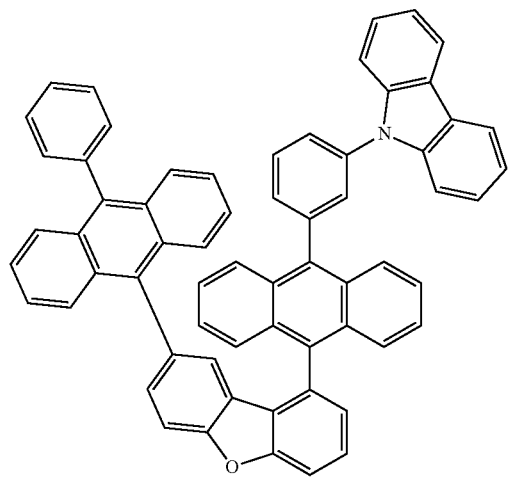
2064
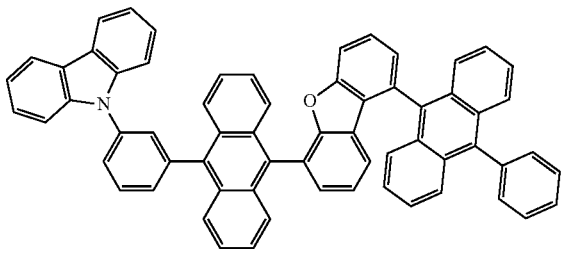
2065
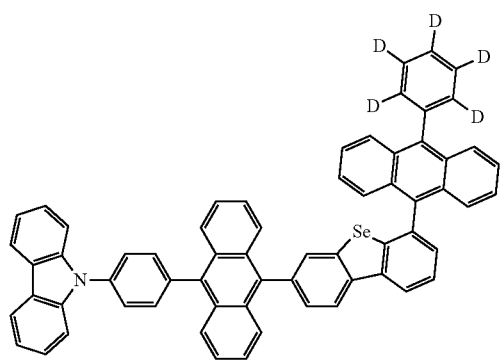
2066
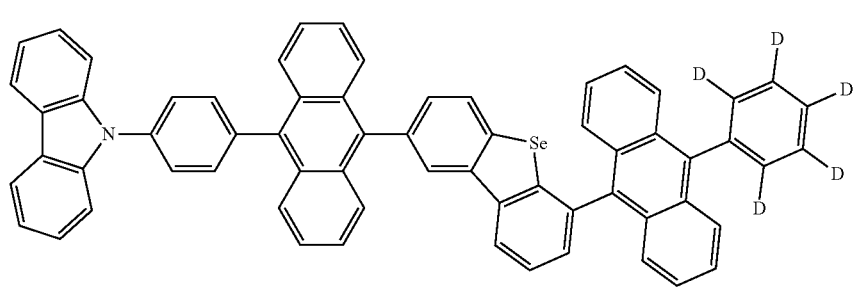

2067
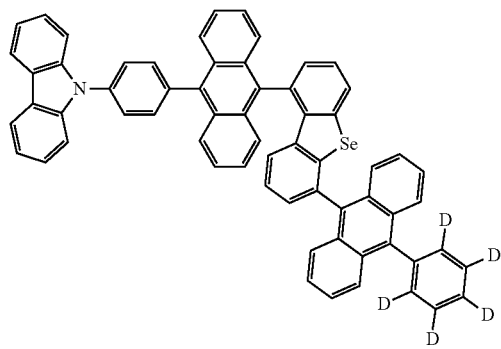
2068
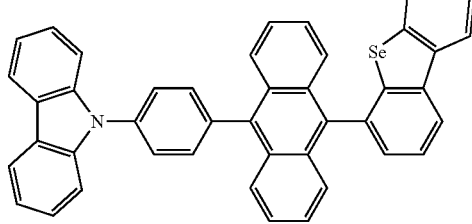
2069
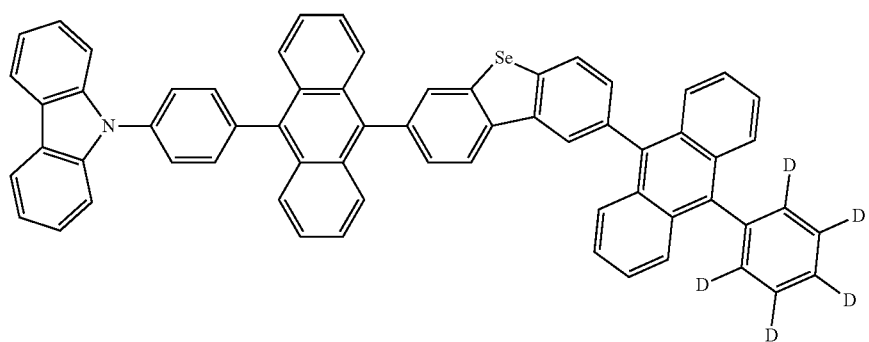
2070
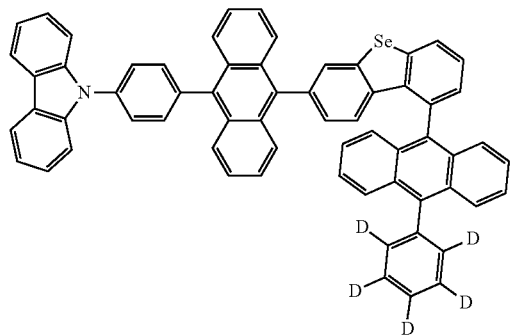

2071
2072
2073
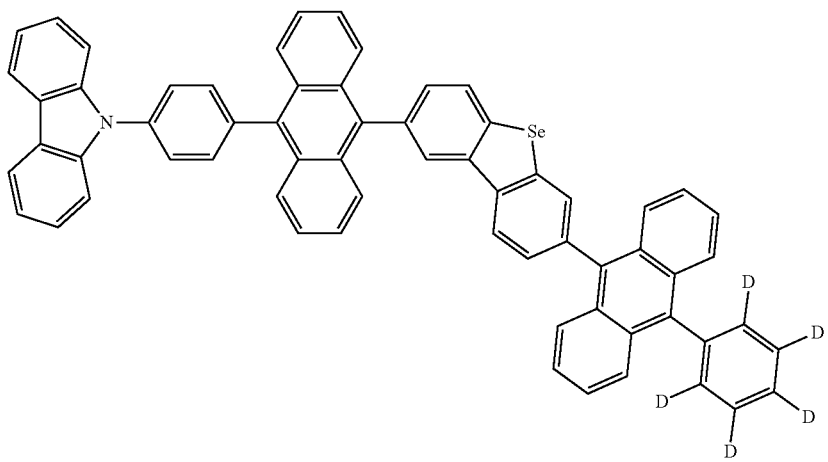

-continued
2223
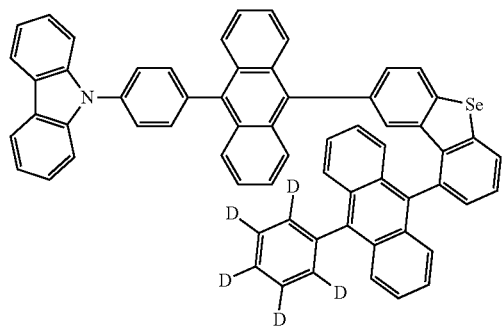
2074
2224
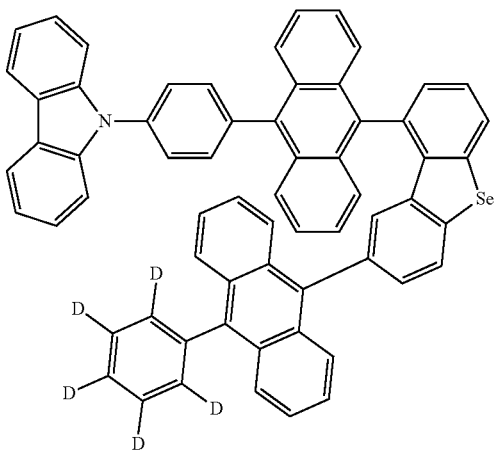
2075
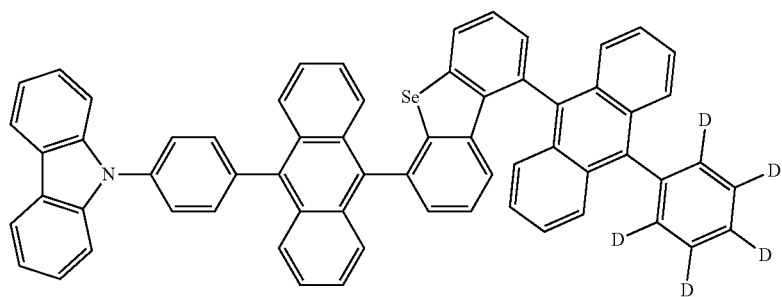
2076
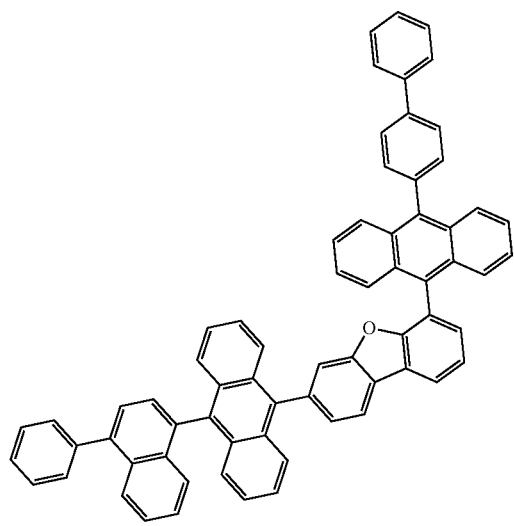
2077

-continued
2078
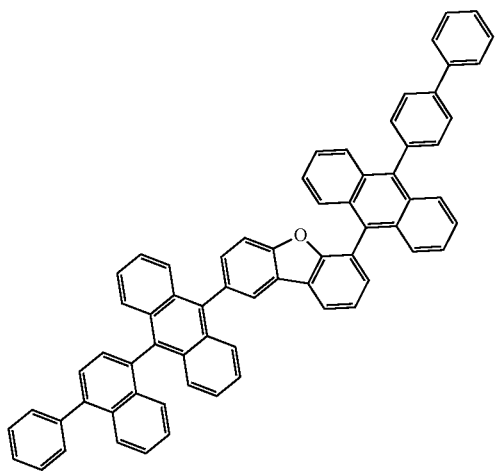
2079
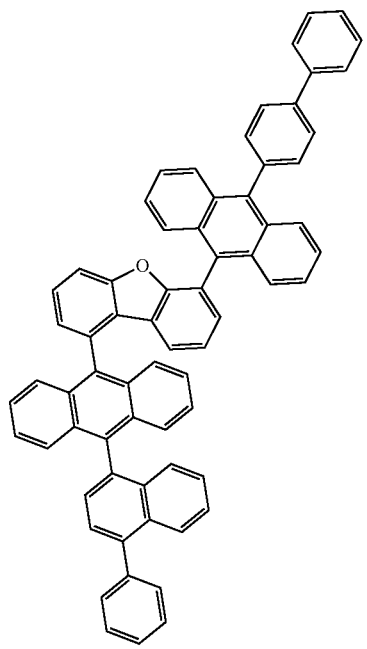
2080
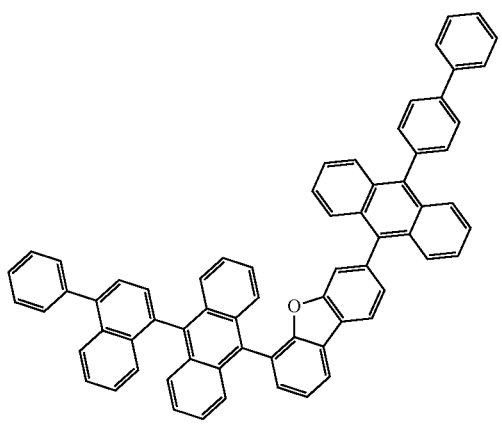
2081
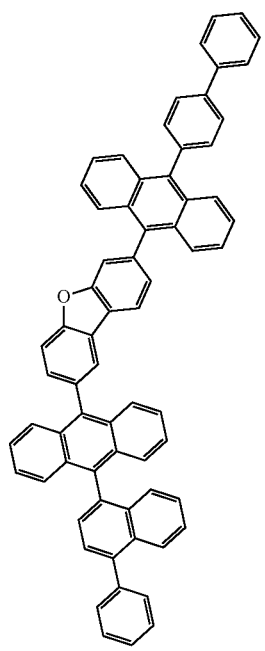

-continued
2082
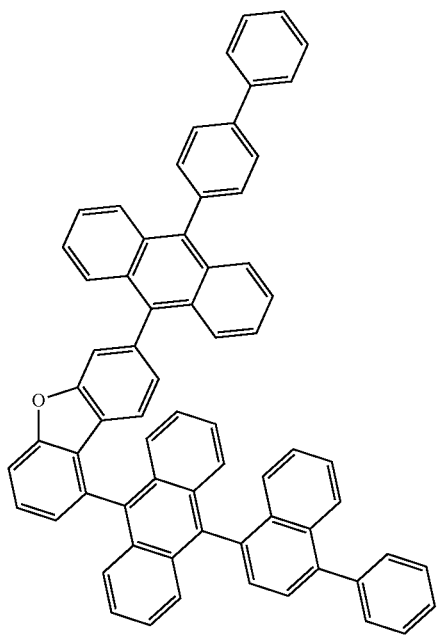
2083
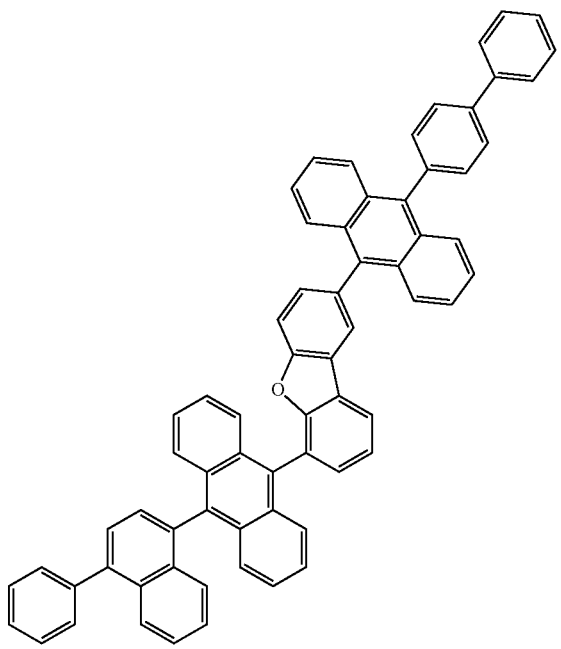
2084
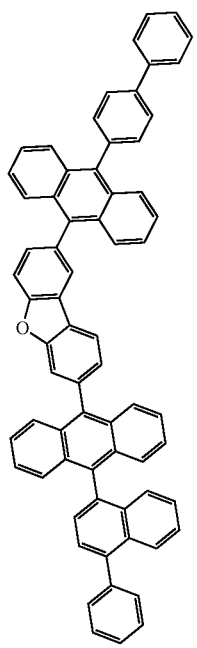
2085
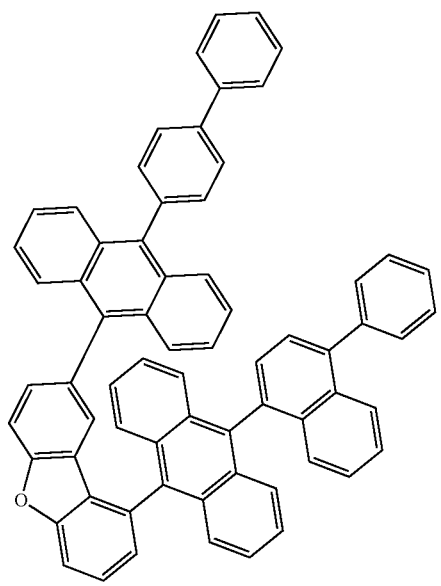

-continued
2086
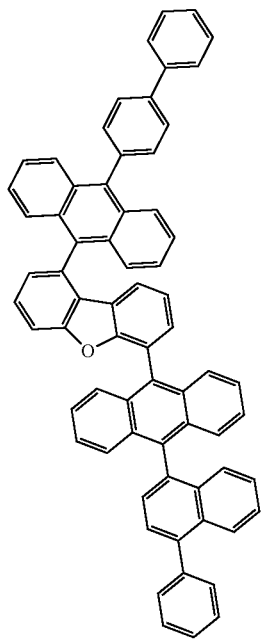
2087
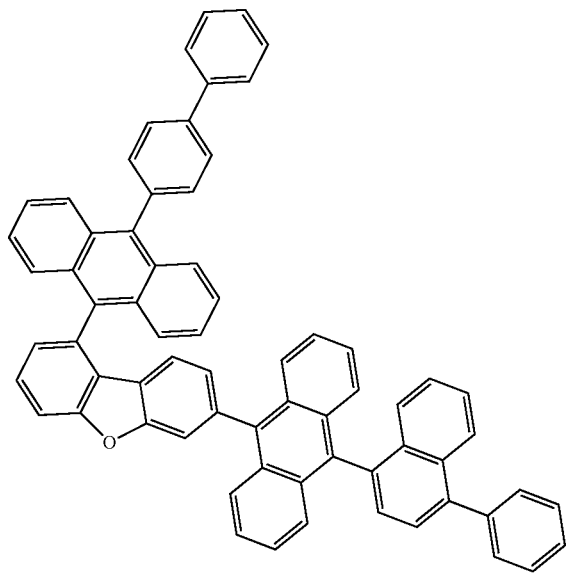
2088
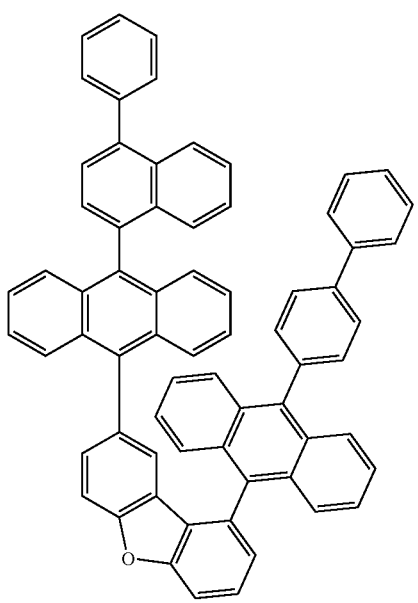
2089
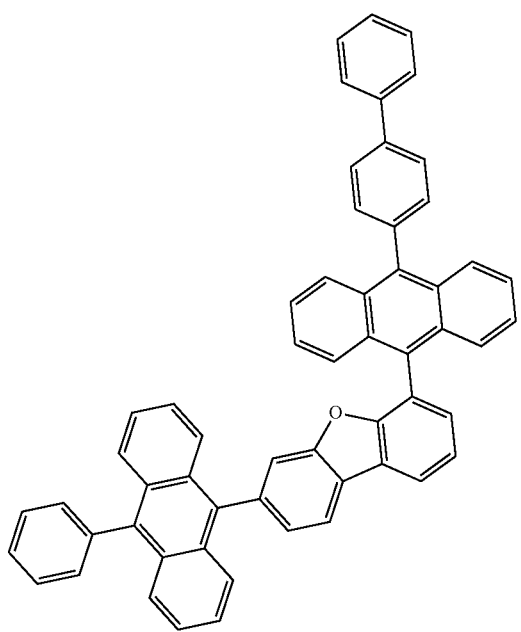

-continued
2090
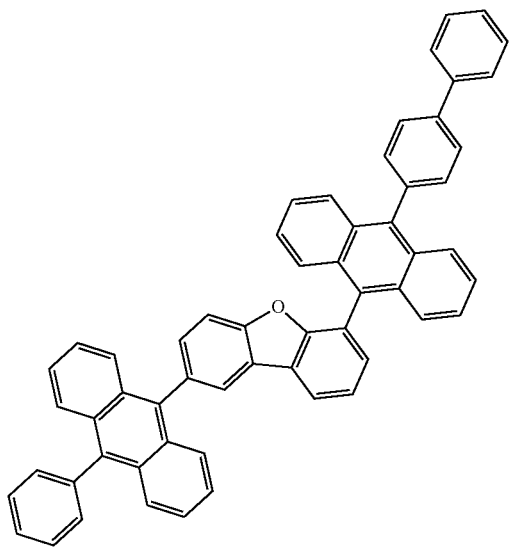
2091
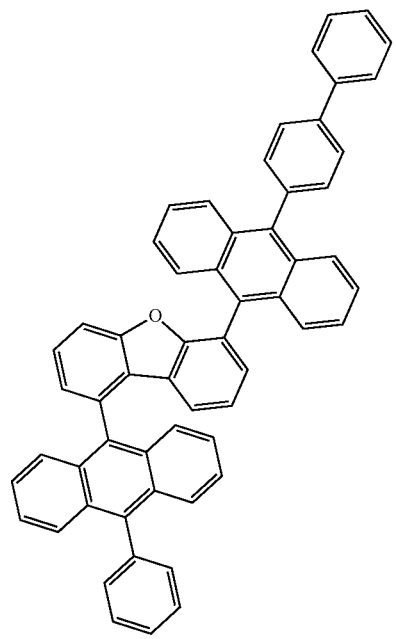
2092
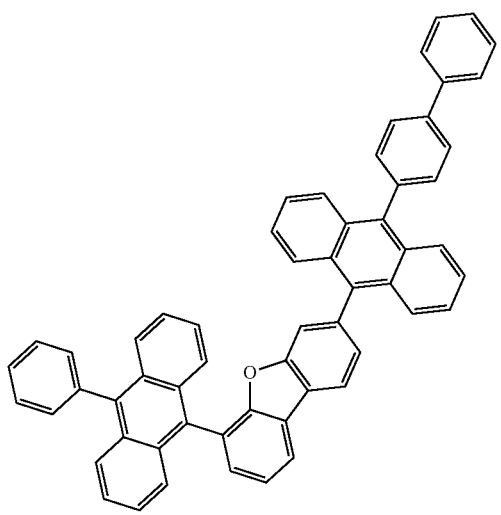
2093
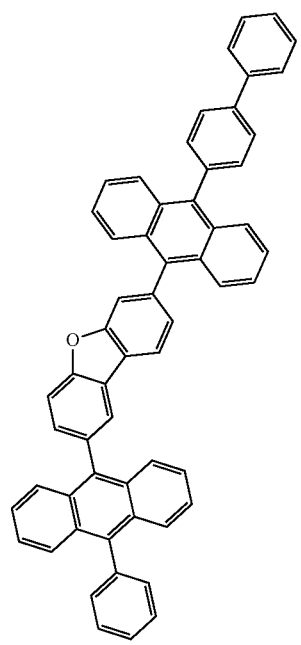

-continued
2094
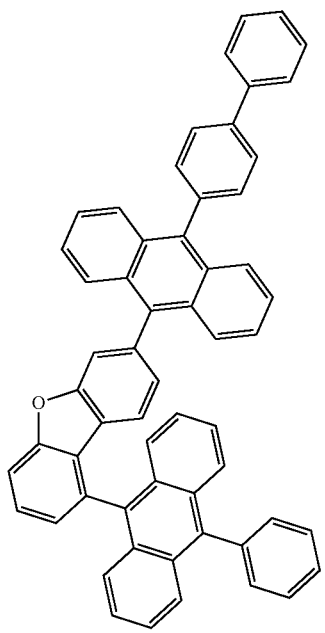
2233
2095
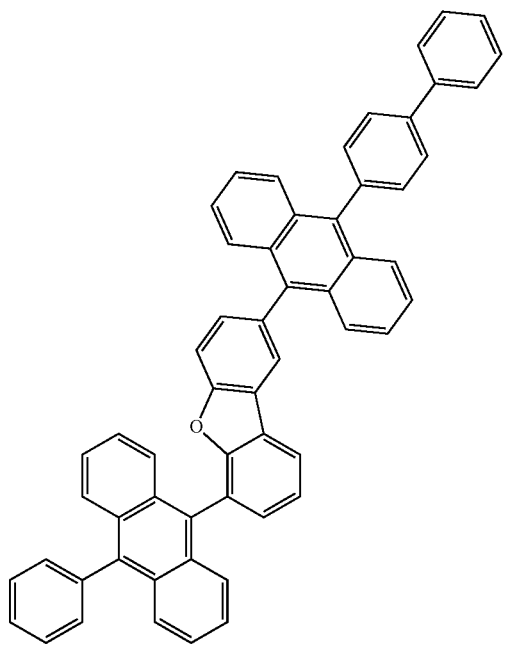
2234
2096
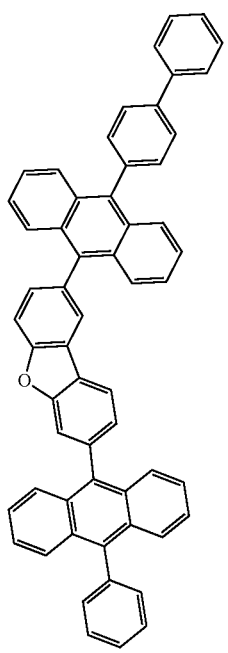
2097
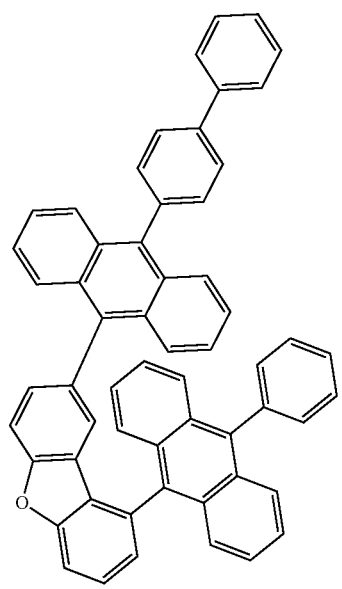

-continued
2235
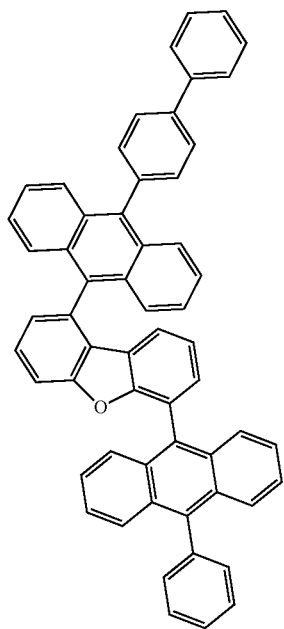
2098
2236
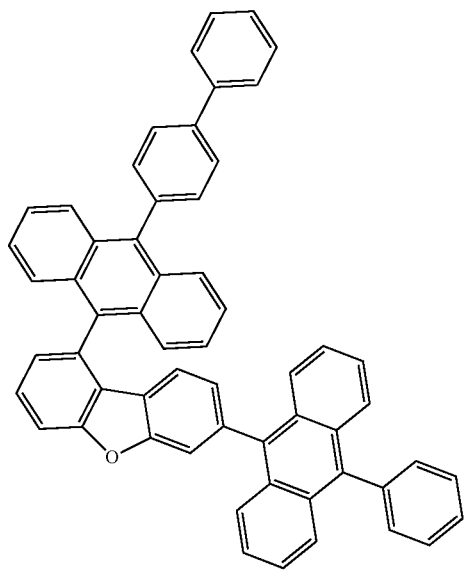
2099
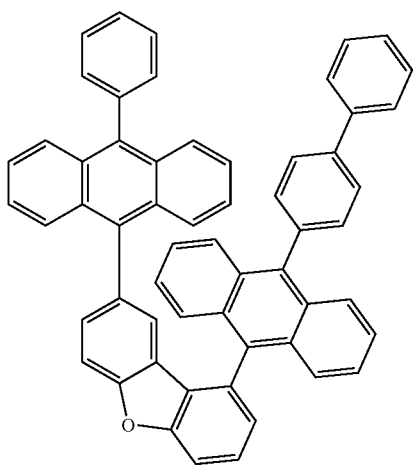
2100
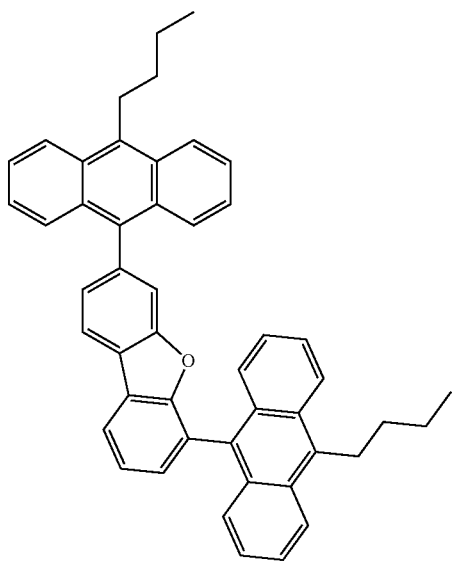
2101

2237
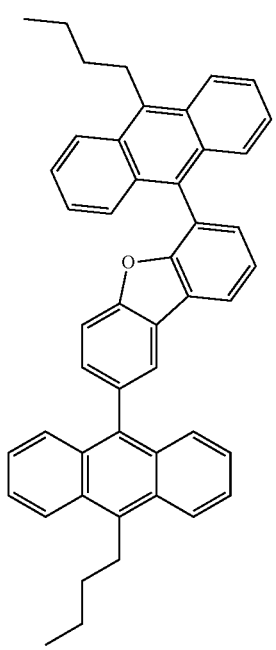
-continued
2102
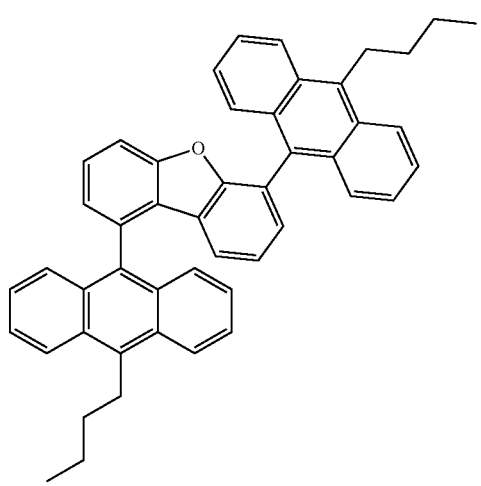
2103
2104
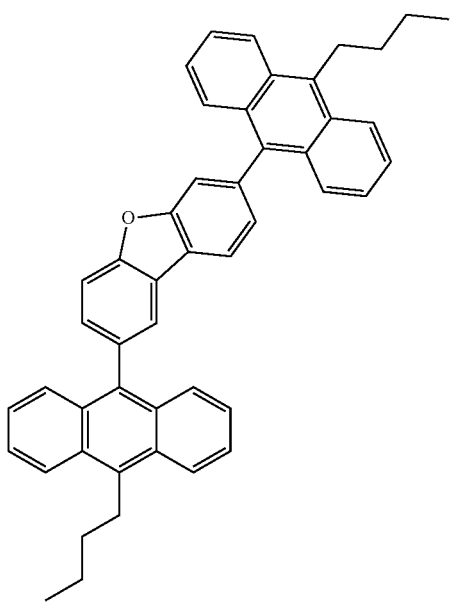
2105
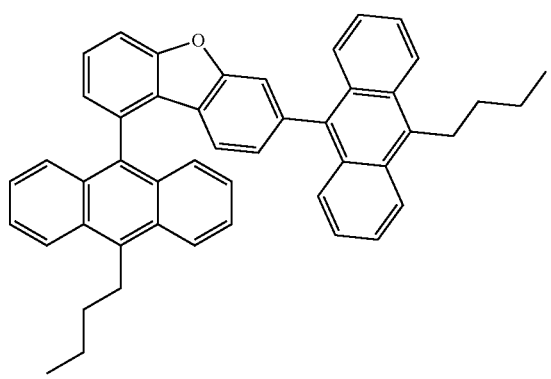
2238

-continued
2239
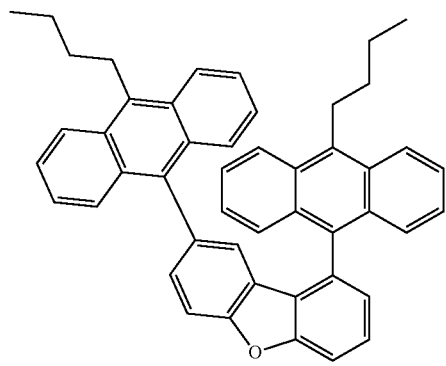
2106
2240
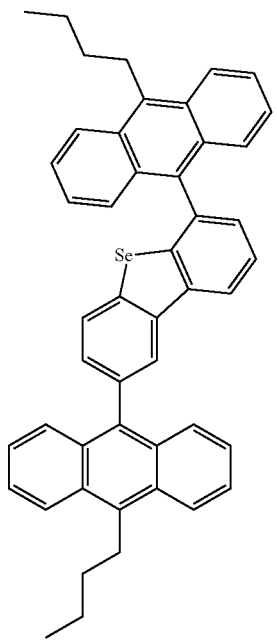
2107
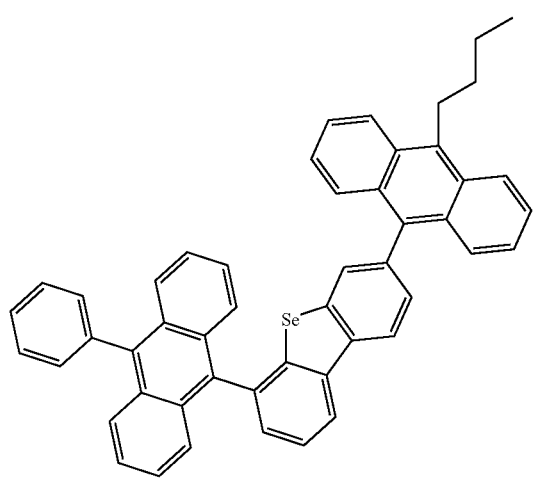
2108
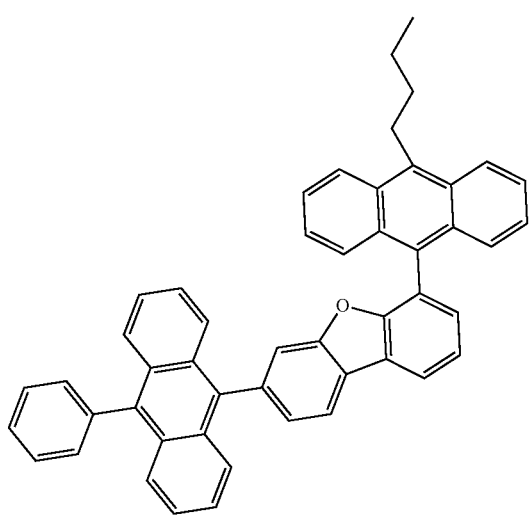
2109

-continued
2241
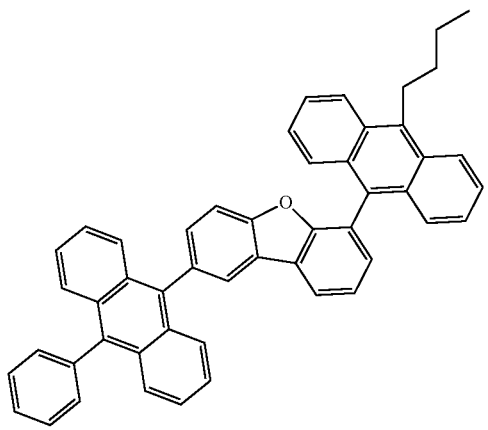
2242
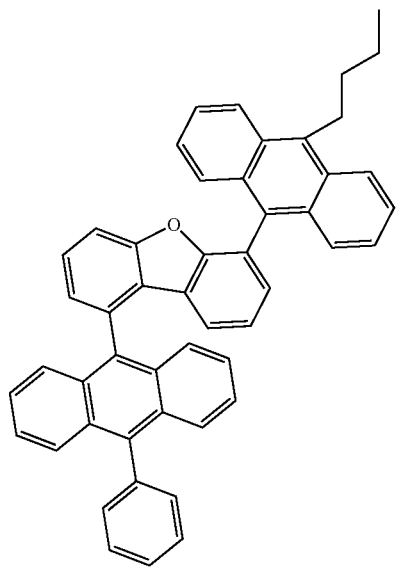
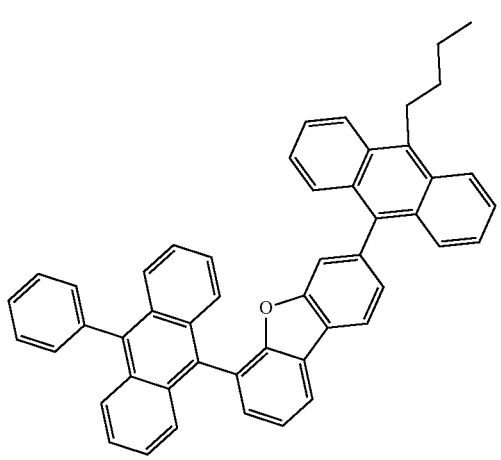
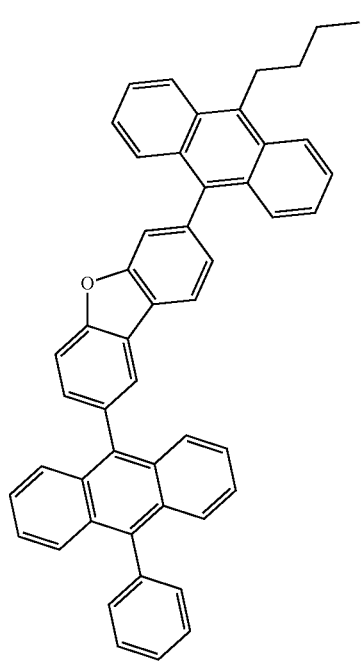

2243 2244
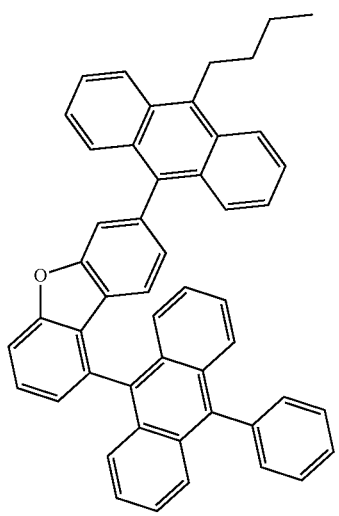
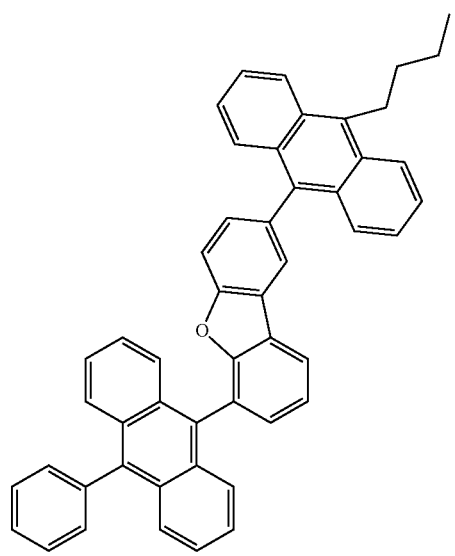
2114 2115
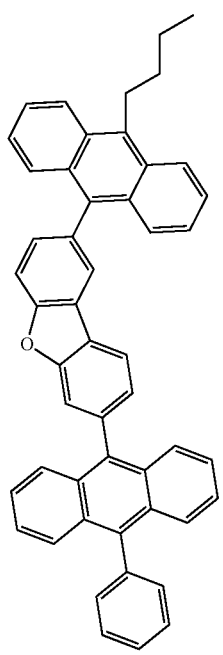
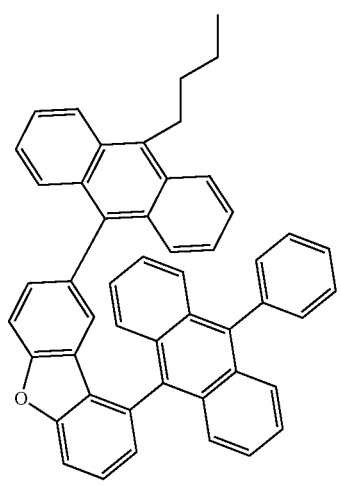
2116 2117

-continued

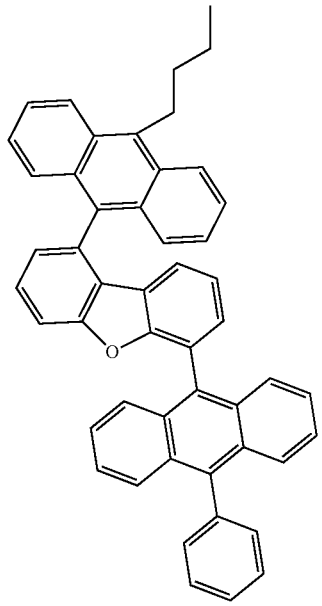
2118

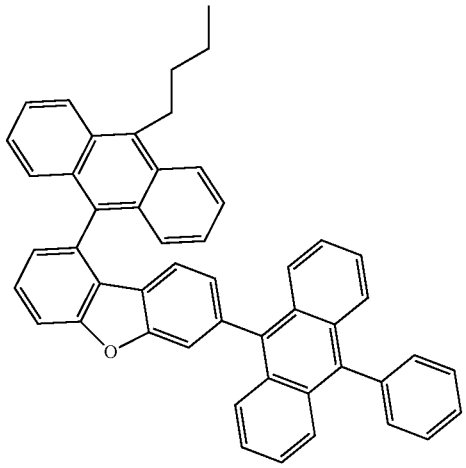
2119

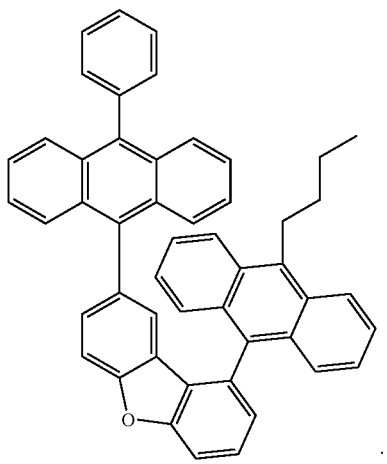
2120

When the host is a mixture of an electron transporting host and a hole transporting host, a weight ratio of the electron transporting host to the hole transporting host may be in a range of about 1:9 to about 9:1, for example, about 2:8 to about 8:2, for example, about 4:6 to about 6:4, or for example, about 5:5. When a weight ratio of the electron transporting host to the hole transporting host is within any of these ranges, holes and electrons transport balance into the emission layer 15 may be achieved.

Dopant in Emission Layer 15

The dopant may include the heterocyclic compound.

Sensitizer in Emission Layer 15

In some embodiments, the sensitizer may be a phosphorescence sensitizer including at least one metal a first-row transition metal, a second-row transition metal, a third-row transition metal, or any combination thereof.

In some embodiments, the sensitizer may include a metal ($M_{11}$) which may include at least one metal of a first-row transition metal, a second-row transition metal, a third-row transition metal, or any combination thereof, and an organic ligand ($L_{11}$), and $L_{11}$ and $M_{11}$ may form 1, 2, 3, or 4 cyclometallated ring.

In some embodiments, the sensitizer may include an organometallic compound represented by Formula 101:

$$M_{11}(L_{11})_{n11}(L_{12})_{n12} \qquad \text{Formula 101}$$

wherein, in Formula 101,
$M_{11}$ may be a first-row transition metal, a second-row transition metal, or a third-row transition metal,
$L_{11}$ may be a ligand represented by one of Formulae 1-1 to 1-4,
$L_{12}$ may be a monodentate ligand or a bidentate ligand,
n11 may be 1, and
n12 may be 0, 1, or 2:

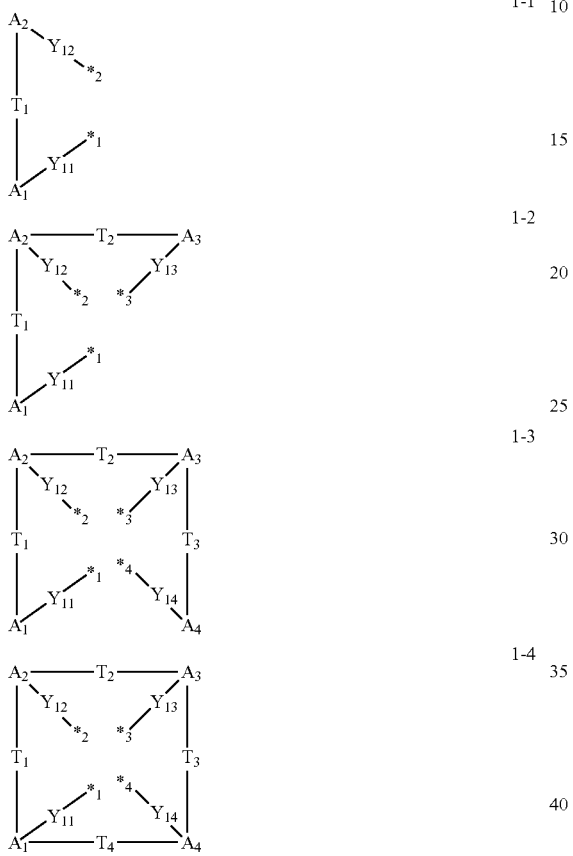

wherein, in Formulae 1-1 to 1-4,
$A_1$ to $A_4$ may each independently be a substituted or unsubstituted $C_5$-$C_{30}$ carbocyclic group, a substituted or unsubstituted $C_1$-$C_{30}$ heterocyclic group, or a non-cyclic group,
$Y_{11}$ to $Y_{14}$ may each independently be a chemical bond, O, S, $N(R_{91})$, $B(R_{91})$, $P(R_{91})$, or $C(R_{91})(R_{92})$,
$T_1$ to $T_4$ may each independently be a single bond, a double bond, *—$N(R_{93})$—*', *—$B(R_{93})$—*', *—$P(R_{93})$—*', *—$C(R_{93})(R_{94})$—*', *—$Si(R_{93})(R_{94})$—*', *—$Ge(R_{93})(R_{94})$—*', *—S—*', *—Se—*', *—O—*', *—C(=O)—*', *—S(=O)—*', *—S(=O)$_2$—*', *—$C(R_{93})$=*', *=$C(R_{93})$—*', *—$C(R_{93})$=$C(R_{94})$—*', *—C(=S)—*', or *—C≡C—*',
a substituent of the substituted $C_5$-$C_{30}$ carbocyclic group, a substituent of the substituted $C_1$-$C_{30}$ heterocyclic group, and $R_{91}$ to $R_{94}$ may each independently be hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent aromatic condensed polycyclic group, a substituted or unsubstituted monovalent aromatic condensed heteropolycyclic group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-Ge(Q_1)(Q_2)(Q_3)$, $-C(Q_1)(Q_2)(Q_3)$, $-B(Q_1)(Q_2)$, $-N(Q_1)(Q_2)$, $-P(Q_1)(Q_2)$, $-C(=O)(Q_1)$, $-S(=O)(Q_1)$, $-S(=O)_2(Q_1)$, $-P(=O)(Q_1)(Q_2)$, or $-P(=S)(Q_1)(Q_2)$, provided that the substituent of the substituted $C_5$-$C_{30}$ carbocyclic group and the substituent of the substituted $C_1$-$C_{30}$ heterocyclic group may not each be hydrogen, and
*1, *2, *3, and *4 each indicate a binding site to $M_{11}$,
wherein $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkyl aryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent aromatic condensed polycyclic group, a monovalent aromatic condensed heteropolycyclic group, a monovalent non-aromatic condensed polycyclic group, a monovalent non-aromatic condensed heteropolycyclic group, a $C_1$-$C_{60}$ alkyl group substituted with at least one deuterium, —F, a cyano group, a $C_1$-$C_{60}$ alkyl group, a $C_6$-$C_{60}$ aryl group, or any combination thereof, or a $C_6$-$C_{60}$ aryl group substituted with at least one deuterium, —F, a cyano group, a $C_1$-$C_{60}$ alkyl group, a $C_6$-$C_{60}$ aryl group, or any combination thereof.

In some embodiments, the sensitizer may be of Groups I to VIII, but embodiments are not limited thereto:

Group I

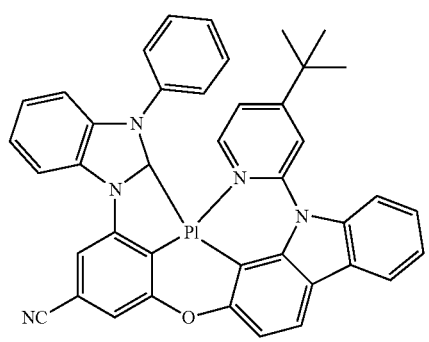

2249
-continued
2250
-continued
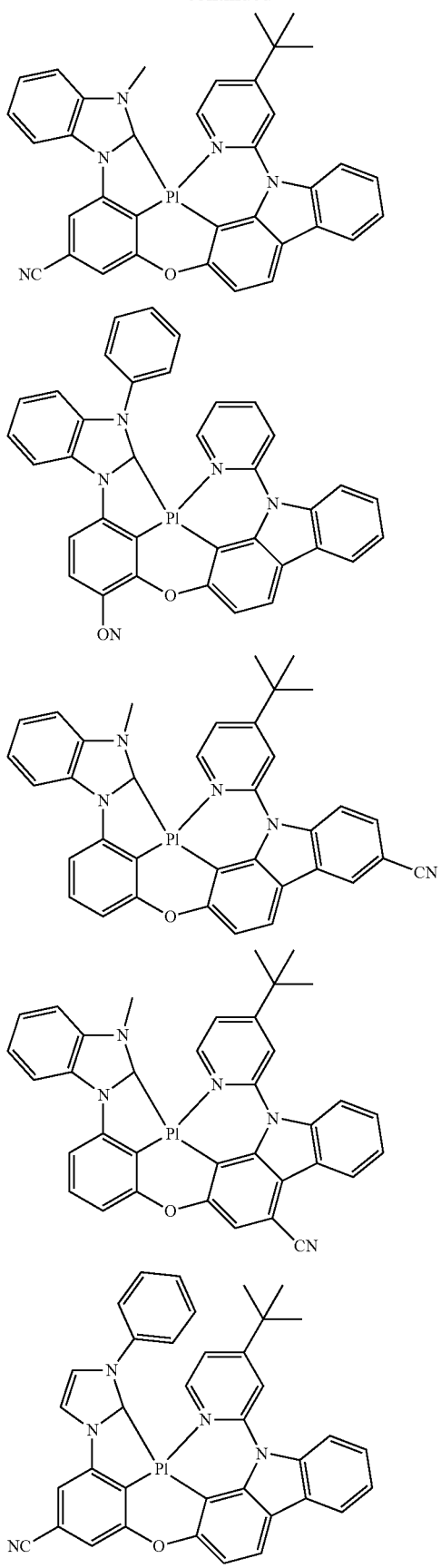
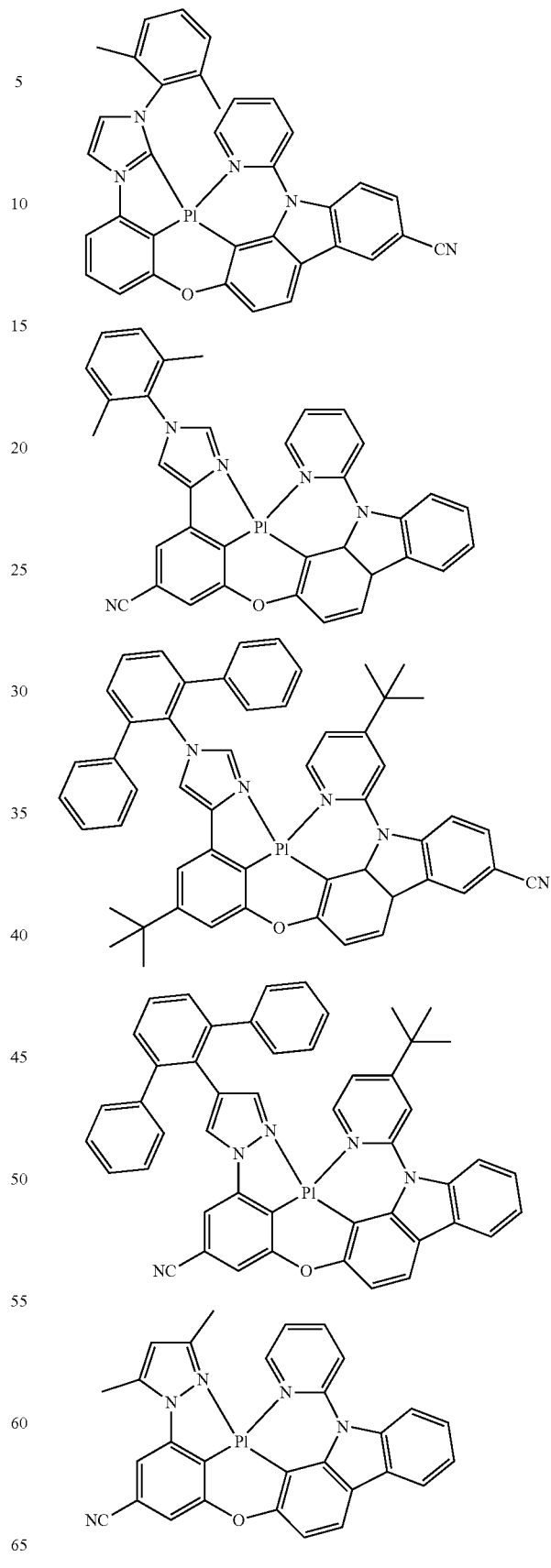

Group II
1
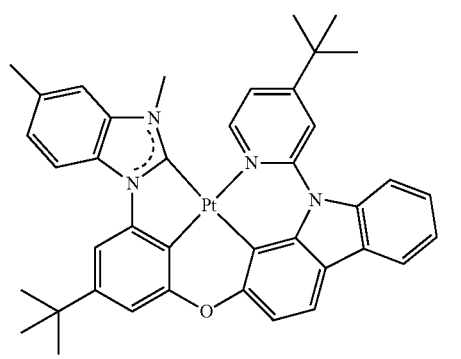
2
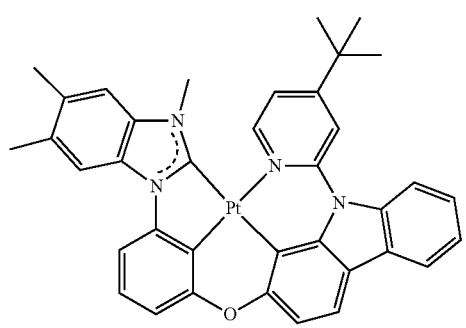
3
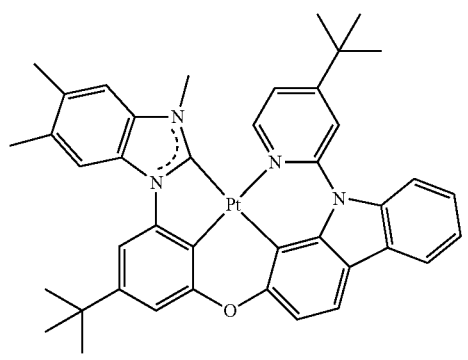
4
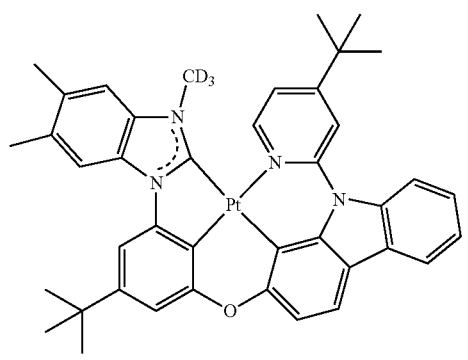
-continued
5
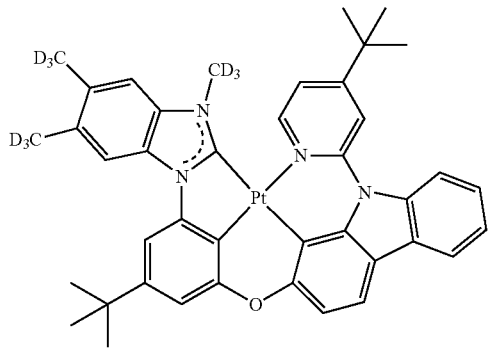
6
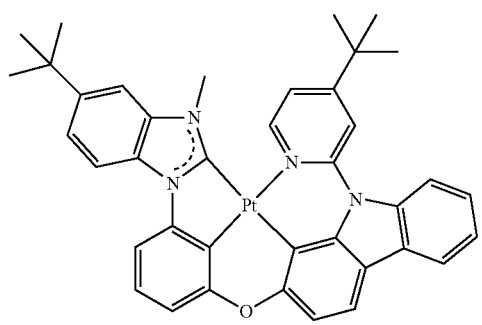
7
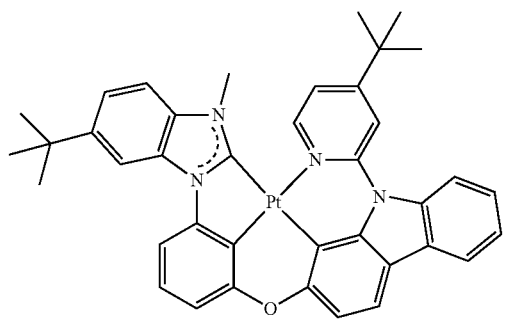
8
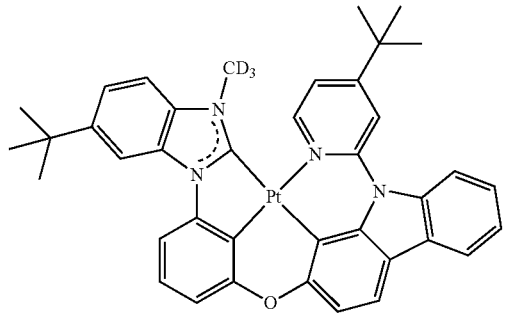

2253
-continued
9
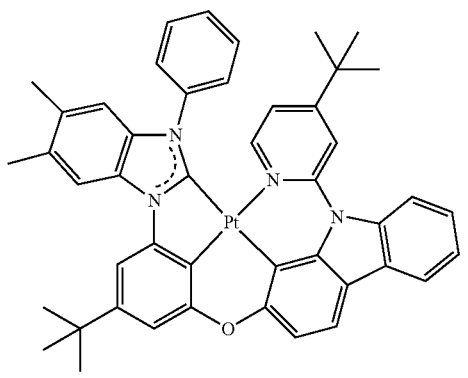
10
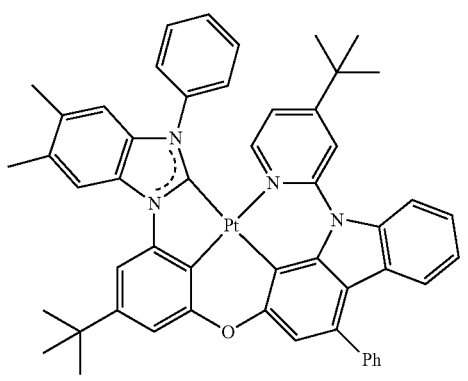
11
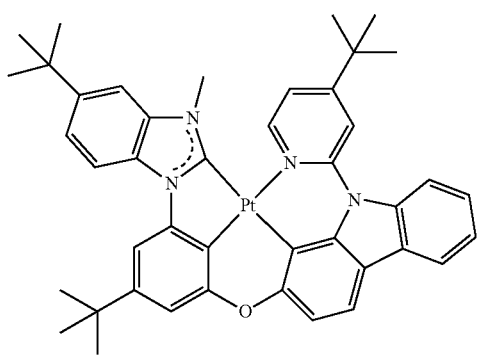
12
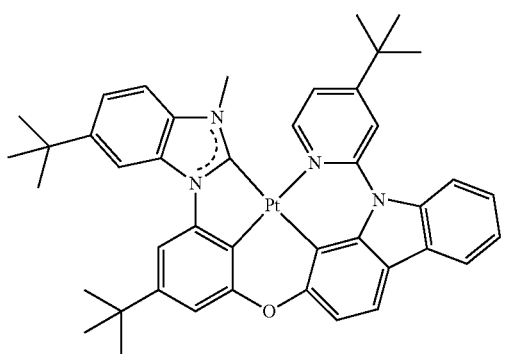
2254
-continued
13
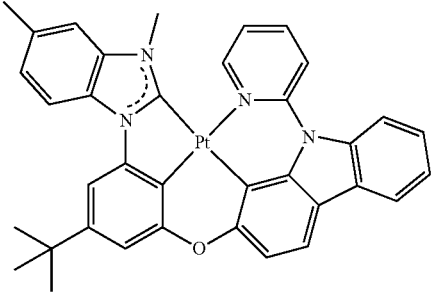
14
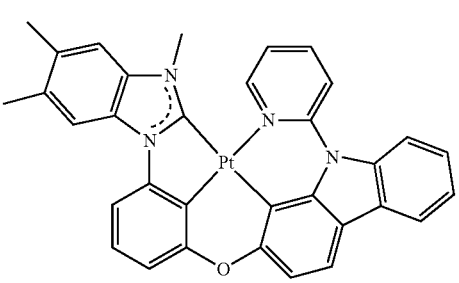
15
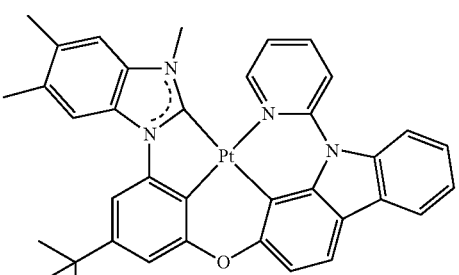
16
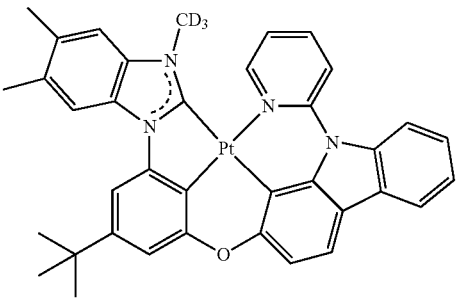
17
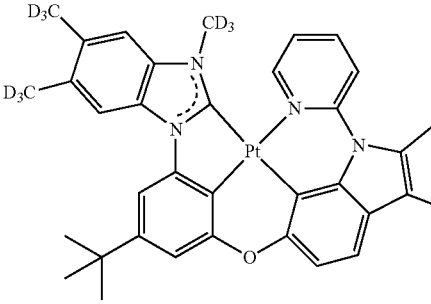

2255
-continued
18
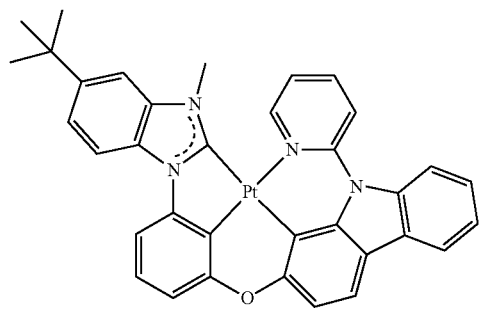
19
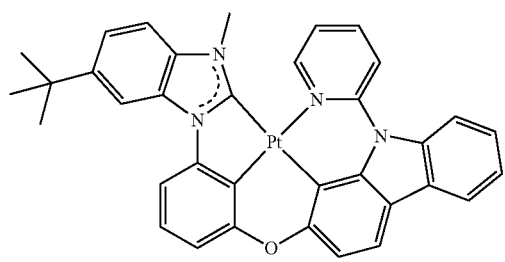
20
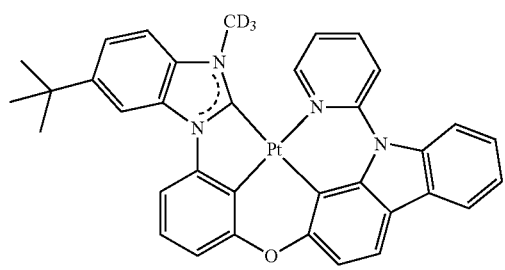
21
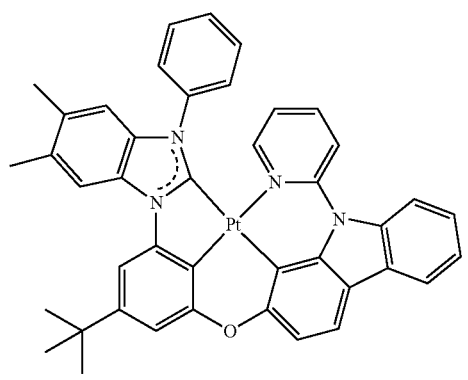
22

2256
-continued
23
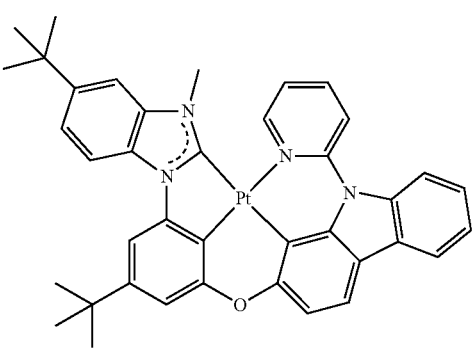
24
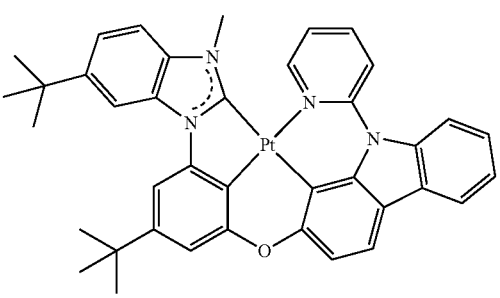
25
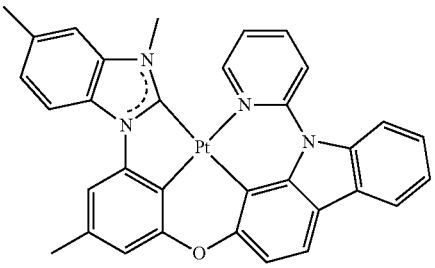
26
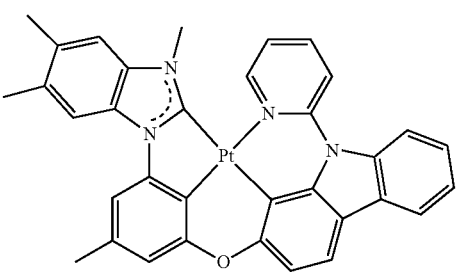
27
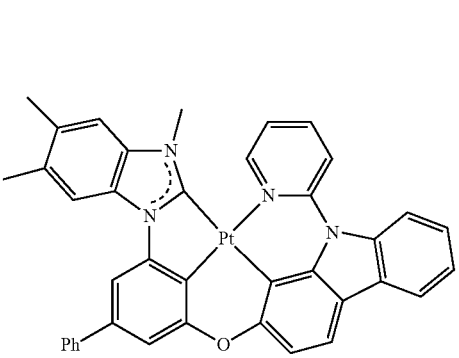

28
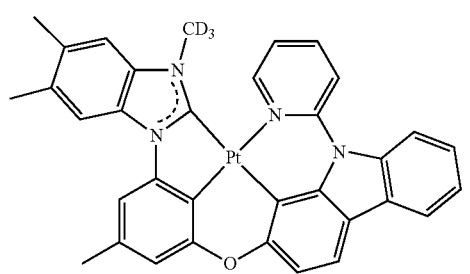
29
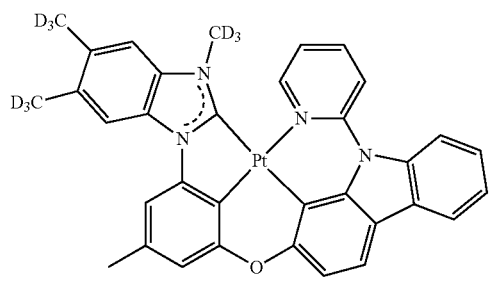
30
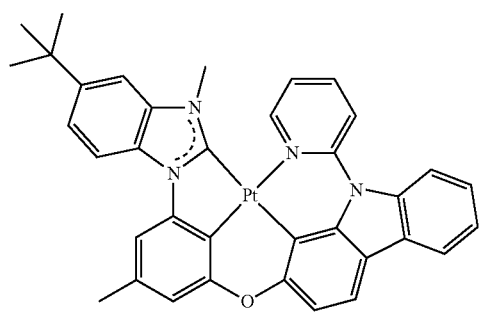
31
32
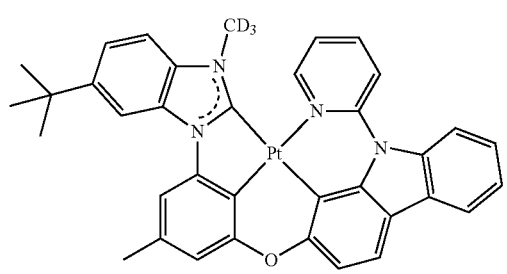
33
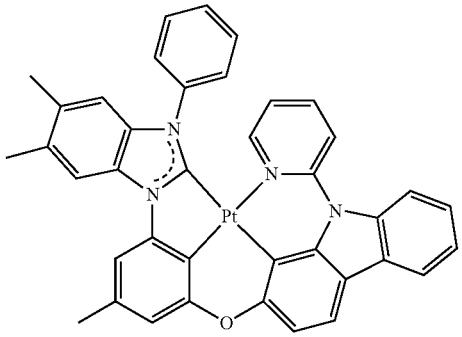
34
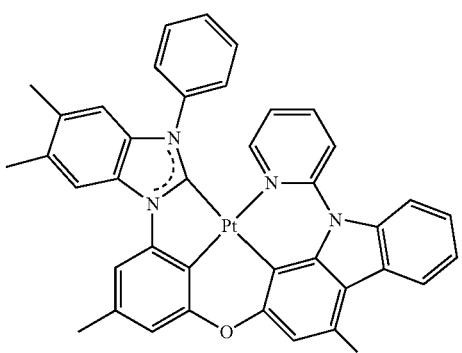
35
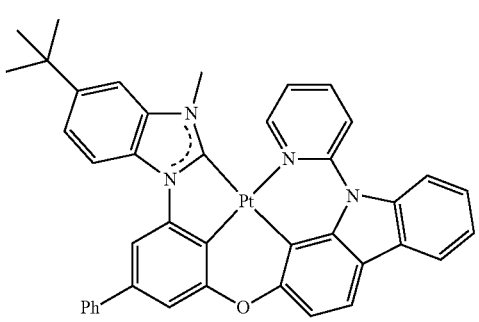
36
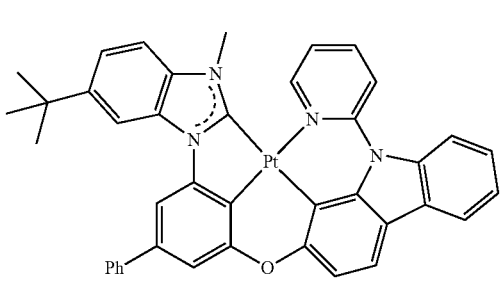

2259
-continued
37
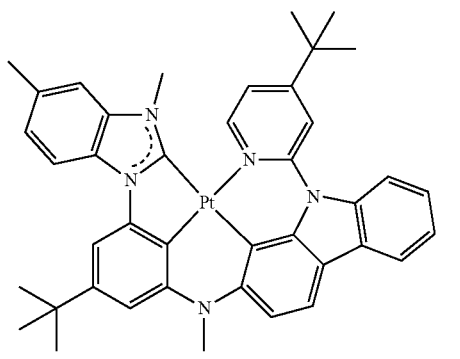
38
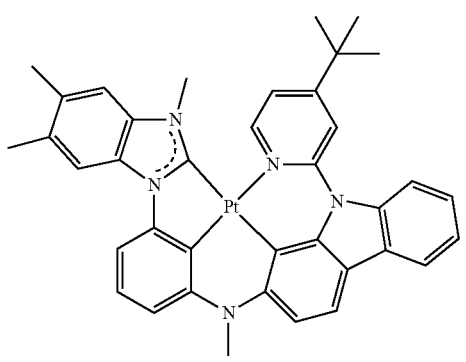
39
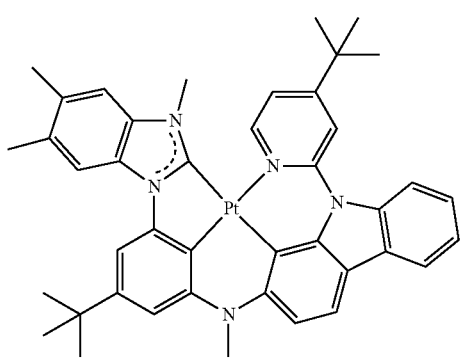
40
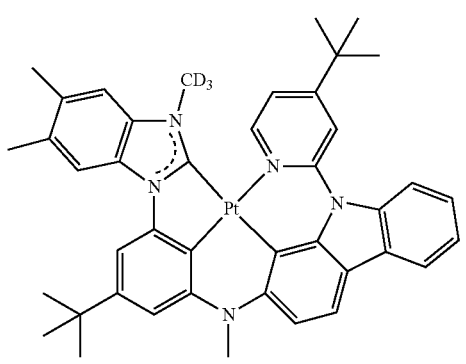
2260
-continued
41
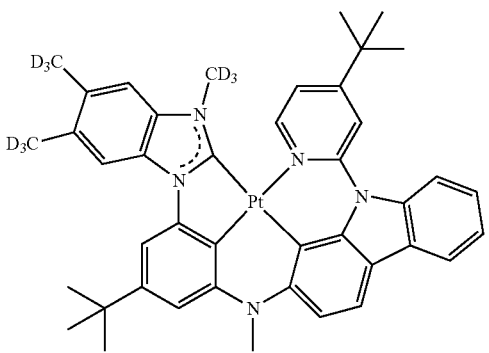
42
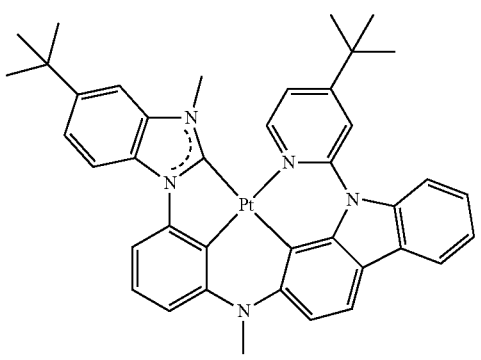
43
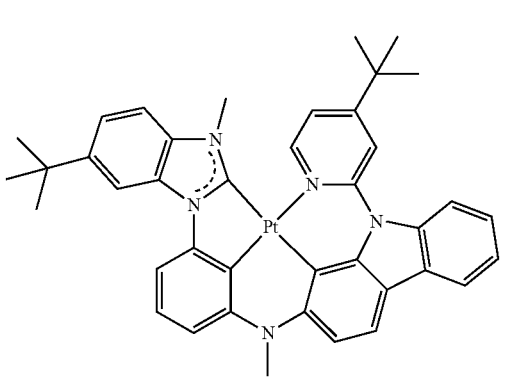
44
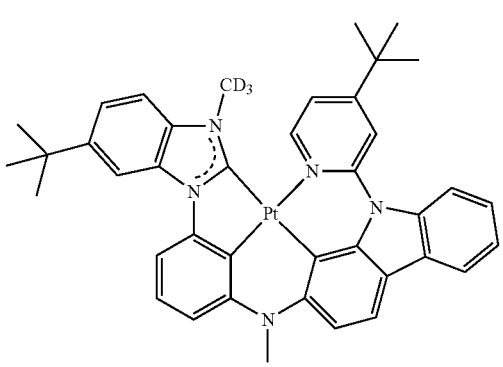

2261
-continued
45
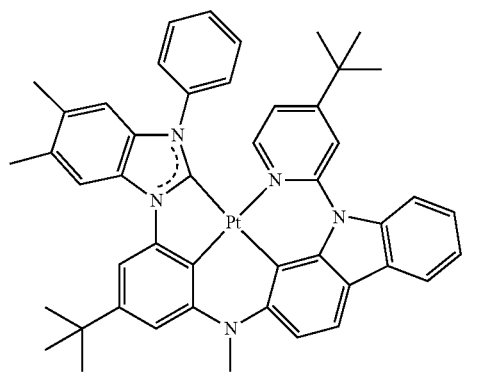
46
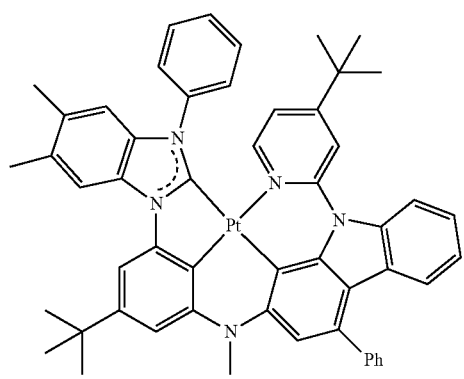
47
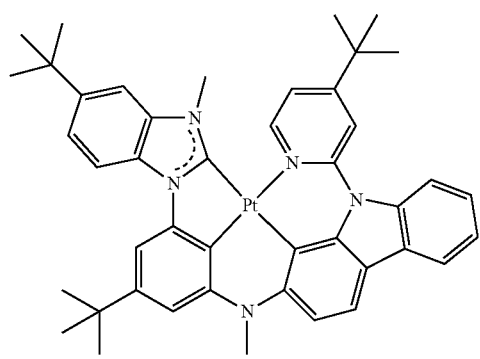
48
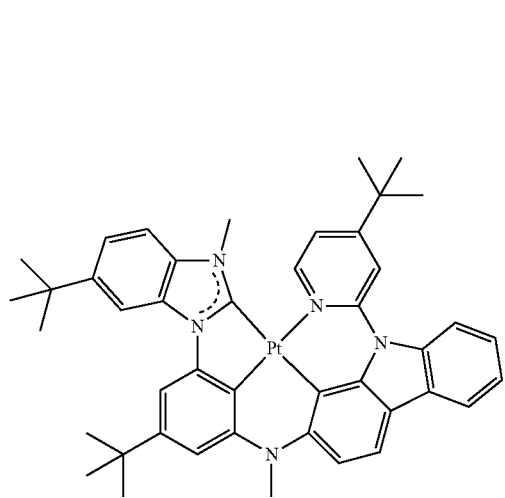
2262
-continued
49
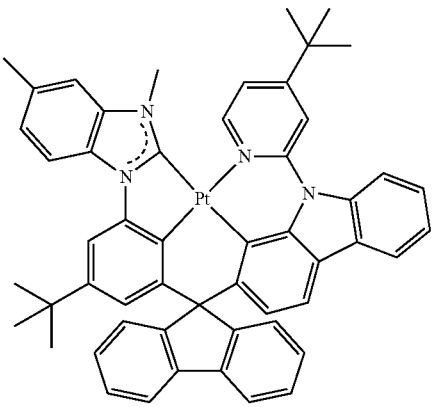
50
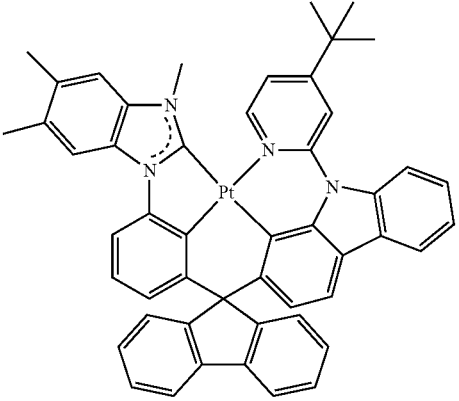
51
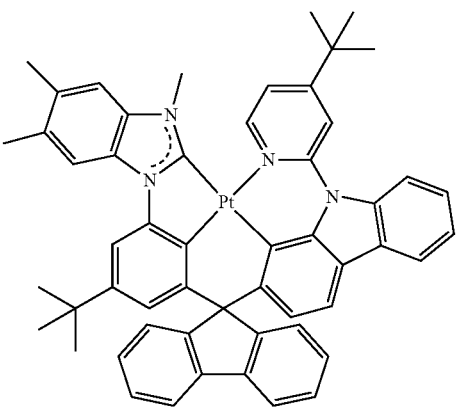
52
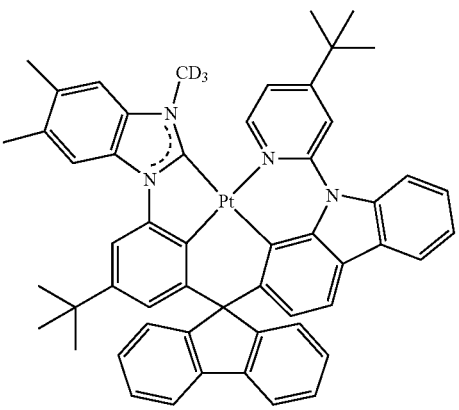

2263
-continued
53
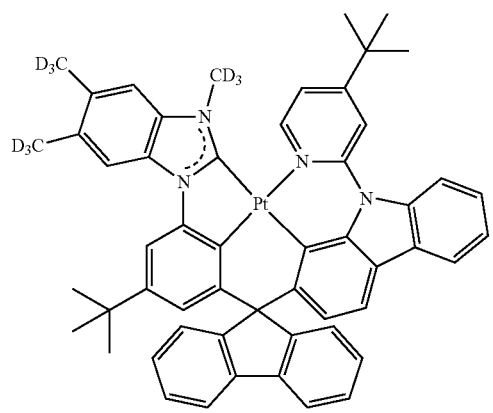
54
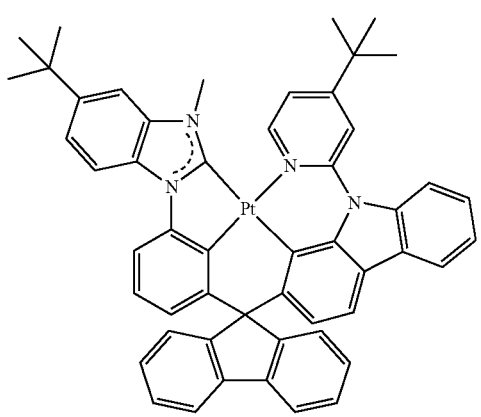
55
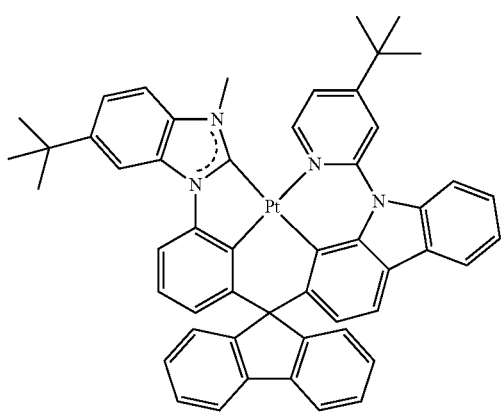
2264
-continued
56
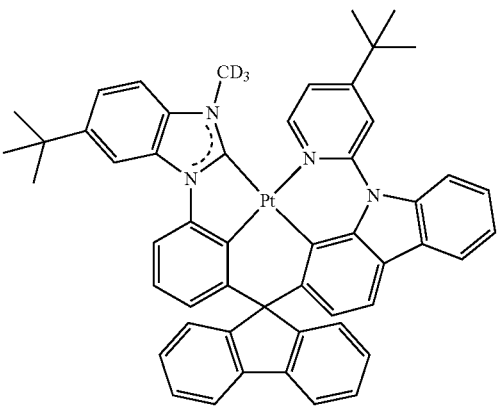
57
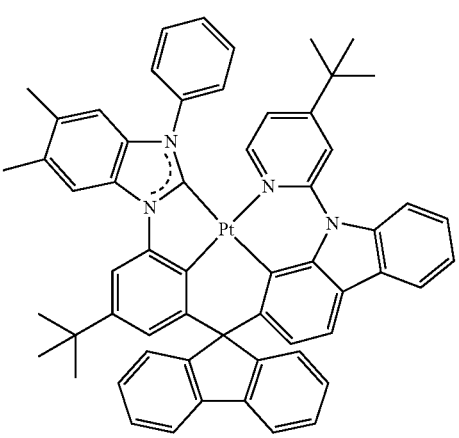
58
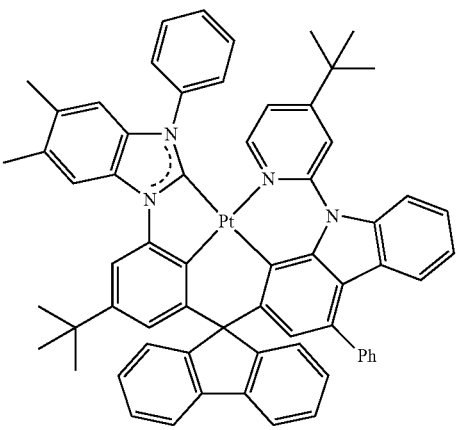

2265
-continued
59
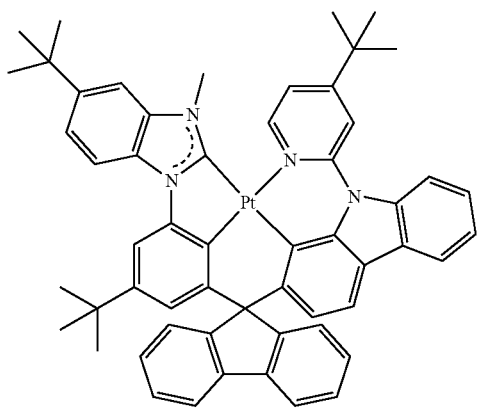
60
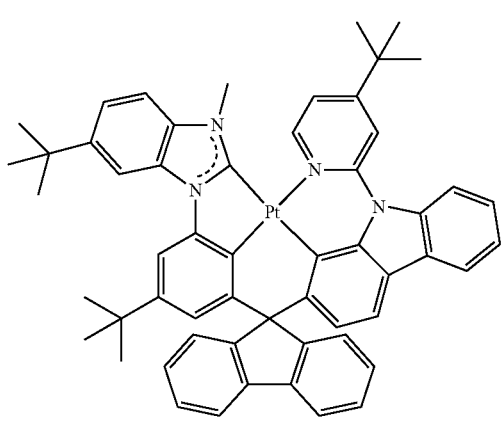
61
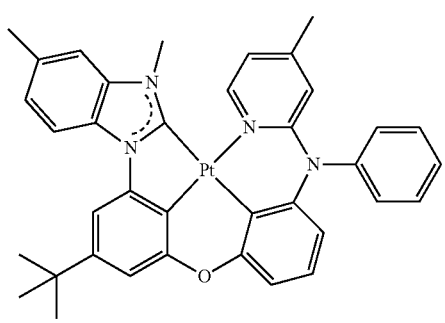
62
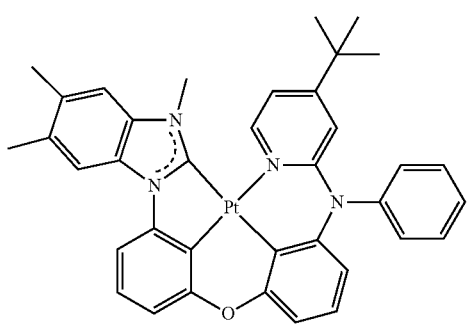
2266
-continued
63
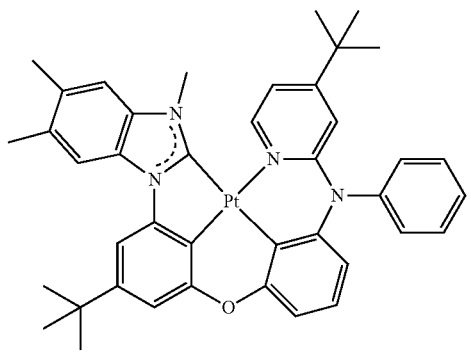
64
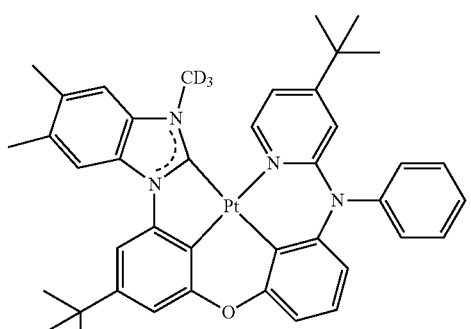
65
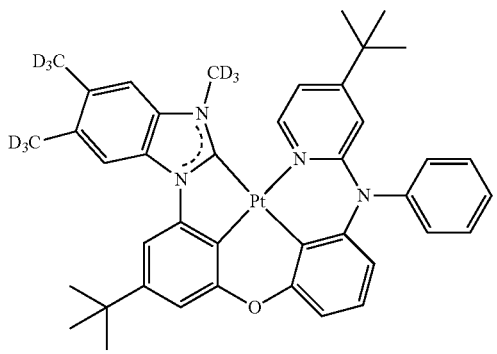
66
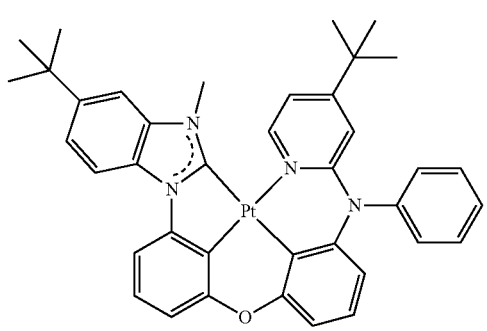

2267
-continued
67
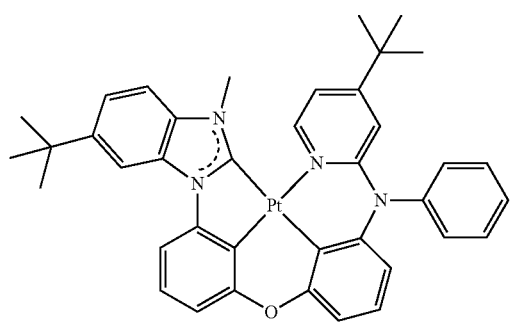
68
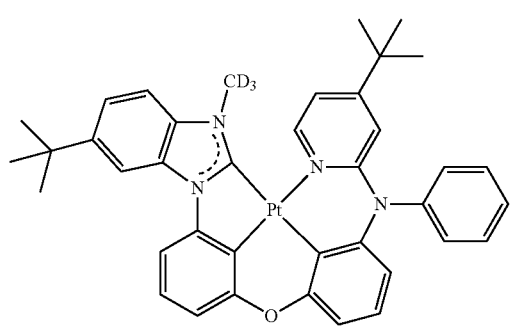
69
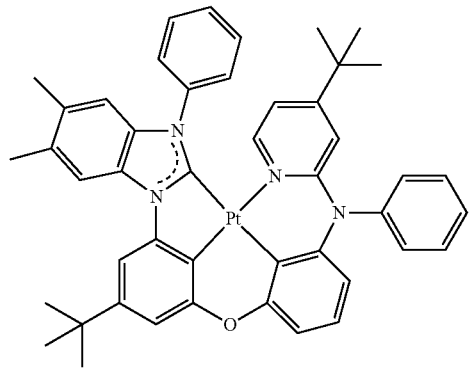
70
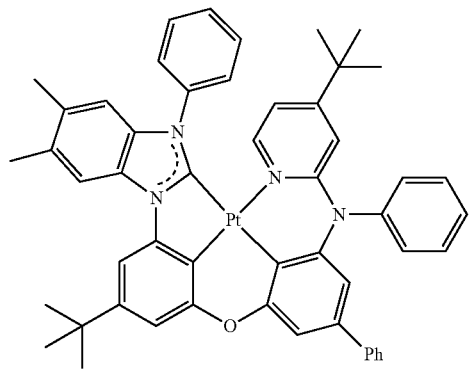
2268
-continued
71
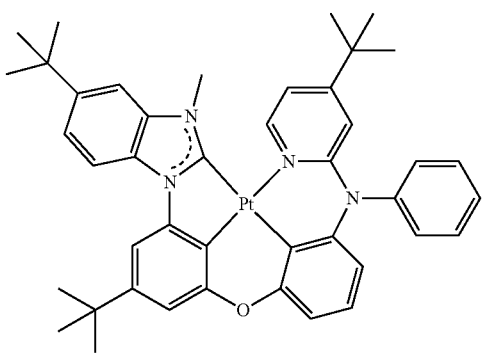
72
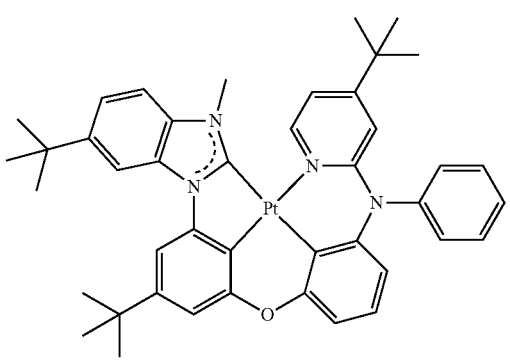
73
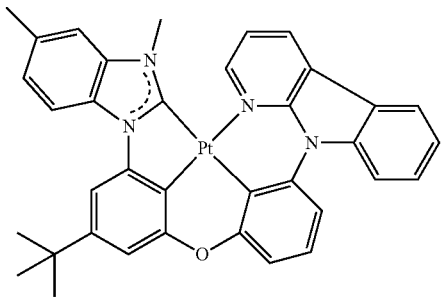
74
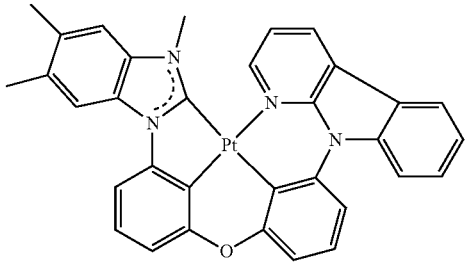
75
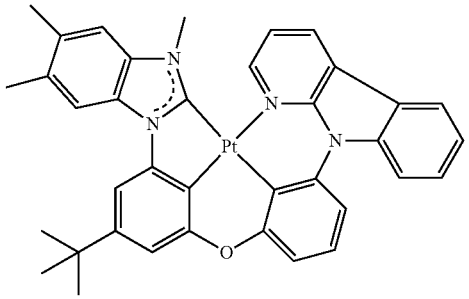

2269
-continued
76
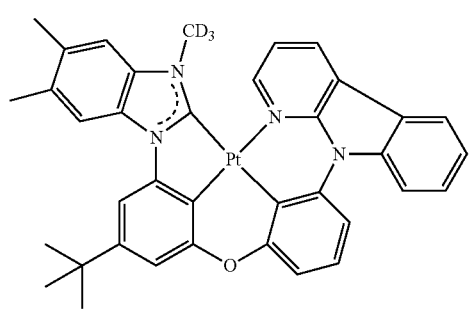
77
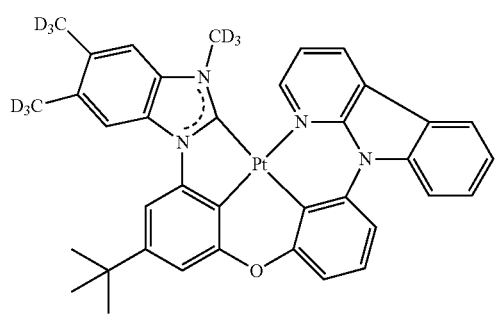
78
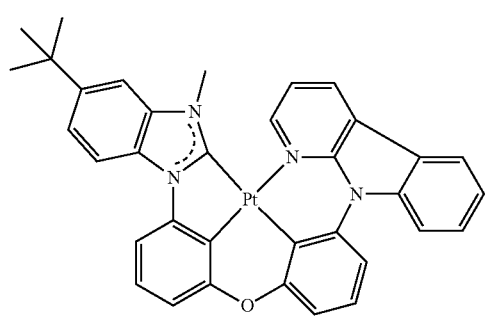
79
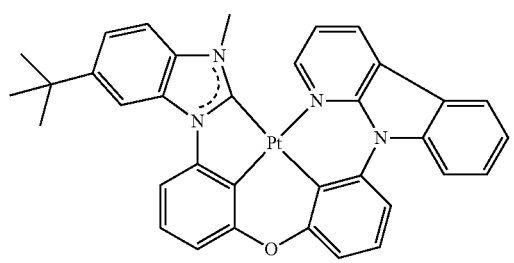
80
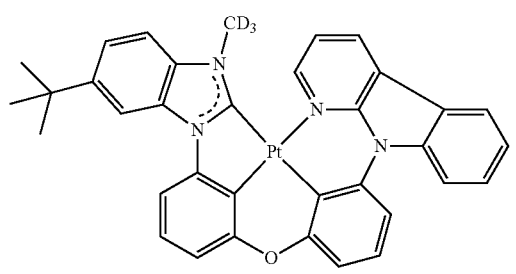
2270
-continued
81
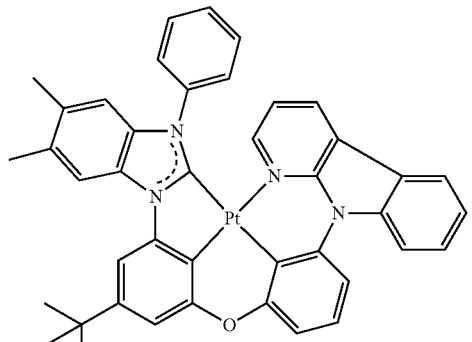
82
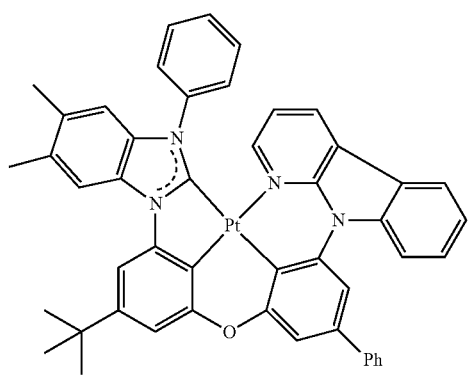
83
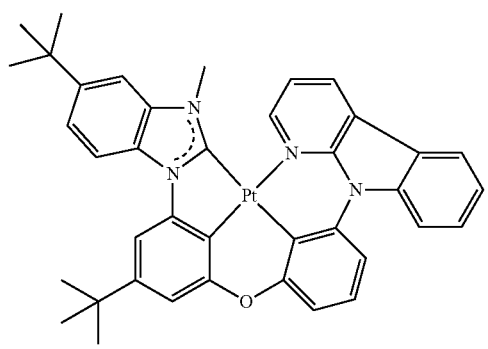
84
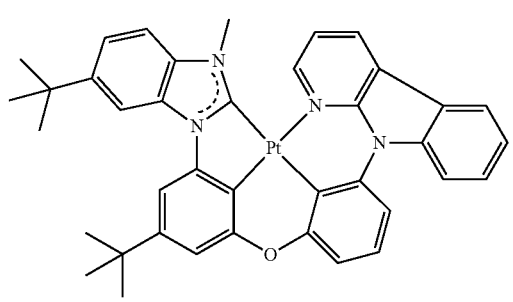

2271
-continued
85 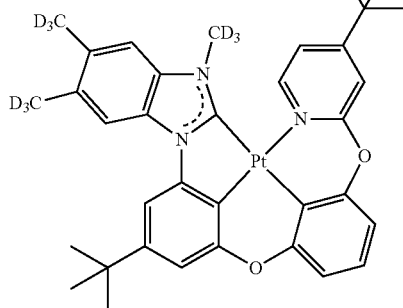
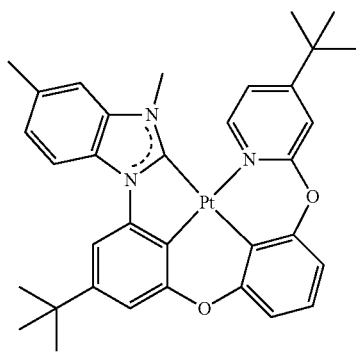
86 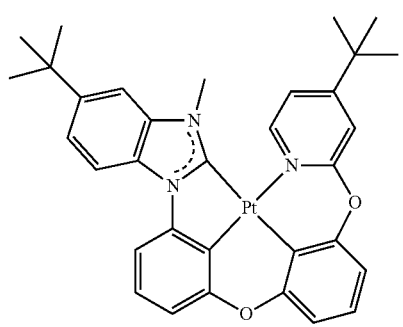
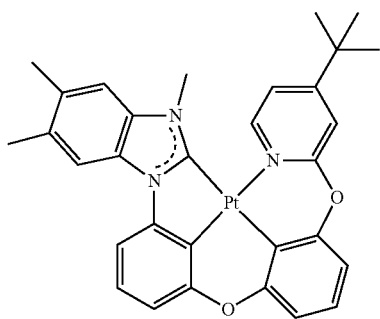
2272
-continued
89 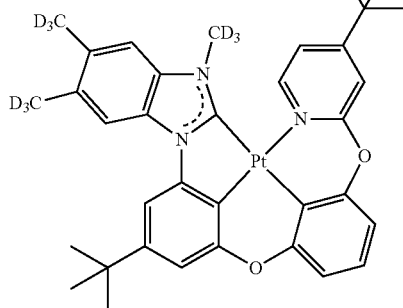
90 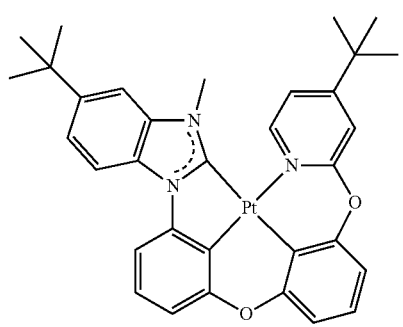
87 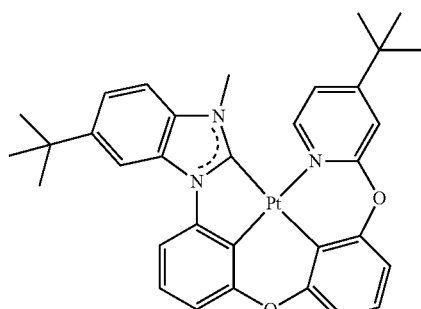

91 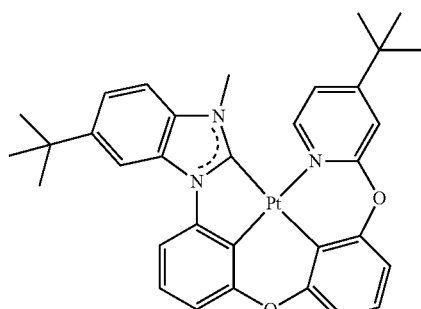
88 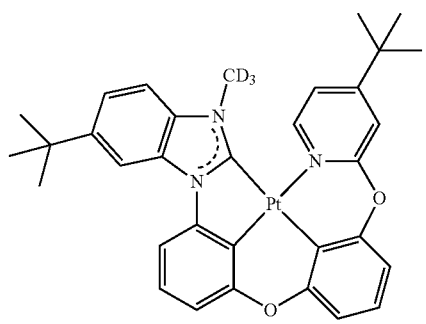

92 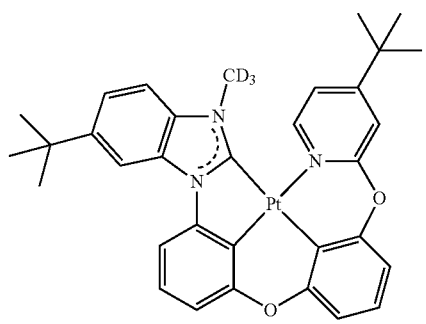

93
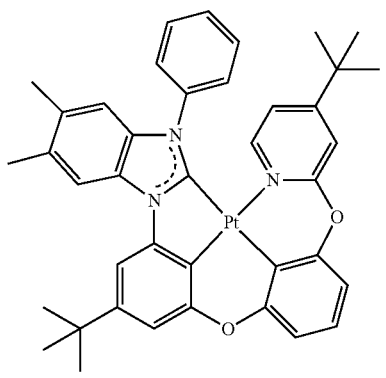
94
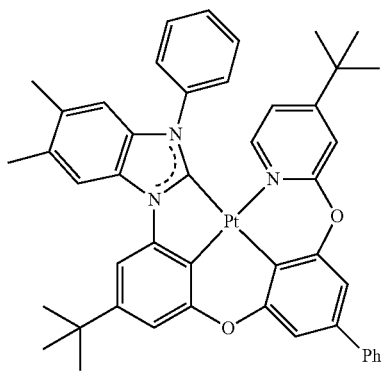
95
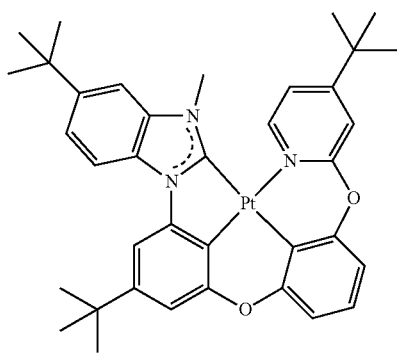
96
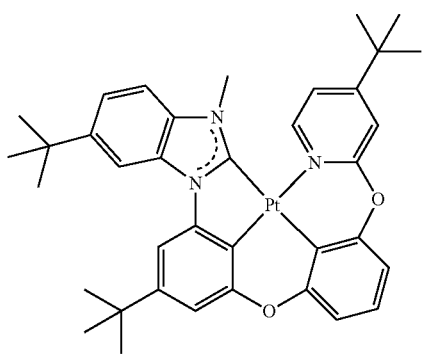
97
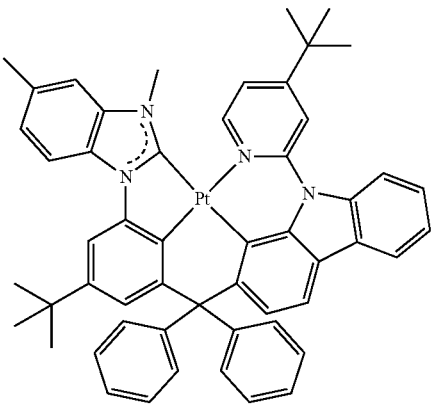
98
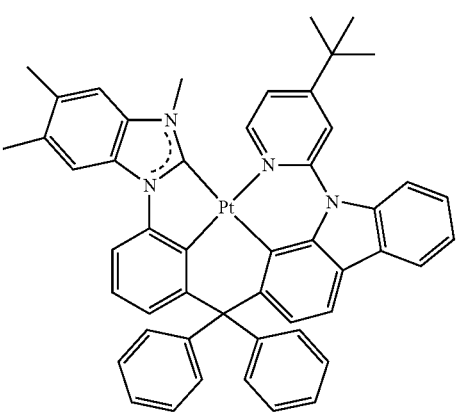
99
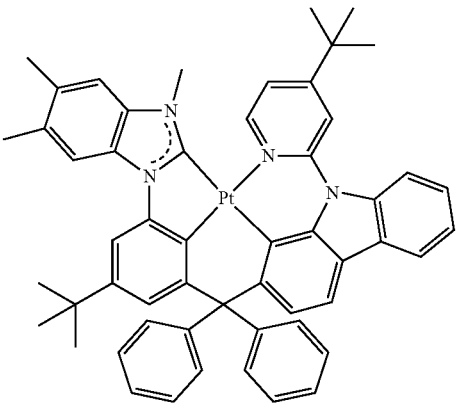
100
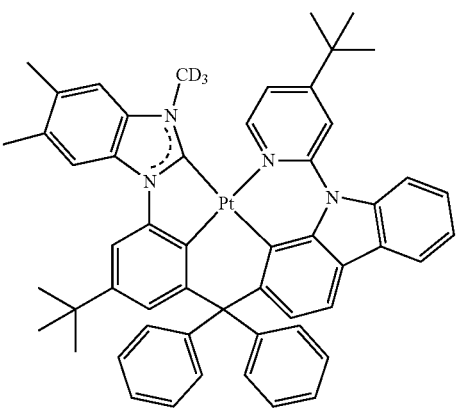

2275
-continued
2276
-continued
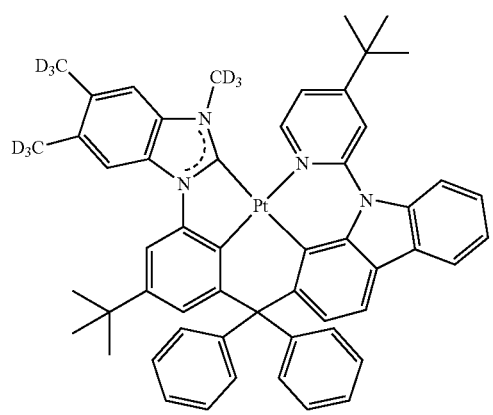
101
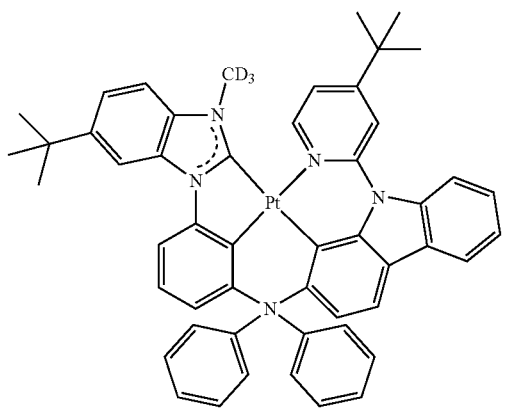
104
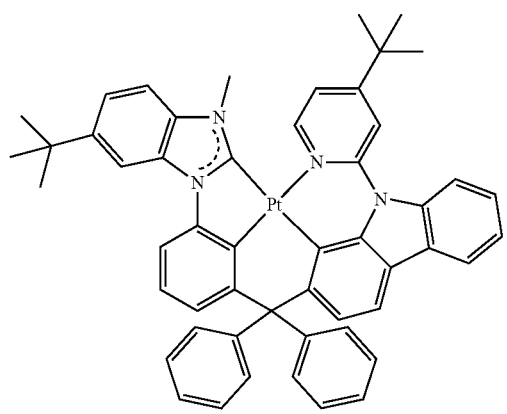
102
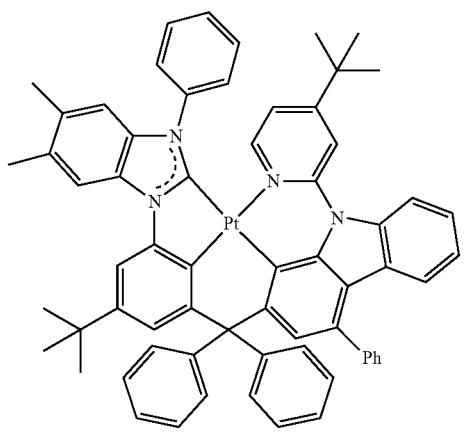
105
103
106

2277
-continued
2278
-continued
107
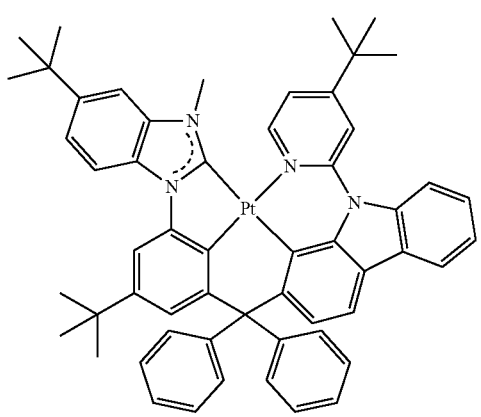
108
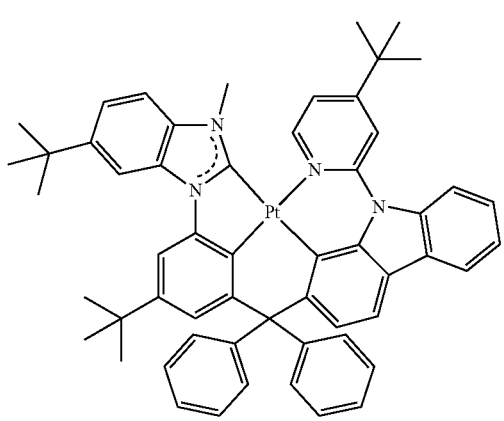
109
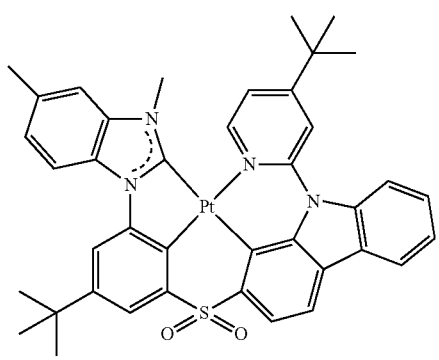
110
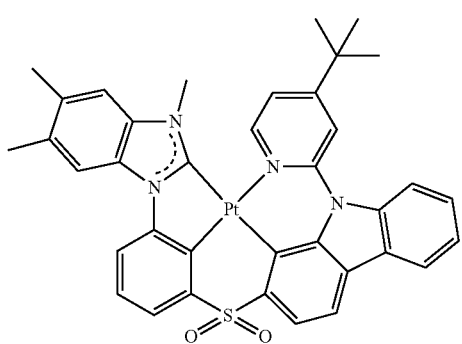
111
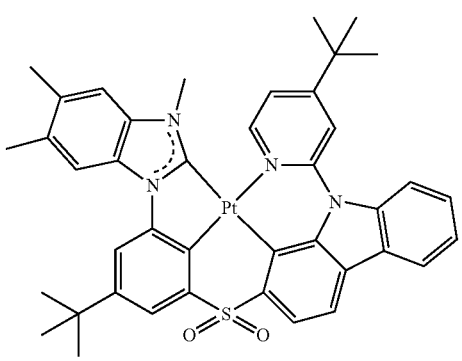
112
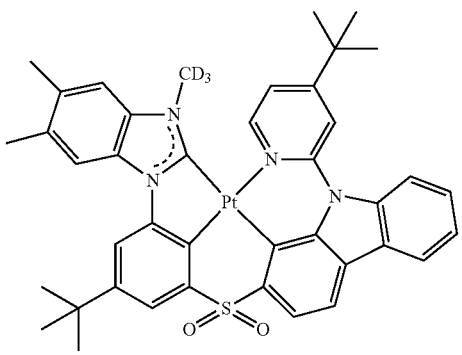
113
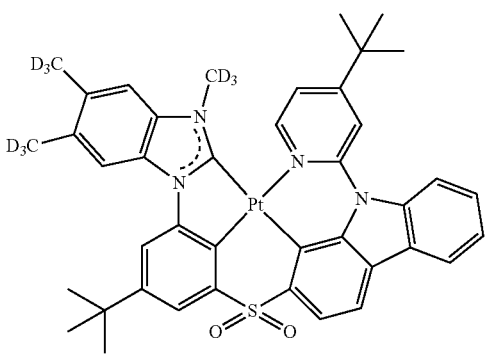
114
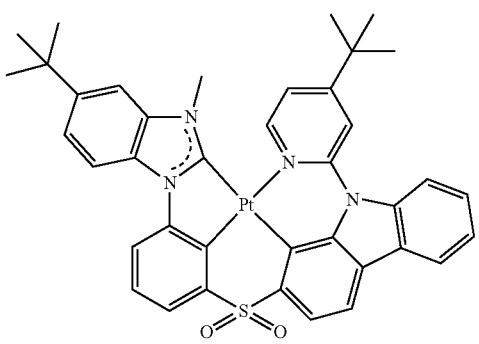

2279
-continued
115
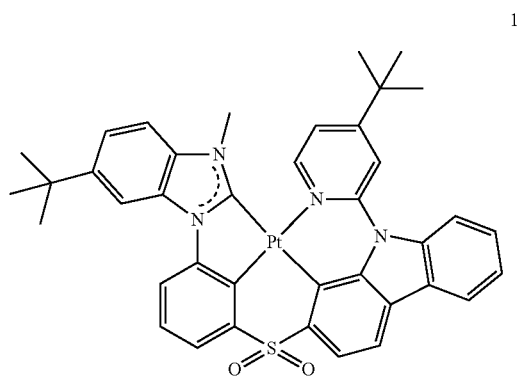
116
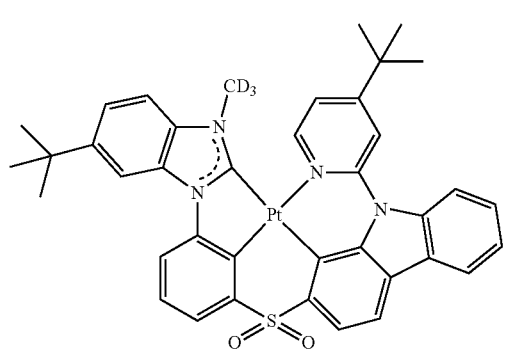
117
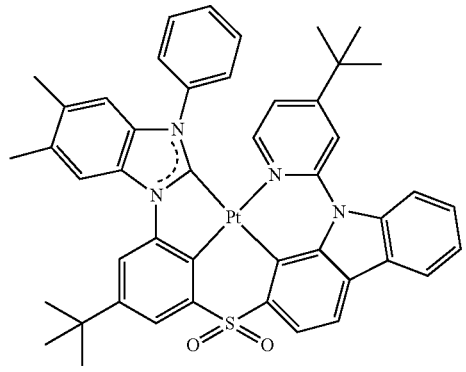
118
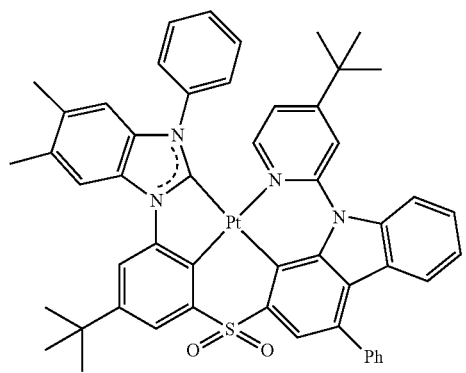
2280
-continued
119
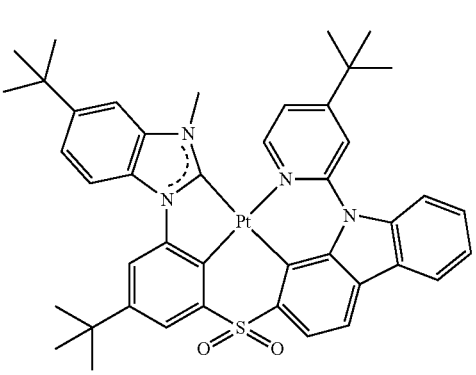
120
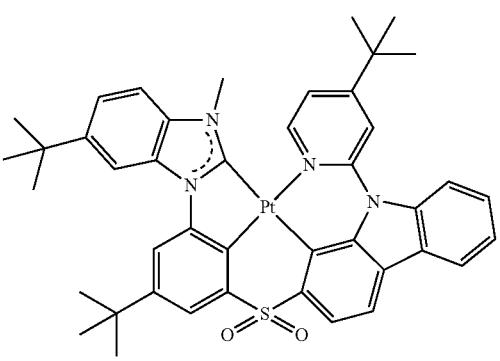
Group III
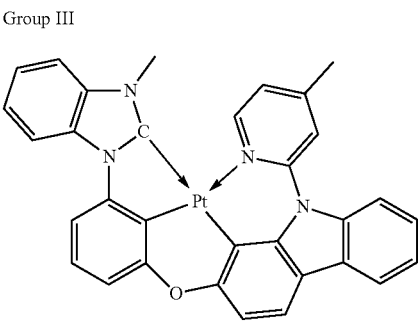
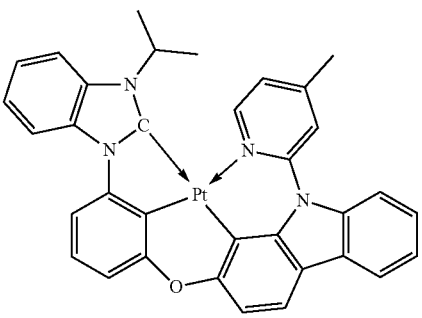

2281
-continued
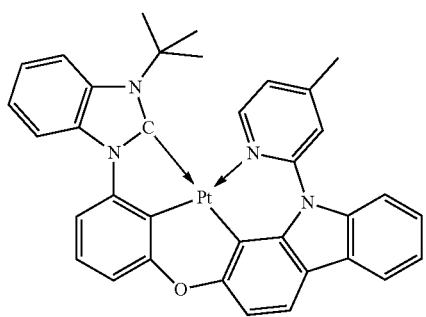
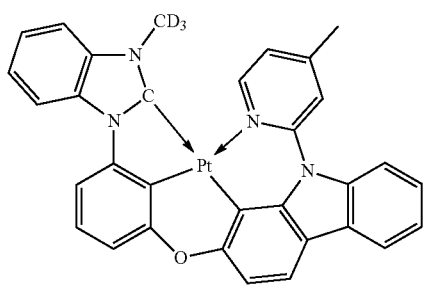
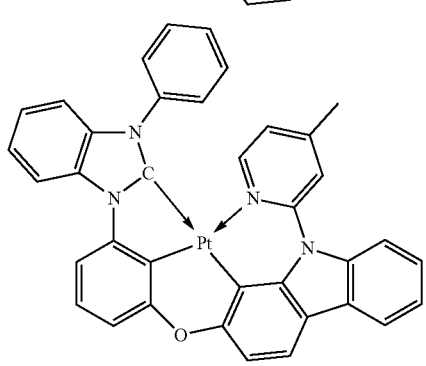
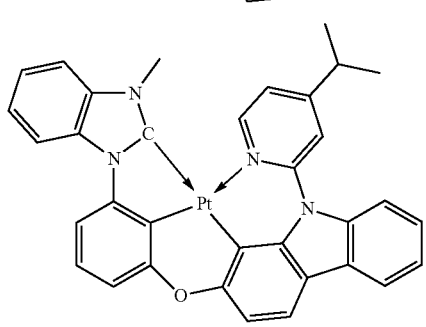
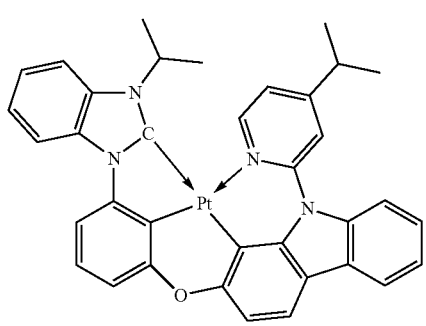
2282
-continued
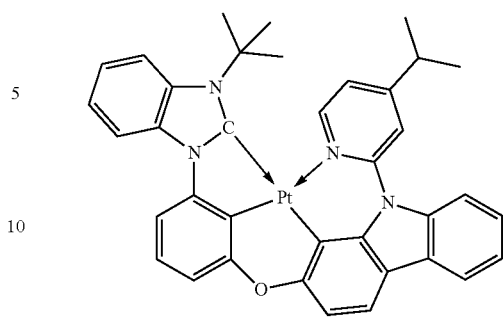
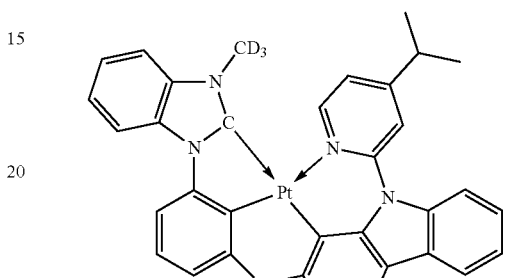
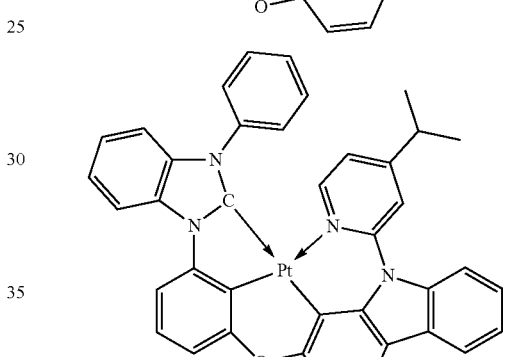
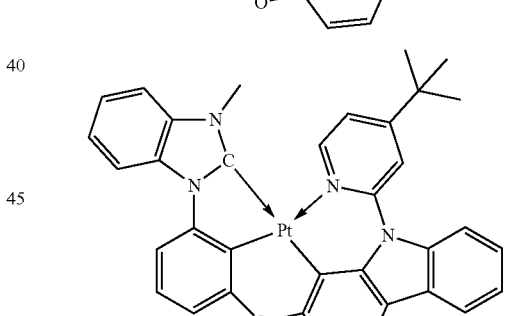
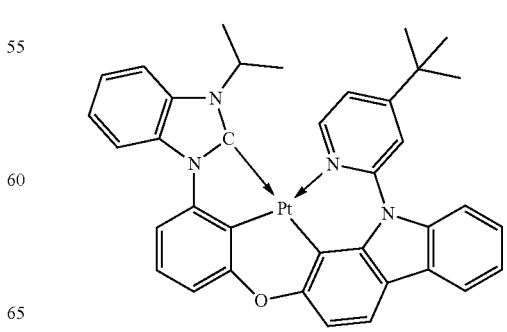

2283
-continued
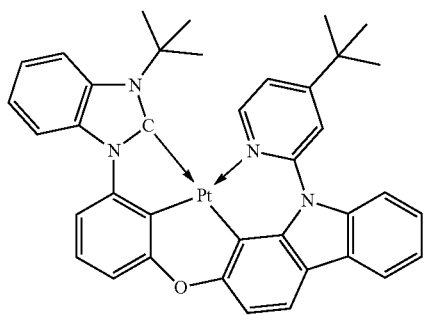
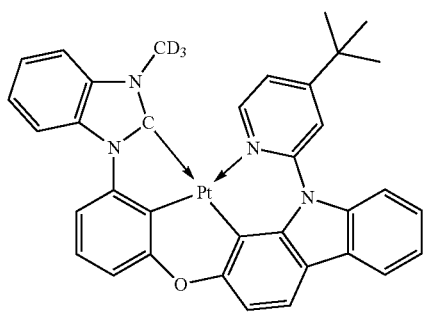
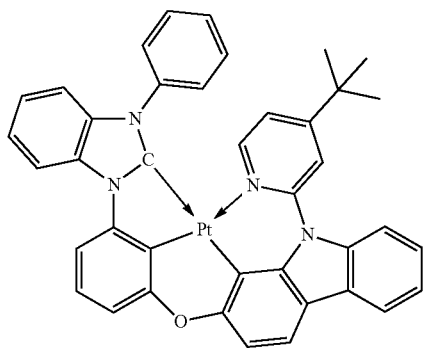
Group III
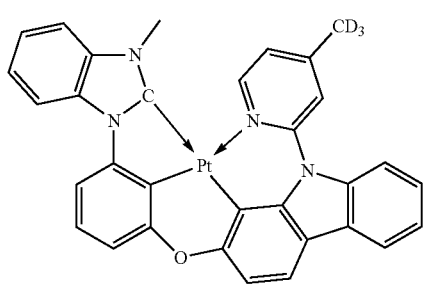
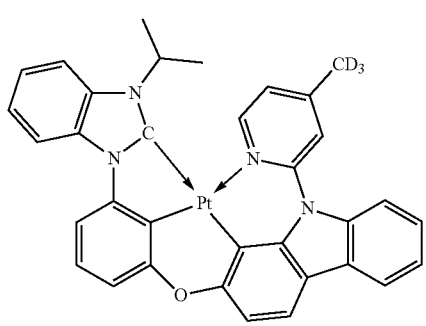
2284
-continued
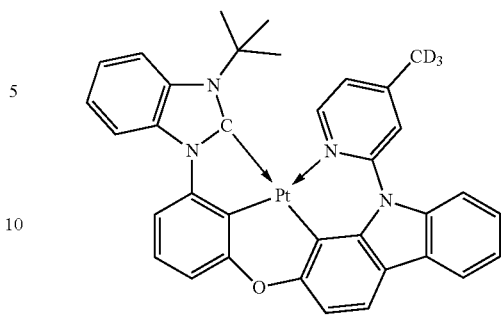
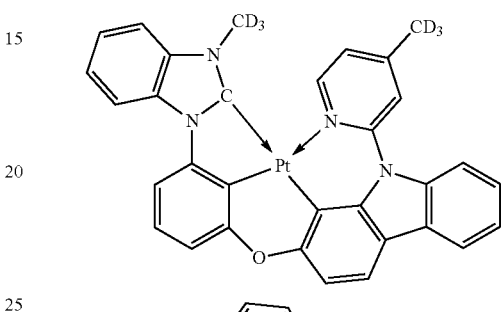
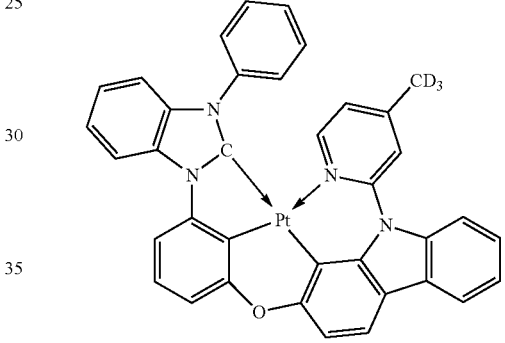
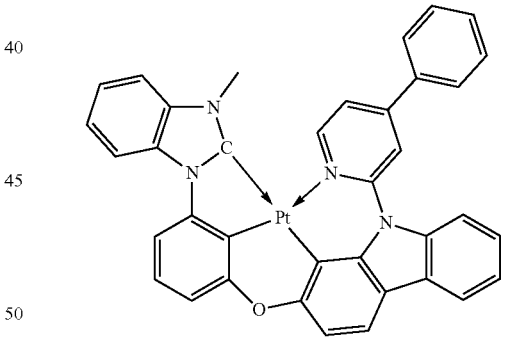
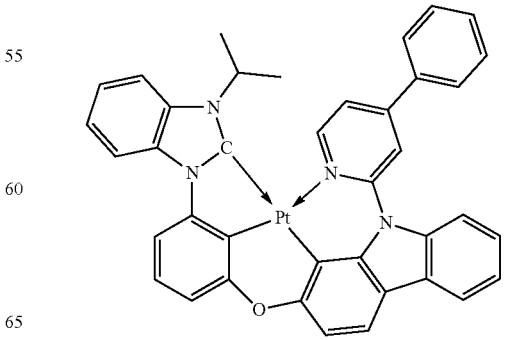

2285
-continued
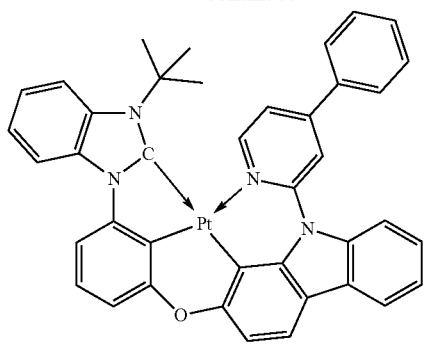
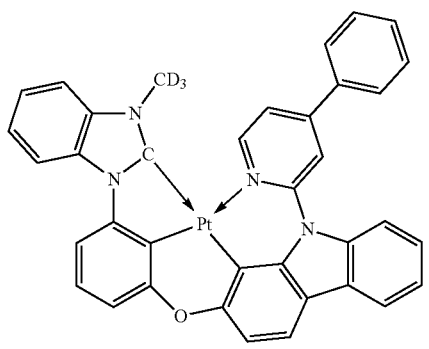
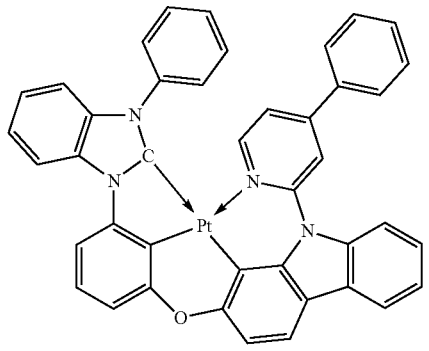
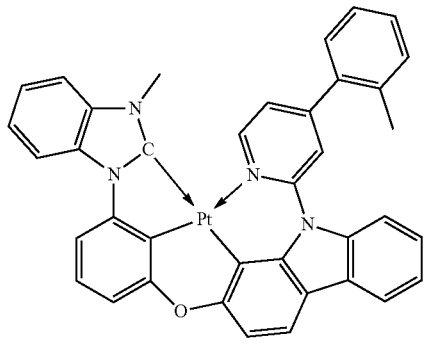
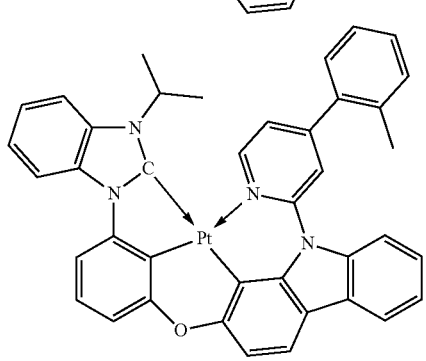
2286
-continued

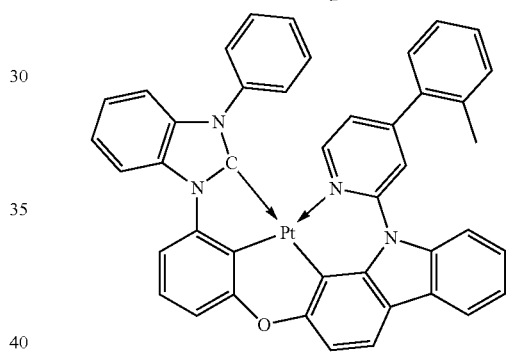

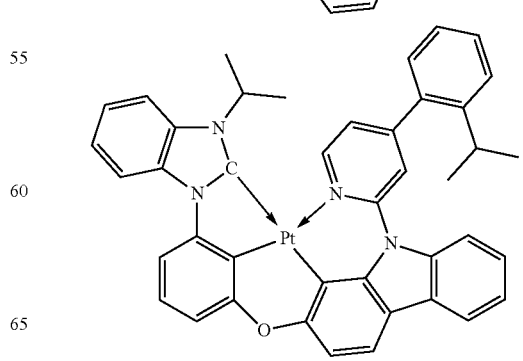

2287
-continued
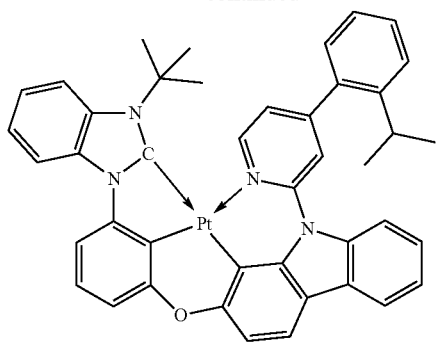
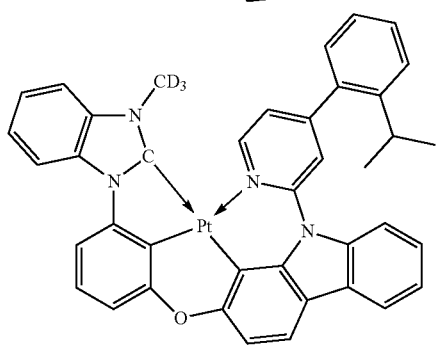
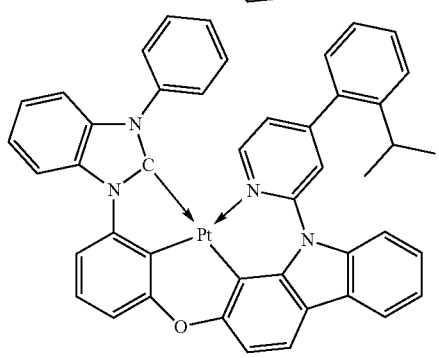
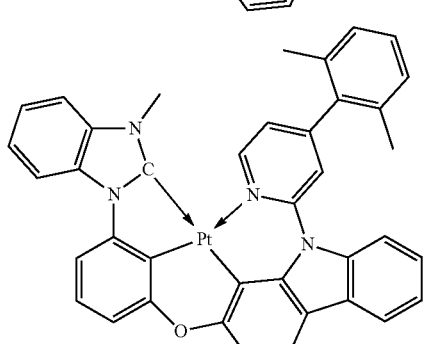
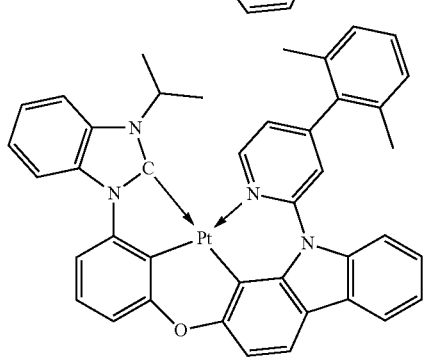
2288
-continued
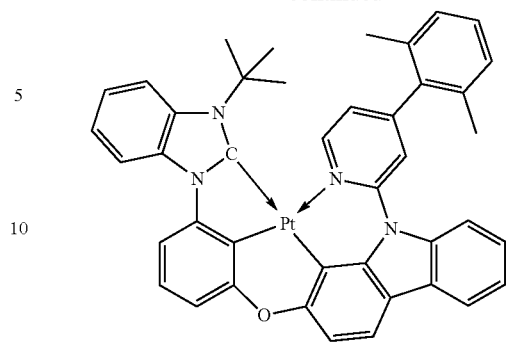
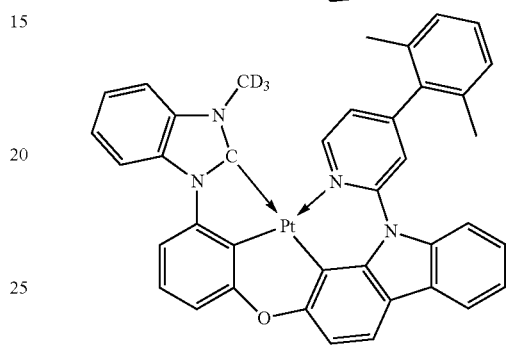
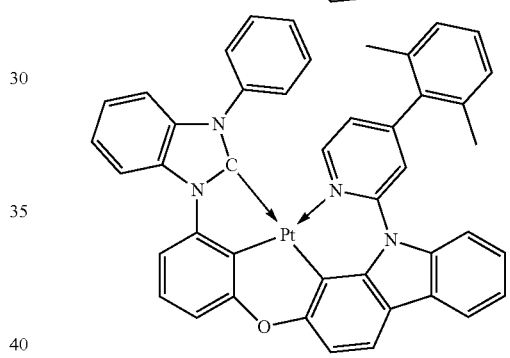
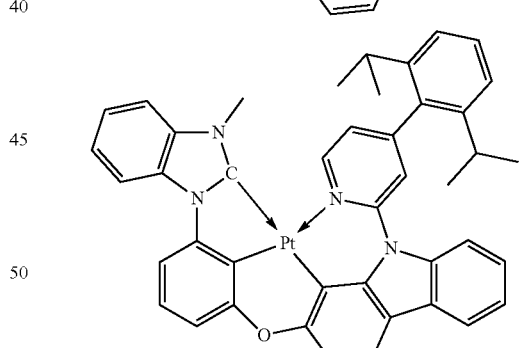
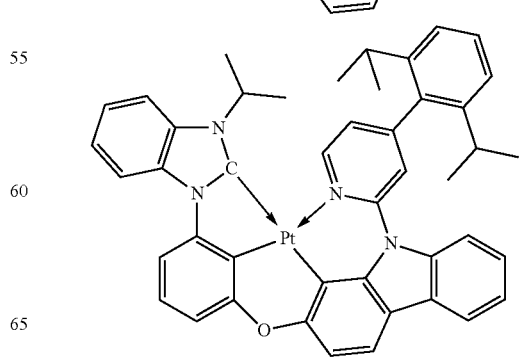

2289
-continued
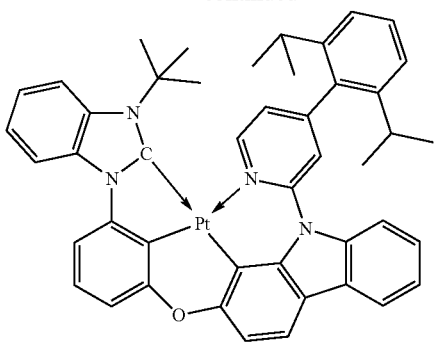
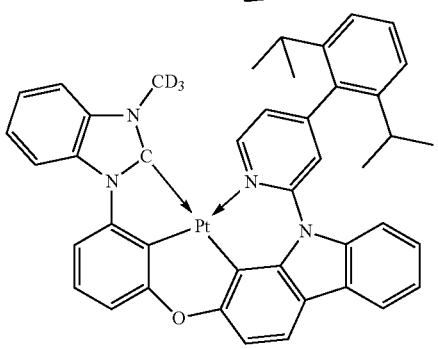
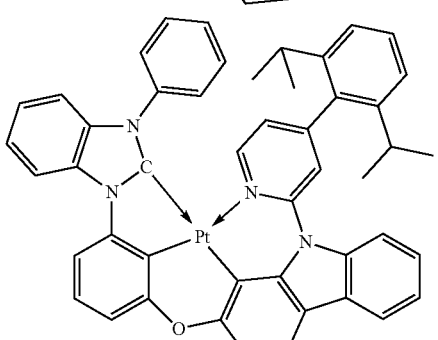
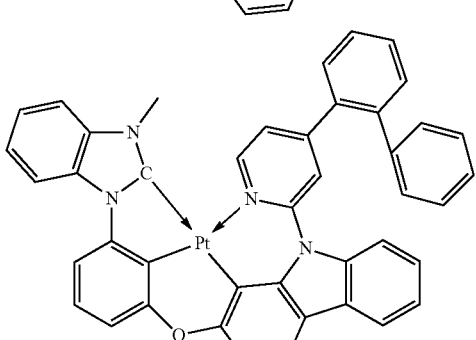
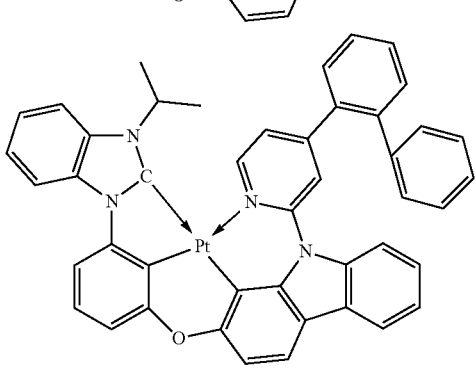
2290
-continued
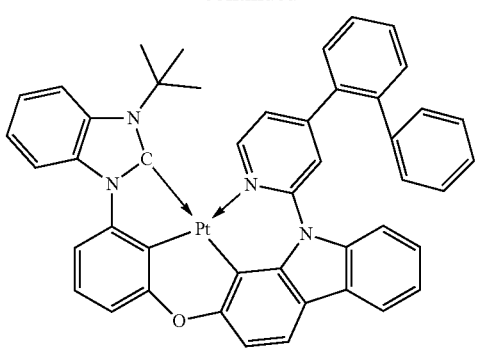
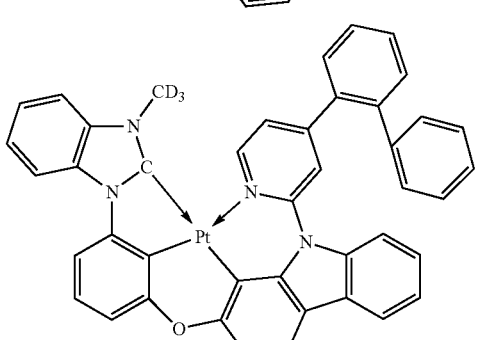
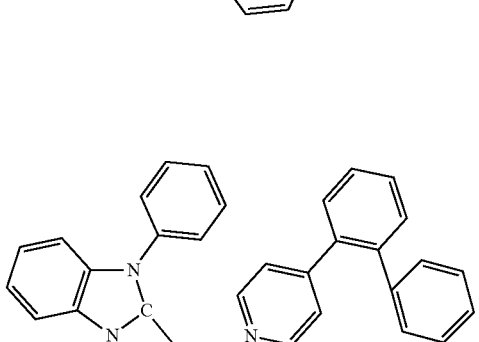
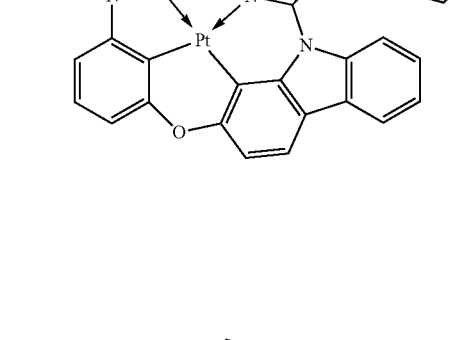
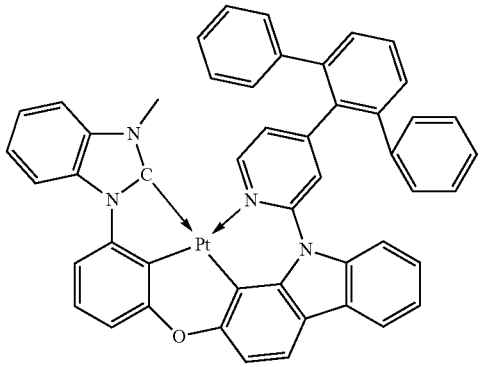

2291
-continued
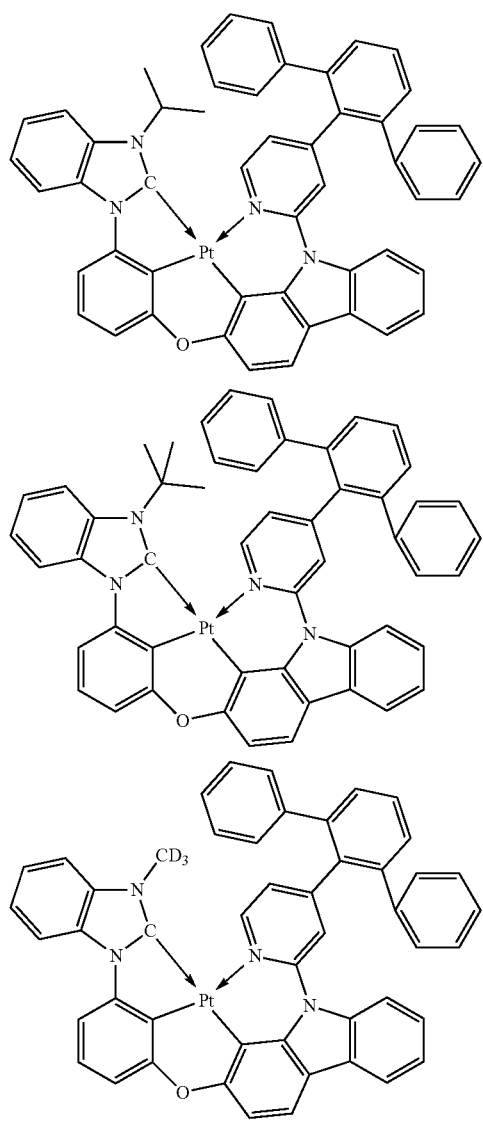
2292
-continued
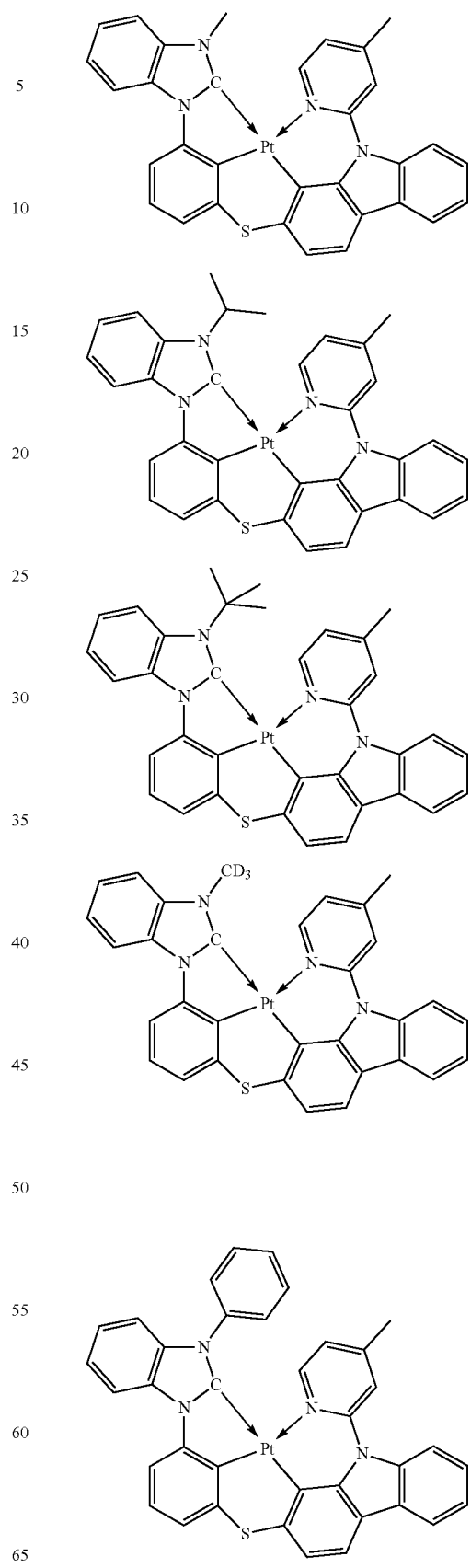

2293
-continued
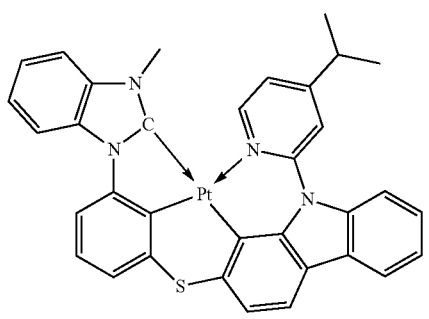
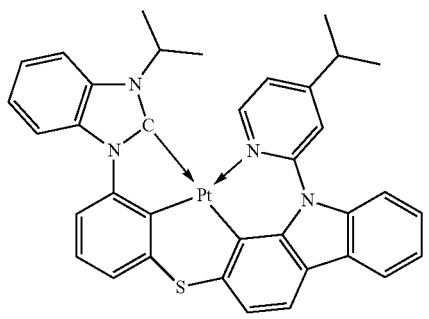
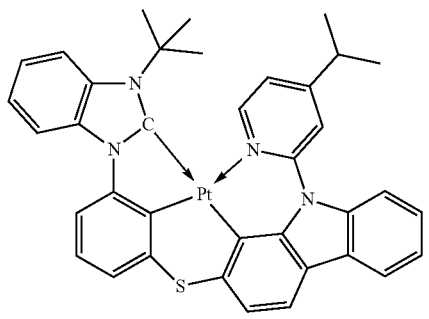
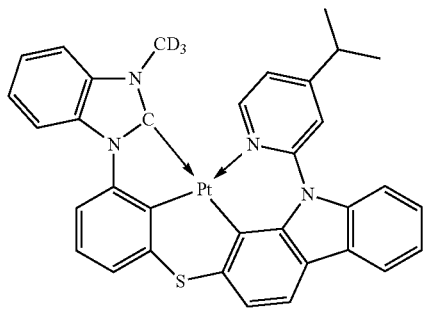
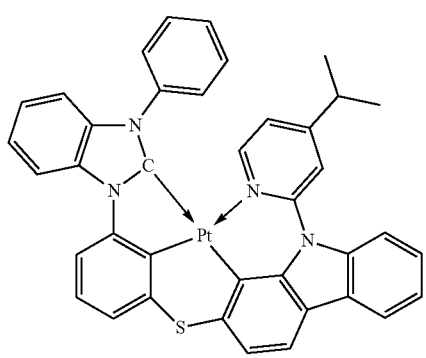
2294
-continued

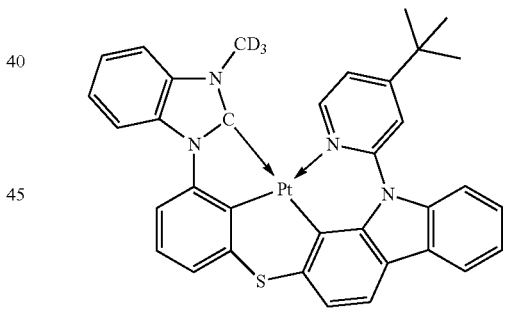
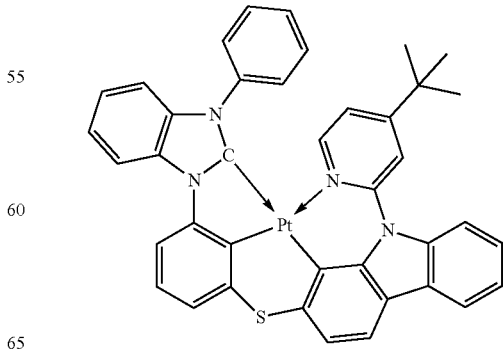

2295
-continued
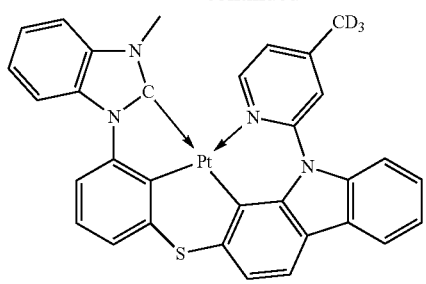
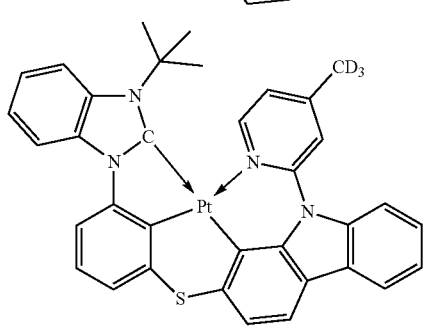
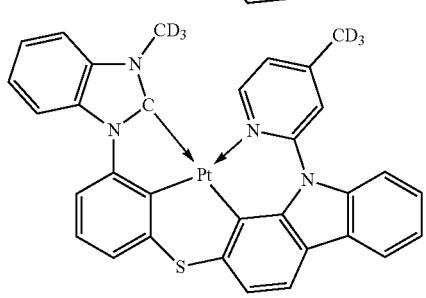
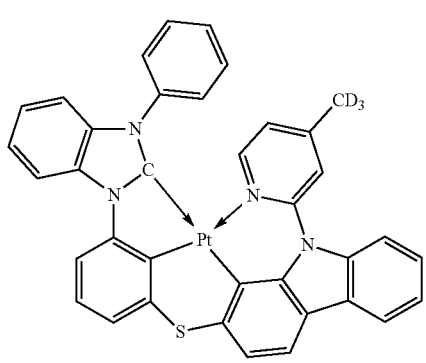
2296
-continued
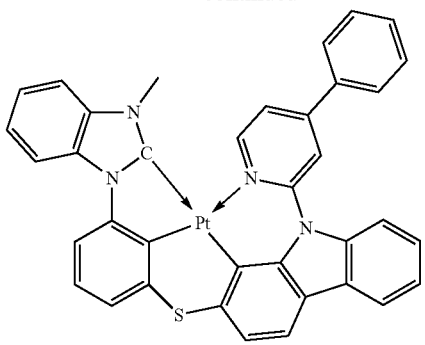
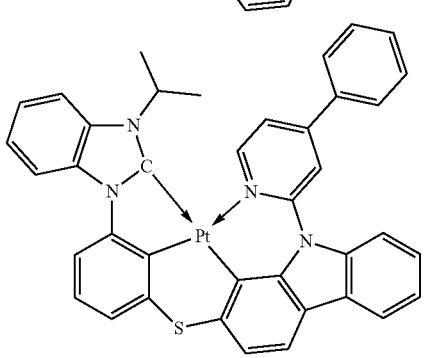
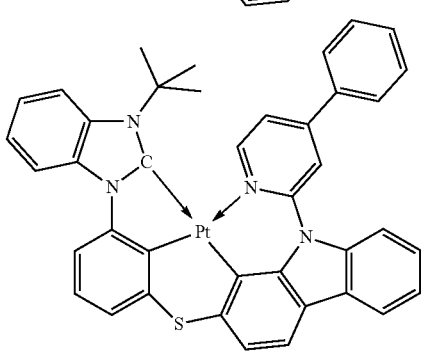
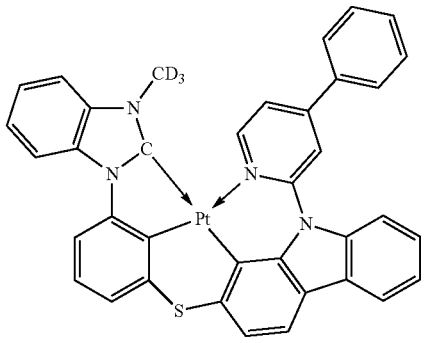
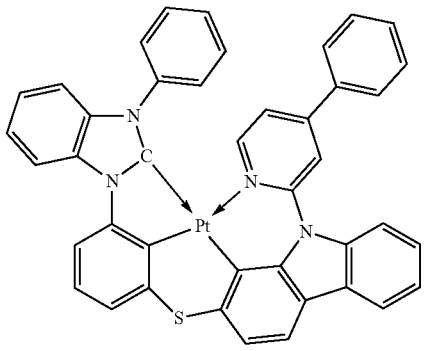

2297
-continued
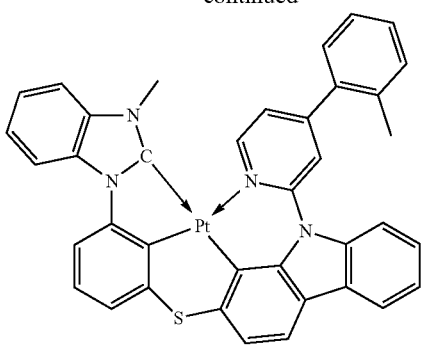
2298
-continued
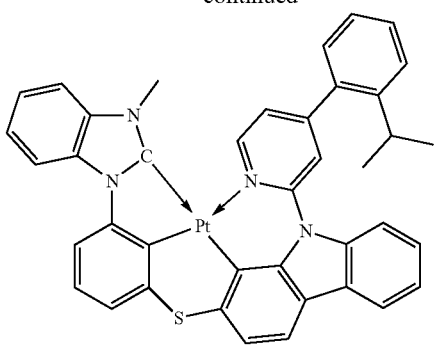
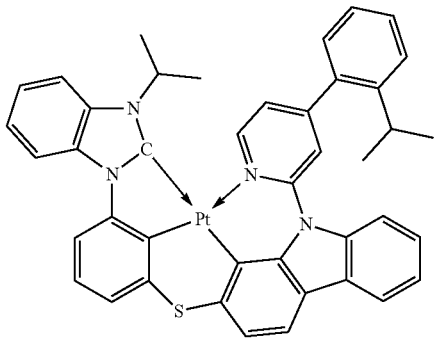
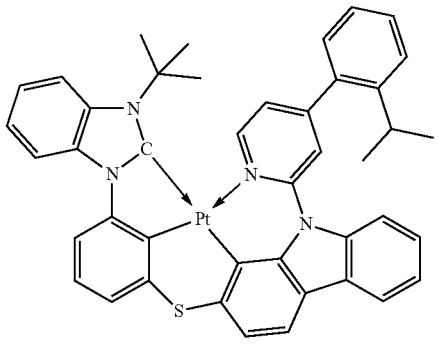
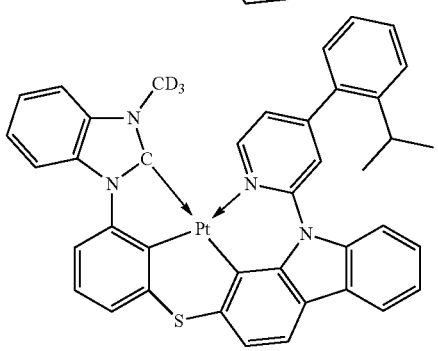
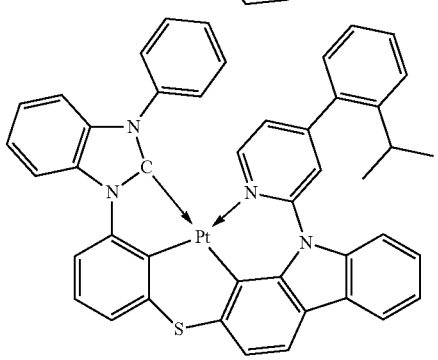

2299
-continued
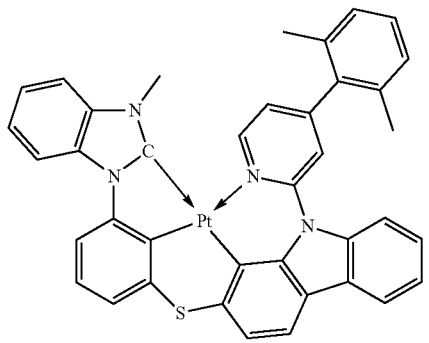
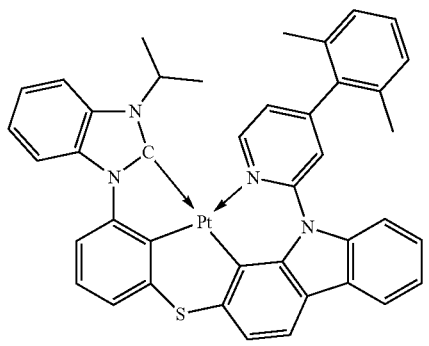
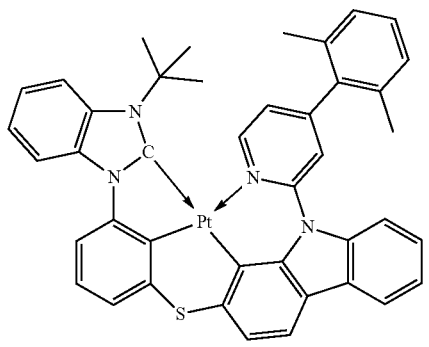
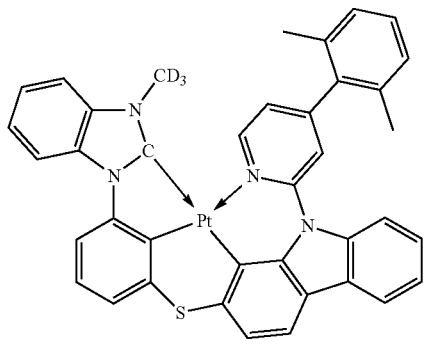
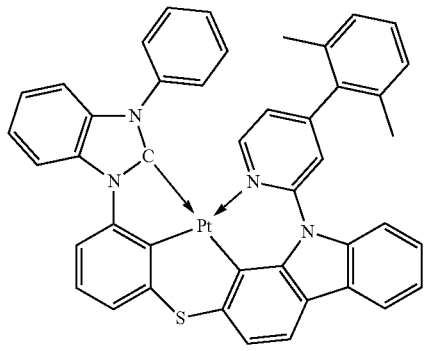
2300
-continued
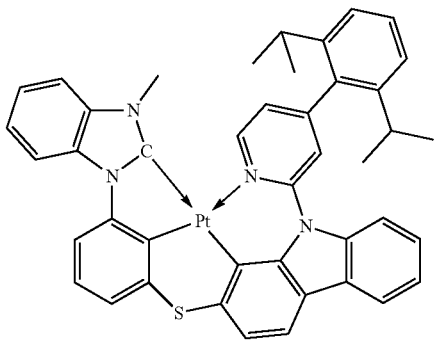
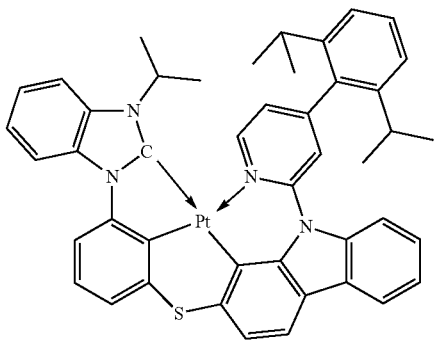
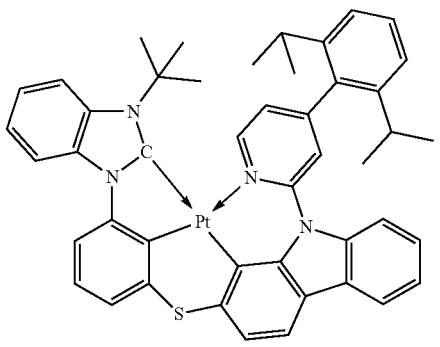
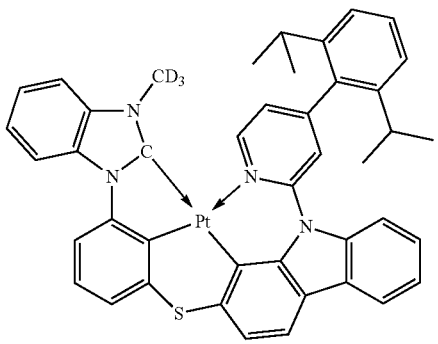
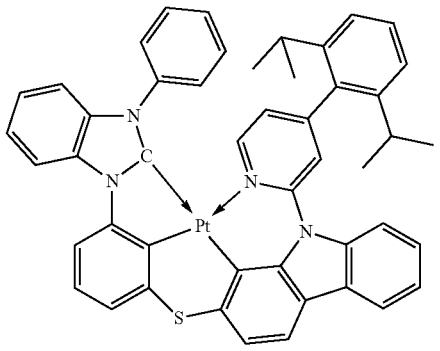

2301
-continued
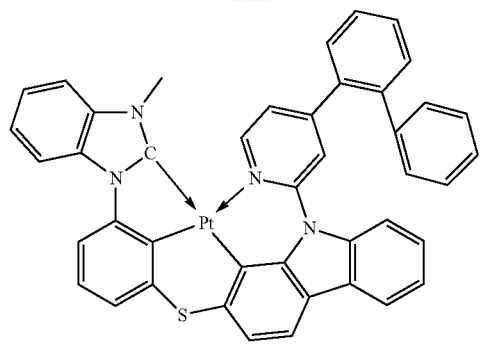
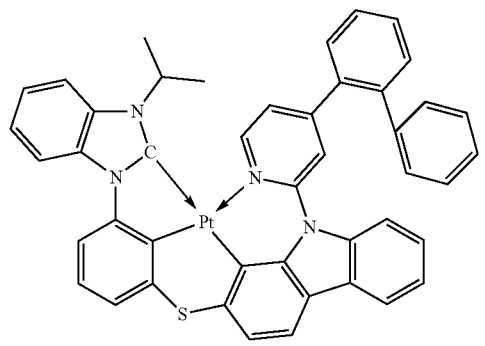
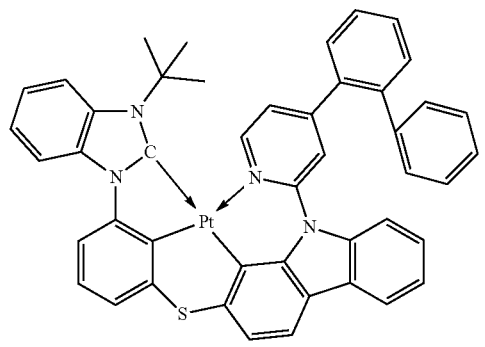
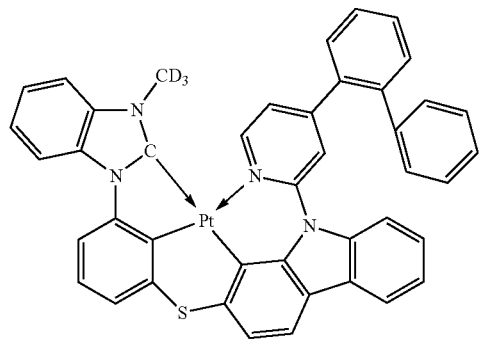
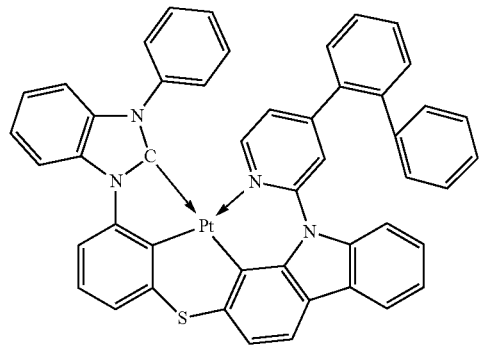
2302
-continued
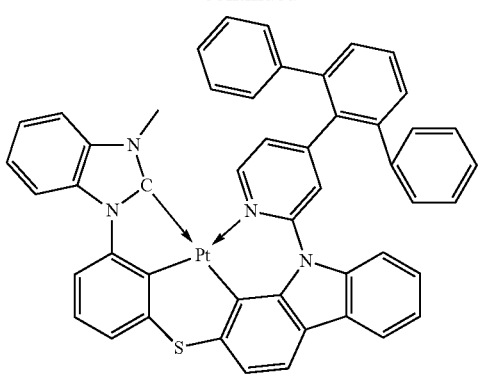
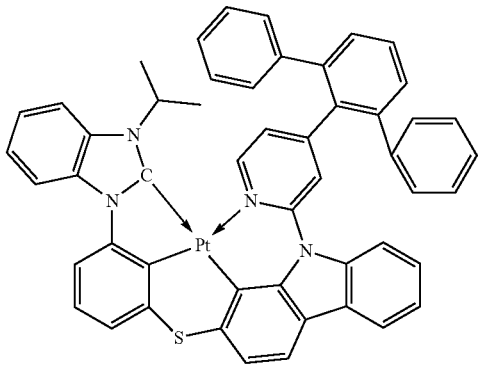
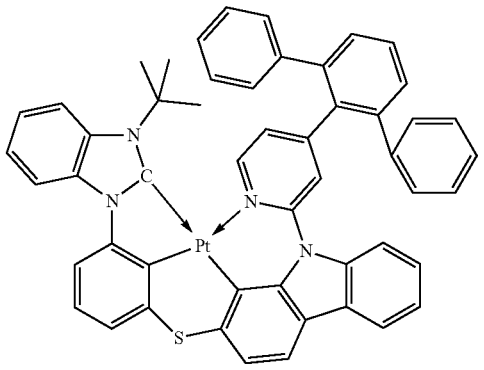
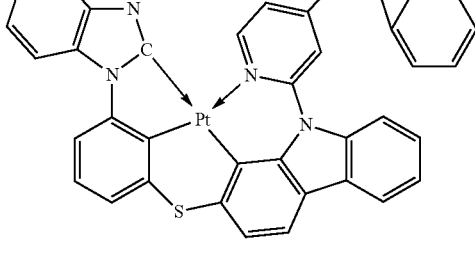

2303
-continued
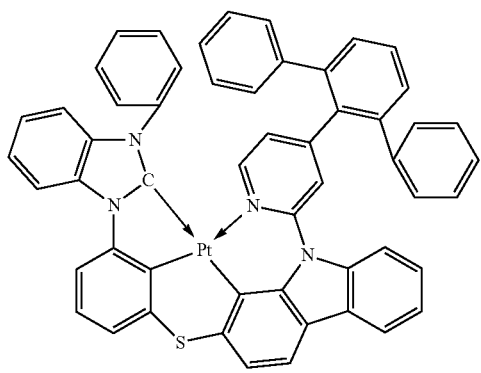
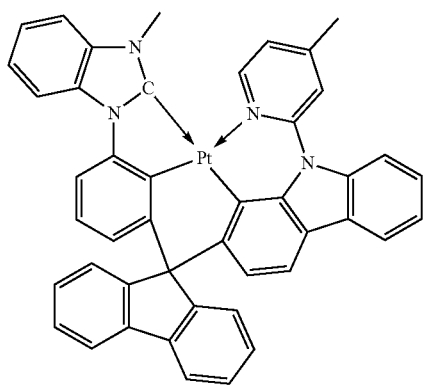
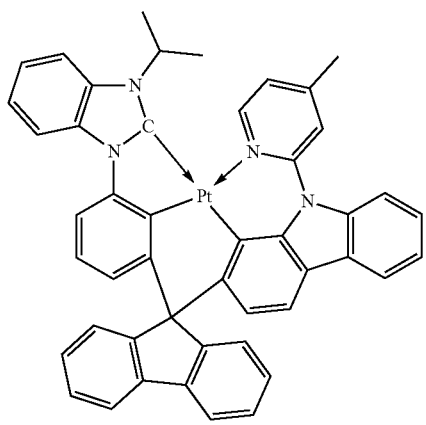
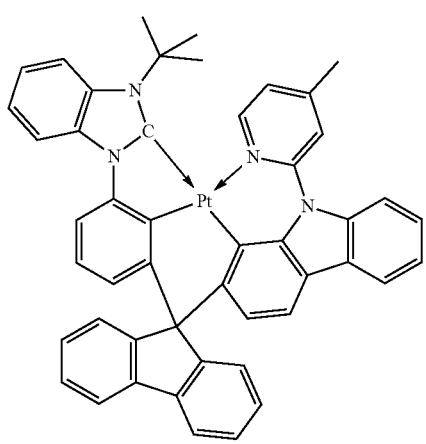
2304
-continued
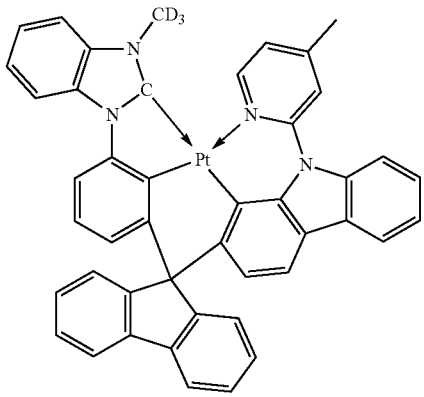
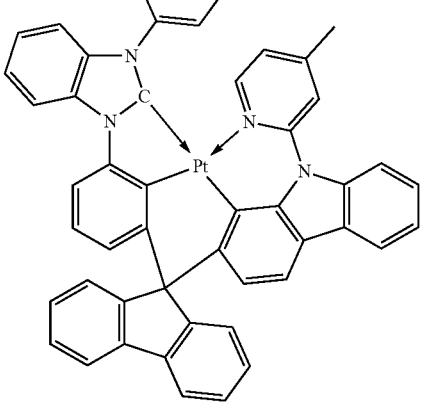
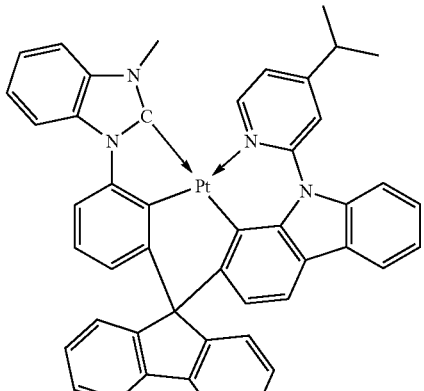
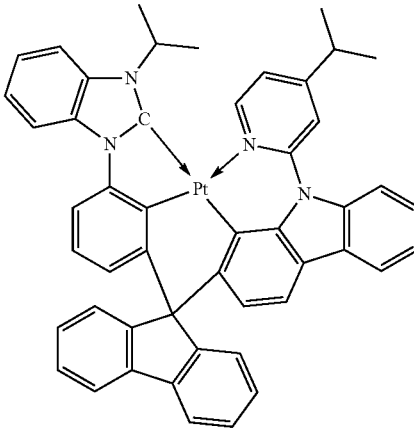

2305
-continued
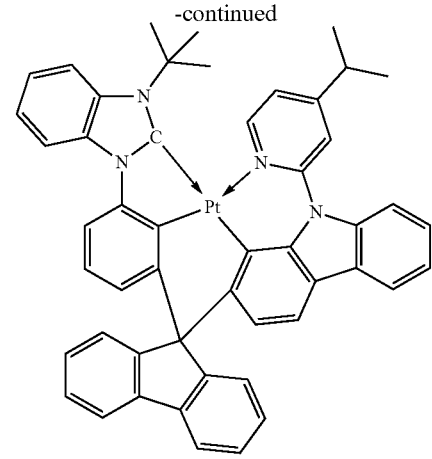
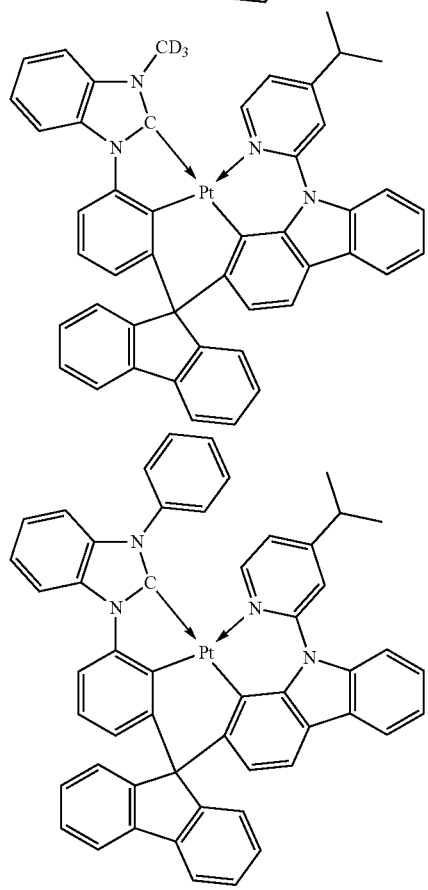
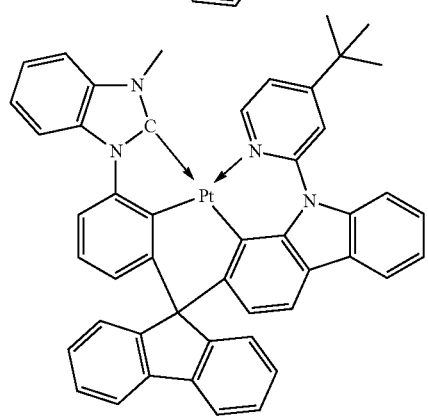
2306
-continued
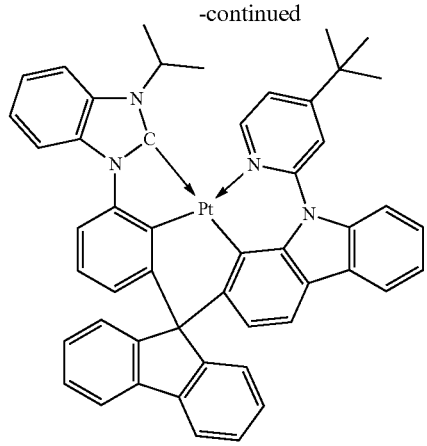
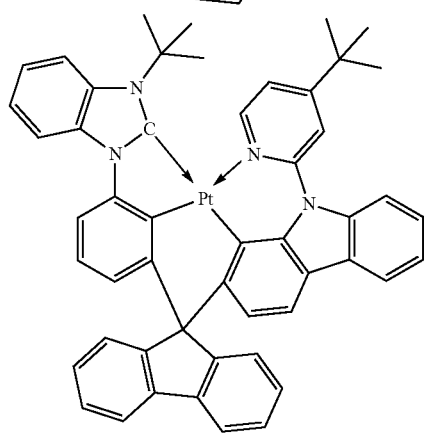
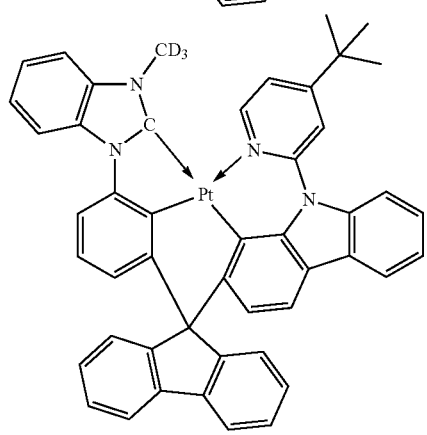
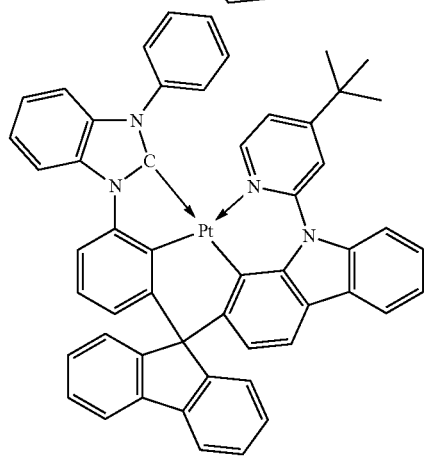

2307
-continued
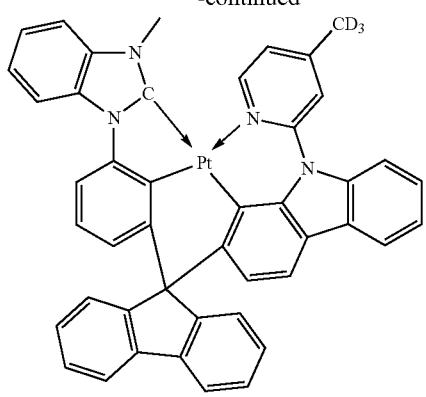
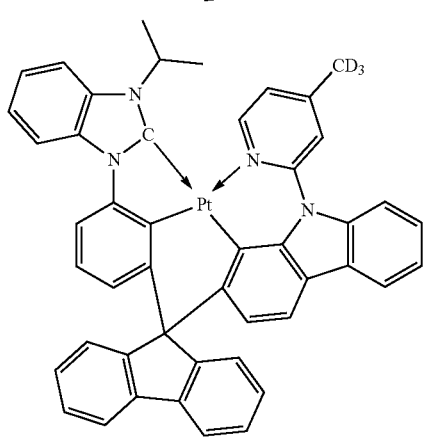
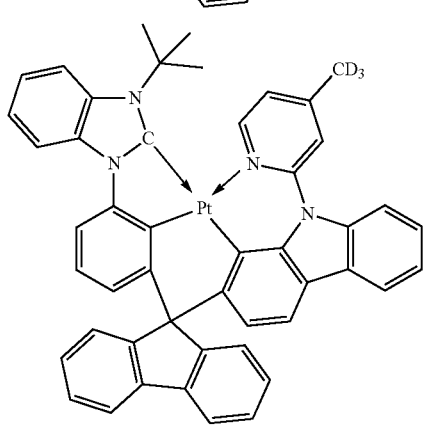
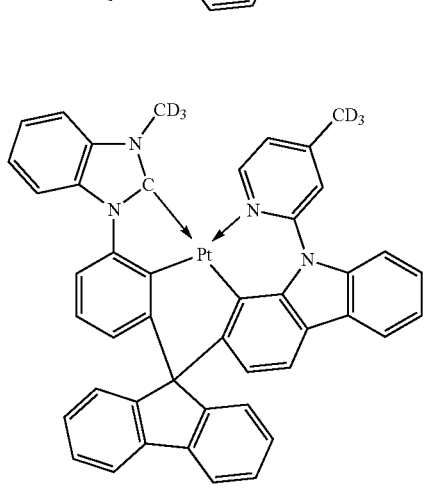
2308
-continued
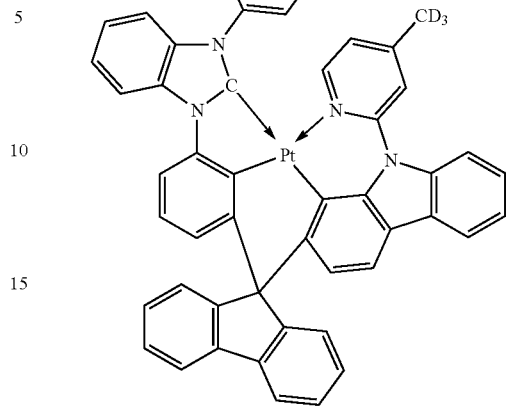
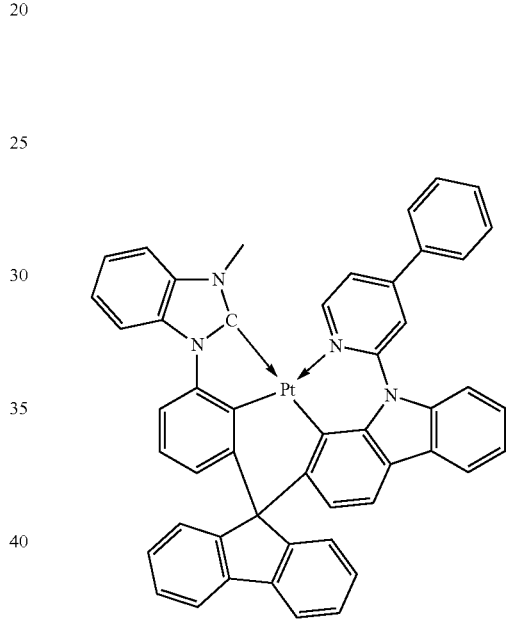
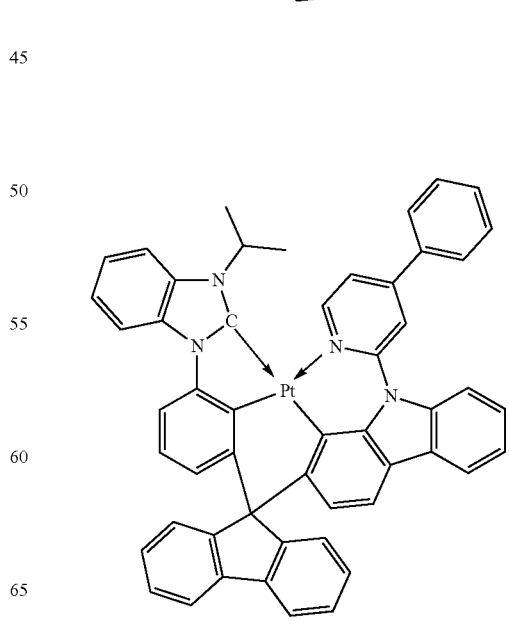

2309
-continued
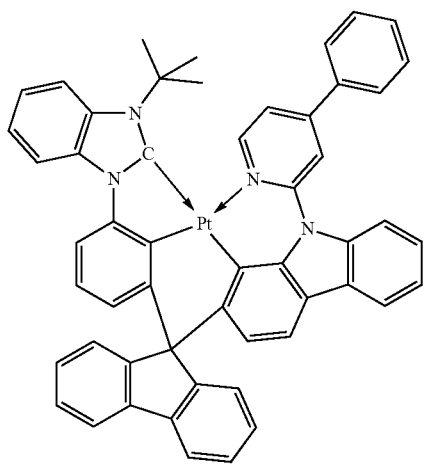
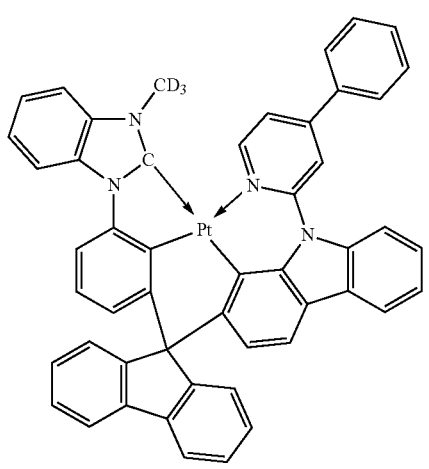
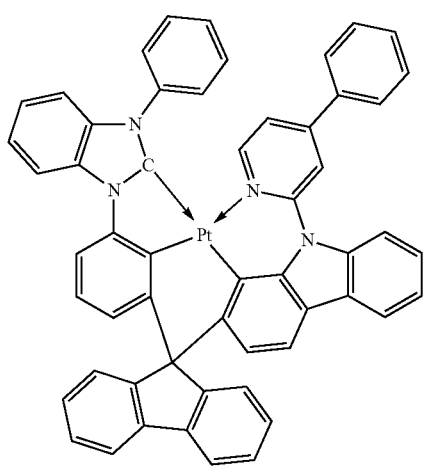
2310
-continued
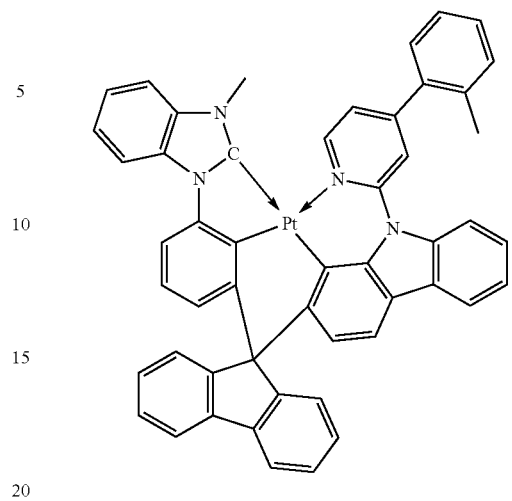
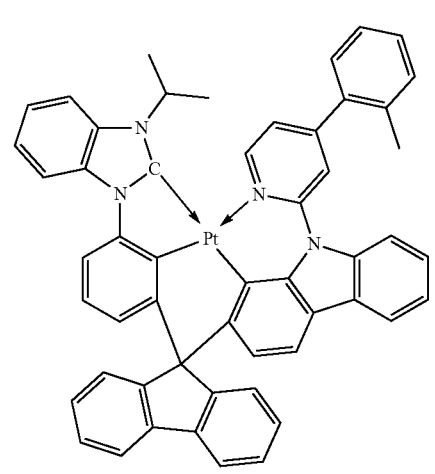
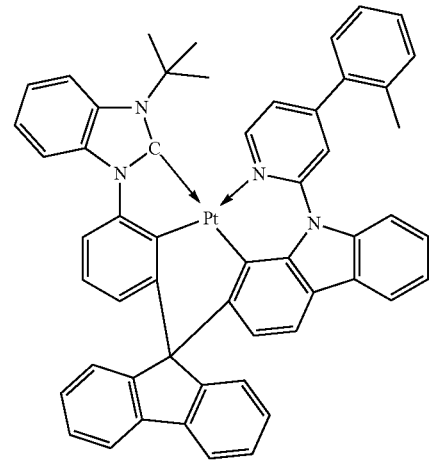

2311
-continued
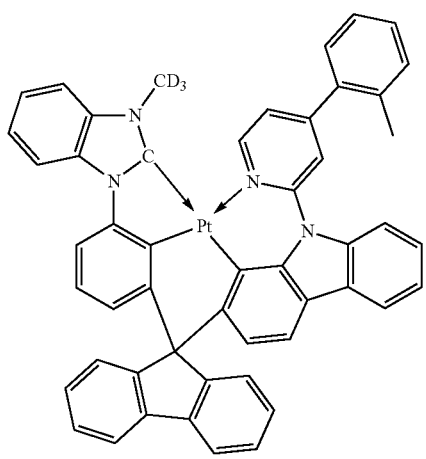
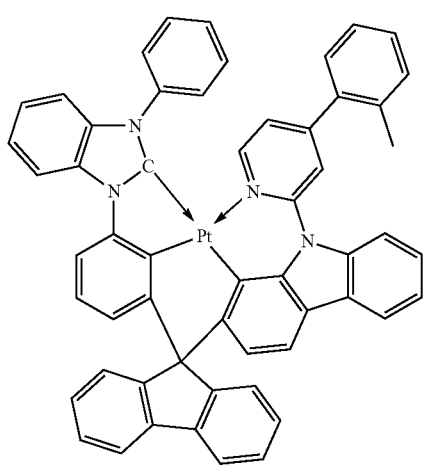
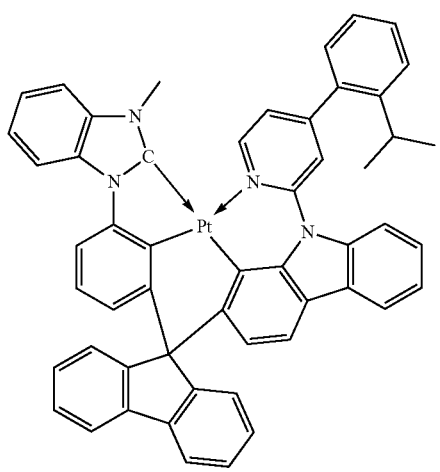
2312
-continued
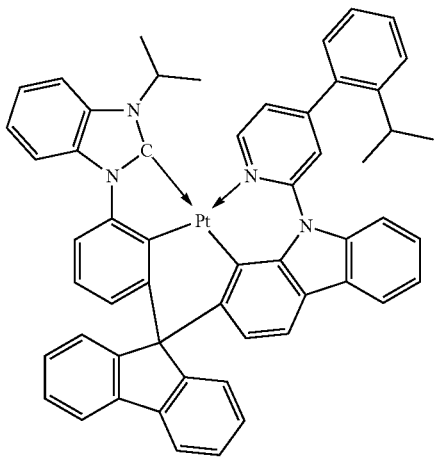
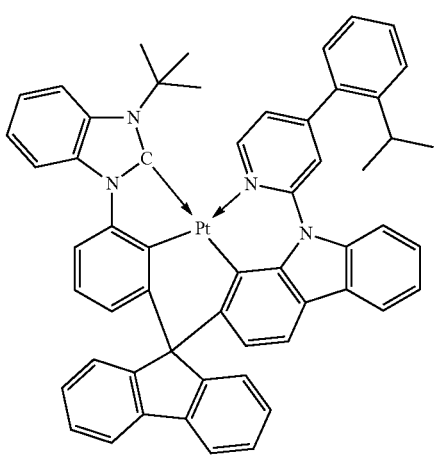
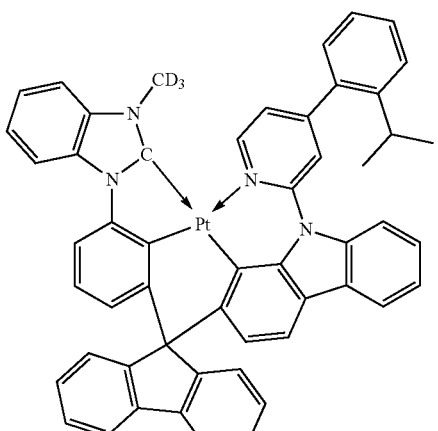

2313
-continued
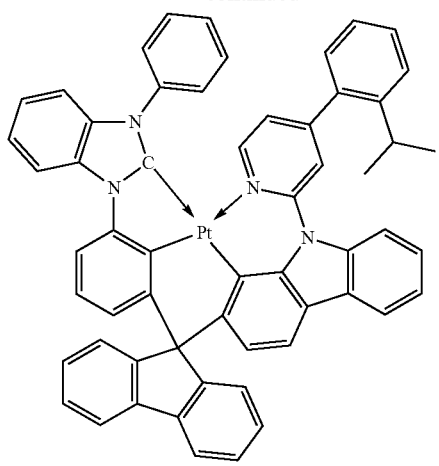
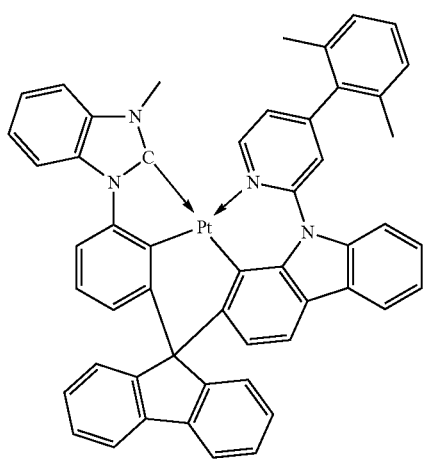
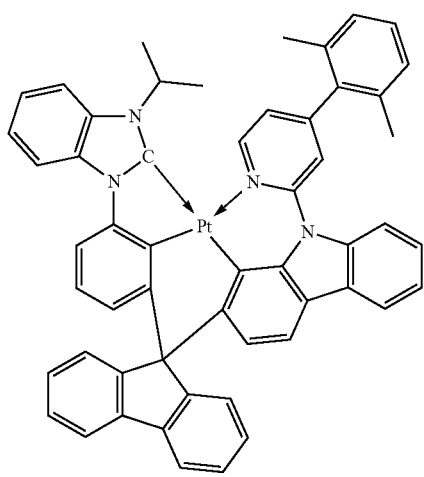
2314
-continued
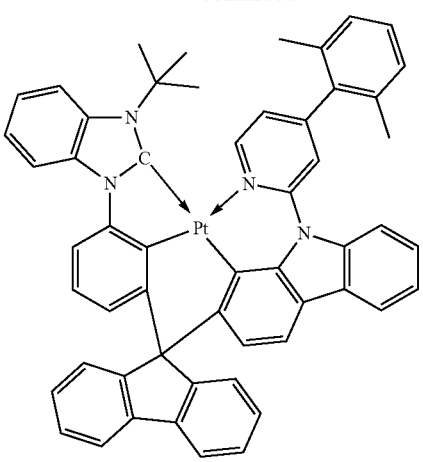
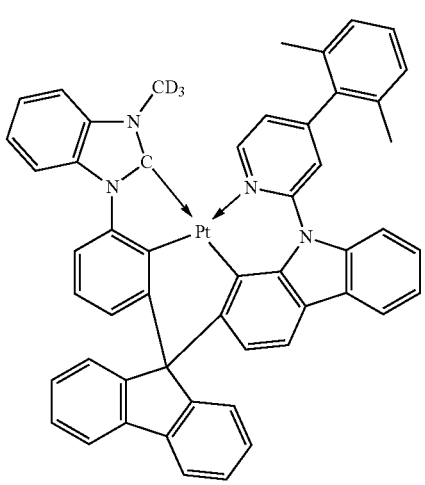
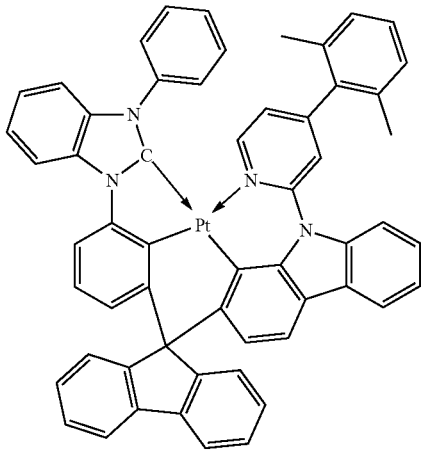

2315
-continued
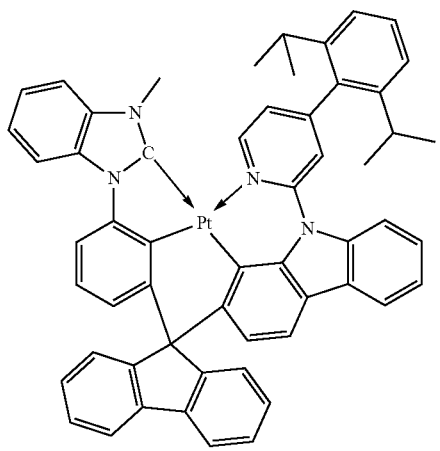
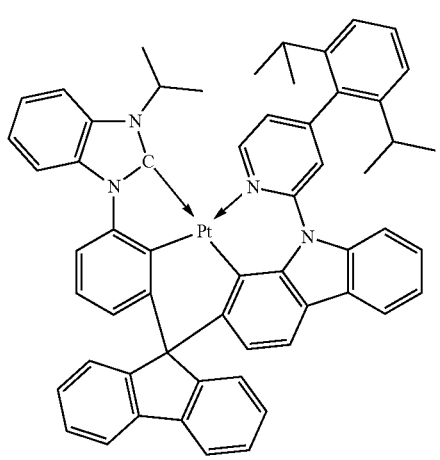
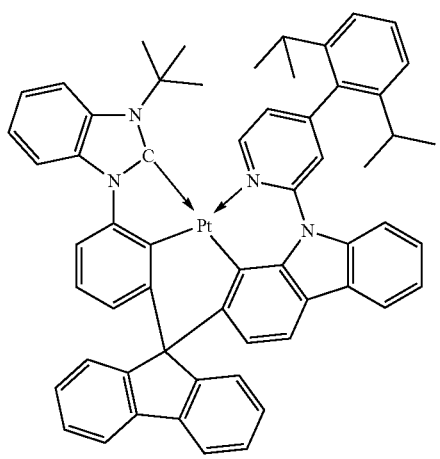
2316
-continued
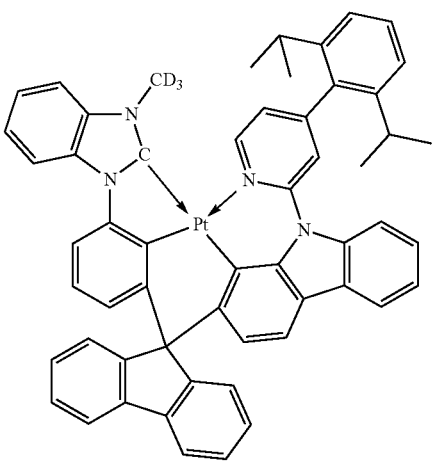
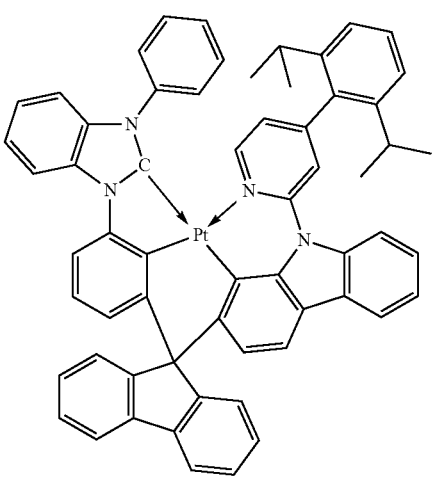
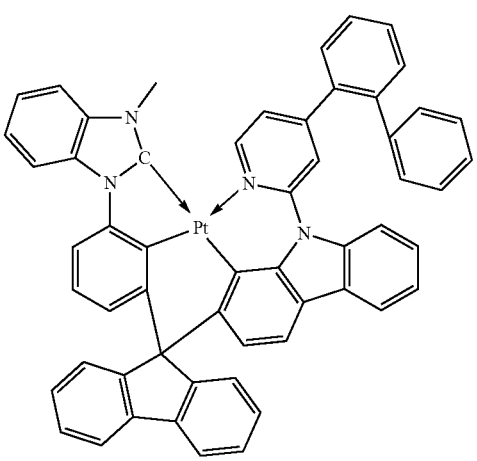

2317
-continued
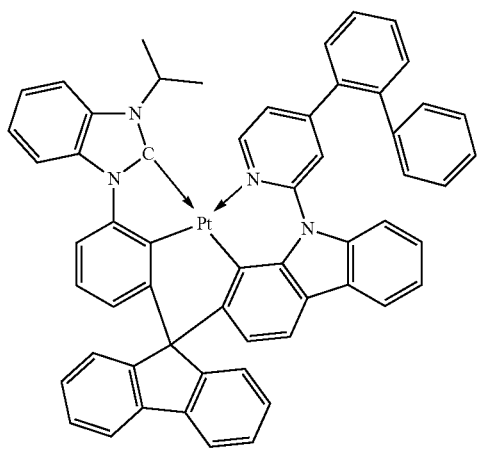
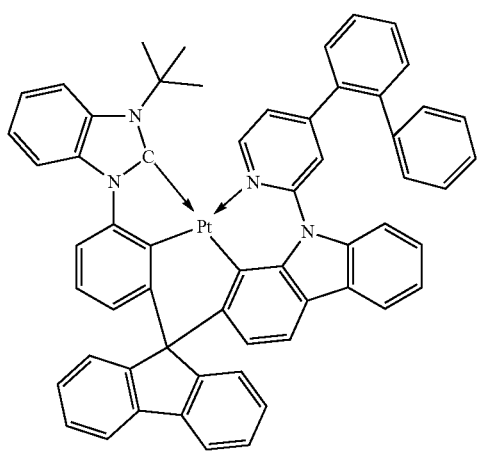
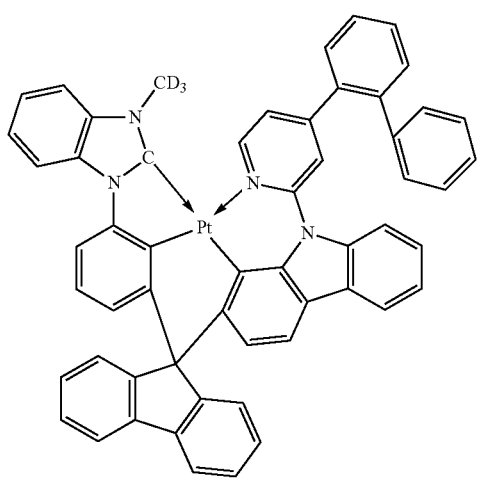
2318
-continued
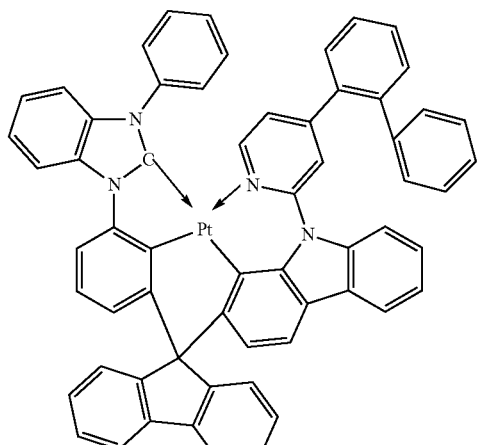
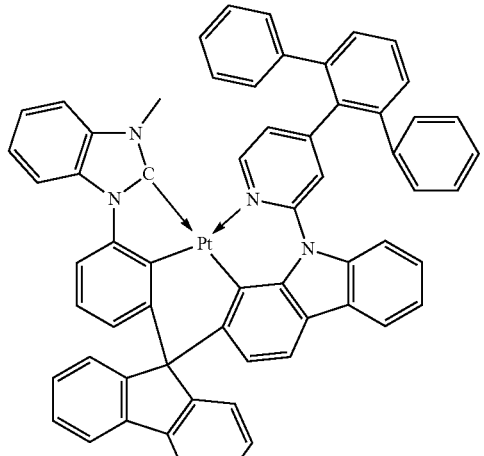
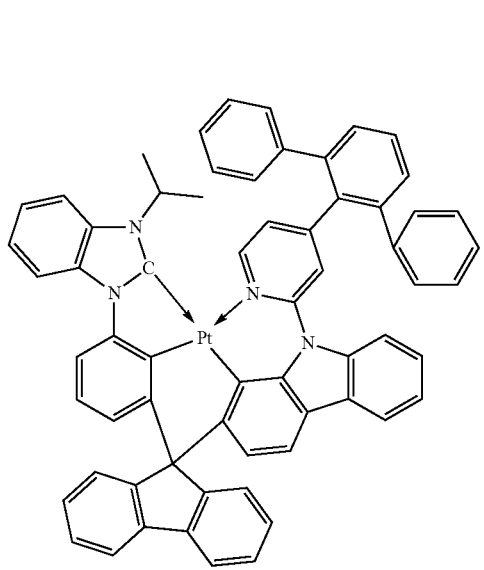

2319
-continued
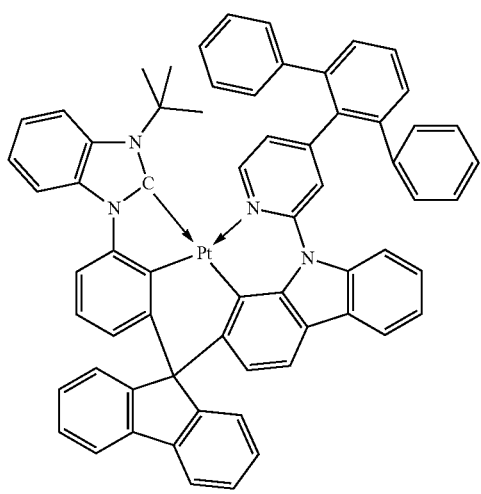
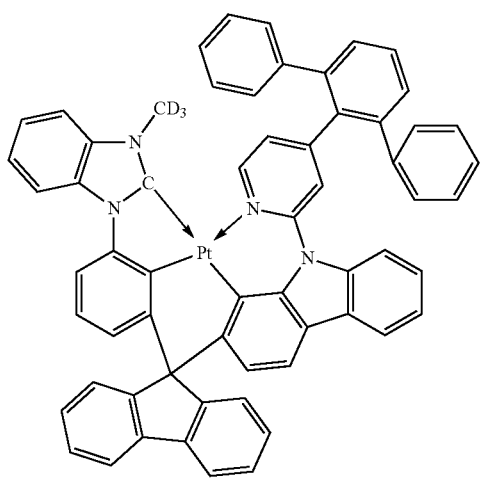
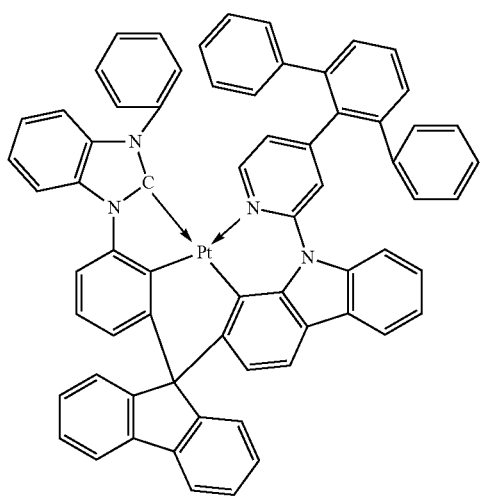
2320
-continued
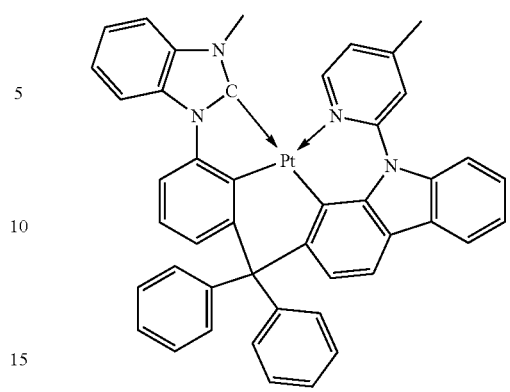
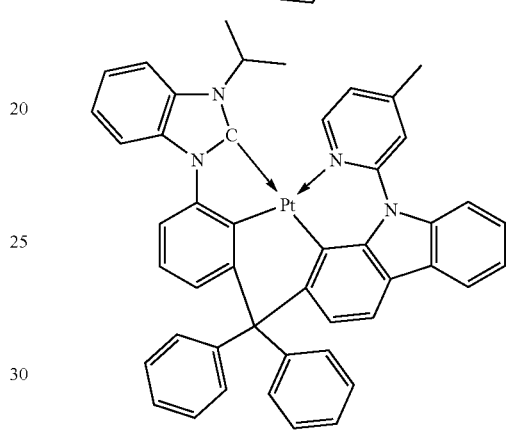
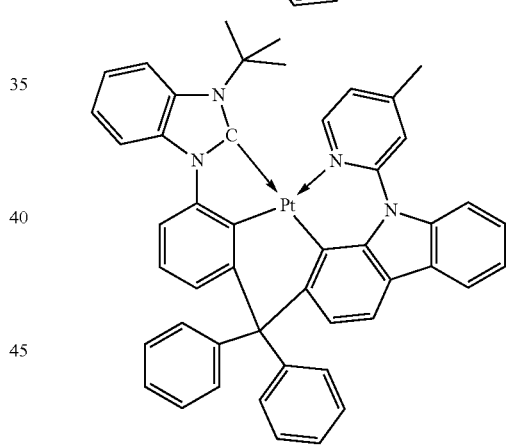
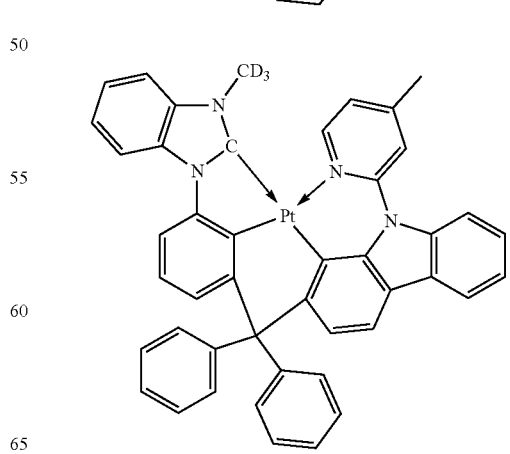

2321
-continued
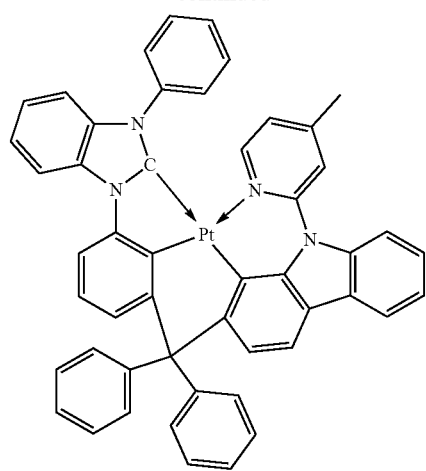
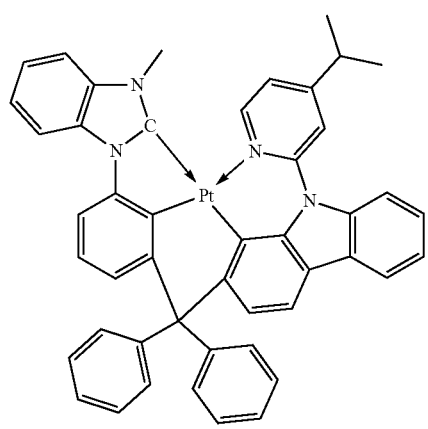
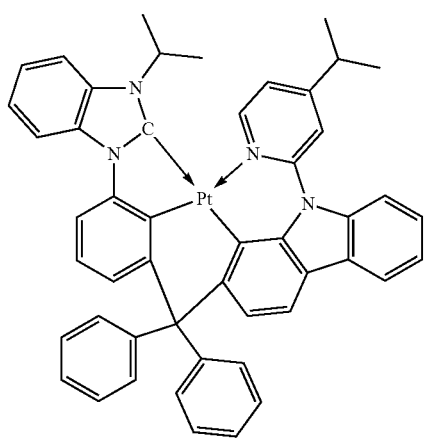
2322
-continued
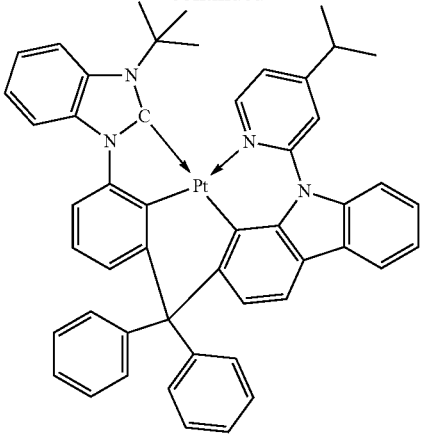
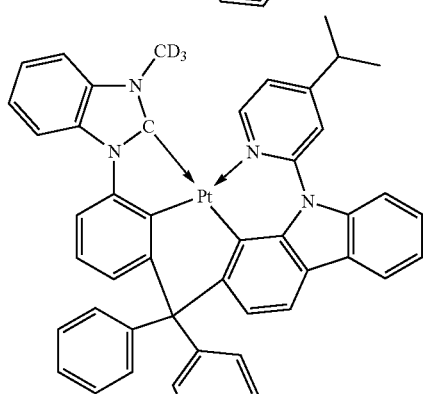
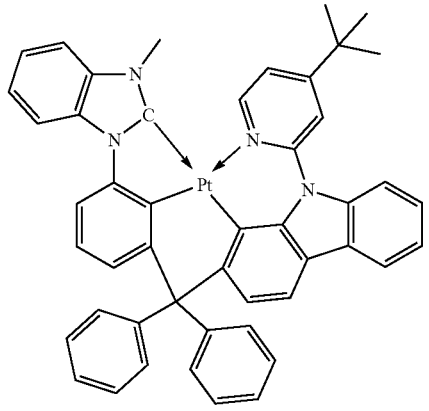

2323
-continued
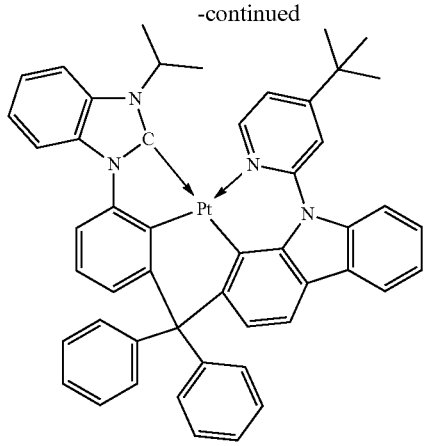
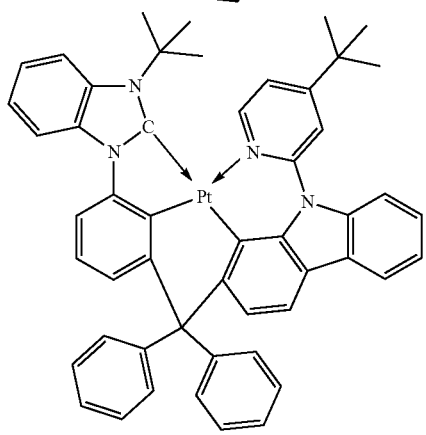
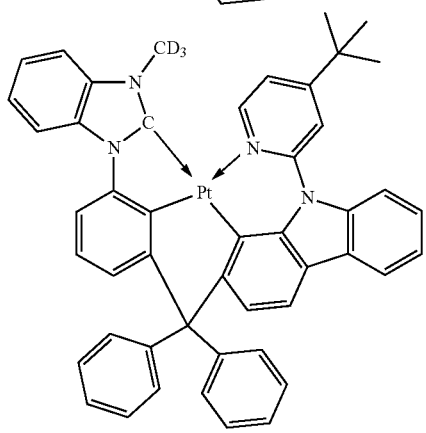
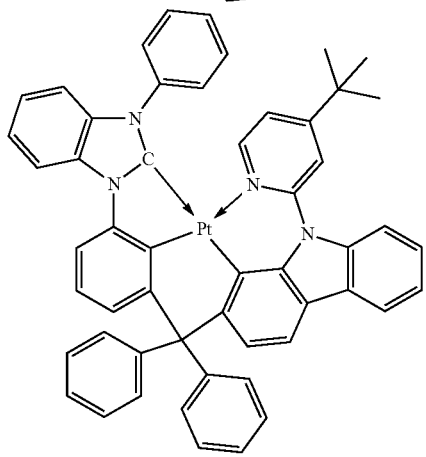
2324
-continued
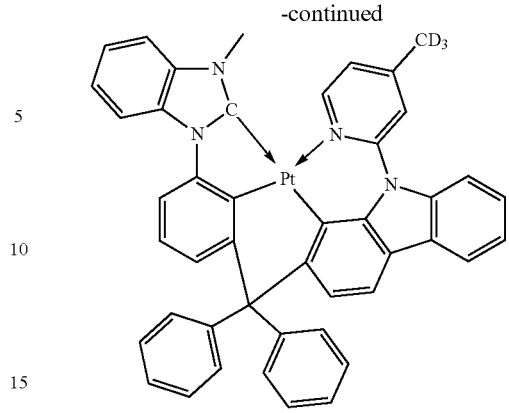
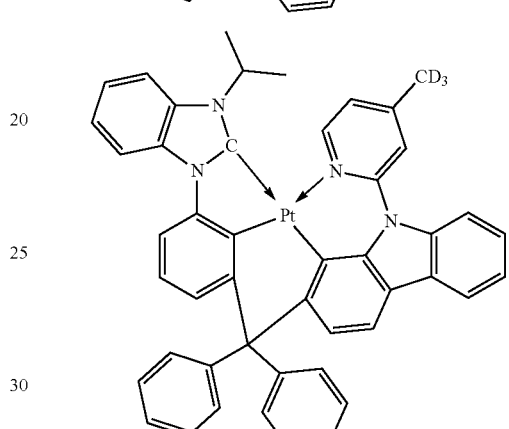
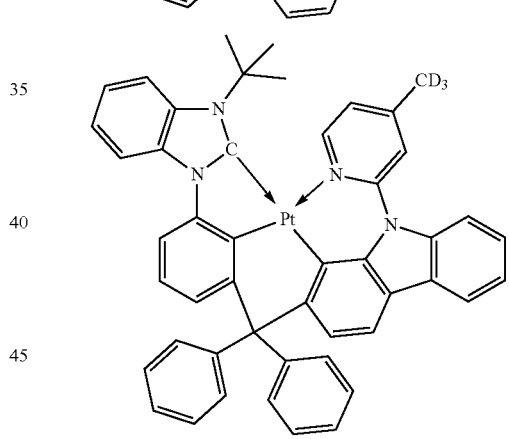
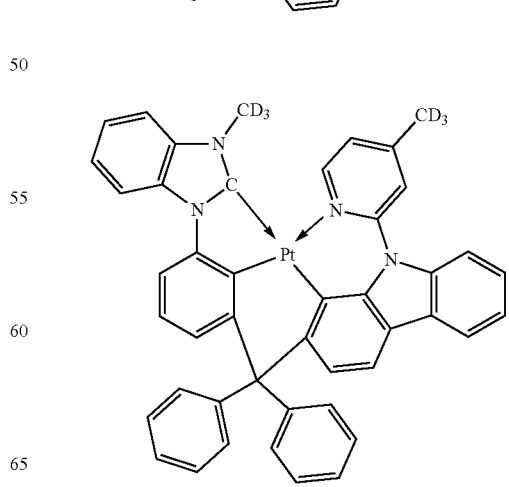

2325
-continued
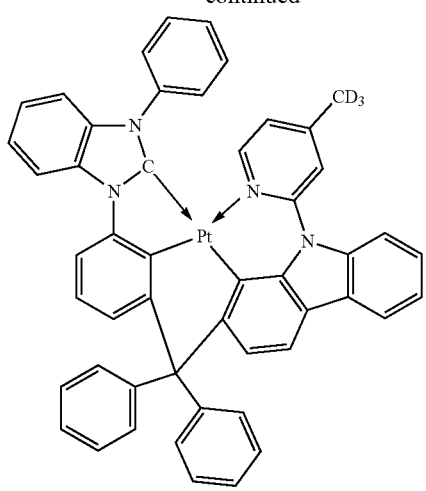
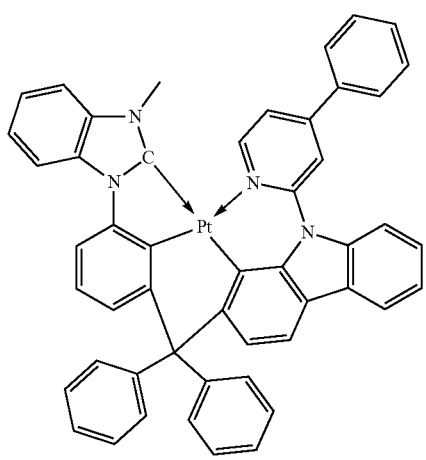
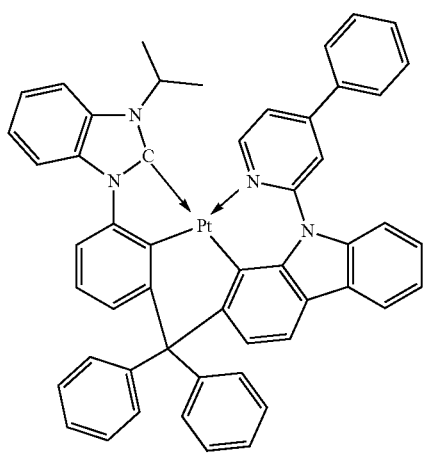
2326
-continued
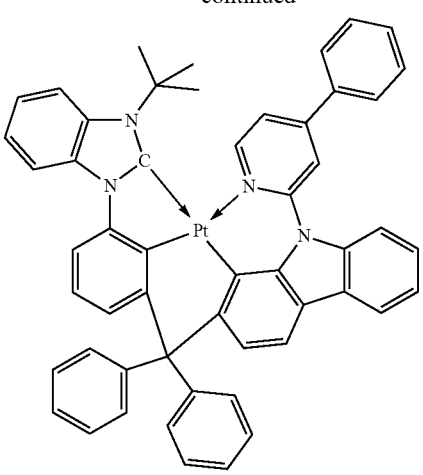
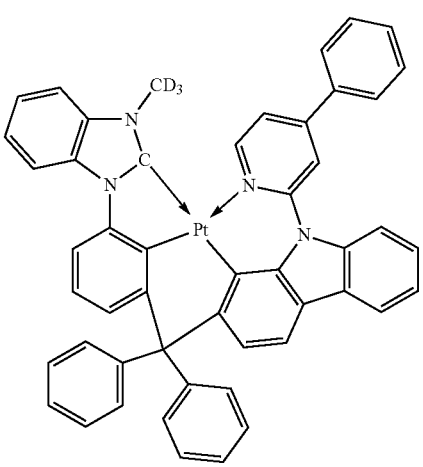
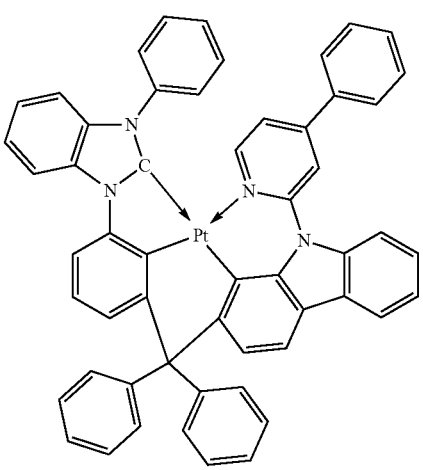

2327
-continued
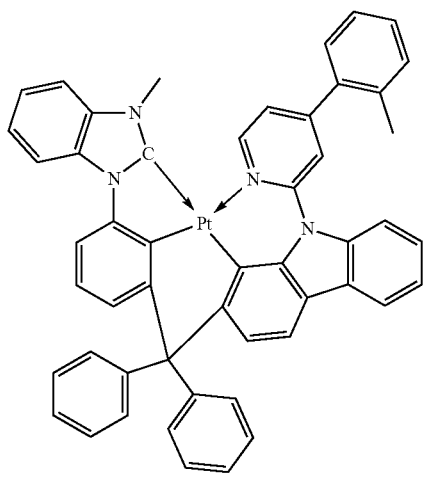
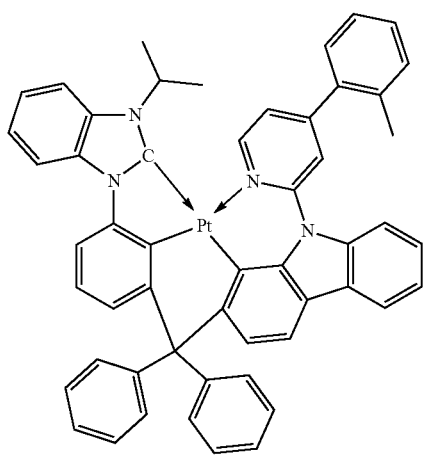
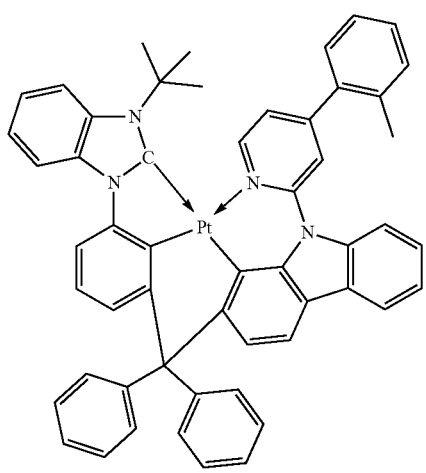
2328
-continued
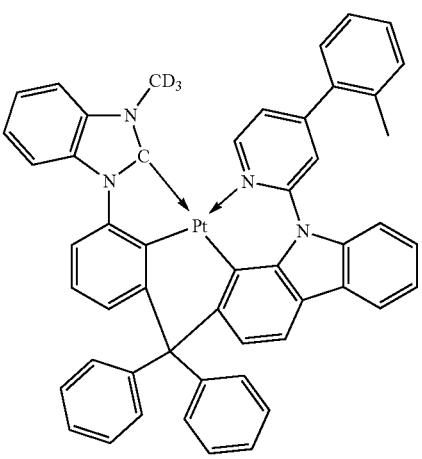
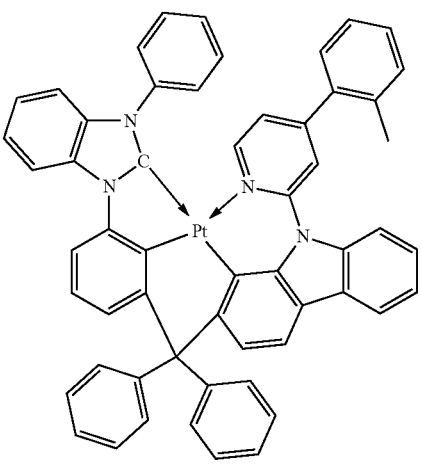
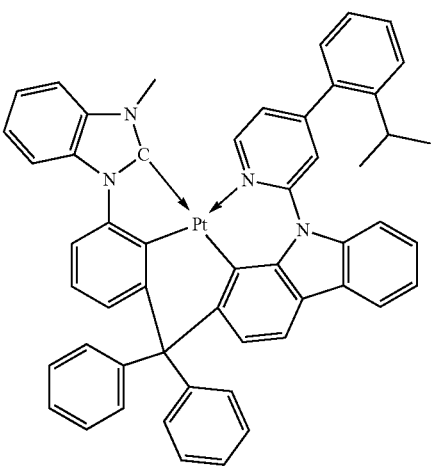

2329
-continued
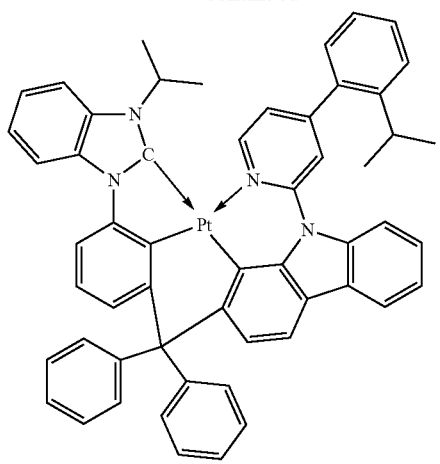
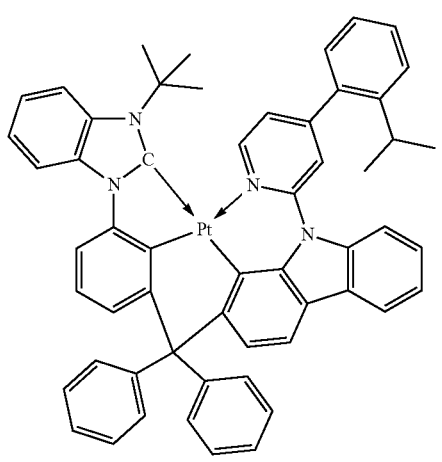
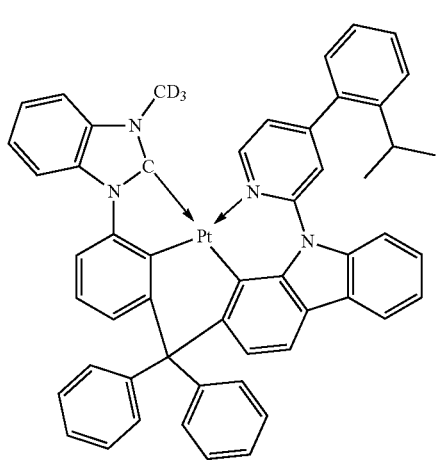
2330
-continued
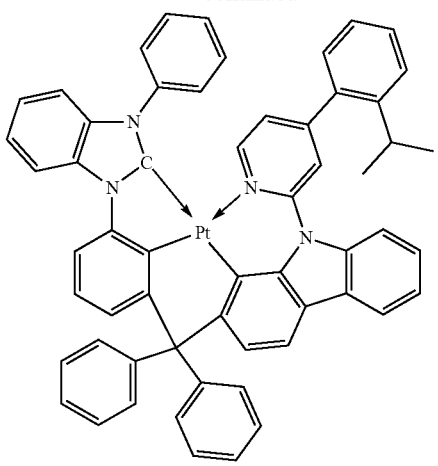
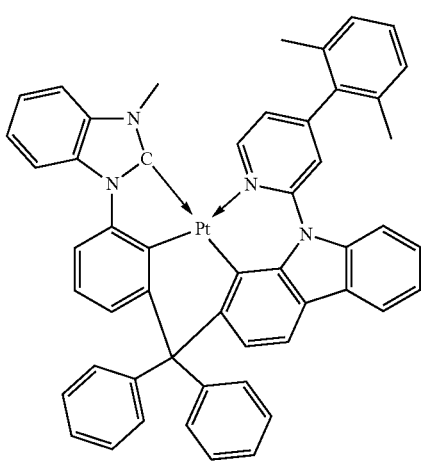
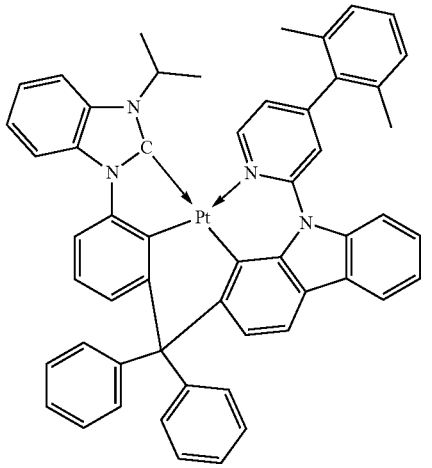

2331
-continued
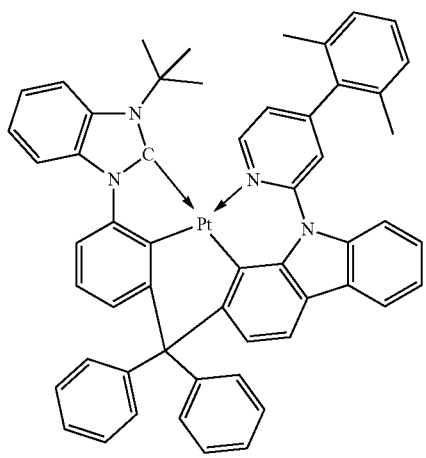
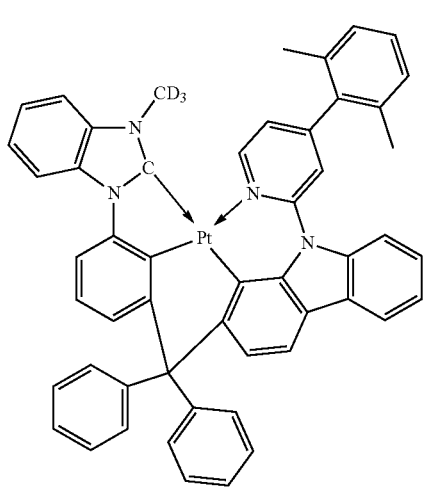
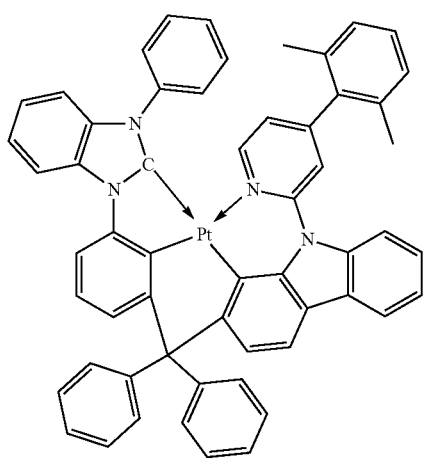
2332
-continued
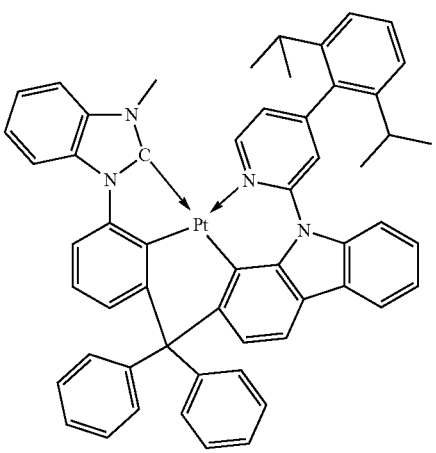
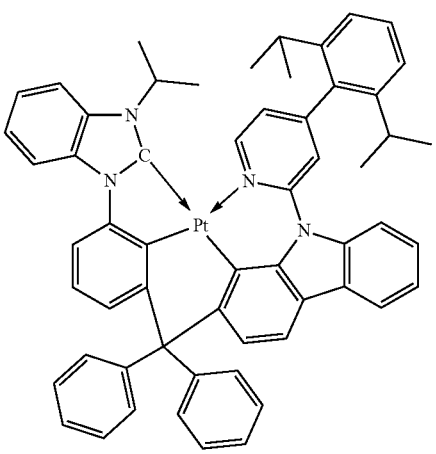
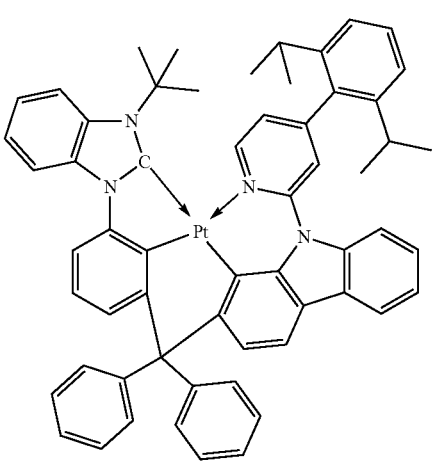

2333
-continued
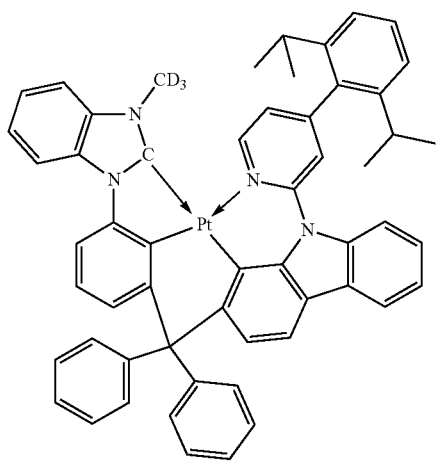
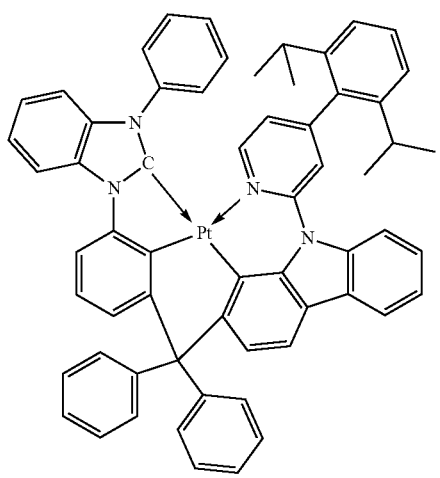
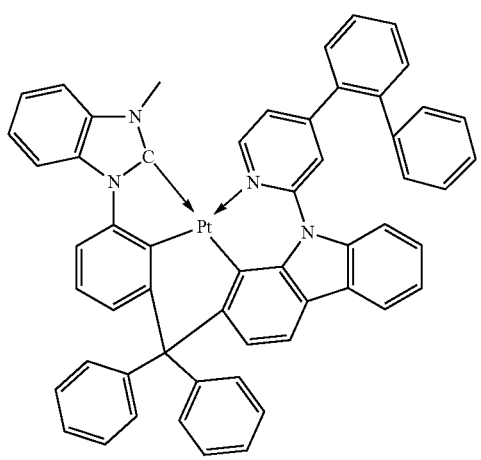
2334
-continued
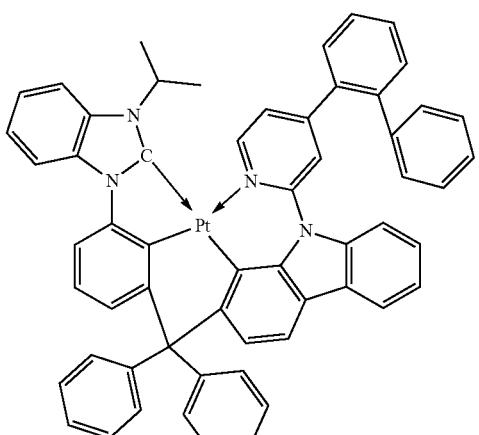
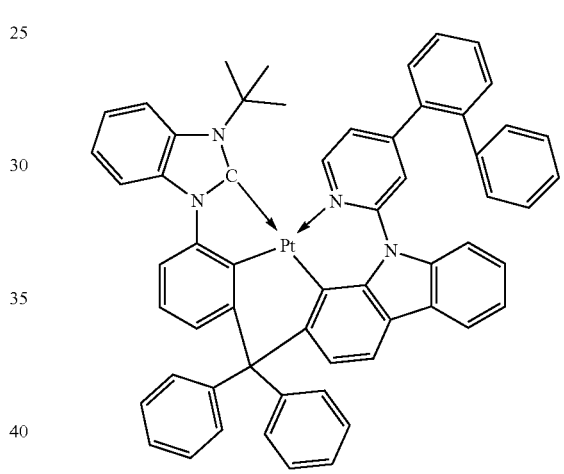
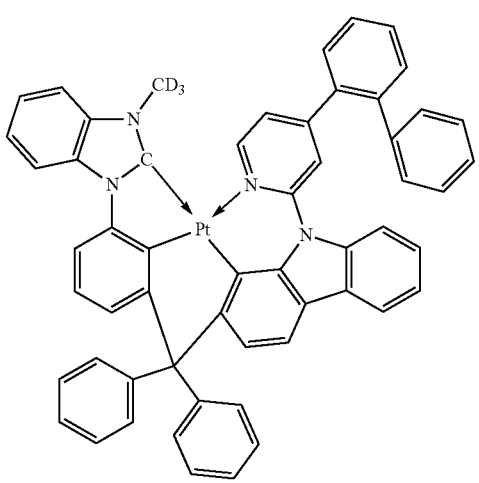

2335
-continued
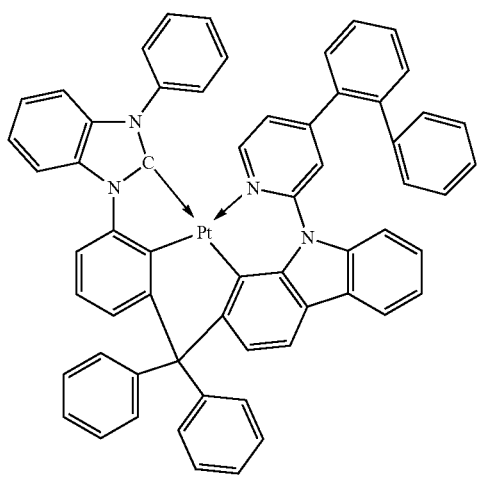
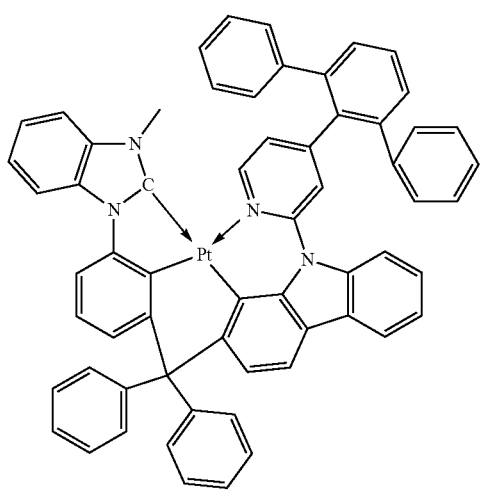
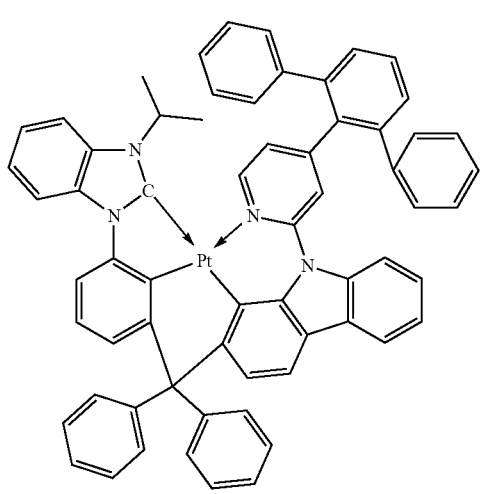
2336
-continued
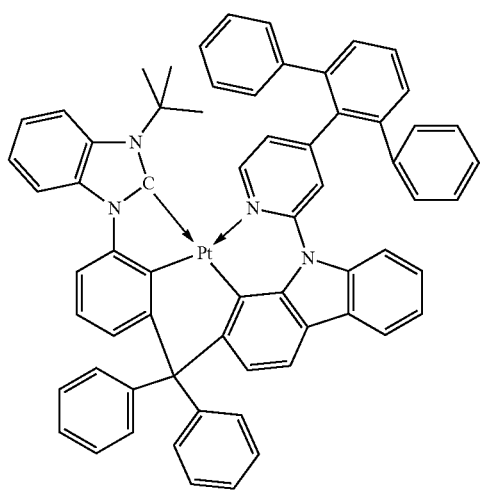
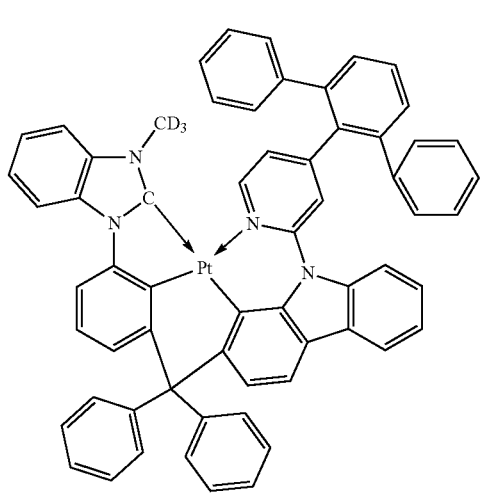
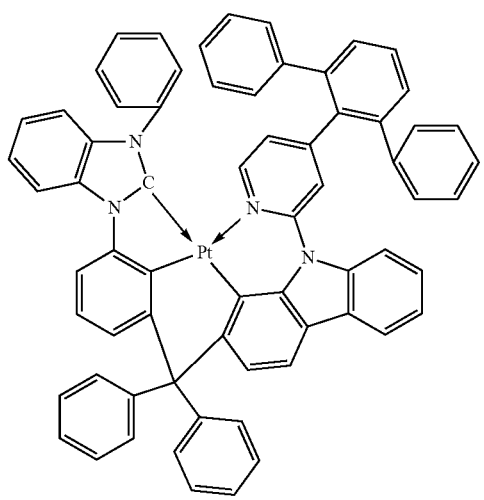

2337
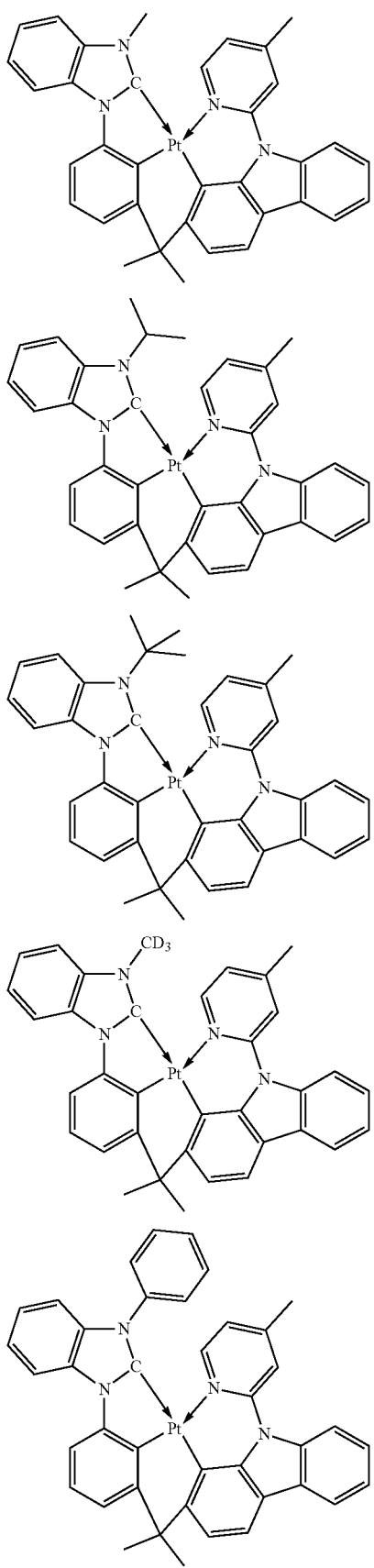
2338
-continued
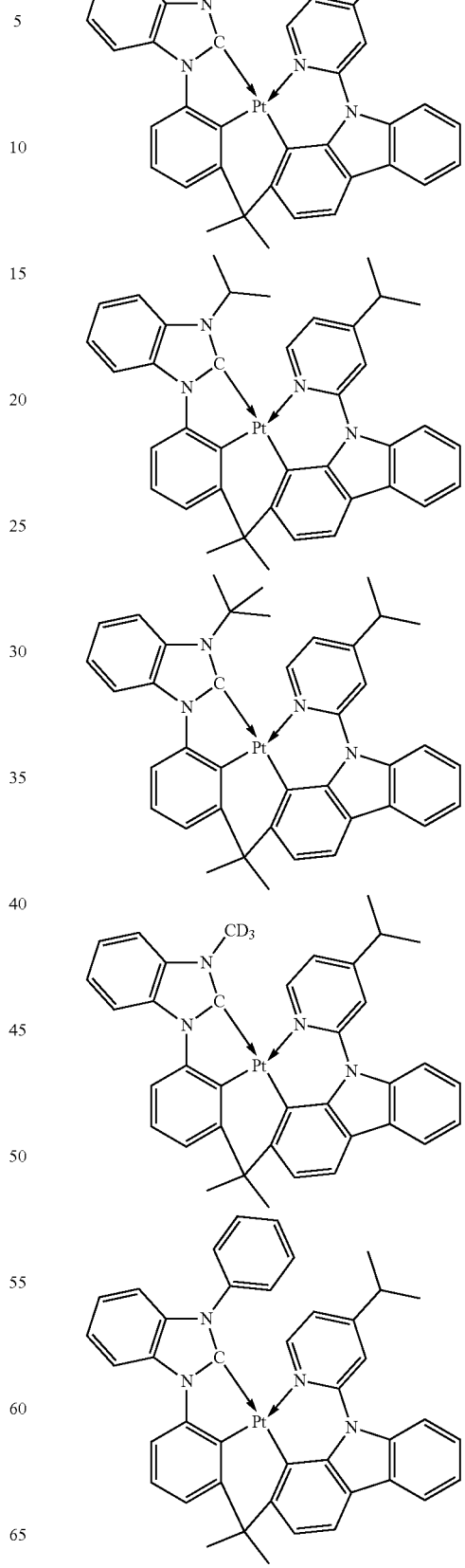

2339
-continued
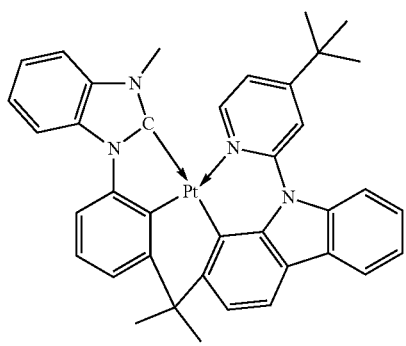
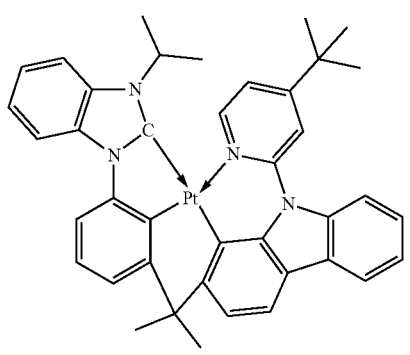
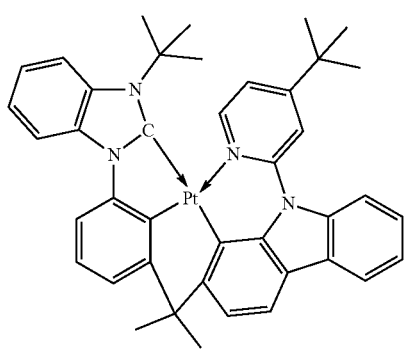
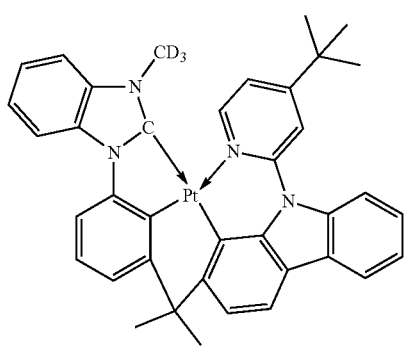
2340
-continued
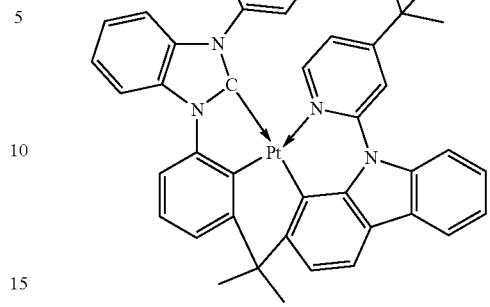
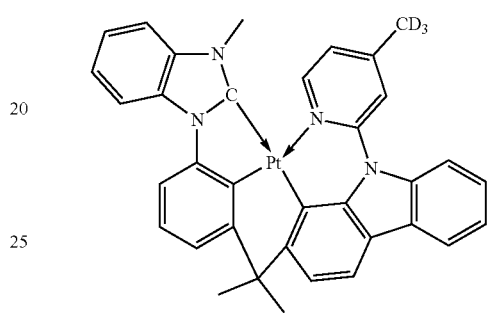
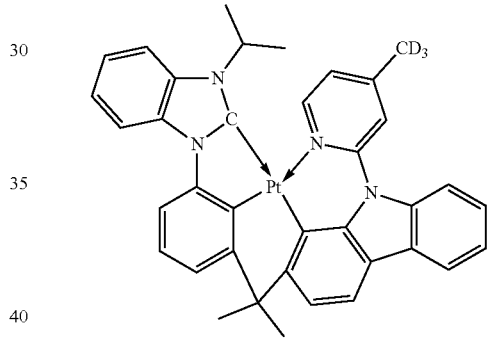
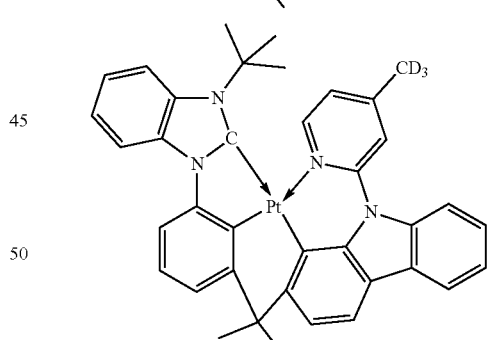
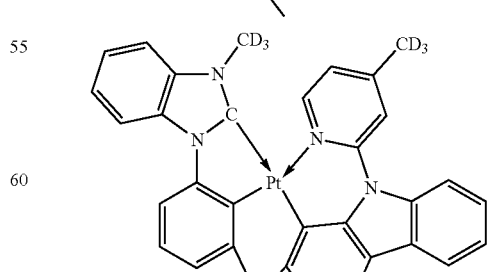

2341
-continued
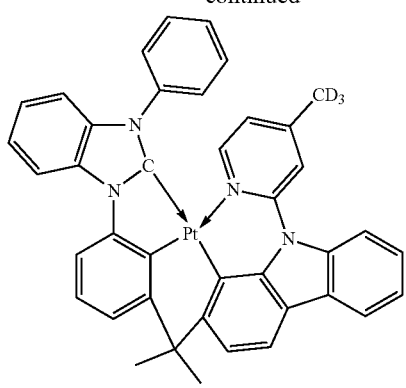
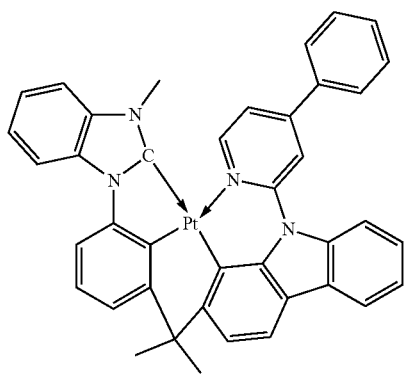
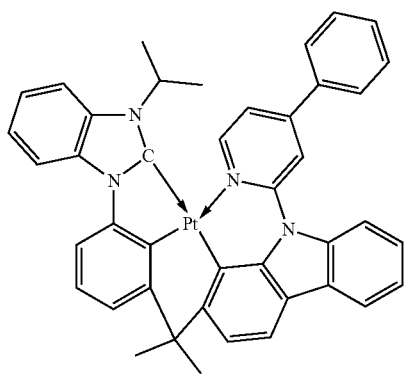
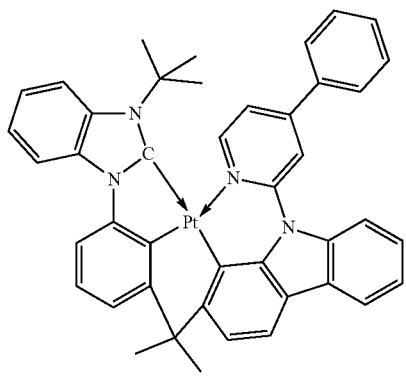
2342
-continued
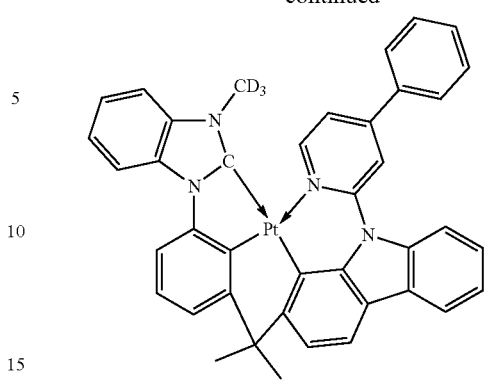
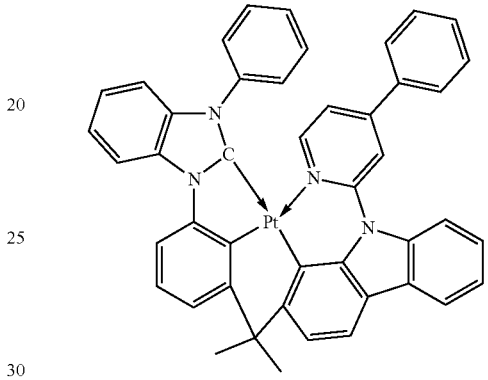
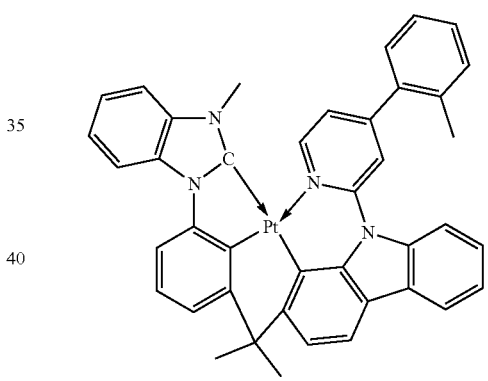
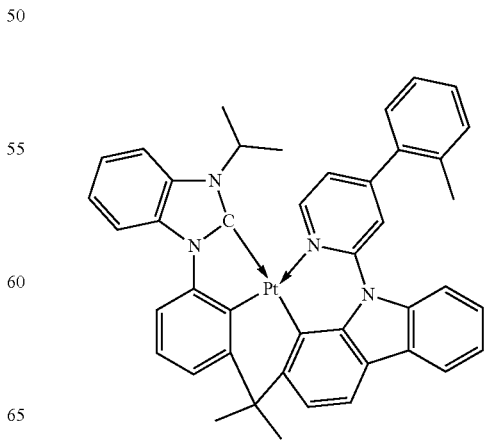

2343
-continued
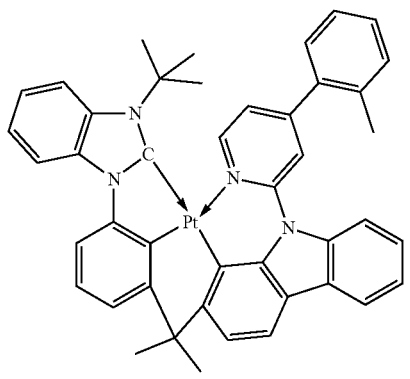
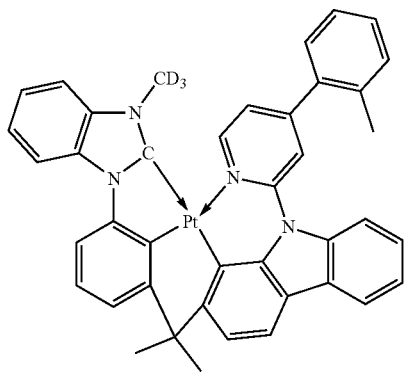
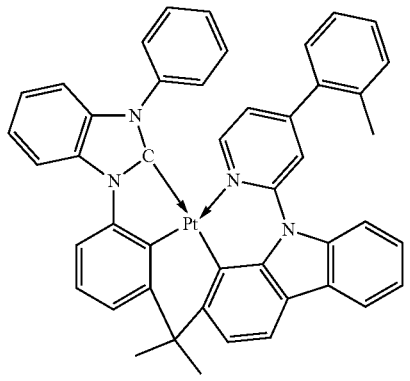
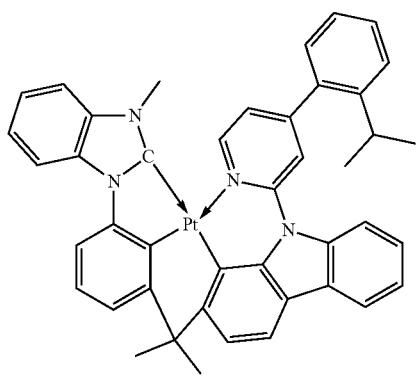
2344
-continued

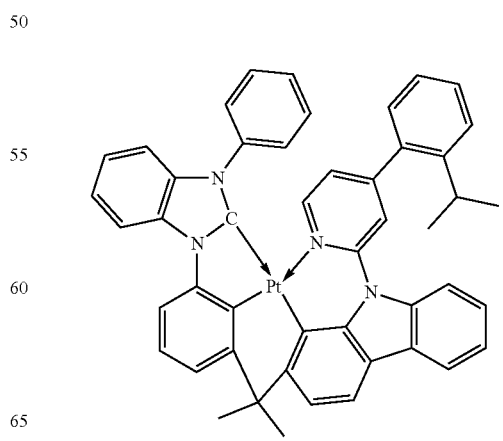

2345
-continued
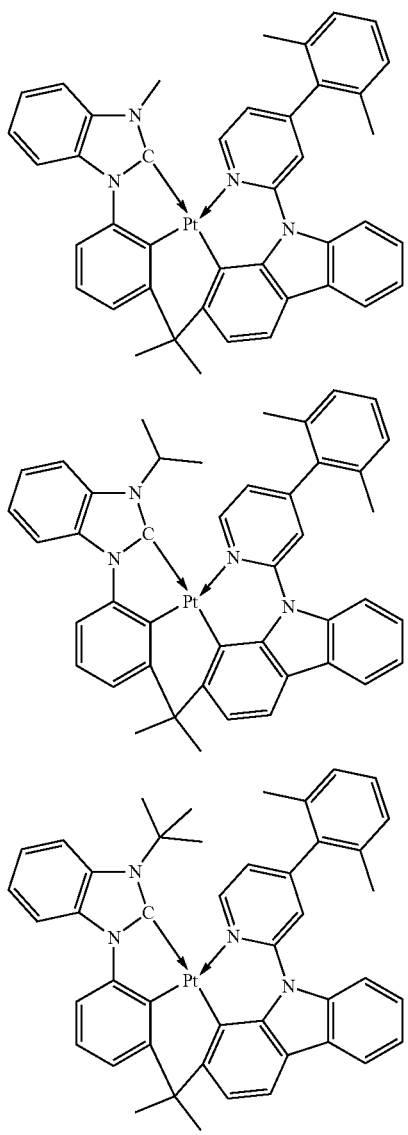
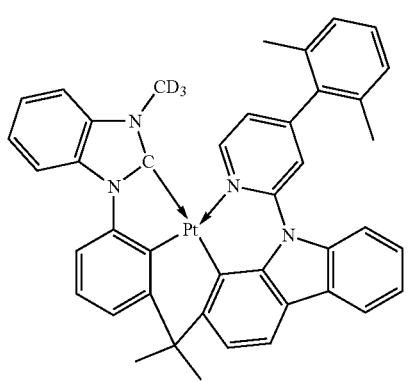
2346
-continued
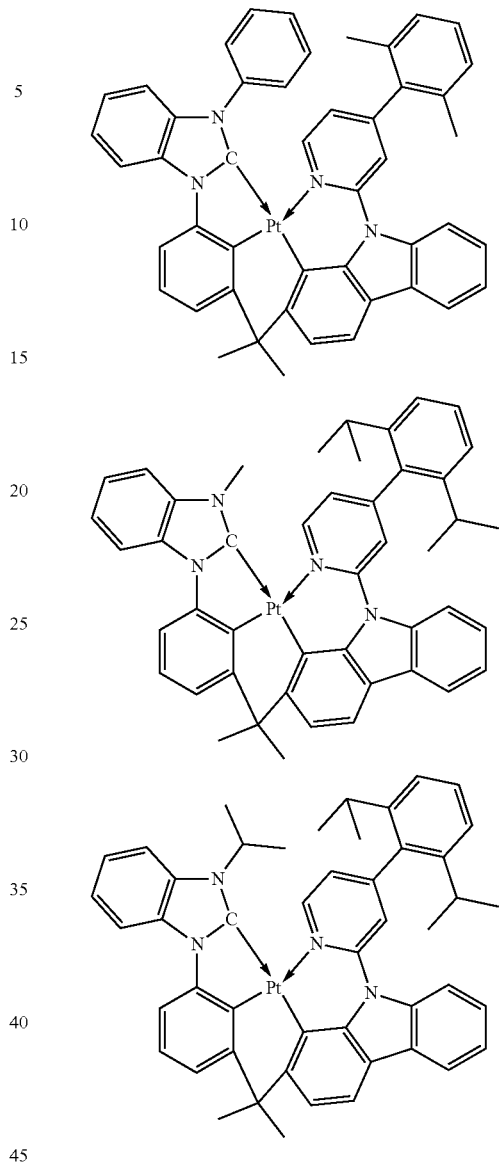
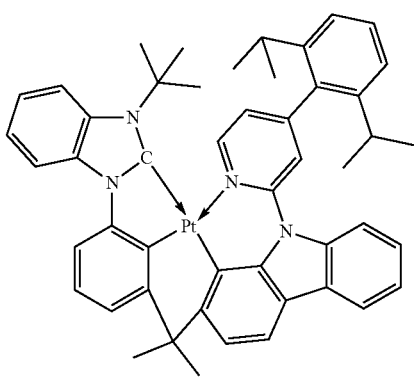

2347
-continued
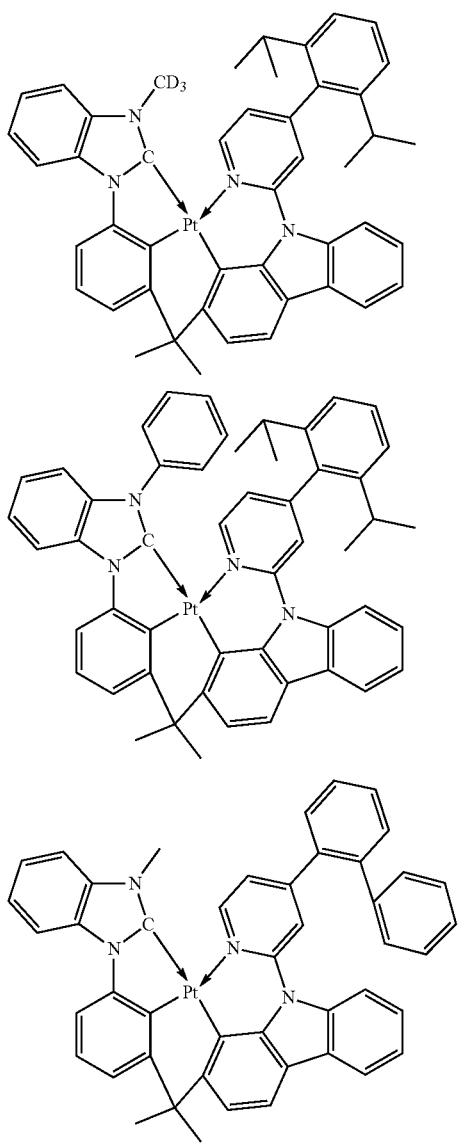
2348
-continued
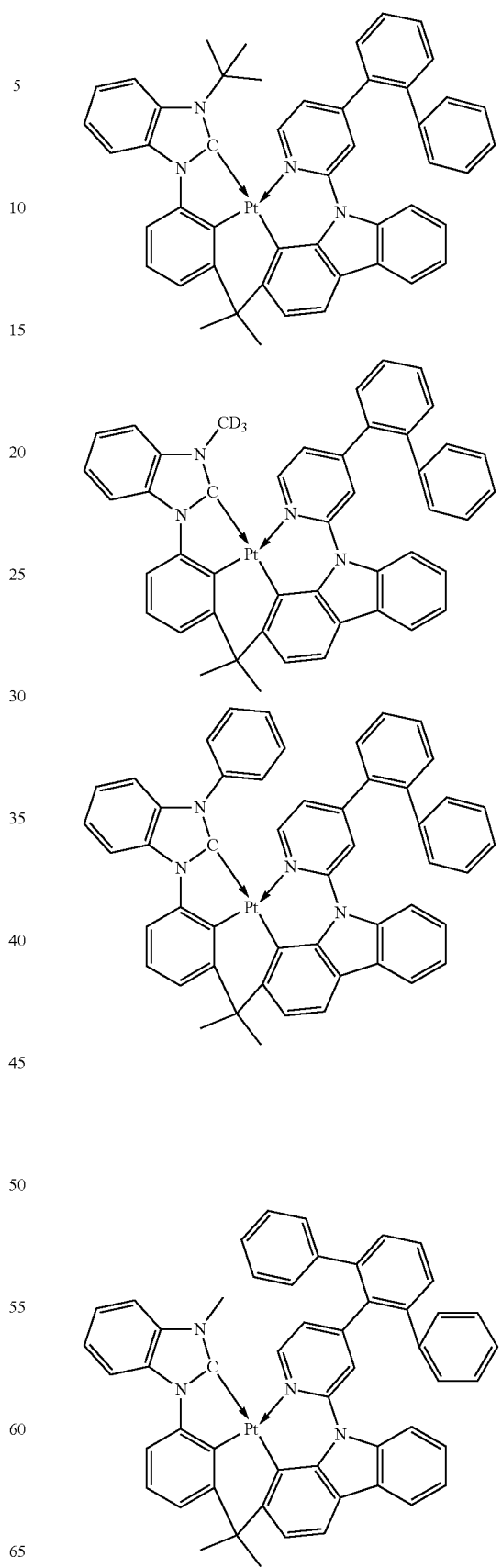

2349
-continued
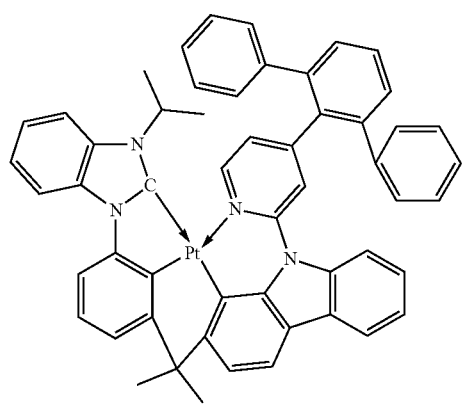
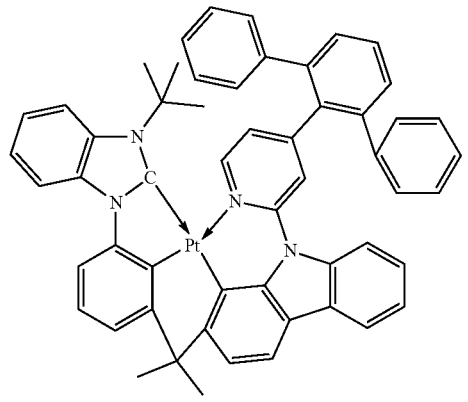
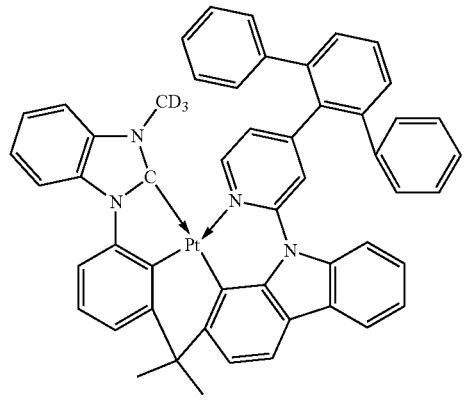
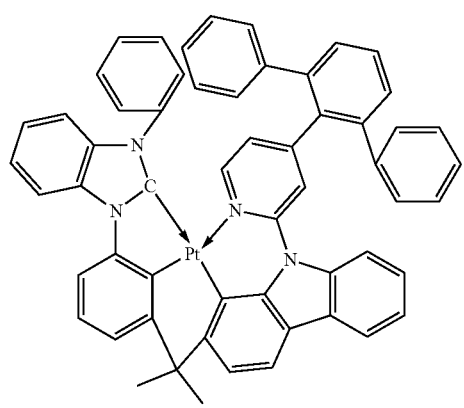
2350
-continued
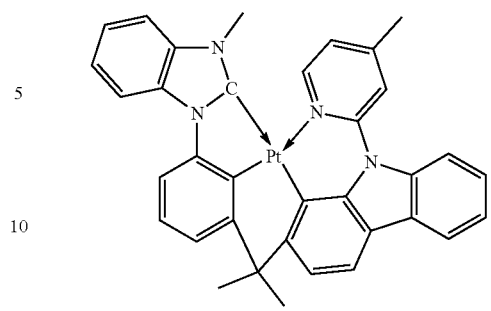
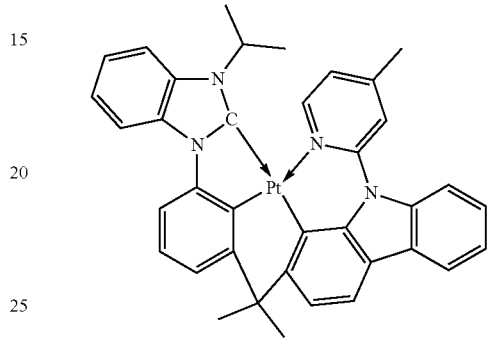
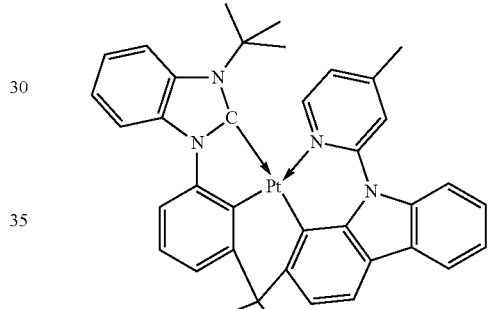
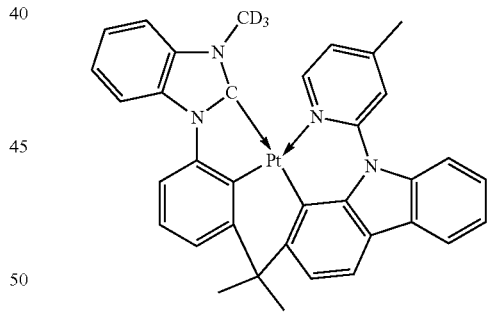
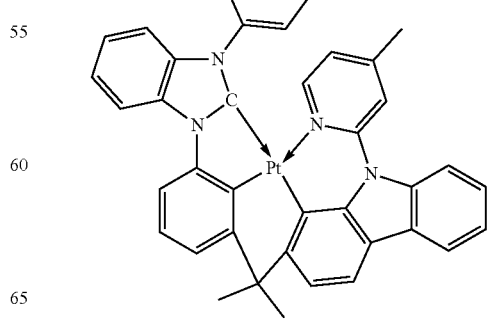

2351
-continued
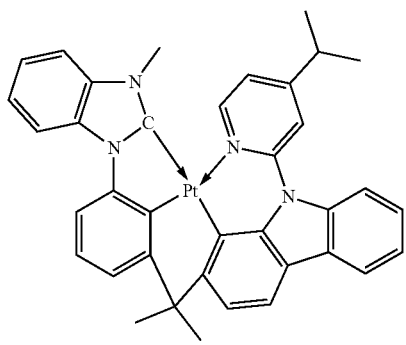
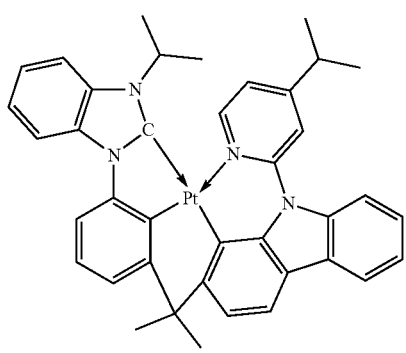
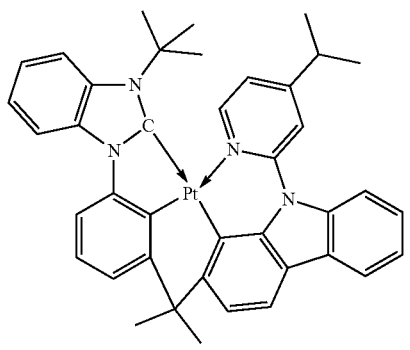
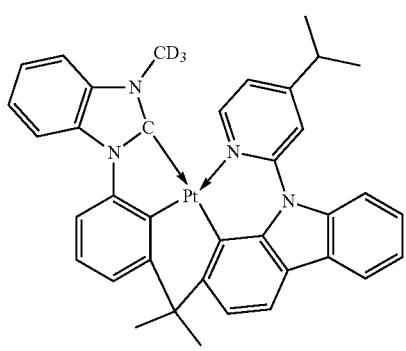
2352
-continued
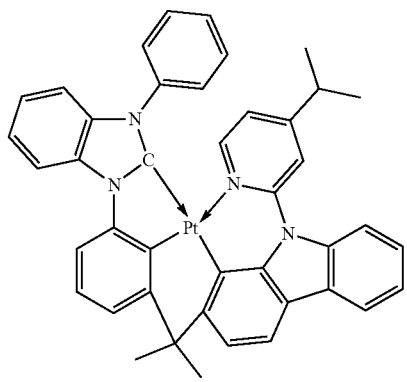
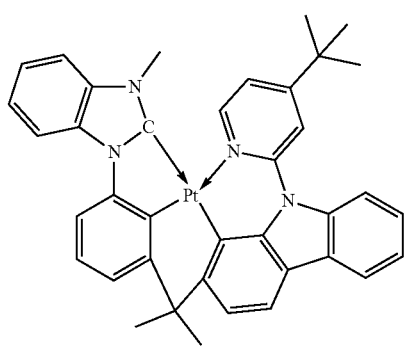
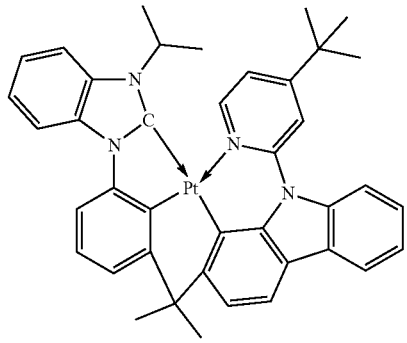
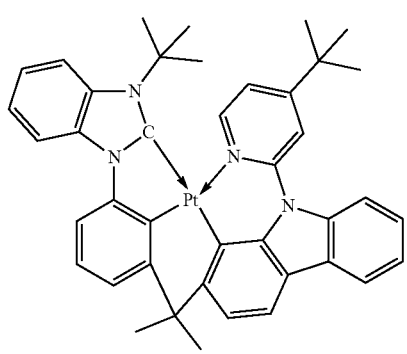

2353
-continued
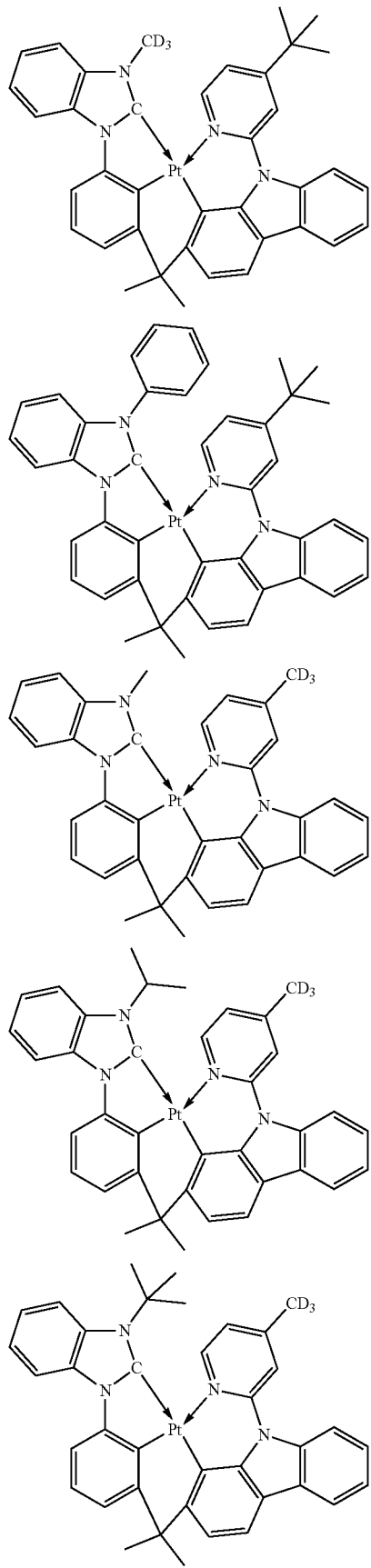
2354
-continued
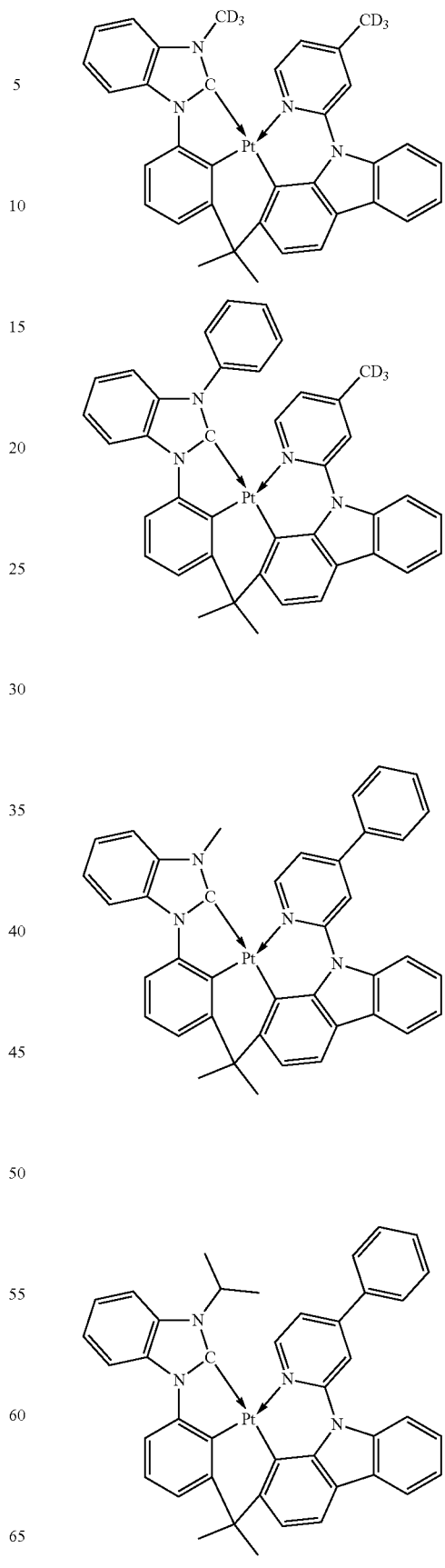

2355
-continued
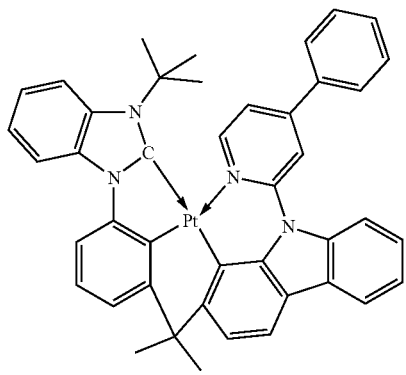
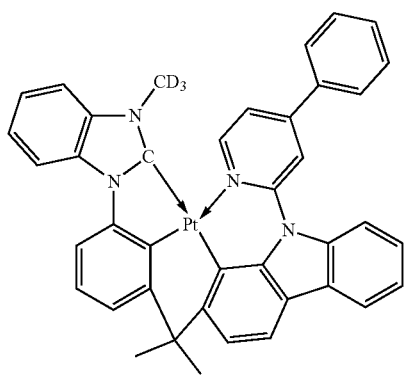
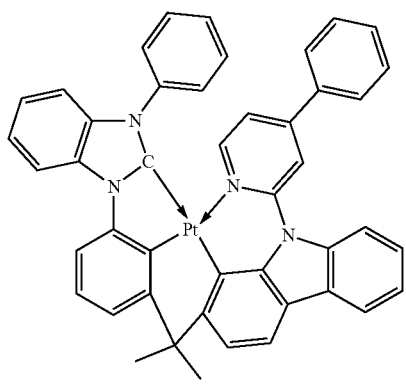
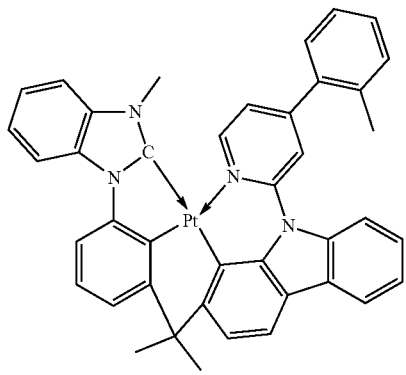
2356
-continued
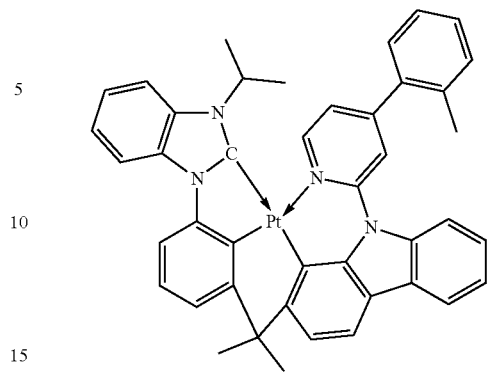
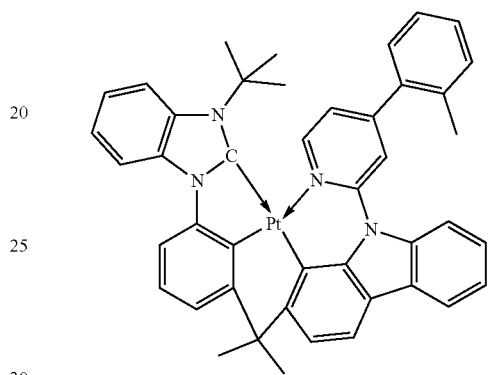
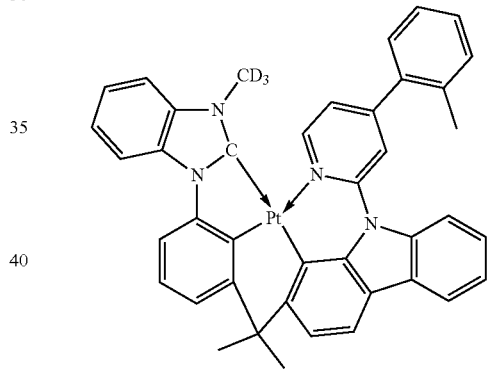
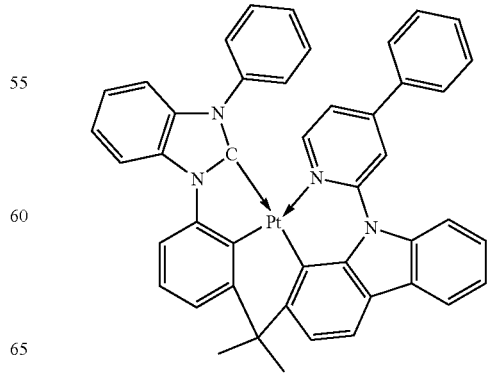

2357
-continued
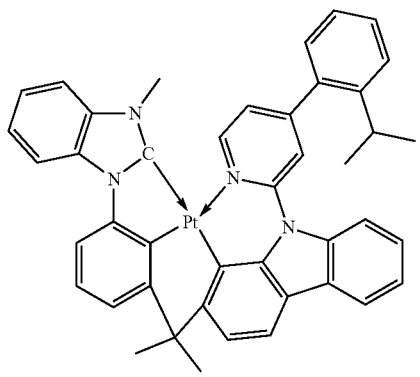
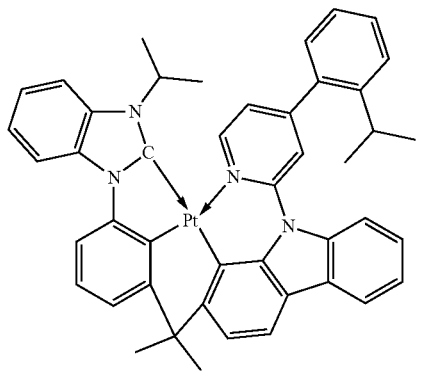
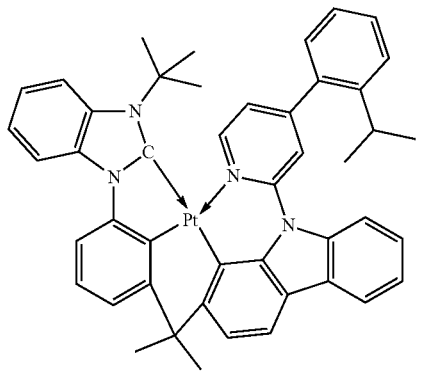
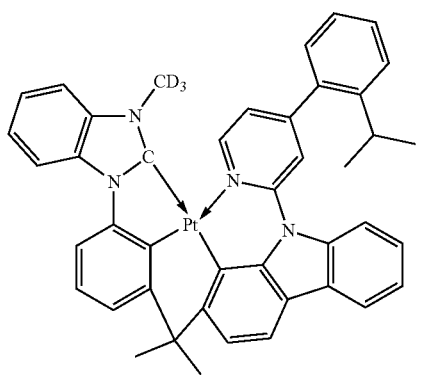
2358
-continued
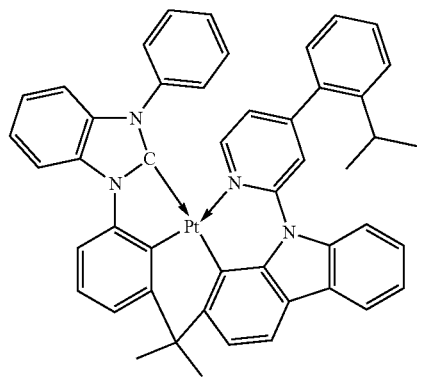
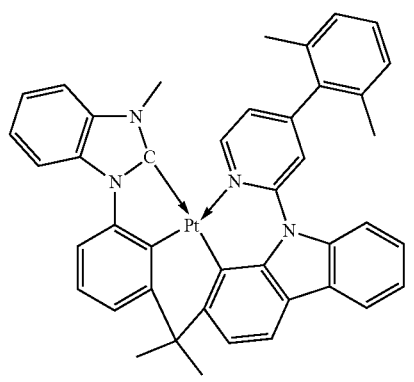
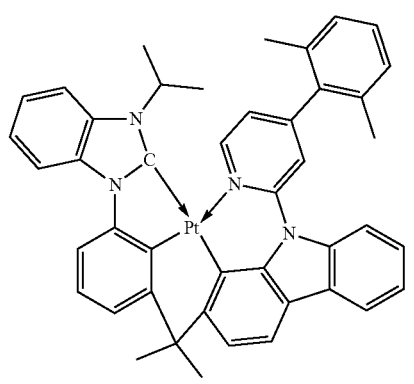
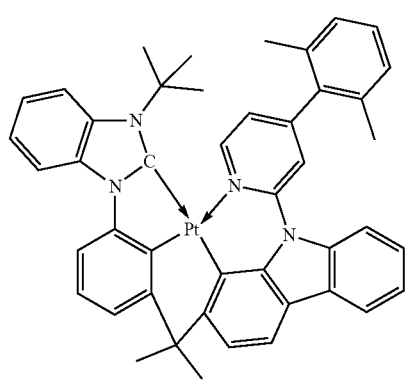

2359
-continued
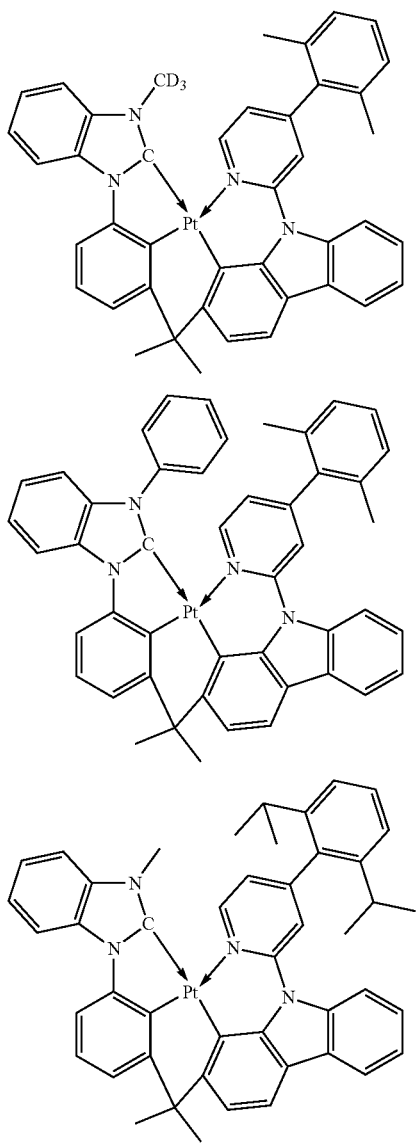
2360
-continued
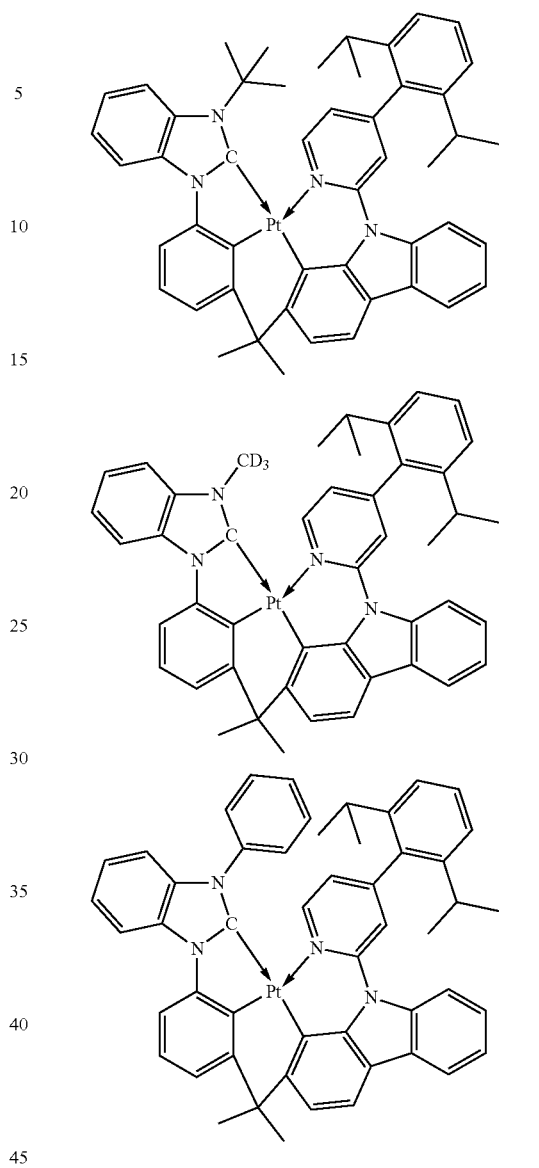
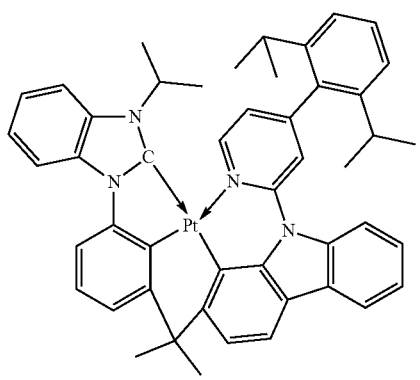
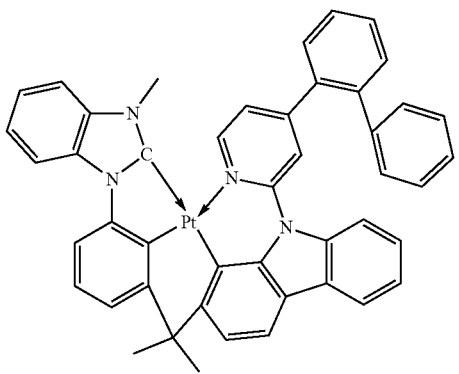

2361
-continued
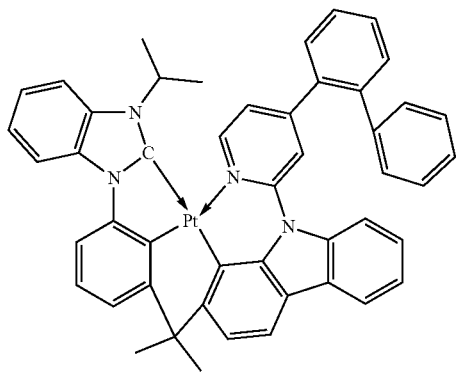
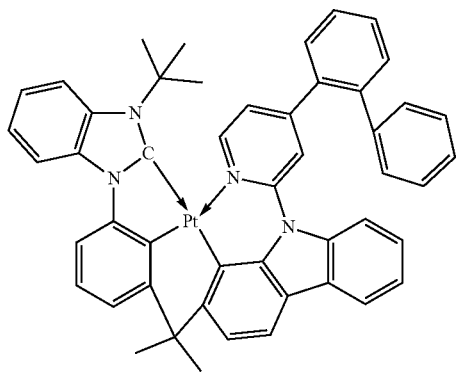
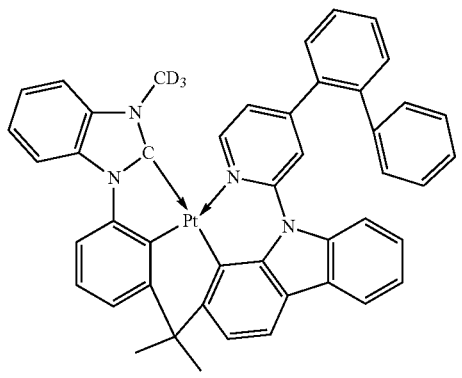
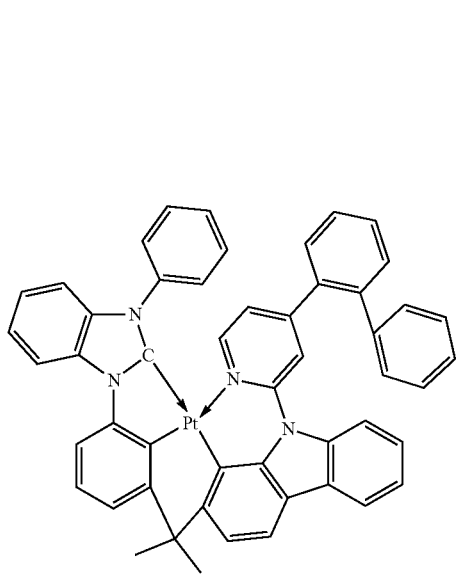
2362
-continued
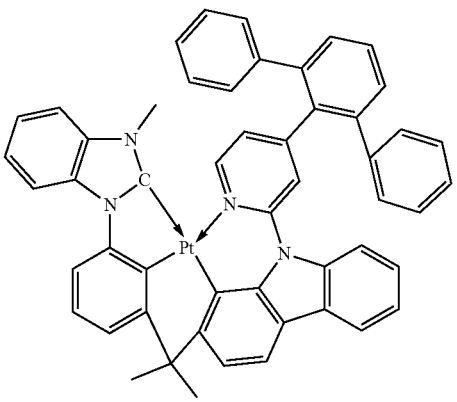
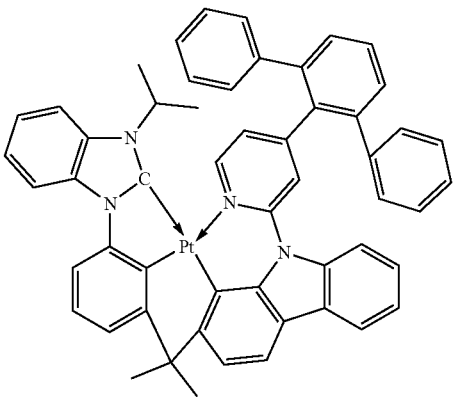
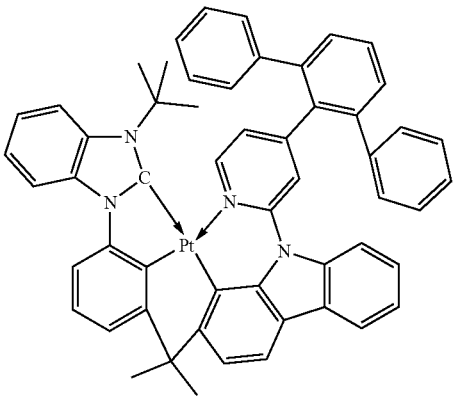
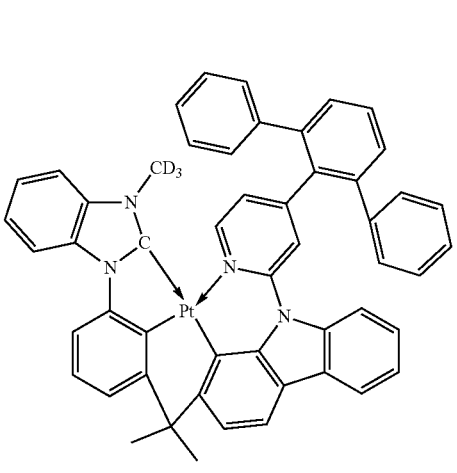

2363
-continued
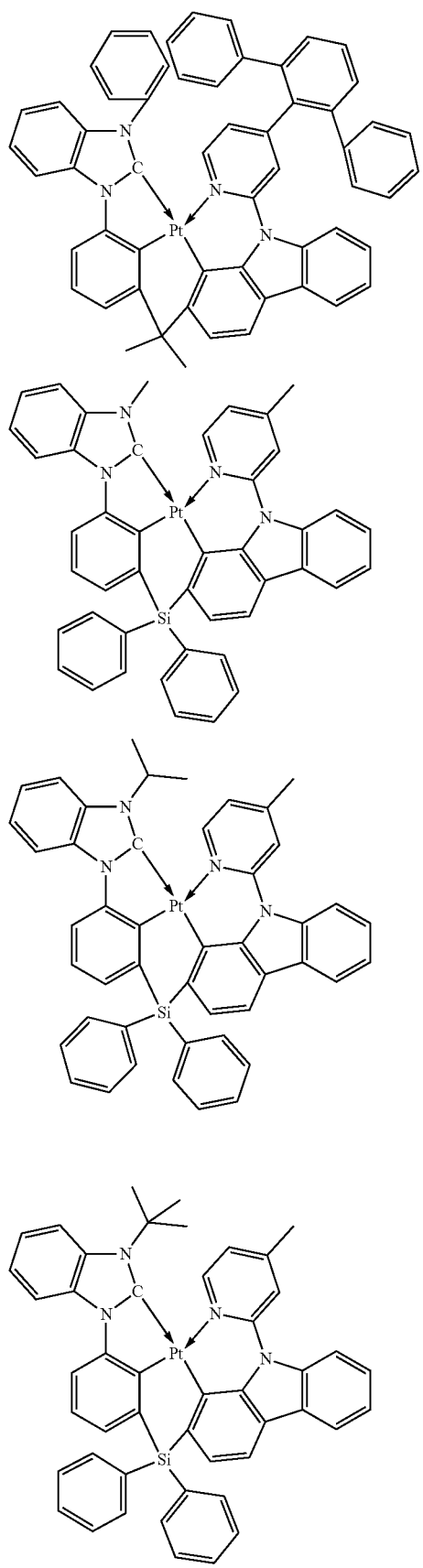
2364
-continued
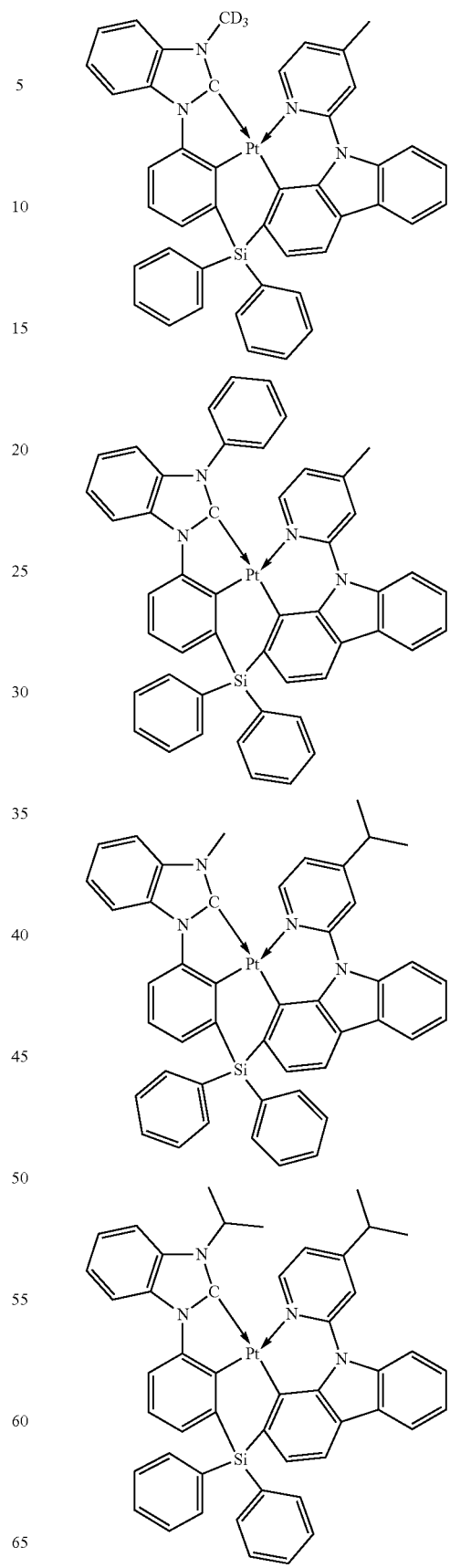

2365
-continued
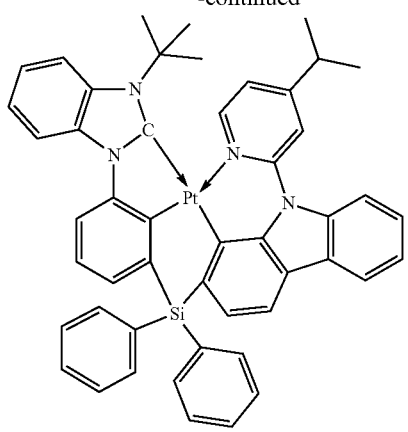
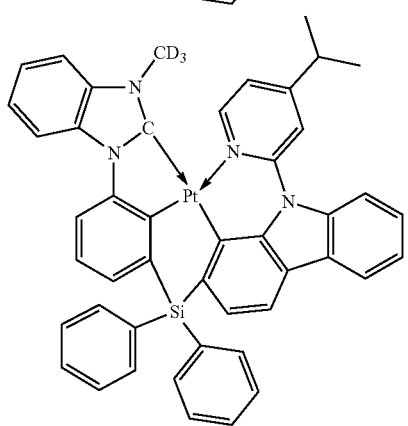
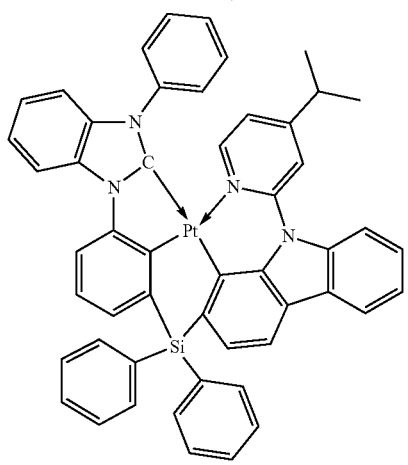
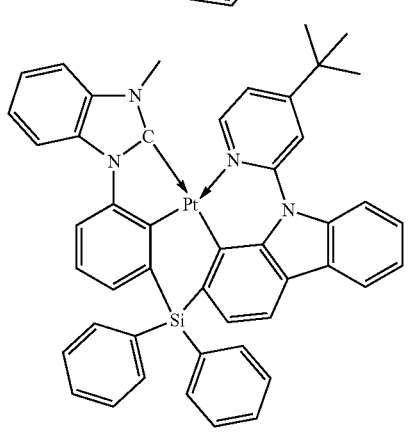
2366
-continued
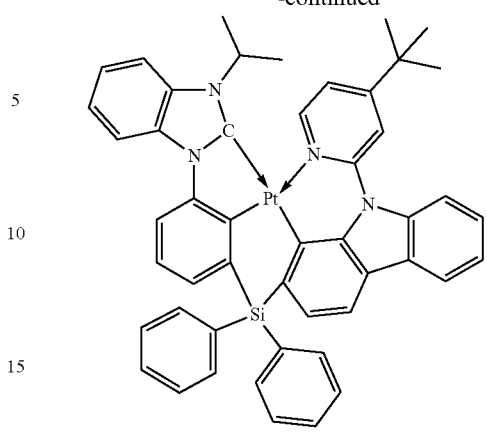
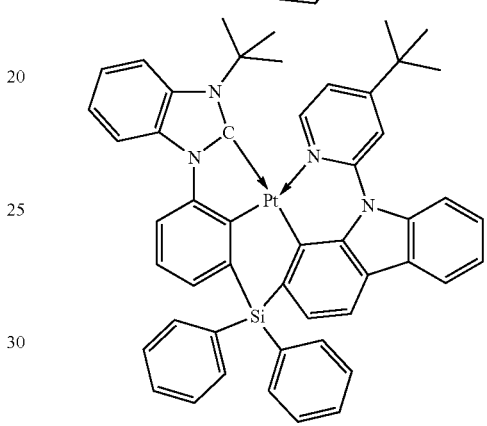
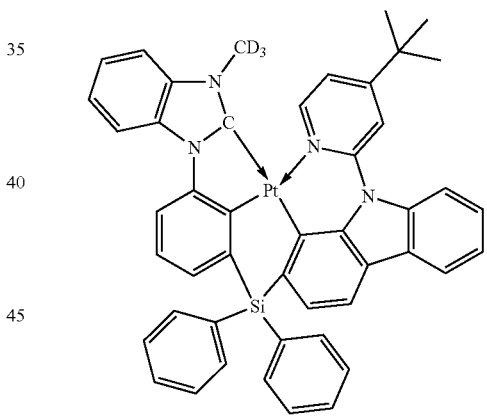
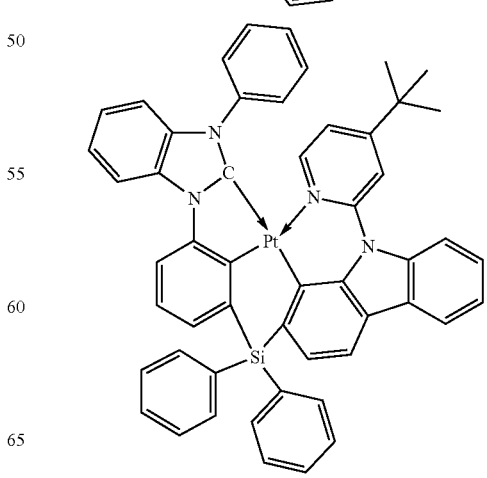

2367
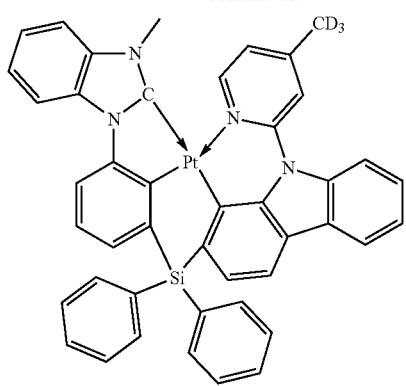
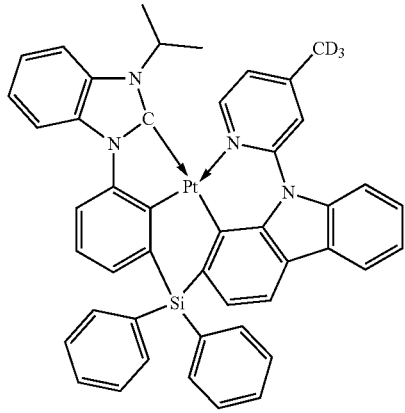
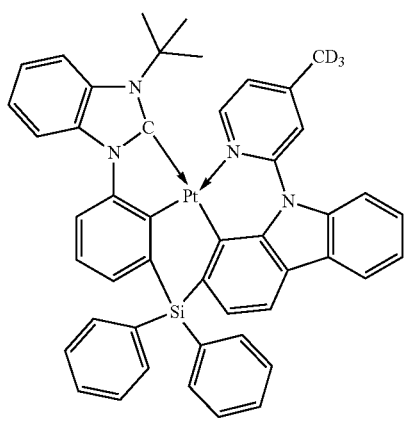
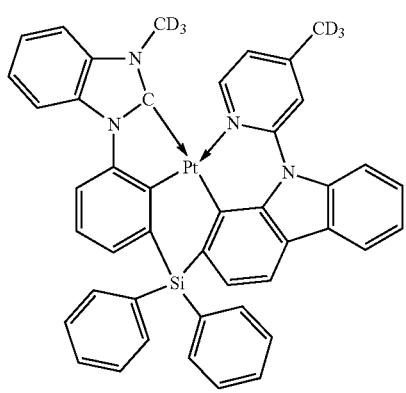
2368
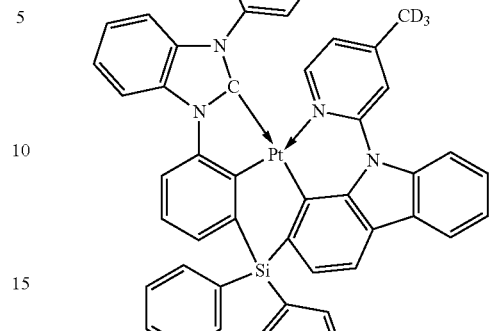
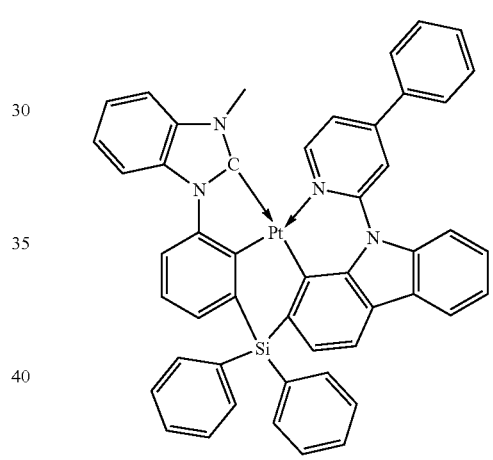
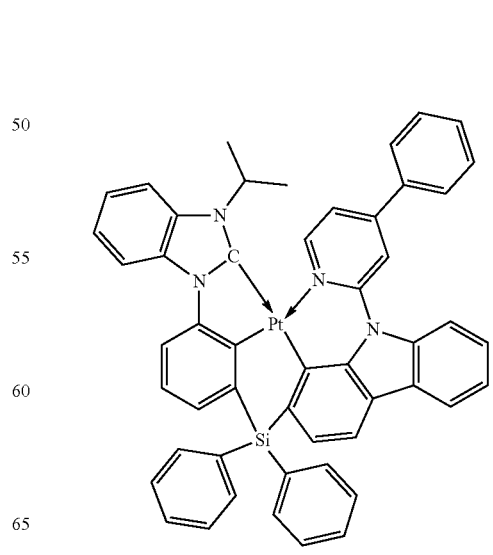

2369
-continued
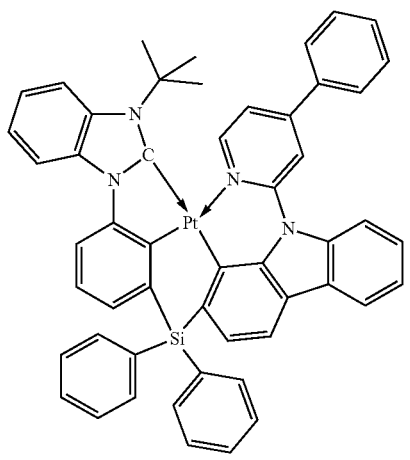
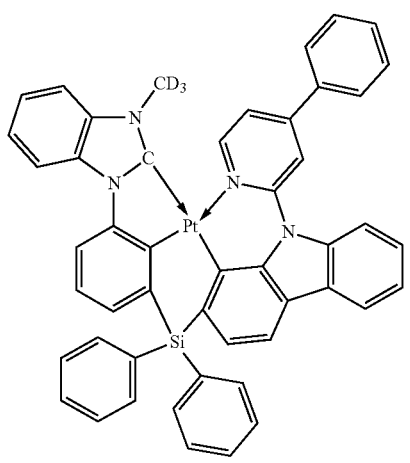
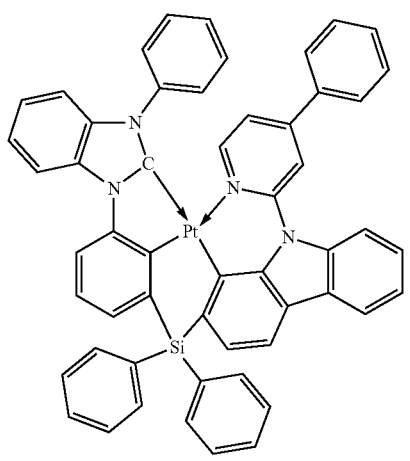
2370
-continued
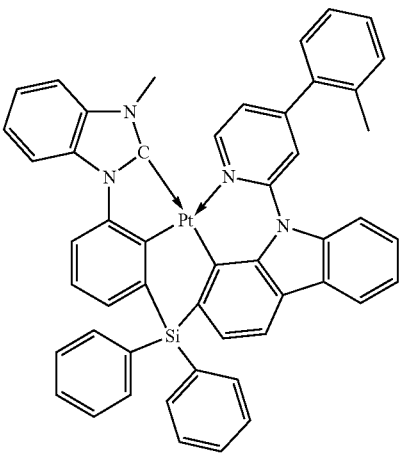
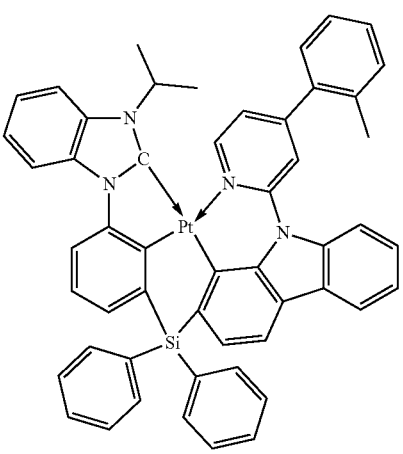
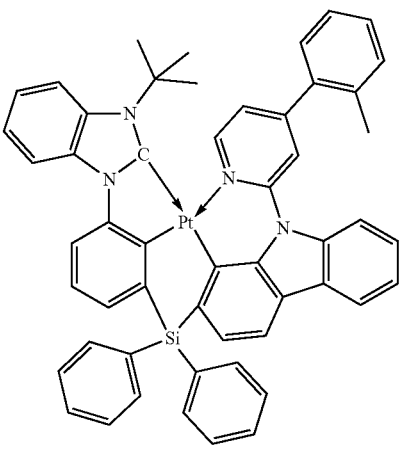

2371
-continued
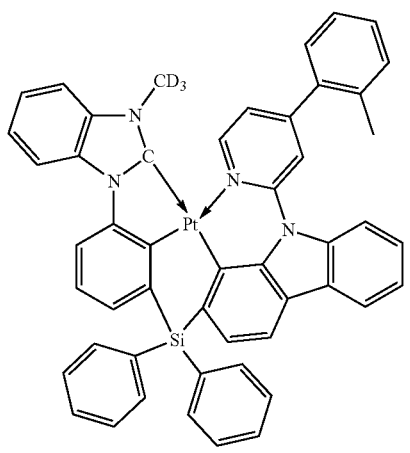
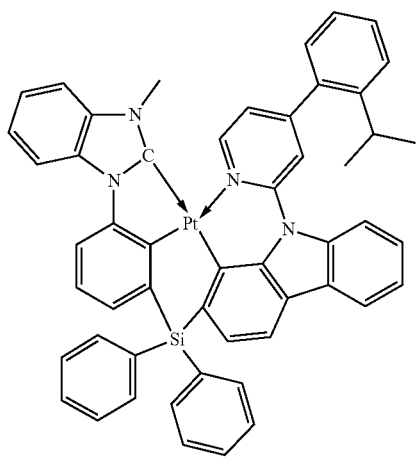
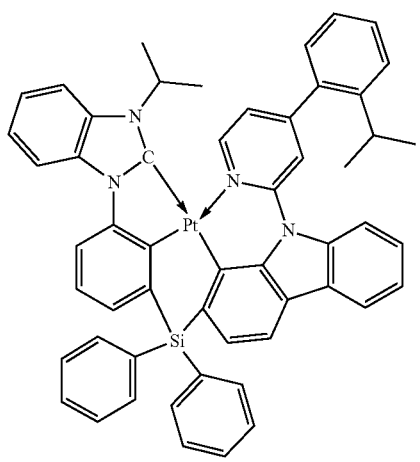
2372
-continued
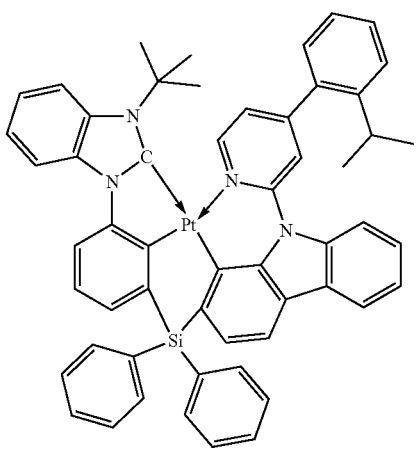
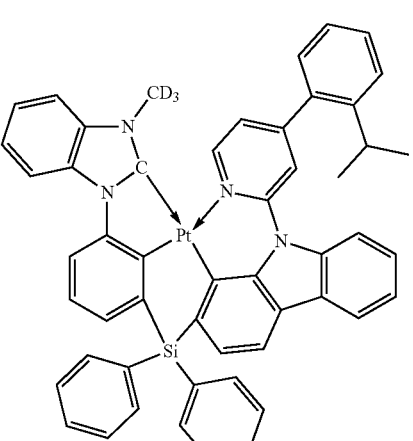
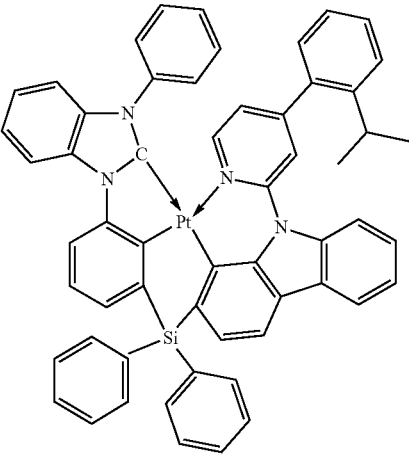

2373
-continued
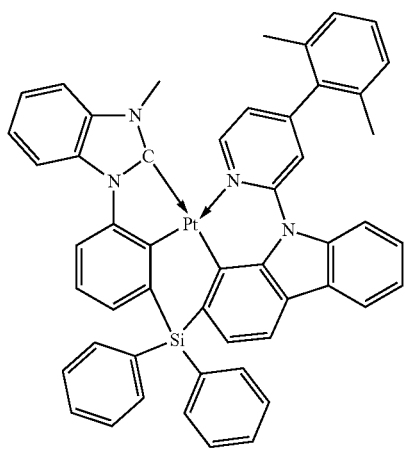
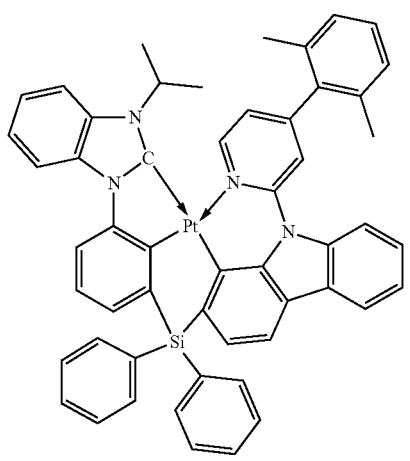
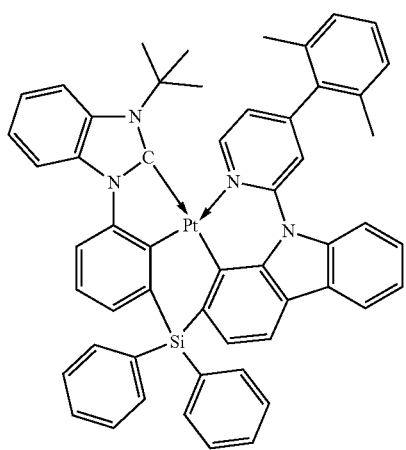
2374
-continued
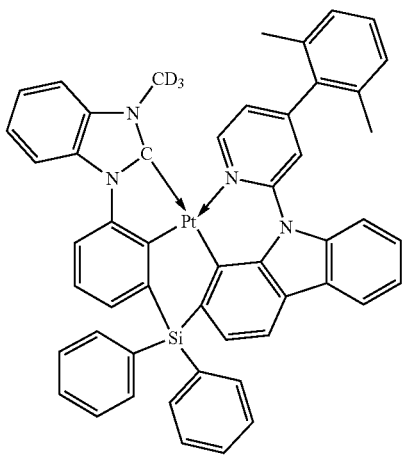
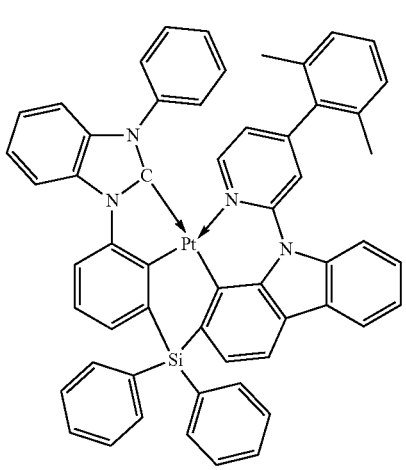
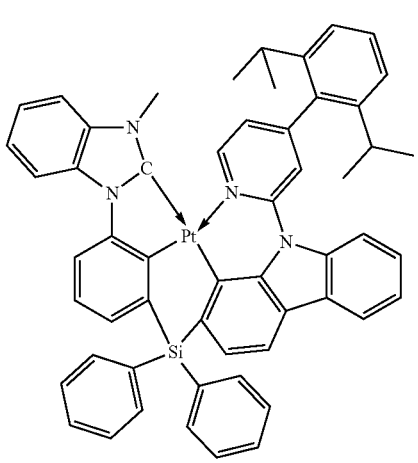

2375
-continued
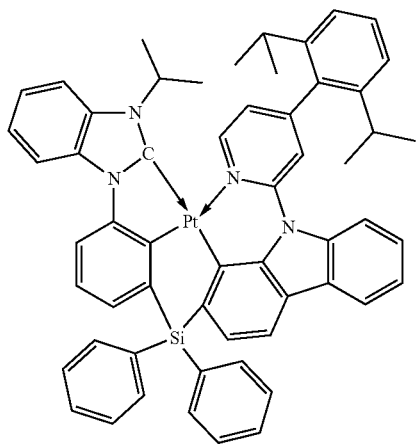
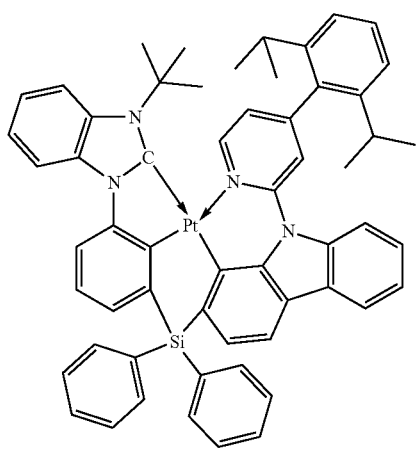
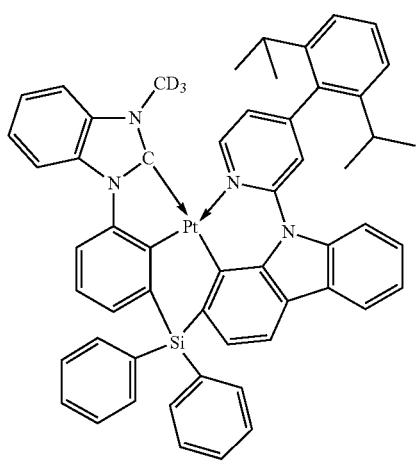
2376
-continued
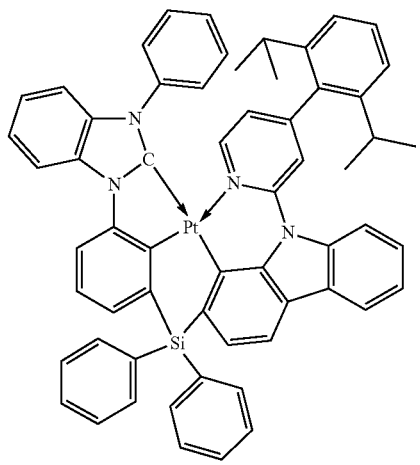
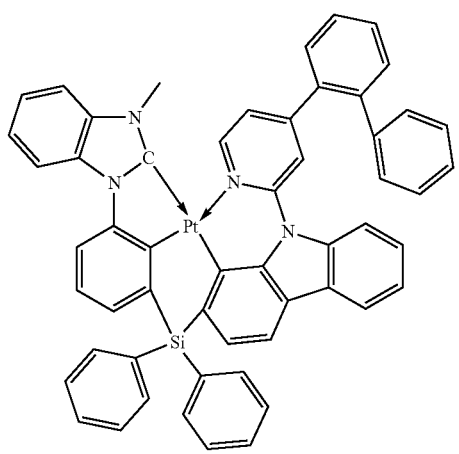
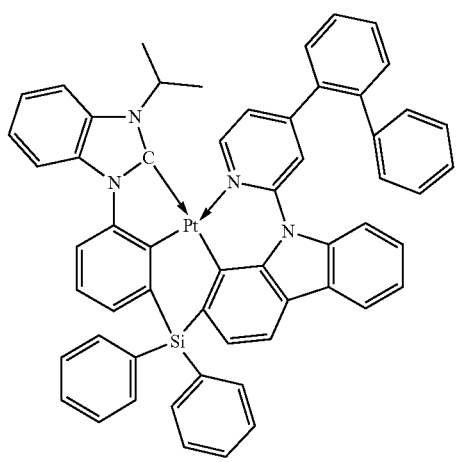

2377
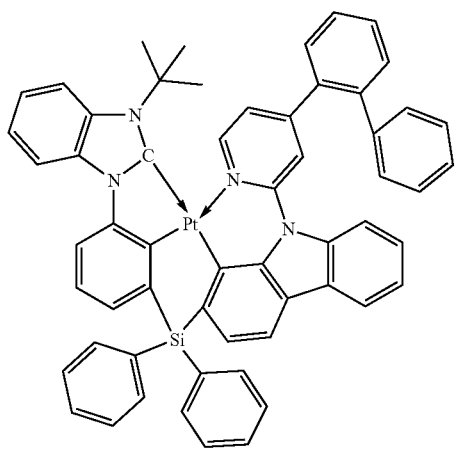
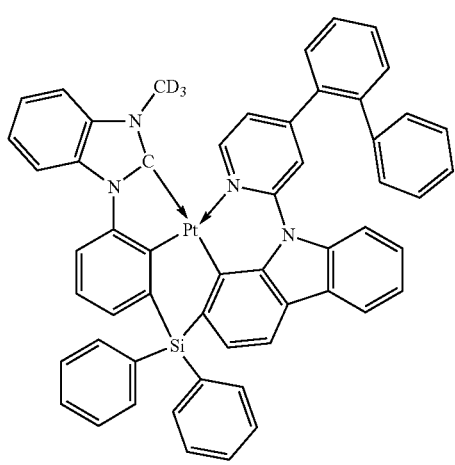
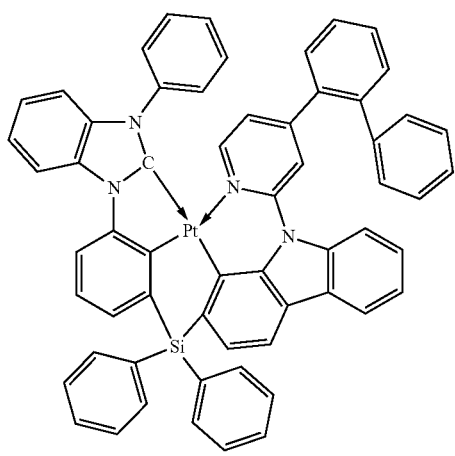
2378
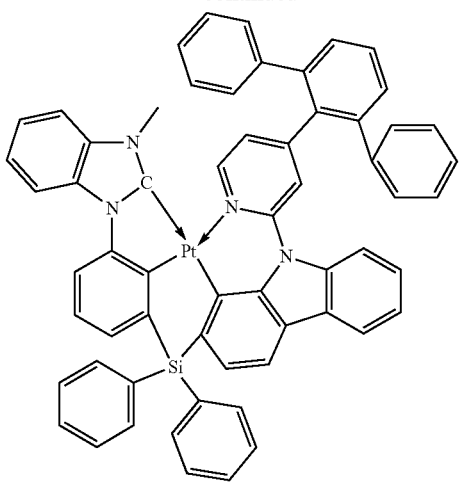
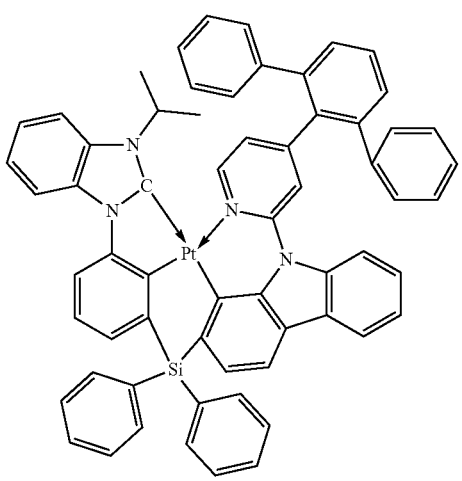
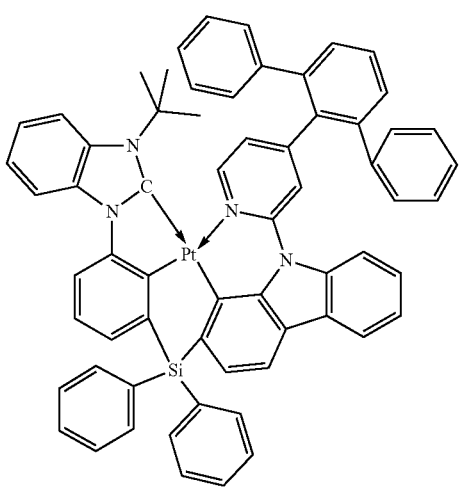

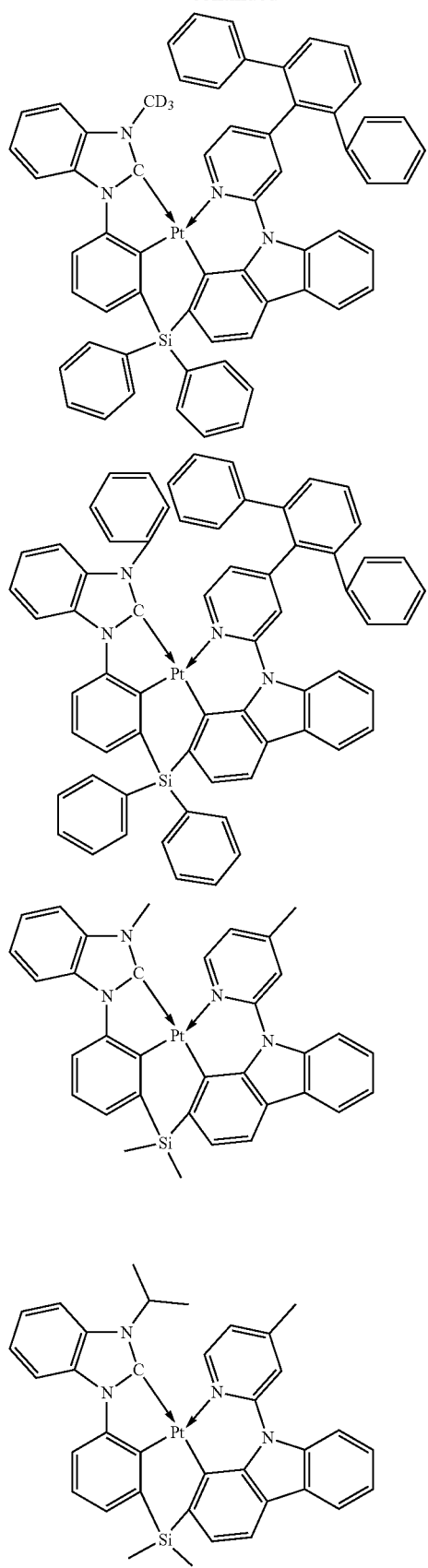
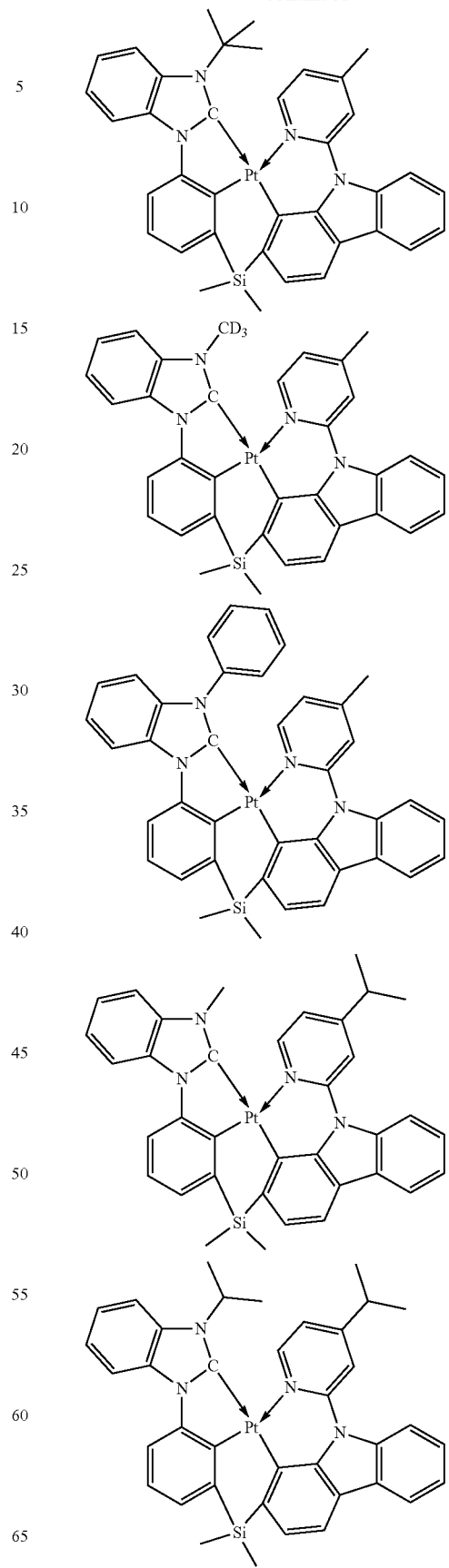

2381
-continued
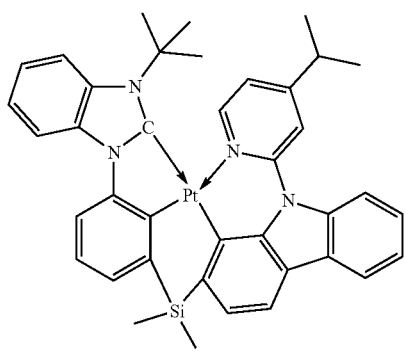
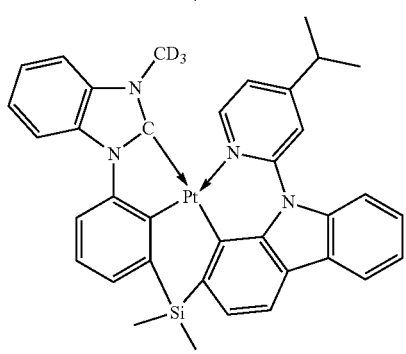
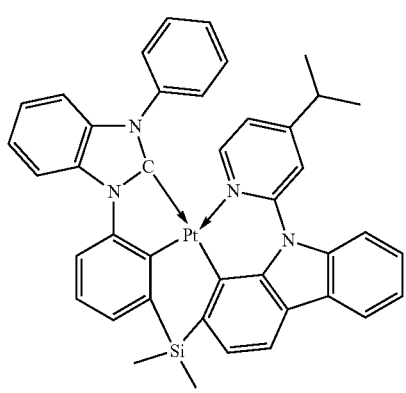
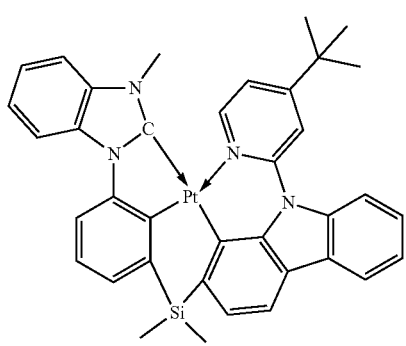
2382
-continued
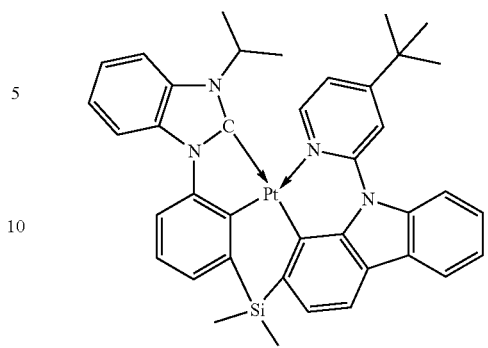
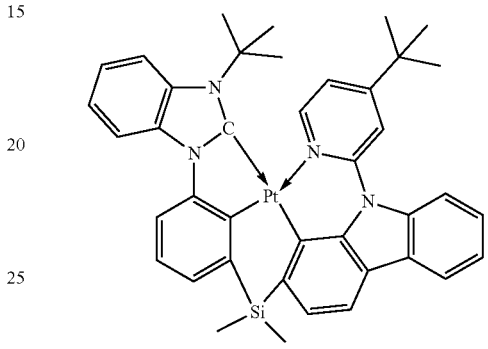
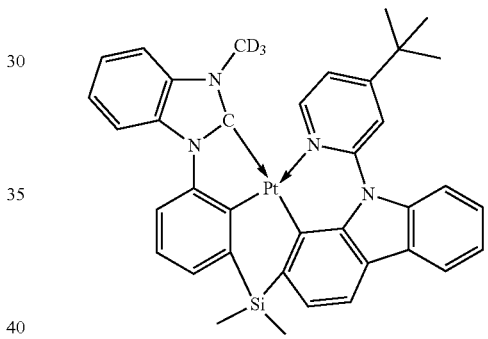
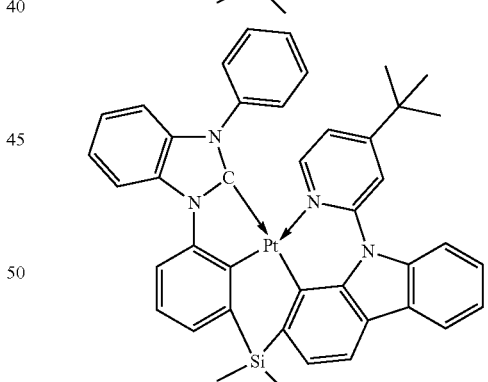
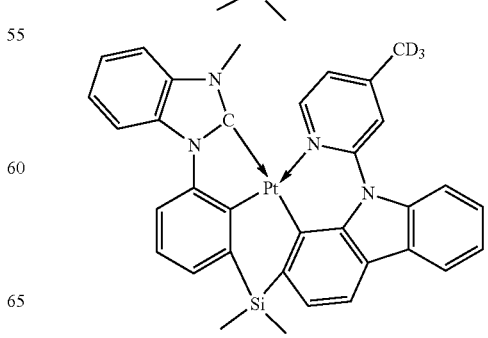

2383
-continued
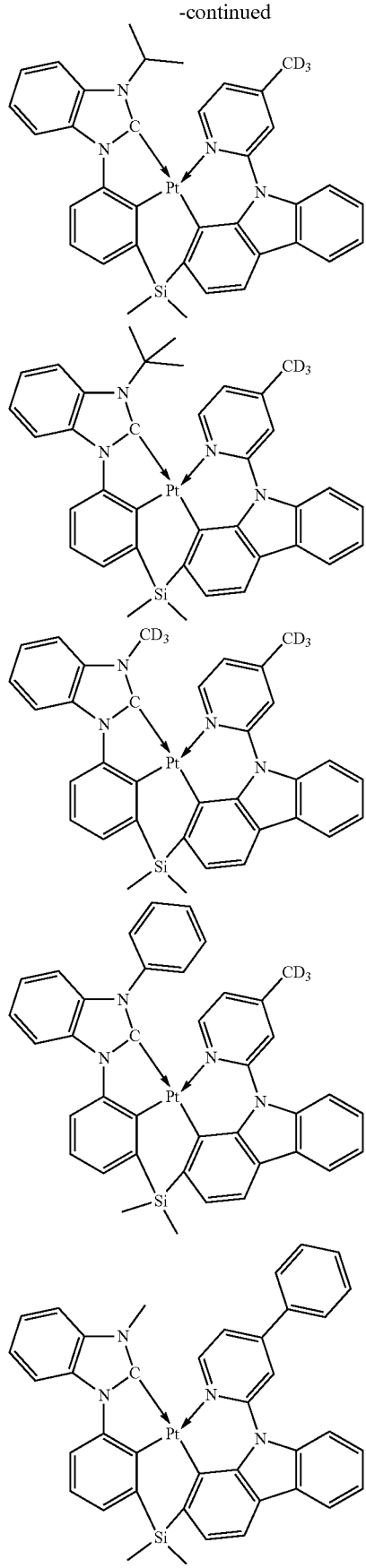
2384
-continued
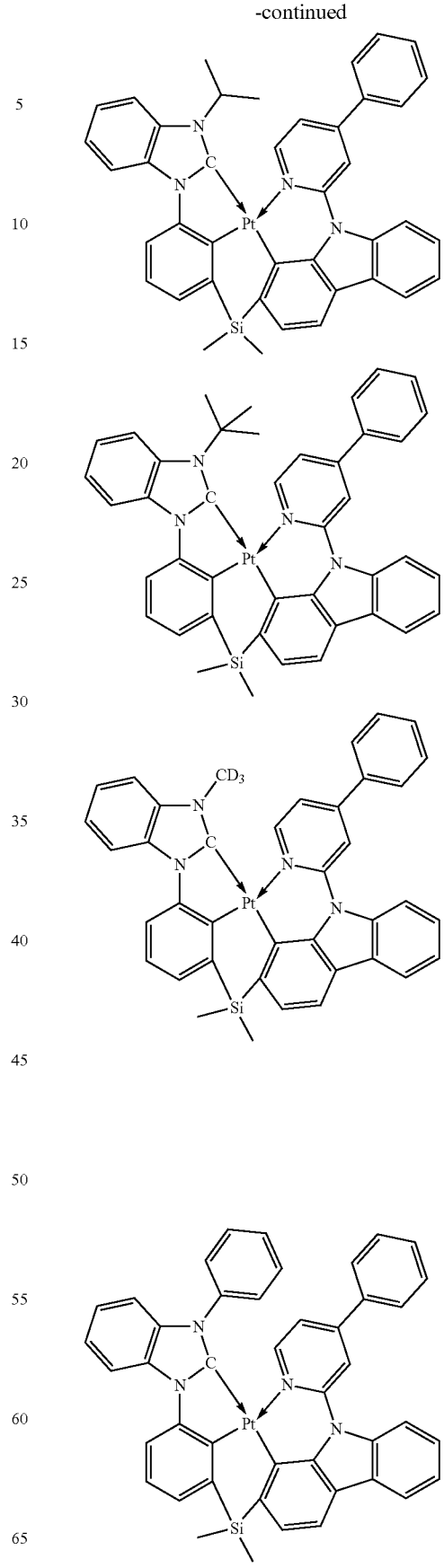

2385
-continued
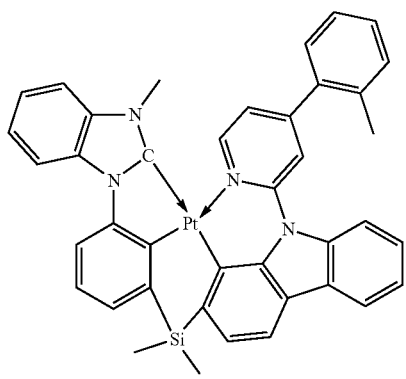
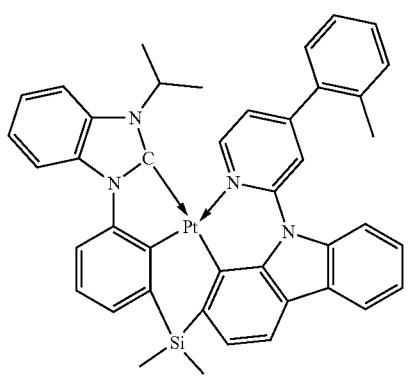
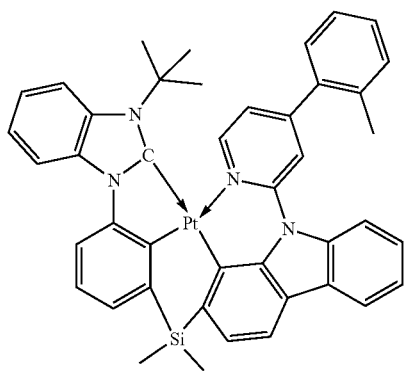
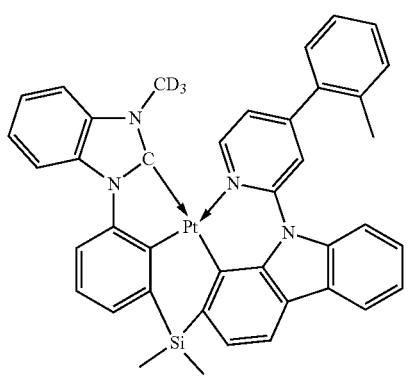
2386
-continued
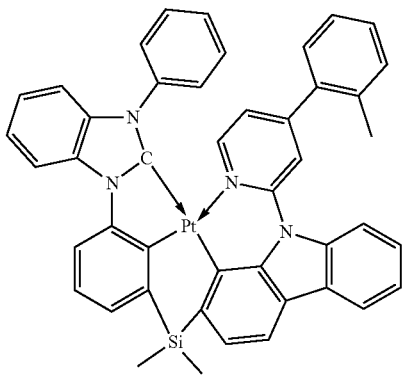
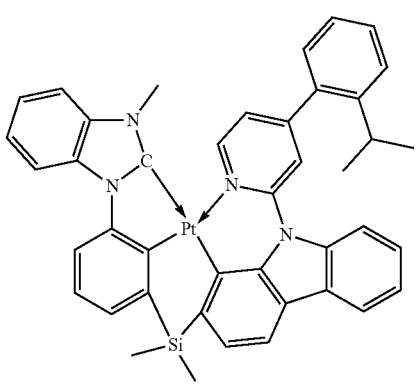
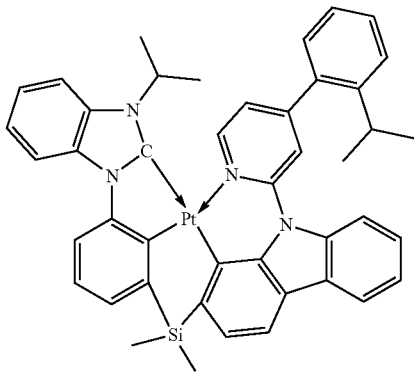
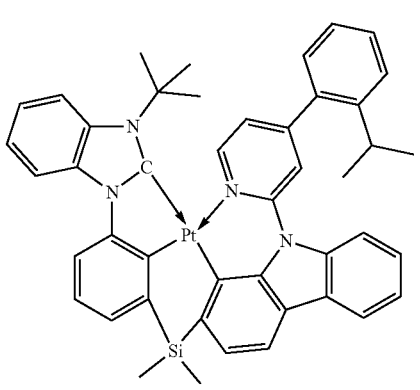

2387
-continued
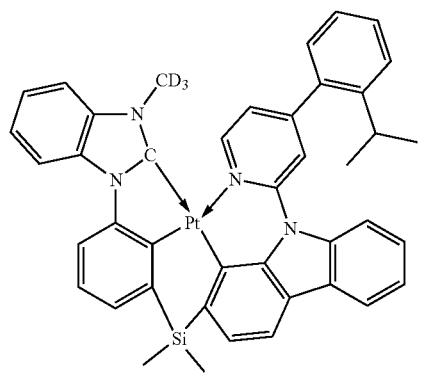
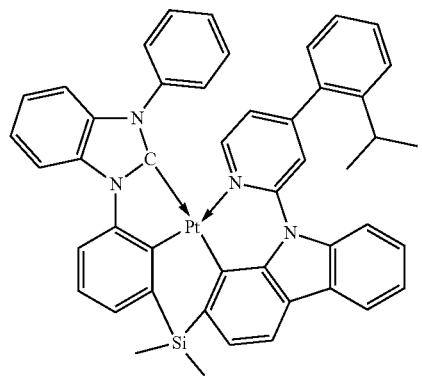
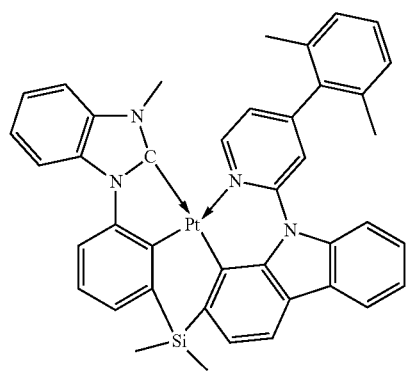
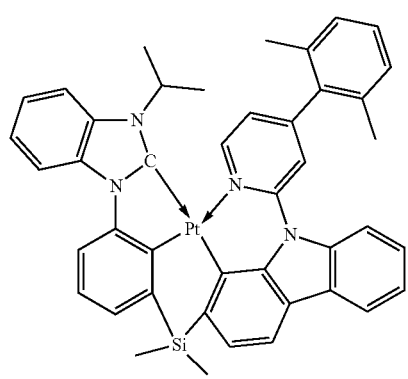
2388
-continued
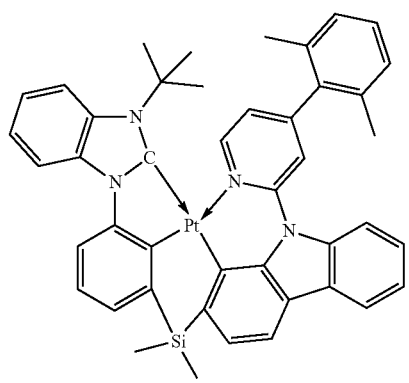
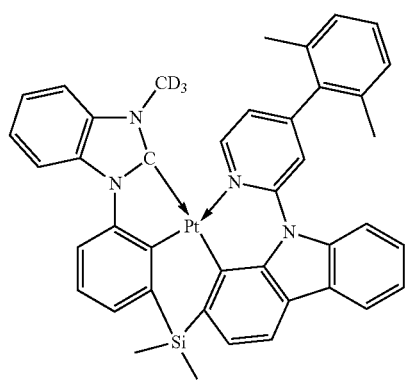
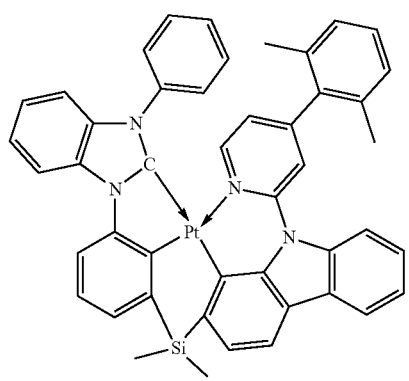
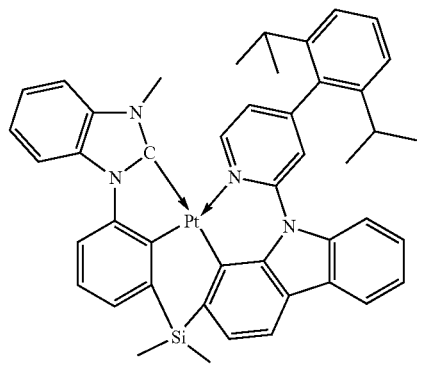

2389
-continued
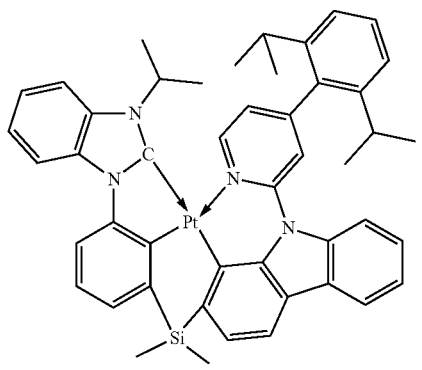
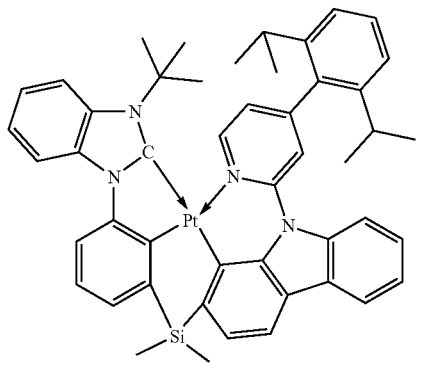
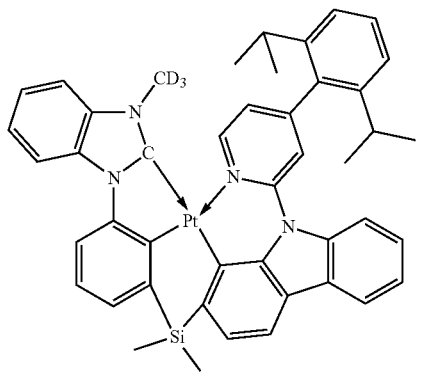
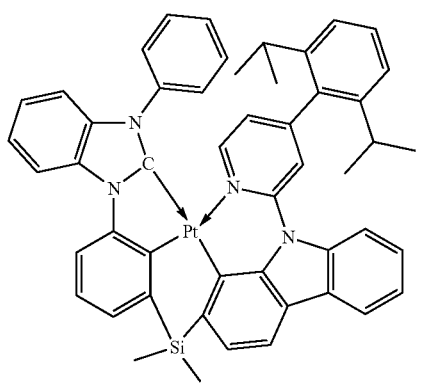
2390
-continued
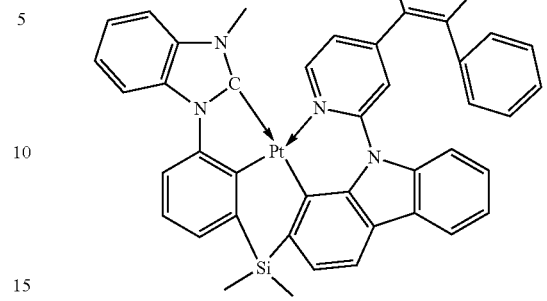
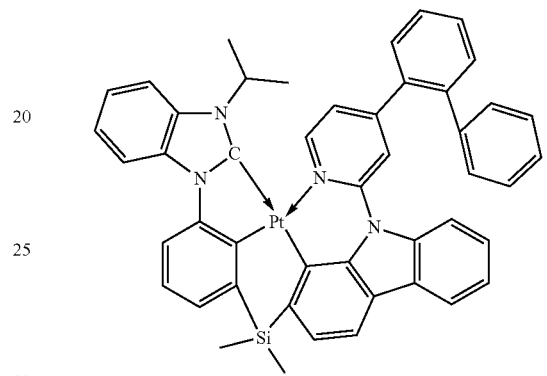
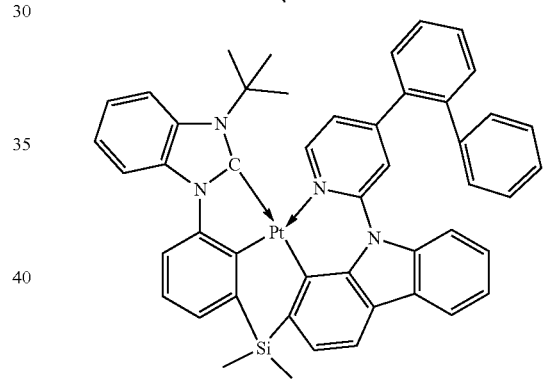

2391
-continued
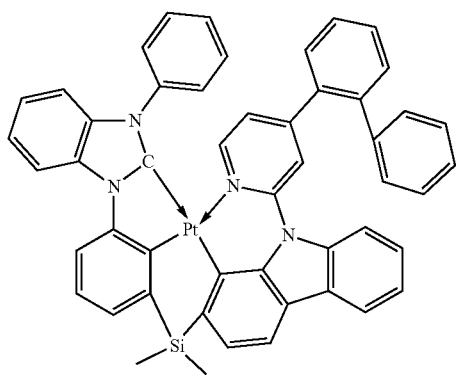
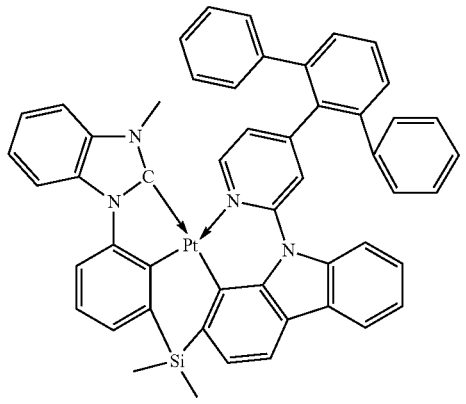
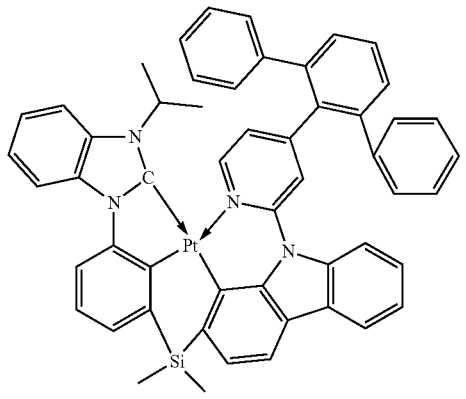
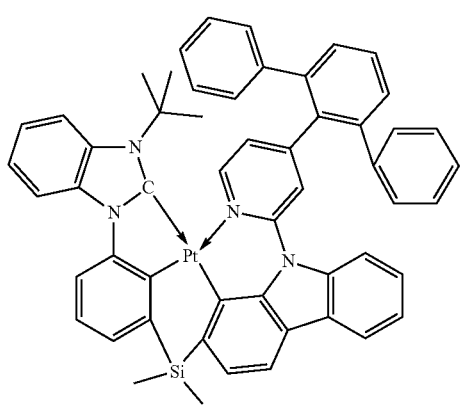
2392
-continued
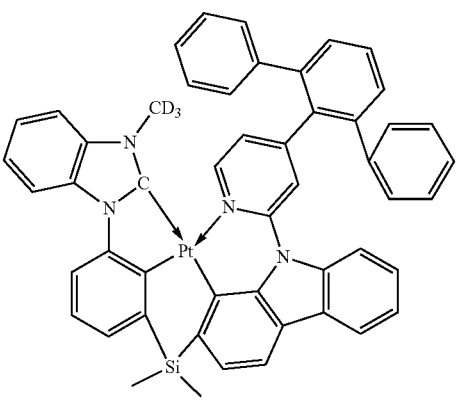
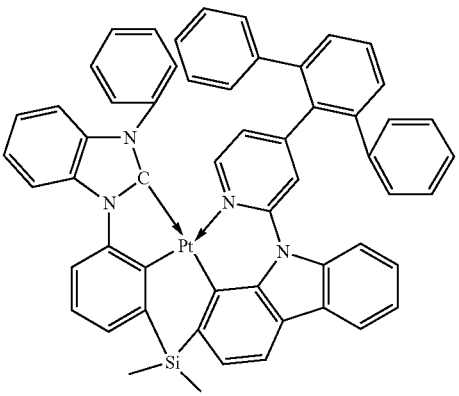
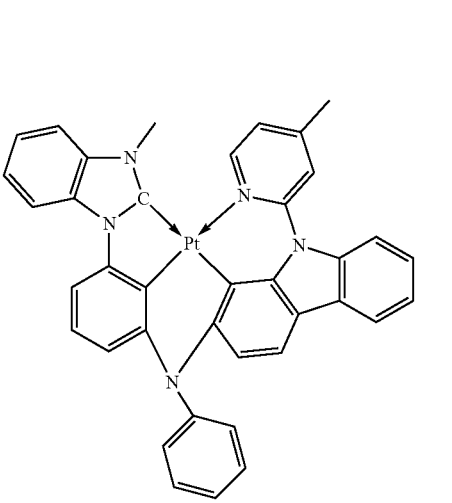
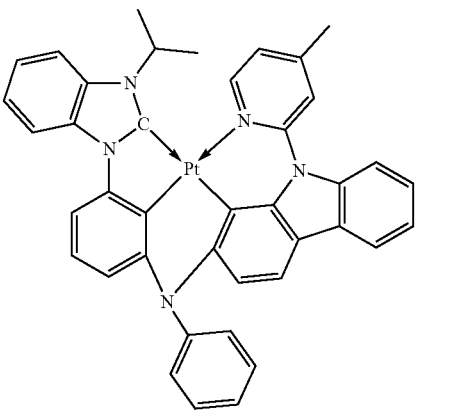

2393
-continued
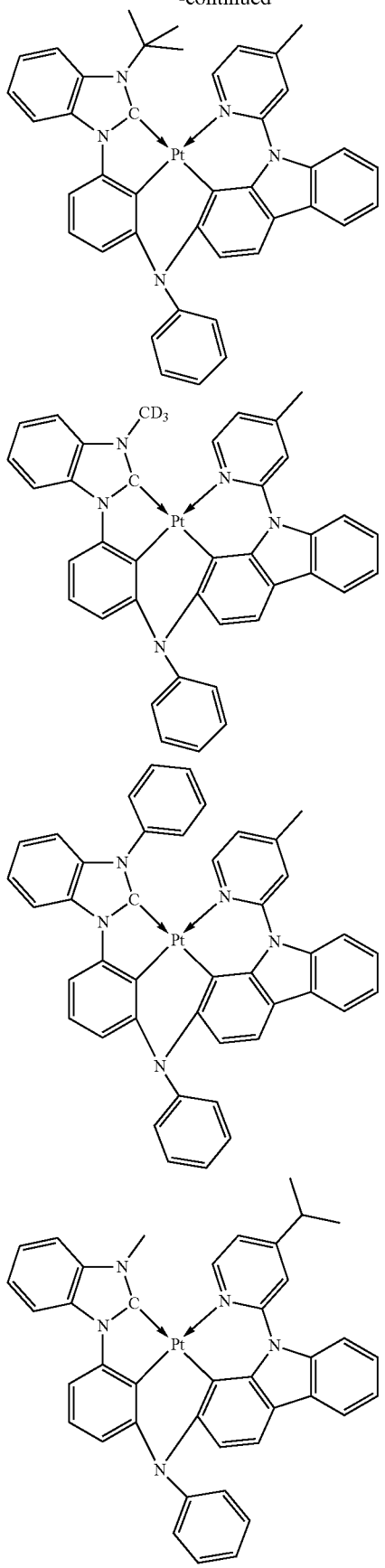
2394
-continued
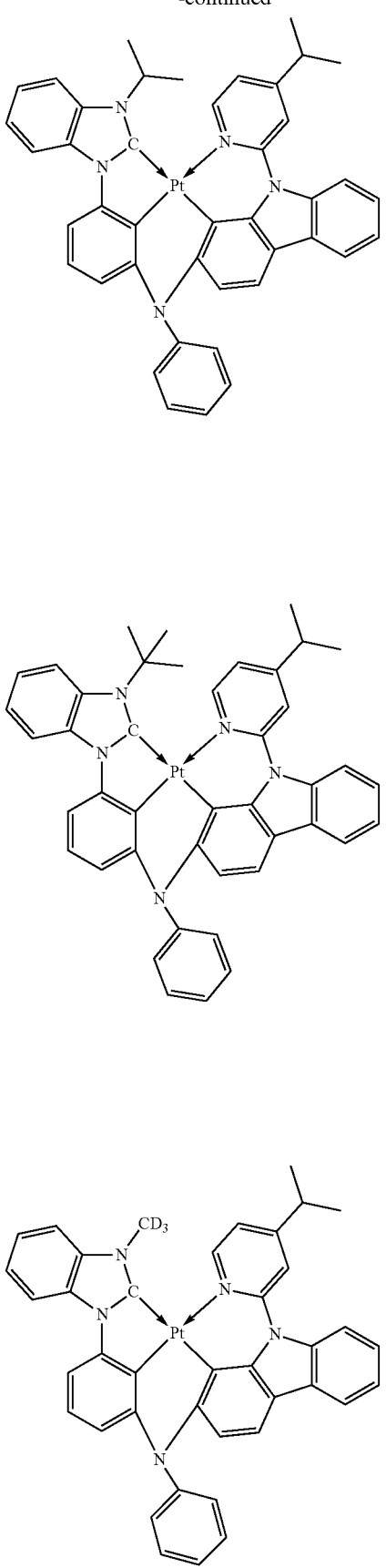

2395
-continued
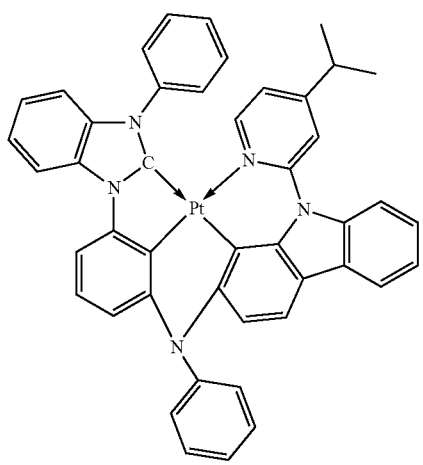
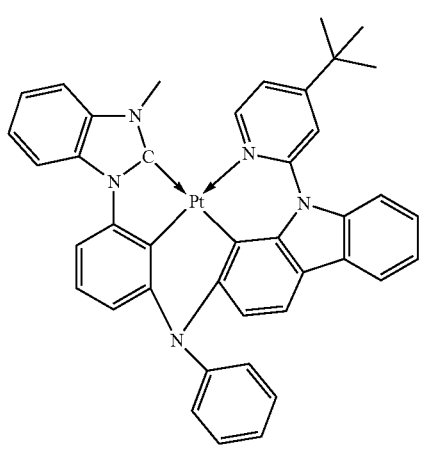
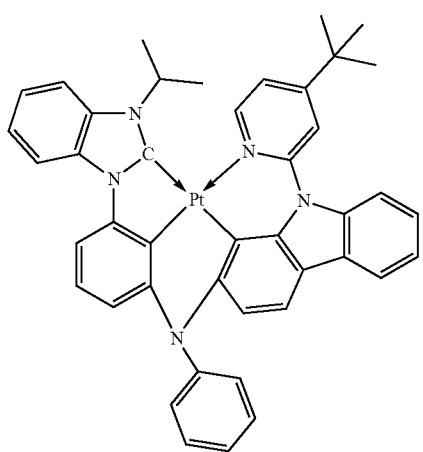
2396
-continued
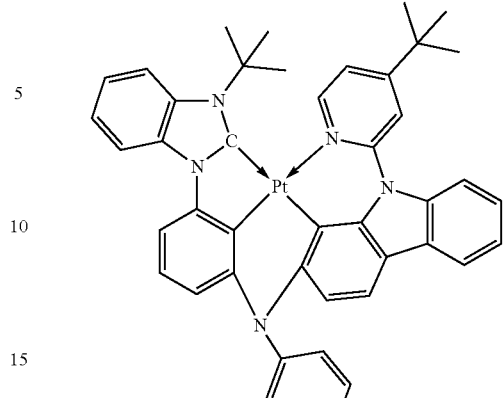
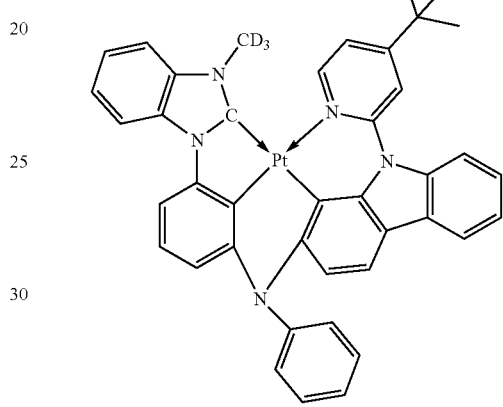
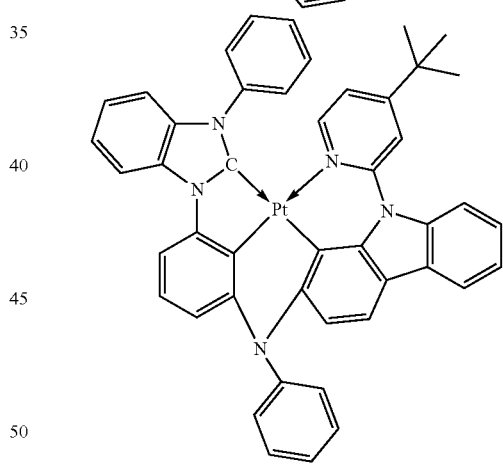
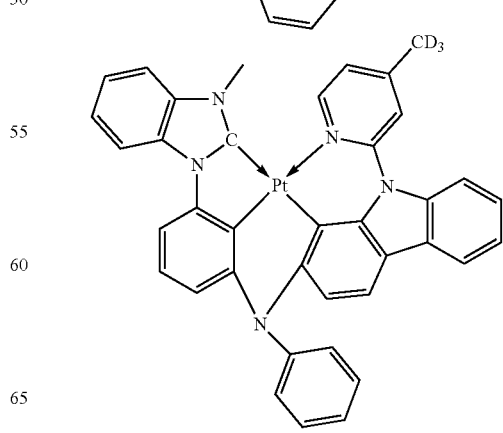

2397
-continued
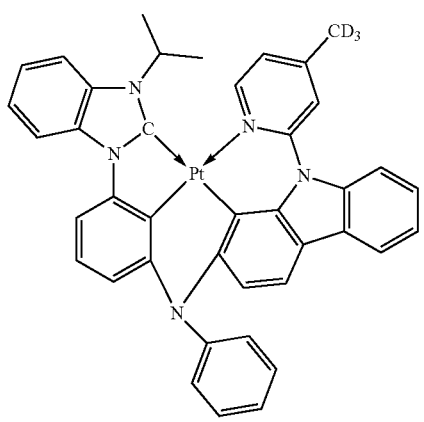
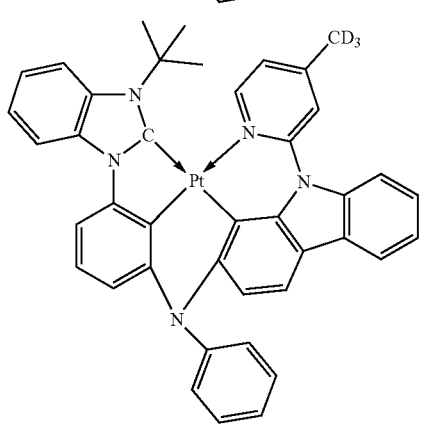
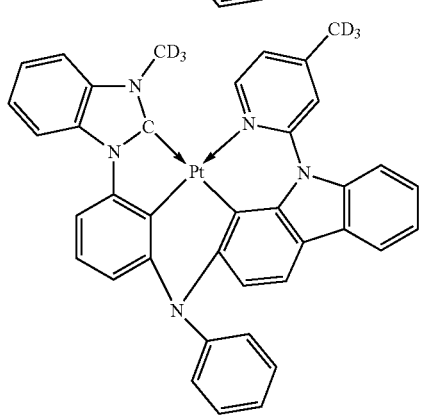
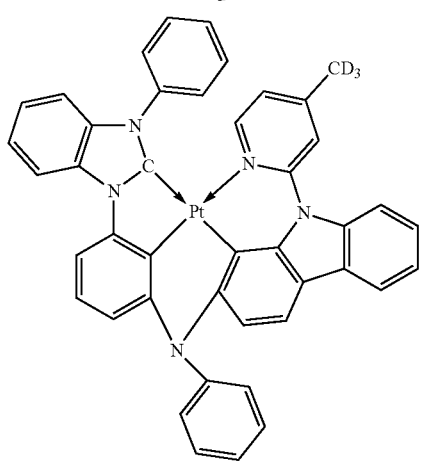
2398
-continued
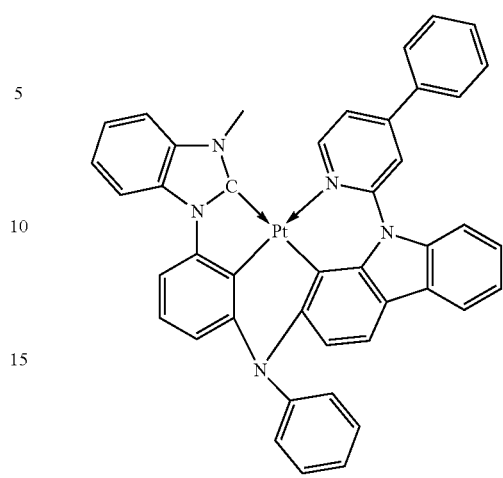
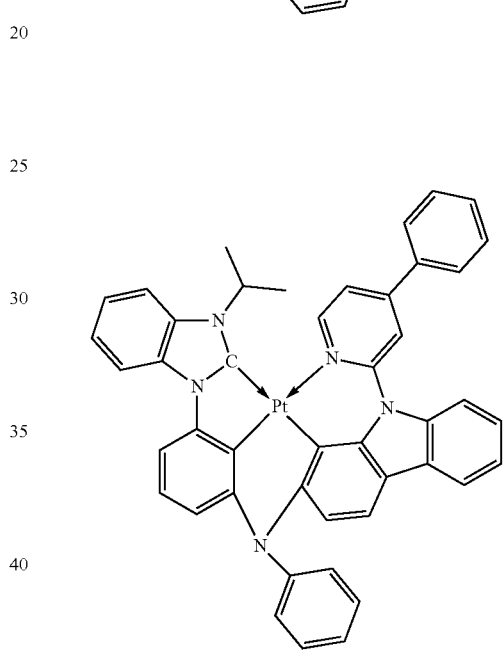
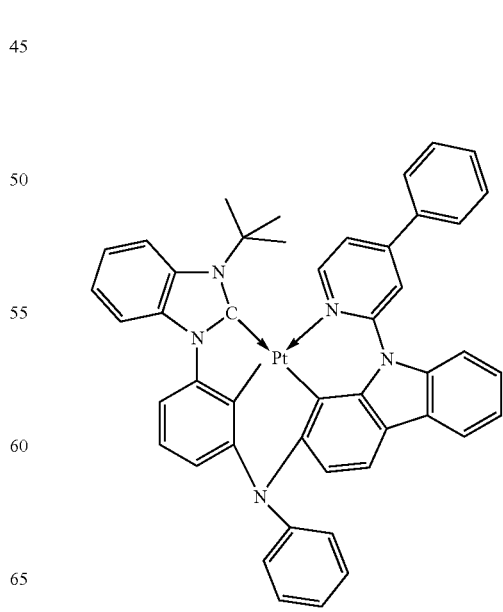

2399
-continued
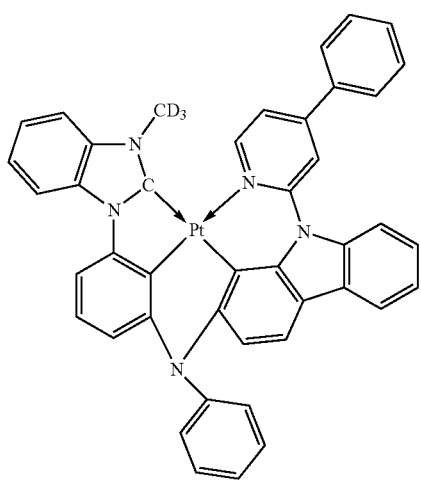
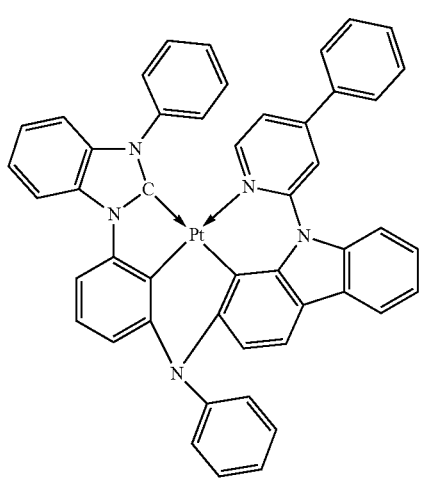
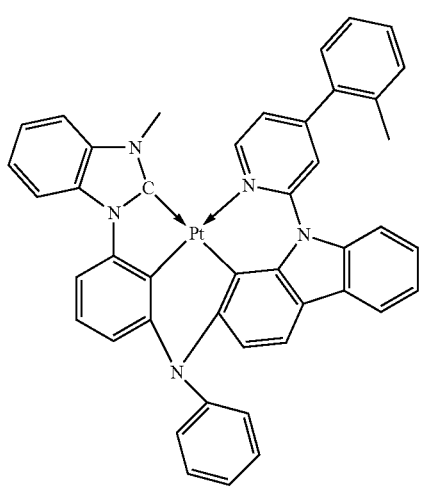
2400
-continued
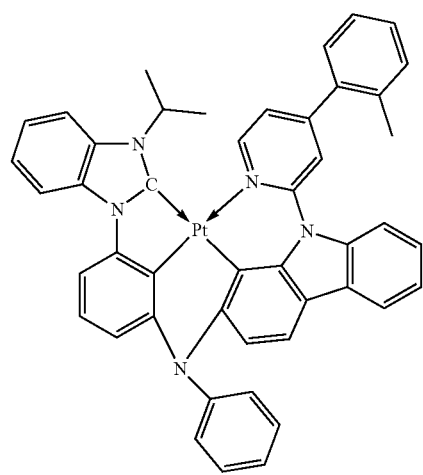
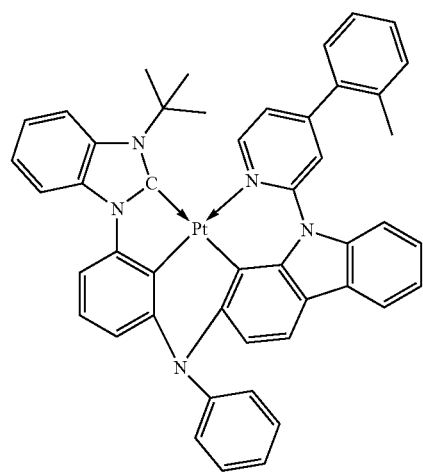
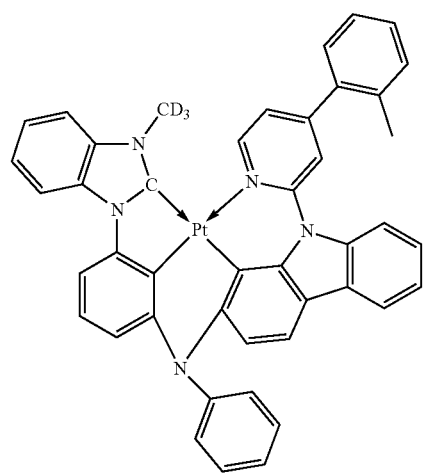

2401
-continued
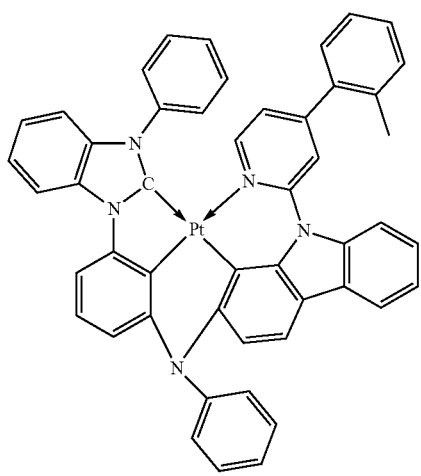
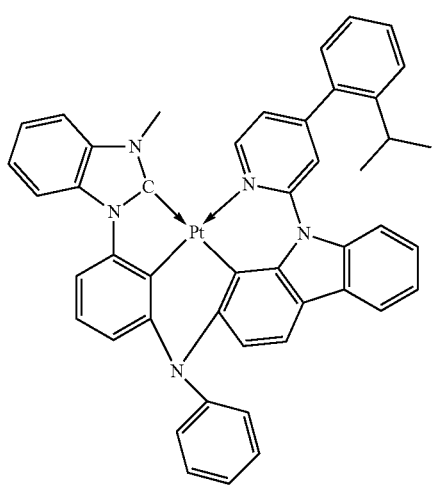
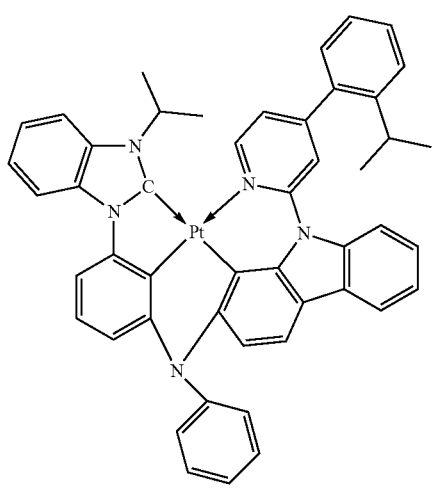
2402
-continued
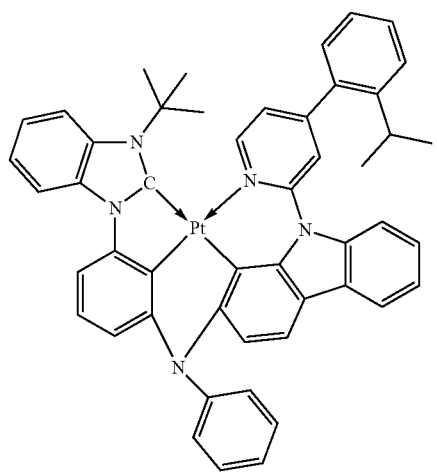
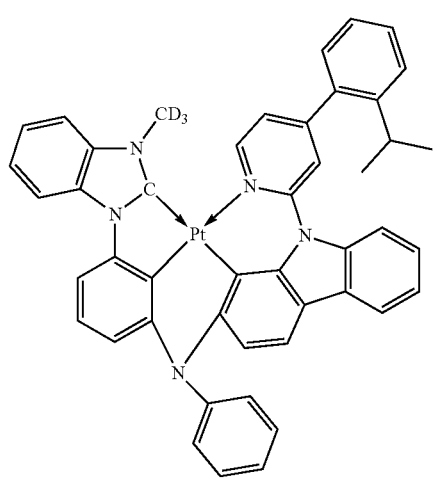
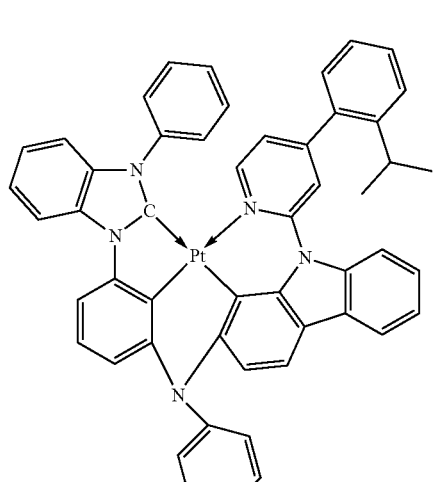

| 2403 | 2404 |
|---|---|
| -continued | -continued |
| 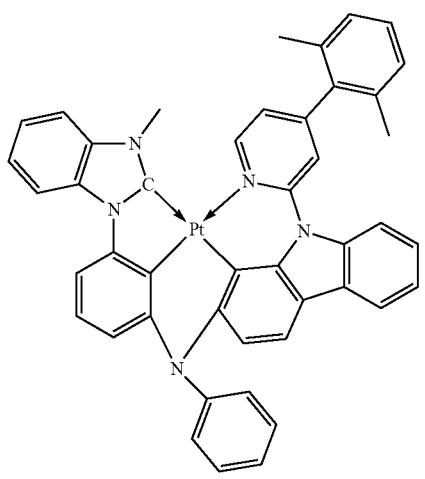 | 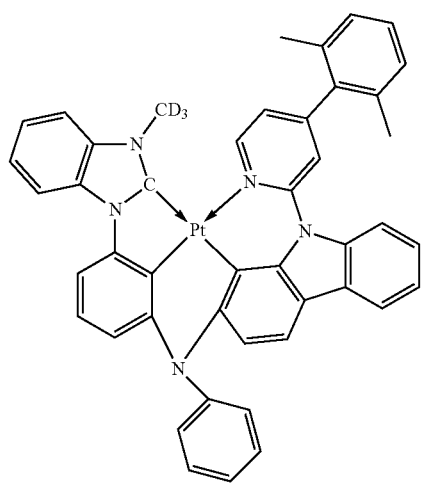 |
| 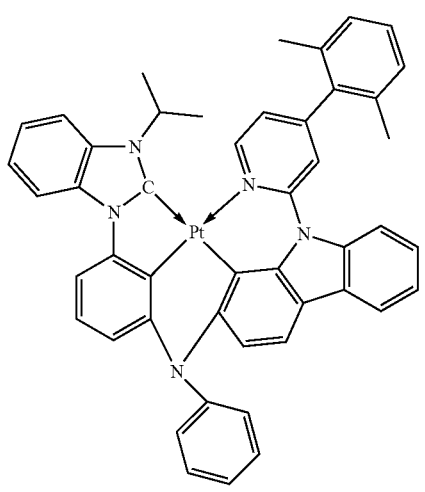 | 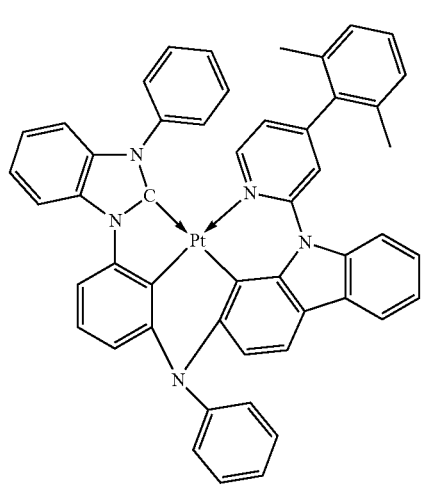 |
| 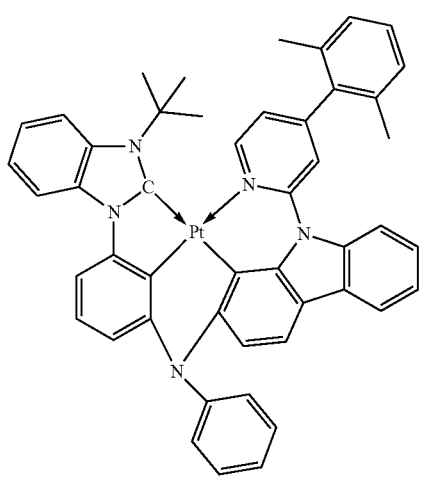 | 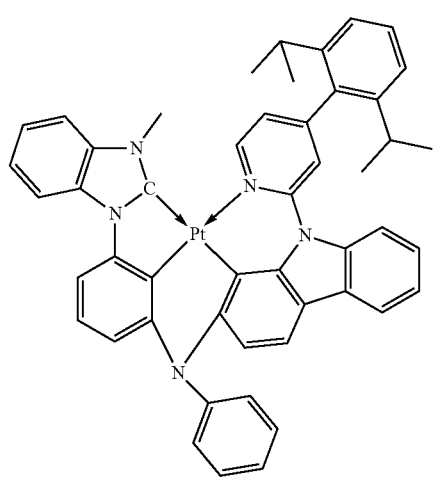 |

2405
-continued
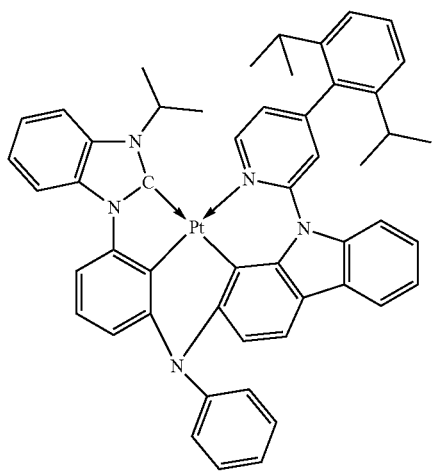
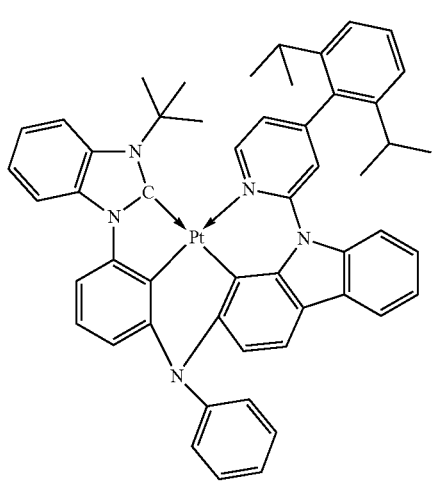
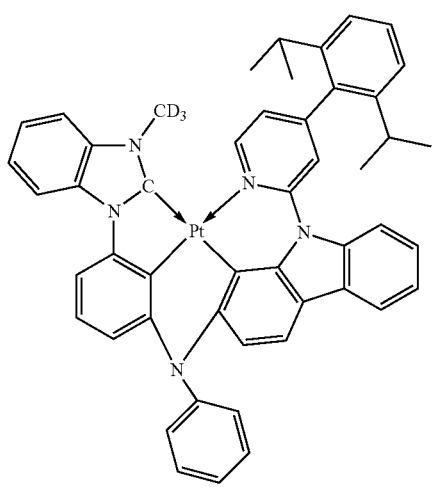
2406
-continued
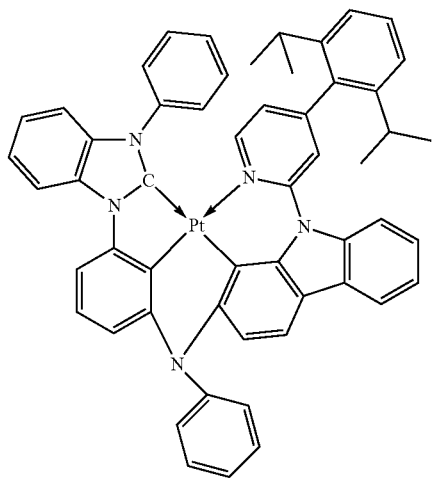
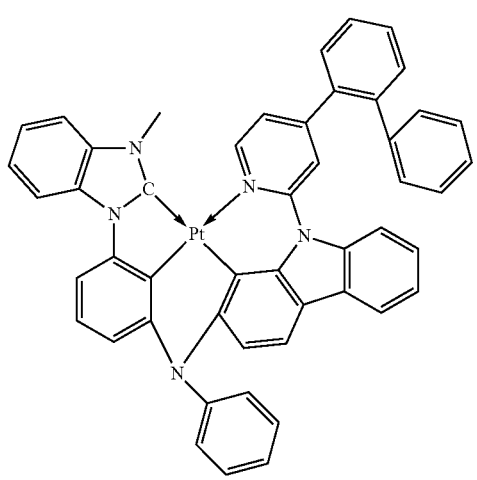
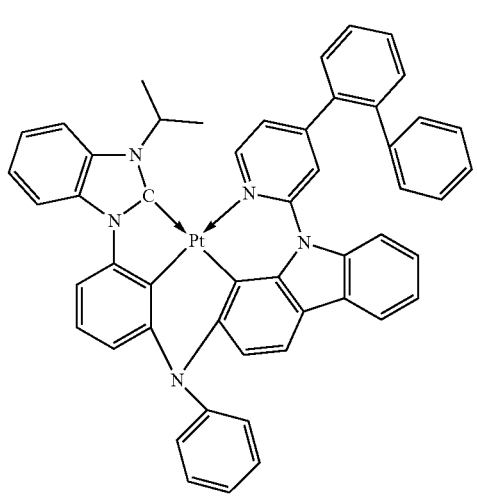

2407
-continued
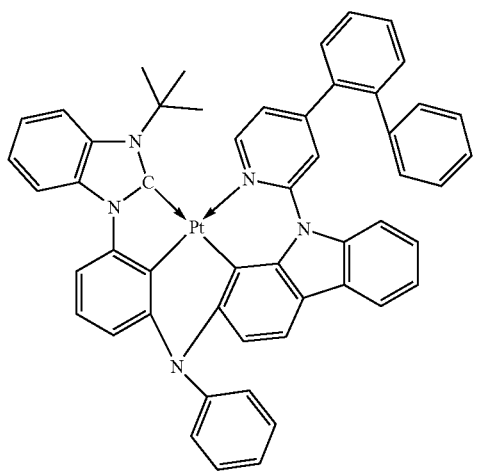
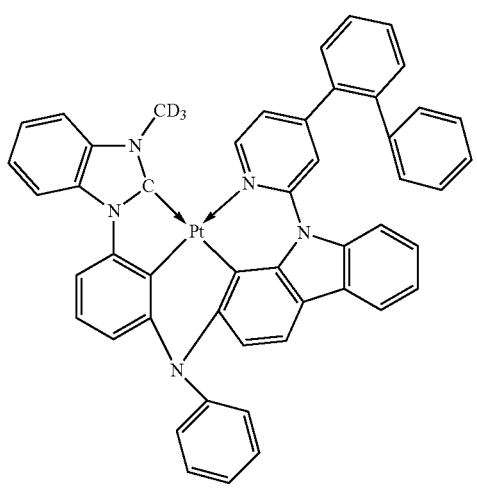
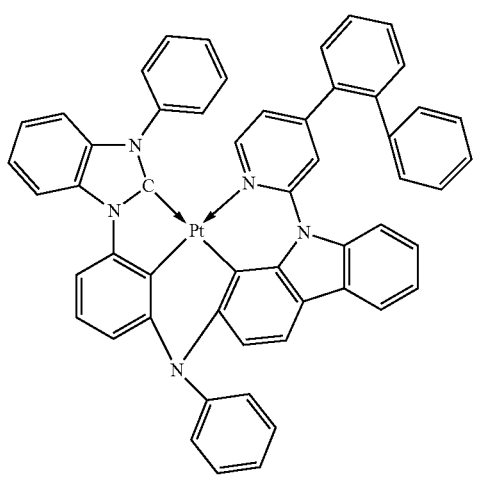
2408
-continued
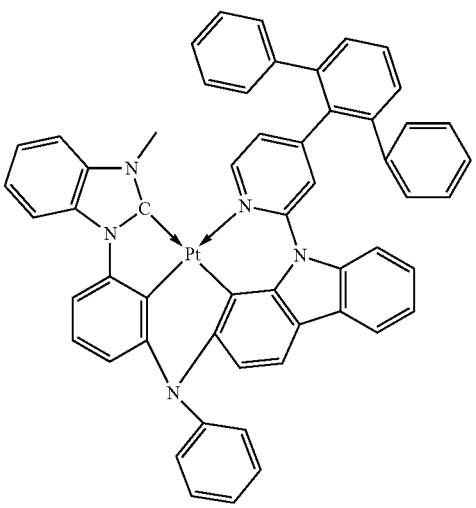
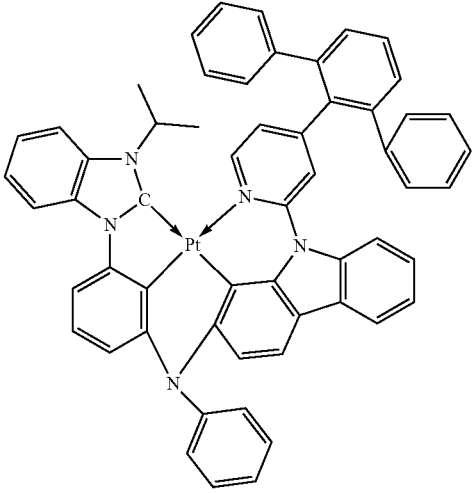
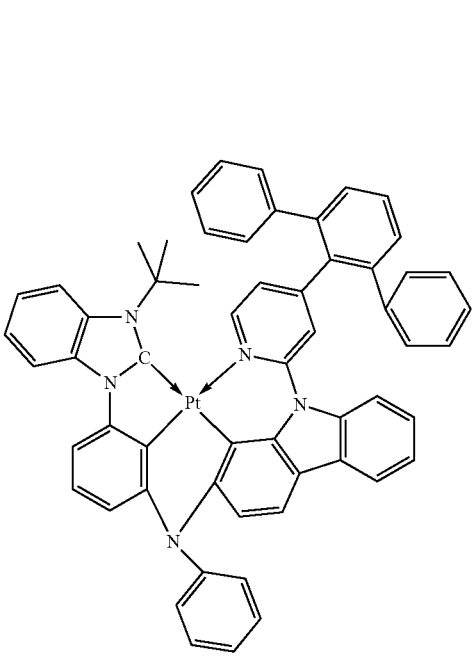

2409
-continued
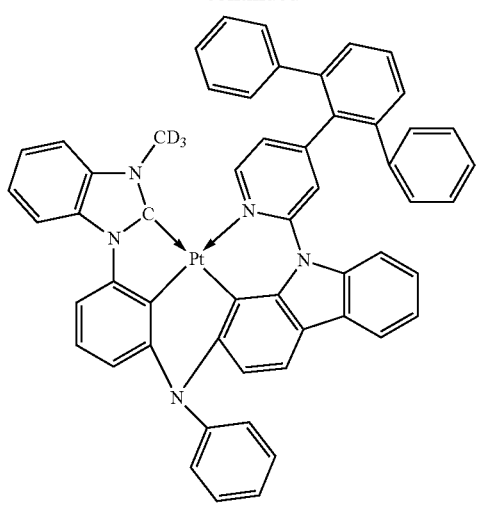
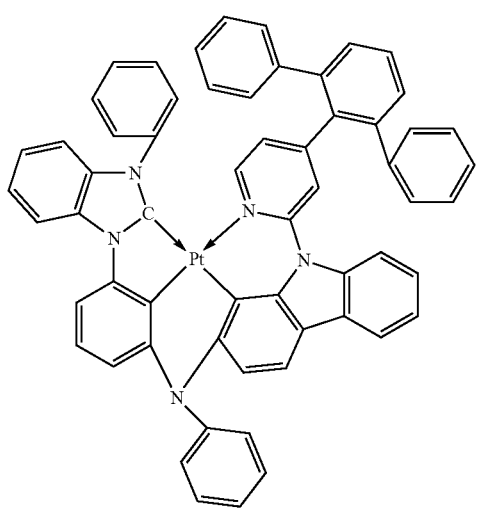
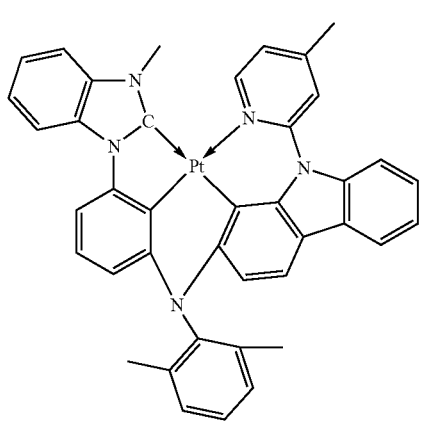
2410
-continued
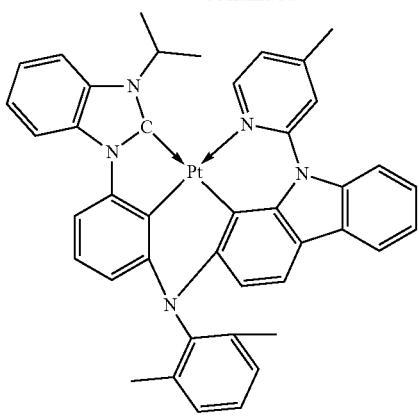
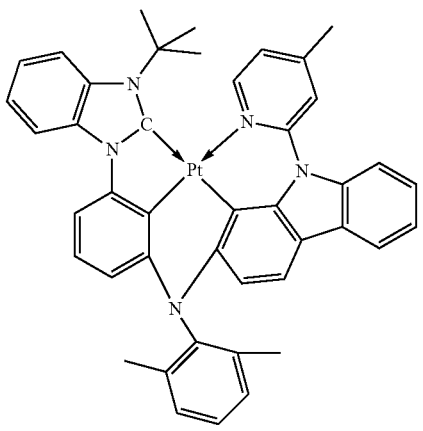
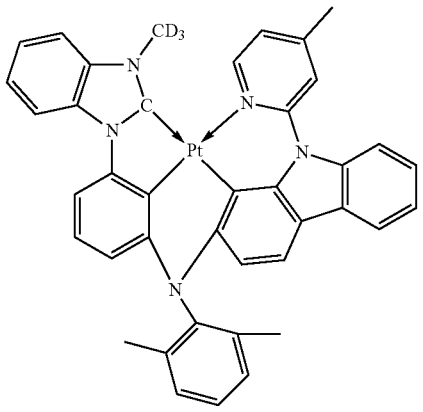
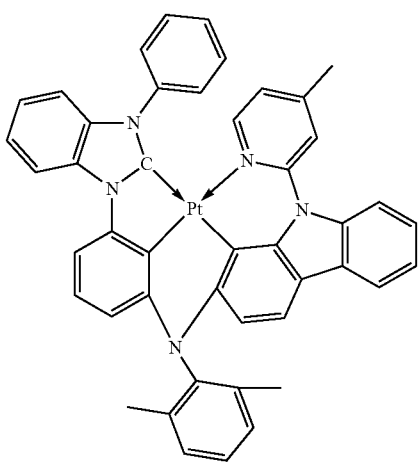

2411
-continued
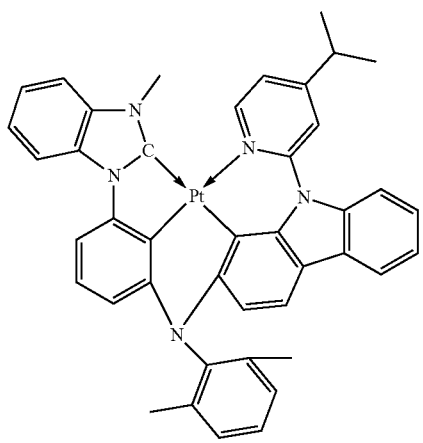
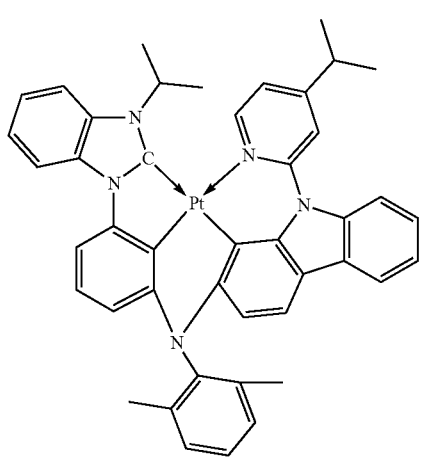
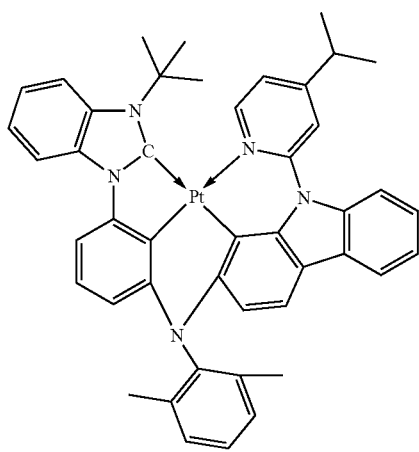
2412
-continued
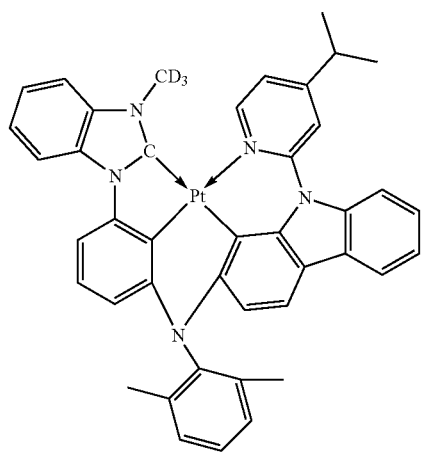
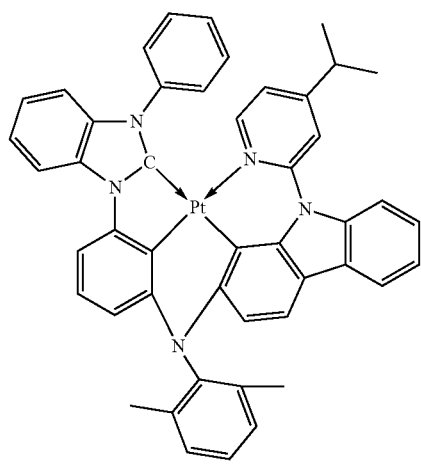
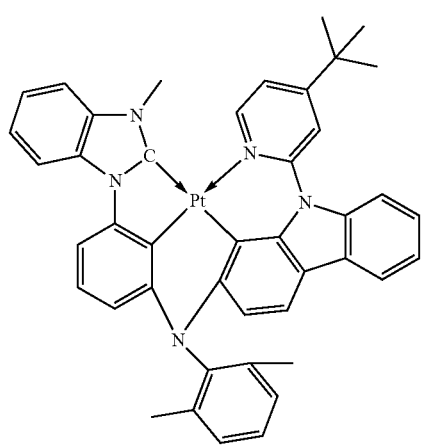

2413
-continued
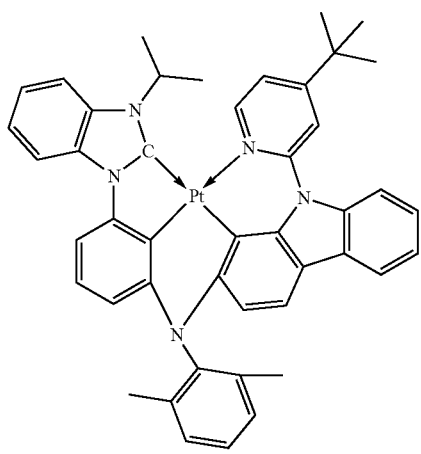
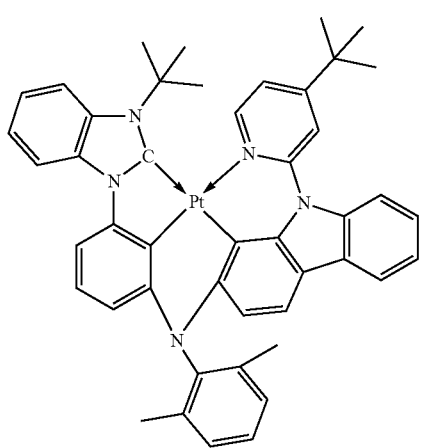
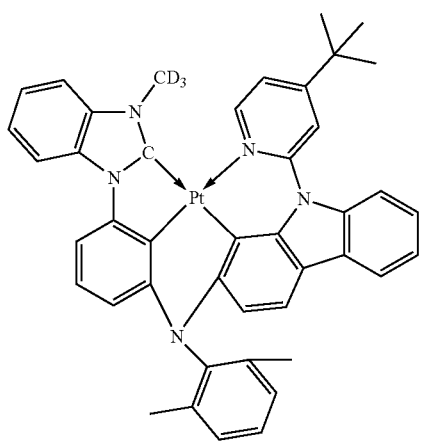
2414
-continued
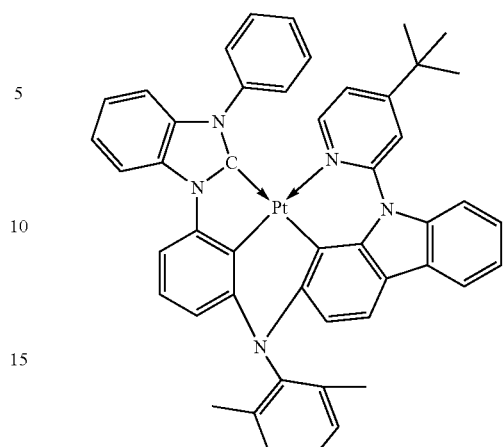
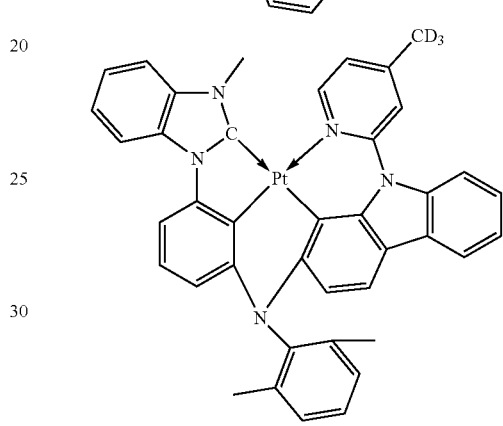
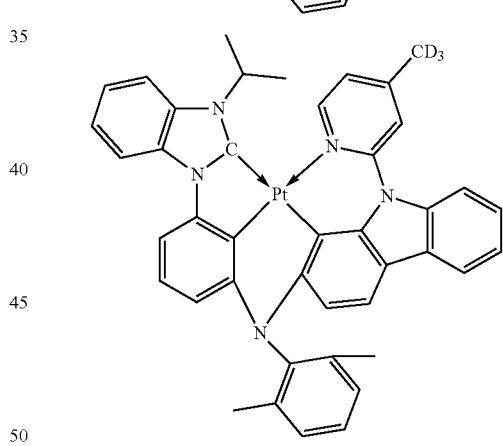
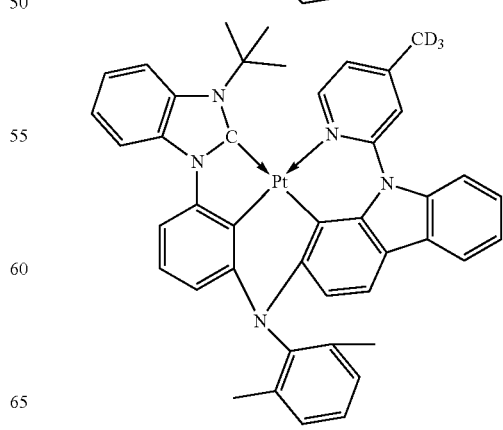

2415
-continued
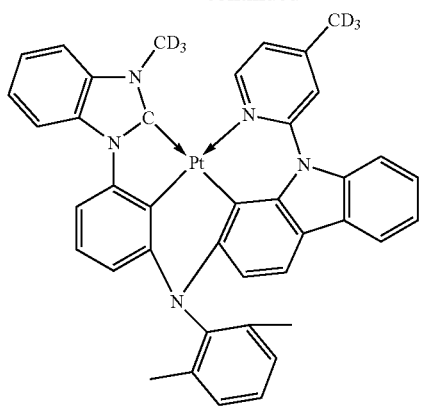
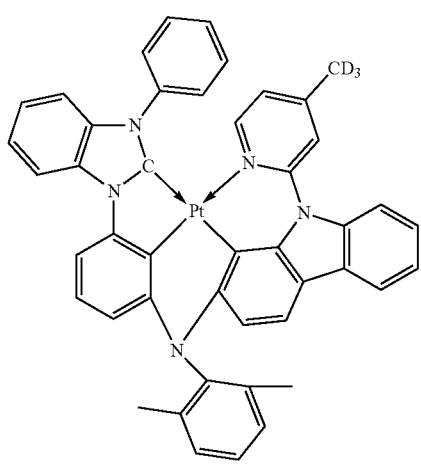
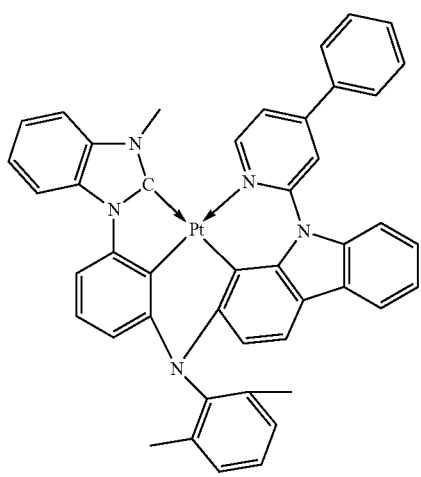
2416
-continued
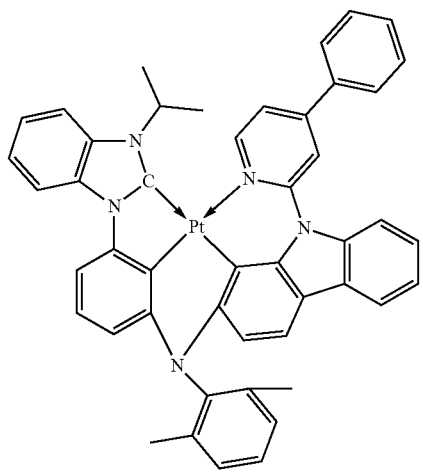
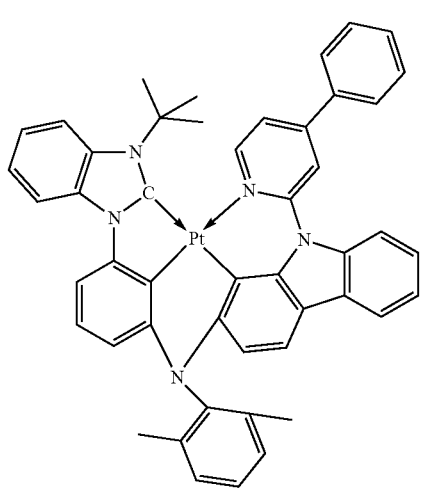
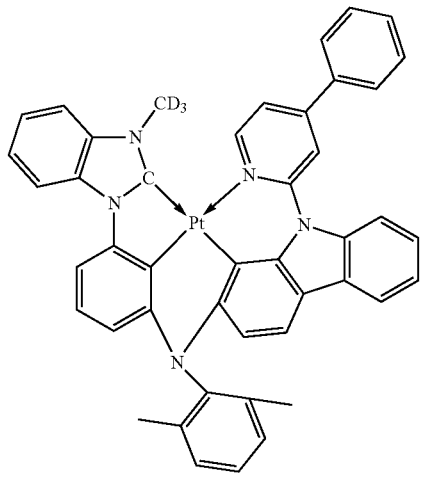

2417
-continued
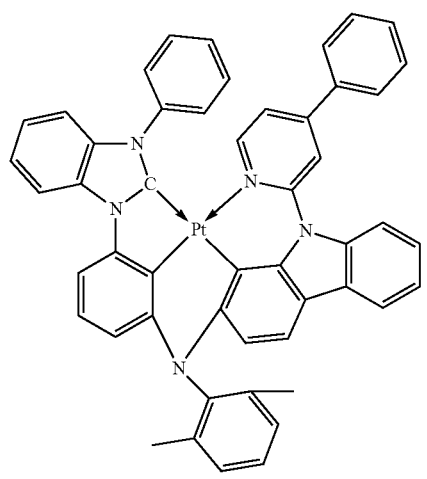
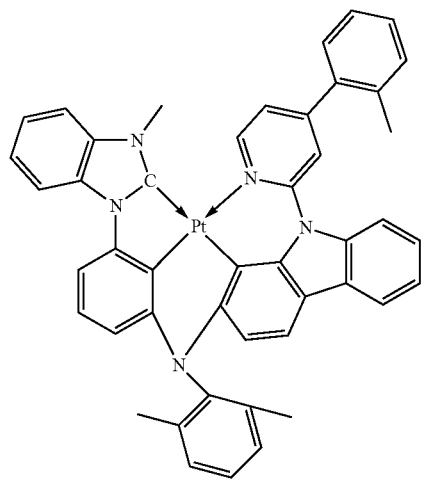
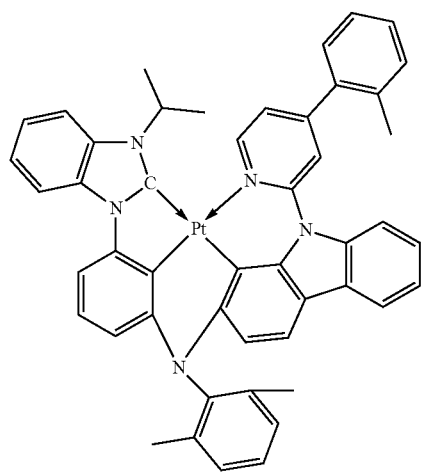
2418
-continued
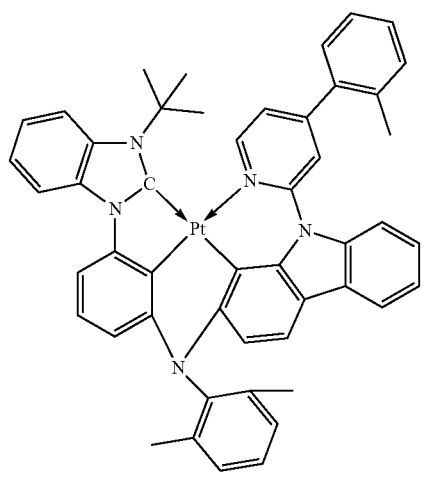
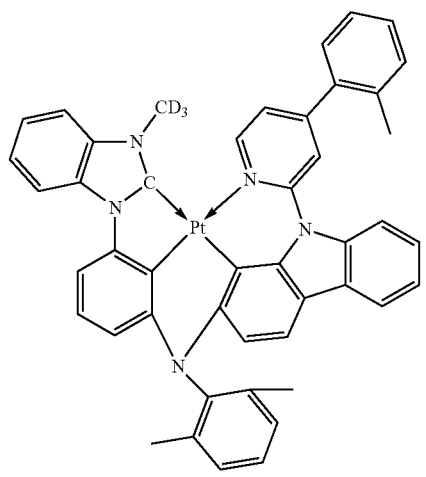
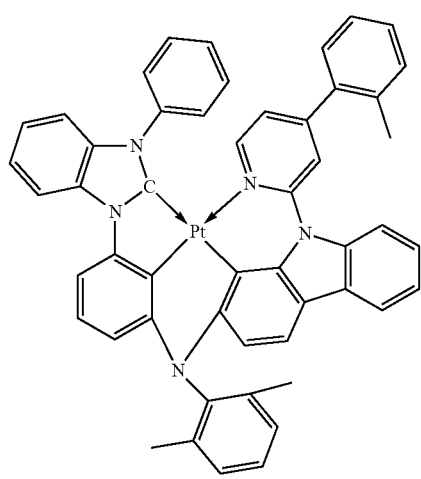

2419
-continued
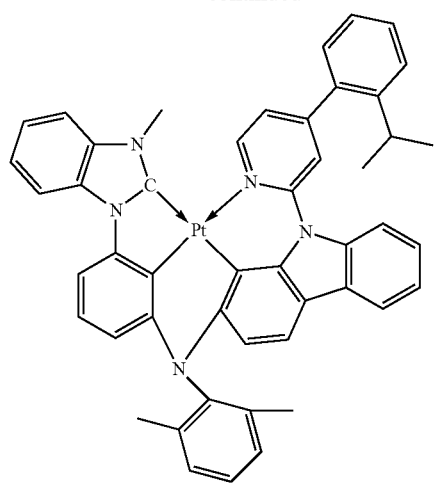
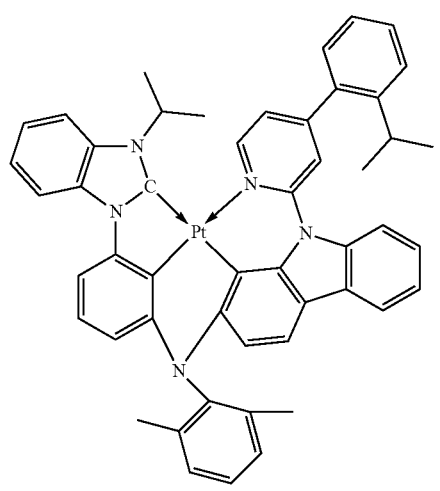
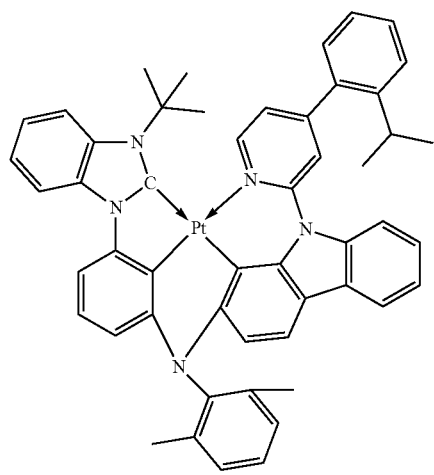
2420
-continued
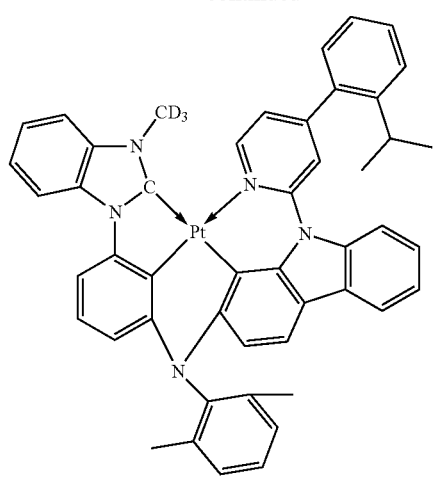
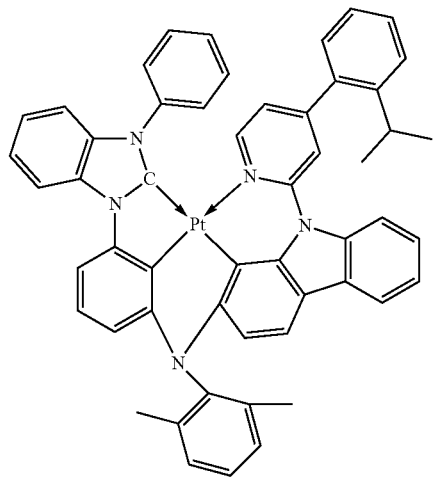
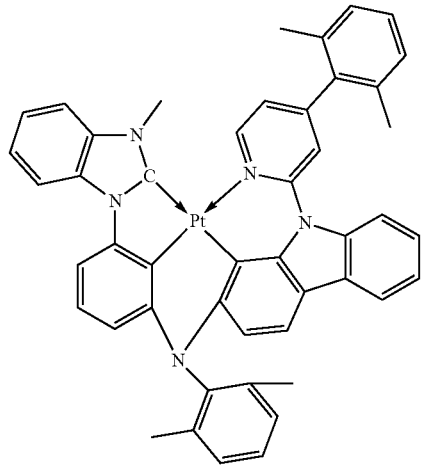

2421
-continued
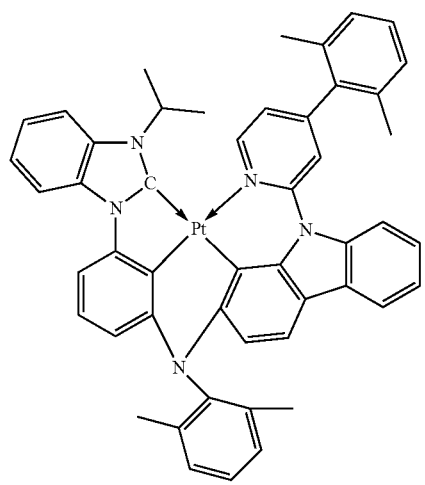
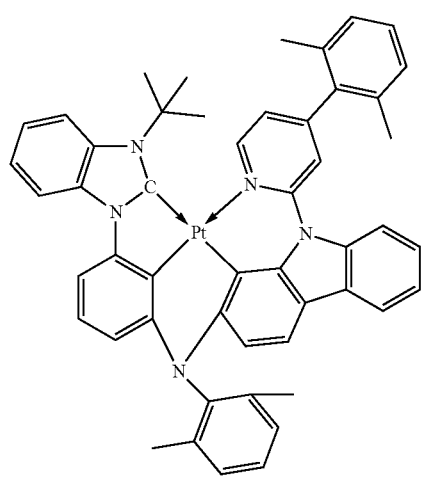
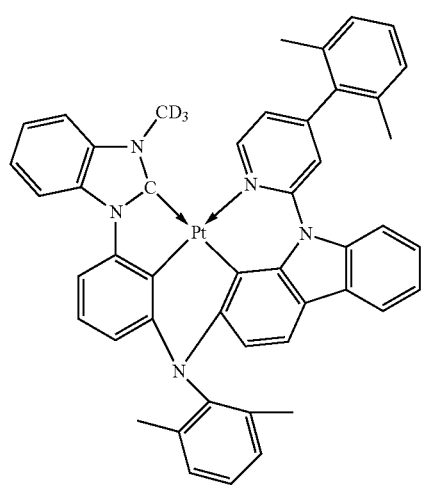
2422
-continued
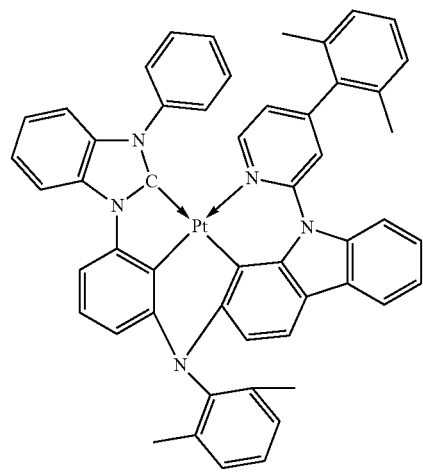
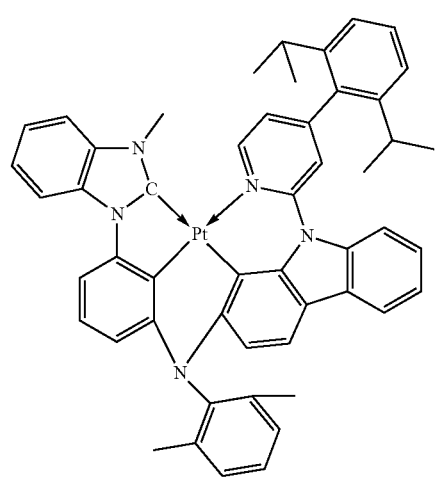
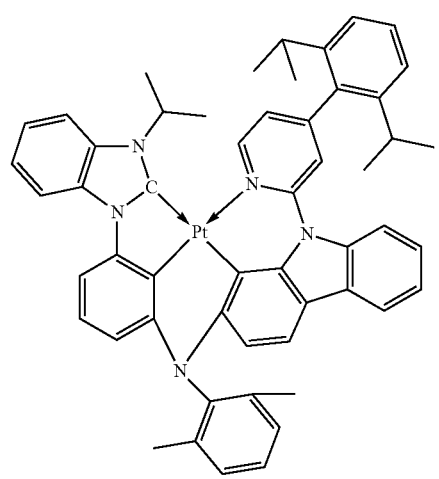

| 2423 | 2424 |
|---|---|
| 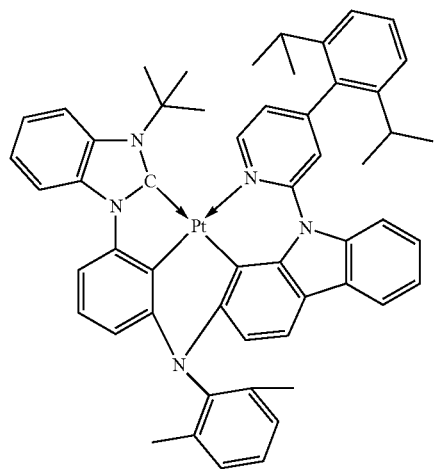 | 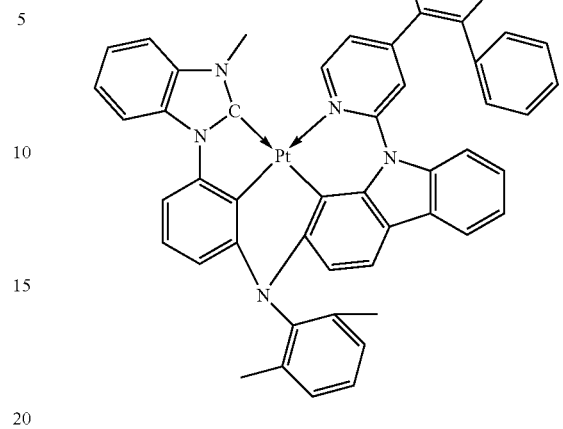 |
| 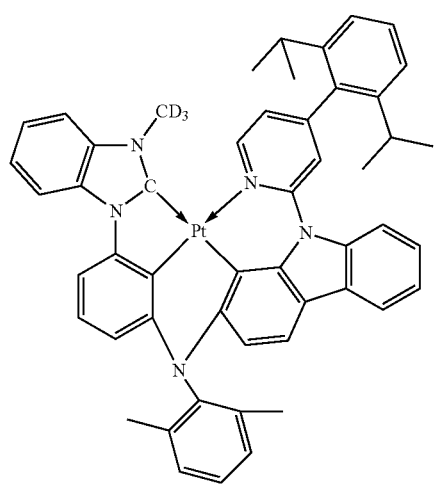 | 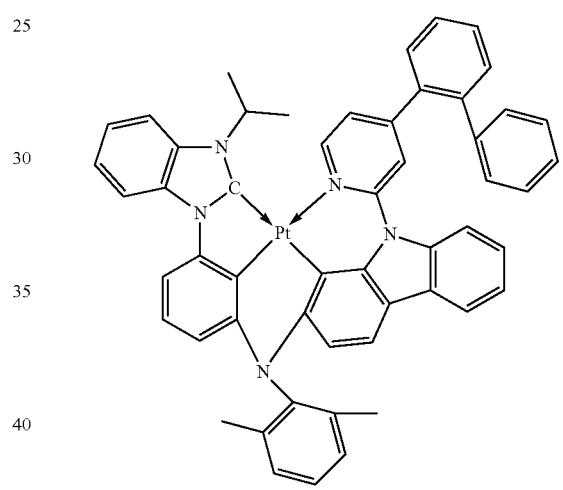 |
| 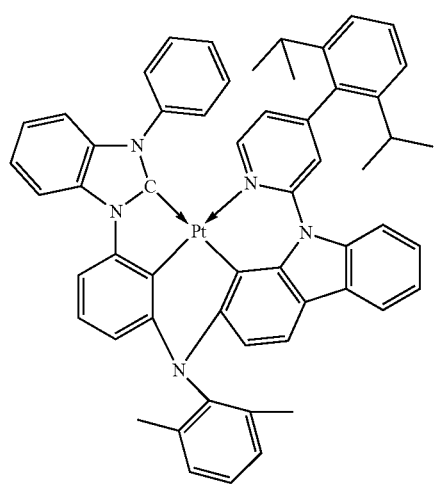 | 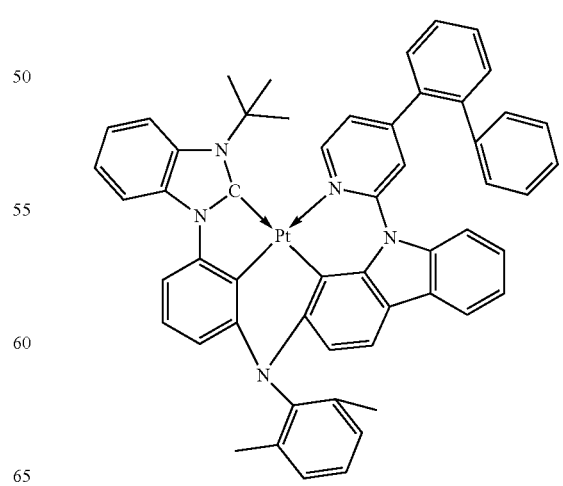 |

2425
-continued
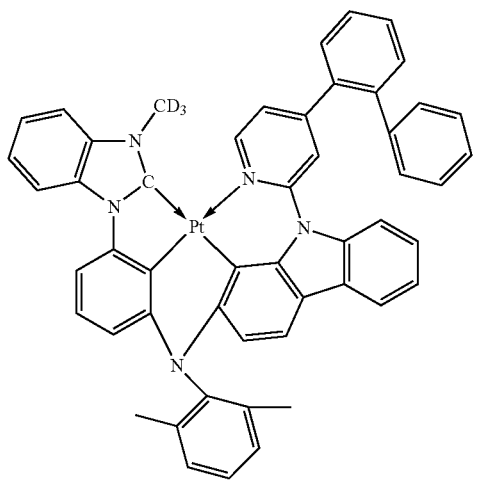
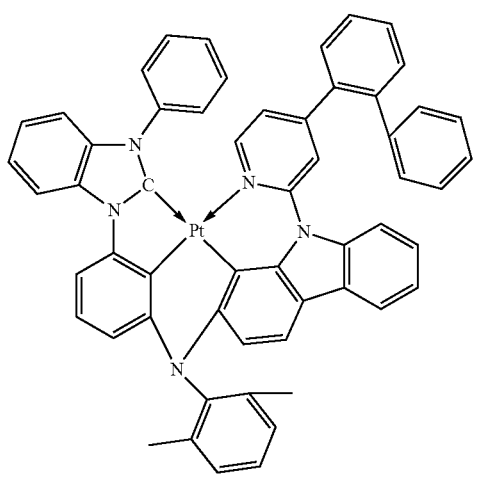
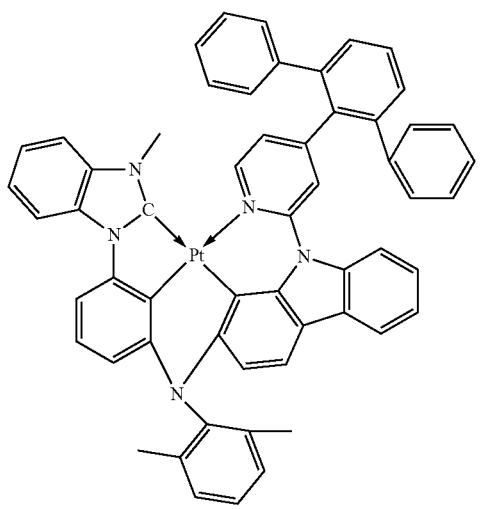
2426
-continued
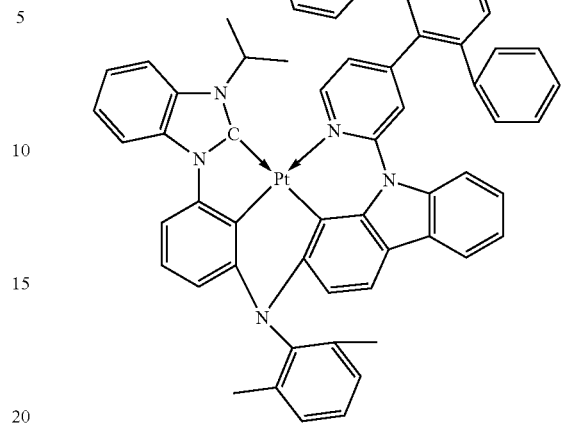
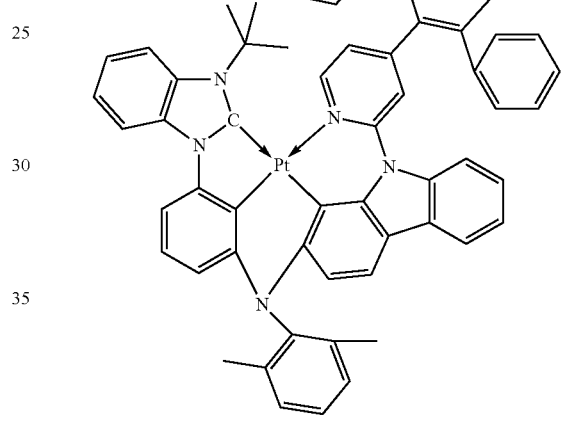
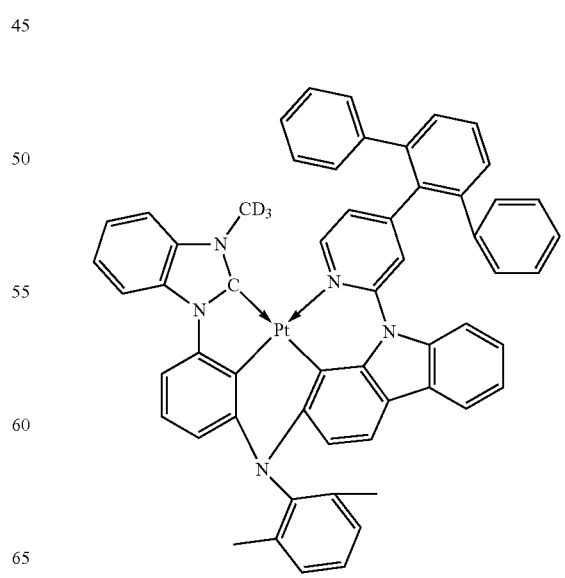

2427
-continued
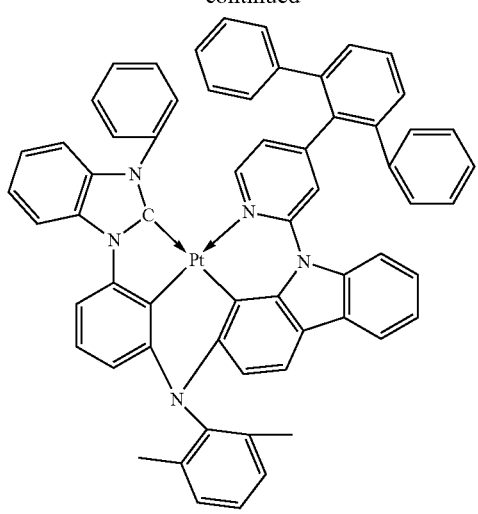
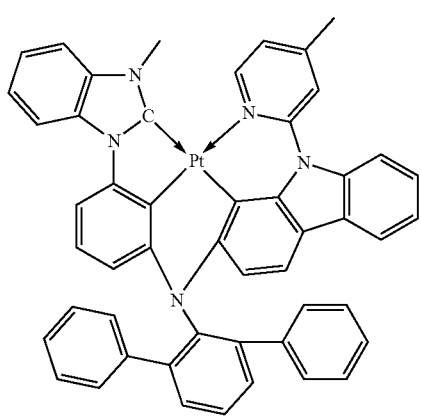
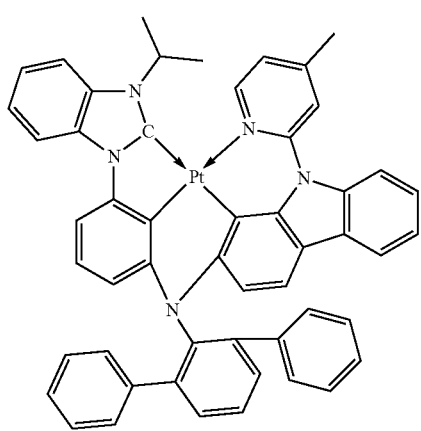
2428
-continued
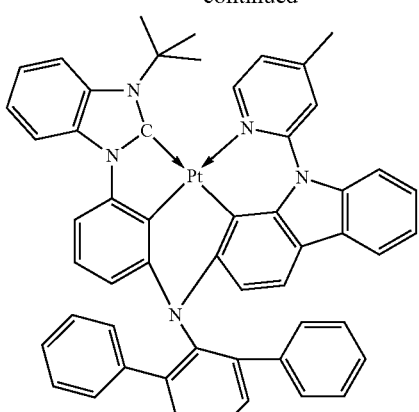
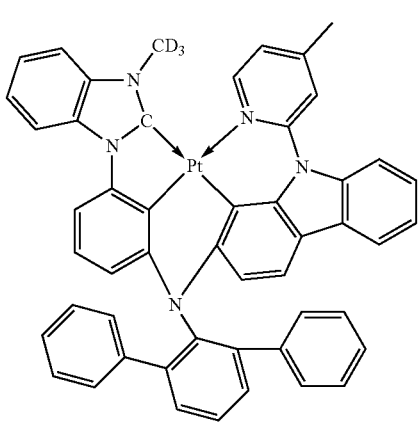
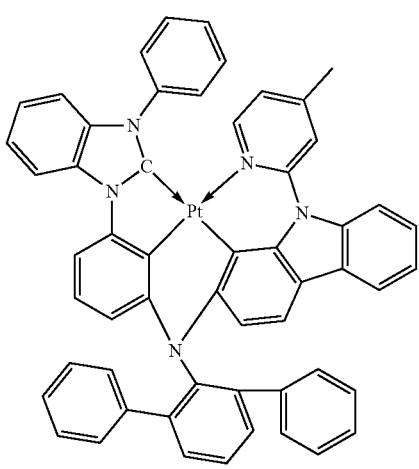

2429
-continued
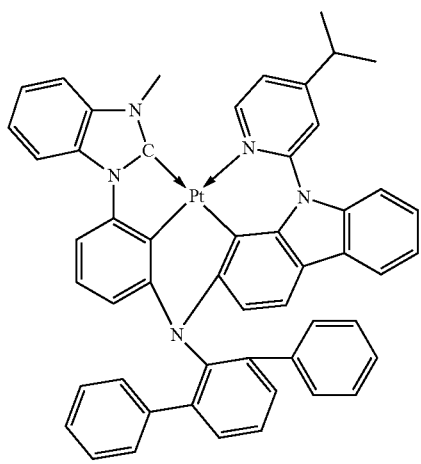
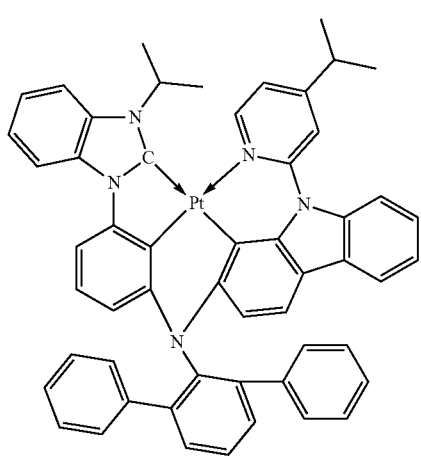
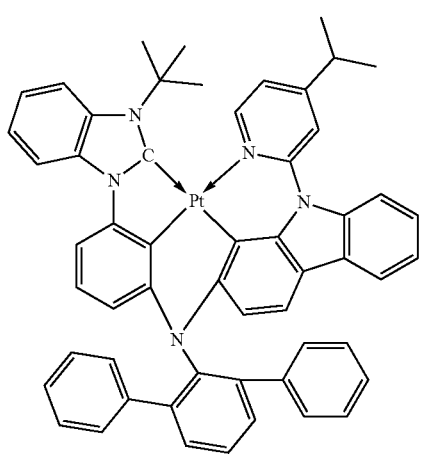
2430
-continued
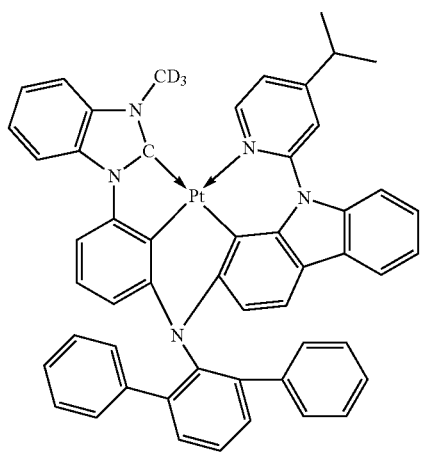
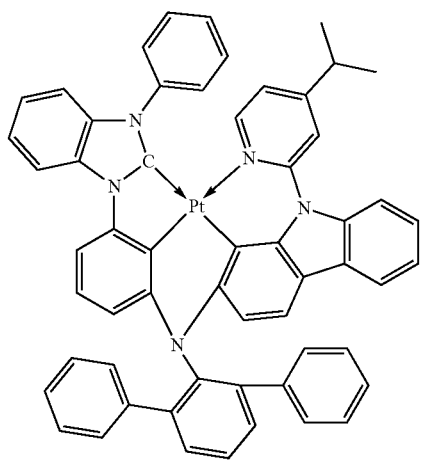
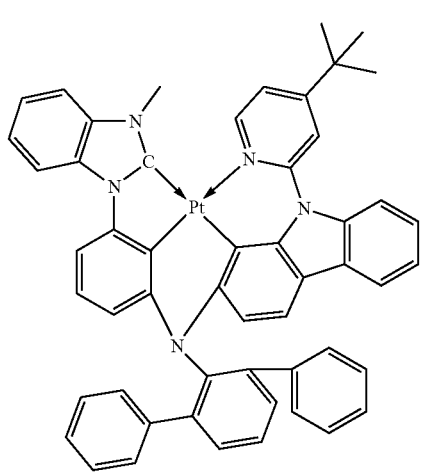

2431
-continued
2432
-continued
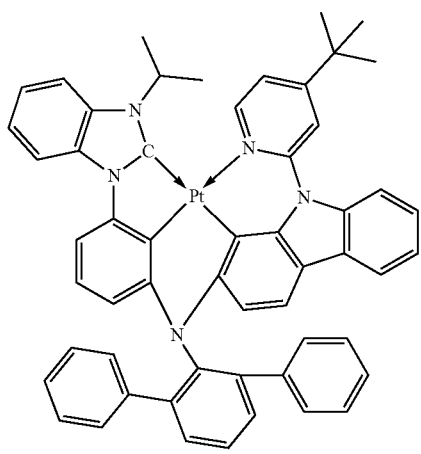
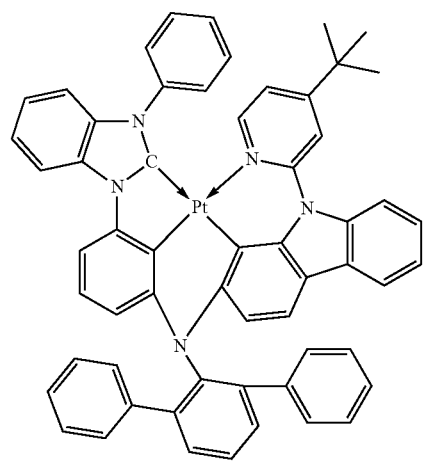
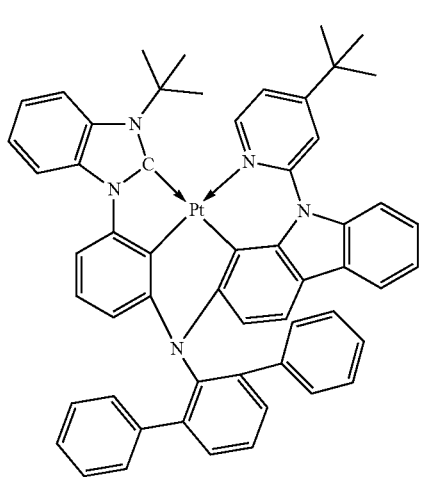
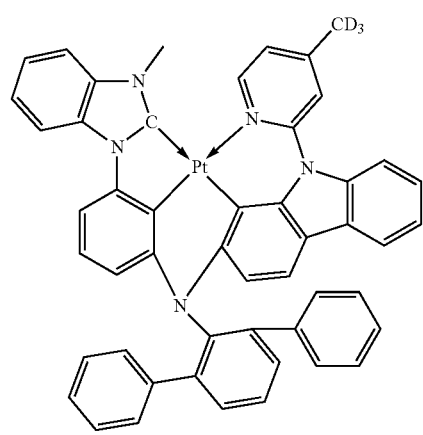
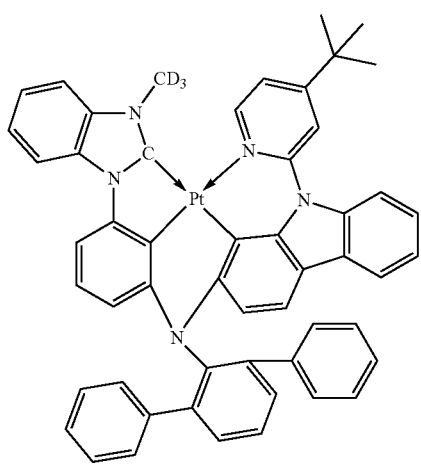
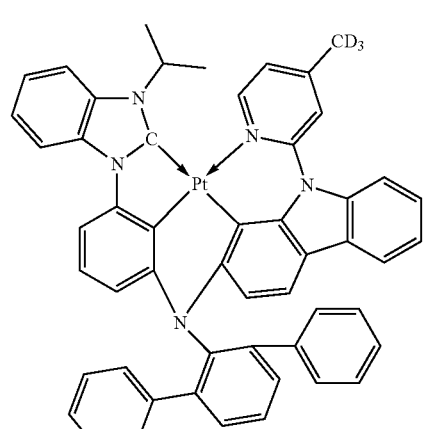

2433
-continued
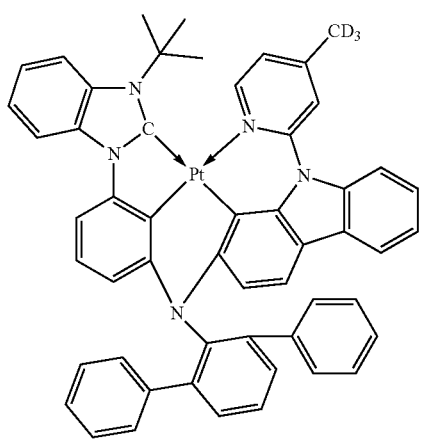
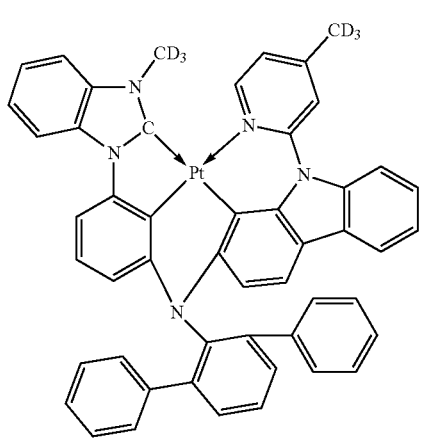
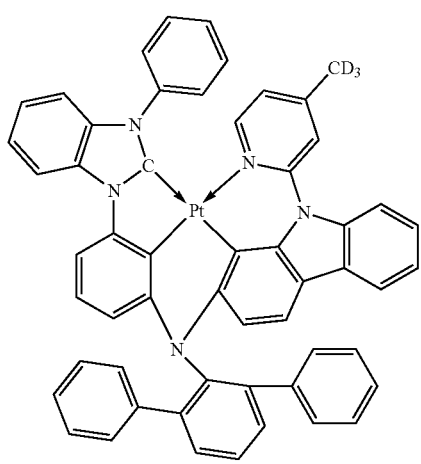
2434
-continued
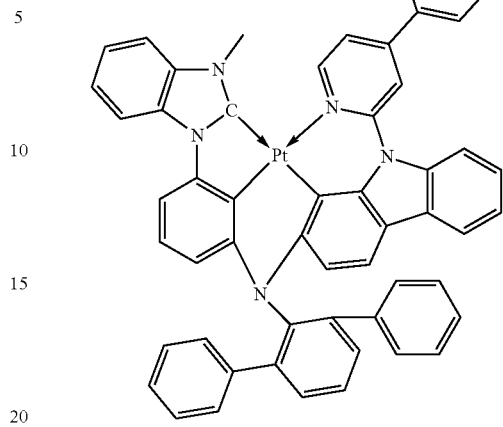
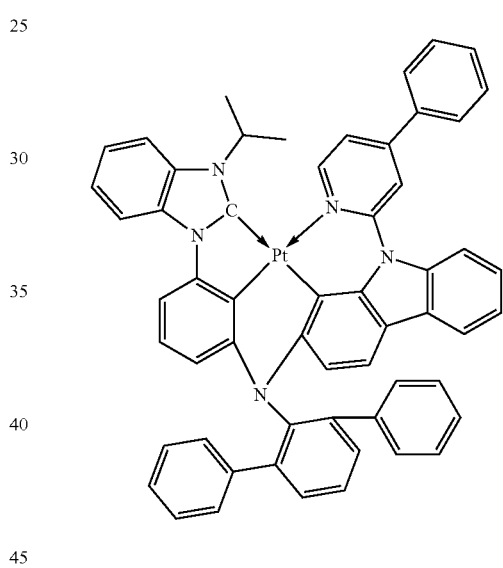
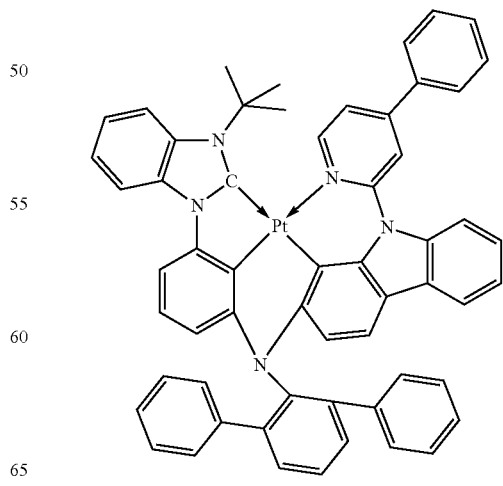

2435
-continued
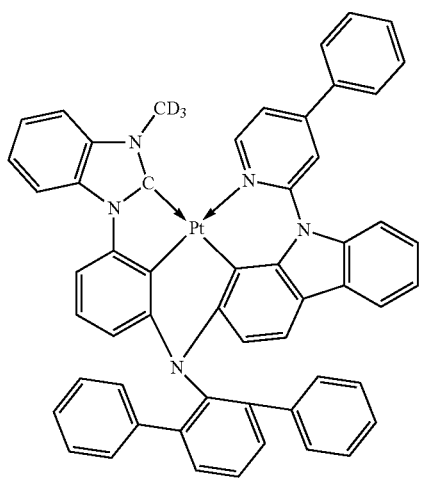
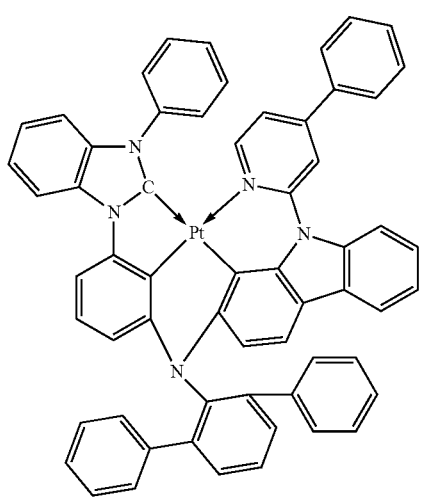
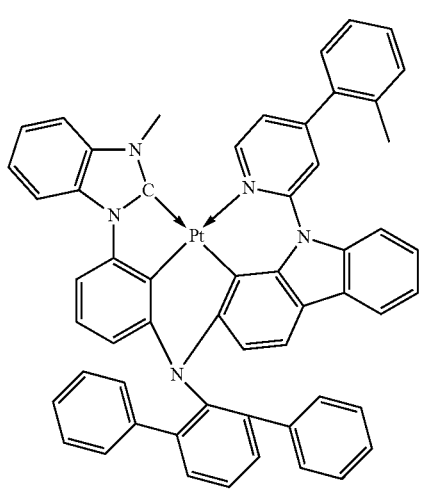
2436
-continued
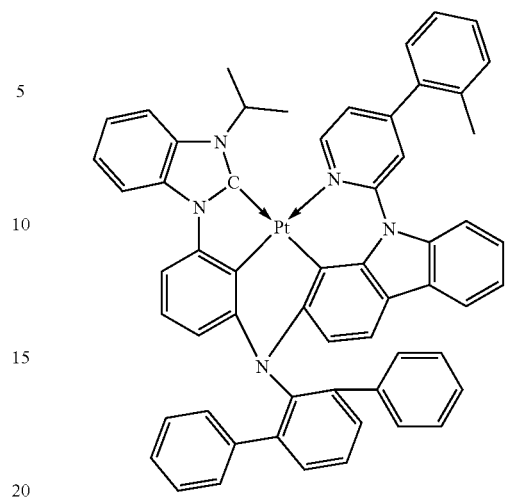
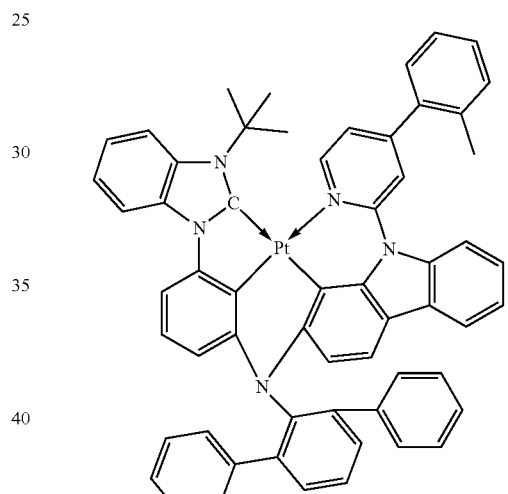
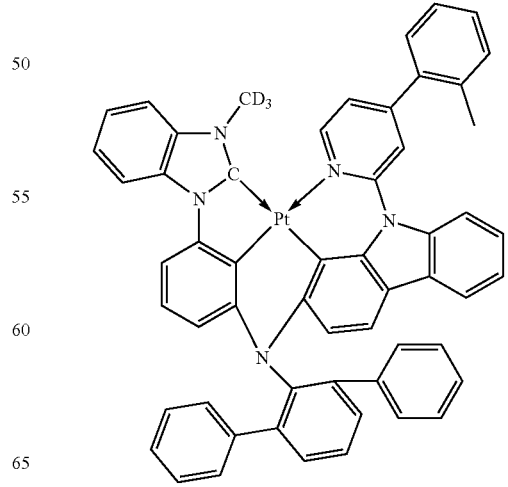

2437
-continued
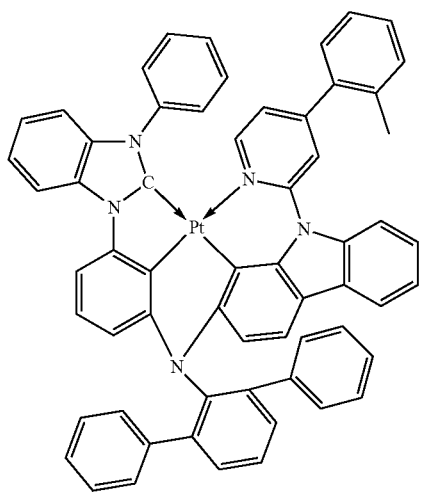
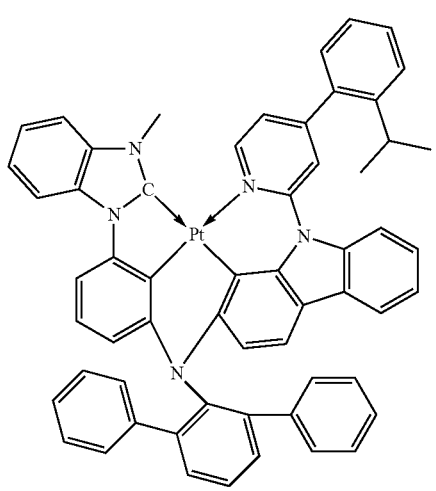
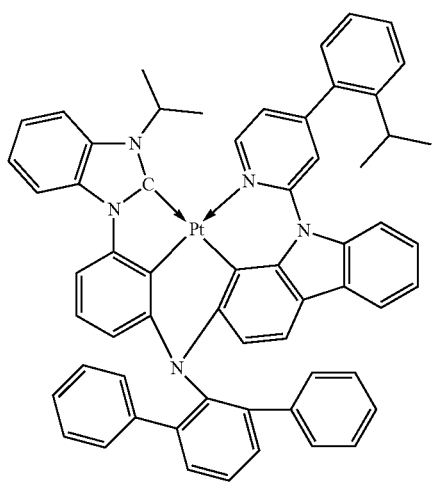
2438
-continued
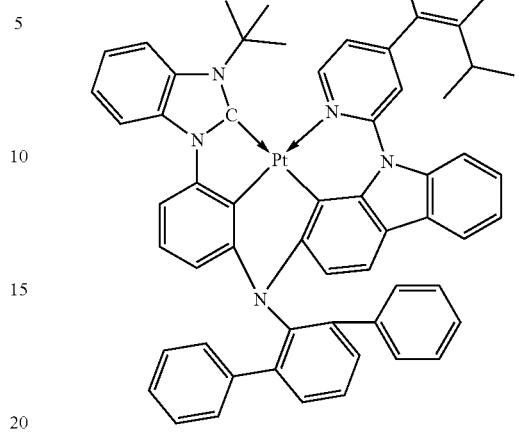
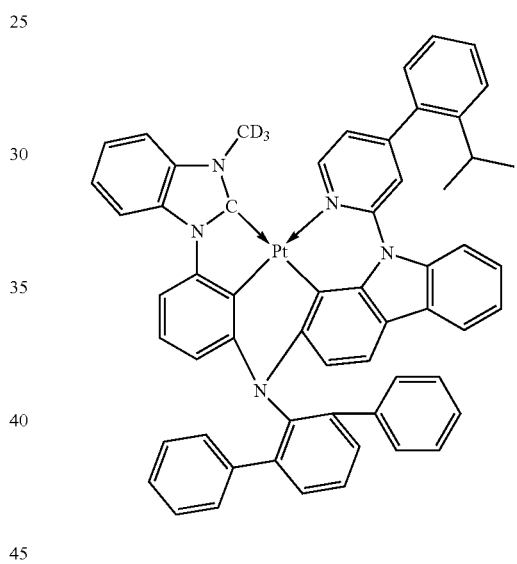
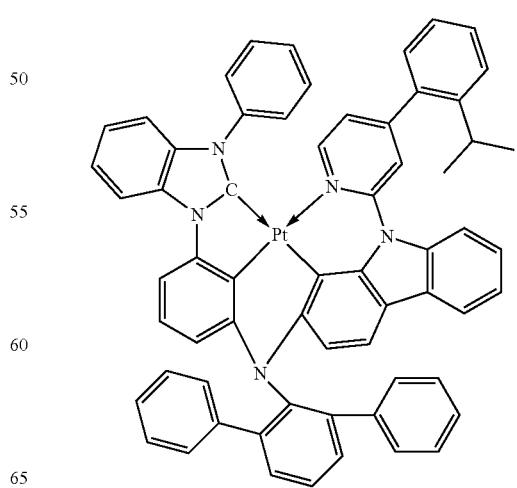

2439
-continued
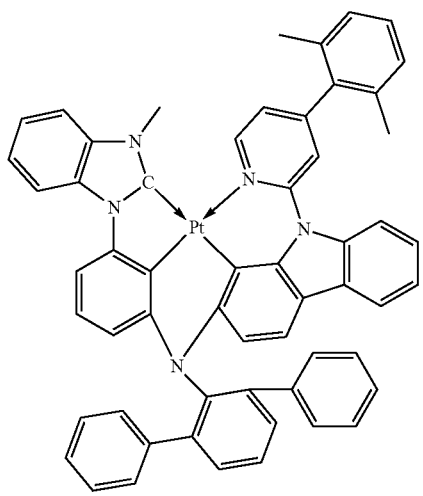
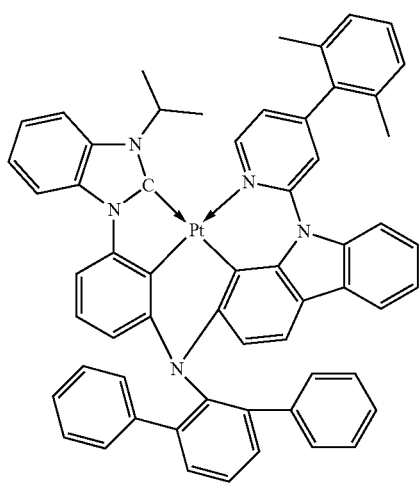
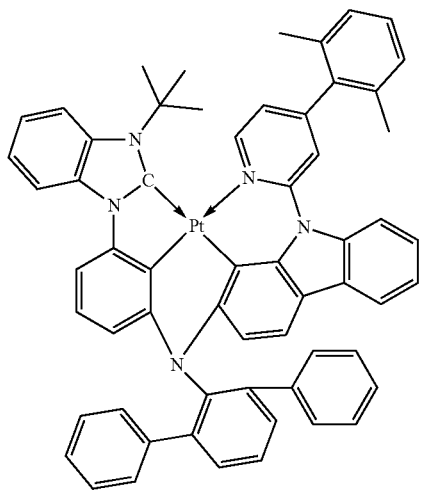
2440
-continued
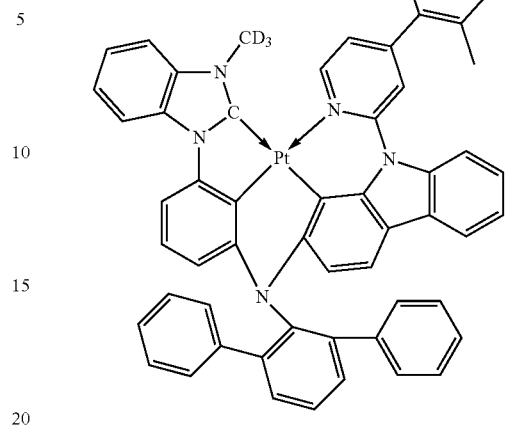
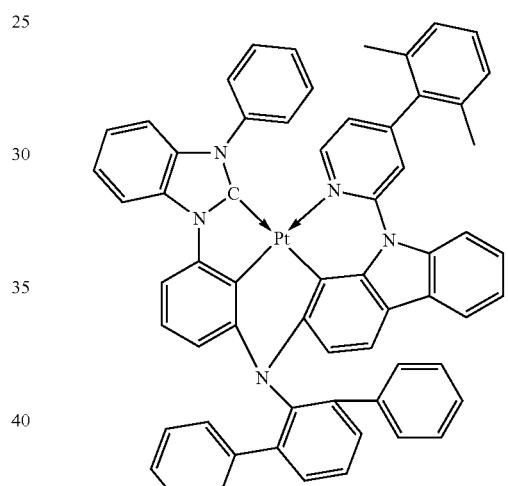
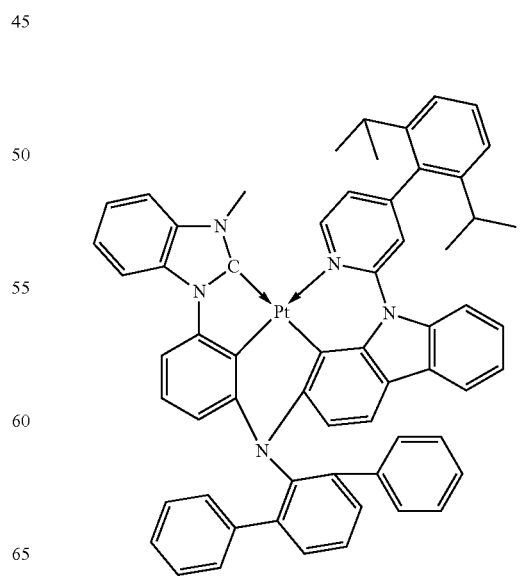

2441
-continued
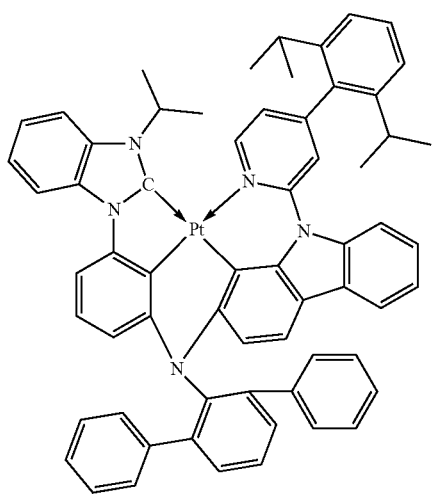
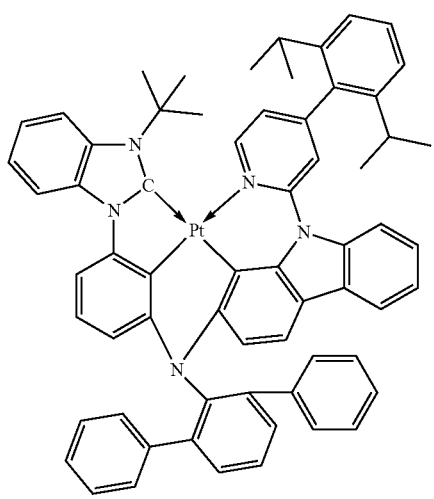
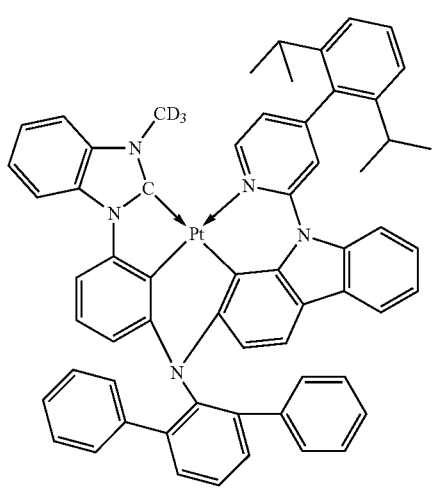
2442
-continued
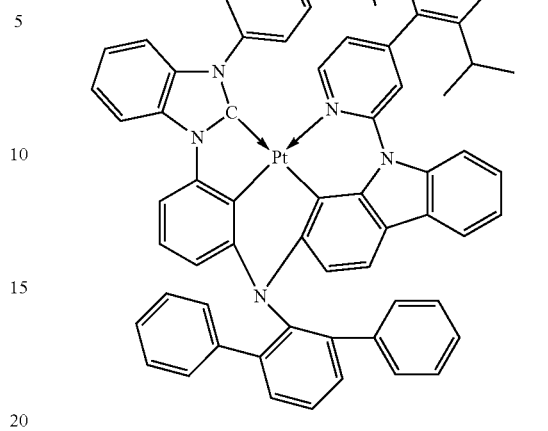
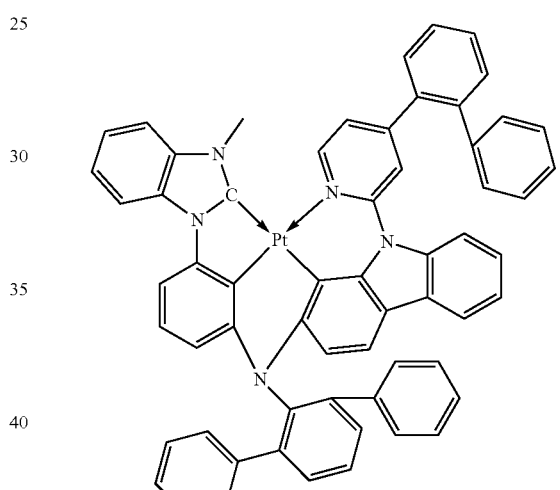
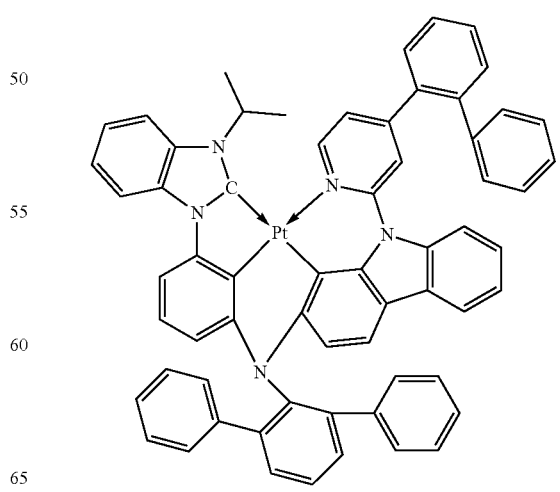

2443
-continued
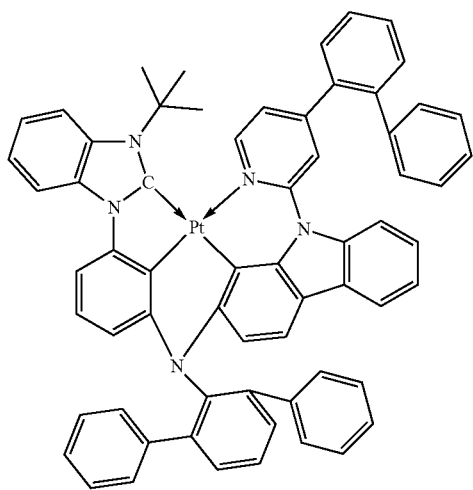
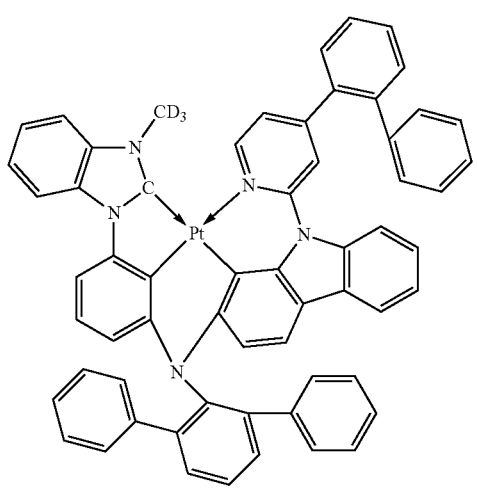
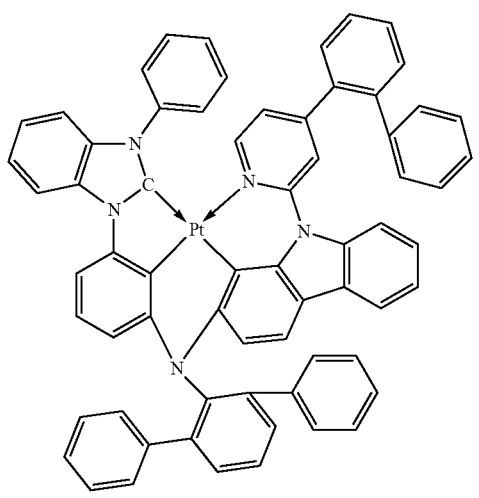
2444
-continued
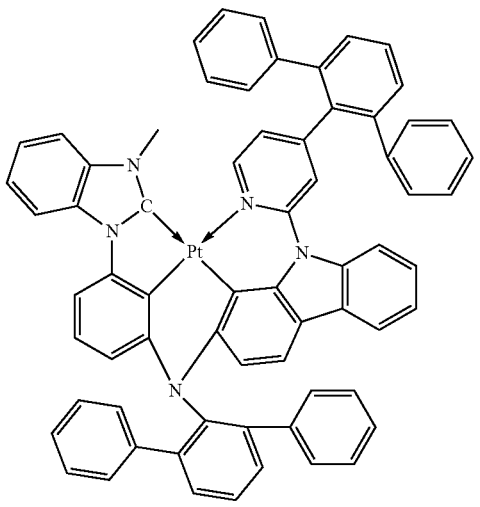
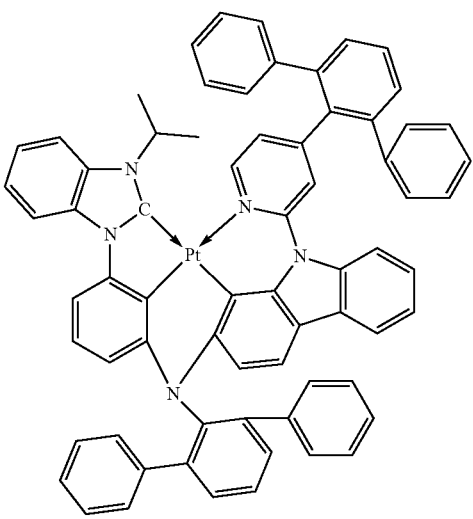
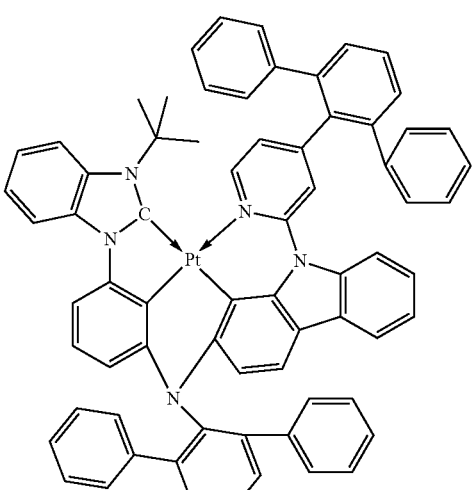

-continued
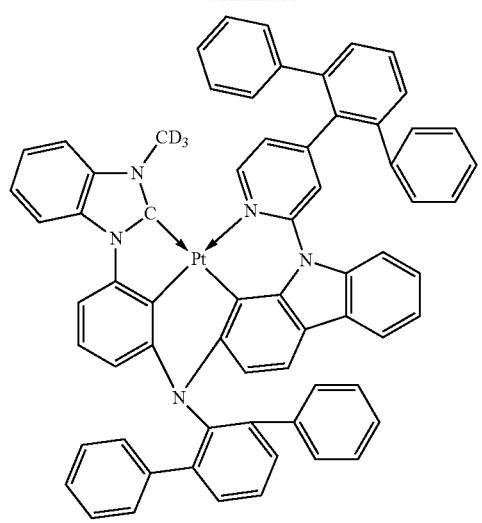
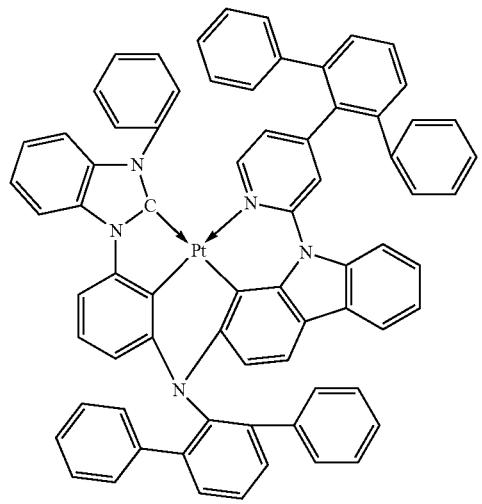
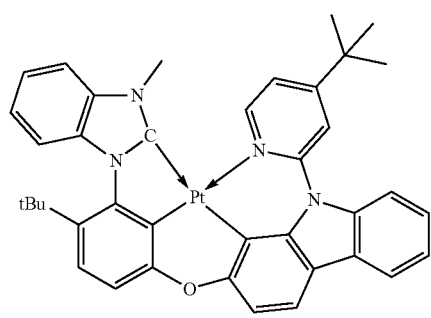
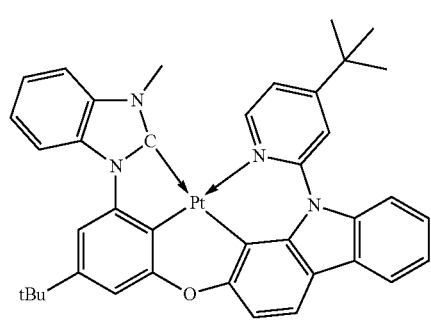
-continued
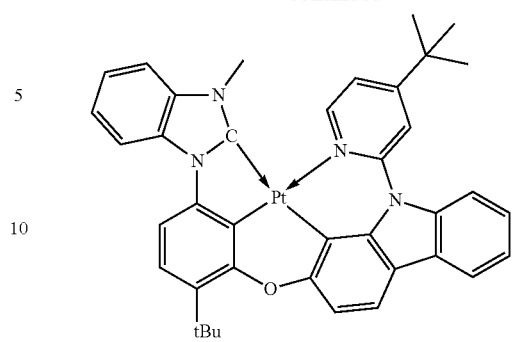
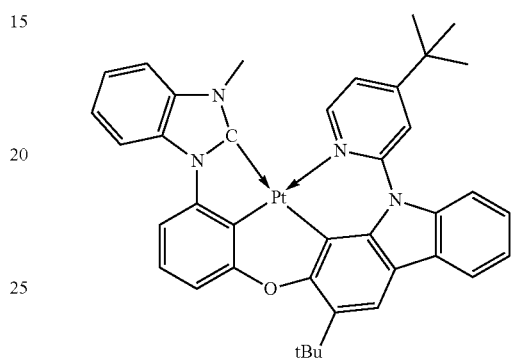
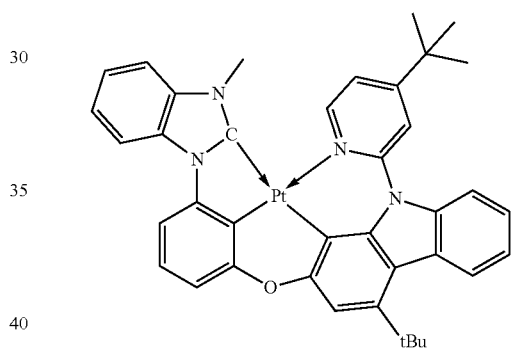
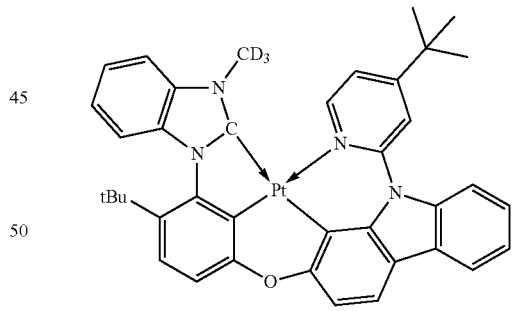
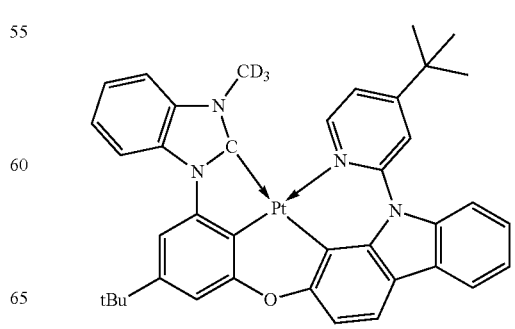

2447
-continued
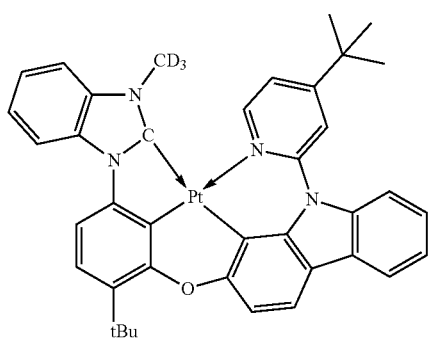
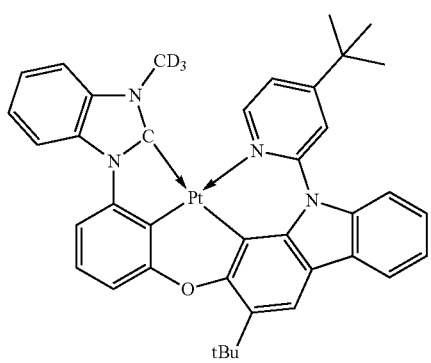
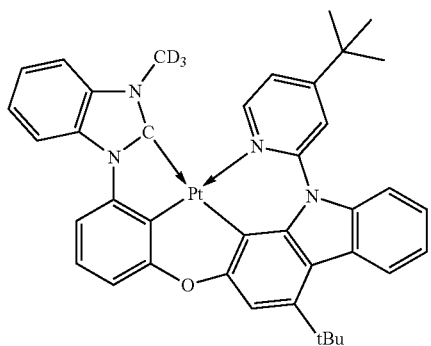
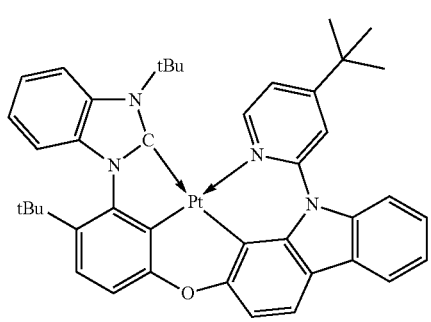
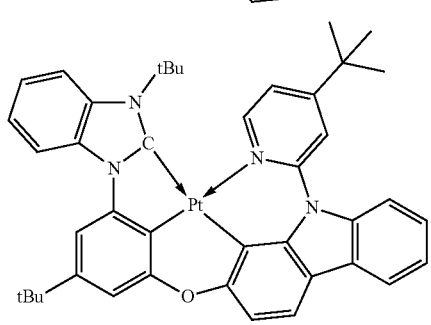
2448
-continued
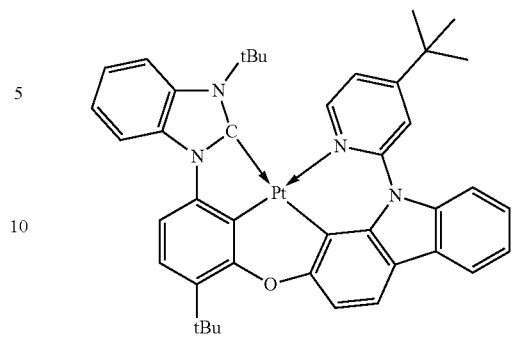
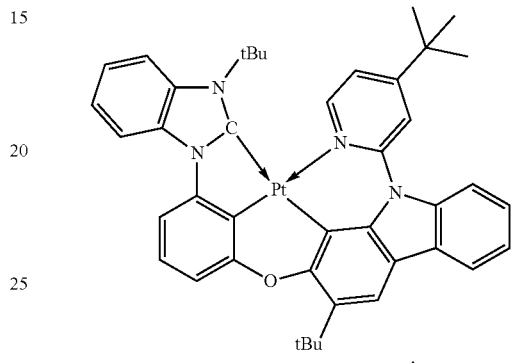
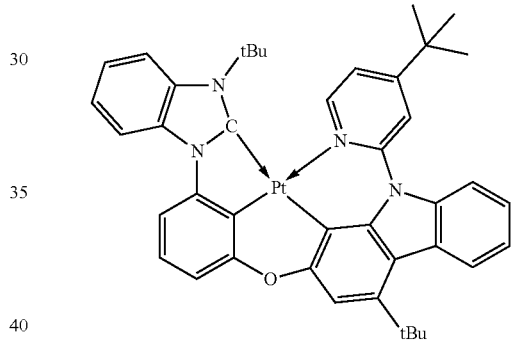
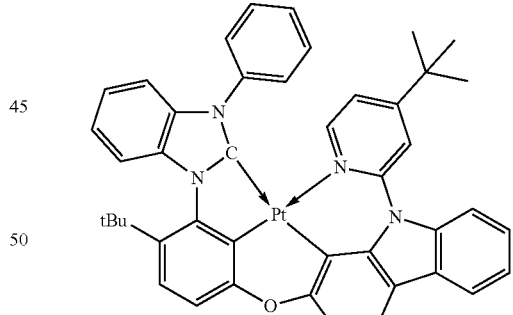
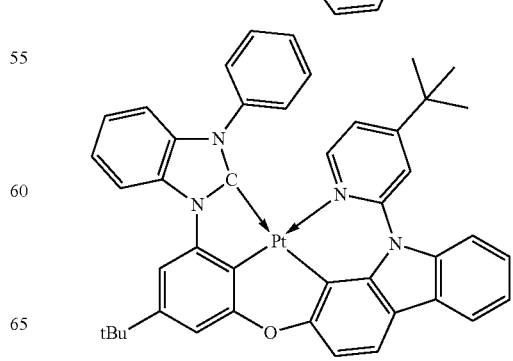

2449
-continued
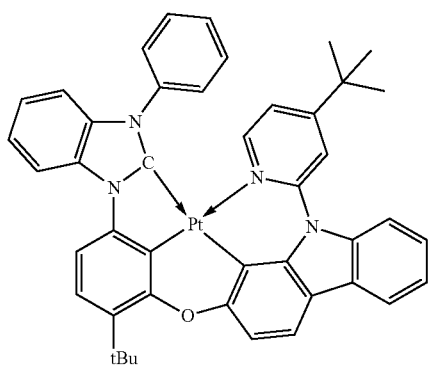
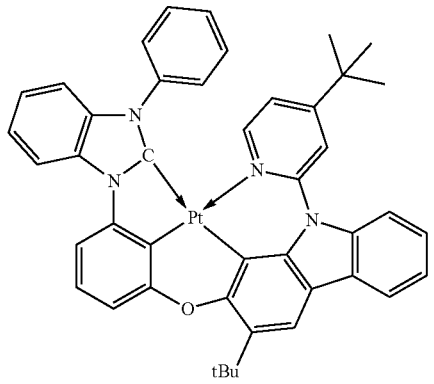
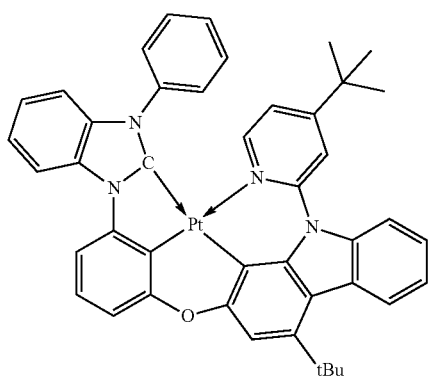
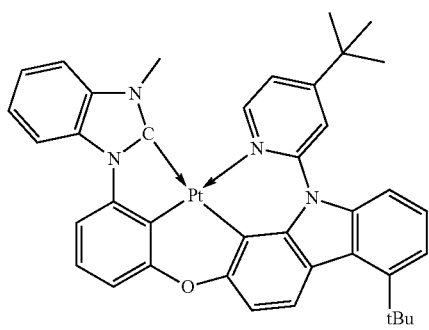
2450
-continued
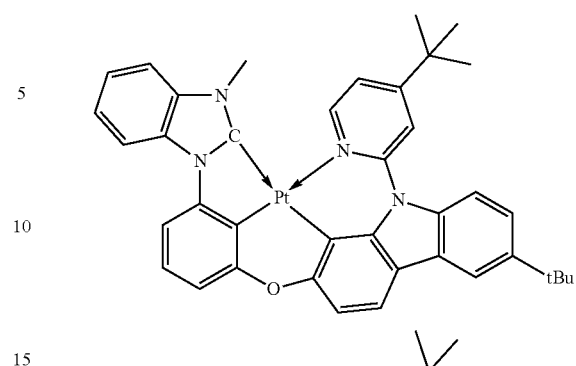
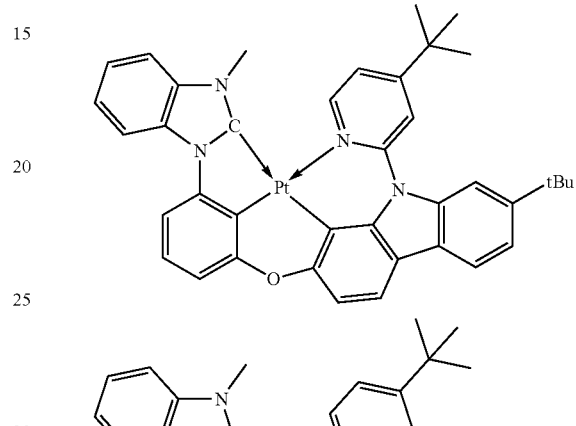
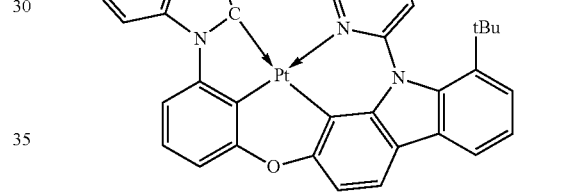
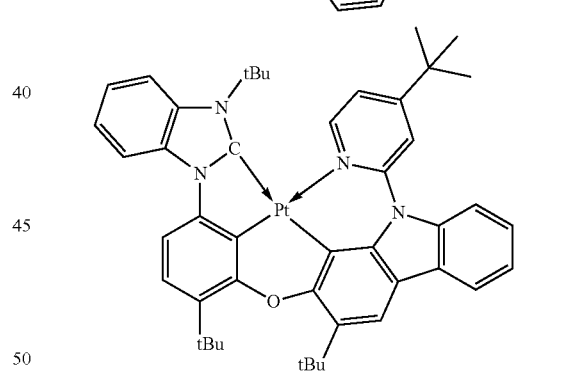
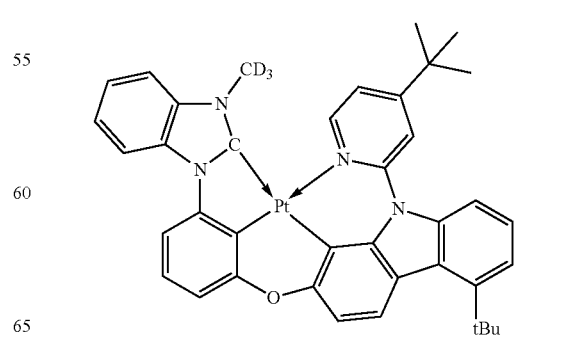

2451
-continued
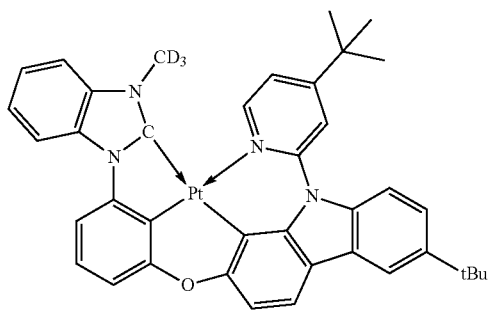
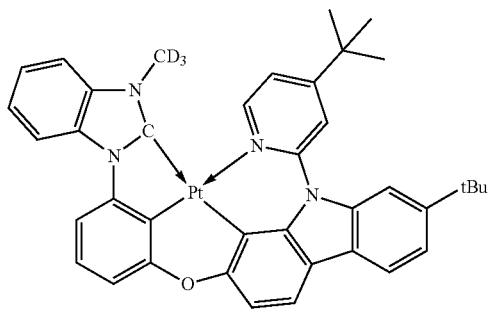
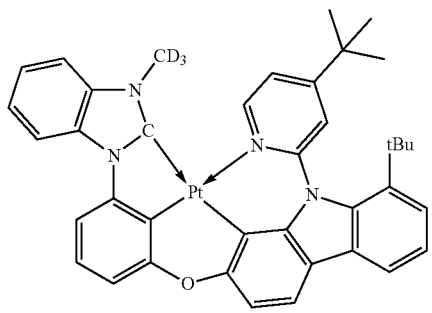
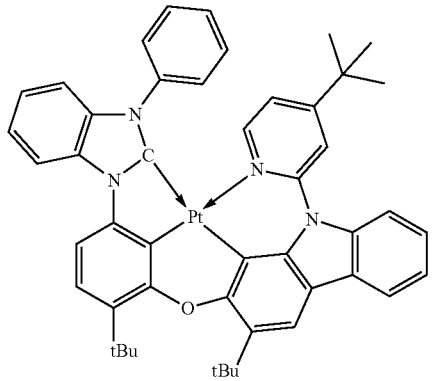
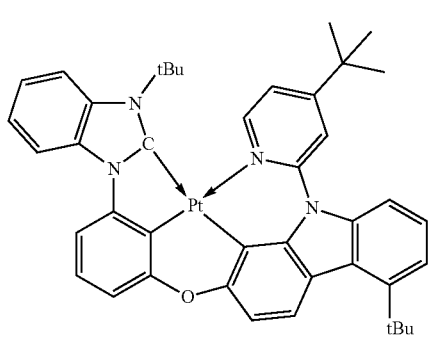
2452
-continued
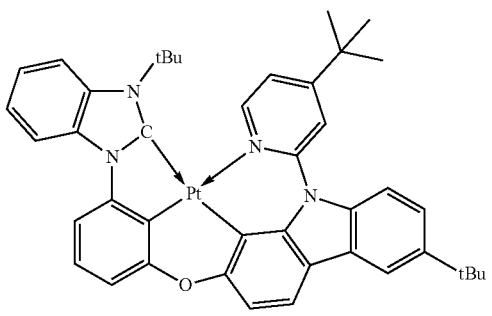
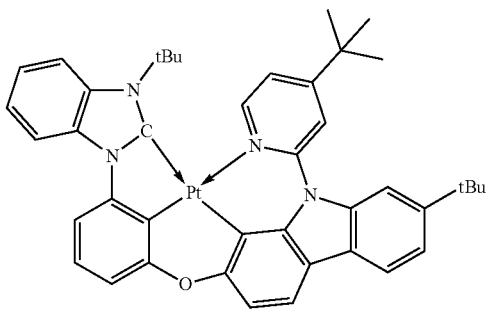
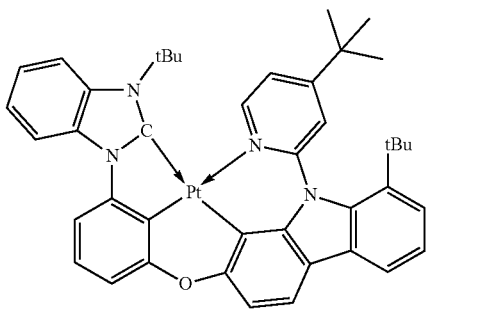
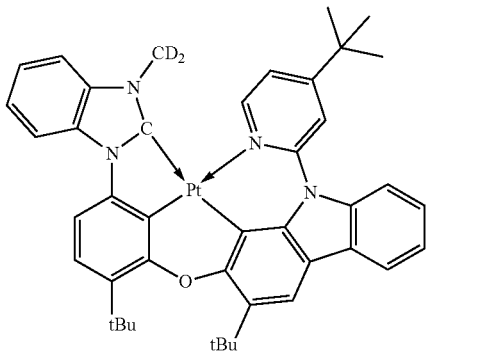
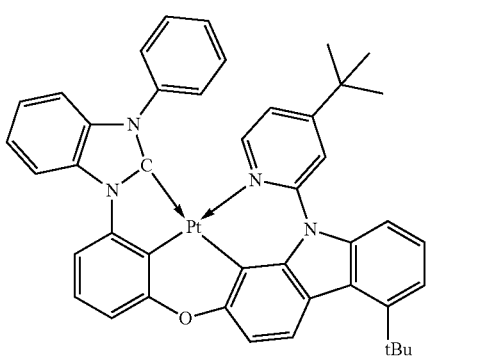

| 2453 | 2454 |
|---|---|
| 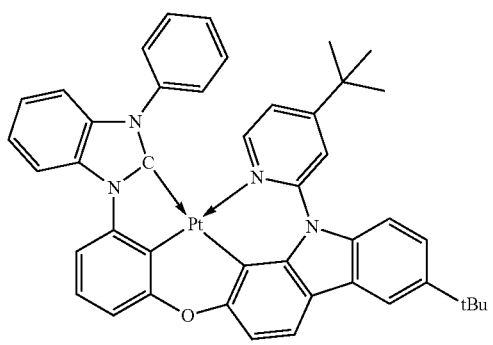 | 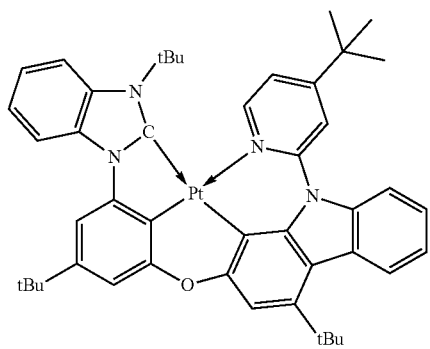 |
| 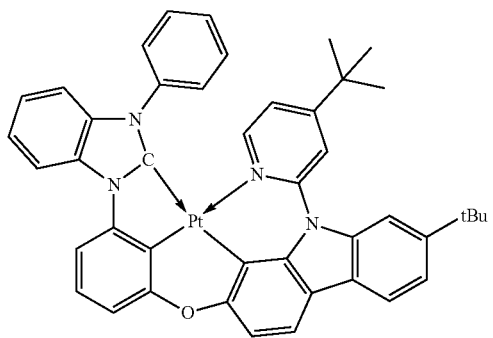 | 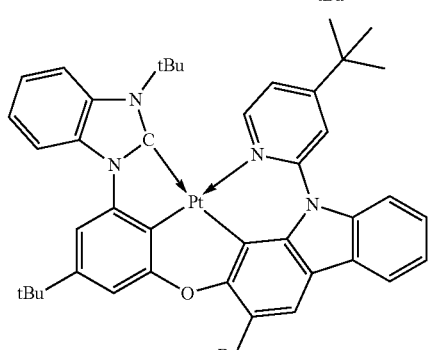 |
| 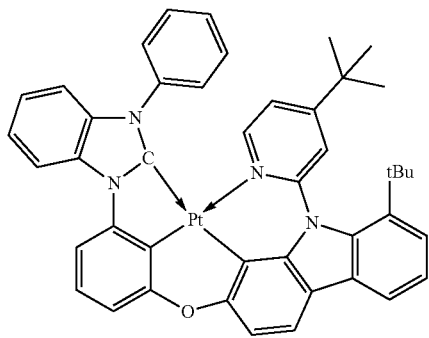 | 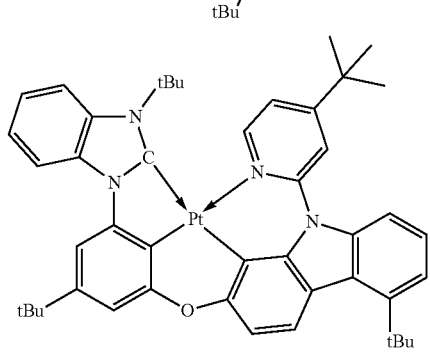 |
| 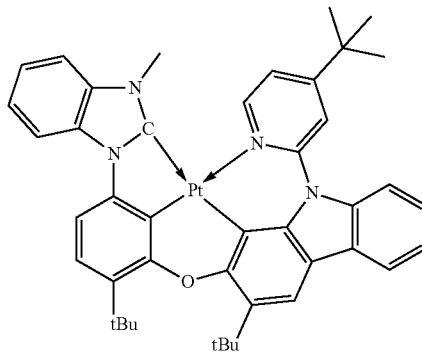 | 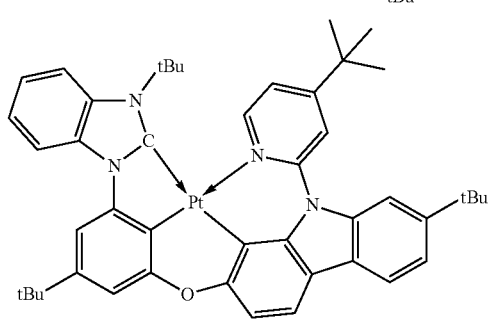 |
| 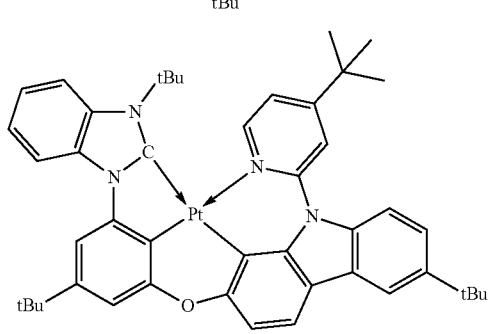 | 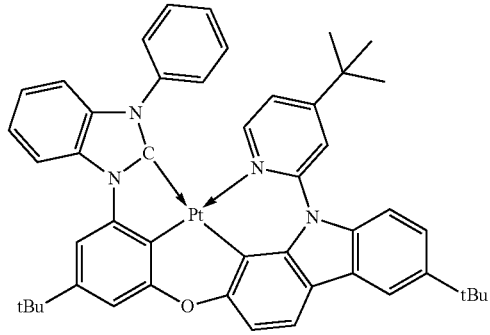 |

2455
-continued
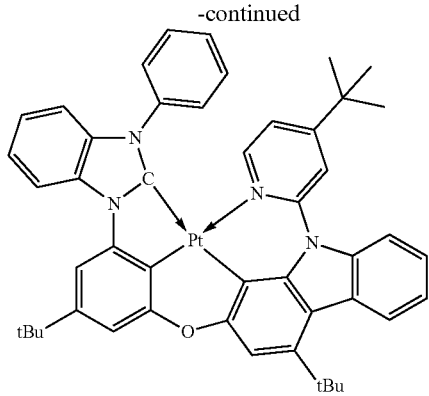
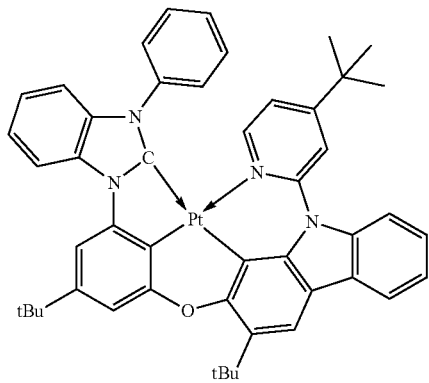
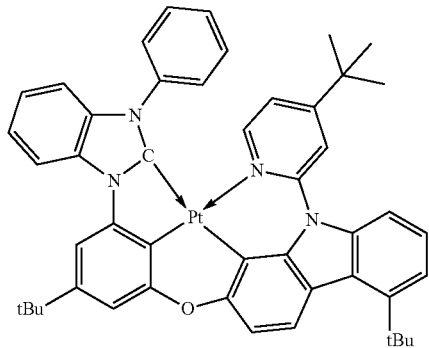
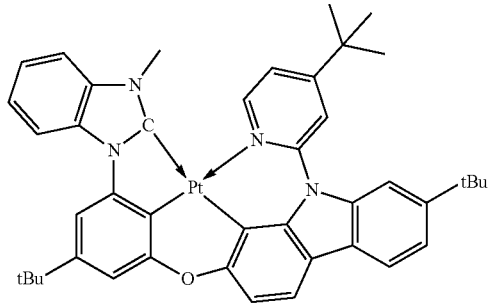
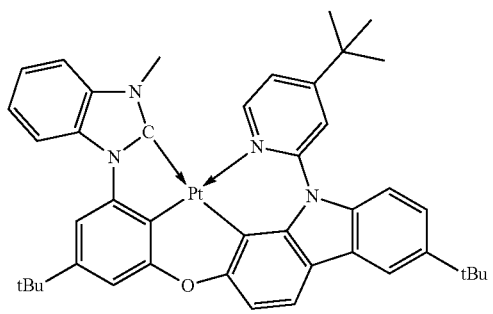
2456
-continued

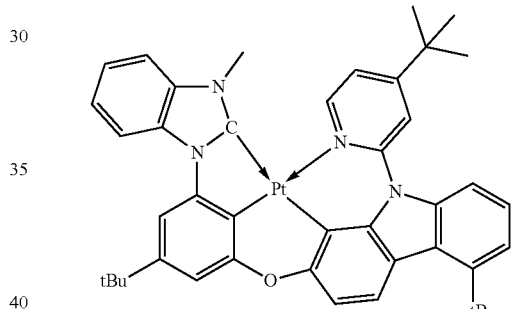
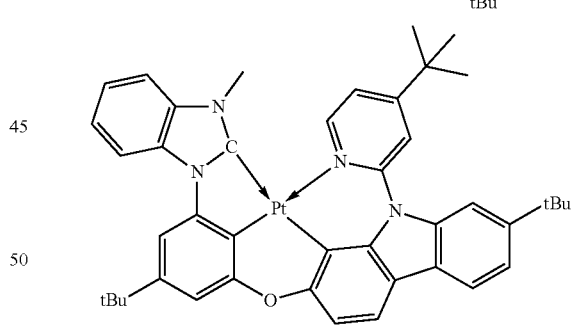
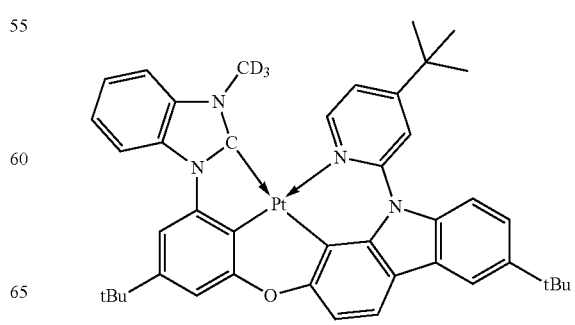

2457
-continued
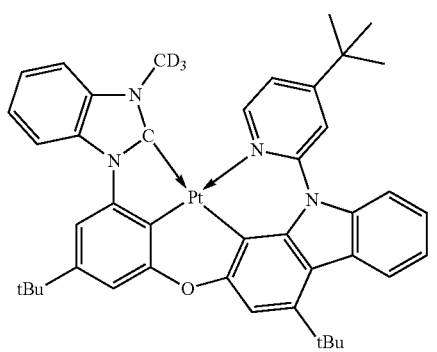
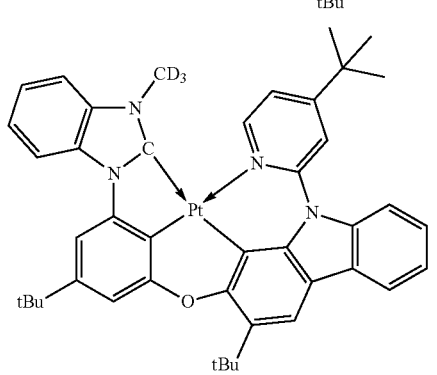
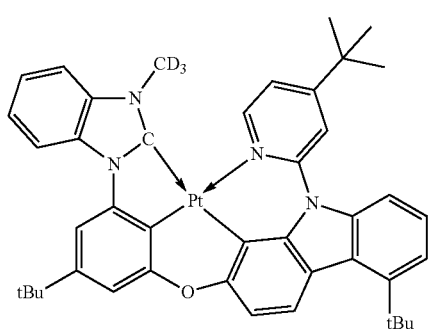
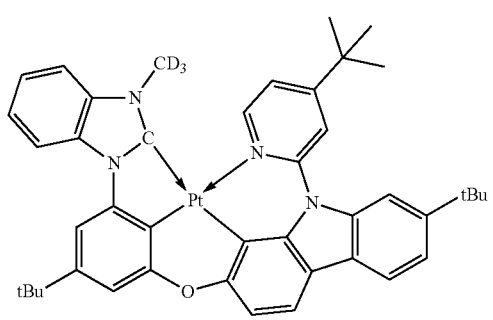
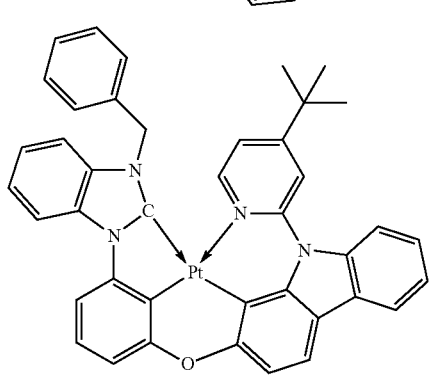
2458
-continued
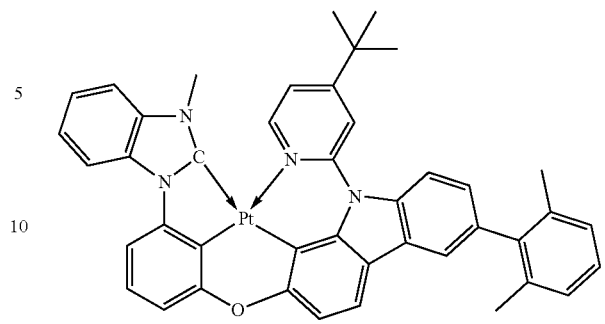
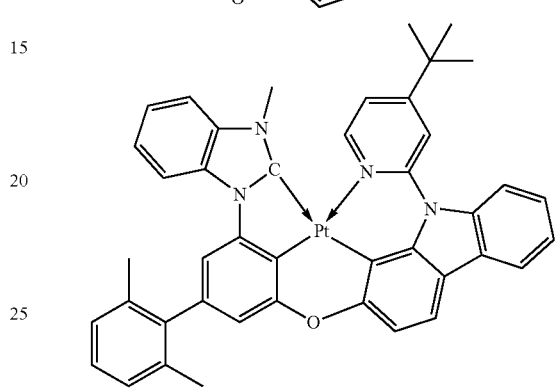
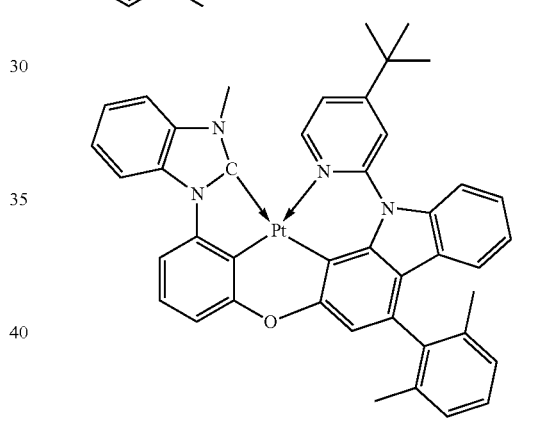
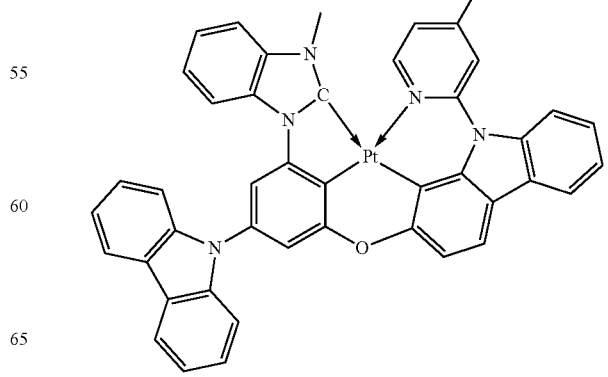

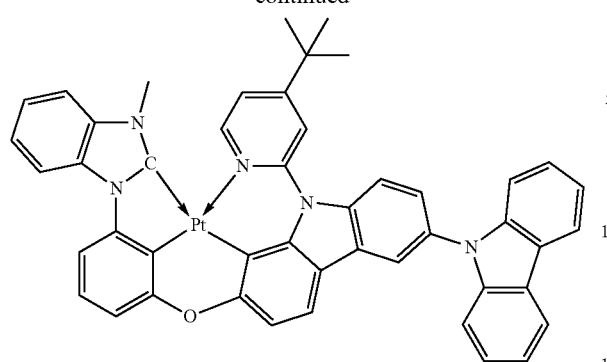
Group IV
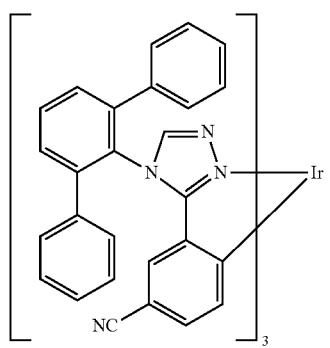
1
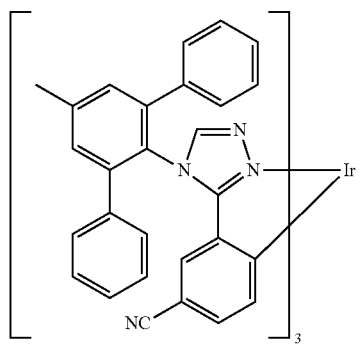
2
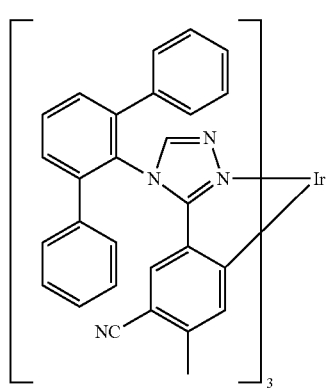
3
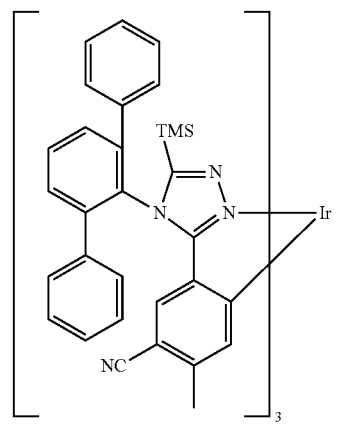
4
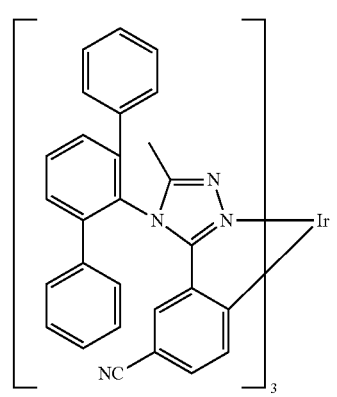
5
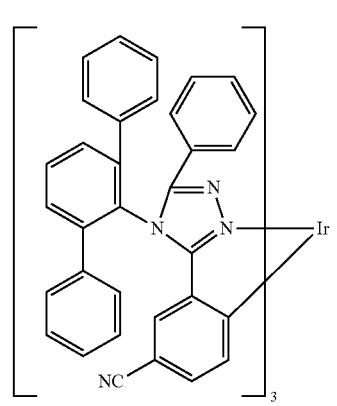
6
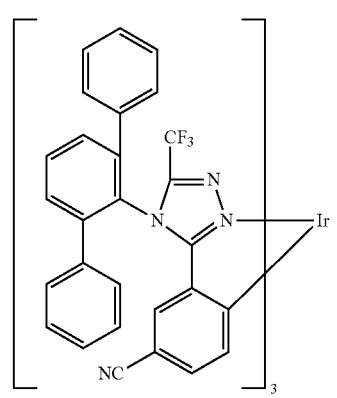
7

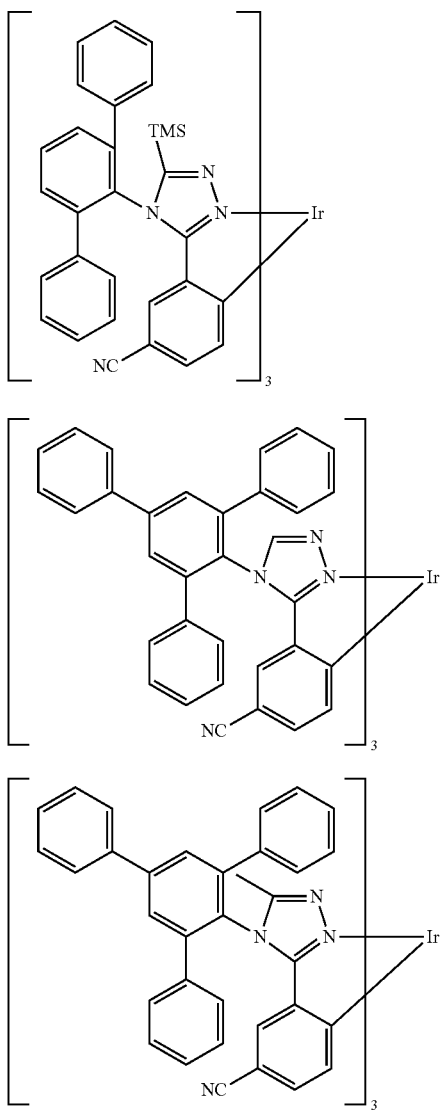

Group V

A compound represented by Formula 1:

$$(L_{101})_{n101}\text{-}M_{101}\text{-}(L_{102})_{m101} \quad \text{Formula A}$$

wherein, in Formula A, $L_{101}$, $n101$, $M_{101}$, $L_{102}$, and $m101$ may be understood by referring to Tables 11 to 13:

TABLE 11

| Compound | $L_{101}$ | n101 | $M_{101}$ | $L_{102}$ | m101 |
|---|---|---|---|---|---|
| BD001 | LM1 | 3 | Ir | — | 0 |
| BD002 | LM2 | 3 | Ir | — | 0 |
| BD003 | LM3 | 3 | Ir | — | 0 |
| BD004 | LM4 | 3 | Ir | — | 0 |
| BD005 | LM5 | 3 | Ir | — | 0 |
| BD006 | LM6 | 3 | Ir | — | 0 |
| BD007 | LM7 | 3 | Ir | — | 0 |
| BD008 | LM8 | 3 | Ir | — | 0 |
| BD009 | LM9 | 3 | Ir | — | 0 |
| BD010 | LM10 | 3 | Ir | — | 0 |
| BD011 | LM11 | 3 | Ir | — | 0 |
| BD012 | LM12 | 3 | Ir | — | 0 |
| BD013 | LM13 | 3 | Ir | — | 0 |
| BD014 | LM14 | 3 | Ir | — | 0 |
| BD015 | LM15 | 3 | Ir | — | 0 |
| BD016 | LM16 | 3 | Ir | — | 0 |
| BD017 | LM17 | 3 | Ir | — | 0 |
| BD018 | LM18 | 3 | Ir | — | 0 |
| BD019 | LM19 | 3 | Ir | — | 0 |
| BD020 | LM20 | 3 | Ir | — | 0 |
| BD021 | LM21 | 3 | Ir | — | 0 |
| BD022 | LM22 | 3 | Ir | — | 0 |
| BD023 | LM23 | 3 | Ir | — | 0 |
| BD024 | LM24 | 3 | Ir | — | 0 |
| BD025 | LM25 | 3 | Ir | — | 0 |
| BD026 | LM26 | 3 | Ir | — | 0 |
| BD027 | LM27 | 3 | Ir | — | 0 |
| BD028 | LM28 | 3 | Ir | — | 0 |
| BD029 | LM29 | 3 | Ir | — | 0 |
| BD030 | LM30 | 3 | Ir | — | 0 |
| BD031 | LM31 | 3 | Ir | — | 0 |
| BD032 | LM32 | 3 | Ir | — | 0 |
| BD033 | LM33 | 3 | Ir | — | 0 |
| BD034 | LM34 | 3 | Ir | — | 0 |
| BD035 | LM35 | 3 | Ir | — | 0 |
| BD036 | LM36 | 3 | Ir | — | 0 |
| BD037 | LM37 | 3 | Ir | — | 0 |
| BD038 | LM38 | 3 | Ir | — | 0 |
| BD039 | LM39 | 3 | Ir | — | 0 |
| BD040 | LM40 | 3 | Ir | — | 0 |
| BD041 | LM41 | 3 | Ir | — | 0 |
| BD042 | LM42 | 3 | Ir | — | 0 |
| BD043 | LM43 | 3 | Ir | — | 0 |
| BD044 | LM44 | 3 | Ir | — | 0 |
| BD045 | LM45 | 3 | Ir | — | 0 |
| BD046 | LM46 | 3 | Ir | — | 0 |
| BD047 | LM47 | 3 | Ir | — | 0 |
| BD048 | LM48 | 3 | Ir | — | 0 |
| BD049 | LM49 | 3 | Ir | — | 0 |
| BD050 | LM50 | 3 | Ir | — | 0 |
| BD051 | LM51 | 3 | Ir | — | 0 |
| BD052 | LM52 | 3 | Ir | — | 0 |
| BD053 | LM53 | 3 | Ir | — | 0 |
| BD054 | LM54 | 3 | Ir | — | 0 |
| BD055 | LM55 | 3 | Ir | — | 0 |
| BD056 | LM56 | 3 | Ir | — | 0 |
| BD057 | LM57 | 3 | Ir | — | 0 |
| BD058 | LM58 | 3 | Ir | — | 0 |
| BD059 | LM59 | 3 | Ir | — | 0 |
| BD060 | LM60 | 3 | Ir | — | 0 |
| BD061 | LM61 | 3 | Ir | — | 0 |
| BD062 | LM62 | 3 | Ir | — | 0 |
| BD063 | LM63 | 3 | Ir | — | 0 |
| BD064 | LM64 | 3 | Ir | — | 0 |
| BD065 | LM65 | 3 | Ir | — | 0 |
| BD066 | LM66 | 3 | Ir | — | 0 |
| BD067 | LM67 | 3 | Ir | — | 0 |
| BD068 | LM68 | 3 | Ir | — | 0 |
| BD069 | LM69 | 3 | Ir | — | 0 |
| BD070 | LM70 | 3 | Ir | — | 0 |
| BD071 | LM71 | 3 | Ir | — | 0 |
| BD072 | LM72 | 3 | Ir | — | 0 |
| BD073 | LM73 | 3 | Ir | — | 0 |
| BD074 | LM74 | 3 | Ir | — | 0 |
| BD075 | LM75 | 3 | Ir | — | 0 |
| BD076 | LM76 | 3 | Ir | — | 0 |
| BD077 | LM77 | 3 | Ir | — | 0 |
| BD078 | LM78 | 3 | Ir | — | 0 |
| BD079 | LM79 | 3 | Ir | — | 0 |
| BD080 | LM80 | 3 | Ir | — | 0 |
| BD081 | LM81 | 3 | Ir | — | 0 |
| BD082 | LM82 | 3 | Ir | — | 0 |
| BD083 | LM83 | 3 | Ir | — | 0 |
| BD084 | LM84 | 3 | Ir | — | 0 |
| BD085 | LM85 | 3 | Ir | — | 0 |
| BD086 | LM86 | 3 | Ir | — | 0 |
| BD087 | LM87 | 3 | Ir | — | 0 |
| BD088 | LM88 | 3 | Ir | — | 0 |
| BD089 | LM89 | 3 | Ir | — | 0 |
| BD090 | LM90 | 3 | Ir | — | 0 |
| BD091 | LM91 | 3 | Ir | — | 0 |

TABLE 11-continued

| Compound | $L_{101}$ | n101 | $M_{101}$ | $L_{102}$ | m101 |
|---|---|---|---|---|---|
| BD092 | LM92 | 3 | Ir | — | 0 |
| BD093 | LM93 | 3 | Ir | — | 0 |
| BD094 | LM94 | 3 | Ir | — | 0 |
| BD095 | LM95 | 3 | Ir | — | 0 |
| BD096 | LM96 | 3 | Ir | — | 0 |
| BD097 | LM97 | 3 | Ir | — | 0 |
| BD098 | LM98 | 3 | Ir | — | 0 |
| BD099 | LM99 | 3 | Ir | — | 0 |
| BD100 | LM100 | 3 | Ir | — | 0 |

TABLE 12

| Compound | $L_{101}$ | n101 | $M_{101}$ | $L_{102}$ | m101 |
|---|---|---|---|---|---|
| BD101 | LM101 | 3 | Ir | — | 0 |
| BD102 | LM102 | 3 | Ir | — | 0 |
| BD103 | LM103 | 3 | Ir | — | 0 |
| BD104 | LM104 | 3 | Ir | — | 0 |
| BD105 | LM105 | 3 | Ir | — | 0 |
| BD106 | LM106 | 3 | Ir | — | 0 |
| BD107 | LM107 | 3 | Ir | — | 0 |
| BD108 | LM108 | 3 | Ir | — | 0 |
| BD109 | LM109 | 3 | Ir | — | 0 |
| BD110 | LM110 | 3 | Ir | — | 0 |
| BD111 | LM111 | 3 | Ir | — | 0 |
| BD112 | LM112 | 3 | Ir | — | 0 |
| BD113 | LM113 | 3 | Ir | — | 0 |
| BD114 | LM114 | 3 | Ir | — | 0 |
| BD115 | LM115 | 3 | Ir | — | 0 |
| BD116 | LM116 | 3 | Ir | — | 0 |
| BD117 | LM117 | 3 | Ir | — | 0 |
| BD118 | LM118 | 3 | Ir | — | 0 |
| BD119 | LM119 | 3 | Ir | — | 0 |
| BD120 | LM120 | 3 | Ir | — | 0 |
| BD121 | LM121 | 3 | Ir | — | 0 |
| BD122 | LM122 | 3 | Ir | — | 0 |
| BD123 | LM123 | 3 | Ir | — | 0 |
| BD124 | LM124 | 3 | Ir | — | 0 |
| BD125 | LM125 | 3 | Ir | — | 0 |
| BD126 | LM126 | 3 | Ir | — | 0 |
| BD127 | LM127 | 3 | Ir | — | 0 |
| BD128 | LM128 | 3 | Ir | — | 0 |
| BD129 | LM129 | 3 | Ir | — | 0 |
| BD130 | LM130 | 3 | Ir | — | 0 |
| BD131 | LM131 | 3 | Ir | — | 0 |
| BD132 | LM132 | 3 | Ir | — | 0 |
| BD133 | LM133 | 3 | Ir | — | 0 |
| BD134 | LM134 | 3 | Ir | — | 0 |
| BD135 | LM135 | 3 | Ir | — | 0 |
| BD136 | LM136 | 3 | Ir | — | 0 |
| BD137 | LM137 | 3 | Ir | — | 0 |
| BD138 | LM138 | 3 | Ir | — | 0 |
| BD139 | LM139 | 3 | Ir | — | 0 |
| BD140 | LM140 | 3 | Ir | — | 0 |
| BD141 | LM141 | 3 | Ir | — | 0 |
| BD142 | LM142 | 3 | Ir | — | 0 |
| BD143 | LM143 | 3 | Ir | — | 0 |
| BD144 | LM144 | 3 | Ir | — | 0 |
| BD145 | LM145 | 3 | Ir | — | 0 |
| BD146 | LM146 | 3 | Ir | — | 0 |
| BD147 | LM147 | 3 | Ir | — | 0 |
| BD148 | LM148 | 3 | Ir | — | 0 |
| BD149 | LM149 | 3 | Ir | — | 0 |
| BD150 | LM150 | 3 | Ir | — | 0 |
| BD151 | LM151 | 3 | Ir | — | 0 |
| BD152 | LM152 | 3 | Ir | — | 0 |
| BD153 | LM153 | 3 | Ir | — | 0 |
| BD154 | LM154 | 3 | Ir | — | 0 |
| BD155 | LM155 | 3 | Ir | — | 0 |
| BD156 | LM156 | 3 | Ir | — | 0 |
| BD157 | LM157 | 3 | Ir | — | 0 |
| BD158 | LM158 | 3 | Ir | — | 0 |
| BD159 | LM159 | 3 | Ir | — | 0 |
| BD160 | LM160 | 3 | Ir | — | 0 |
| BD161 | LM161 | 3 | Ir | — | 0 |

TABLE 12-continued

| Compound | $L_{101}$ | n101 | $M_{101}$ | $L_{102}$ | m101 |
|---|---|---|---|---|---|
| BD162 | LM162 | 3 | Ir | — | 0 |
| BD163 | LM163 | 3 | Ir | — | 0 |
| BD164 | LM164 | 3 | Ir | — | 0 |
| BD165 | LM165 | 3 | Ir | — | 0 |
| BD166 | LM166 | 3 | Ir | — | 0 |
| BD167 | LM167 | 3 | Ir | — | 0 |
| BD168 | LM168 | 3 | Ir | — | 0 |
| BD169 | LM169 | 3 | Ir | — | 0 |
| BD170 | LM170 | 3 | Ir | — | 0 |
| BD171 | LM171 | 3 | Ir | — | 0 |
| BD172 | LM172 | 3 | Ir | — | 0 |
| BD173 | LM173 | 3 | Ir | — | 0 |
| BD174 | LM174 | 3 | Ir | — | 0 |
| BD175 | LM175 | 3 | Ir | — | 0 |
| BD176 | LM176 | 3 | Ir | — | 0 |
| BD177 | LM177 | 3 | Ir | — | 0 |
| BD178 | LM178 | 3 | Ir | — | 0 |
| BD179 | LM179 | 3 | Ir | — | 0 |
| BD180 | LM180 | 3 | Ir | — | 0 |
| BD181 | LM181 | 3 | Ir | — | 0 |
| BD182 | LM182 | 3 | Ir | — | 0 |
| BD183 | LM183 | 3 | Ir | — | 0 |
| BD184 | LM184 | 3 | Ir | — | 0 |
| BD185 | LM185 | 3 | Ir | — | 0 |
| BD186 | LM186 | 3 | Ir | — | 0 |
| BD187 | LM187 | 3 | Ir | — | 0 |
| BD188 | LM188 | 3 | Ir | — | 0 |
| BD189 | LM189 | 3 | Ir | — | 0 |
| BD190 | LM190 | 3 | Ir | — | 0 |
| BD191 | LM191 | 3 | Ir | — | 0 |
| BD192 | LM192 | 3 | Ir | — | 0 |
| BD193 | LM193 | 3 | Ir | — | 0 |
| BD194 | LM194 | 3 | Ir | — | 0 |
| BD195 | LM195 | 3 | Ir | — | 0 |
| BD196 | LM196 | 3 | Ir | — | 0 |
| BD197 | LM197 | 3 | Ir | — | 0 |
| BD198 | LM198 | 3 | Ir | — | 0 |
| BD199 | LM199 | 3 | Ir | — | 0 |
| BD200 | LM200 | 3 | Ir | — | 0 |

TABLE 13

| Compound | $L_{101}$ | n101 | $M_{101}$ | $L_{102}$ | m101 |
|---|---|---|---|---|---|
| BD201 | LM201 | 3 | Ir | — | 0 |
| BD202 | LM202 | 3 | Ir | — | 0 |
| BD203 | LM203 | 3 | Ir | — | 0 |
| BD204 | LM204 | 3 | Ir | — | 0 |
| BD205 | LM205 | 3 | Ir | — | 0 |
| BD206 | LM206 | 3 | Ir | — | 0 |
| BD207 | LM207 | 3 | Ir | — | 0 |
| BD208 | LM208 | 3 | Ir | — | 0 |
| BD209 | LM209 | 3 | Ir | — | 0 |
| BD210 | LM210 | 3 | Ir | — | 0 |
| BD211 | LM211 | 3 | Ir | — | 0 |
| BD212 | LM212 | 3 | Ir | — | 0 |
| BD213 | LM213 | 3 | Ir | — | 0 |
| BD214 | LM214 | 3 | Ir | — | 0 |
| BD215 | LM215 | 3 | Ir | — | 0 |
| BD216 | LM216 | 3 | Ir | — | 0 |
| BD217 | LM217 | 3 | Ir | — | 0 |
| BD218 | LM218 | 3 | Ir | — | 0 |
| BD219 | LM219 | 3 | Ir | — | 0 |
| BD220 | LM220 | 3 | Ir | — | 0 |
| BD221 | LM221 | 3 | Ir | — | 0 |
| BD222 | LM222 | 3 | Ir | — | 0 |
| BD223 | LM223 | 3 | Ir | — | 0 |
| BD224 | LM224 | 3 | Ir | — | 0 |
| BD225 | LM225 | 3 | Ir | — | 0 |
| BD226 | LM226 | 3 | Ir | — | 0 |
| BD227 | LM227 | 3 | Ir | — | 0 |
| BD228 | LM228 | 3 | Ir | — | 0 |
| BD229 | LM229 | 3 | Ir | — | 0 |
| BD230 | LM230 | 3 | Ir | — | 0 |
| BD231 | LM231 | 3 | Ir | — | 0 |

TABLE 13-continued

| Compound | $L_{101}$ | n101 | $M_{101}$ | $L_{102}$ | m101 |
|---|---|---|---|---|---|
| BD232 | LM232 | 3 | Ir | — | 0 |
| BD233 | LM233 | 3 | Ir | — | 0 |
| BD234 | LM234 | 3 | Ir | — | 0 |
| BD235 | LM235 | 3 | Ir | — | 0 |
| BD236 | LM236 | 3 | Ir | — | 0 |
| BD237 | LM237 | 3 | Ir | — | 0 |
| BD238 | LM238 | 3 | Ir | — | 0 |
| BD239 | LM239 | 3 | Ir | — | 0 |
| BD240 | LM240 | 3 | Ir | — | 0 |
| BD241 | LM241 | 3 | Ir | — | 0 |
| BD242 | LM242 | 3 | Ir | — | 0 |
| BD243 | LM243 | 3 | Ir | — | 0 |
| BD244 | LFM1 | 3 | Ir | — | 0 |
| BD245 | LFM2 | 3 | Ir | — | 0 |
| BD246 | LFM3 | 3 | Ir | — | 0 |
| BD247 | LFM4 | 3 | Ir | — | 0 |
| BD248 | LFM5 | 3 | Ir | — | 0 |
| BD249 | LFM6 | 3 | Ir | — | 0 |
| BD250 | LFM7 | 3 | Ir | — | 0 |
| BD251 | LFP1 | 3 | Ir | — | 0 |
| BD252 | LFP2 | 3 | Ir | — | 0 |
| BD253 | LFP3 | 3 | Ir | — | 0 |
| BD254 | LFP4 | 3 | Ir | — | 0 |
| BD255 | LFP5 | 3 | Ir | — | 0 |
| BD256 | LFP6 | 3 | Ir | — | 0 |
| BD257 | LFP7 | 3 | Ir | — | 0 |
| BD258 | LM47 | 2 | Ir | AN1 | 1 |
| BD259 | LM47 | 2 | Ir | AN2 | 1 |
| BD260 | LM47 | 2 | Ir | AN3 | 1 |
| BD261 | LM47 | 2 | Ir | AN4 | 1 |
| BD262 | LM47 | 2 | Ir | AN5 | 1 |
| BD263 | LM11 | 2 | Pt | — | 0 |
| BD264 | LM13 | 2 | Pt | — | 0 |
| BD265 | LM15 | 2 | Pt | — | 0 |
| BD266 | LM45 | 2 | Pt | — | 0 |
| BD267 | LM47 | 2 | Pt | — | 0 |
| BD268 | LM49 | 2 | Pt | — | 0 |
| BD269 | LM98 | 2 | Pt | — | 0 |
| BD270 | LM100 | 2 | Pt | — | 0 |
| BD271 | LM102 | 2 | Pt | — | 0 |
| BD272 | LM132 | 2 | Pt | — | 0 |
| BD273 | LM134 | 2 | Pt | — | 0 |
| BD274 | LM136 | 2 | Pt | — | 0 |
| BD275 | LM151 | 2 | Pt | — | 0 |
| BD276 | LM153 | 2 | Pt | — | 0 |
| BD277 | LM158 | 2 | Pt | — | 0 |
| BD278 | LM180 | 2 | Pt | — | 0 |
| BD279 | LM182 | 2 | Pt | — | 0 |
| BD280 | LM187 | 2 | Pt | — | 0 |
| BD281 | LM201 | 2 | Pt | — | 0 |
| BD282 | LM206 | 2 | Pt | — | 0 |
| BD283 | LM211 | 2 | Pt | — | 0 |
| BD284 | LM233 | 2 | Pt | — | 0 |
| BD285 | LM235 | 2 | Pt | — | 0 |
| BD286 | LM240 | 2 | Pt | — | 0 |
| BD287 | LFM5 | 2 | Pt | — | 0 |
| BD288 | LFM6 | 2 | Pt | — | 0 |
| BD289 | LFM7 | 2 | Pt | — | 0 |
| BD290 | LFP5 | 2 | Pt | — | 0 |
| BD291 | LFP6 | 2 | Pt | — | 0 |
| BD292 | LFP7 | 2 | Pt | — | 0 |
| BD293 | LM47 | 1 | Pt | AN1 | 1 |
| BD294 | LM47 | 1 | Pt | AN2 | 1 |
| BD295 | LM47 | 1 | Pt | AN3 | 1 |
| BD296 | LM47 | 1 | Pt | AN4 | 1 |
| BD297 | LM47 | 1 | Pt | AN5 | 1 |

In Tables 11 to 13, LM1 to LM243 may be understood by referring to Formulae 1-1 to 1-3 and Tables 14 to 16:

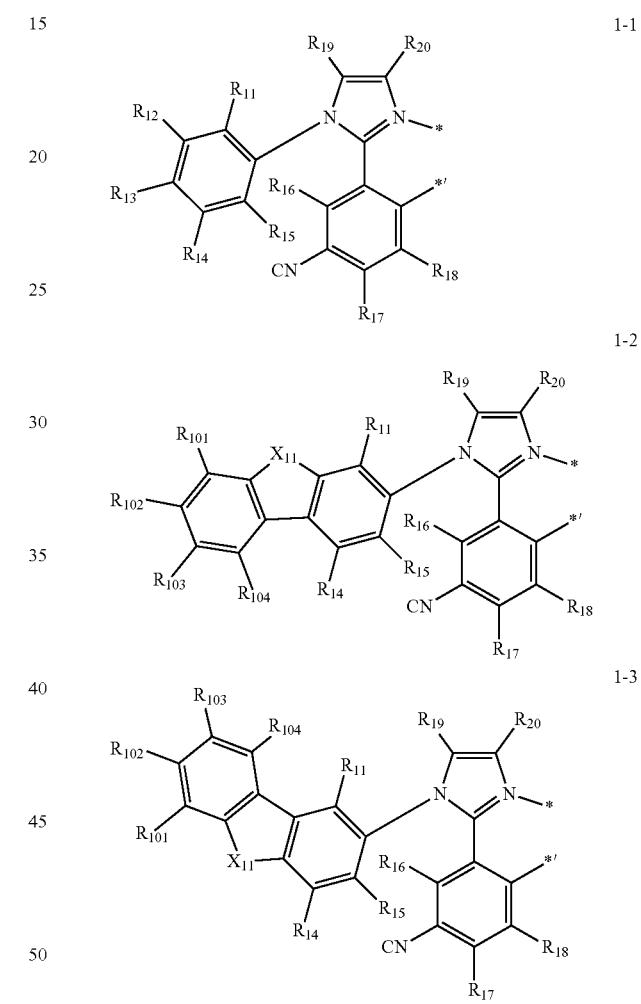

TABLE 14

| | Formula 1-1 | | | | | | | | | |
|---|---|---|---|---|---|---|---|---|---|---|
| Ligand | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
| LM1 | X1 | H | X3 | H | X1 | H | H | H | H | D |
| LM2 | X1 | H | X3 | H | X1 | H | H | H | D | H |
| LM3 | X1 | H | X3 | H | X1 | H | H | H | D | D |
| LM4 | Y1 | H | X3 | H | Y1 | H | H | H | D | D |
| LM5 | Y2 | H | X3 | H | Y2 | H | H | H | D | D |
| LM6 | Y3 | H | X3 | H | Y3 | H | H | H | D | D |
| LM7 | Y3 | D | X3 | D | Y3 | H | H | H | D | D |
| LM8 | Y3 | D | X3 | D | Y3 | D | H | H | D | D |

TABLE 14-continued

| Formula 1-1 | | | | | | | | | |
|---|---|---|---|---|---|---|---|---|---|
| Ligand | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
| LM9 | Y3 | D | X3 | D | Y3 | D | D | H | D | D |
| LM10 | Y3 | D | X3 | D | Y3 | D | D | D | D | D |
| LM11 | Y3 | D | Y11 | D | Y3 | D | D | D | D | D |
| LM12 | Y3 | D | Y11 | D | Y3 | H | X1 | H | D | D |
| LM13 | Y3 | D | Y11 | D | Y3 | D | Y3 | D | D | D |
| LM14 | Y3 | D | Y11 | D | Y3 | H | X4 | H | D | D |
| LM15 | Y3 | D | Y11 | D | Y3 | D | Y12 | D | D | D |
| LM16 | X2 | H | X3 | H | X2 | H | H | H | H | D |
| LM17 | X2 | H | X3 | H | X2 | H | H | H | D | H |
| LM18 | X2 | H | X3 | H | X2 | H | H | H | D | D |
| LM19 | Y4 | H | X3 | H | Y4 | H | H | H | D | D |
| LM20 | Y5 | H | X3 | H | Y5 | H | H | H | D | D |
| LM21 | Y6 | H | X3 | H | Y6 | H | H | H | D | D |
| LM22 | Y7 | H | X3 | H | Y7 | H | H | H | D | D |
| LM23 | Y8 | H | X3 | H | Y8 | H | H | H | D | D |
| LM24 | Y9 | H | X3 | H | Y9 | H | H | H | D | D |
| LM25 | Y10 | H | X3 | H | Y10 | H | H | H | D | D |
| LM26 | Y10 | D | X3 | D | Y10 | H | H | H | D | D |
| LM27 | Y10 | D | X3 | D | Y10 | D | H | H | D | D |
| LM28 | Y10 | D | X3 | D | Y10 | D | D | H | D | D |
| LM29 | Y10 | D | X3 | D | Y10 | D | D | D | D | D |
| LM30 | Y10 | D | Y11 | D | Y10 | D | D | D | D | D |
| LM31 | Y10 | D | Y11 | D | Y10 | H | X1 | H | D | D |
| LM32 | Y10 | D | Y11 | D | Y10 | D | Y3 | D | D | D |
| LM33 | Y10 | D | Y11 | D | Y10 | H | X4 | H | D | D |
| LM34 | Y10 | D | Y11 | D | Y10 | D | Y12 | D | D | D |
| LM35 | X1 | H | X4 | H | X1 | H | H | H | H | D |
| LM36 | X1 | H | X4 | H | X1 | H | H | H | D | H |
| LM37 | X1 | H | X4 | H | X1 | H | H | H | D | D |
| LM38 | Y1 | H | X4 | H | Y1 | H | H | H | D | D |
| LM39 | Y2 | H | X4 | H | Y2 | H | H | H | D | D |
| LM40 | Y3 | H | X4 | H | Y3 | H | H | H | D | D |
| LM41 | Y3 | D | X4 | D | Y3 | H | H | H | D | D |
| LM42 | Y3 | D | X4 | D | Y3 | D | H | H | D | D |
| LM43 | Y3 | D | X4 | D | Y3 | D | D | H | D | D |
| LM44 | Y3 | D | X4 | D | Y3 | D | D | D | D | D |
| LM45 | Y3 | D | Y12 | D | Y3 | D | D | D | D | D |
| LM46 | Y3 | D | Y12 | D | Y3 | H | X1 | H | D | D |
| LM47 | Y3 | D | Y12 | D | Y3 | D | Y3 | D | D | D |
| LM48 | Y3 | D | Y12 | D | Y3 | H | X4 | H | D | D |
| LM49 | Y3 | D | Y12 | D | Y3 | D | Y12 | D | D | D |
| LM50 | X2 | H | X4 | H | X2 | H | H | H | H | D |
| LM51 | X2 | H | X4 | H | X2 | H | H | H | D | H |
| LM52 | X2 | H | X4 | H | X2 | H | H | H | D | D |
| LM53 | Y4 | H | X4 | H | Y4 | H | H | H | D | D |
| LM54 | Y5 | H | X4 | H | Y5 | H | H | H | D | D |
| LM55 | Y6 | H | X4 | H | Y6 | H | H | H | D | D |
| LM56 | Y7 | H | X4 | H | Y7 | H | H | H | D | D |
| LM57 | Y8 | H | X4 | H | Y8 | H | H | H | D | D |
| LM58 | Y9 | H | X4 | H | Y9 | H | H | H | D | D |
| LM59 | Y10 | H | X4 | H | Y10 | H | H | H | D | D |
| LM60 | Y10 | D | X4 | D | Y10 | H | H | H | D | D |
| LM61 | Y10 | D | X4 | D | Y10 | D | H | H | D | D |
| LM62 | Y10 | D | X4 | D | Y10 | D | D | H | D | D |
| LM63 | Y10 | D | X4 | D | Y10 | D | D | D | D | D |
| LM64 | Y10 | D | Y12 | D | Y10 | D | D | D | D | D |
| LM65 | Y10 | D | Y12 | D | Y10 | H | X1 | H | D | D |
| LM66 | Y10 | D | Y12 | D | Y10 | D | Y3 | D | D | D |
| LM67 | Y10 | D | Y12 | D | Y10 | H | X4 | H | D | D |
| LM68 | Y10 | D | Y12 | D | Y10 | D | Y12 | D | D | D |
| LM69 | X1 | H | X5 | H | X1 | H | H | H | H | D |
| LM70 | X1 | H | X5 | H | X1 | H | H | H | D | H |
| LM71 | X1 | H | X5 | H | X1 | H | H | H | D | D |
| LM72 | Y1 | H | X5 | H | Y1 | H | H | H | D | D |
| LM73 | Y2 | H | X5 | H | Y2 | H | H | H | D | D |
| LM74 | Y3 | H | X5 | H | Y3 | H | H | H | D | D |
| LM75 | Y3 | D | X5 | D | Y3 | H | H | H | D | D |
| LM76 | Y3 | D | X5 | D | Y3 | D | H | H | D | D |
| LM77 | Y3 | D | X5 | D | Y3 | D | D | H | D | D |
| LM78 | Y3 | D | X5 | D | Y3 | D | D | D | D | D |
| LM79 | Y3 | D | Y13 | D | Y3 | D | D | D | D | D |
| LM80 | Y3 | D | Y13 | D | Y3 | H | X1 | H | D | D |
| LM81 | Y3 | D | Y13 | D | Y3 | D | Y3 | D | D | D |
| LM82 | Y3 | D | Y13 | D | Y3 | H | X4 | H | D | D |
| LM83 | Y3 | D | Y13 | D | Y3 | D | Y12 | D | D | D |
| LM84 | X2 | H | X5 | H | X2 | H | H | H | H | D |

TABLE 14-continued

Formula 1-1

| Ligand | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
|---|---|---|---|---|---|---|---|---|---|---|
| LM85 | X2 | H | X5 | H | X2 | H | H | H | D | H |
| LM86 | X2 | H | X5 | H | X2 | H | H | H | D | D |
| LM87 | Y4 | H | X5 | H | Y4 | H | H | H | D | D |
| LM88 | Y5 | H | X5 | H | Y5 | H | H | H | D | D |
| LM89 | Y6 | H | X5 | H | Y6 | H | H | H | D | D |
| LM90 | Y7 | H | X5 | H | Y7 | H | H | H | D | D |
| LM91 | Y8 | H | X5 | H | Y8 | H | H | H | D | D |
| LM92 | Y9 | H | X5 | H | Y9 | H | H | H | D | D |
| LM93 | Y10 | H | X5 | H | Y10 | H | H | H | D | D |
| LM94 | Y10 | D | X5 | D | Y10 | H | H | H | D | D |
| LM95 | Y10 | D | X5 | D | Y10 | D | H | H | D | D |
| LM96 | Y10 | D | X5 | D | Y10 | D | D | H | D | D |
| LM97 | Y10 | D | X5 | D | Y10 | D | D | D | D | D |
| LM98 | Y10 | D | Y13 | D | Y10 | D | D | D | D | D |
| LM99 | Y10 | D | Y13 | D | Y10 | H | X1 | H | D | D |
| LM100 | Y10 | D | Y13 | D | Y10 | D | Y3 | D | D | D |
| LM101 | Y10 | D | Y13 | D | Y10 | H | X4 | H | D | D |
| LM102 | Y10 | D | Y13 | D | Y10 | D | Y12 | D | D | D |
| LM103 | X1 | H | X6 | H | X1 | H | H | H | H | D |
| LM104 | X1 | H | X6 | H | X1 | H | H | H | D | H |
| LM105 | X1 | H | X6 | H | X1 | H | H | H | D | D |
| LM106 | Y1 | H | X6 | H | Y1 | H | H | H | D | D |
| LM107 | Y2 | H | X6 | H | Y2 | H | H | H | D | D |
| LM108 | Y3 | H | X6 | H | Y3 | H | H | H | D | D |
| LM109 | Y3 | D | X6 | D | Y3 | H | H | H | D | D |
| LM110 | Y3 | D | X6 | D | Y3 | D | H | H | D | D |
| LM111 | Y3 | D | X6 | D | Y3 | D | D | H | D | D |
| LM112 | Y3 | D | X6 | D | Y3 | D | D | D | D | D |
| LM113 | Y3 | D | Y14 | D | Y3 | D | D | D | D | D |
| LM114 | Y3 | D | Y14 | D | Y3 | H | X1 | H | D | D |
| LM115 | Y3 | D | Y14 | D | Y3 | D | Y3 | D | D | D |
| LM116 | Y3 | D | Y14 | D | Y3 | H | X4 | H | D | D |
| LM117 | Y3 | D | Y14 | D | Y3 | D | Y12 | D | D | D |
| LM118 | X2 | H | X6 | H | X2 | H | H | H | H | D |
| LM119 | X2 | H | X6 | H | X2 | H | H | H | D | H |
| LM120 | X2 | H | X6 | H | X2 | H | H | H | D | D |
| LM121 | Y4 | H | X6 | H | Y4 | H | H | H | D | D |
| LM122 | Y5 | H | X6 | H | Y5 | H | H | H | D | D |
| LM123 | Y6 | H | X6 | H | Y6 | H | H | H | D | D |
| LM124 | Y7 | H | X6 | H | Y7 | H | H | H | D | D |
| LM125 | Y8 | H | X6 | H | Y8 | H | H | H | D | D |
| LM126 | Y9 | H | X6 | H | Y9 | H | H | H | D | D |
| LM127 | Y10 | H | X6 | H | Y10 | H | H | H | D | D |
| LM128 | Y10 | D | X6 | D | Y10 | H | H | H | D | D |
| LM129 | Y10 | D | X6 | D | Y10 | D | H | H | D | D |
| LM130 | Y10 | D | X6 | D | Y10 | D | D | H | D | D |
| LM131 | Y10 | D | X6 | D | Y10 | D | D | D | D | D |
| LM132 | Y10 | D | Y14 | D | Y10 | D | D | D | D | D |
| LM133 | Y10 | D | Y14 | D | Y10 | H | X1 | H | D | D |
| LM134 | Y10 | D | Y14 | D | Y10 | D | Y3 | D | D | D |
| LM135 | Y10 | D | Y14 | D | Y10 | H | X4 | H | D | D |
| LM136 | Y10 | D | Y14 | D | Y10 | D | Y12 | D | D | D |
| LM137 | X1 | H | X7 | H | X1 | H | H | H | H | D |
| LM138 | X1 | H | X7 | H | X1 | H | H | H | D | H |
| LM139 | X1 | H | X7 | H | X1 | H | H | H | D | D |
| LM140 | Y1 | H | X7 | H | Y1 | H | H | H | D | D |
| LM141 | Y2 | H | X7 | H | Y2 | H | H | H | D | D |
| LM142 | Y3 | H | X7 | H | Y3 | H | H | H | D | D |
| LM143 | Y3 | D | X7 | D | Y3 | H | H | H | D | D |
| LM144 | Y3 | D | X7 | D | Y3 | D | H | H | D | D |
| LM145 | Y3 | D | X7 | D | Y3 | D | D | H | D | D |
| LM146 | Y3 | D | X7 | D | Y3 | D | D | D | D | D |
| LM147 | Y3 | D | X8 | D | Y3 | D | D | D | D | D |
| LM148 | Y3 | D | Y16 | D | Y3 | D | D | D | D | D |
| LM149 | Y3 | D | Y17 | D | Y3 | D | D | D | D | D |
| LM150 | Y3 | D | Y18 | D | Y3 | D | D | D | D | D |
| LM151 | Y3 | D | Y15 | D | Y3 | D | D | D | D | D |
| LM152 | Y3 | D | Y15 | D | Y3 | H | X1 | H | D | D |
| LM153 | Y3 | D | Y15 | D | Y3 | D | Y3 | D | D | D |
| LM154 | Y3 | D | Y16 | D | Y3 | D | Y3 | D | D | D |
| LM155 | Y3 | D | Y17 | D | Y3 | D | Y3 | D | D | D |
| LM156 | Y3 | D | Y18 | D | Y3 | D | Y3 | D | D | D |
| LM157 | Y3 | D | Y15 | D | Y3 | H | X4 | H | D | D |
| LM158 | Y3 | D | Y15 | D | Y3 | D | Y12 | D | D | D |
| LM159 | Y3 | D | Y16 | D | Y3 | D | Y12 | D | D | D |
| LM160 | Y3 | D | Y17 | D | Y3 | D | Y12 | D | D | D |

TABLE 14-continued

Formula 1-1

| Ligand | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
|---|---|---|---|---|---|---|---|---|---|---|
| LM161 | Y3 | D | Y18 | D | Y3 | D | Y12 | D | D | D |
| LM162 | X2 | H | X7 | H | X2 | H | H | H | H | D |
| LM163 | X2 | H | X7 | H | X2 | H | H | H | D | H |
| LM164 | X2 | H | X7 | H | X2 | H | H | H | D | D |
| LM165 | Y4 | H | X7 | H | Y4 | H | H | H | D | D |
| LM166 | Y5 | H | X7 | H | Y5 | H | H | H | D | D |
| LM167 | Y6 | H | X7 | H | Y6 | H | H | H | D | D |
| LM168 | Y7 | H | X7 | H | Y7 | H | H | H | D | D |
| LM169 | Y8 | H | X7 | H | Y8 | H | H | H | D | D |
| LM170 | Y9 | H | X7 | H | Y9 | H | H | H | D | D |
| LM171 | Y10 | H | X7 | H | Y10 | H | H | H | D | D |
| LM172 | Y10 | D | X7 | D | Y10 | H | H | H | D | D |
| LM173 | Y10 | D | X7 | D | Y10 | D | H | H | D | D |
| LM174 | Y10 | D | X7 | D | Y10 | D | D | H | D | D |
| LM175 | Y10 | D | X7 | D | Y10 | D | D | D | D | D |
| LM176 | Y10 | D | X8 | D | Y10 | D | D | D | D | D |
| LM177 | Y10 | D | Y16 | D | Y10 | D | D | D | D | D |
| LM178 | Y10 | D | Y17 | D | Y10 | D | D | D | D | D |
| LM179 | Y10 | D | Y18 | D | Y10 | D | D | D | D | D |
| LM180 | Y10 | D | Y15 | D | Y10 | D | D | D | D | D |
| LM181 | Y10 | D | Y15 | D | Y10 | H | X1 | H | D | D |
| LM182 | Y10 | D | Y15 | D | Y10 | D | Y3 | D | D | D |
| LM183 | Y10 | D | Y16 | D | Y10 | D | Y3 | D | D | D |
| LM184 | Y10 | D | Y17 | D | Y10 | D | Y3 | D | D | D |
| LM185 | Y10 | D | Y18 | D | Y10 | D | Y3 | D | D | D |
| LM186 | Y10 | D | Y15 | D | Y10 | H | X4 | H | D | D |
| LM187 | Y10 | D | Y15 | D | Y10 | D | Y12 | D | D | D |
| LM188 | Y10 | D | Y16 | D | Y10 | D | Y12 | D | D | D |
| LM189 | Y10 | D | Y17 | D | Y10 | D | Y12 | D | D | D |
| LM190 | Y10 | D | Y18 | D | Y10 | D | Y12 | D | D | D |
| LM191 | X1 | X7 | H | H | X1 | H | H | H | H | D |
| LM192 | X1 | X7 | H | H | X1 | H | H | H | D | H |
| LM193 | X1 | X7 | H | H | X1 | H | H | H | D | D |
| LM194 | Y1 | X7 | H | H | Y1 | H | H | H | D | D |
| LM195 | Y2 | X7 | H | H | Y2 | H | H | H | D | D |
| LM196 | Y3 | X7 | H | H | Y3 | H | H | H | D | D |
| LM197 | Y3 | X7 | D | D | Y3 | H | H | H | D | D |
| LM198 | Y3 | X7 | D | D | Y3 | D | H | H | D | D |
| LM199 | Y3 | X7 | D | D | Y3 | D | D | H | D | D |
| LM200 | Y3 | X7 | D | D | Y3 | D | D | D | D | D |
| LM201 | Y3 | Y15 | D | D | Y3 | D | D | D | D | D |
| LM202 | Y3 | Y16 | D | D | Y3 | D | D | D | D | D |
| LM203 | Y3 | Y17 | D | D | Y3 | D | D | D | D | D |
| LM204 | Y3 | Y18 | D | D | Y3 | D | D | D | D | D |
| LM205 | Y3 | Y15 | D | D | Y3 | H | X1 | H | D | D |
| LM206 | Y3 | Y15 | D | D | Y3 | D | Y3 | D | D | D |
| LM207 | Y3 | Y16 | D | D | Y3 | D | Y3 | D | D | D |
| LM208 | Y3 | Y17 | D | D | Y3 | D | Y3 | D | D | D |
| LM209 | Y3 | Y18 | D | D | Y3 | D | Y3 | D | D | D |
| LM210 | Y3 | Y15 | D | D | Y3 | H | X4 | H | D | D |
| LM211 | Y3 | Y15 | D | D | Y3 | D | Y12 | D | D | D |
| LM212 | Y3 | Y16 | D | D | Y3 | D | Y12 | D | D | D |
| LM213 | Y3 | Y17 | D | D | Y3 | D | Y12 | D | D | D |
| LM214 | Y3 | Y18 | D | D | Y3 | D | Y12 | D | D | D |
| LM215 | X2 | X7 | H | H | X2 | H | H | H | H | D |
| LM216 | X2 | X7 | H | H | X2 | H | H | H | D | H |
| LM217 | X2 | X7 | H | H | X2 | H | H | H | D | D |
| LM218 | Y4 | X7 | H | H | Y4 | H | H | H | D | D |
| LM219 | Y5 | X7 | H | H | Y5 | H | H | H | D | D |
| LM220 | Y6 | X7 | H | H | Y6 | H | H | H | D | D |
| LM221 | Y7 | X7 | H | H | Y7 | H | H | H | D | D |
| LM222 | Y8 | X7 | H | H | Y8 | H | H | H | D | D |
| LM223 | Y9 | X7 | H | H | Y9 | H | H | H | D | D |
| LM224 | Y10 | X7 | H | H | Y10 | H | H | H | D | D |
| LM225 | Y10 | X7 | D | D | Y10 | H | H | H | D | D |
| LM226 | Y10 | X7 | D | D | Y10 | D | H | H | D | D |
| LM227 | Y10 | X7 | D | D | Y10 | D | D | H | D | D |
| LM228 | Y10 | X7 | D | D | Y10 | D | D | D | D | D |
| LM229 | Y10 | X8 | D | D | Y10 | D | D | D | D | D |
| LM230 | Y10 | Y16 | D | D | Y10 | D | D | D | D | D |
| LM231 | Y10 | Y17 | D | D | Y10 | D | D | D | D | D |
| LM232 | Y10 | Y18 | D | D | Y10 | D | D | D | D | D |
| LM233 | Y10 | Y15 | D | D | Y10 | D | D | D | D | D |
| LM234 | Y10 | Y15 | D | D | Y10 | H | X1 | H | D | D |
| LM235 | Y10 | Y15 | D | D | Y10 | D | Y3 | D | D | D |
| LM236 | Y10 | Y16 | D | D | Y10 | D | Y3 | D | D | D |

TABLE 14-continued

| | Formula 1-1 | | | | | | | | | |
|---|---|---|---|---|---|---|---|---|---|---|
| Ligand | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
| LM237 | Y10 | Y17 | D | D | Y10 | D | Y3 | D | D | D |
| LM238 | Y10 | Y18 | D | D | Y10 | D | Y3 | D | D | D |
| LM239 | Y10 | Y15 | D | D | Y10 | H | X4 | H | D | D |
| LM240 | Y10 | Y15 | D | D | Y10 | D | Y12 | D | D | D |
| LM241 | Y10 | Y16 | D | D | Y10 | D | Y12 | D | D | D |
| LM242 | Y10 | Y17 | D | D | Y10 | D | Y12 | D | D | D |
| LM243 | Y10 | Y18 | D | D | Y10 | D | Y12 | D | D | D |

TABLE 15

| | Formula 1-2 | | | | | | | | | | | | |
|---|---|---|---|---|---|---|---|---|---|---|---|---|---|
| Ligand | $R_{11}$ | $X_{11}$ | $R_{101}$ | $R_{102}$ | $R_{103}$ | $R_{104}$ | $R_{14}$ | $R_{15}$ | $R_{16}$ | $R_{17}$ | $R_{18}$ | $R_{19}$ | $R_{20}$ |
| LFM1 | Y10 | N—Ph | D | D | D | D | D | Y10 | D | D | D | D | D |
| LFM2 | Y10 | S | D | D | D | D | D | Y10 | D | D | D | D | D |
| LFM3 | Y10 | O | D | D | D | D | D | Y10 | D | D | D | D | D |
| LFM4 | Y3 | O | D | D | D | D | D | Y3 | D | D | D | D | D |
| LFM5 | Y10 | O | D | D | D | D | D | Y10 | D | D | D | D | D |
| LFM6 | Y10 | O | D | D | D | D | D | Y10 | D | Y3 | D | D | D |
| LFM7 | Y10 | O | D | D | D | D | D | Y10 | D | Y12 | D | D | D |

TABLE 16

| | Formula 1-3 | | | | | | | | | | | | |
|---|---|---|---|---|---|---|---|---|---|---|---|---|---|
| Ligand | $R_{11}$ | $X_{11}$ | $R_{101}$ | $R_{102}$ | $R_{103}$ | $R_{104}$ | $R_{14}$ | $R_{15}$ | $R_{16}$ | $R_{17}$ | $R_{18}$ | $R_{19}$ | $R_{20}$ |
| LFP1 | Y10 | N—Ph | D | D | D | D | D | Y10 | D | D | D | D | D |
| LFP2 | Y10 | S | D | D | D | D | D | Y10 | D | D | D | D | D |
| LFP3 | Y10 | O | D | D | D | D | D | Y10 | D | D | D | D | D |
| LFP4 | Y3 | O | D | D | D | D | D | Y3 | D | D | D | D | D |
| LFP5 | Y10 | O | D | D | D | D | D | Y10 | D | D | D | D | D |
| LFP6 | Y10 | O | D | D | D | D | D | Y10 | D | Y3 | D | D | D |
| LFP7 | Y10 | O | D | D | D | D | D | Y10 | D | Y12 | D | D | D |

In Tables 14 to 16, X1 to X10 and Y1 to Y18 may be as follows, and "Ph" represents a phenyl group:

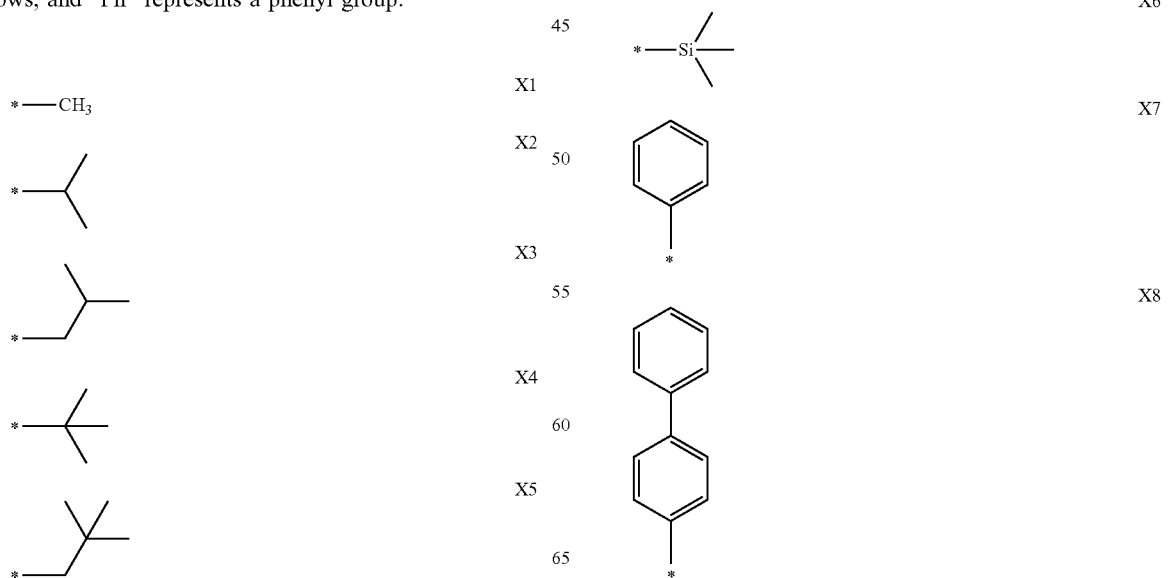

2475
-continued
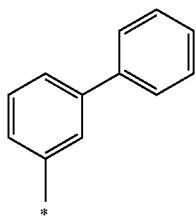
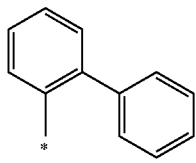
*—CH₂D
*—CHD₂
*—CD₃
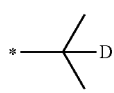
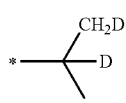
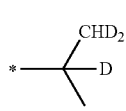
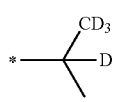
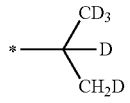
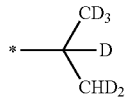
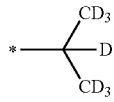
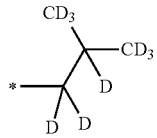
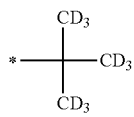
2476
-continued
X9
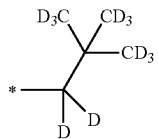
X10
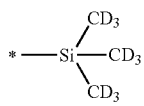
Y1
Y2
Y3
Y4
Y5
Y6
Y7
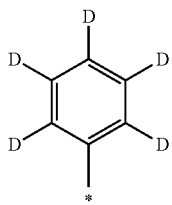
Y8
Y9
Y10
Y11
Y12
Y13
Y14
Y15
Y16
Y17
Y18

2477 Group VI
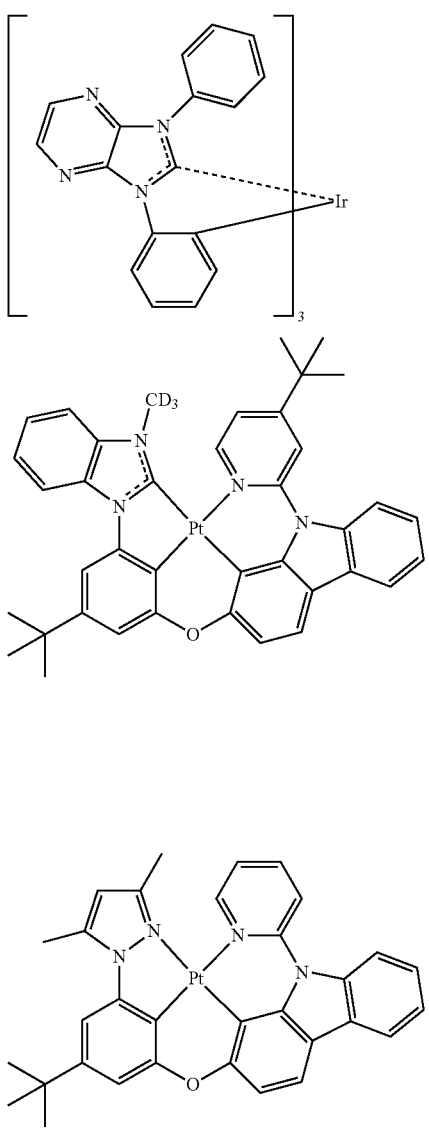
2478 -continued
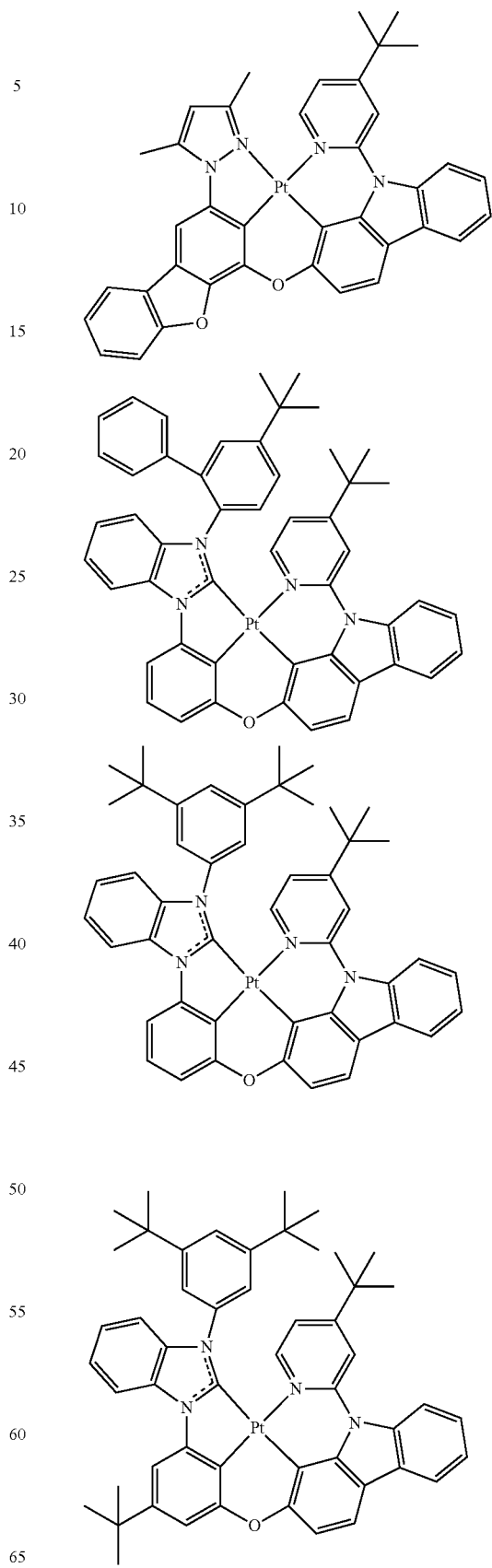

Group VII
1
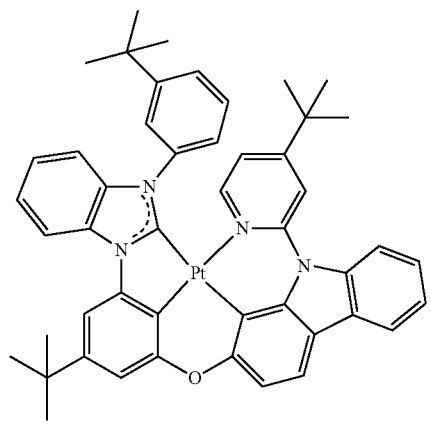
4
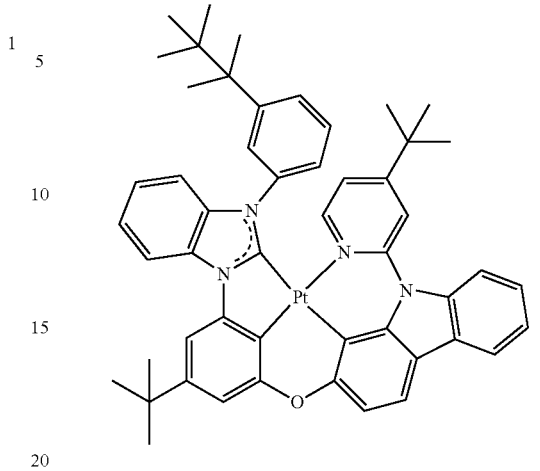
2
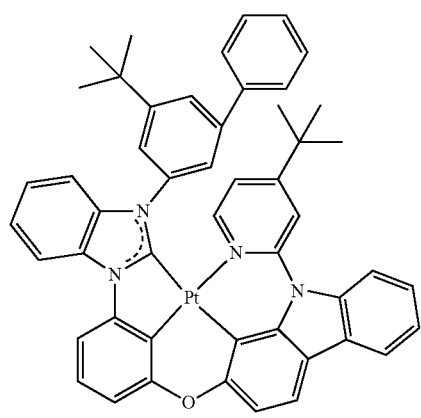
5
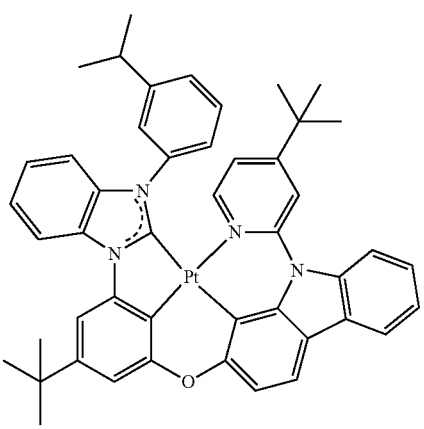
3
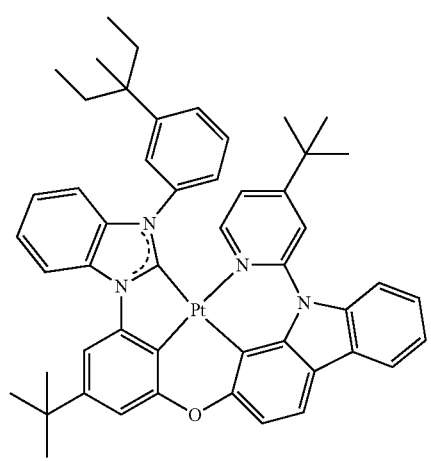
6
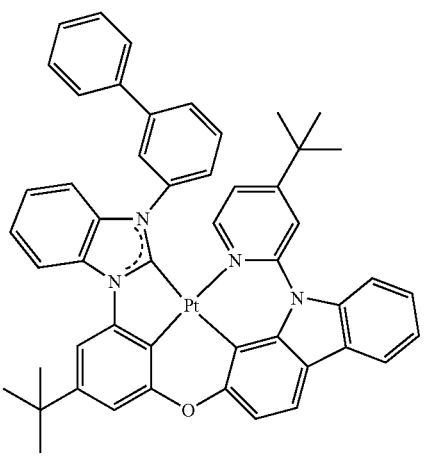

2481
-continued
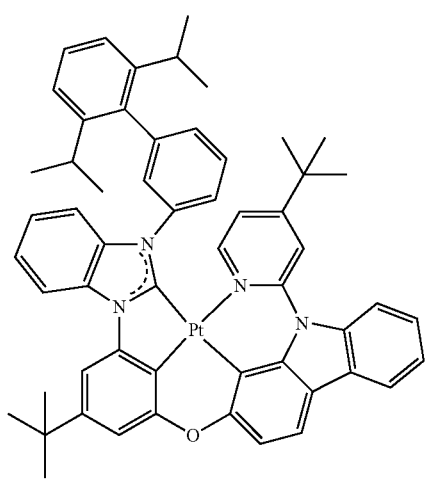
7
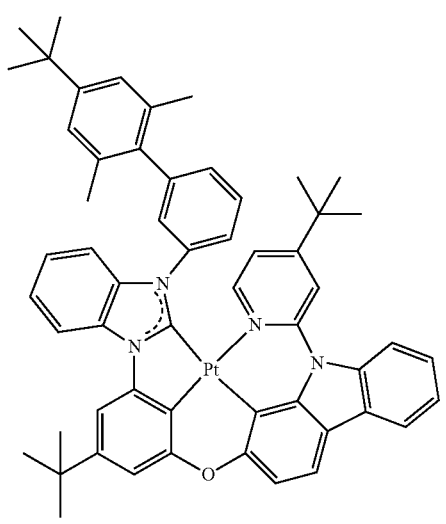
8
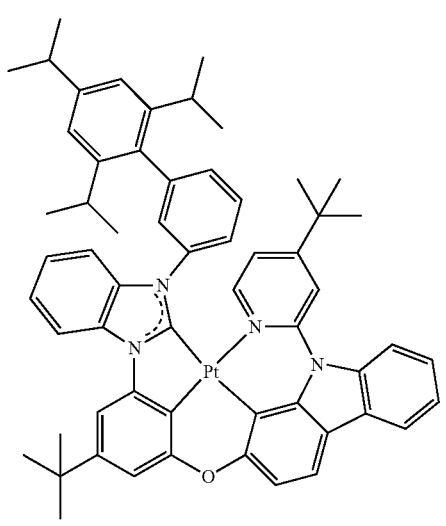
9
2482
-continued
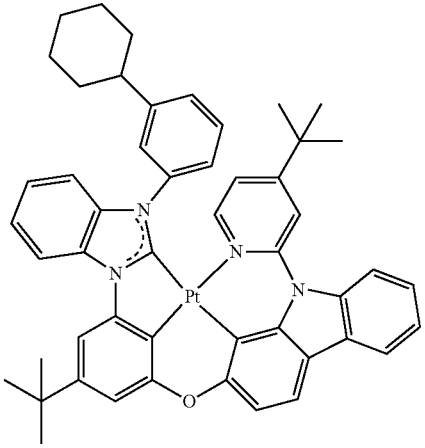
10
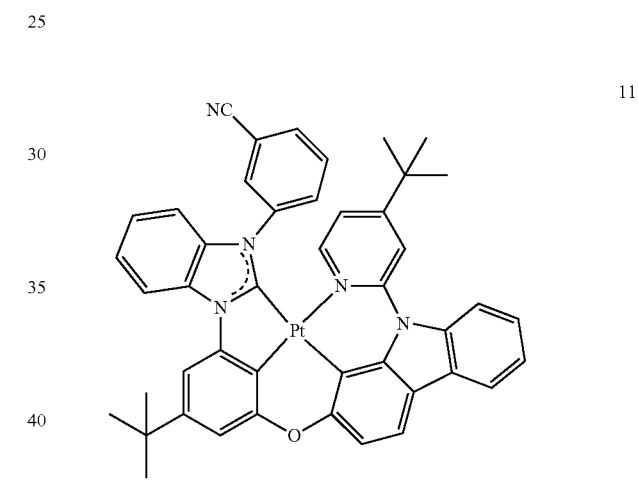
11
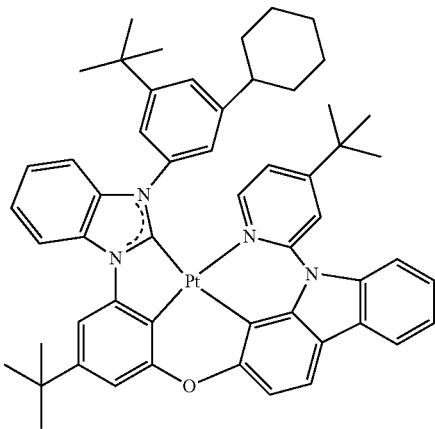
12

13
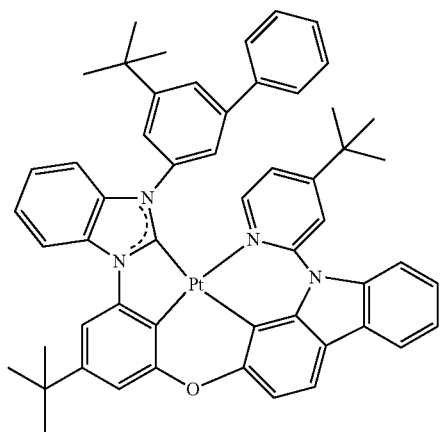
14
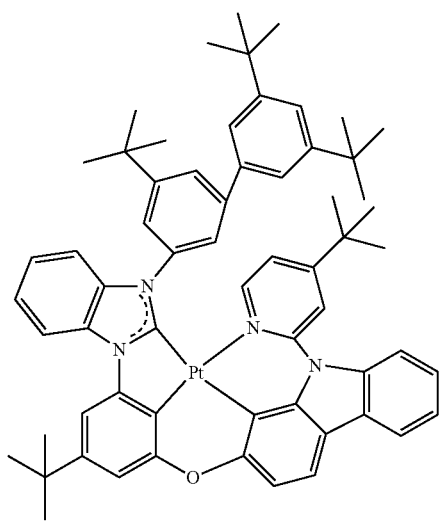
15
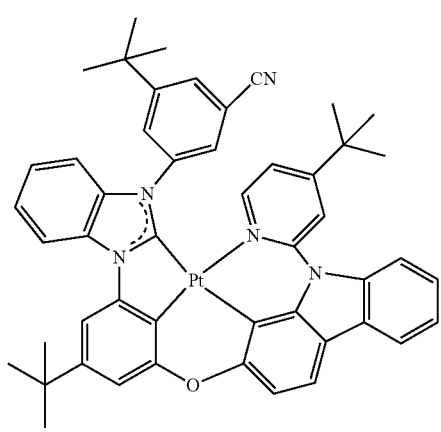
16
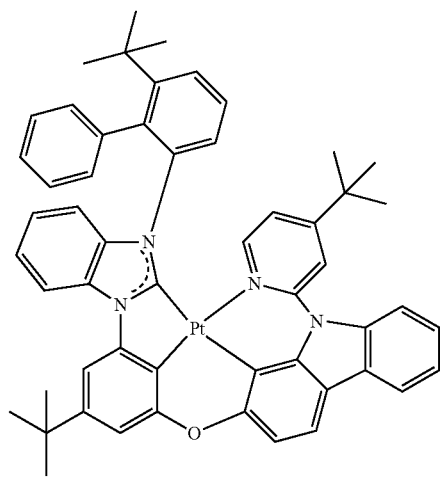
17
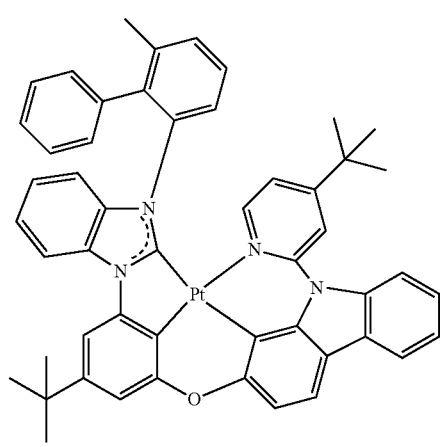
18
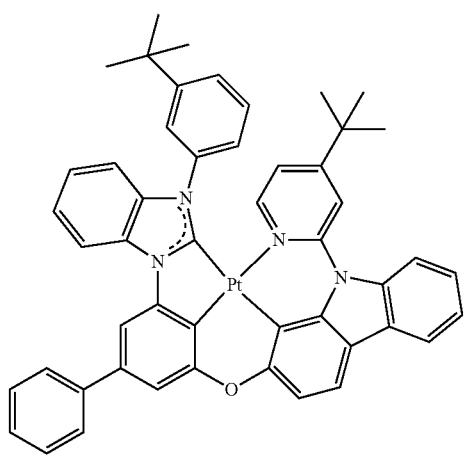

-continued
19
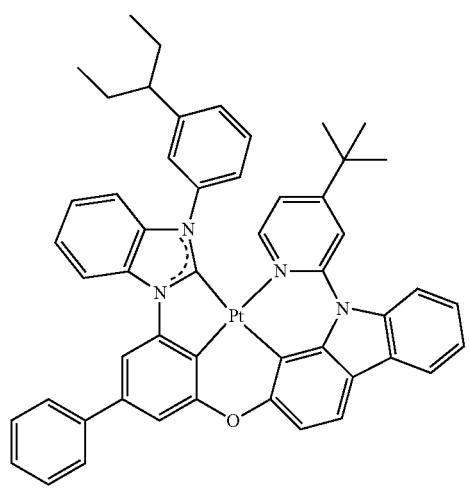
20
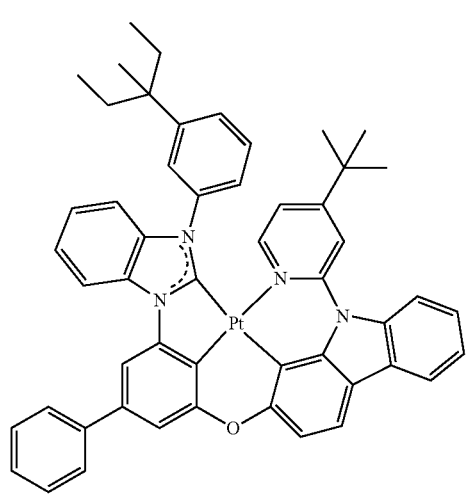
21
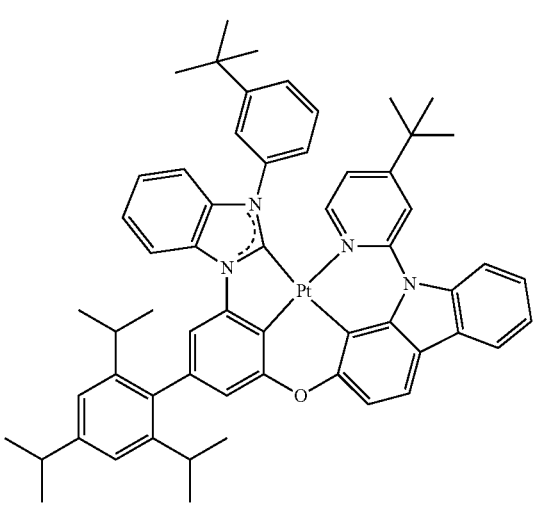
-continued
22
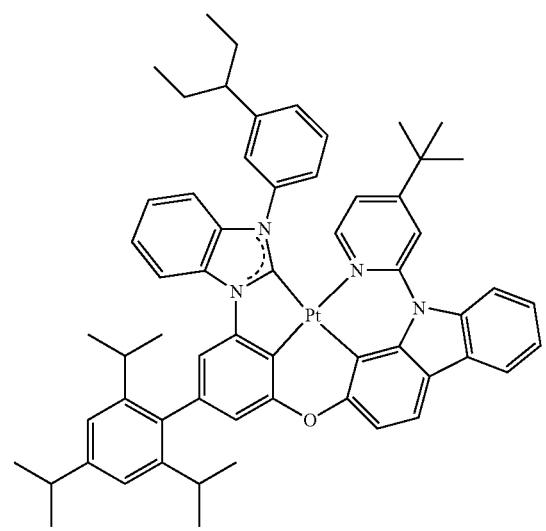
23
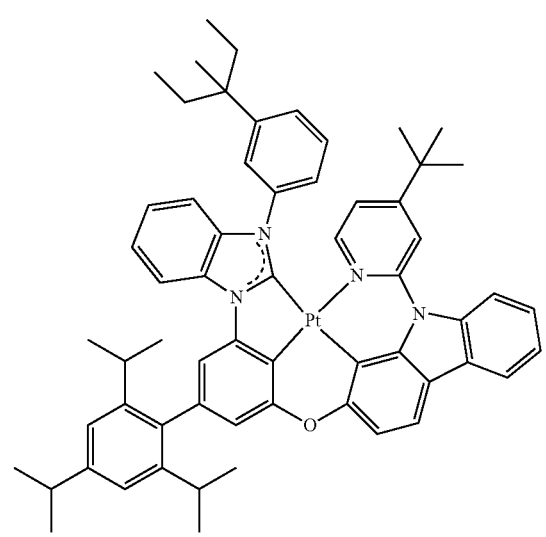
24
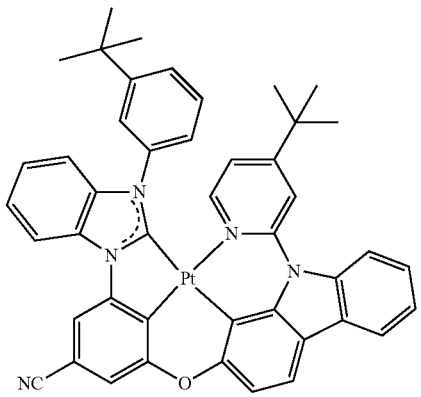

2487
-continued
25
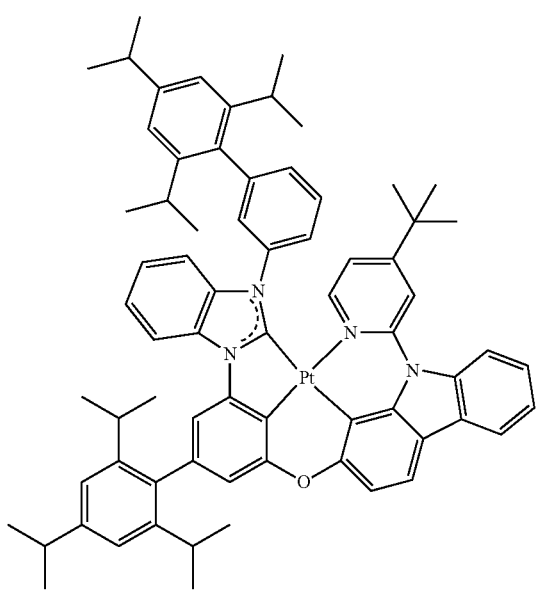
26
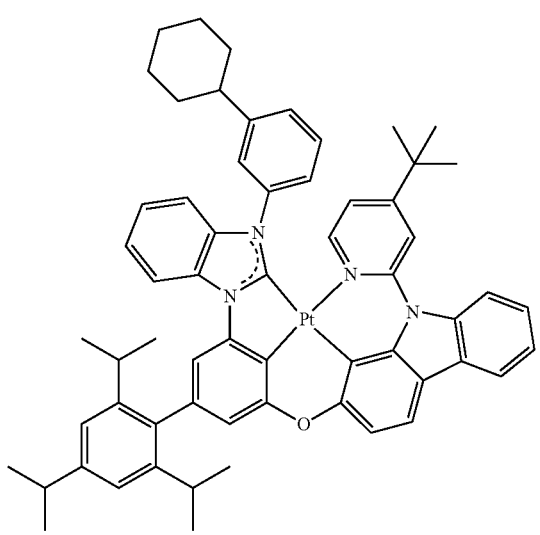
27
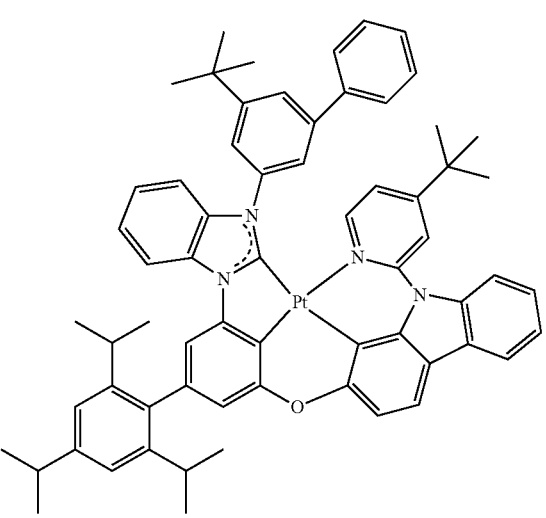
2488
-continued
28
29
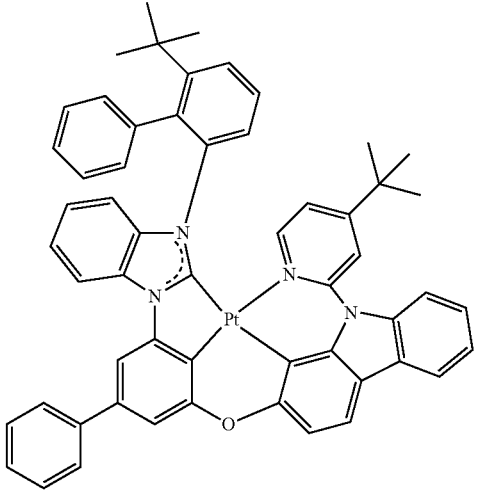
30

-continued
31
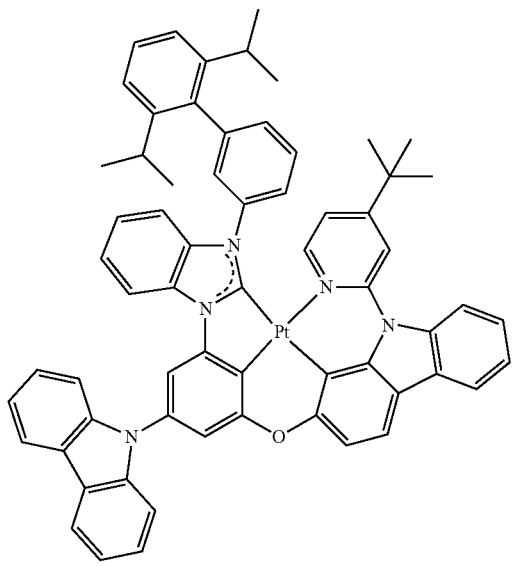
32
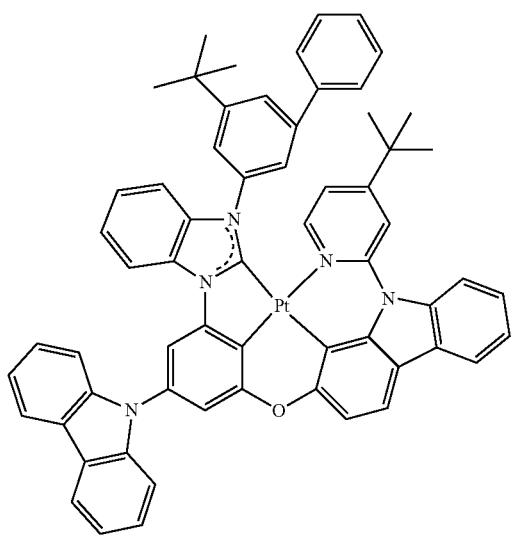
33
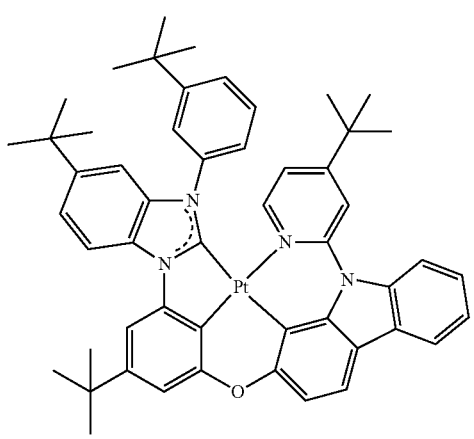
-continued
34
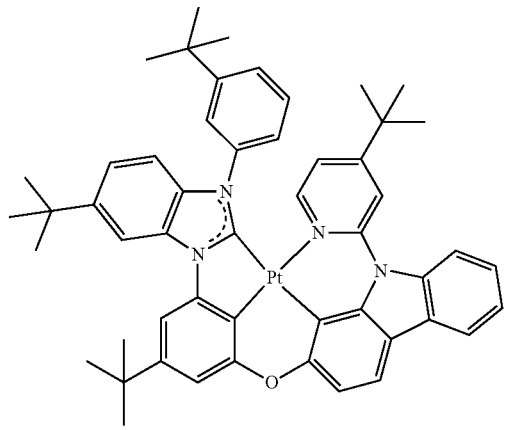
35
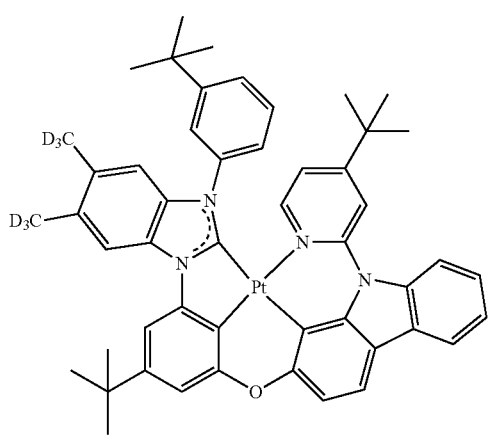
36
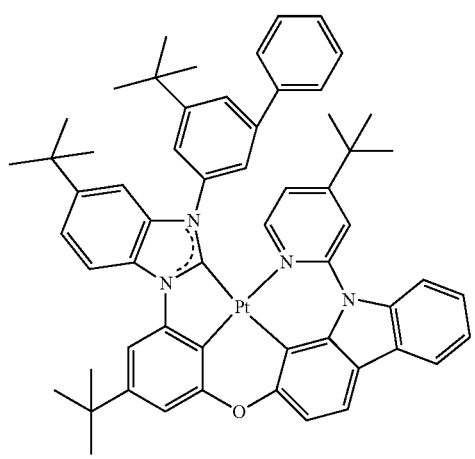

2491
-continued
37
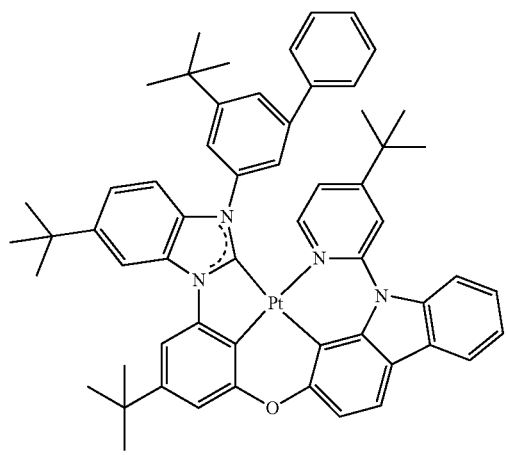
38
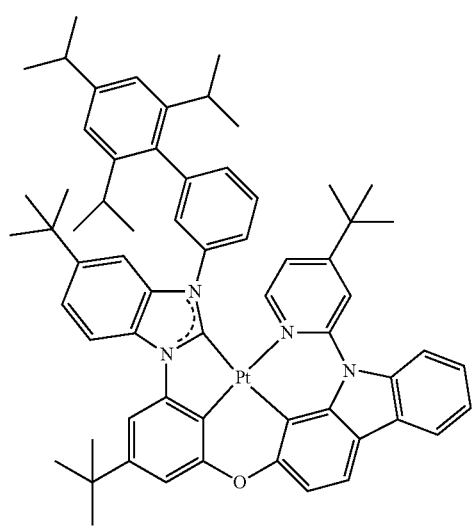
39
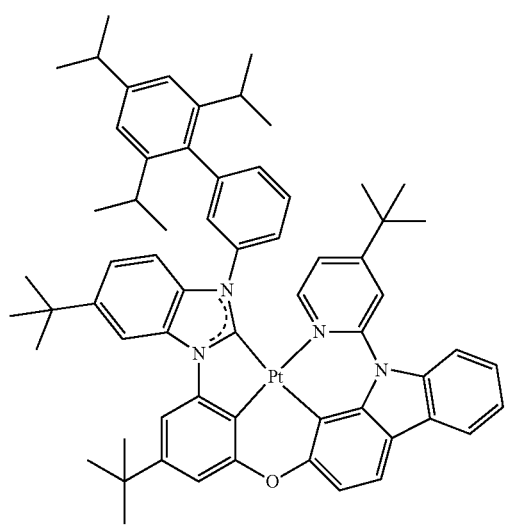
2492
-continued
40
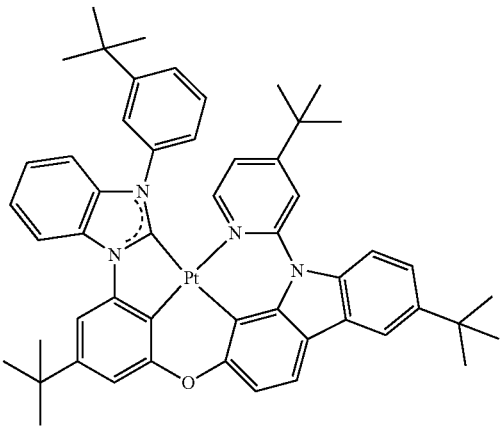
41
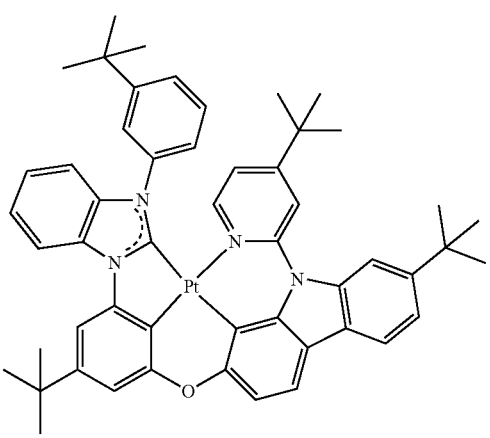
42
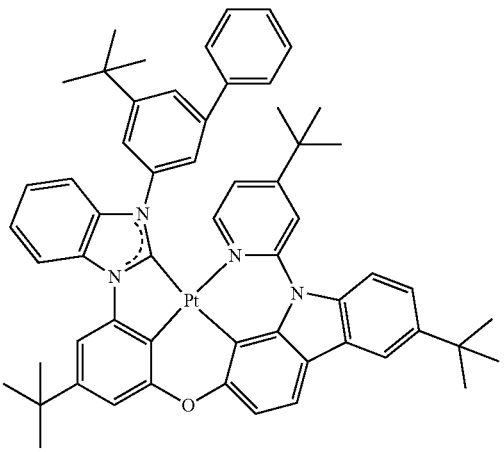

43
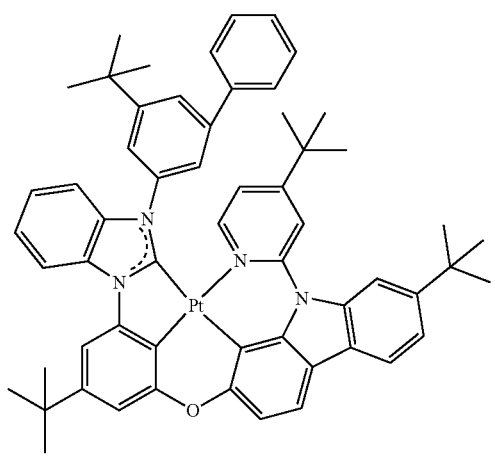
44
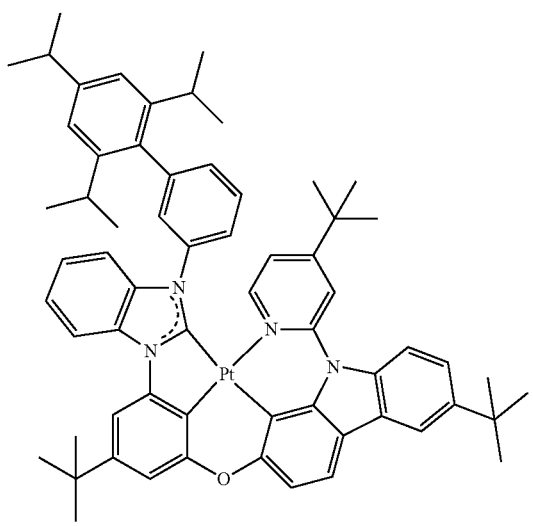
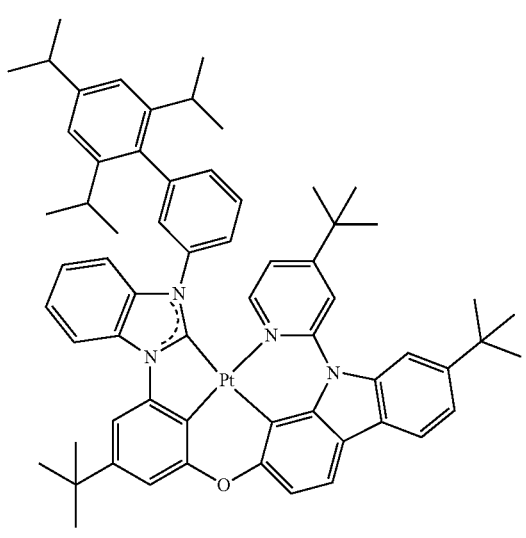
46
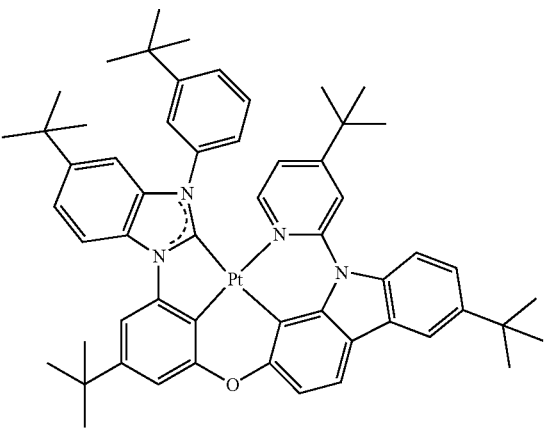
47
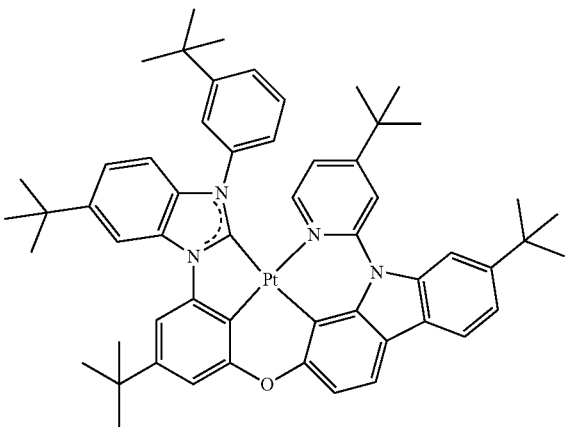
48
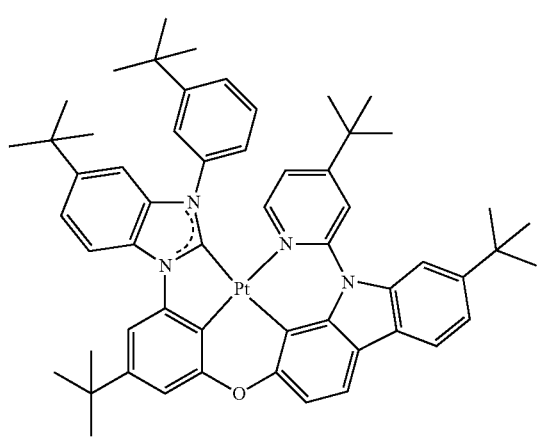

49
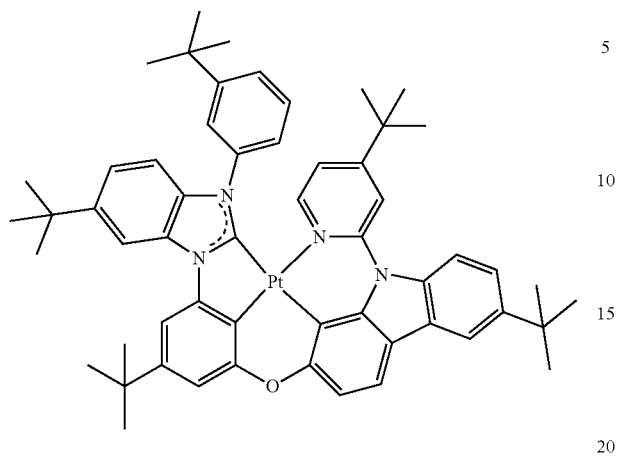
50
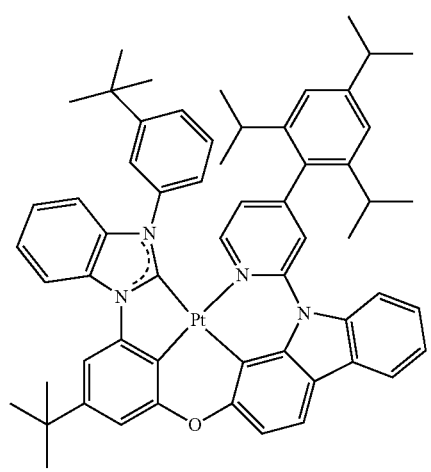
51
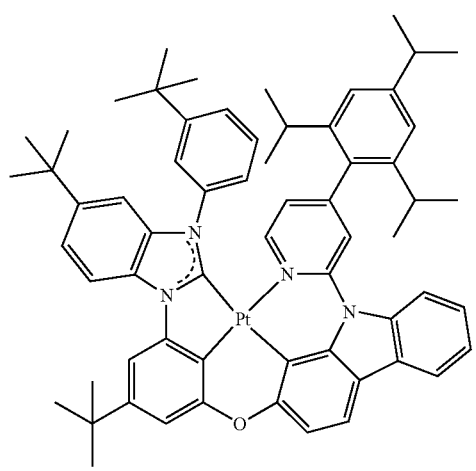
52
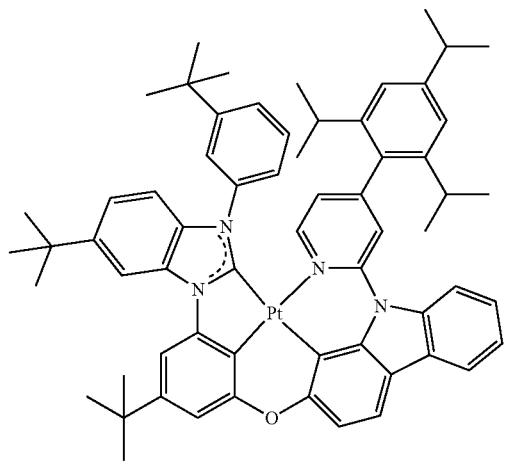
53
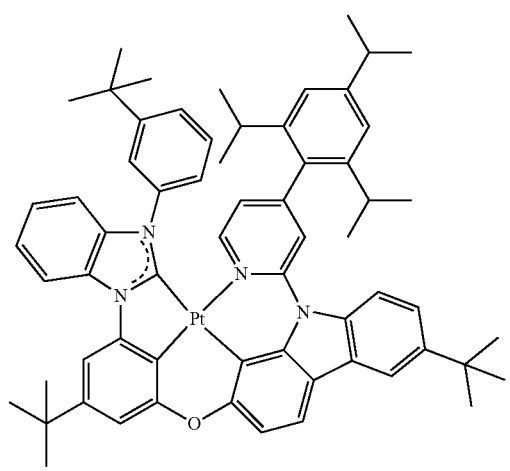
54
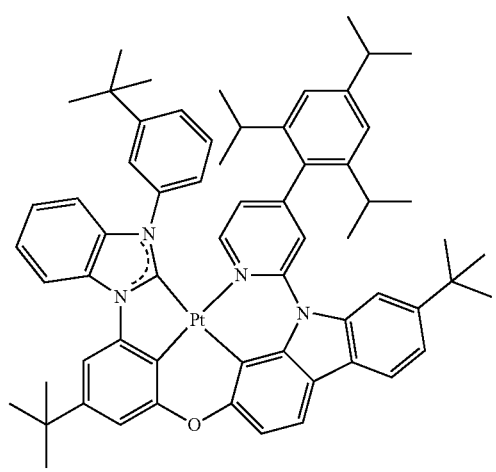

55
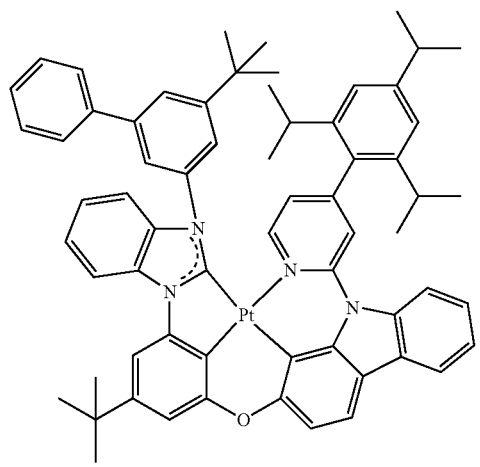
56
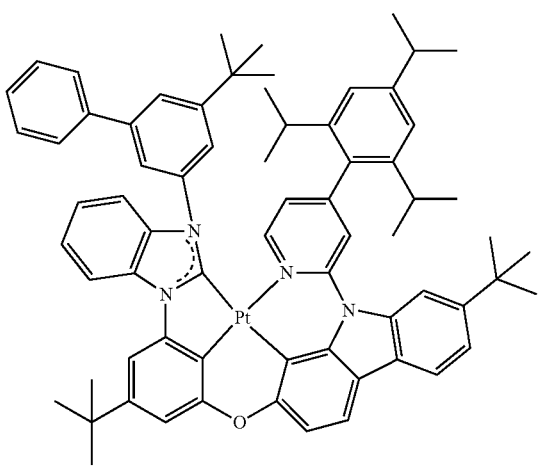
57
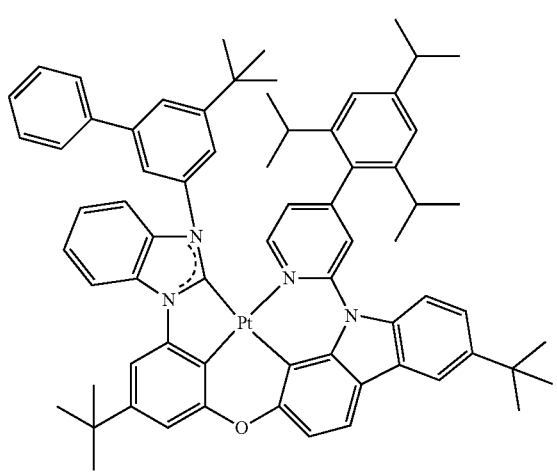
58
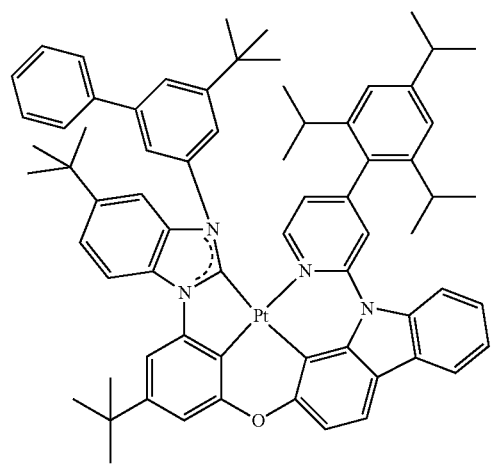
59
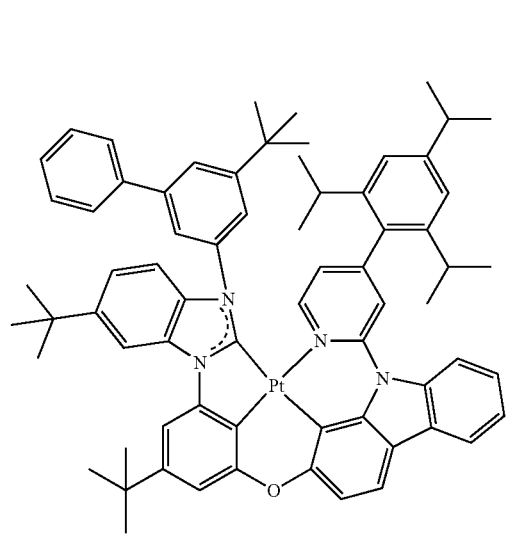
60
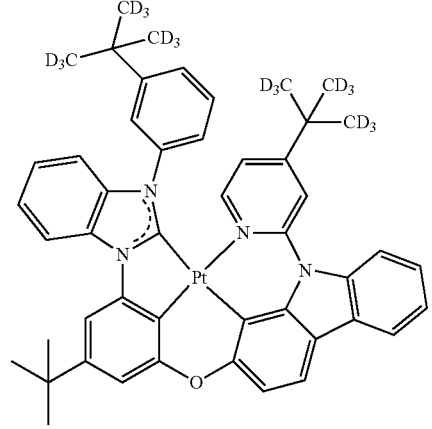

61
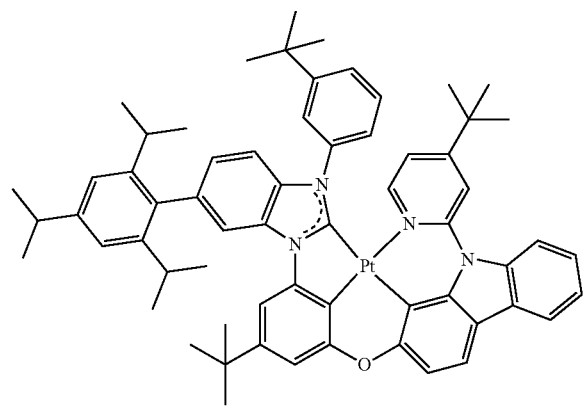
62
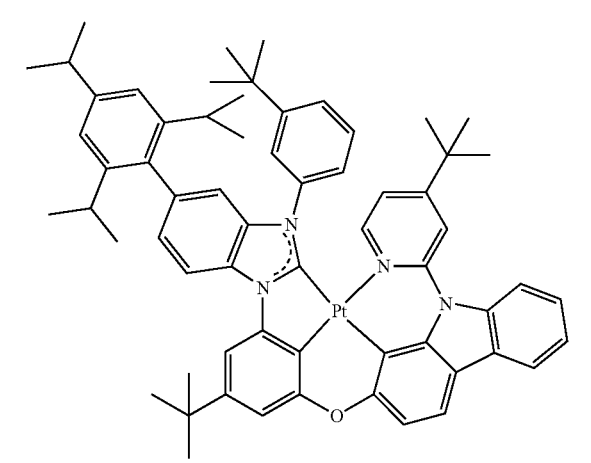
63
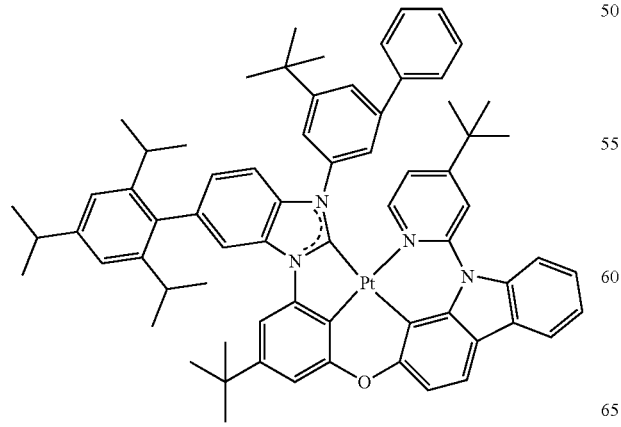
64
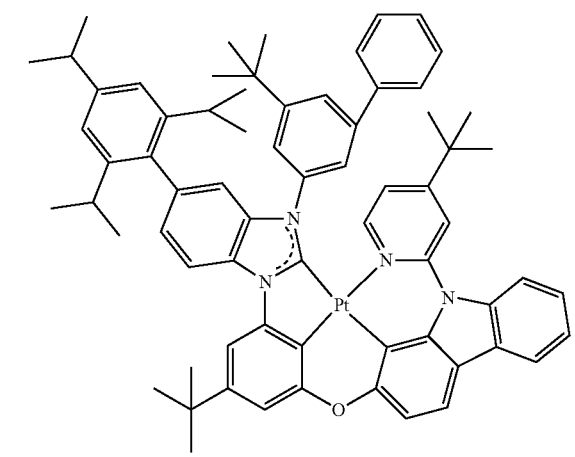
65
66
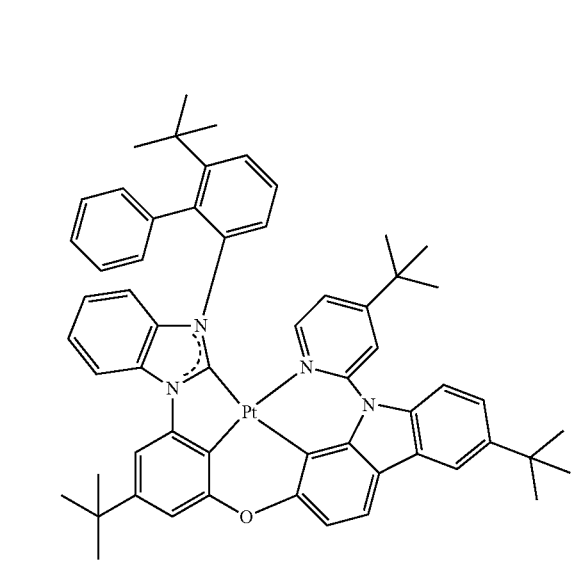

2501
-continued
67
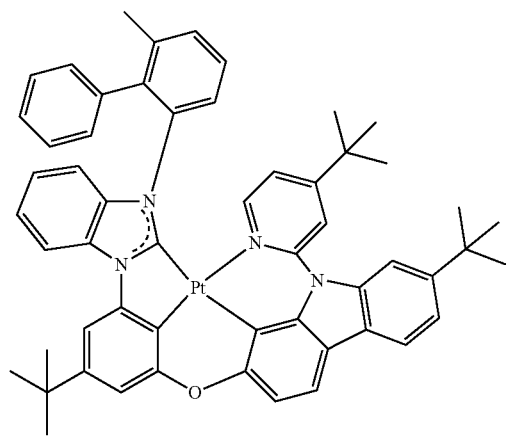
68
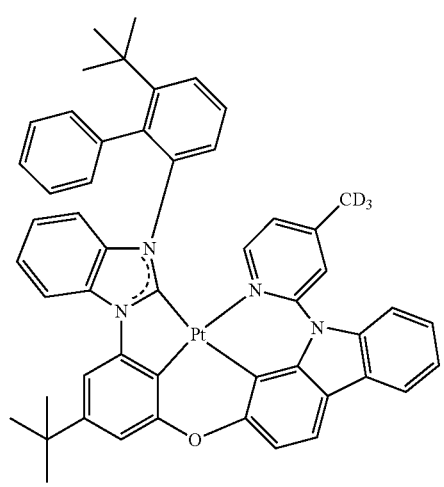
69
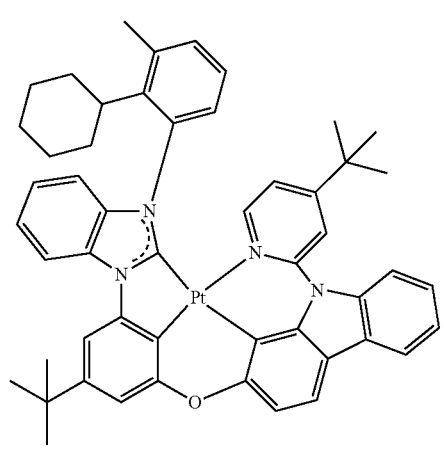
2502
-continued
70
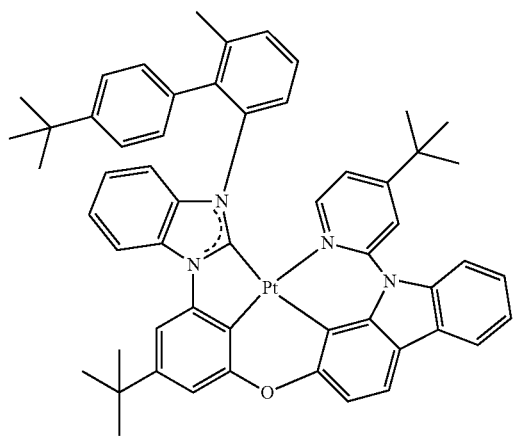
71
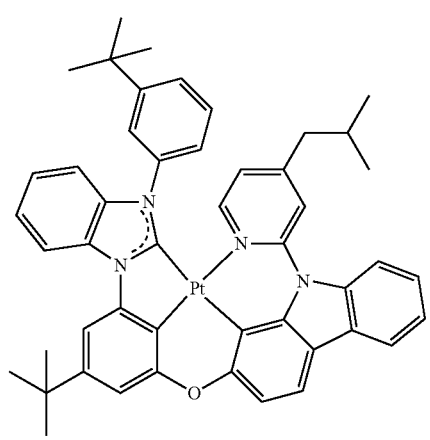
72
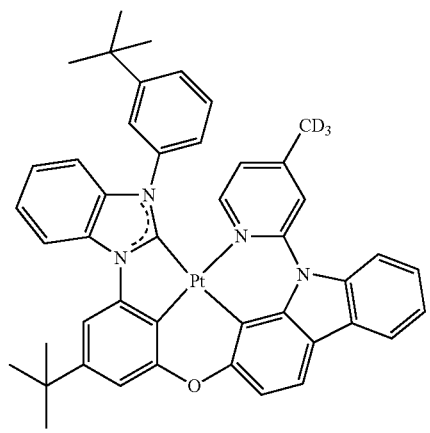

2503
-continued
73
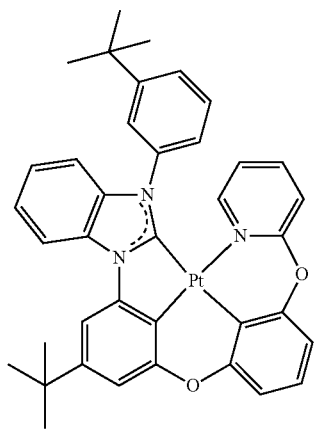
74
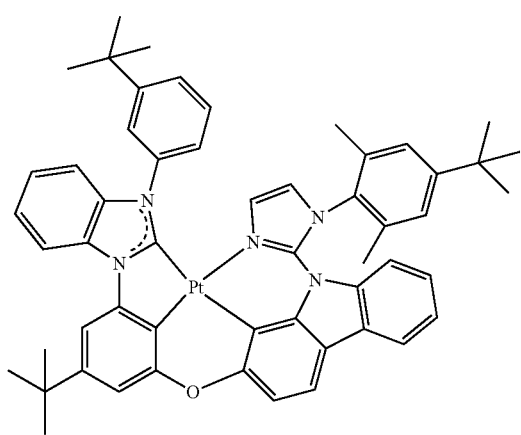
75
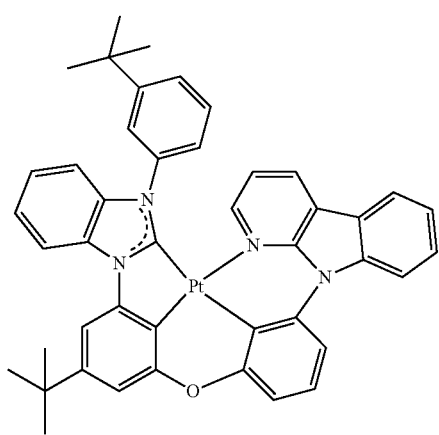
2504
-continued
76
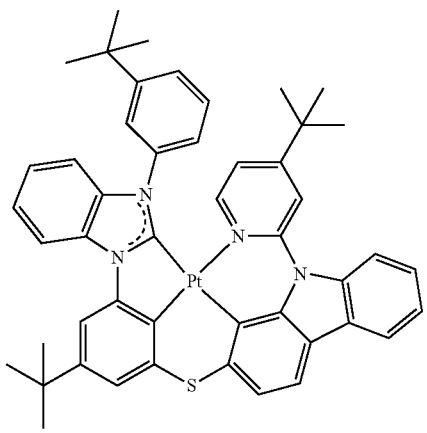
77
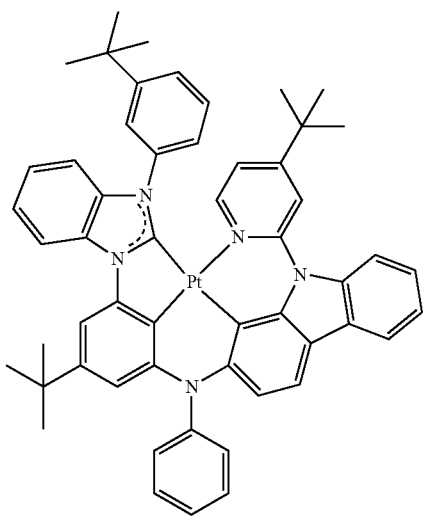
78
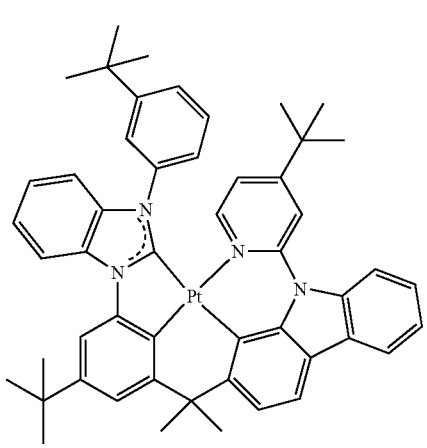

2505
-continued
79
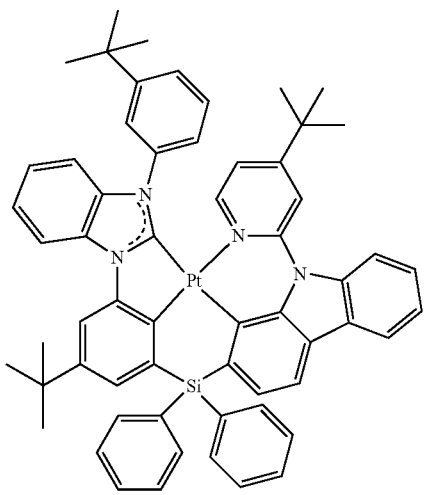
80
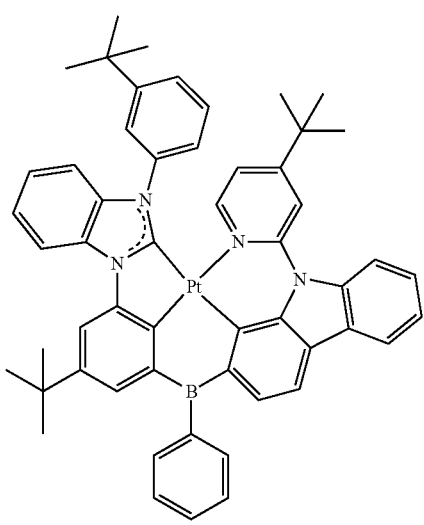
81
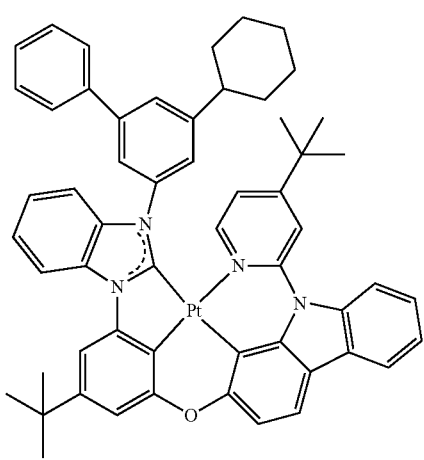
2506
-continued
82
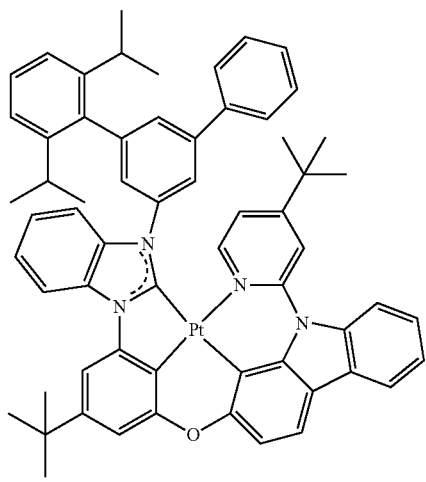
83
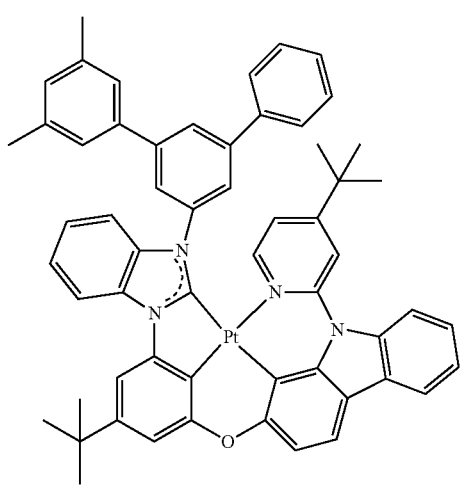
84
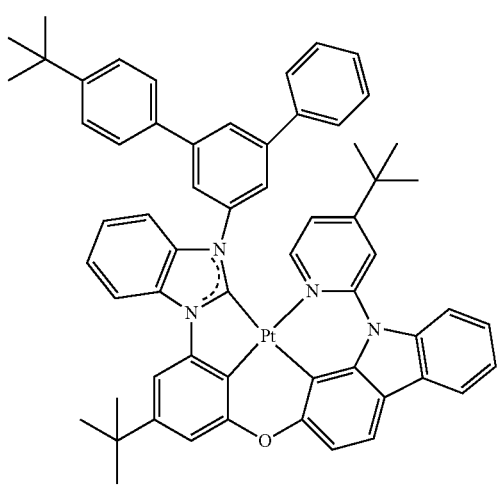

2507
-continued
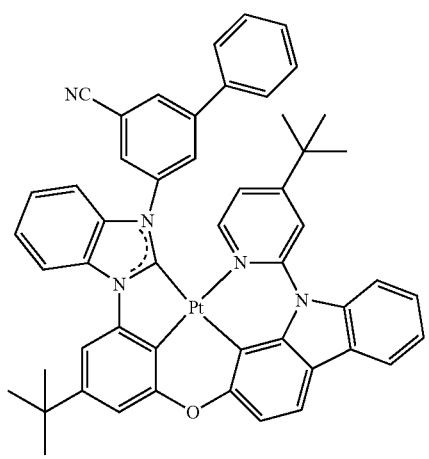
85
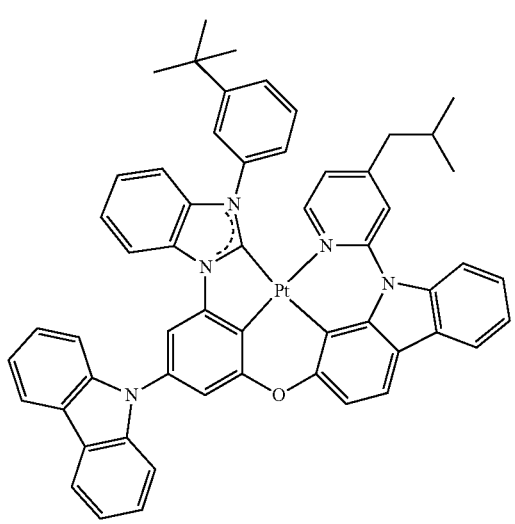
86
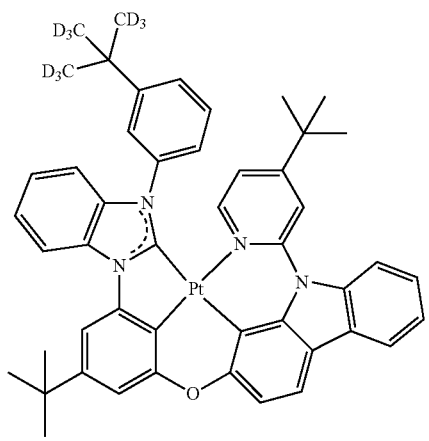
87
2508
-continued
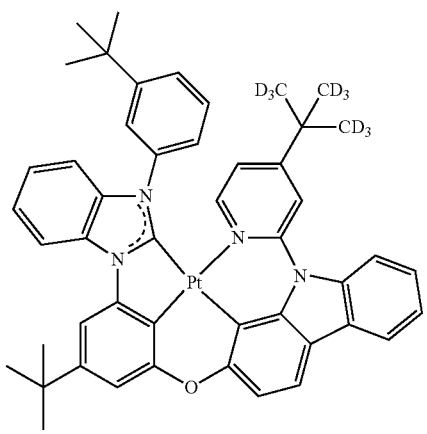
88
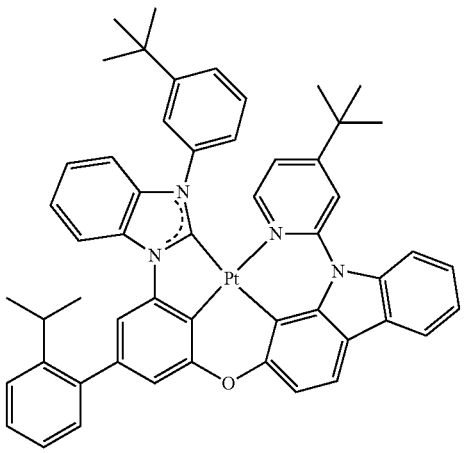
89
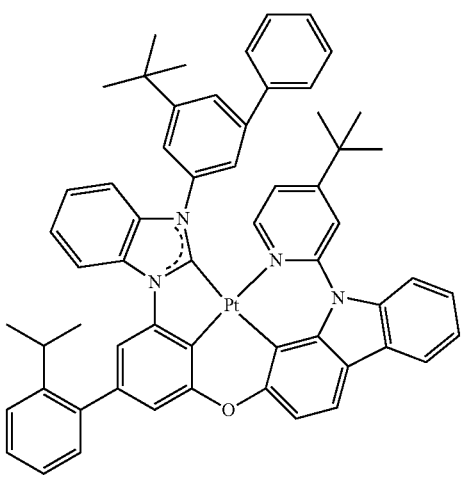
90

91
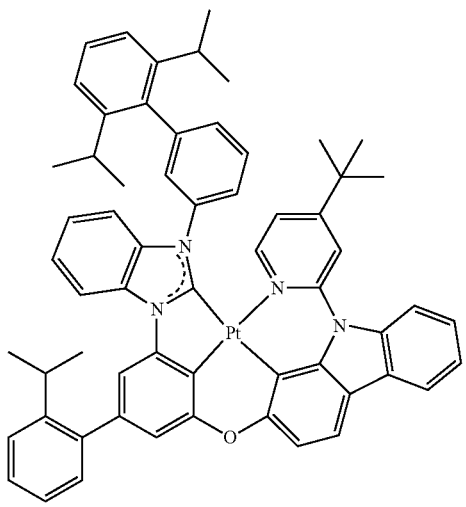
92
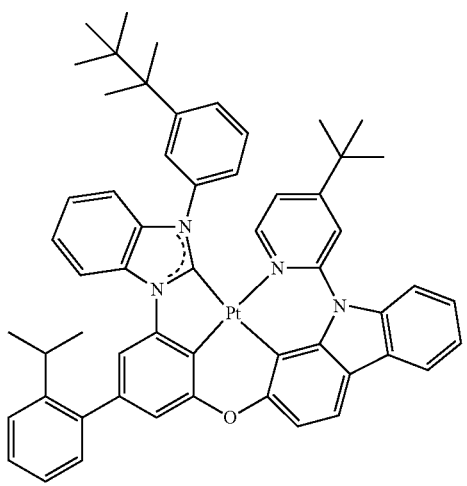
93
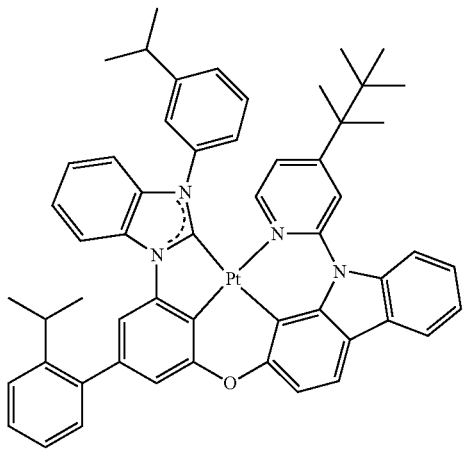
94
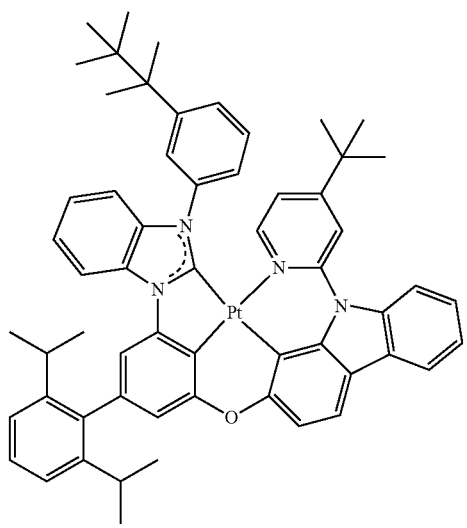
95
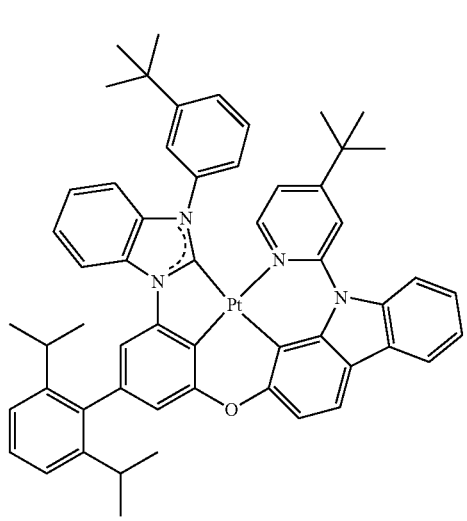
96
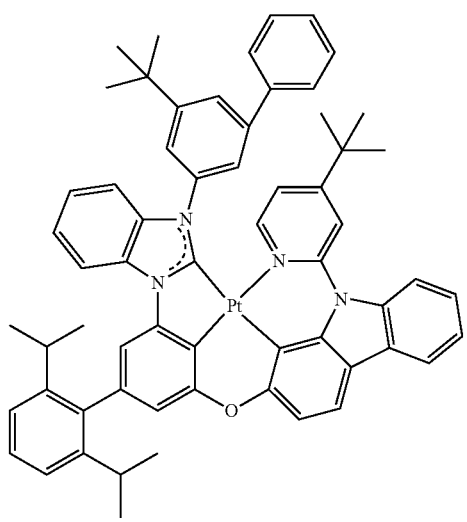

2511
-continued
97
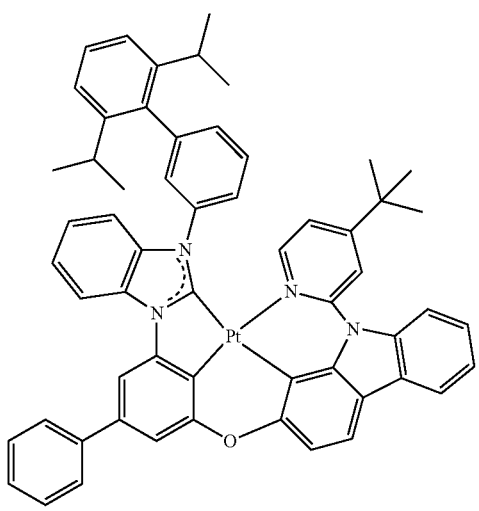
98
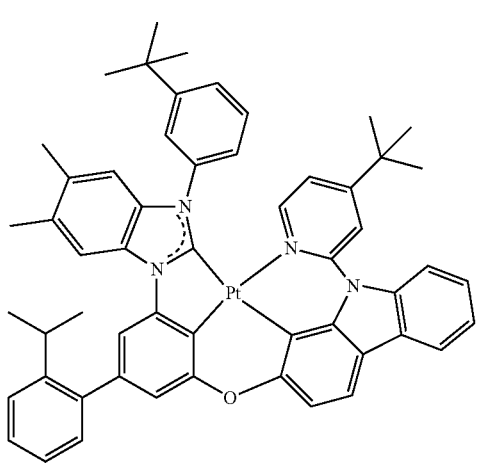
99
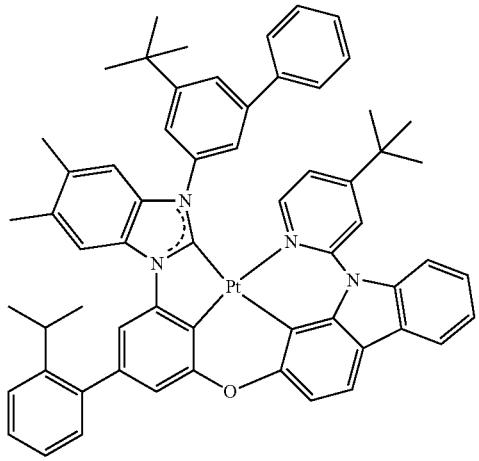
2512
-continued
100
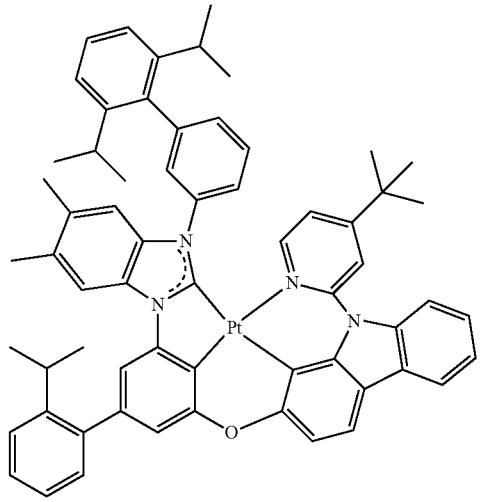
101
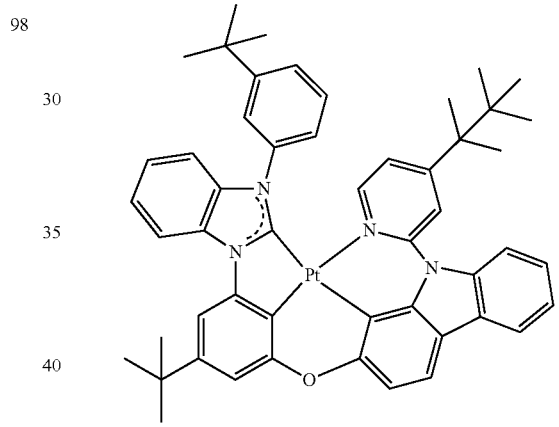
102
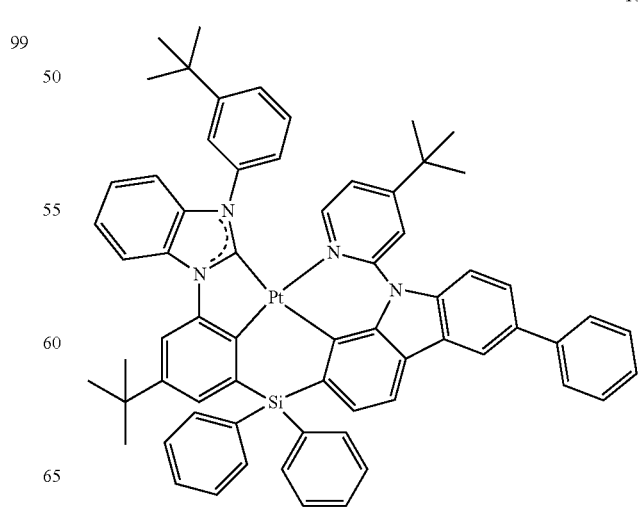

2513
-continued
103
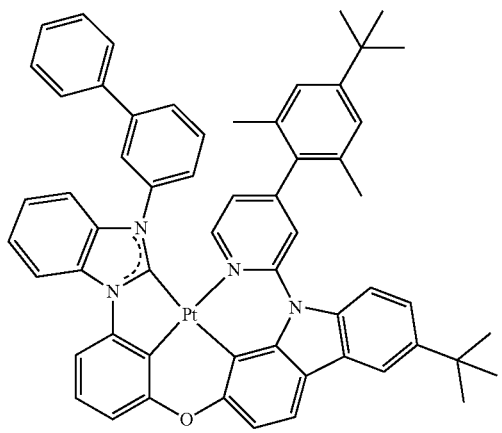
104
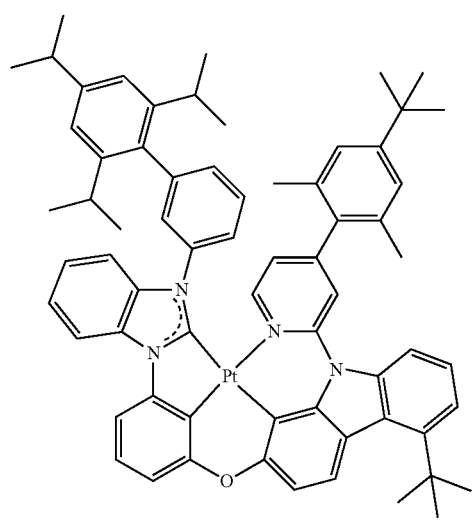
105
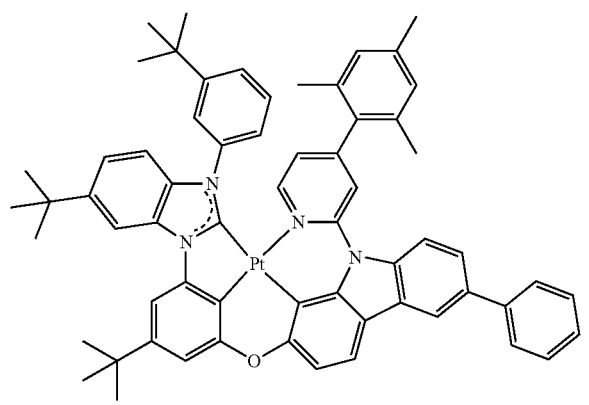
2514
-continued
106
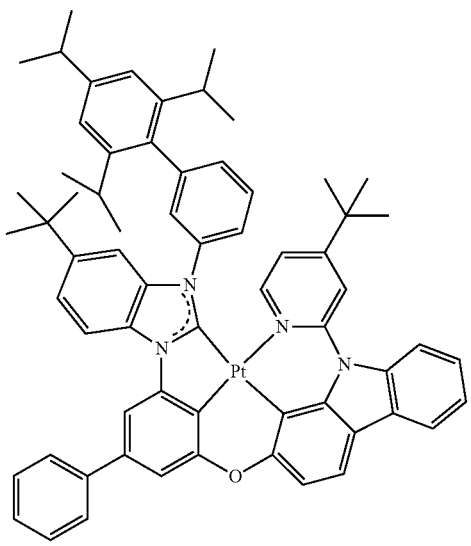
107
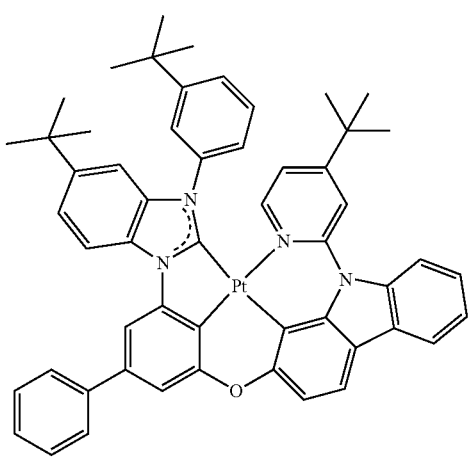
108
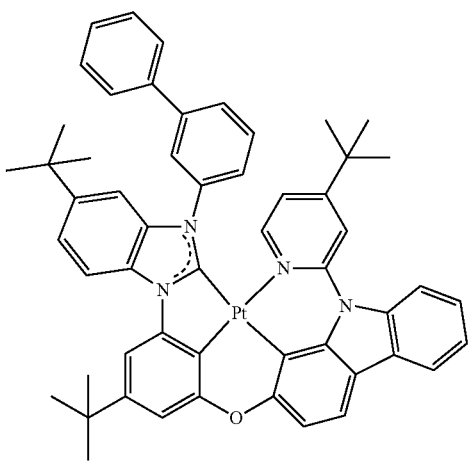

109
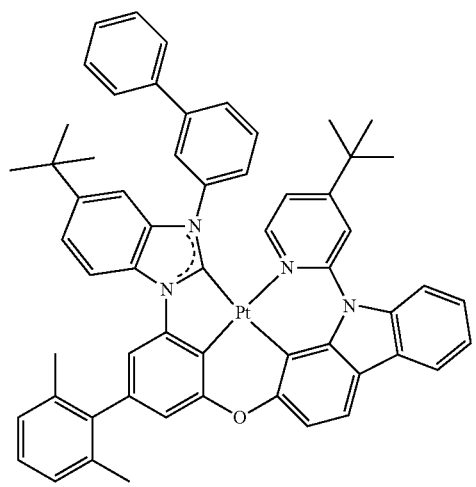
110
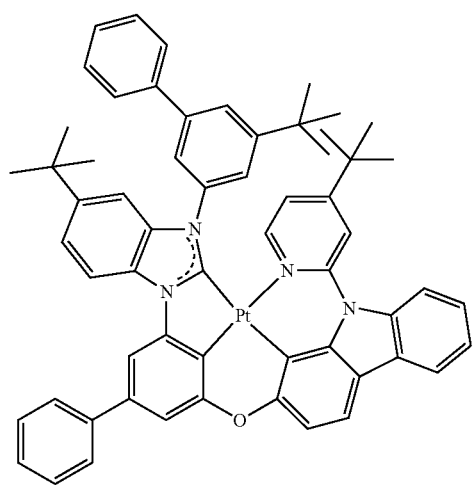
111
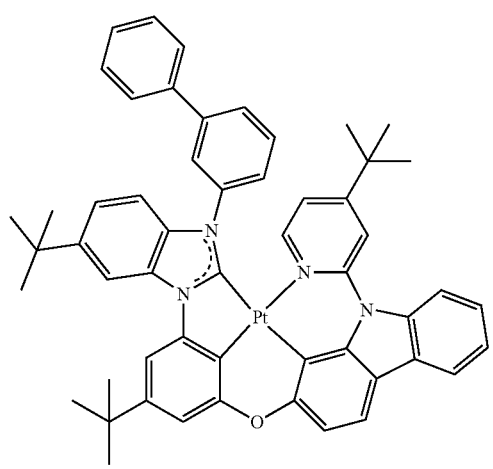
112
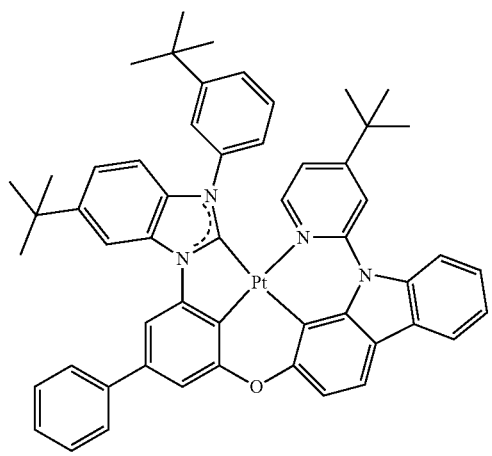
113
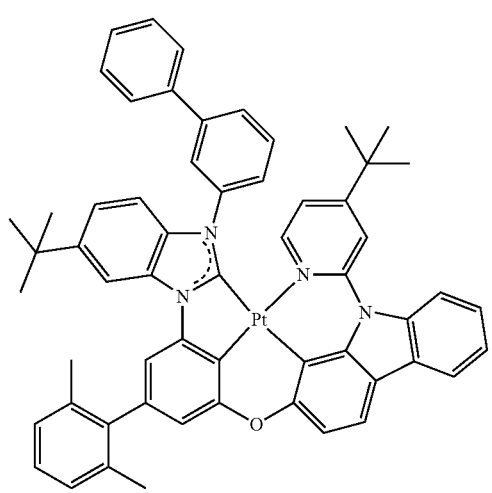
114
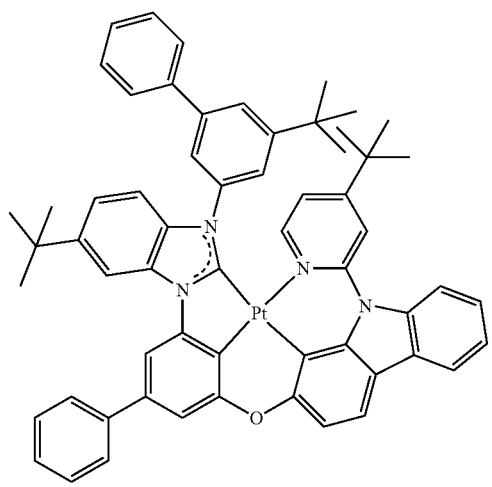

2517
-continued
2518
-continued
115
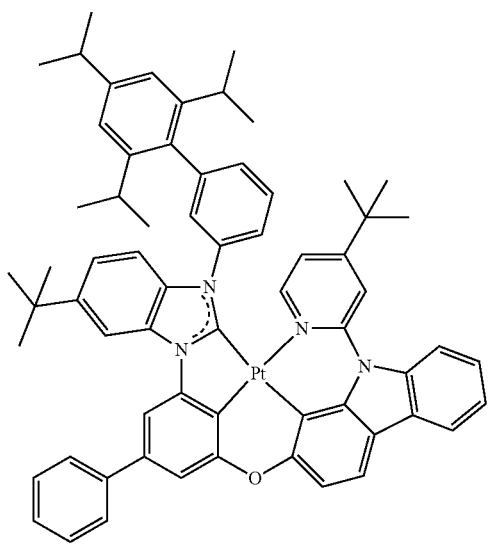
118
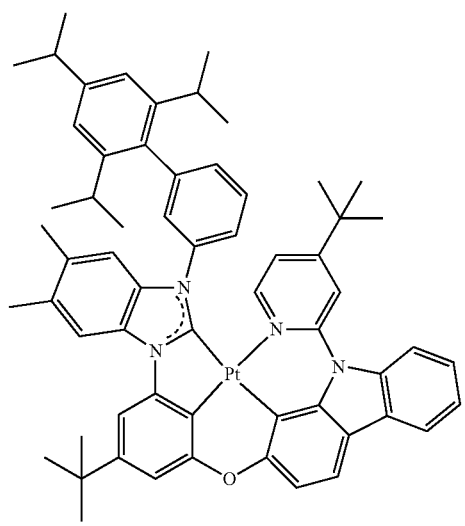
116
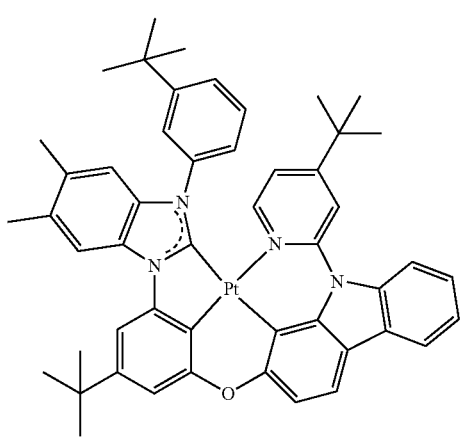
119
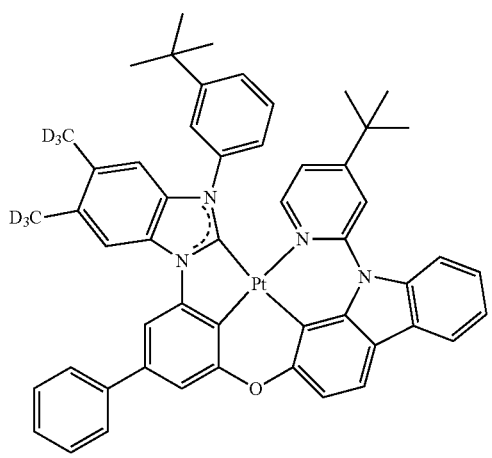
117
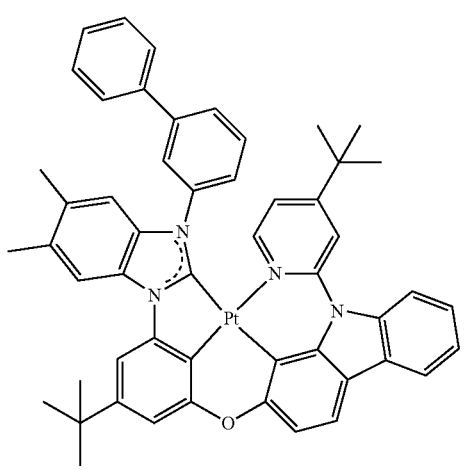
120
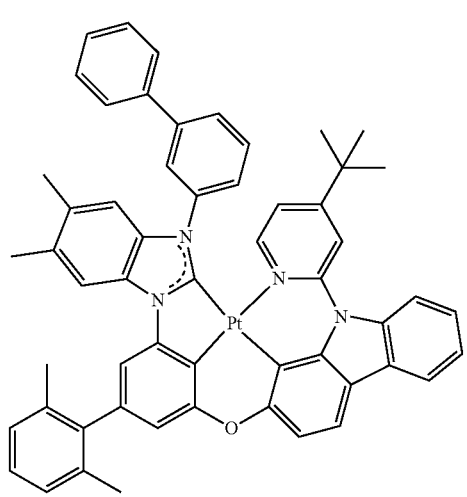

-continued
121
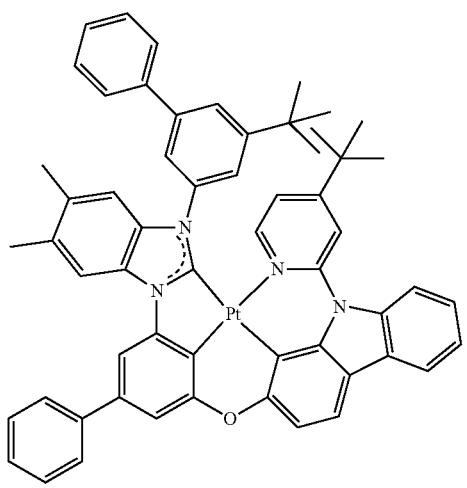
122
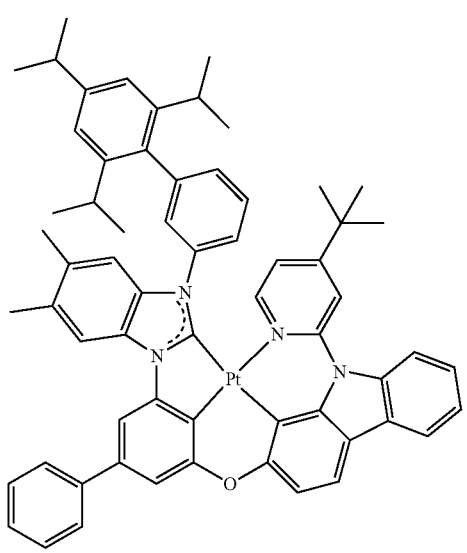
123
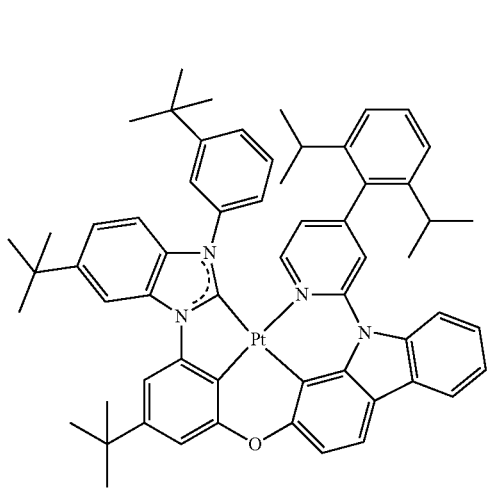
-continued
124
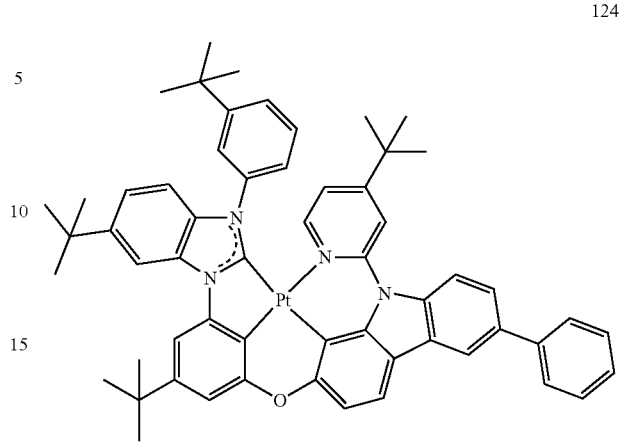
125
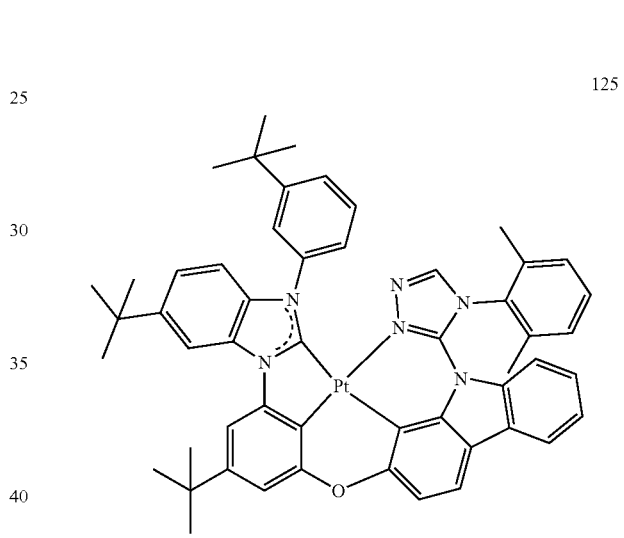
126
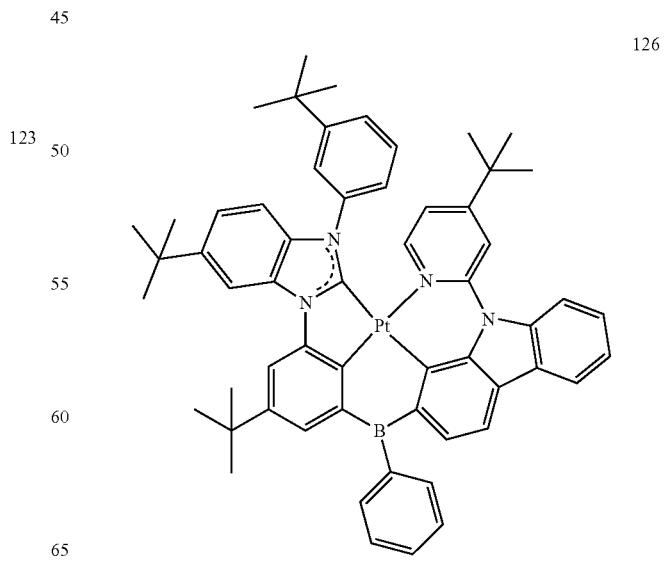

2521
-continued
127
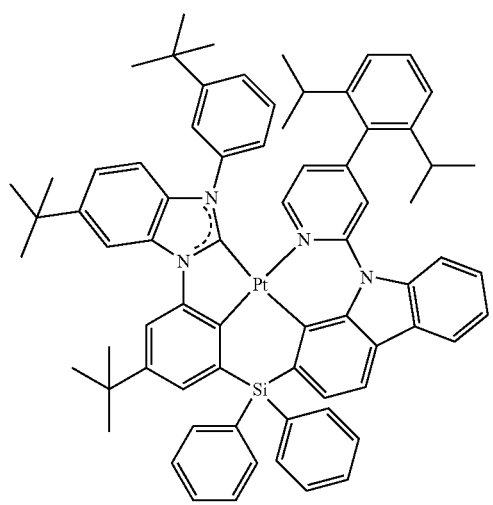
128
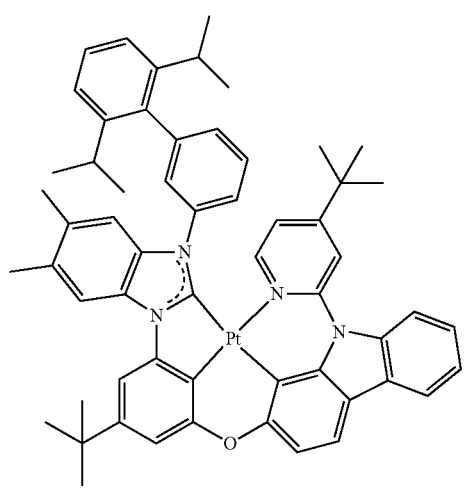
129
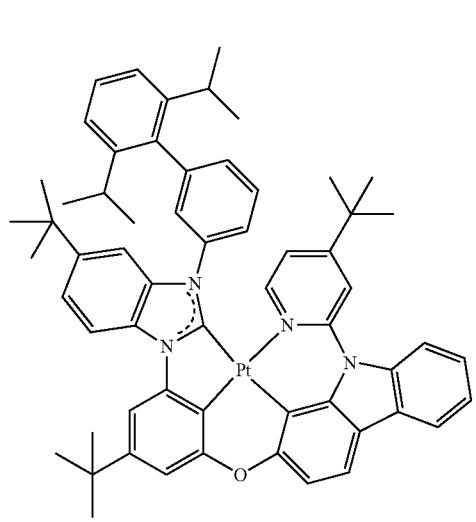
2522
-continued
130
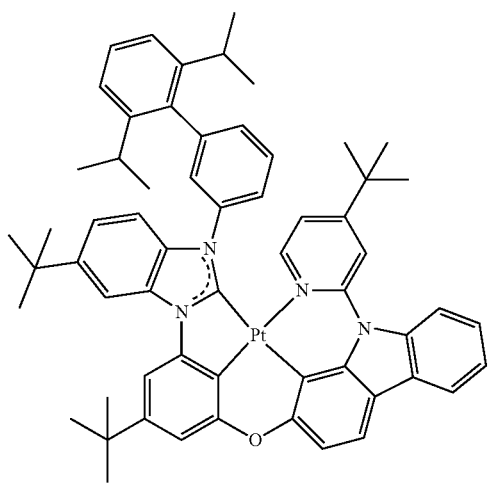
131
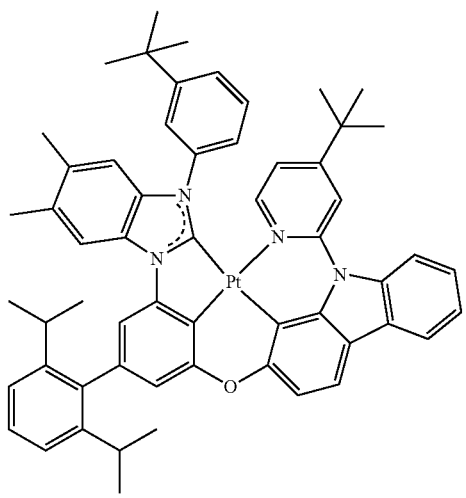
132
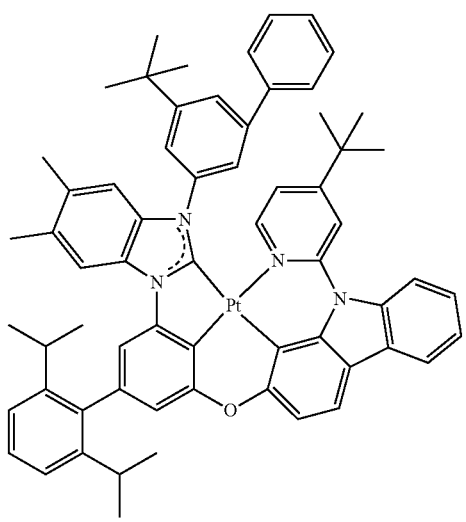

133
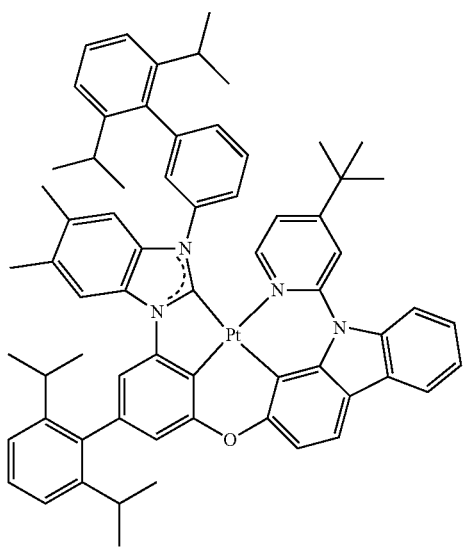
134
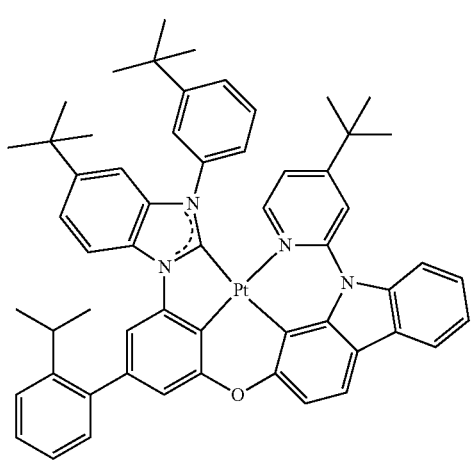
135
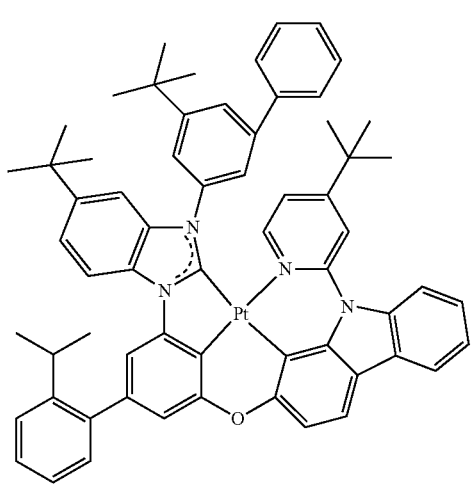
136
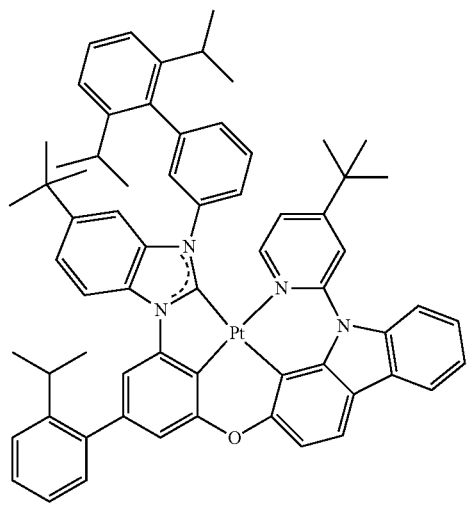
137
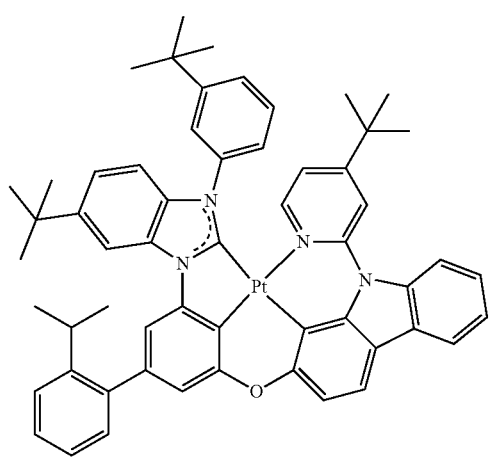
138
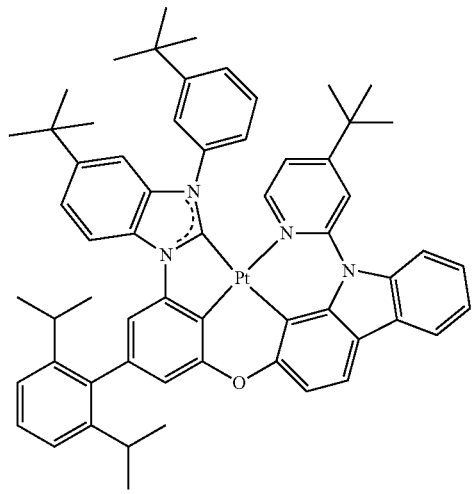

2525
139
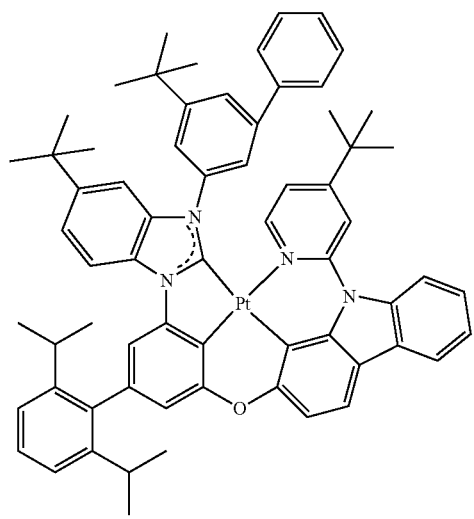
140
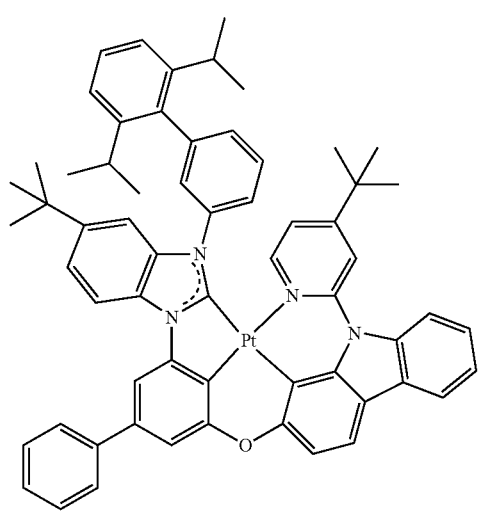
141
2526
142
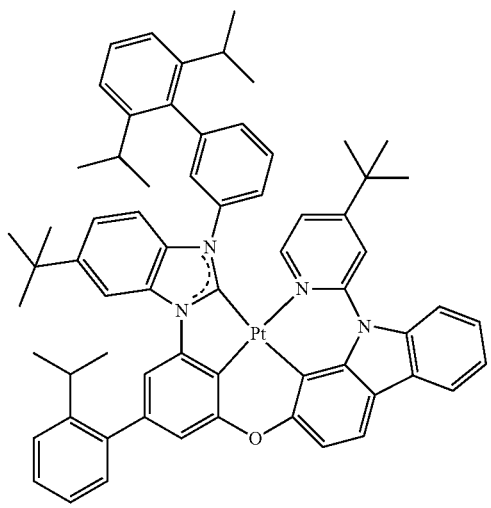
143
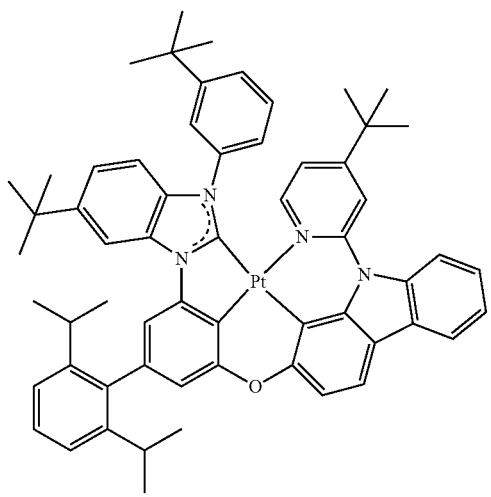
144
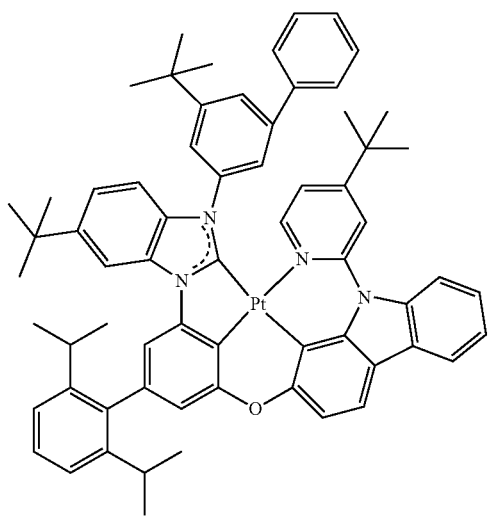

2527
-continued
145
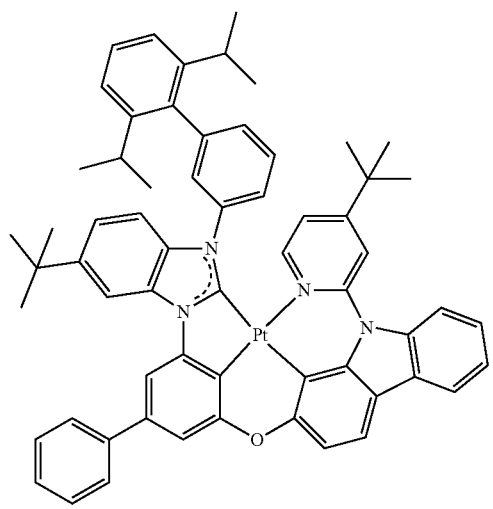
146
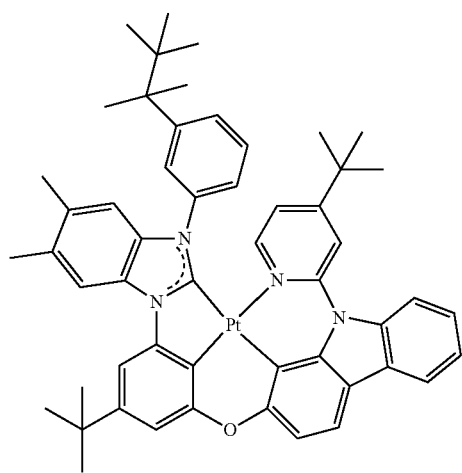
147
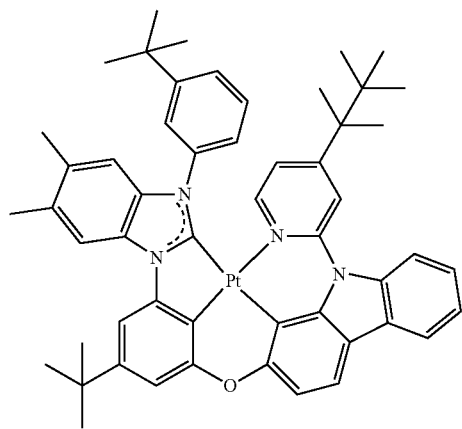
2528
-continued
148
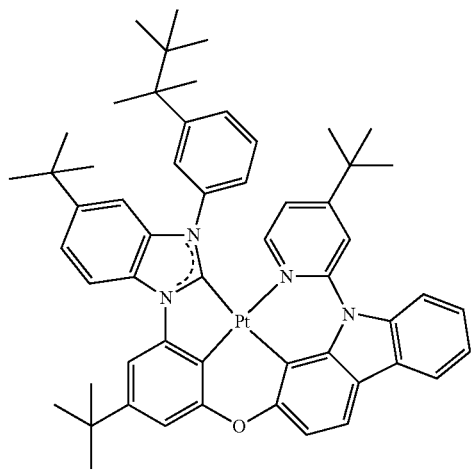
149
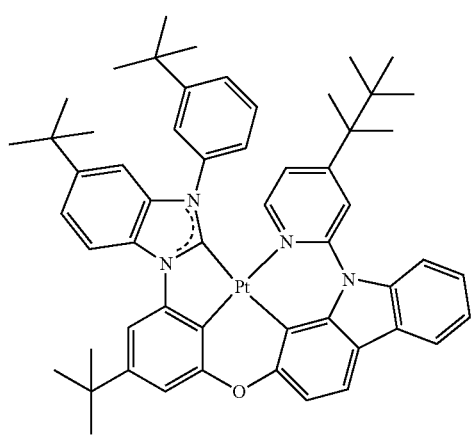
150
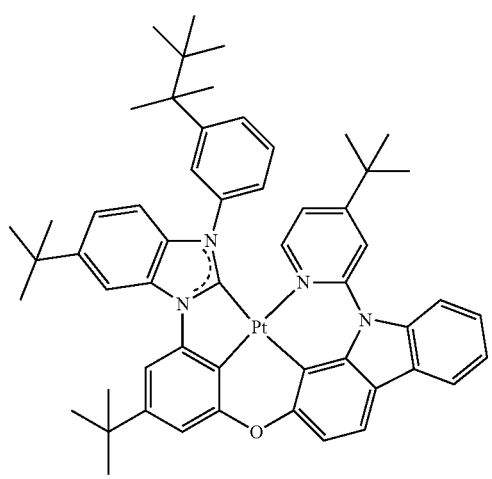

2529
151
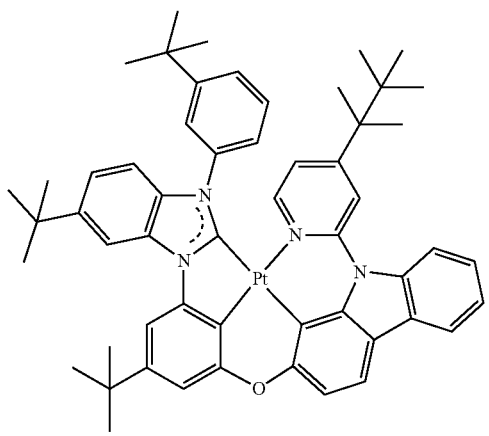
152
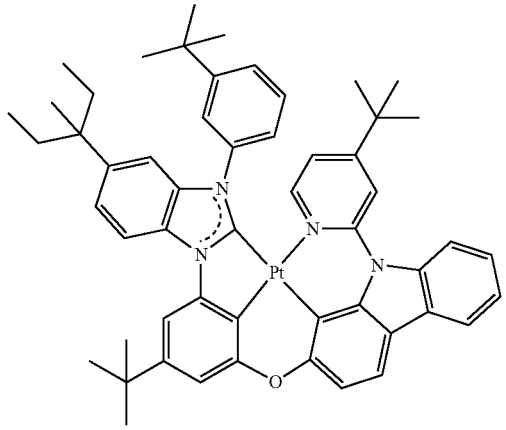
153
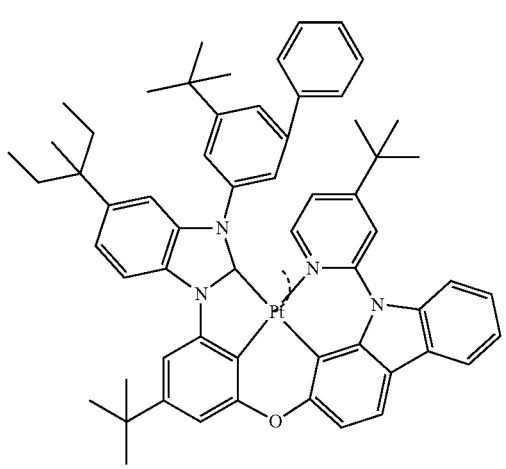
2530
-continued
154
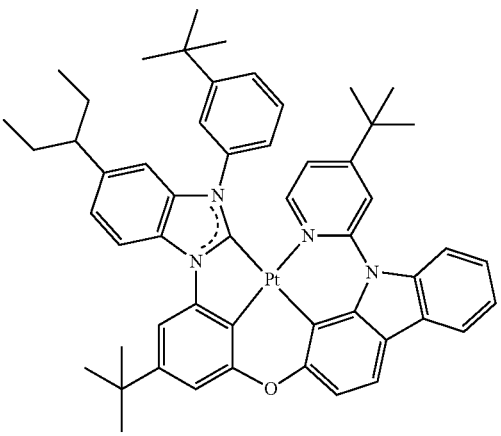
155
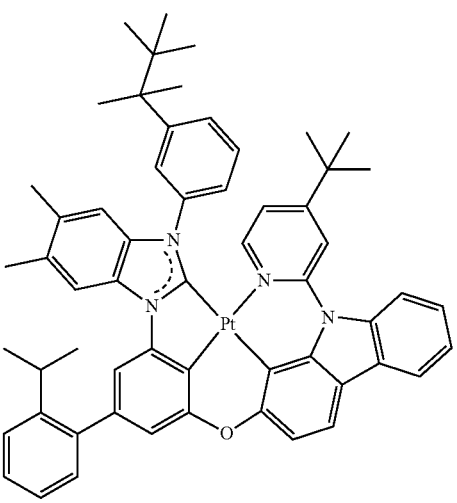
156
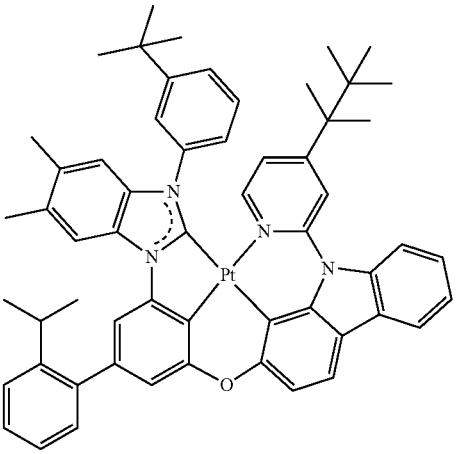

2531 -continued
157
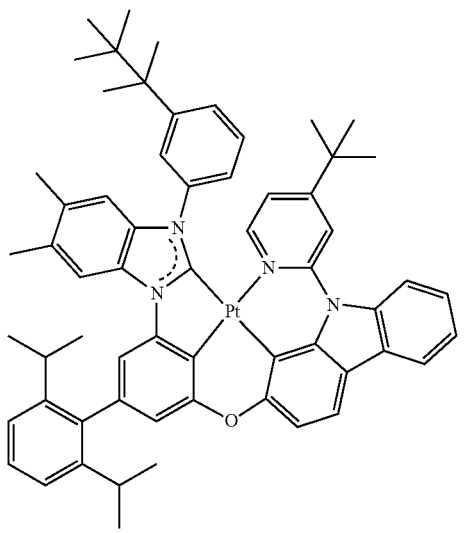
158
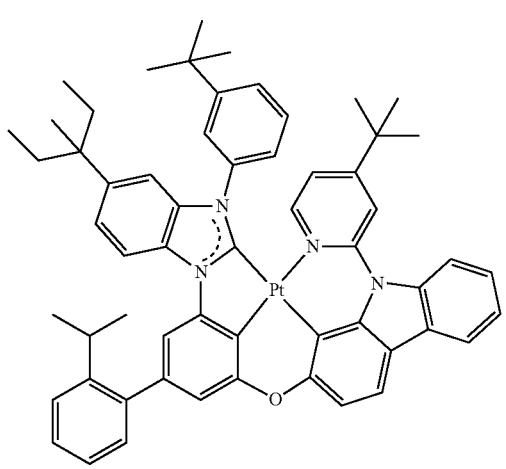
159
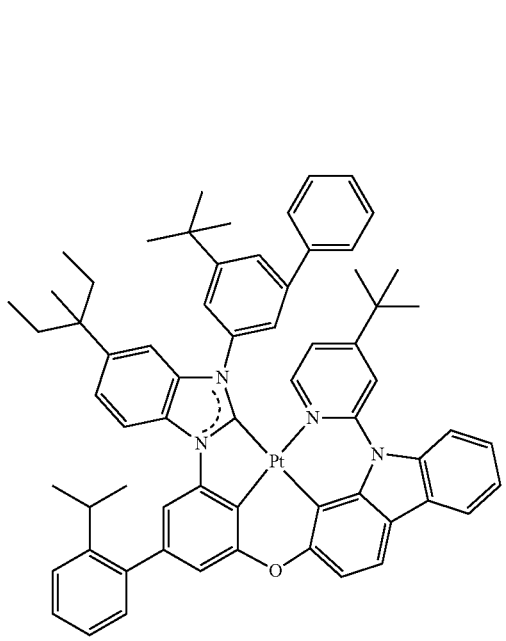
2532 -continued
160
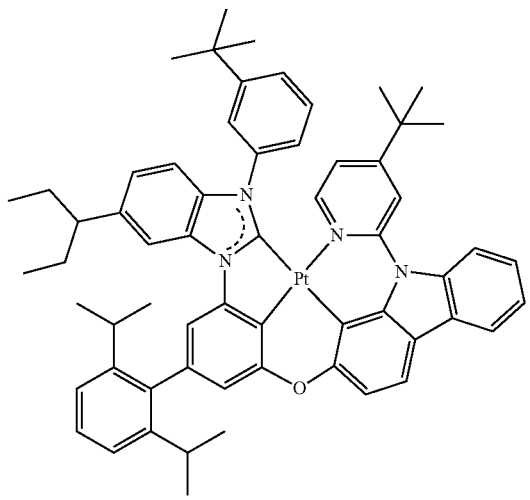
161
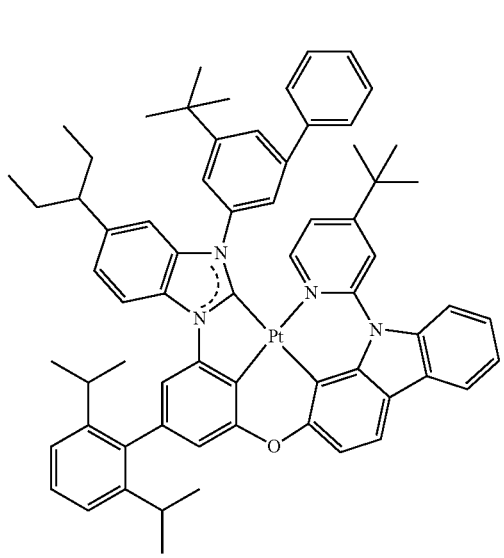
162
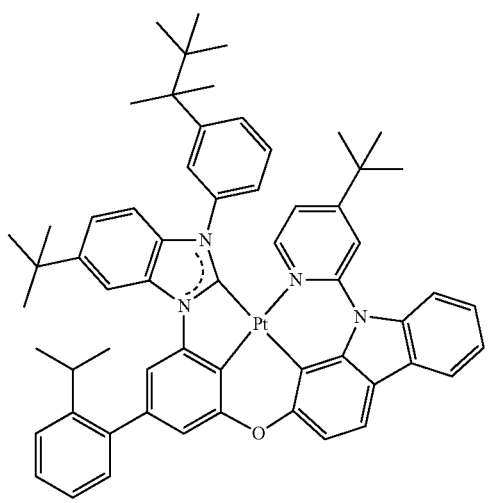

2533
-continued
163
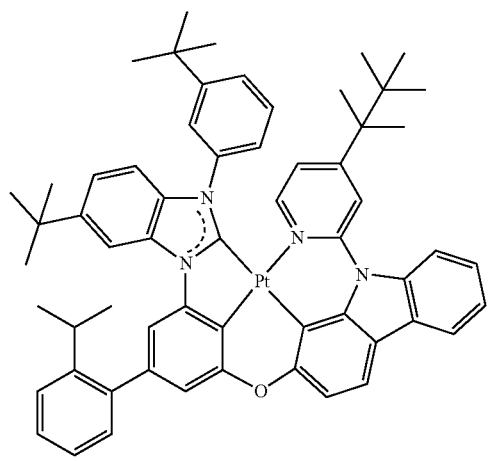
164
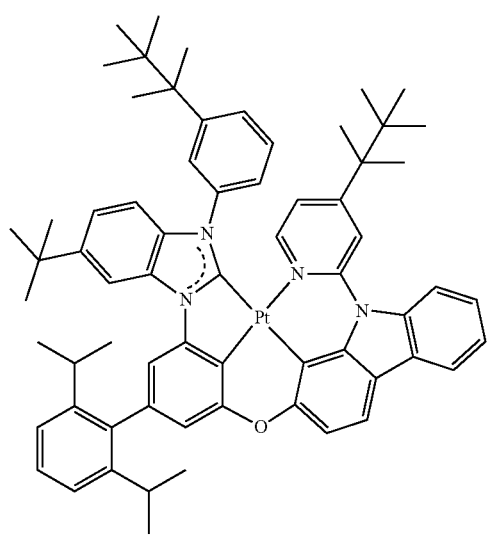
165
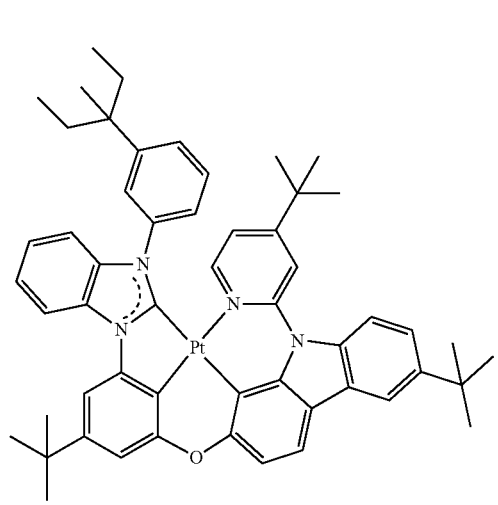
2534
-continued
166
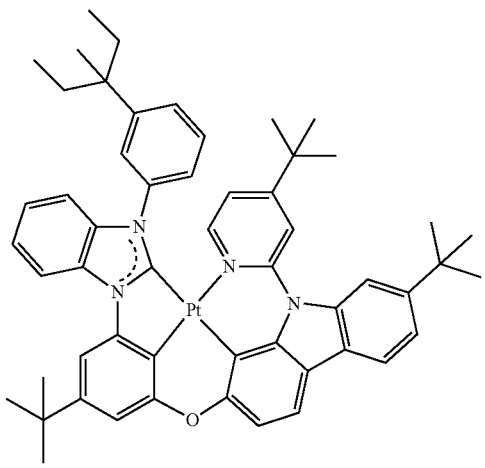
167
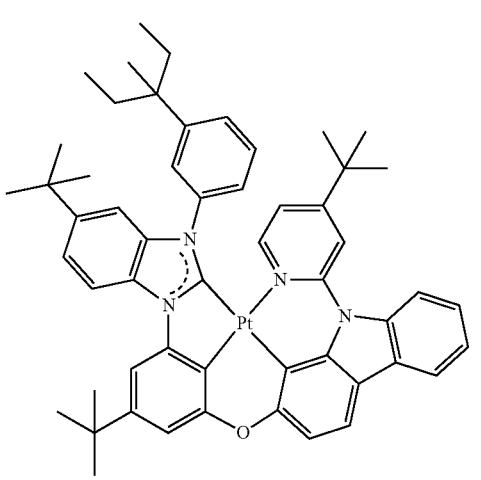
168
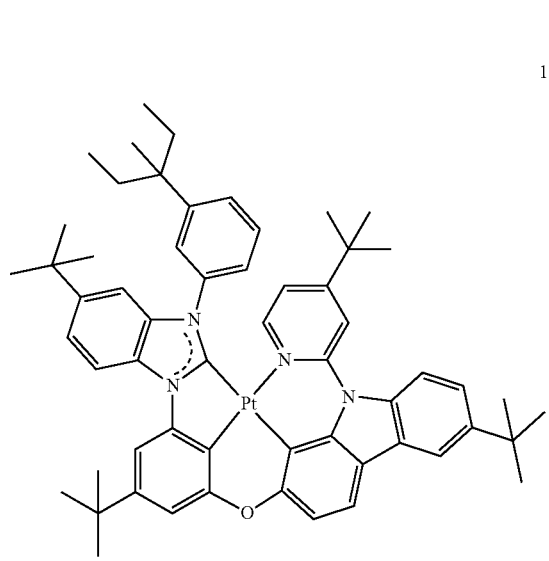

2535
-continued
169
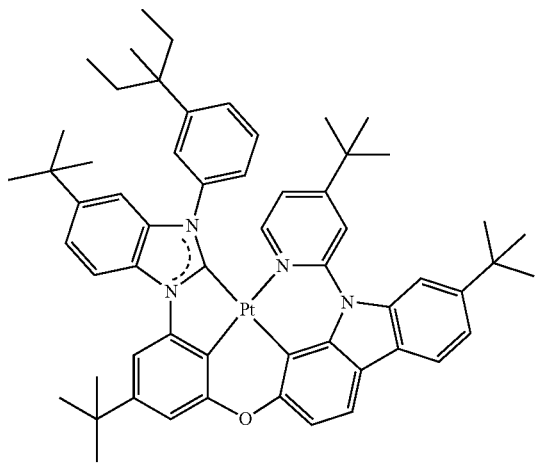
170
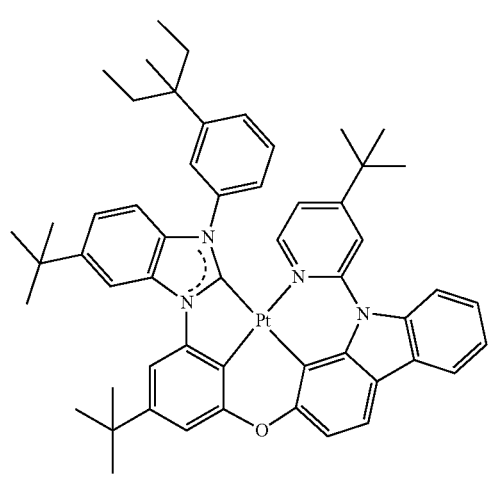
171
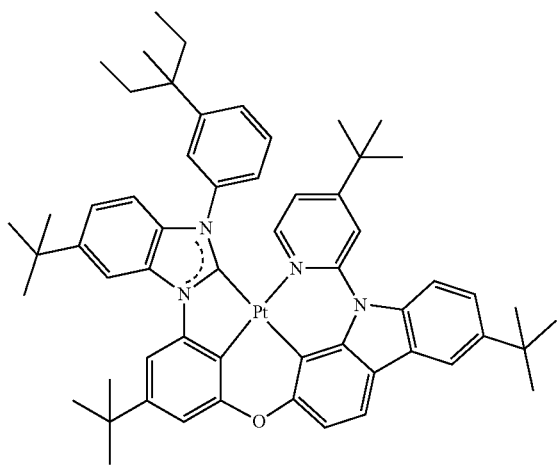
2536
-continued
172
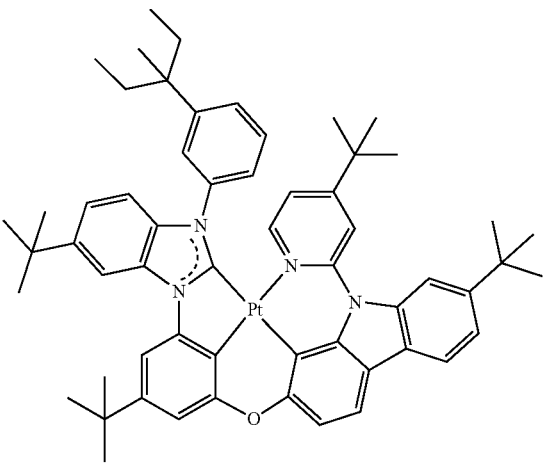
173
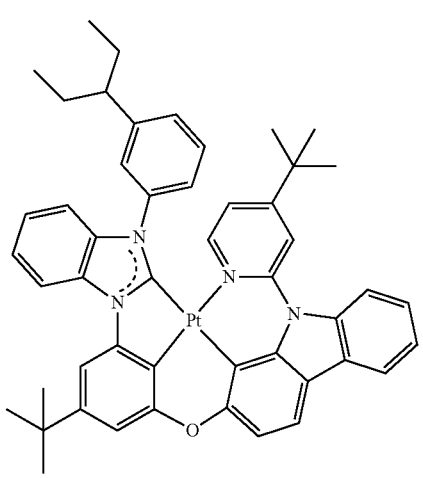
174
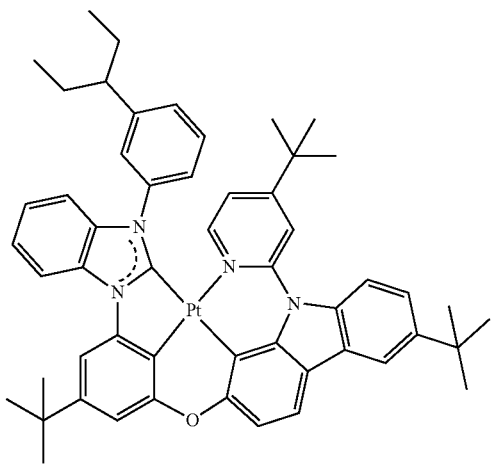

2537
-continued
175
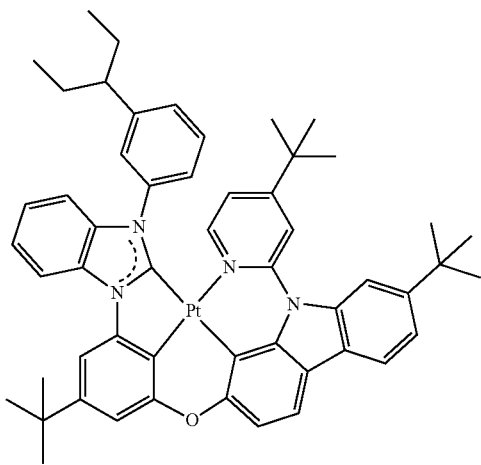
176
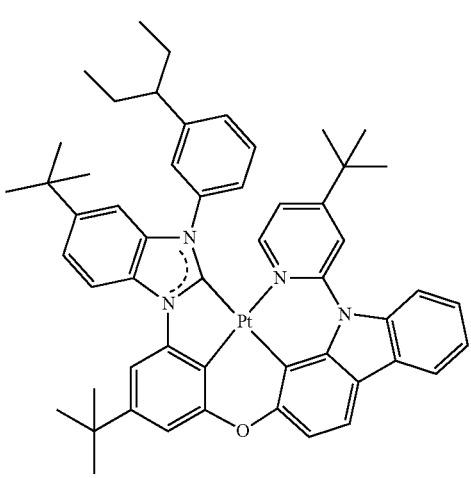
177
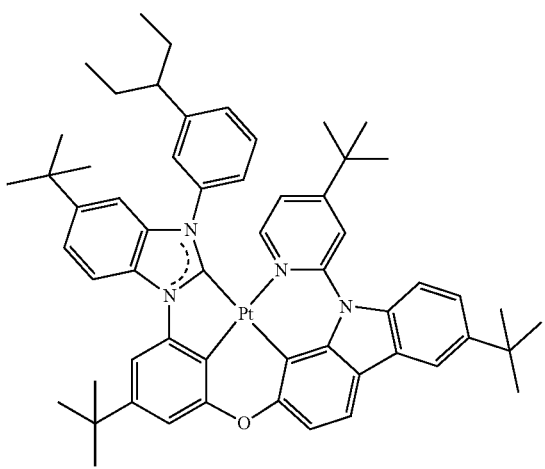
2538
-continued
178
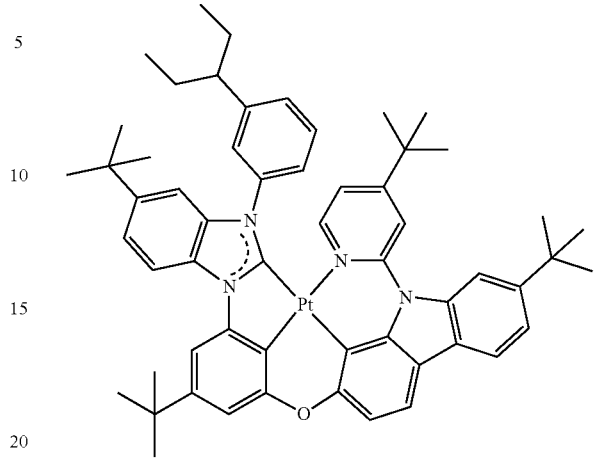
179
180
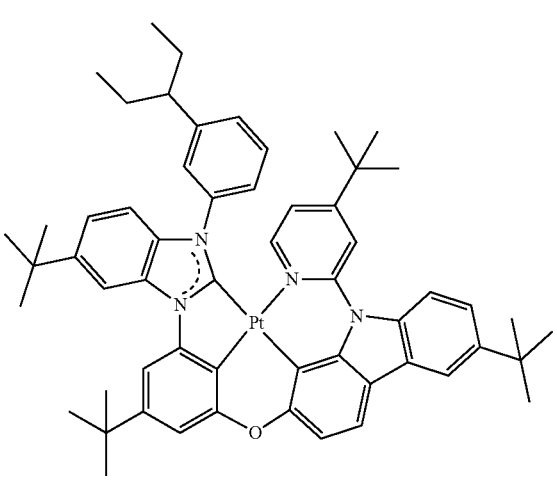

2539
-continued
181
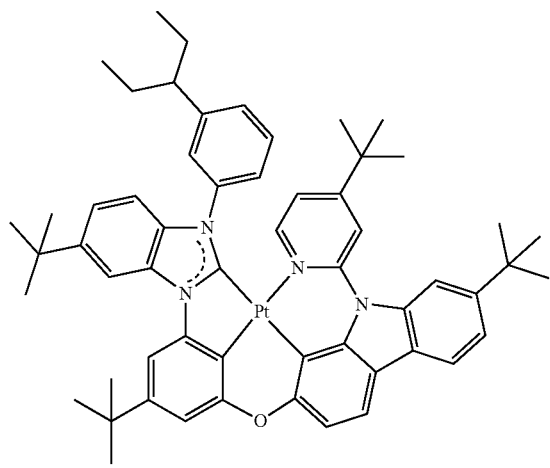
182
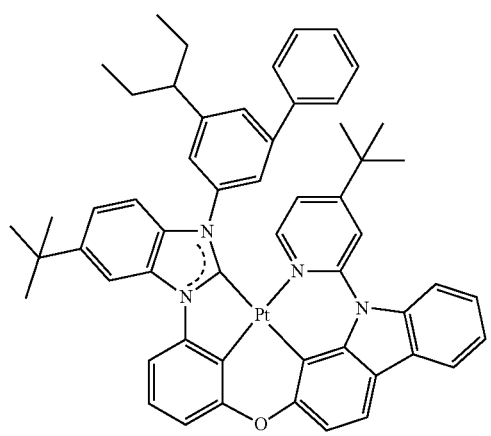
183
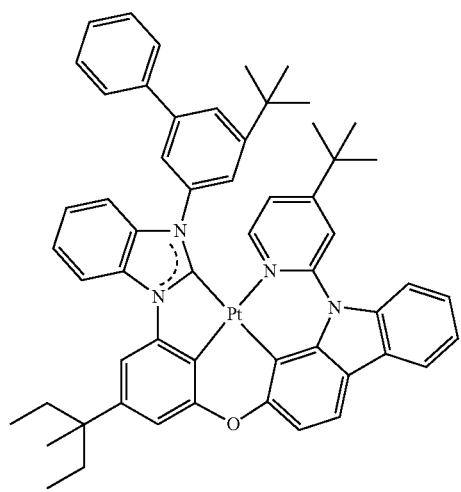
2540
-continued
184
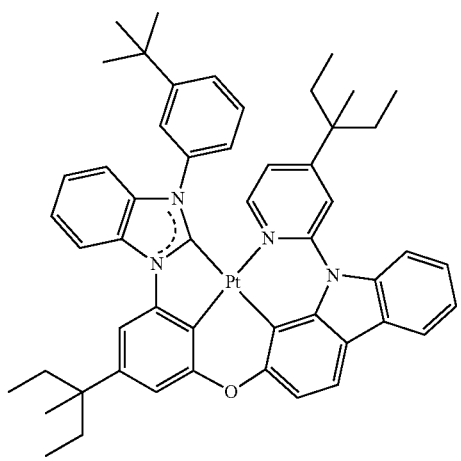
185
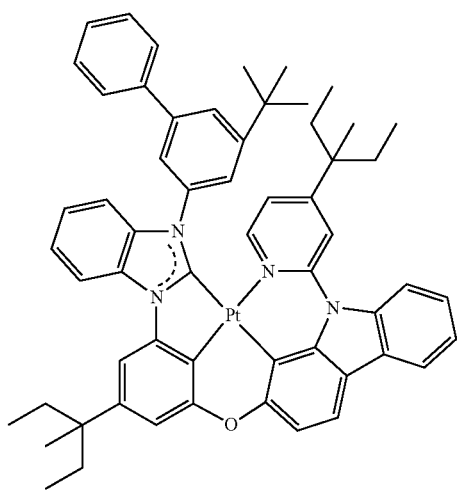
186
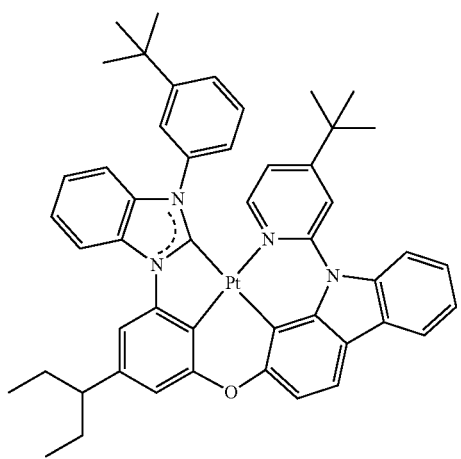

2541
-continued
187
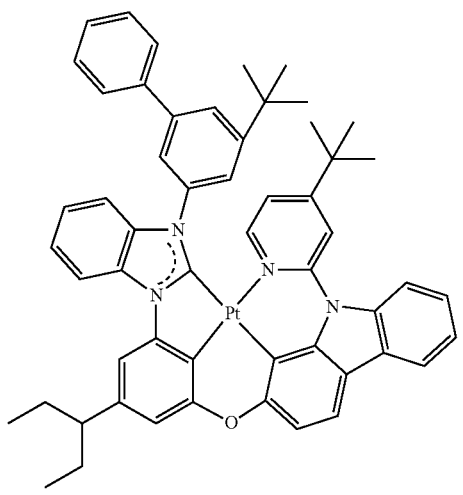
188
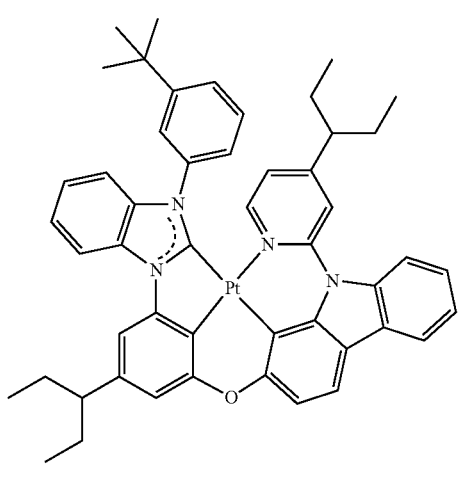
189
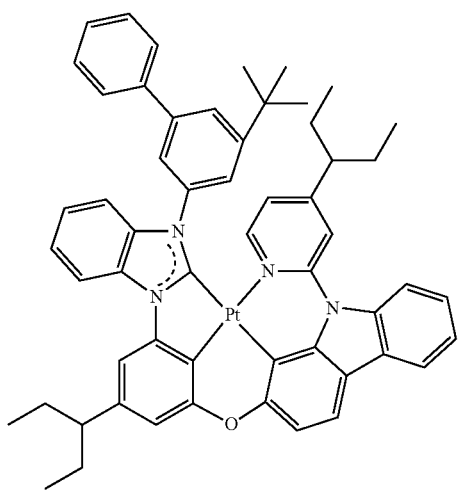
2542
-continued
190
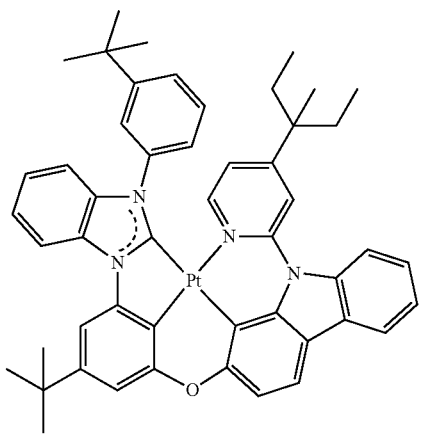
191
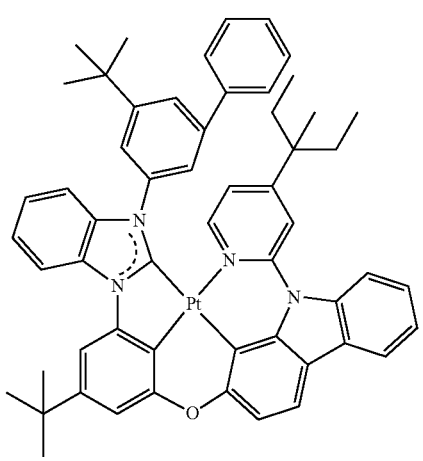
192
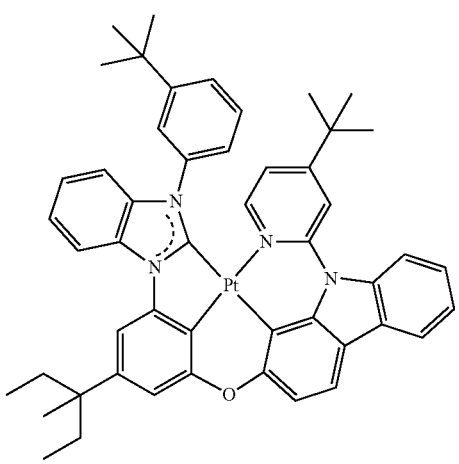

193
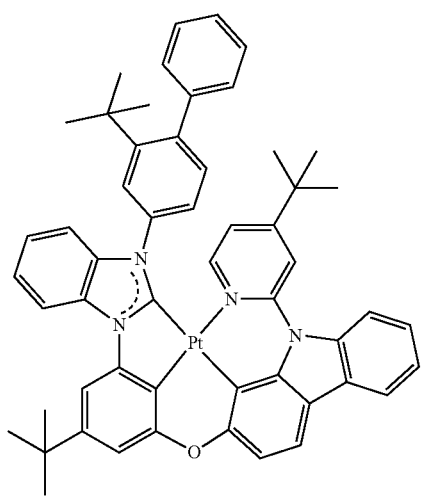
194
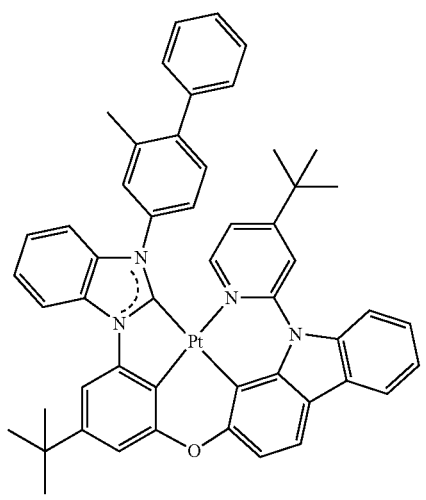
195
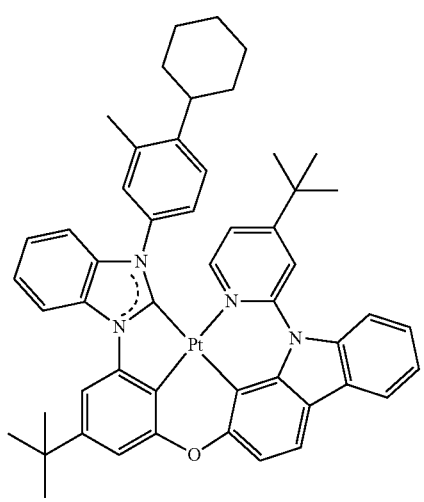
196
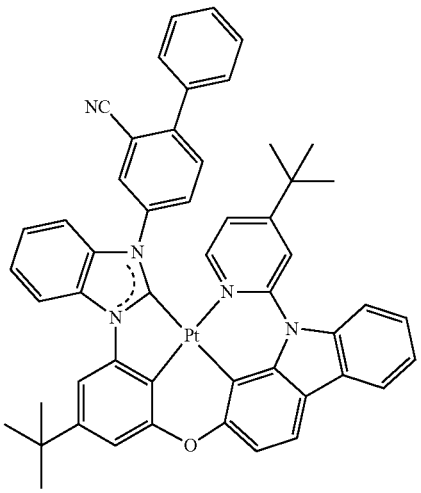
197
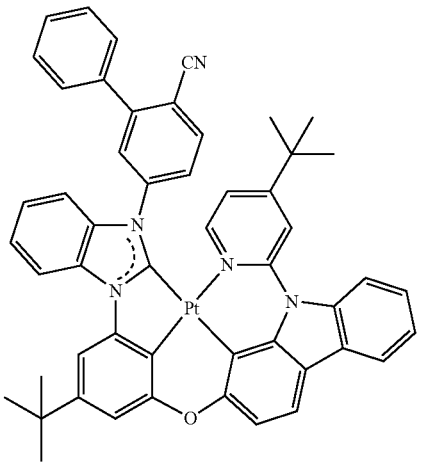
198
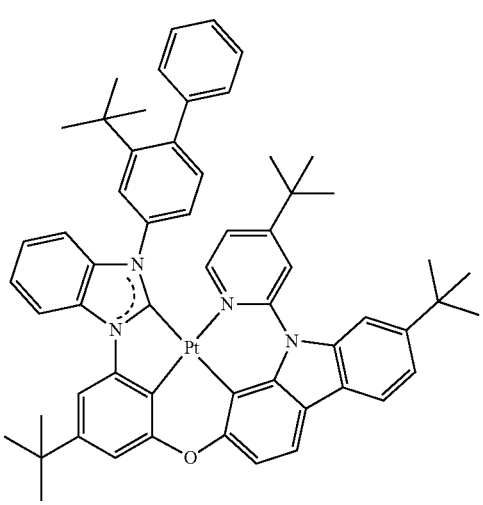

2545
-continued
199
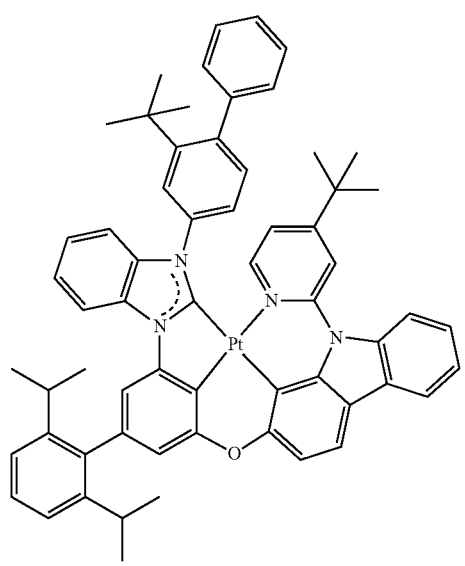
200
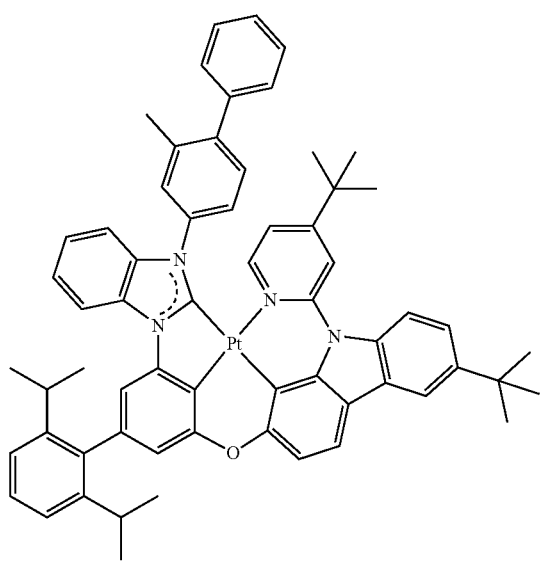
201
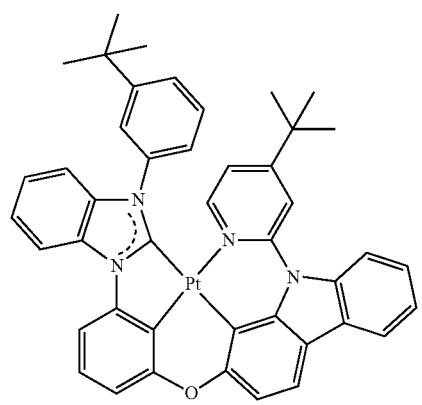
2546
-continued
202
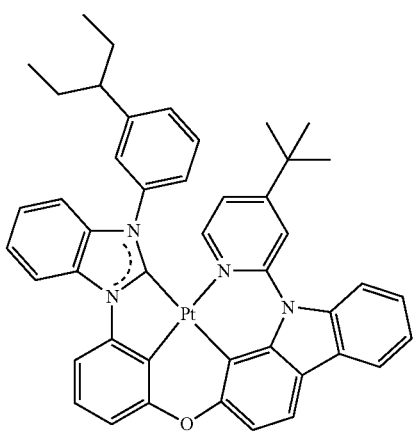
203
204
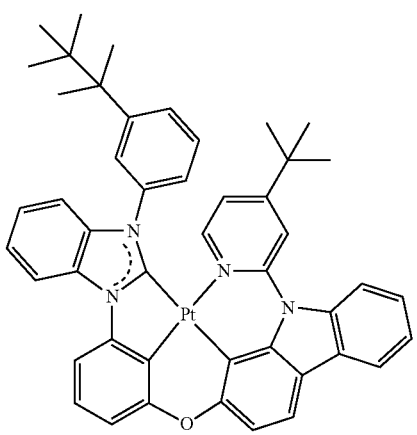

2547-continued
205
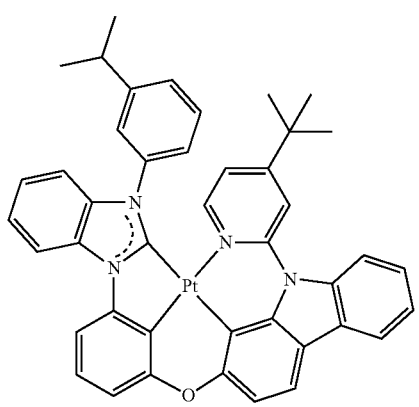
206
207
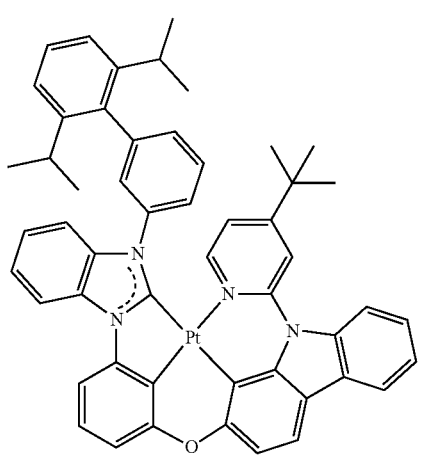
2548-continued
208
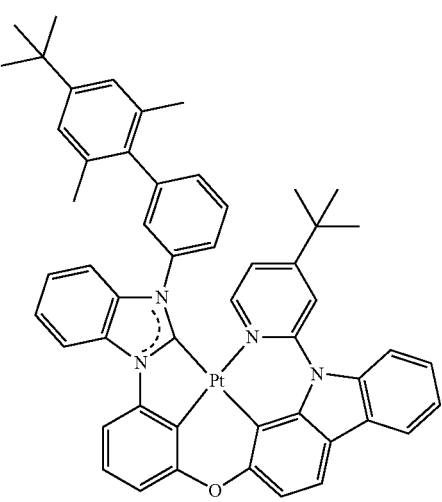
209
210
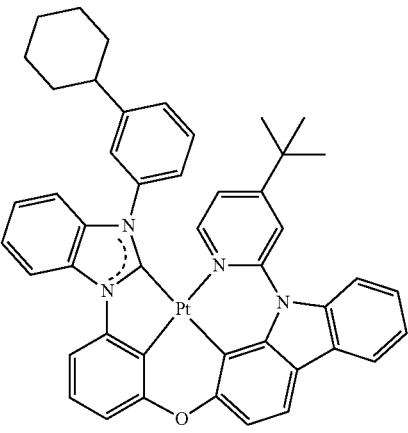

2549
-continued
211
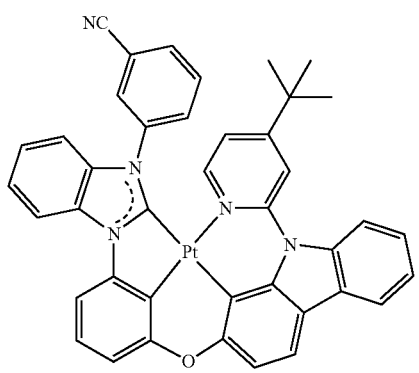
212
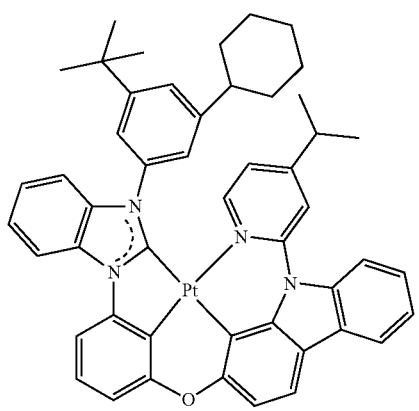
213
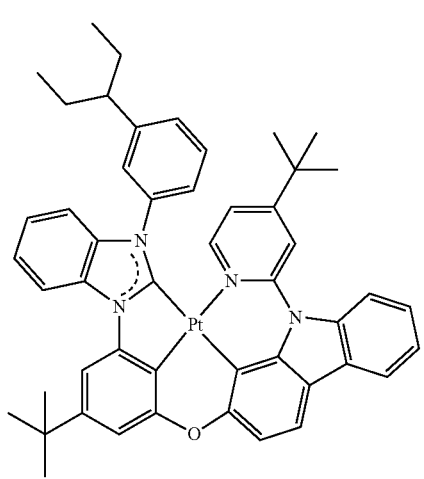
2550
-continued
214
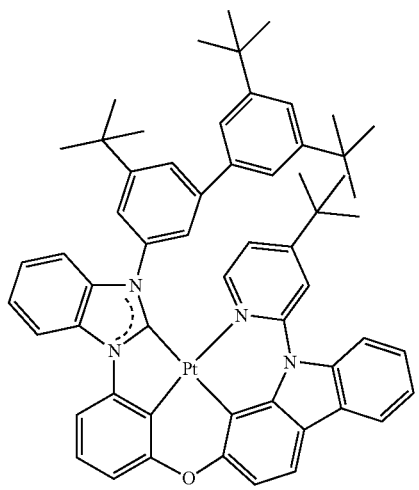
215
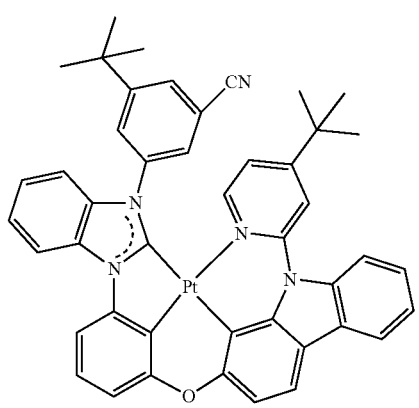
216
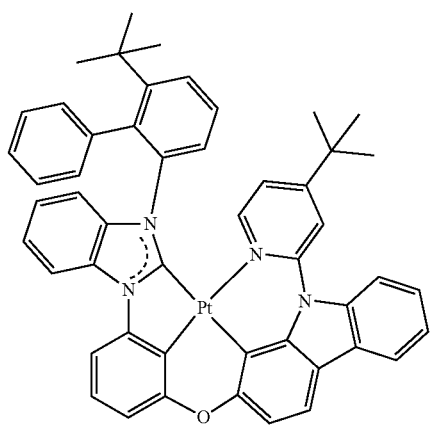

2551
-continued
217
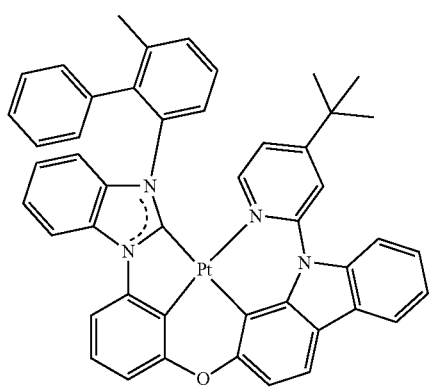
218
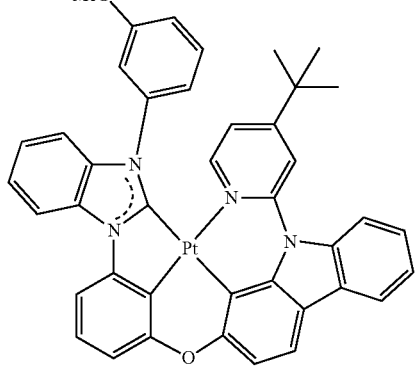
219
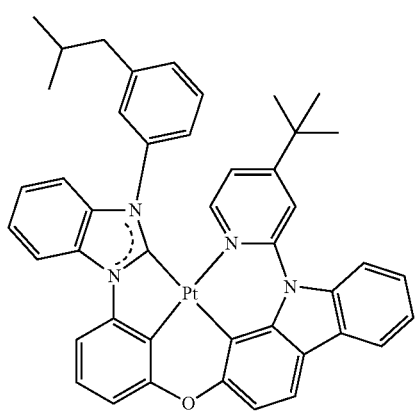
220
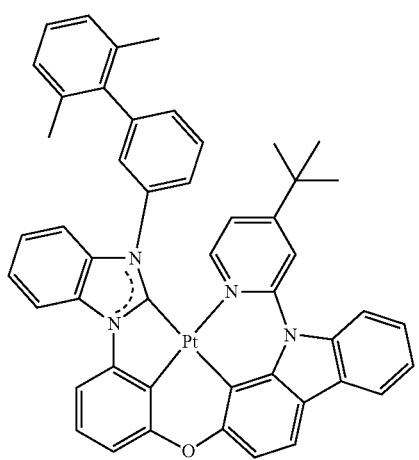
2552
-continued
221
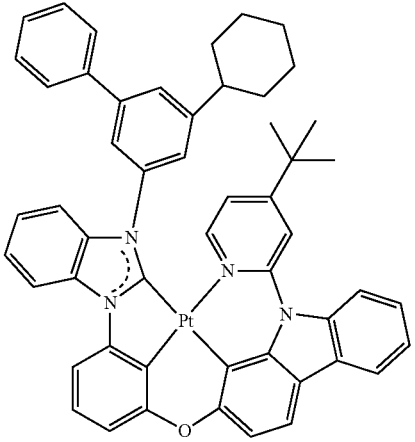
222
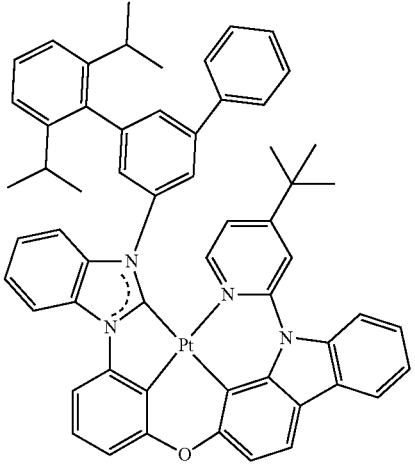
223
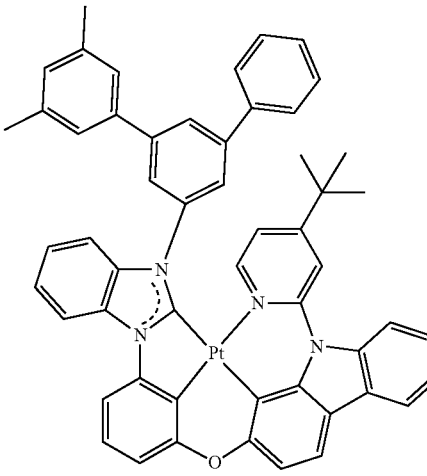

2553
-continued
224
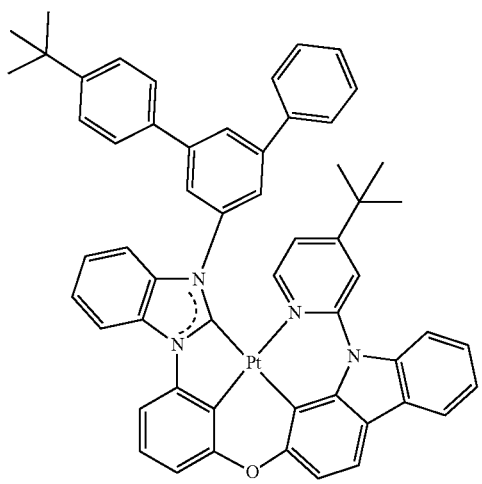
225
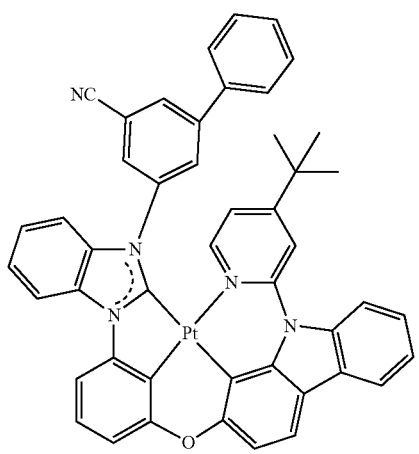
226
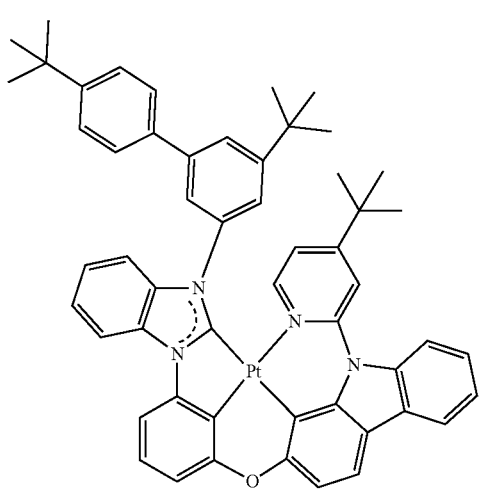
2554
-continued
227
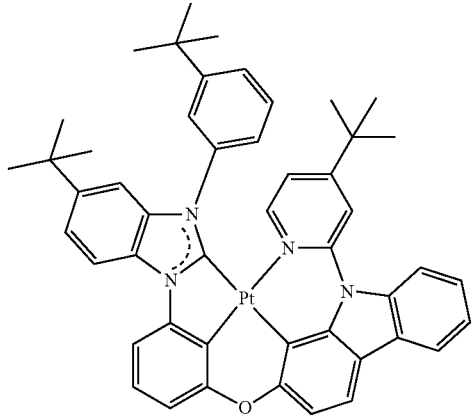
228
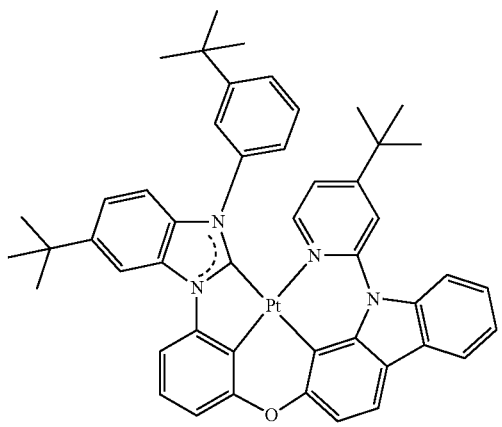
229
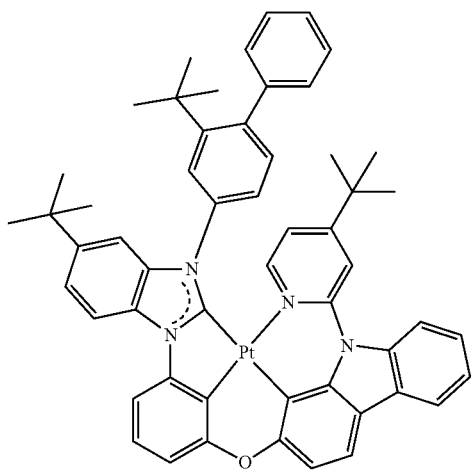

2555
-continued
230
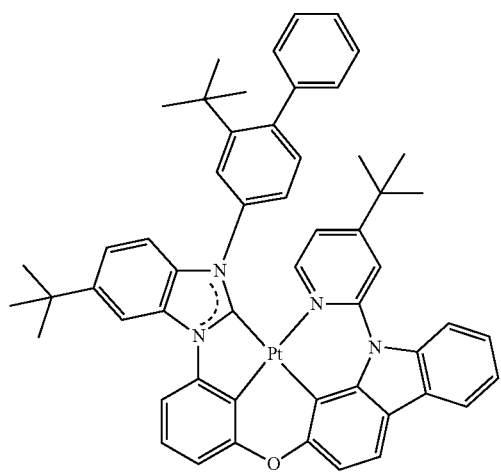
231
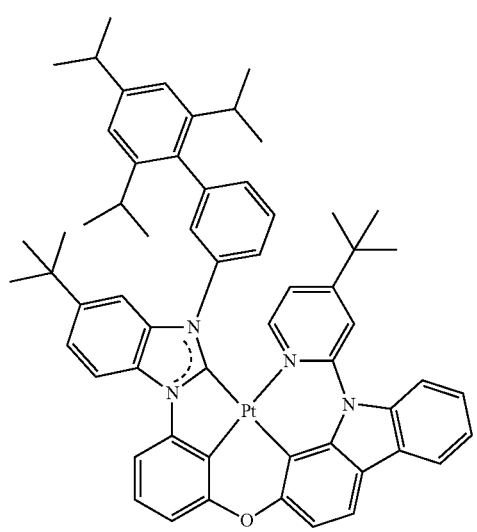
232
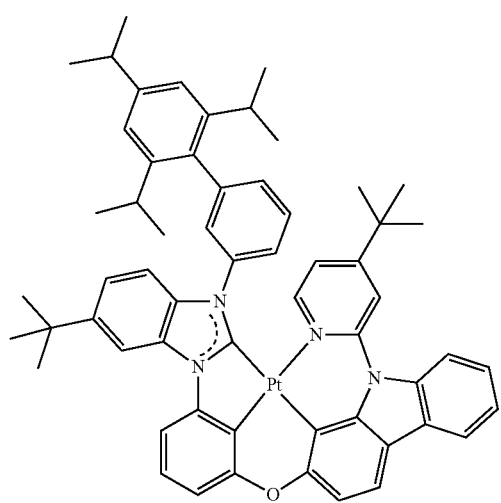
2556
-continued
233
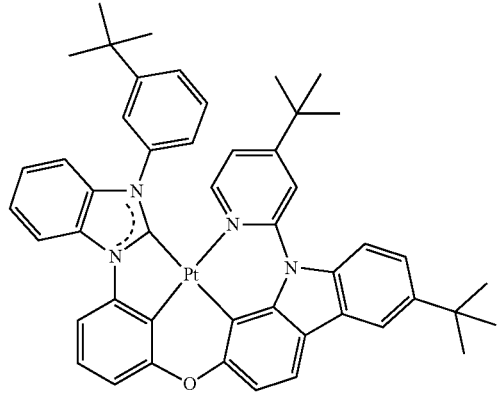
234
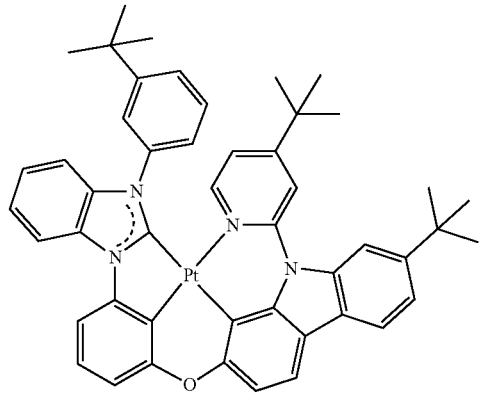
235
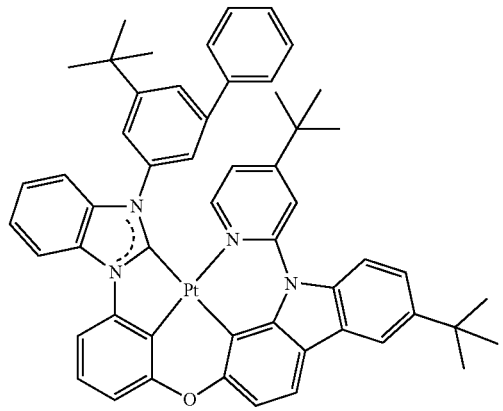
236
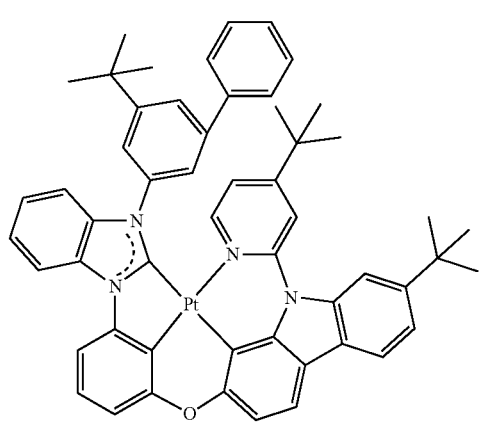

2557
-continued
237
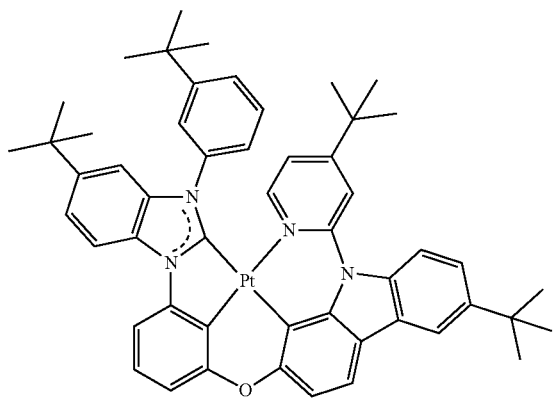
238
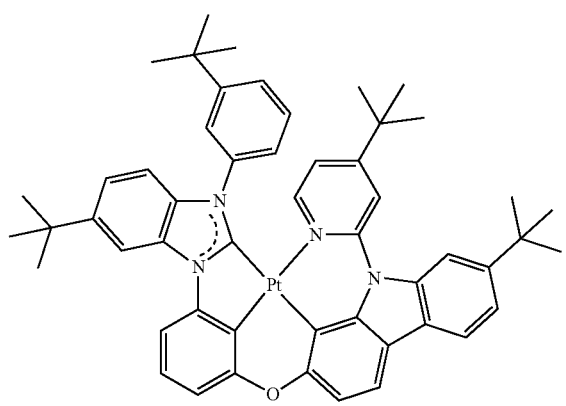
239
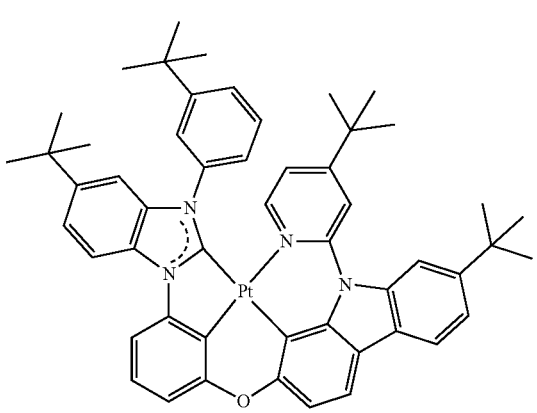
2558
-continued
240
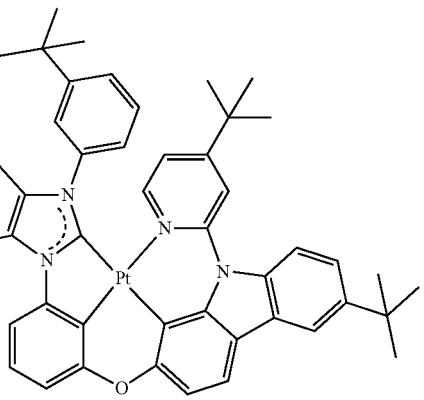
241
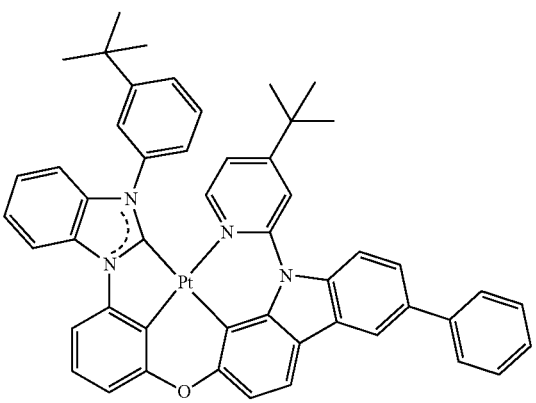
242
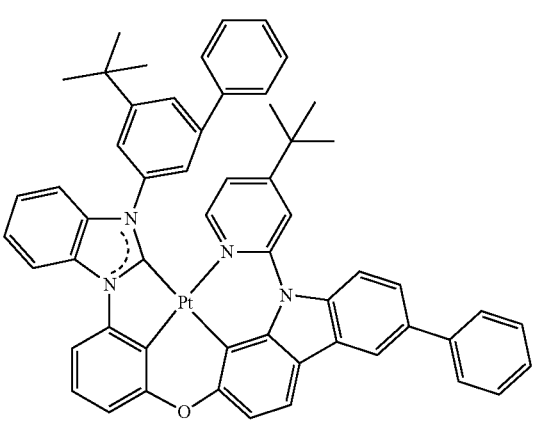

2559
-continued
243
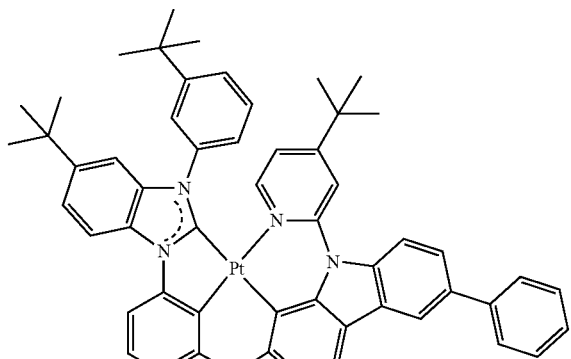
244
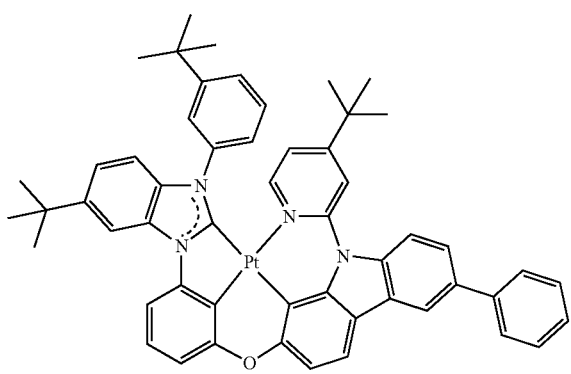
245
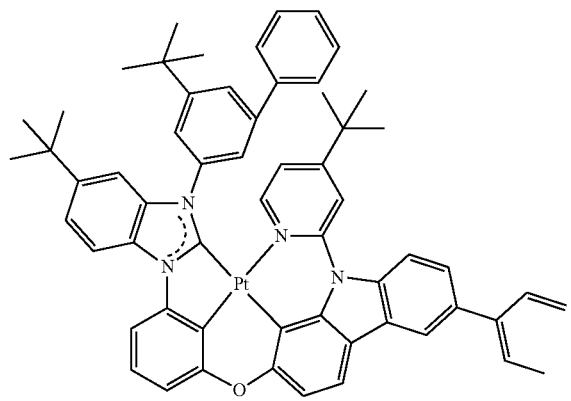
246
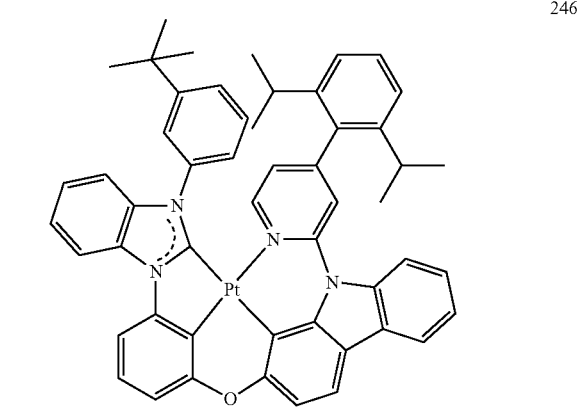
2560
-continued
247
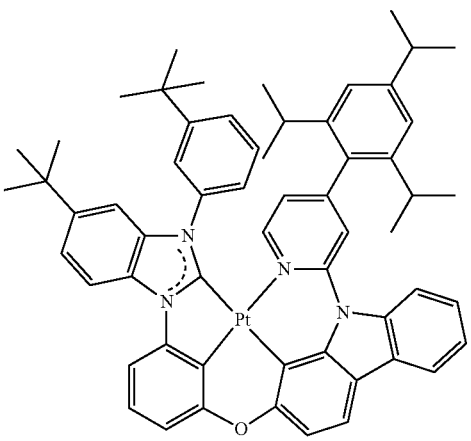
248
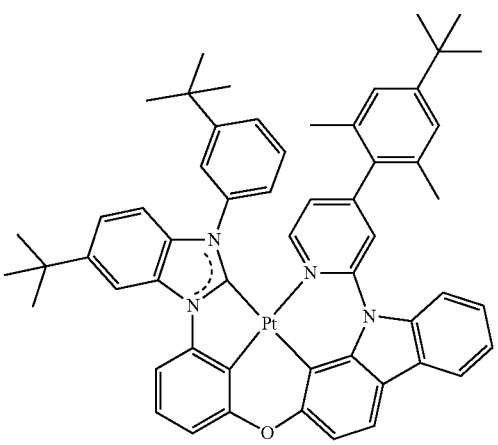
249
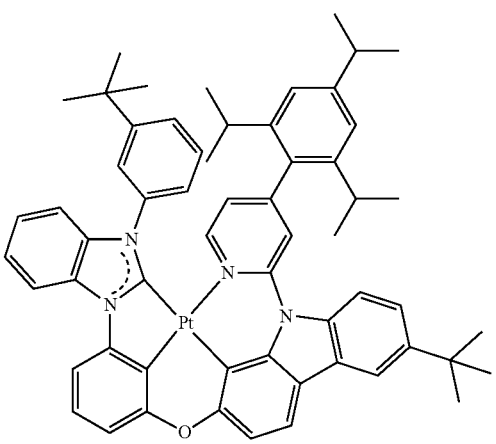

2561
-continued
250
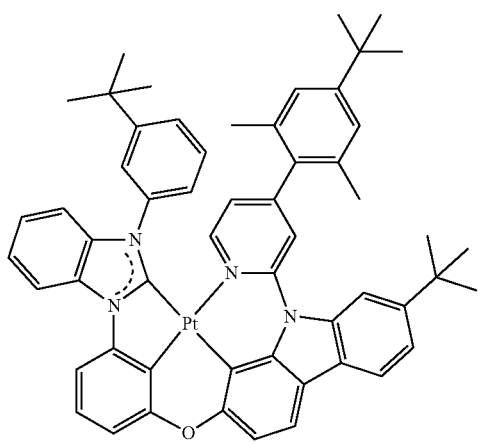
251
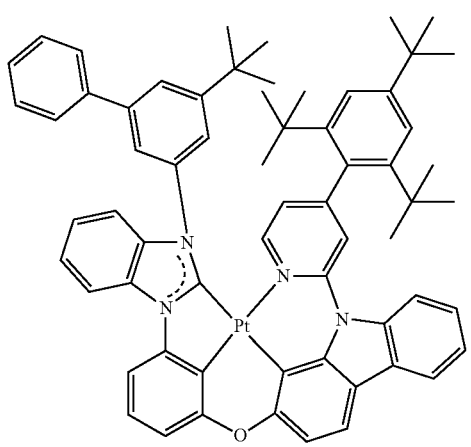
252
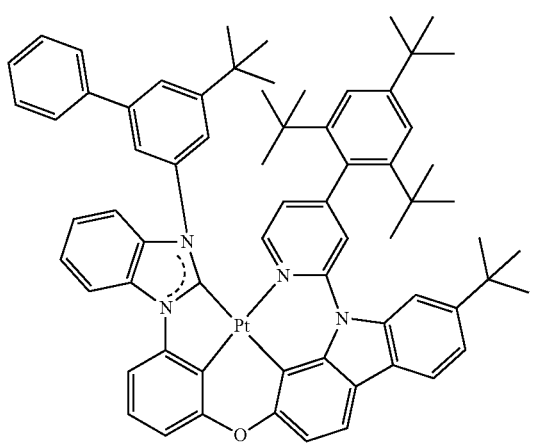
2562
-continued
253
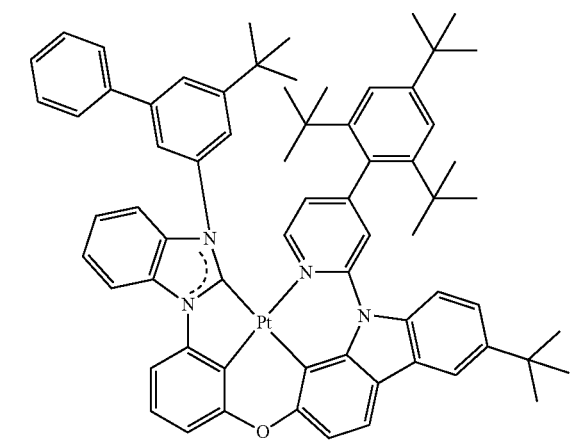
254
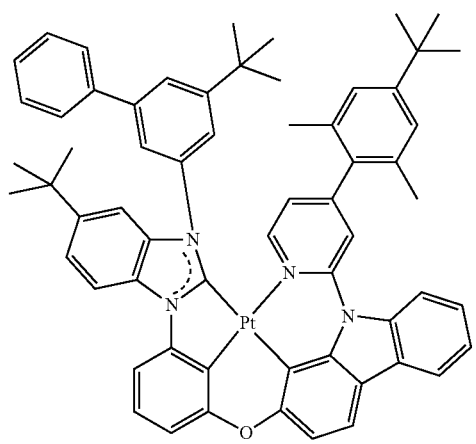
255
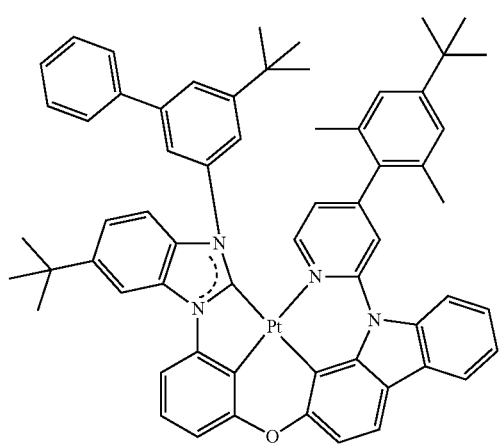

256
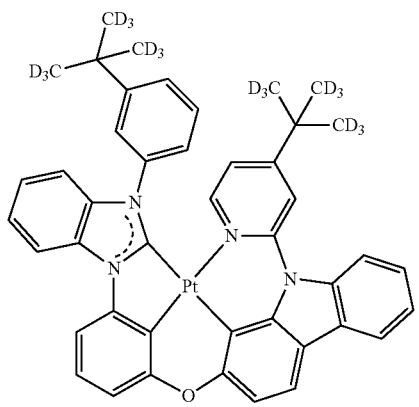
257
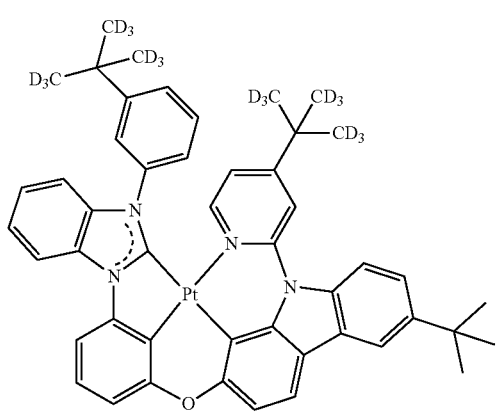
258
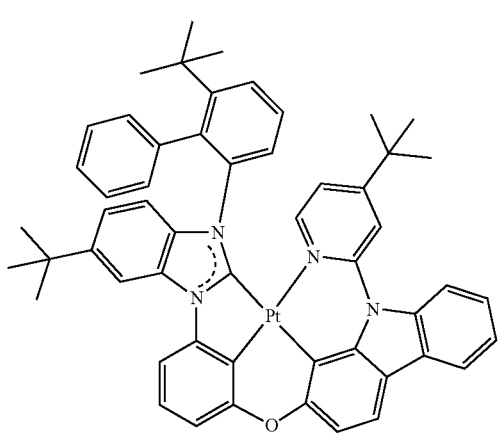
259
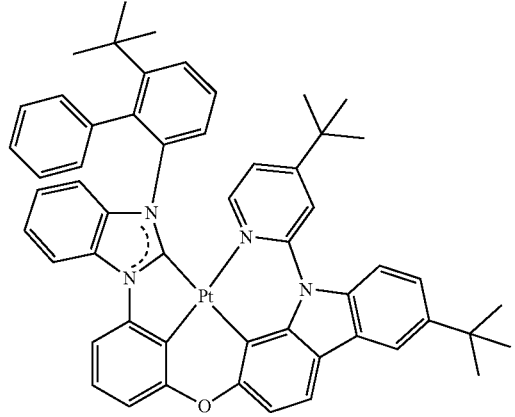
260
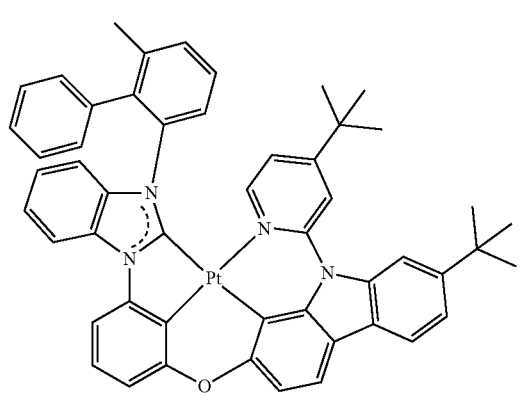
261
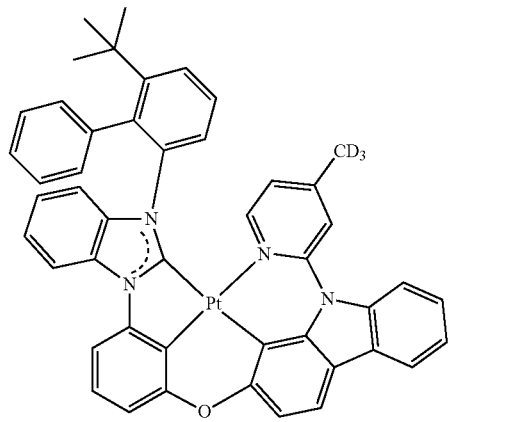
262
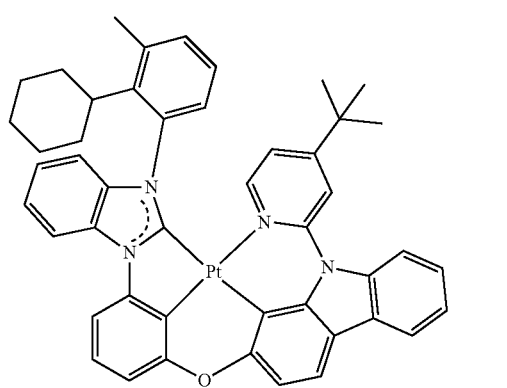

2565
-continued
2566
-continued
263
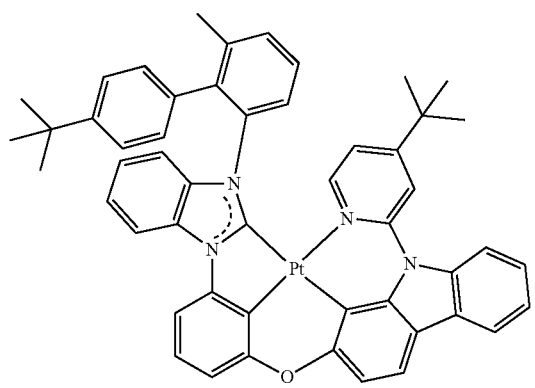
266
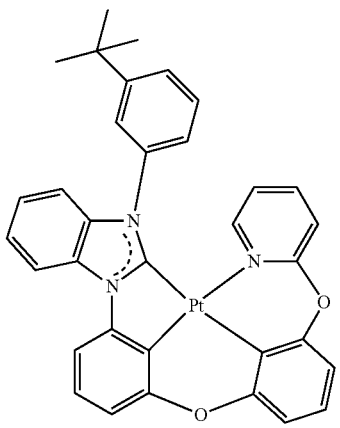
264
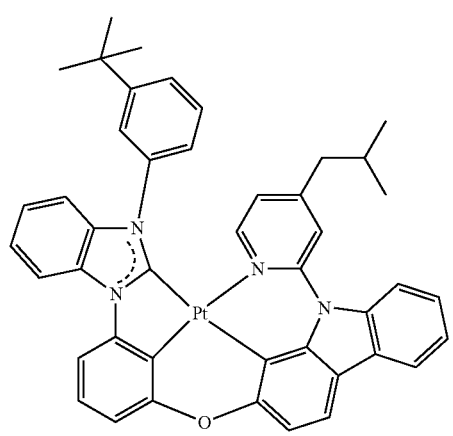
267
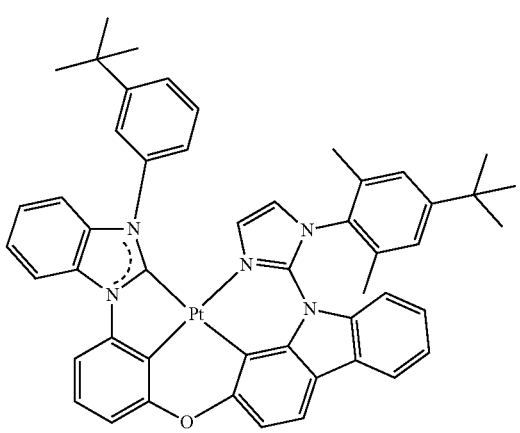
265
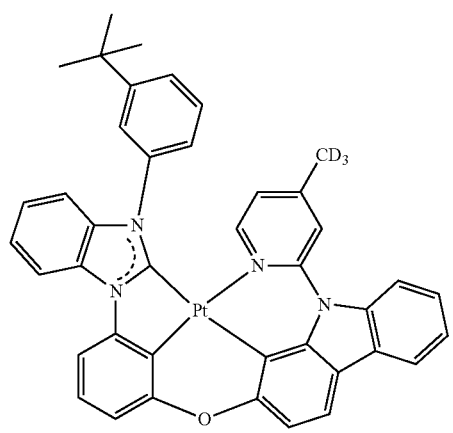
268

2567
-continued
269
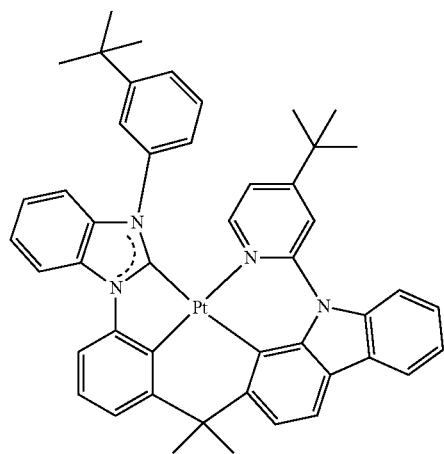
270
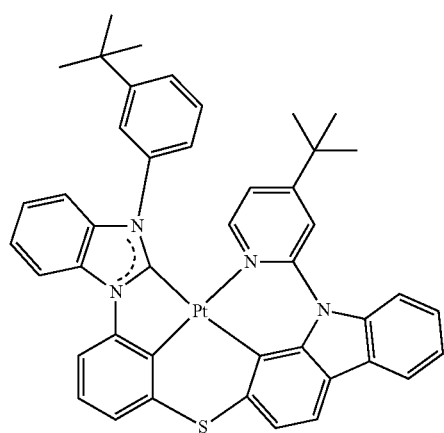
271
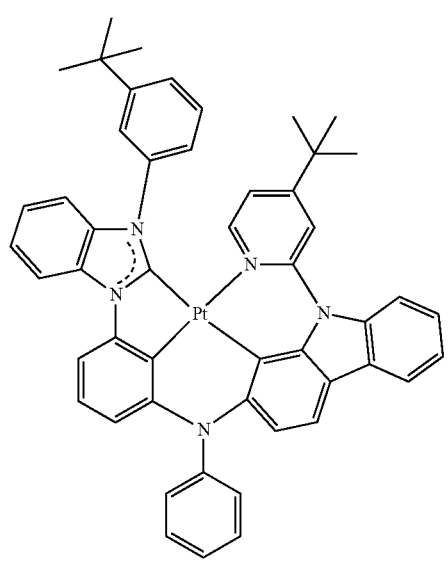
2568
-continued
272
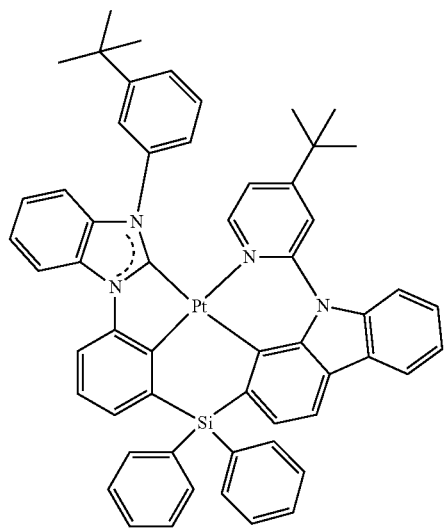
273
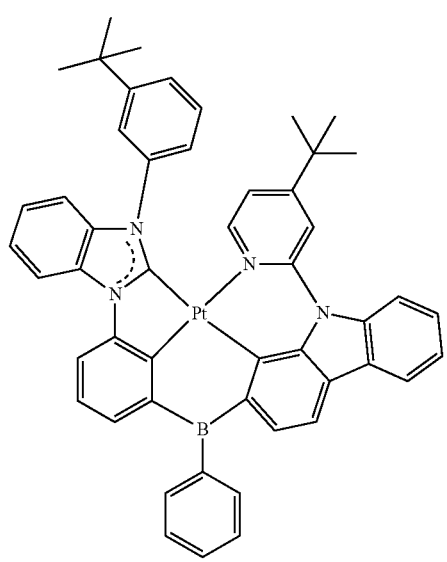
274
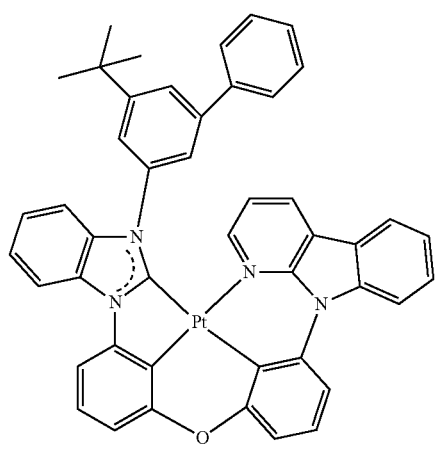

2569
-continued
275
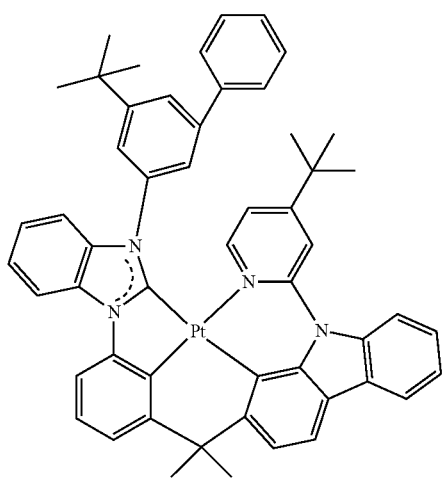
276
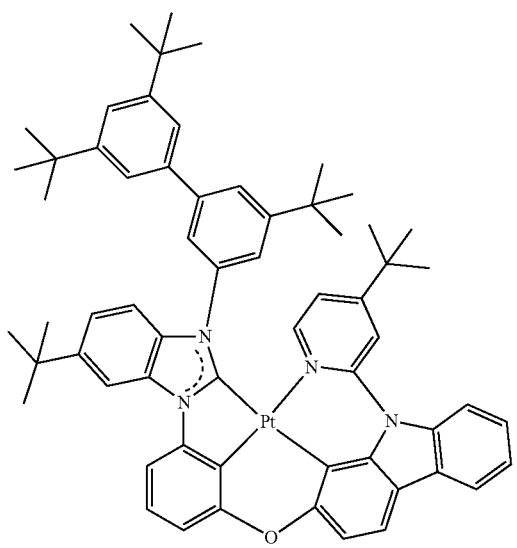
277
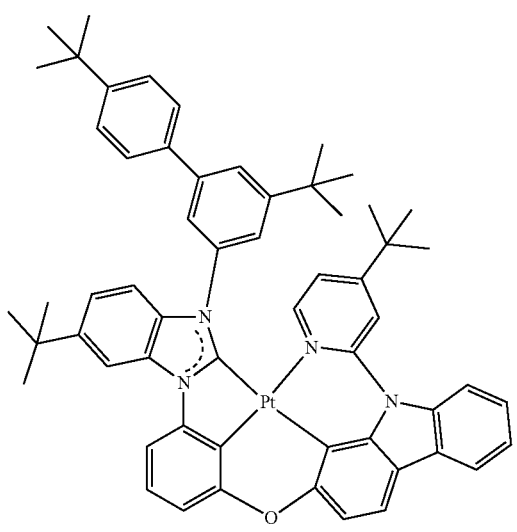
2570
-continued
278
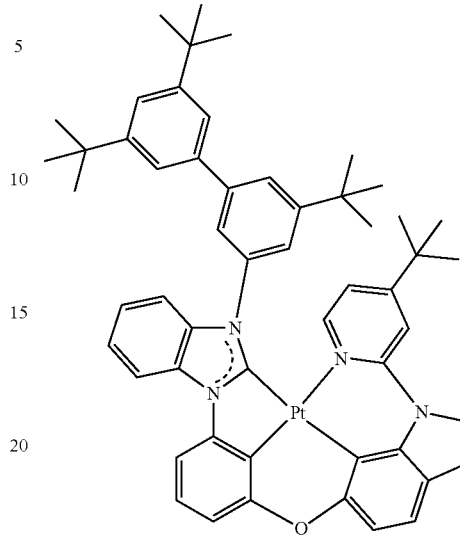
279
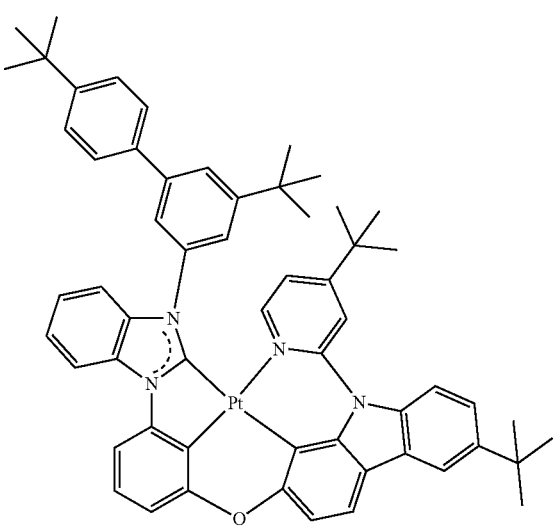
280
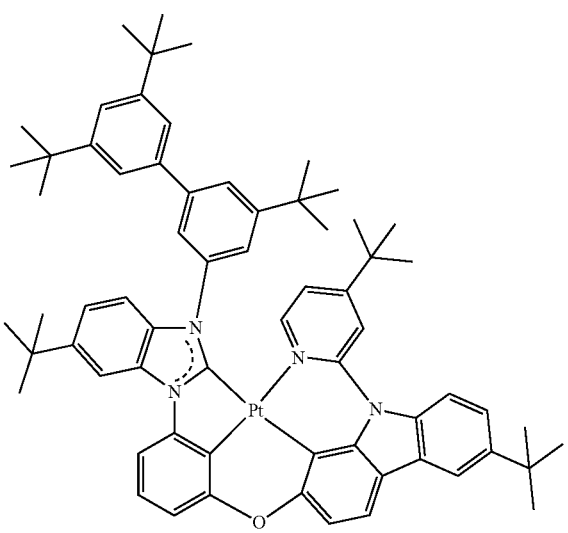

281
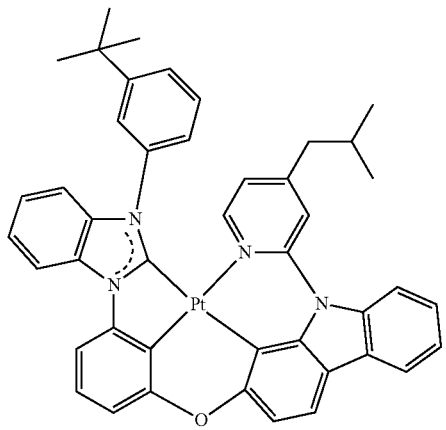
282
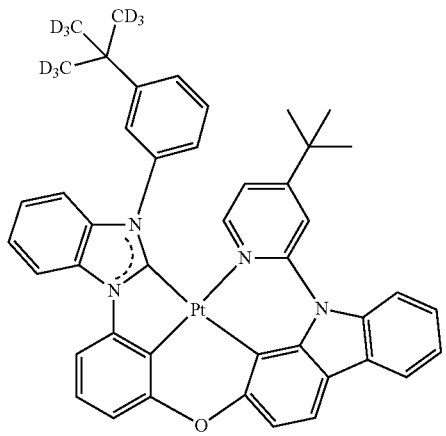
283
284
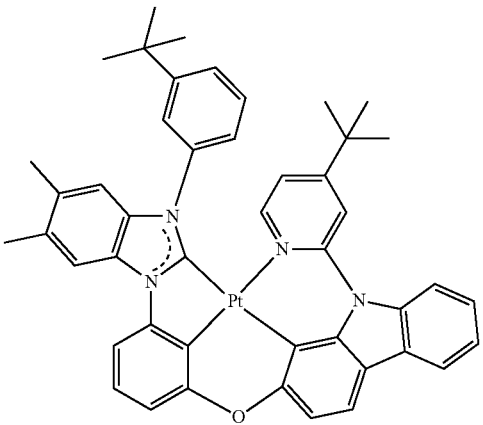
285
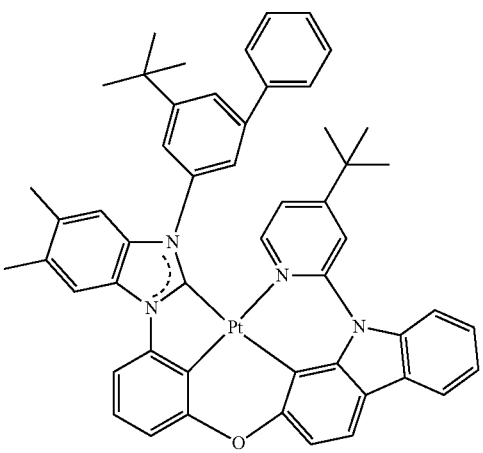
286
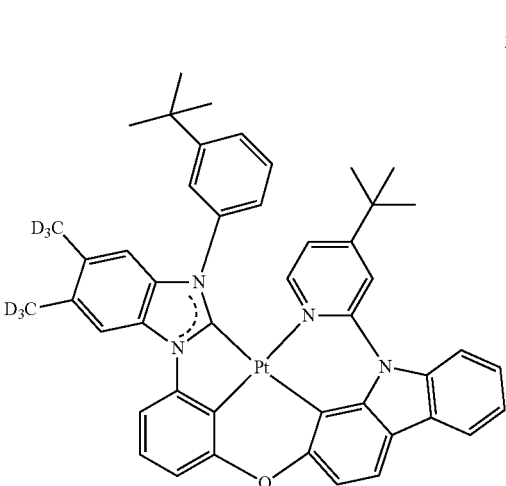

287
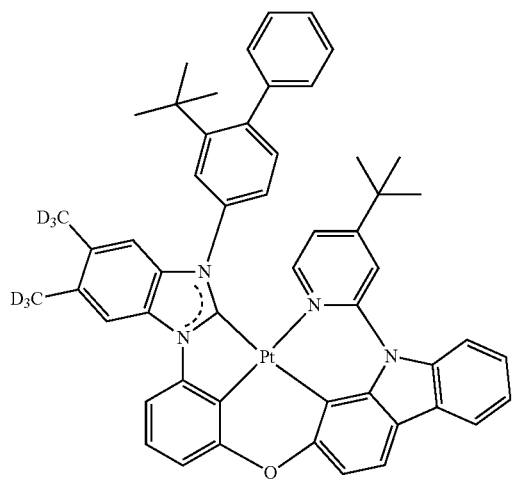
288
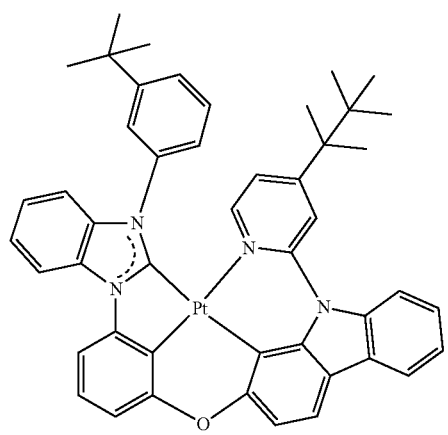
289
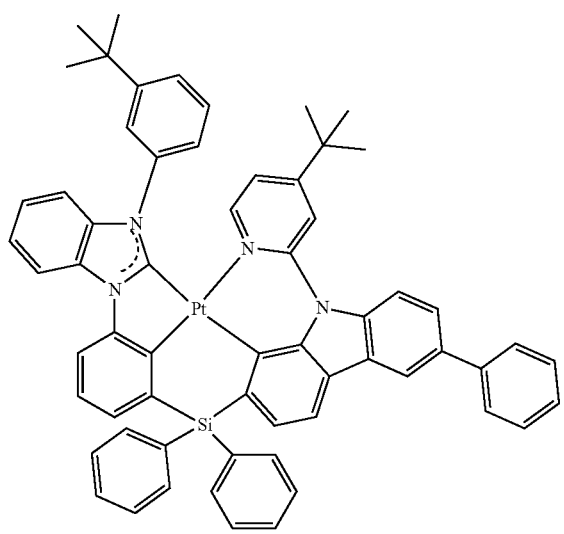
290
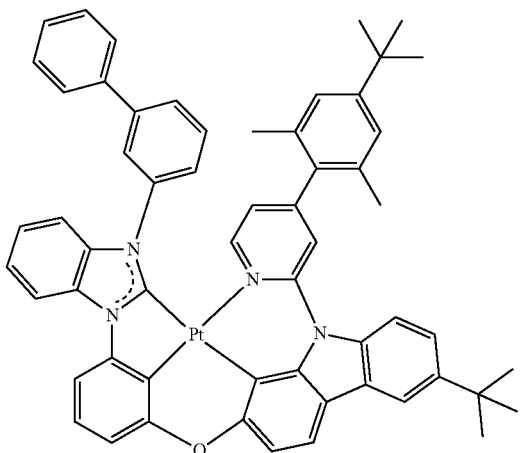
291
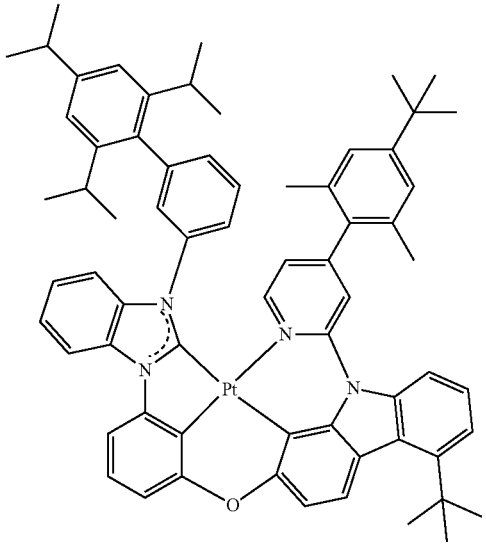
292
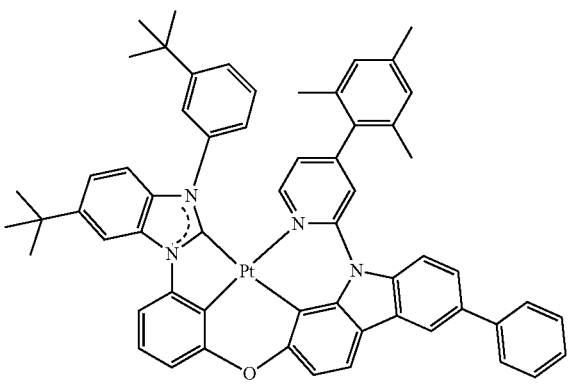

2575
-continued
293
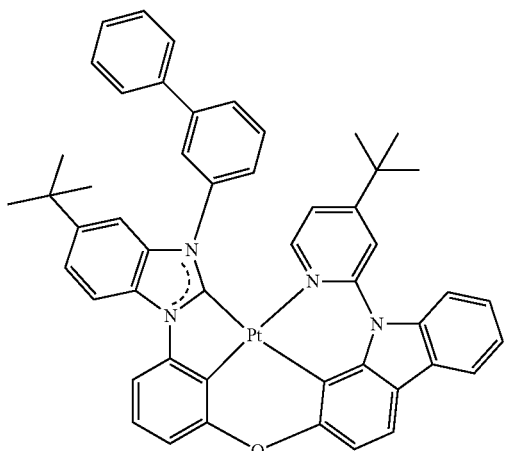
294
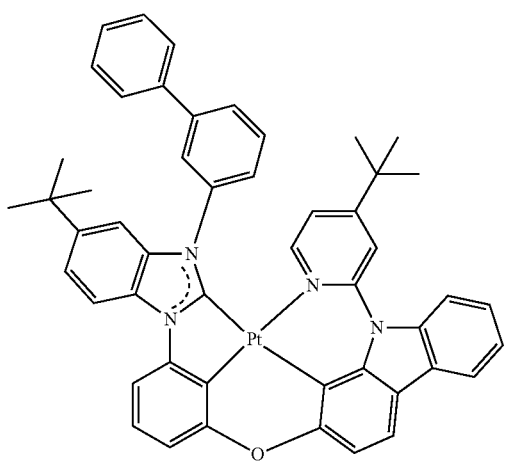
295
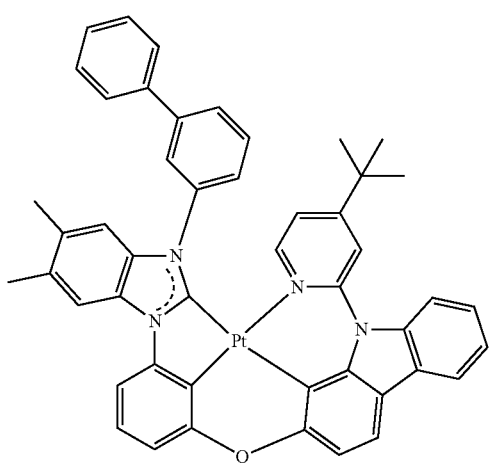
2576
-continued
296
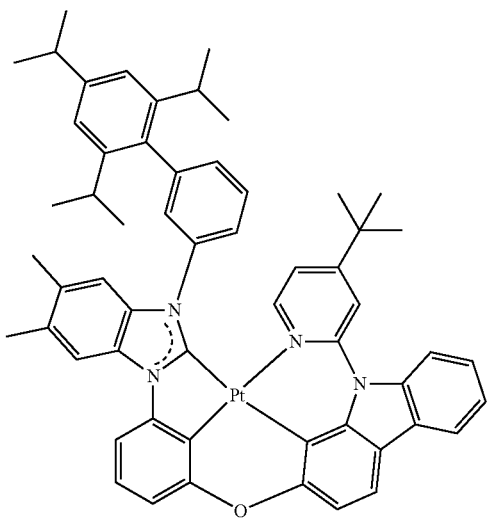
297
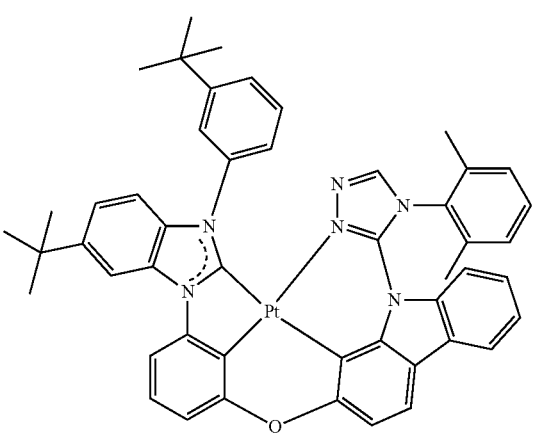
298
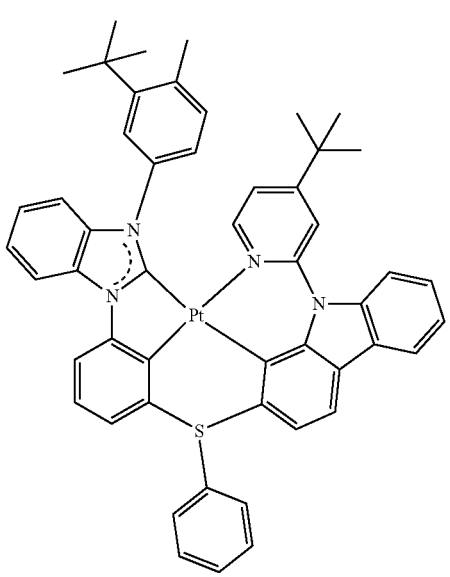

2577
-continued
299
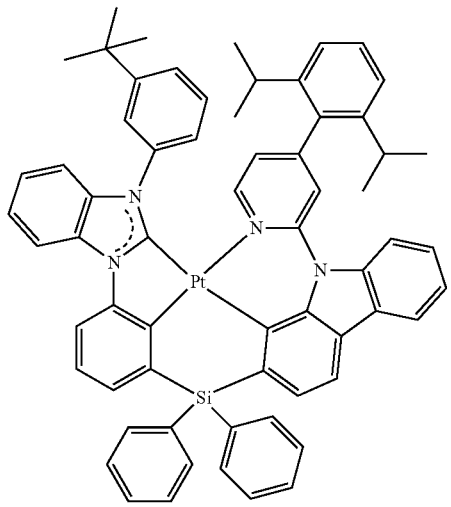
300
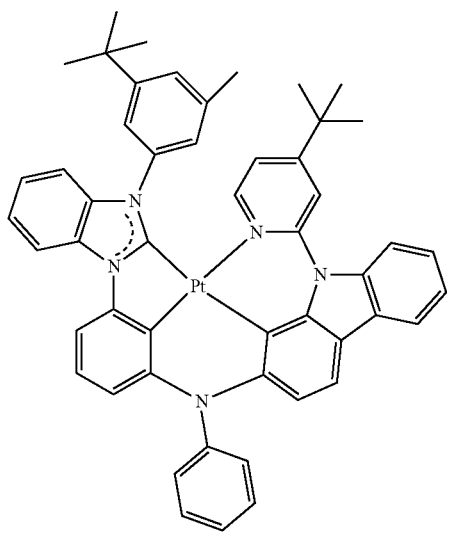
301
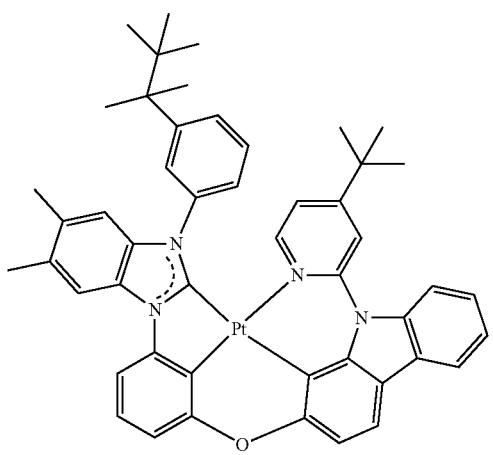
2578
-continued
302
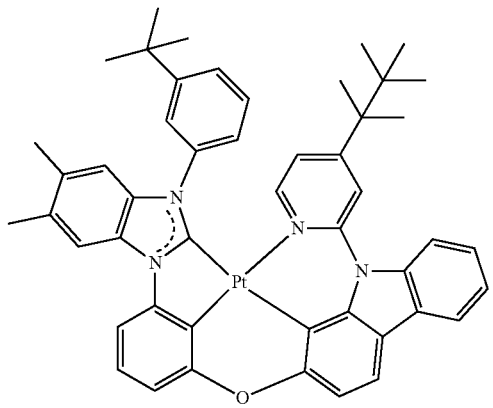
303
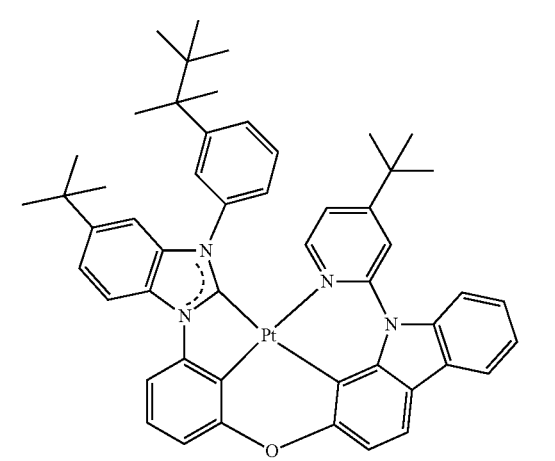
304
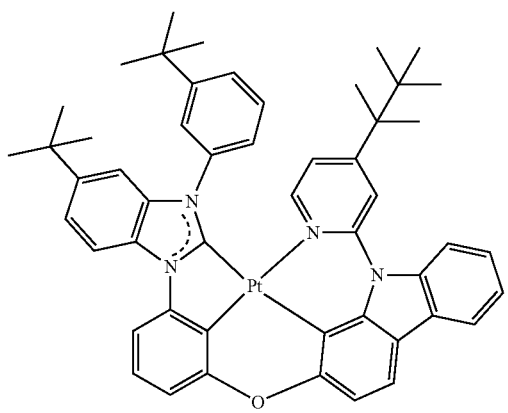

2579
-continued
305
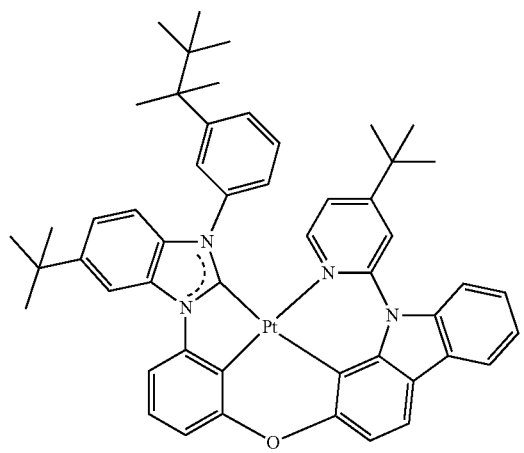
306
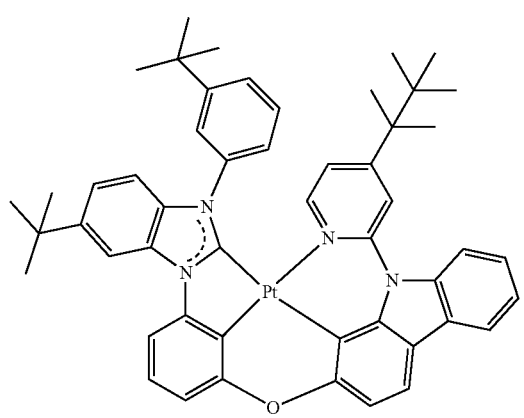
307
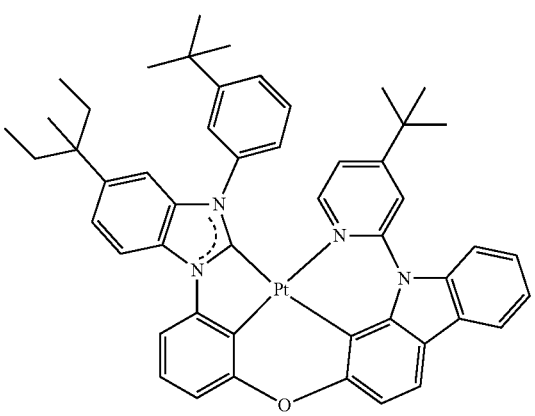
2580
-continued
308
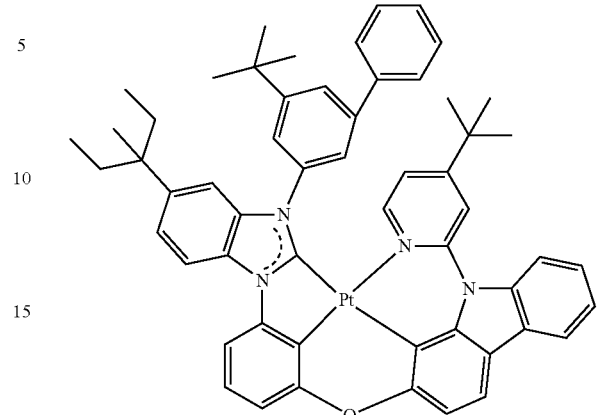
309
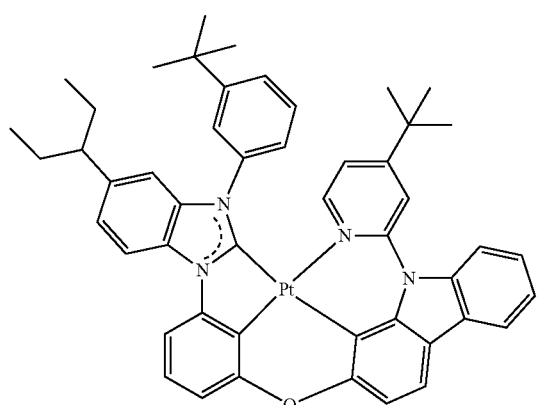
310
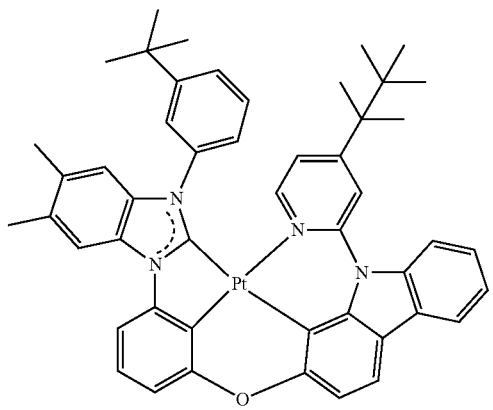

2581
-continued
311
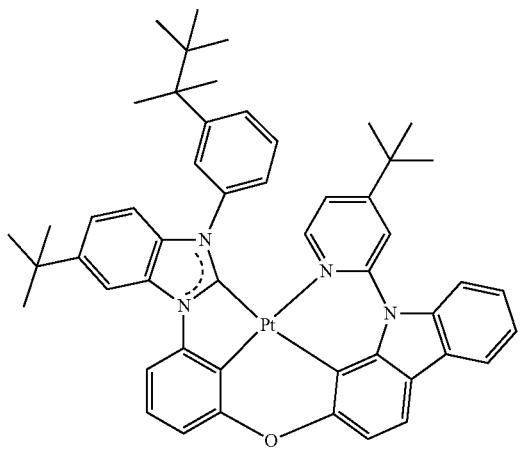
312
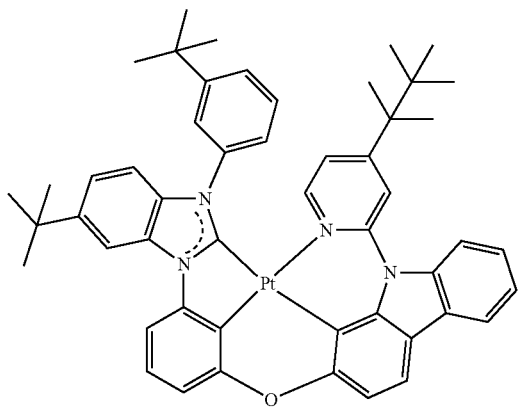
313
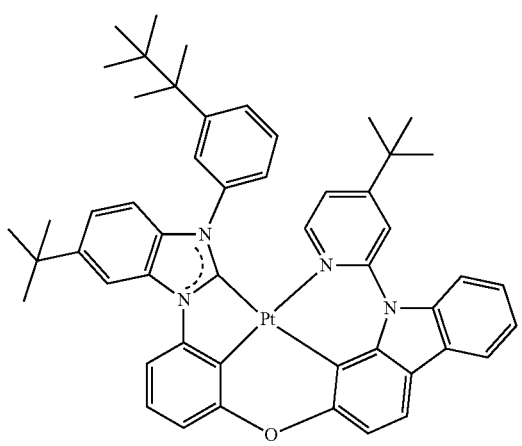
2582
-continued
314
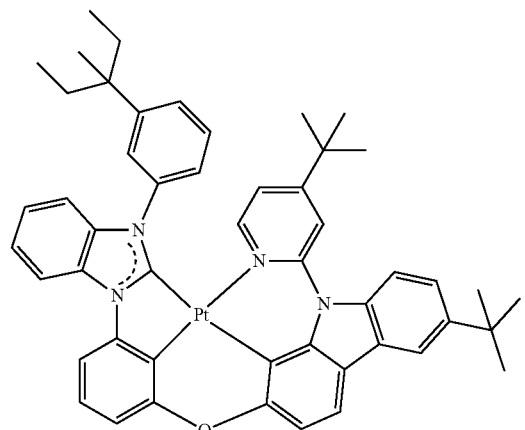
315
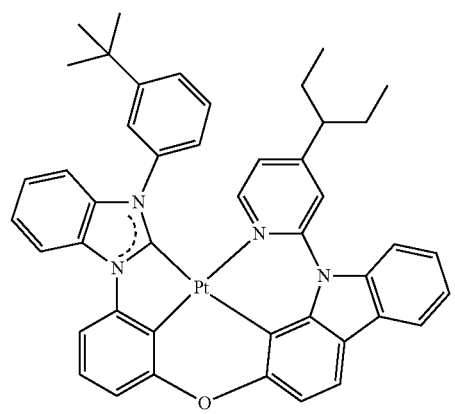
316
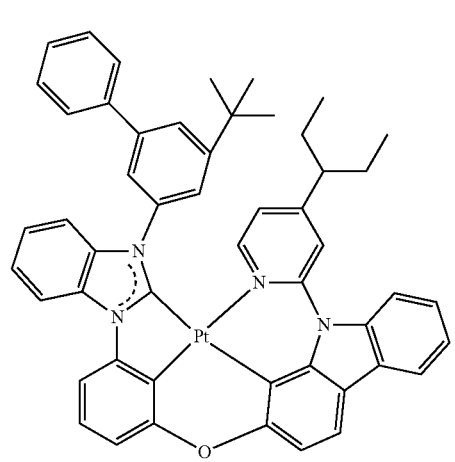

2583
-continued
317
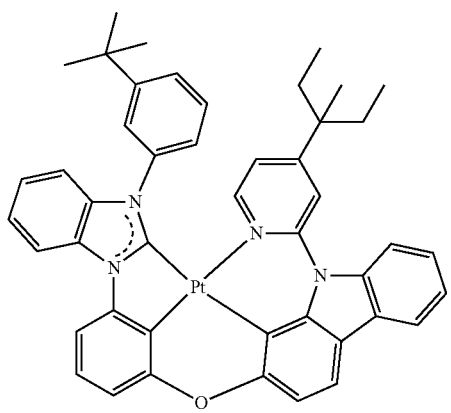
318
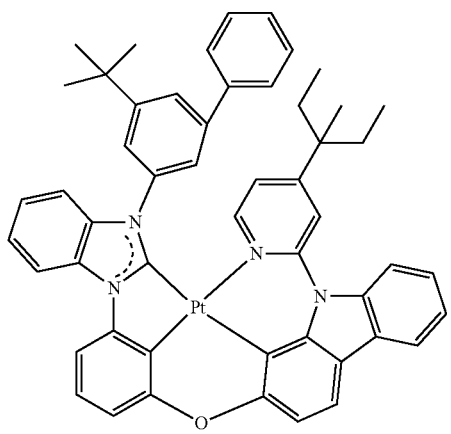
319
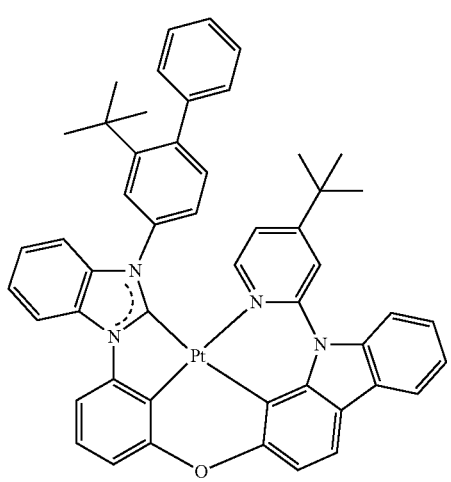
2584
-continued
320
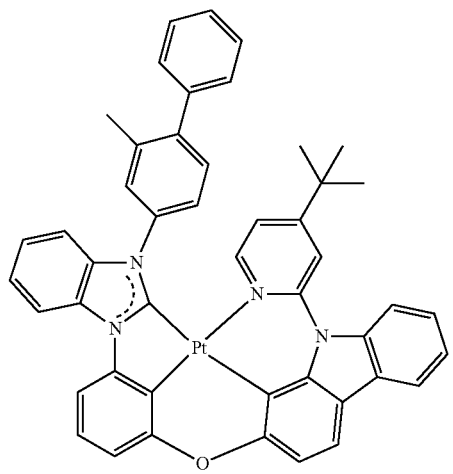
321
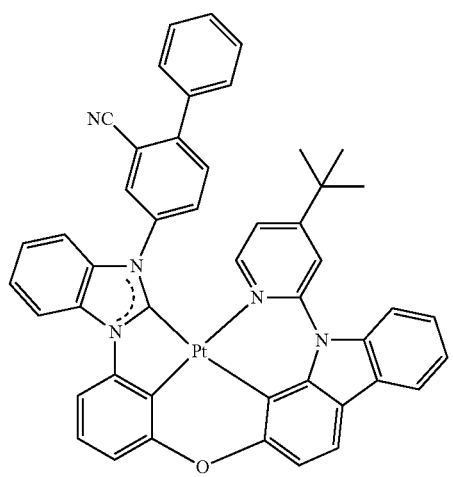
322
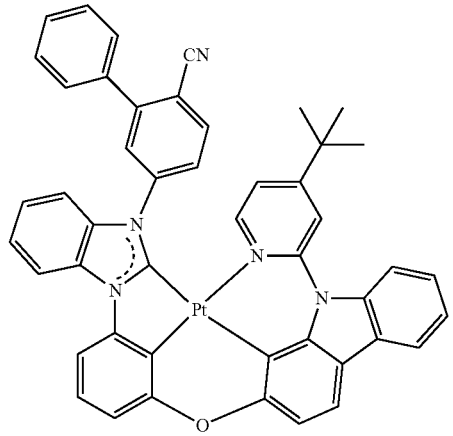

-continued
323
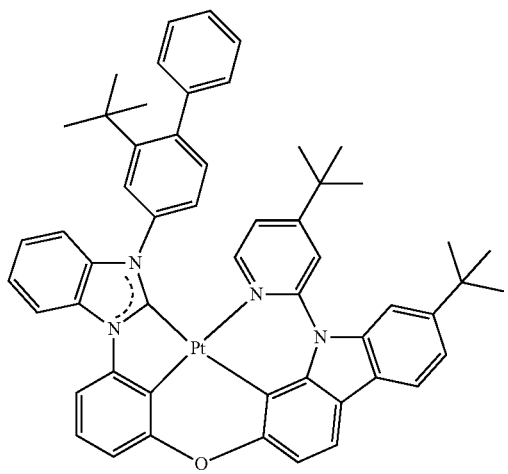
324
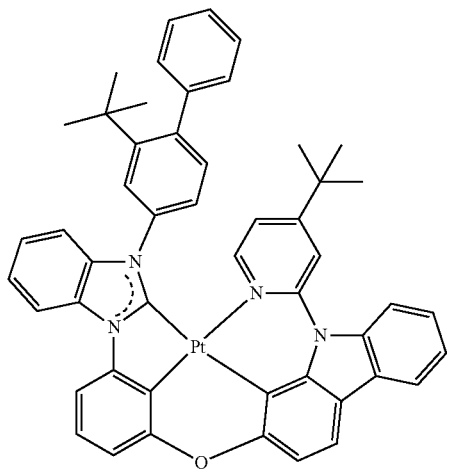
325
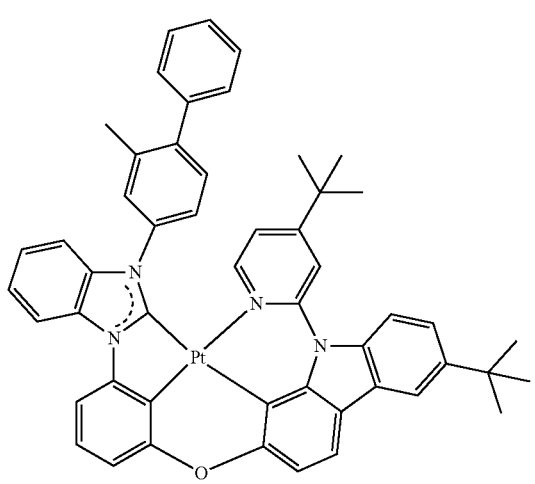
Group VIII
1
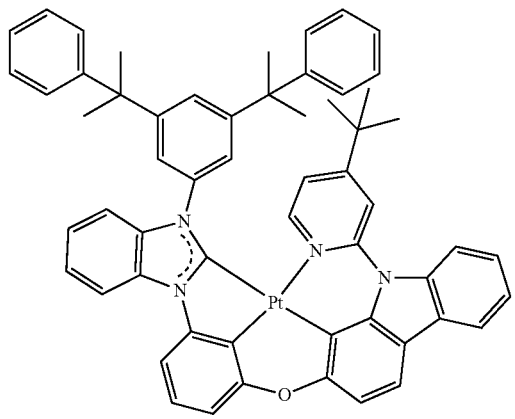
2
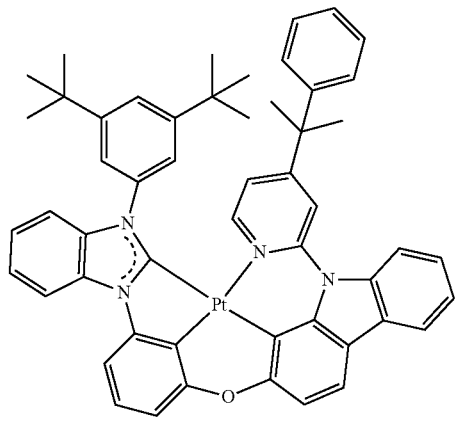
3
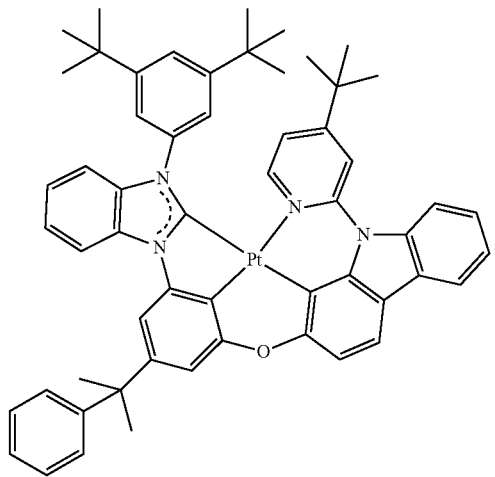

4
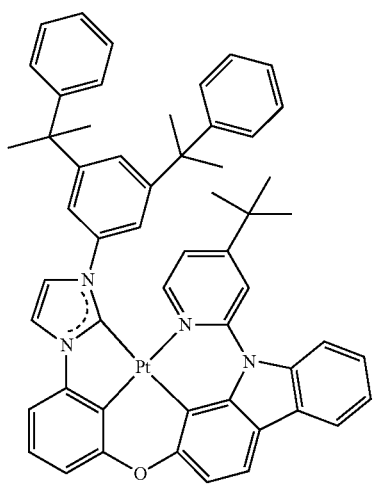
5
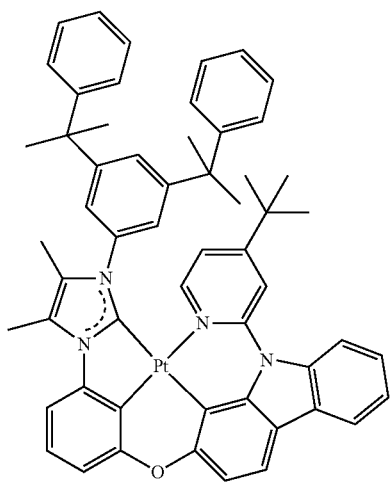
6
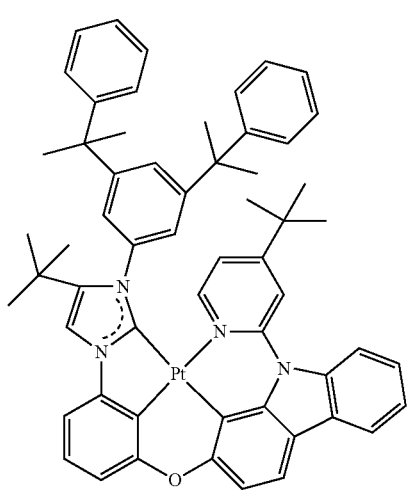
7
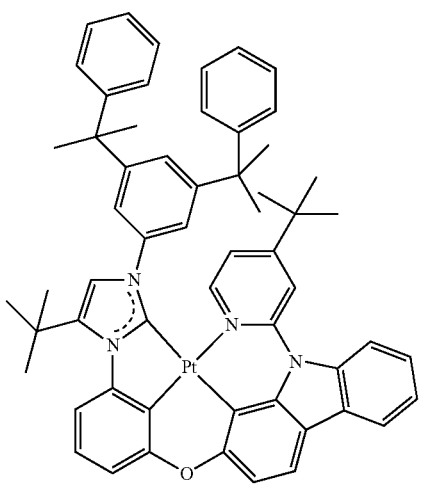
8
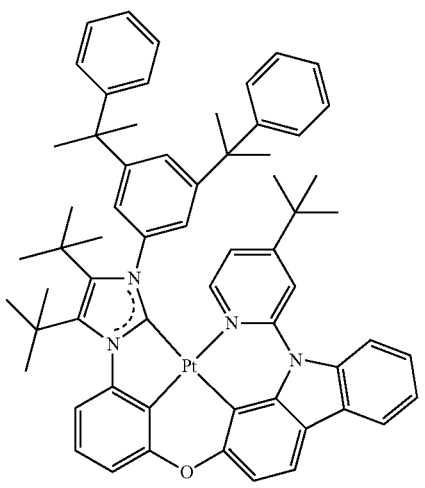
9
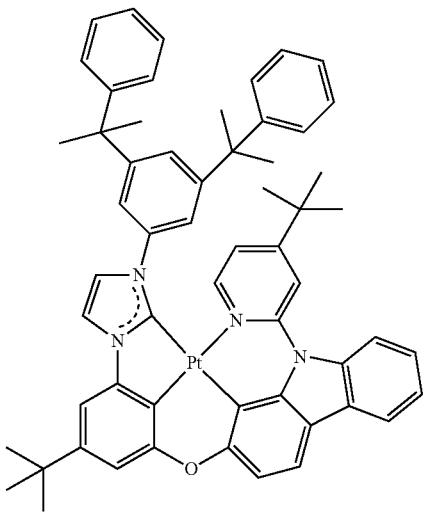

2589
-continued
10
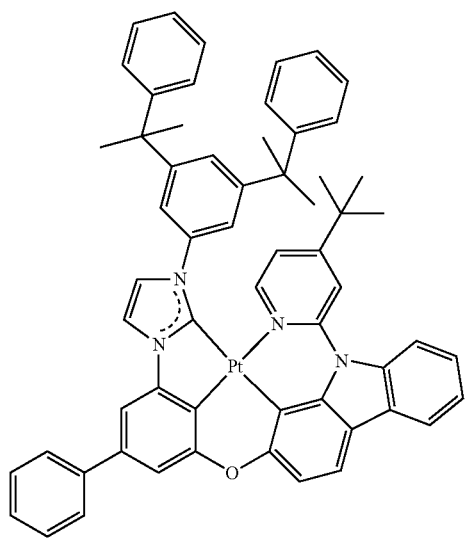
11
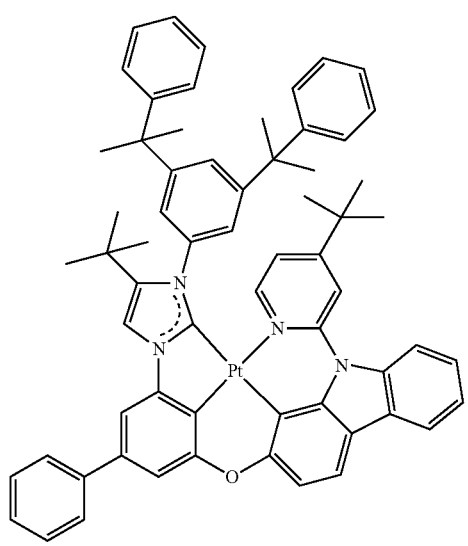
12
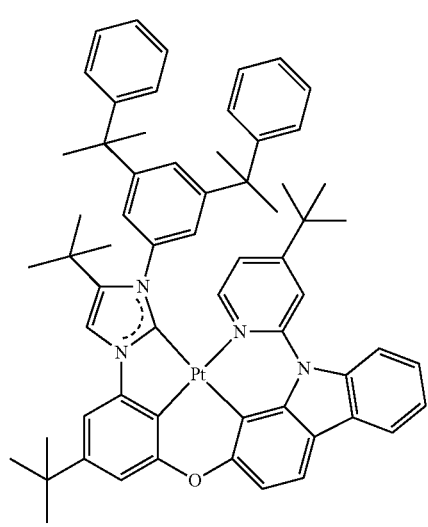
2590
-continued
13
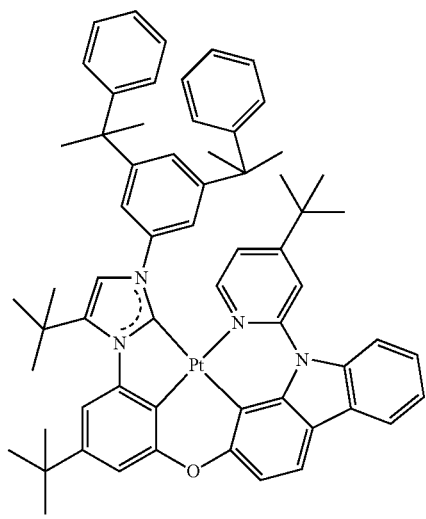
14
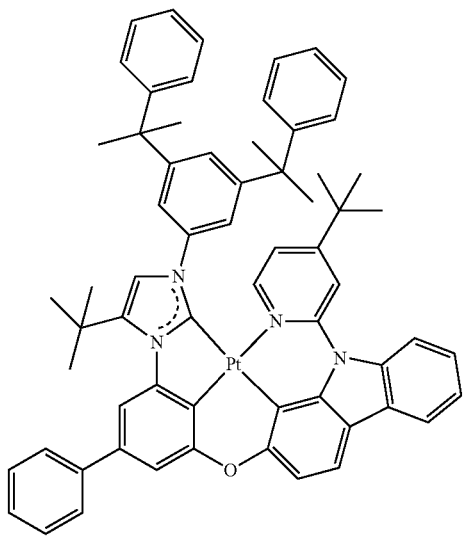
15

16
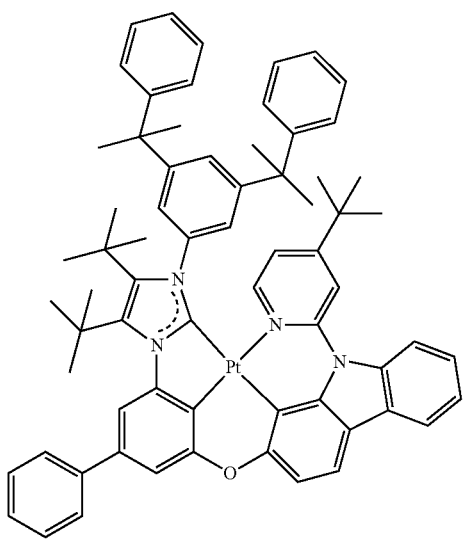
17
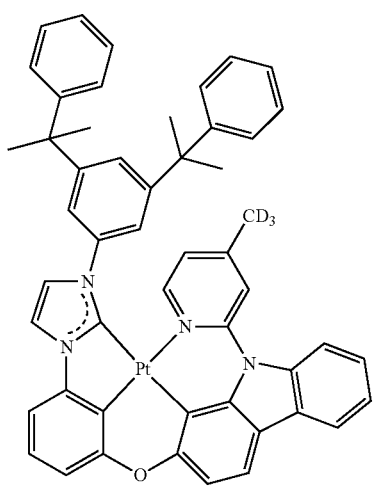
18
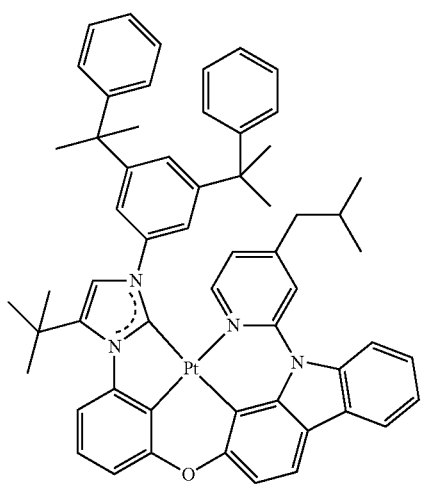
19
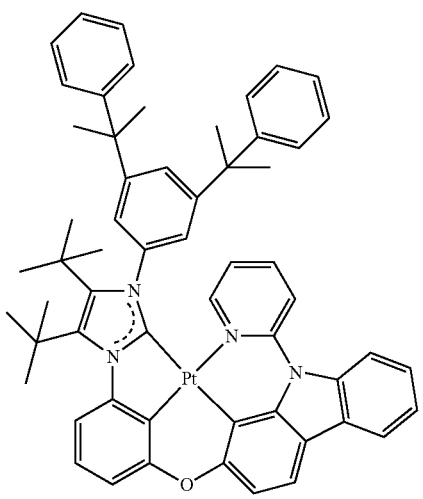
20
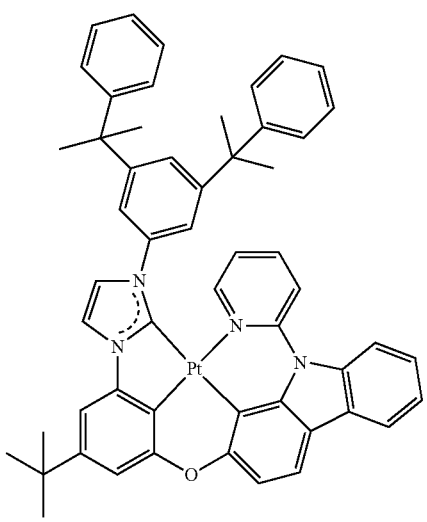
21
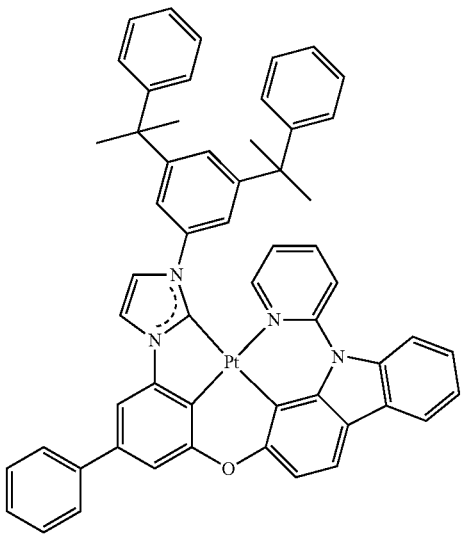

22
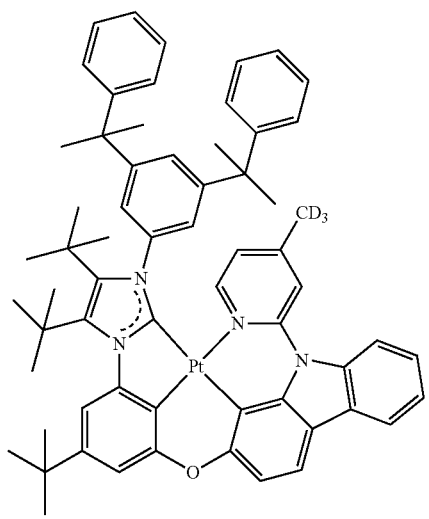
23
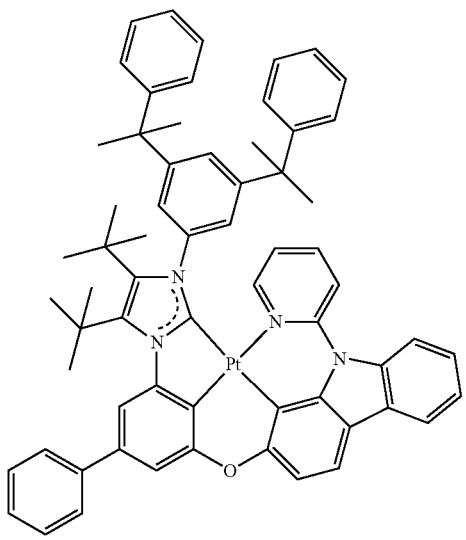
24
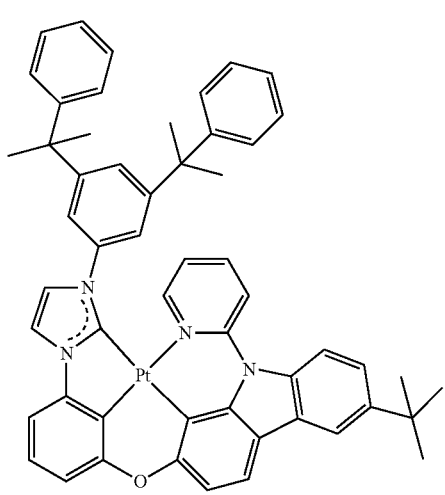
25
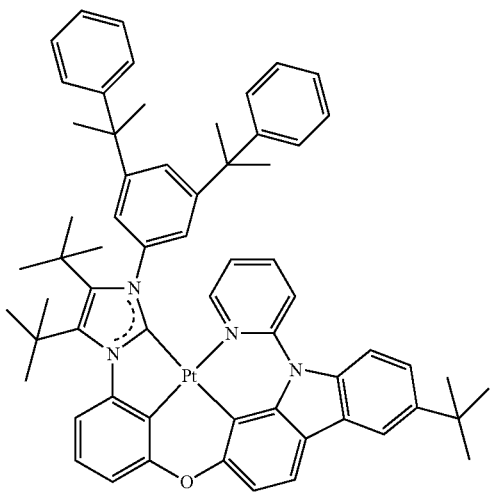
26
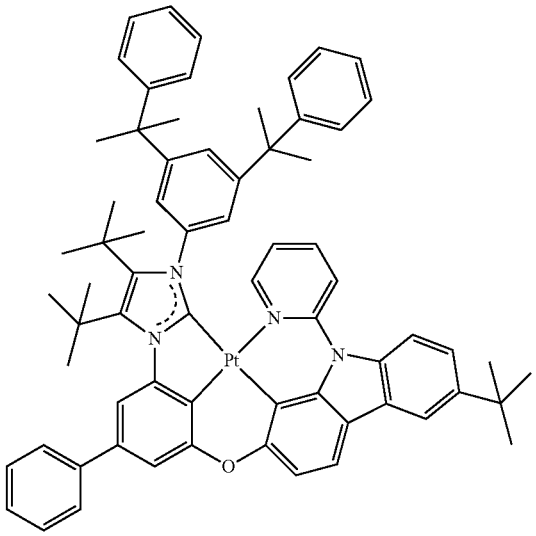
27
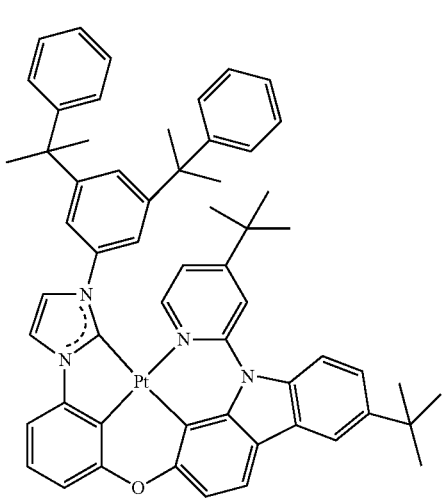

2595
-continued
28
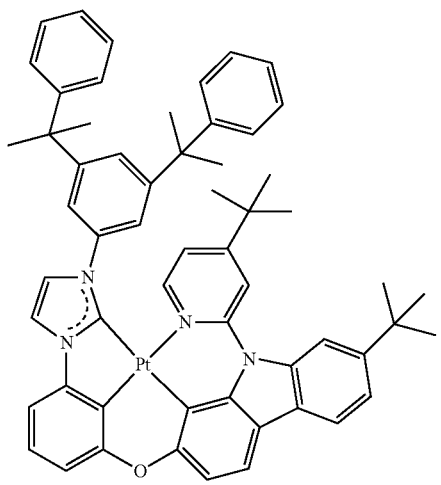
29
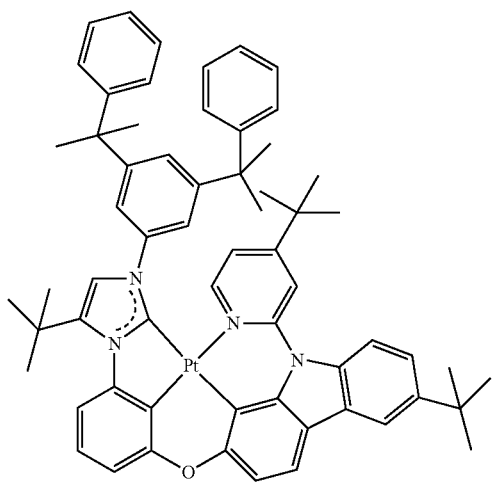
30
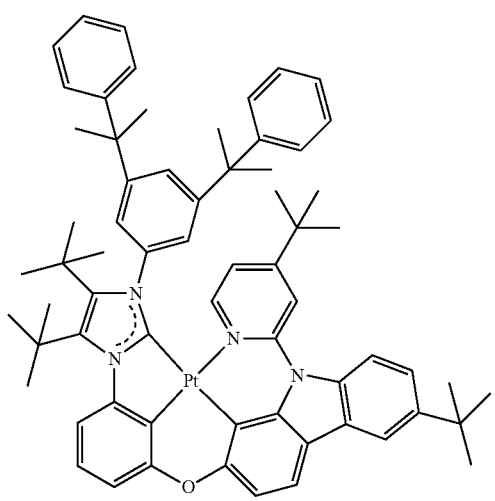
2596
-continued
31
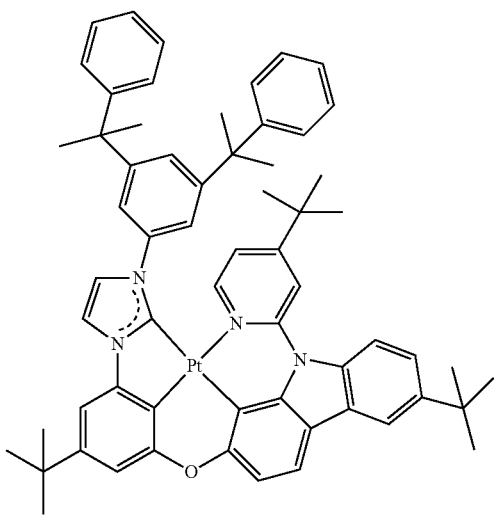
32
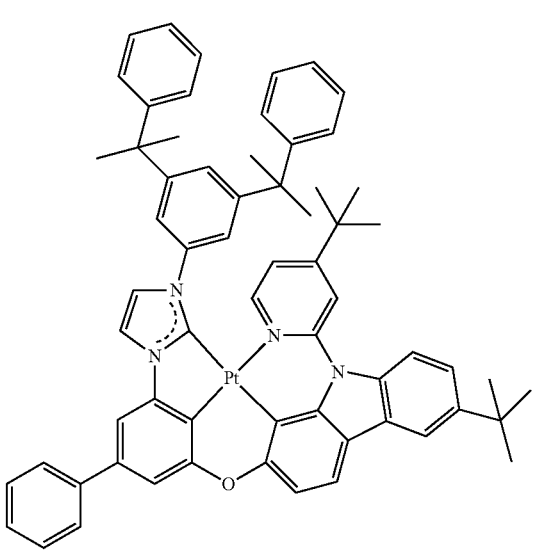
33
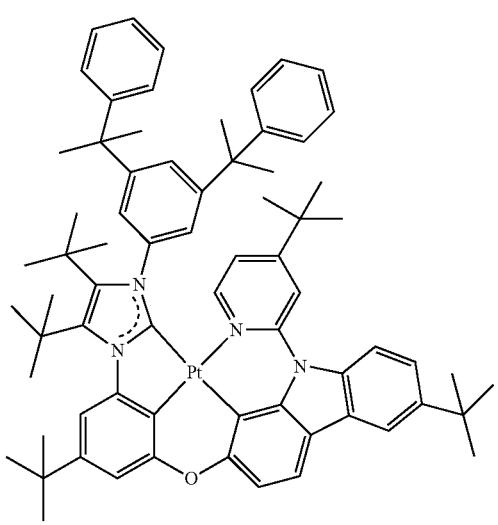

2597
-continued
34
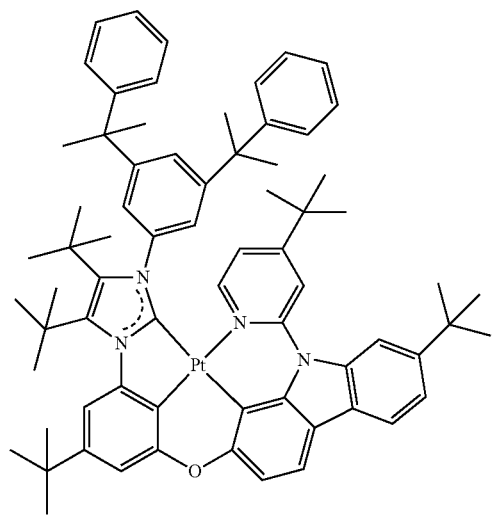
35
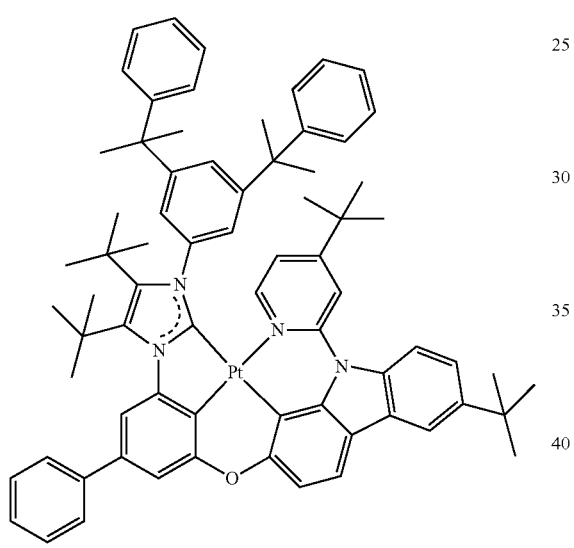
36
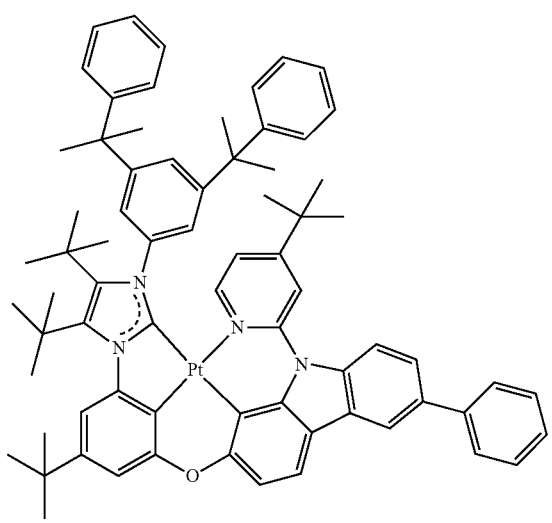
2598
-continued
37
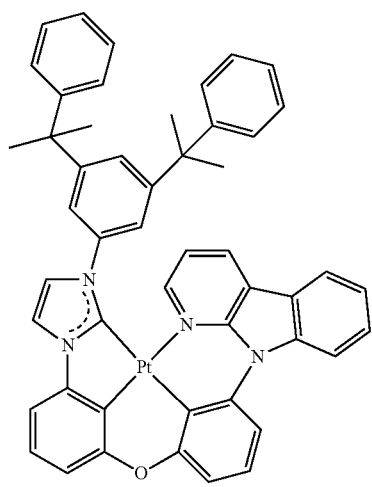
38
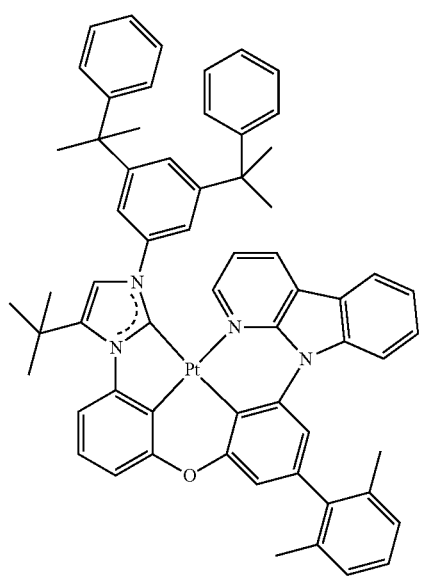
39
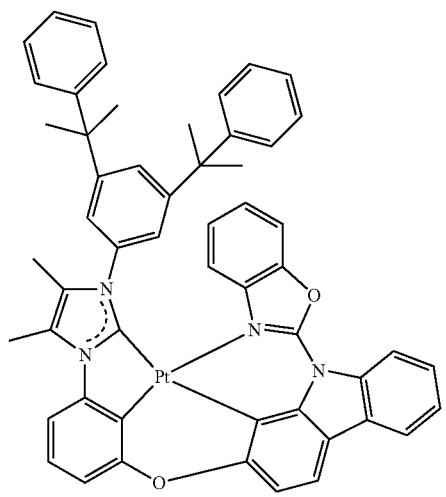

2599
-continued
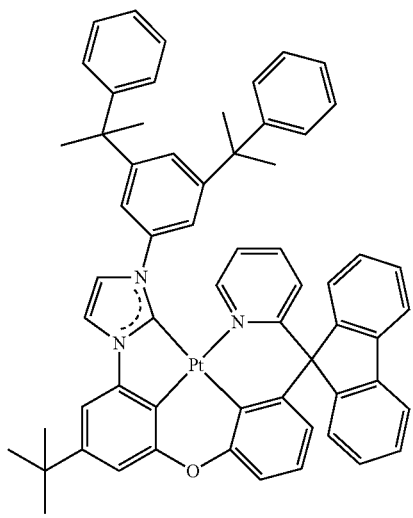
40
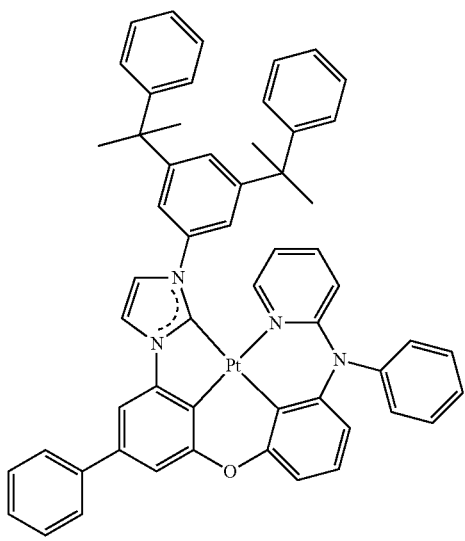
41
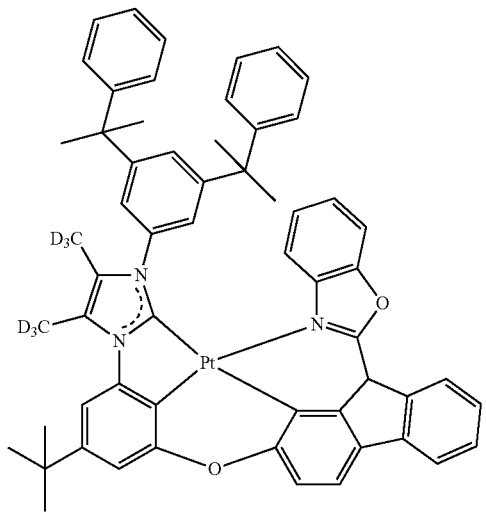
42
2600
-continued
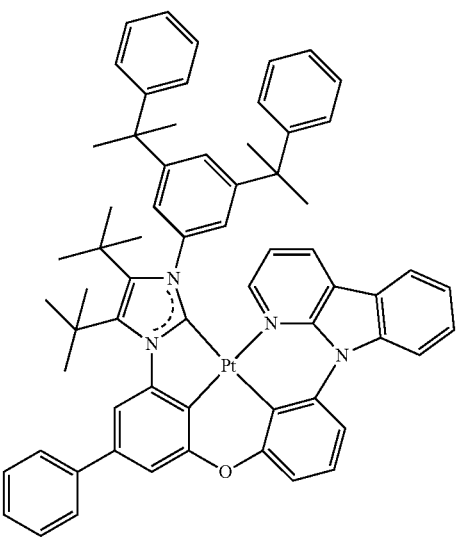
43
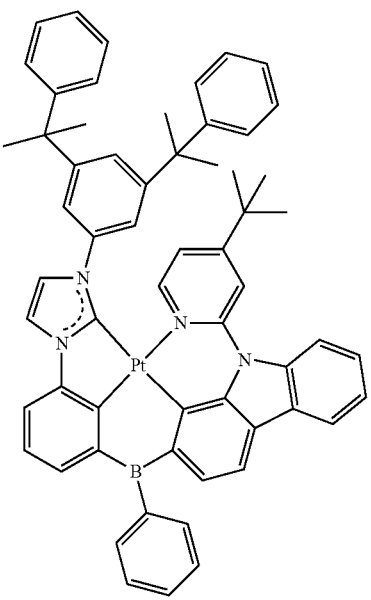
44

2601
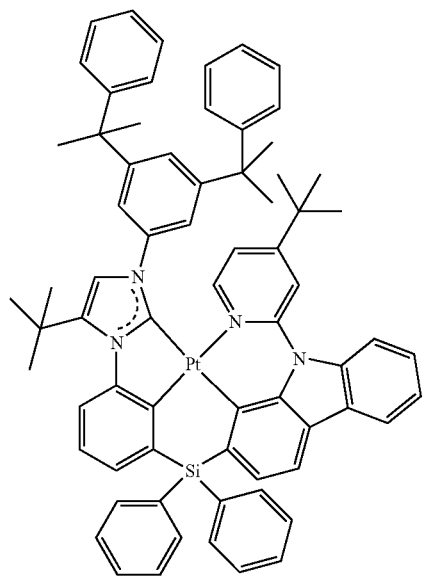
45
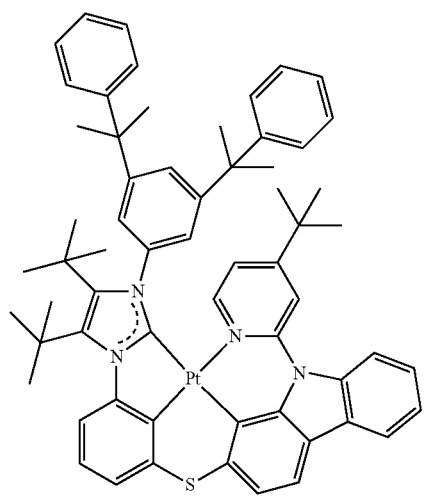
46
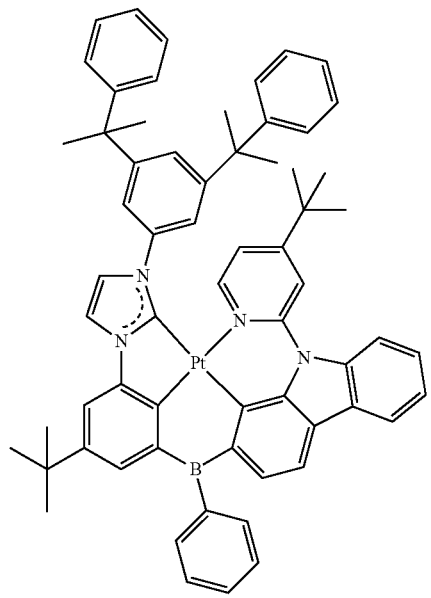
47
2602
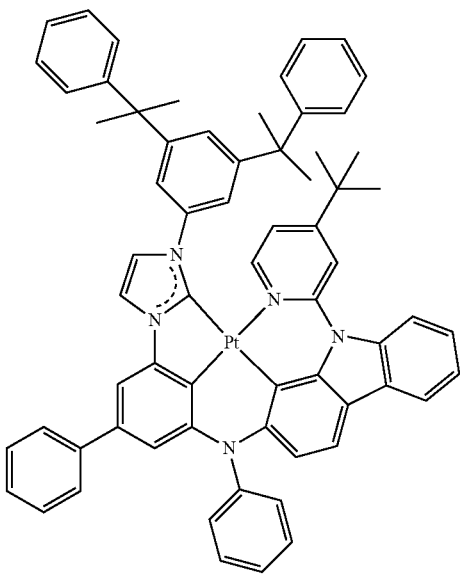
48
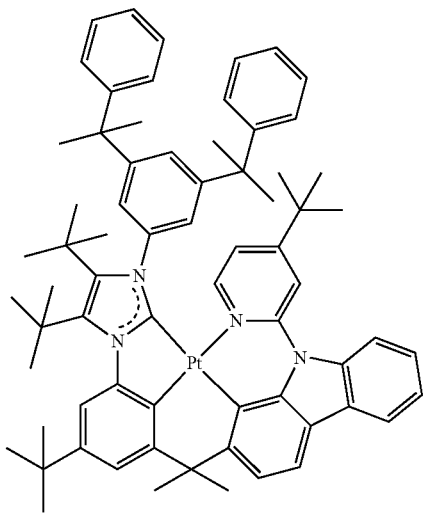
49
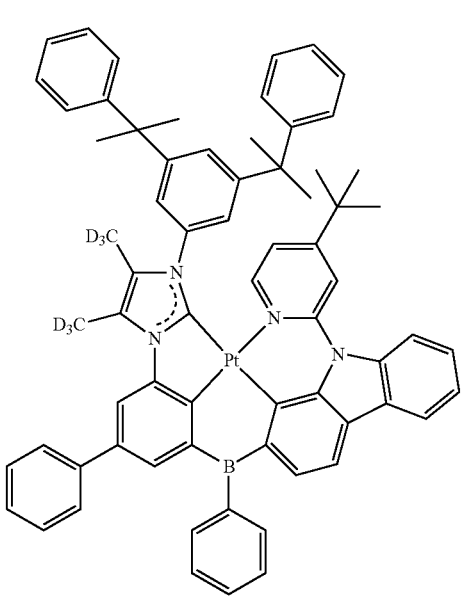
50

2603
-continued
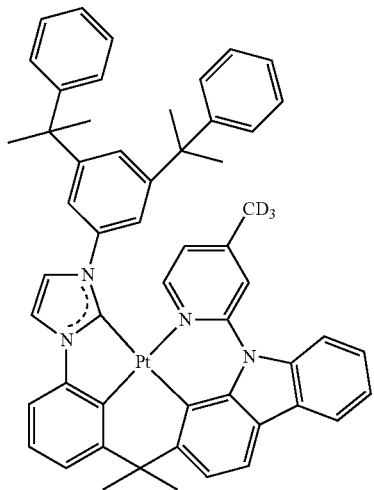
2604
-continued
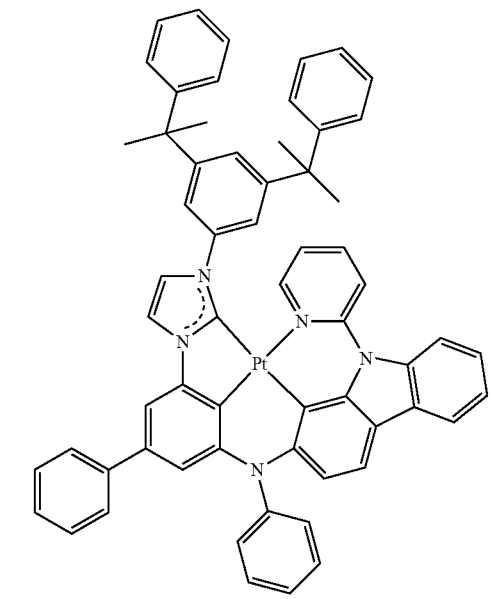
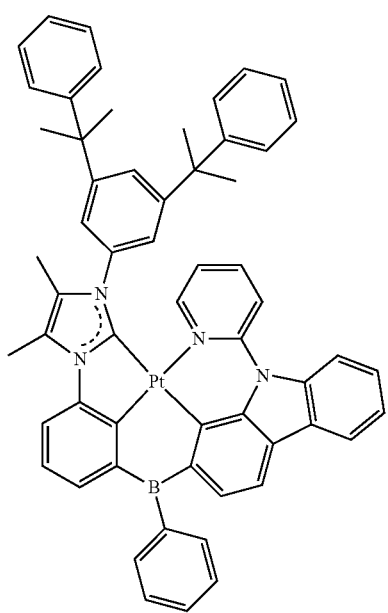

2605
-continued
55
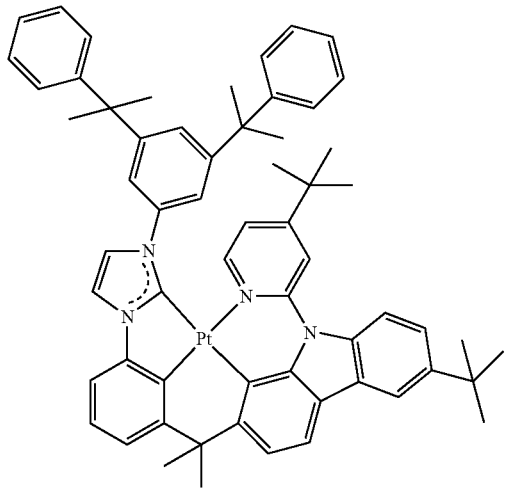
56
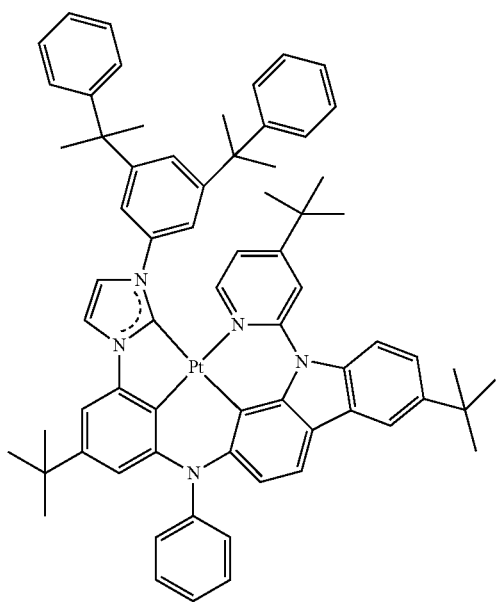
2606
-continued
57
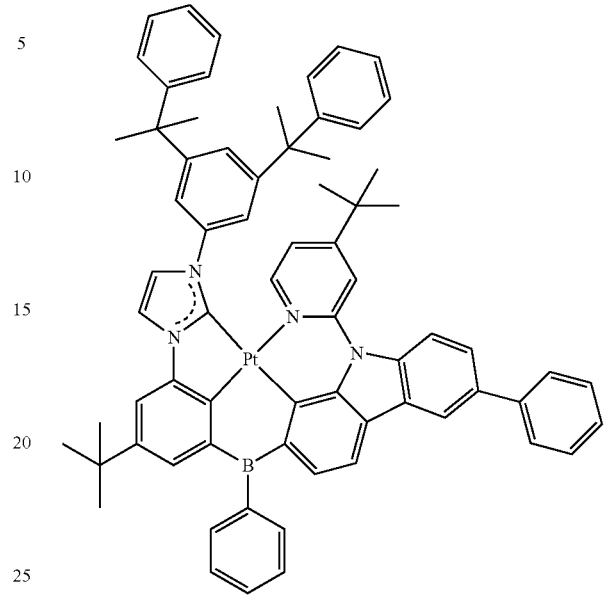
58
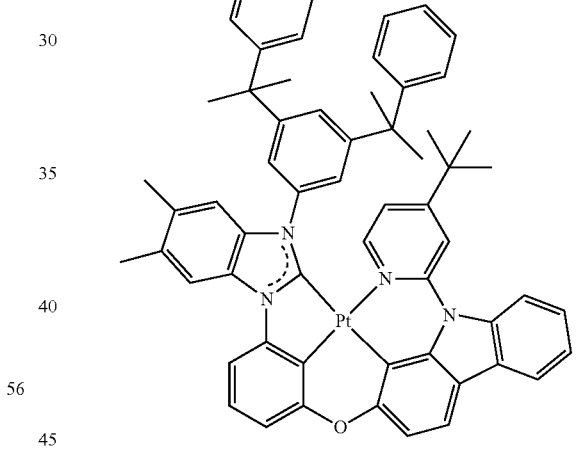
59
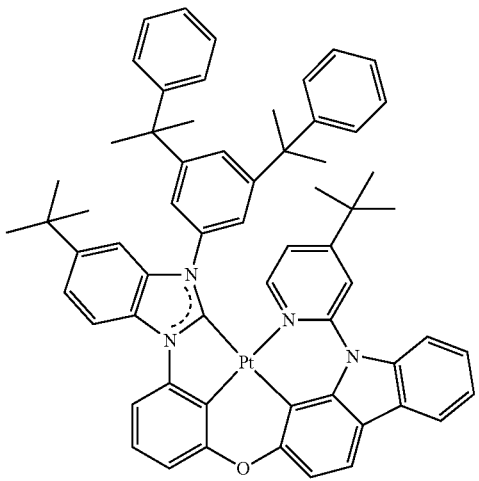

2607
-continued
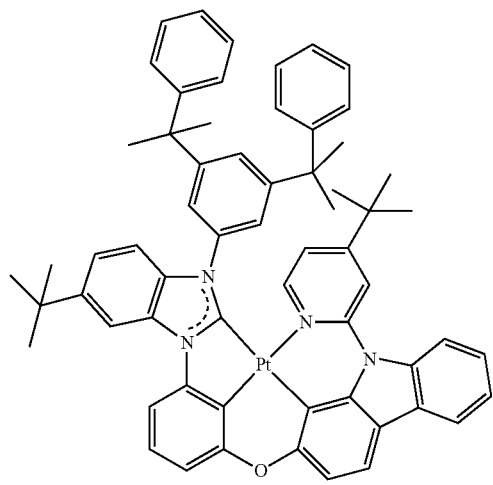
60
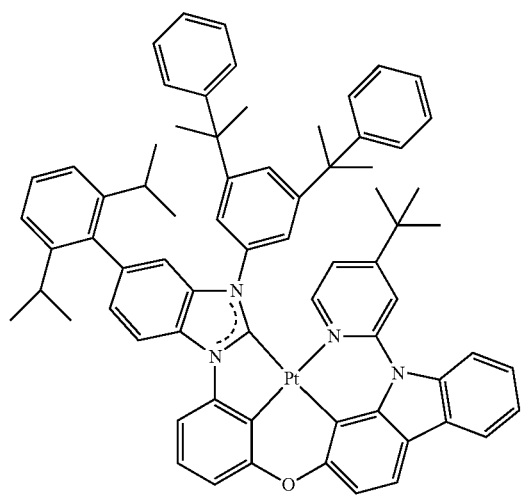
61
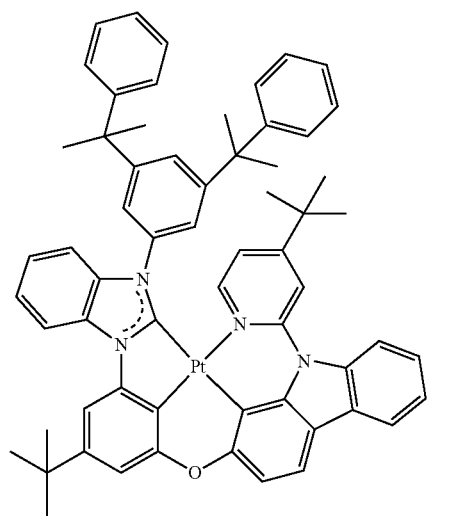
62
2608
-continued
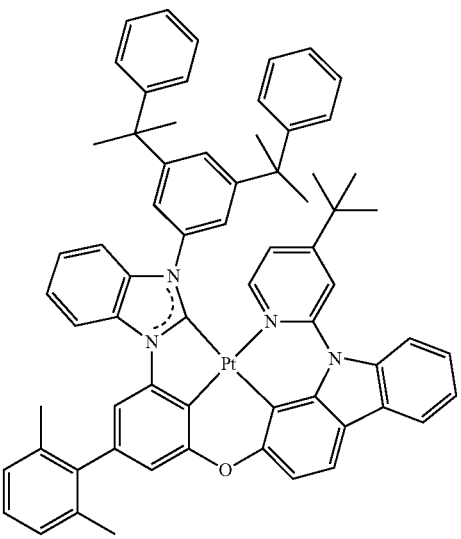
63
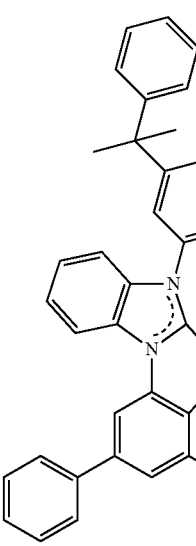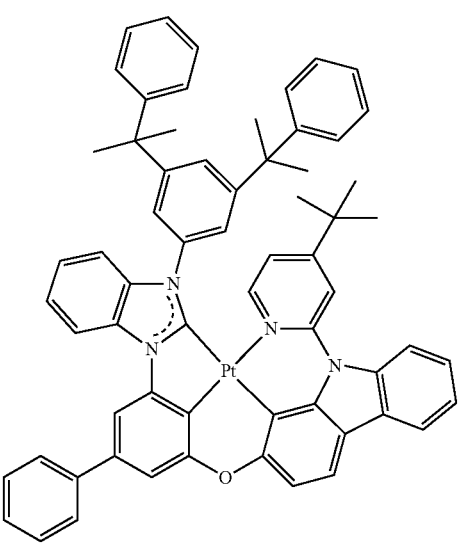
64
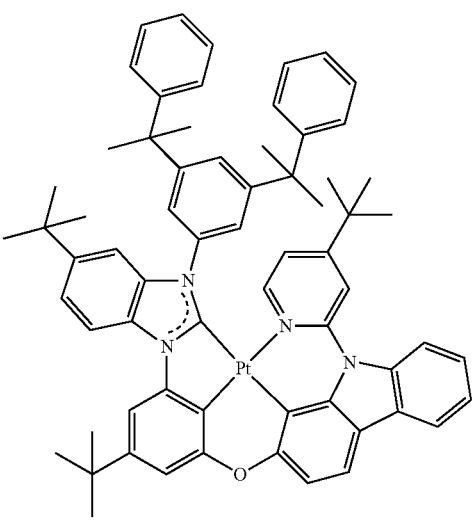
65

2609
-continued
66
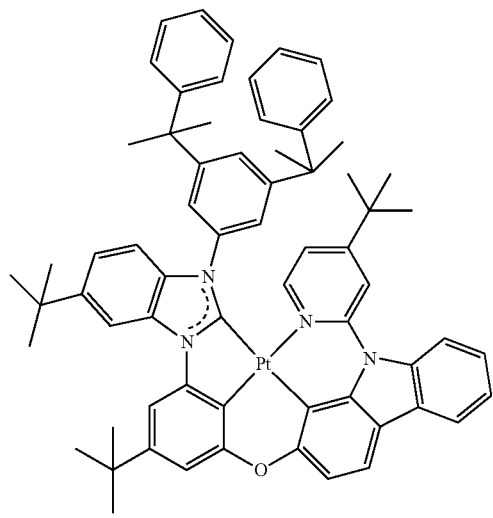
67
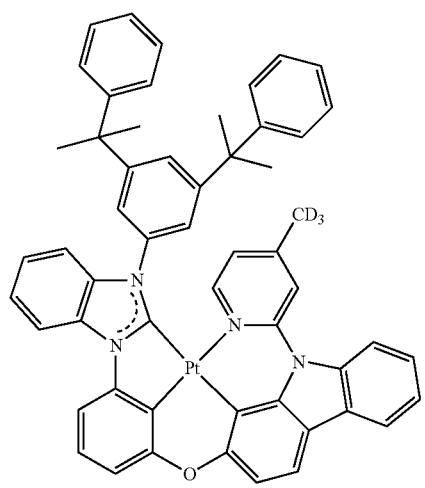
68
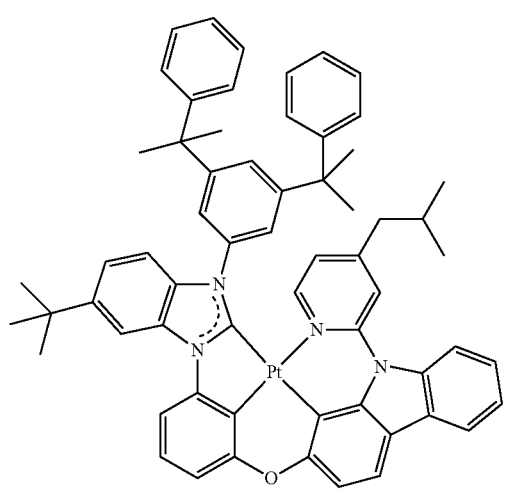
2610
-continued
69
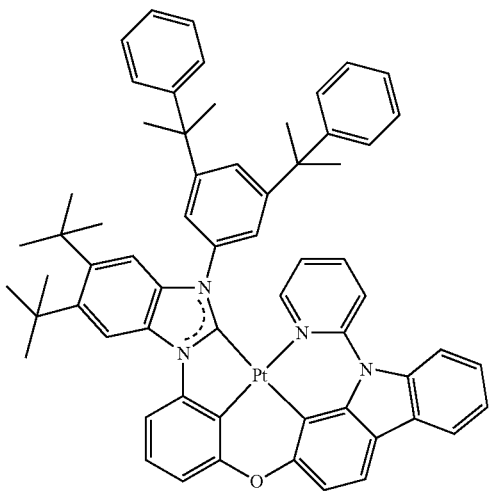
70
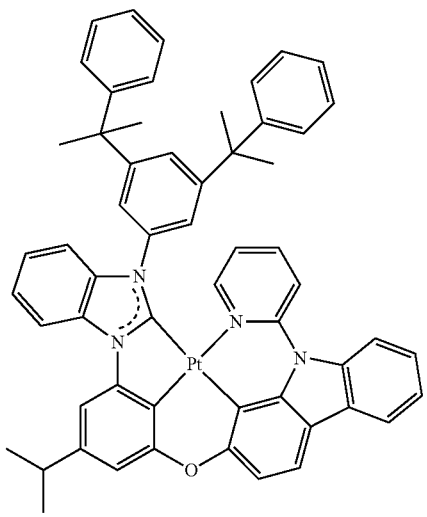
71
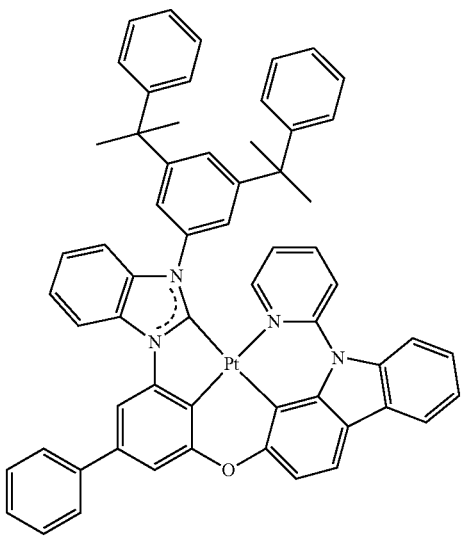

2611
-continued
72
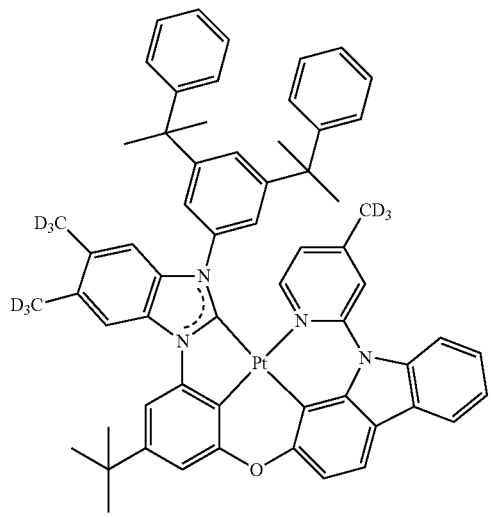
73
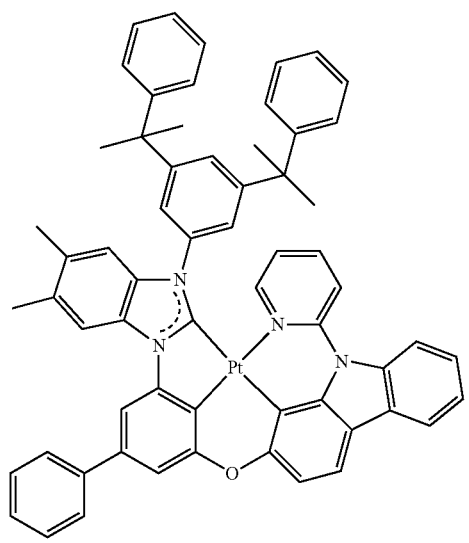
74
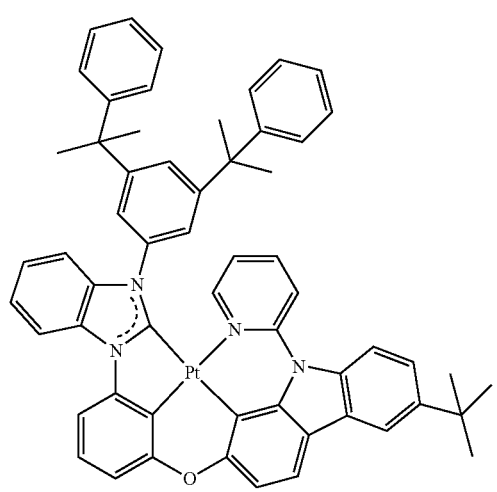
2612
-continued
75
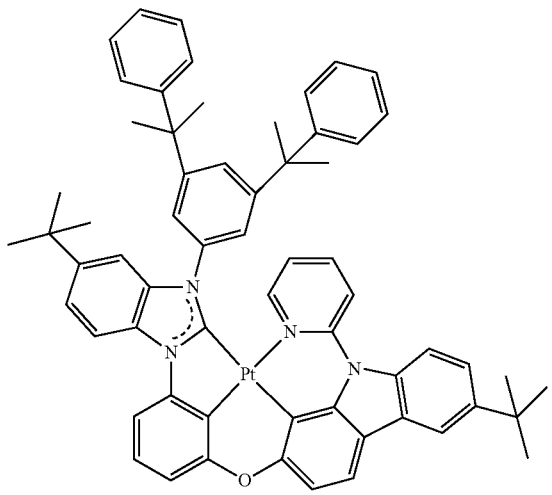
76
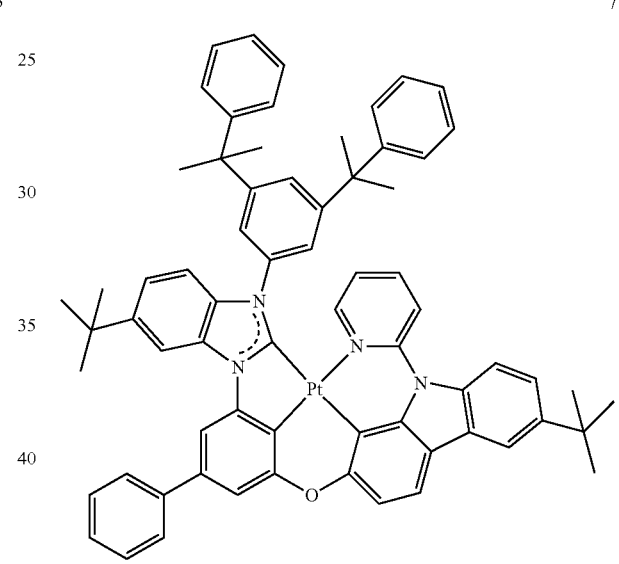
77
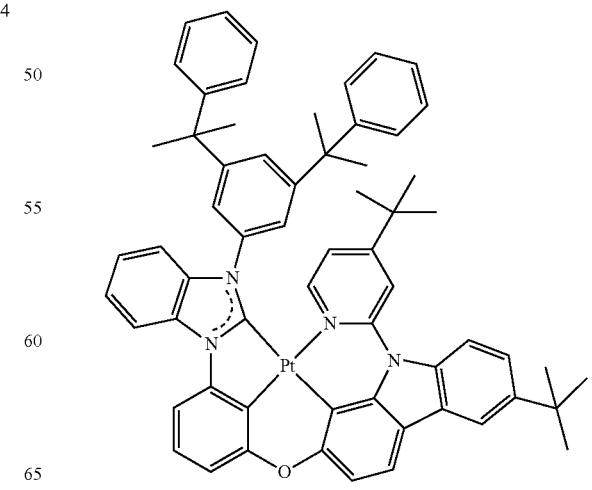

2613
-continued
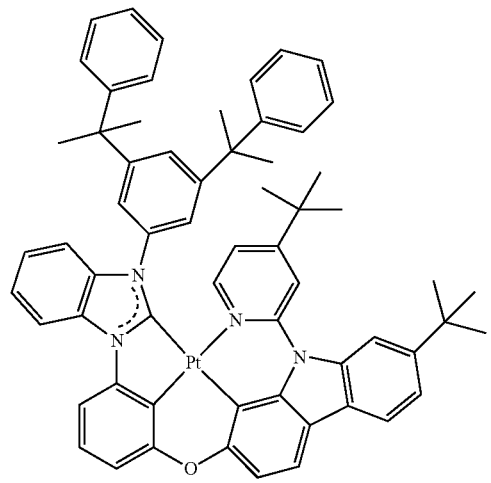
78
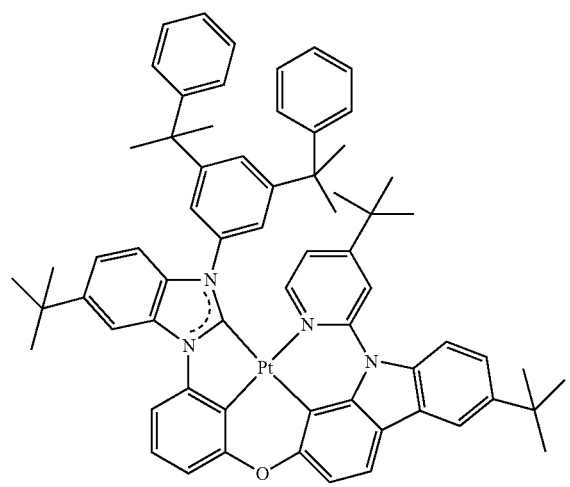
79
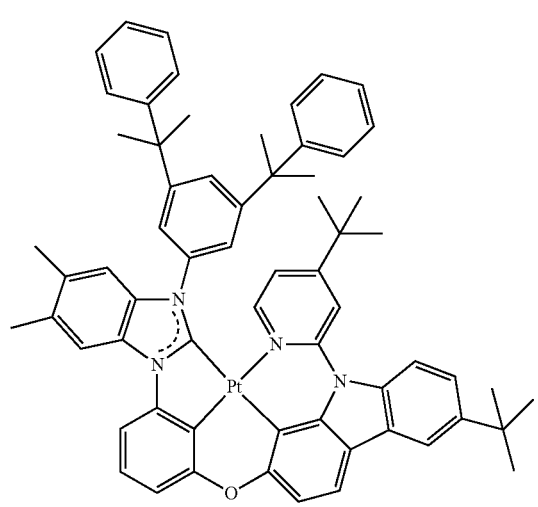
80
2614
-continued
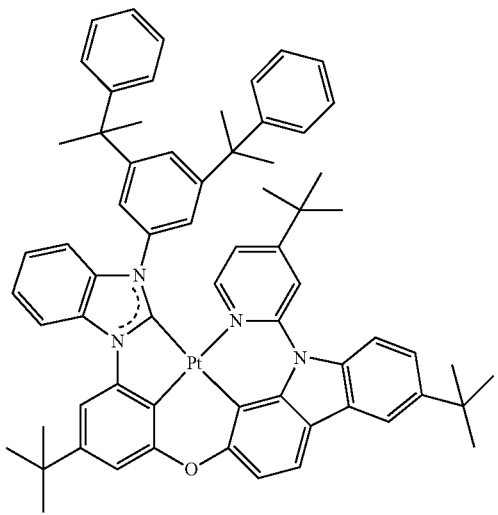
81
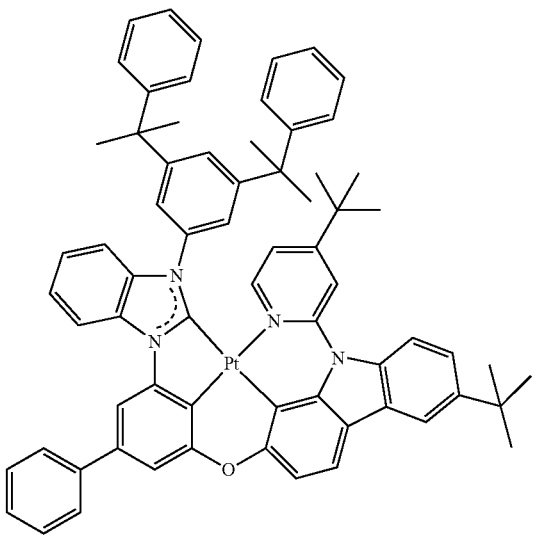
82
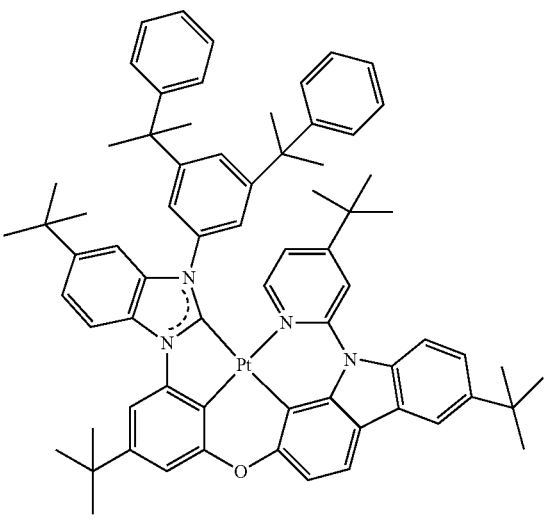
83

2615
-continued
84
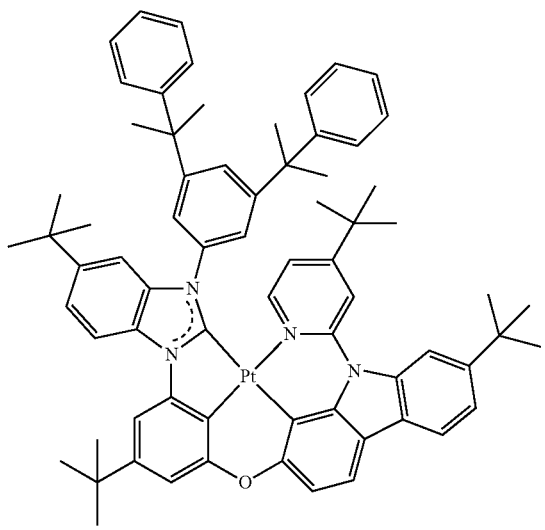
85
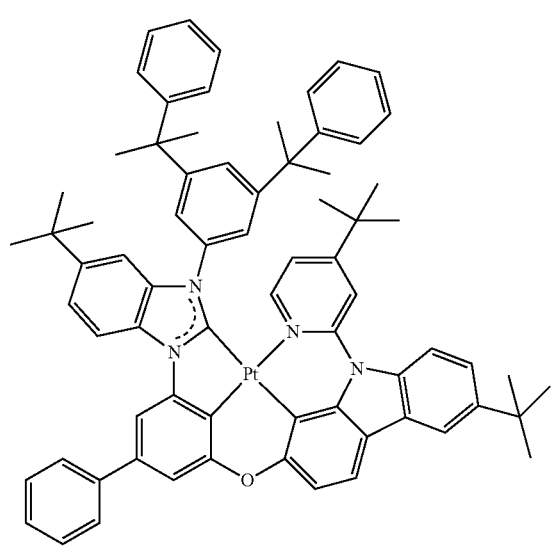
86
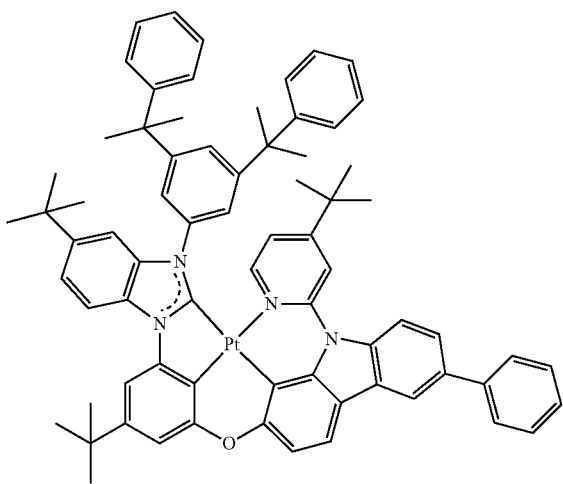
2616
-continued
87
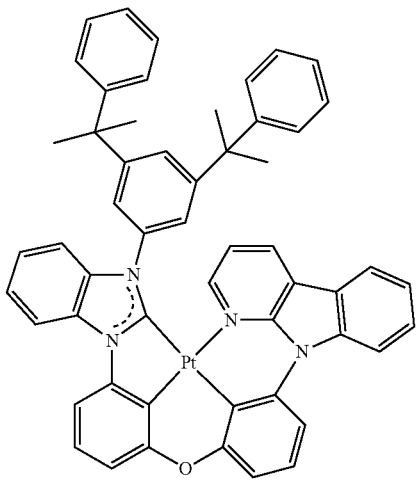
88
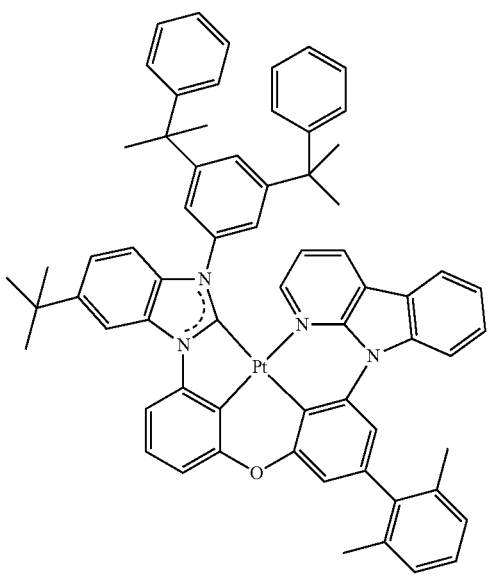
89
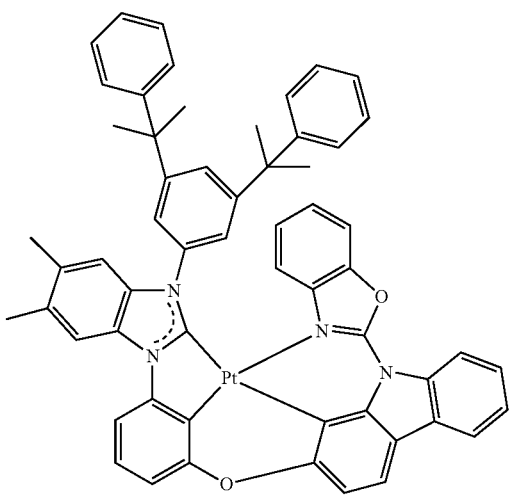

2617
-continued
2618
-continued
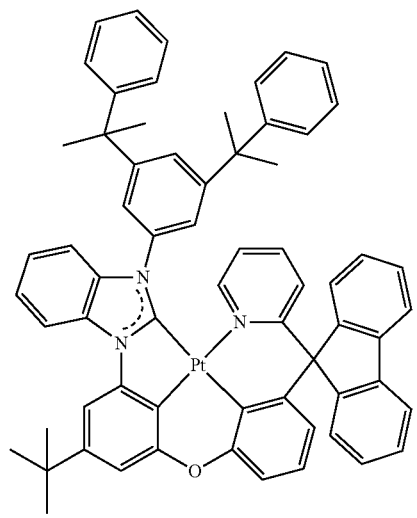
90
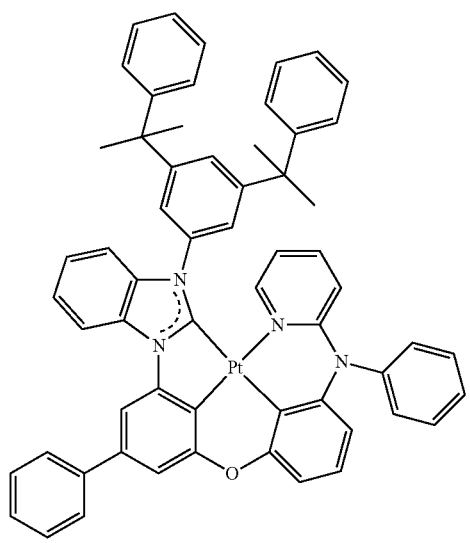
91
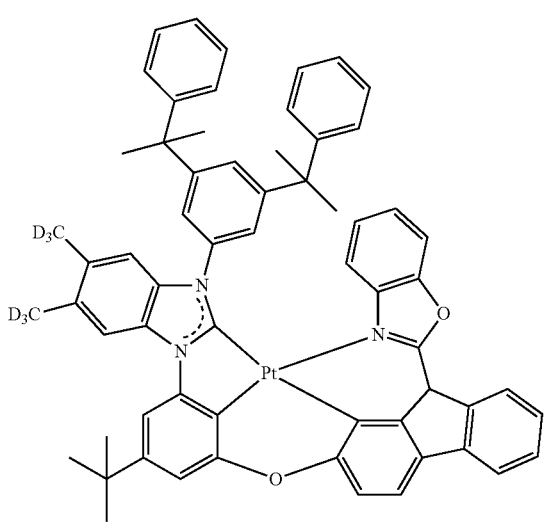
92
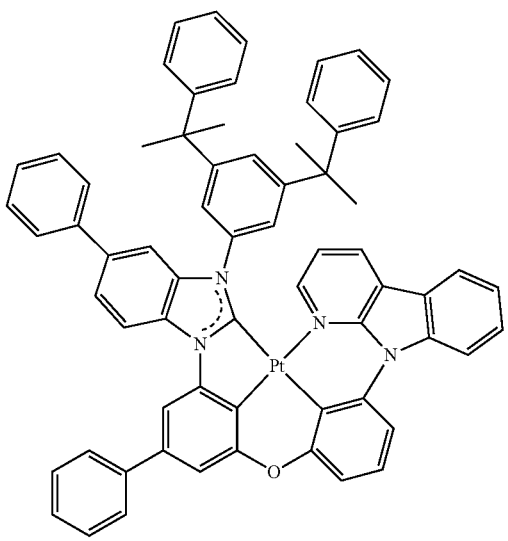
93
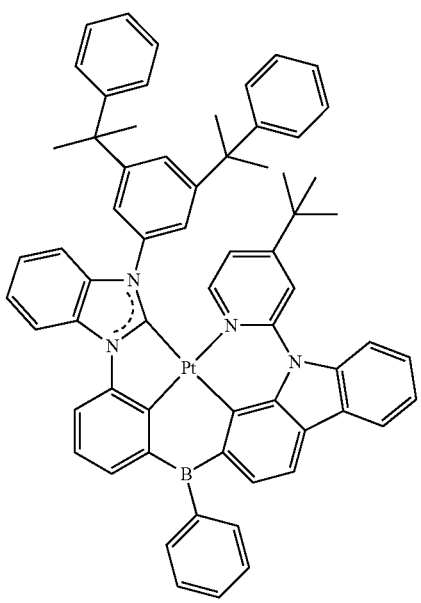
94

2619
-continued
95
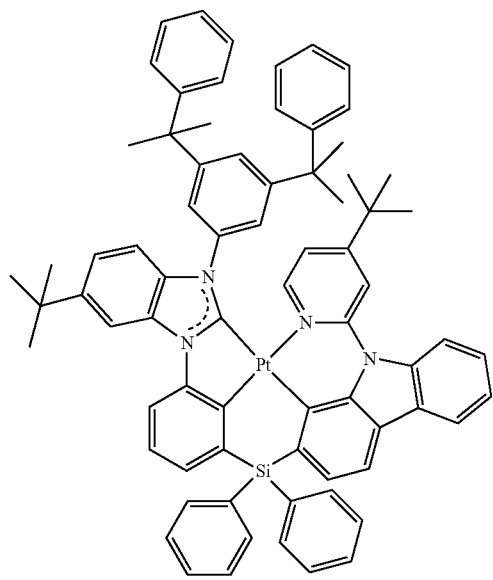
96
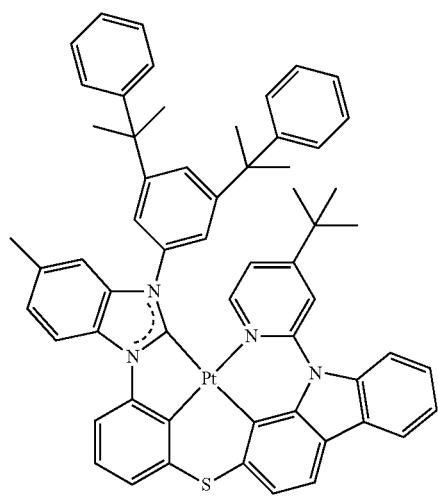
97
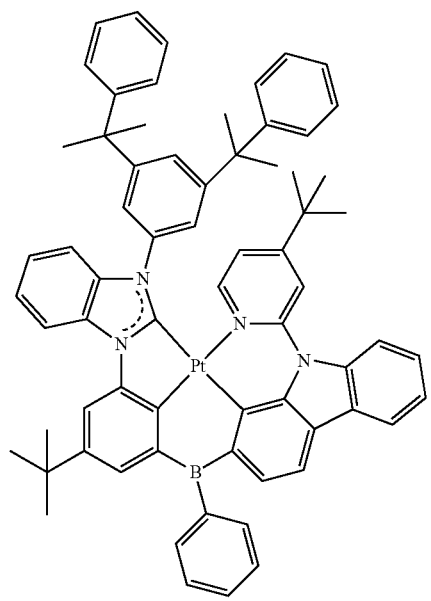
2620
-continued
98
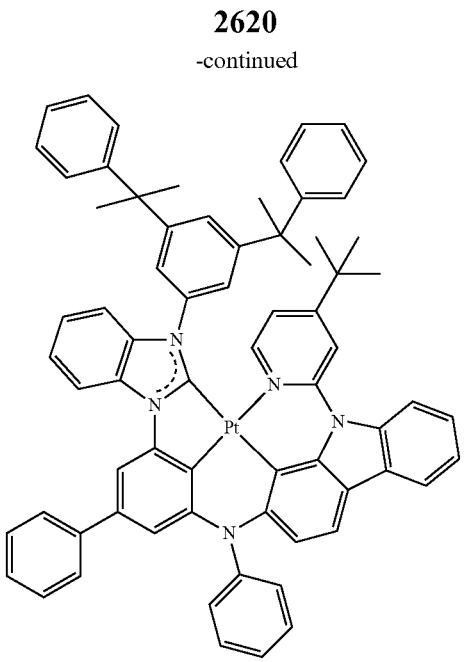
99
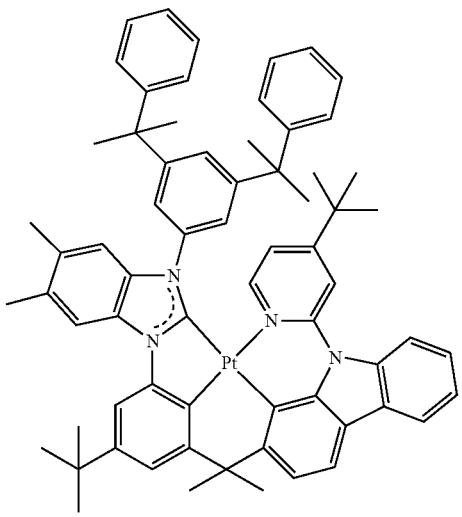
100
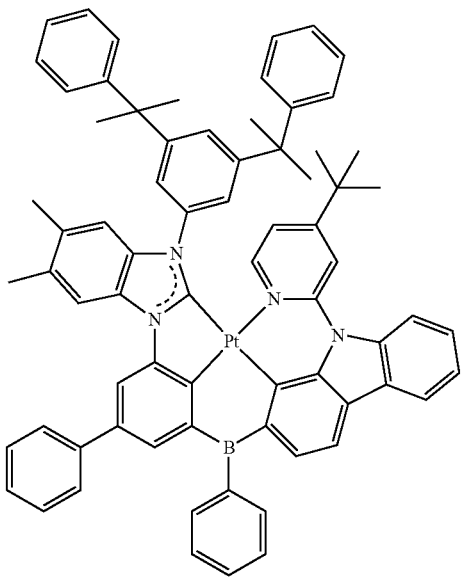

2621
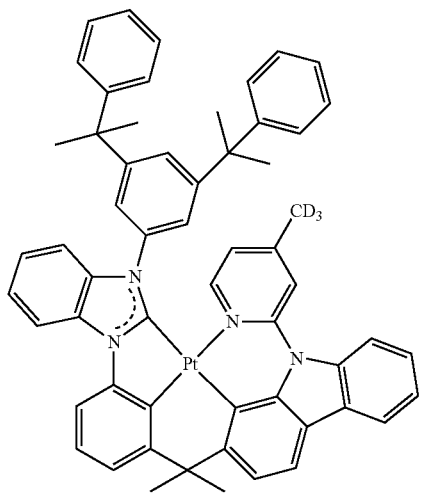
2622
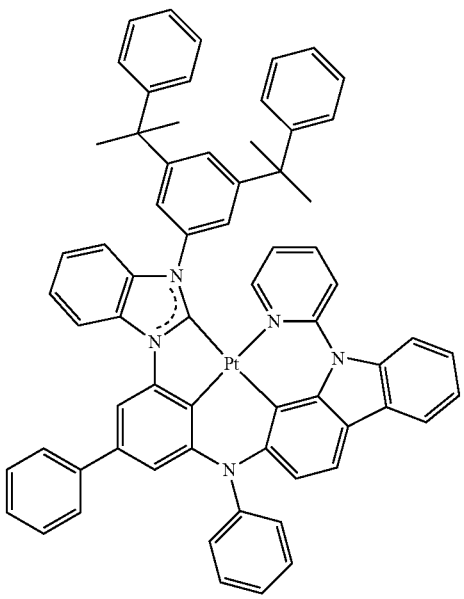
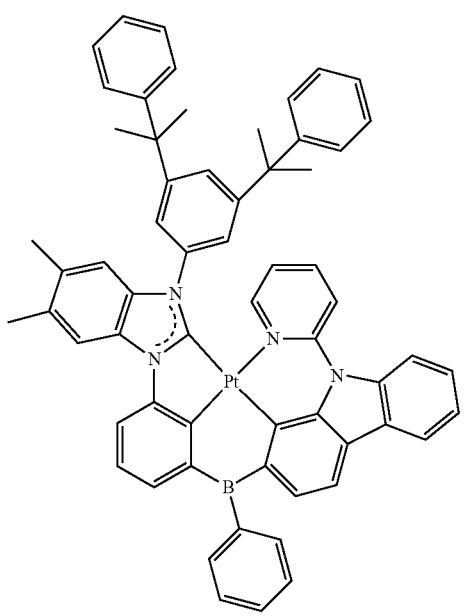
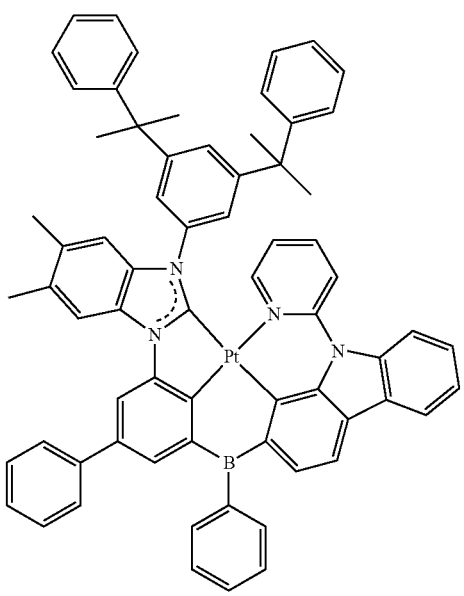

2623
-continued
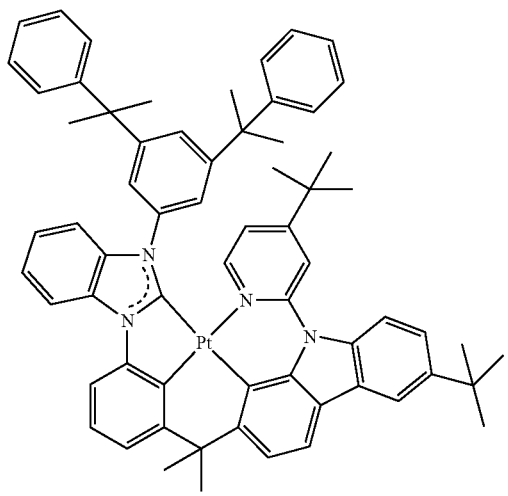
105
2624
-continued
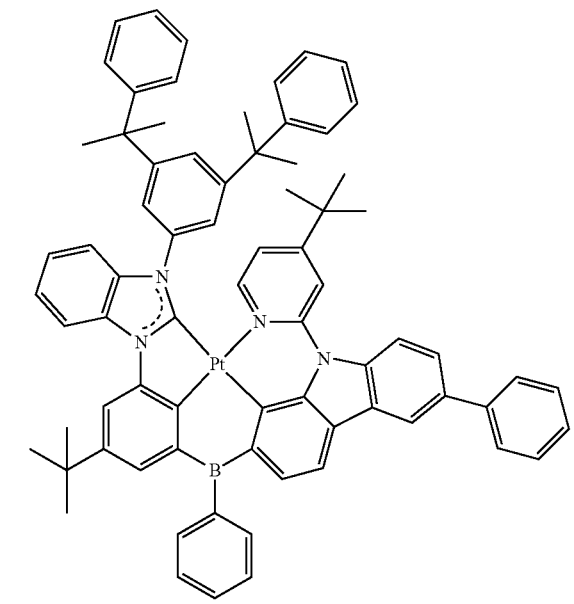
107
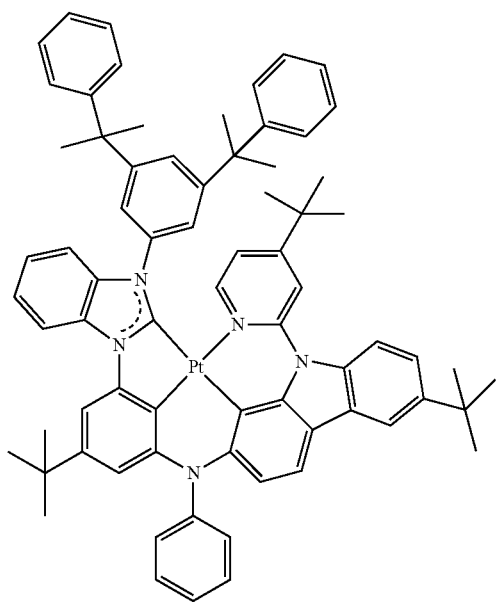
106
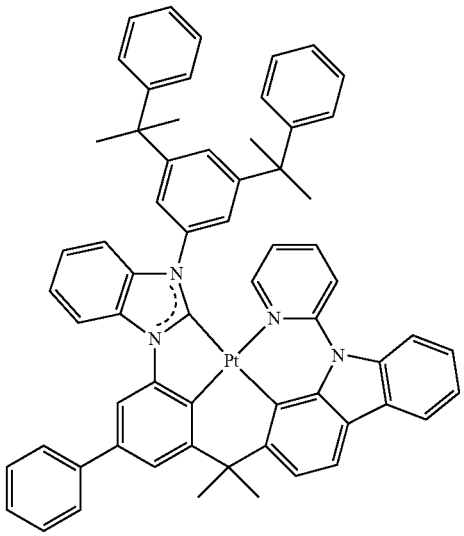
108

Group IX
1
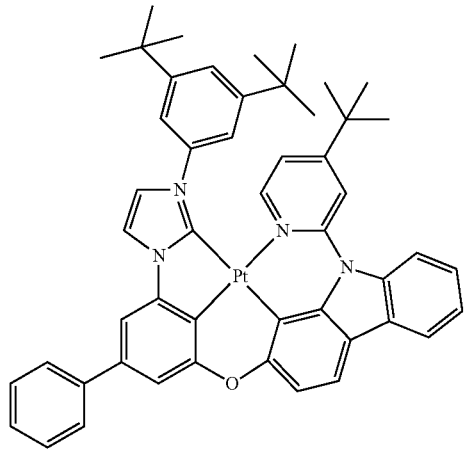
2
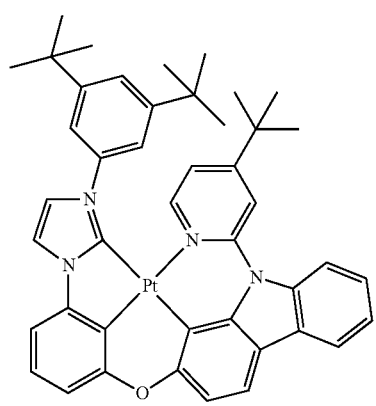
3
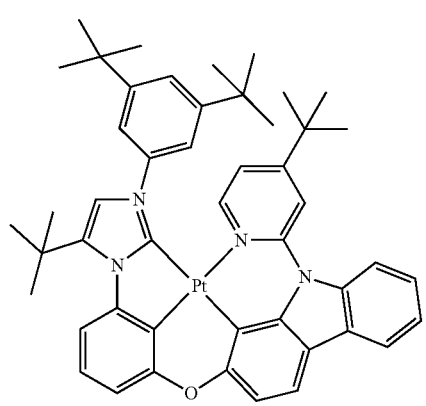
4
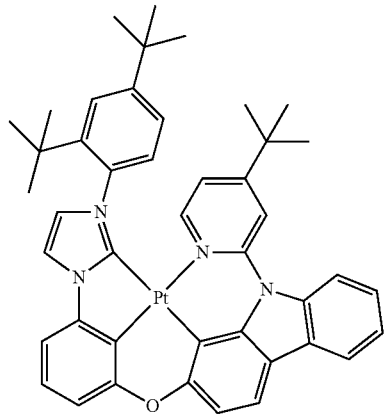
5
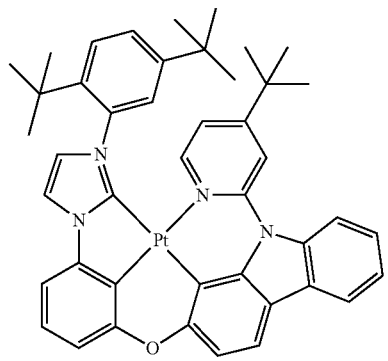
6
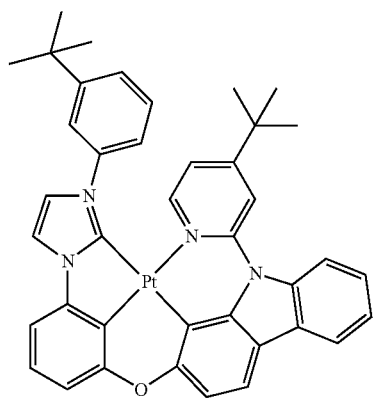
7
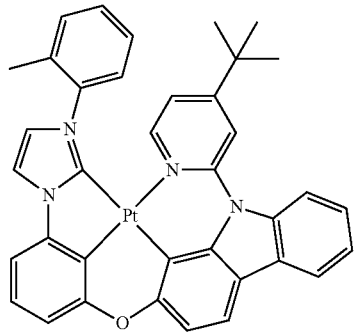

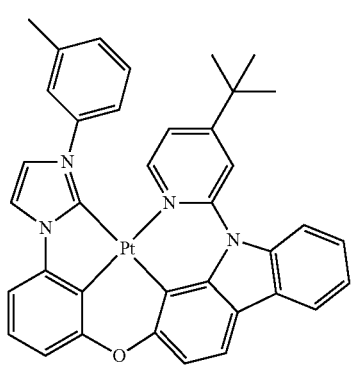
8
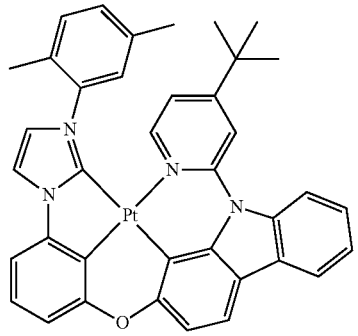
9
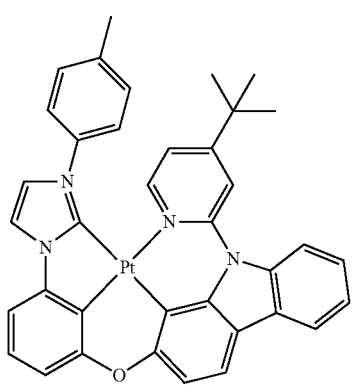
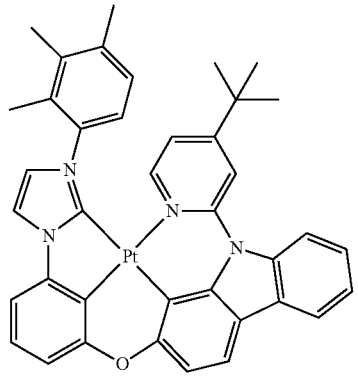
10
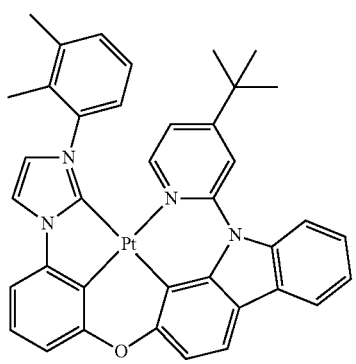
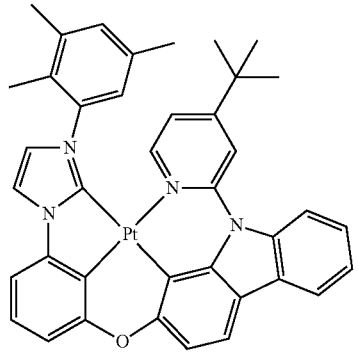
11
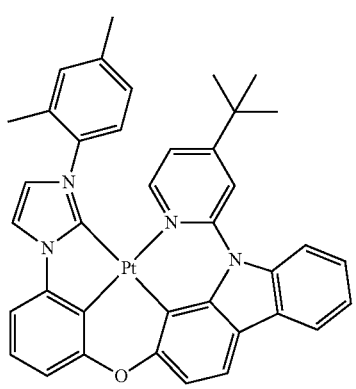
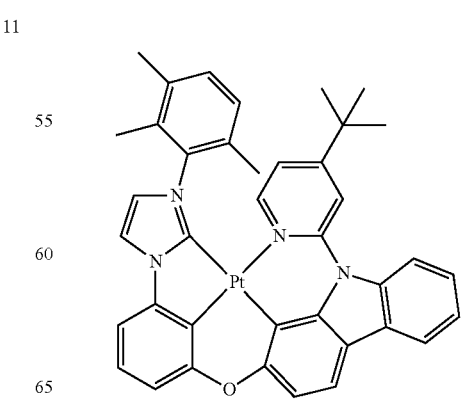

2629
-continued
16
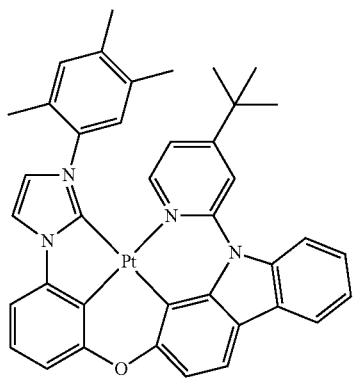
17
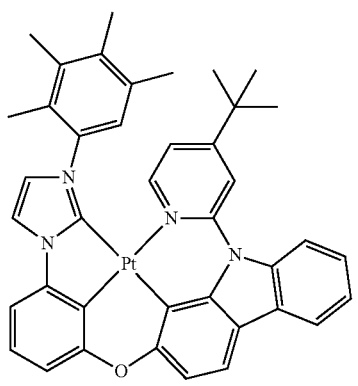
18
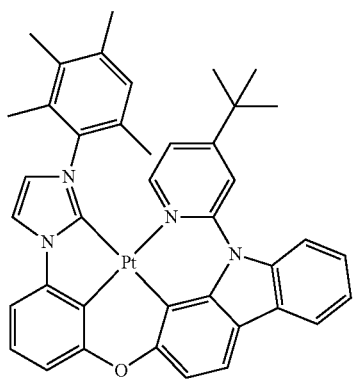
19
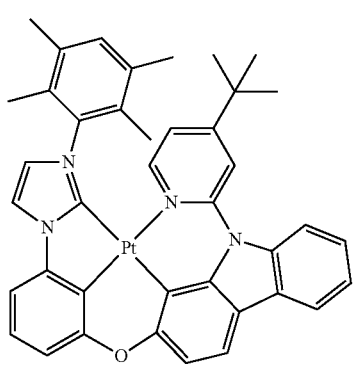
2630
-continued
20
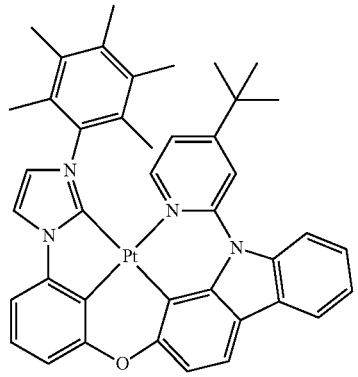
21
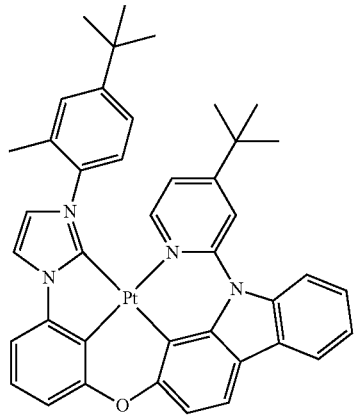
22
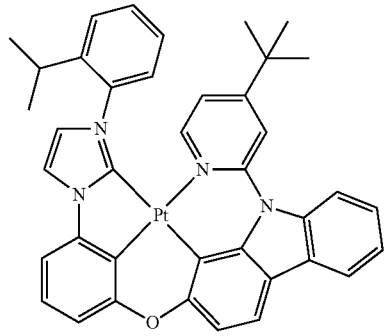
23
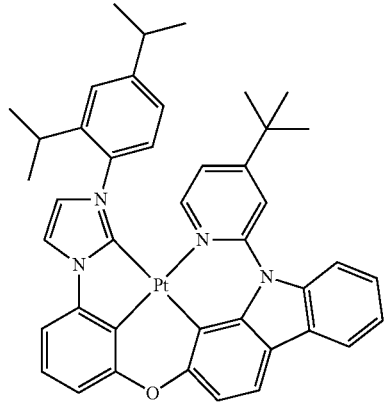

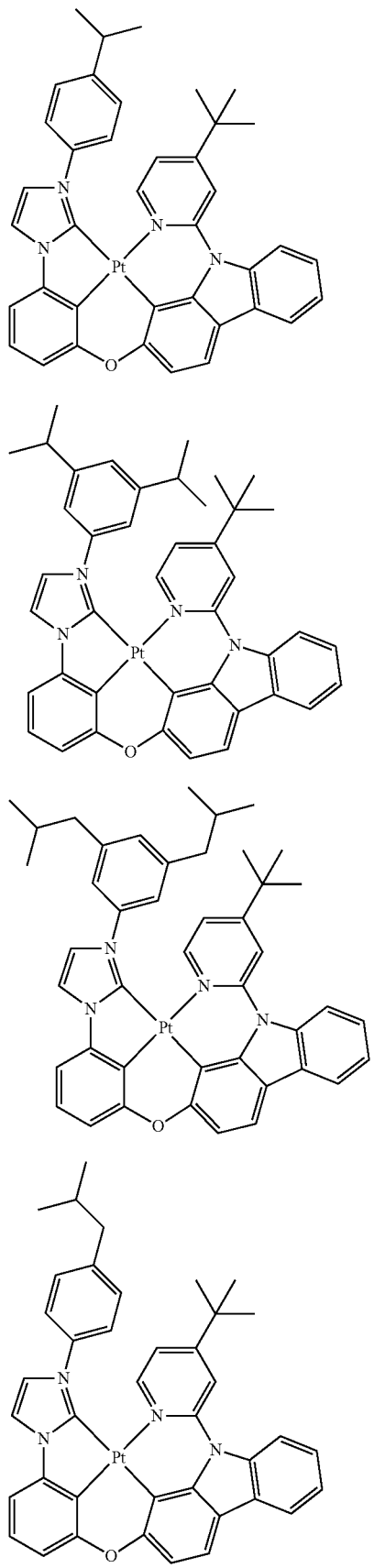
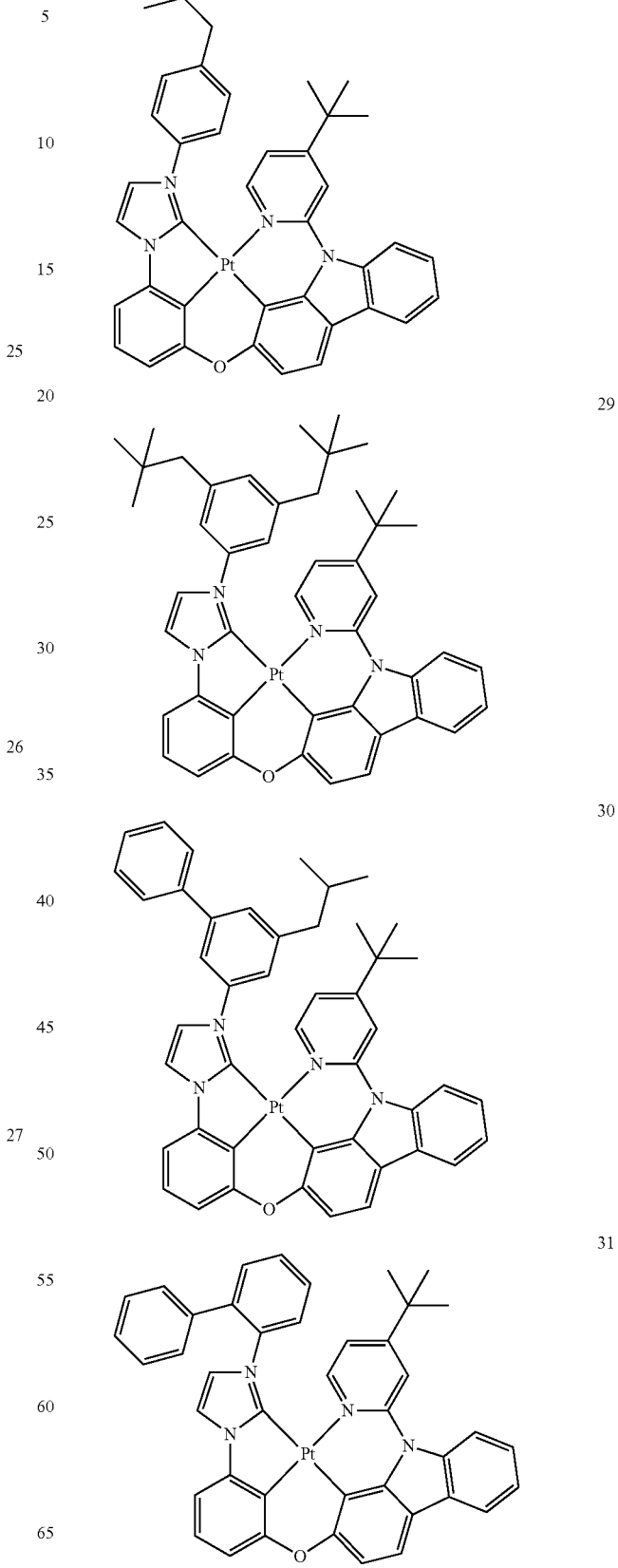

2633
-continued
32
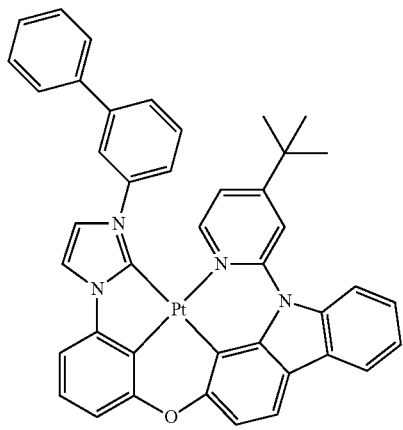
33
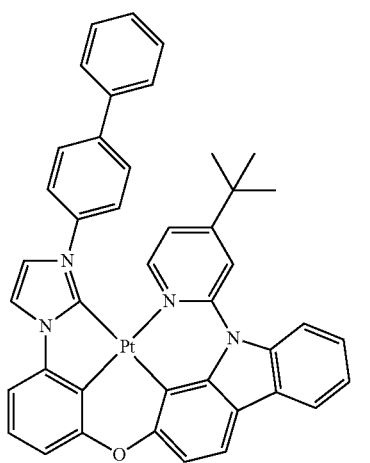
34
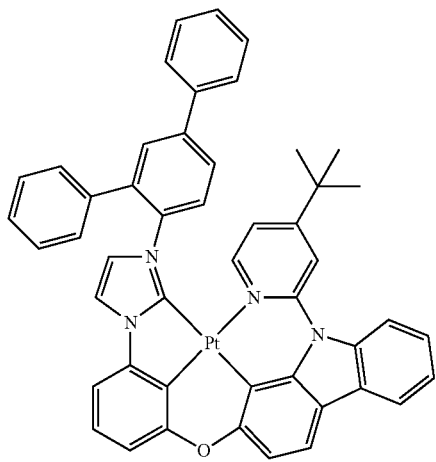
2634
-continued
35
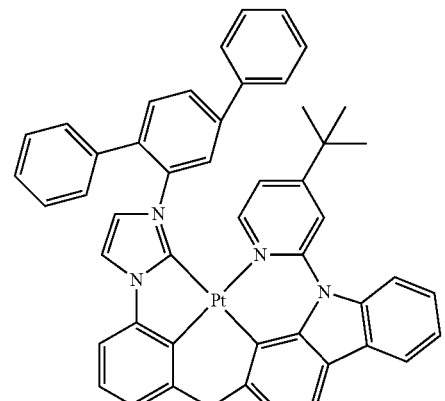
36
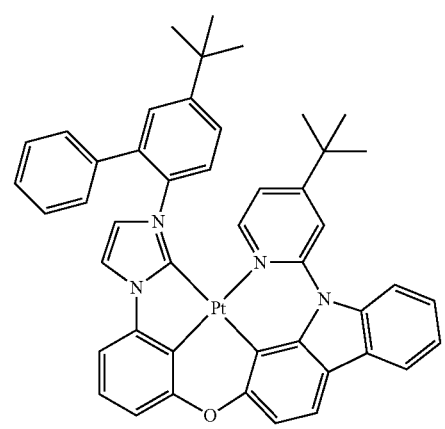
37
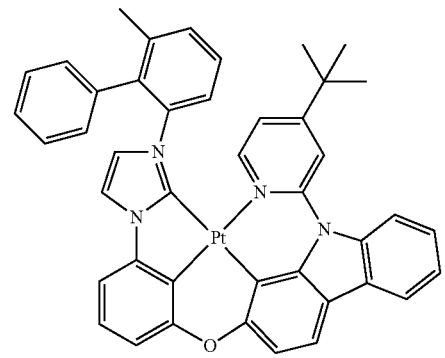
38
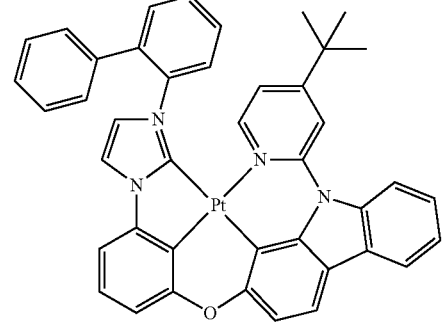

2635 -continued
39
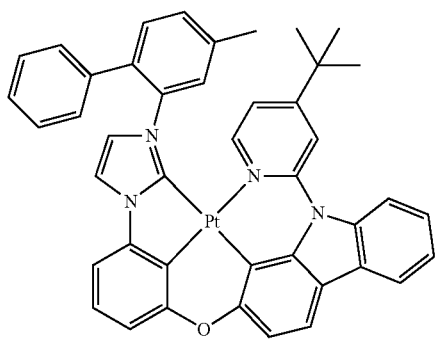
40
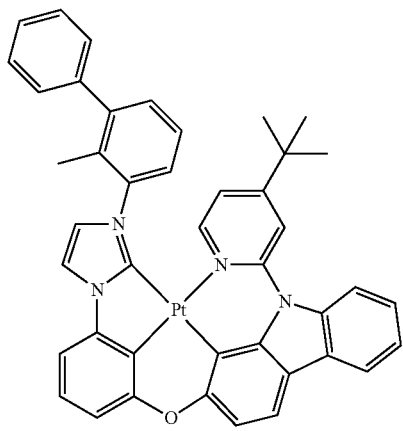
41
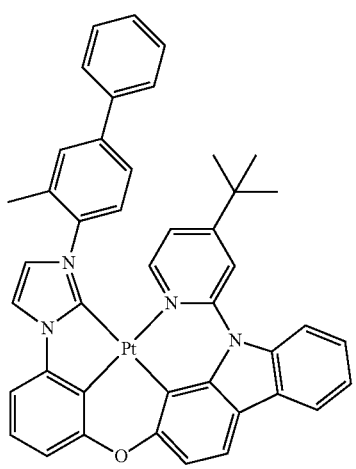
42
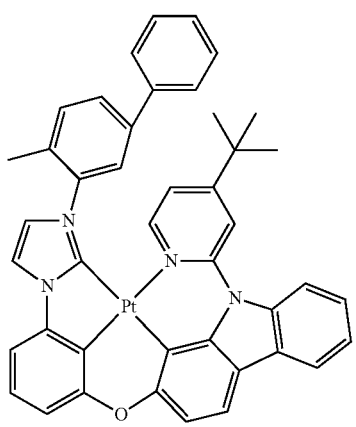
2636 -continued
43
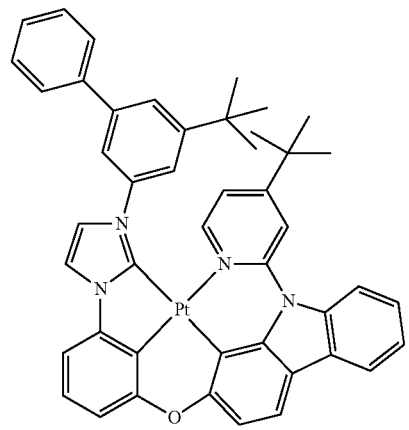
44
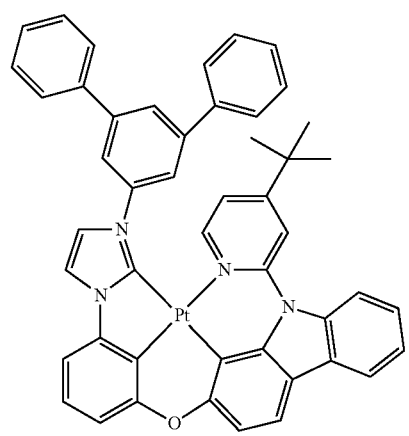
45
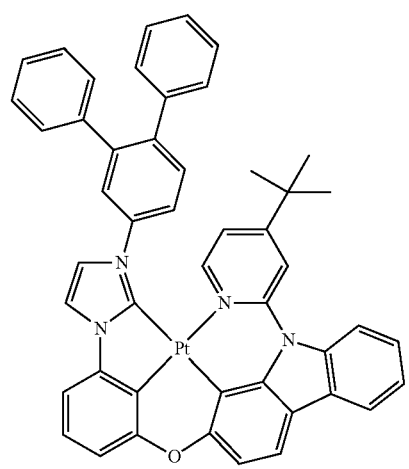

46
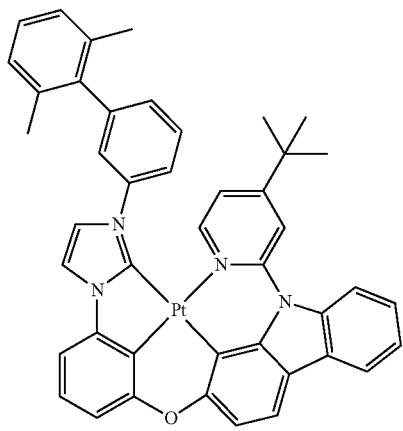
47
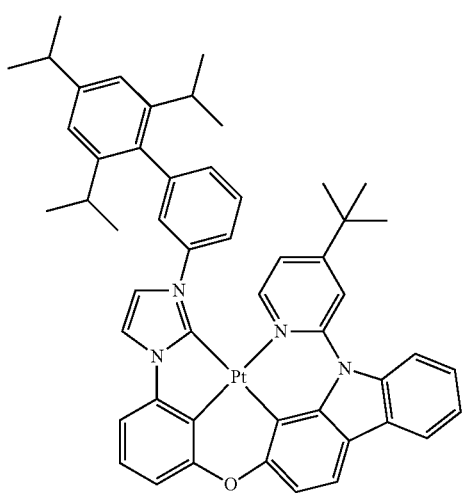
48
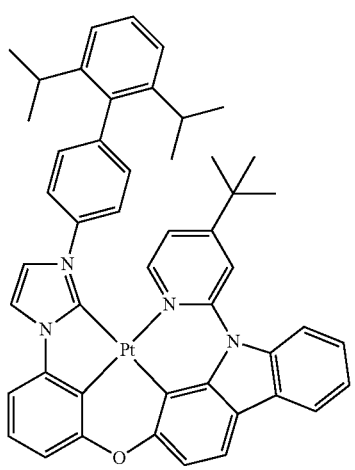
49
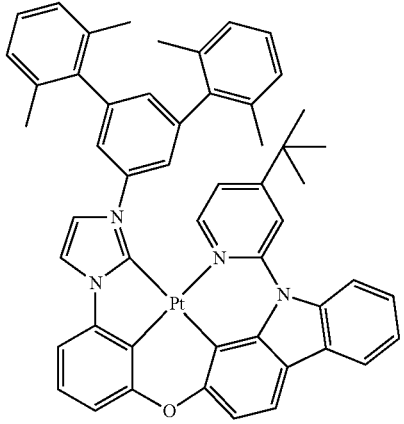
50
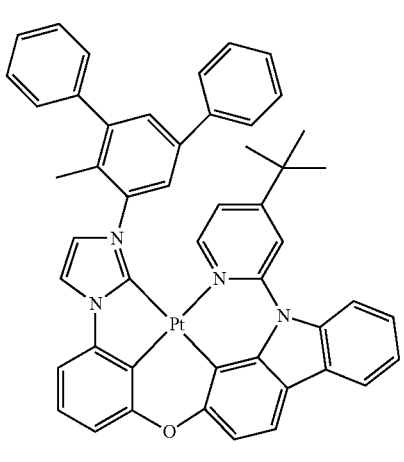

2639
-continued
52
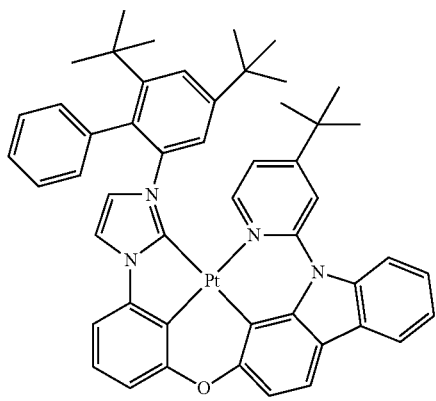
53
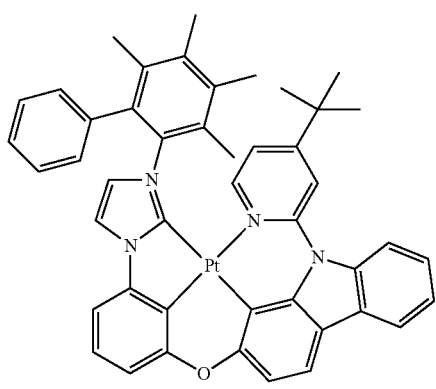
54
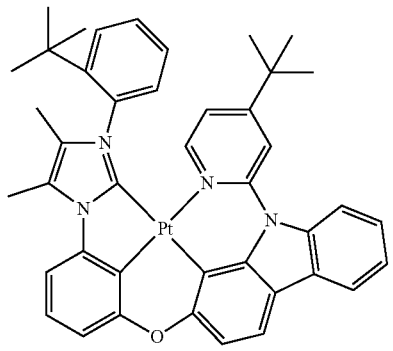
55
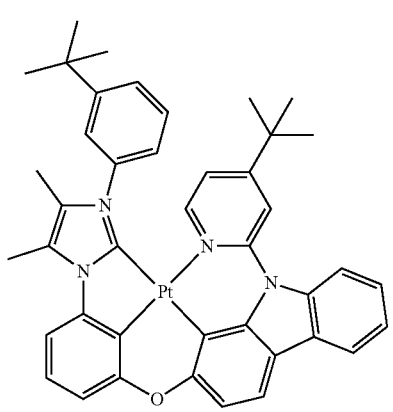
2640
-continued
56
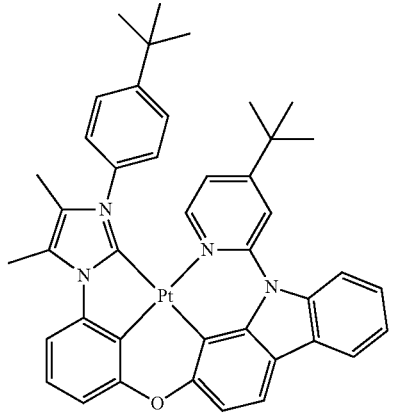
57
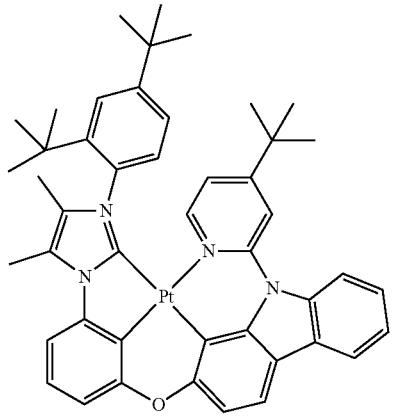
58
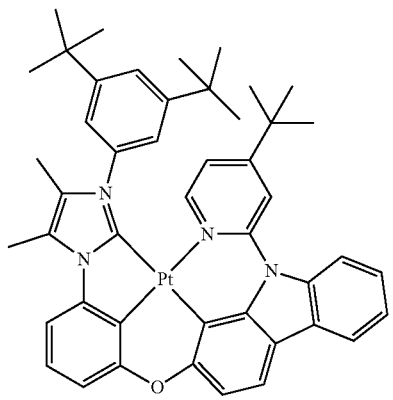
59
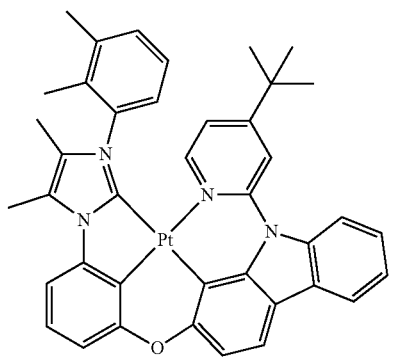

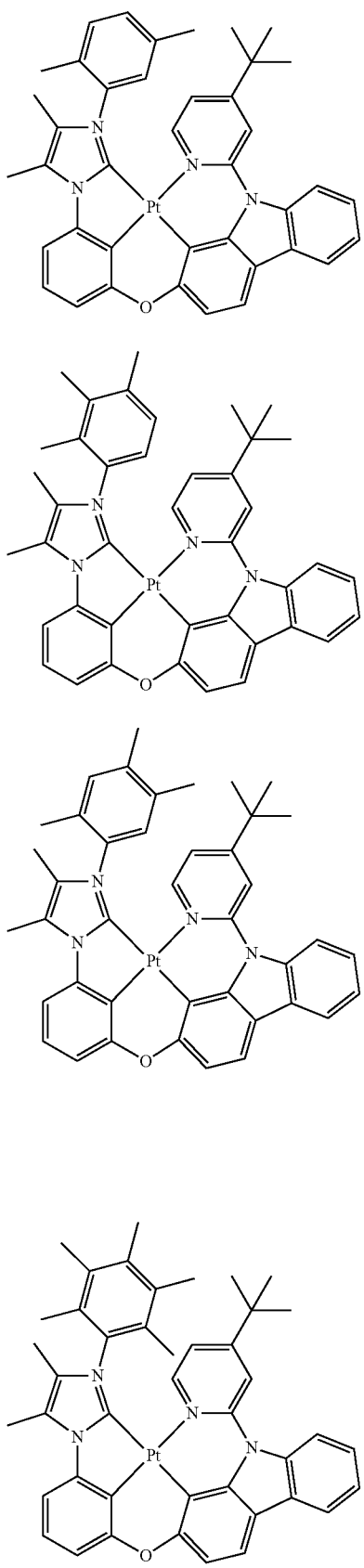
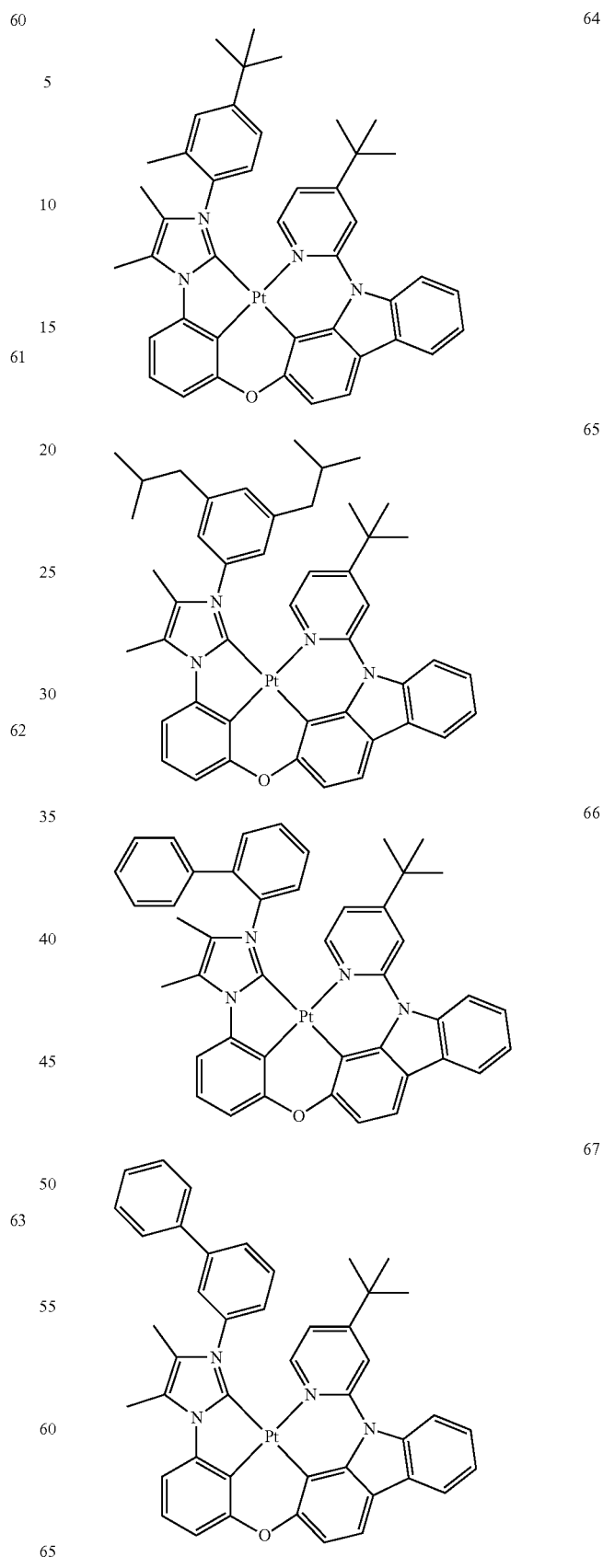

2643
-continued
68
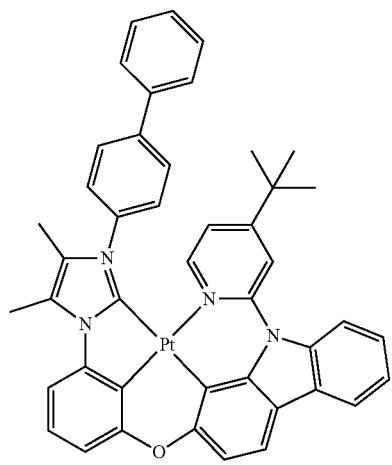
69
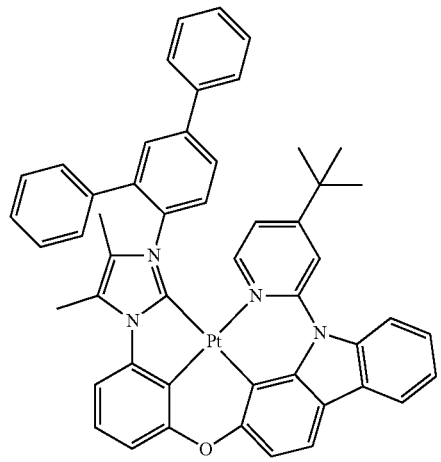
70
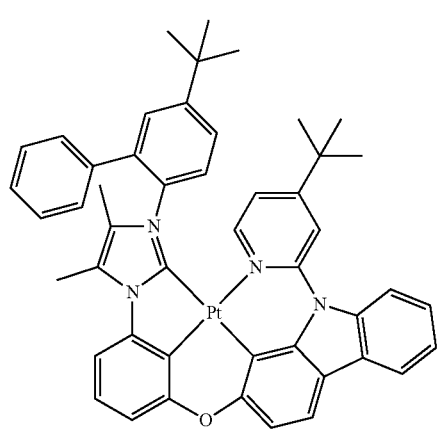
2644
-continued
71
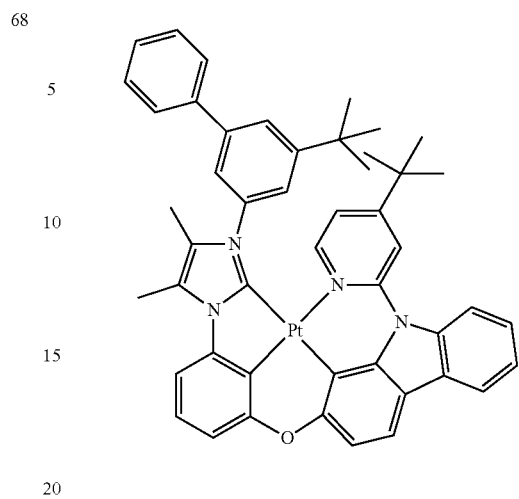
72
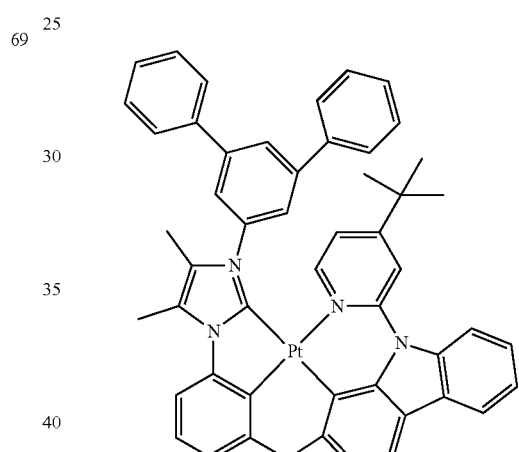
73
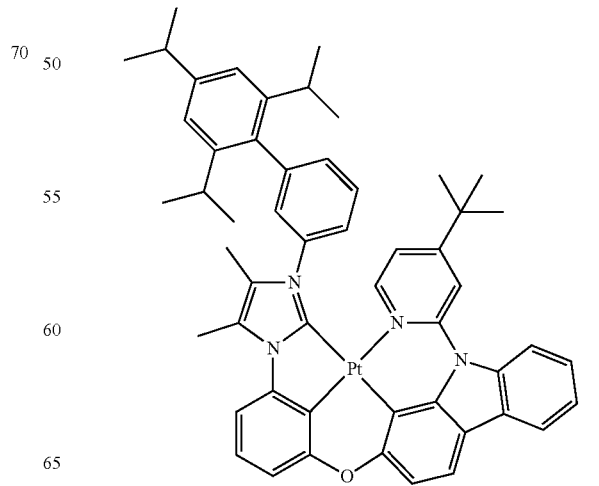

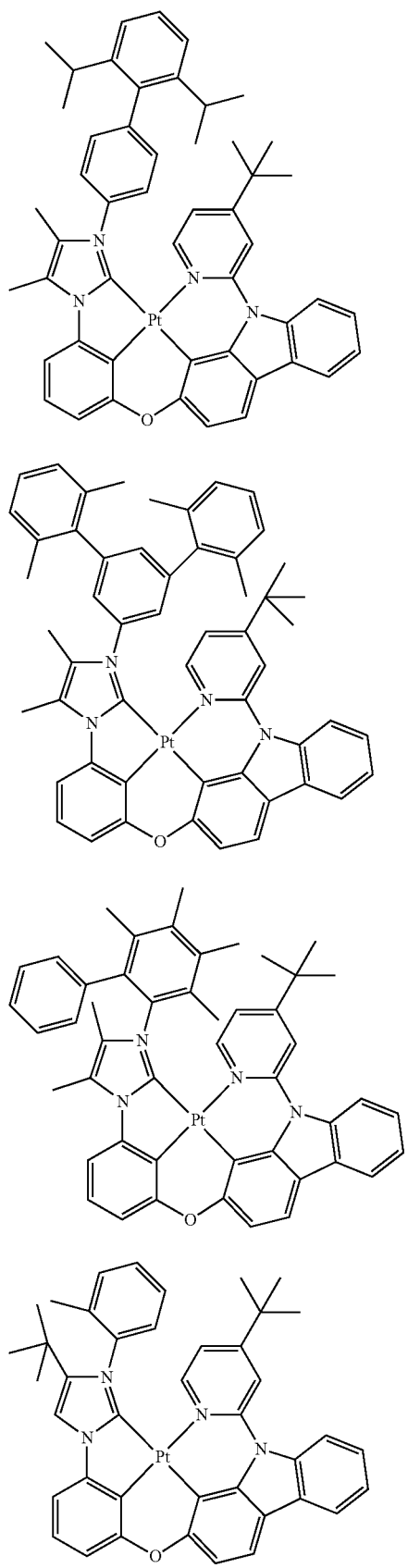
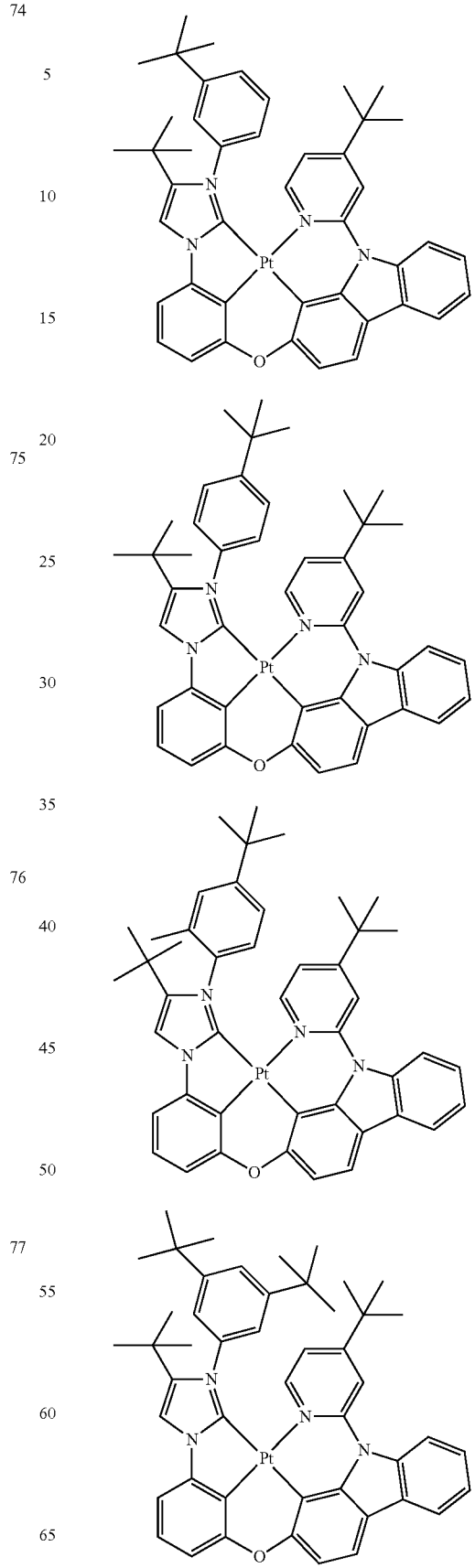

2647
-continued
82
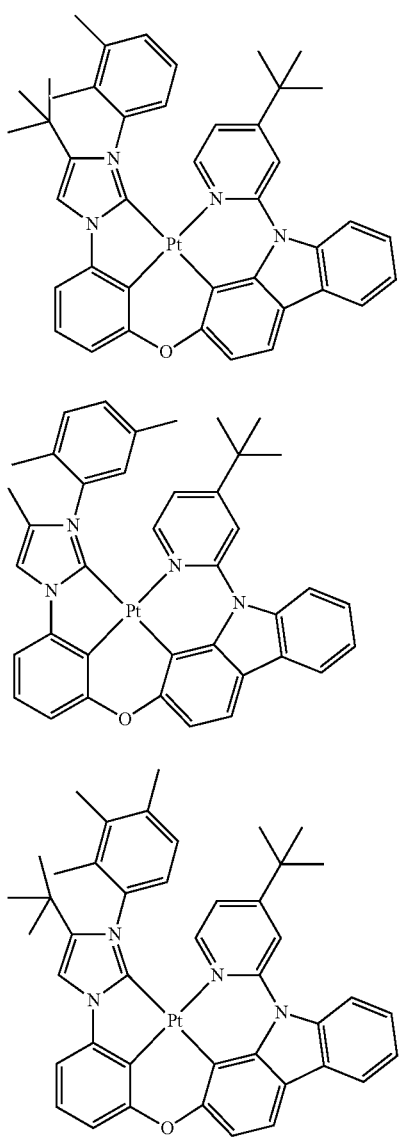
2648
-continued
86
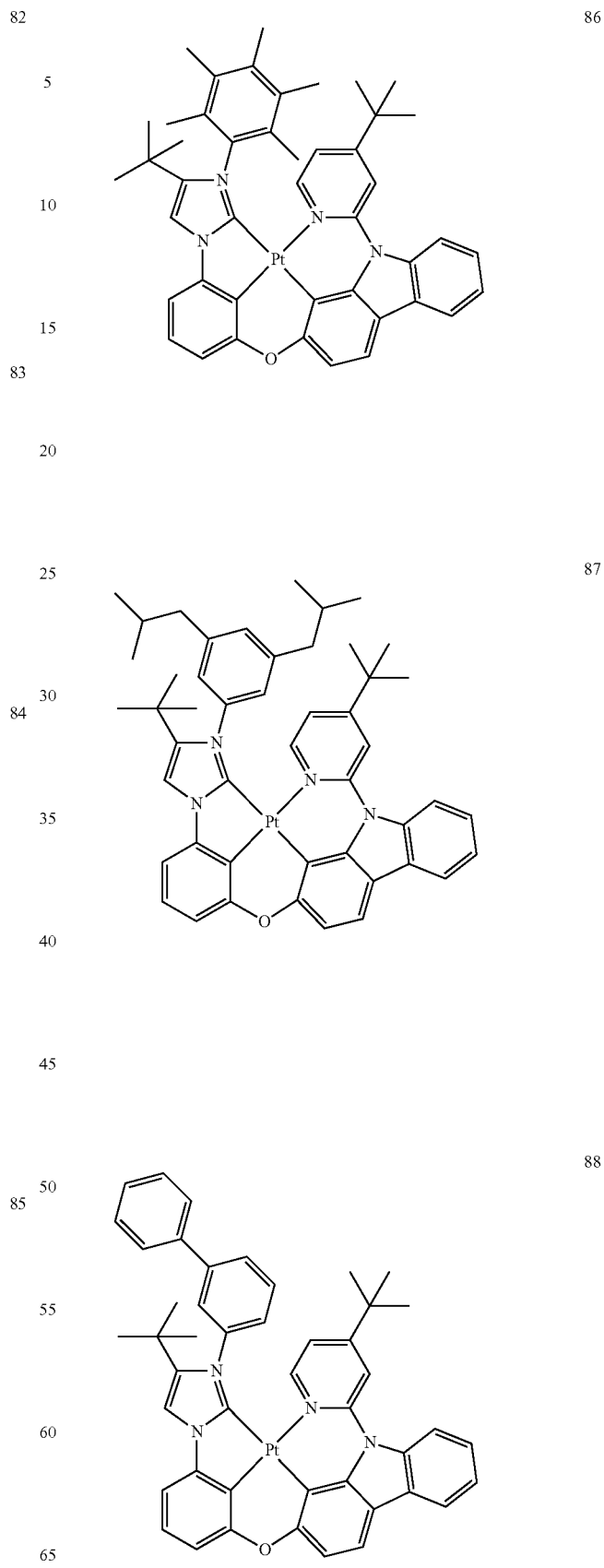

89
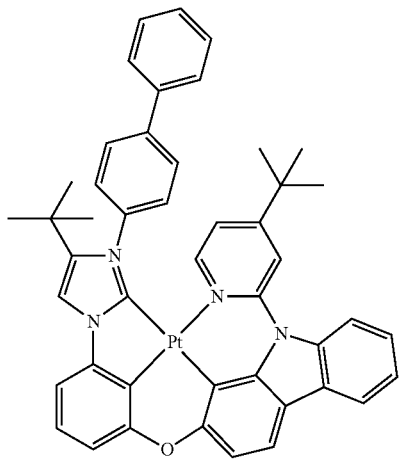
90
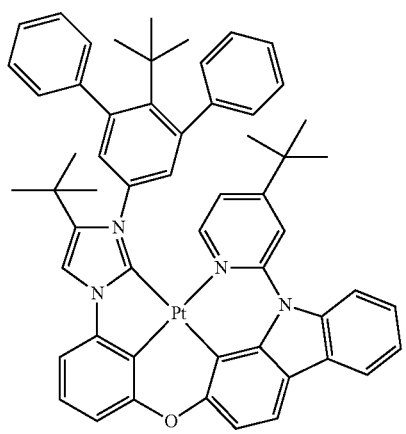
91
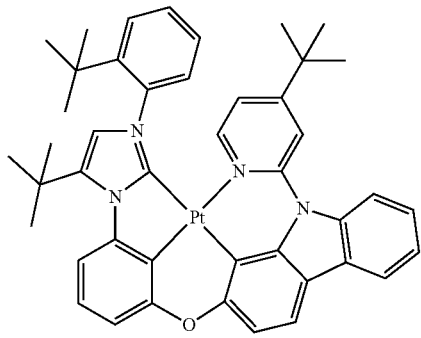
92
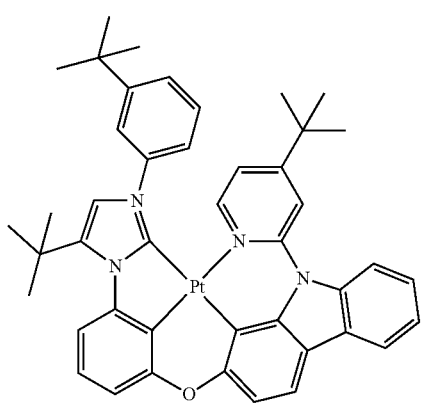
93
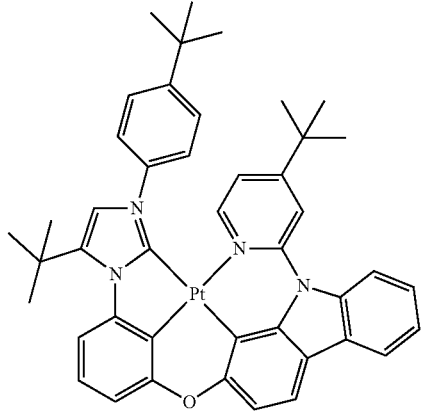
94

95
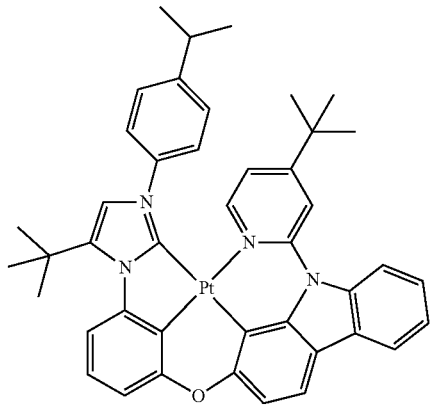
96
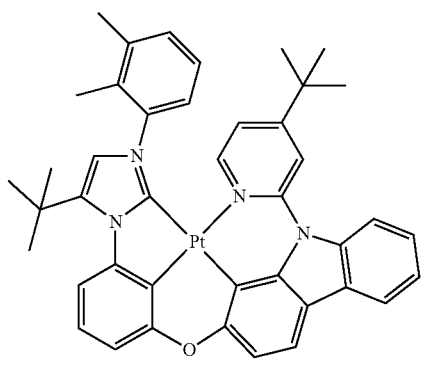

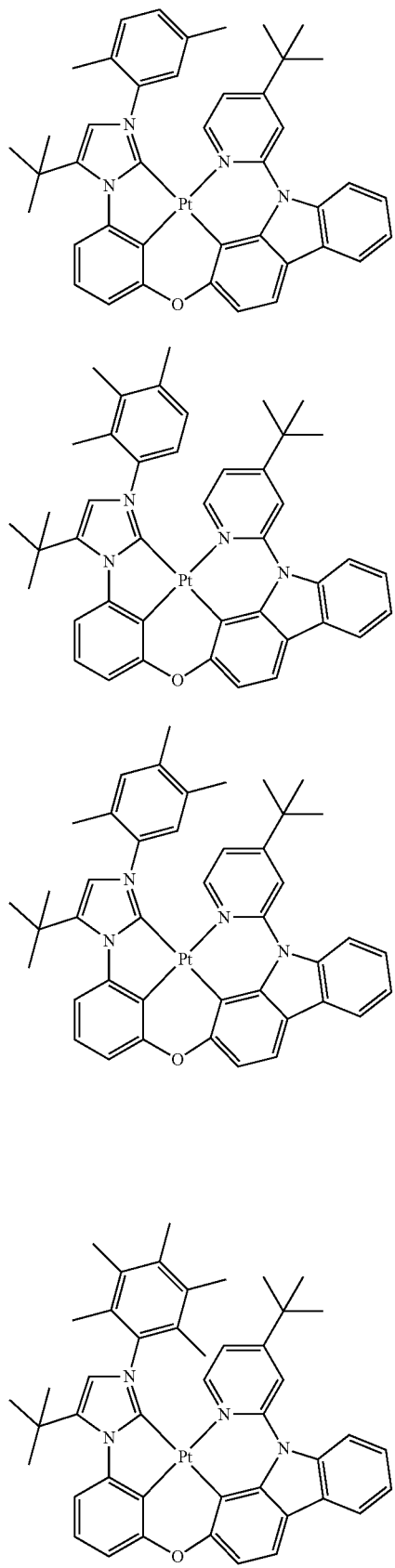
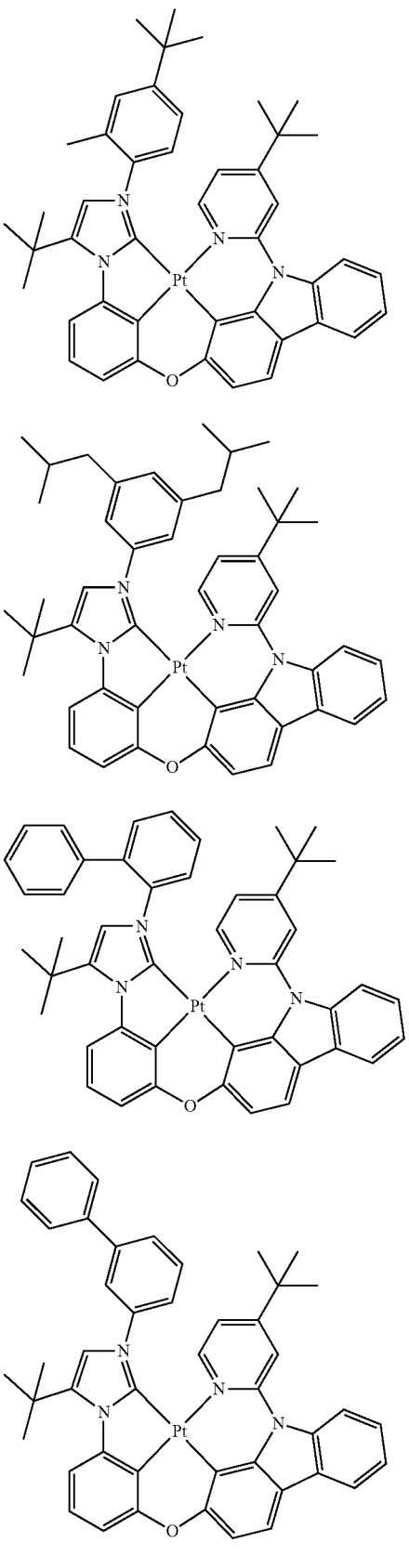

2653
-continued
105
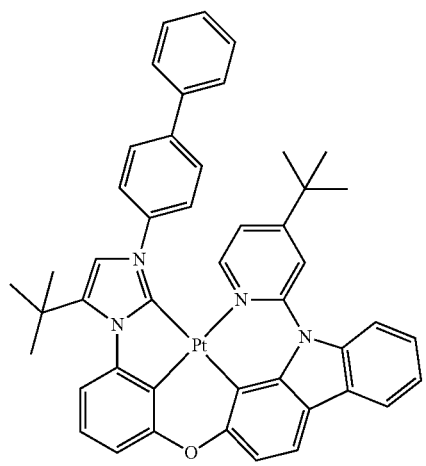
106
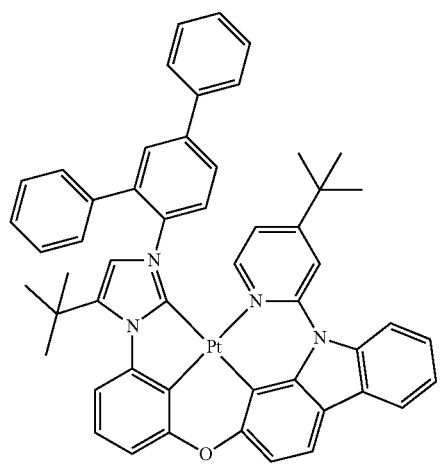
107
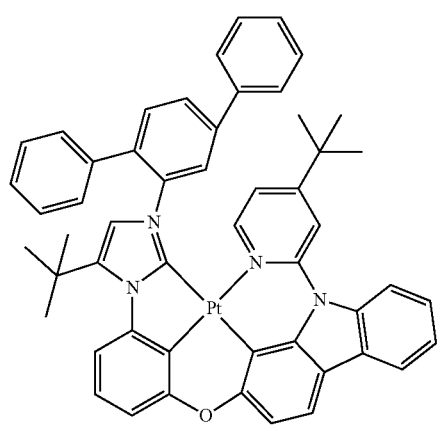
2654
-continued
108
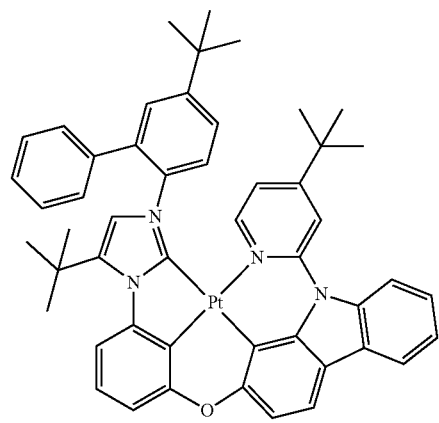
109
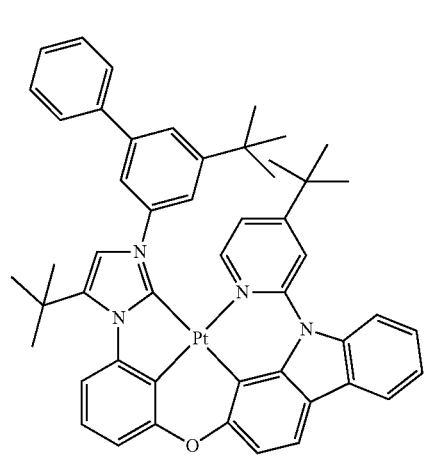
110
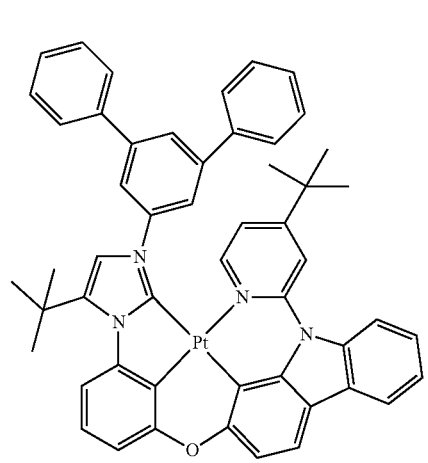

2655
-continued
111
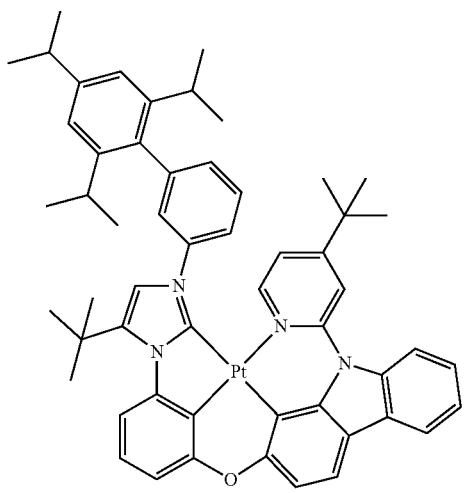
112
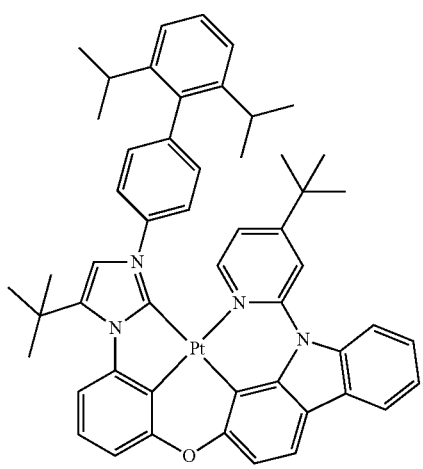
113
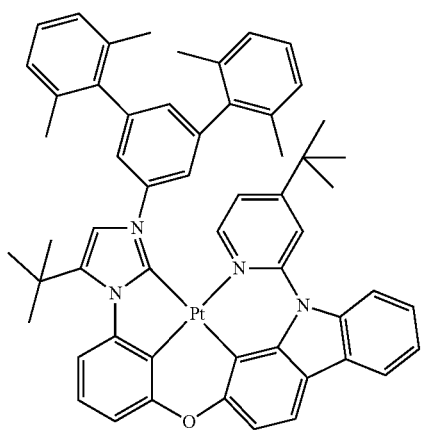
2656
-continued
114
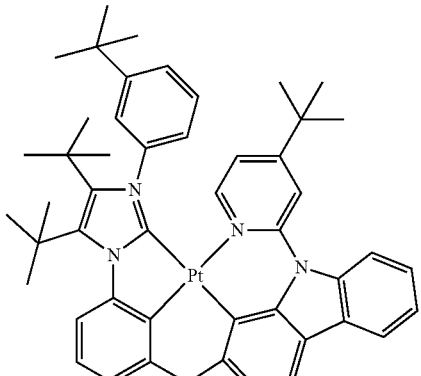
115
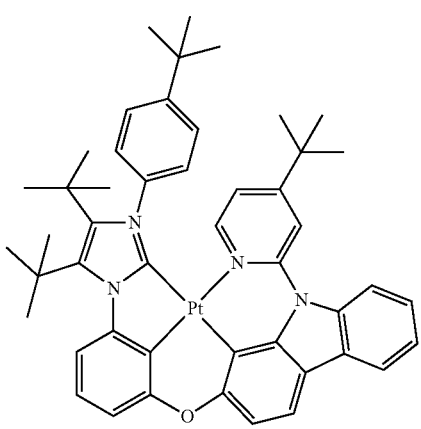
116
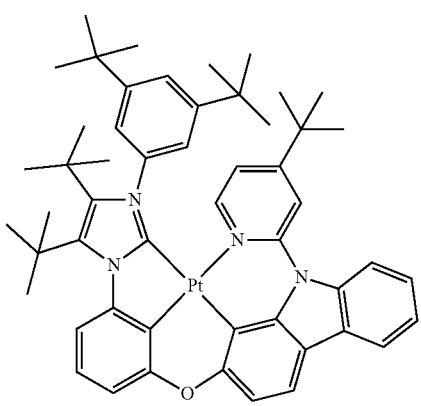
117
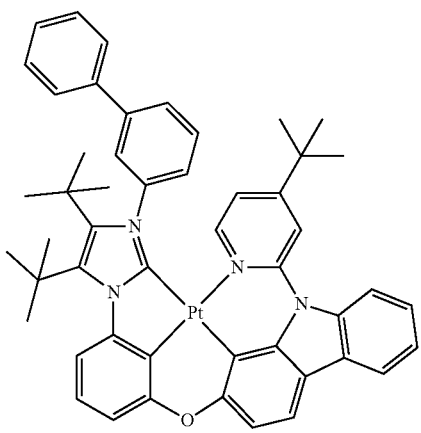

2657
-continued
118
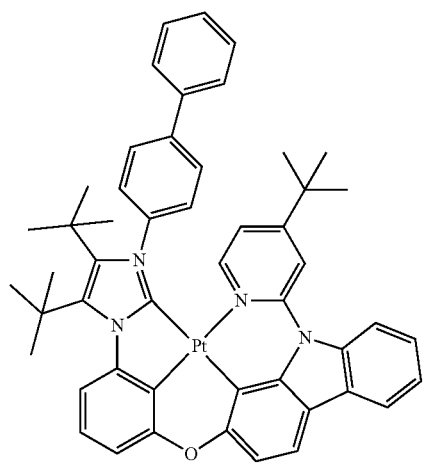
119
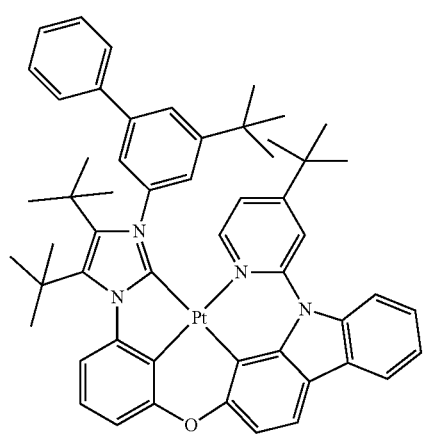
120
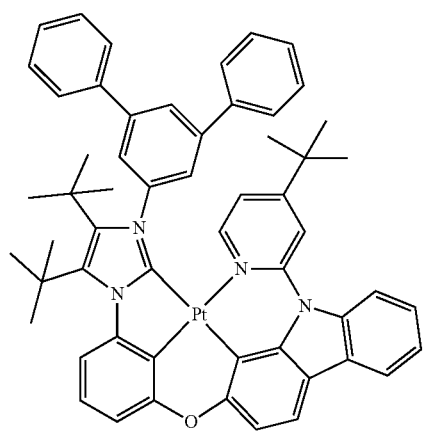
2658
-continued
121
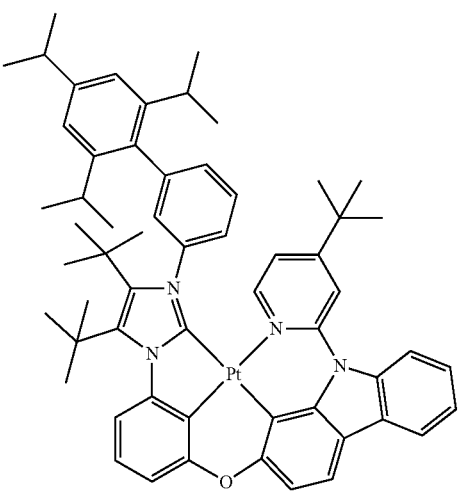
122
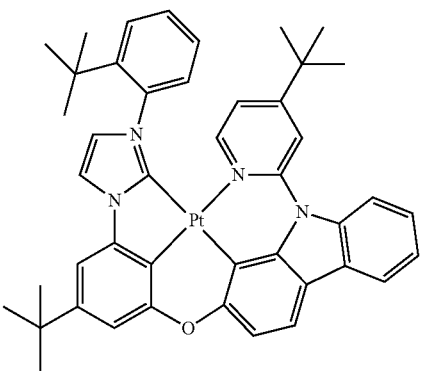
123
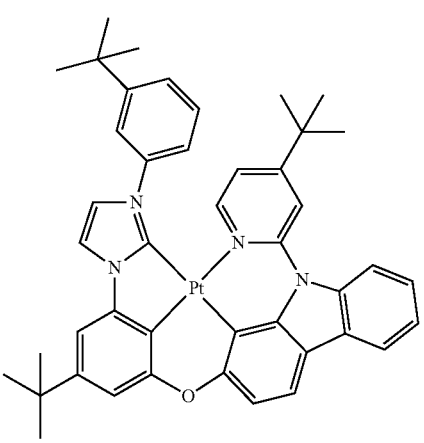

2659
-continued
124
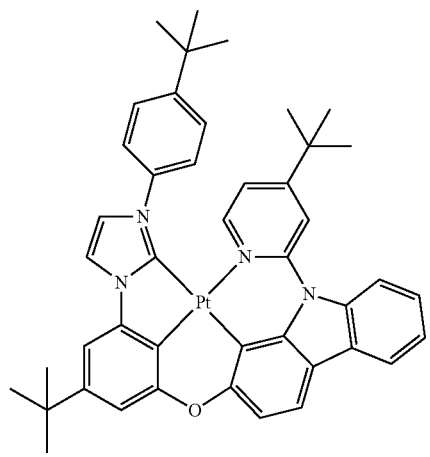
125
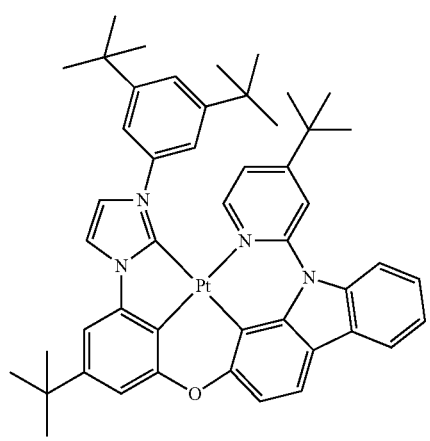
126
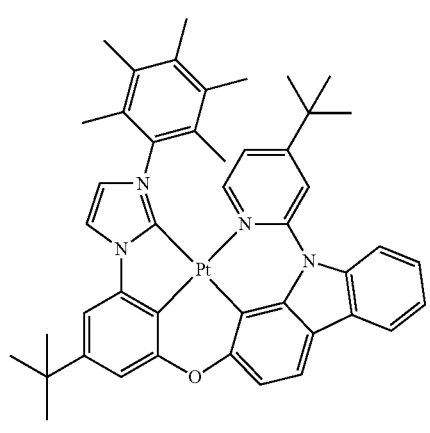
2660
-continued
127
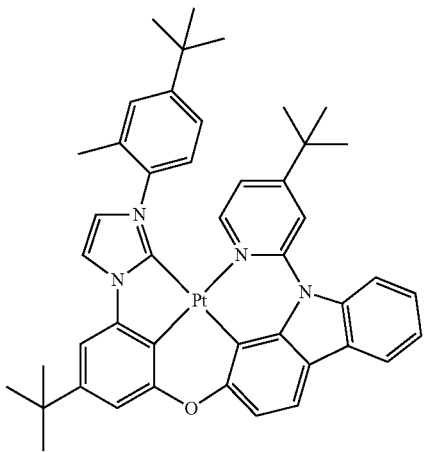
128
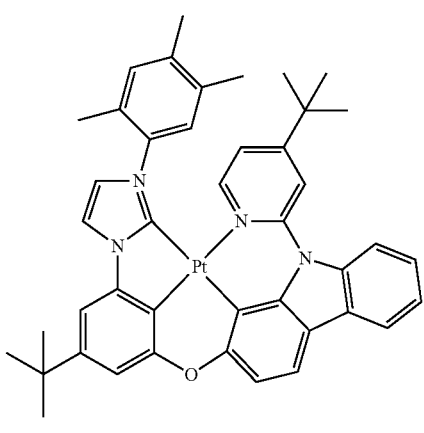
129
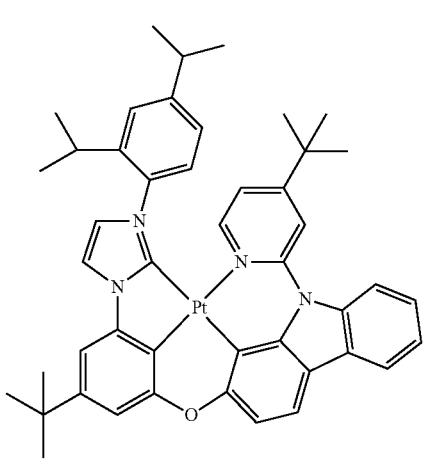

2661
-continued
130
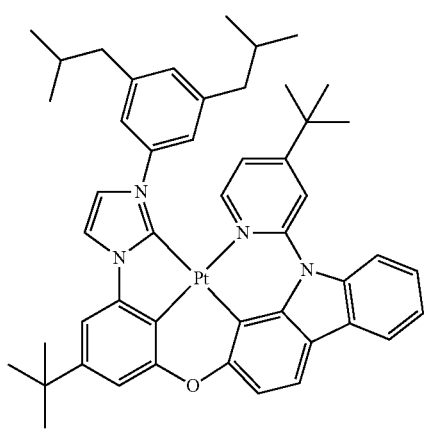
131
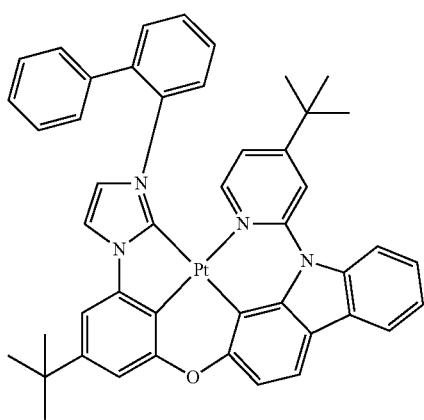
132
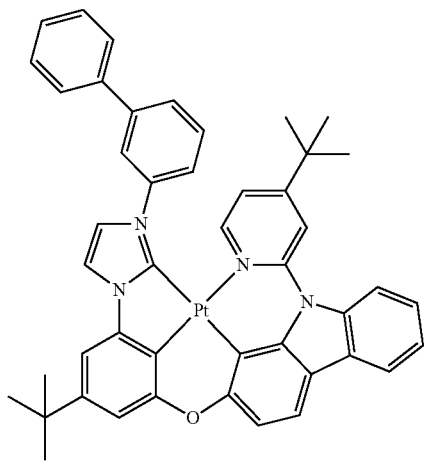
2662
-continued
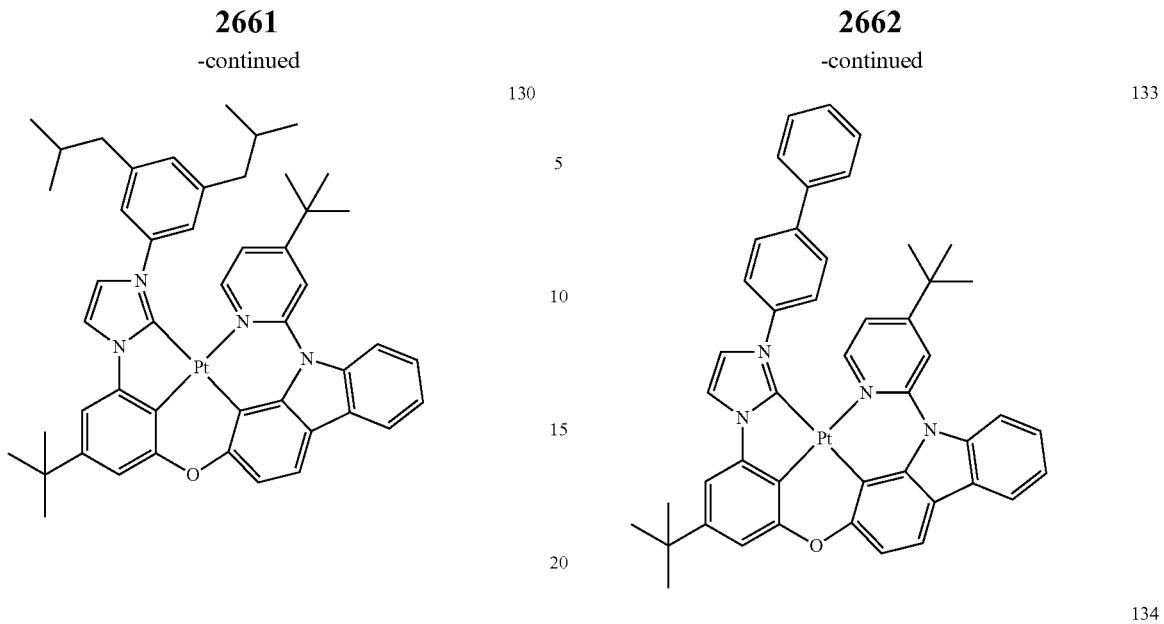
133
134
135

2663
-continued
136
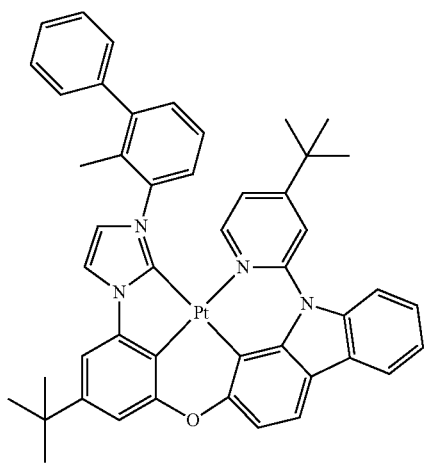
137
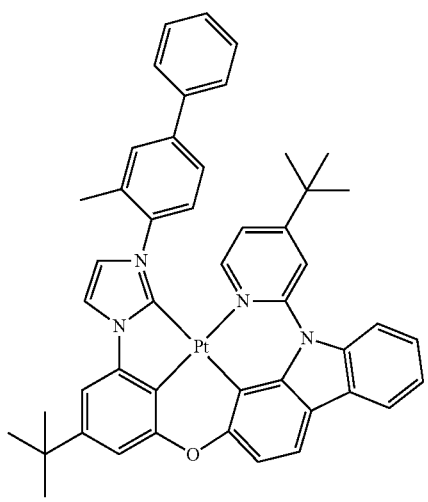
138
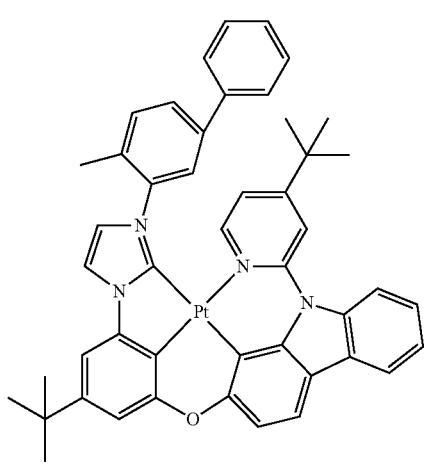
2664
-continued
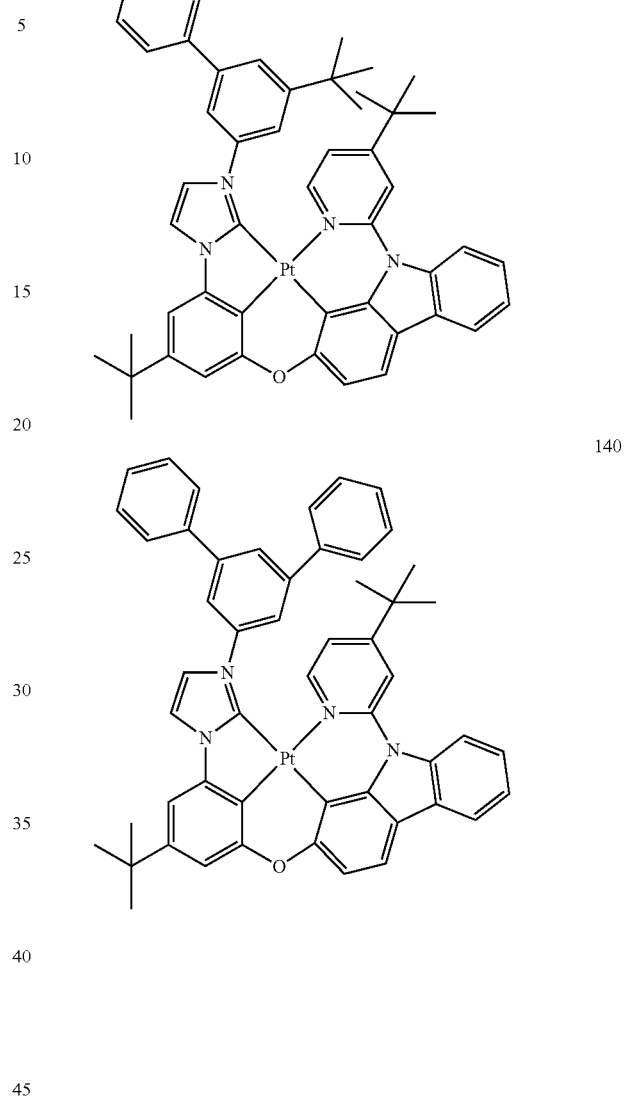
139
140
141
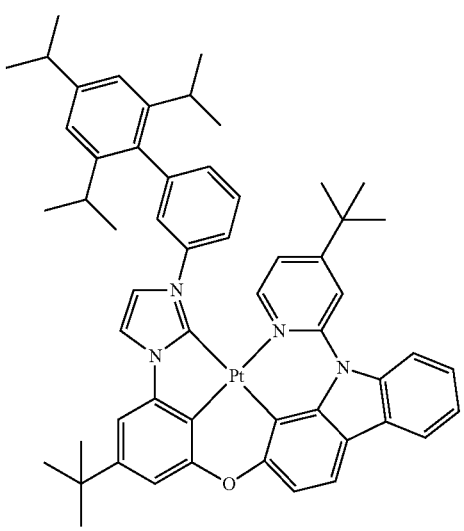

2665
-continued
142
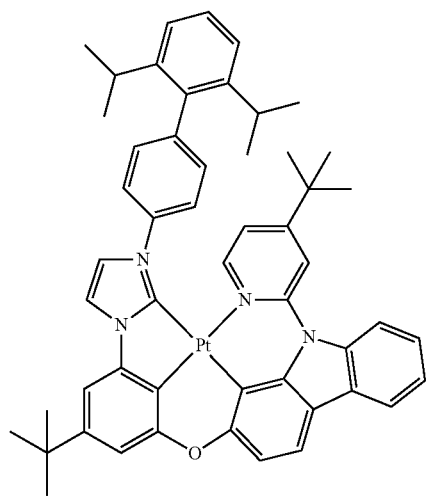
143
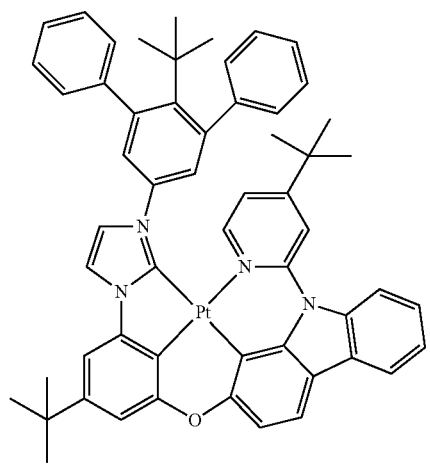
144
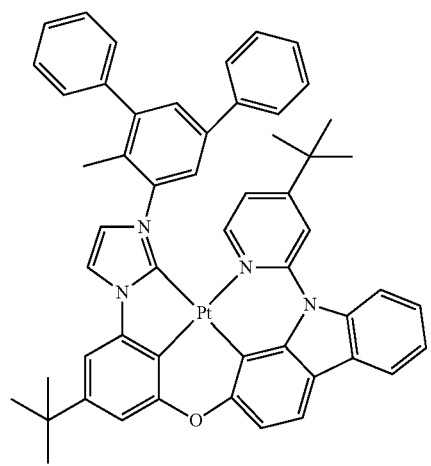
2666
-continued
145
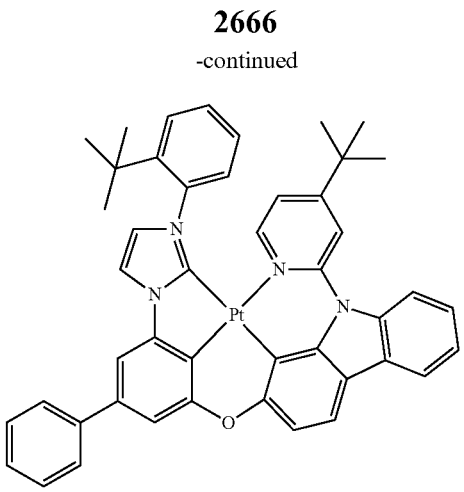
146
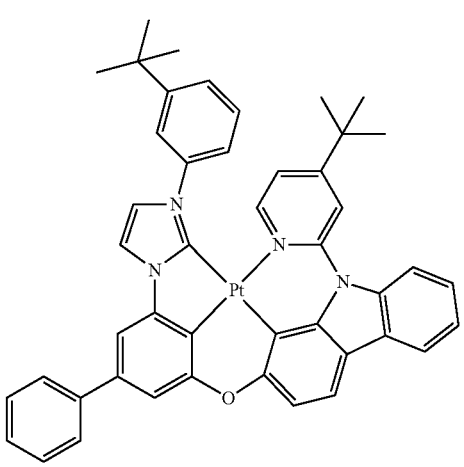
147
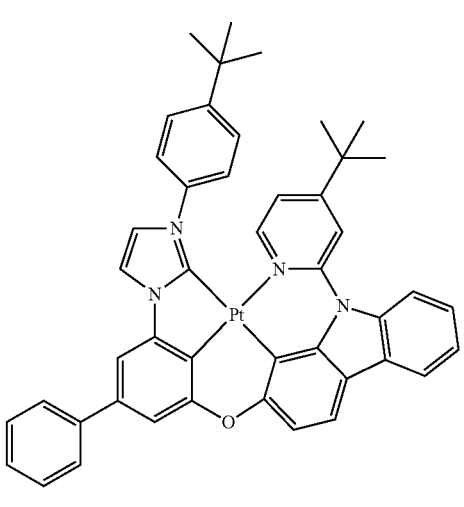

2667
-continued
148
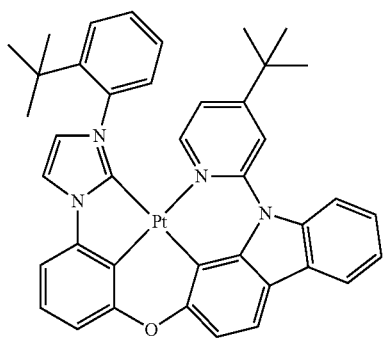
149
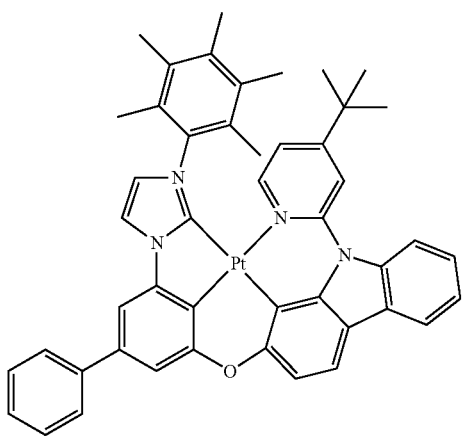
150
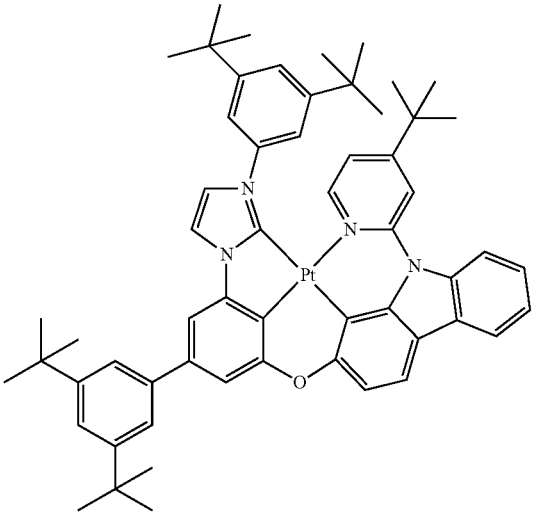
2668
-continued
151
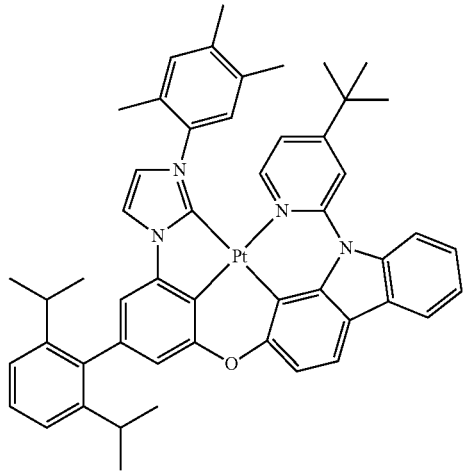
152
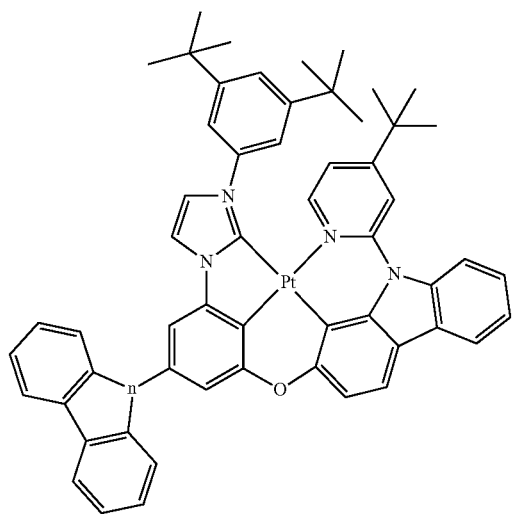
153
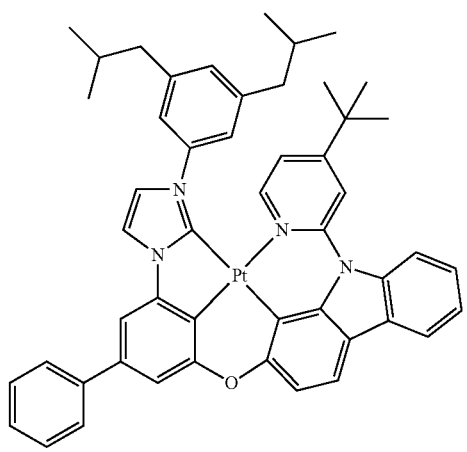

2669
-continued
154
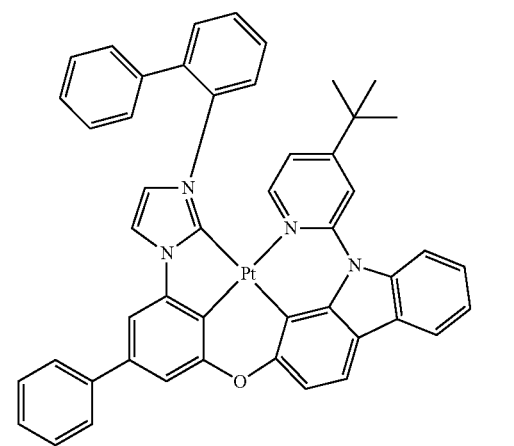
155
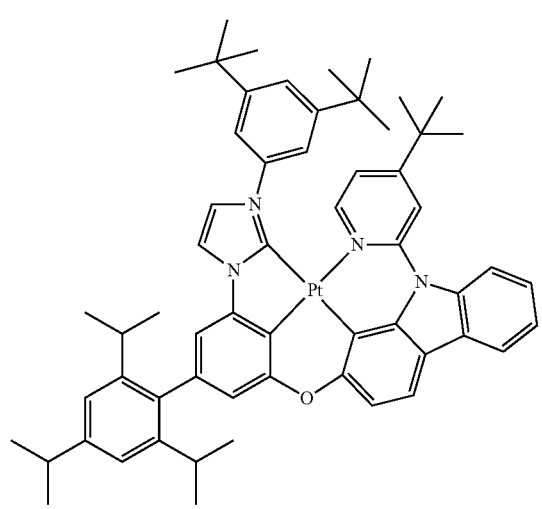
156
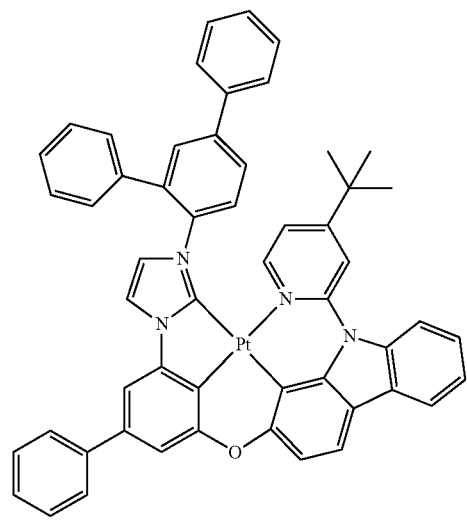
2670
-continued
157
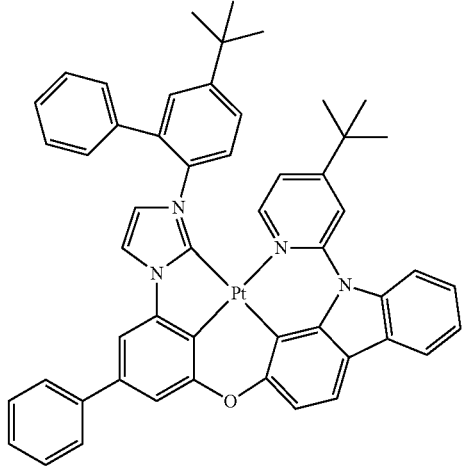
158
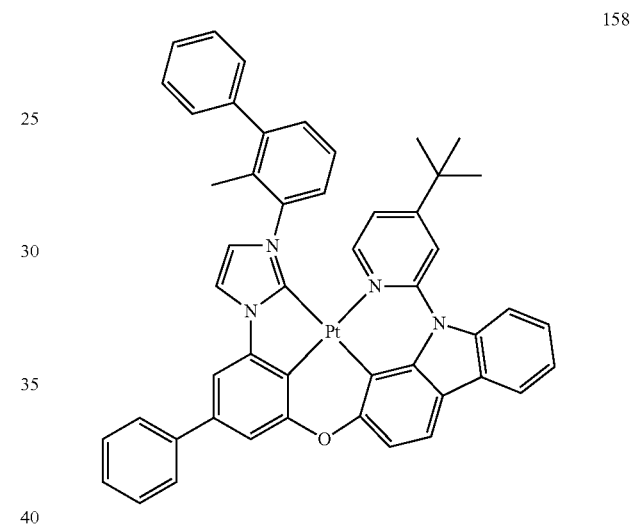
159
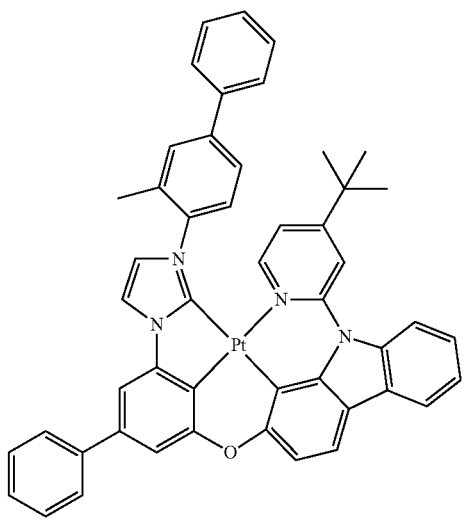

2671
-continued
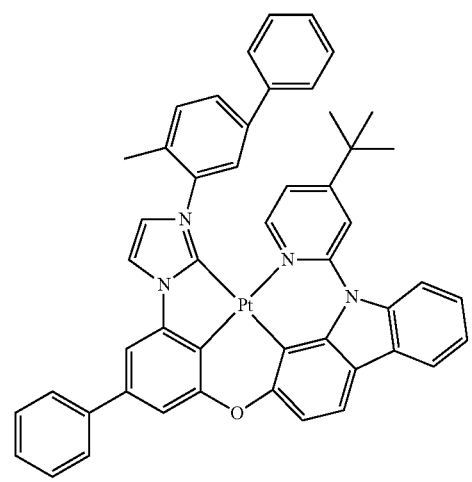
160
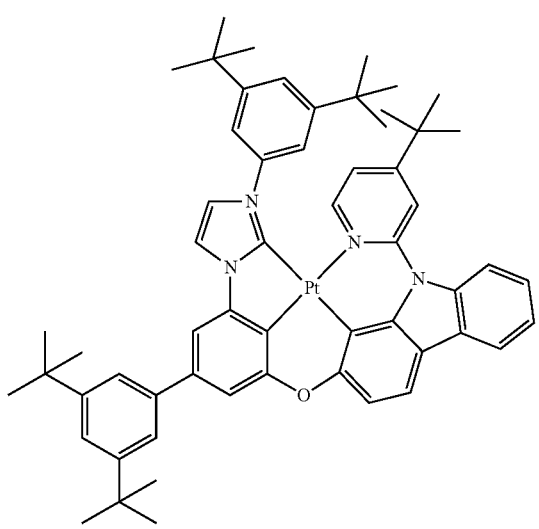
161
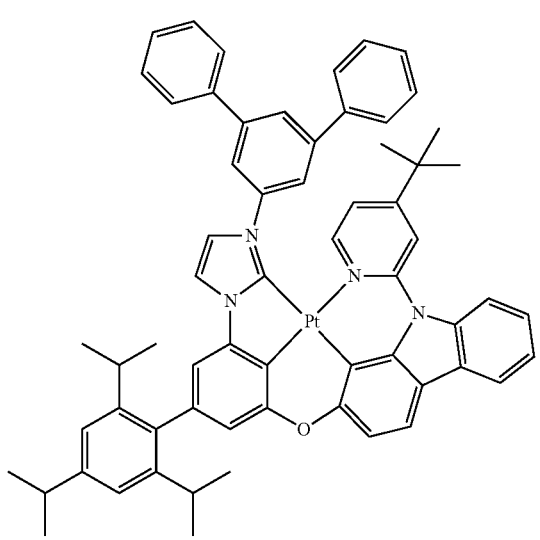
162
2672
-continued
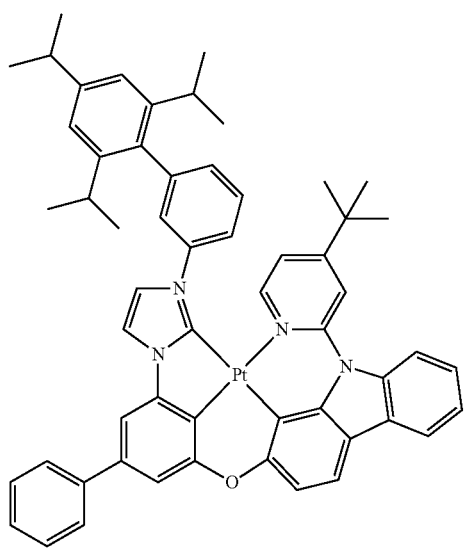
163
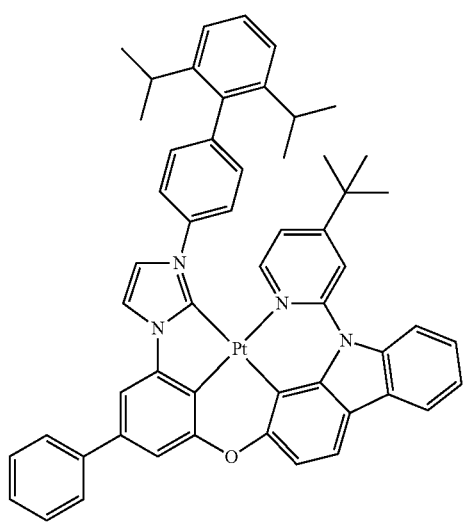
164
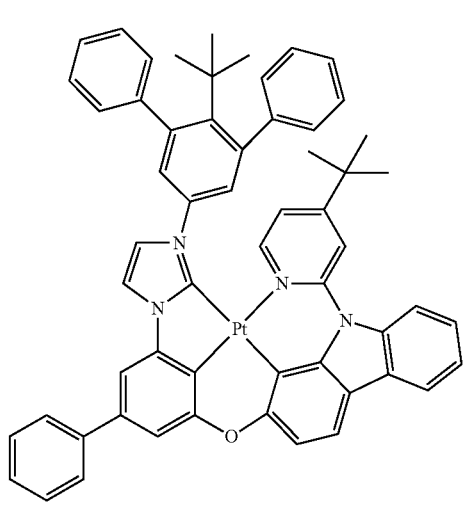
165

2673
-continued
166
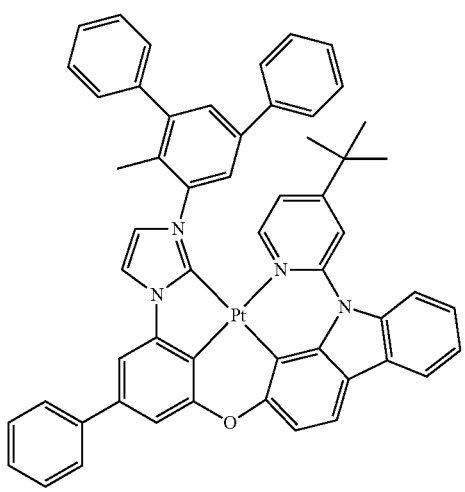
167
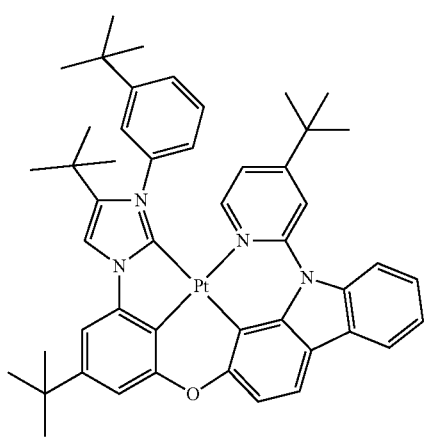
168
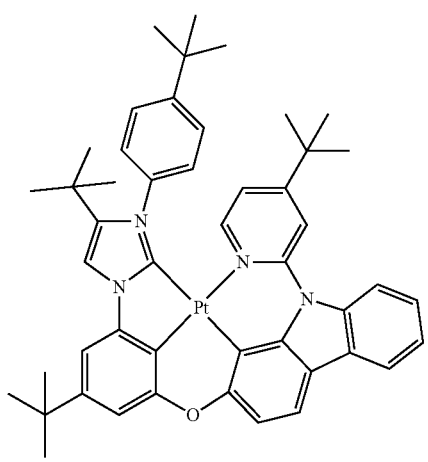
2674
-continued
169
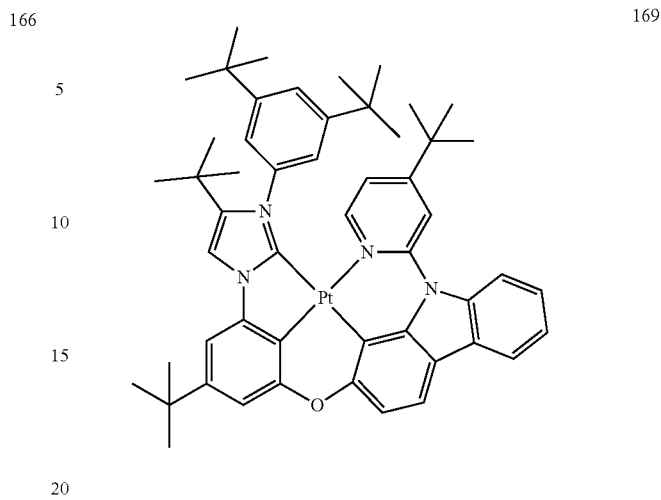
170
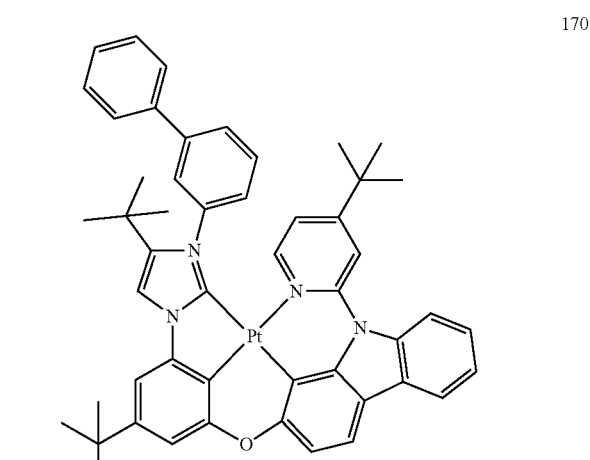
171
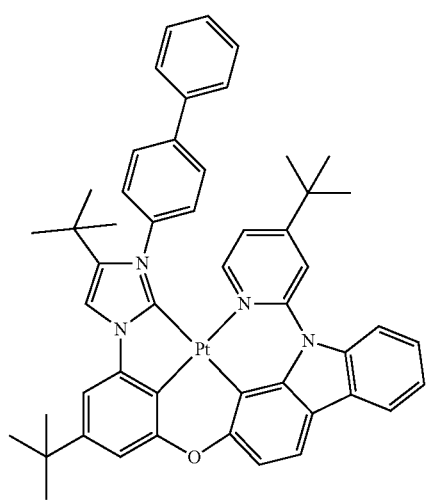

2675
-continued
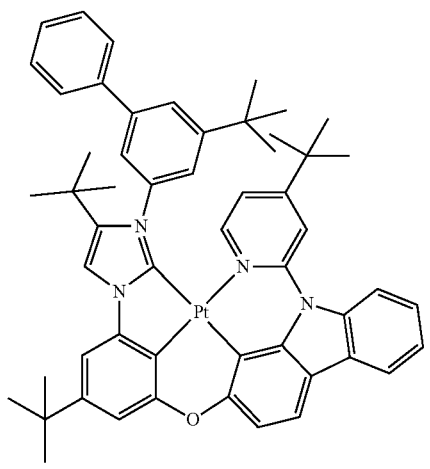
172
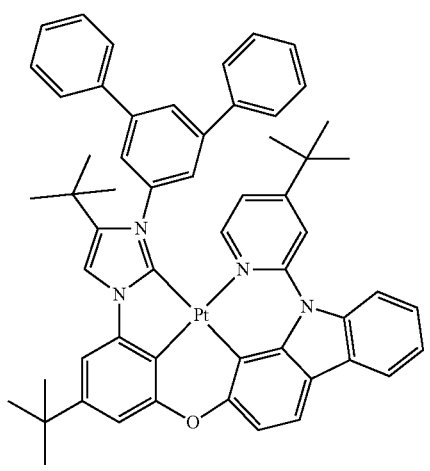
173
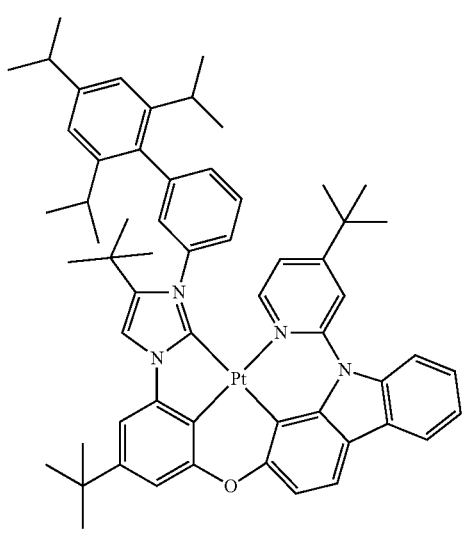
174
2676
-continued
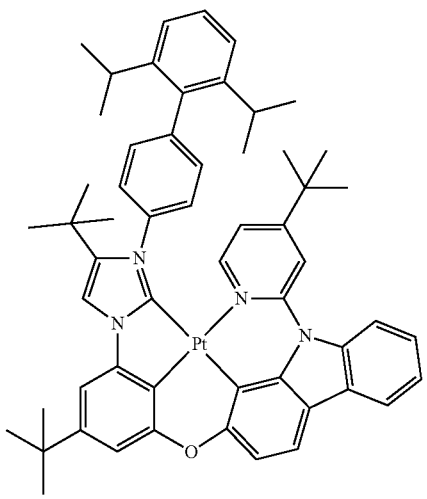
175
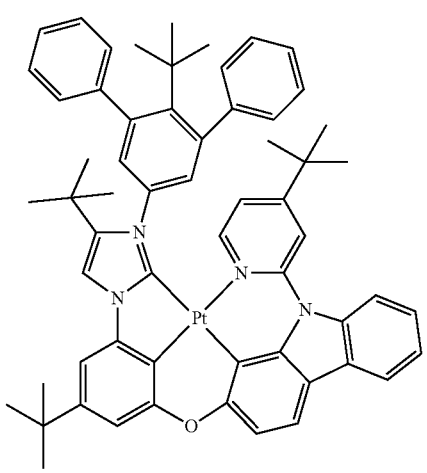
176
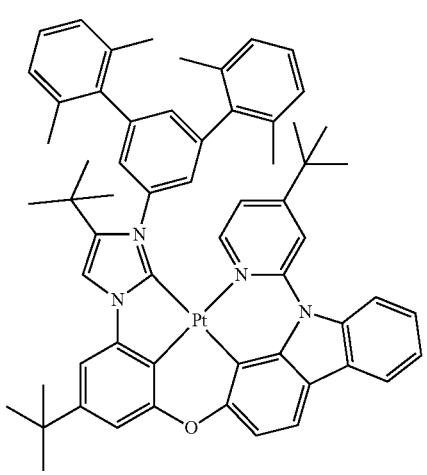
177

2677
-continued
178
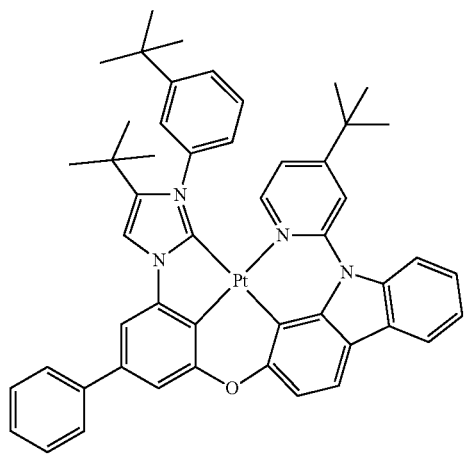
179
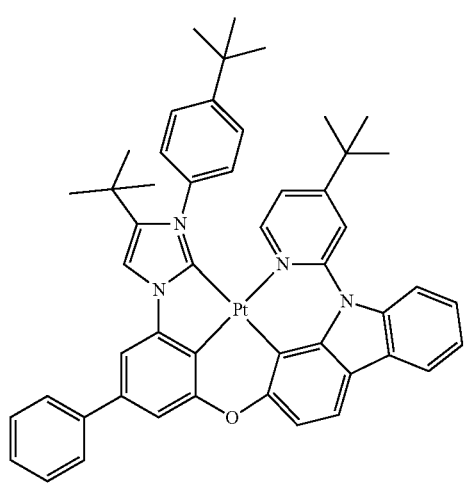
180
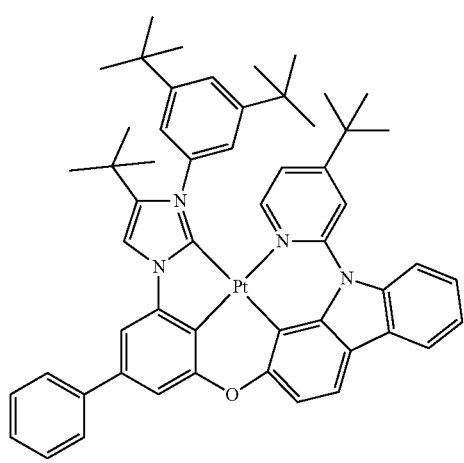
2678
-continued
181
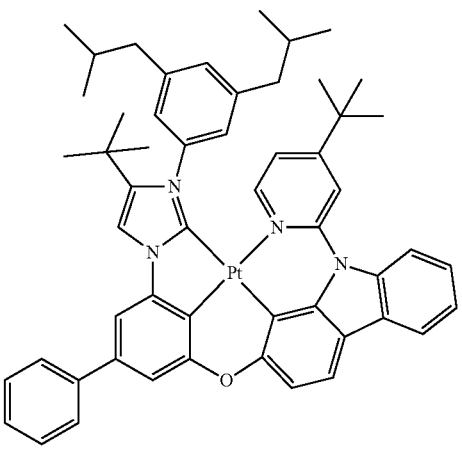
182
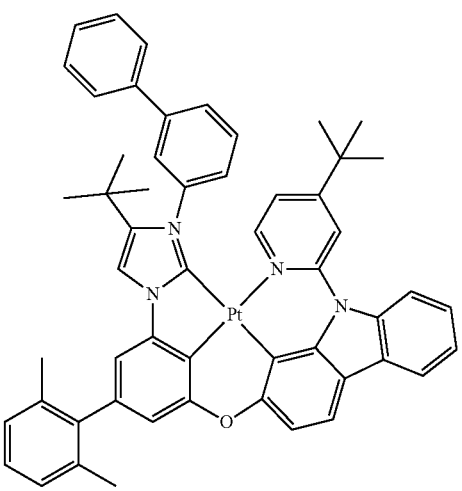
183
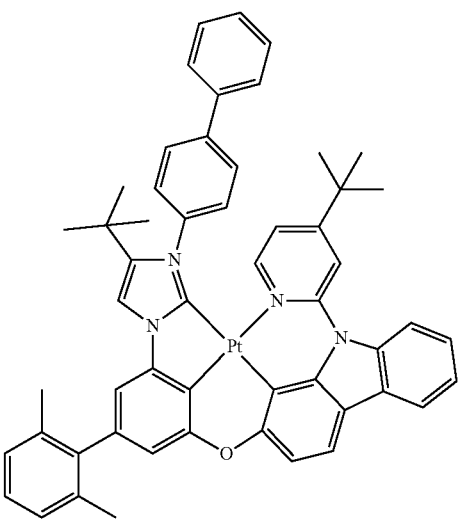

184
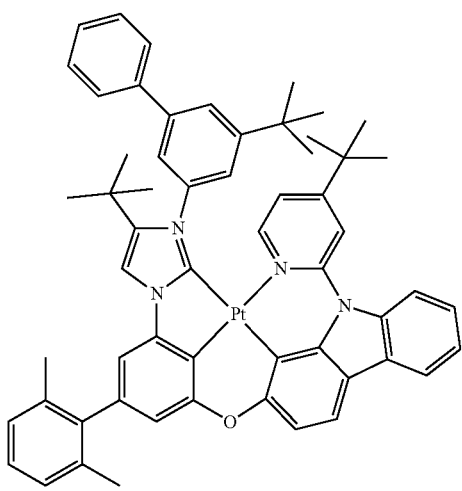
185
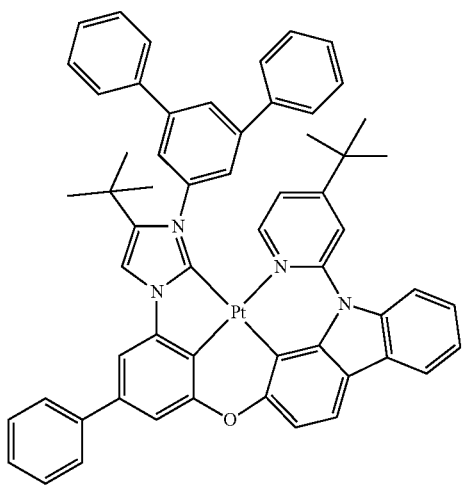
186
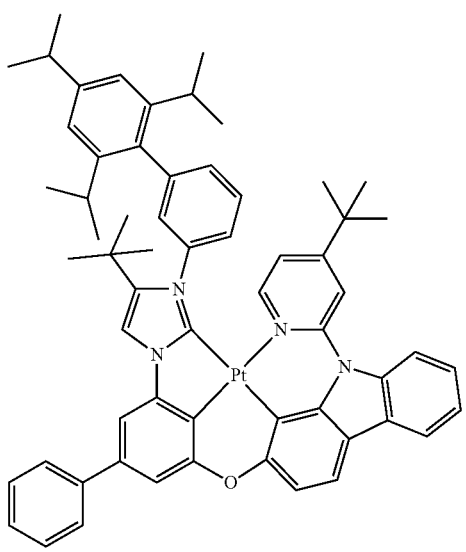
187
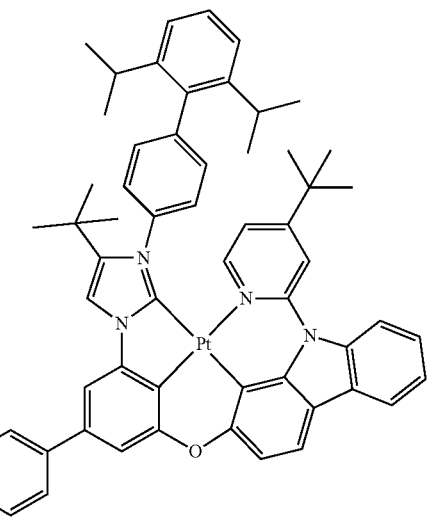
188
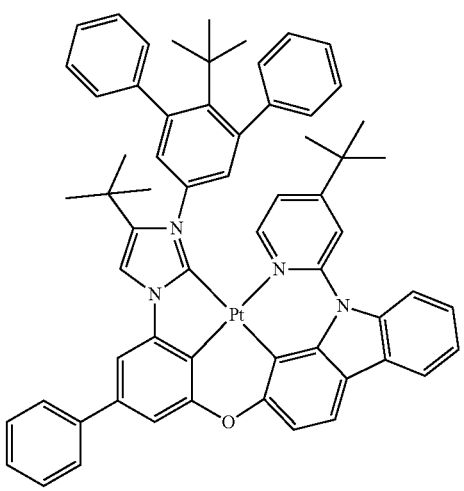
189
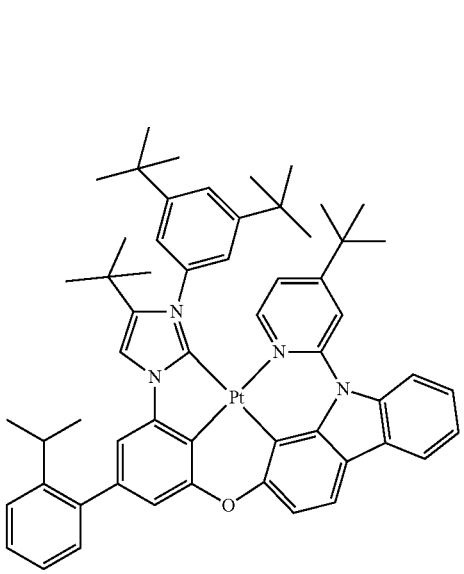

2681
-continued
190
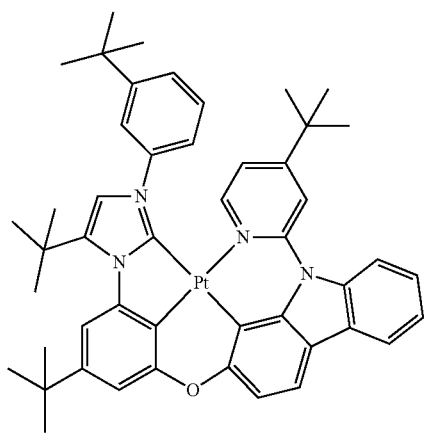
191
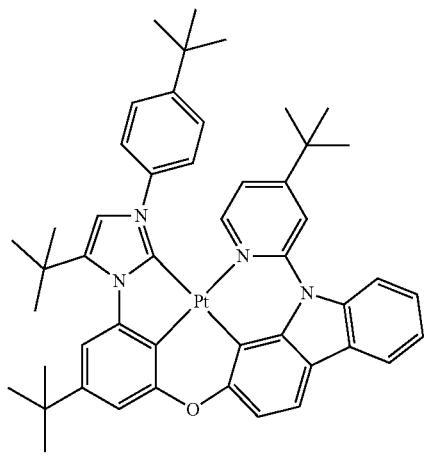
192
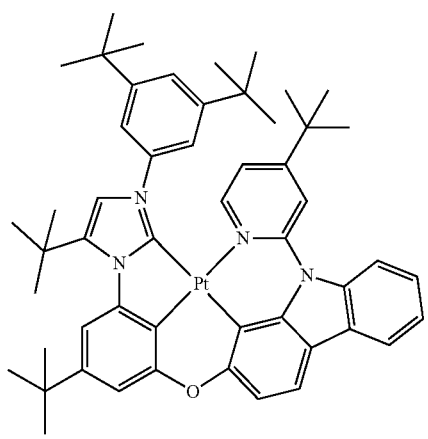
2682
-continued
193
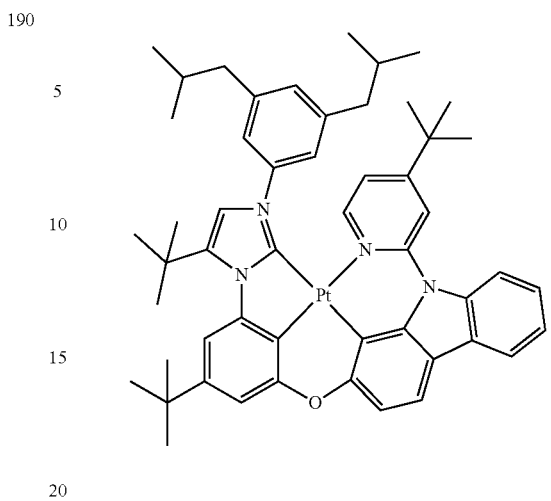
194
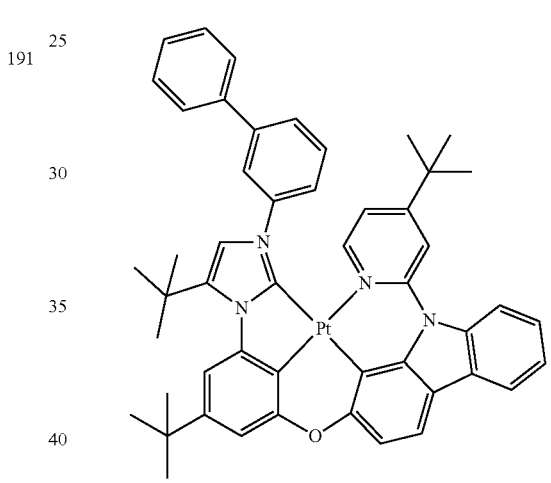
195
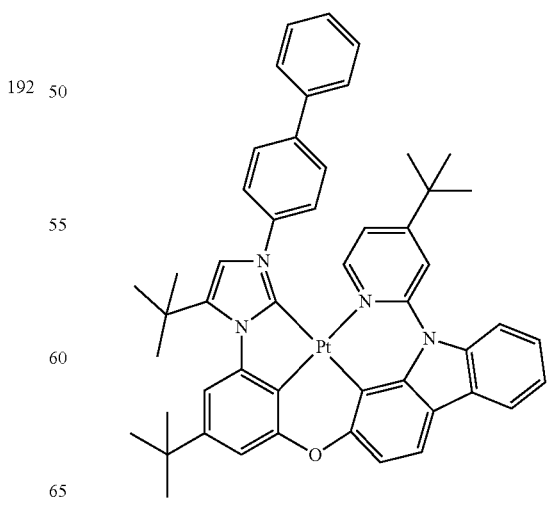

2683
-continued
196
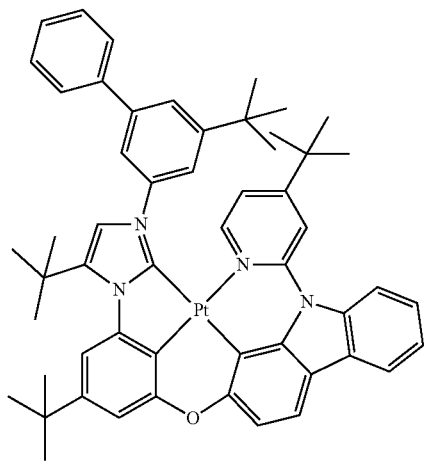
197
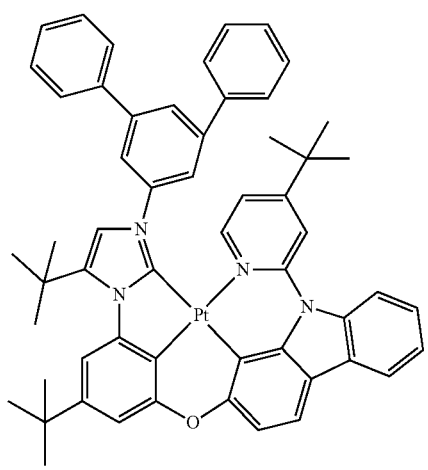
198
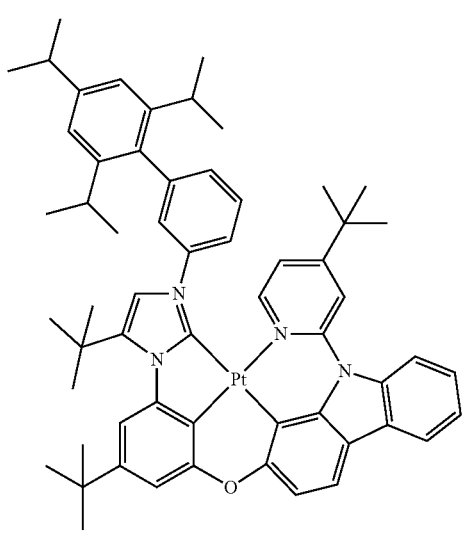
2684
-continued
199
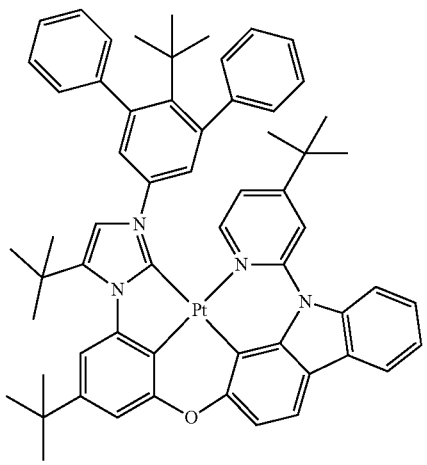
200
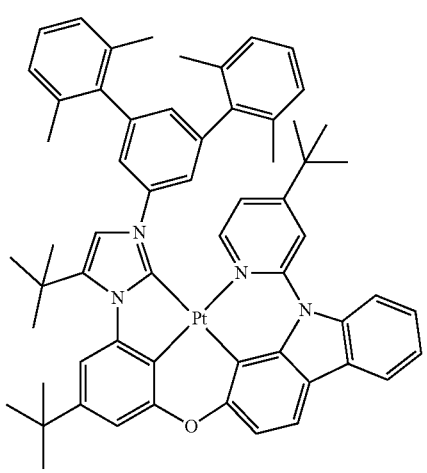
201
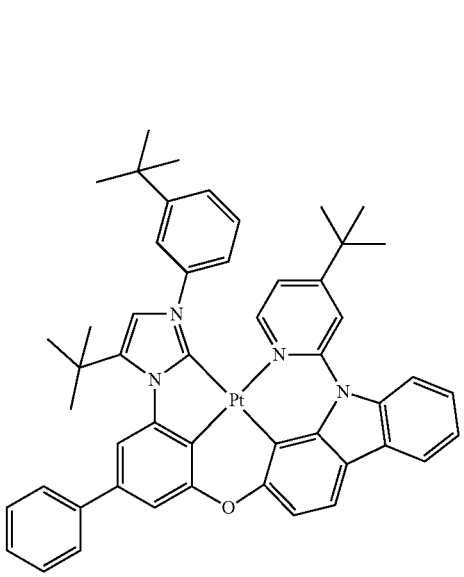

2685
-continued
202
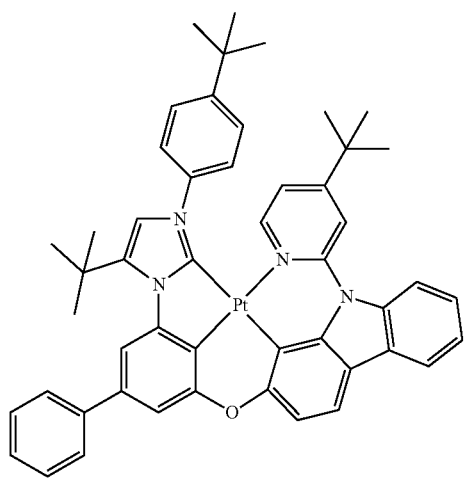
203
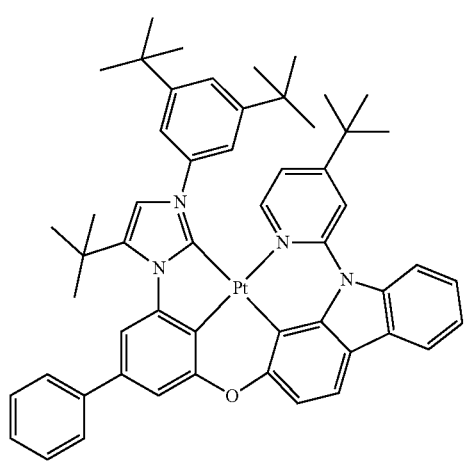
204
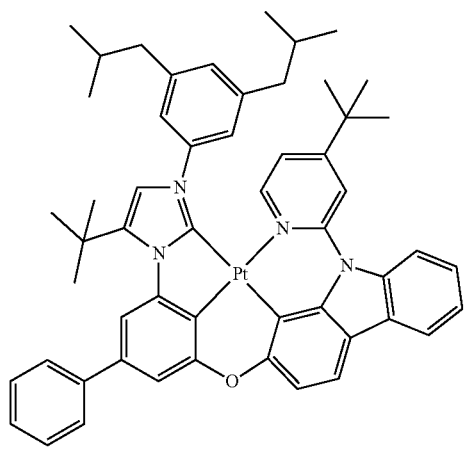
2686
-continued
205
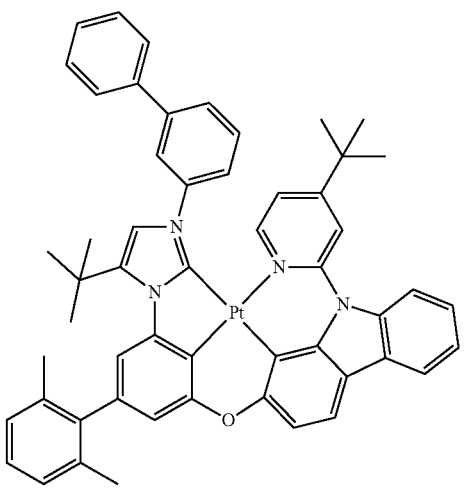
206
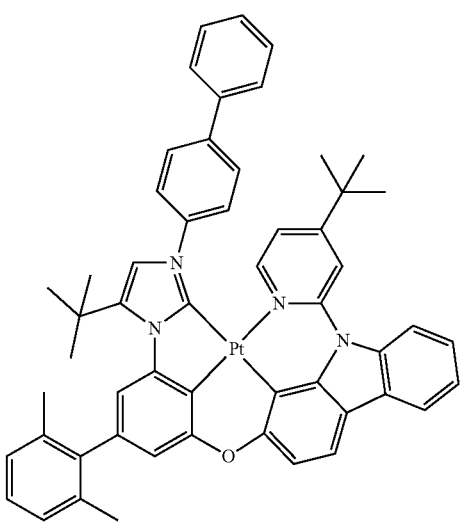
207
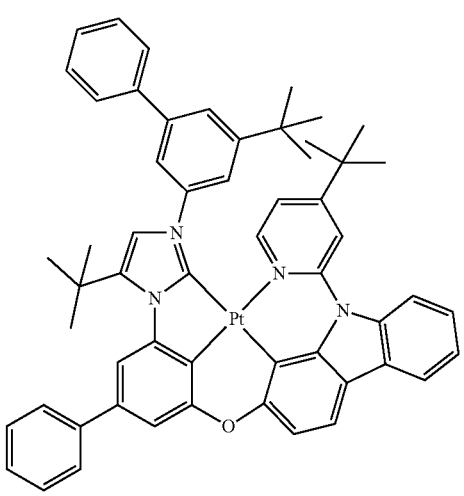

2687
-continued
208
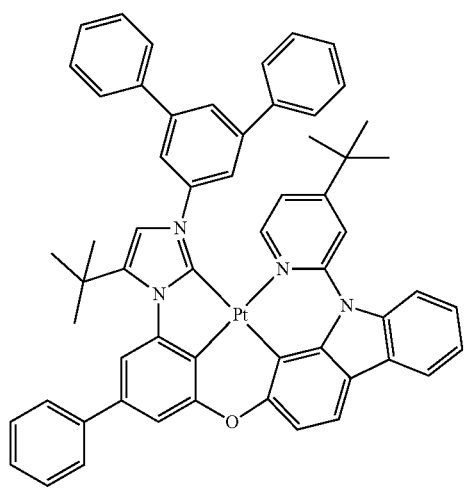
209
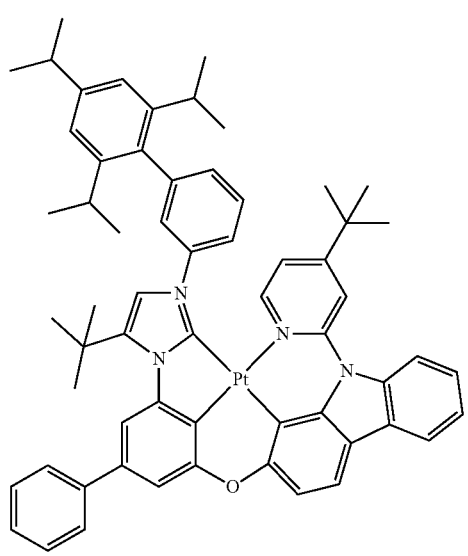
210
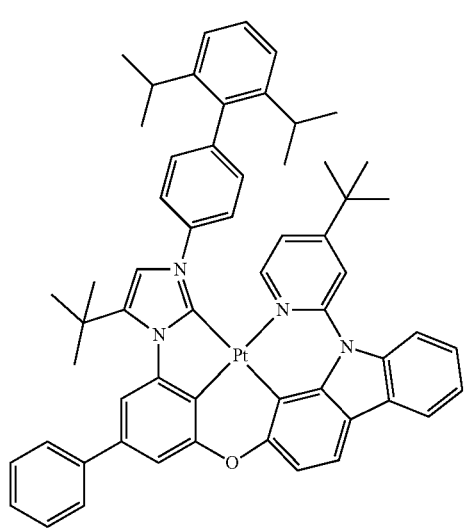
2688
-continued
211
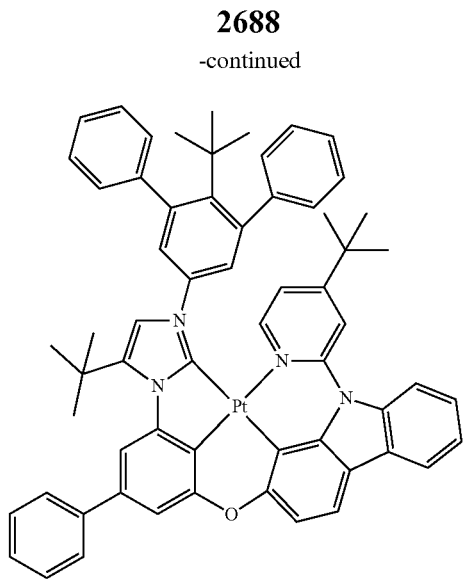
212
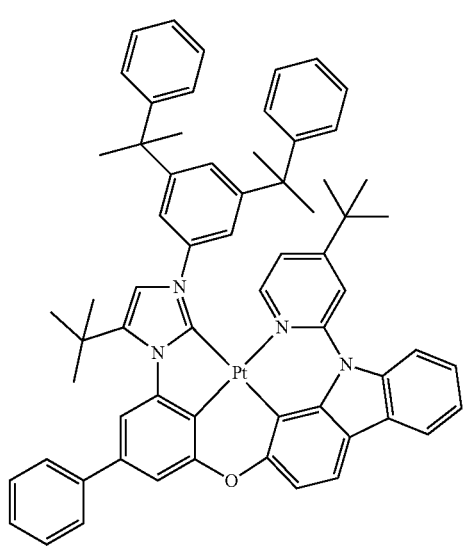
213
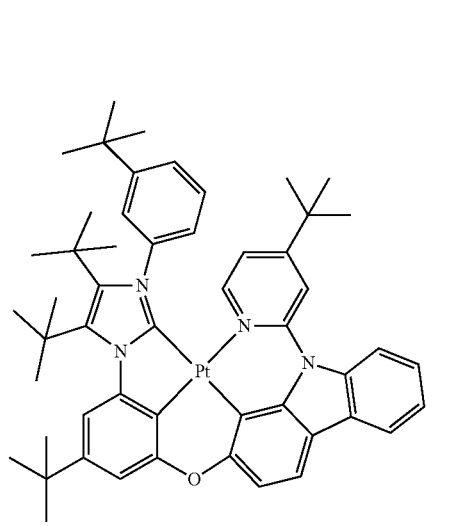

214
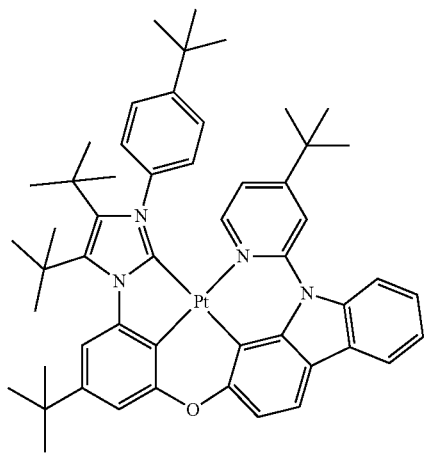
215
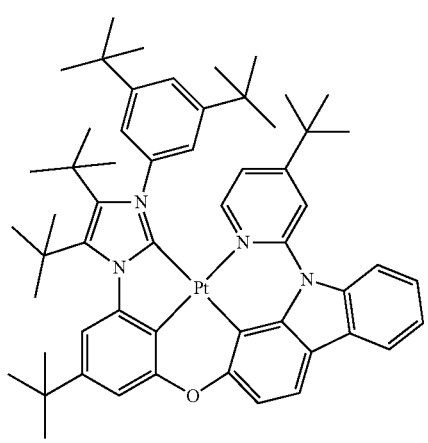
216
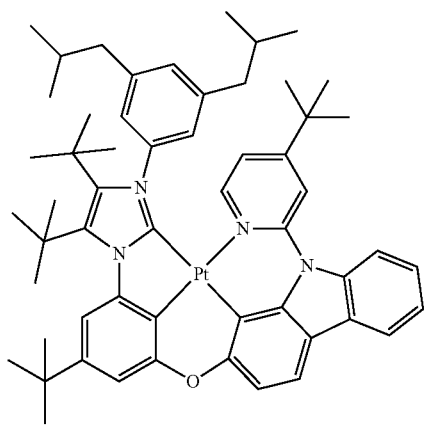
217
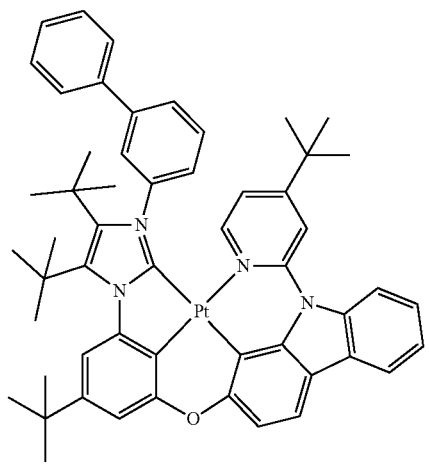
218
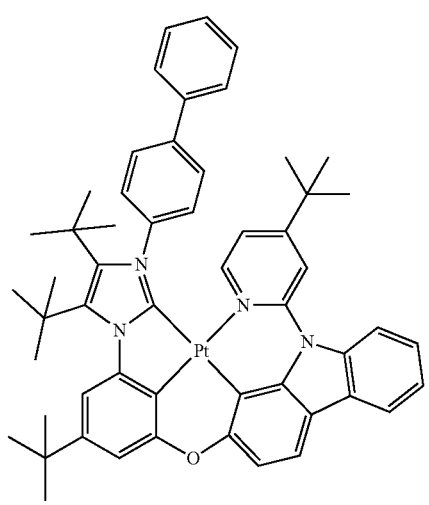
219
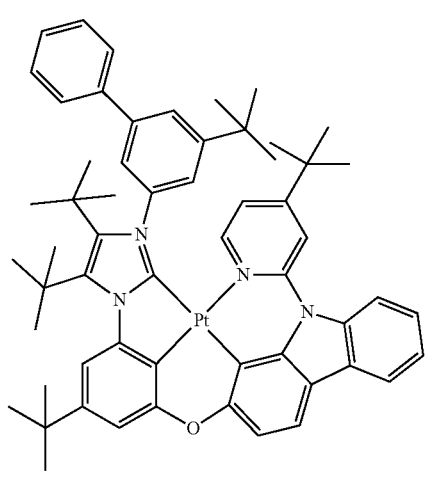

2691
-continued
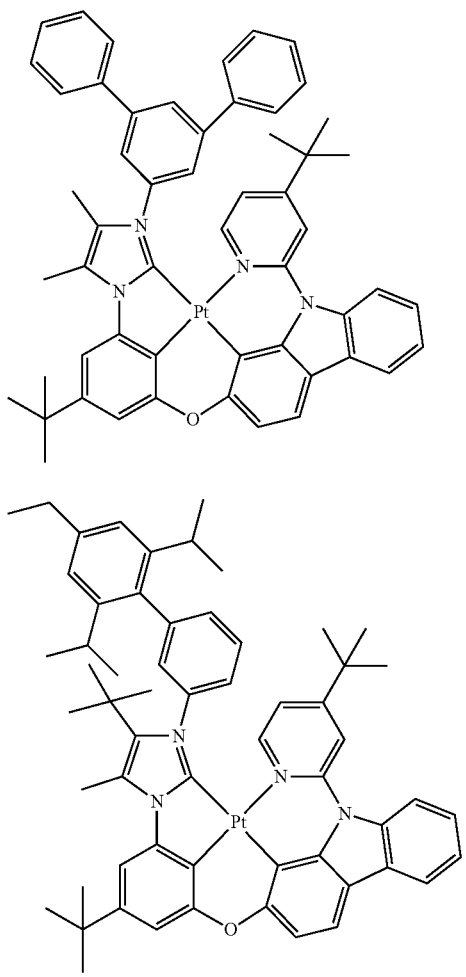
220
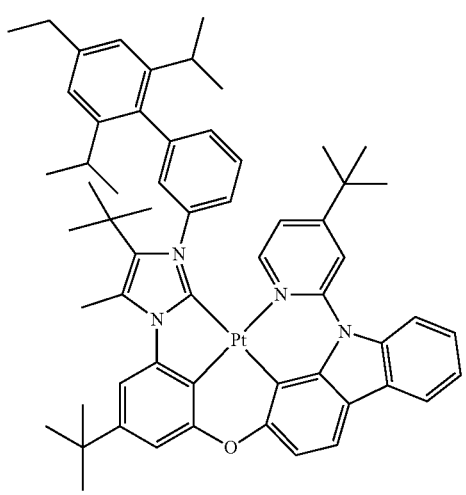
221
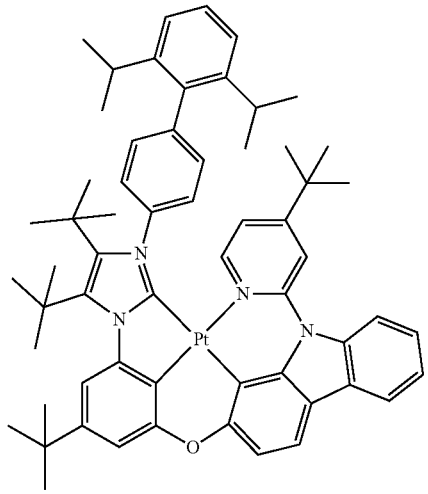
222
2692
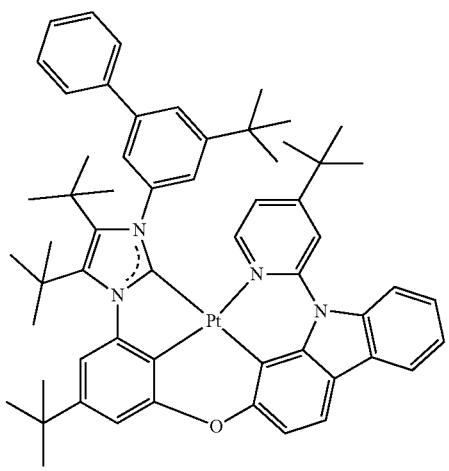
223
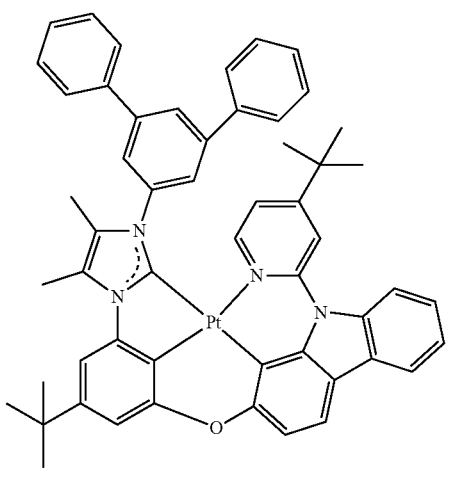
224
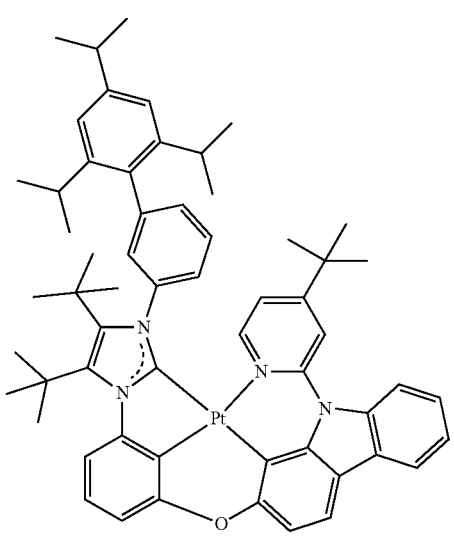
225

226
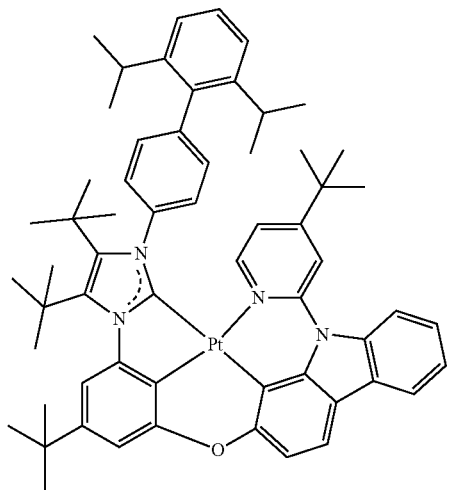
227
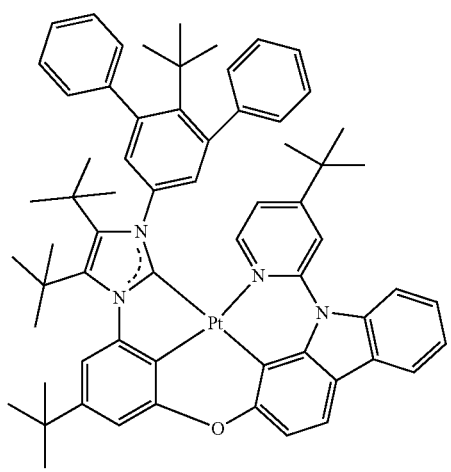
228
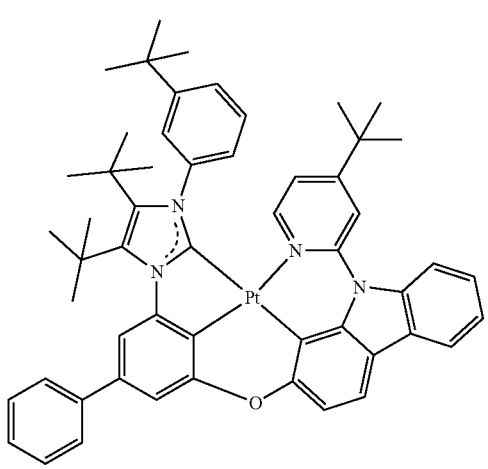
229
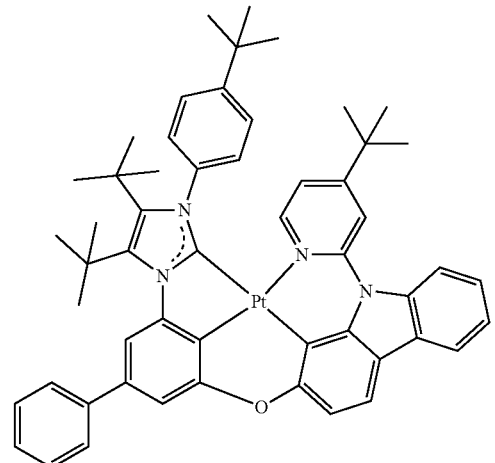
230
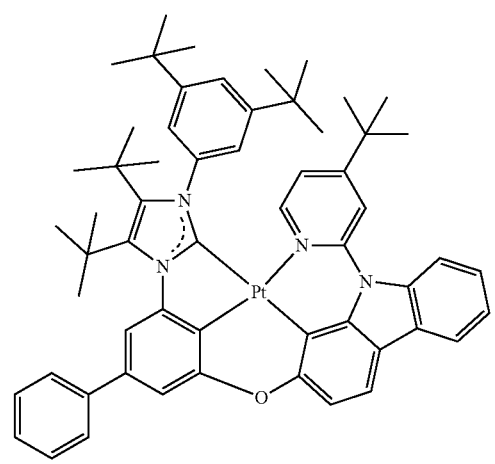
231
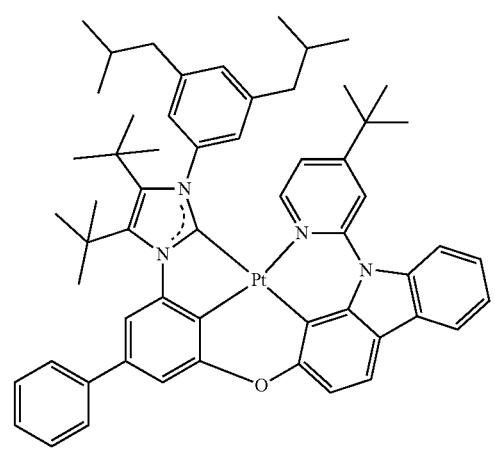

232
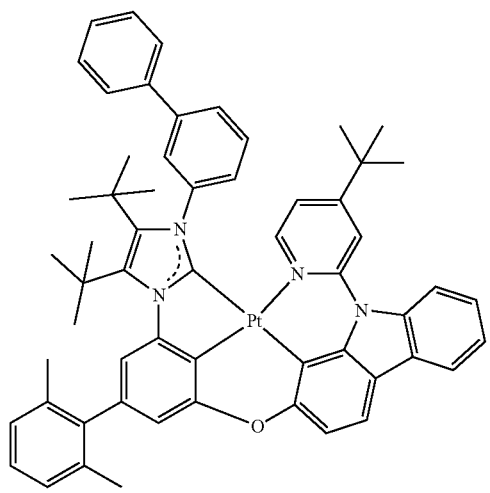
233
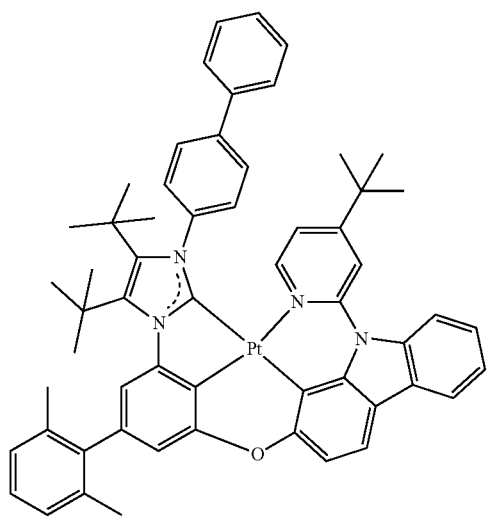
234
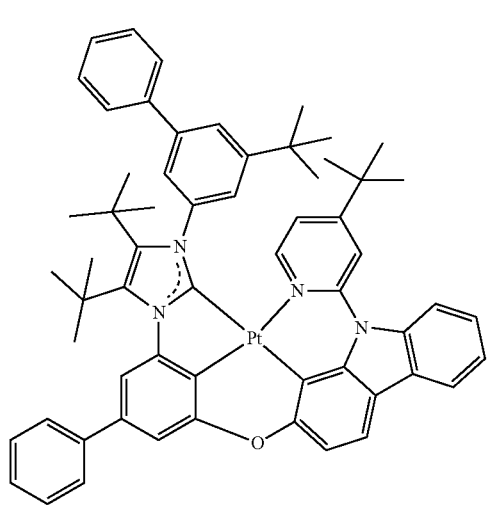
235
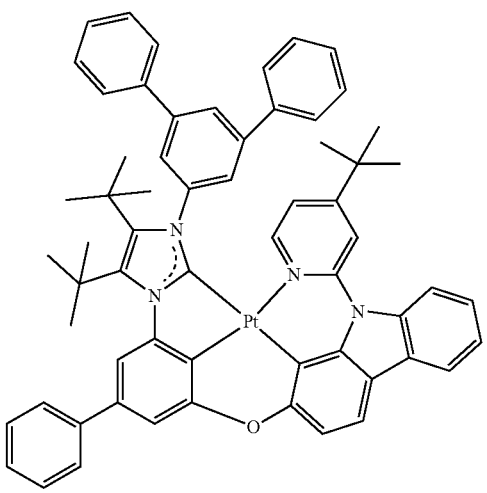
236
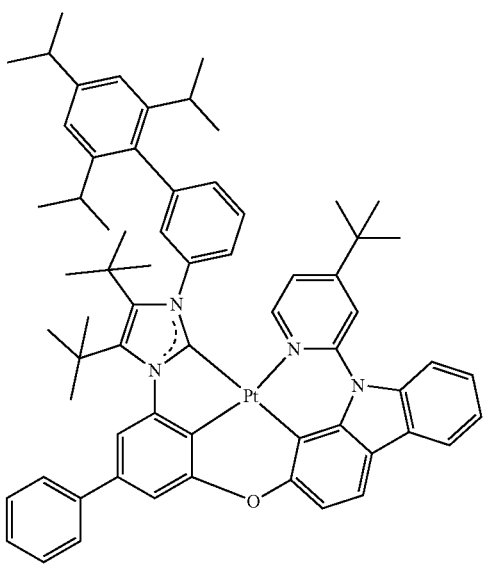
237
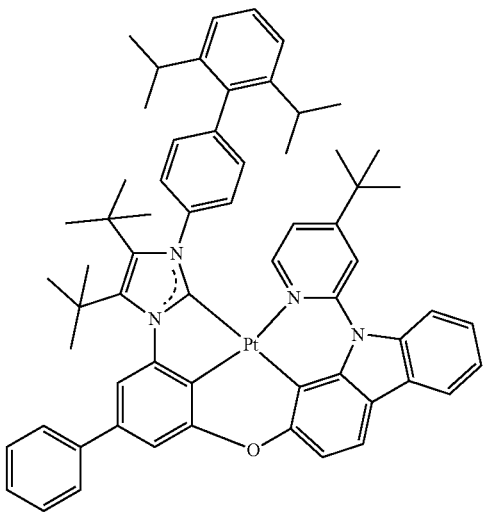

2697
-continued
238
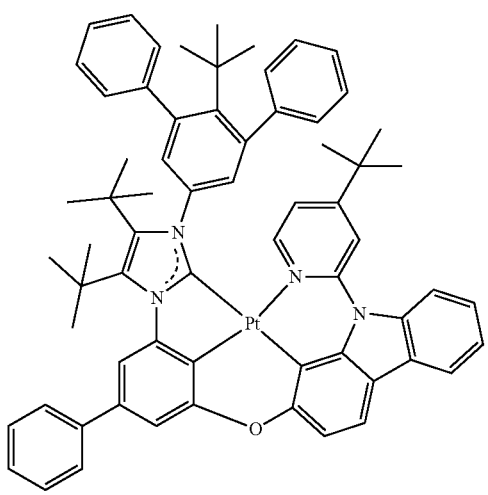
239
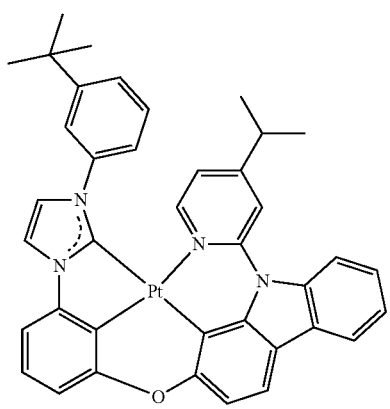
240
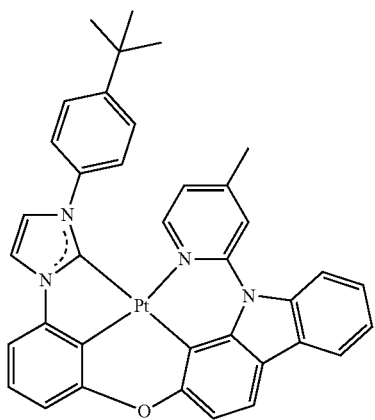
2698
-continued
241
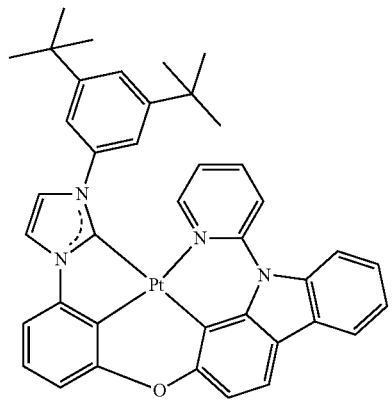
242
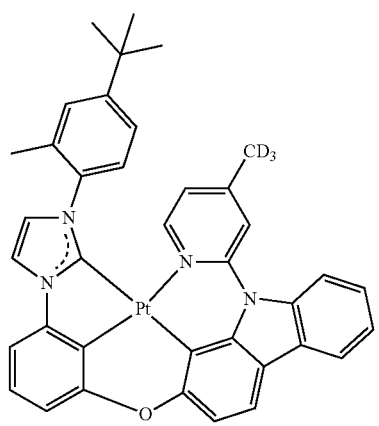
243
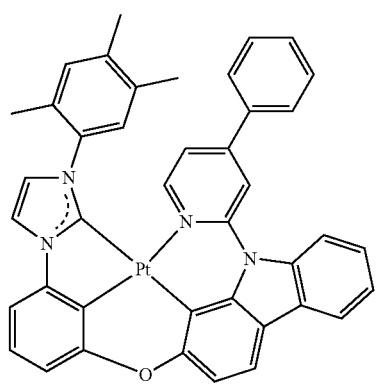
244

245 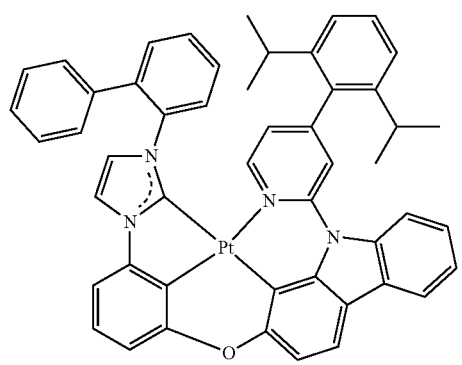
246 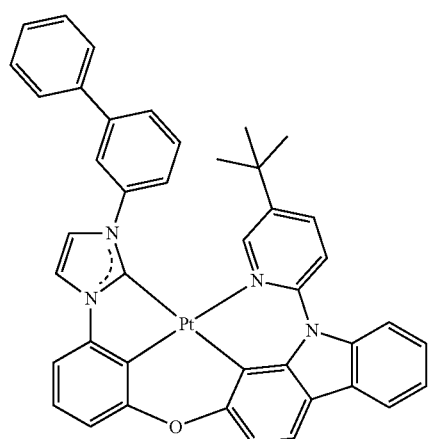
247 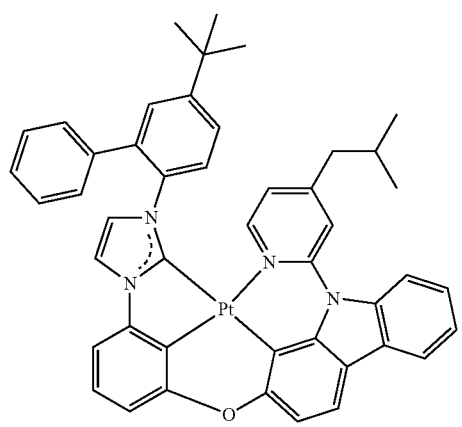
248 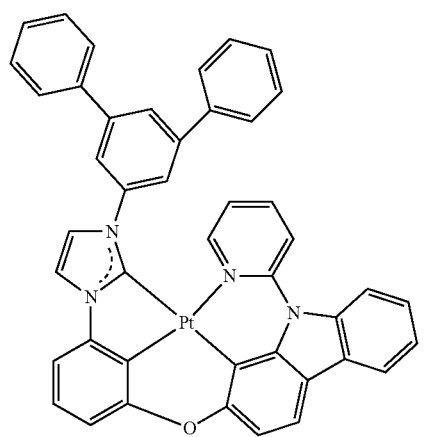
249 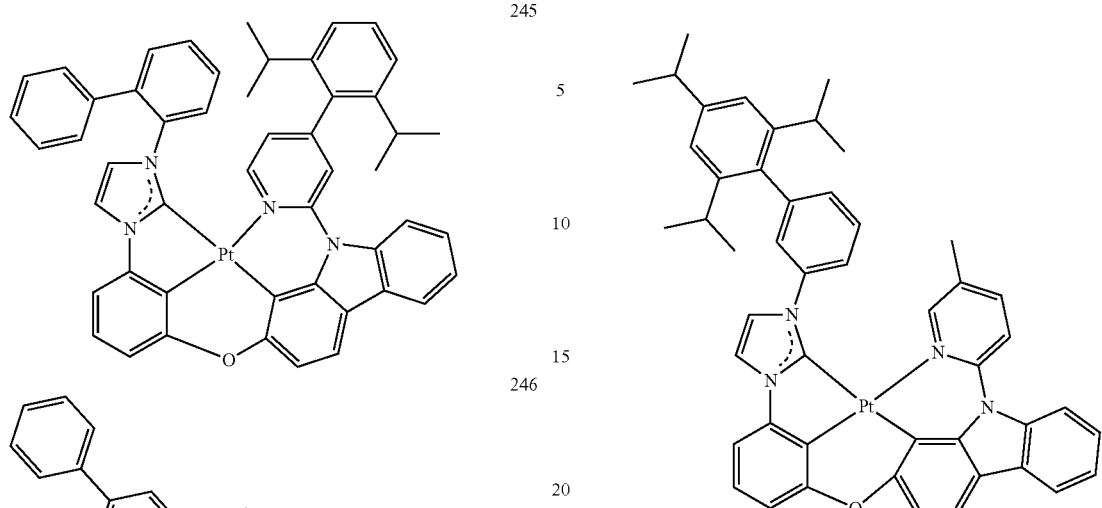
250 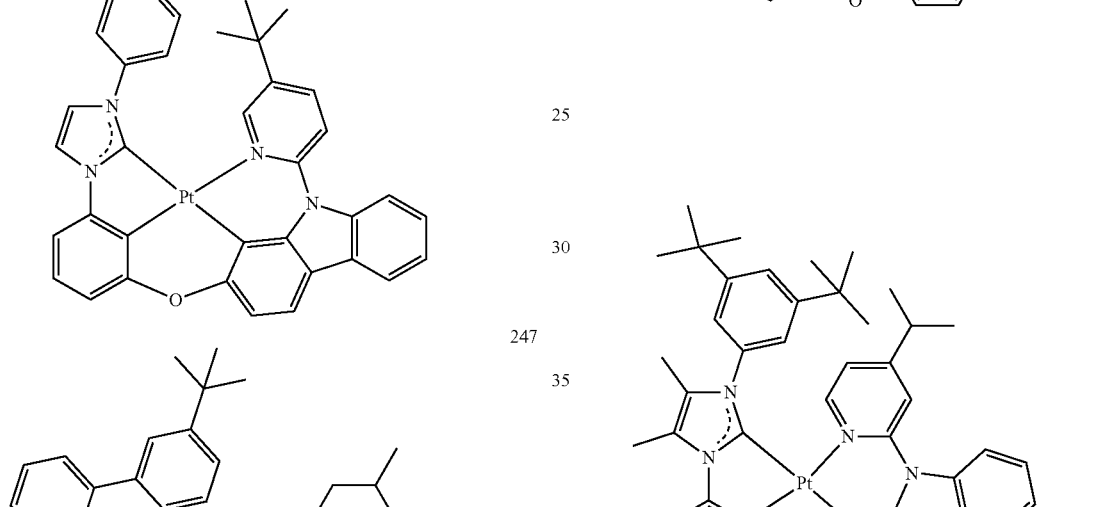
251 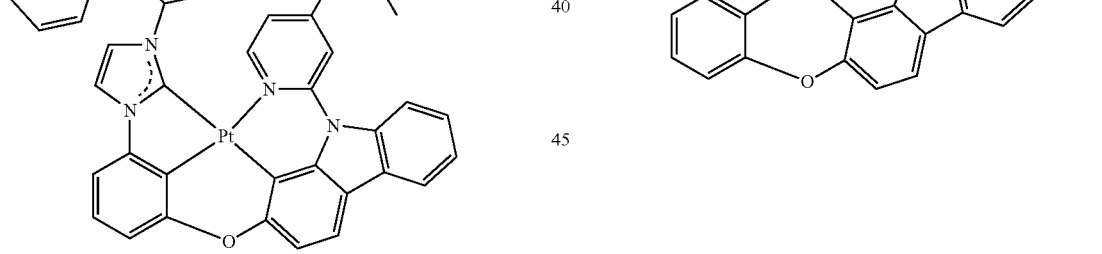

2701
-continued
252
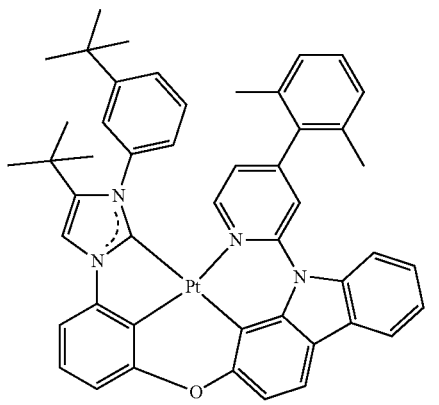
253
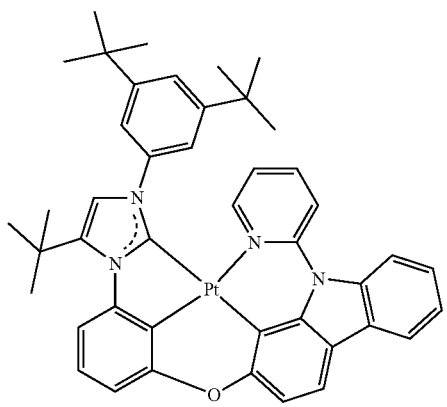
254
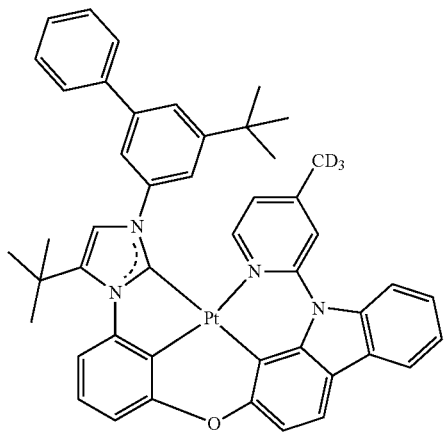
255
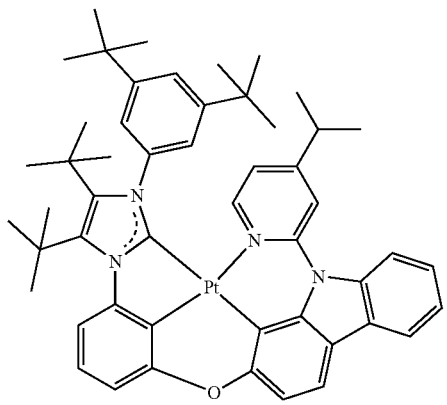
2702
-continued
256
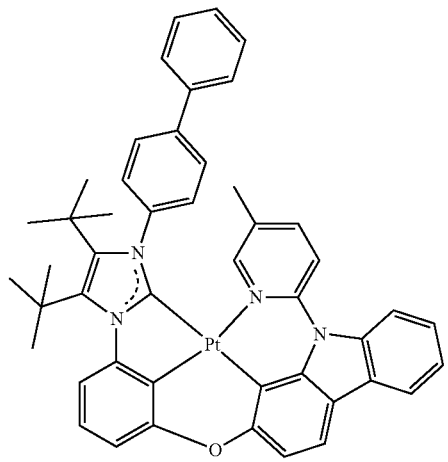
257
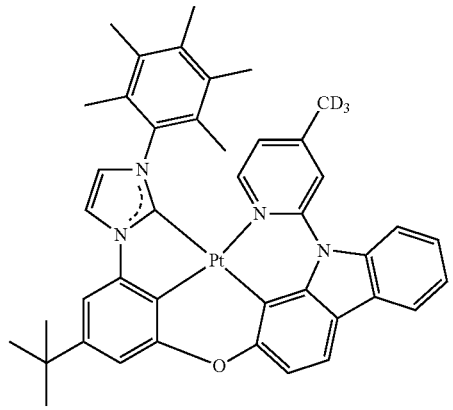
258
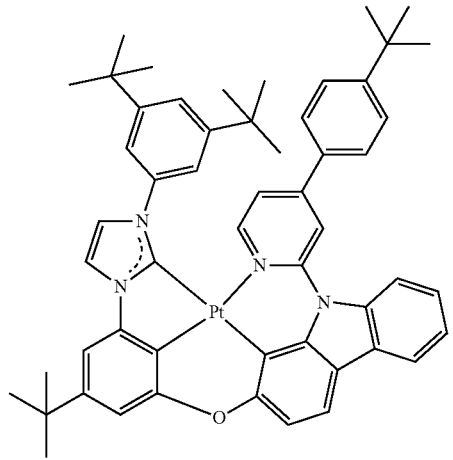

2703
-continued
259
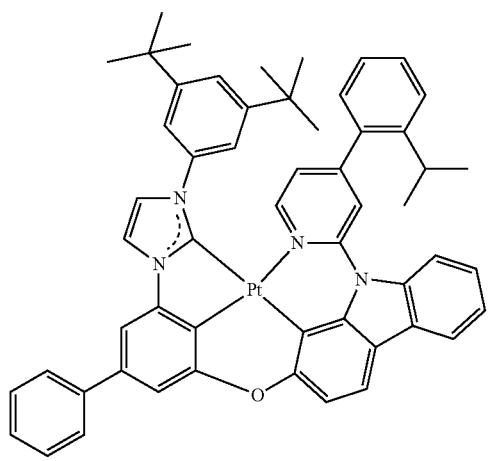
260
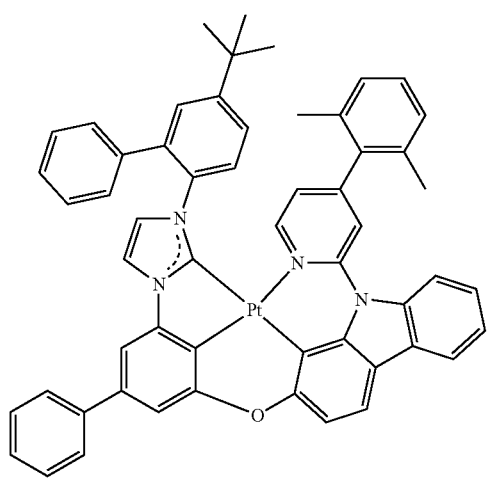
261
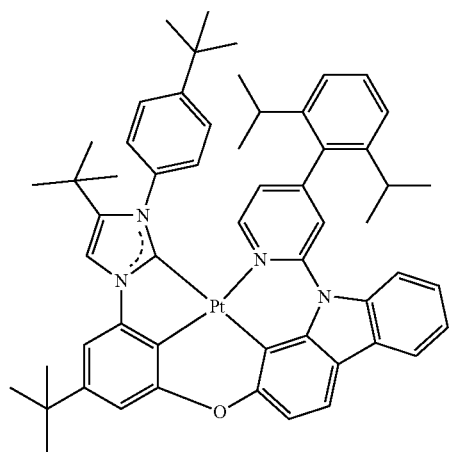
2704
-continued
262
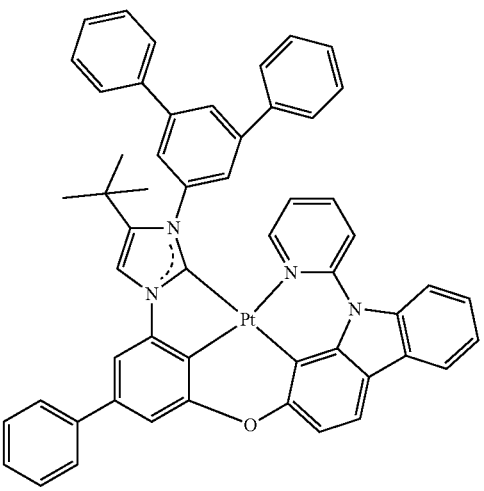
263
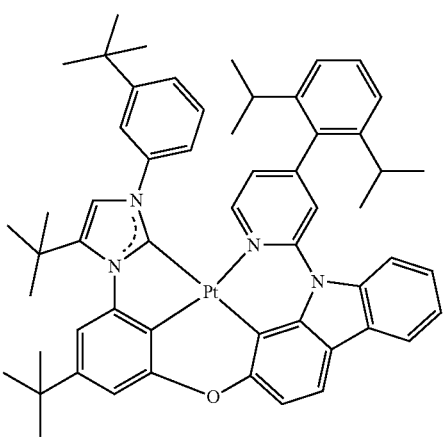
264
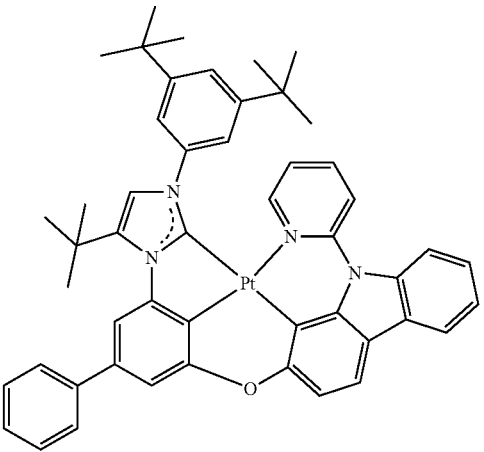

2705
-continued
265
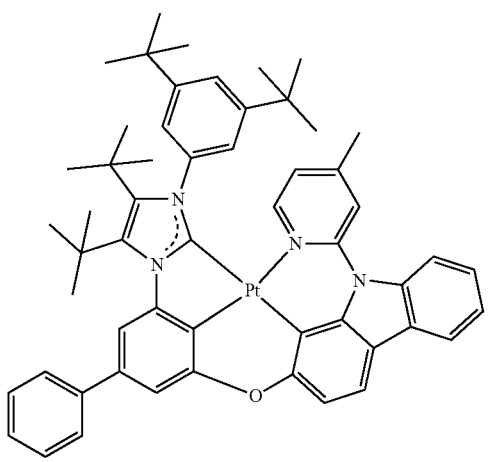
266
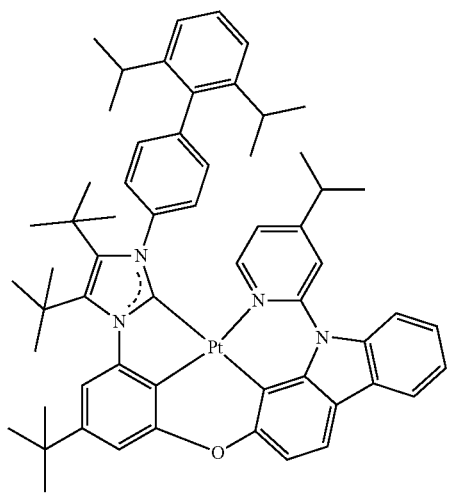
267
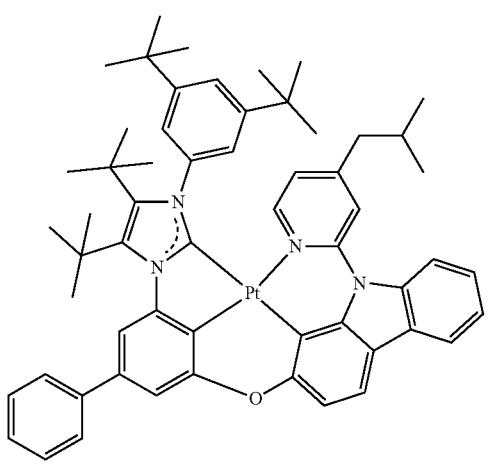
2706
-continued
268
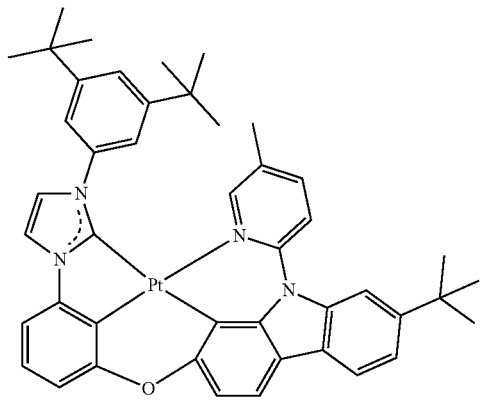
269
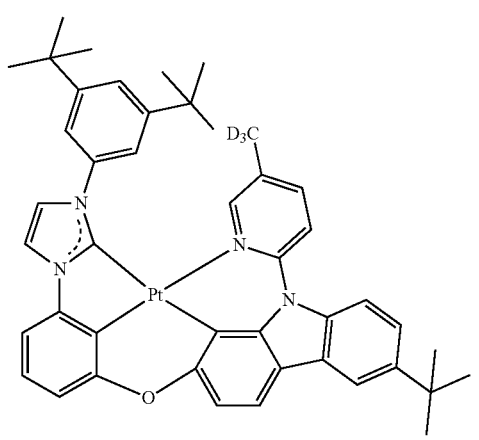
270
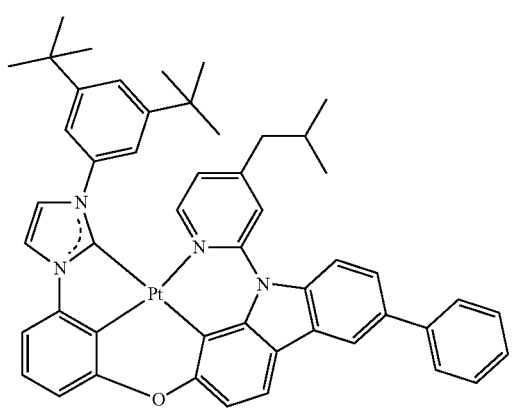

2707
-continued
271
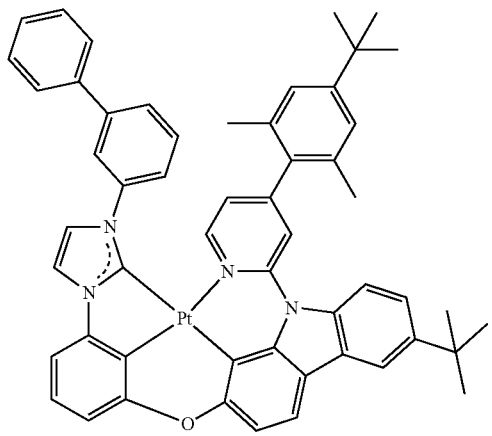
272
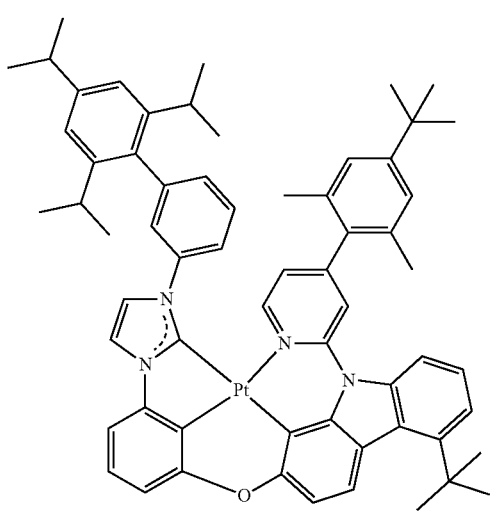
273
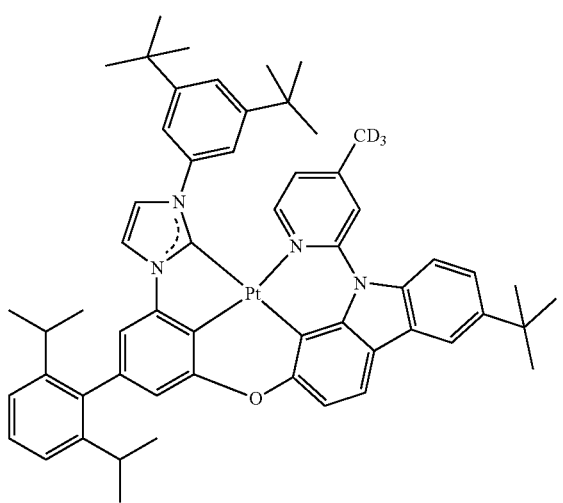
2708
-continued
274
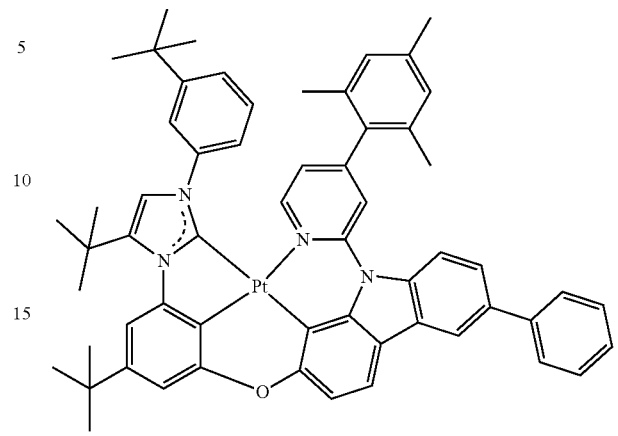
275
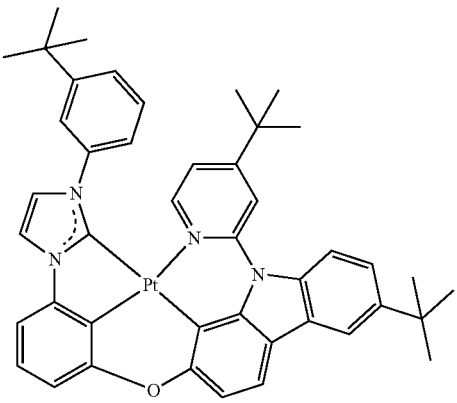
276
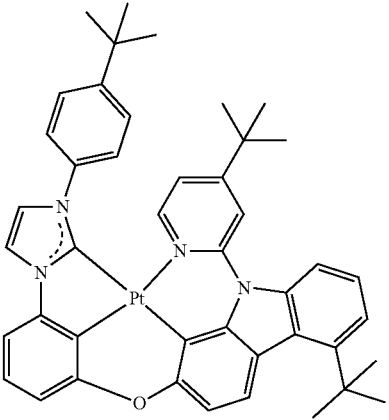

277
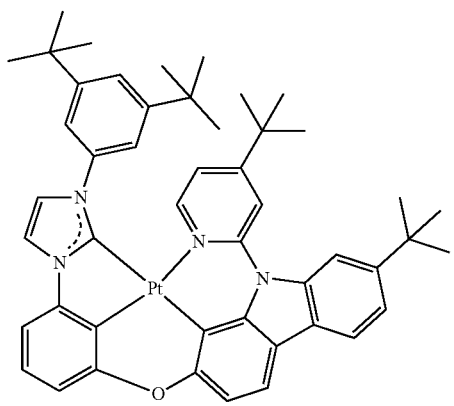
278
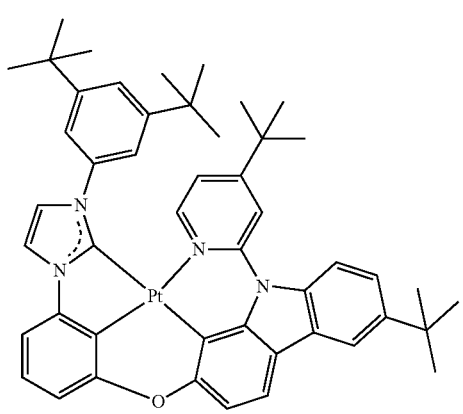
279
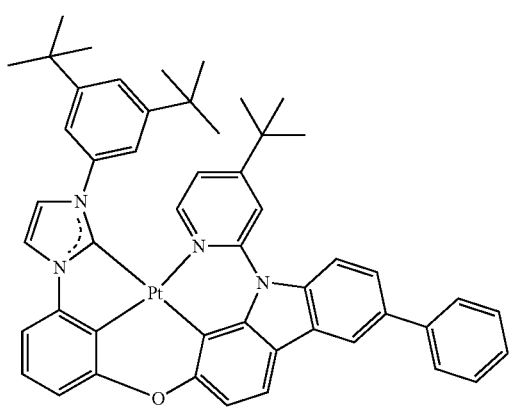
280
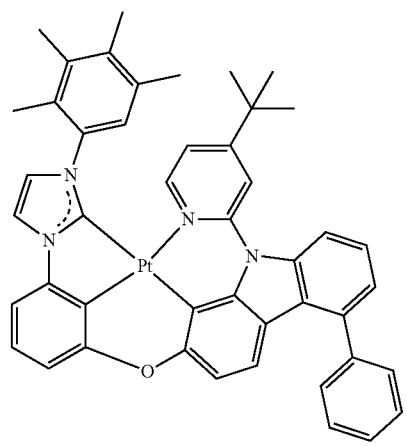
281
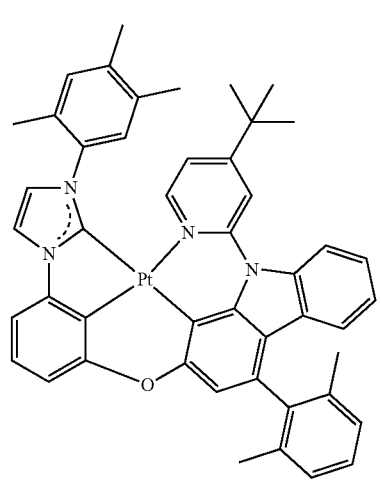
282
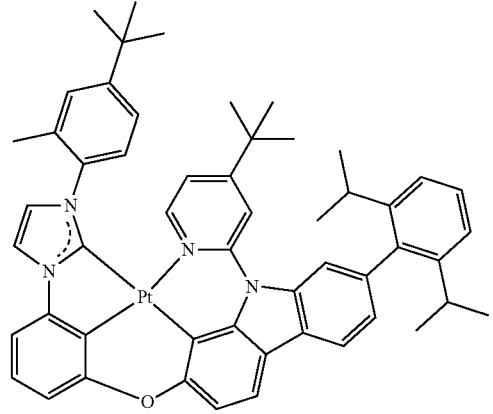

2711
-continued
283
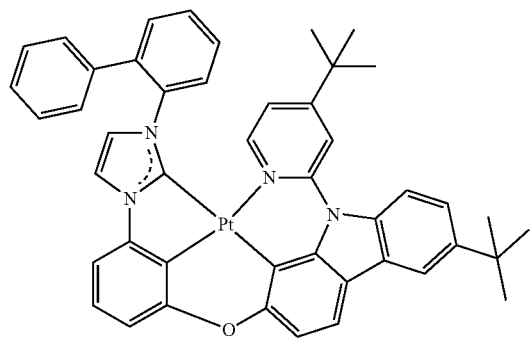
284
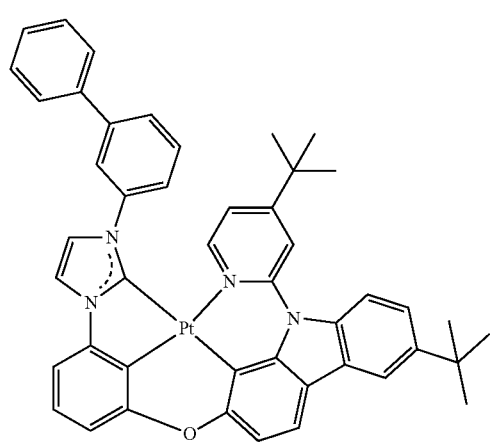
285
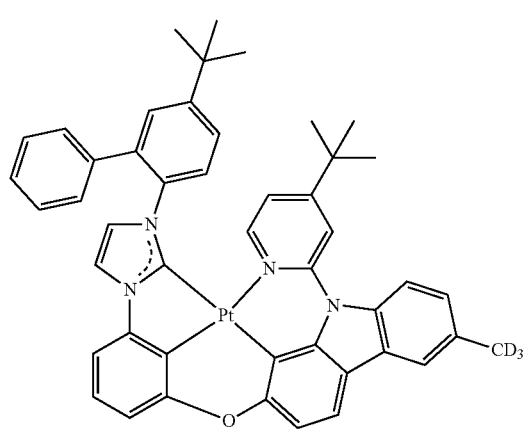
2712
-continued
286
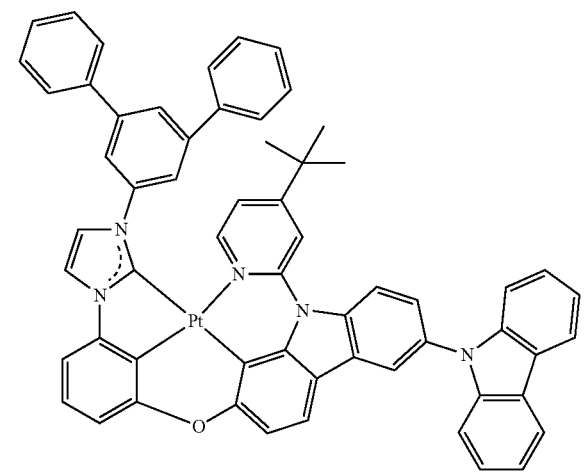
287
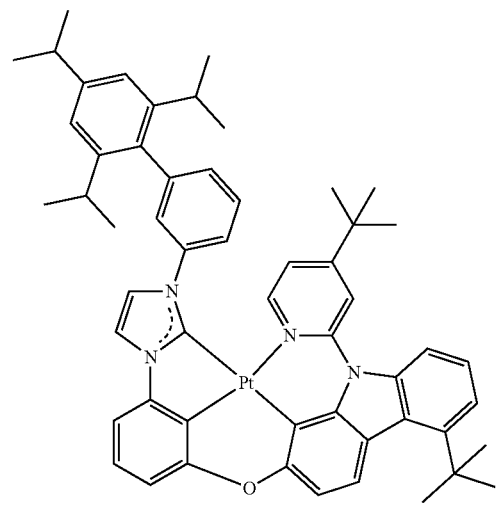
288
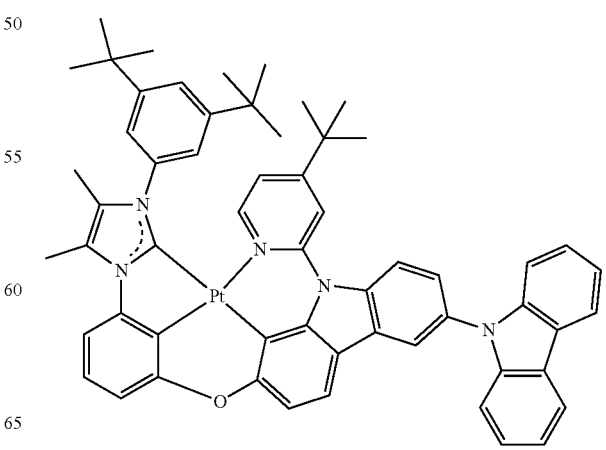

289
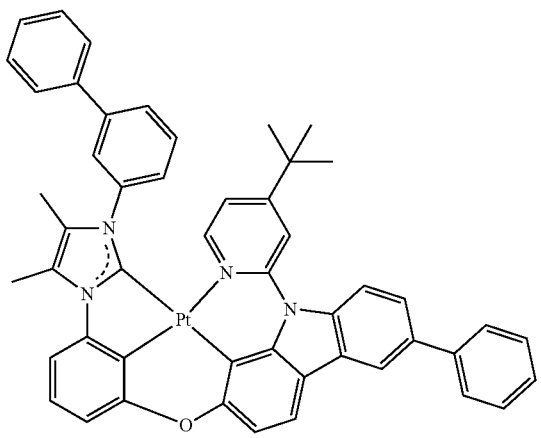
292
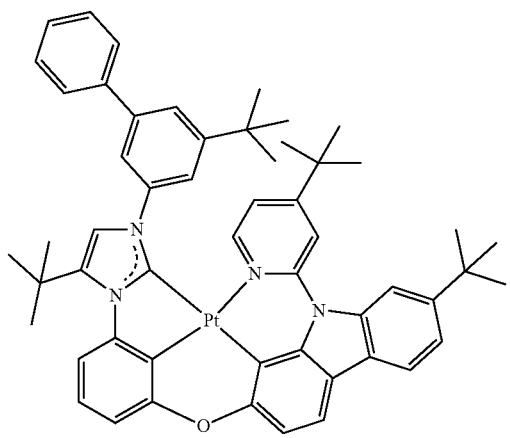
290
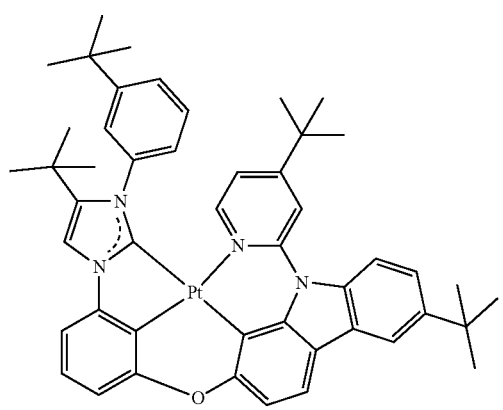
293
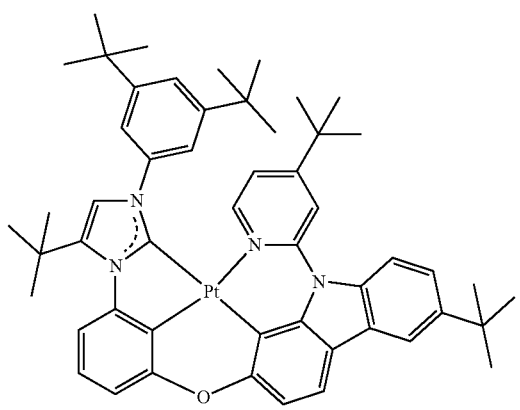
291
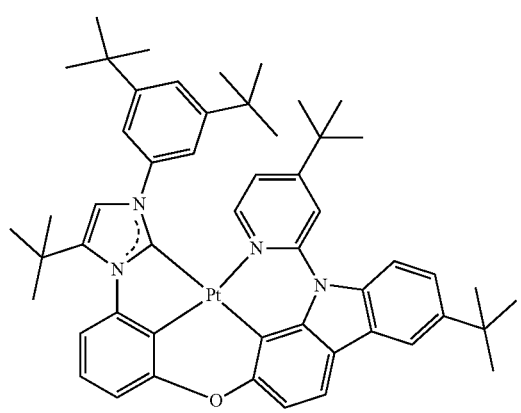
294
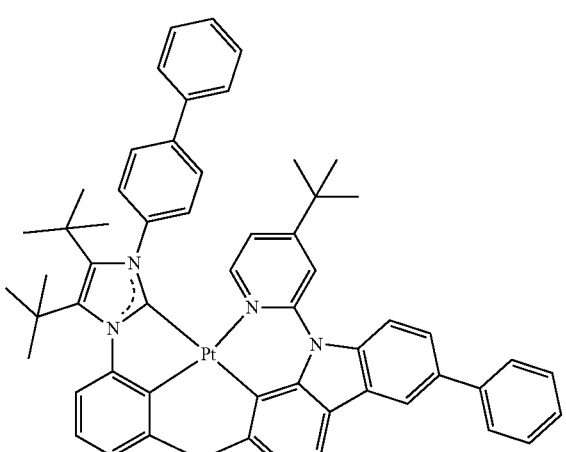

2715
-continued
295
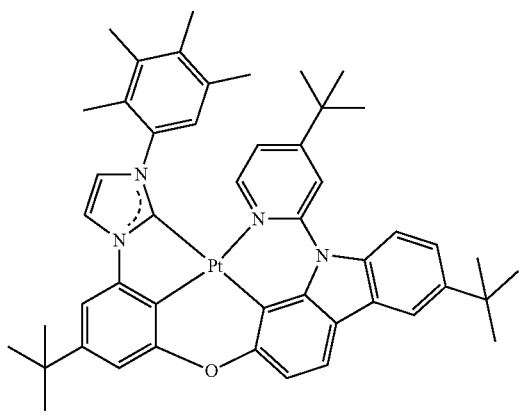
296
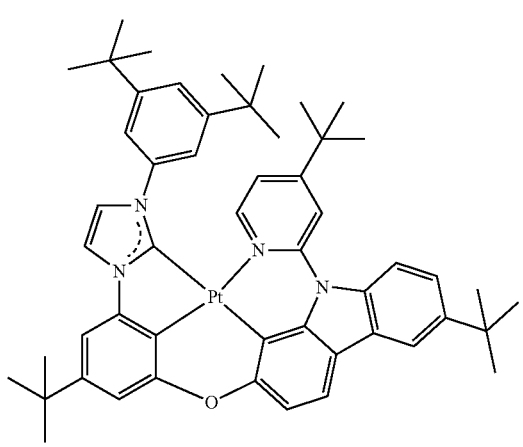
297
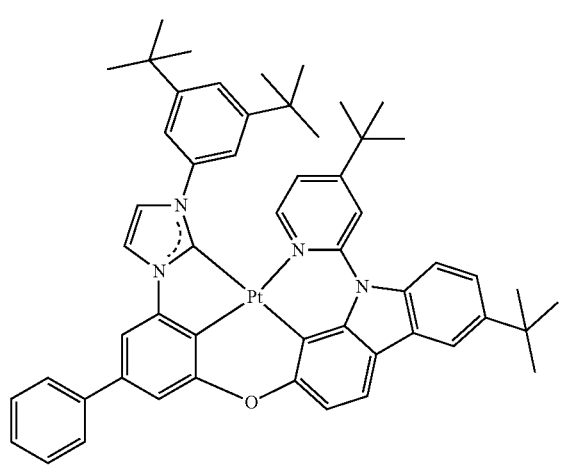
2716
-continued
298
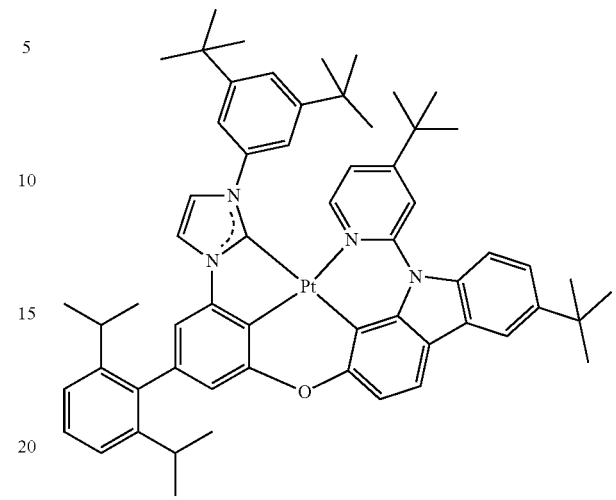
299
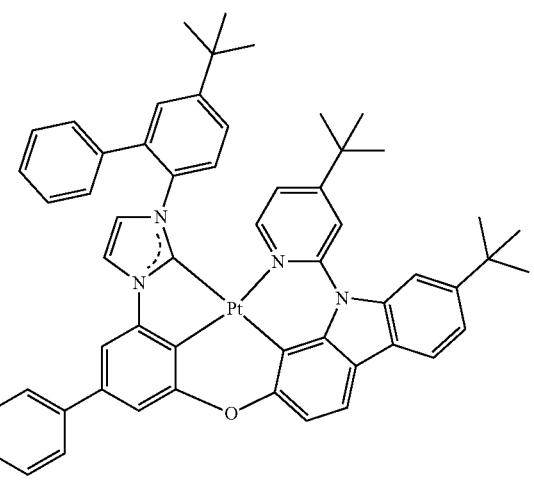
300
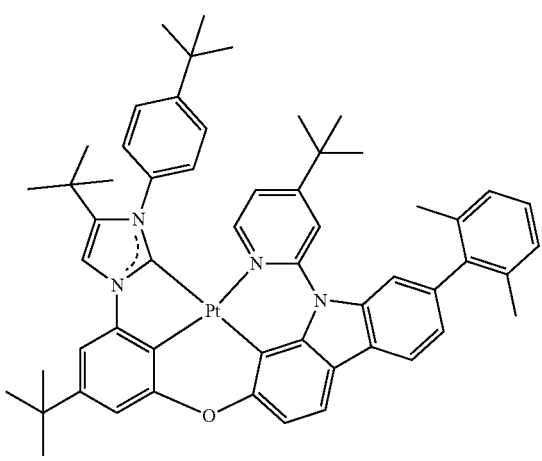

301
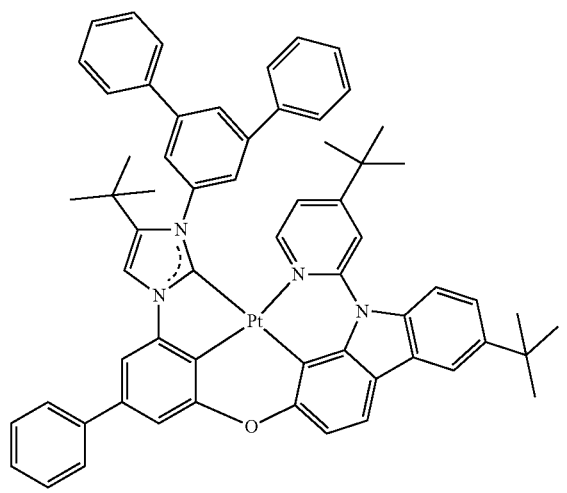
302
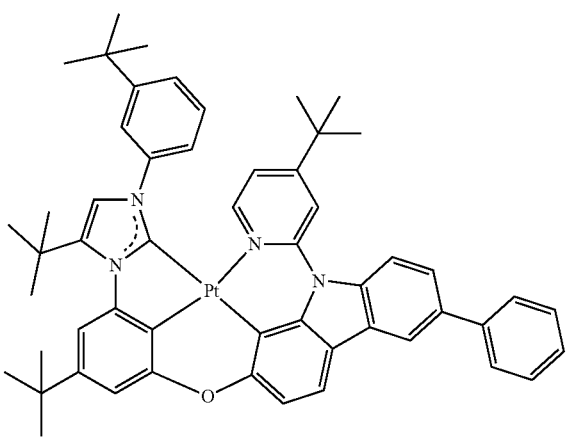
303
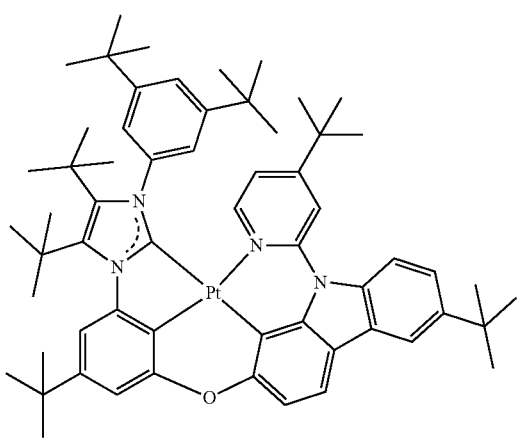
304
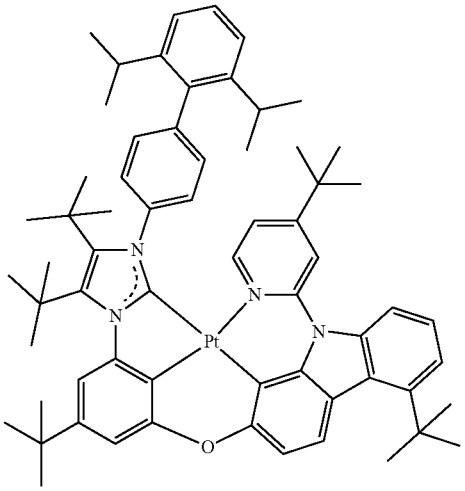
305
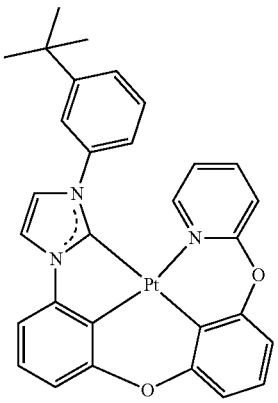
306
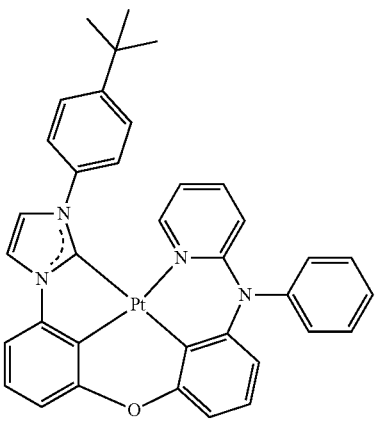

2719
-continued
307
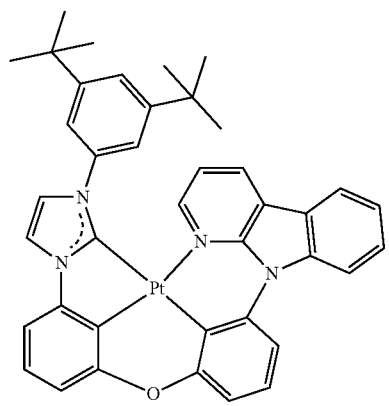
308
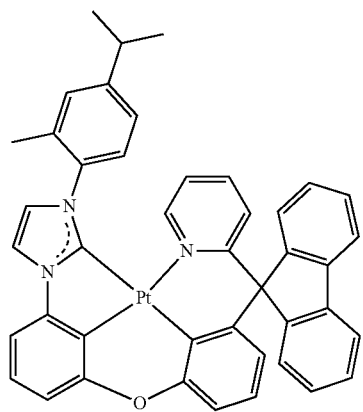
309
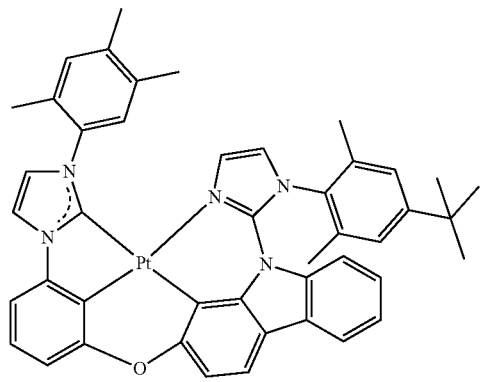
310
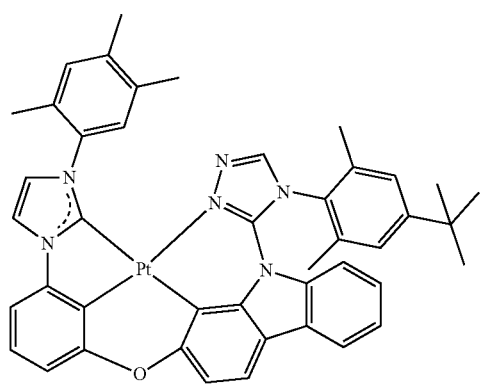
2720
-continued
311
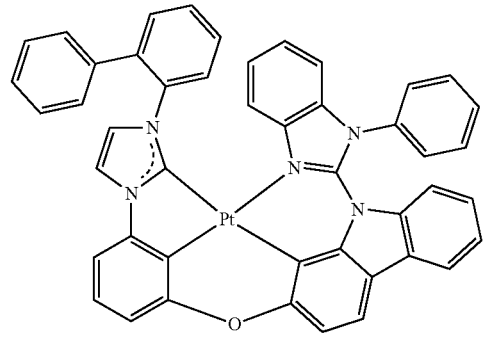
312
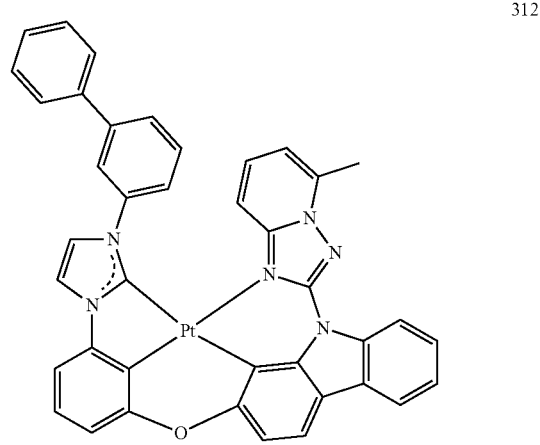
313
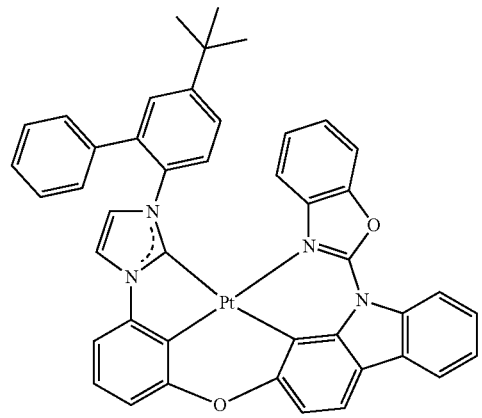
314
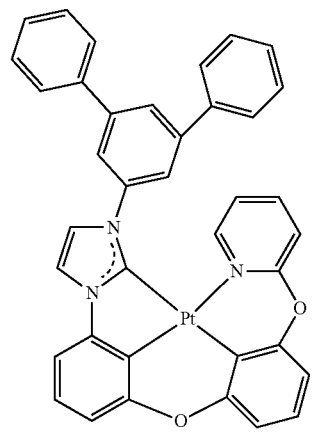

2721
-continued
315
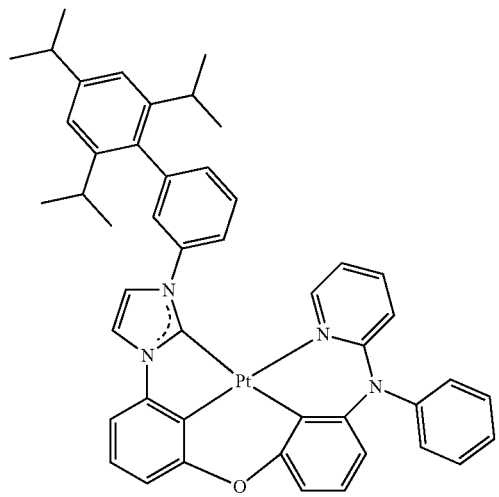
316
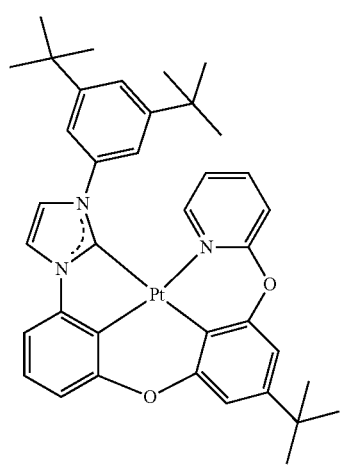
317
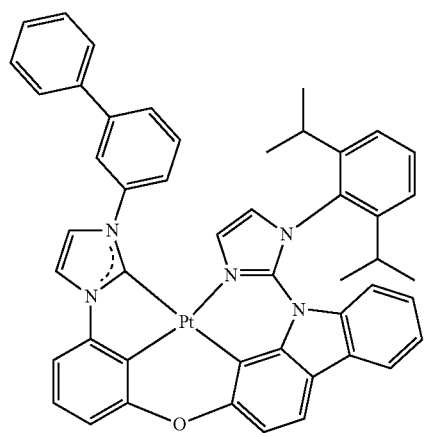
2722
-continued
318
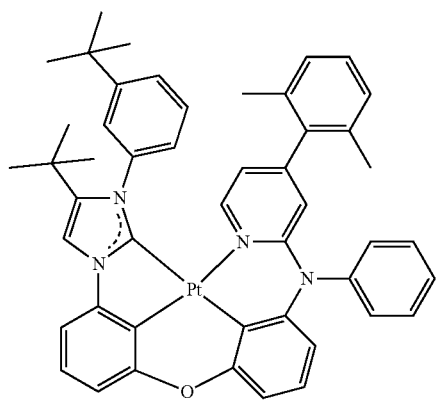
319
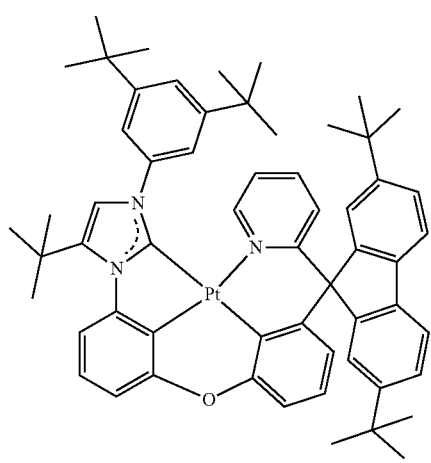
320
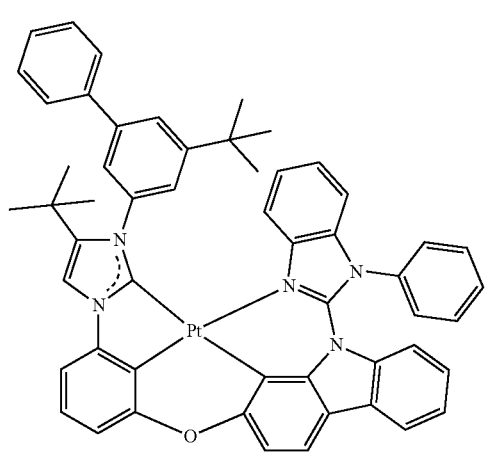

2723
-continued
2724
-continued
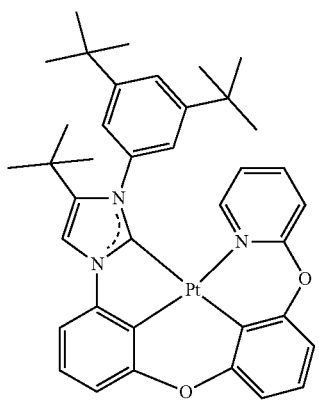
321
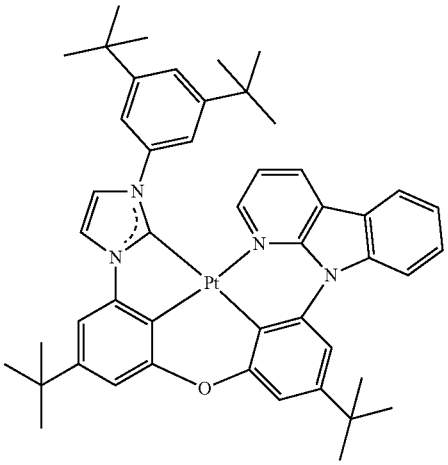
324
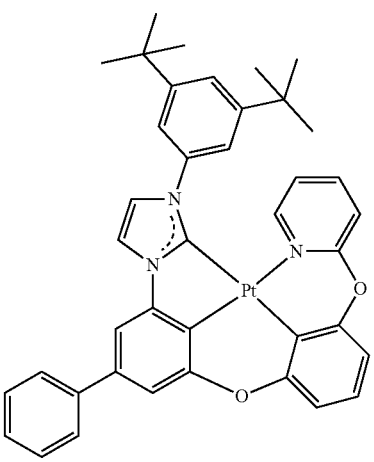
322
325
323
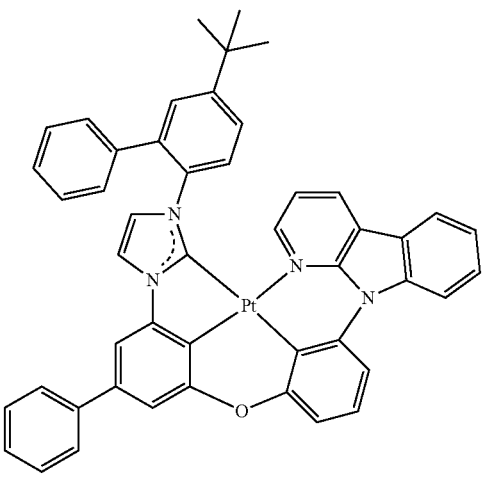
326

2725
-continued
327
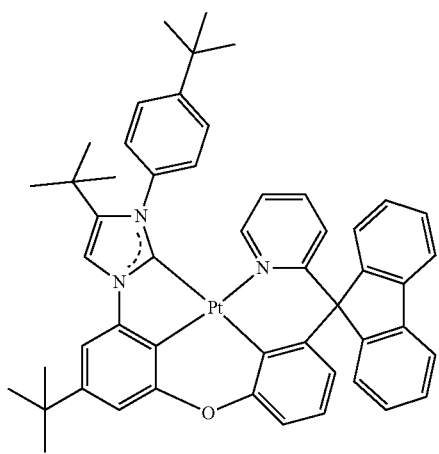
328
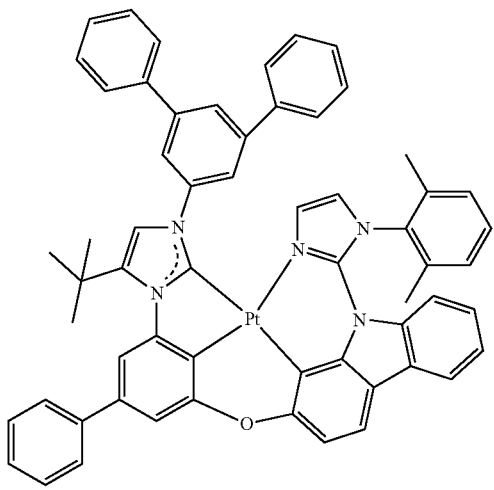
329
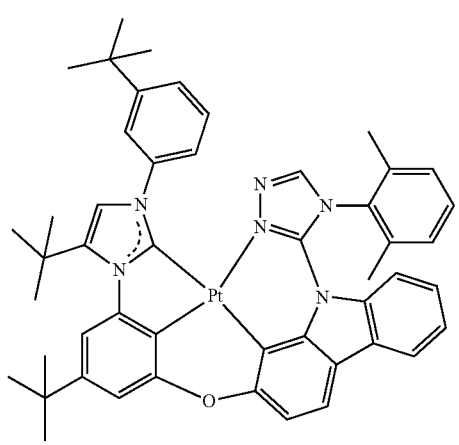
2726
-continued
330
331
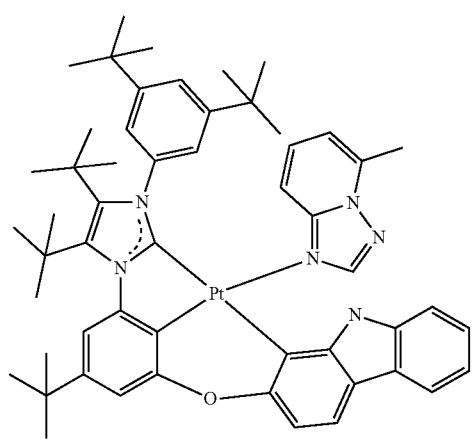
332
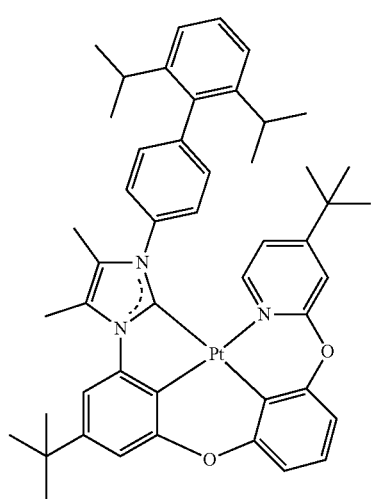

2727
-continued
333
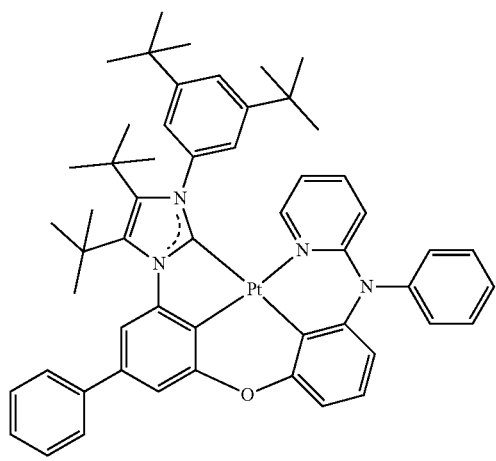
334
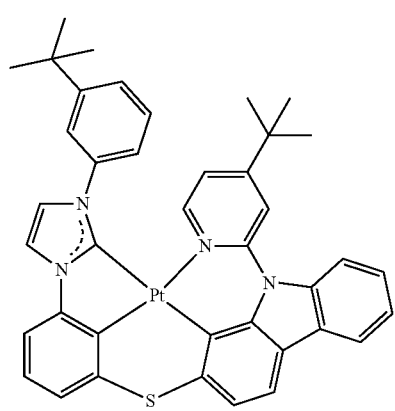
335
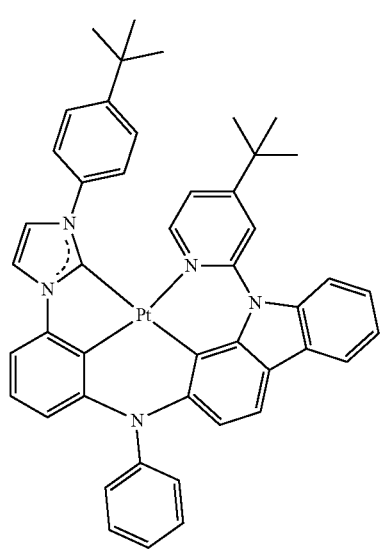
2728
-continued
336
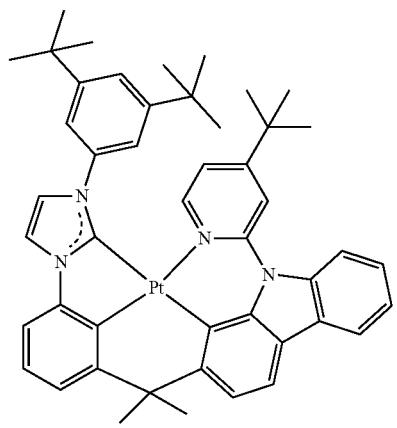
337
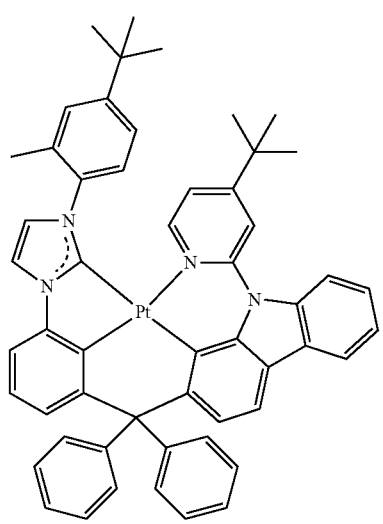
338
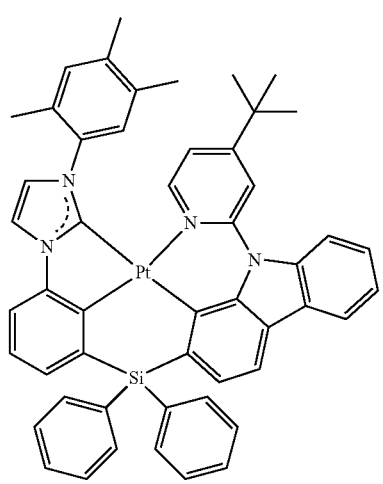

2729
-continued
339
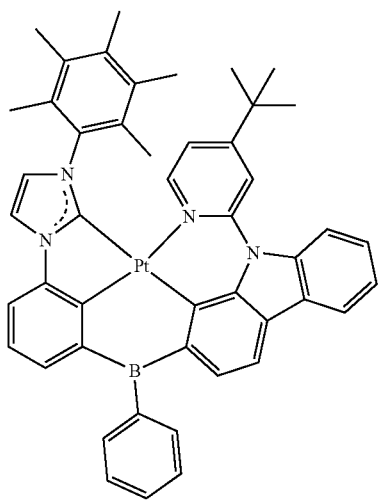
340
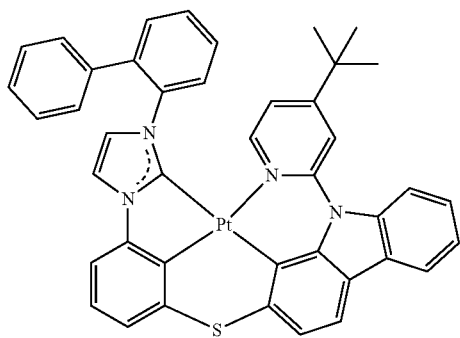
341
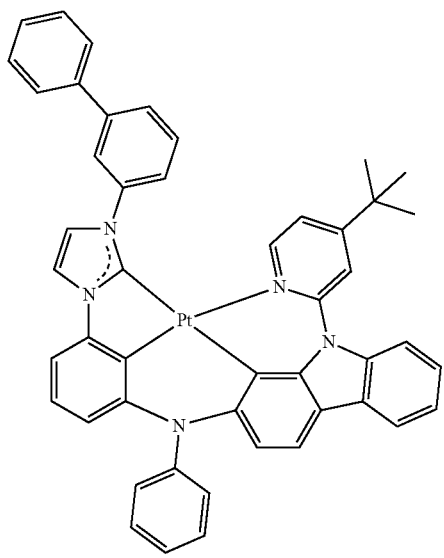
2730
-continued
342
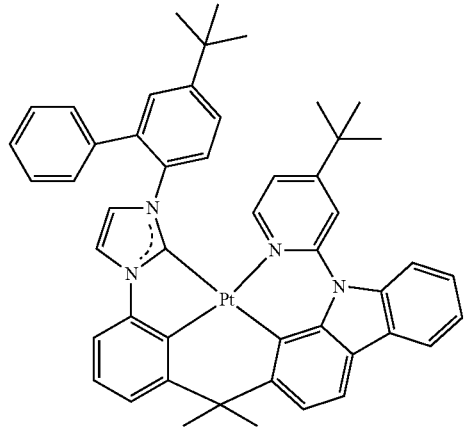
343
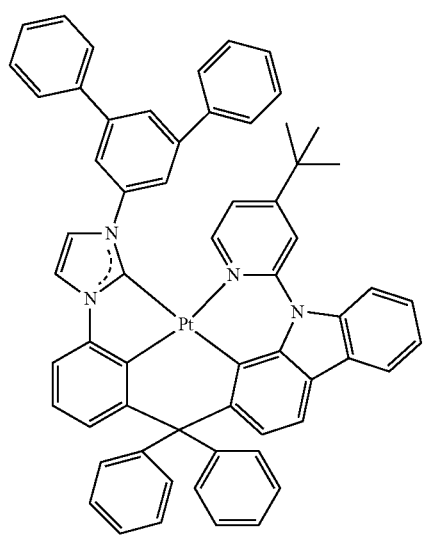
344
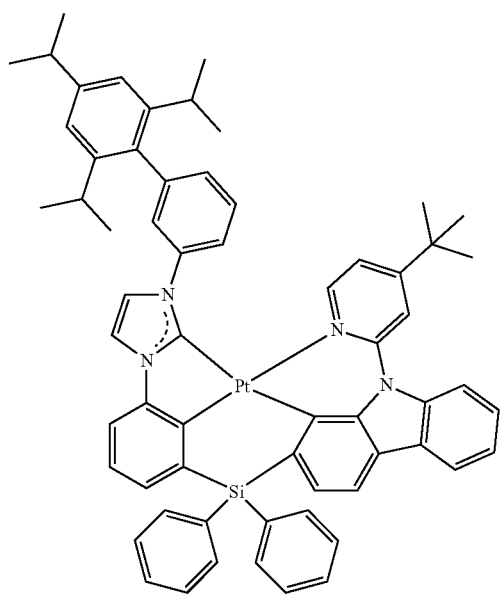

2731
-continued
345
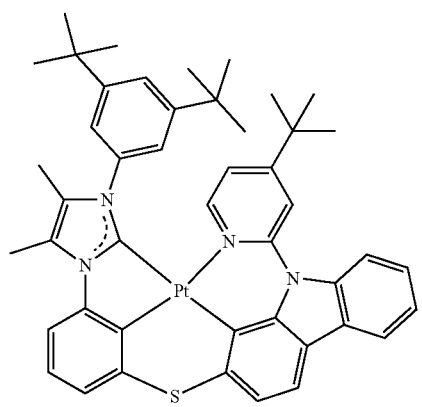
346
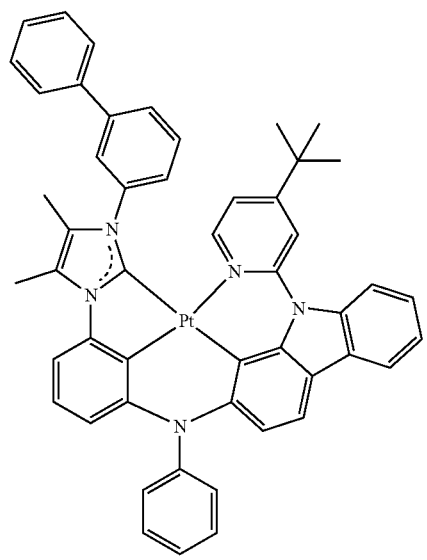
347
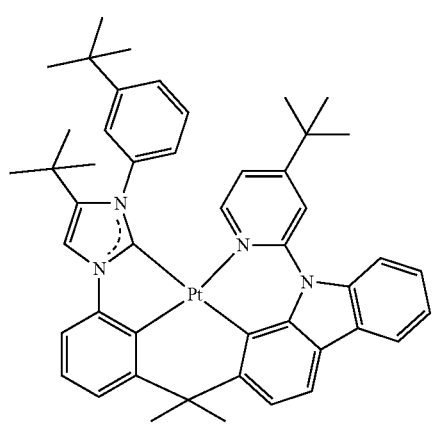
2732
-continued
348
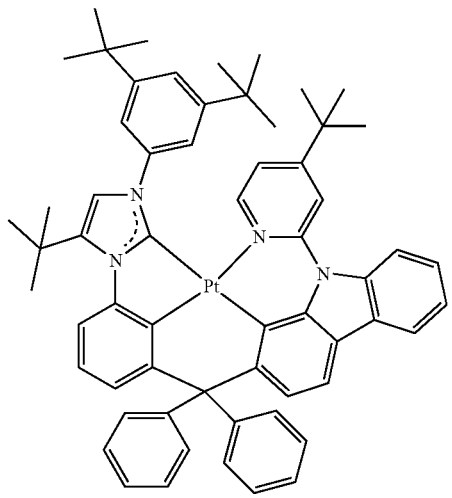
349
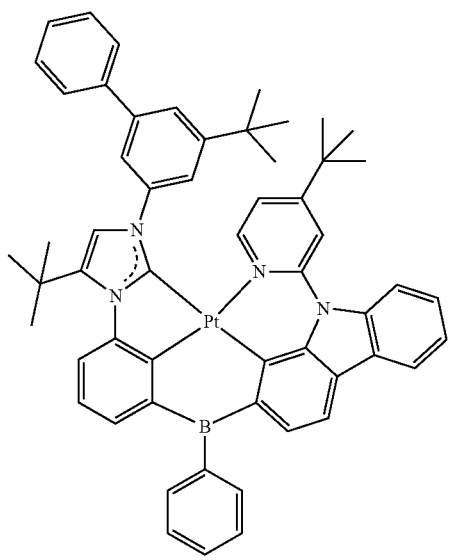
350
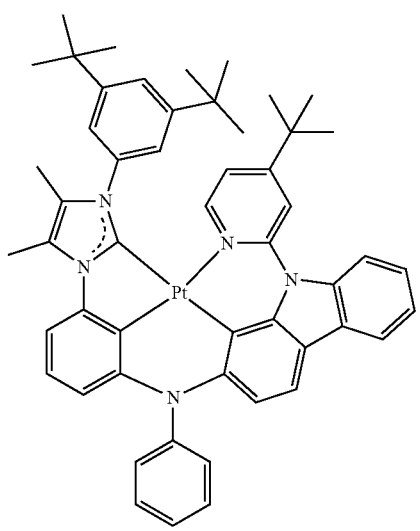

2733
-continued
351
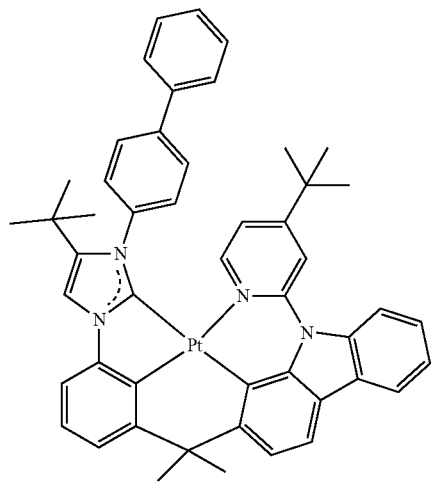
352
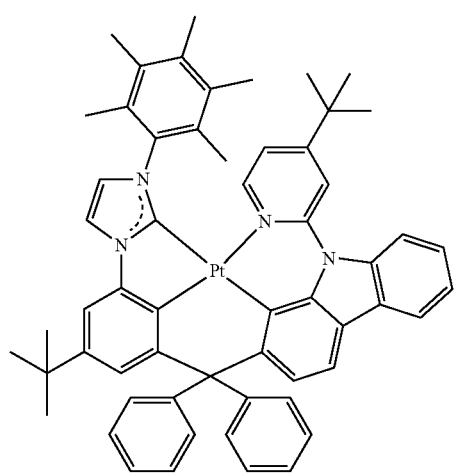
353
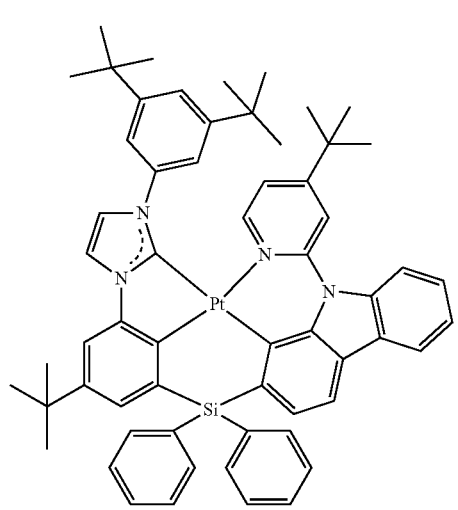
2734
-continued
354
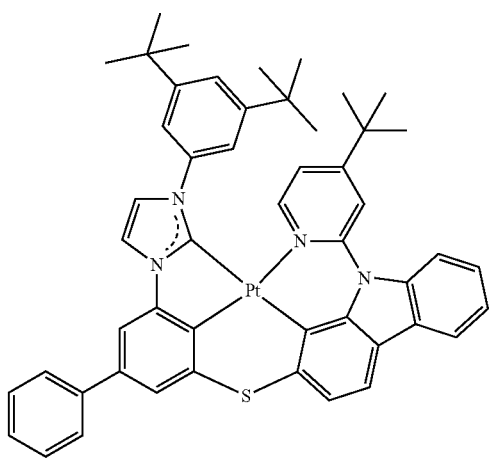
355
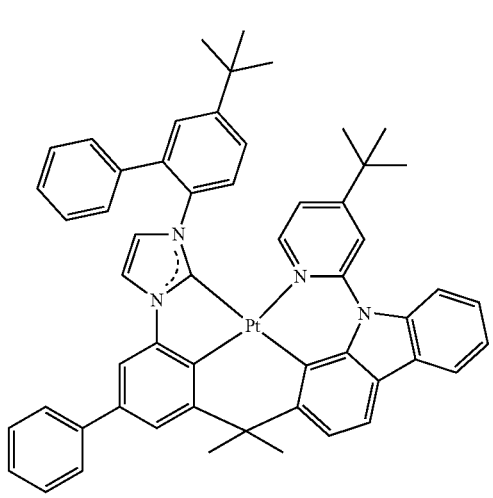
356
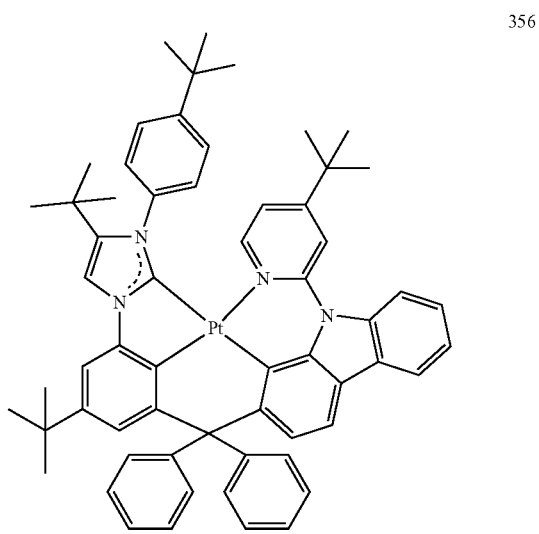

2735
-continued
357
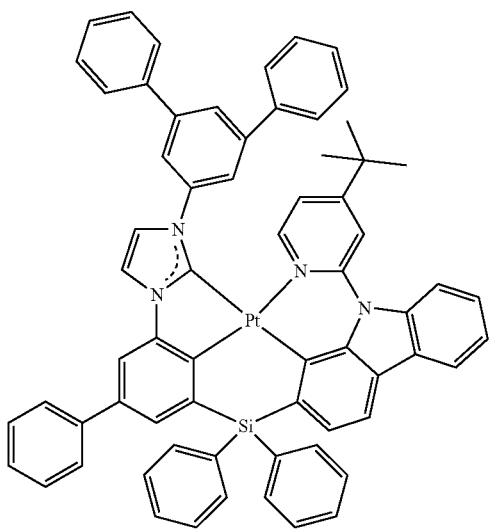
358
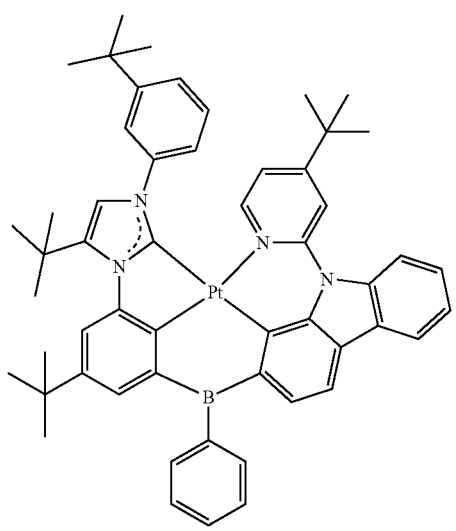
359
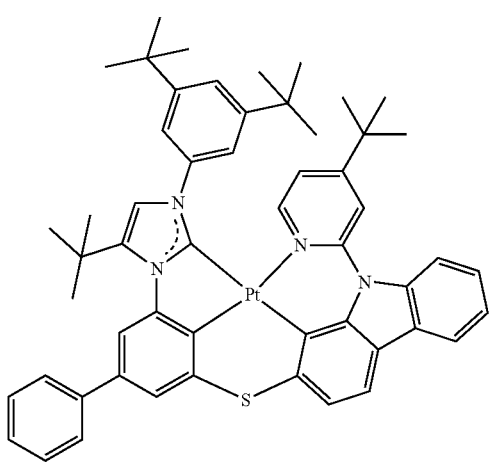
2736
-continued
360
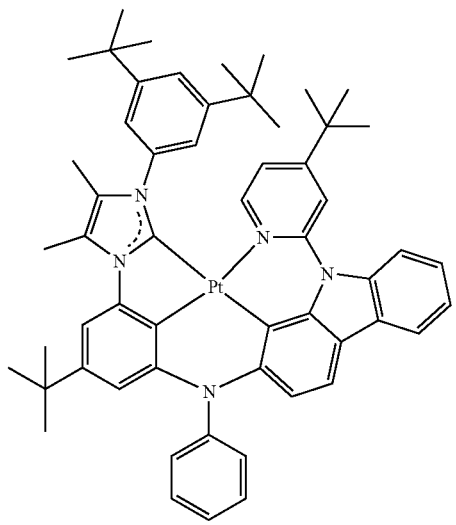
361
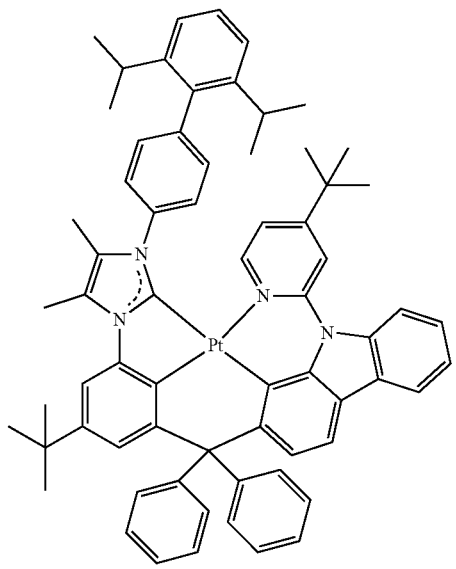
362
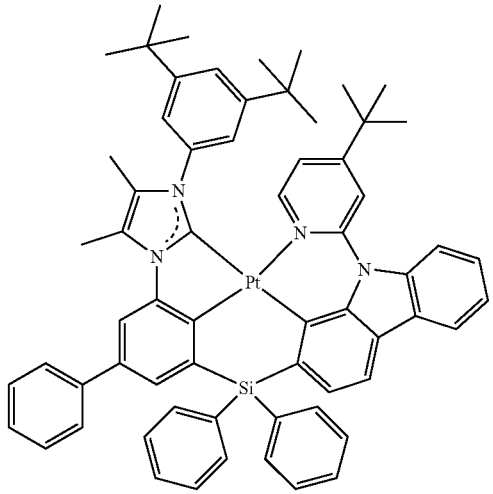

2737
-continued
2738
-continued
363
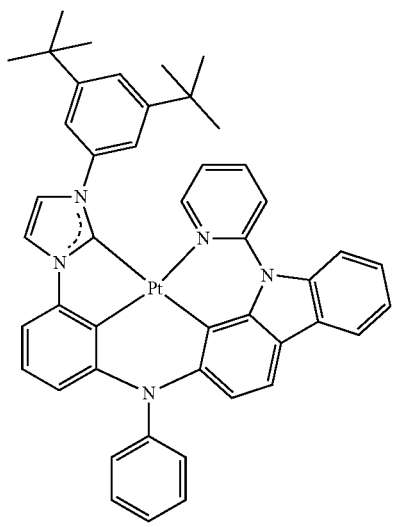
366
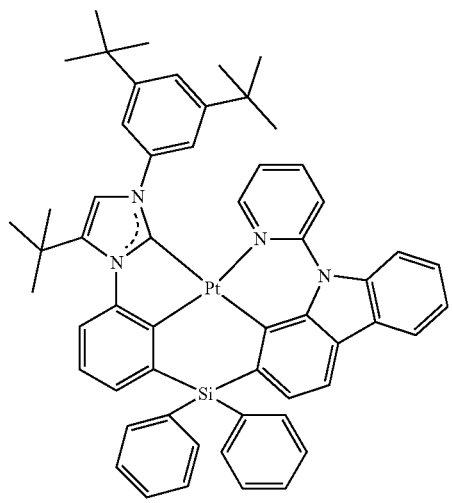
364
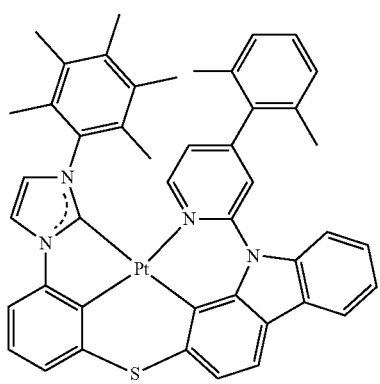
367
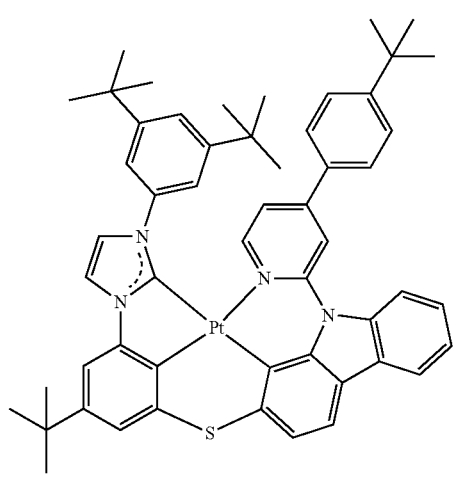
365
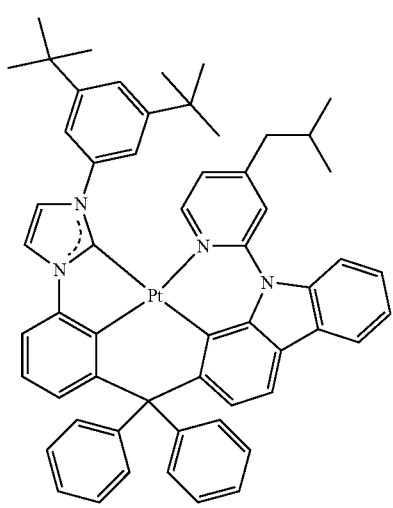
368
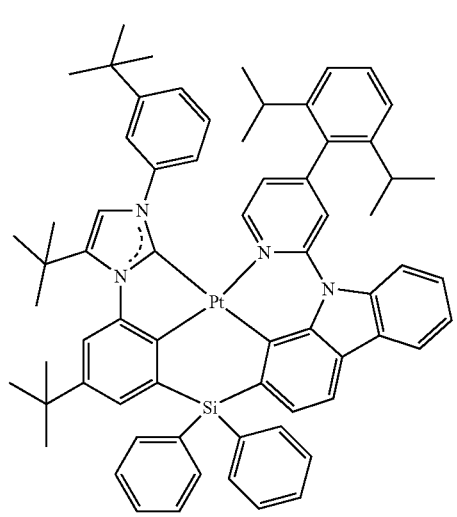

2739
-continued
369
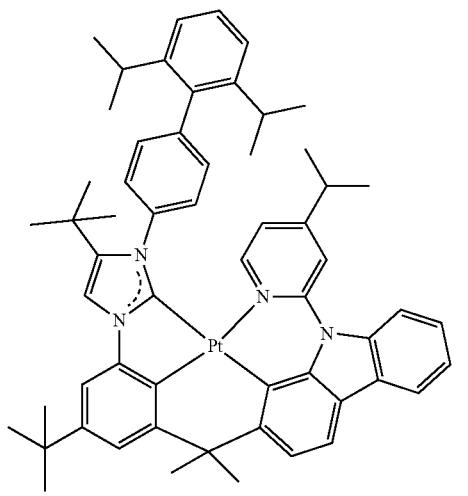
370
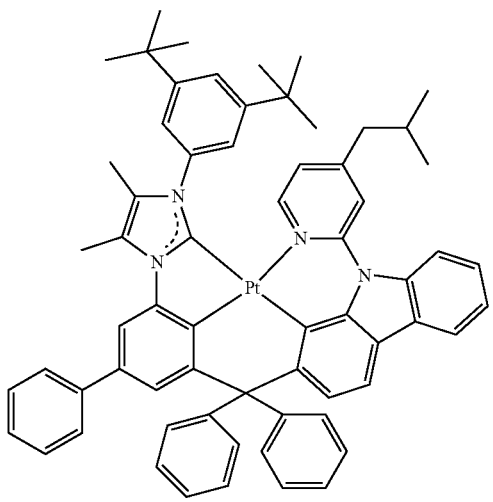
371
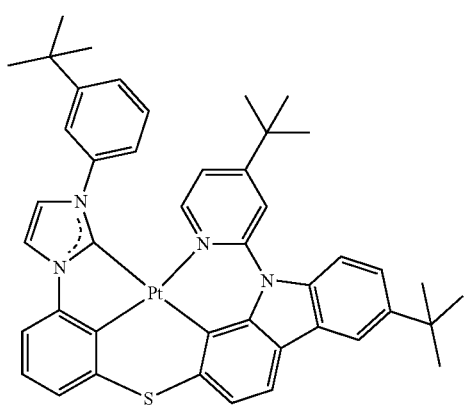
2740
-continued
372
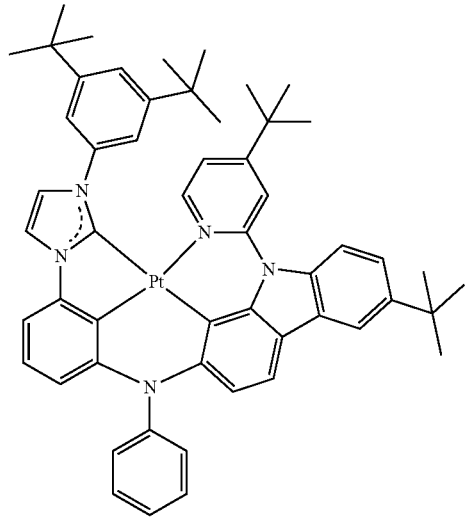
373
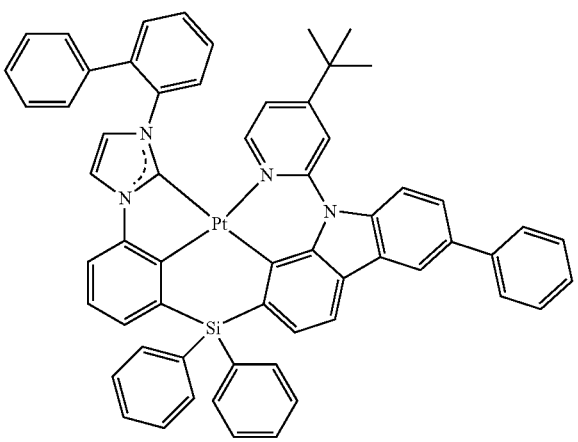
374
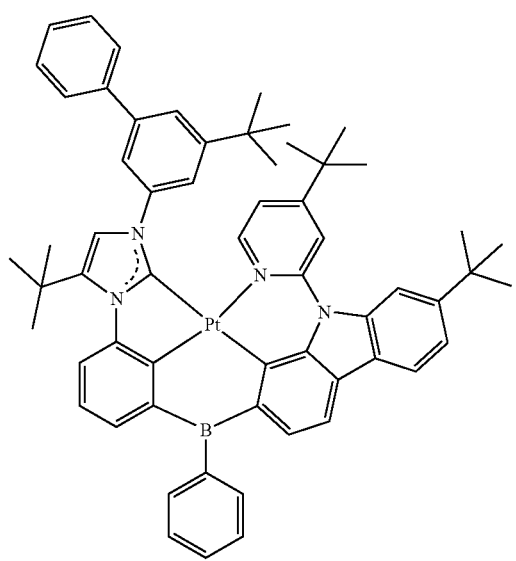

375
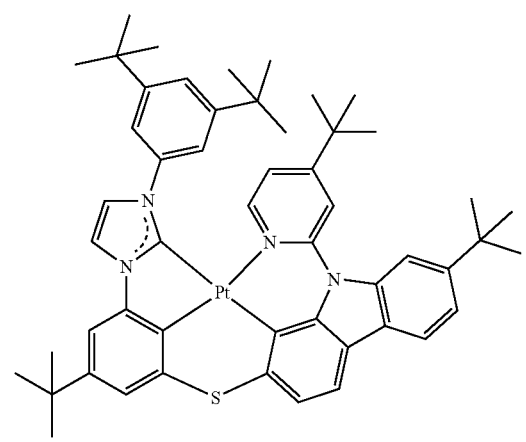
376
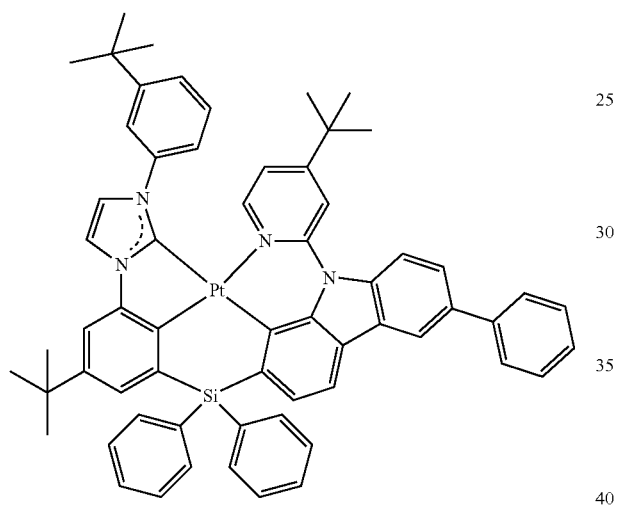
377
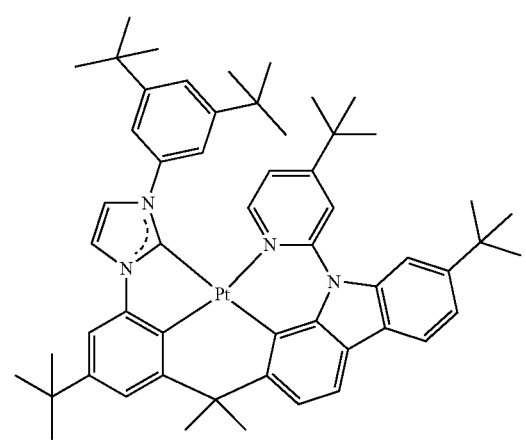
378
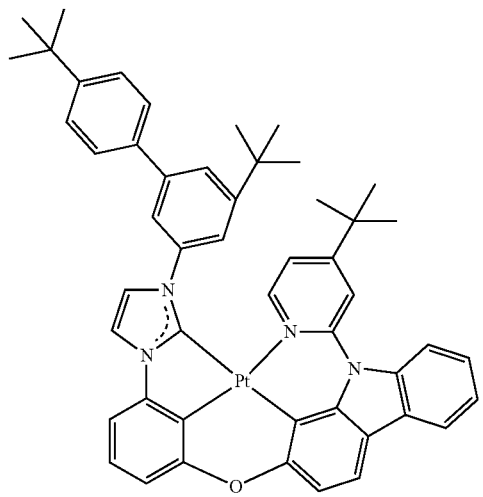
379
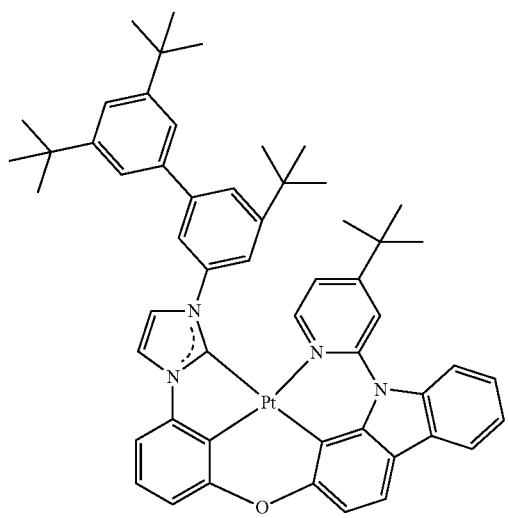
380
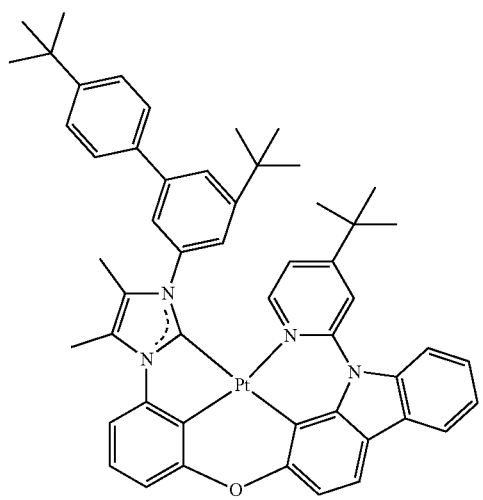

2743
-continued
381
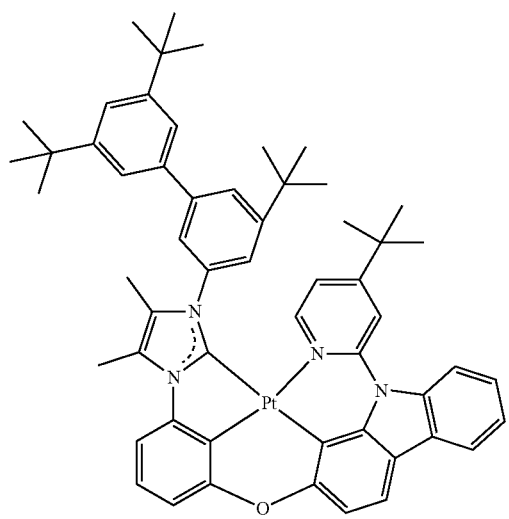
382
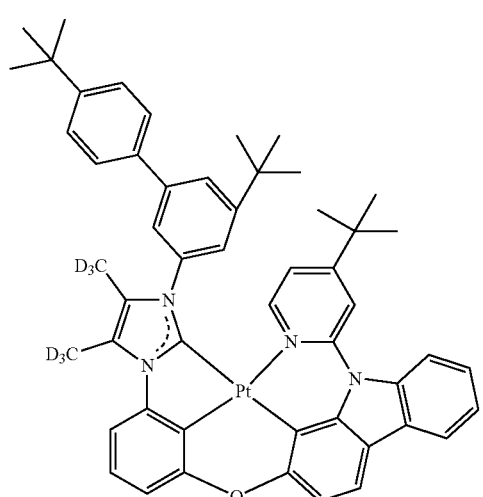
383
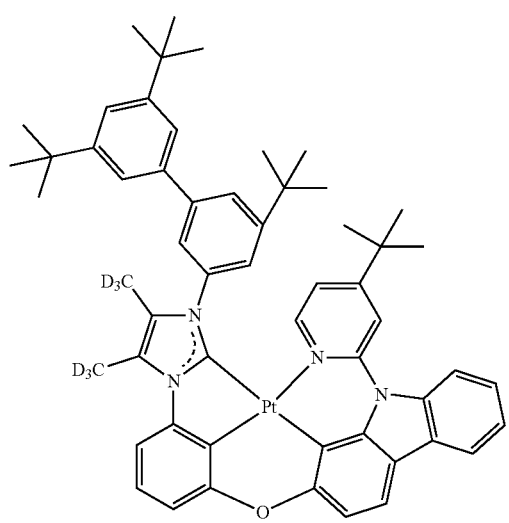
2744
-continued
384
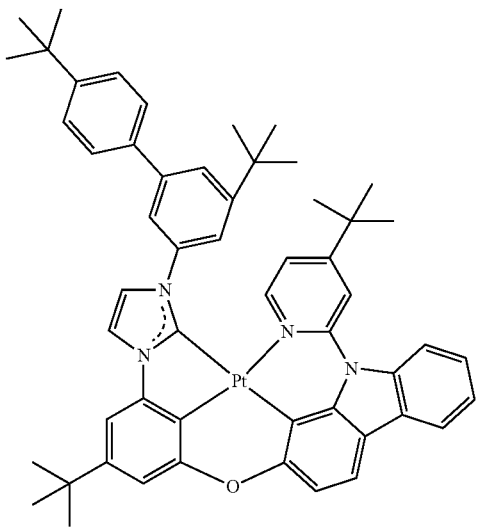
385
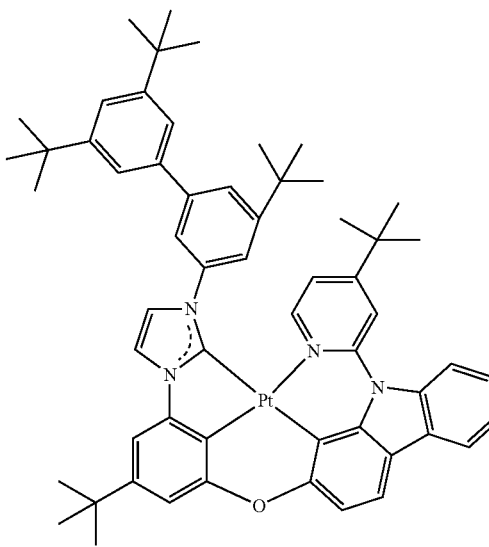
386
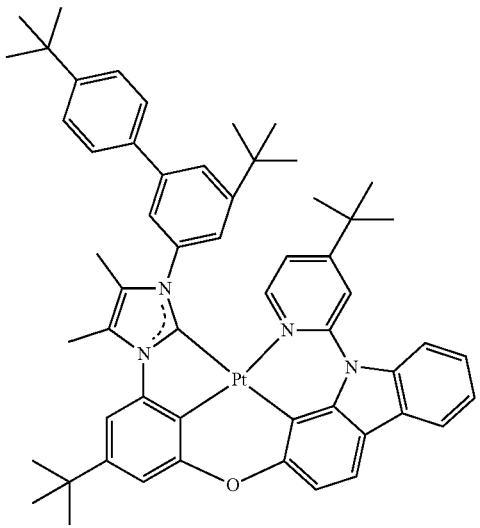

2745
-continued
387
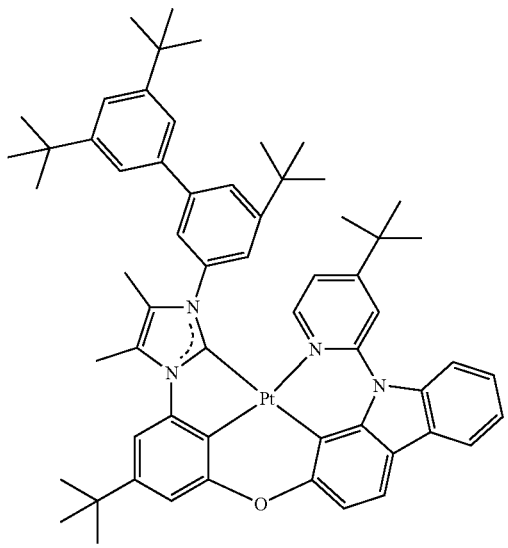
388
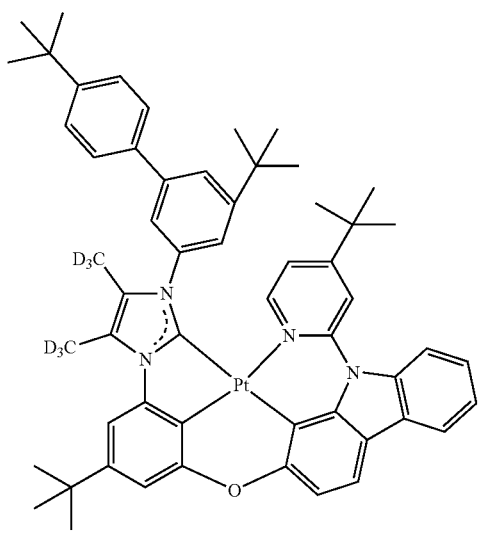
389
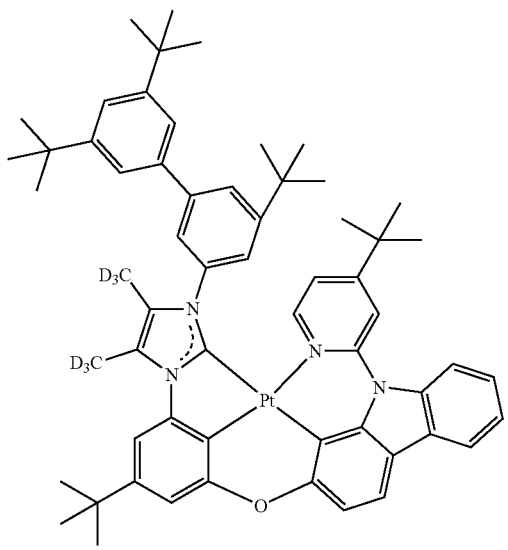
2746
-continued
390
391
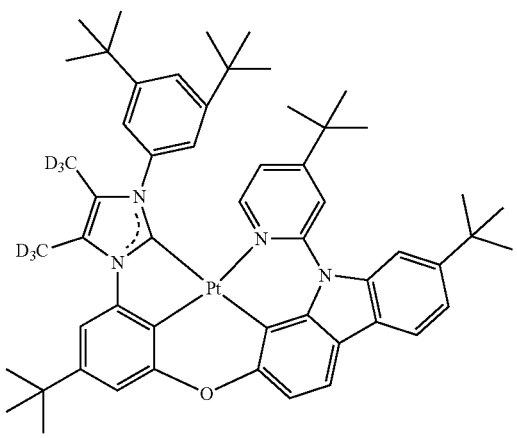
392
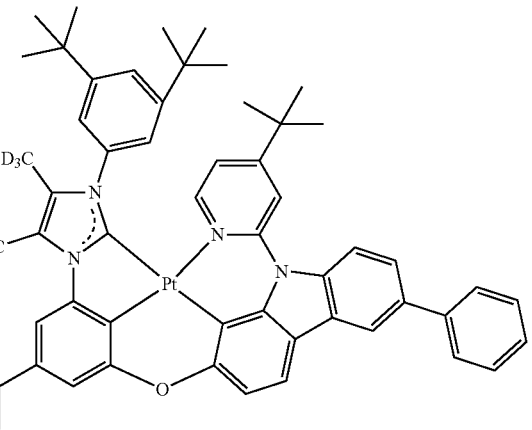

2747
-continued
393
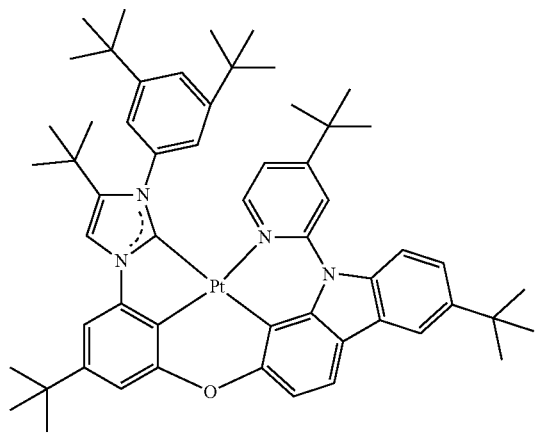
394
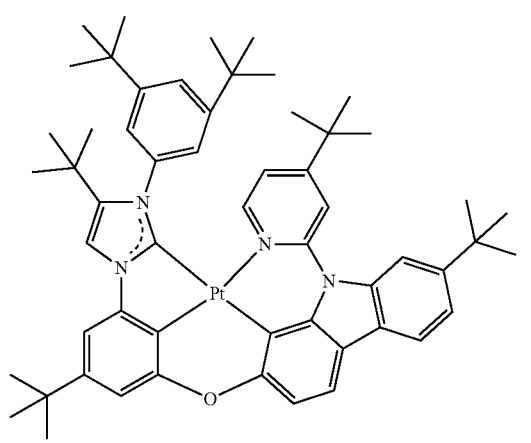
395
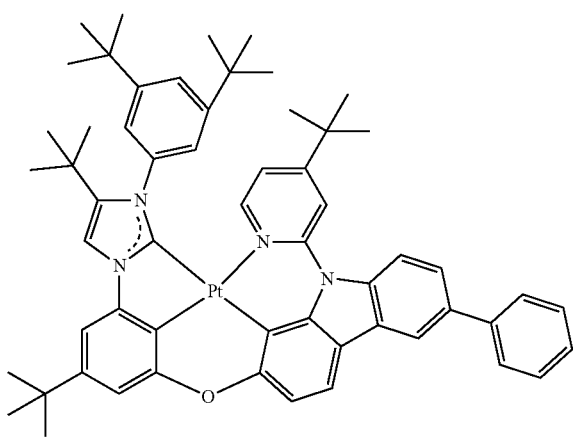
2748
-continued
396
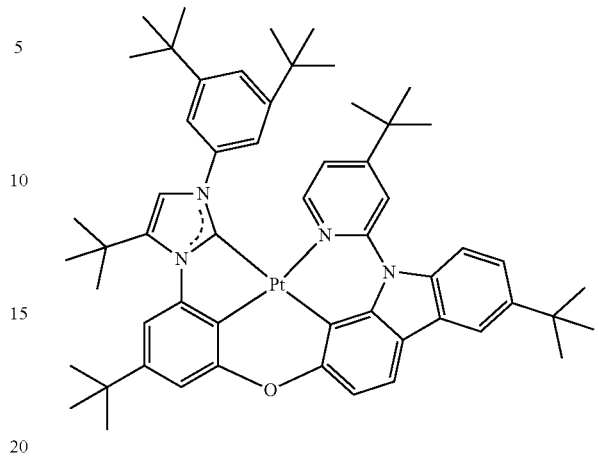
397
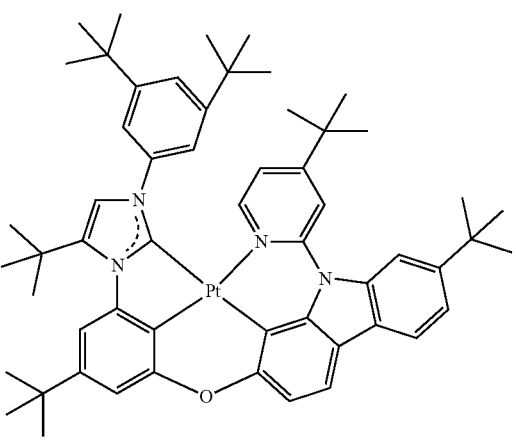
398
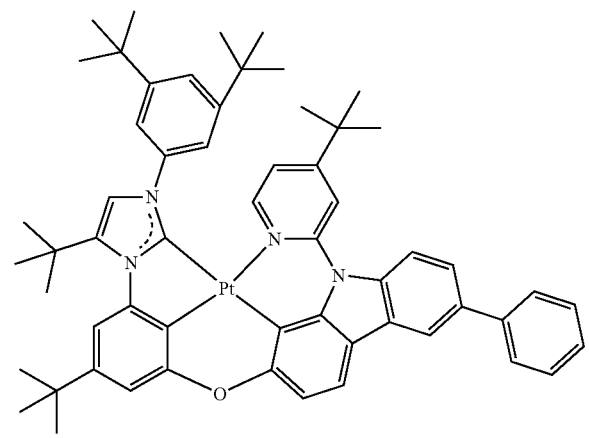

2749
-continued
399
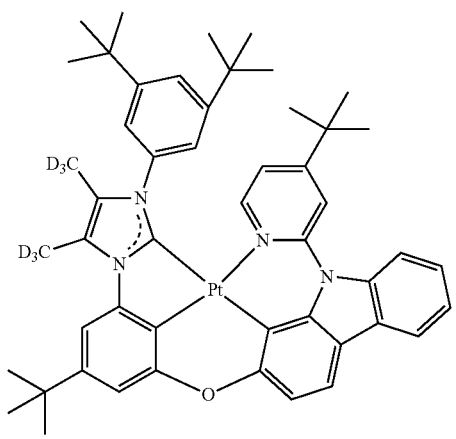
400
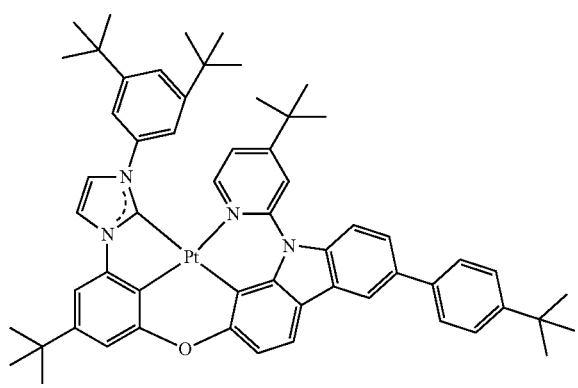
401
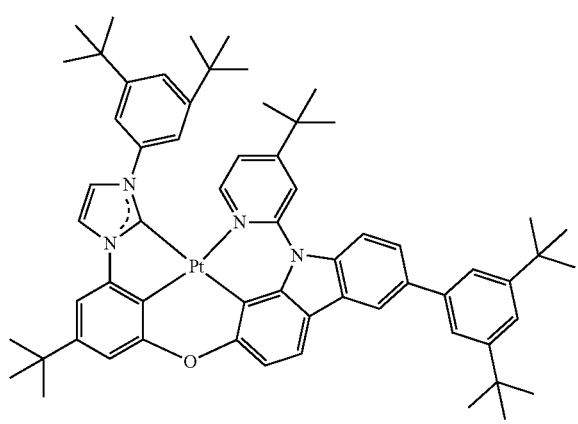
2750
-continued
402
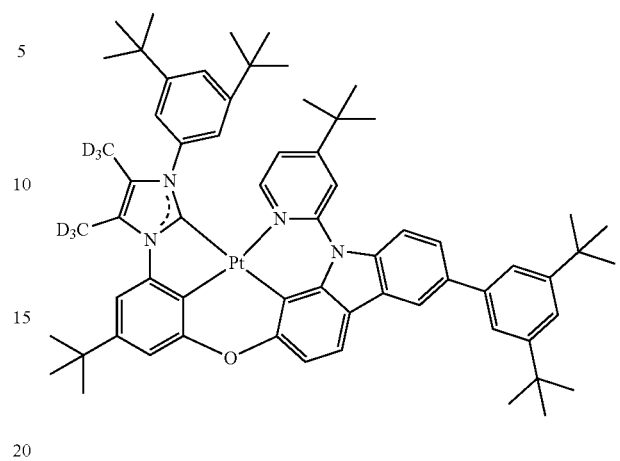
403
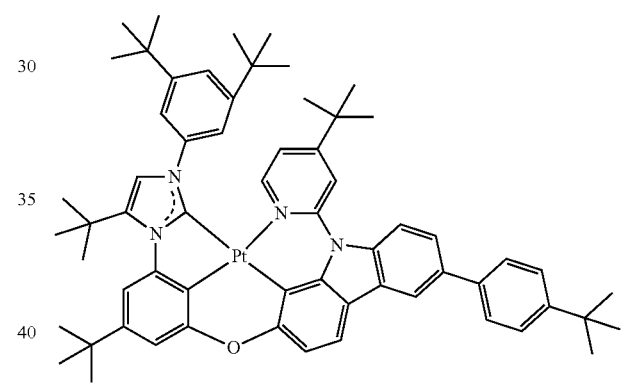
404
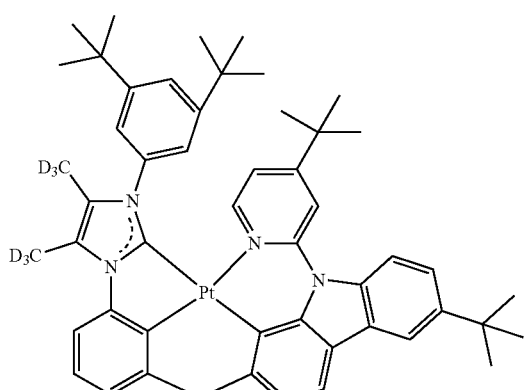

405
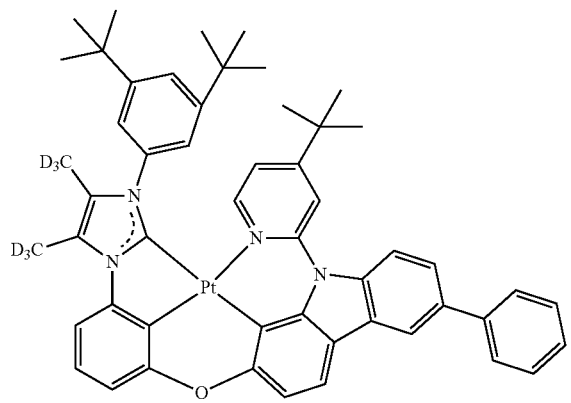
406
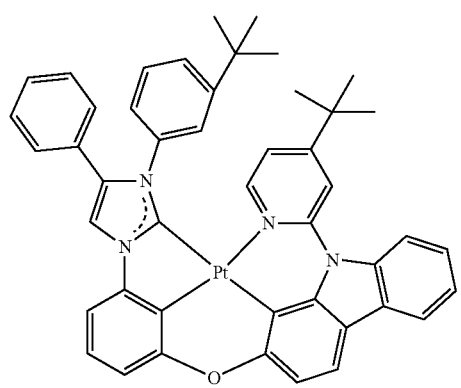
407
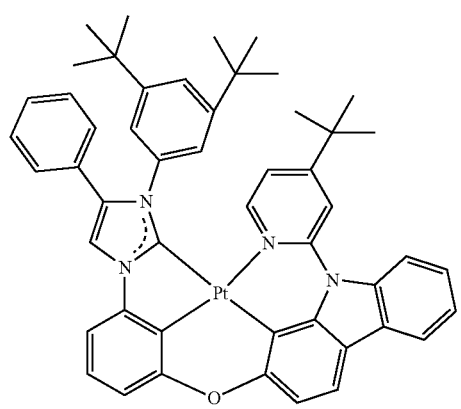
408
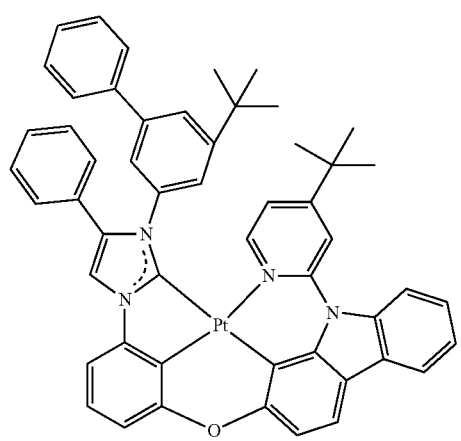
409
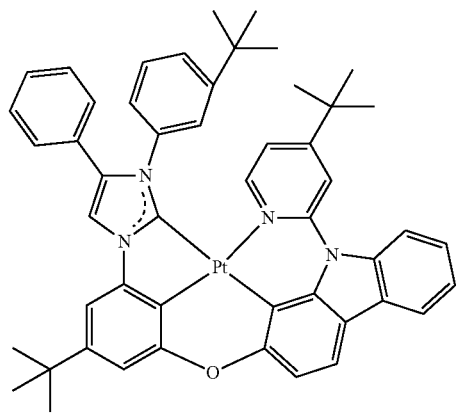
410
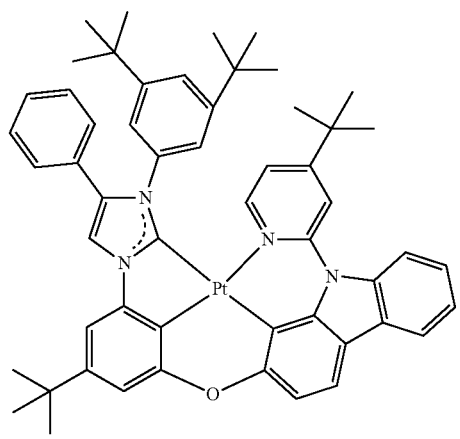
411

2753
-continued
412
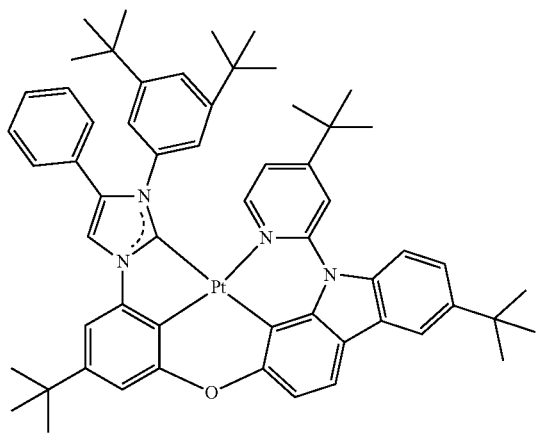
413
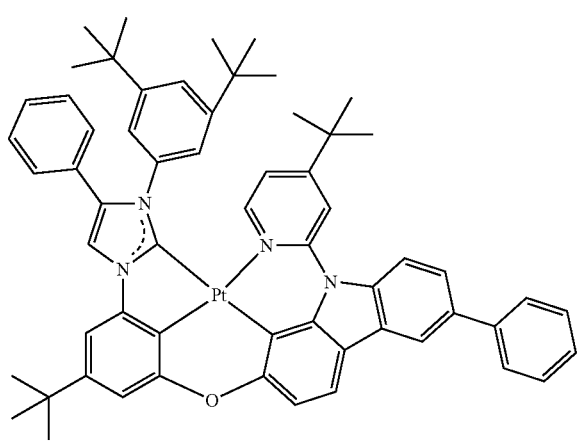
414
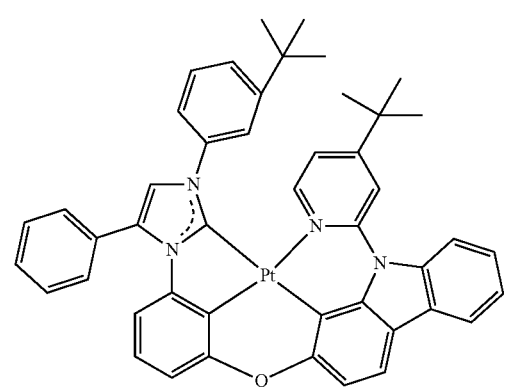
2754
-continued
415
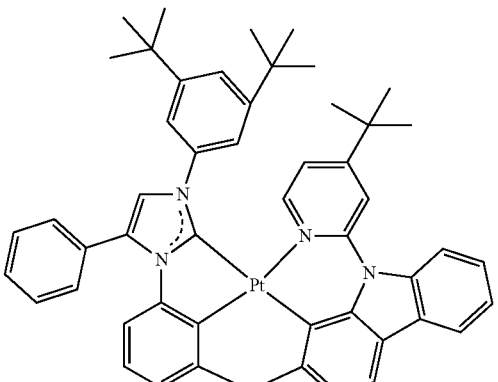
416
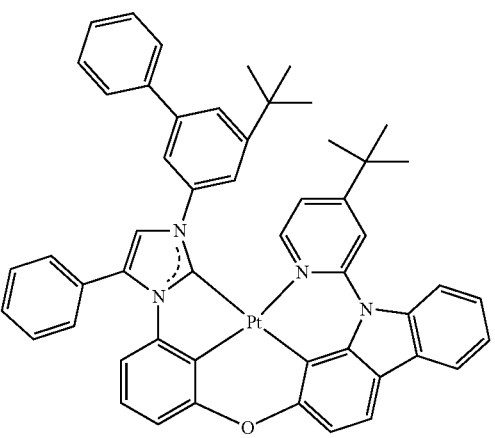
417
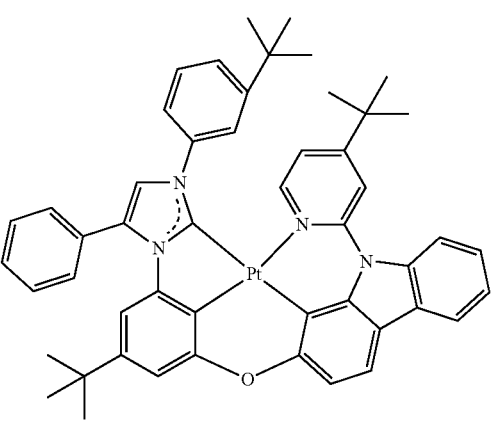

2755
-continued
418
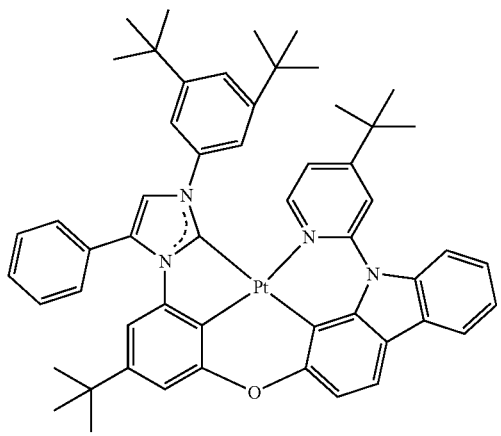
419
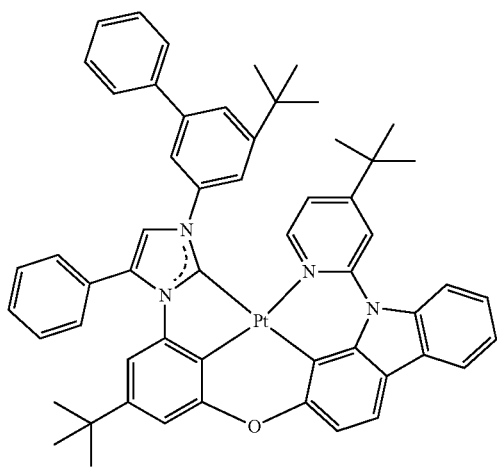
420
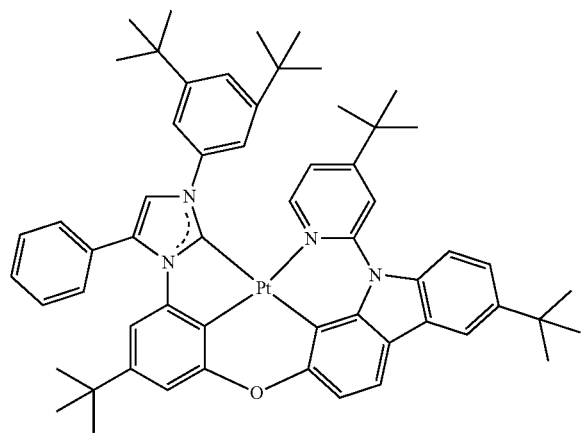
2756
-continued
421
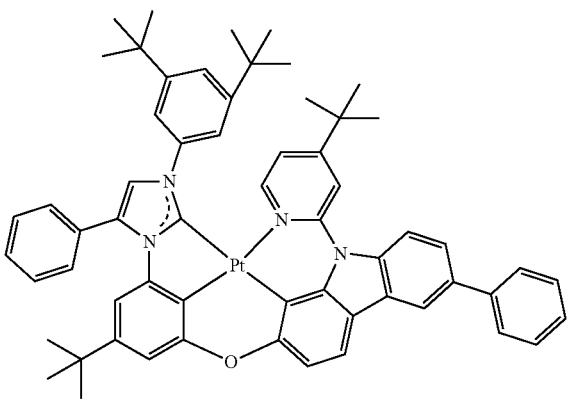
422
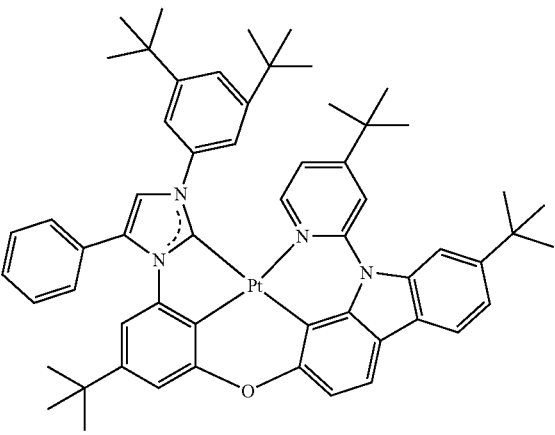
423
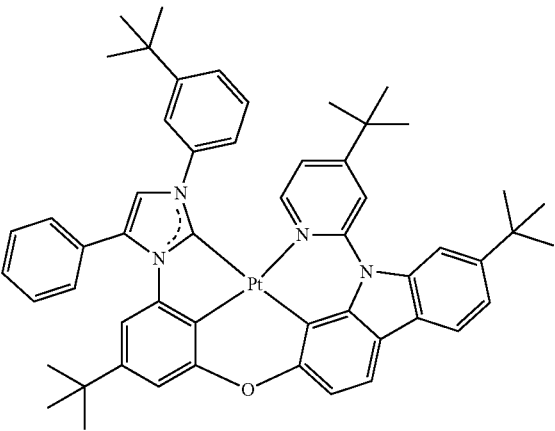

2757
-continued
424
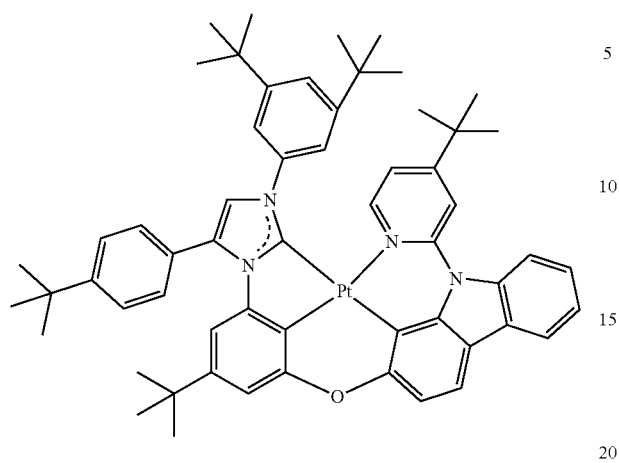
425
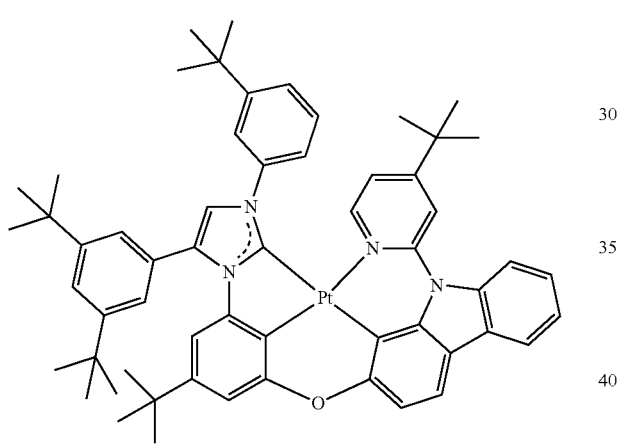
426
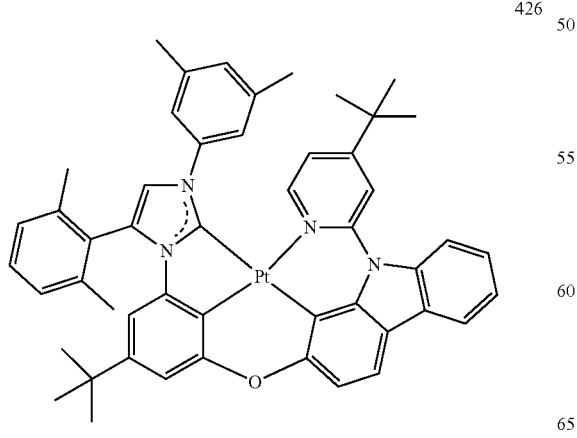
2758
-continued
427
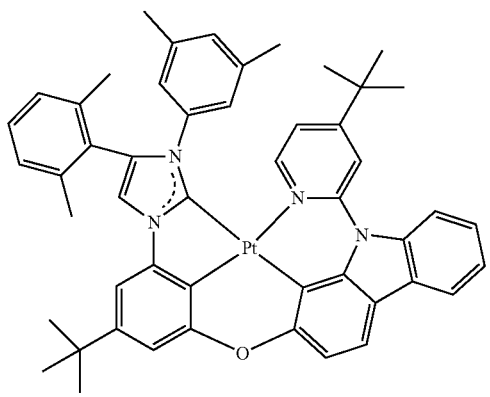
428
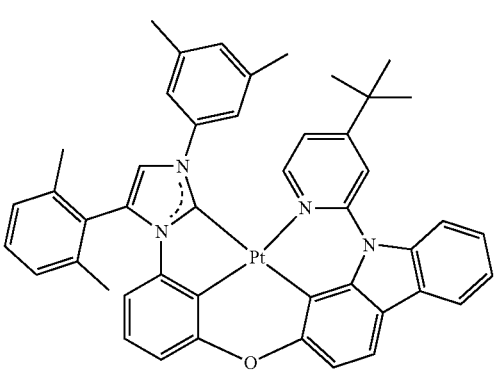
Group X
1
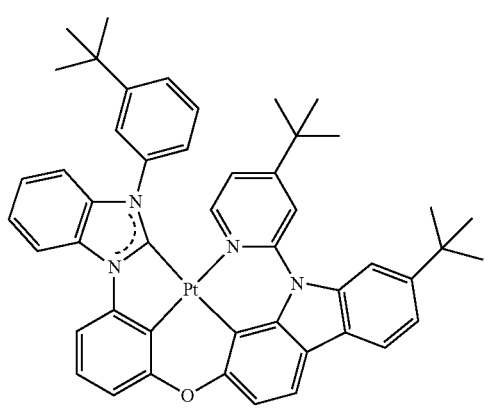

2
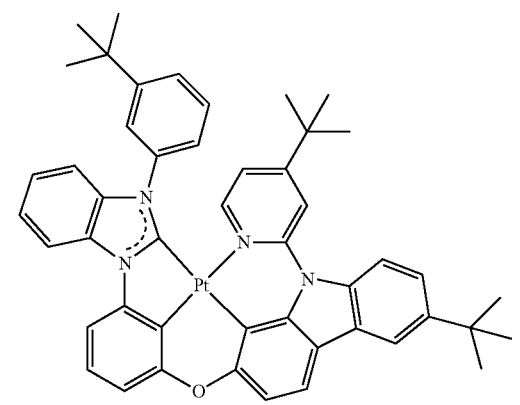
3
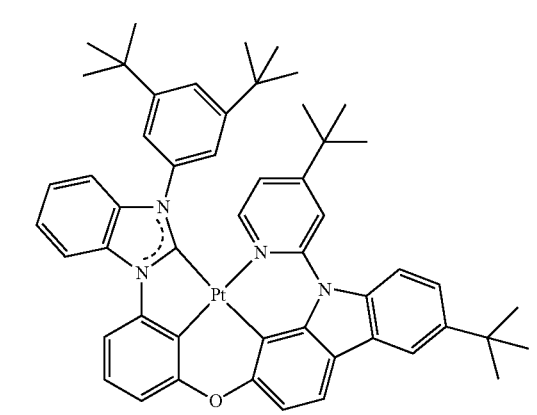
4
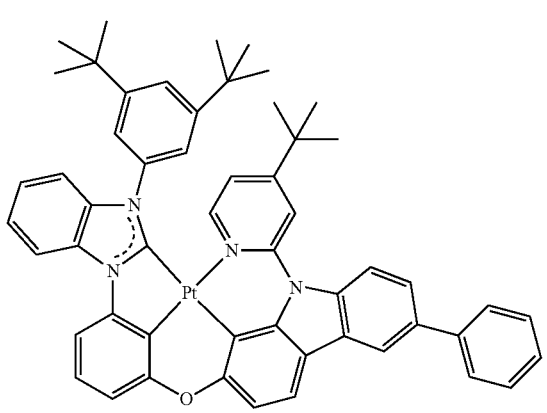
5
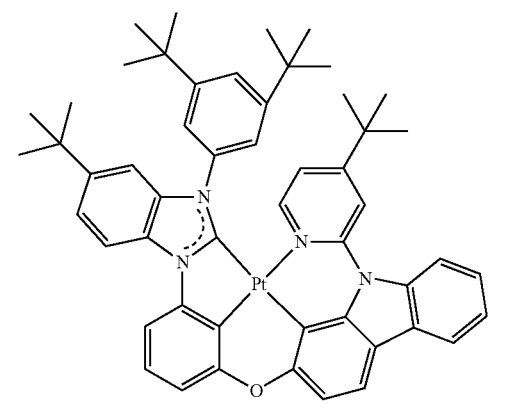
6
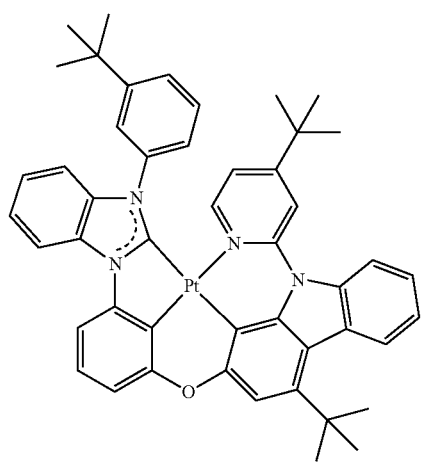
7
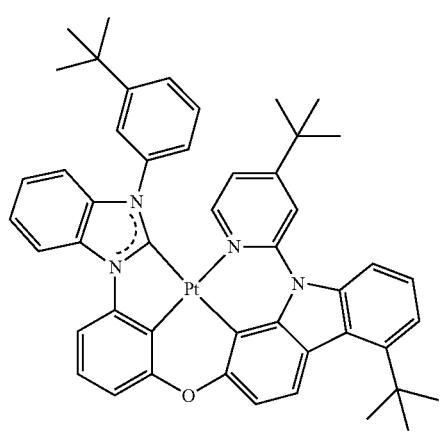
8
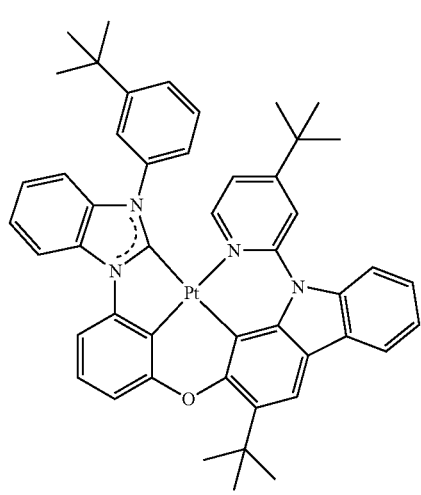

2761
-continued
9
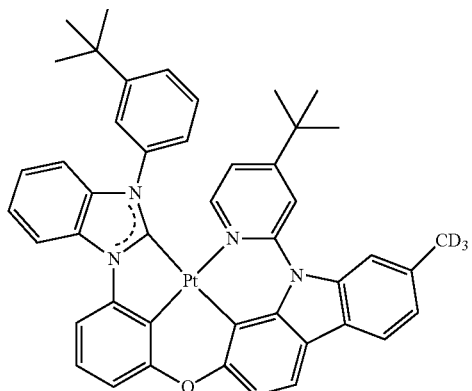
10
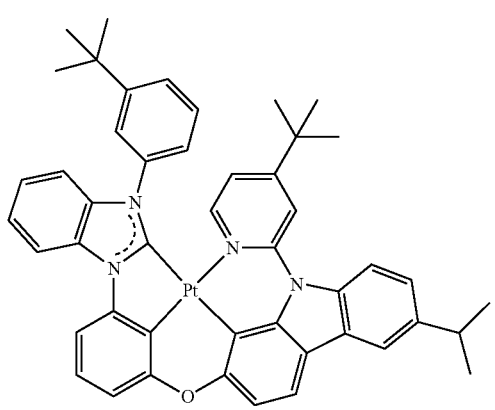
11
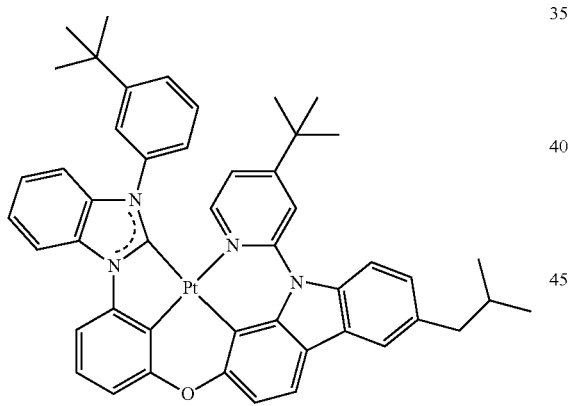
12
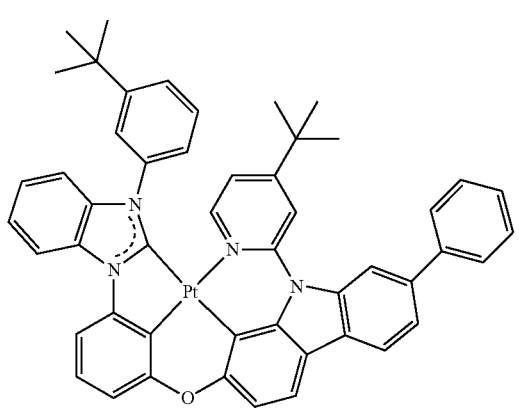
2762
-continued
13
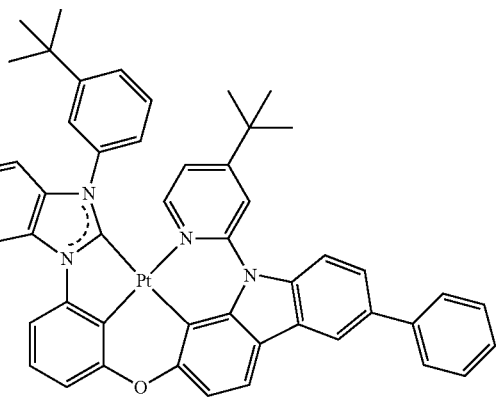
14
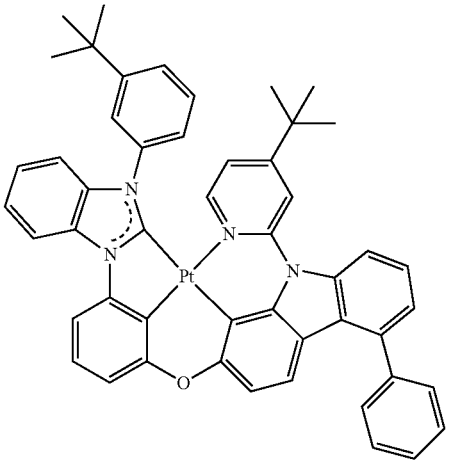
15
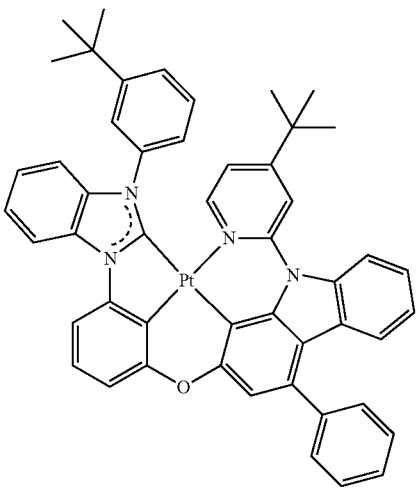

16
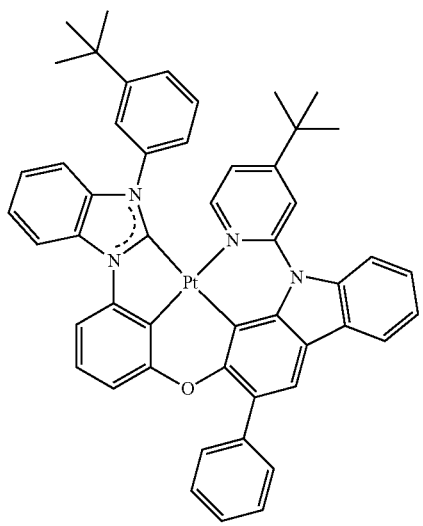
17
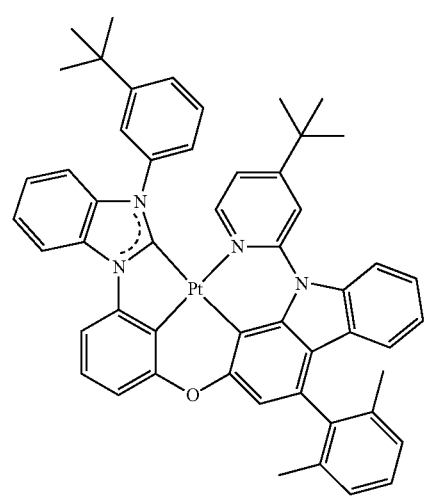
18
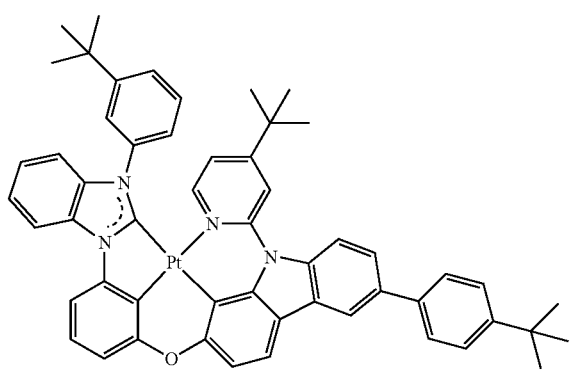
19
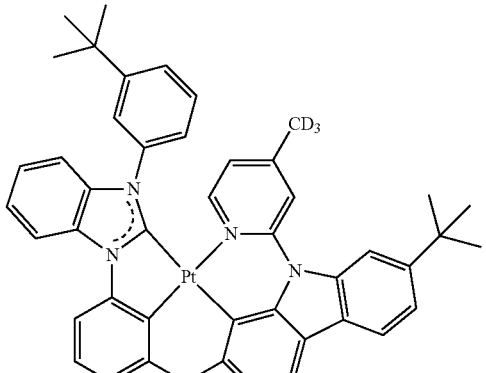
20
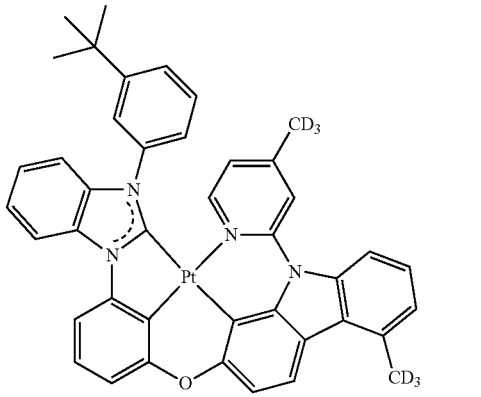
21
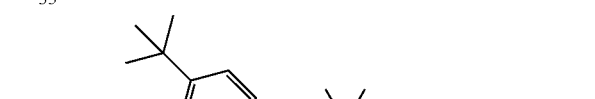
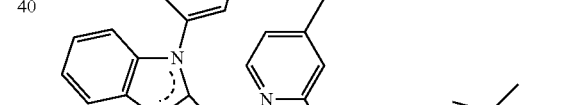
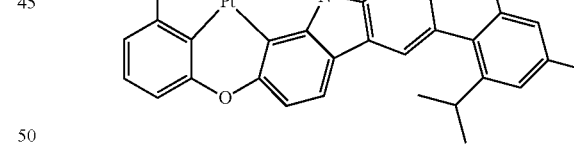

22
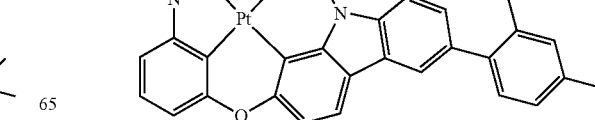
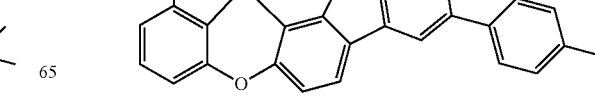

23
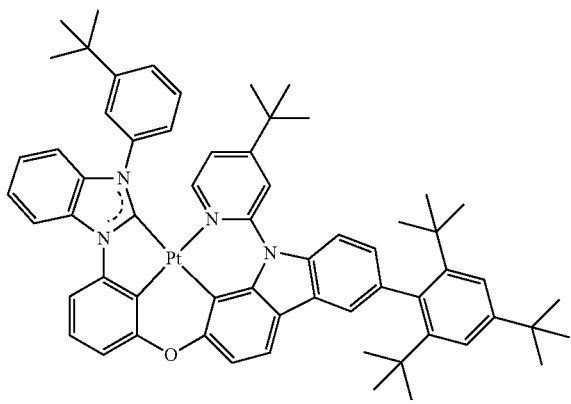
24
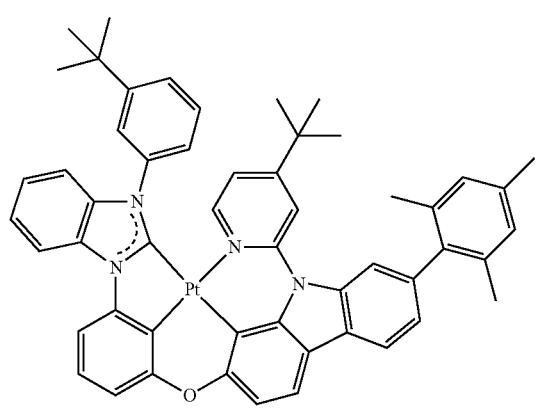
25
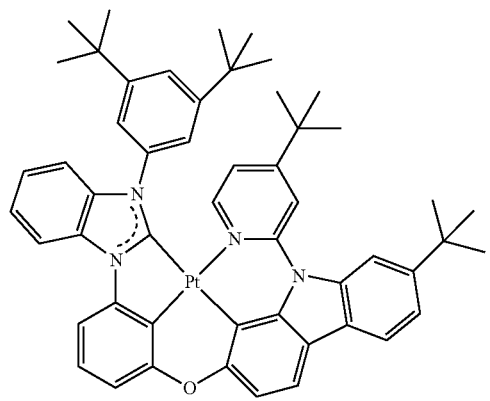
26
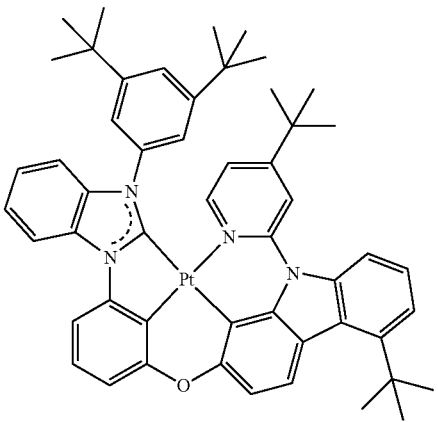
27
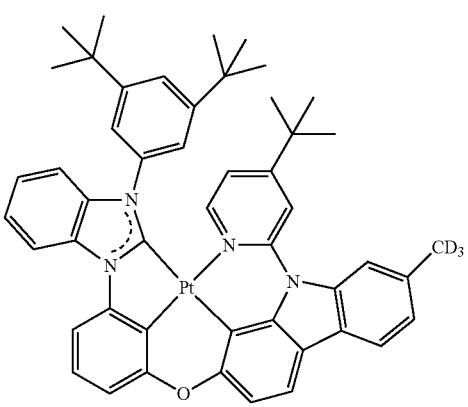
28
29
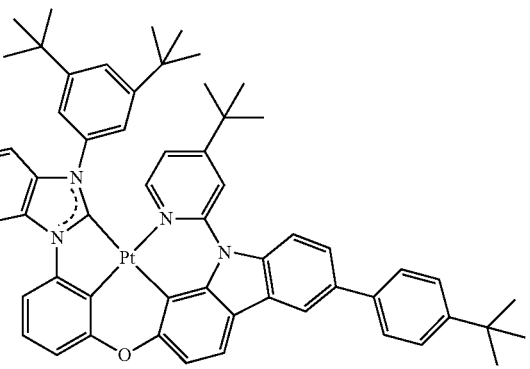

2767
-continued
30
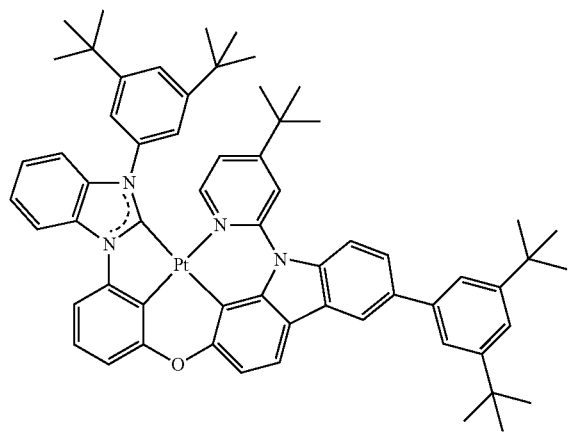
31
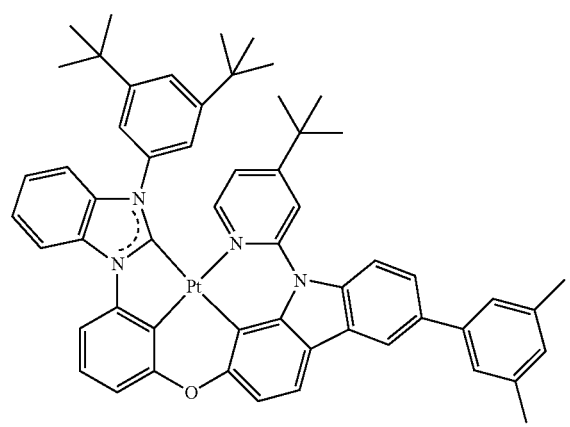
32
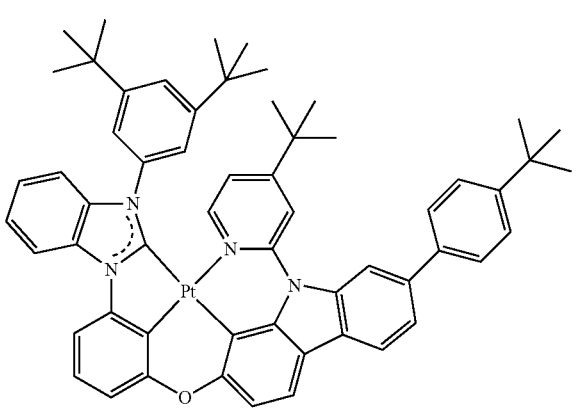
2768
-continued
33
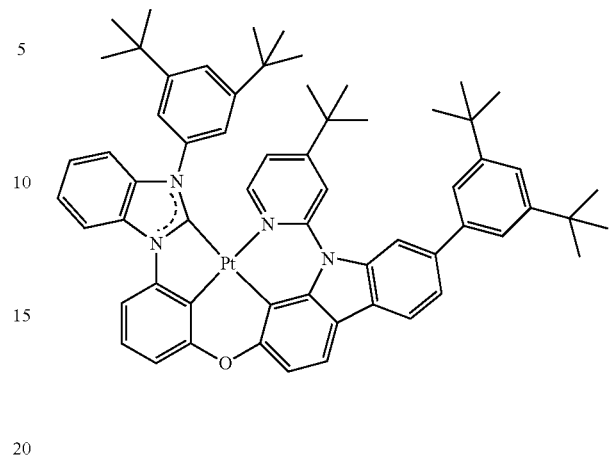
34
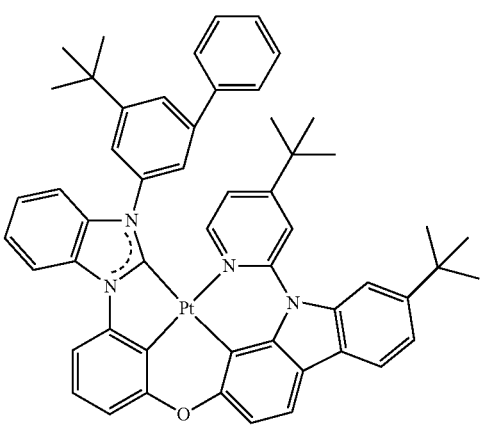
35
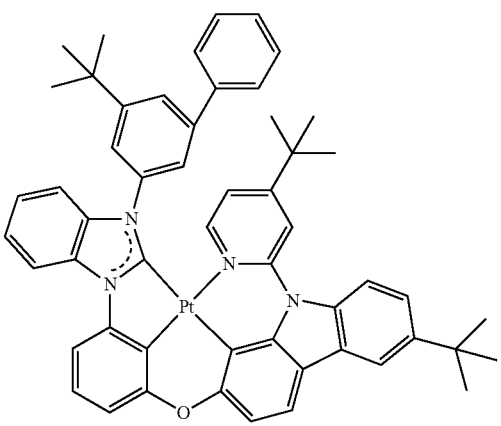

2769
-continued
36
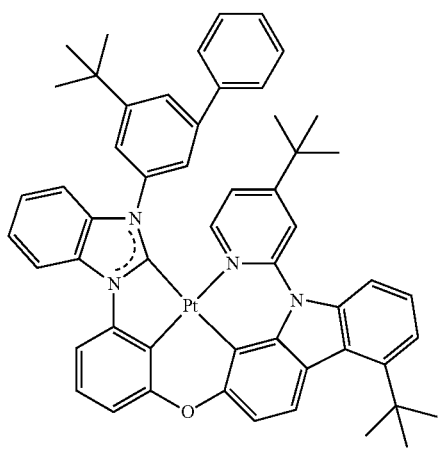
37
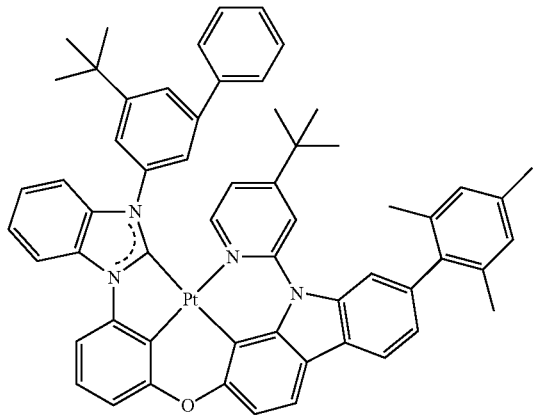
38
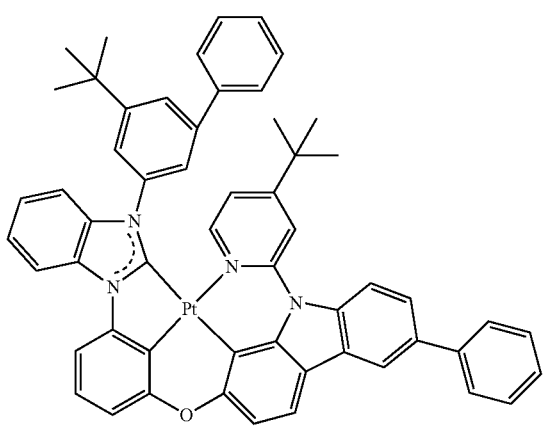
2770
-continued
39
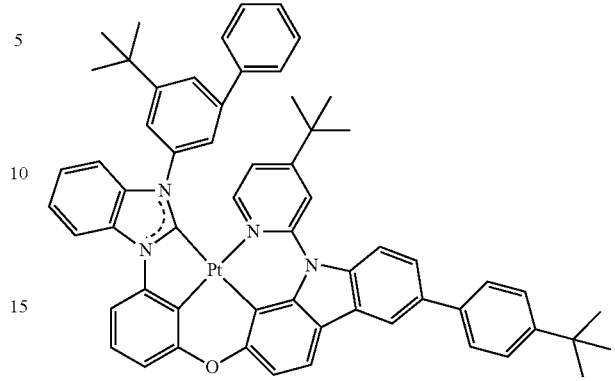
40
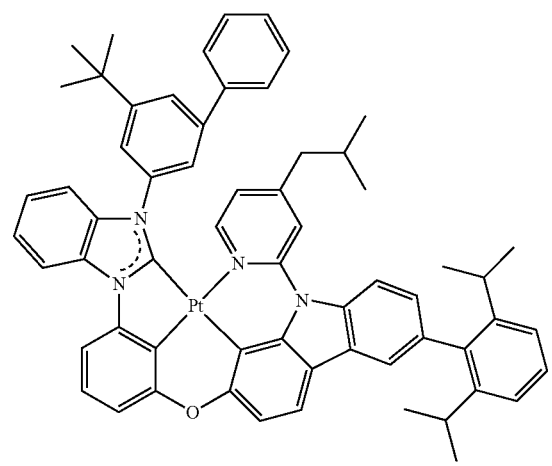
41
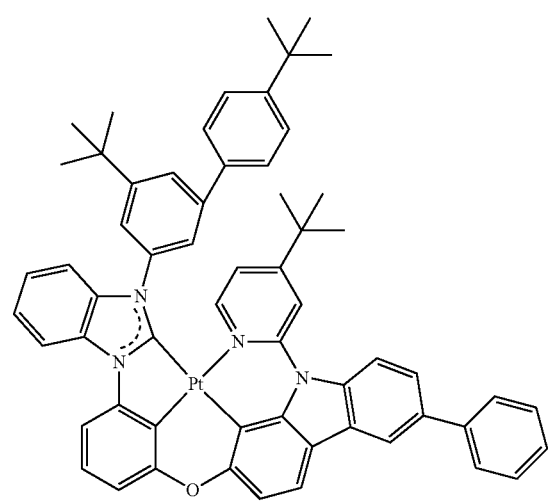

2771
-continued
42
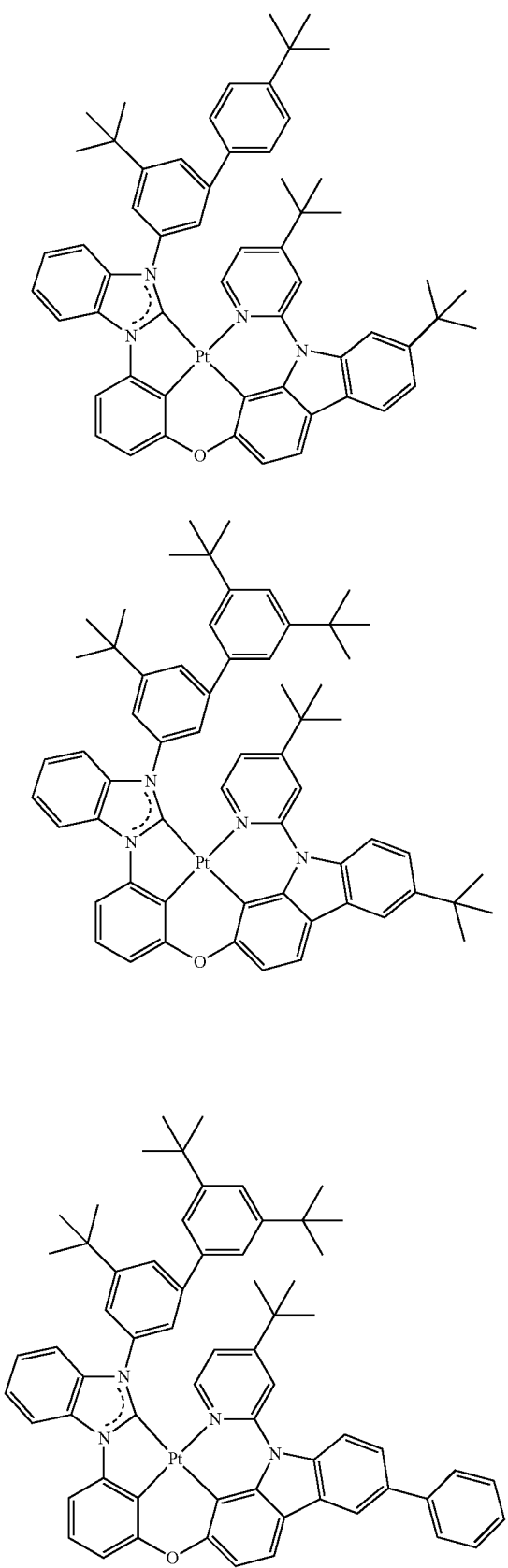
43
44
2772
-continued
45
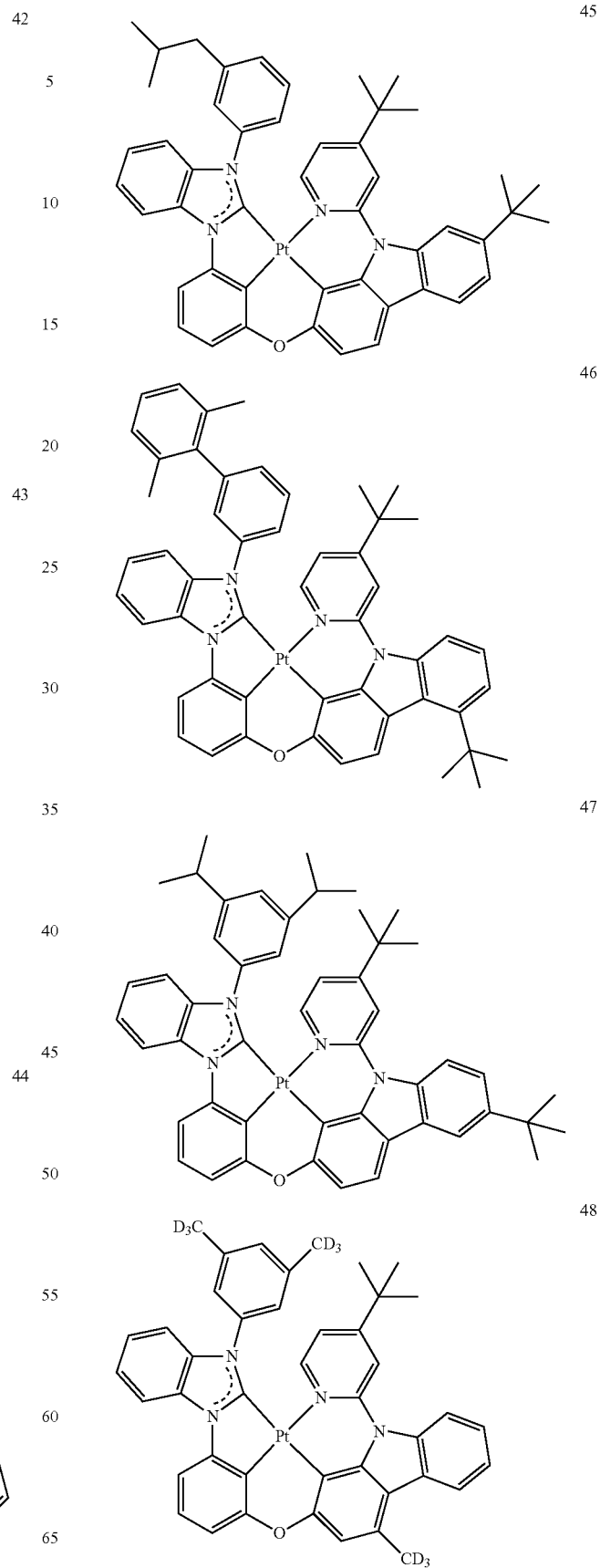
46
47
48

49
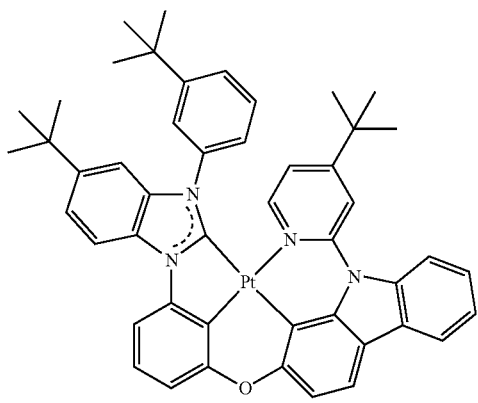
50
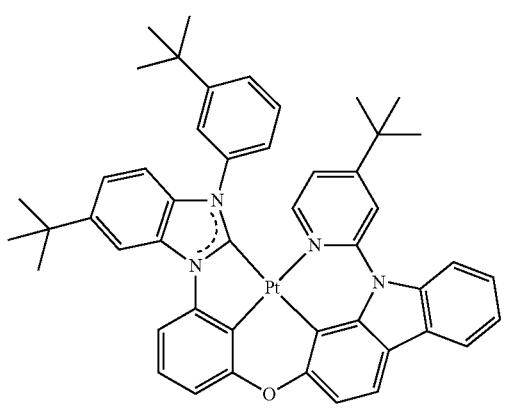
51
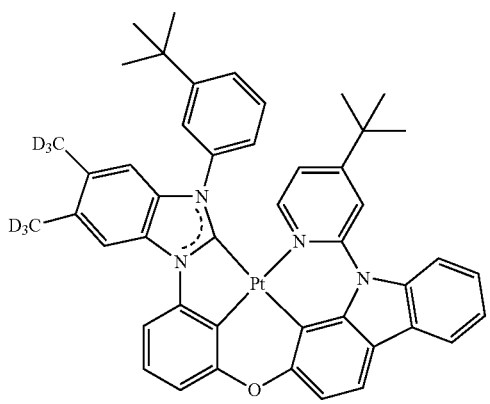
52
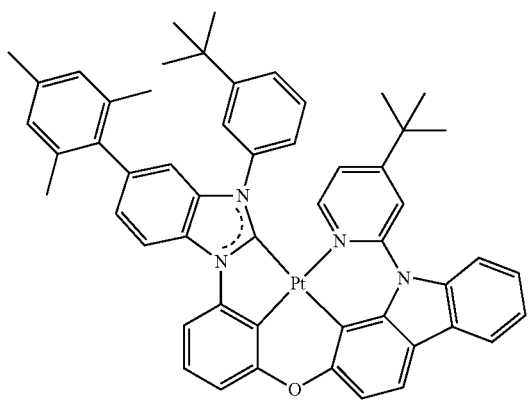
53
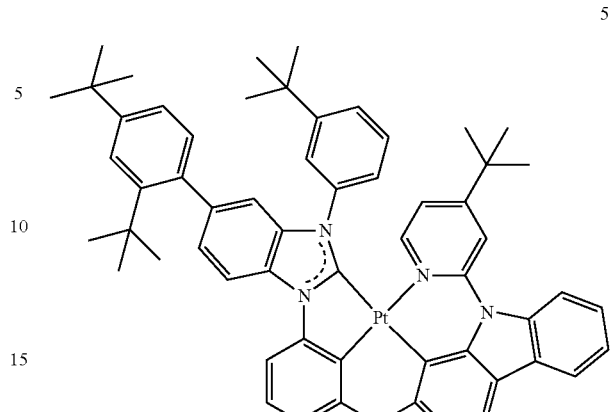
54
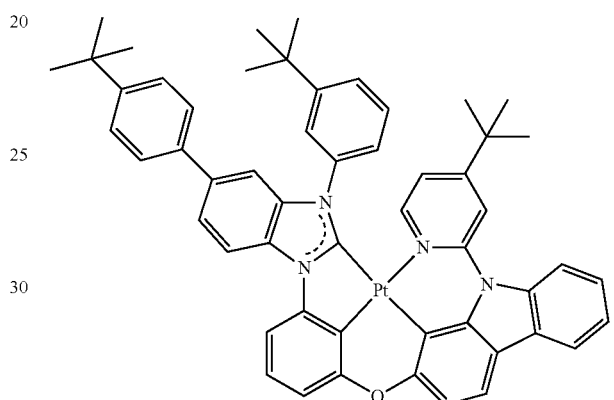
55
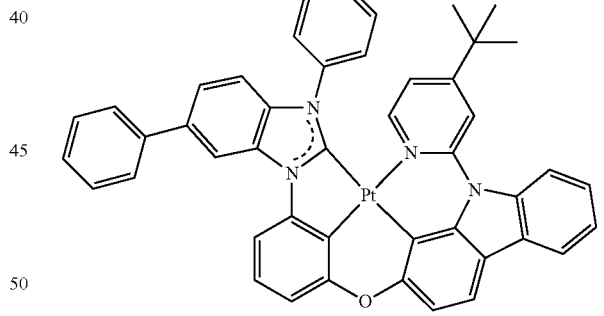
56

2775
-continued
57
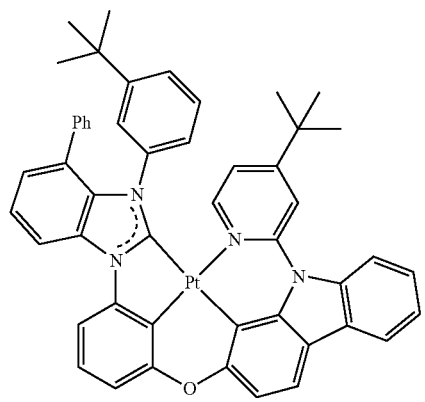
58
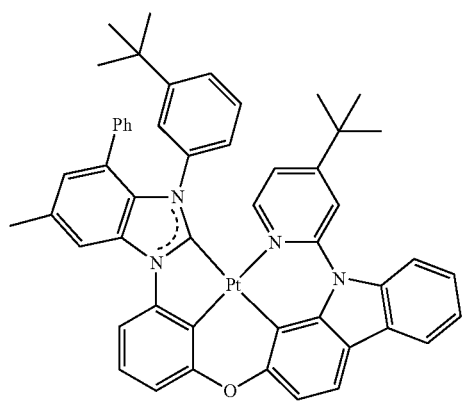
59
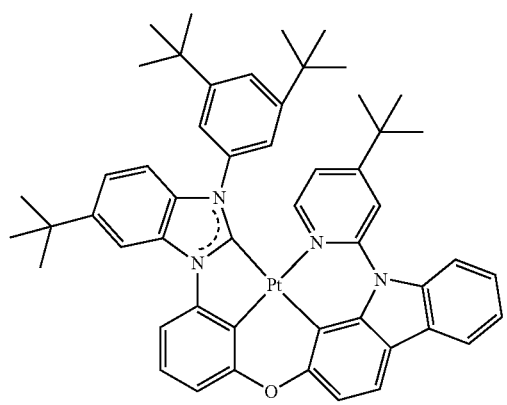
60
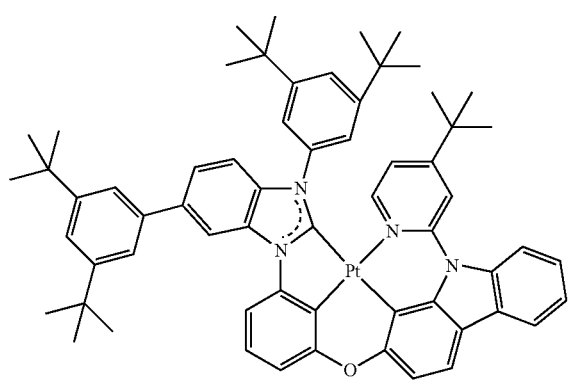
2776
-continued
61
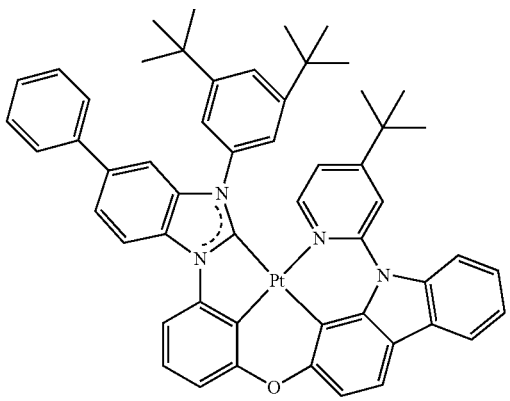
62
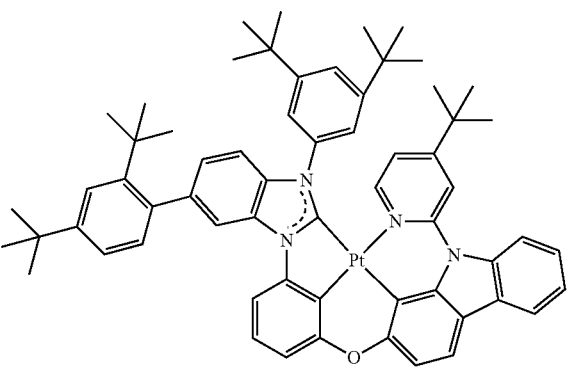
63
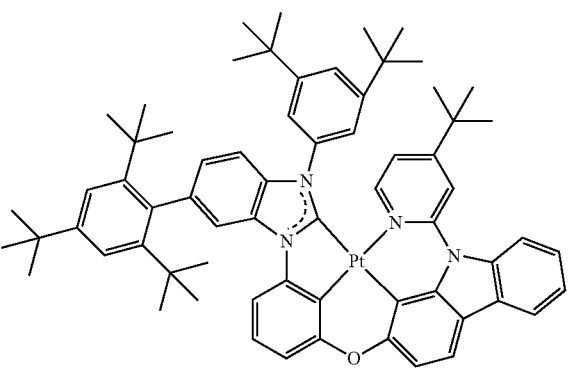
64
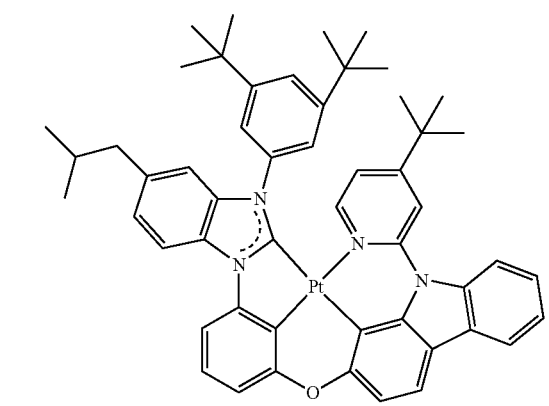

2777
-continued
65
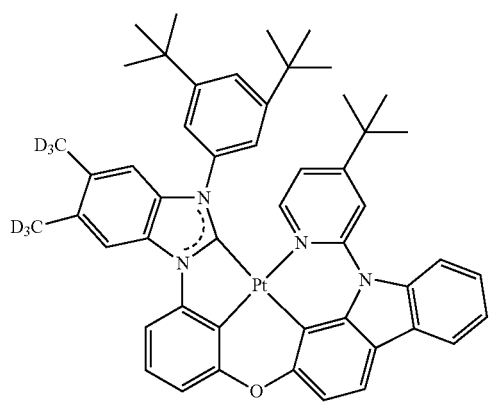
66
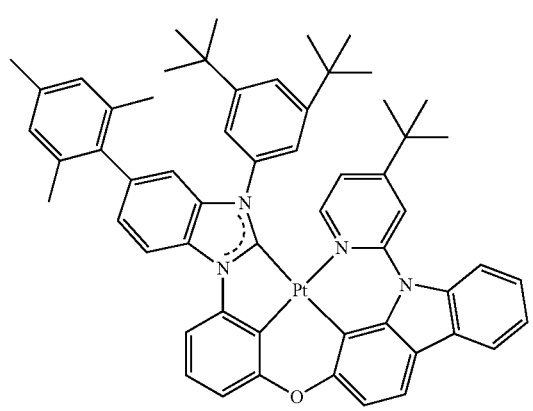
67
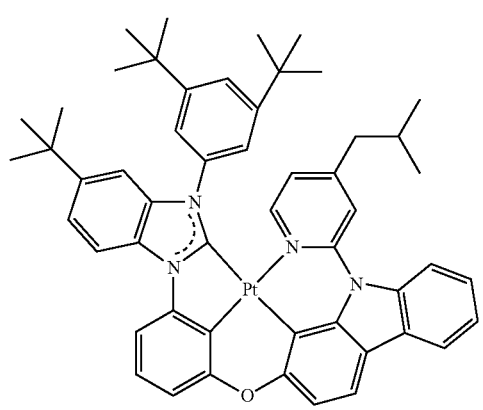
68
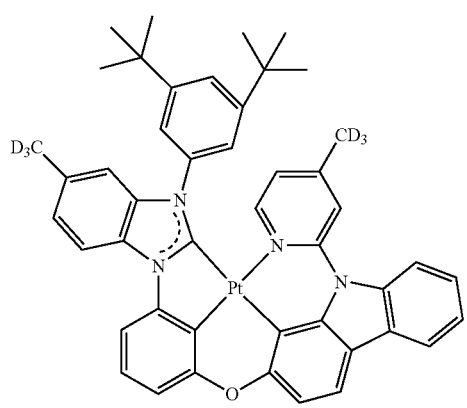
2778
-continued
69
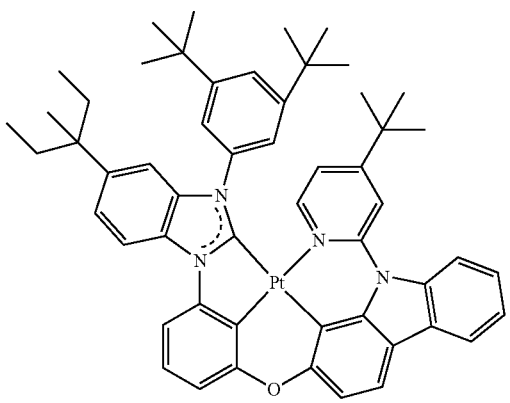
70
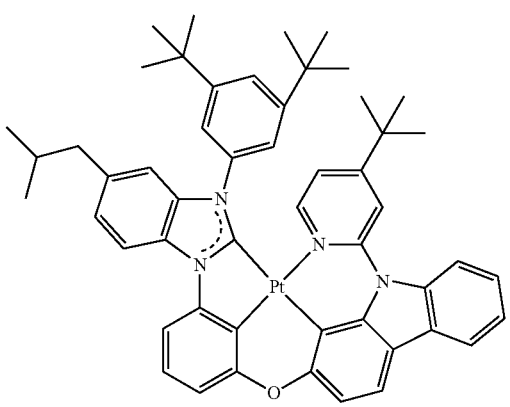
71
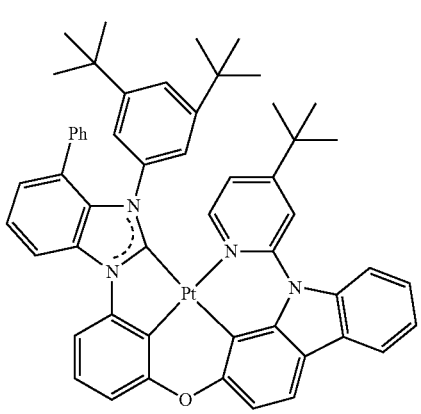

72
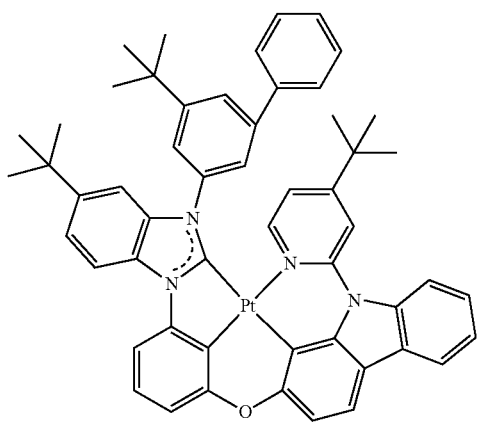
73
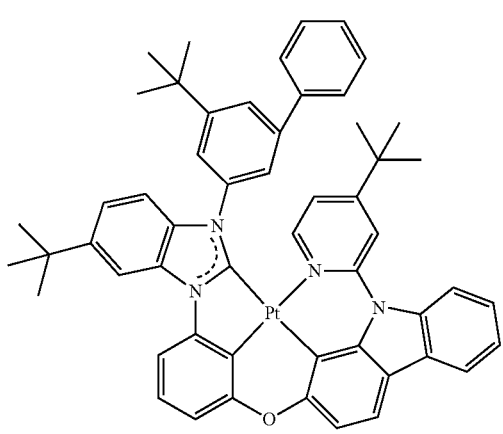
74
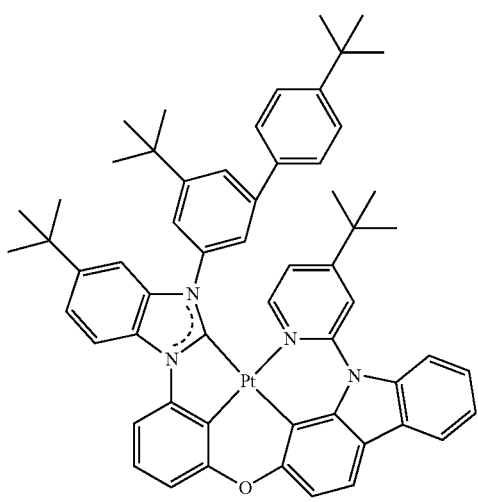
75
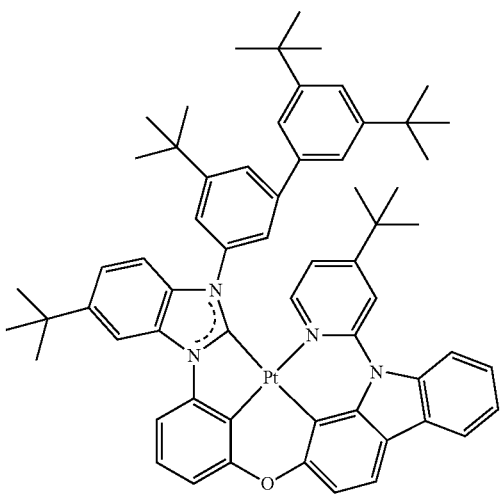
76
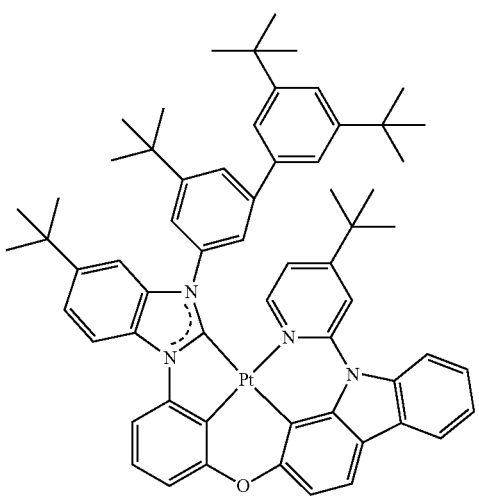
77
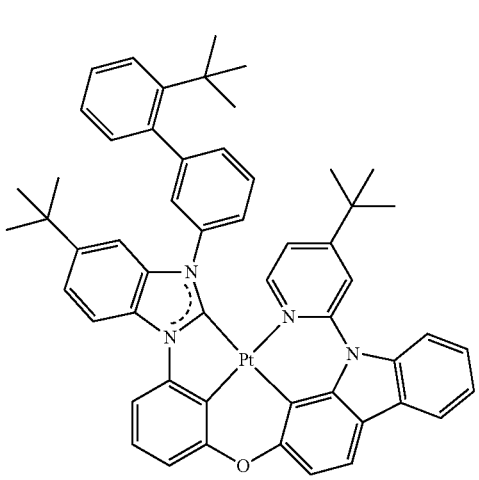

2781
-continued
78
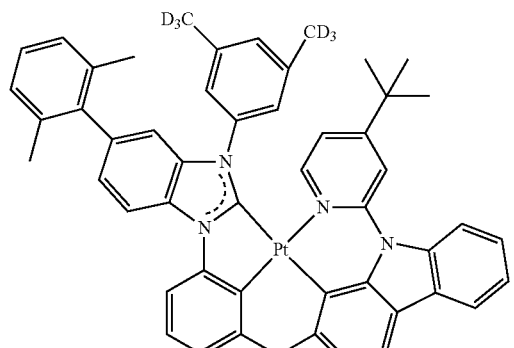
79
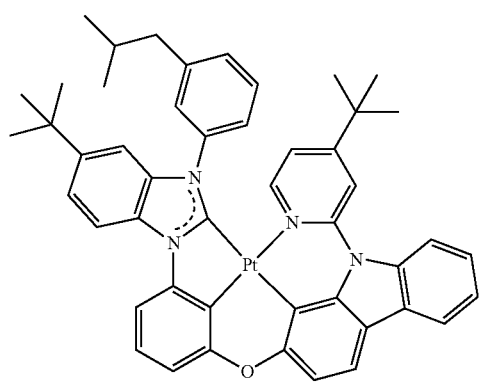
80
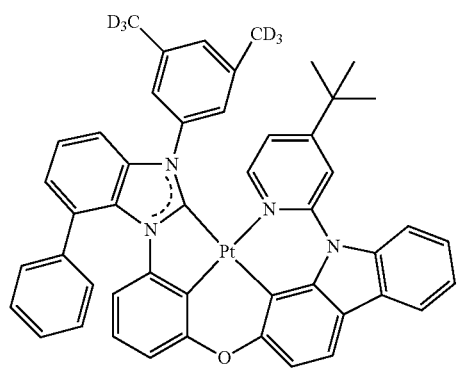
81
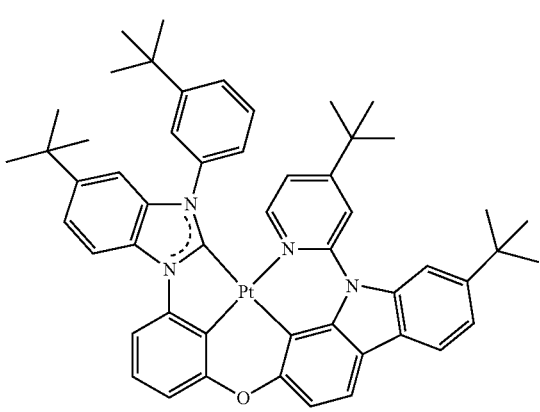
2782
-continued
82
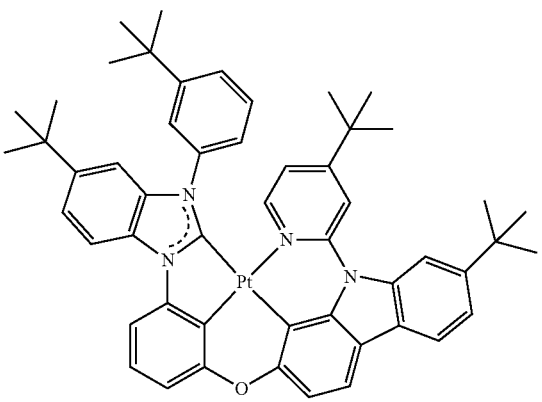
83
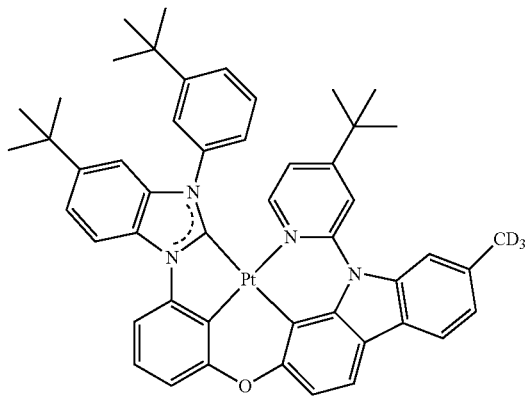
84
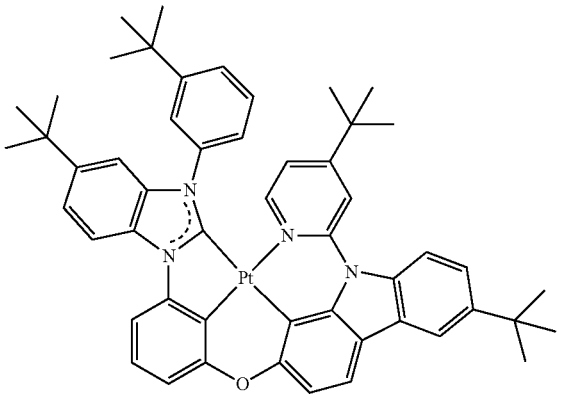

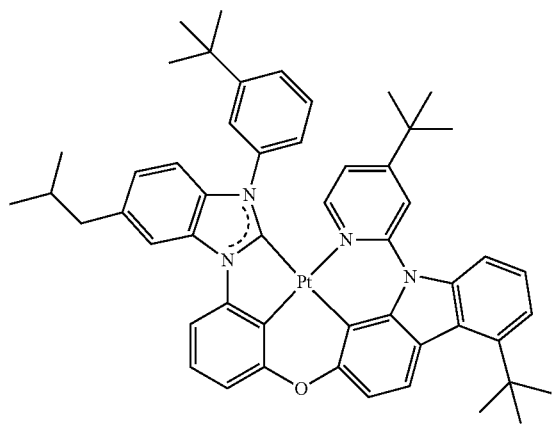
85
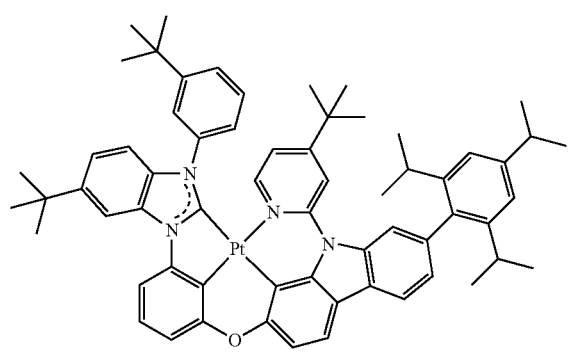
86
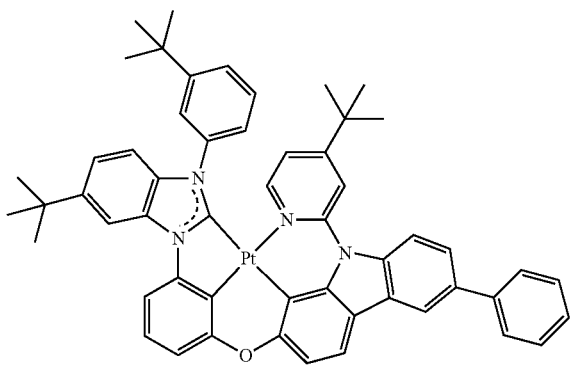
87
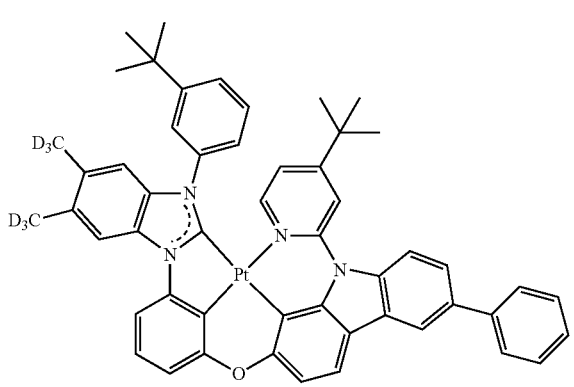
88
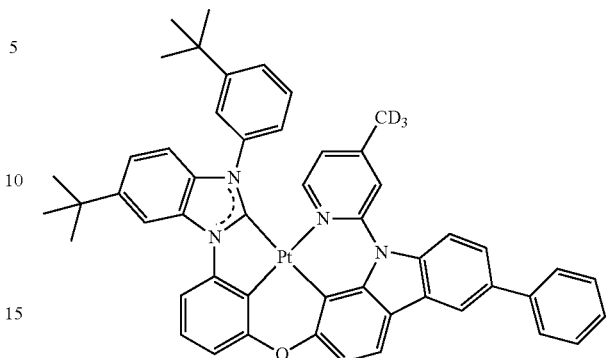
89
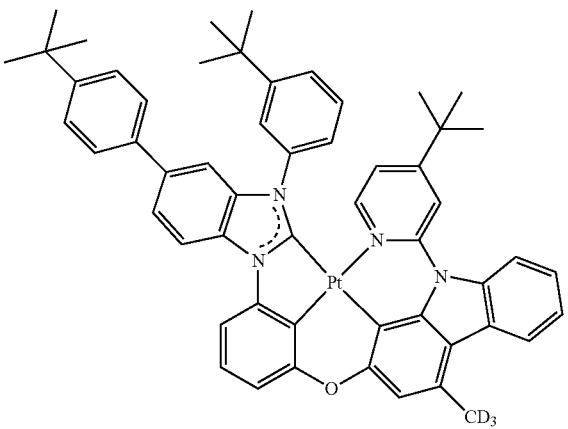
90
91

92
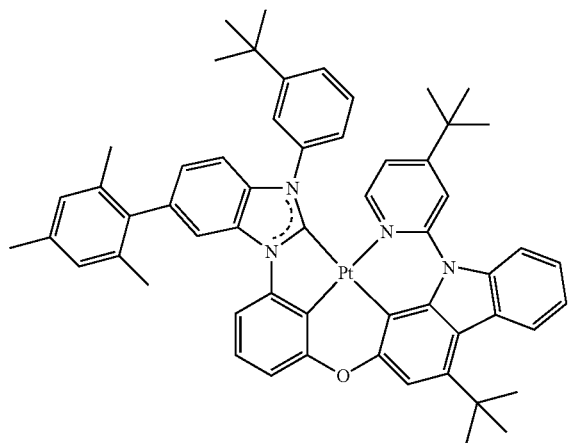
93
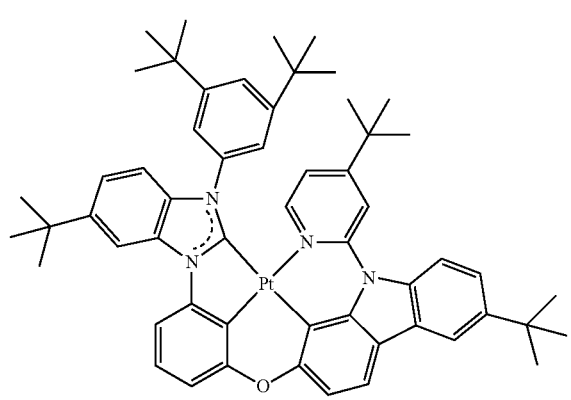
94
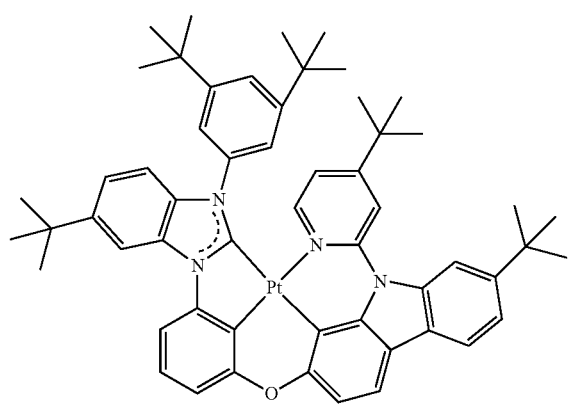
95
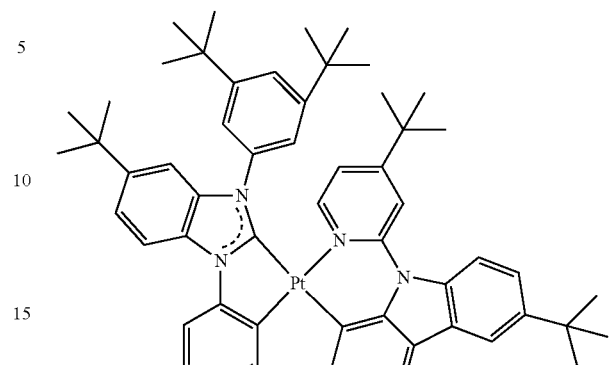
96
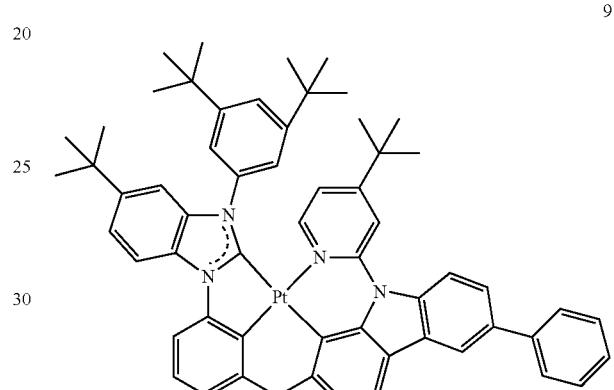
97
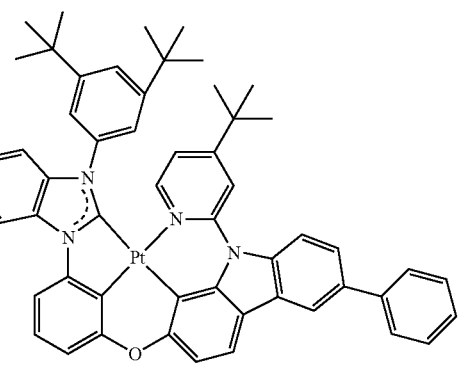
98
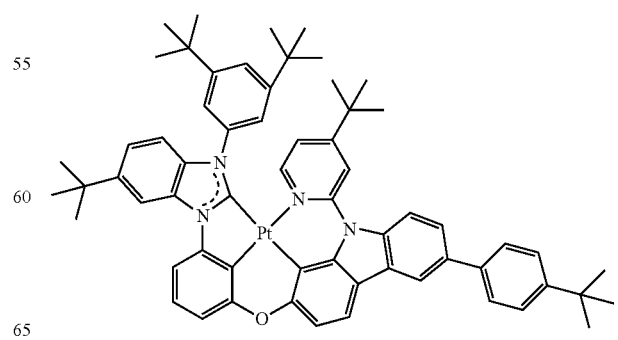

99
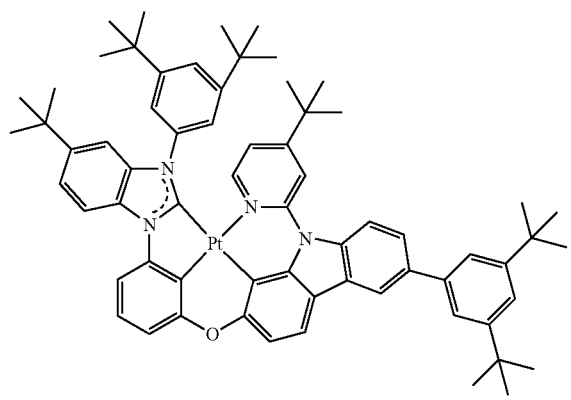
100
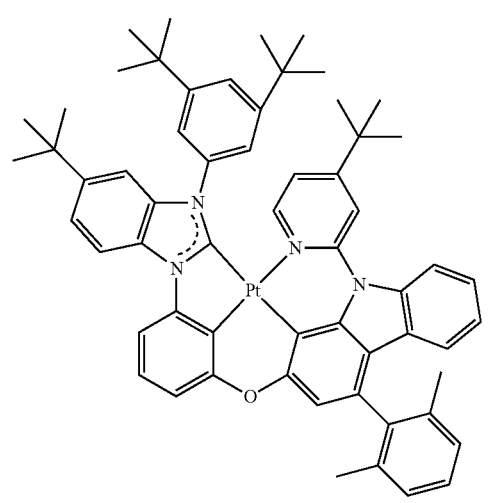
101
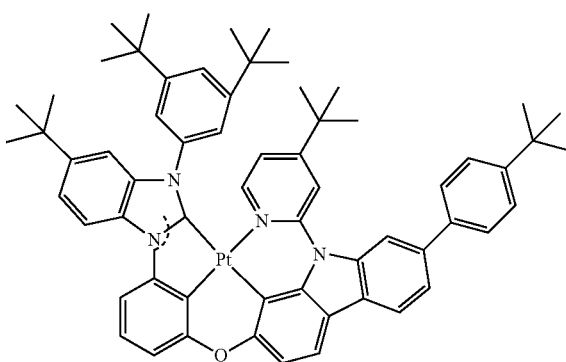
102
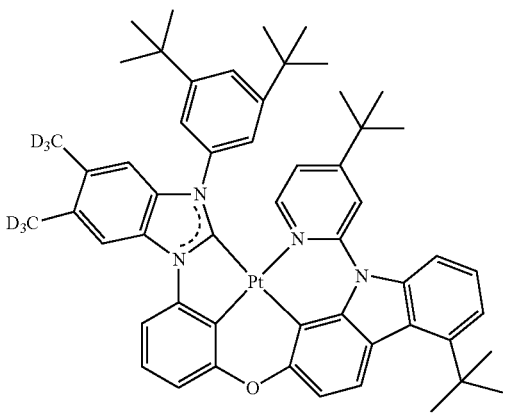
103
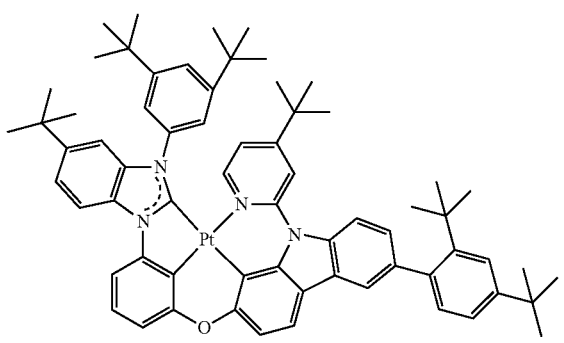
104

105
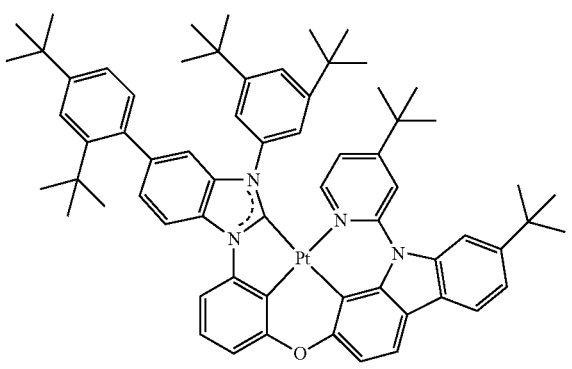

106
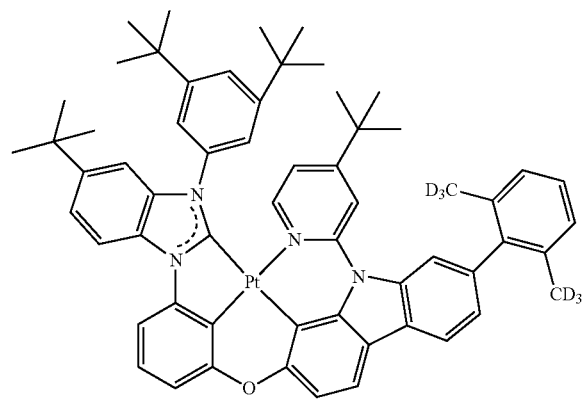
107
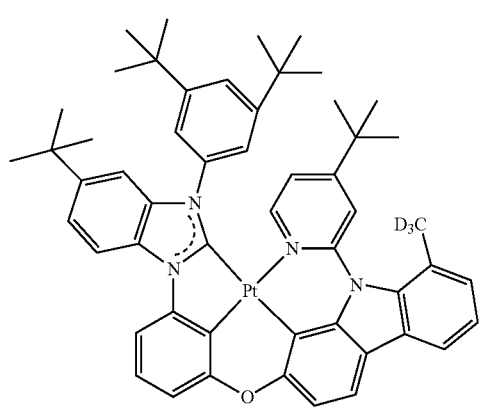
108
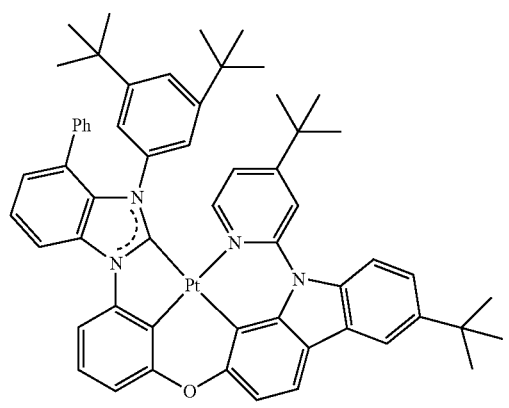
109
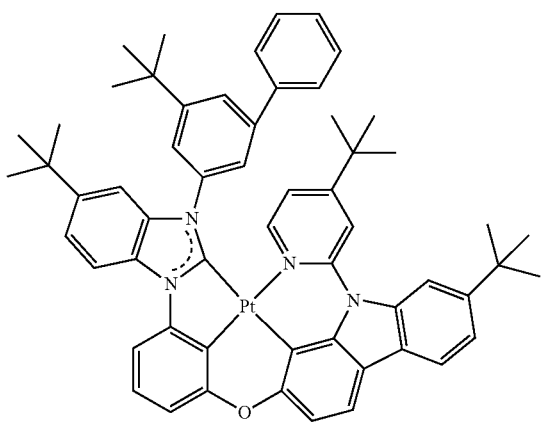
110

111

2791
-continued
2792
-continued
112
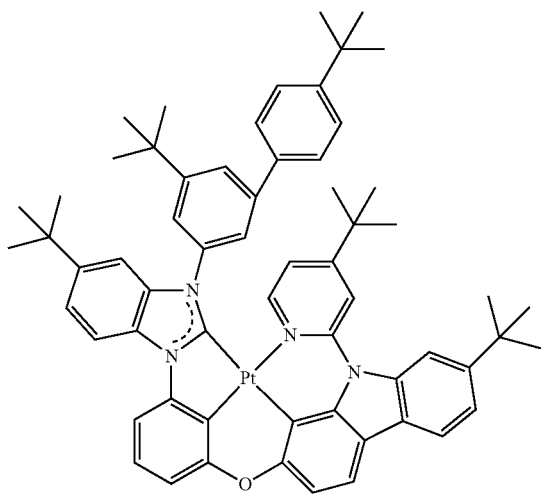
113
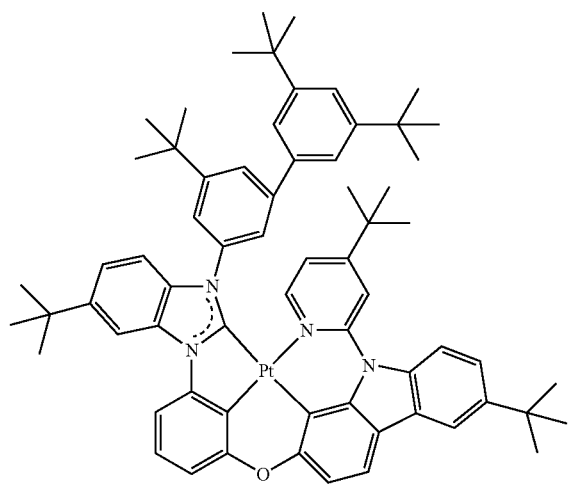
114
115
116
117
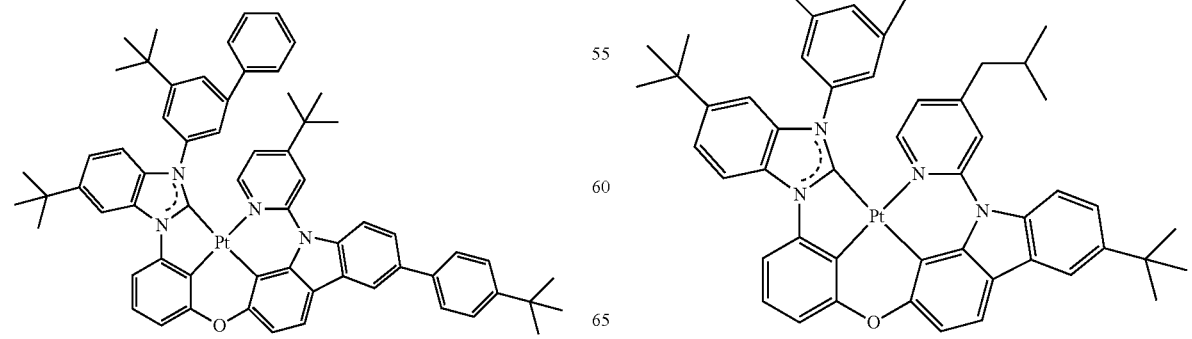

118
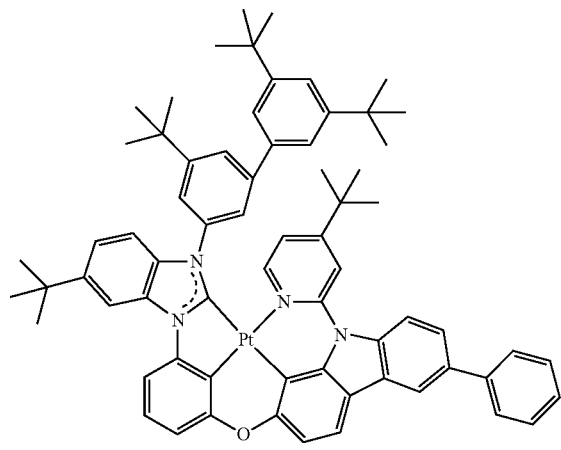
119
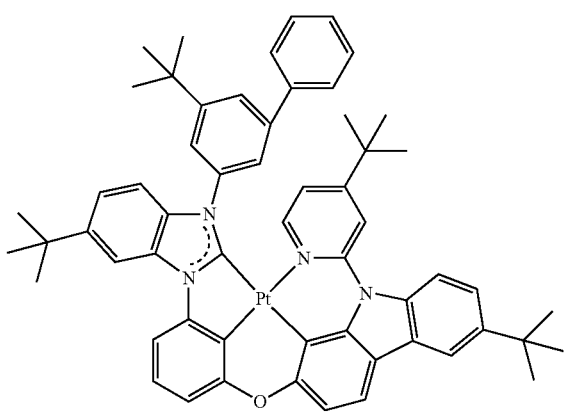
120
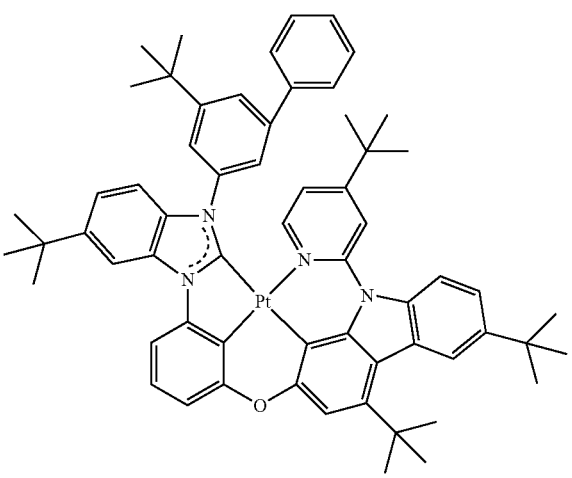
121
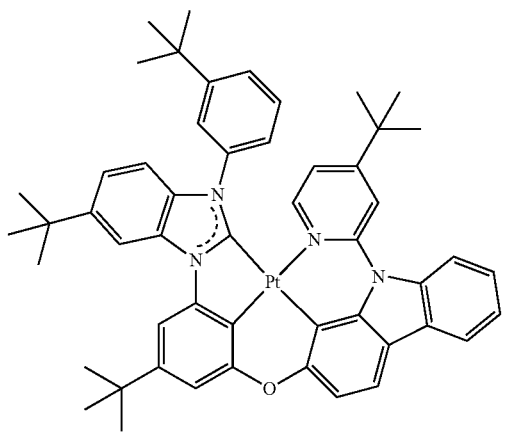
122
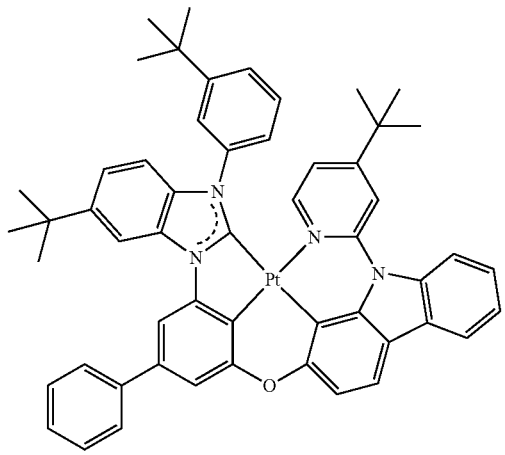
123
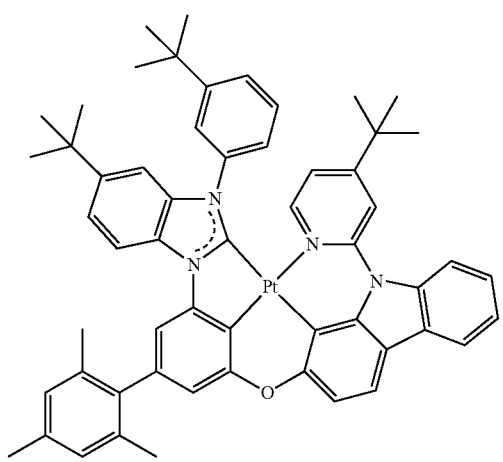

2795 -continued
124
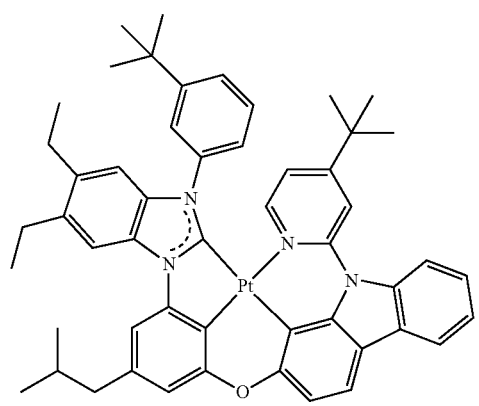
125
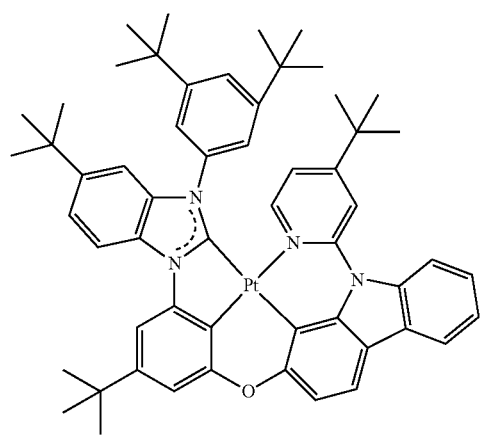
126
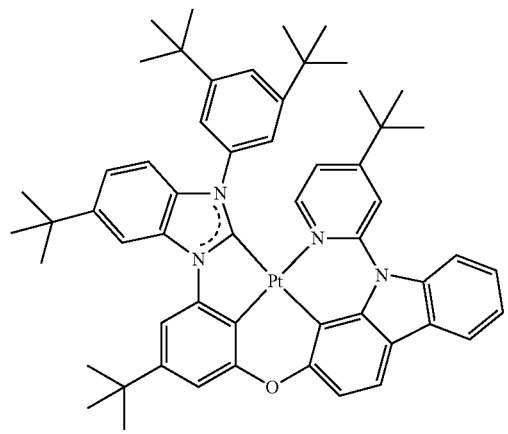
2796 -continued
127
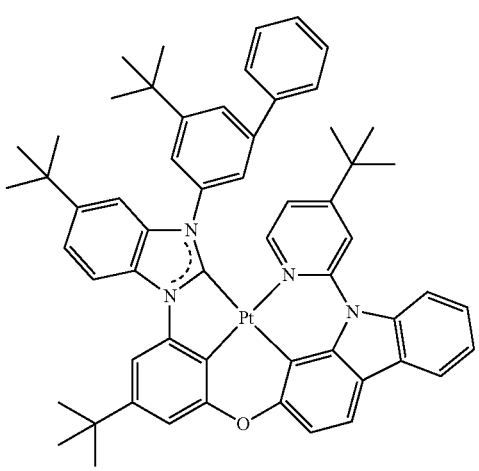
128
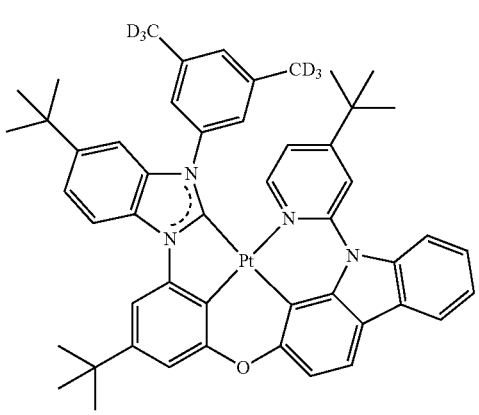
129
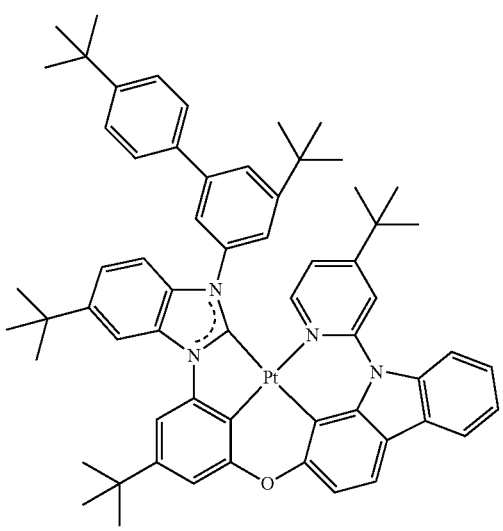

2797
-continued
130
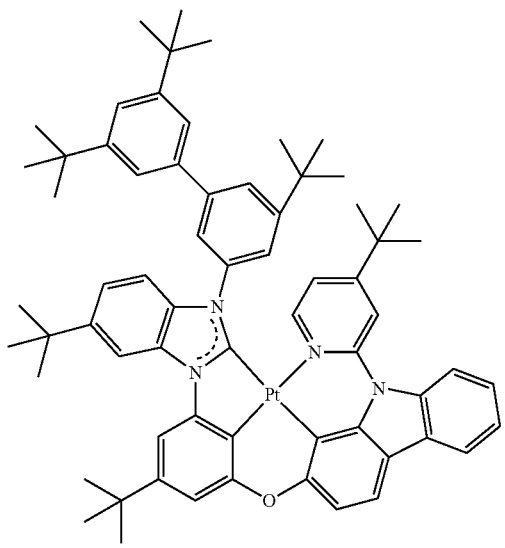
131
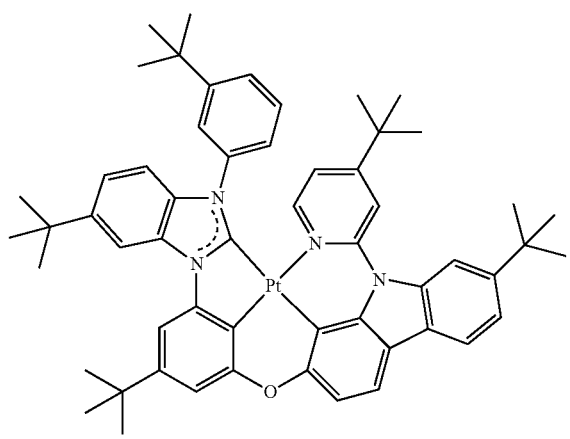
132
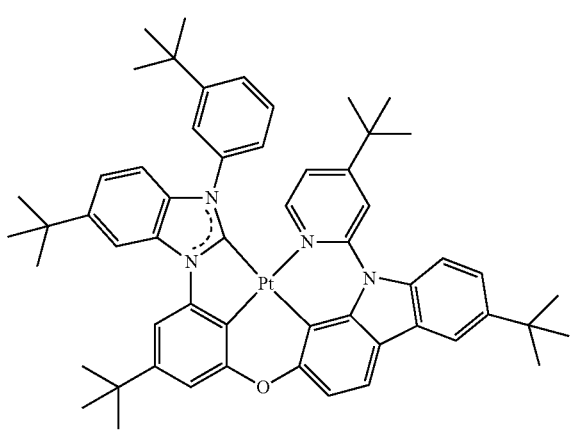
2798
-continued
133
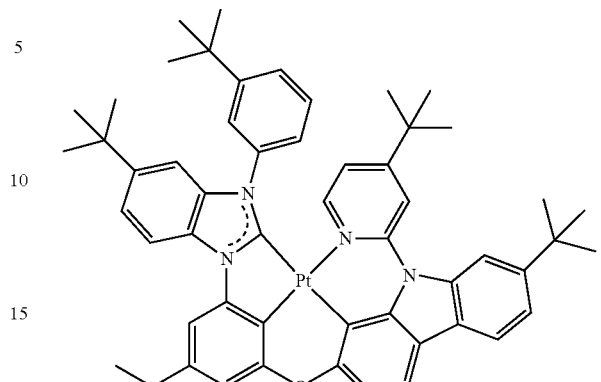
134
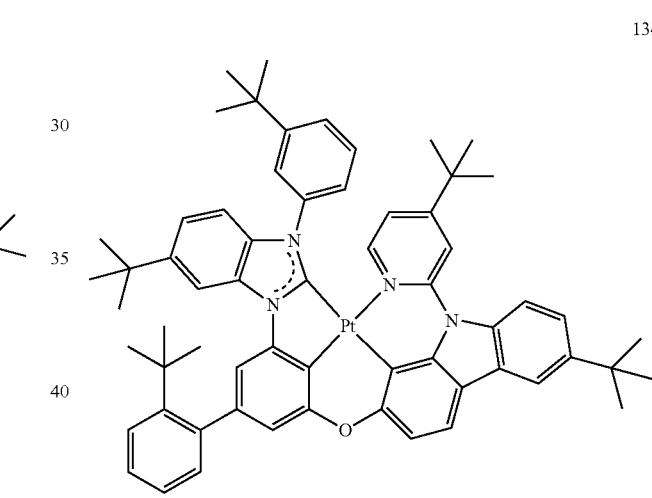
135
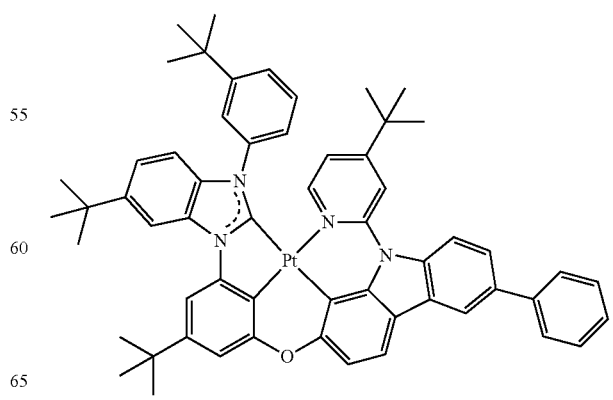

136
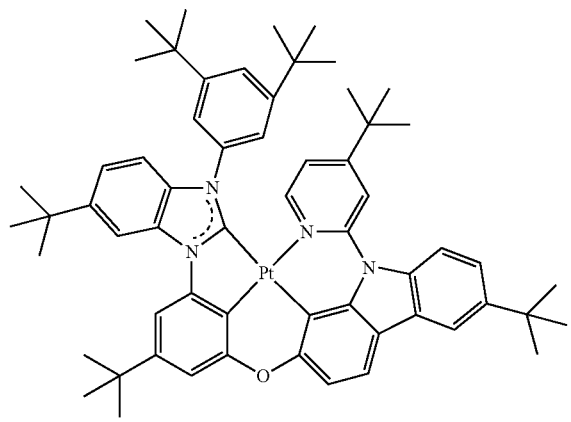
137
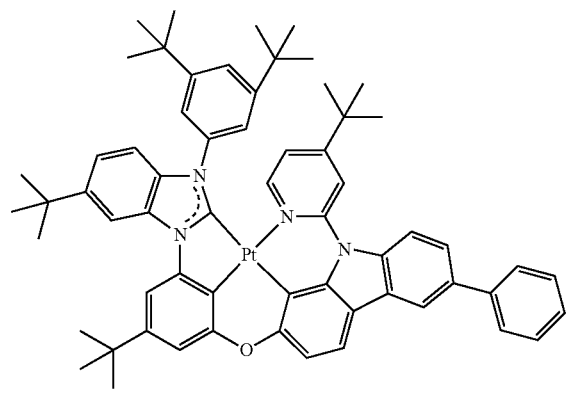
138
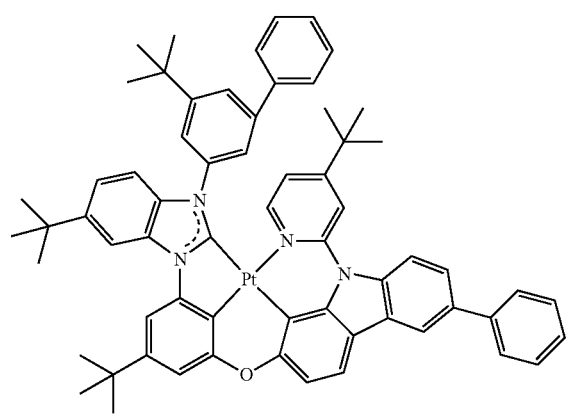
139
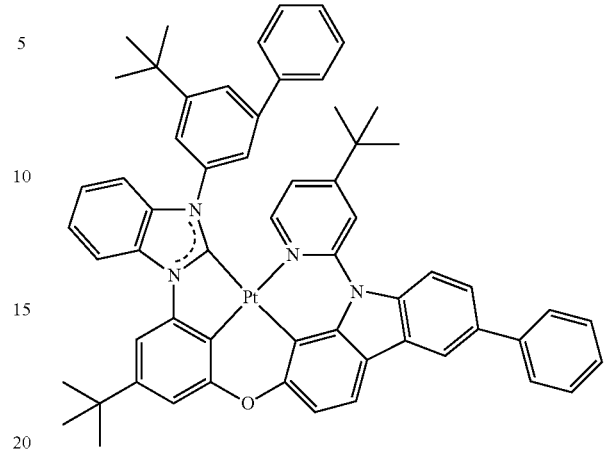
140
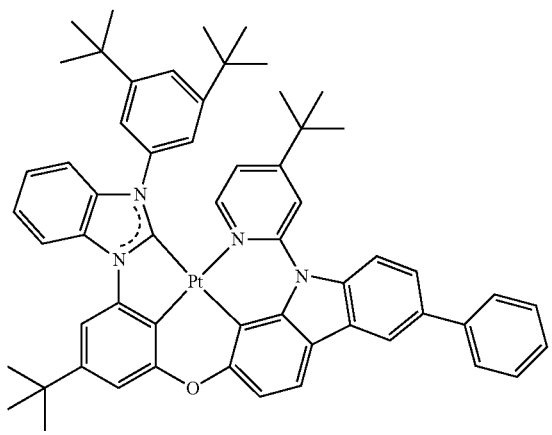
141
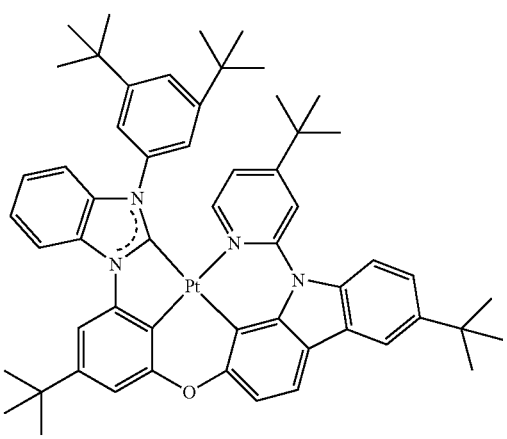

142
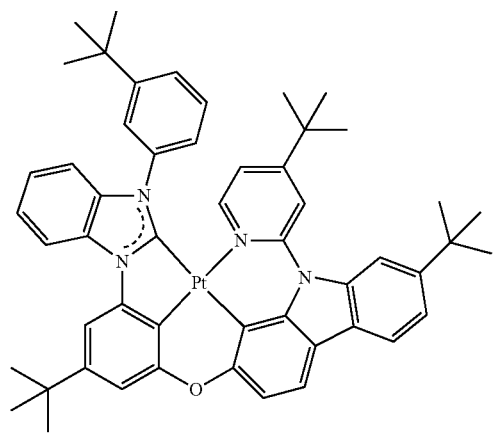
143
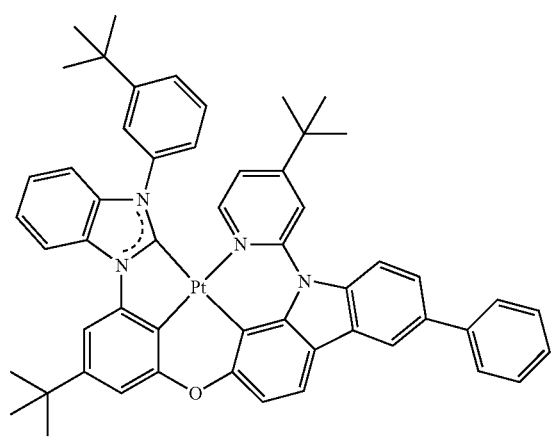
144
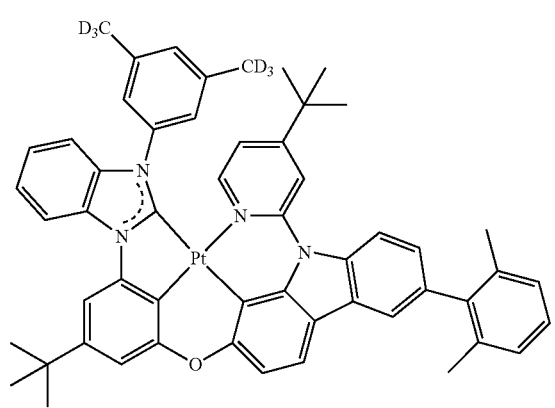
145
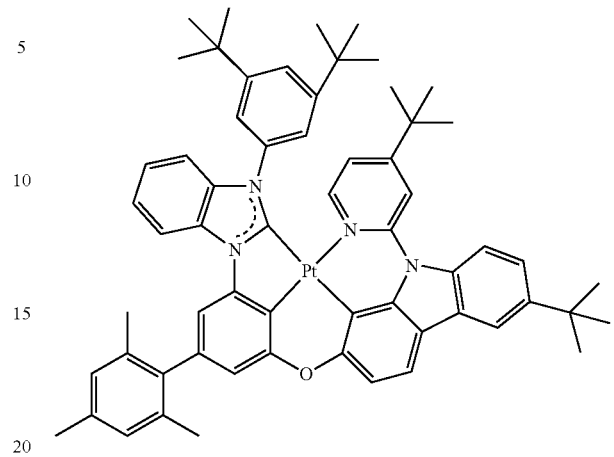
146
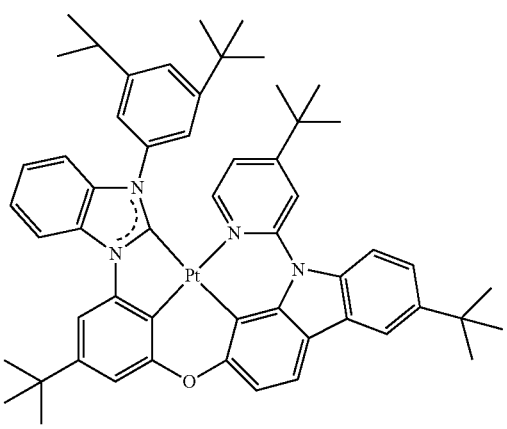
147
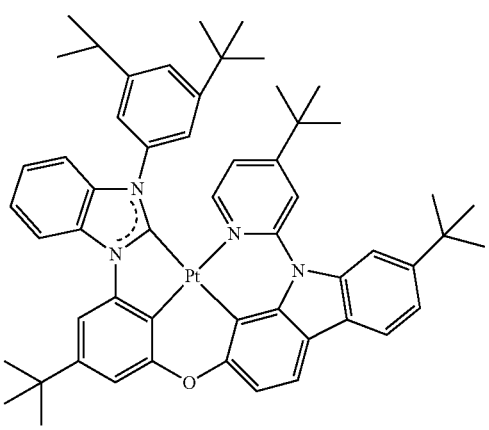

148
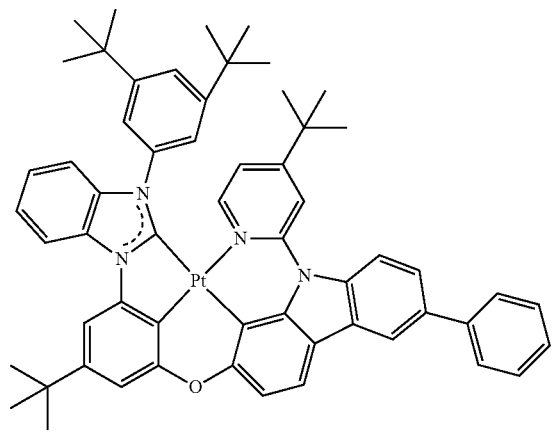
149
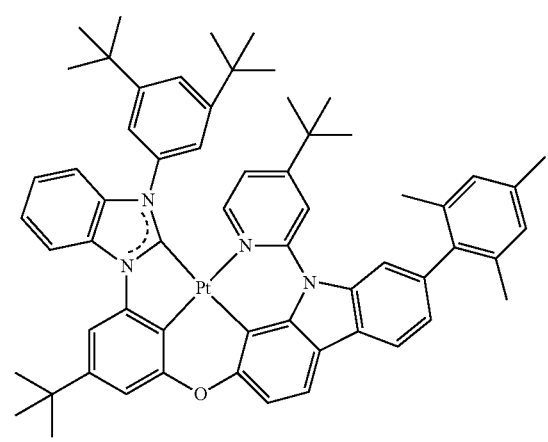
150
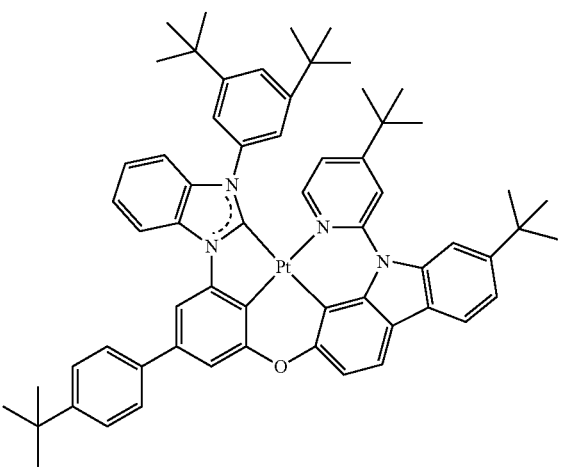
151
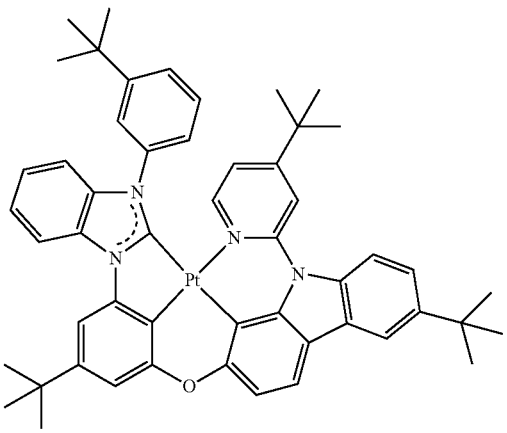
152
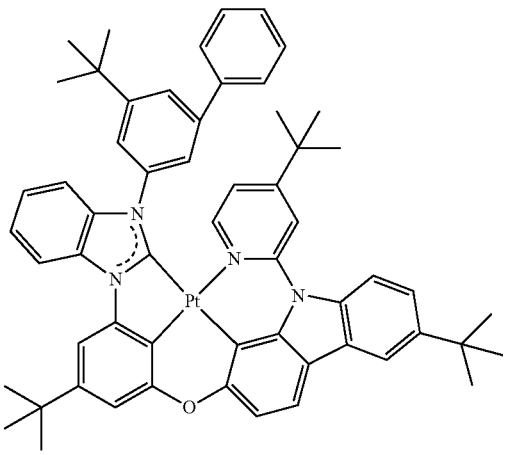
153
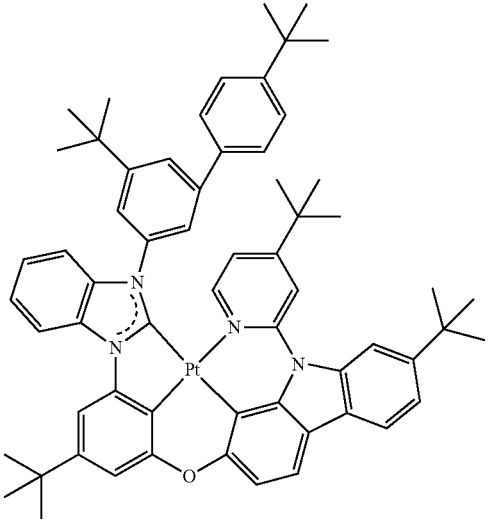

2805
-continued
154
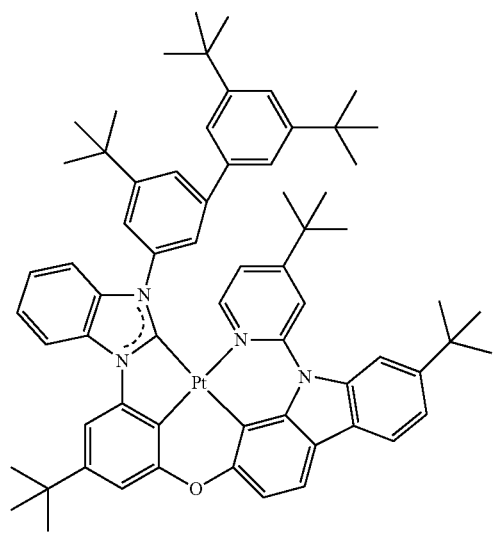
155
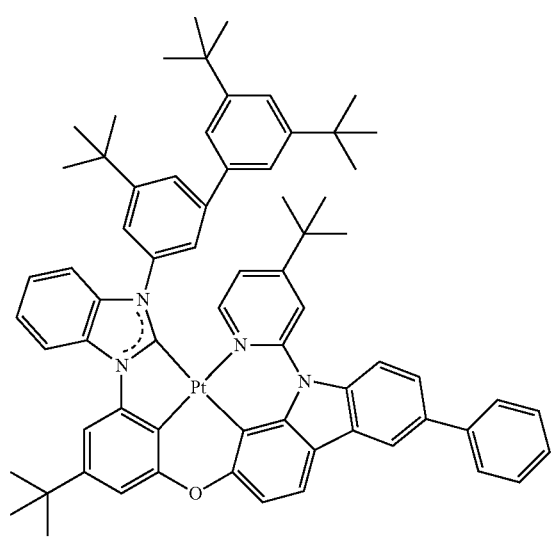
156
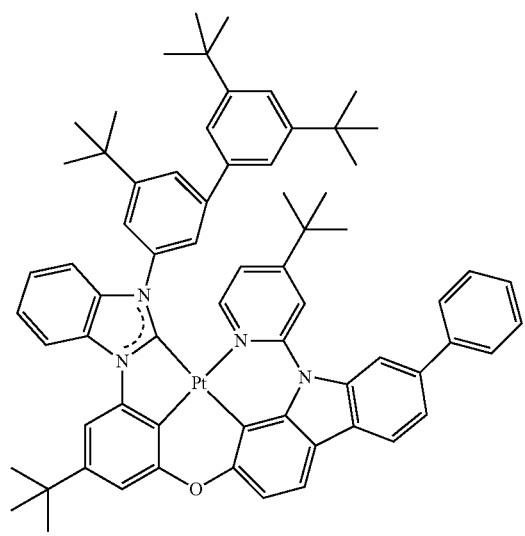
2806
-continued
157
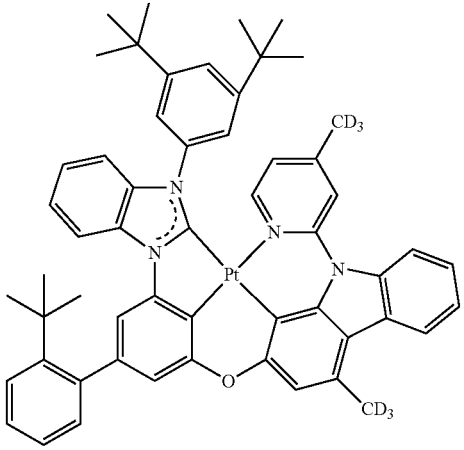
158
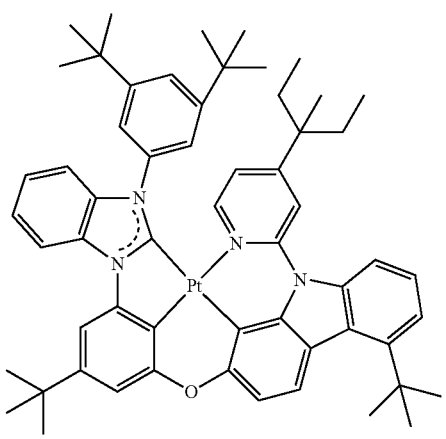
159
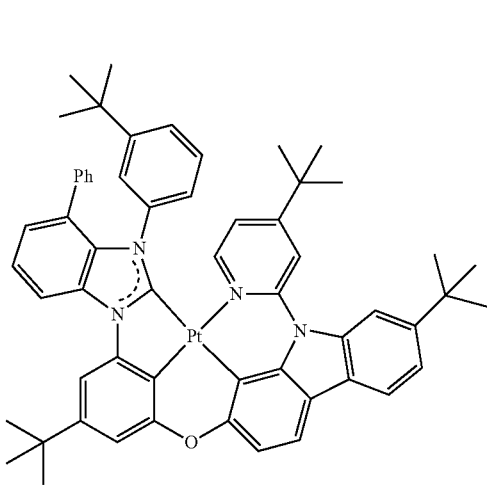

2807
-continued
160
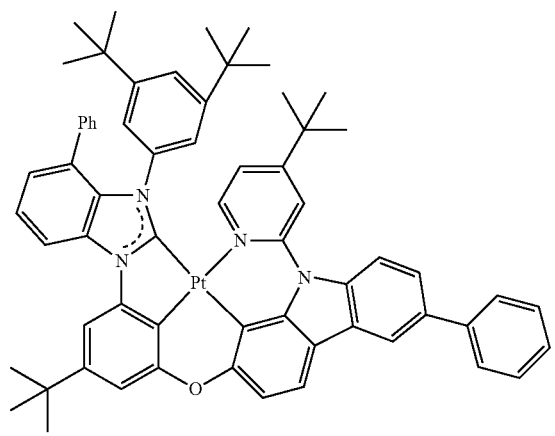
161
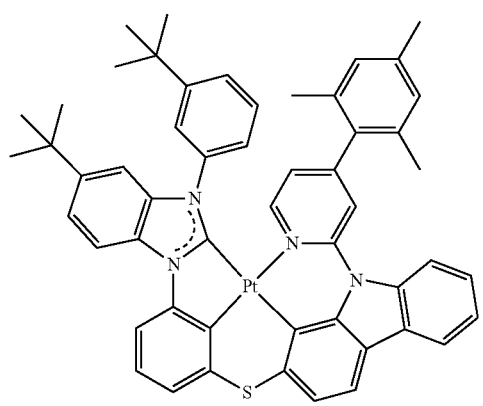
162
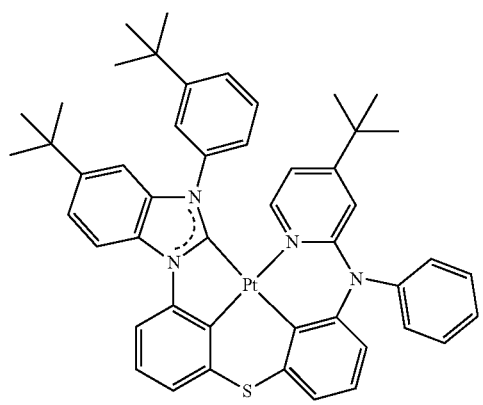
2808
-continued
163
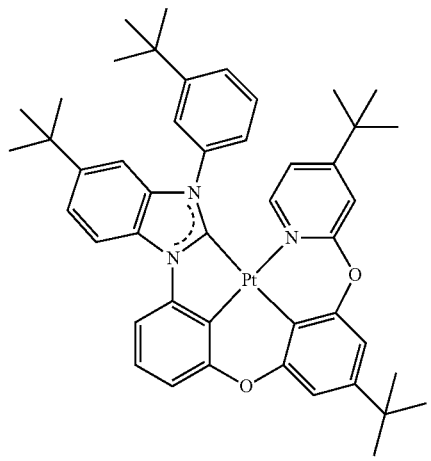
164
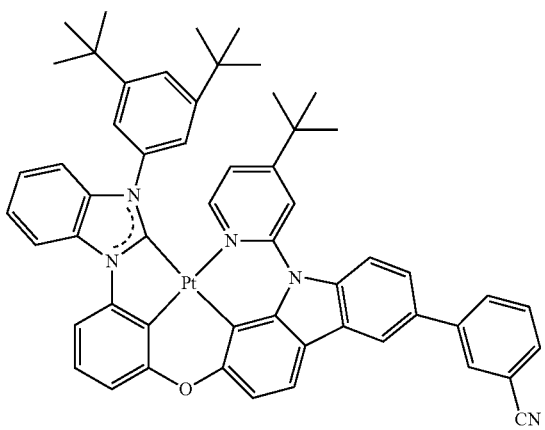
165
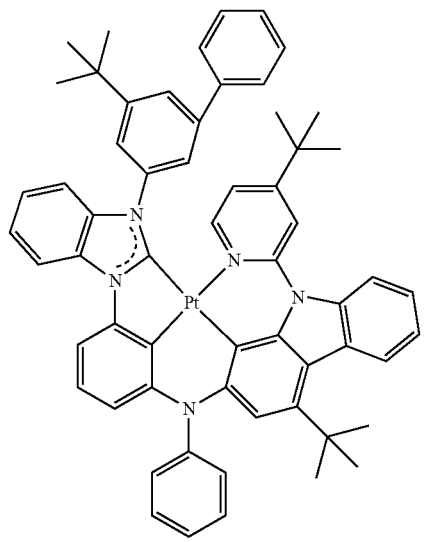

2809
-continued
166
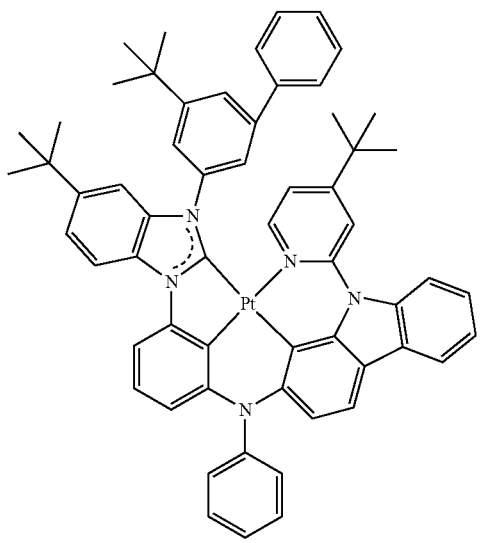
167
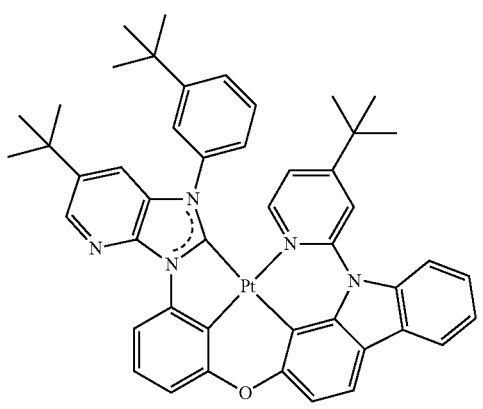
168
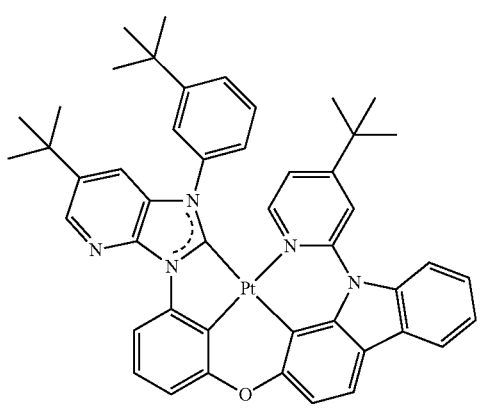
2810
-continued
169
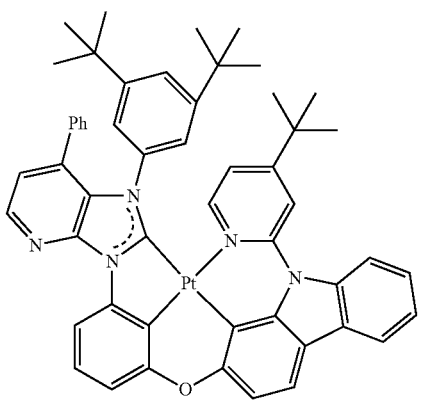
170
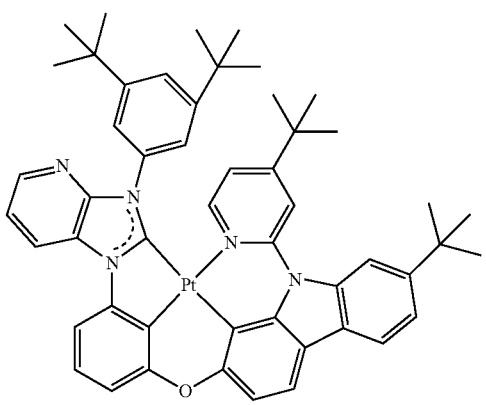
171
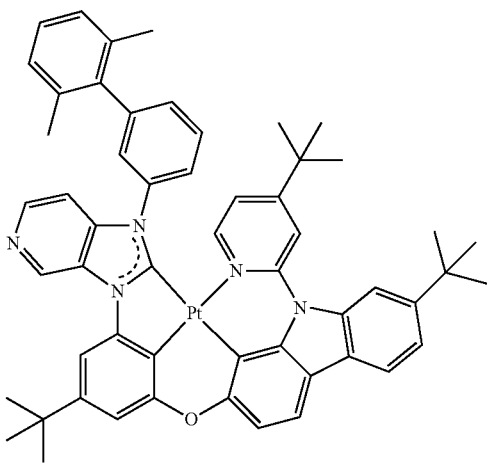

172
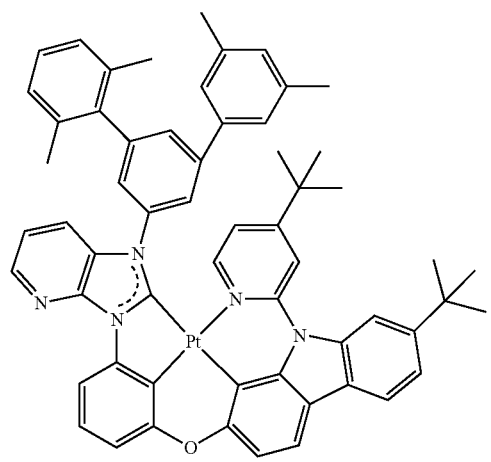
173
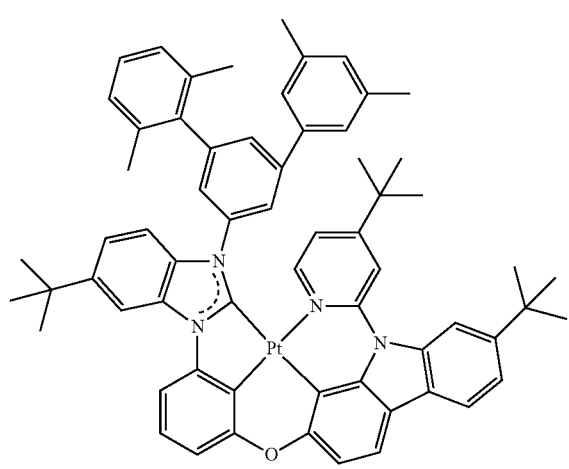
174
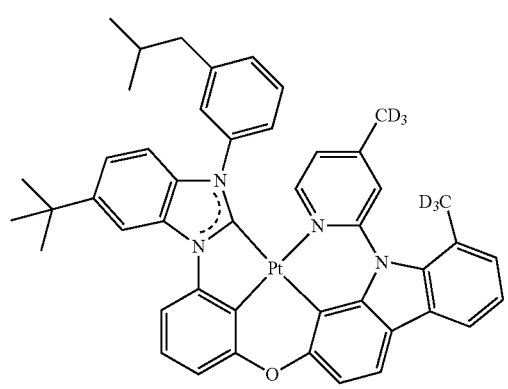
175
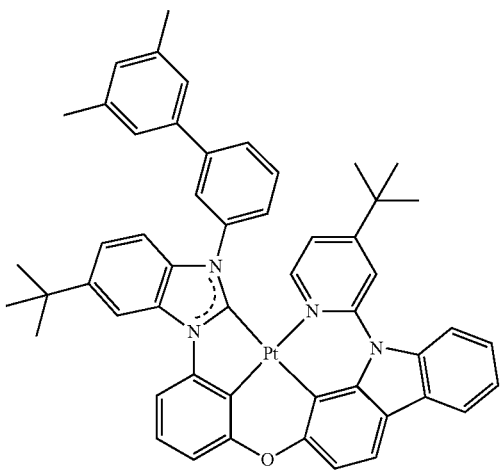
176
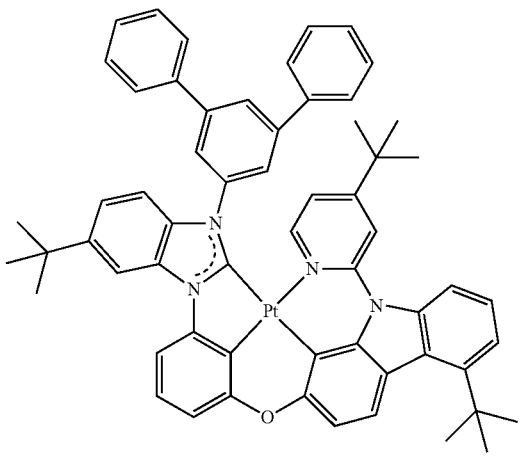
In some embodiments, the sensitizer may be represented by Formula 111 or Formula 112, and in this embodiment, the sensitizer may be referred to as a delayed fluorescence sensitizer:
Formula 111
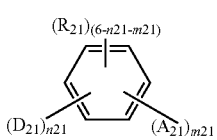
Formula 112
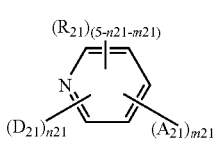
wherein, in Formulae 111 and 112,
$A_{21}$ may be an acceptor,
$D_{21}$ may be a donor,
m21 may be 1, 2, or 3, and n21 may b 1, 2, or 3,
in Formula 111, a sum of n21 and m21 may be 6 or less, and in Formula 112, a sum of n21 and m21 may be 5 or less, and $R_{21}$ may be hydrogen, deuterium, —F, —Cl, —Br, —I, —SF$_5$, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkyl aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkyl heteroaryl group, a substituted or unsubstituted $C_1$-$C_{60}$ hetero aryloxy group, a substituted or unsubstituted $C_1$-$C_{60}$ hetero arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —Ge($Q_1$)($Q_2$)($Q_3$), —C($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), and a plurality of $R_{21}$(s) may optionally be bound to each other to form a substituted or unsubstituted $C_5$-$C_{30}$ carbocyclic group or a substituted or unsubstituted $C_1$-$C_{30}$ heterocyclic group, wherein $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkyl aryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent aromatic condensed polycyclic group, a monovalent aromatic condensed heteropolycyclic group, a monovalent non-aromatic condensed polycyclic group, a monovalent non-aromatic condensed heteropolycyclic group, a $C_1$-$C_{60}$ alkyl group substituted with at least one deuterium, —F, a cyano group, a $C_1$-$C_{60}$ alkyl group, a $C_6$-$C_{60}$ aryl group, or any combination thereof, or a $C_6$-$C_{60}$ aryl group substituted with at least one deuterium, —F, a cyano group, a $C_1$-$C_{60}$ alkyl group, a $C_6$-$C_{60}$ aryl group, or any combination thereof.

For example, in Formulae 111 and 112, $A_{21}$ may be a substituted or unsubstituted π electron-depleted nitrogen-free cyclic group.

In some embodiments, the π electron-depleted nitrogen-free cyclic group may be a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a triindolobenzene group; or a condensed ring of at least two π electron-depleted nitrogen-free cyclic groups, but embodiments are not limited thereto.

In some embodiments, in Formulae 111 and 112, $D_{21}$ may be:—F, a cyano group, or a π electron-depleted nitrogen-containing cyclic group;

a $C_1$-$C_{60}$ alkyl group, a π electron-depleted nitrogen-containing cyclic group, or electron-depleted nitrogen-free cyclic group, each substituted with at least one of —F, a cyano group, or any combination thereof; or a π electron-depleted nitrogen-containing cyclic group substituted with at least one of deuterium, a $C_1$-$C_{60}$ alkyl group, a π electron-depleted nitrogen-containing cyclic group, π electron-depleted nitrogen-free cyclic group, or any combination thereof.

In some embodiments, the π electron-depleted nitrogen-free cyclic group may be understood by referring to the description of the π electron-depleted nitrogen-free cyclic group provided herein.

The π electron-depleted nitrogen-containing cyclic group may be a cyclic group having at least one *—N=*' moiety. Examples thereof may include: an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, and a benzimidazolobenzimidazole group; and a condensed ring of at least two π electron-depleted nitrogen-containing cyclic groups.

In some embodiments, the sensitizer may be Groups VII to XII, but embodiments are not limited thereto:

Group VII

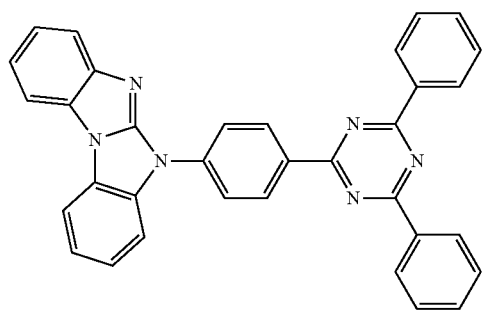

2815 -continued
2
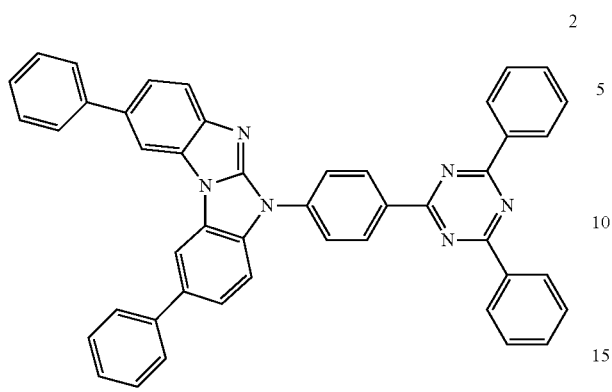
3
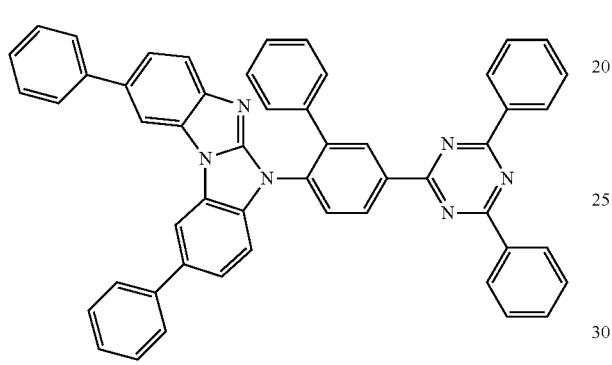
4
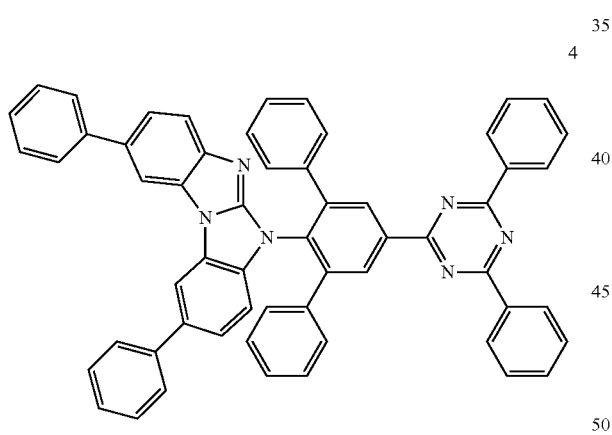
1
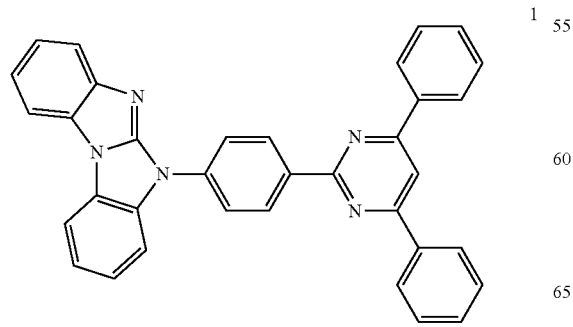
2816 -continued
2
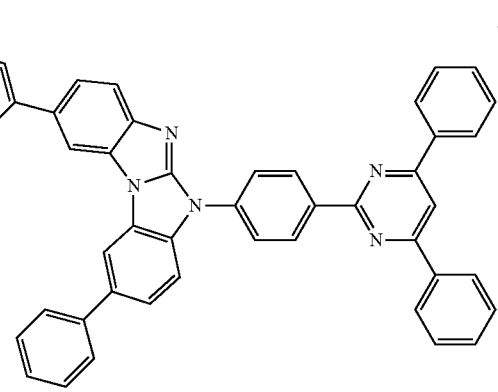
3
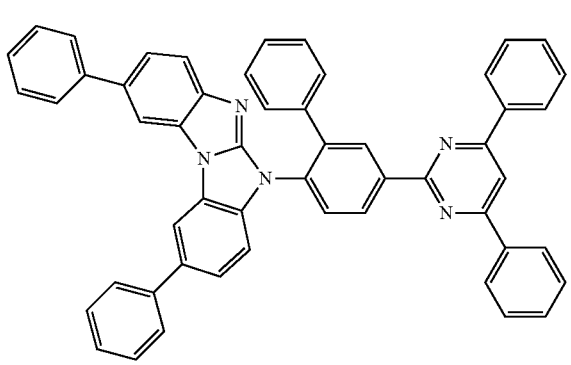
4
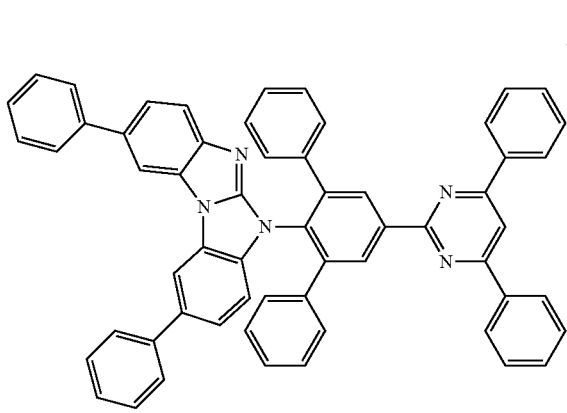
9
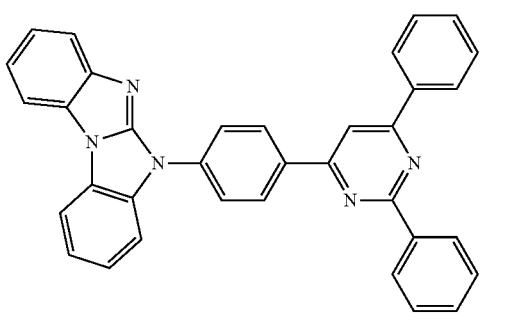

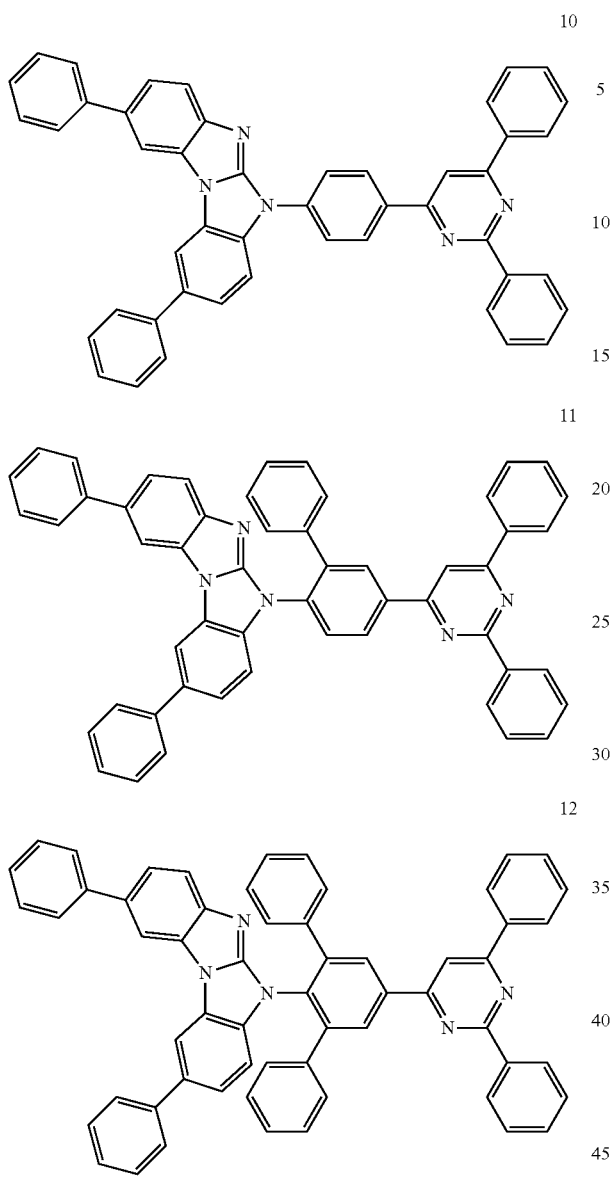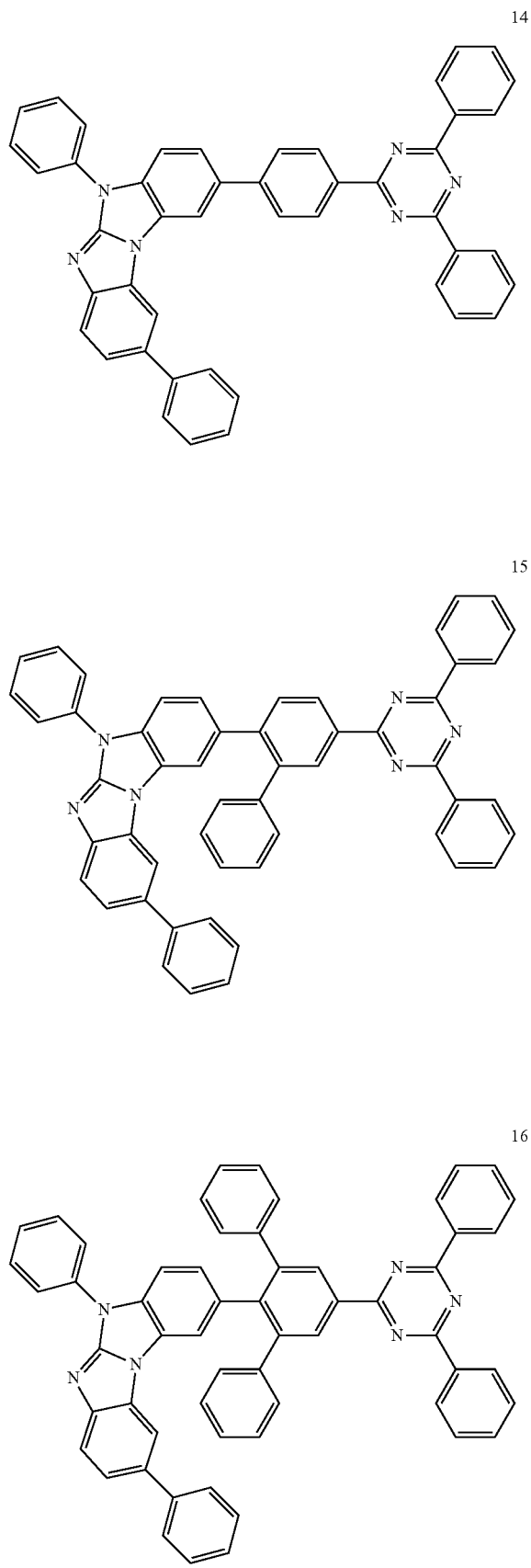

17
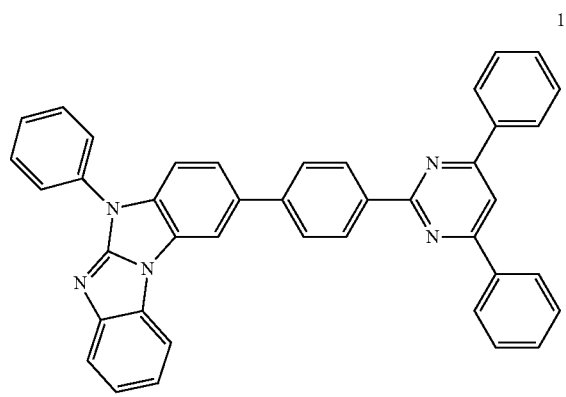
18
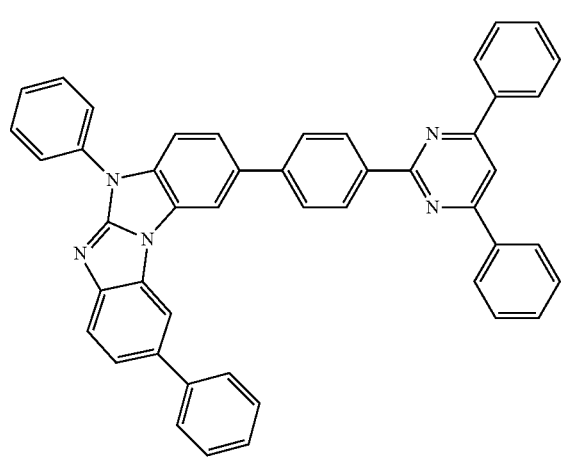
19
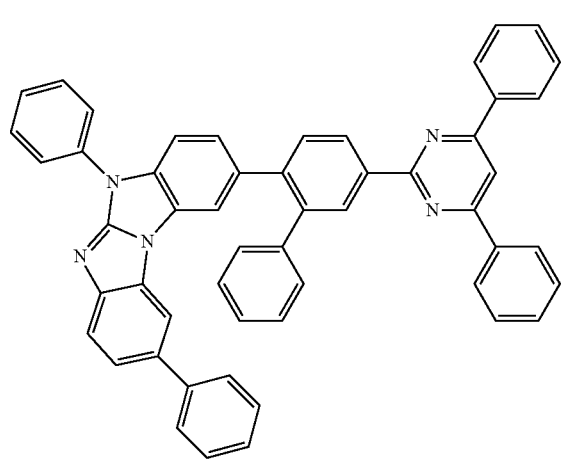
20
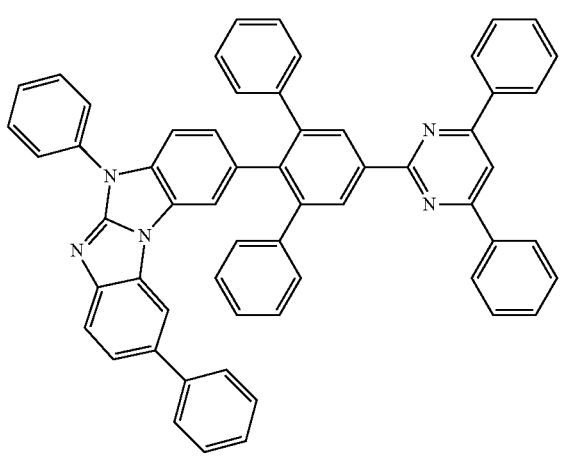
21
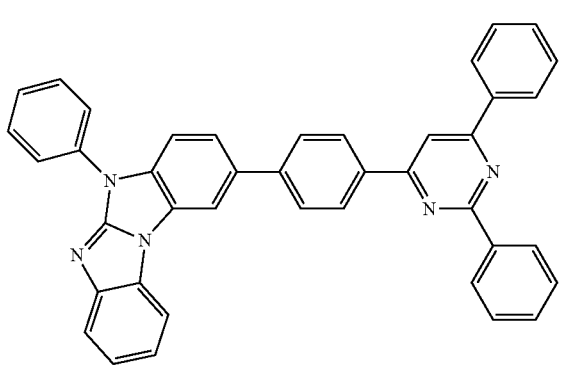
22
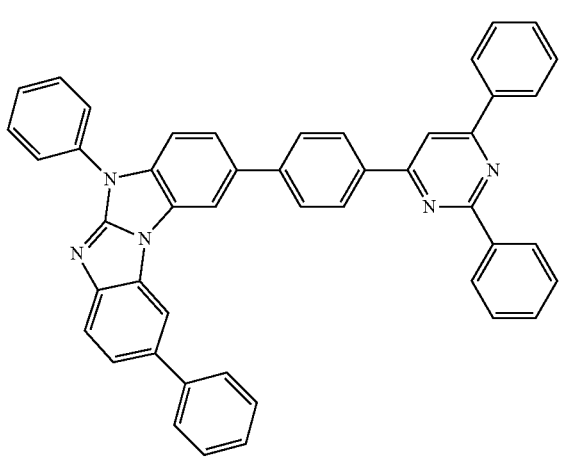

2821
-continued
23
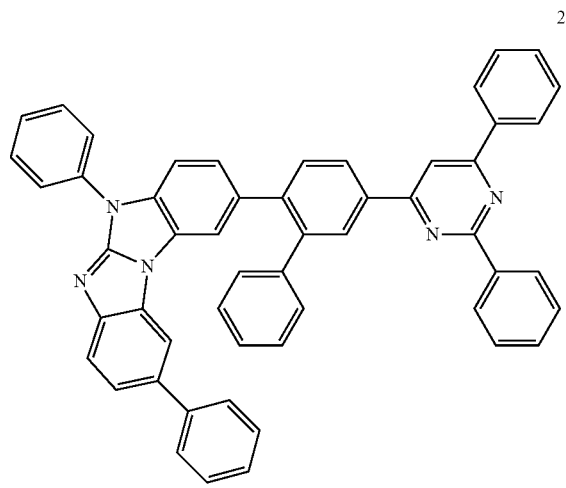
24
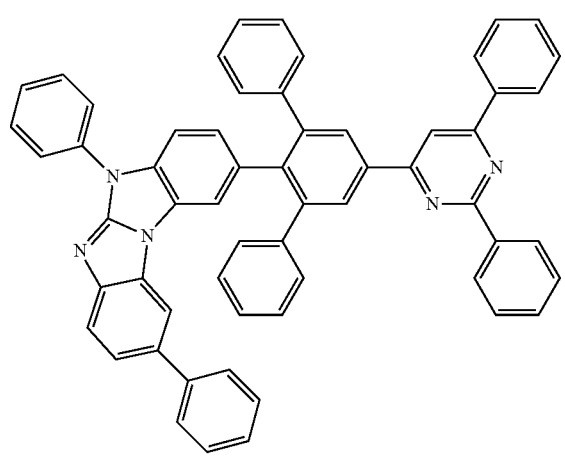
25
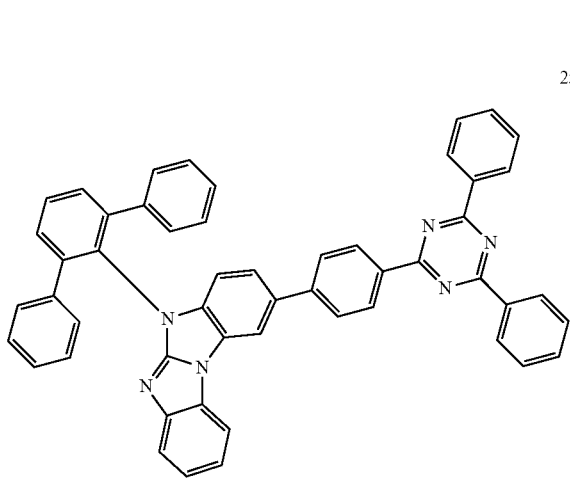
2822
-continued
26
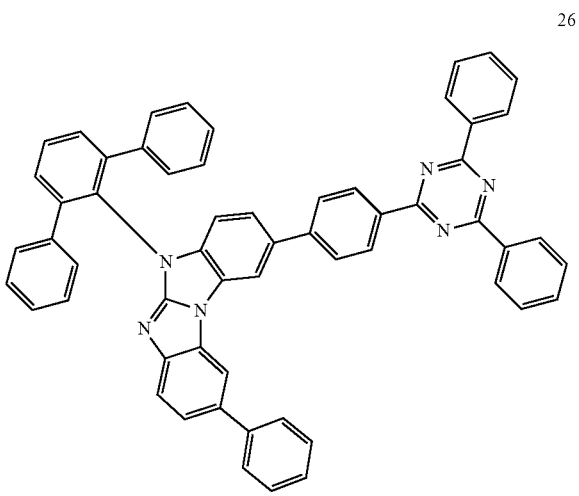
27
28
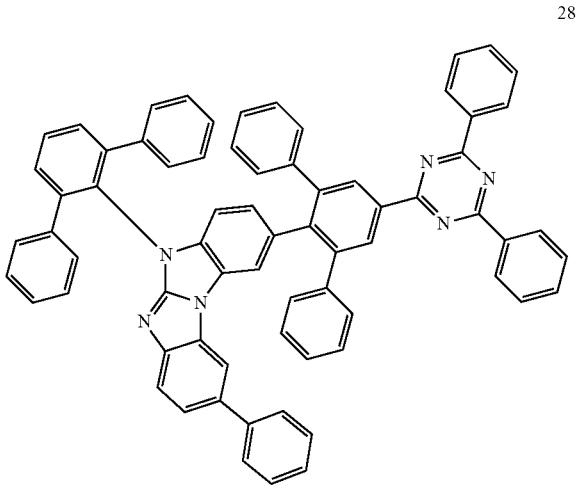

29
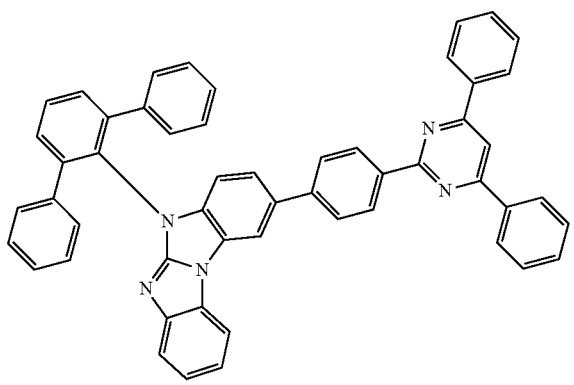
30
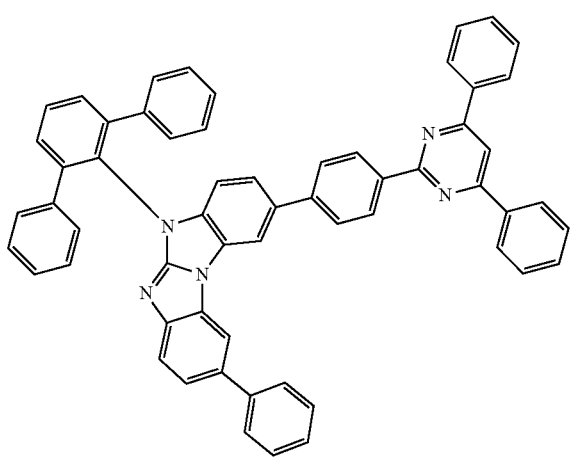
31
32
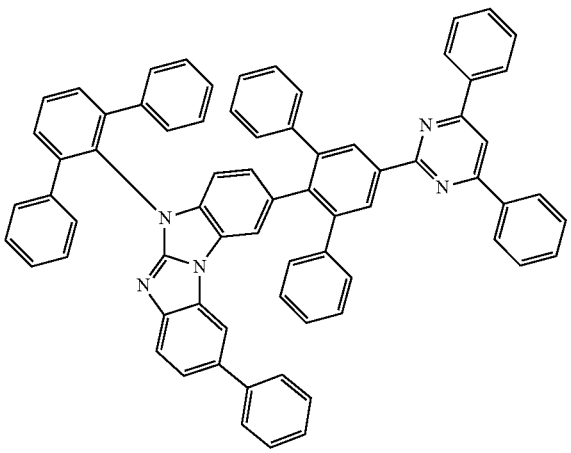
33
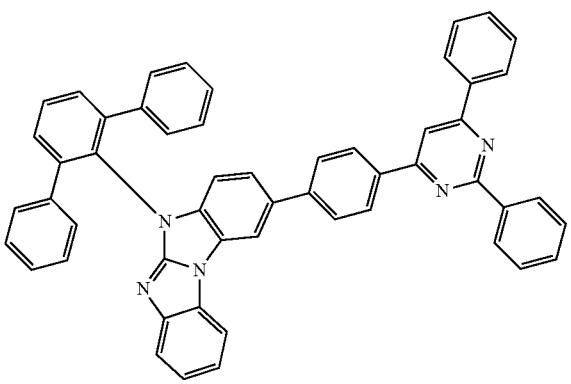
34
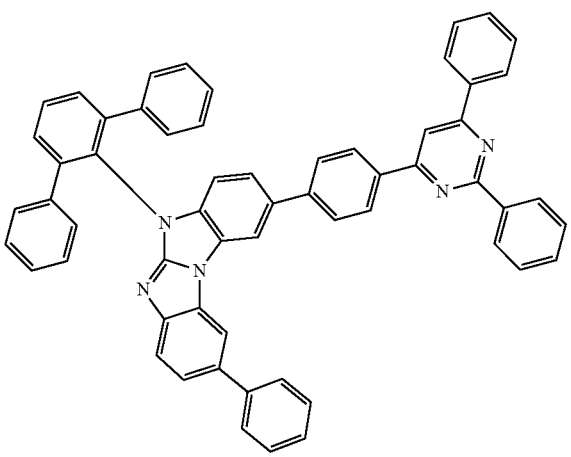

2825
-continued
35
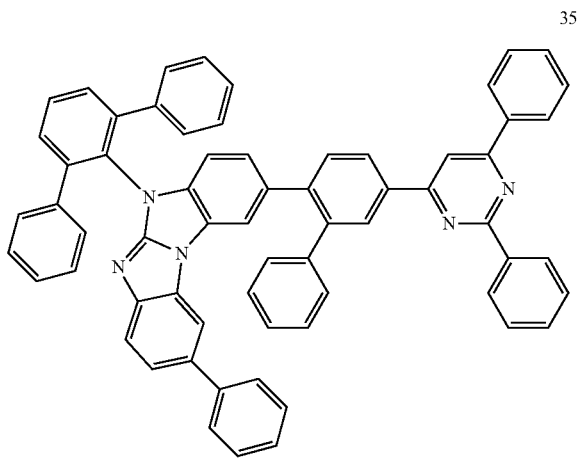
36
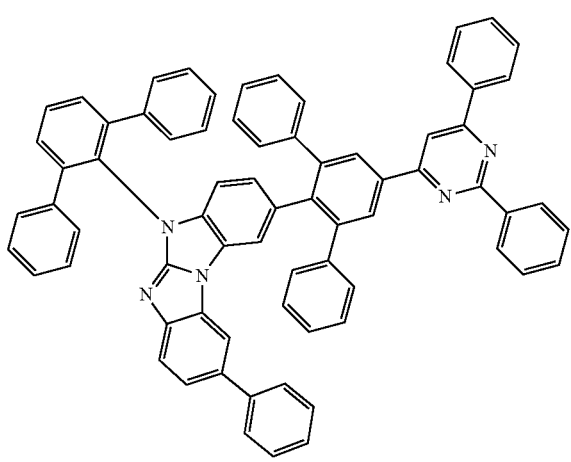
37
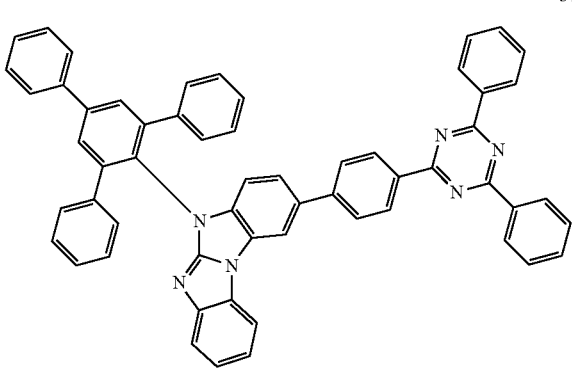
2826
-continued
38
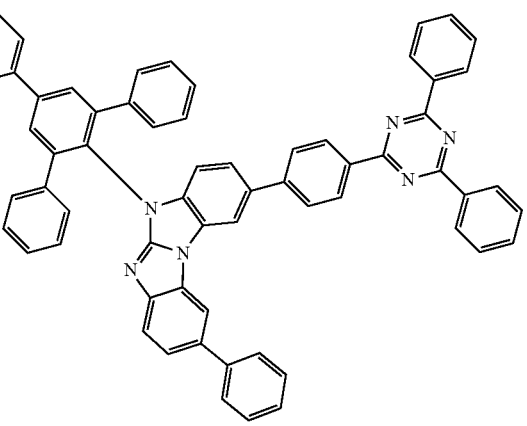
39
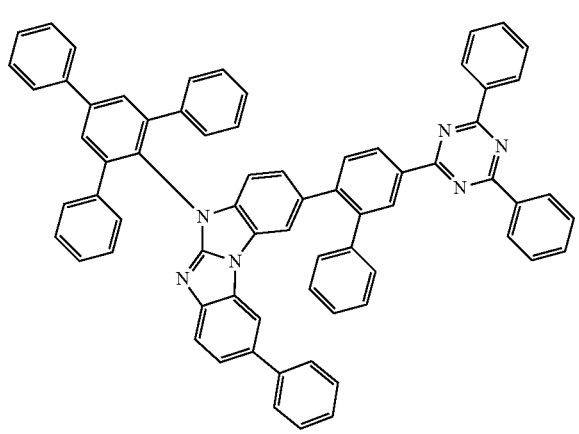
40
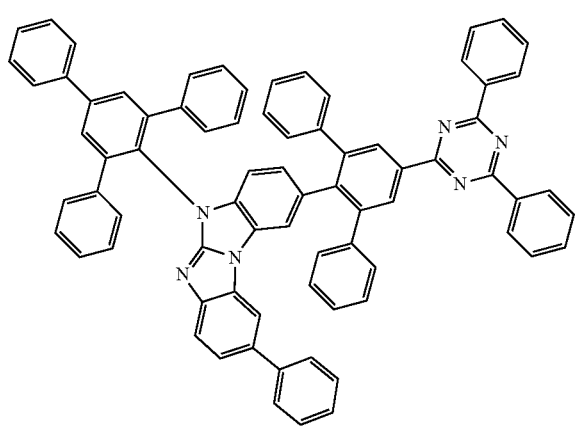

2827
-continued
41
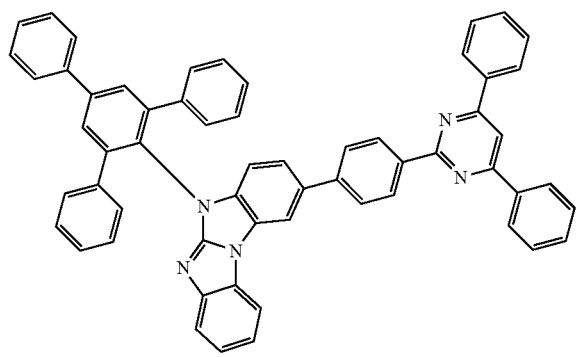
42
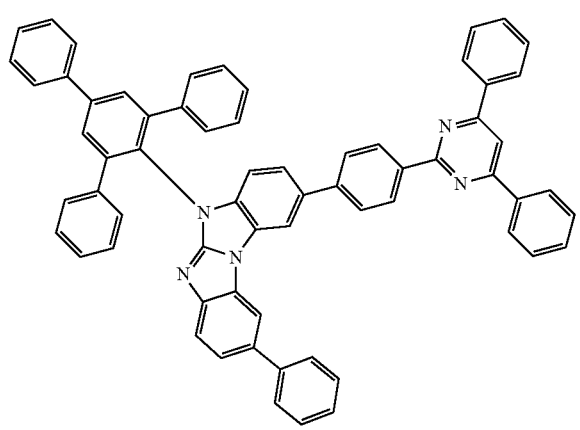
43
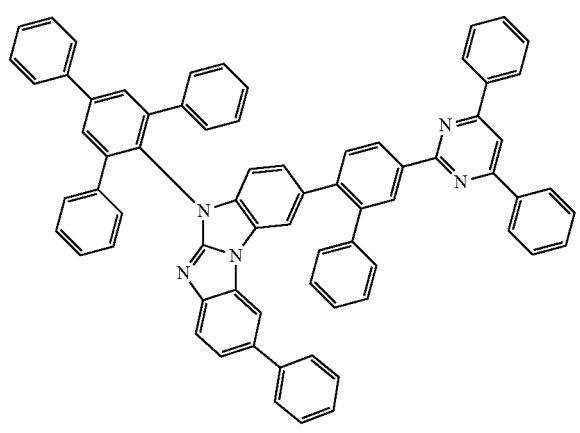
2828
-continued
44
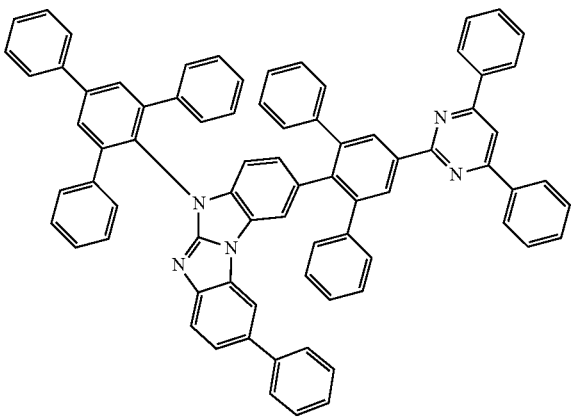
45
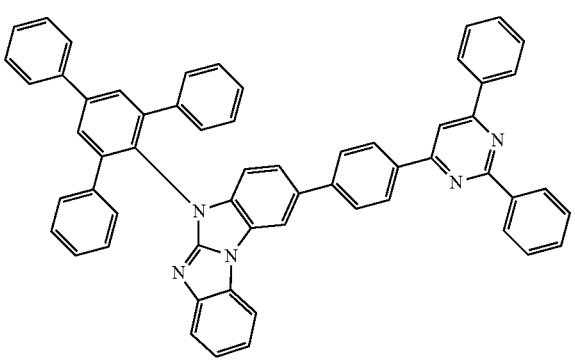
46
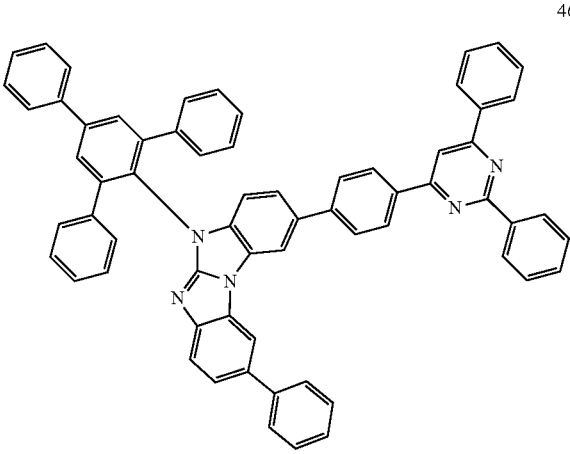

2829
-continued
47
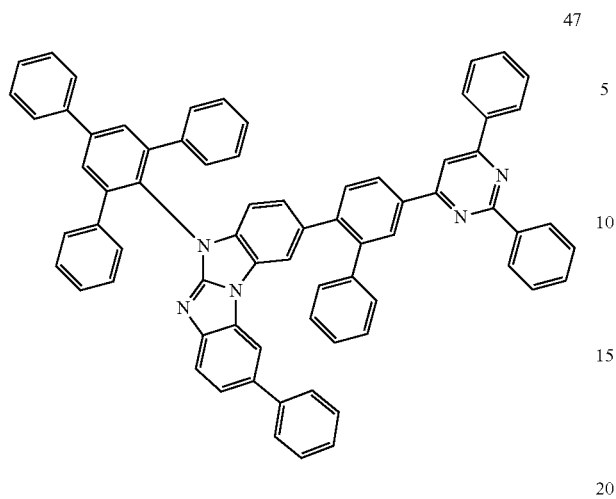
48
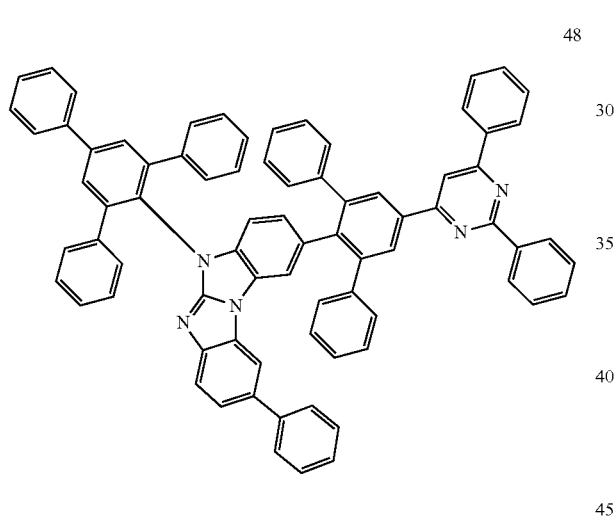
49
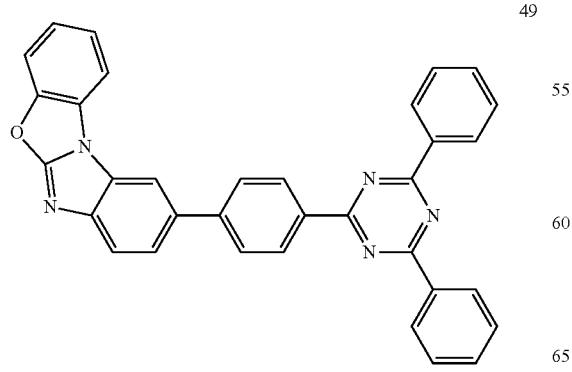
2830
-continued
50
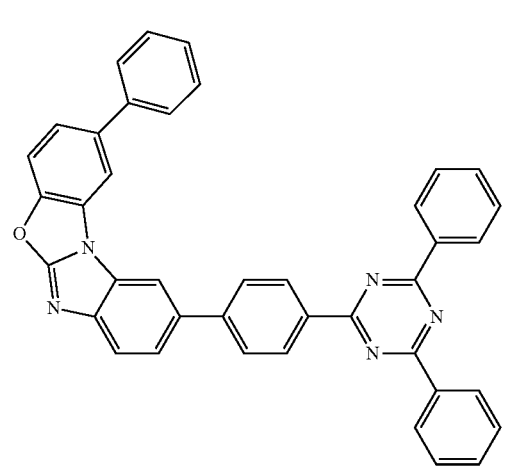
51
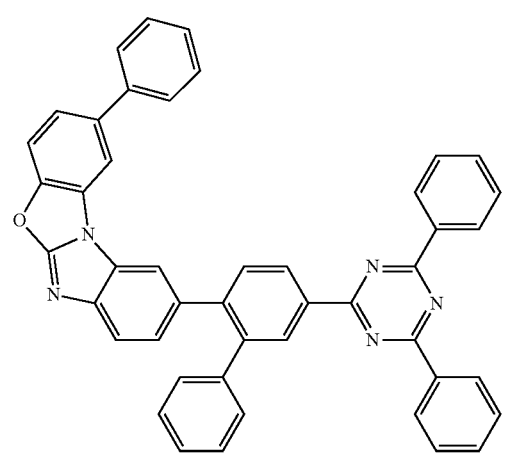
52
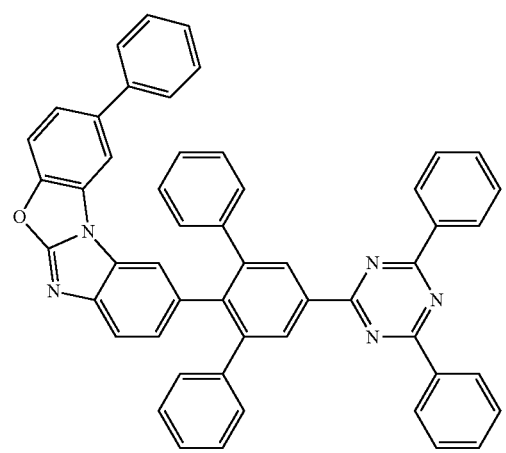

2831
-continued
2832
-continued
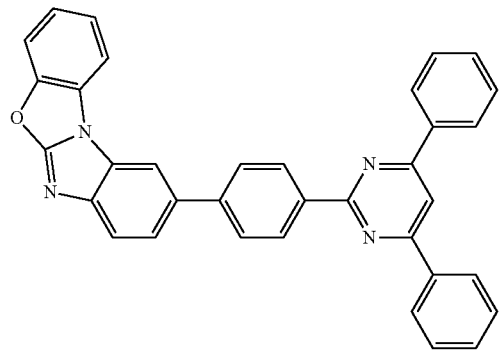
53
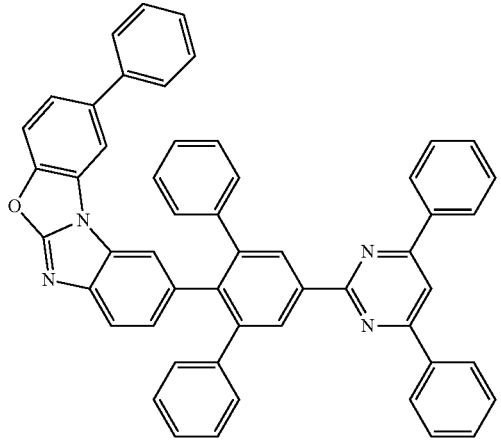
56
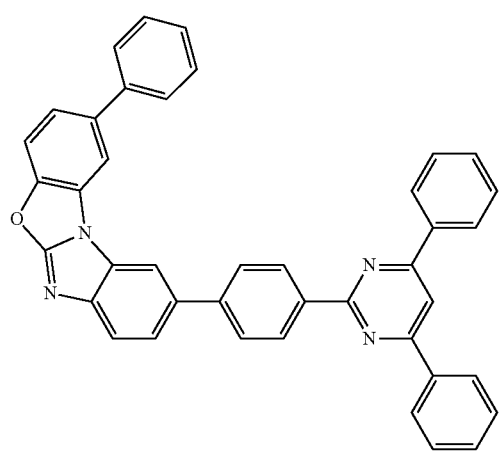
54
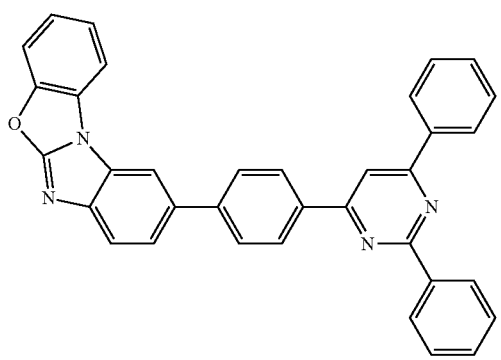
57
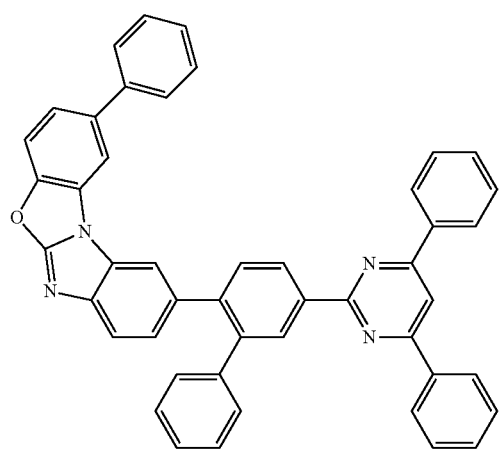
55
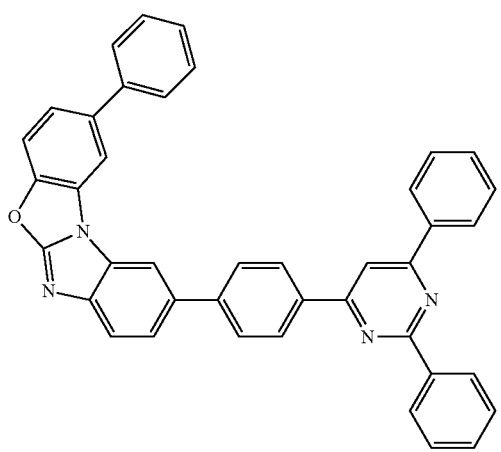
58

59
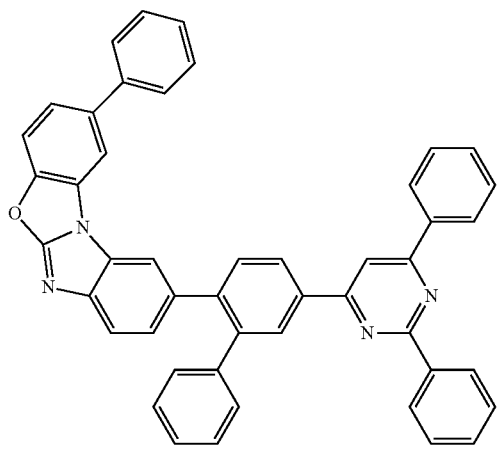
60
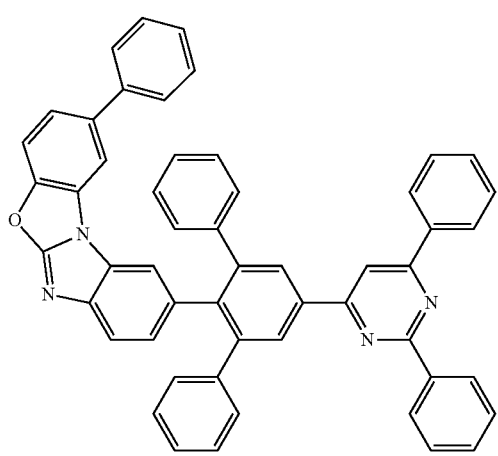
61
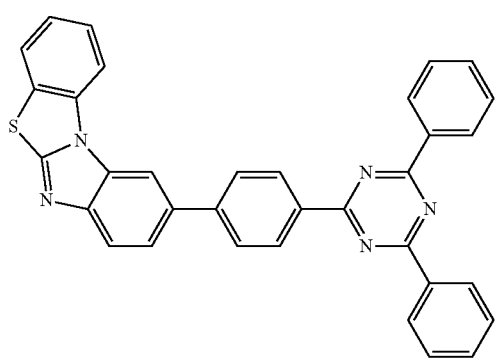
62
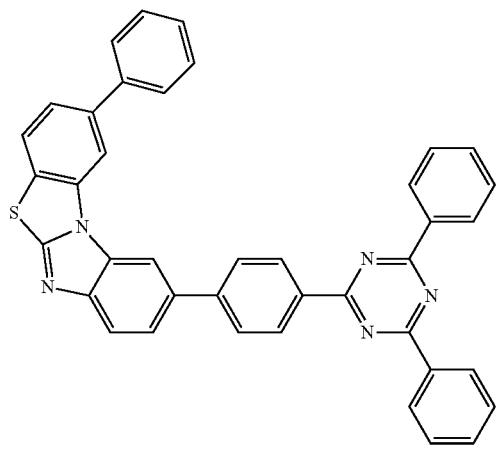
63
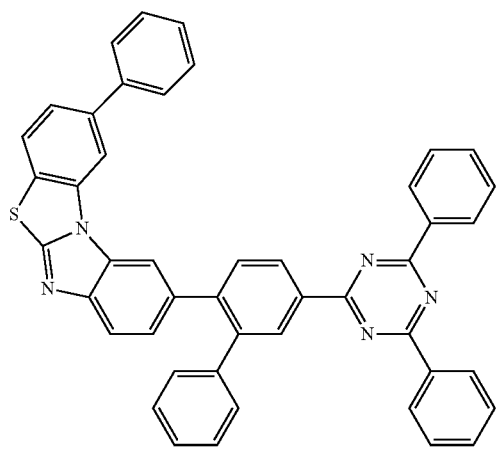
64
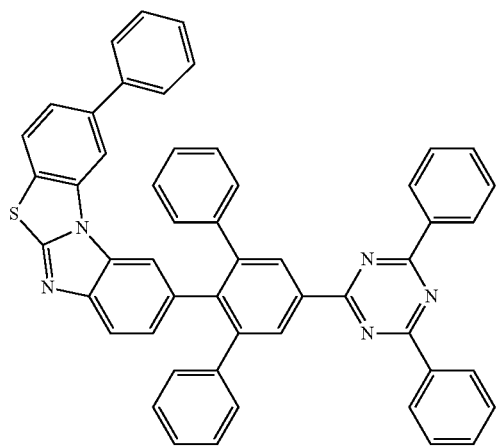

2835
-continued
65
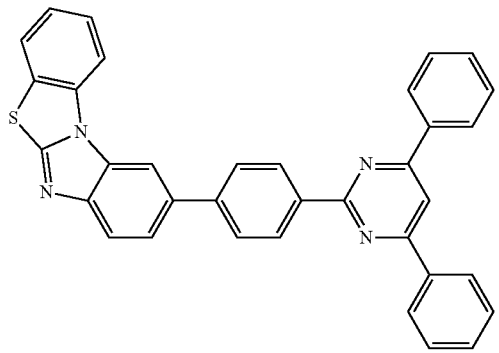
66
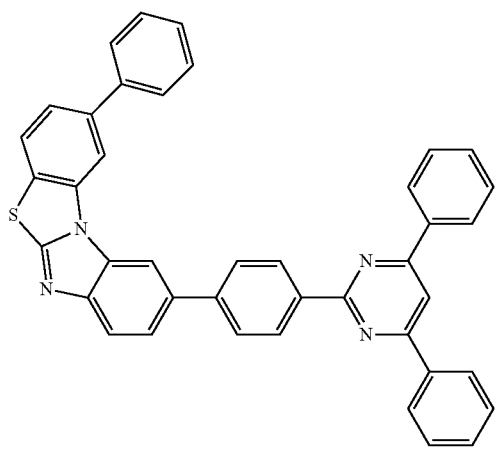
67
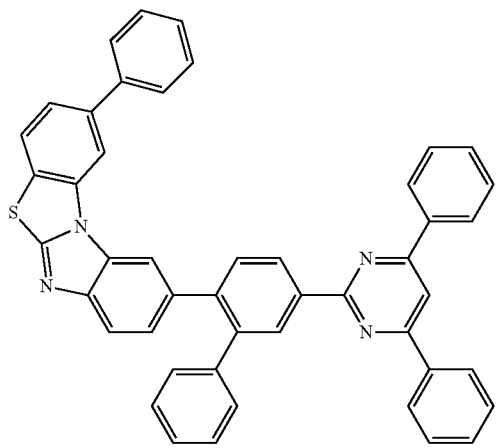
2836
-continued
68
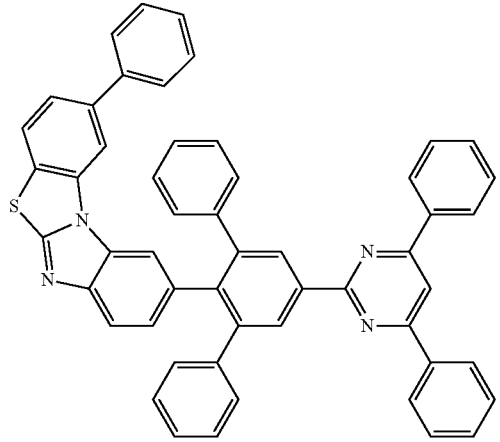
69
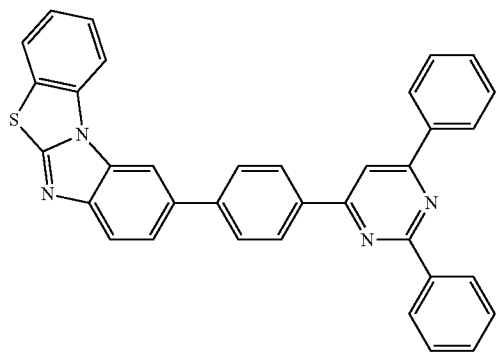
70
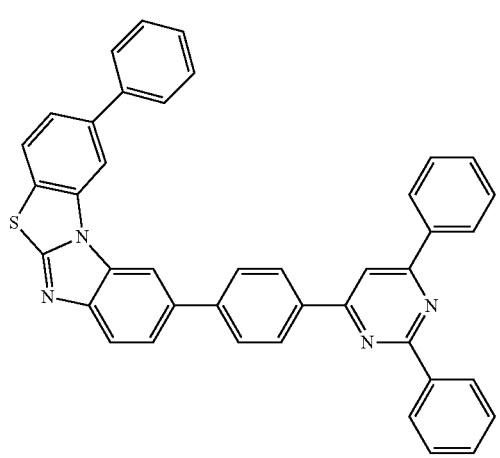

2837
-continued
71
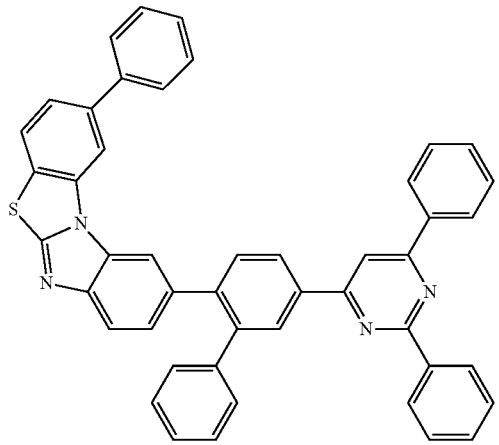
72
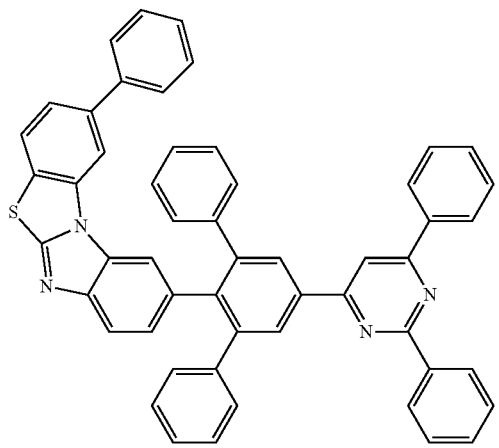
73
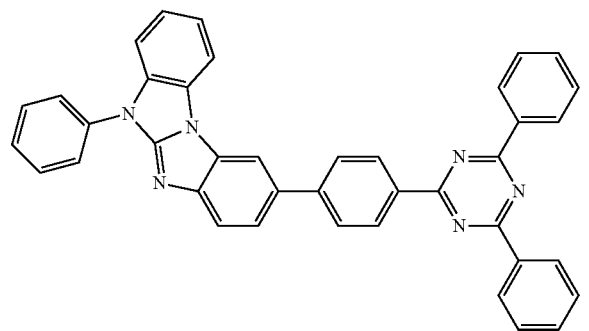
2838
-continued
74
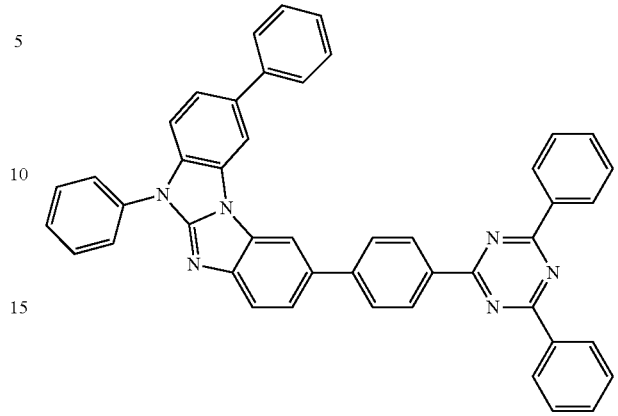
75
76

2839
-continued
77
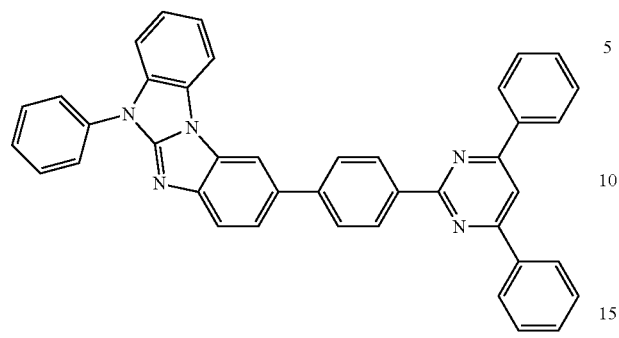
78
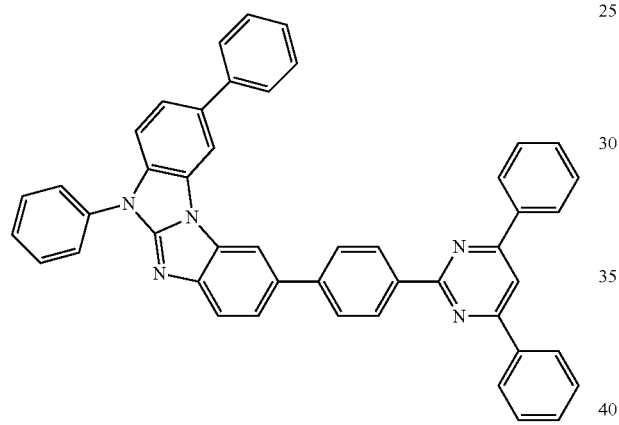
79
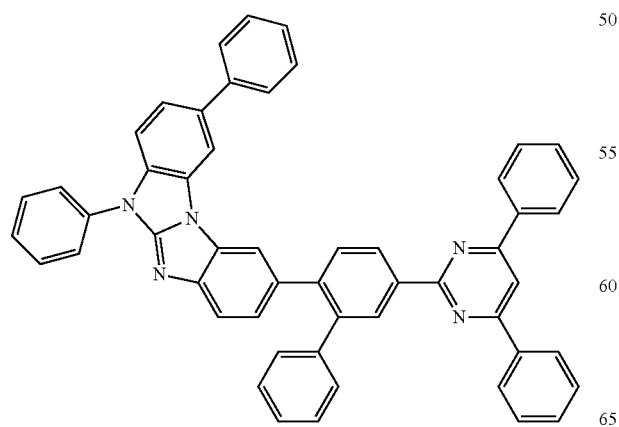
2840
-continued
80
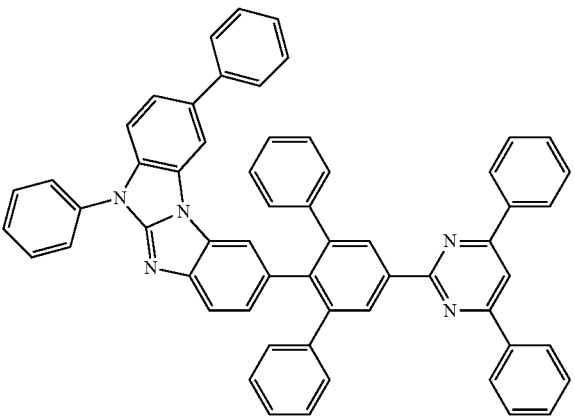
81
82

2841
-continued
83
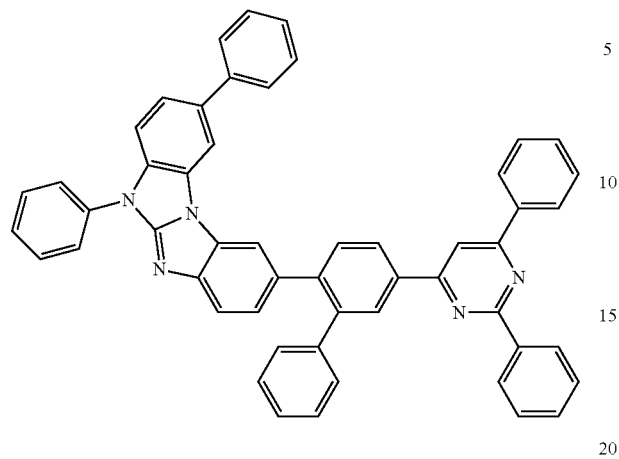
84
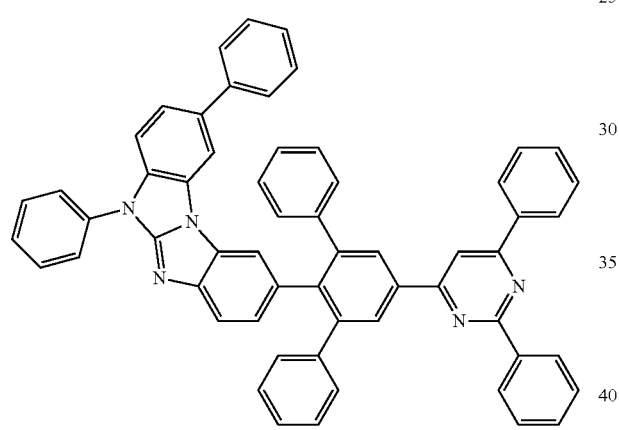
85
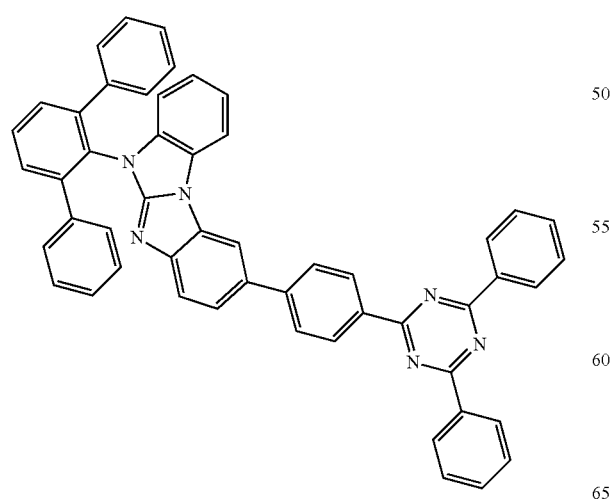
2842
-continued
86
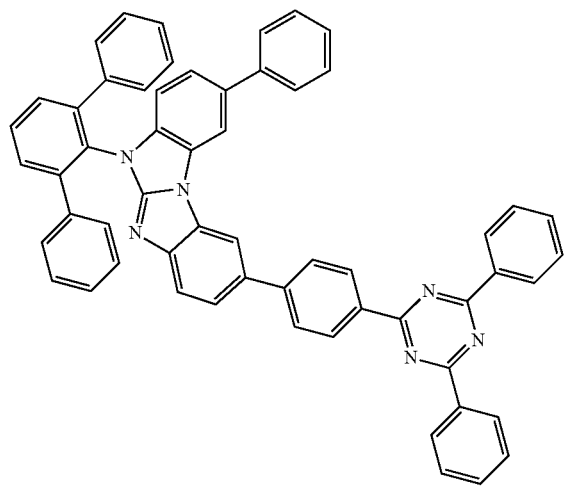
87
88
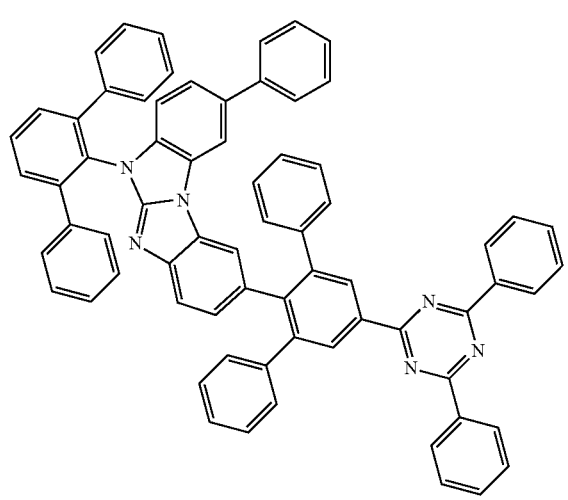

89
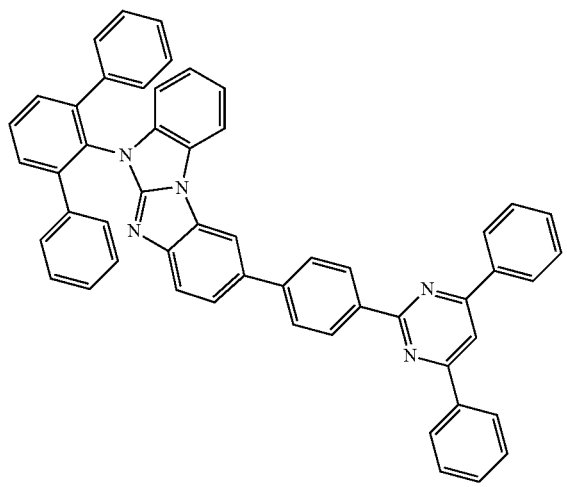
90
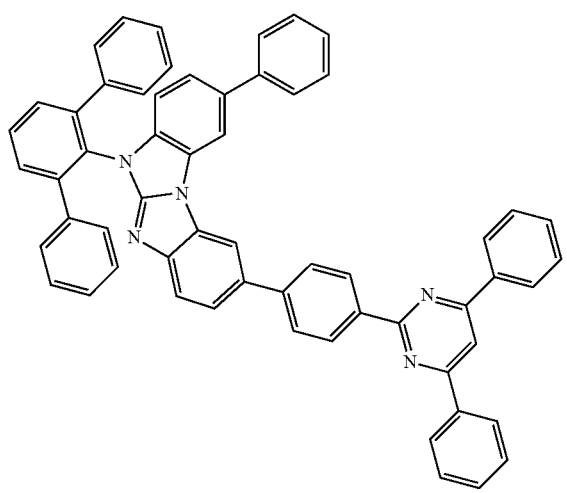
91
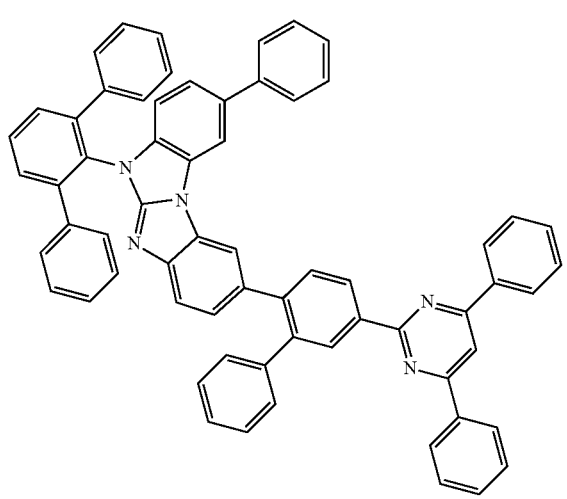
92
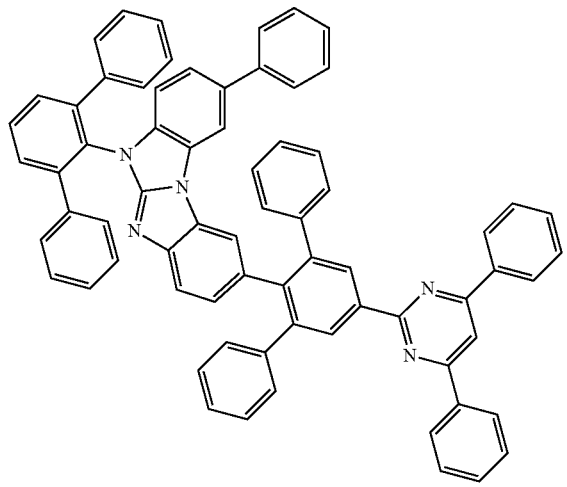
93
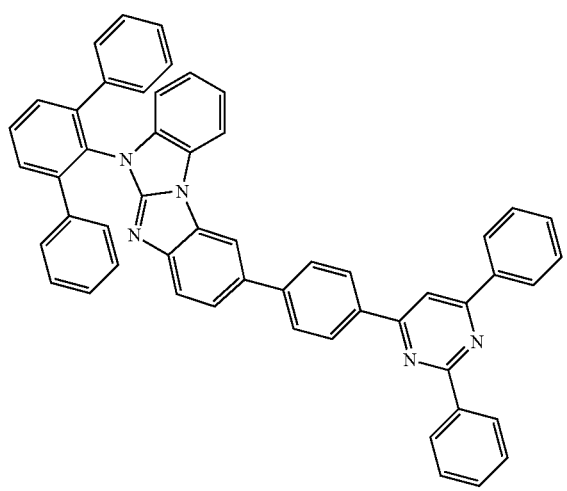
94
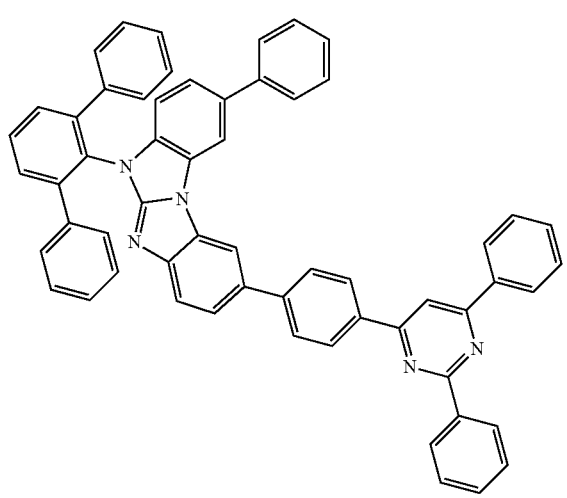

95
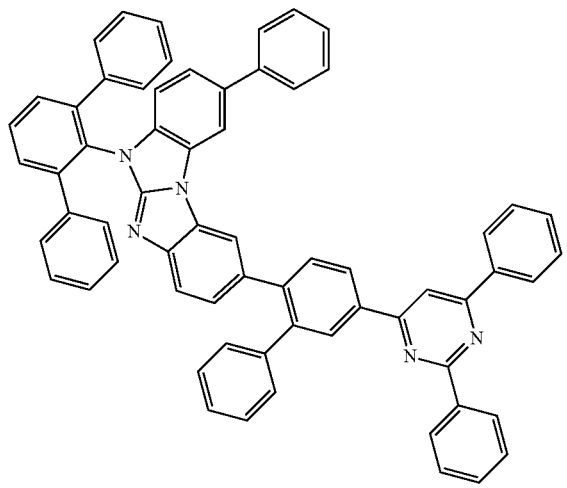
96
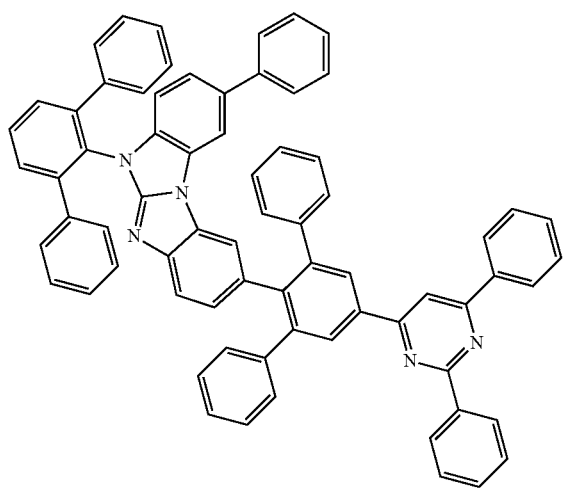
97
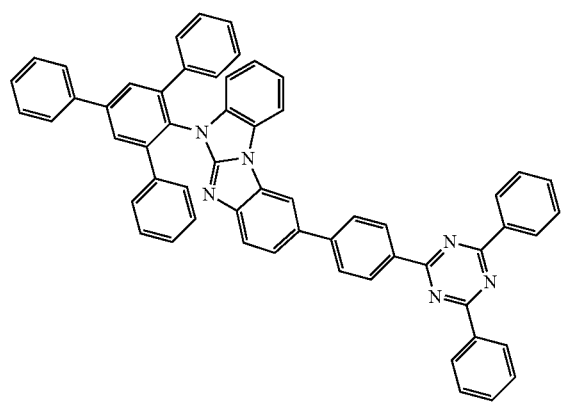
98
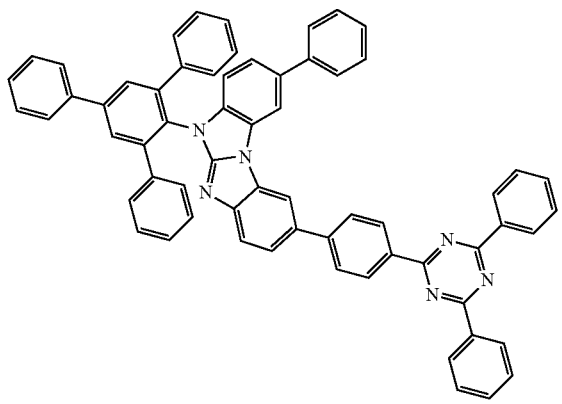
99
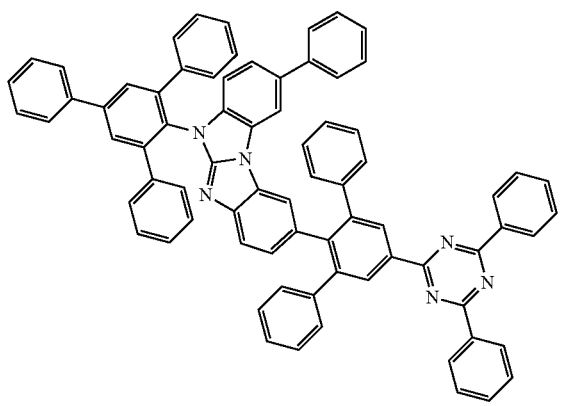
100

2847
-continued
101
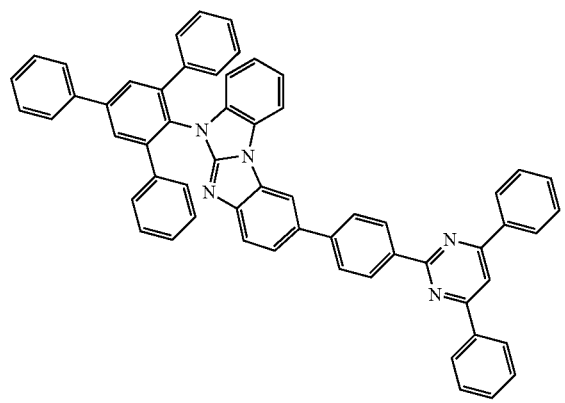
102
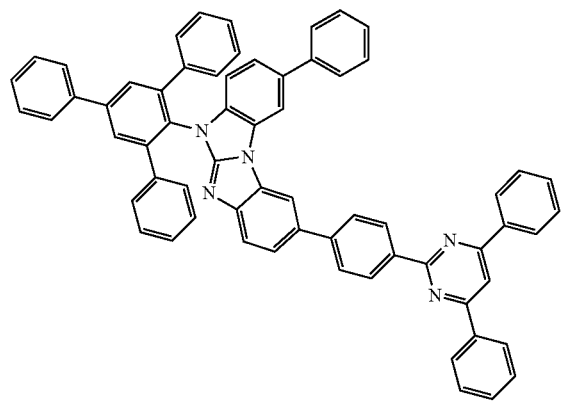
103
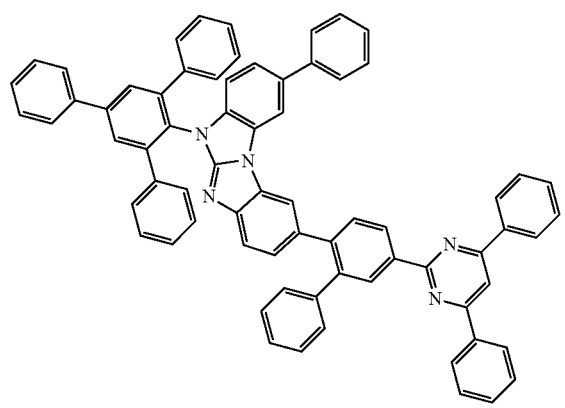
2848
-continued
104
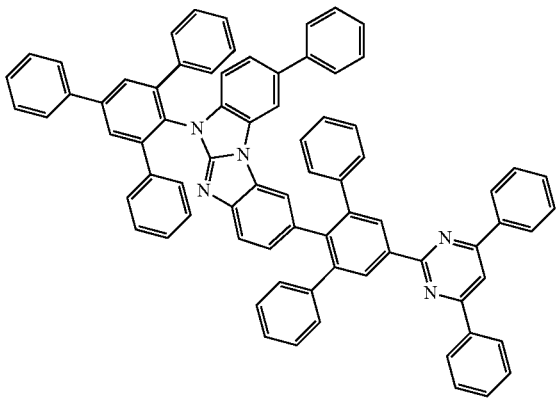
105
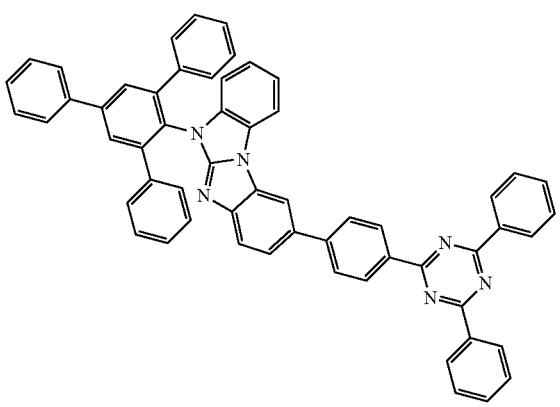
106
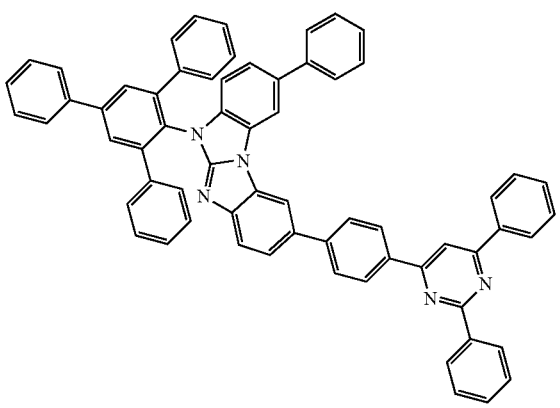

107
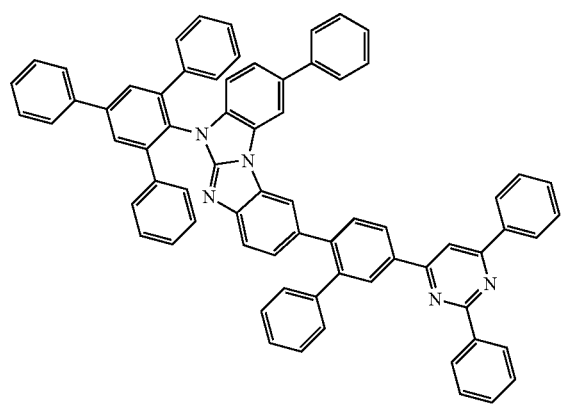
108
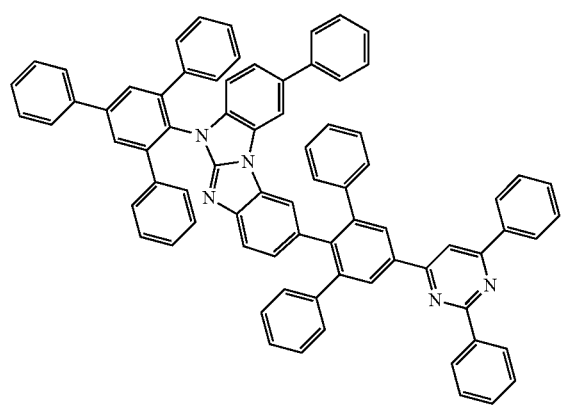
109
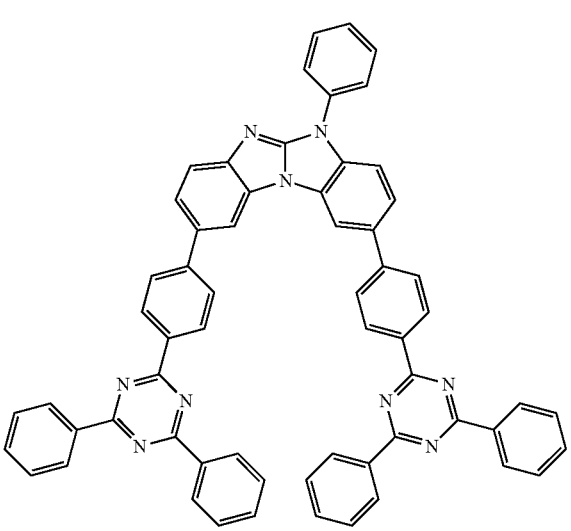
110
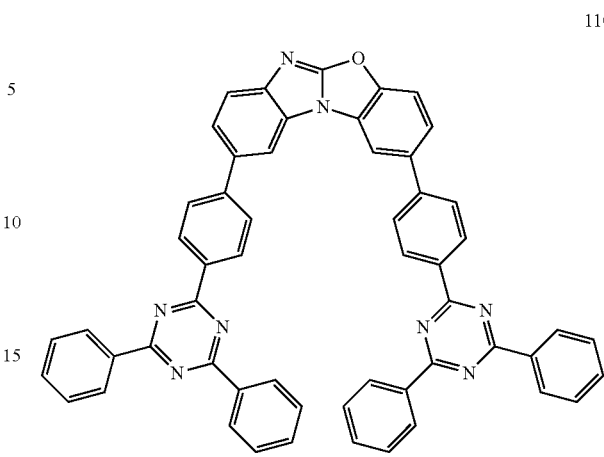
111
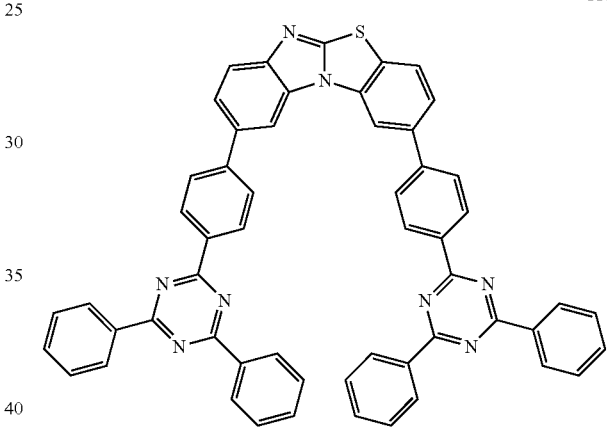
112
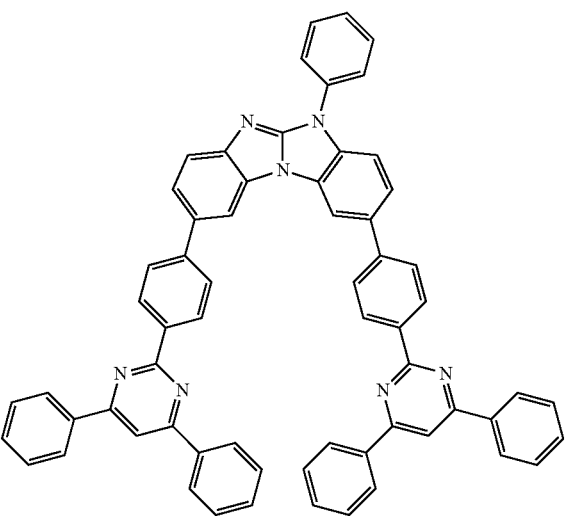

113
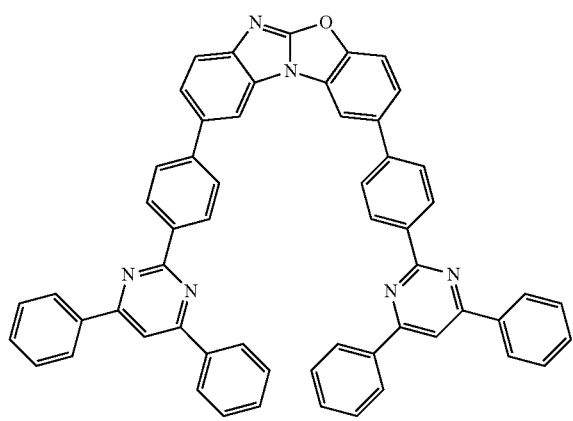
114
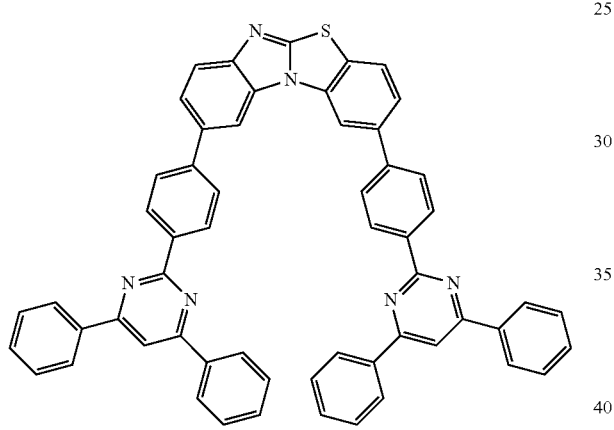
115
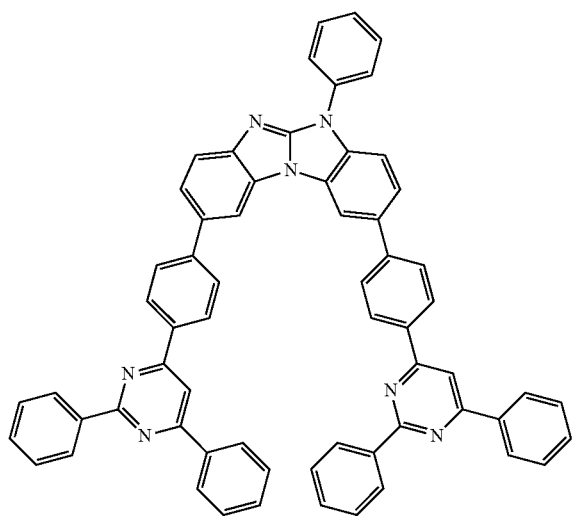
116
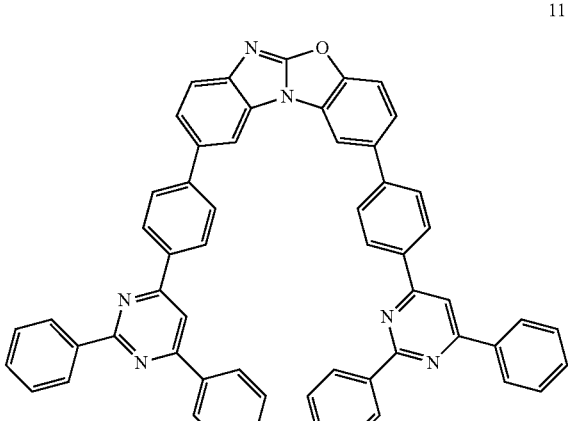
117
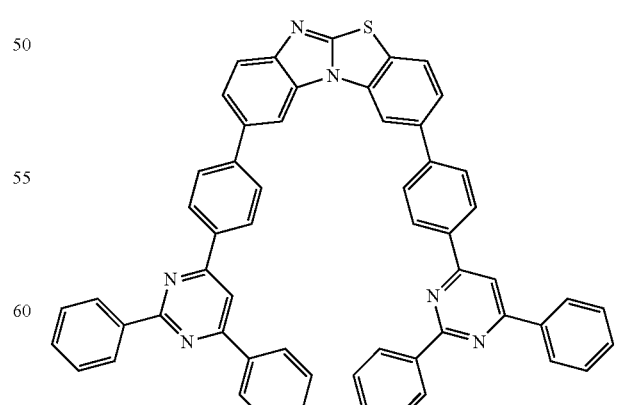

Group VIII
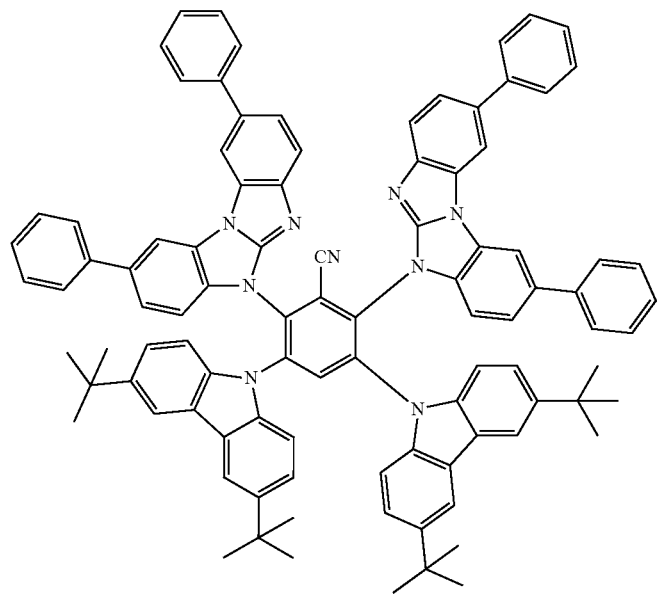
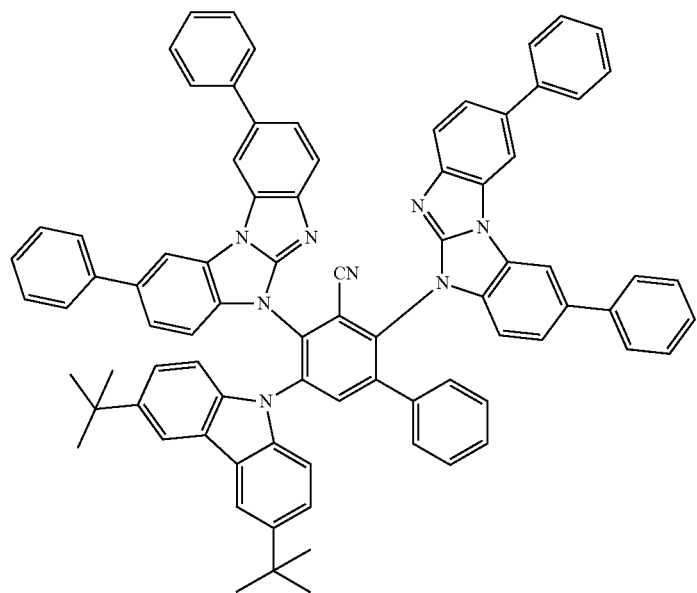

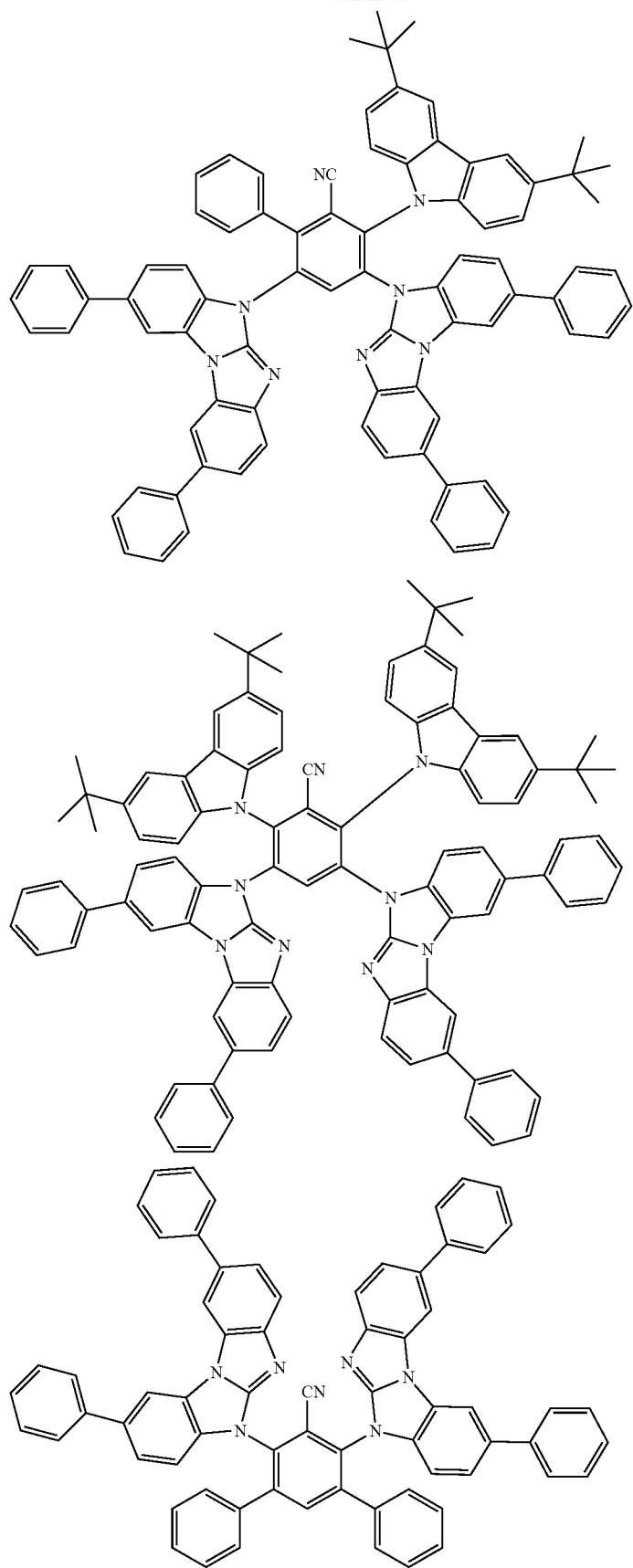
-continued

2857
-continued
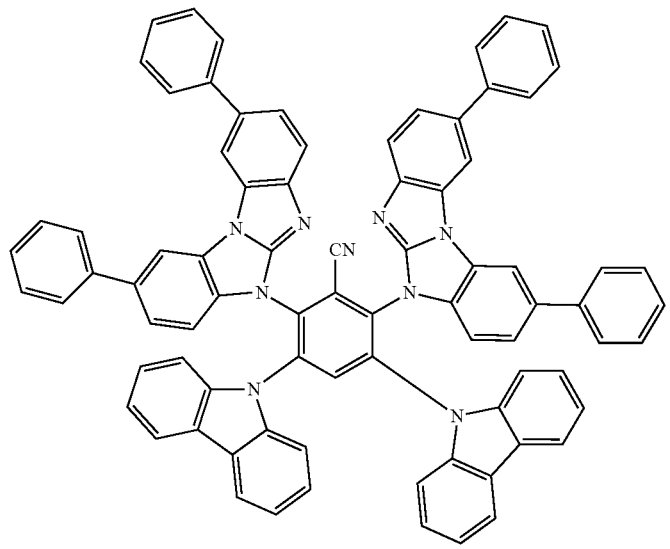
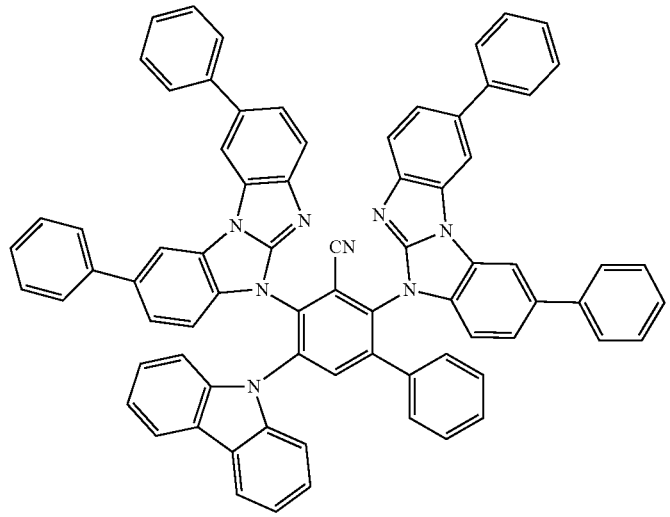
2858
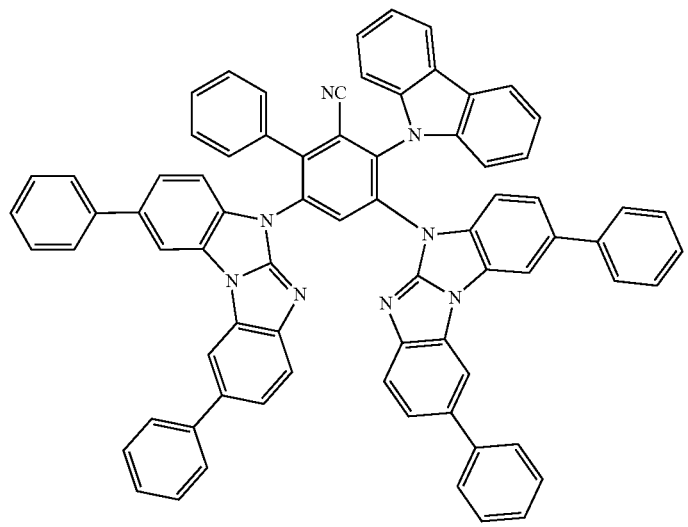

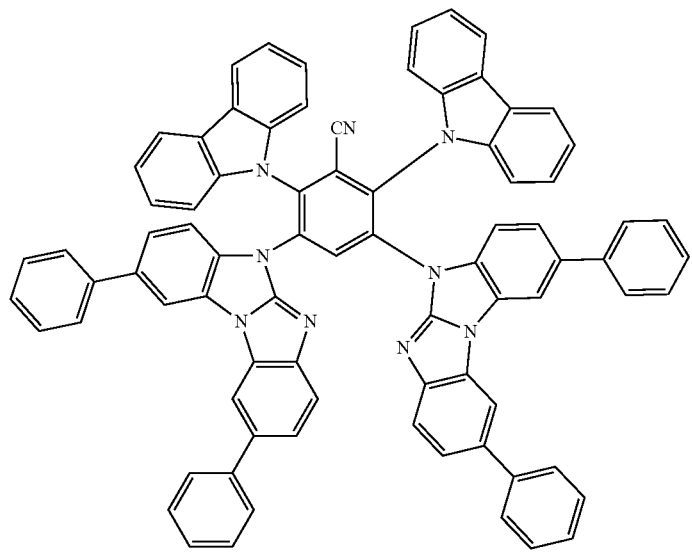
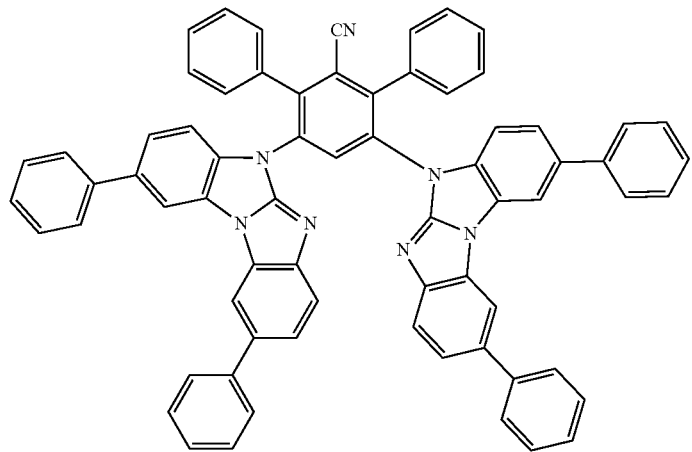
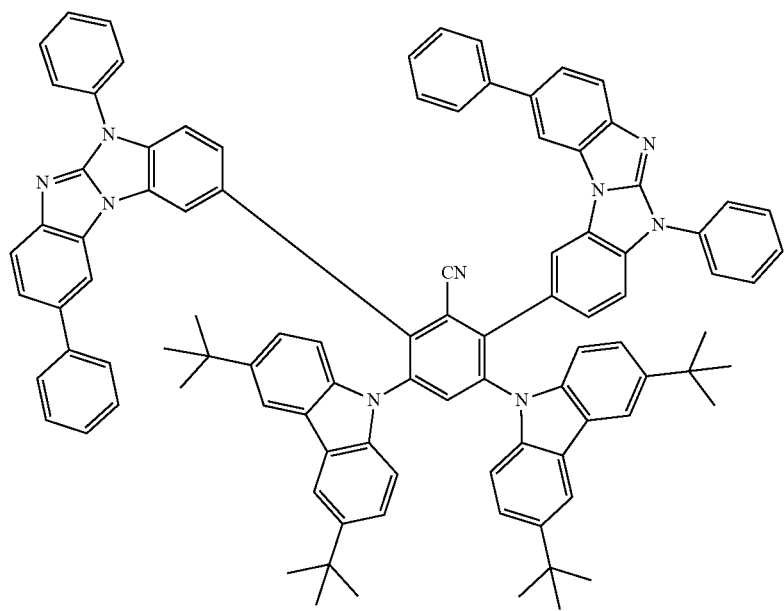

2861 2862
-continued
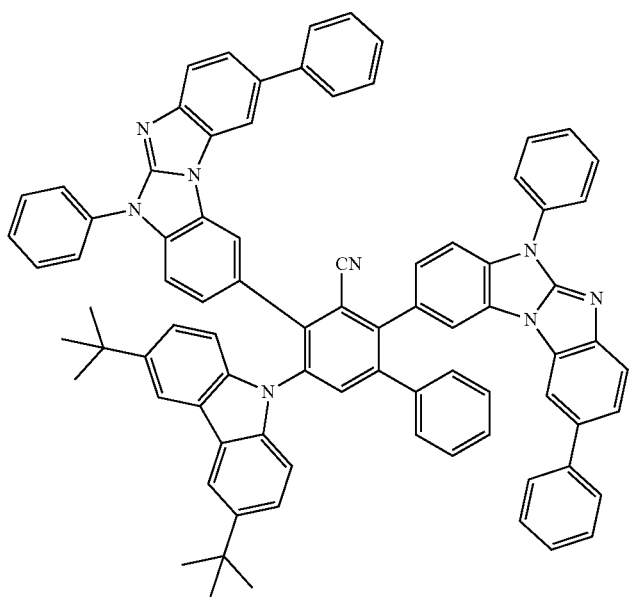
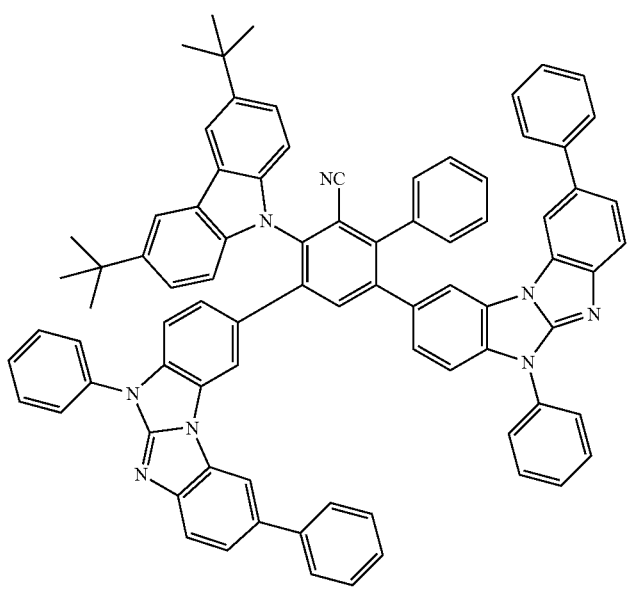

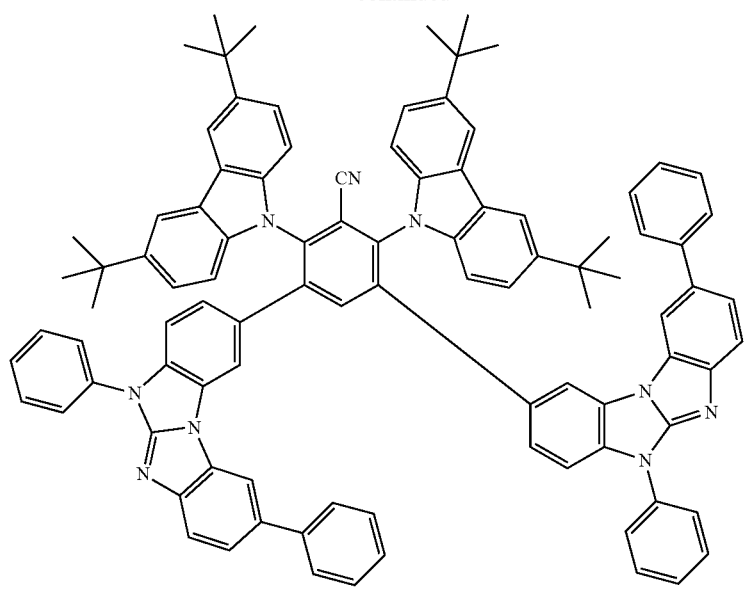
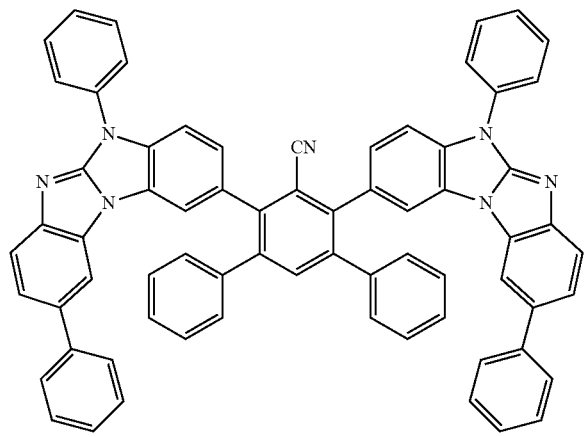
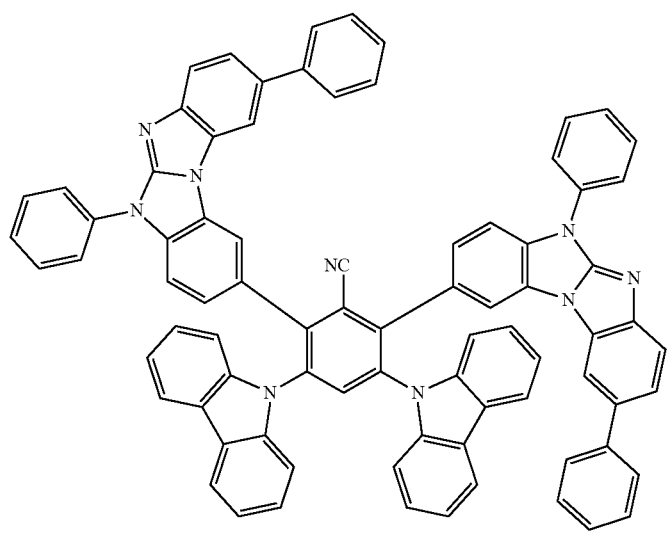

2865
-continued
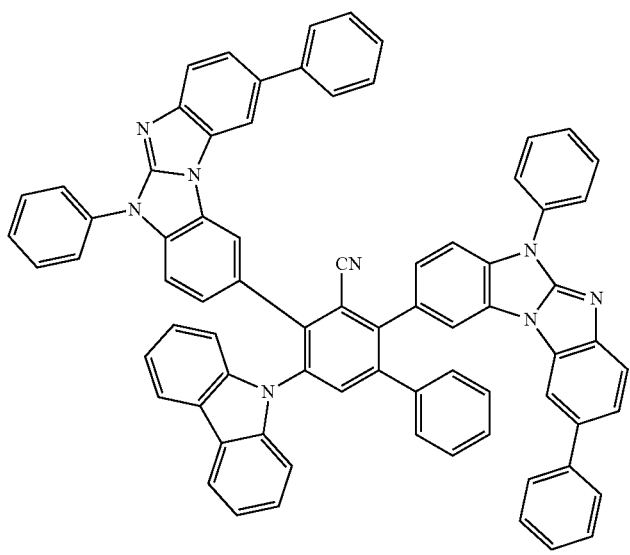
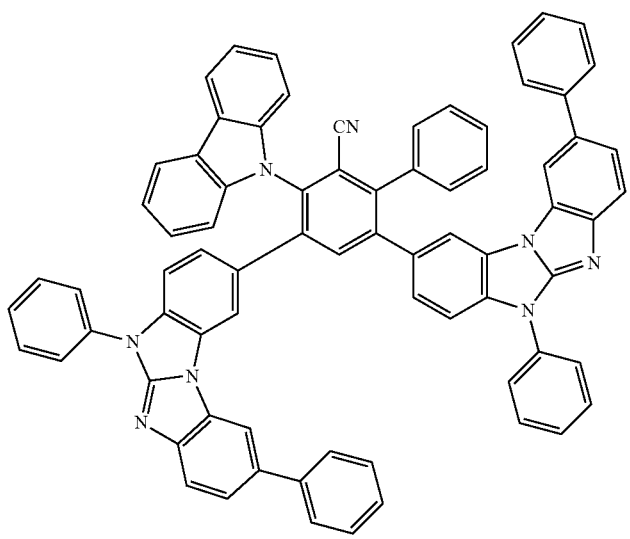
2866
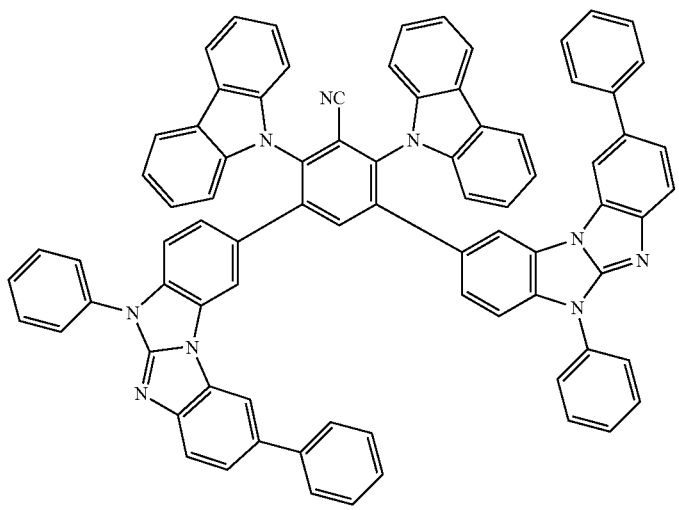

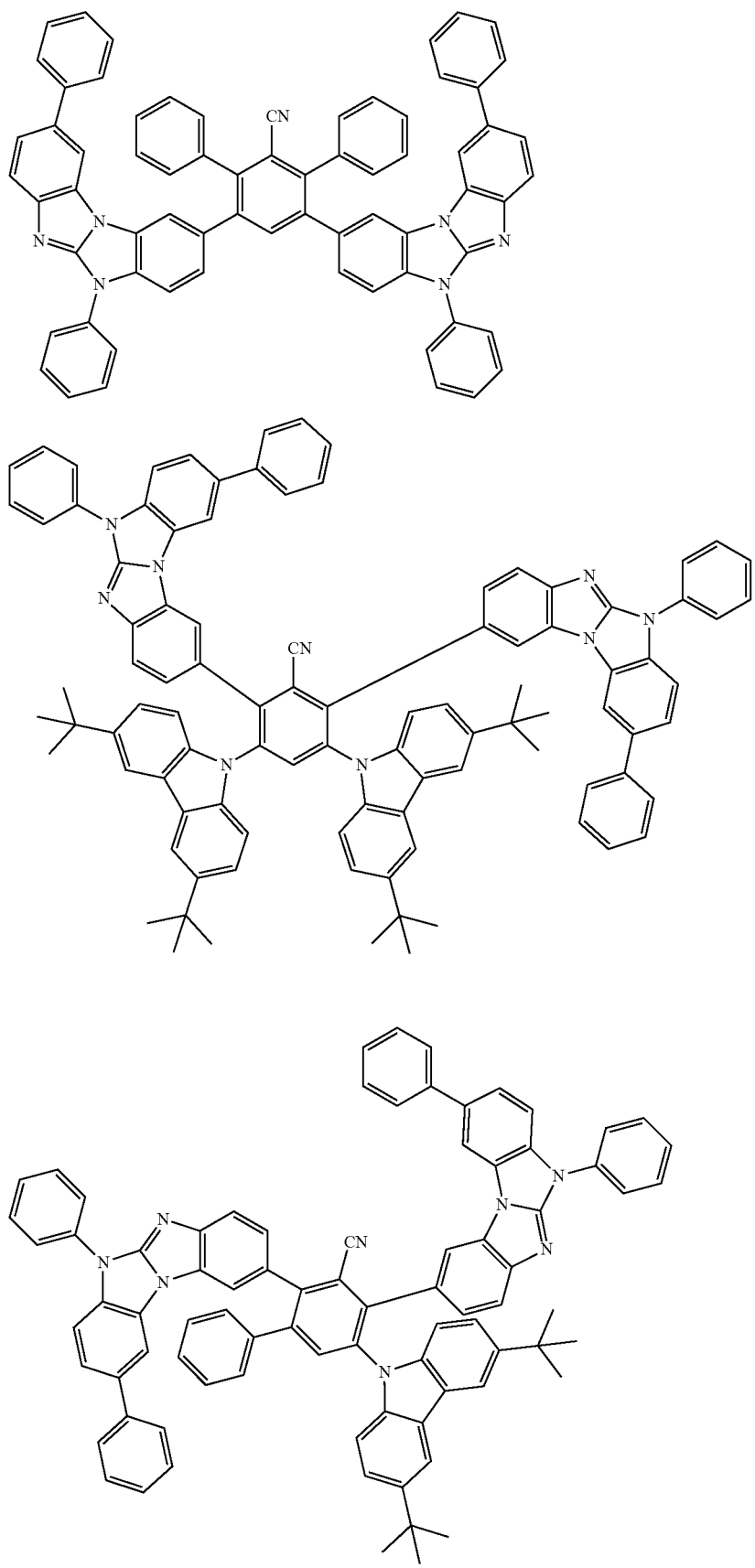

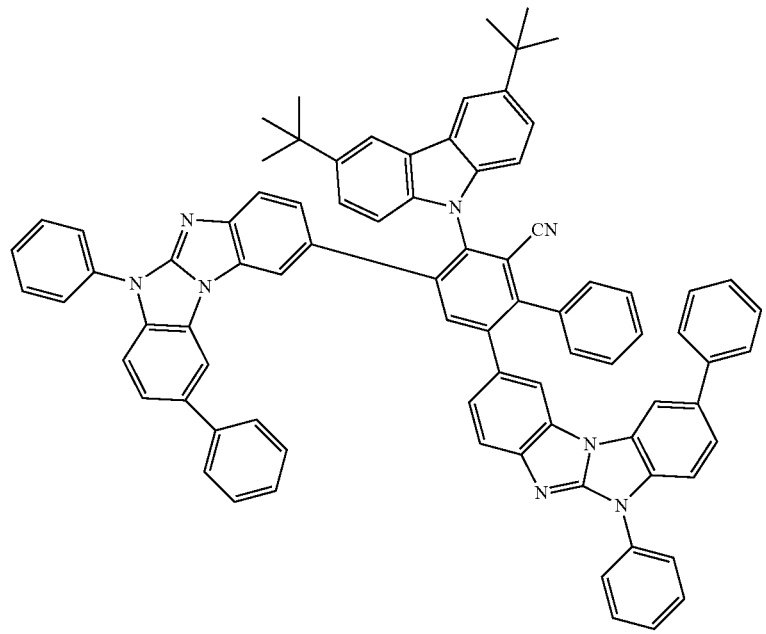
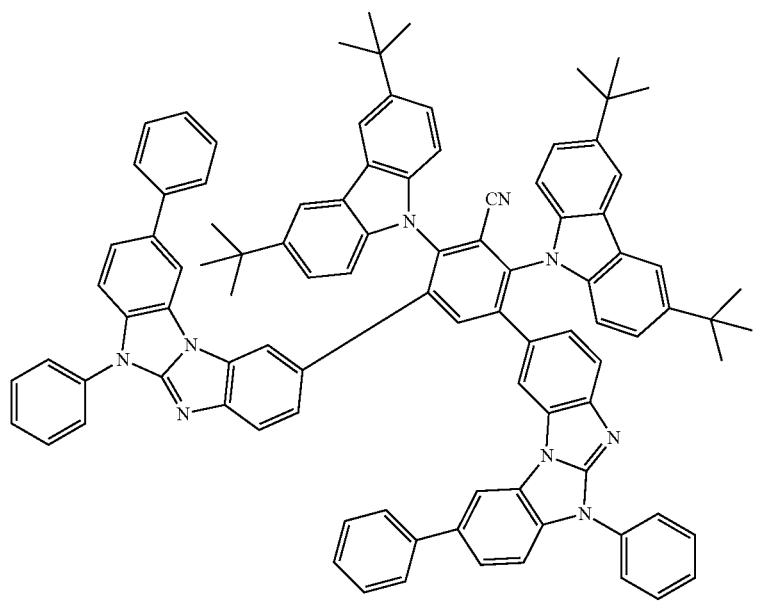

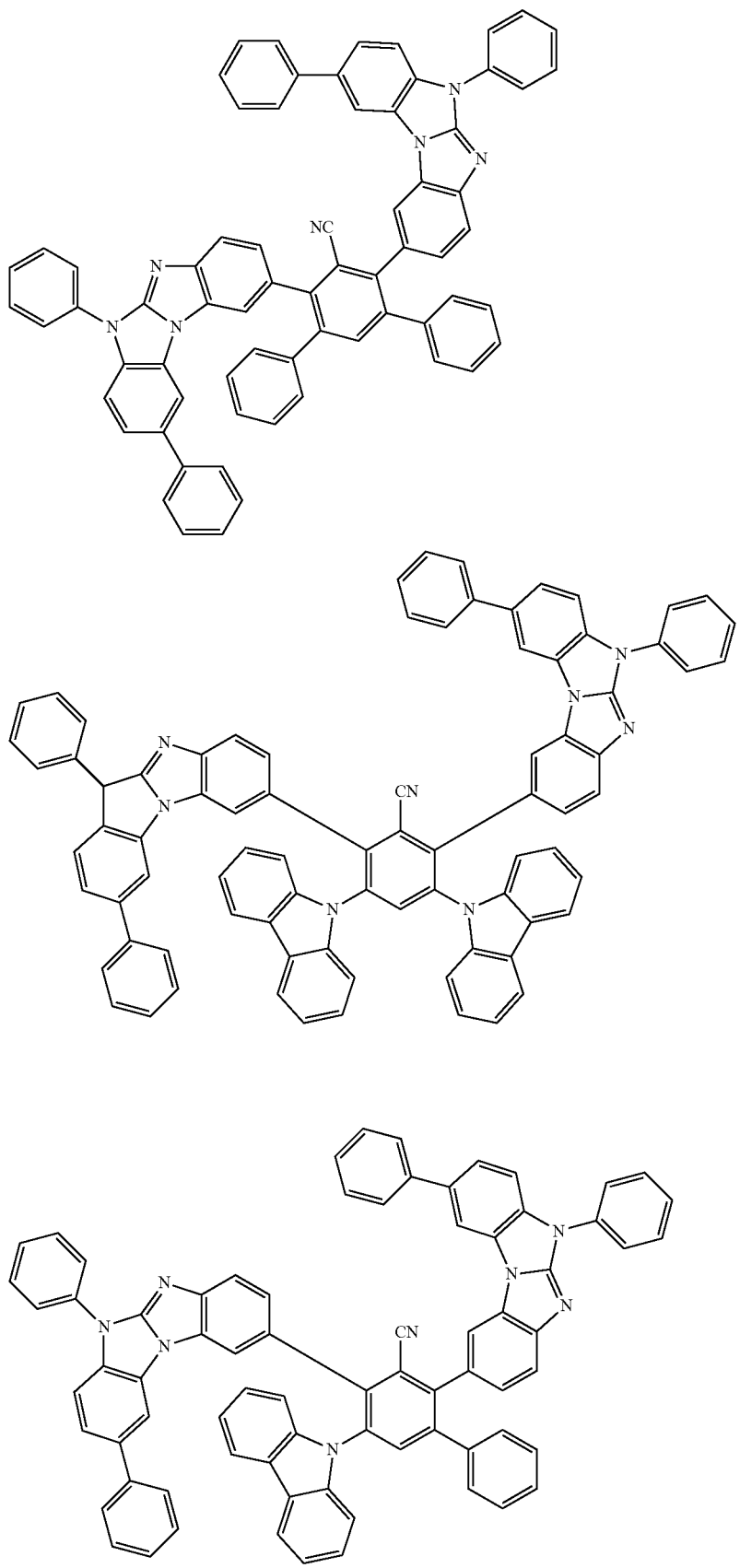

2873
-continued
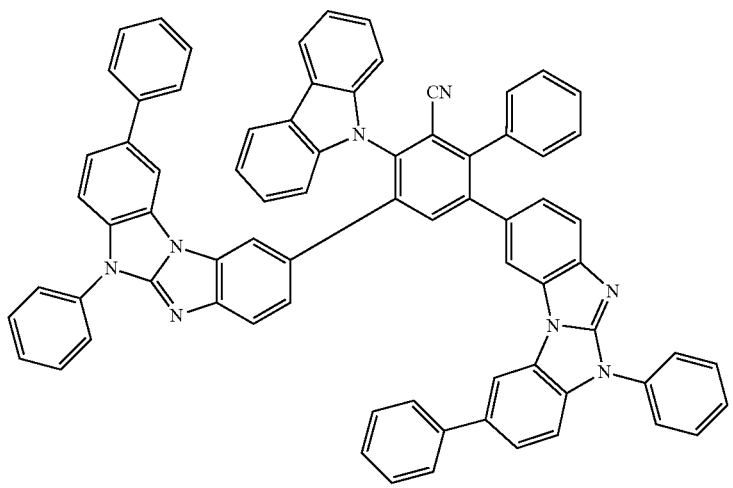
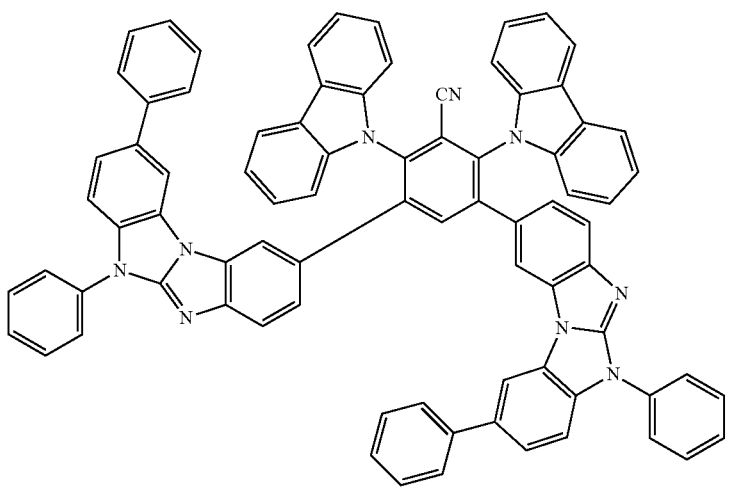
2874
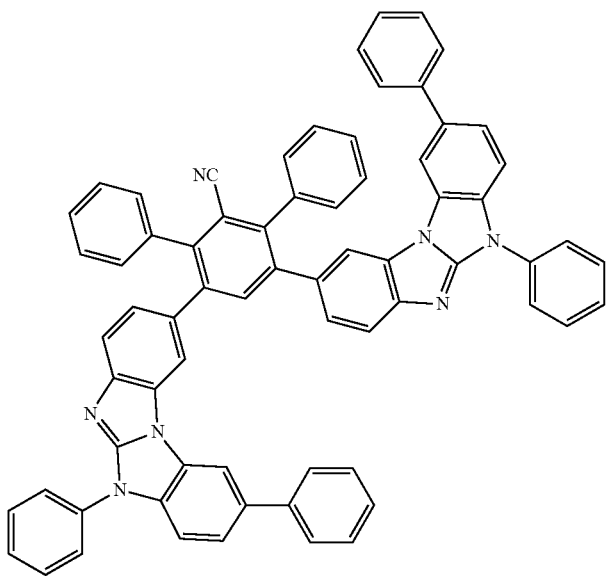

2875
-continued
2876
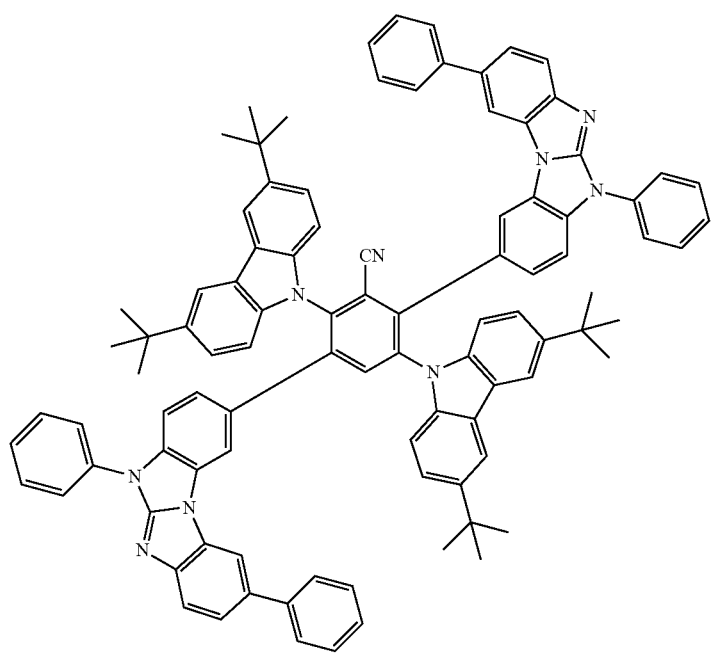
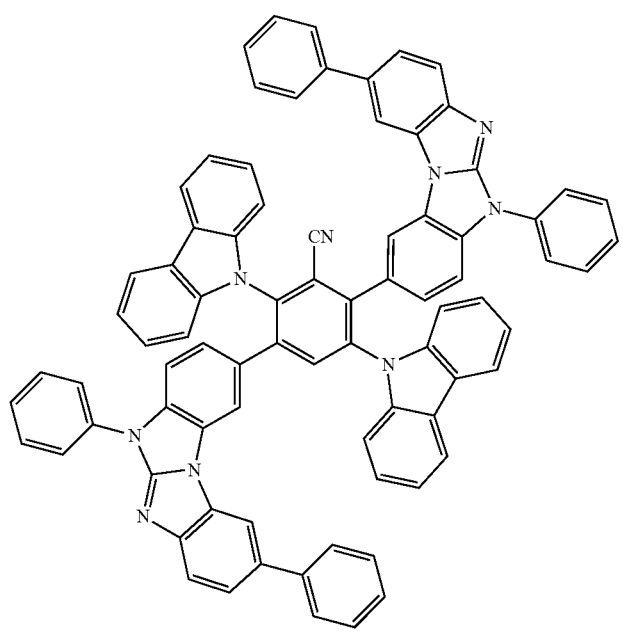

2877
-continued
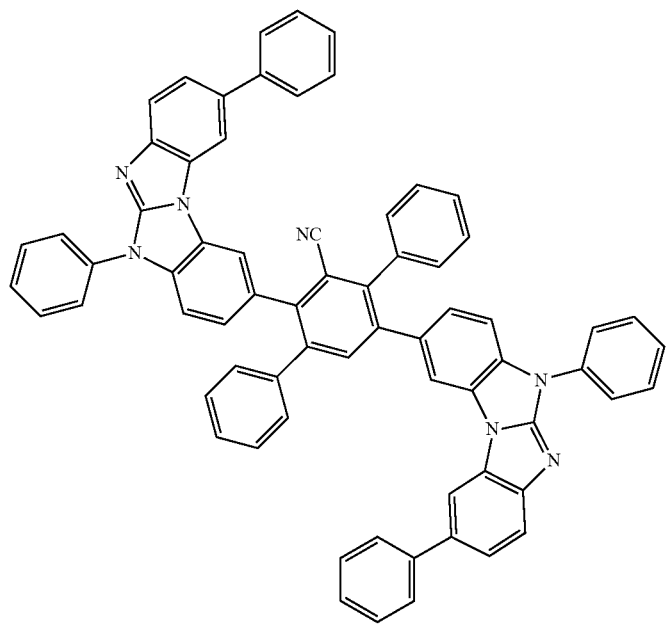
2878
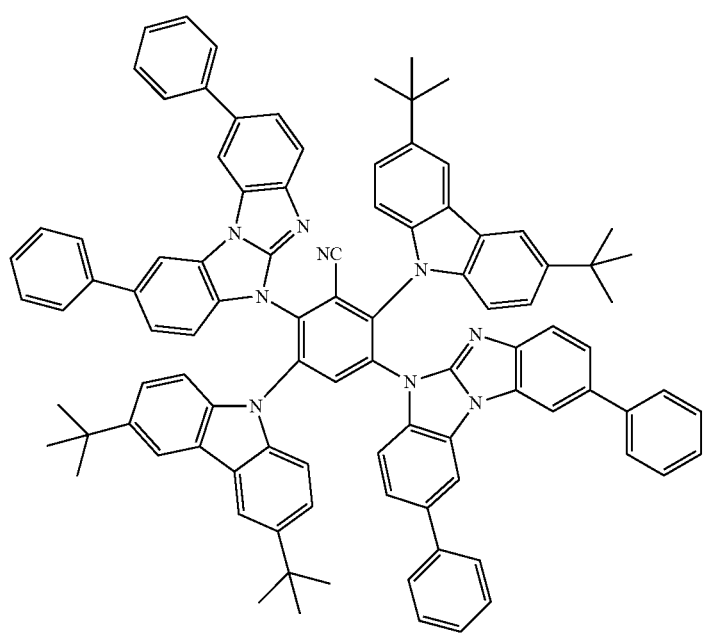

2879
-continued
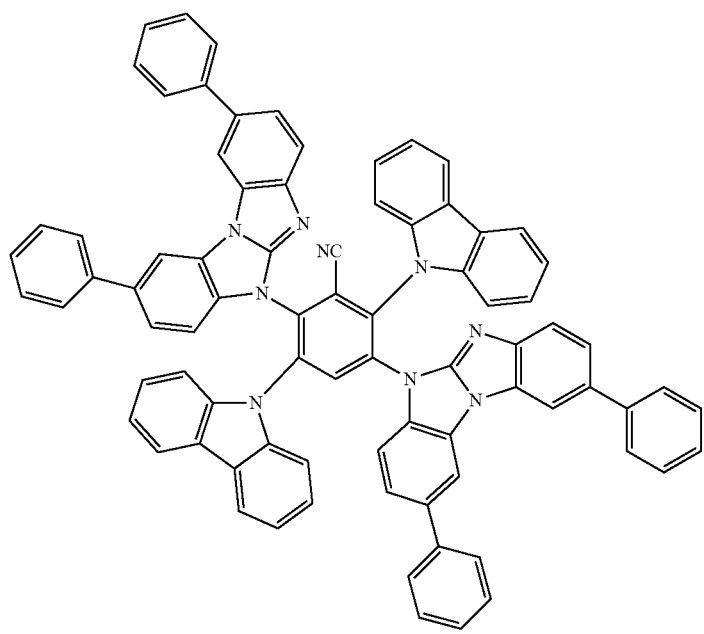
2880
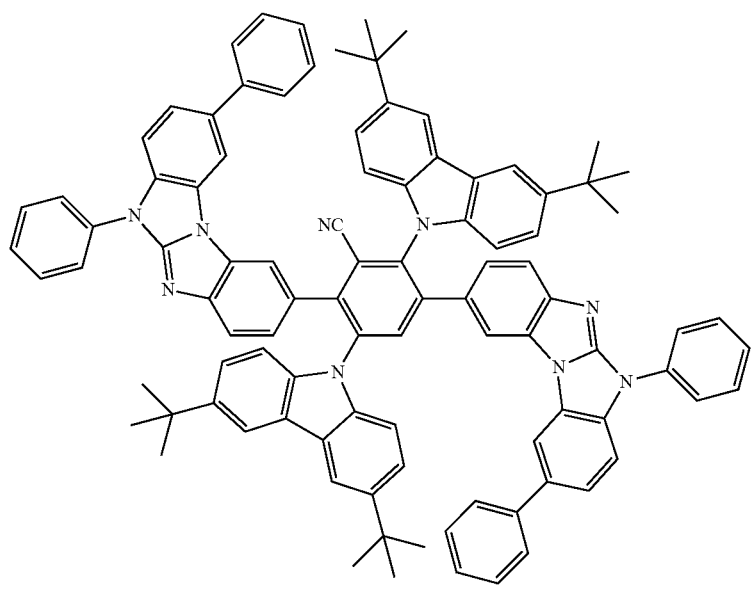

-continued
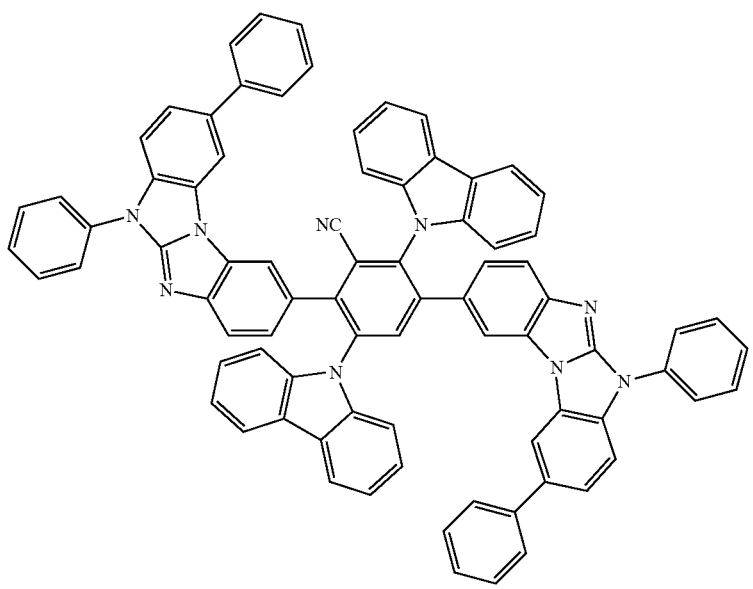
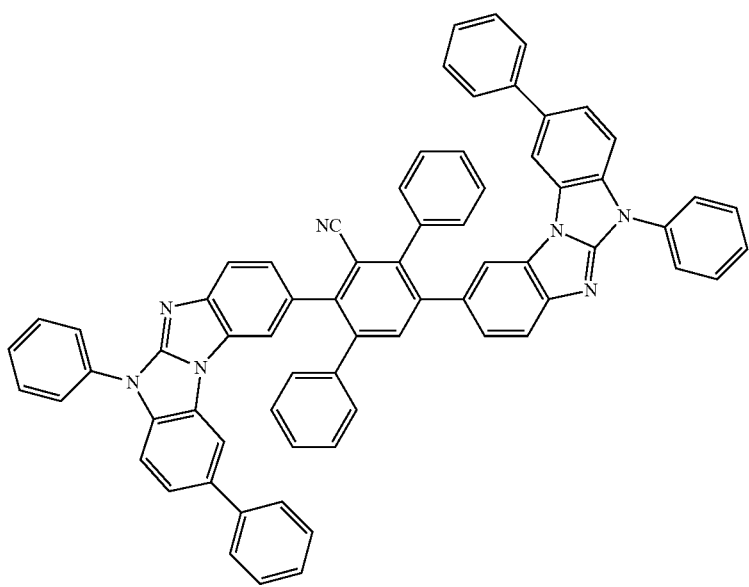

2883
-continued
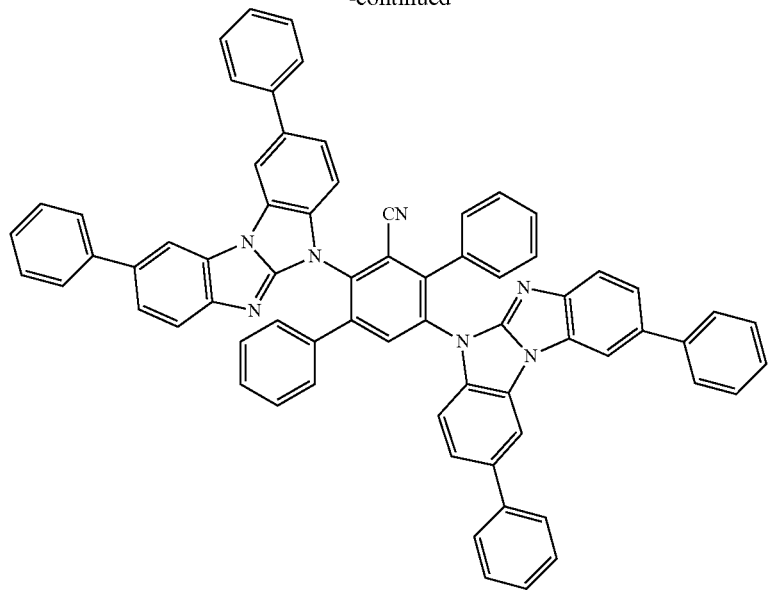
Group IX
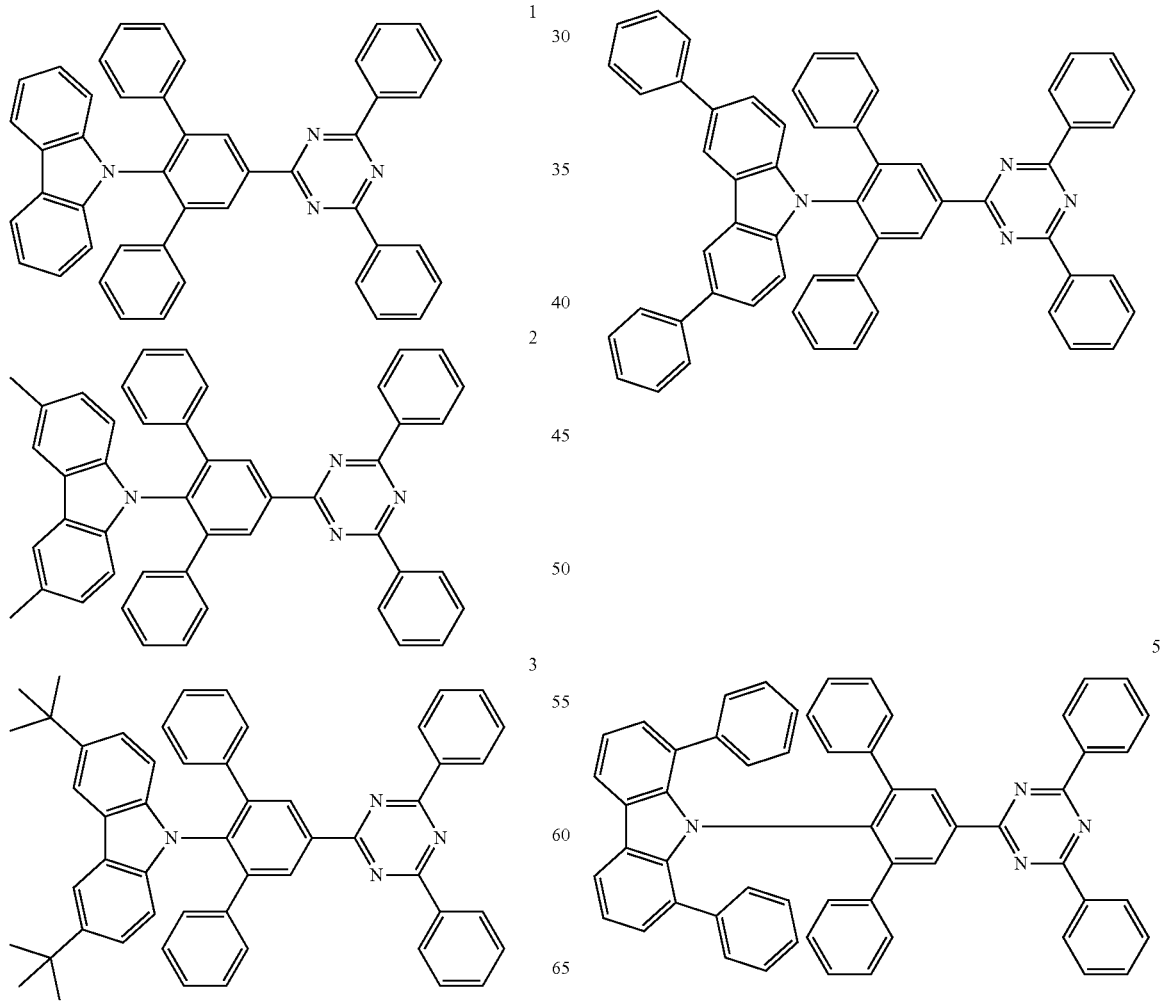

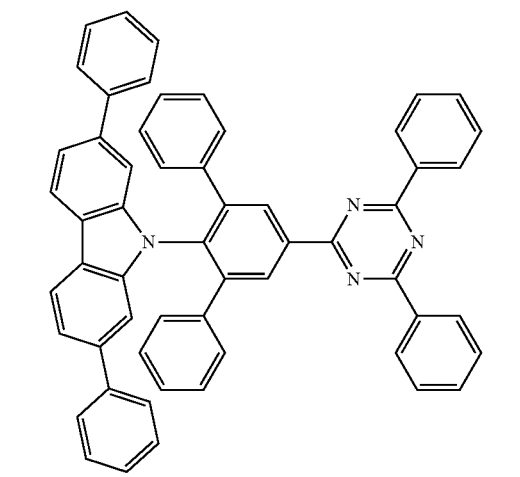
6

7

8
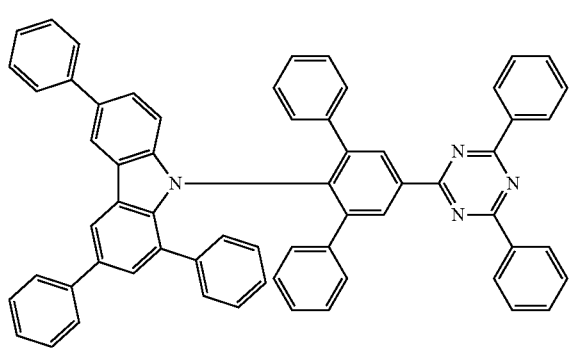
9
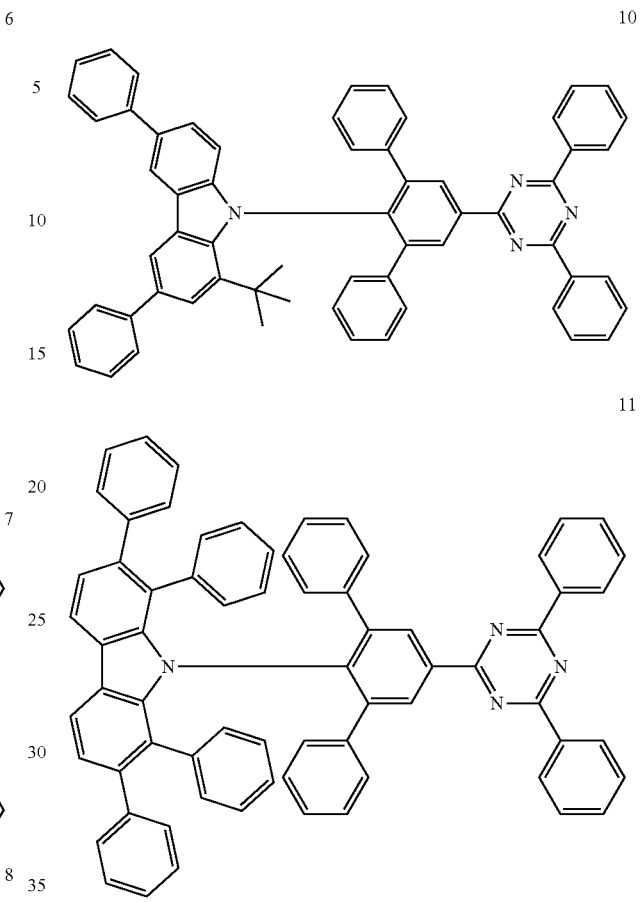
10
11
12
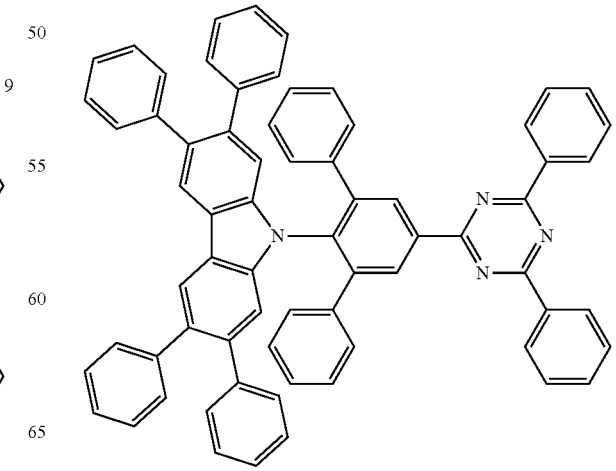
13

14
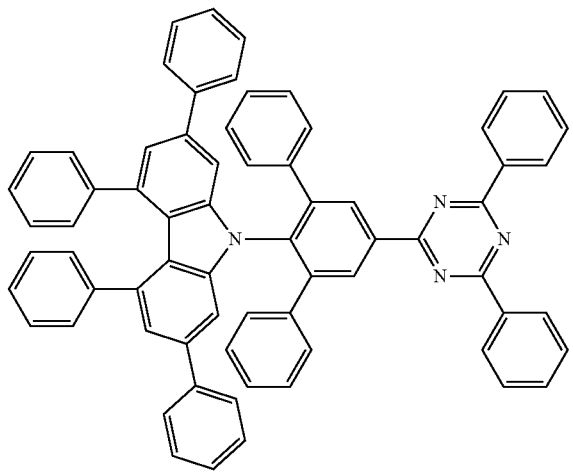
15
18
19
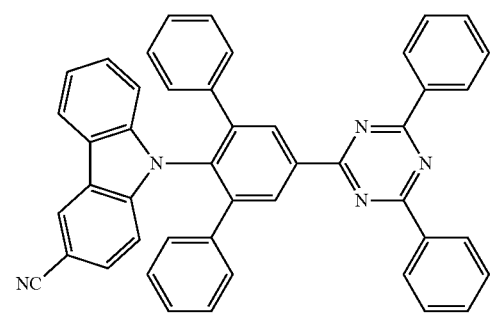
16
20
17
21
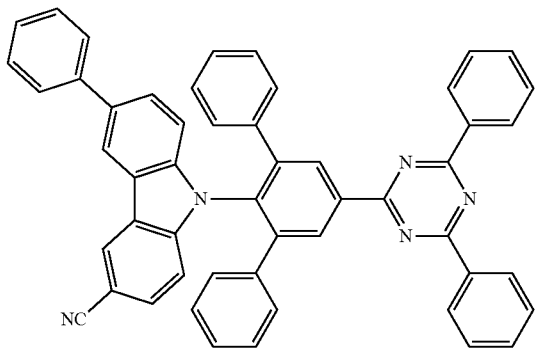

2889 -continued
22
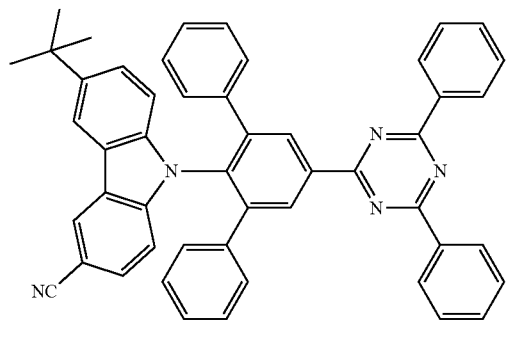
23
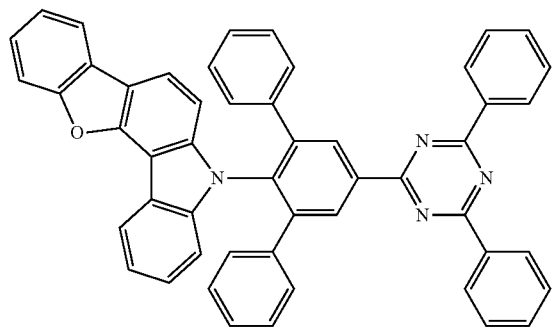
24
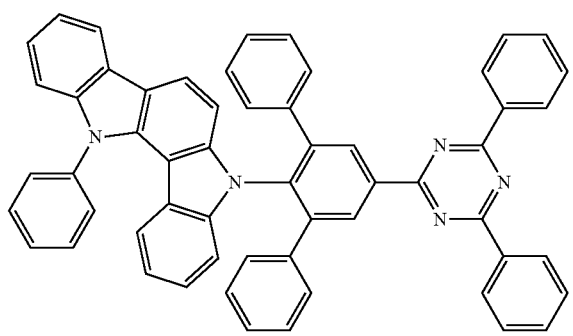
25
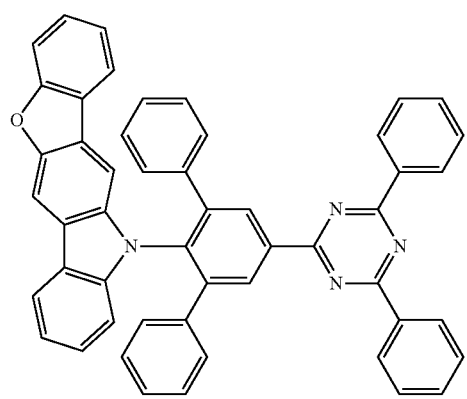
2890 -continued
26
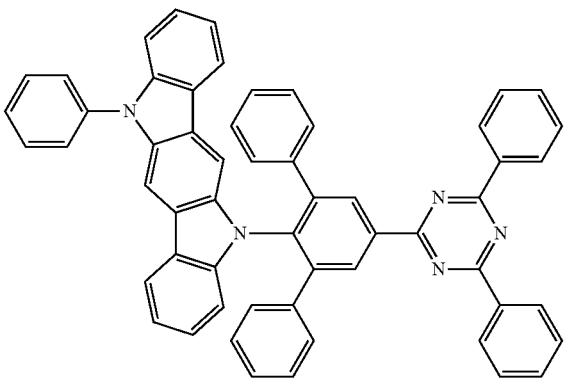
27
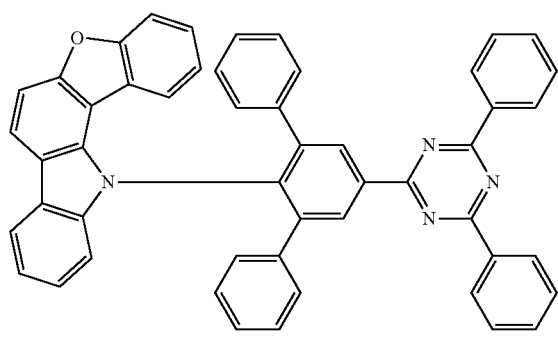
28
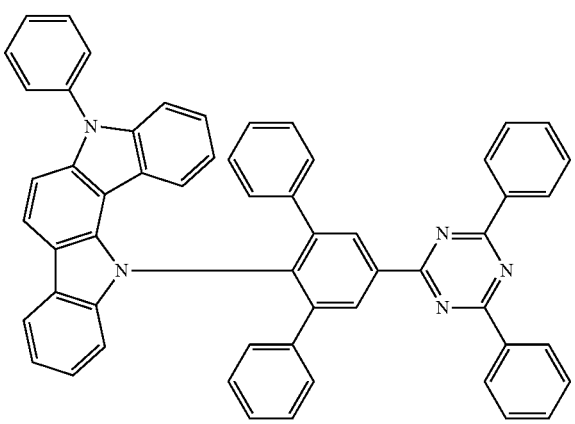
29
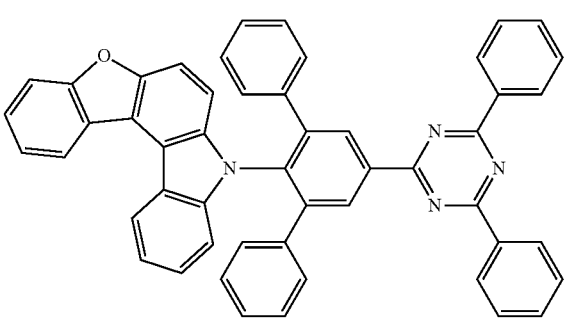

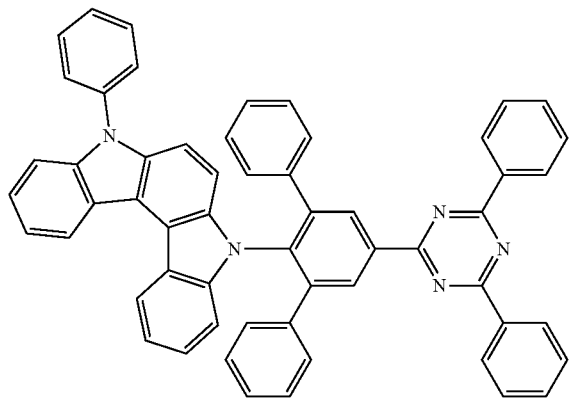
30
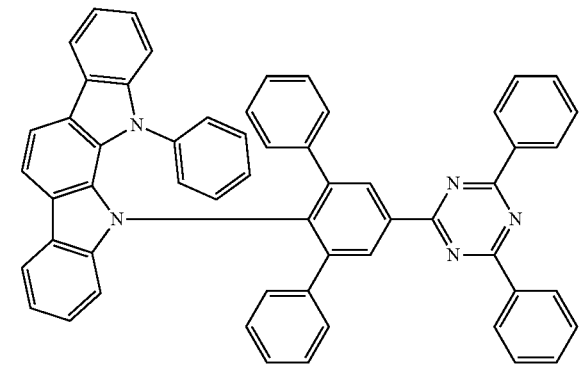
34
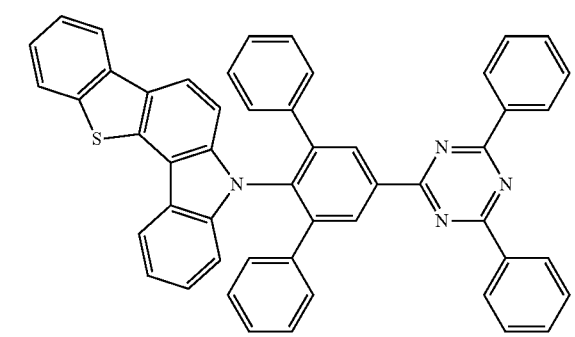
35
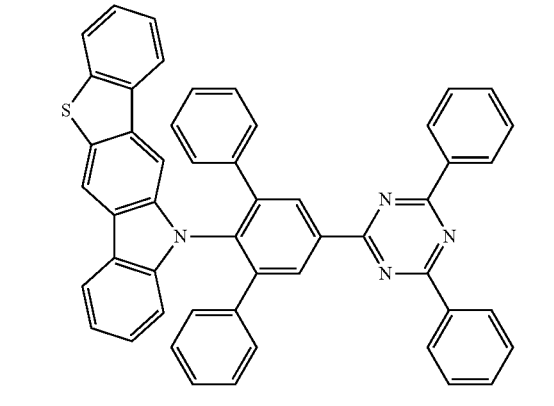
36
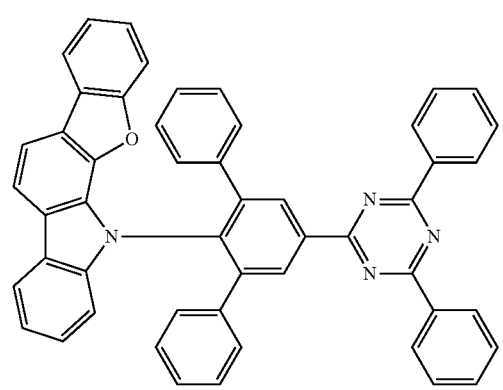
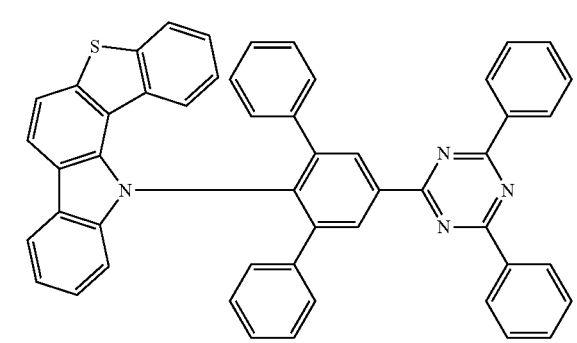

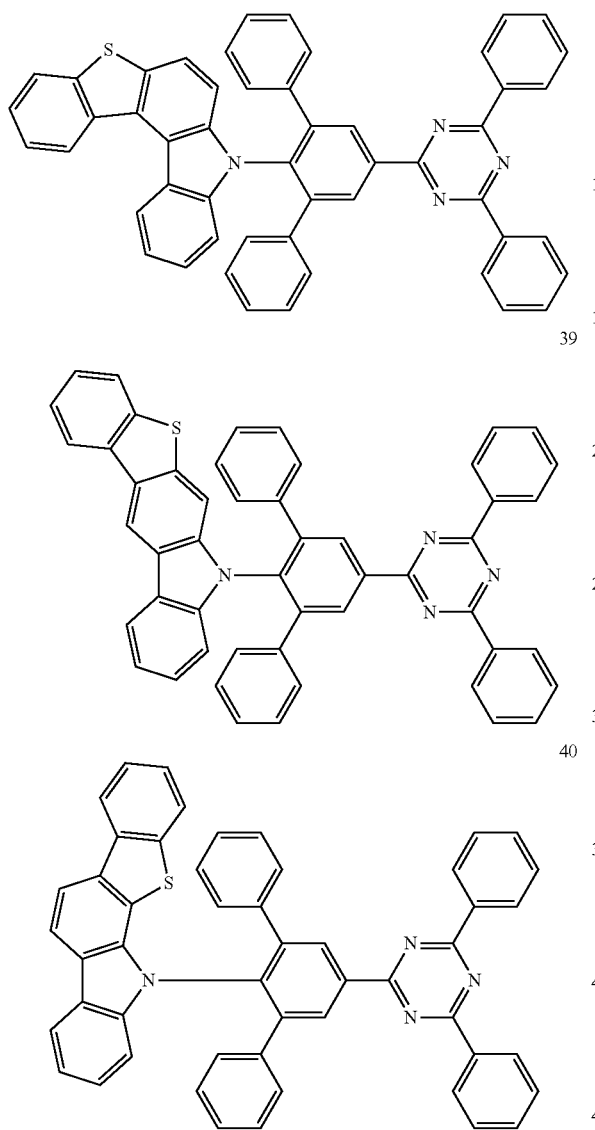
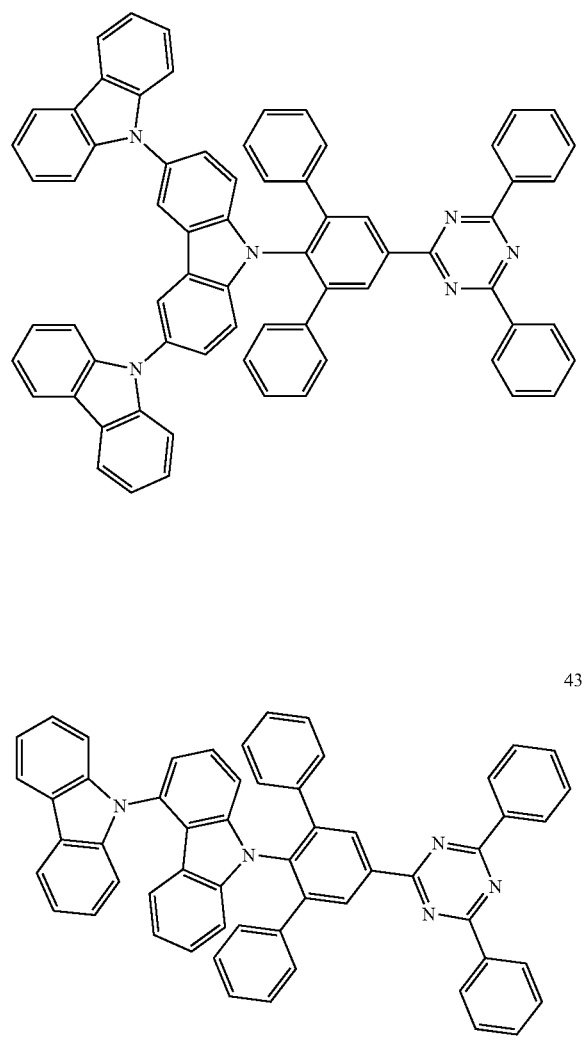
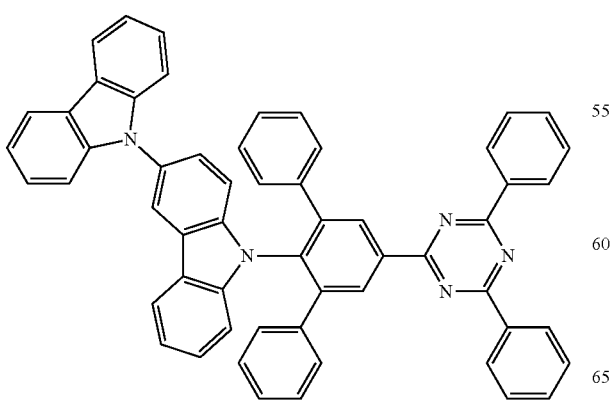
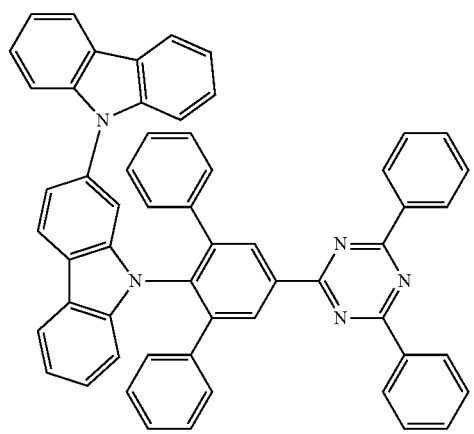

45
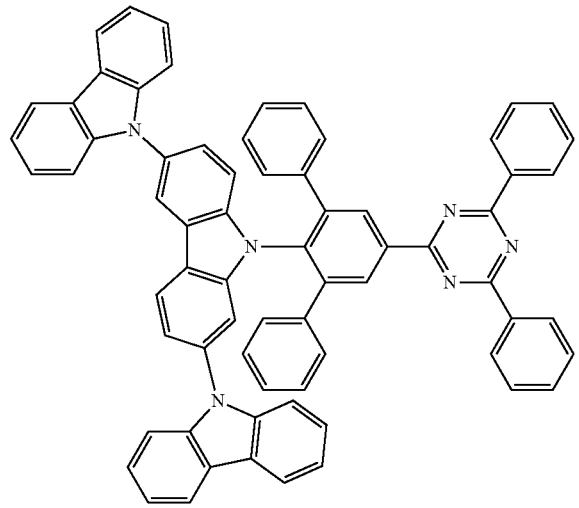
46
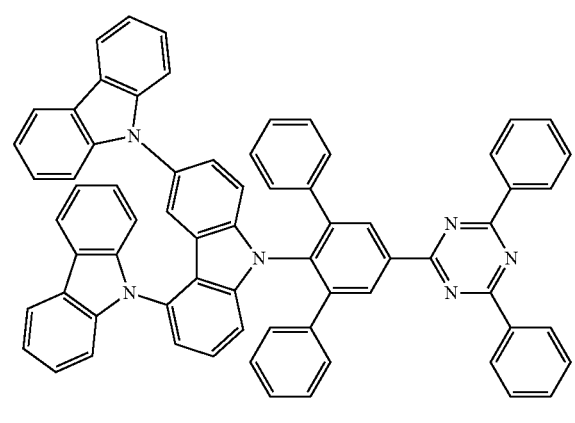
47
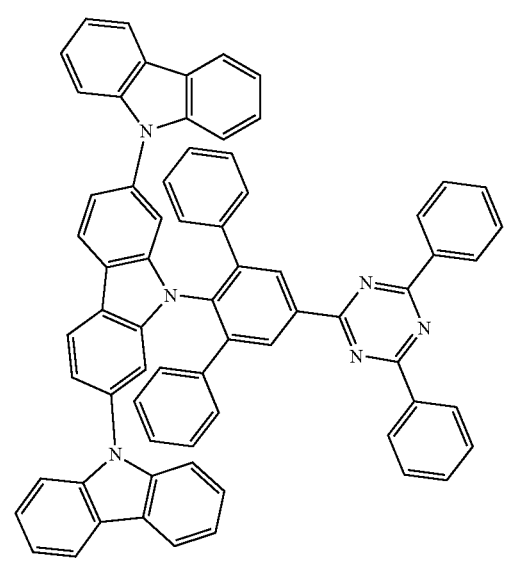
48
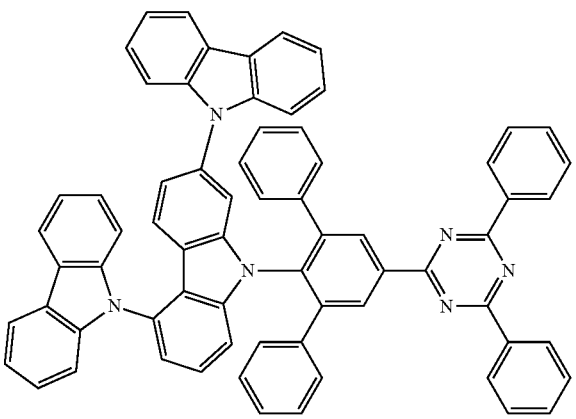
49
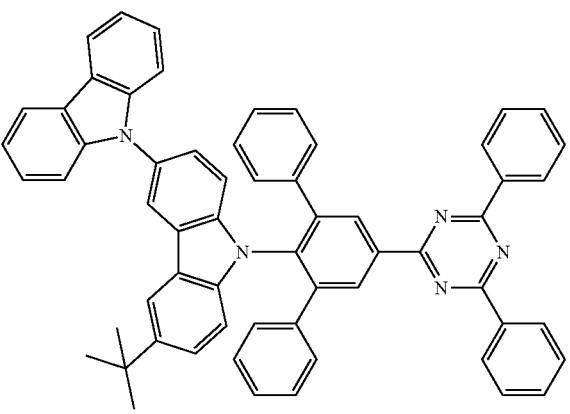
50
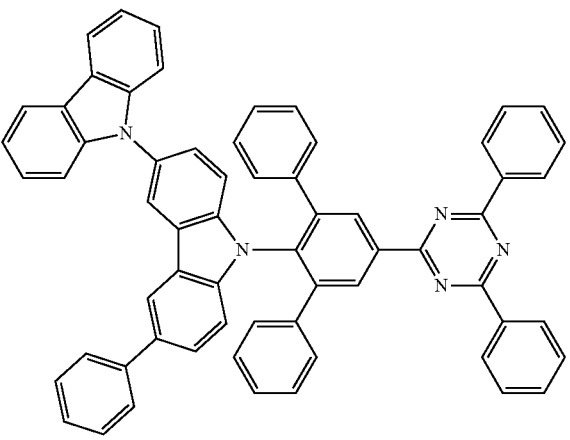

2897
-continued
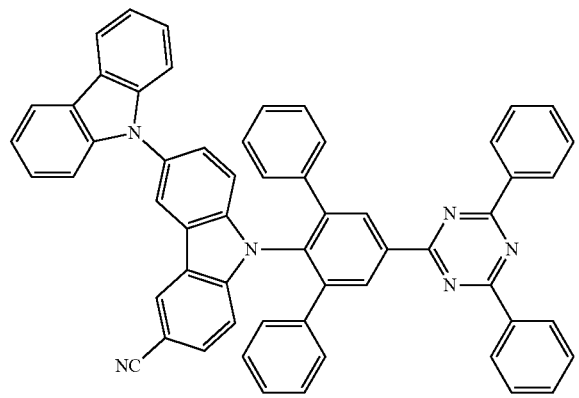
51
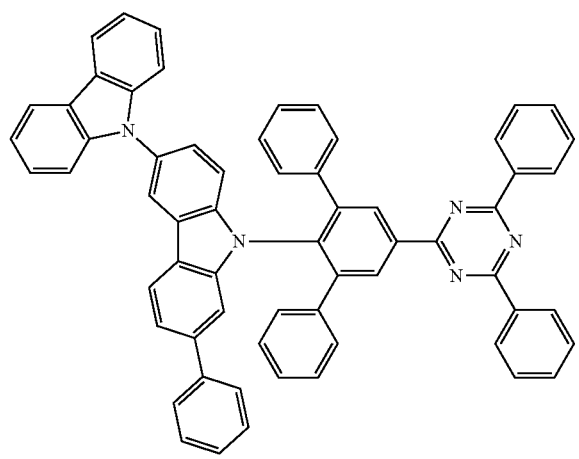
52
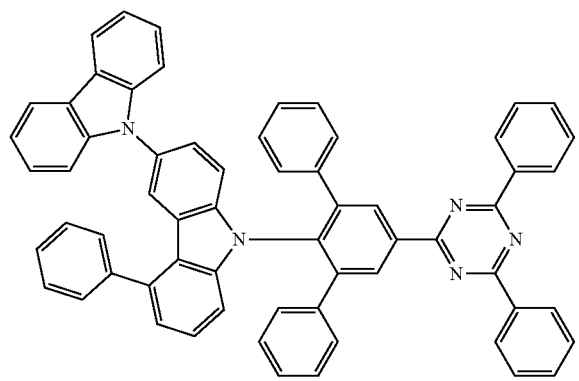
53
2898
-continued
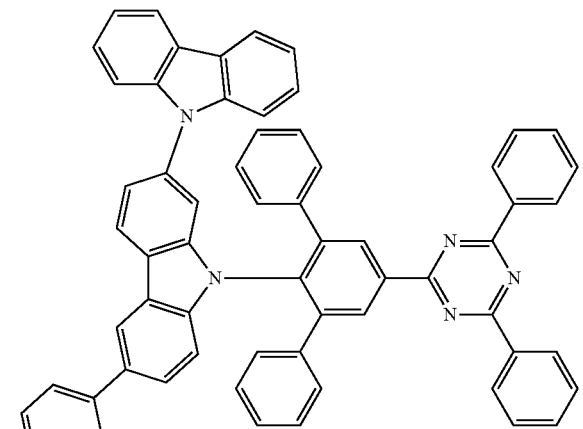
54
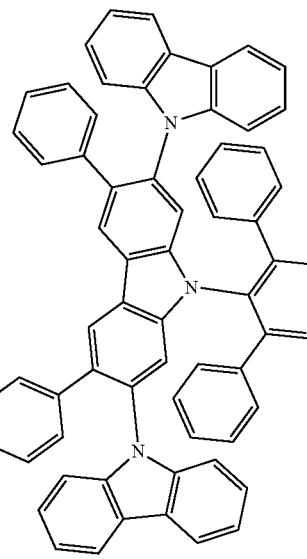
55
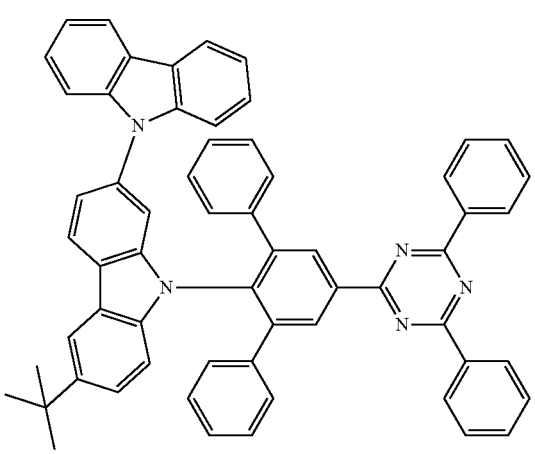
56

57
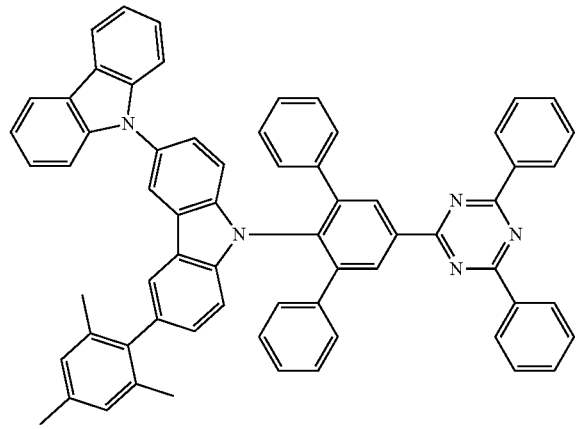
58
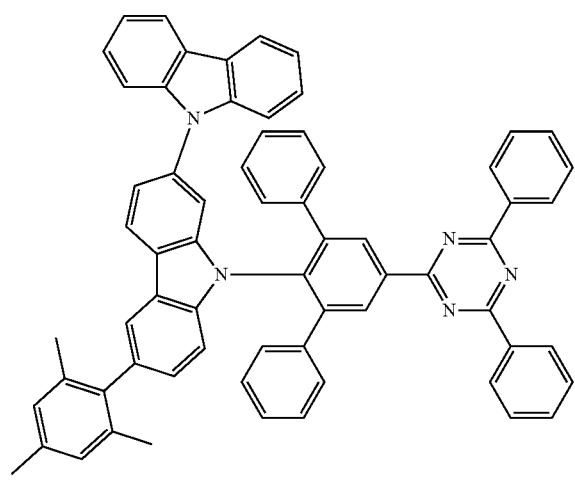
59
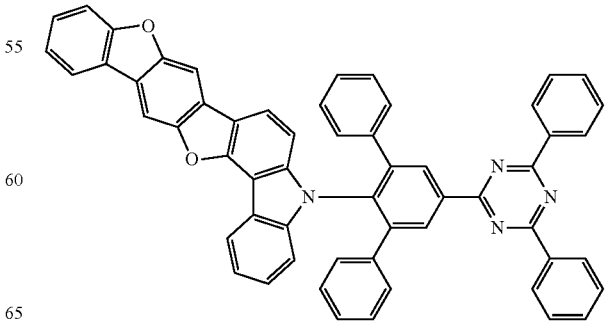
60
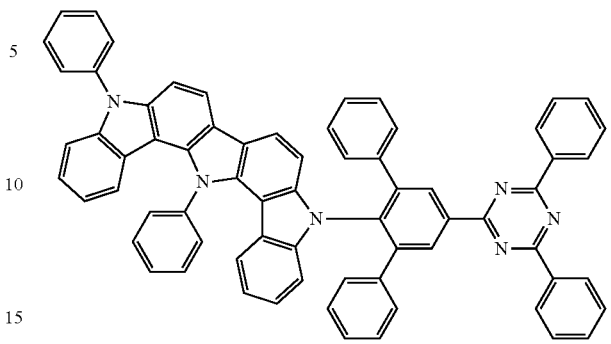
61
62
63

2901
-continued
64
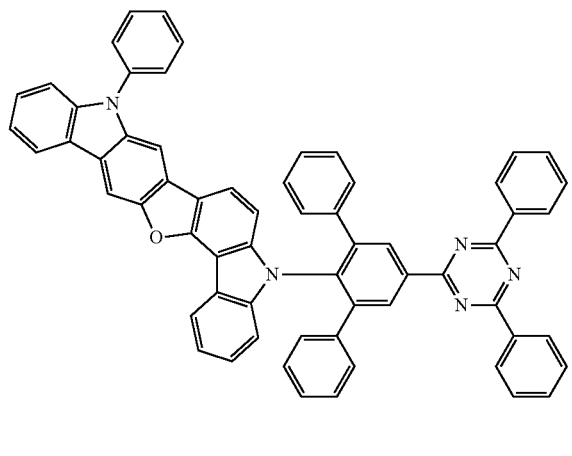
65
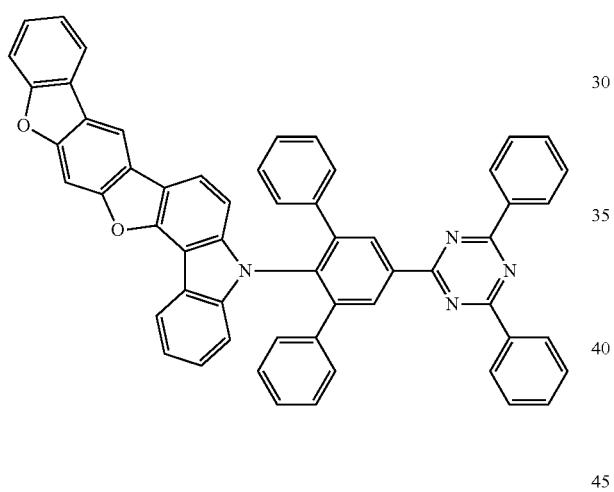
66
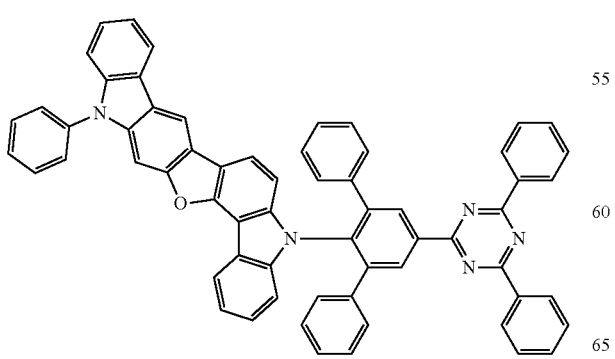
2902
-continued
67
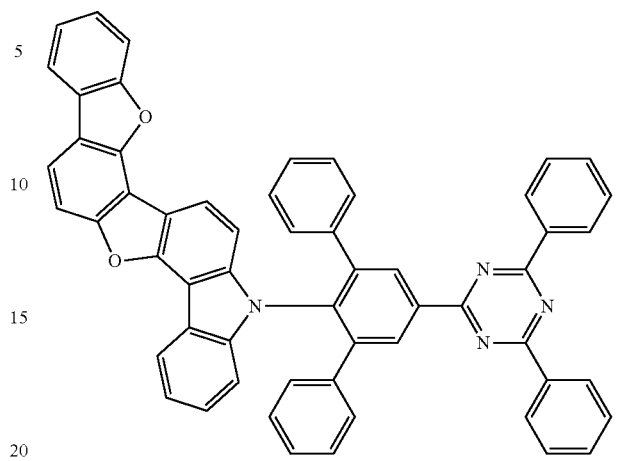
68
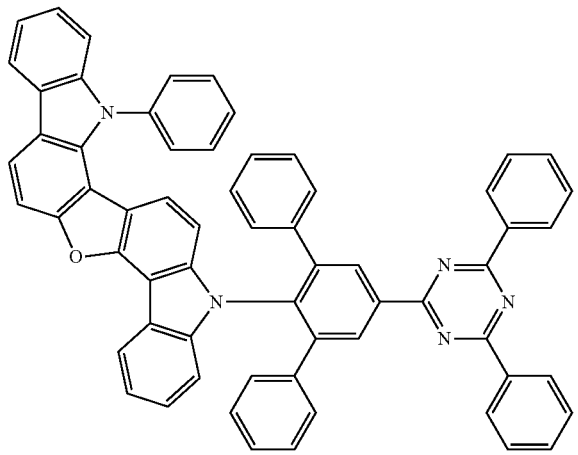
69
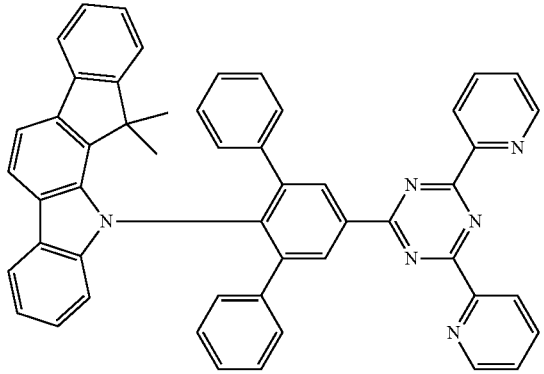

2903
-continued
70
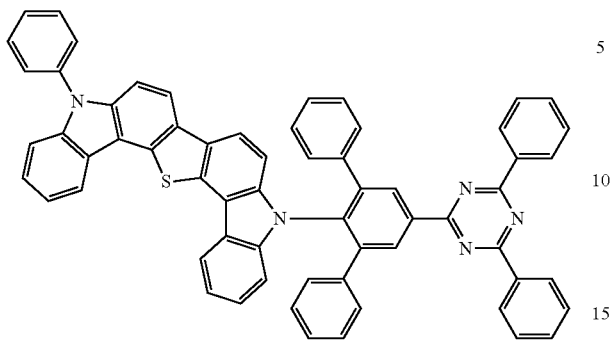
71
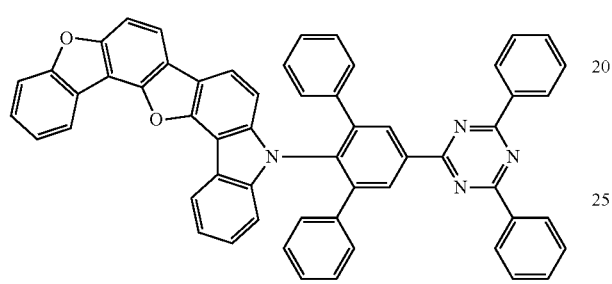
72
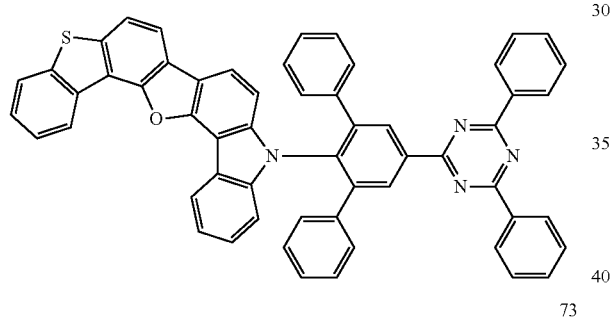
73
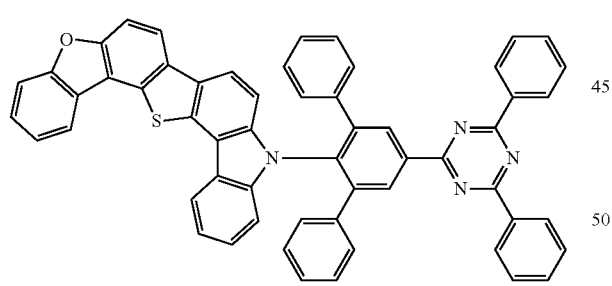
74
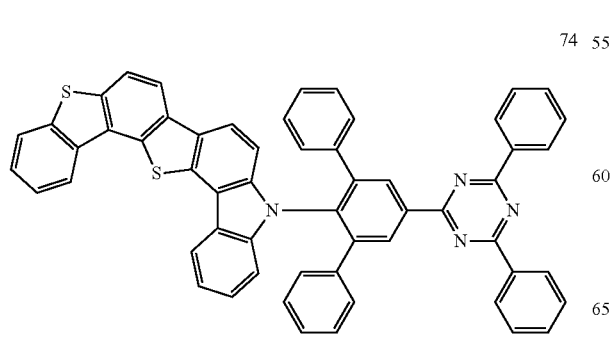
2904
-continued
75
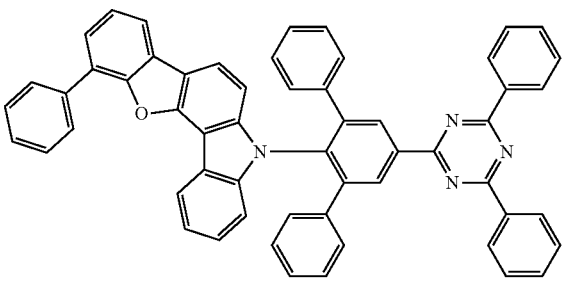
76
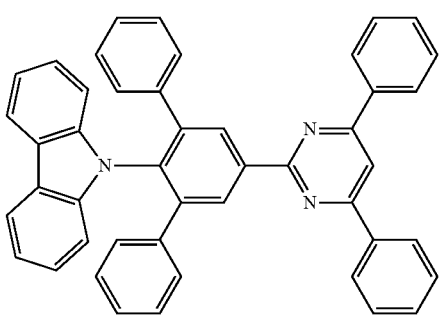
77
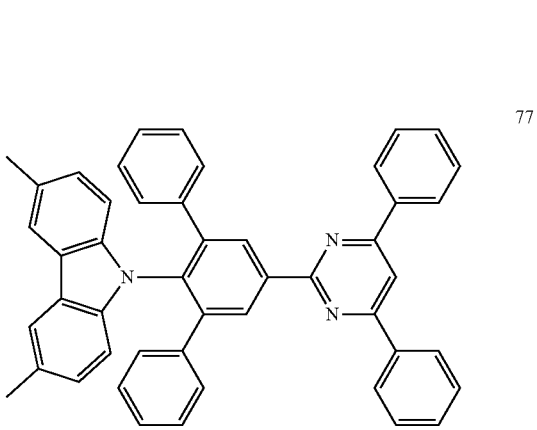
78
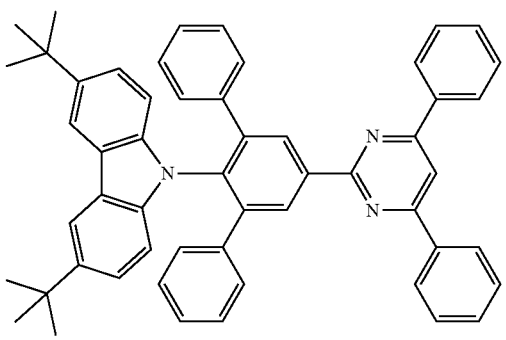

2905
-continued
79
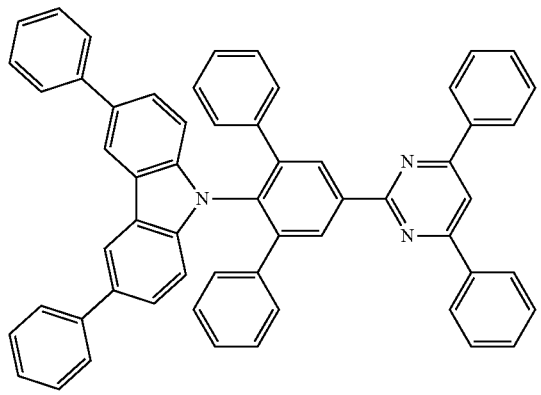
80
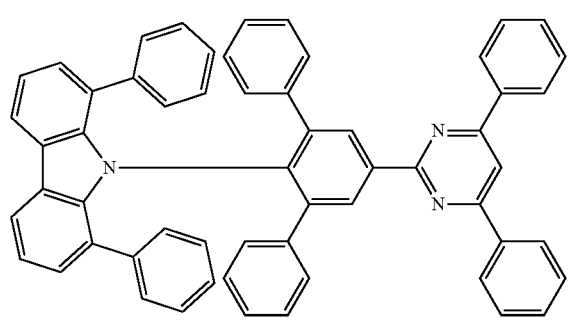
81
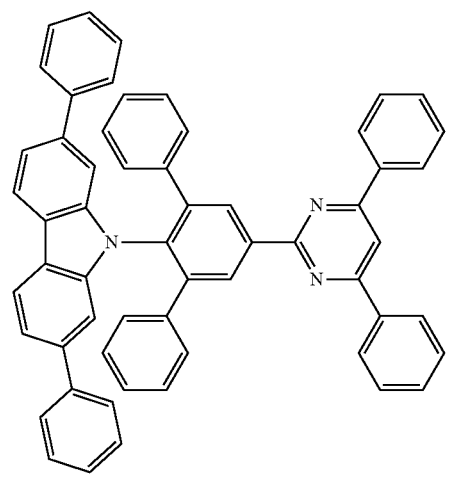
82
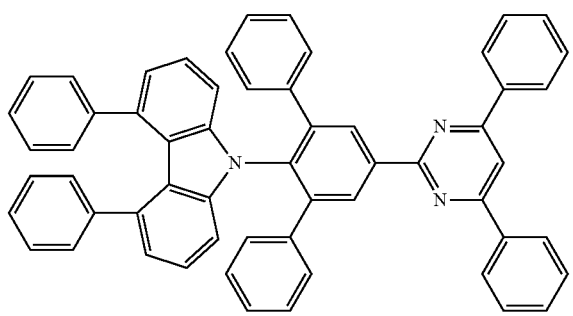
2906
-continued
83
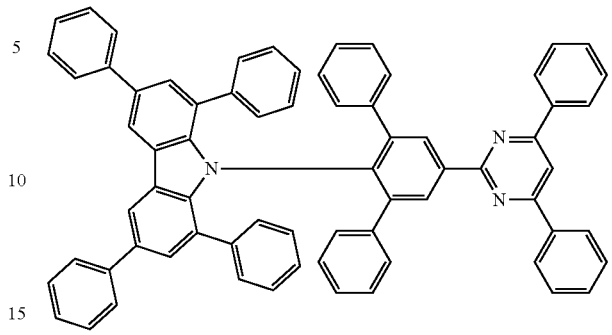
84
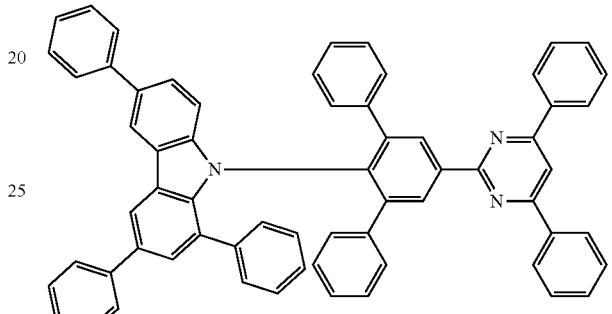
85
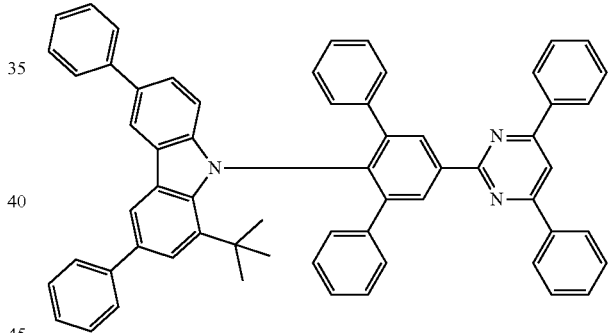
86
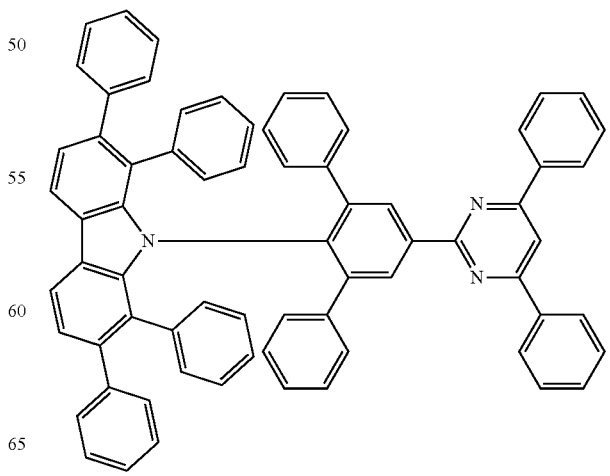

-continued
87
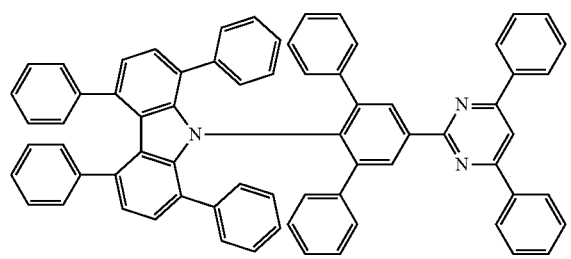
88
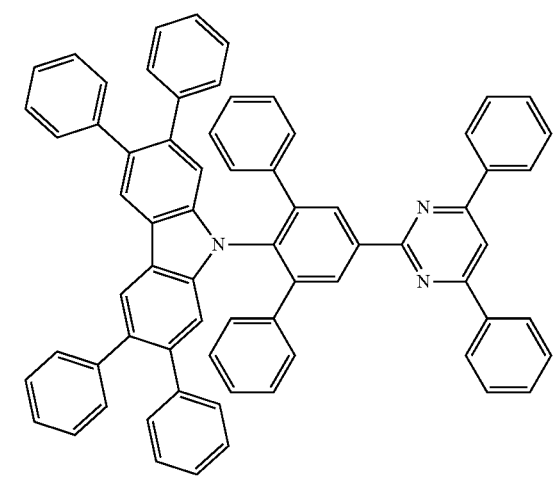
89
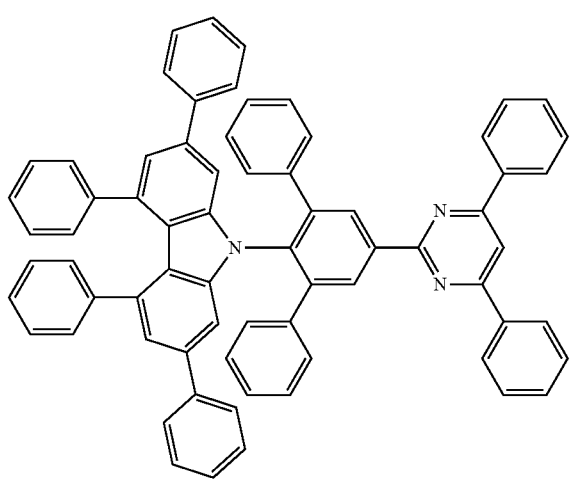
90
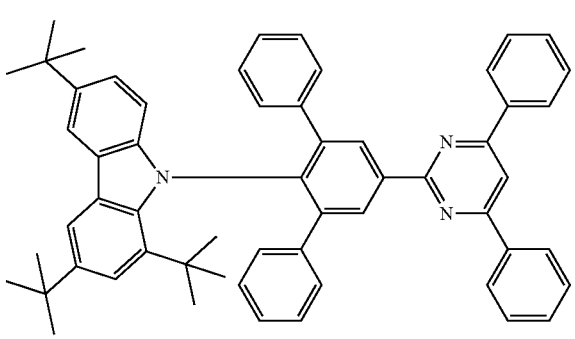
-continued
91
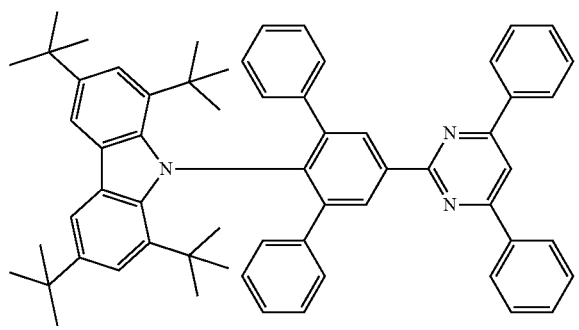
92
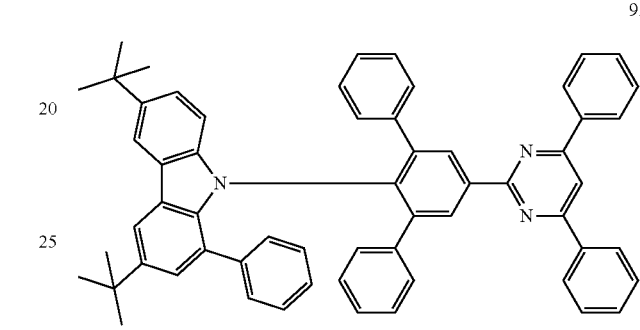
93
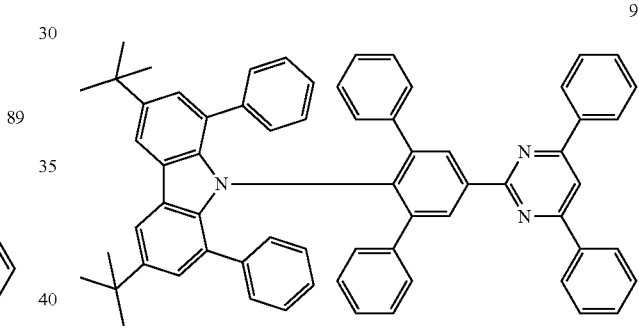
94
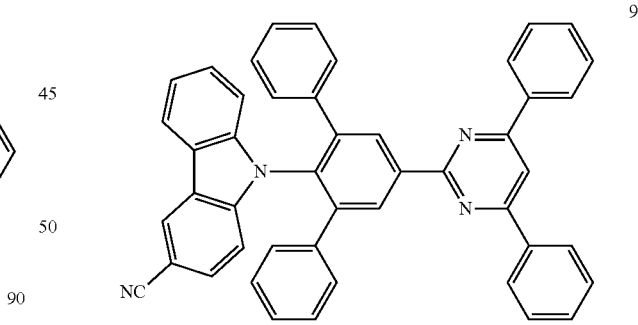
95
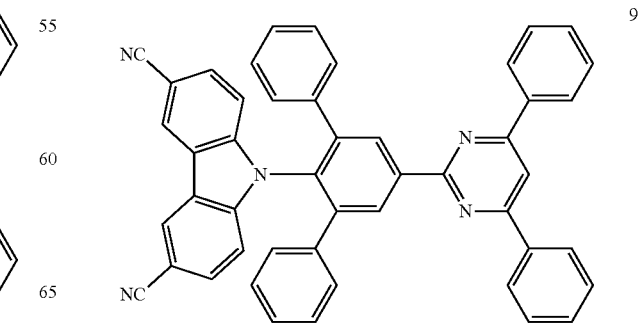

2909
-continued
96
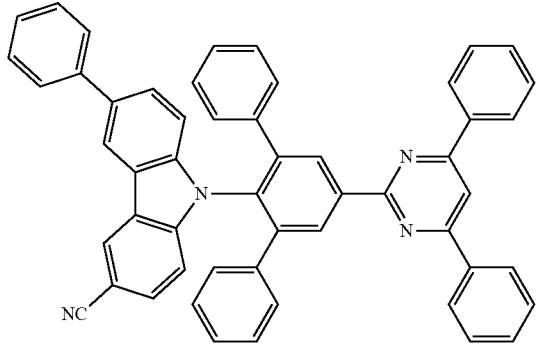
97
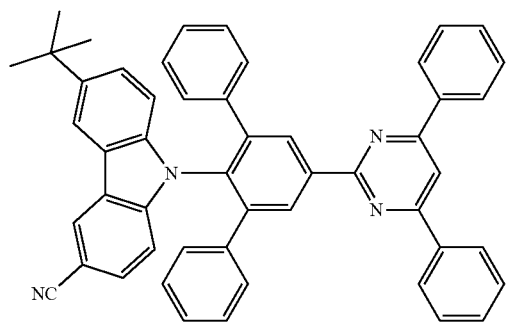
98
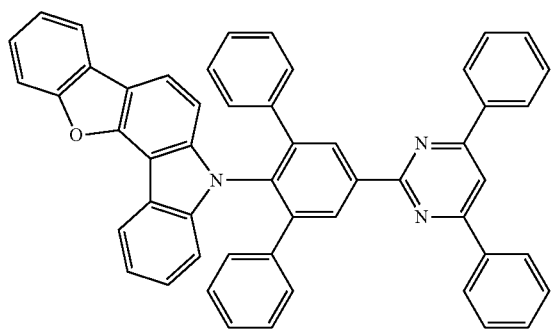
99
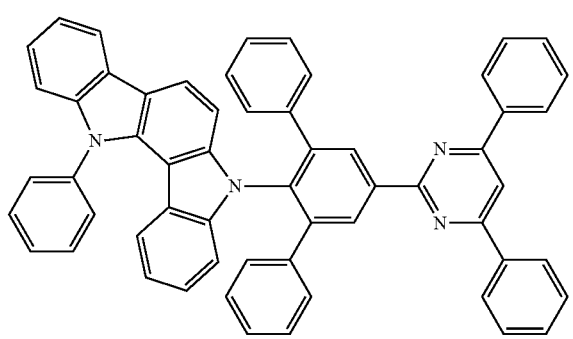
2910
-continued
100
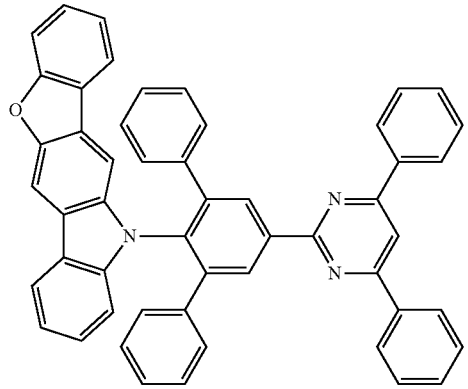
101
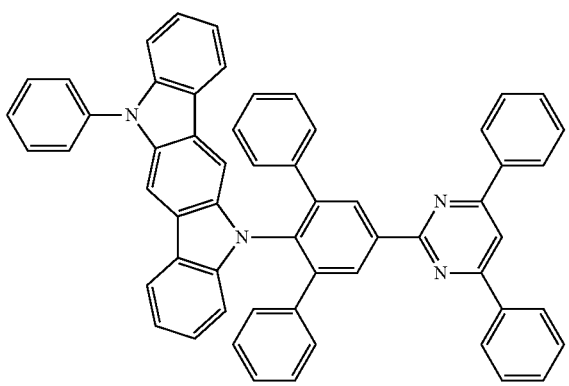
102
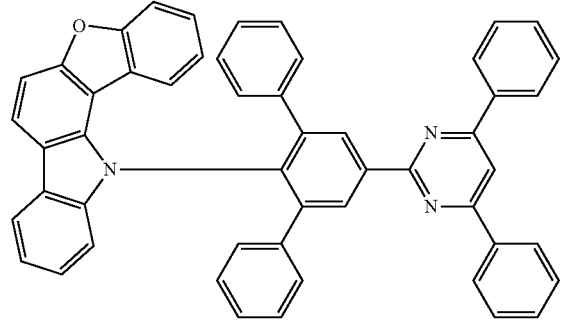
103
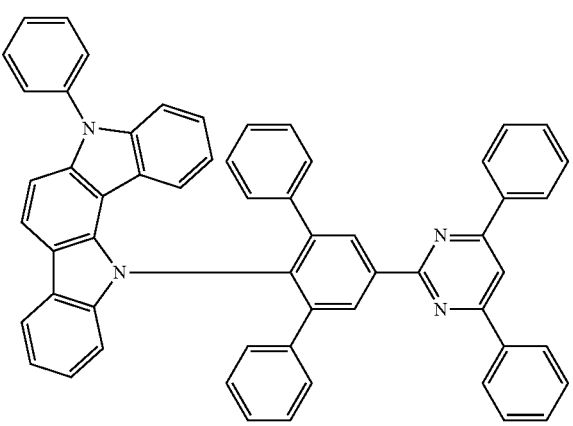

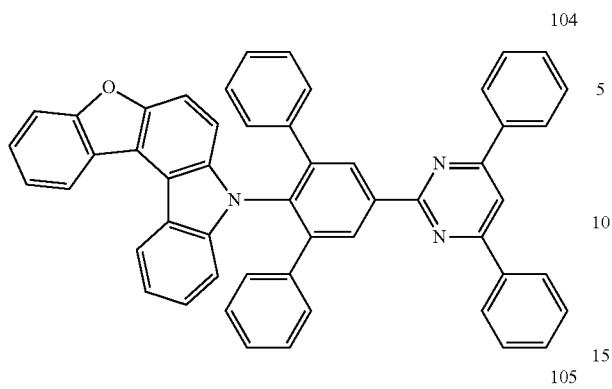
104
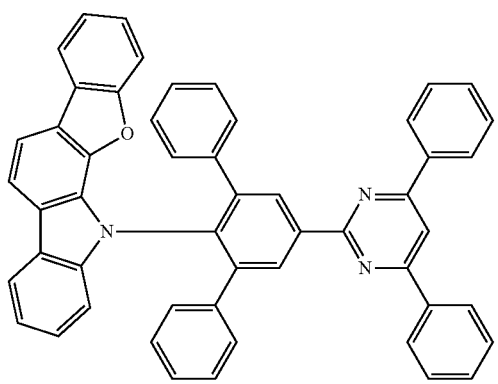
108
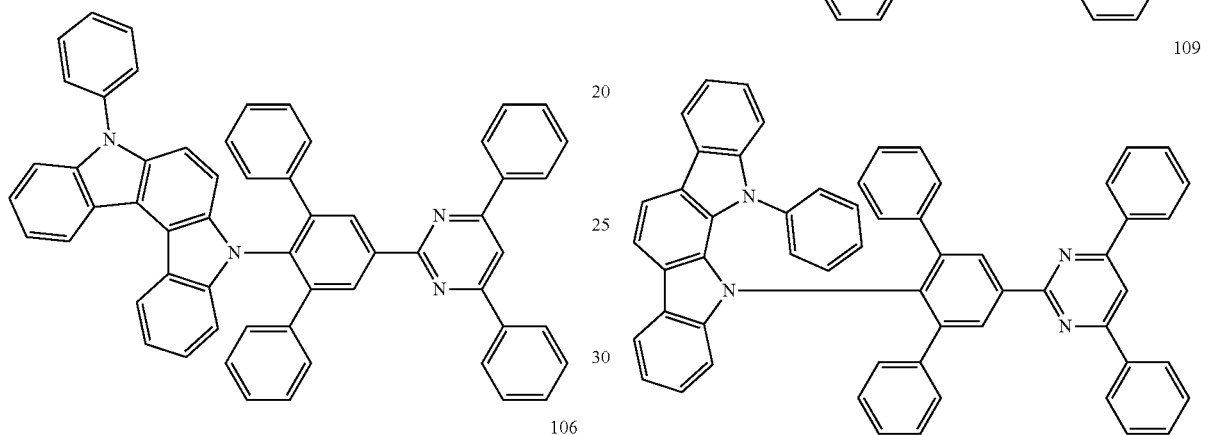
105
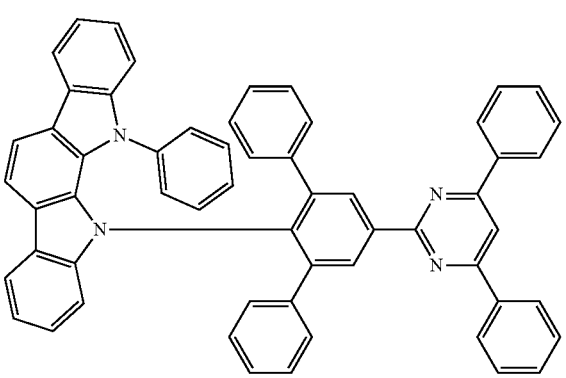
109
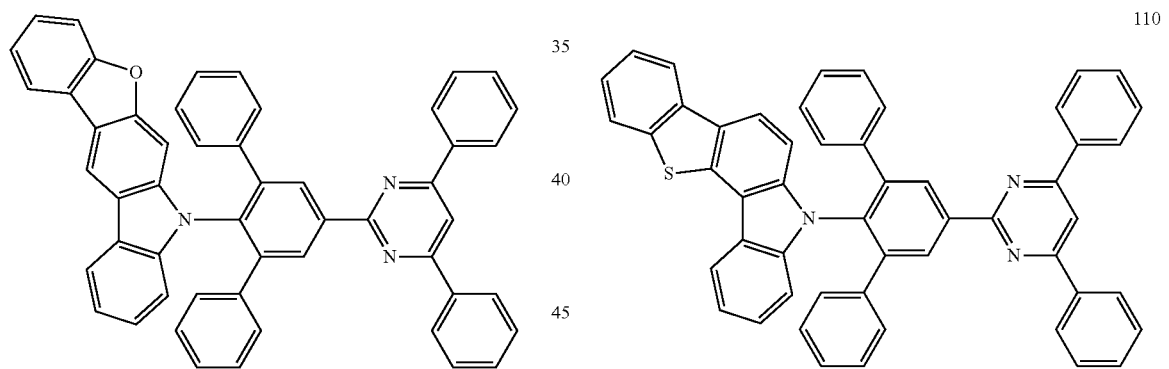
106
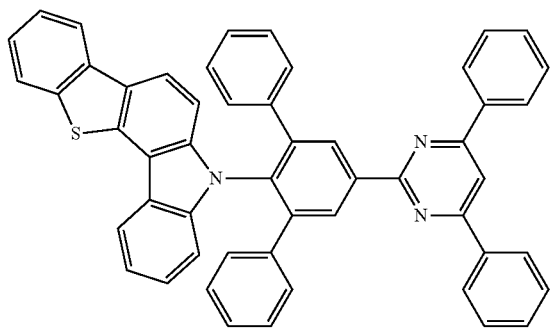
110
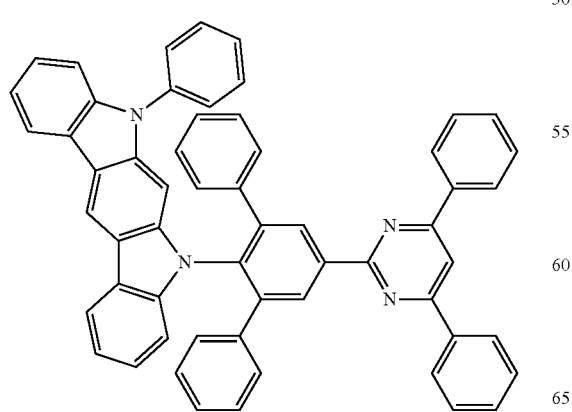
107
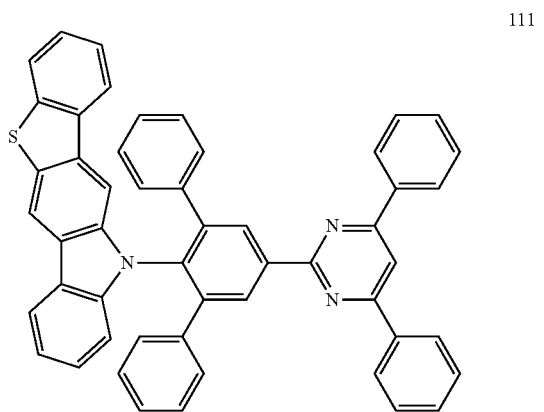
111

2913
-continued
112
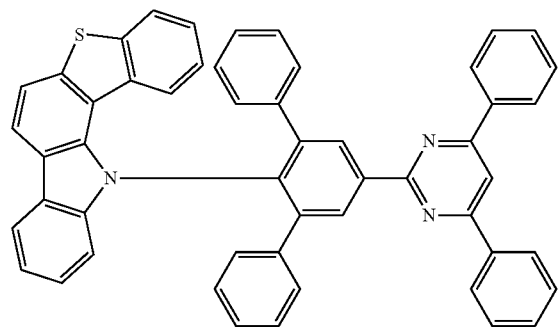
113
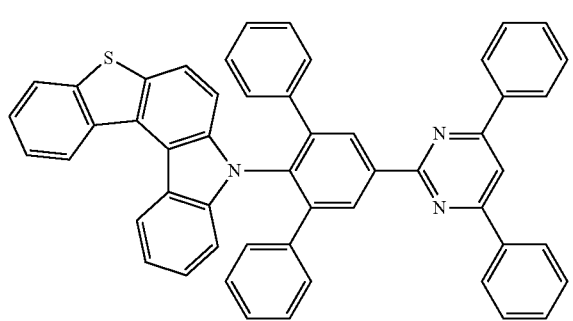
114
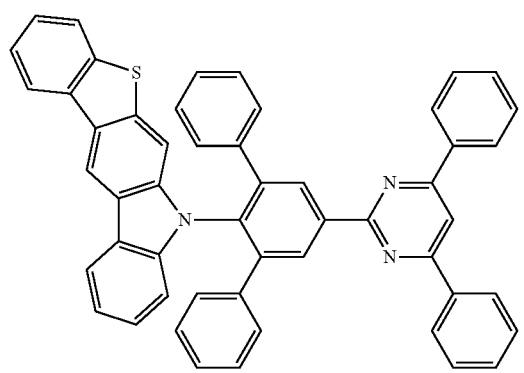
115
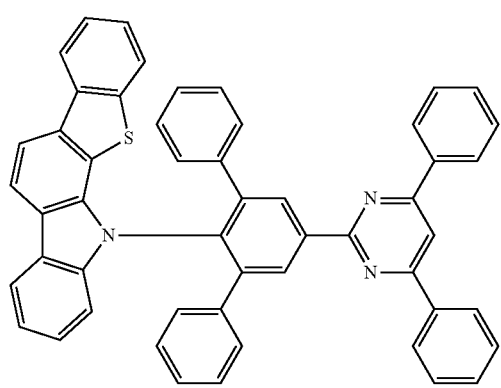
2914
-continued
116
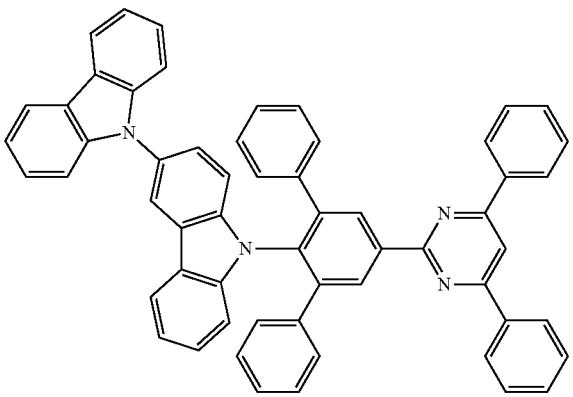
117
118
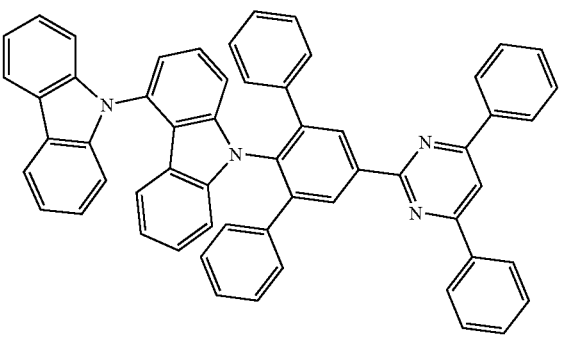

2915
-continued
119
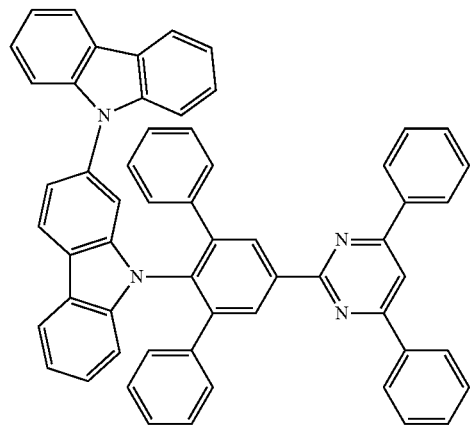
120
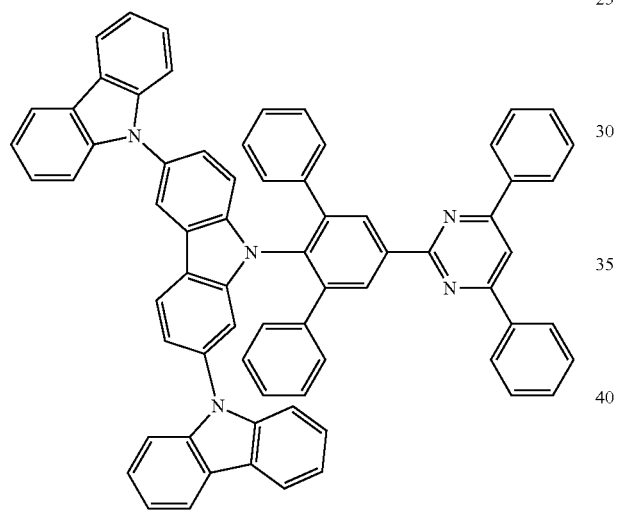
121
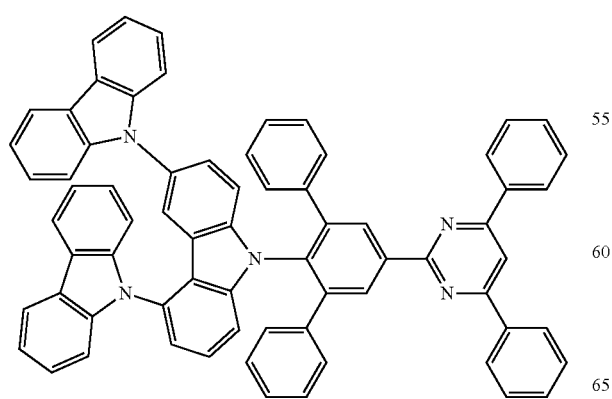
2916
-continued
122
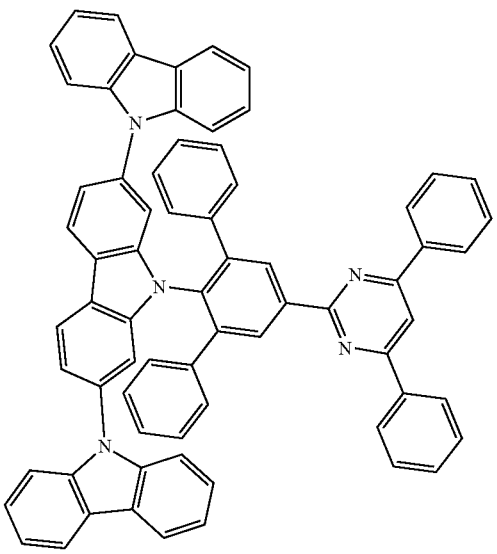
123
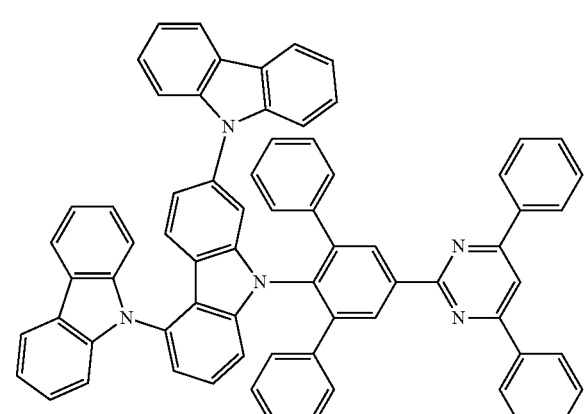
124
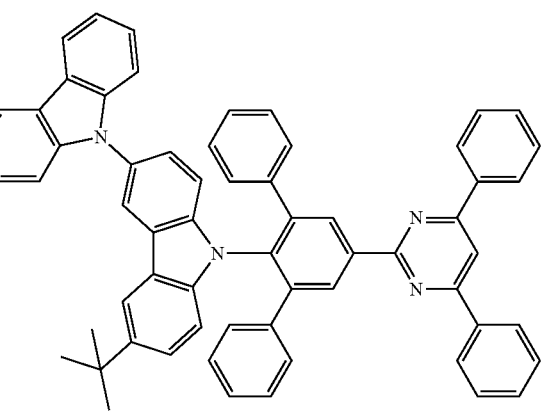

2917
-continued
125
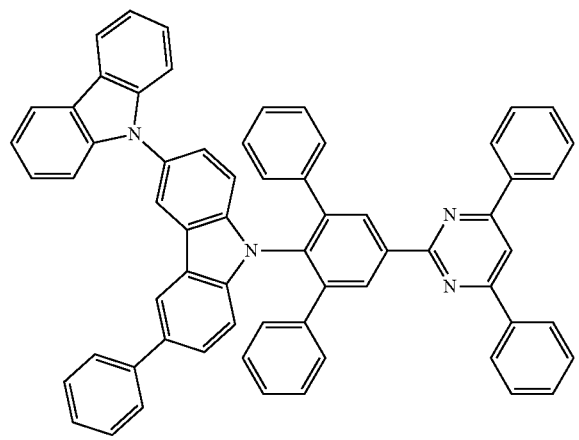
126
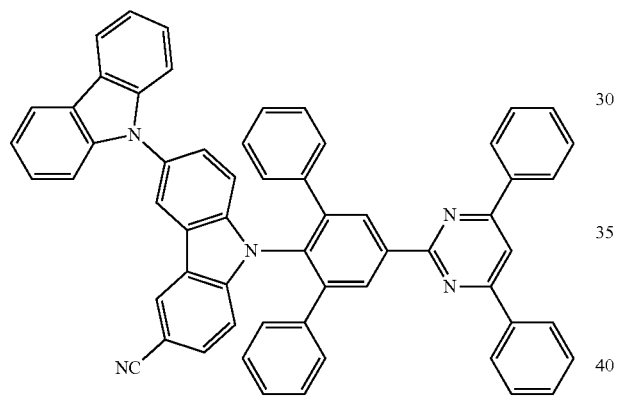
127
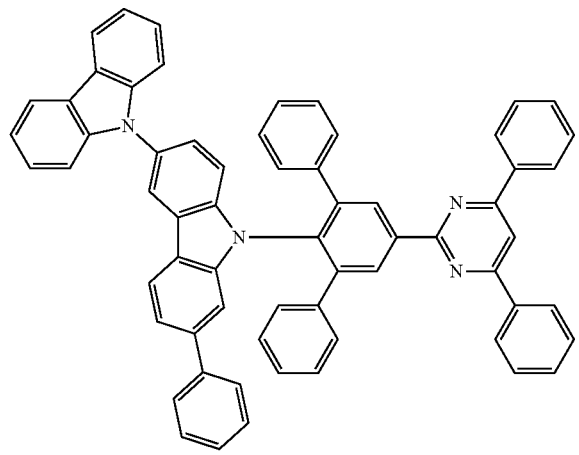
2918
-continued
128
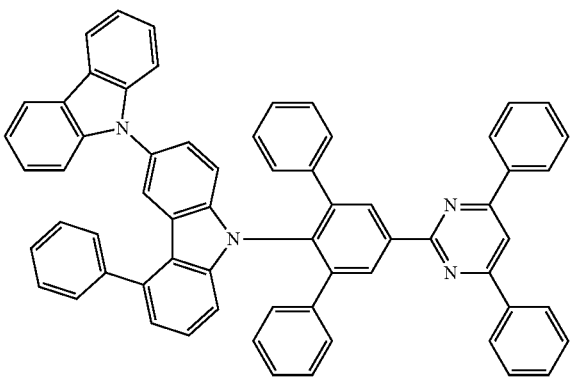
129
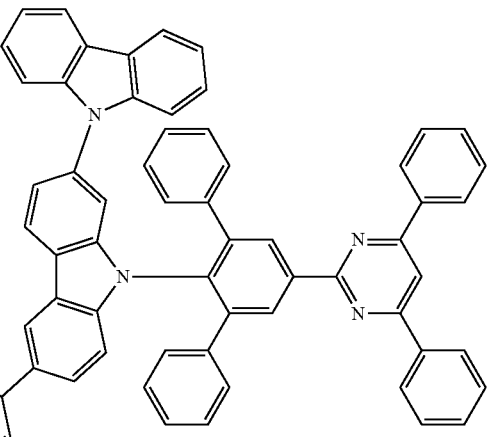
130
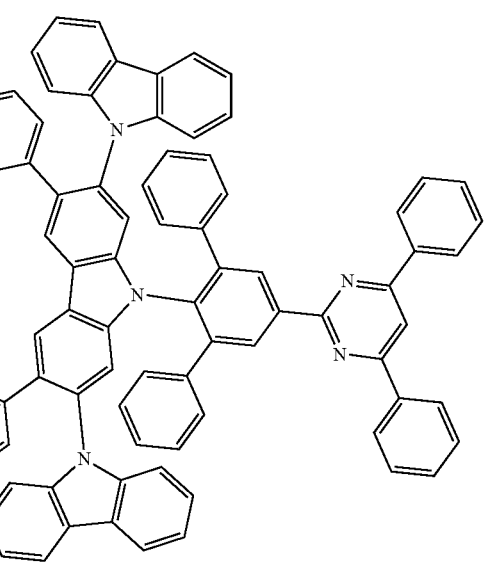

2919 -continued
131
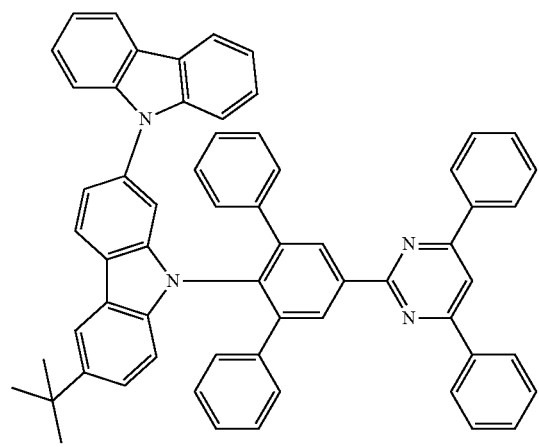
132
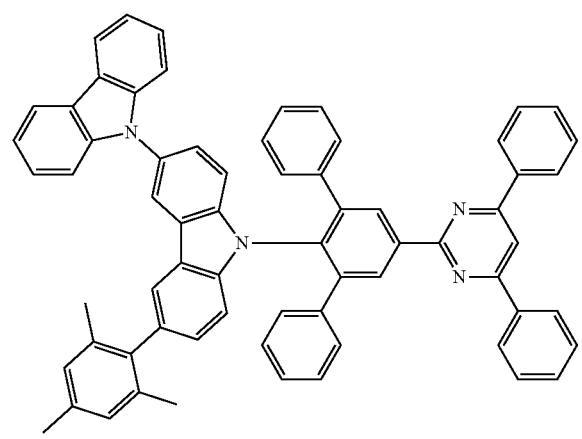
133
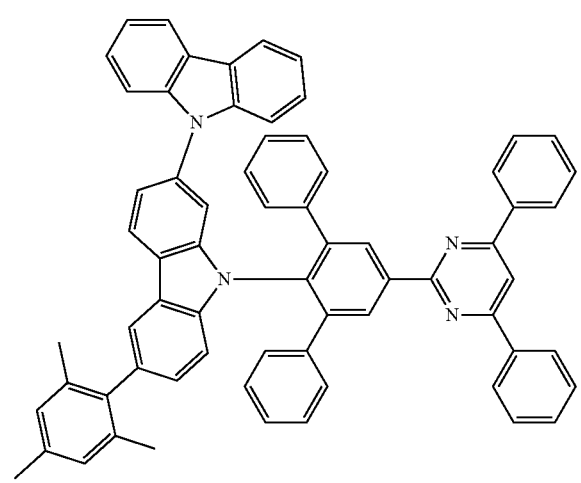
2920 -continued
134
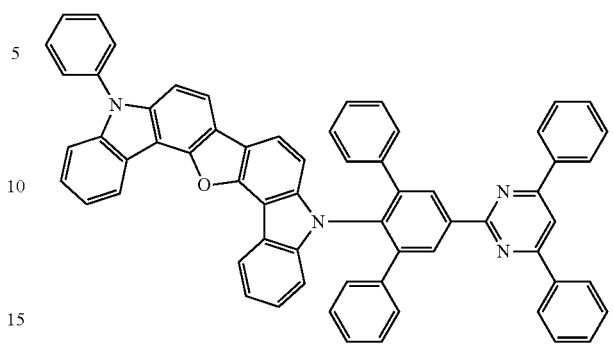
135
136
137
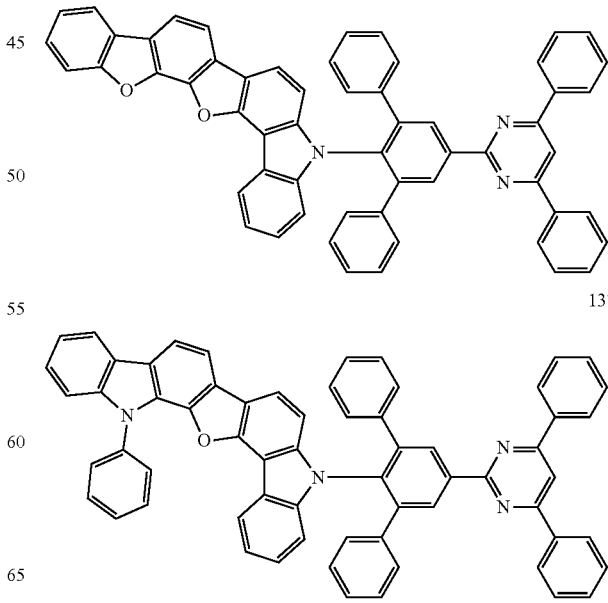

138
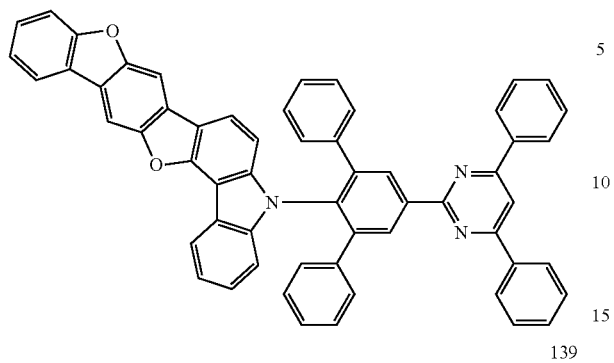
139
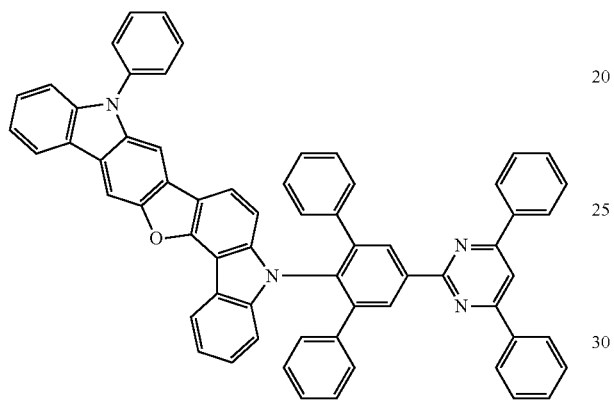
140
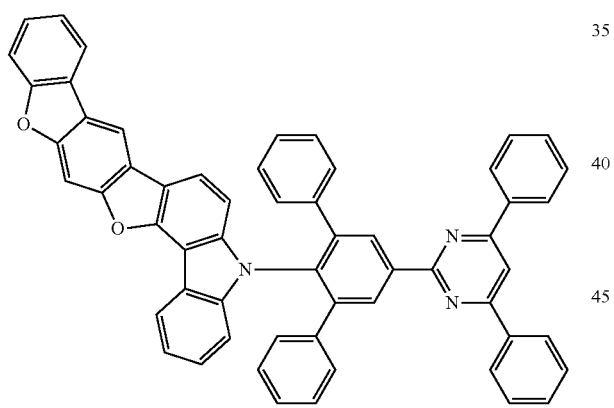
141
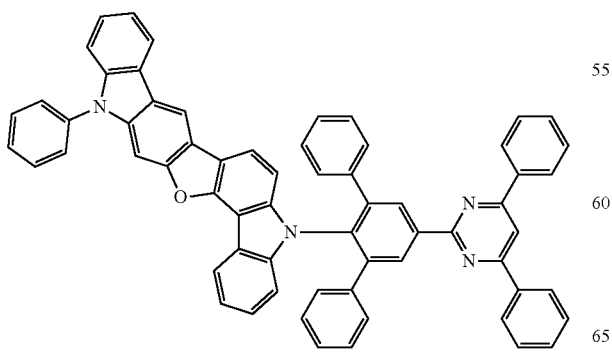
142
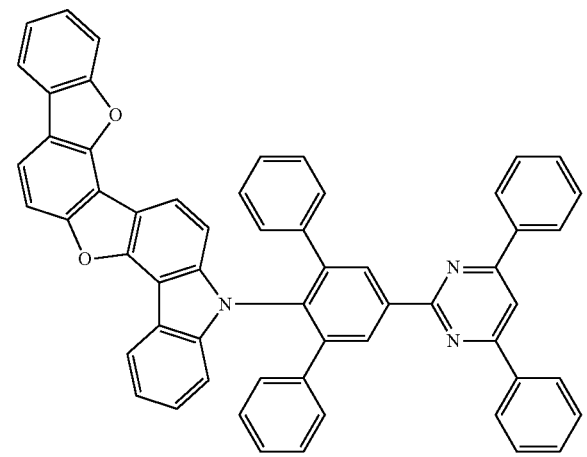
143
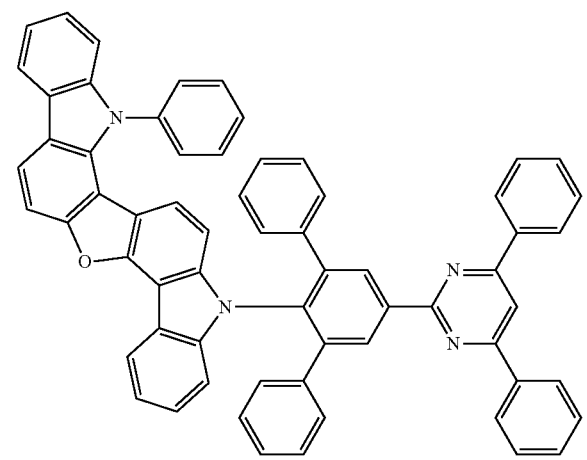
144
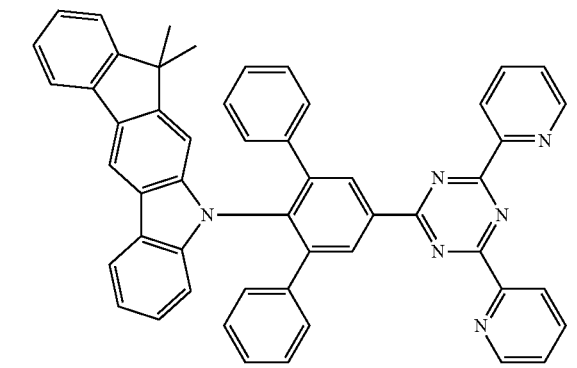

2923
-continued
145
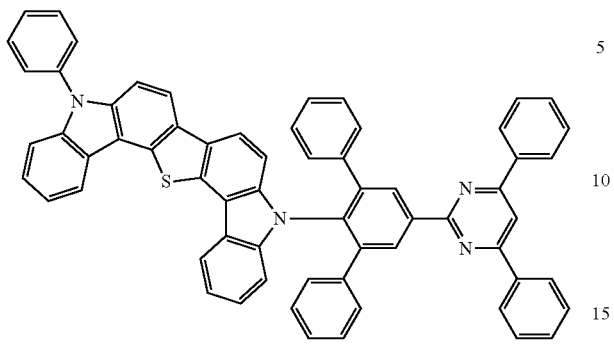
146
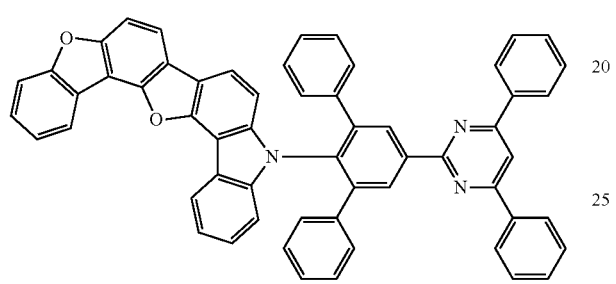
147

148

149
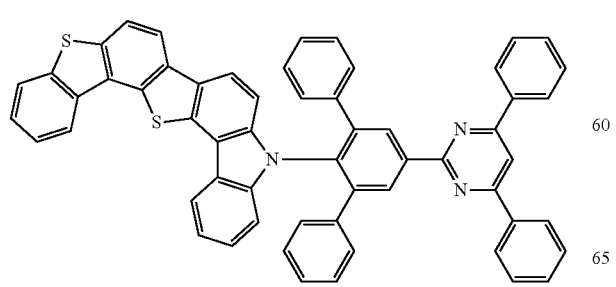
2924
-continued
150
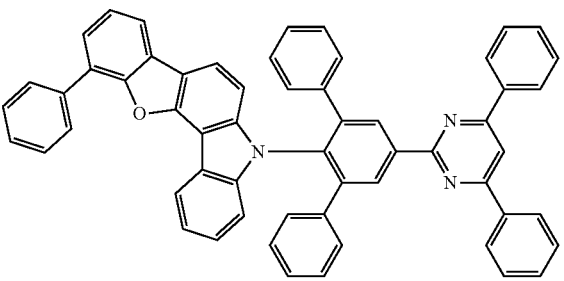
151
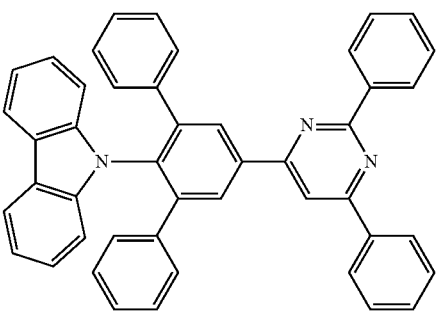
152
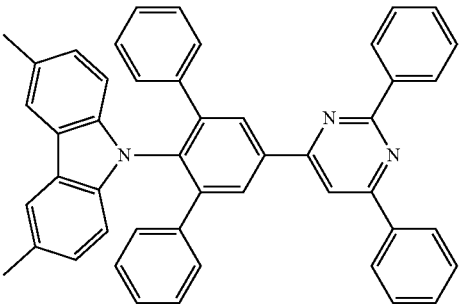
153
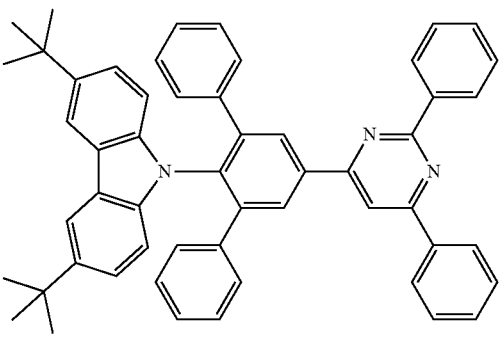

2925
-continued
154
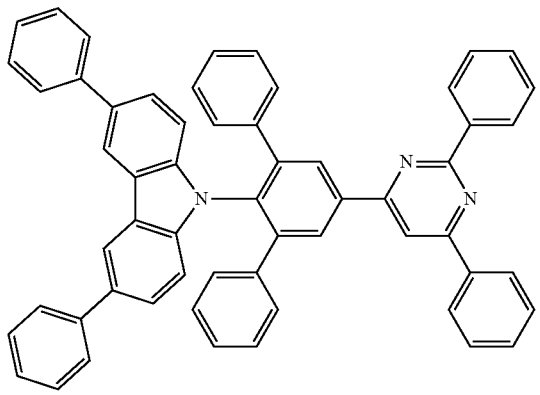
155
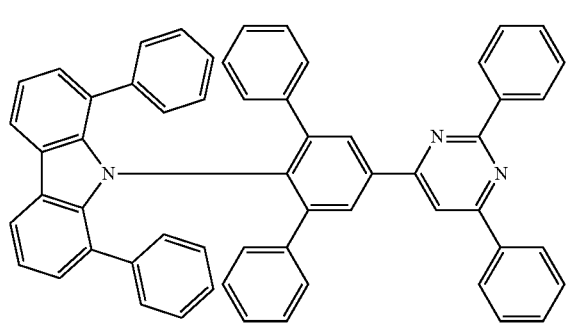
156
157
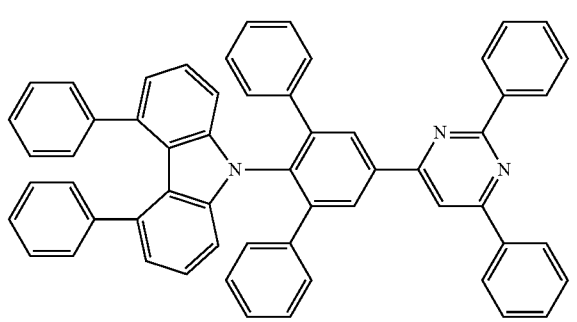
2926
-continued
158
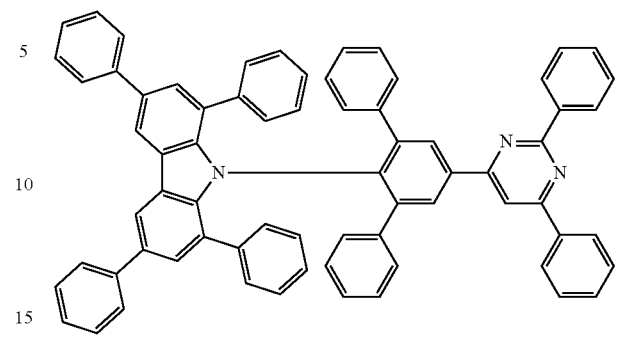
159
160
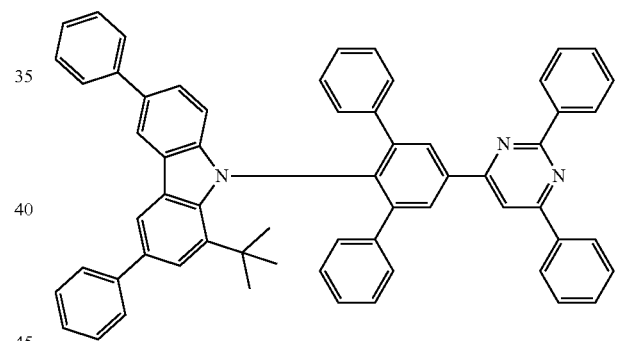
161

2927
-continued
162
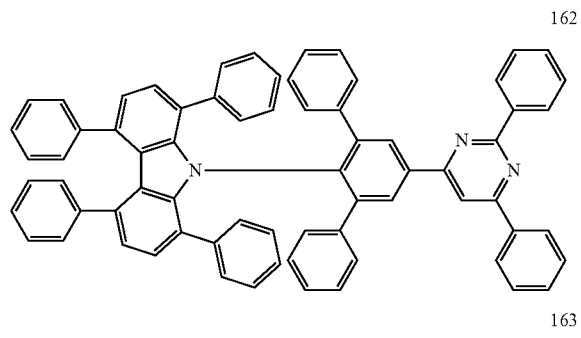
163
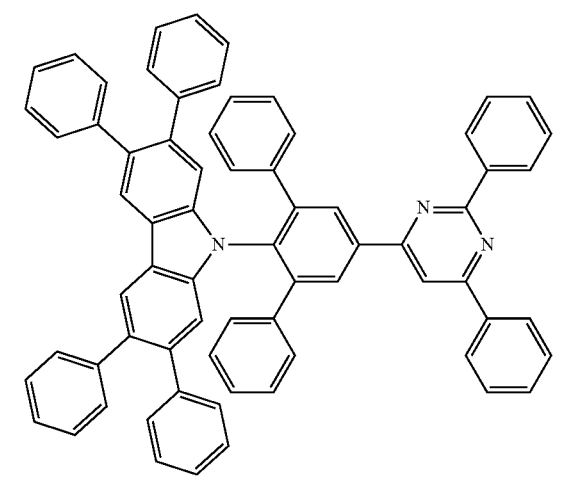
164
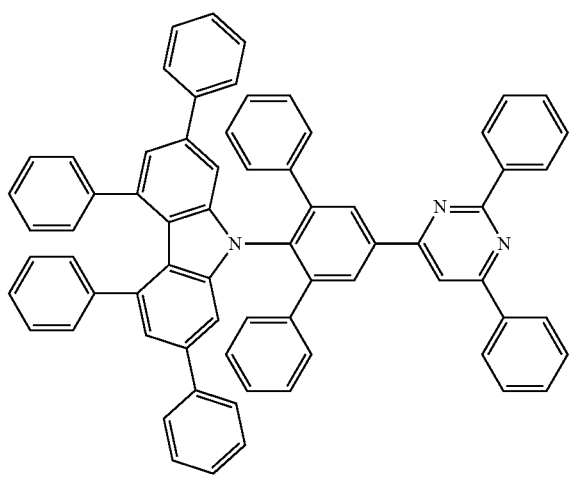
165
2928
-continued
166
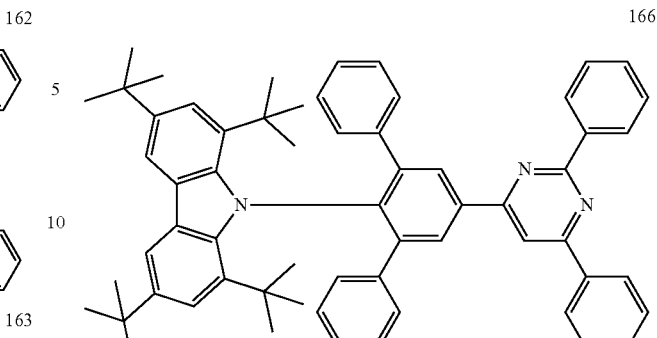
167
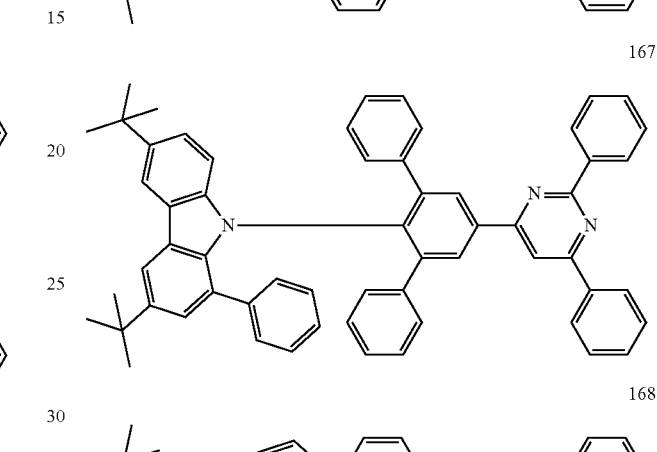
168
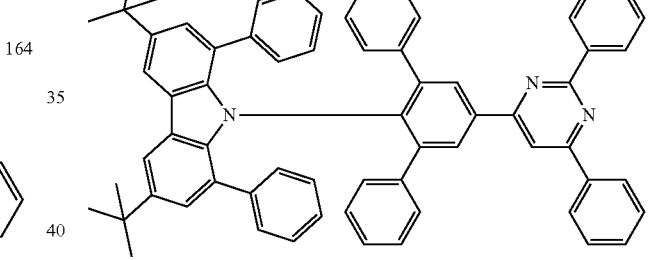
169
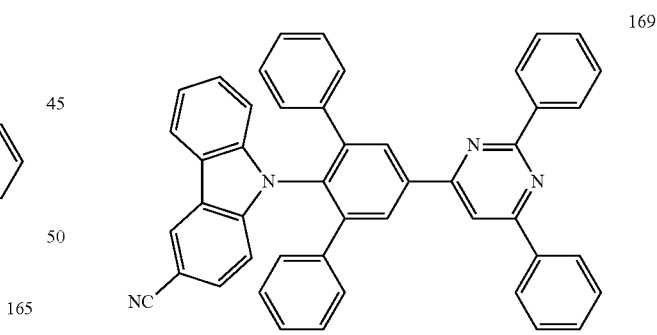
170
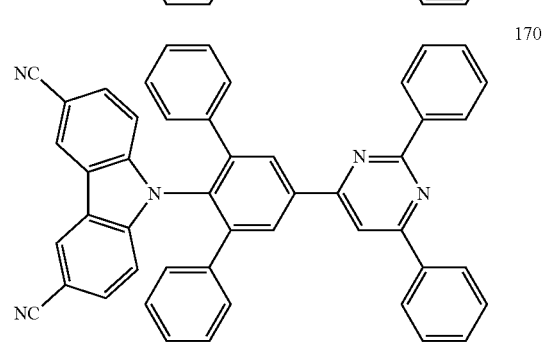

2929
-continued
171
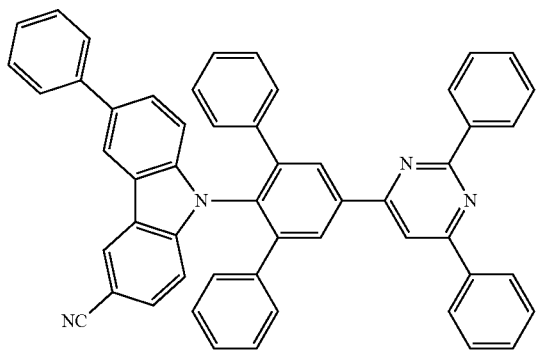
172
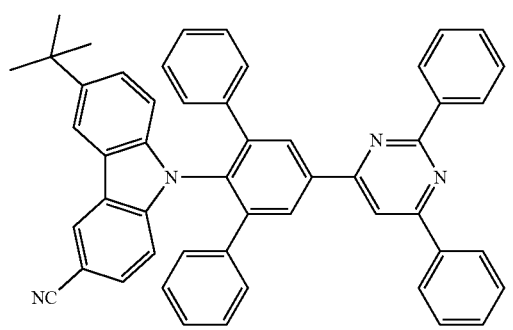
173
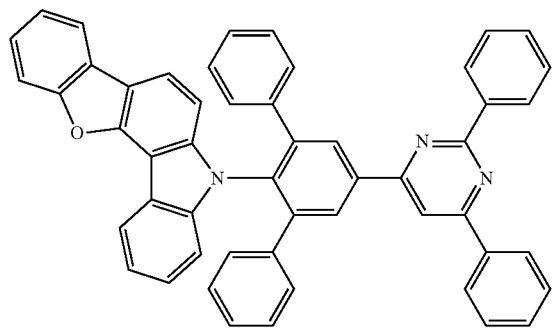
174
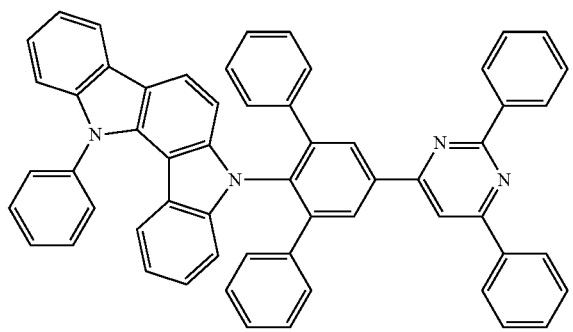
2930
-continued
175
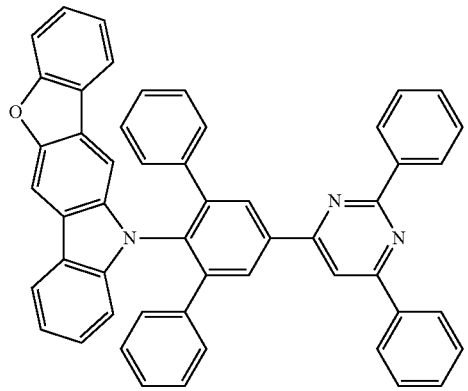
176
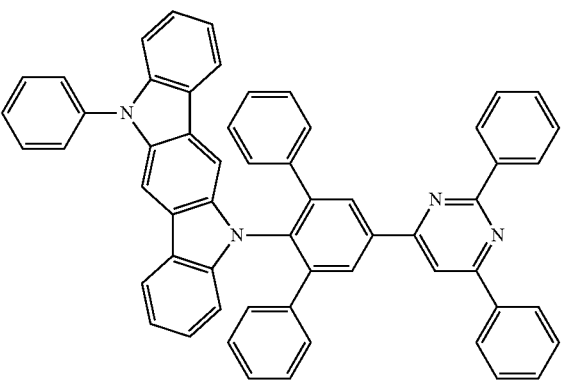
177
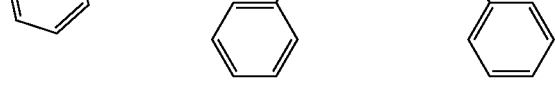
178
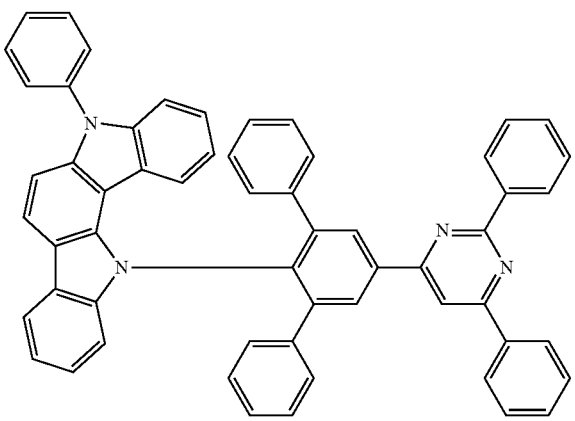

2931
-continued
2932
-continued
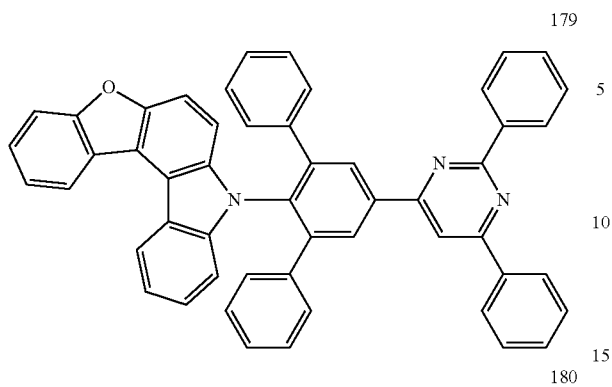
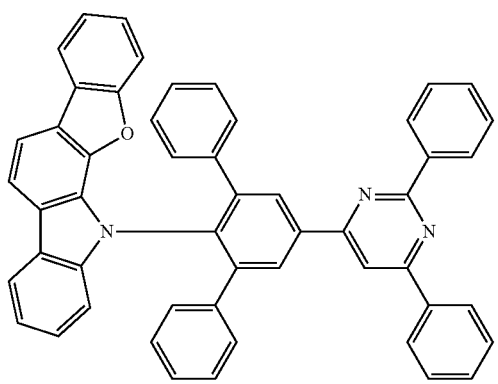

2933
-continued
187
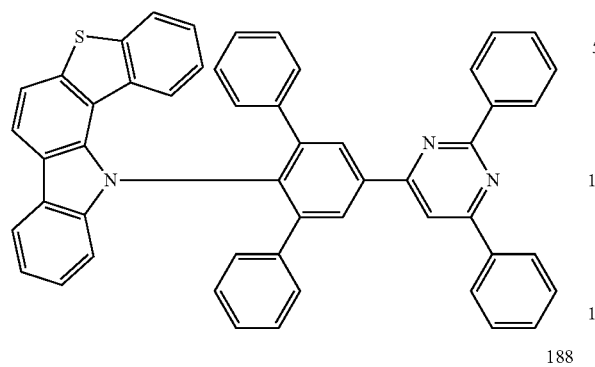
188
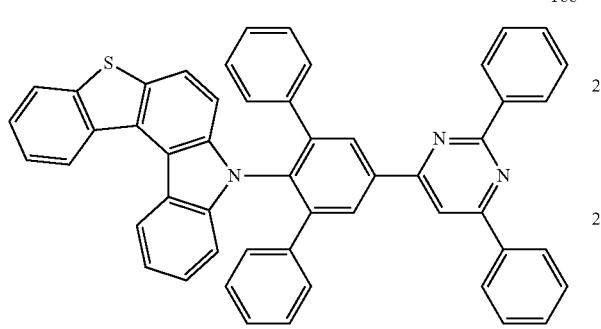
189
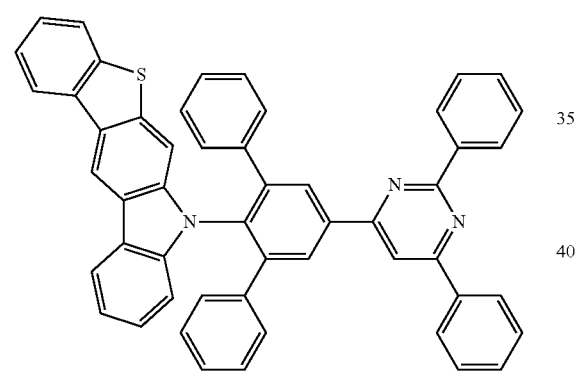
190
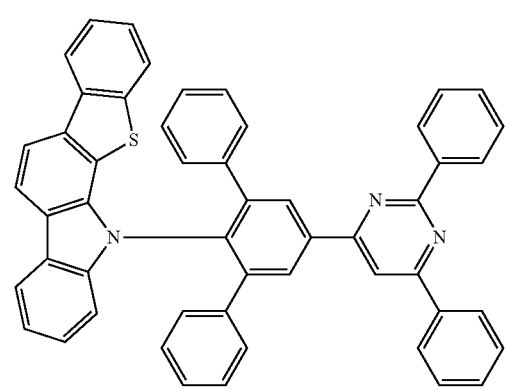
2934
-continued
191
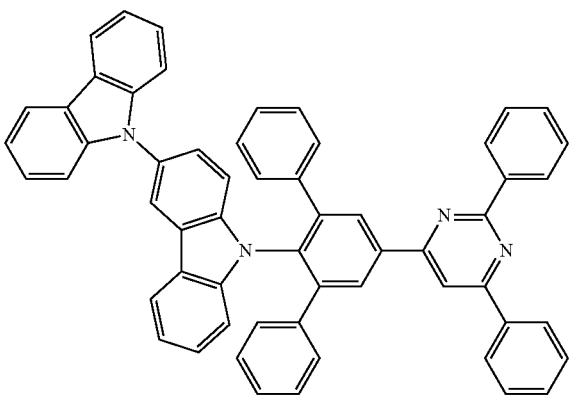
192
193

2935
-continued
194
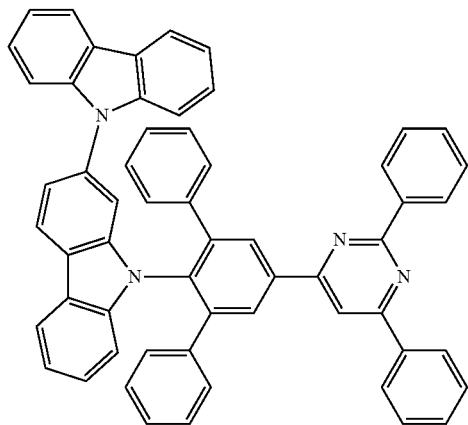
195
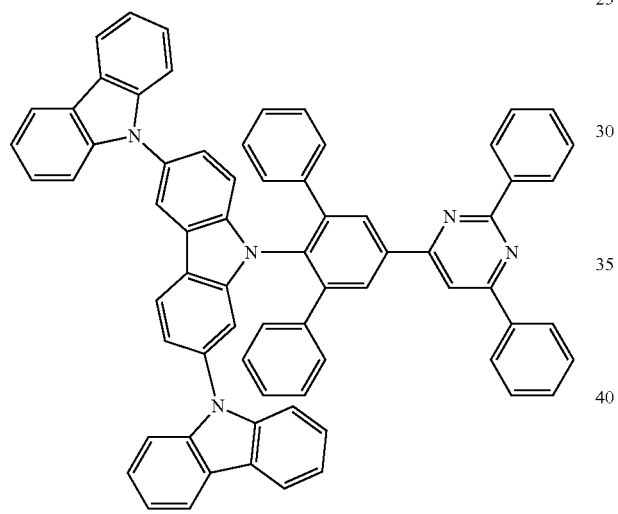
196
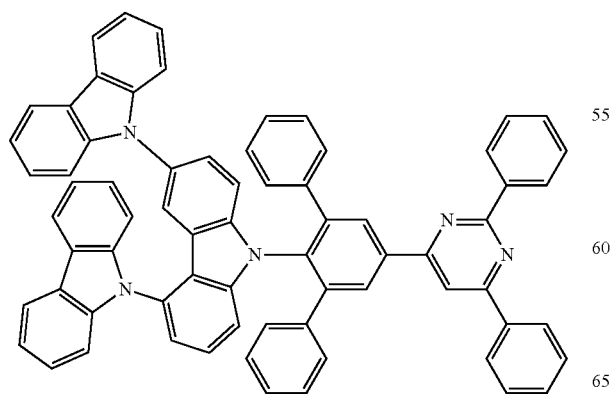
2936
-continued
197
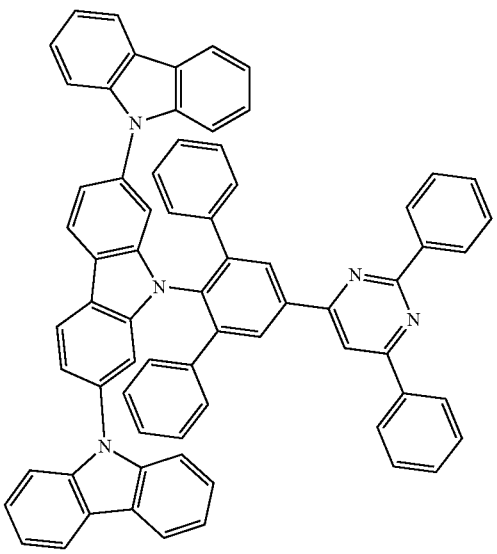
198
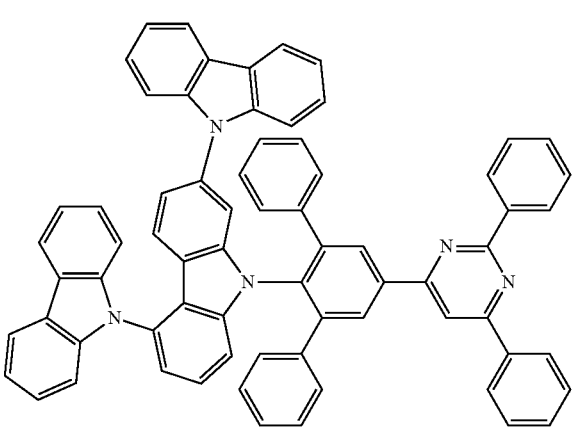
199
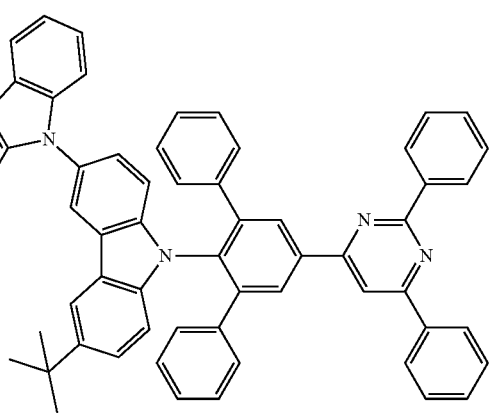

2937
-continued
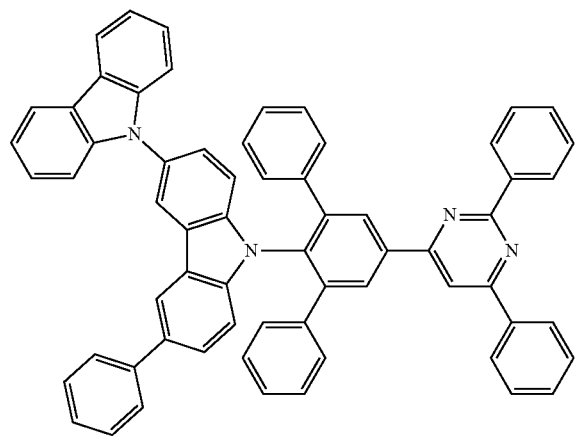
200
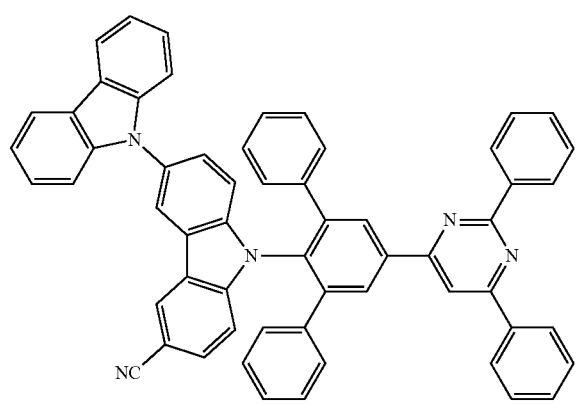
201
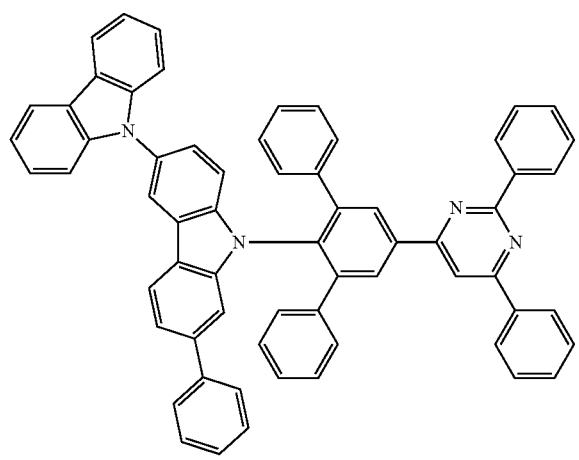
202
2938
-continued
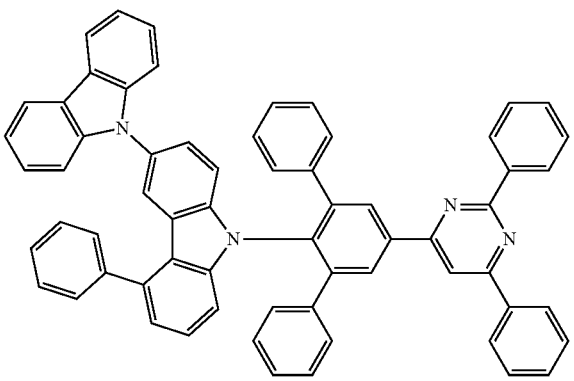
203
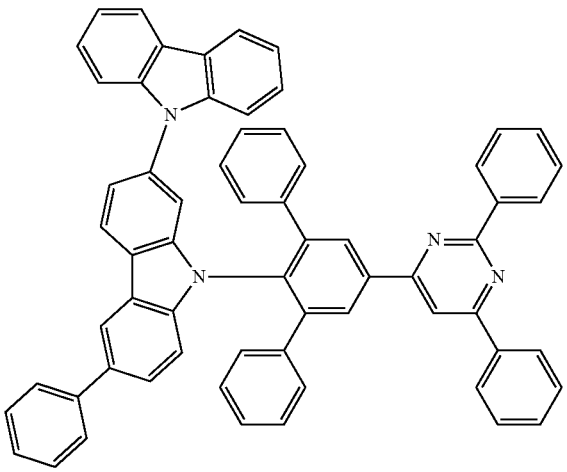
204
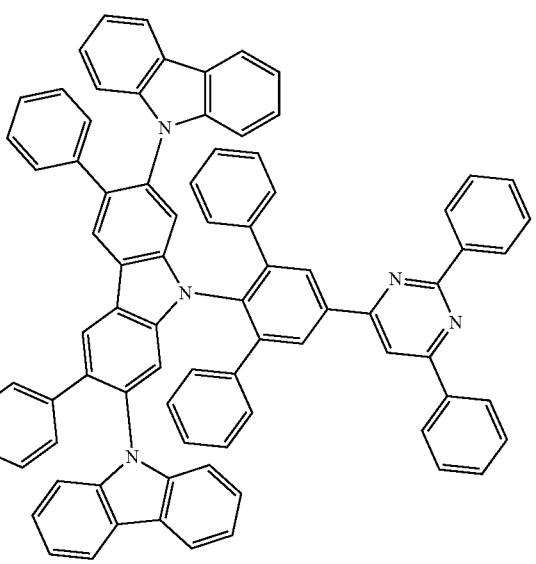
205

2939
-continued
206
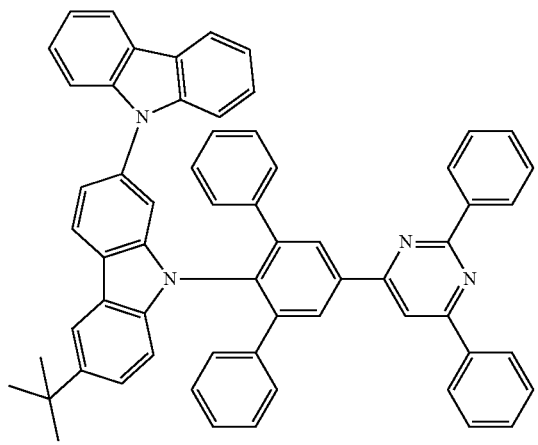
207
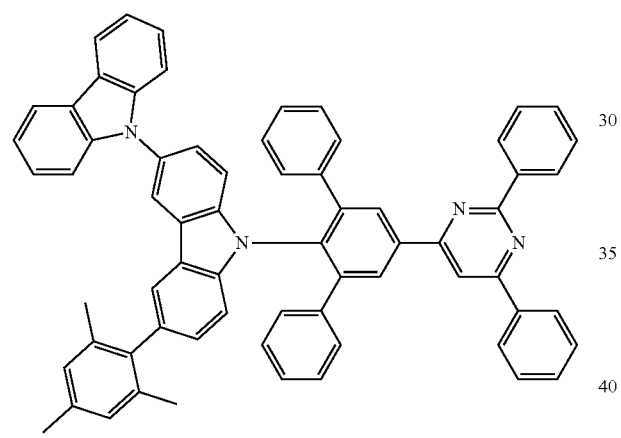
208
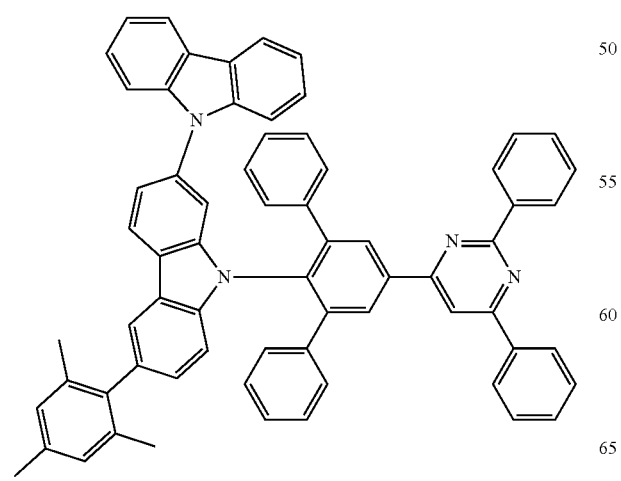
2940
-continued
209
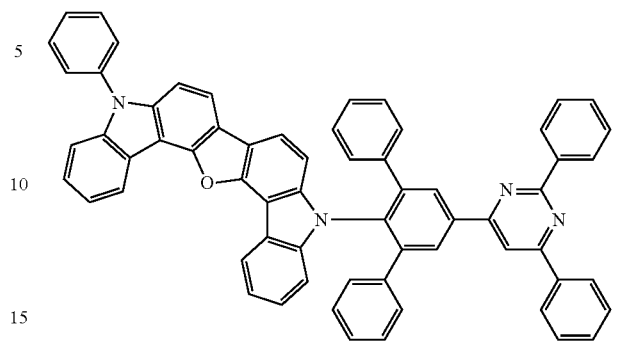
210
211
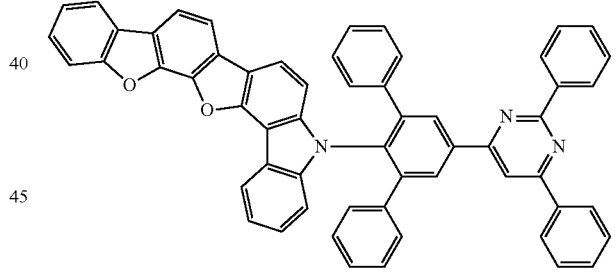
212
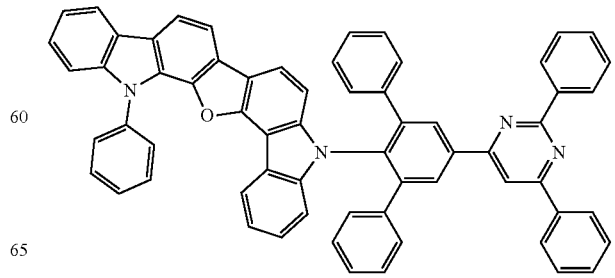

2941
-continued
2942
-continued
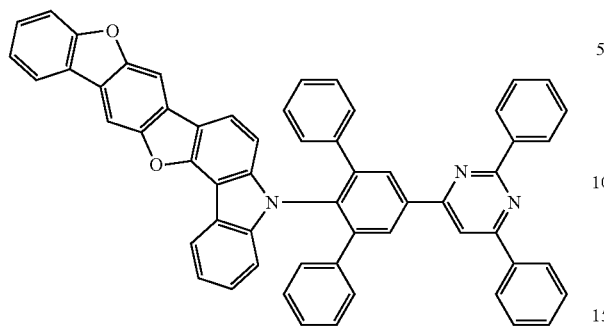
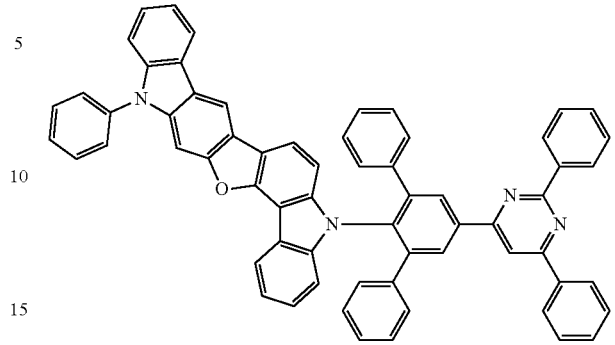
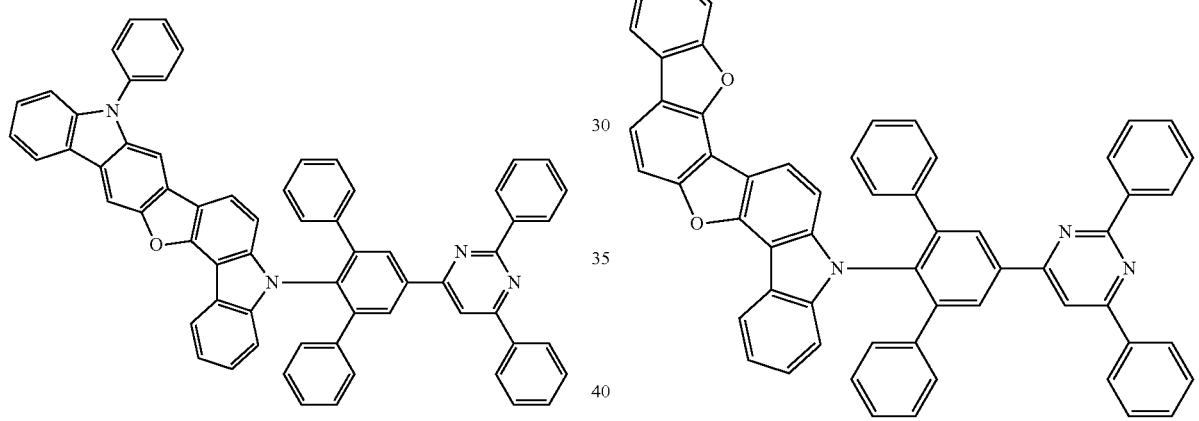
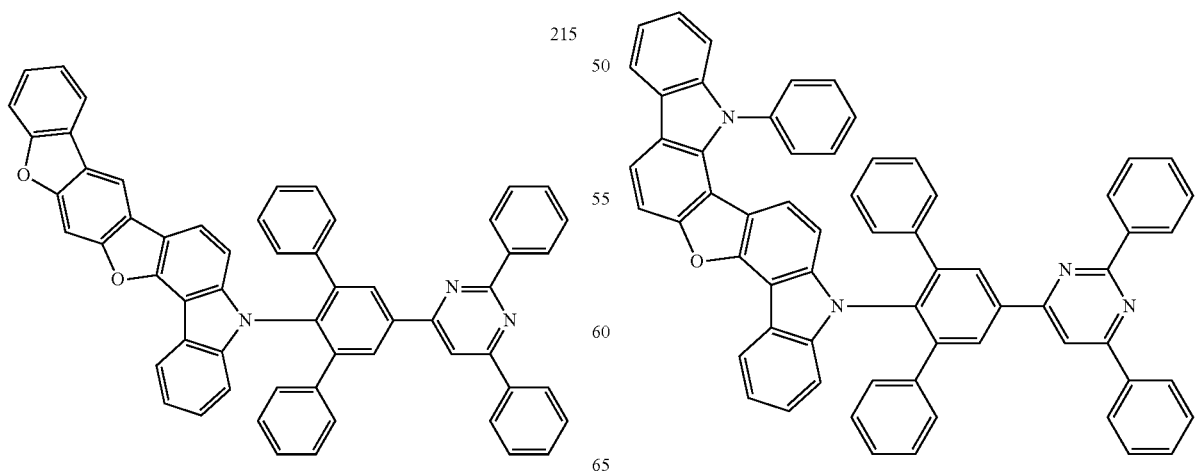

2943 2944
219
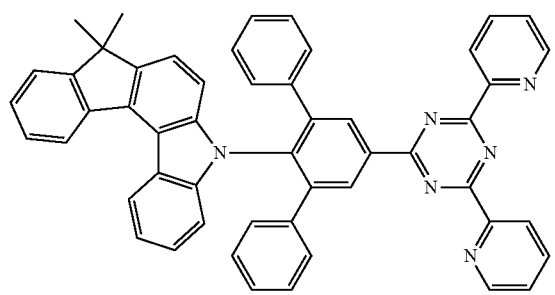
220
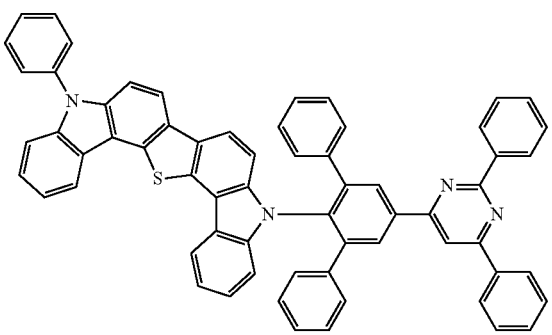
221
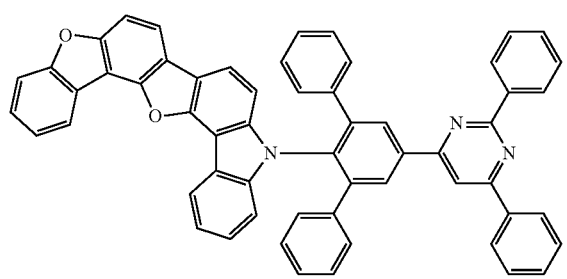
222
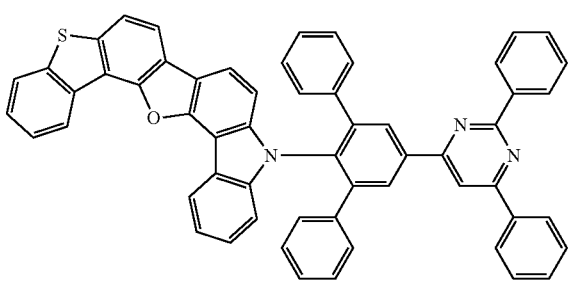
223
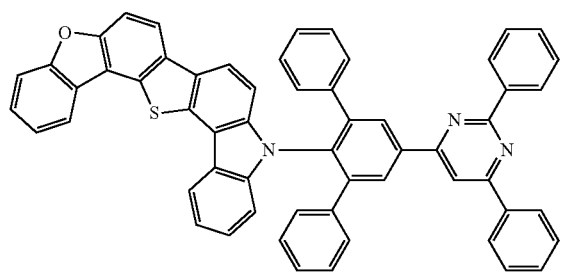
224
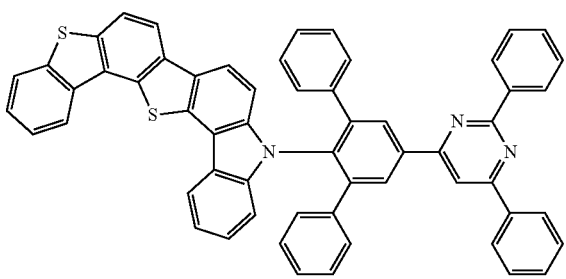
225
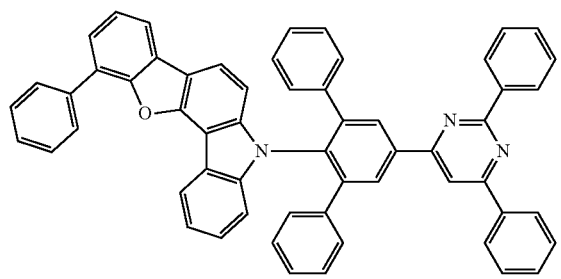
226
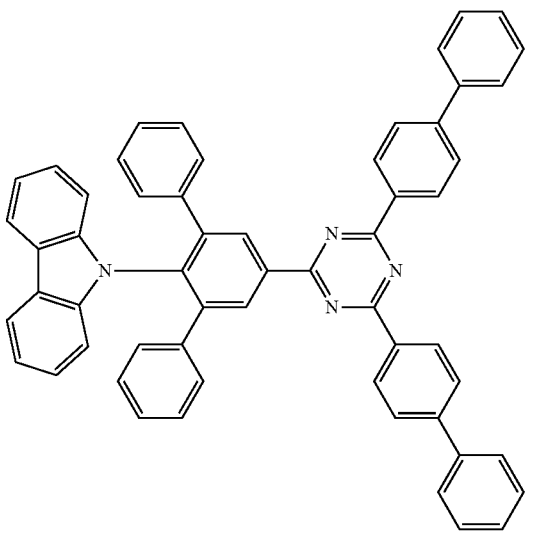

-continued
227
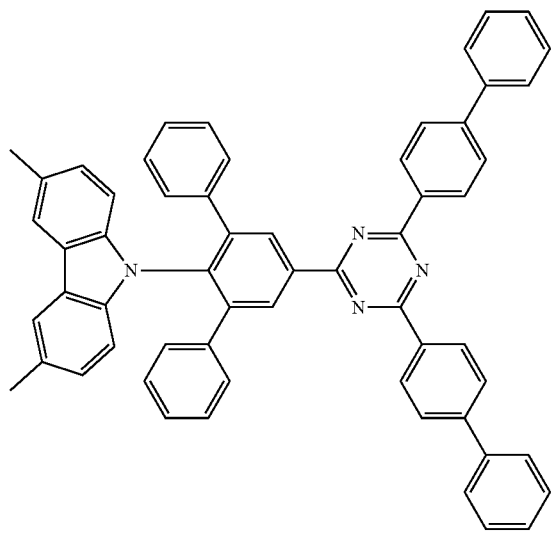
228
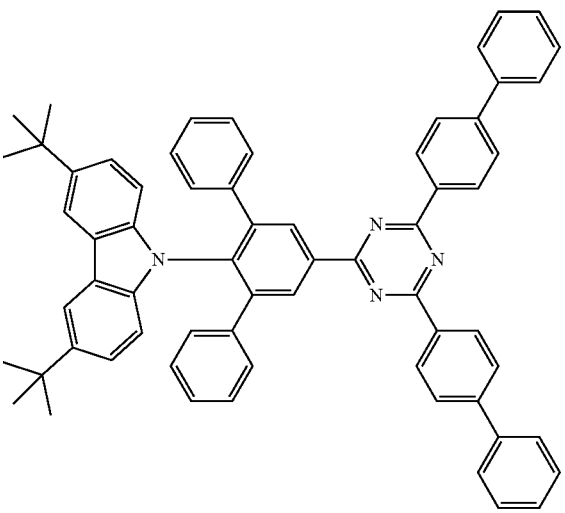
229
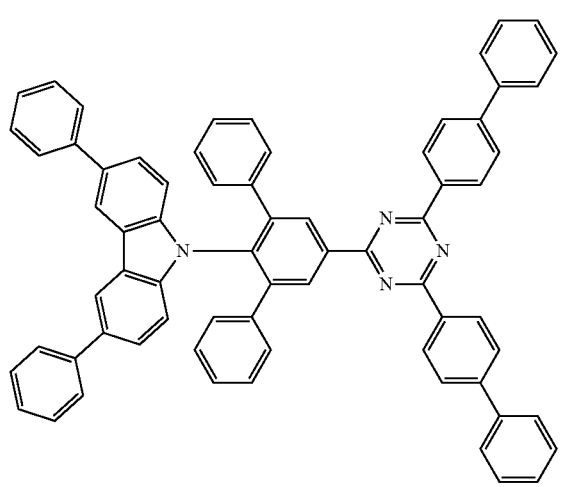
230
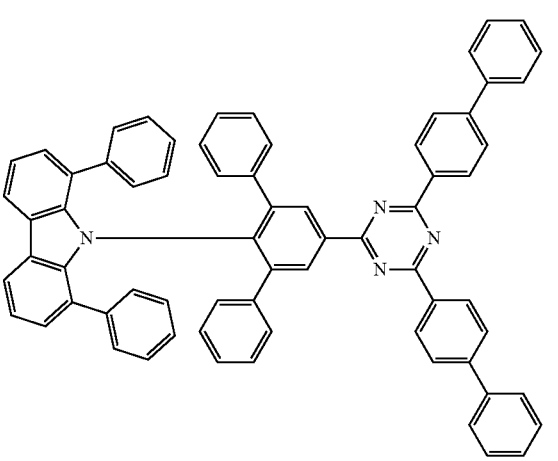
231
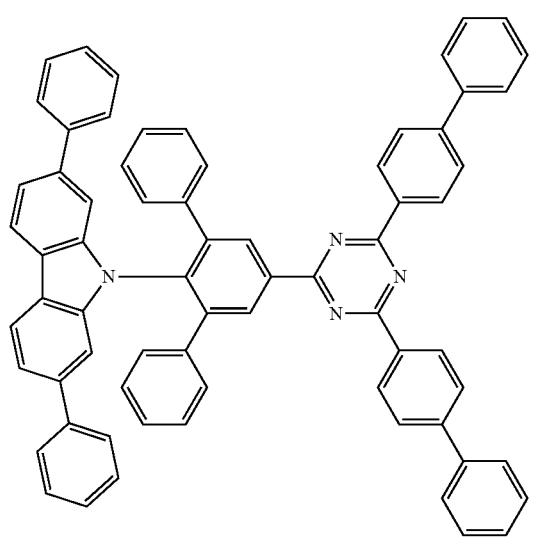
232
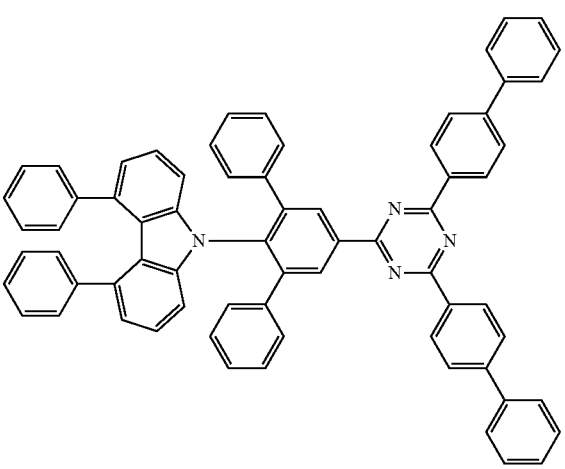

233
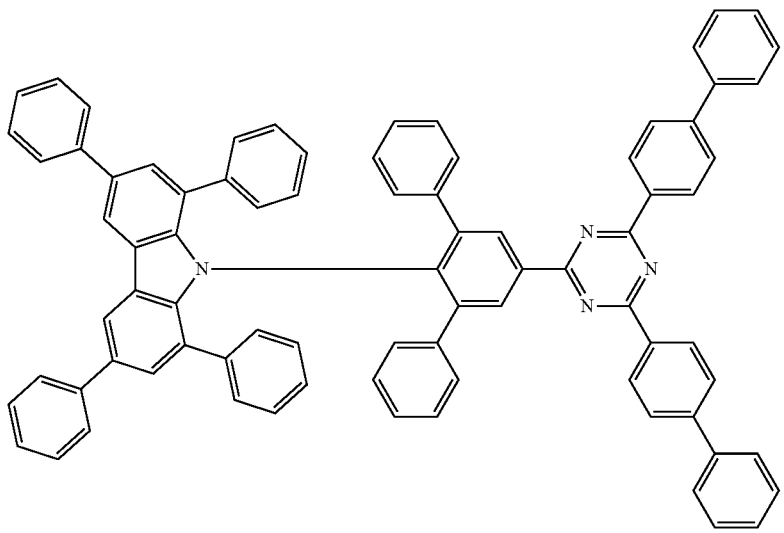
234
235
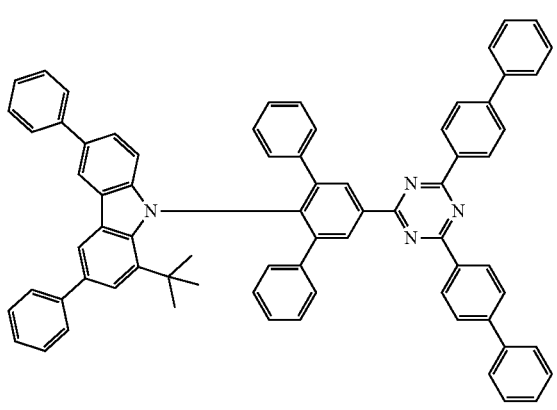
236
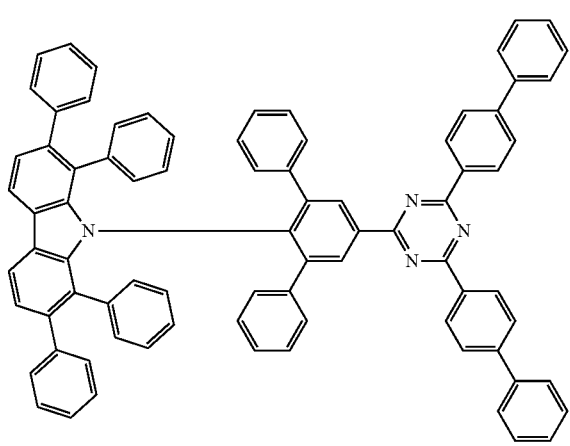

237
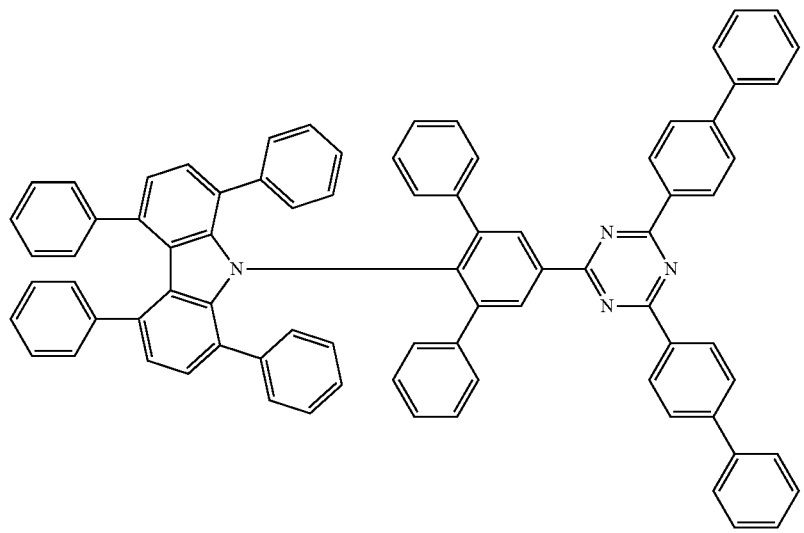
238 239
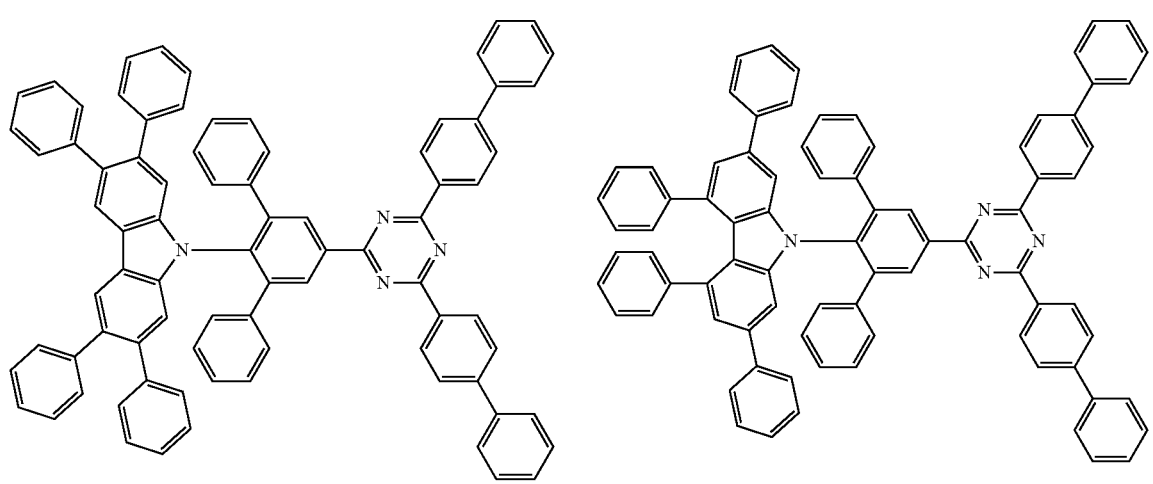
240 241
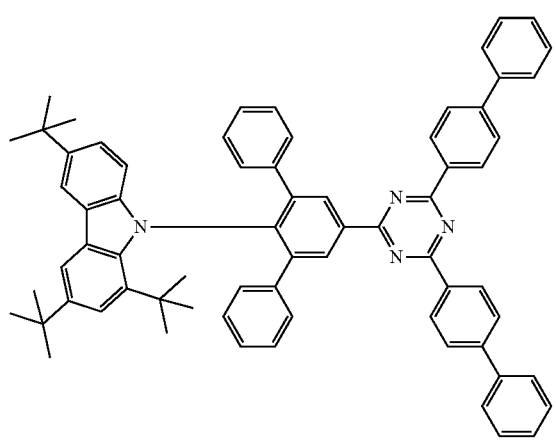 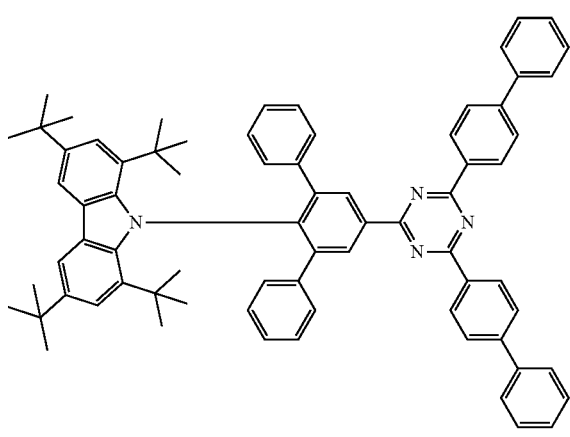

-continued
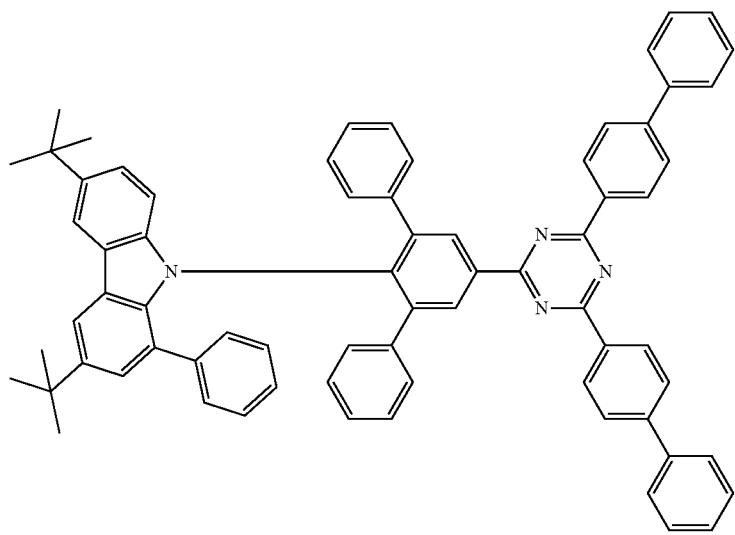
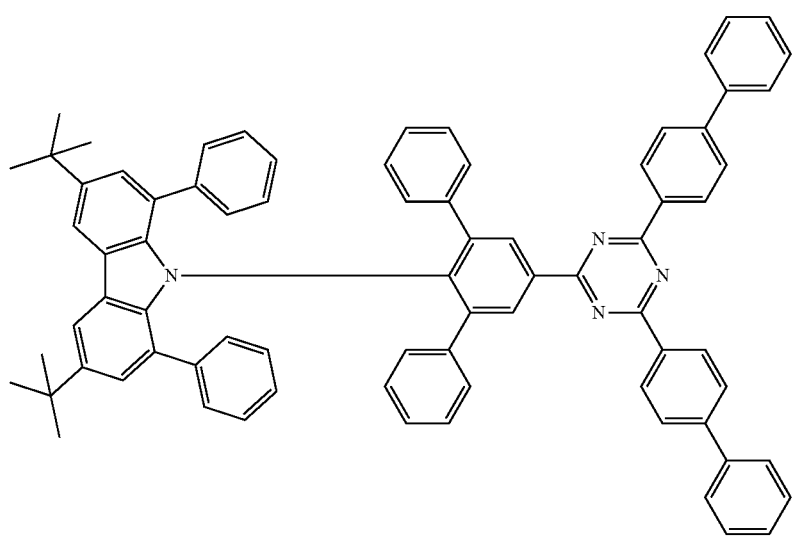
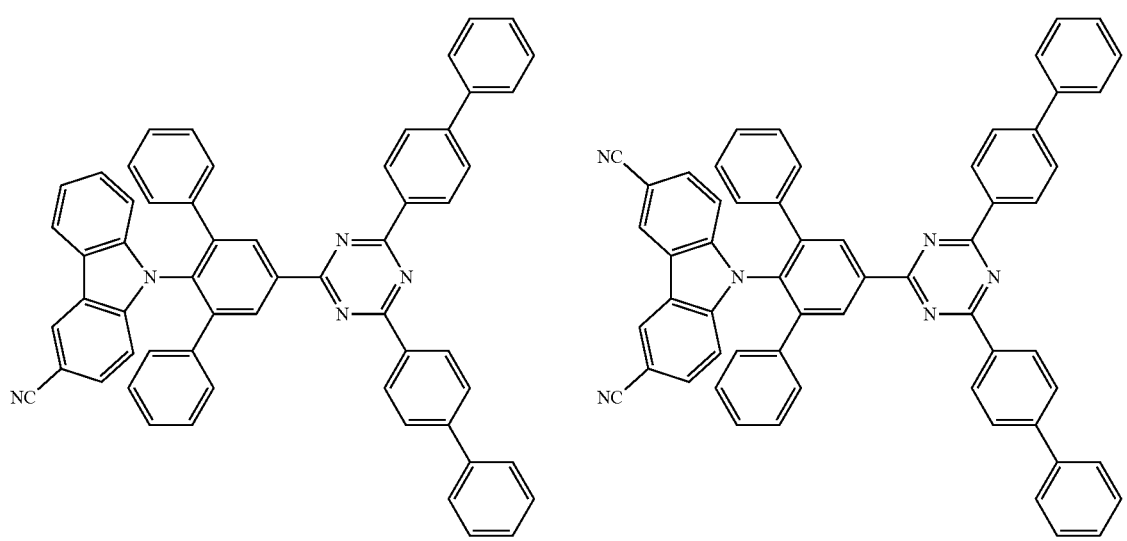

246
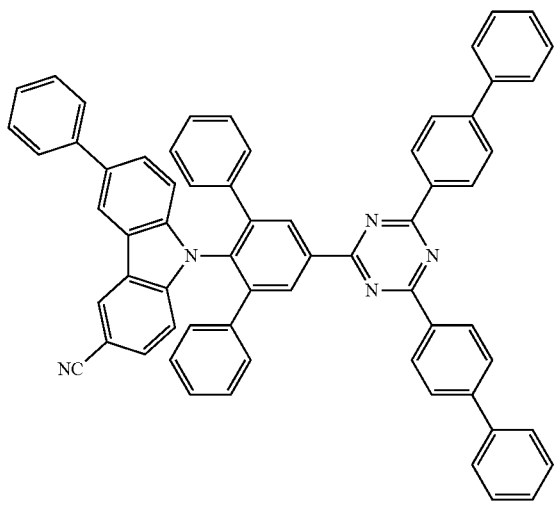
247
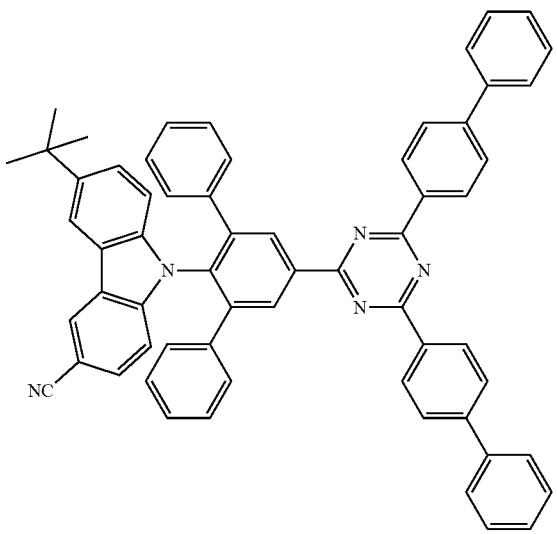
248
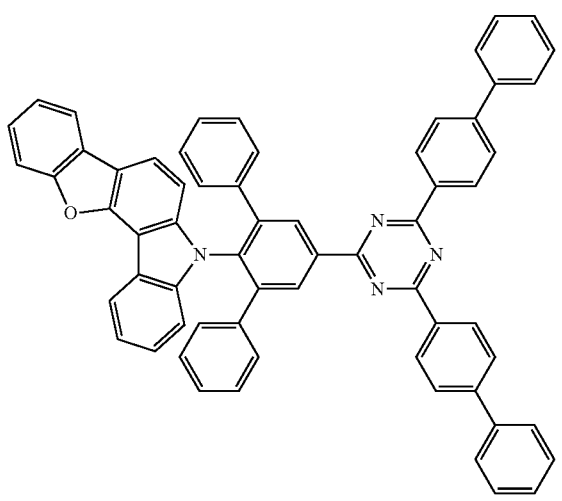
249
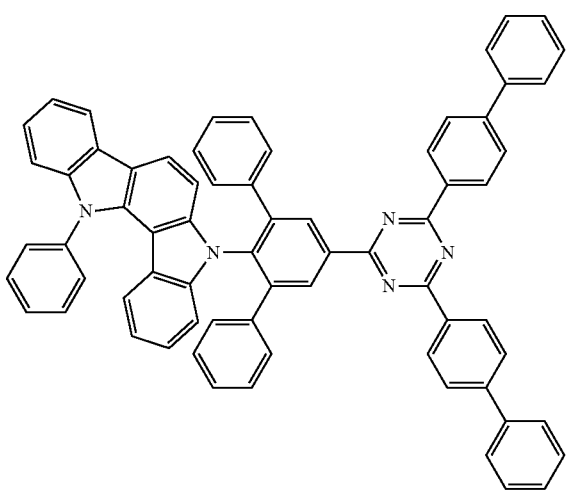
250
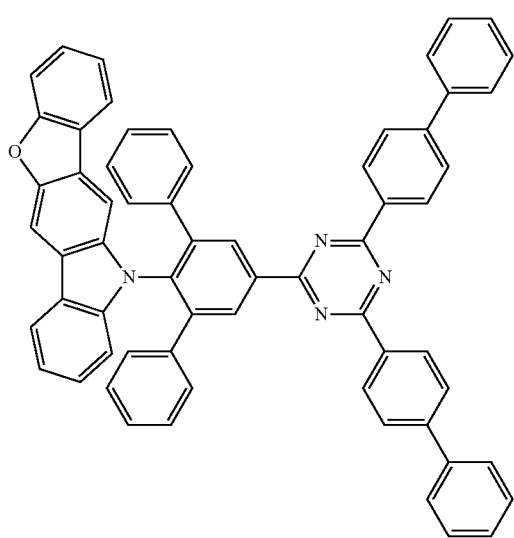
251
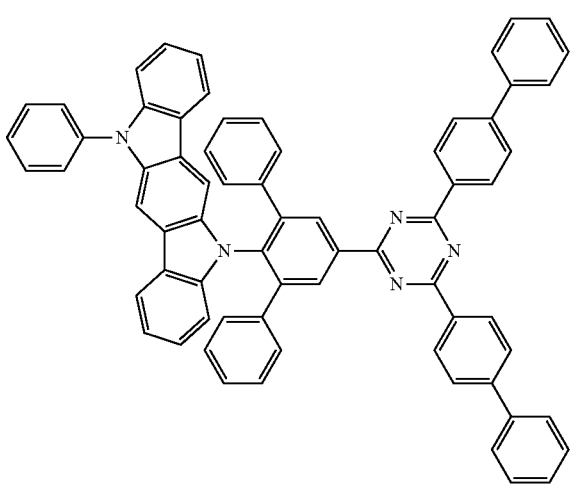

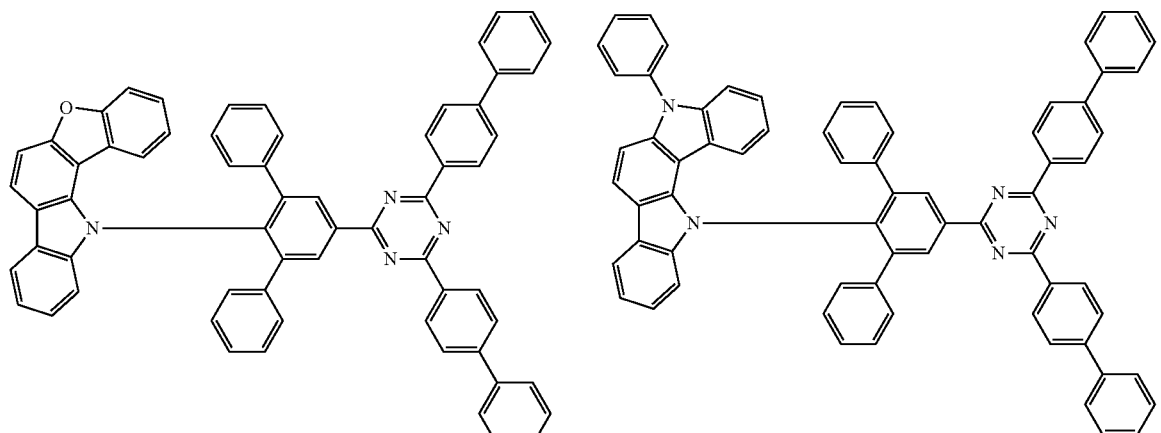
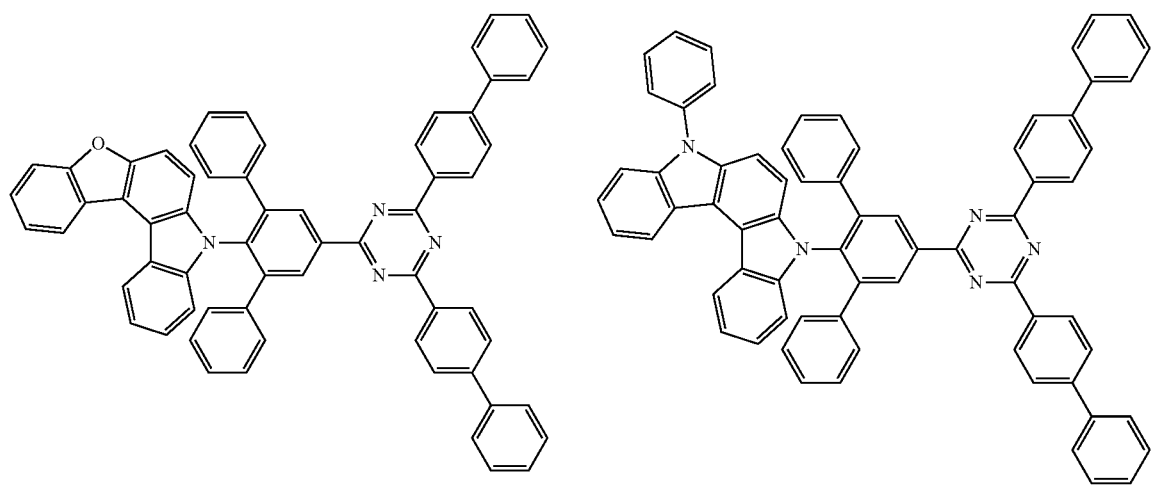
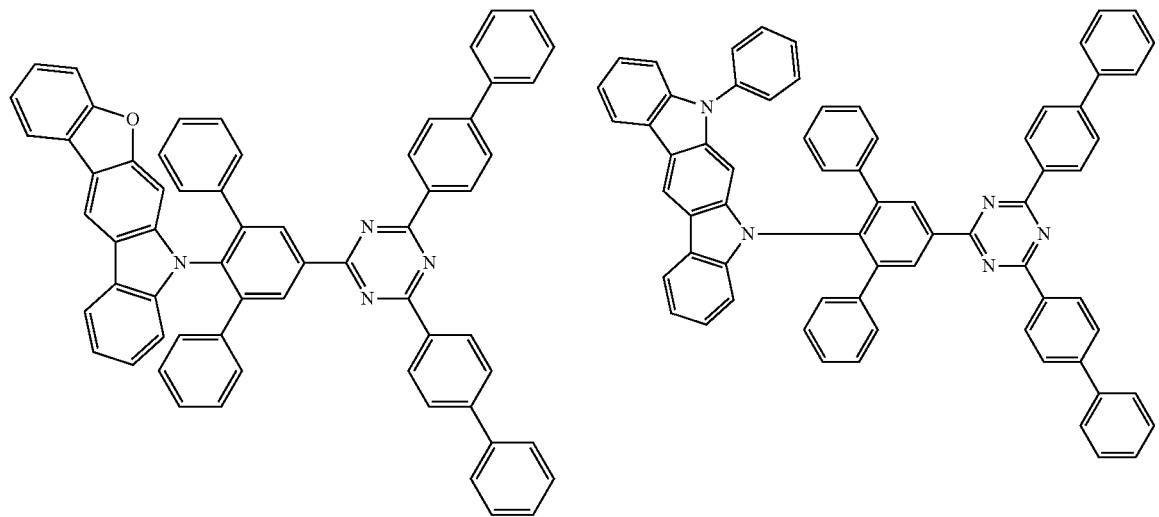

258
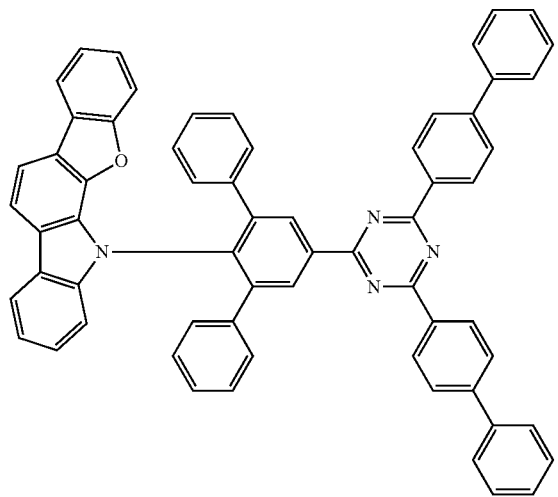
259
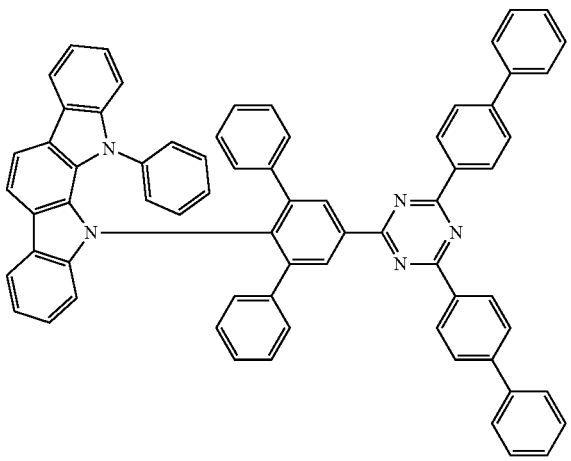
260
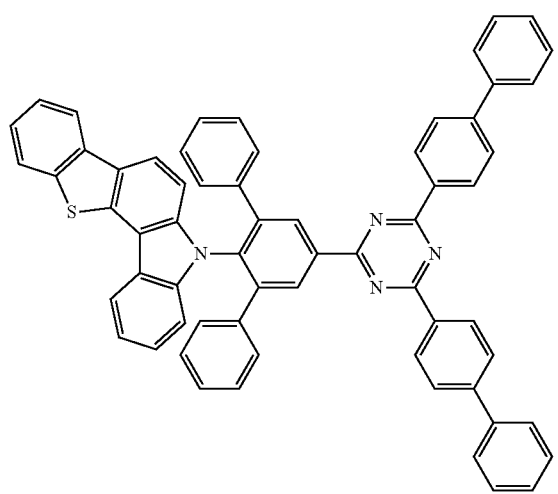
261
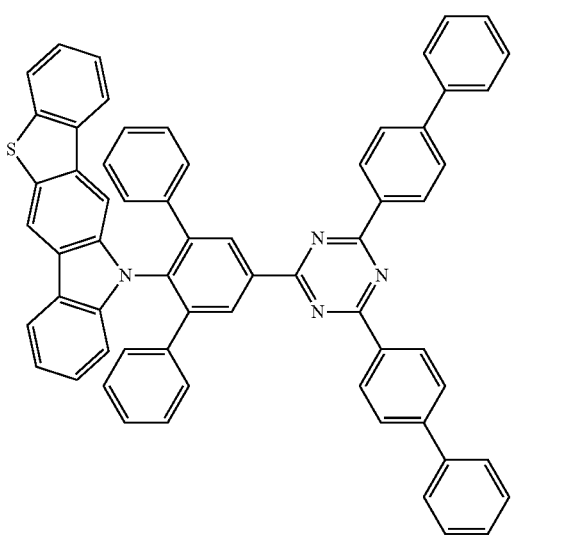
262
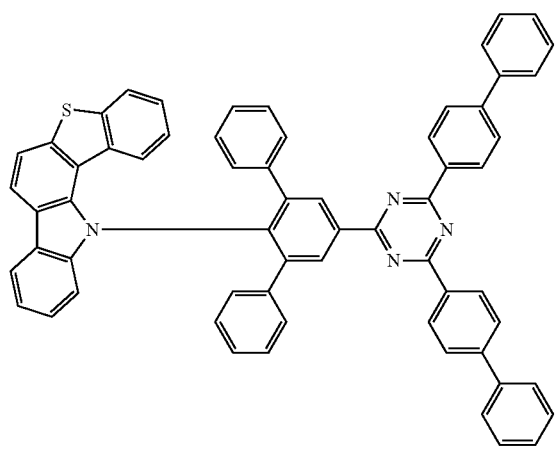
263
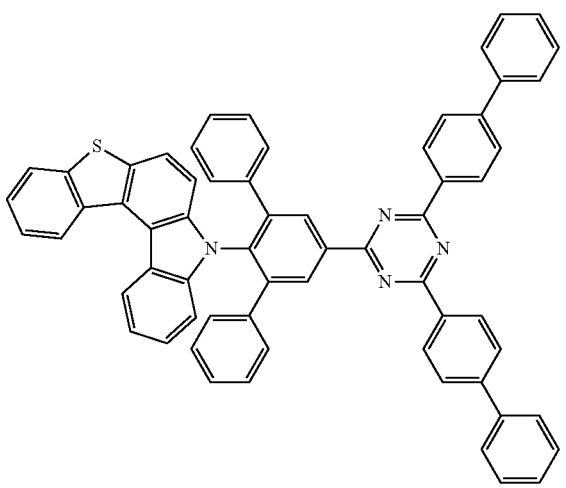

-continued
264
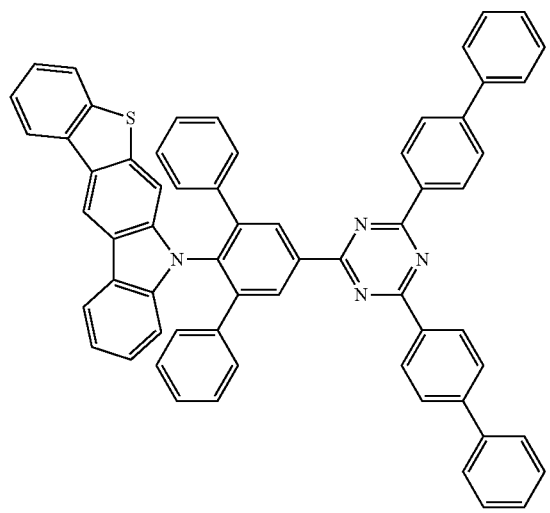
265
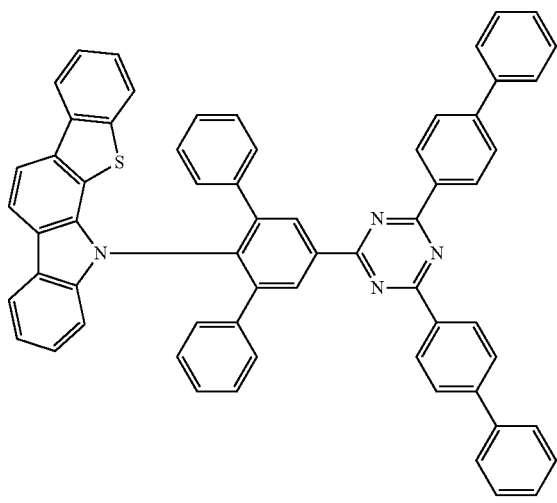
266
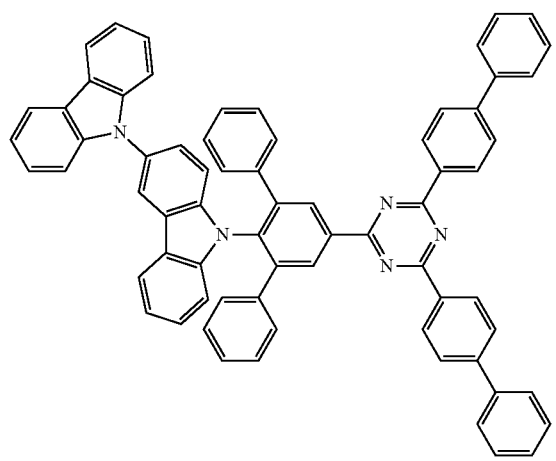
267
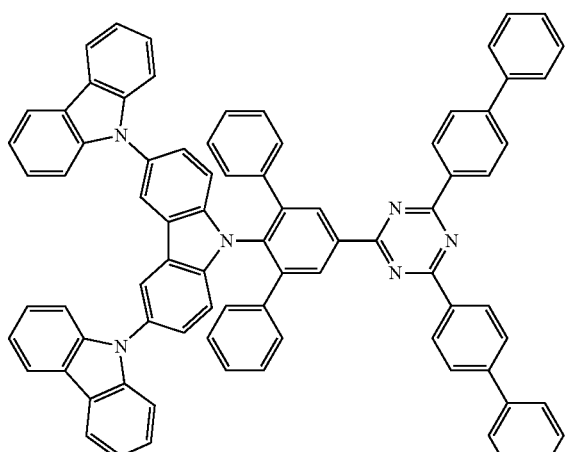
268
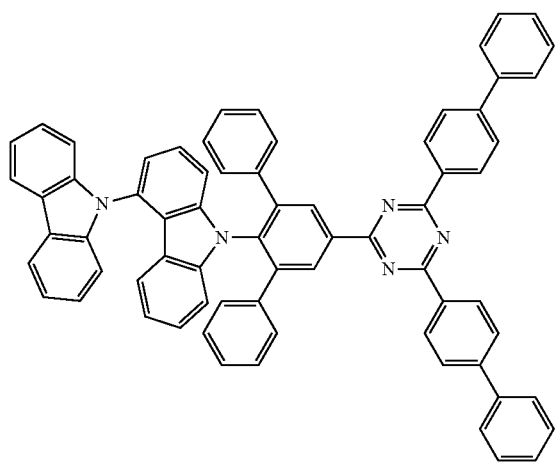
269
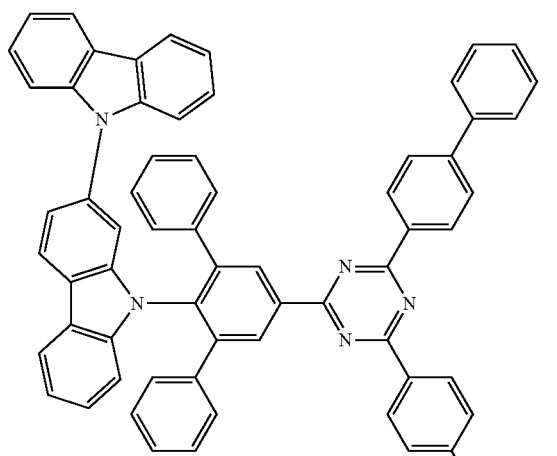

270
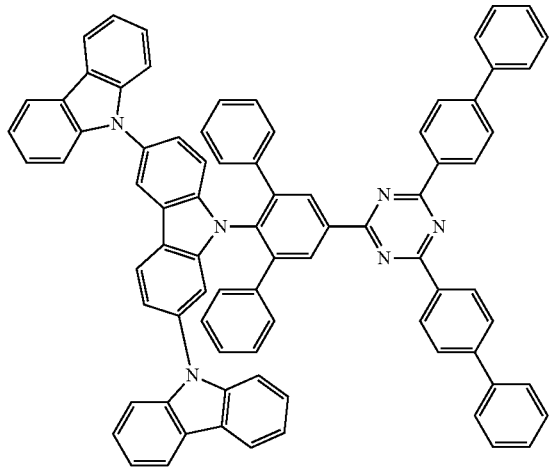
271
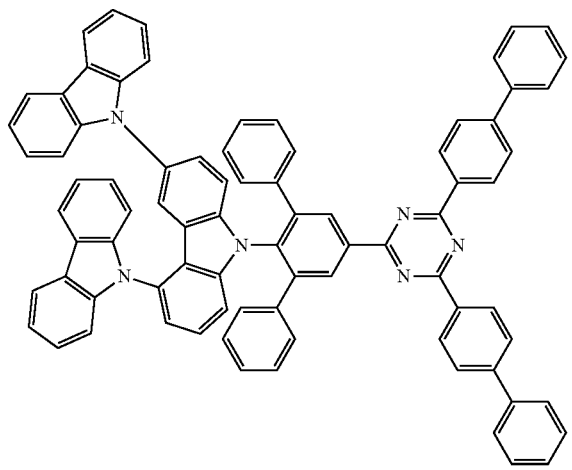
272
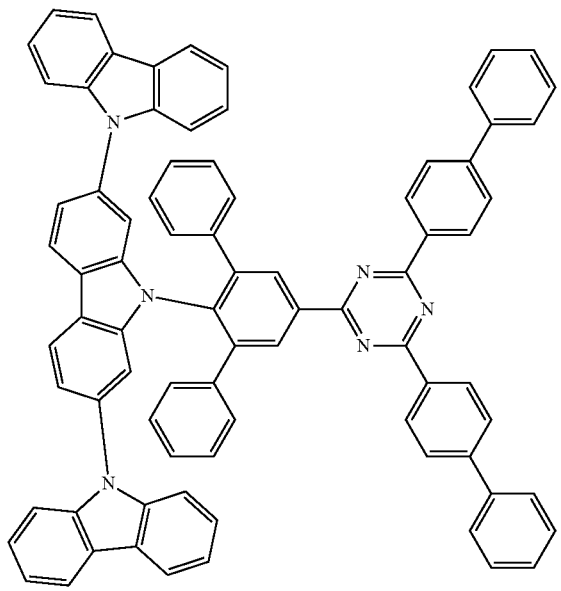
273
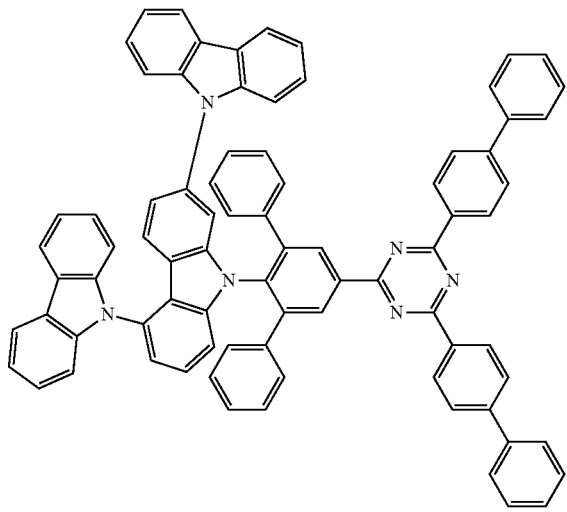
274
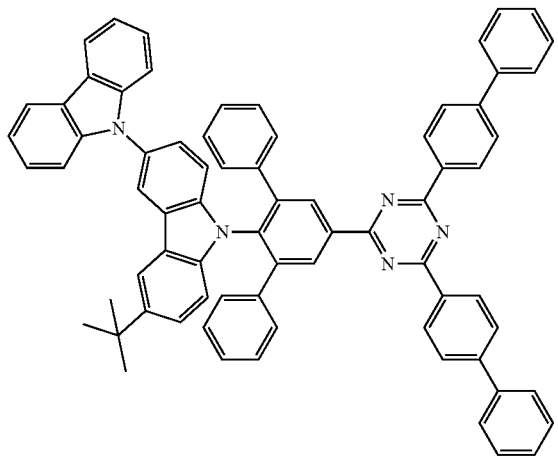
275
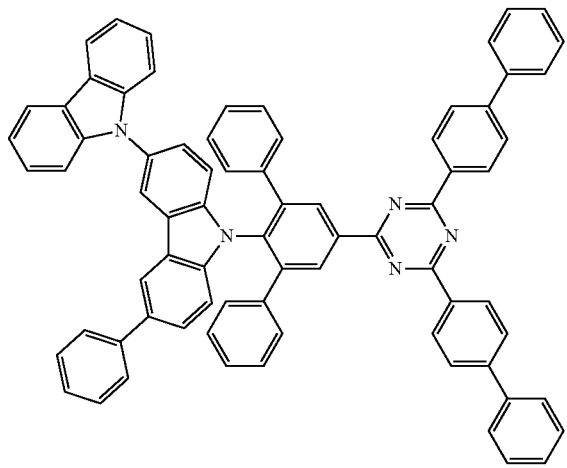

-continued
276
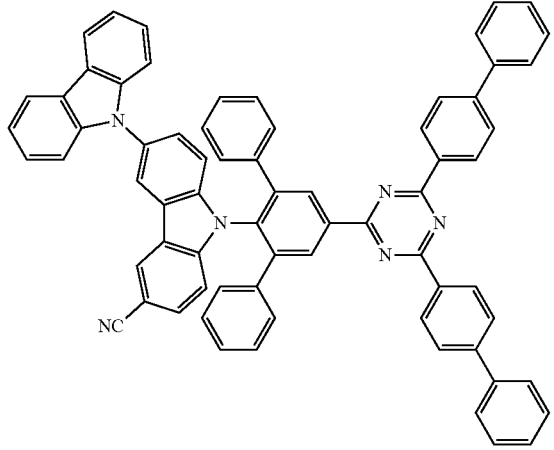
277
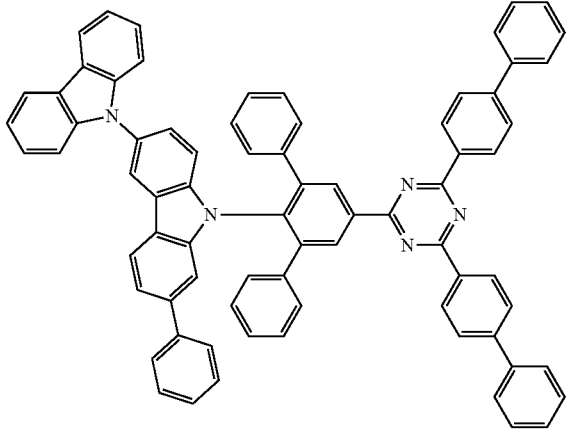
278
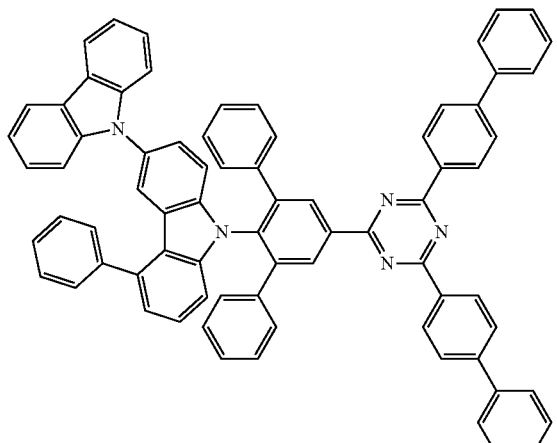
279
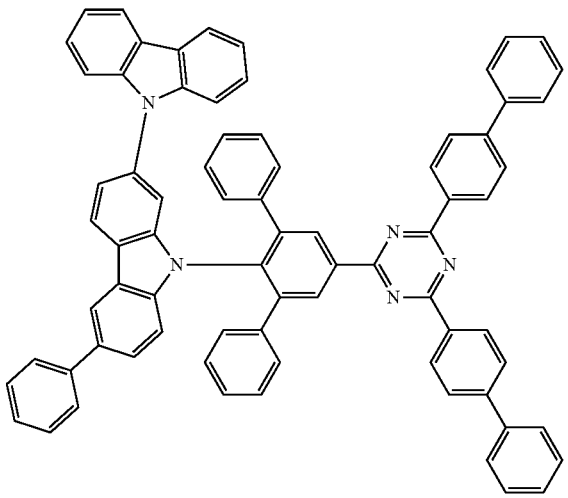
280
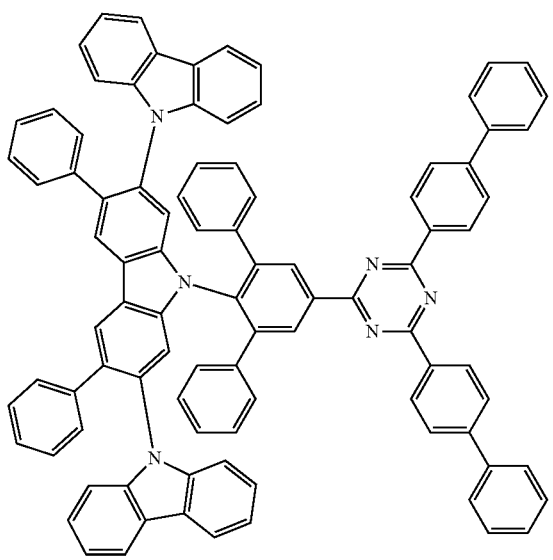
281
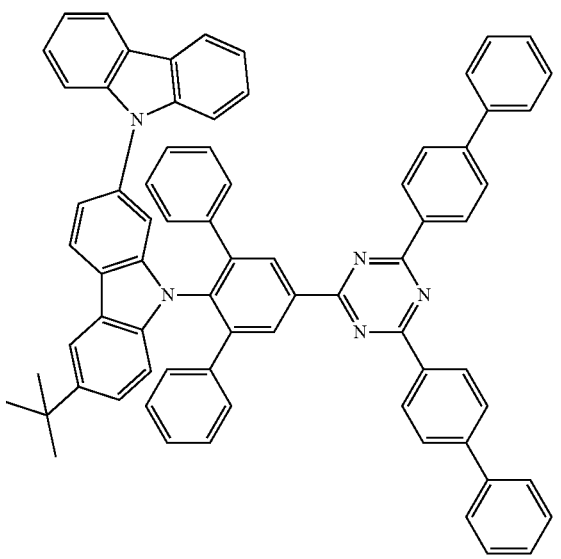

-continued
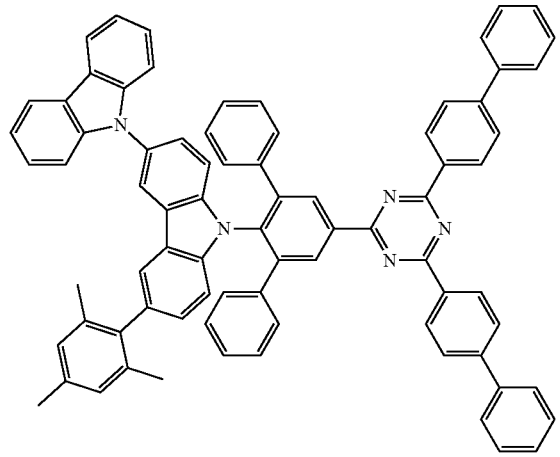
282
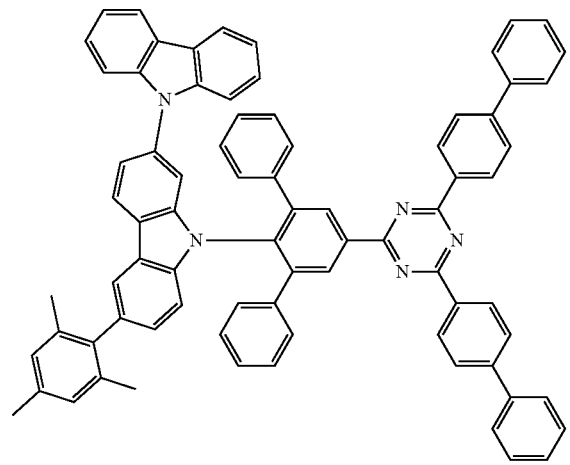
283
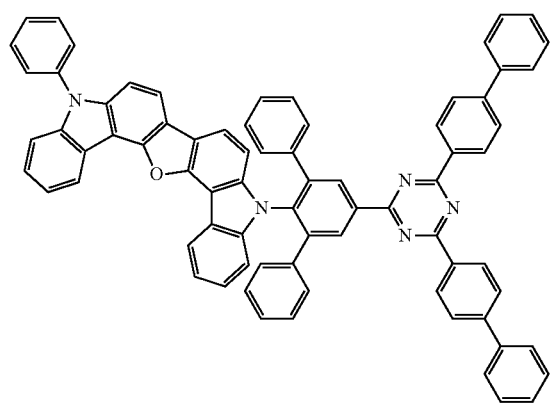
284
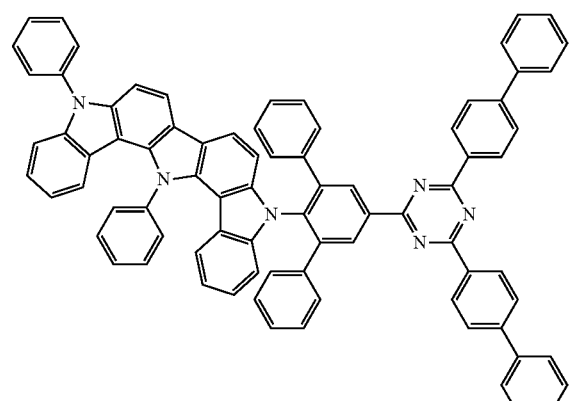
285
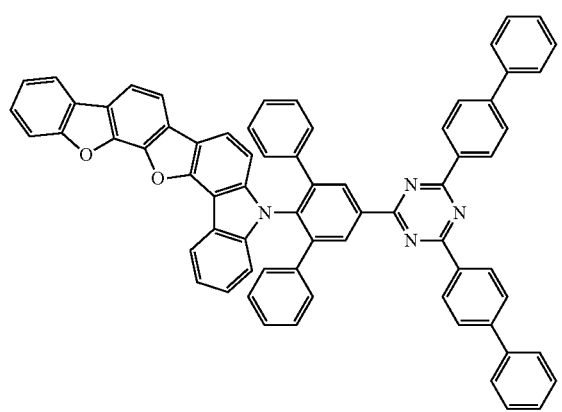
286
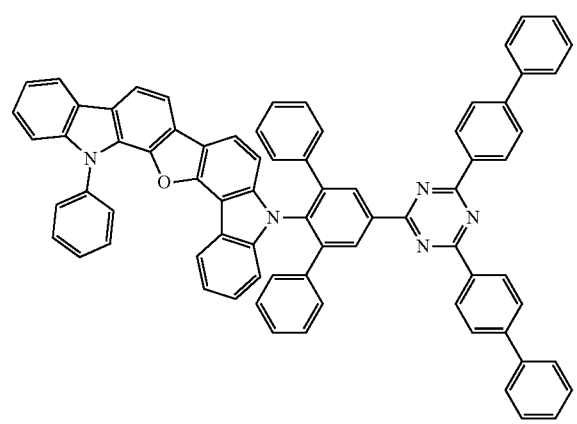
287

288
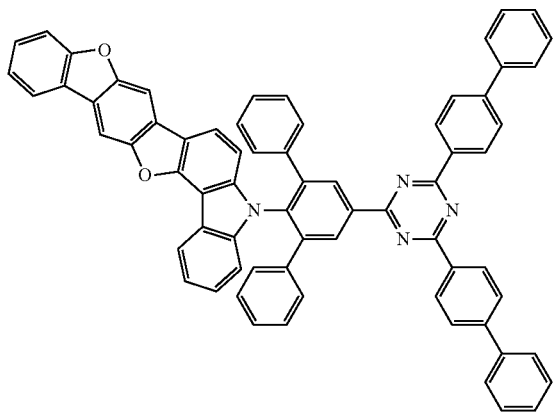
289
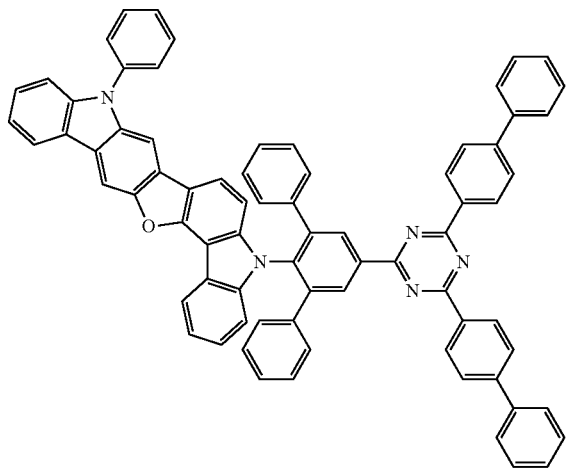
290
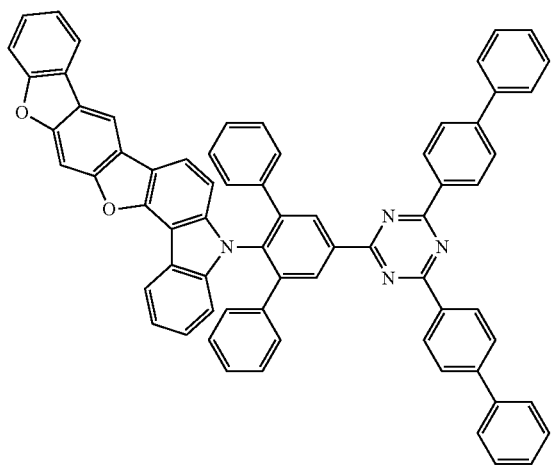
291
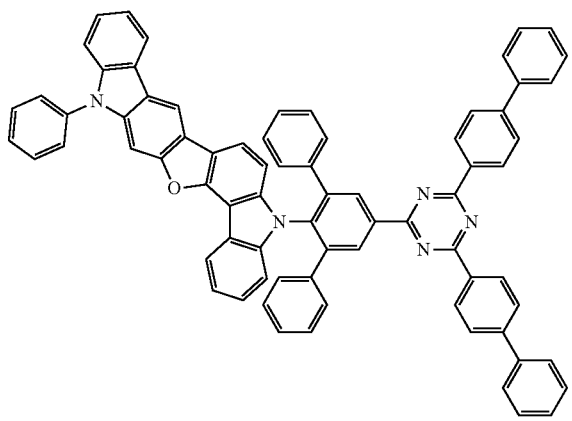
292
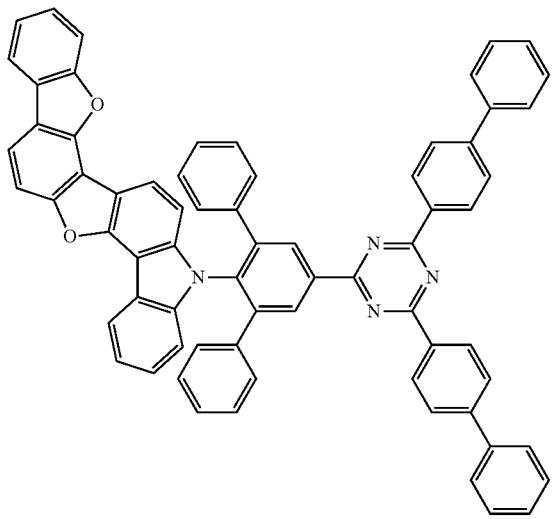
293
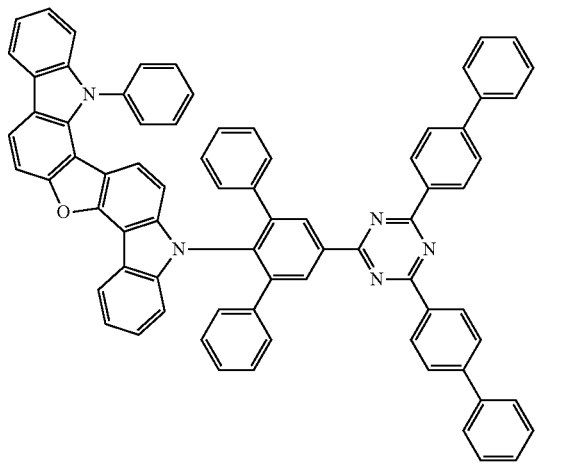

-continued
294
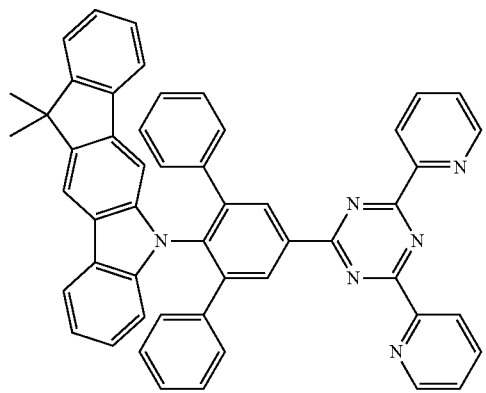
295
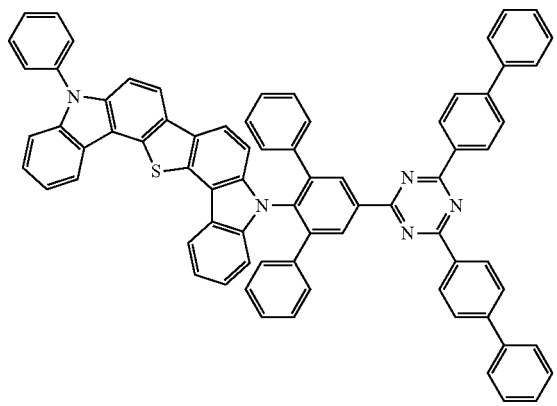
296
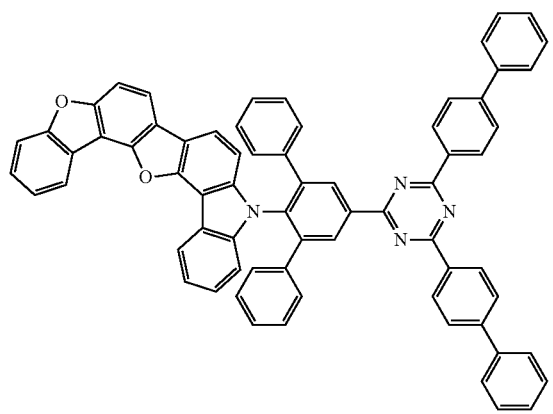
297
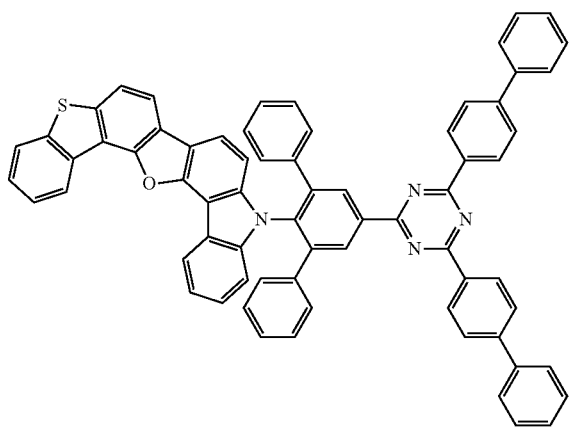
298
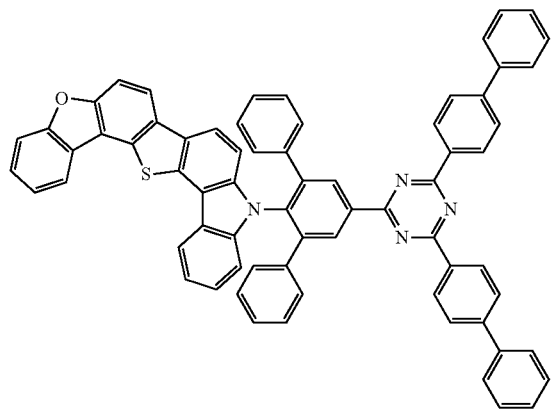
299
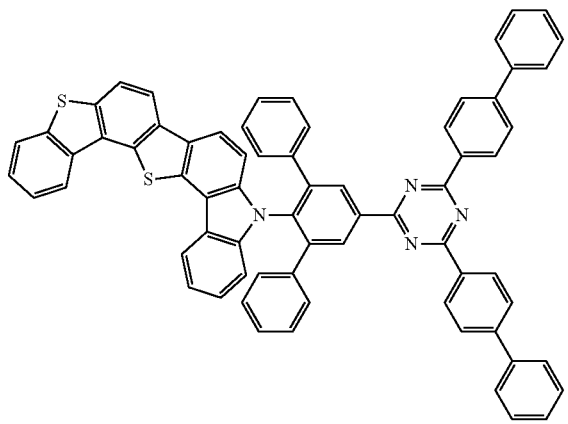

-continued
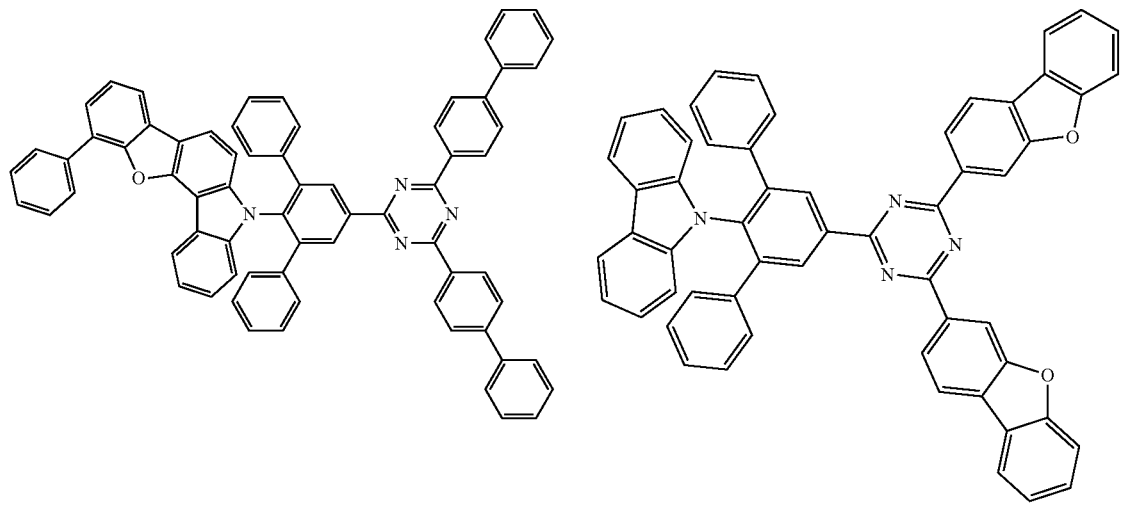
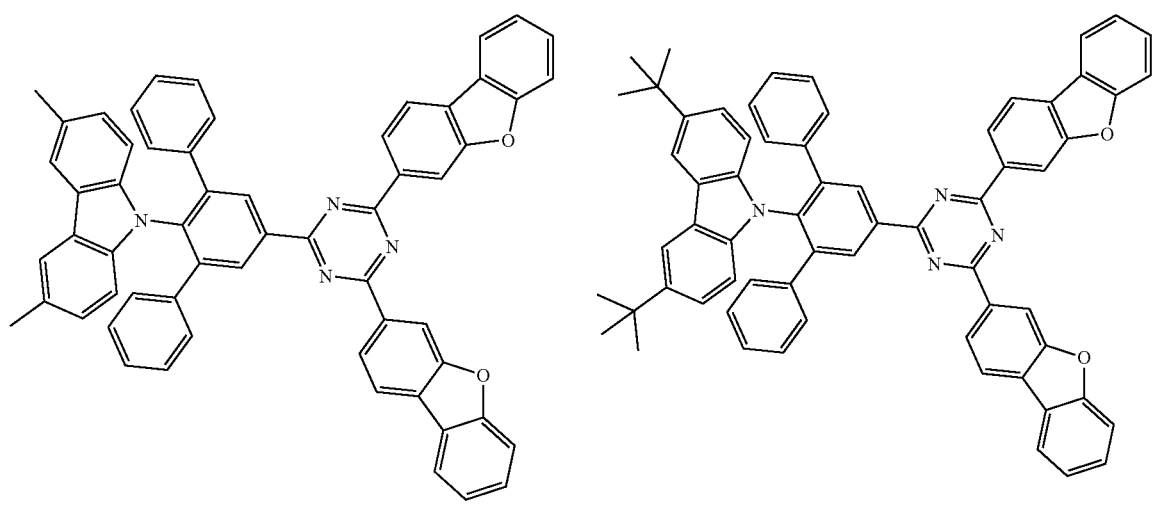
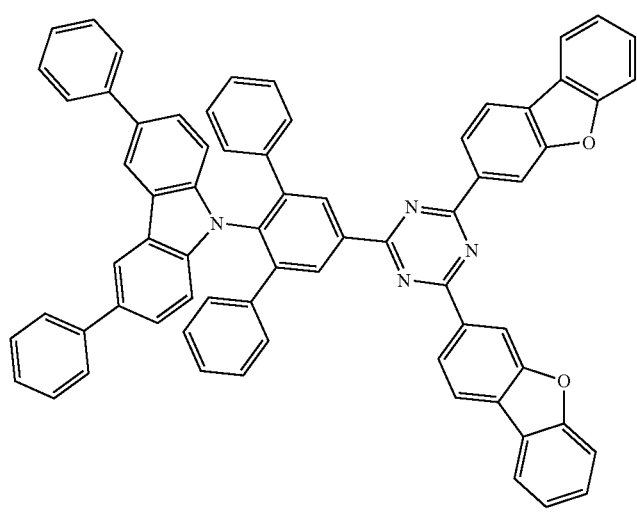

305
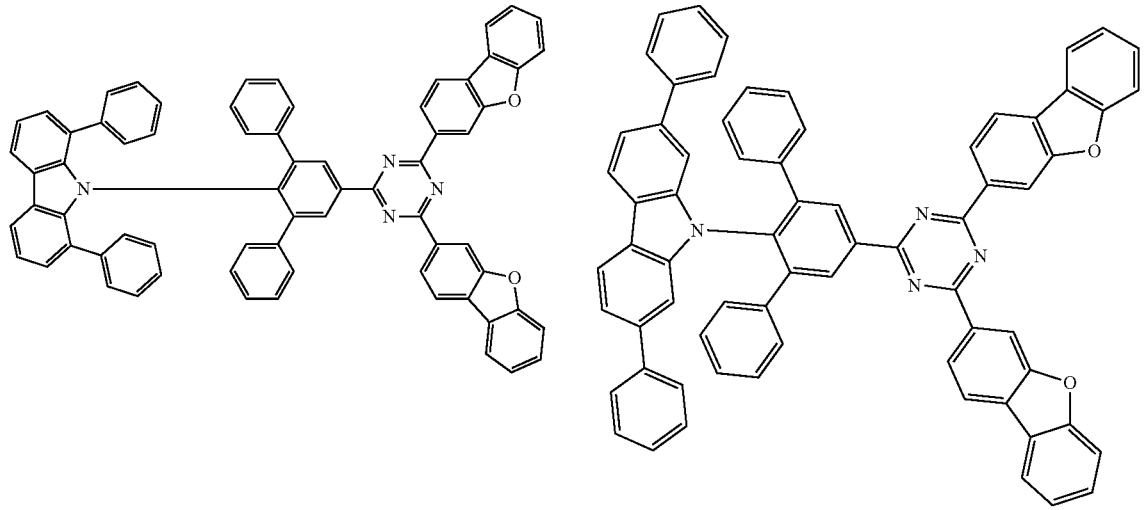
306
307
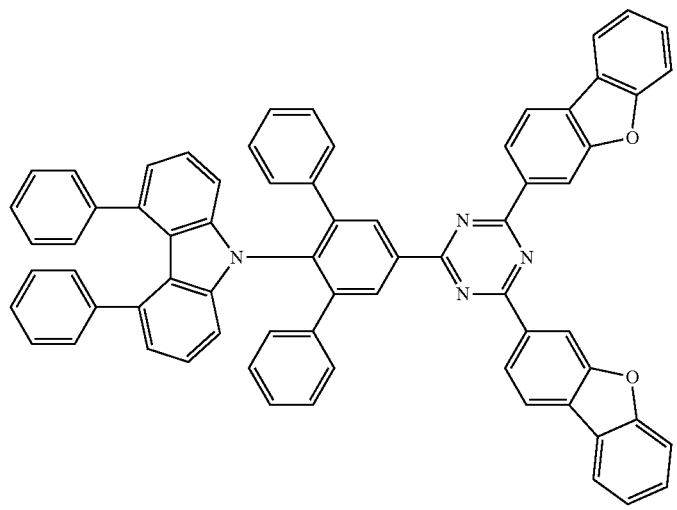
308
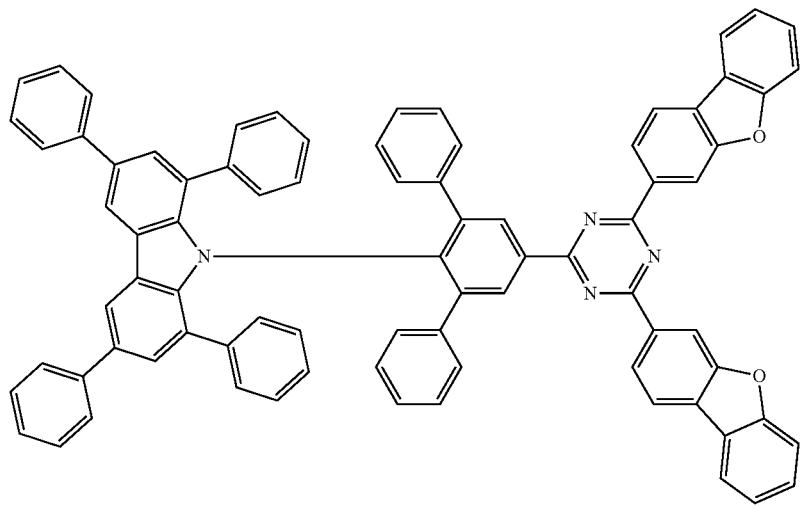

309
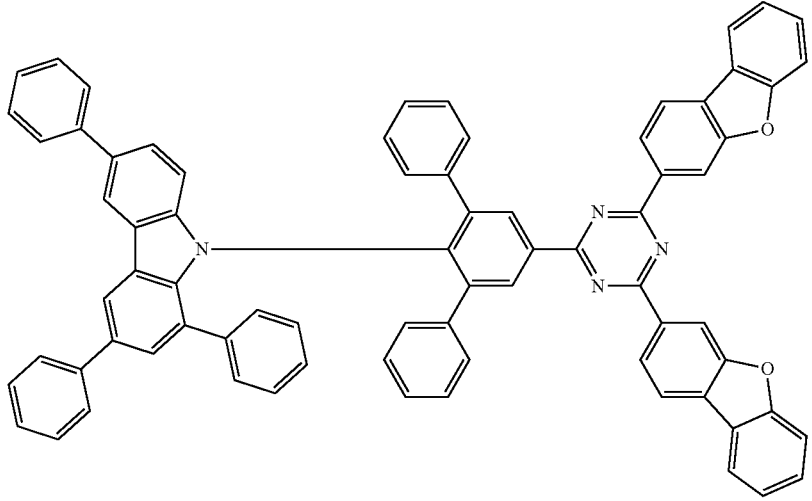
310
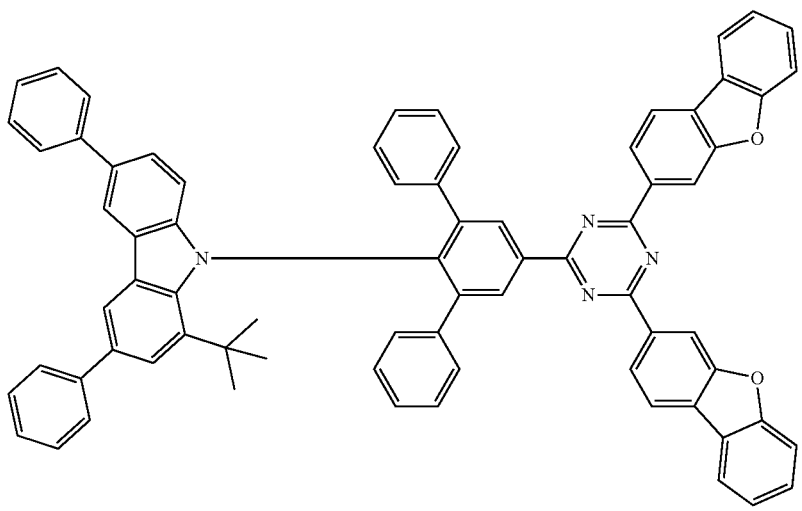
311
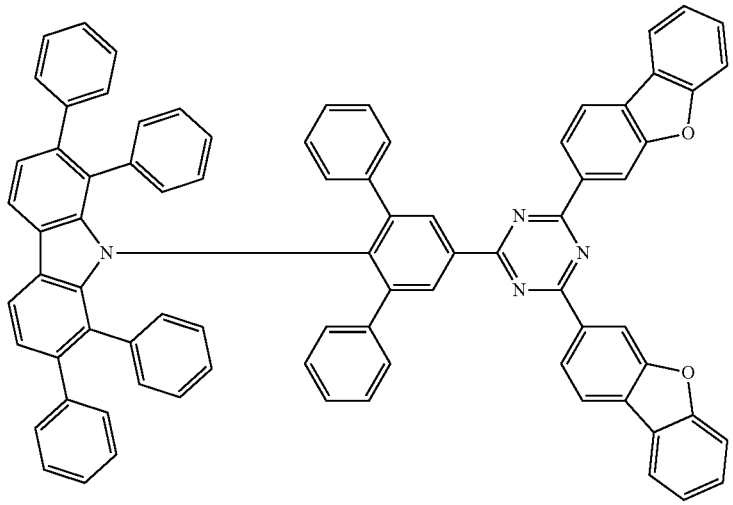

-continued
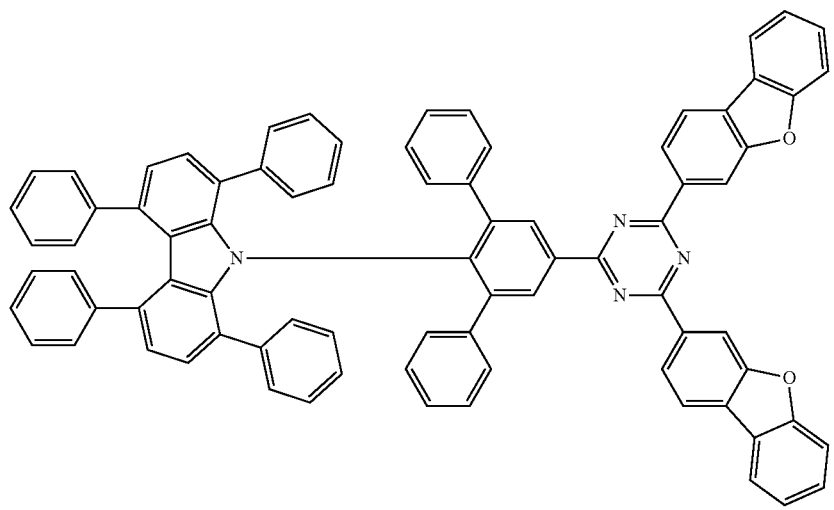
312
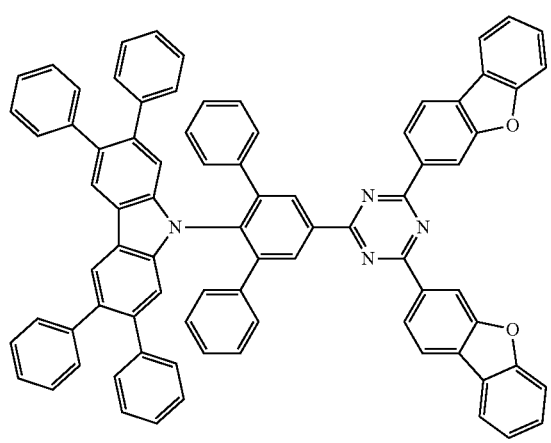
313
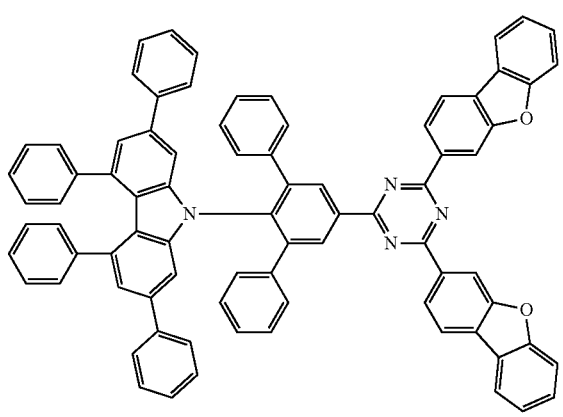
314
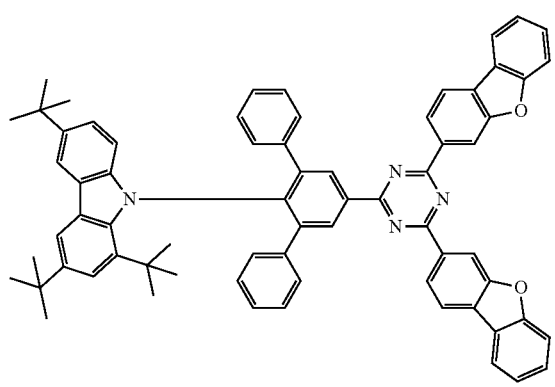
315
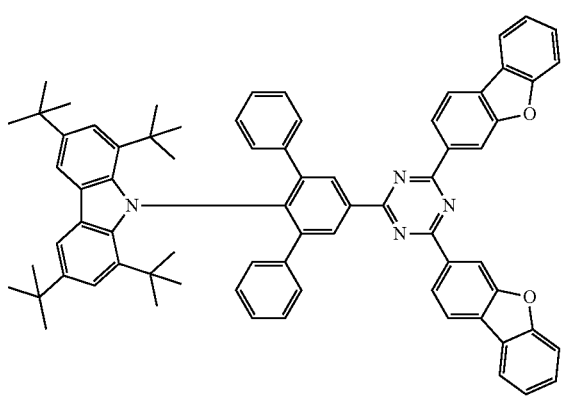
316

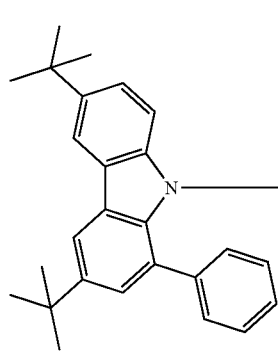
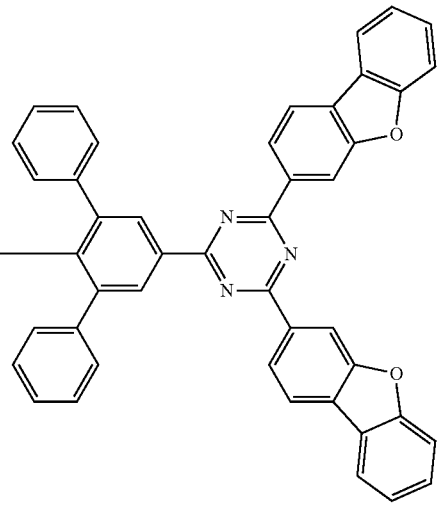
317
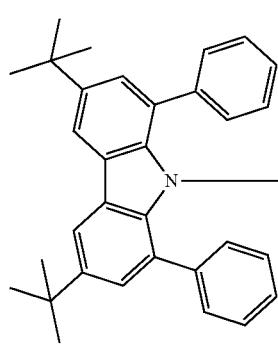
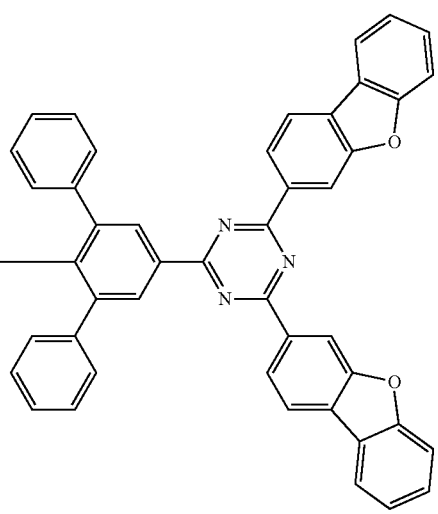
318
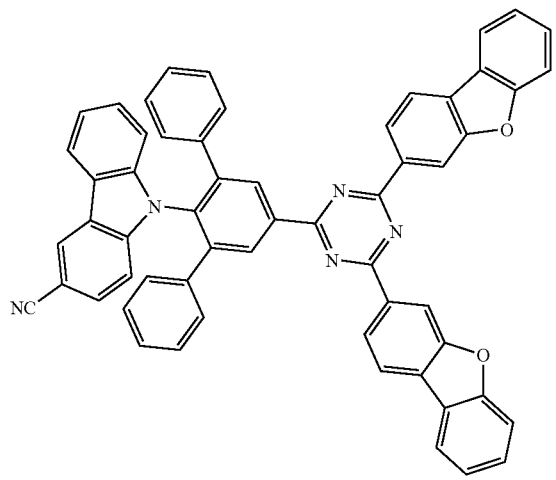
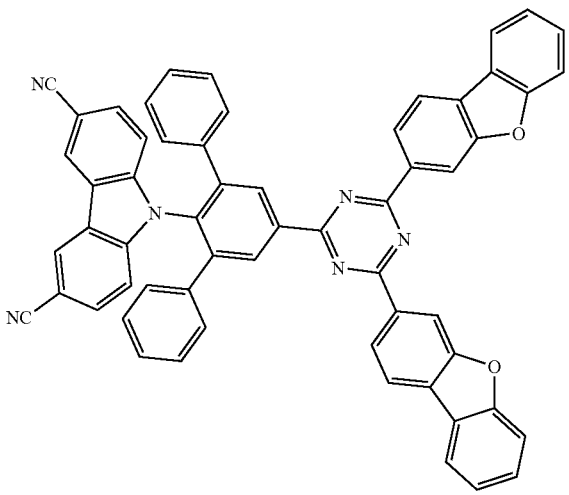
319 320

321
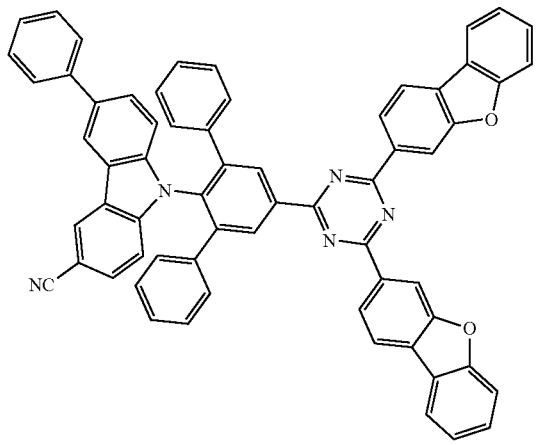
322
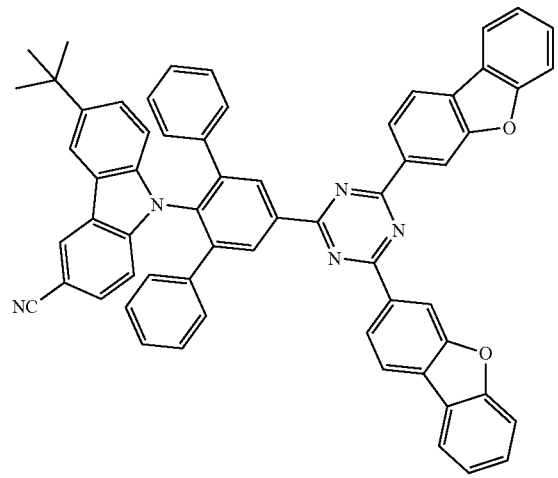
323
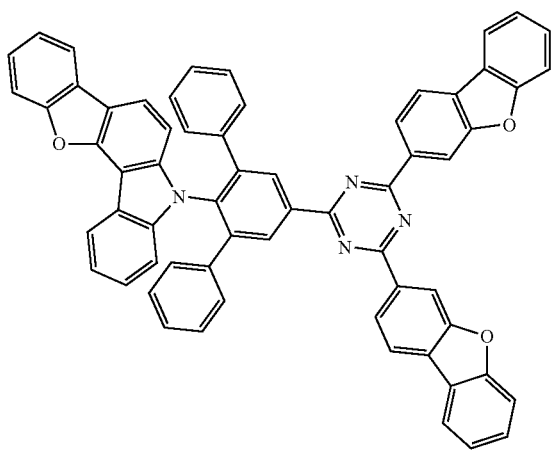
324
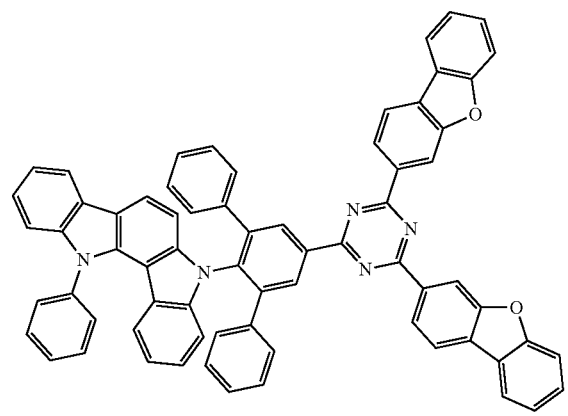
325
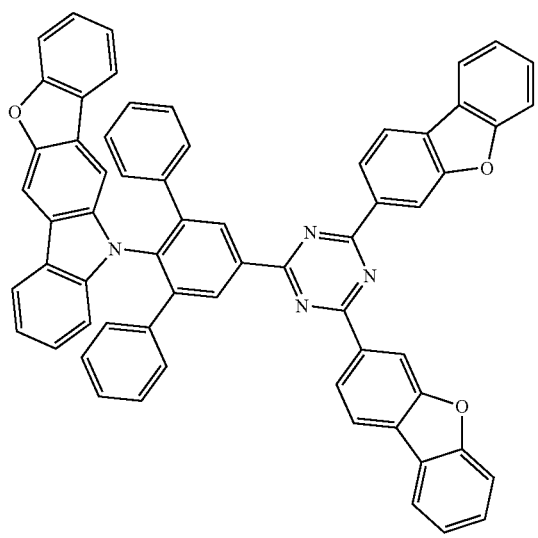
326
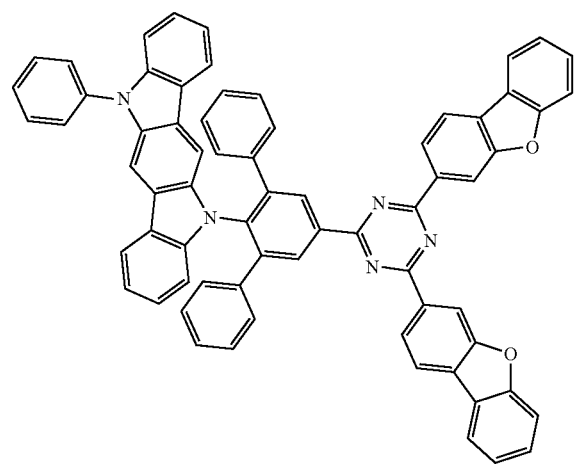

-continued
327
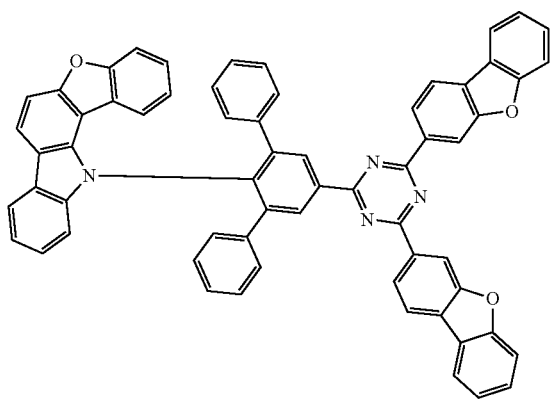
328
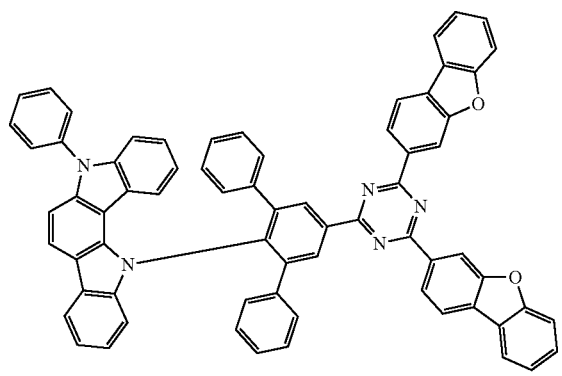
329
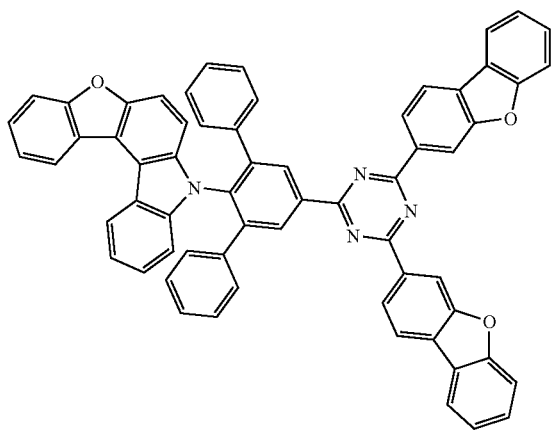
330
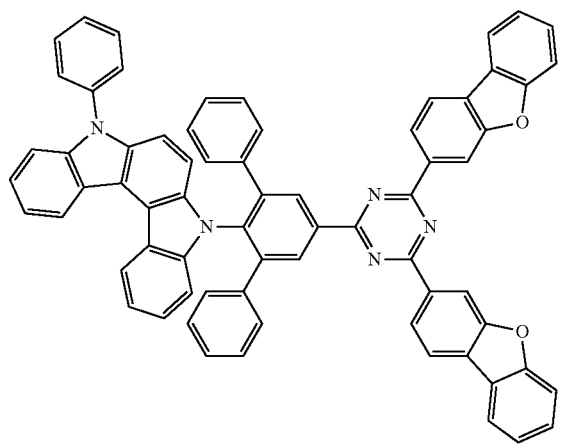
331
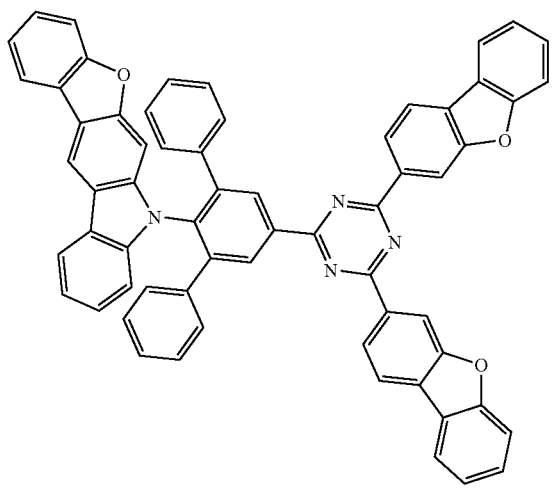
332
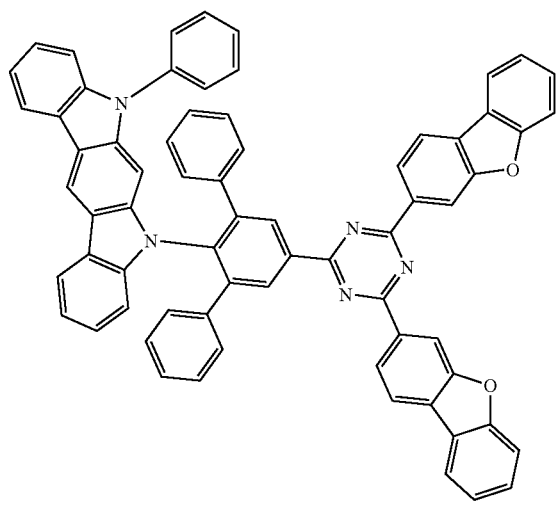

333
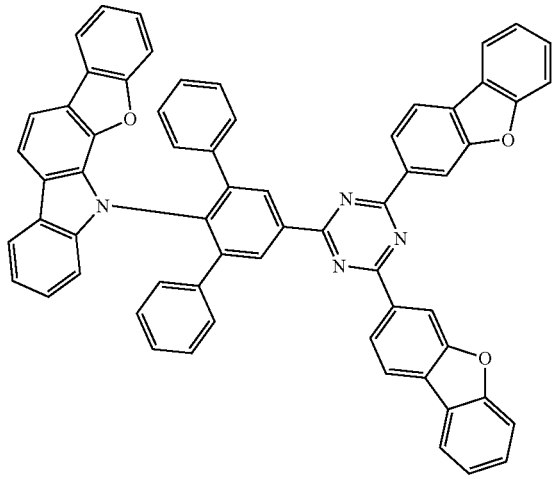
334
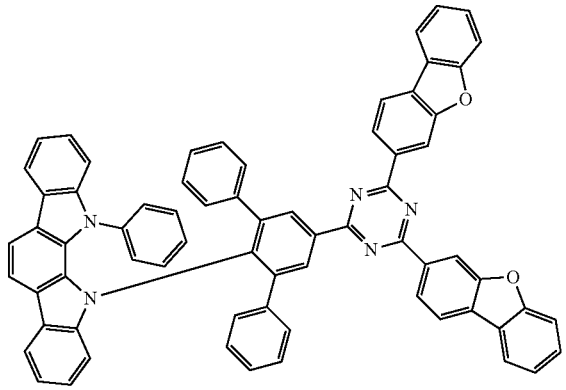
335
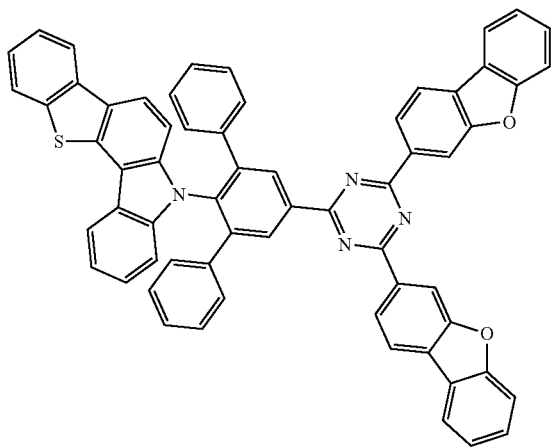
336
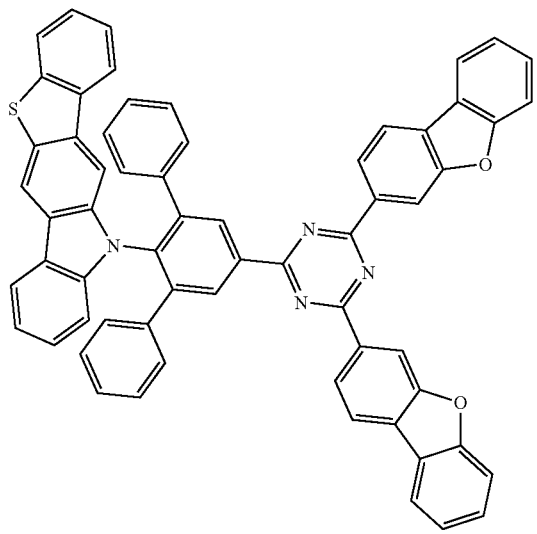
337
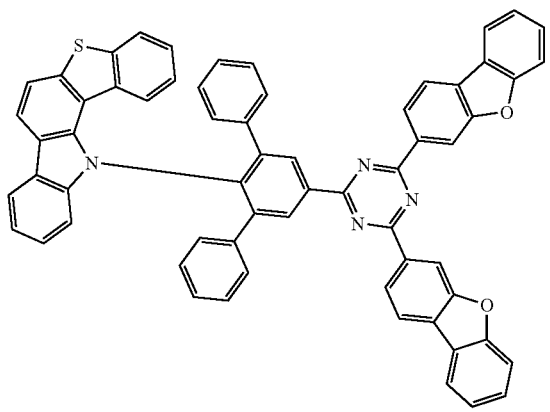
338
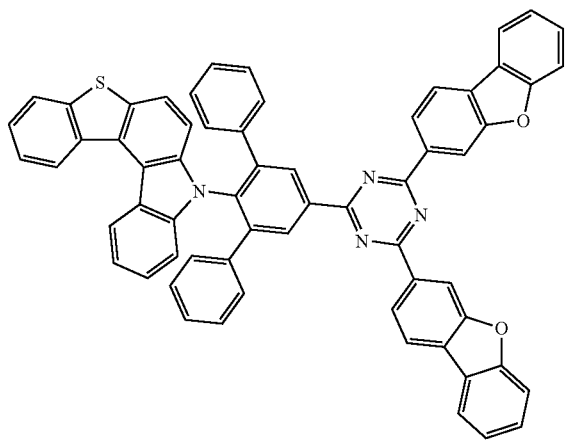

-continued
339
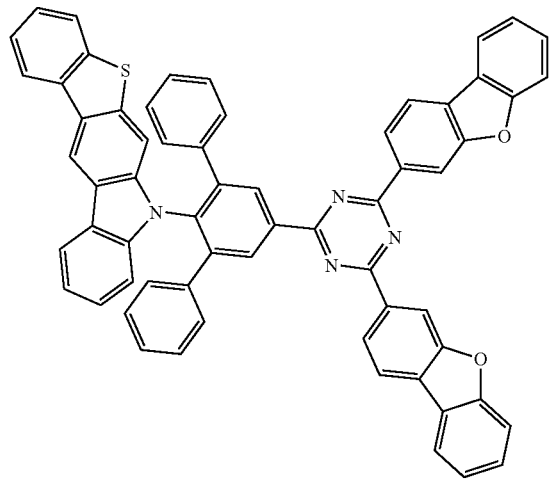
340
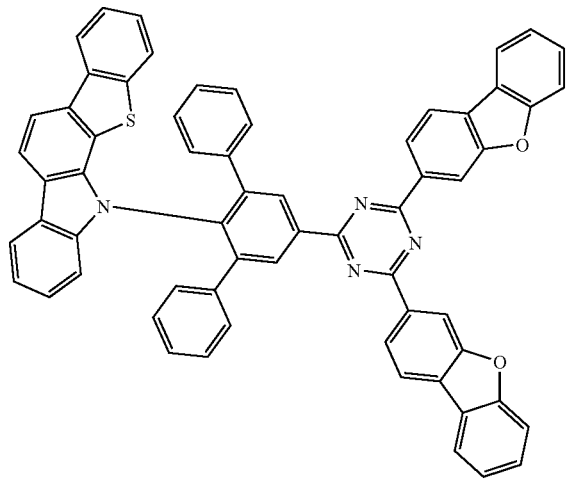
341
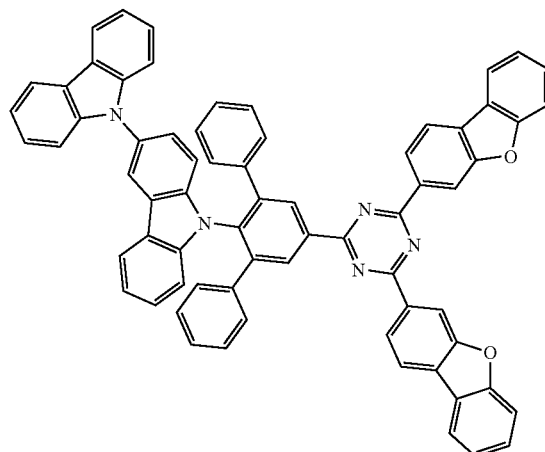
342
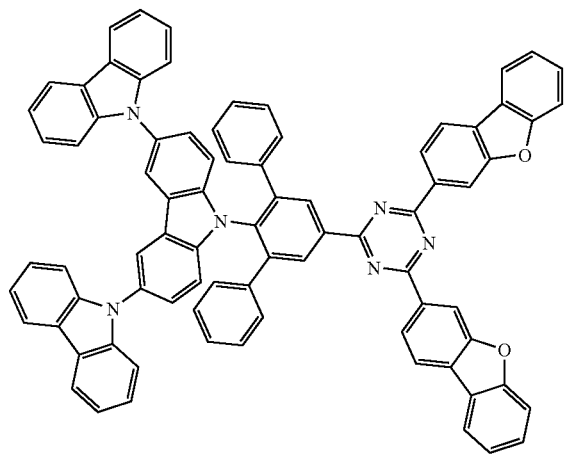
343
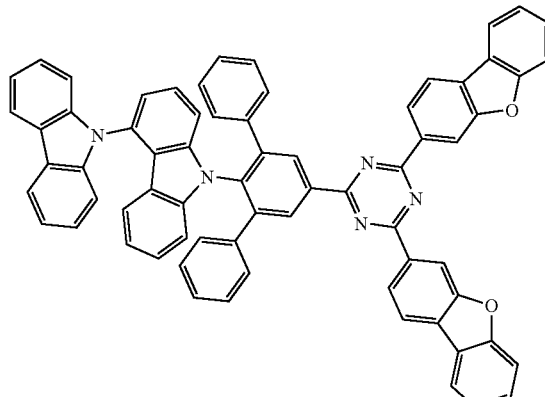
344
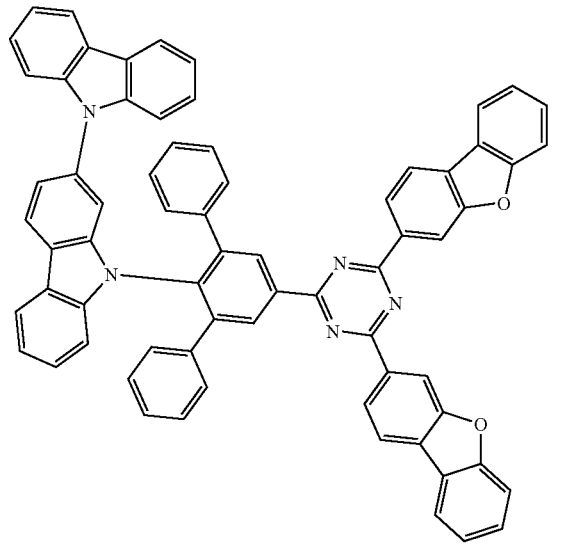

345
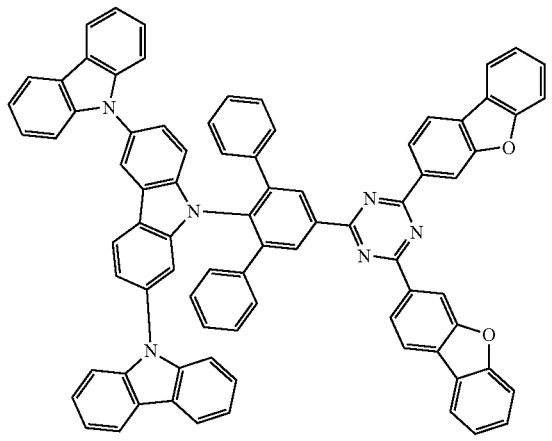
346
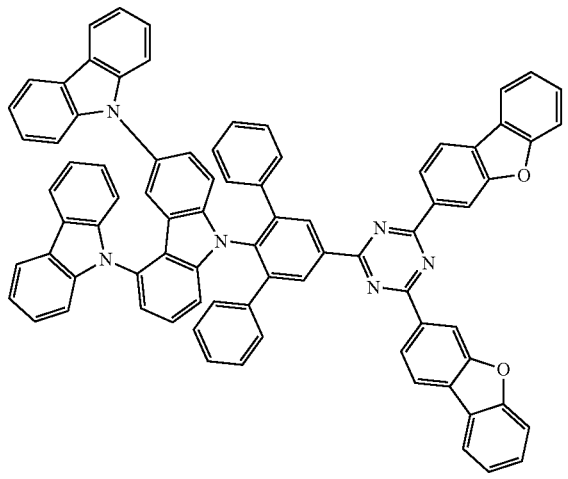
347
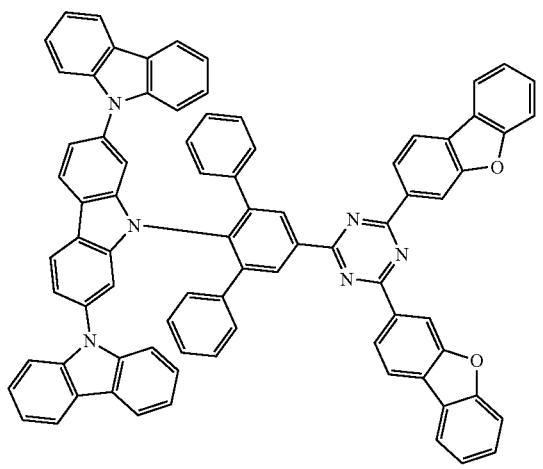
348
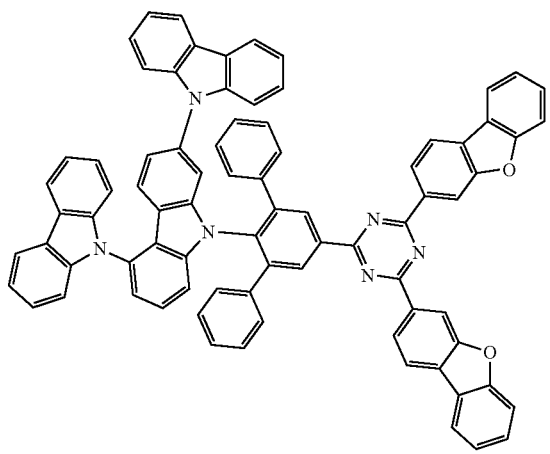
349
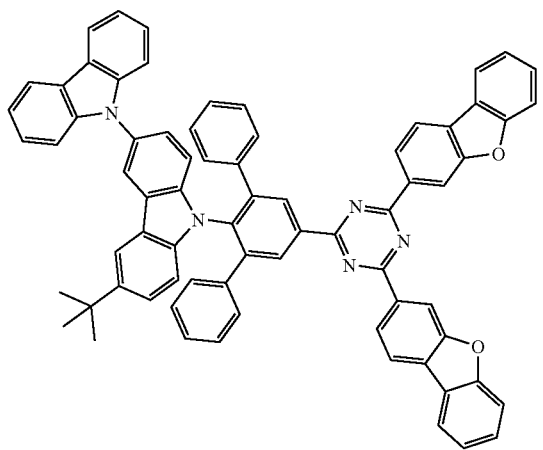
350
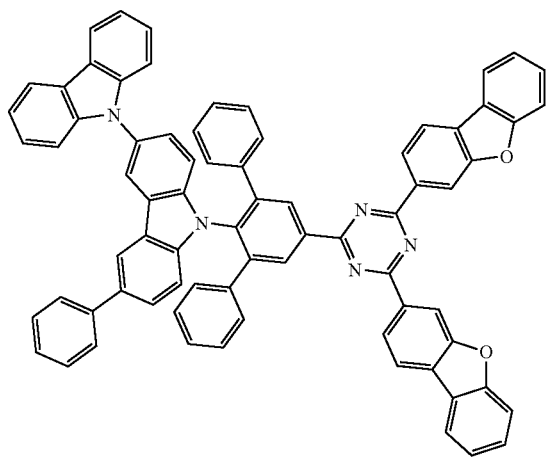

|351|352|
|---|---|
| 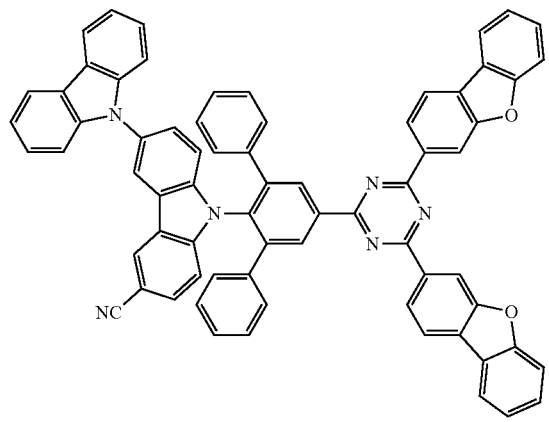 | 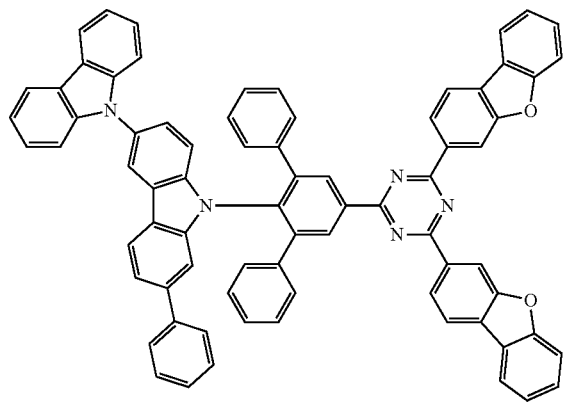 |
|353|354|
| 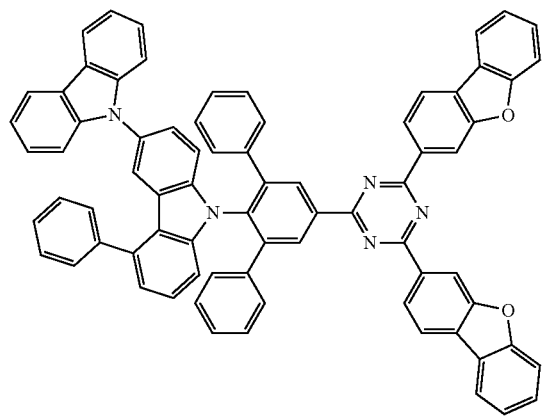 | 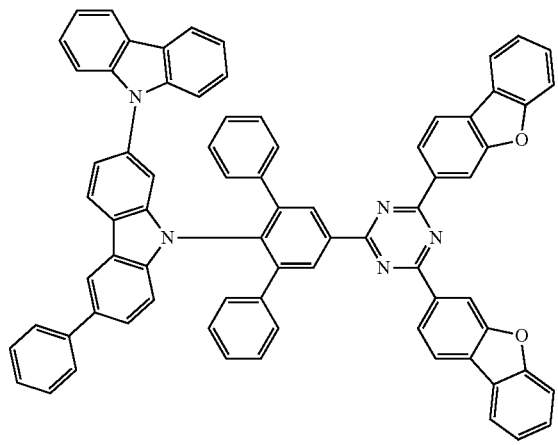 |
|355|356|
| 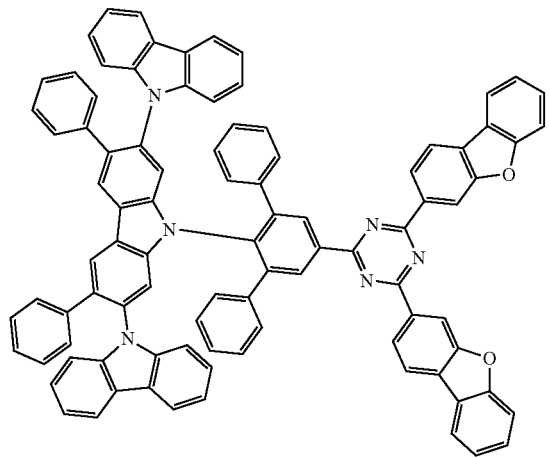 | 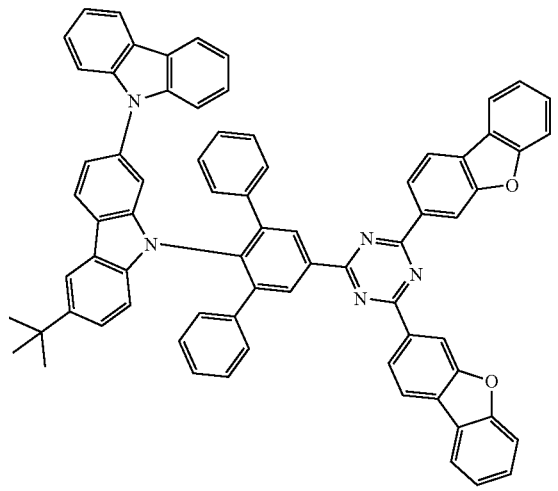 |

2993 2994
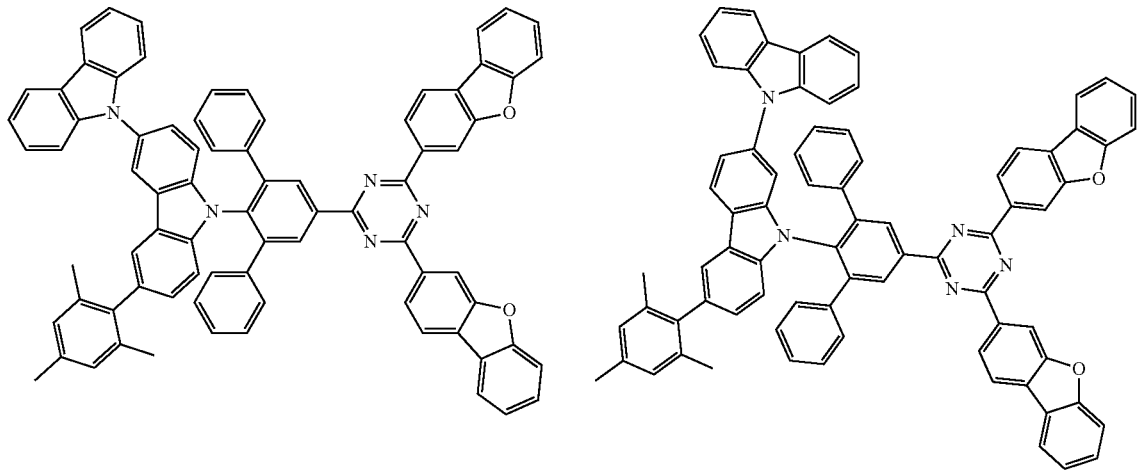
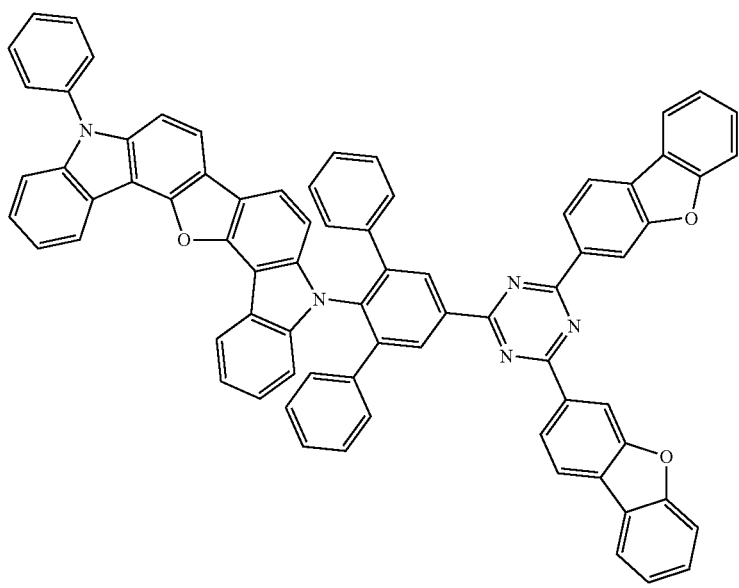
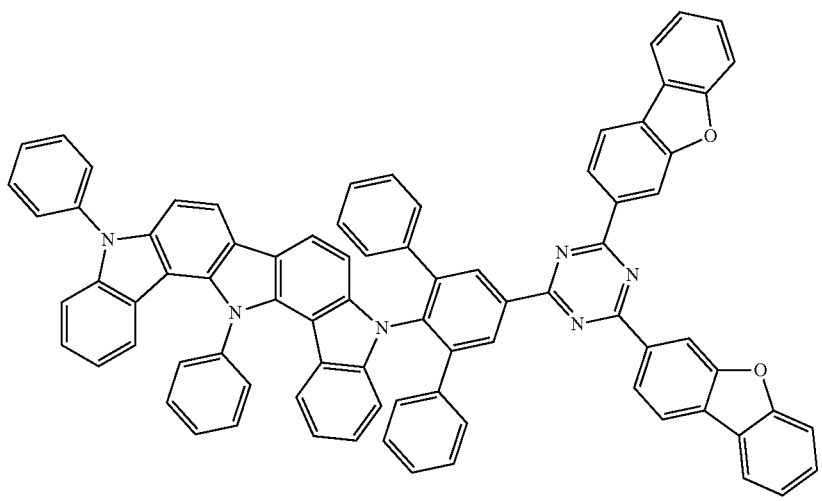

361
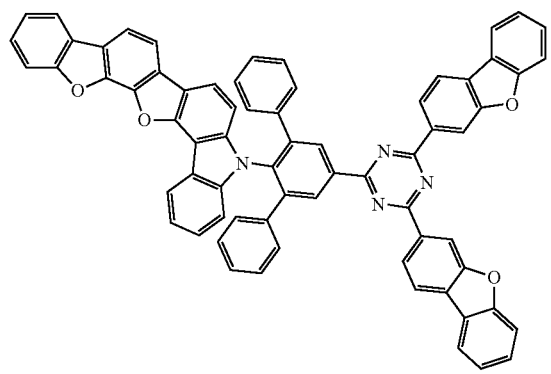
362
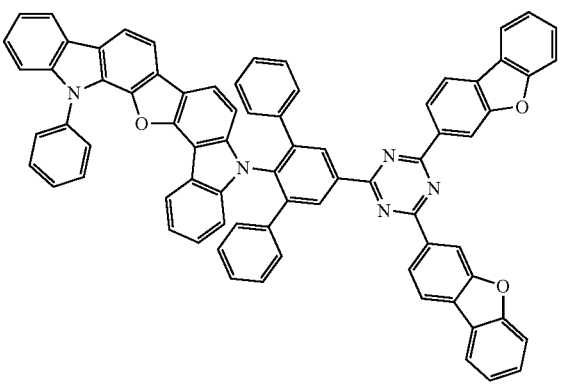
363
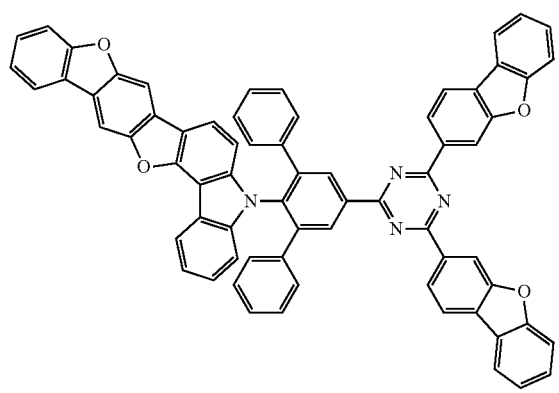
364
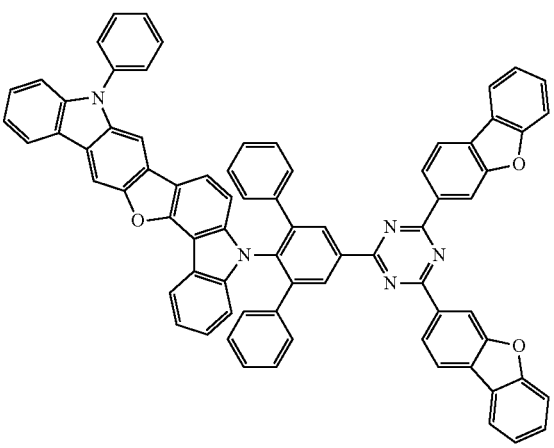
365
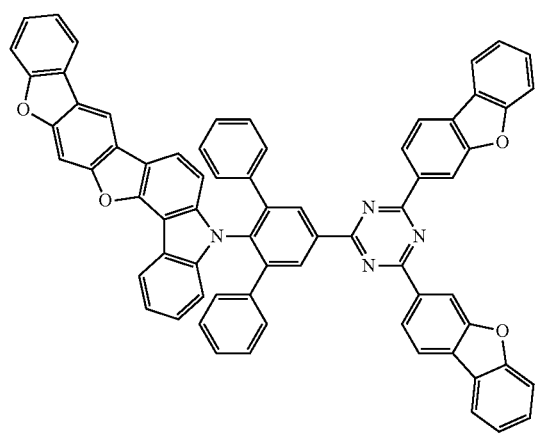
366
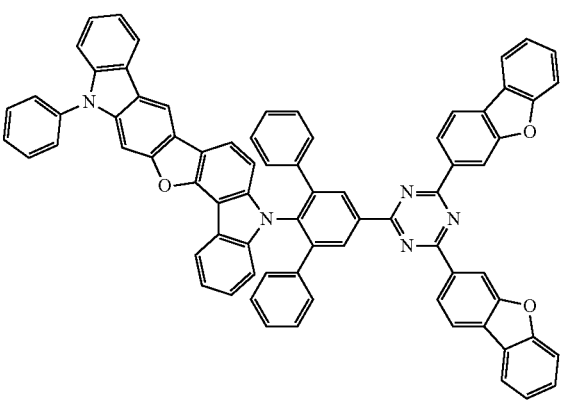

-continued
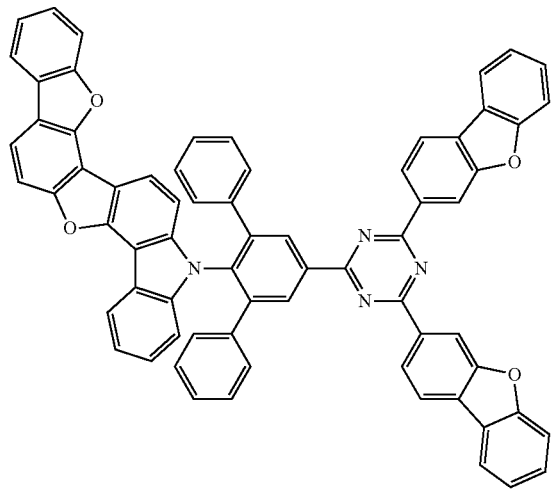
367
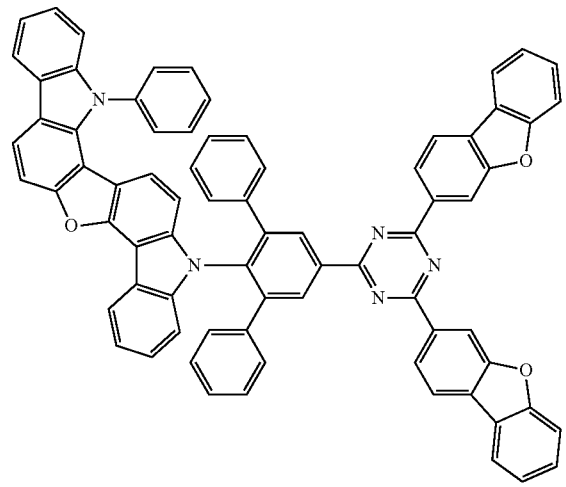
368
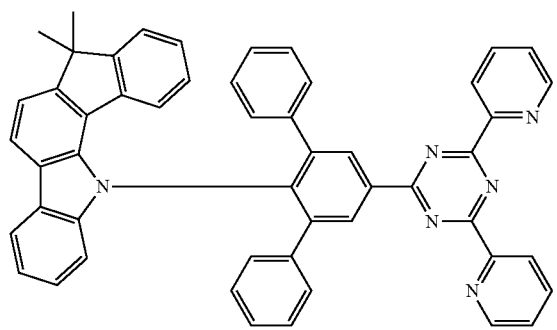
369
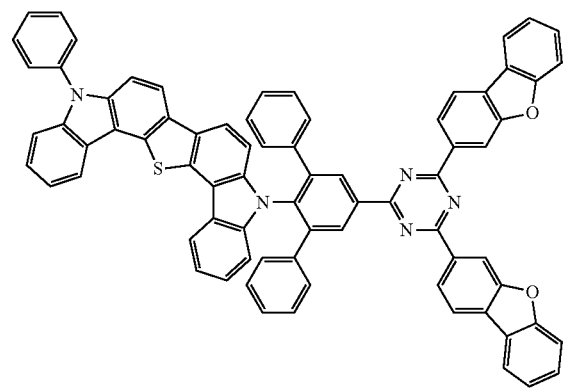
370
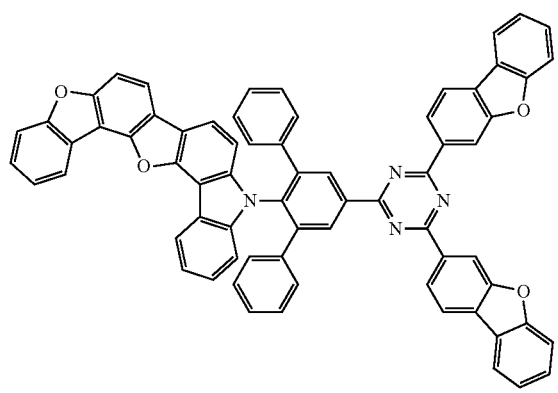
371
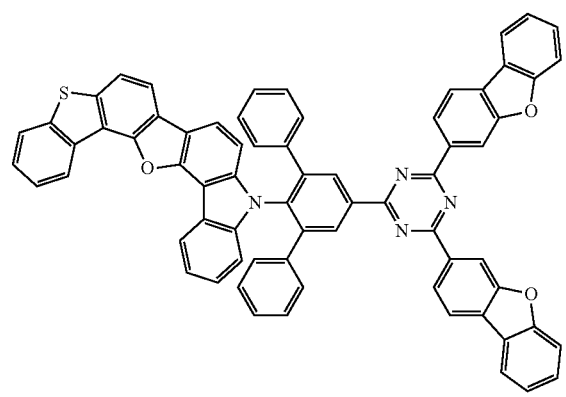
372

373
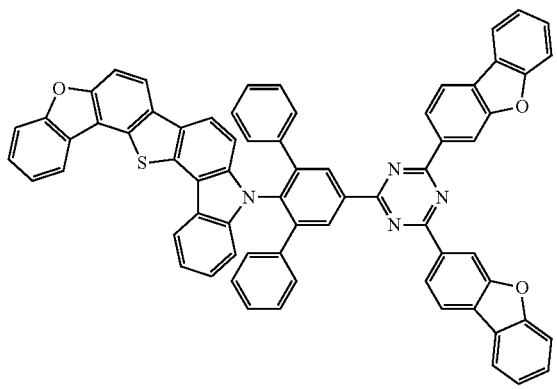
374
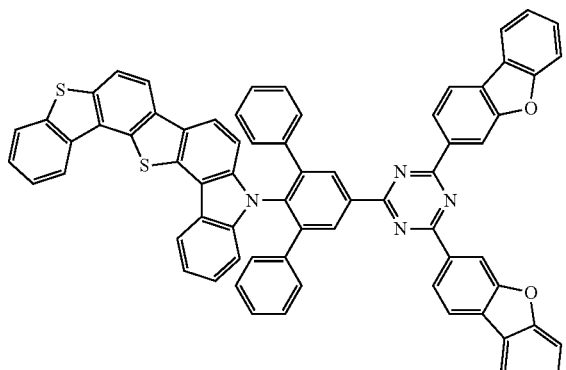
375
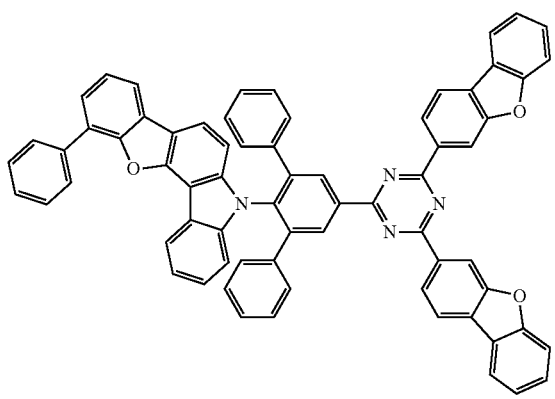
376
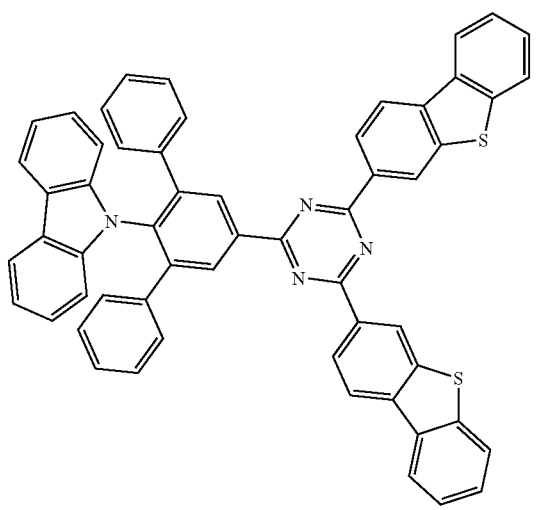
377
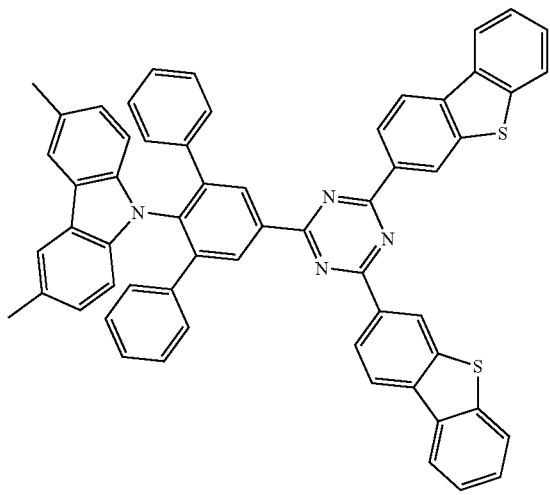
378
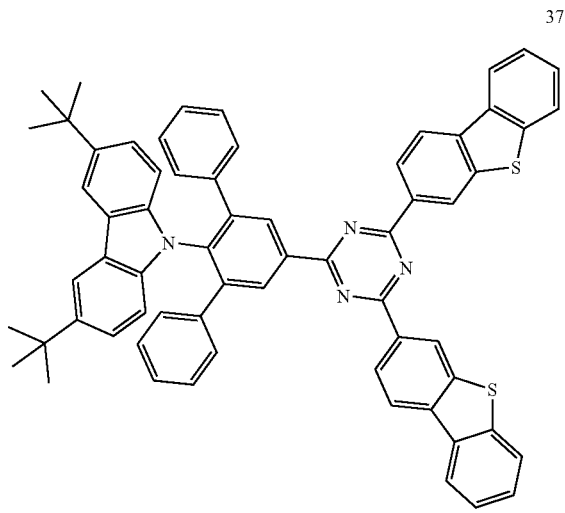

-continued
379
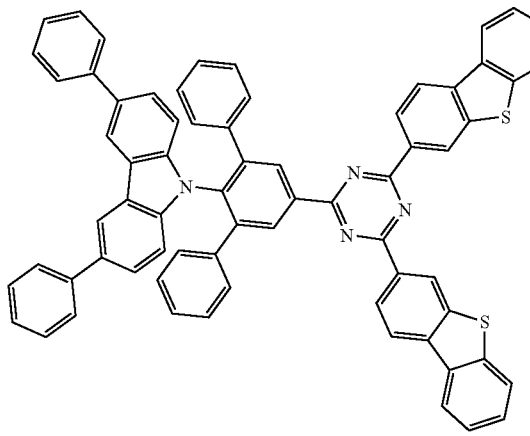
380
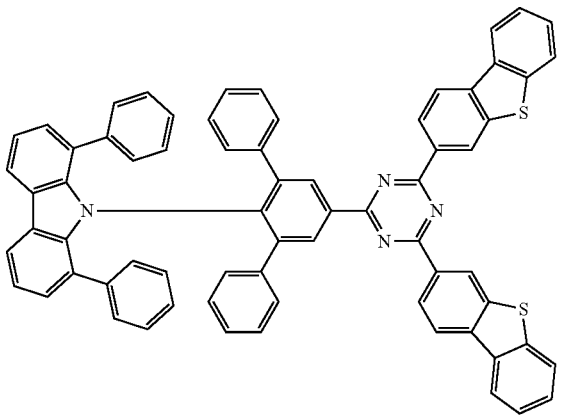
381
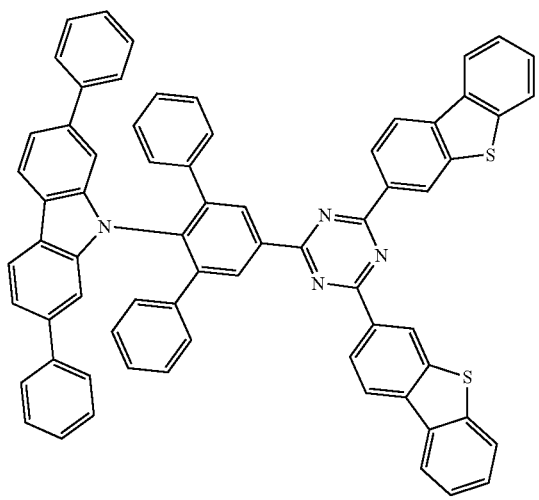
382
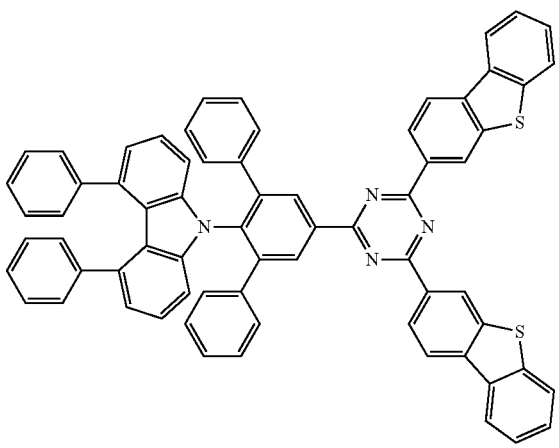
383
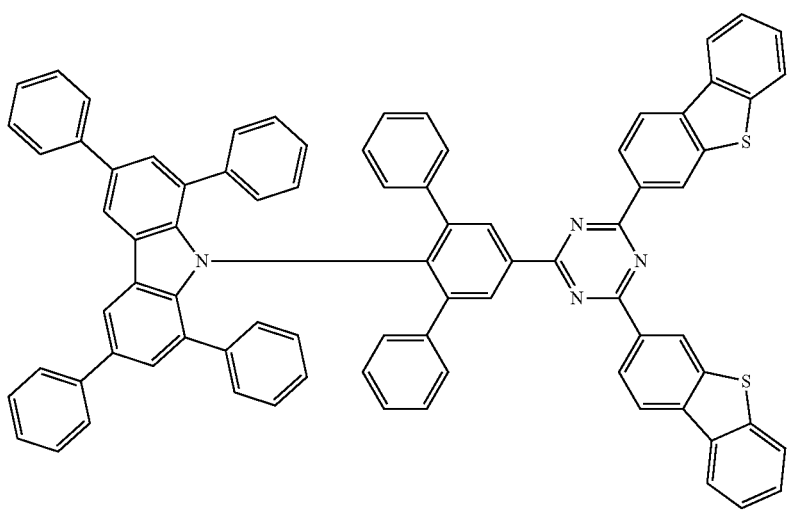

384
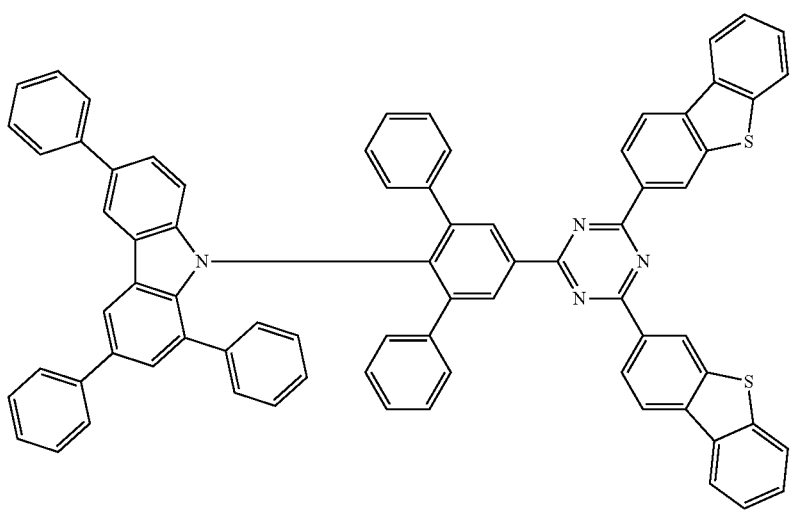
385
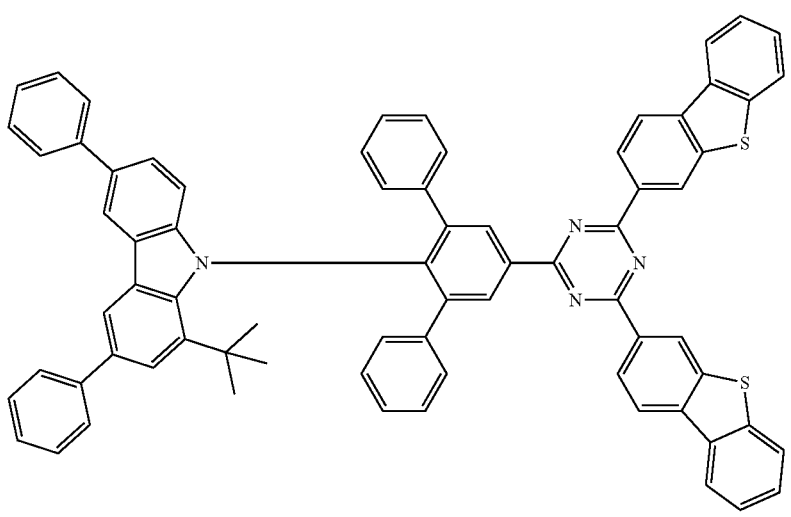
386
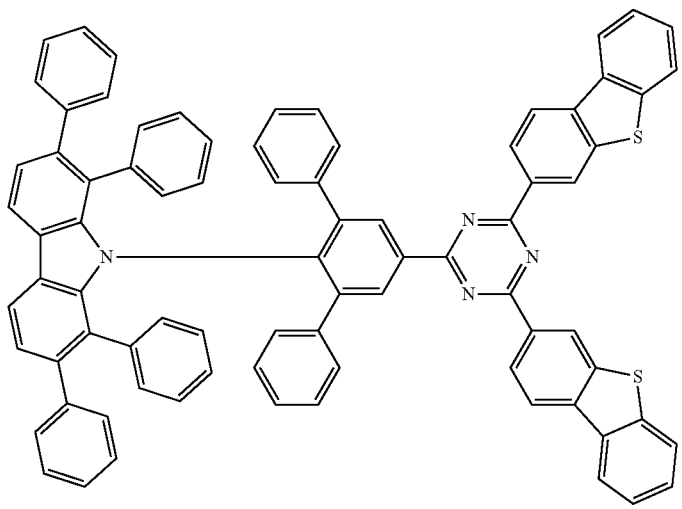

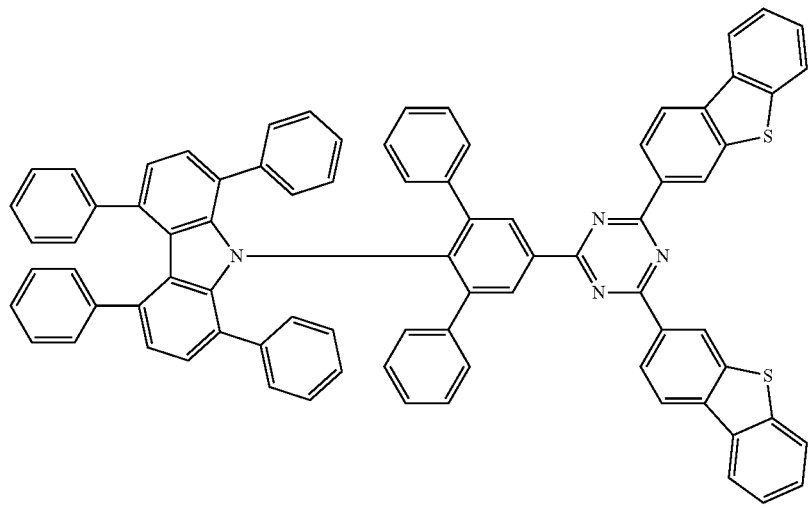
387
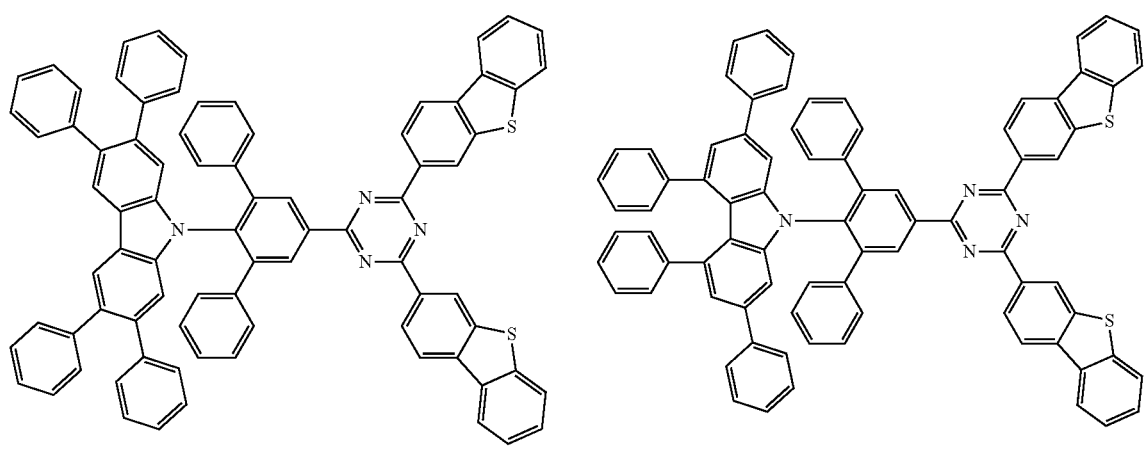
388 389
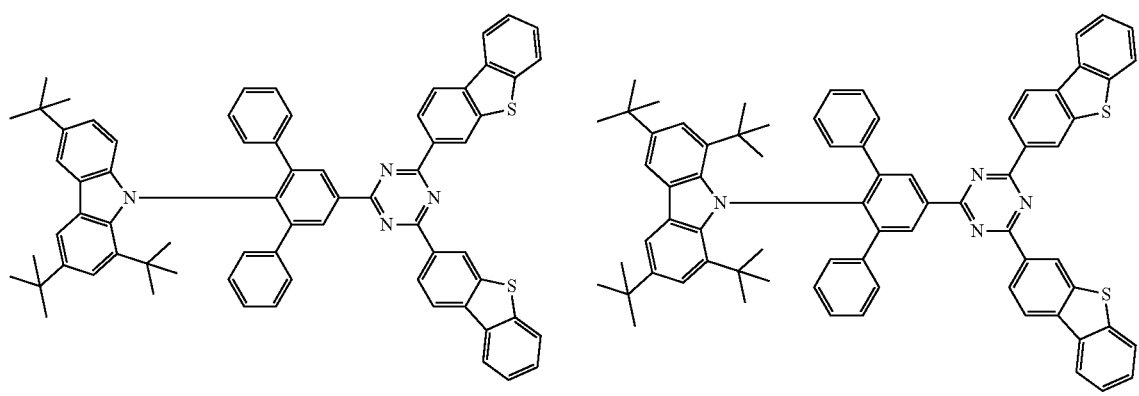
390 391

-continued
392
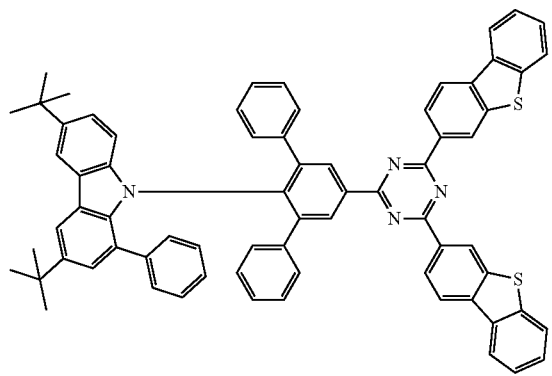
393
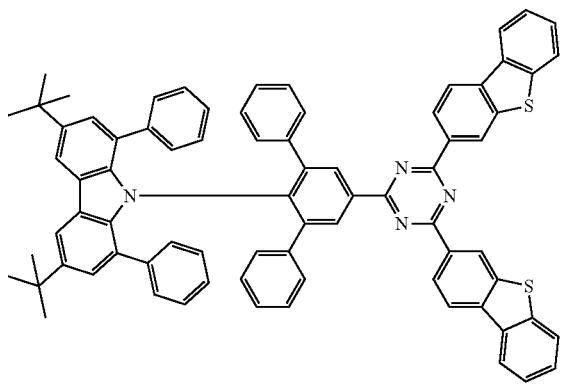
394
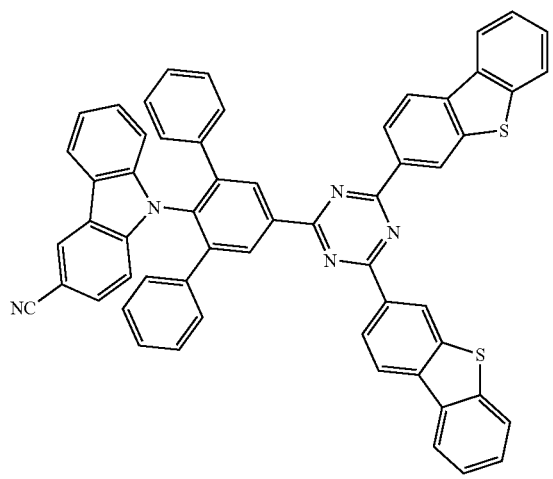
395
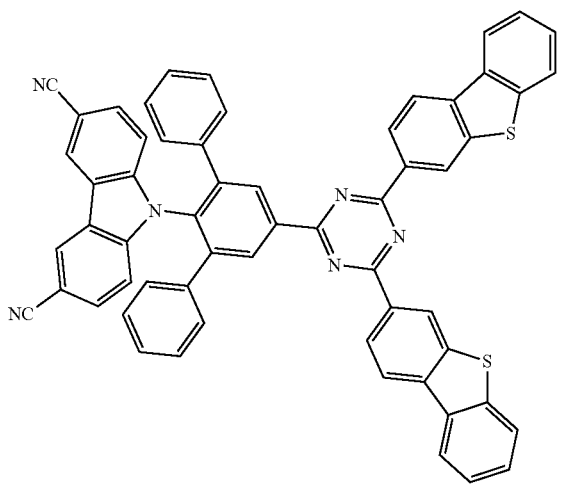
396
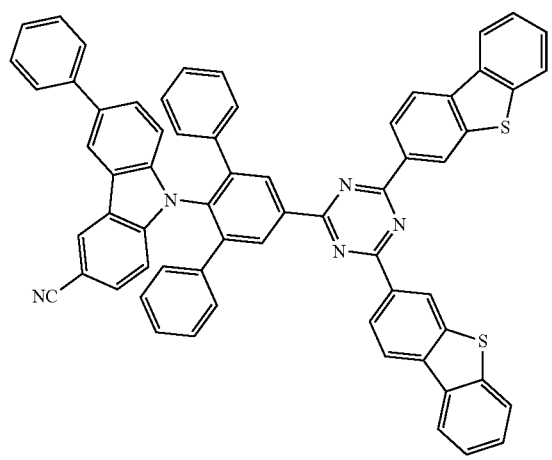
397
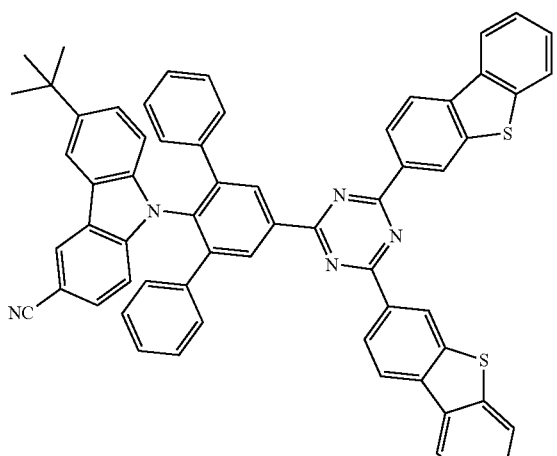

-continued
398
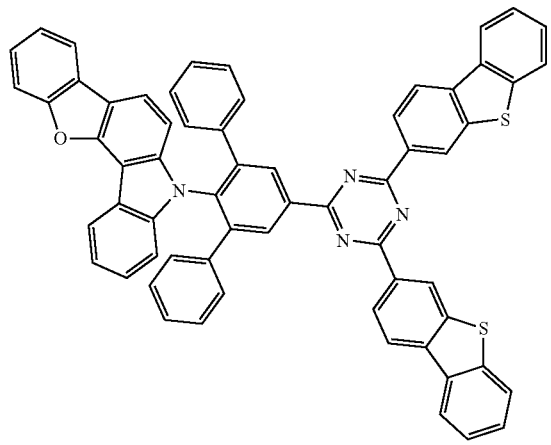
399
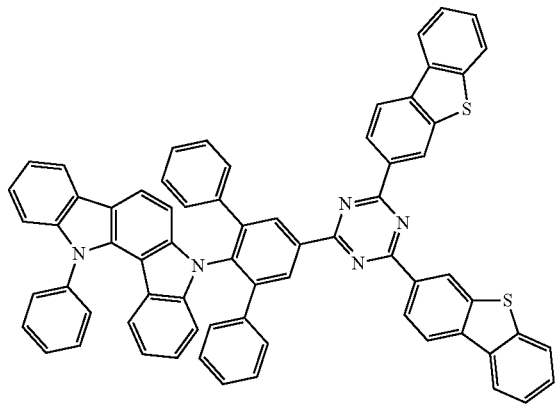
400
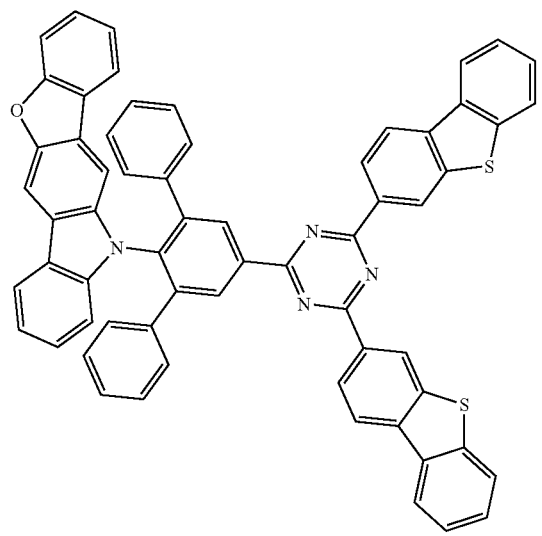
401
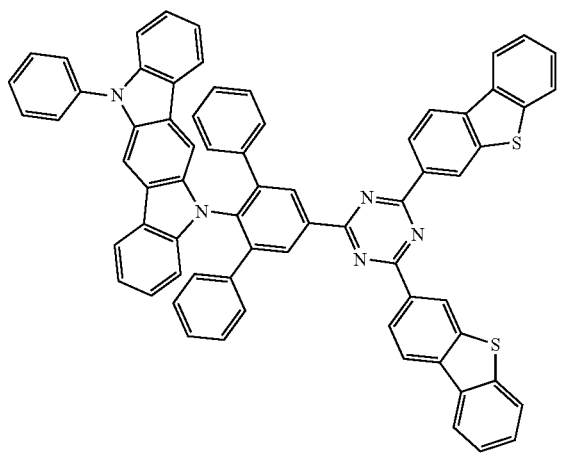
402
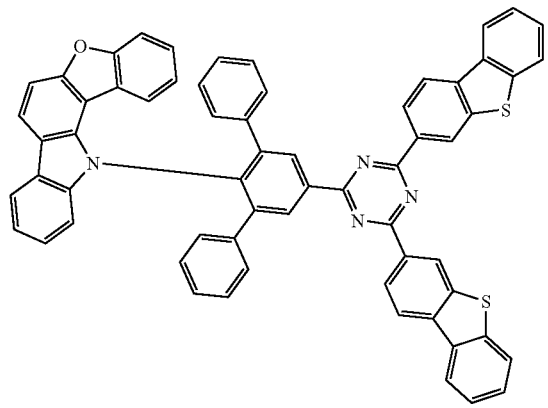
403
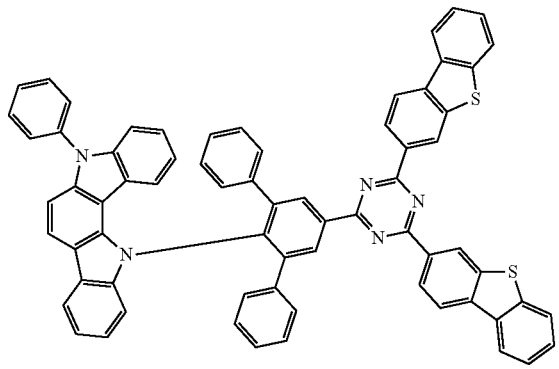

-continued
3011
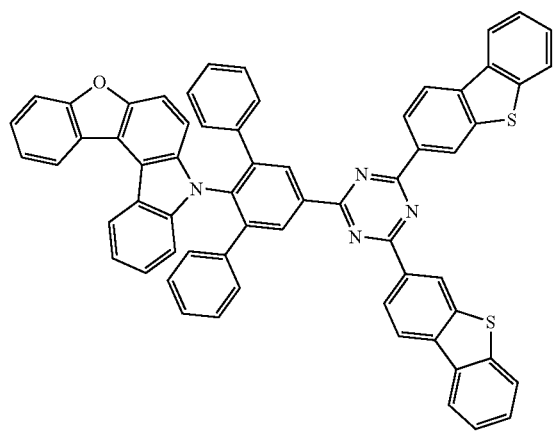
404
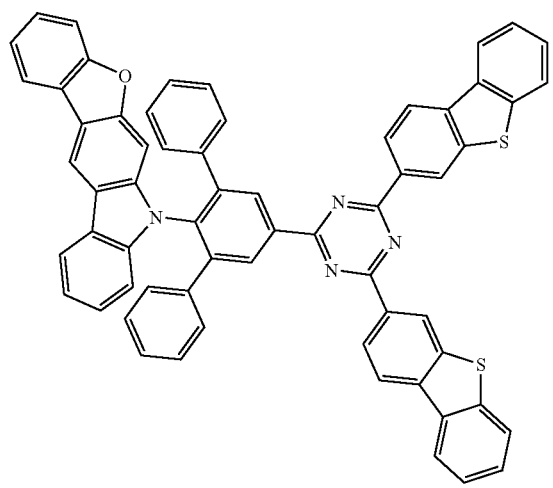
406
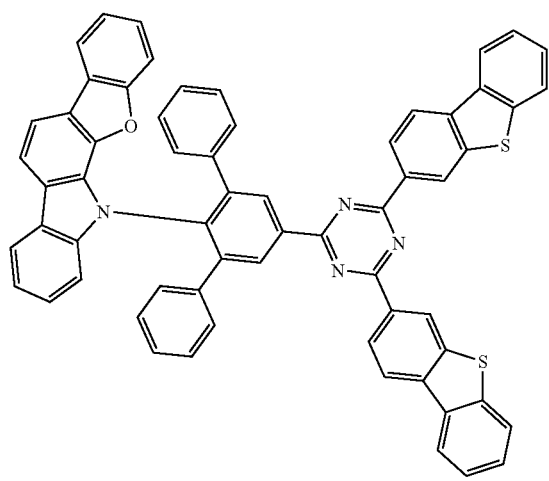
408
3012
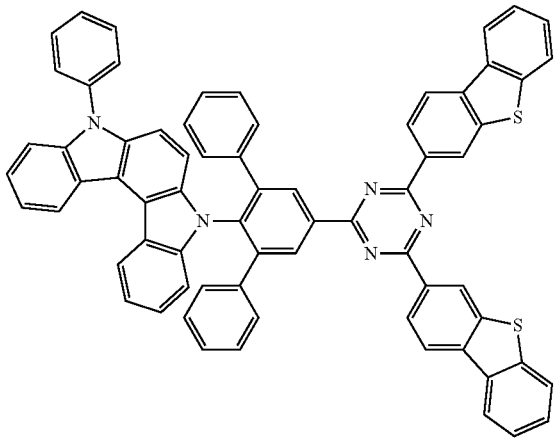
405
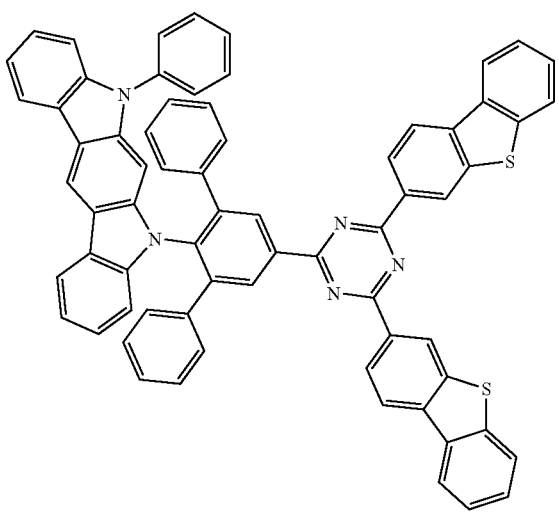
407
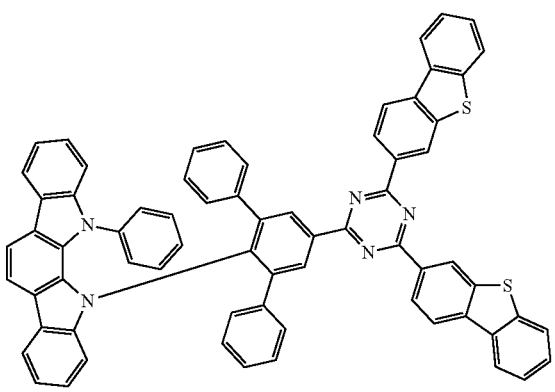
409

-continued
410
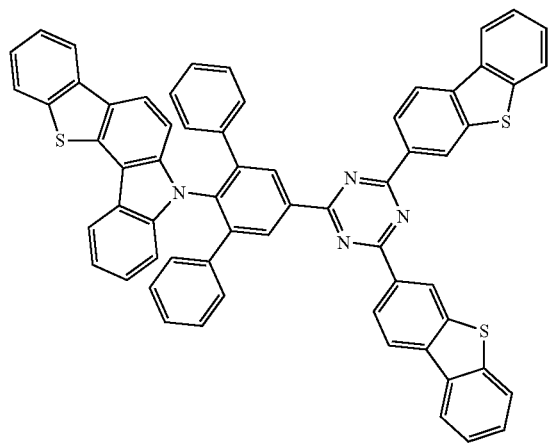
411
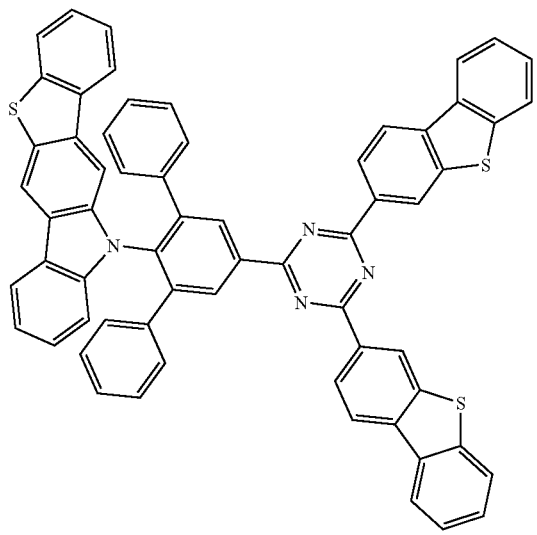
412
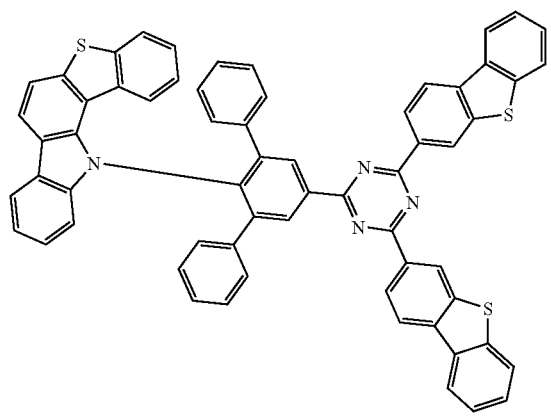
413
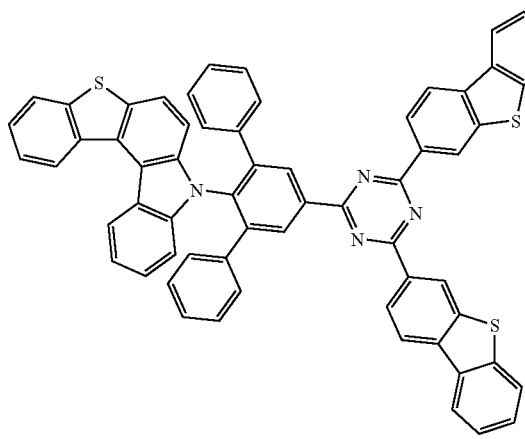
414
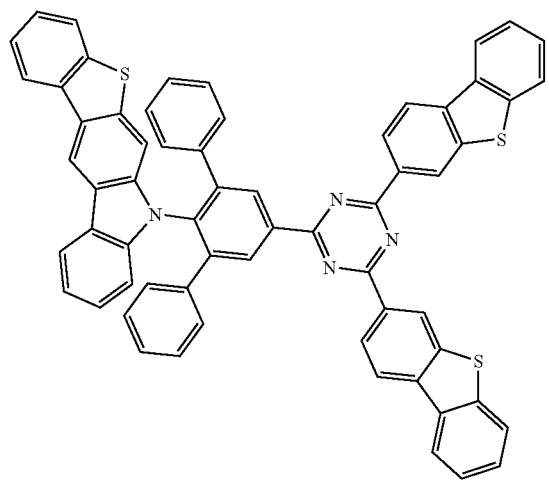
415
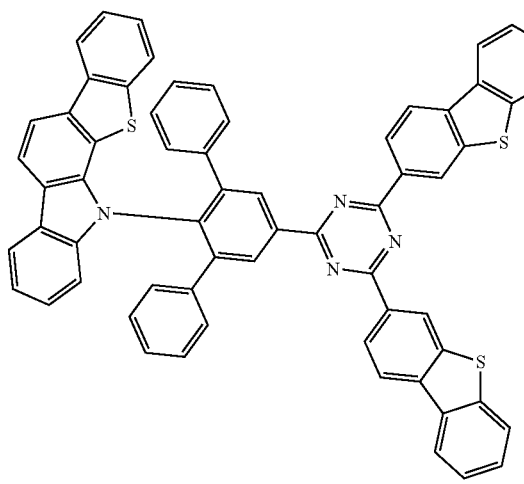

-continued
416
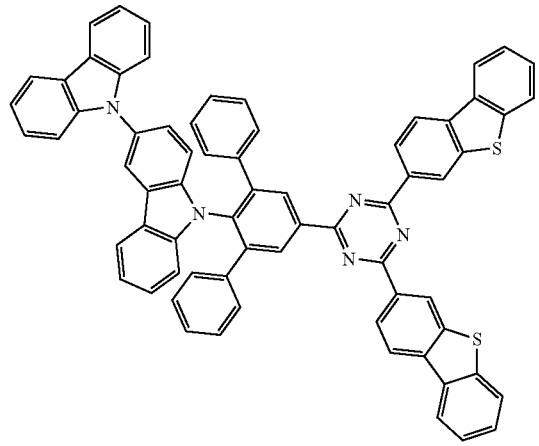
417
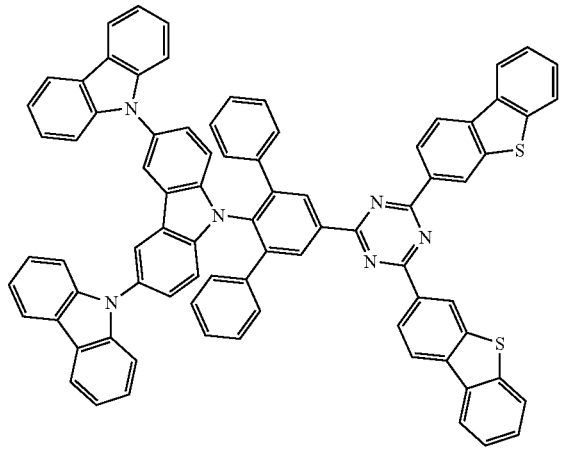
418
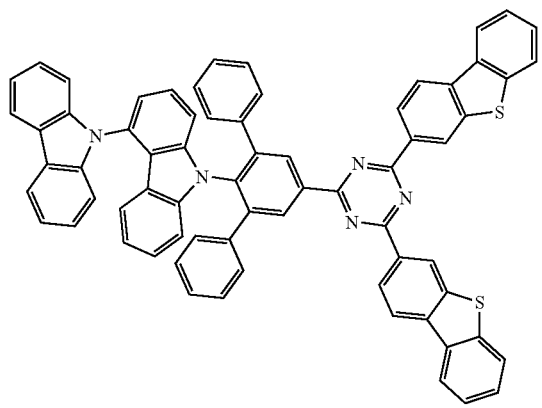
419
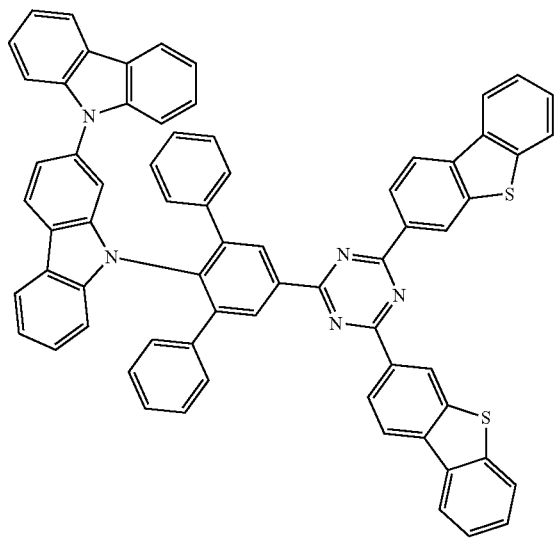
420
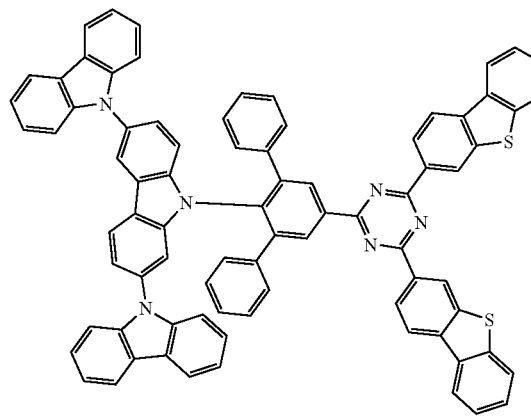
421
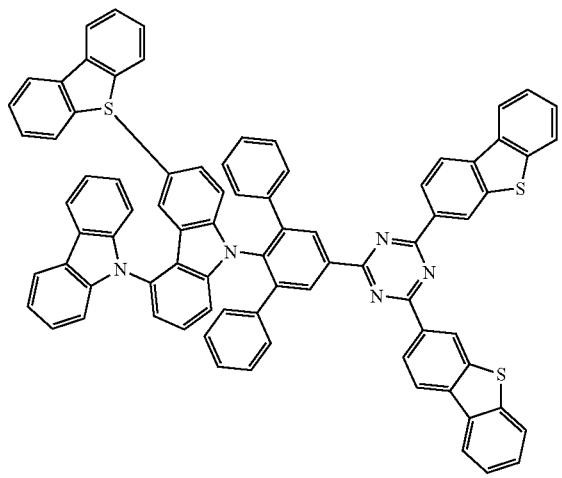

422
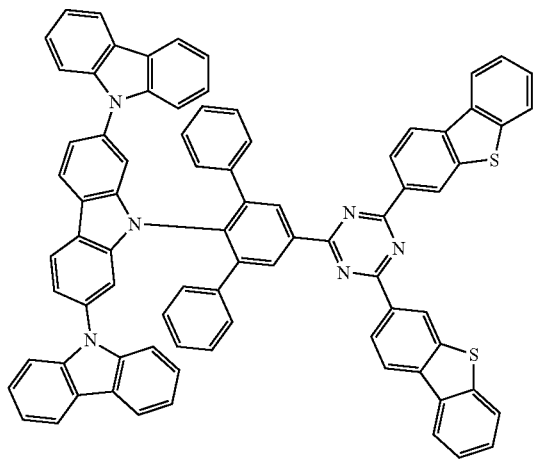
423
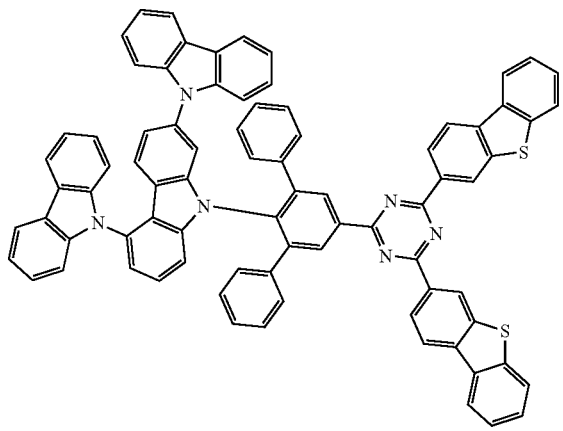
424
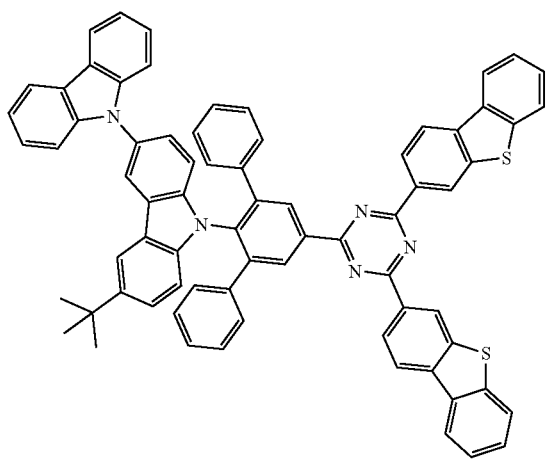
425
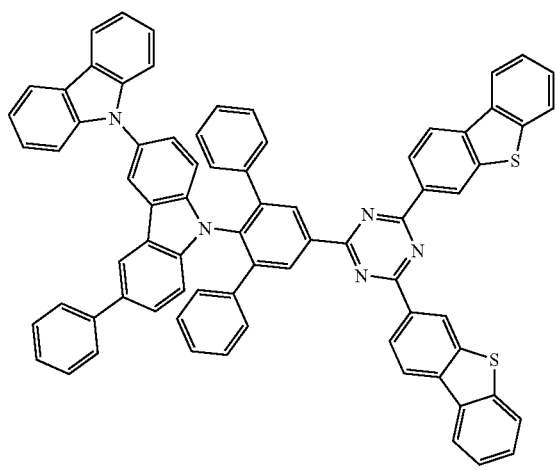
426
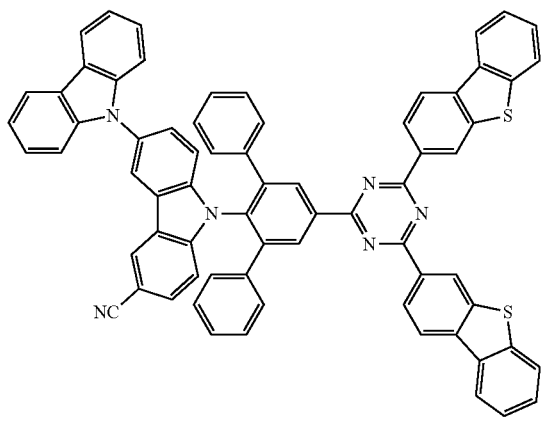
427
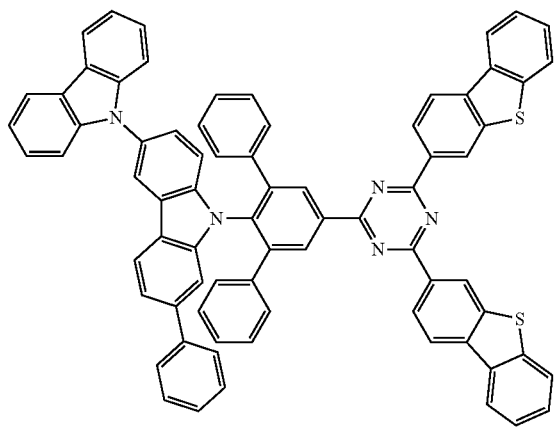

3019 3020
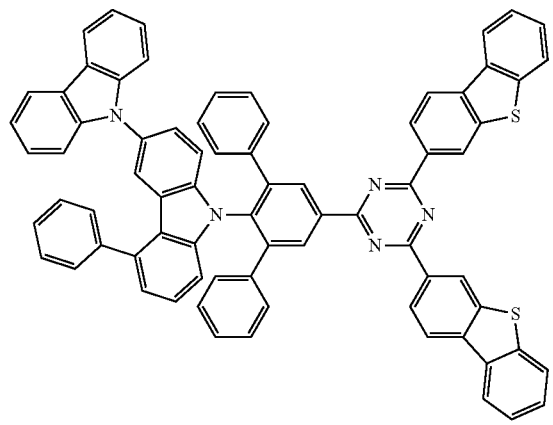
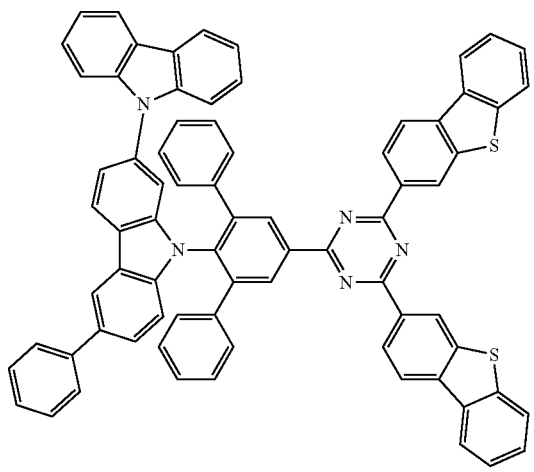
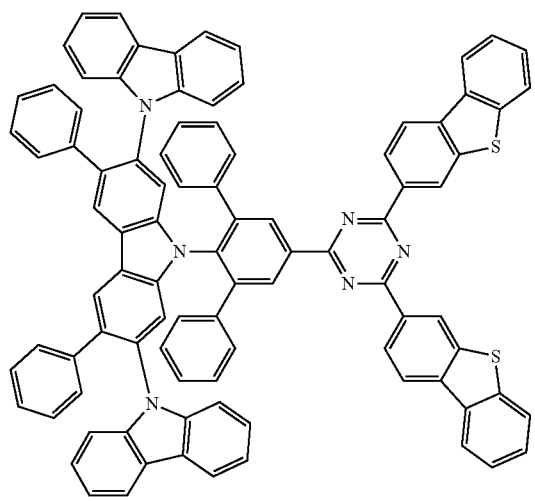
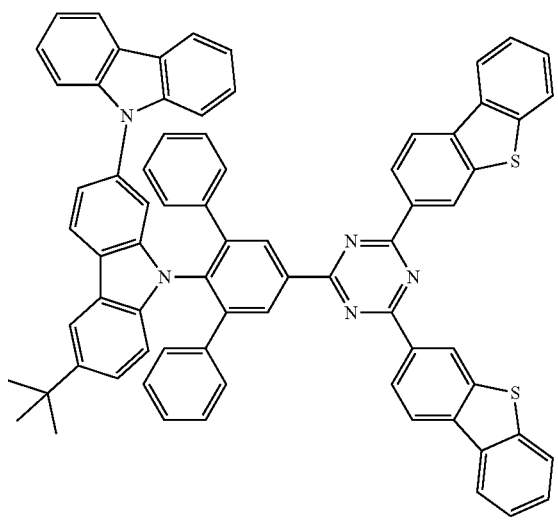
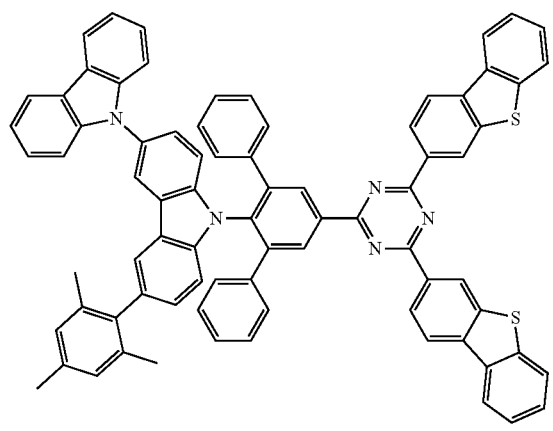
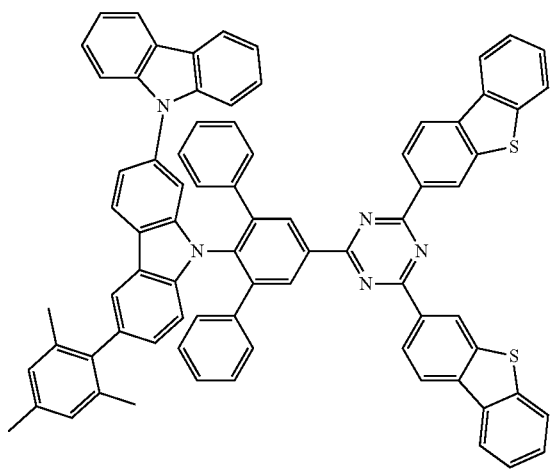

-continued
434
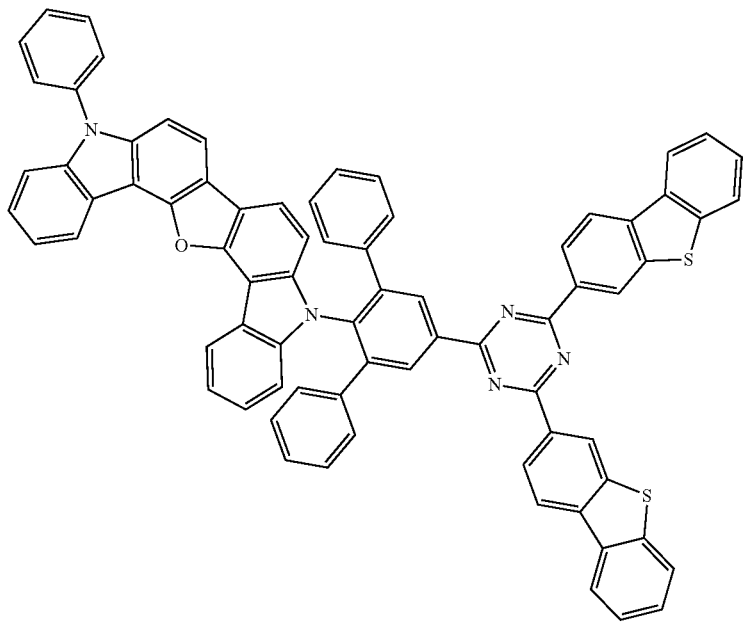
435
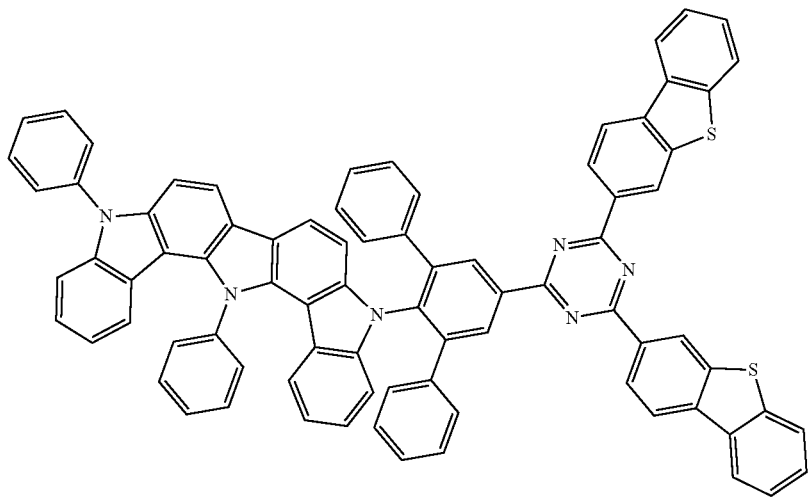
436
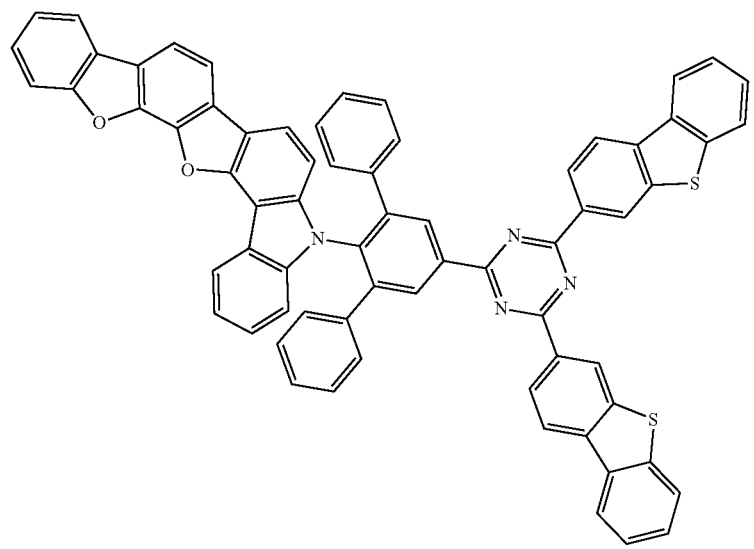

437
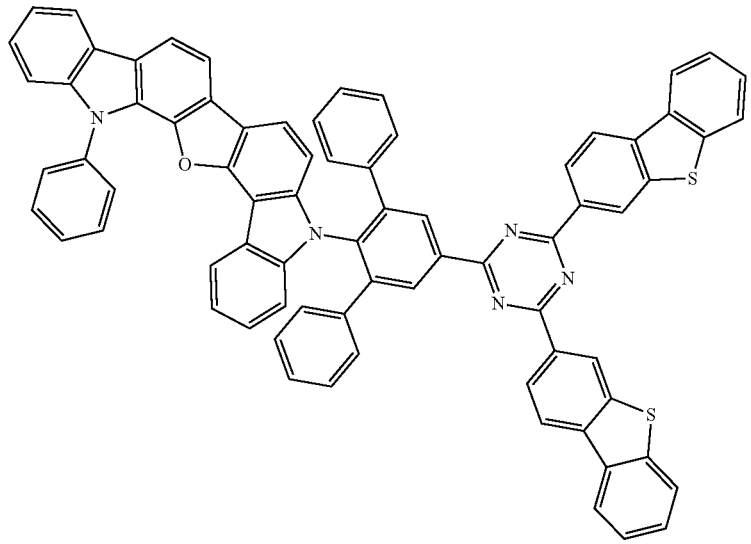
438
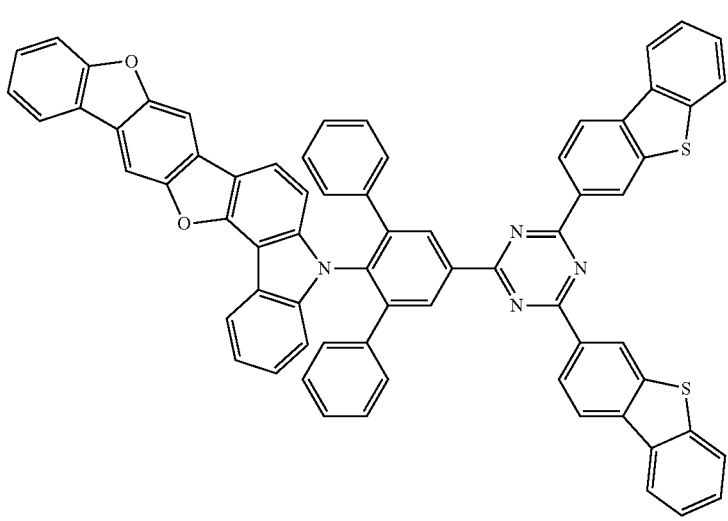
439
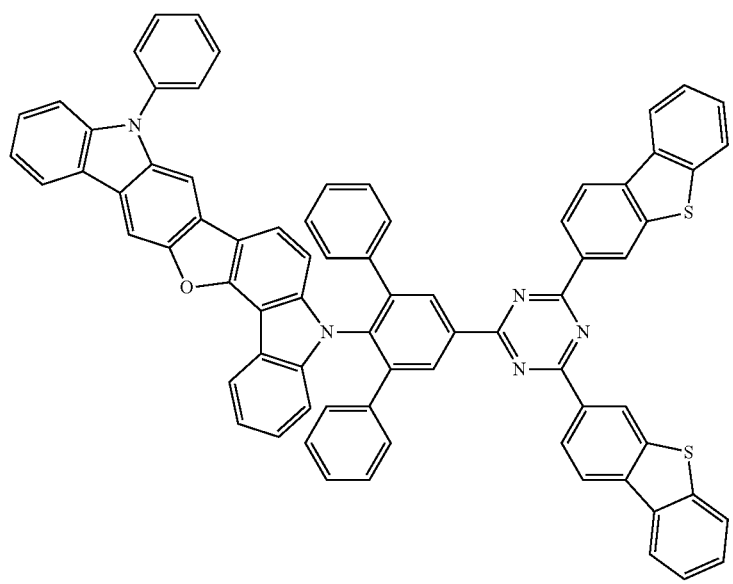

440
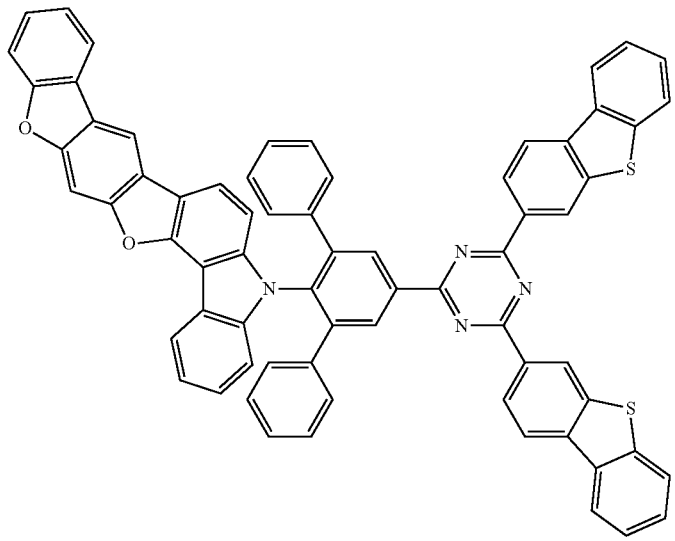
441
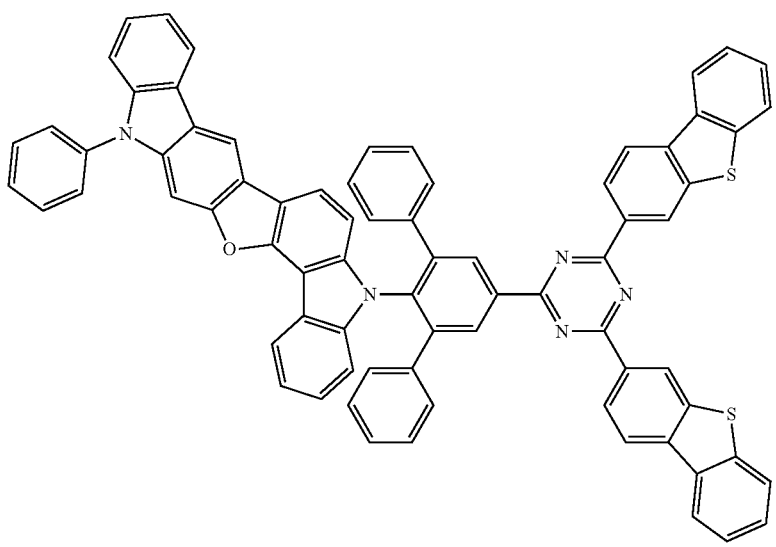
442 443
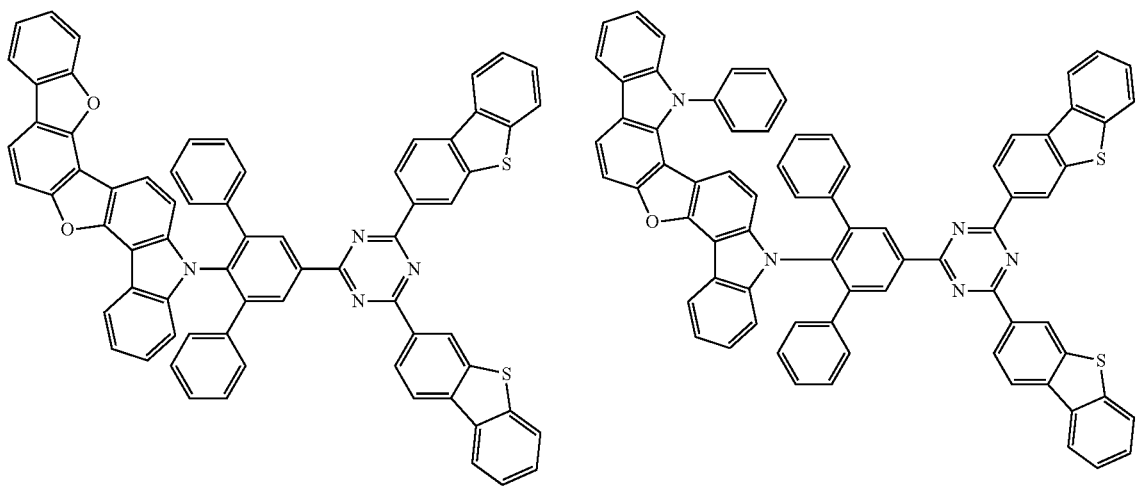

444
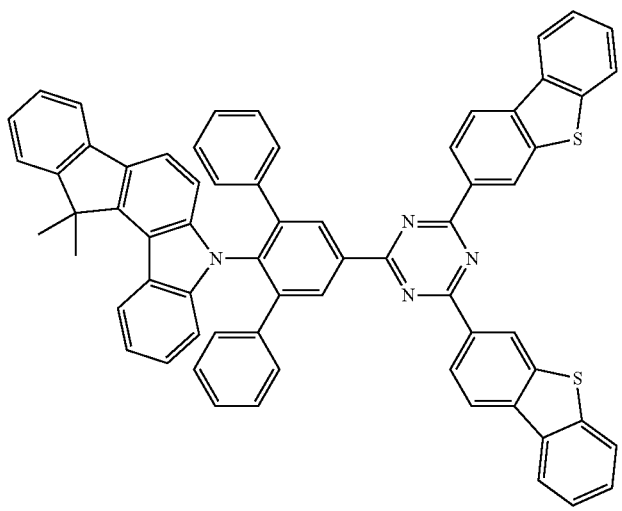
445
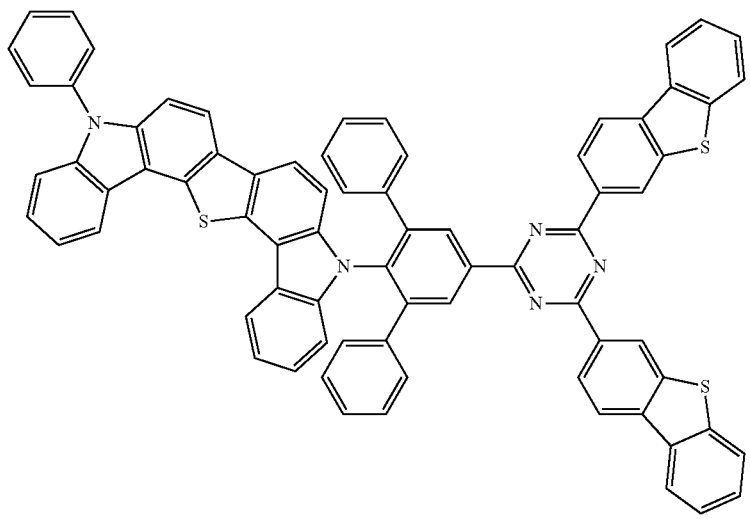
446
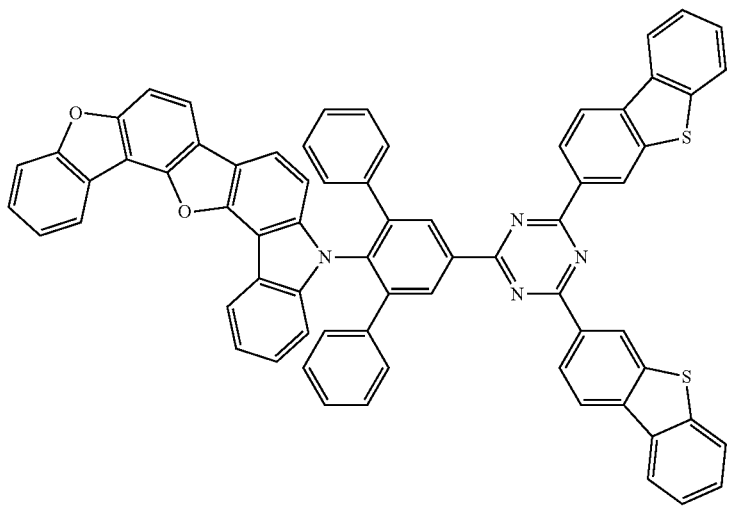

447
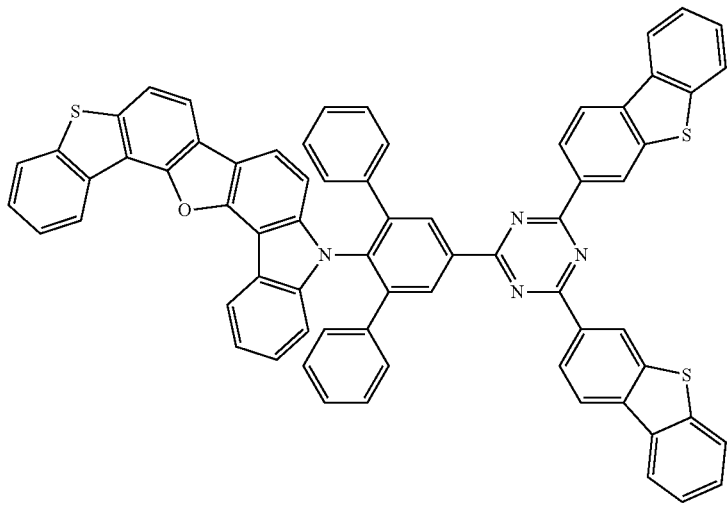
448
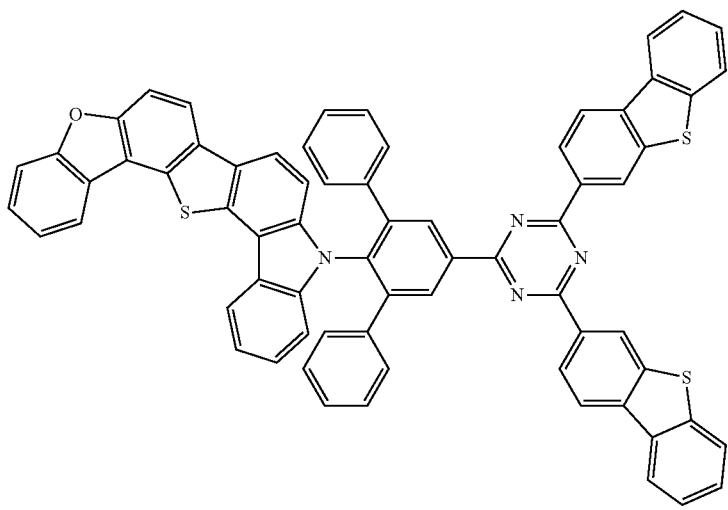
449
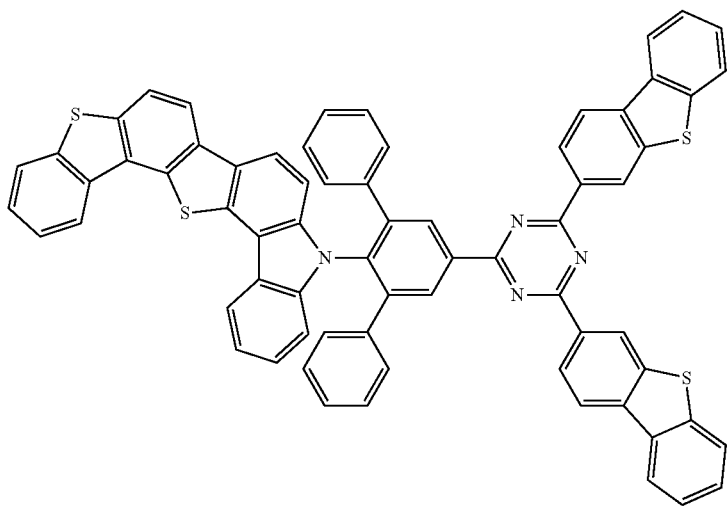

450
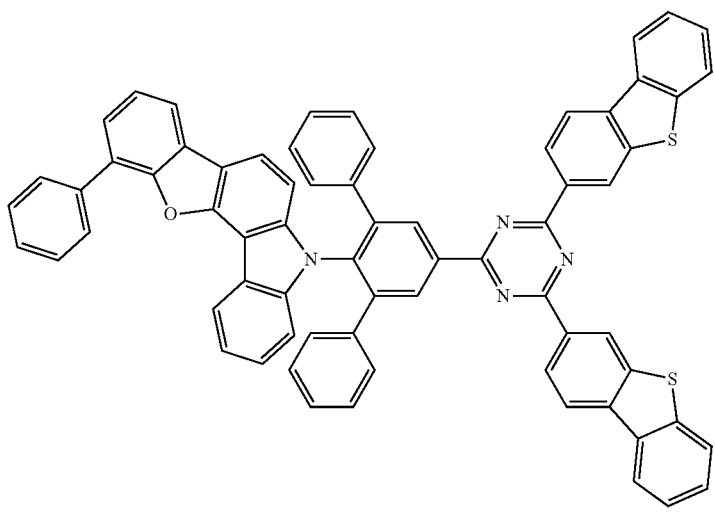
451
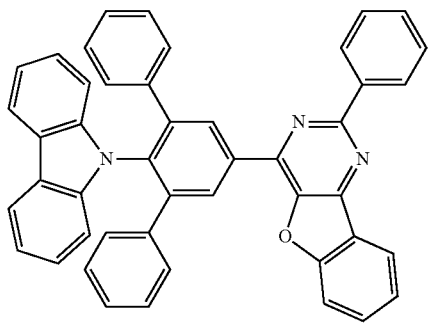
452
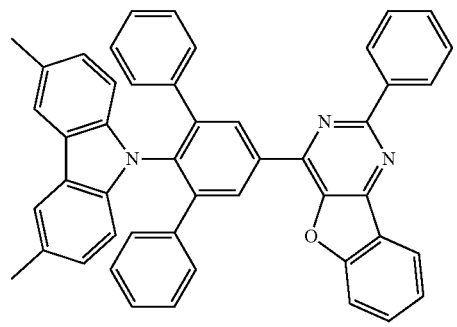
453
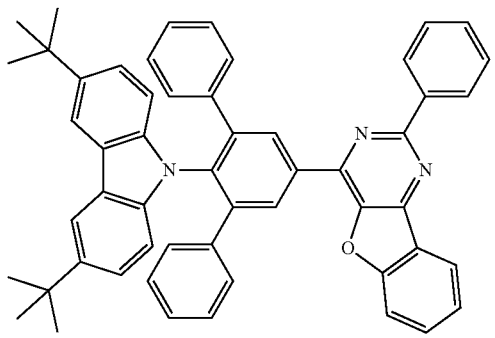
454
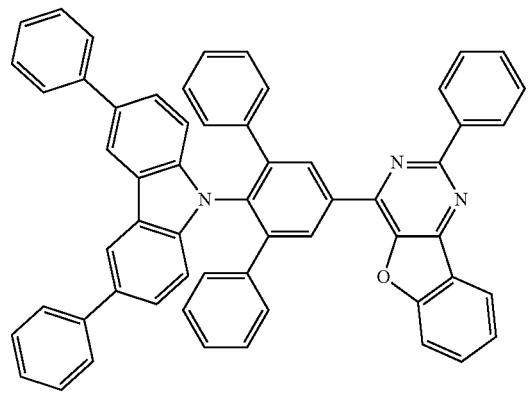

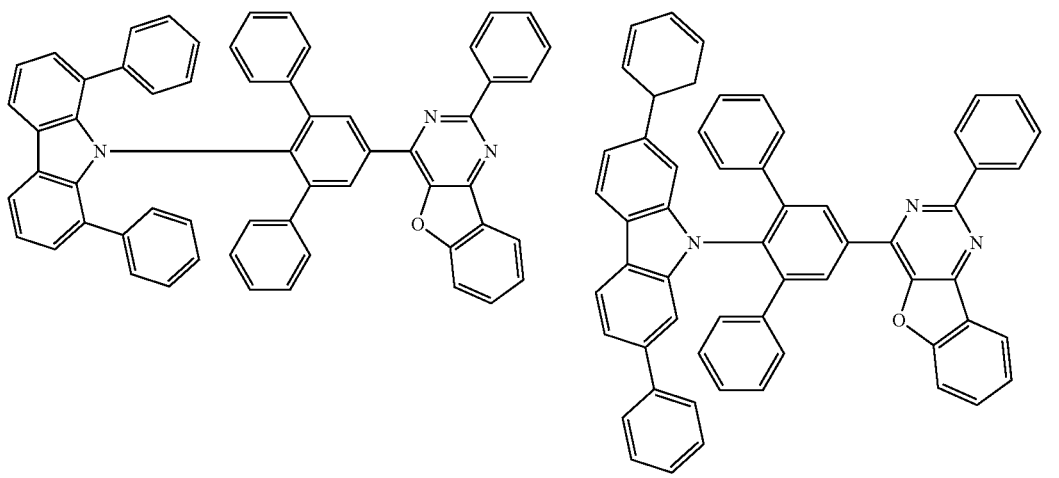
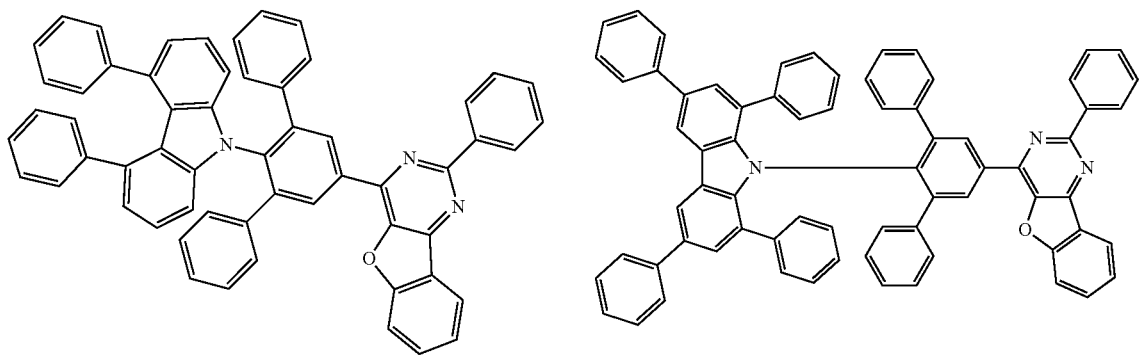
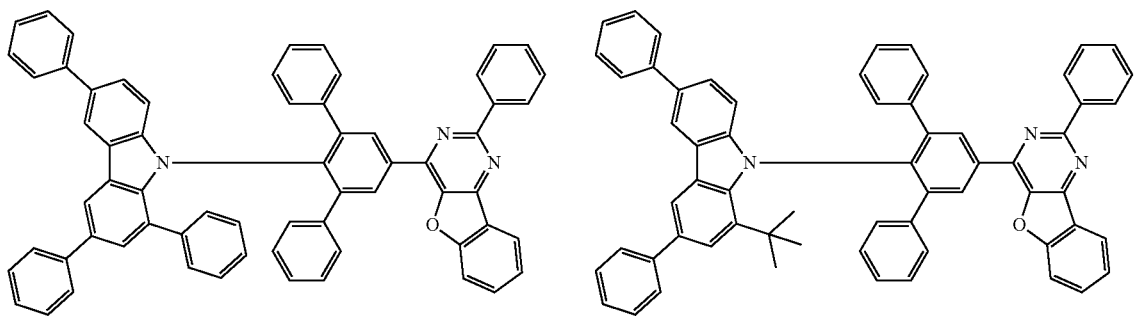
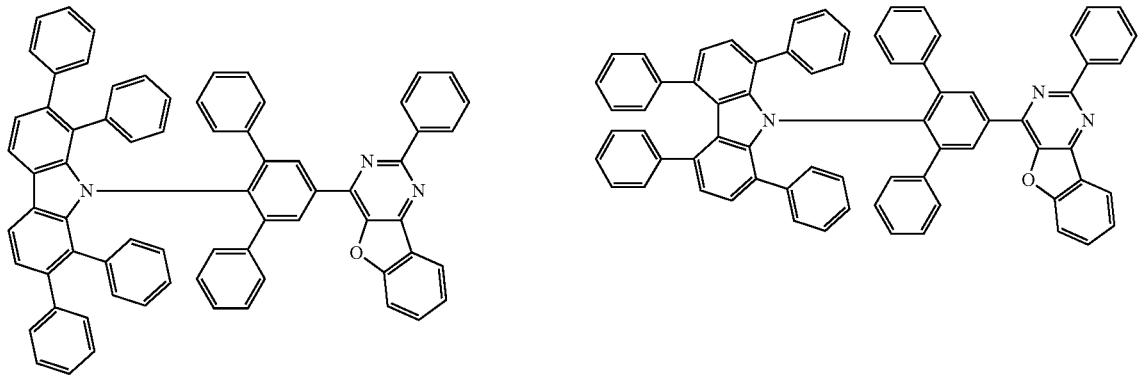

-continued
463
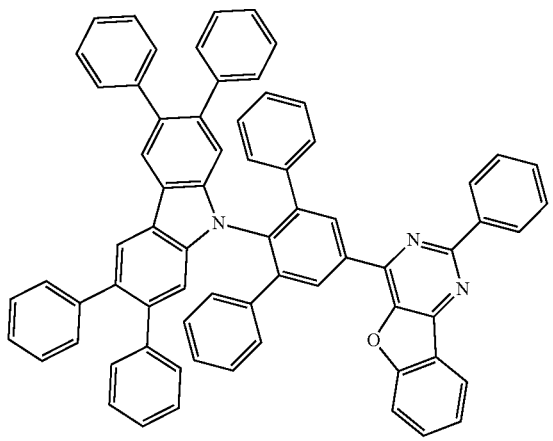
464
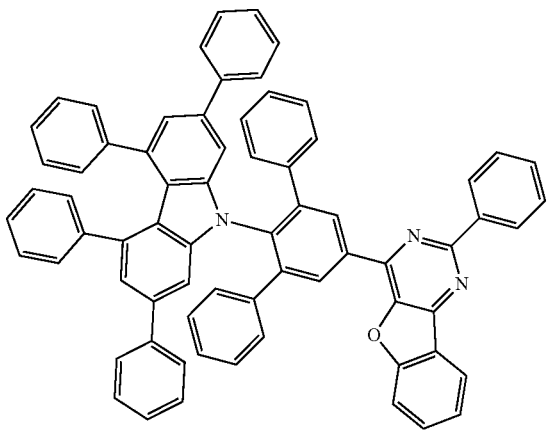
465
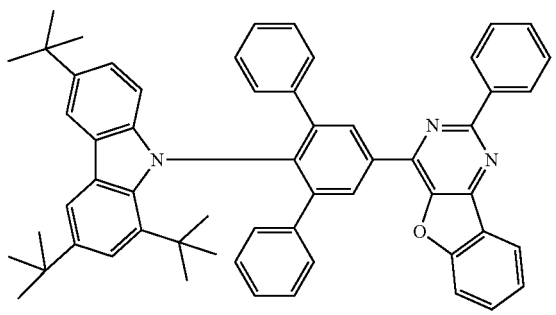
466
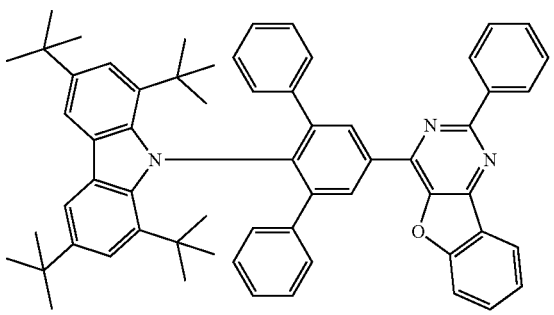
467
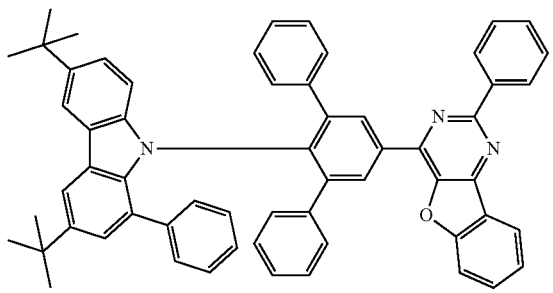
468
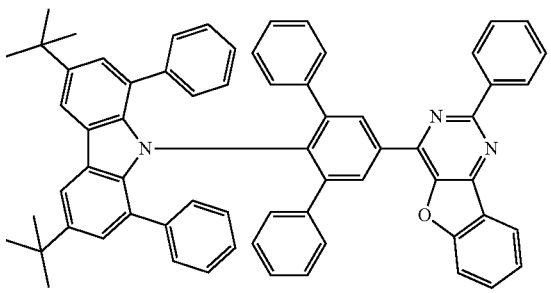
470
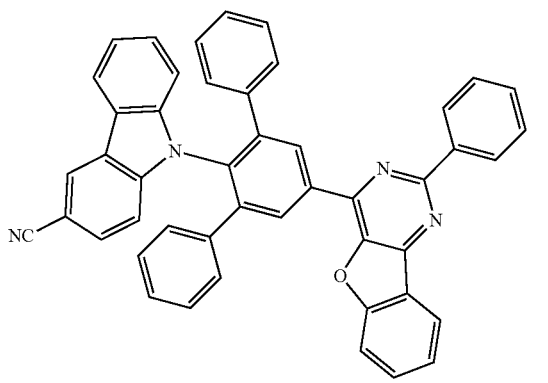
469
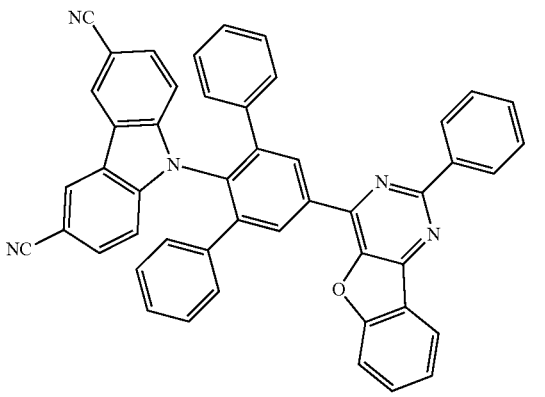

471
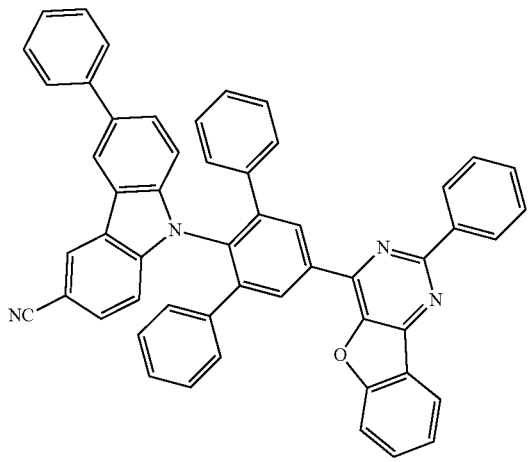
472
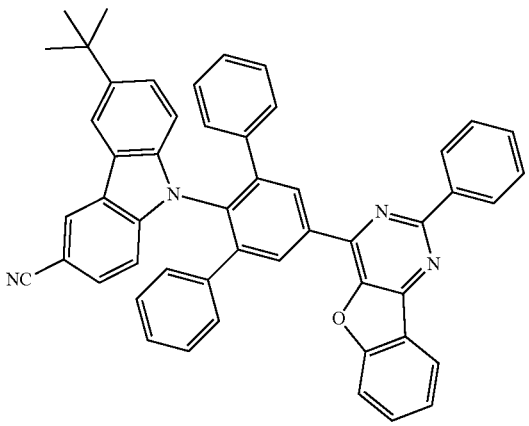
473
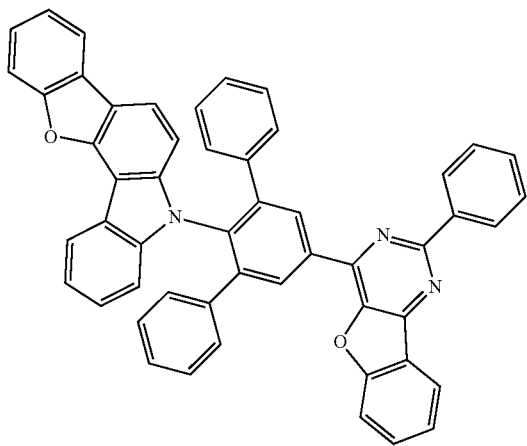
474
475
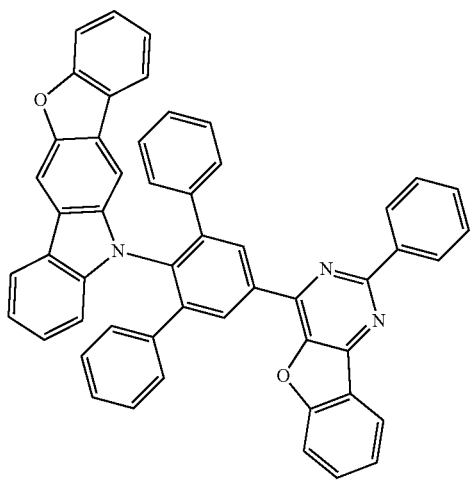
476
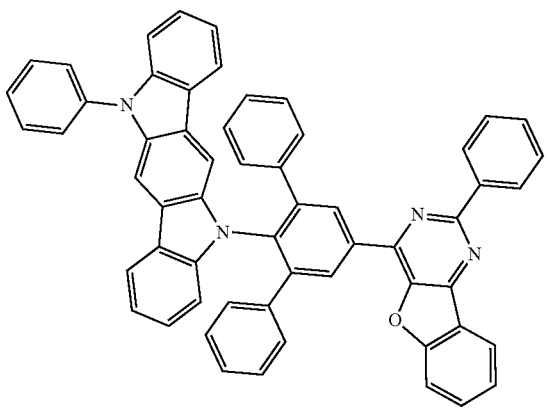

477
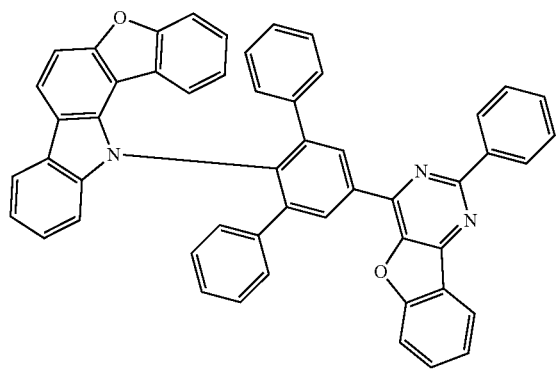
478
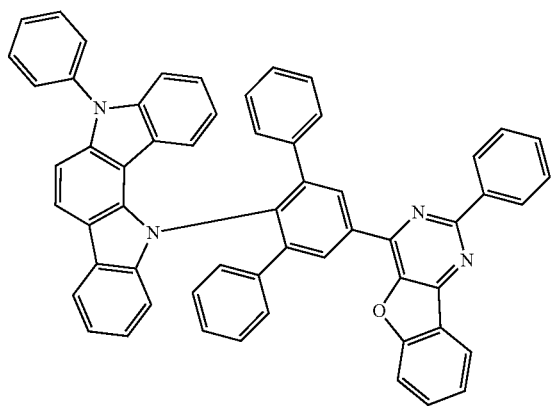
479
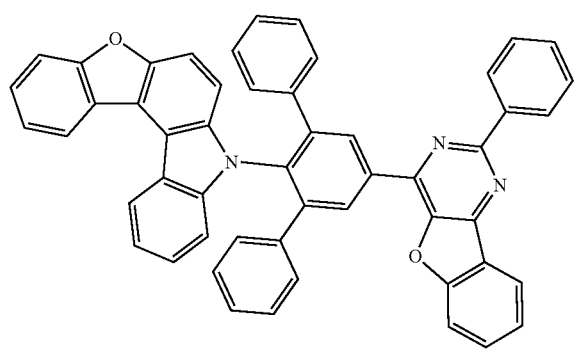
480
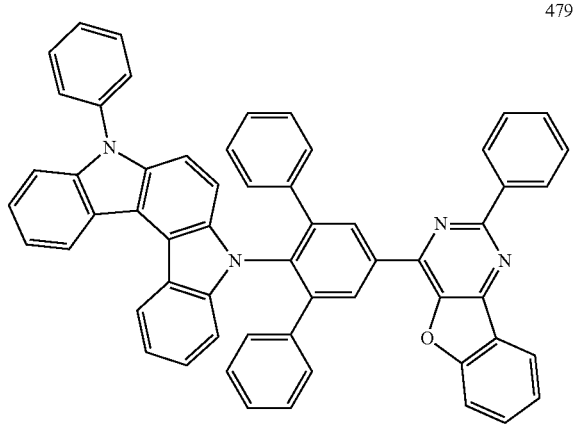
481
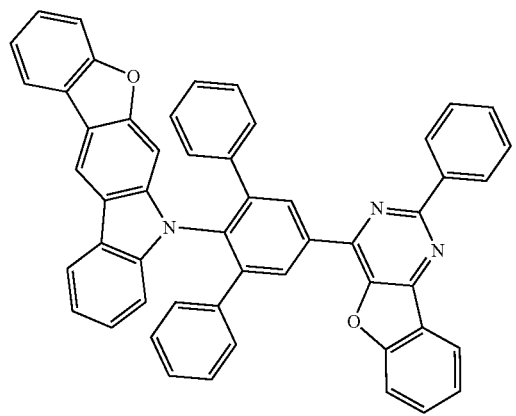
482
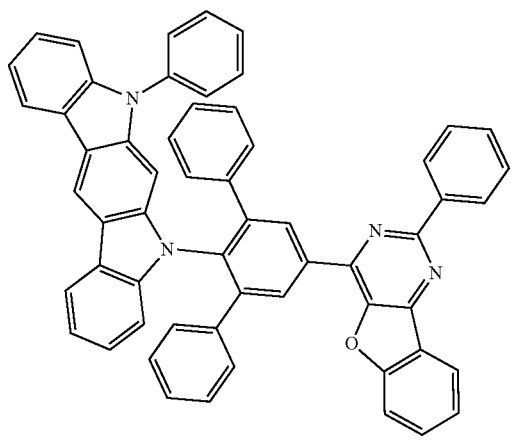

-continued
483
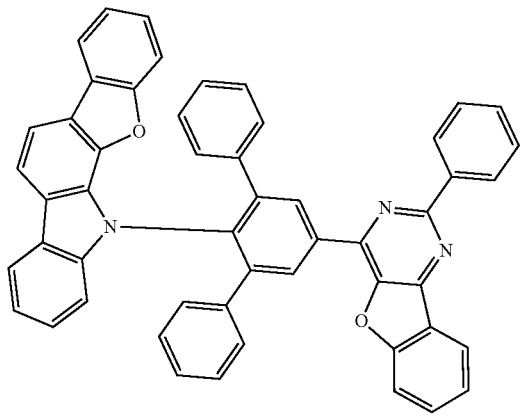
484
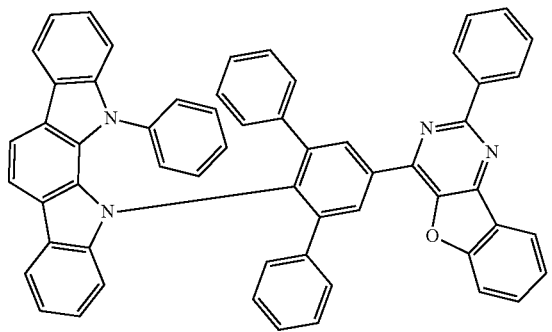
485
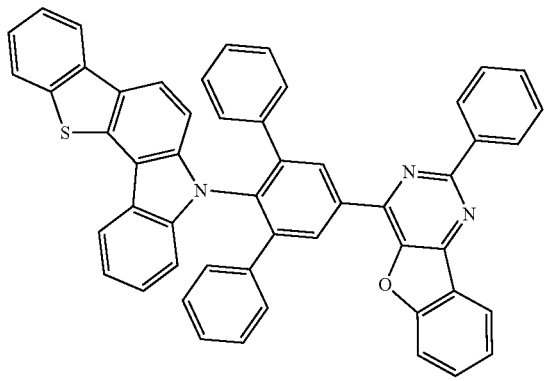
486
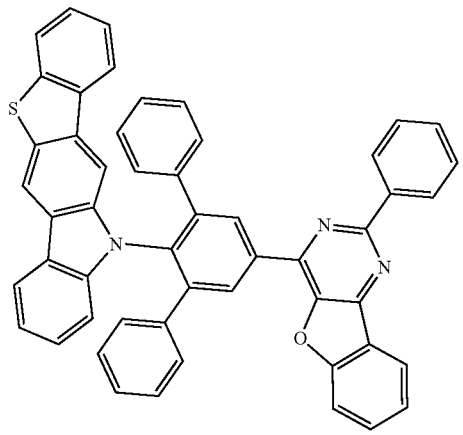
487
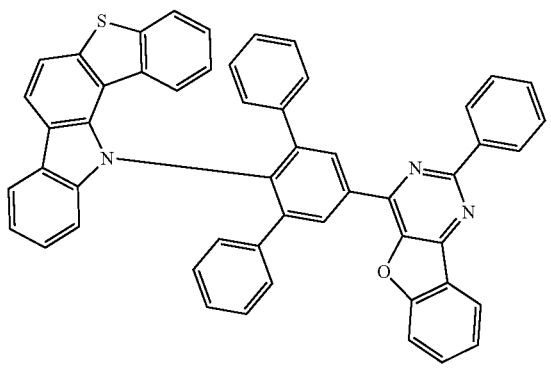
488
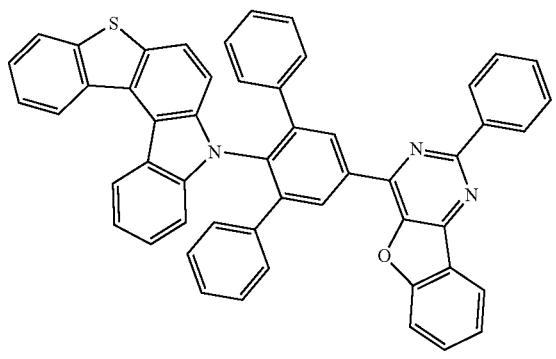

-continued
489
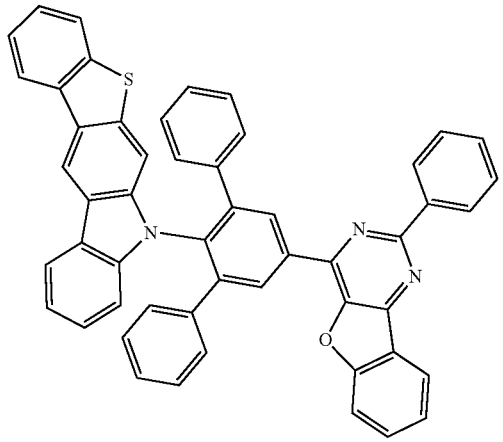
490
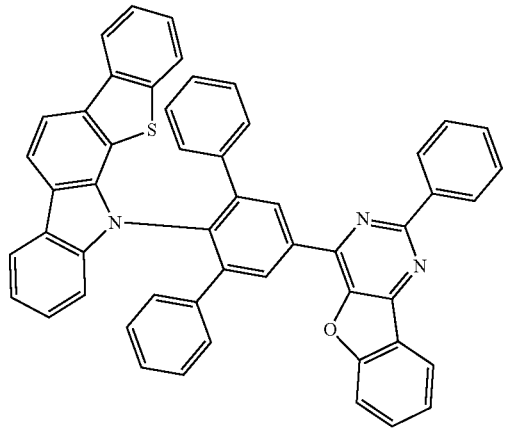
491
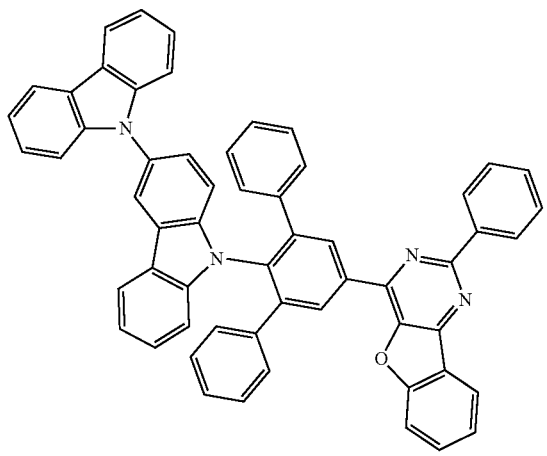
492
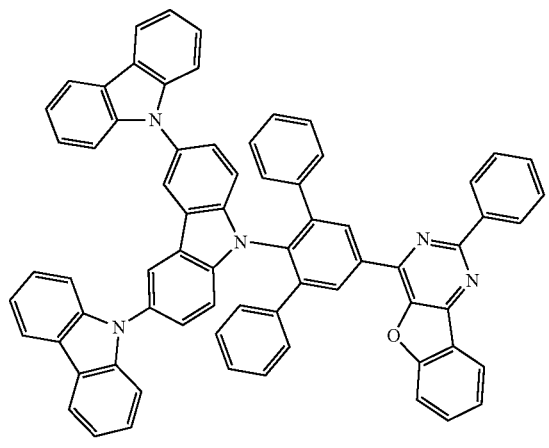
493
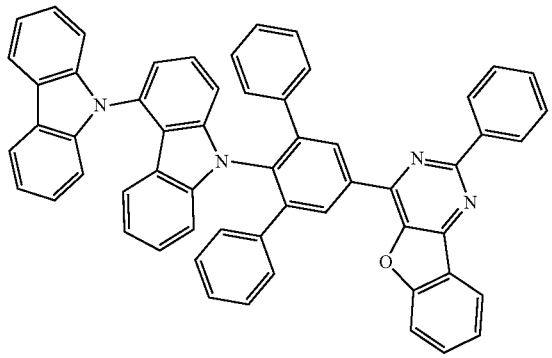
494
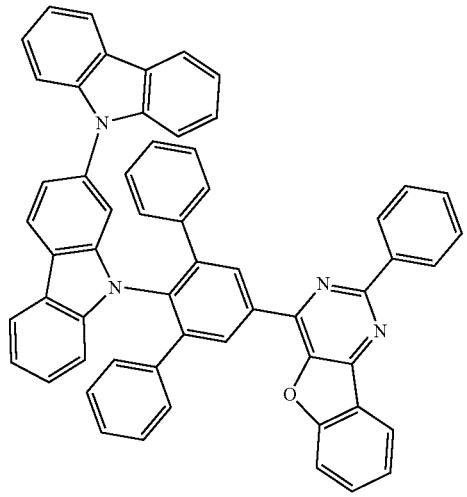

495
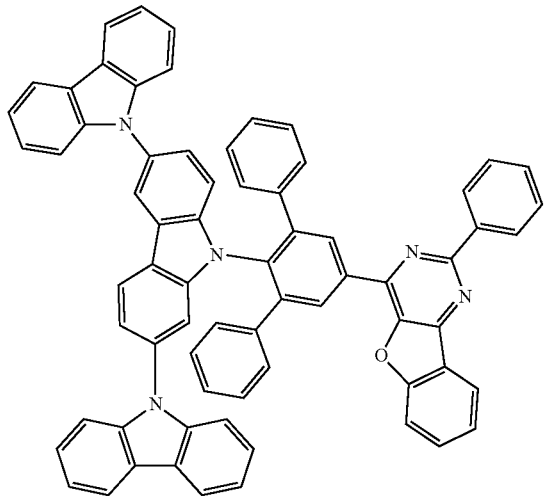
496
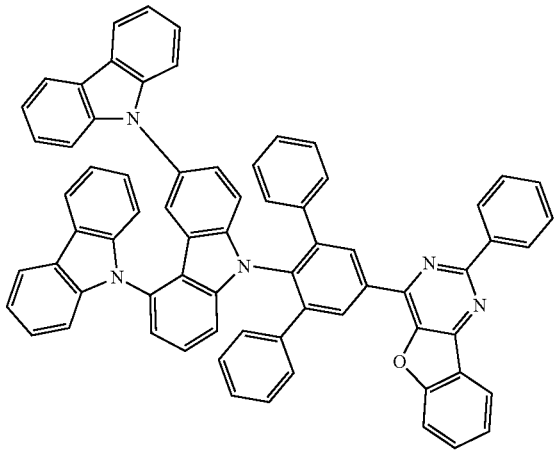
497
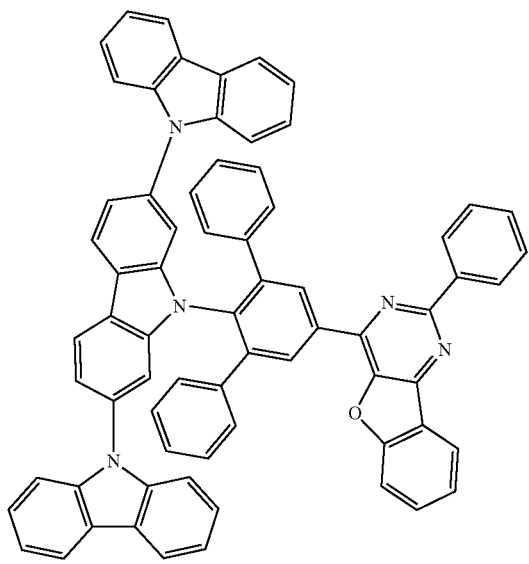
498
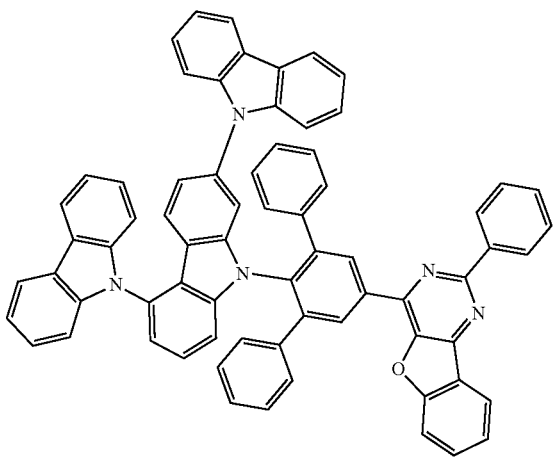
499
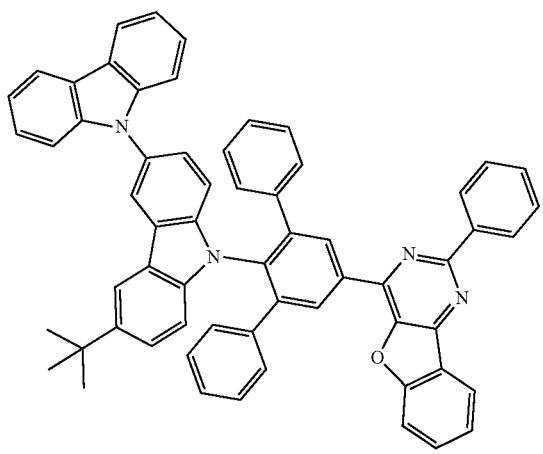
500
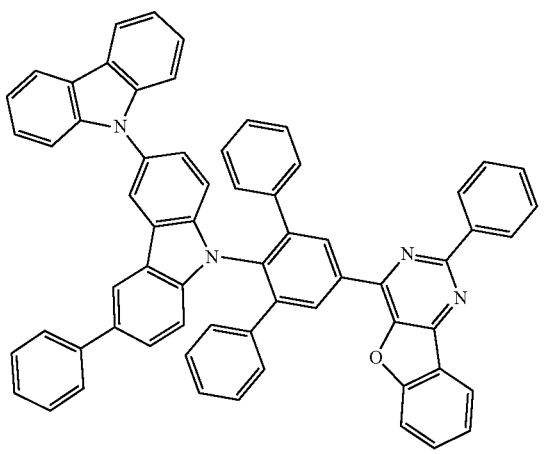

-continued
501
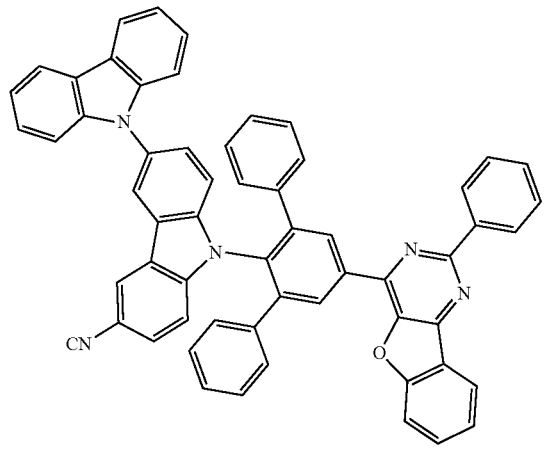
502
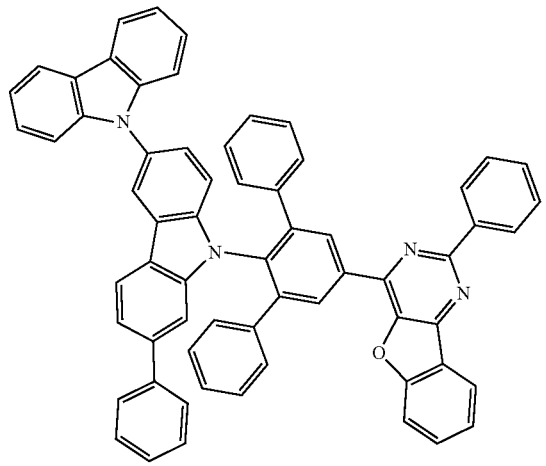
503
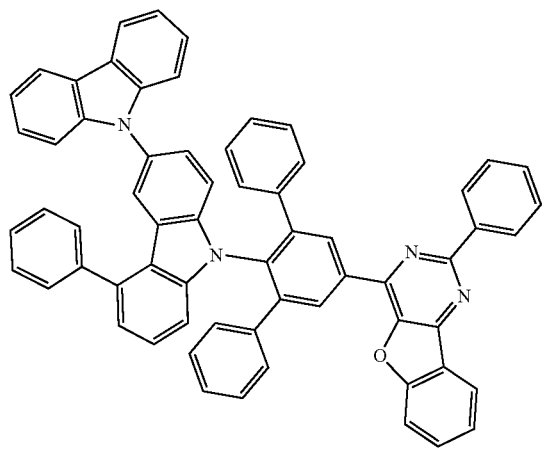
504
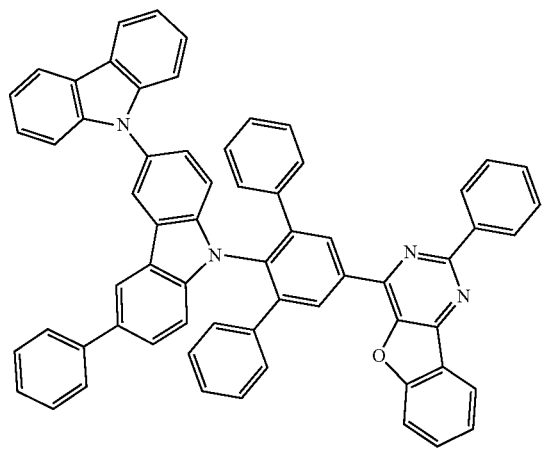
505
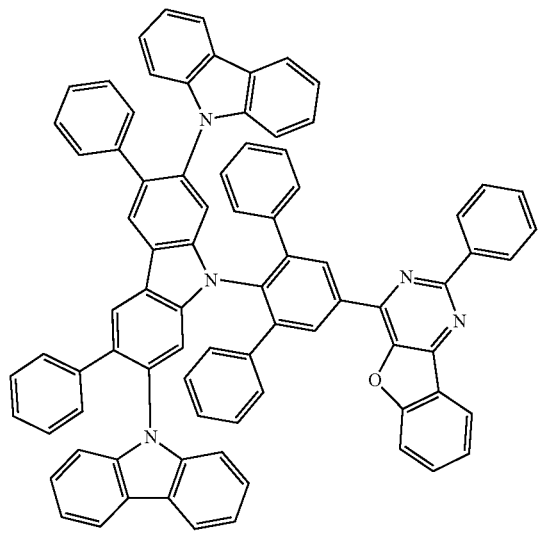
506
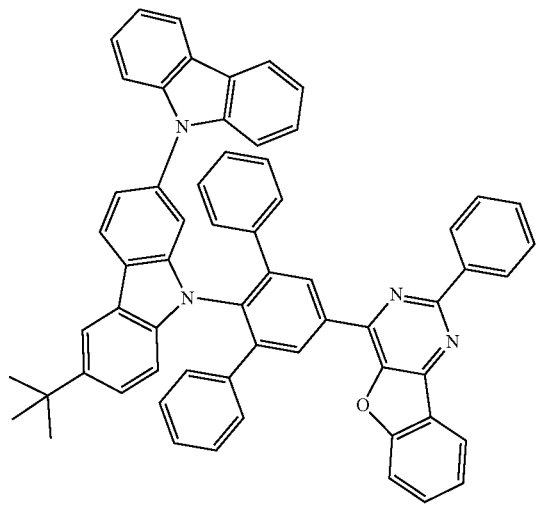

-continued
507
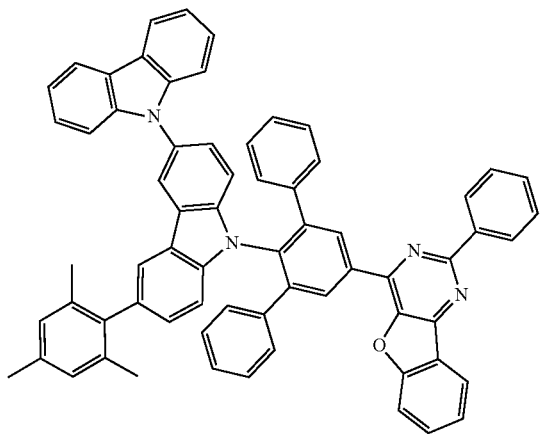
508
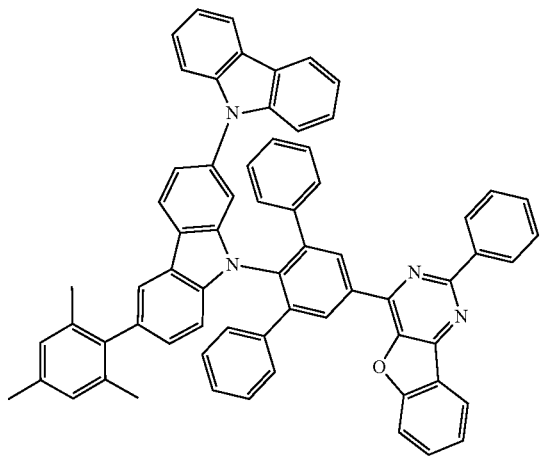
509
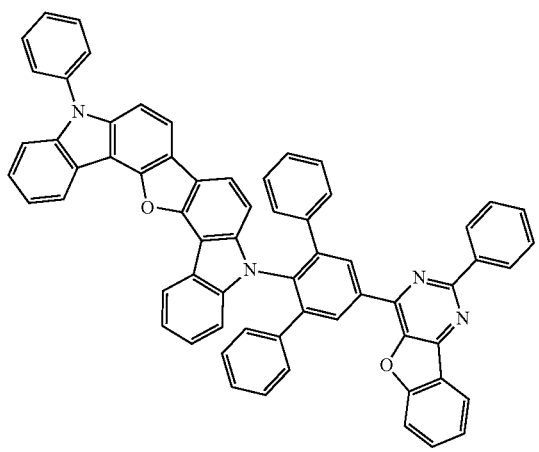
510
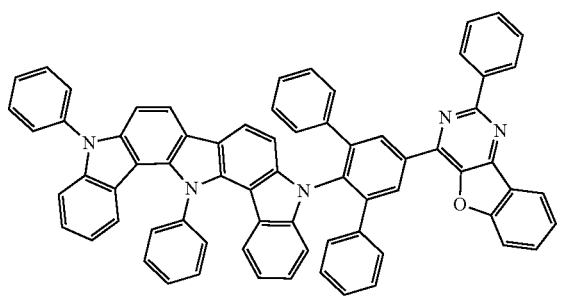
511
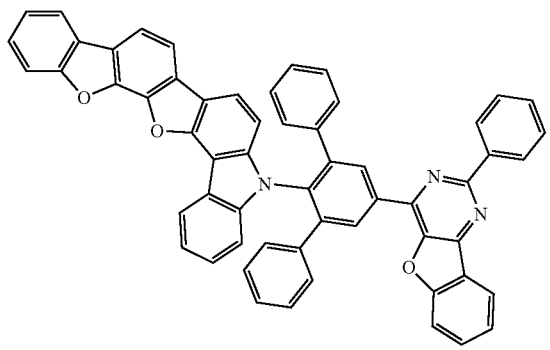
512
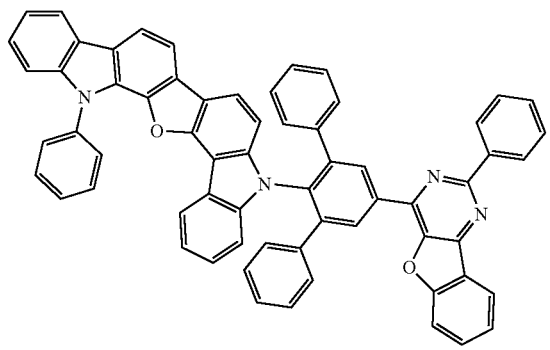

513
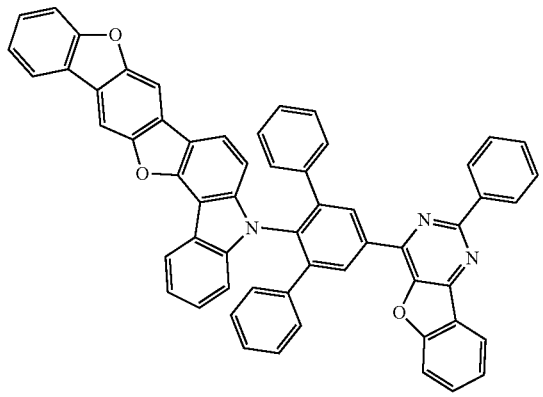
514
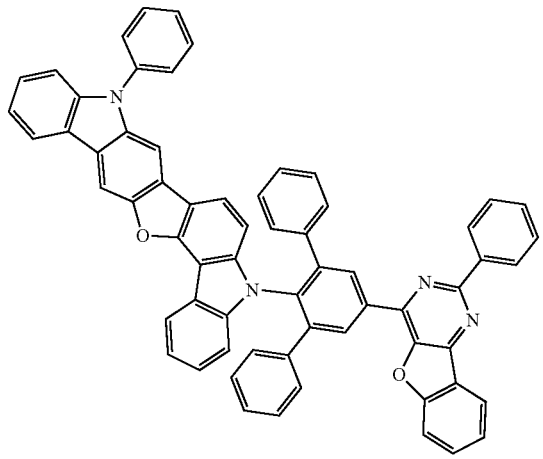
515
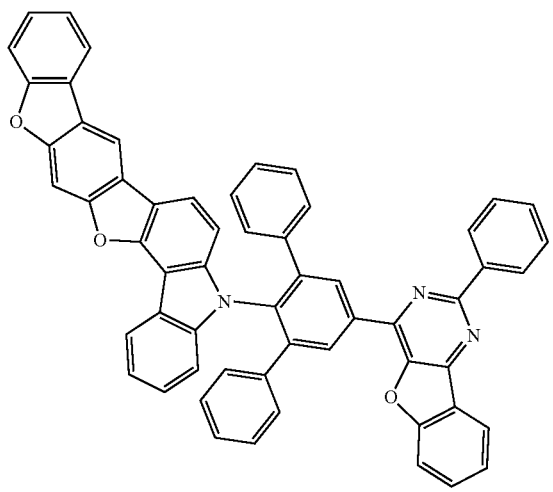
516
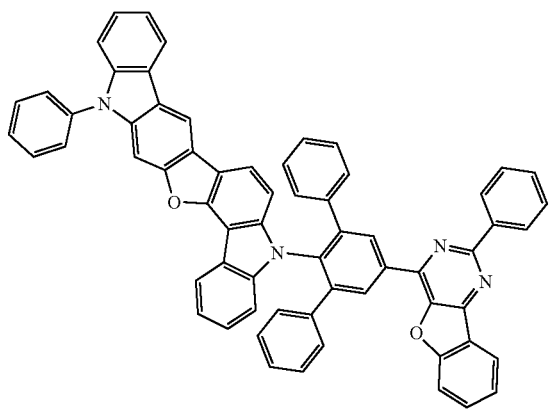
517
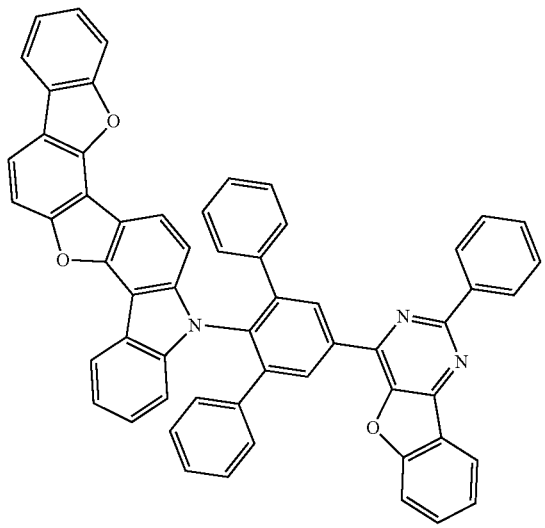
518
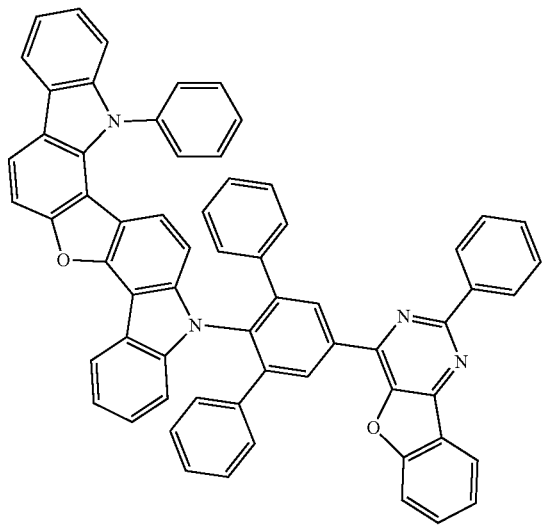

-continued
519
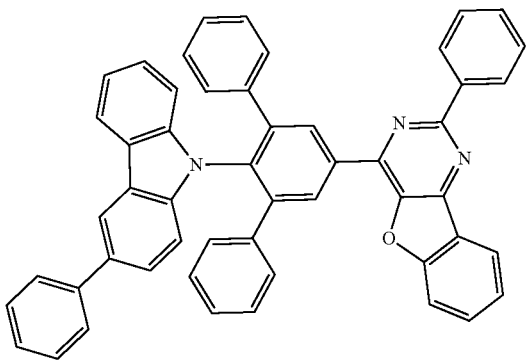
520
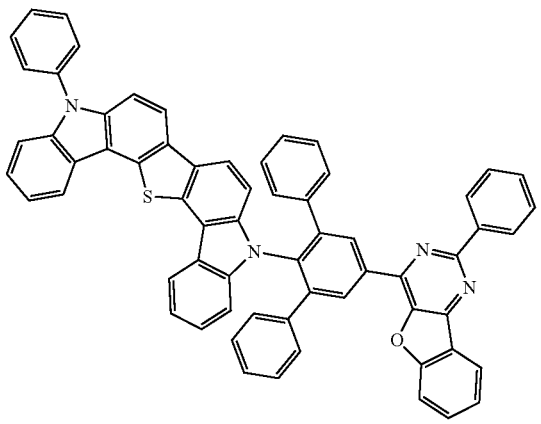
521
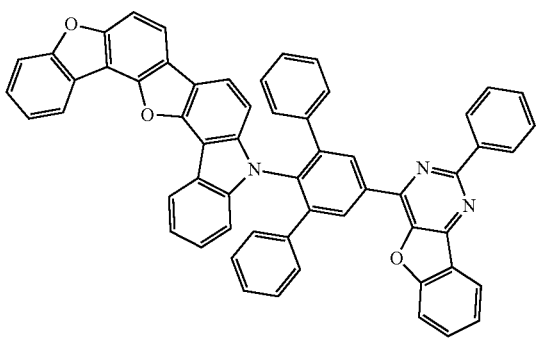
522
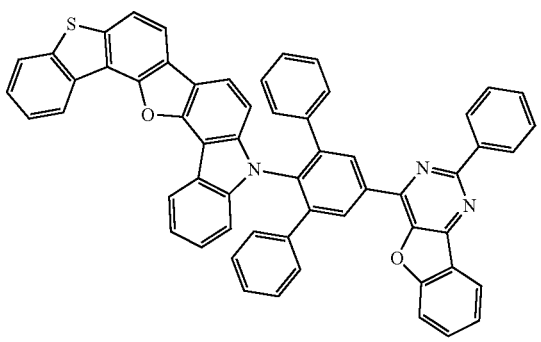
523
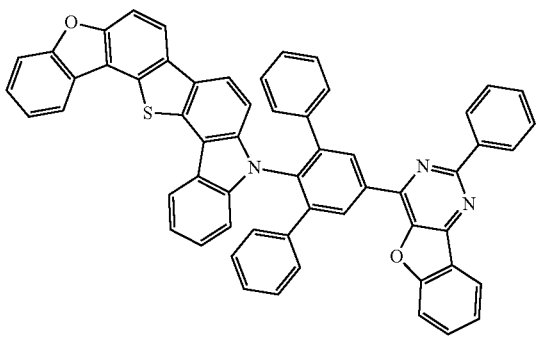
524
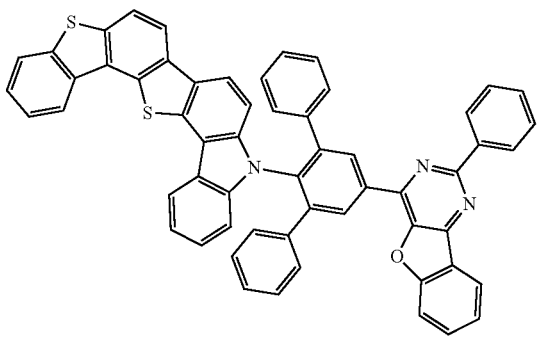
525
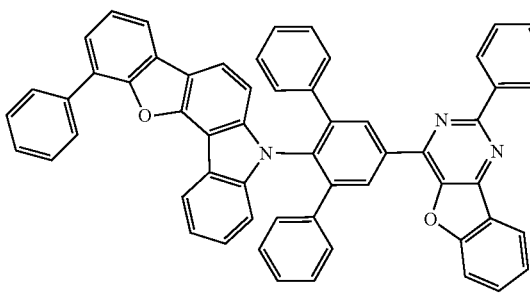
526
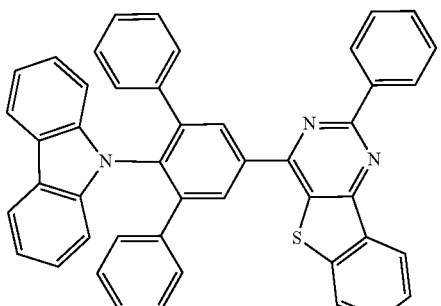

-continued
| 527 | 528 |
|---|---|
| 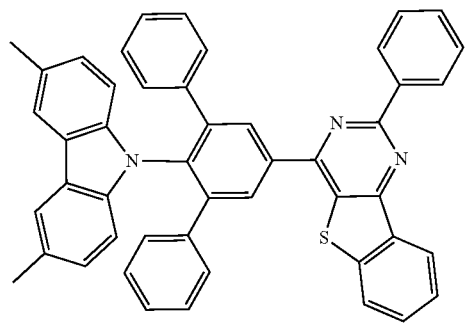 | 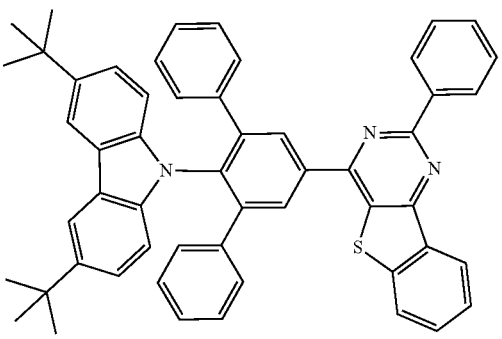 |
| 529 | 530 |
| 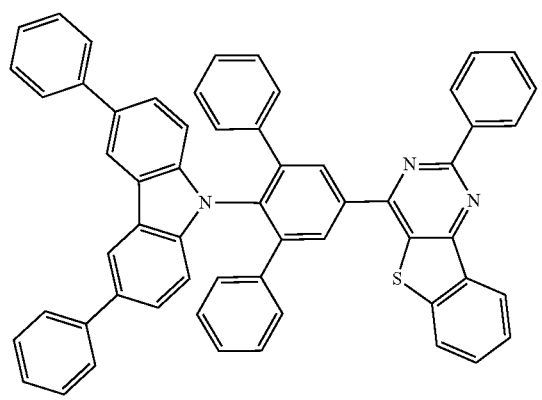 | 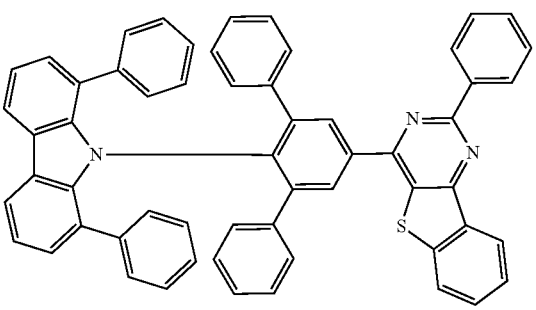 |
| 530 | 532 |
| 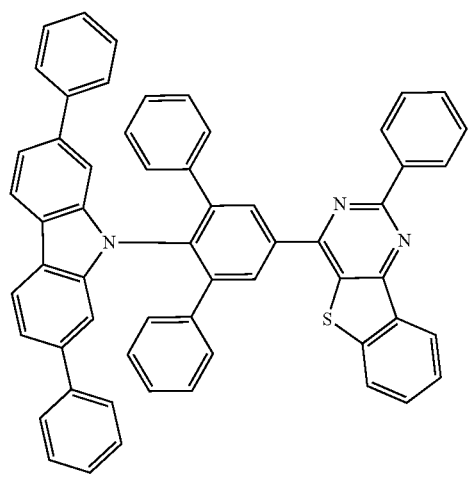 | 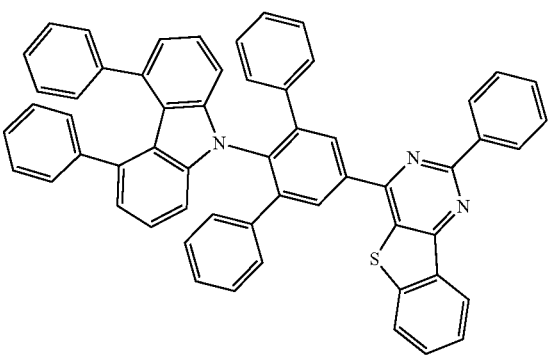 |
| 533 | 534 |
| 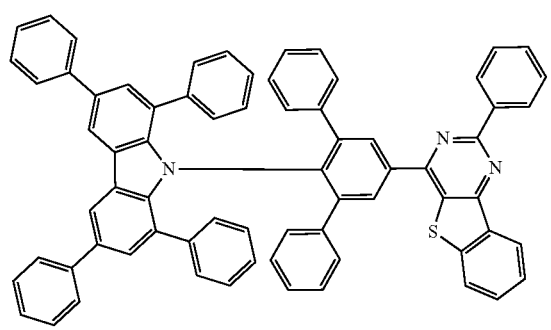 | 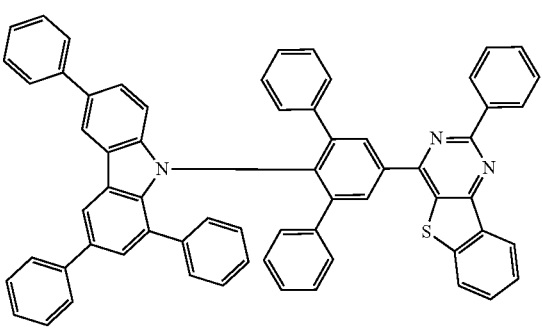 |

535 536
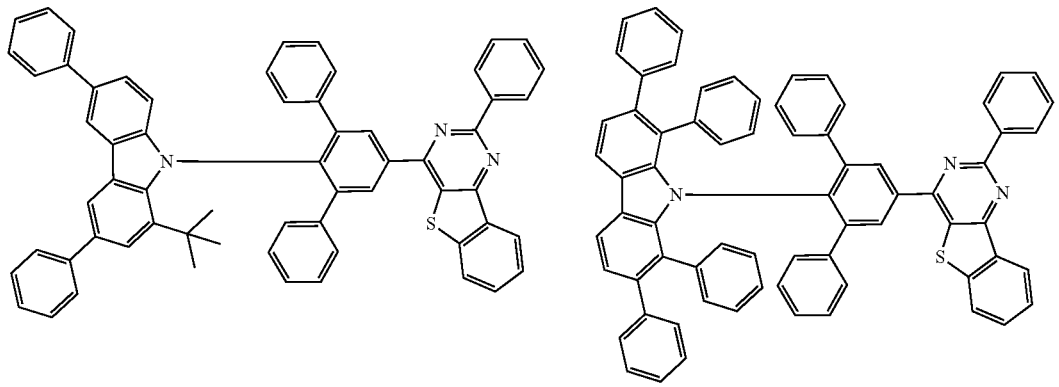
537
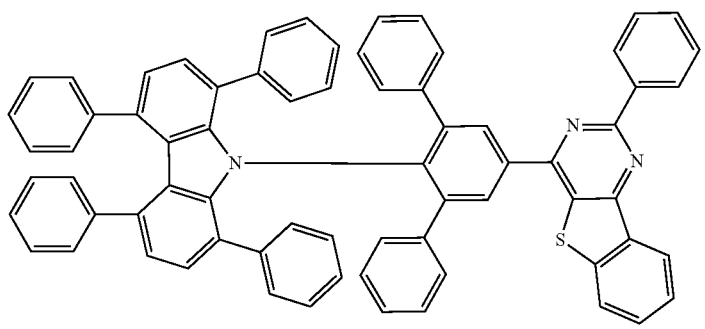
538 539
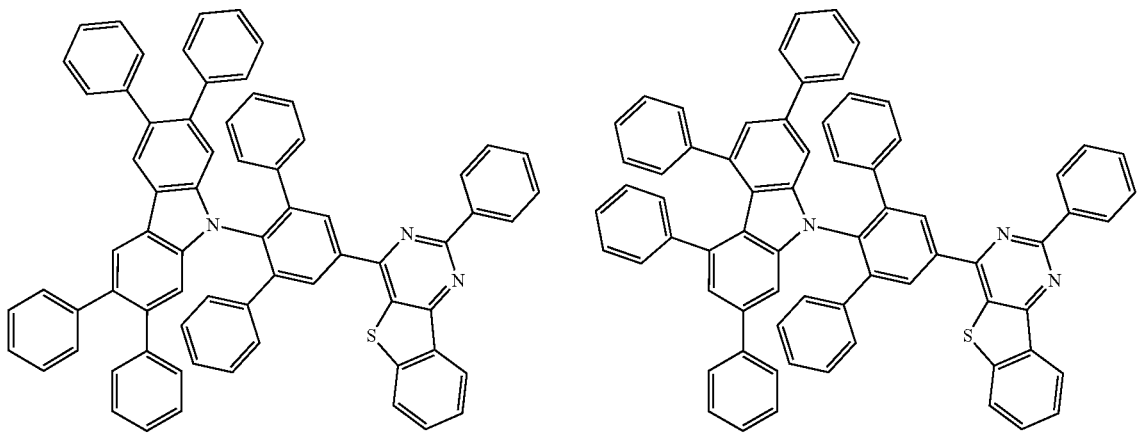
540 541
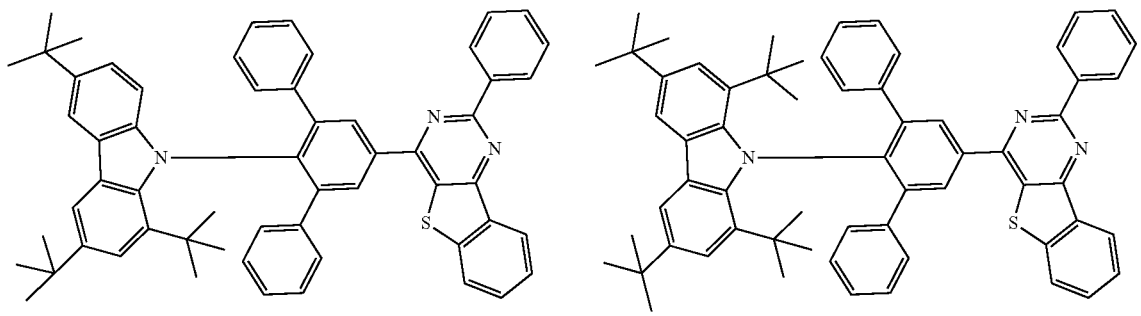

-continued
542
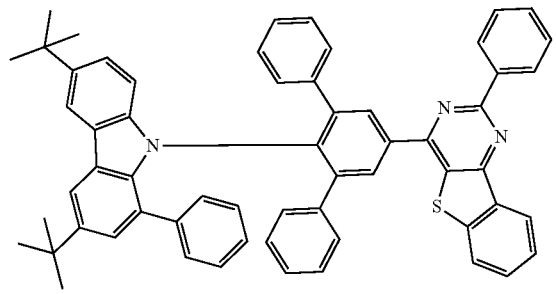
543
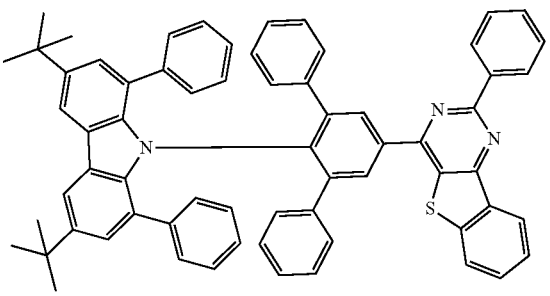
544
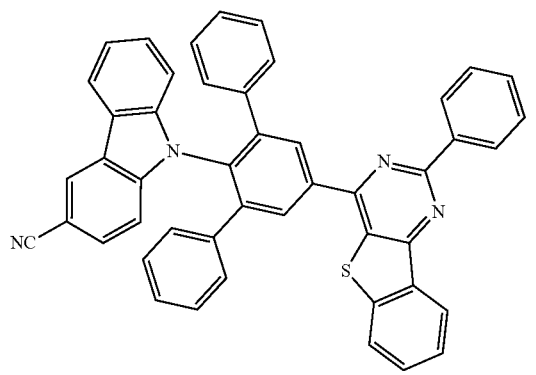
545
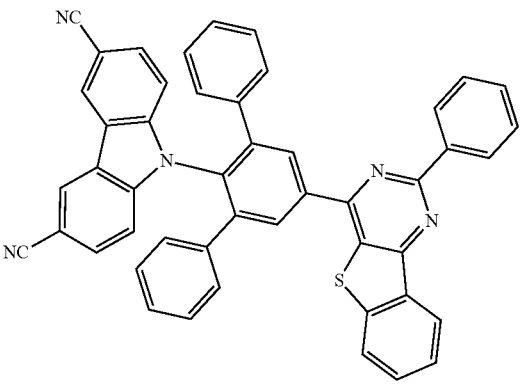
546
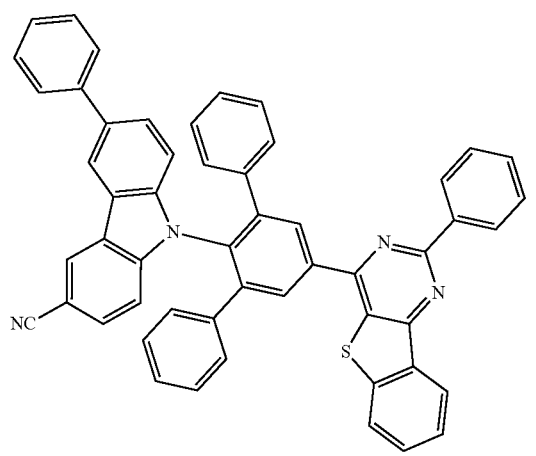
547
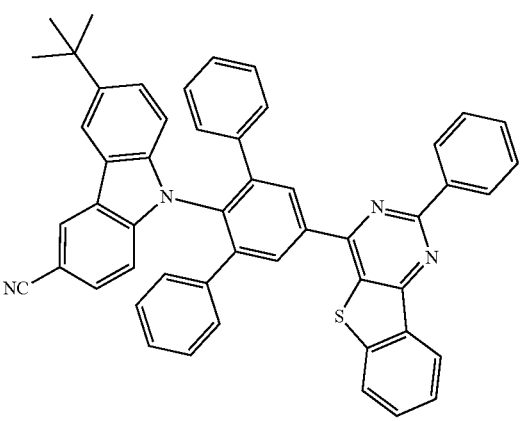
548
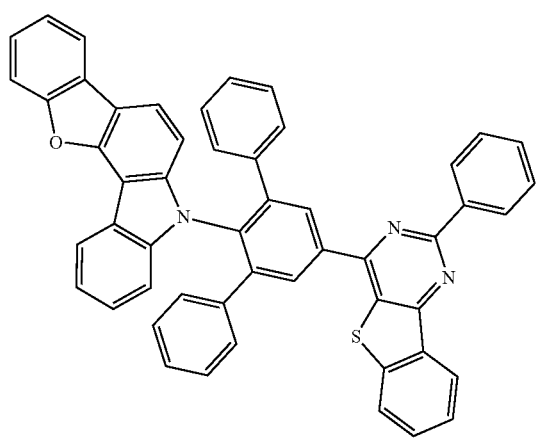
549
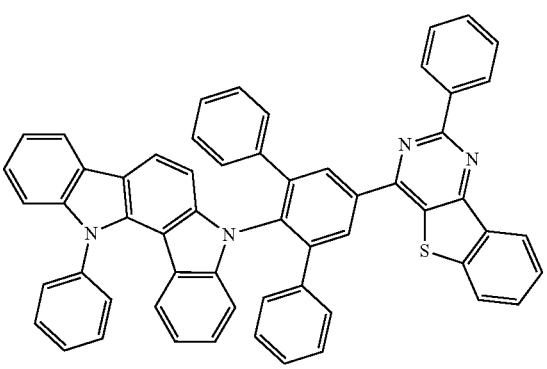

-continued
| 3061 | 3062 |
|---|---|
| 550 | 551 |
| 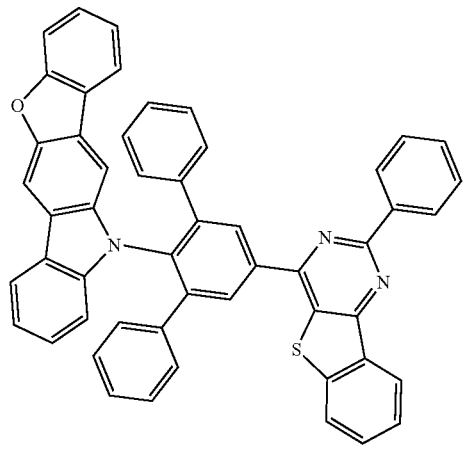 | 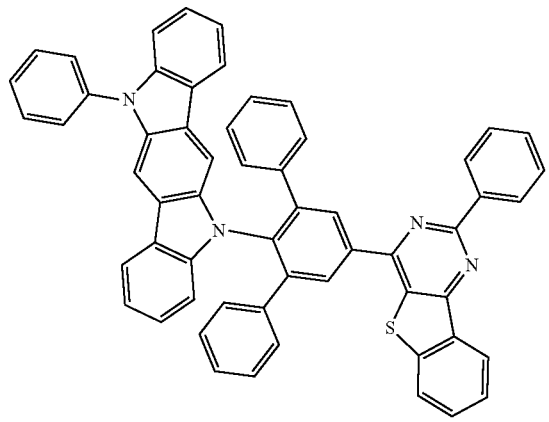 |
| 552 | 553 |
| 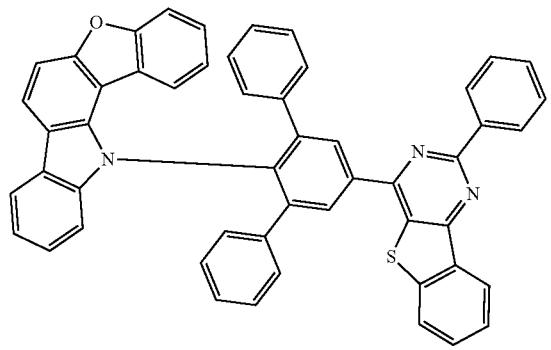 | 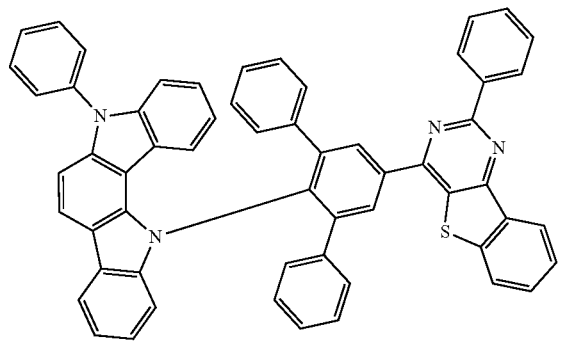 |
| 554 | 555 |
| 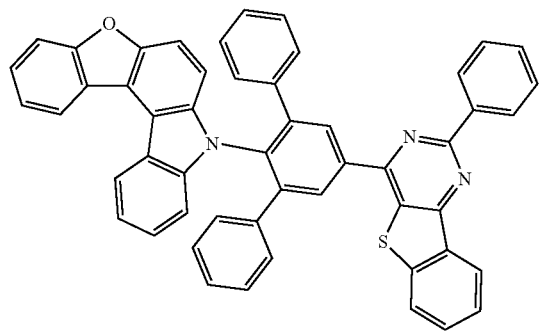 | 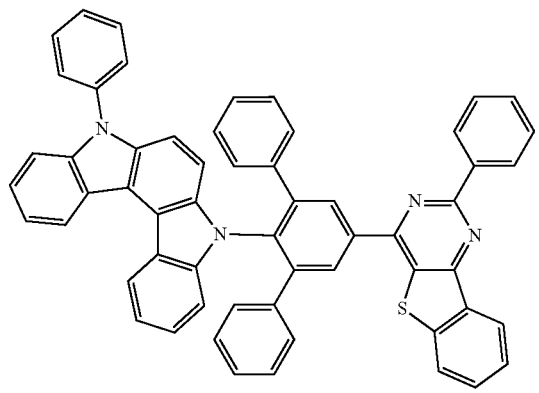 |

-continued
556
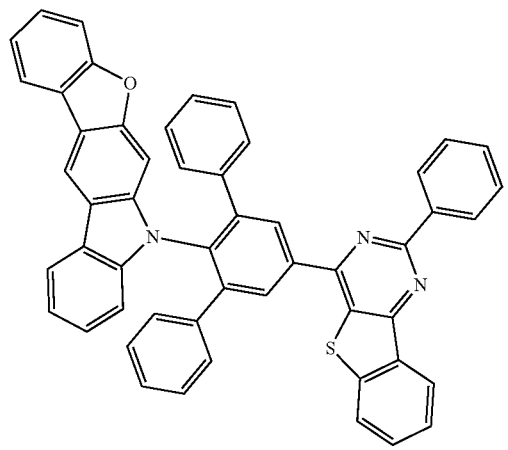
557
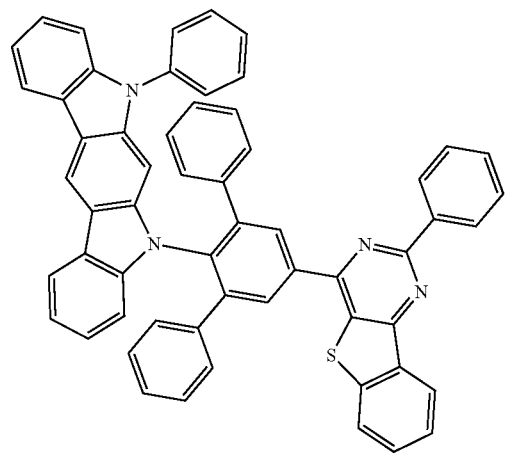
558
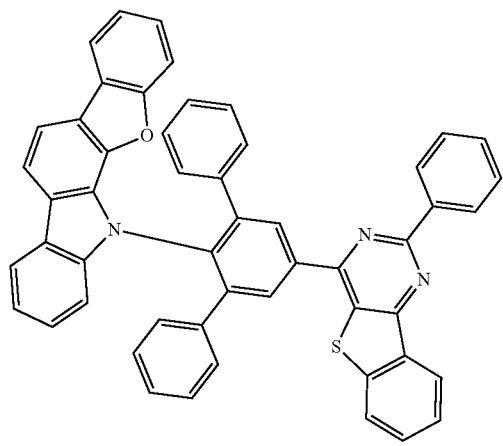
559
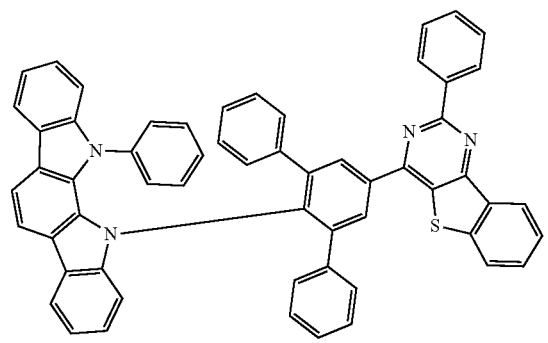
560
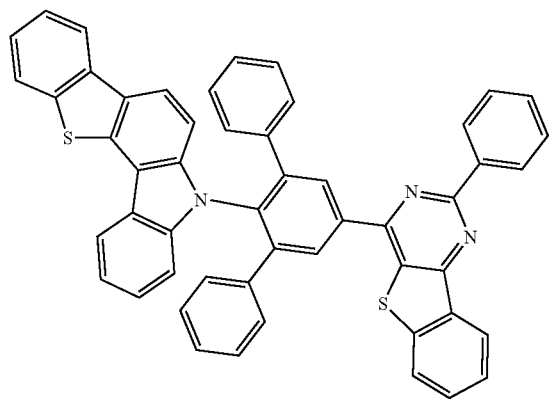
561
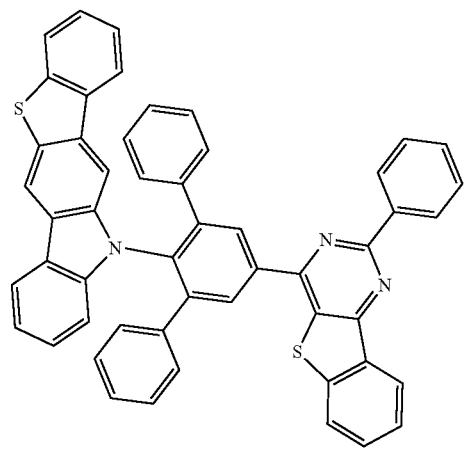

562
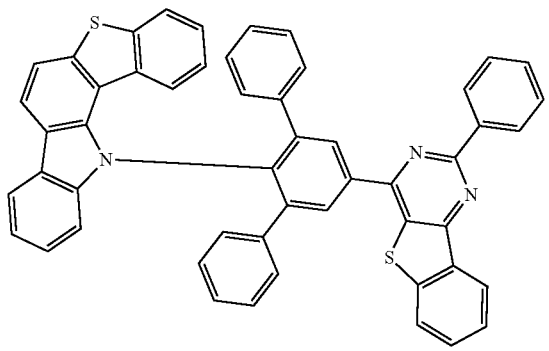
563
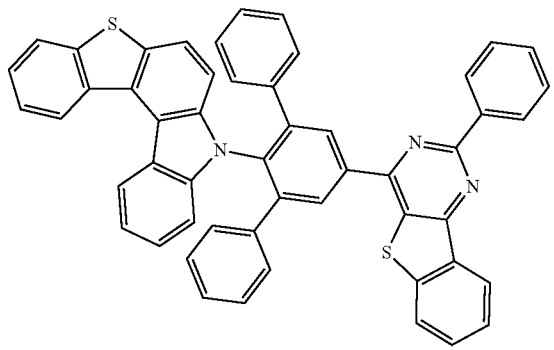
564
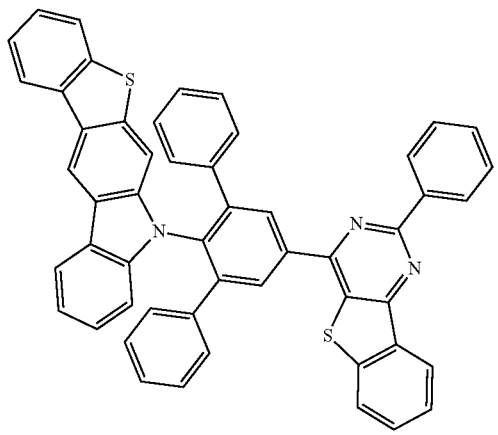
565
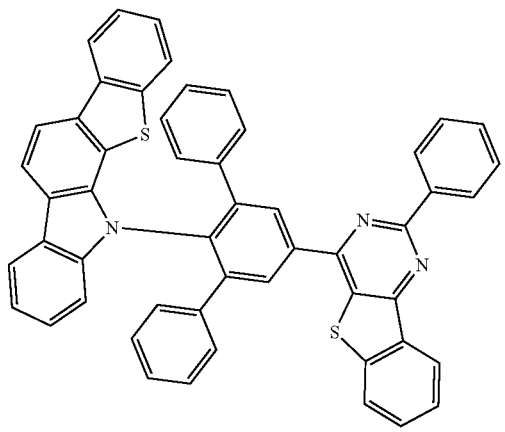
565
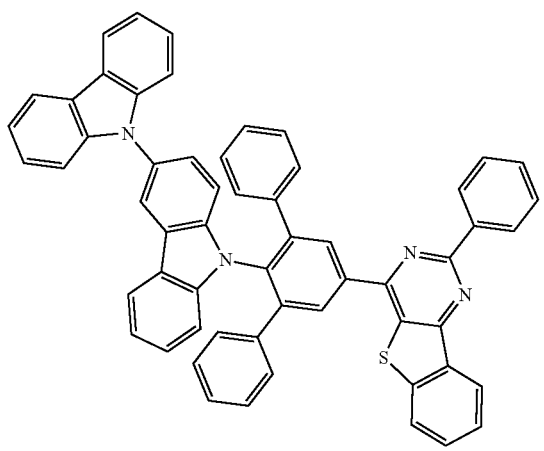
567
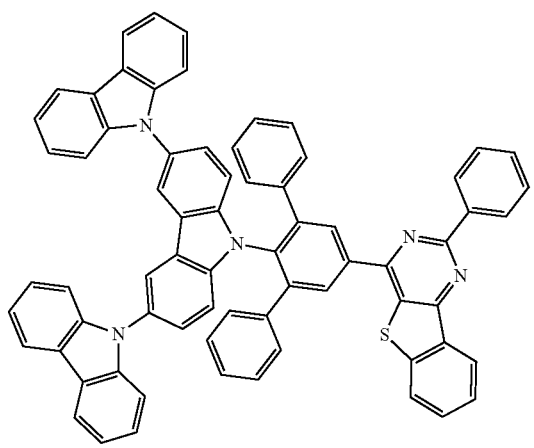

-continued
568
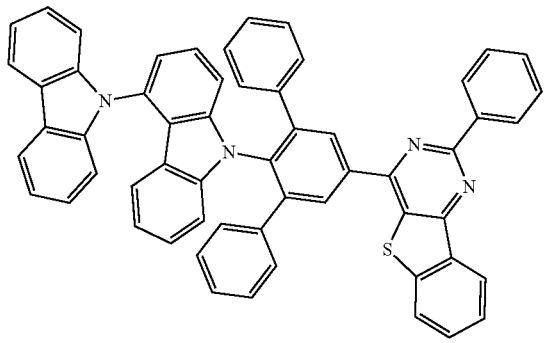
569
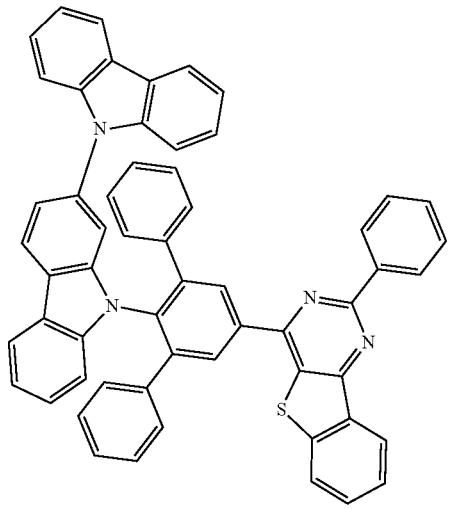
570
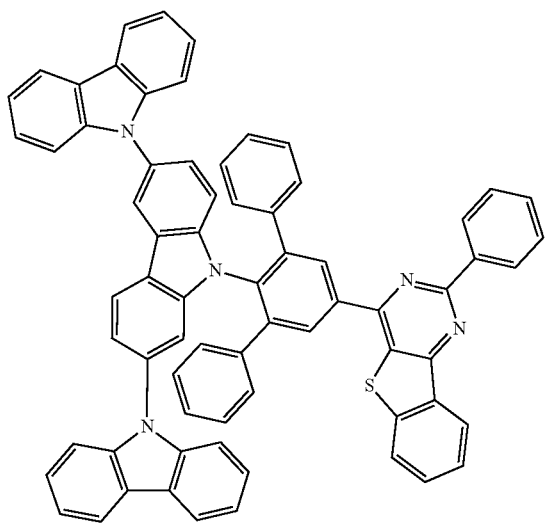
571
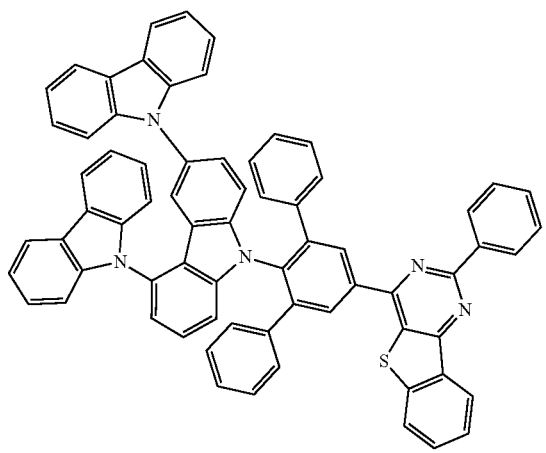
572
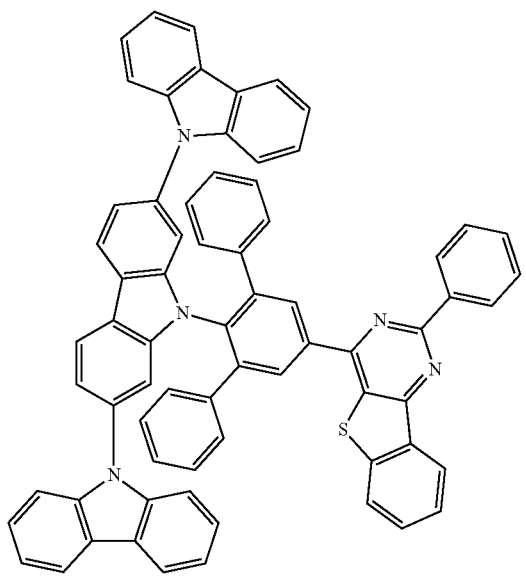
573
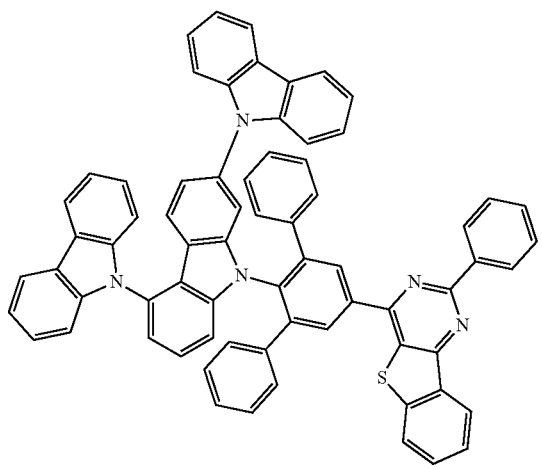

-continued
574
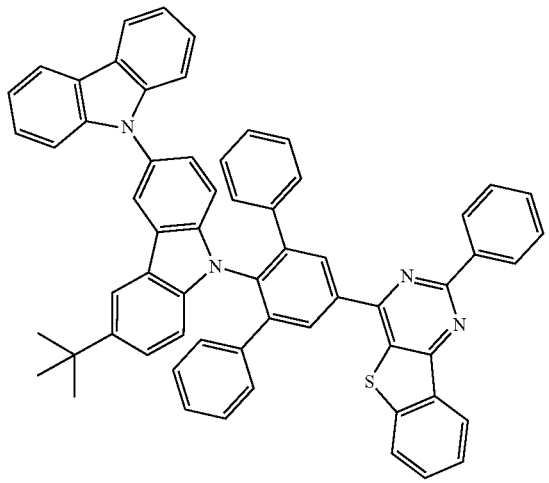
575
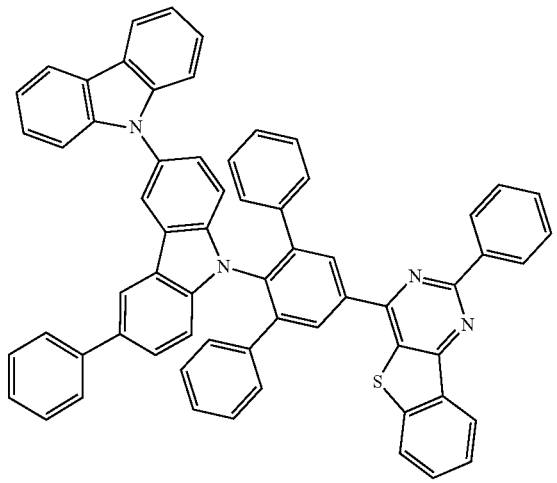
576
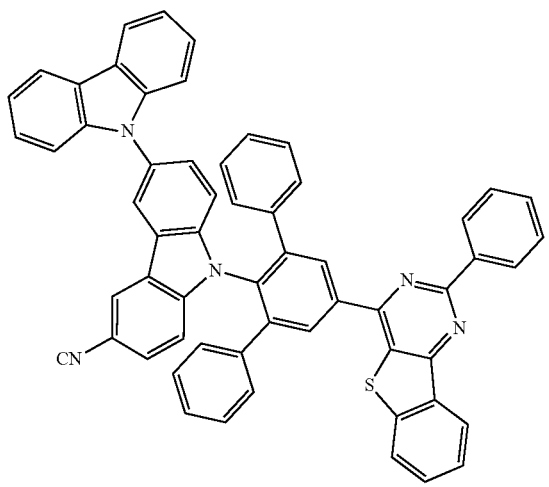
577
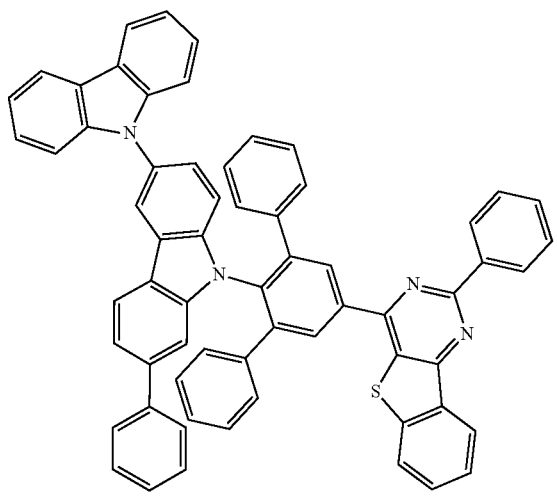
578
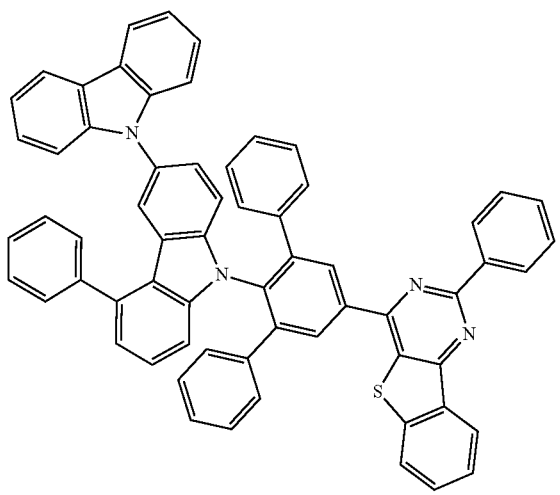
579
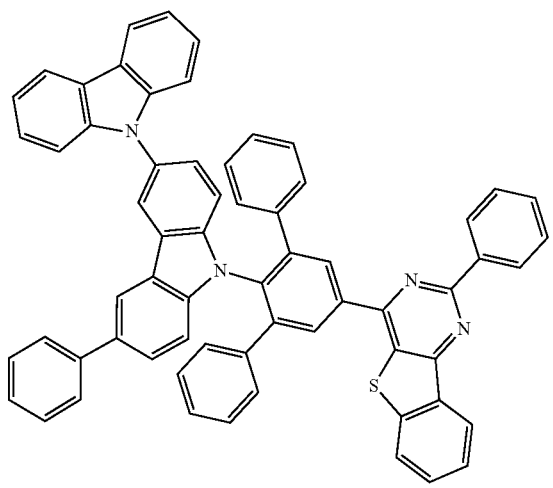

-continued
580
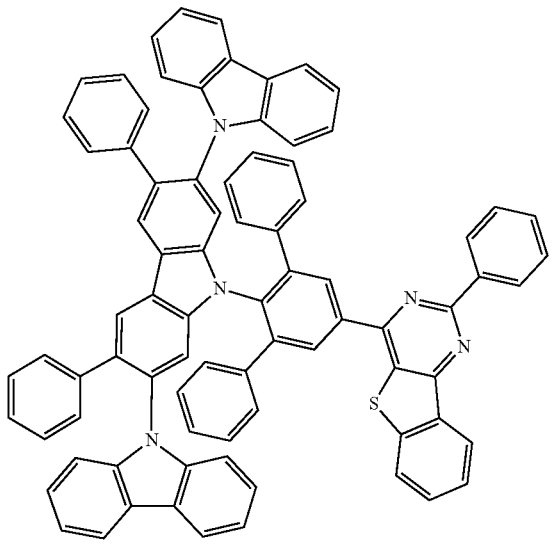
581
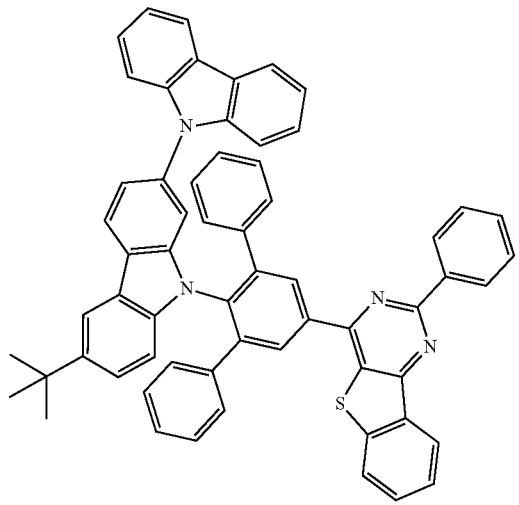
582
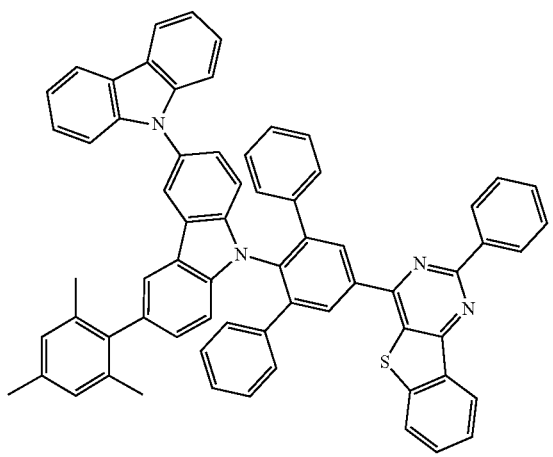
583
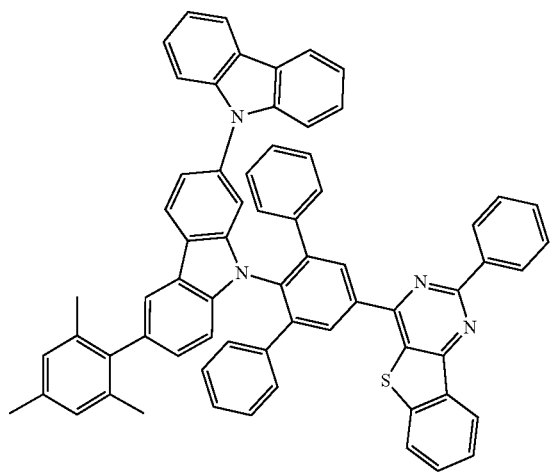
584
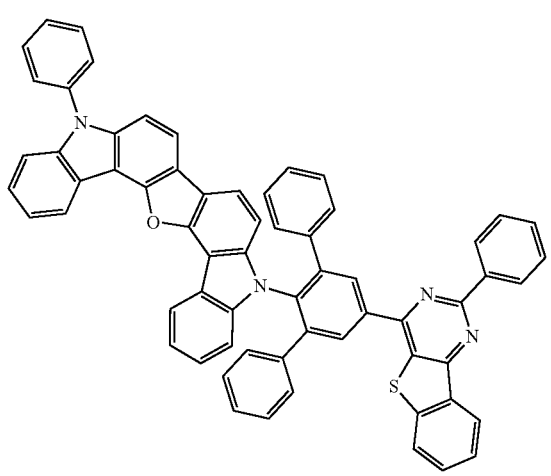

585
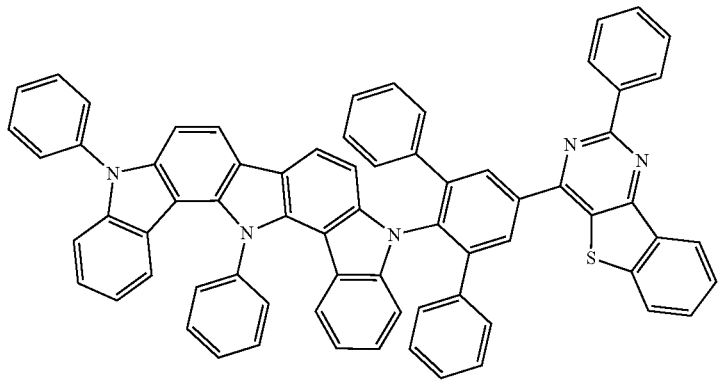
586 587
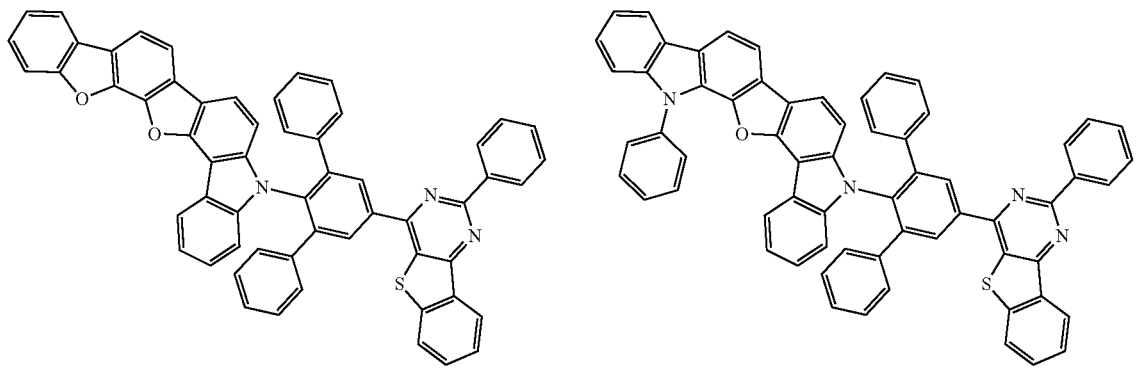
588 589
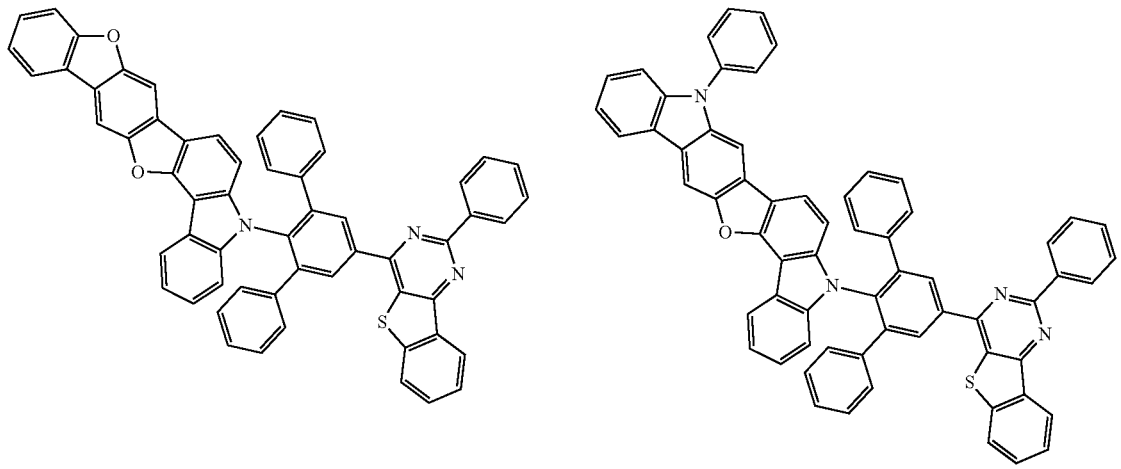

-continued
590
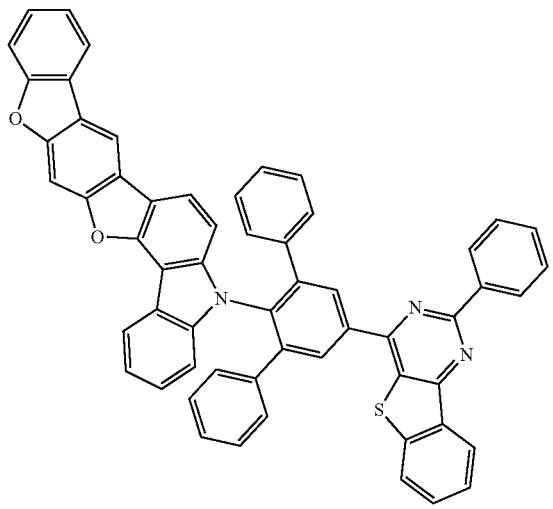
591
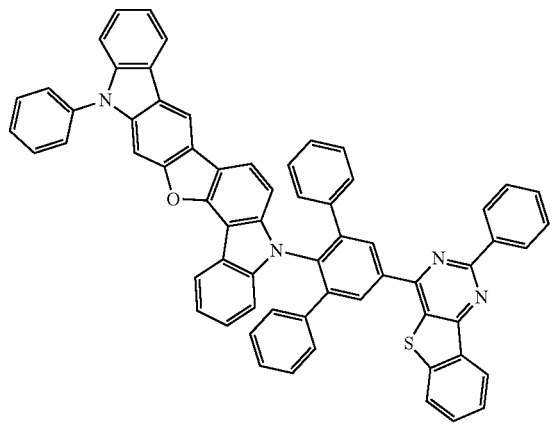
592
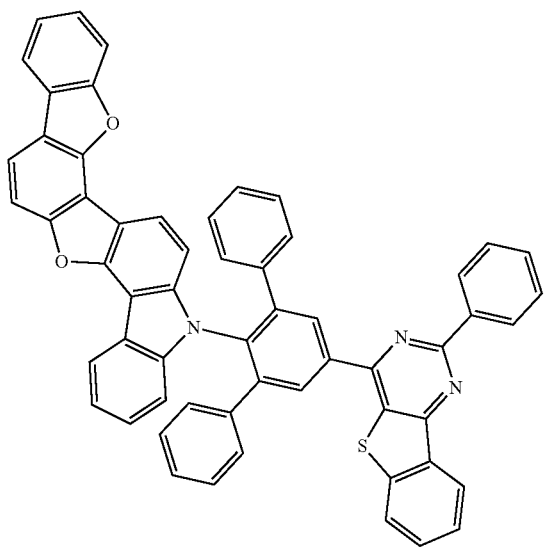
593
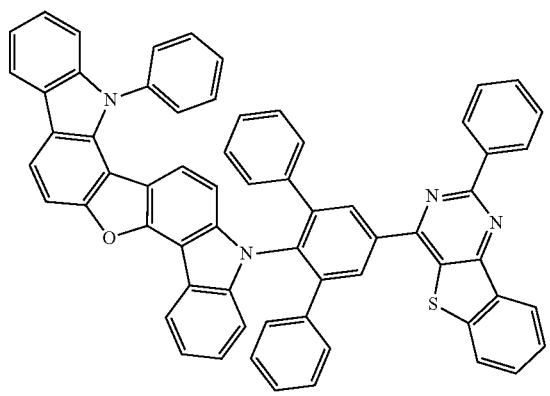
594
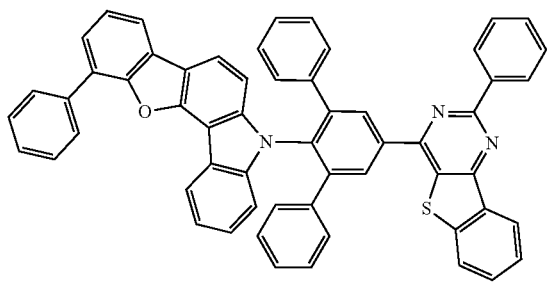
595
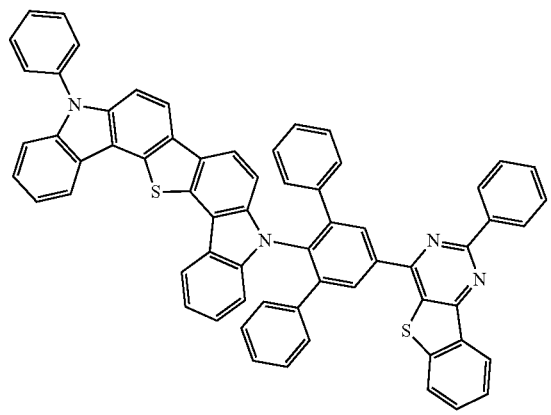

-continued
596
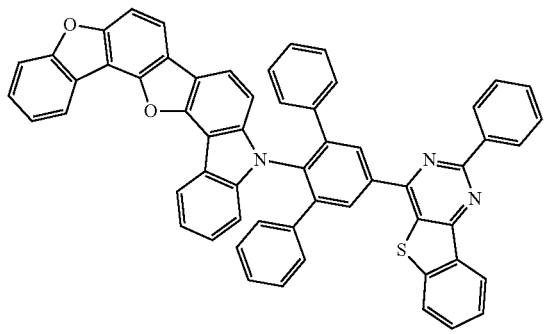
597
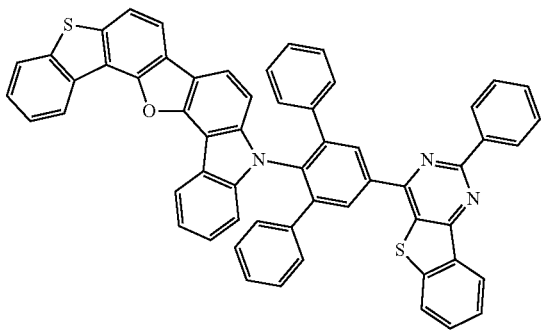
598
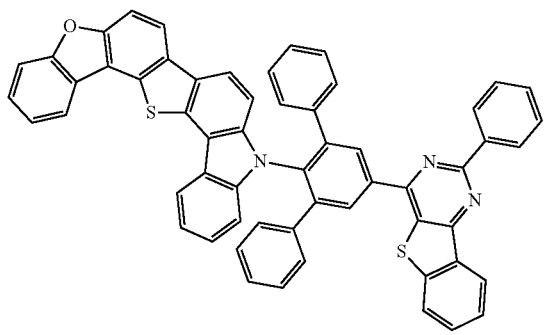
599
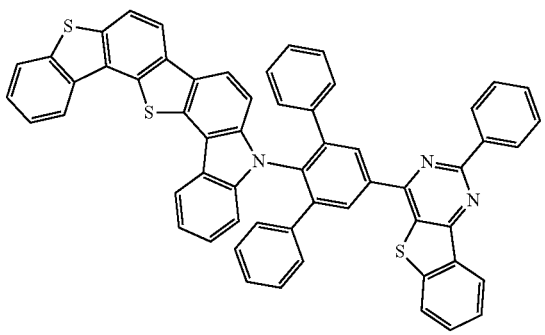
600
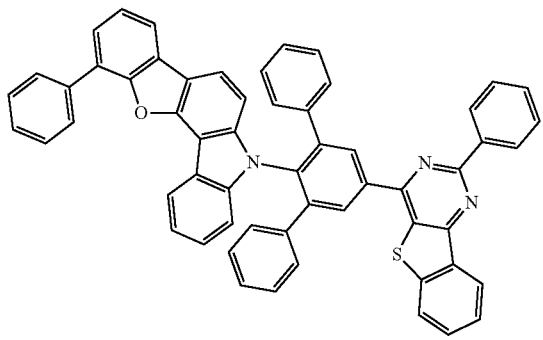
601
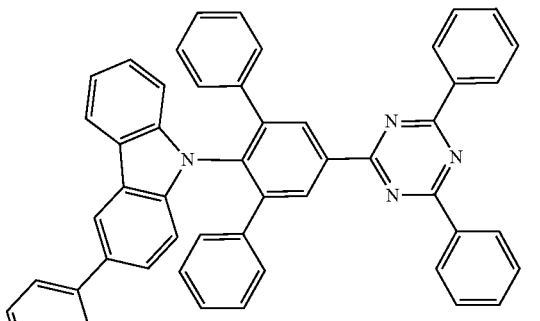
602
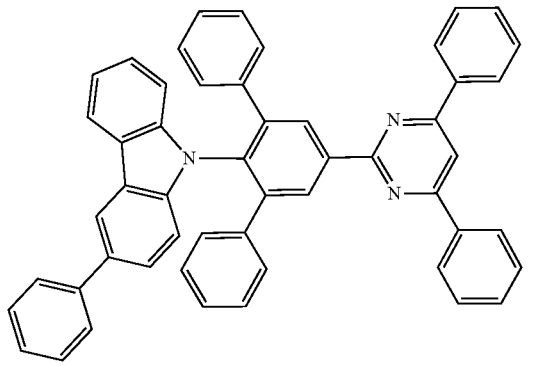
603
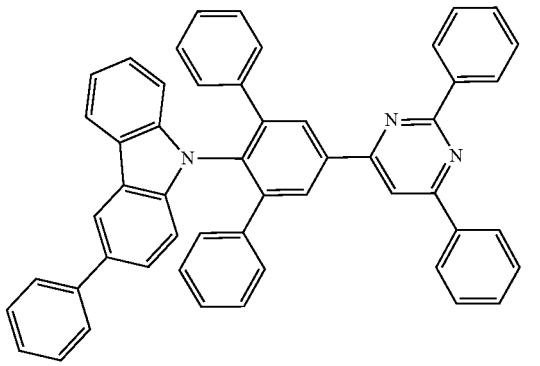

604
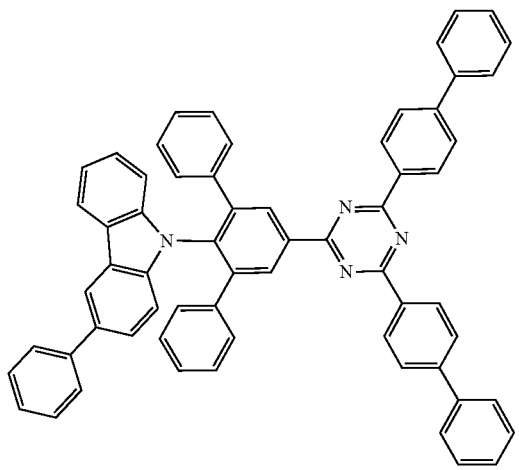
605
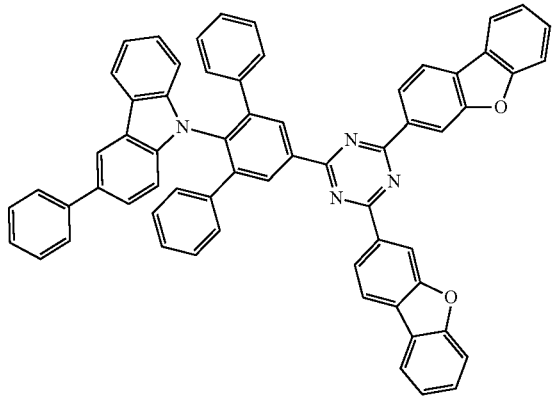
606
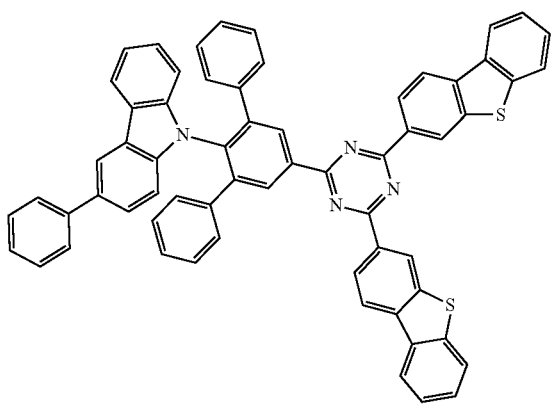
607
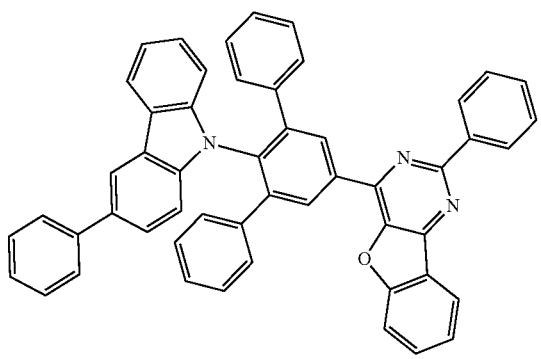
608
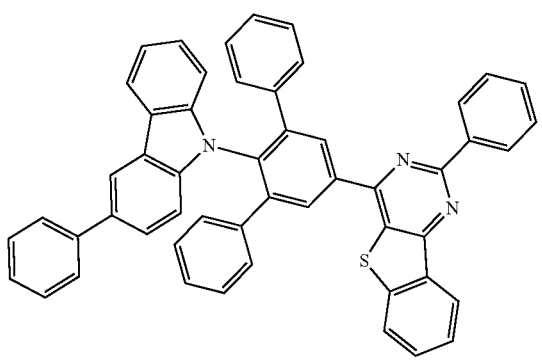

609
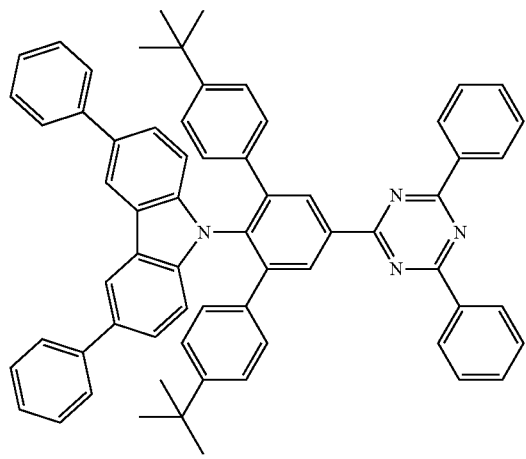
610
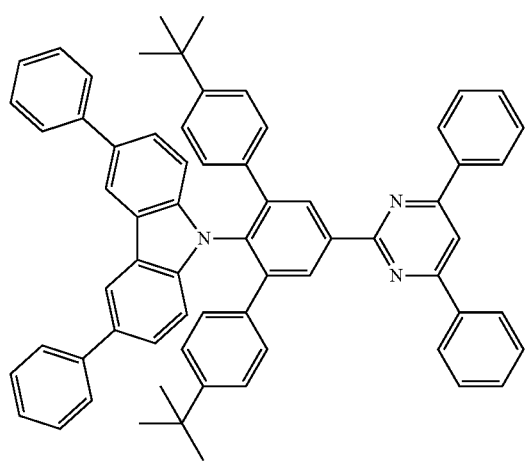
611
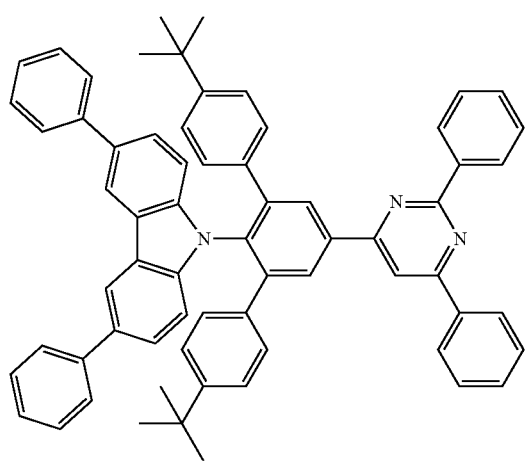

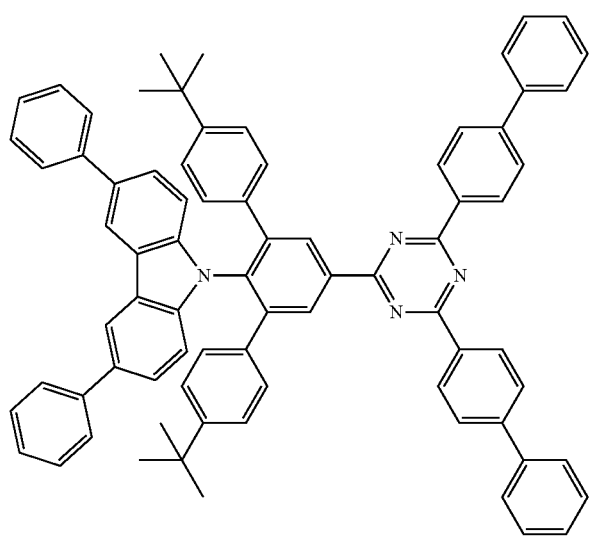
612
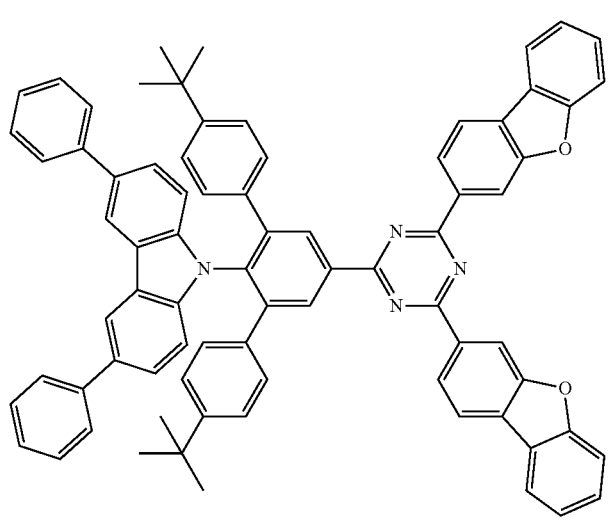
613
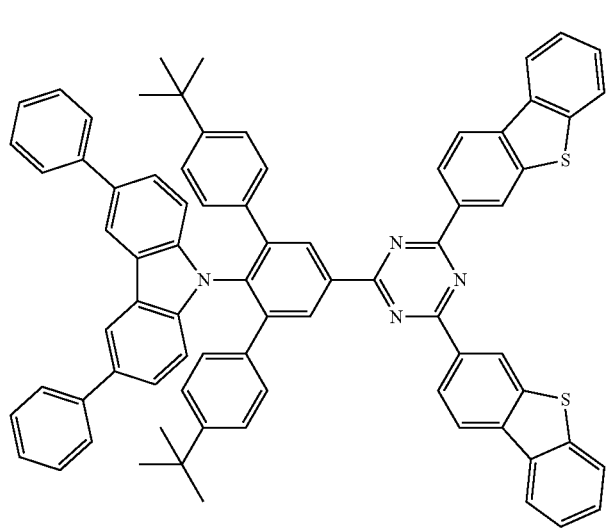
614

615
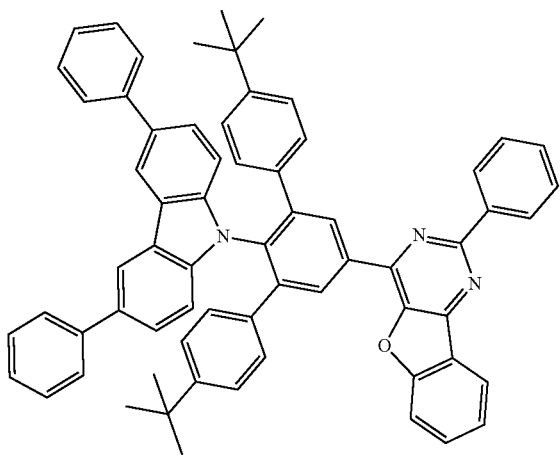
616
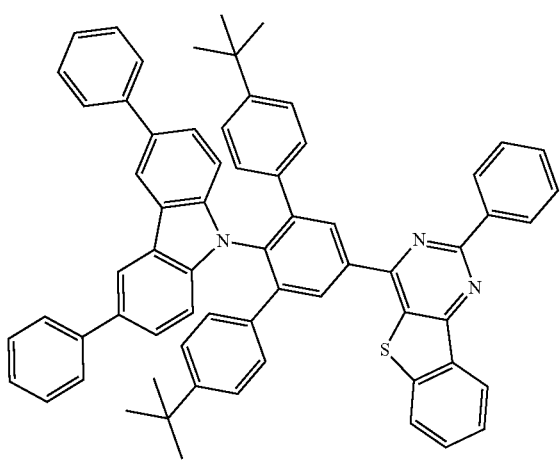
617
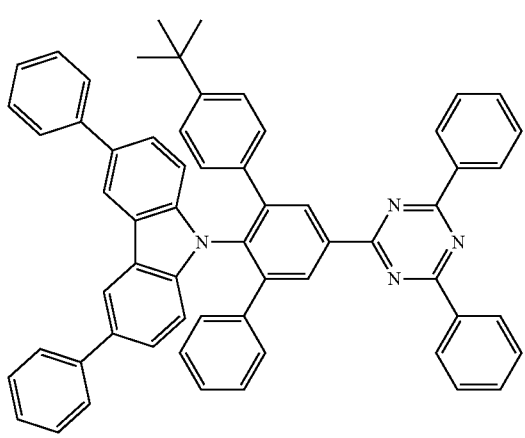

-continued
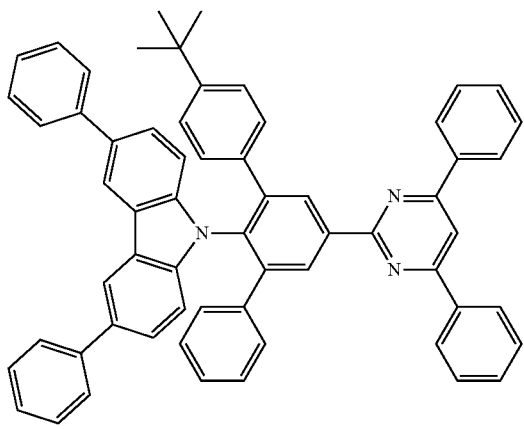
618
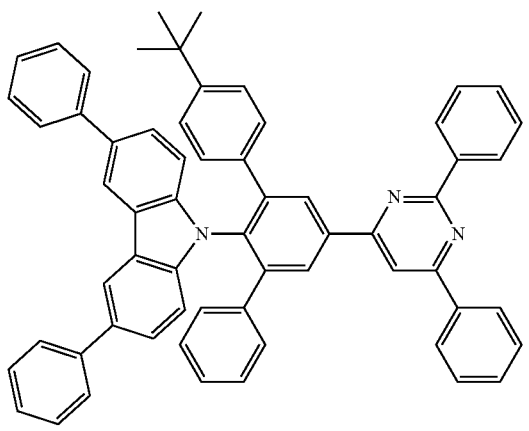
619
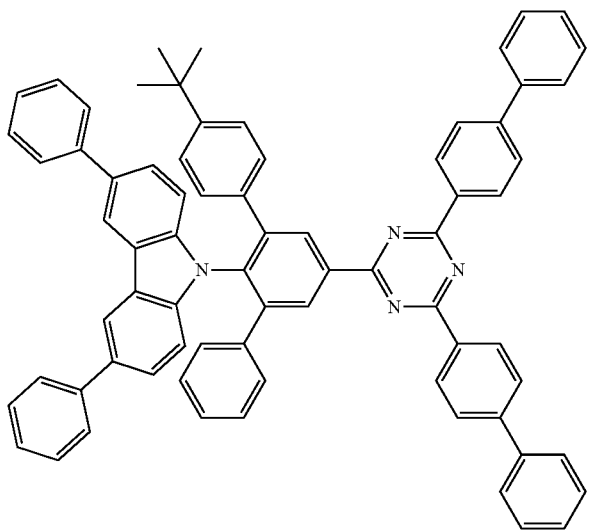
620

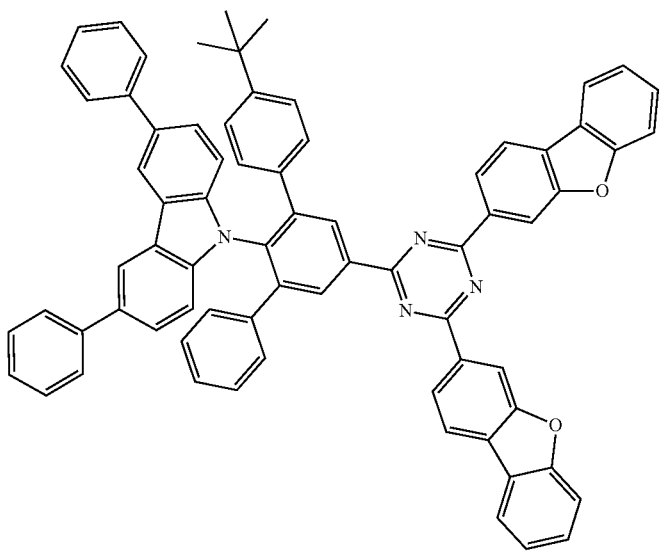
621

622
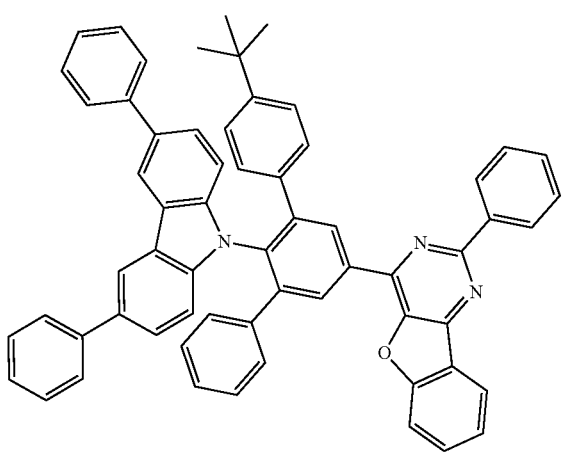
623

-continued
624
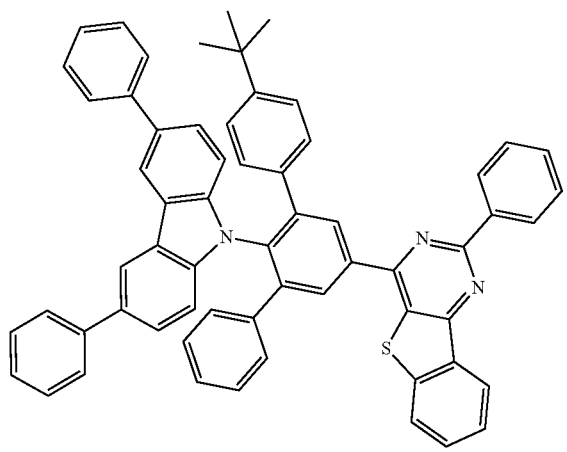
625
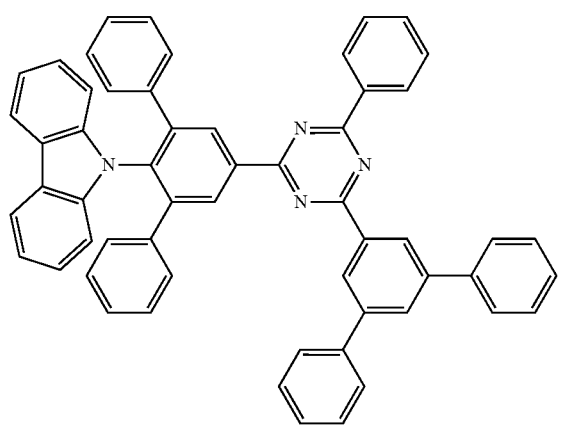
626
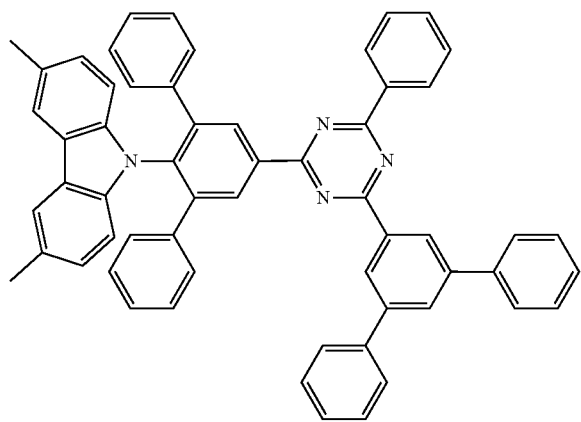

627
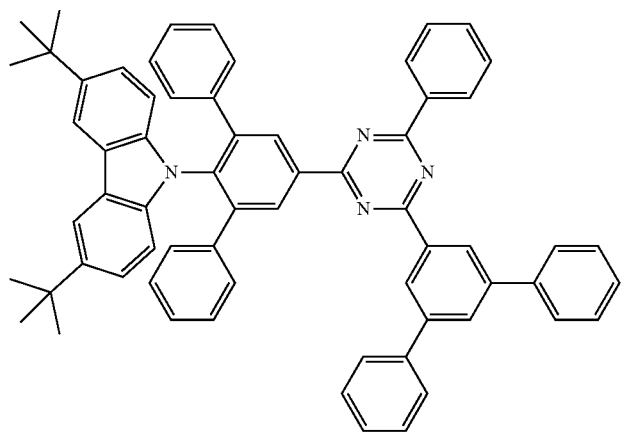
628
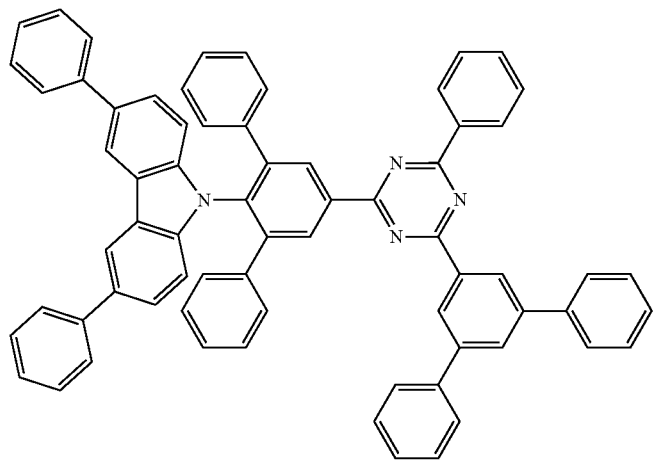
629
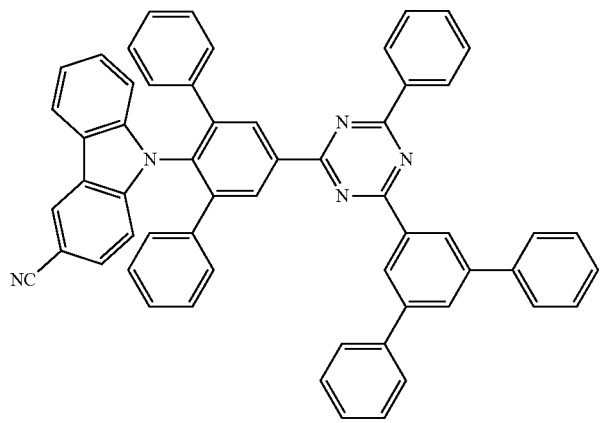

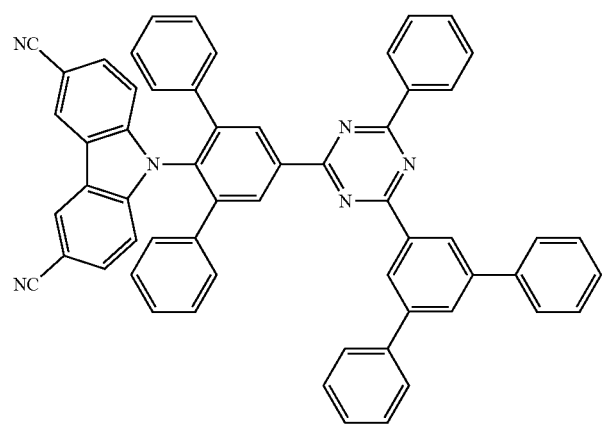
630
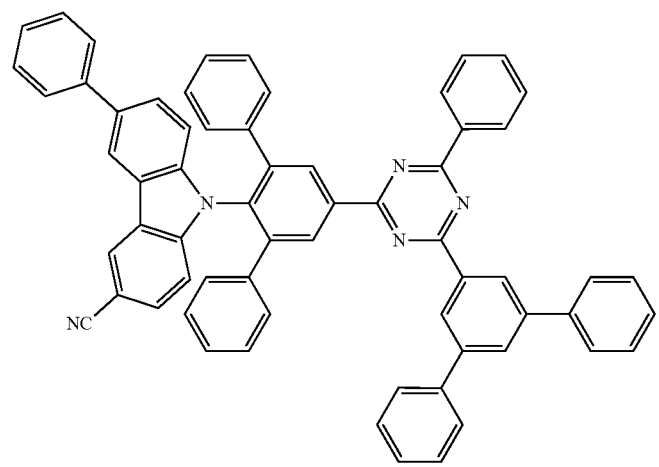
631
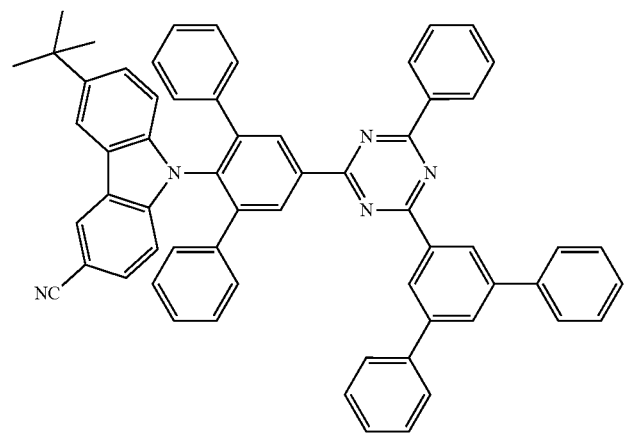
632

633
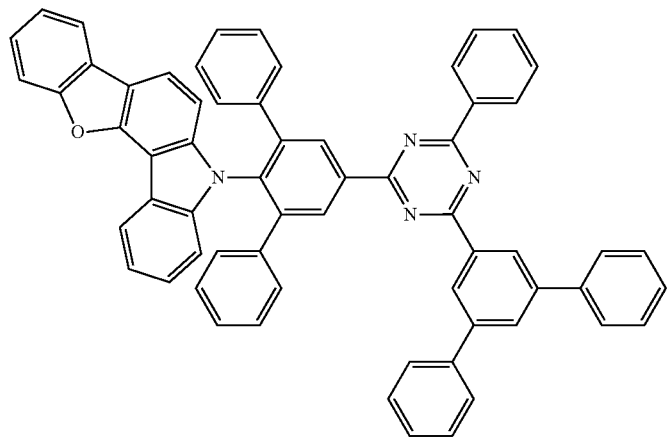
634
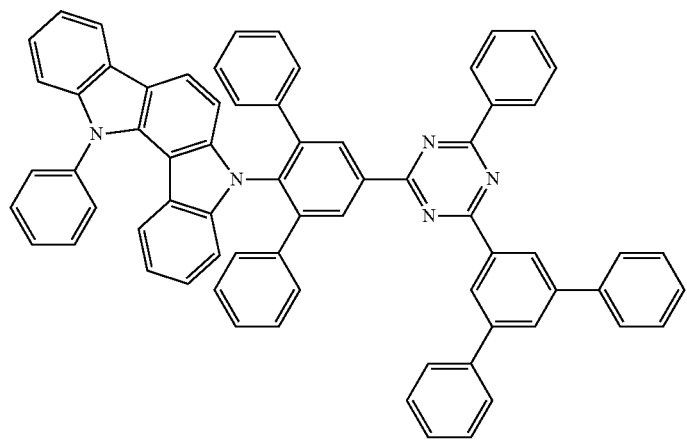
635
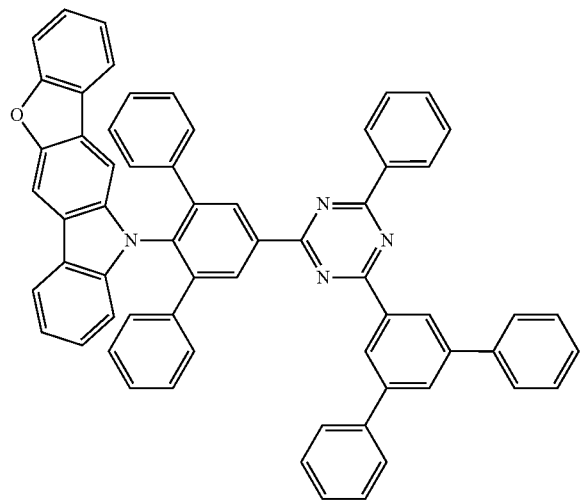

-continued
636
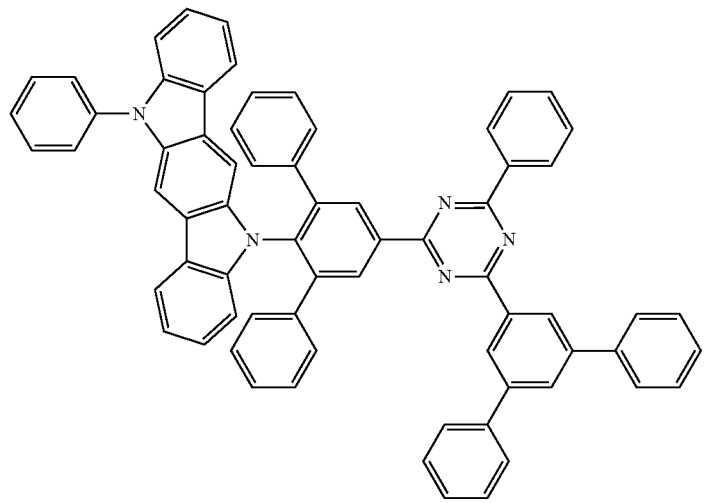
637
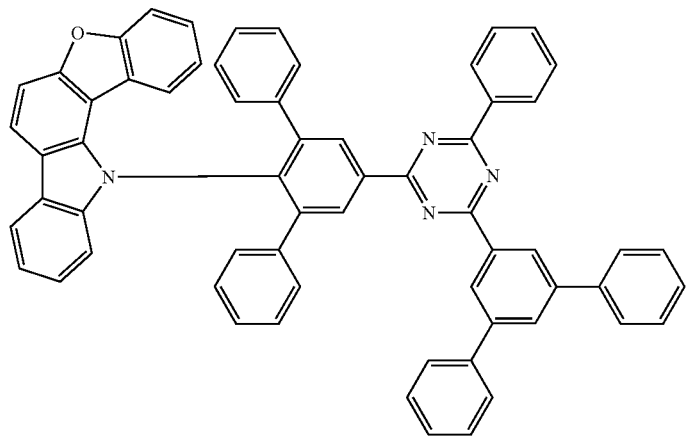
638
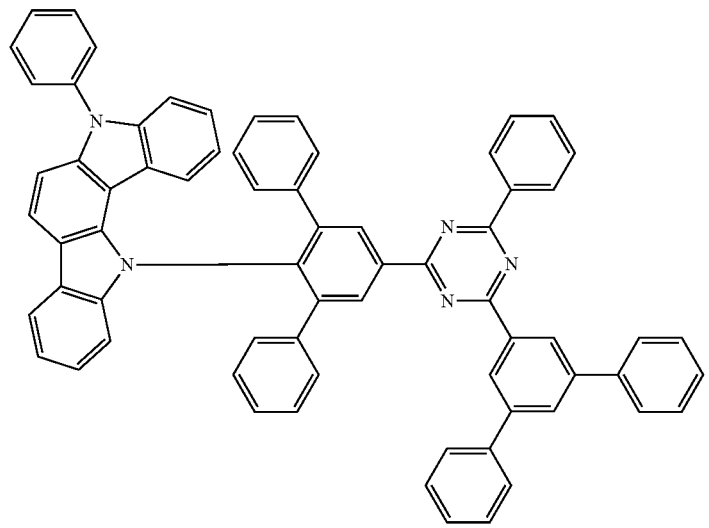

-continued
639
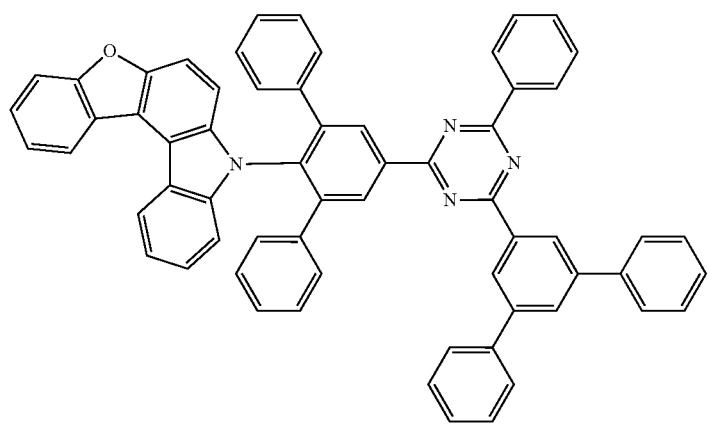
640
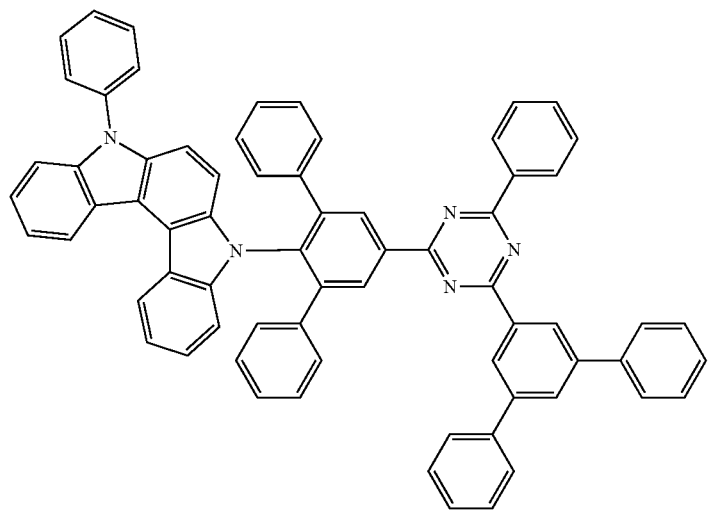
641
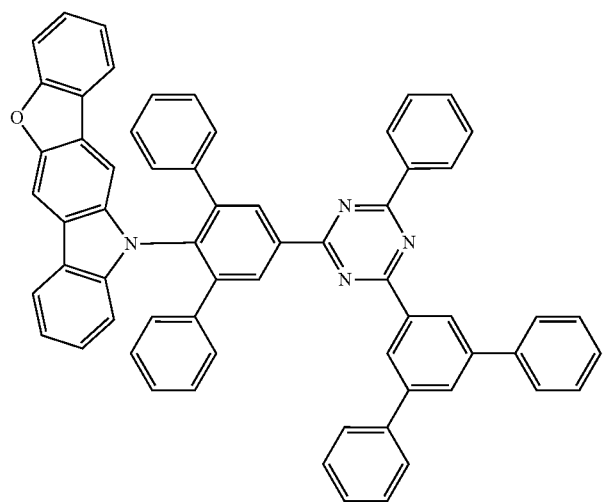

-continued
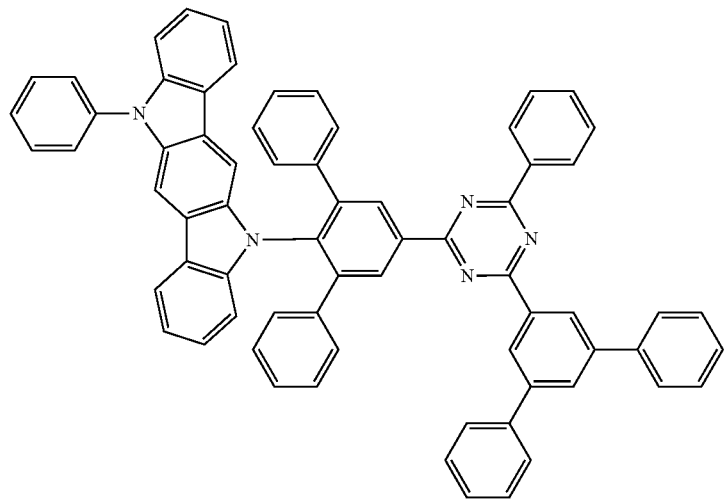
642
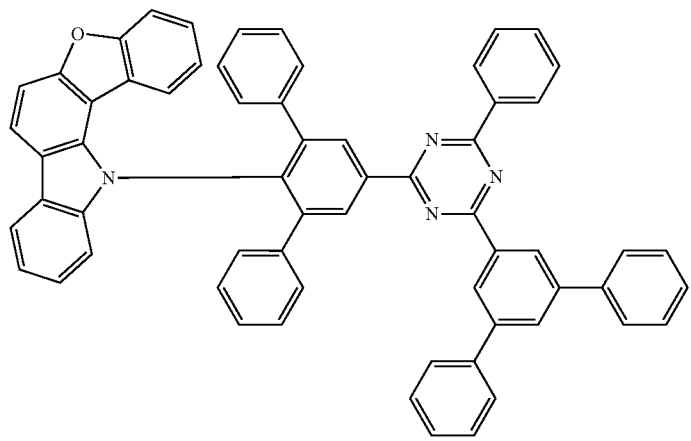
643
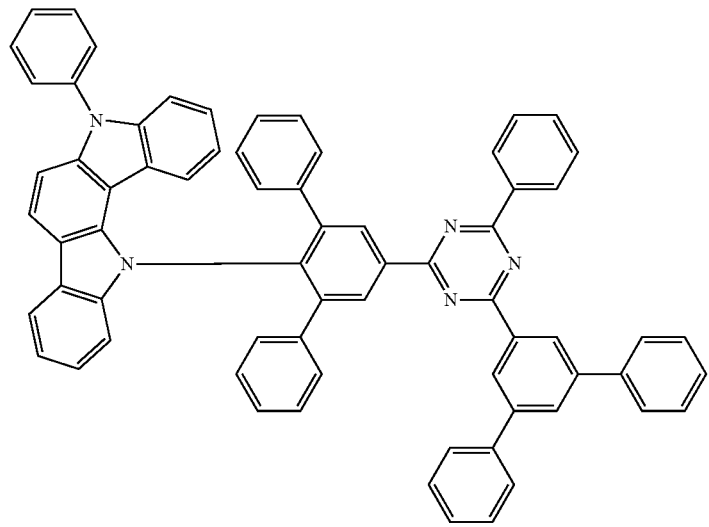
644

-continued
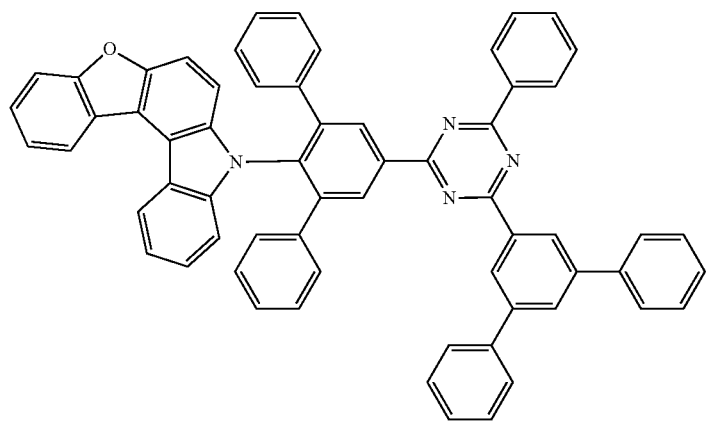
645
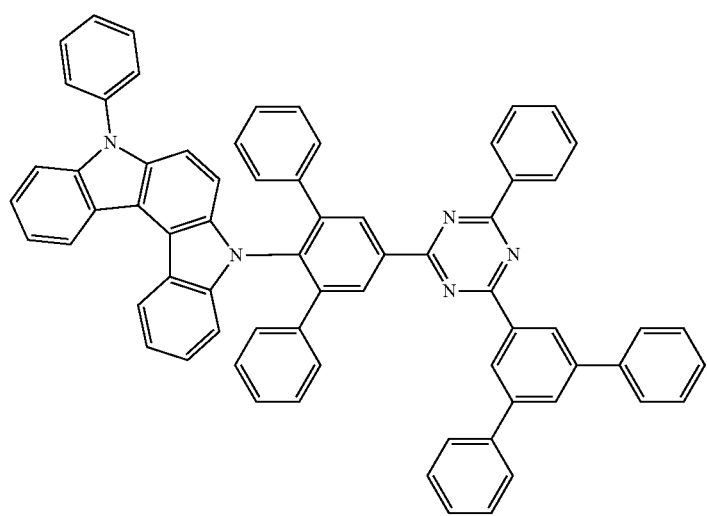
646
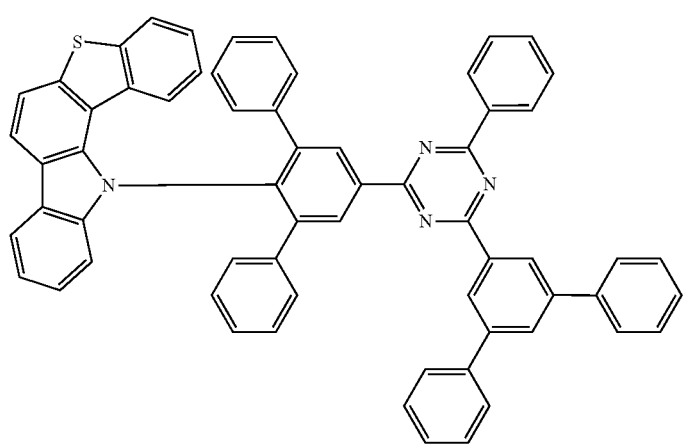
647

648
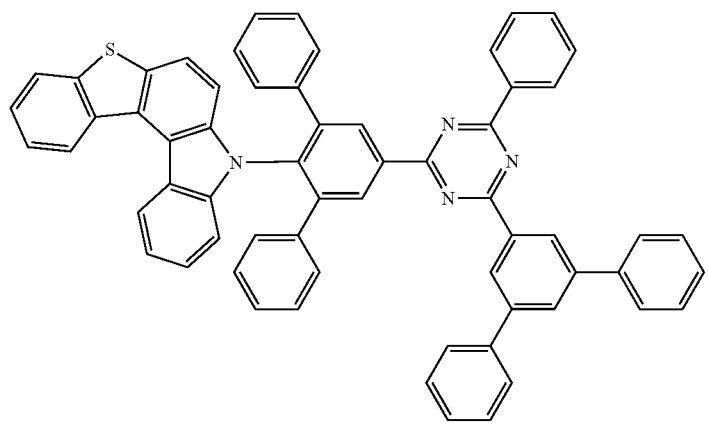
649
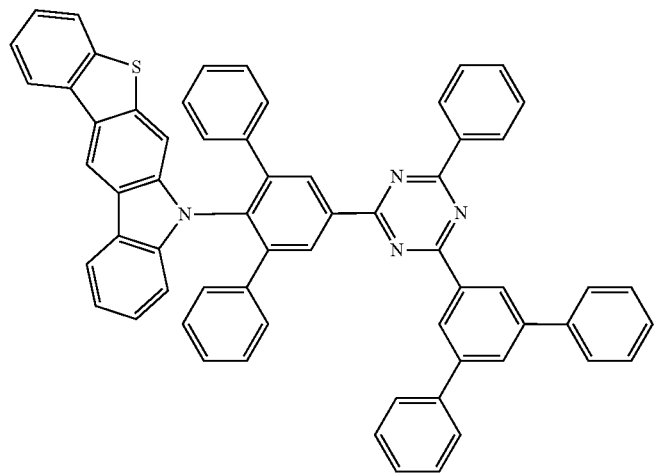
650
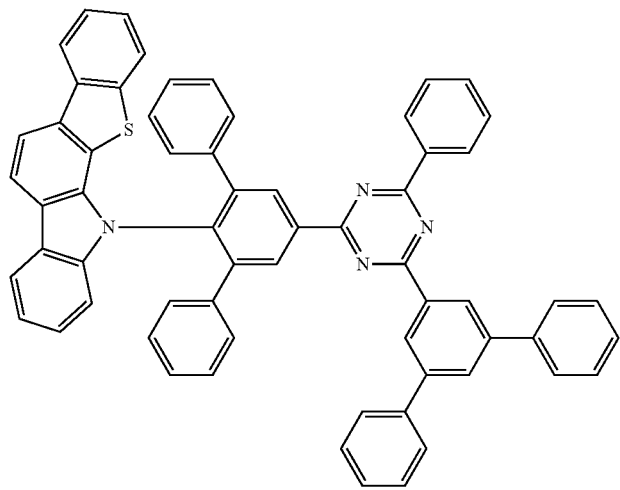

-continued
651
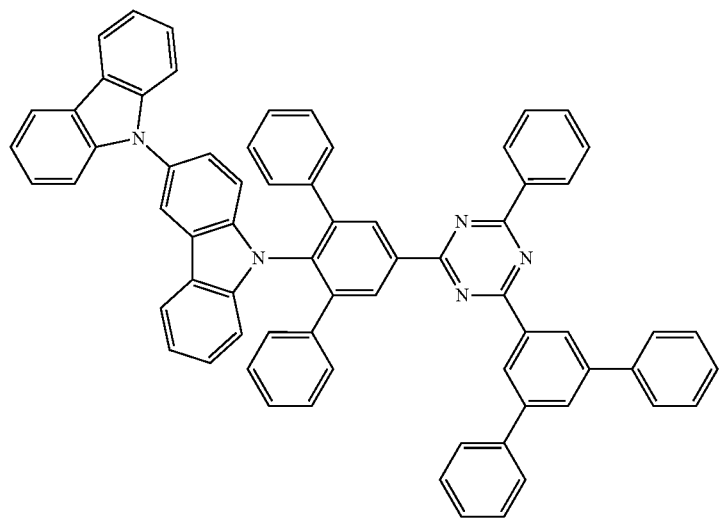
652
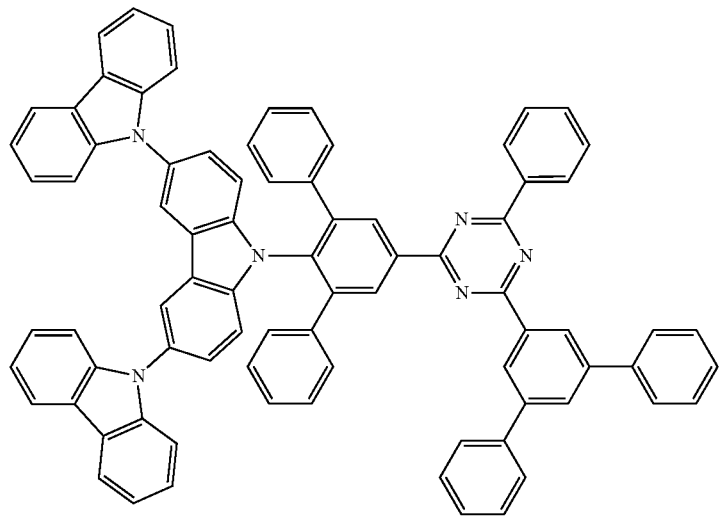
653
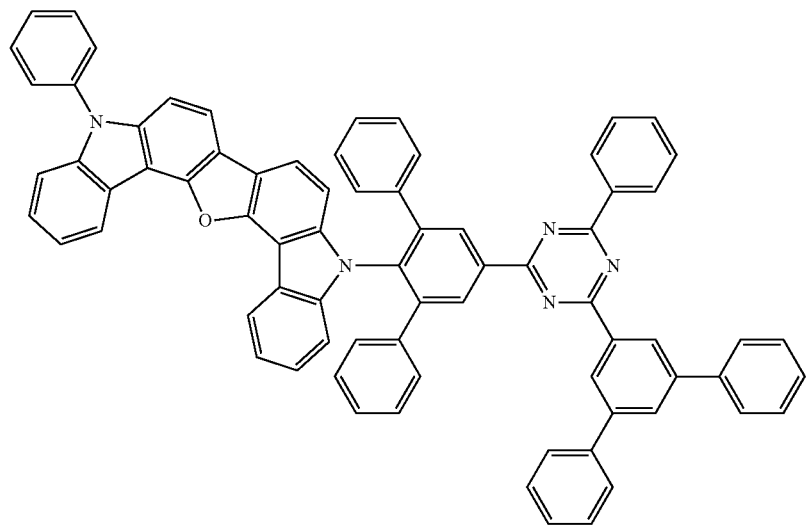

-continued
654
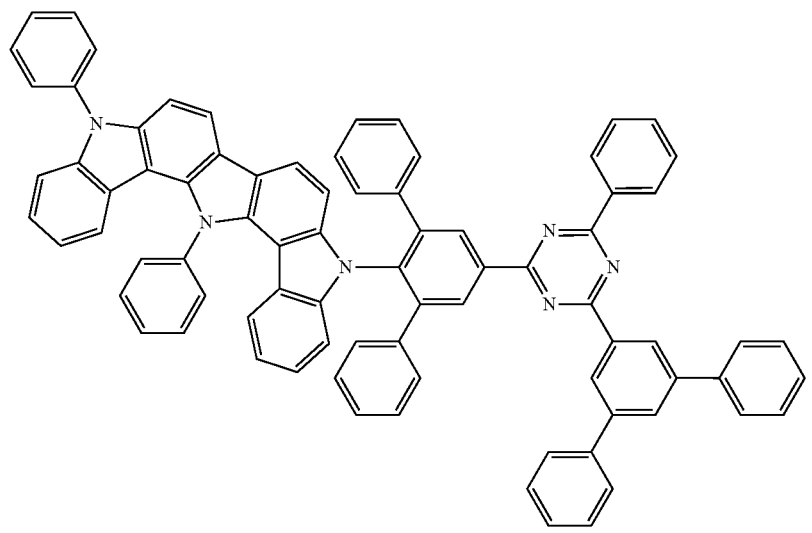
655
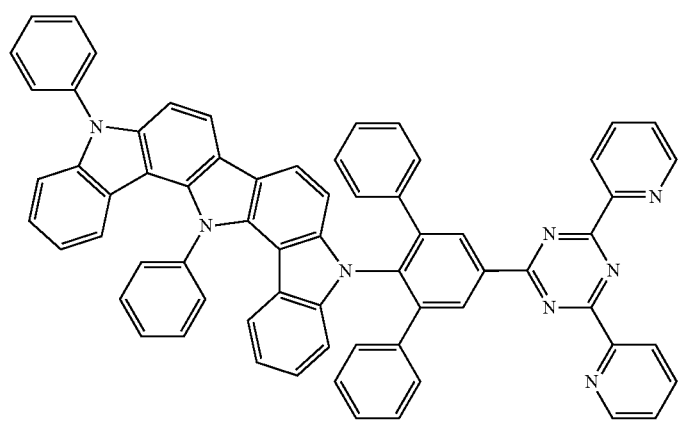
656
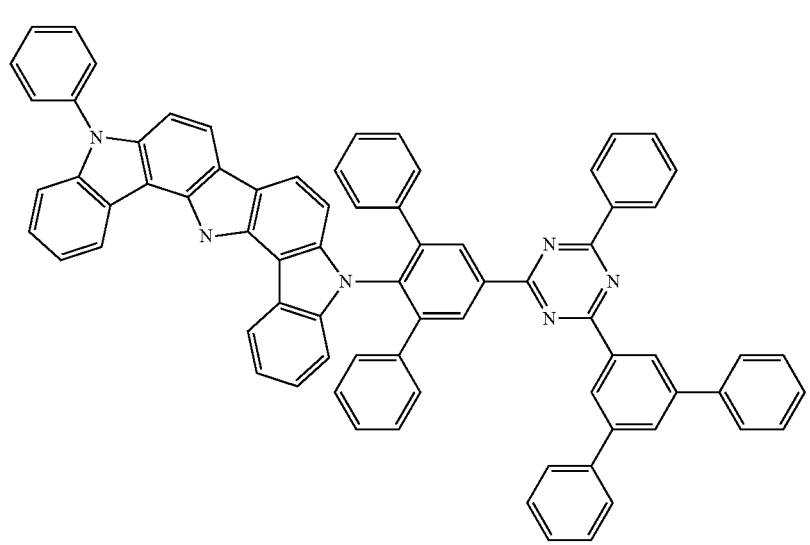

657
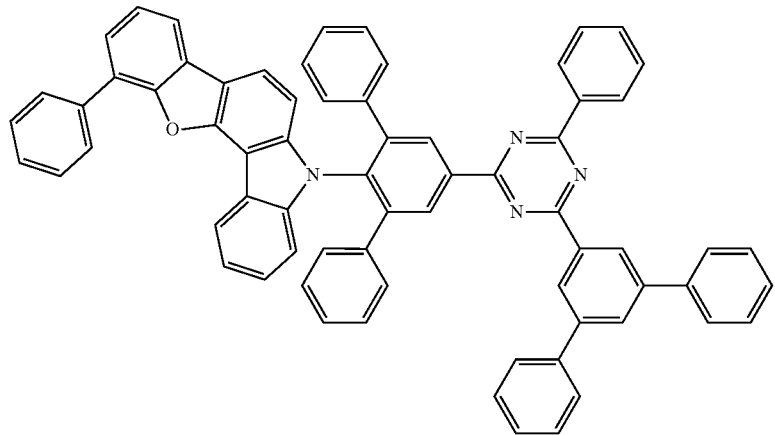
658
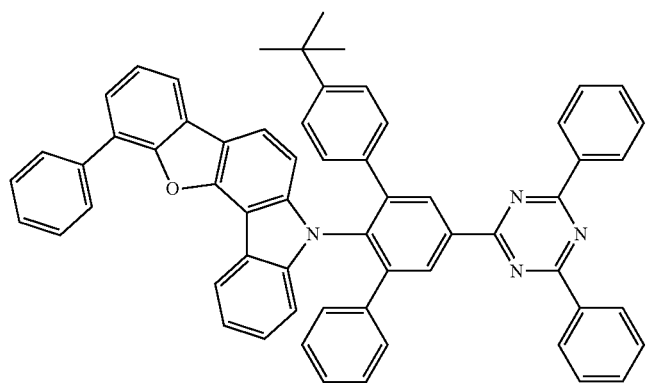
659
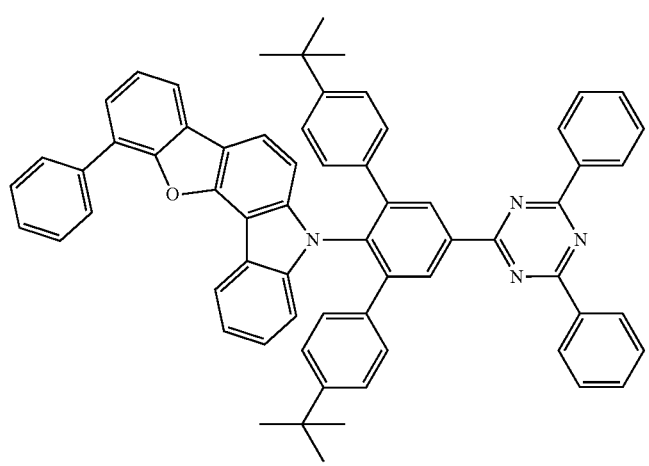

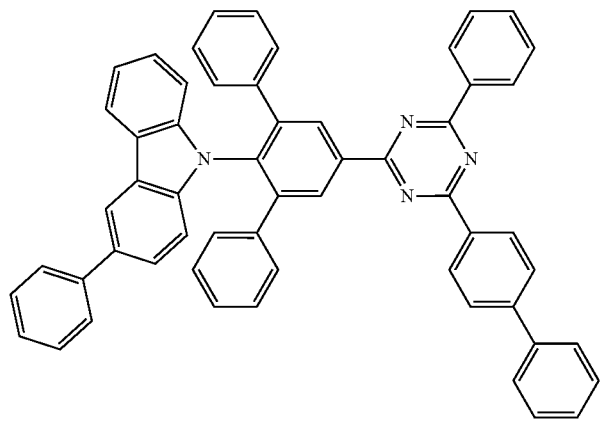
660
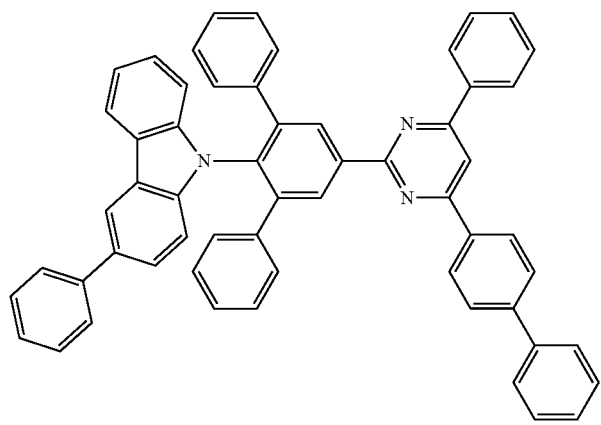
661
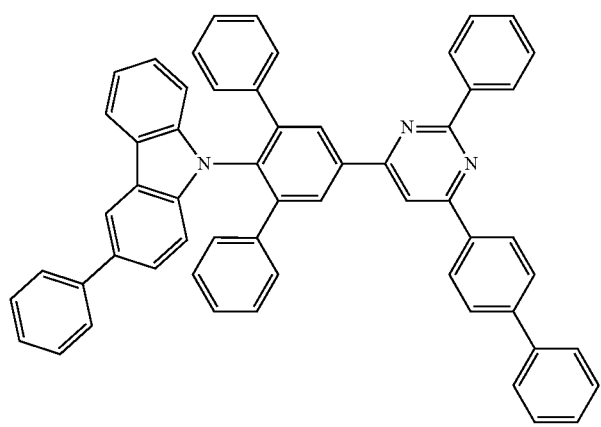
662

-continued
663
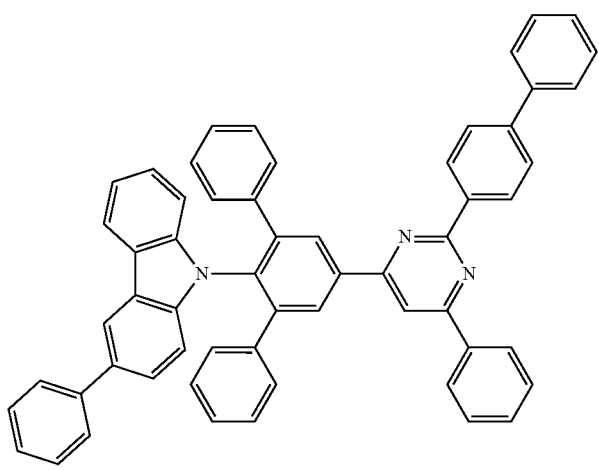
664
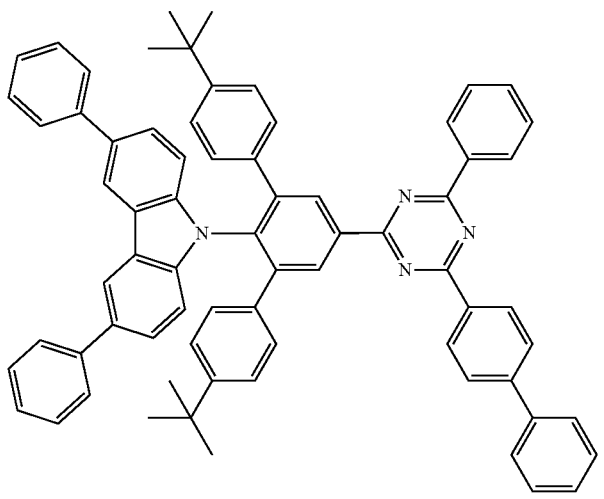
665
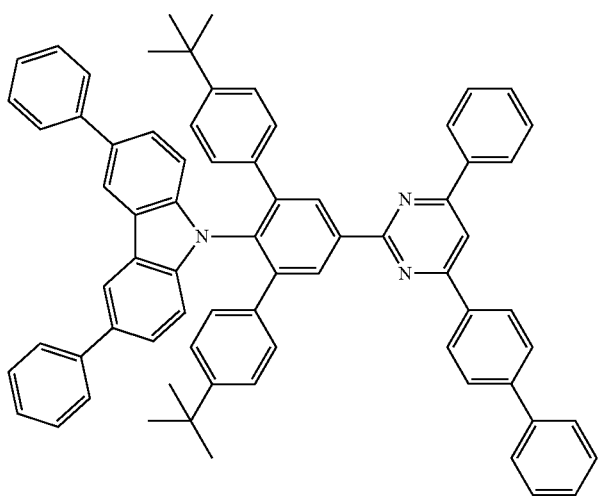

-continued
666
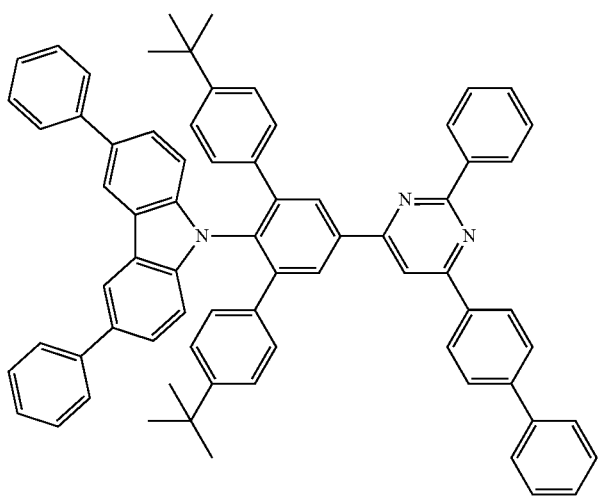
667
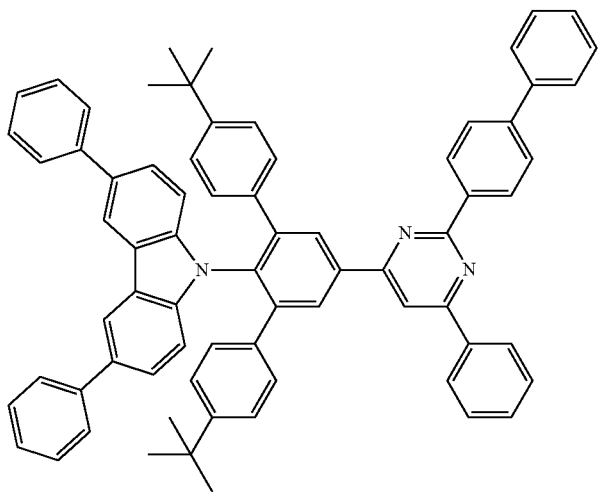
668
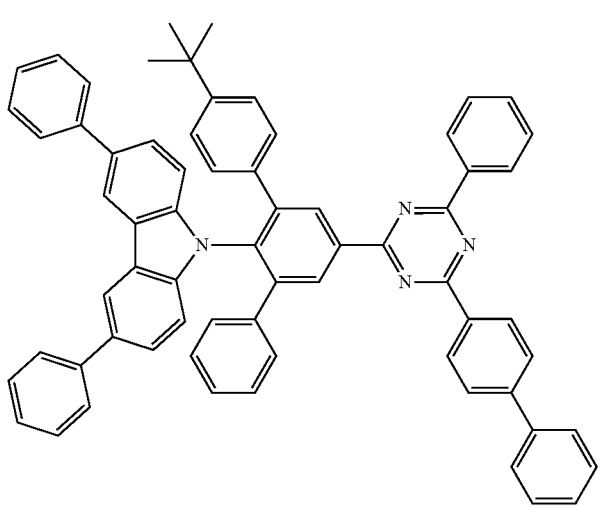

-continued
669
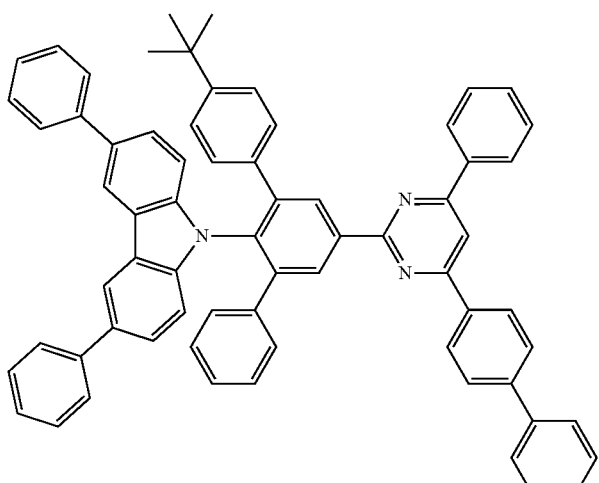
670
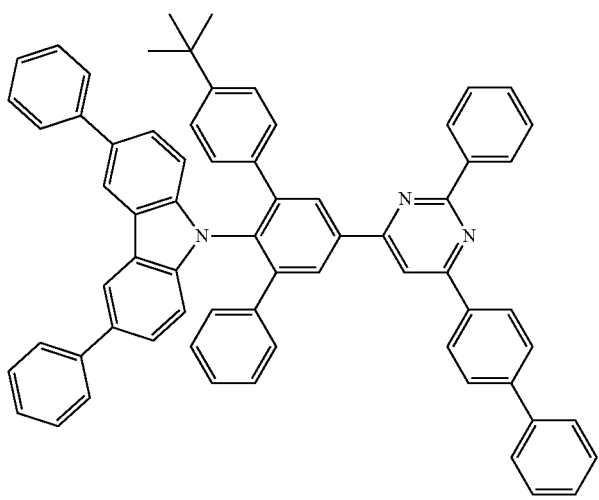
671
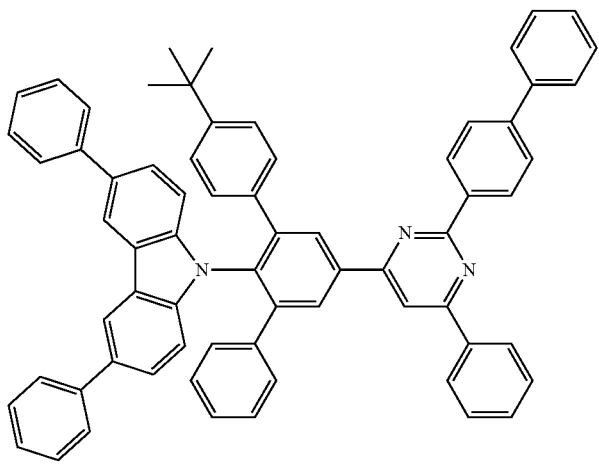

-continued
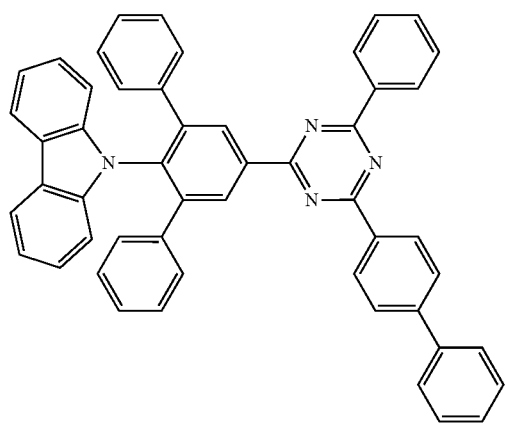
672
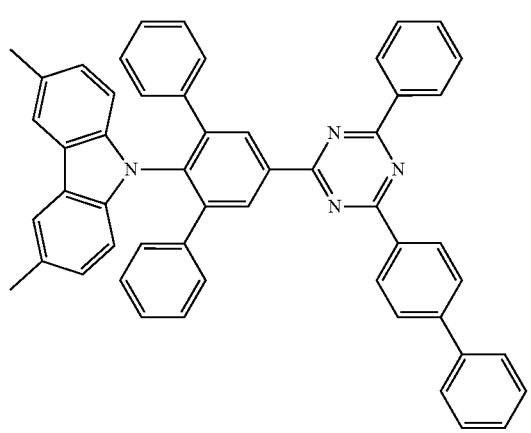
673
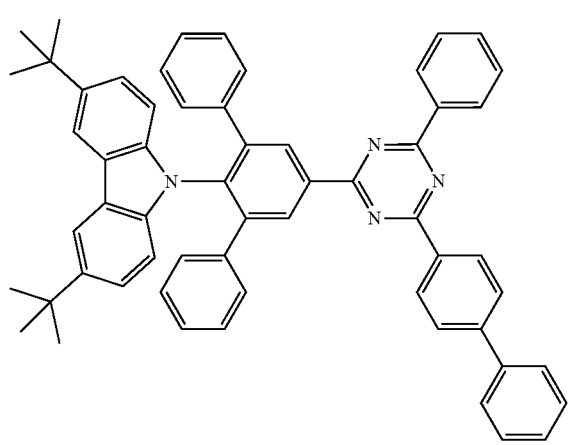
674

-continued
675
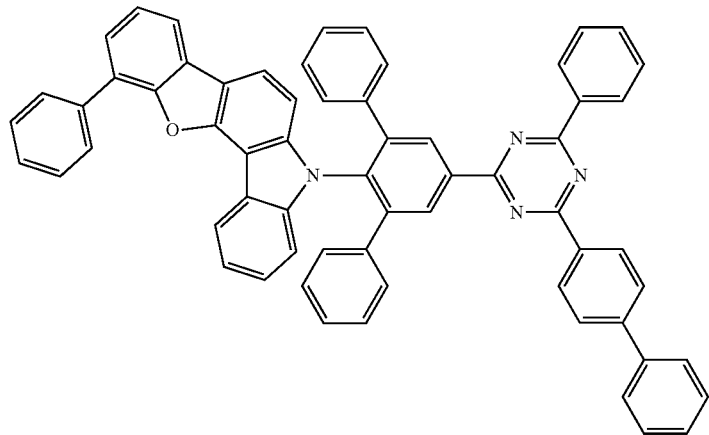
676
677
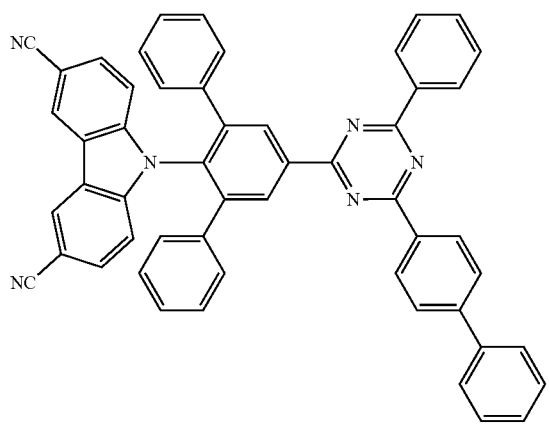

678
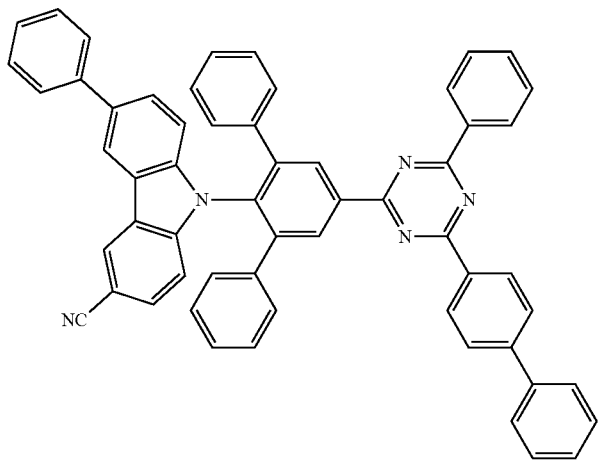
679
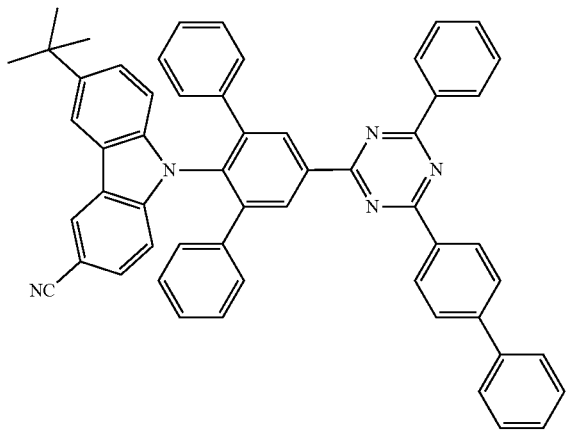
680
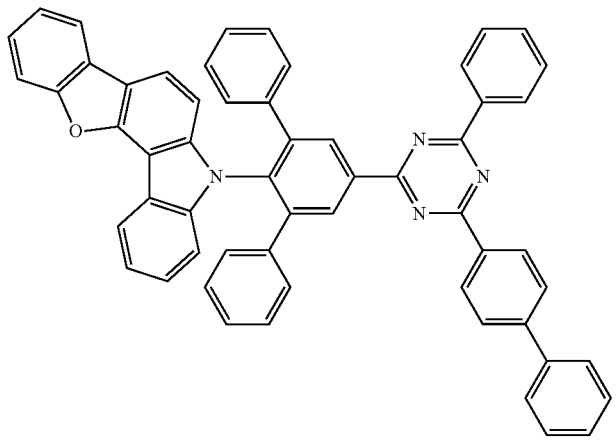

681
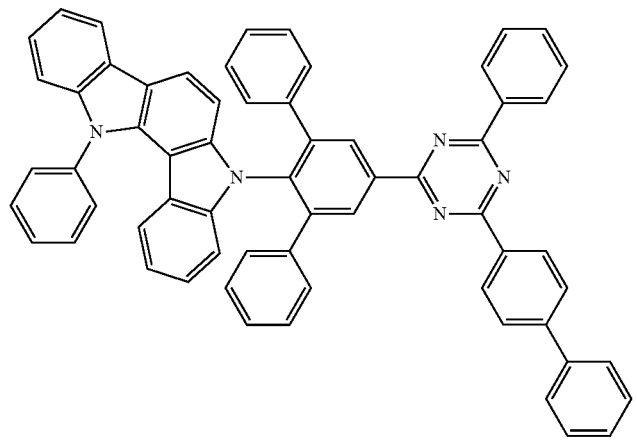
682
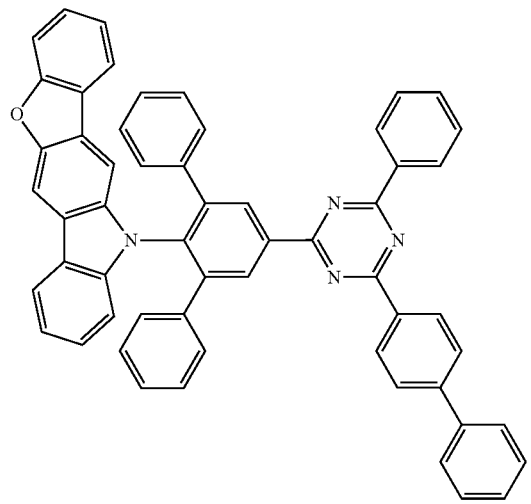
683
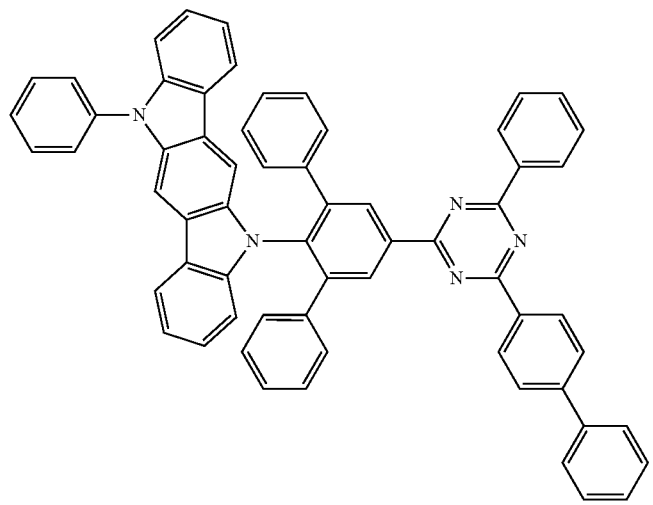

684
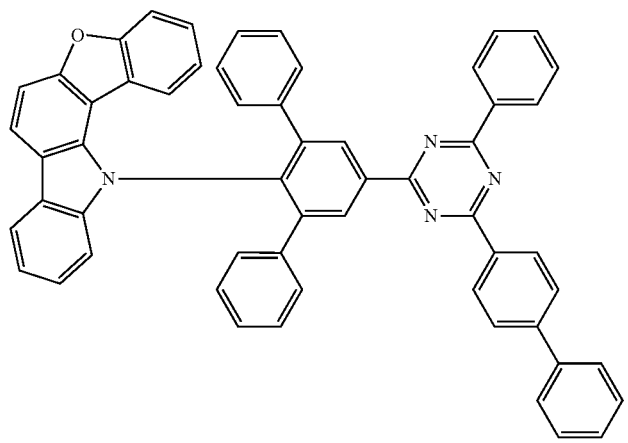
685
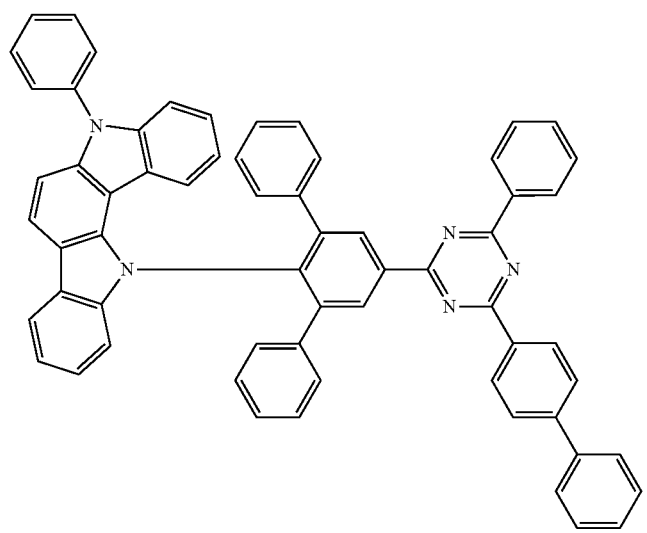
686
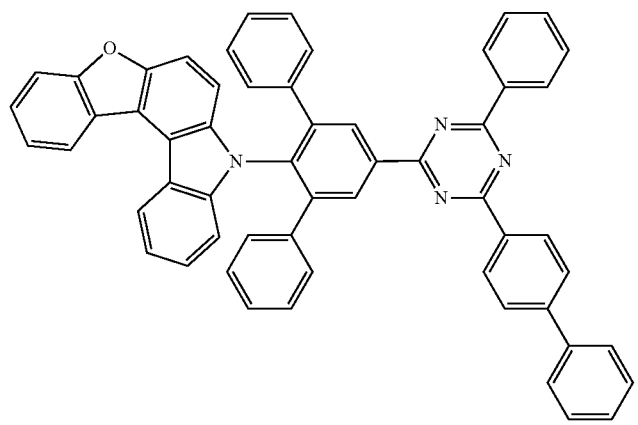

687
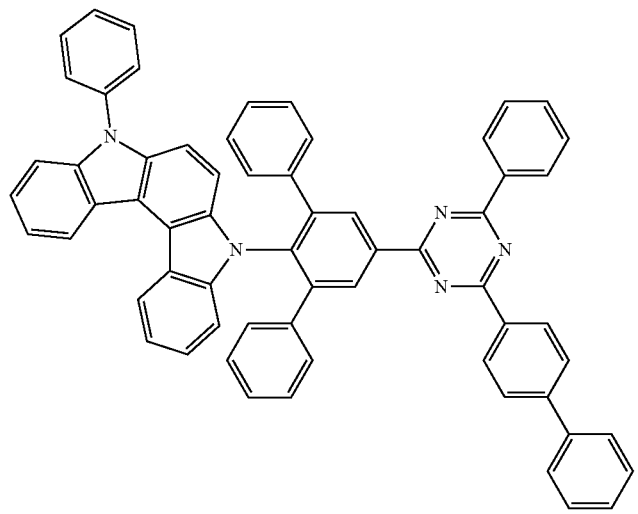
688
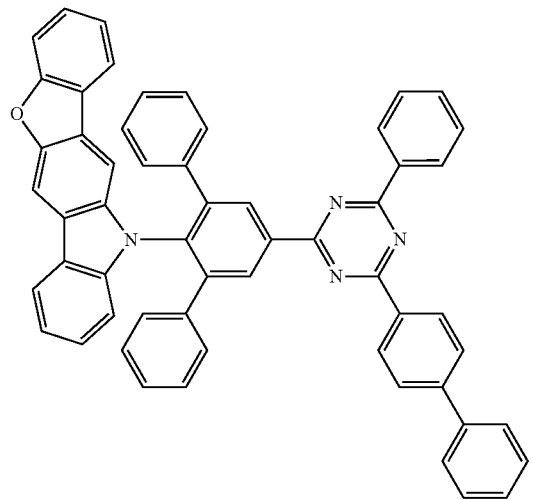
689
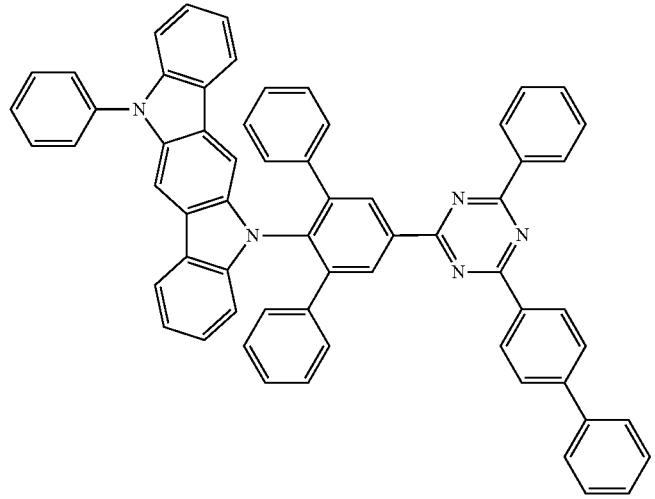

-continued
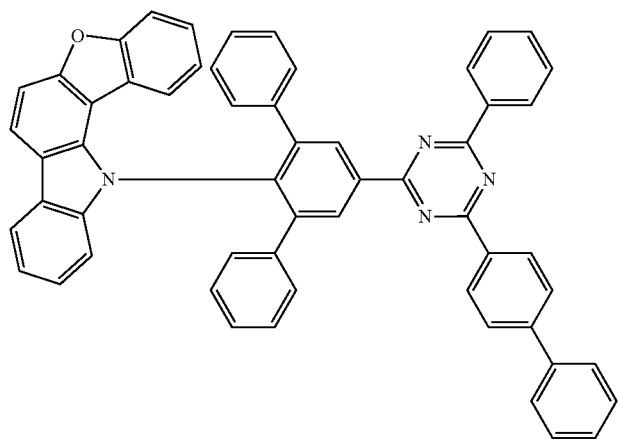
690
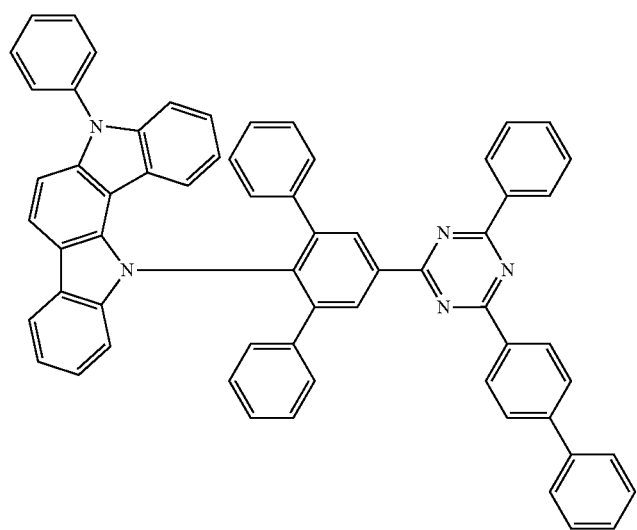
691
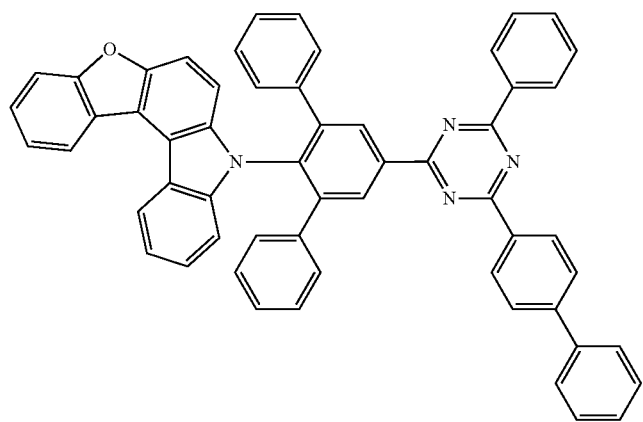
692

693
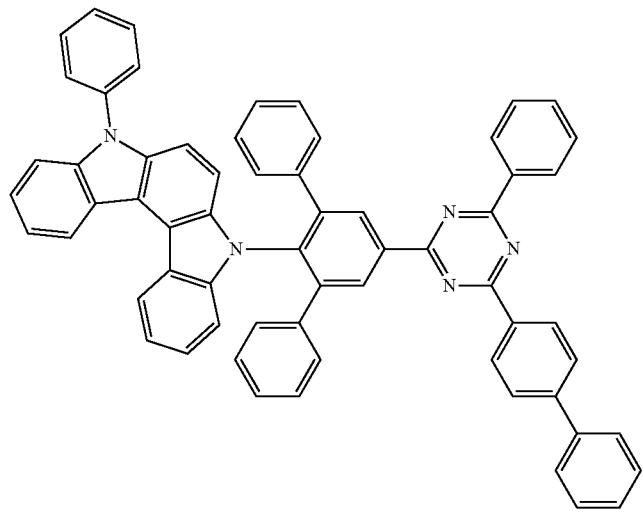
694
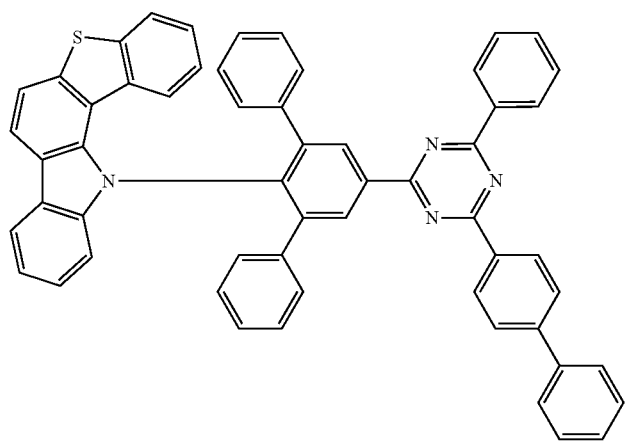
695
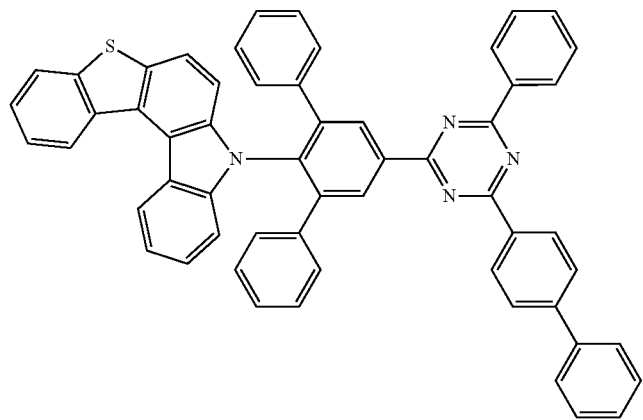

-continued
696
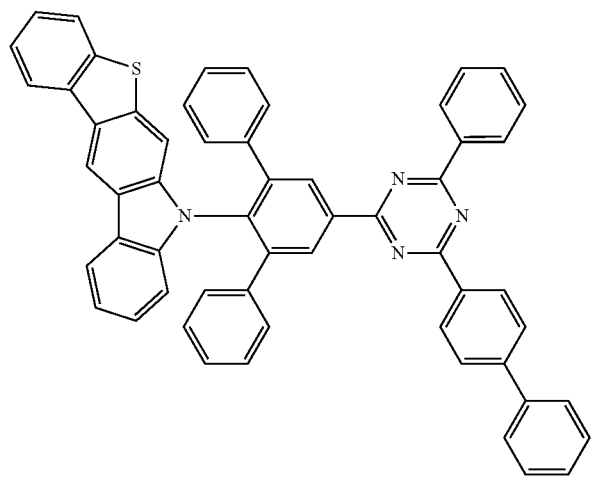
697
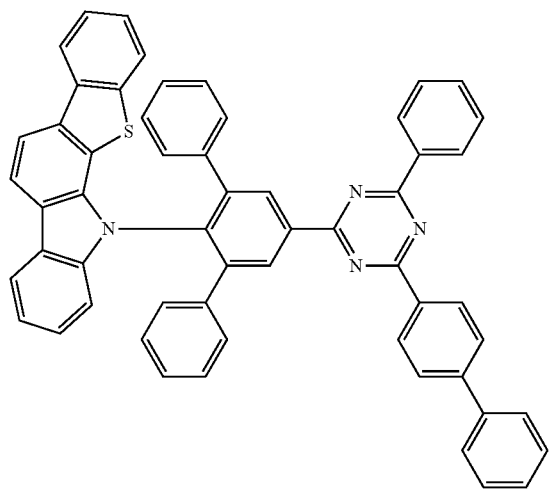
698
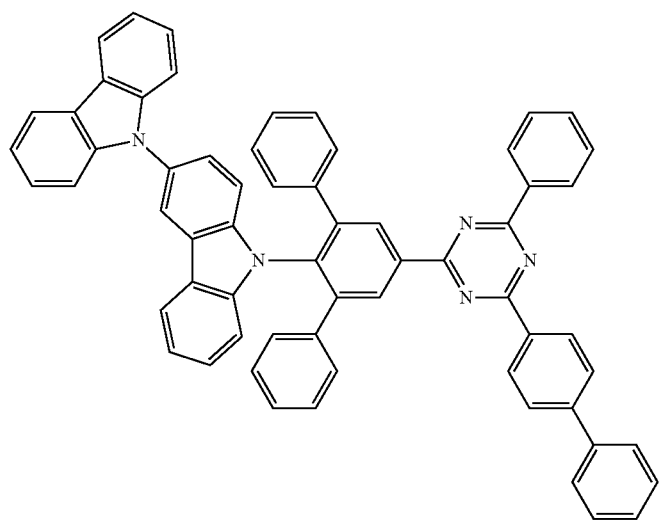

699
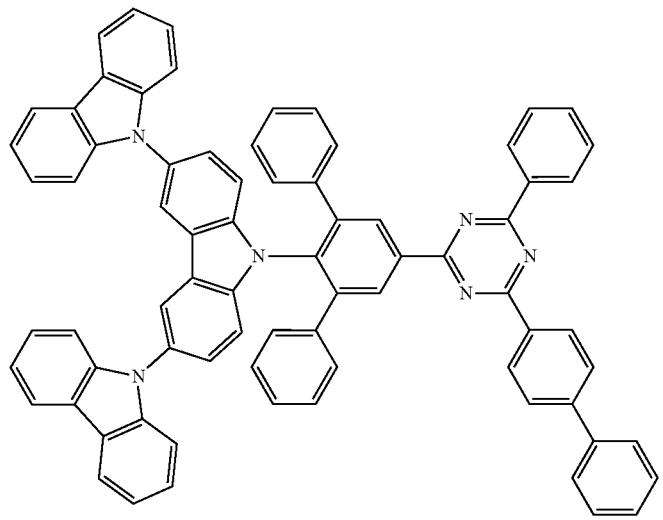
700
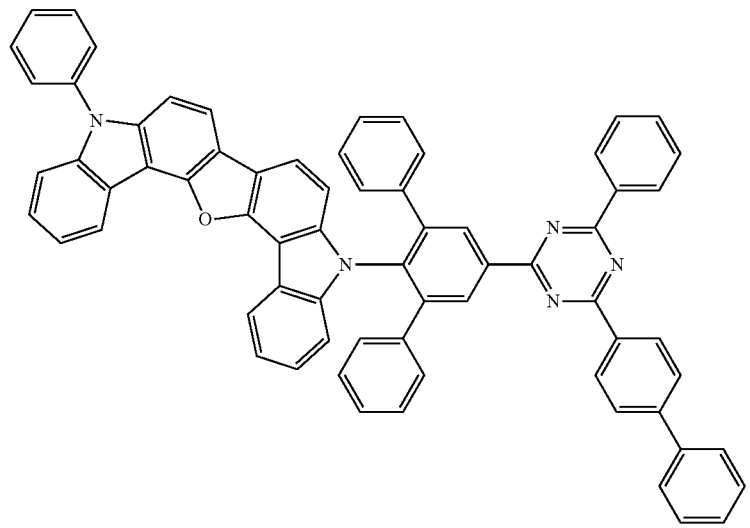
701
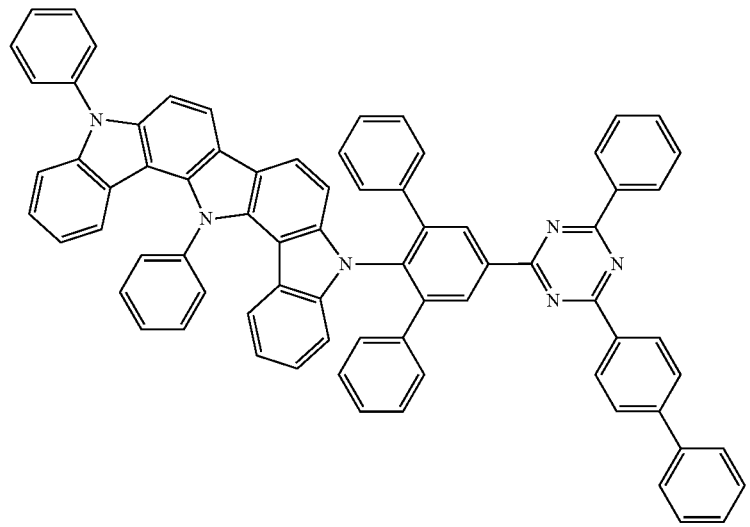

-continued
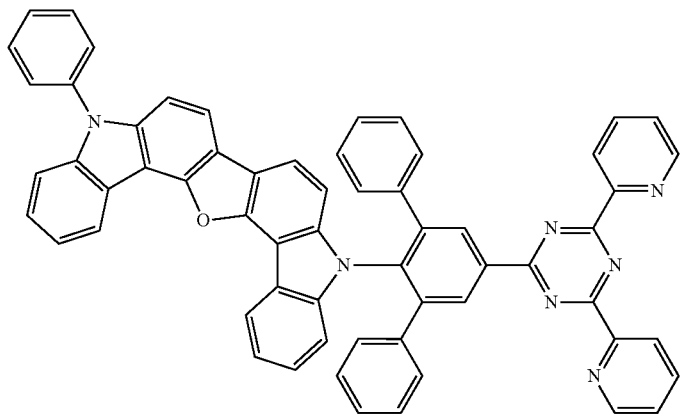
702
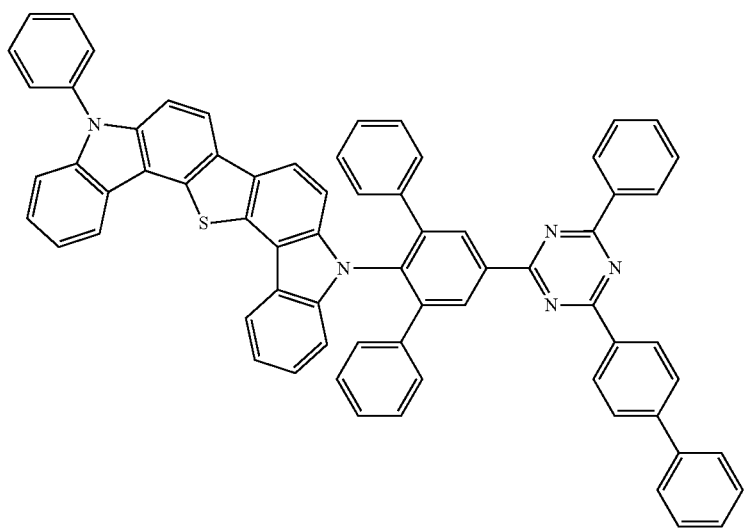
703
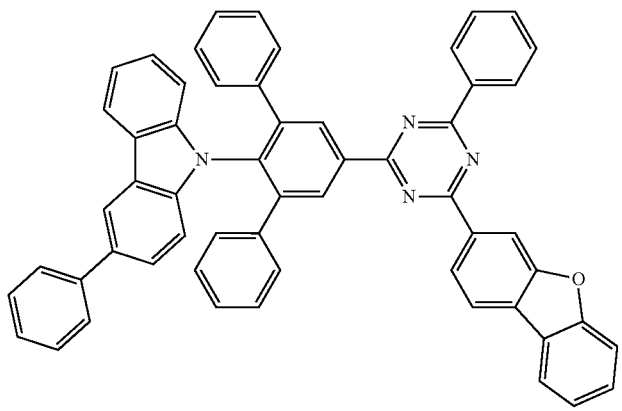
704

-continued
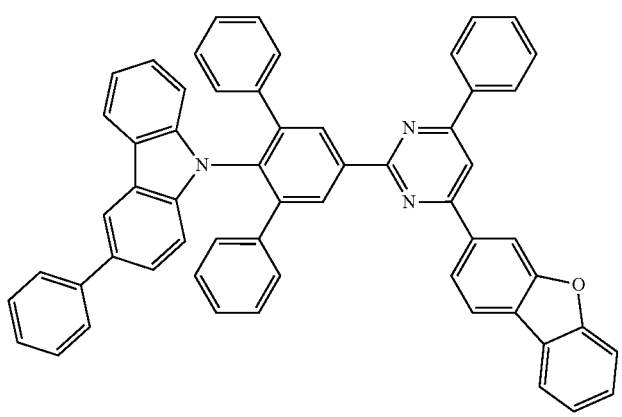
705
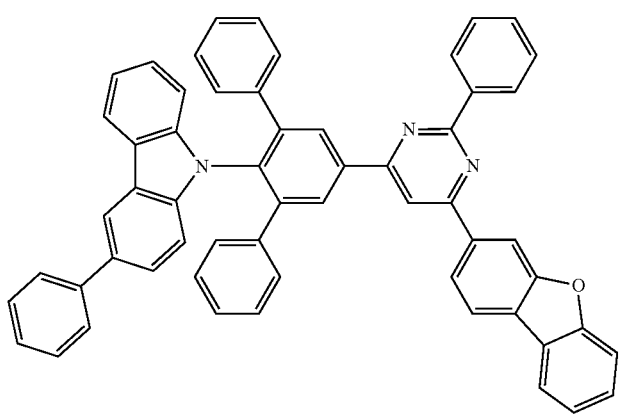
706
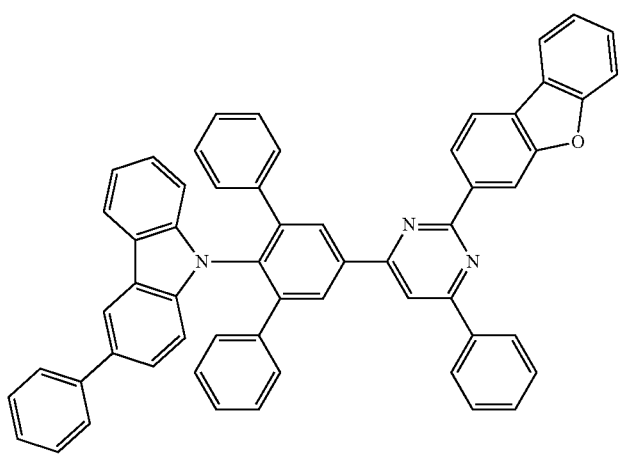
707

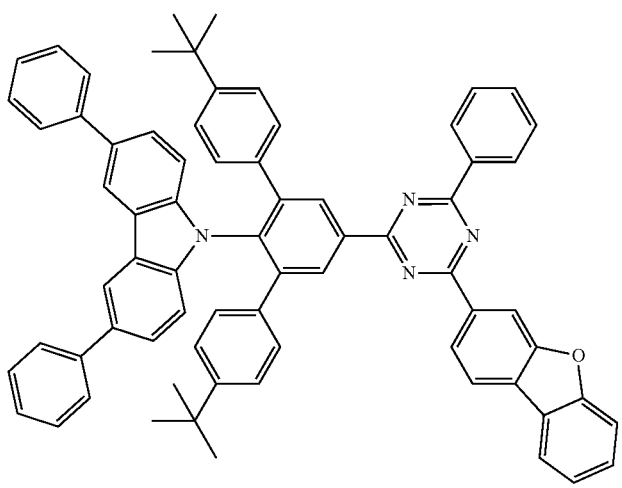
708
709
710

-continued
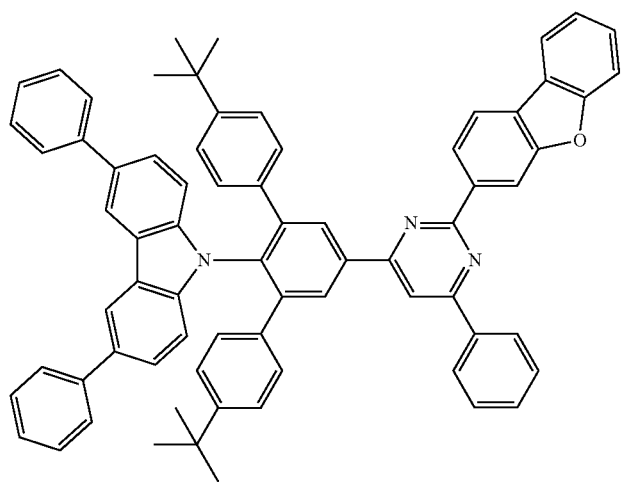
711
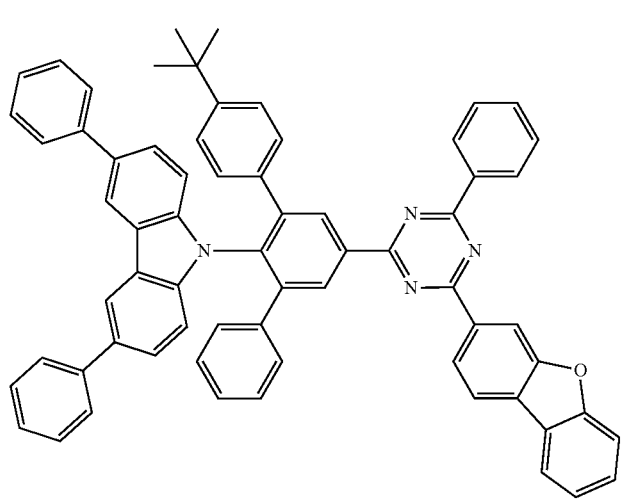
712
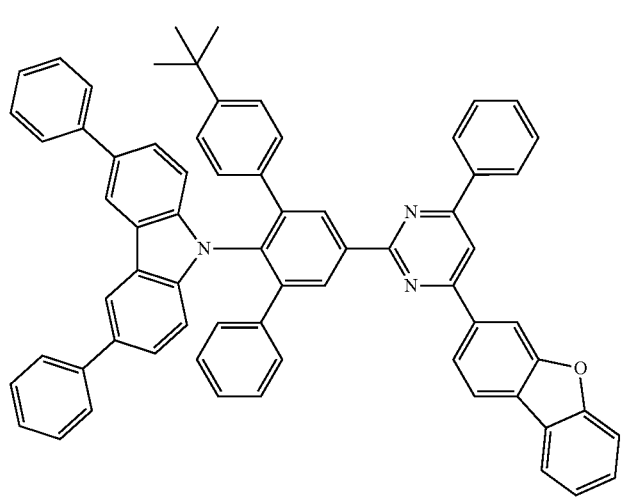
713

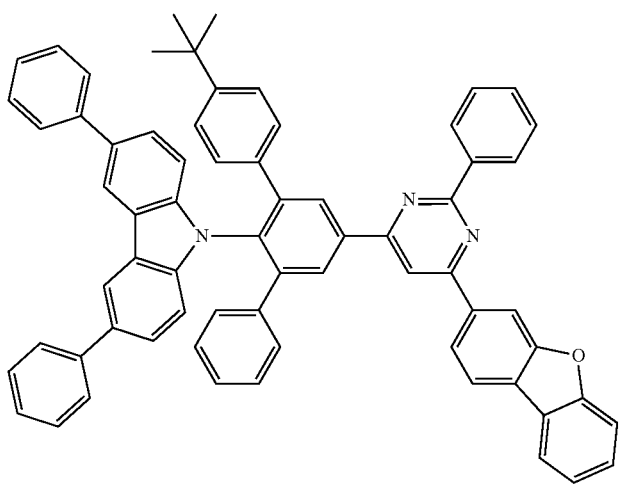
714
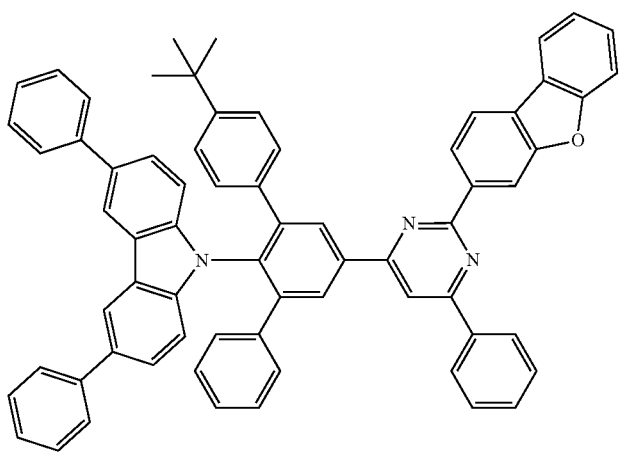
715
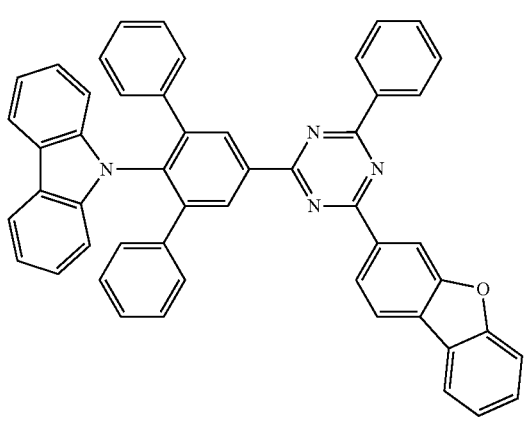
716

717
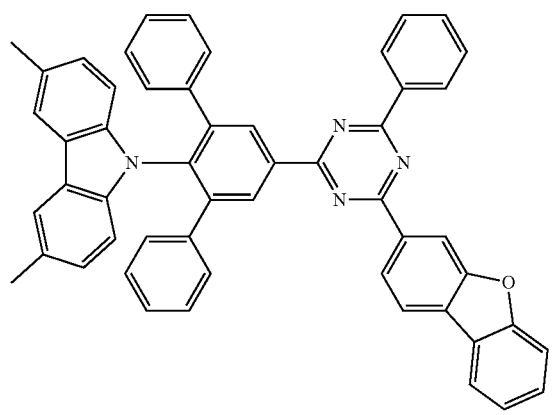
718
719

-continued
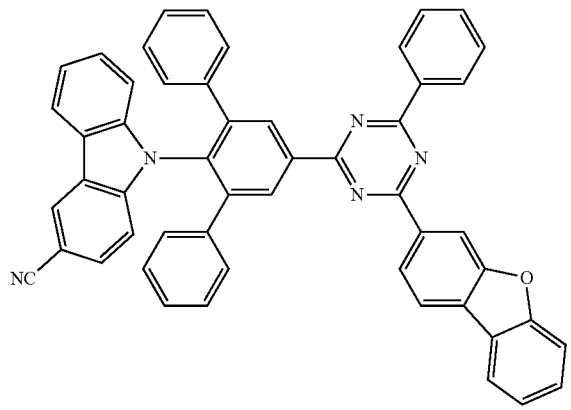
720
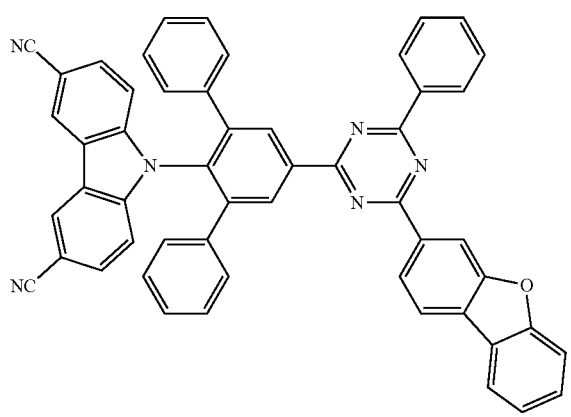
721
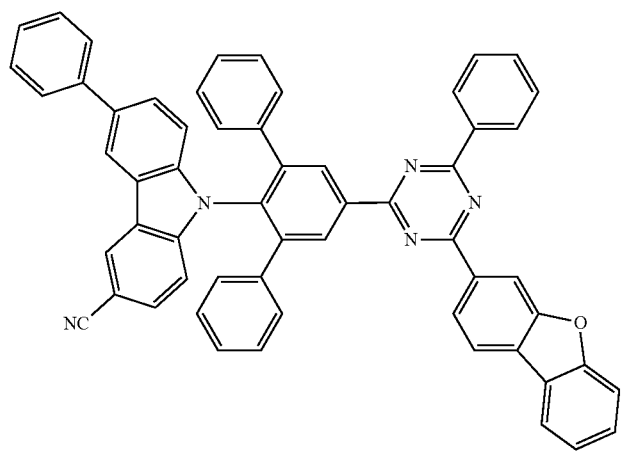
722

-continued
723
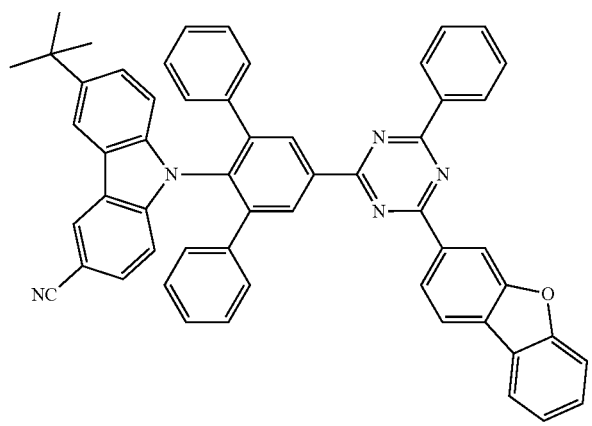
724
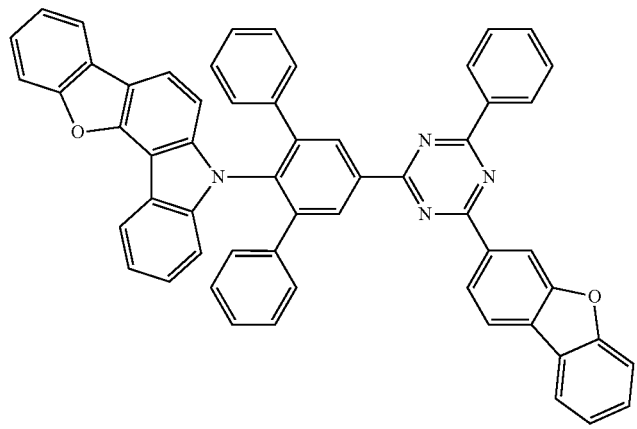
725
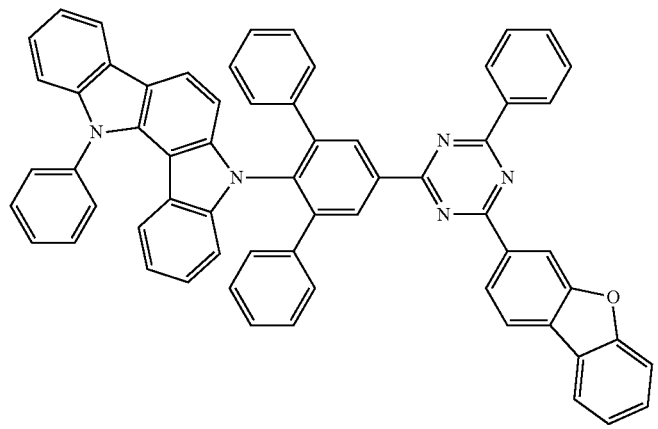

-continued
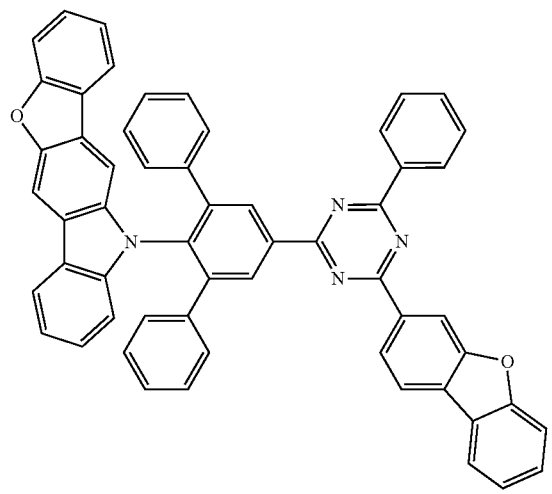
726
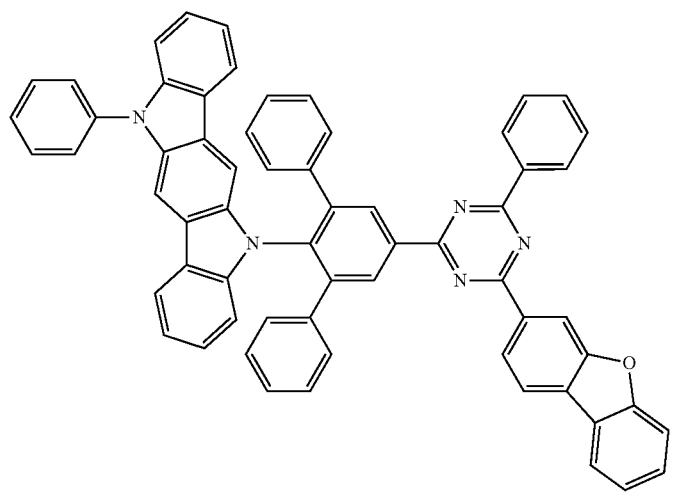
727
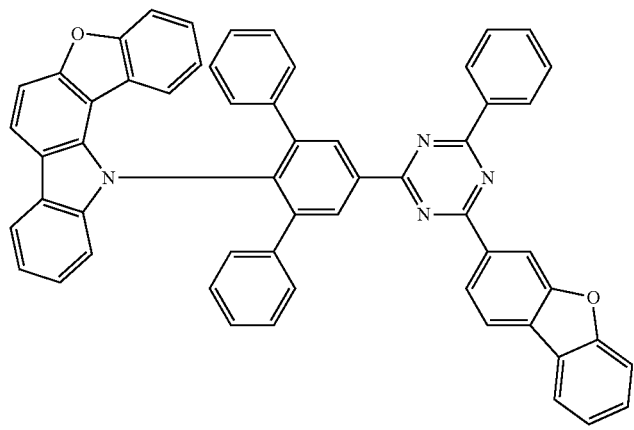
728

729
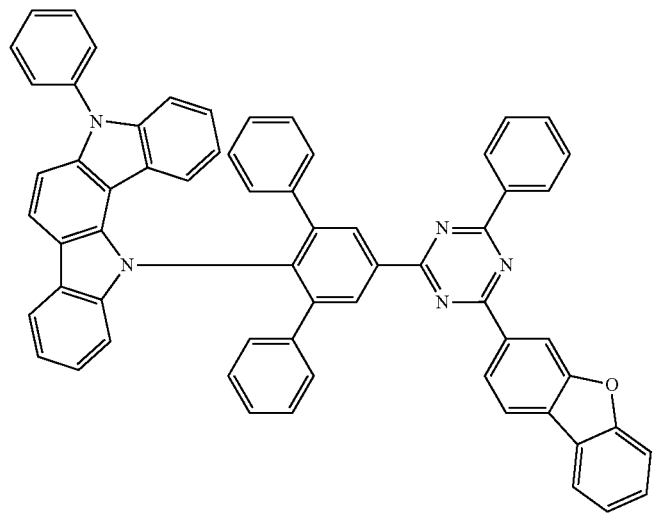
730
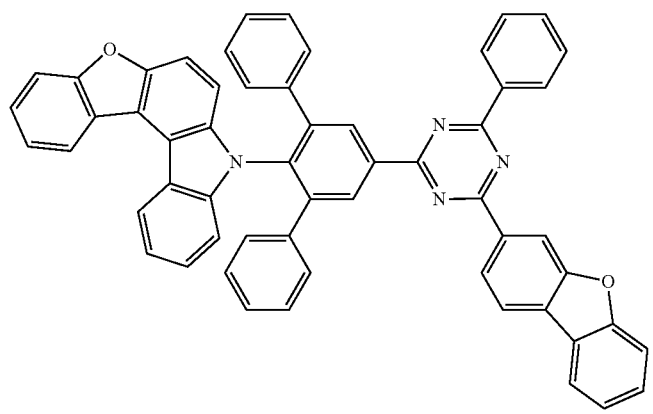
731
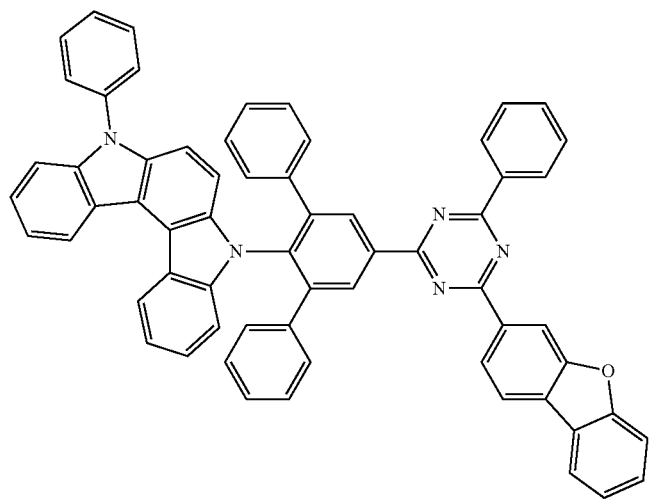

732
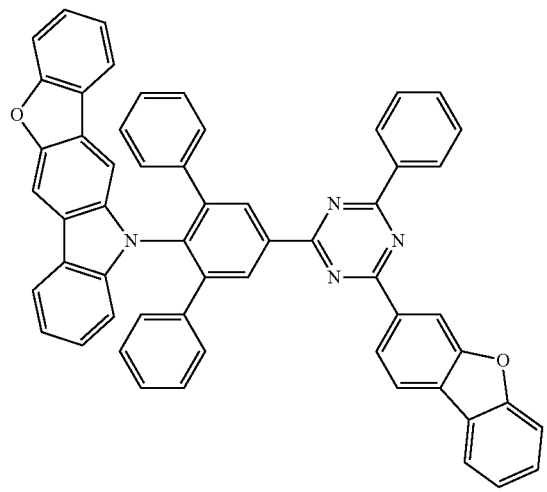
733
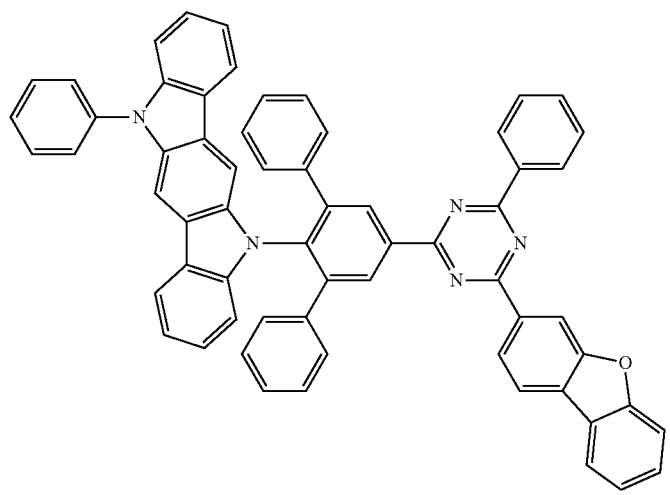
734
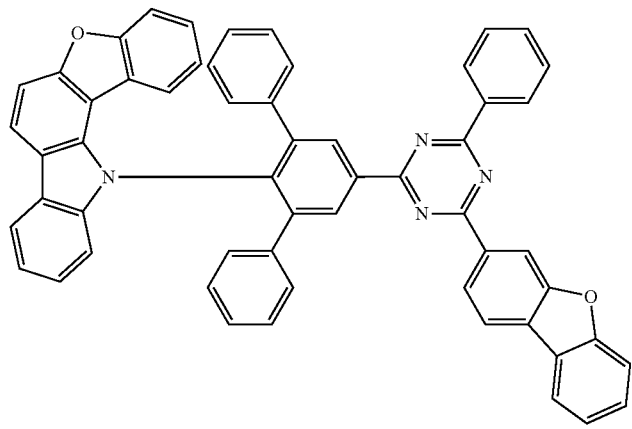

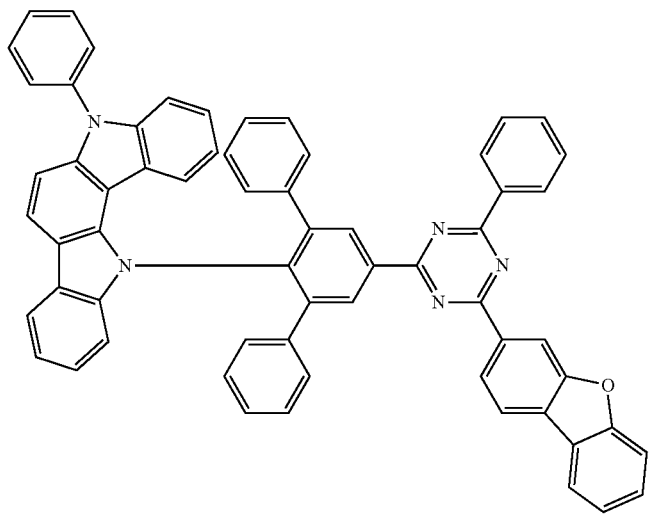
735
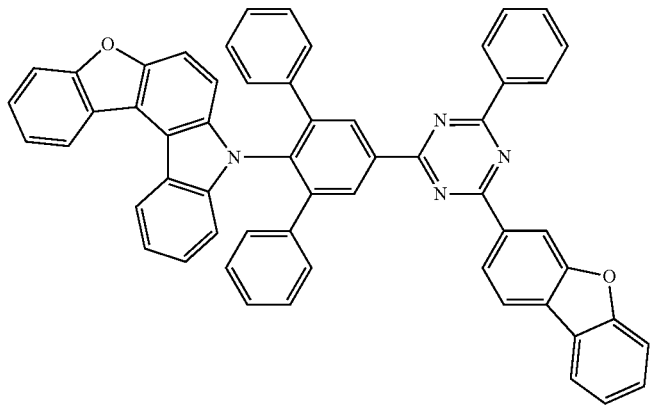
736
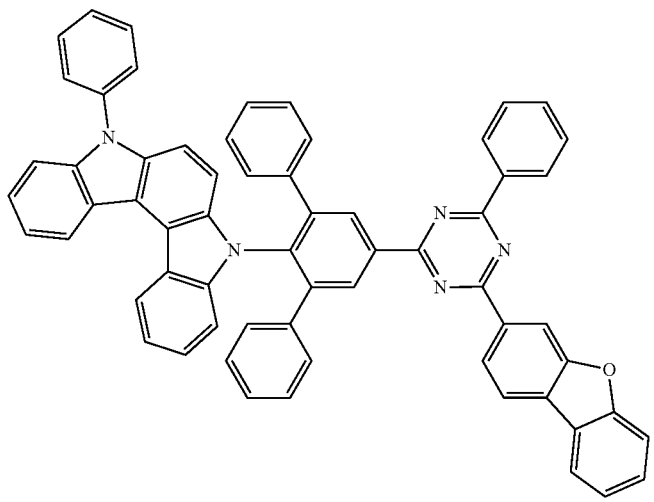
737

-continued
738
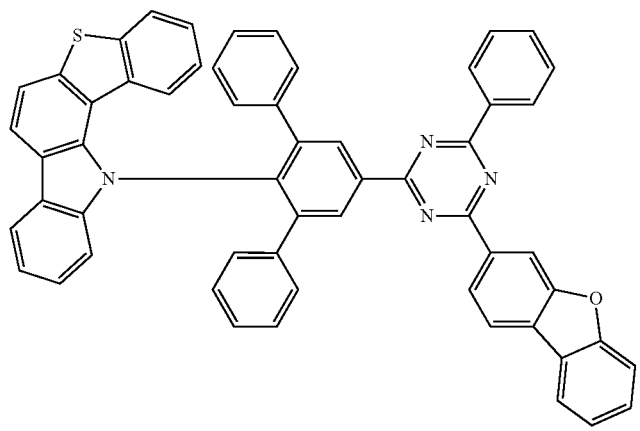
739
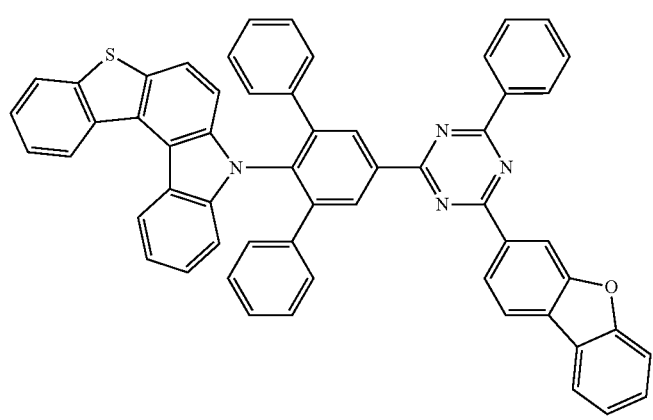
740
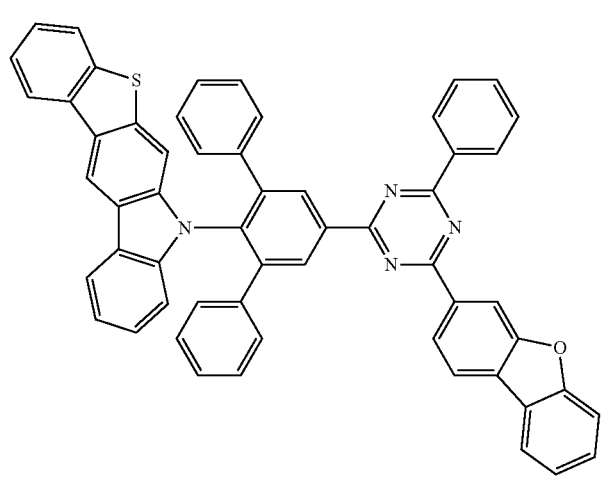

-continued
741
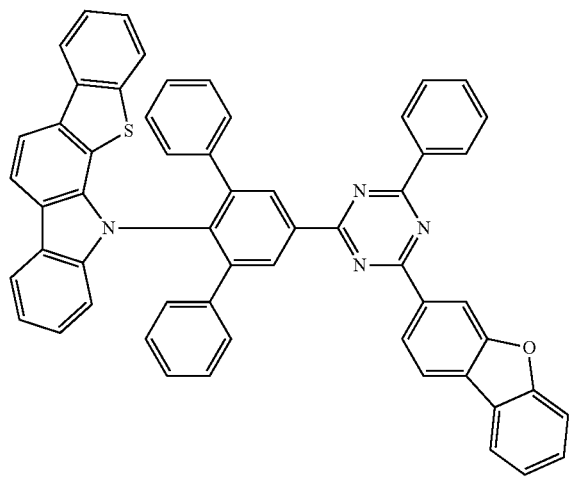
742
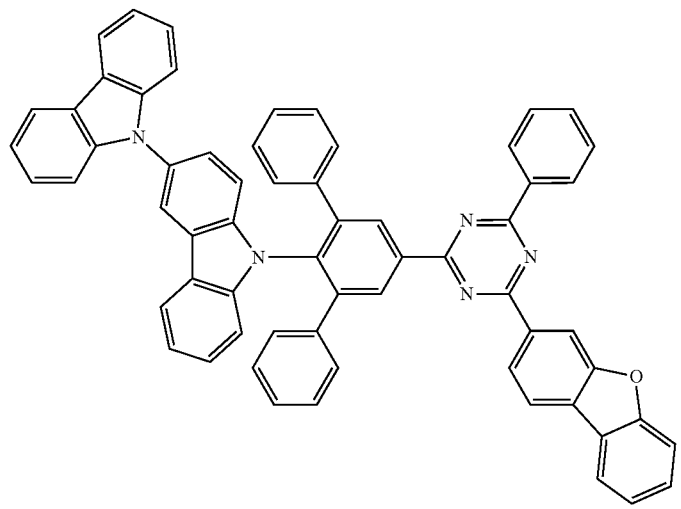
743
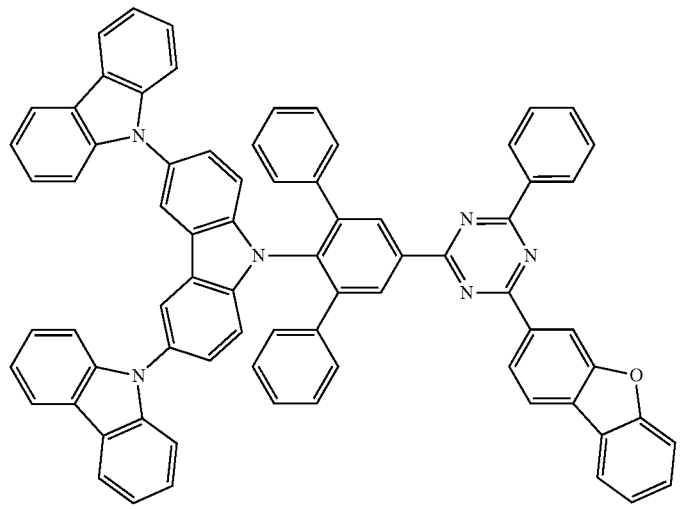

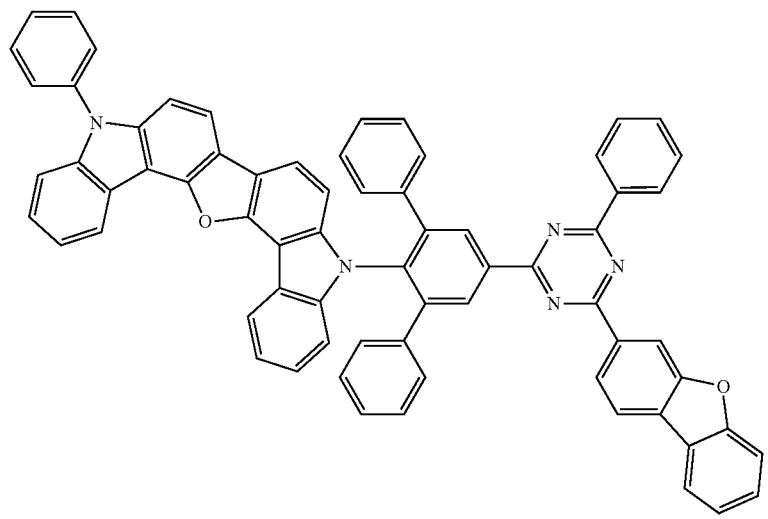
744
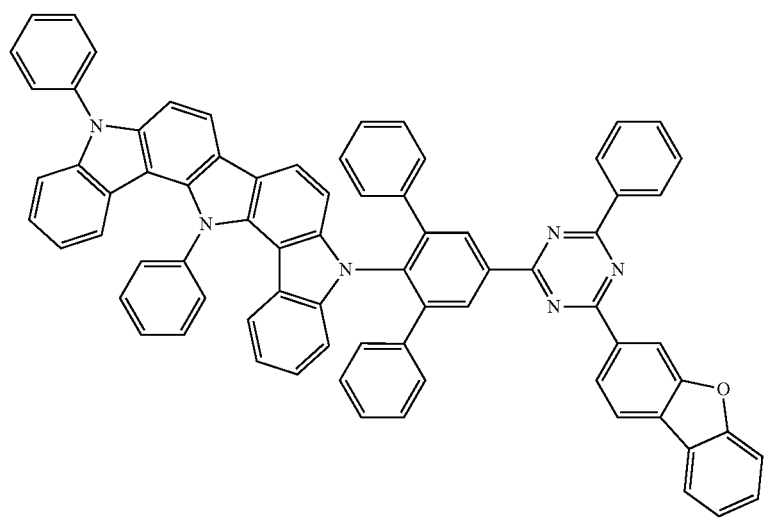
745
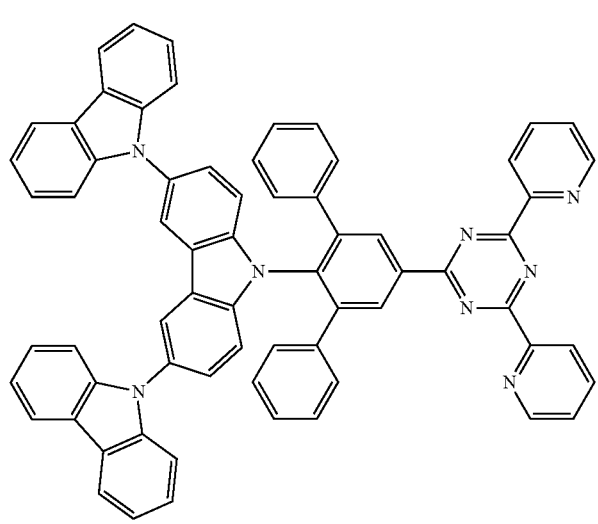
746

747
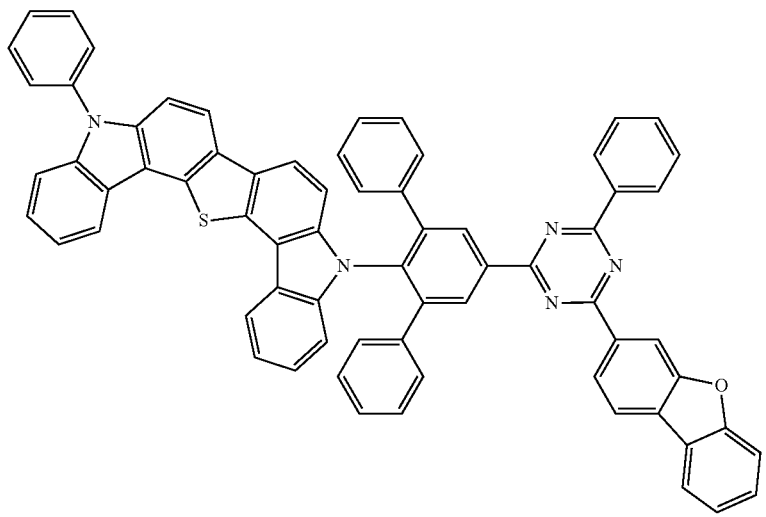
748
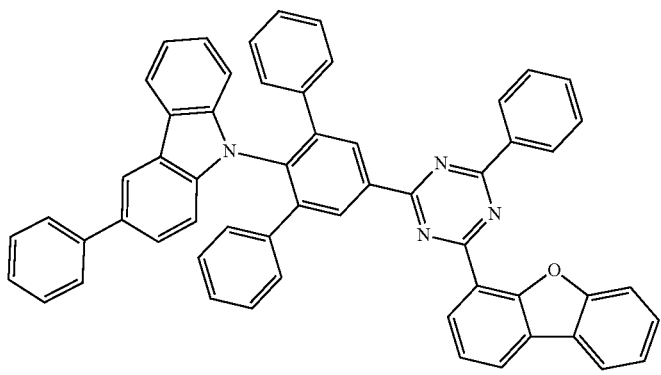
749
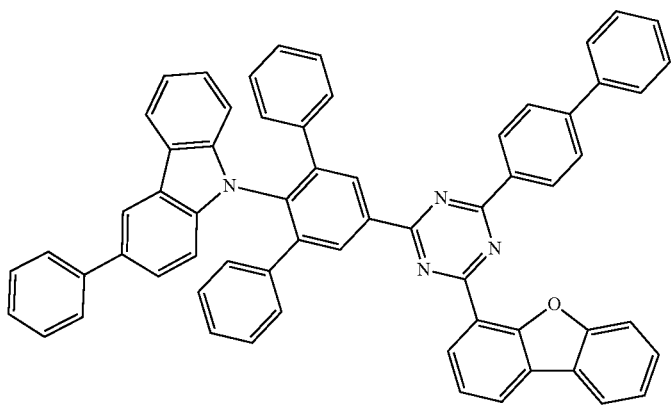

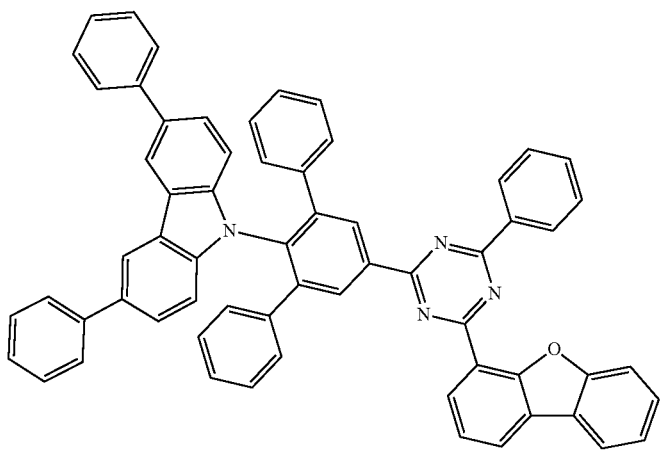
750
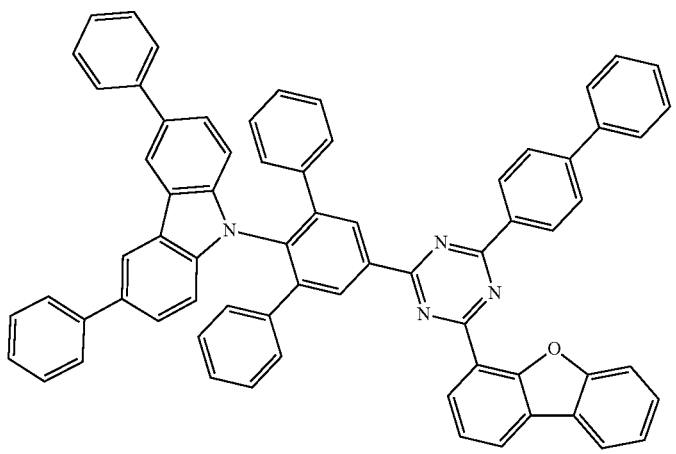
751
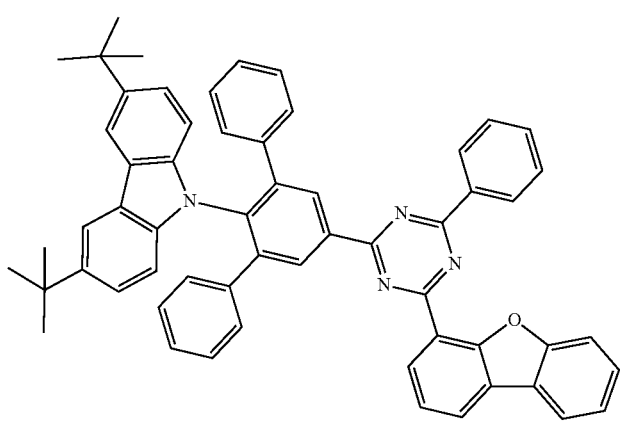
752

753
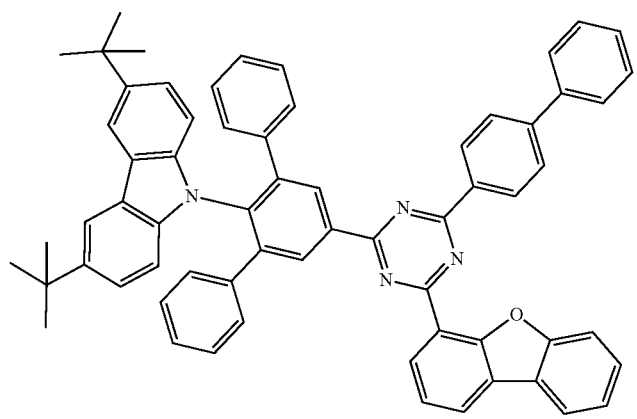
754
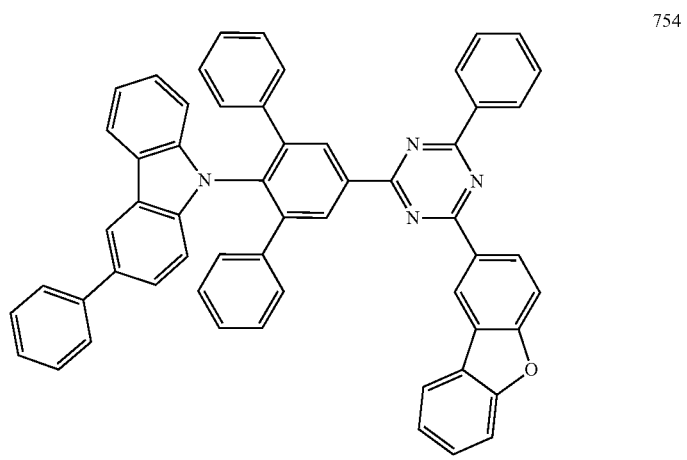
755
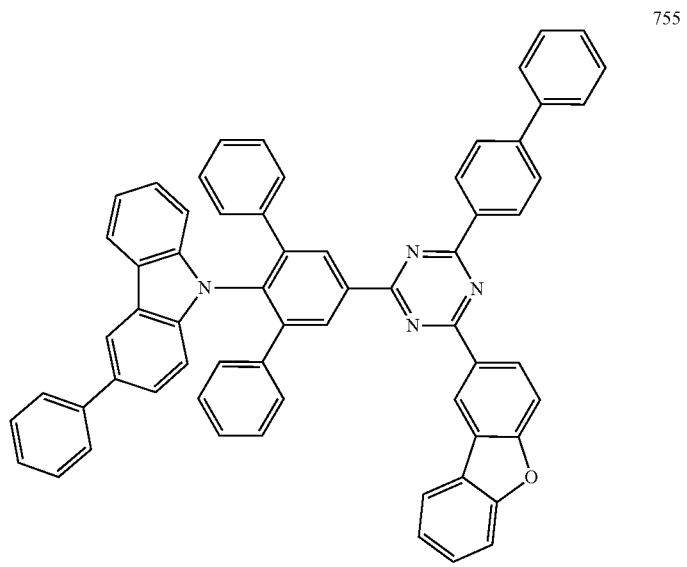

-continued
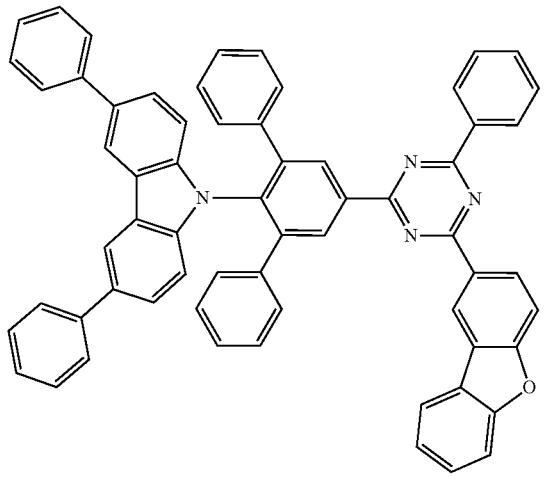
756
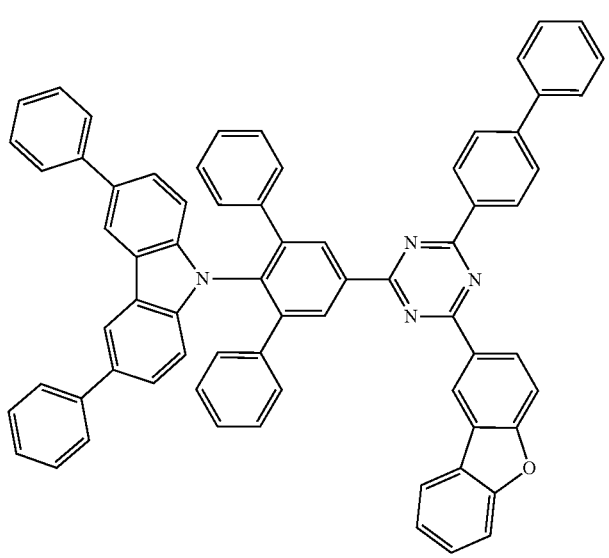
757
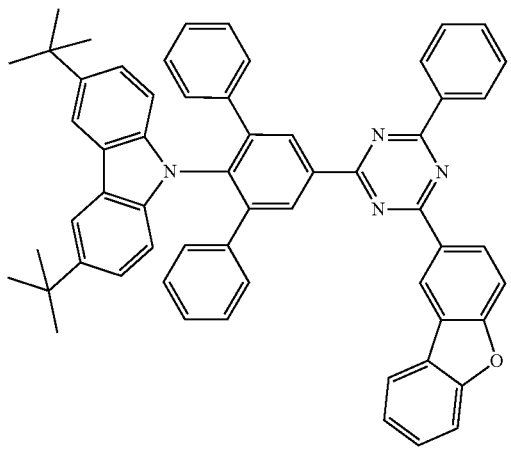
758

-continued
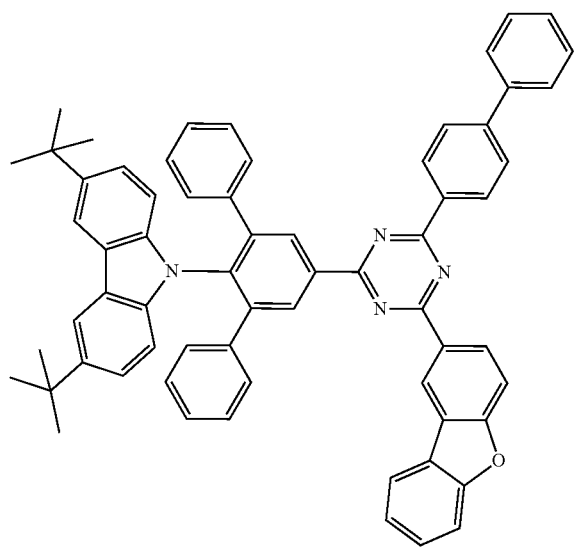
759
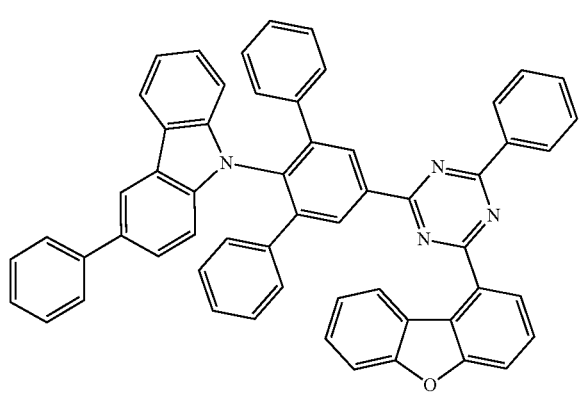
760
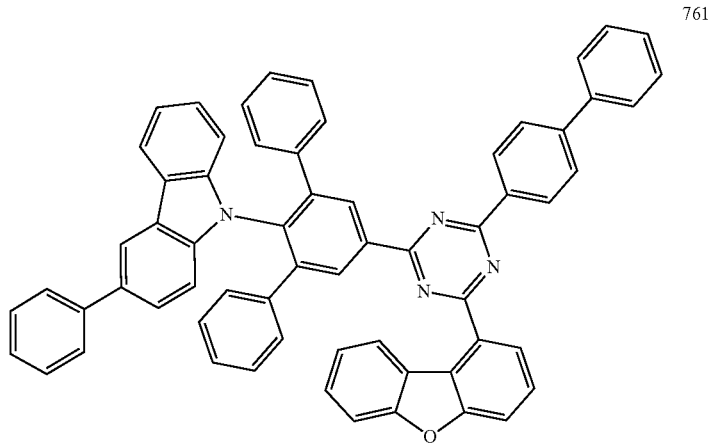
761

-continued
762
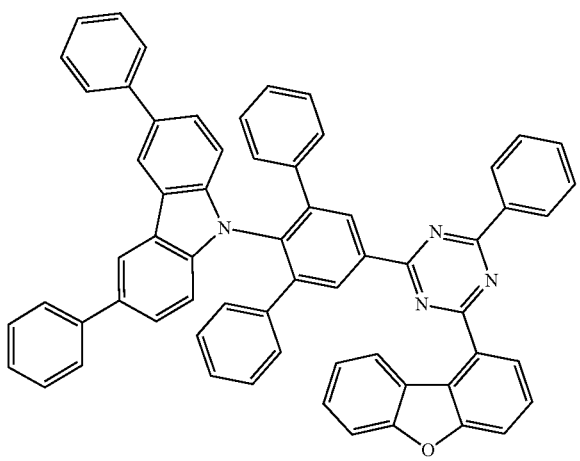
763
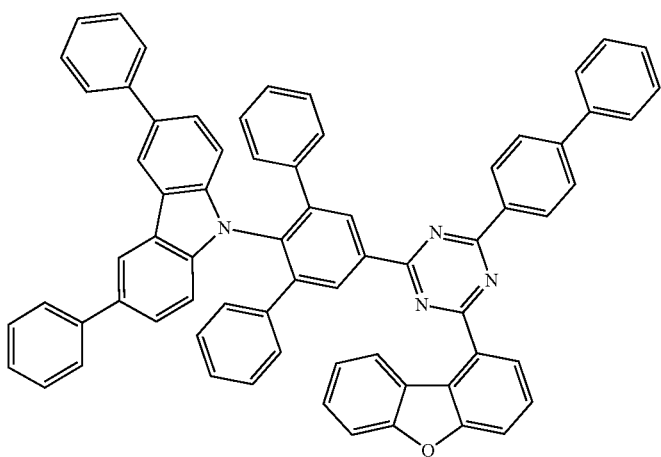
764
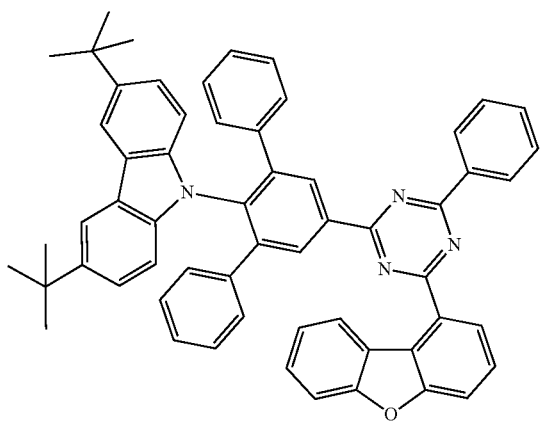

-continued
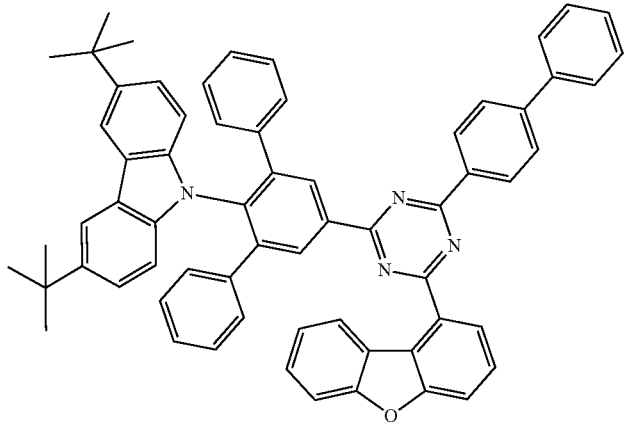
765
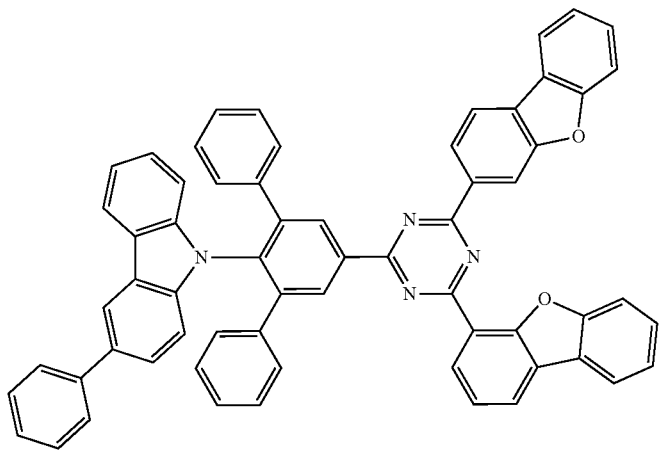
766
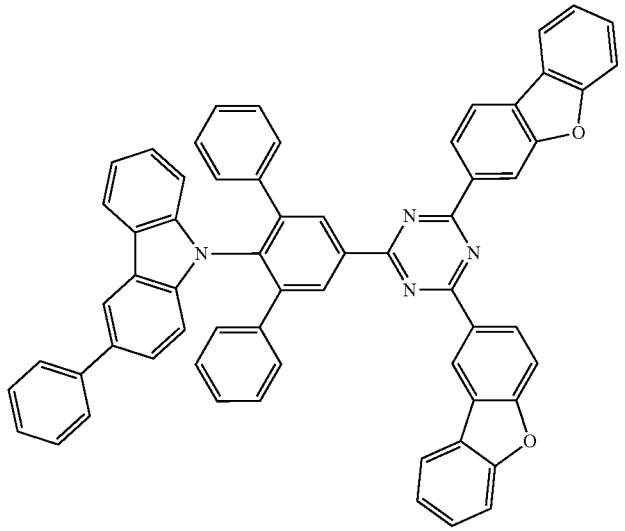
767

-continued
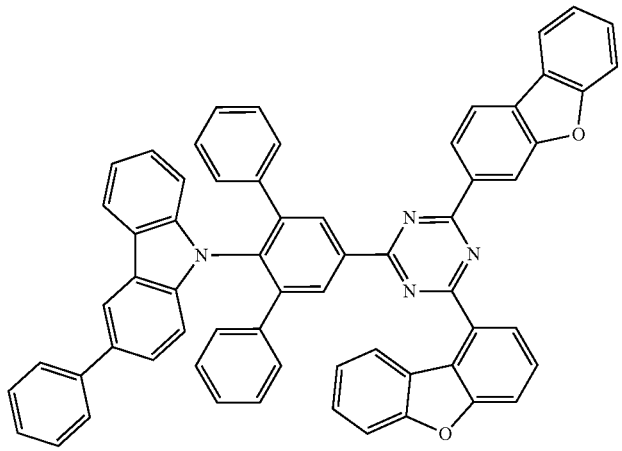
768
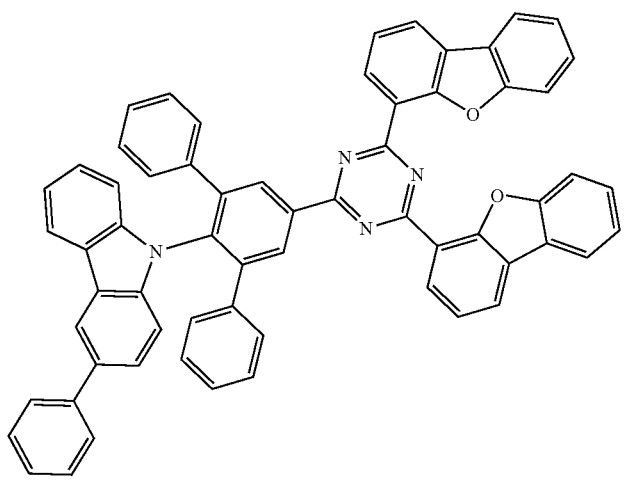
769
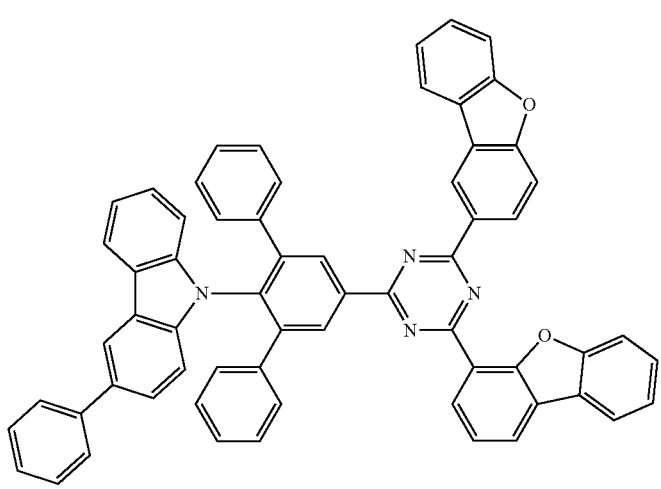
770

-continued
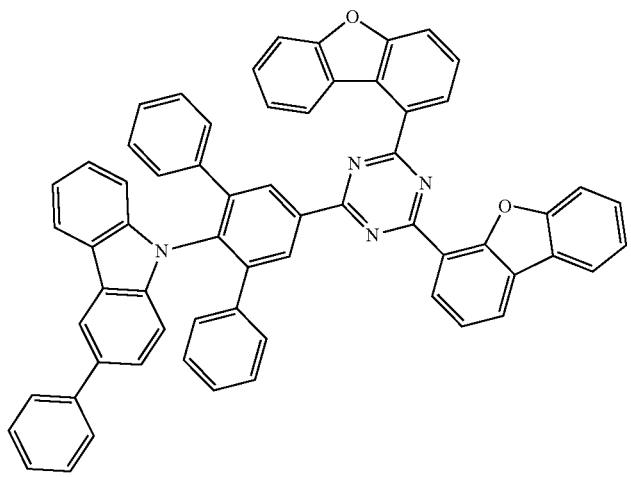
771
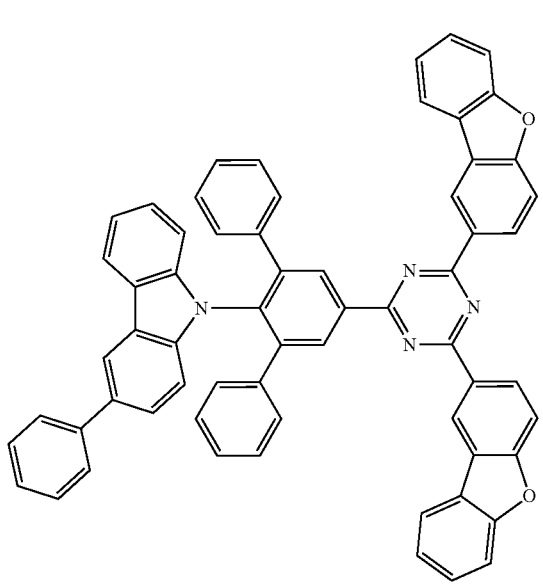
772
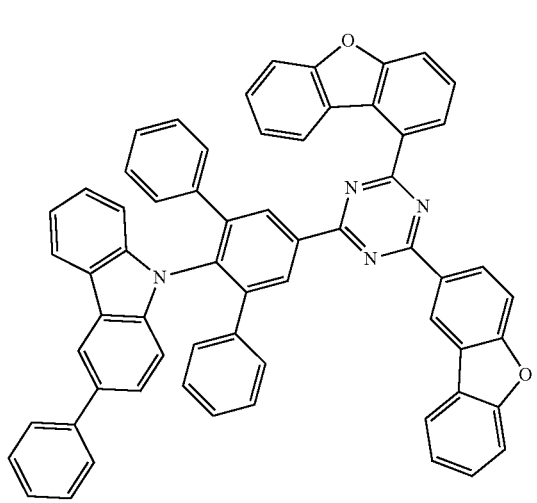
773

774
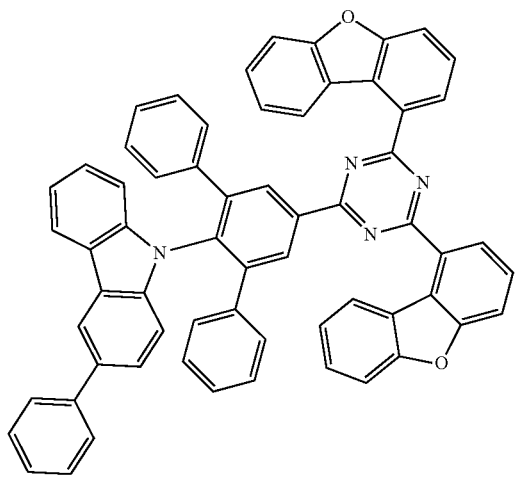
775
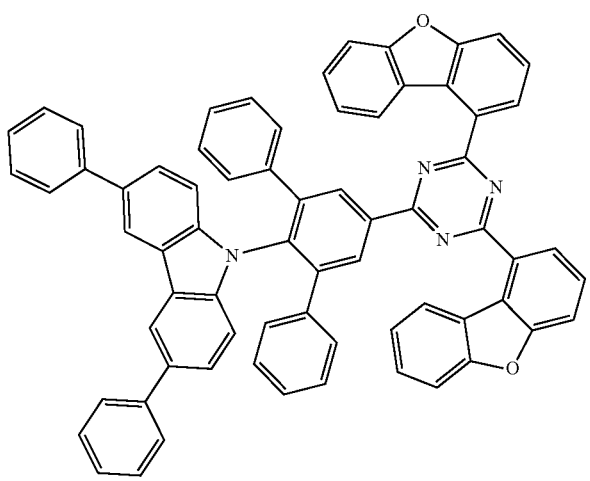
776
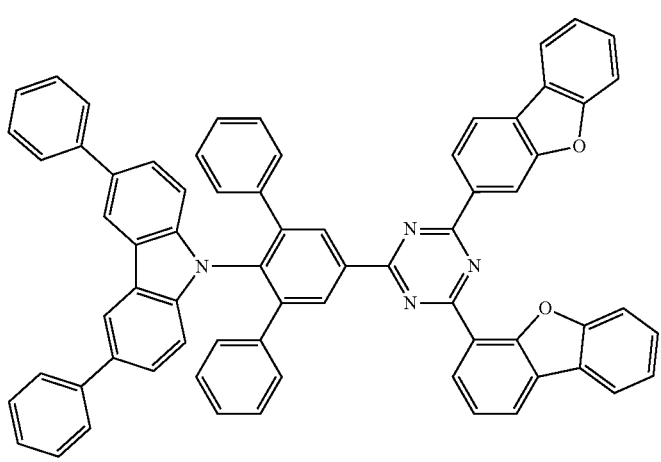

777
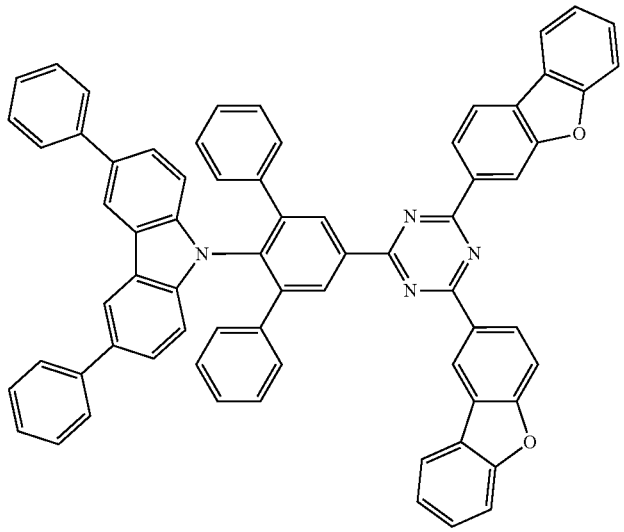
778
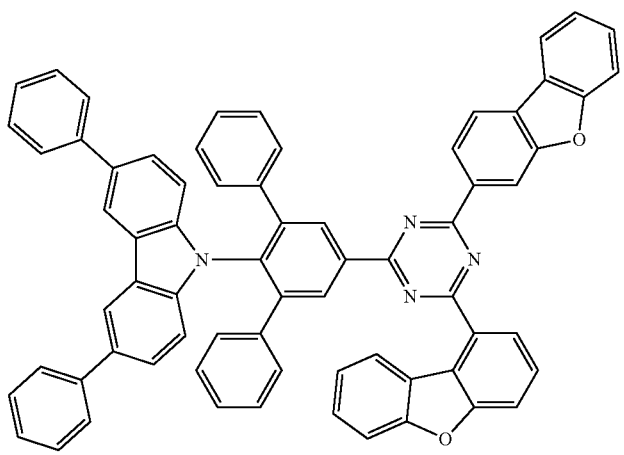
779
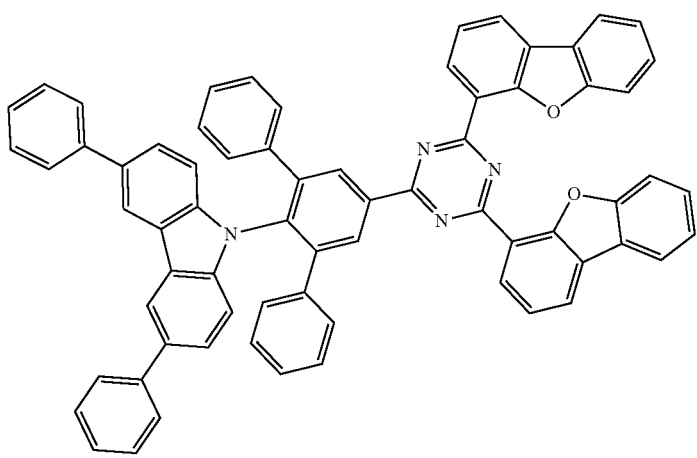

-continued
780
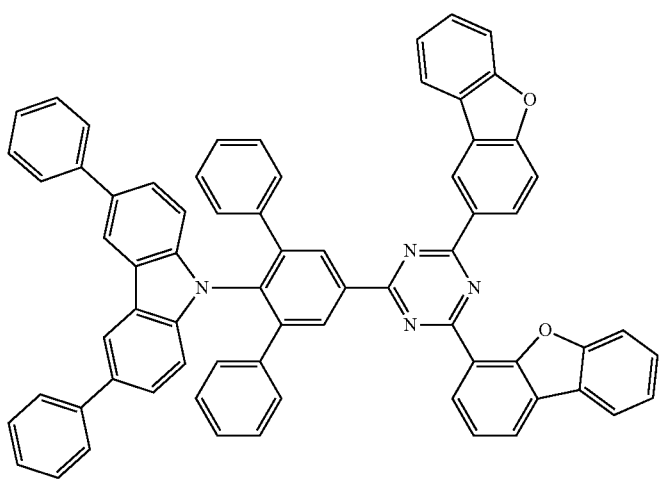
781
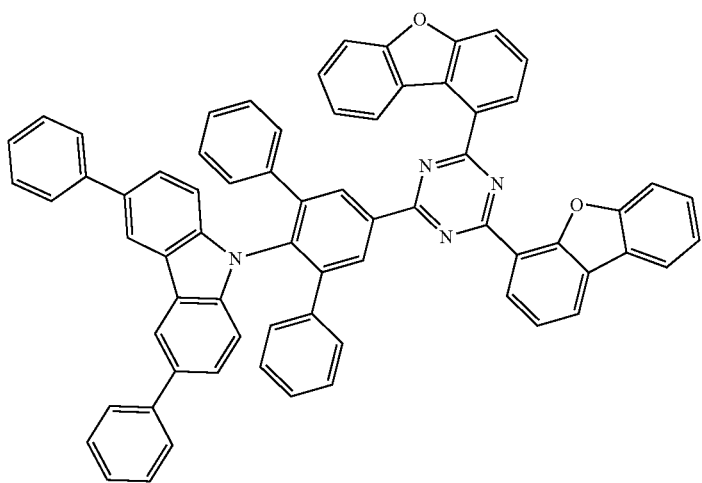
782
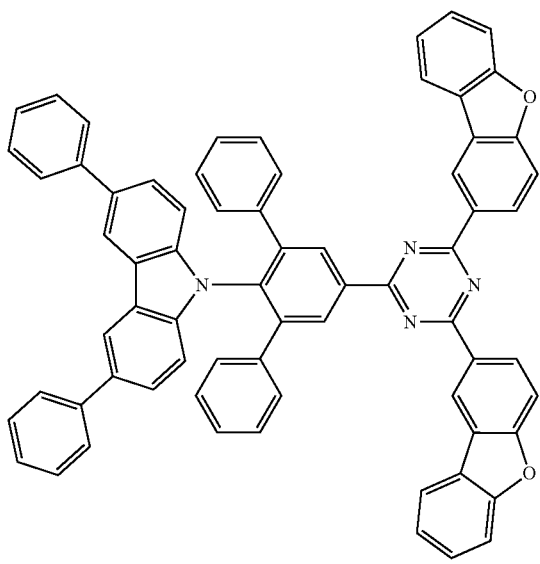

783
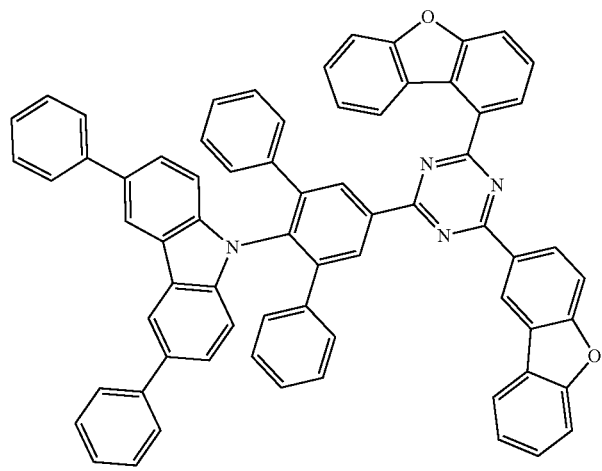
784
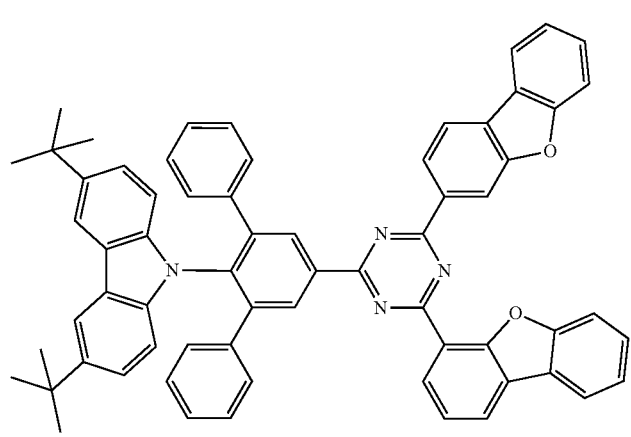
785
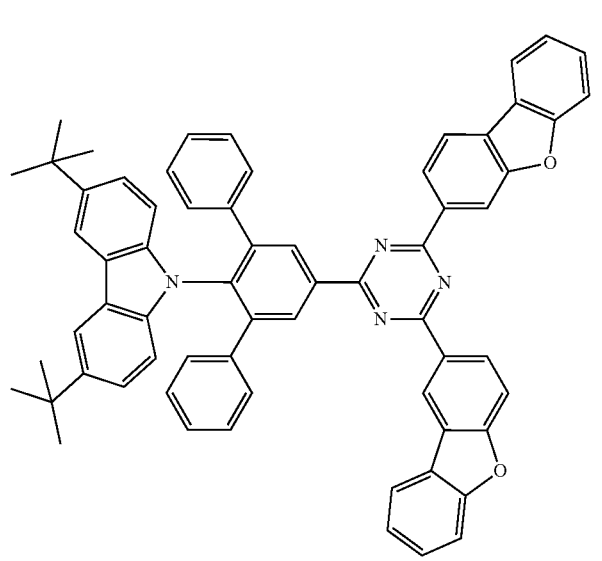

786
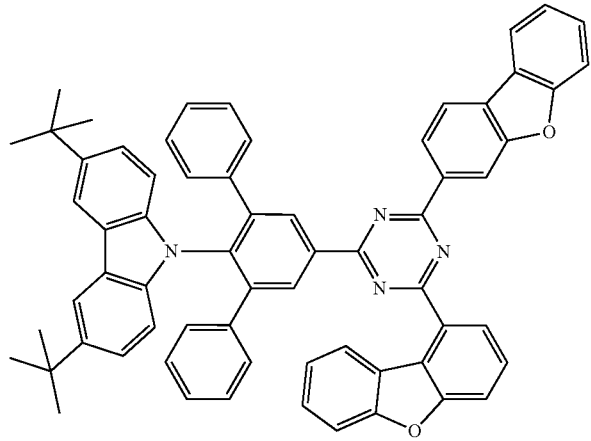
787
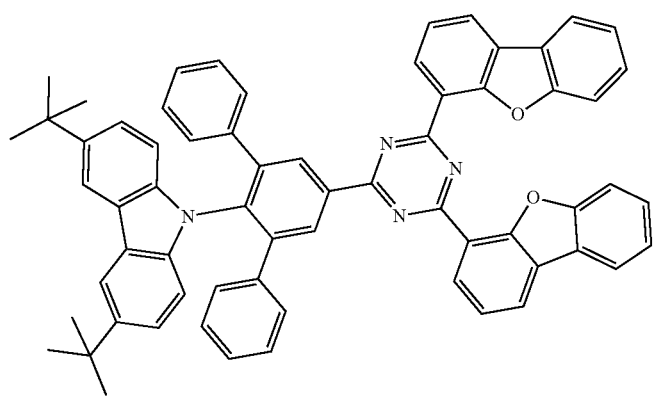
788
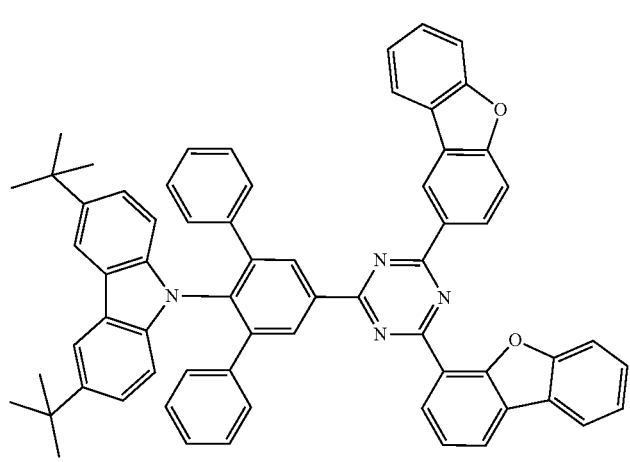

-continued
789
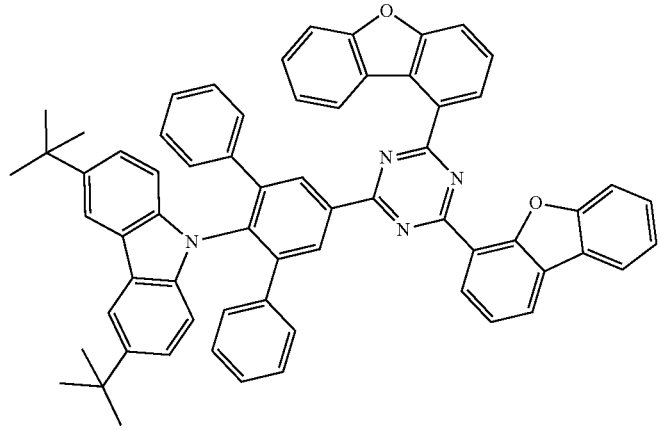
790
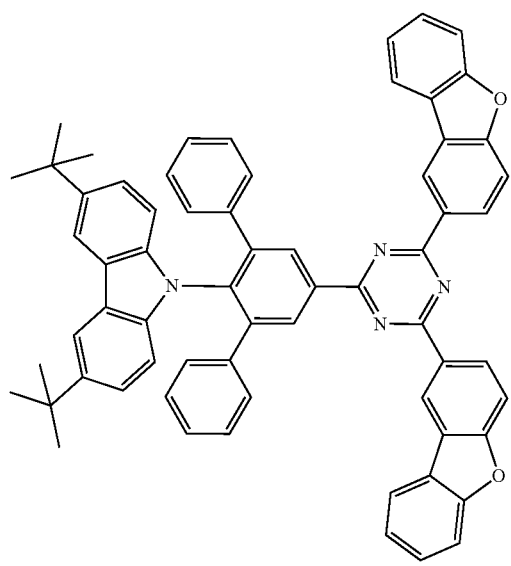
791
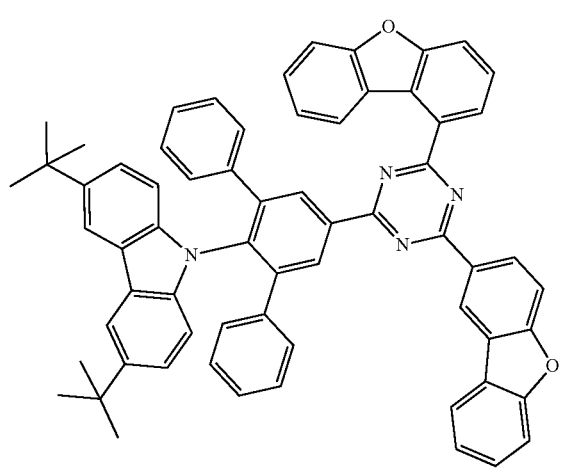

-continued
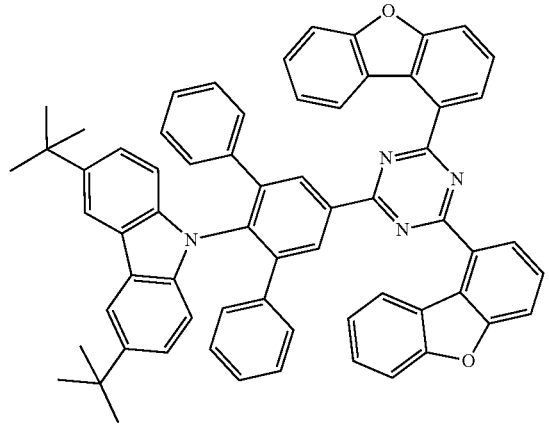
792
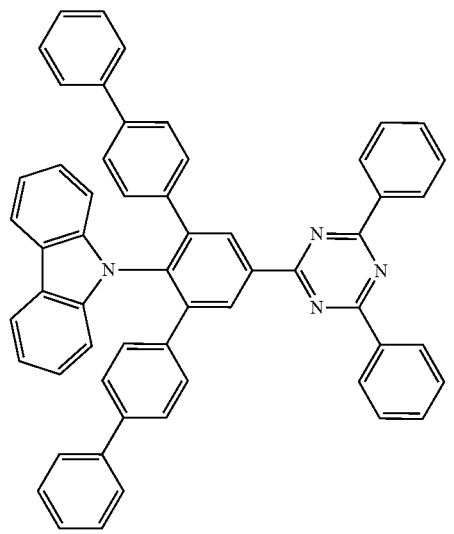
793
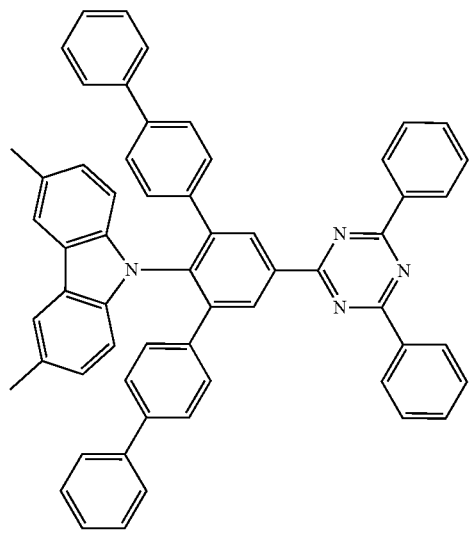
794

795
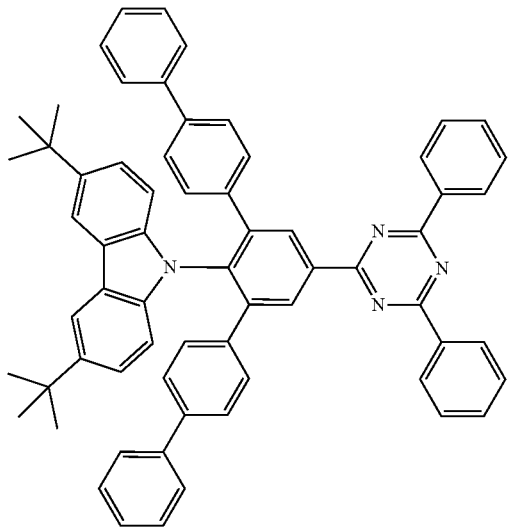
796
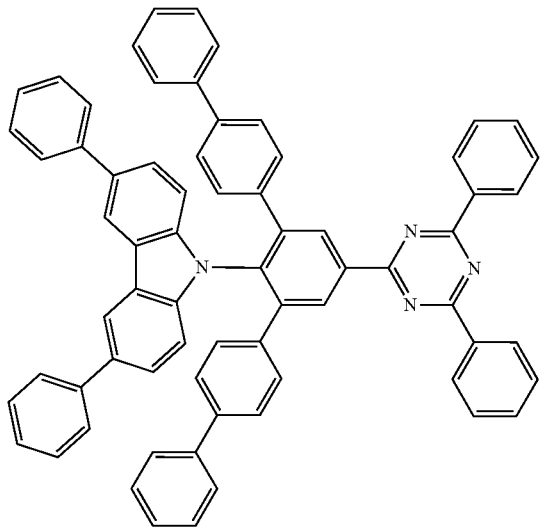
797
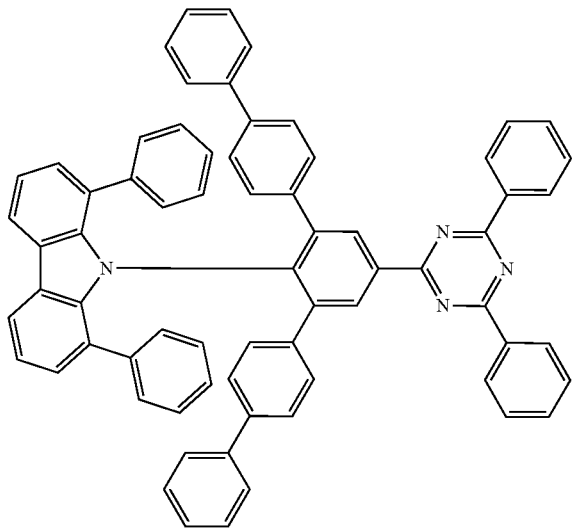

-continued
798
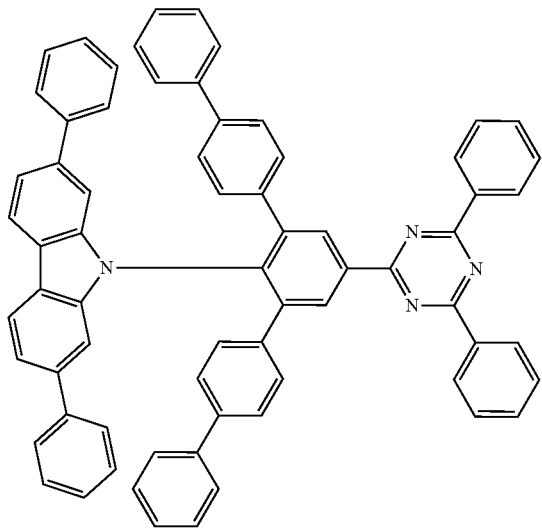
799
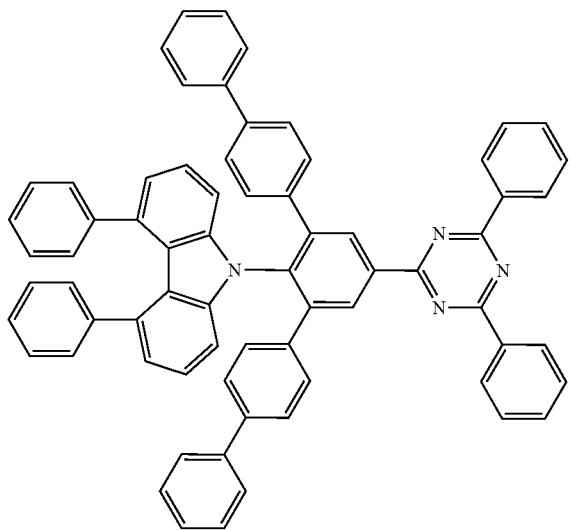
800
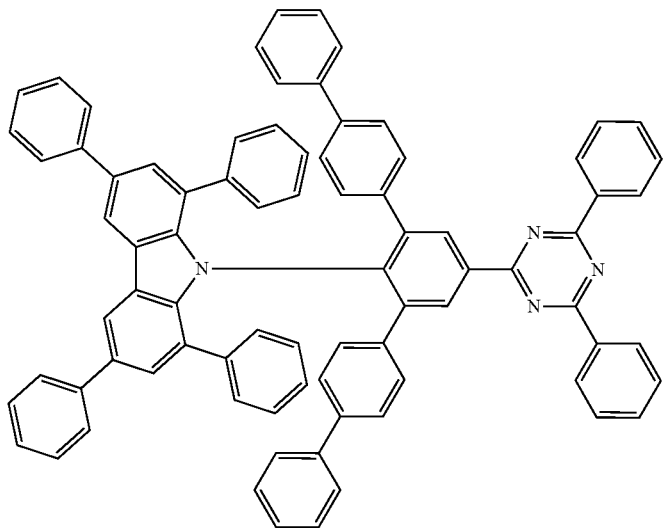

-continued
801
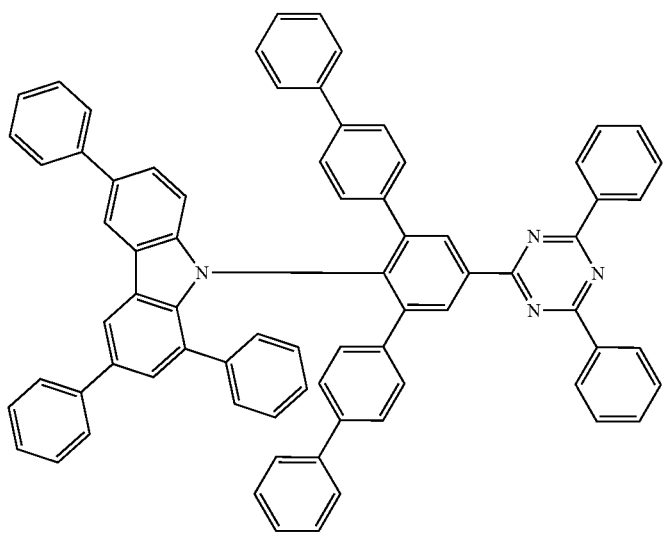
802
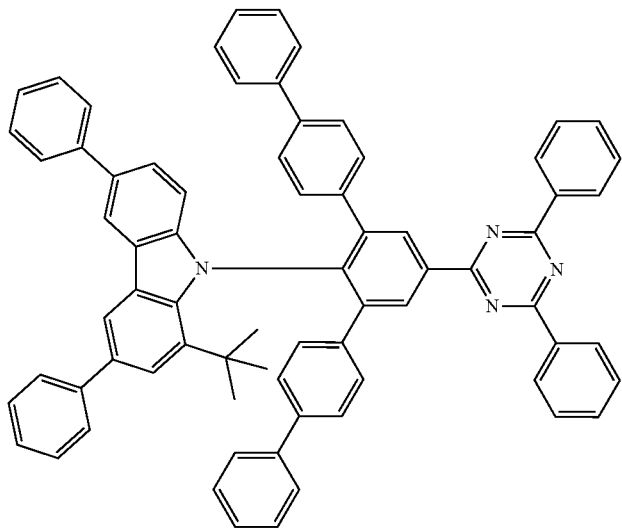
803
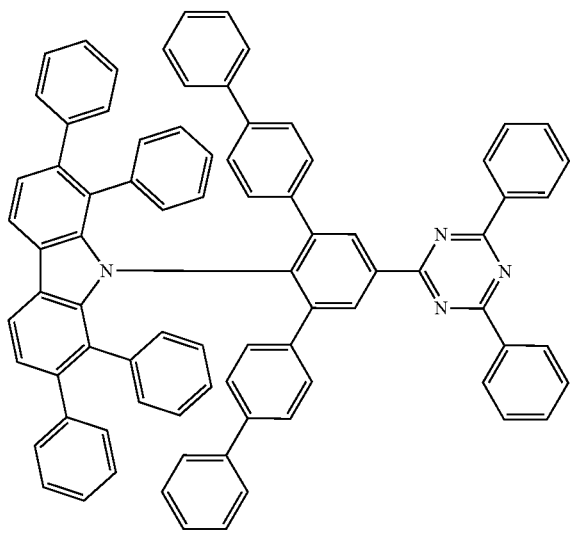

804
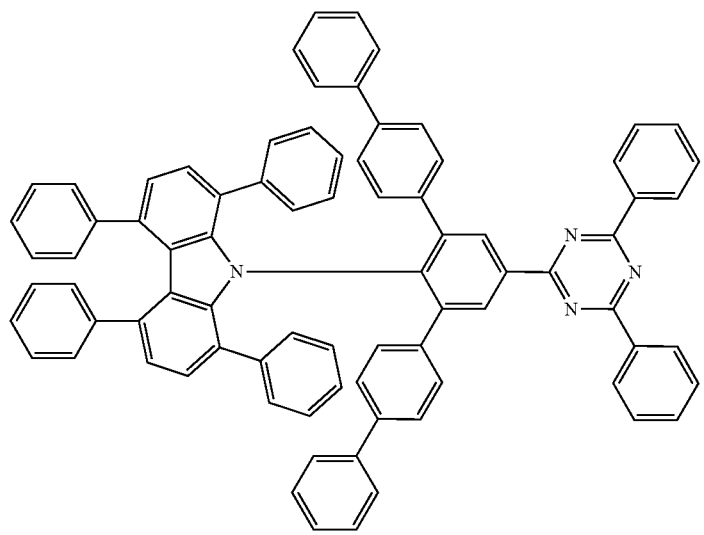
805
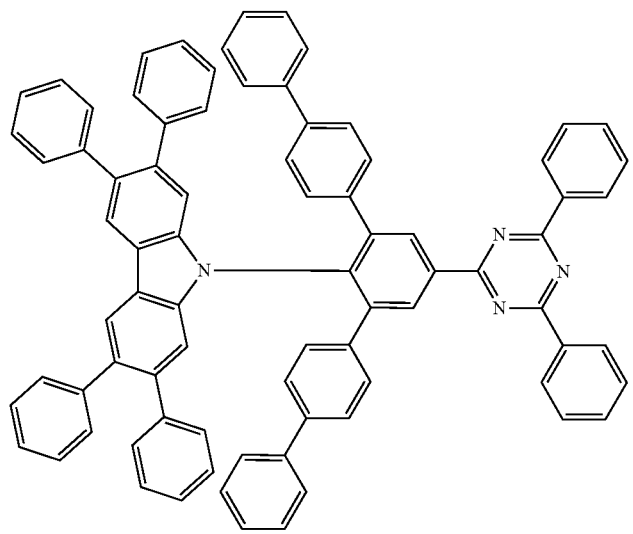
806
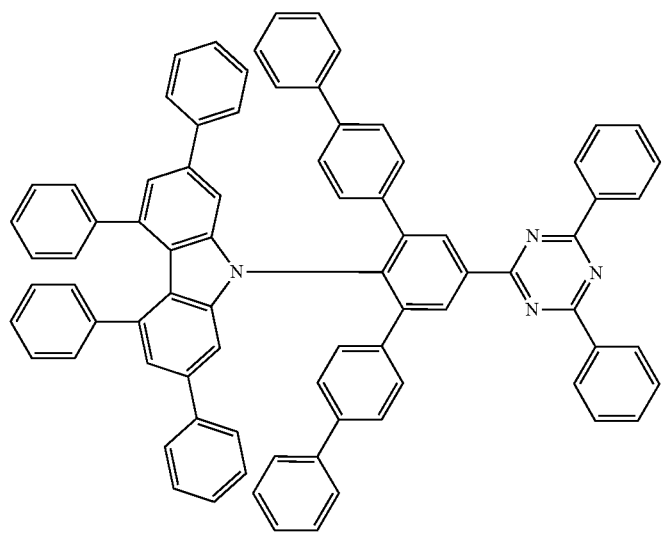

-continued
807
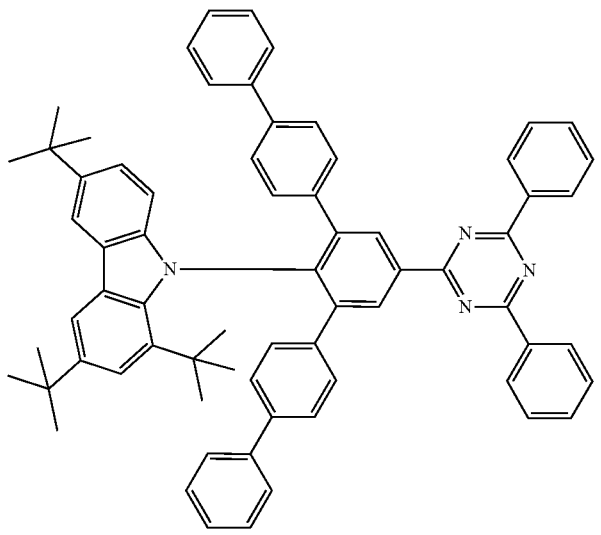
808
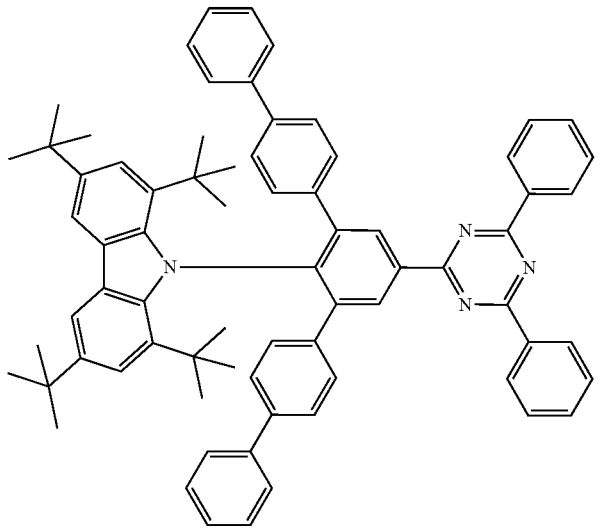
809
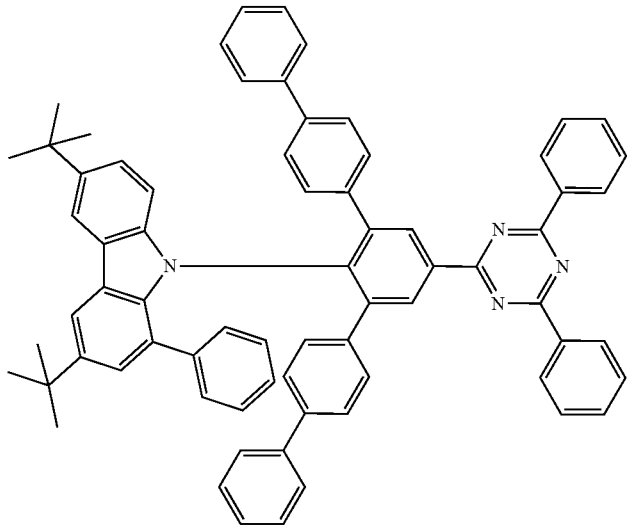

-continued
810
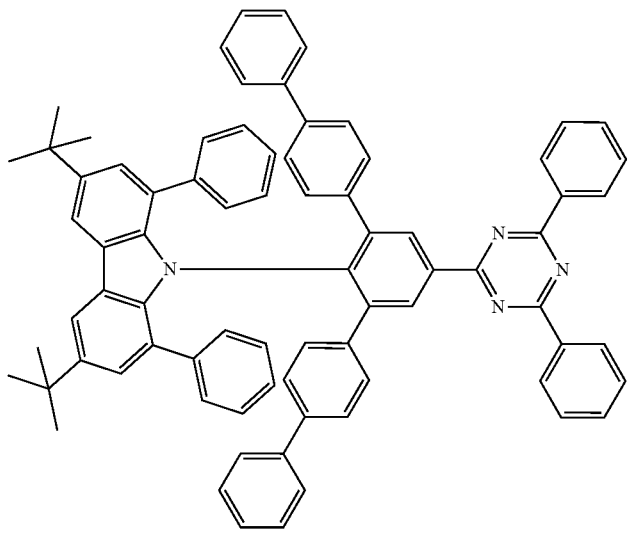
811
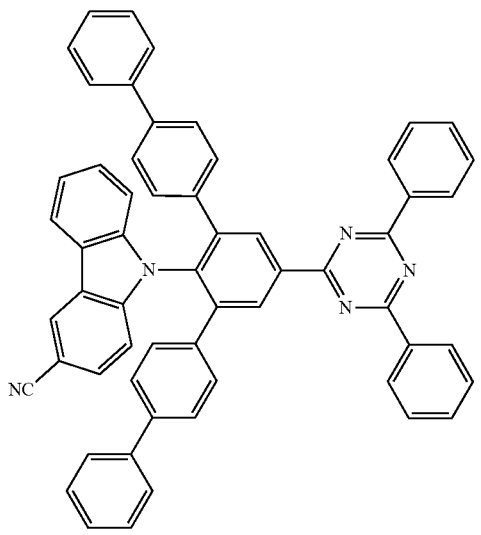
812
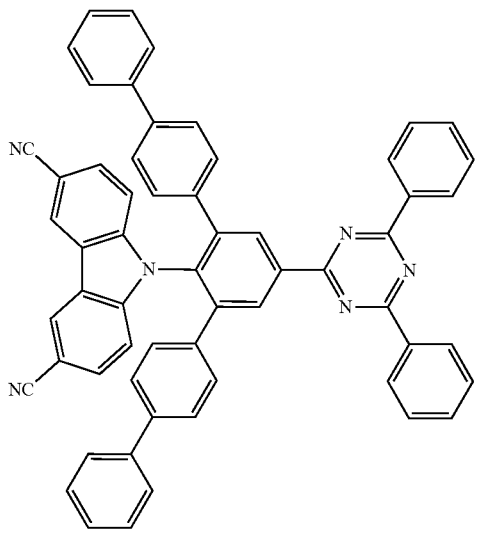

-continued
813
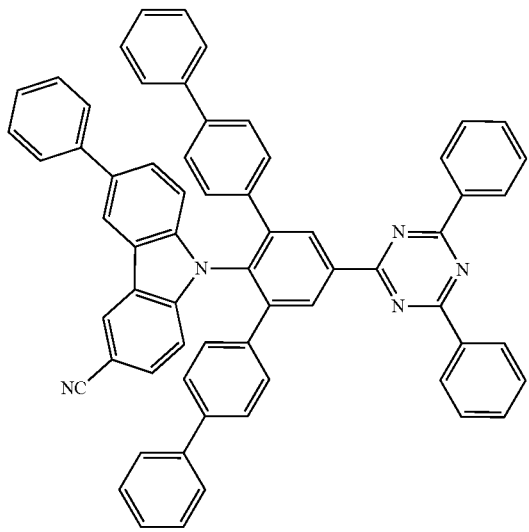
814
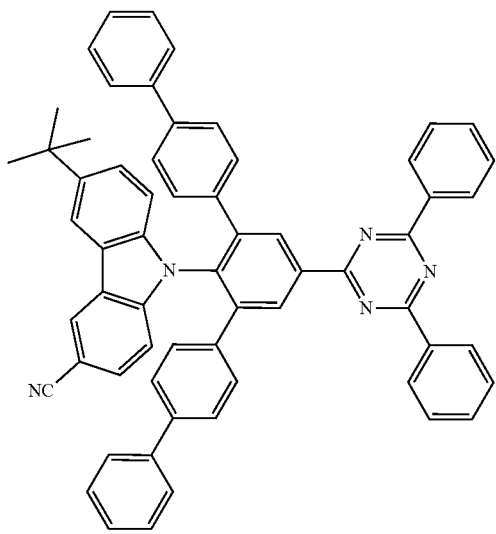
815
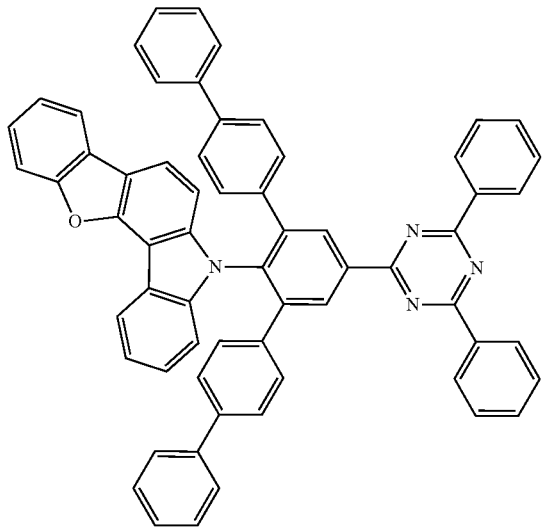

-continued
816
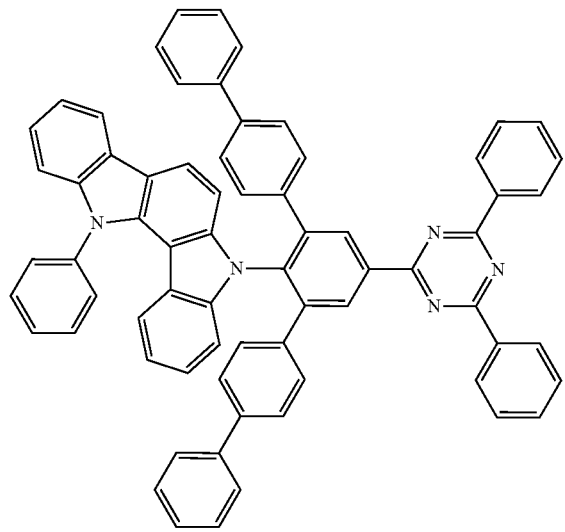
817
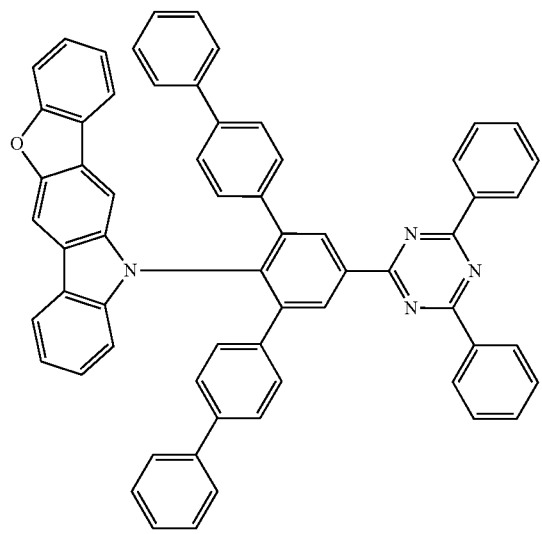
818
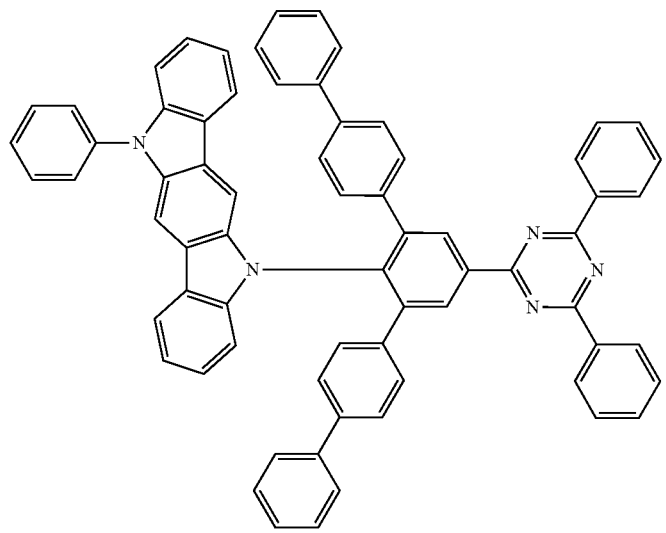

-continued
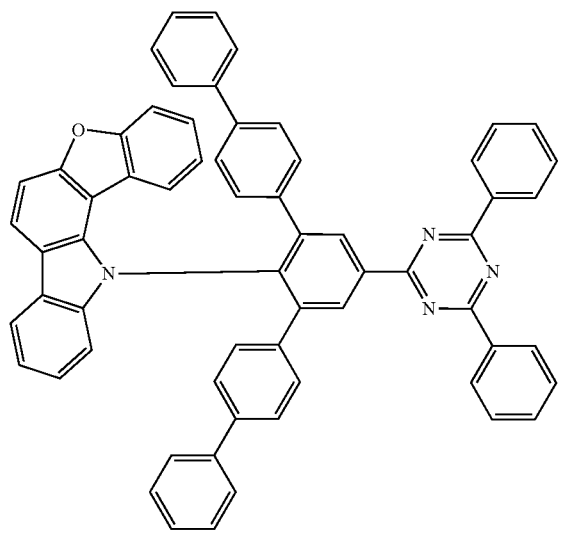
819
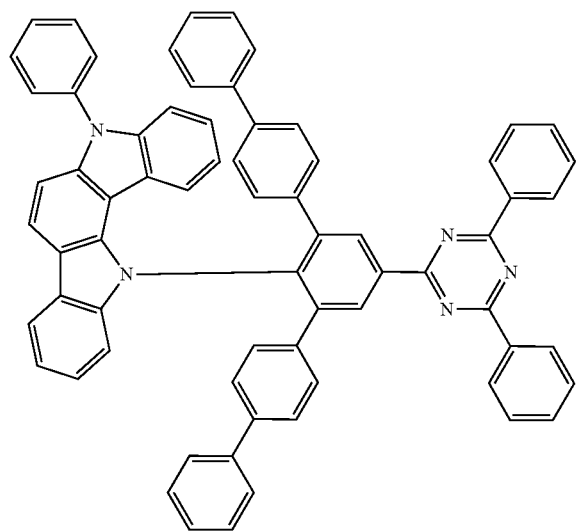
820

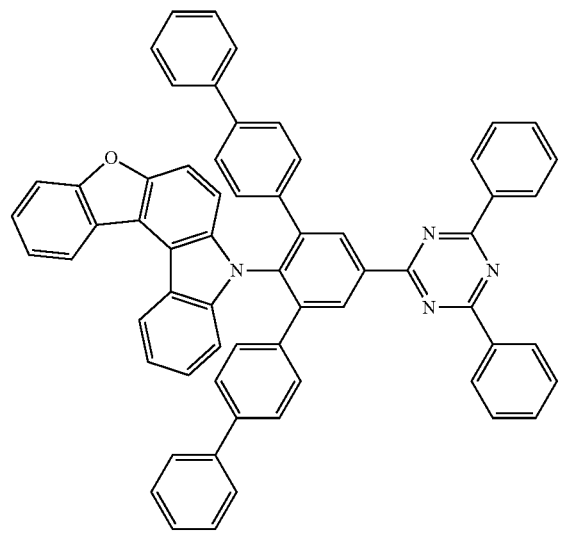
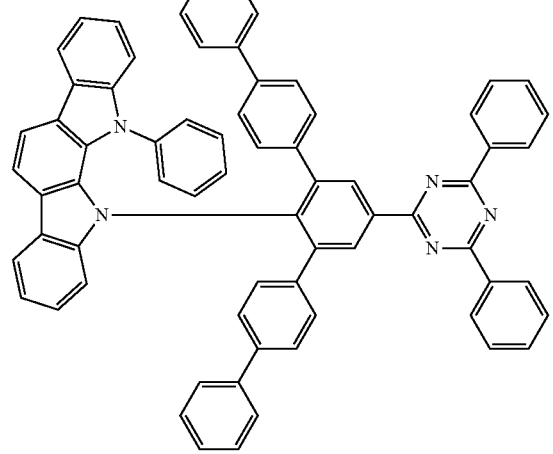

-continued
827
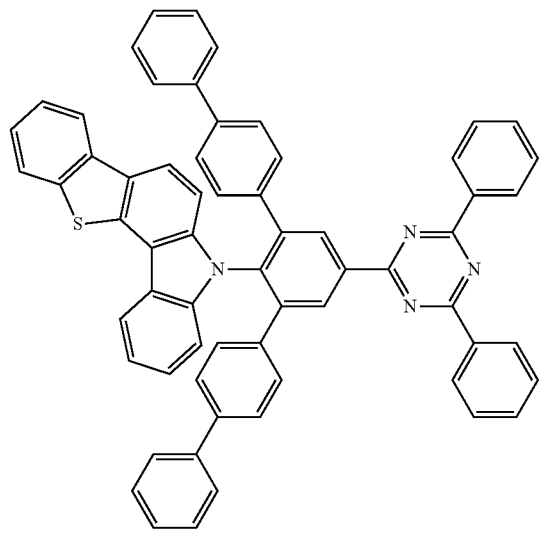
828
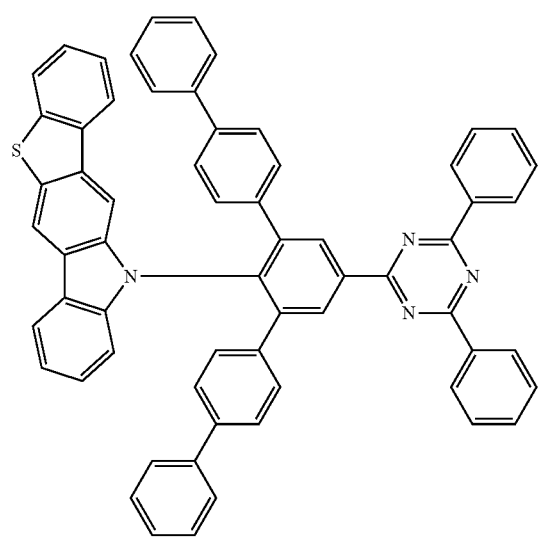
829
-continued
830
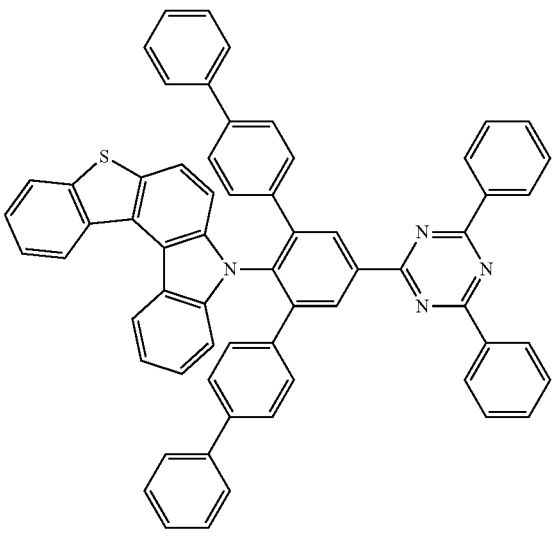
831
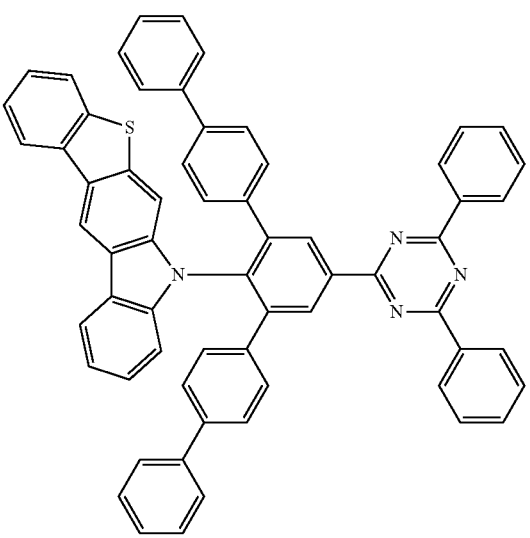
832
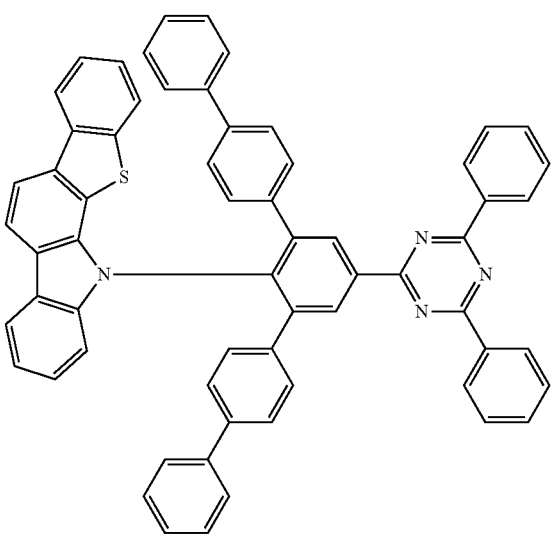

3227
-continued
833
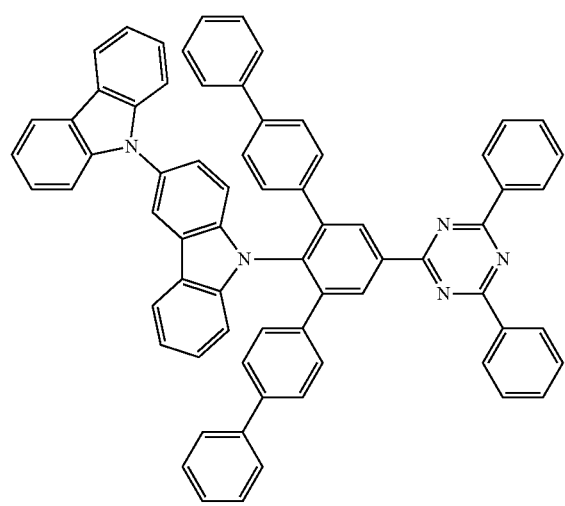
834
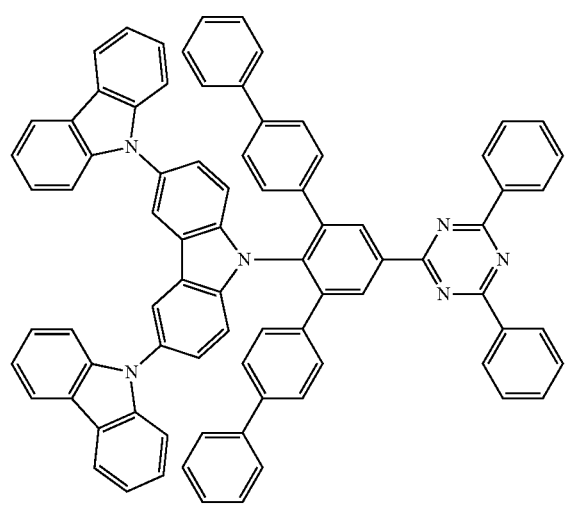
835
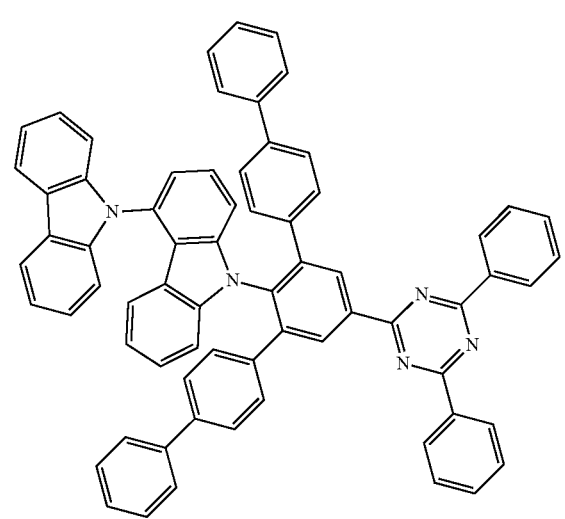
3228
-continued
836
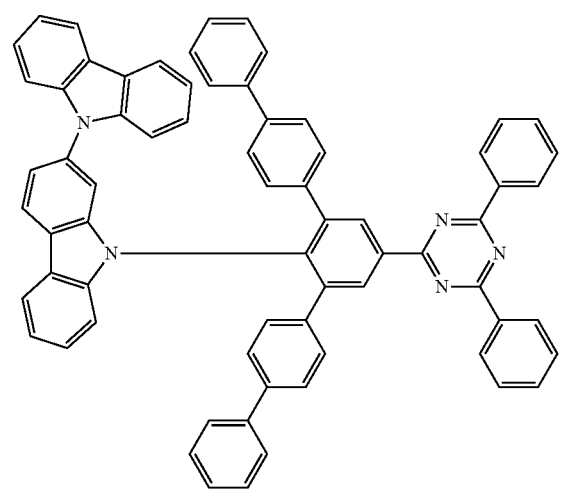
837
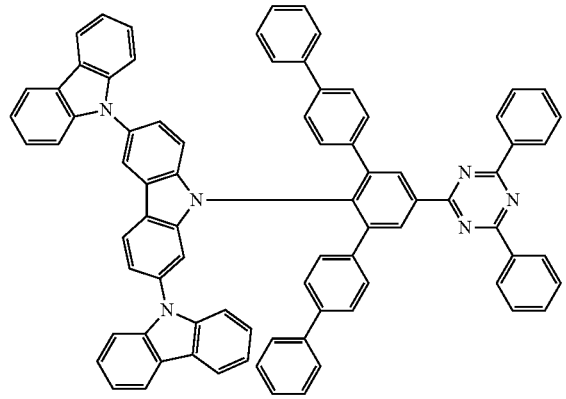
838
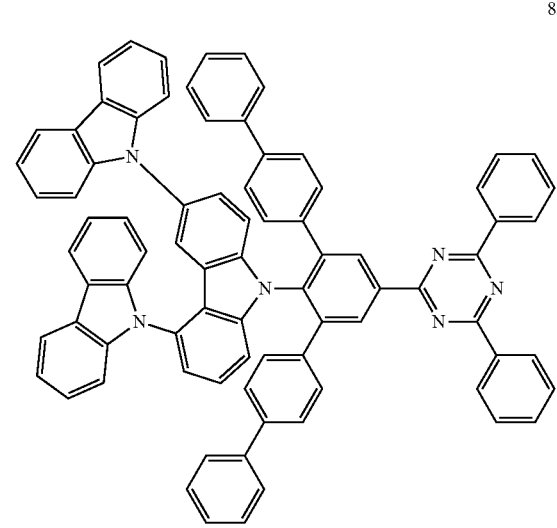

839
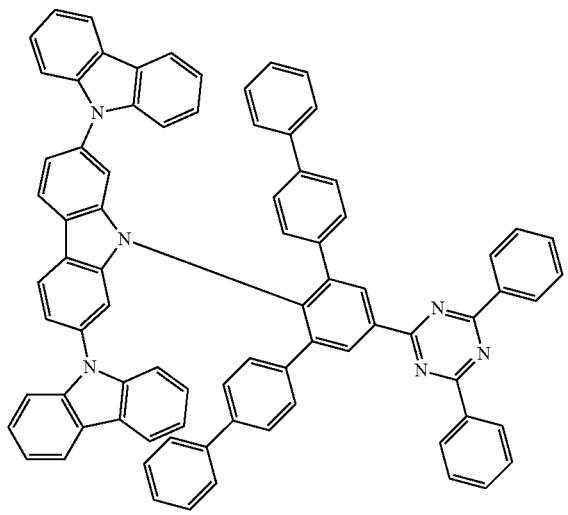
840
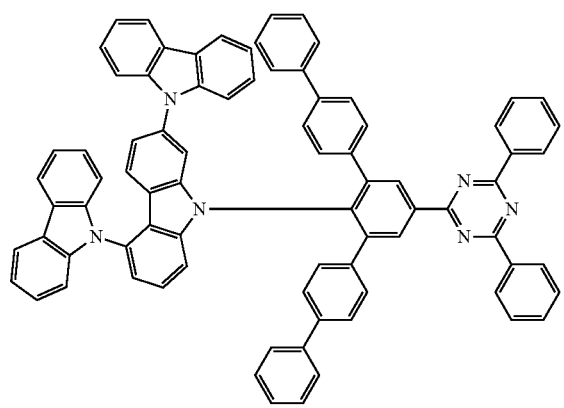
841
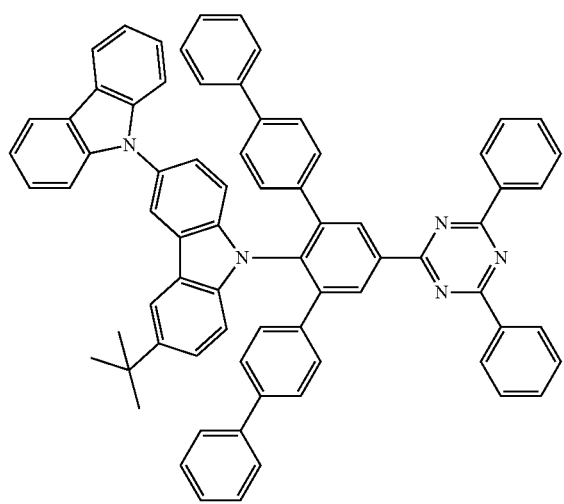
842
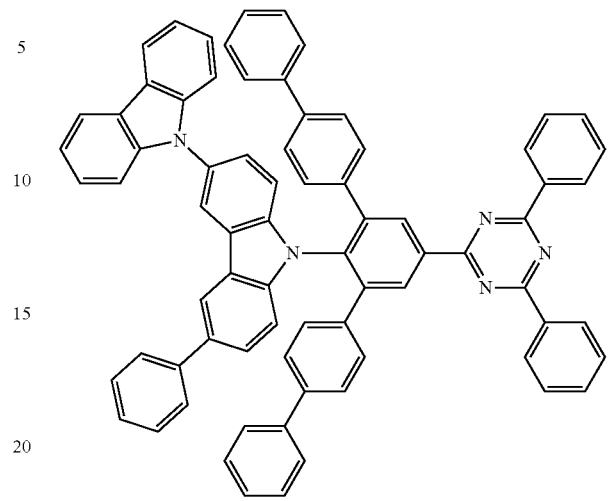
843
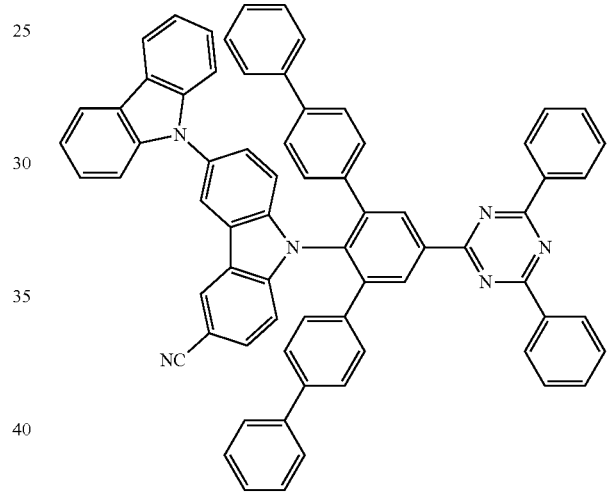
844
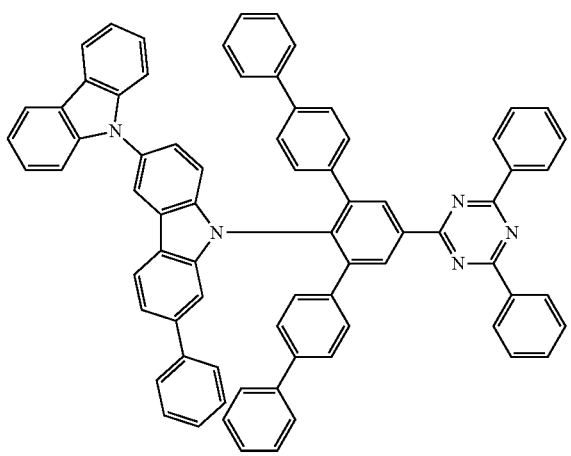

3231
-continued
845
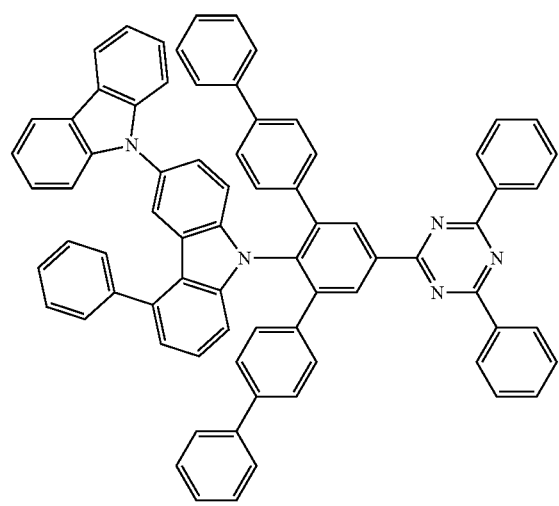
846
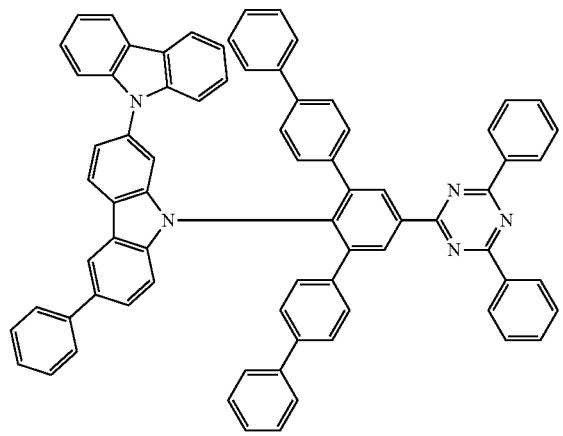
847
3232
-continued
848
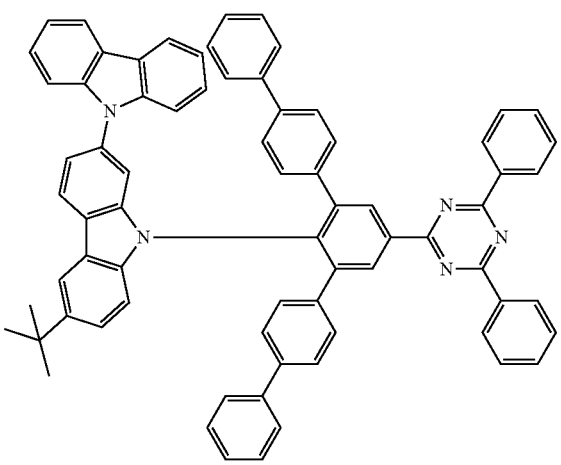
849
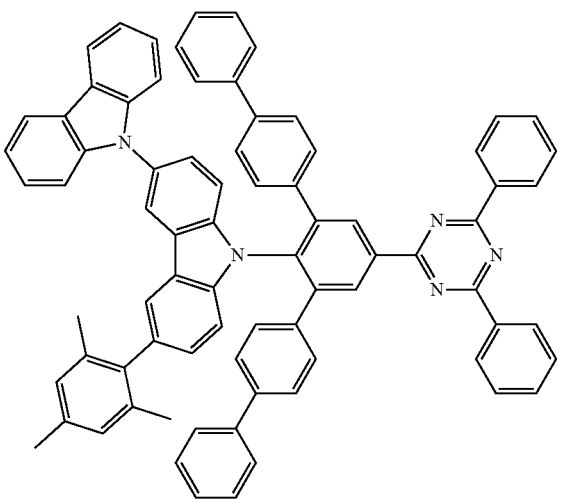
850
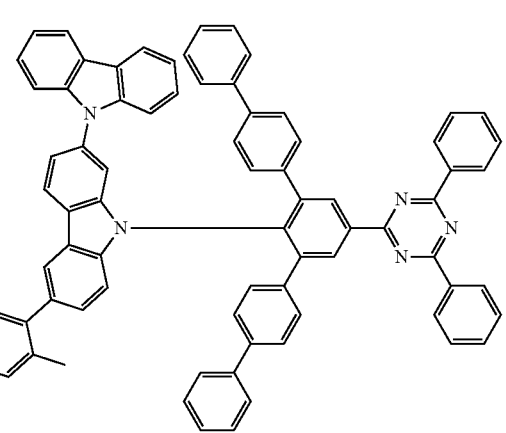

851
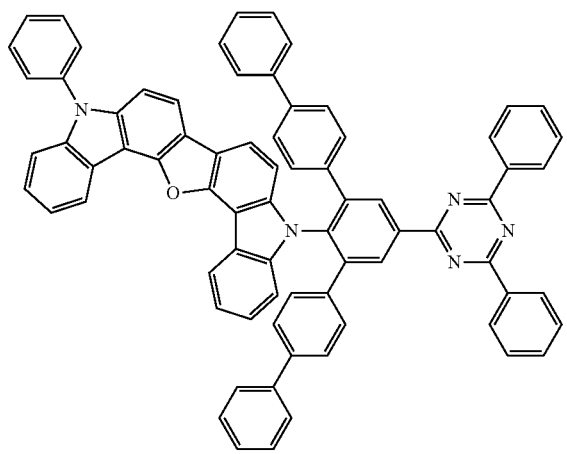
852
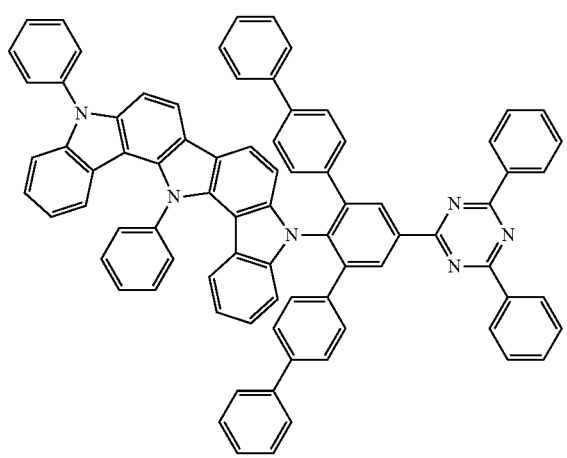
853
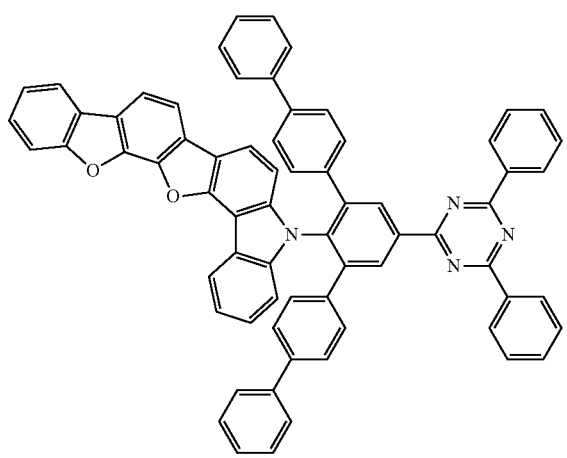
854
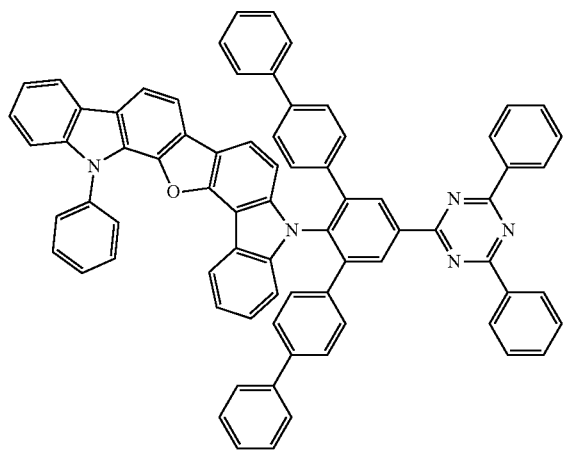
855
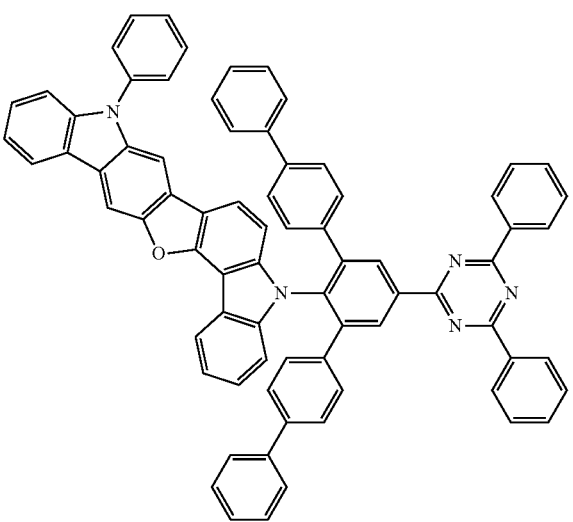
856

3235
-continued
857
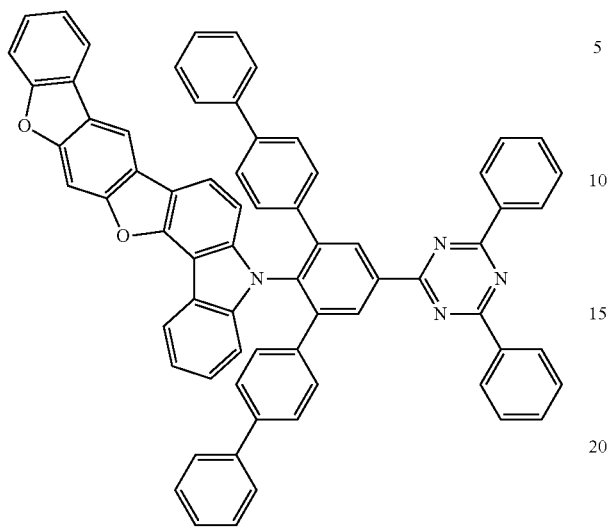
858
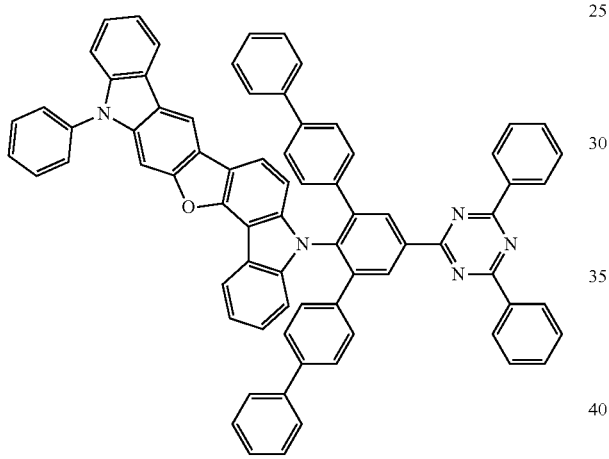
859
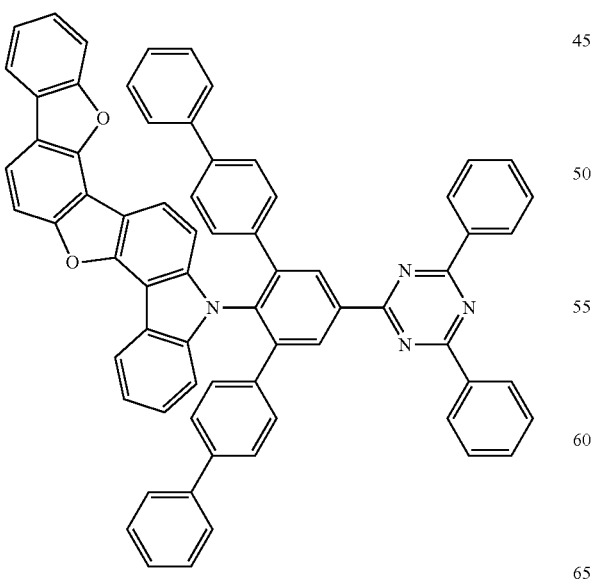
3236
-continued
860
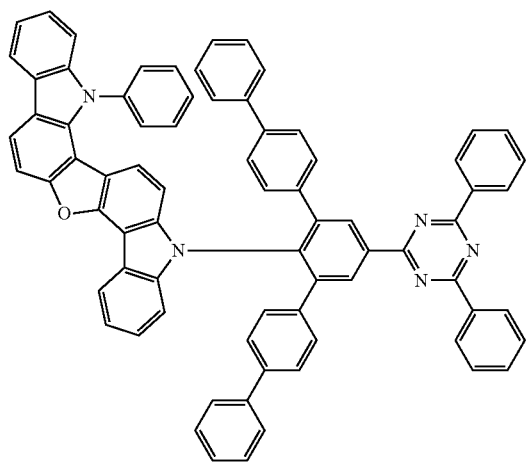
861
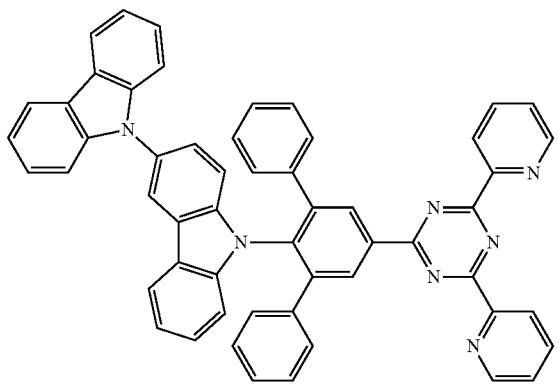
862
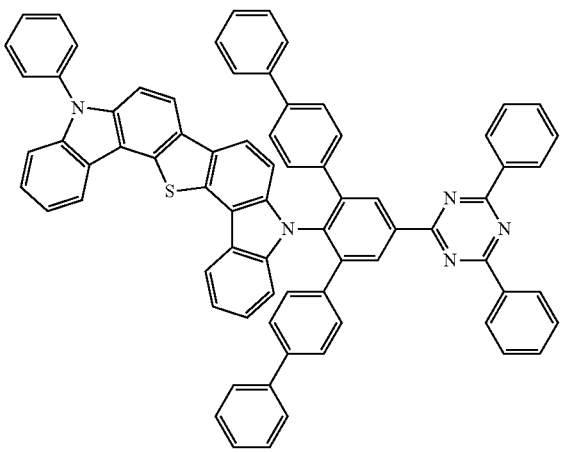

3237
-continued
863
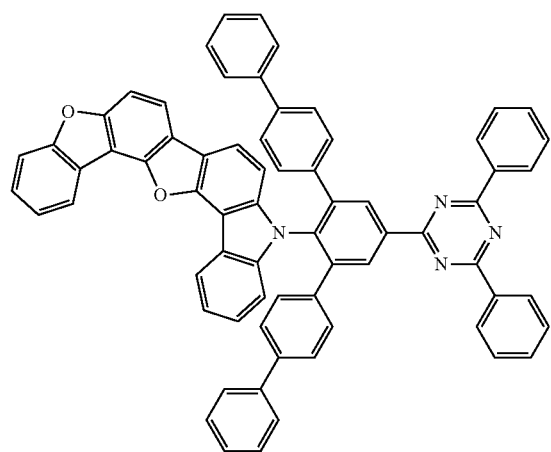
864
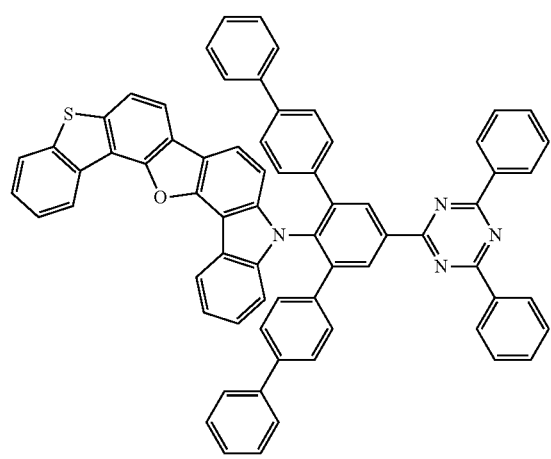
865
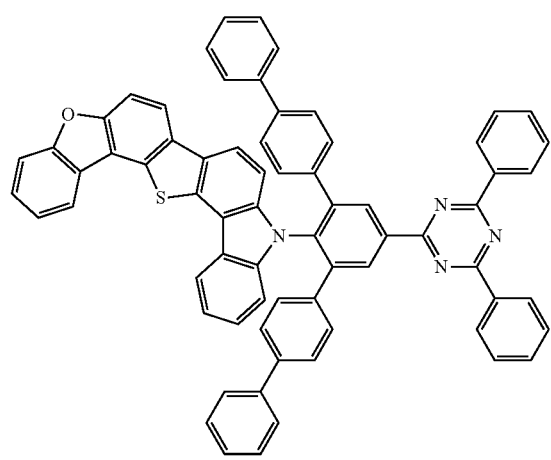
3238
-continued
866
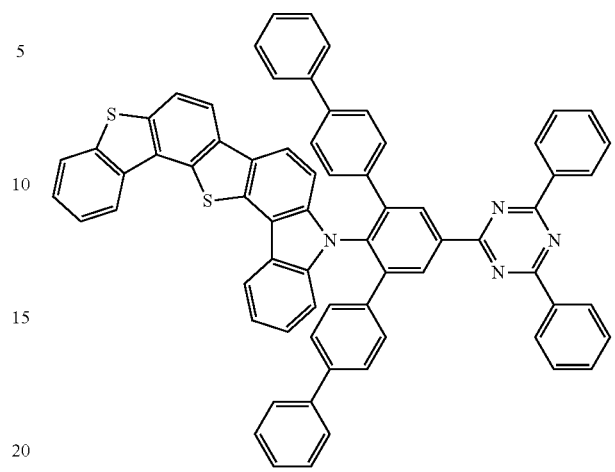
867
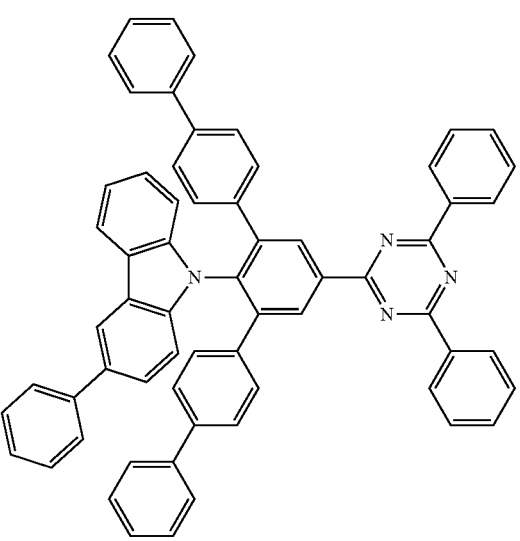
868
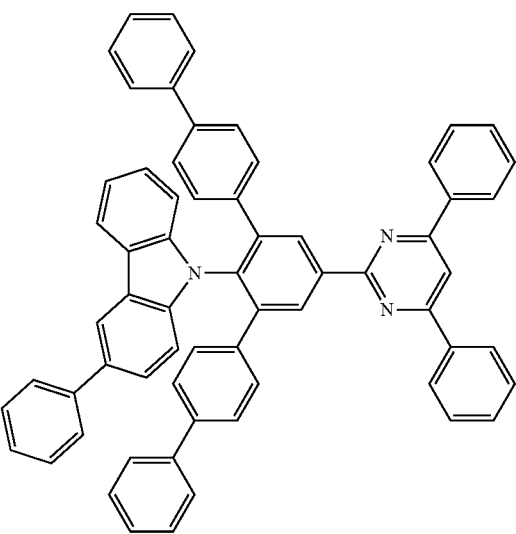

3239
-continued
869
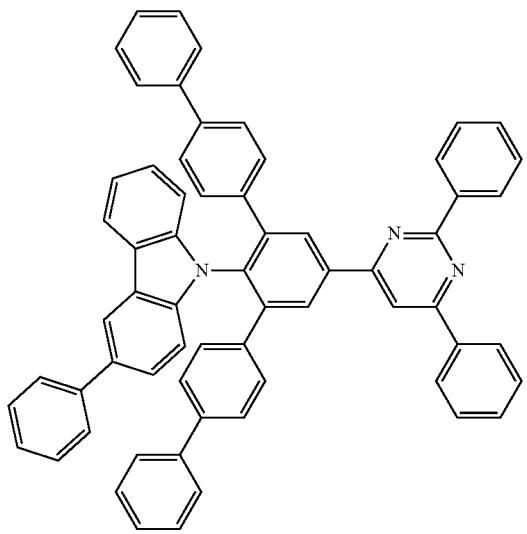
870
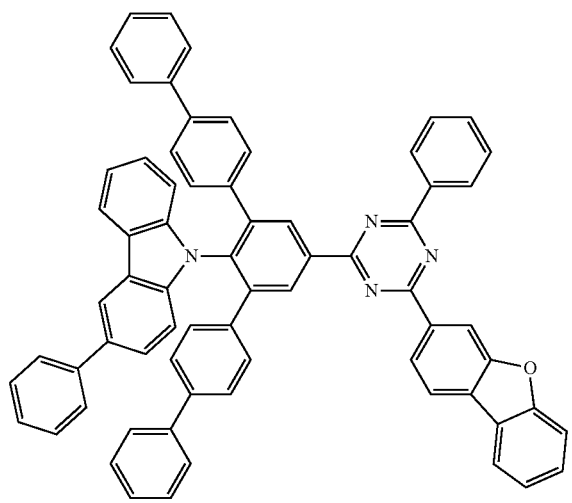
871
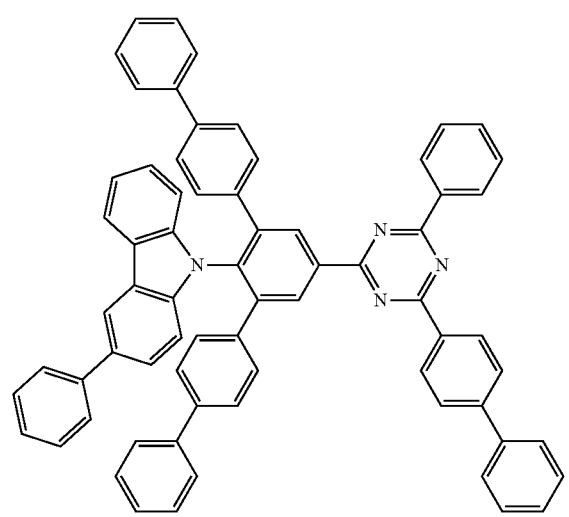
3240
-continued
872
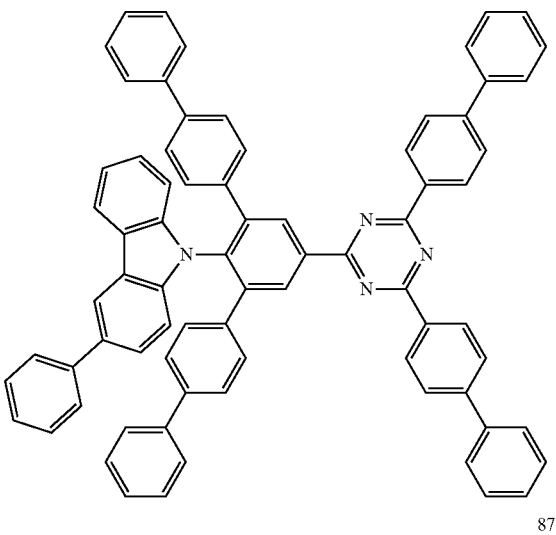
873
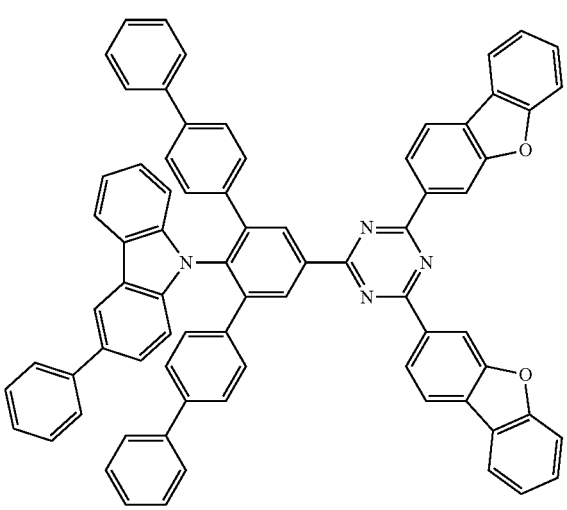
874
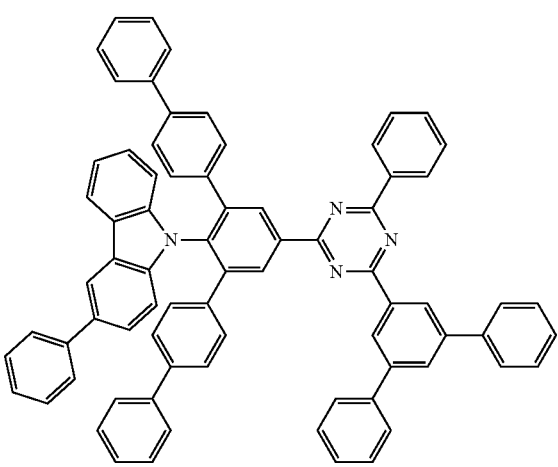

3241
-continued
875
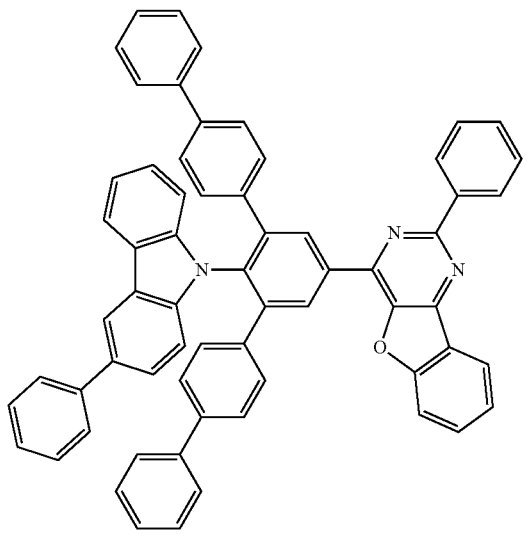
876
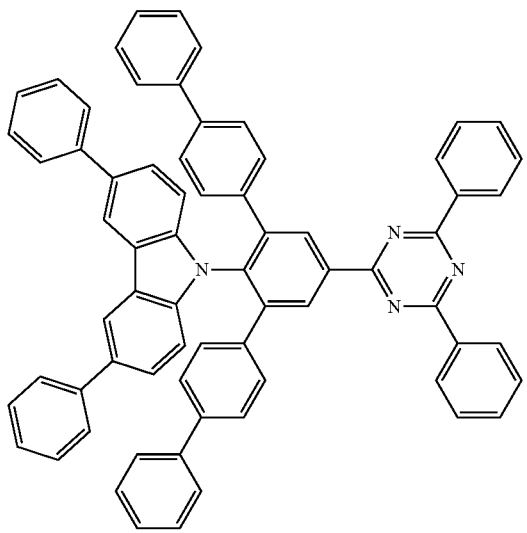
877
3242
-continued
878
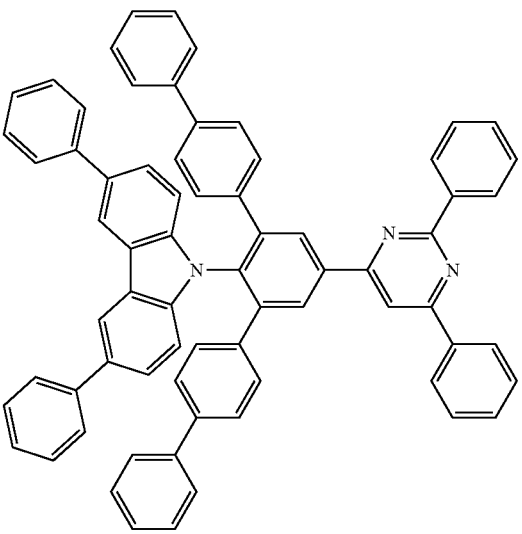
879
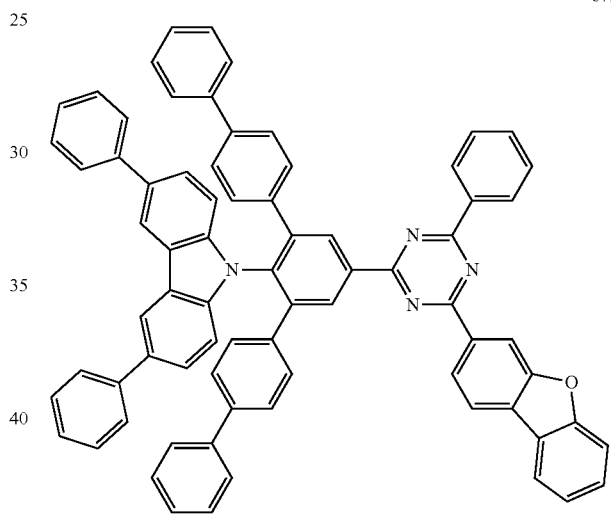
880

3243
-continued
881
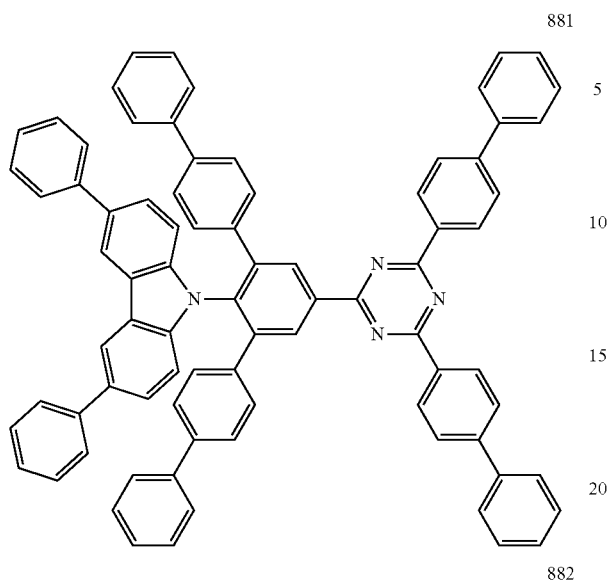
882
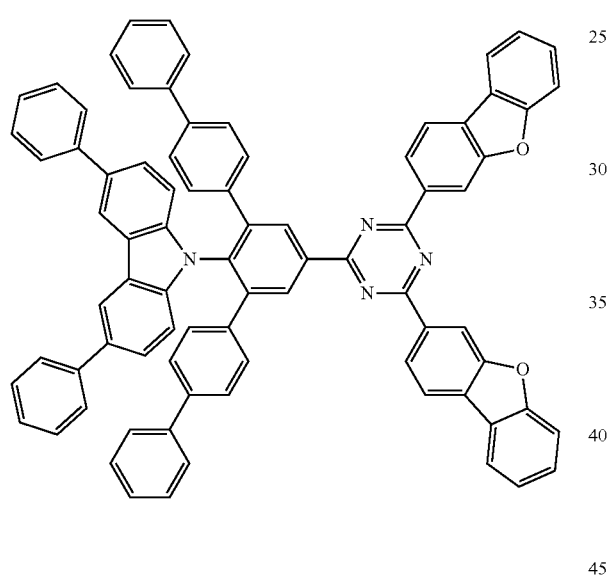
883
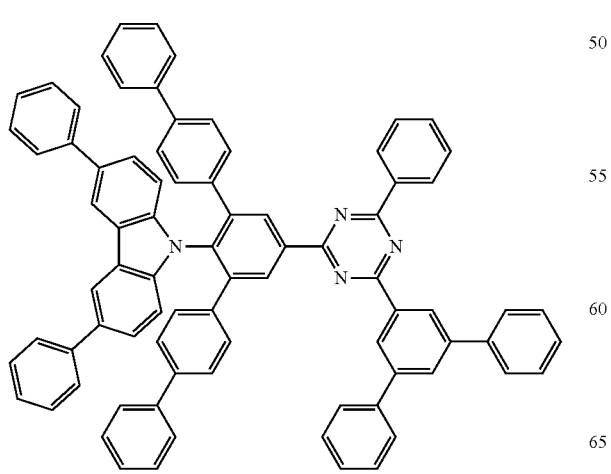
3244
-continued
884
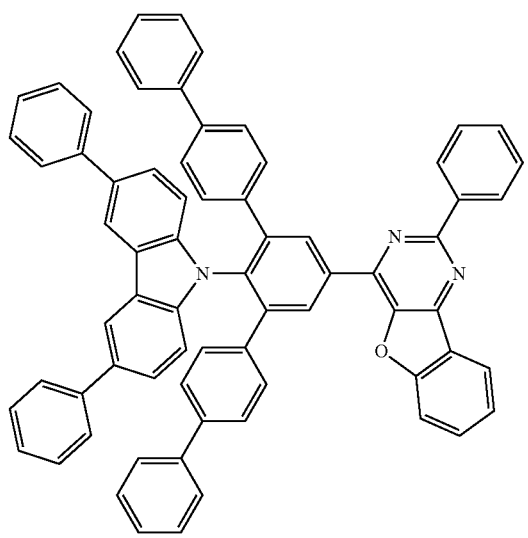
885
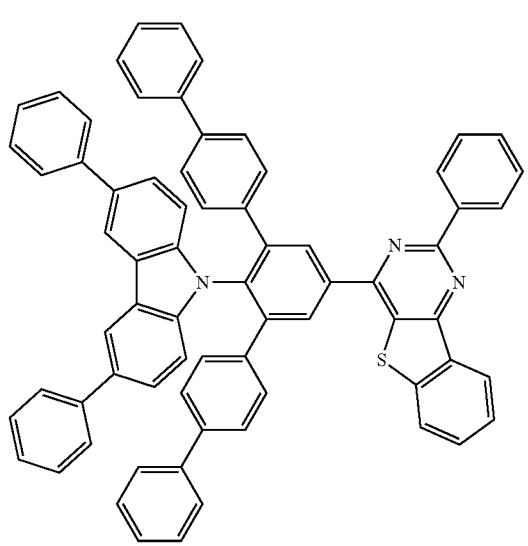
886
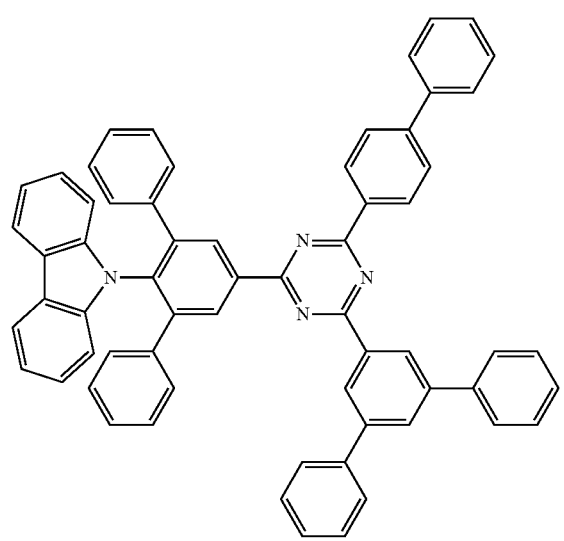

887
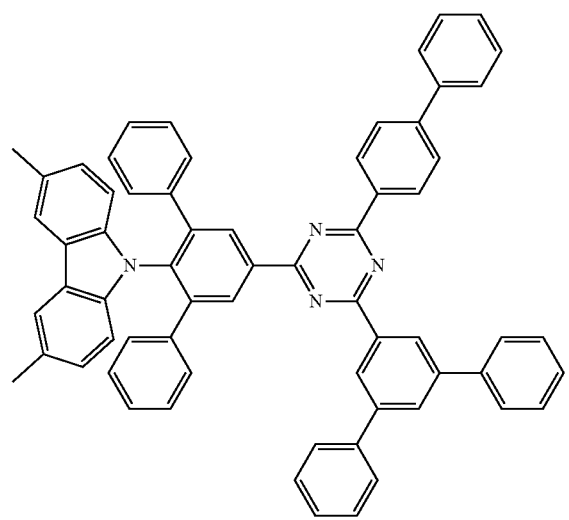
890
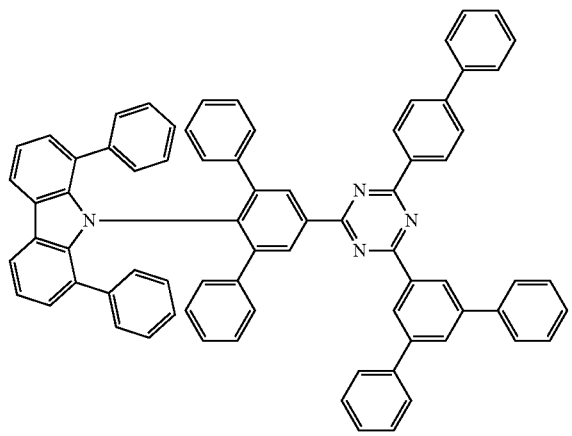
888
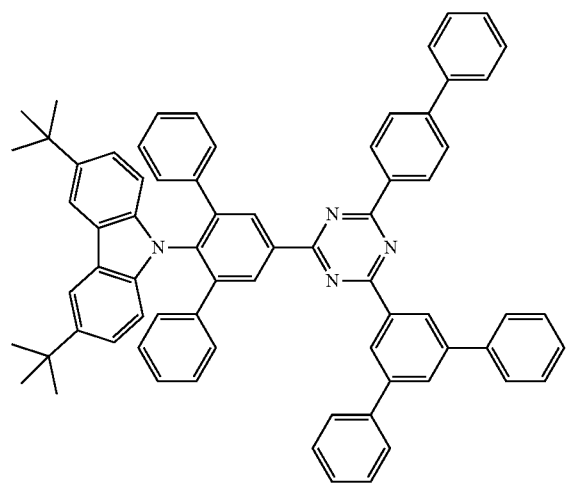
891
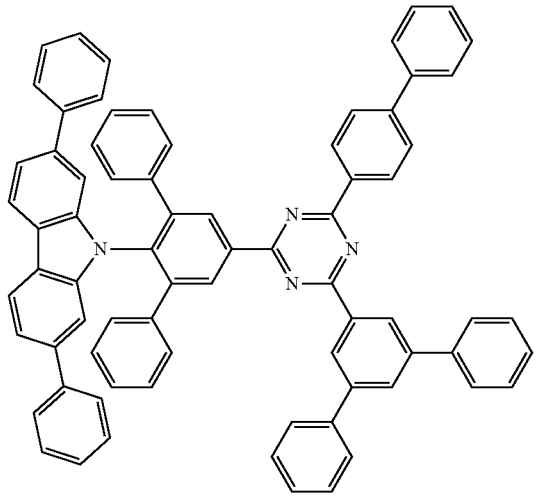
889
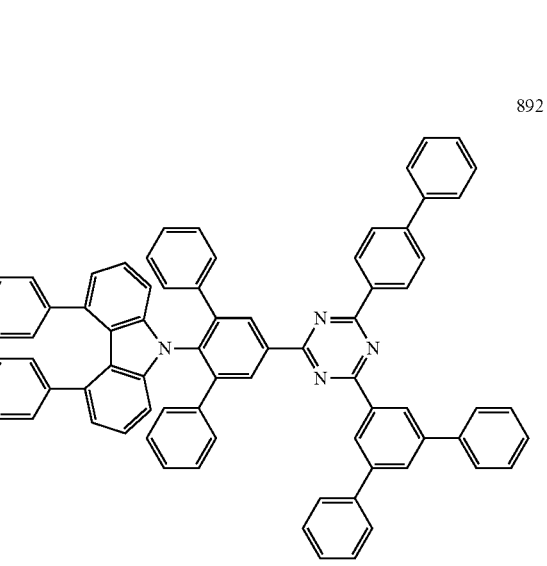

3247
-continued
893
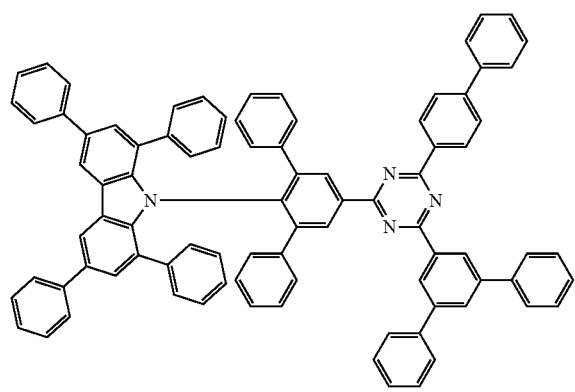
894
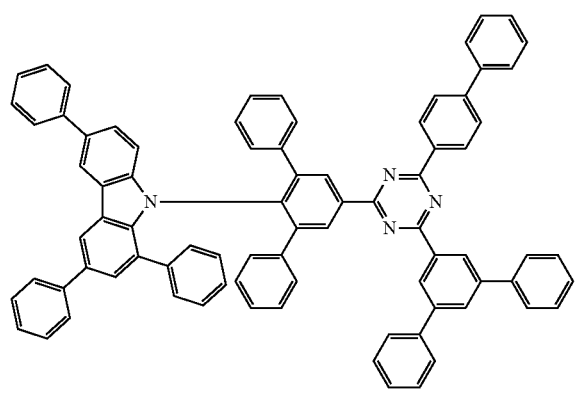
895
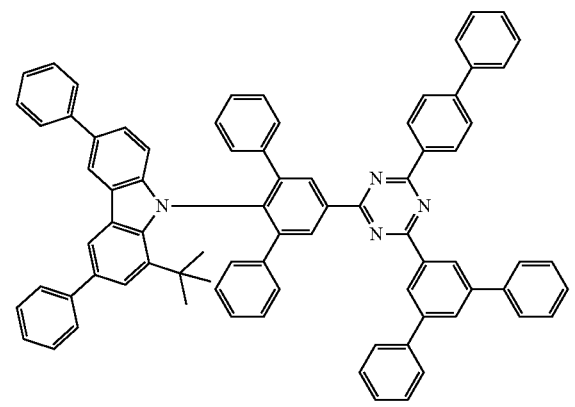
3248
-continued
896
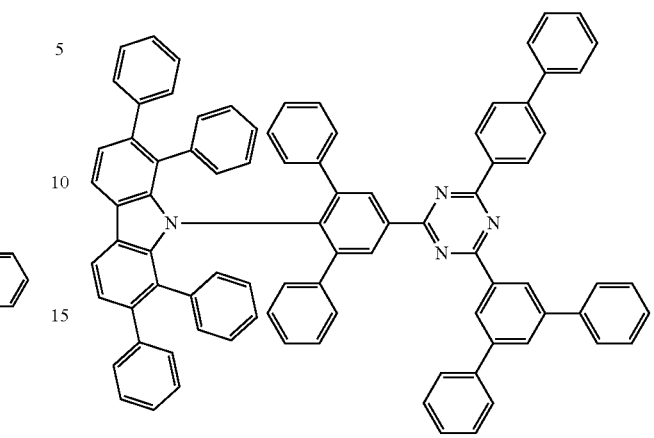
897
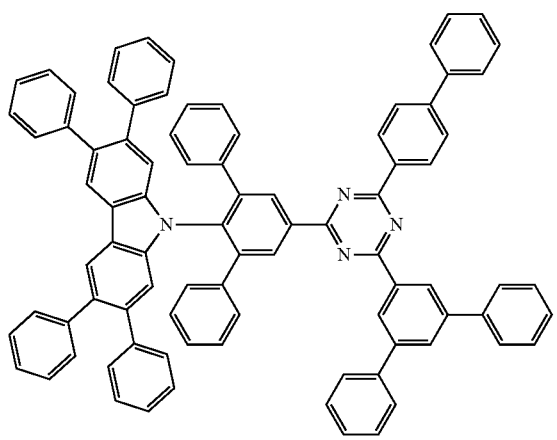
898

3249
-continued
899
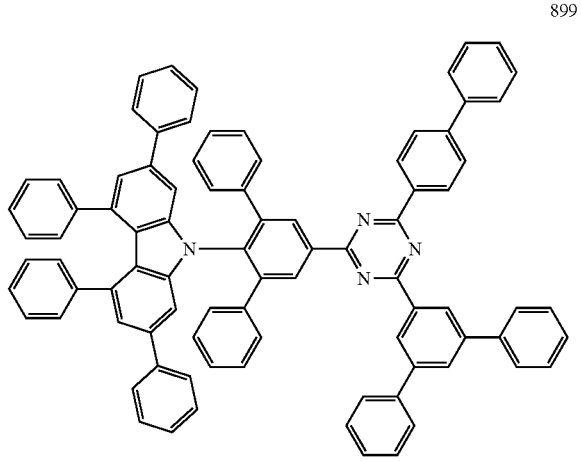
900
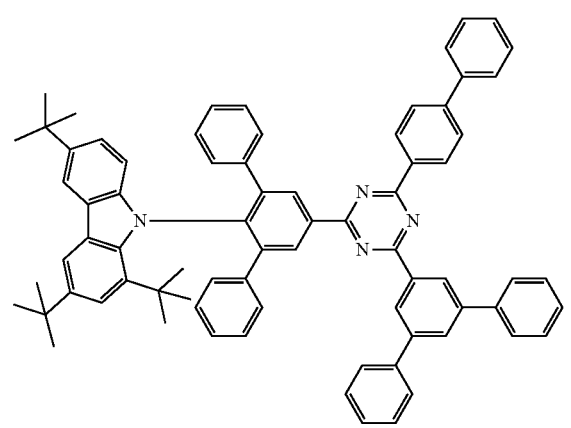
901
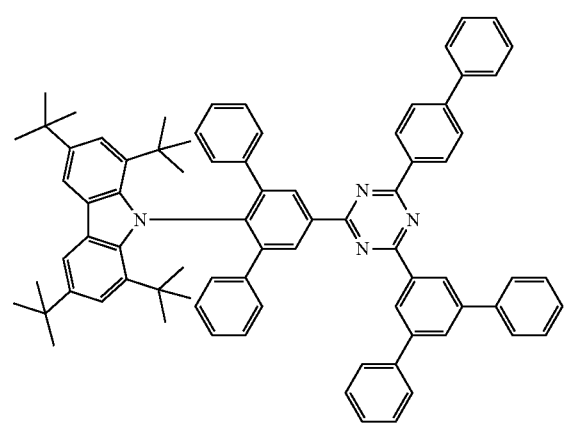
3250
-continued
902
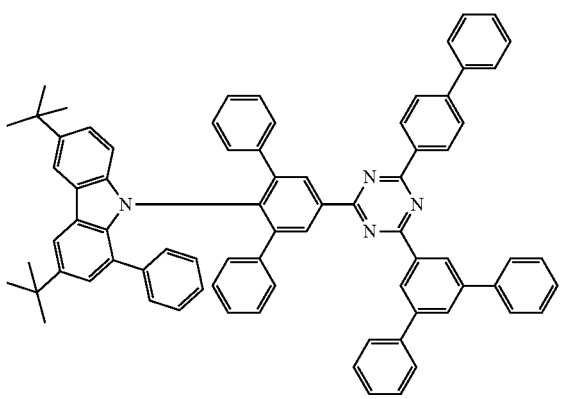
903
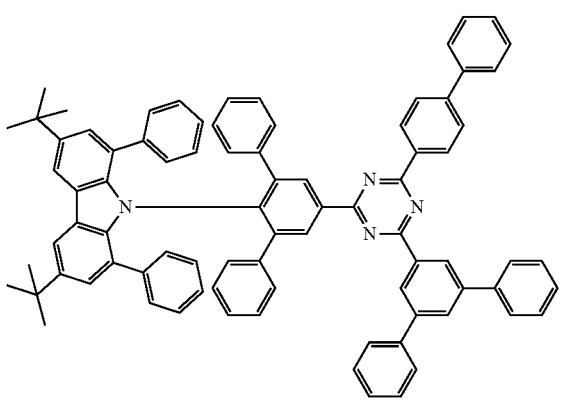
904
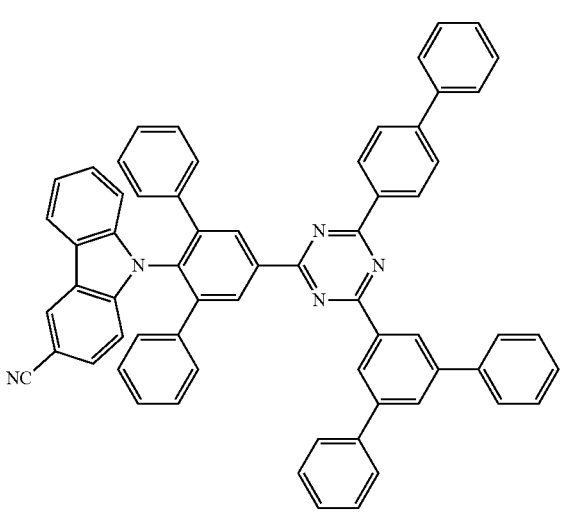

905
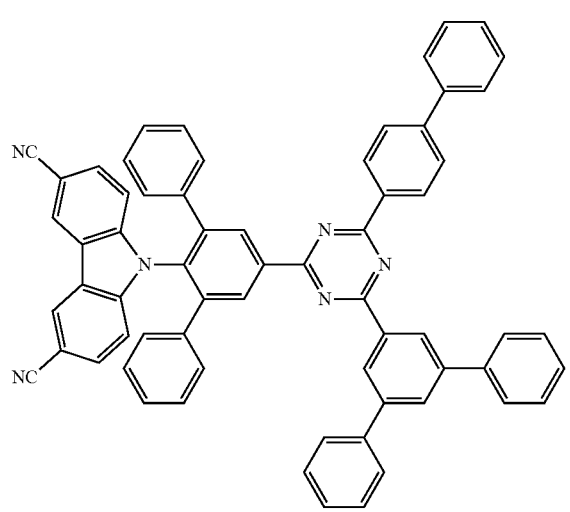
906
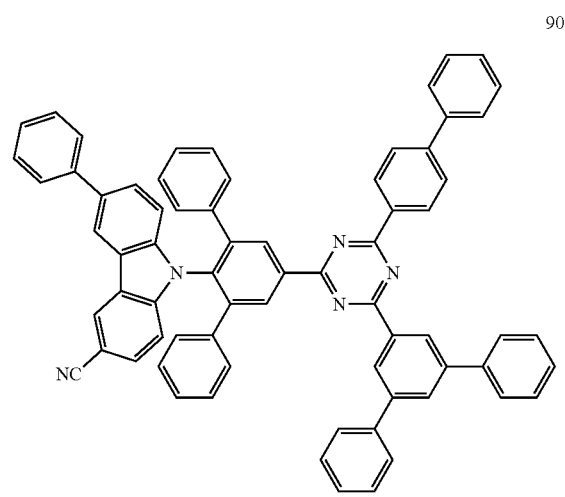
907
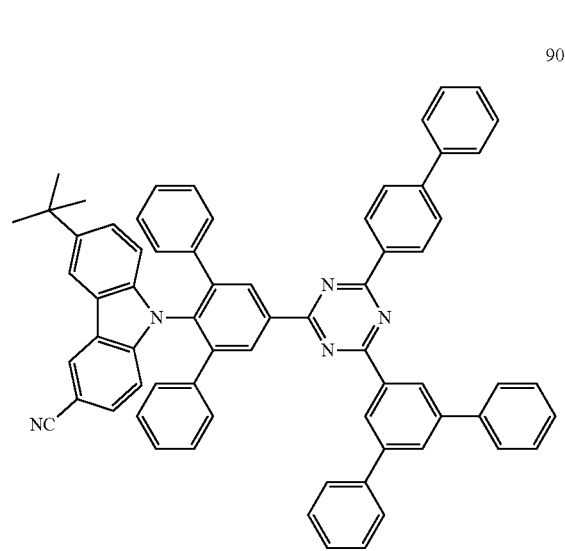
908
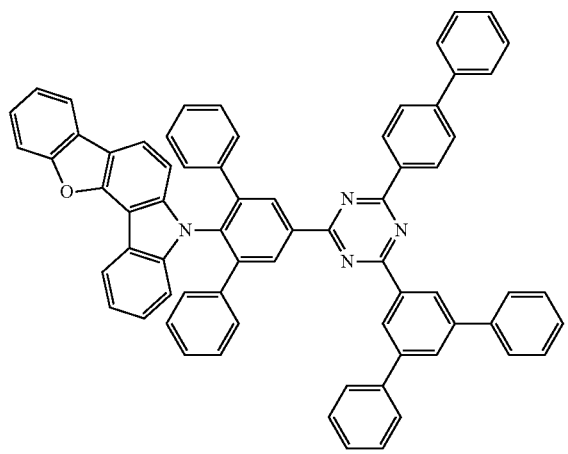
909
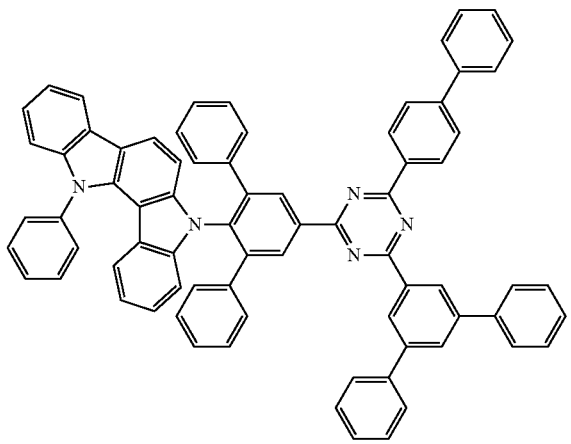
910
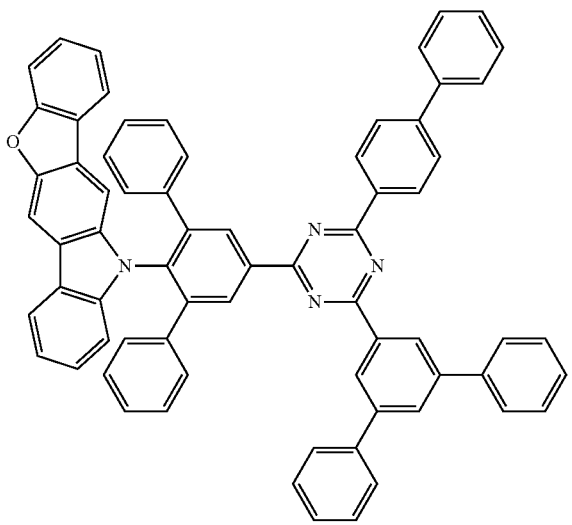

911
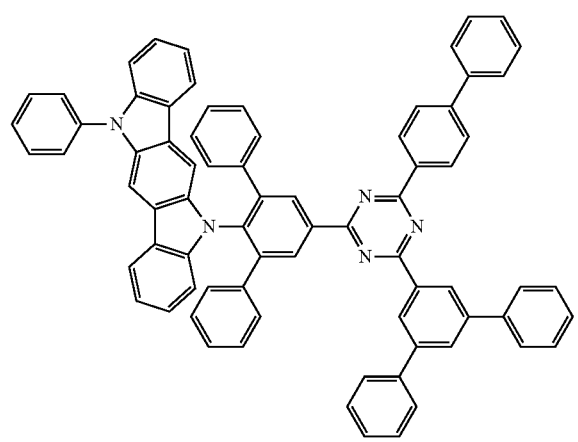
912
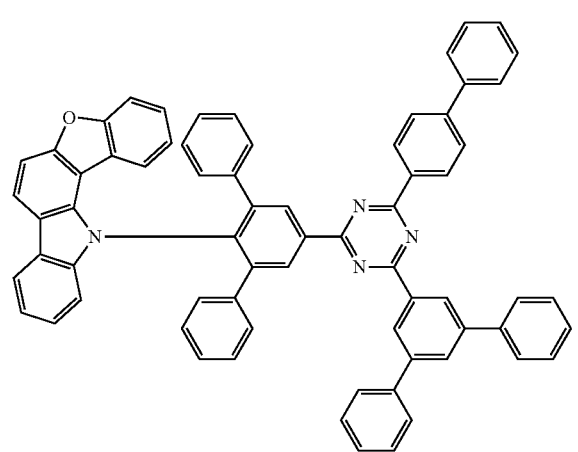
913
914
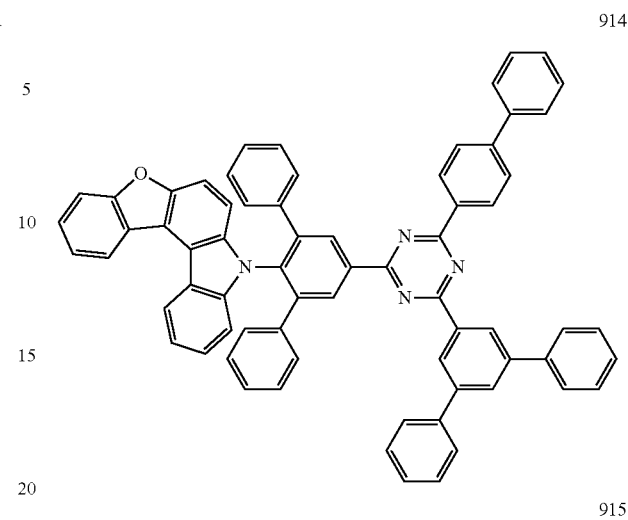
915
916
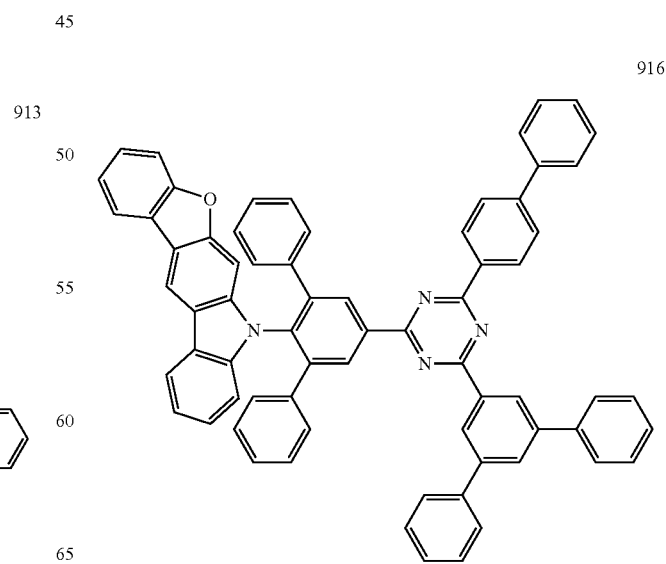

3255
-continued
917
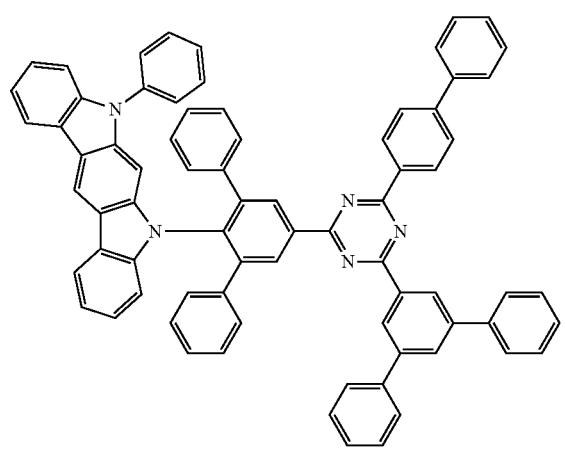
918
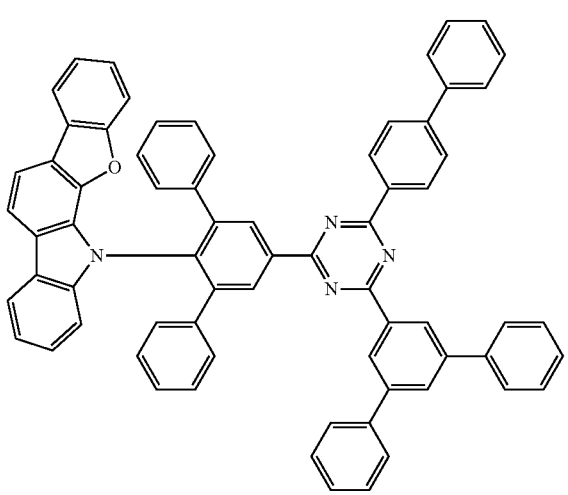
919
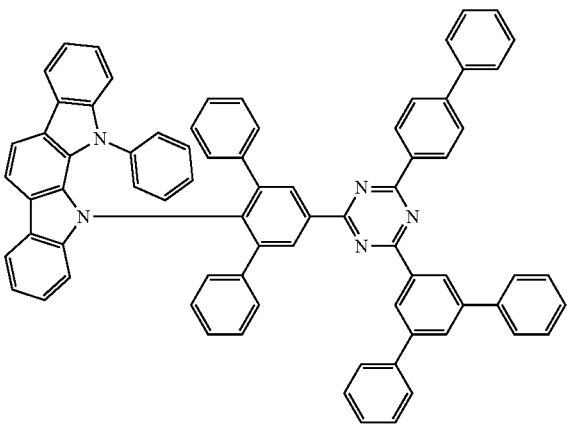
3256
-continued
920
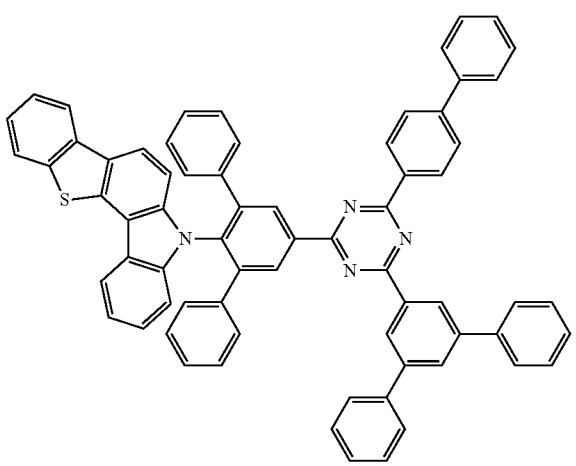
921
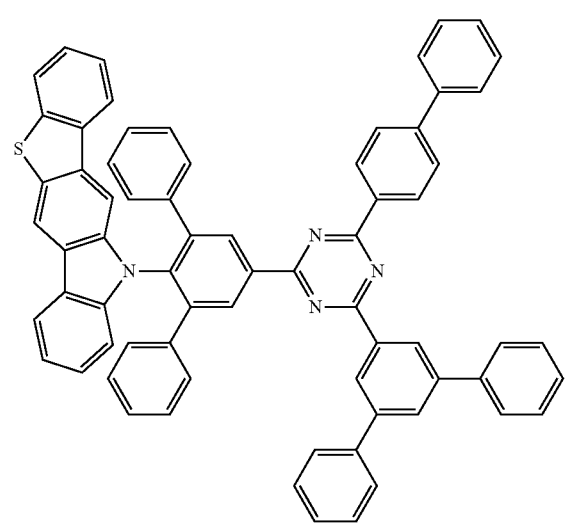
922
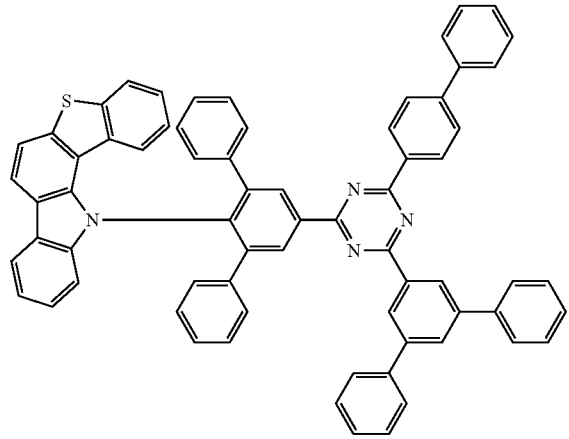

3257
-continued
923
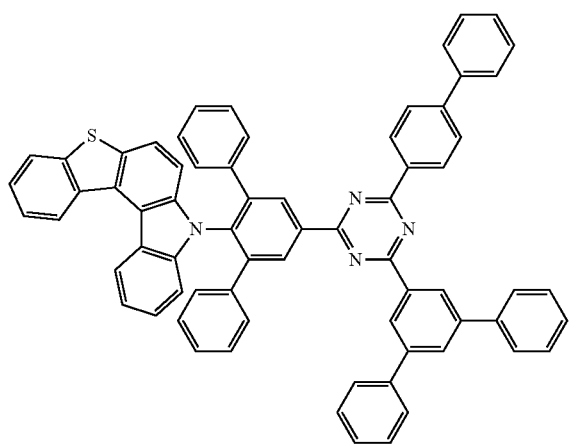
924
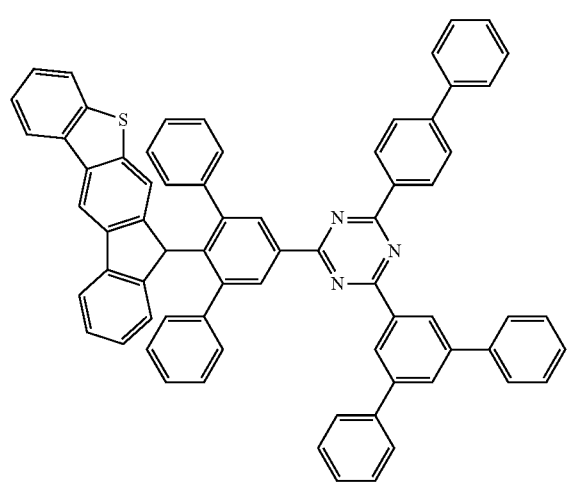
925
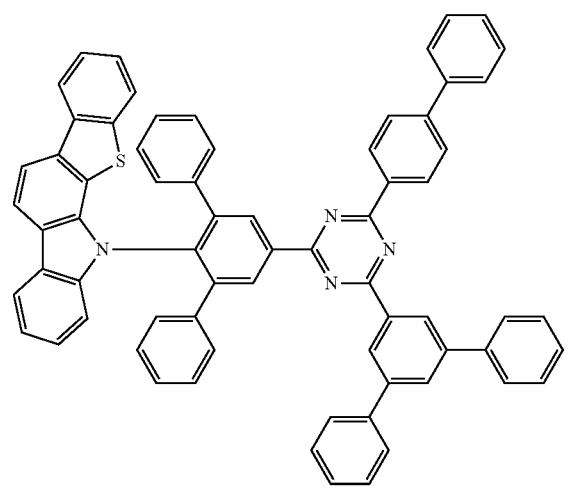
3258
-continued
926
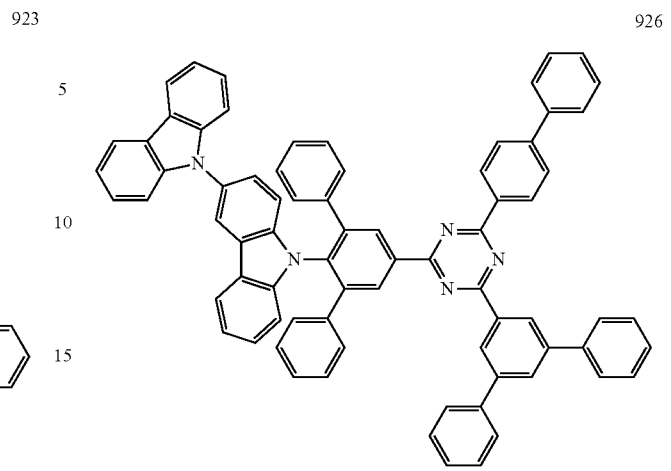
927
928
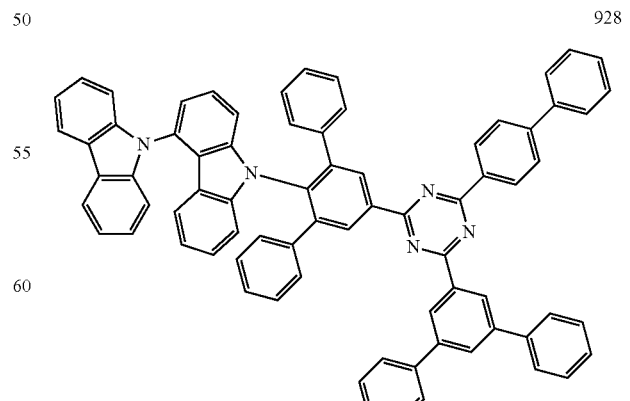

3259
-continued
929
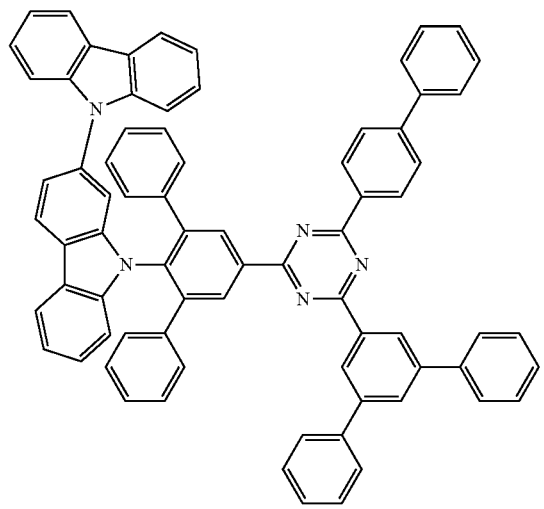
930
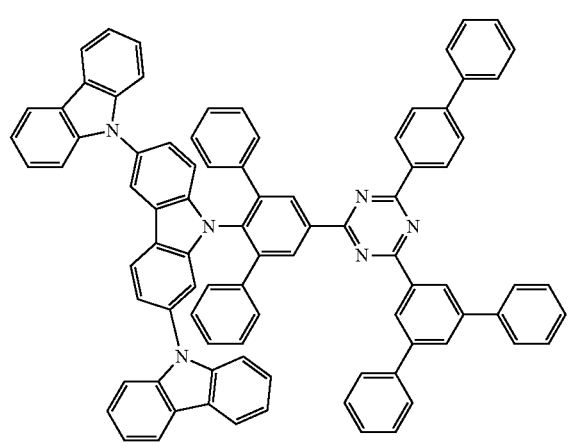
931
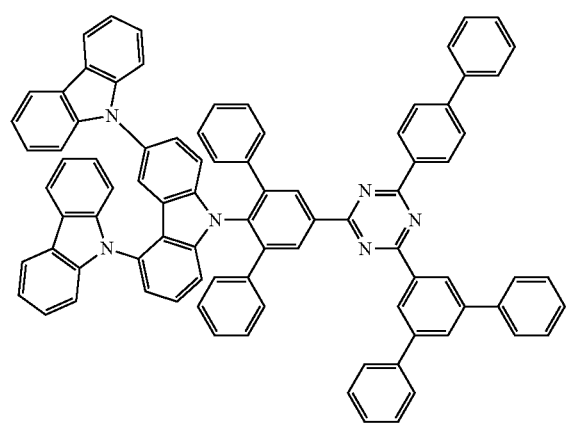
3260
-continued
932
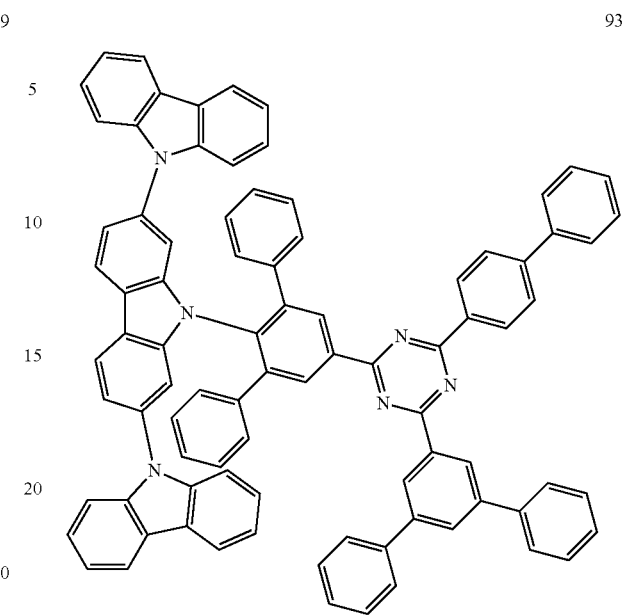
933
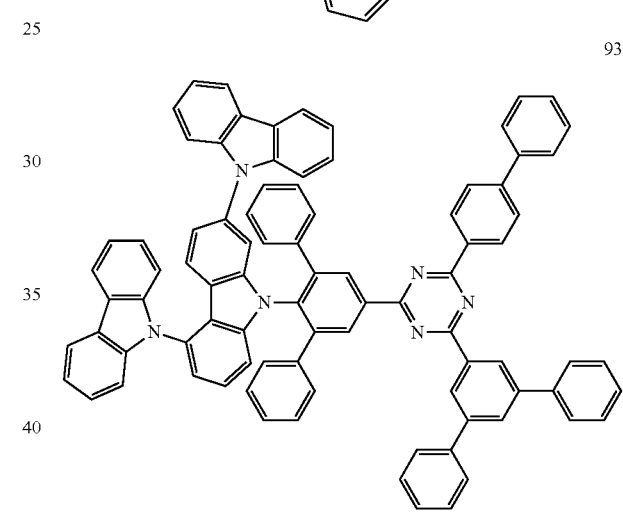
934
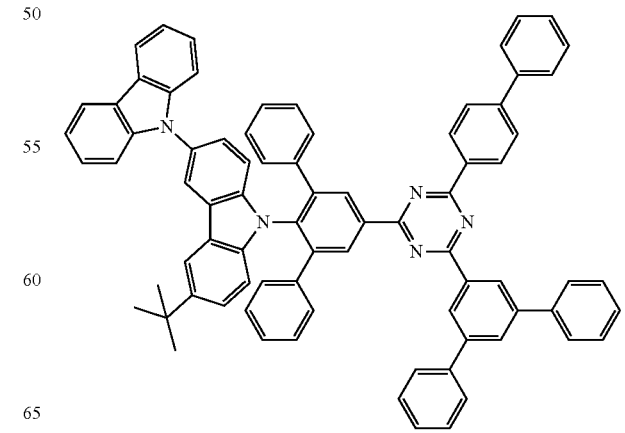

3261
-continued
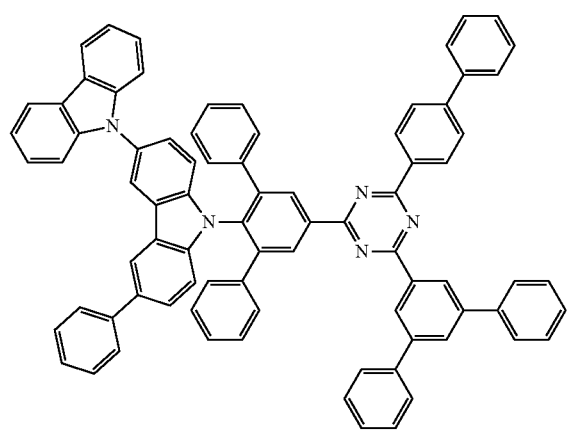
935
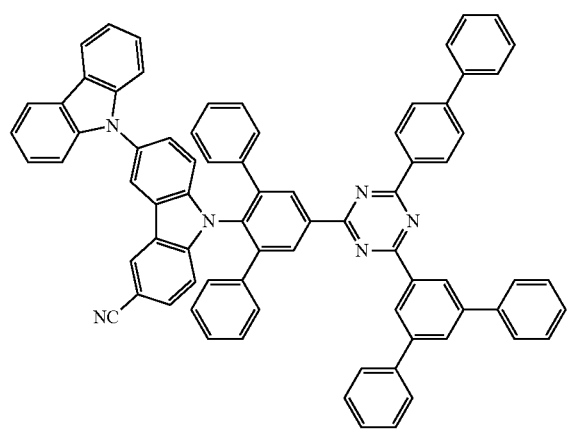
936
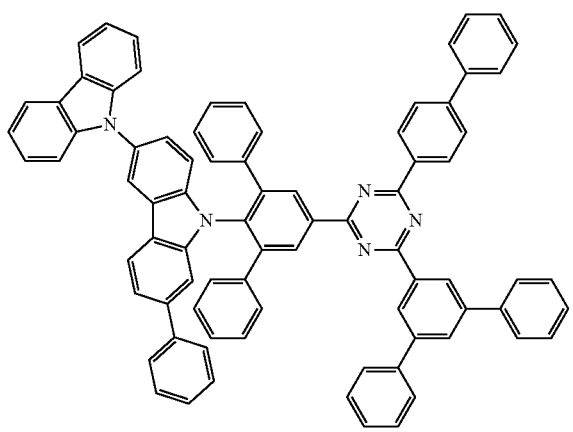
937
3262
-continued
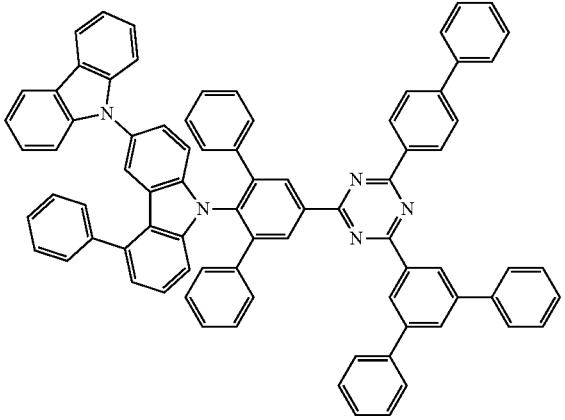
938
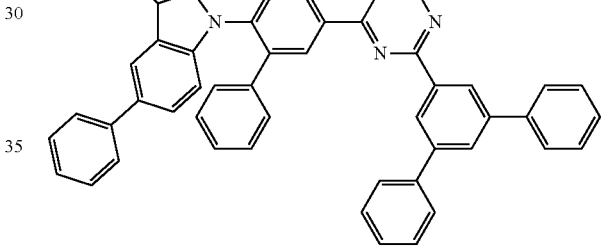
939
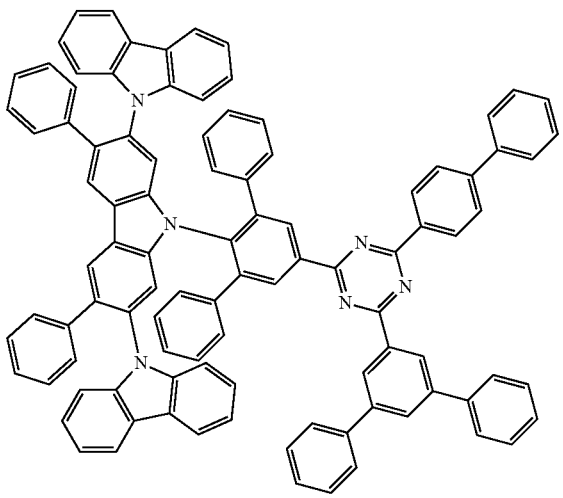
940

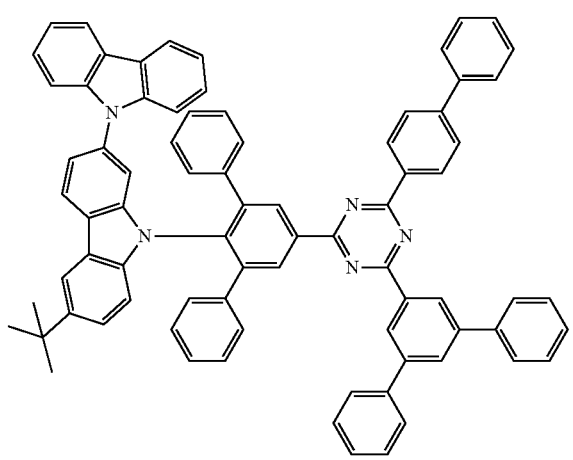
941
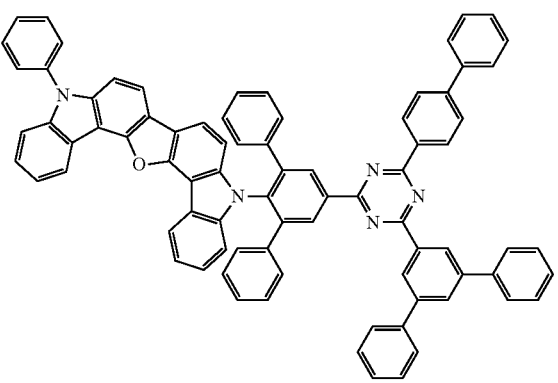
944
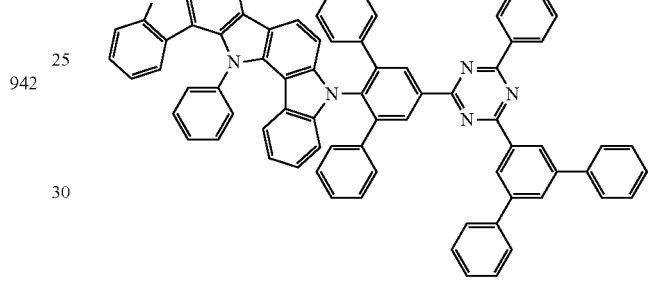
945
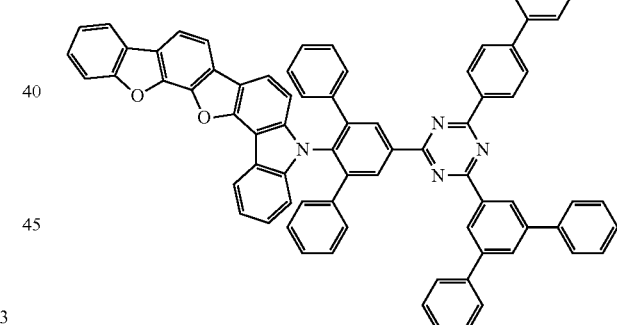
942
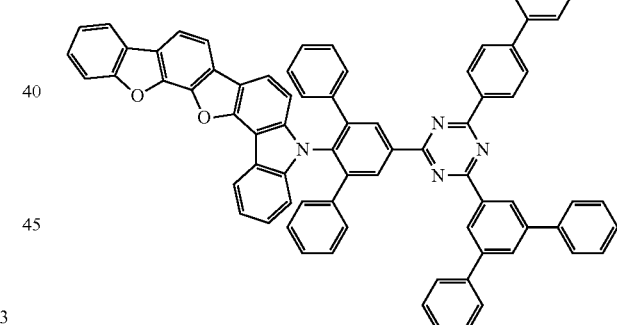
946
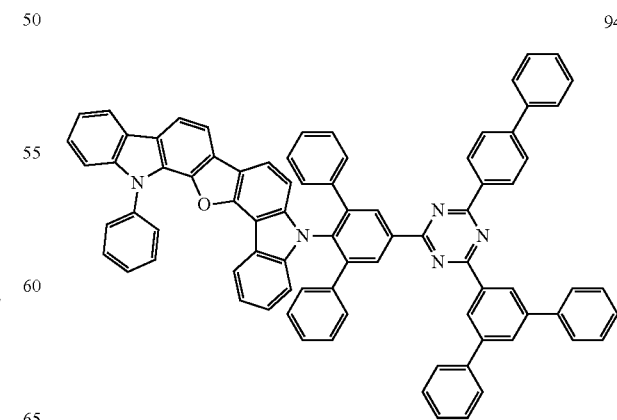
943
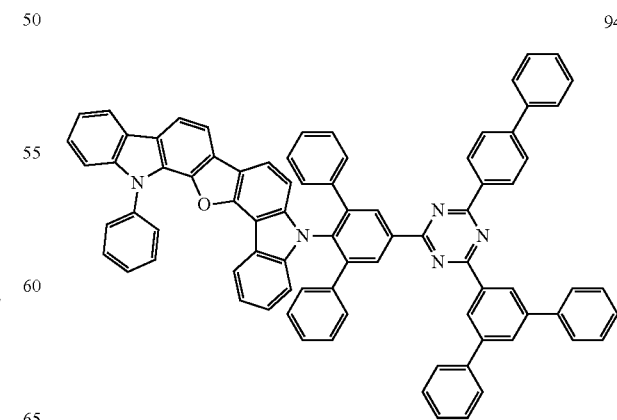
947

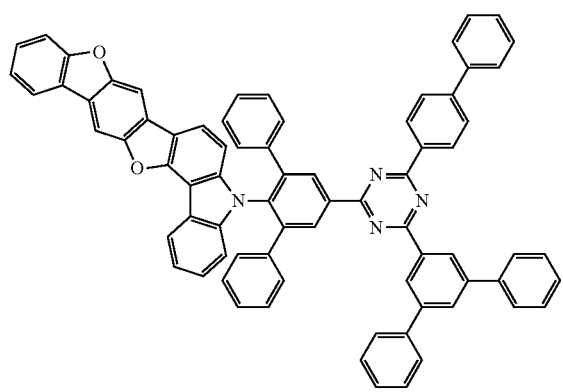
948
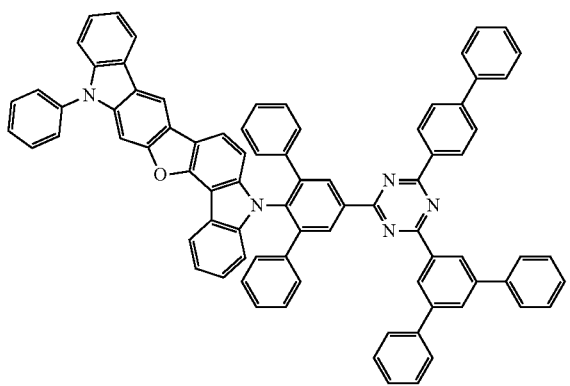
951
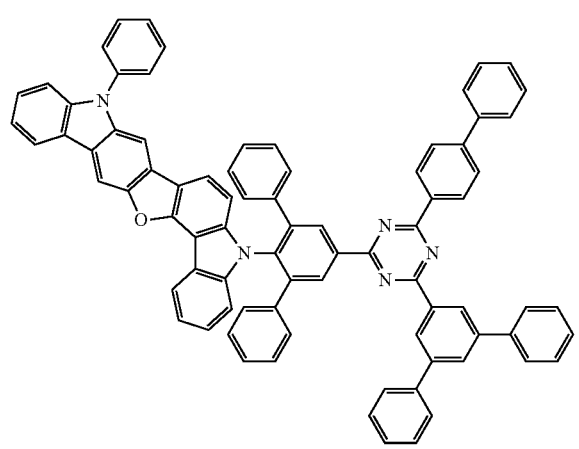
949
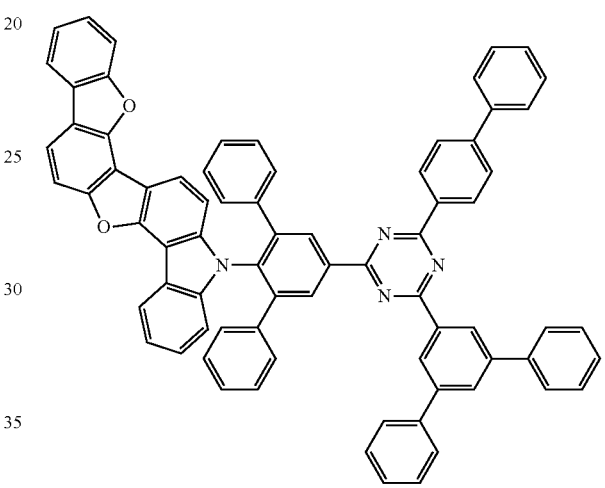
952
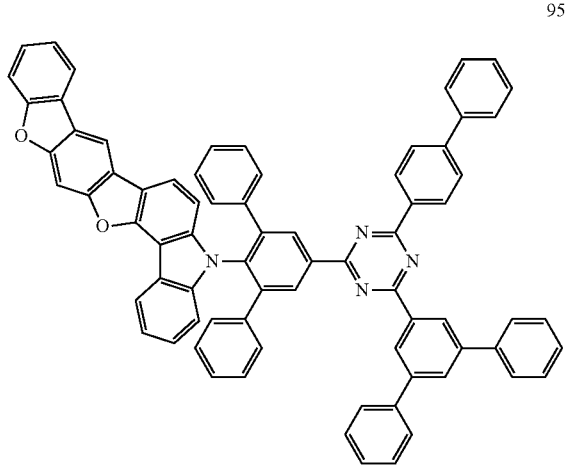
950
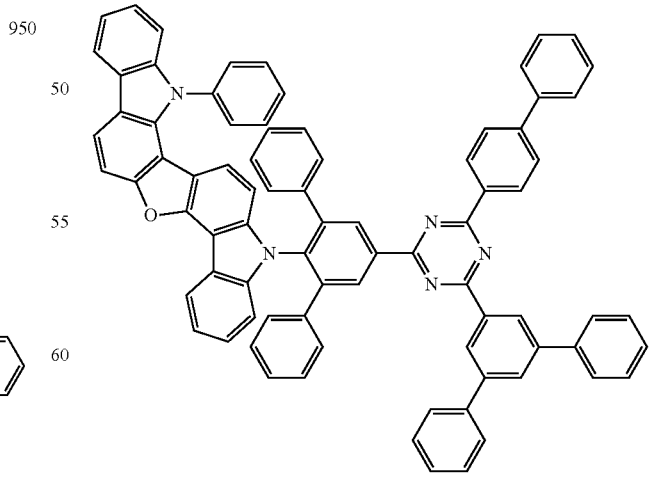
953

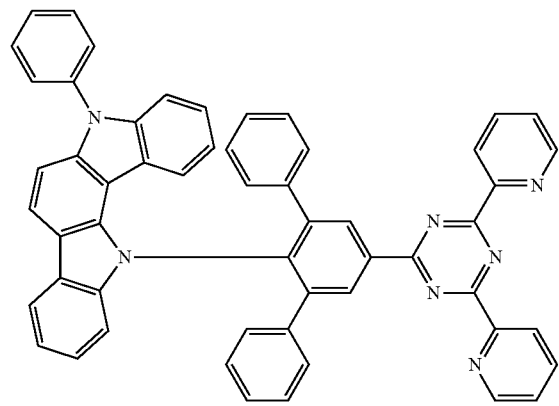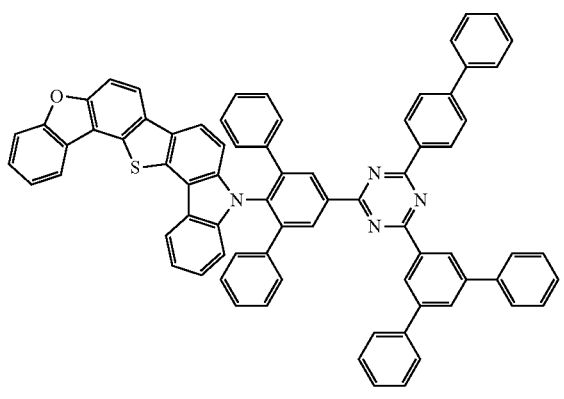

3269
-continued
961
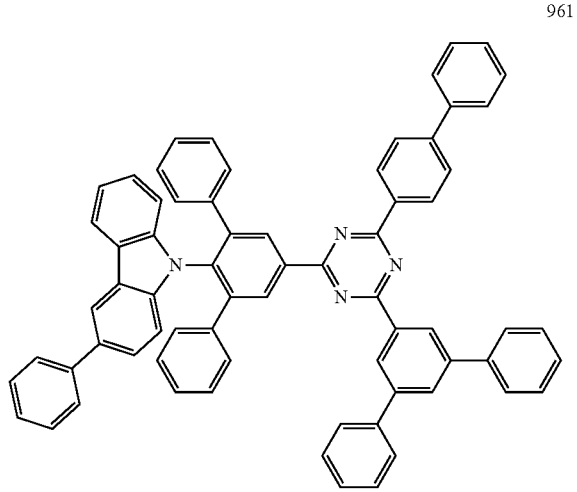
962
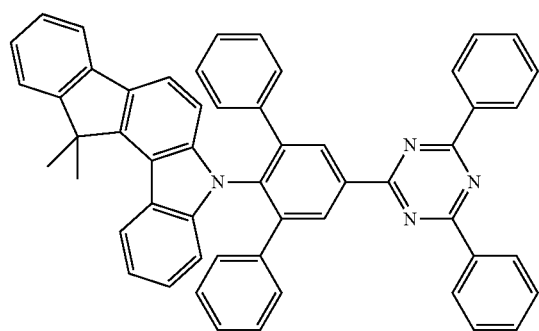
963
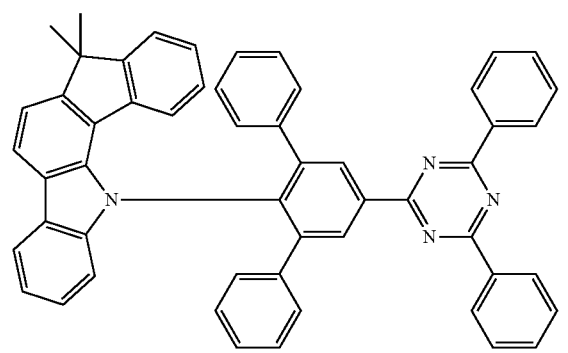
964
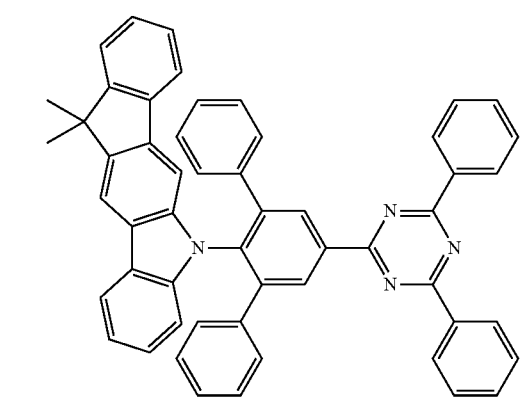
3270
-continued
965
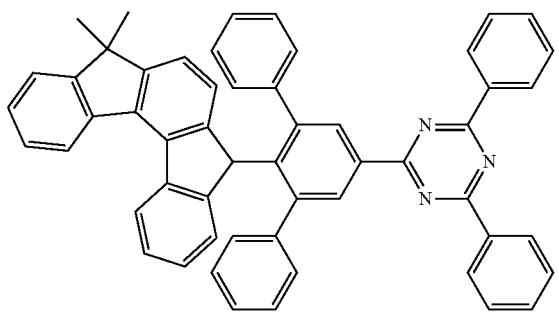
966
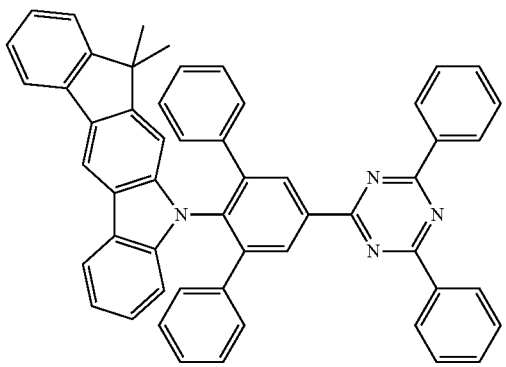
967
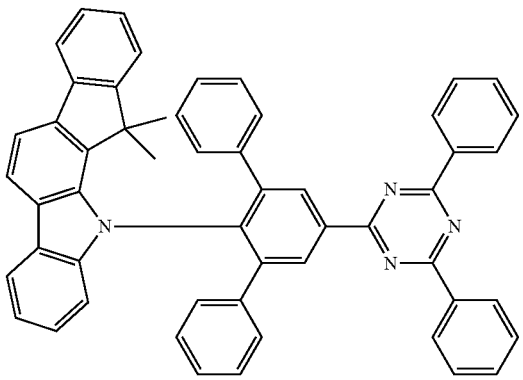
968
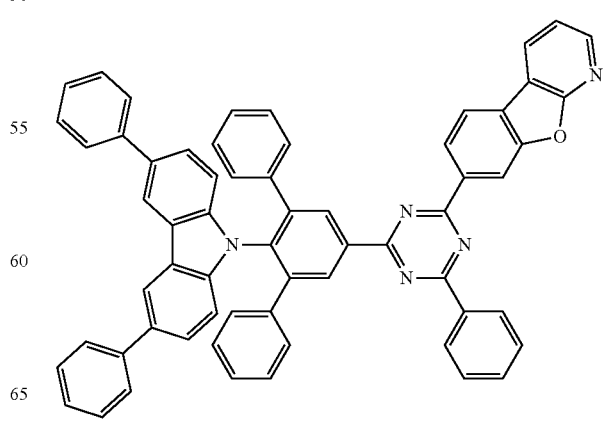

3271
-continued
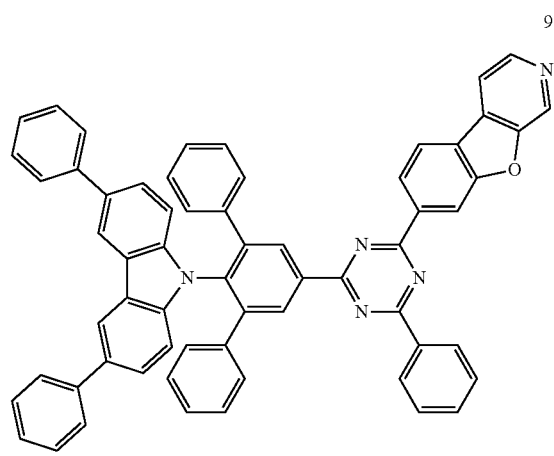
969
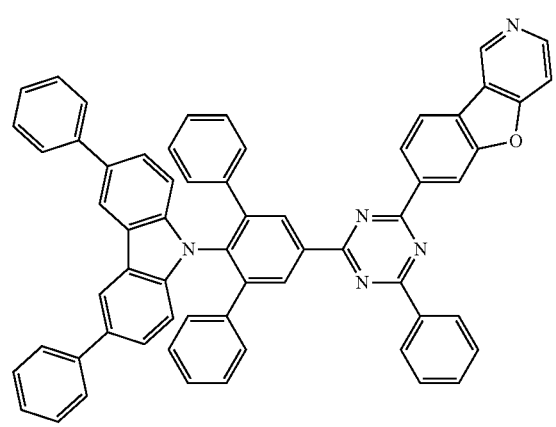
970
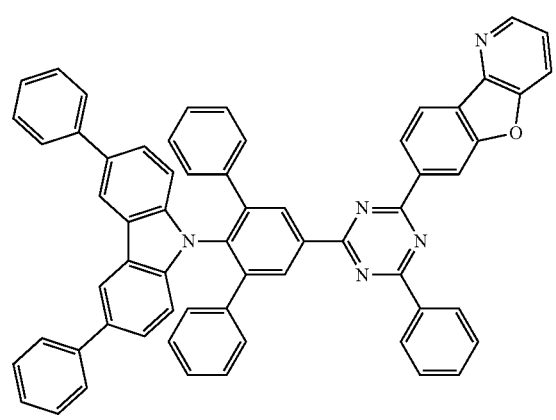
971
3272
-continued
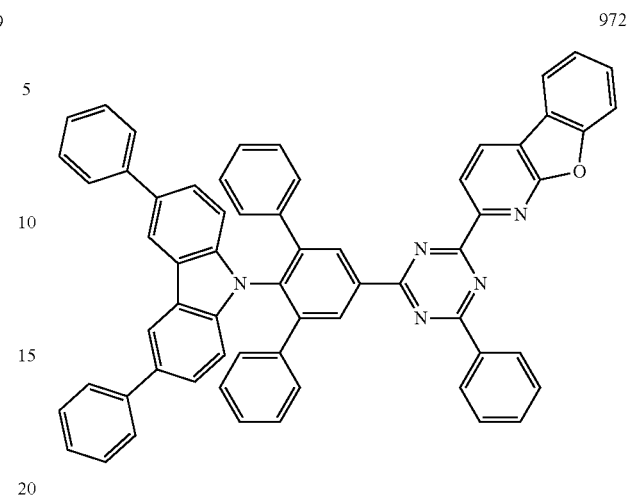
972
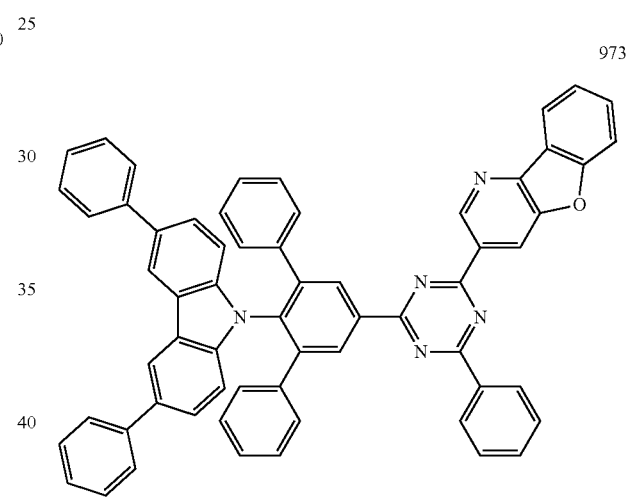
973
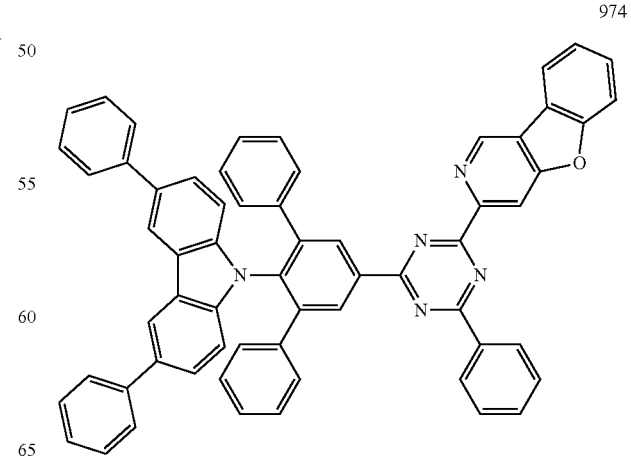
974

975
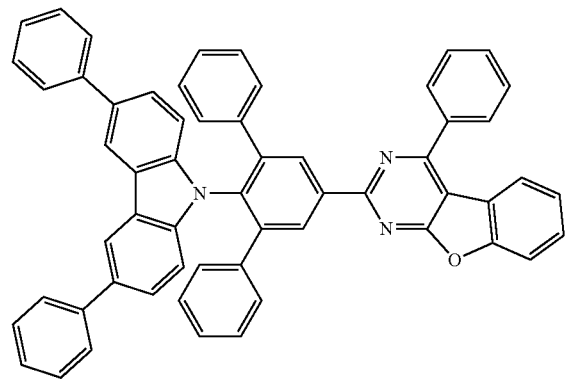
976
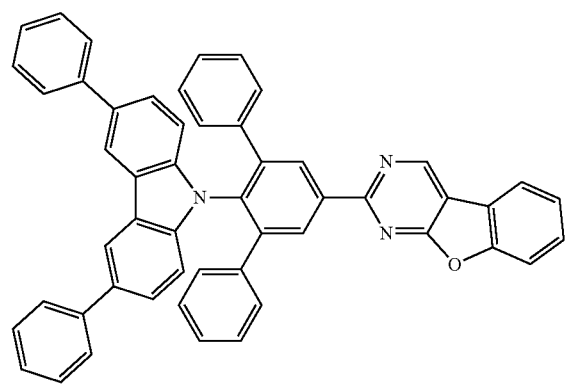
977
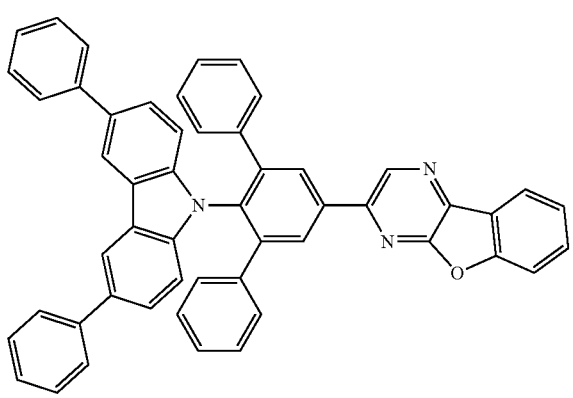
978
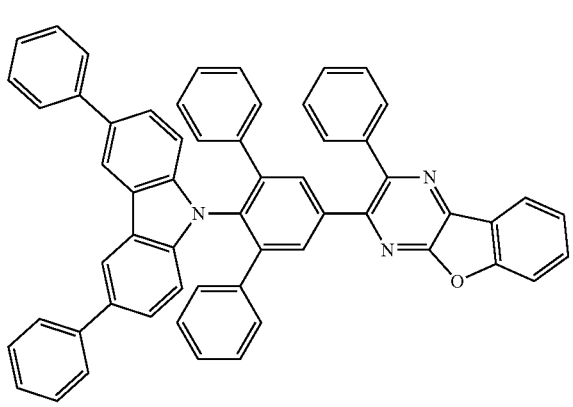
979
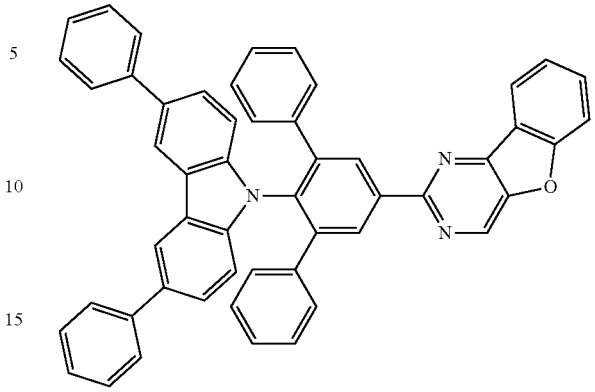
980
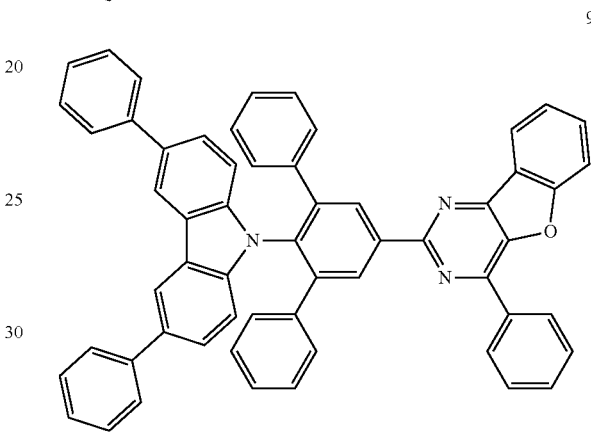
981
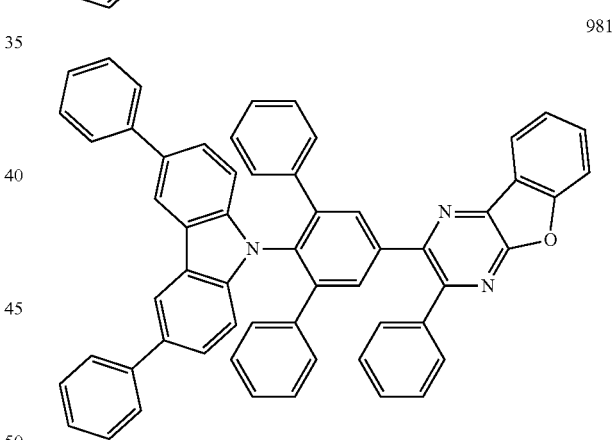
982
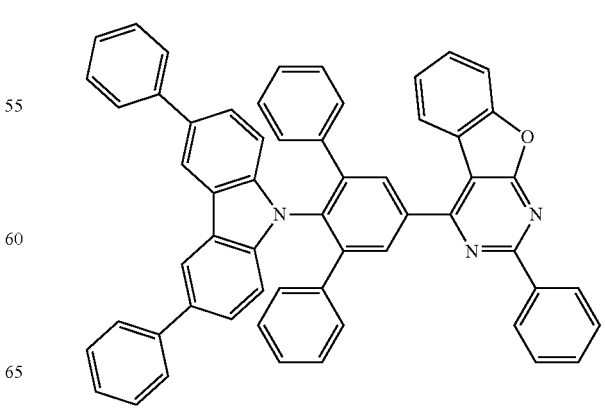

3275
-continued
983
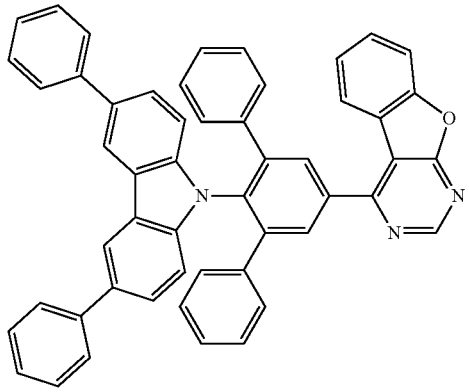
984
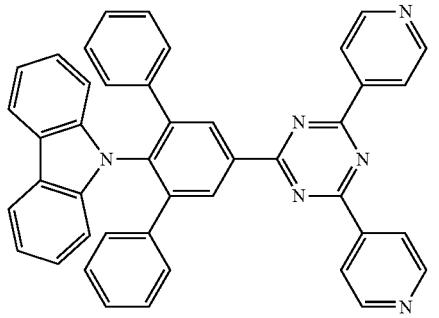
985
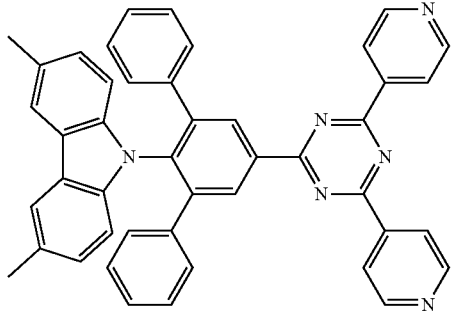
986
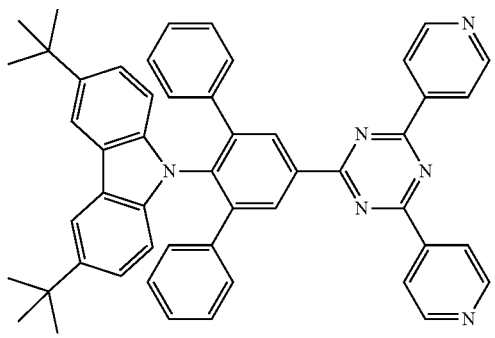
3276
-continued
987
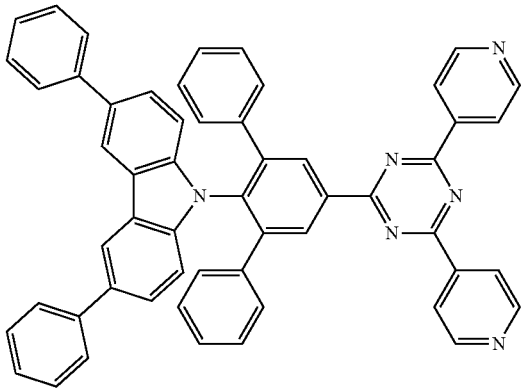
988
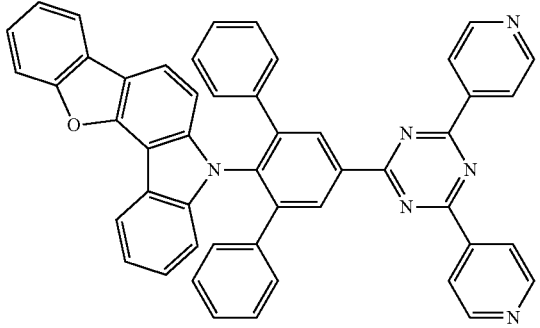
989
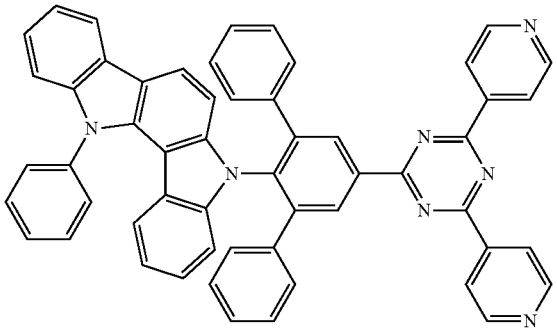
990
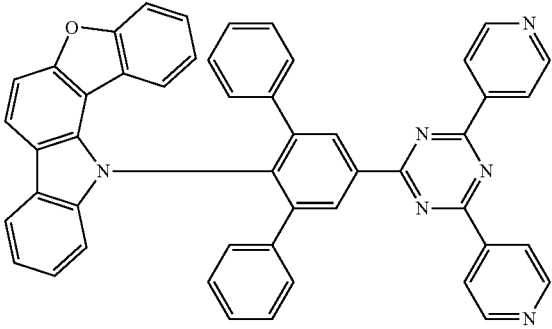

3277
-continued
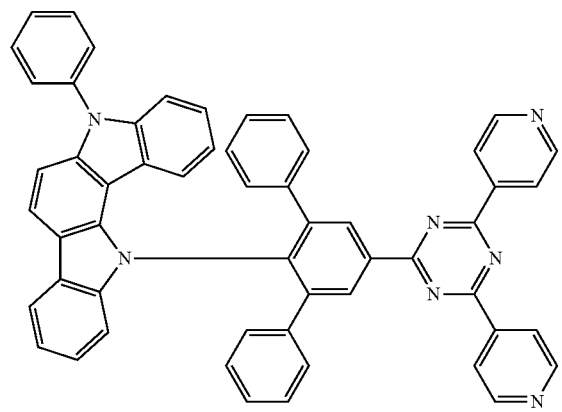
991
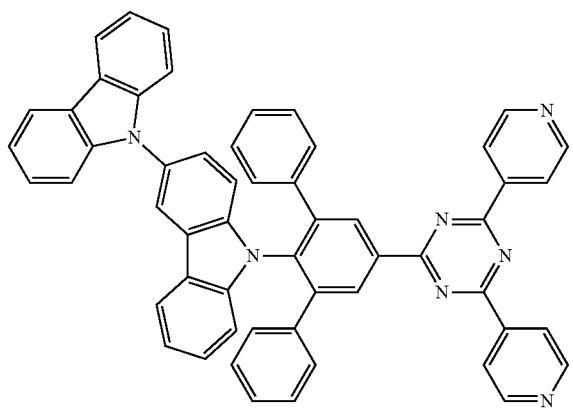
992
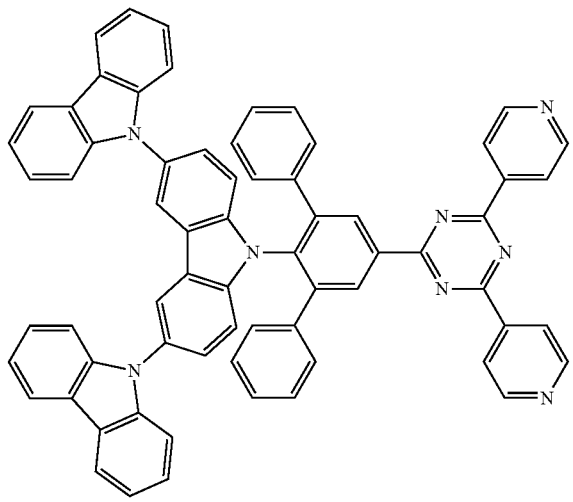
993
3278
-continued
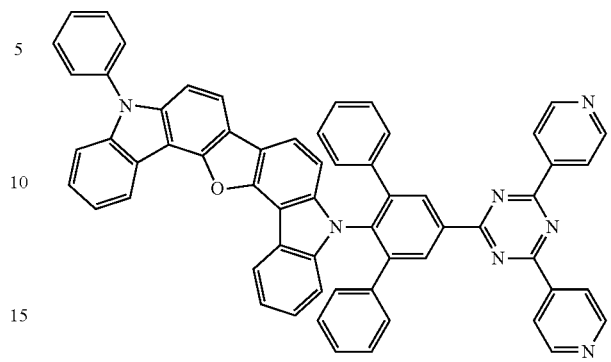
994
995
996
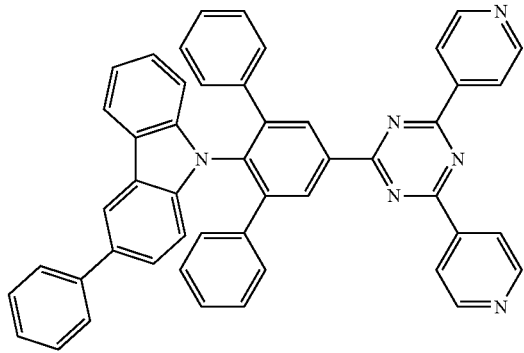
997

3279
-continued
998
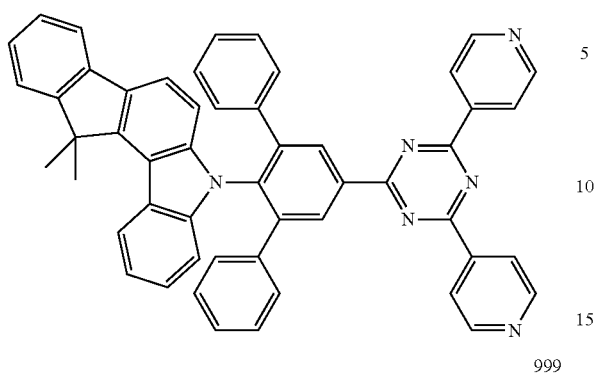
999
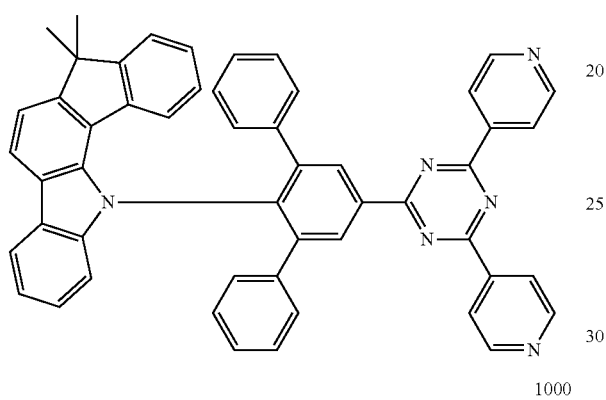
1000
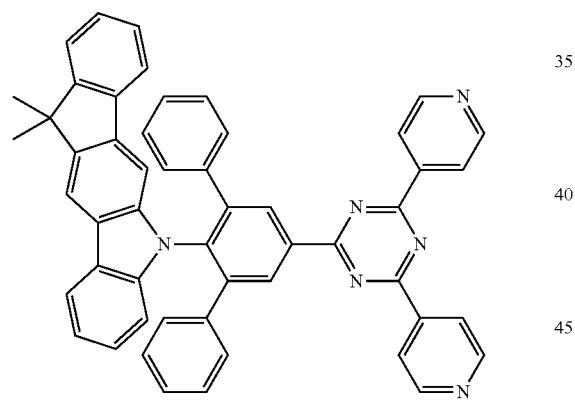
1001
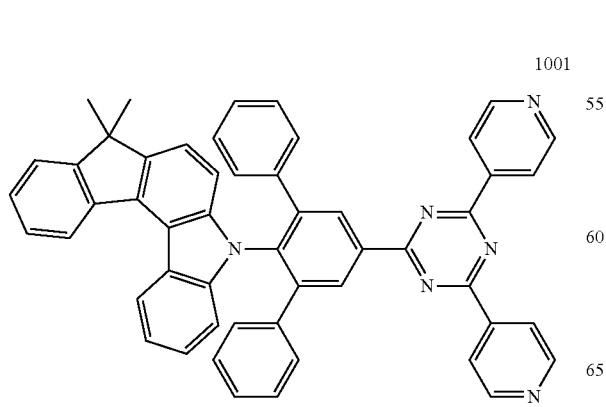
3280
-continued
1002
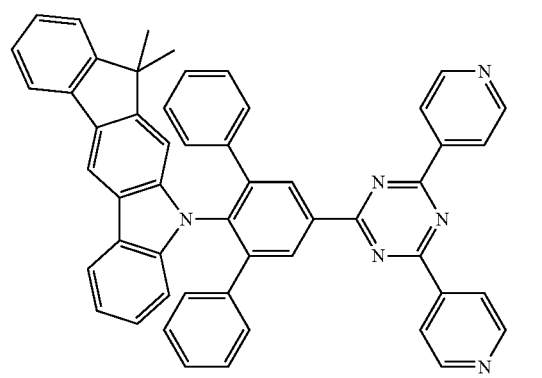
1003
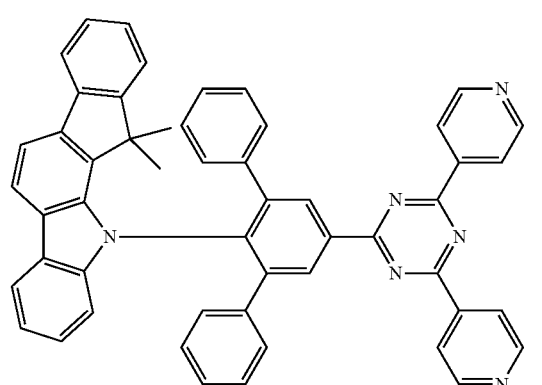
1004
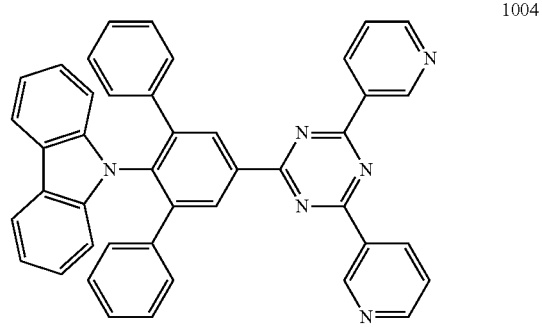
1005
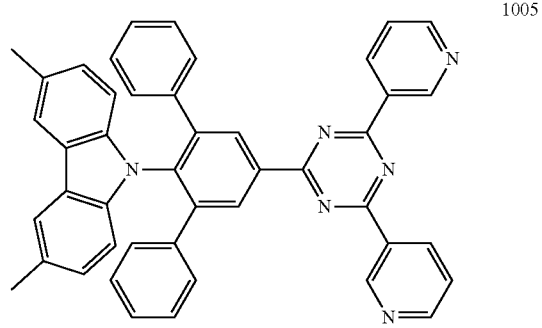

1006
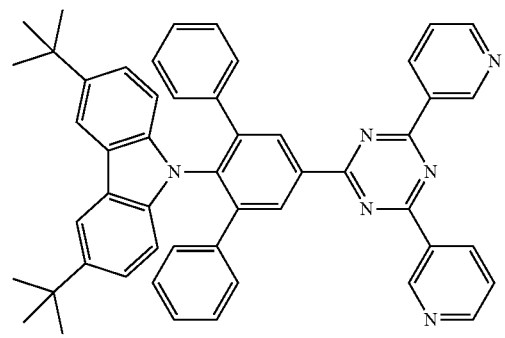
1007
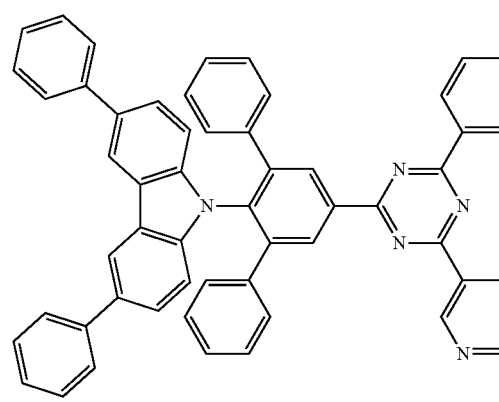
1008
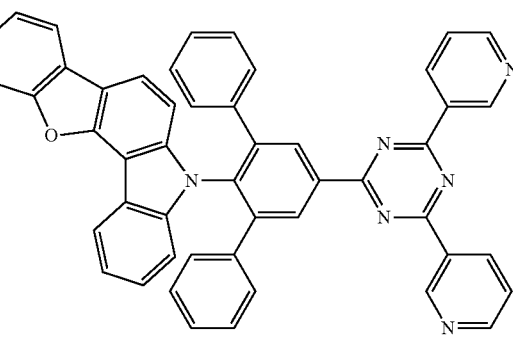
1009
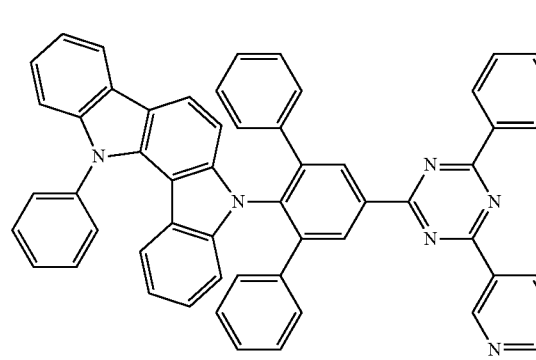
1010
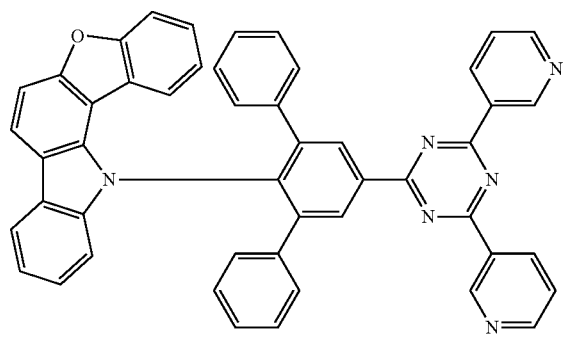
1011
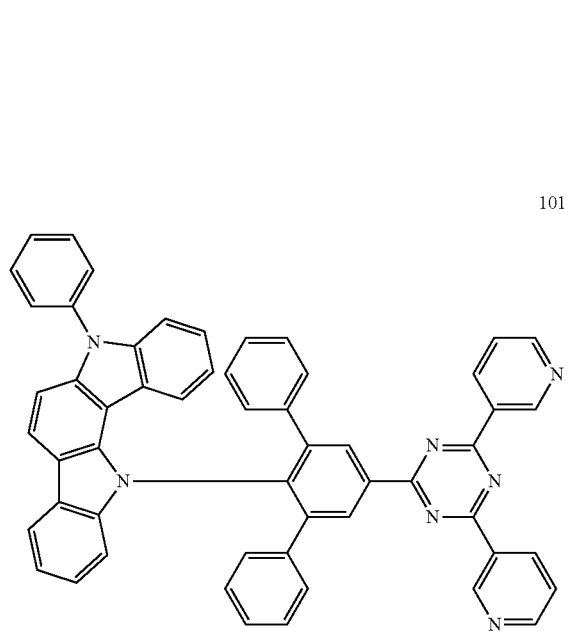
1012
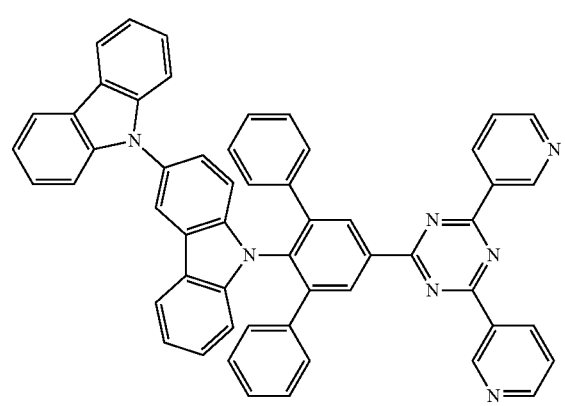

1013
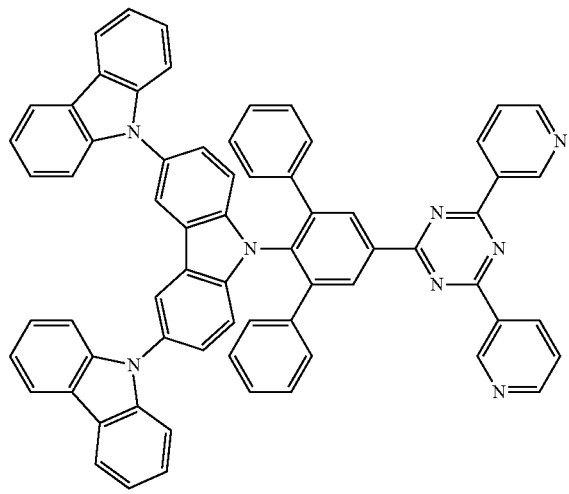
1014
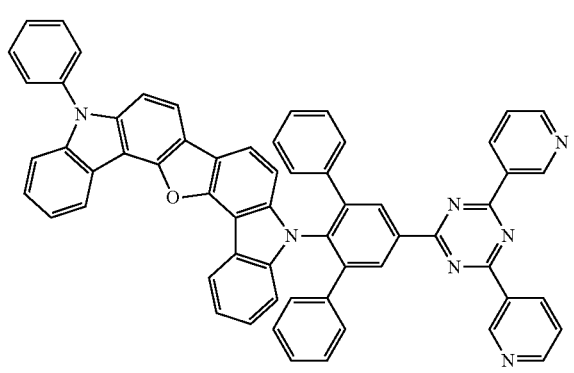
1015
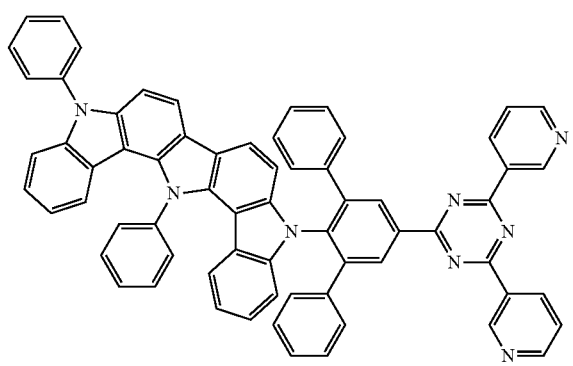
1016
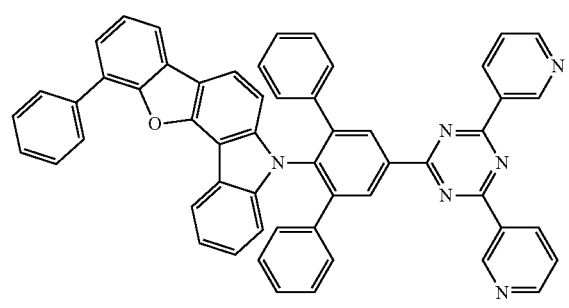
1017
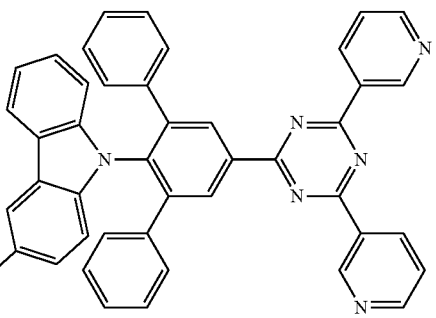
1018
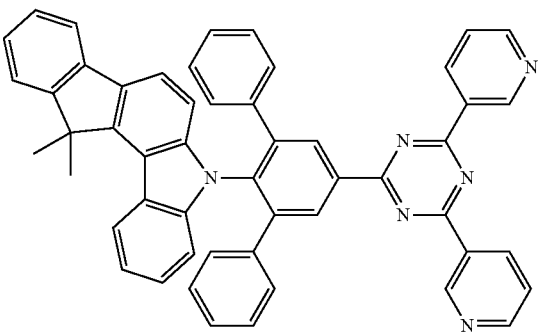
1019
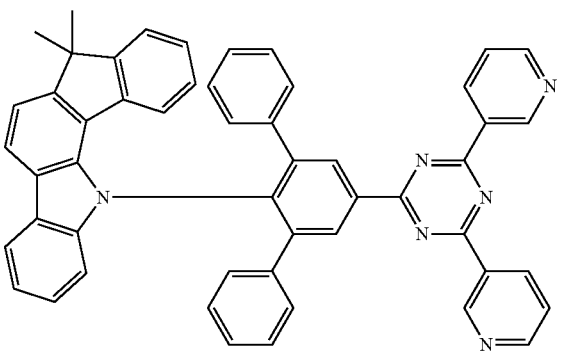
1020
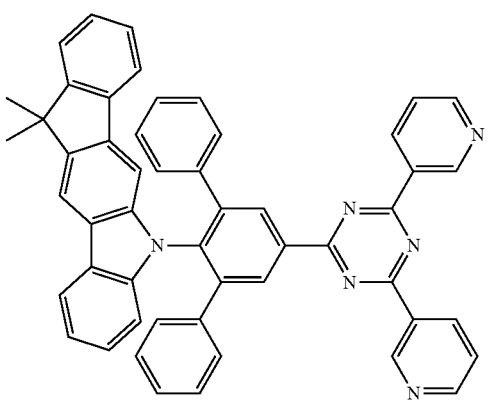

3285 -continued
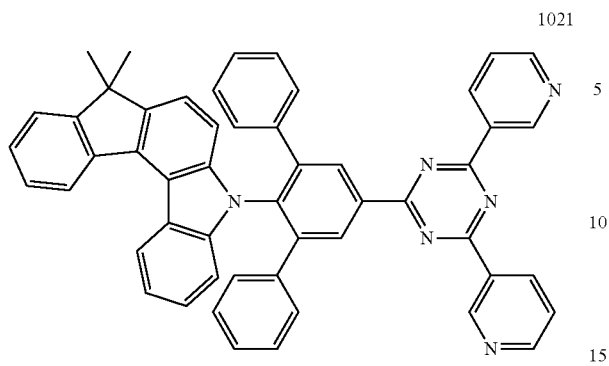
1021
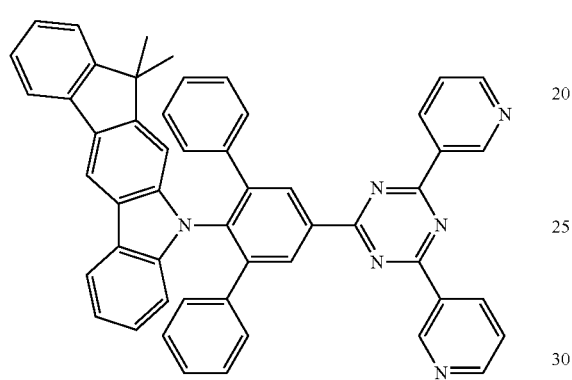
1022
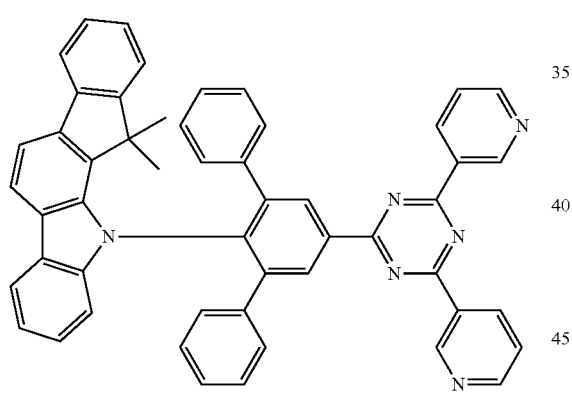
1023
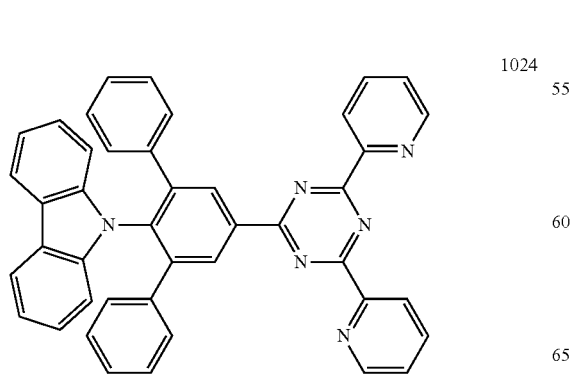
1024
3286 -continued
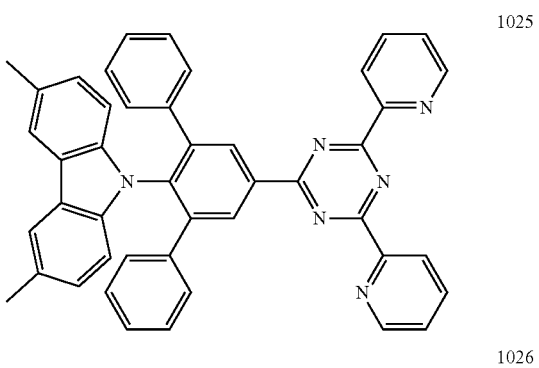
1025
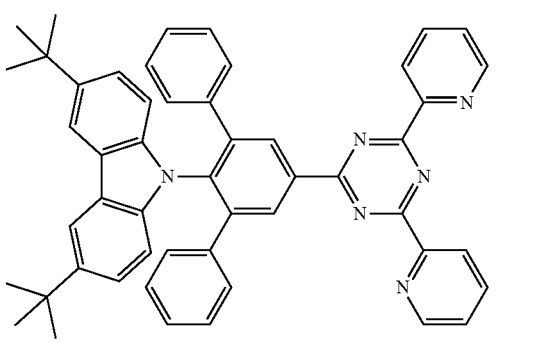
1026
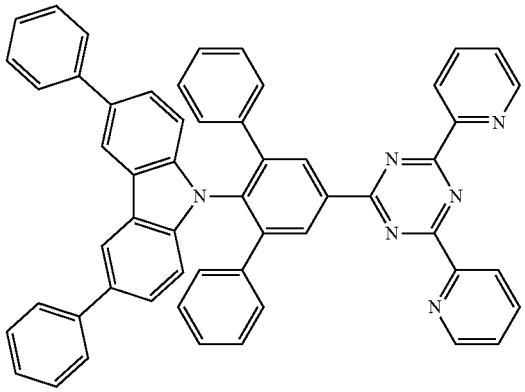
1027
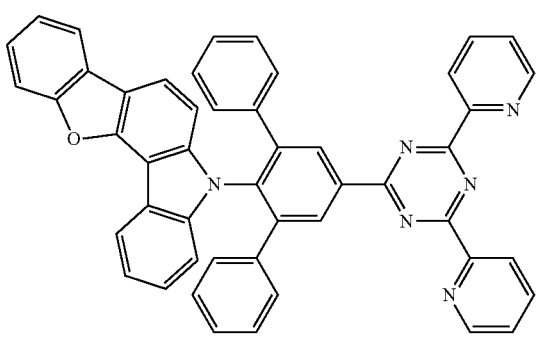
1028

3287
-continued
1029
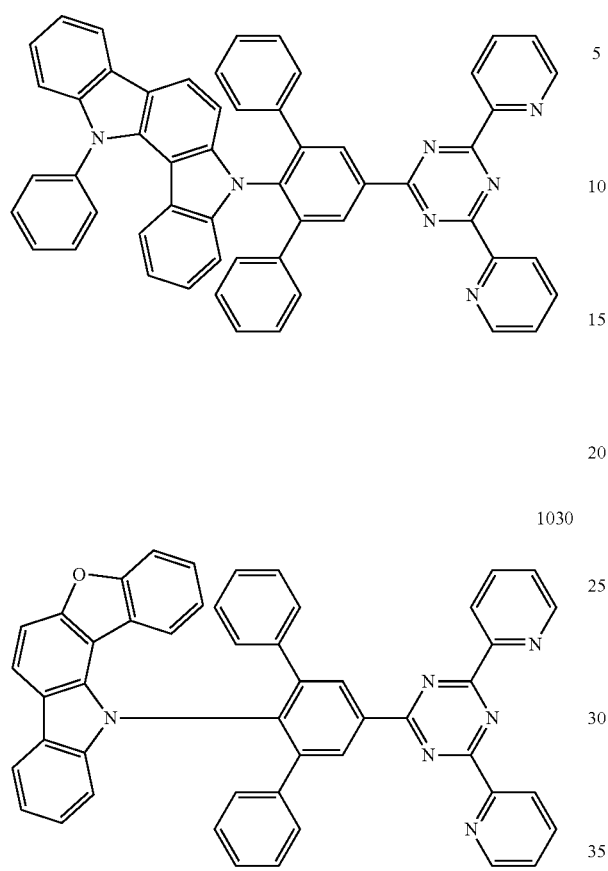
1030
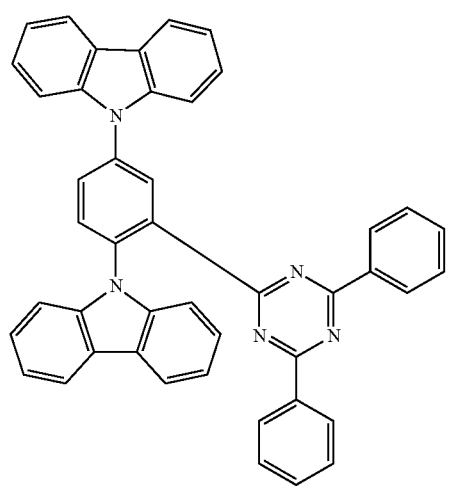
Group X
1
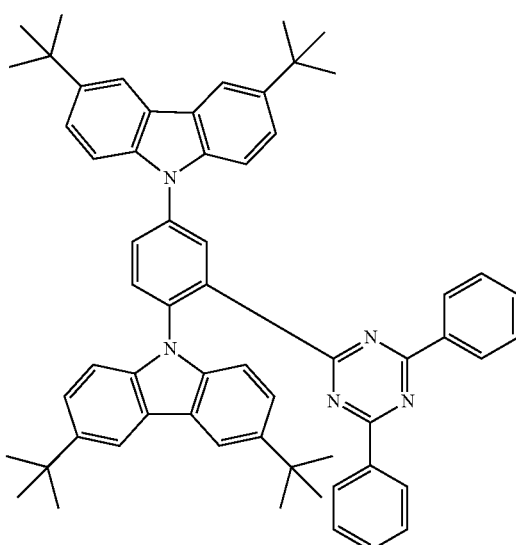
3288
-continued
2
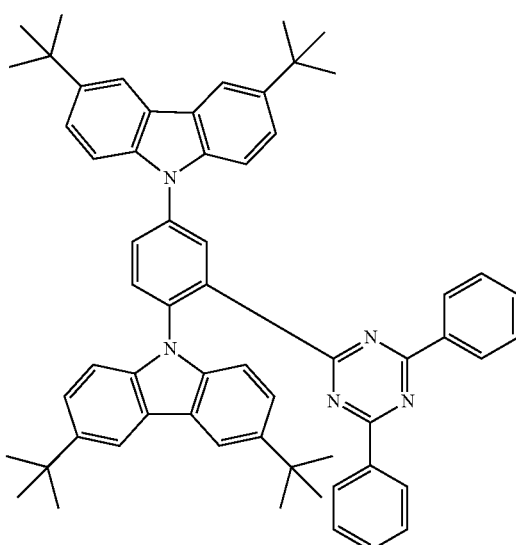
3
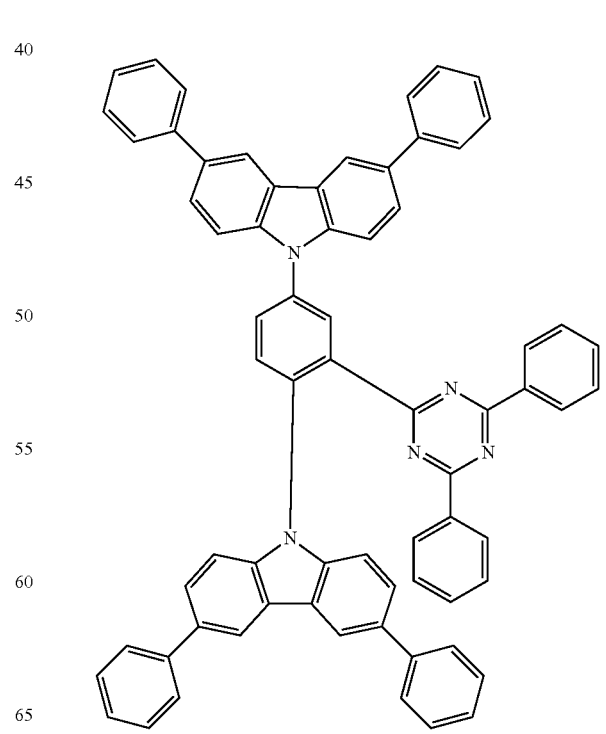

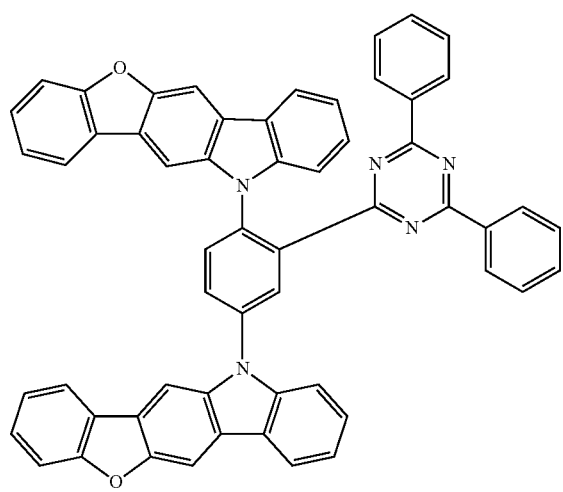
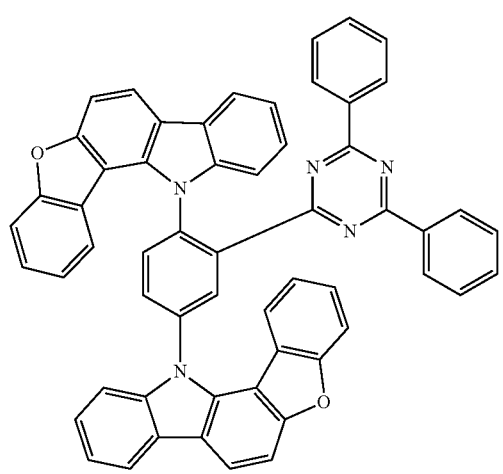
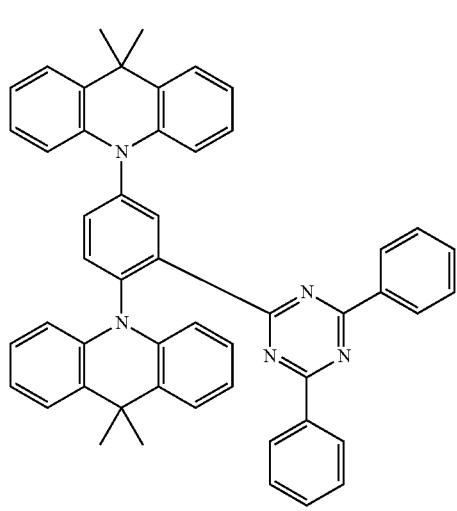
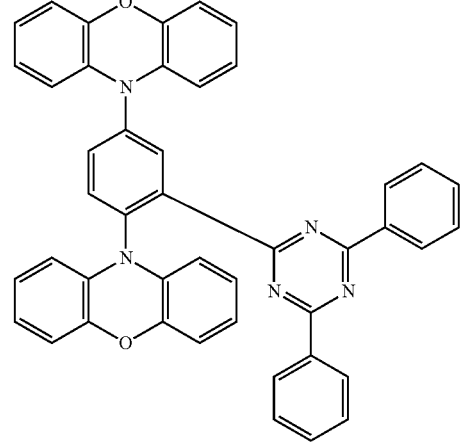
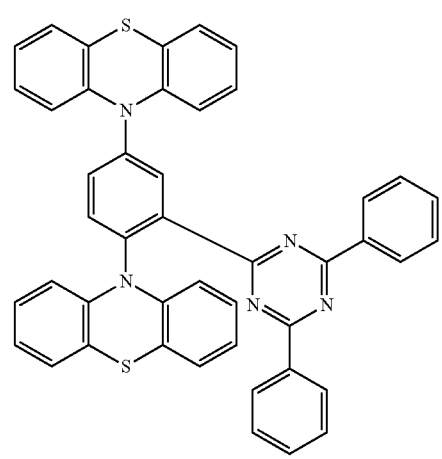
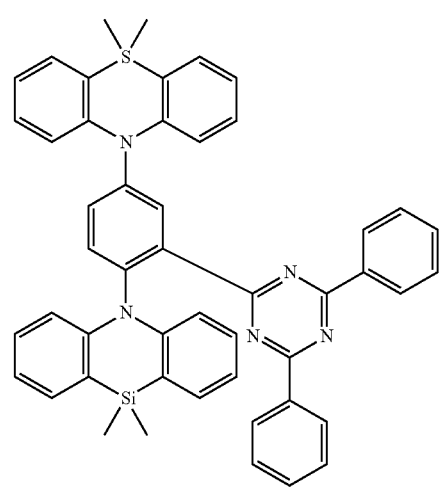

3291
-continued
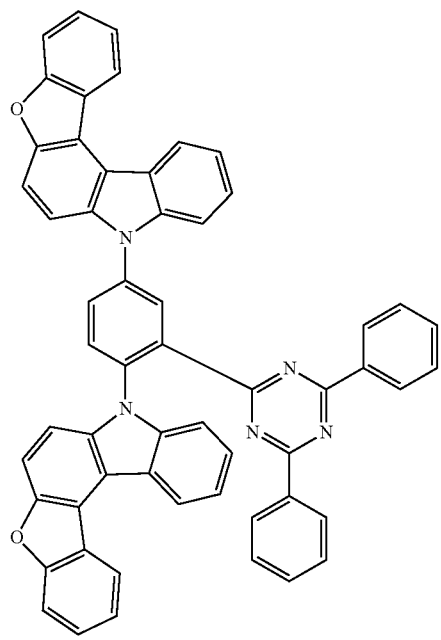
10
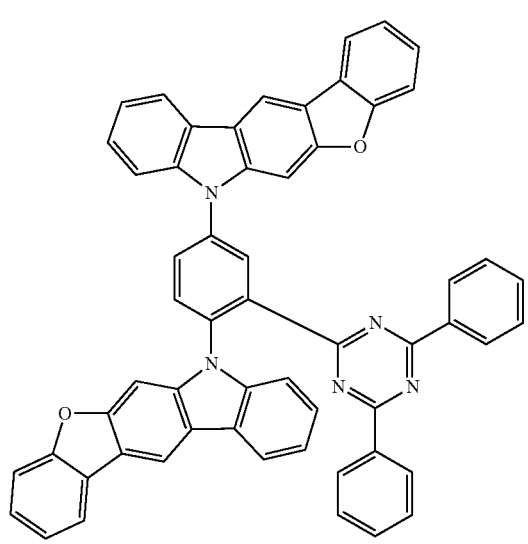
11
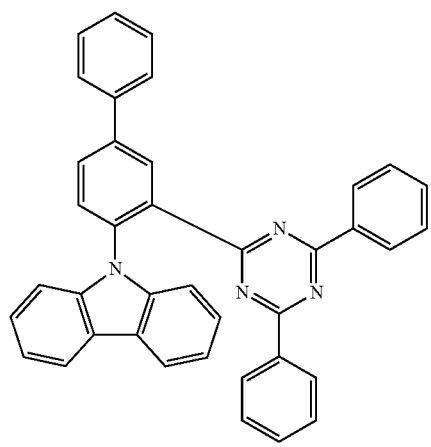
12
3292
-continued
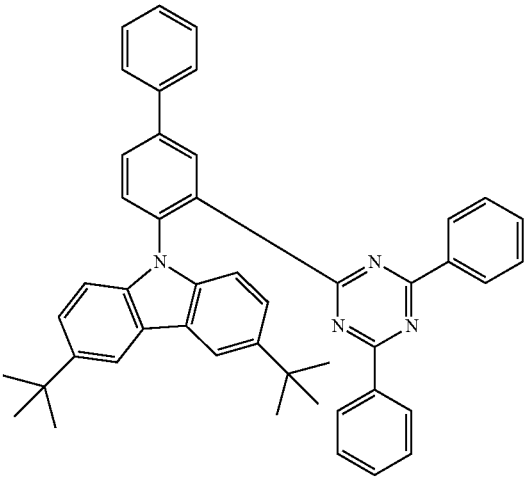
13
14
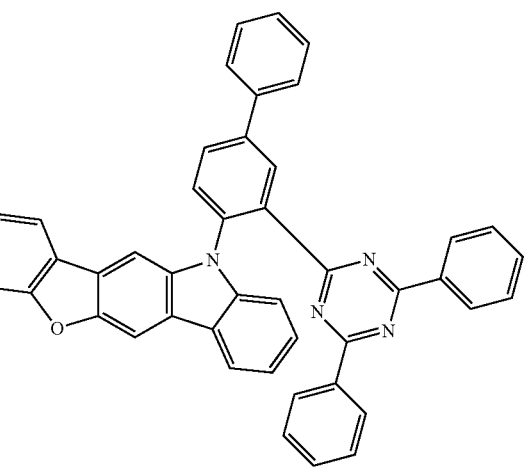
15

-continued
16
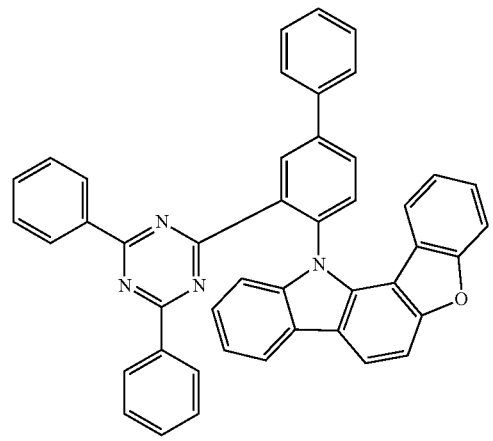
17
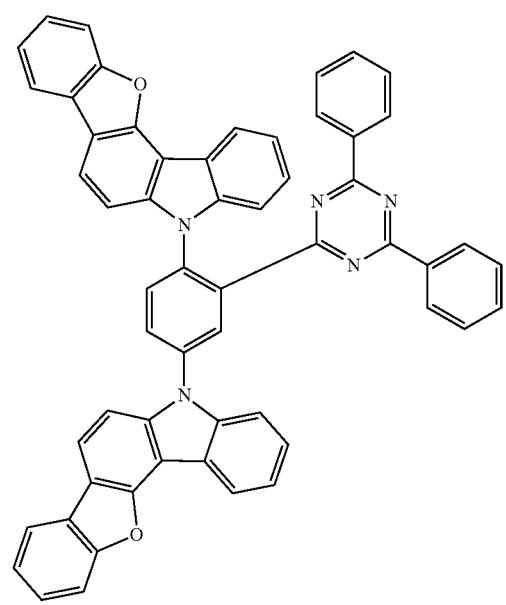
18
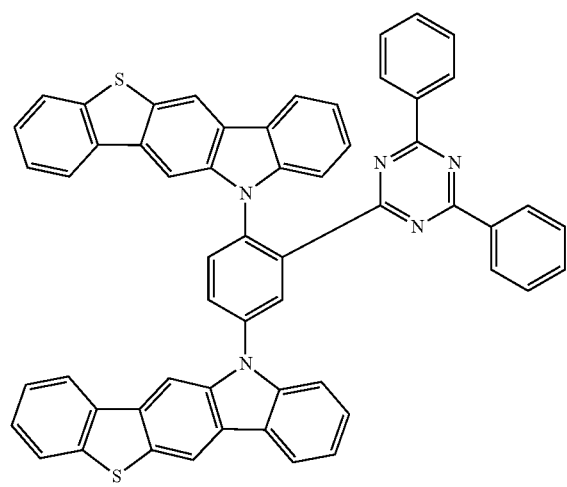
-continued
19
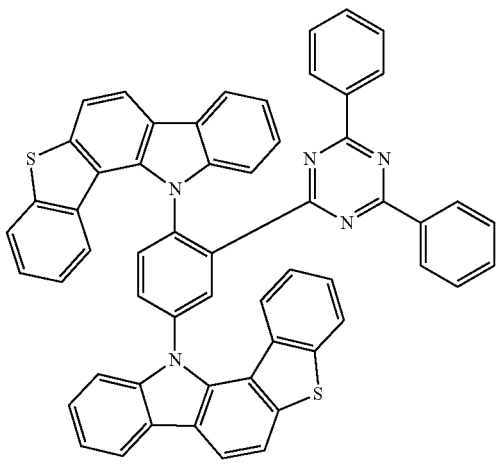
20
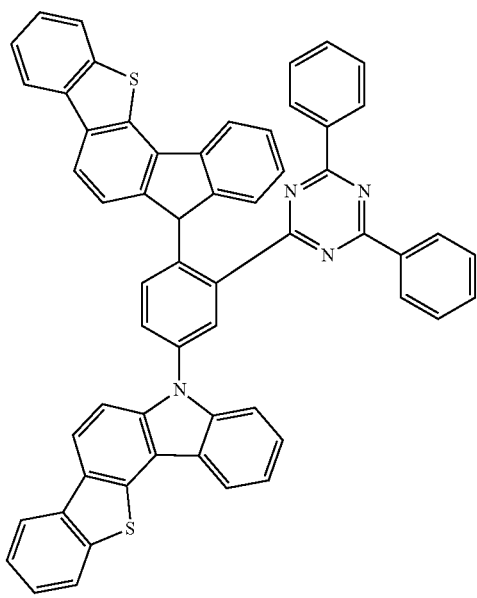
21
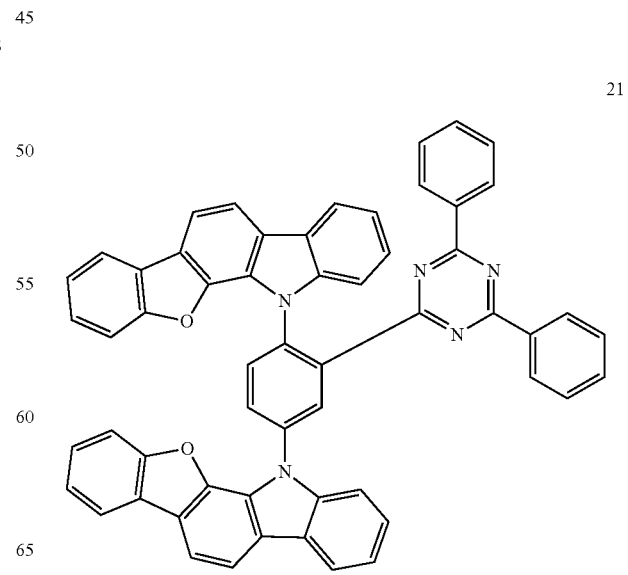

22
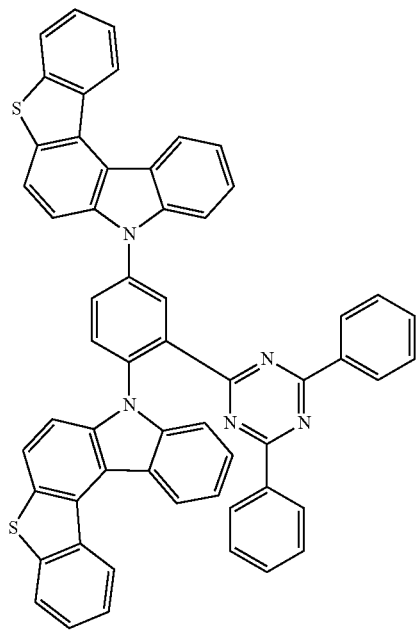
23
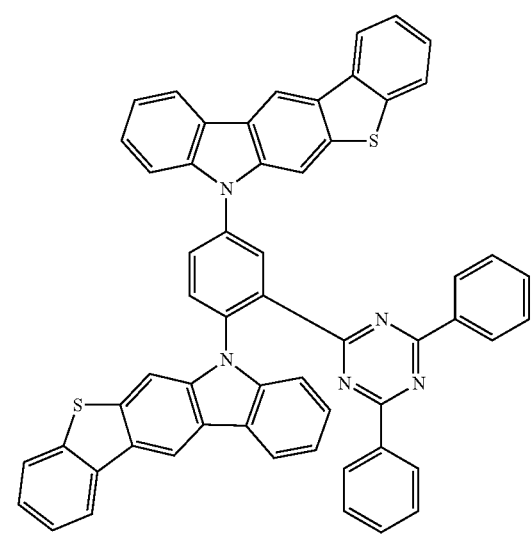
24
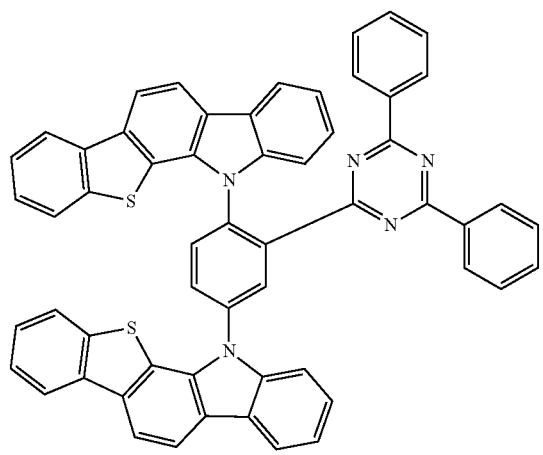
25
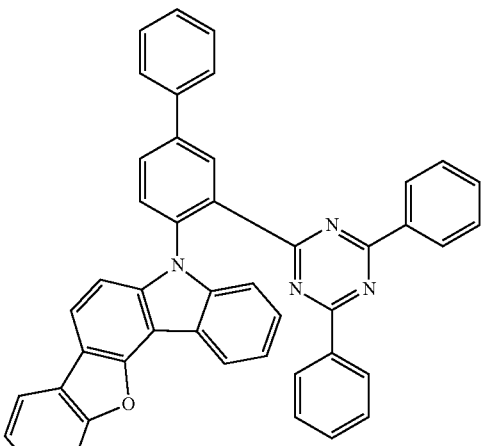
26
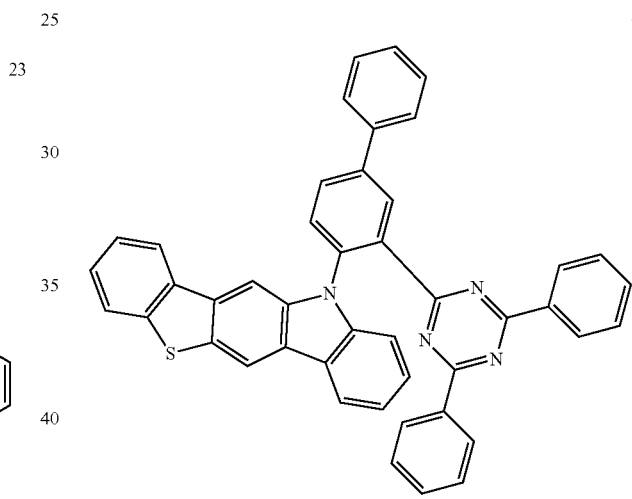
27
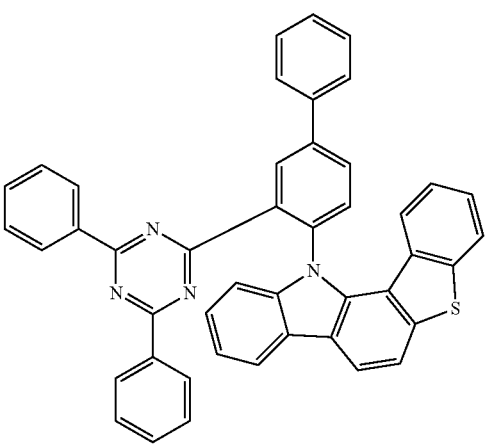

3297
-continued
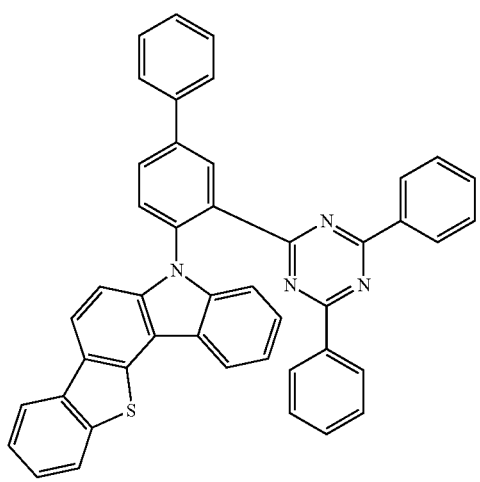
28
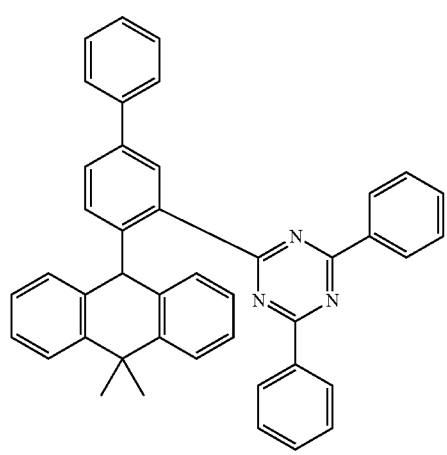
29
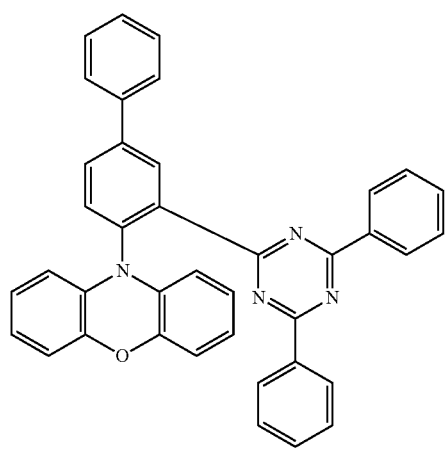
30
3298
-continued
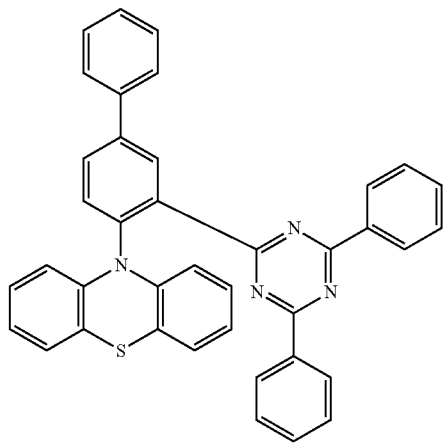
31
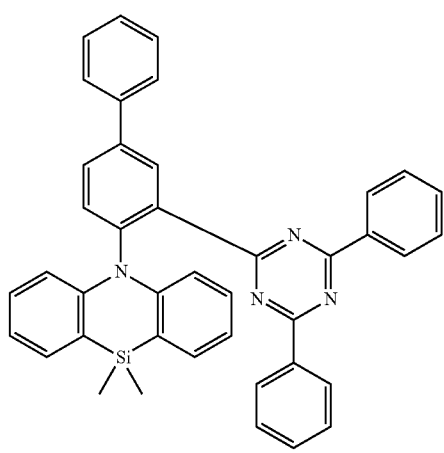
32
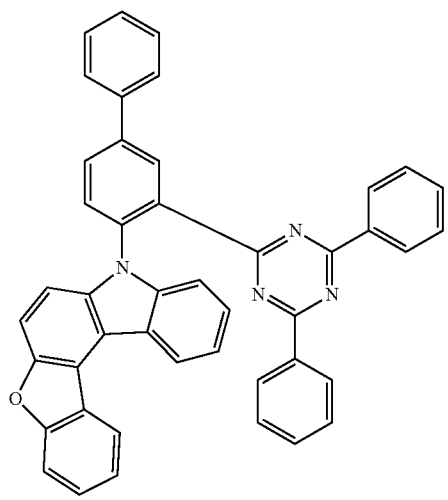
33

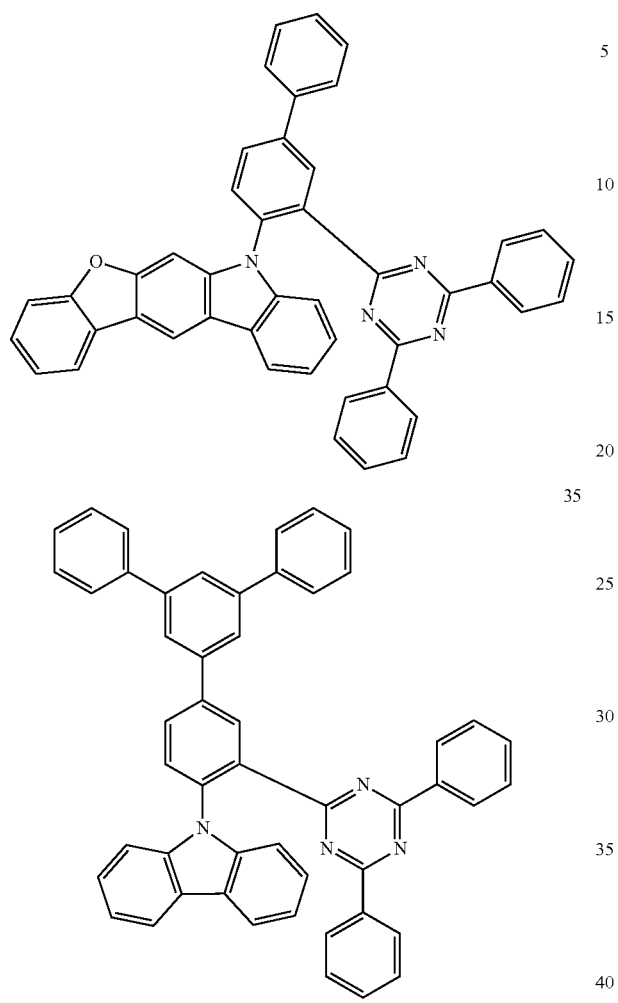
34
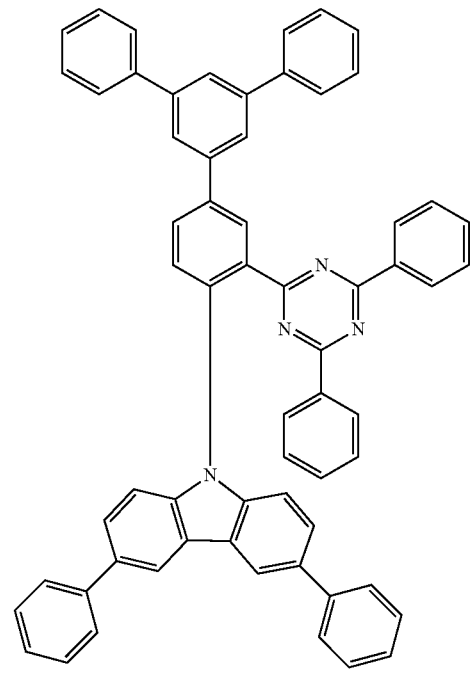
37
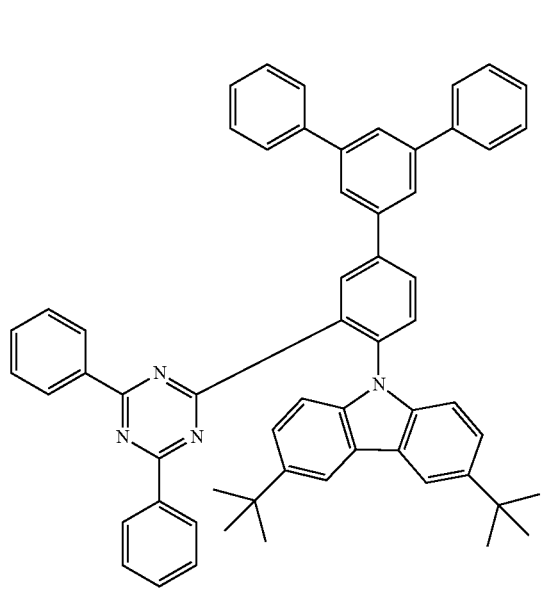
35
36
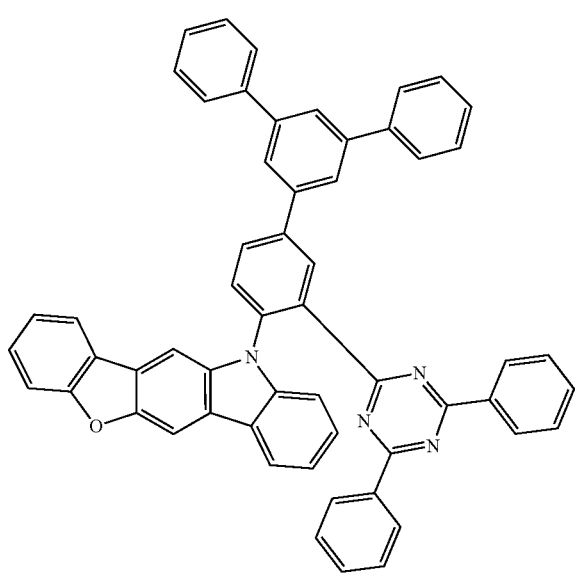
38

3301
-continued
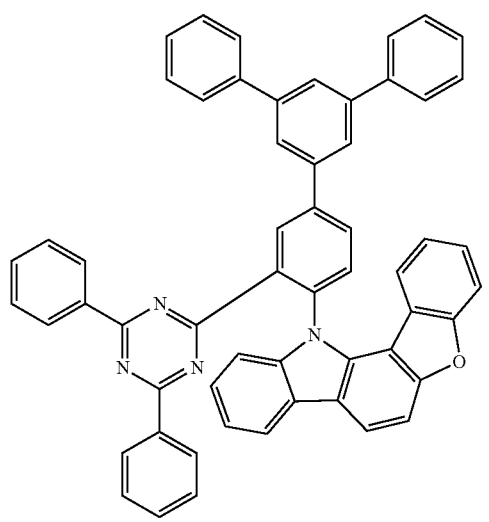
39
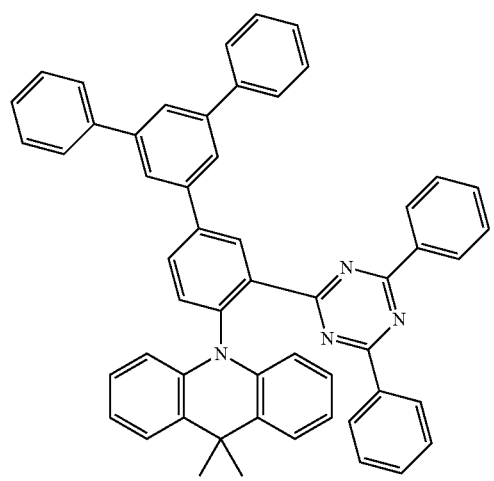
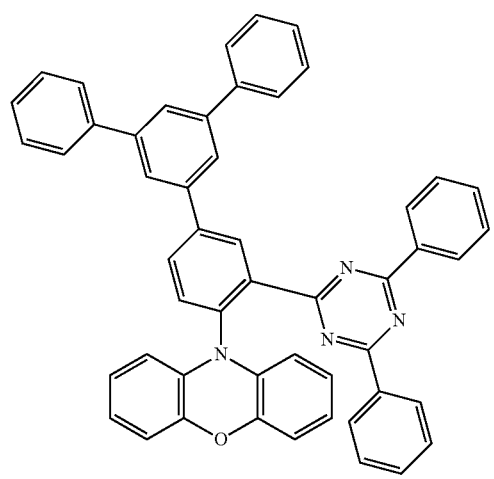
3302
-continued
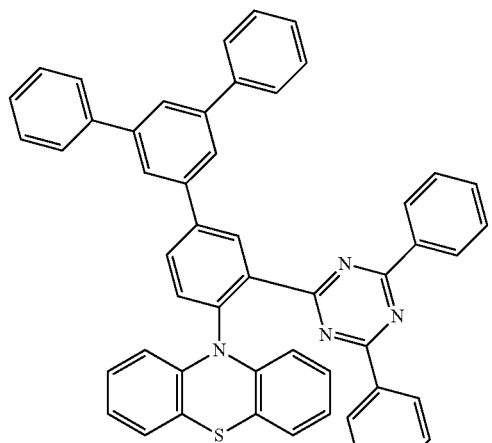
5
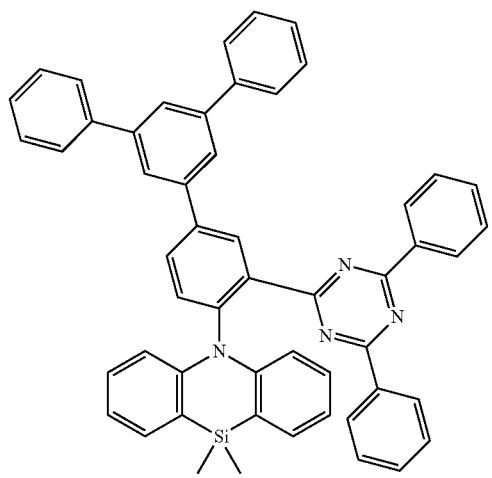
40
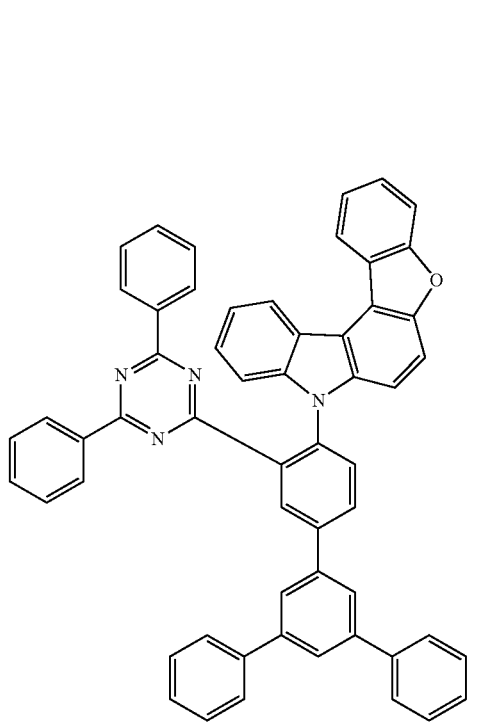
44

3303
-continued
45
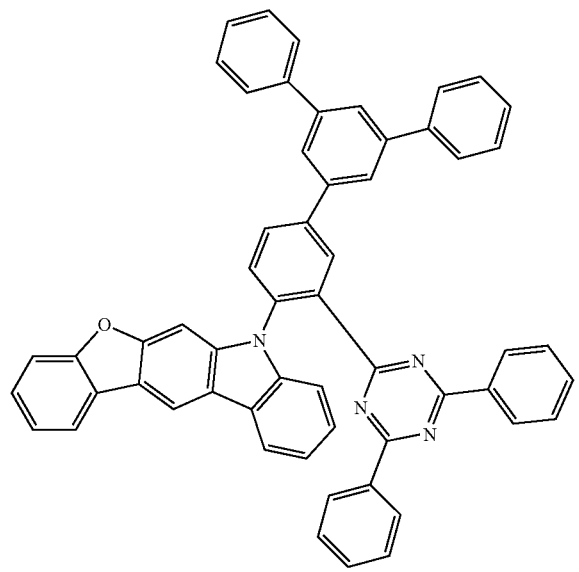
46
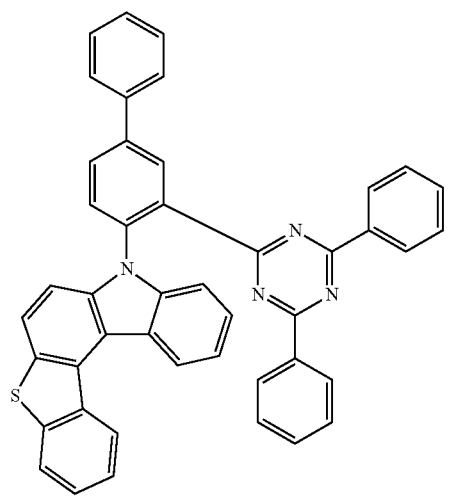
47
3304
-continued
48
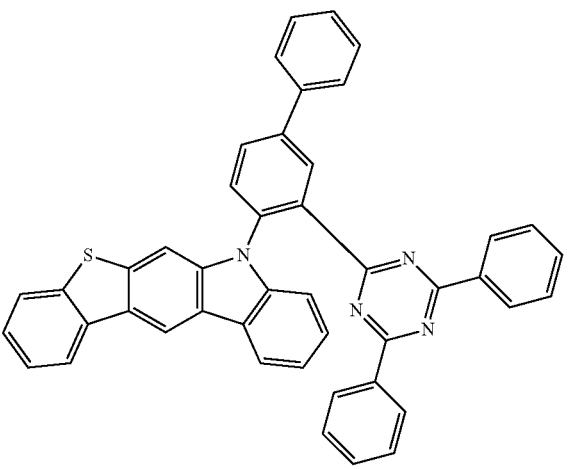
49
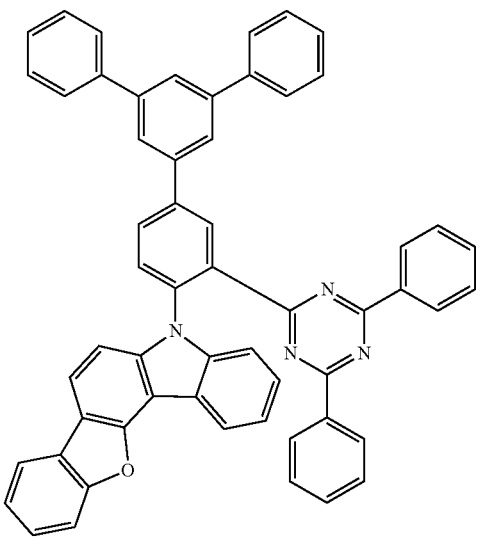
50

3305
-continued
51
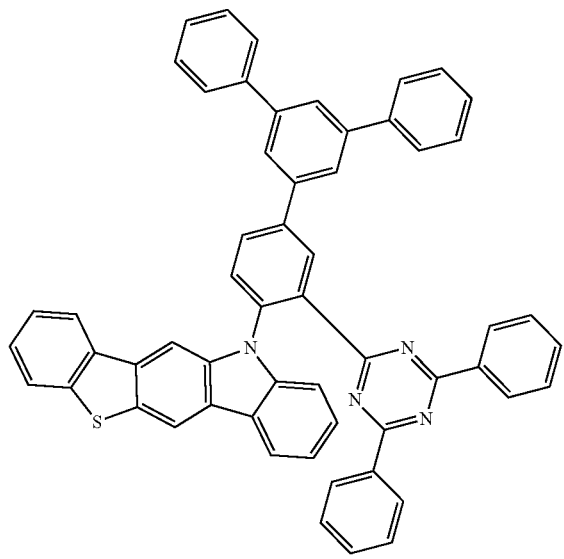
52
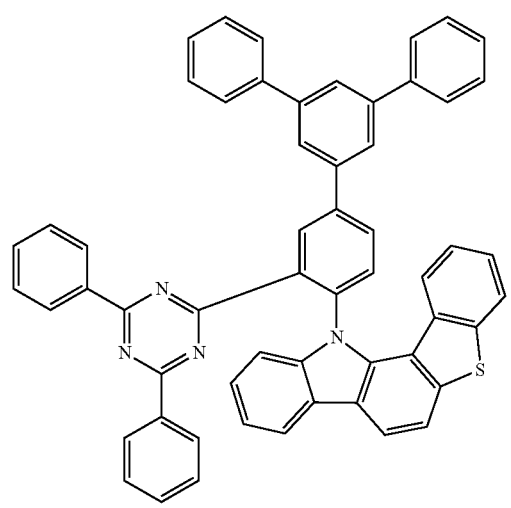
53
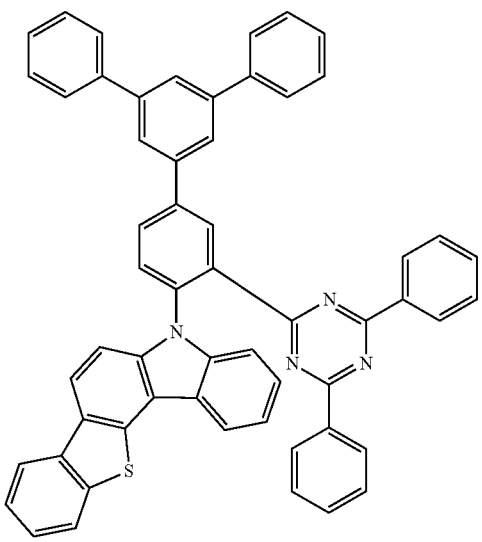
3306
-continued
54
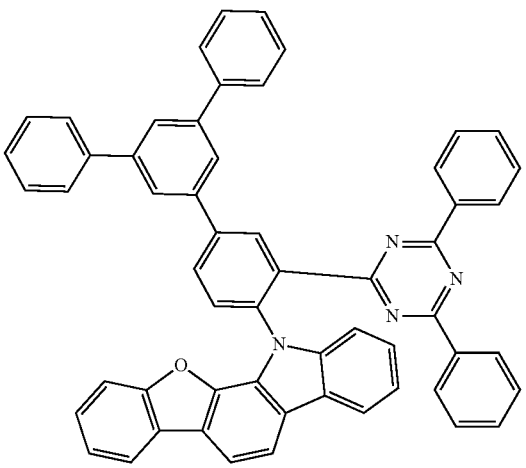
55
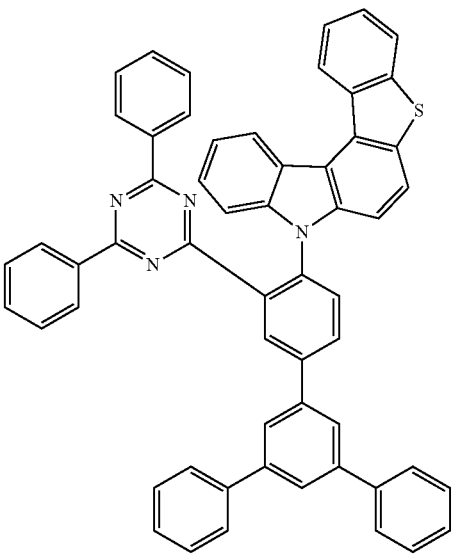
56
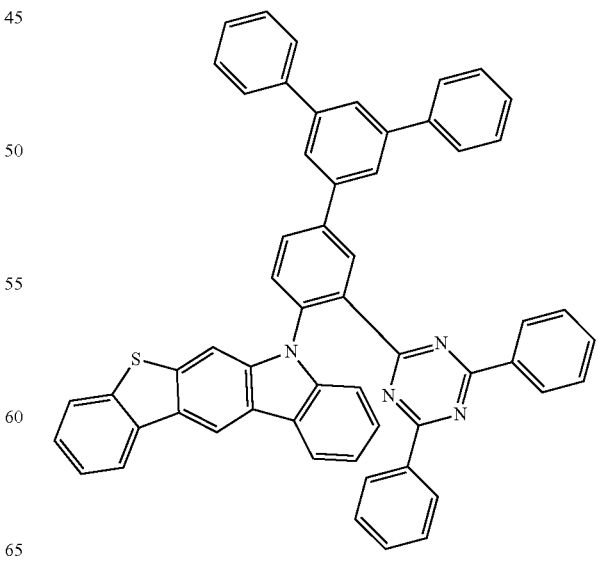

3307
-continued
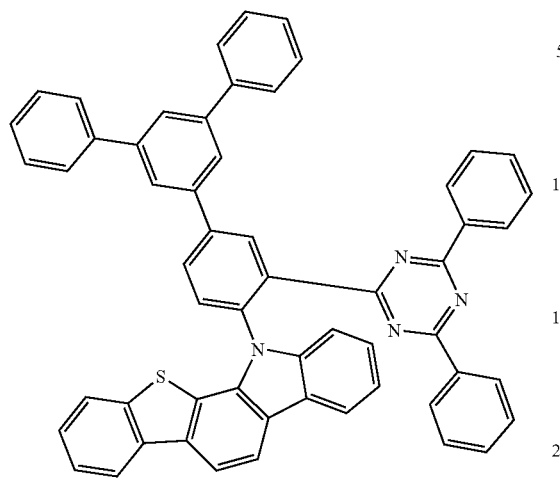
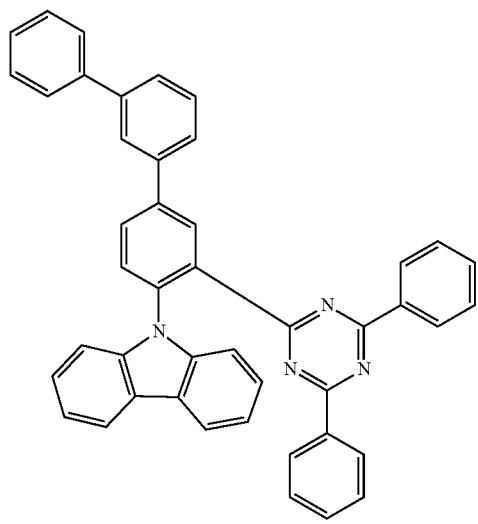
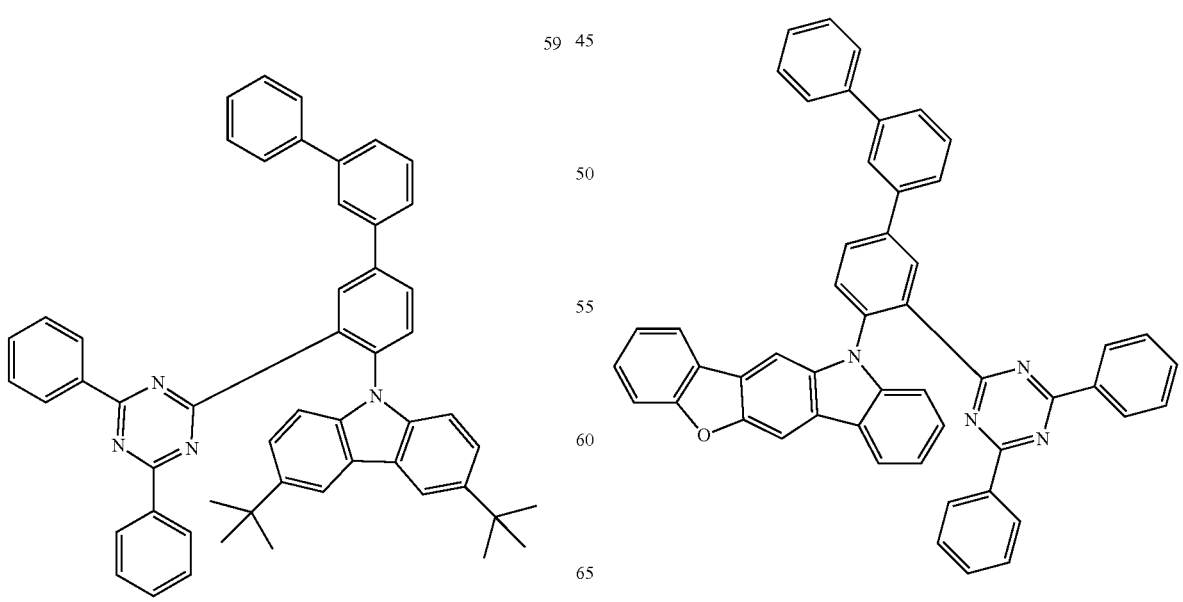
3308
-continued
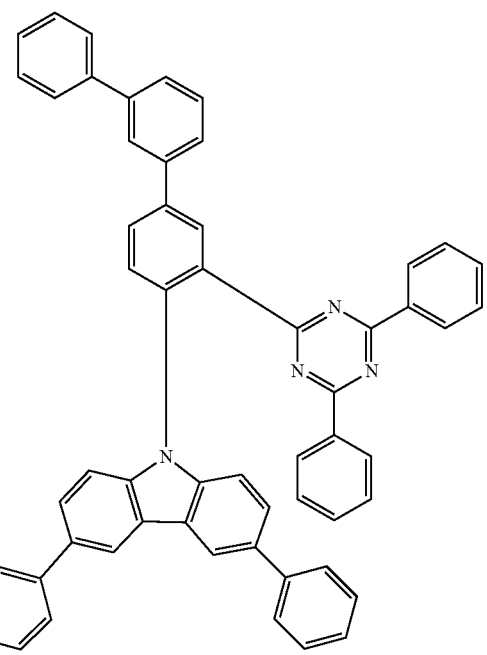

3309
-continued
61
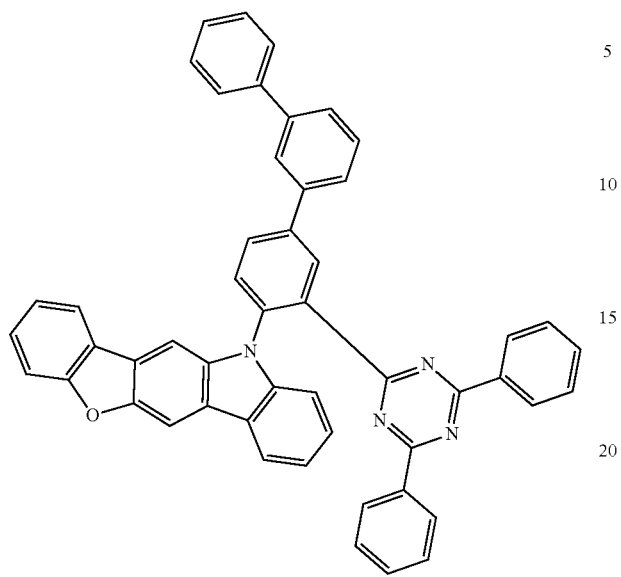
62
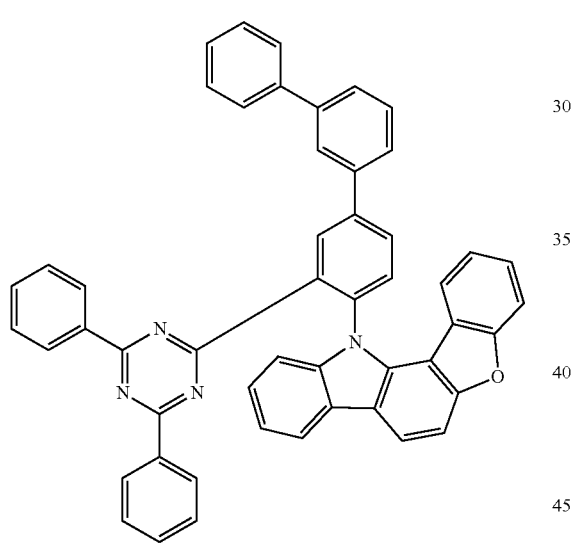
63
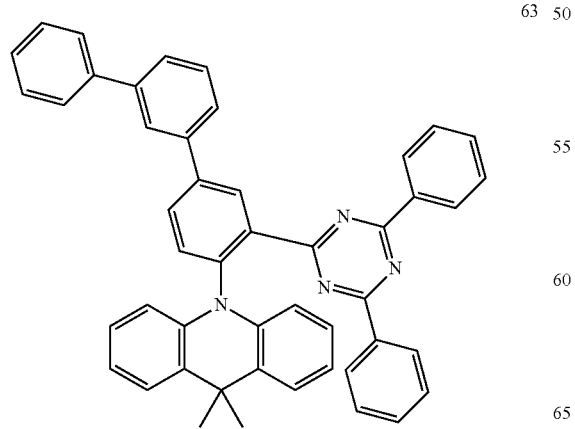
3310
-continued
64
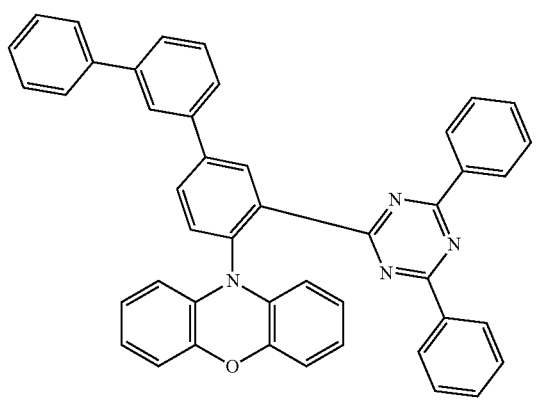
65
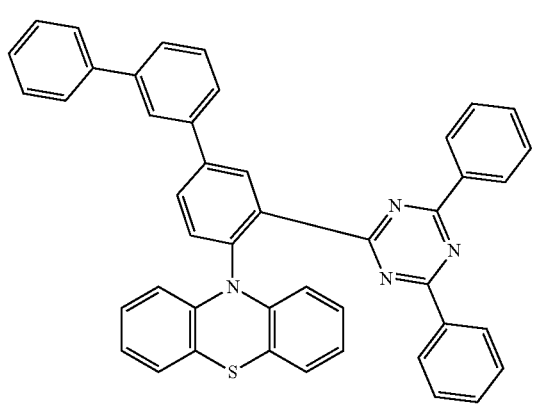
66
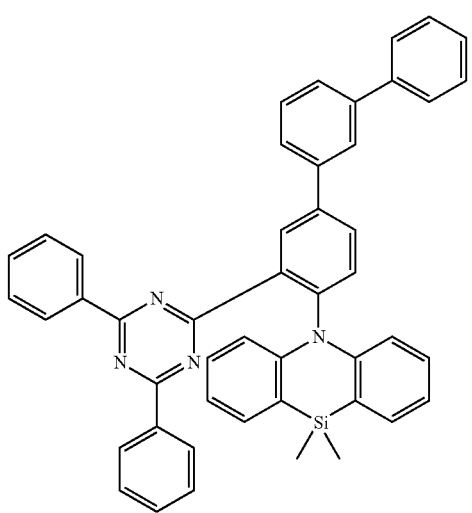

3311
-continued
67
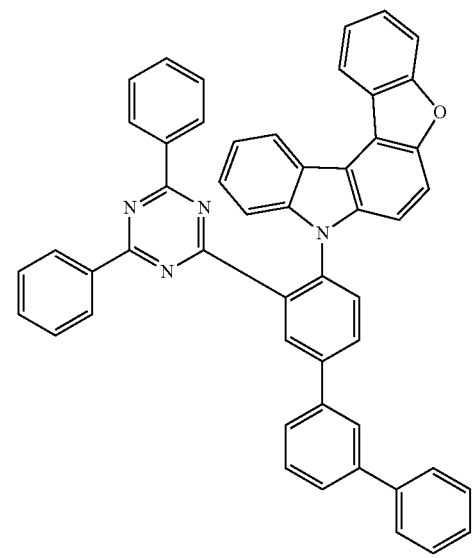
68
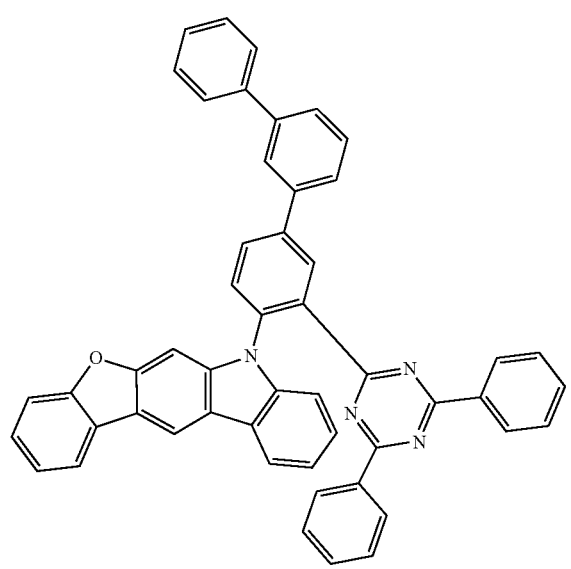
69
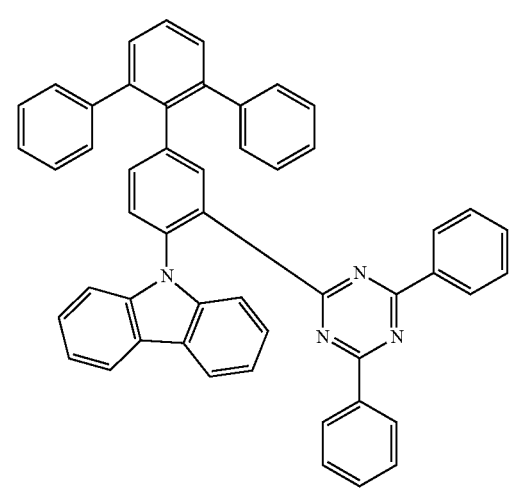
3312
-continued
70
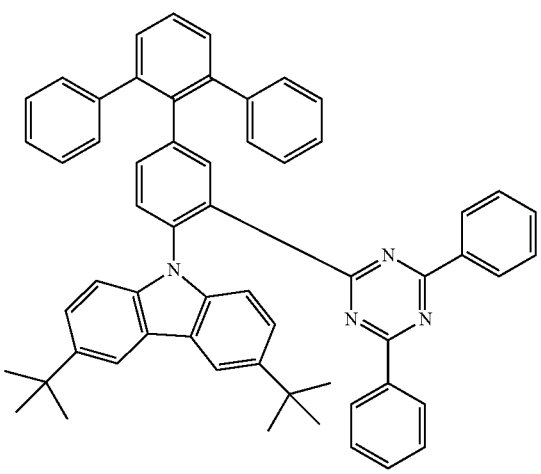
71
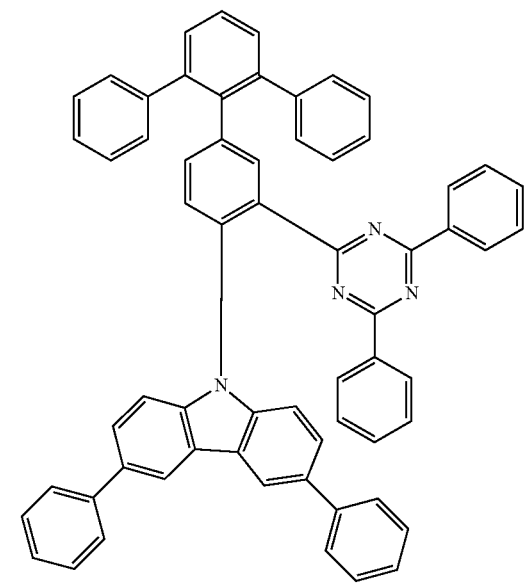
72
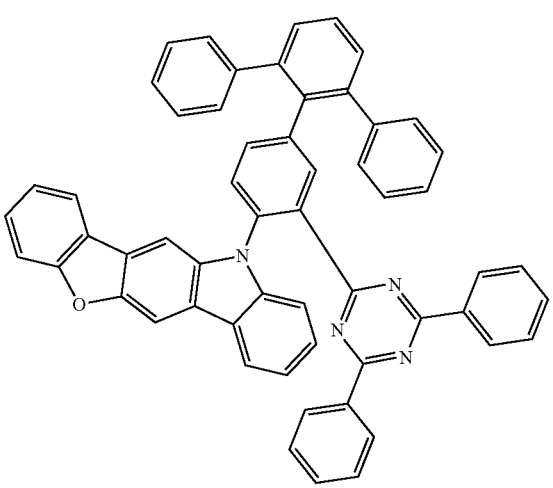

73
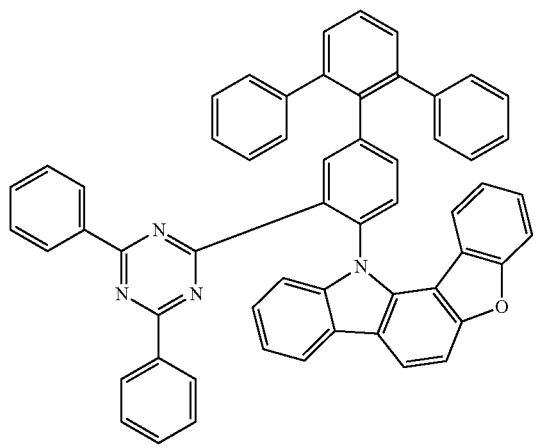
74
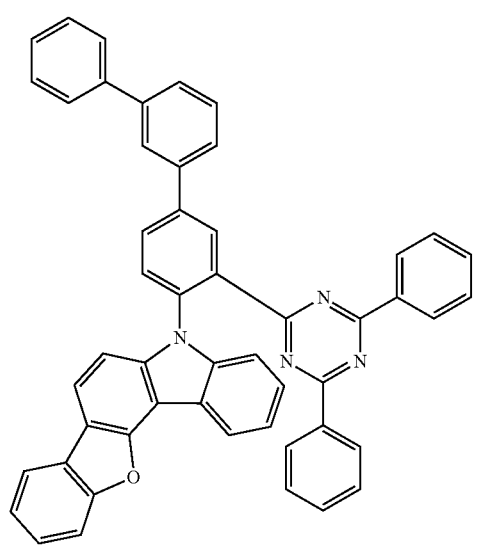
75
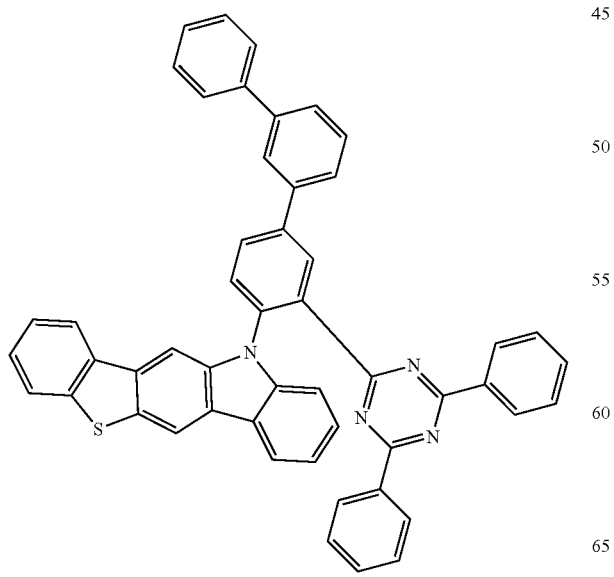
76
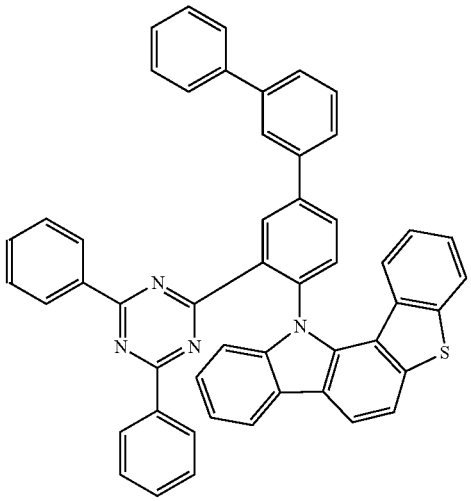
77
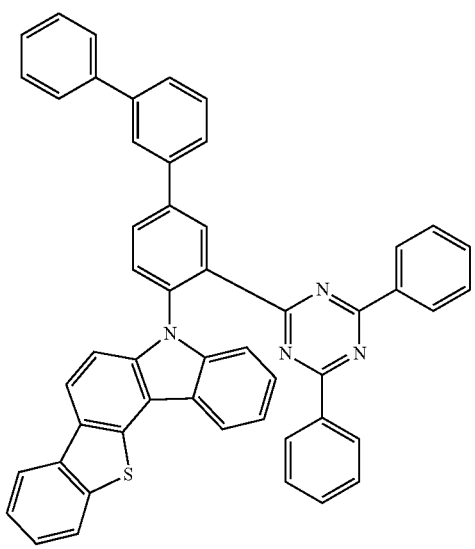
78
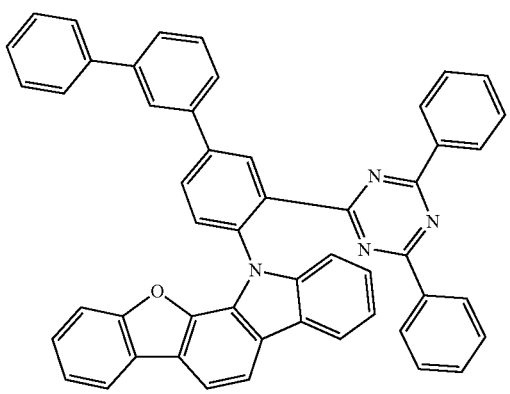

3315
-continued
79
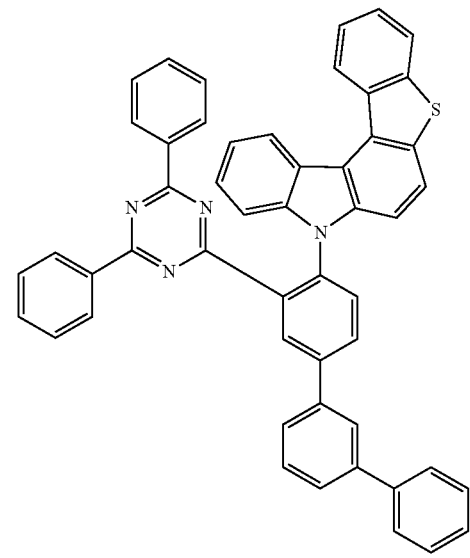
80
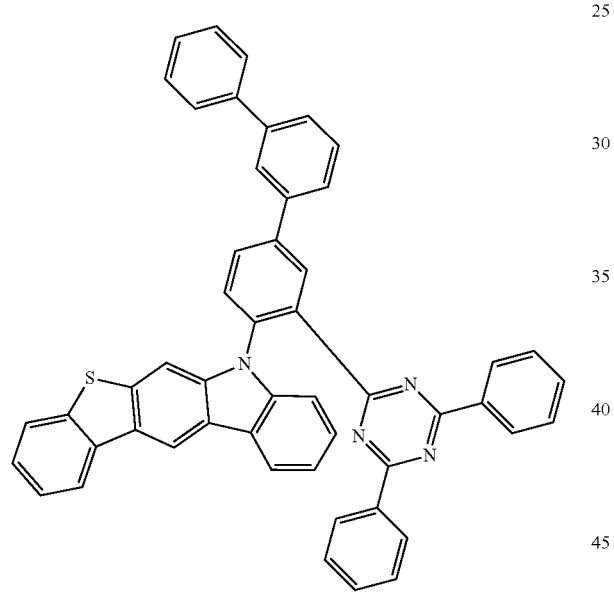
81
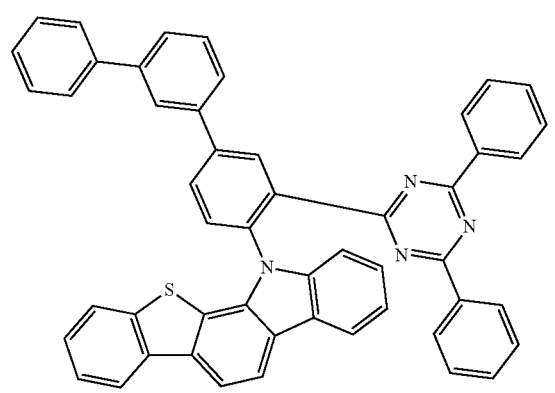
3316
-continued
82
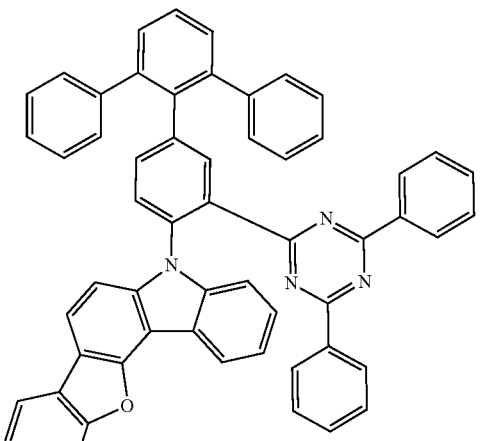
83
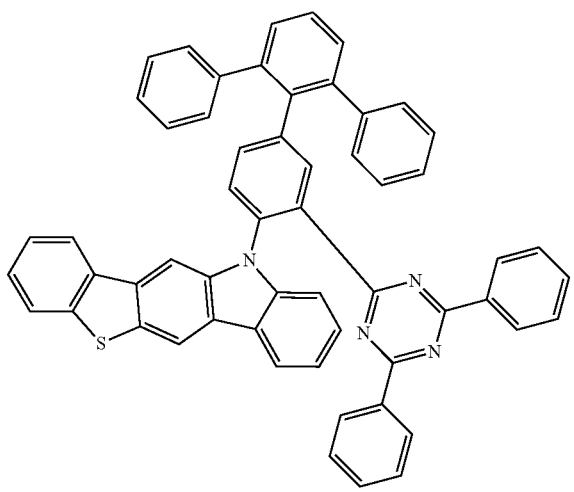
84
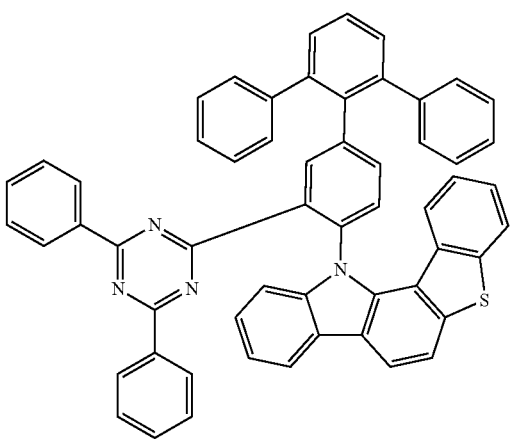

3317
-continued
85
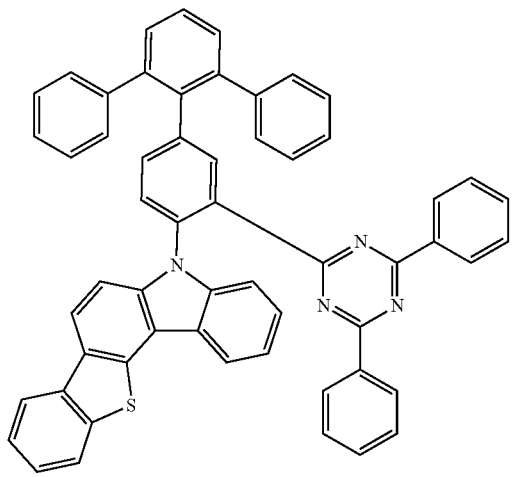
86
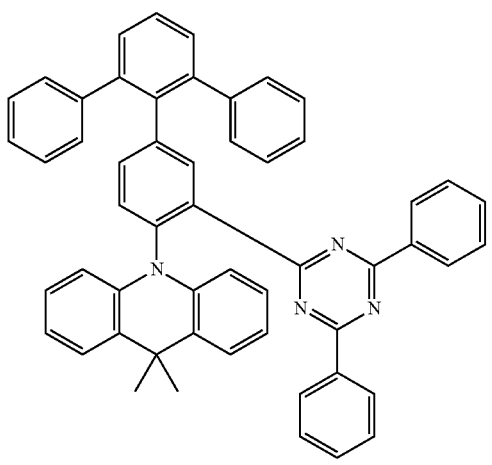
87
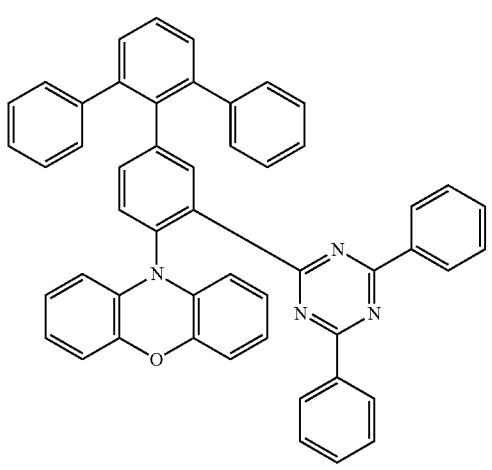
3318
-continued
88
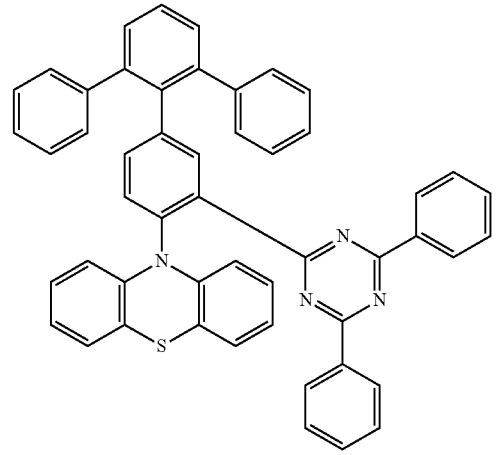
89
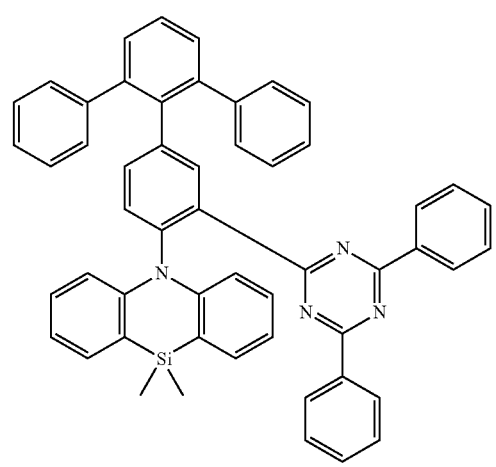
90
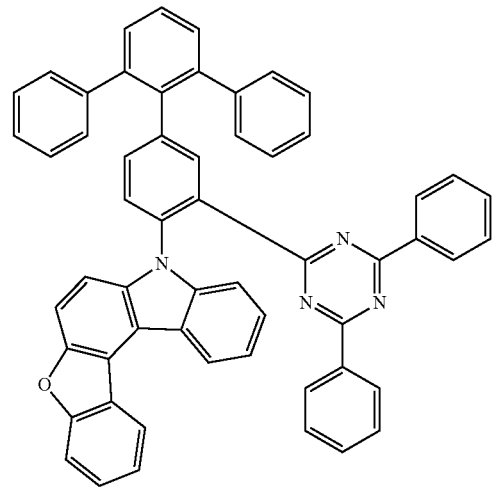

3319
-continued
91
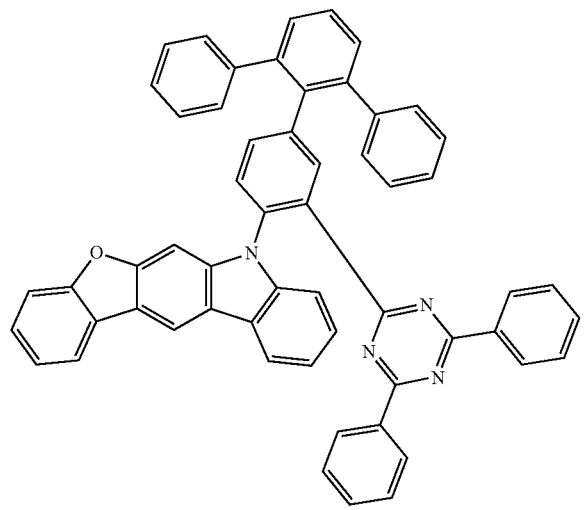
92
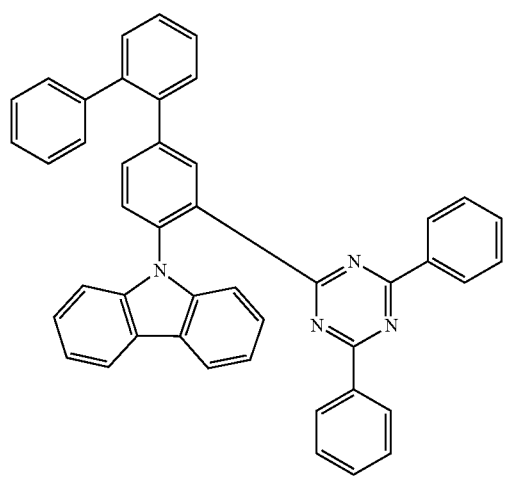
93
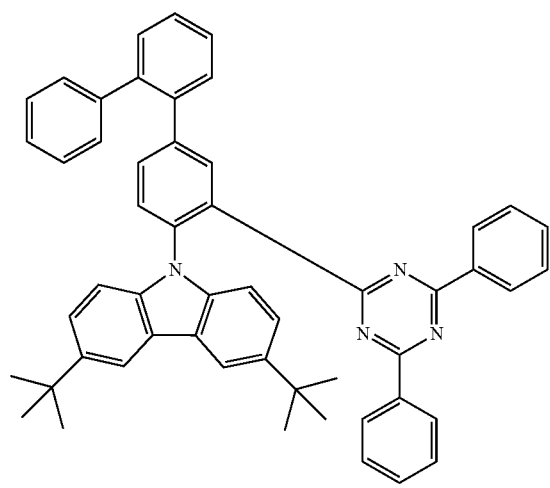
3320
-continued
94
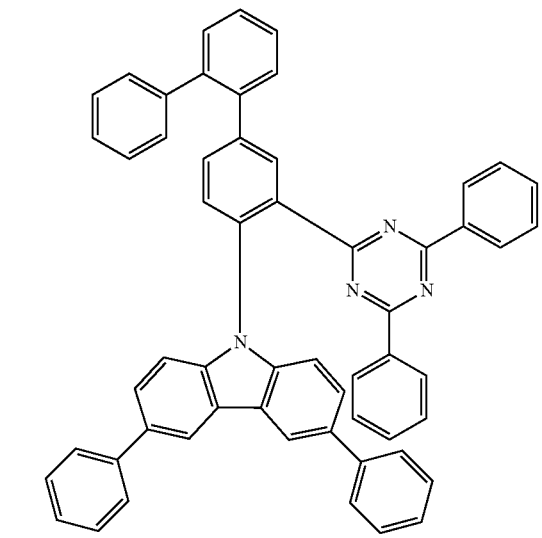
95
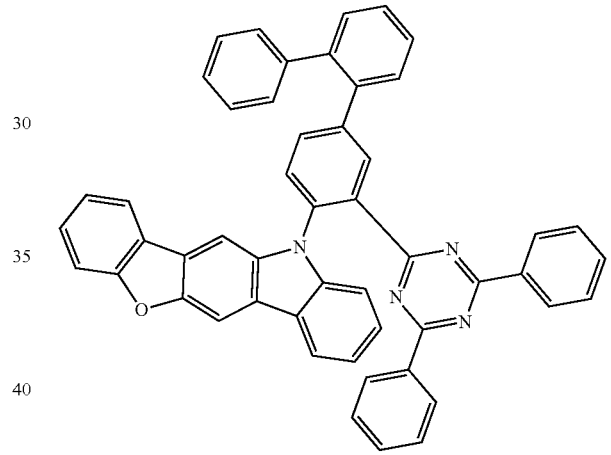
96
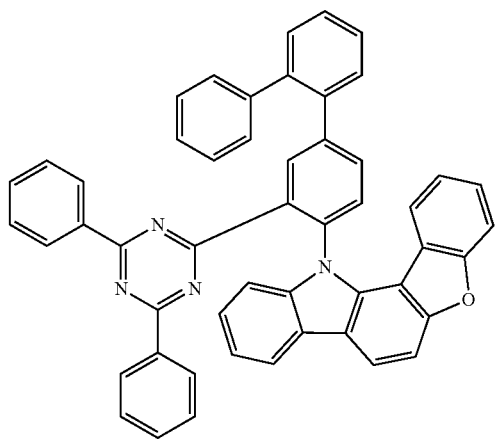

3321
-continued
97
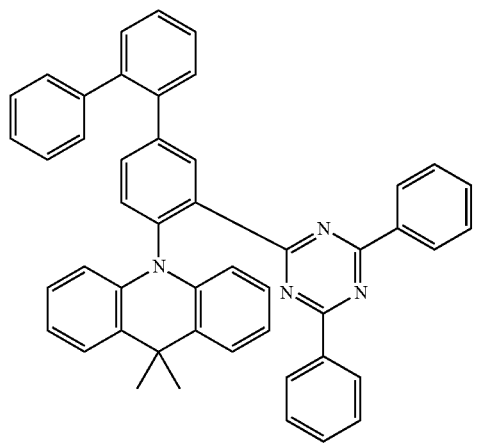
98
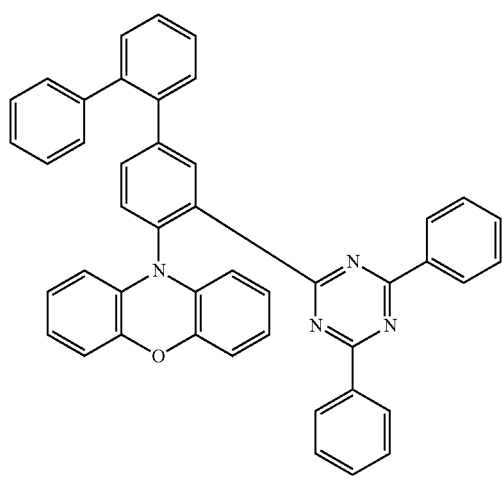
99
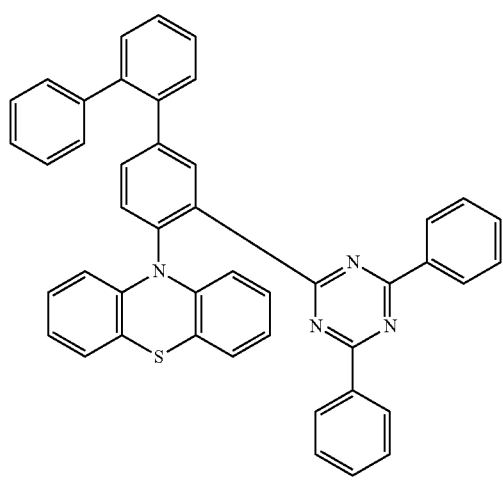
3322
-continued
100
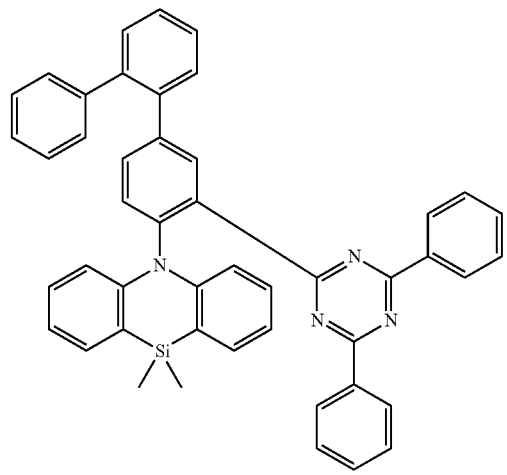
101
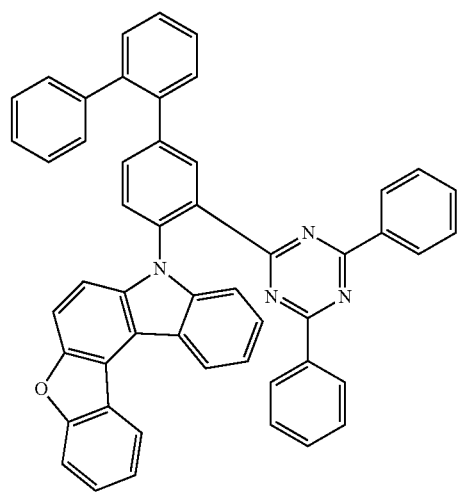
102
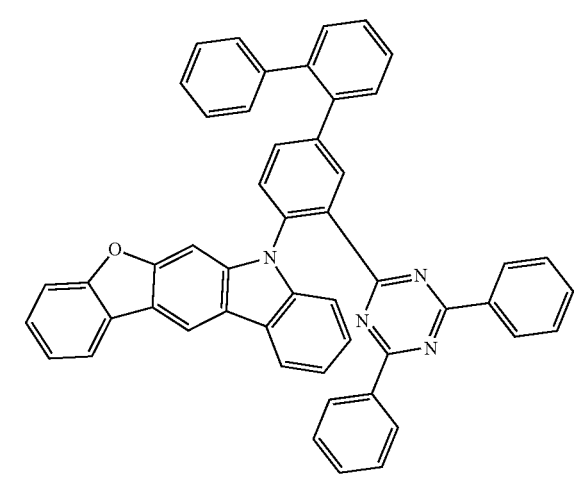

3323
-continued
3324
-continued
103
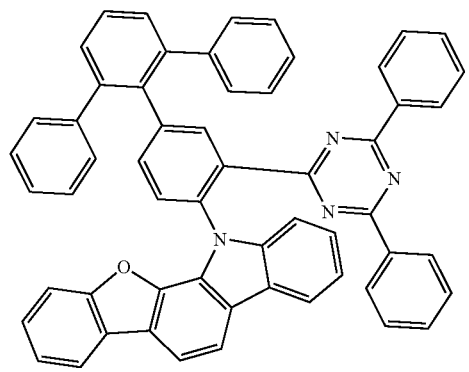
106
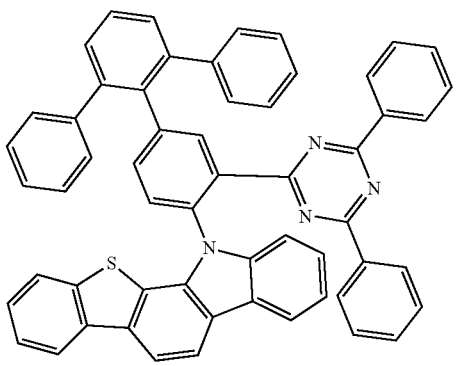
104
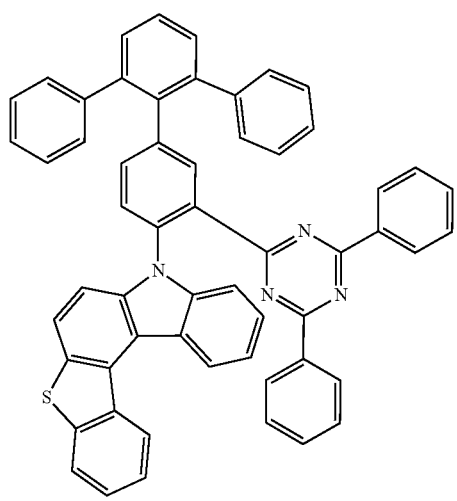
107
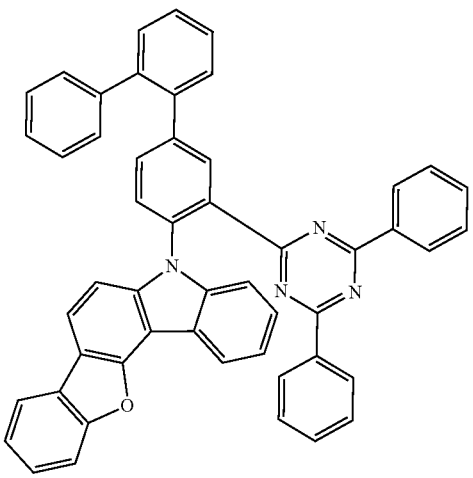
105
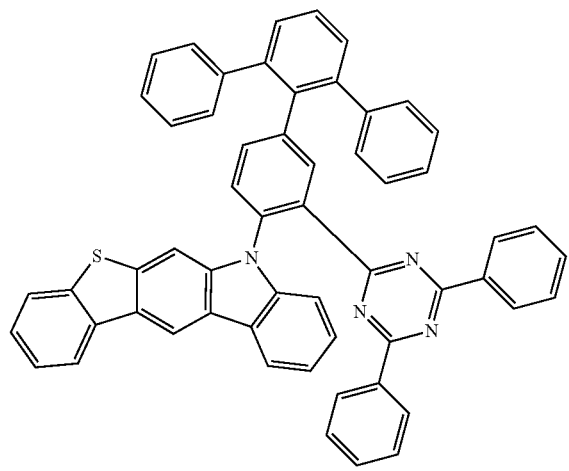
108
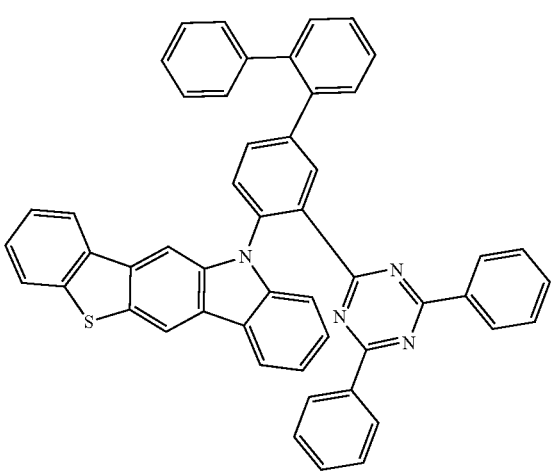

3325
-continued
109
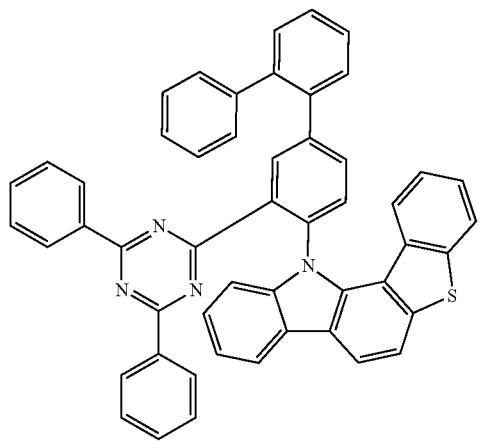
110
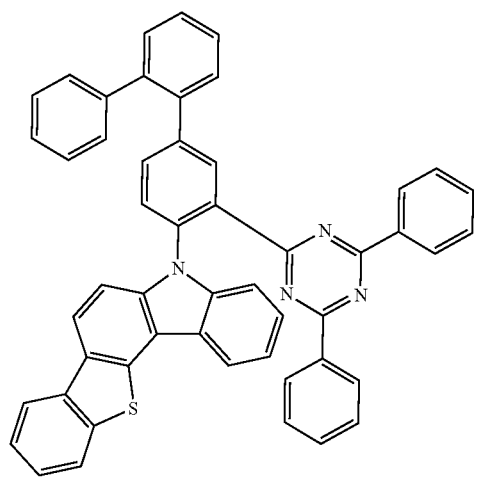
111
3326
-continued
112
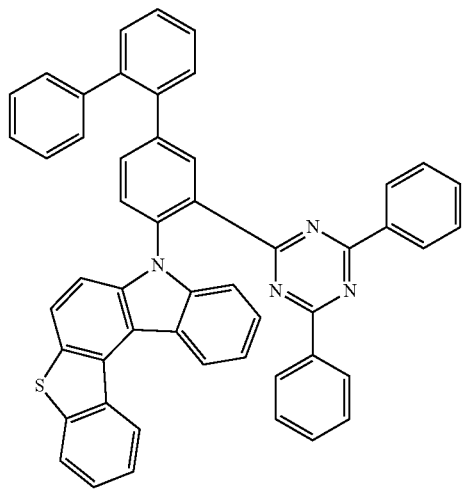
113
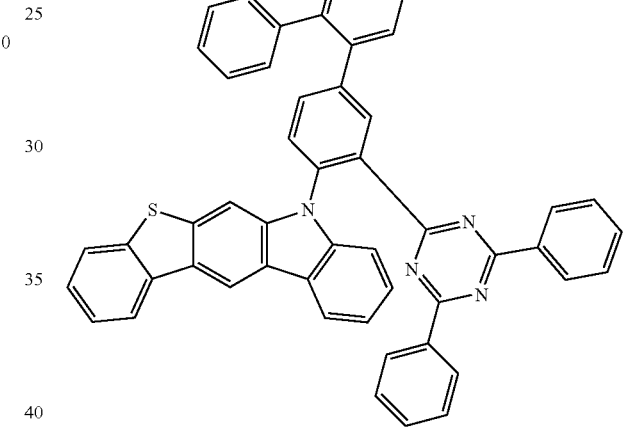
114
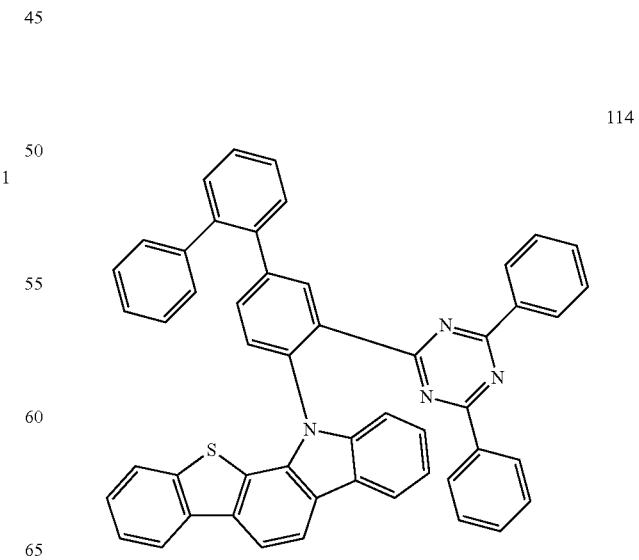

3327
-continued
3328
-continued
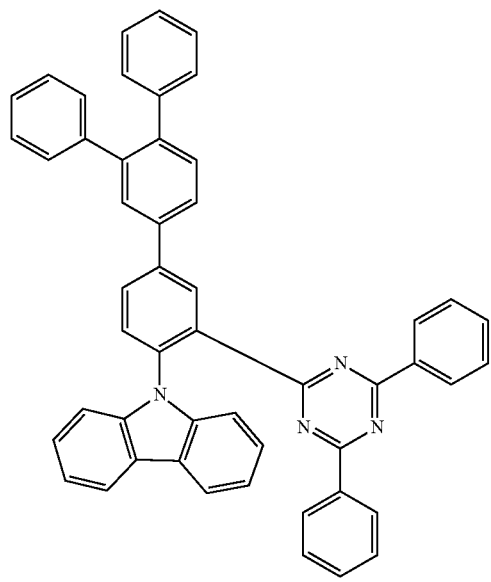
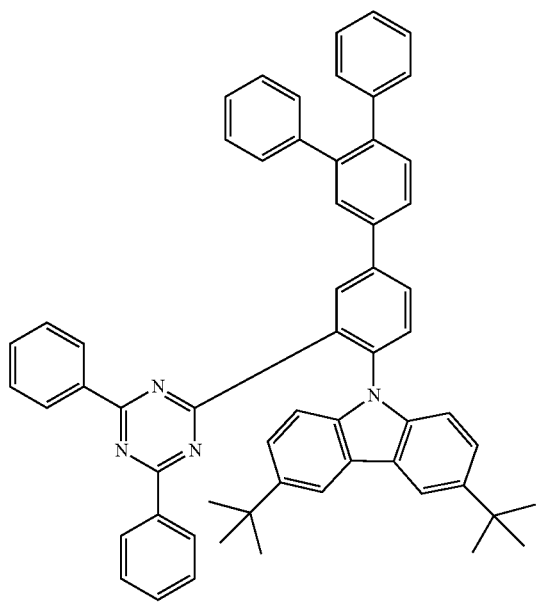

3329
-continued
119
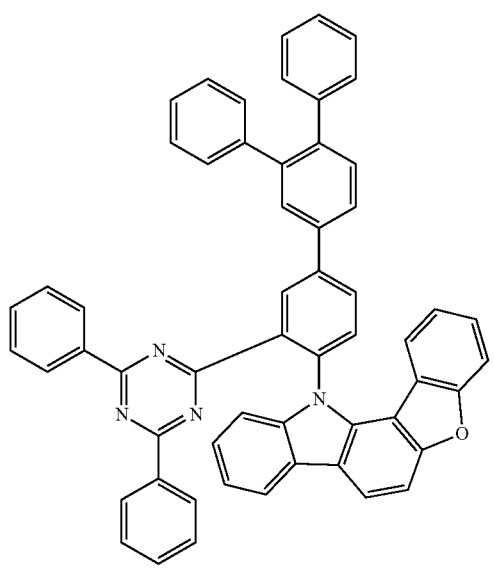
120
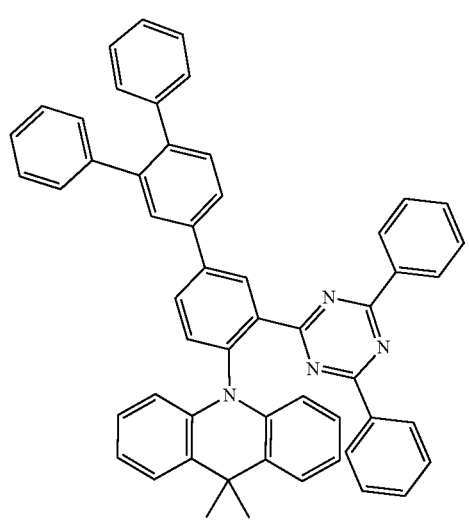
121
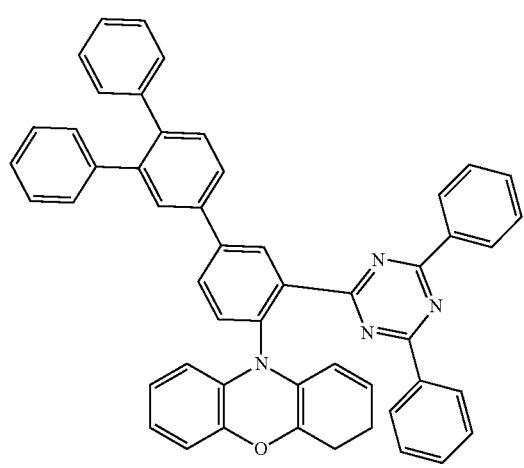
3330
-continued
122
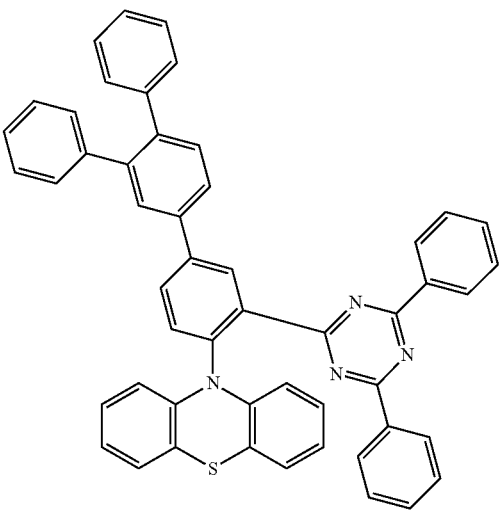
123
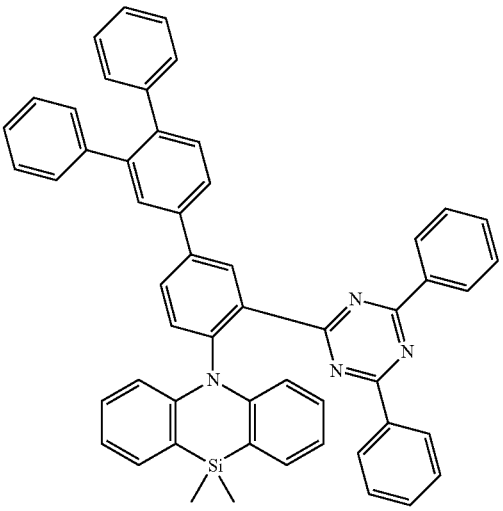

3331
-continued
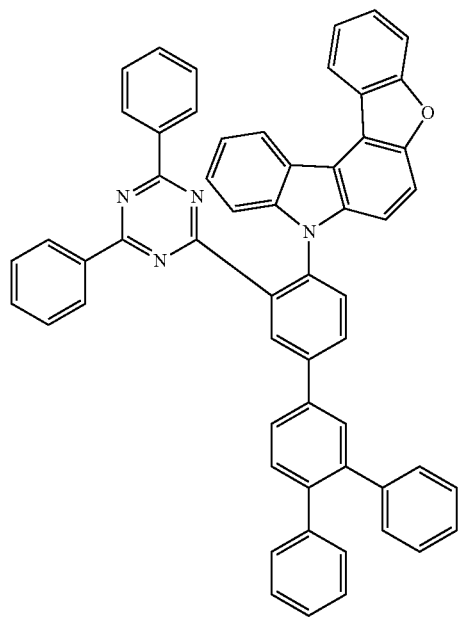
124
3332
-continued
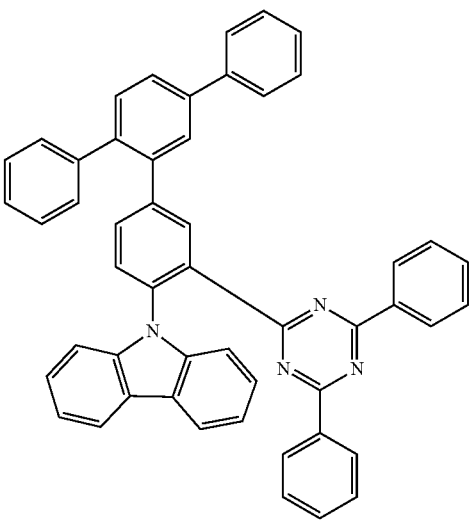
126
125
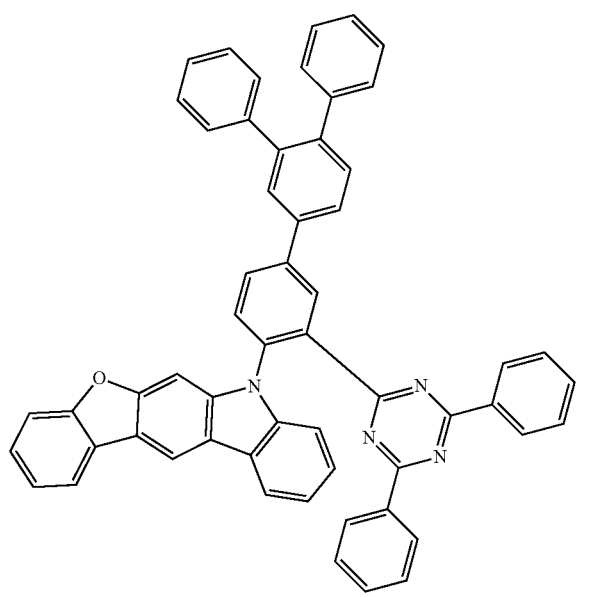
127
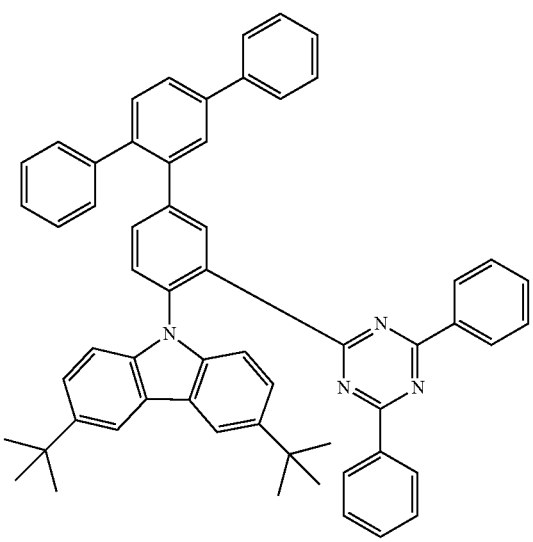

3333
-continued
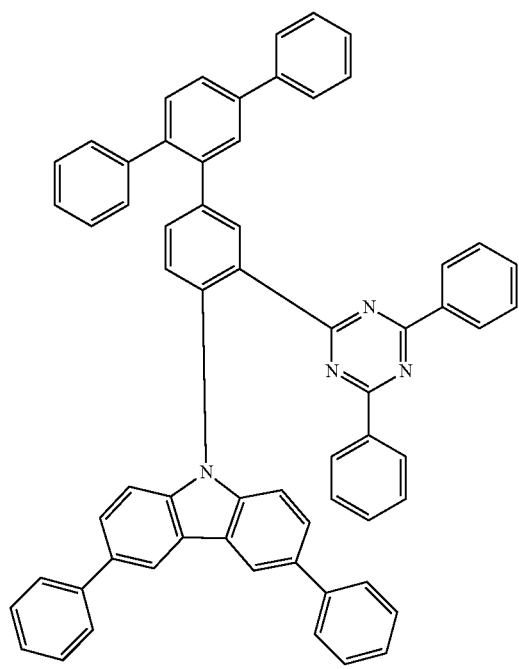
128
3334
-continued
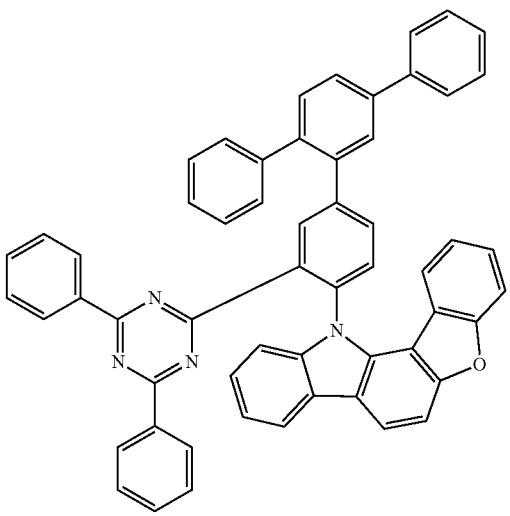
130
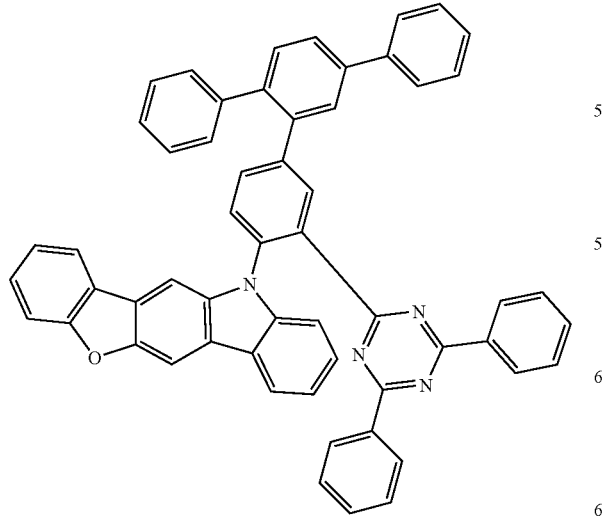
129
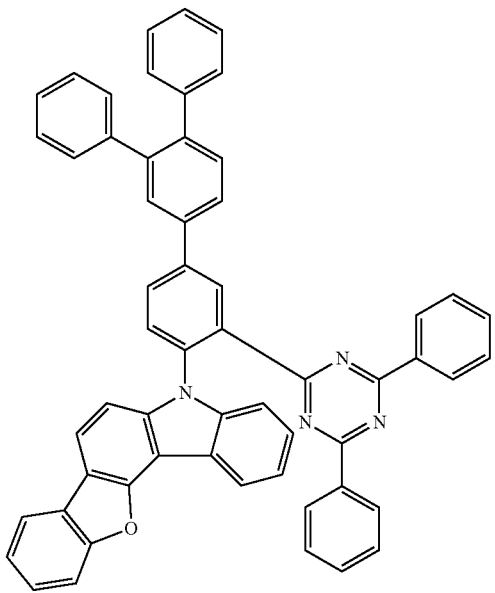
131

132
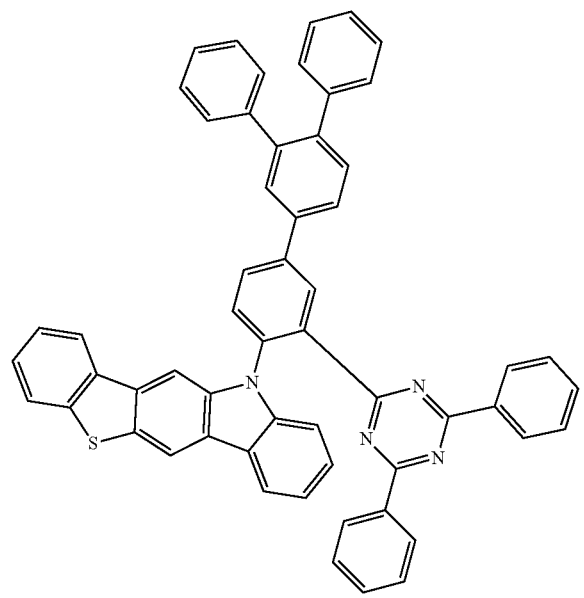
134
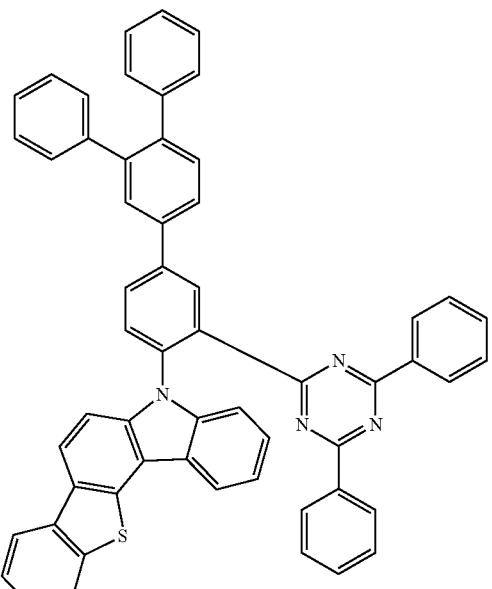
133
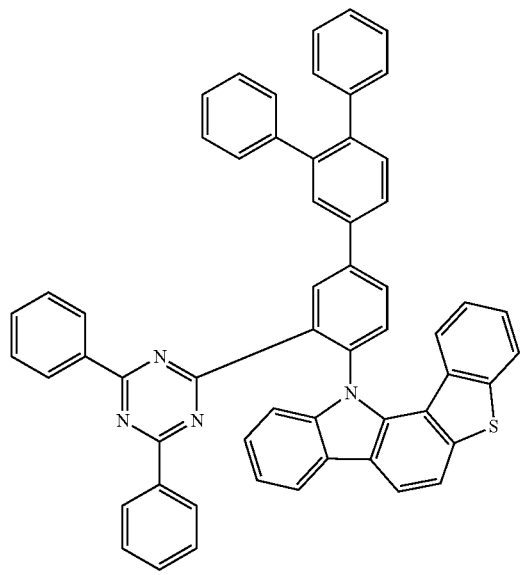
135
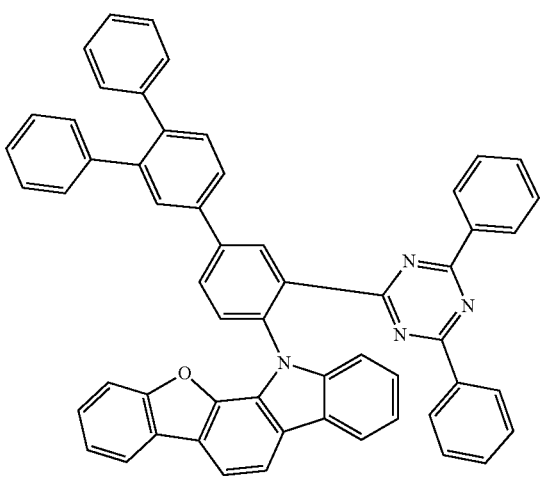

3337
-continued
3338
-continued
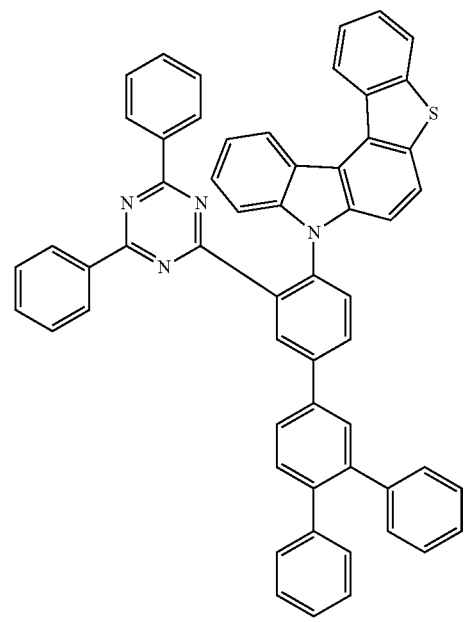
136
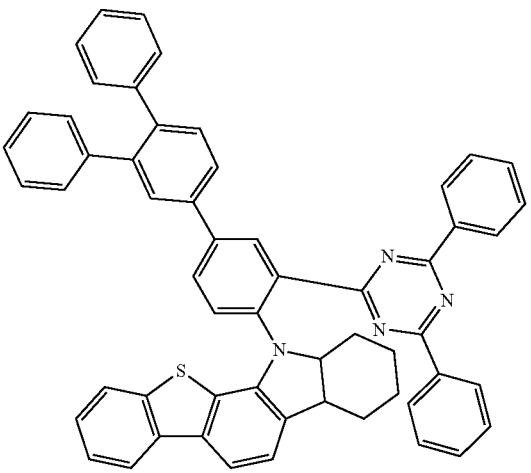
138
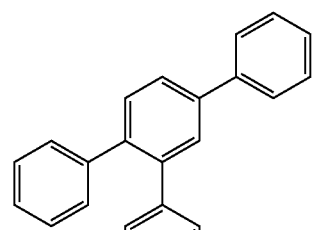
139
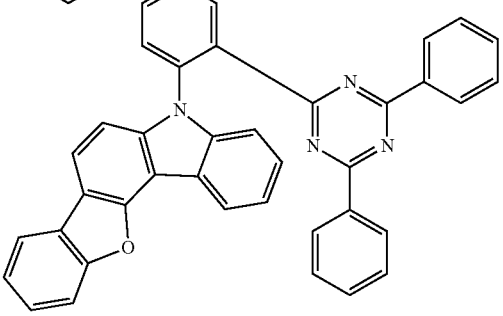
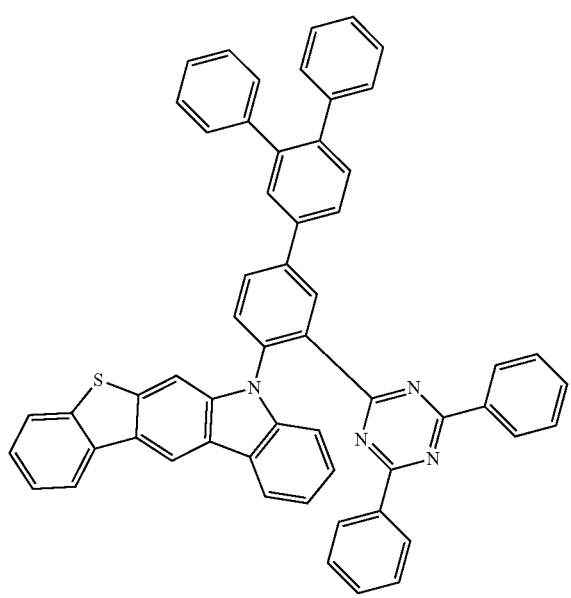
137
140

-continued
141
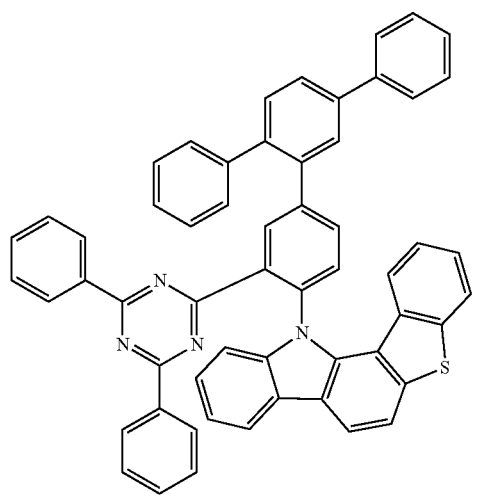
142
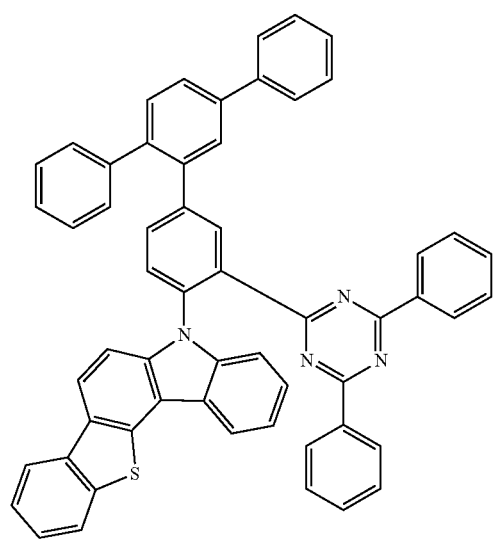
143
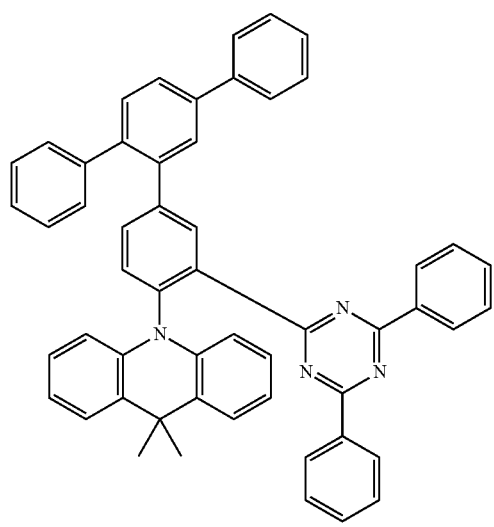
-continued
144
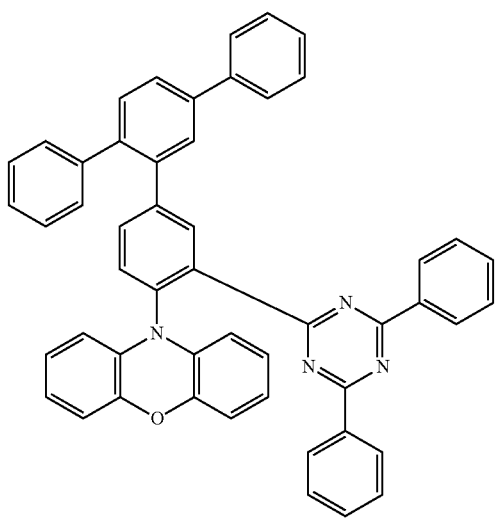
145
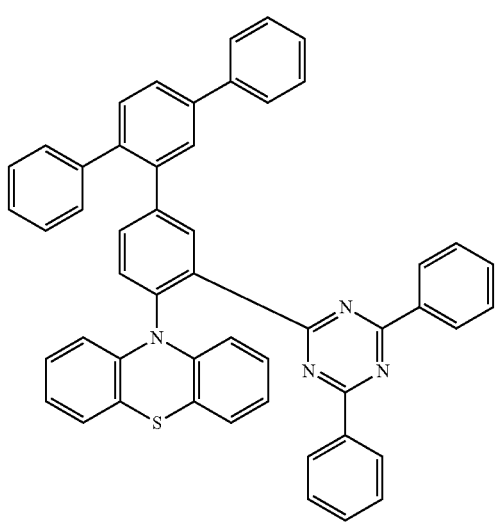
146
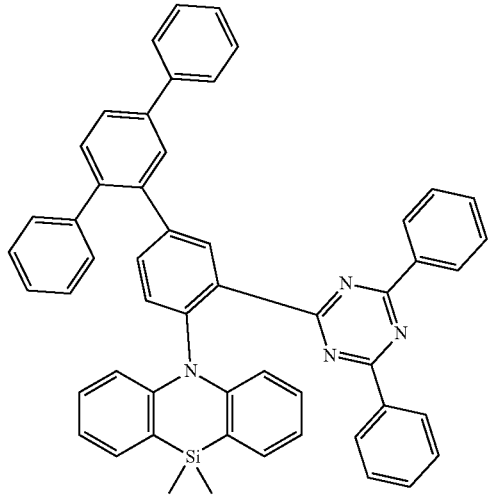

3341
-continued
147
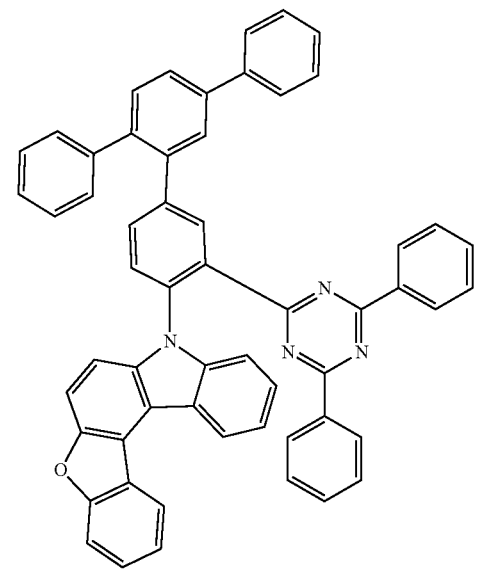
148
3342
-continued
149
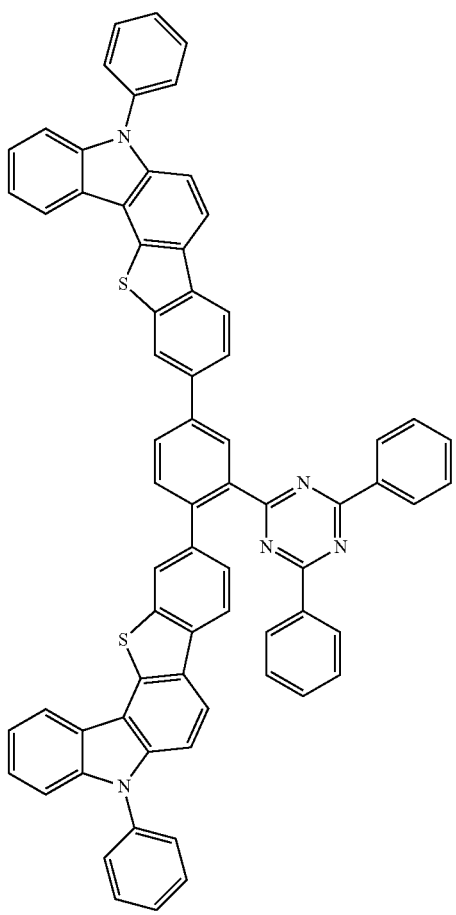

-continued
150
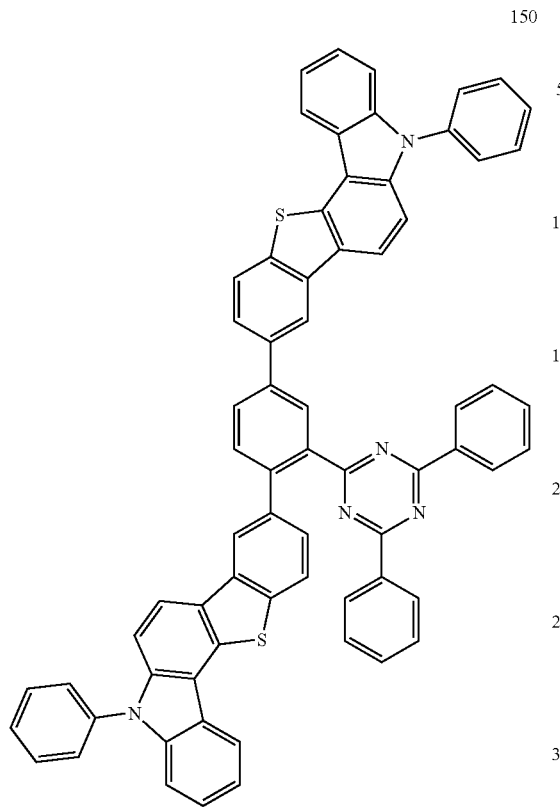
151
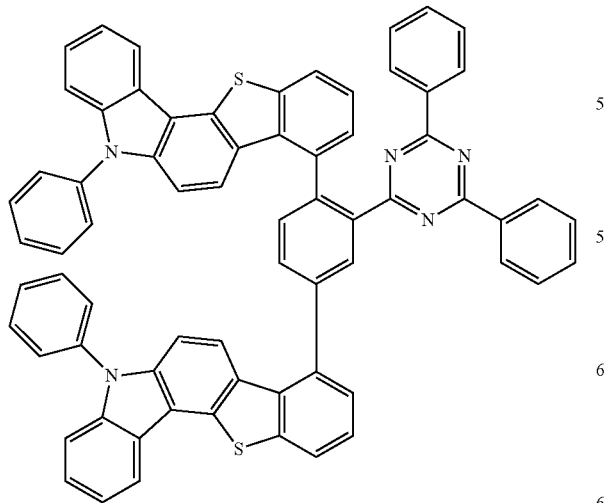
-continued
152
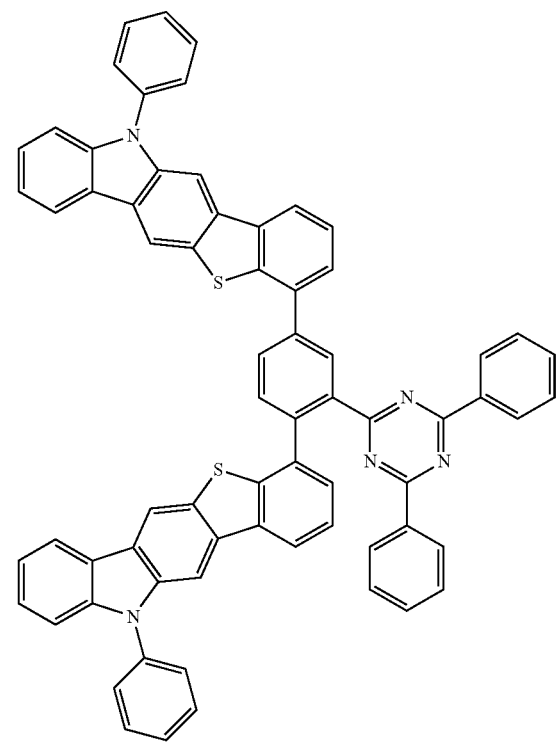
153
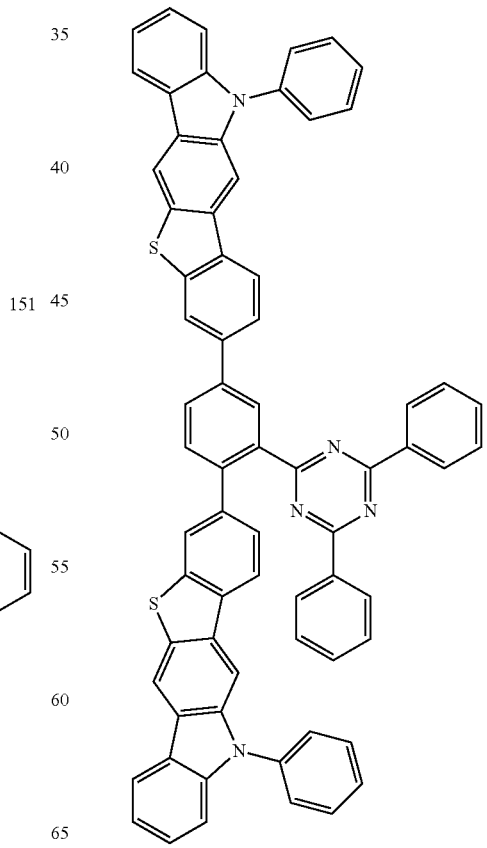

154
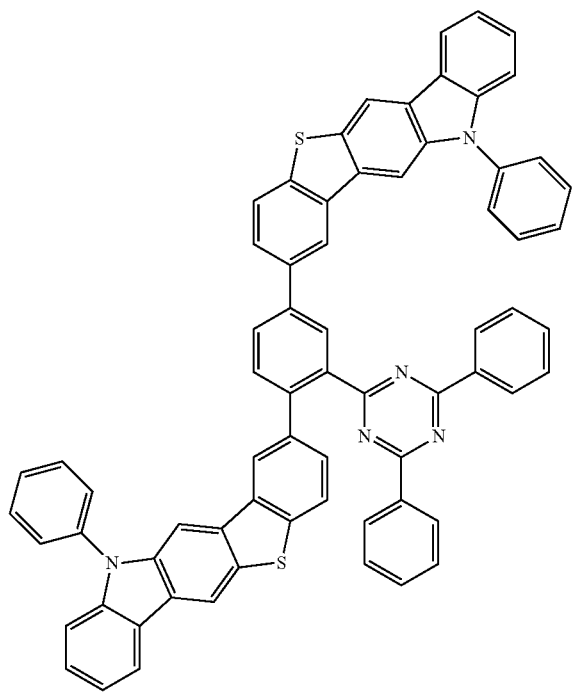
155
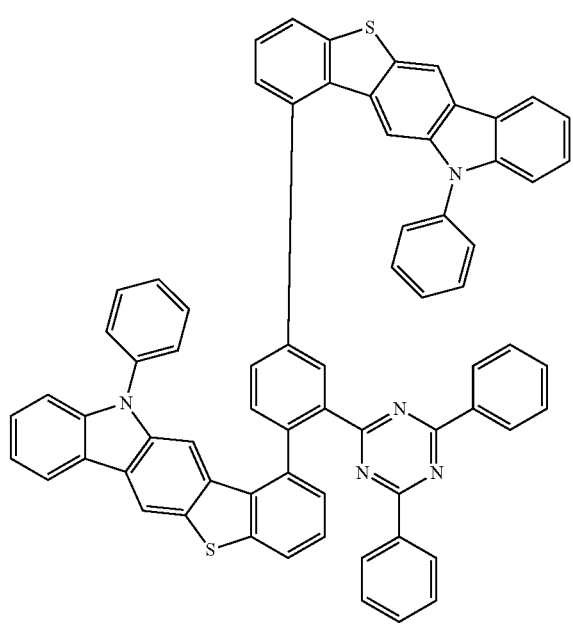
156
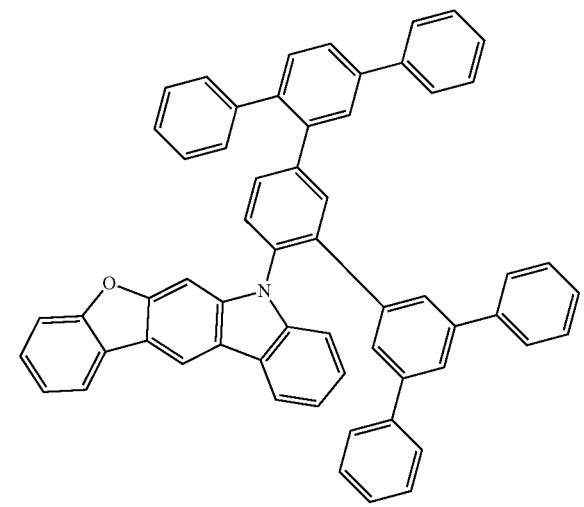
157
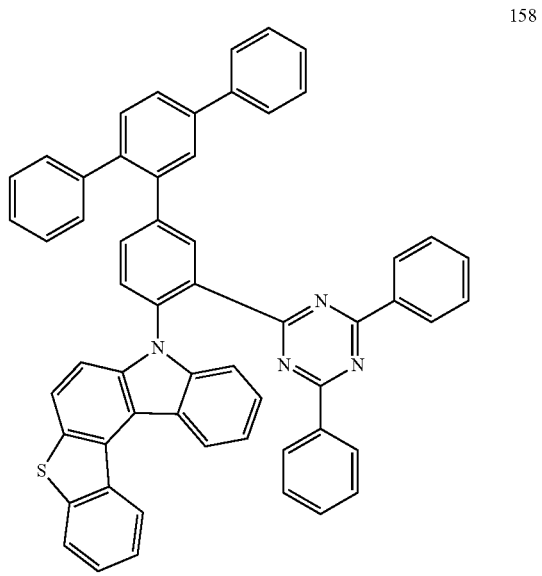
158

159
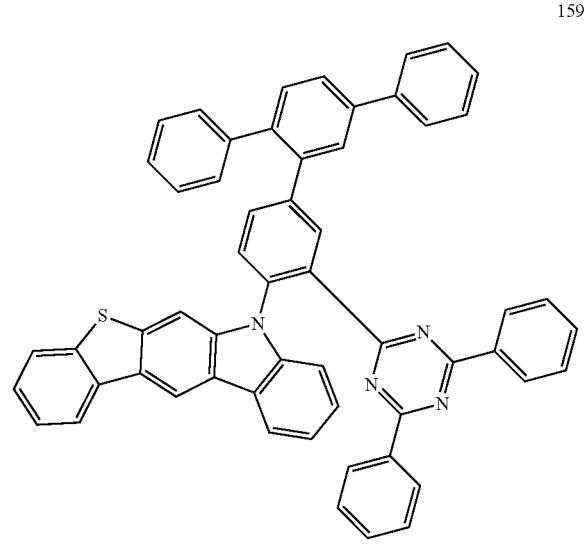
160
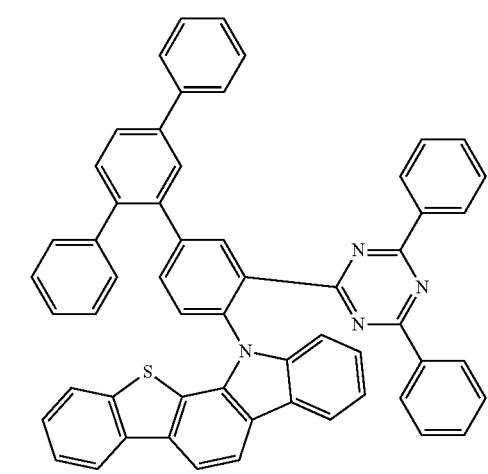
161
162
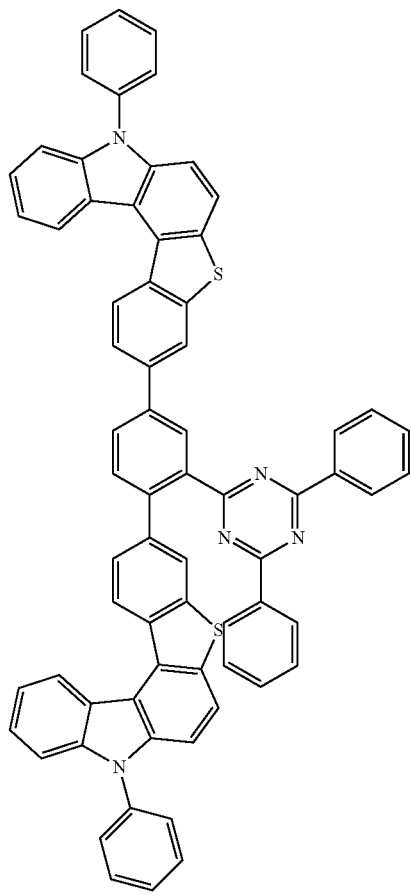

3349
-continued
163
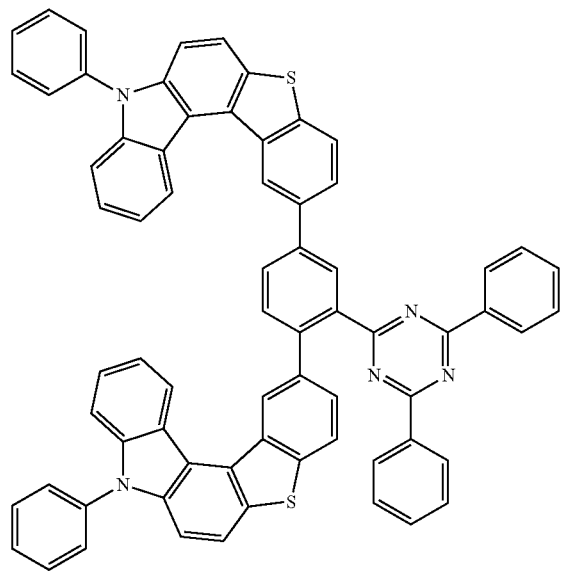
3350
-continued
165
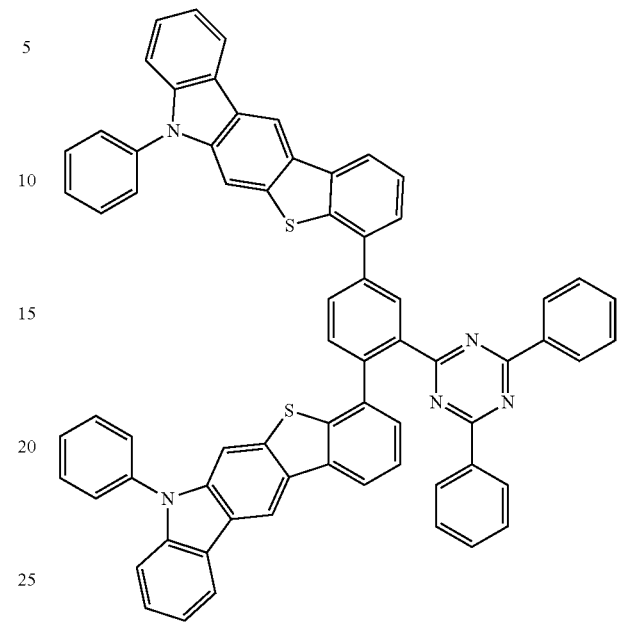
164
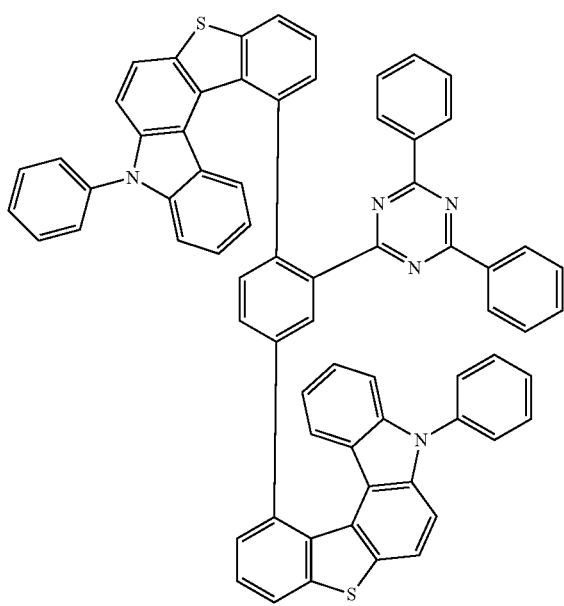
166
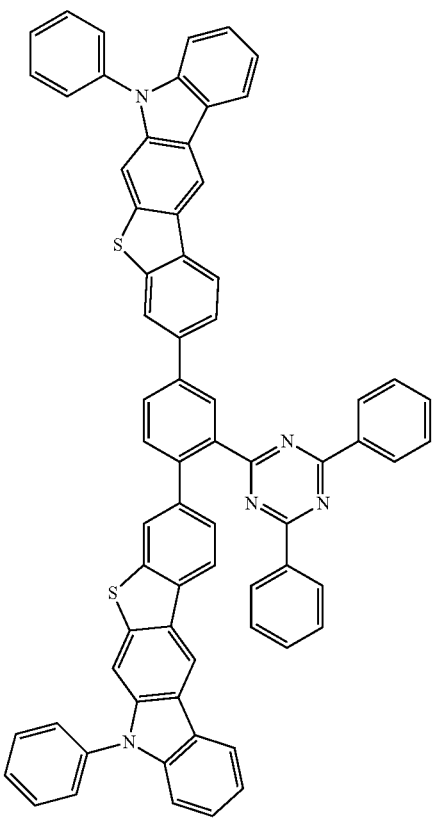

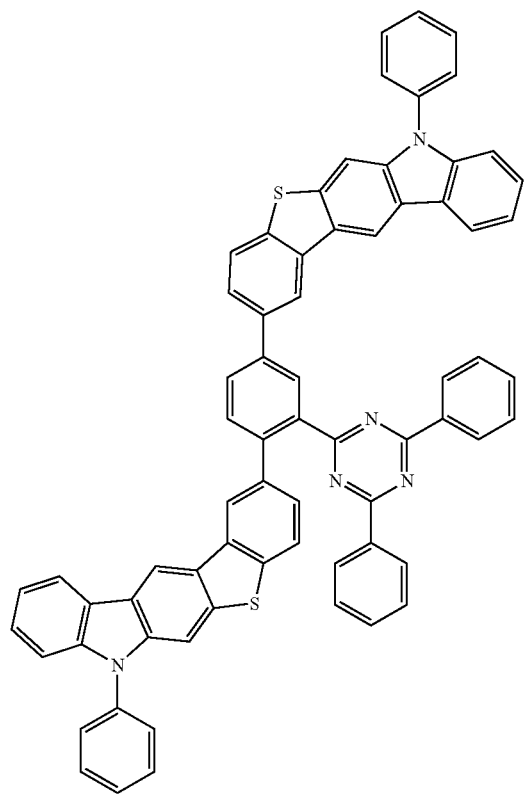
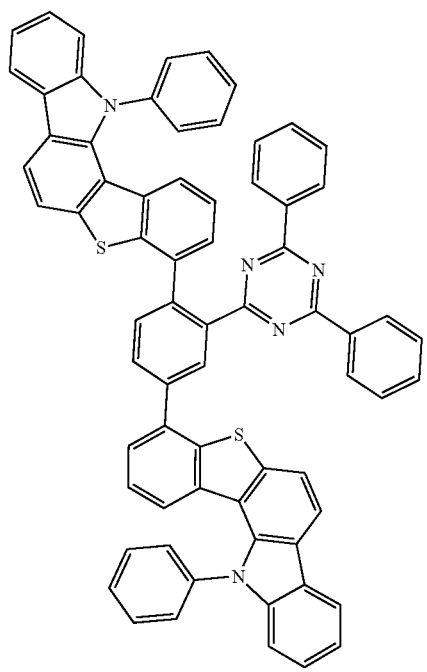
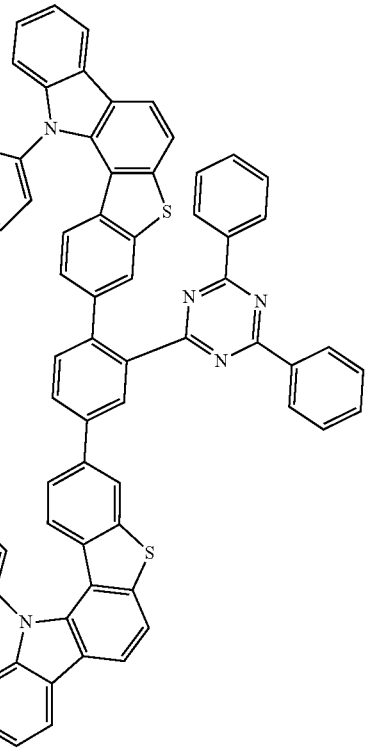

3353
-continued
171
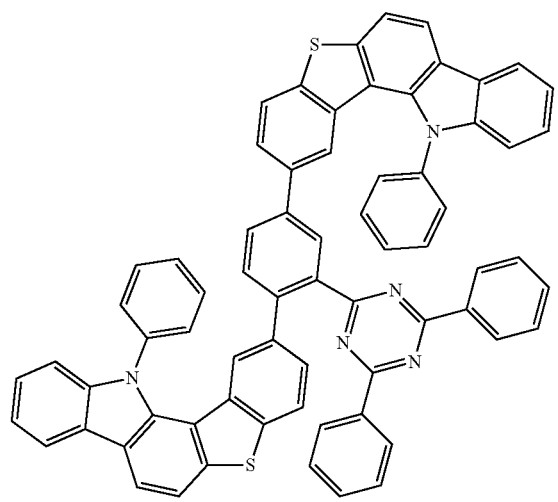
172
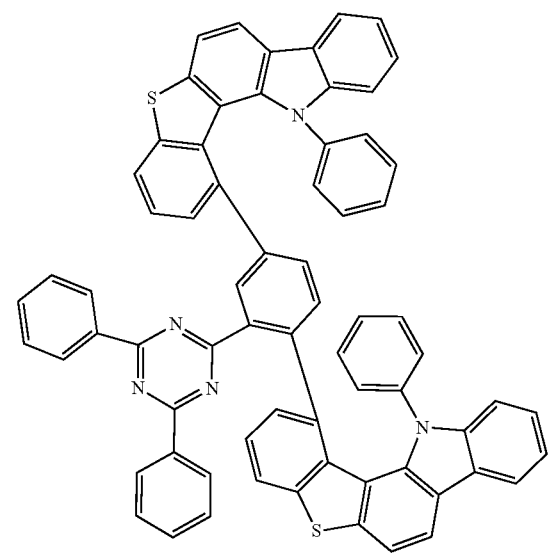
173
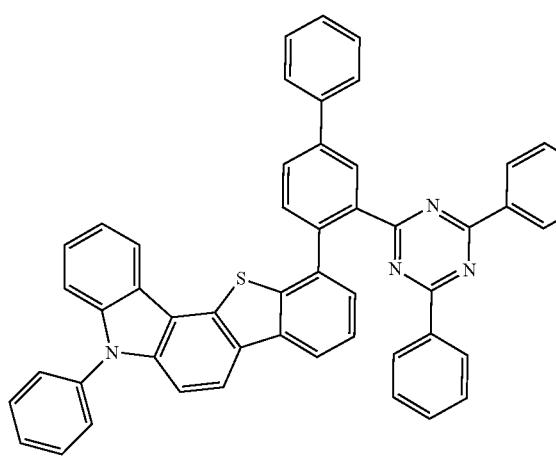
3354
-continued
174
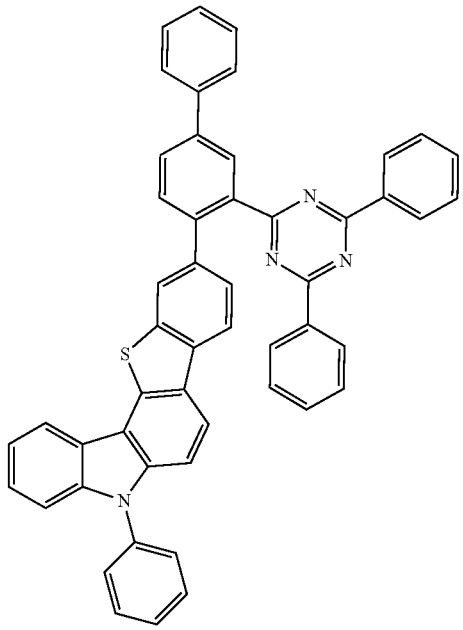
175
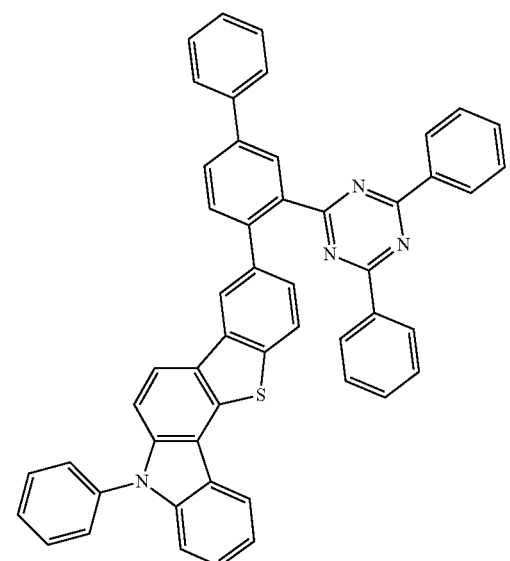
176
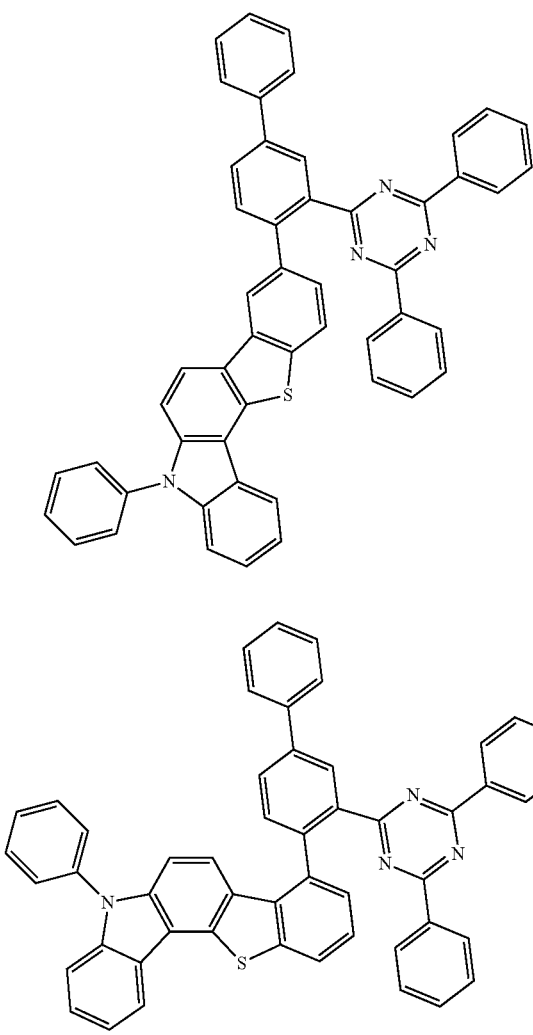

177
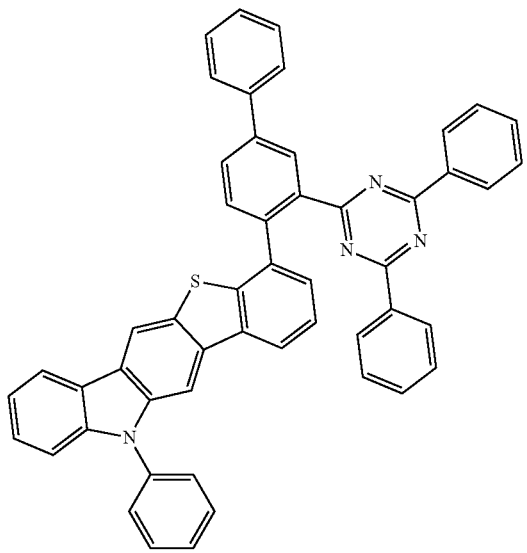
178
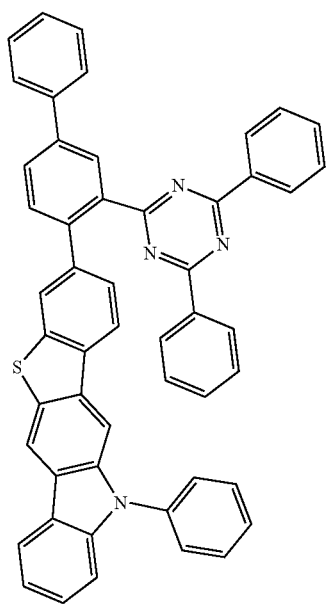
179
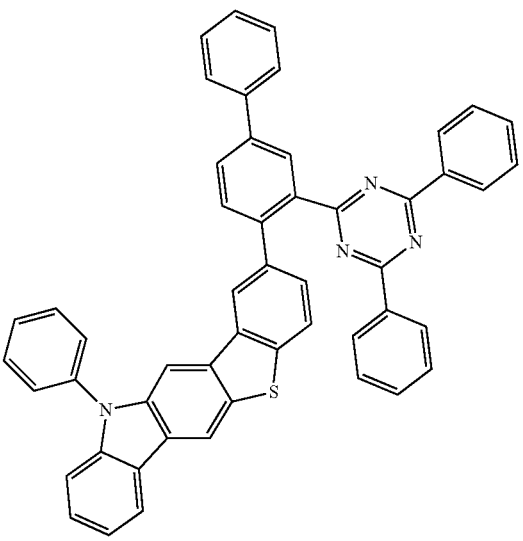
180
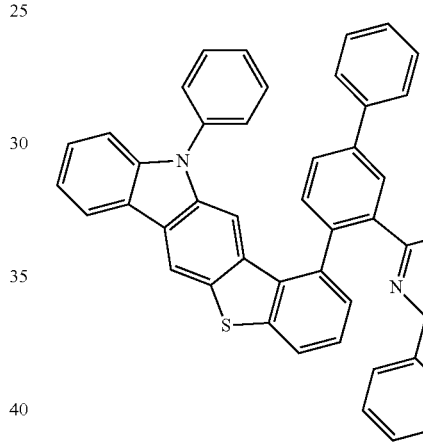
181
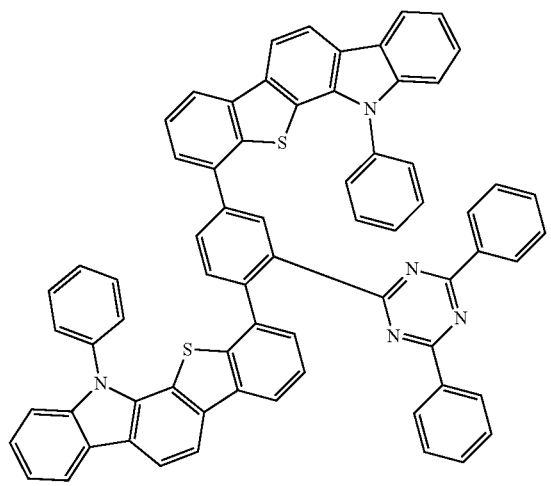

3357
-continued
3358
-continued
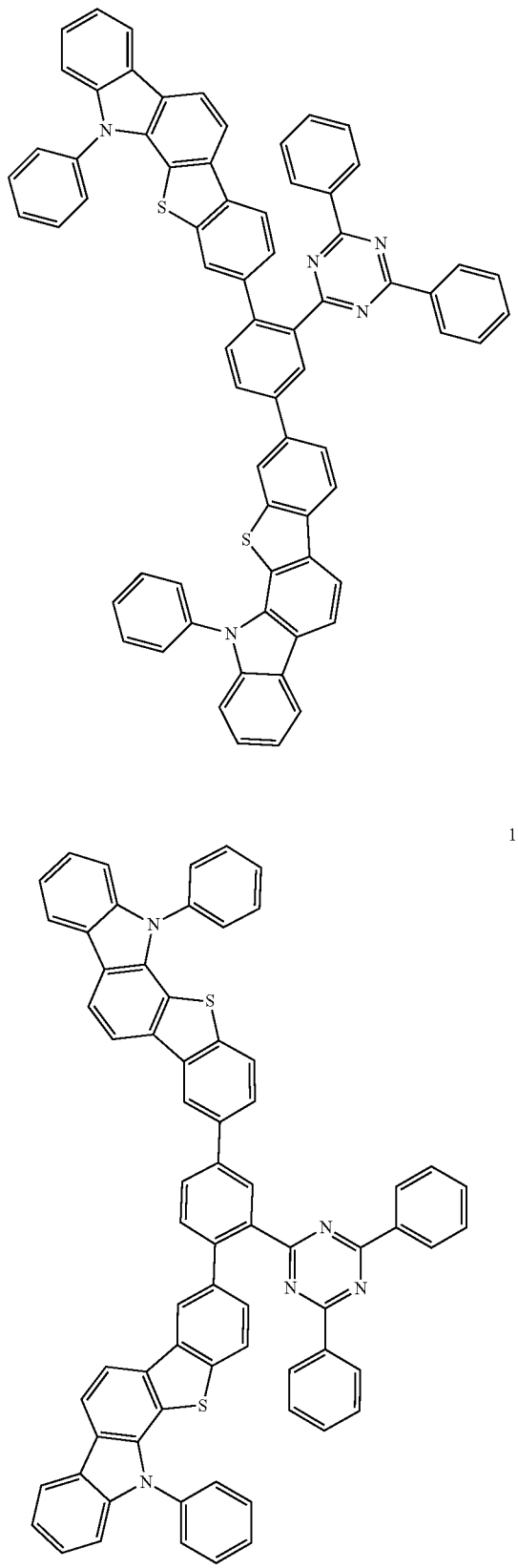
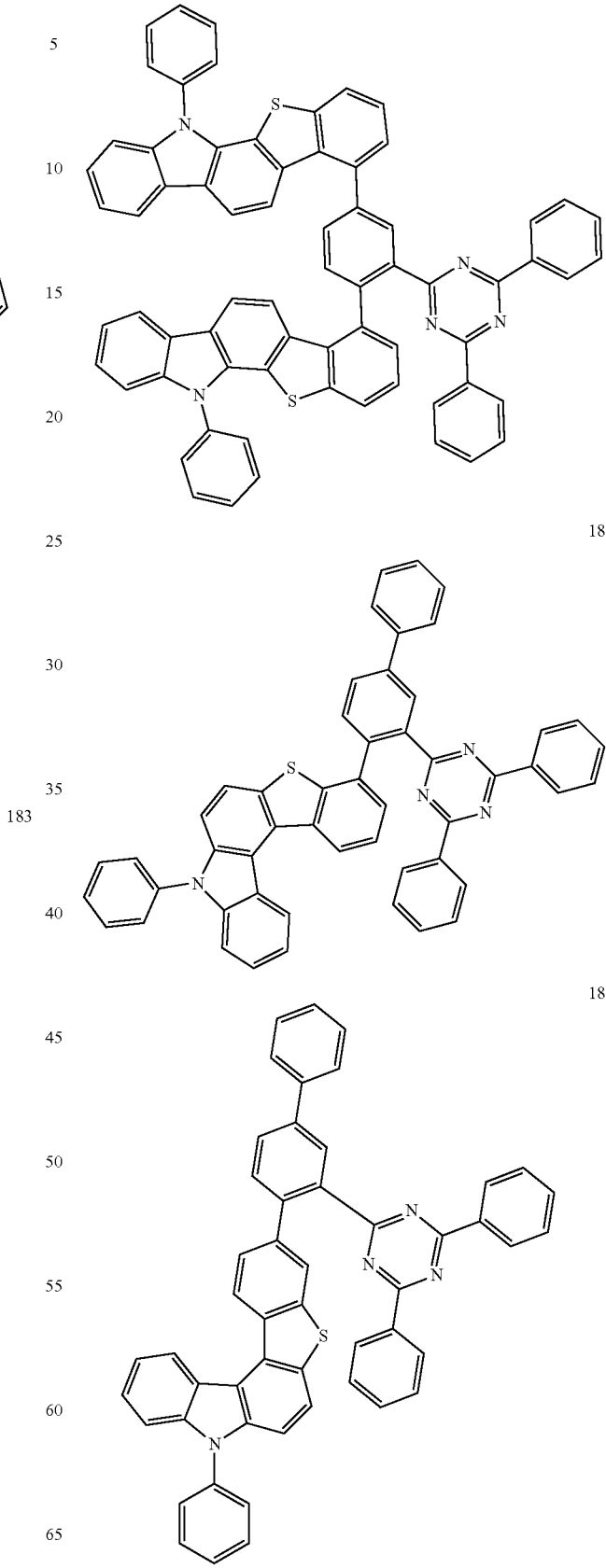

187
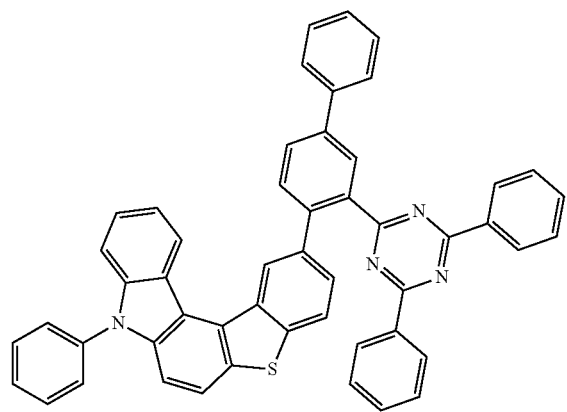
188
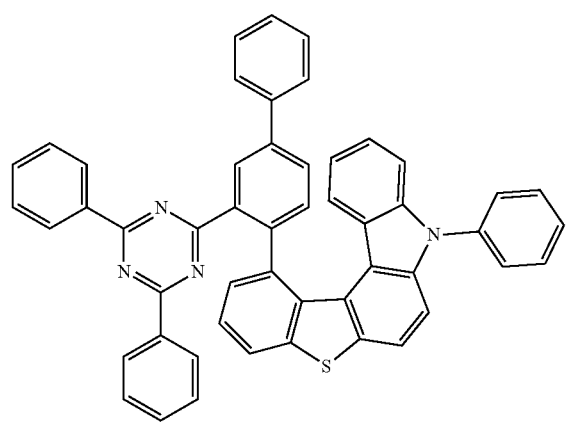
189
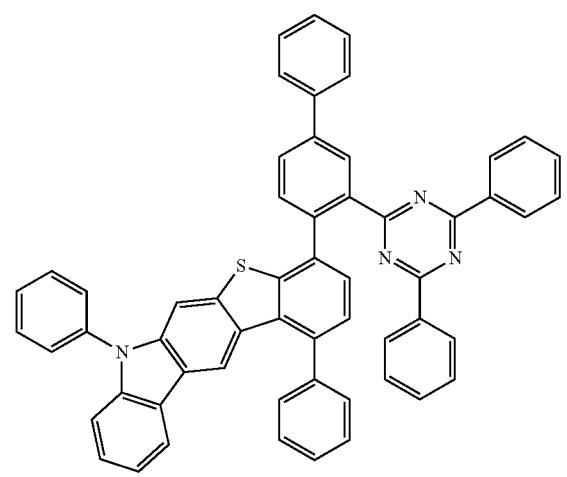
190
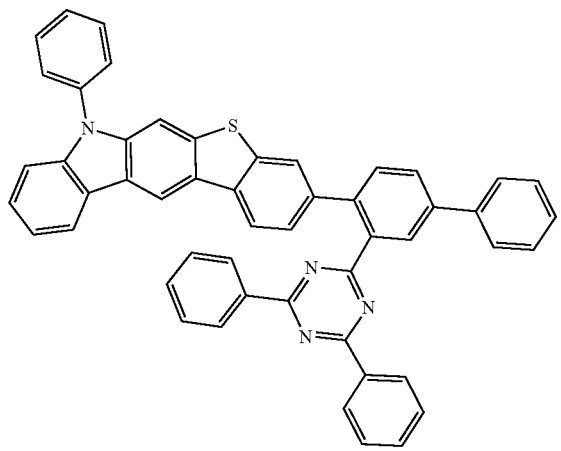
191
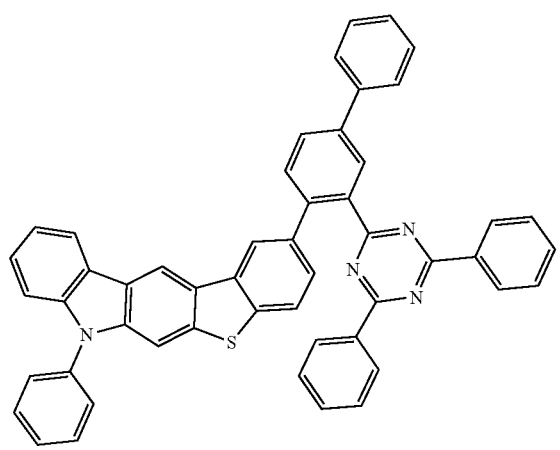
192
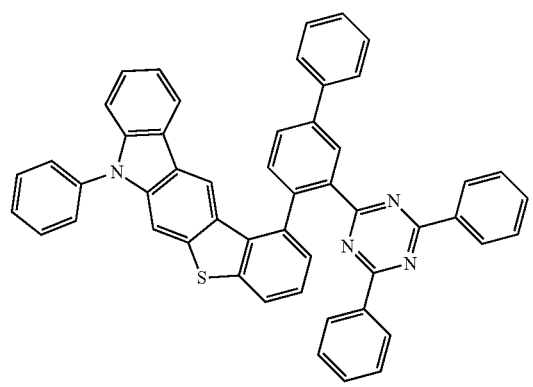

3361
-continued
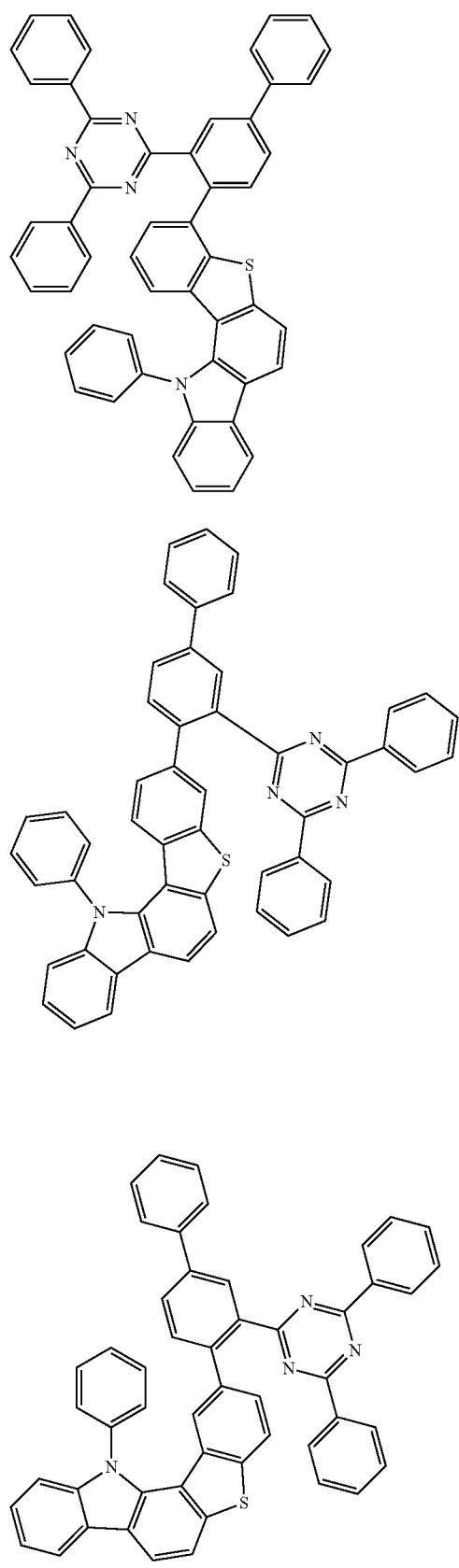
193
194
195
3362
-continued
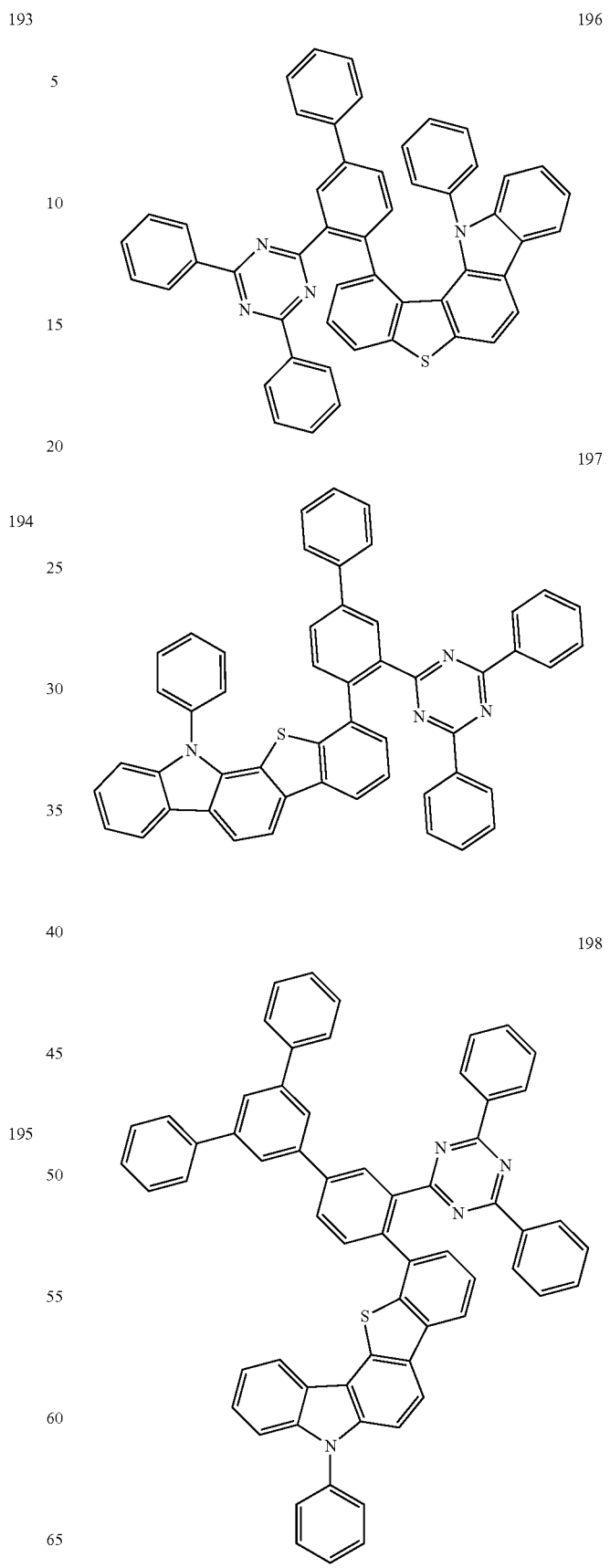
196
197
198

3363
-continued
199
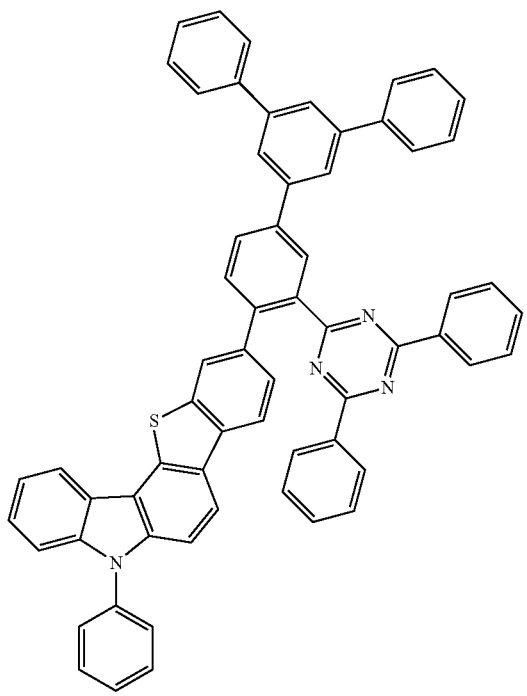
200
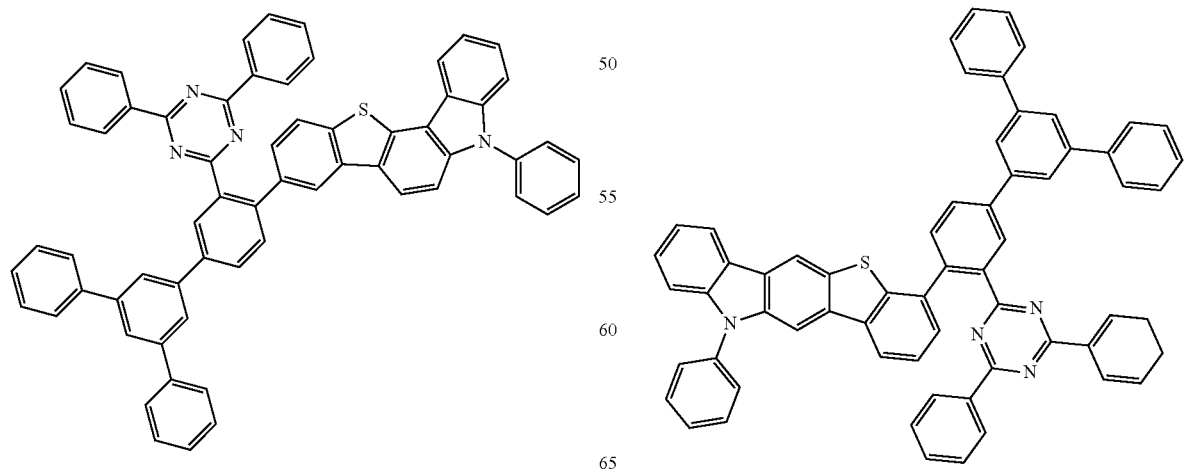
3364
-continued
201
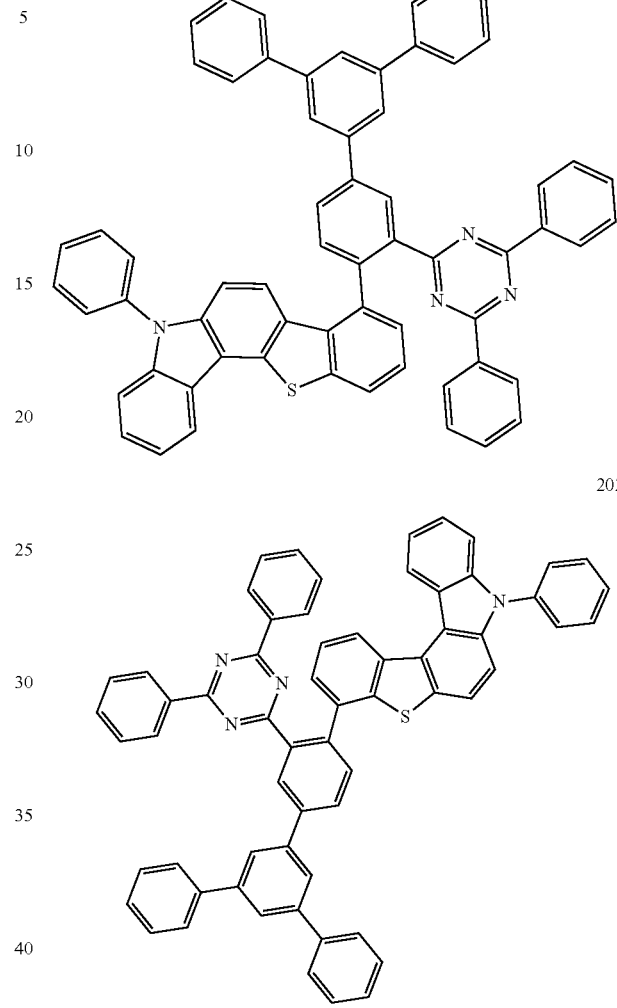
202
203

3365
-continued
204
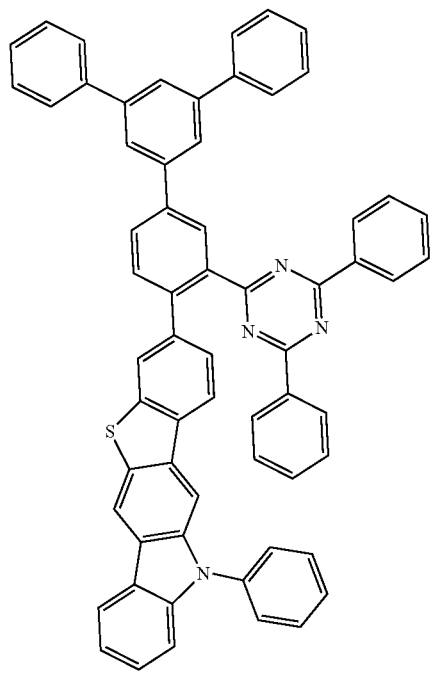
205
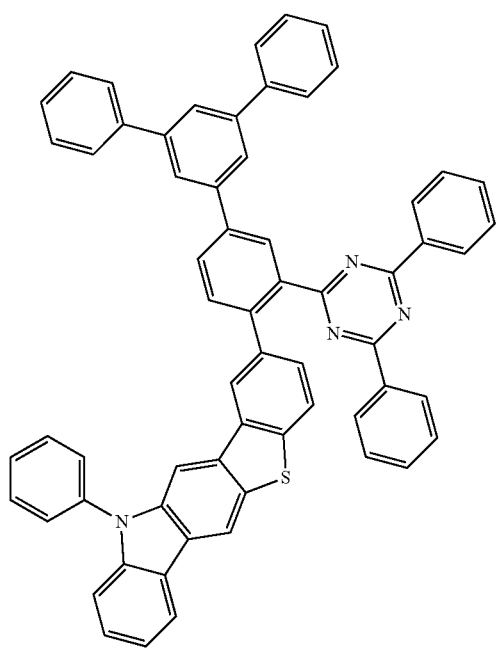
3366
-continued
206
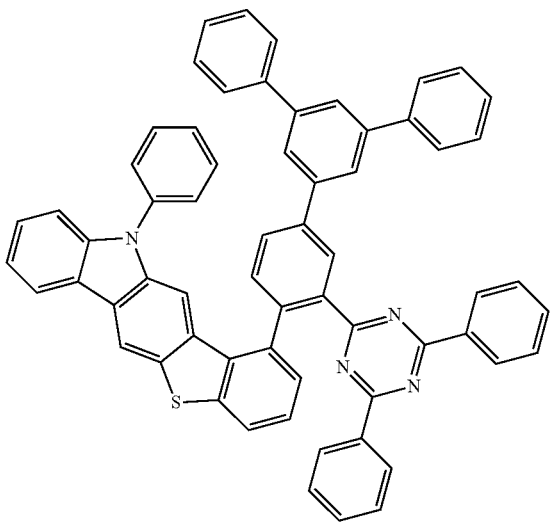
207
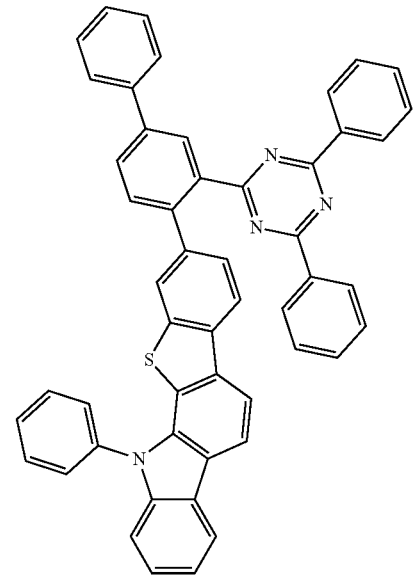

3367
-continued
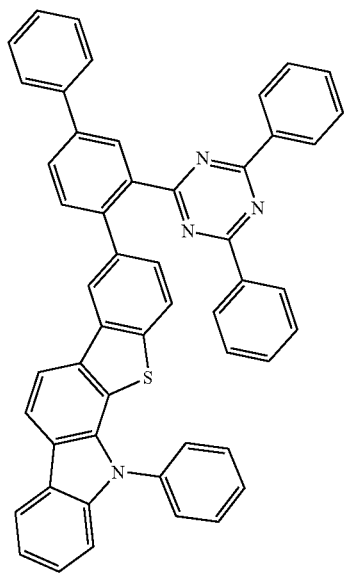
208
3368
-continued
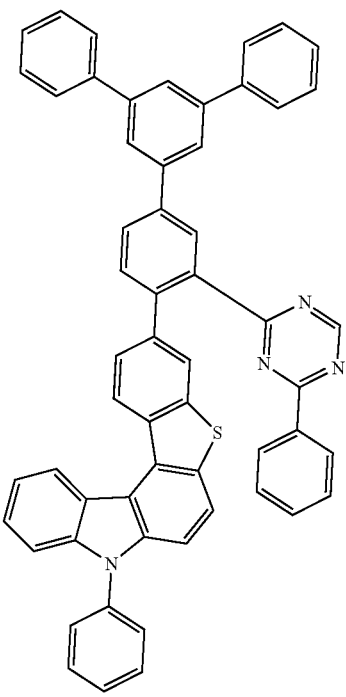
210
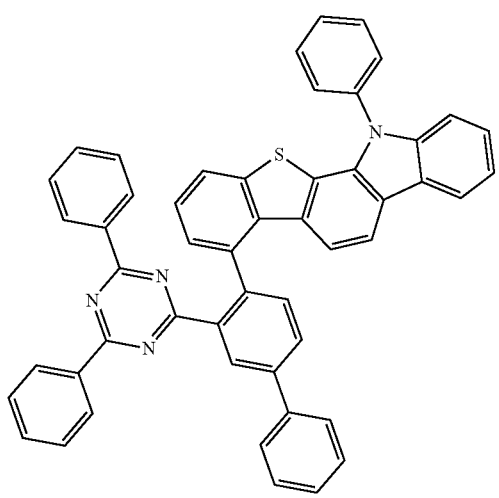
209
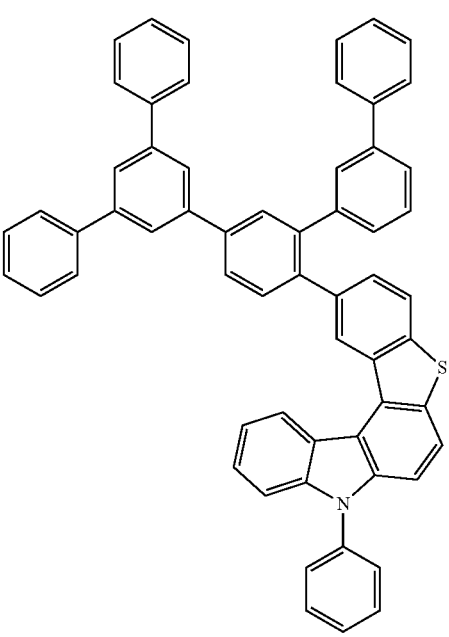
211

3369
-continued
3370
-continued
212
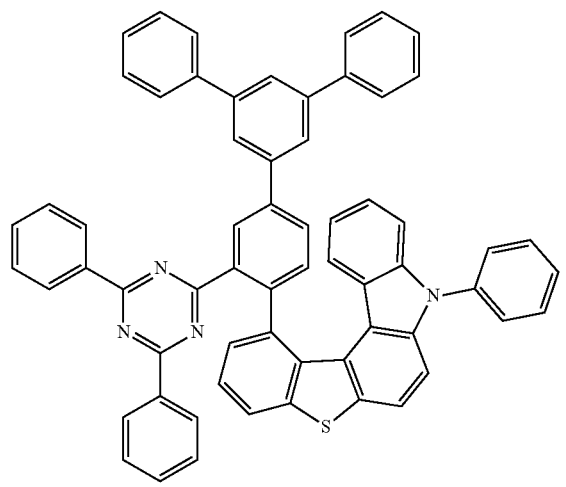
215
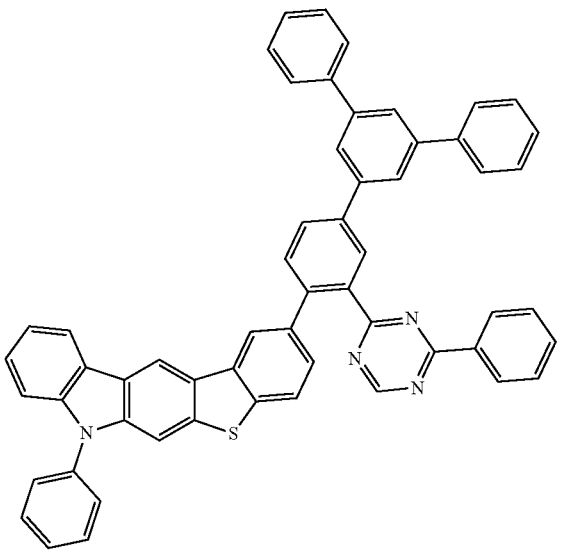
213
214
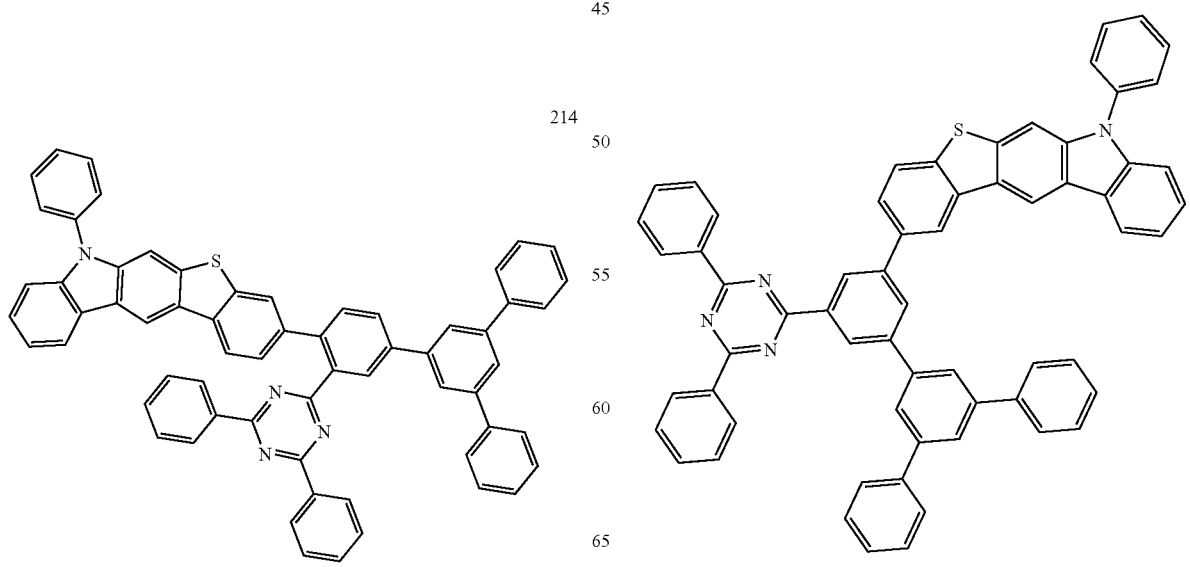
216

3371
-continued
217
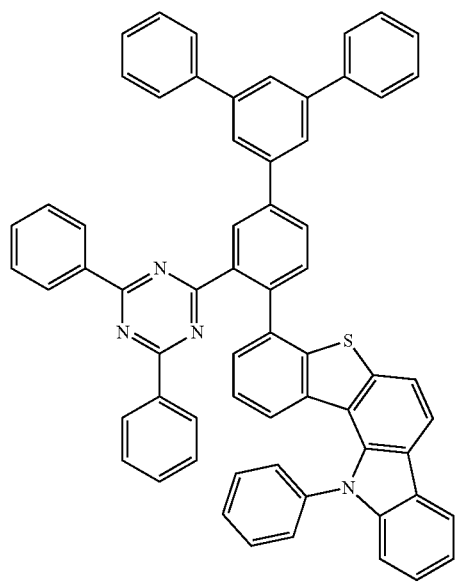
218
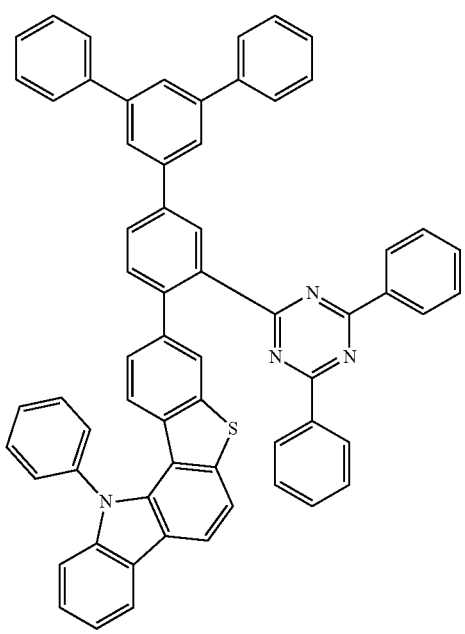
3372
-continued
219
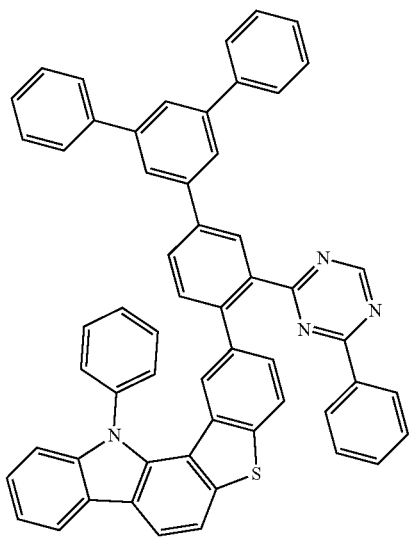
220
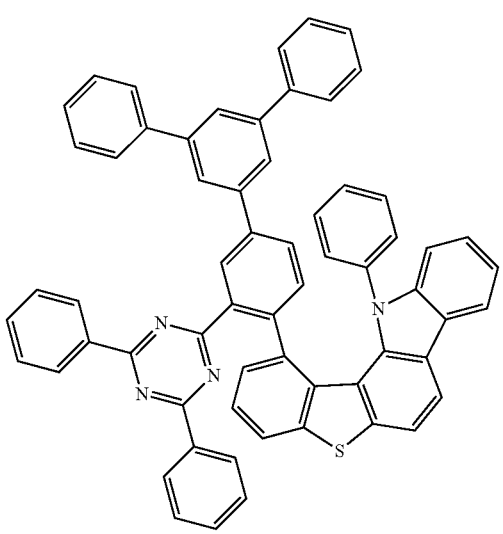
221
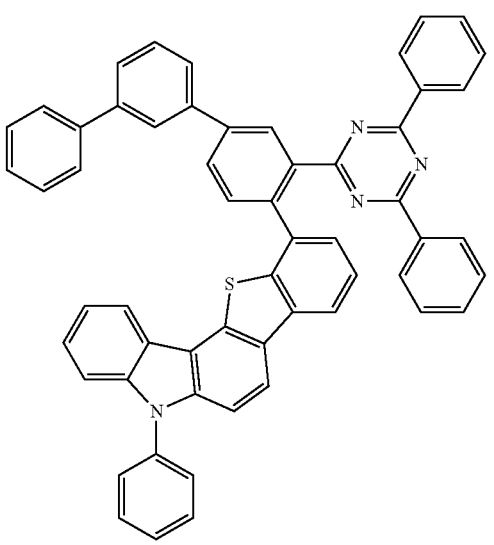

3373
-continued
3374
-continued
222
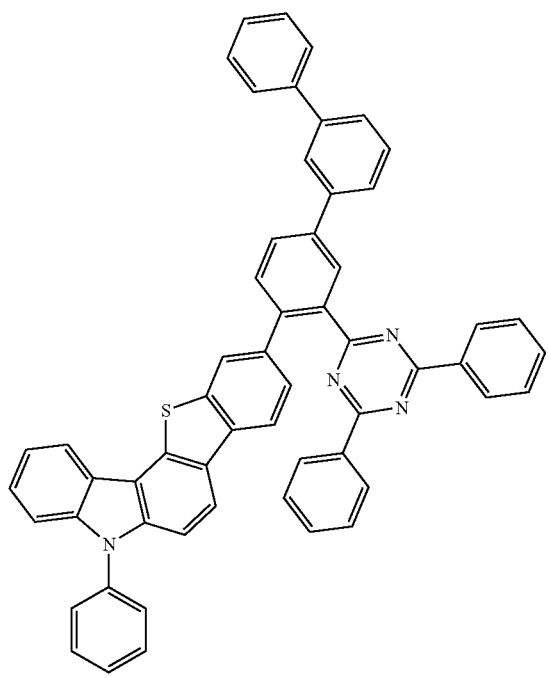
223
225
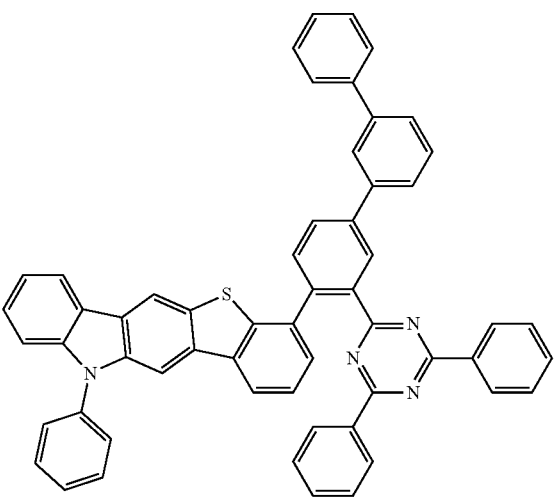
226
224
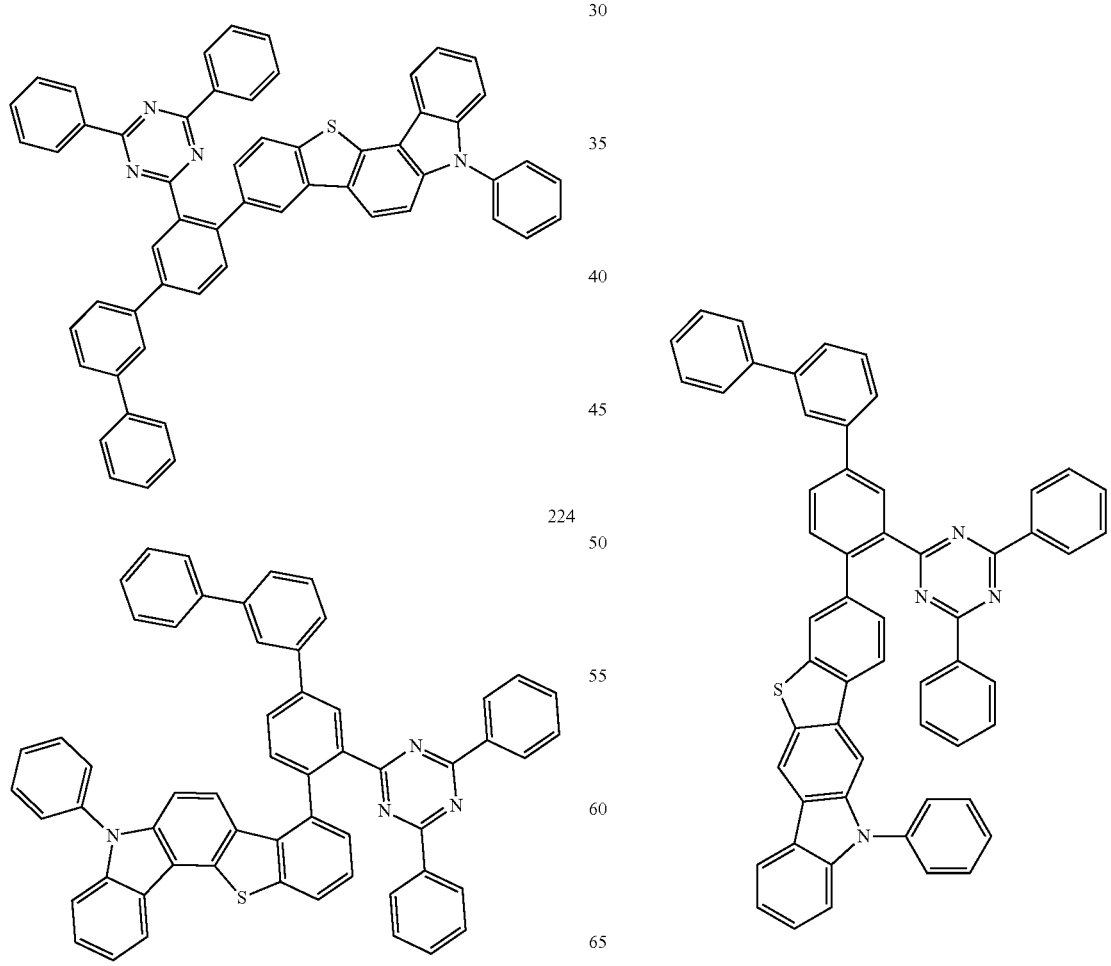

227
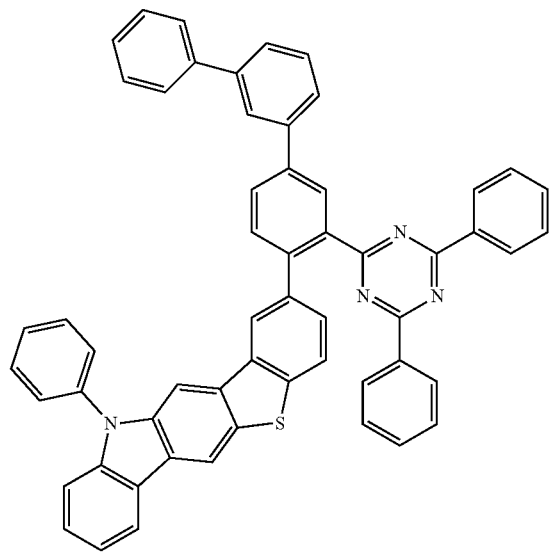
228
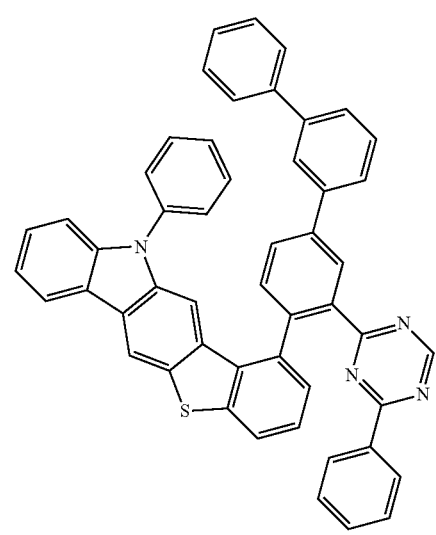
229
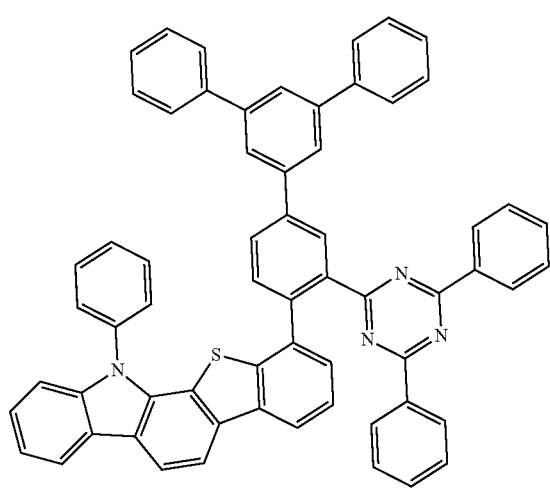
230
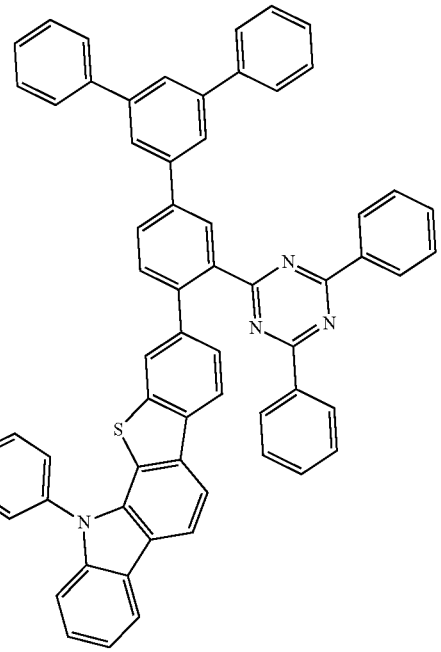
231
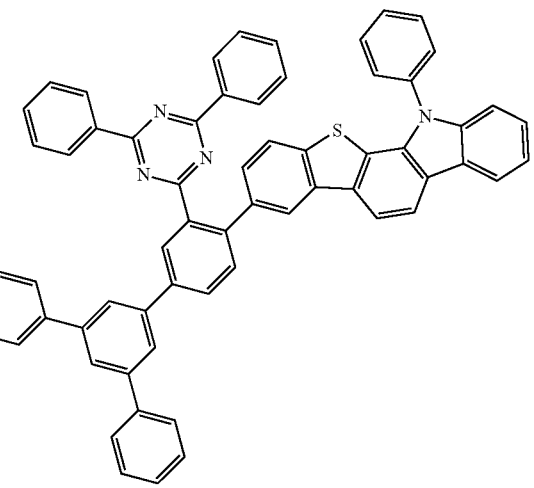

-continued
232
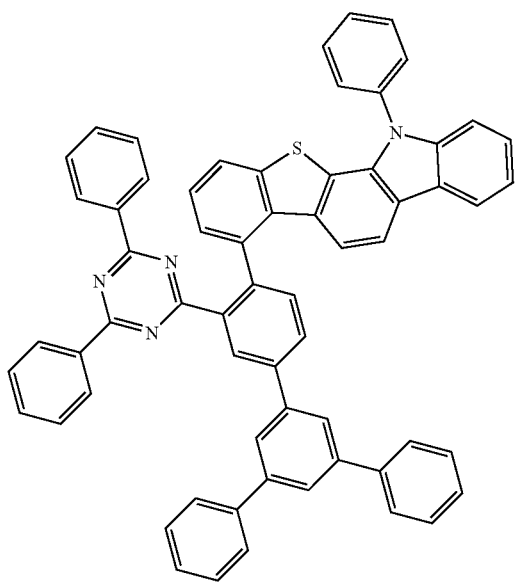
233
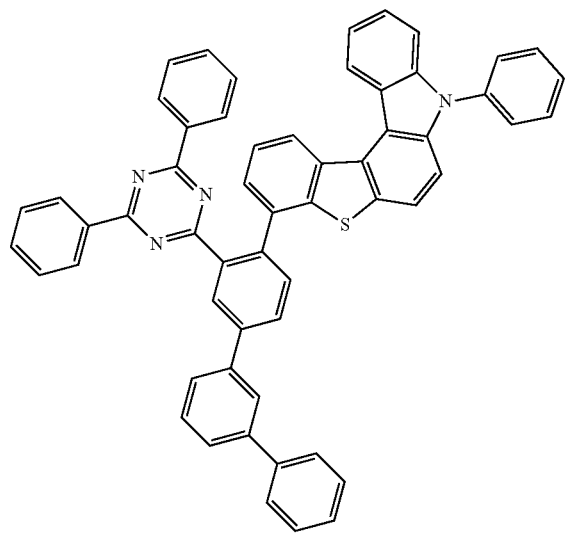
-continued
234
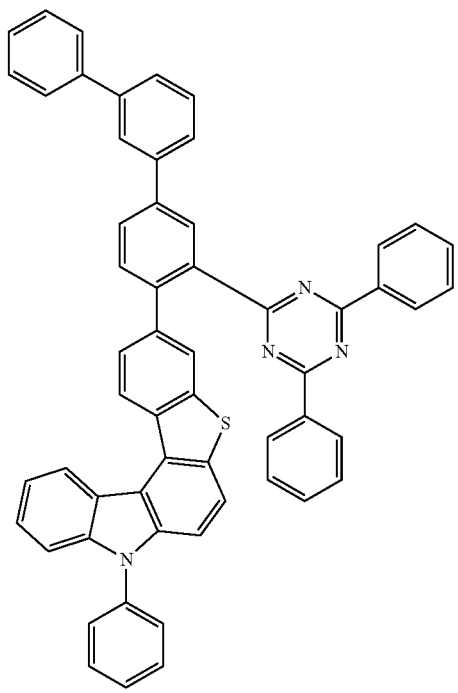
235
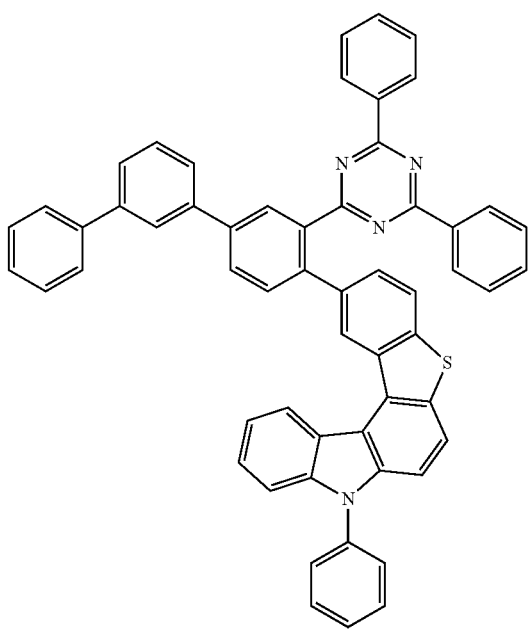

3379
-continued
236
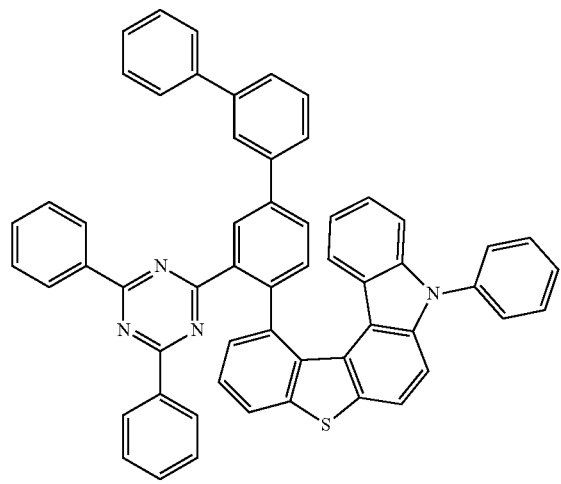
237
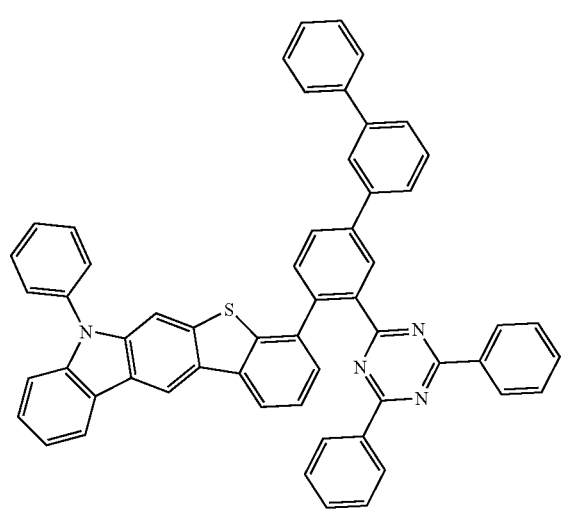
238
3380
-continued
239
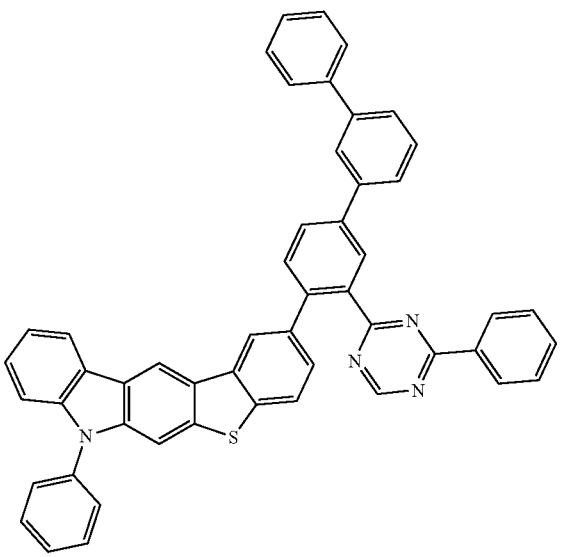
240
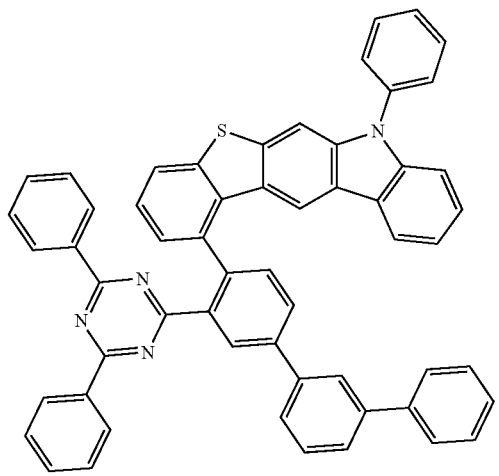
241
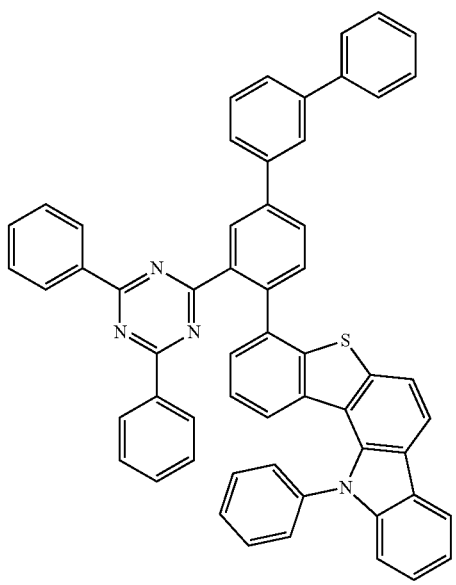

3381
-continued
242
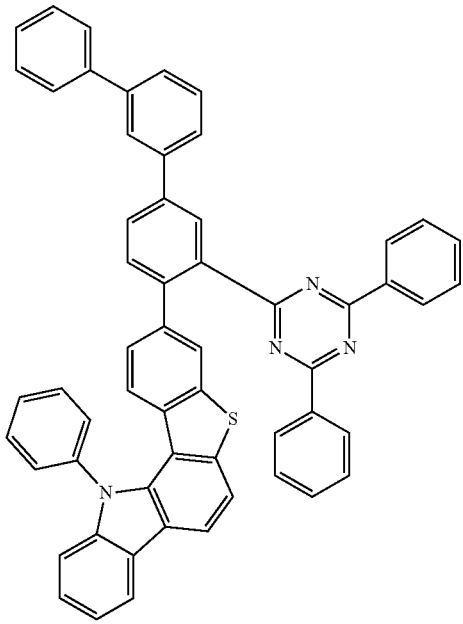
243
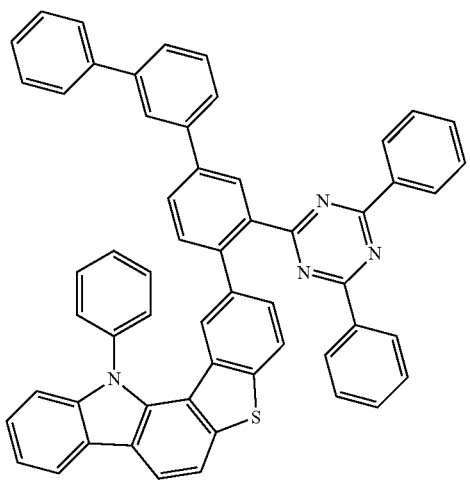
244
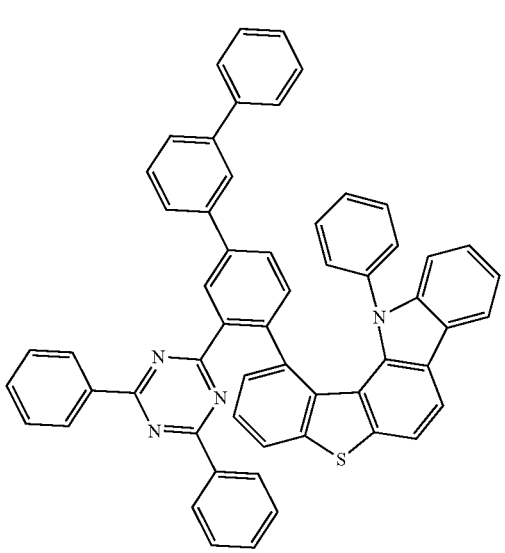
3382
-continued
245
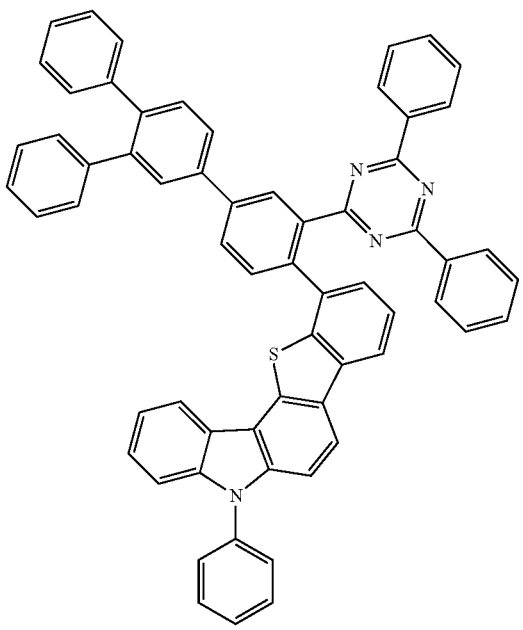
246
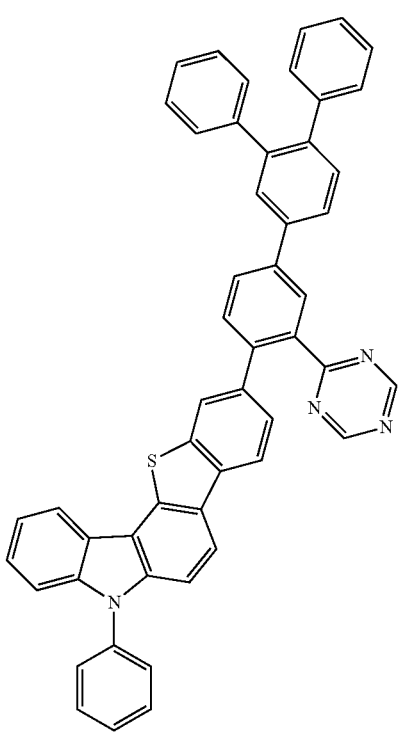

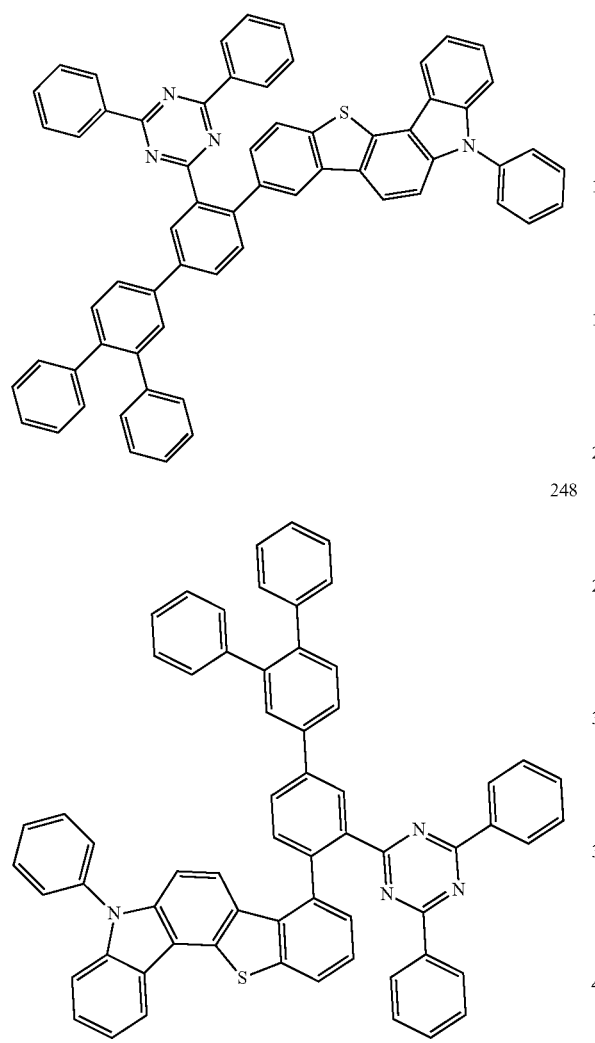
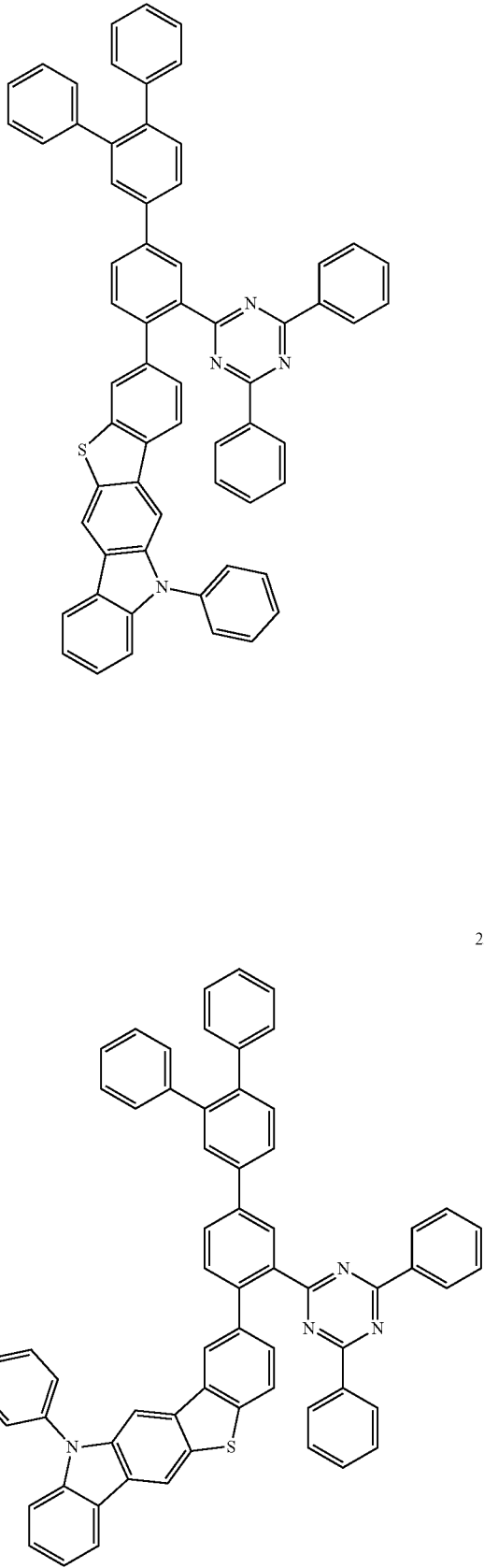

3385
-continued
252
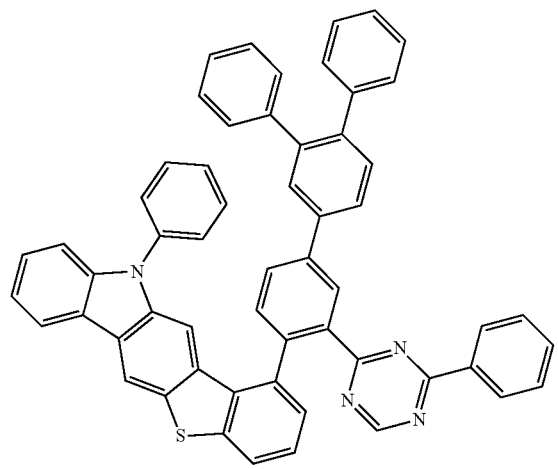
253
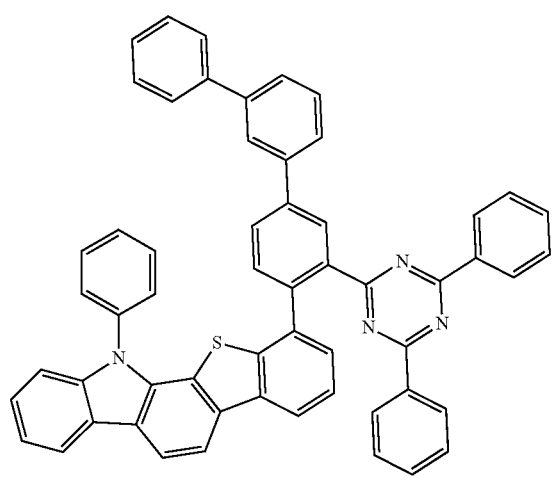
254
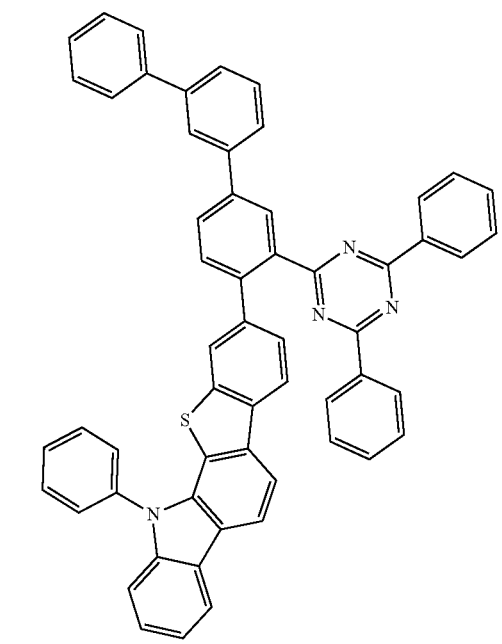
3386
-continued
255
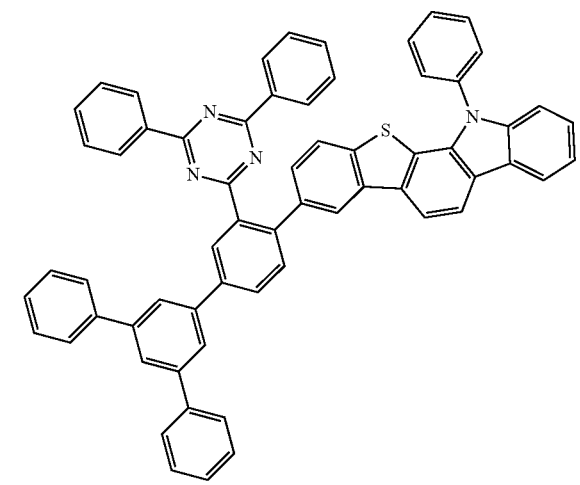
256
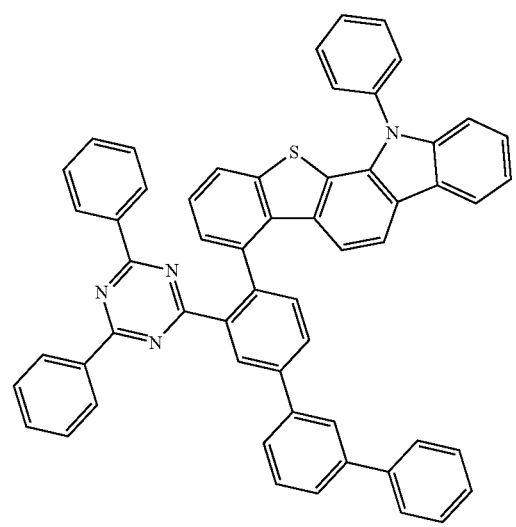
257
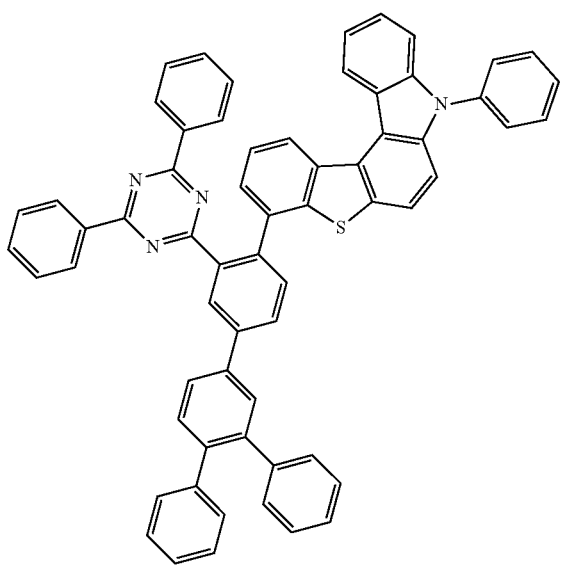

3387
-continued
258
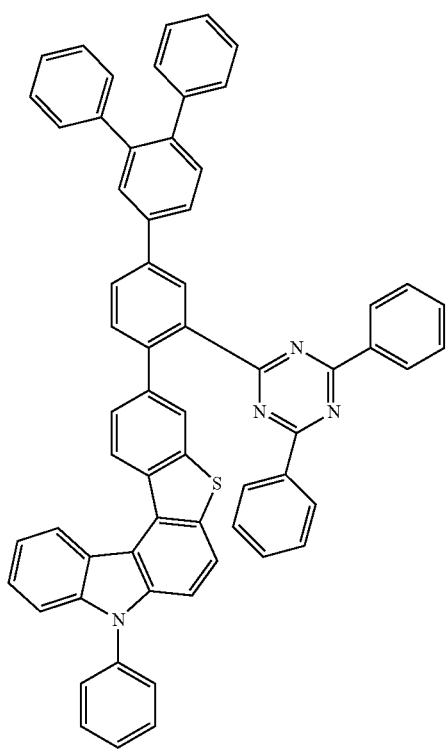
259
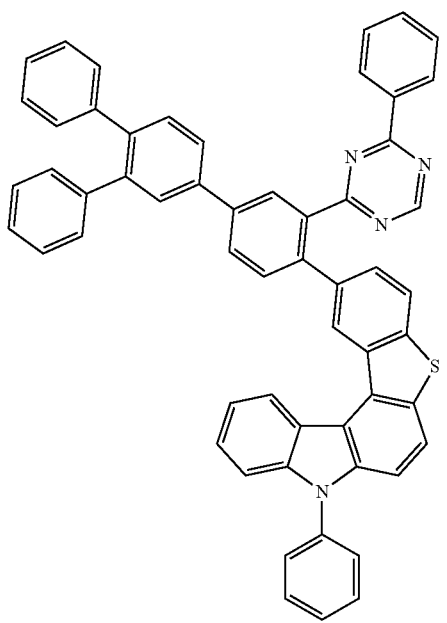
3388
-continued
260
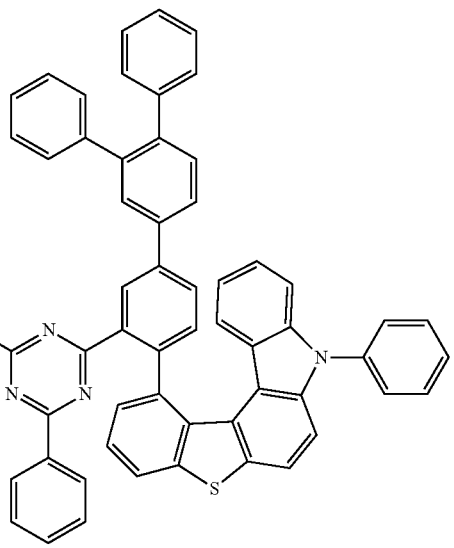
261
262
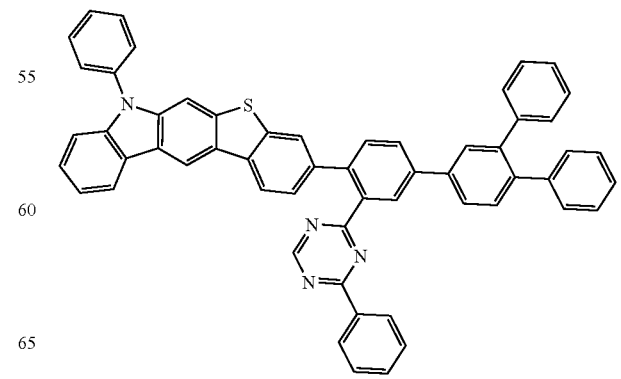

3389
-continued
263
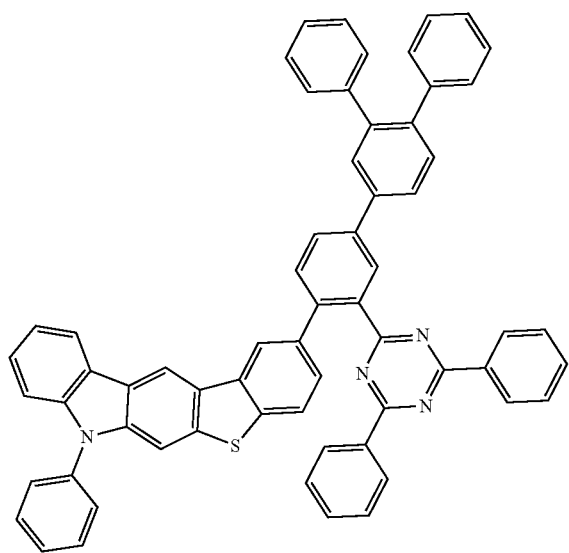
264
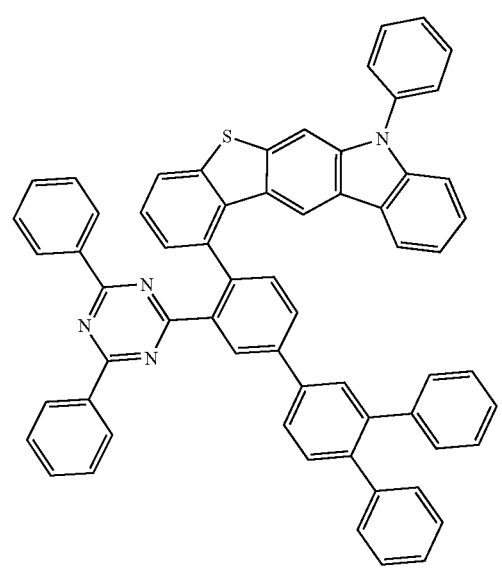
3390
-continued
265
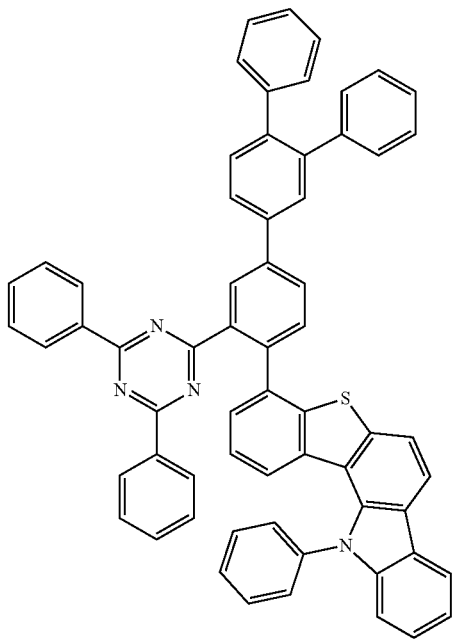
266
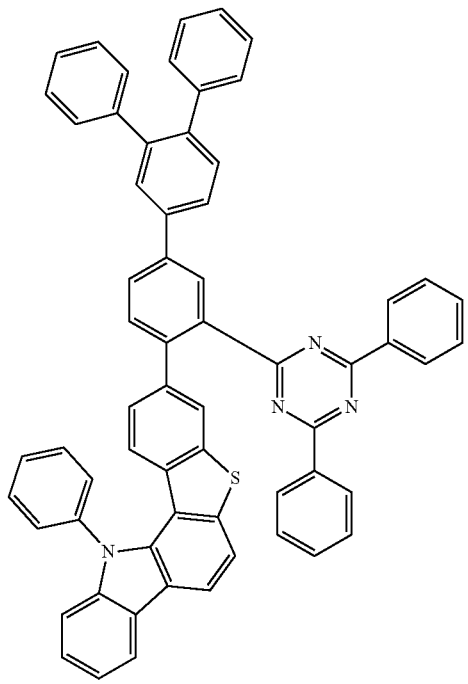

3391
-continued
3392
-continued
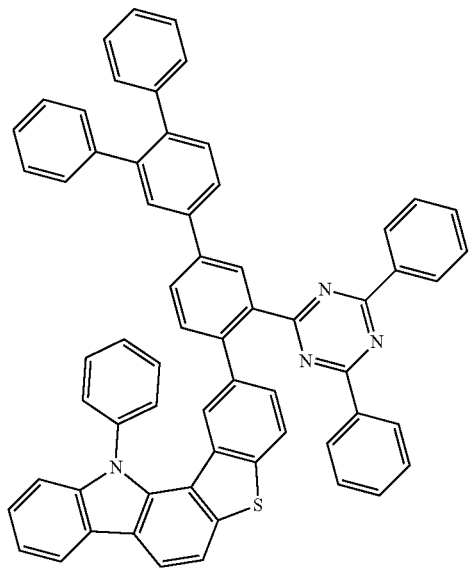
267
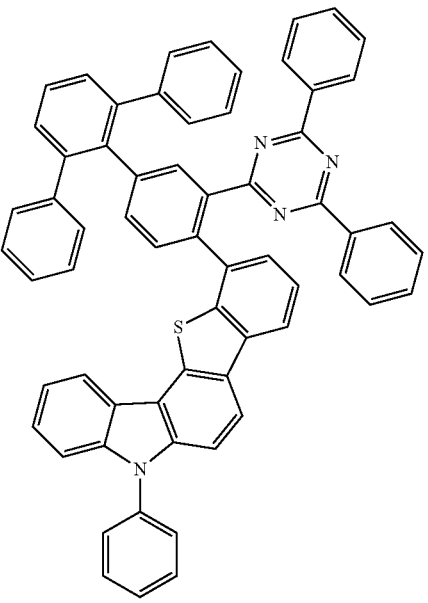
269
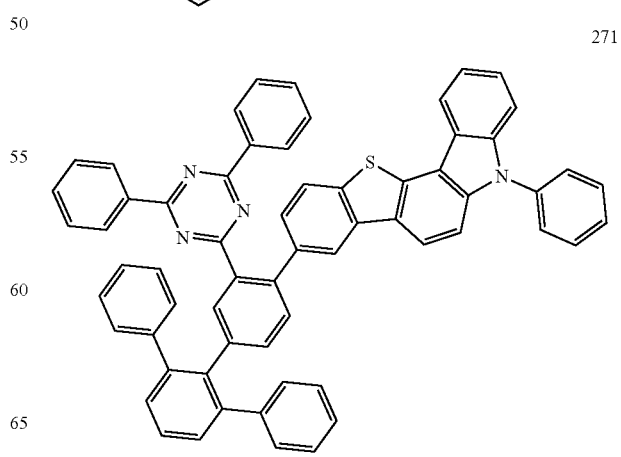
268
270
271

3393
-continued
272
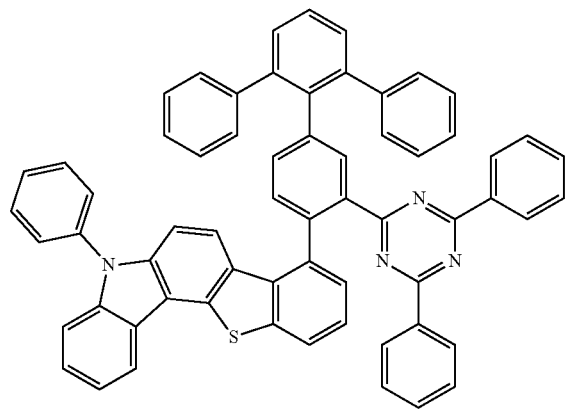
273
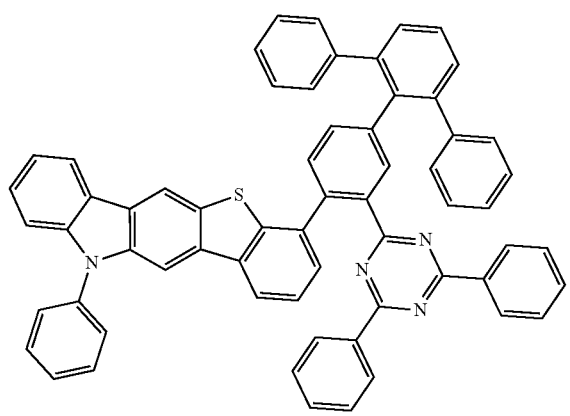
274
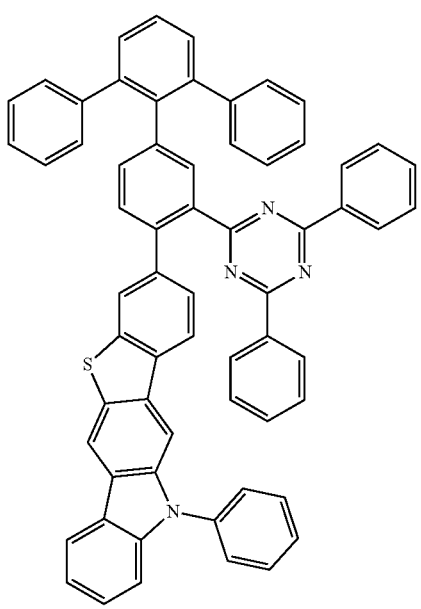
3394
-continued
275
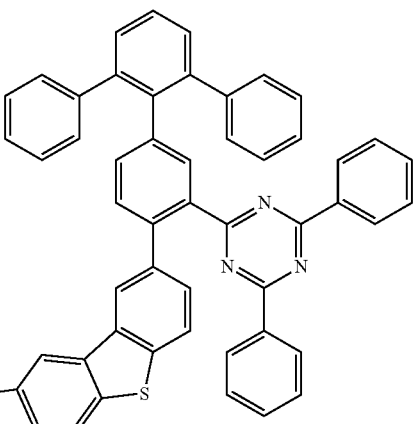
276
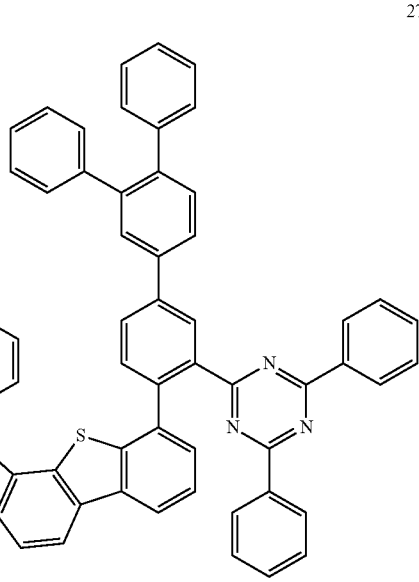
277

278
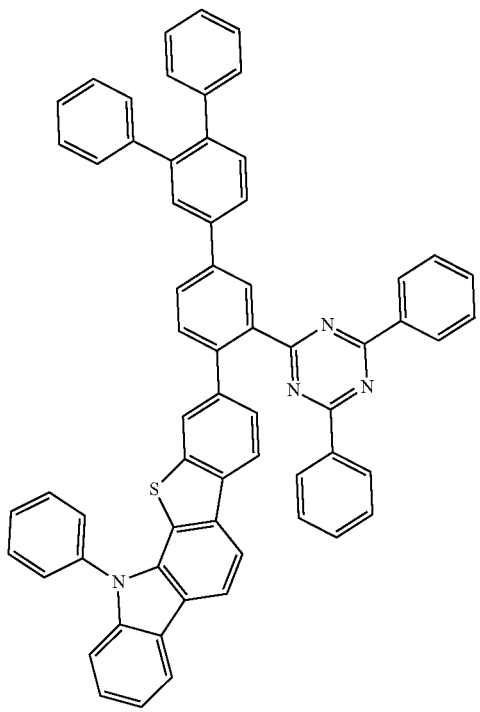
279
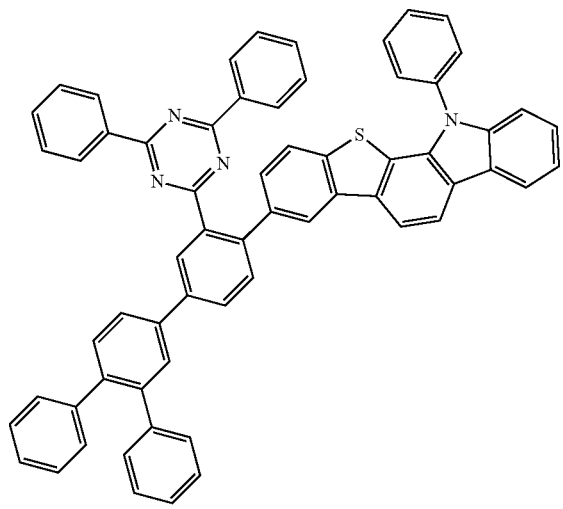
280
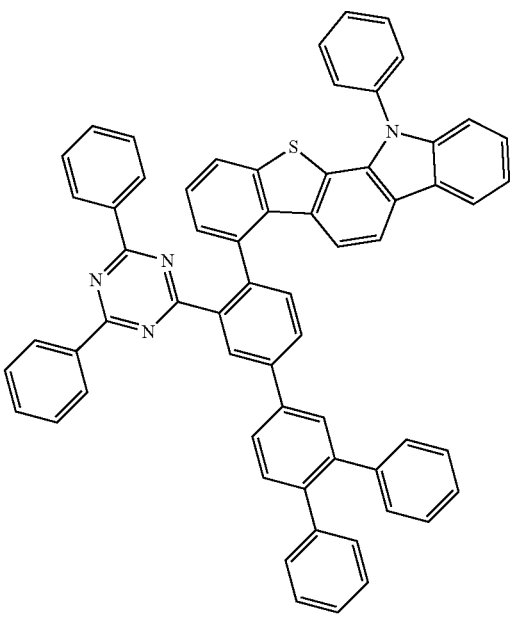
281
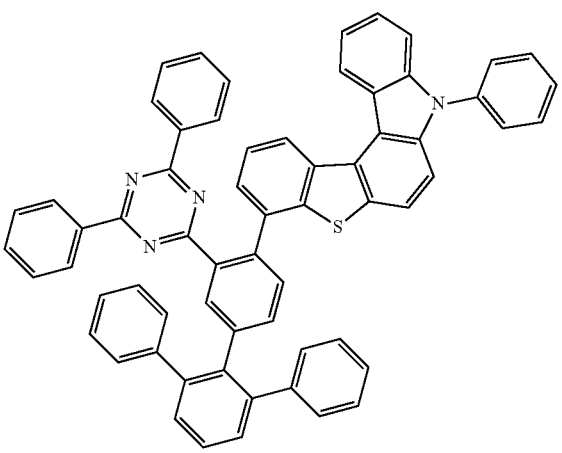

3397
-continued
282
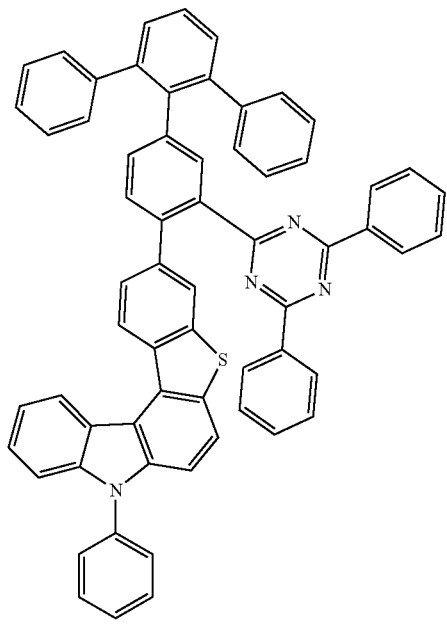
283
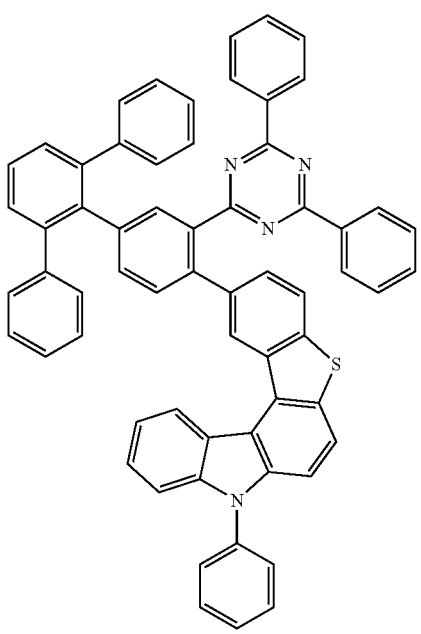
3398
-continued
284
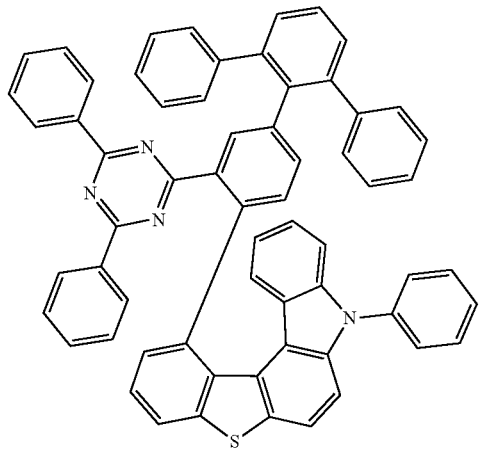
285
286
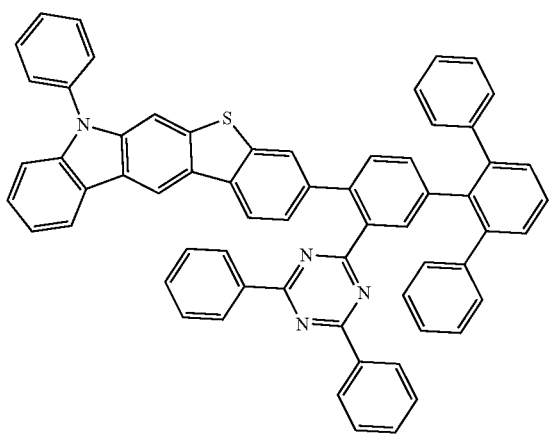

287
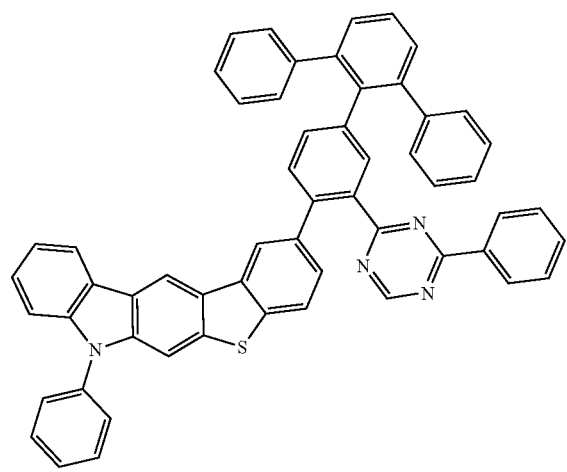
288
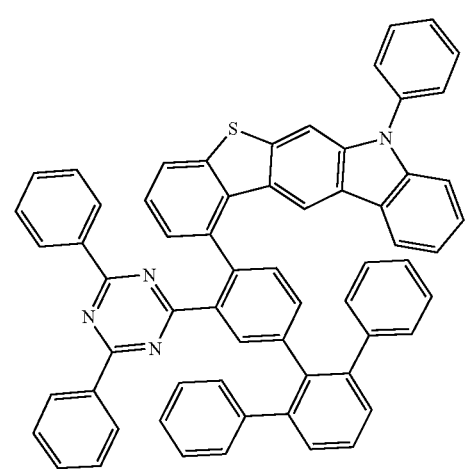
289
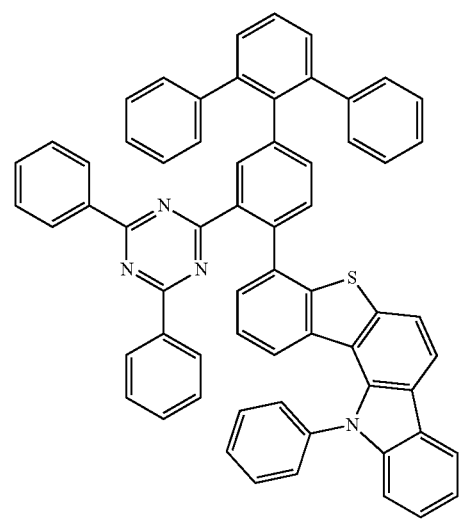
290
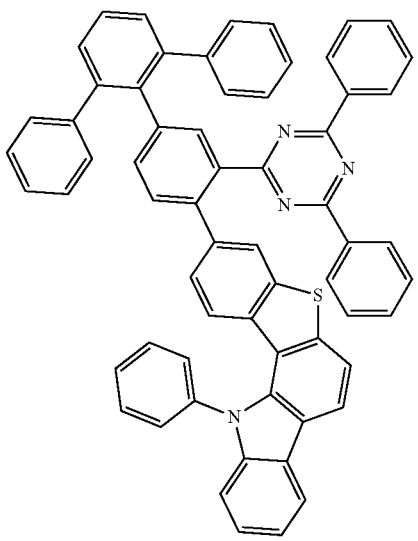
291
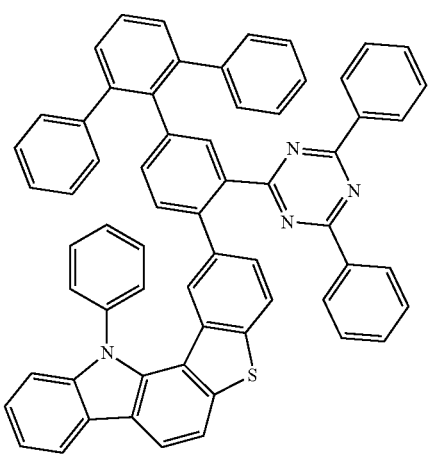
292
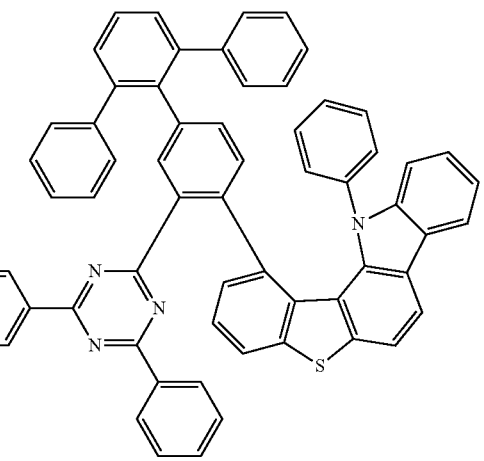

-continued
293
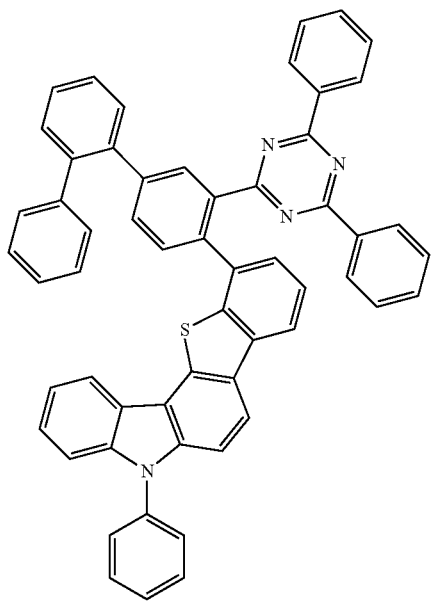
294
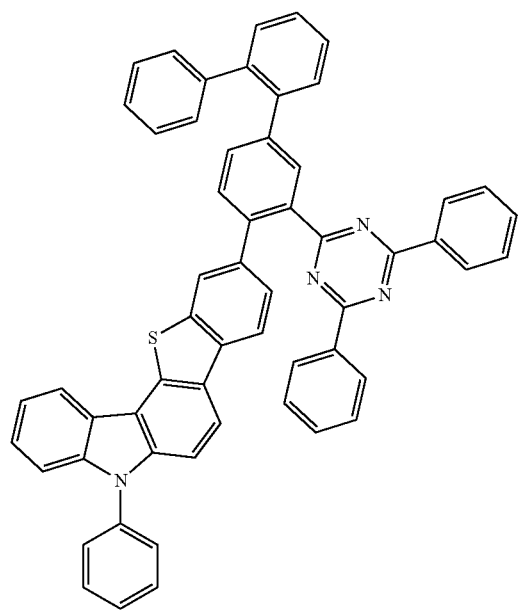
295
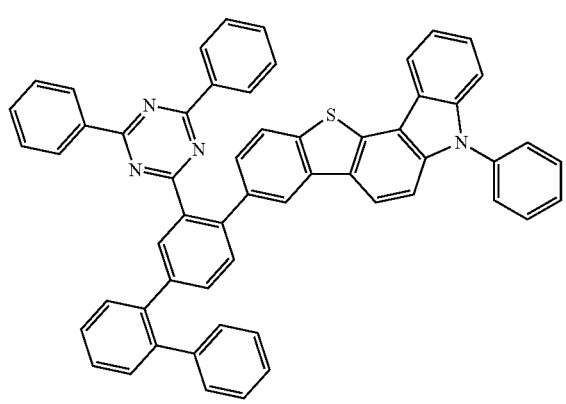
-continued
296
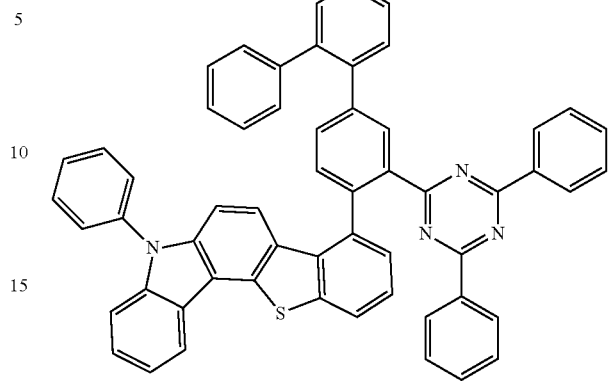
297
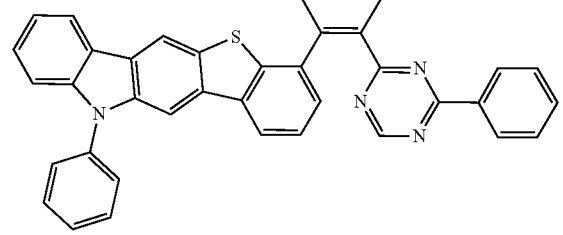
298
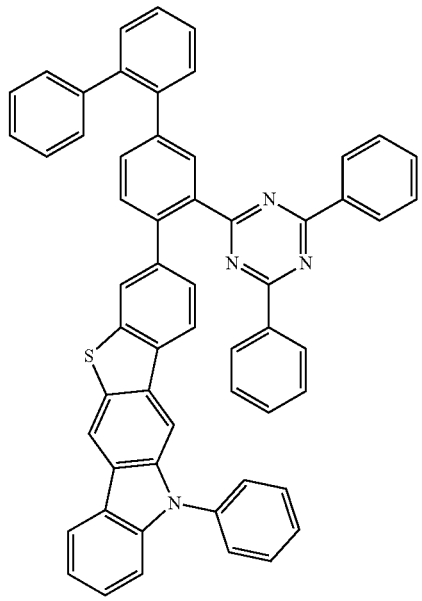

3403
-continued
299
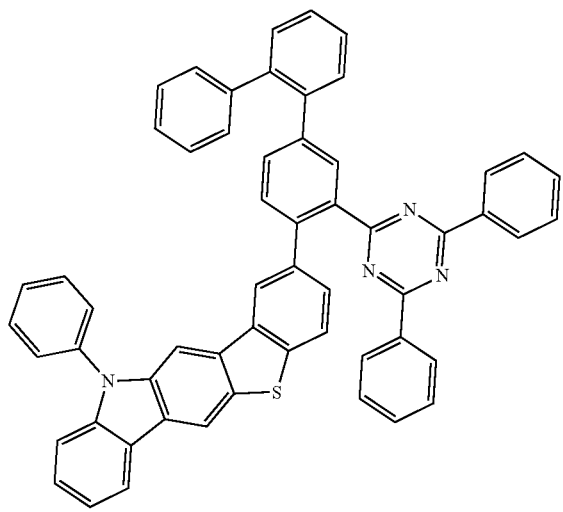
300
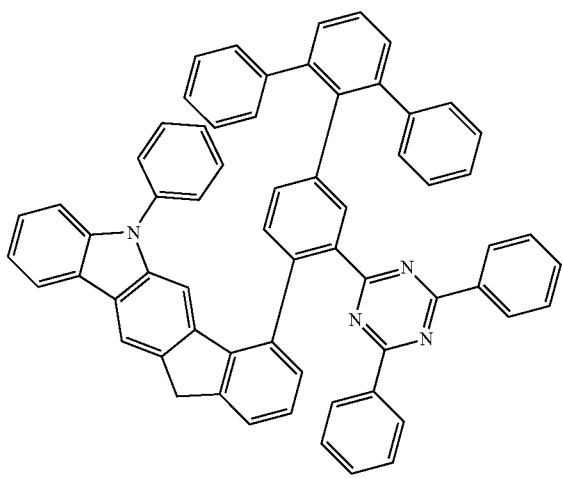
301
3404
-continued
302
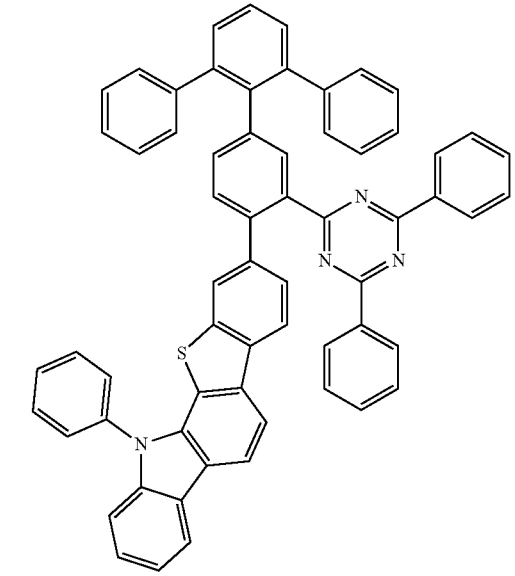
303
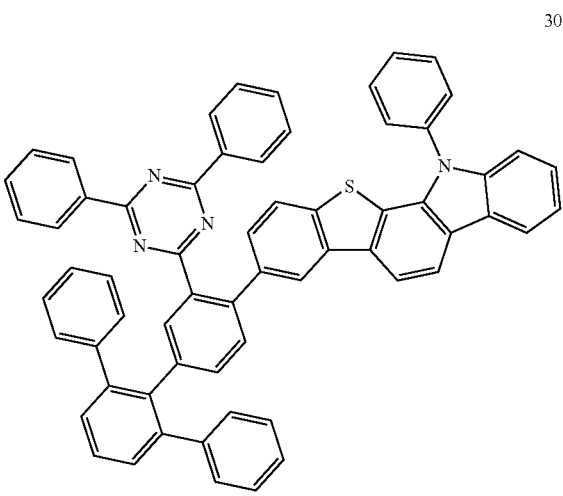
304
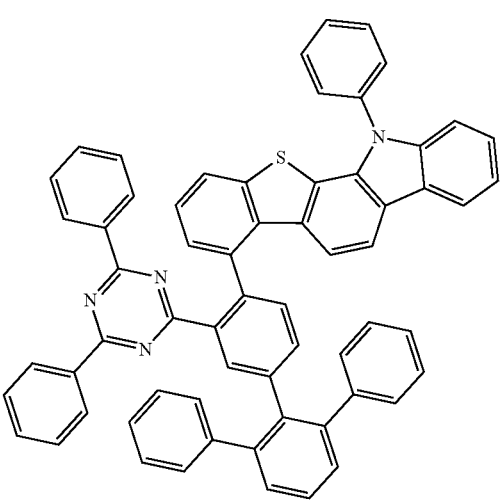

3405
-continued
305
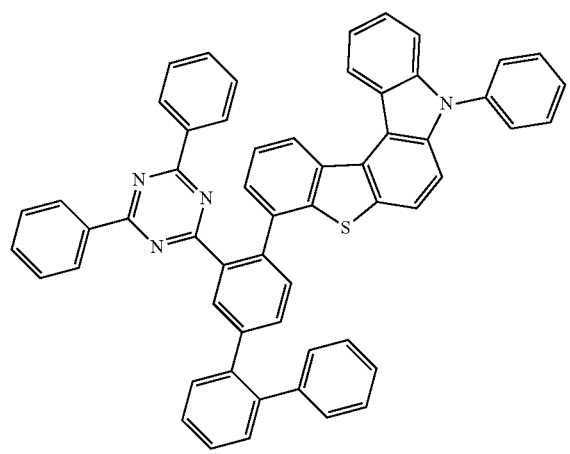
306
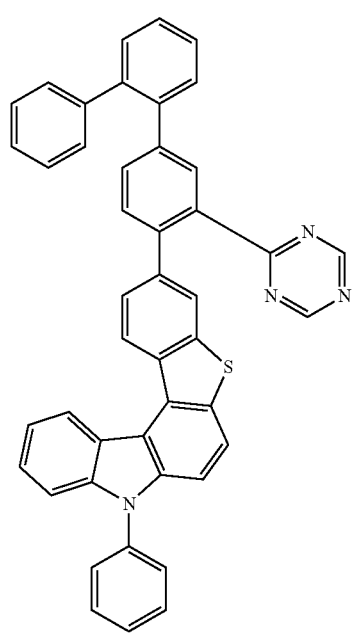
3406
-continued
307
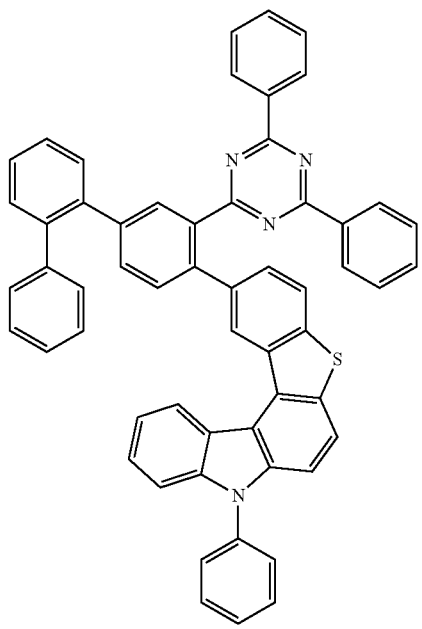
308
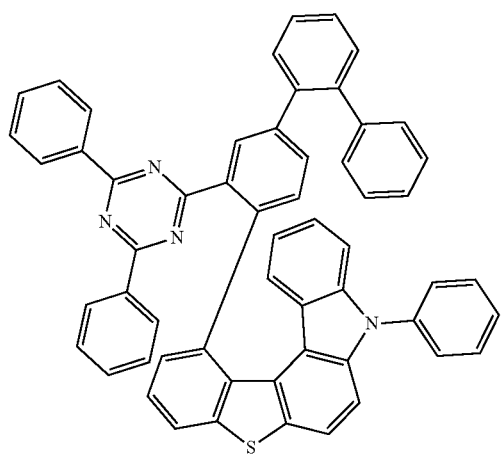
309
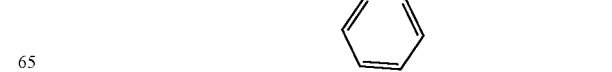

3407
-continued
310
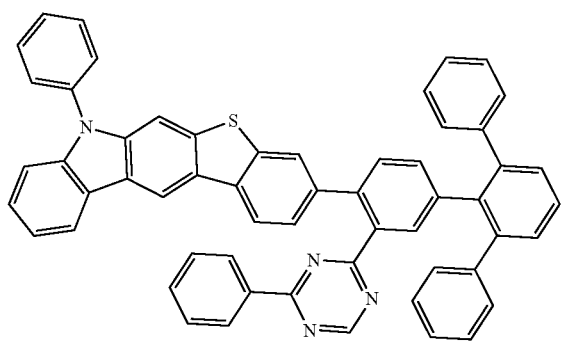
311
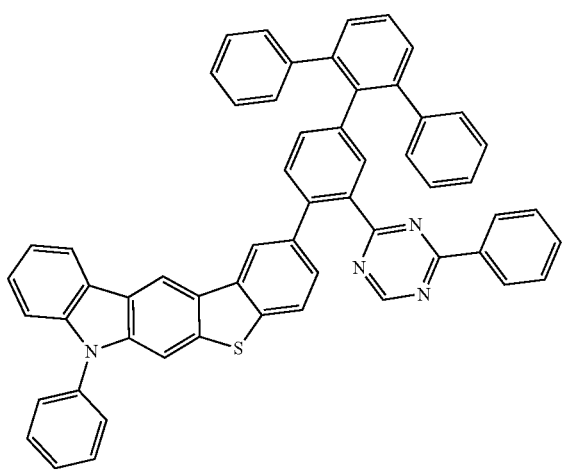
312
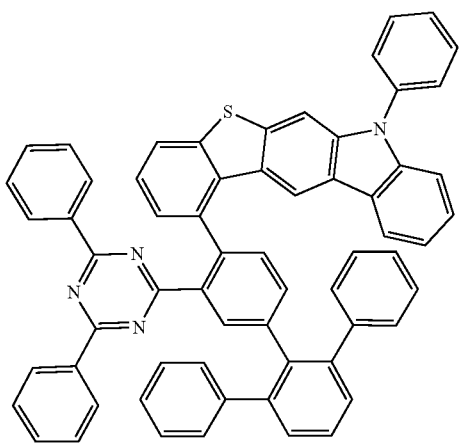
3408
-continued
313
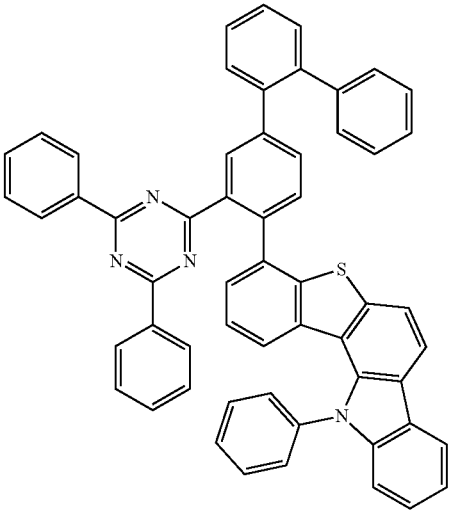
314
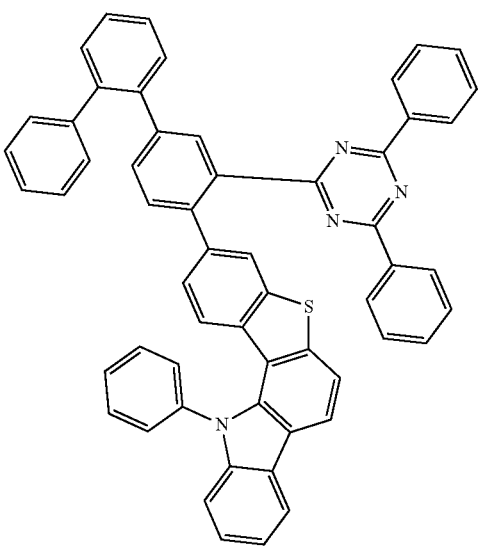
315
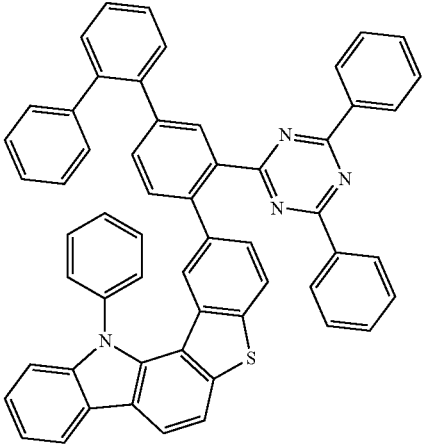

3409
-continued
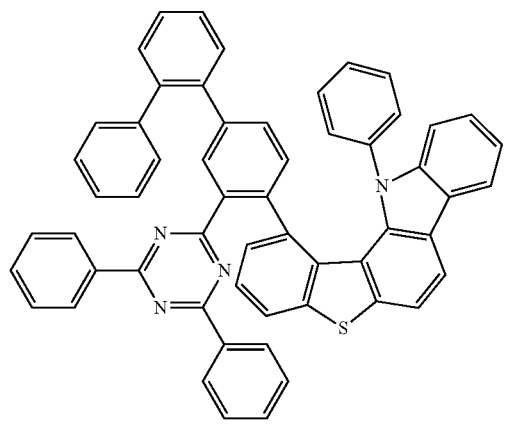
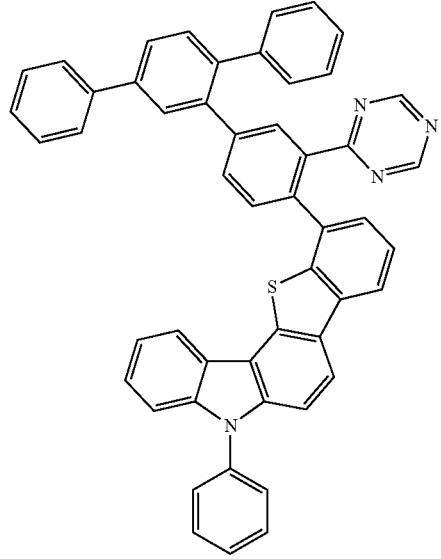
3410
-continued
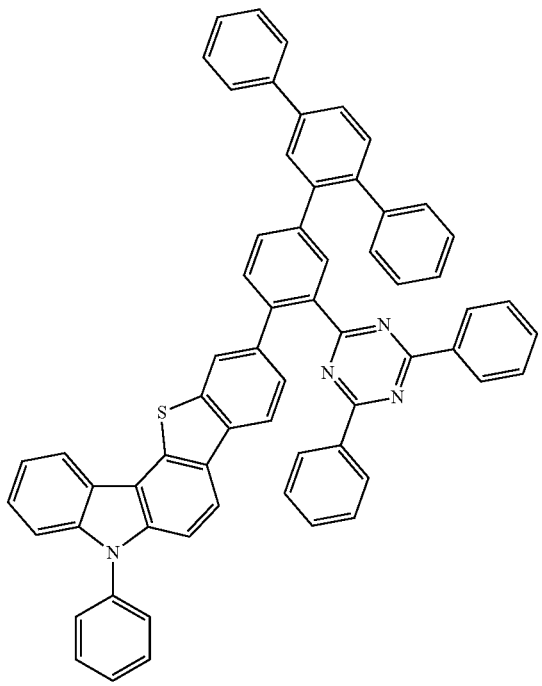
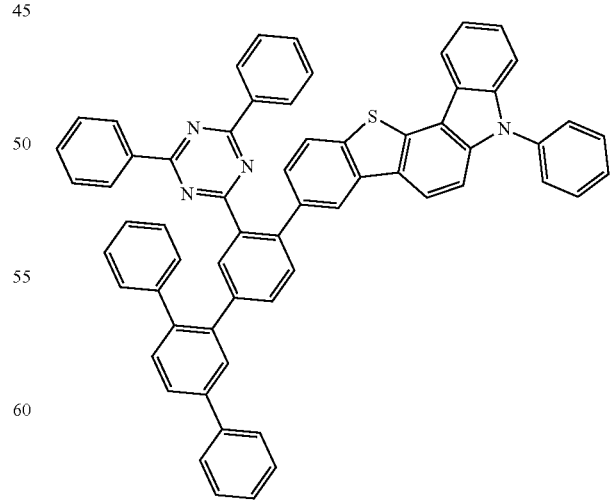

-continued
320
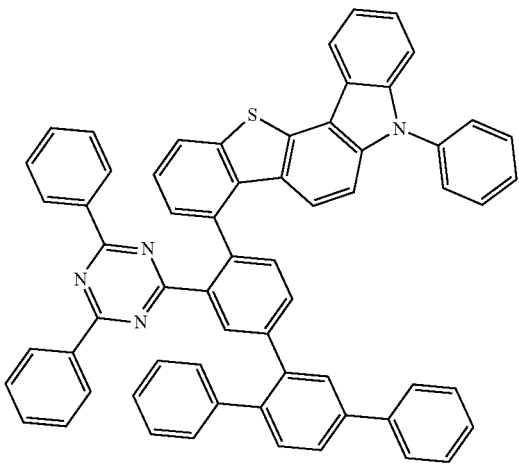
321
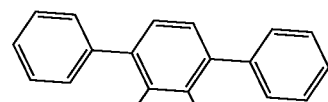
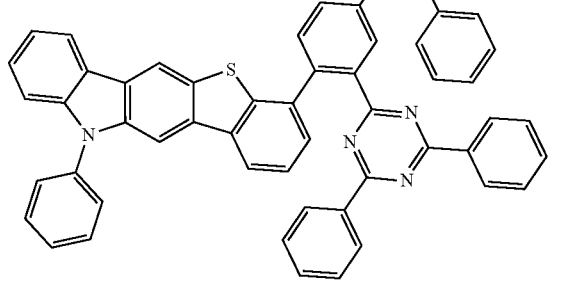
322
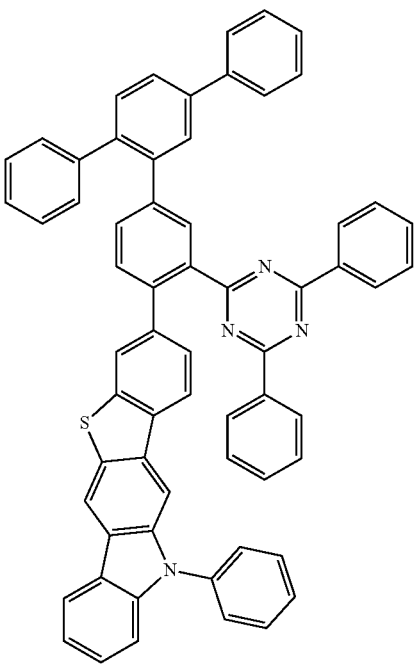
-continued
323
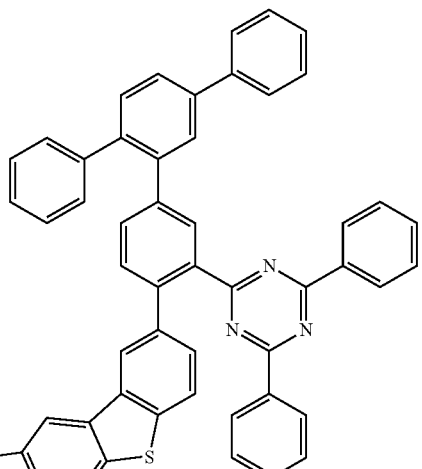
324
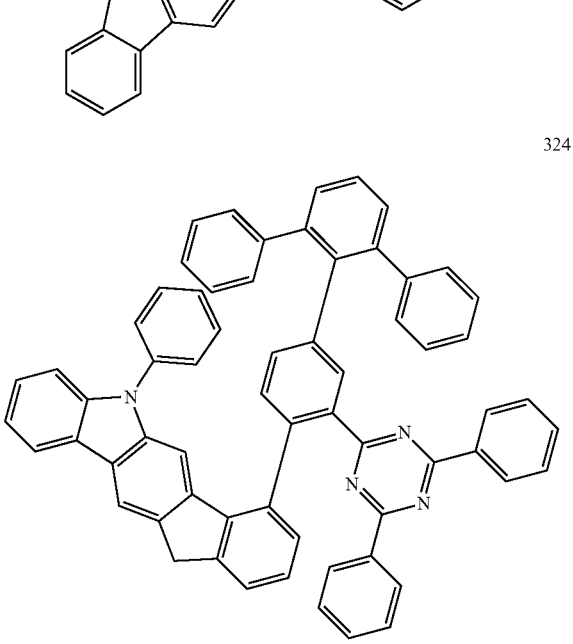
325
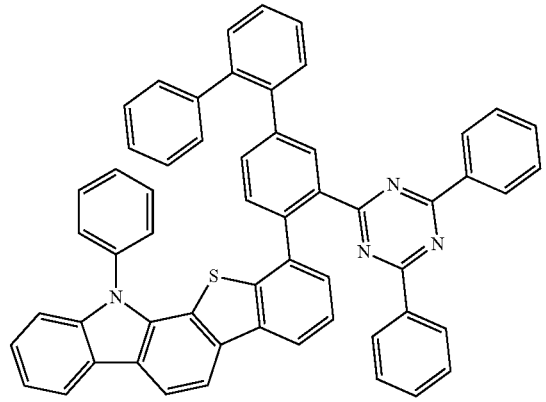

326
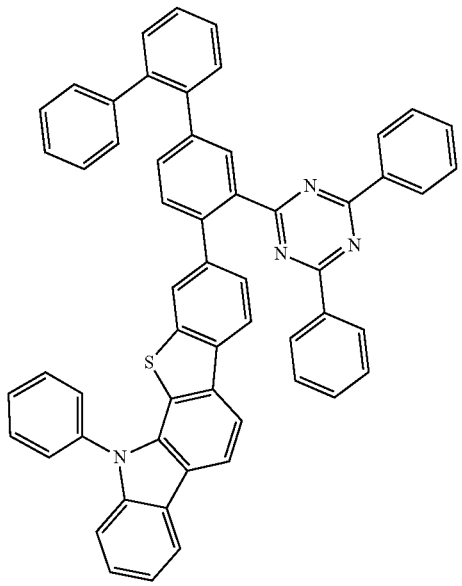
327
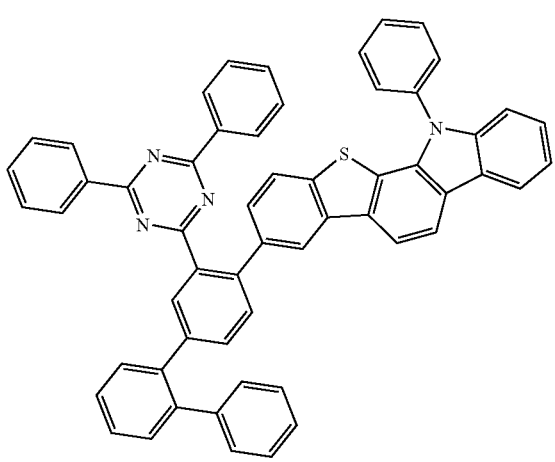
328
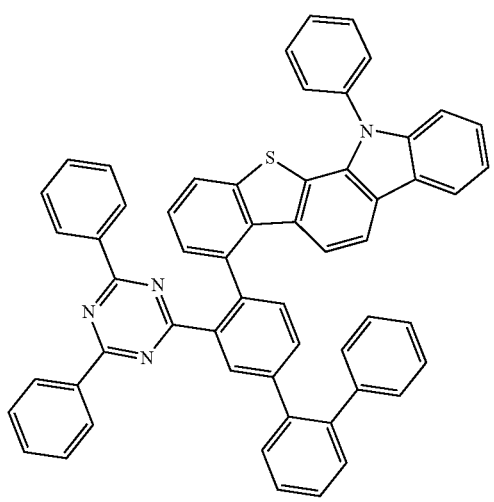
329
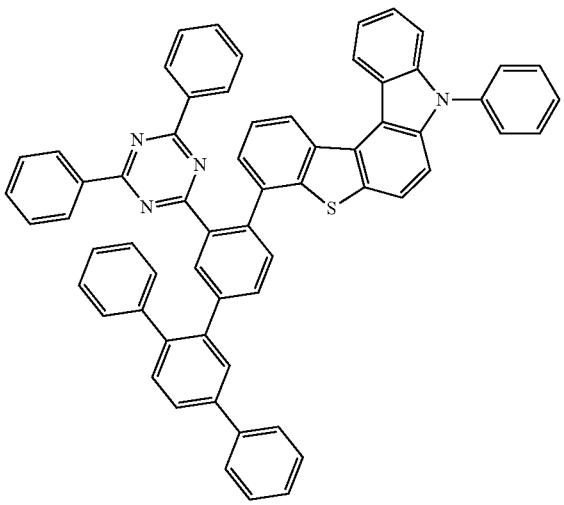
330
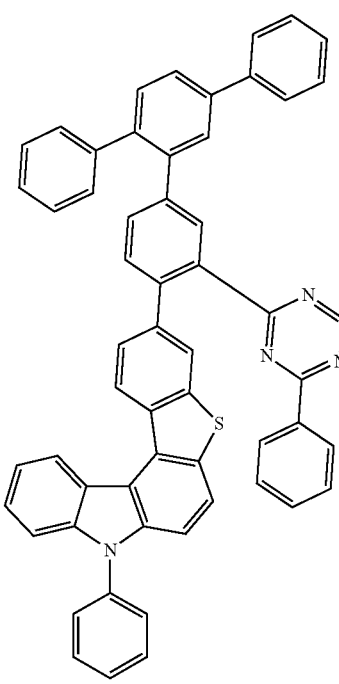

3415
-continued
331
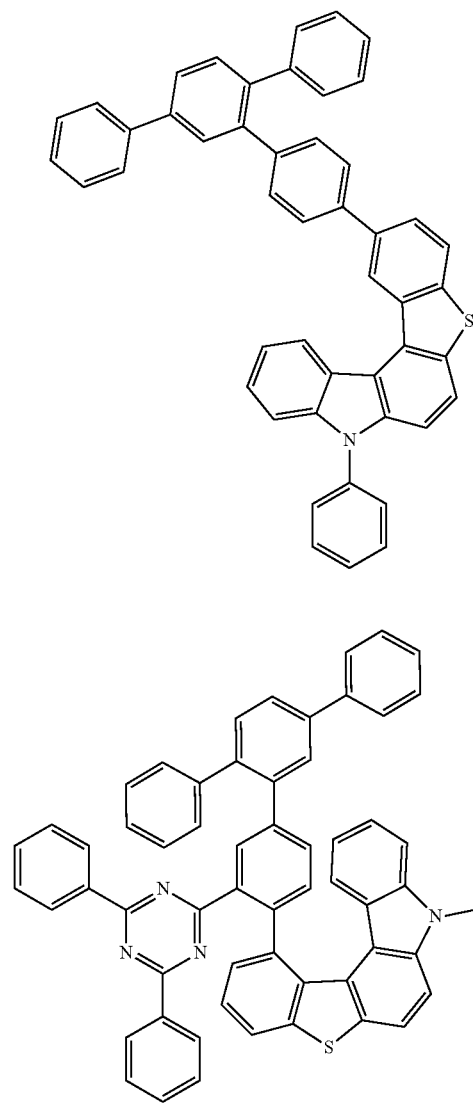
332
333
3416
-continued
334
335
336
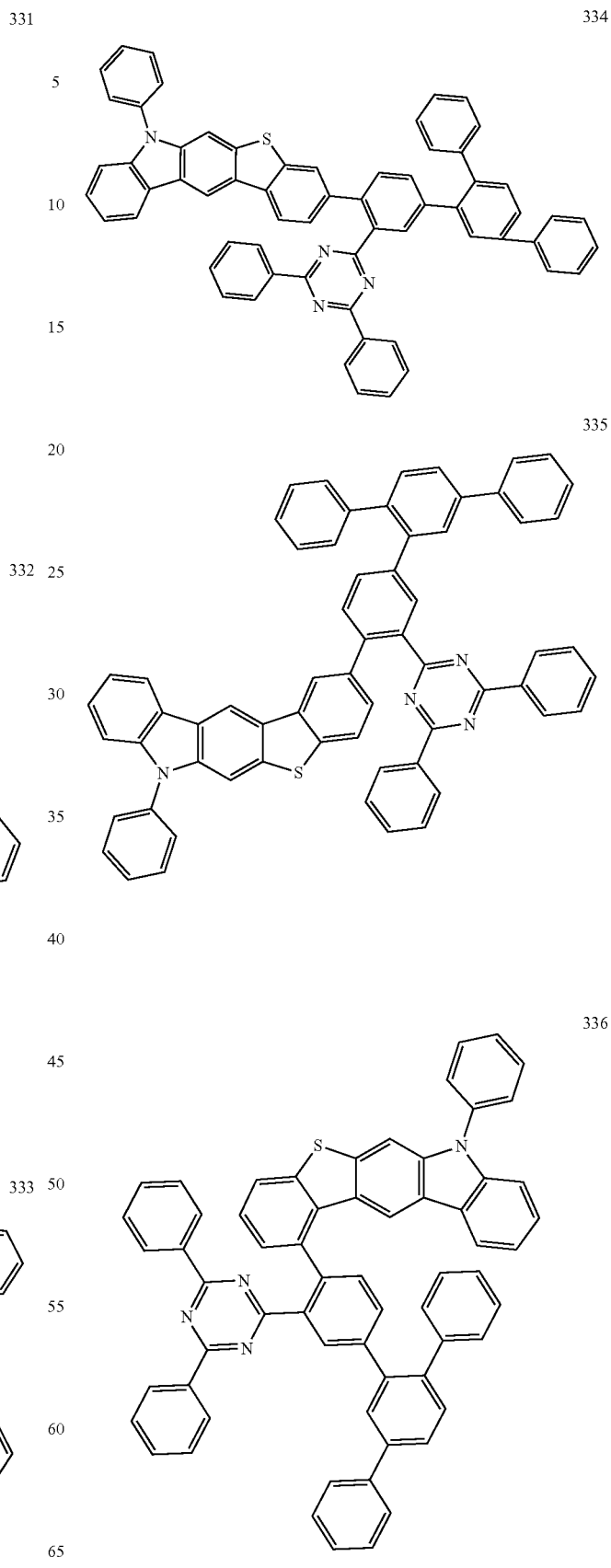

3417
-continued
337
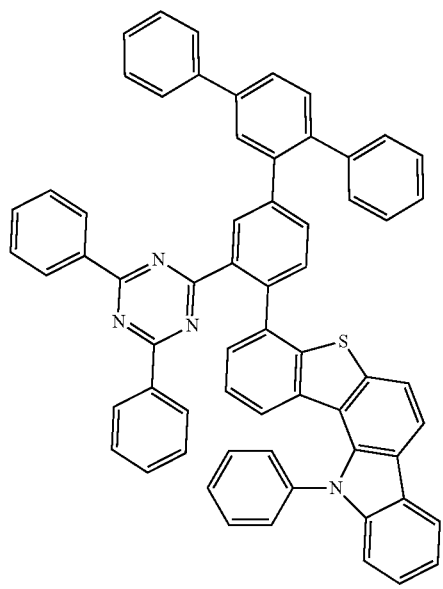
338
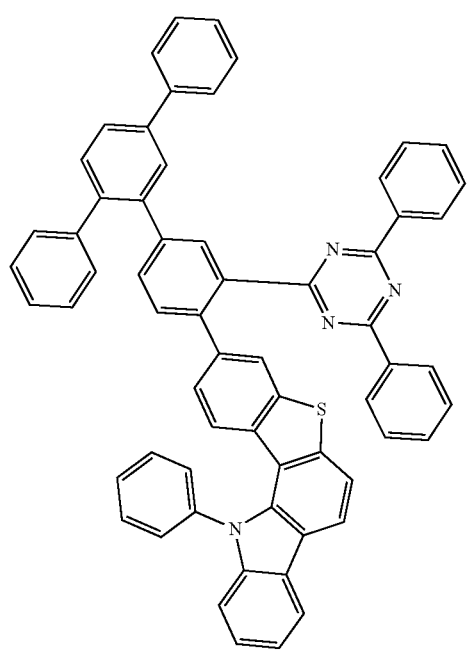
3418
-continued
339
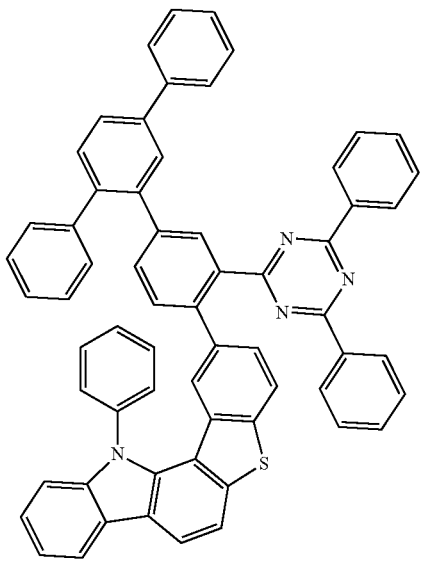
340
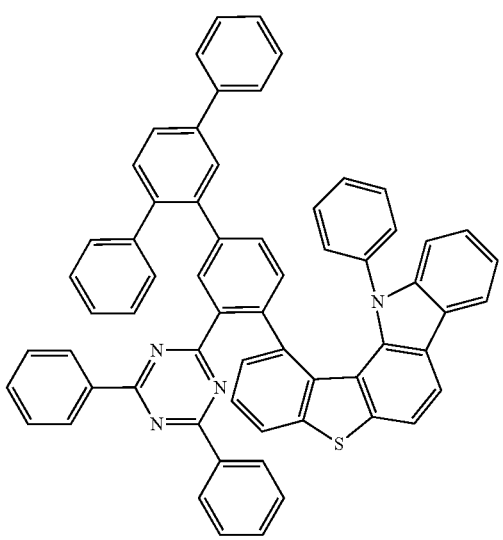
341
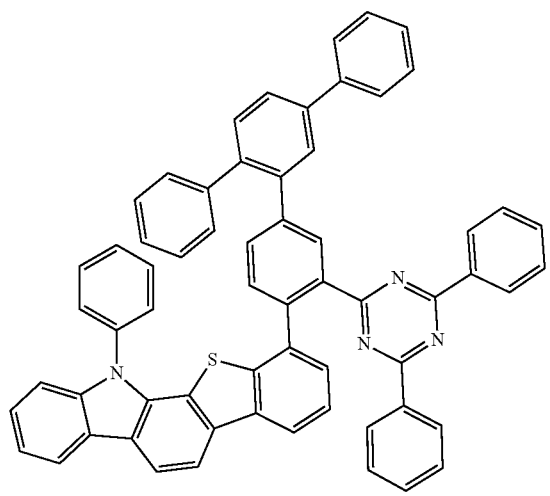

3419
-continued
342
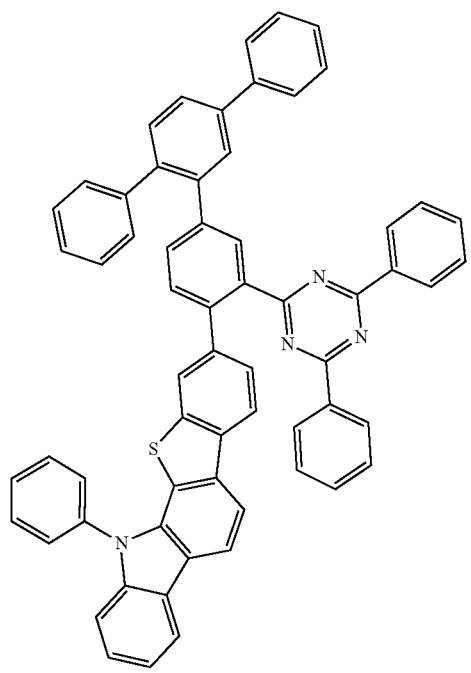
343
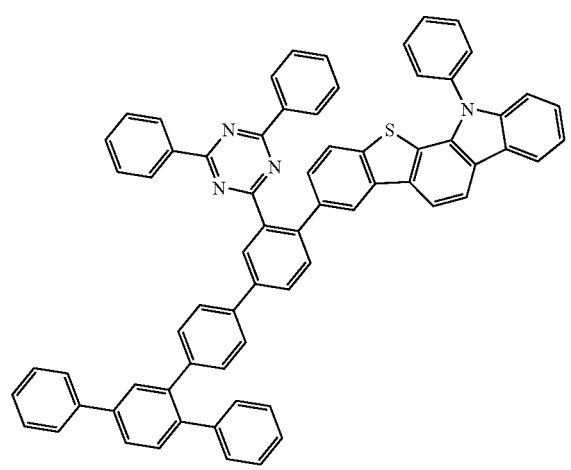
3420
-continued
344
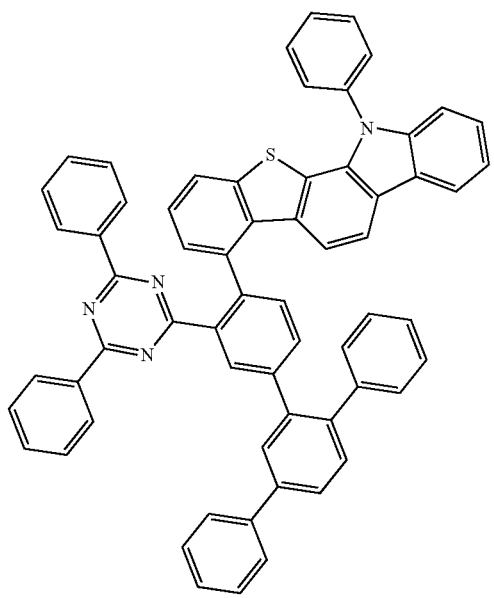
345
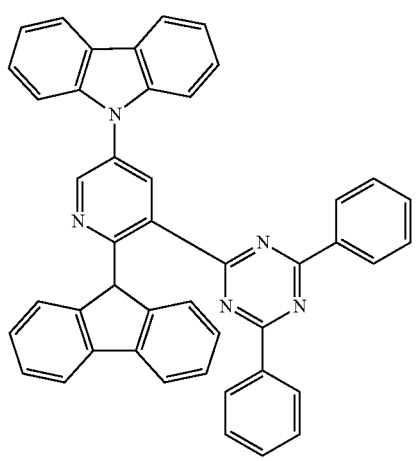
346
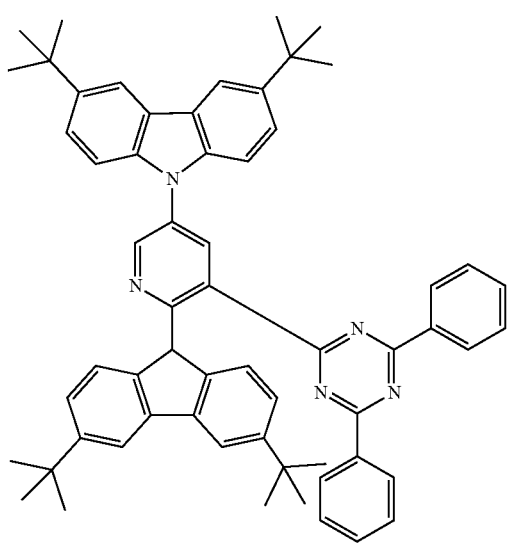

3421
-continued
347
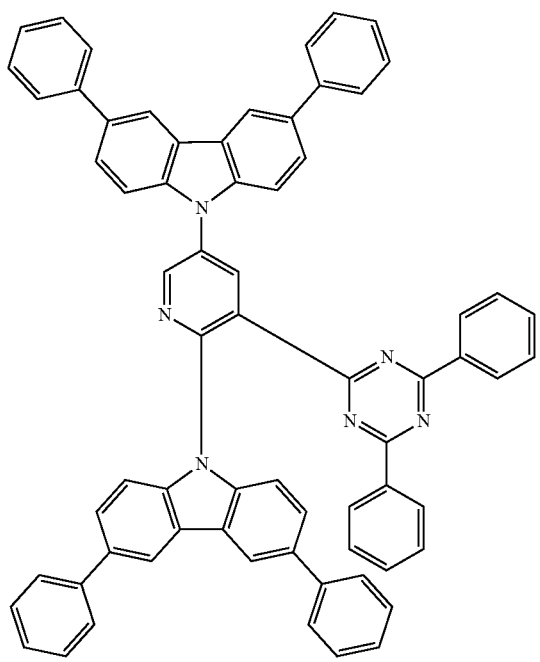
348
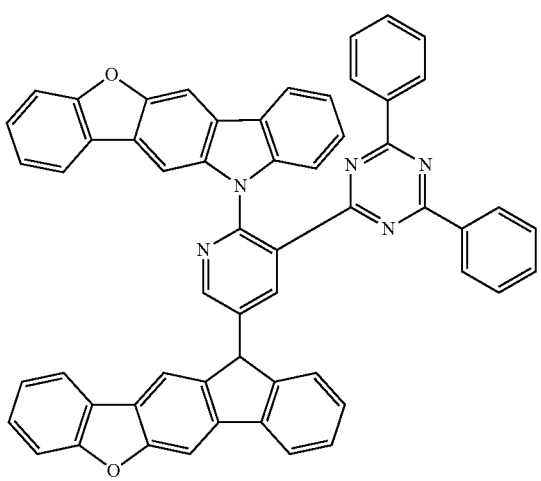
349
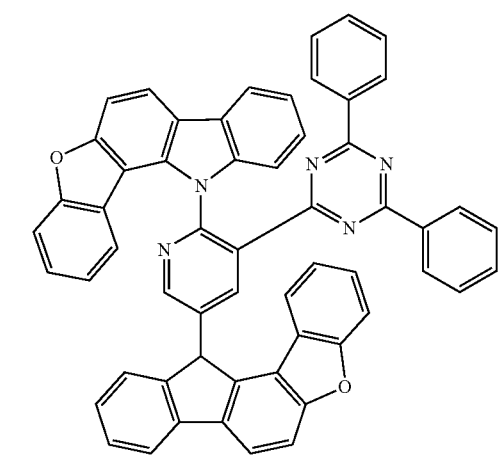
3422
-continued
350
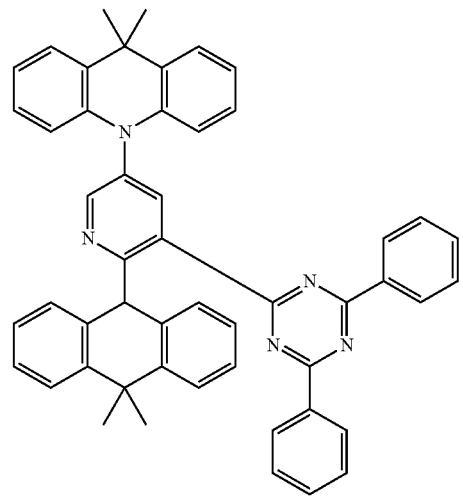
351
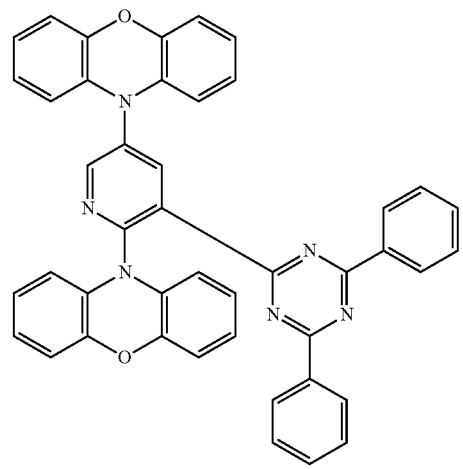
352
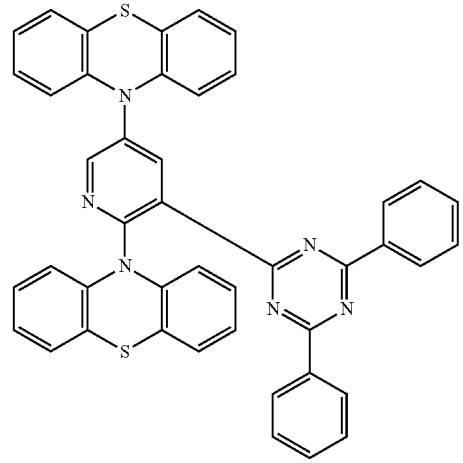

3423
-continued
353
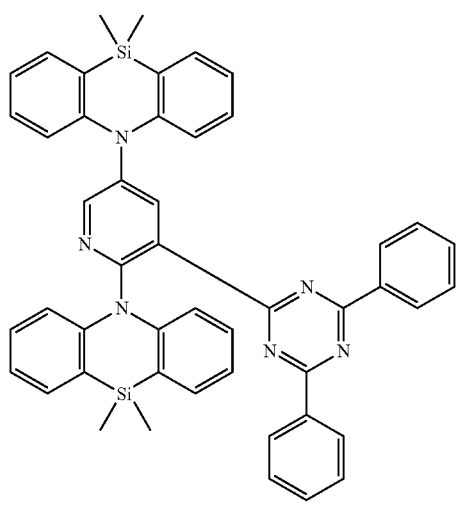
354
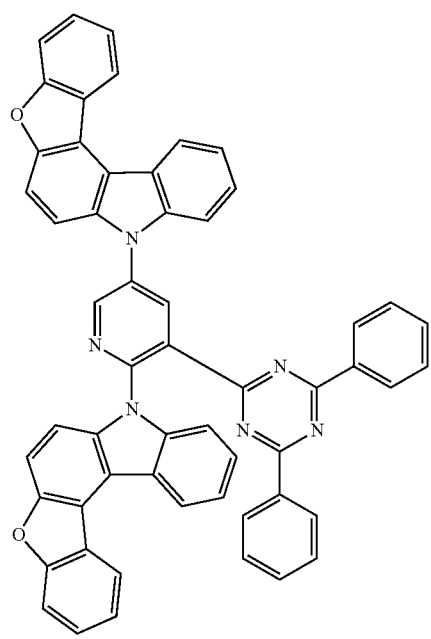
3424
-continued
355
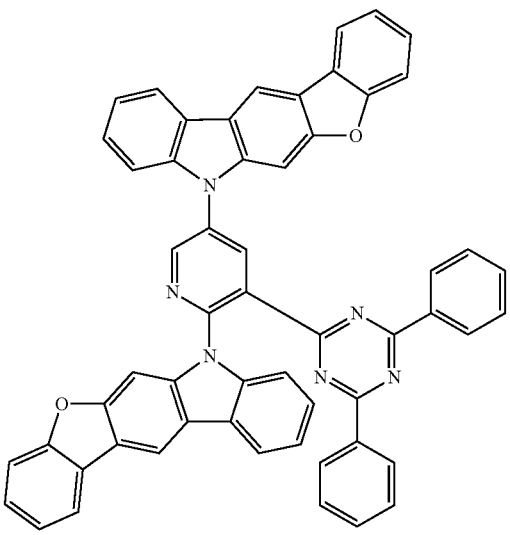
356
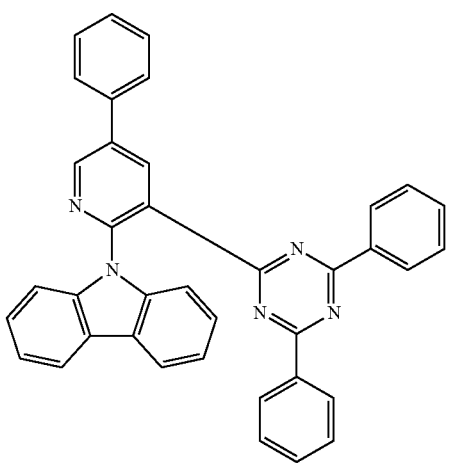
357
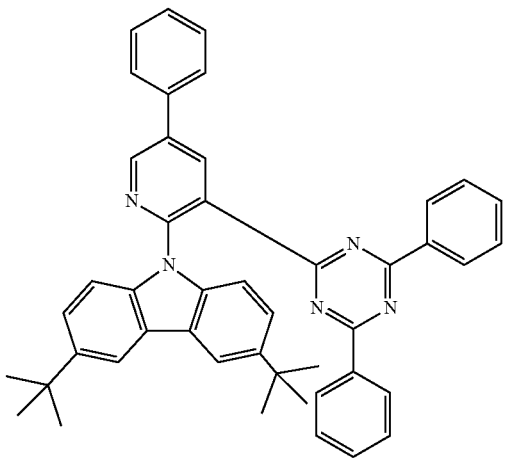

3425 -continued
358
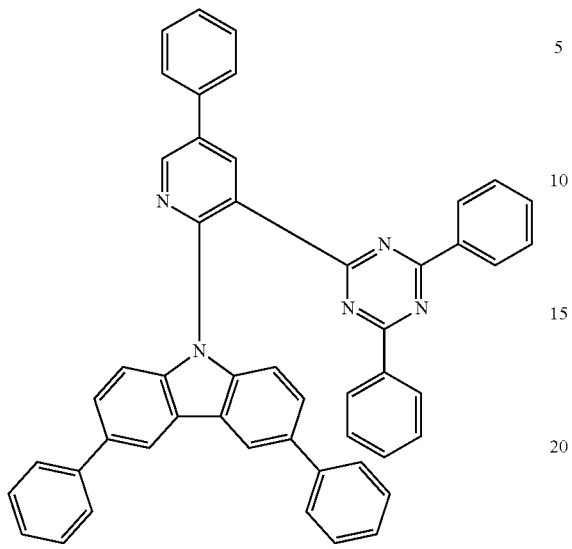
359
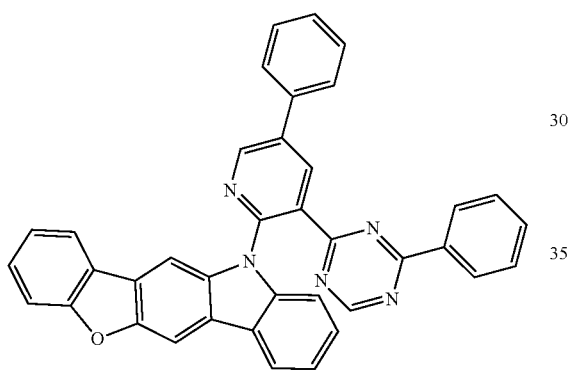
360
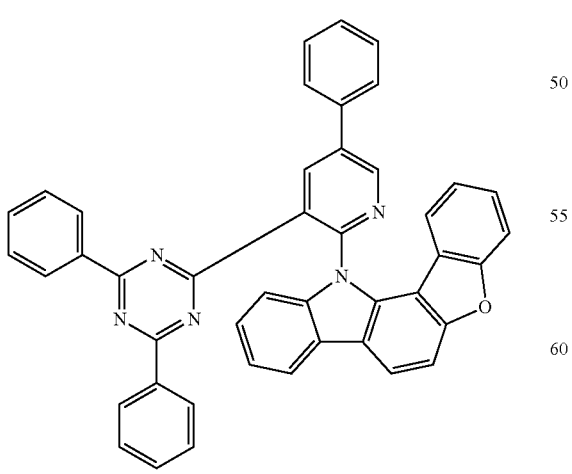
3426 -continued
361
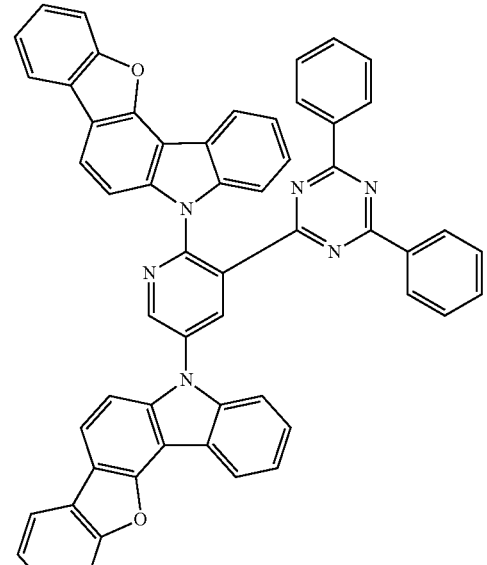
362
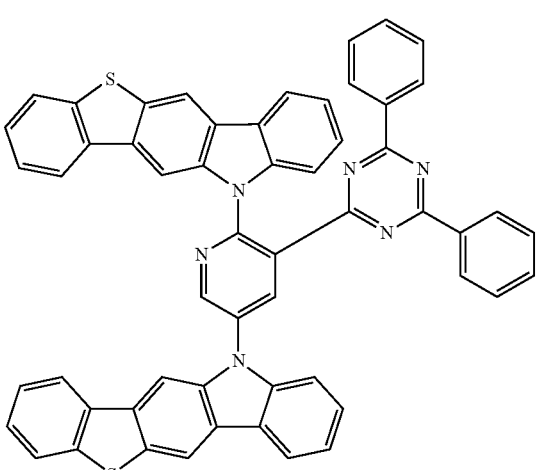
363
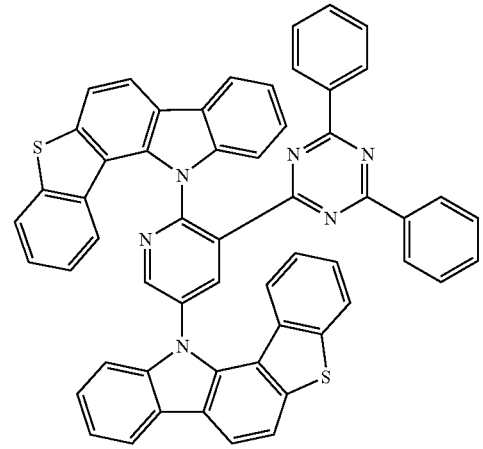

3427
-continued
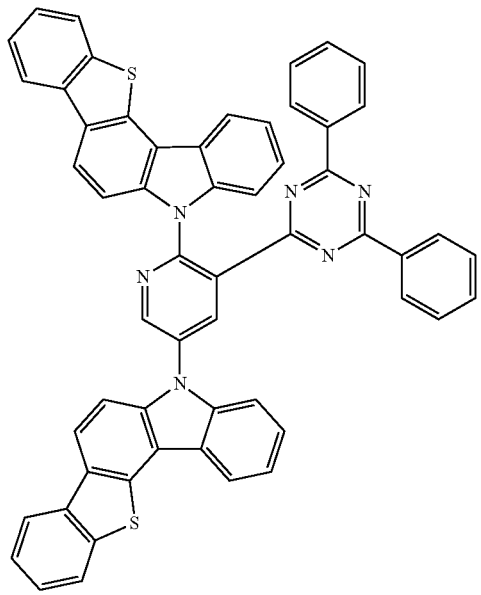
364
3428
-continued
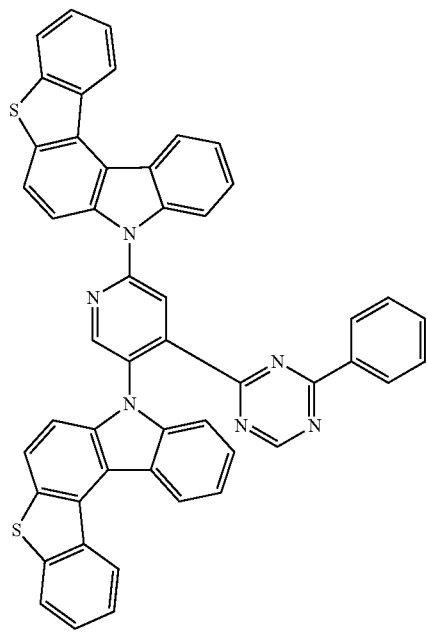
366
365
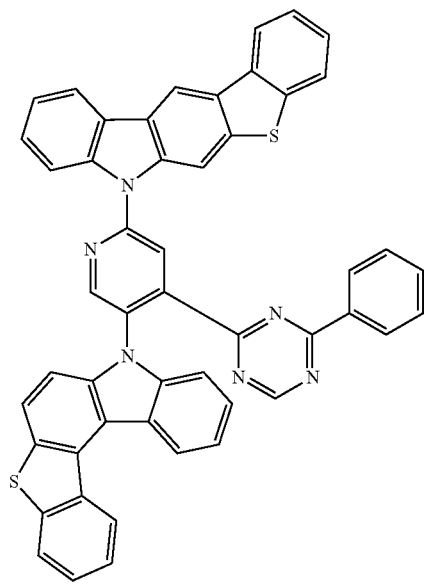
367

3429
-continued
368
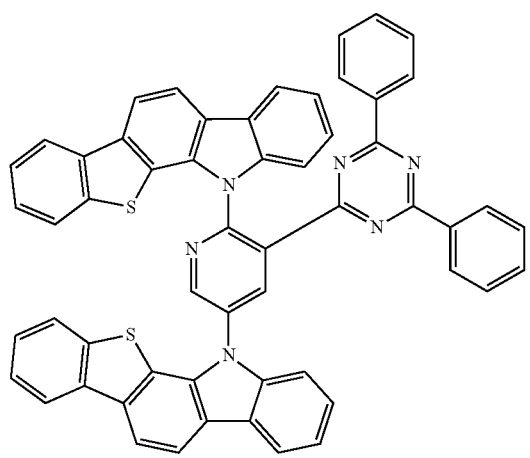
369
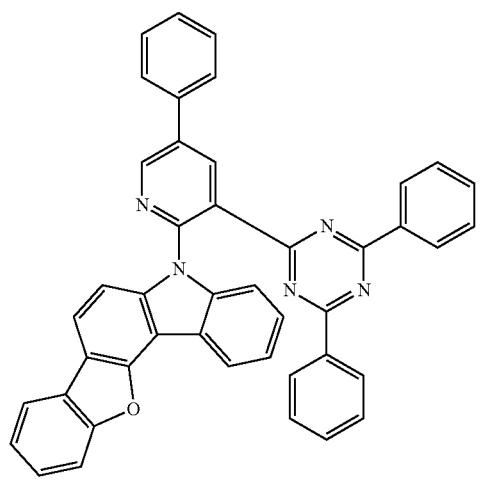
370
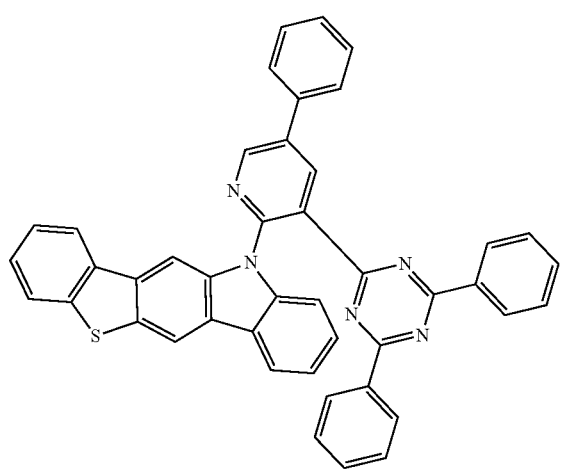
3430
-continued
371
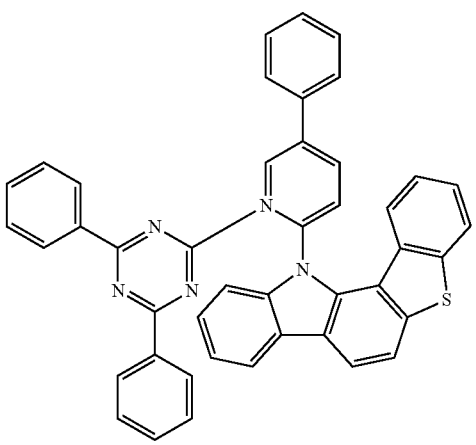
372
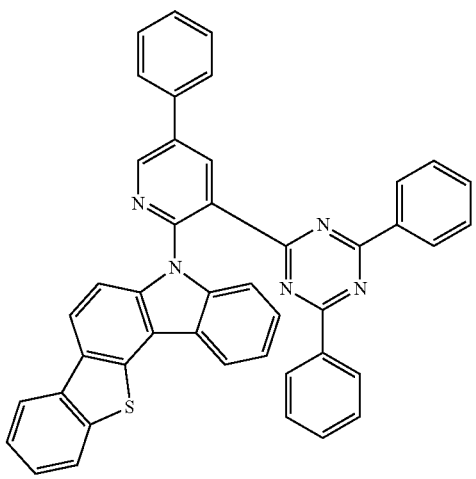
373
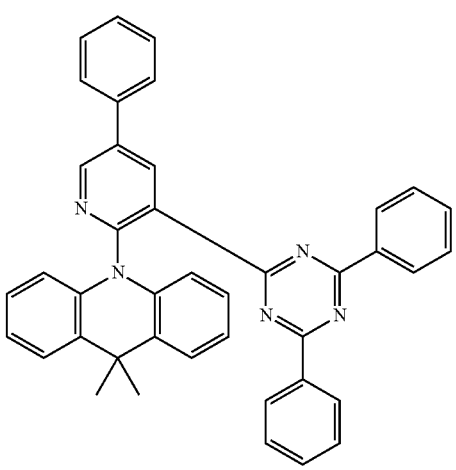

3431
-continued
374
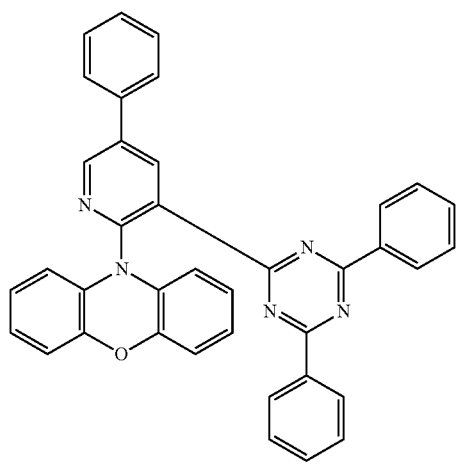
375
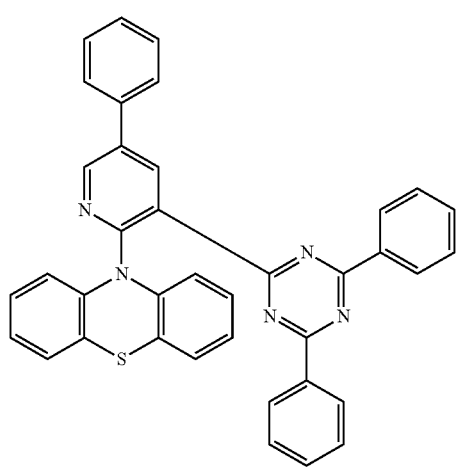
376
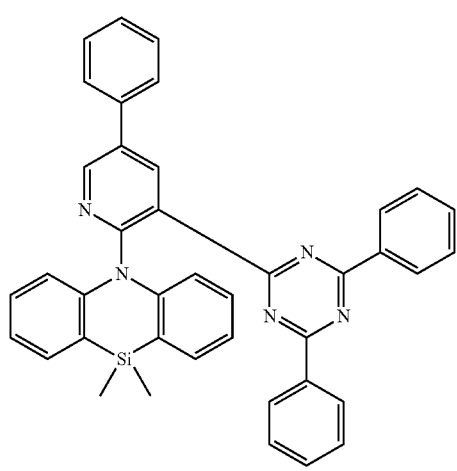
3432
-continued
377
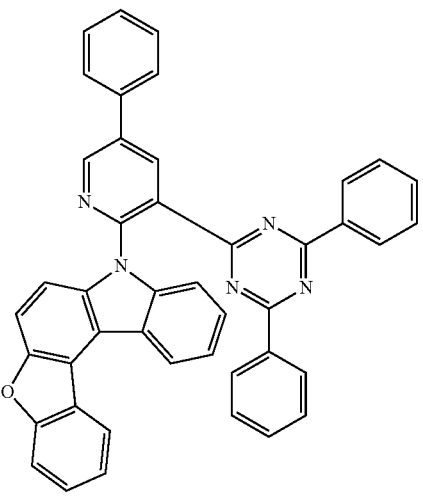
378
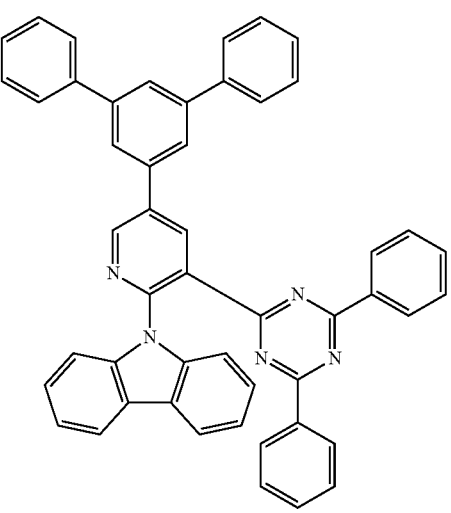
379
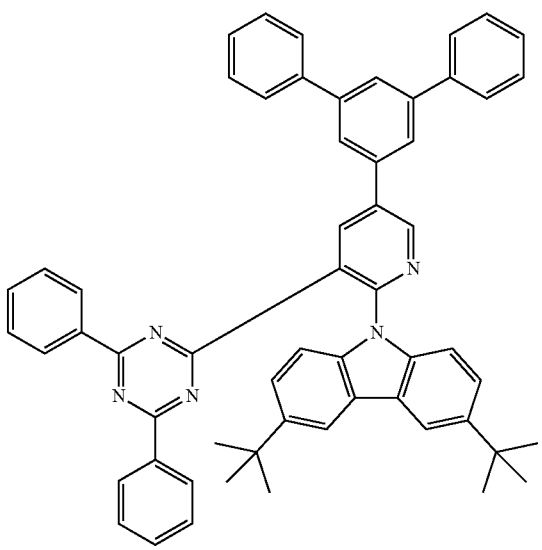

3433
-continued
380
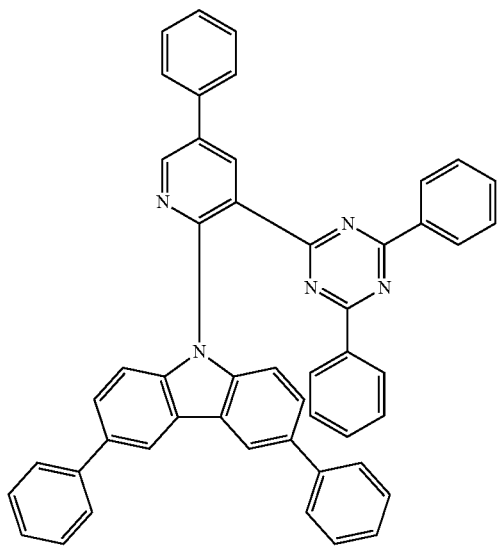
381
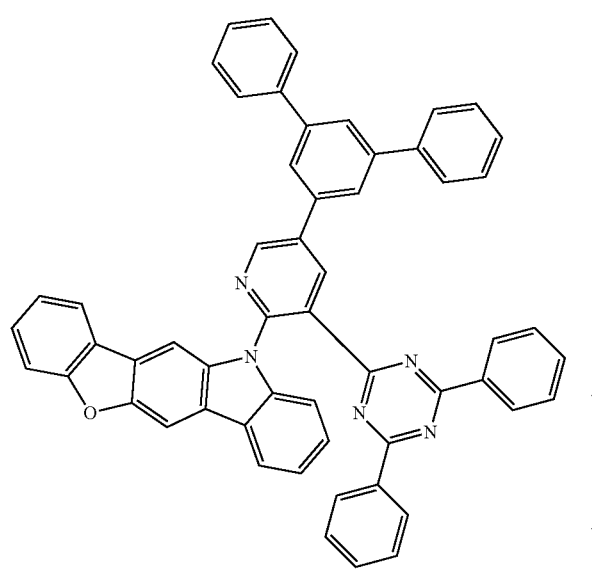
382
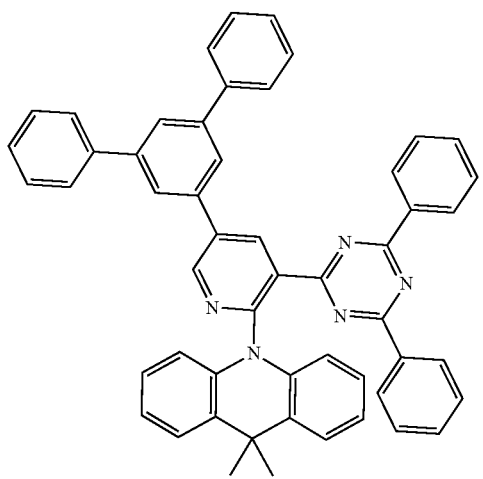
3434
-continued
383
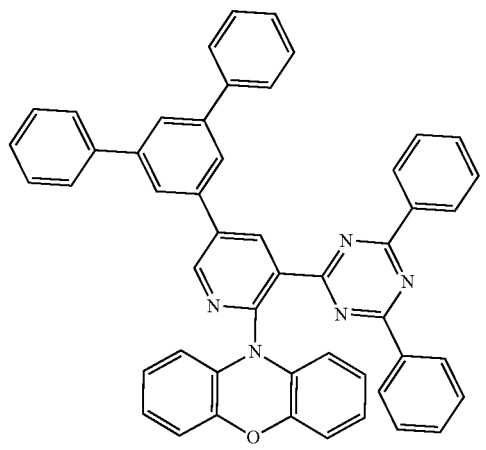
384
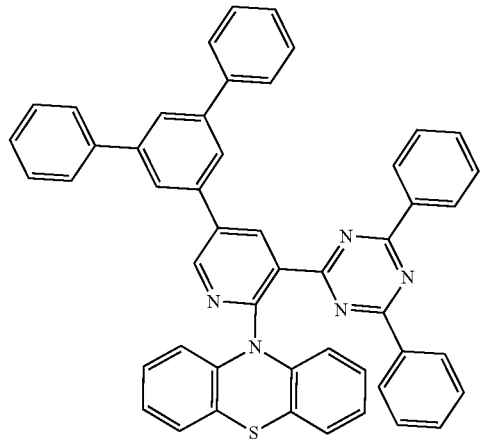
385
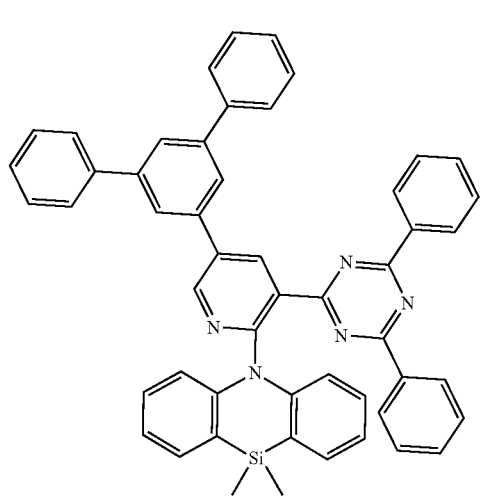

3435
-continued
386
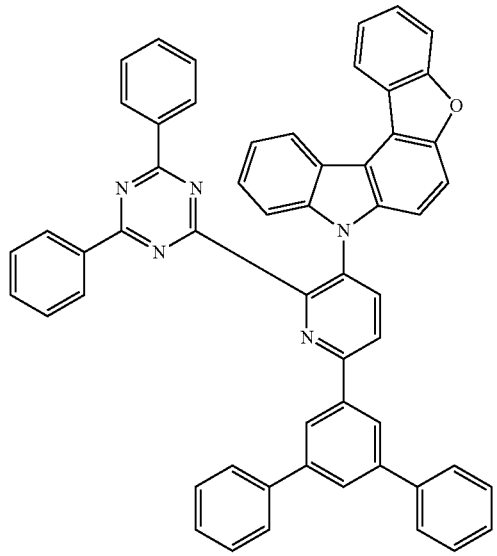
387
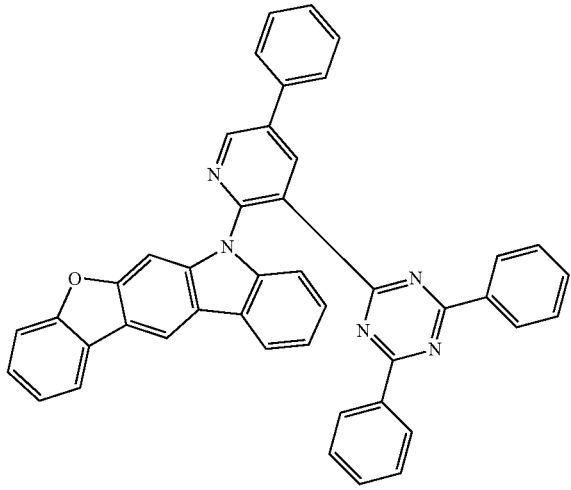
388
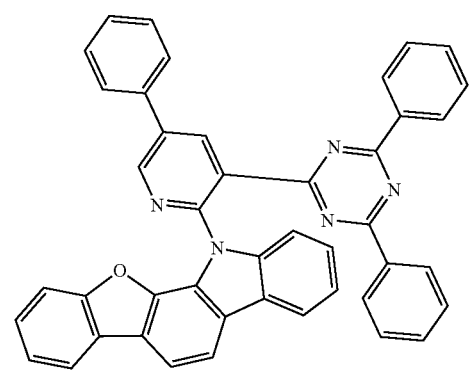
3436
-continued
389
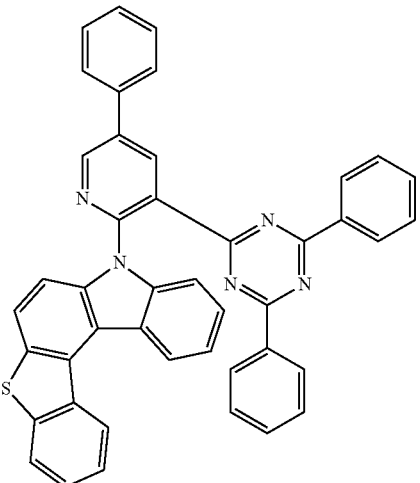
390
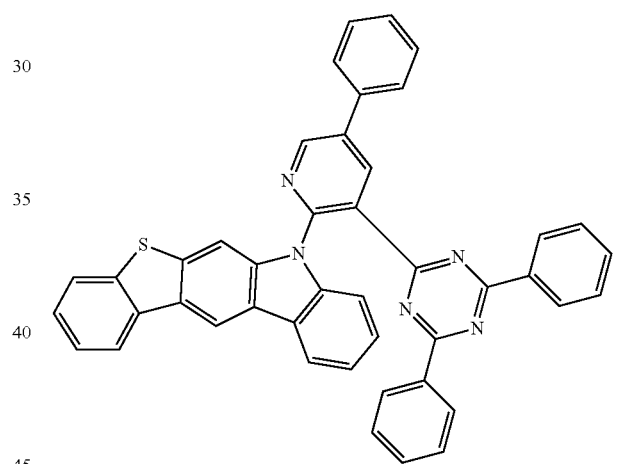
391
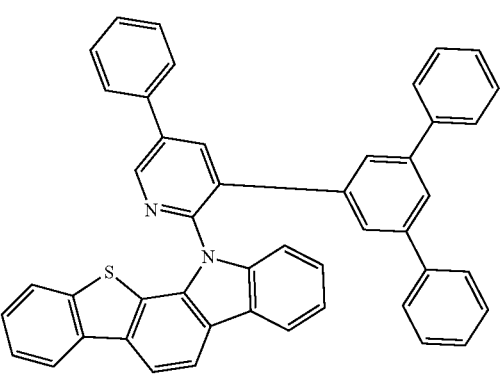

3437
-continued
392
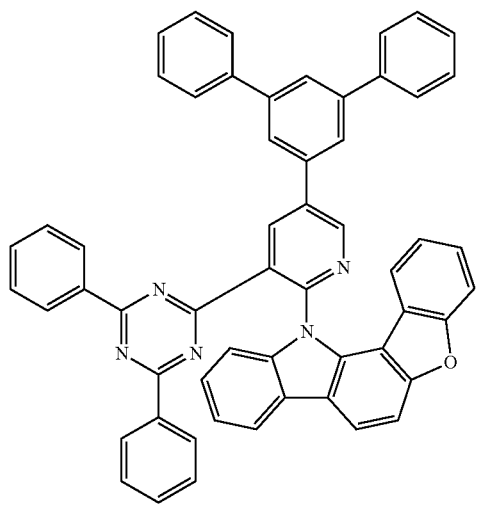
393
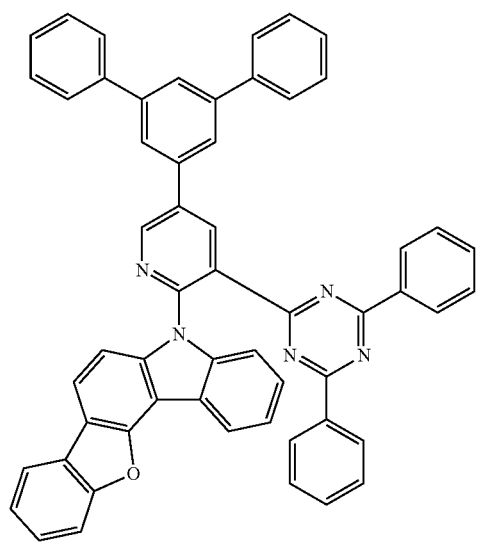
394
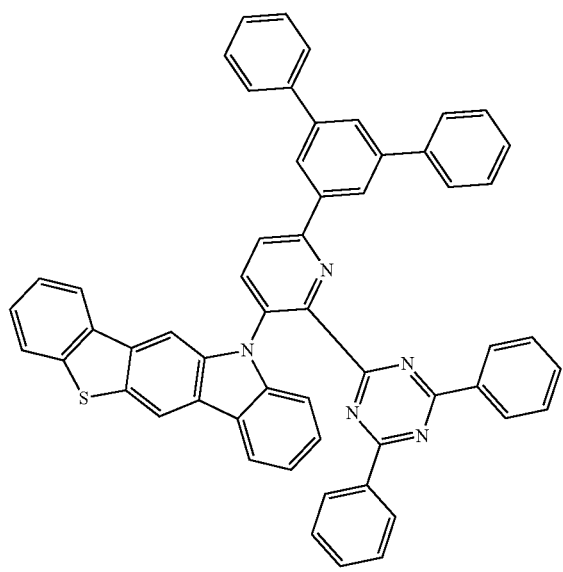
3438
-continued
395
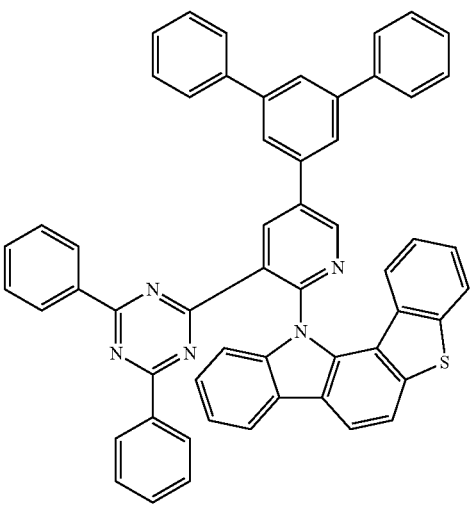
396
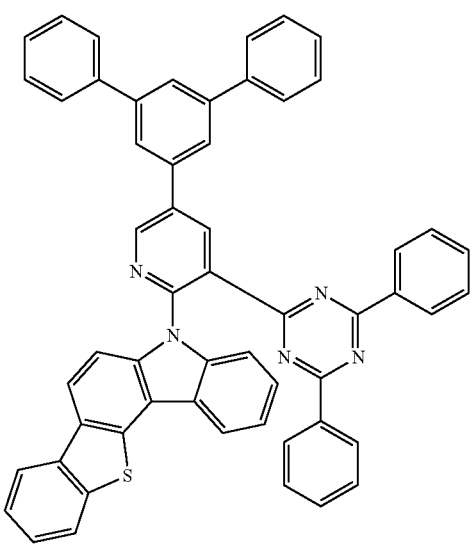
397
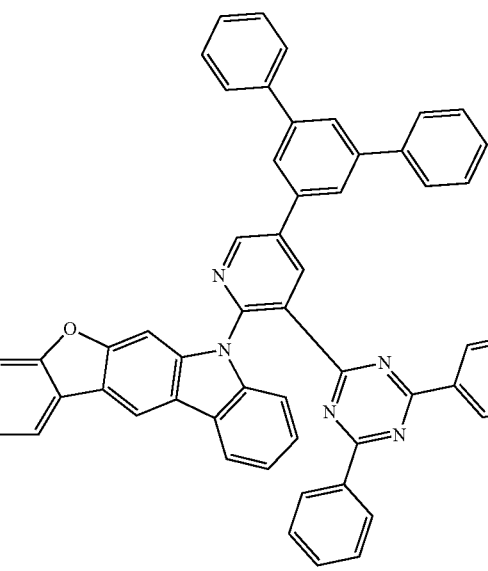

3439
-continued
398
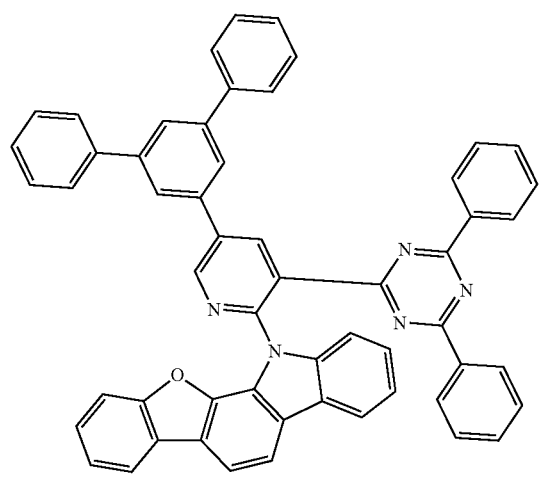
399
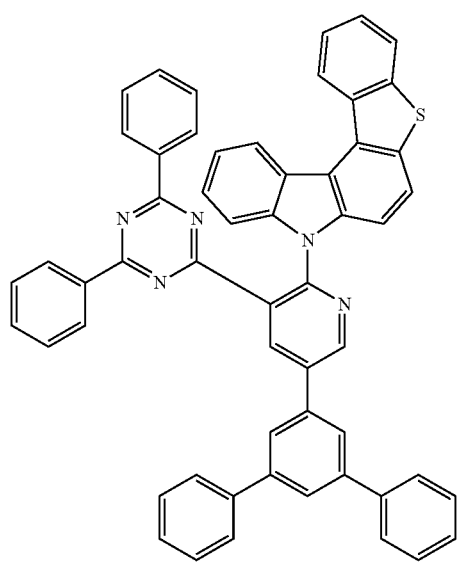
3440
-continued
400
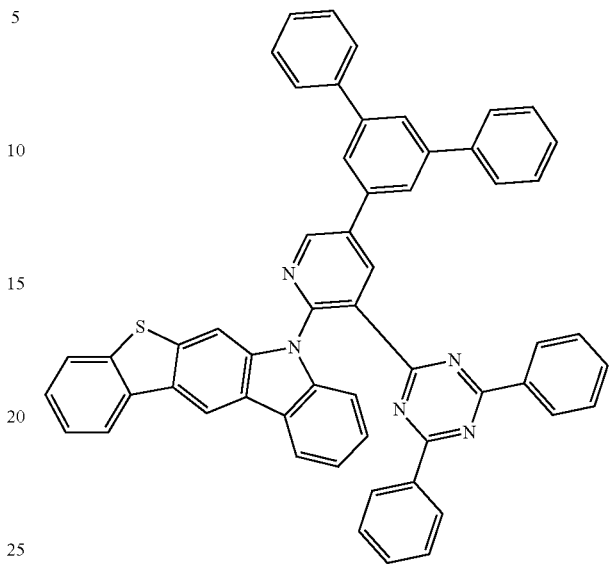
401
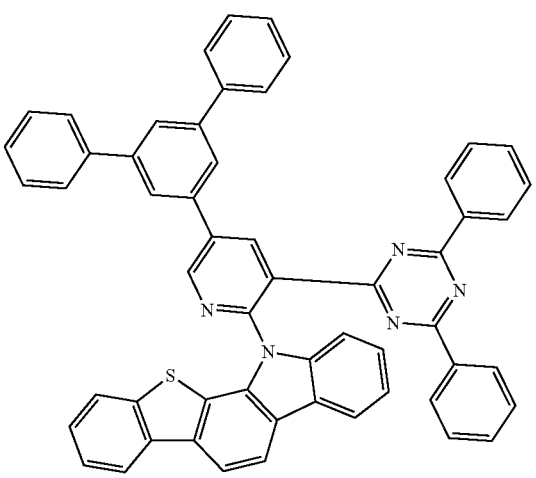

3441
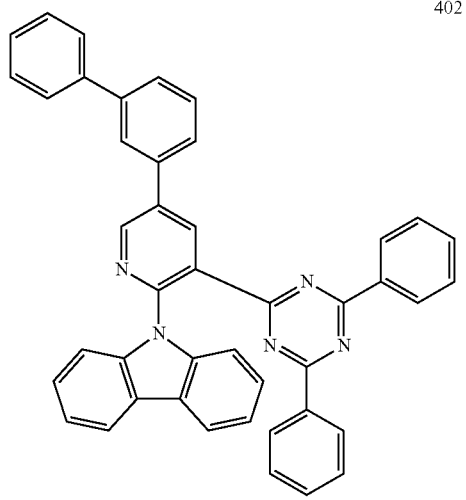
3442
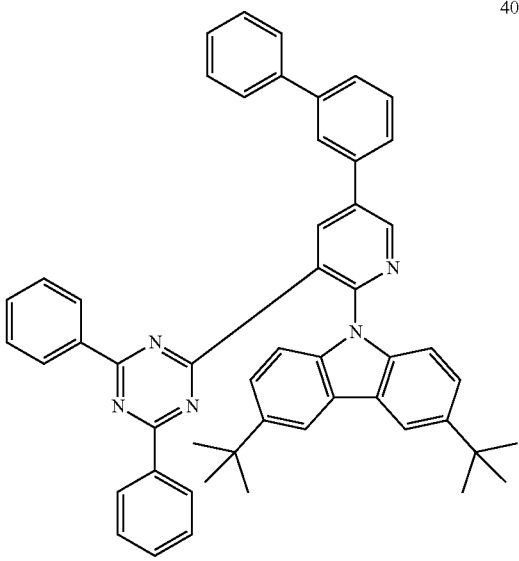
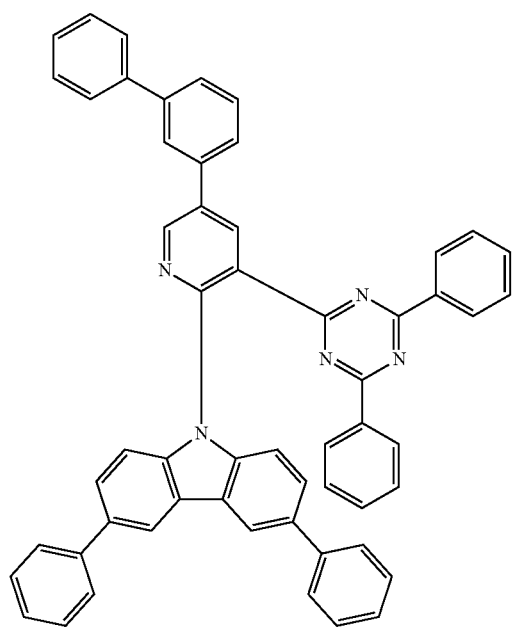
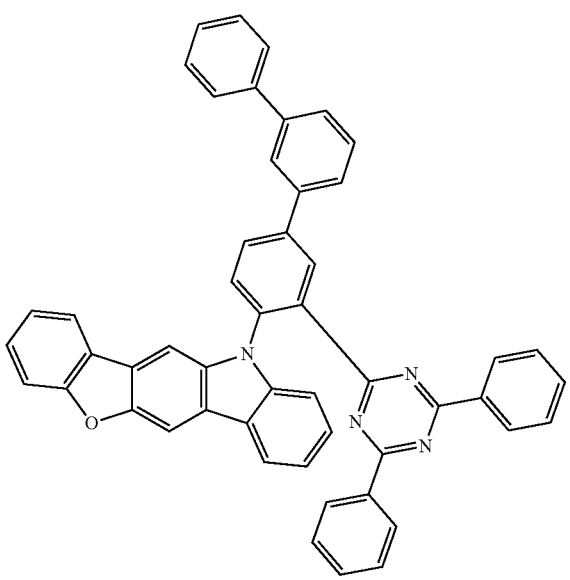
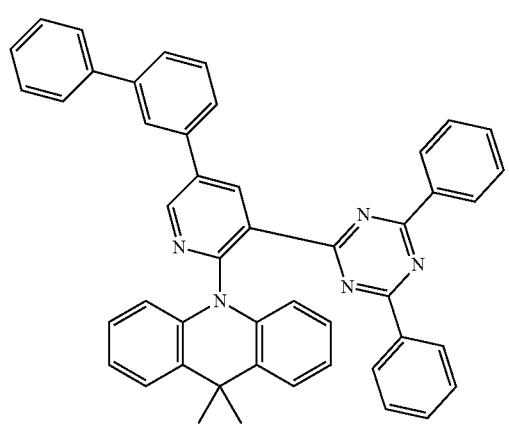
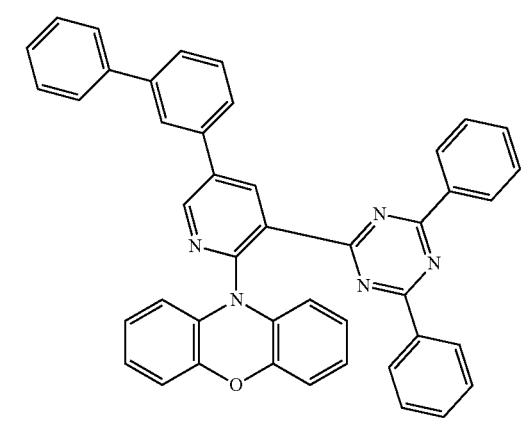

-continued
408
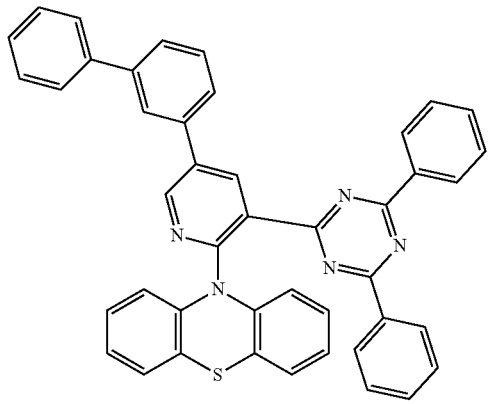
409
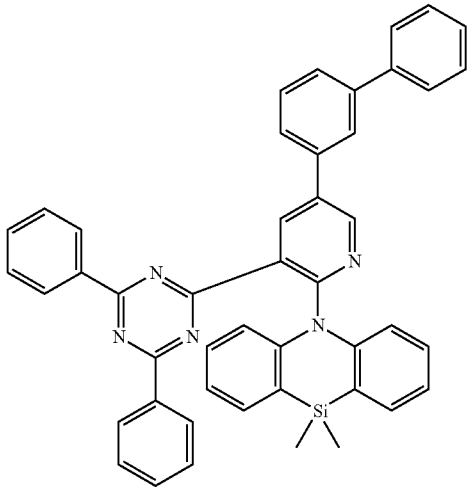
410
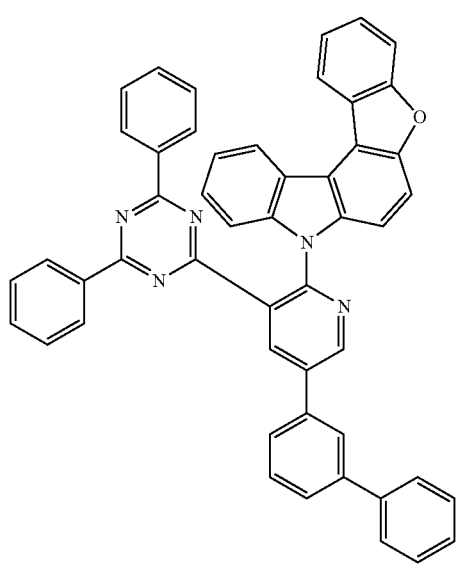
411
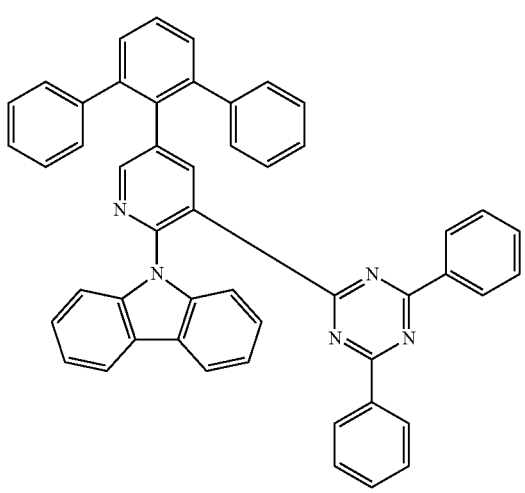

-continued
412
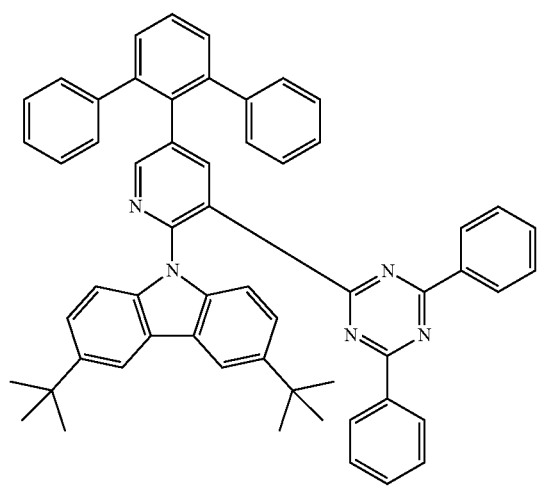
413
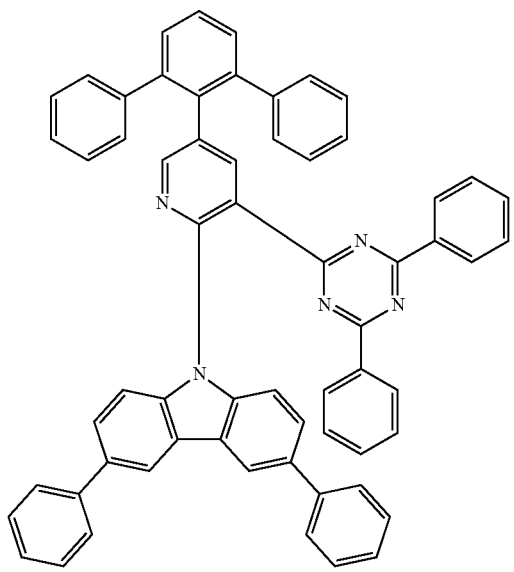
414
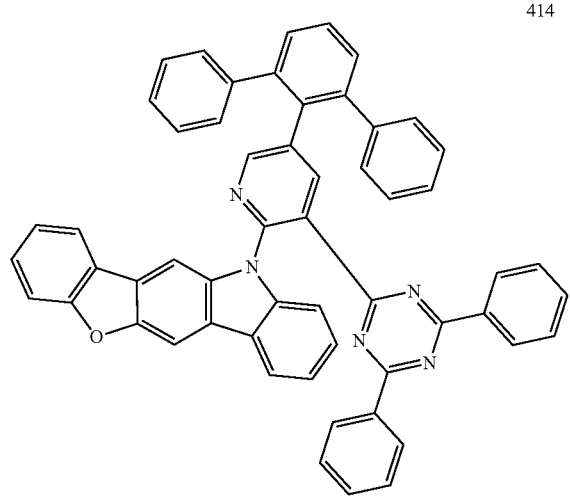
415
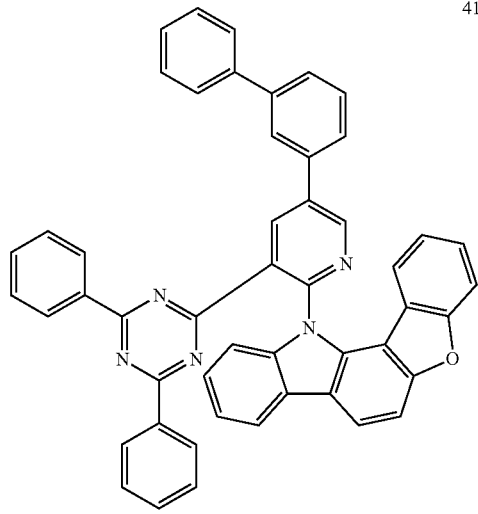

-continued
416
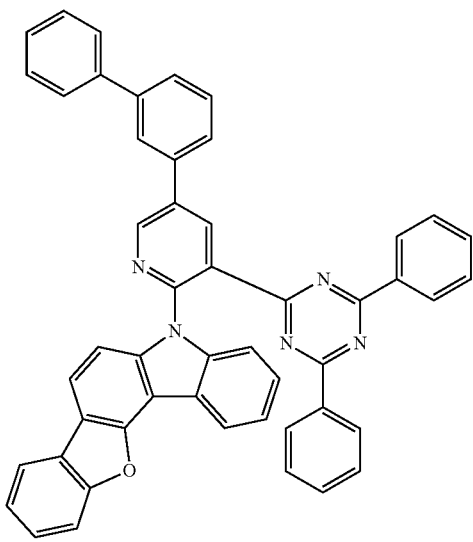
417
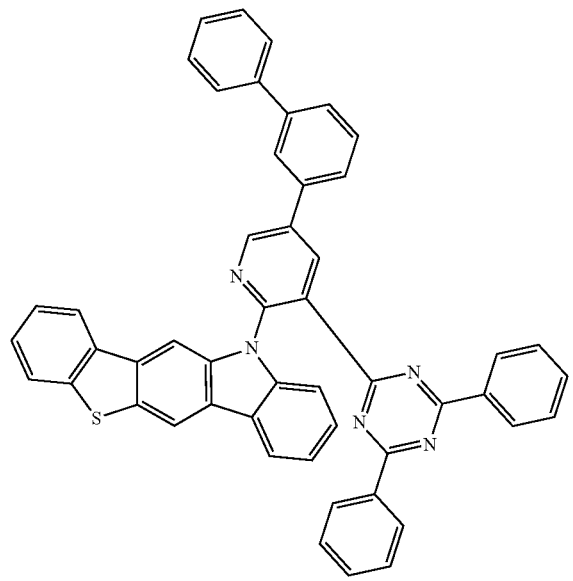
418
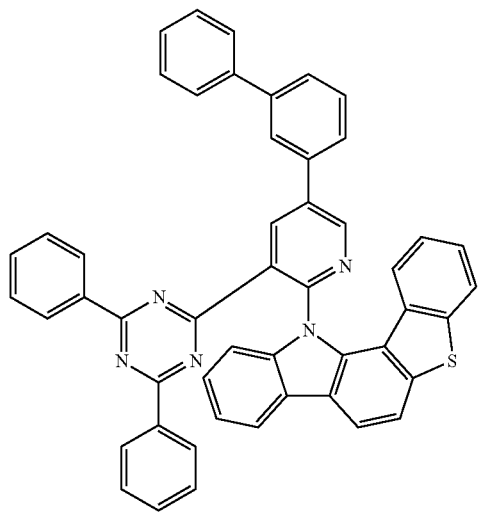
419
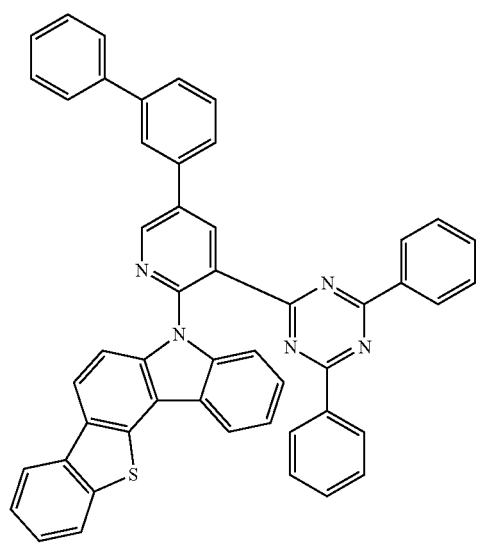

-continued
420
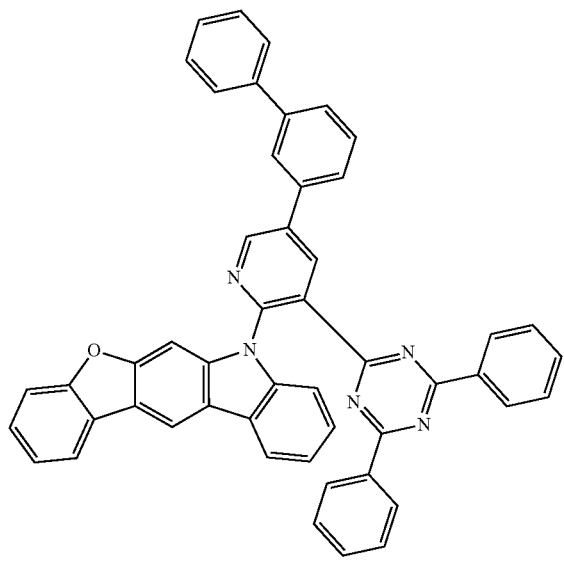
421
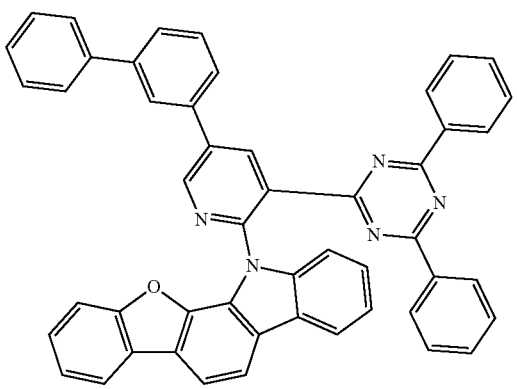
423
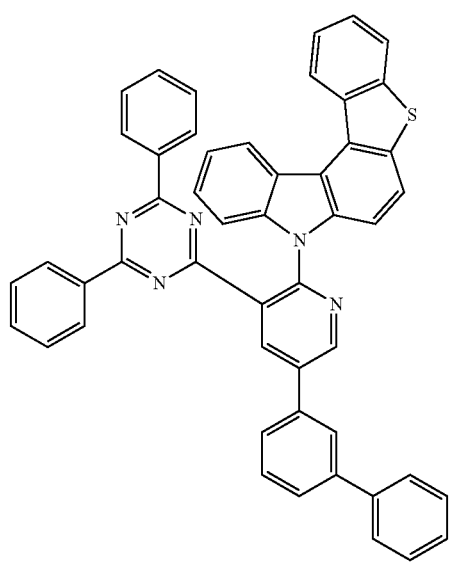
424
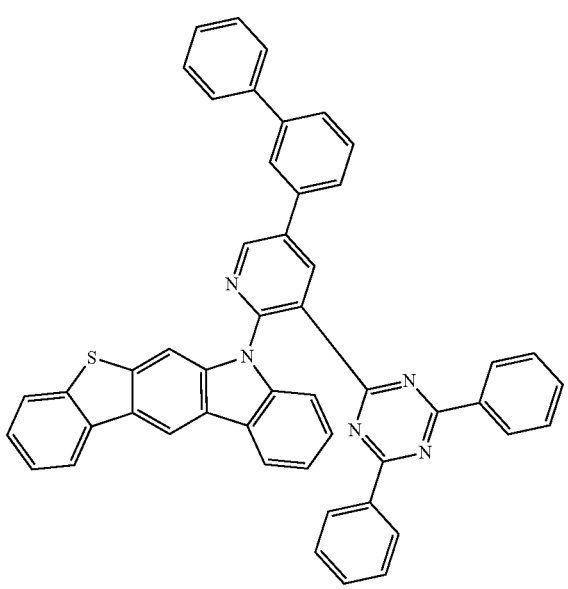
425
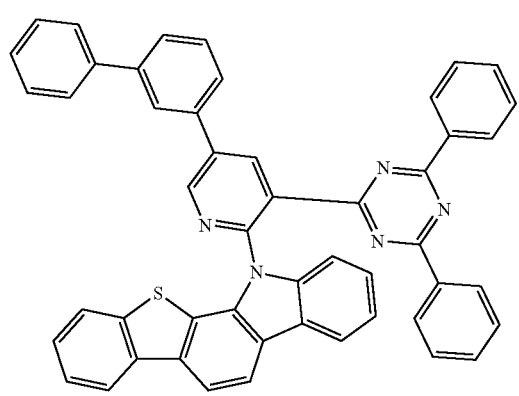
426
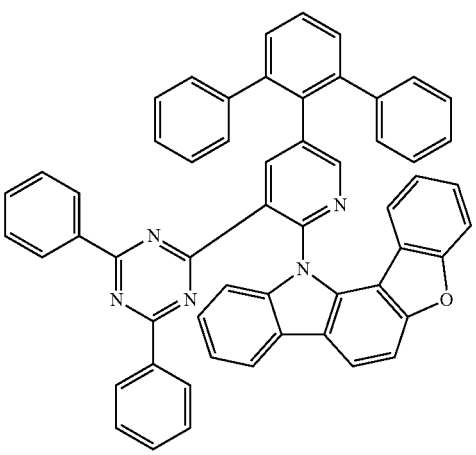

427
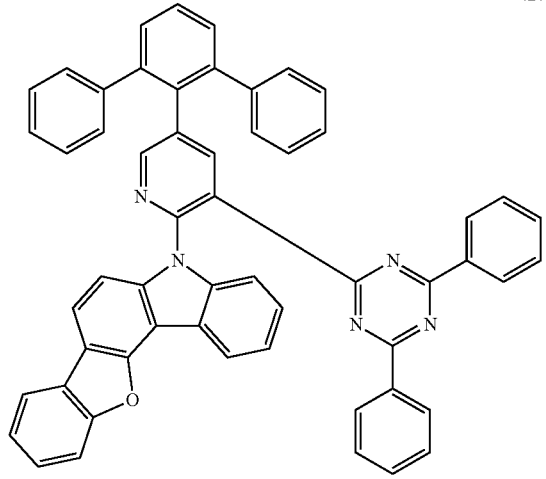
428
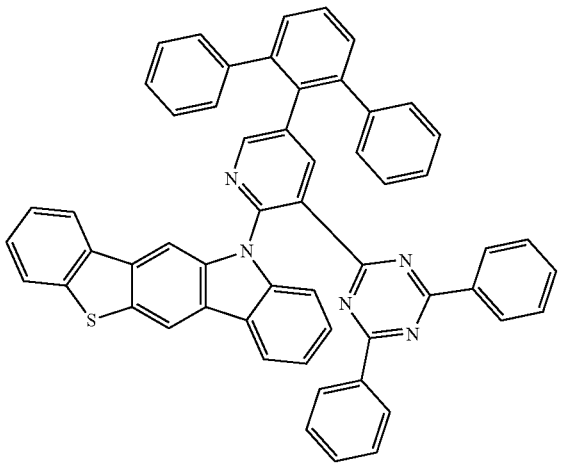
429
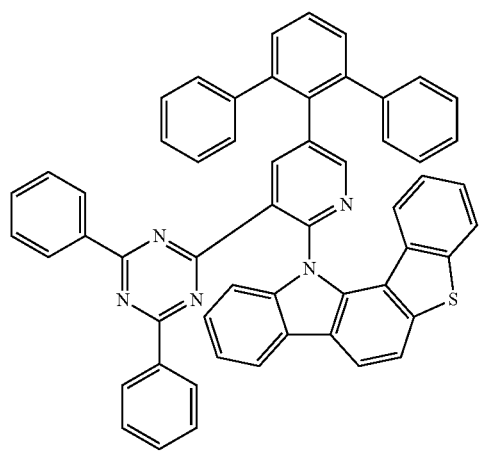
430
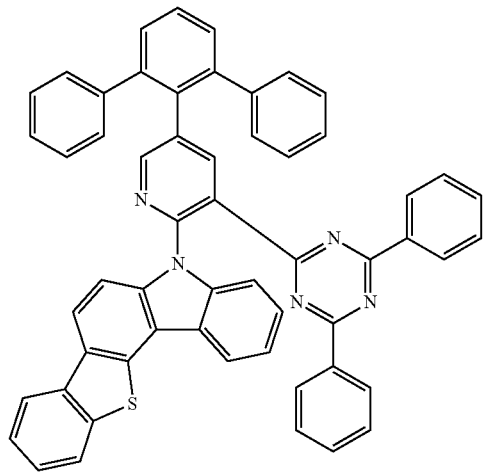
431
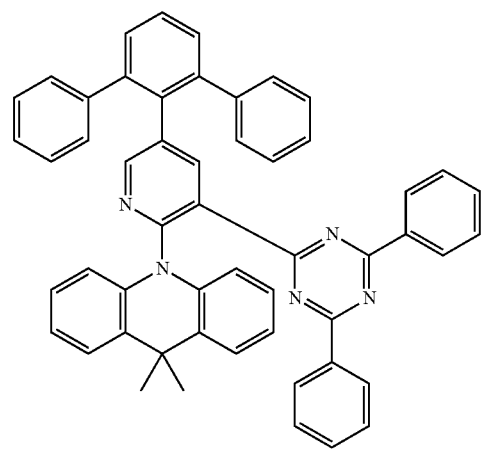
432
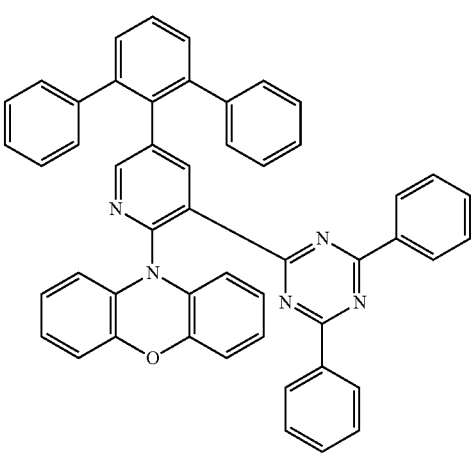

-continued
433
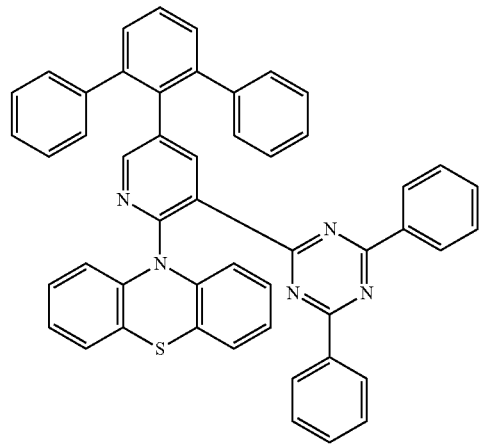
434
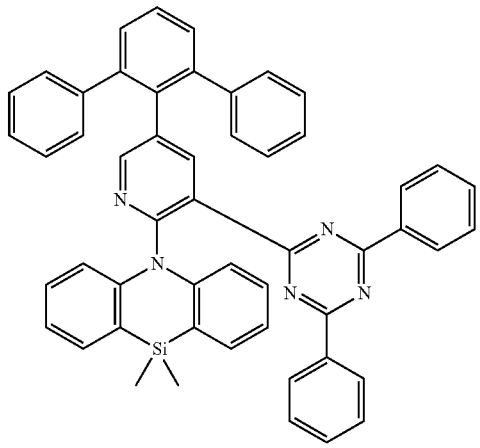
435
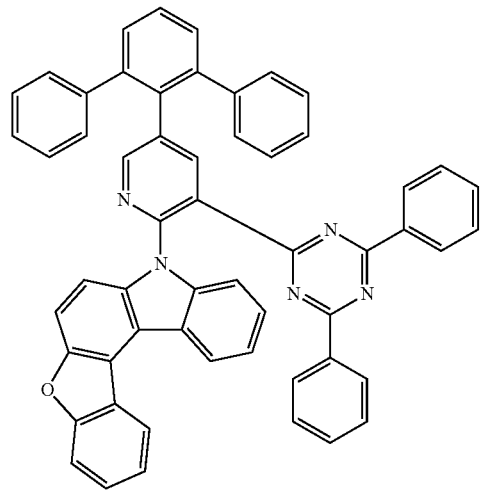
436
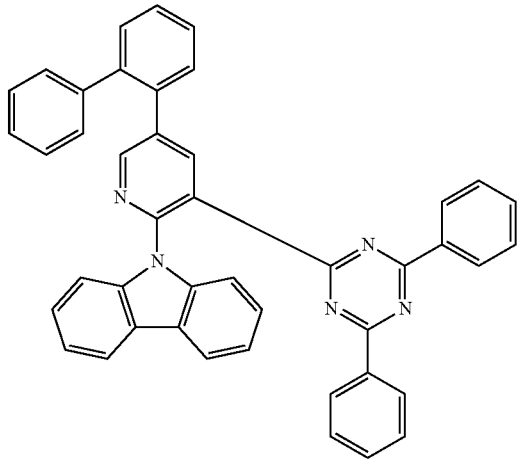
437
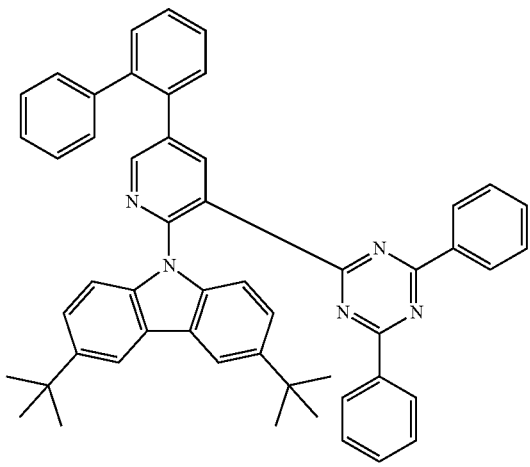
438
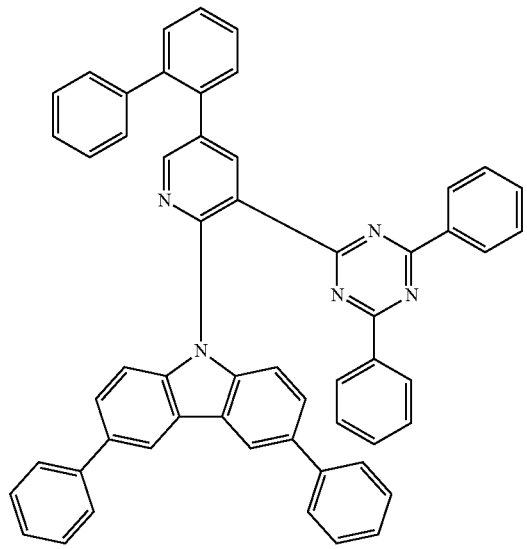

-continued
439
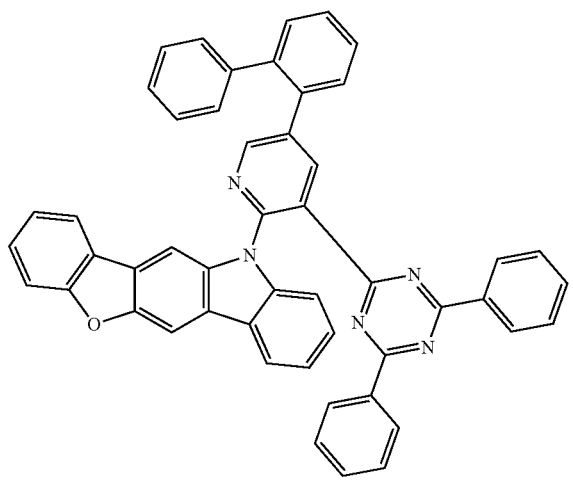
440
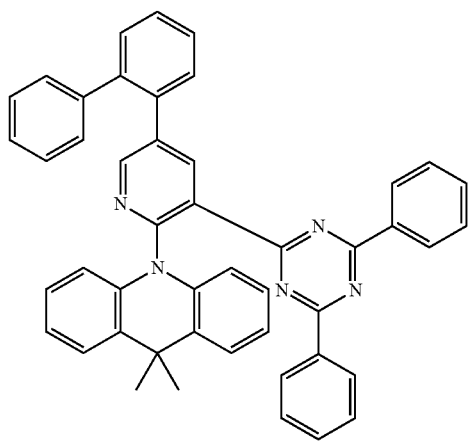
441
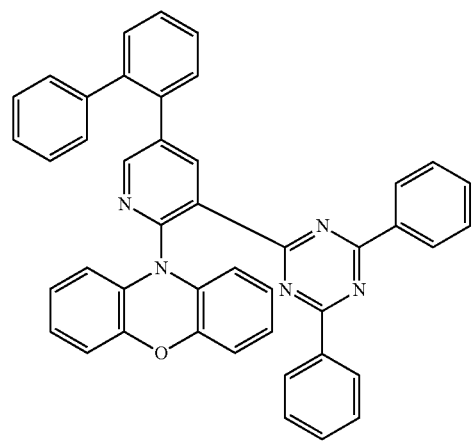
442
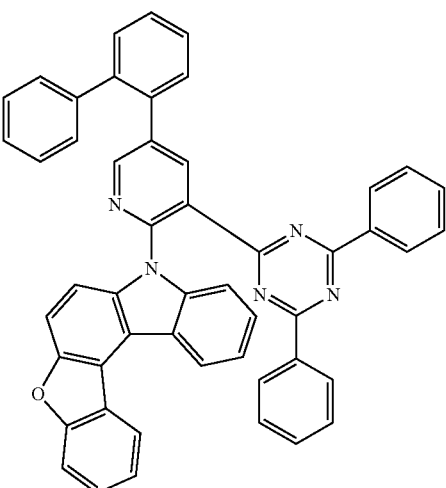
443
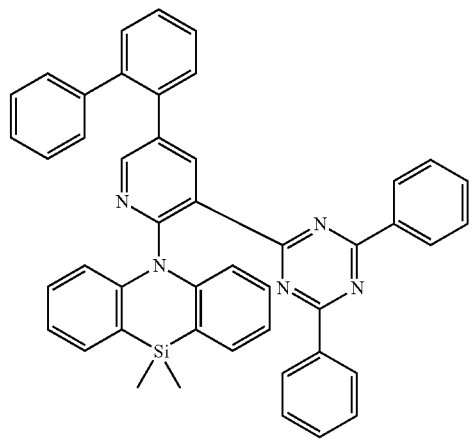
444
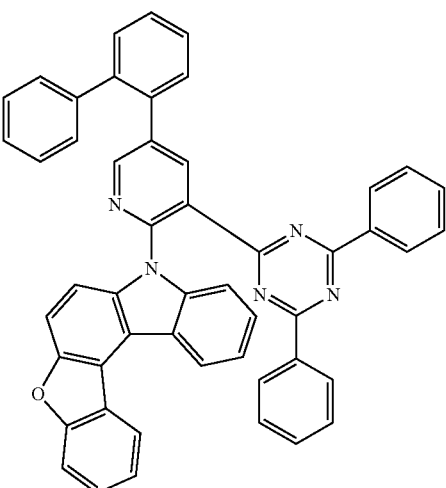

| 3457 | 3458 |
|---|---|
445
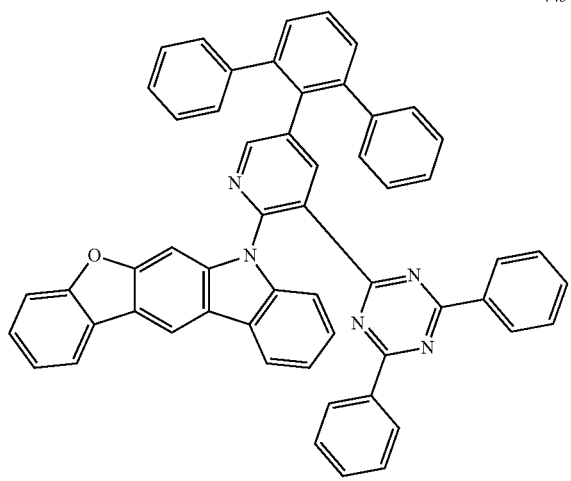
446
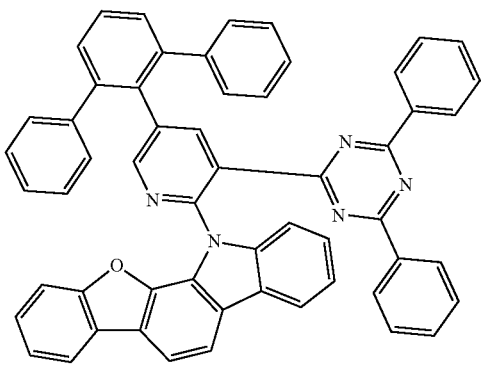
447
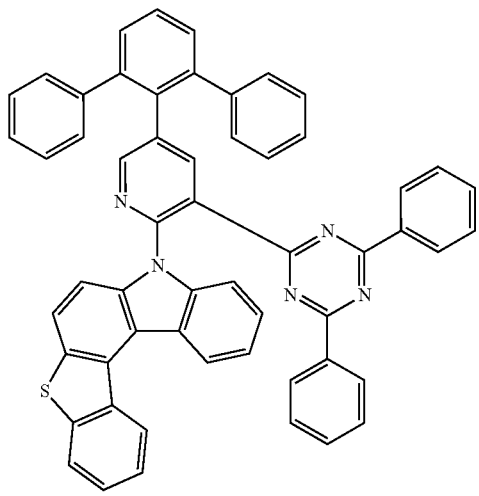
448
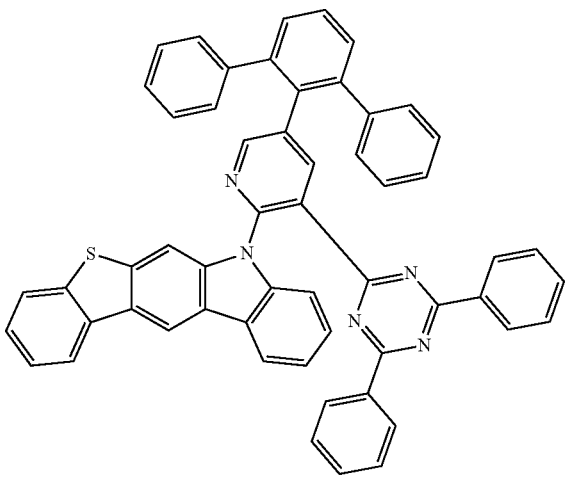
449
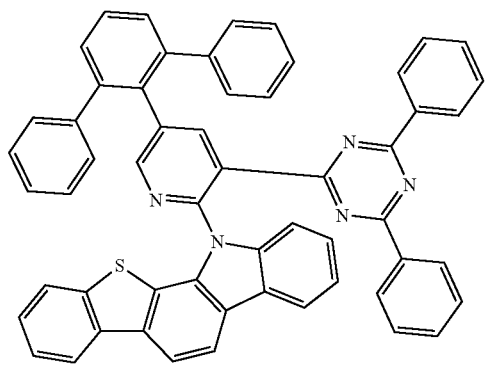
450
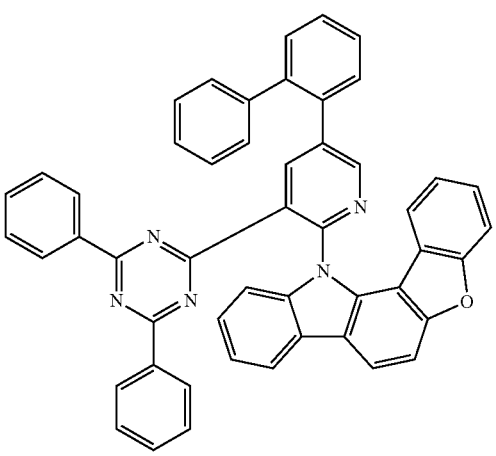

451
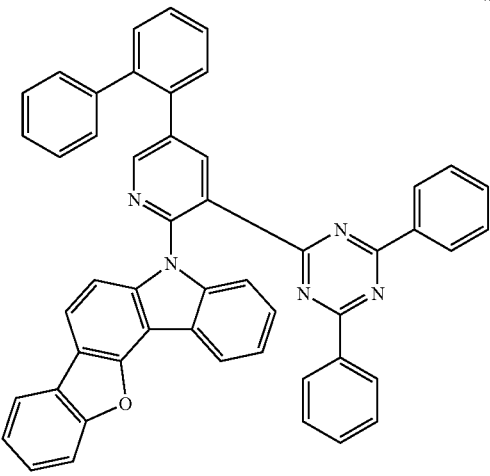
452
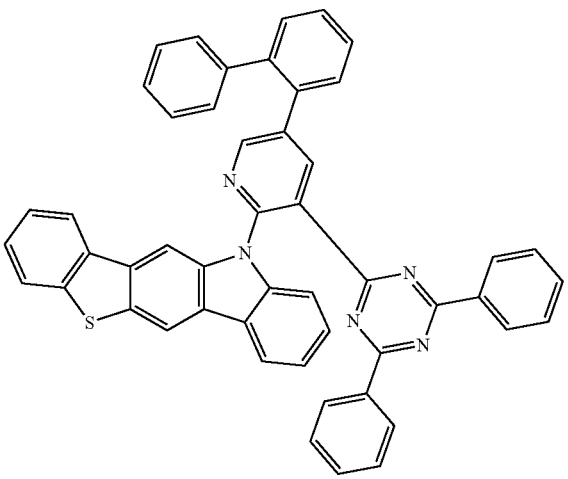
453
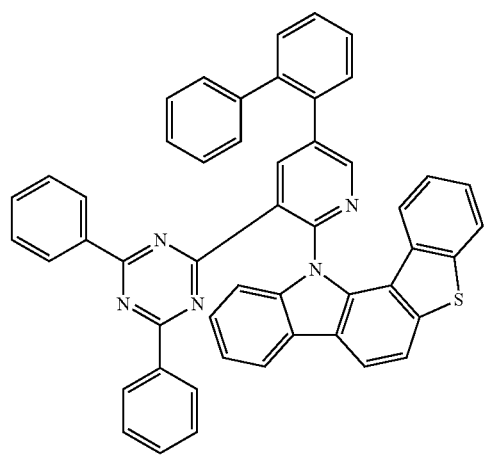
454
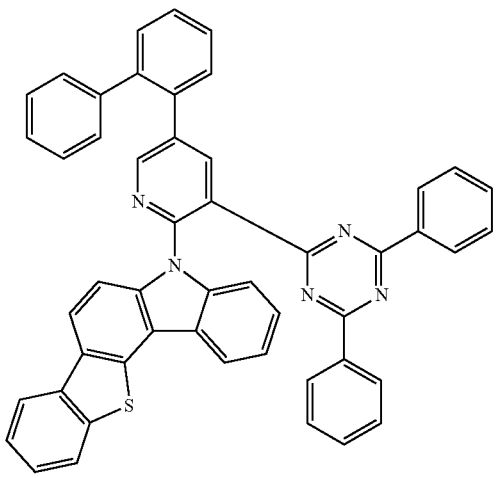
455
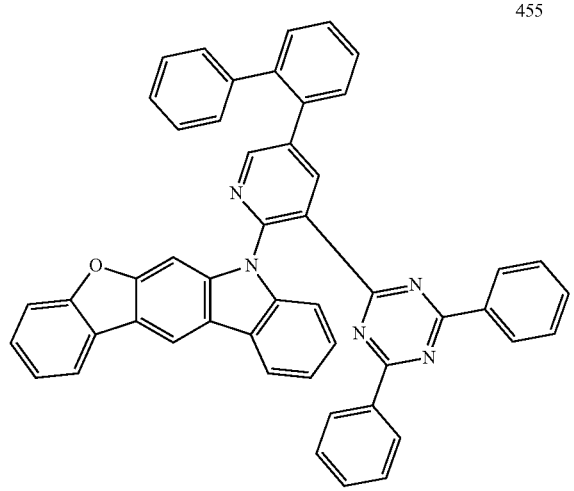
456
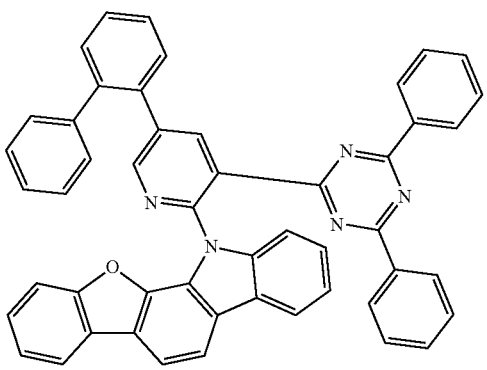

457
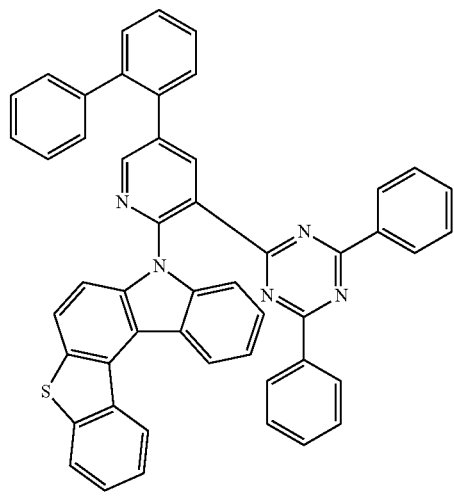
458
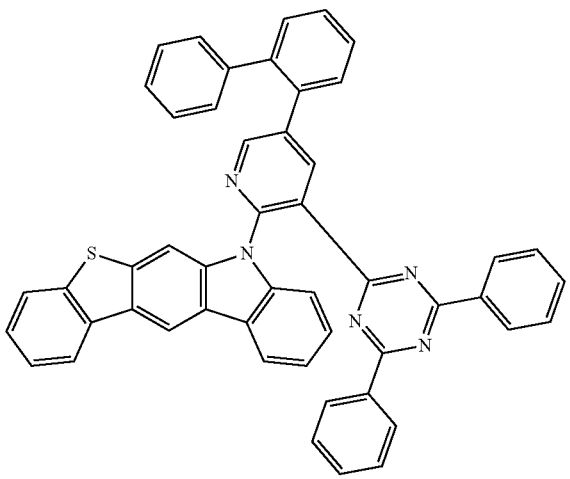
459
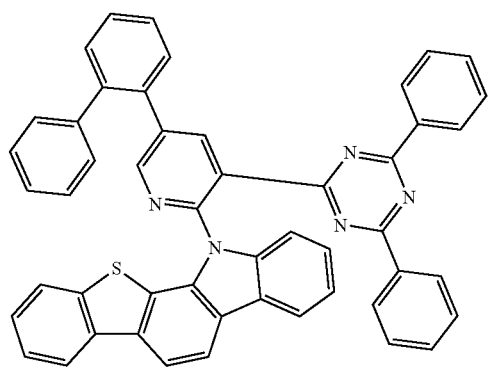
460
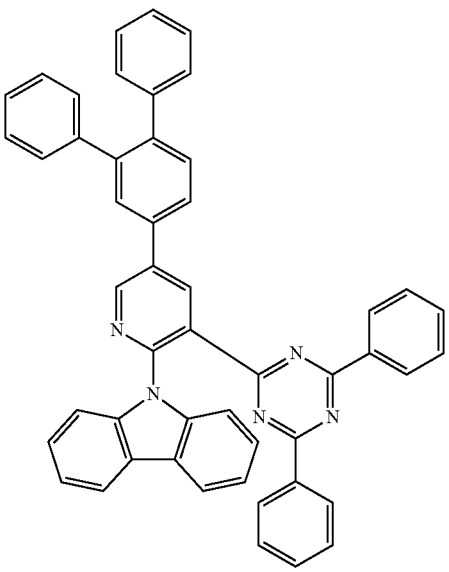

3463
461
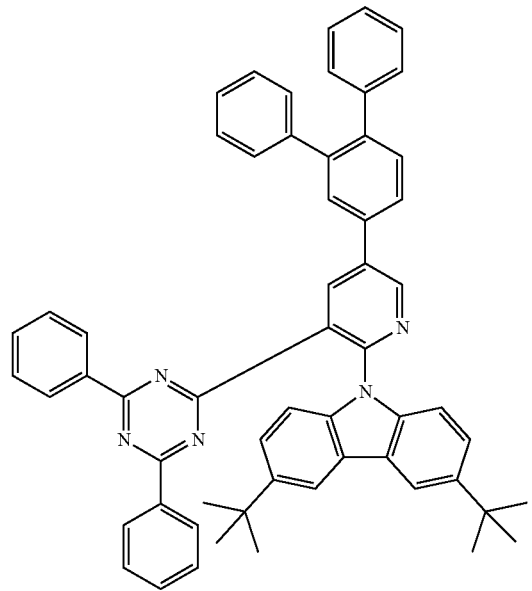
3464
462
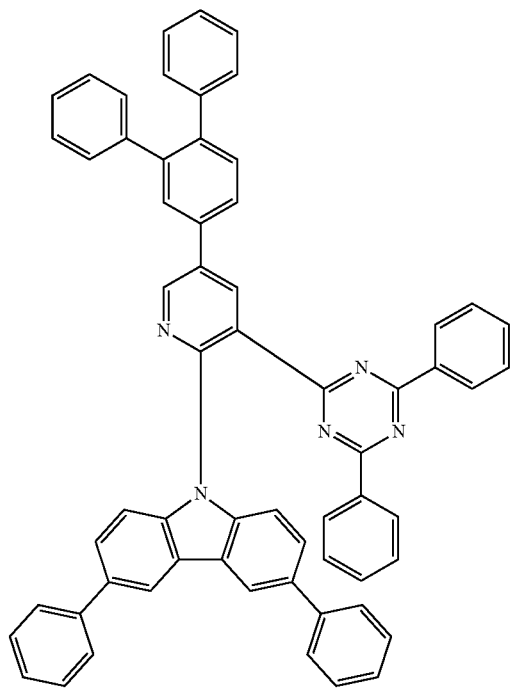
463
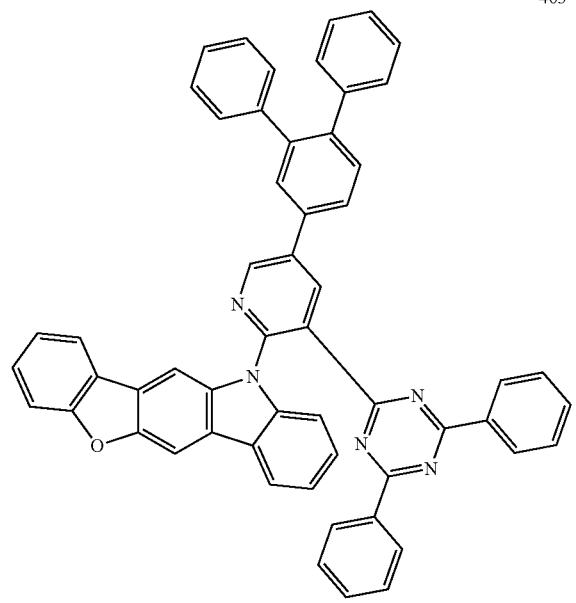
464
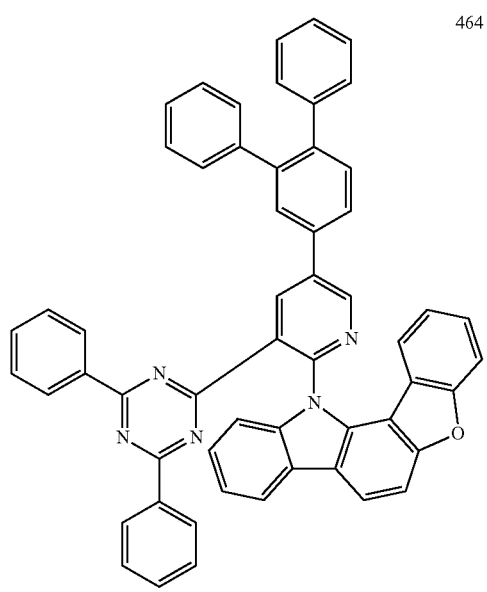

3465
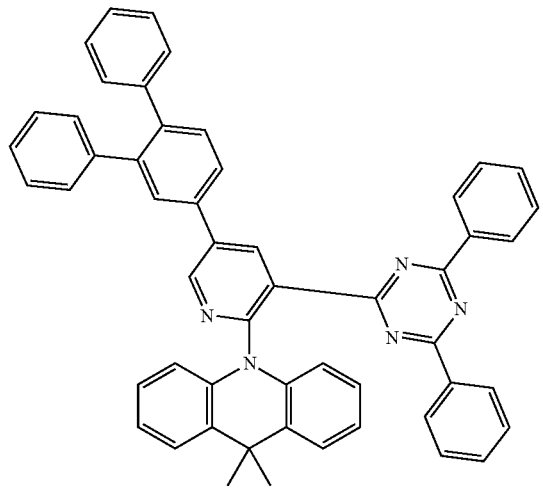
3466
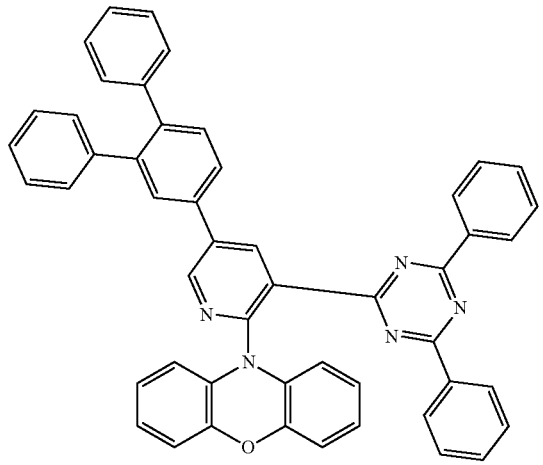
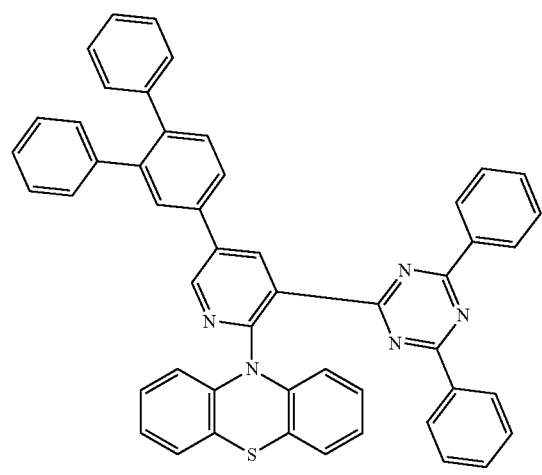
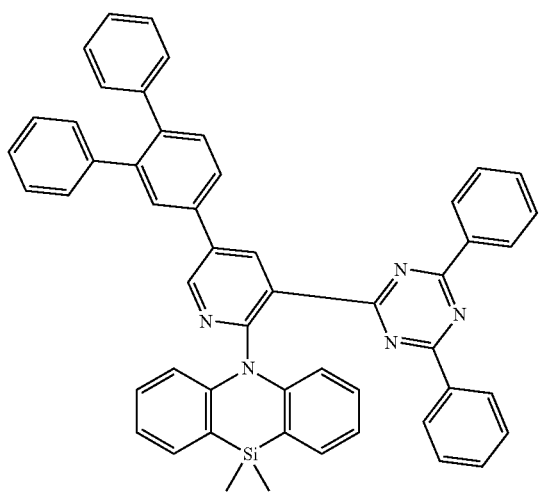

-continued
469
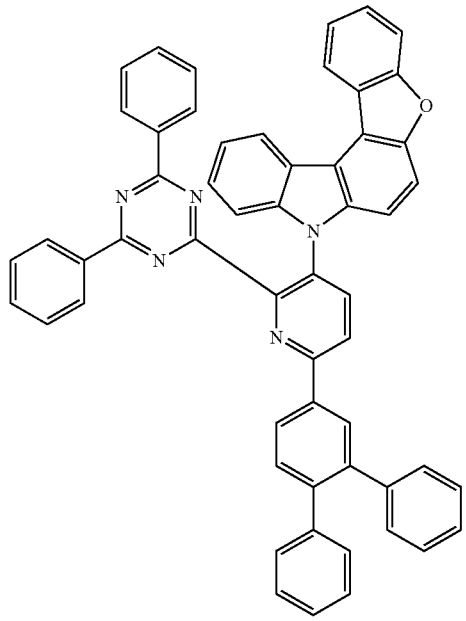
470
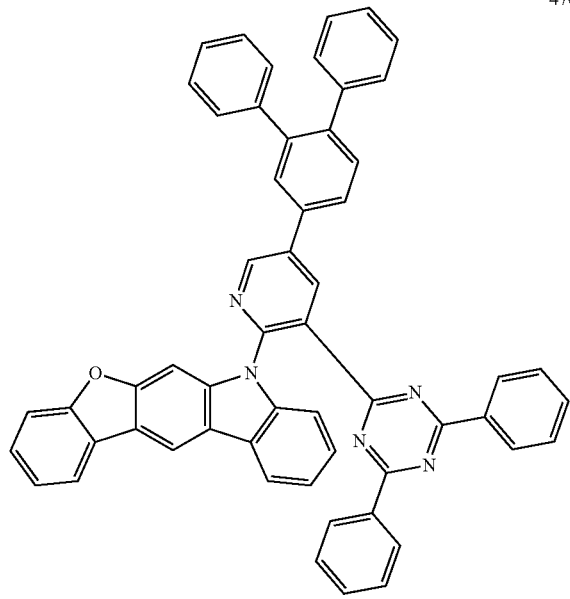
471
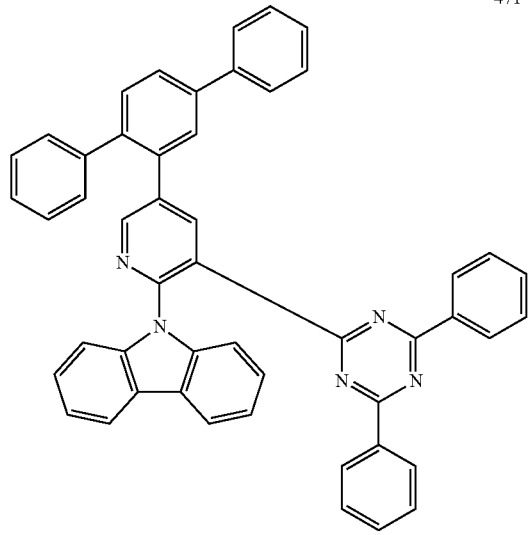
472
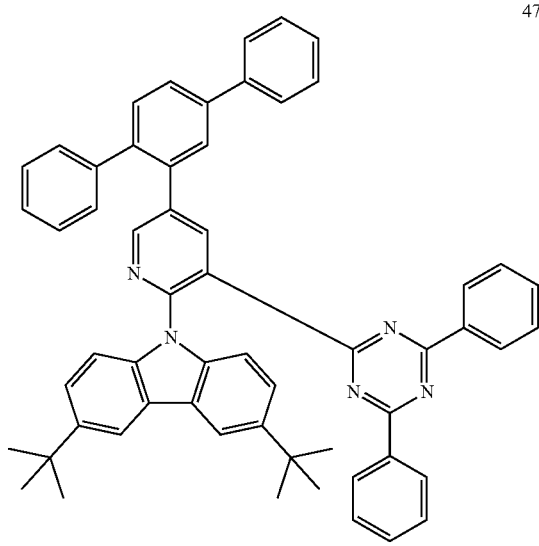

-continued
473
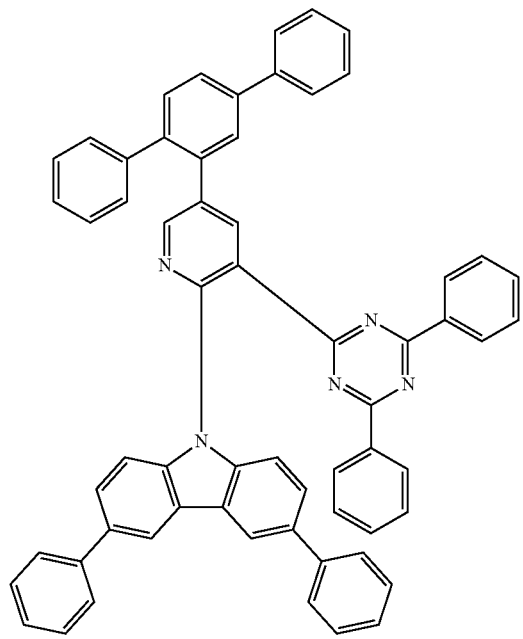
474
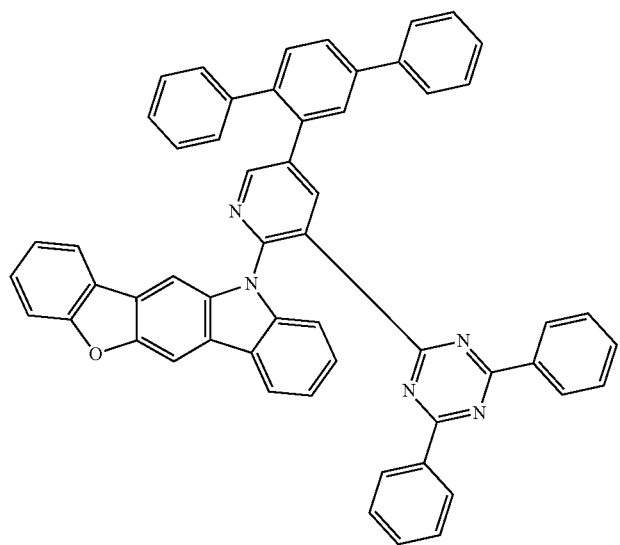

3471
-continued
475
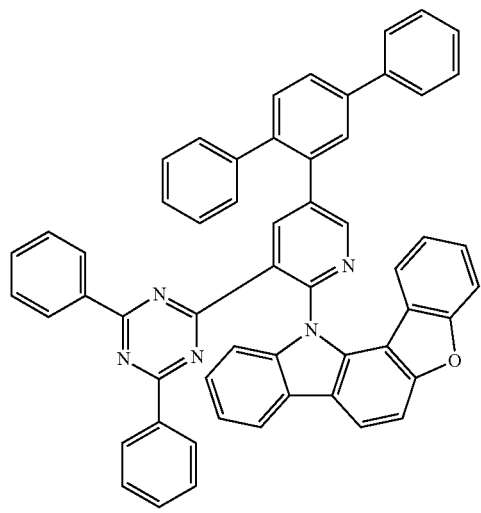
476
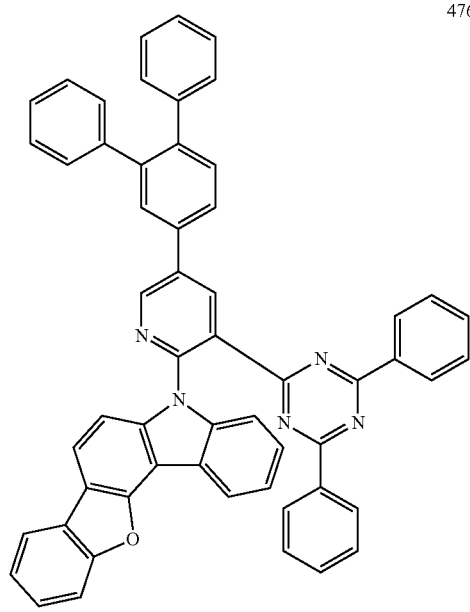
3472
477
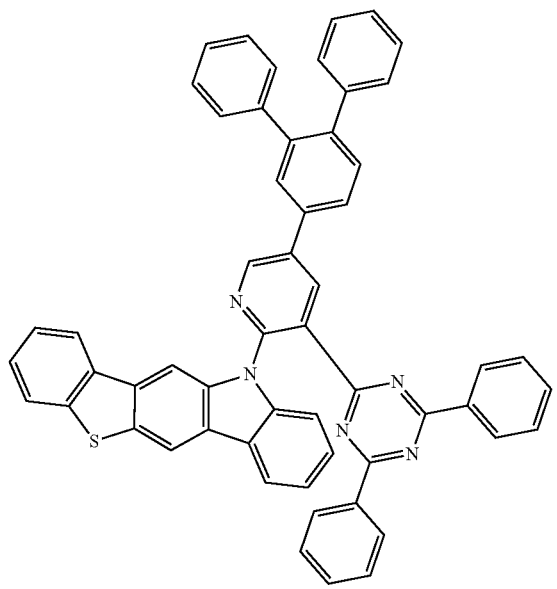
478
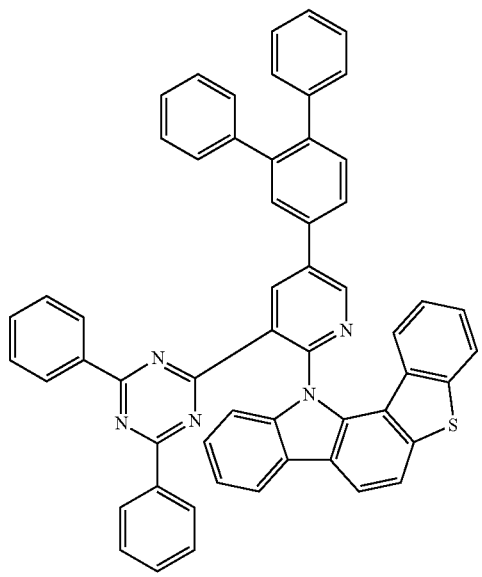

3473
479
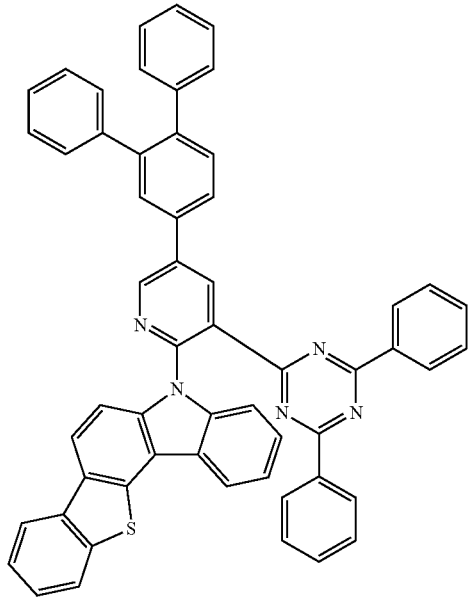
3474
480
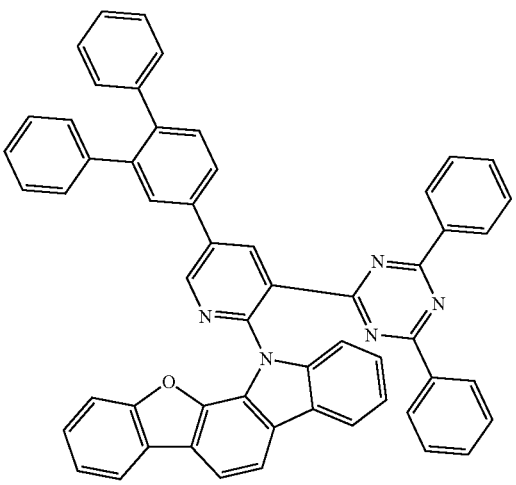
481
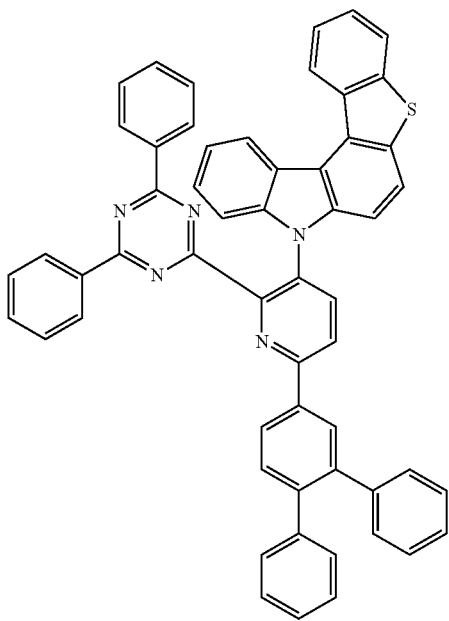
482
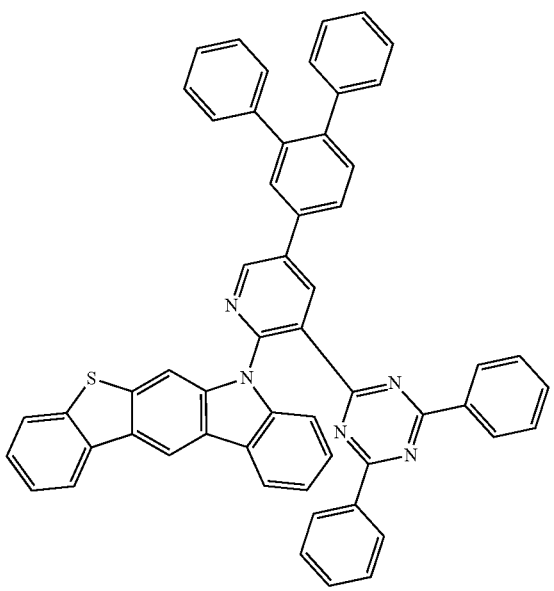

483
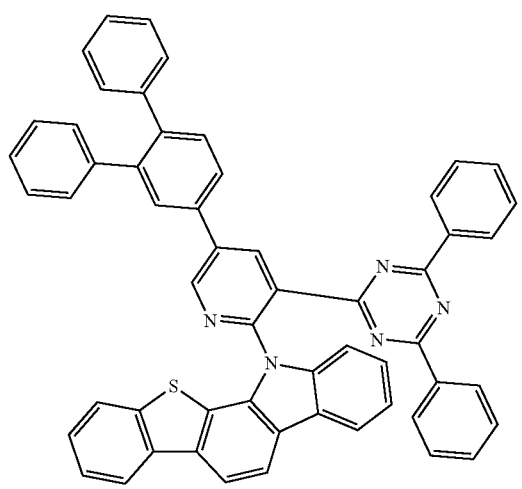
484
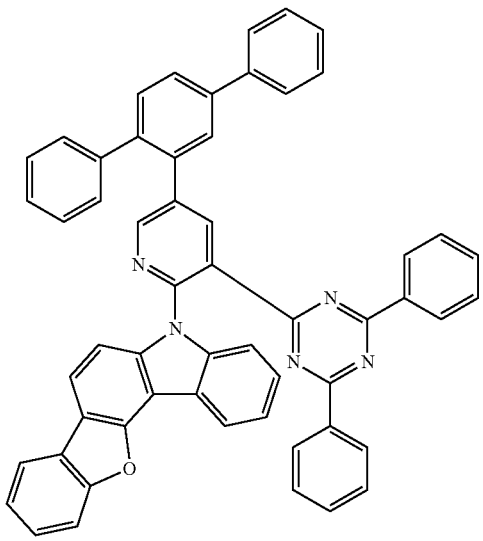
485
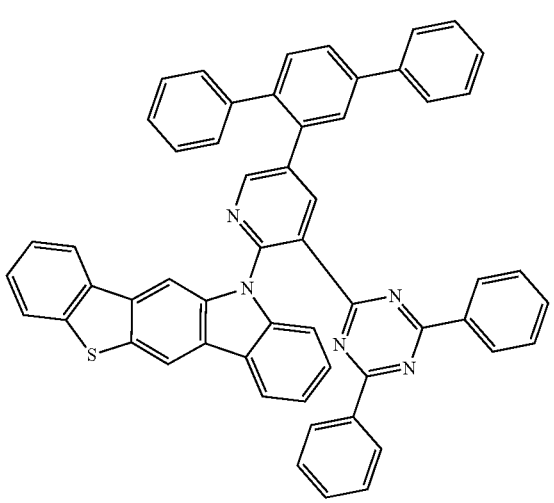
486
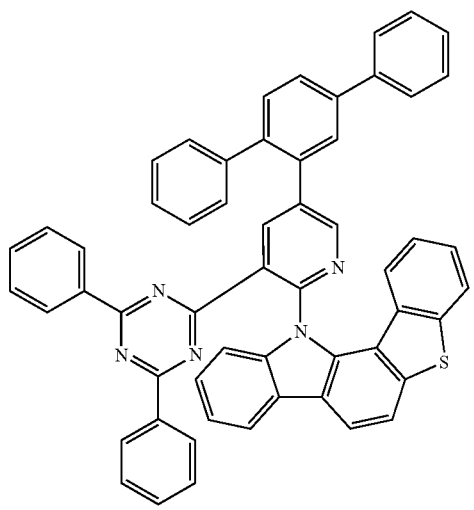
487
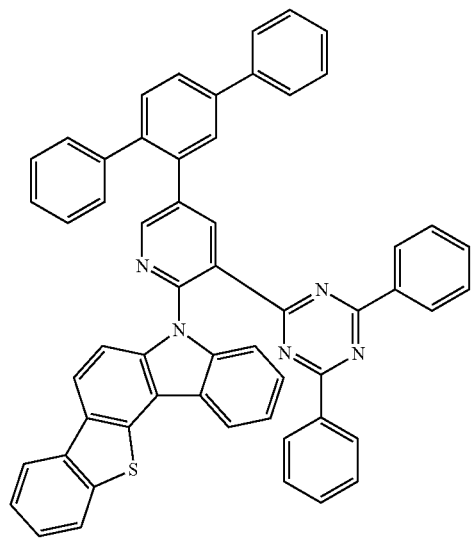
488
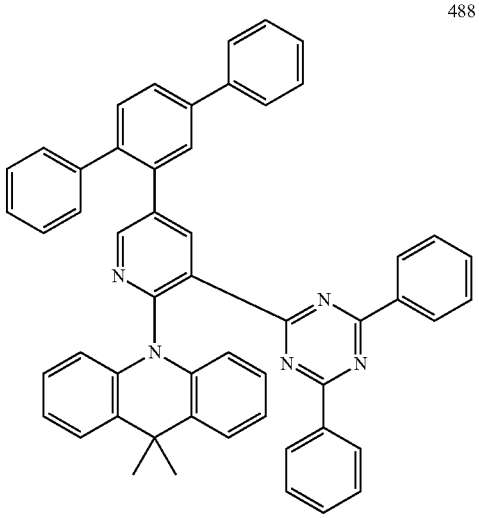

-continued
489
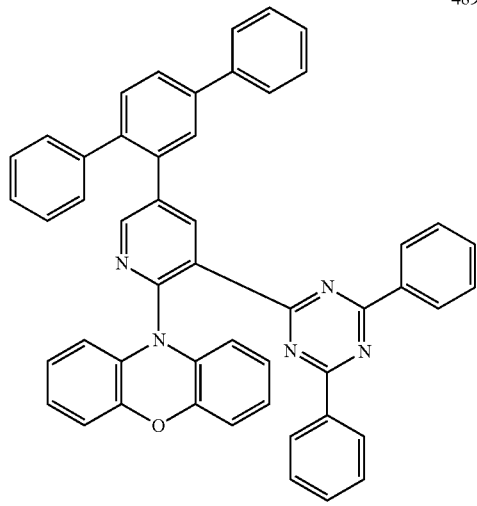
490
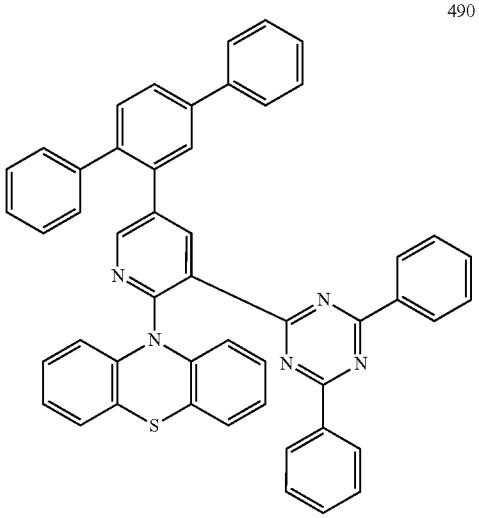
491
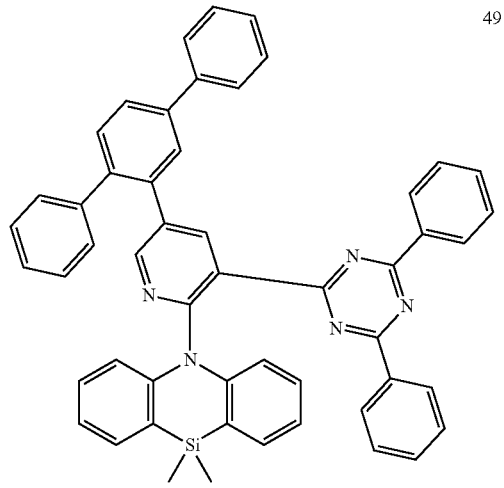
492
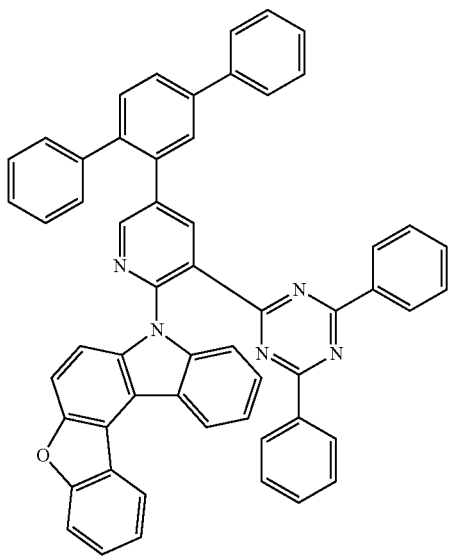

-continued
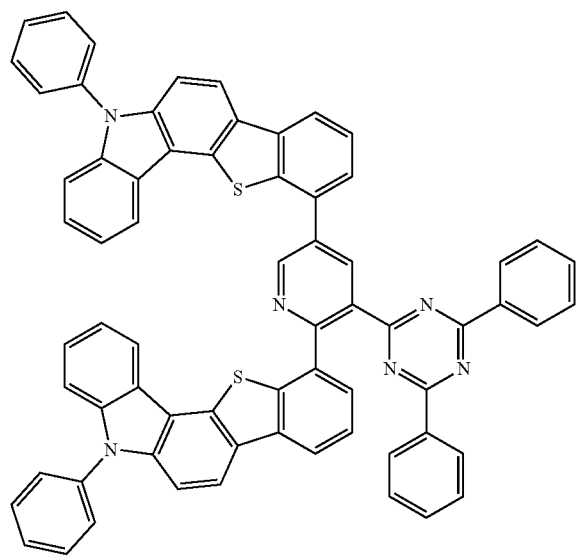
493
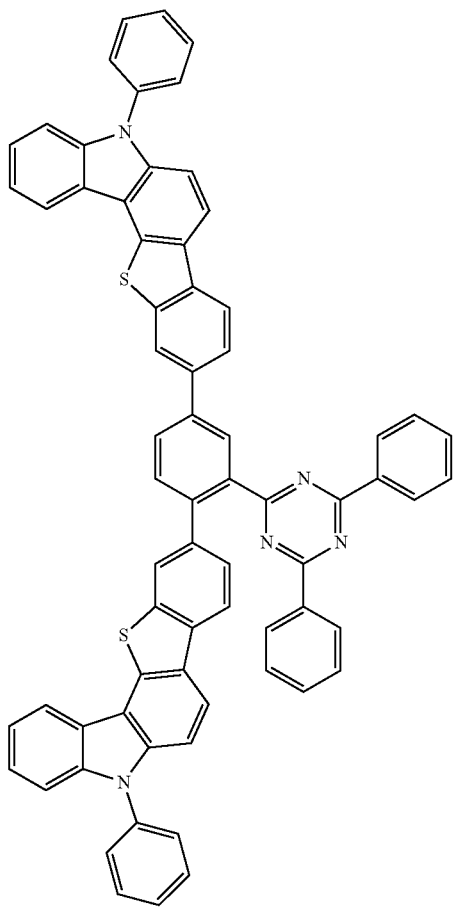
494

-continued
495
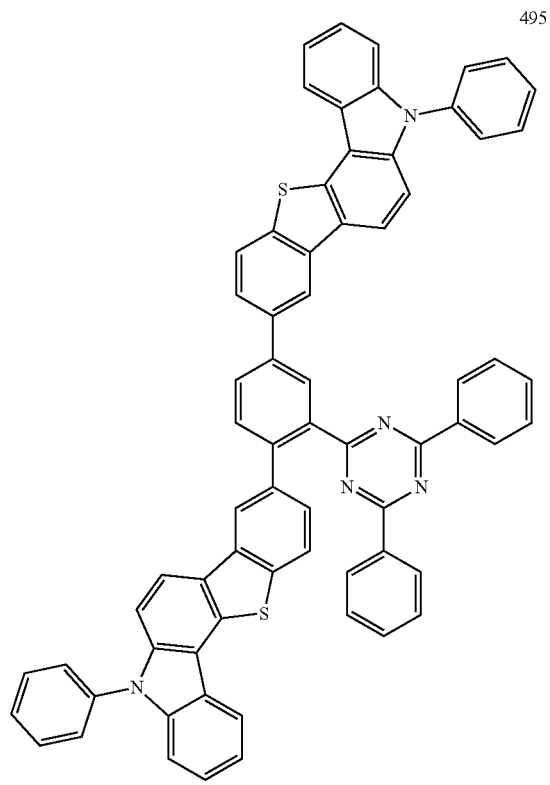
496
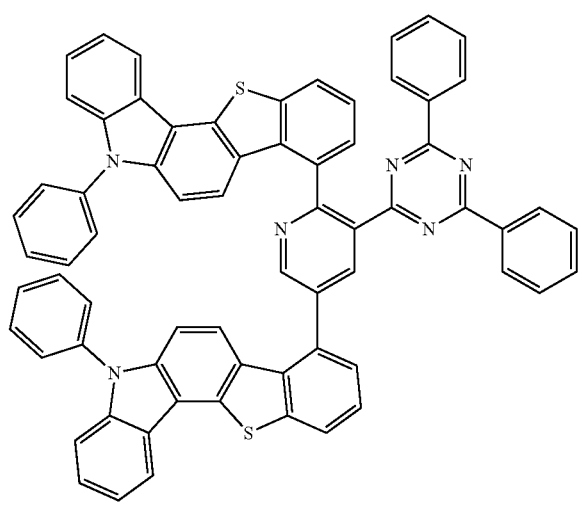

497
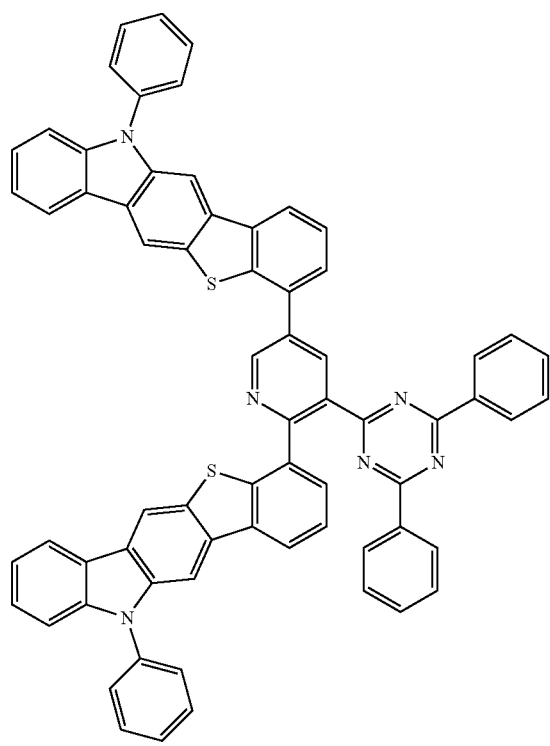
498
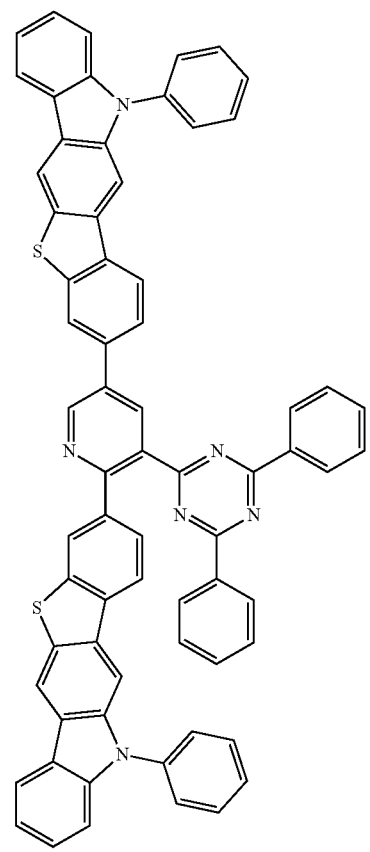

499
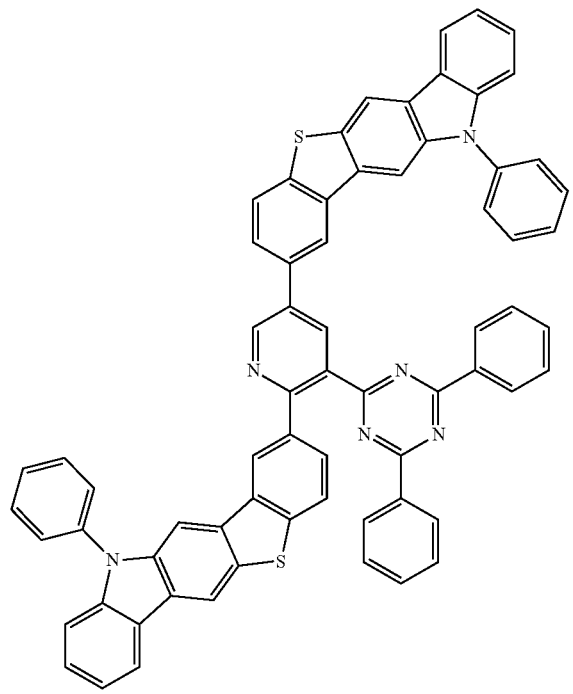
500
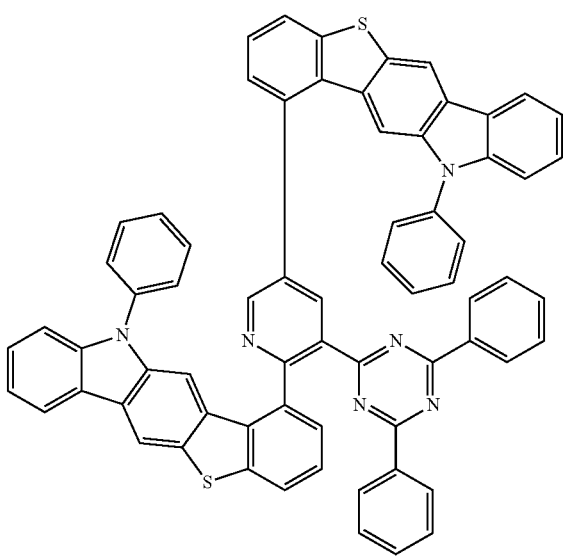
501
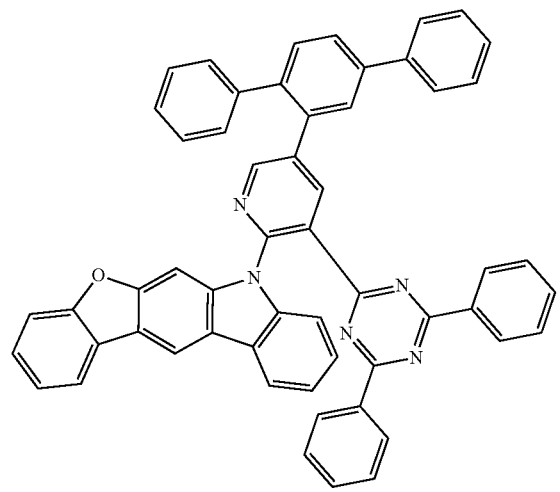
502
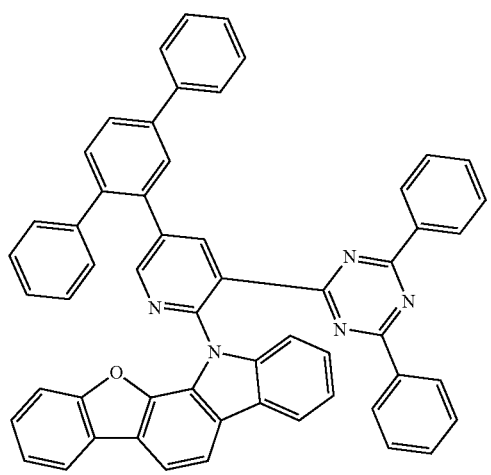

-continued
3487
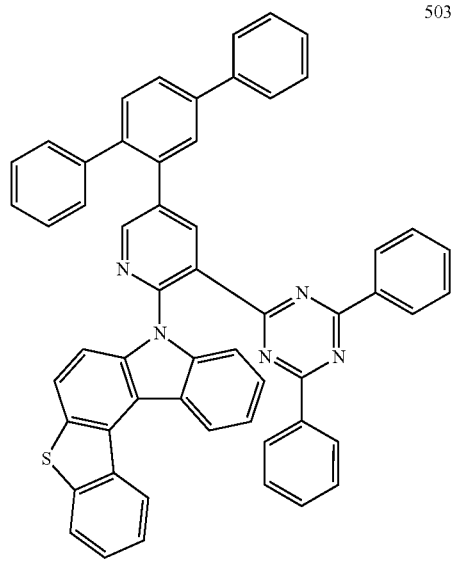
503
3488
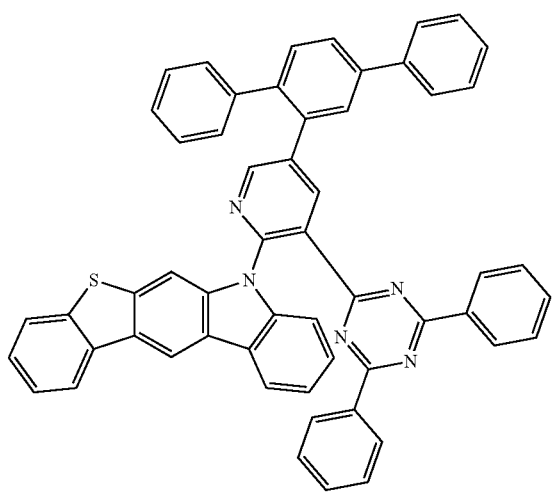
504
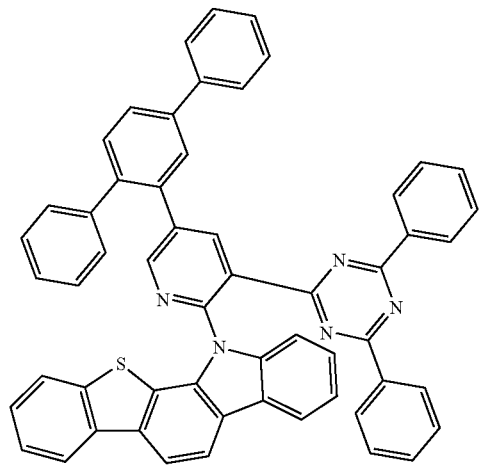
505
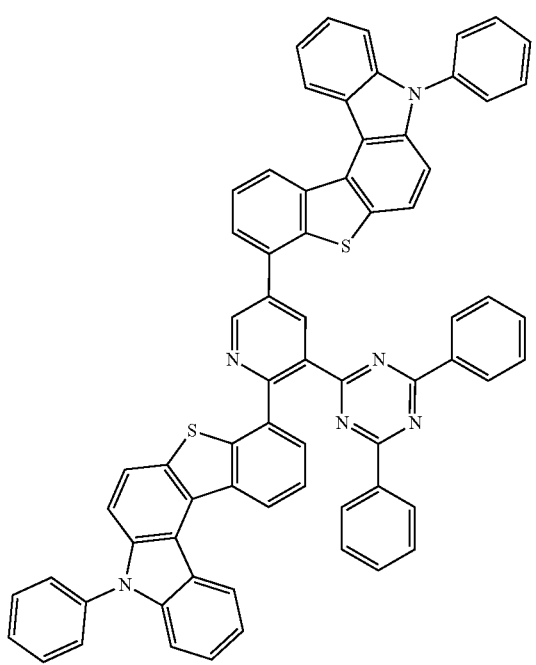
506

507
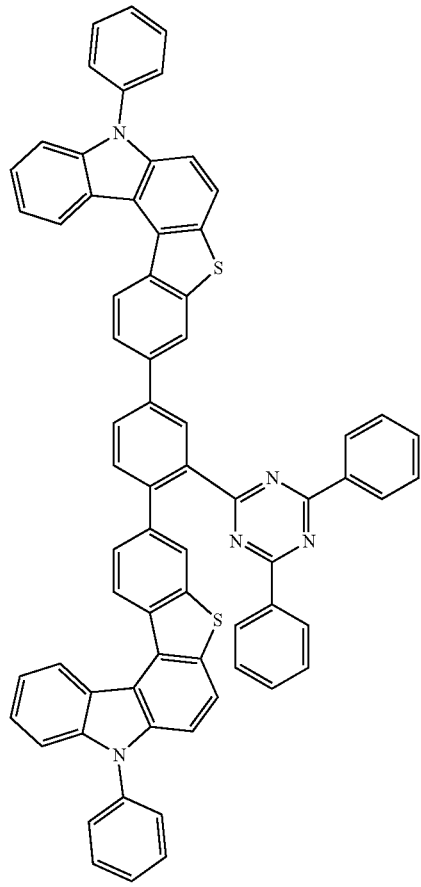
508
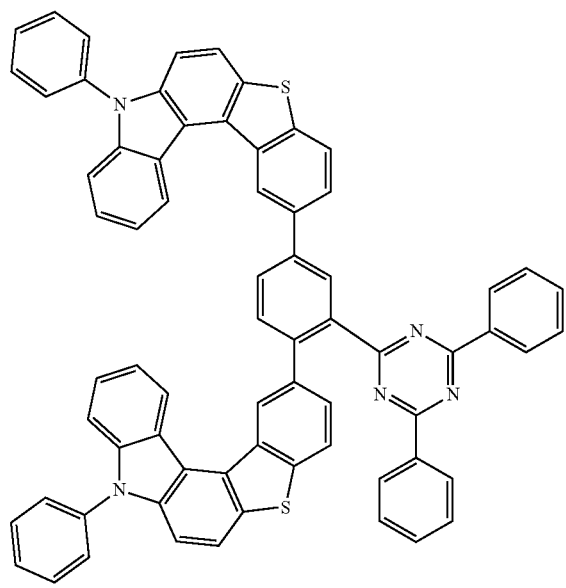
509
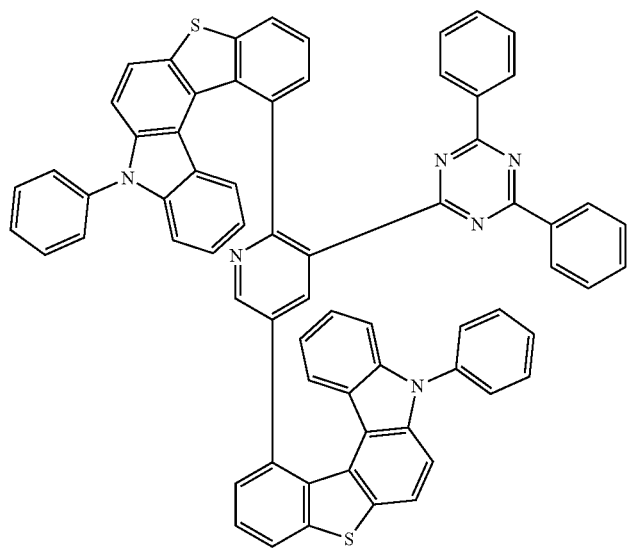

-continued
510
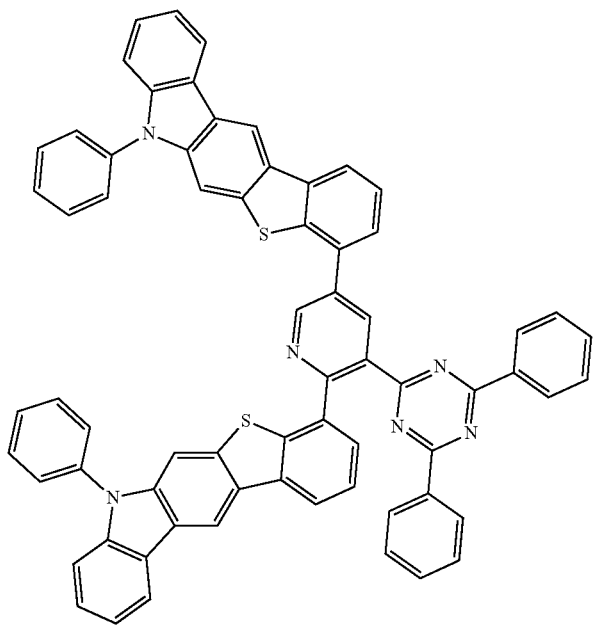
511
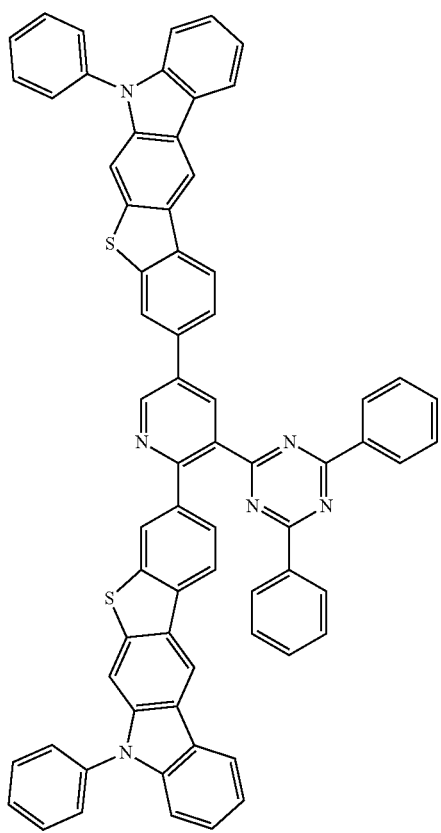
512
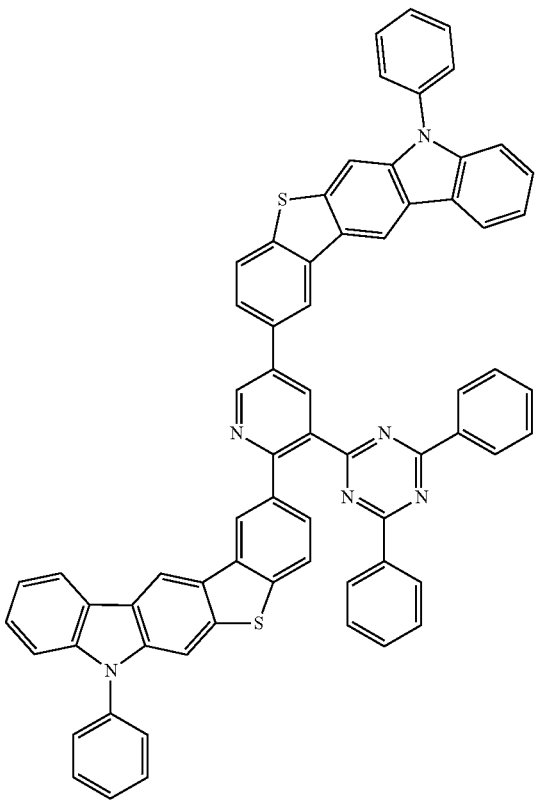

513
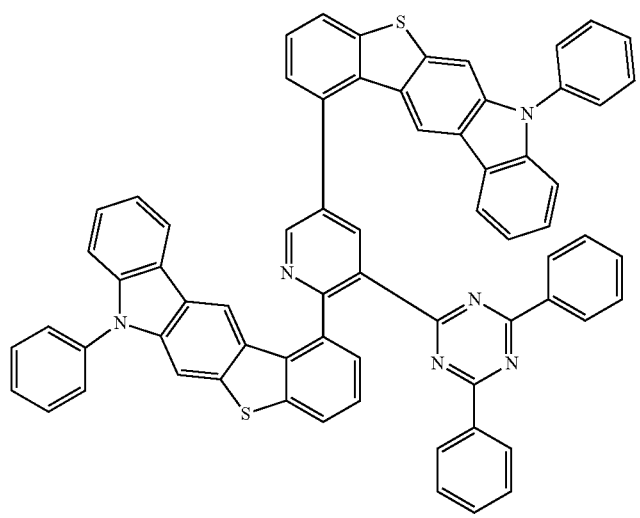
514
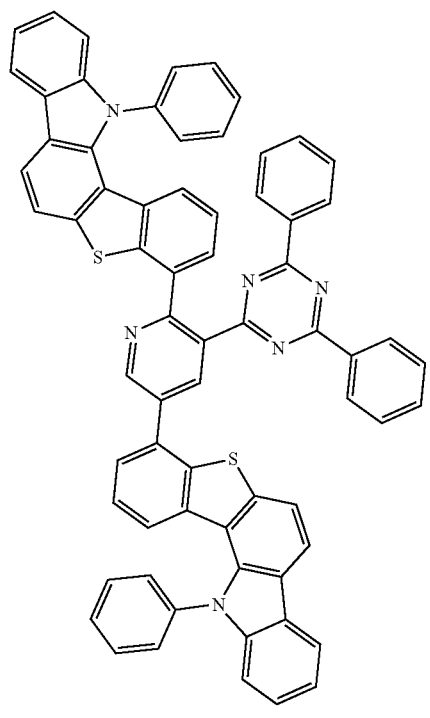
515
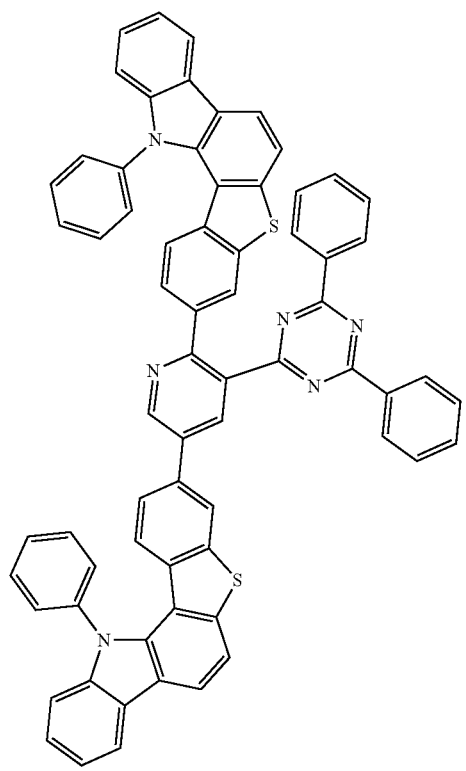

-continued
516
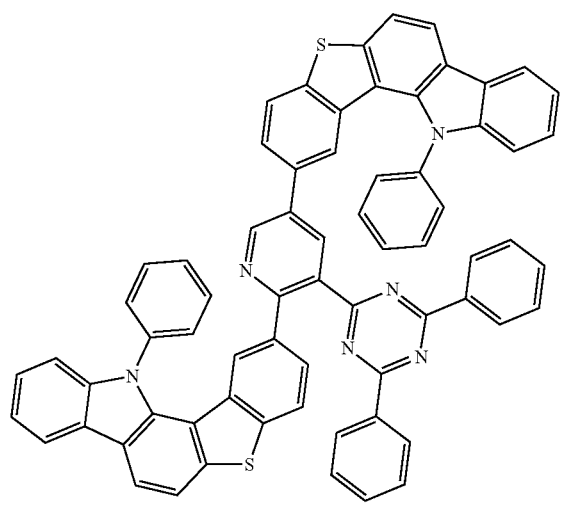
517
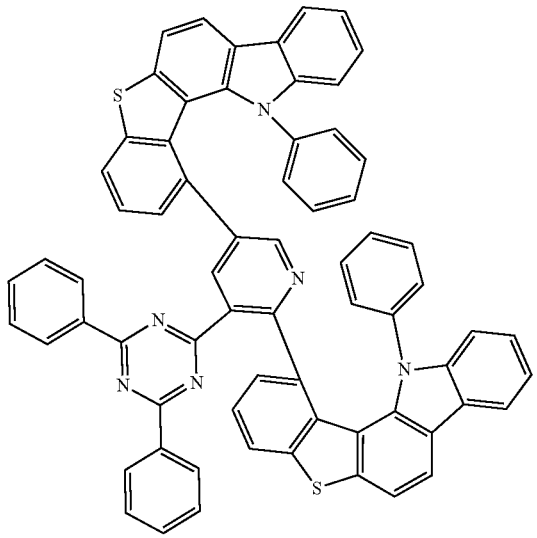
518
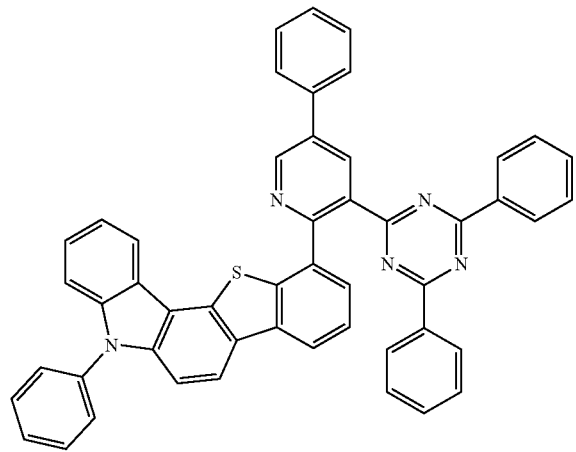
519
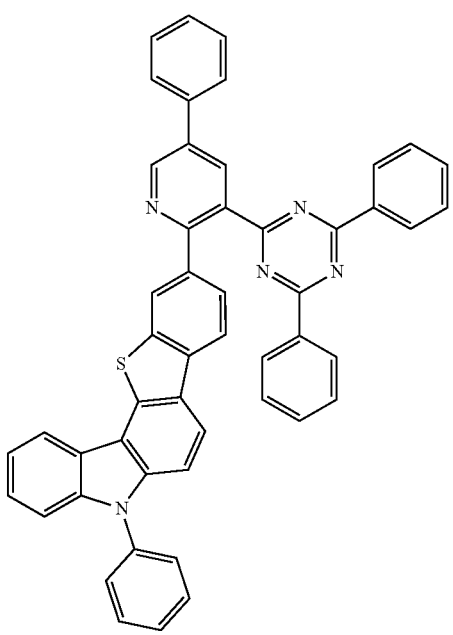

-continued
520
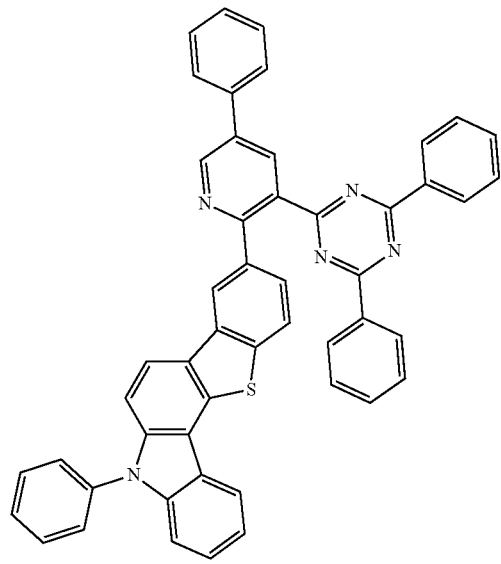
521
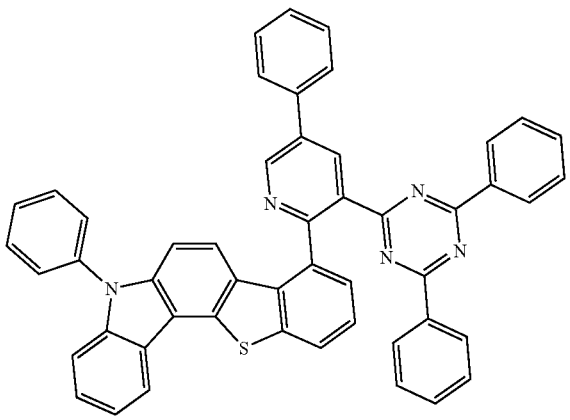
522
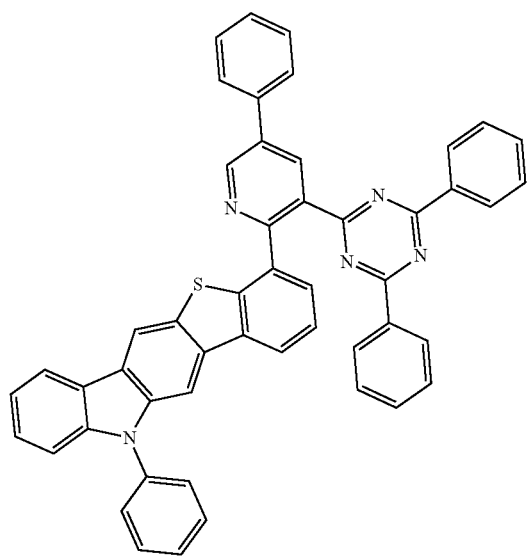
523
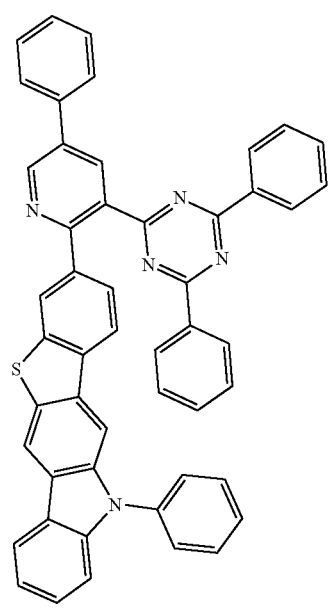

-continued
524
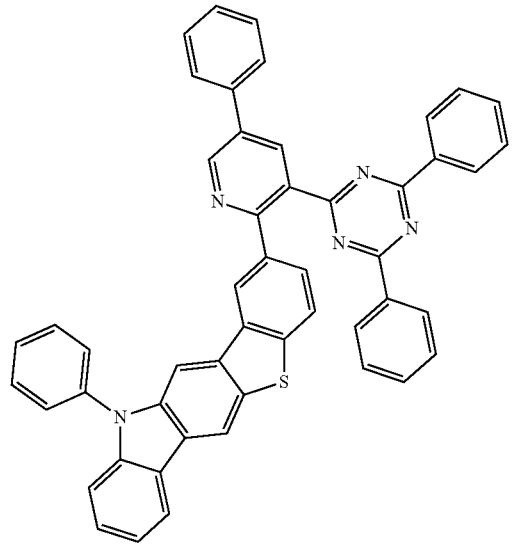
525
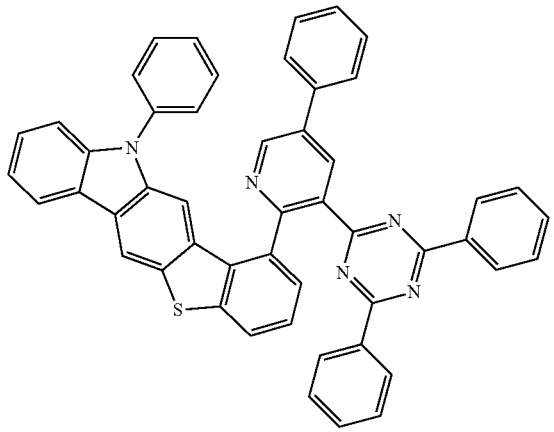
526
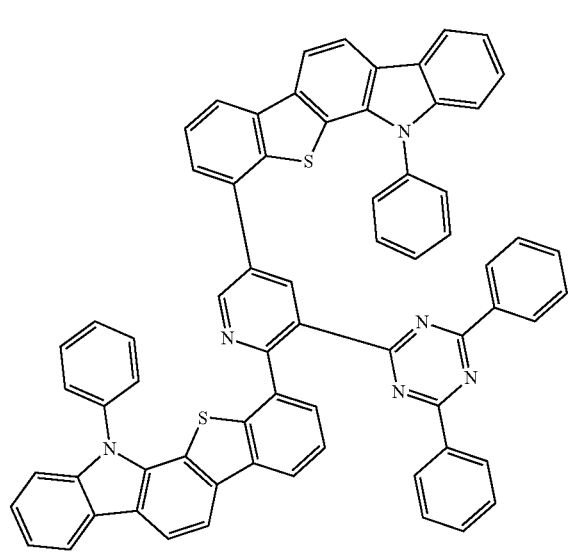
527
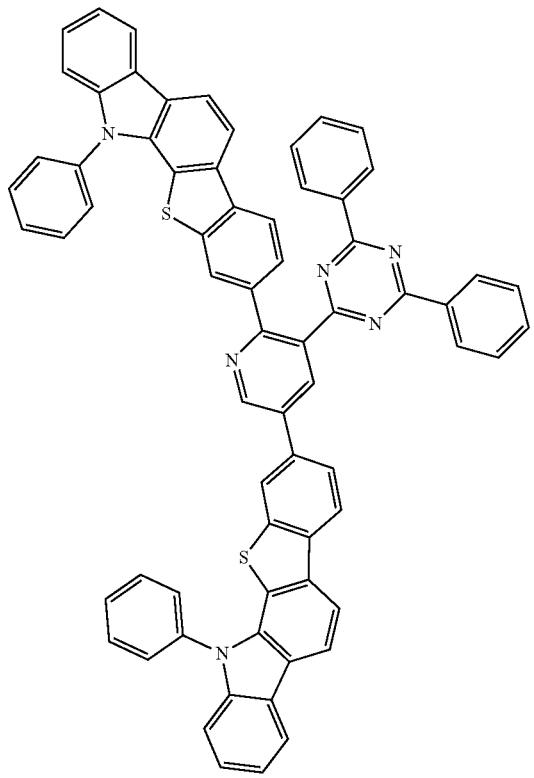

-continued
3501
528
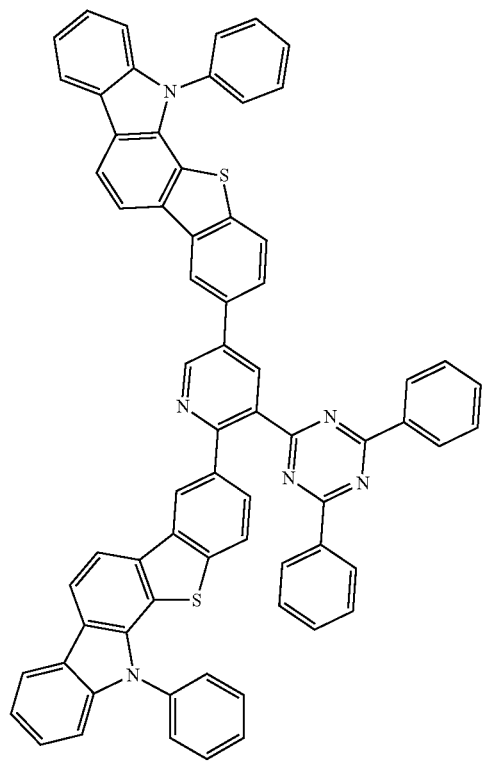
3502
529
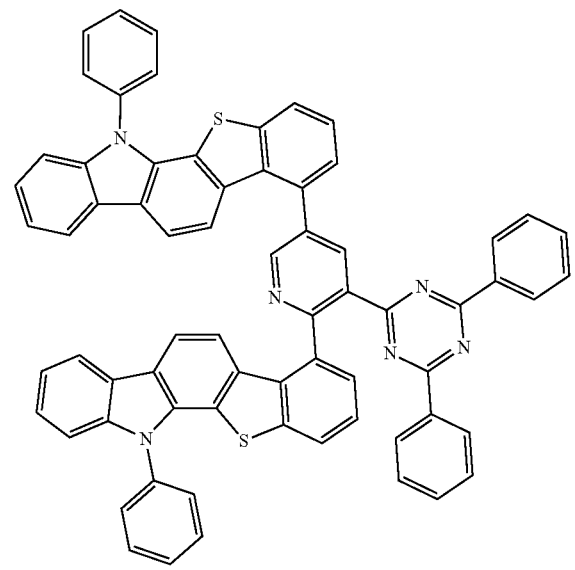
530
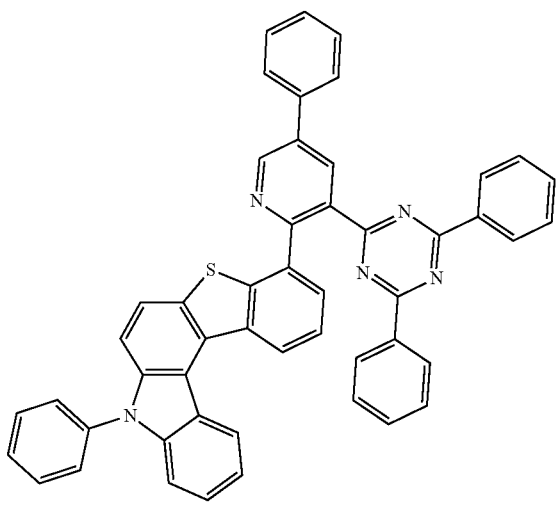
531
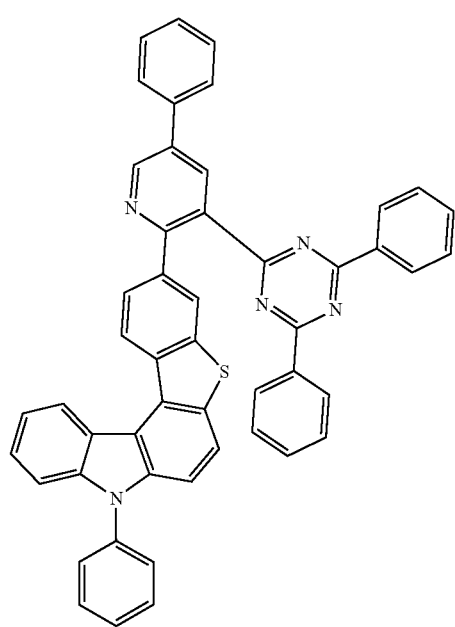

-continued
532
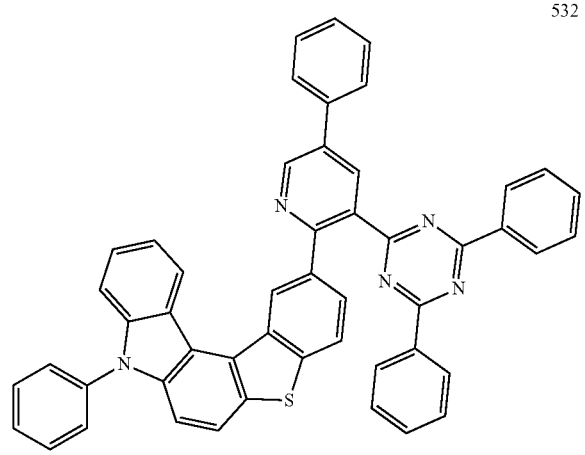
533
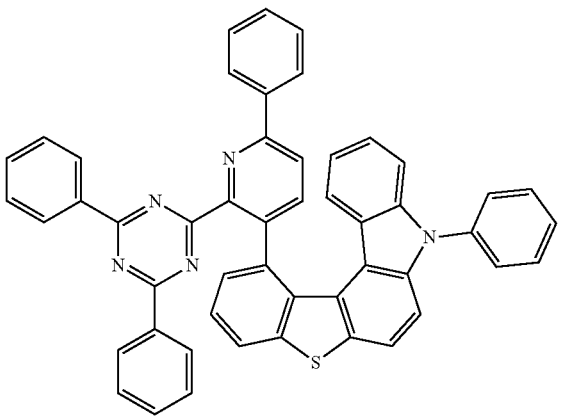
534
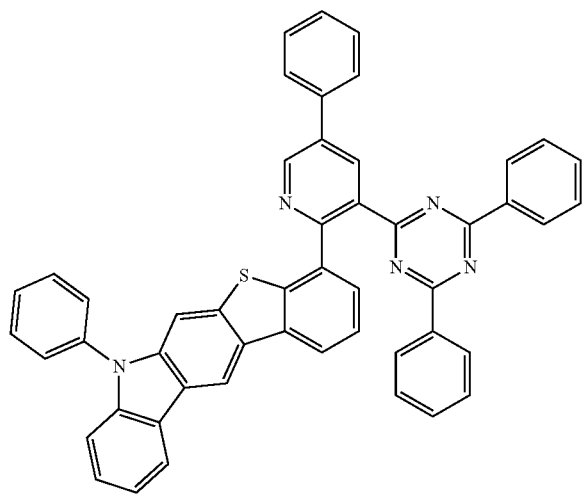
535
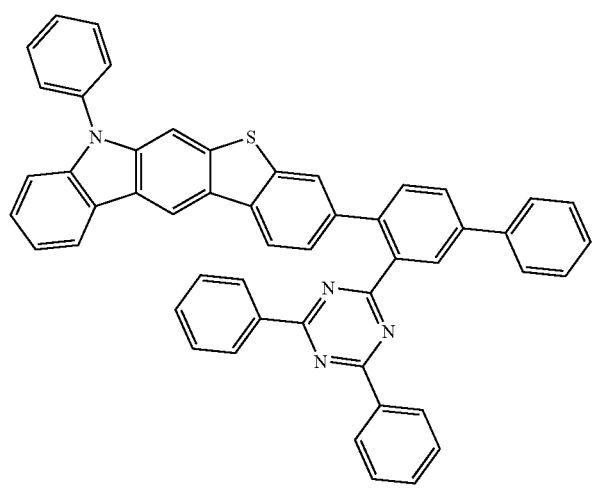

-continued
536
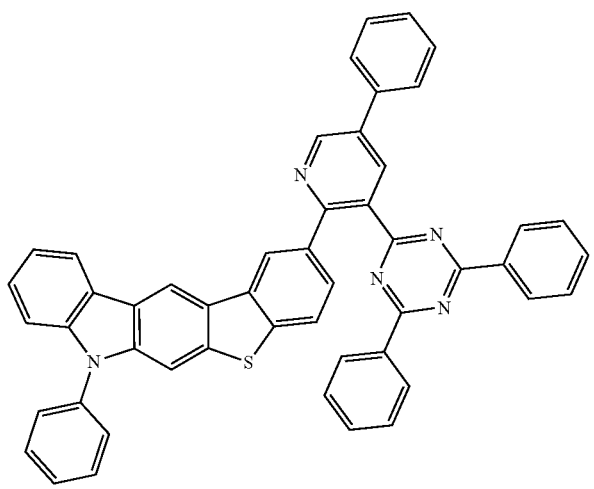
537
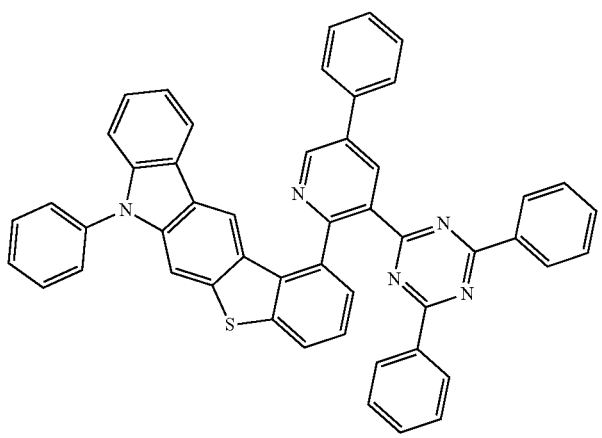
538
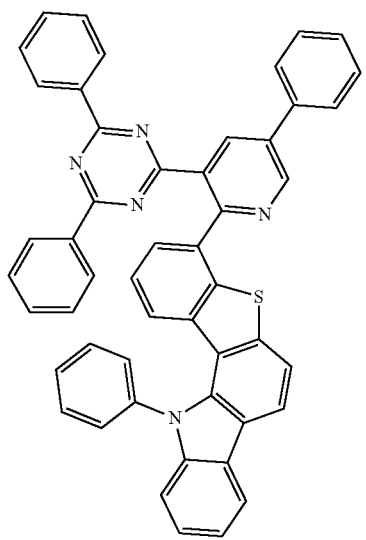
539
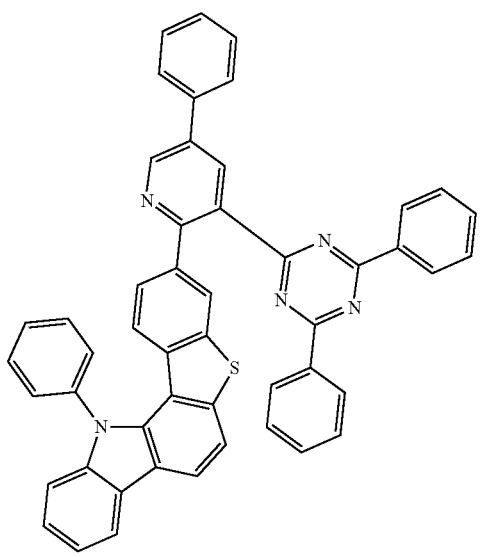

-continued
540
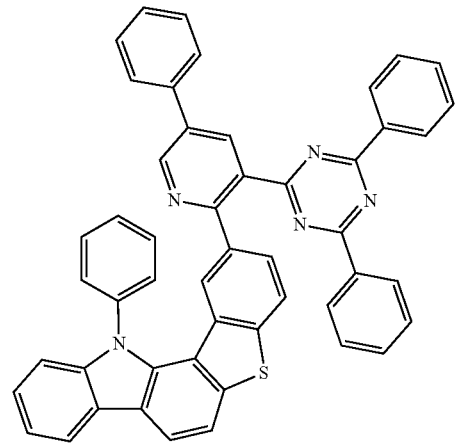
541
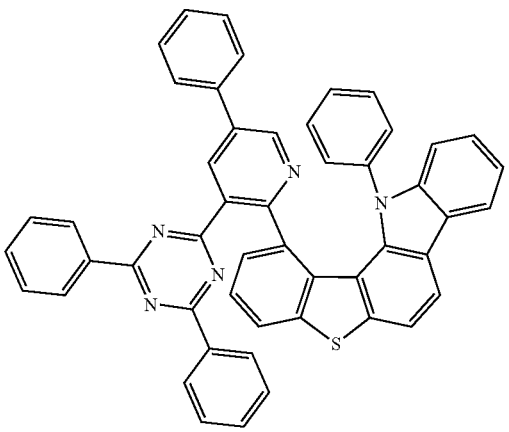
542
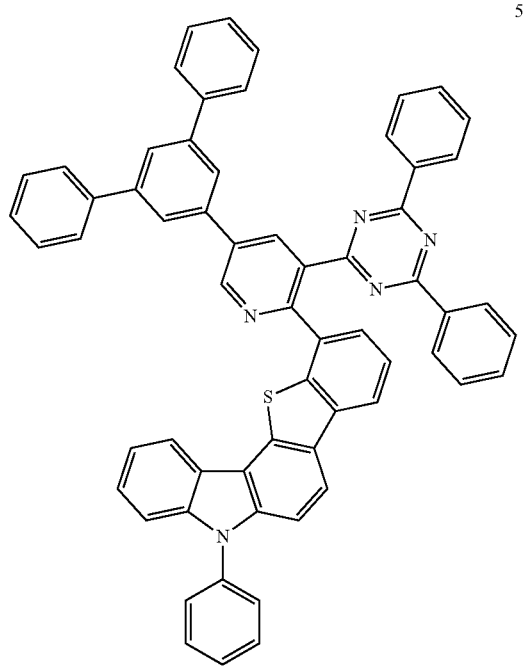
543
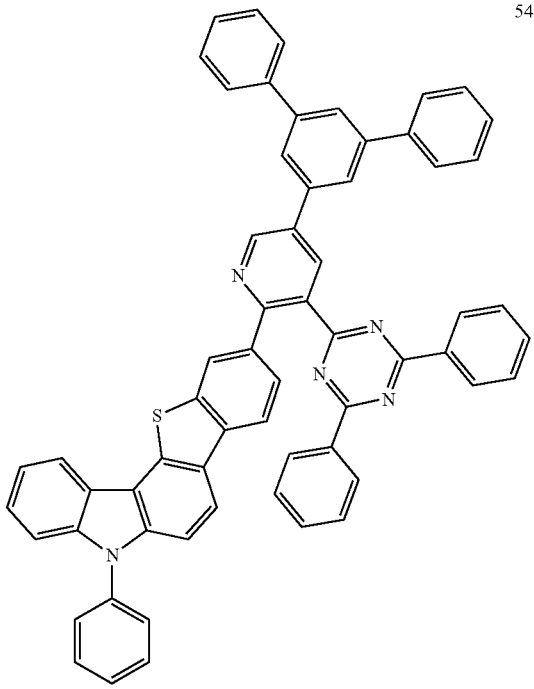
544
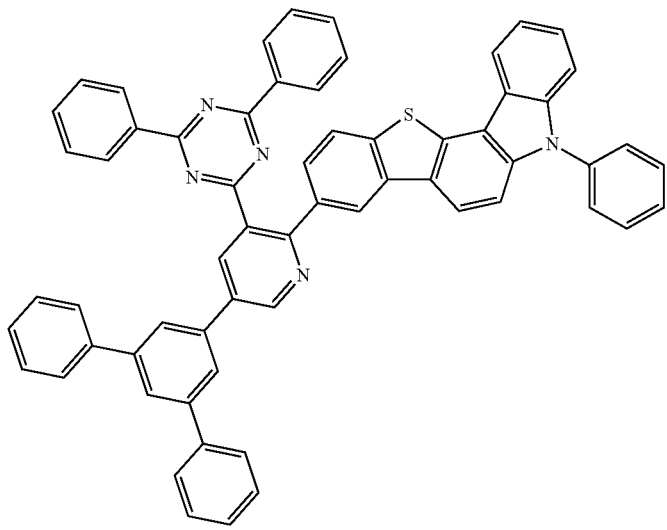

545
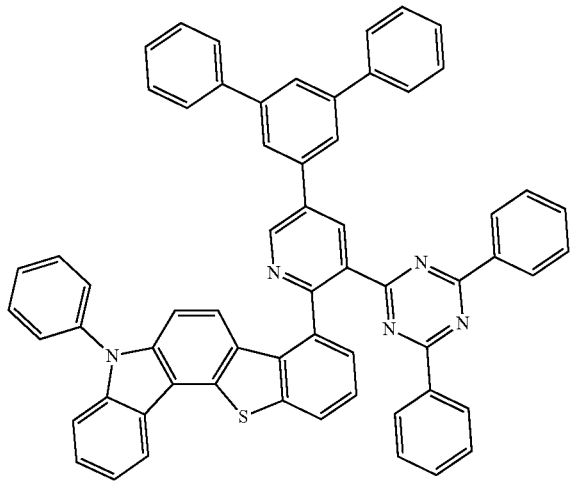
546
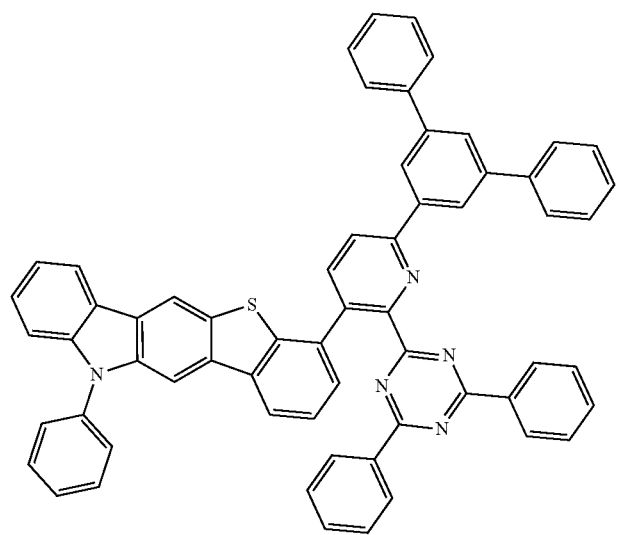

-continued
3511
547
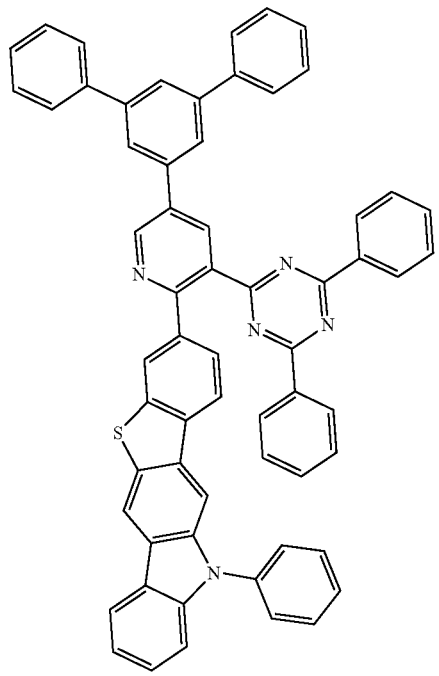
3512
548
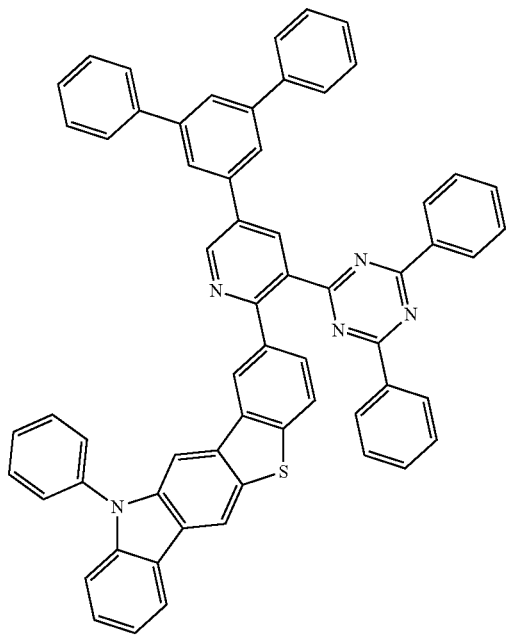
549
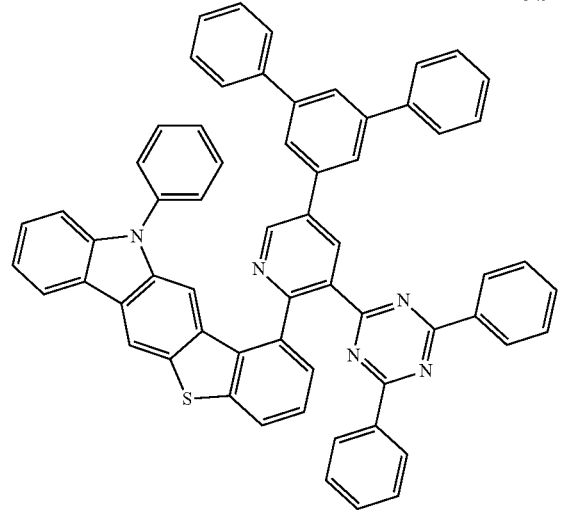
550
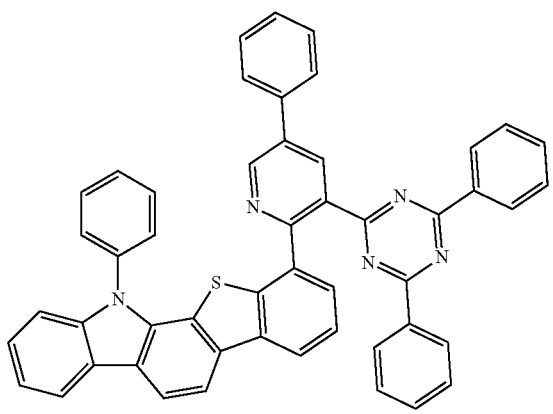

551
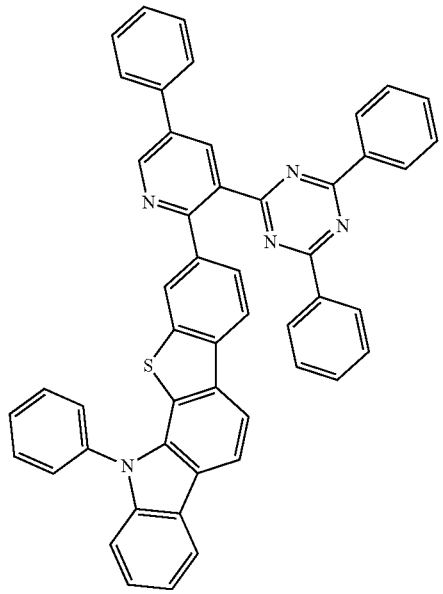
552
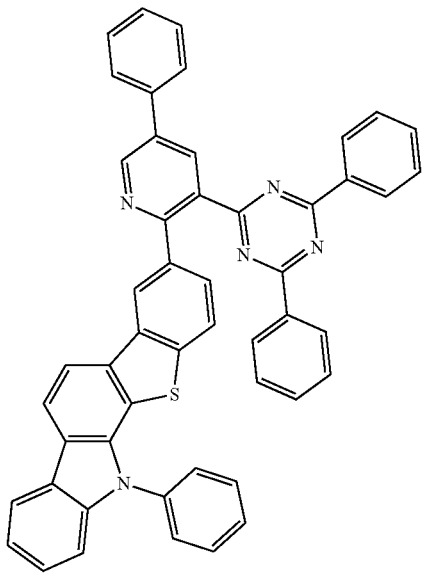
553
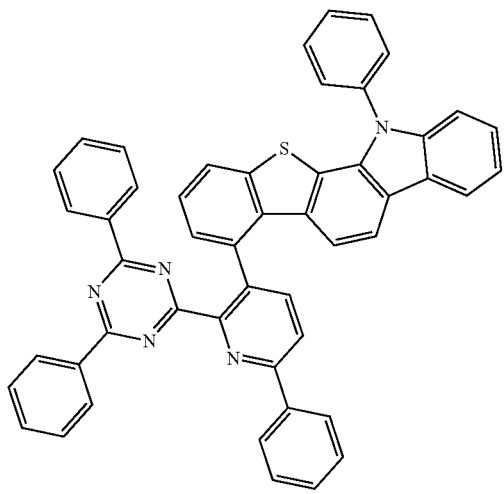
554
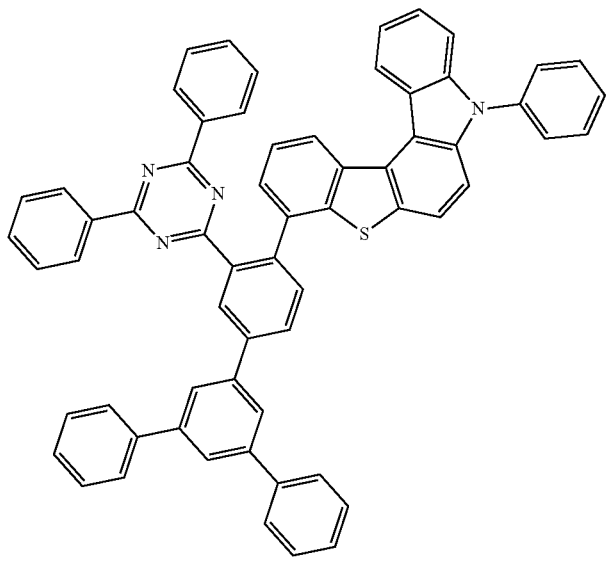

-continued
3515
555
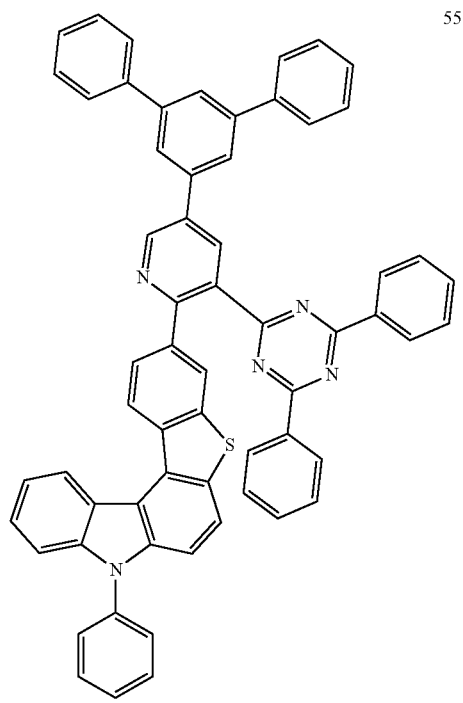
3516
556
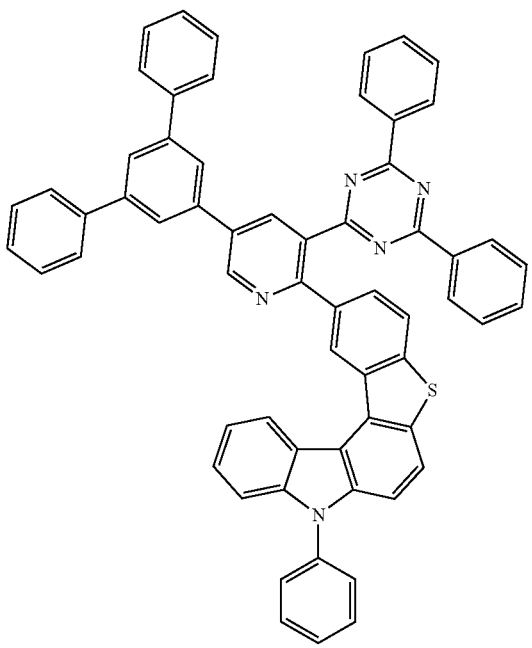
557
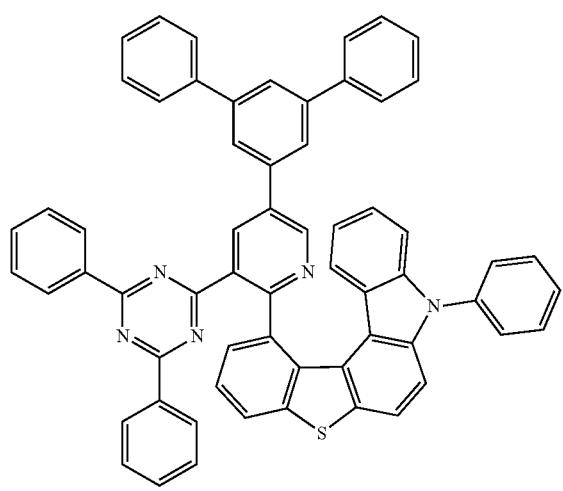

558
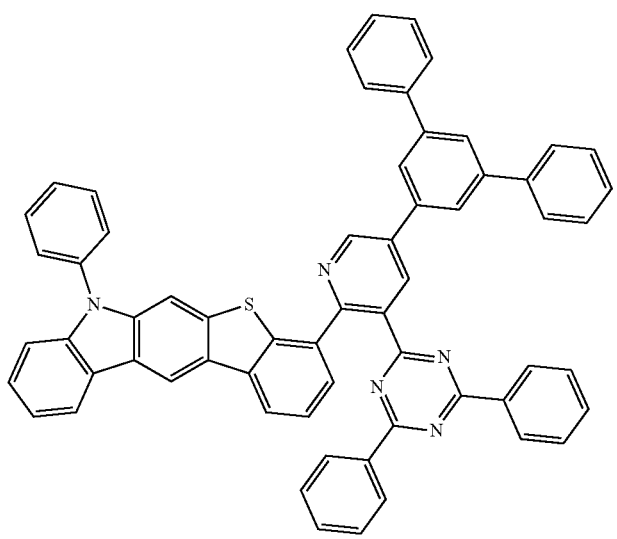
559
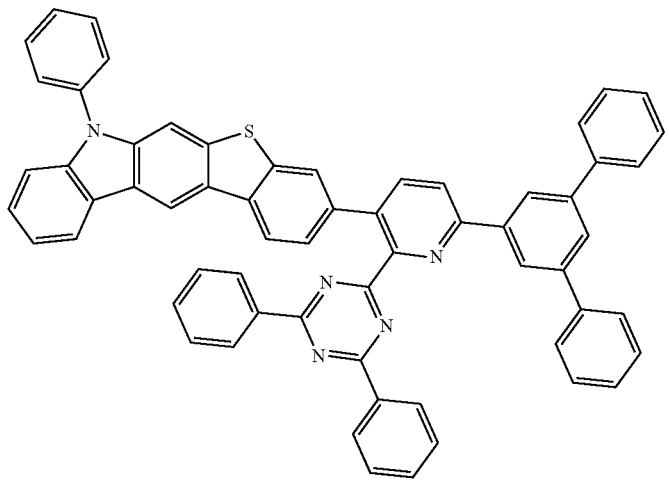
560
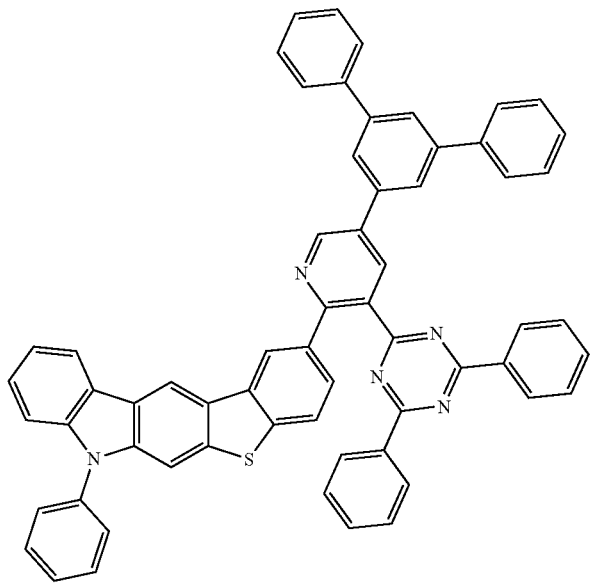

-continued
561
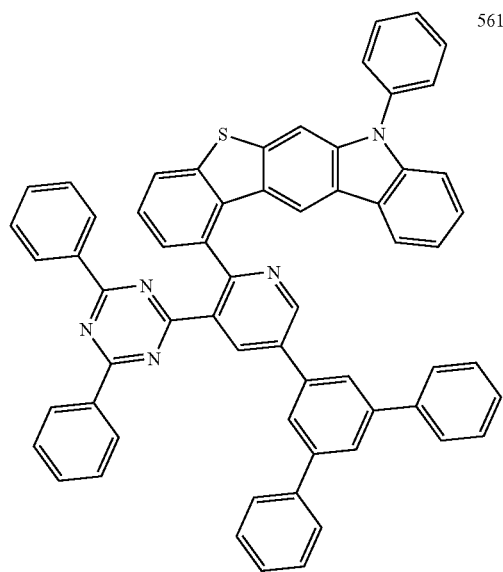
562
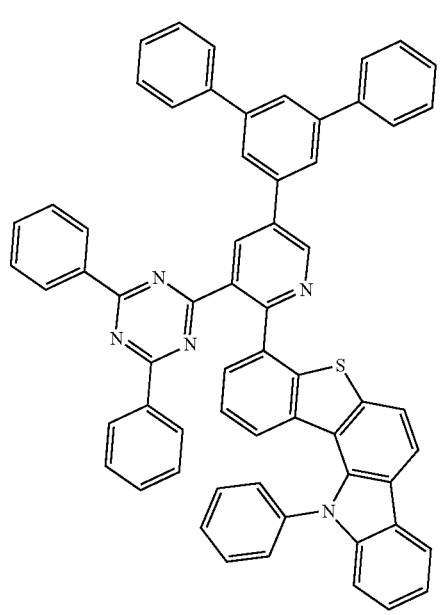
563
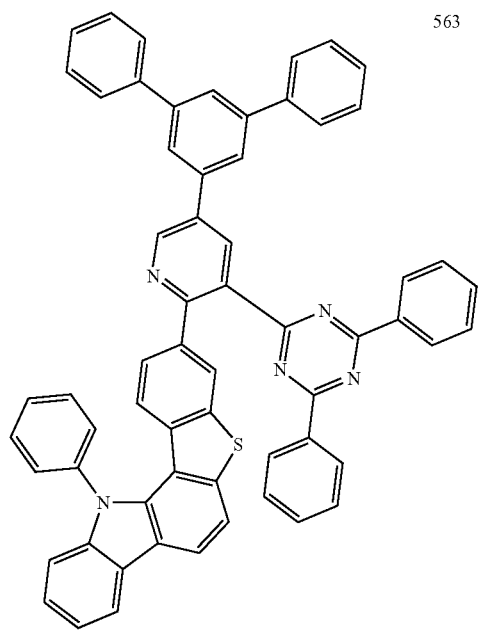
564
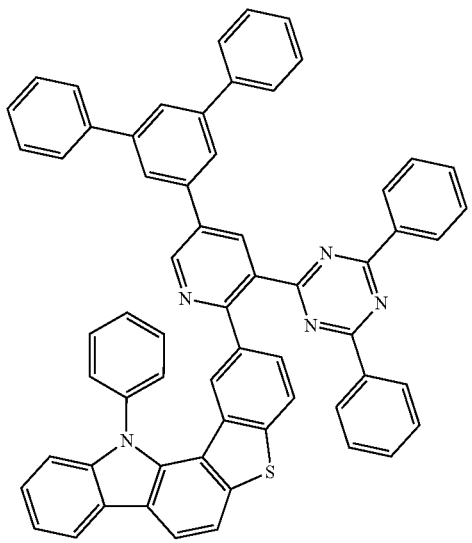

3521
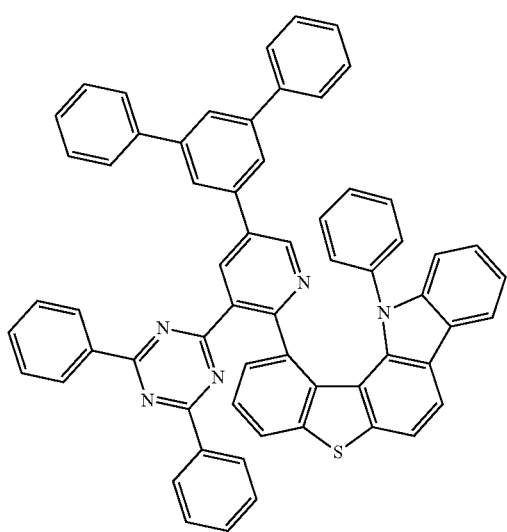
3522
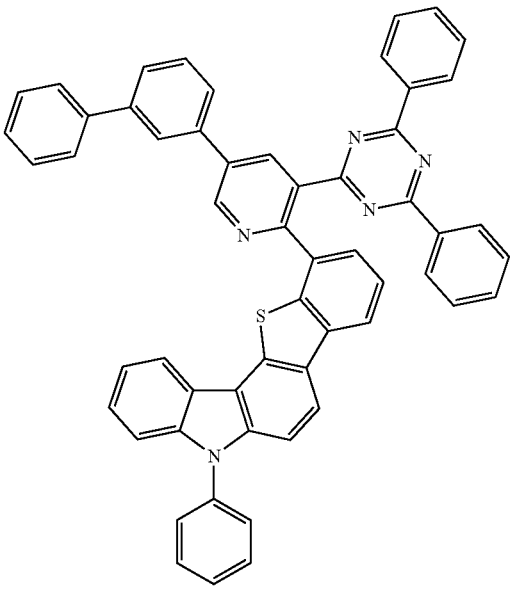
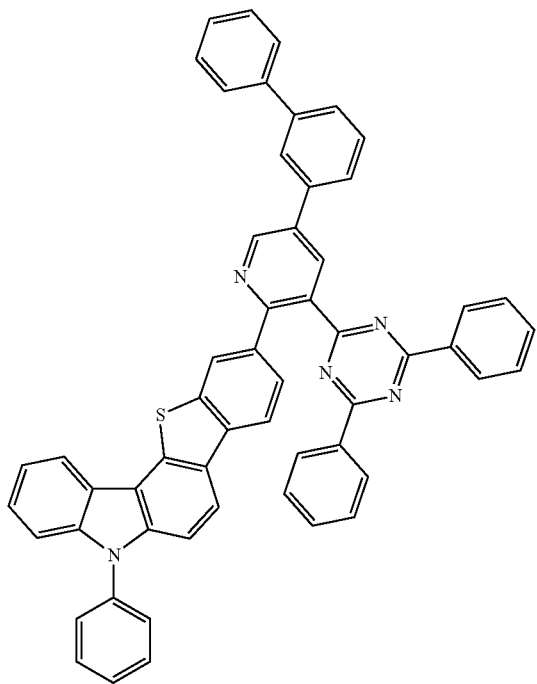

-continued
568
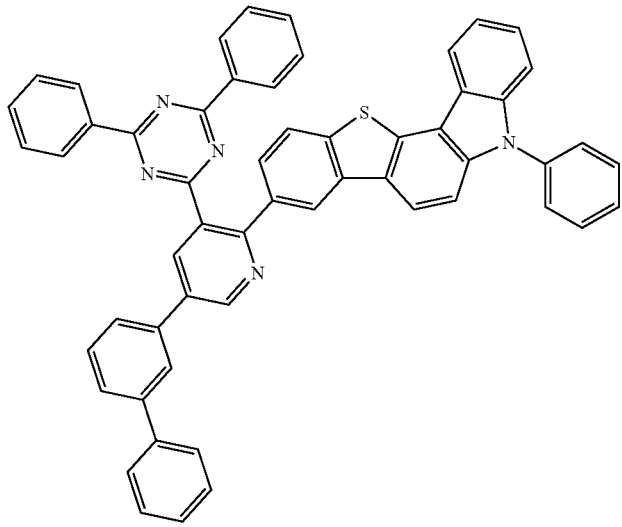
569
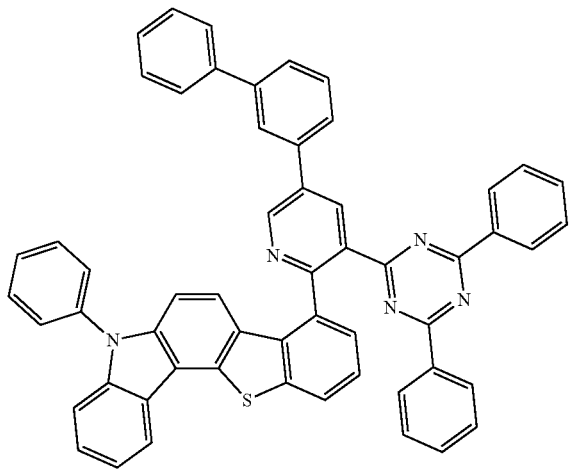
570
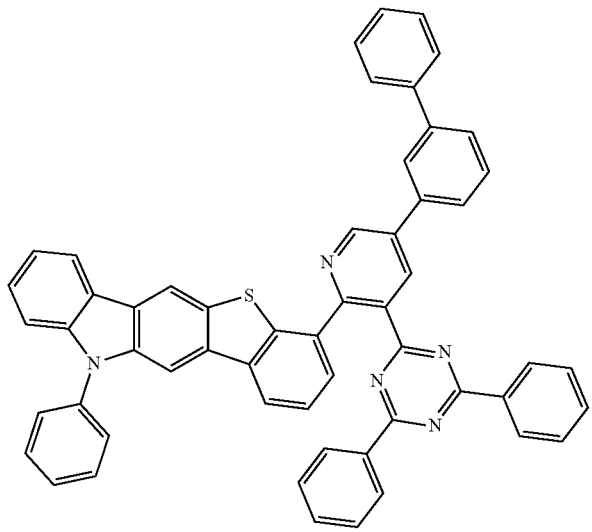

-continued
3525
571
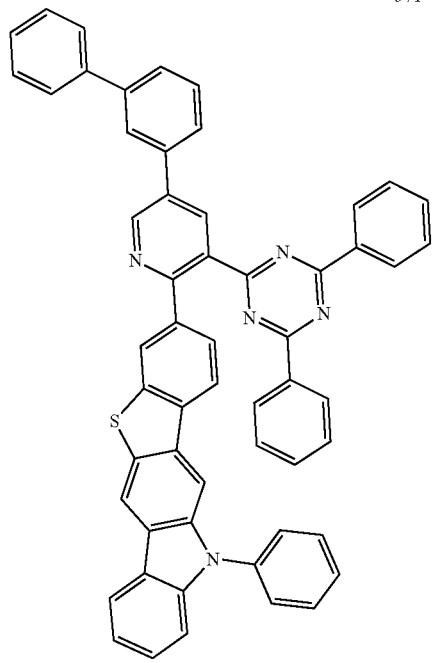
3526
572
573
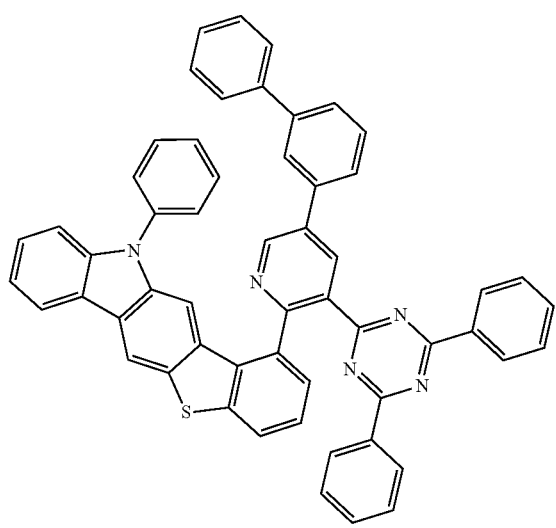
574
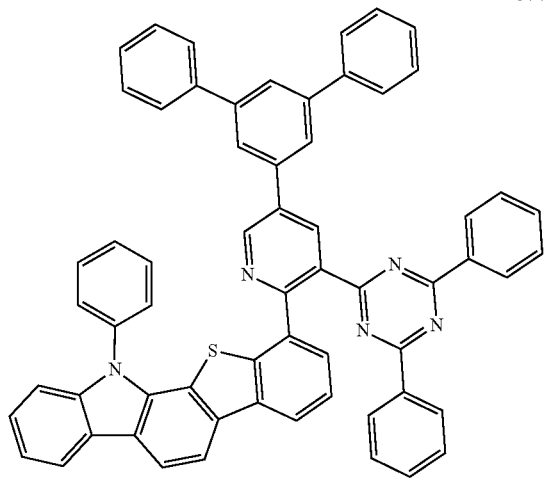

-continued
575
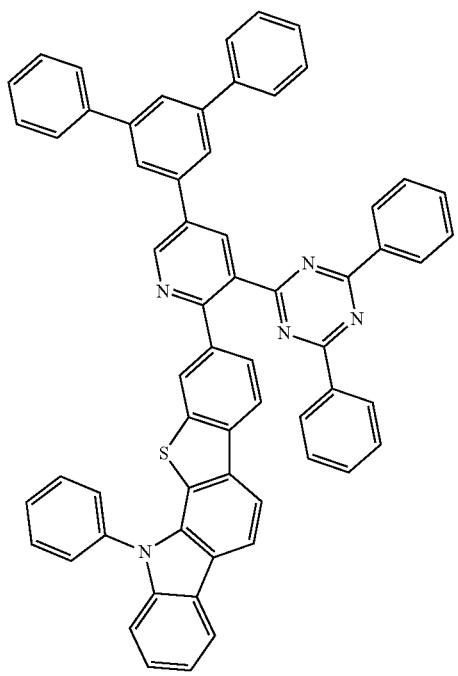
576
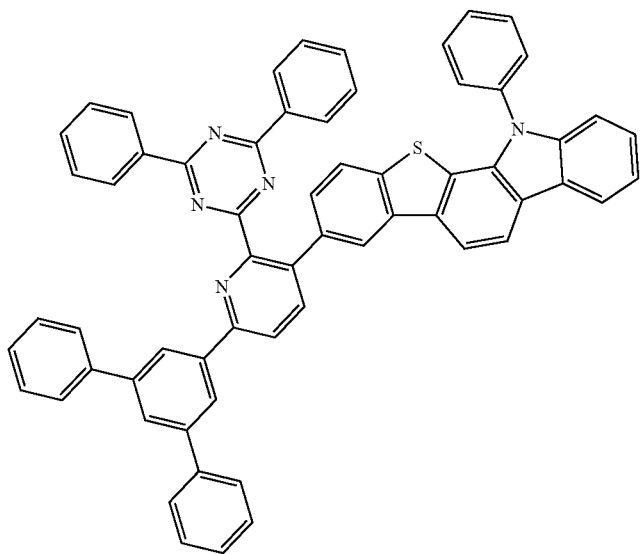

577
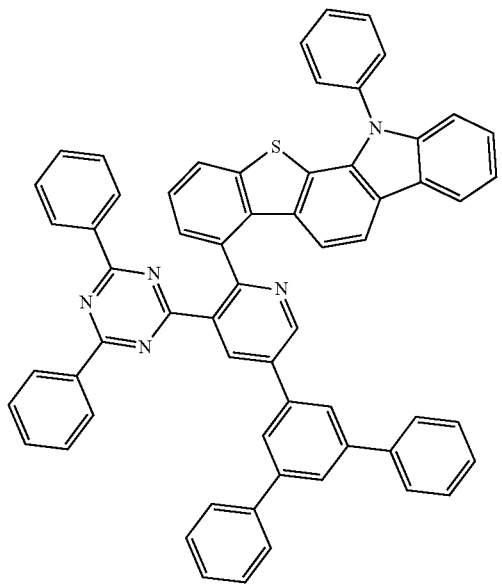
578
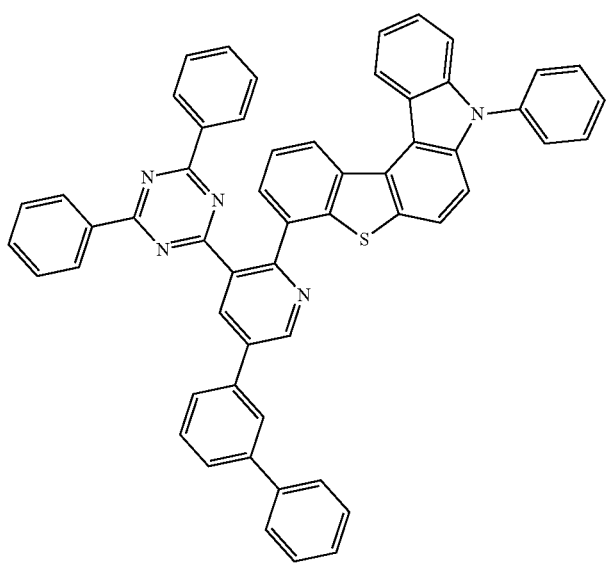

-continued
579
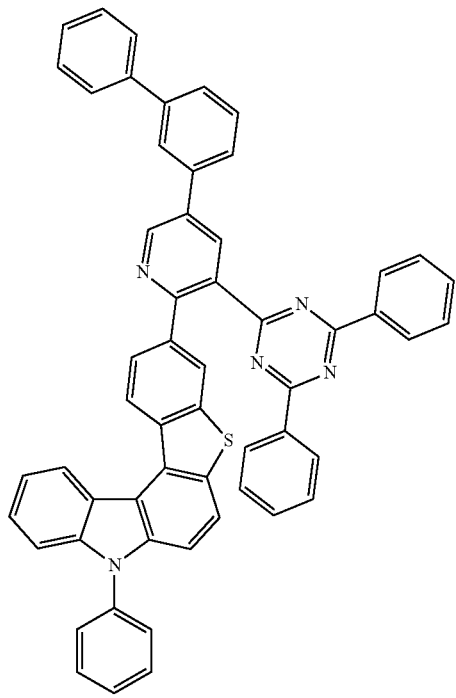
580
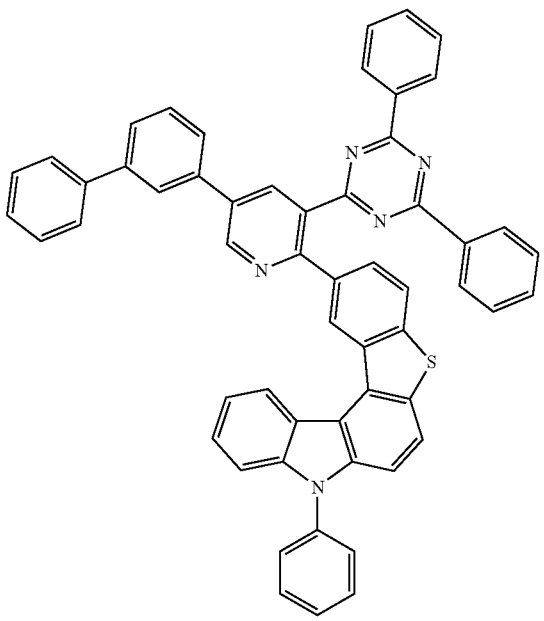
581
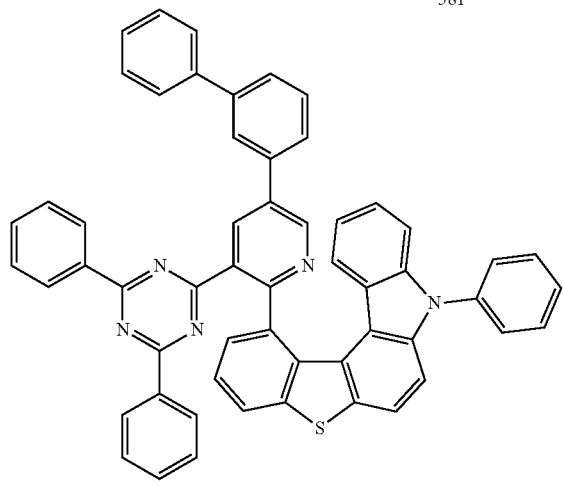

582
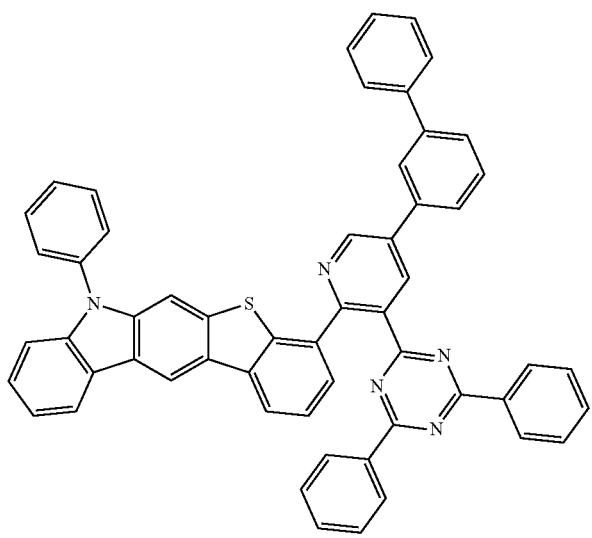
583
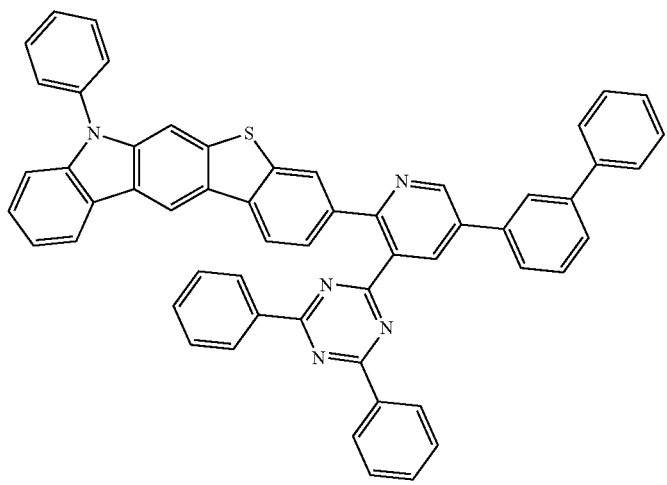
584
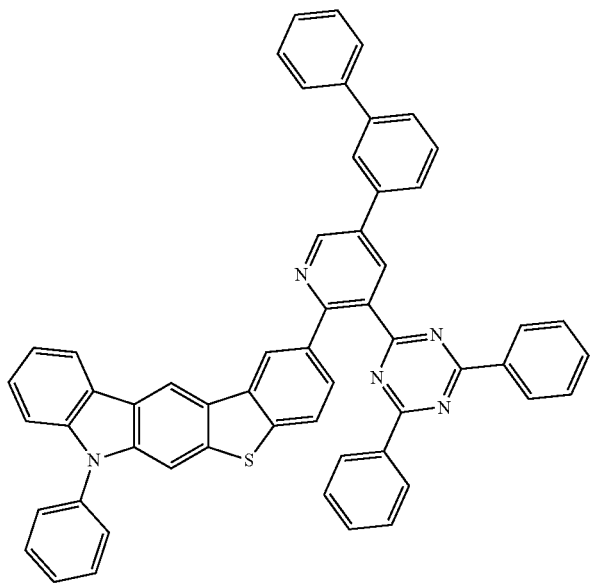

3535
585
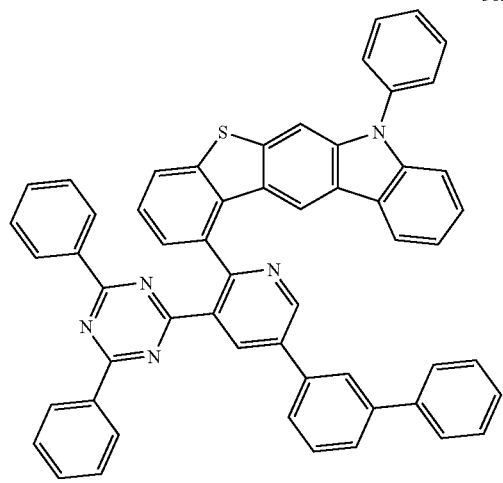
3536
586
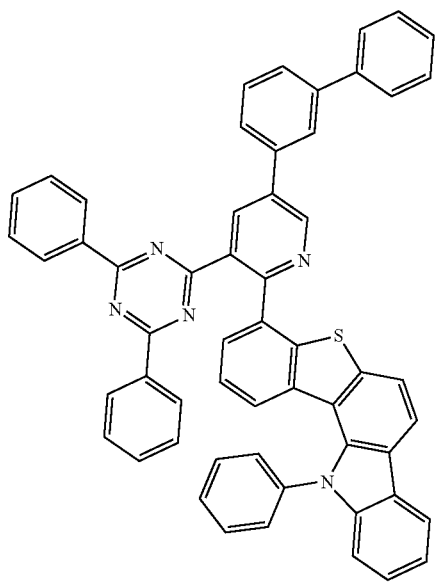
587
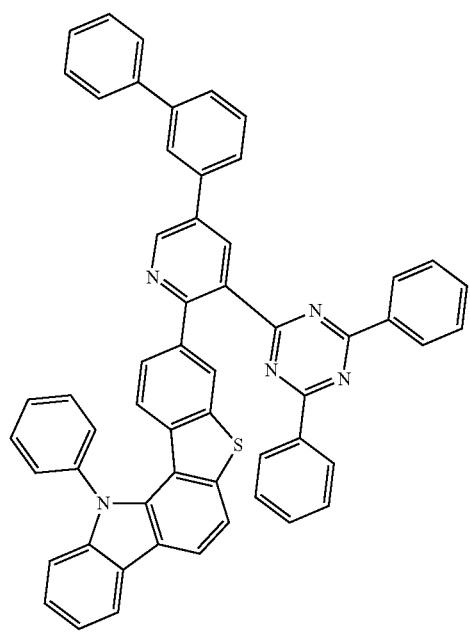
588
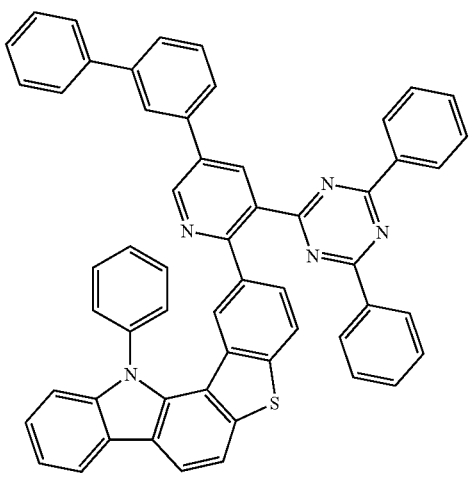

3537
-continued
589
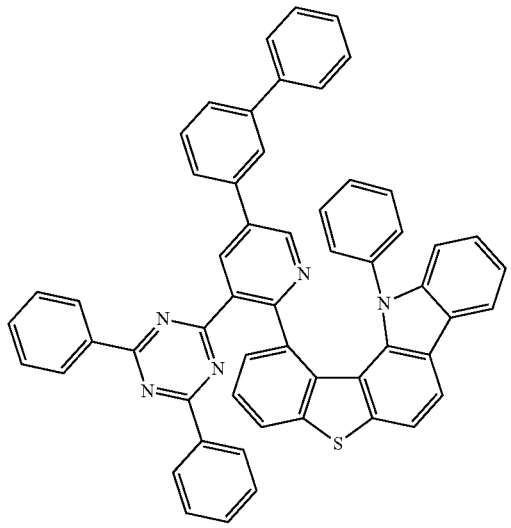
3538
590
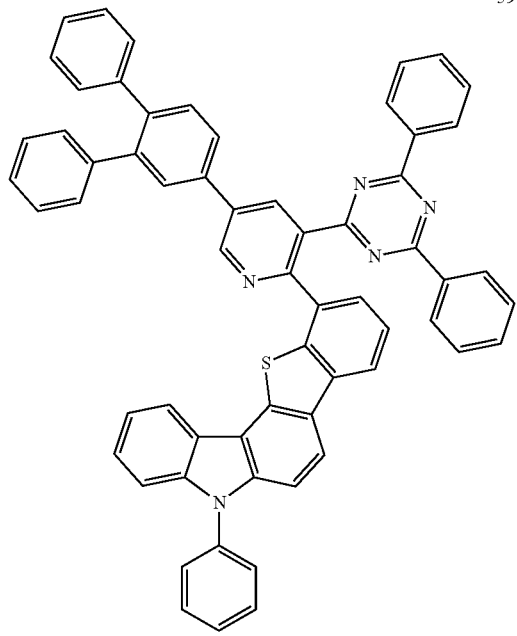
591
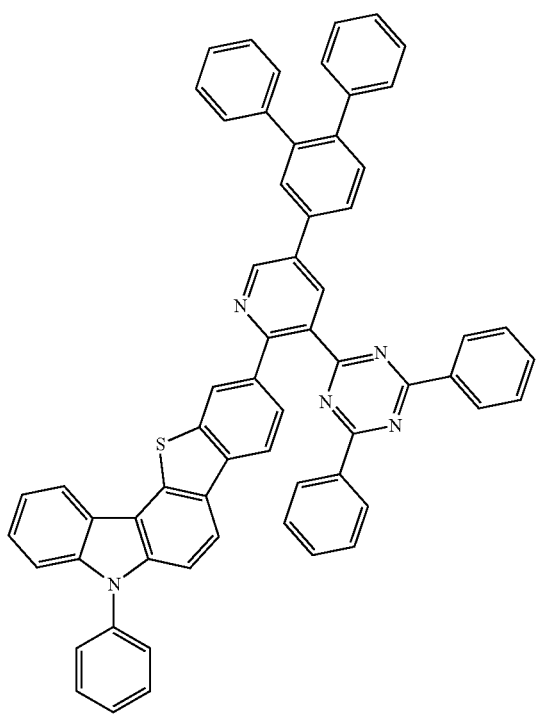

-continued
592
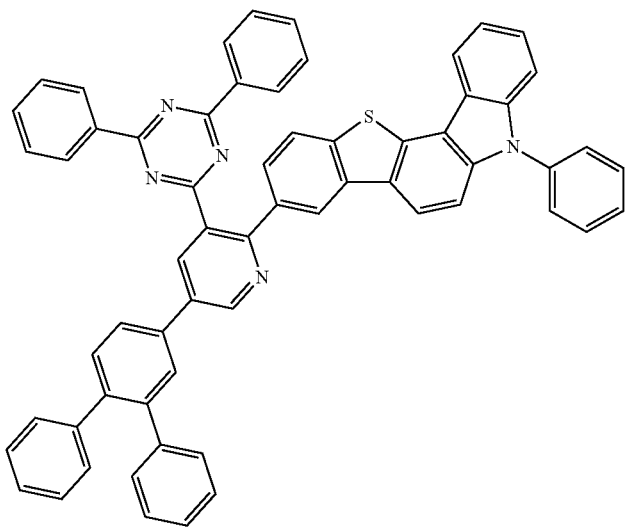
593
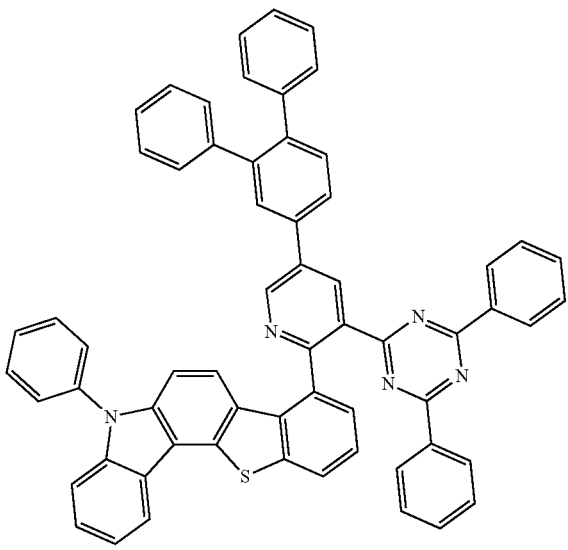
594
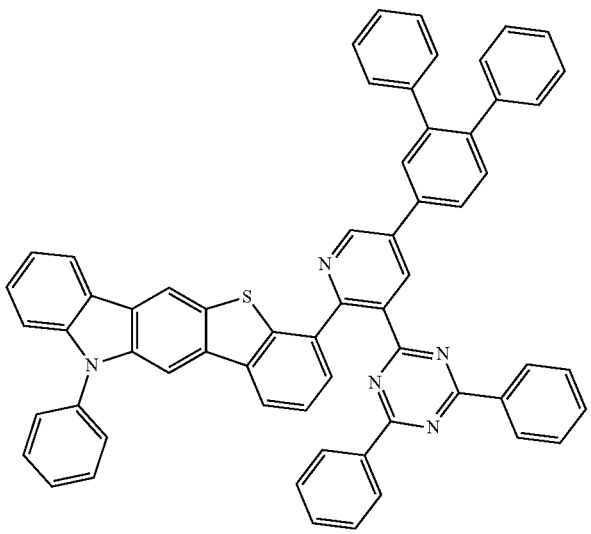

595
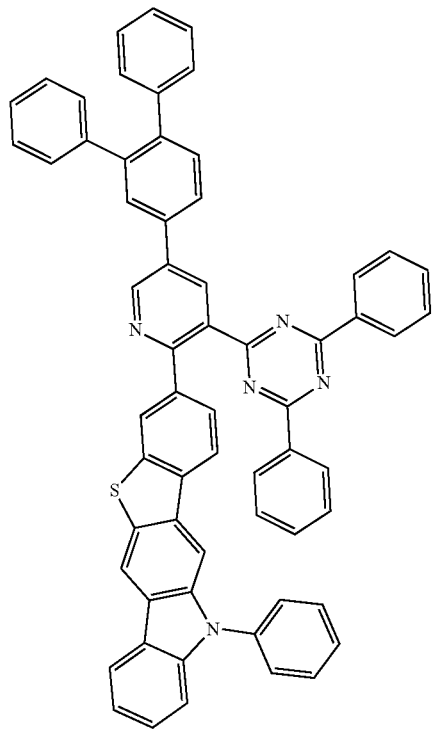
596
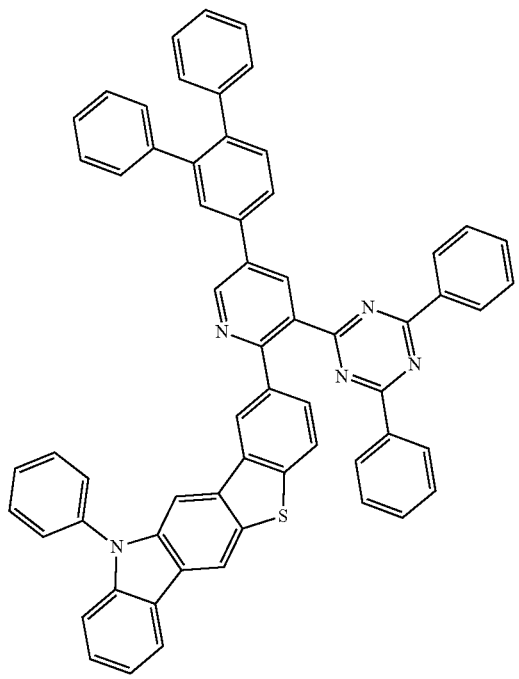
597
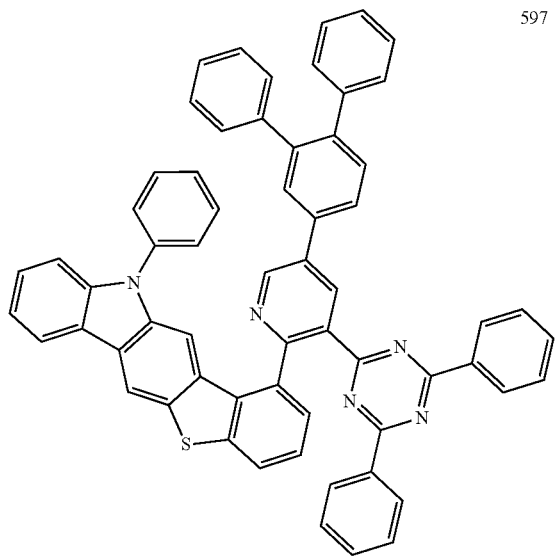
598
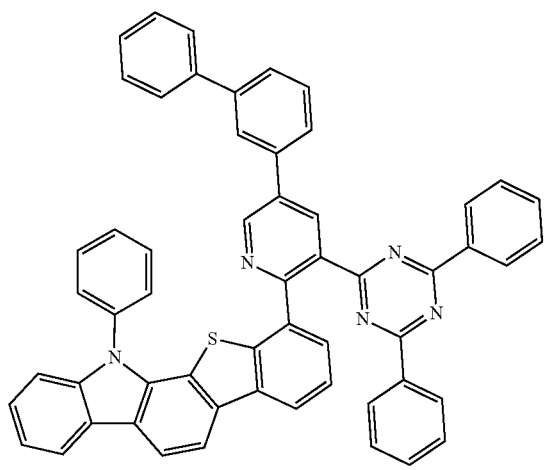

599
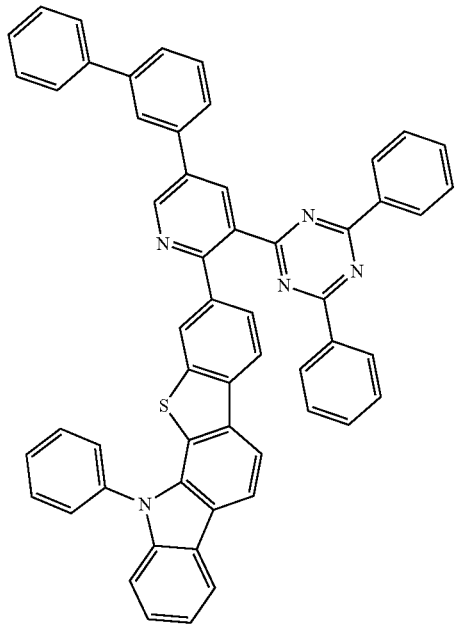
600
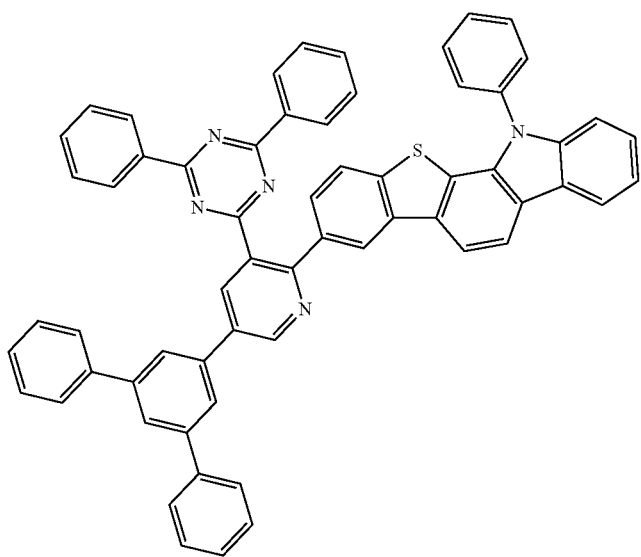

601
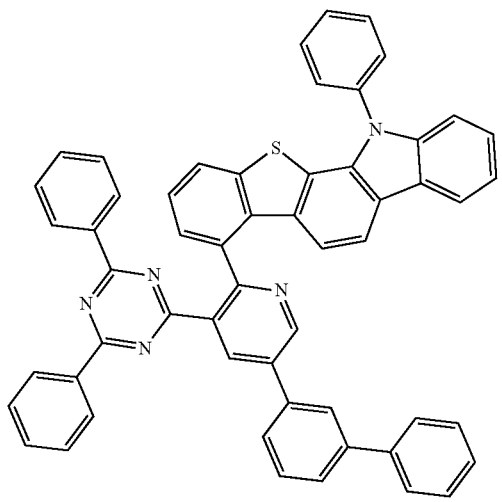
602
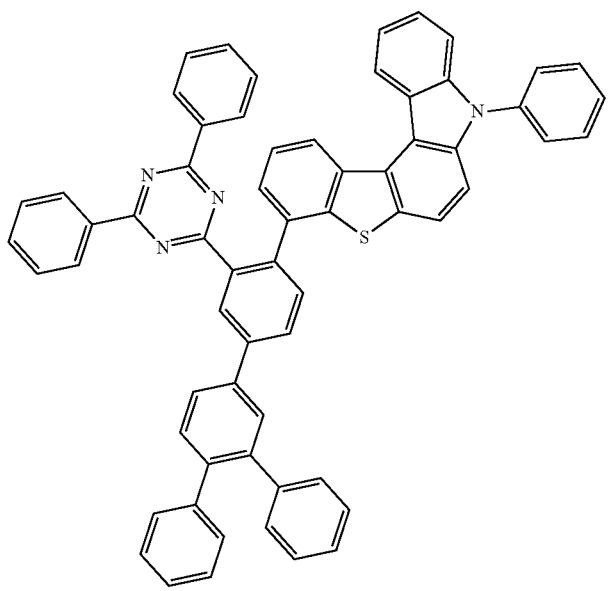

3547
603
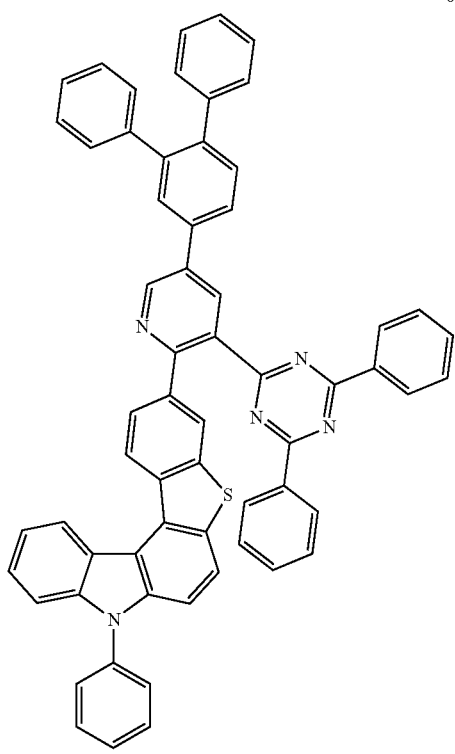
3548
604
605

-continued
606
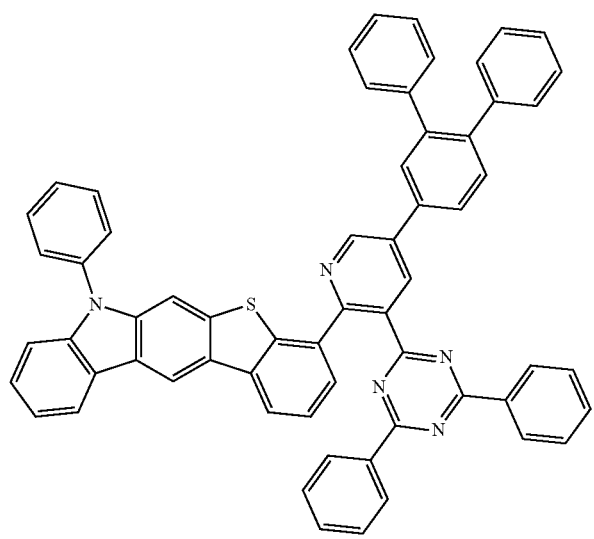
607
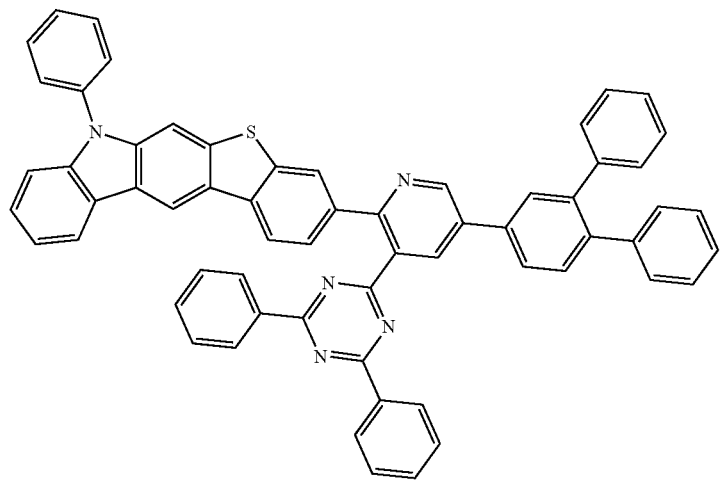
608
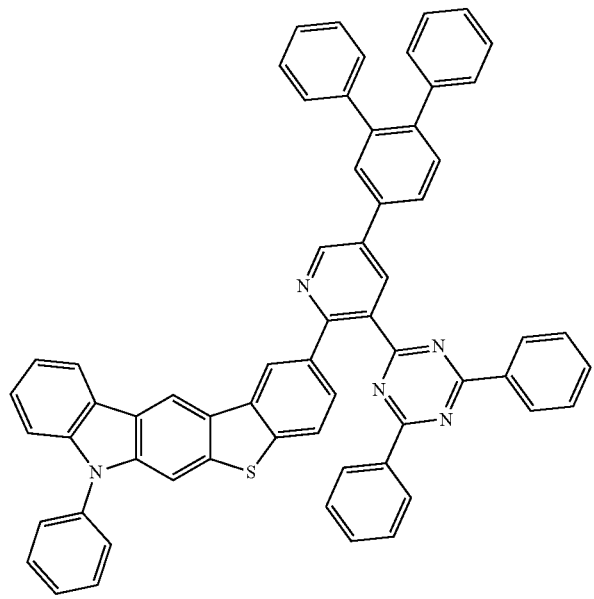

609
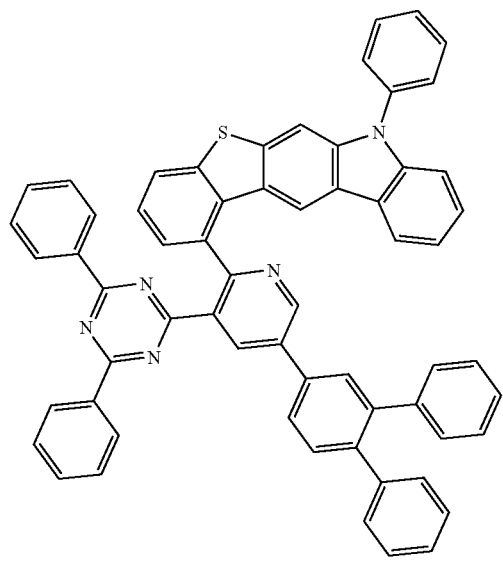
610
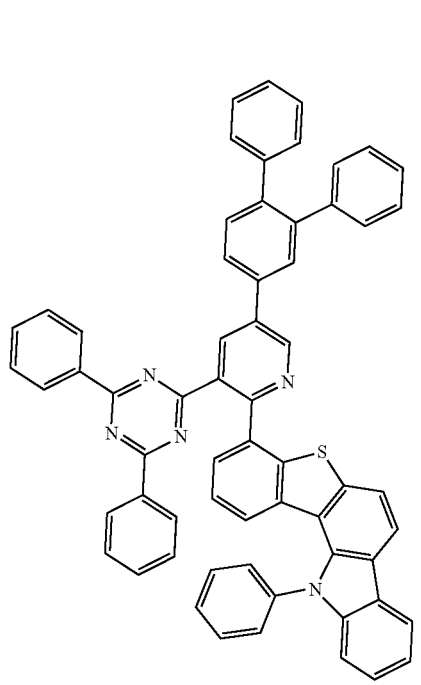
611
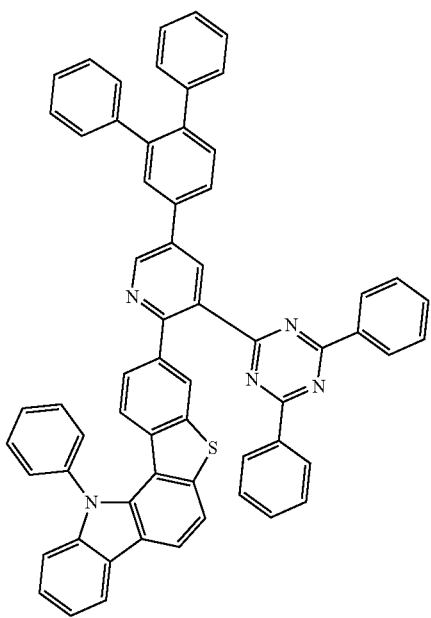

3553
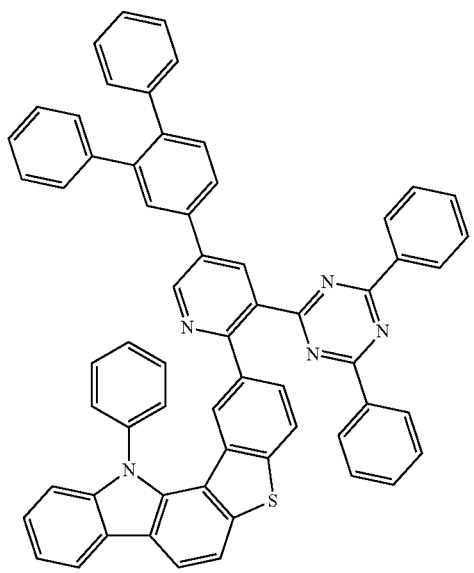
612
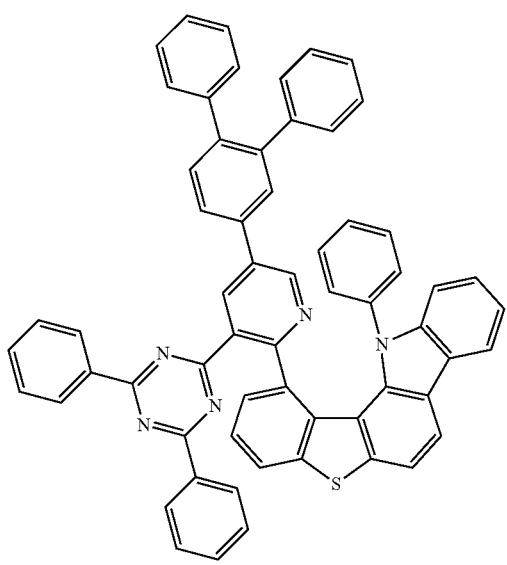
613
3554
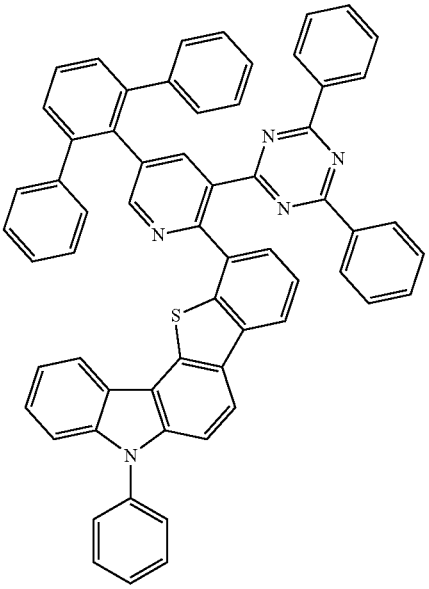
614
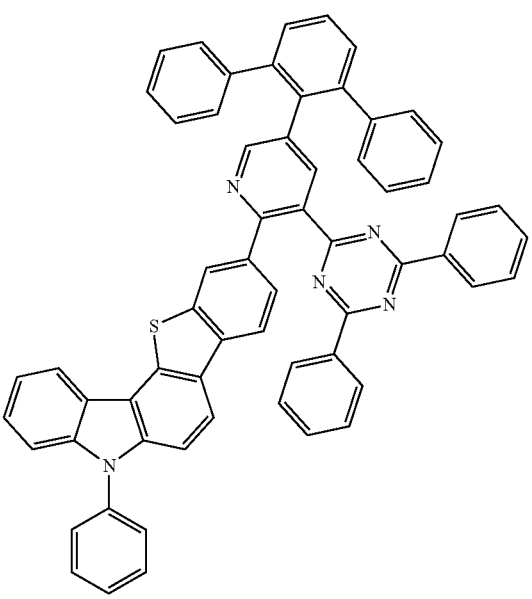
615
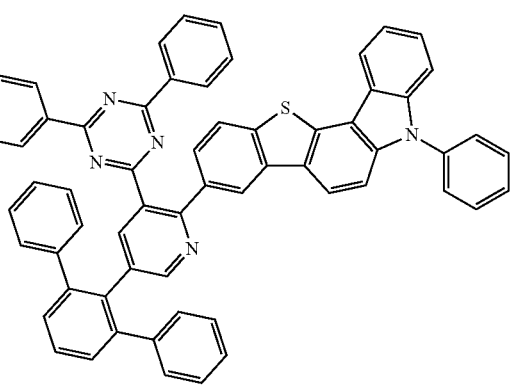
616

-continued
617
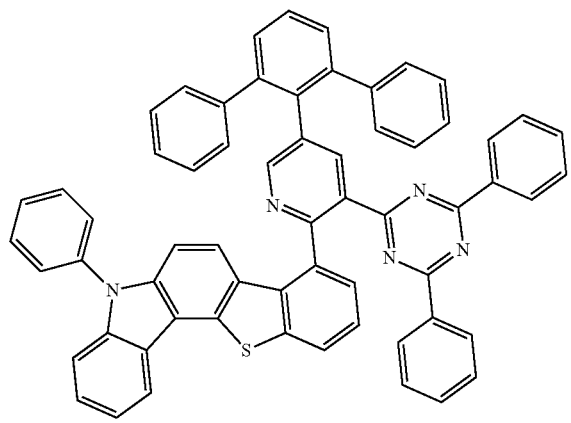
618
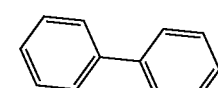
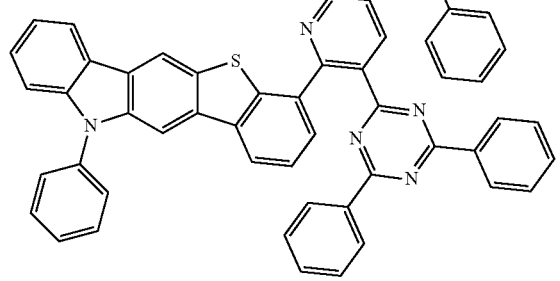
619
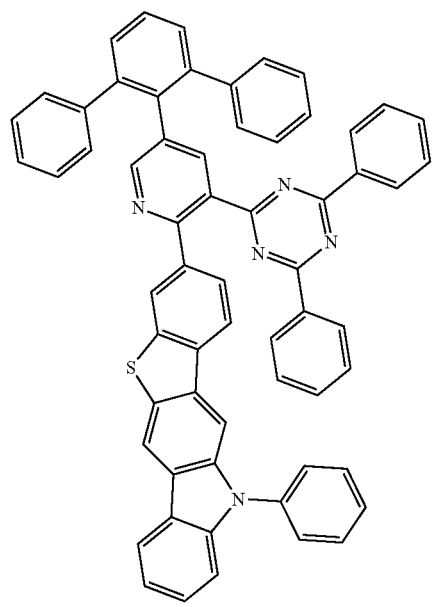
-continued
620
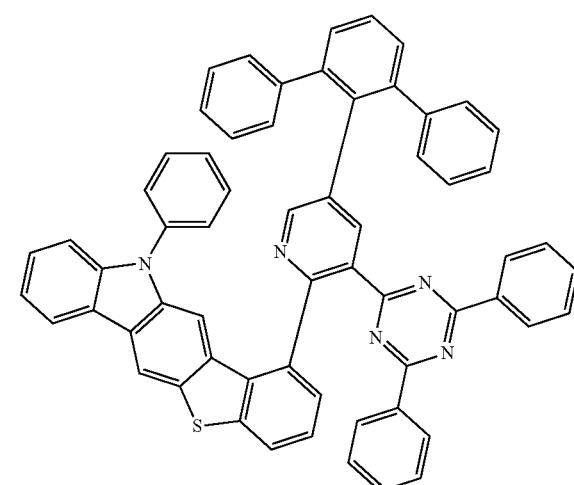
621
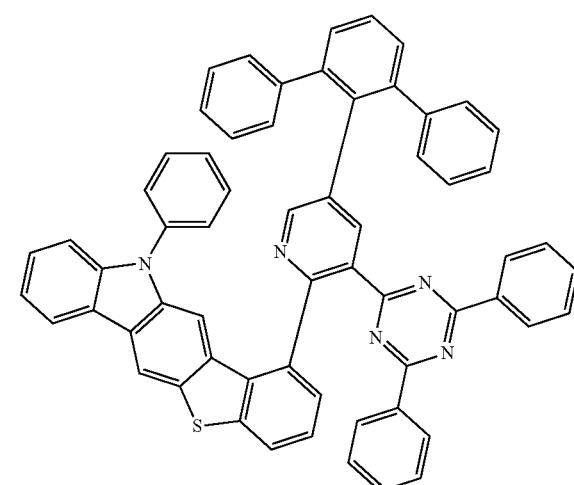
622
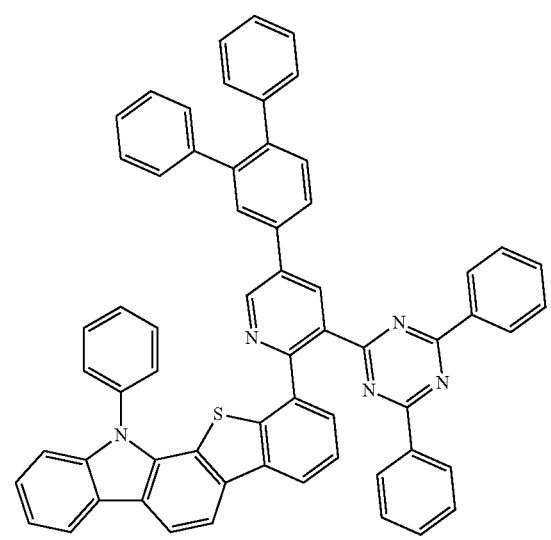

623
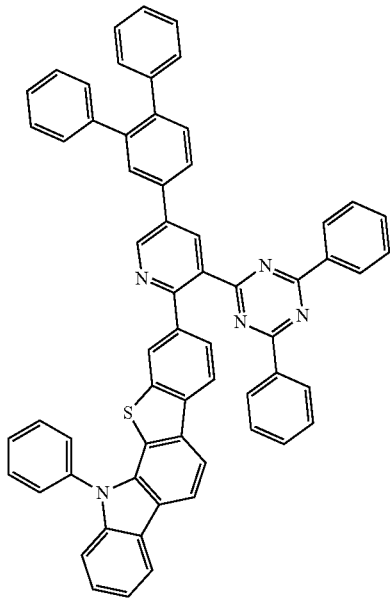
624
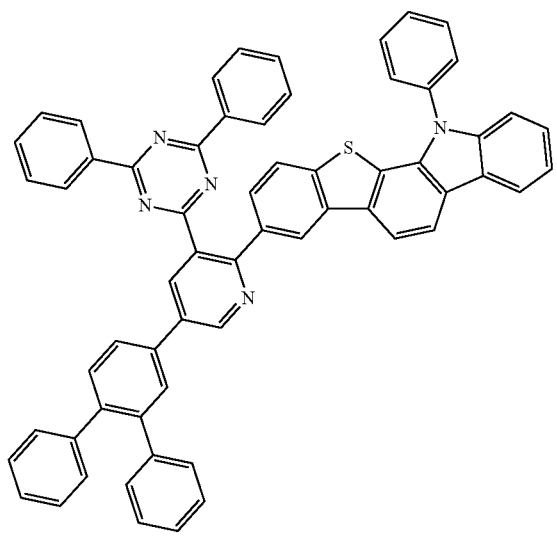
625
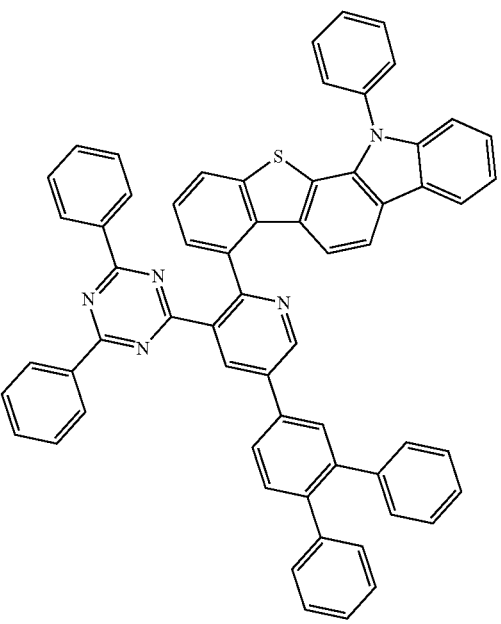
626
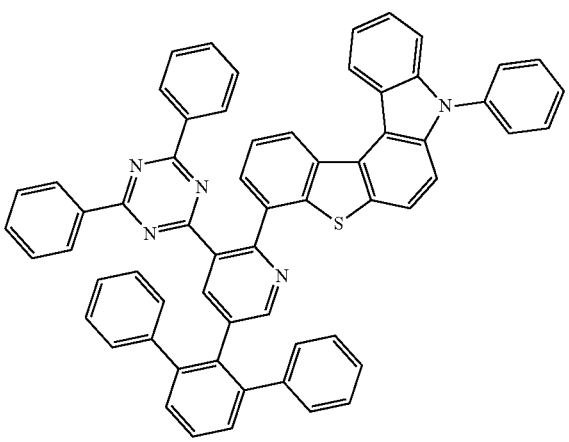

3559
-continued
627
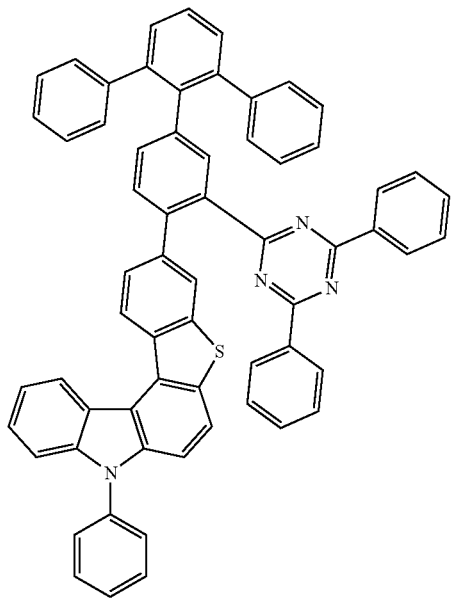
628
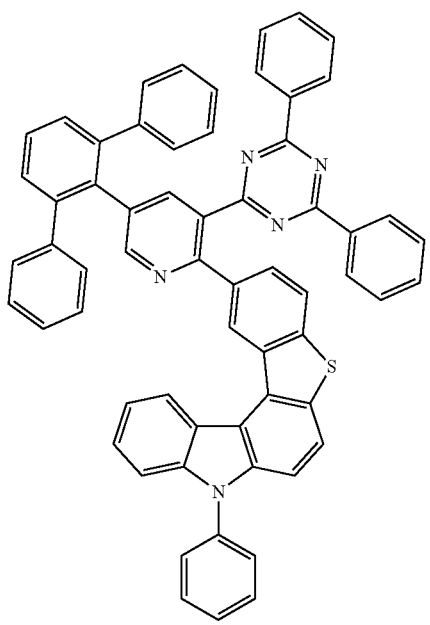
3560
-continued
629
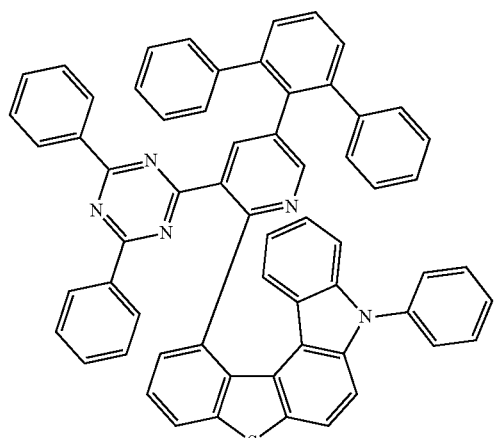
630
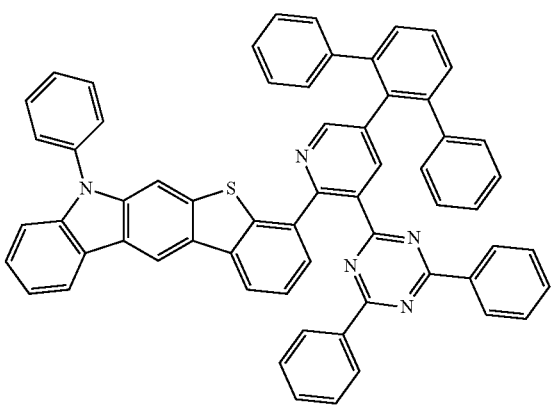
631
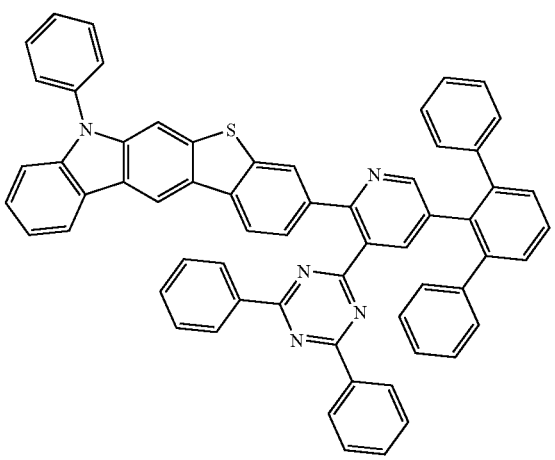

632
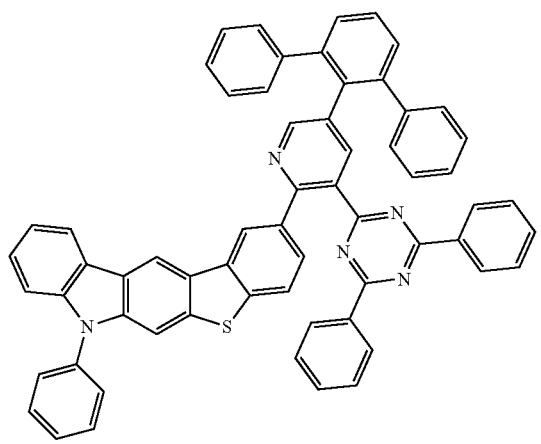
633
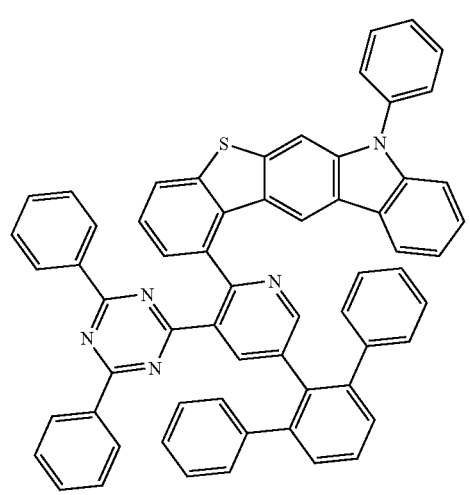
634
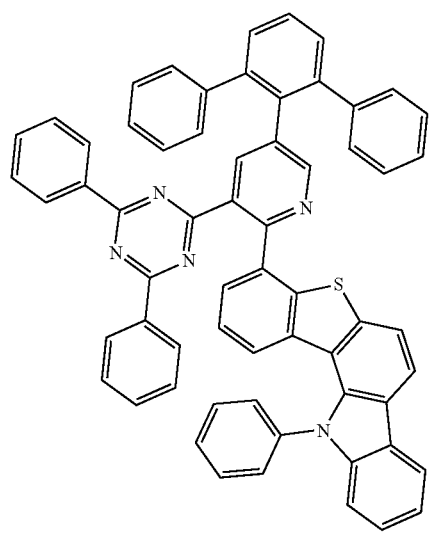
635
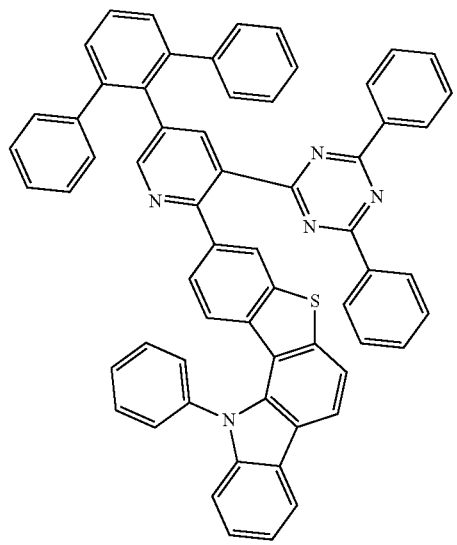
636
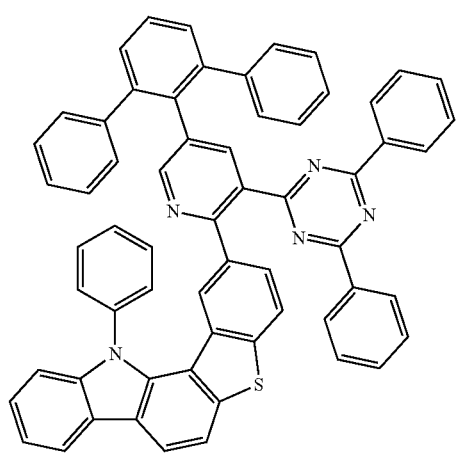
637
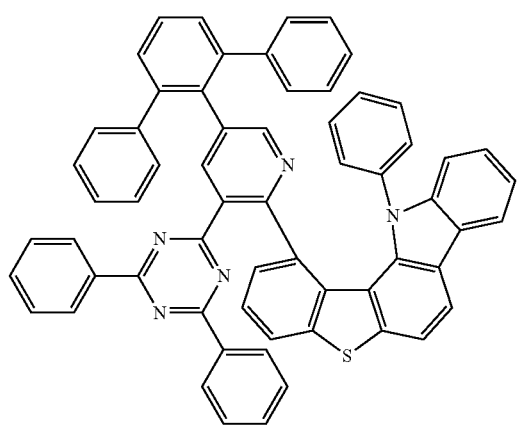

3563
-continued
638
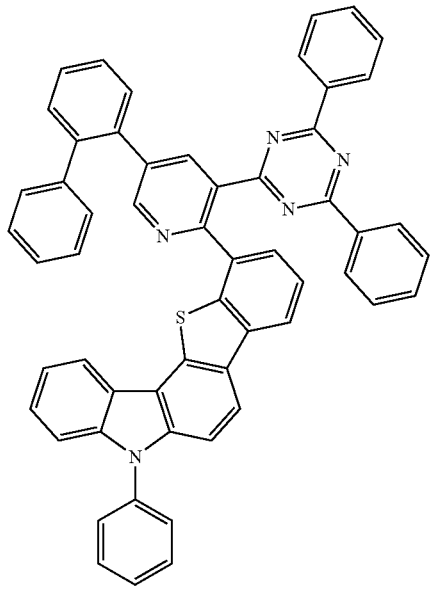
639
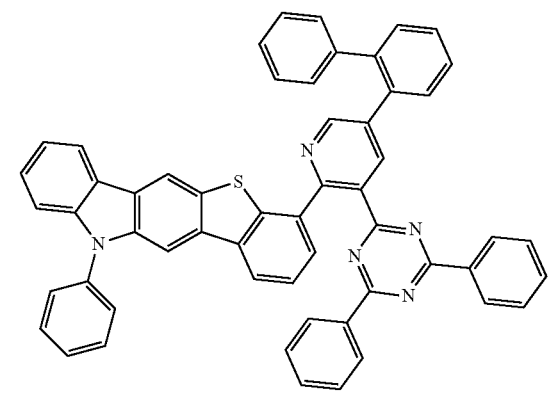
640
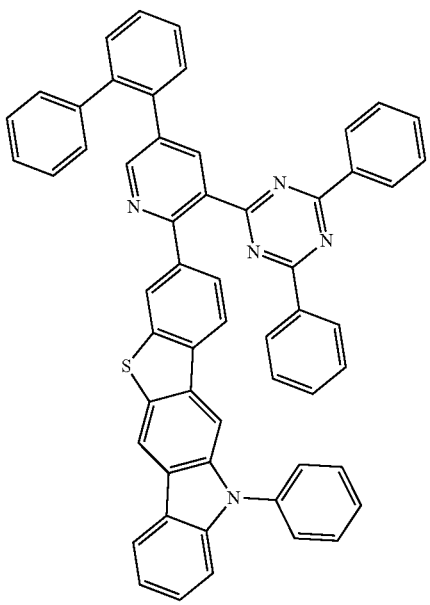
3564
-continued
641
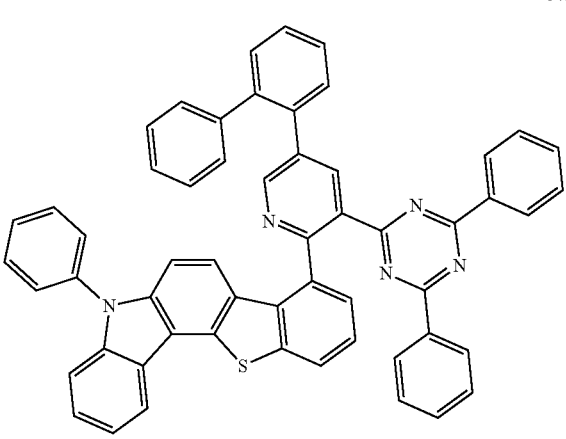
642
643

644
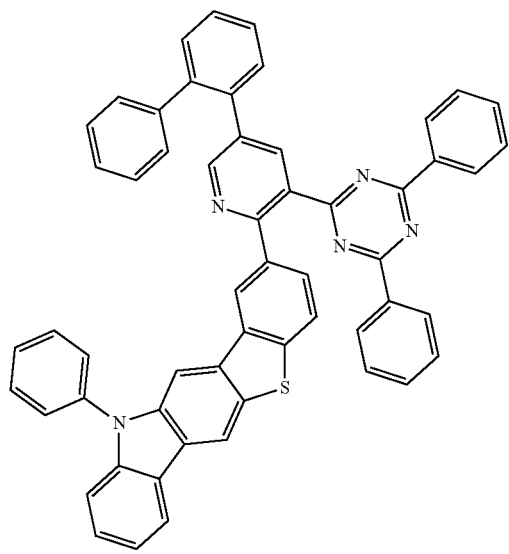
645
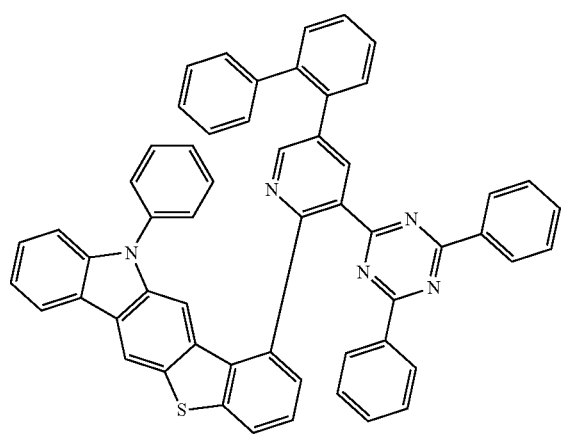
646
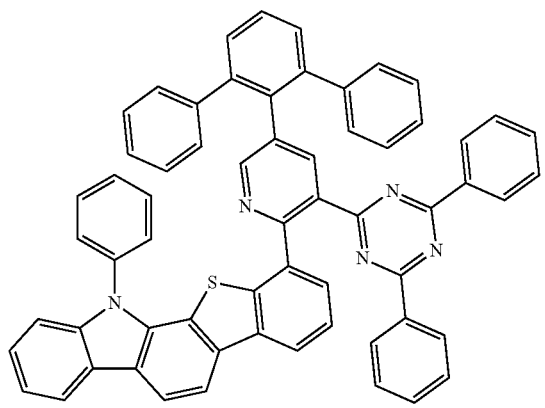
647
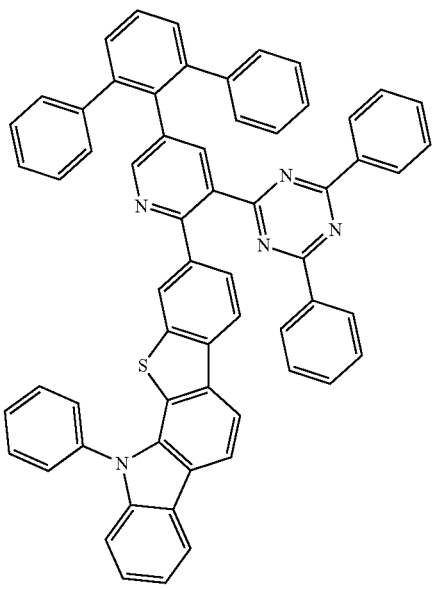
648
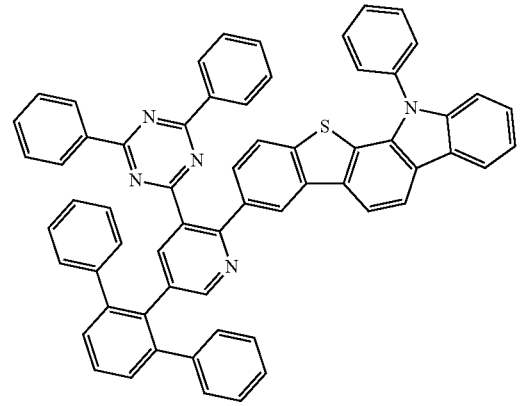
649
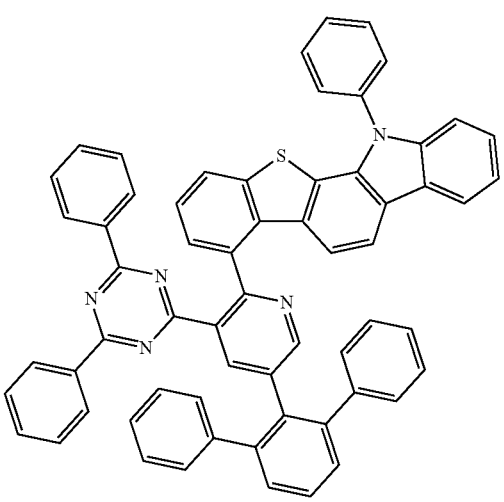

3567
-continued
650
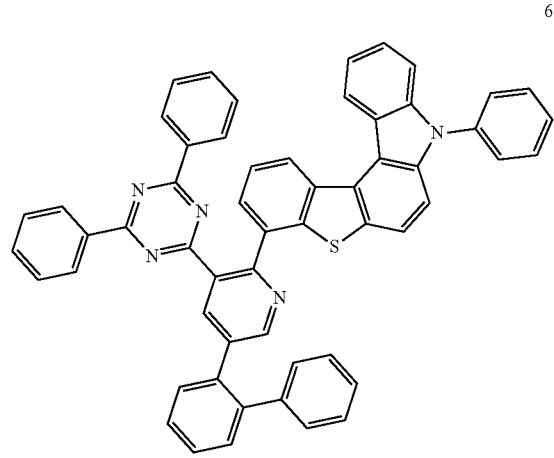
651
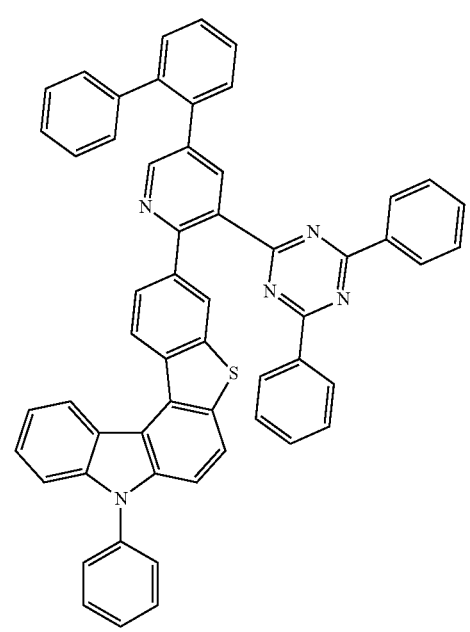
3568
-continued
652
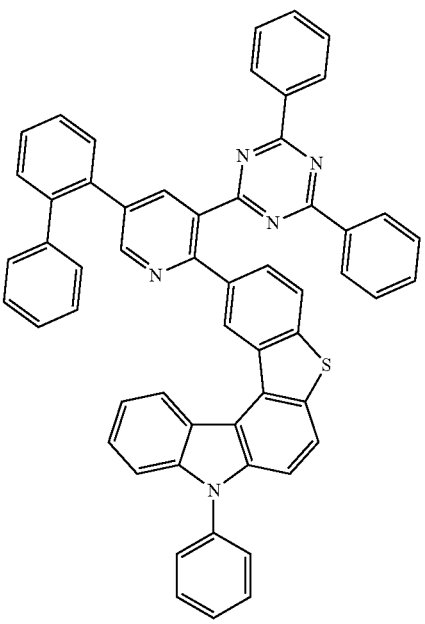
653
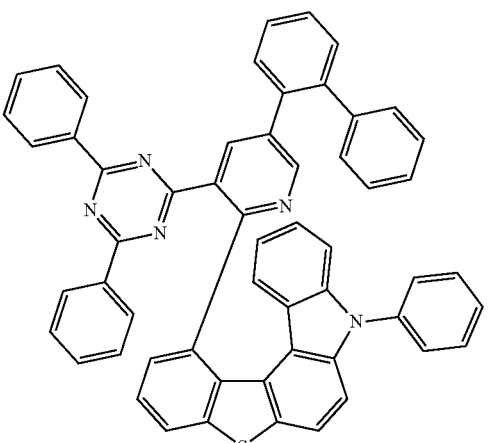
654
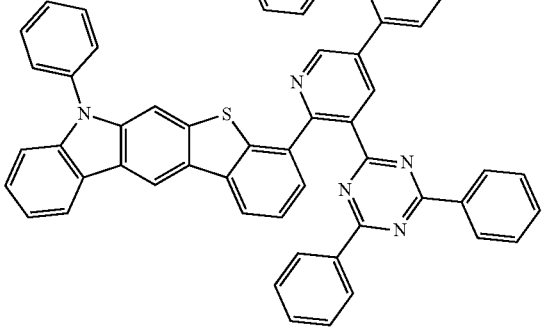

3569
-continued
655
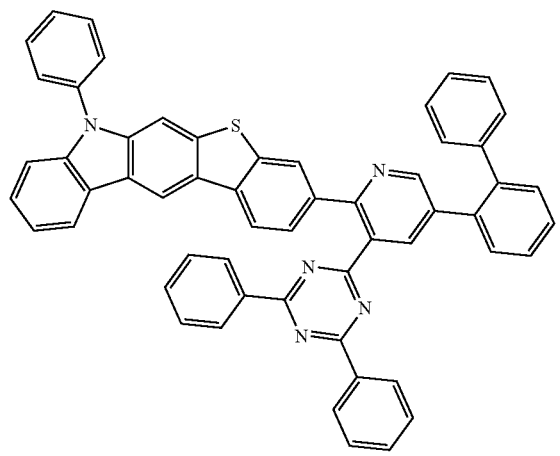
656
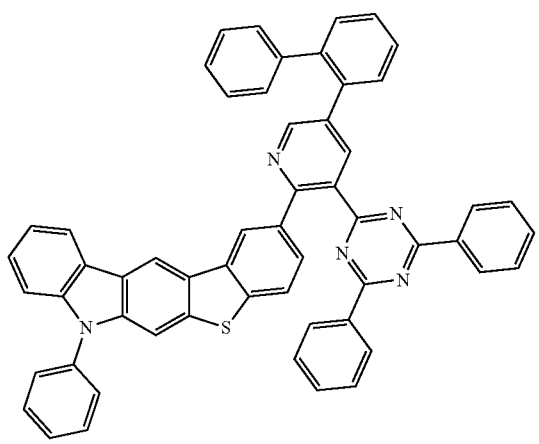
657
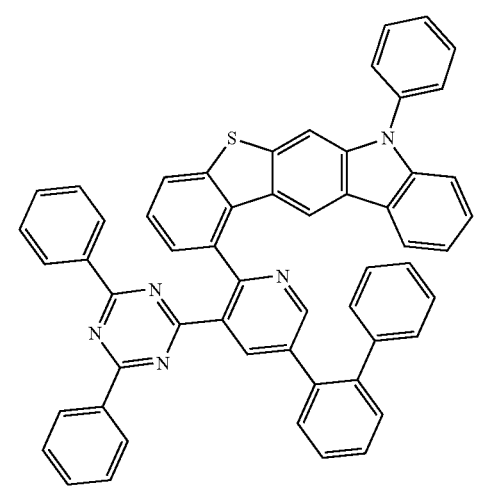
3570
-continued
658
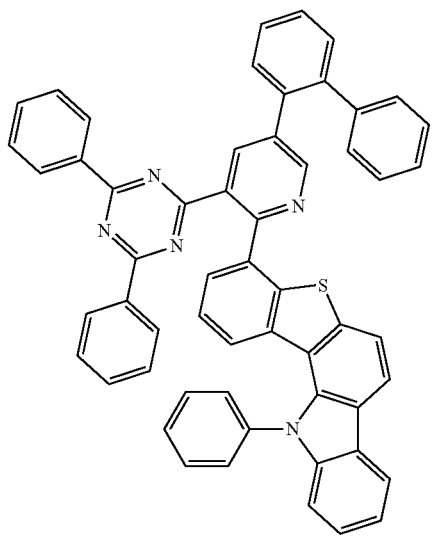
659
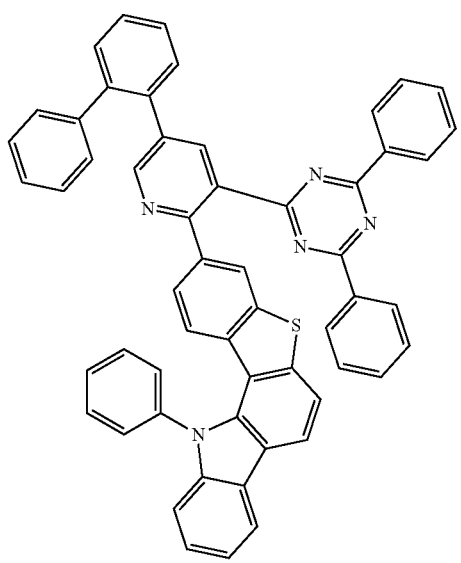
660
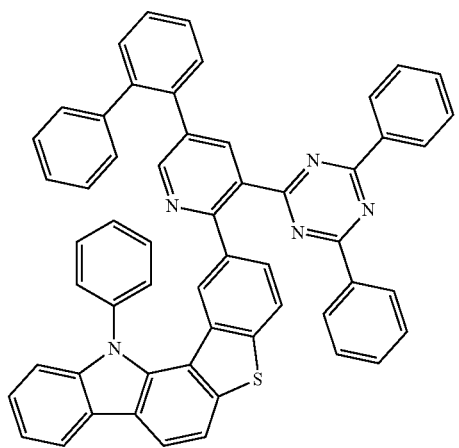

3571
-continued
661
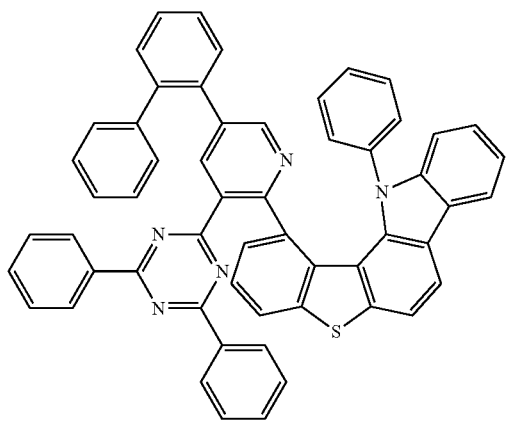
662
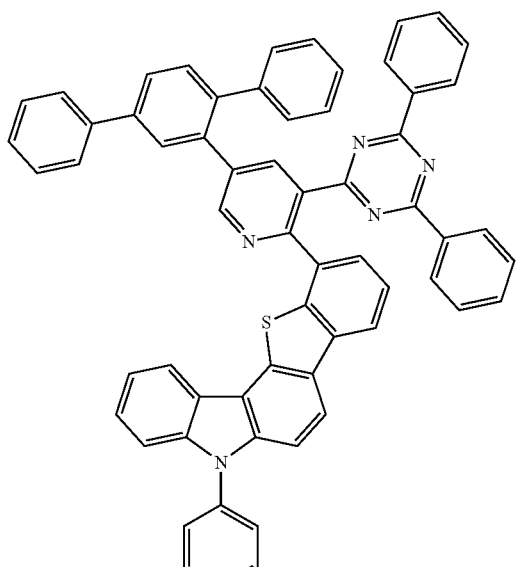
663
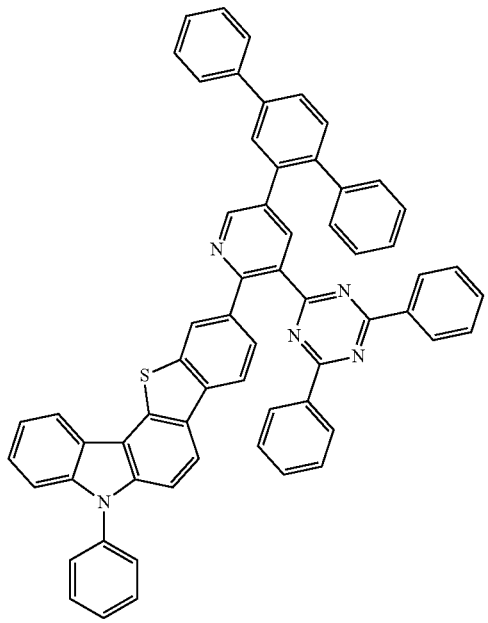
3572
-continued
664
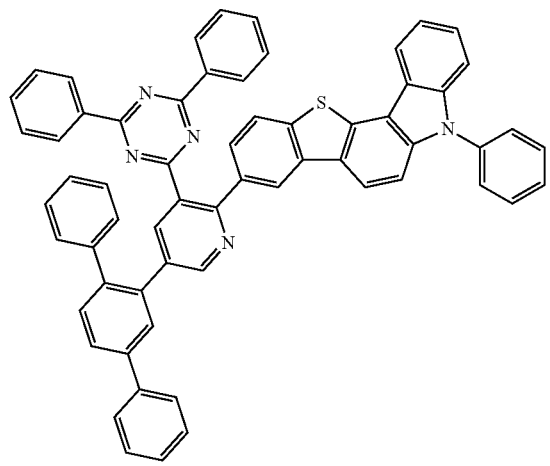
665
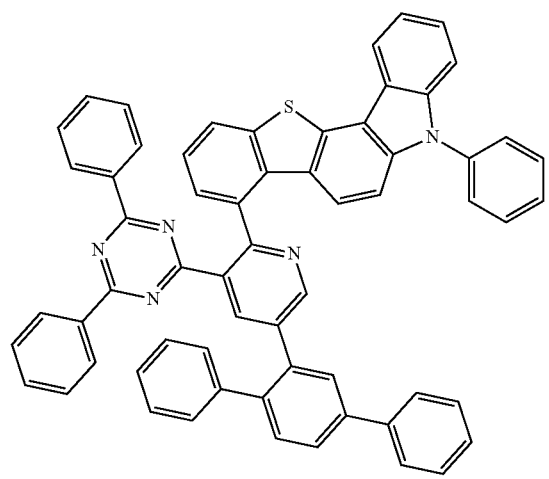
666
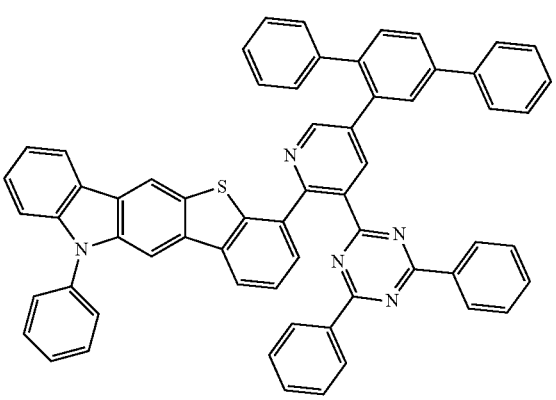

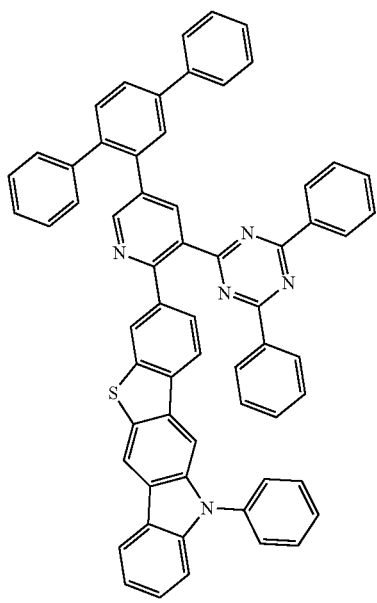
667
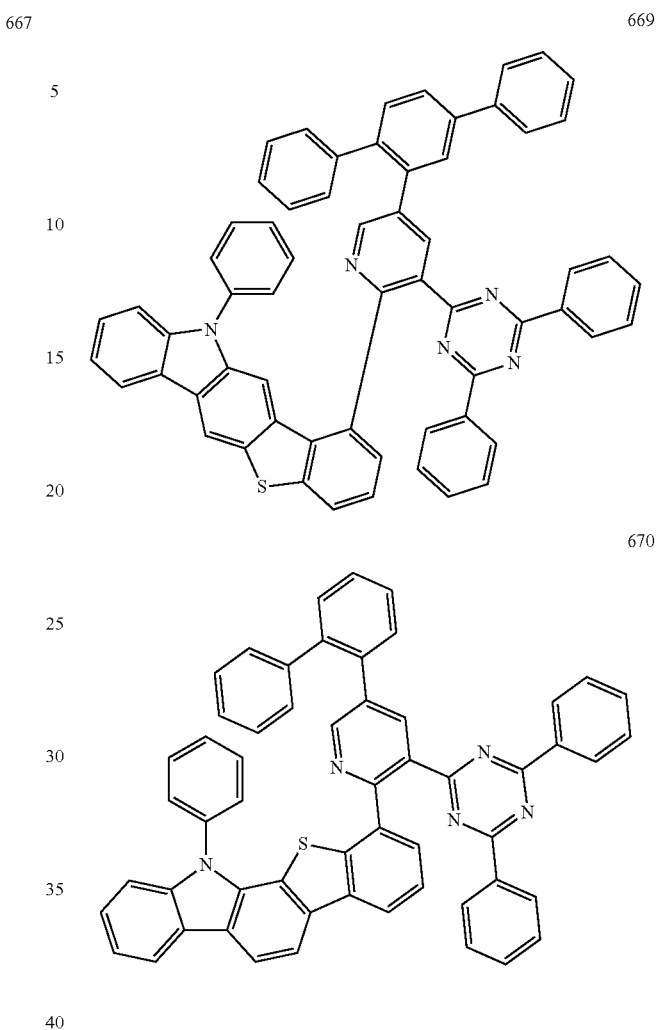
669
670
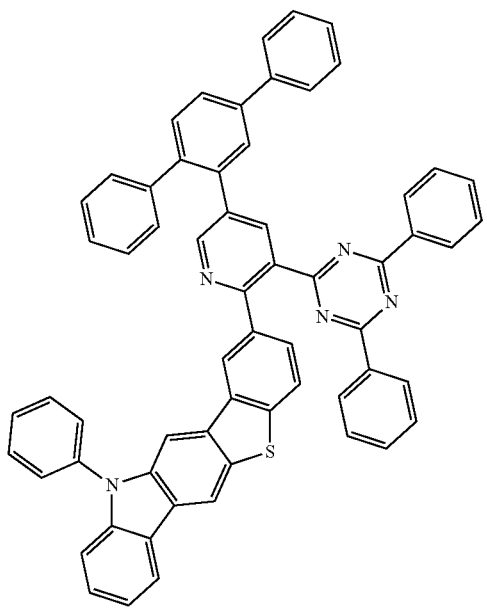
668
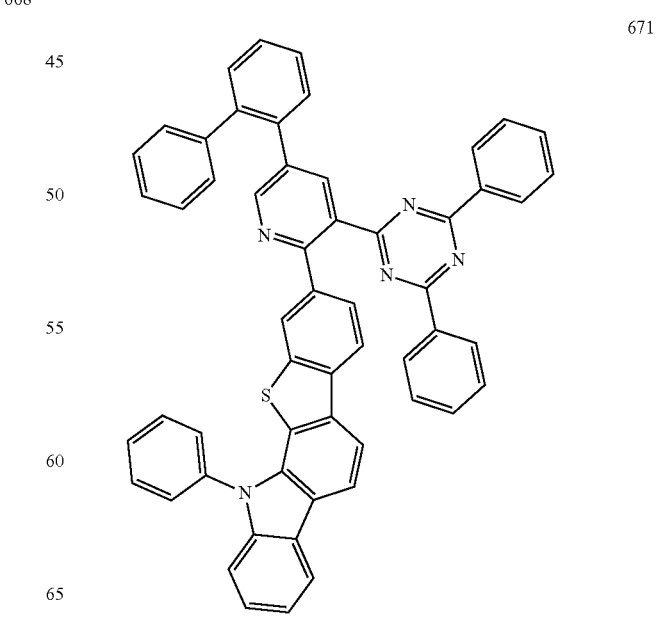
671

3575
-continued
672
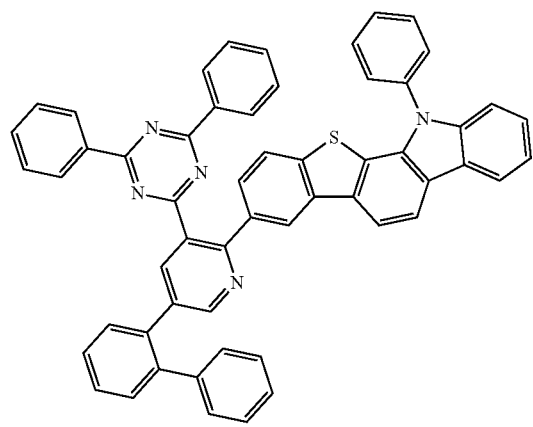
673
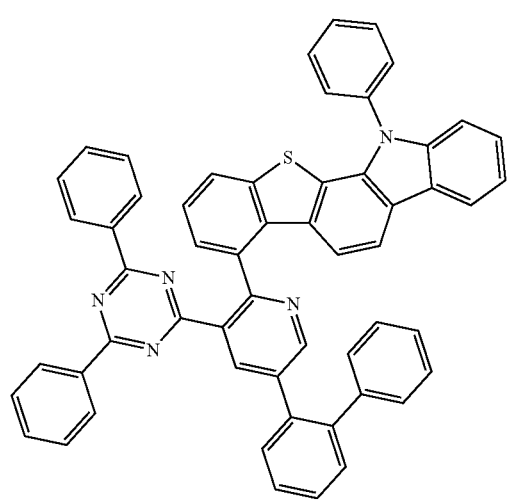
674
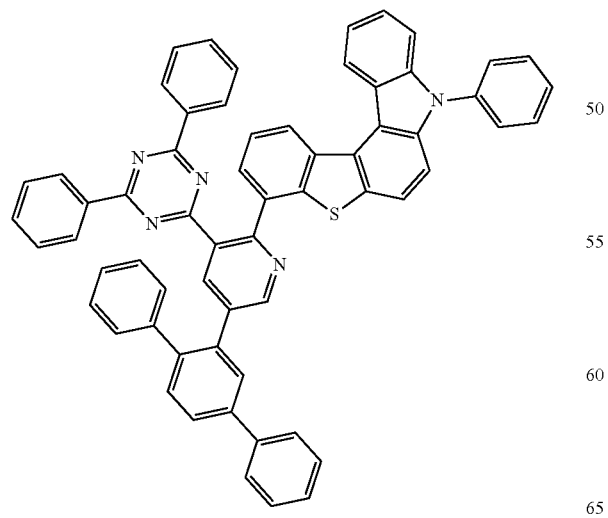
3576
-continued
675
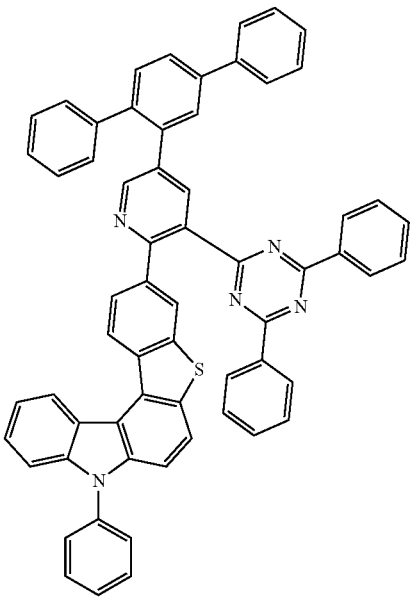
676
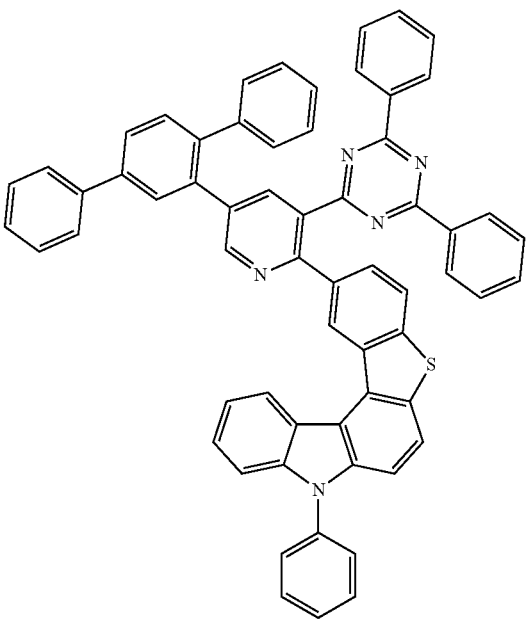

3577
-continued
677
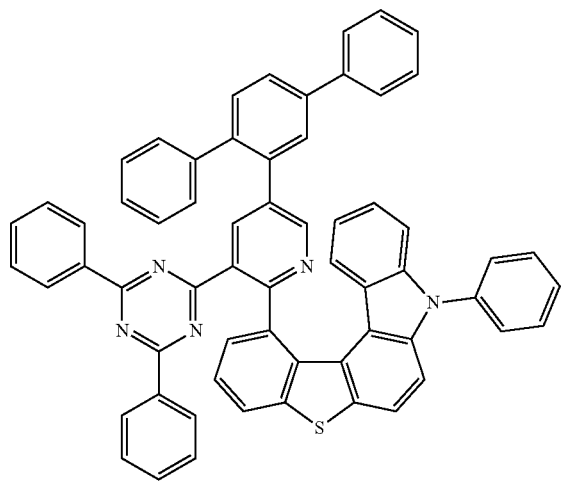
678
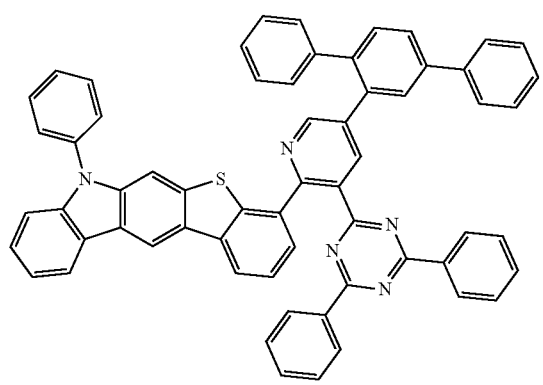
679
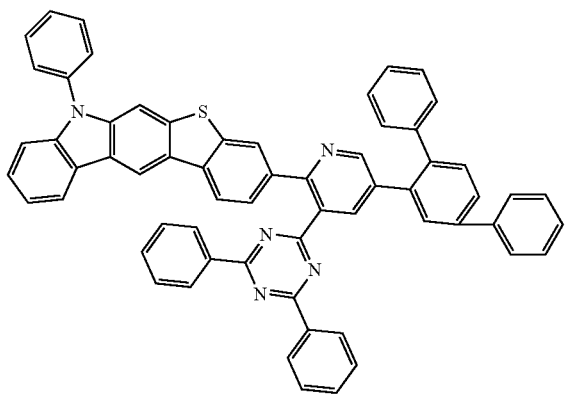
3578
-continued
680
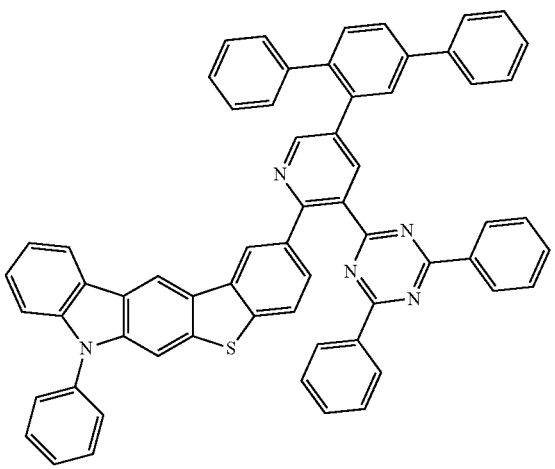
681
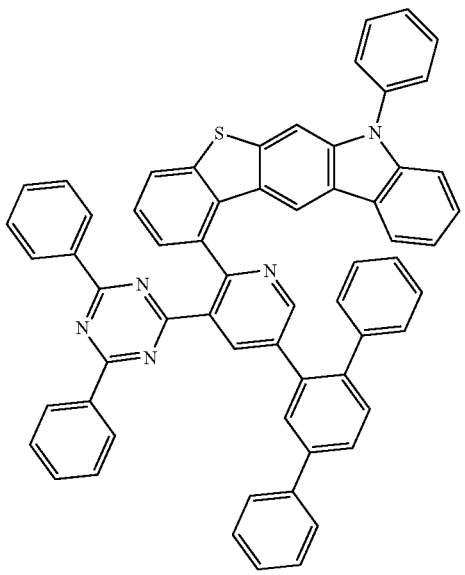
682
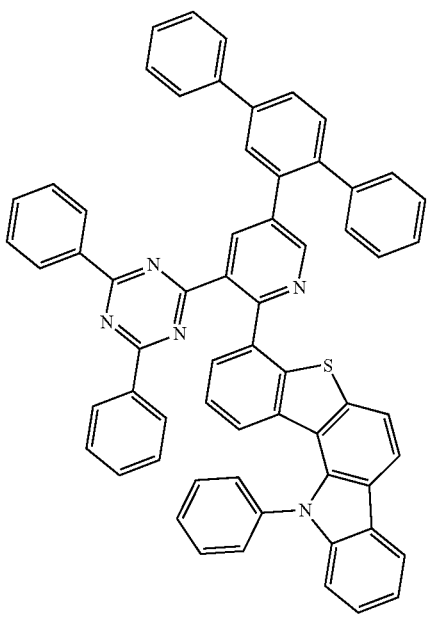

3579
-continued
683
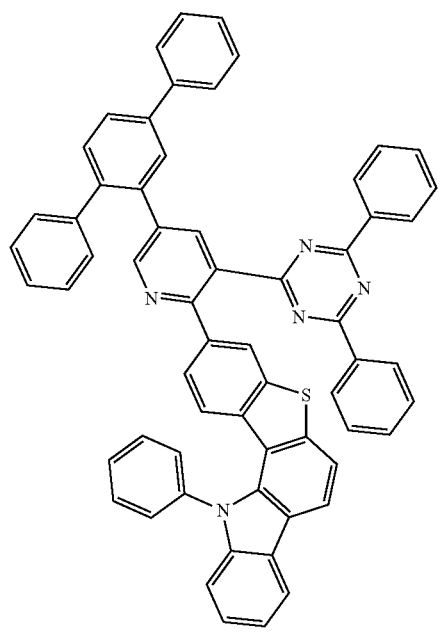
684
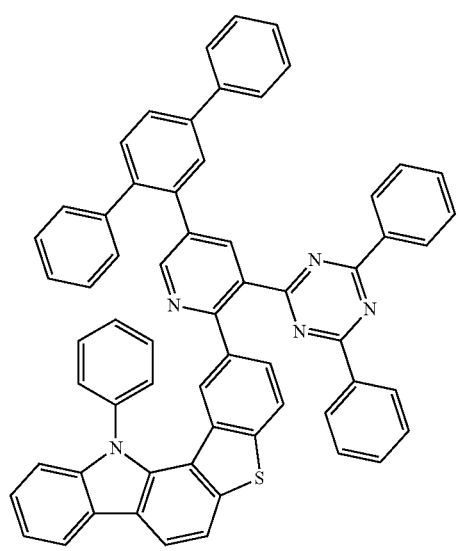
3580
-continued
685
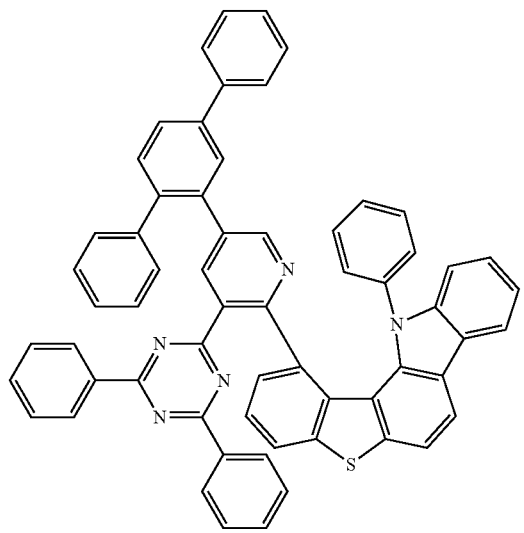
686
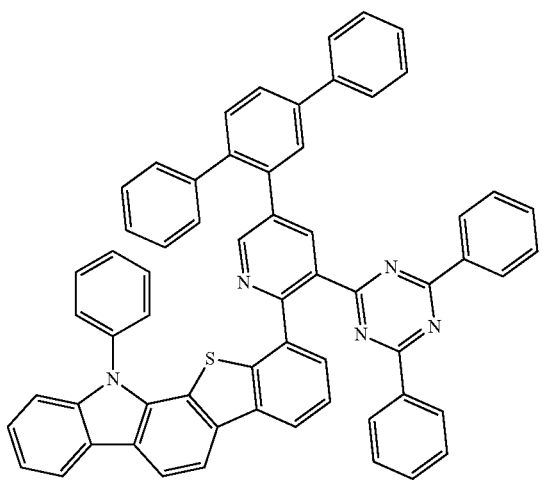
687
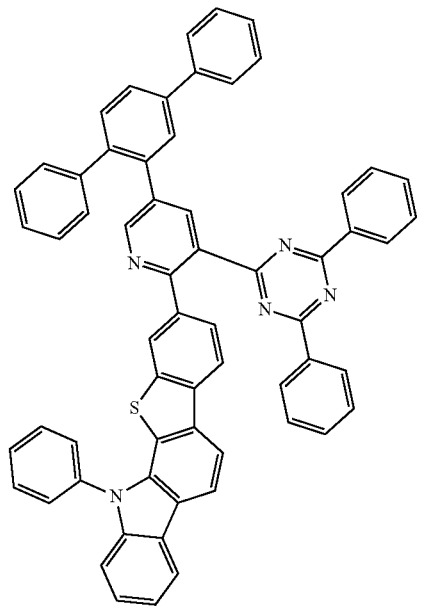

688
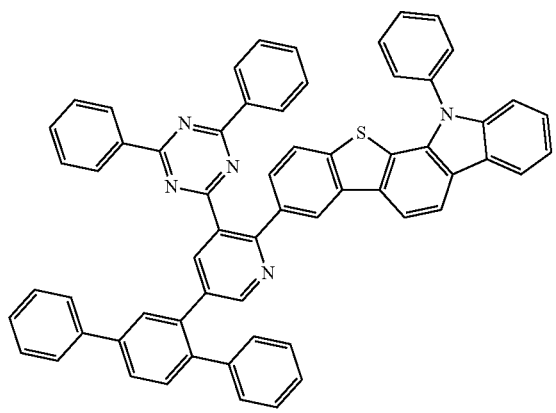
689
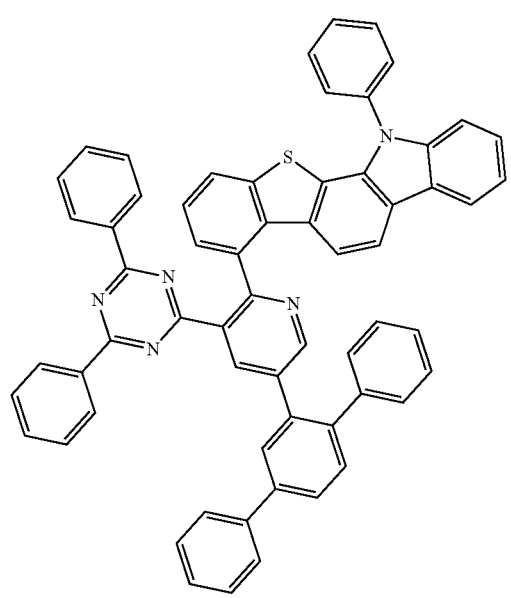
690
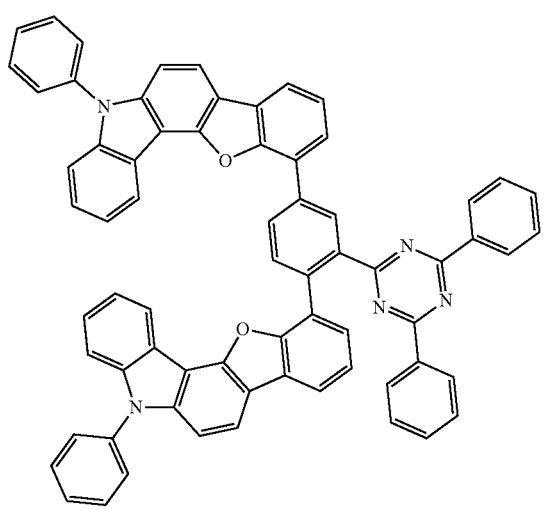
691
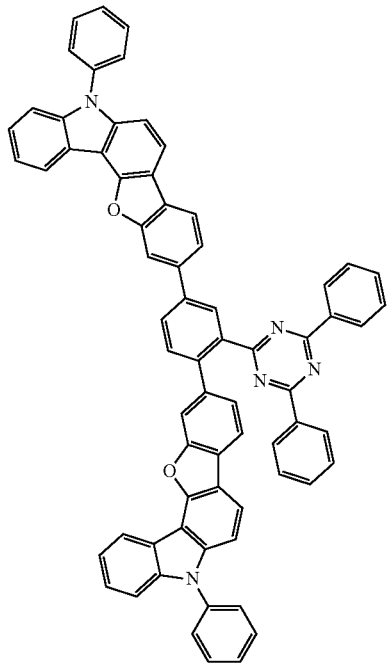
692
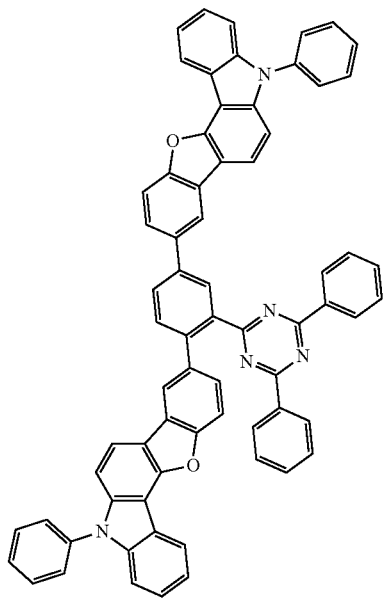

3583
-continued
693
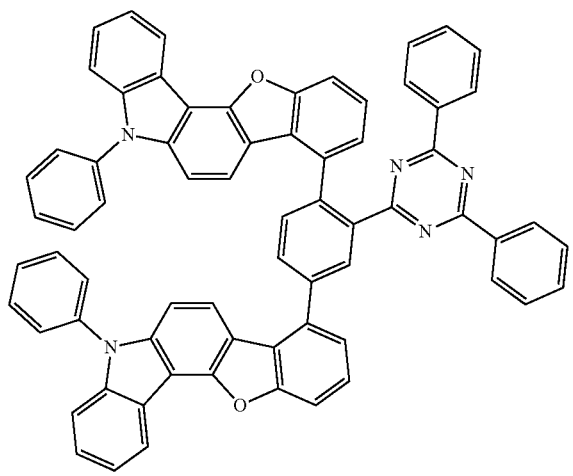
3584
-continued
695
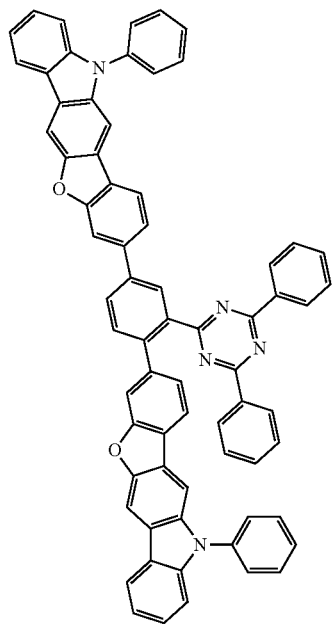
694
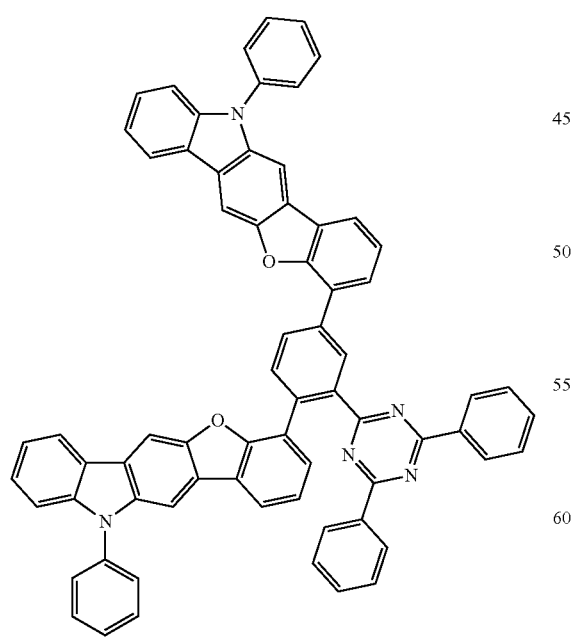
696
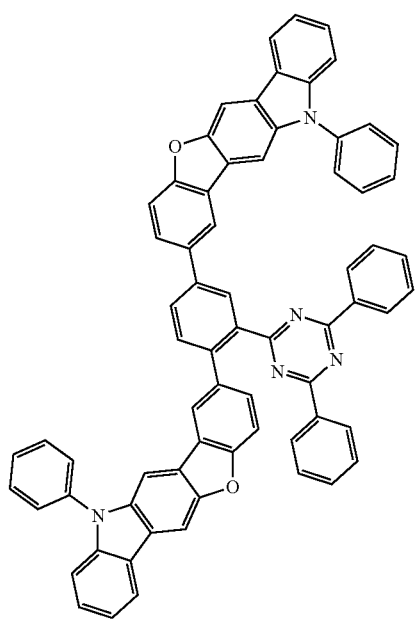

3585
-continued
3586
-continued
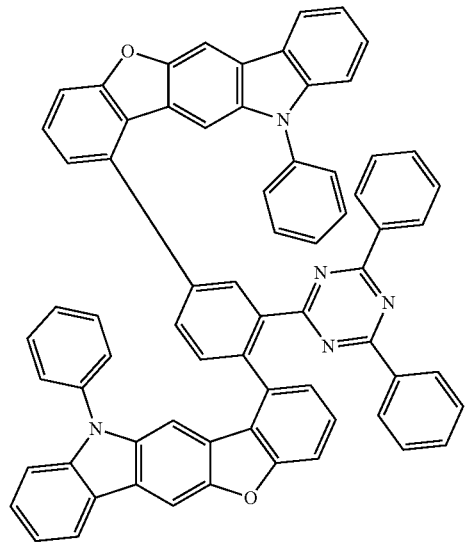
697
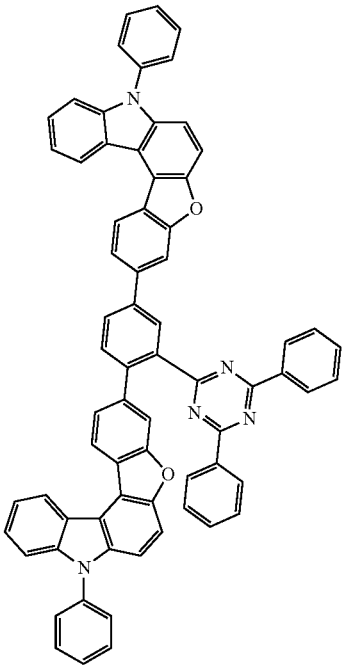
699
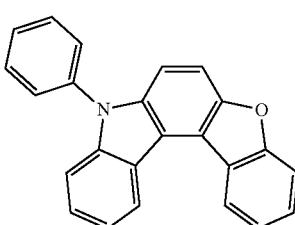
698
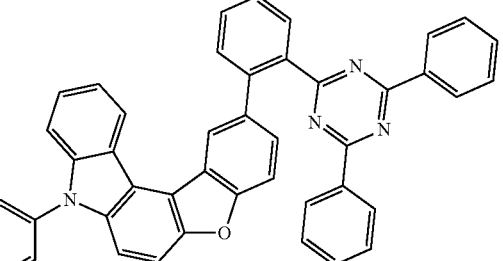
700

3587
-continued
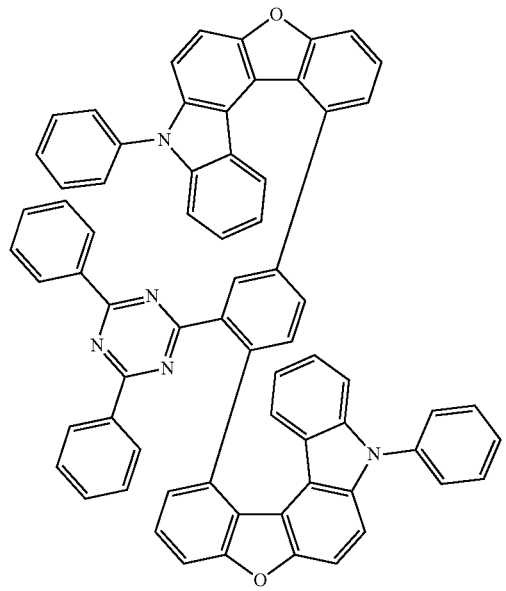
3588
-continued
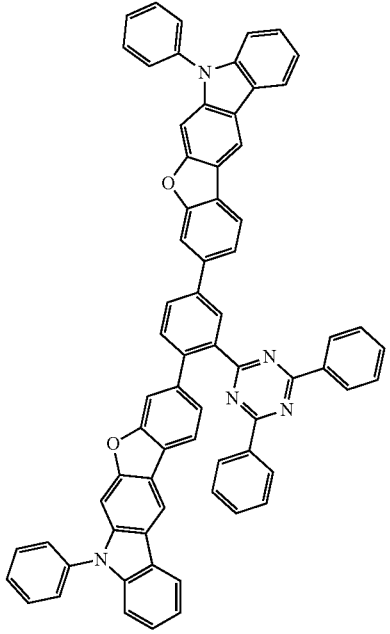
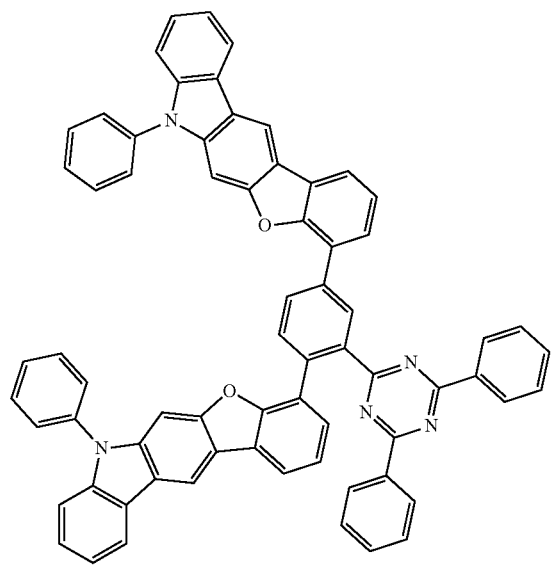
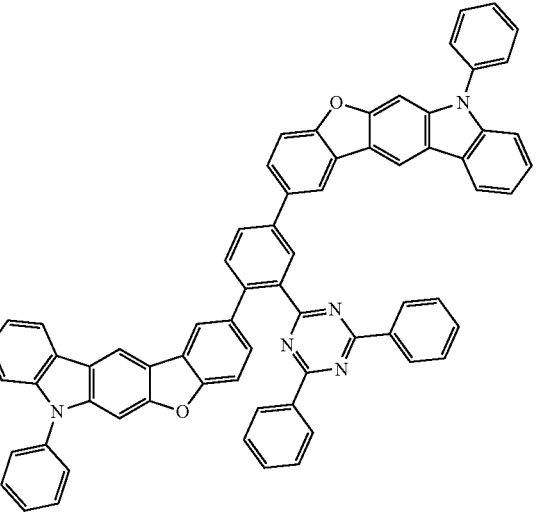

705
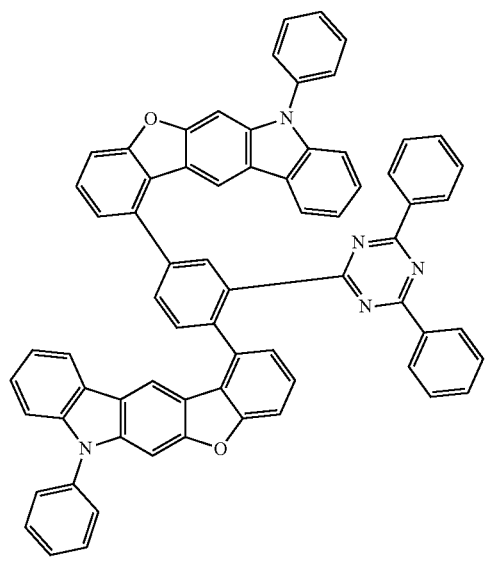
706
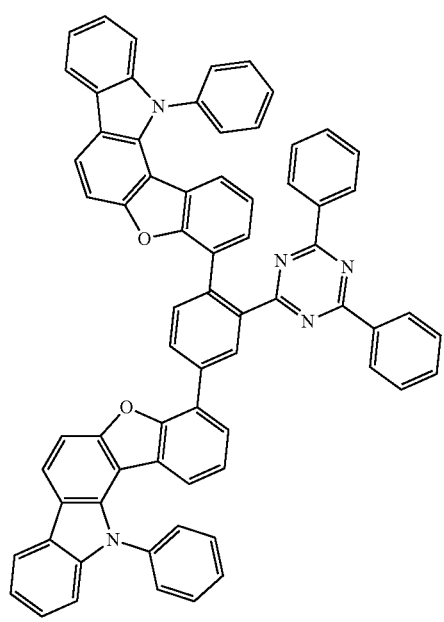
707
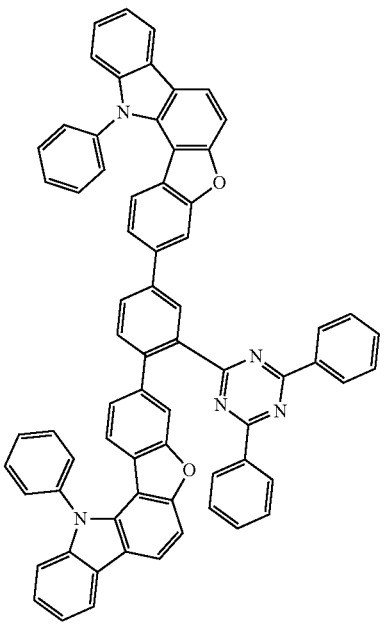
708
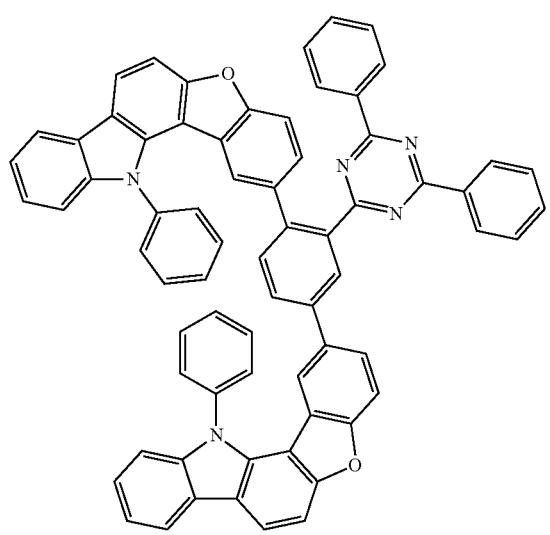
709
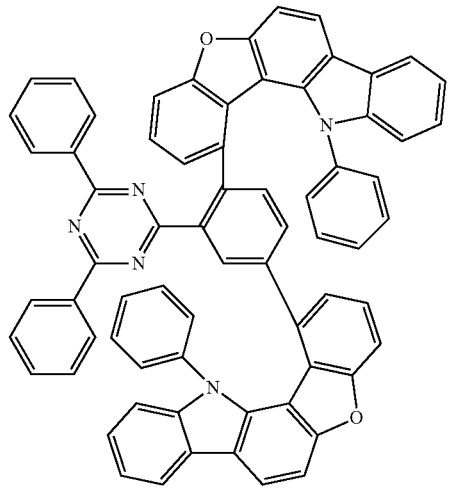

3591
-continued
710
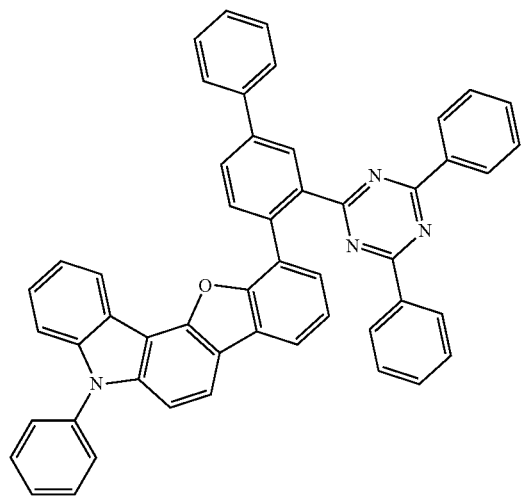
711
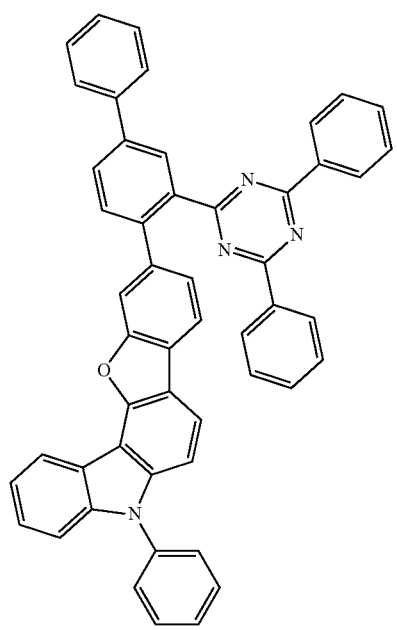
3592
-continued
712
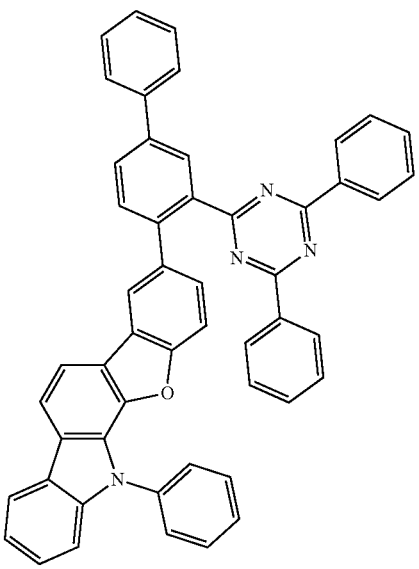
713
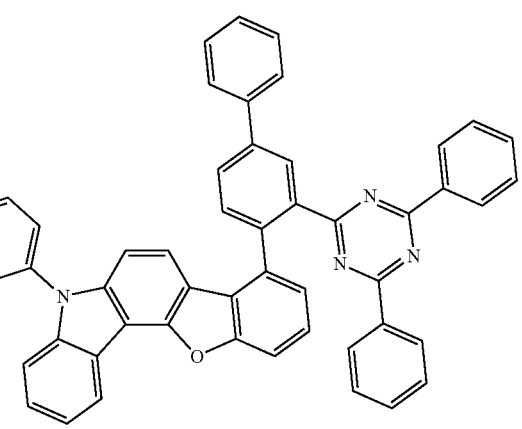
714
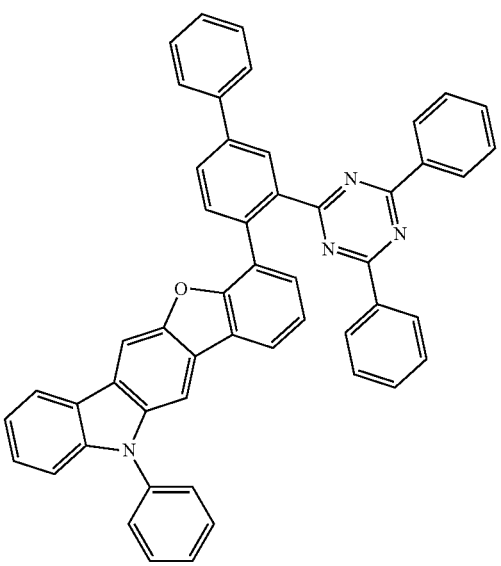

3593
-continued
715
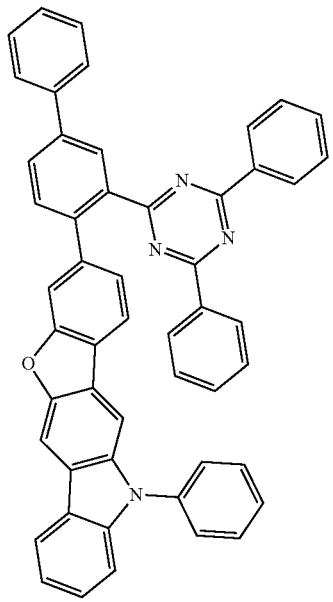
716
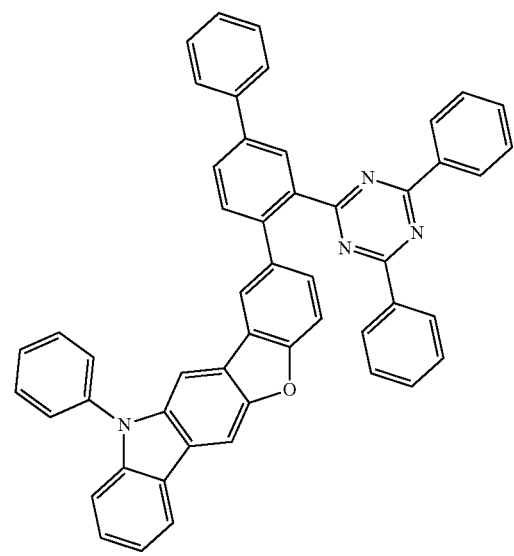
717
3594
-continued
718
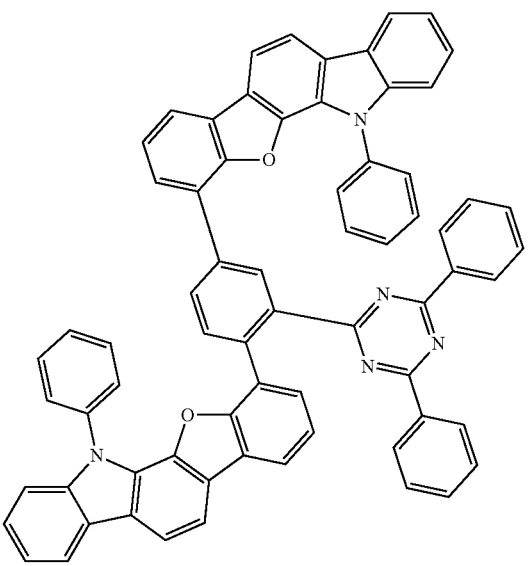
719
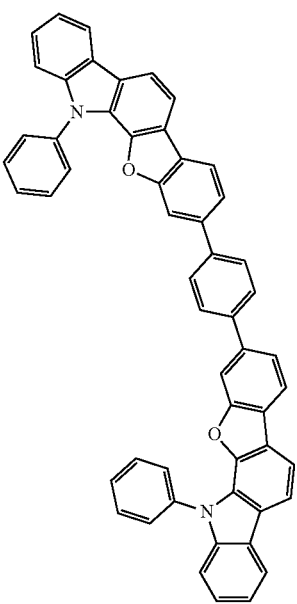

720
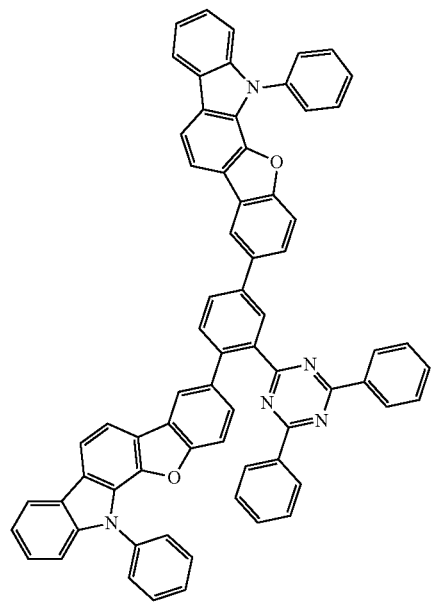
721
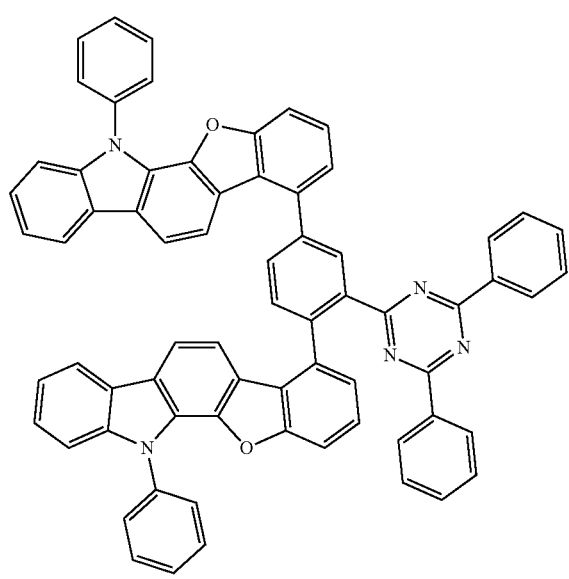
722
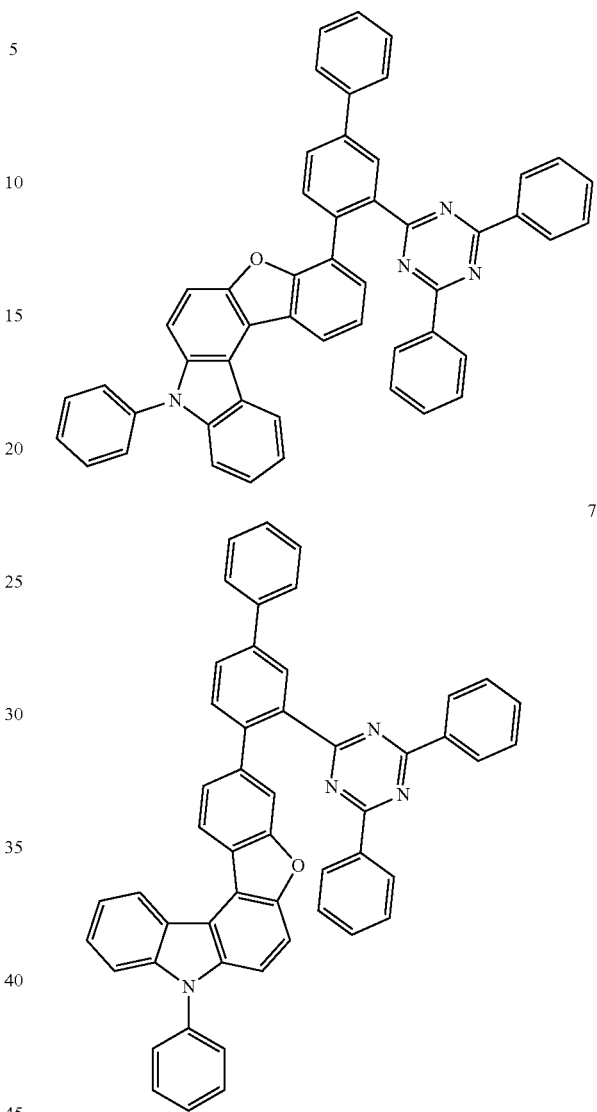
723
724
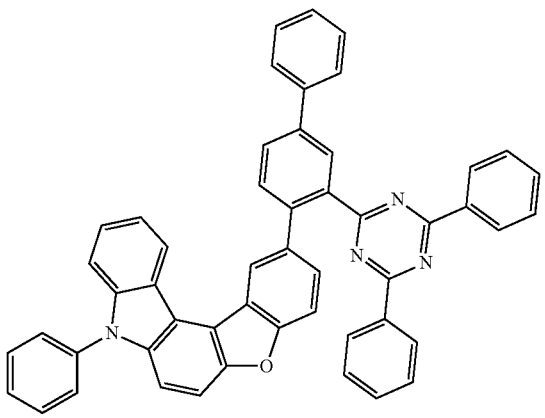

3597
-continued
725
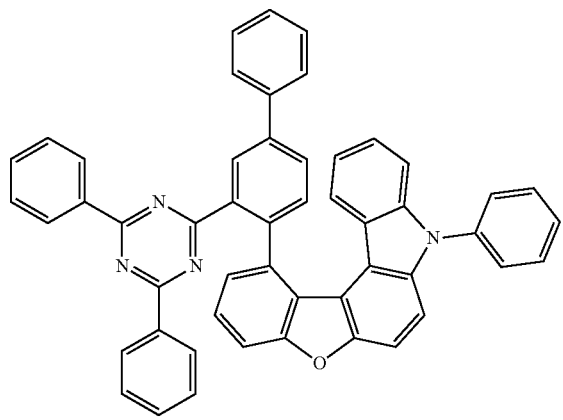
726
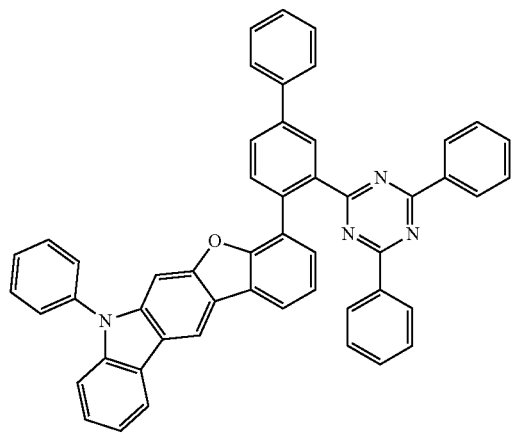
727
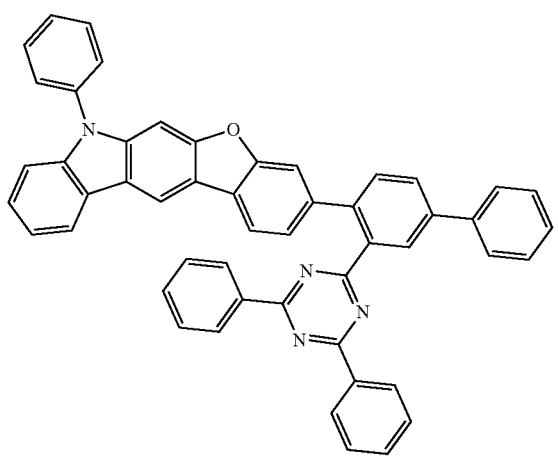
3598
-continued
728
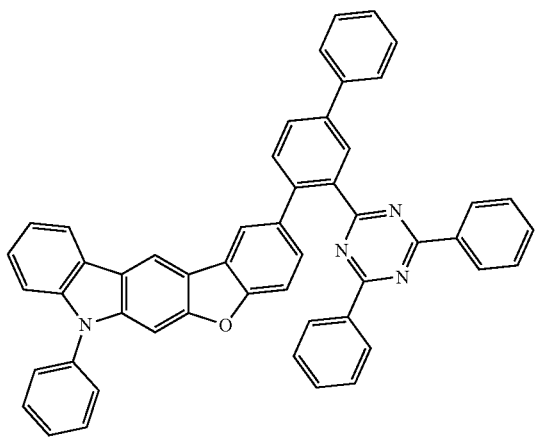
729
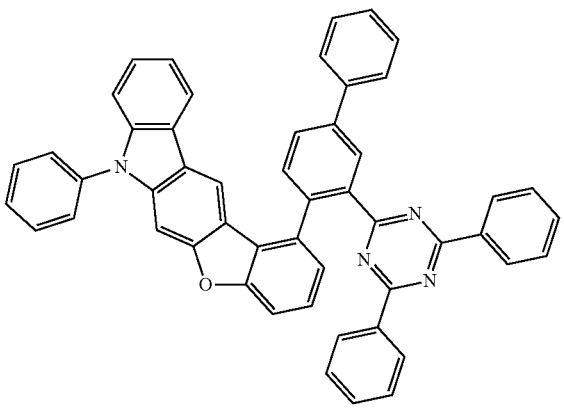
730
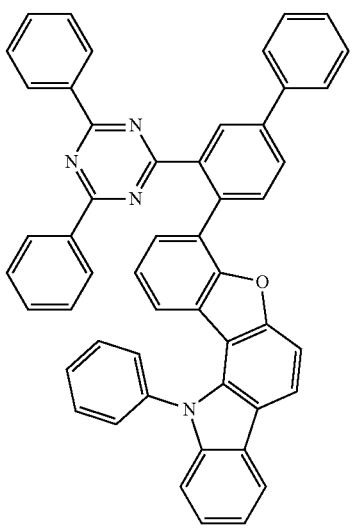

3599
-continued
731
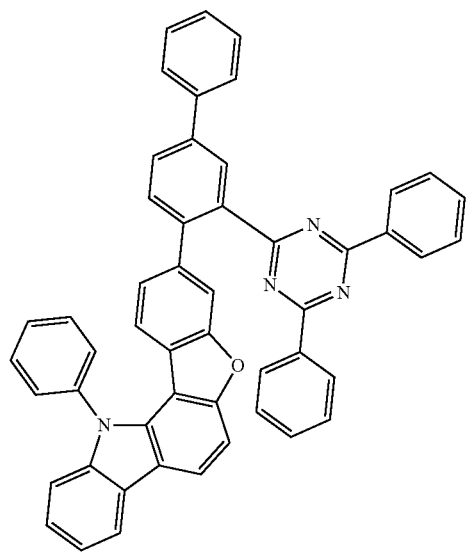
732
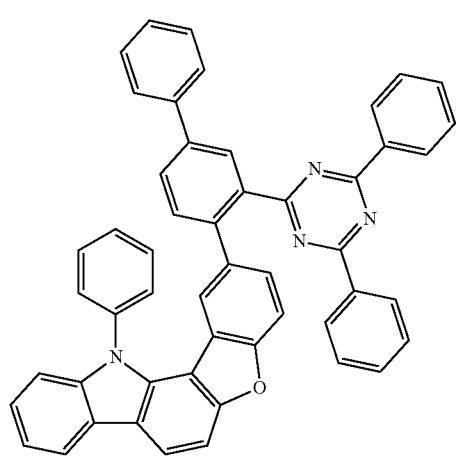
733
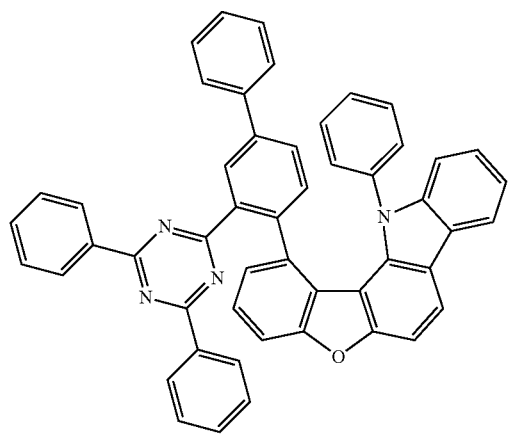
3600
-continued
734
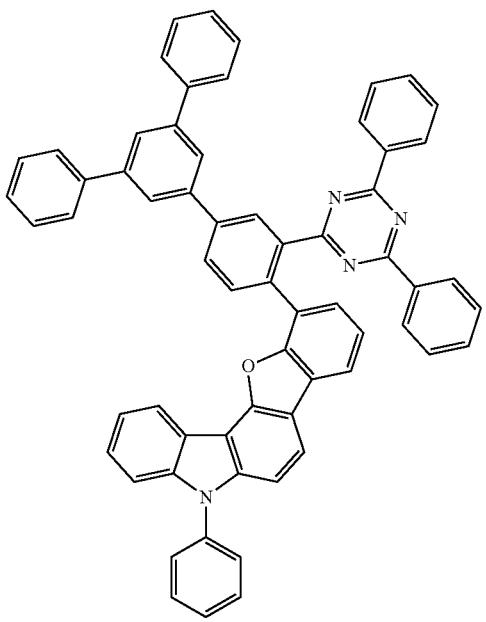
735
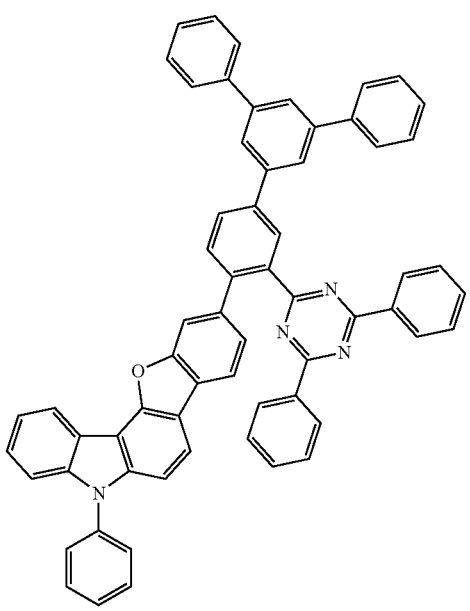
736
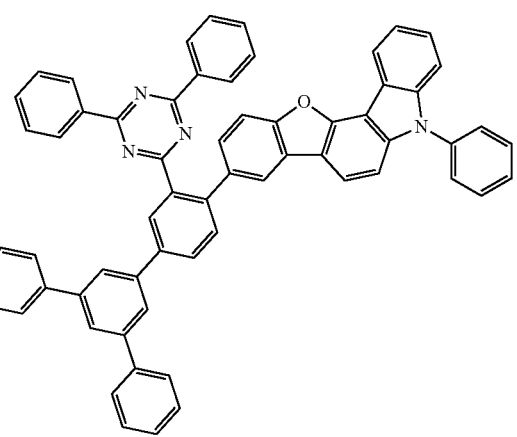

3601
-continued
737
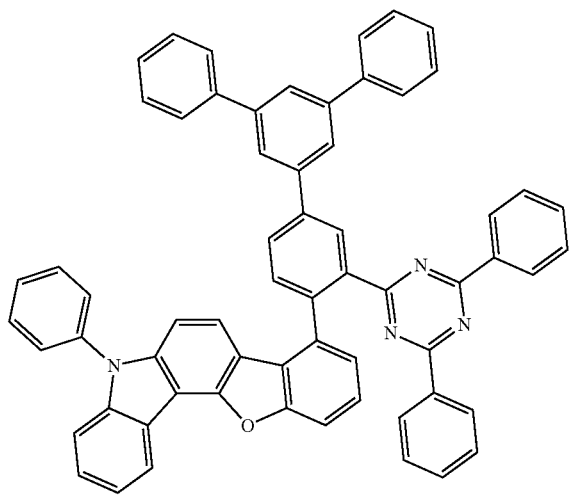
738
739
3602
-continued
740
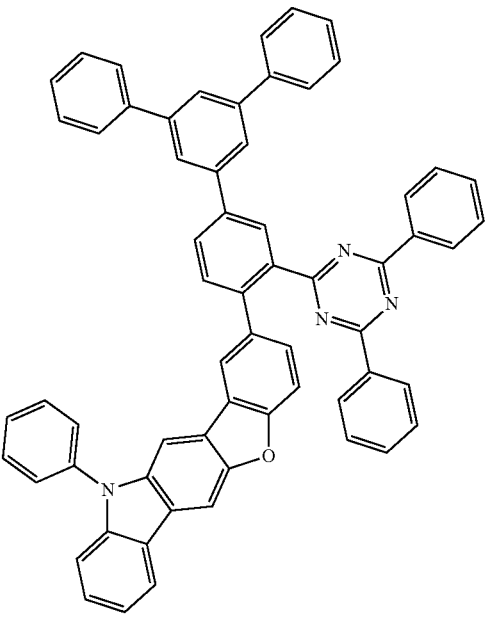
741
742
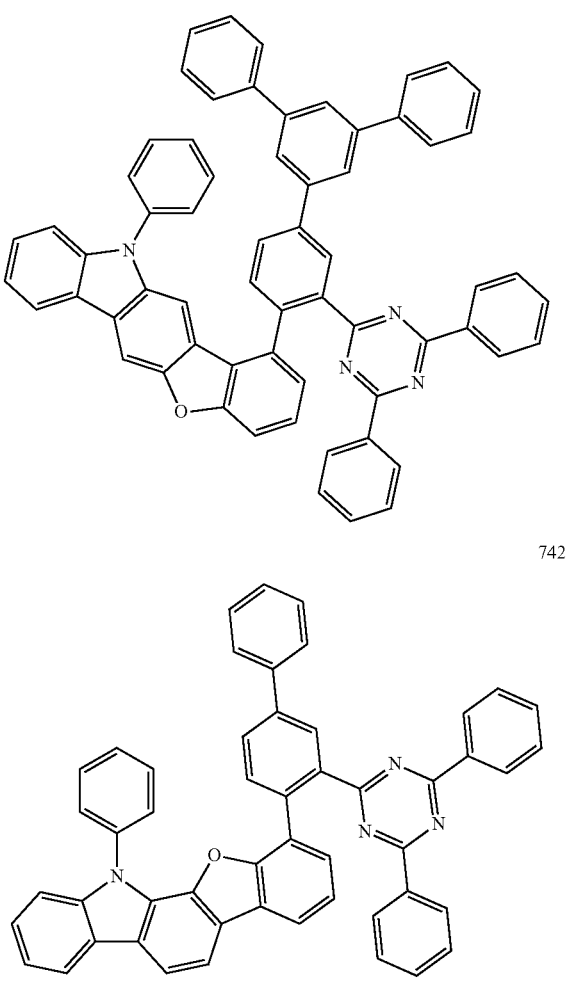

3603
-continued
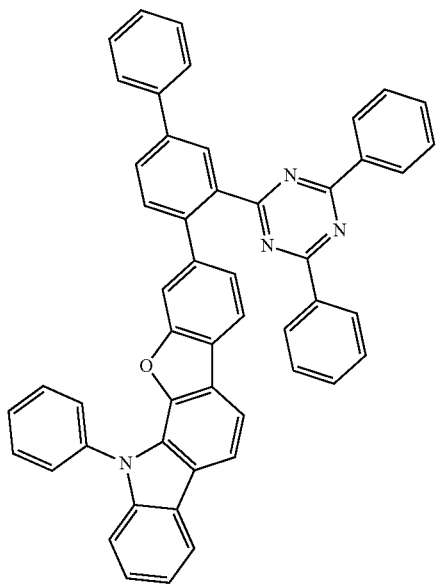
743
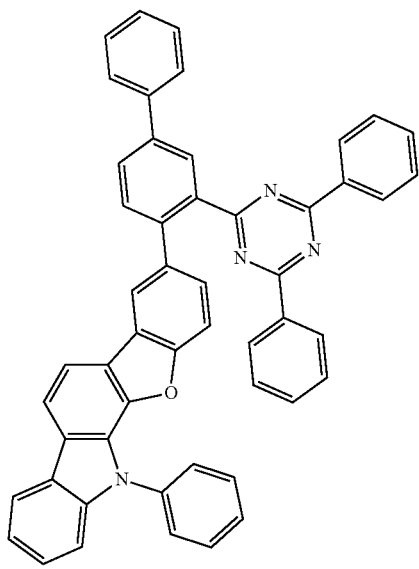
744
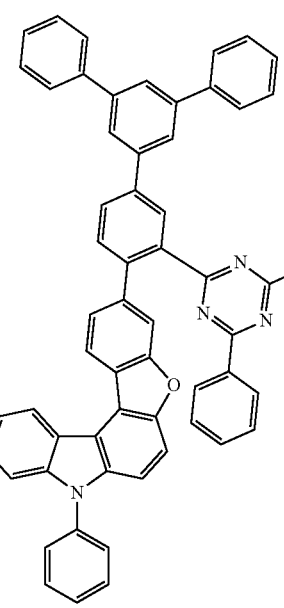
745
3604
-continued
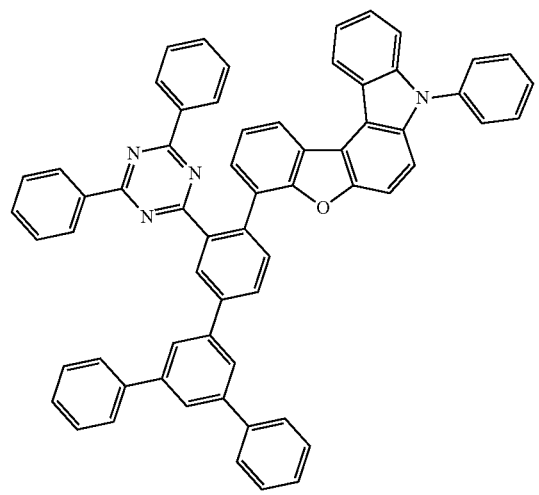
746
747

3605
-continued
748
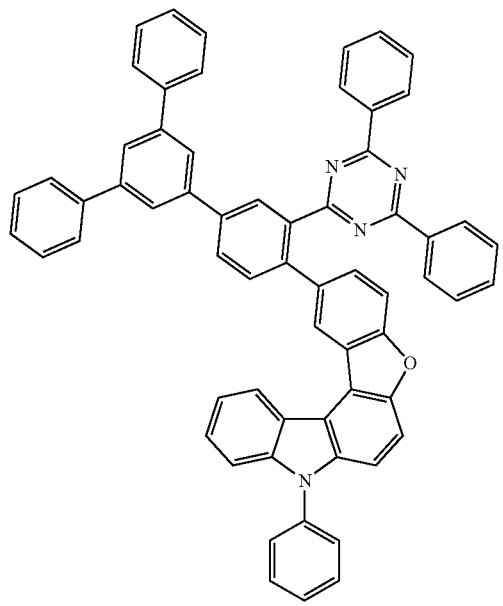
749
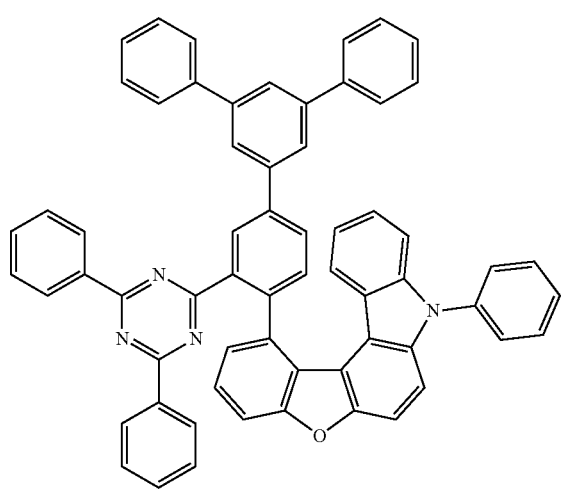
750
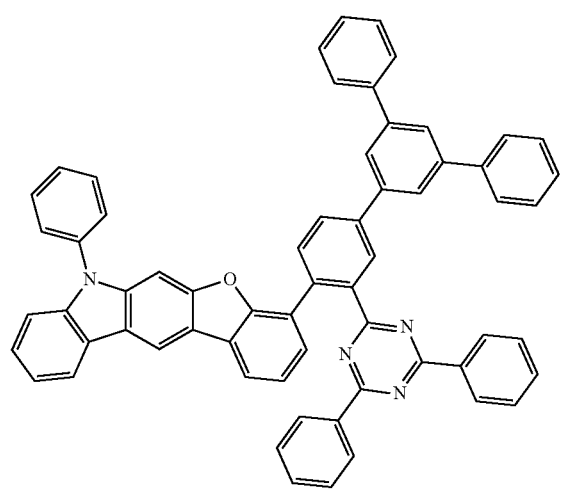
3606
-continued
751
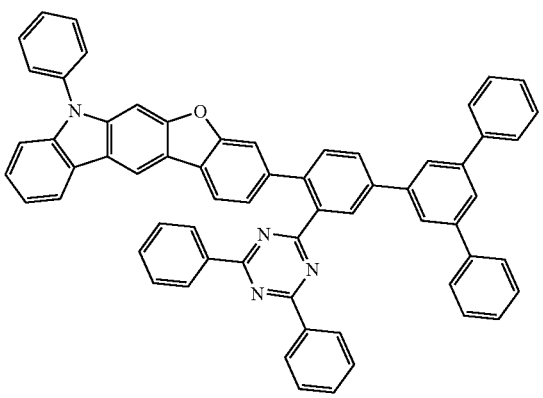
752
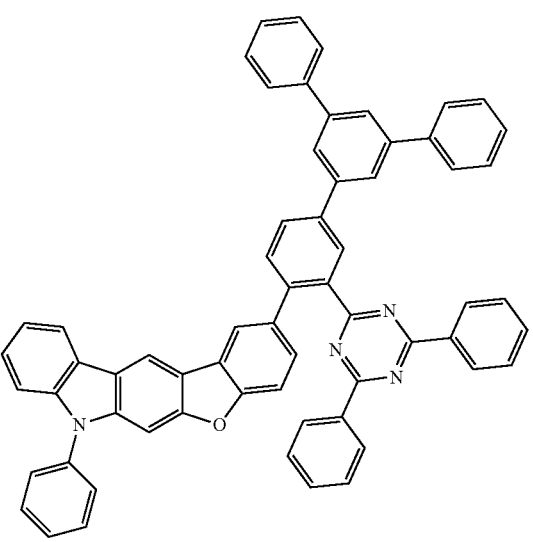
753
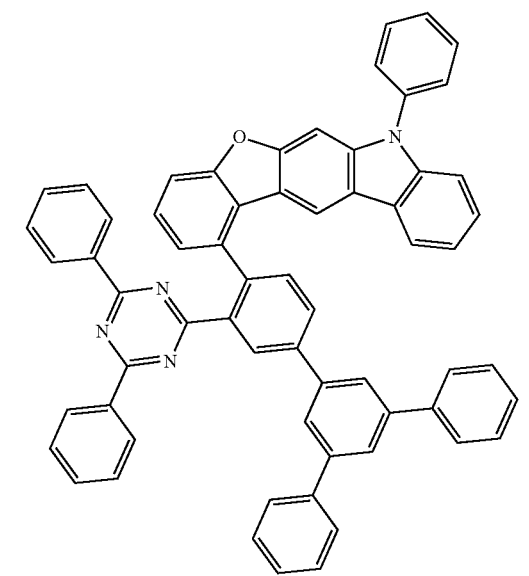

3607
-continued
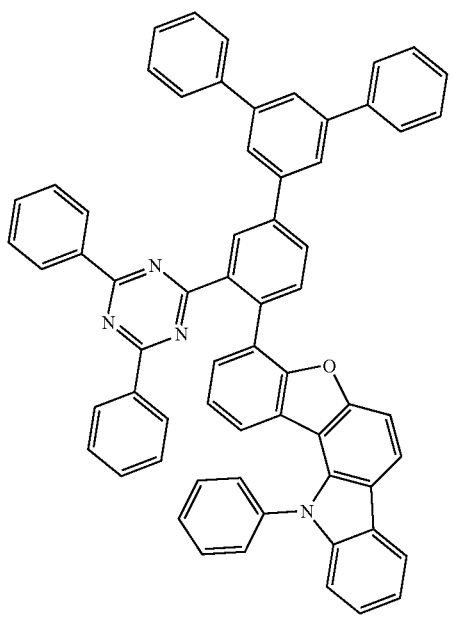
754
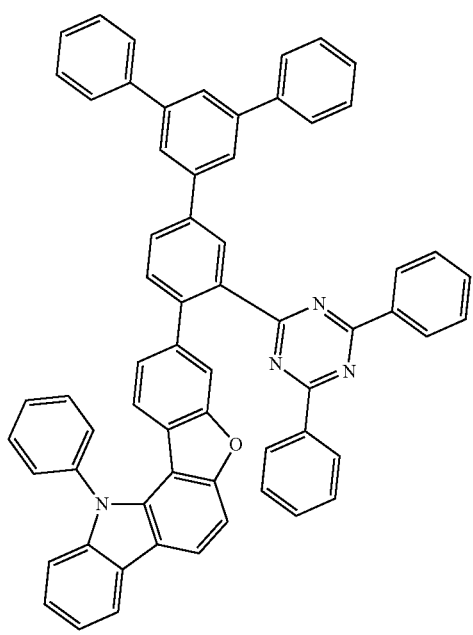
755
3608
-continued
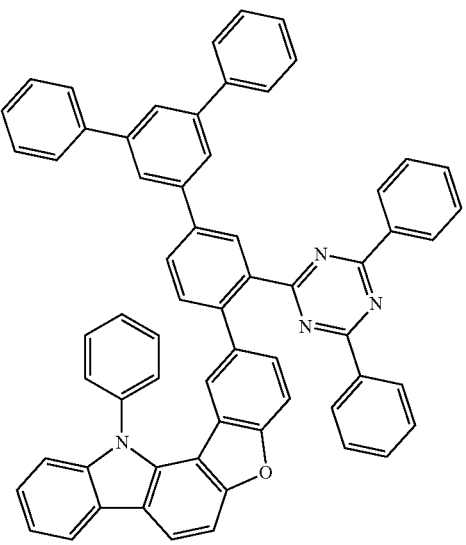
756
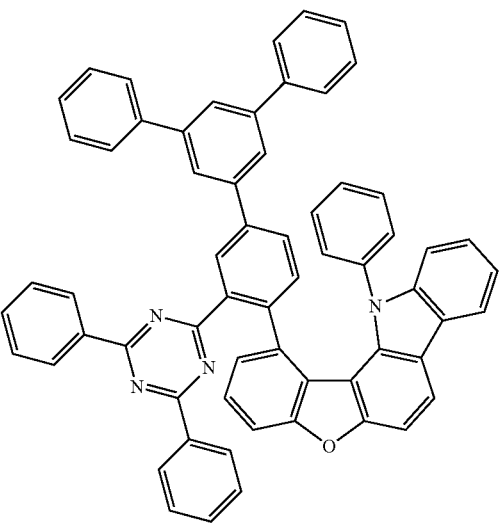
757

3609
-continued
758
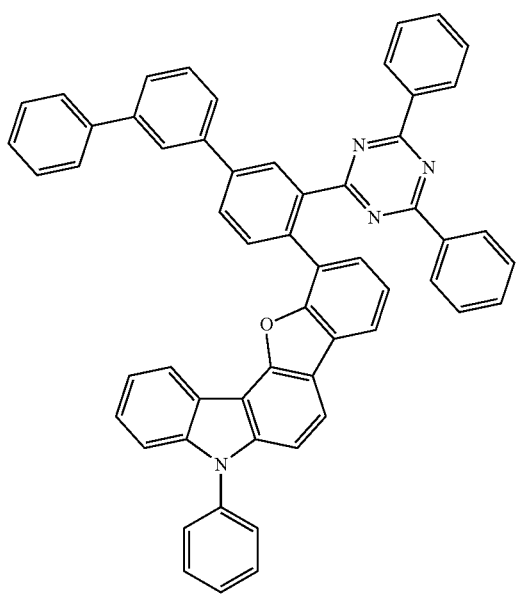
759
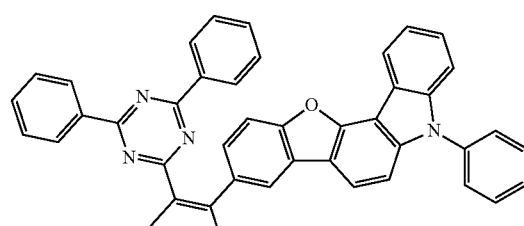
3610
-continued
760
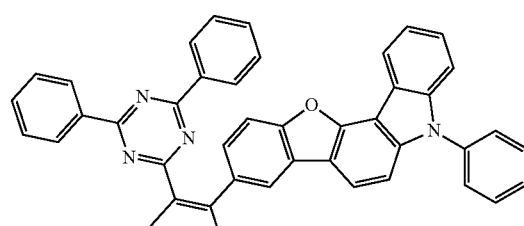
761
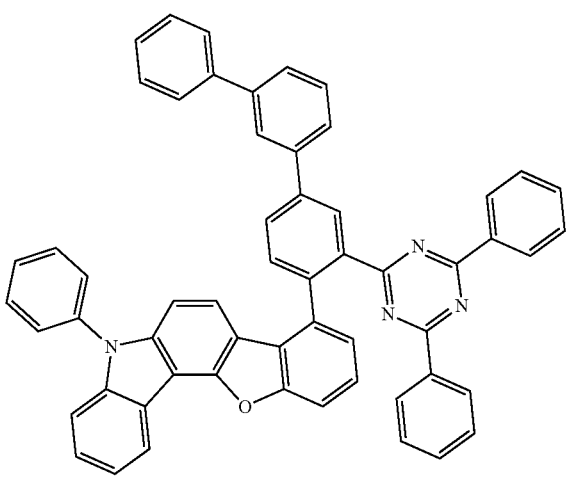
762
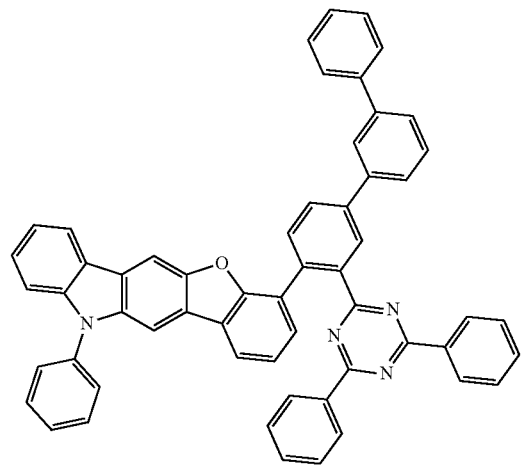

3611
-continued
763
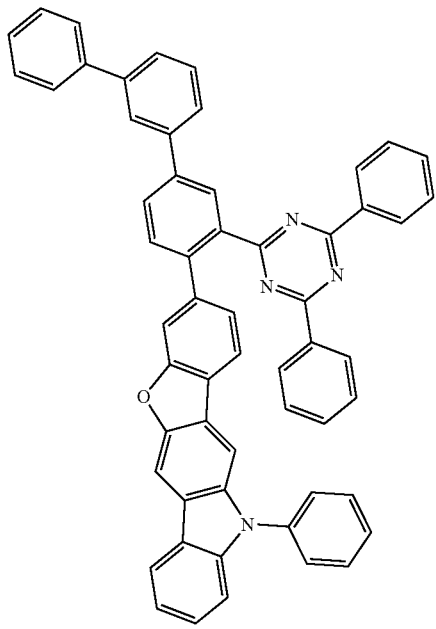
764
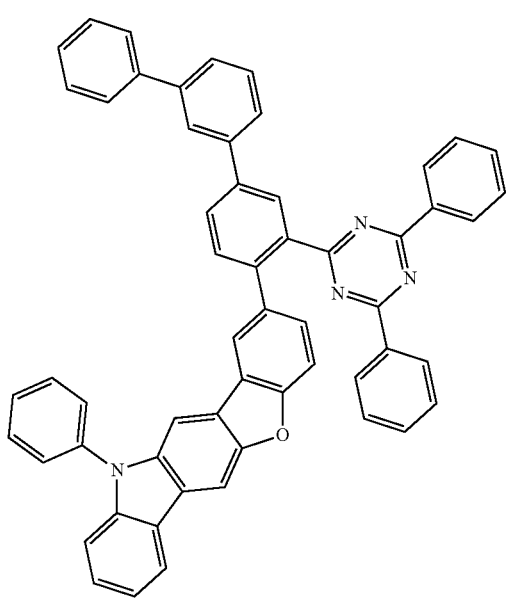
3612
-continued
765
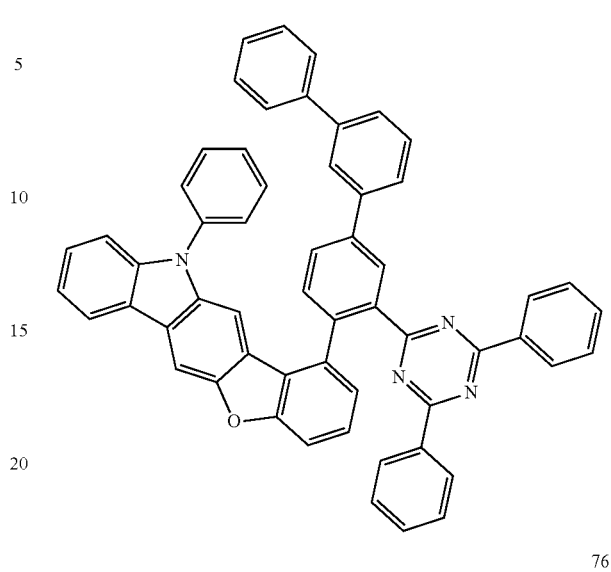
766
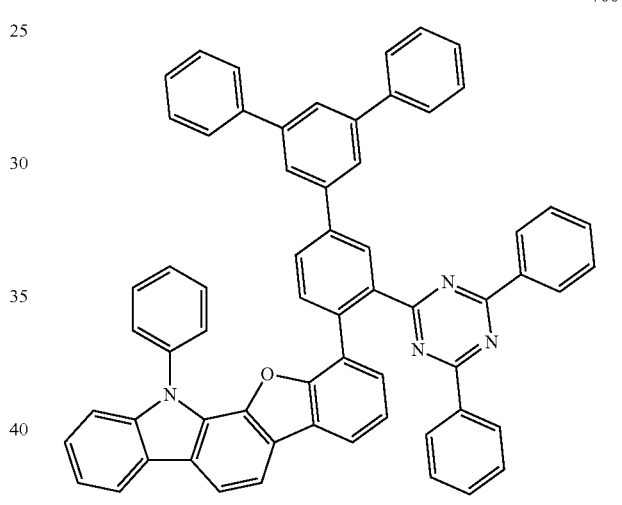
767
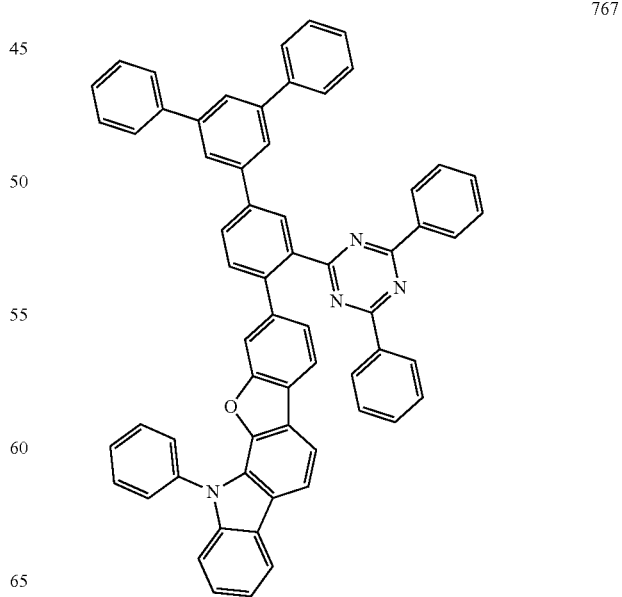

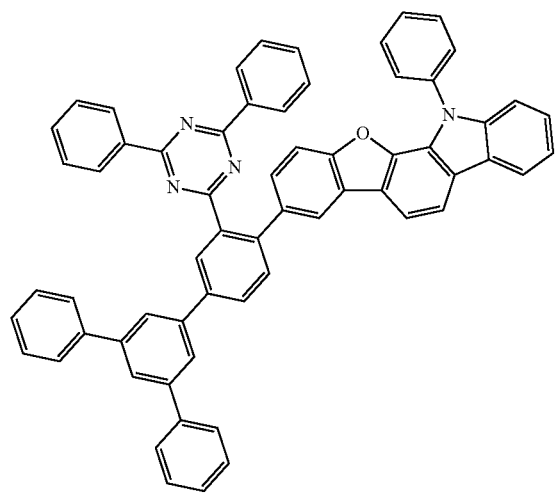
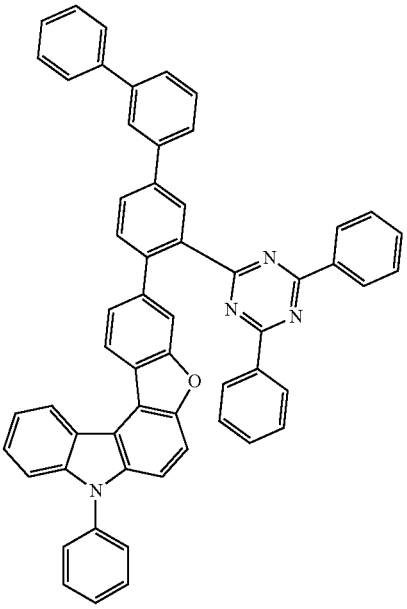
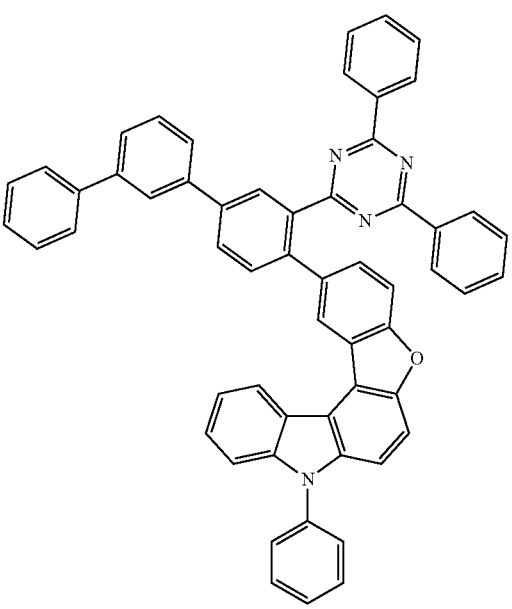

3615
-continued
3616
-continued
773
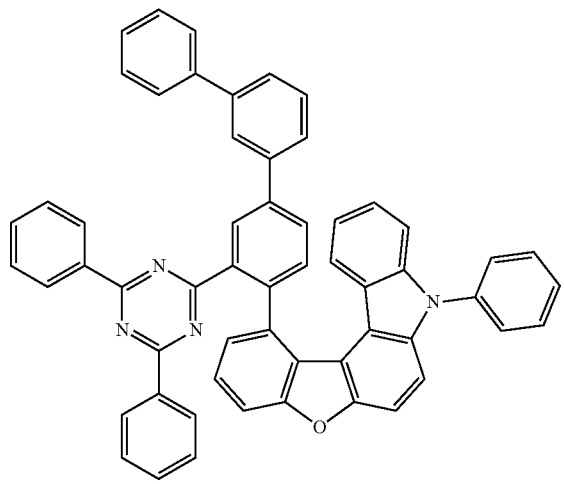
776
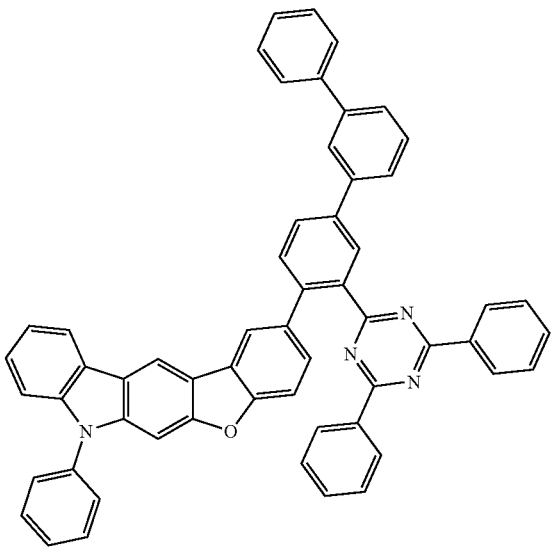
774
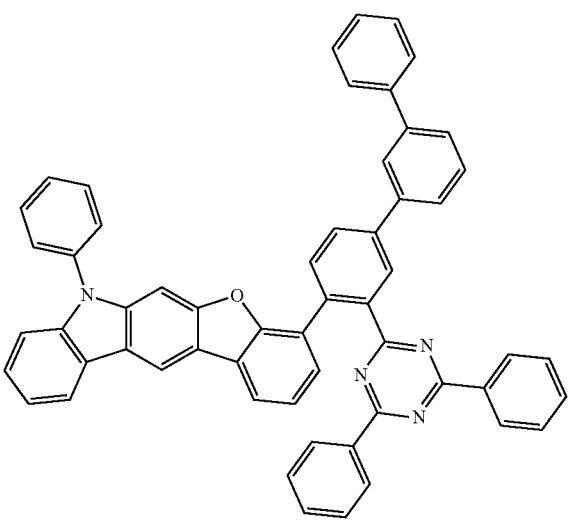
777
775
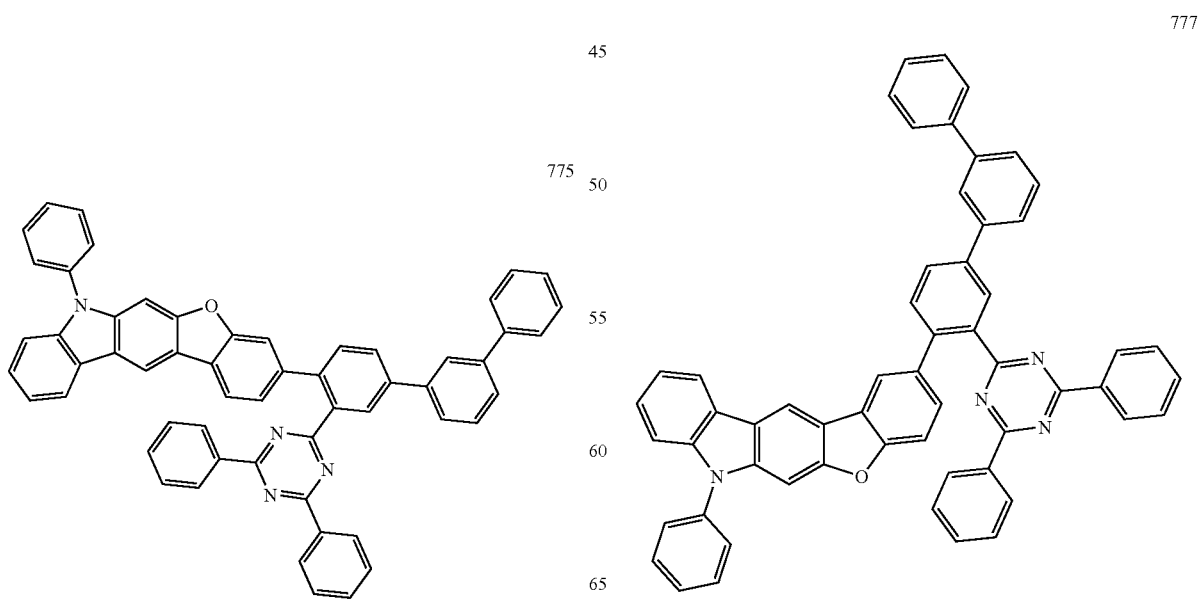

3617
-continued
778
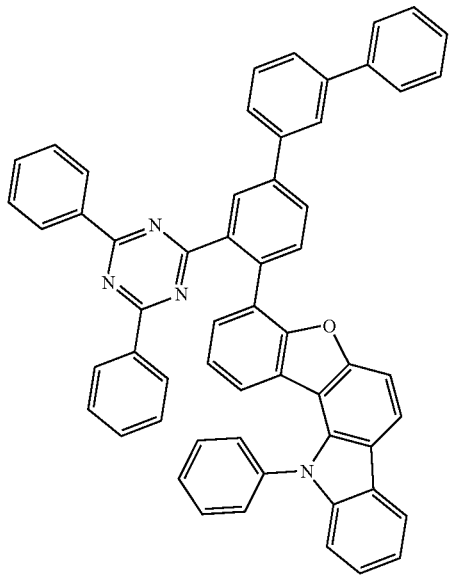
779
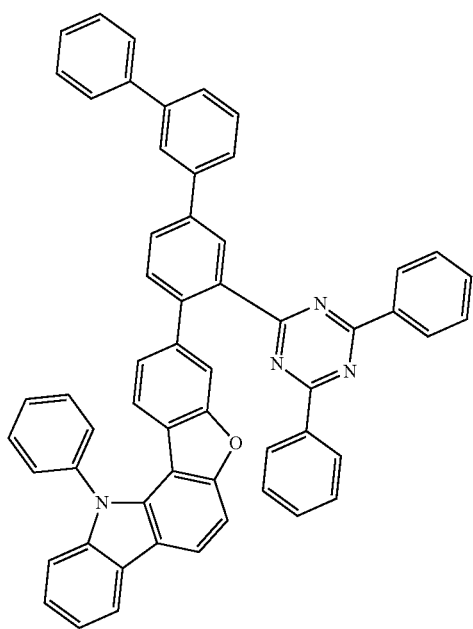
3618
-continued
780
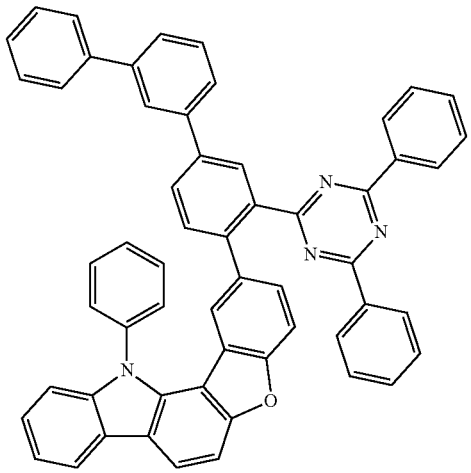
781
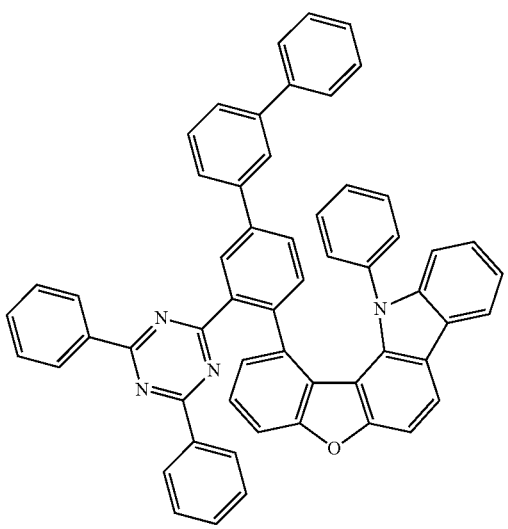
782
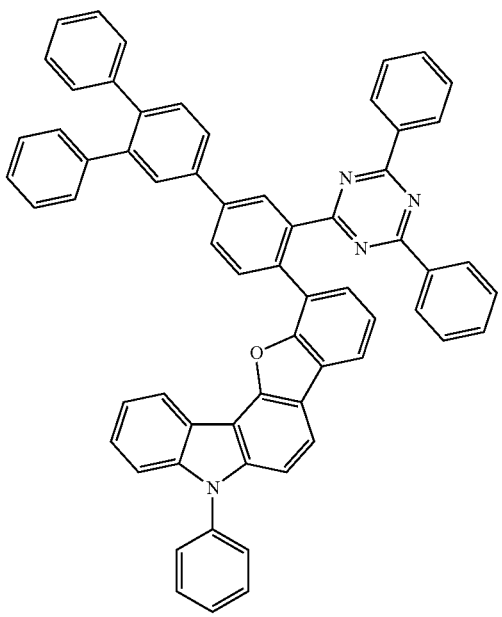

3619
-continued
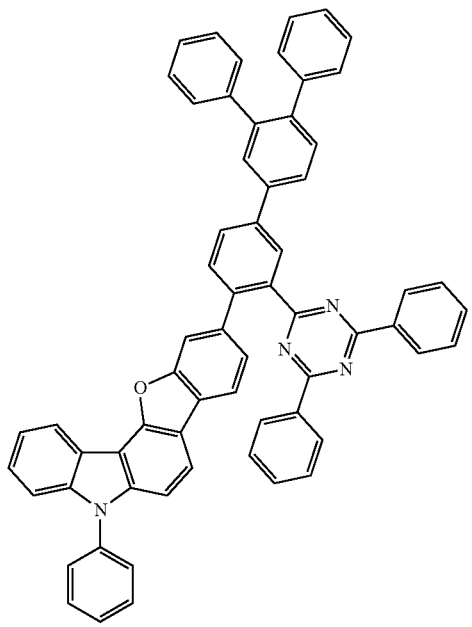
783
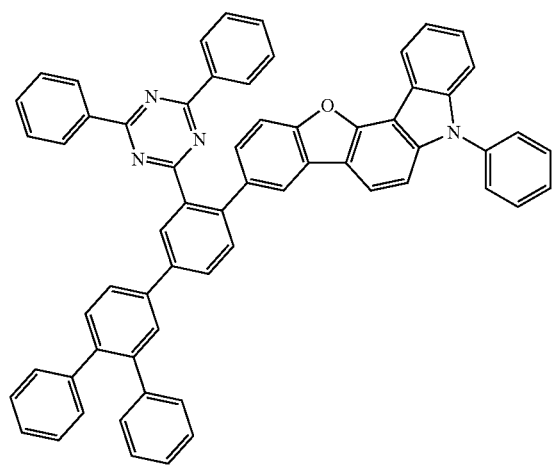
784
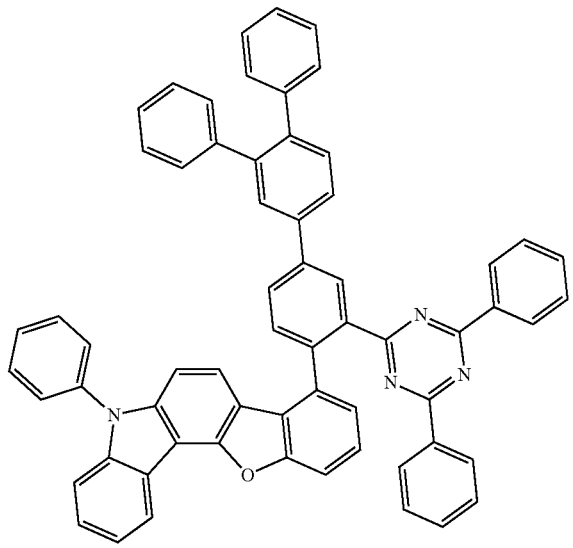
785
3620
-continued
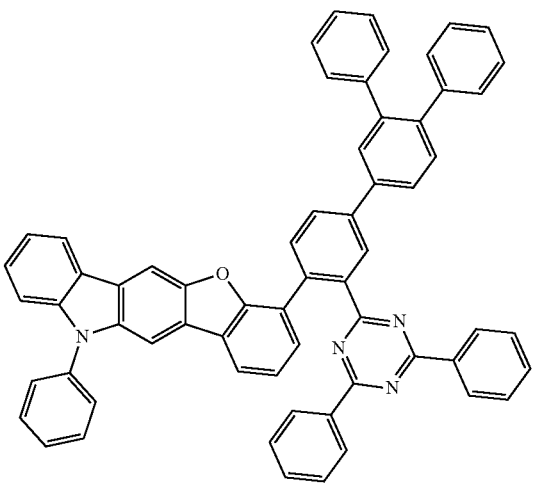
786
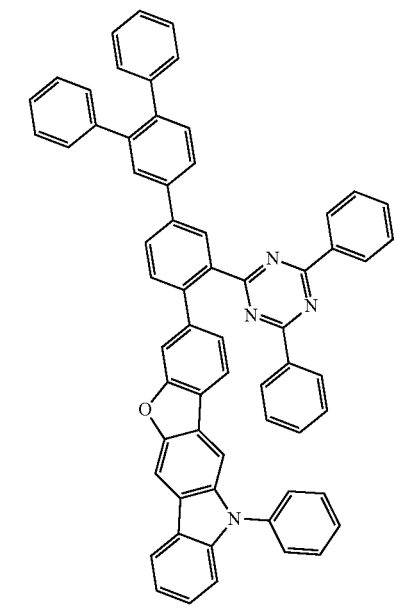
787

3621
-continued
788
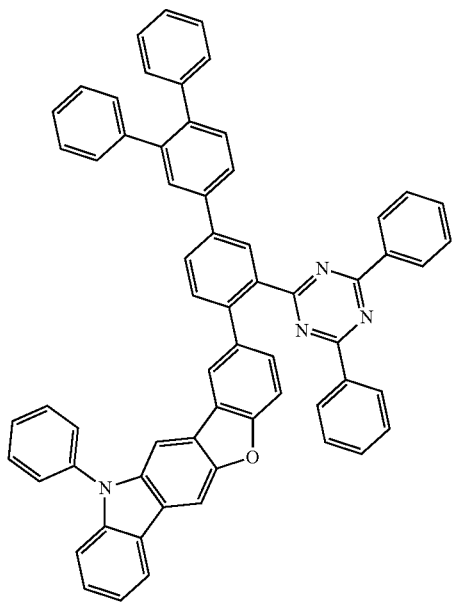
789
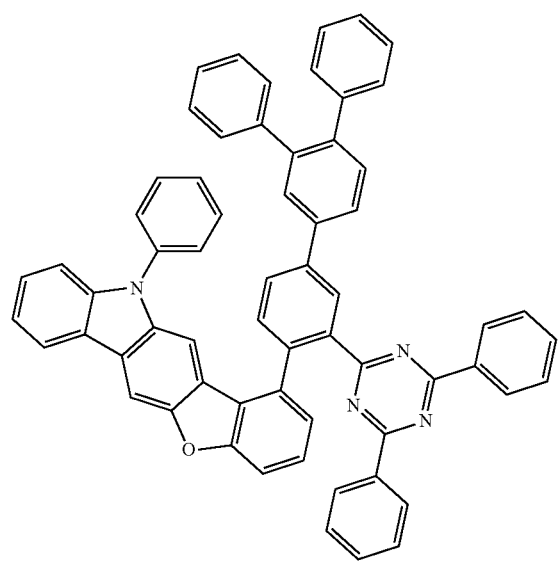
790
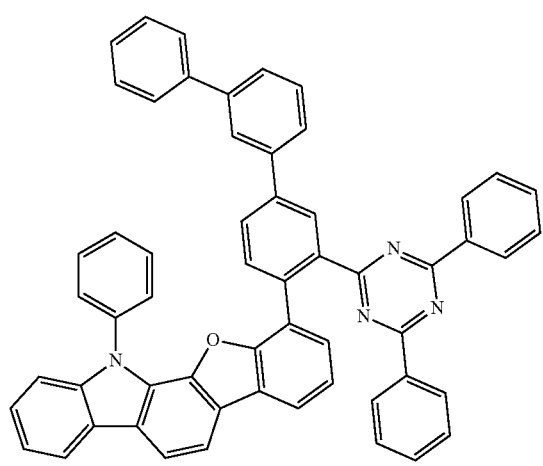
3622
-continued
791
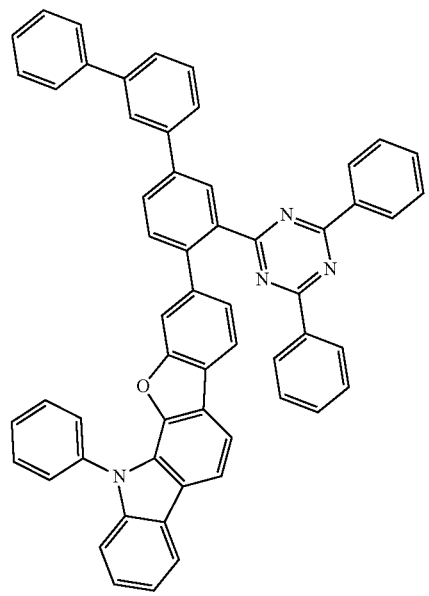
792
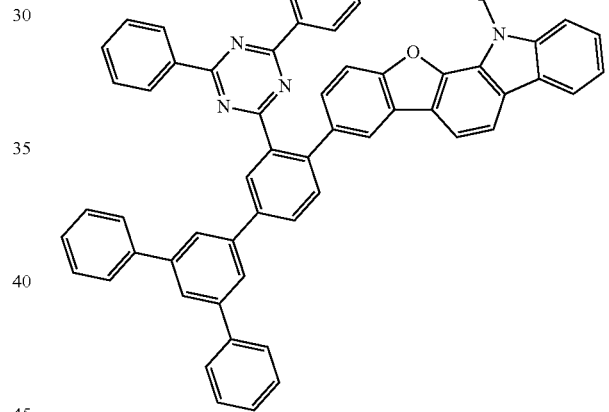
793
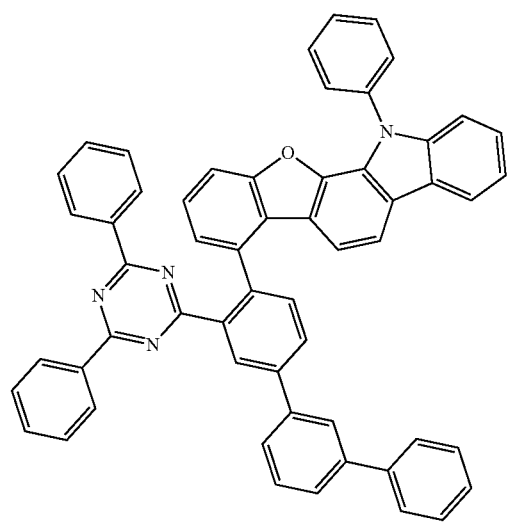

3623
-continued
794
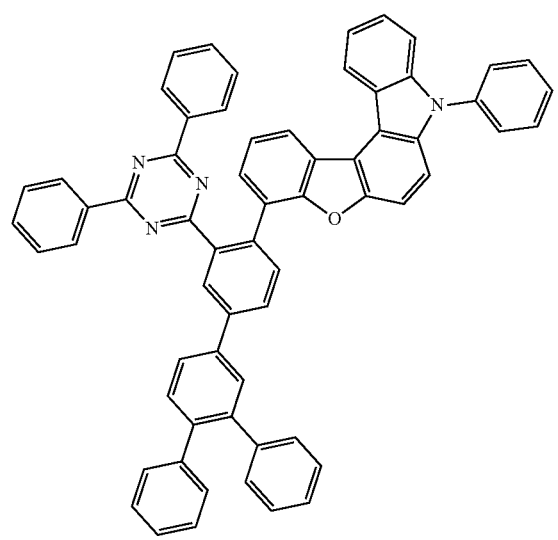
795
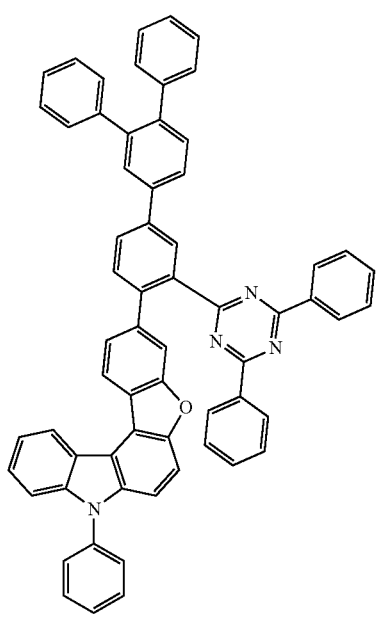
3624
-continued
796
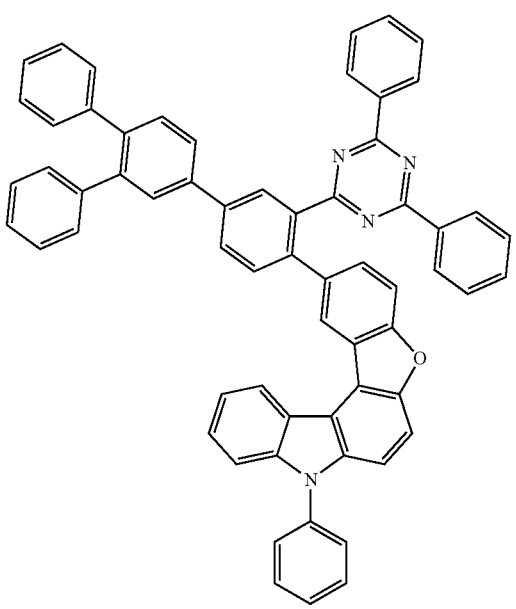
797
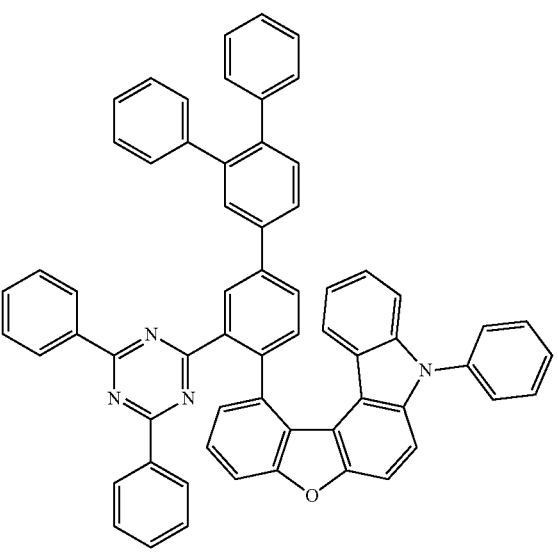

3625
-continued
798
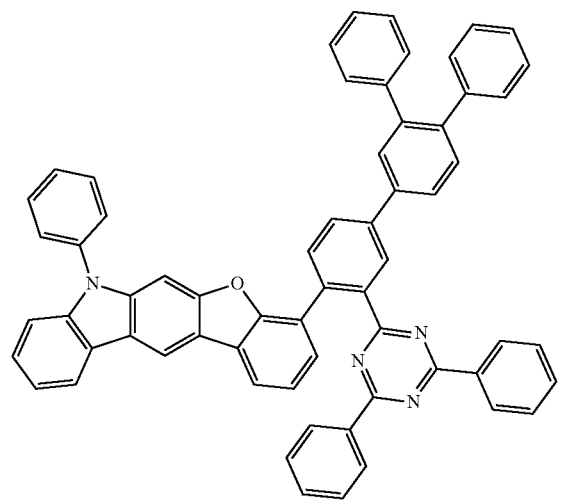
799
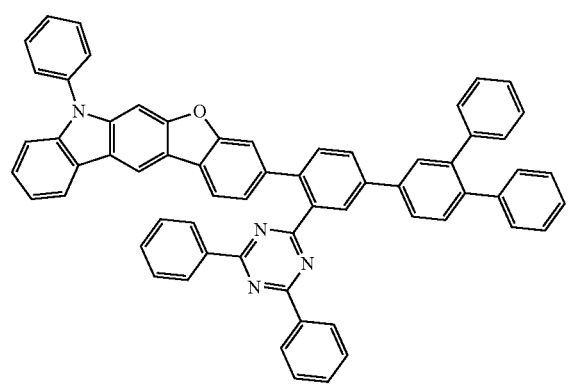
800
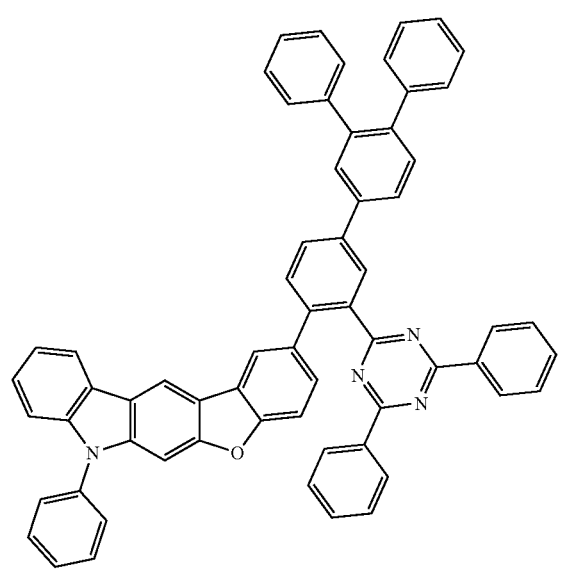
3626
-continued
801
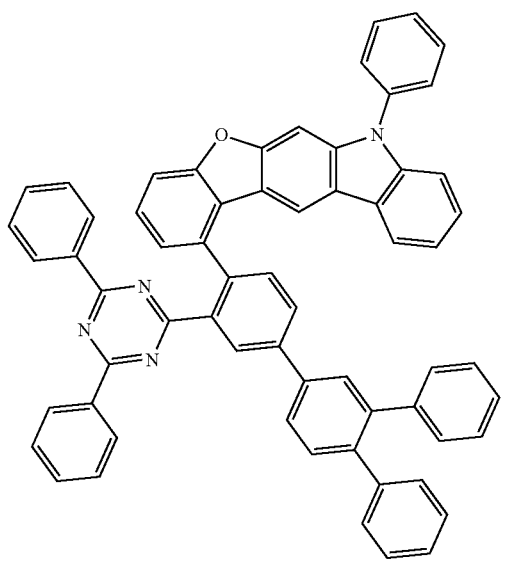
802
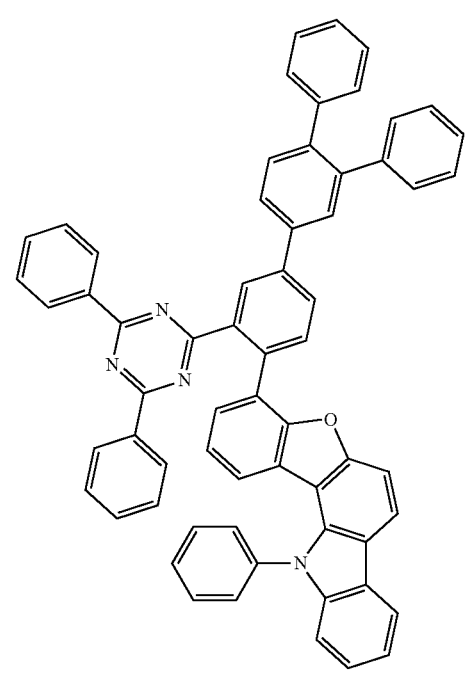

3627
-continued
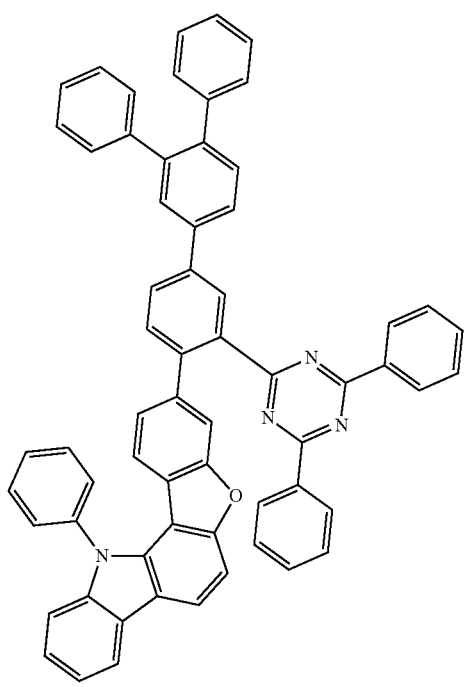
803
3628
-continued
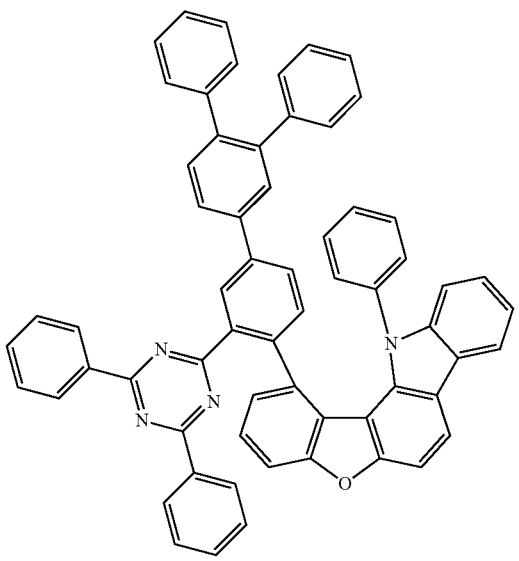
805
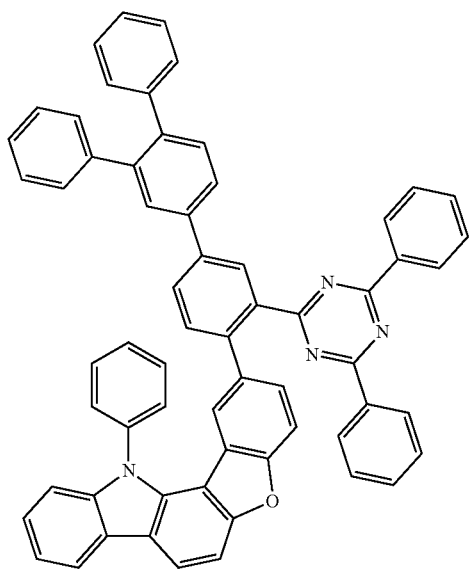
804
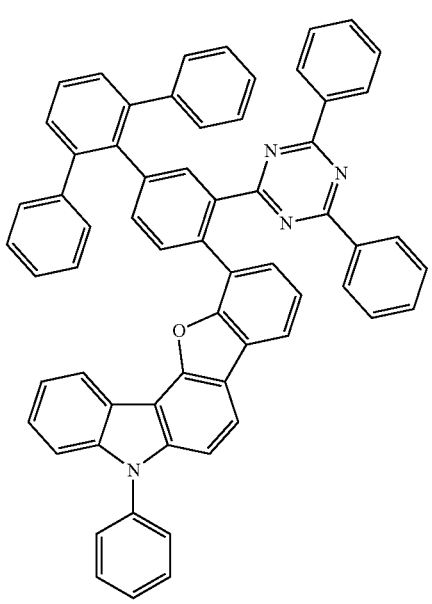
806

3629
-continued
807
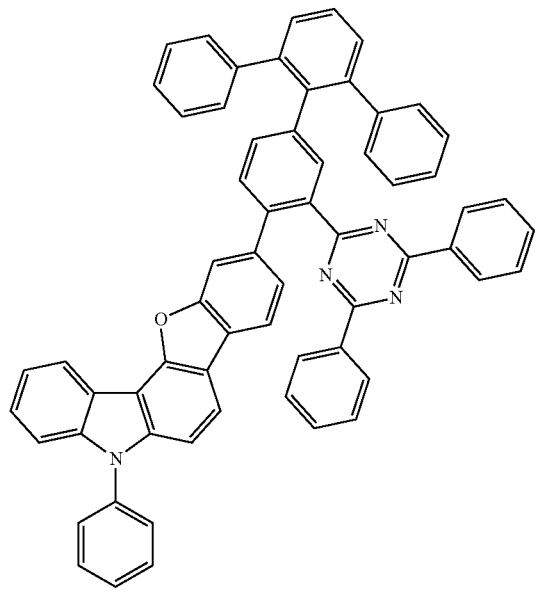
808
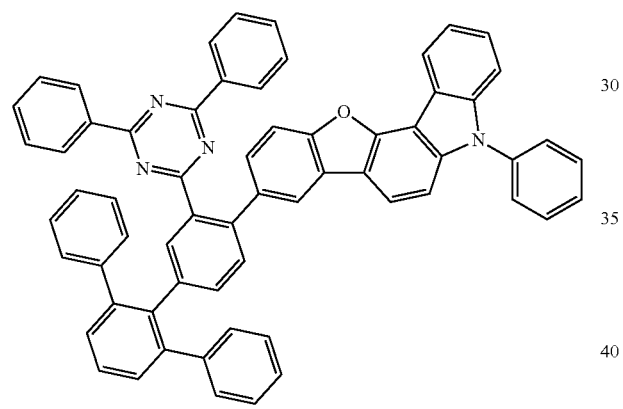
809
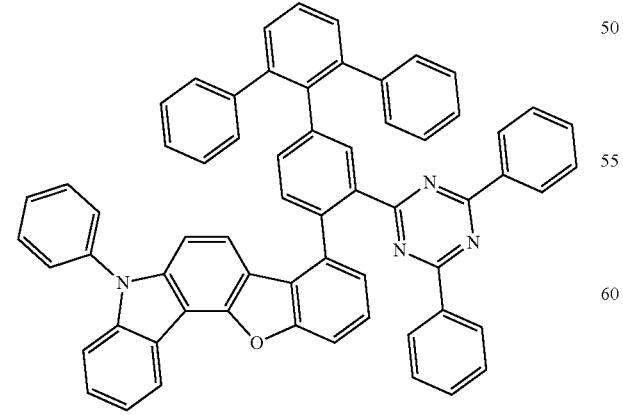
3630
-continued
810
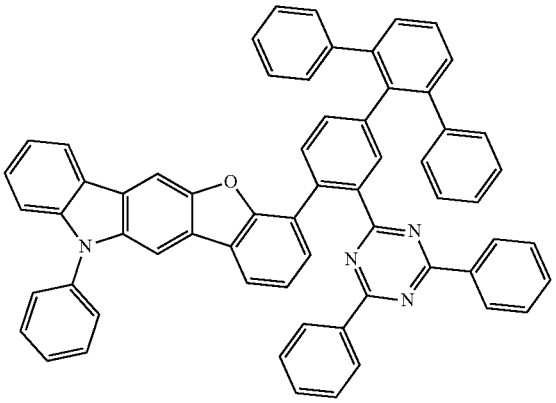
811
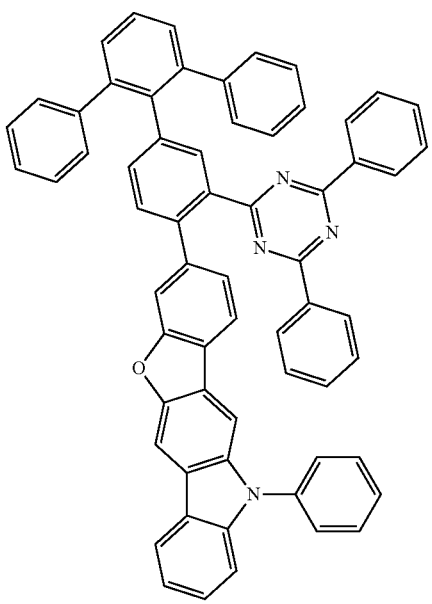
812
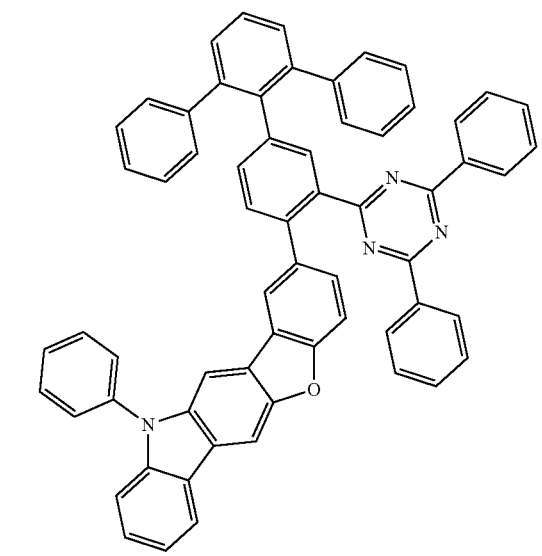

3631
-continued
3632
-continued
813
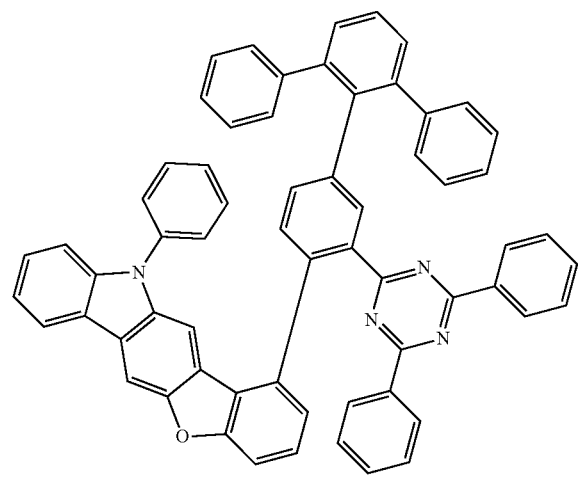
816
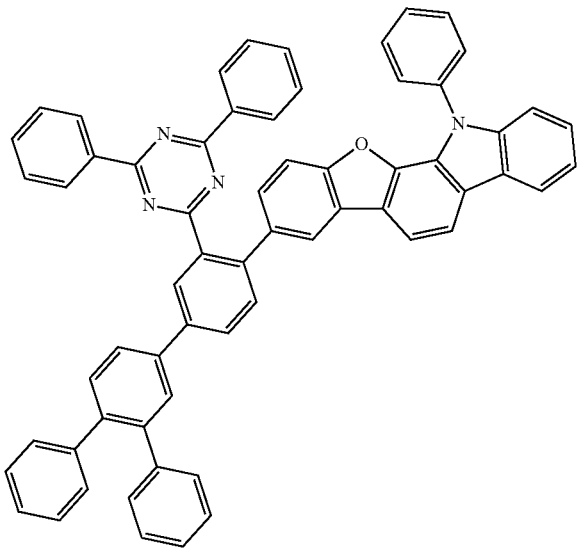
814
817
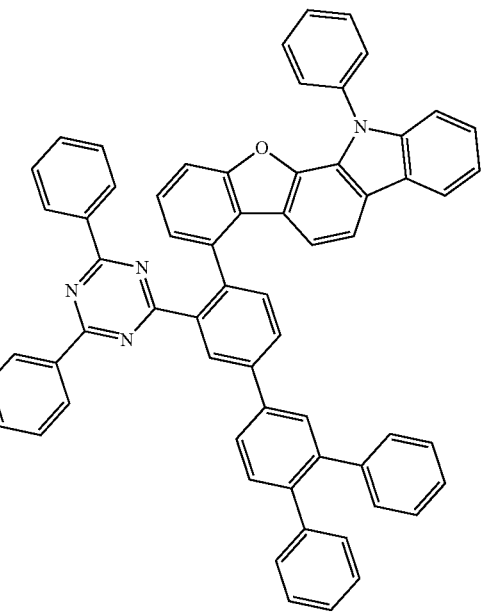
815
818
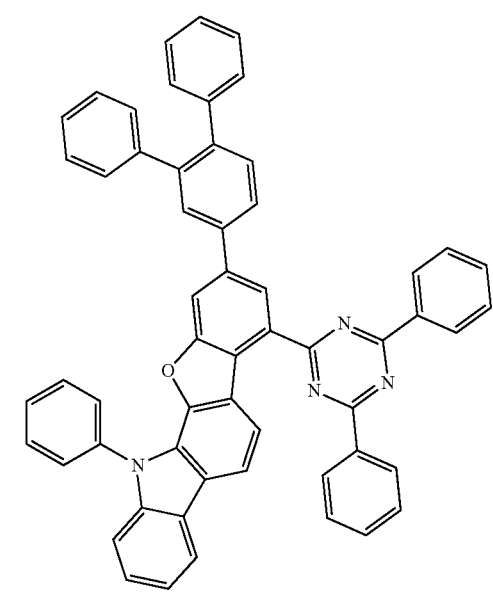
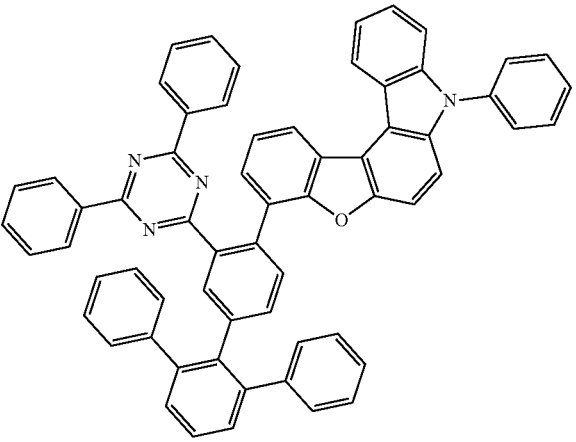

3633
-continued
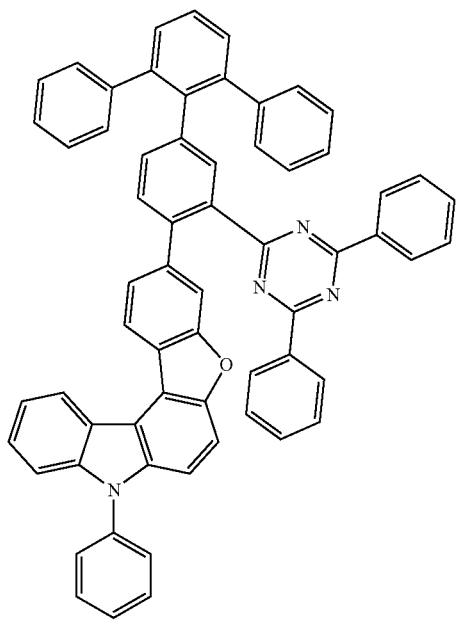
3634
-continued
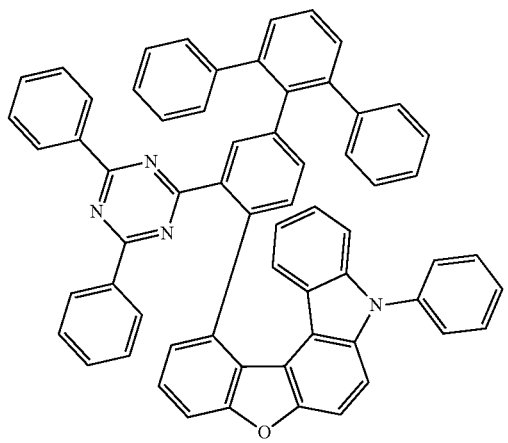
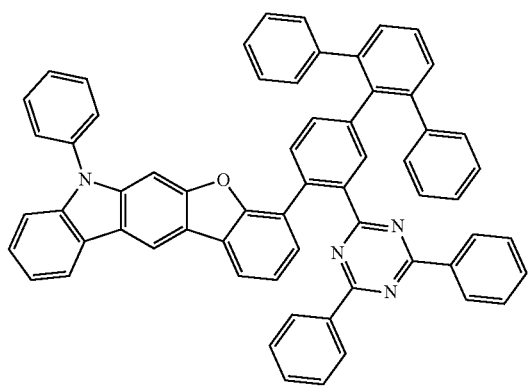
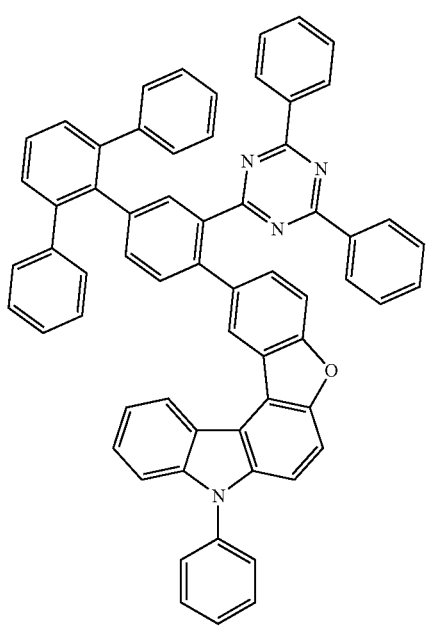
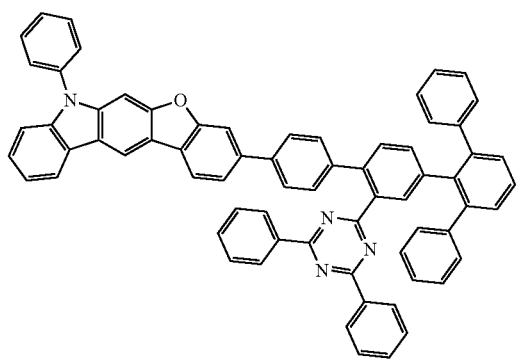

3635
-continued
824
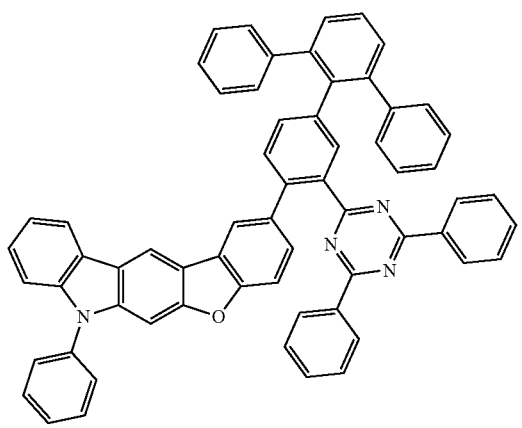
825
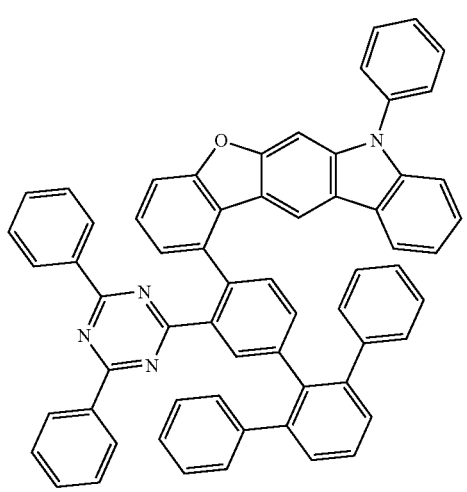
826
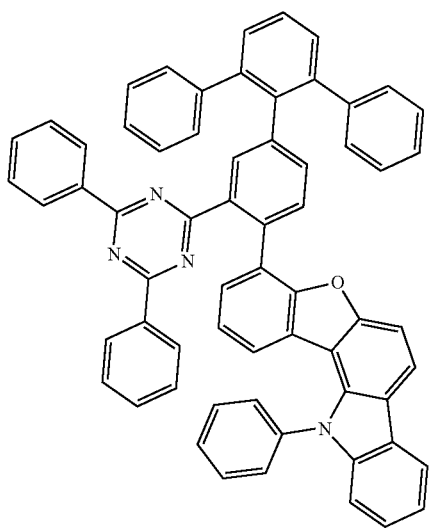
3636
-continued
827
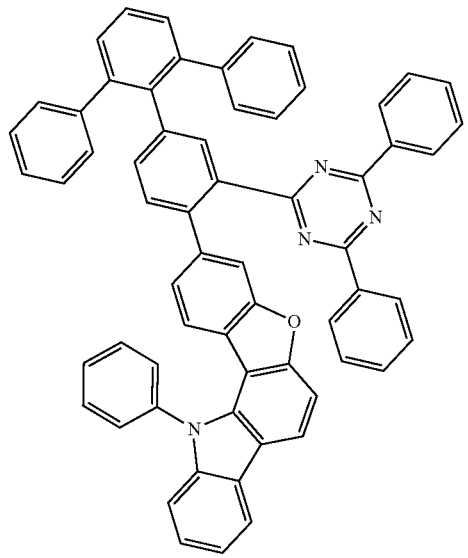
828
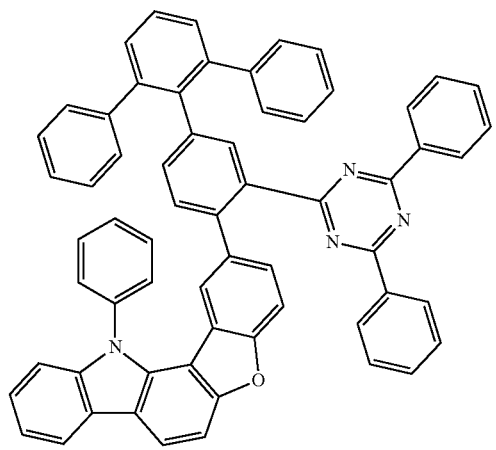
829
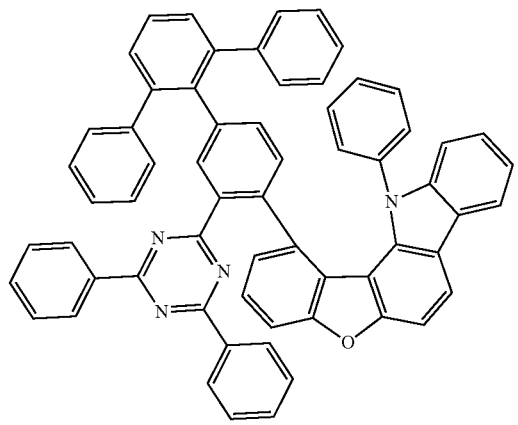

3637
-continued
830
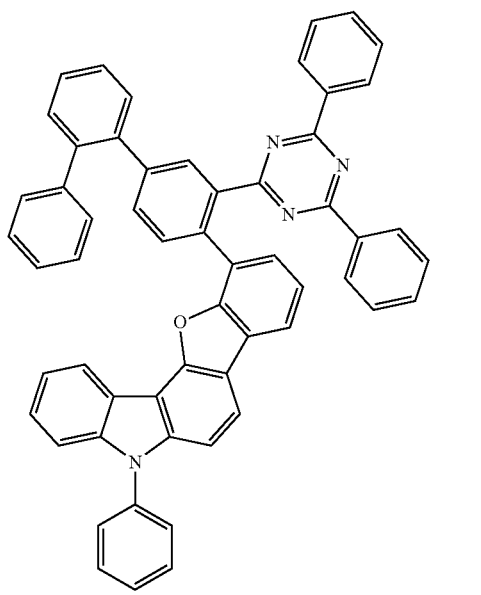
831
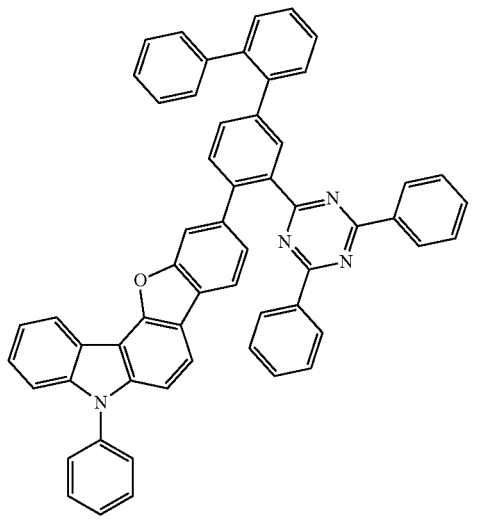
832
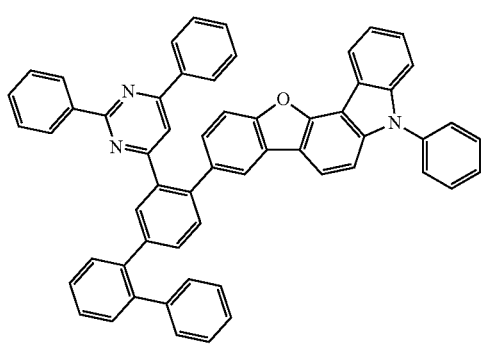
3638
-continued
833
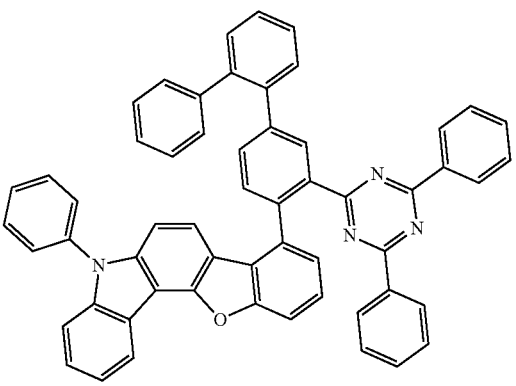
834
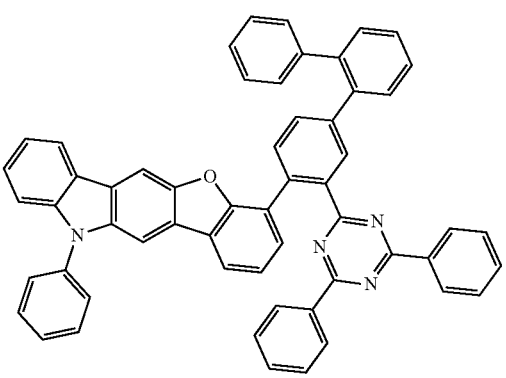
835
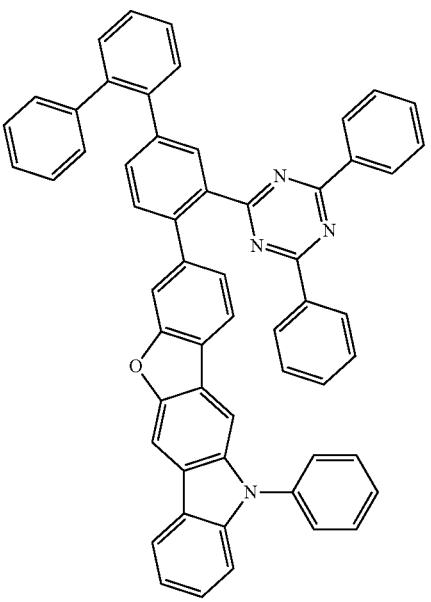

-continued
836
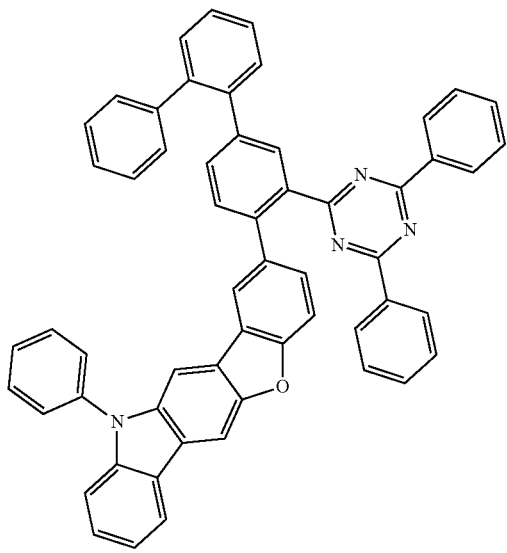
837
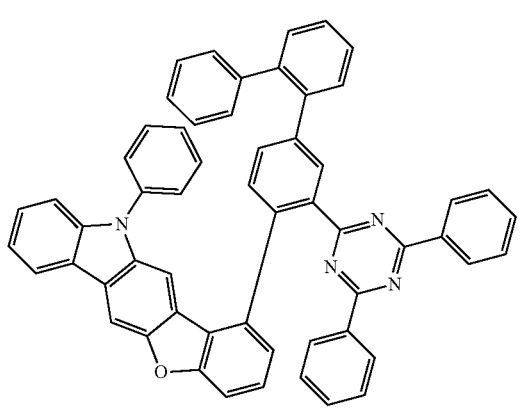
838
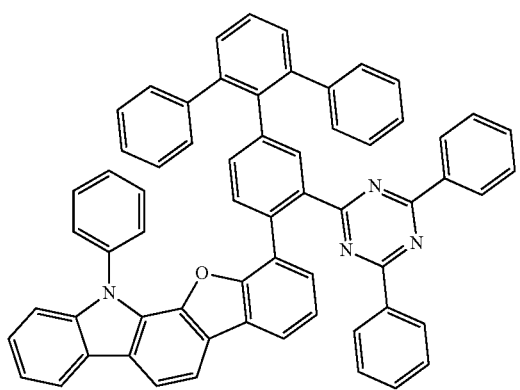
-continued
839
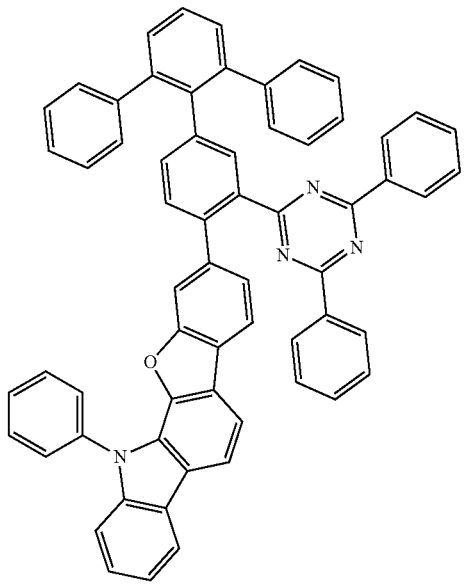
840
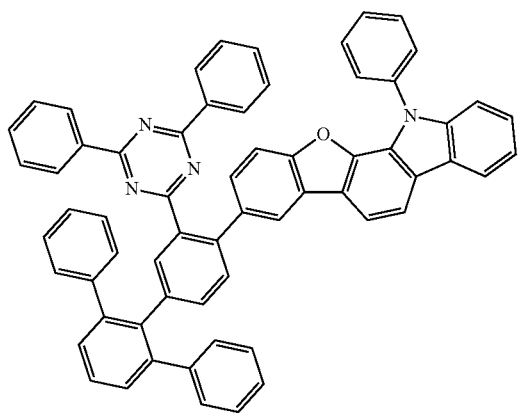
841
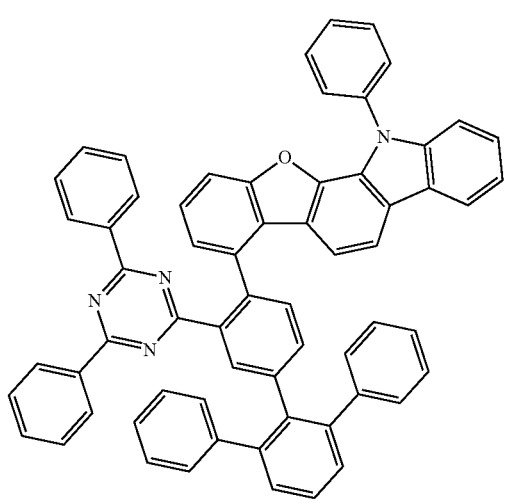

3641
-continued
842
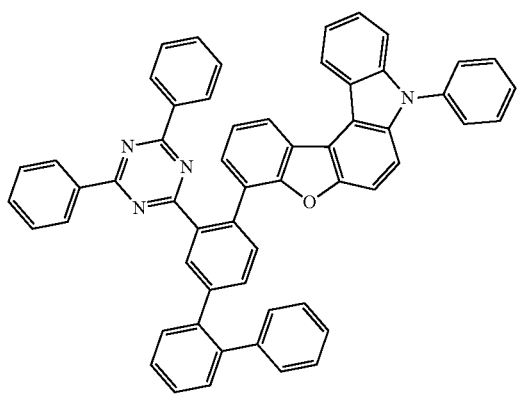
843
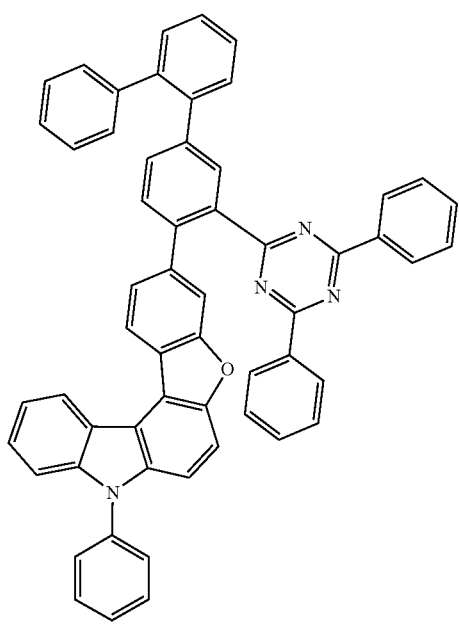
844
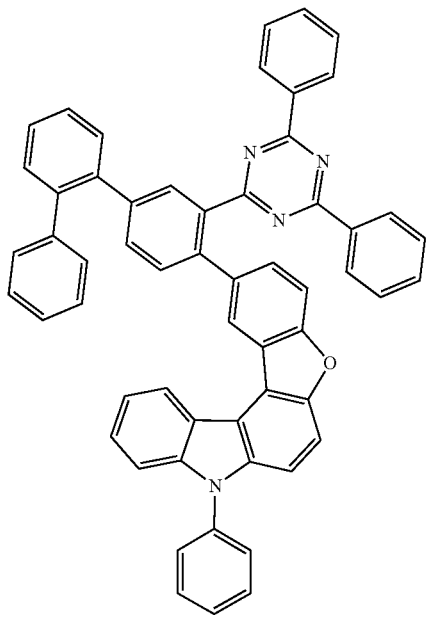
3642
-continued
845
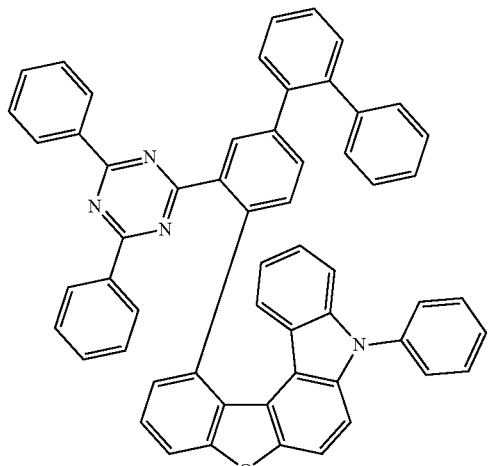
846
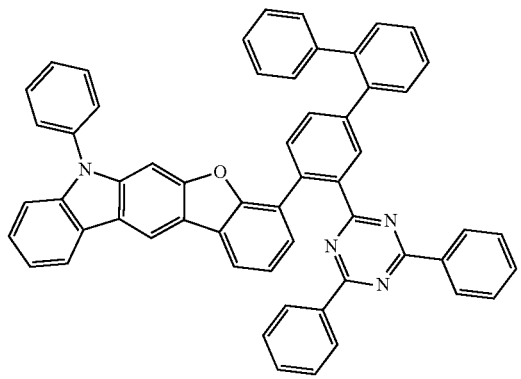
847
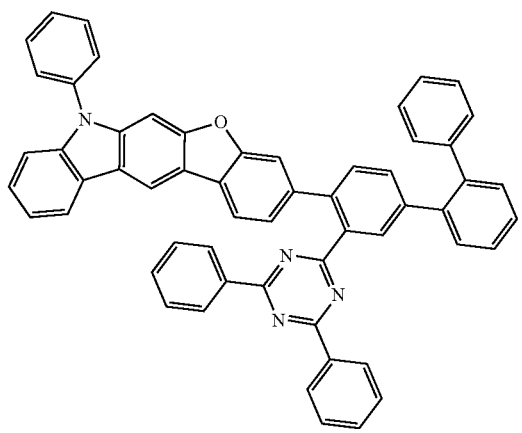

-continued
848
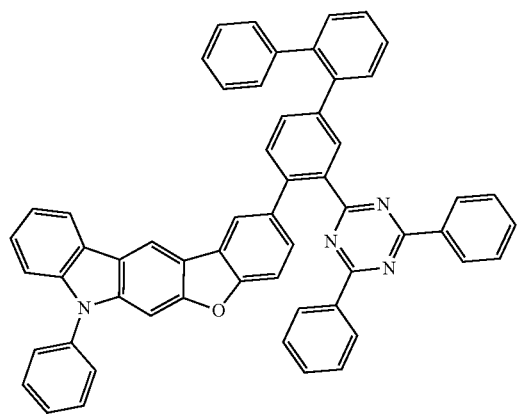
849
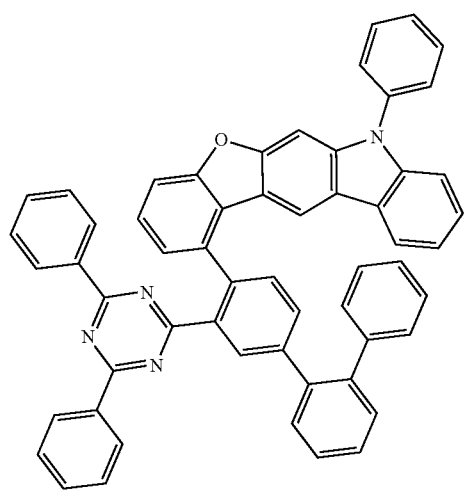
850
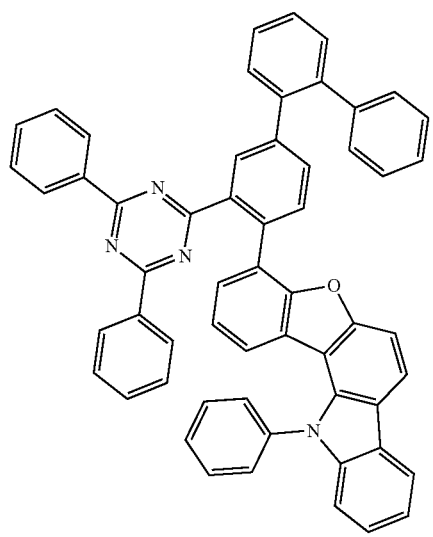
-continued
851
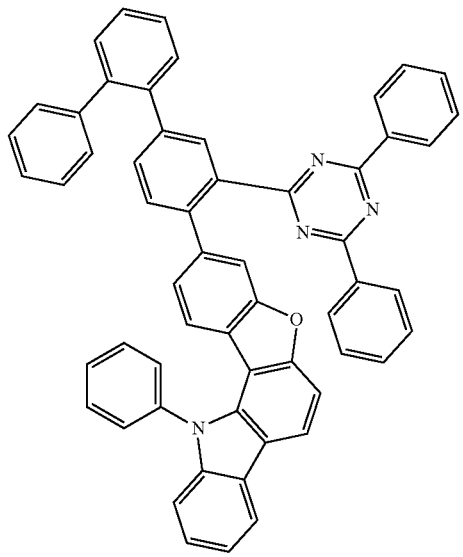
852
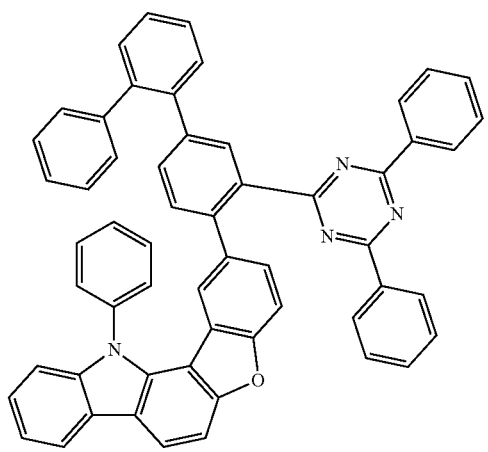
853
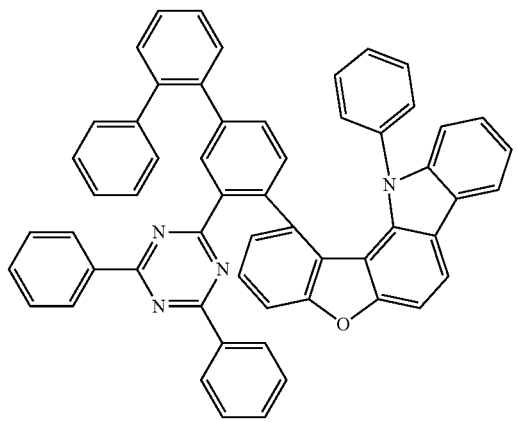

-continued
854
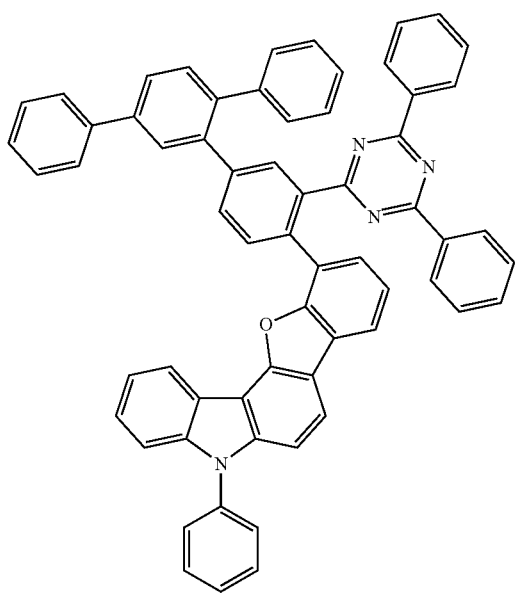
855
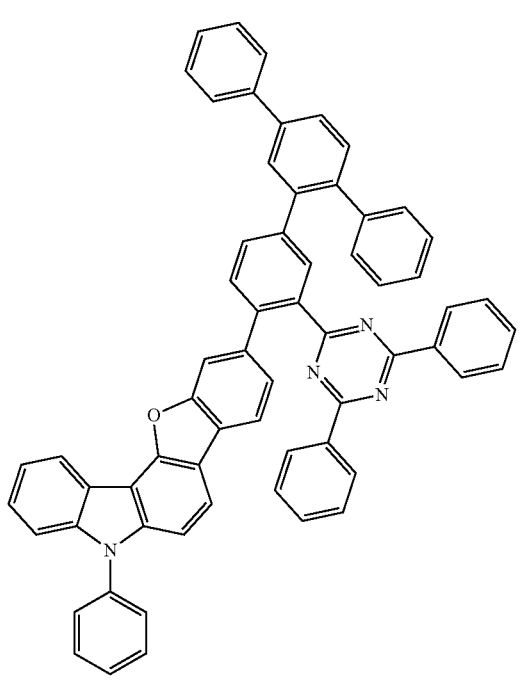
856
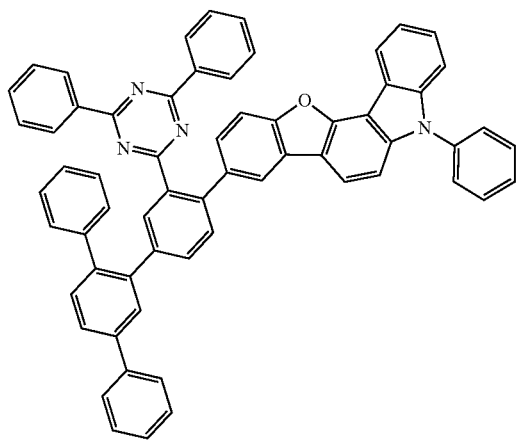
857
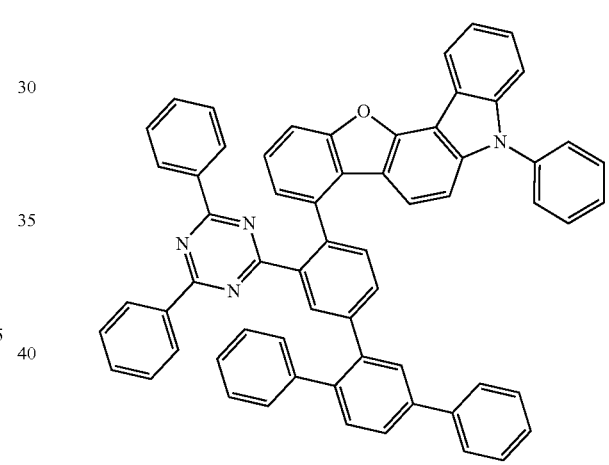
858
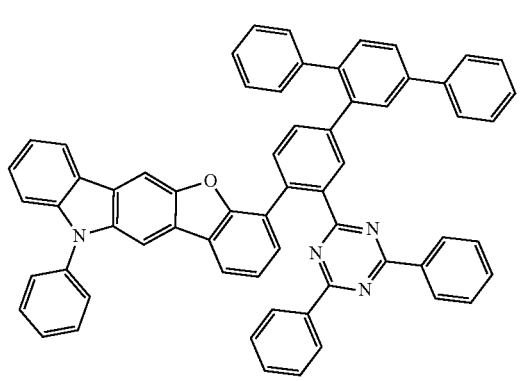

3647
-continued
859
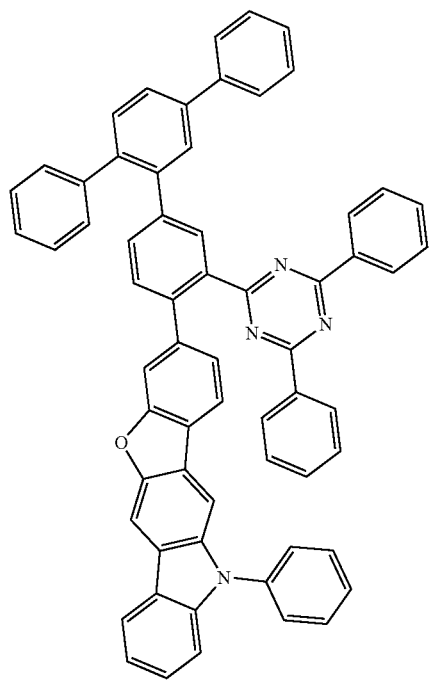
3648
-continued
861
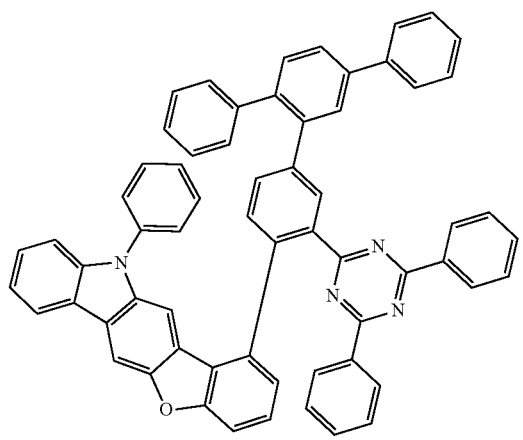
862
860
863
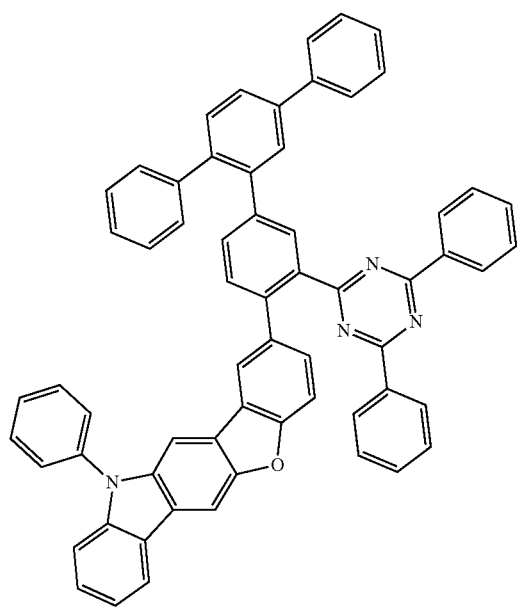

864
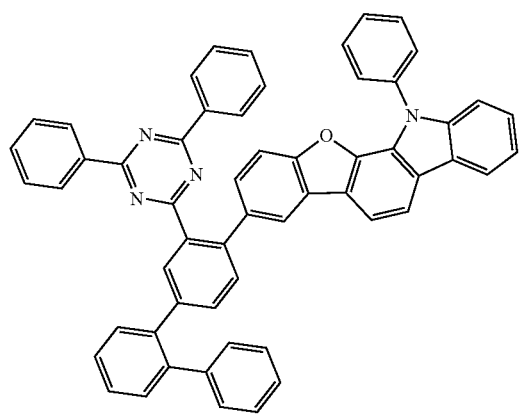
865
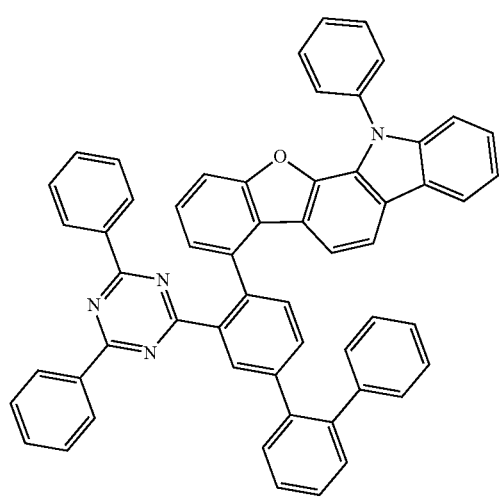
866
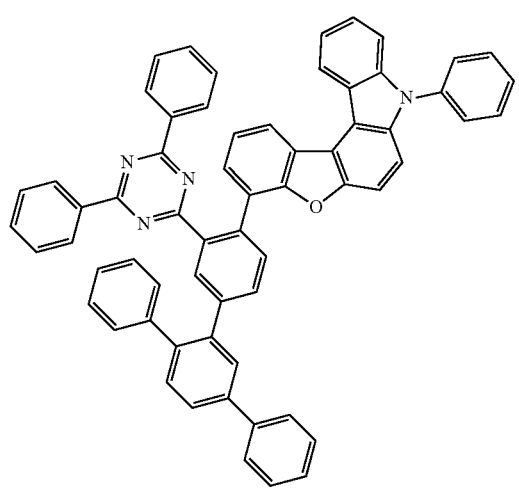
867
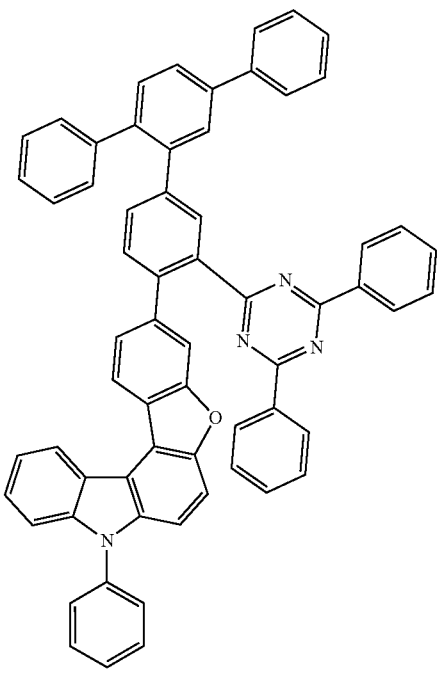
868
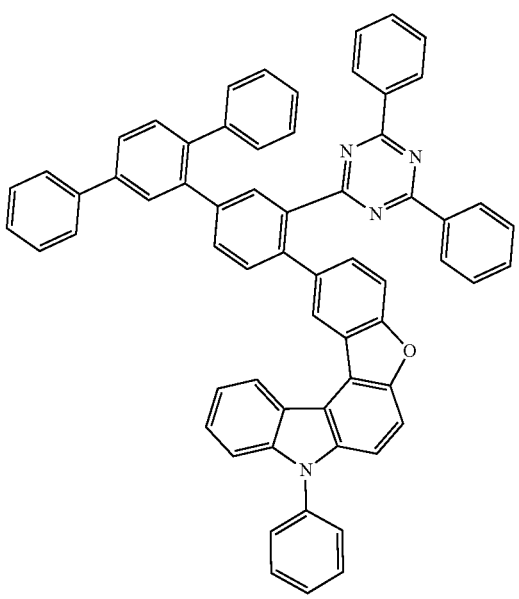

3651
-continued
869
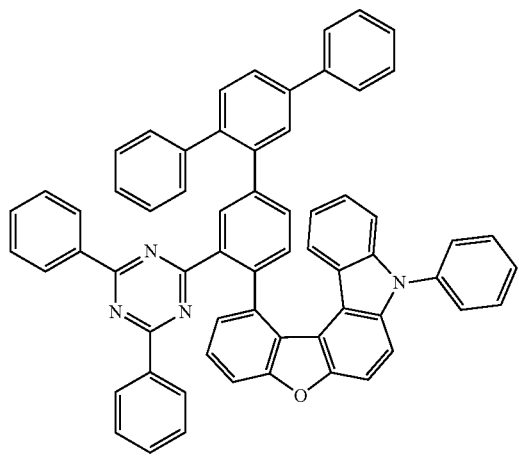
870
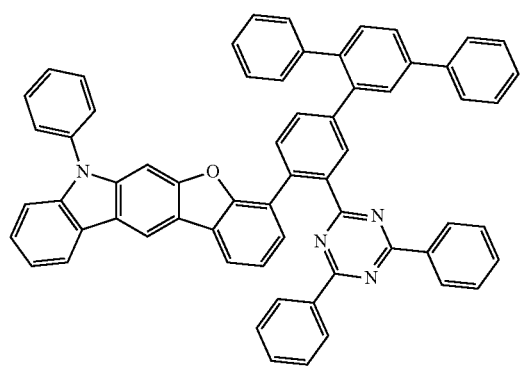
871
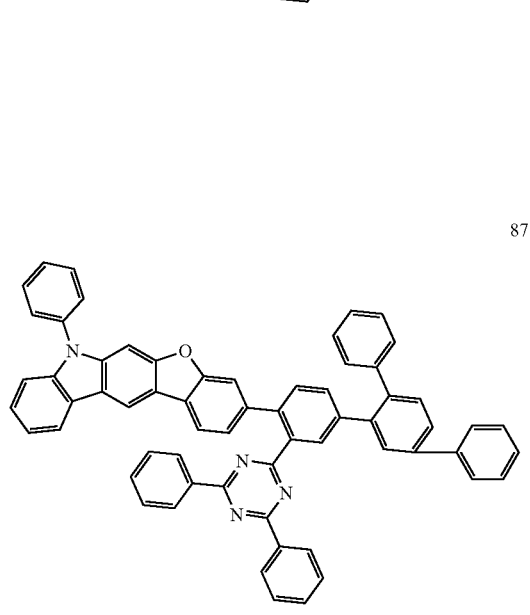
3652
-continued
872
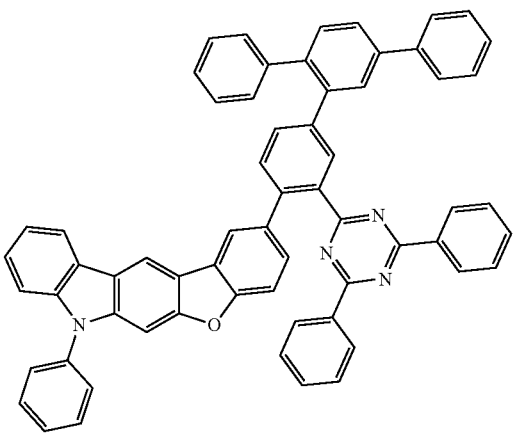
873
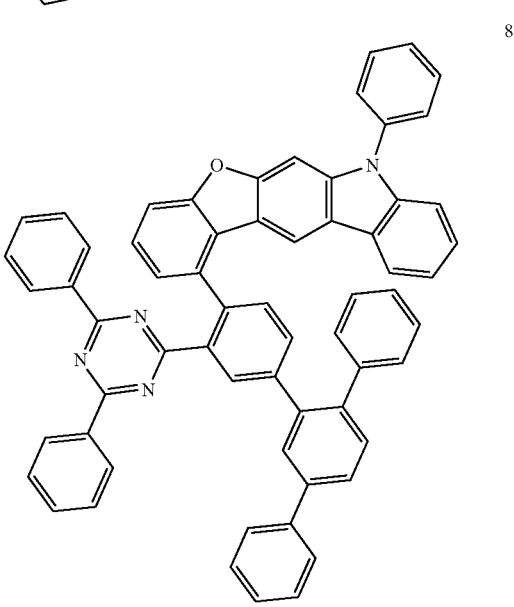
874
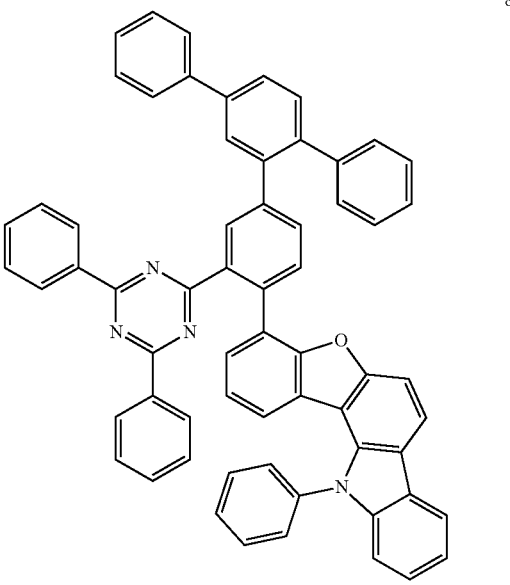

3653
-continued
875
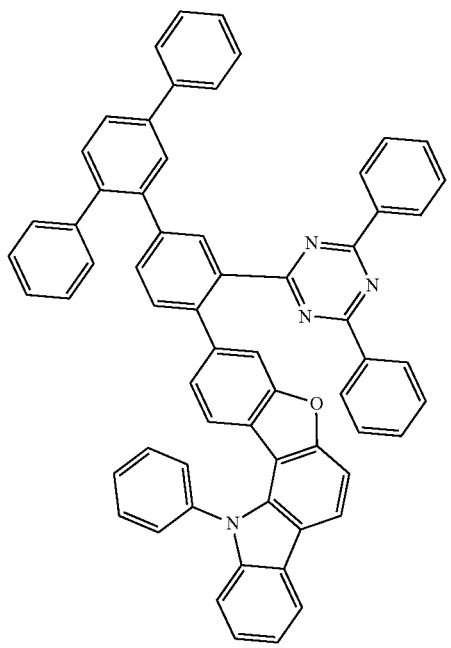
876
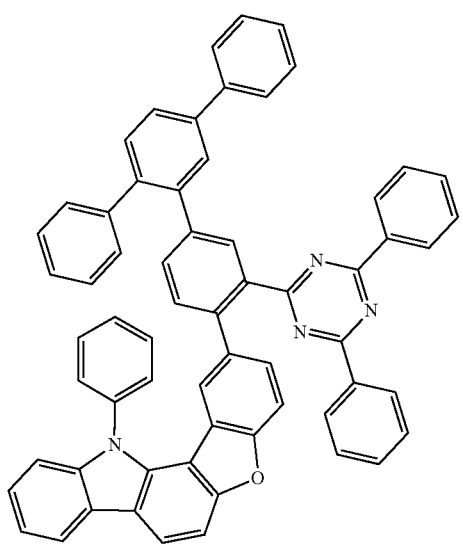
3654
-continued
877
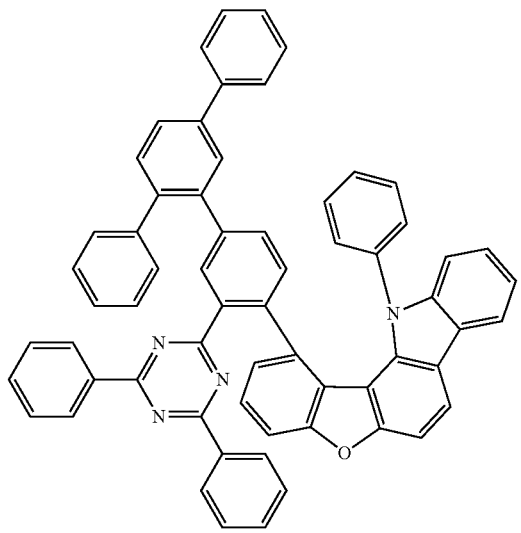
878
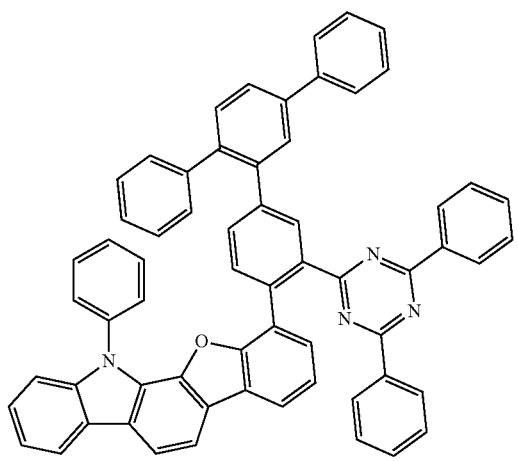

879
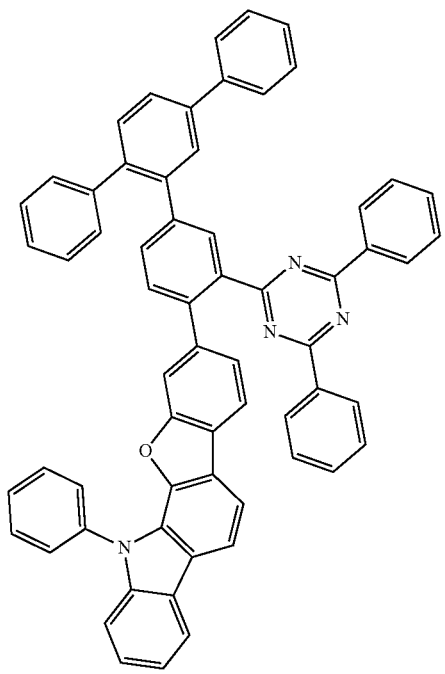
881
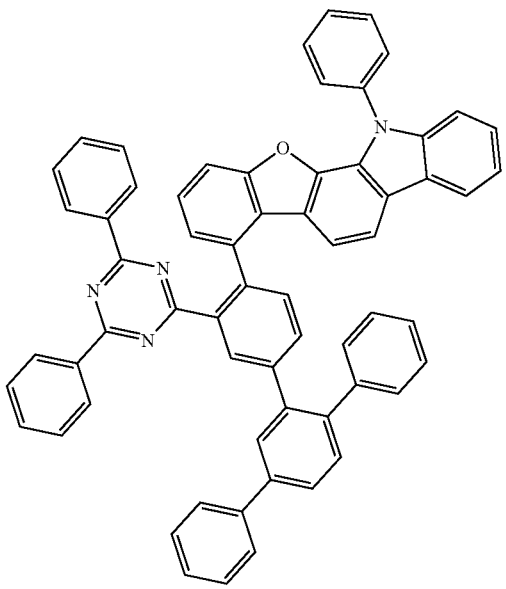
880
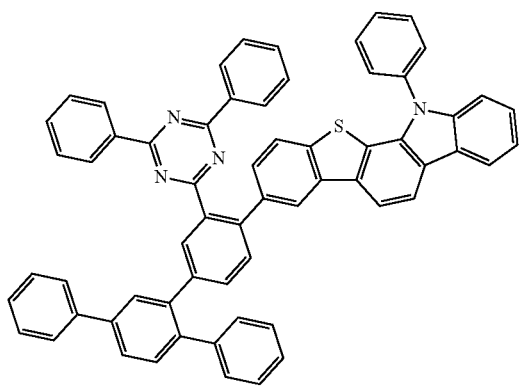
882
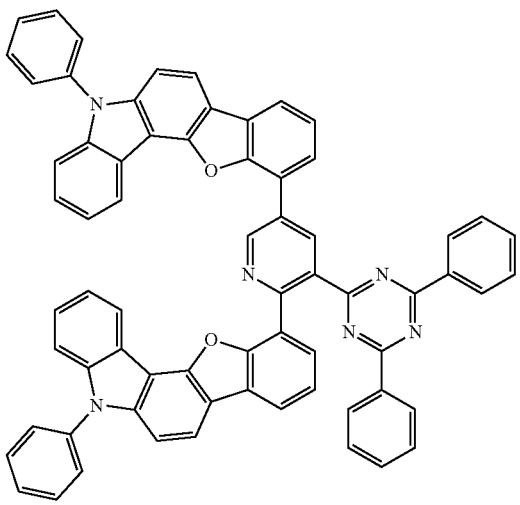

3657
-continued
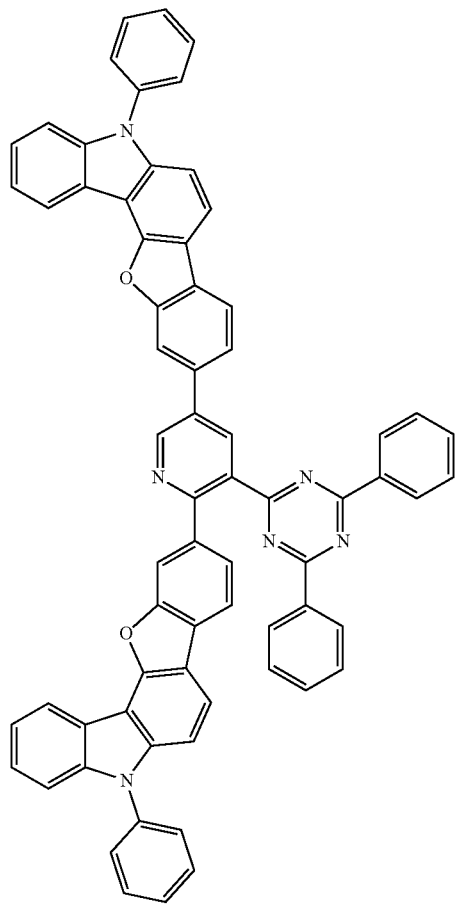
883
3658
-continued
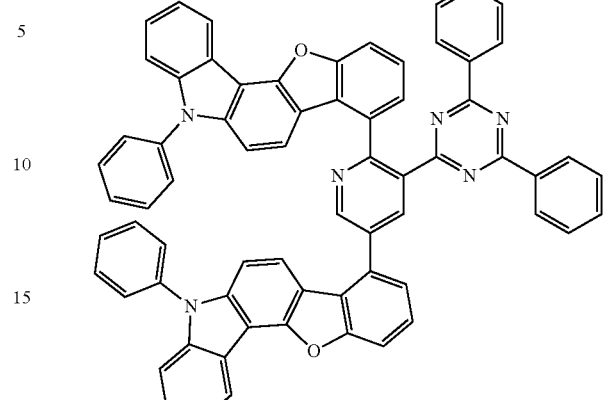
885
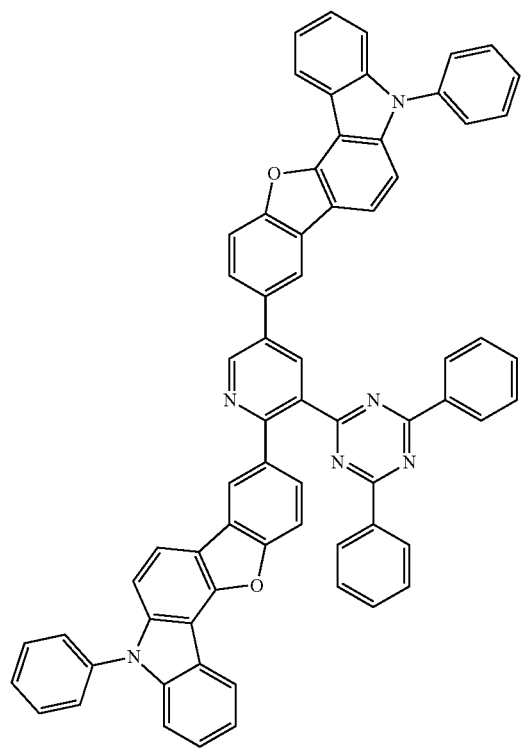
884
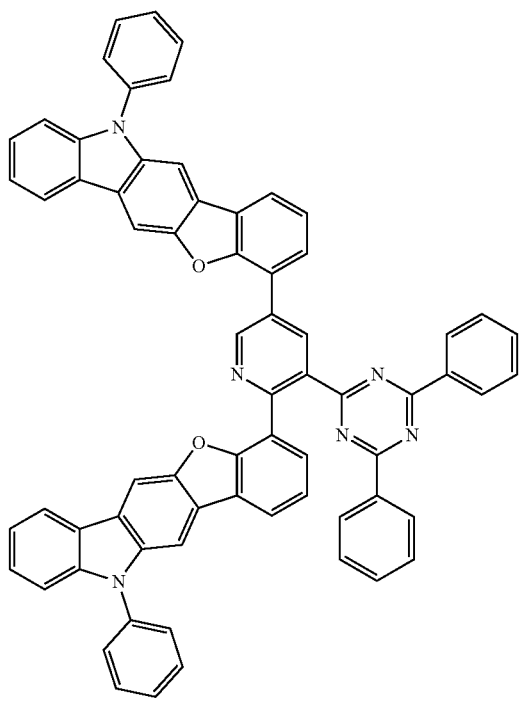
886

3659
-continued
887
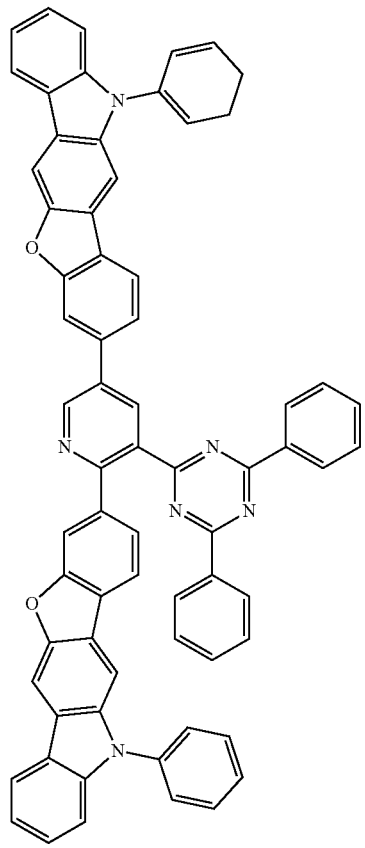
888
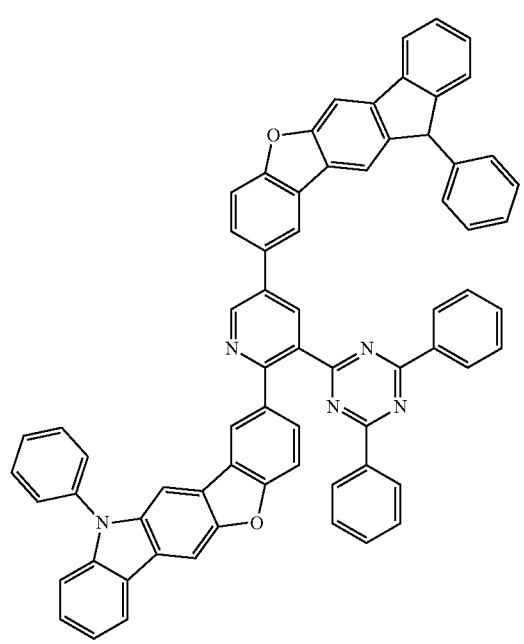
3660
-continued
889
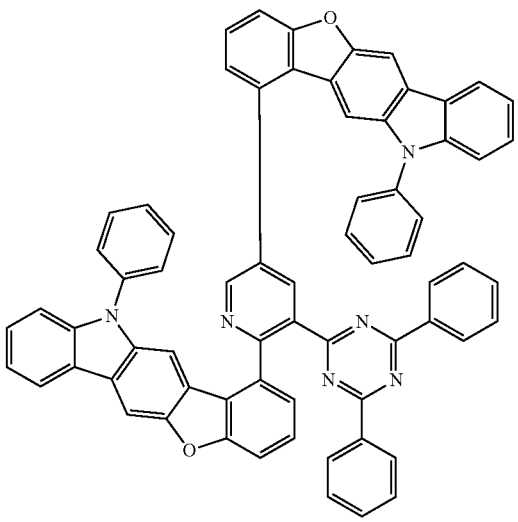
890
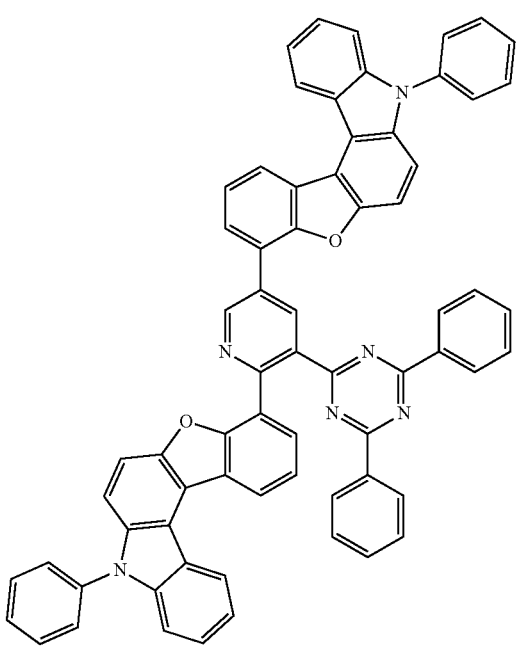

3661
-continued
891
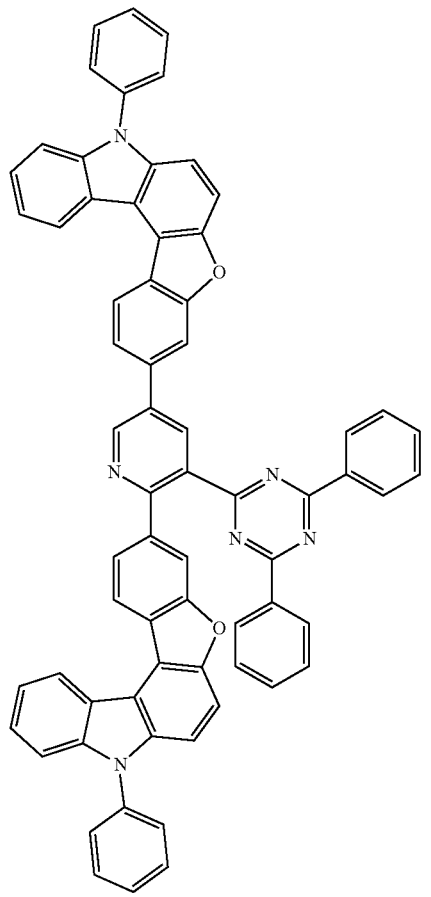
3662
-continued
893
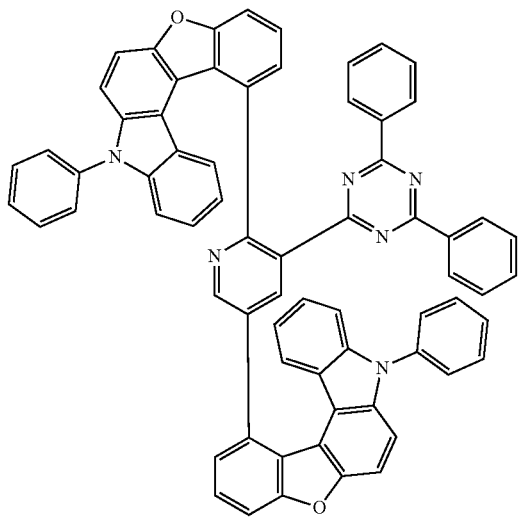
892
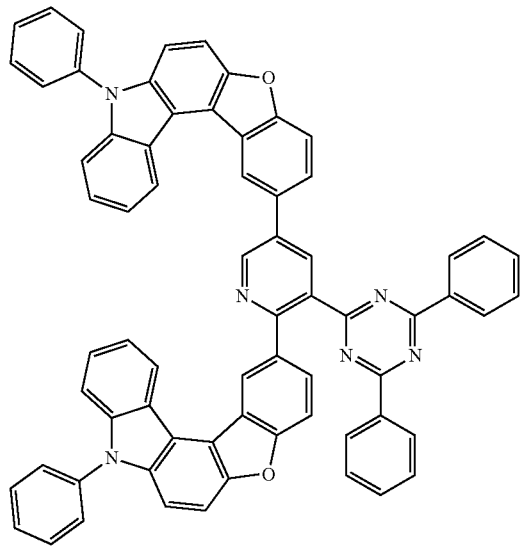
894
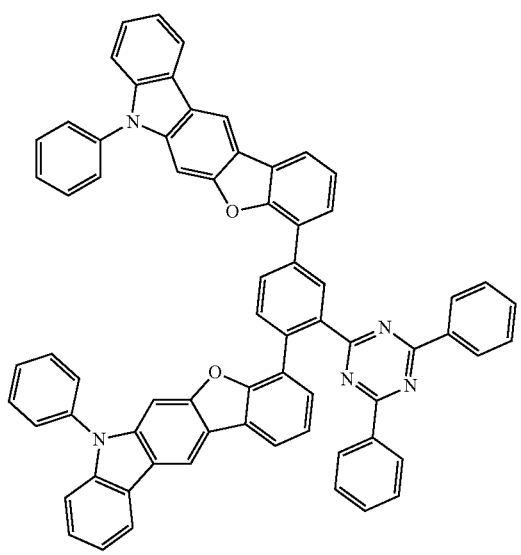

3663
-continued
3664
-continued
895
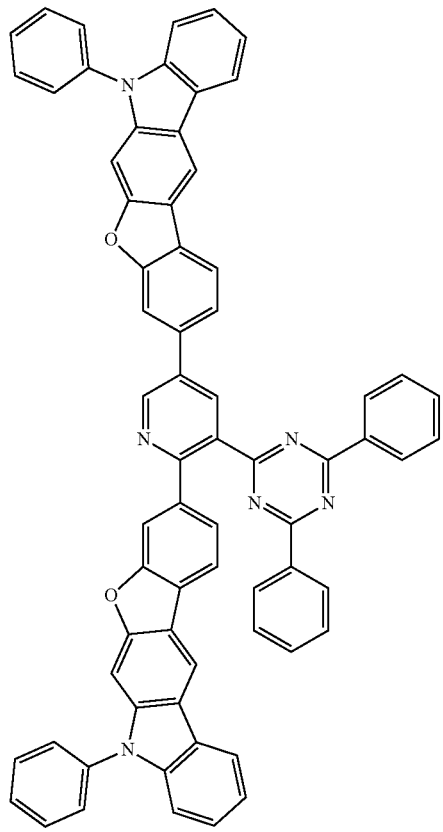
897
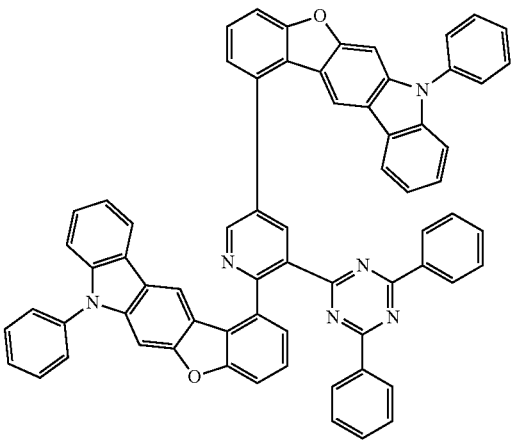
896
898
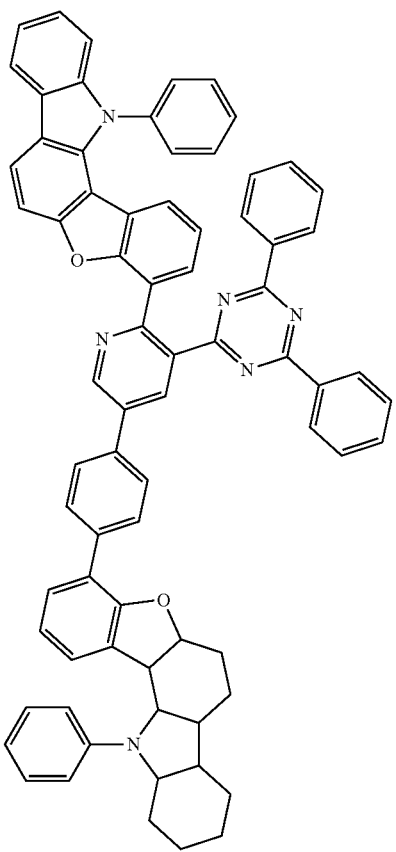

899
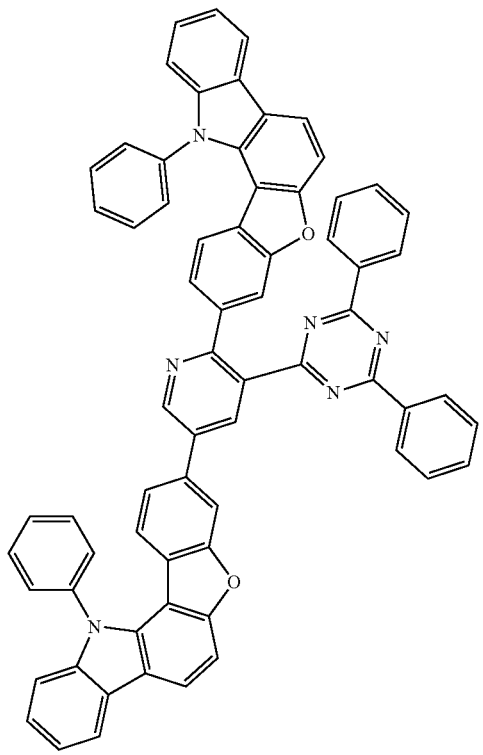
900
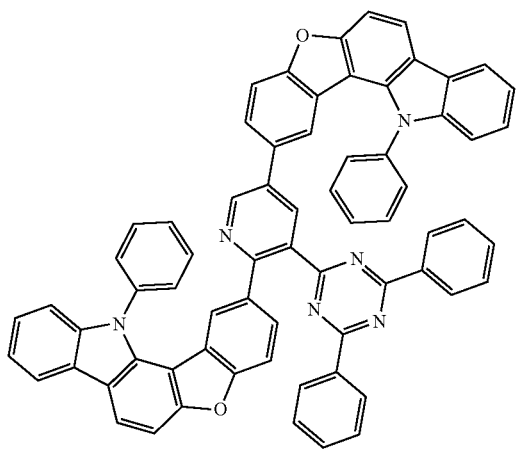
901
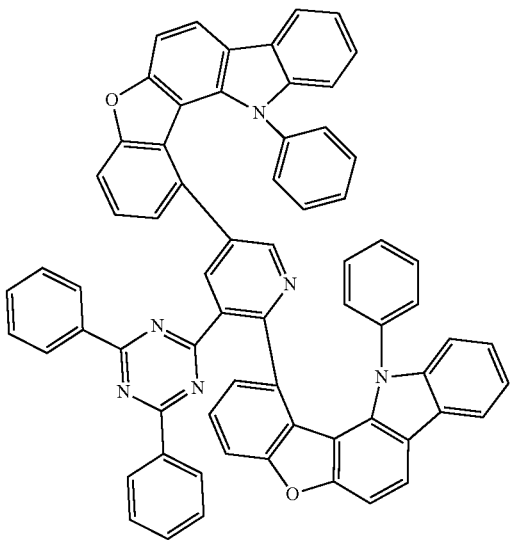
902
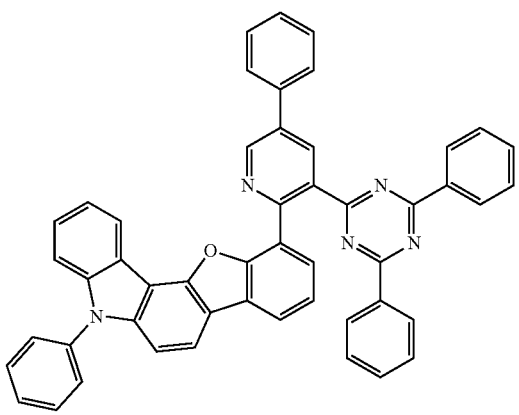
903
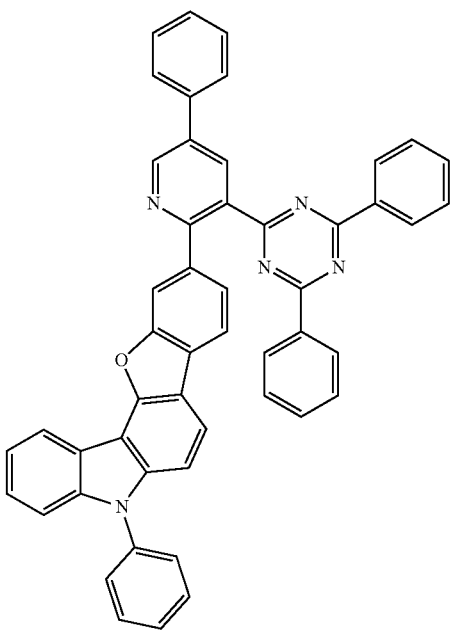

904
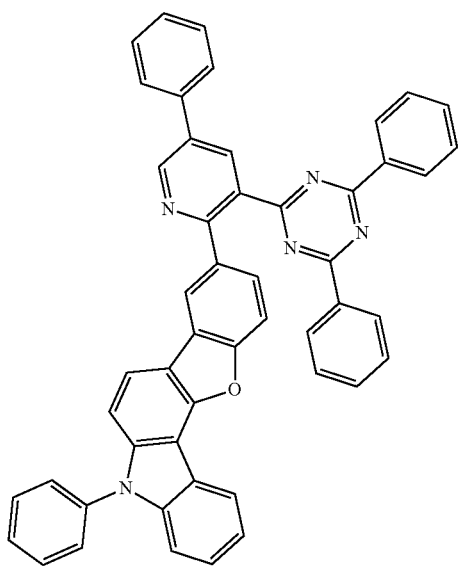
905
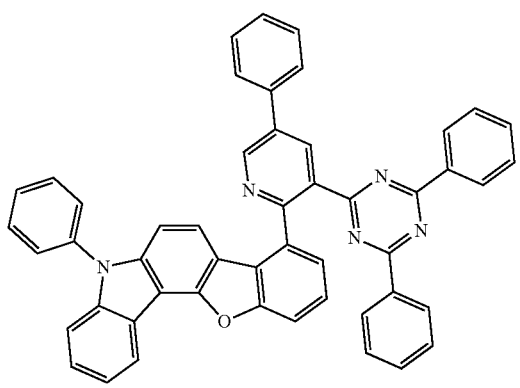
906
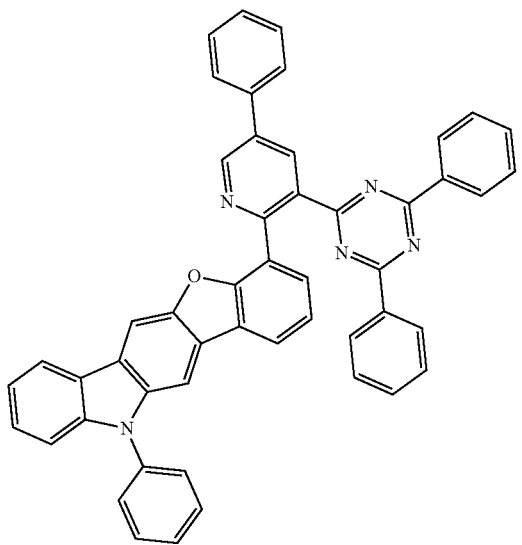
907
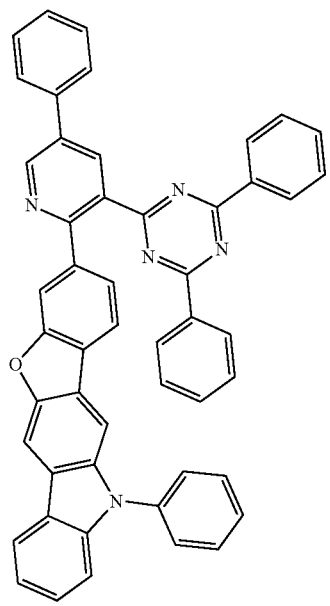
908
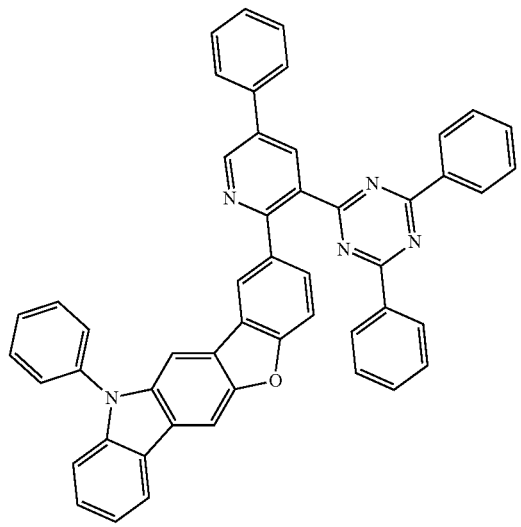
909
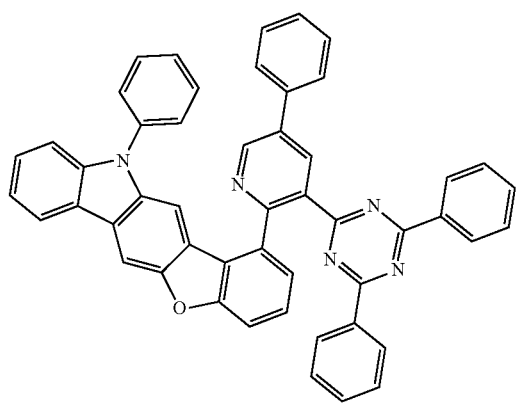

3669
-continued
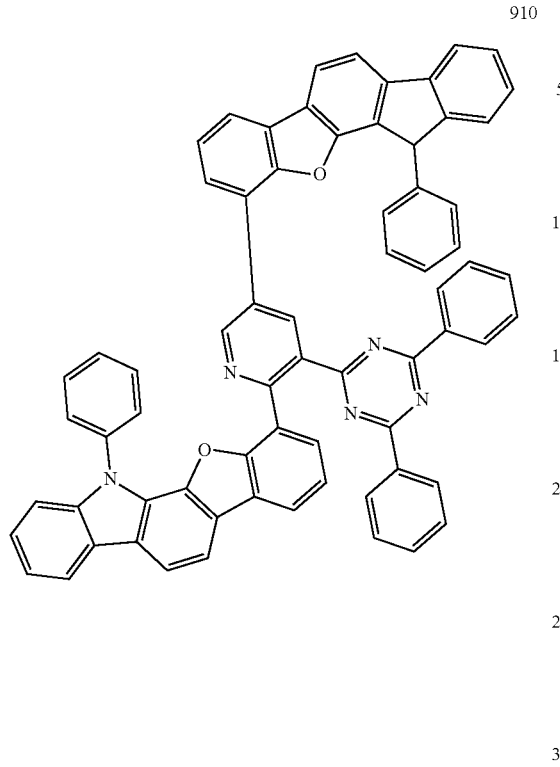
910
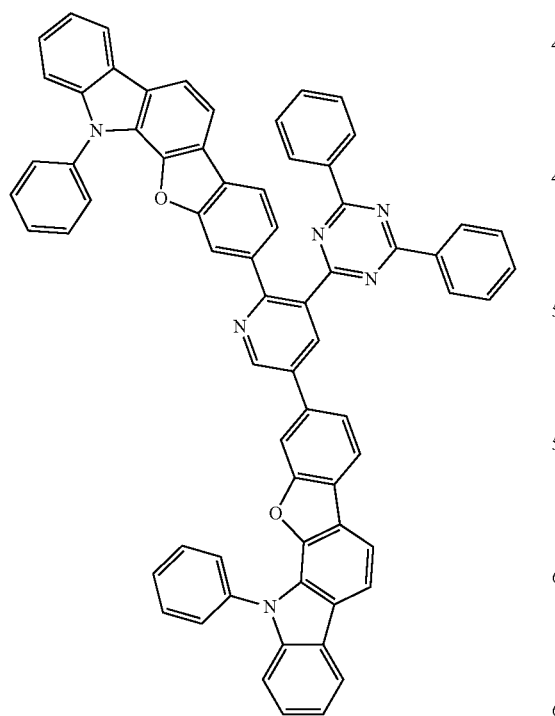
911
3670
-continued
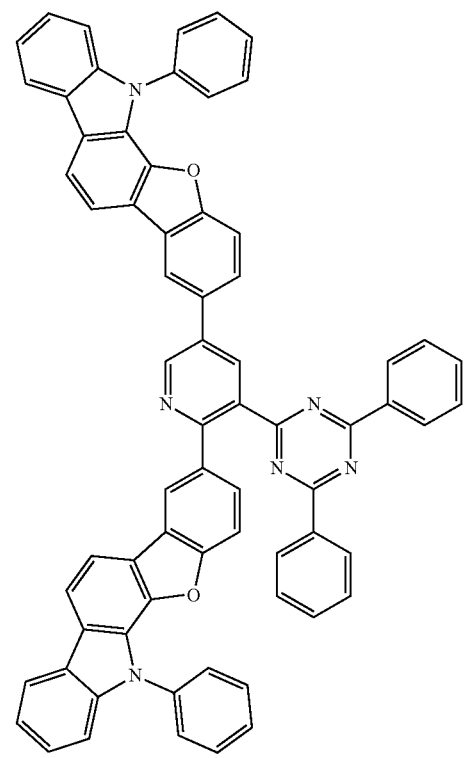
912
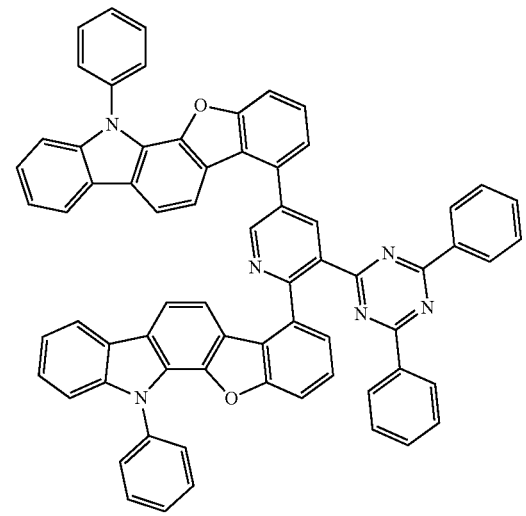
913

3671
-continued
914
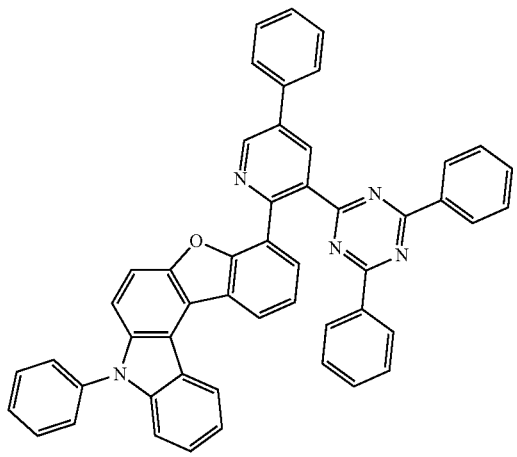
915
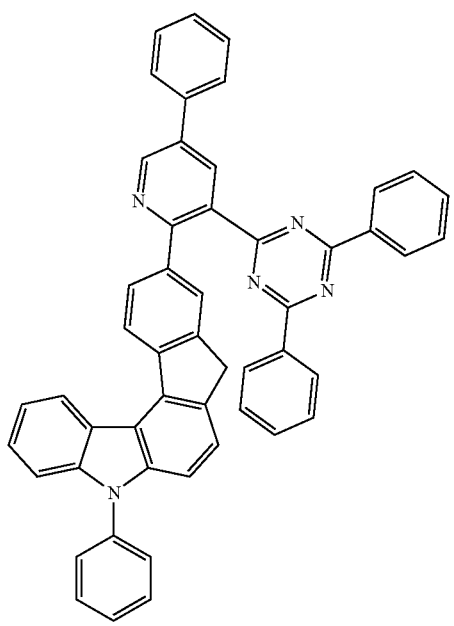
916
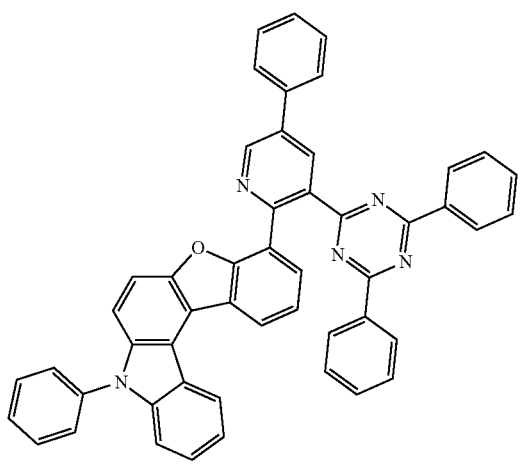
3672
-continued
917
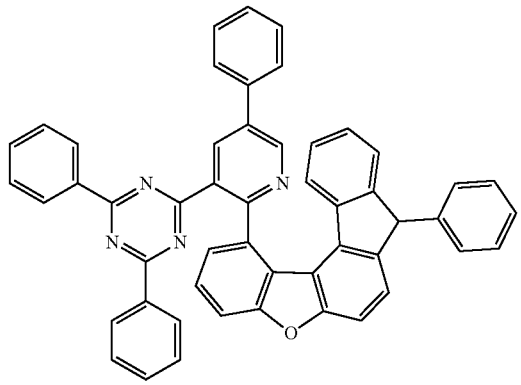
918
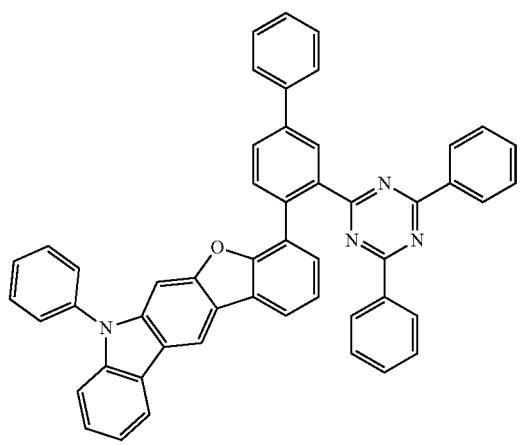
919
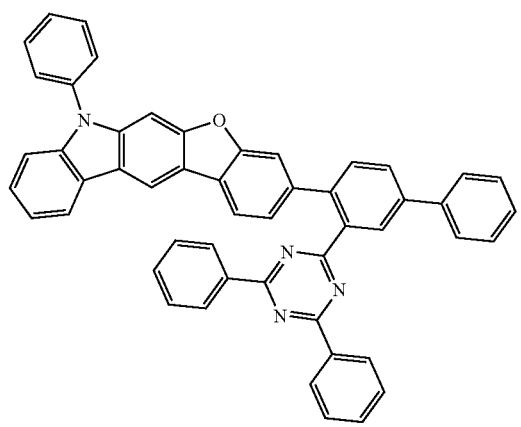

-continued
920
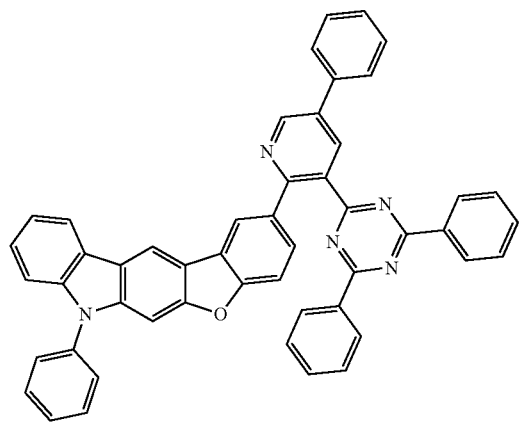
921
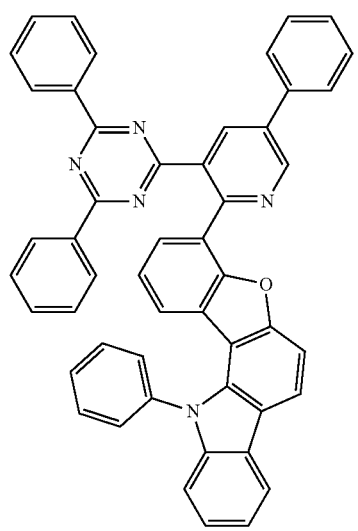
922
-continued
923
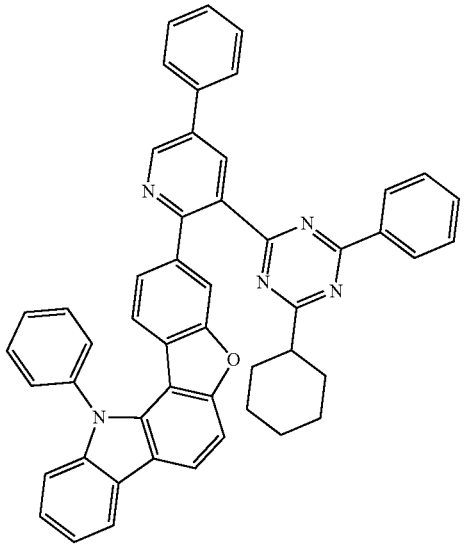
924
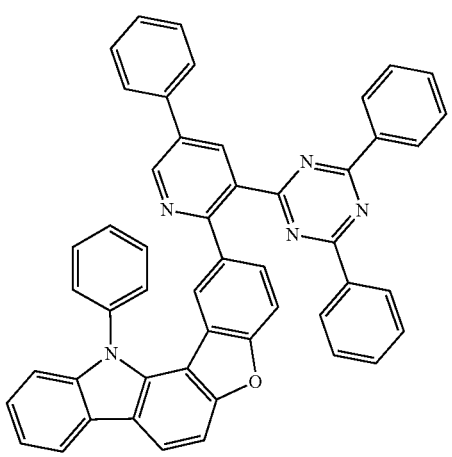
925
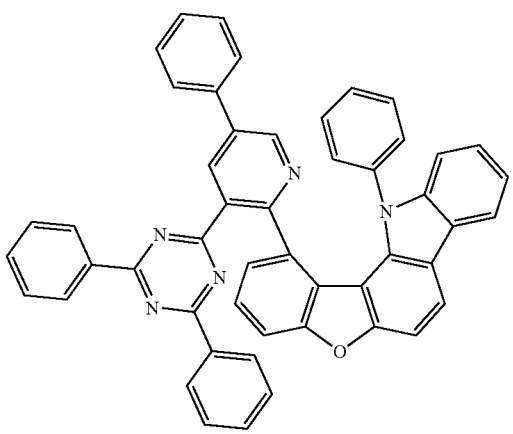

926
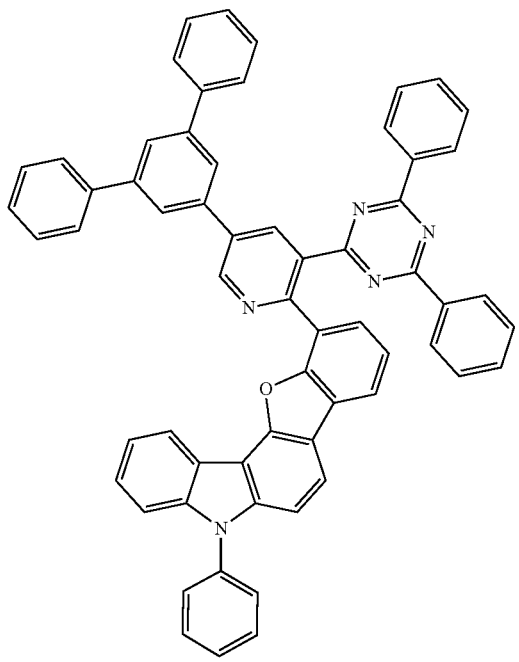
927
928
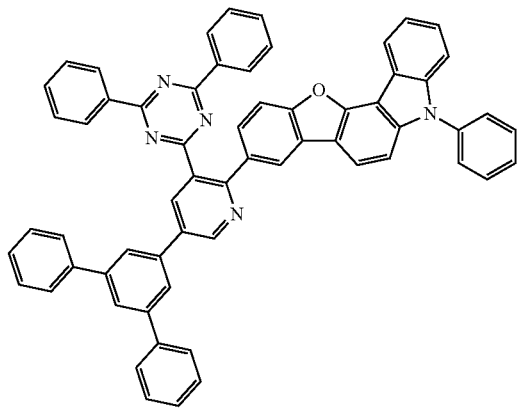
929
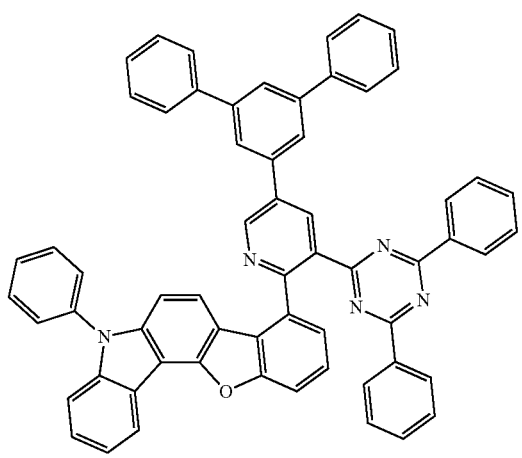
930
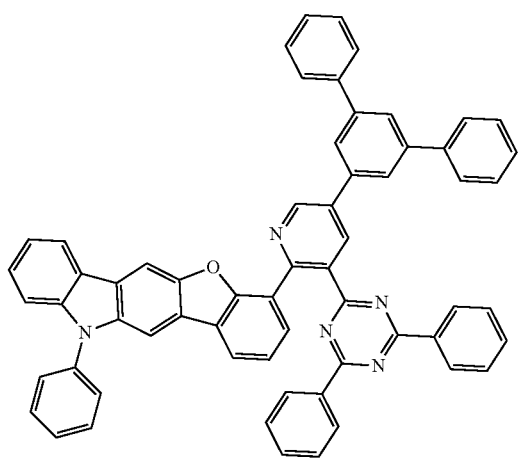

3677
-continued
931
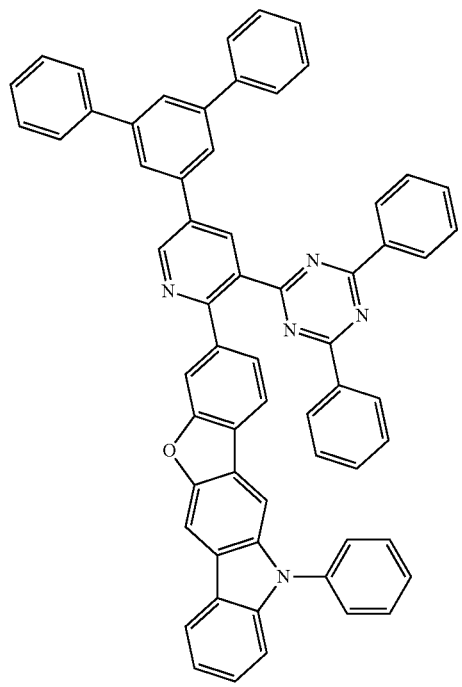
932
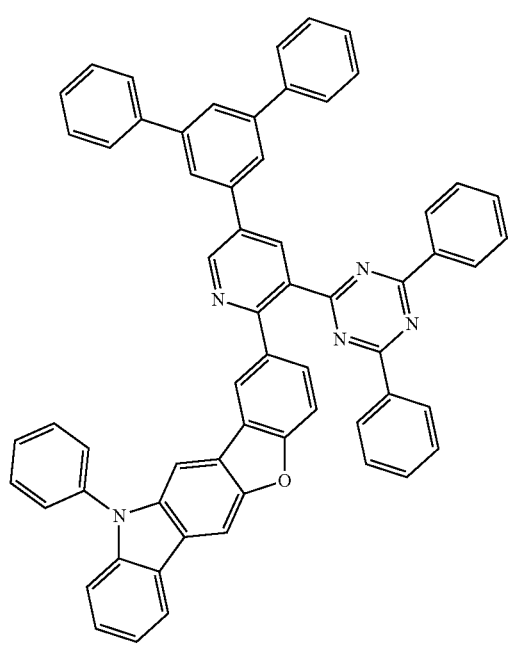
3678
-continued
933
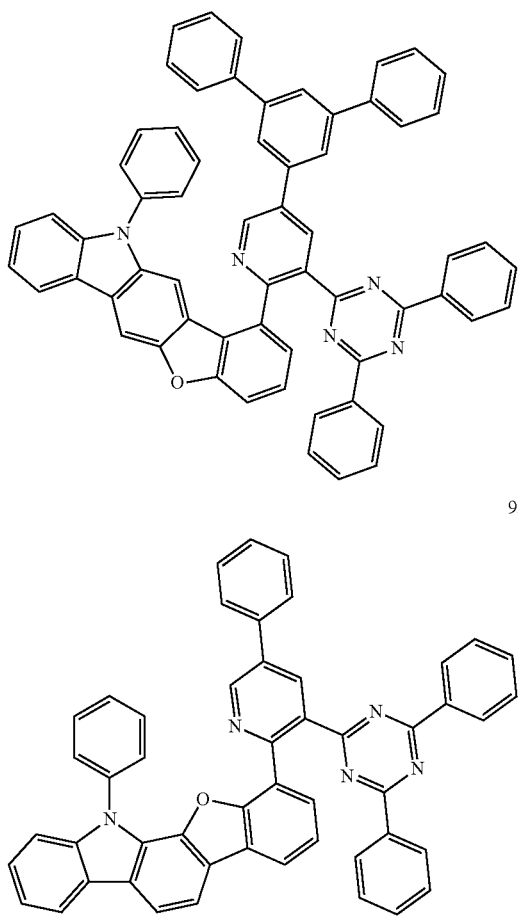
934
935
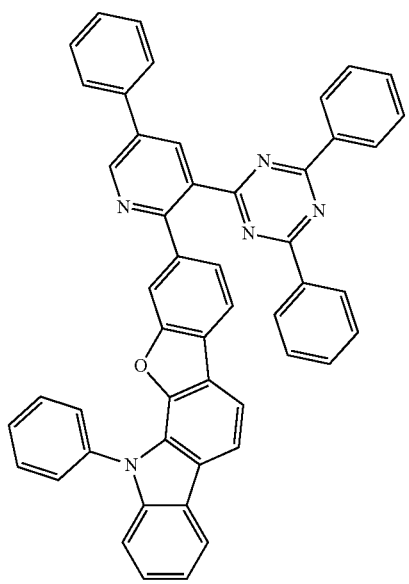

3679
-continued
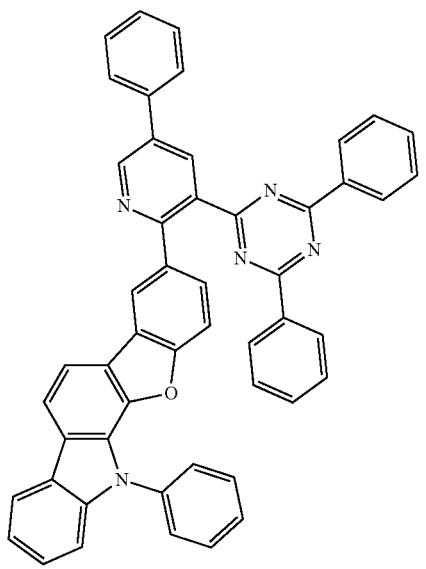
936
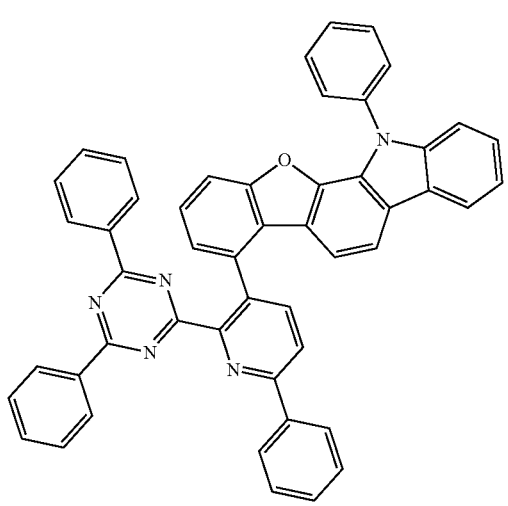
937
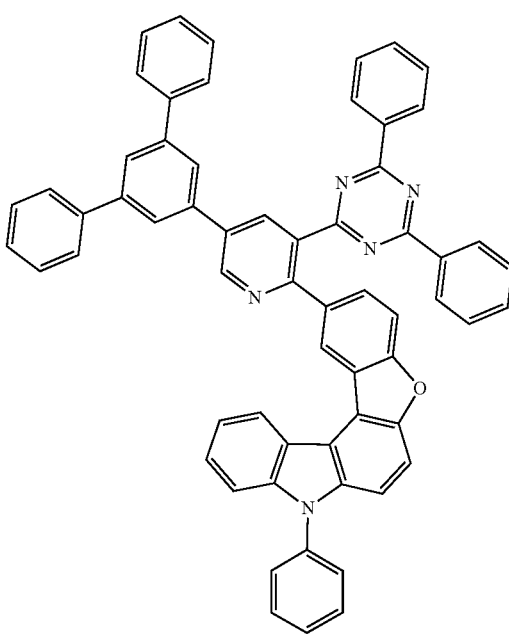
938
3680
-continued
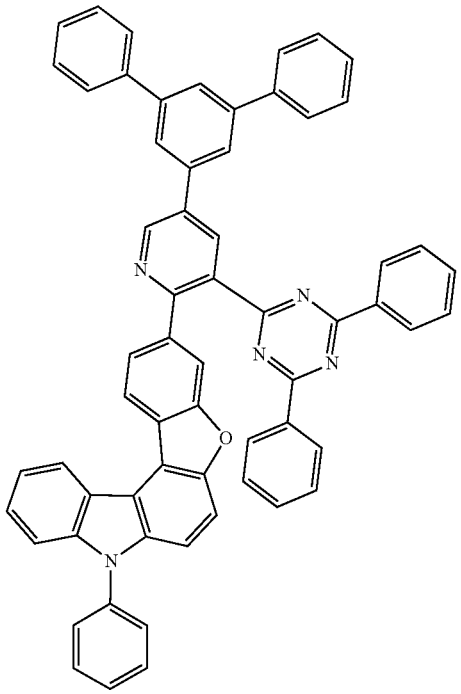
939
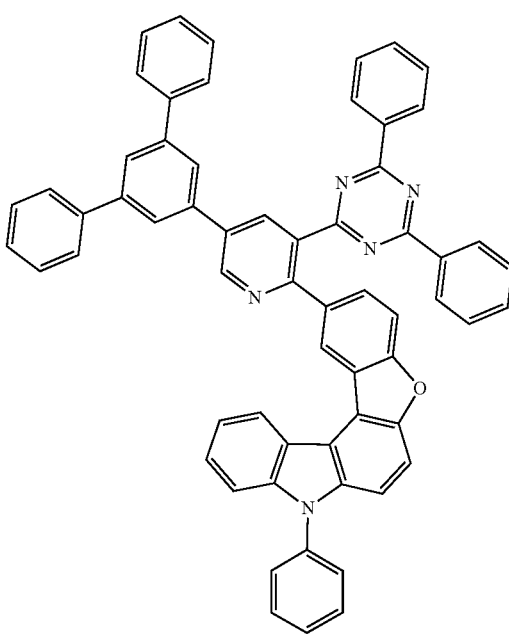
940

3681
-continued
941
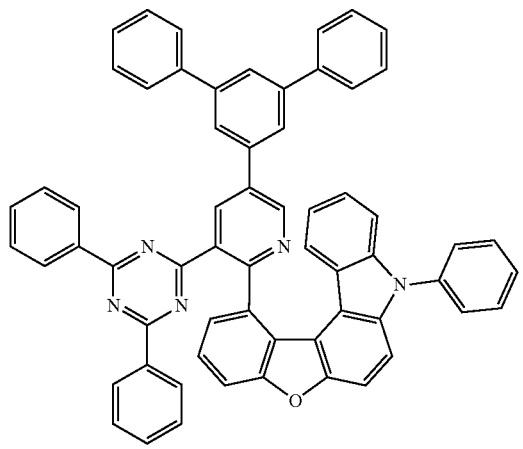
942
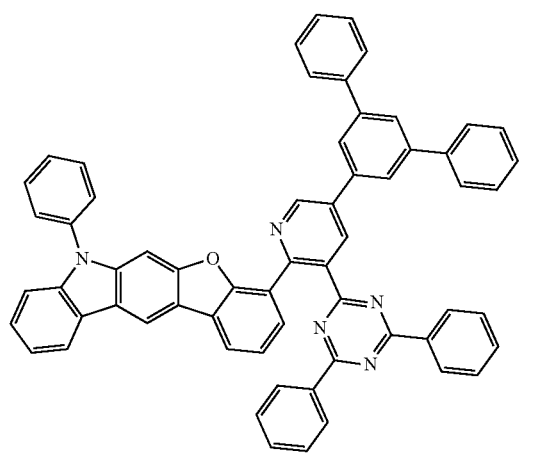
943
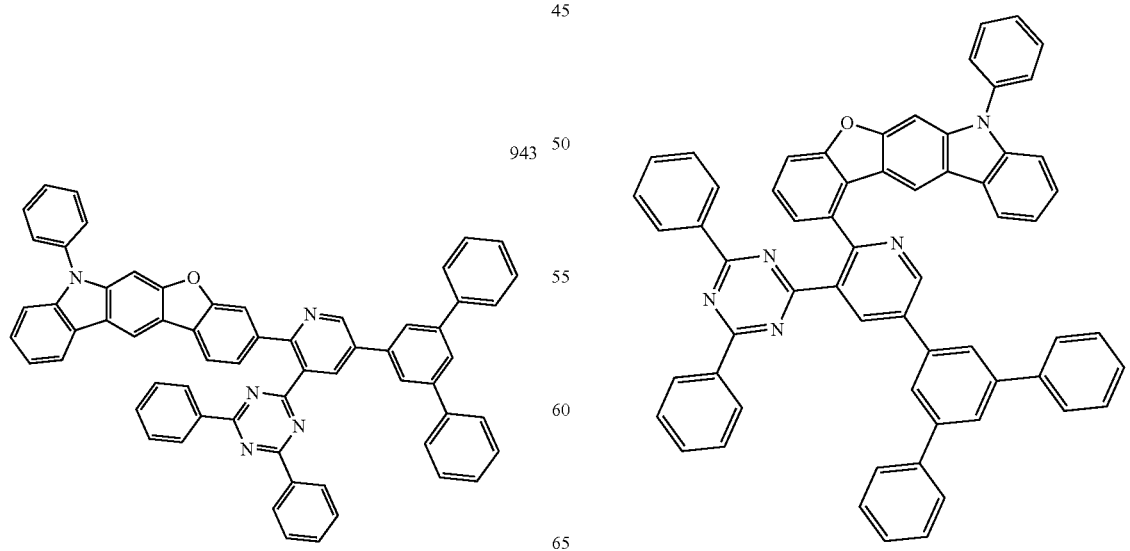
3682
-continued
944
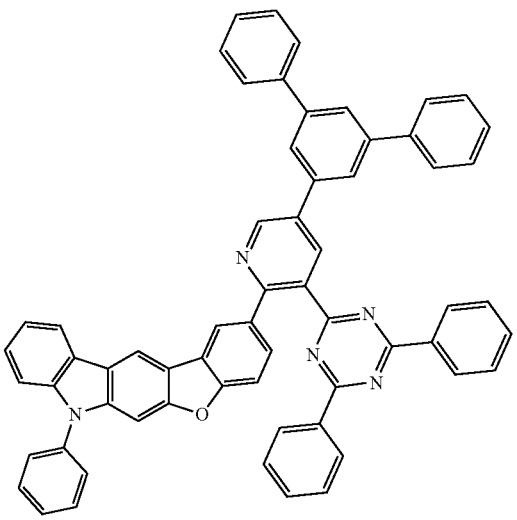
945
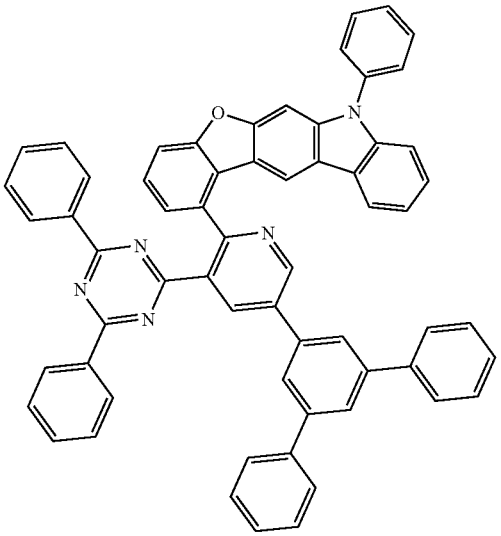

3683
-continued
946
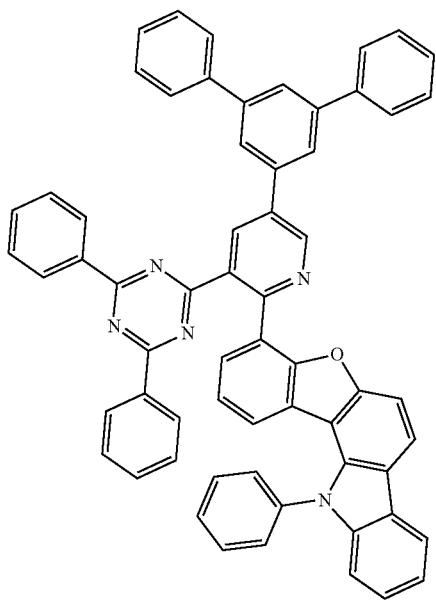
947
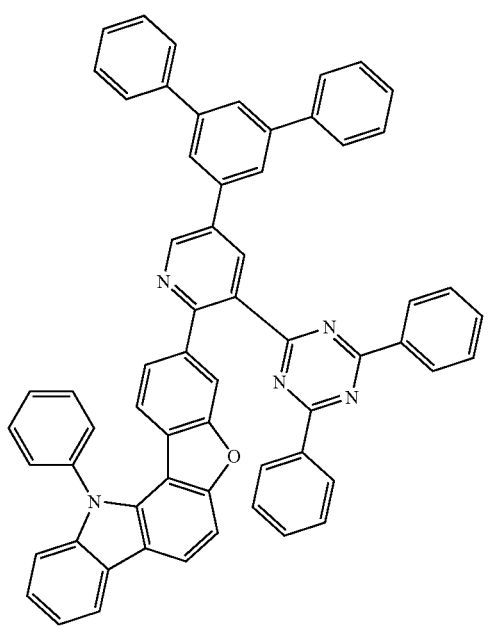
3684
-continued
948
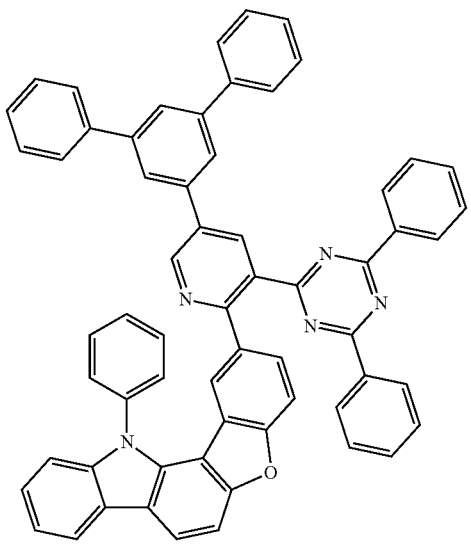
949
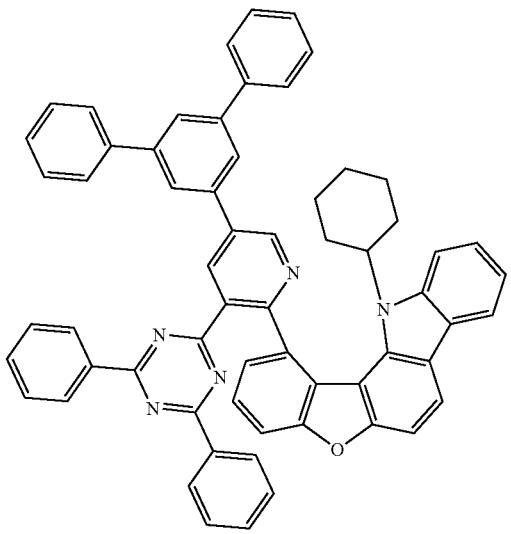

3685
-continued
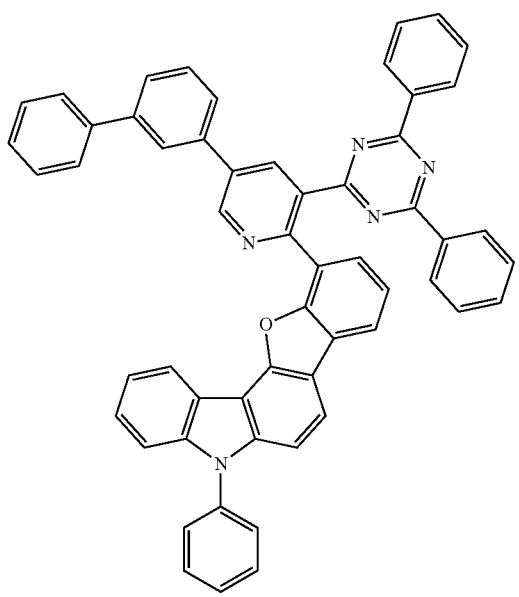
950
3686
-continued
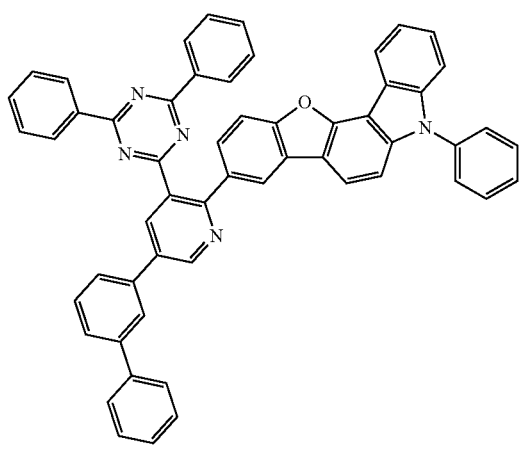
952
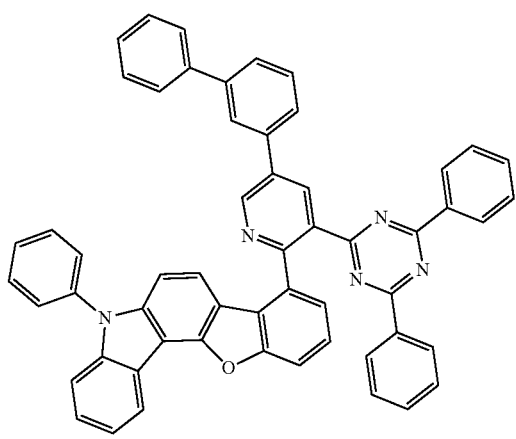
953
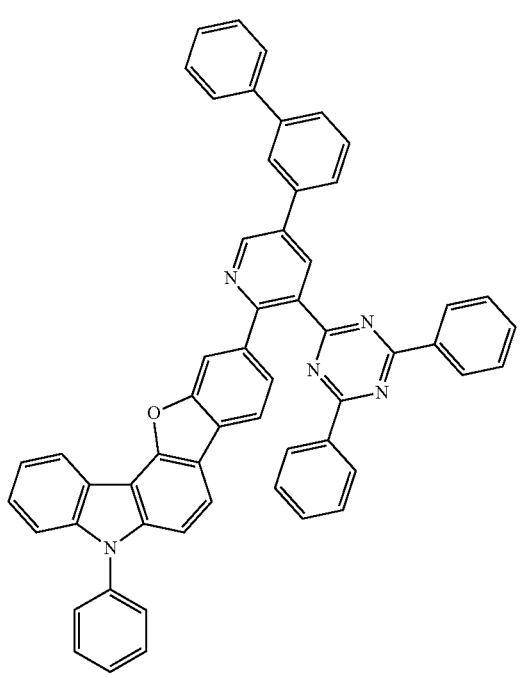
951
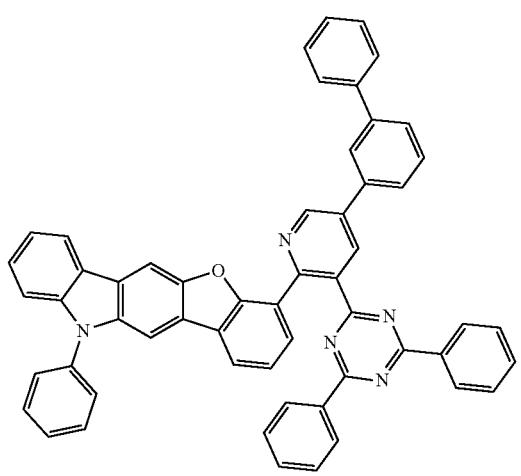
954

3687
-continued
955
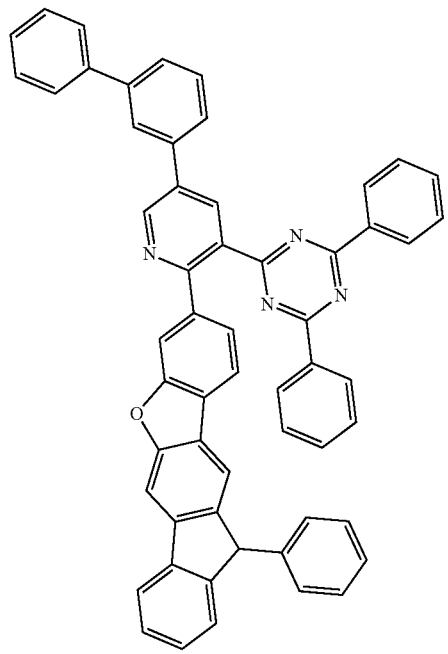
956
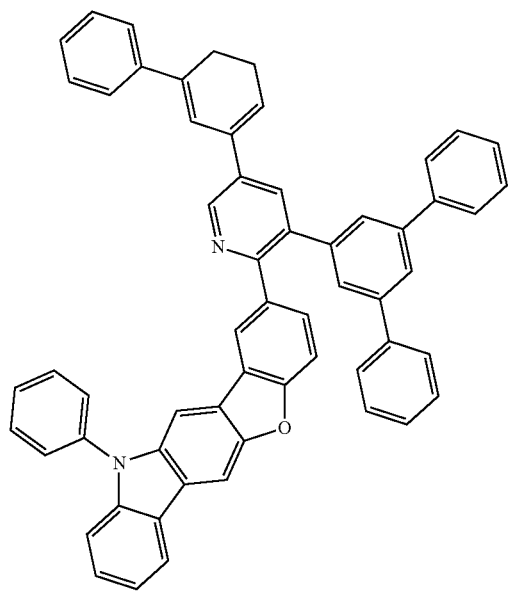
3688
-continued
957
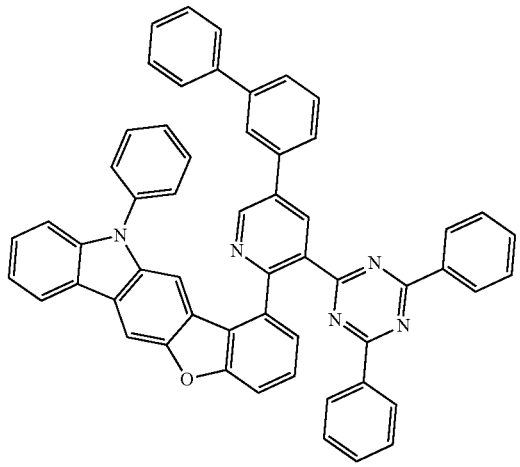
958
959
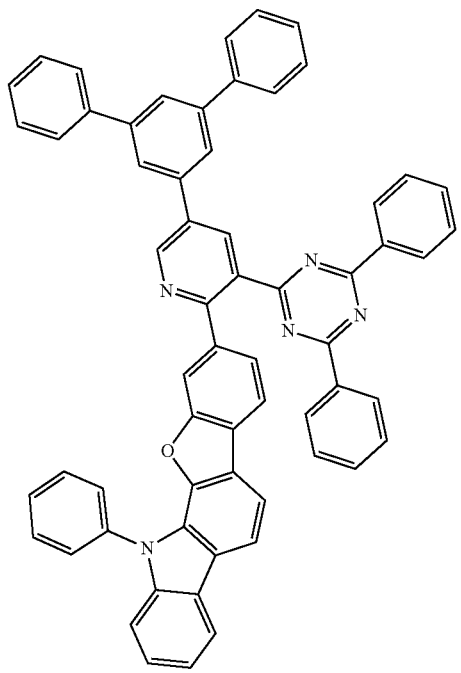

3689
-continued
960
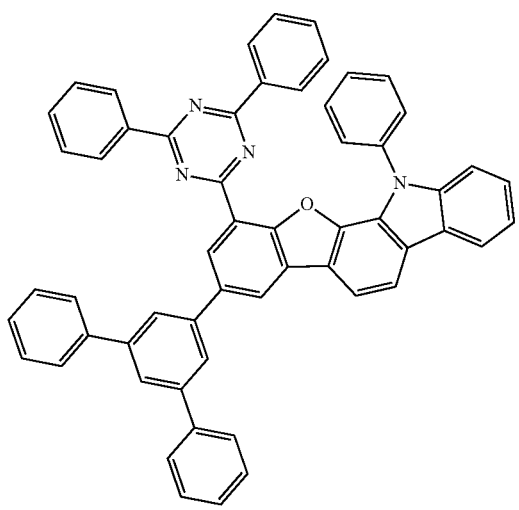
961
3690
-continued
963
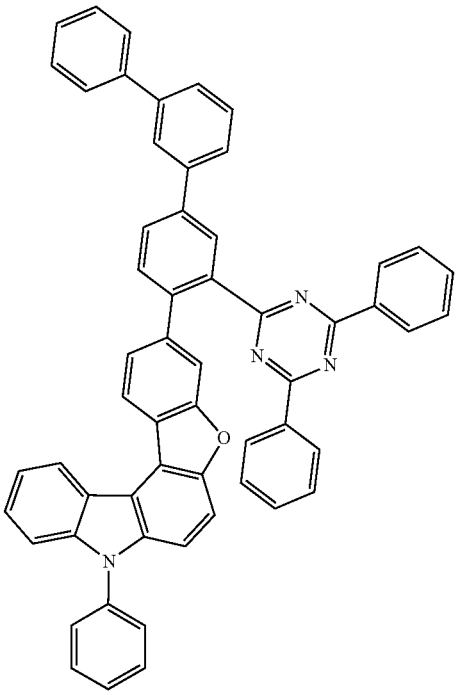
964
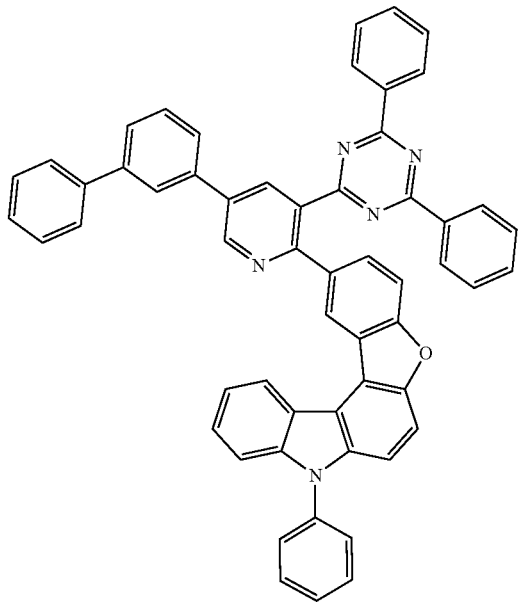
962

3691
-continued
965
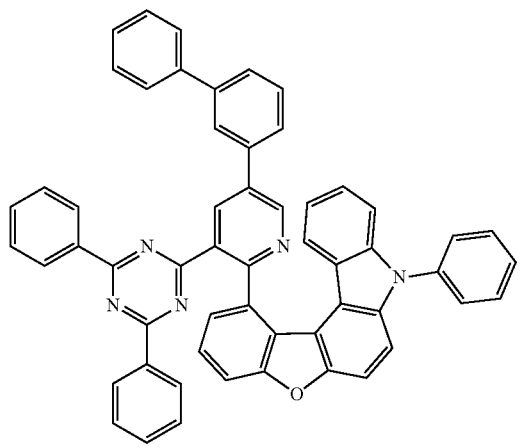
966
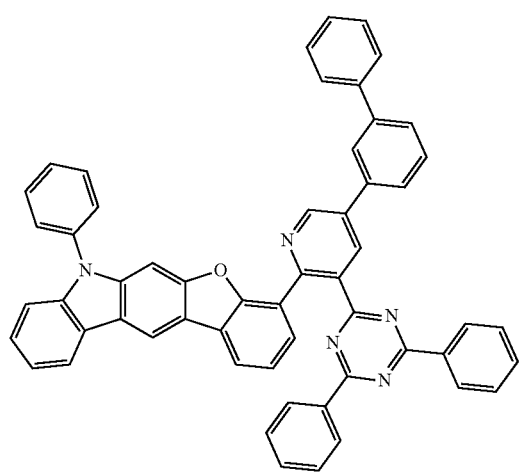
967
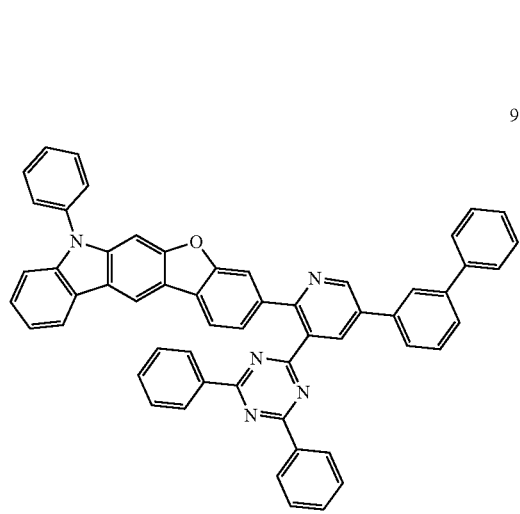
3692
-continued
968
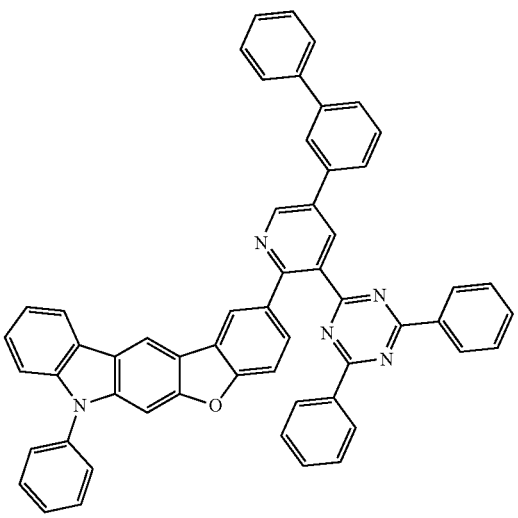
969
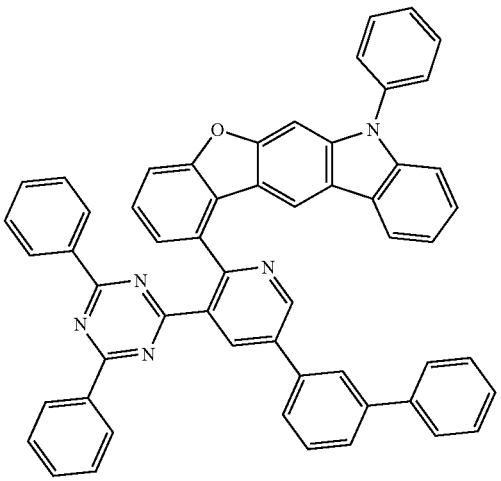

3693
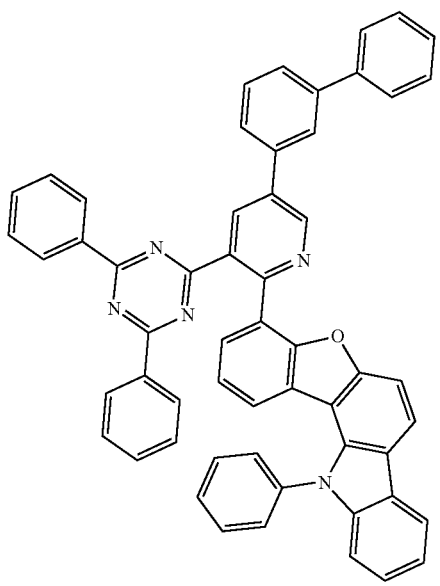
970
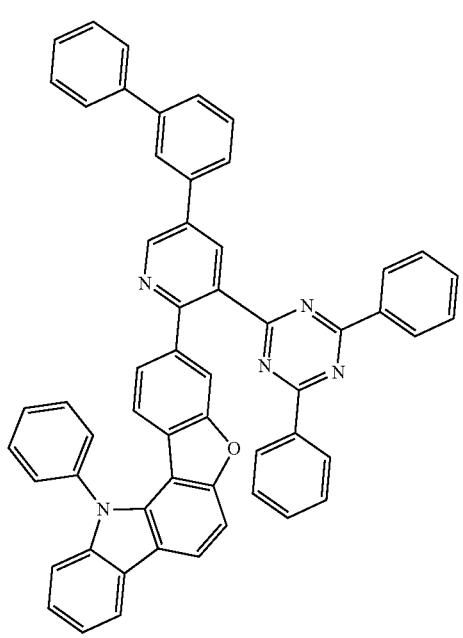
971
-continued
3694
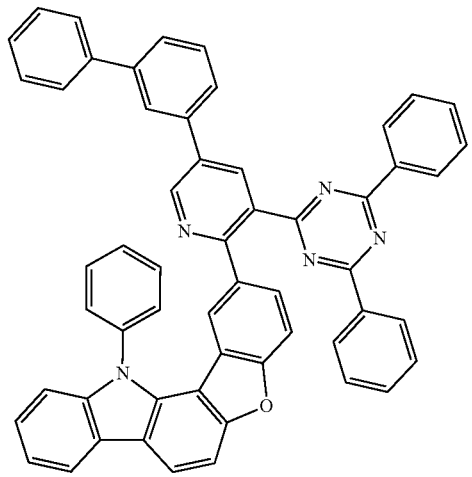
972
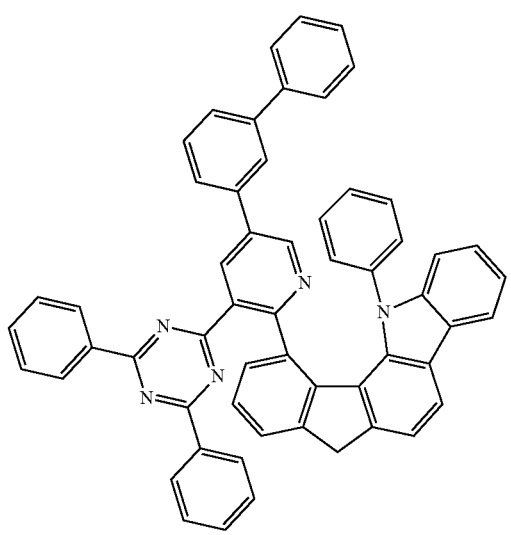
973
974

3695
-continued
3696
-continued
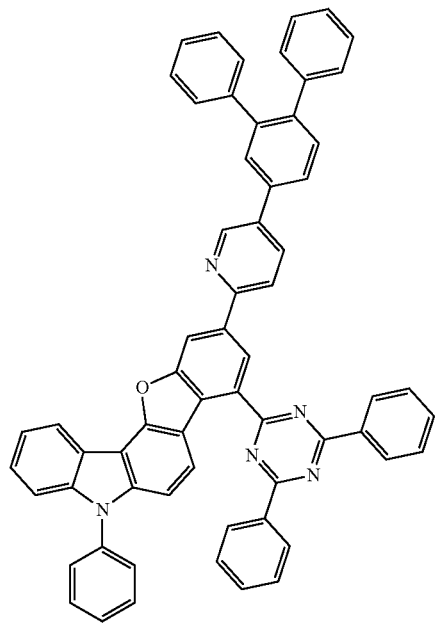
975
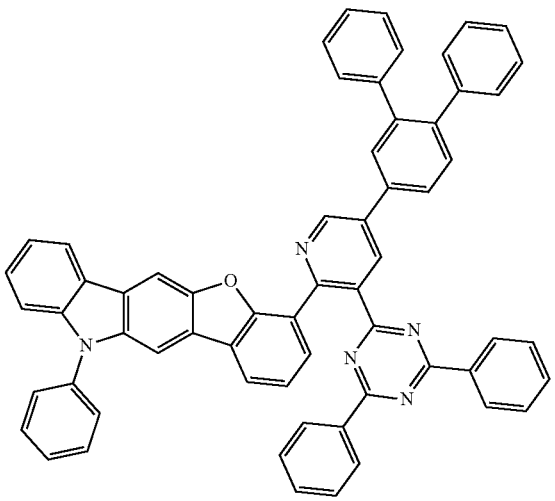
978
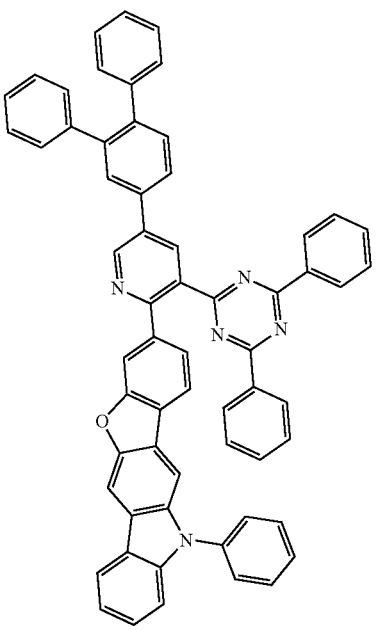
977
976
979

3697
-continued
980
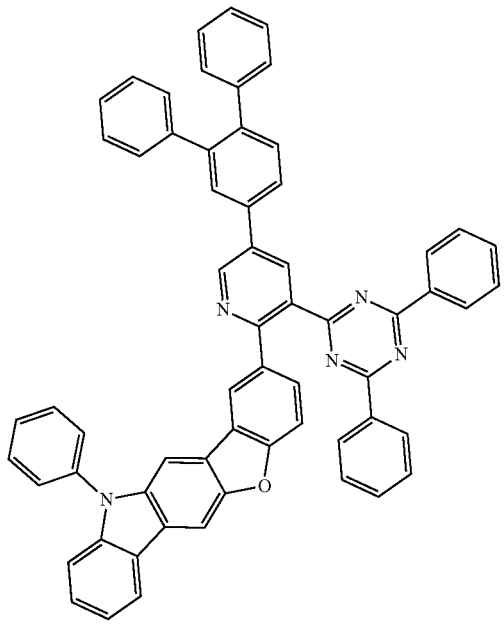
981
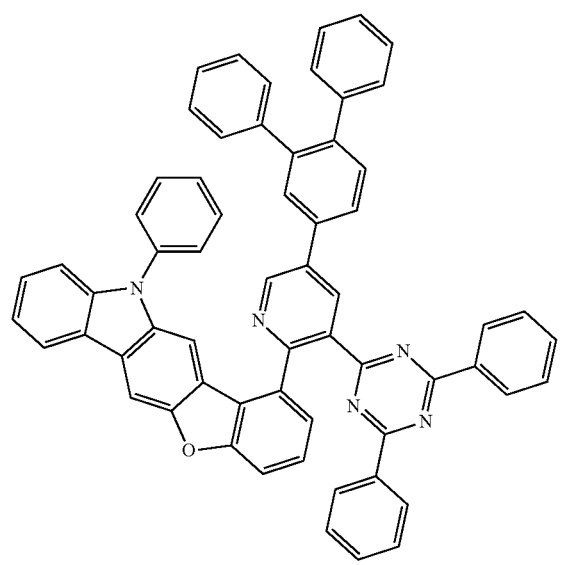
3698
-continued
982
983
984
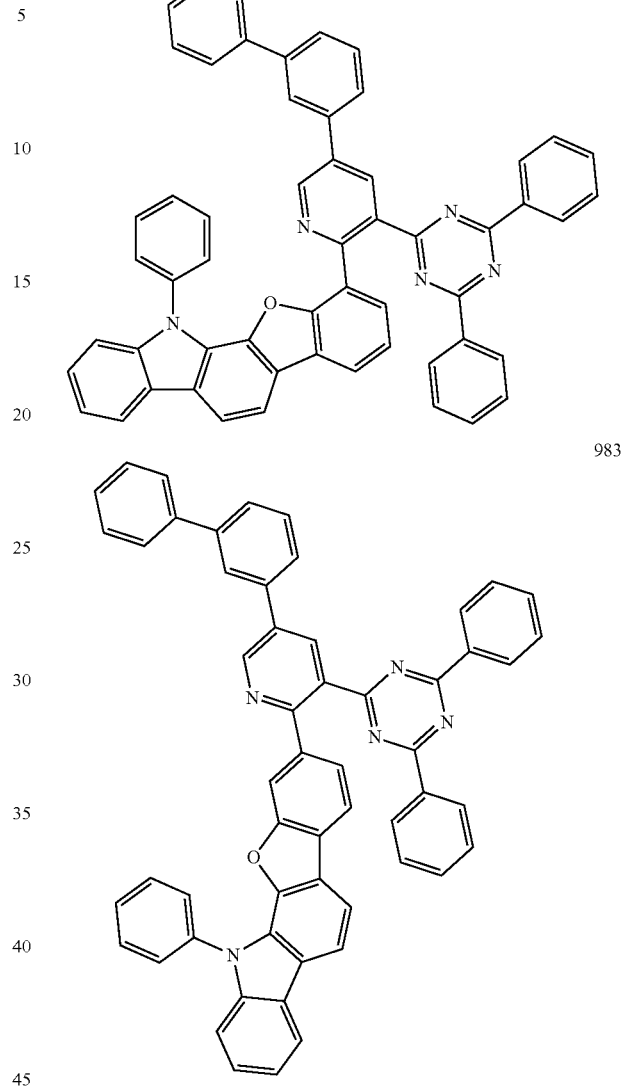
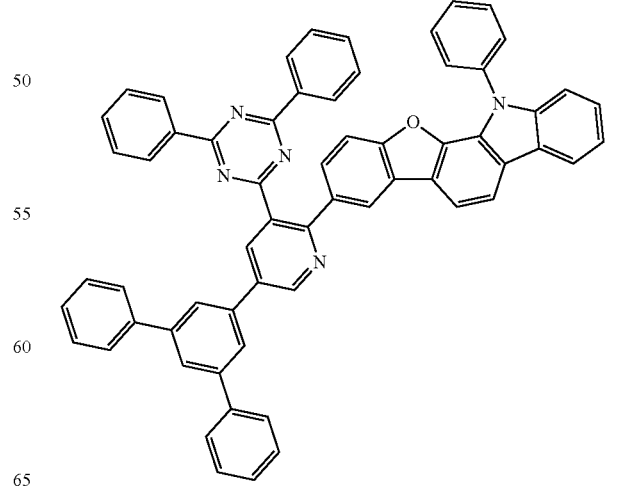

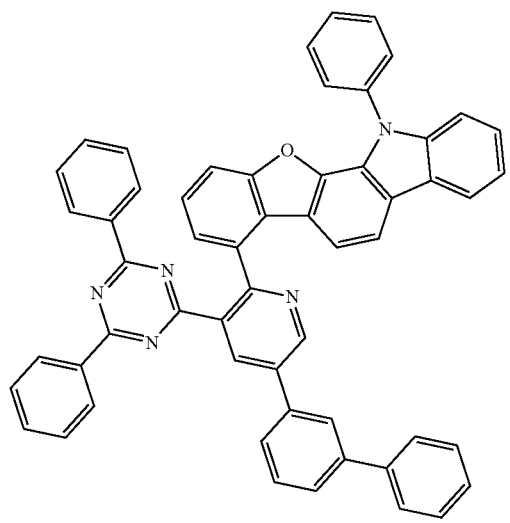
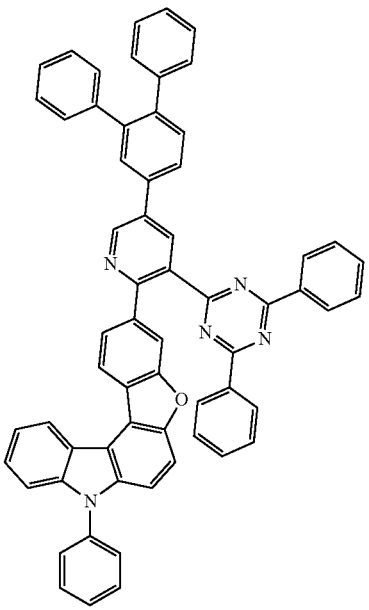
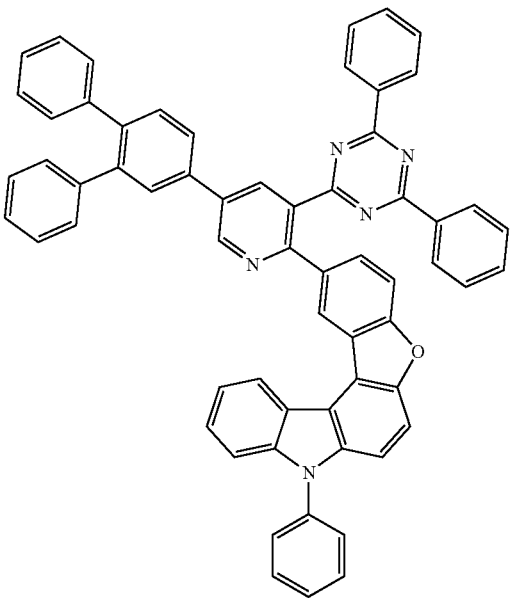

3701
-continued
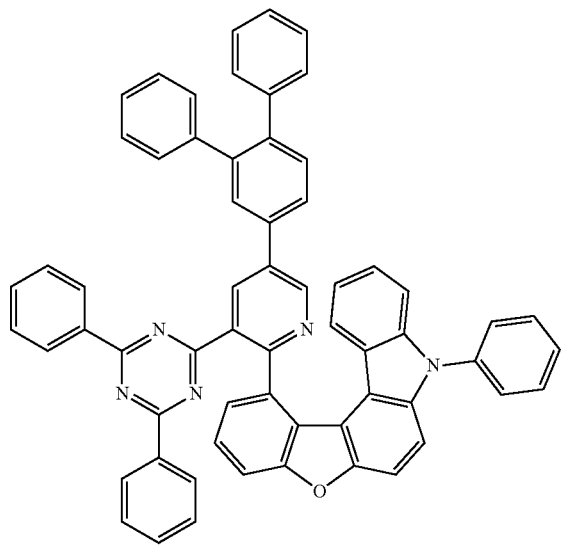
989
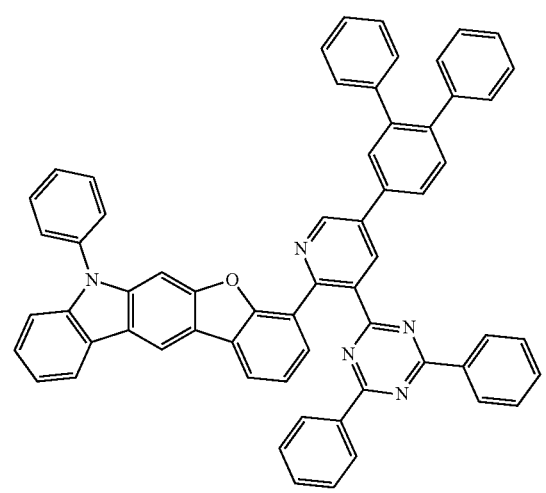
990
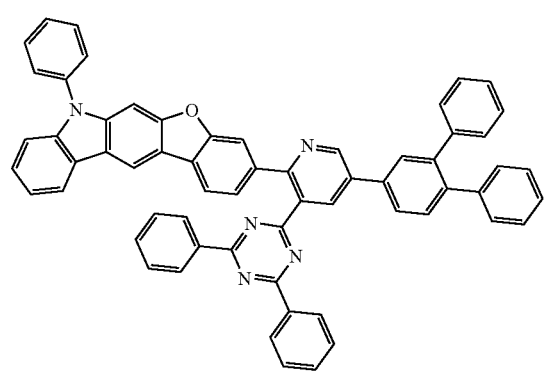
991
3702
-continued
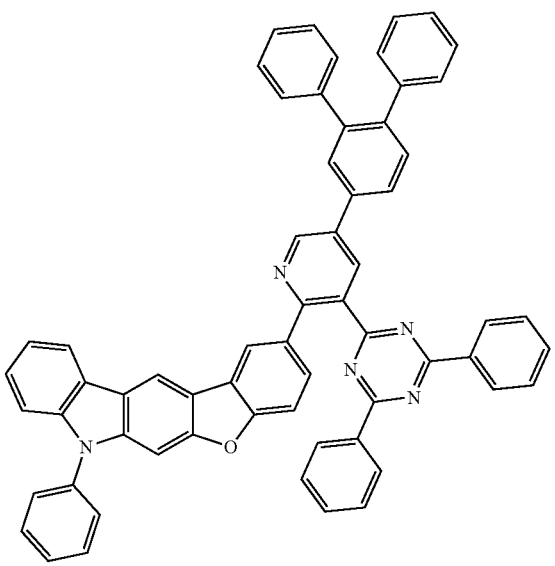
992
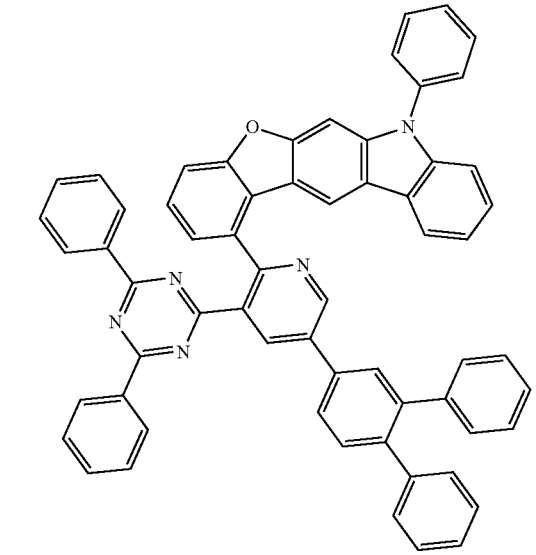
993

3703
-continued
994
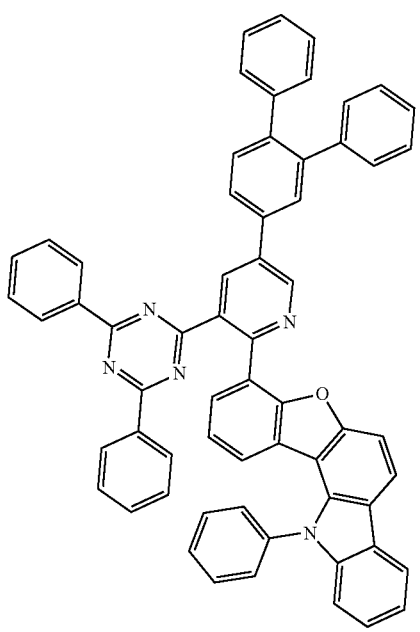
995
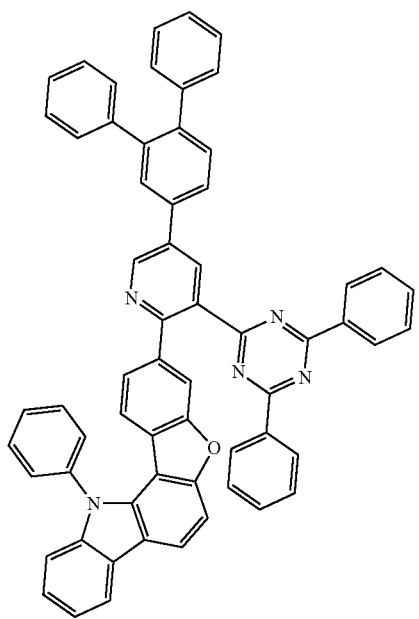
3704
-continued
996
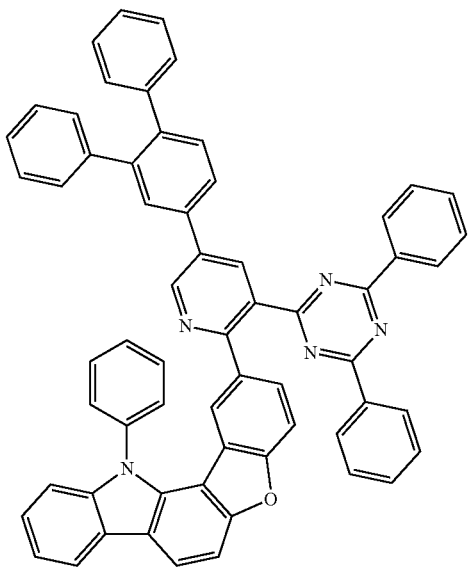
997
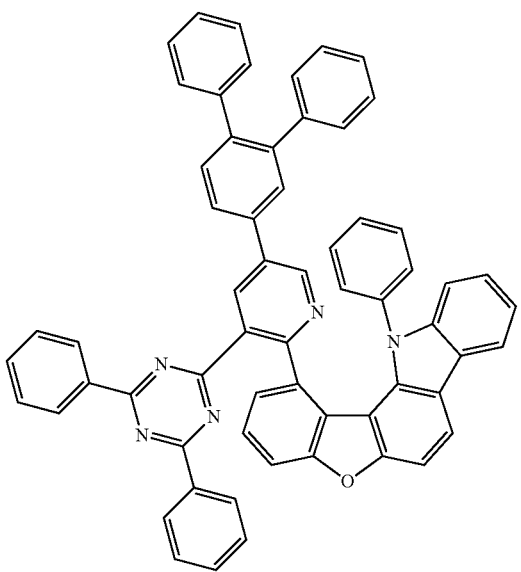

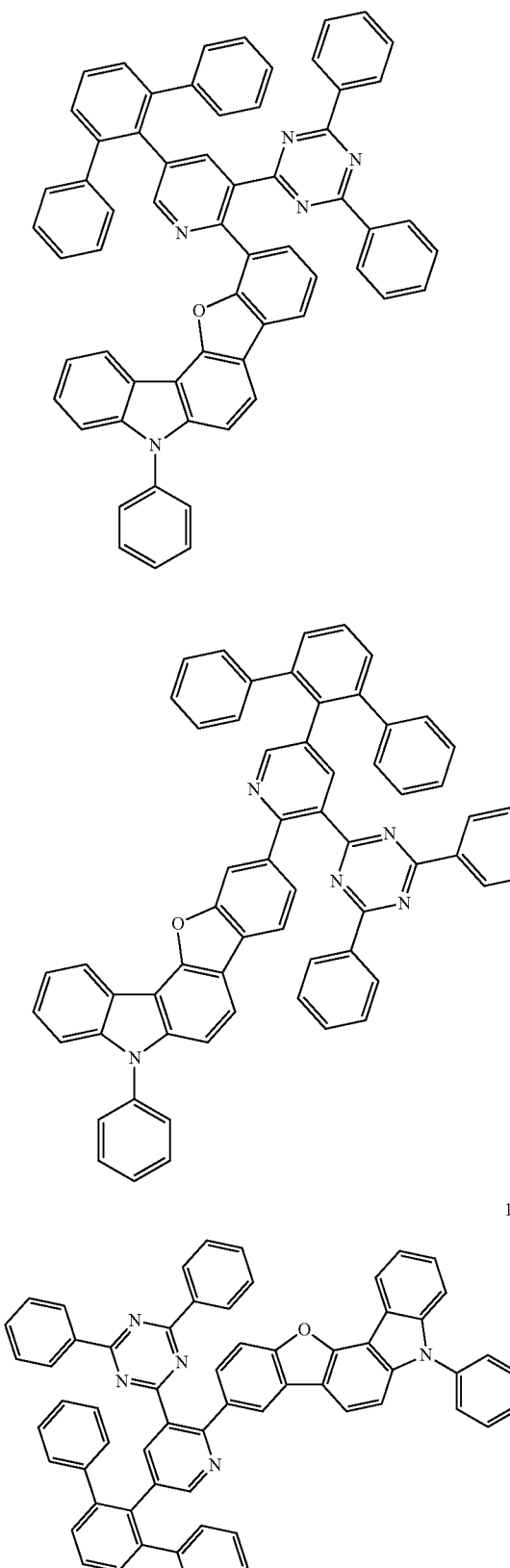
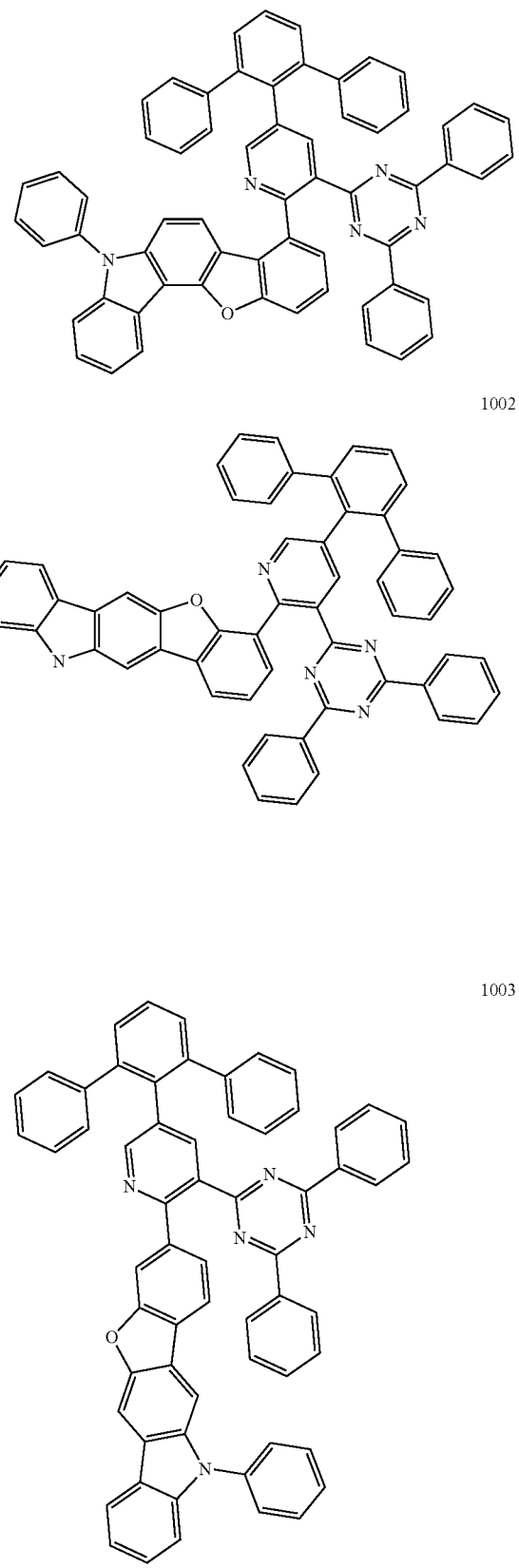

1004
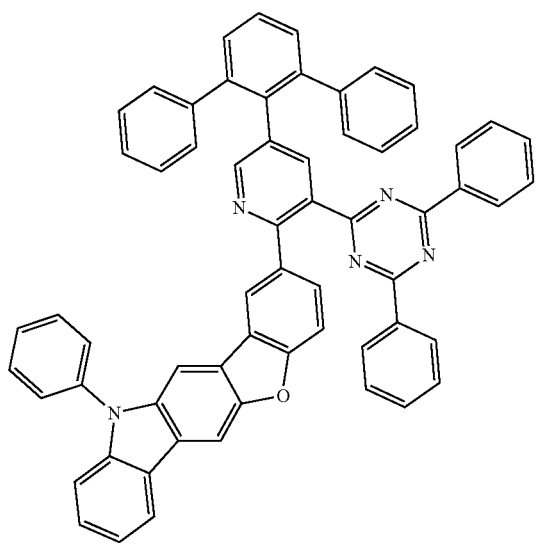
1005
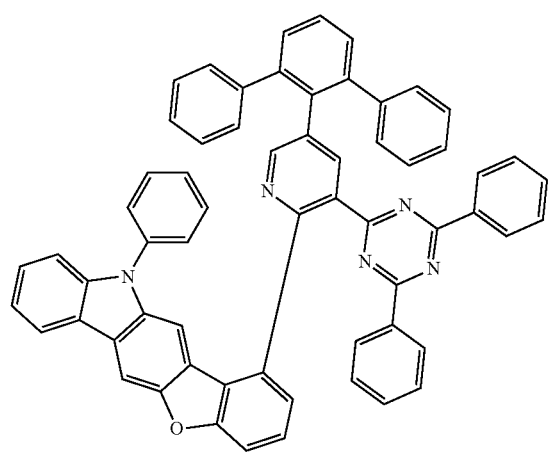
1006
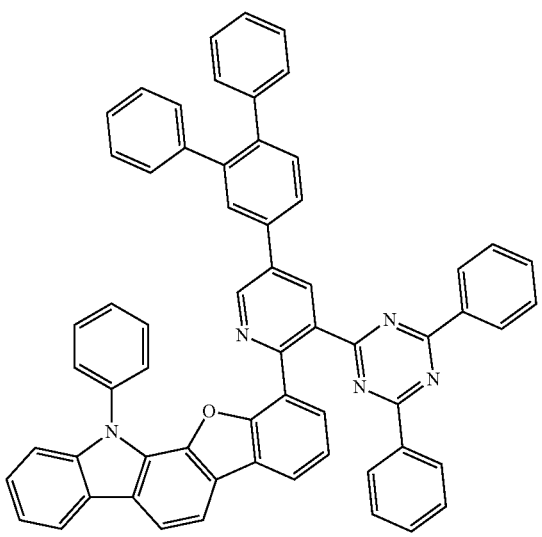
1007
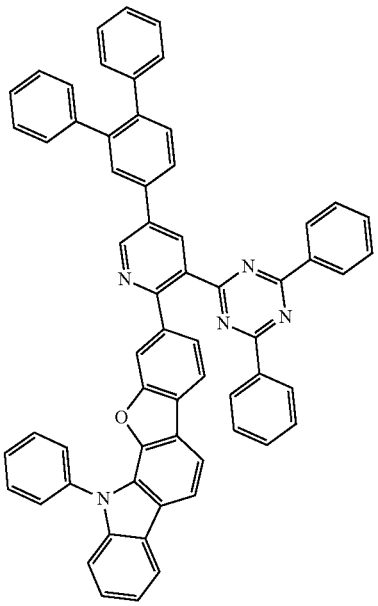
1008
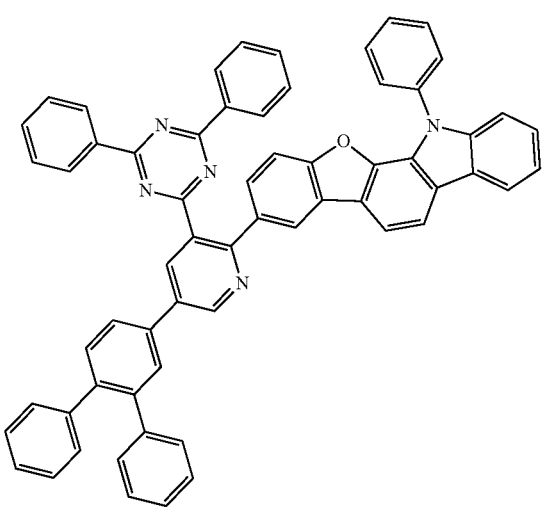

3709
-continued
1009
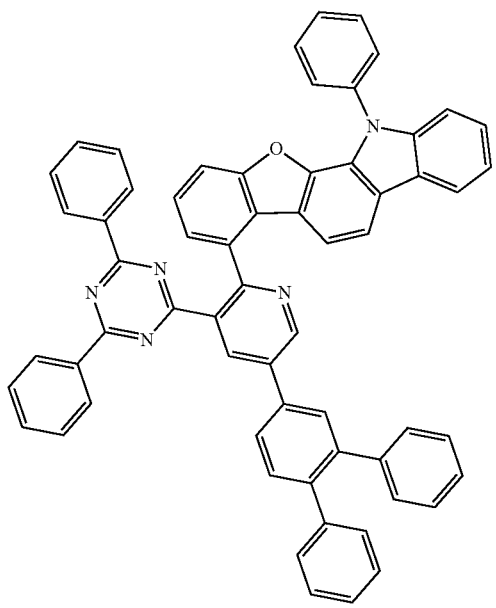
1010
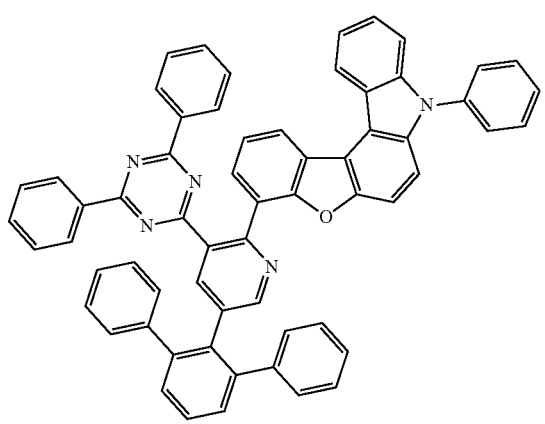
1011
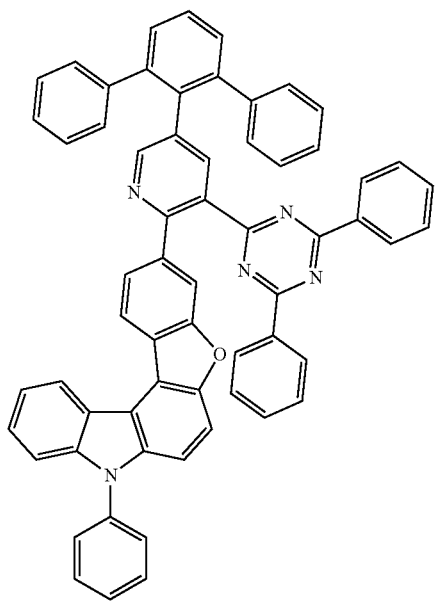
3710
-continued
1012
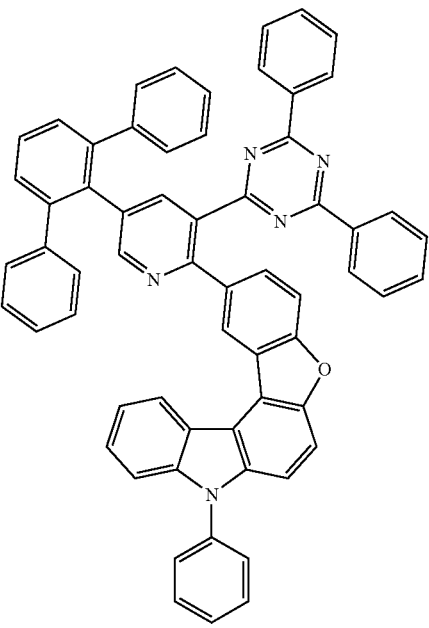
1013
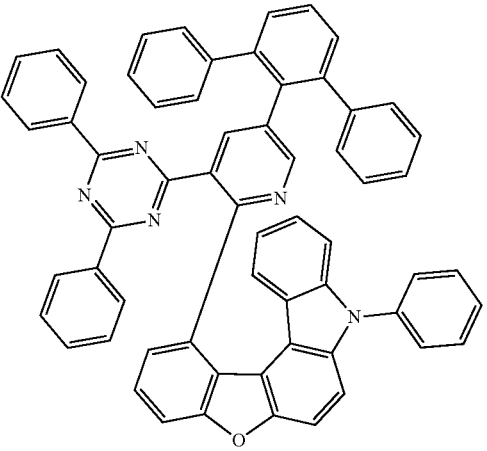
1014
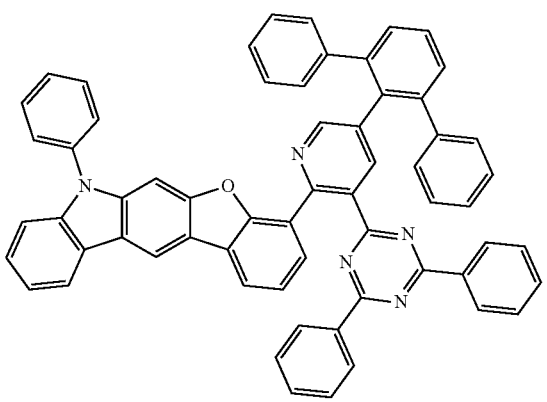

3711
-continued
1015
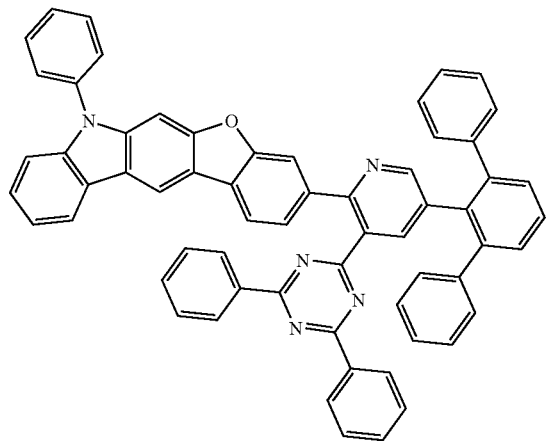
1016
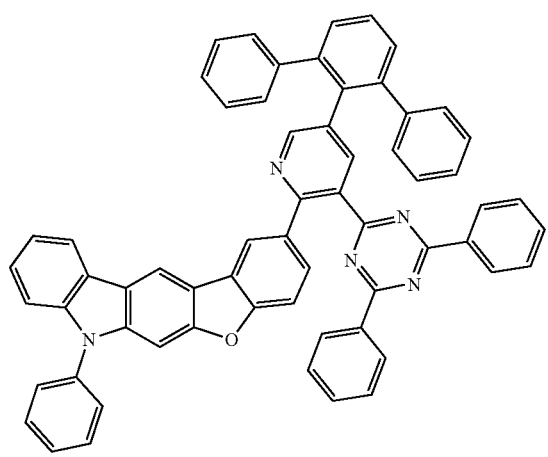
1017
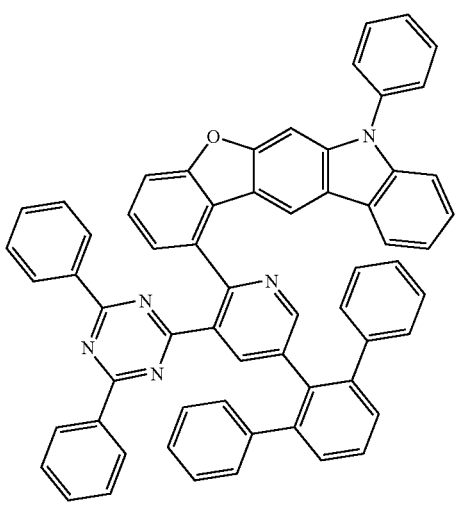
3712
-continued
1018
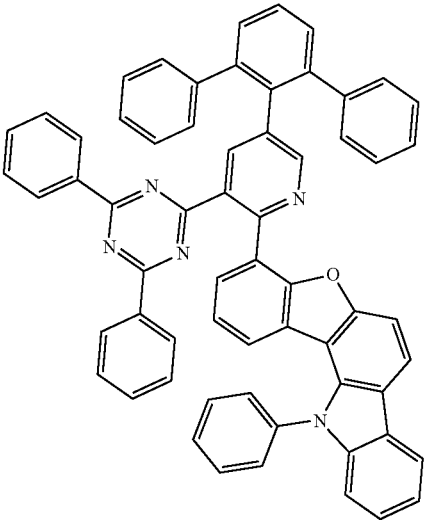
1019
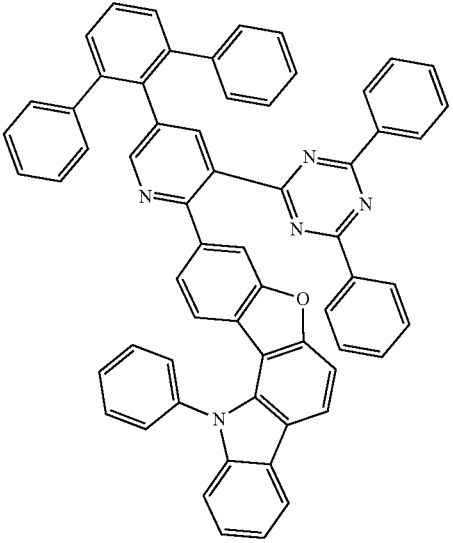
1020
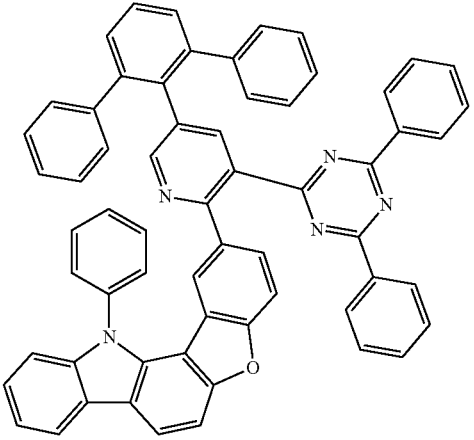

1021
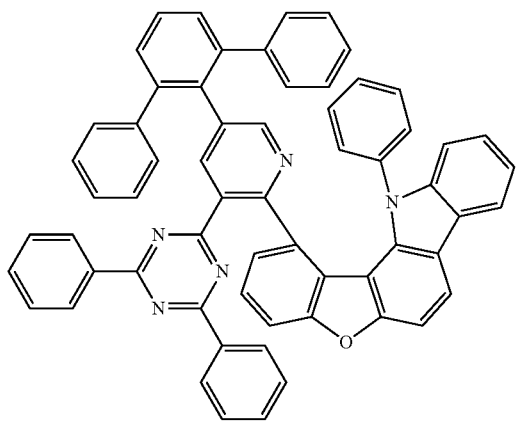
1022
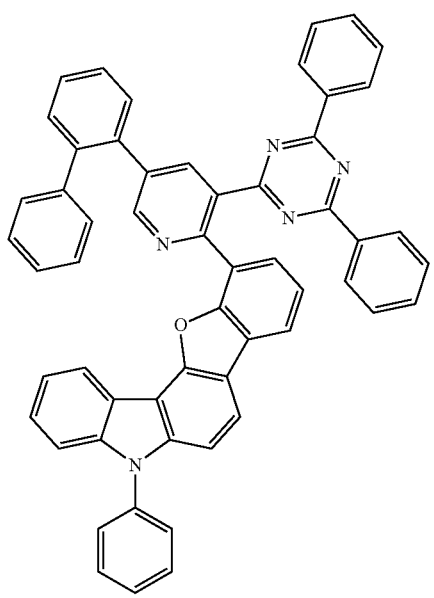
1023
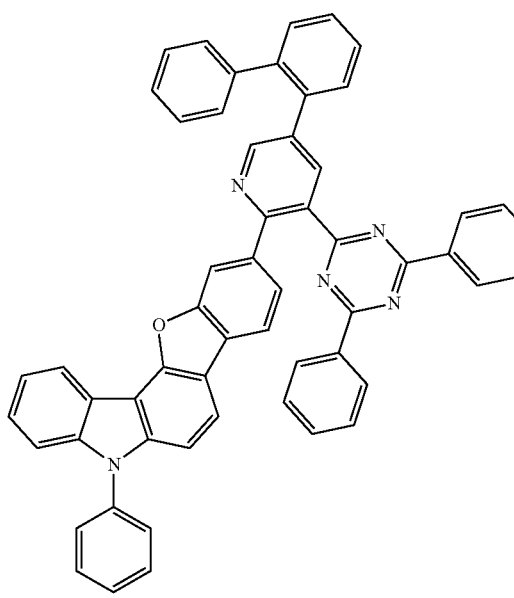
1024
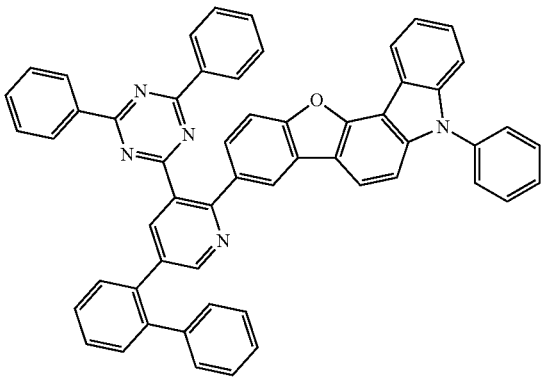
1025
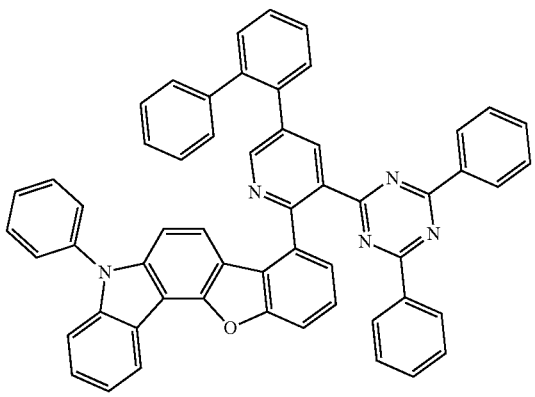
1026
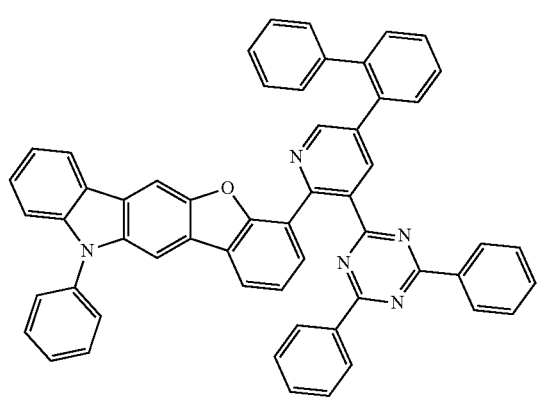

-continued
1027
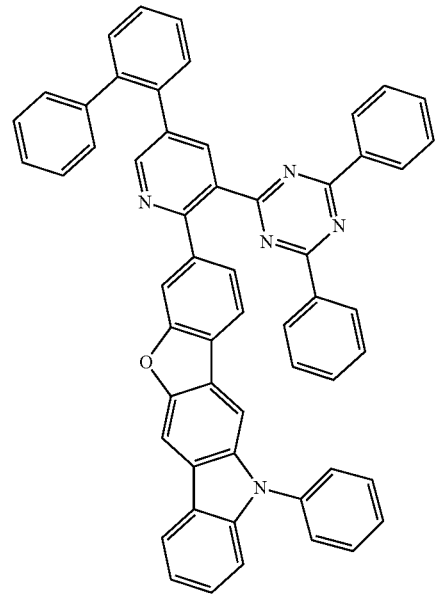
1028
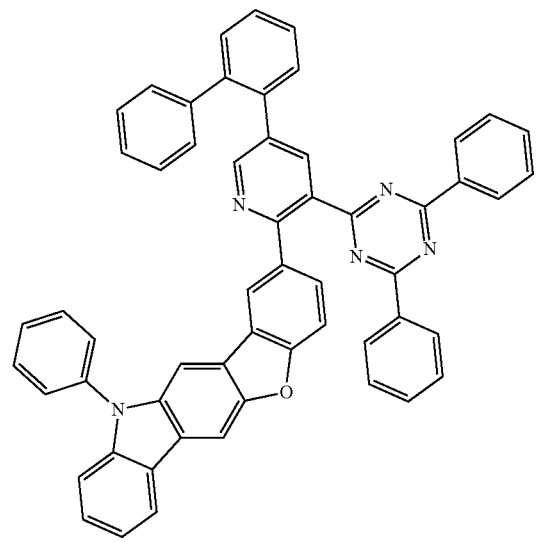
1029
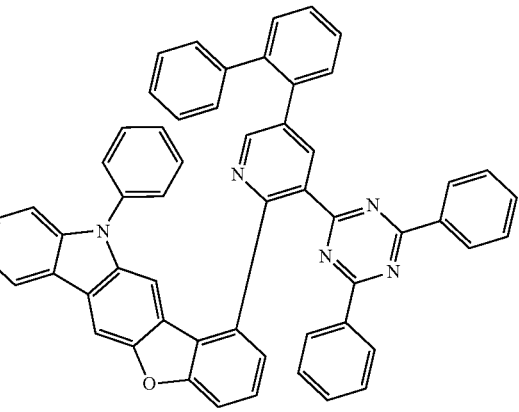
-continued
1030
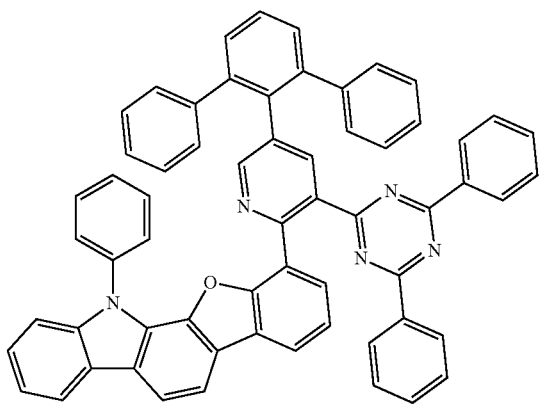
1031
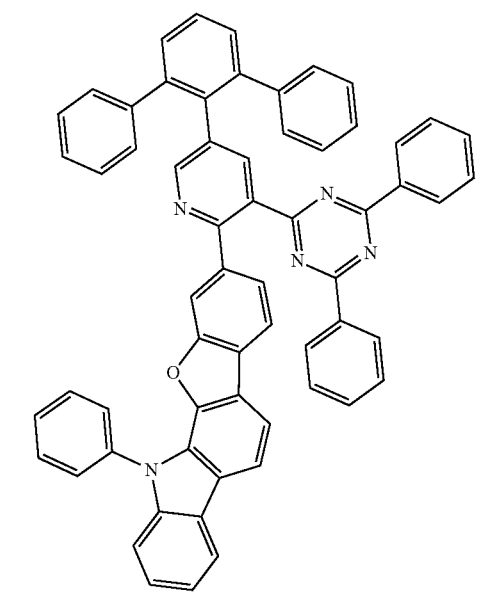
1032
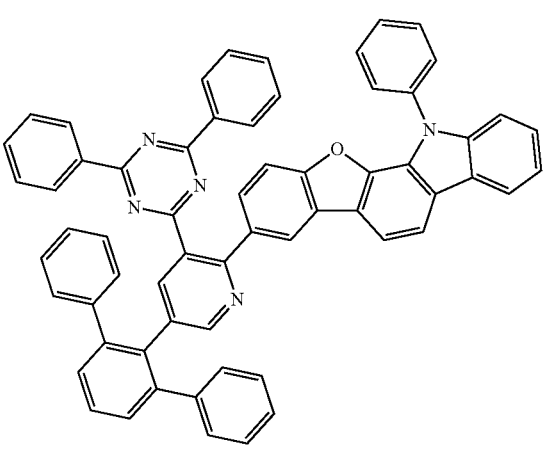

3717
-continued
1033
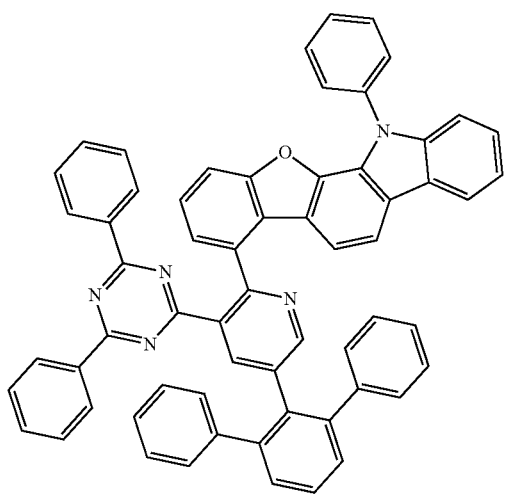
1034
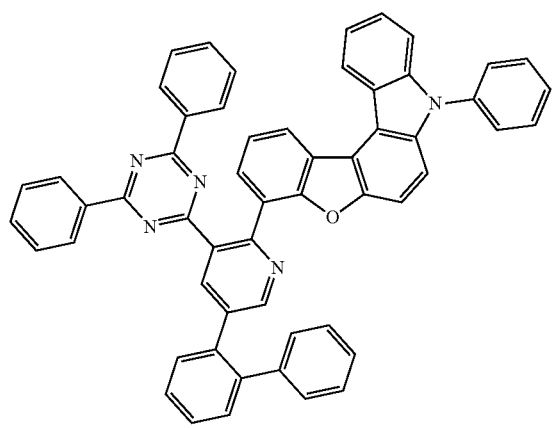
1035
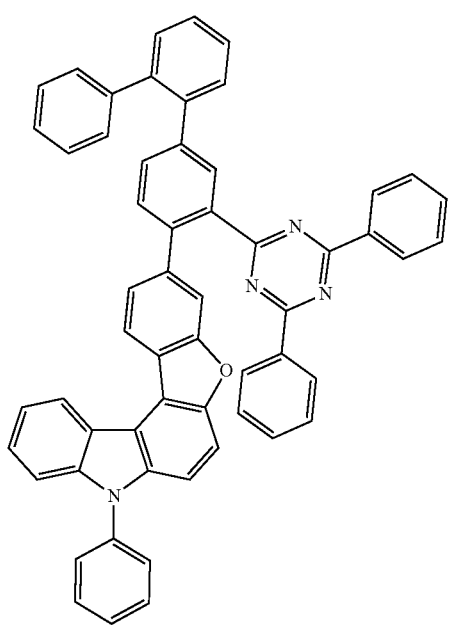
3718
-continued
1036
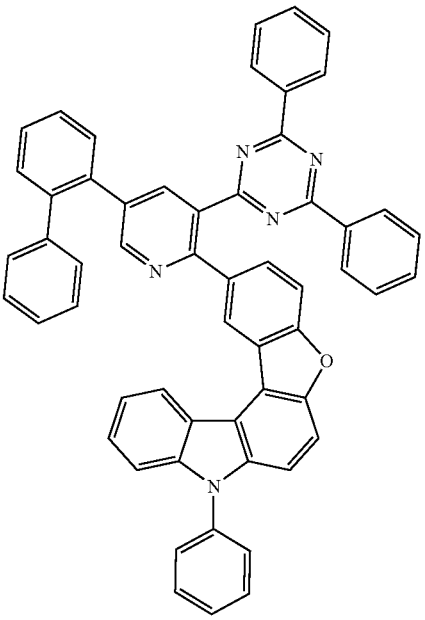
1037
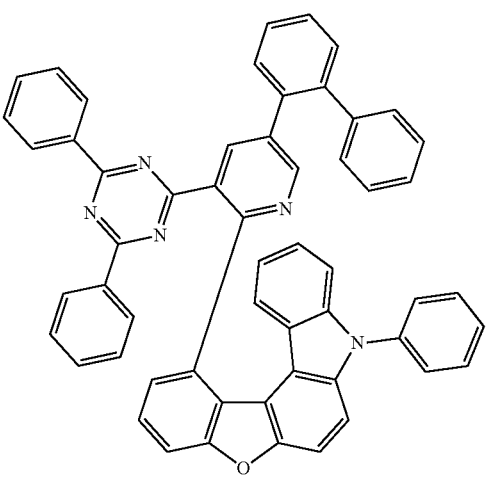
1038
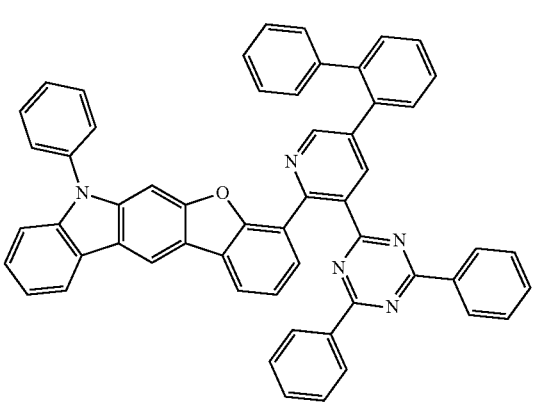

3719
-continued
1039
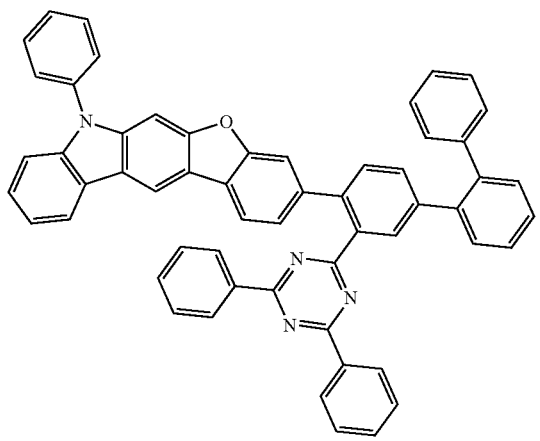
1040
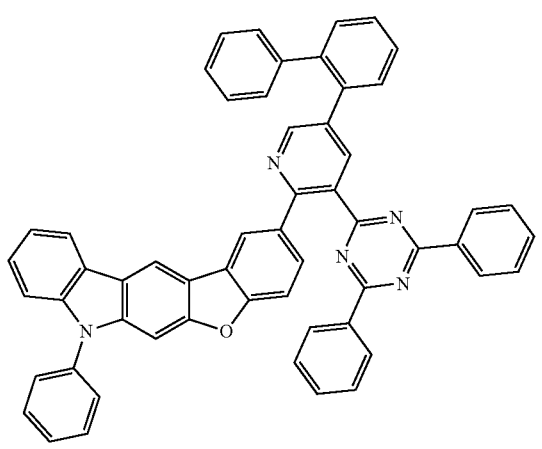
1041
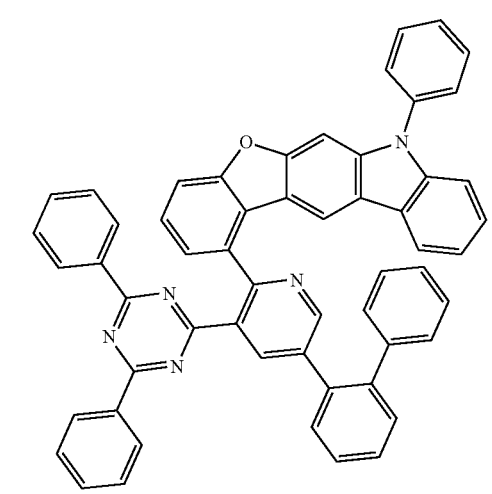
3720
-continued
1042
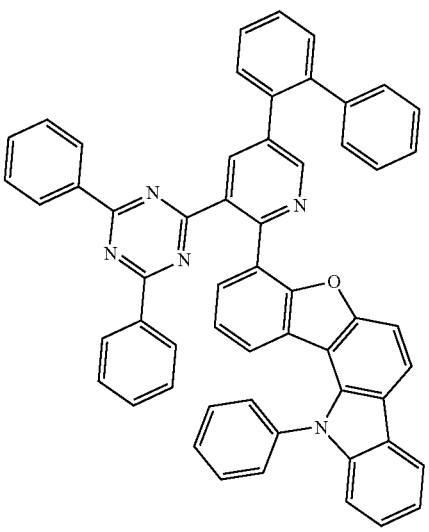
1043
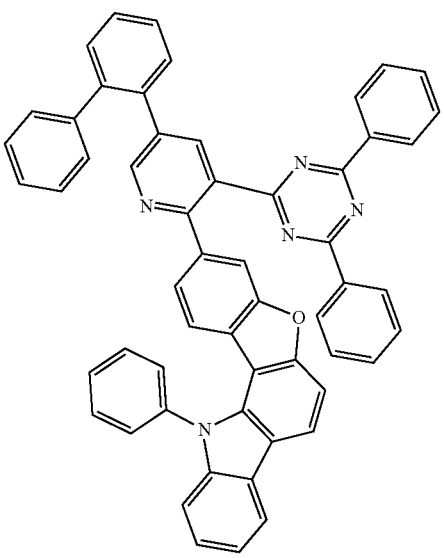
1044
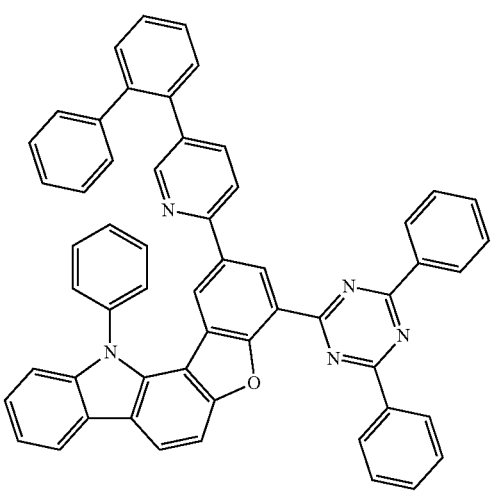

1045
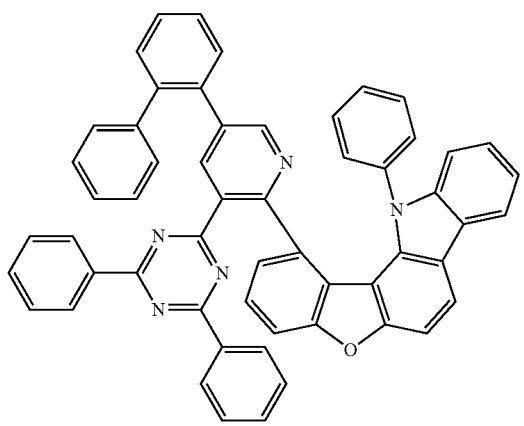
1046
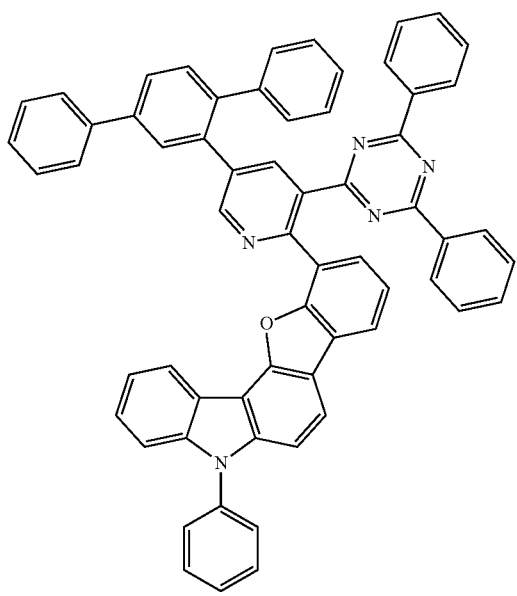
1047
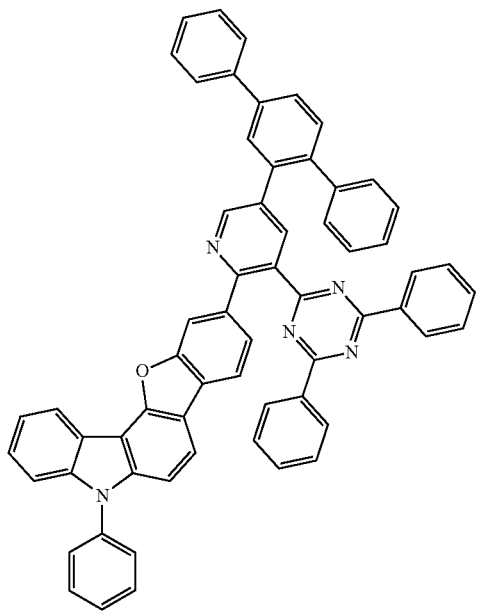
1048
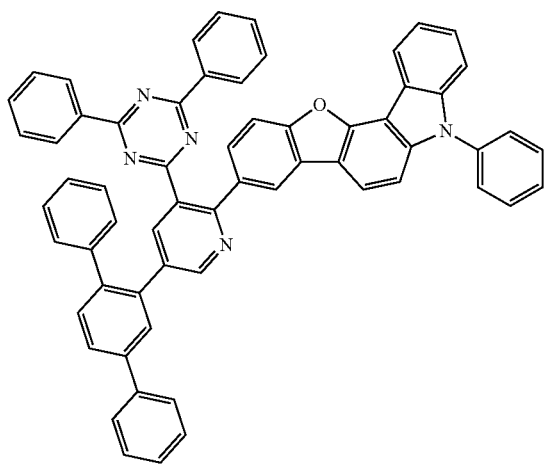
1049 1050
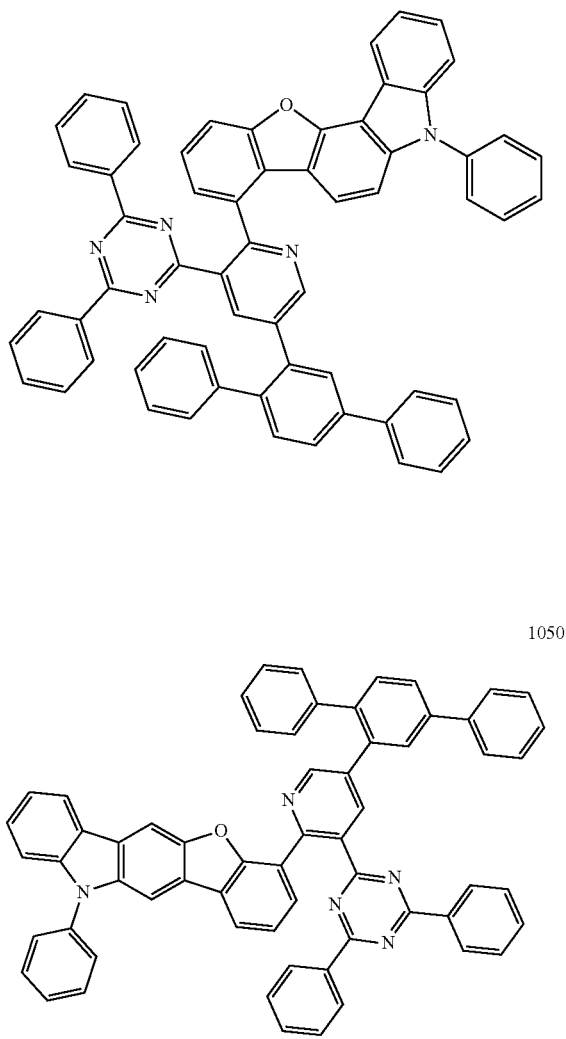

-continued
1051
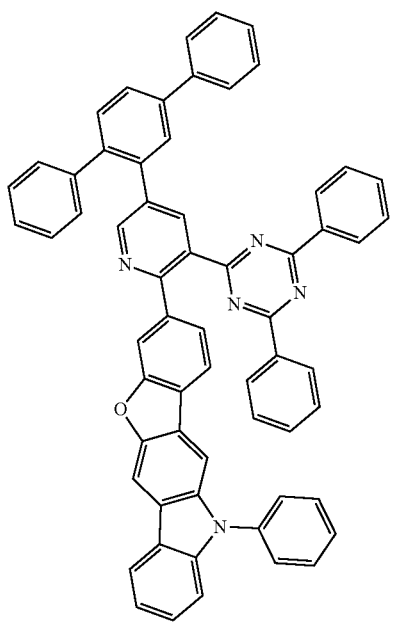
1052
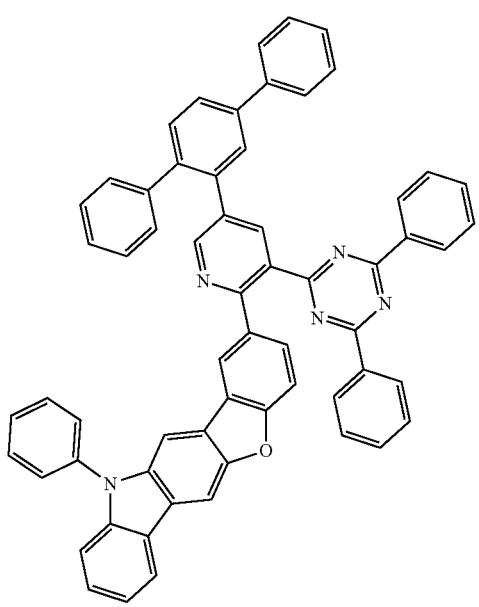
-continued
1053
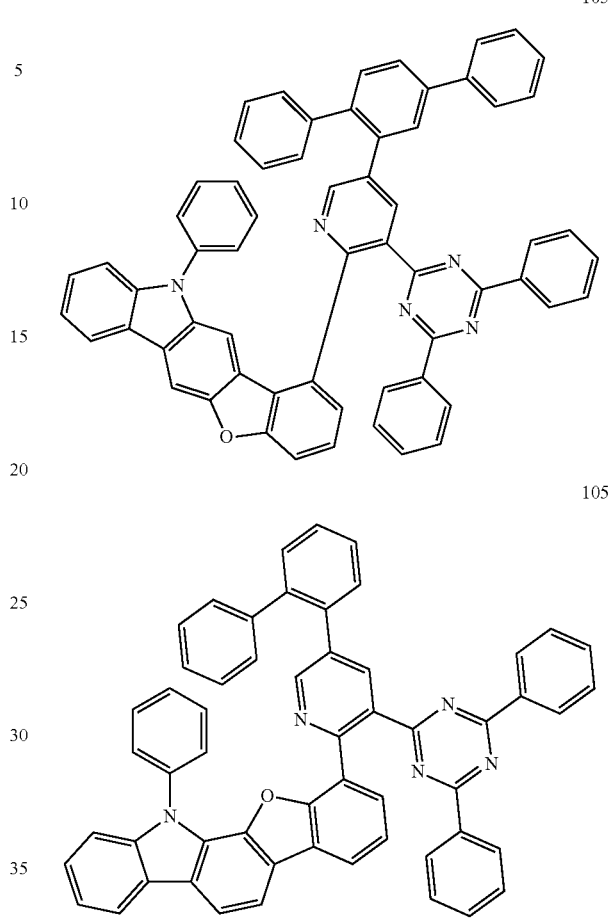
1054
1055
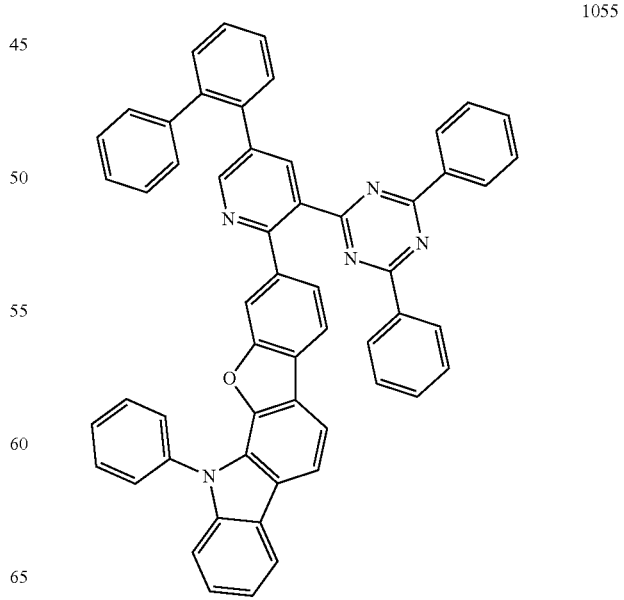

-continued
1056
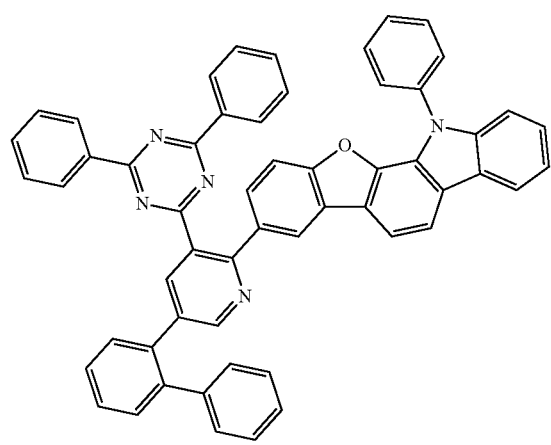
1057
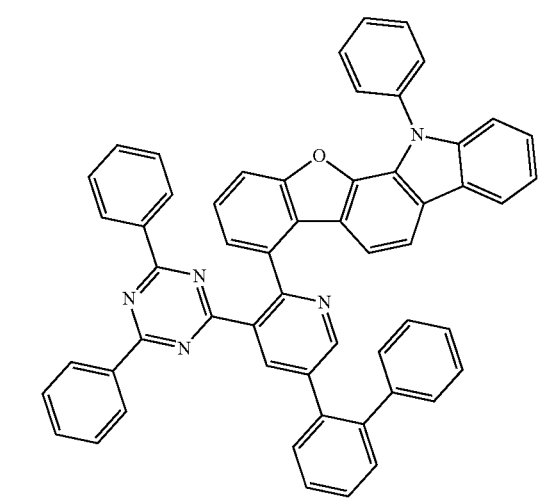
-continued
1059
1060
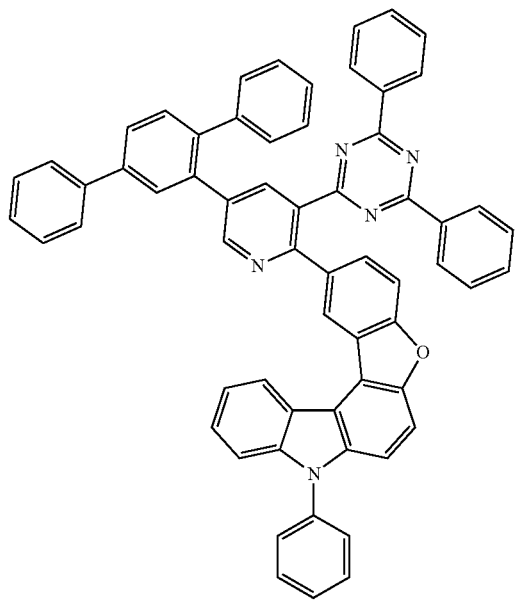

3727
-continued
1061
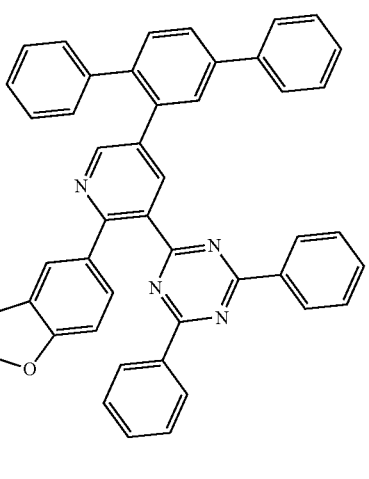
1062
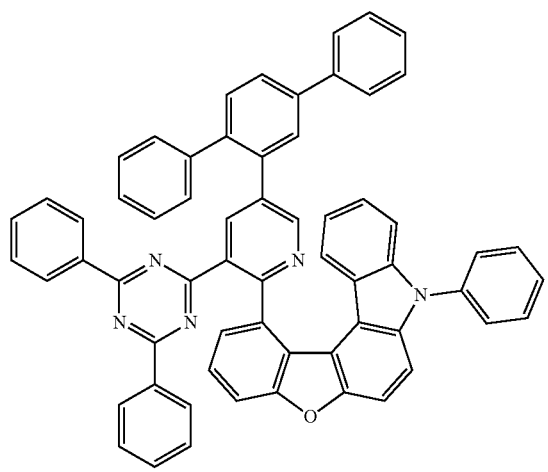
1063
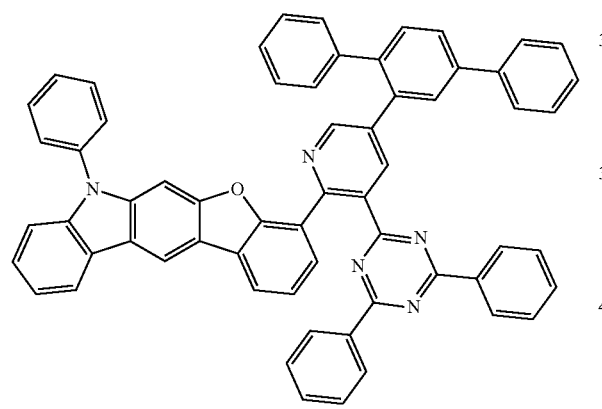
3728
-continued
1064
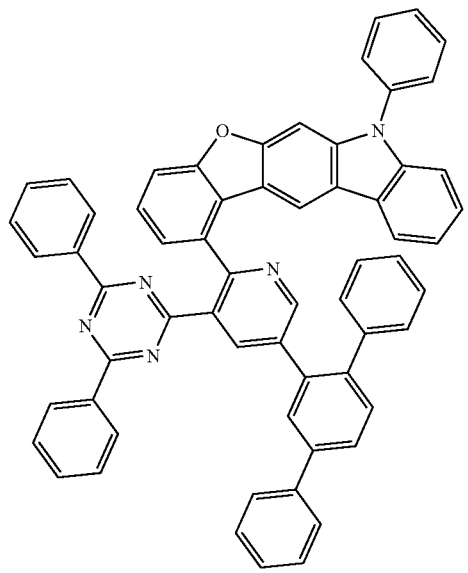
1065

3729
-continued
1066
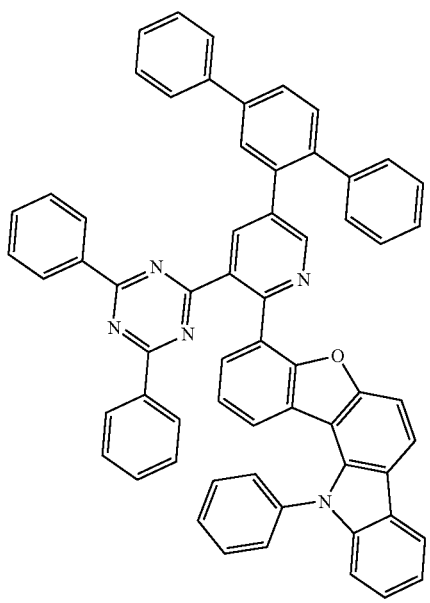
1067
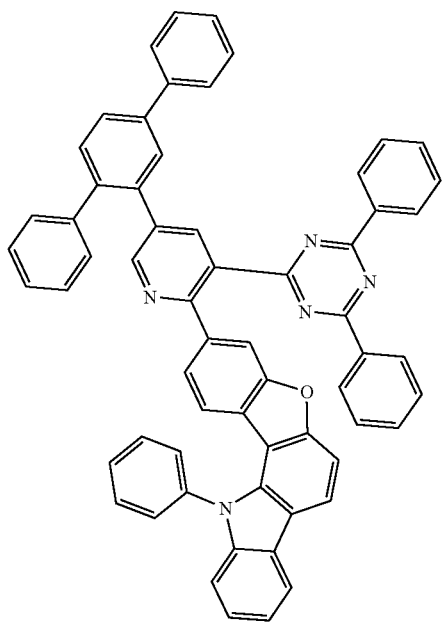
3730
-continued
1068
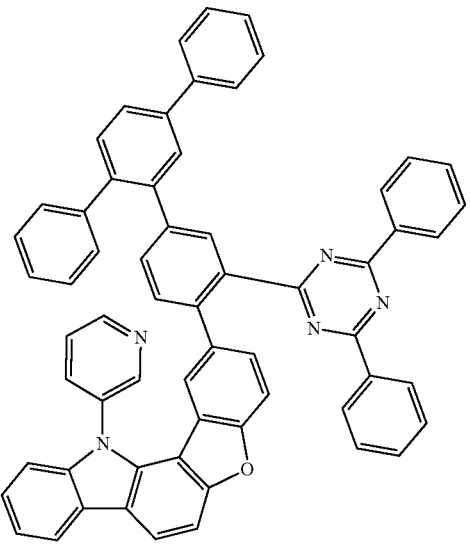
1069
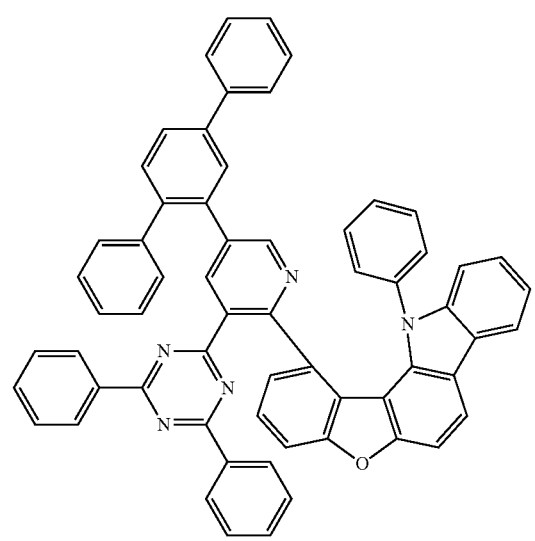
1070
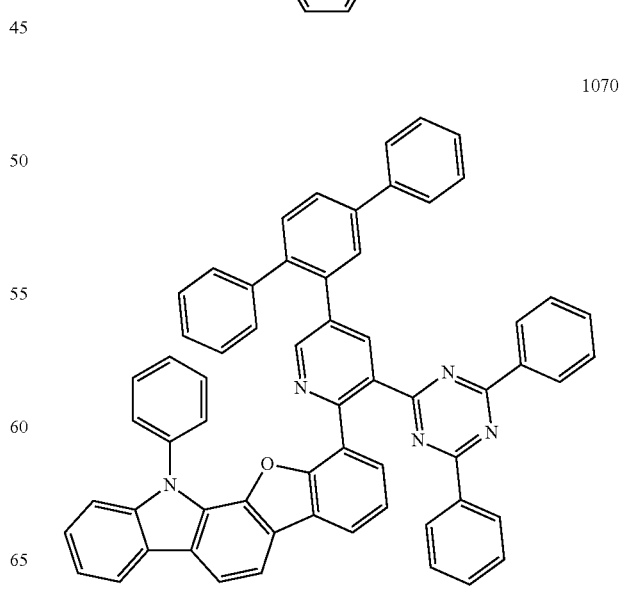

3731
-continued
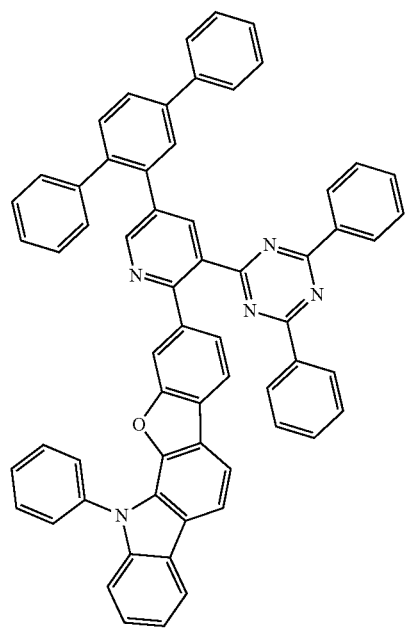
1071
3732
-continued
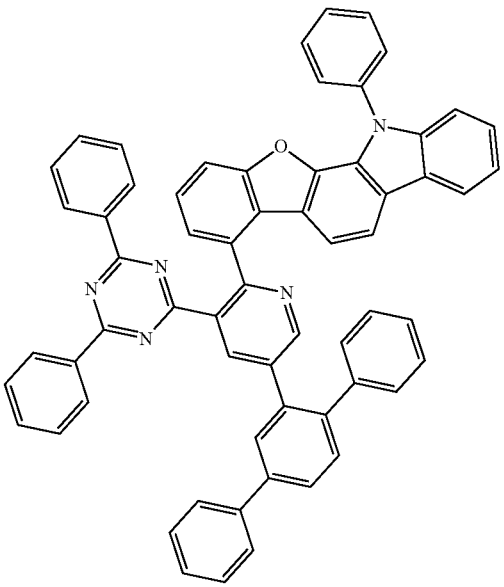
1073
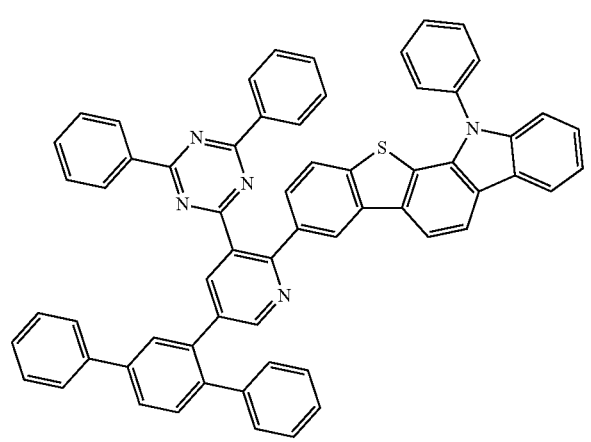
1072
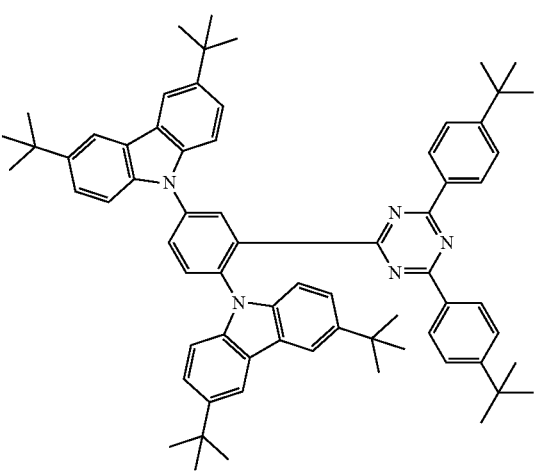
1074

3733
-continued
1075
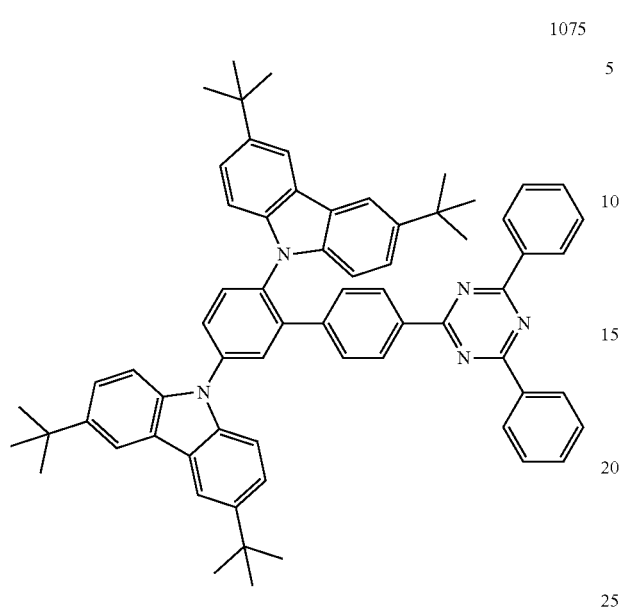
3734
-continued
1077
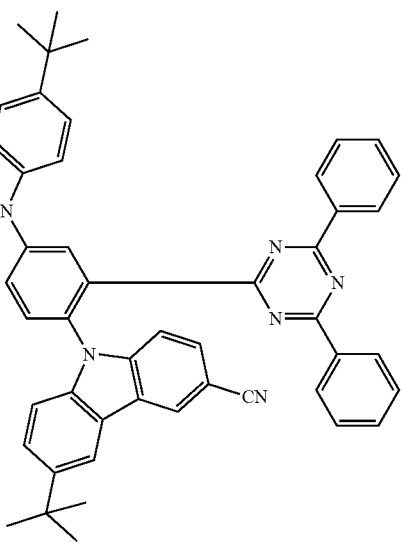
1076
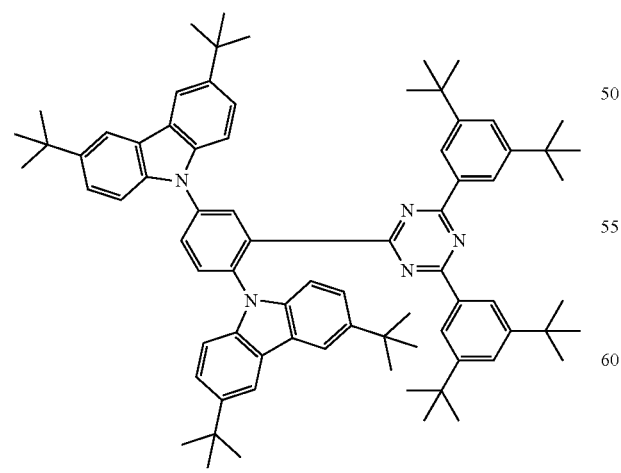
1078
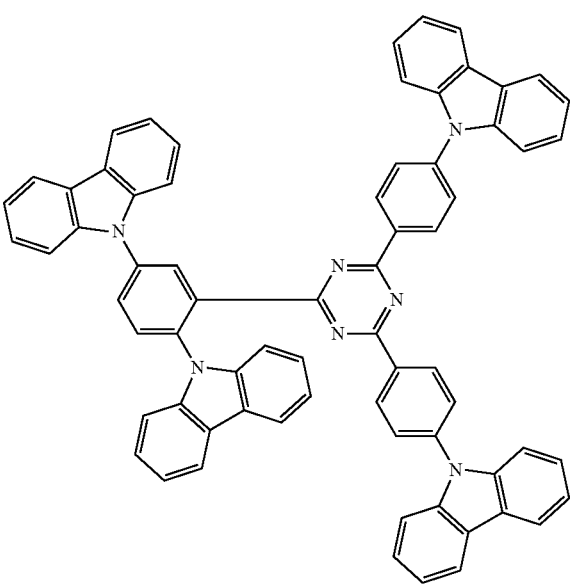

Group XI
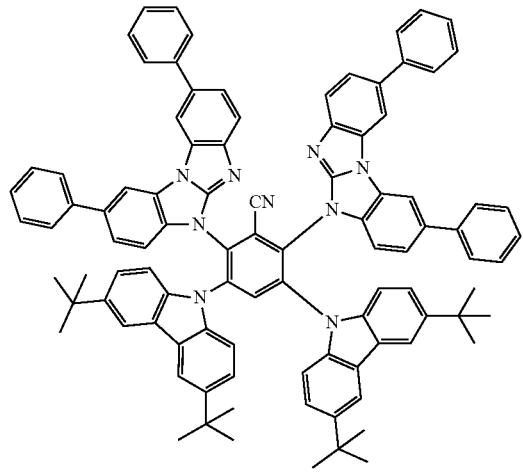
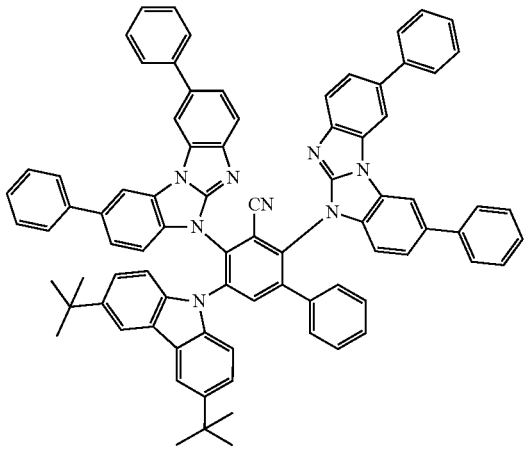
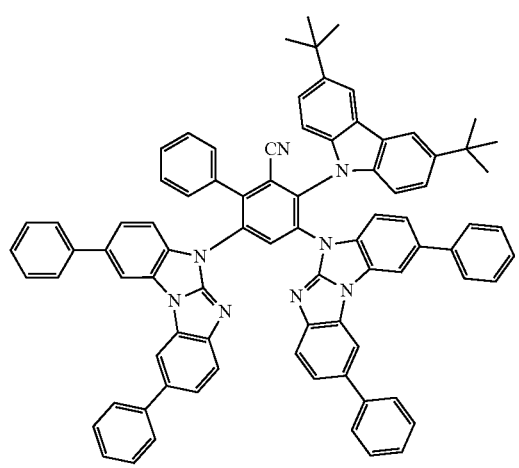
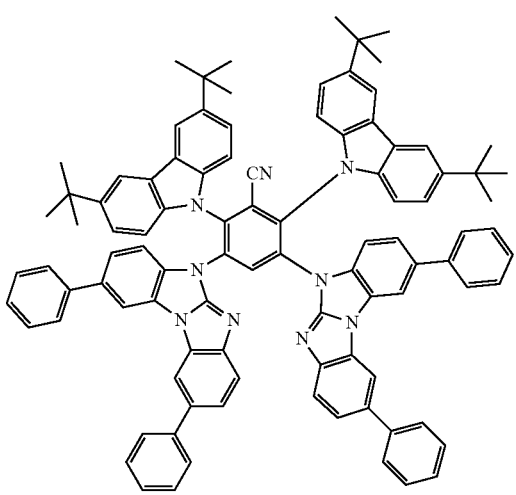
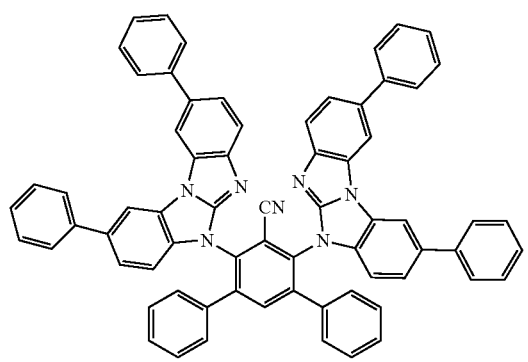
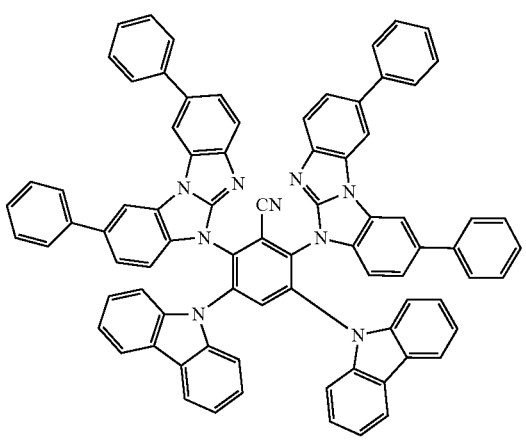

-continued
7
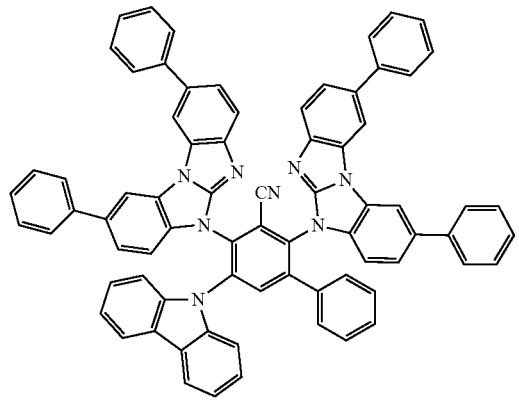
8
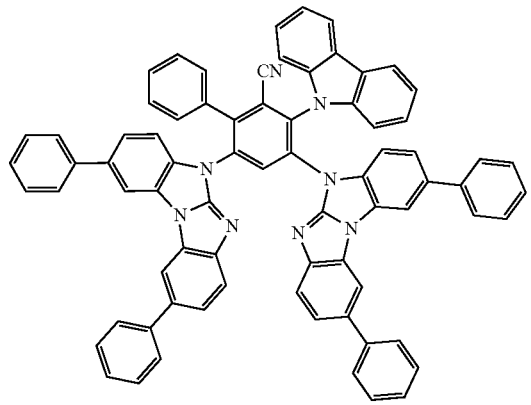
9
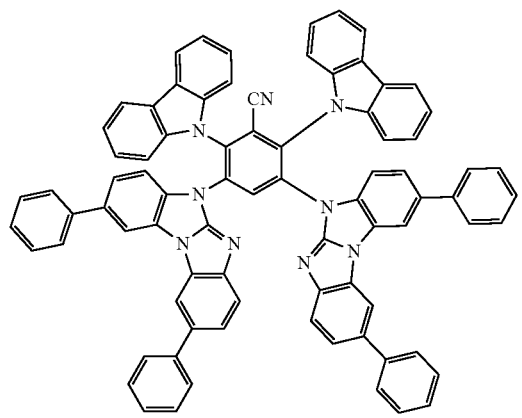
10
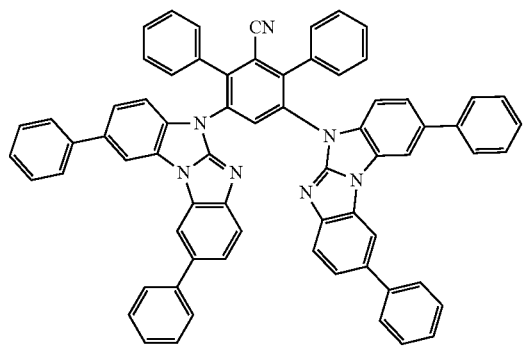
11
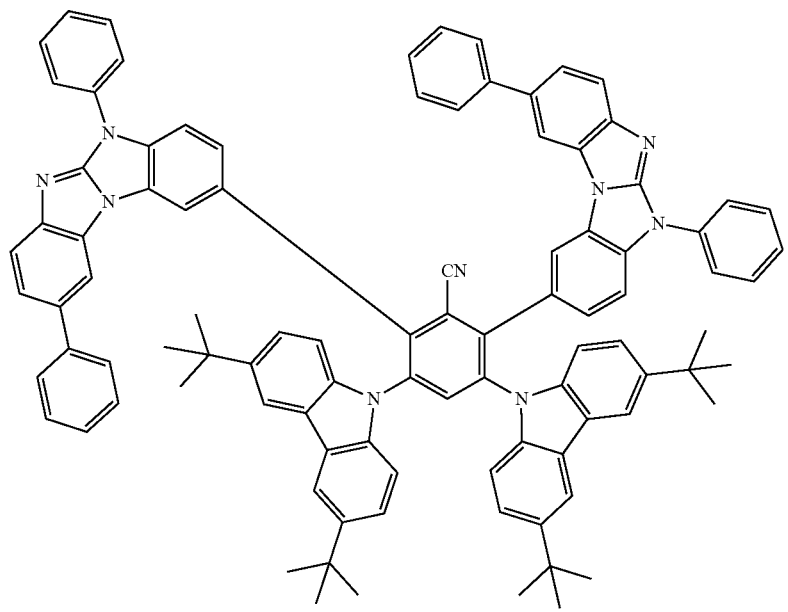

-continued
12
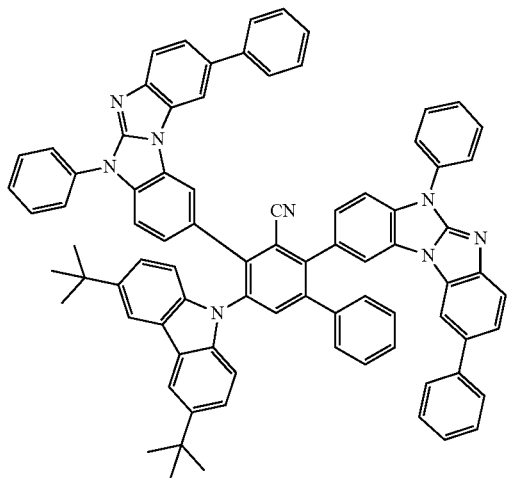
13
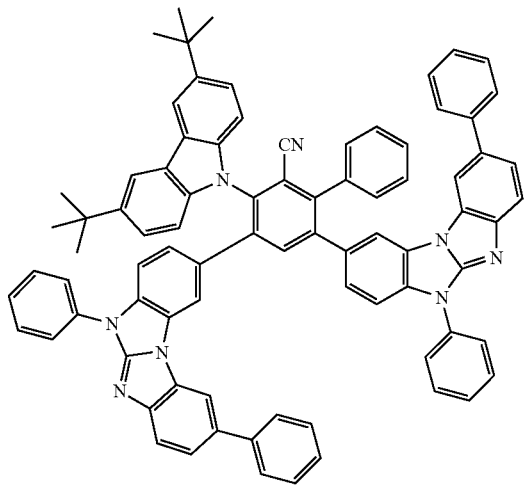
14
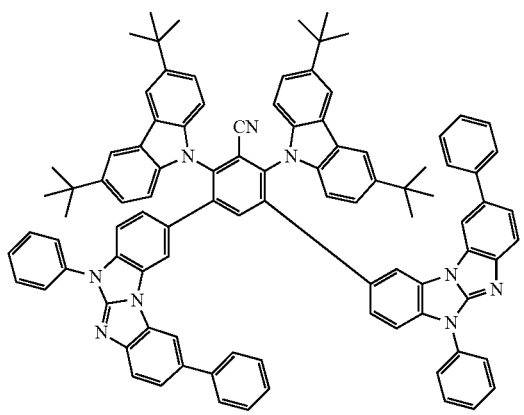
15
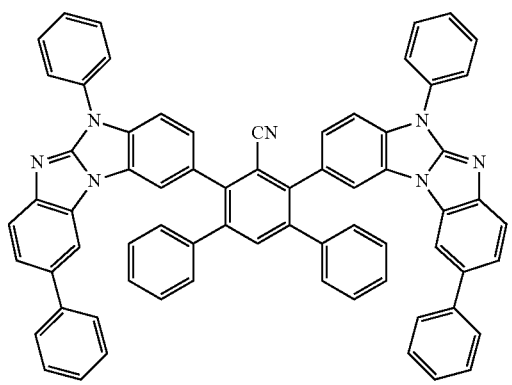
16
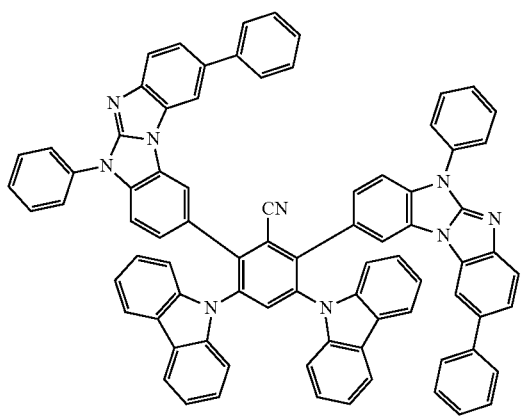
17
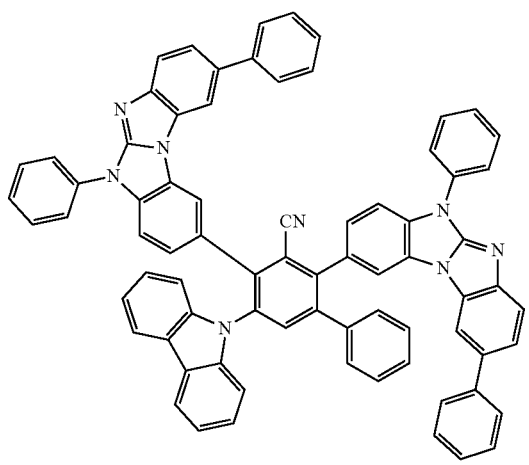

-continued
3741
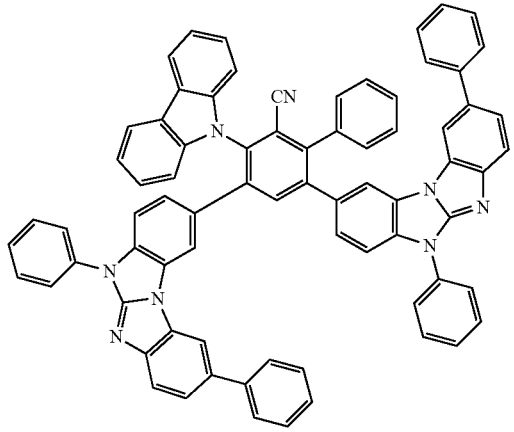
18
3742
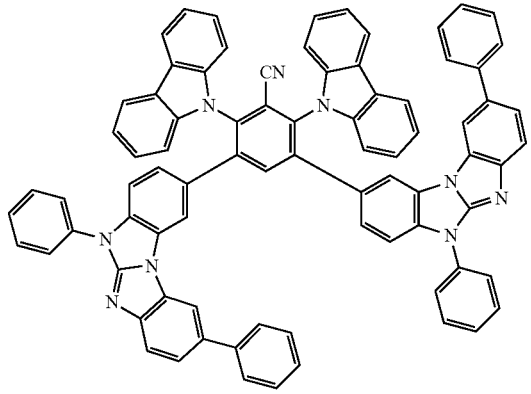
19
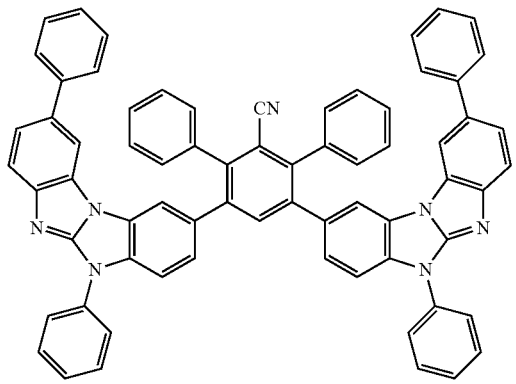
20
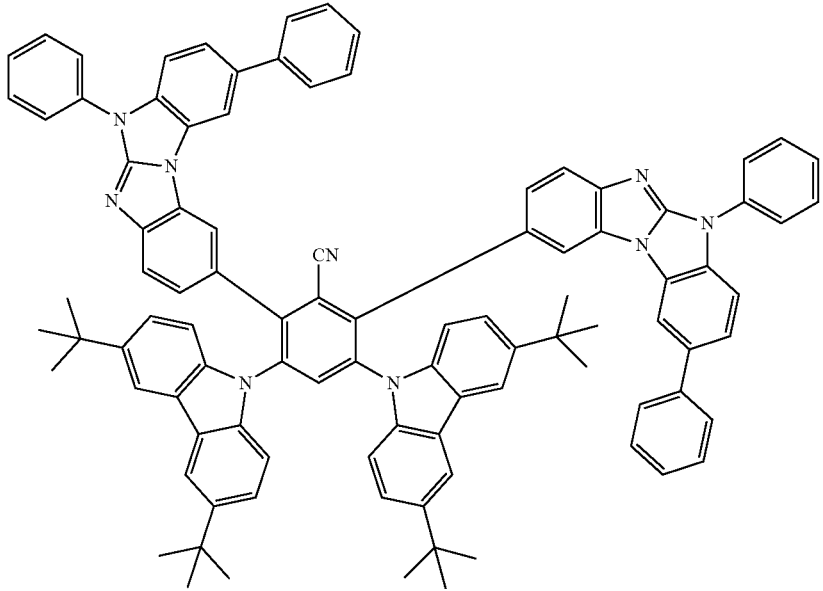
21

22
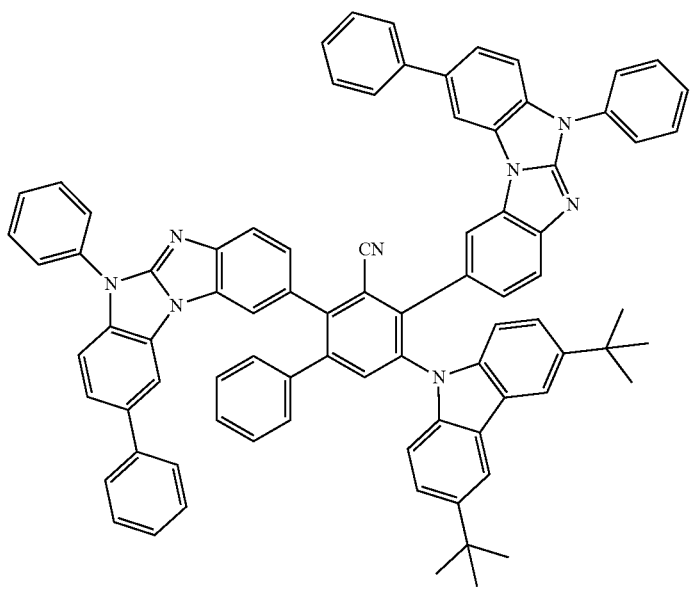
23
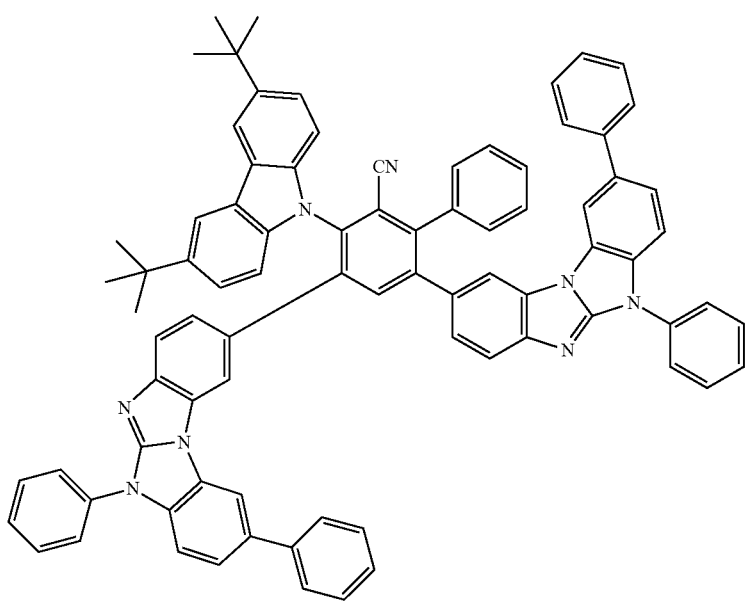

24
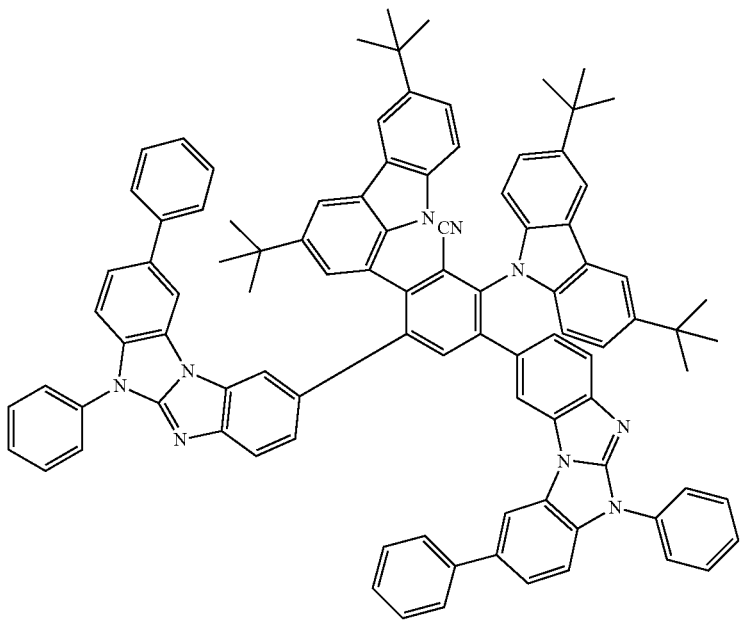
25
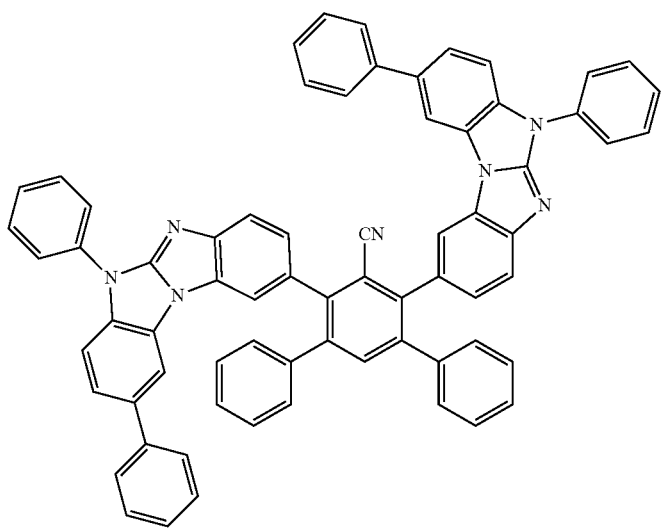
26
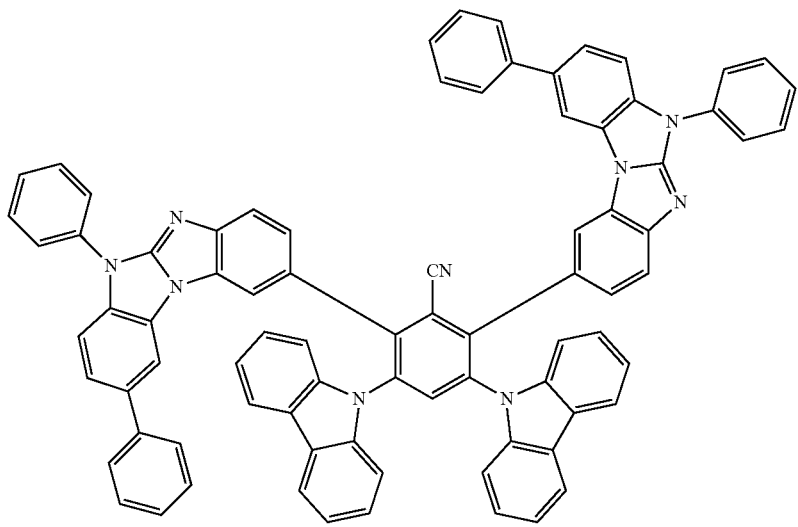

27
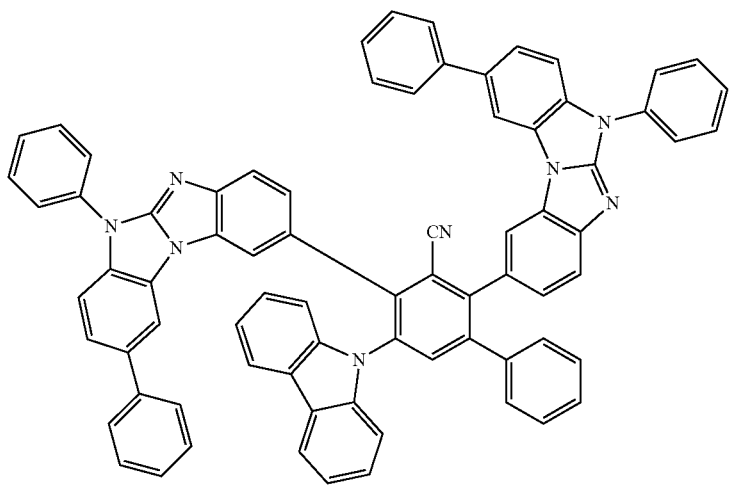
28
29

30
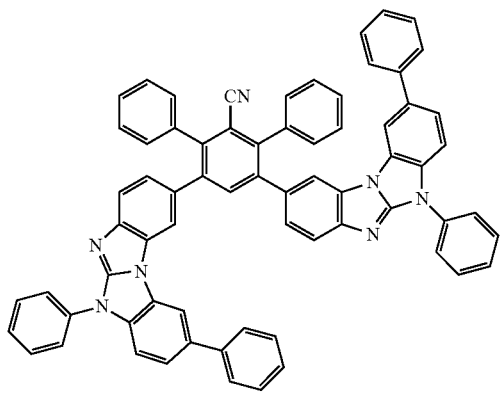
31
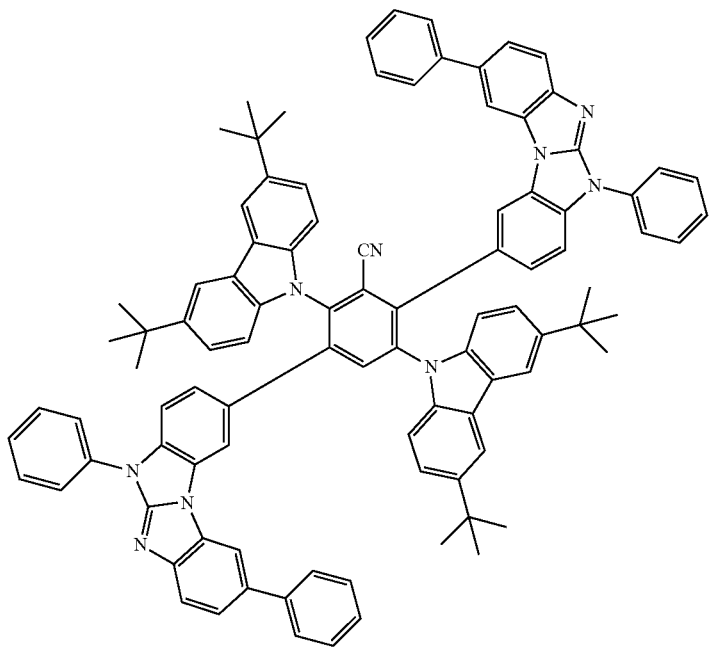
32
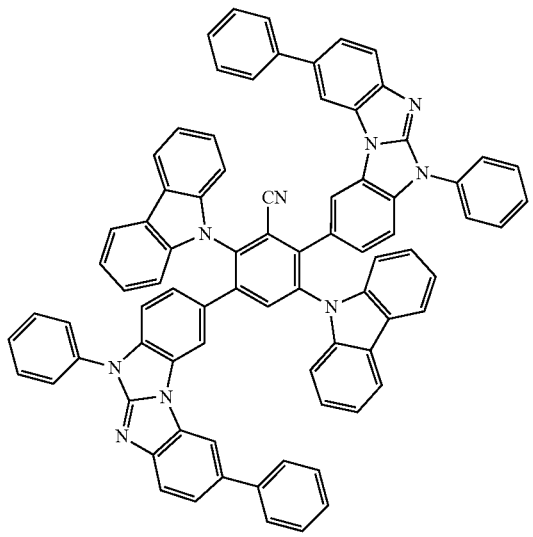
33
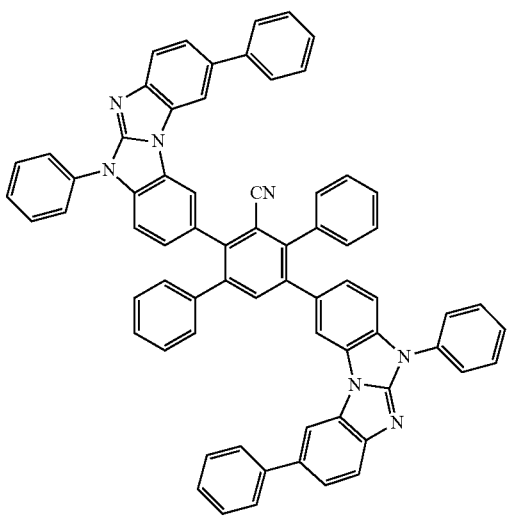

-continued
34
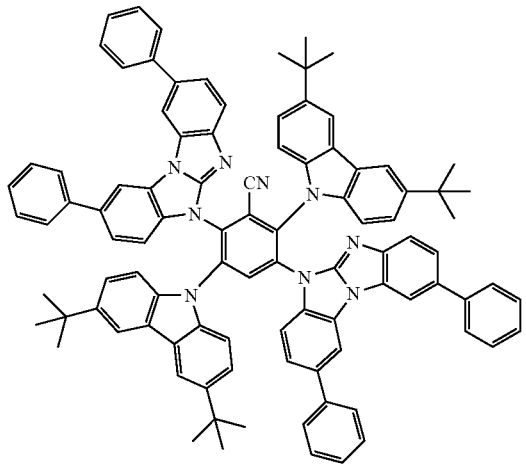
35
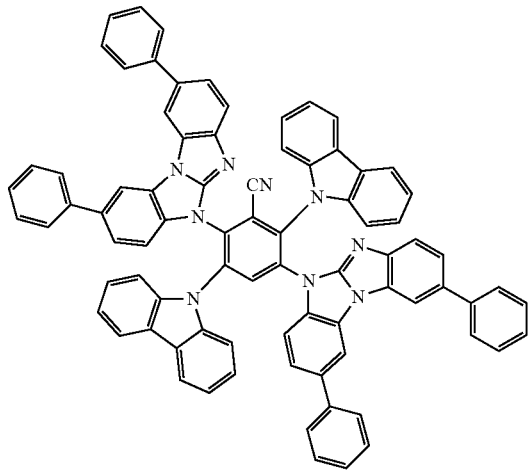
36
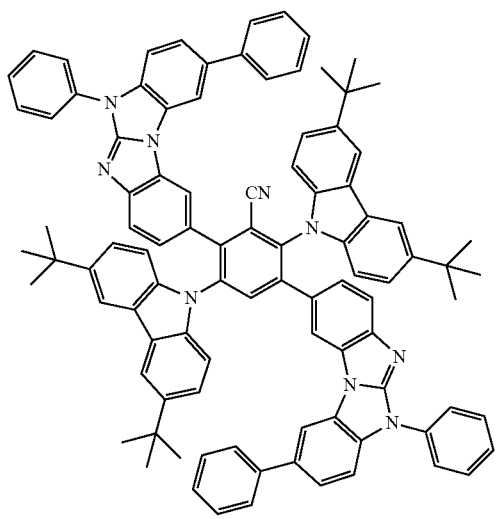
37
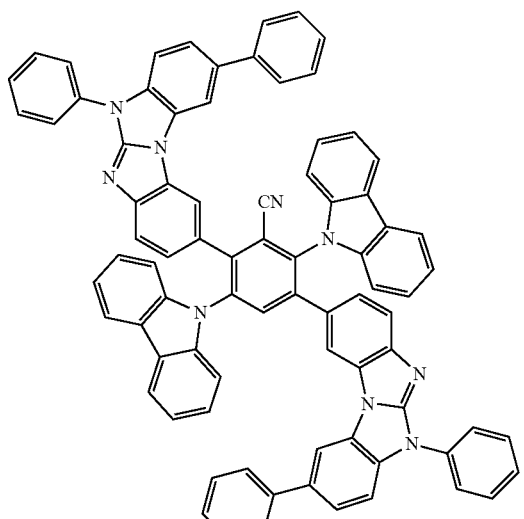
38
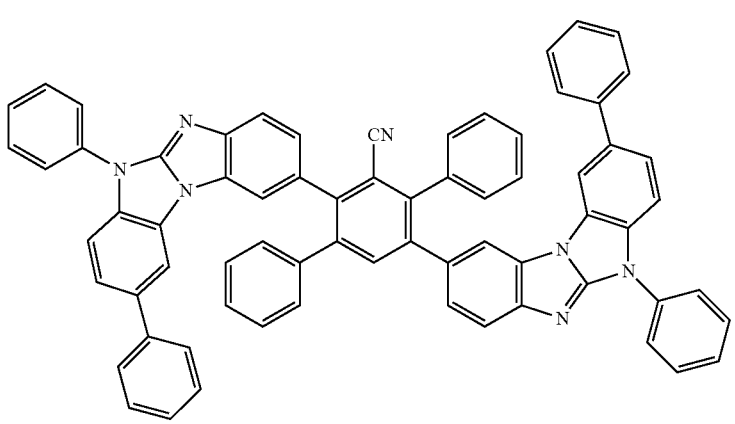

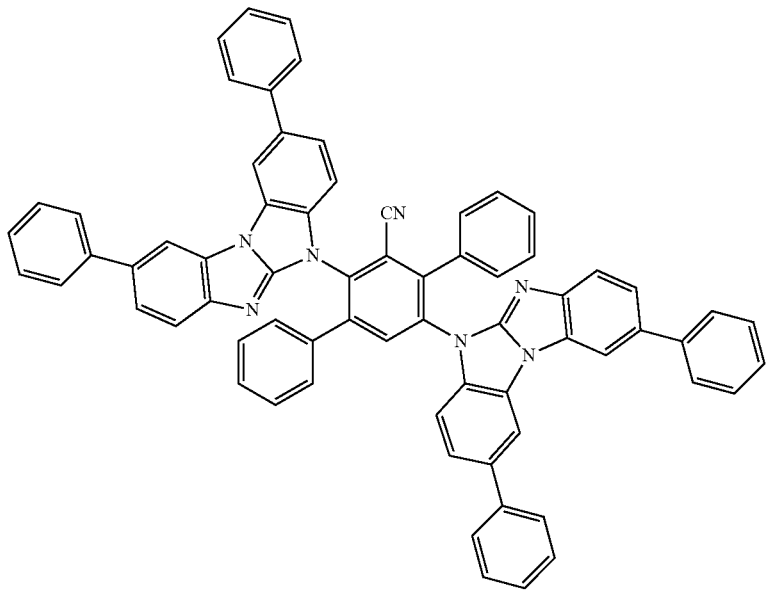

Group XII

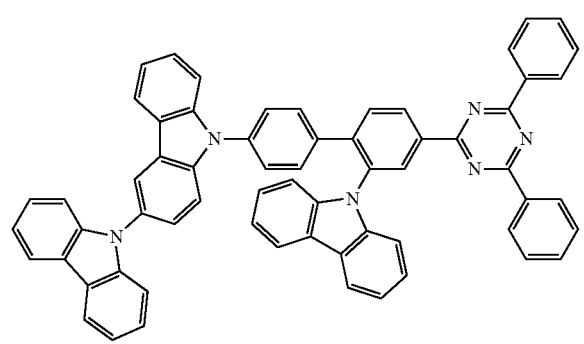

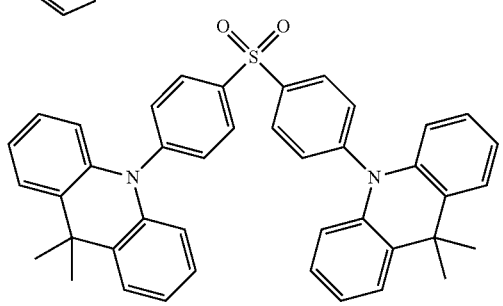

Hole Transport Region 12

In the organic light-emitting device 10, the hole transport region 12 may be between the first electrode 11 and the emission layer 15.

The hole transport region 12 may have a single-layered structure or a multi-layered structure.

For example, the hole transport region 12 may have a structure of hole injection layer, a structure of hole transport layer, a structure of hole injection layer/hole transport layer, a structure of hole injection layer/first hole transport layer/second hole transport layer, a structure of hole transport layer/intermediate layer, a structure of hole injection layer/hole transport layer/intermediate layer, a structure of hole transport layer/electron blocking layer, or a structure of hole injection layer/hole transport layer/electron blocking layer, but embodiments are not limited thereto.

The hole transport region 12 may include a compound having hole transport characteristics.

For example, the hole transport region 12 may include an amine-based compound.

In an embodiment, the hole transport region 12 may include at least one compound represented by Formulae 201 to 205, but embodiments are not limited thereto:

Formula 201
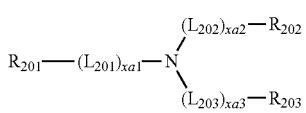

Formula 202
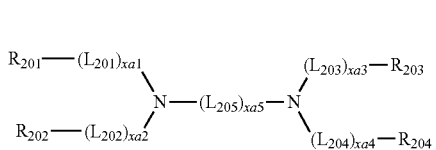

Formula 203
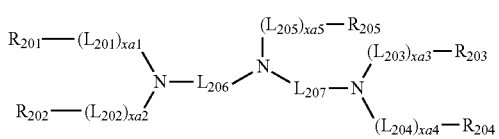

Formula 204
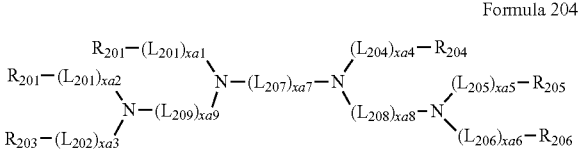

Formula 205

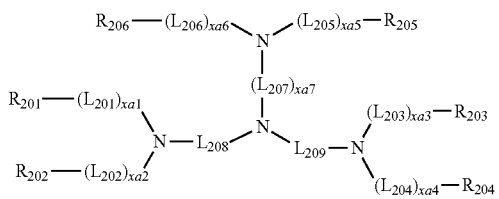

wherein, in Formulae 201 to 205, $L_{201}$ to $L_{209}$ may each independently be *—O—*', *—S—*', a substituted or unsubstituted $C_5$-$C_{60}$ carbocyclic group or a substituted or unsubstituted $C_1$-$C_{60}$ heterocyclic group, xa1 to xa9 may each independently be an integer from 0 to 5, $R_{201}$ to $R_{206}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent aromatic condensed polycyclic group, a substituted or unsubstituted monovalent aromatic condensed heteropolycyclic group, a substituted or unsubstituted monovalent non-aromatic condensed polycyclic group, and a substituted or unsubstituted monovalent non-aromatic condensed heteropolycyclic group, and two adjacent groups $R_{201}$ to $R_{206}$ may optionally be bound to each other via a single bond, a dimethyl-methylene group, or a diphenyl-methylene group.

In some embodiments, $L_{201}$ to $L_{209}$ may be a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone (dibenzothiophene sulfone) group, a carbazole group, a dibenzosilole group, an indenocarbazole group, an indolocarbazole group, a benzofurocarbazole group, a benzothienocarbazole group or a triindolobenzene group, each unsubstituted or substituted with at least one of deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —Si($Q_{11}$)($Q_{12}$)($Q_{13}$), or any combination thereof, xa1 to xa9 may each independently be 0, 1, or 2, and $R_{201}$ to $R_{206}$ may each independently be a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an indenocarbazolyl group, an indolocarbazolyl group, a benzofurocarbazolyl group, or a benzothienocarbazolyl group, each unsubstituted or substituted with at least one of deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), —N($Q_{31}$)($Q_{32}$), or any combination thereof, wherein $Q_{11}$ to $Q_{13}$ and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

According to an embodiment, the hole transport region 12 may include a carbazole-containing amine-based compound.

In one or more embodiments, the hole transport region 12 may include a carbazole-containing amine-based compound and a carbazole-free amine-based compound.

The carbazole-containing amine-based compound may be, for example, a compound represented by Formula 201 including a carbazole group and further including at least one of a dibenzofuran group, a dibenzothiophene group, a fluorene group, a spirofluorene group, an indenocarbazole group, an indolocarbazole group, a benzofurocarbazole group, a benzothienocarbazole group, or any combination thereof.

The carbazole-free amine-based compound may be, for example, compounds represented by Formula 201 not including a carbazole group and including at least one of a dibenzofuran group, a dibenzothiophene group, a fluorene group, a spirofluorene group, an indenocarbazole group, an indolocarbazole group, a benzofurocarbazole group, a benzothienocarbazole group, or any combination thereof.

In one or more embodiments, the hole transport region 12 may include at least one compound represented by Formula 201, 202, or a combination thereof.

In an embodiment, the hole transport region 12 may include at least one compound represented by Formulae 201-1, 202-1, 201-2, or any combination thereof, but embodiments are not limited thereto:

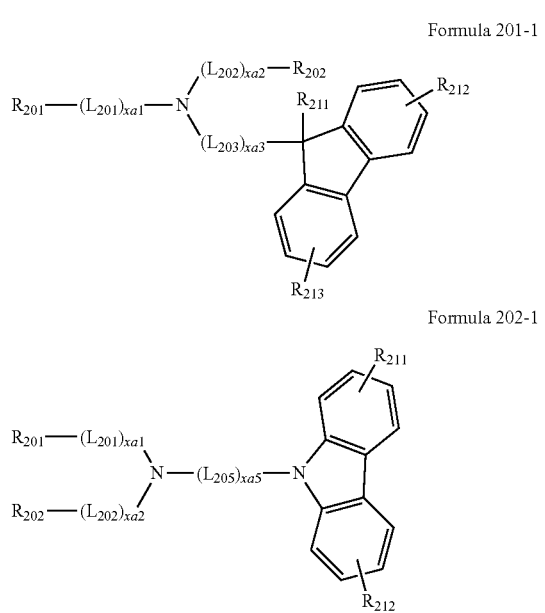

Formula 201-1

Formula 202-1

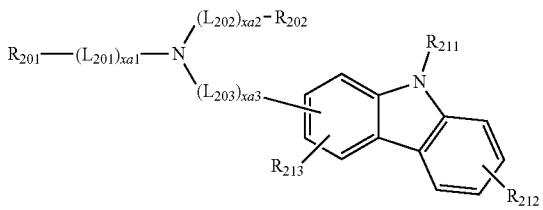

Formula 201-2 wherein in Formulae 201-1, 202-1, and 201-2, $L_{201}$ to $L_{203}$, $L_{205}$, xa1 to xa3, xa5, $R_{201}$, and $R_{202}$ may respectively be understood by referring to the descriptions of $L_{201}$ to $L_{203}$, $L_{205}$, xa1 to xa3, xa5, $R_{201}$, and $R_{202}$ provided herein, and $R_{211}$ to $R_{213}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a dimethylfluorenyl group, a diphenylfluorenyl group, a triphenylenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group.

In some embodiments, the hole transport region 12 may include at least one of Compounds HT1 to HT39, but embodiments are not limited thereto:

HT1

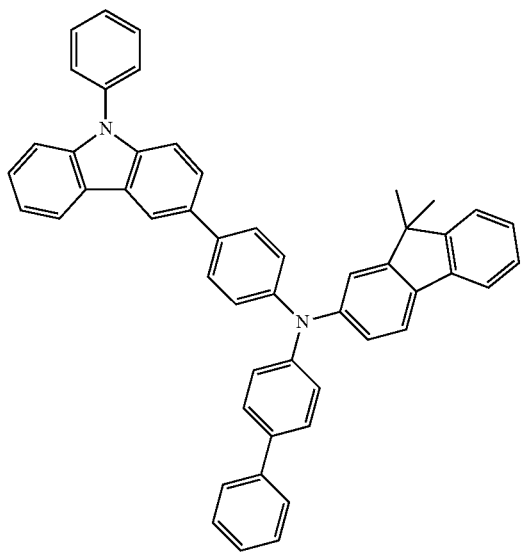

HT2

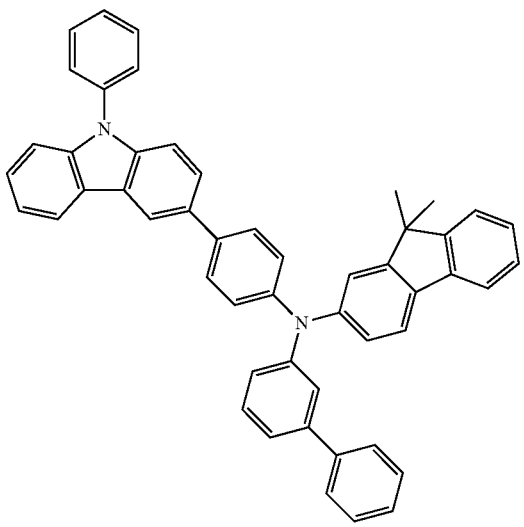

-continued
HT3
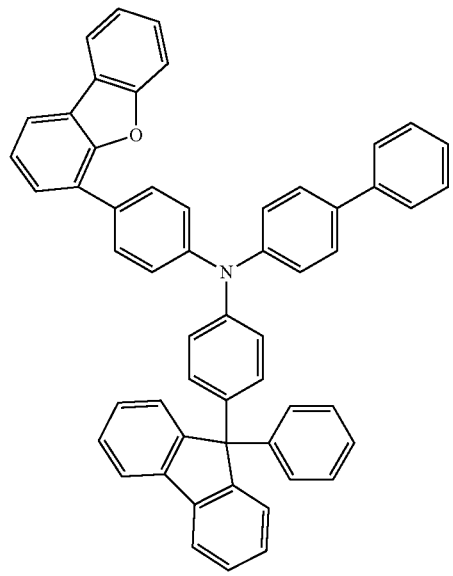
HT4
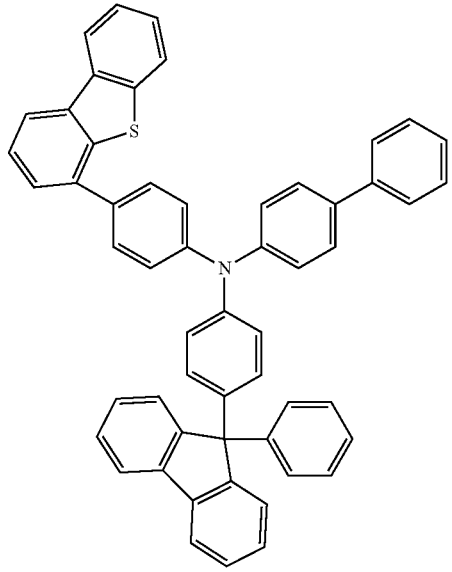
HT5
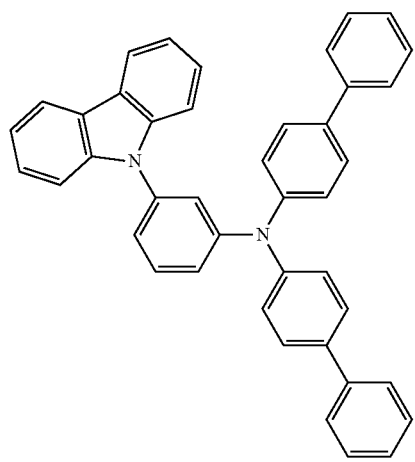
HT6
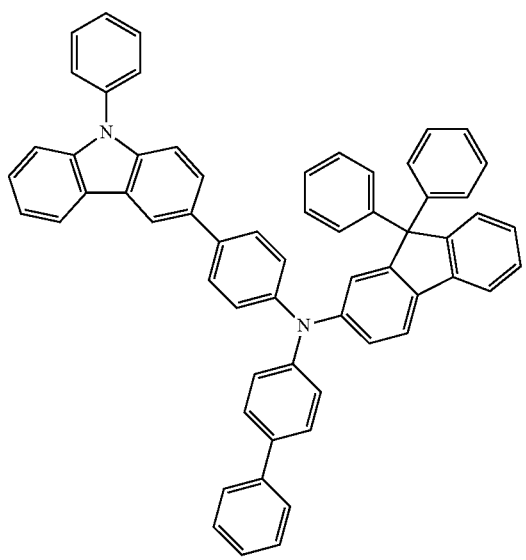

-continued
| HT7 | HT8 |
|---|---|
| 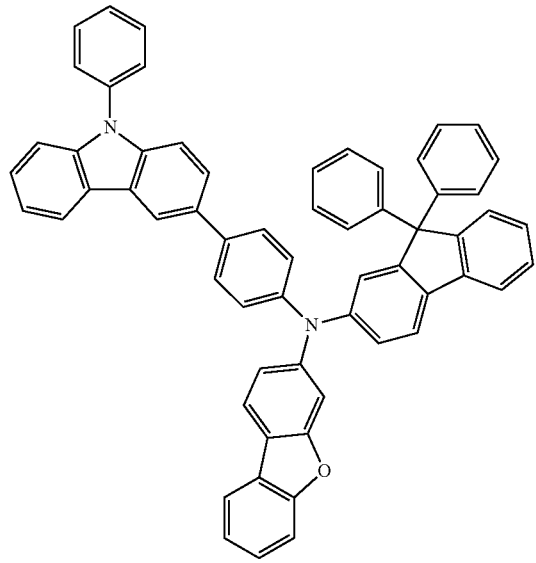 | 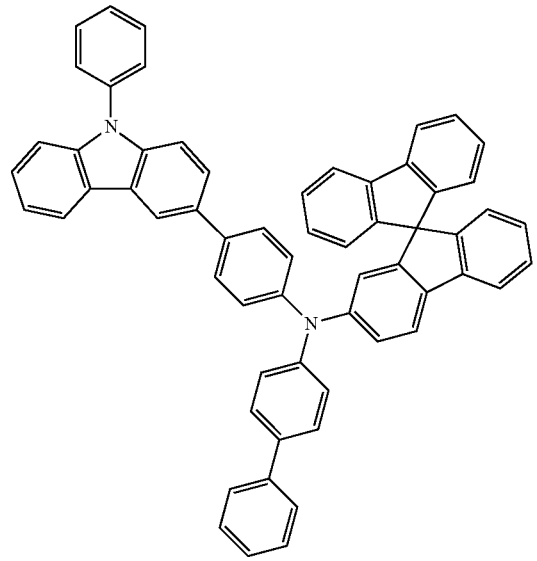 |
| HT9 | HT10 |
| 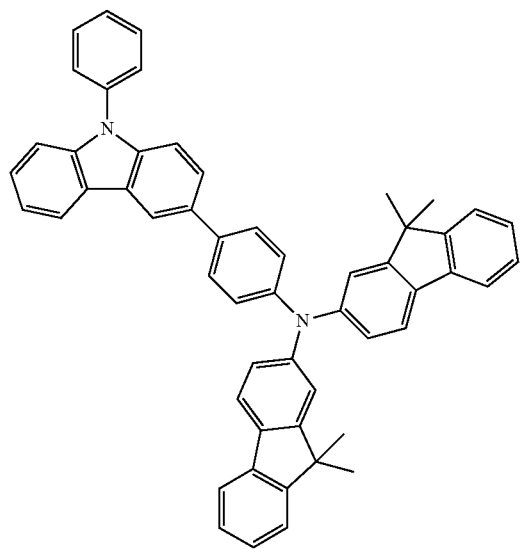 | 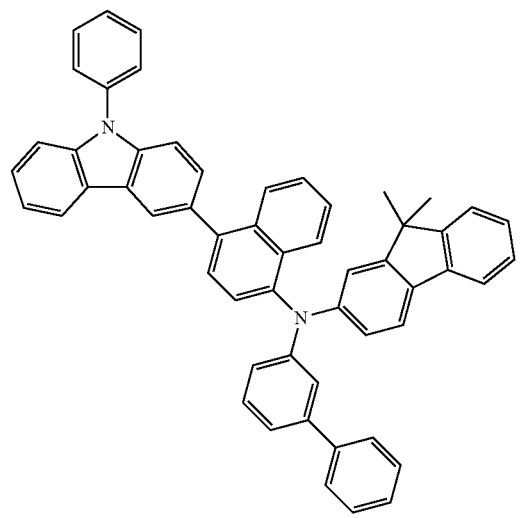 |
| HT11 | HT12 |
| 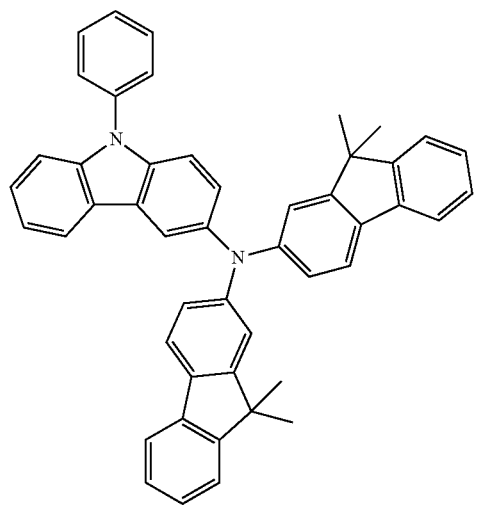 | 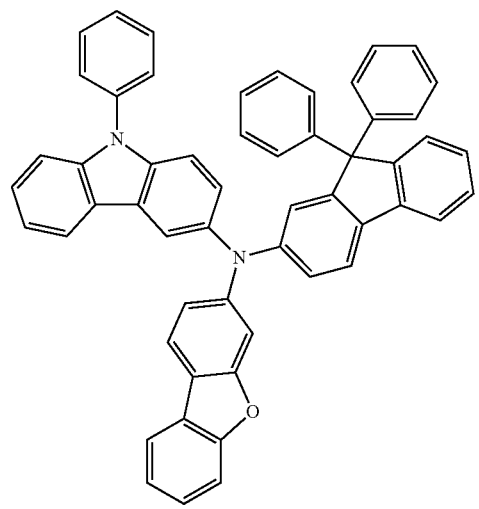 |

-continued
HT13
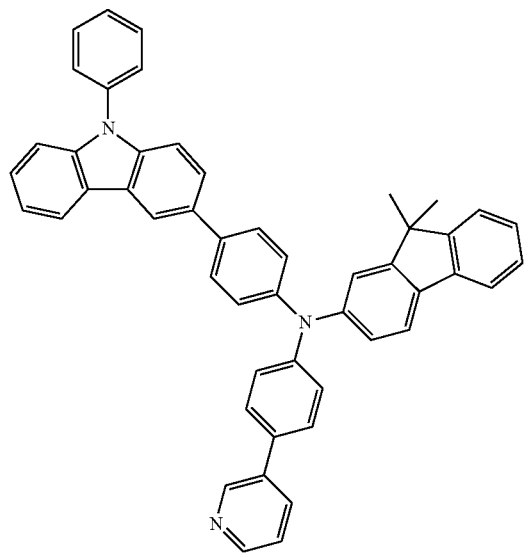
HT14
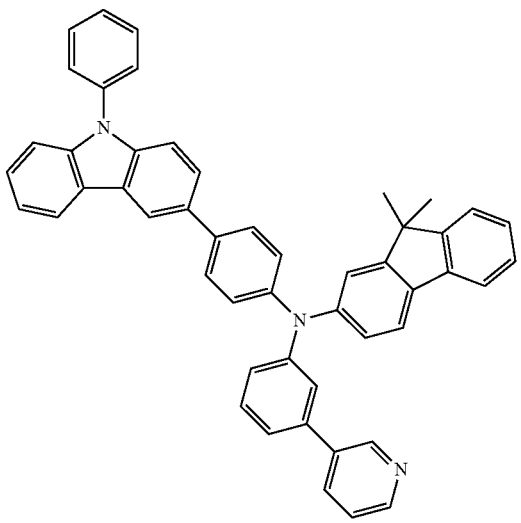
HT15
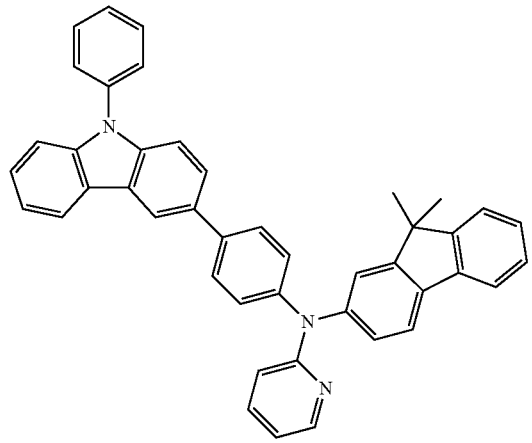
HT16
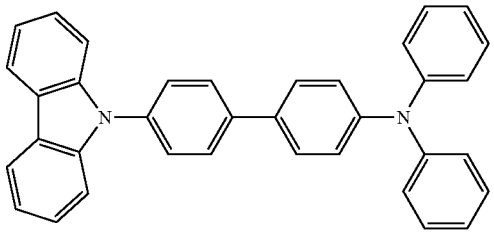
HT17
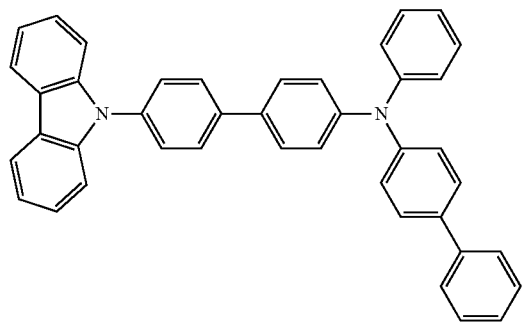
HT18
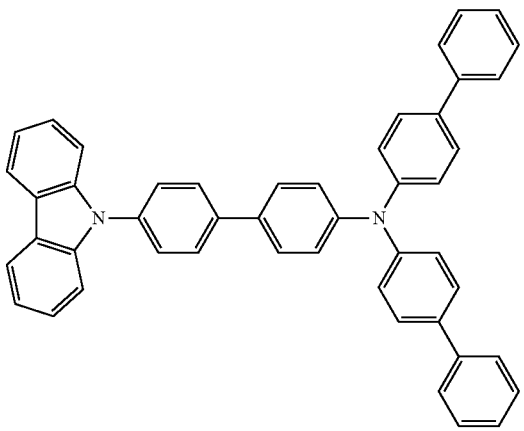

-continued
HT19
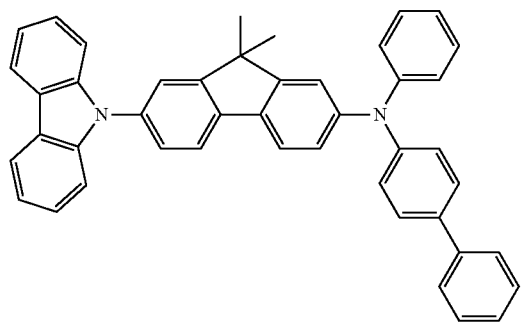
HT20
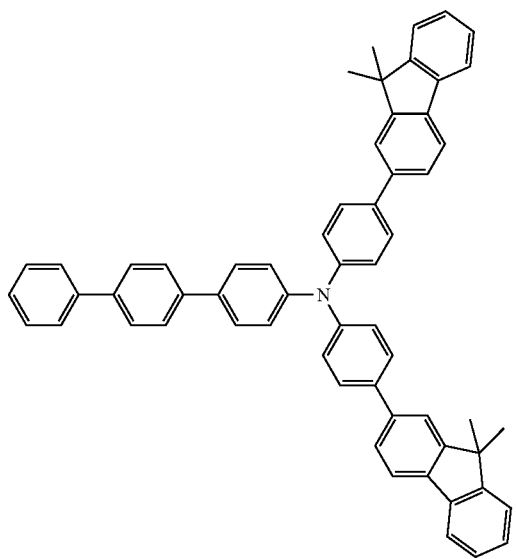
HT21
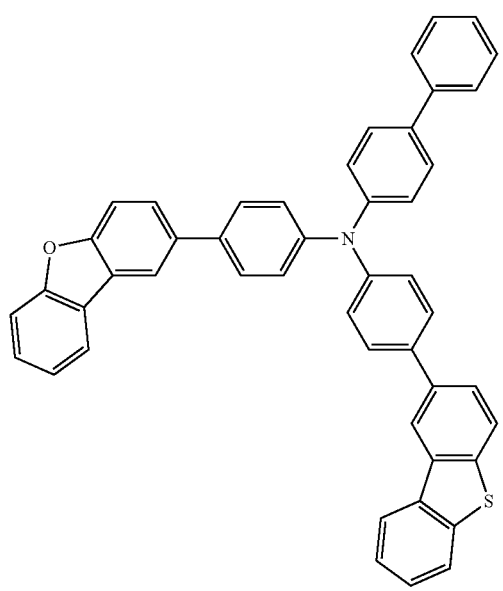
HT22
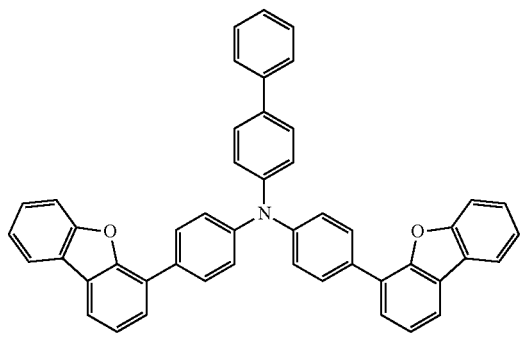
HT23
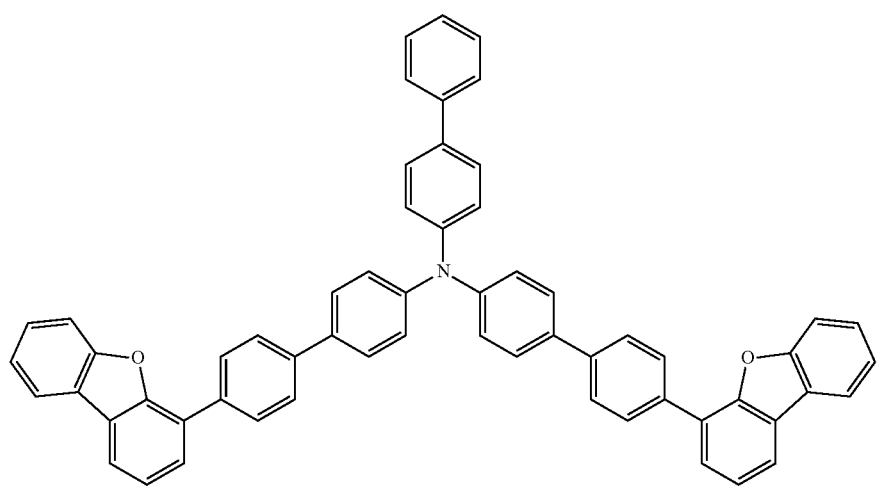

-continued
HT24
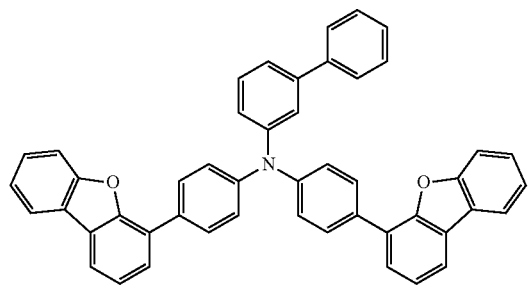
HT25
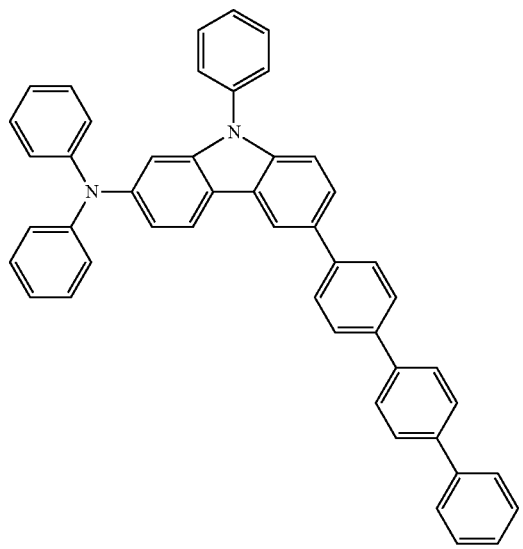
HT26
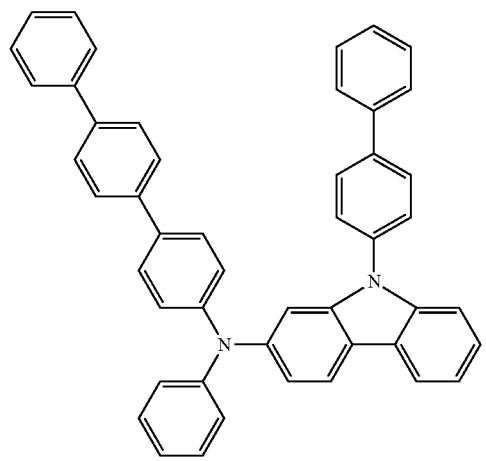
HT27
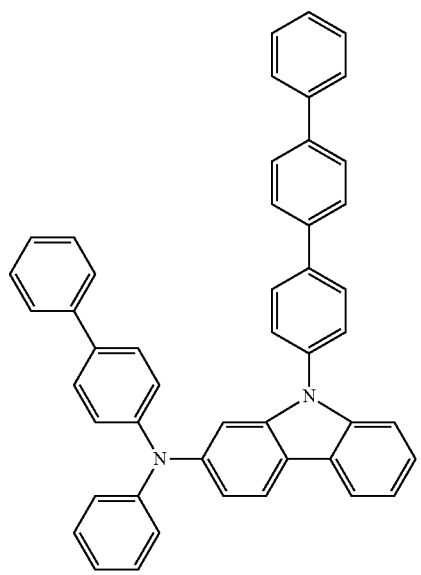
HT28
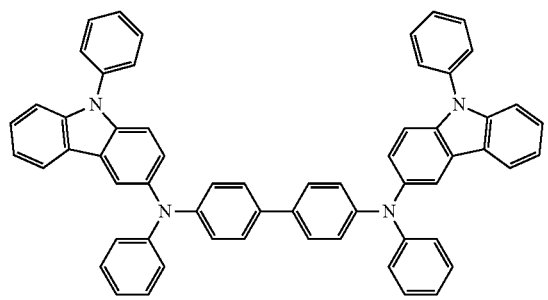
HT29
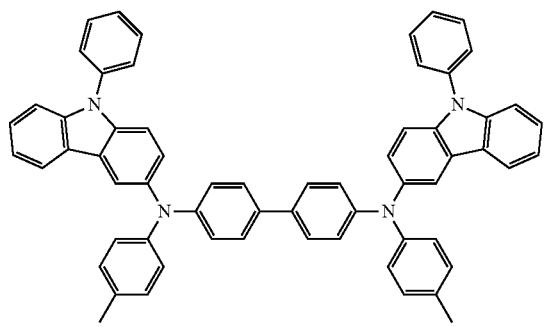

-continued
HT30
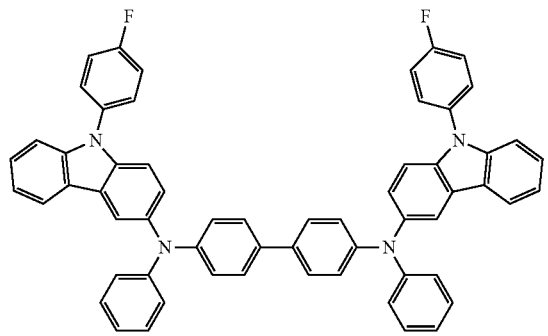
HT31
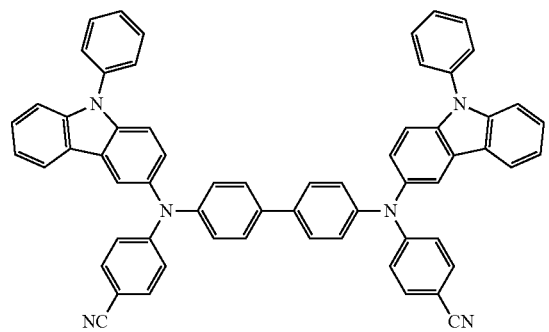
HT32
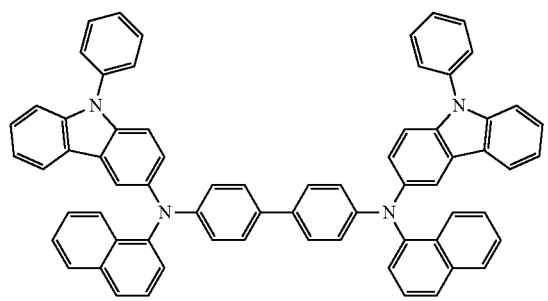
HT33
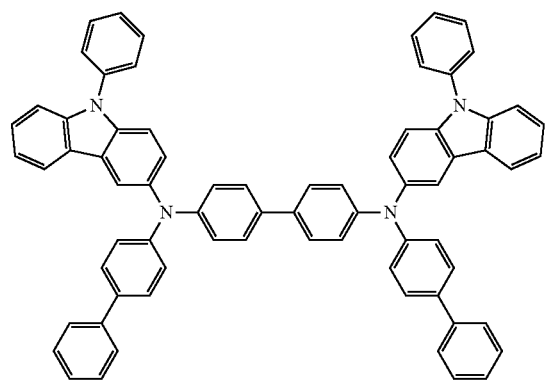
HT34
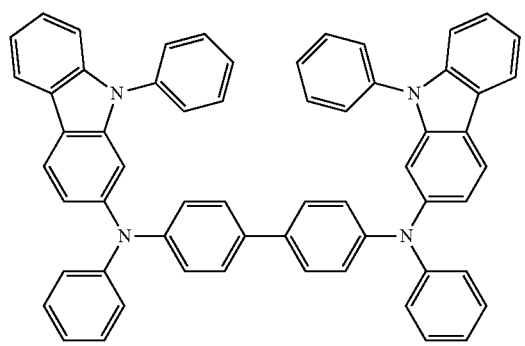
HT35
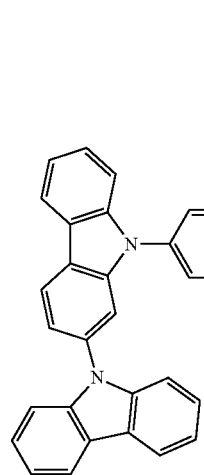

-continued

HT36
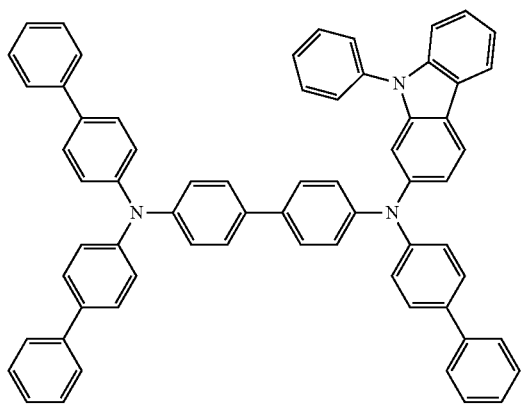

HT37
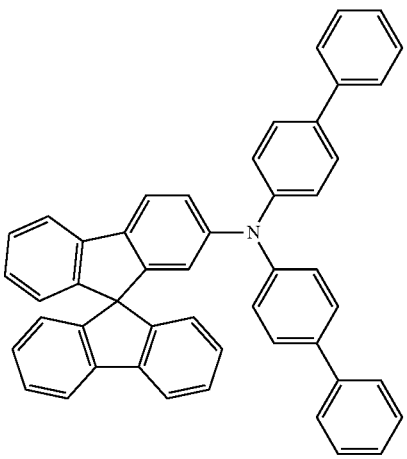

HT38
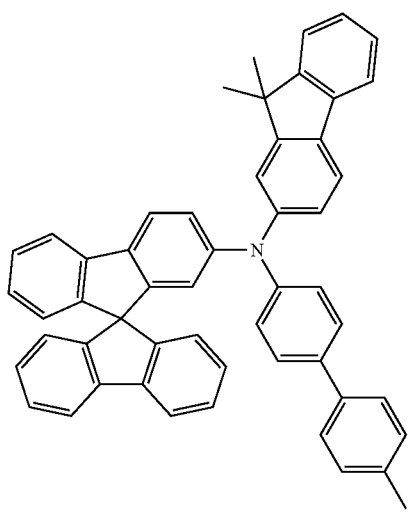

HT39
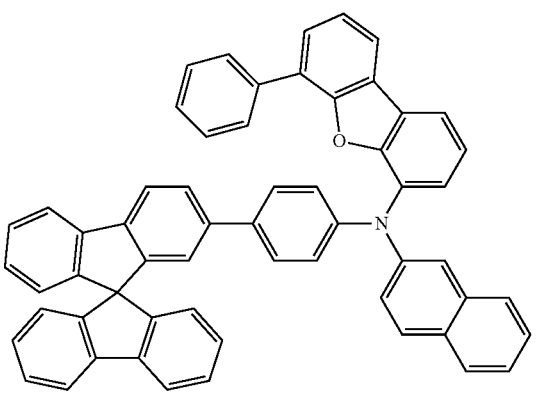

TAPC
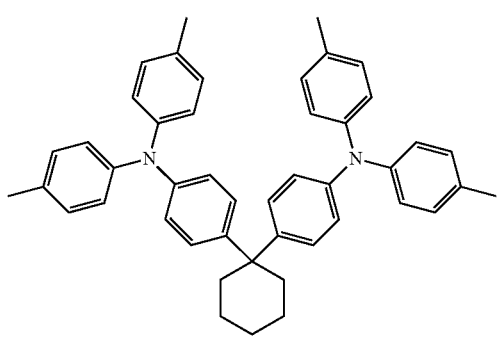

TCTA
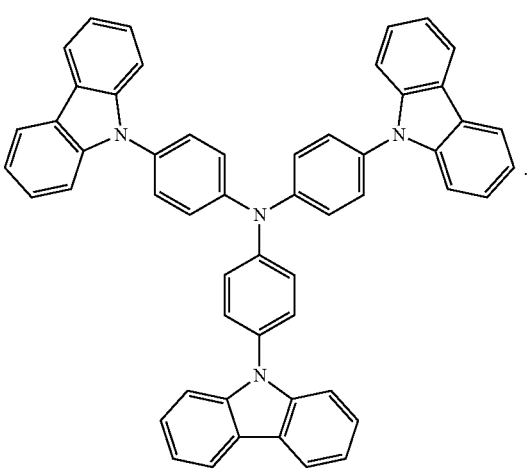

In some embodiments, the hole transport region may include at least one compound of 4,4'-cyclohexylidenebis [N,N-bis(4-methylphenyl)benzenamine] (TAPC), tris(4-carbazoyl-9-ylphenyl)amine (TCTA), or any combination thereof.

The hole transport region 12 of the organic light-emitting device 10 may further include a p-dopant. When the hole transport region 12 further includes a p-dopant, the hole transport region 12 may have a structure including a matrix (for example, at least one compound represented by Formulae 201 to 205) and a p-dopant included in the matrix. The p-dopant may be homogeneously or non-homogeneously doped in the hole transport region 12.

In some embodiments, a LUMO energy level of the p-dopant may be about-3.5 eV or less.

The p-dopant may include at least one of a quinone derivative, a metal oxide, a cyano group-containing compound, or any combination thereof, but embodiments are not limited thereto.

In some embodiments, the p-dopant may include:
- a quinone derivative such as tetracyanoquinodimethane (TCNQ), 2,3,5,6-tetrafluoro-7,7,8,8-tetracyanoquinodimethane (F4-TCNQ), or F6-TCNNQ;
- a metal oxide such as tungsten oxide or molybdenum oxide;
- 1,4,5,8,9,12-hexaazatriphenylene-hexacarbonitrile (HAT-CN); and
- a compound represented by Formula 221, but embodiments are not limited thereto:

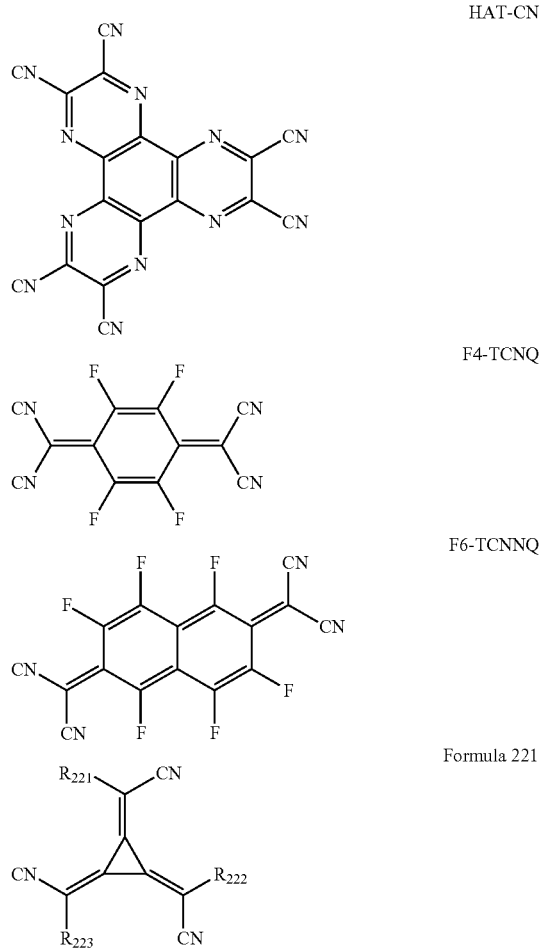

wherein, in Formula 221,
$R_{221}$ to $R_{223}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent aromatic condensed polycyclic group, a substituted or unsubstituted monovalent aromatic condensed heteropolycyclic group, a substituted or unsubstituted monovalent non-aromatic condensed polycyclic group, or a substituted or unsubstituted monovalent non-aromatic condensed heteropolycyclic group, wherein at least one $R_{221}$ to $R_{223}$ may include at least one a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, a $C_1$-$C_{20}$ alkyl group substituted with —I, or any combination thereof.

A thickness of the hole transport region 12 may be in a range of about 100 Angstroms (Å) to about 10,000 Å, for example, about 400 Å to about 2,000 Å, and a thickness of the emission layer 15 may be in a range of about 100 Å to about 3,000 Å, for example, about 300 Å to about 1,000 Å. When the thicknesses of the hole transport region 12 and the emission layer 15 are within any of these ranges, satisfactory hole transporting characteristics and/or luminescence characteristics may be obtained without a substantial increase in driving voltage.

Electron Transport Region 17

In the organic light-emitting device 10, the electron transport region 17 may be between the emission layer 15 and the second electrode 19.

The electron transport region 17 may have a single-layered structure or a multi-layered structure.

For example, the electron transport region 17 may have a structure of electron transport layer, a structure of electron transport layer/electron injection layer, a structure of buffer layer/electron transport layer, a structure of hole blocking layer/electron transport layer, a structure of buffer layer/electron transport layer/electron injection layer, or a structure of hole blocking layer/electron transport layer/electron injection layer, but embodiments are not limited thereto. The electron transport region 17 may include an electron control layer.

The electron transport region 17 may include a known electron transport material.

The electron transport region 17 (for example, the buffer layer, the hole blocking layer, the electron control layer, or the electron transport layer in the electron transport region 17) may include a metal-free compound including at least one π electron-depleted nitrogen-containing cyclic group. The π electron-depleted nitrogen-containing cyclic group may be understood by referring to the description for those provided herein.

In some embodiments, the electron transport region may include a compound represented by Formula 601:

$$[Ar_{601}]_{xe11}-[(L_{601})_{xe1}-R_{601}]_{xe21}$$  Formula 601 wherein, in Formula 601,
$Ar_{601}$ and $L_{601}$ may each independently be a substituted or unsubstituted $C_5$-$C_{60}$ carbocyclic group or a substituted or unsubstituted $C_1$-$C_{60}$ heterocyclic group,
xe11 may be 1, 2, or 3,
xe1 may be an integer from 0 to 5,
$R_{601}$ may be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent aromatic condensed polycyclic group, a substituted or unsubstituted monovalent aromatic condensed heteropolycyclic group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In some embodiments, at least one $Ar_{601}$(s) in the number of xe11 and $R_{601}$(s) in the number of xe21 may include the π electron-depleted nitrogen-containing cyclic group.

In some embodiments, in Formula 601, ring $Ar_{601}$ and $L_{601}$ may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), —P(=O)($Q_{31}$)($Q_{32}$), or any combination thereof, wherein $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

When xe11 in Formula 601 is 2 or greater, at least two $Ar_{601}$(s) may be bound via a single bond.

In one or more embodiments, $Ar_{601}$ in Formula 601 may be an anthracene group.

In some embodiments, the compound represented by Formula 601 may be represented by Formula 601-1:

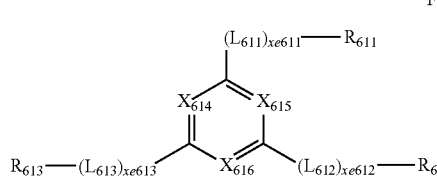

Formula 601-1 wherein, in Formula 601-1, $X_{614}$ may be N or C($R_{614}$), $X_{615}$ may be N or C($R_{615}$), $X_{616}$ may be N or C($R_{616}$), at least one $X_{614}$ to $X_{616}$ may be N, $L_{611}$ to $L_{613}$ may each independently be understood by referring to the description of $L_{601}$ provided herein, xe611 to xe613 may each independently be understood by referring to the description of xe1 provided herein, $R_{611}$ to $R_{613}$ may each independently be understood by referring to the description of $R_{601}$ provided herein, and $R_{614}$ to $R_{616}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, or a naphthyl group.

In one or more embodiments, in Formulae 601 and 601-1, xe1 and xe611 to xe613 may each independently be 0, 1, or 2.

In one or more embodiments, in Formulae 601 and 601-1, $R_{601}$ and $R_{611}$ to $R_{613}$ may each independently be: a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, or any combination thereof; or —S(=O)$_2$(Q$_{601}$) or —P(=O)(Q$_{601}$)(Q$_{602}$), wherein Q$_{601}$ and Q$_{602}$ may respectively be understood by referring to the descriptions of Q$_{601}$ and Q$_{602}$ provided herein.

The electron transport region may include at least one compound of Compounds ET1 to ET36, but embodiments are not limited thereto:

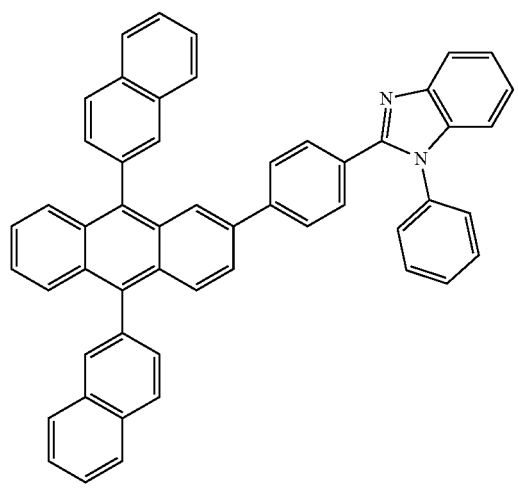

ET1

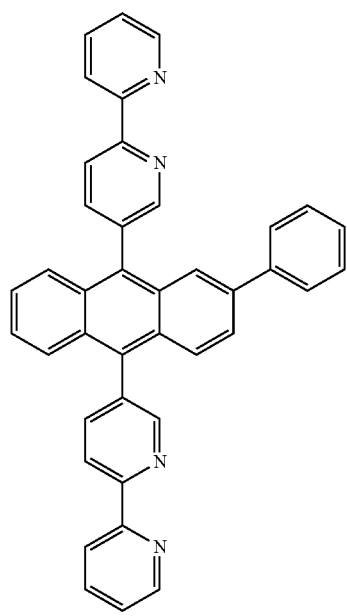

ET2

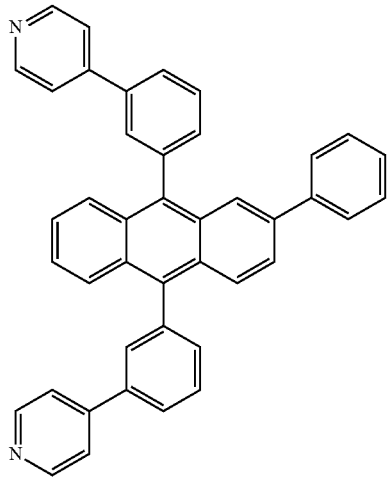

ET3

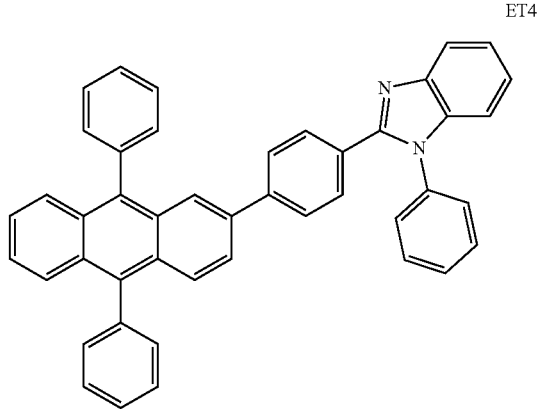

ET4

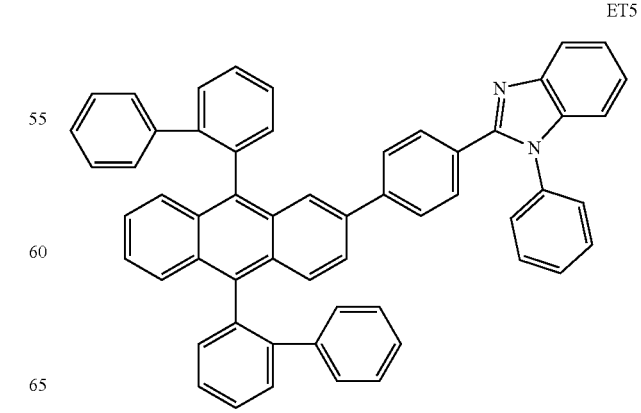

ET5

ET6
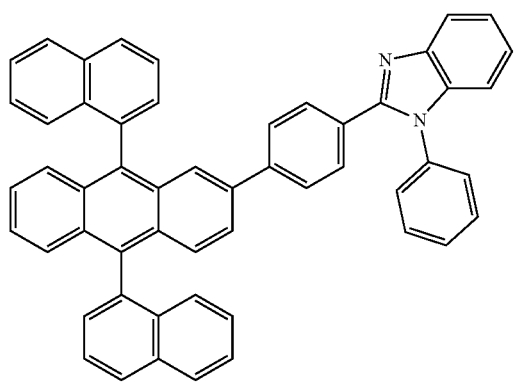
ET7
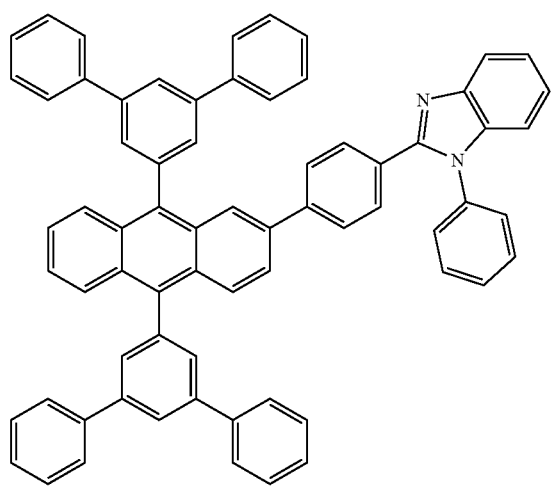
ET8
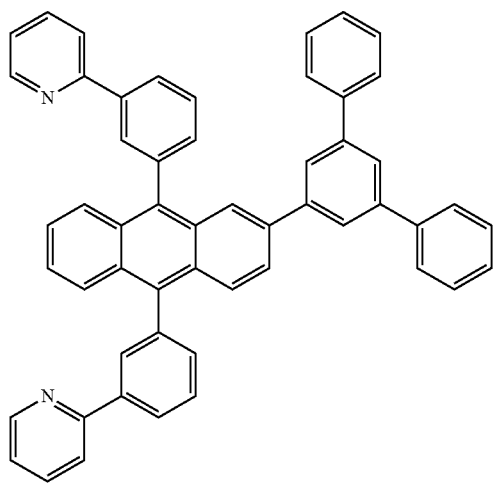
ET9
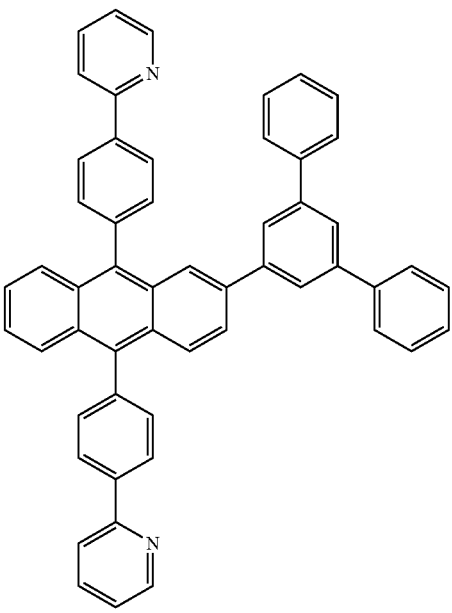
ET10
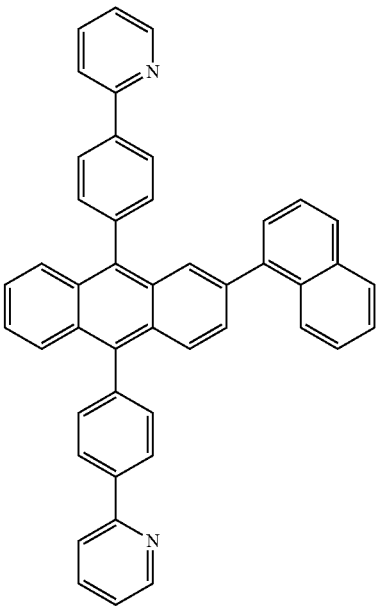

ET11
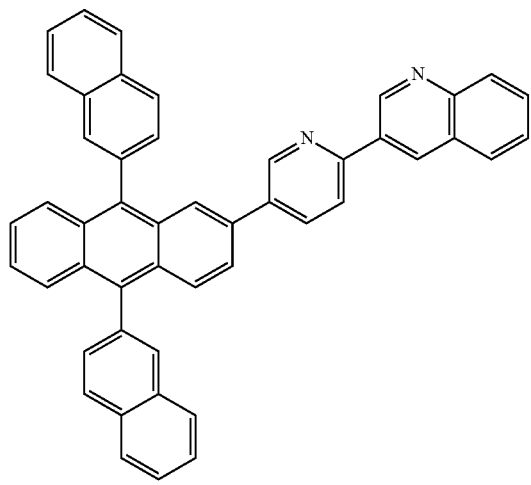
ET12
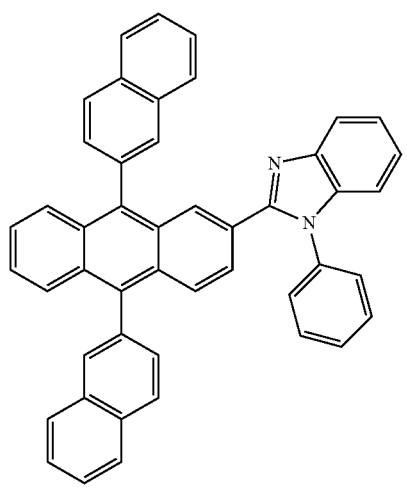
ET13
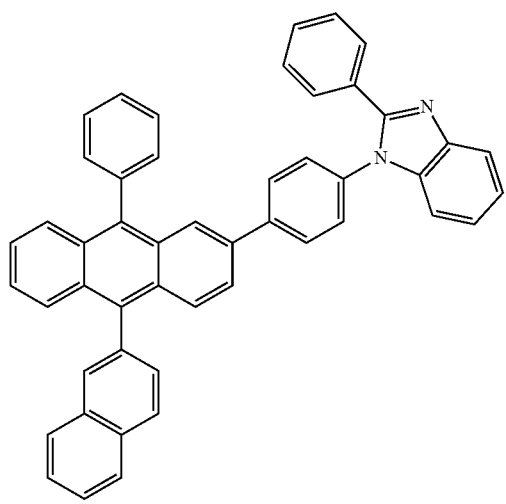
ET14
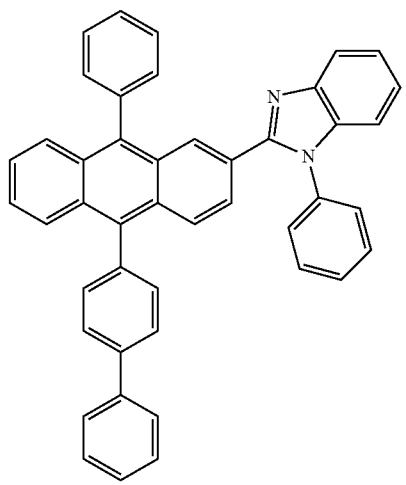
ET15
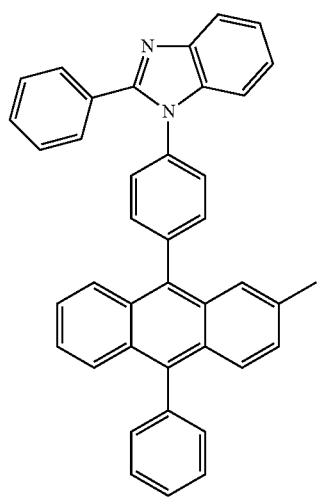
ET16
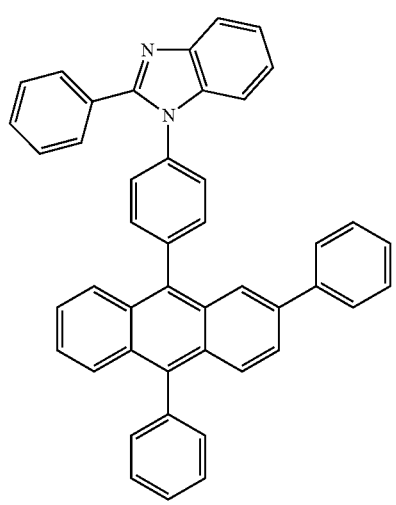

ET17
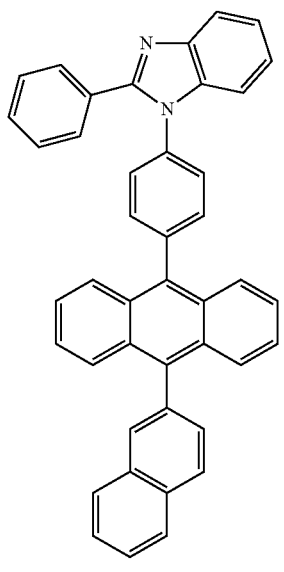
ET18
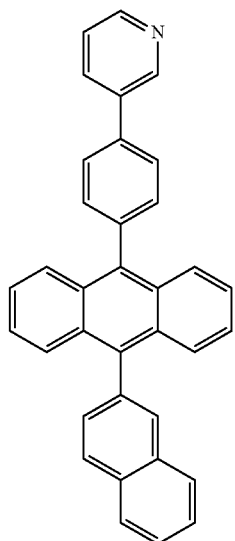
ET19
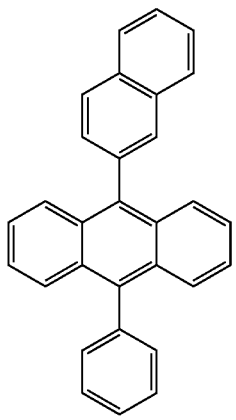
ET20
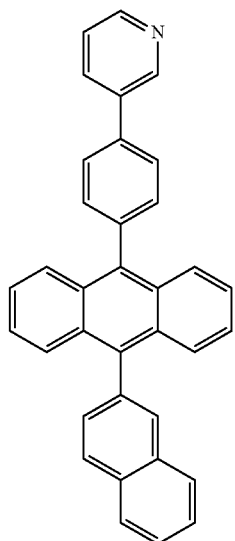
ET21
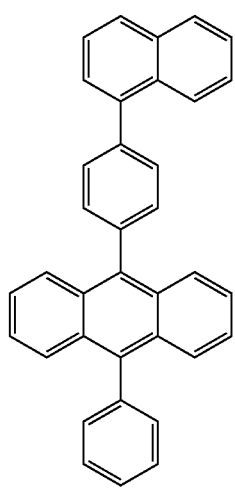
ET22
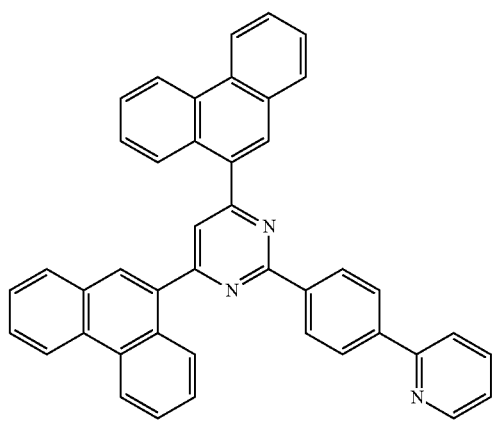

ET23
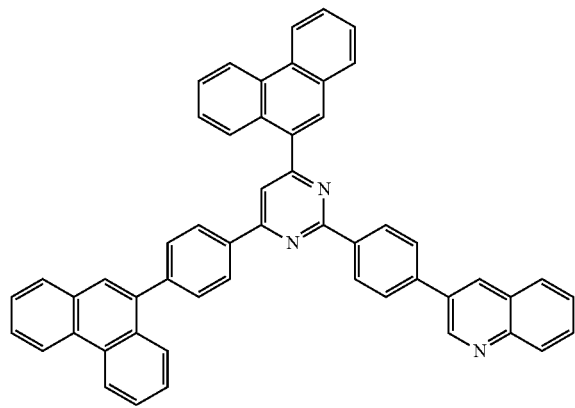
ET24
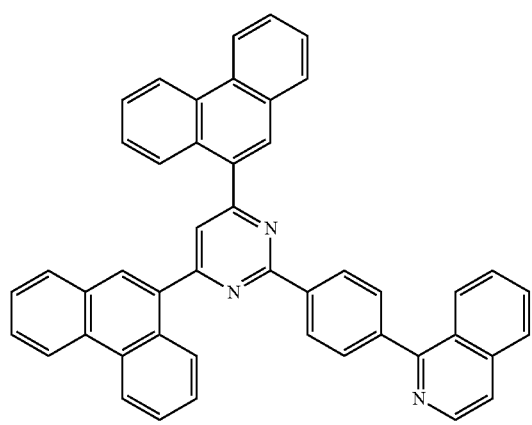
ET25
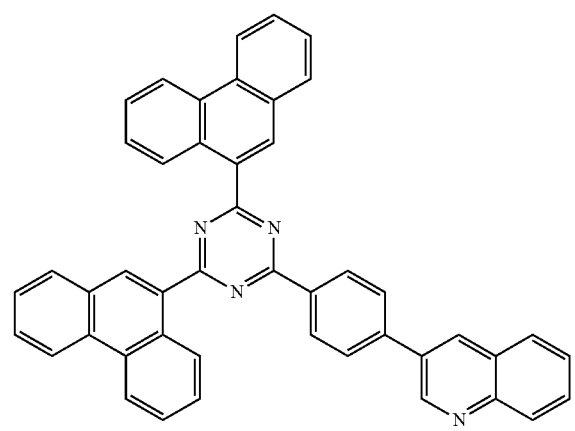
ET26
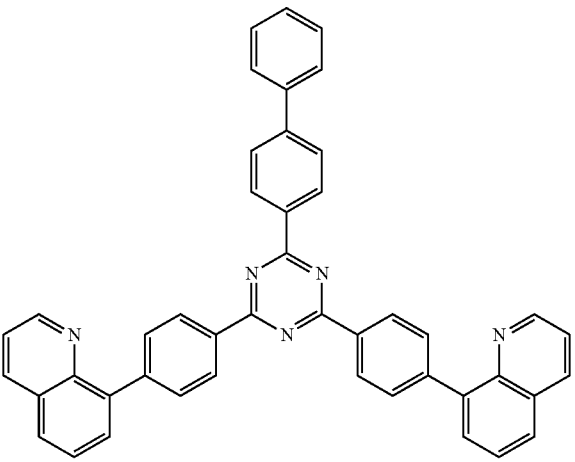
ET27
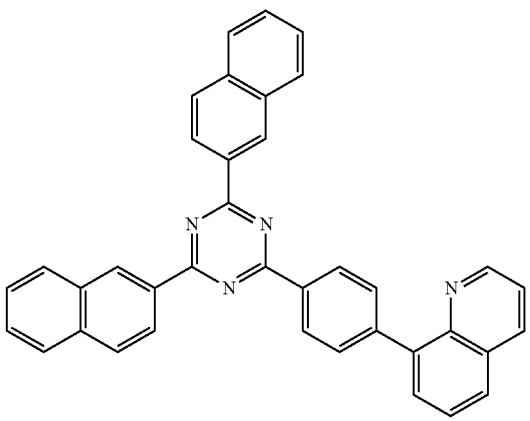
ET28
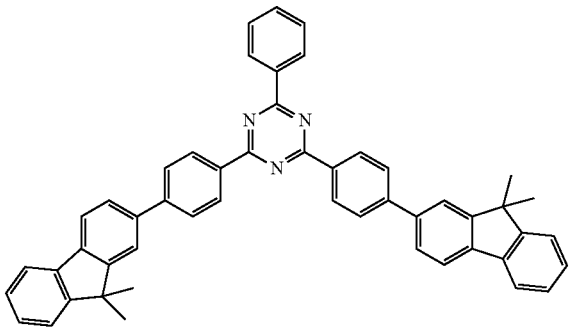

-continued
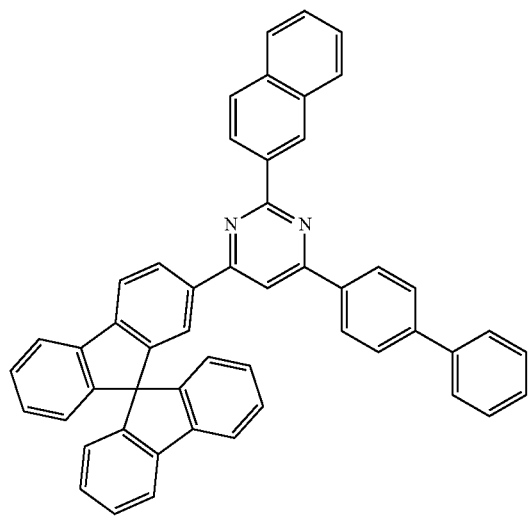
ET29
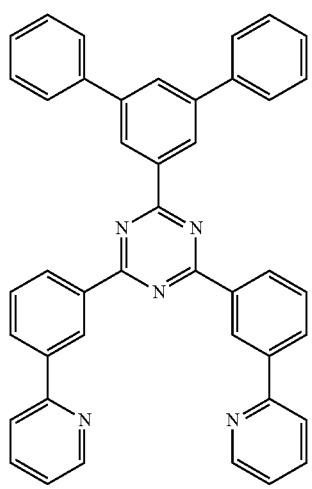
ET30
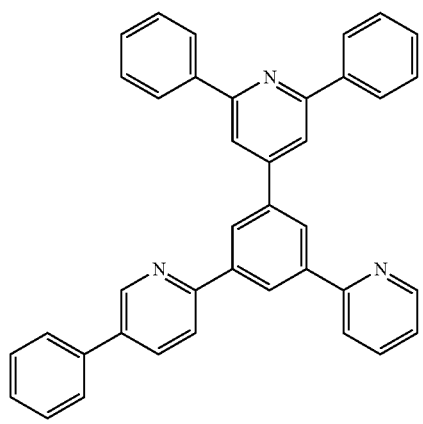
ET31
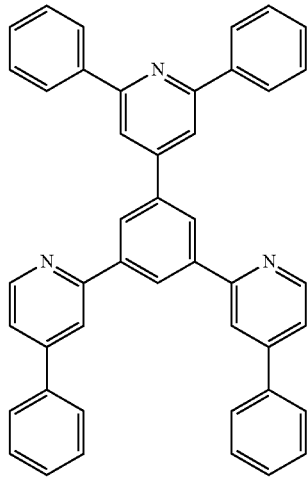
ET32
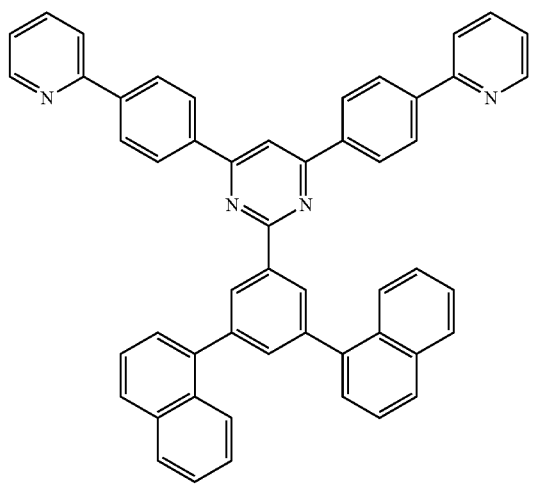
ET33
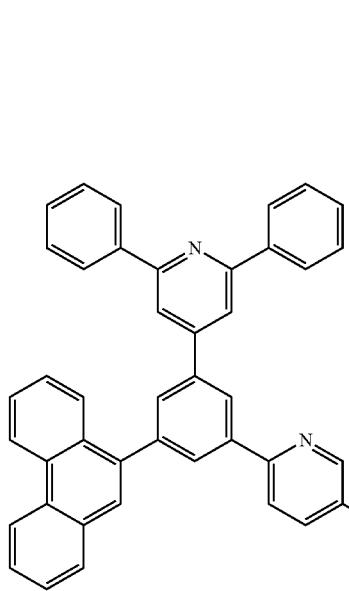
ET34

-continued

ET35

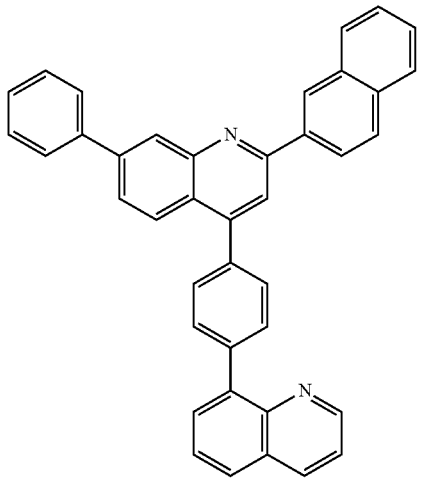

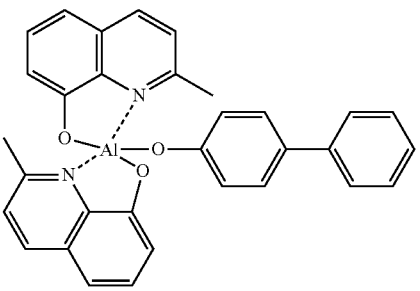

BAlq

TAZ

ET36

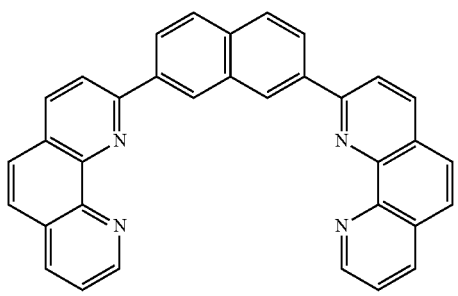

NTAZ

TPBi

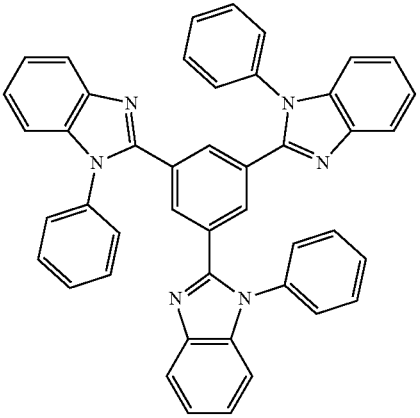

In some embodiments, the electron transport region may include at least one compound of 2,9-dimethyl-4,7-diphenyl-1,10-phenanthroline (BCP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), 2,2',2"-(1,3,5-benzinetriyl)-tris(1-phenyl-1-H-benzimidazole) (TPBi), NTAZ, or any combinations thereof:

Alq$_3$

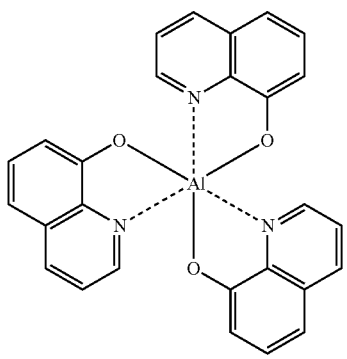

The thicknesses of the buffer layer, the hole blocking layer, or the electron control layer may each independently be in a range of about 20 Å to about 1,000 Å, and in some embodiments, about 30 Å to about 300 Å. When the thicknesses of the buffer layer, the hole blocking layer or the electron control layer are within any of these ranges, excellent hole blocking characteristics or excellent electron controlling characteristics may be obtained without a substantial increase in driving voltage.

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport region 17 (e.g., the electron transport layer in the electron transport region 17) may further include, in addition to the materials described above, a material including metal.

The metal-containing material may include at least one an alkali metal complex, an alkaline earth metal complex, or any combination thereof. The alkali metal complex may include a metal ion of a lithium (Li) ion, a sodium (Na) ion, a potassium (K) ion, a rubidium (Rb) ion, a cesium (Cs) ion, or any combination thereof. The alkaline earth metal complex may include a metal ion a beryllium (Be) ion, a magnesium (Mg) ion, a calcium (Ca) ion, a strontium (Sr) ion, a barium (Ba) ion, or any combination thereof. Each ligand coordinated with the metal ion of the alkali metal complex and the alkaline earth metal complex may independently be hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, or cyclopentadiene, but embodiments are not limited thereto.

For example, the metal-containing material may include a Li complex. The Li complex may include, e.g., Compound ET-D1 (LiQ) or Compound ET-D2:

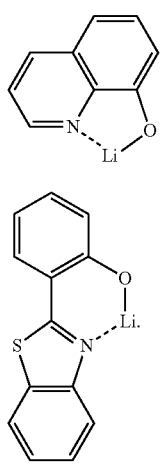

ET-D1

ET-D2

The electron transport region 17 may include an electron injection layer that facilitates injection of electrons from the second electrode 19. The electron injection layer may be in direct contact with the second electrode 19.

The electron injection layer may have i) a single-layered structure consisting of a single layer consisting of a single material, ii) a single-layered structure consisting of a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be Li, Na, K, Rb, or Cs. In some embodiments, the alkali metal may be Li, Na, or Cs. In one or more embodiments, the alkali metal may be Li or Cs, but embodiments are not limited thereto.

The alkaline earth metal may be Mg, Ca, Sr, or Ba.

The rare earth metal may be Sc, Y, Ce, Tb, Yb, or Gd.

The alkali metal compound, the alkaline earth metal compound, and the rare earth metal compound may each independently be an oxide and a halides (e.g., fluorides, chlorides, bromides, or iodides) of the alkali metal, the alkaline earth metal, and the rare earth metal, respectively.

The alkali metal compound may be alkali metal oxides, such as $Li_2O$, $Cs_2O$, or $K_2O$, and alkali metal halides, such as LiF, NaF, CsF, KF, LiI, NaI, CsI, or KI. In some embodiments, the alkali metal compound may be LiF, $Li_2O$, NaF, LiI, NaI, CsI, or KI, but embodiments are not limited thereto.

The alkaline earth-metal compound may be an alkaline earth-metal compound, such as BaO, SrO, CaO, $Ba_xSr_{1-x}O$ (wherein 0<x<1), or $Ba_xCa_{1-x}O$ (wherein 0<x<1). In some embodiments, the alkaline earth metal compound may be BaO, SrO, or CaO, but embodiments are not limited thereto.

The rare earth metal compound may be $YbF_3$, $ScF_3$, $ScO_3$, $Y_2O_3$, $Ce_2O_3$, $GdF_3$, or $TbF_3$. In some embodiments, the rare earth metal compound may be $YbF_3$, $ScF_3$, $TbF_3$, $YbI_3$, $ScI_3$, or $TbI_3$, but embodiments are not limited thereto.

The alkali metal complex, the alkaline earth metal complex, and the rare earth metal complex may each include ions of the above-described alkali metal, alkaline earth metal, and rare earth metal. Each ligand coordinated with the metal ion of the alkali metal complex, the alkaline earth metal complex, and the rare earth metal complex may independently be hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, or cyclopentadiene, but embodiments are not limited thereto.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, as described above. In some embodiments, the electron injection layer may further include an organic material. When the electron injection layer further includes an organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof, the foregoing may be homogeneously or non-homogeneously dispersed in a matrix including the organic material.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

Second Electrode 19

The second electrode 19 may be on the organic layer 10A. In an embodiment, the second electrode 19 may be a cathode that is an electron injection electrode. In this embodiment, a material for forming the second electrode 19 may be a material having a low work function, for example, a metal, an alloy, an electrically conductive compound, or a combination thereof.

The second electrode 19 may include at least one lithium (Li), silver (Ag), magnesium (Mg), aluminum (Al), aluminum-lithium (Al—Li), calcium (Ca), magnesium-indium (Mg—In), magnesium-silver (Mg—Ag), ITO, IZO, or any combination thereof, but embodiments are not limited thereto. The second electrode 19 may be a transmissive electrode, a semi-transmissive electrode, or a reflective electrode.

The second electrode 19 may have a single-layered structure or a multi-layered structure including two or more layers.

Hereinbefore the organic light-emitting device 10 has been described with reference to FIG. 1, but embodiments are not limited thereto.

Figure 3:
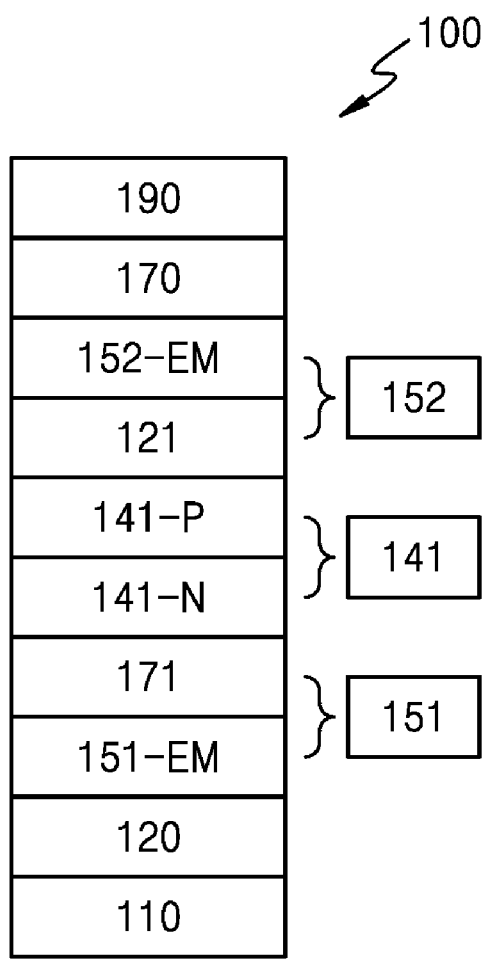
FIG. 3 illustrates a schematic view of an organic light-emitting device 100 according to an exemplary embodiment.

Description of FIG. 3

FIG. 3 is a schematic view of an organic light-emitting device 100 according to an exemplary embodiment.

The organic light-emitting device 100 in FIG. 3 may include a first electrode 110, a second electrode 190 facing the first electrode 110, and a first light-emitting unit 151 and a second light-emitting unit 152 between the first electrode 100 and the second electrode 190. A charge generating layer 141 may be between the first light-emitting unit 151 and the second light-emitting unit 152, and the charge generating layer 141 may include an n-type charge generating layer 141-N and a p-type charge generating layer 141-P. The charge generating layer 141 is a layer serving to generate charges and supply the generated charges to the adjacent light-emitting unit, and may include a known material.

The first light-emitting unit 151 may include a first emission layer 151-EM, and the second light-emitting unit 152 may include a second emission layer 152-EM. A maximum emission wavelength of light emitted by the first light-emitting unit 151 may be different from a maximum emission wavelength of light emitted by the second light-emitting unit 152. For example, mixed light of the light emitted by the first light-emitting unit 151 and the light emitted by the second light-emitting unit 152 may be white light, but embodiments are not limited thereto.

A hole transport region 120 may be between the first light-emitting unit 151 and the first electrode 110, and the second light-emitting unit 152 may include a first hole transport region 121 toward the first electrode 110.

An electron transport region 170 may be between the second light-emitting unit 152 and the second electrode 190, and the first light-emitting unit 151 may include a first electron transport region 171 between the charge generating layer 141 and the first emission layer 151-EM.

In some embodiments, the first emission layer 151-EM may include the heterocyclic compound.

In some embodiments, the second emission layer 152-EM may include the heterocyclic compound.

In FIG. 3, the first electrode 110 and the second electrode 190 may each be understood by referring to the descriptions for the first electrode 110 and the second electrode 19 in FIG. 1, respectively.

In FIG. 3, the first emission layer 151-EM and the second emission layer 152-EM may each be understood by referring to the descriptions for the emission layer 15 in FIG. 3.

In FIG. 3, the hole transport region 120 and the first hole transport region 121 may each be understood by referring to the descriptions for the hole transport region 12 in FIG. 1.

In FIG. 3, the electron transport region 170 and the first electron transport region 171 may each be understood by referring to the descriptions for the electron transport region 17 in FIG. 1.

Hereinbefore, by referring to FIG. 3, the first light-emitting unit 151 and the second light-emitting unit 152 has been described as being included in an organic light-emitting device including an emission layer including the host, the dopant, and the sensitizer described herein. However, the organic light-emitting device 100 in FIG. 3 may be subjected to various modifications, for example, at least one of the first light-emitting unit 151 and the second light-emitting unit 152 of the organic light-emitting device 100 in FIG. 3 may be replaced by any suitable known light-emitting unit, or three or more light-emitting units may be included.

Figure 4:
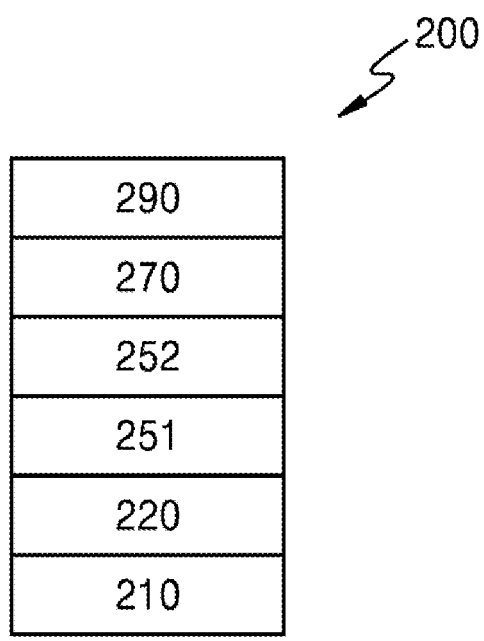
FIG. 4 is a schematic view of an organic light-emitting device 200 according to an exemplary embodiment.

Description of FIG. 4

FIG. 4 is a schematic view of an organic light-emitting device 200 according to an exemplary embodiment.

The organic light-emitting device 100 in FIG. 4 includes a first electrode 210, a second electrode 290 facing the first electrode 210, and a first emission layer 251 and a second emission layer 252 between the first electrode 210 and the second electrode 290.

A maximum emission wavelength of light emitted by the first emission layer 251 may be different from a maximum emission wavelength of light emitted by the second emission layer 252. For example, mixed light of the light emitted by the first emission layer 251 and the light emitted by the second emission layer 252 may be white light, but embodiments are not limited thereto.

A hole transport region 220 may be between the first emission layer 251 and the first electrode 210, and an electron transport region 270 may be between the second emission layer 252 and the second electrode 290.

In some embodiments, the first emission layer 251 may include the heterocyclic compound.

In some embodiments, the second emission layer 252 may include the heterocyclic compound.

In FIG. 4, the first electrode 210, the hole transport region 220, and the second electrode 290 may each be understood by referring to the descriptions for the first electrode 11, the hole transport region 12, and the second electrode 19 in FIG. 1, respectively.

In FIG. 4, the first emission layer 251 and the second emission layer 252 may each be understood by referring to the descriptions for the emission layer 15 in FIG. 1.

In FIG. 4, the electron transport region 170 may be understood by referring to the descriptions for the electron transport region 17 in FIG. 1.

Hereinbefore, by referring to FIG. 4, the first emission layer 251 and the second emission layer 252 has been described as being included in an organic light-emitting device including the heterocyclic compound described herein. However, the organic light-emitting device in FIG. 4 may be subjected to various modifications, for example, one of the first emission layer 251 and the second emission layer 252 may be replaced by any suitable known layer, three or more layers may be included, or an interlayer may be further located between neighboring emission layers.

Electronic Apparatus

The organic light-emitting device may be included in various electronic apparatuses.

The electronic apparatus may further include a thin-film transistor, in addition to the organic light-emitting device. The thin-film transistor may include a source electrode, a drain electrode, and an activation layer, wherein one of the source electrode and the drain electrode may be electrically connected to one of the first electrode and the second electrode of the organic light-emitting device.

General Definitions of Terms

The term "$C_1$-$C_{60}$ alkyl group" as used herein refers to a linear or branched saturated aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is a $C_1$-$C_1$ alkyl group). Examples thereof include a methoxy group, an ethoxy group, and an isopropyloxy group.

The term "$C_2$-$C_{60}$ alkenyl group" as used herein refers to a group formed by placing at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a group formed by placing at least one carbon-carbon triple bond in the middle or at the terminus of the $C_2$-$C_{60}$ alkyl group. Examples thereof include an ethenyl group and a propenyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group including at least one heteroatom of N, O, P, $S_1$, S, B, Se, Ge, Te, or any combination thereof as a ring-forming atom and 1 to 10 carbon atoms. Examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in its ring, wherein the molecular structure as a whole is non-aromatic. Examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group including at least one heteroatom of N, O, P, $S_1$, S, B, Se, Ge, Te, or any combination thereof as a ring-forming atom, 1 to 10 carbon atoms, and at least one double bond in its ring. Examples of the $C_1$-$C_{10}$ heterocycloalkenyl group include a 2,3-dihydrofuranyl group and a 2,3-dihydrothiophenyl group. The term "$C_1$-$C_{10}$ heterocycloalkylene group" as used herein refers to a divalent group having the same structure as the $C_1$-$C_{10}$ heterocycloalkyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the plurality of rings may be fused to each other.

The term "$C_1$-$C_{60}$ heteroaryl group" as used herein refers to a monovalent group having a heterocyclic aromatic system having at least one heteroatom N, O, P, $S_1$, S, B, Se, Ge, Te, or any combination thereof as a ring-forming atom and 1 to 60 carbon atoms. The term "$C_1$-$C_{60}$ heteroarylene group" as used herein refers to a divalent group having a heterocyclic aromatic system having at least one heteroatom N, O, P, $S_1$, S, B, Se, Ge, Te, or any combination thereof as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

The term "$C_6$-$C_{60}$ aryloxy group" as used herein is represented by —$OA_{102}$ (wherein $A_{102}$ is the $C_6$-$C_{60}$ aryl group). The term "$C_6$-$C_{60}$ arylthio group" as used herein is represented by —$SA_{103}$ (wherein $A_{103}$ is the $C_6$-$C_{60}$ aryl group).

The term "monovalent aromatic condensed polycyclic group" as used herein refers to a monovalent group having two or more rings condensed and only carbon atoms (for example, the number of carbon atoms may be in a range of 8 to 60) as ring-forming atoms, wherein the molecular structure as a whole is aromatic. The term "divalent aromatic condensed polycyclic group" as used herein refers to a divalent group having substantially the same structure as the monovalent aromatic condensed polycyclic group.

The term "monovalent aromatic condensed heteropolycyclic group" as used herein refers to a monovalent group having at least two rings condensed and a heteroatom N, O, P, Si, S, B, Se, Ge, Te, or any combination thereof as well as carbon atoms (for example, the number of carbon atoms may be in a range of 1 to 60) as ring-forming atoms, wherein the molecular structure as a whole is aromatic. The term "divalent aromatic condensed heteropolycyclic group" as used herein refers to a divalent group having substantially the same structure as the monovalent aromatic condensed heteropolycyclic group.

The term "monovalent non-aromatic condensed polycyclic group" as used herein refers to a monovalent group having two or more rings condensed and only carbon atoms (for example, the number of carbon atoms may be in a range of 8 to 60) as ring-forming atoms, wherein the molecular structure as a whole is non-aromatic. Examples of the non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group having at least two rings condensed and a heteroatom N, O, P, Si, S, B, Se, Ge, Te, or any combination thereof as well as carbon atoms (for example, the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

The term "$C_5$-$C_{30}$ carbocyclic group" as used herein refers to a saturated or unsaturated cyclic group including 5 to 30 carbon atoms only as ring-forming atoms. The $C_5$-$C_{30}$ carbocyclic group may be a monocyclic group or a polycyclic group. Depending on formula structure, the $C_5$-$C_{30}$ carbocyclic group may be monovalent, divalent, trivalent, quadrivalent, pentavalent, or hexavalent.

The term "$C_1$-$C_{30}$ heterocyclic group" as used herein refers to saturated or unsaturated cyclic group including 1 to 30 carbon atoms and at least one heteroatom N, O, P, Si, S, B, Se, Ge, Te, or any combination thereof as ring-forming atoms. The $C_1$-$C_{30}$ heterocyclic group may be a monocyclic group or a polycyclic group. Depending on formula structure, the $C_1$-$C_{30}$ heterocyclic group may be monovalent, divalent, trivalent, quadrivalent, pentavalent, or hexavalent.

A substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent aromatic condensed polycyclic group, the substituted monovalent aromatic condensed heteropolycyclic group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, monovalent aromatic condensed polycyclic group, monovalent aromatic condensed heteropolycyclic group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), —P(=O)($Q_{18}$)($Q_{19}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent aromatic condensed polycyclic group, a monovalent aromatic condensed heteropolycyclic group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent aromatic condensed polycyclic group, a monovalent aromatic condensed heteropolycyclic group, a monovalent non-aromatic condensed polycyclic group, or a monovalent non-aromatic condensed heteropolycyclic group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent aromatic condensed polycyclic group, a monovalent aromatic condensed heteropolycyclic group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), —P(=O)($Q_{28}$)($Q_{29}$), or any combination thereof; or —N($Q_{31}$)($Q_{32}$), —Si($Q_{33}$)($Q_{34}$)($Q_{35}$), —B($Q_{36}$)($Q_{37}$), or —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ may each independently be a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent aromatic condensed polycyclic group, a monovalent aromatic condensed heteropolycyclic group, a monovalent non-aromatic condensed polycyclic group, or a monovalent non-aromatic condensed heteropolycyclic group, each substituted with at least one of hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ alkyl group, a $C_6$-$C_{60}$ aryl group, or any combination thereof.

The term "room temperature" as used herein refers to a temperature of about 25° C.

As used herein, the number of carbons in each group that is substituted (e.g., $C_1$-$C_{60}$) excludes the number of carbons in the substituent. For example, a $C_1$-$C_{60}$ alkyl group can be substituted with a $C_1$-$C_{60}$ alkyl group. The total number of carbons included in the $C_1$-$C_{60}$ alkyl group substituted with the $C_1$-$C_{60}$ alkyl group is not limited to 60 carbons. In addition, more than one $C_1$-$C_{60}$ alkyl substituent may be present on the $C_1$-$C_{60}$ alkyl group. This definition is not limited to the $C_1$-$C_{60}$ alkyl group and applies to all substituted groups that recite a carbon range.

The terms "a biphenyl group, a terphenyl group, and a tetraphenyl group" as used herein each refer to a monovalent group having two, three, and four phenyl groups linked via a single bond, respectively.

The terms "a cyano group-containing phenyl group, a cyano group-containing biphenyl group, a cyano group-containing terphenyl group, and a cyano group-containing tetraphenyl group" as used herein each refer to a phenyl group, a biphenyl group, a terphenyl group, and a tetraphenyl group, each substituted with at least one cyano group. In "the cyano group-containing phenyl group, the cyano group-containing biphenyl group, the cyano group-containing terphenyl group, and the cyano group-containing tetraphenyl group", a cyano group may be substituted at any position, and "the cyano group-containing phenyl group, the cyano group-containing biphenyl group, the cyano group-containing terphenyl group, and the cyano group-containing tetraphenyl group" may further include a substituent in addition to a cyano group. For example, 'a phenyl group substituted with a cyano group' and 'a phenyl group substituted with a methyl group' all belong to "a cyano group-containing phenyl group".

Hereinafter, an organic light-emitting device, according to an embodiment, will be described in more detail with reference to Synthesis Examples and Examples; however, the present disclosure is not limited thereto. The wording "B was used instead of A" used in describing Synthesis Examples means that an identical molar equivalent of B was used in place of A.

EXAMPLES

The following compounds are synthesized in Synthesis Examples 1 to 21:

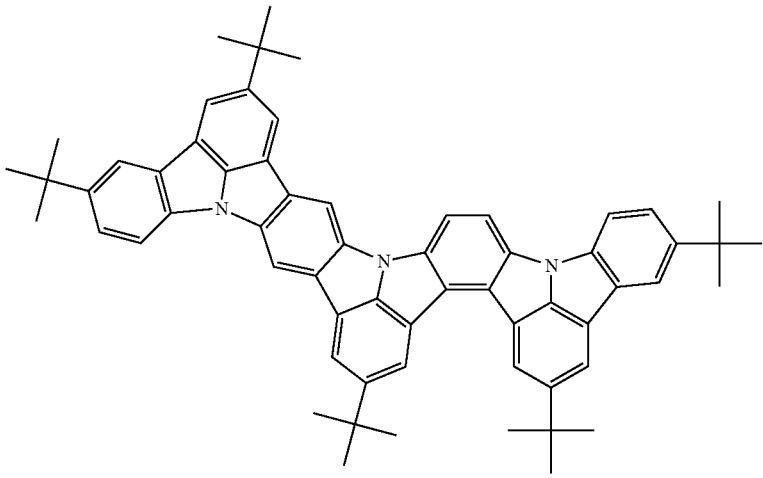

112001

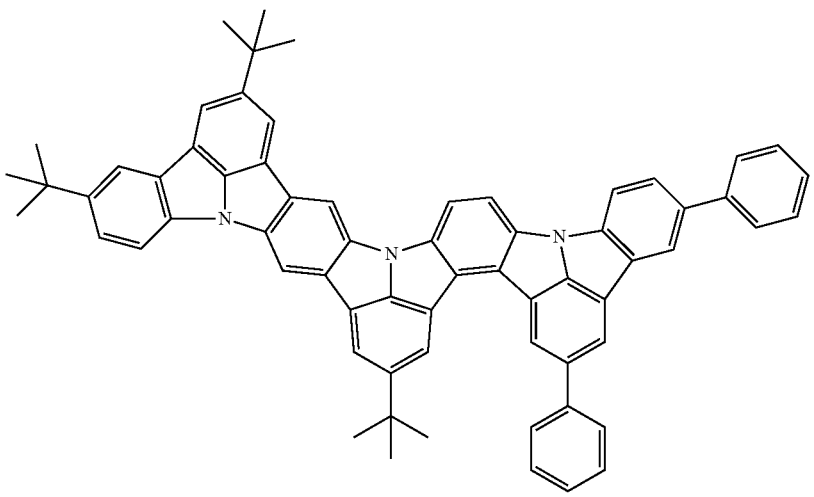

112002

3801
-continued
3802
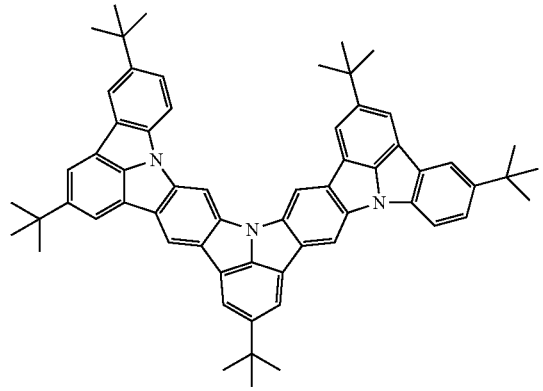
115001
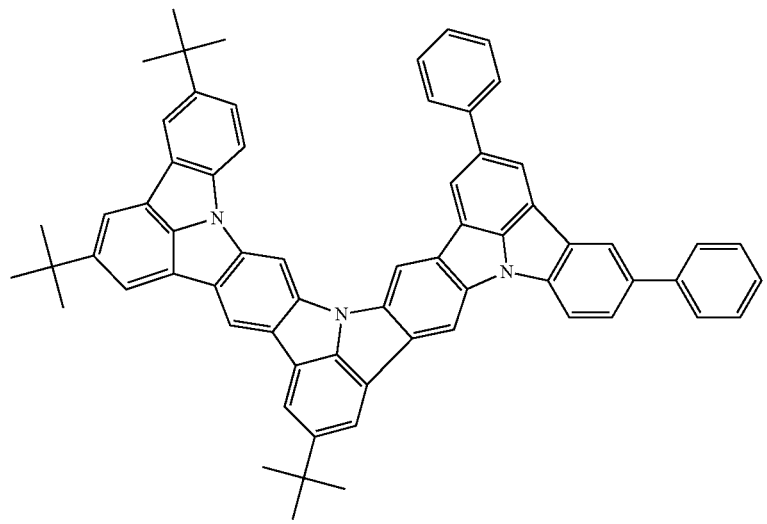
115002
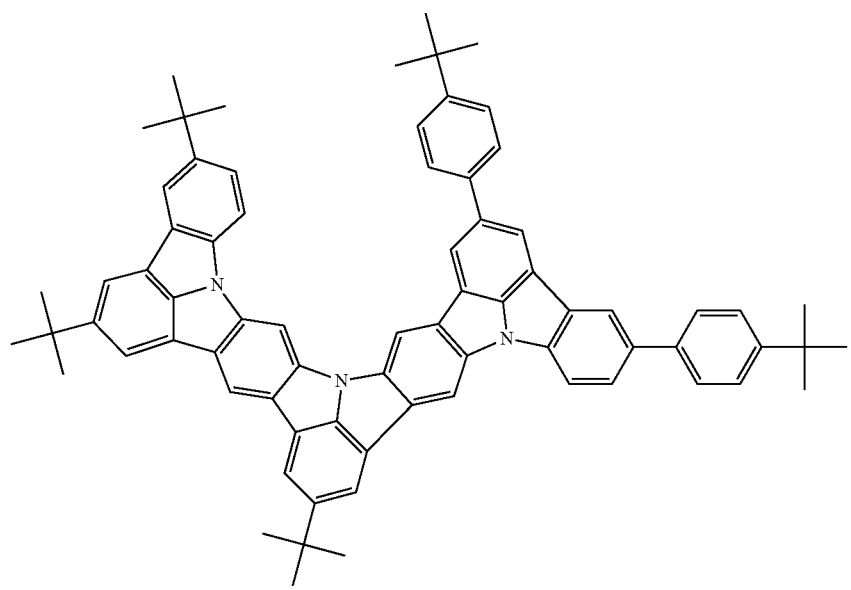
115003

-continued
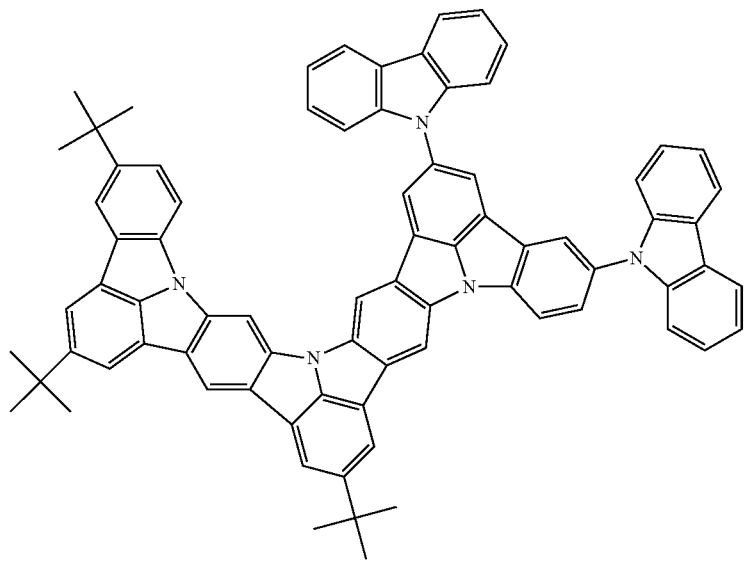
115004
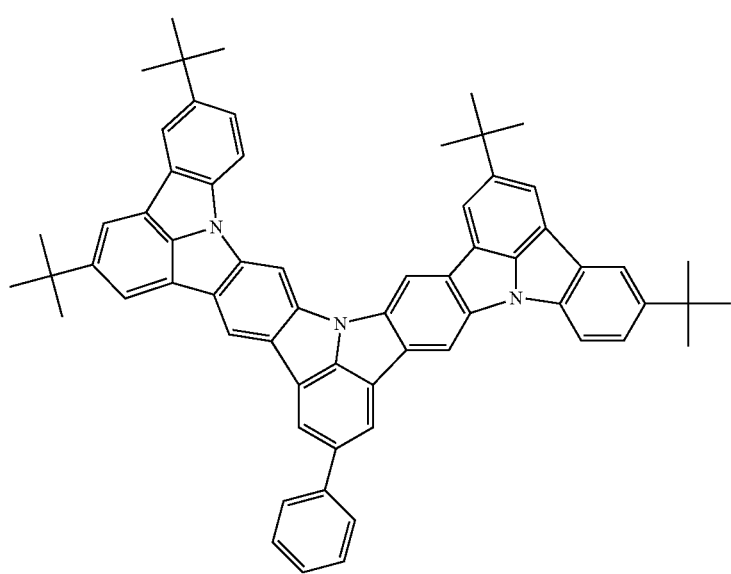
115005

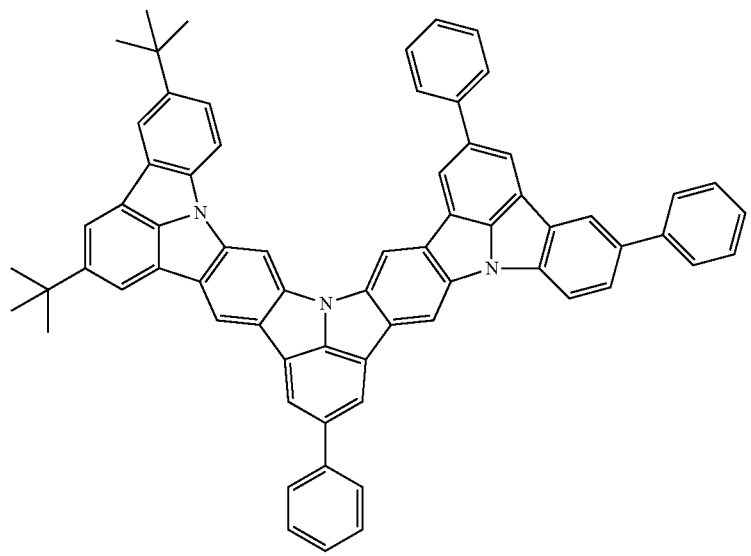
115006
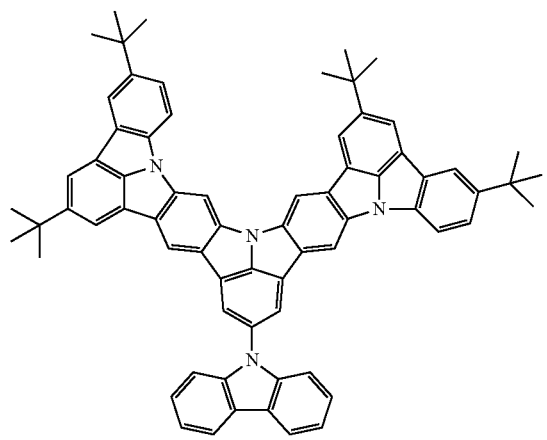
115007
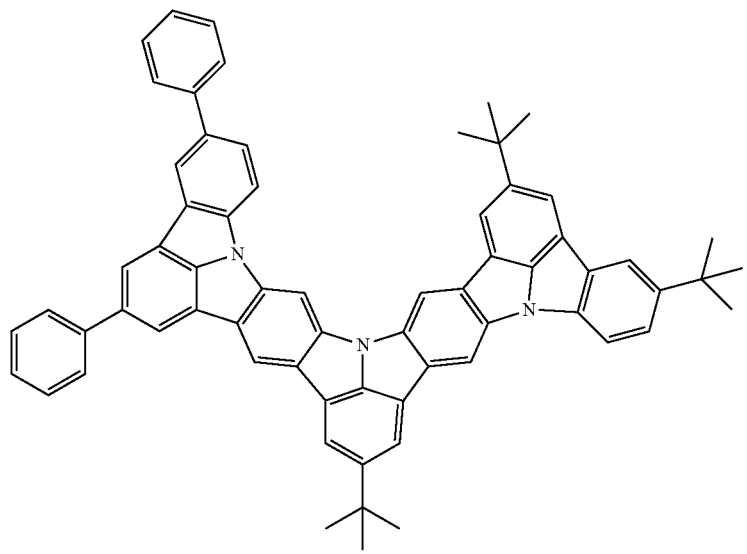
115008

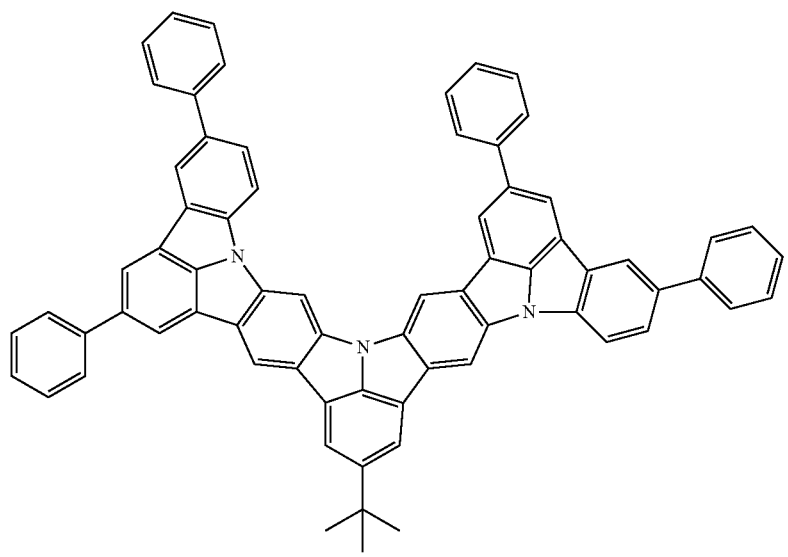
115009
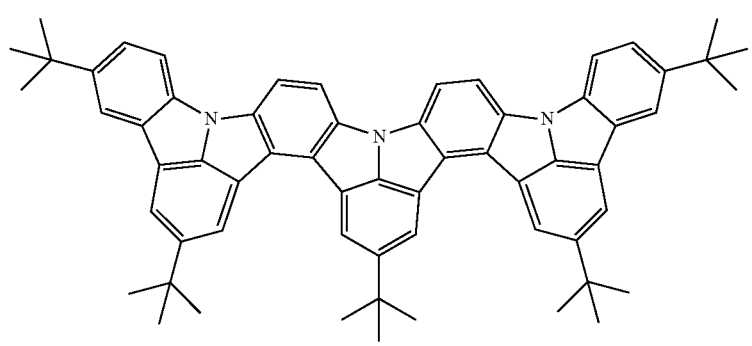
121001
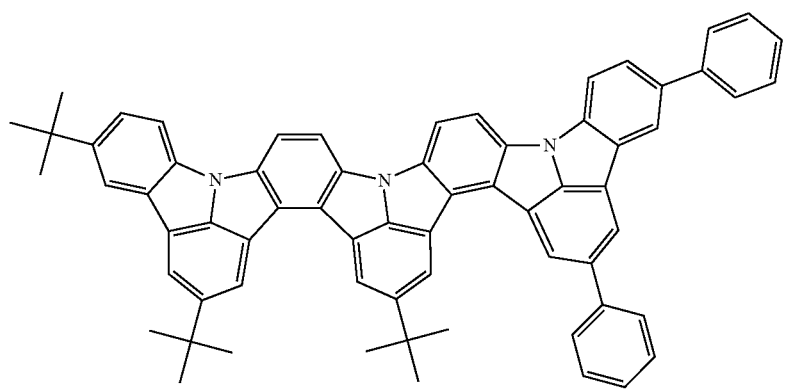
121002

-continued
122001
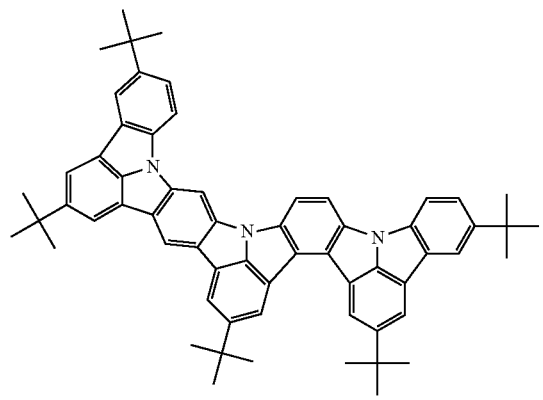
122002
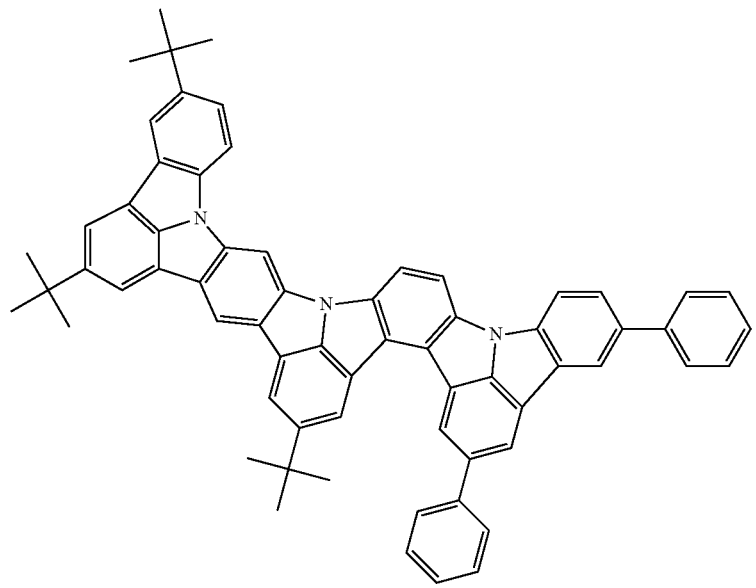
124001
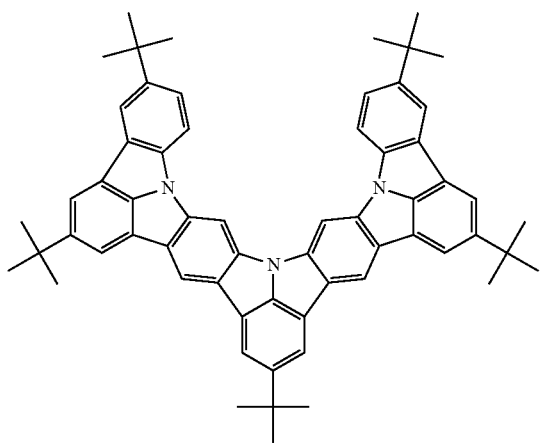
141001
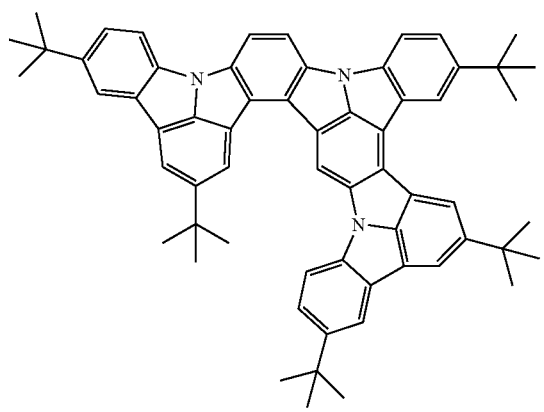

3811
3812
-continued
143001
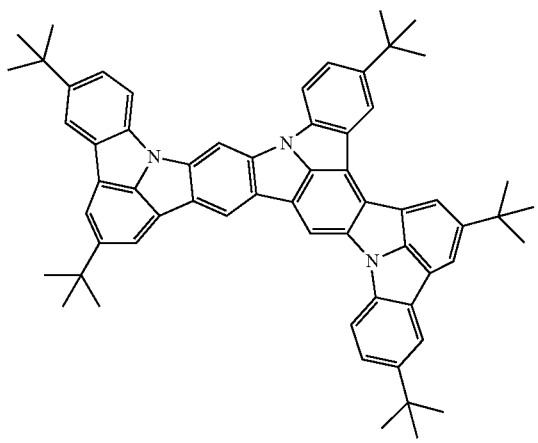
153001
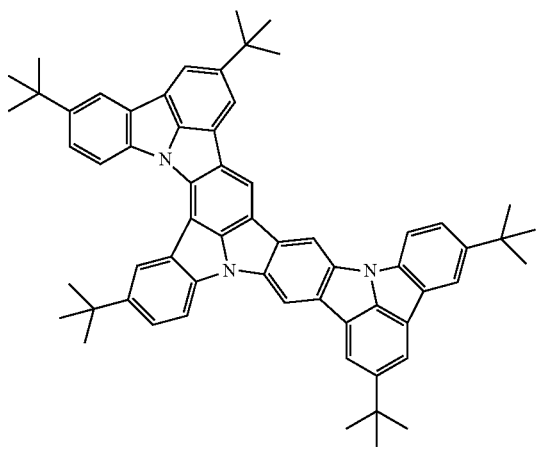
164001
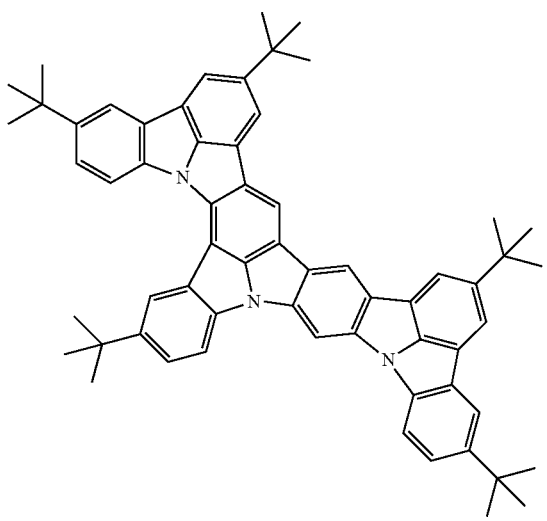
174001
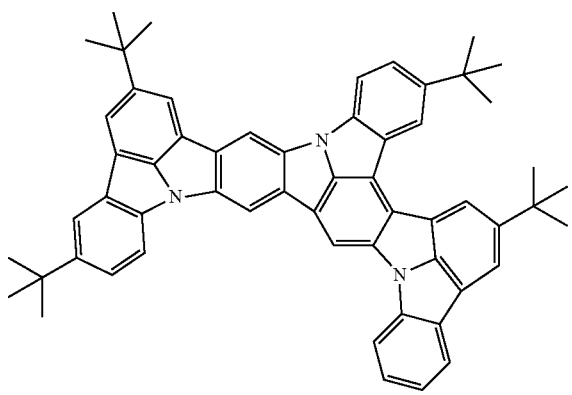
Synthesis Example 1: Synthesis of Compound 112001
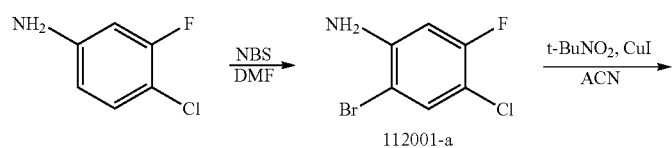

-continued
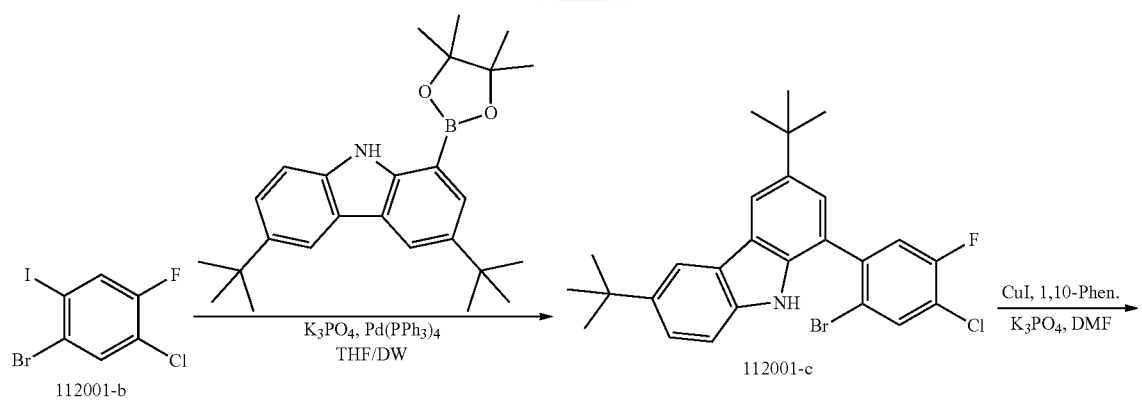
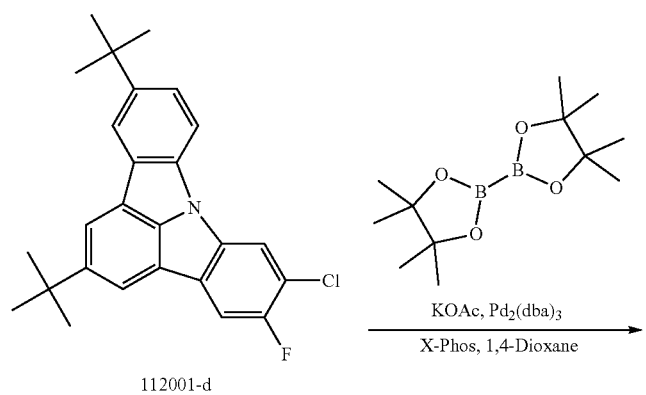
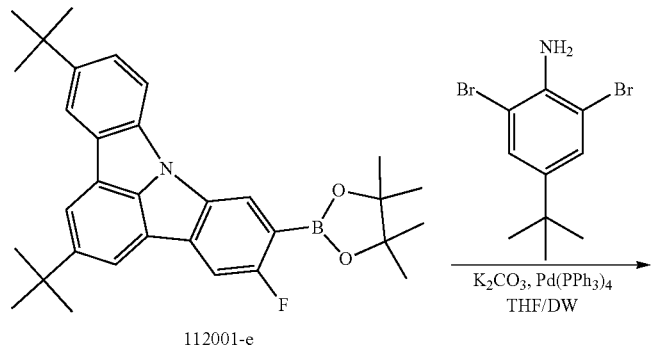
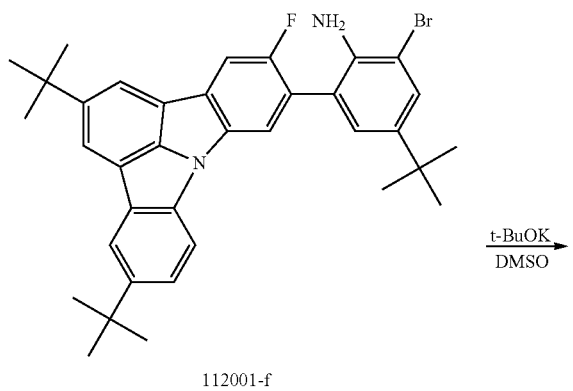

-continued
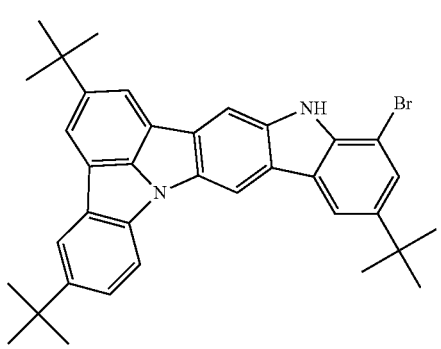
112001-g
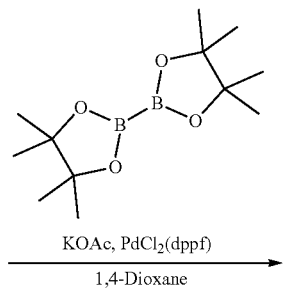
KOAc, PdCl$_2$(dppf)
1,4-Dioxane
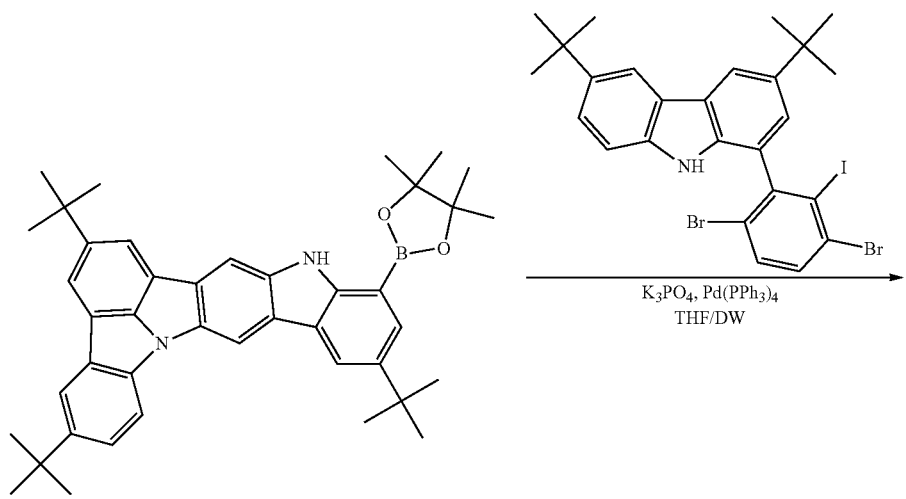
112001-h
K$_3$PO$_4$, Pd(PPh$_3$)$_4$
THF/DW
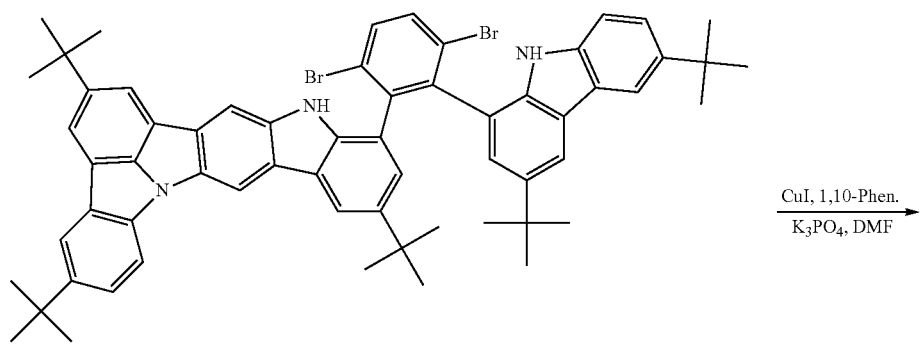
112001-i
CuI, 1,10-Phen.
K$_3$PO$_4$, DMF -continued

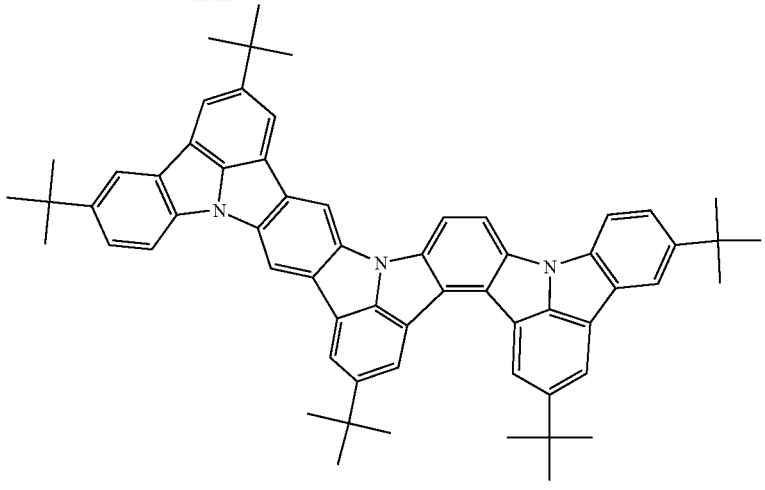

112001

Synthesis of Intermediate 112001-a 20.0 grams (g)(137 millimoles (mmol)) of 4-chloro-3-fluoroaniline, 25.7 g (144 mmol) of N-bromosuccinimide, and N,N-dimethylformamide (DMF) were stirred at room temperature to allow a reaction to occur. Once the reaction was complete, a sodium thiosulfate aqueous solution (2M) was added dropwise thereto. Distilled water and dichloromethane (DCM) were added thereto, followed by extraction. Then, an aqueous solution layer was removed therefrom. The resulting filtrate was concentrated under reduced pressure. The product was separated through column chromatography to obtain 29.3 g of Intermediate 112001 (yield: 95%).

LC-Mass (calculated value: 223.93 g/mol, found value: 223.16 (M+1))

Synthesis of Intermediate 112001-b 36.0 g (160 mmol) of Intermediate 112001-a, 45.7 g (240 mmol) of copper(I) iodide (CuI), 19.8 g (192 mmol) of tert-butyl nitrite, and 800 mL of acetonitrile were stirred under reflux at a temperature of 150° C. Once the reaction was complete, the resulting mixture was cooled to room temperature and filtrated through silica gel under reduced pressure to obtain a filtrate. The resulting filtrate was concentrated under reduced pressure and separated through silica gel column chromatography to thereby obtain 21.3 g of Intermediate 112001-b (yield: 40%).

LC-Mass (calculated value: 334.81 g/mol, found value: 334.25 (M+1))

Synthesis of Intermediate 112001-c 37.2 g (111 mmol) of Intermediate 112001-b, 15.0 g (37.0 mmol) of 3,6-di-tert-butyl-1-(4,4,5,5-tetramethyl-1,3,2-dioxaborolan-2-yl)-9H-carbazole, and 1.28 g (1.11 mmol) of tetrakis(triphenylphosphine)palladium(0), Pd(PPh$_3$)$_4$) were added to 300 ml of tetrahydrofuran (THF), followed by stirring under reflux. The mixture was added dropwise to 150 mL of 2 M potassium triphosphate (K$_3$PO$_4$) solution and stirred. Once the reaction was complete, an organic layer was separated using dichloromethane and distilled water. Then, the separated organic layer was concentrated under reduced pressure and separated through silica gel column chromatography to thereby 8.72 g of Intermediate 112001-c (yield: 48%).

LC-Mass (calculated value: 486.10 g/mol, found value: 486.75 (M+1))

Synthesis of Intermediate 112001-d 8.70 g (17.9 mmol) of Intermediate 112001-c, 1.70 g (8.95 mmol) of CuI, 1.61 g (8.95 mmol) of 1,10-phenanthroline, 11.4 g (54.7 mmol) of potassium phosphate, and 100 ml of DMF were heated at a temperature of 100° C. and stirred. Once the reaction was complete, the resulting mixture was filtrated under reduced pressure using silica gel. Then, the filtrate was concentrated under reduced pressure. Subsequently, a precipitate obtained by using dichloromethane and methanol was filtered, and the resulting solid was dried in a vacuum oven to thereby obtain 6.53 g of Intermediate 112001-d (yield: 90%).

LC-Mass (calculated value: 405.17 g/mol, found value: 405.59 (M+1))

Synthesis of Intermediate 112001-e 6.50 g (16.0 mmol) of Intermediate 112001-d, 6.10 g (24.1 mmol) of 4,4,4',4',5,5,5',5'-octamethyl-2,2'-bi(1,3,2-dioxaborolane), 4.71 g (47.8 mmol) of potassium acetate (KOAc), 0.733 g (0.801 mmol) of tris(dibenzylideneacetone) dipalladium(0) (Pd$_2$(dba)$_3$), 0.764 g (1.60 mmol) of X-Phos, and 120 mL of 1,4-dioxane were added to a round flask. Then, a reaction was allowed to occur while heating at a temperature of 170° C. and stirring. Once the reaction was complete, the resulting mixture was filtrated under reduced pressure using silica gel. Then, the filtrate was concentrated. A precipitate obtained by using dichloromethane and methanol was filtered, and the resulting solid was dried in a vacuum oven to thereby obtain 6.87 g of Intermediate 112001-e (yield: 86%).

LC-Mass (calculated value: 498.30 g/mol, found value: 498.67 (M+1))

Synthesis of Intermediate 112001-f 4.00 g (8.04 mmol) of Intermediate 112001-e, 7.40 g (24.2 mmol) of 2,6-dibromo-4-(tert-butyl) aniline, 0.278 g (0.242 mmol) of Pd(PPh$_3$)$_4$, and 120 mL of THF were stirred together. Then, 60 mL of 2 M potassium carbonate (K$_2$CO$_3$) aqueous solution was added thereto, followed by stirring under reflux. Once the mixture was cooled to room temperature, an extraction process was performed using dichloromethane and distilled water, and the extracted organic layer was concentrated and adsorbed to silica gel. Then, a purification process was performed by using column chromatography charged with silica gel to thereby obtain 1.73 g of Intermediate I12001-f (yield: 36%).

LC-Mass (calculated value: 597.23 g/mol, found value: 597.20 (M+1))

Synthesis of Intermediate 112001-g 1.70 g (2.84 mmol) of Intermediate 112001-f, 0.958 g (8.53 mmol) of potassium tert-butoxide (t-BuOK), and 20 mL of dimethyl sulfoxide (DMSO) were added to a round flask and stirred under reflux while heating. Once the reaction was complete, distilled water was added thereto, and an extraction process was performed using dichloromethane. Then, adsorption to silica gel occurred. Next, impurities were removed by using column chromatography and dried to thereby obtain 1.31 g of Intermediate 112001-g (yield: 80%).

LC-Mass (calculated value: 577.22 g/mol, found value: 577.86 (M+1))

Synthesis of Intermediate 112001-h 1.30 g (2.25 mmol) of Intermediate 112001-g, 0.871 g (3.38 mmol) of 4,4,4',4',5,5,5',5'-octamethyl-2,2'-bi (1,3,2-dioxaborolane), 0.662 g (6.75 mmol) of KOAc, and 0.049 g (0.068 mmol) of [1,1'-bis(diphenylphosphino)ferrocene]dichloropalladium(II), (PdCl$_2$(dppf)), and 30 mL of 1,4-dioxane were mixed together and stirred under reflux while heating. Once the reaction was complete, dichloromethane was added thereto, and filtration under reduced pressure was performed by using a filter charged with silica gel for concentration. Subsequently, a precipitate obtained by using dichloromethane and methanol was filtered, and the resulting solid was dried in a vacuum oven to thereby obtain 1.25 g of Intermediate 112001-h (yield: 89%).

LC-Mass (calculated value: 625.40 g/mol, found value: 625.10 (M+1))

Synthesis of Intermediate 112001-i 0.550 g of Intermediate 112001-i was synthesized in substantially the same manner as in Synthesis of Intermediate 112001-c in Synthesis Example 1, except that 3,6-di-tert-butyl-1-(3,6-dibromo-2-iodophenyl)-9H-carbazole was used instead of Intermediate 112001-b (yield: 57%).

LC-Mass (calculated value: 1008.35 g/mol, found value: 1009.55 (M+1))

Synthesis of Compound 112001

0.400 g (0.396 mmol) of Intermediate 112001-i, 0.075 g (0.396 mmol) of CuI, 0.071 g (0.396 mmol) of 1,10-phenanthroline, 0.336 g (1.58 mmol) of potassium phosphate, and 15 ml of DMF were heated and stirred. Once the reaction was complete, the mixture was heated and dissolved in 2 liters (L) of chloroform. Then, a filtration process was performed using silica gel and purified to thereby obtain 0.252 g of Compound 112001 (yield: 74%).

LC-Mass (calculated value: 847.4865 g/mol, found value: 847.4866 (M+1))

Synthesis Example 2: Synthesis of Compound 112002

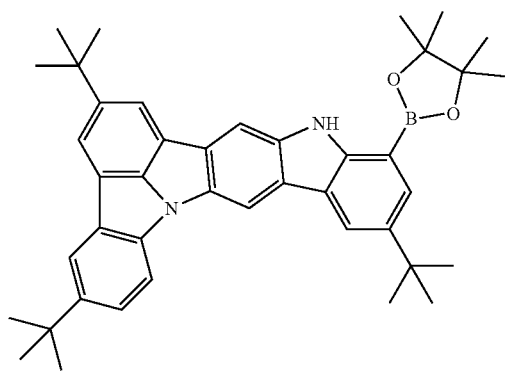

112001-h

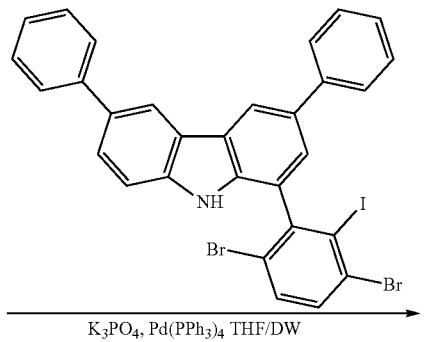

K$_3$PO$_4$, Pd(PPh$_3$)$_4$ THF/DW

-continued

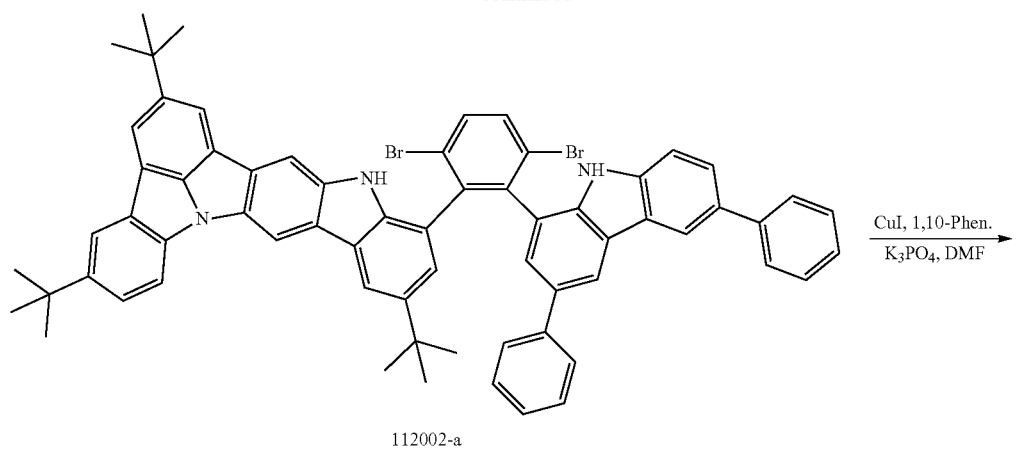
112002-a

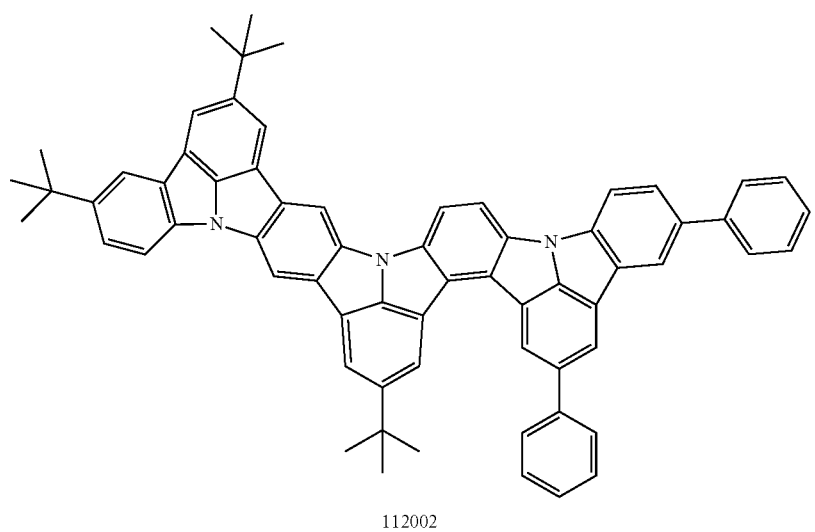
112002

Synthesis of Intermediate 112002-a 0.581 g of Intermediate 112002-a was obtained in substantially the same manner as in Synthesis of Intermediate 112001-c in Synthesis Example 1 using 0.600 g (0.961 mmol) of Intermediate 112001-h, except that 0.979 g (1.44 mmol) of 1-(2,5-dibromo-4-iodophenyl)-3,6-diphenyl-9H-carbazole was used instead of the Intermediate, i.e., 3,6-di-t-butyl-1-(3,6-dibromo-2-iodophenyl)-9 H-carbazole (yield: 58%).

LC-Mass (calculated value: 1048.28 g/mol, found value: 1049.05 (M+1))

Synthesis of Compound 112002

0.293 g of Compound 112002 was obtained in substantially the same manner in Synthesis of Compound 112001 in Synthesis Example 1, except that Intermediate 112002-a was used instead of Intermediate 112001-i (yield: 88%).

LC-Mass (calculated value: 887.4239 g/mol, found value: 887.4239 (M+1))

Synthesis Example 3: Synthesis of Compound 115001

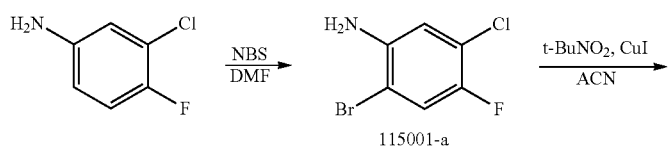
115001-a

-continued
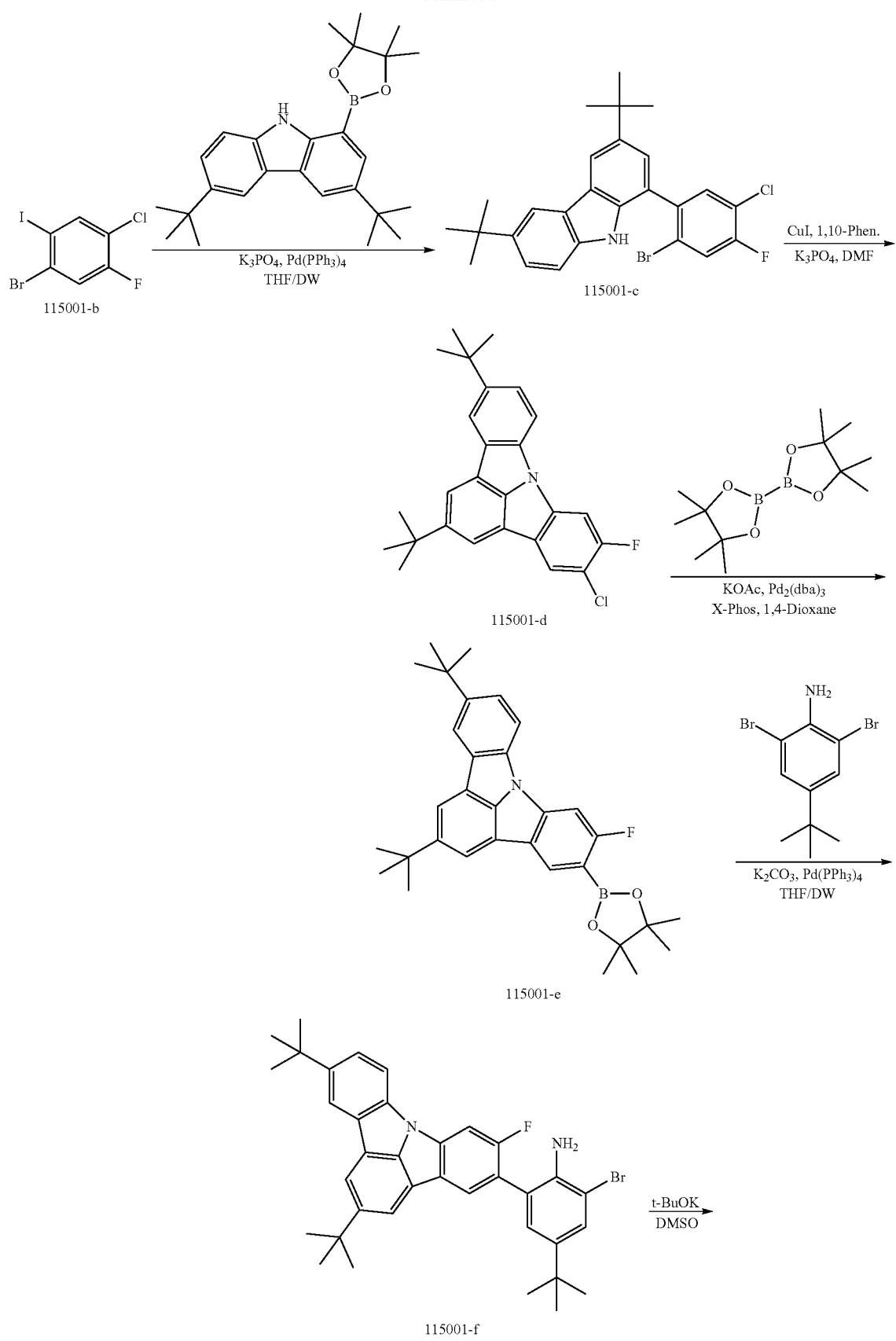

-continued
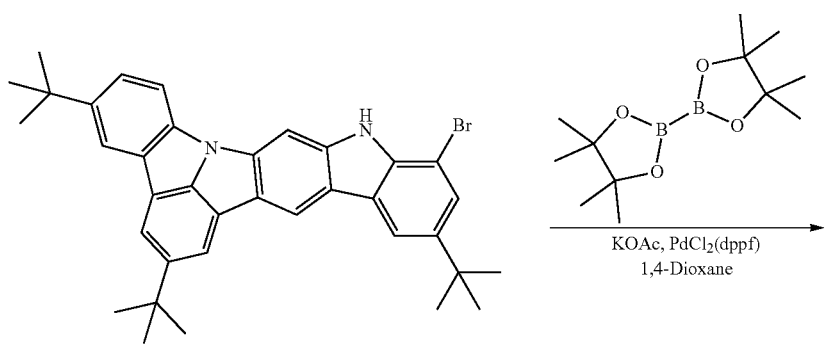
115001-g
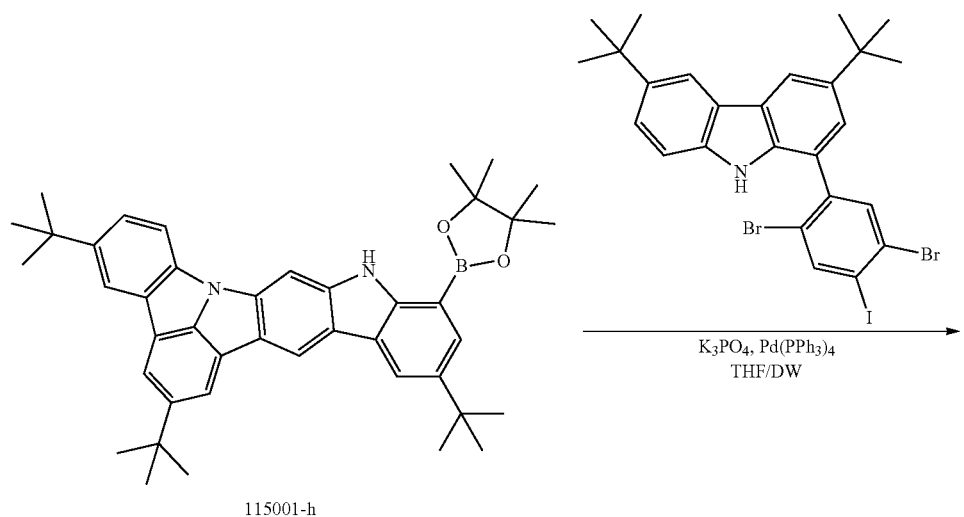
115001-h
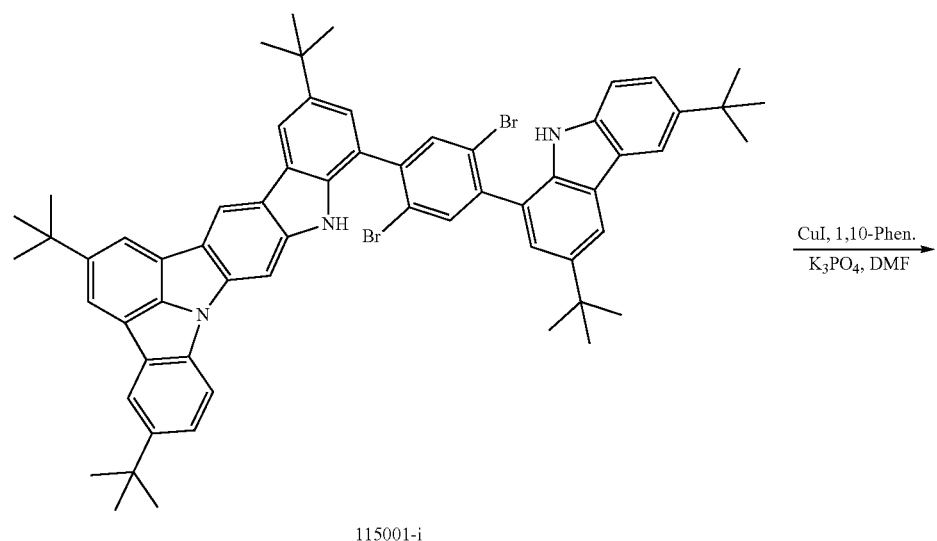
115001-i

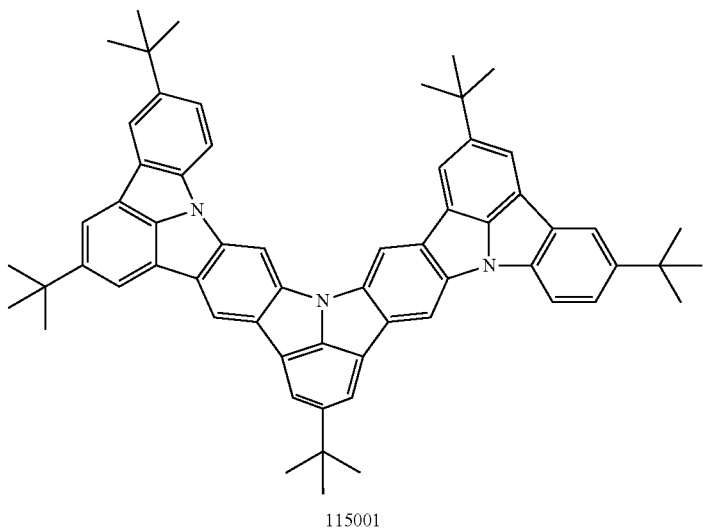

115001

Synthesis of Intermediate 115001-a 34.0 g of Intermediate 115001-a was obtained in substantially the same manner as in Synthesis of Intermediate 112001-a in Synthesis Example 1, except that 40.0 g (275 mmol) of 3-chloro-4-fluoroaniline was used instead of 4-chloro-3-fluoroaniline (yield: 55%).

LC-Mass (calculated value: 223.93 g/mol, found value: 223.17 (M+1))

Synthesis of Intermediate 115001-b 9.32 g of Intermediate 115001-b was obtained in substantially the same manner as in Synthesis of Intermediate 112001-b in Synthesis Example 1, except that 15.0 g (66.8 mmol) of Intermediate 115001-a was used instead of Intermediate 112001-a (yield: 42%).

LC-Mass (calculated value: 334.81 g/mol, found value: 334.15 (M+1))

Synthesis of Intermediate 115001-c 3.12 g of Intermediate 115001-c was obtained in substantially the same manner as in Synthesis of Intermediate 112001-c in Synthesis Example 1, except that Intermediate 115001-b was used instead of Intermediate 112001-b (yield: 43%).

LC-Mass (calculated value: 486.10 g/mol, found value: 486.62 (M+1))

Synthesis of Intermediate 115001-d 2.43 g of Intermediate 115001-d was obtained in substantially the same manner as in Synthesis of Intermediate 112001-d in Synthesis Example 1, except that 3.00 g (6.16 mmol) of Intermediate 115001-c was used instead of Intermediate 112001-c (yield: 97%).

LC-Mass (calculated value: 405.17 g/mol, found value: 405.63 (M+1))

Synthesis of Intermediate 115001-e 4.20 g of Intermediate 115001-e was obtained in substantially the same manner as in Synthesis of Intermediate 112001-e in Synthesis Example 1, except that 3.70 g (9.11 mmol) of Intermediate 115001-d was used instead of Intermediate 112001-d (yield: 93%).

LC-Mass (calculated value: 498.30 g/mol, found value: 498.89 (M+1))

Synthesis of Intermediate 115001-f 1.30 g of Intermediate 115001-f was obtained in substantially the same manner as in Synthesis of Intermediate 112001-f in Synthesis Example 1, except that 2.00 g (4.02 mmol) of Intermediate 115001-e was used instead of Intermediate 112001-e (yield: 54%).

LC-Mass (calculated value: 597.23 g/mol, found value: 597.98 (M+1))

Synthesis of Intermediate 115001-g 1.01 g of Intermediate 115001-g was obtained in substantially the same manner as in Synthesis of Intermediate 112001-g in Synthesis Example 1, except that Intermediate 115001-f was used instead of Intermediate 112001-f (yield: 69%).

LC-Mass (calculated value: 577.22 g/mol, found value: 577.20 (M+1))

Synthesis of Intermediate 115001-h 0.972 g of Intermediate 115001-h was obtained in substantially the same manner as in Synthesis of Intermediate 112001-h in Synthesis Example 1, except that 1.00 g (1.73 mmol) of Intermediate 115001-g was used instead of Intermediate 112001-g (yield: 90%).

LC-Mass (calculated value: 625.40 g/mol, found value: 625.28 (M+1))

Synthesis of Intermediate 115001-i 0.440 g of Intermediate 115001-i was obtained in substantially the same manner as in Synthesis of Intermediate 112001-i in Synthesis Example 1, except that Intermediate 115001-h was used (yield: 45%).

LC-Mass (calculated value: 1008.35 g/mol, found value: 1007.95 (M+1))

Synthesis of Compound 115001

0.281 g of Compound 115001 was obtained in substantially the same manner as in Synthesis of Compound 112001 in Synthesis Example 1, except that 0.400 g (0.396 mmol) of Intermediate 115001-i was used instead of Intermediate 112001-i (yield: 83%).

LC-Mass (calculated value: 847.4865 g/mol, found value: 847.4870 (M+1))

Synthesis Example 4: Synthesis of Compound 115002

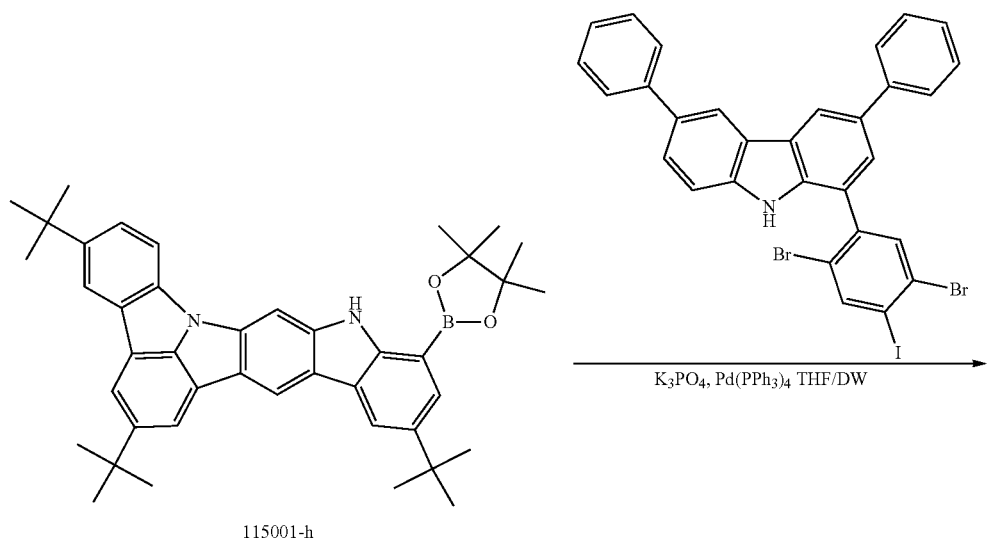

115001-h

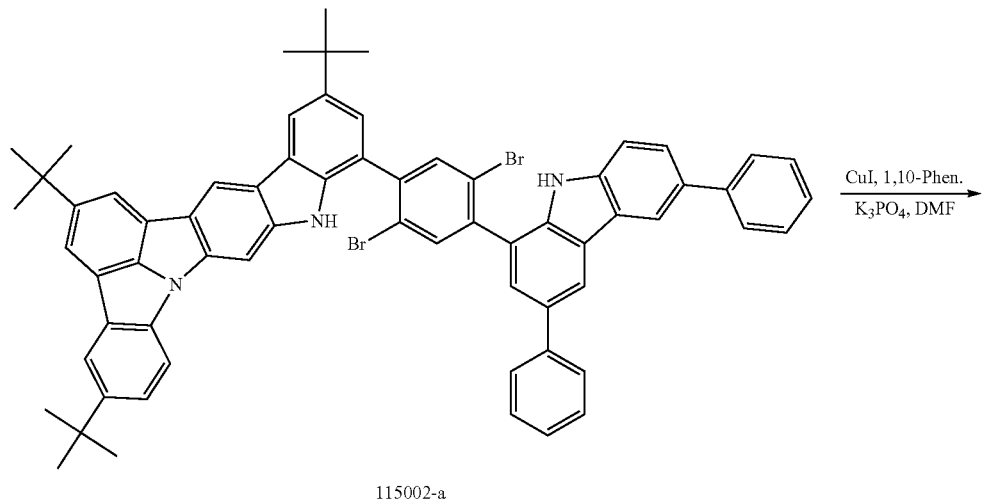

115002-a

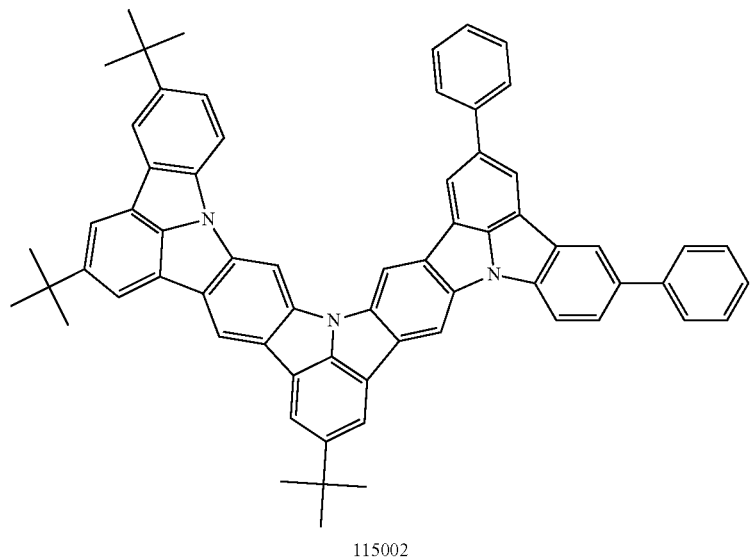
115002

Synthesis of Intermediate 115002-a 0.516 g of Intermediate 115002-a was obtained in substantially the same manner as in Synthesis of Intermediate 112002-a in Synthesis Example 2, except that 0.600 g (0.961 mmol) of Intermediate 115001-h was used as a start material (yield: 51%).

LC-Mass (calculated value: 1048.28 g/mol, found value: 1047.40 (M+1))

Synthesis of Compound 115002

0.310 g of Compound 115002 was obtained in substantially the same manner as in Synthesis of Compound 112001 in Synthesis Example 1, except that Intermediate 115002-a was used (yield: 92%).

LC-Mass (calculated value: 887.4239 g/mol, found value: 887.4252 (M+1))

Synthesis Example 5: Synthesis of Compound 115003

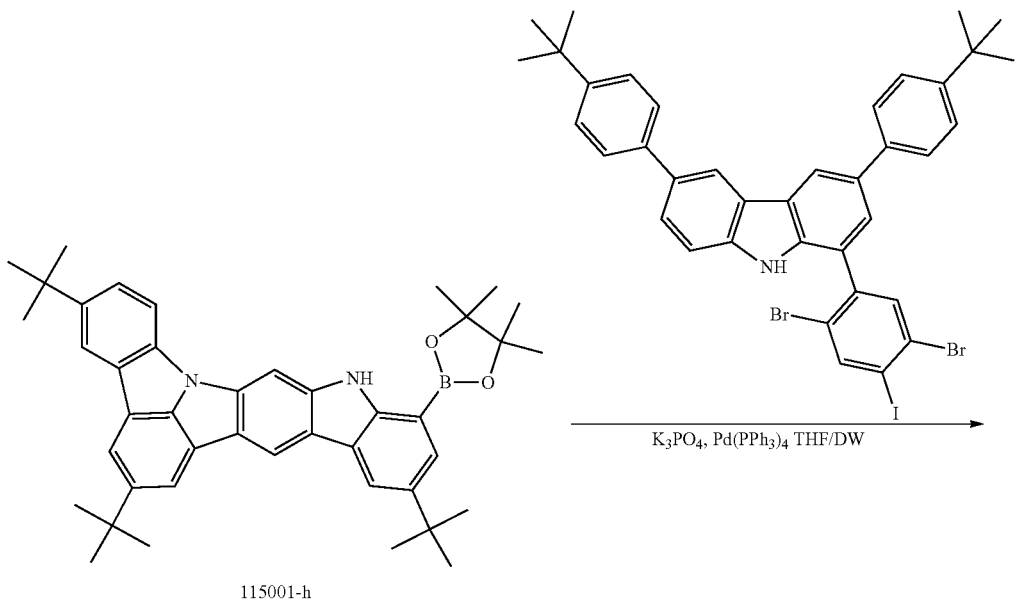
115001-h

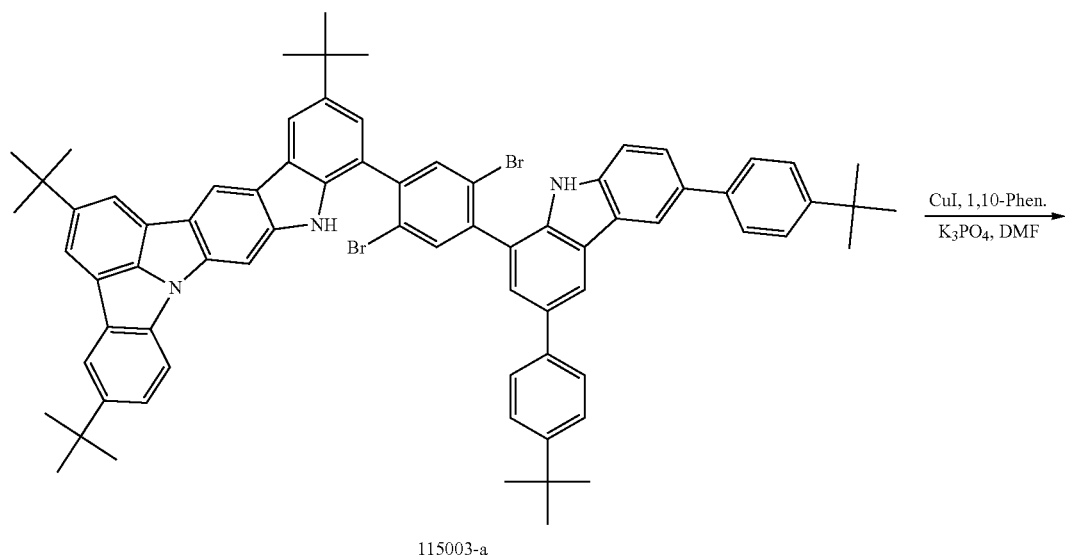

115003-a

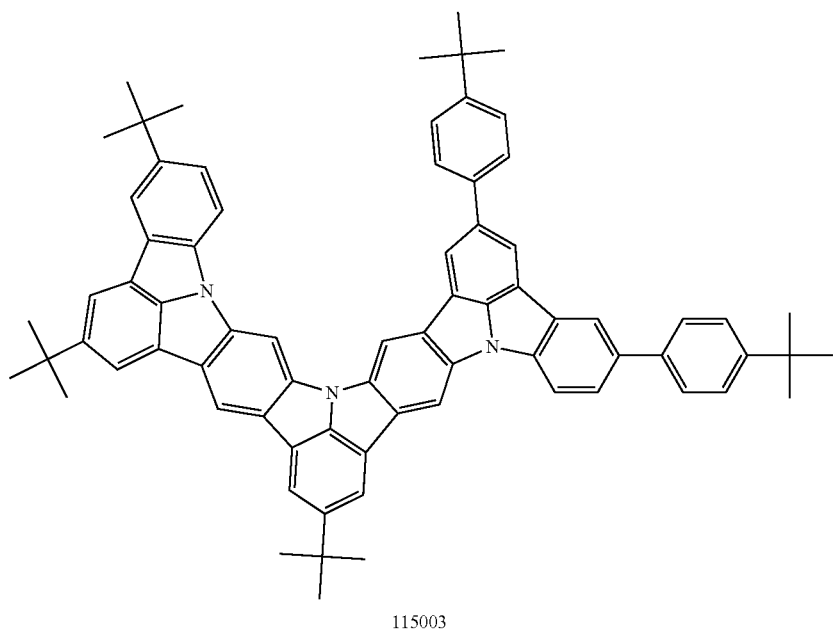

115003

Synthesis of Intermediate 115003-a 0.536 g of Intermediate 115003-a was obtained in substantially the same manner as in Synthesis of Intermediate 112001-a in Synthesis Example 1, except that 3,6-bis(4-(tert-butyl)phenyl)-1-(2,5-dibromo-4-iodophenyl)-9H-carbazole was used instead of 3,6-di-t-butyl-1-(3,6-dibromo-2-iodophenyl)-9H-cabazole to react with 0.600 g of Intermediate 115001-h (0.961 mmol)(yield: 48%).

LC-Mass (calculated value: 1160.41 g/mol, found value: 1161.21 (M+1))

Synthesis of Compound 115003

0.387 g of Compound 115003 was obtained in substantially the same manner as in Synthesis of Compound 112001 in Synthesis Example 1, except that Intermediate 115003-a was used in reaction (yield: 90%).

LC-Mass (calculated value: 1000.5570 g/mol, found value: 1000.5573 (M+1))

Synthesis Example 6: Synthesis of Compound 115004
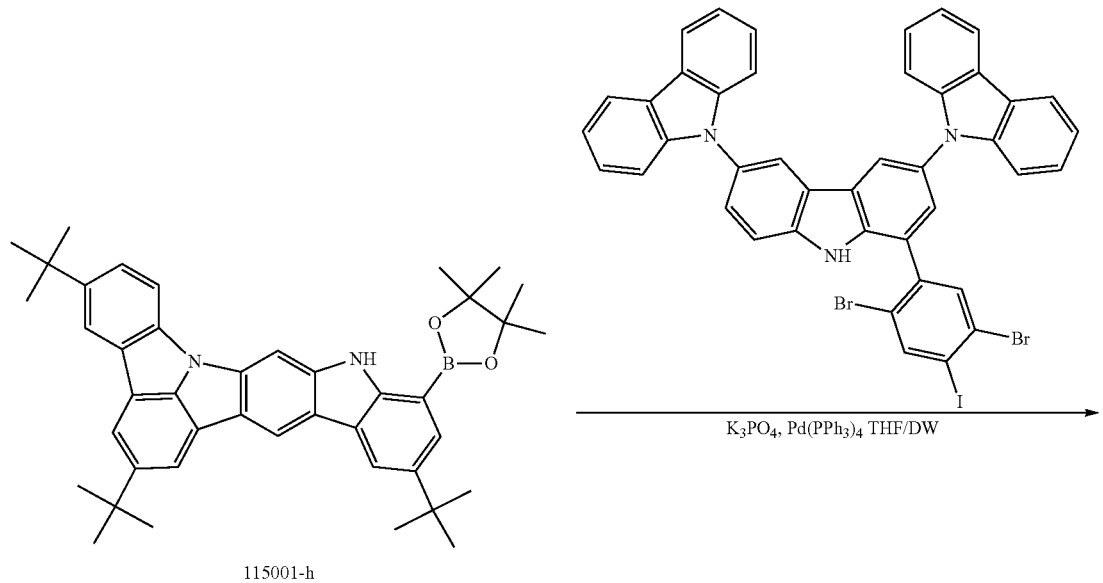
115001-h
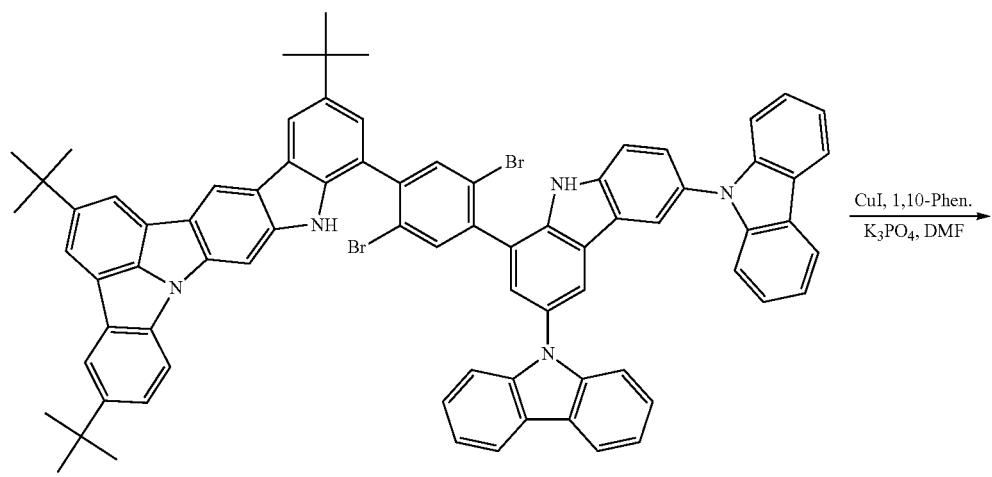
115004-a

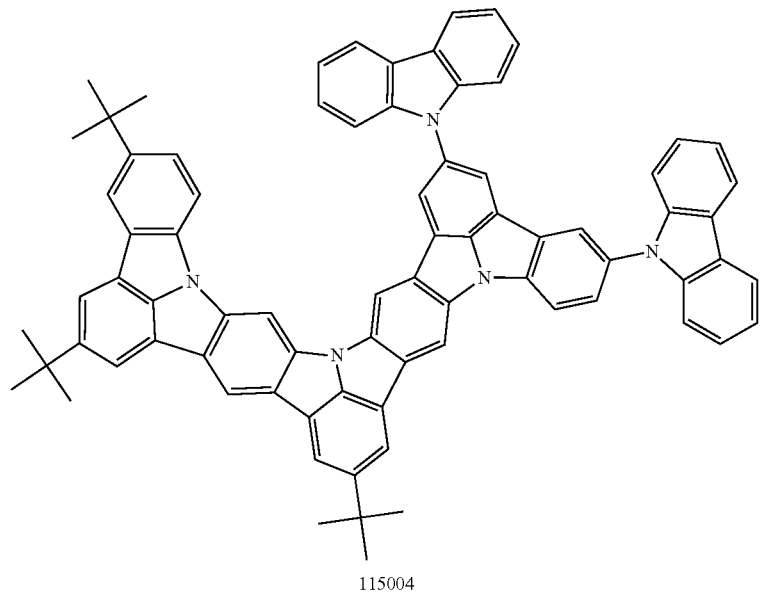

115004

Synthesis of Intermediate 115004-a 0.507 g of Intermediate 115004-a was synthesized in substantially the same manner as in Synthesis of Intermediate 112001-a in Synthesis Example 1, except that Intermediate 1'-(2,5-dibromo-4-iodophenyl)-9'H-9,3': 6',9"-tert-carbazole was used instead of Intermediate 3,6-di-t-butyl-1-(3,6-dibromo-2-iodophenyl)-9H-carbazole to react with Intermediate 115001-h (0.600 g, 0.961 mmol), followed by purification (yield: 43%).

LC-Mass (calculated value: 1226.34 g/mol, found value: 1225.88 (M+1))

Synthesis of Compound 115004

0.395 g of Compound 115004 was obtained in substantially the same manner as in Synthesis of Compound 112001 in Synthesis Example 1, except that Intermediate 115004-a was used in reaction (yield: 91%).

LC-Mass (calculated value: 1066.4849 g/mol, found value: 1066.4848 (M+1))

Synthesis Example 7: Synthesis of Compound 115005

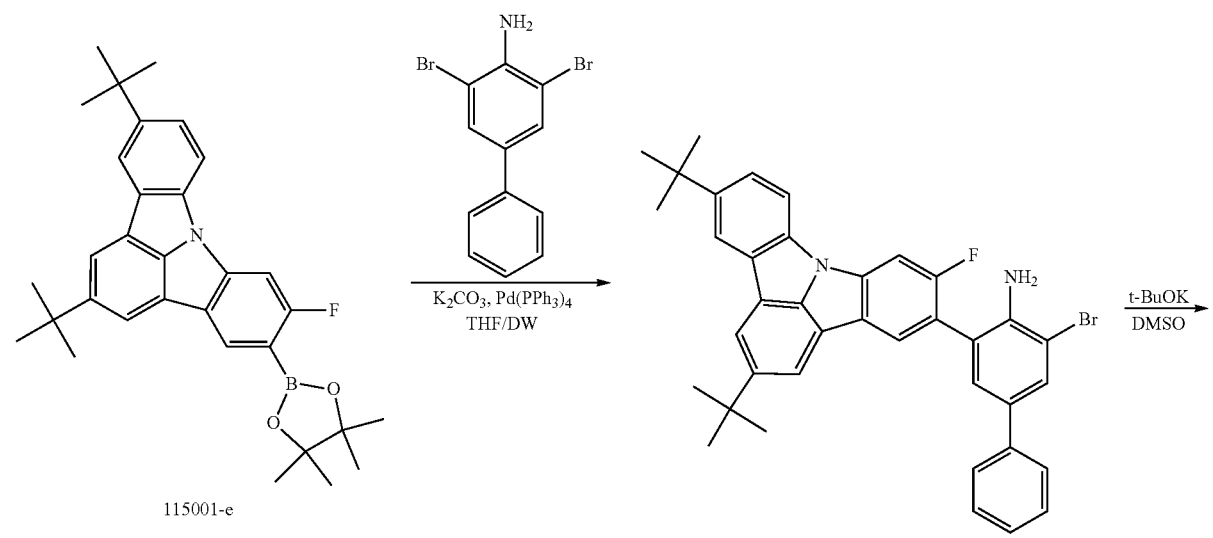

3839  3840
-continued
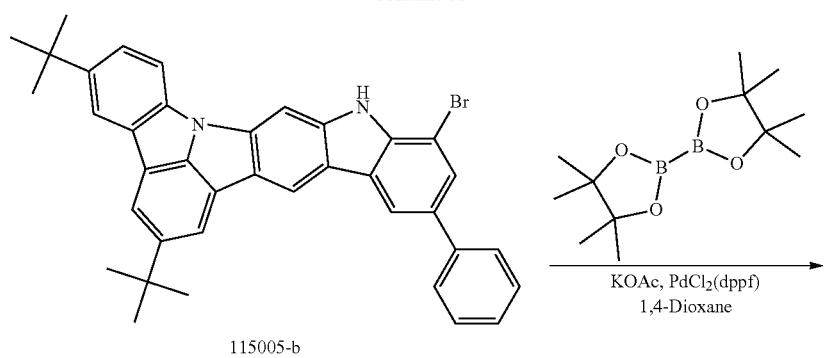
115005-b
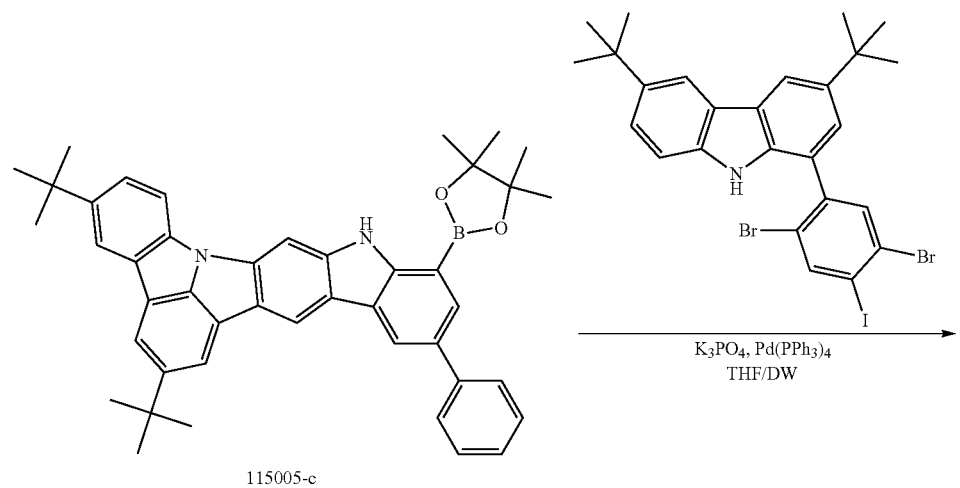
115005-c
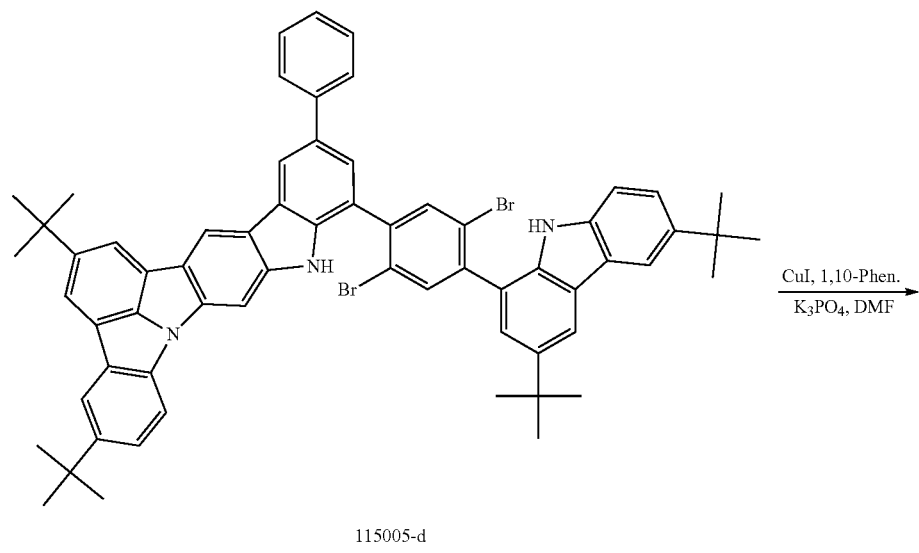
115005-d -continued

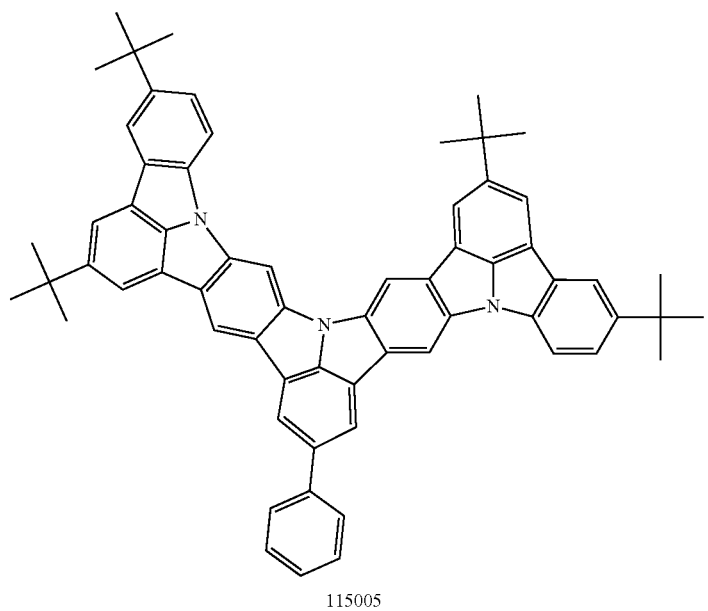

115005

Synthesis of Intermediate 115005-a 1.17 g of Intermediate 115005-a was obtained in substantially the same manner as in Synthesis of Intermediate 112001-f in Synthesis Example 1, except that 3.96 g (12.1 mmol) of 3,5-dibromo-[1,1'-biphenyl]-4-amine was used instead of Intermediate 2,6-dibromo-4-(t-butyl) aniline to react with Intermediate 115001-e (yield: 47%).

LC-Mass (calculated value: 617.20 g/mol, found value: 617.44 (M+1))

Synthesis of Intermediate 115005-b 1.37 g of Intermediate 115005-b was obtained in substantially the same manner as in Synthesis of Intermediate 112001-g in Synthesis Example 1, except that Intermediate 115005-a was used (yield: 71%).

LC-Mass (calculated value: 597.19 g/mol, found value: 597.72 (M+1))

Synthesis of Intermediate 115005-c 0.949 g of Intermediate 115005-c was obtained in substantially the same manner as in Synthesis of Intermediate 112001-h in Synthesis Example 1, except that Intermediate 115005-b was used in reaction (yield: 88%).

LC-Mass (calculated value: 645.37 g/mol, found value: 646.01 (M+1))

Synthesis of Intermediate 115005-d 0.751 g of Intermediate 115005-d was obtained in substantially the same manner as in Synthesis of Intermediate 112001-c in Synthesis Example 1, except that Intermediate 115005-c was used as a start material (yield: 61%).

LC-Mass (calculated value: 1028.32 g/mol, found value: 1029.22 (M+1))

Synthesis of Compound 115005

0.421 g of Compound 115005 was obtained in substantially the same manner as in Synthesis of Compound 112001 in Synthesis Example 1, except that Intermediate 115005-d was used in reaction (yield: 86%).

LC-Mass (calculated value: 868.4631 g/mol, found value: 868.4633 (M+1))

Synthesis Example 8: Synthesis of Compound 115006
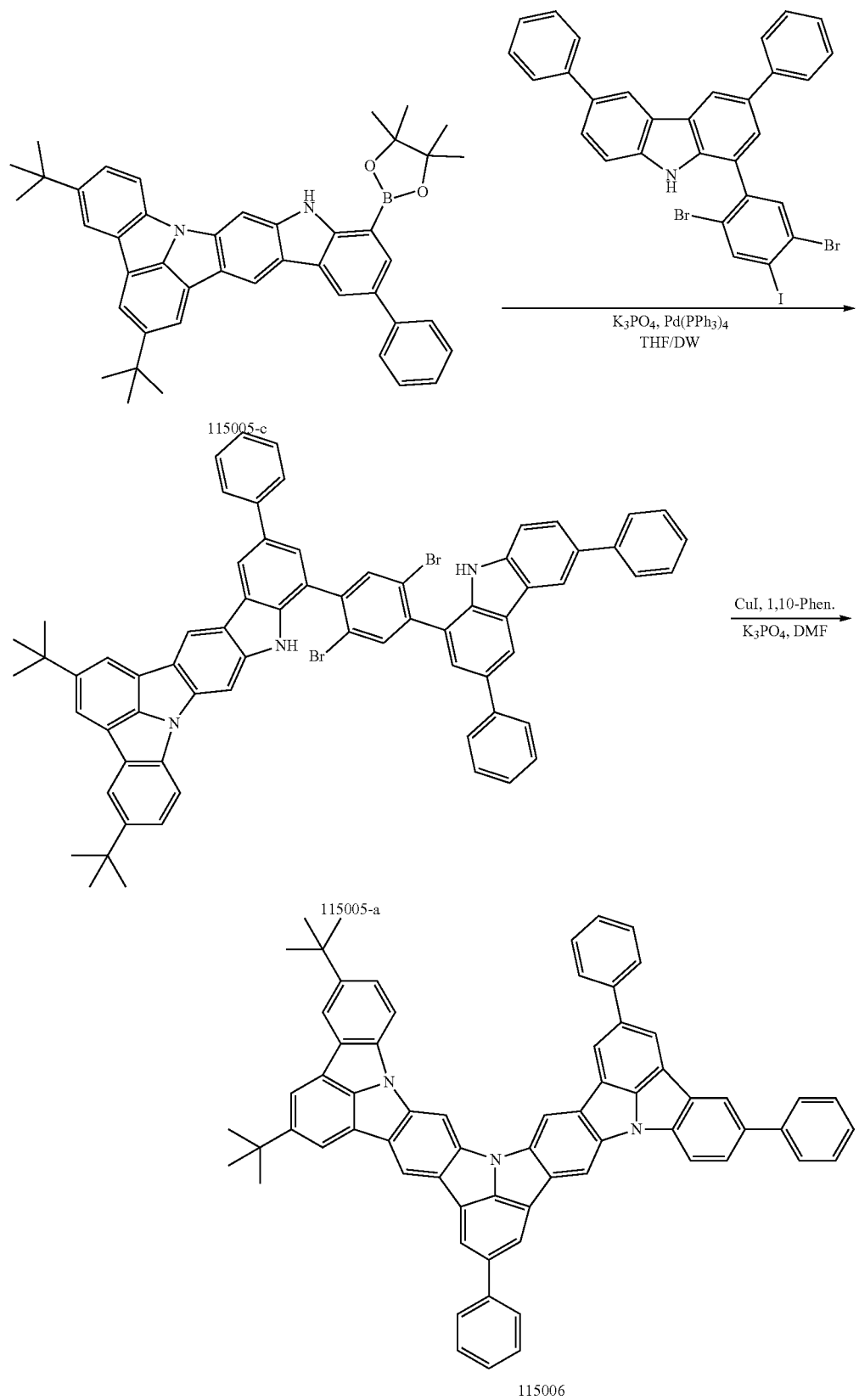

3845

Synthesis of Intermediate 115006-a 1.28 g of Intermediate 115006-a was obtained in substantially the same manner as in Synthesis of Intermediate 112002-a in Synthesis Example 2, except that Intermediate 115005-b was used in reaction (yield: 52%).

LC-Mass (calculated value: 1068.25 g/mol, found value: 1067.78 (M+1))

3846

Synthesis of Compound 115006

0.243 g of Compound 115006 was obtained in substantially the same manner as in Synthesis of Compound 112001 in Synthesis Example 1, except that Intermediate 115006-a was used in reaction (yield: 95%).

LC-Mass (calculated value: 908.4005 g/mol, found value: 908.4010 (M+1))

Synthesis Example 9: Synthesis of Compound 115007

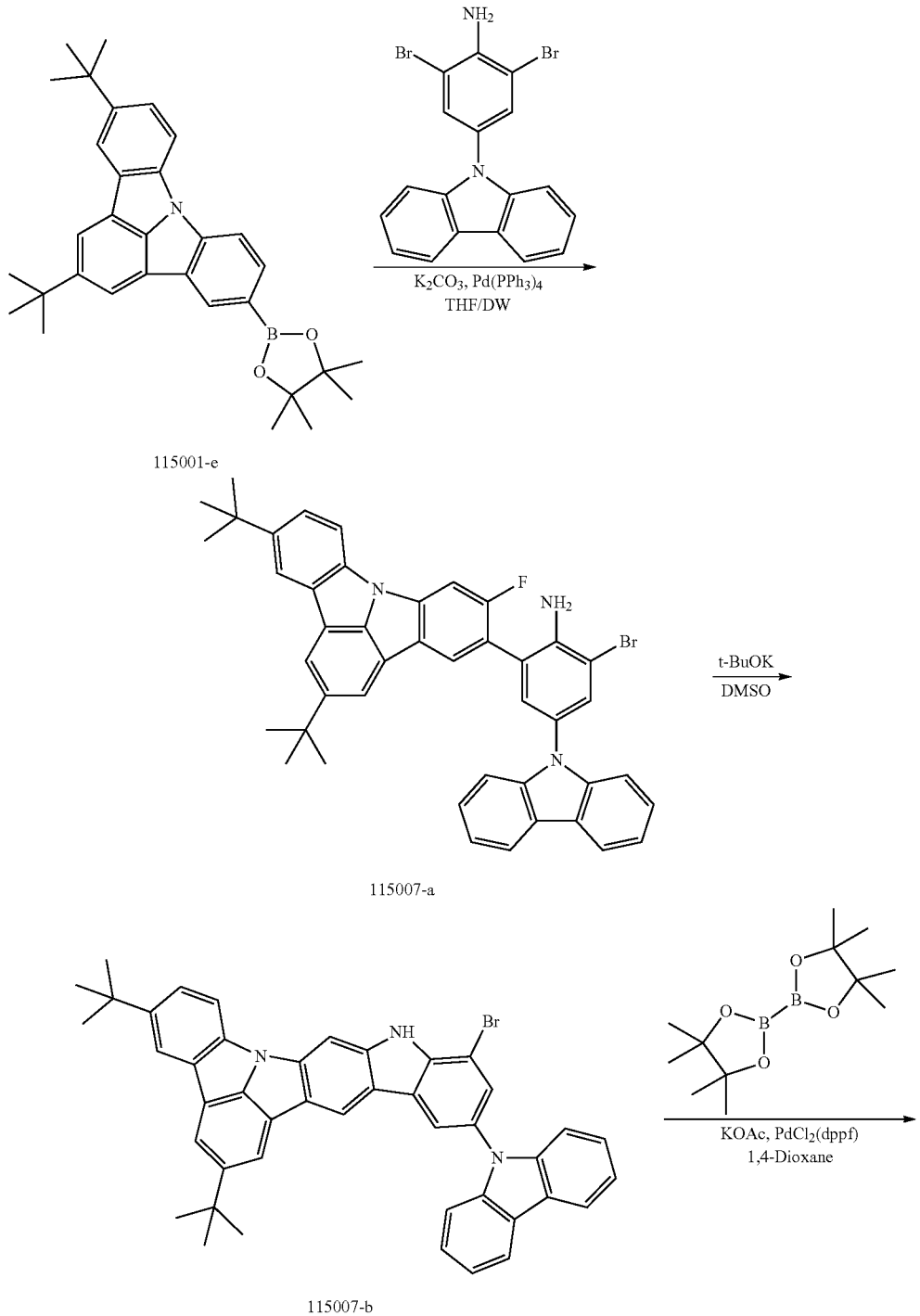

-continued
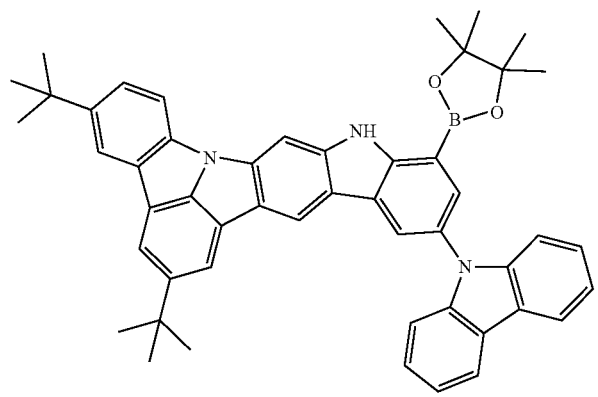
115005-c
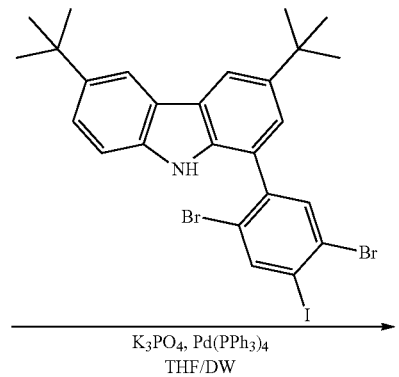
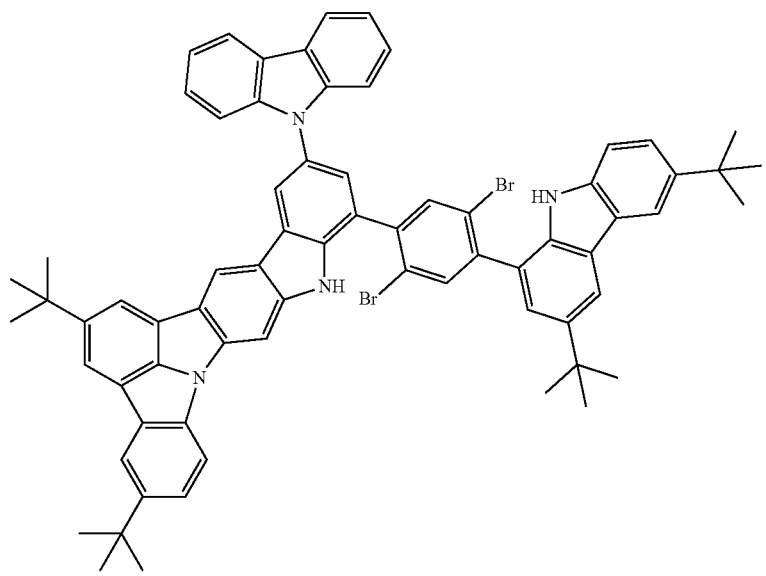
115007-d
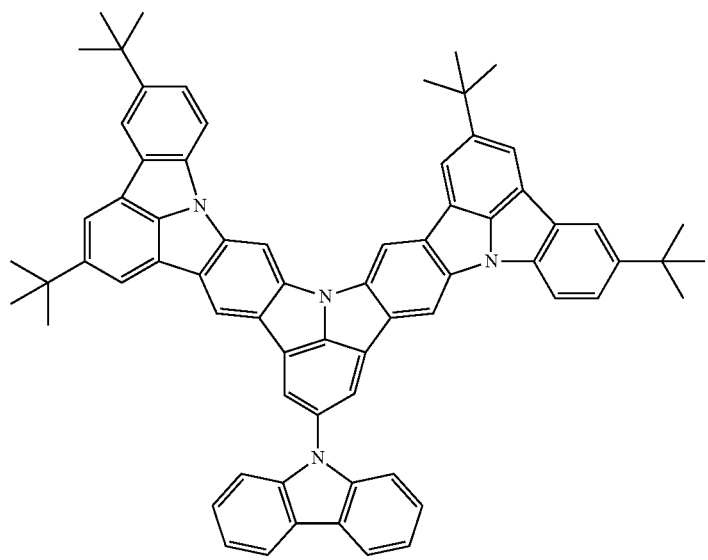
115007

Synthesis of Intermediate 115007-a 1.08 g of Intermediate 115007-a was obtained in substantially the same manner as in Synthesis of 112001-f in Synthesis Example 1, except that 2,6-dibromo-4-(9H-carbazole-9-yl) aniline was used instead of Intermediate 2,6-dibromo-4-(tert-butyl) aniline to react with Intermediate 115001-e, followed by purification (yield: 38%).

LC-Mass (calculated value: 706.22 g/mol, found value: 707.01 (M+1))

Synthesis of Intermediate 115007-b 1.53 g of Intermediate 115007-b was obtained in substantially the same manner as in Synthesis of Intermediate 112001-g in Synthesis Example 1, except that Intermediate 115007-a was used in reaction (yield: 63%).

LC-Mass (calculated value: 686.22 g/mol, found value: 686.75 (M+1))

Synthesis of Intermediate 115007-c 1.13 g of Intermediate 115007-c was obtained in substantially the same manner as in Synthesis of Intermediate 112001-h in Synthesis Example 1, except that Intermediate 115007-b was used (yield: 85%).

LC-Mass (calculated value: 734.39 g/mol, found value: 734.52 (M+1))

Synthesis of Intermediate 115007-d 0.821 g of Intermediate 115007-d was obtained in substantially the same manner as in Synthesis of Intermediate 112001-c in Synthesis Example 1, except that Intermediate 115007-c was used in reaction (yield: 48%).

LC-Mass (calculated value: 1117.34 g/mol, found value: 1118.52 (M+1))

Synthesis of Compound 115007

0.642 g of Compound 115007 was obtained in substantially the same manner as in Synthesis of Compound 112001 in Synthesis Example 1, except that Intermediate 115007-d was used in reaction (yield: 81%).

LC-Mass (calculated value: 957.4896 g/mol, found value: 957.4900 (M+1))

Synthesis Example 10: Synthesis of Compound 115008

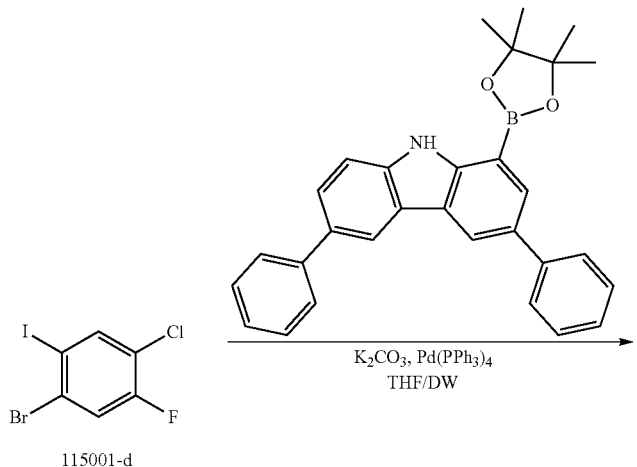

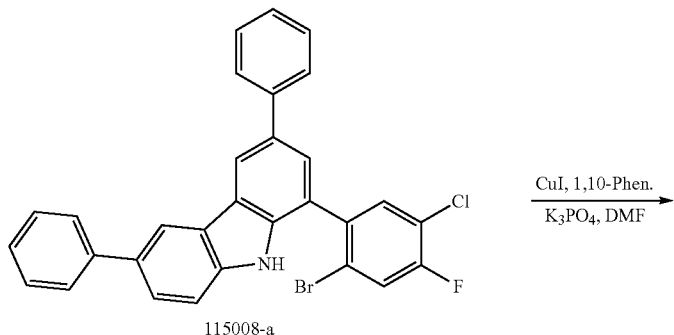

-continued
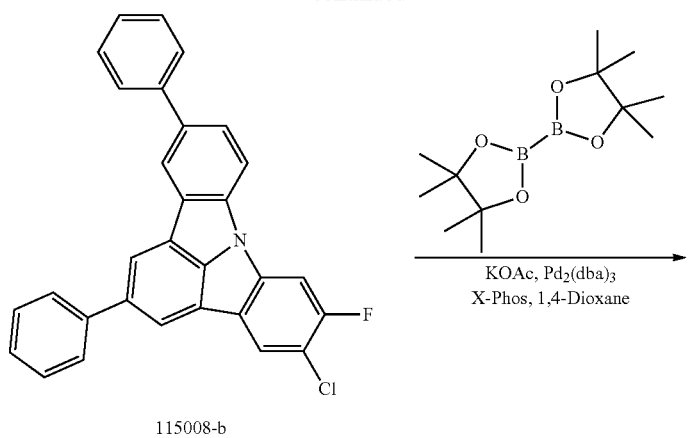
115008-b
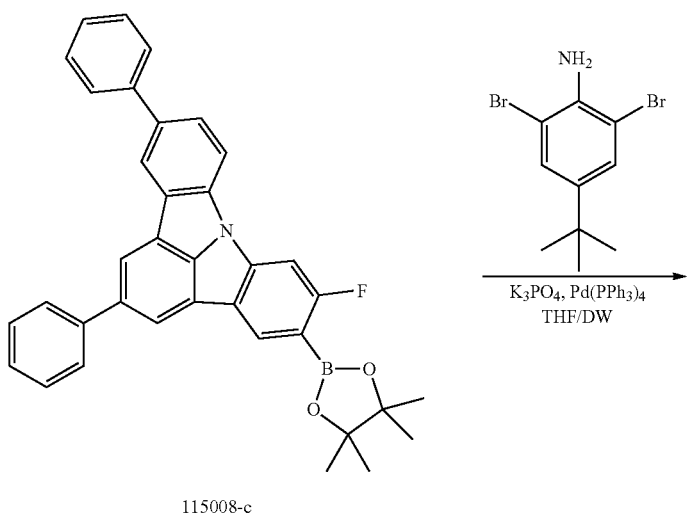
115008-c
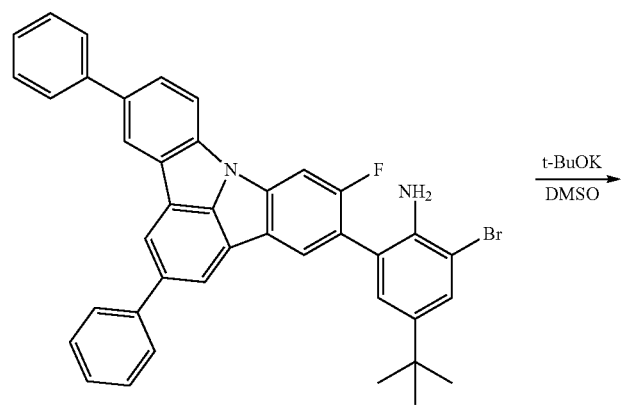
115008-d

-continued
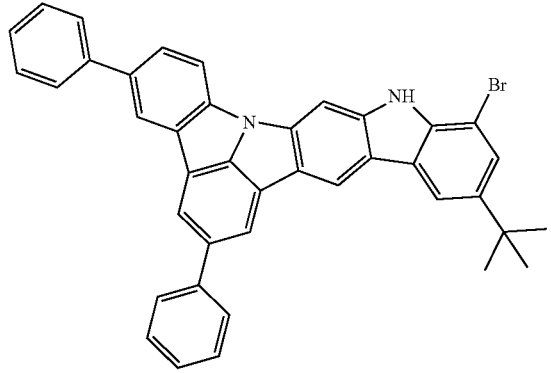
115008-e
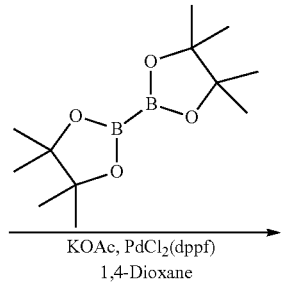
KOAc, PdCl$_2$(dppf)
1,4-Dioxane
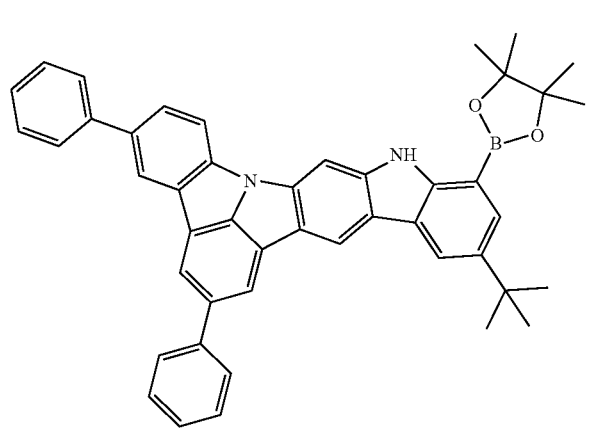
115008-e
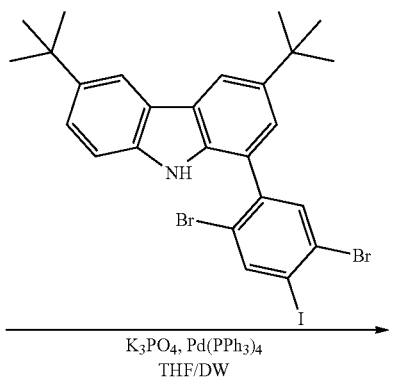
K$_3$PO$_4$, Pd(PPh$_3$)$_4$
THF/DW
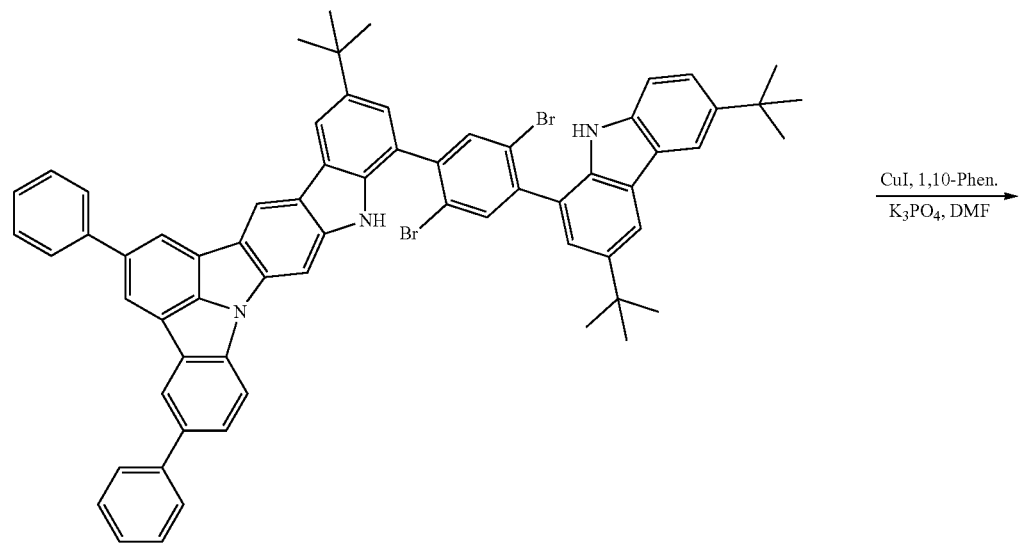
115008-g
CuI, 1,10-Phen.
K$_3$PO$_4$, DMF

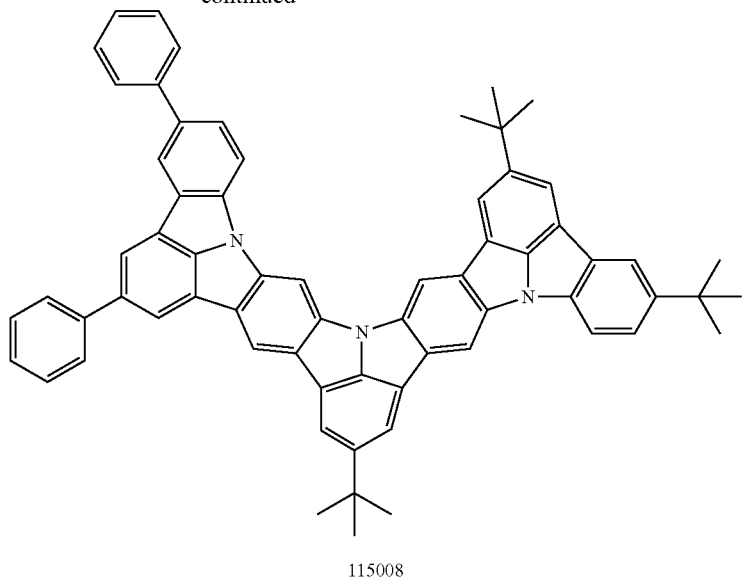

115008

Synthesis of Intermediate 115008-a 1.35 g of Intermediate 115008-a was obtained in substantially the same manner as in Synthesis of Intermediate 112001-c in Synthesis Example 1, except that 3,6-diphenyl-1-(4,4,5,5-tetramethyl-1,3,2-dioxaborolan-2-yl)-9H-carbazole was used as a start material instead of 3,6-di-tert-butyl-1-(4,4,5,5-tetramethyl-1,3,2-dioxaborolan-2-yl)-9H-carbazole to react with Intermediate 115001-b (yield: 42%).

LC-Mass (calculated value: 526.04 g/mol, found value: 527.00 (M+1))

Synthesis of Intermediate 115008-b 3.5213 g of Intermediate 115008-b was obtained in substantially the same manner as in Synthesis of Intermediate 112001-c in Synthesis Example 1, except that Intermediate 115008-a was used in reaction (yield: 91%).

LC-Mass (calculated value: 446.11 g/mol, found value: 446.29 (M+1))

Synthesis of Intermediate 115008-c 2.13 g of Intermediate 115008-c was obtained in substantially the same manner as in Synthesis of Intermediate 112001-e in Synthesis Example 1, except that Intermediate 115008-b was used instead of Intermediate 112001-d (yield: 71%).

LC-Mass (calculated value: 538.24 g/mol, found value: 538.78 (M+1))

Synthesis of Intermediate 115008-d 1.73 g of Intermediate 115008-d was obtained in substantially the same manner as in Synthesis of Intermediate 112001-f in Synthesis Example 1, except that Intermediate 115008-c was used (yield: 45%).

LC-Mass (calculated value: 637.17 g/mol, found value: 638.05 (M+1))

Synthesis of Intermediate 115008-e 1.32 g of Intermediate 115008-e was obtained in substantially the same manner as in Synthesis of Intermediate 112001-g in Synthesis Example 1, except that Intermediate 115008-d was used in reaction (yield: 65%).

LC-Mass (calculated value: 617.16 g/mol, found value: 617.85 (M+1))

Synthesis of Intermediate 115008-f 1.02 g of Intermediate 115008-f was obtained in substantially the same manner as in Synthesis of Intermediate 112001-h in Synthesis Example 1, except that Intermediate 115008-e was used in reaction (yield: 81%).

LC-Mass (calculated value: 665.33 g/mol, found value: 666.11 (M+1))

Synthesis of Intermediate 115008-g

Intermediate 115008-f was subjected to synthesis in substantially the same manner as in Synthesis of Intermediate 112001-c in Synthesis Example 1. Once the reaction and purification were complete, 1.00 g of Intermediate 115008-g was obtained (yield: 47%).

LC-Mass (calculated value: 1048.28 g/mol, found value: 1047.99 (M+1))

Synthesis of Compound 115008

0.441 g of Compound 115008 was obtained in substantially the same manner as in Synthesis of Compound 112001 in Synthesis Example 1 (yield: 83%).

LC-Mass (calculated value: 888.4318 g/mol, found value: 888.4320 (M+1)) Synthesis Example 11: Synthesis of Compound 115009

3857 3858
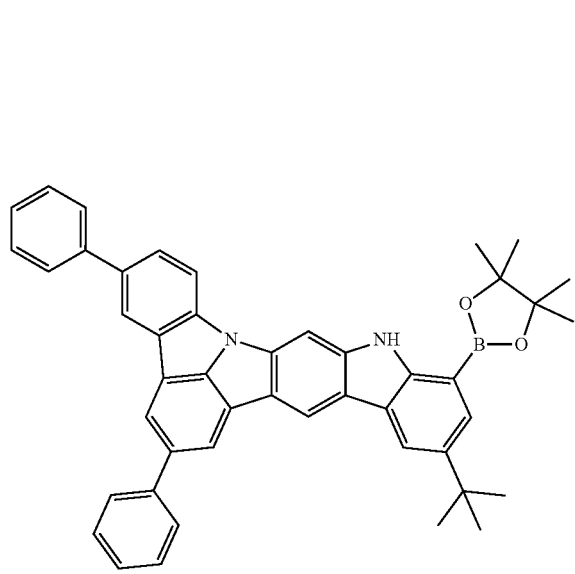
115001-f
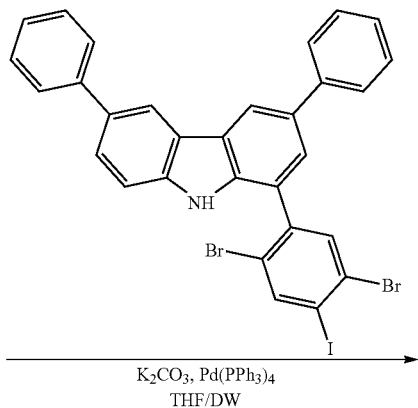
K₂CO₃, Pd(PPh₃)₄
THF/DW
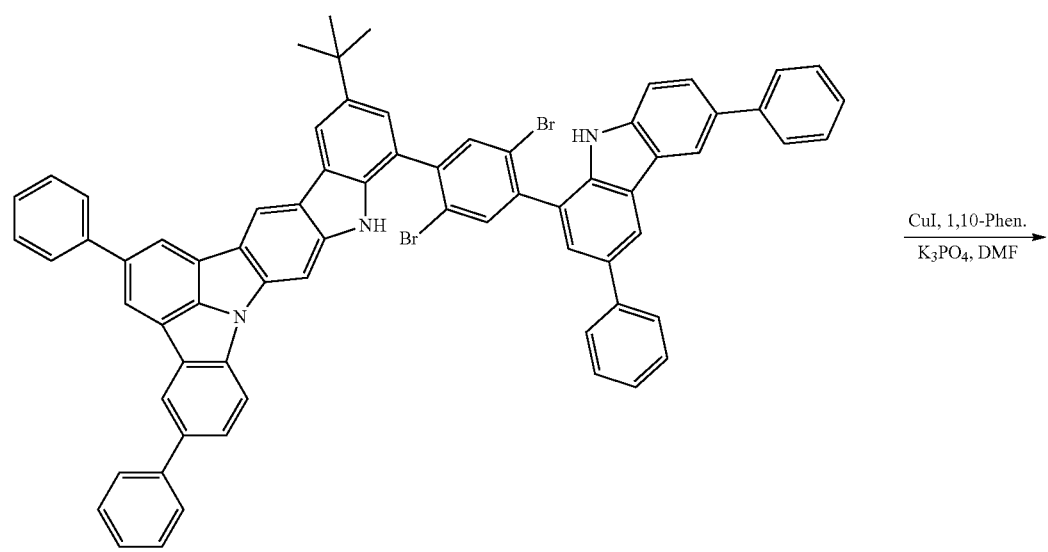
115009-a
CuI, 1,10-Phen.
K₃PO₄, DMF -continued

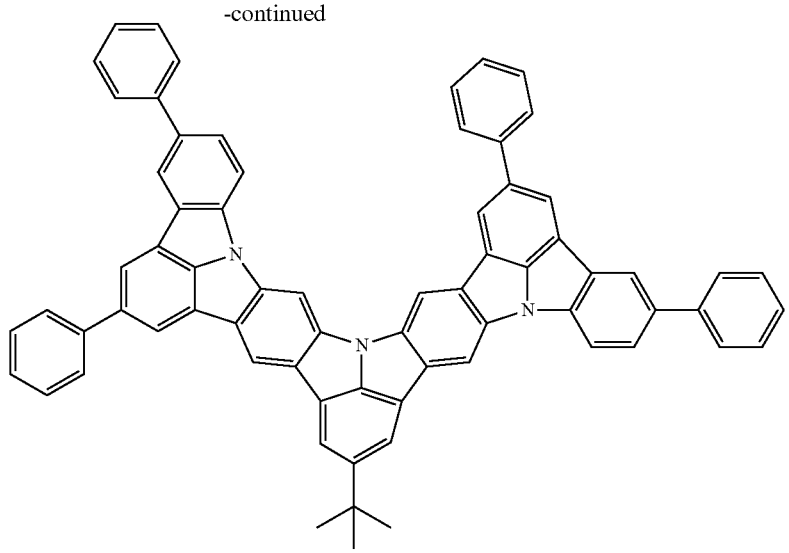

115009

Synthesis of Intermediate 115009-a

Intermediate 115008-f was subjected to synthesis in substantially the same manner as in Synthesis of Intermediate 112002-a in Synthesis Example 2. 1.23 g of Intermediate 115009-a was obtained after purification completed (yield: 44%).

LC-Mass (calculated value: 1088.22 g/mol, found value: 1089.11 (M+1))

Synthesis of Compound 115009

0.333 g of Compound 115009 was obtained in substantially the same manner as in Synthesis of Compound 112001 in Synthesis Example 1, except that Intermediate 115009-a was used in reaction (yield: 91%).

LC-Mass (calculated value: 928.3692 g/mol, found value: 928.3690 (M+1))

Synthesis Example 12: Synthesis of Compound 121001

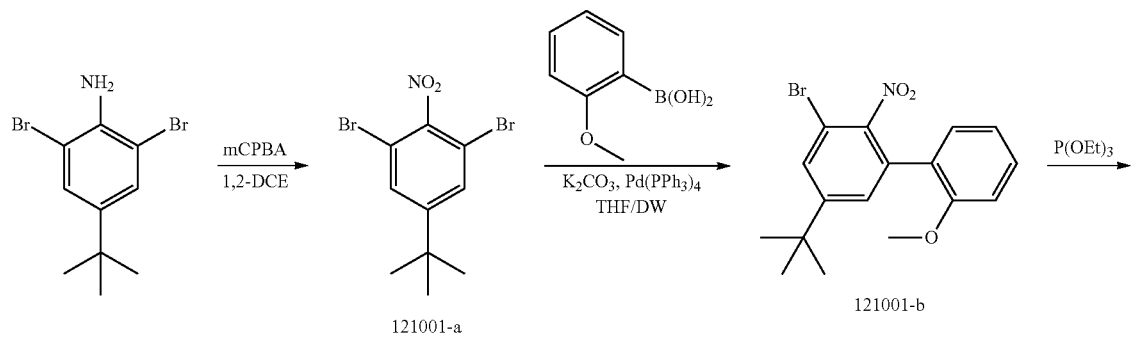

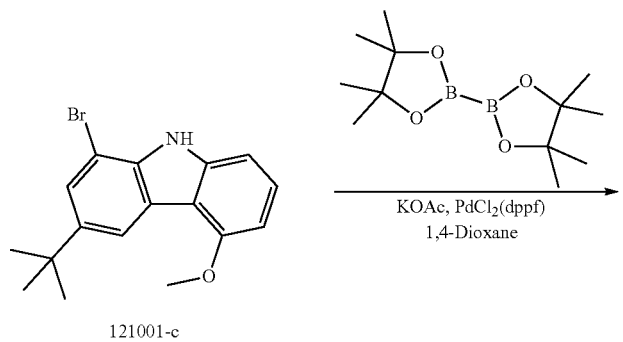

121001-c

-continued
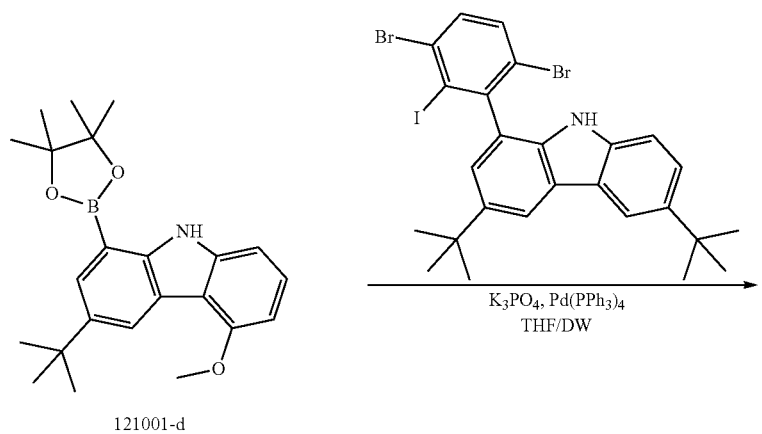
121001-d
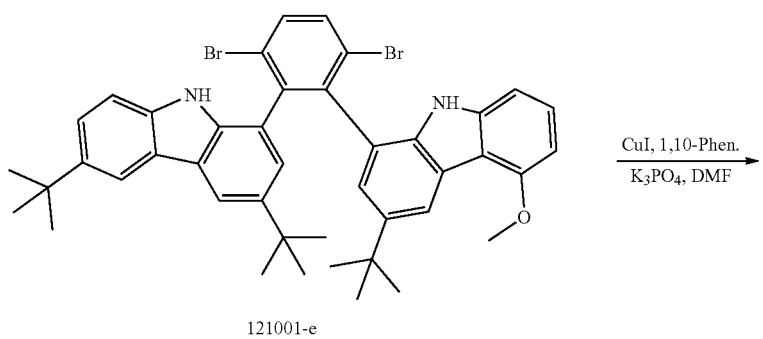
121001-e
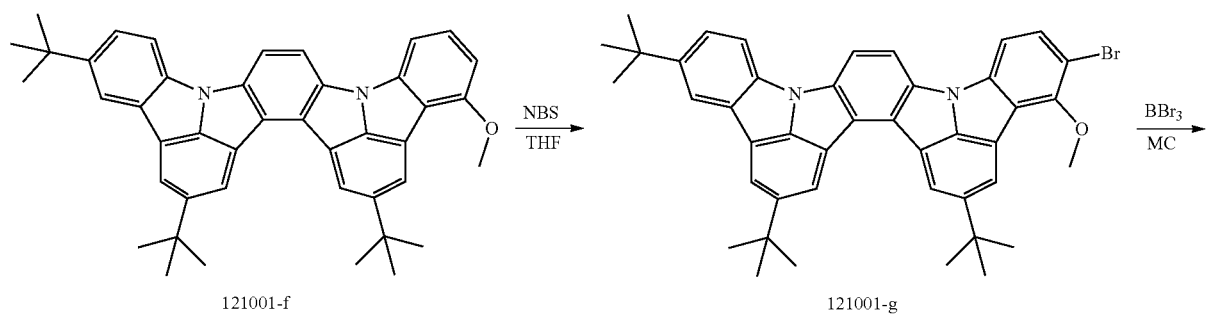
121001-f  →(NBS/THF)→  121001-g  →(BBr₃/MC)→
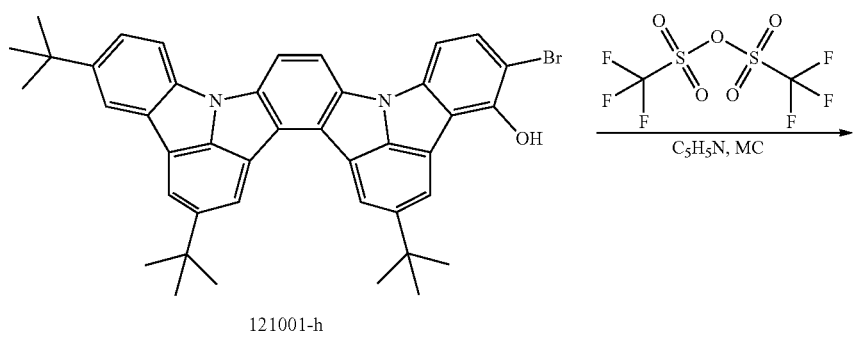
121001-h

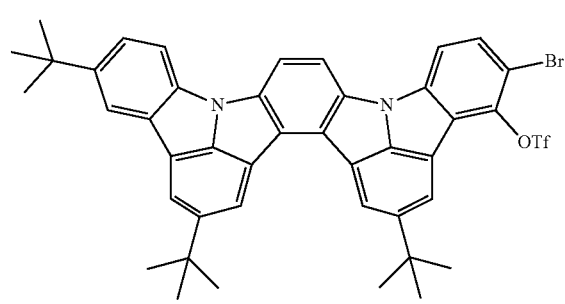

121001-i

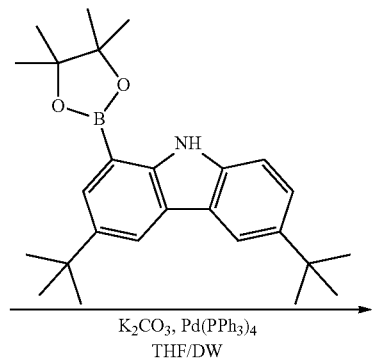

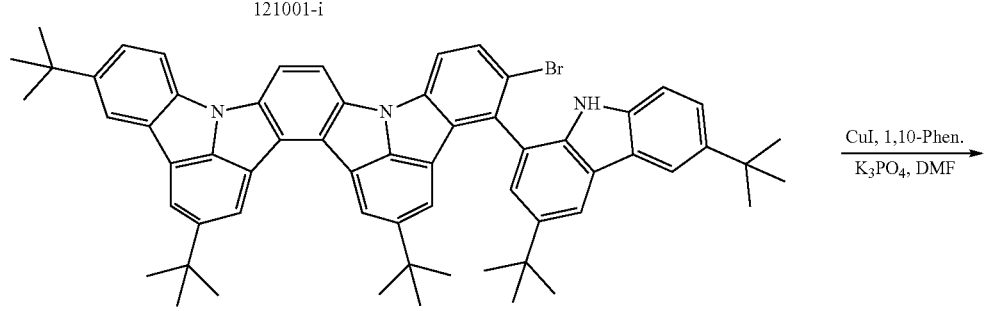

121001-j

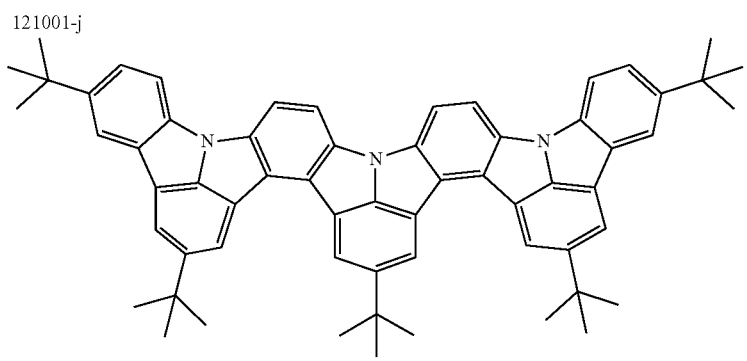

121001

Synthesis of Intermediate 121001-a 100 g (326 mmol) of 2,6-dibromo-4-(tert-butyl) aniline, 276 g (1.30 mol) of m-chloroperbenzoic acid (mCPBA), and 1,500 mL of 1,2-dichloroethane (1,2-DCE) were added to a round flask and stirred. After heating for reflux and cooling for 16 hours, a sodium thiosulfate aqueous solution was added thereto. Then an extraction process was performed using dichloromethane and distilled water. The extracted organic layer was purified using column chromatography and dried to thereby obtain 62.1 g of Intermediate 121001-a (yield: 56%).

LC-Mass (calculated value: 335.92 g/mol, found value: 336.02 (M+1))

Synthesis of Intermediate 121001-b 12.5 g of Intermediate 121001-b was obtained in substantially the same manner as in Synthesis of Intermediate 112001-f in Synthesis Example 1, except that 15.0 g (98.9 mmol) of (2-methoxyphenyl) boronic acid was used as a start material instead of 50.0 g (148 mmol) of Intermediate 121001-a (yield: 35%).

LC-Mass (calculated value: 364.05 g/mol, found value: 365.11 (M+1))

Synthesis of Intermediate 121001-c 20.0 g (54.9 mmol) of Intermediate 121001-b and 200 mL of triethyl phosphite were stirred in a round flask and heated for 3 days at a temperature of 200° C. to allow a reaction to occur. Once the reaction was complete, 1,000 mL of ethanol was added thereto, followed by stirring for 3 hours. After an extraction process was complete, separation and purification were performed through column chromatography to remove impurities. 4.01 g of Intermediate 121001-c was obtained after drying (yield: 22%).

LC-Mass (calculated value: 332.07 g/mol, found value: 332.55 (M+1))

Synthesis of Intermediate 121001-d 15.0 g (45.1 mmol) of Intermediate 121001-c was used in substantially the same manner as in Synthesis of Intermediate 112001-h in Synthesis Example 1. 15.3 g of Intermediate 121001-d was obtained after purification completed (yield: 89%).
LC-Mass (calculated value: 380.24 g/mol, found value: 379.98 (M+1))

Synthesis of Intermediate 121001-e 8.27 g of Intermediate 121001-e was obtained in substantially the same manner as in Synthesis of Intermediate 112001-i in Synthesis Example 1, except that Intermediate 121001-d was used instead of Intermediate 112001-h (yield: 41%).
LC-Mass (calculated value: 763.19 g/mol, found value: 763.15 (M+1))

Synthesis of Intermediate 121001-f 5.91 g of Intermediate 121001-f was obtained in substantially the same manner as in Synthesis of Compound 112001 in Synthesis Example 1, except that Intermediate 121001-d was used in reaction (yield: 94%).
LC-Mass (calculated value: 603.34 g/mol, found value: 604.21 (M+1))

Synthesis of Intermediate 121001-g

A reaction was performed in substantially the same manner as in Synthesis of Intermediate 112001-a in Synthesis Example 1, except that THF was used instead of DMF as a solvent, and Intermediate 121001-f was used in reaction. 1.62 g of Intermediate 121001-g was obtained (yield: 48%).
LC-Mass (calculated value: 681.25 g/mol, found value: 681.77 (M+1))

Synthesis of Intermediate 121001-h 5.00 g (7.33 mmol) of Intermediate 121001-g was dissolved in 100 ml of dichloromethane and cooled to −78° C. Then, 3.67 g (14.7 mmol) of boron tribromide (BBr$_3$) was slowly added thereto. 24 hours after stirring, distilled water was added thereto to quench excess BBr$_3$. Then, neutralization was performed until pH 7 was reacted by using a sodium hydroxide aqueous solution. An extraction process was performed using dichloromethane and distilled water. Then, precipitation was performed using n-hexane, followed by filtering and drying. 3.12 g of Intermediate 121001-h was thus obtained (yield: 64%).
LC-Mass (calculated value: 667.23 g/mol, found value: 667.01 (M+1))

Synthesis of Intermediate 121001-i 12.0 g (18.0 mmol) of Intermediate 121001-h, 2.84 g (35.9 mmol) of pyridine, and 120 mL of dichloromethane were added to a round flask, and the temperature was adjusted to 0° C. 6.08 g (21.6 mmol) of triflic anhydride was dissolved in 60 mL of dichloromethane, and the solution was slowly added to a round flask and stirred at room temperature for three hours. Once the reaction was complete, diethyl ether and a hydrochloride (HCl) aqueous solution were used for quenching and extraction. Then, a purification process was performed using column chromatography. Once the drying complete, 10.2 g of Intermediate 121001-i was obtained (yield: 71%).
LC-Mass (calculated value: 799.18 g/mol, found value: 800.01 (M+1))

Synthesis of Intermediate 121001-j 2.64 g of Intermediate 121001-j was obtained in substantially the same manner as in Synthesis of Intermediate 112001-f in Synthesis Example 1, except that Intermediate 121001-i was used in reaction, followed by purification (yield: 50%).
LC-Mass (calculated value: 928.42 g/mol, found value: 927.97 (M+1))

Synthesis of Compound 121001

1.65 g of Compound 121001 was obtained in substantially the same manner as in Synthesis of Intermediate 112001-d in Synthesis Example 1, except that Intermediate 121001-j was used in reaction (yield: 90%).
LC-Mass (calculated value: 848.4944 g/mol, found value: 848.4949 (M+1))

Synthesis Example 13: Synthesis of Compound 121002

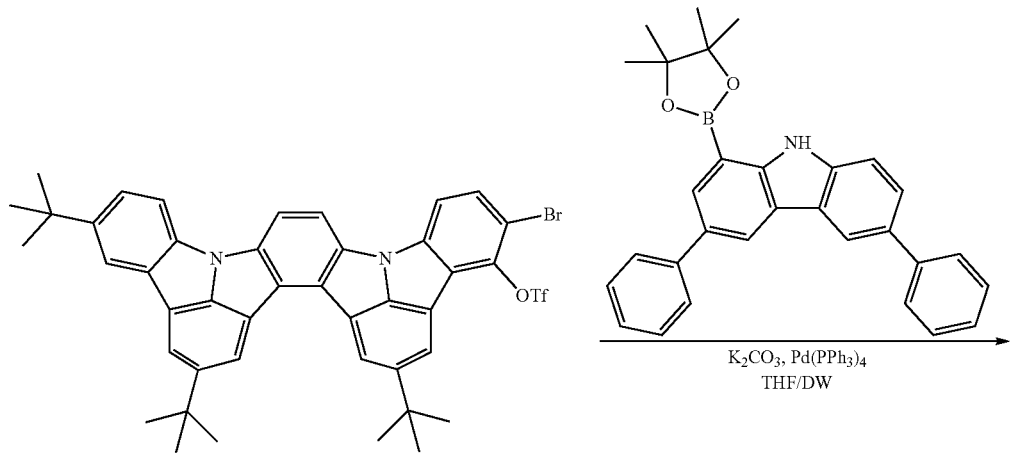

-continued

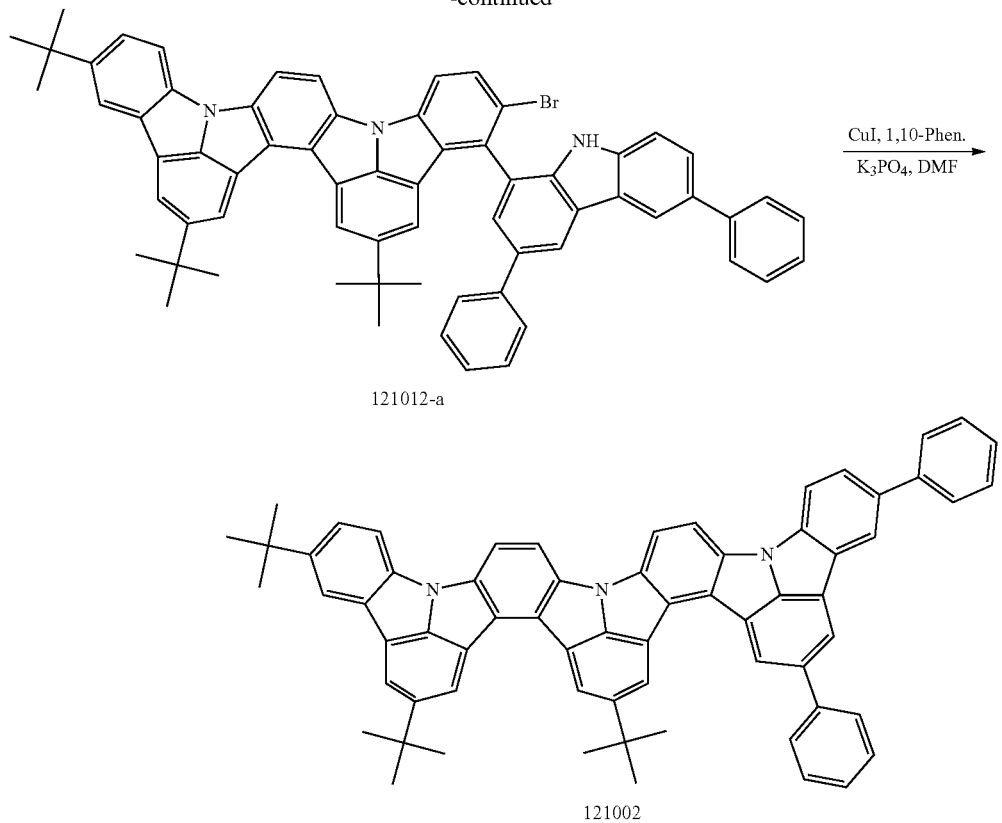

121012-a

121002

Synthesis of Intermediate 121002-a 1.32 g of Intermediate 121001-a was obtained in substantially the same manner as in Synthesis of Intermediate 112001-f in Synthesis Example 1, except that Intermediate 121002-i was used in reaction (yield: 42%).

LC-Mass (calculated value: 968.36 g/mol, found value: 968.72 (M+1))

Synthesis of Compound 121002

0.87 g of Compound 121002 was obtained in substantially the same manner as in Synthesis of Intermediate 112001-d in Synthesis Example 1, except that Intermediate 121002-a was used in reaction (yield: 88%).

LC-Mass (calculated value: 888.4318 g/mol, found value: 888.4317 (M+1))

Synthesis Example 14: Synthesis of Compound 122001

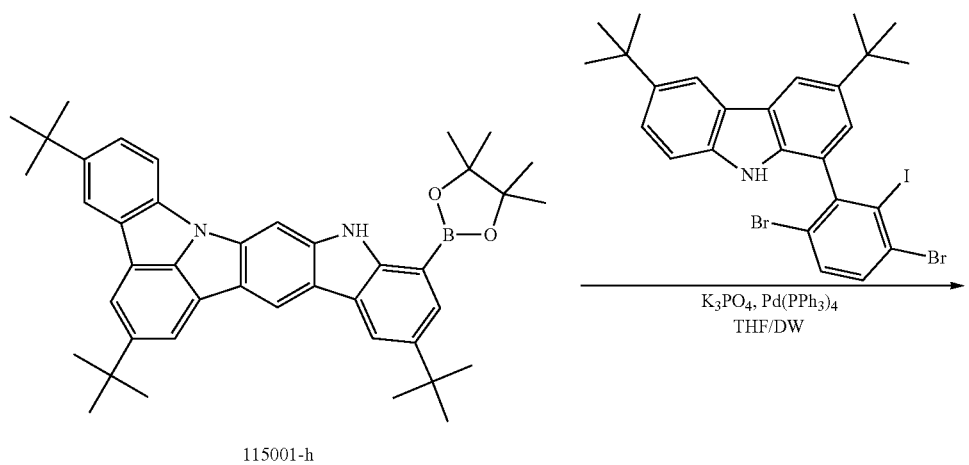

115001-h

-continued

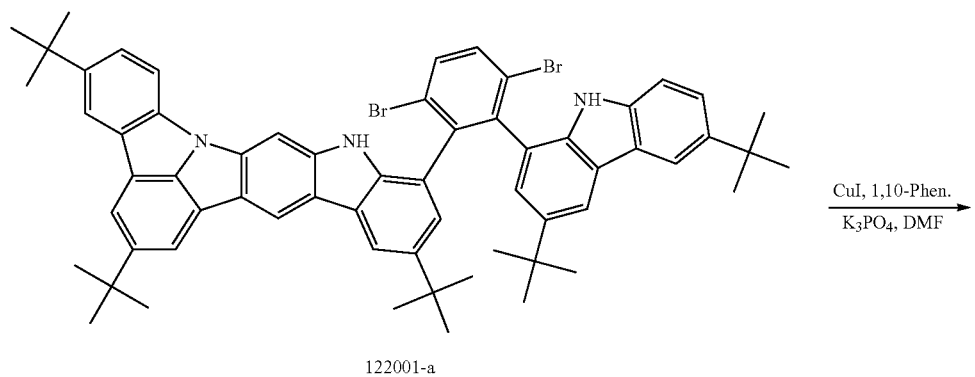
122001-a

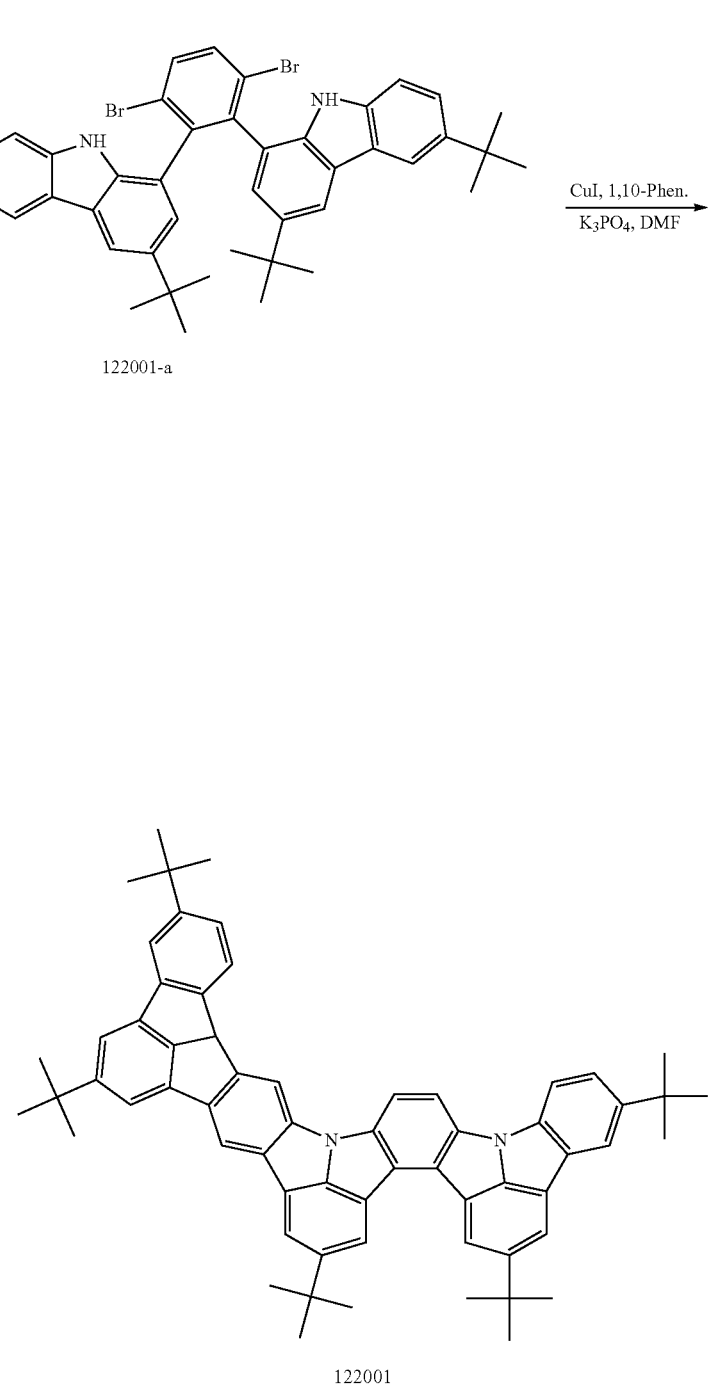
122001

Synthesis of Intermediate 122001-a

A reaction was performed in substantially the same manner as in Synthesis of Intermediate 112001-c in Synthesis Example 1, except that Intermediate 115001-h was used. 1.11 g of Intermediate 122001-a was obtained after purification completed (yield: 43%).

LC-Mass (calculated value: 1008.35 g/mol, found value: 1007.77 (M+1))

Synthesis of Compound 122001

0.52 g of Compound 122001 was obtained in substantially the same manner as in Synthesis of Compound 112001 in Synthesis Example 1, except that Intermediate 122001-a was used in reaction (yield: 89%).

LC-Mass (calculated value: 848.4944 g/mol, found value: 848.4953 (M+1))

Synthesis Example 15: Synthesis of Compound 122002
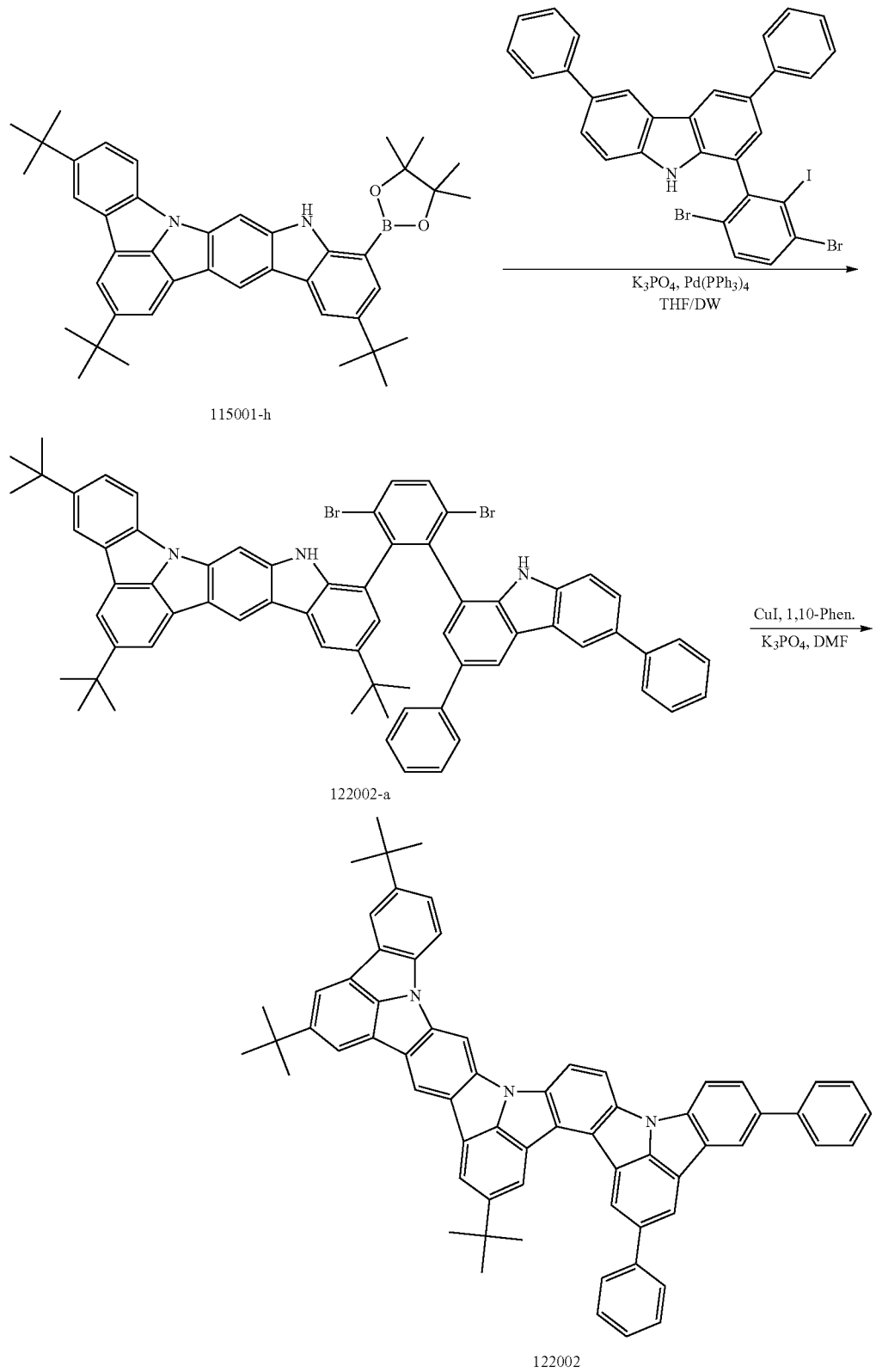

3873

Synthesis of Intermediate 122002-a 0.95 g of Intermediate 122002-a was obtained in substantially the same manner as in Synthesis of Intermediate 112001-c in Synthesis Example 1, except that Intermediate 115001-h was used in reaction (yield: 46%).

LC-Mass (calculated value: 1048.28 g/mol, found value: 1049.01 (M+1))

3874

Synthesis of Compound 122002

0.532 g of Compound 122002 was obtained in substantially the same manner as in Synthesis of Compound 112001 in Synthesis Example 1, except that Intermediate 122002-a was used in reaction (yield: 79%).

LC-Mass (calculated value: 888.4318 g/mol, found value: 888.4320 (M+1))

Synthesis Example 16: Synthesis of Compound 124001

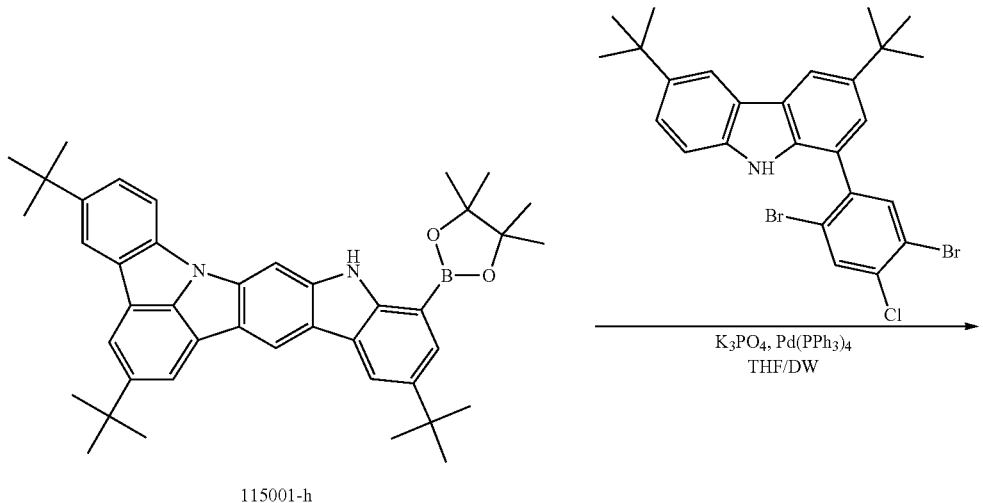

115001-h

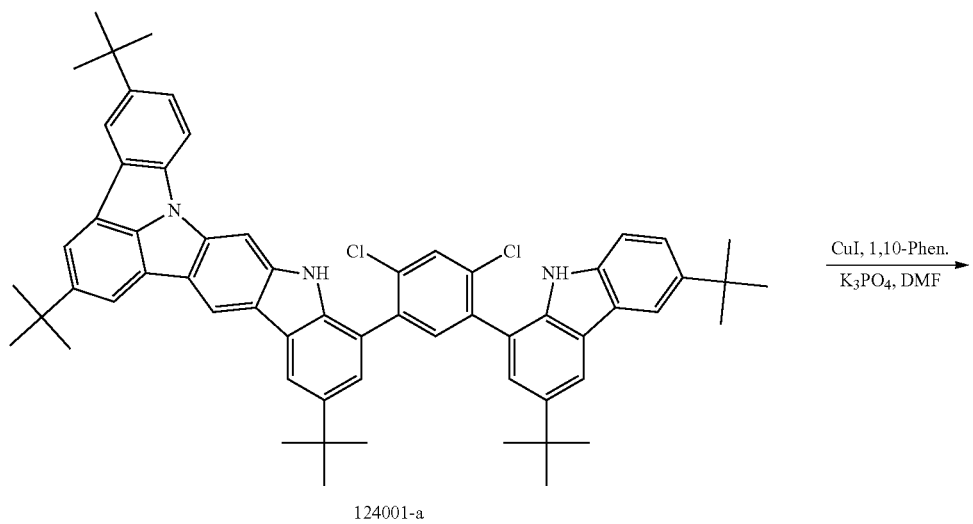

124001-a

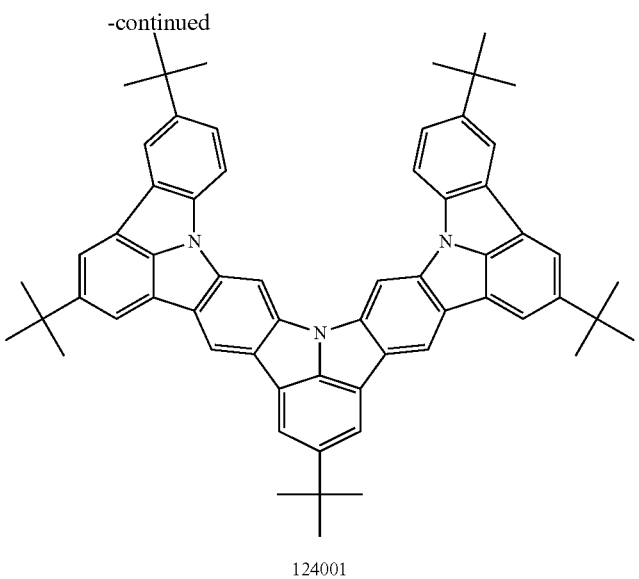

124001

Synthesis of Intermediate 124001-a

A reaction was performed in substantially the same manner as in Synthesis of Intermediate 112001-i in Synthesis Example 1, except that 1-(5-bromo-2,4-dichlorophenyl)-3,6-di-tert-butyl-9H-carbazole was used instead of 3,6-di-tert-butyl-1-(3,6-dibromo-2-iodophenyl)-9H-carbazole. Then, 1.23 g of Intermediate 124001-a was obtained (yield: 65%).

LC-Mass (calculated value: 920.45 g/mol, found value: 921.54 (M+1))

Synthesis of Compound 124001

0.71 g of Compound 124001 was obtained in substantially the same manner as in Synthesis of Compound 112001 in Synthesis Example 1, except that dimethyl sulfoxide was used instead of DMF was used in reaction (yield: 64%).

LC-Mass (calculated value: 848.4944 g/mol, found value: 848.4946 (M+1))

Synthesis Example 17: Synthesis of Compound 141001

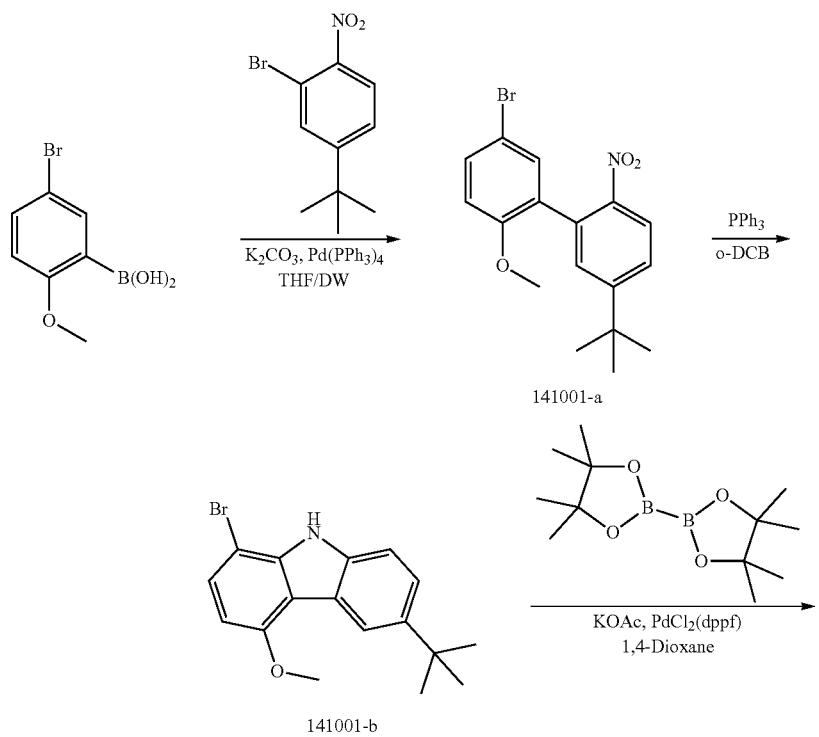

-continued
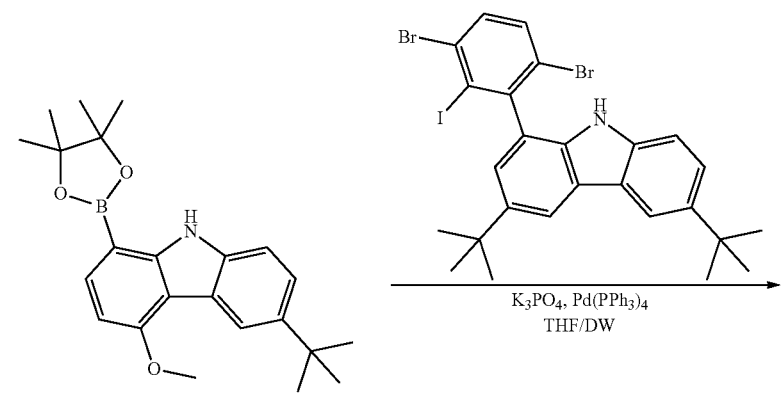
141001-c
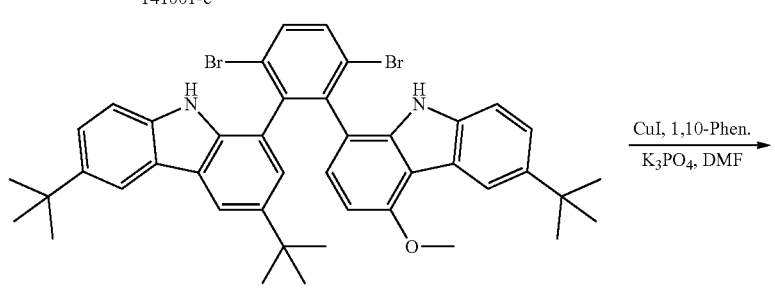
141001-d
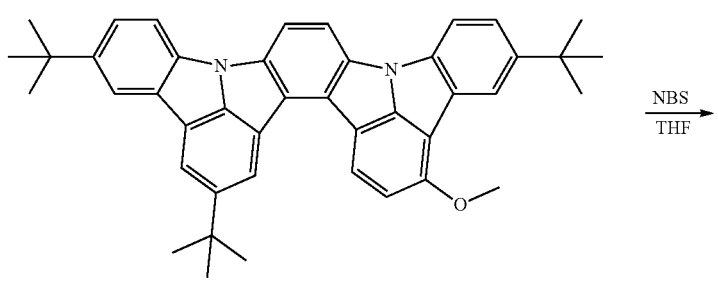
141001-e
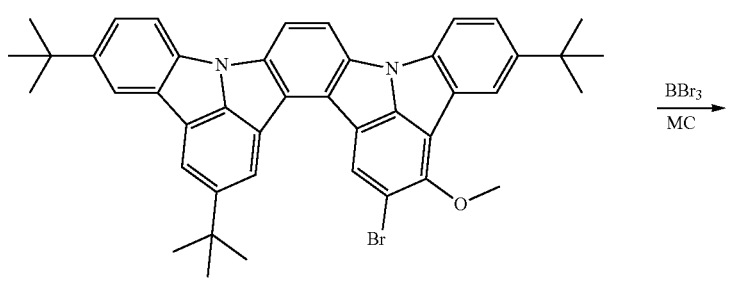
141001-f
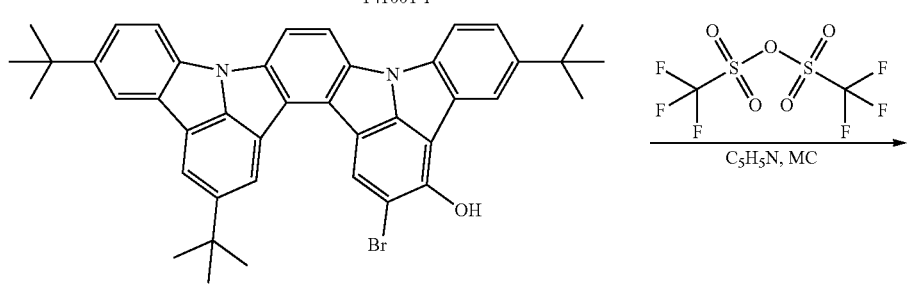
141001-g -continued
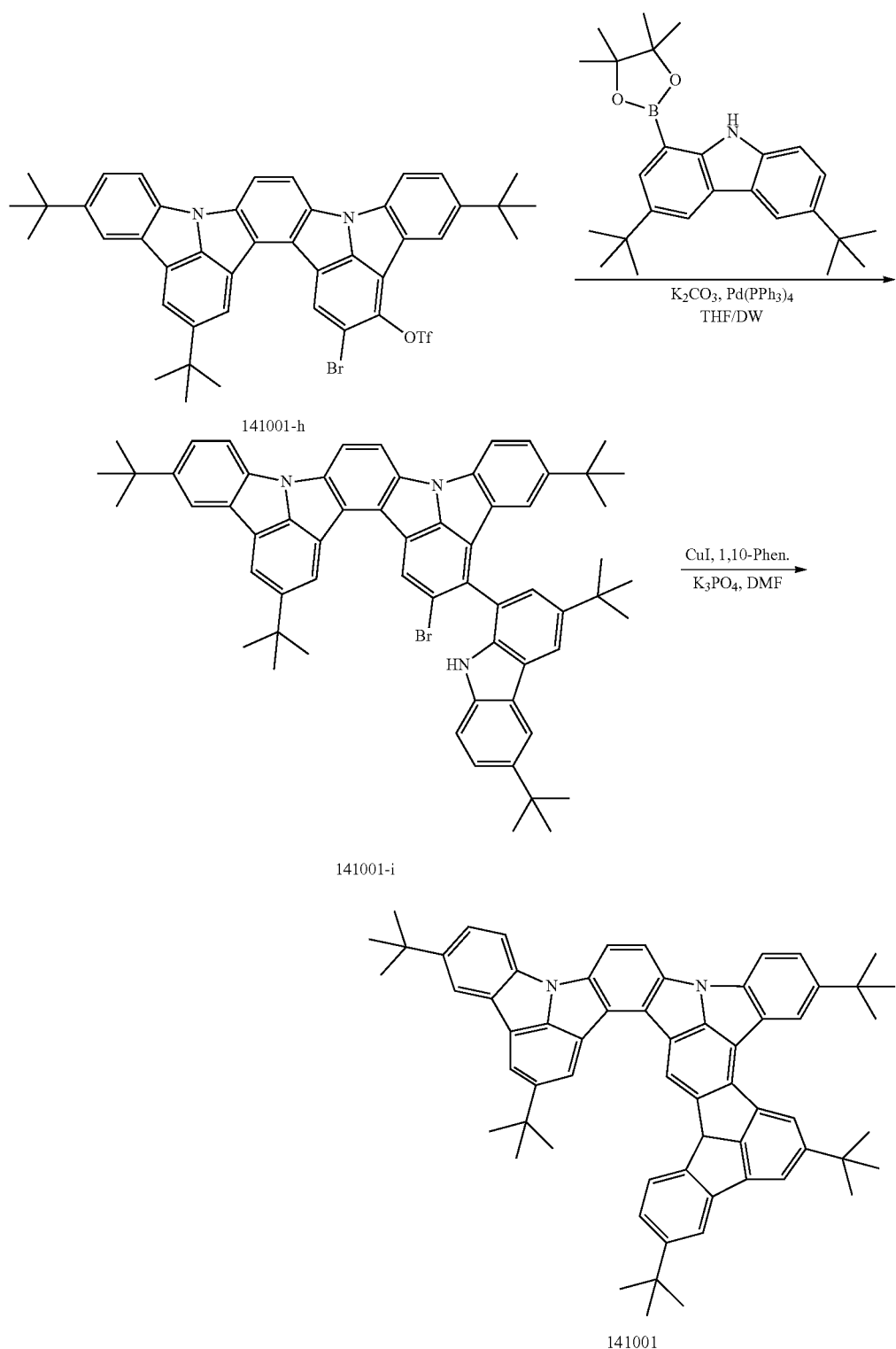
Synthesis of Intermediate 141001-a
245 g of Intermediate 141001-a was obtained in substantially the same manner as in Synthesis of Intermediate 121001-b in Synthesis Example 12, except that 268 g (1.04 mol) of 2-bromo-4-(tert-butyl)-1-nitrobenzene was used instead of Intermediate 121001-a, followed by purification (yield: 78%).
LC-Mass (calculated value: 364.05 g/mol, found value: 364.72 (M+1))

Synthesis of Intermediate 141001-b 100 g (0.275 mol) of Intermediate 141001-a, 216 g (0.824 mol) of triphenylphosphine (PPh₃), and 750 ml of 1,2-dichlorobenzne (o-DCB) were stirred together while heating at a temperature of 200° C. 5 hours later, 72.0 g (0.275 mol) of PPh₃ was added thereto to perform a reaction. Once the reaction was complete, excess o-DCB and PPh₃ were removed by using silica filter, and then, impurities were separated and purified through column chromatography. 73.9 g of Intermediate 141001-b was thus obtained (yield: 81%).

LC-Mass (calculated value: 332.07 g/mol, found value: 331.99 (M+1))

Synthesis of Intermediate 141001-c 66.8 g of Intermediate 141001-c was obtained in substantially the same manner as in Synthesis of Intermediate 112001-h in Synthesis Example 1, except that 75.0 g (0.226 mmol) of Intermediate 141001-b was used instead of Intermediate 112001-g in reaction (yield: 78%).

LC-Mass (calculated value: 380.24 g/mol, found value: 381.01 (M+1))

Synthesis of Intermediate 141001-d 38.3 g of Intermediate 141001-d was obtained in substantially the same manner as in Synthesis of Intermediate 112001-i in Synthesis Example 1, except that Intermediate 141001-c was used instead of Intermediate 112001-h (yield: 38%).

LC-Mass (calculated value: 763.19 g/mol, found value: 763.88 (M+1))

Synthesis of Intermediate 141001-e

A reaction was performed in substantially the same manner as in Synthesis of Compound 112001 in Synthesis Example 1, except that 42.0 g (54.9 mmol) of Intermediate 141001-d was used as a start material. 30.8 g of Intermediate 141001-e was thus obtained (yield: 93%).

LC-Mass (calculated value: 603.34 g/mol, found value: 603.97 (M+1))

Synthesis of Intermediate 141001-f 14.2 g of Intermediate 141001-f was obtained in substantially the same manner as in Synthesis of Intermediate 121001-g in Synthesis Example 12, except that 20.0 g (33.2 mmol) of Intermediate 141001-e was used in reaction (yield: 63%).

LC-Mass (calculated value: 681.25 g/mol, found value: 682.01 (M+1))

Synthesis of Intermediate 141001-g 9.99 g of Intermediate 141001-g was obtained in substantially the same manner as in Synthesis of Intermediate 121001-h in Synthesis Example 12, except that 15.0 g (22.0 mmol) of Intermediate 141001-f was used instead of Intermediate 121001-h in reaction (yield: 68%).

LC-Mass (calculated value: 667.23 g/mol, found value: 667.33 (M+1))

Synthesis of Intermediate 141001-h

A reaction was performed n substantially the same manner as in Synthesis of Intermediate 121001-i in Synthesis Example 12, except that 5.00 g (7.49 mmol) of Intermediate 141001-g was used as a start material. 3.77 g of Intermediate 141001-h was thus obtained (yield: 63%).

LC-Mass (calculated value: 799.18 g/mol, found value: 800.01 (M+1))

Synthesis of Intermediate 141001-i 1.05 g of Intermediate 141001-i was obtained in substantially the same manner as in Synthesis of Intermediate 121001-i in Synthesis Example 12, except that 2.00 g (2.50 mmol) of Intermediate 141001-h was used instead of Intermediate 121001-i in reaction (yield: 45%).

LC-Mass (calculated value: 928.42 g/mol, found value: 928.51 (M+1))

Synthesis of Compound 141001

0.642 g of Compound 141001 was obtained in substantially the same manner as in Synthesis of Intermediate 112001-d in Synthesis Example 1, except that 0.800 g (0.861 mmol) of Intermediate 141001-i was in reaction (yield: 88%).

LC-Mass (calculated value: 848.4944 g/mol, found value: 848.4948 (M+1))

Synthesis Example 18: Synthesis of Compound 143001

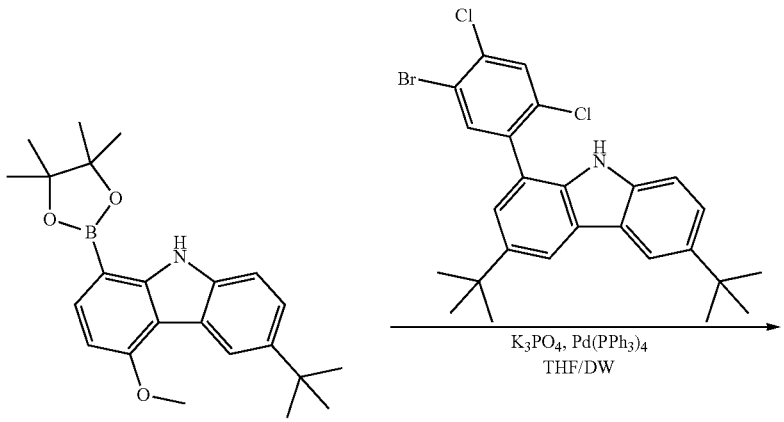

-continued
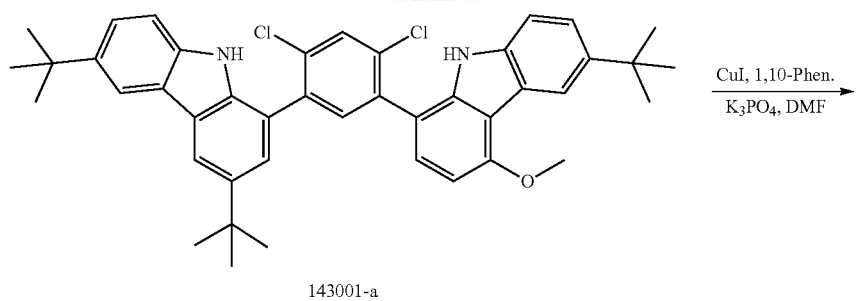
143001-a
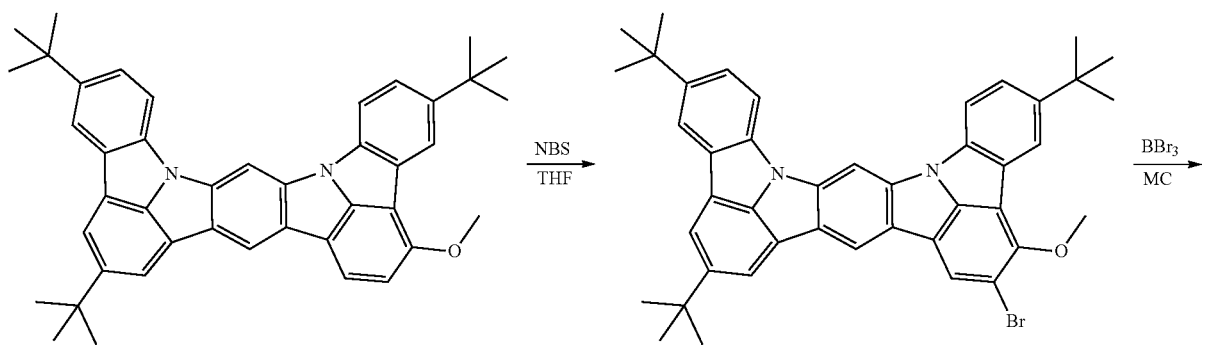
143001-b
143001-c
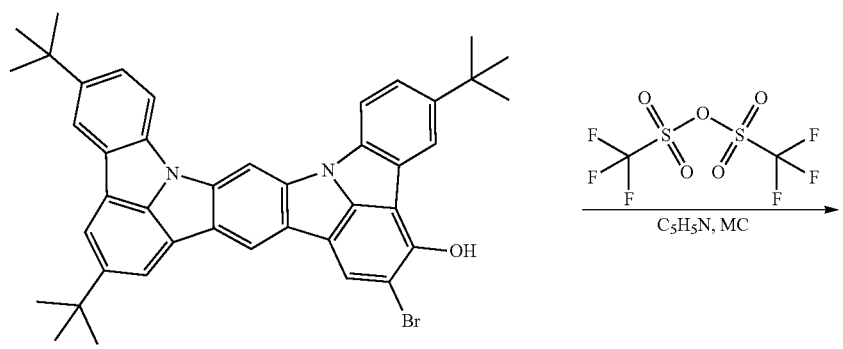
143001-d
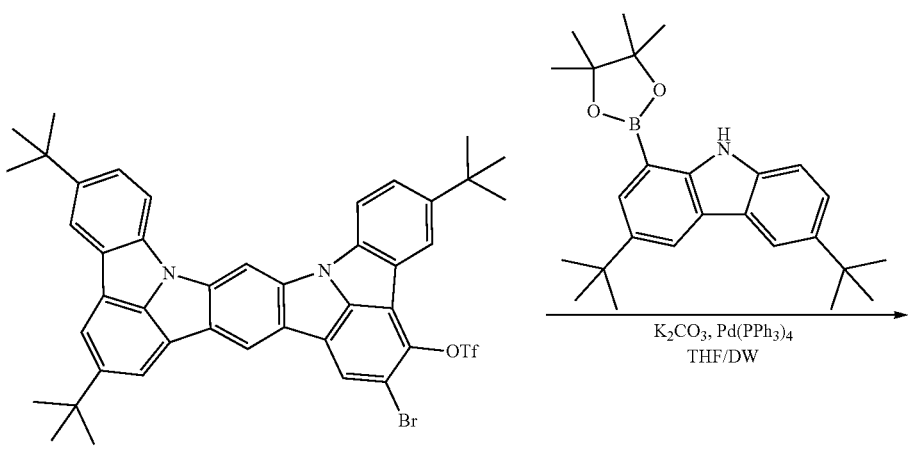
143001-e

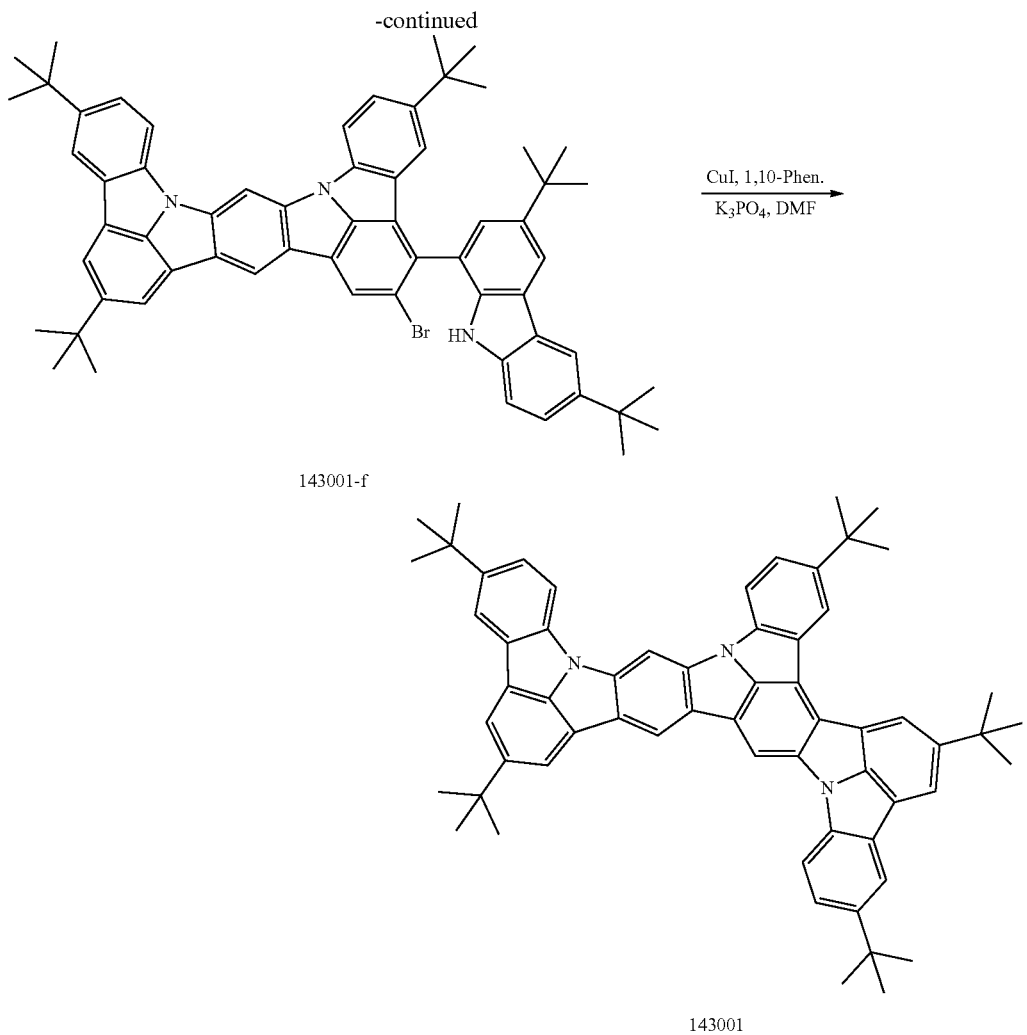

Synthesis of Intermediate 143001-a 13.7 g of Intermediate 143001-a was obtained in substantially the same manner as in Synthesis of Intermediate 124001-a in Synthesis Example 2, except that Intermediate 141001-c was used in reaction (yield: 65%).

LC-Mass (calculated value: 675.29 g/mol, found value: 674.98 (M+1))

Synthesis of Intermediate 143001-b

A reaction was performed in substantially the same manner as in Synthesis of Compound 124001 in Synthesis Example, except that Intermediate 143001-a was used. 10.2 g of Intermediate 143001-b was thus obtained (yield: 78%).

LC-Mass (calculated value: 603.34 g/mol, found value: 603.44 (M+1))

Synthesis of Intermediate 143001-c 3.51 g of Intermediate 141001-c was obtained in substantially the same manner as in Synthesis of Intermediate 121001-g in Synthesis Example 12 (yield: 37%).

LC-Mass (calculated value: 681.25 g/mol, found value: 680.78 (M+1))

Synthesis of Intermediate 143001-d 2.12 g of Intermediate 143001-d was obtained in substantially the same manner as in Synthesis of Intermediate 121001-h in Synthesis Example 12 (yield: 71%).

LC-Mass (calculated value: 667.23 g/mol, found value: 667.75 (M+1))

Synthesis of Intermediate 143001-e 1.78 g of Intermediate 143001-e was obtained in substantially the same manner as in Synthesis of Intermediate 121001-i in Synthesis Example 12, except that Intermediate 143001-d was used in reaction (yield: 65%).

LC-Mass (calculated value: 799.18 g/mol, found value: 799.82 (M+1))

Synthesis of Intermediate 143001-f 0.521 g of Intermediate 143001-f was obtained in substantially the same manner as in Synthesis of Intermediate 121001-j in Synthesis Example 12, except that Intermediate 143001-e was used in reaction (yield: 32%).

LC-Mass (calculated value: 928.42 g/mol, found value: 927.98 (M+1))

3887
Synthesis of Compound 143001
0.432 g of Compound 143001 was obtained in substantially the same manner as in Synthesis of Intermediate 112001-d in Synthesis Example 1 (yield: 89%).
LC-Mass (calculated value: 848.4944 g/mol, found value: 848.4944 (M+1))
Synthesis Example 19: Synthesis of Compound 153001
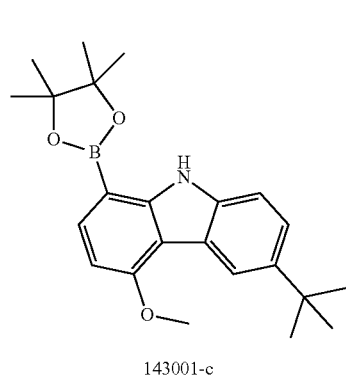
143001-c
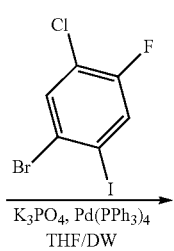
K$_3$PO$_4$, Pd(PPh$_3$)$_4$
THF/DW
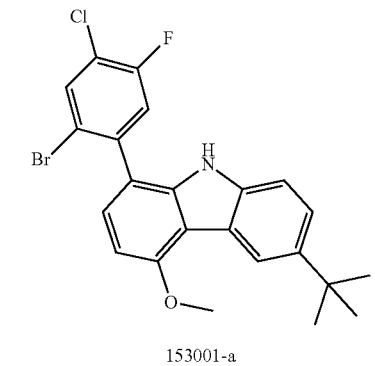
153001-a
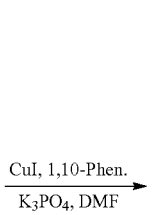
CuI, 1,10-Phen.
K$_3$PO$_4$, DMF
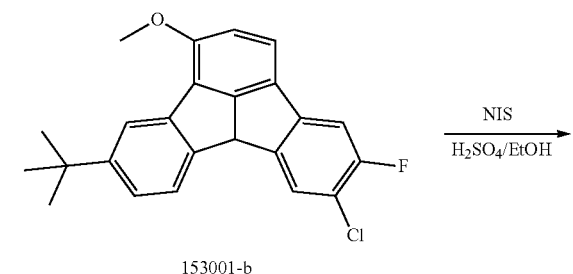
153001-b
NIS
H$_2$SO$_4$/EtOH
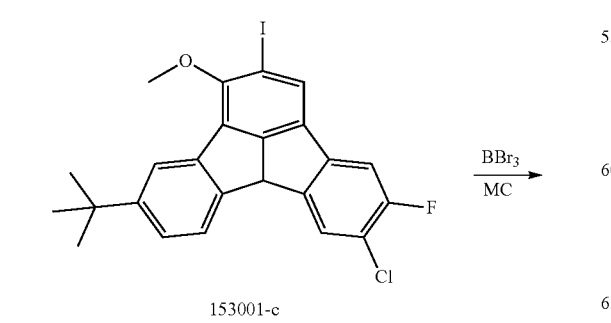
153001-c
BBr$_3$
MC
3888
-continued
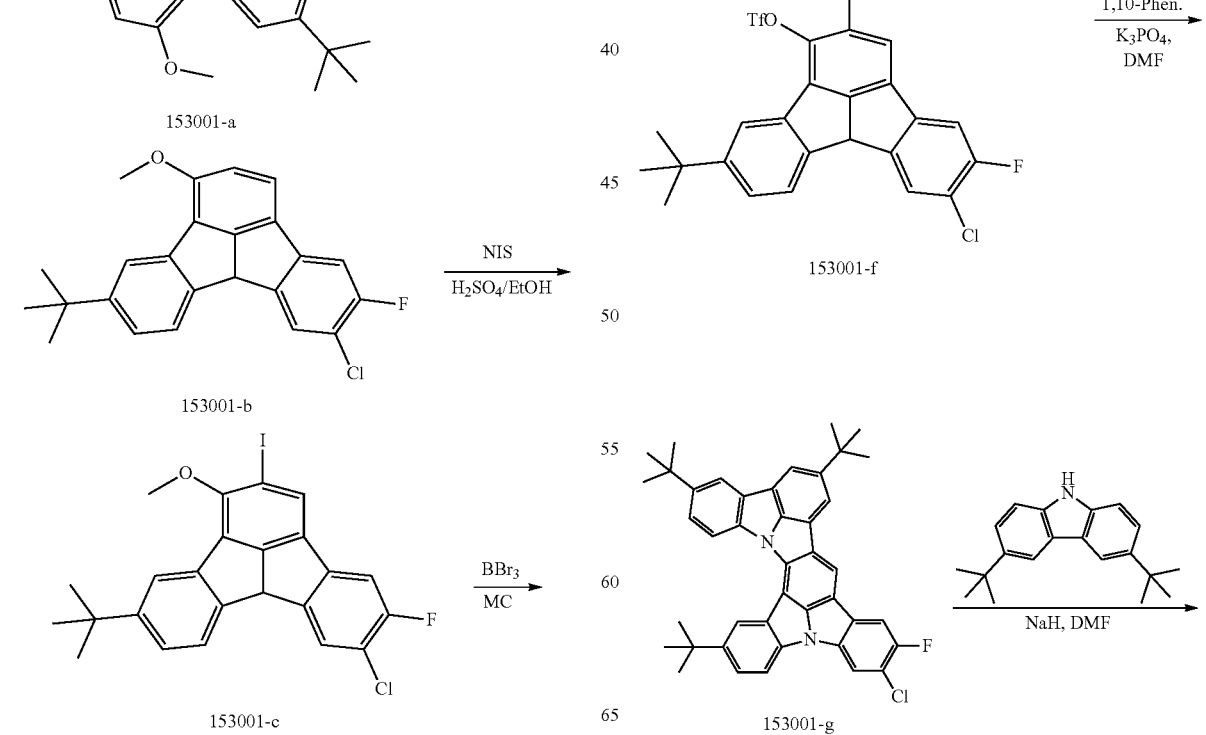

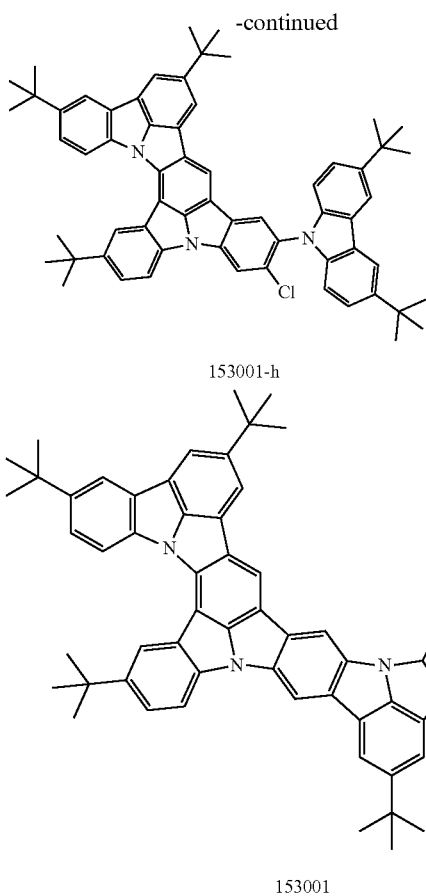

Synthesis of Intermediate 153001-a 16.7 g of Intermediate 153001-a was obtained in substantially the same manner as in Synthesis of Intermediate 112001-c in Synthesis Example 1, except that Intermediate 141001-c and Intermediate 112001-b were used in reaction (yield: 42%).

LC-Mass (calculated value: 460.05 g/mol, found value: 461.01 (M+1))

Synthesis of Intermediate 153001-b 10.2 g of Intermediate 153001-b was obtained in substantially the same manner as in Synthesis of Intermediate 112001-d in Synthesis Example 1, except that Intermediate 153001-a was used in reaction (yield: 91%).

LC-Mass (calculated value: 380.12 g/mol, found value: 380.55 (M+1))

Synthesis of Intermediate 153001-c 25.0 g (65.8 mmol) of 153001-b and 400 mL of ethanol were added to a round flask and stirred. 65.8 mmol of sulfuric acid ($H_2SO_4$) was slowly added thereto, and 16.3 g (72.4 mmol) of N-iodosuccinimide (NIS) was dissolved in ethanol. The solution was slowly added to the reaction product. After stirring for 6 hours at room temperature, sodium hydrogen carbonate ($NaHCO_3$) and sodium thiosulfate ($Na_2S_2O_3$) were used for neutralization and quenching. An extraction performed using dichloromethane and distilled water. Then, impurities were separated and purified using column chromatography to thereby obtain 23.6 g of Intermediate 153001-c (yield: 71%).

LC-Mass (calculated value: 506.02 g/mol, found value: 506.44 (M+1))

Synthesis of Intermediate 153001-d 11.7 g of Intermediate 153001-d was obtained in substantially the same manner as in Synthesis of Intermediate 121001-h in Synthesis Example 12 (yield: 55%).

LC-Mass (calculated value: 492.00 g/mol, found value: 491.88 (M+1))

Synthesis of Intermediate 153001-e 12.1 g of Intermediate 153001-e was obtained in substantially the same manner as in Synthesis of Intermediate 121001-i in Synthesis Example 12, except that Intermediate 153001-d was used in reaction (yield: 66%).

LC-Mass (calculated value: 623.95 g/mol, found value: 624.11 (M+1))

Synthesis of Intermediate 153001-f 5.31 g of Intermediate 153001-f was obtained in substantially the same manner as in Synthesis of Intermediate 112001-i in Synthesis Example 1, except that Intermediate 153001-e was used (yield: 41%).

LC-Mass (calculated value: 775.24 g/mol, found value: 775.98 (M+1))

Synthesis of Intermediate 153001-g 2.21 g of Intermediate 153001-g was obtained in substantially the same manner as in Synthesis of Intermediate 112001-d in Synthesis Example 1, except that Intermediate 153001-f was used in reaction (yield: 65%).

LC-Mass (calculated value: 625.28 g/mol, found value: 625.88 (M+1))

Synthesis of Intermediate 153001-h 0.192 g (8.00 mmol) of sodium hydride (NaH) and 10 mL of DMF were added to a round flask and stirred. Then, a solution in which 1.07 g (3.84 mmol) of 3,6-di-tert-butyl-9H-carbazole was dissolved in 20 mL of DMF was slowly added thereto and stirred until the solution became transparent. Subsequently, 2.00 g (3.20 mmol) of Intermediate 153001-g was added thereto, followed by heating at a temperature of 150° C. to allow a reaction to occur. Once the reaction was complete, excess distilled water was added thereto, and a solid obtained by filtration was dissolved in dichloromethane. Then, precipitation was performed by using methanol. This process was performed repeatedly for filtration. After drying, 2.21 g of Intermediate 153001-h was obtained (yield: 78%).

LC-Mass (calculated value: 884.47 g/mol, found value: 885.02 (M+1))

Synthesis of Compound 153001

1.50 g (1.70 mmol) of Intermediate 153001-h, 0.193 g (0.848 mmol) of benzyltriethylammonium chloride ($BnEt_3NCl$), 1.80 g (8.48 mmol) of potassium phosphate, 0.170 mmol of tri-tert-butylphosphine ($P(t-Bu)_3$), 0.078 g (0.085 mmol) of tris(dibenzylideneacetone) dipalladium(0)

($Pd_2(dba)_3$), and 50 ml of N,N-dimethylacetamide (DMA) were stirred and heated at a temperature of 200° C. Once the reaction was complete, excess chloroform was dissolved therein by heating. Then, the resulting mixture was subjected to filtration under reduced pressure using a filter charged with silica. The filtrate was then concentrated and precipitated using methanol. 1.11 g of Compound 153001 was obtained after drying (yield: 77%).

LC-Mass (calculated value: 848.4944 g/mol, found value: 848.4941 (M+1))

Synthesis Example 20: Synthesis of Compound 164001

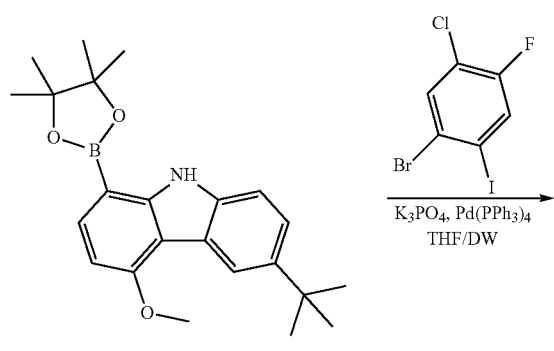

141001-c

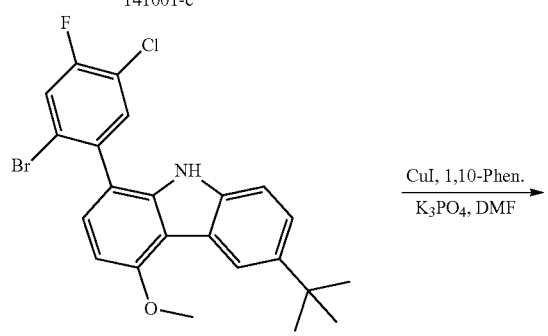

164001-a

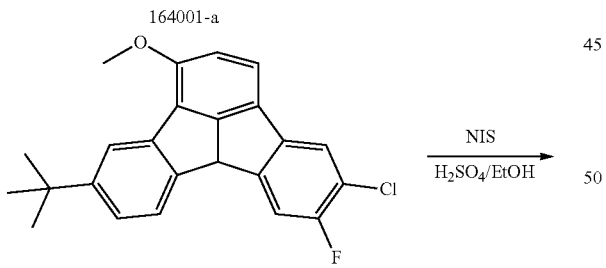

164001-b

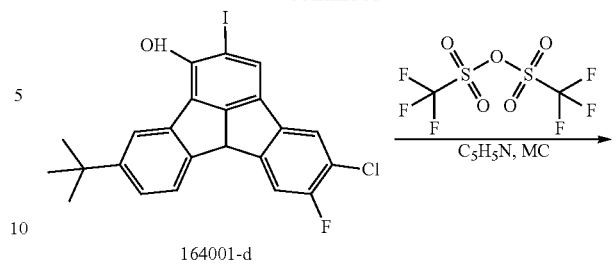

164001-c

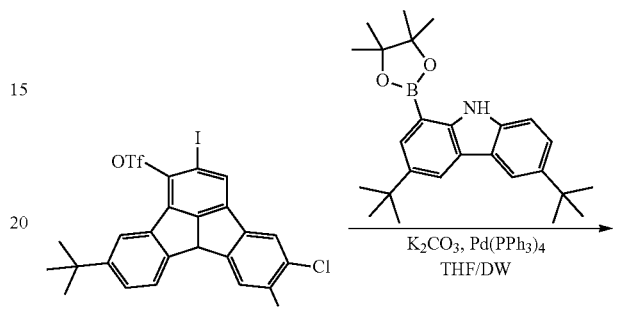

164001-d

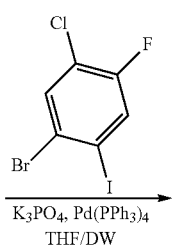

164001-e

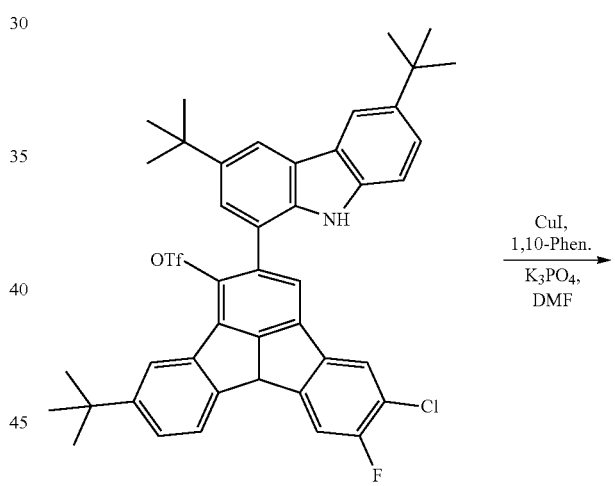

164001-f

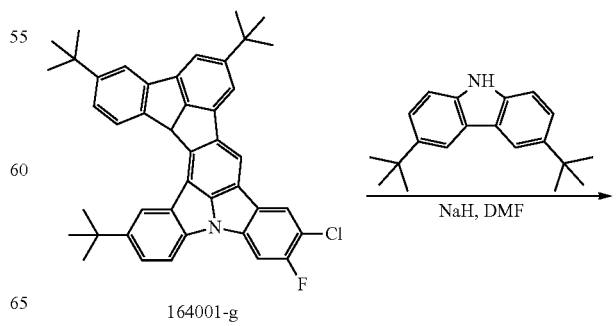

164001-g

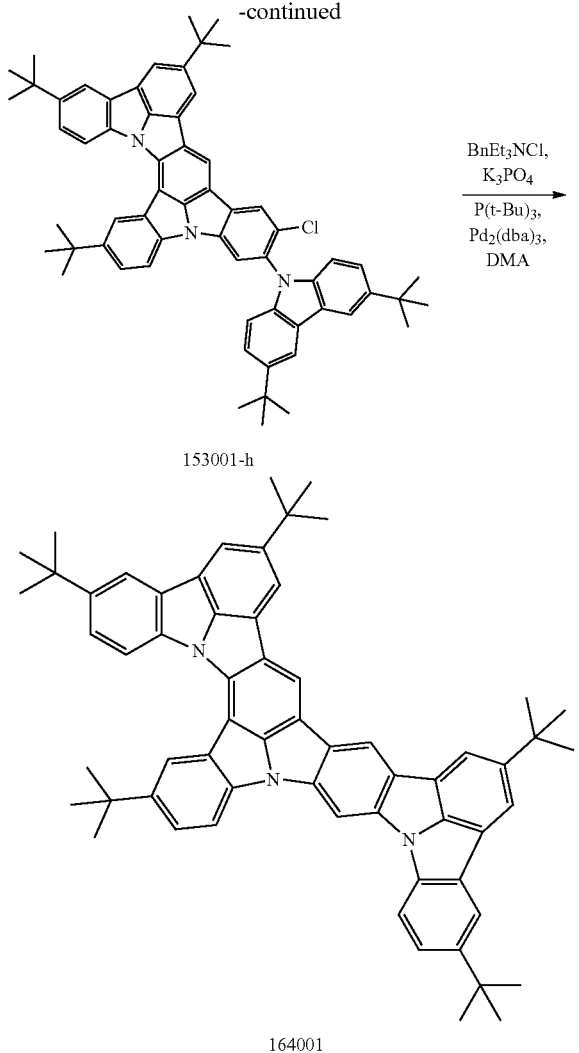

153001-h

164001

Synthesis of Intermediate 164001-a

A reaction was performed in substantially the same manner as in Synthesis of Intermediate 153001-a in Synthesis Example 19, except that Intermediate 115001-b was used instead of Intermediate 112001-b. 20.8 g of Intermediate 164001-a was thus obtained (yield: 45%).

LC-Mass (calculated value: 460.05 g/mol, found value: 460.77 (M+1))

Synthesis of Intermediate 164001-b

A reaction was performed in substantially the same manner as in Synthesis of Intermediate 153001-b in Synthesis Example 19, except that Intermediate 164001-a was used instead of Intermediate 153001-a. 15.3 g of Intermediate 164001-b was thus obtained (yield: 88%).

LC-Mass (calculated value: 380.12 g/mol, found value: 380.41 (M+1)

Synthesis of Intermediate 164001-c

A reaction was performed in substantially the same manner as in Synthesis of Intermediate 153001-c in Synthesis Example 19, except that Intermediate 164001-b was used instead of Intermediate 153001-b. 10.2 g of Intermediate 164001-c was thus obtained (yield: 66%).

LC-Mass (calculated value: 506.02 g/mol, found value: 506.14 (M+1))

Synthesis of Intermediate 164001-d

A reaction was performed in substantially the same manner as in Synthesis of Intermediate 153001-d in Synthesis Example 19, except that Intermediate 164001-c was used instead of Intermediate 153001-c. 8.53 g of Intermediate 164001-d was thus obtained (yield: 71%).

LC-Mass (calculated value: 492.00 g/mol, found value: 491.95 (M+1))

Synthesis of Intermediate 164001-e

A reaction was performed in substantially the same manner as in Synthesis of Intermediate 153001-e in Synthesis Example 19, except that Intermediate 164001-d was used instead of Intermediate 153001-d. Once the reaction and purification were complete, 5.42 g of Intermediate 164001-e was obtained (yield: 74%).

LC-Mass (calculated value: 623.95 g/mol, found value: 624.51 (M+1))

Synthesis of Intermediate 164001-f

A reaction was performed in substantially the same manner as in Synthesis of Intermediate 153001-f in Synthesis Example 19, except that Intermediate 164001-e was used as a start material. 2.51 g of Intermediate 164001-f was thus obtained (yield: 32%).

LC-Mass (calculated value: 775.24 g/mol, found value: 775.57 (M+1))

Synthesis of Intermediate 164001-g

A reaction was performed in substantially the same manner as in Synthesis of Intermediate 153001-g in Synthesis Example 19, except that Intermediate 164001-f was used instead of Intermediate 153001-f. 1.57 g of Intermediate 164001-g was thus obtained (yield: 75%).

LC-Mass (calculated value: 625.28 g/mol, found value: 625.93 (M+1))

Synthesis of Intermediate 164001-h 1.12 g of Intermediate 164001-h was obtained in substantially the same manner as in Synthesis of Intermediate 153001-h in Synthesis Example 19, except that Intermediate 164001-g was used in reaction (yield: 65%).

LC-Mass (calculated value: 884.47 g/mol, found value: 884.91 (M+1))

Synthesis of Compound 164001

A reaction was performed in substantially the same manner as in Synthesis of Compound 153001 in Synthesis Example 19, except that Intermediate 164001-h was used in reaction. Once the synthesis was complete, 0.579 g of Compound 164001 was thus obtained (yield: 68%).

LC-Mass (calculated value: 848.4944 g/mol, found value: 848.4943 (M+1))

Synthesis Example 21: Synthesis of Compound 174001
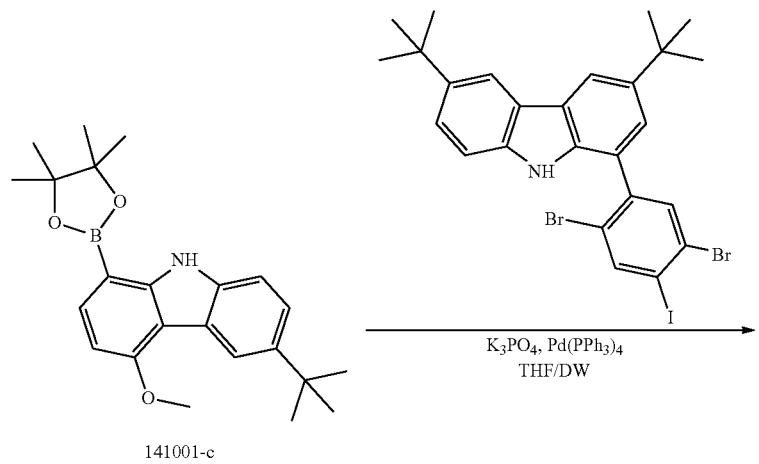
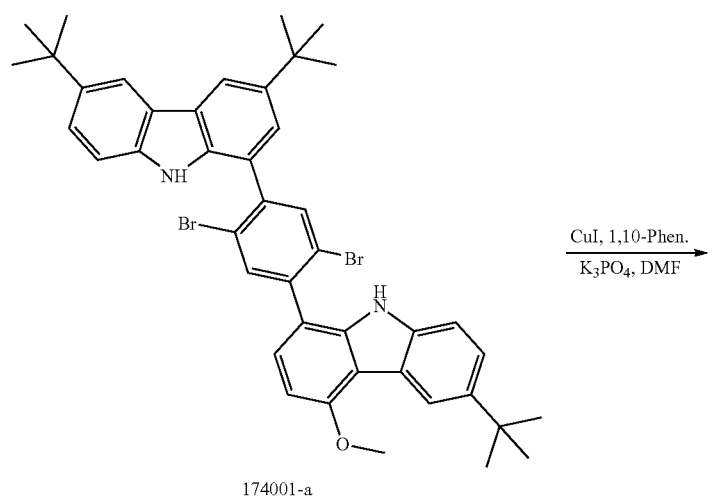
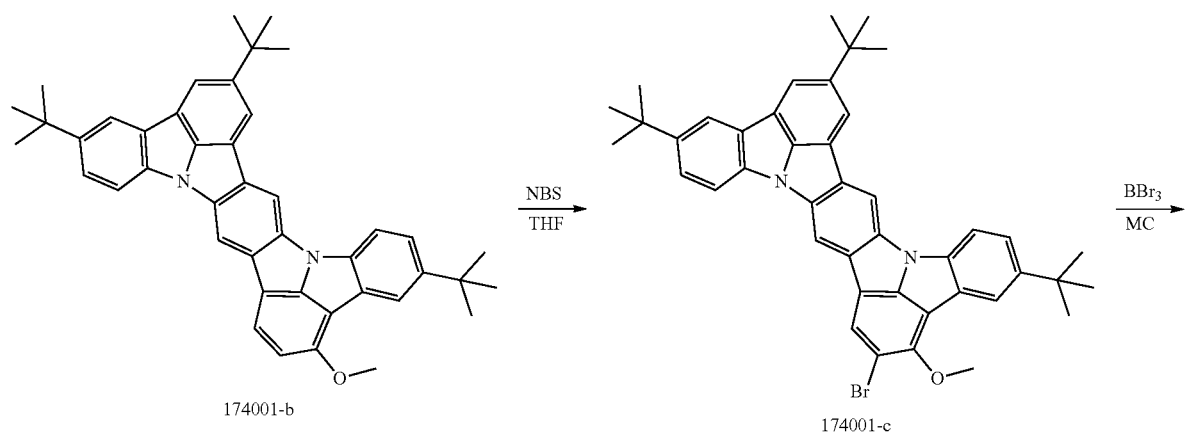

-continued
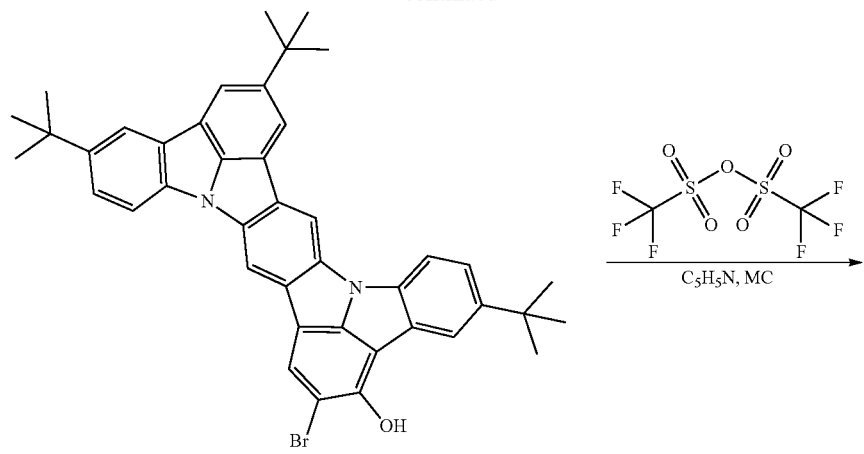
174001-d
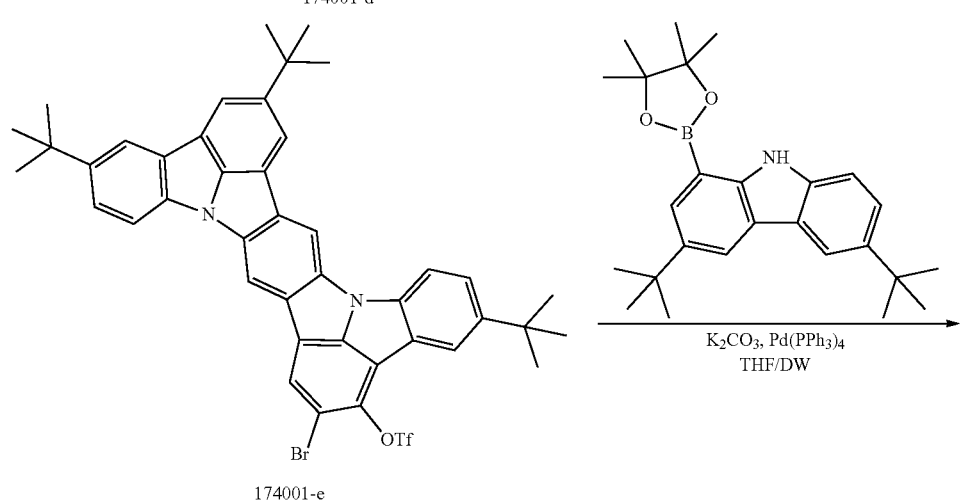
174001-e
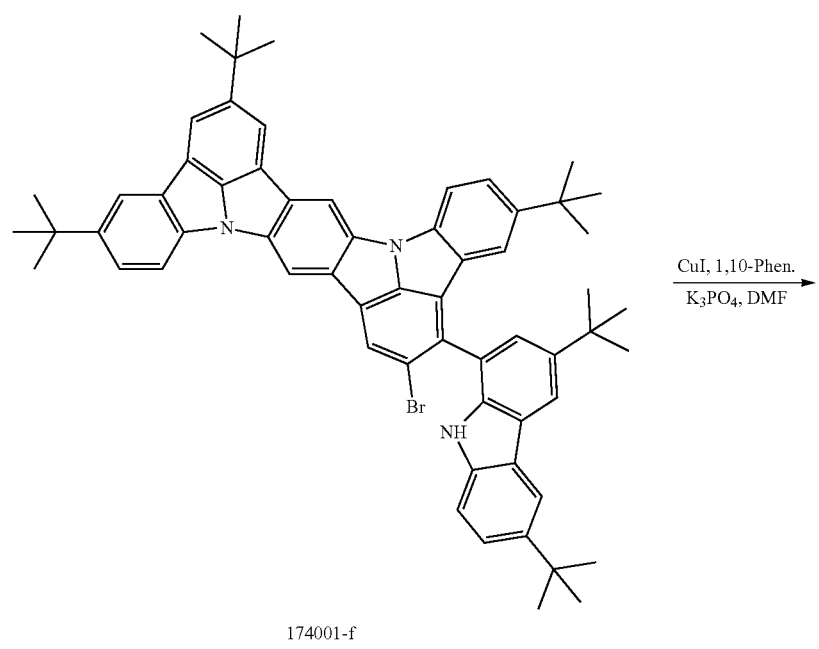
174001-f

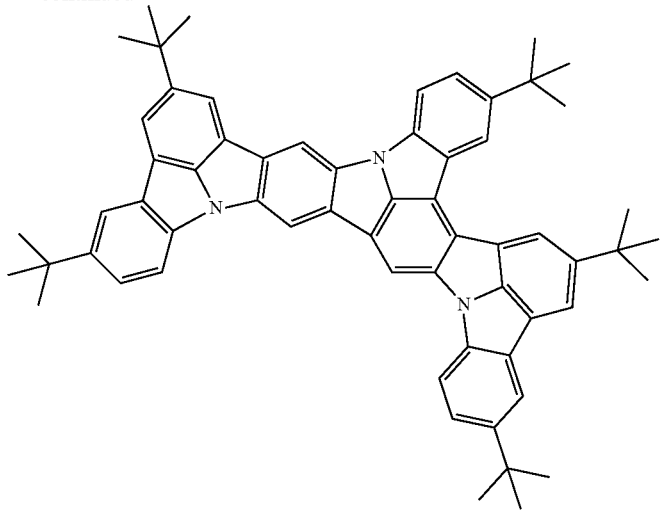

174001

Synthesis of Intermediate 174001-a 3.24 g of Intermediate 174001-a was obtained in substantially the same manner as in Synthesis of Intermediate 115001-i in Synthesis Example 3, except that Intermediate 141001-c and Intermediate 115001-h were used in reaction (yield: 42%).

LC-Mass (calculated value: 763.19 g/mol, found value: 762.87 (M+1))

Synthesis of Intermediate 174001-b 2.89 g of Intermediate 174001-b was obtained in substantially the same manner as in Synthesis of Compound 112001 in Synthesis Example 1, except that Intermediate 174001-a was used in reaction (yield: 97%).

LC-Mass (calculated value: 603.34 g/mol, found value: 602.98 (M+1))

Synthesis of Intermediate 174001-c

A reaction was performed in substantially the same manner as in Synthesis of Intermediate 121001-g in Synthesis Example 12, except that Intermediate 174001-b was used in reaction. 1.79 g of Intermediate 174001-c was obtained (yield: 75%).

LC-Mass (calculated value: 681.25 g/mol, found value: 681.82 (M+1))

Synthesis of Intermediate 174001-d 1.42 g of Intermediate 174001-d was obtained in substantially the same manner as in Synthesis of Intermediate 121001-h in Synthesis Example 12, except that Intermediate 174001-c was used instead of Intermediate 121001-g (yield: 63%).

LC-Mass (calculated value: 667.23 g/mol, found value: 667.42 (M+1))

Synthesis of Intermediate 174001-e

A reaction was performed in substantially the same manner as in Synthesis of Intermediate 121001-i in Synthesis Example 12, except that Intermediate 174001-d was used. 1.23 g of Intermediate 174001-e was obtained (yield: 58%).

LC-Mass (calculated value: 799.18 g/mol, found value: 800.21 (M+1))

Synthesis of Intermediate 174001-f 0.852 g of Intermediate 174001-f was obtained in substantially the same manner as in Synthesis of Intermediate 112001-f in Synthesis Example 1, except that Intermediate 174001-e was used in reaction (yield: 59%).

LC-Mass (calculated value: 928.42 g/mol, found value: 928.66 (M+1))

Synthesis of Compound 1

0.512 g of Compound 174001 was obtained in substantially the same manner as in Synthesis of Intermediate 112001-d in Synthesis Example 1, except that Intermediate 174001-f was used in reaction (yield: 92%).

LC-Mass (calculated value: 848.4944 g/mol, found value: 848.4944 (M+1)) Evaluation Example 1: Evaluation on HOMO, LUMO, $T_1$, and $S_1$ energy levels The HOMO, LUMO, $T_1$ and $S_1$ energy levels of the compounds shown in Table 2 were measured according to the method described in Table 17. The results thereof are shown in Table 18:

TABLE 17

| | |
|---|---|
| HOMO energy level evaluation method | A potential (Volts, V) versus current (Amperes, A) graph of each compound was obtained by using cyclic voltammetry (CV) (electrolyte: 0.1M TBAP/solvent: ACN/electrode: 3-electrode system (working electrode: carbon, reference electrode: Ag/AgCl, auxiliary electrode: Pt)). Subsequently, from oxidation onset of the graph, a HOMO energy level of the compound was calculated. |
| LUMO energy level evaluation method | Each compound was diluted at a concentration of $1 \times 10^{-5}$ M in tetrahydrofuran, and an UV absorption spectrum thereof was measured at room temperature by using JASCO V-730 UV-visible spectrometer. A LUMO energy level thereof was calculated by using an optical band gap ($E_g$) from an edge of the absorption spectrum and a HOMO energy level. |

TABLE 17-continued

| | |
|---|---|
| $T_1$ energy level evaluation method | Each compound was dissolved at a concentration of $1 \times 10^{-5}$M in tetrahydrofuran and placed in a quartz cell, followed by cooling by using nitrogen (77 Kelvins (K)). Then, 1 millisecond (ms) of delay time was given by using a fluorescence spectrometer (PerkinElmer, LS-55) to measure a photoluminescence spectrum. |
| $S_1$ energy level evaluation method | $S_1$ energy level was measured in substantially the same manner as in $T_1$ energy level evaluation method, except that delay time was not given, and the maximum emission peak was determined as $S_1$ energy level. |

TABLE 18

| Compound No. | HOMO (eV) | LUMO (eV) | $T_1$ (eV) | $S_1$ (eV) | $\Delta E_{ST}$ (eV) |
|---|---|---|---|---|---|
| 115001 | −5.63 | −2.85 | 2.54 | 2.84 | 0.30 |
| 115002 | −5.63 | −2.89 | 2.54 | 2.80 | 0.26 |
| C1 | −5.72 | −2.93 | 2.55 | 2.84 | 0.29 |
| C2 | −5.89 | −3.15 | 2.54 | 2.80 | 0.26 |
| C3 | −5.53 | −2.88 | 2.70 | 2.49 | 0.21 |

Referring to the results of Table 18, Compounds 115001 and 115002 were each found to have improved electrical characteristics.

Evaluation Example 2: Evaluation of Full Width at Half Maximum (FWHM)

As the method described in Table 19, photoluminescence spectra of the compounds shown in Table 20 were measured, and the FWHM of each compound was evaluated. The results thereof are shown in Table 20.

TABLE 19

| | |
|---|---|
| Measurement of photoluminescence (PL) spectrum | Each compound and mCP and TSPO1 were co-deposited on a quartz substrate at a weight ratio of 50:50 (wherein, the weight of the evaluated compound of the total weight of the host and each evaluated compound was 1 wt %) to form a thin film having a thickness of 40 nm. Then, the spectrum thereof was measured at room temperature by using a fluorescence spectrometer (PerkinElmer, LS-55). |

TABLE 20

| Compound No. | FWHM (nm) |
|---|---|
| 115001 | 21 |
| 115002 | 23 |
| C1 | 22 |
| C2 | 21 |
| C3 | 28 |

Referring to the results of Table 20, Compounds 115001 and 115002 were each found to have improved color characteristics.

Evaluation Example 3: Evaluation of Photoluminescent Quantum Yield (PLQY) and Decay Time (1) Preparation of Thin Film A quartz substrate was prepared by washing with chloroform and pure water. Then, as shown in Table 21, each compound and Host Compound mCP and TSPO1 were co-deposited at a weight ratio of 5:5 (wherein, the weight of each evaluated compound of the total weight of the host and each evaluated compound was 1 wt %) at a vacuum pressure of $10^{-7}$ torr to thereby form a thin film having a thickness of 40 nm. (Co-deposition was performed in the same manner as described in Table 19.)

(2) Evaluation of Photoluminescent Quantum Yield

Photoluminescent quantum yields in the thin film was evaluated by using Hamamatsu Photonics absolute PL quantum yield measurement system employing PLQY measurement software (Hamamatsu Photonics, Ltd., Shizuoka, Japan), in which a xenon light source, a monochromator, a photonic multichannel analyzer, and an integrating sphere are mounted. Thus, PLQY of the compounds shown in Table 21 were measured accordingly.

(3) Decay Time Evaluation

TRPL measurement system C11367-31 (Hamamatsu Photonics) and a mounted LED lamp (excitation wavelength of 280 nanometers) were used to evaluate the PL spectrum of each thin film under nitrogen atmosphere at room temperature to thereby determine the maximum emission peak. A repetition rate of excitation on the thin film by the LED lamp was set to 1 kilohertz (KHz), and the number of photons emitted from the wavelength of the maximum emission peak was counted repeatedly to thereby obtain a TRPL curve that may be analyzed. $T_{decay}$(Ex)(decay time) of the thin film was obtained by fitting at least two exponential decay functions to the results thereof. The functions used for the fitting are as described in Equation 1, and a decay time $T_{decay}$ having the largest value among values for each of the exponential decay functions used for the fitting was taken as $T_{decay}$(Ex), i.e., a decay time. The results thereof are shown in Table 21. The remaining decay time $T_{decay}$ values were used to determine the lifetime of typical fluorescence to be decayed. Here, during the same measurement time as the measurement time for obtaining TRPL curves, the same measurement was repeated once more in a dark state (i.e., a state where a pumping signal incident on each of the films was blocked), thereby obtaining a baseline or a background signal curve available as a baseline for the fitting:

$$f(t) = \sum_{i=1}^{n} A_i \exp(-t/T_{decay,i}) \quad \text{Equation 1}$$

TABLE 21

| Compound No. | PLQY | $T_{decay}$ (Ex) (µs) (decay time) |
|---|---|---|
| 115001 | 99 | 4060 |
| 115002 | 97 | 1760 |
| C1 | 95 | 12500 |
| C2 | 98 | 1460 |
| C3 | 97 | 183 |

Referring to the results of Table 21, Compounds 115001 and 115002 were each found to have improved PLQY thin film characteristics and excellent device characteristics, although Compounds 115001 and 115002 had a relatively long decay time.

Example 1-1

An ITO glass substrate was cut to a size of 50 millimeters (mm)×50 mm×0.5 mm. Then the glass substrate was sonicated in acetone isopropyl alcohol and pure water for about 15 minutes each, and cleaned by exposure to ultraviolet rays and ozone for 30 minutes.

Subsequently, PEDOT: PSS was spin-coated on an ITO electrode (anode) on a glass substrate to form a first hole injection layer having a thickness of 40 nm. TAPC was then deposited on the first hole injection layer to form a second hole injection layer having a thickness of 5 nm. TCTA was deposited on the second hole injection layer to form a first hole transport layer having a thickness of 5 nm. PCzAc was deposited on the first hole transport layer to form a second hole transport layer having a thickness of 5 nm. Then, mCP was deposited on the second hole transport layer to form an electron blocking layer having a thickness of 5 nm. Thus, a hole transport region was formed.

mCP (as a first host), TSPO1 (as a second host), and Compound 115001 (as a dopant) were co-deposited on the hole transport region (wherein, the weight of the dopant of the total weight of the first host, the second host, and the dopant was 1 wt %) to thereby form an emission layer having a thickness of 25 nm.

Thereafter, TSPO1 was deposited on the emission layer to form an electron transport layer having a thickness of 25 nm, LiF was deposited on the electron transport layer to form an electron injection layer having a thickness of 1.5 nm, and Al was deposited on the electron injection layer to a thickness of 200 nm, thereby completing the manufacture of an organic light-emitting device.

TAPC

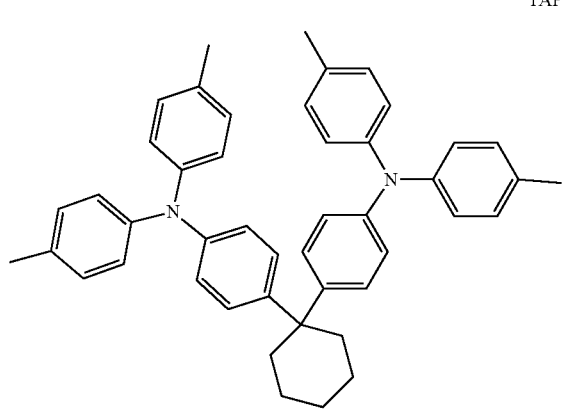

TCTA

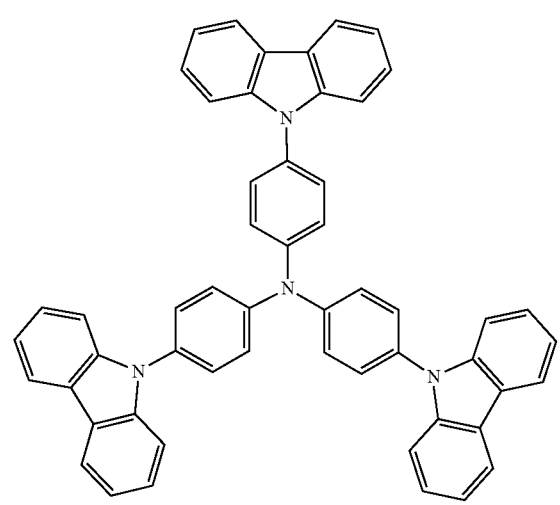

PCZAC mCP

TSPO1

Example 1-2 and Comparative Examples 1-1 to 1-3

Organic light-emitting devices were manufactured in substantially the same manner as in Example 1-1, except that compounds shown in Table 22 were used as a dopant in the formation of an emission layer.

Example 2-1

An ITO glass substrate was cut to a size of 50 millimeters (mm)×50 mm×0.5 mm. Then the glass substrate was sonicated in acetone isopropyl alcohol and pure water for about 15 minutes each, and cleaned by exposure to ultraviolet rays and ozone for 30 minutes.

Subsequently, PEDOT: PSS was spin-coated on an ITO electrode (anode) on a glass substrate to form a first hole injection layer having a thickness of 40 nm. BDCFL was then deposited on the first hole injection layer to form a second hole injection layer having a thickness of 10 nm. TNPA was deposited on the second hole injection layer to form a first hole transport layer having a thickness of 10 nm. PCzAc was deposited on the first hole transport layer to form a second hole transport layer having a thickness of 5 nm. Then, mCP was deposited on the second hole transport layer to form an electron blocking layer having a thickness of 5 nm. Thus, a hole transport region was formed.

Compound Host* and Compound 115001 (as a dopant) were co-deposited on the hole transport region (wherein, the total weight of the host and the dopant was 1 wt %) to thereby form an emission layer having a thickness of 30 nm.

TNPT was deposited on the emission layer to form a hole blocking layer having a thickness of 5 nm, and ZADN was deposited on the hole blocking layer to form an electron transport layer having a thickness of 20 nm. Next, LiF was deposited on the electron transport layer to form an electron injection layer having a thickness of 1.5 nm, and aluminum (Al) was then deposited on the electron injection layer to a thickness of 200 nm, thereby completing the manufacture of an organic light-emitting device.

Host*

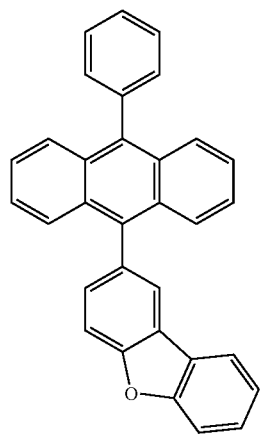

BDCFL

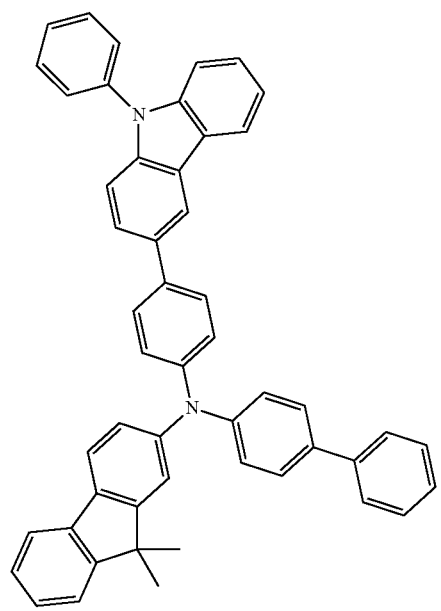

-continued

TNPA

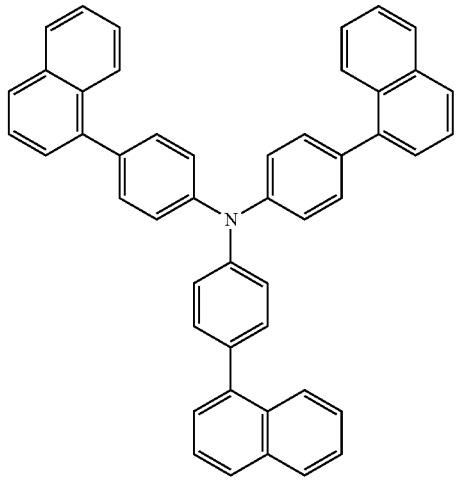

TNPT

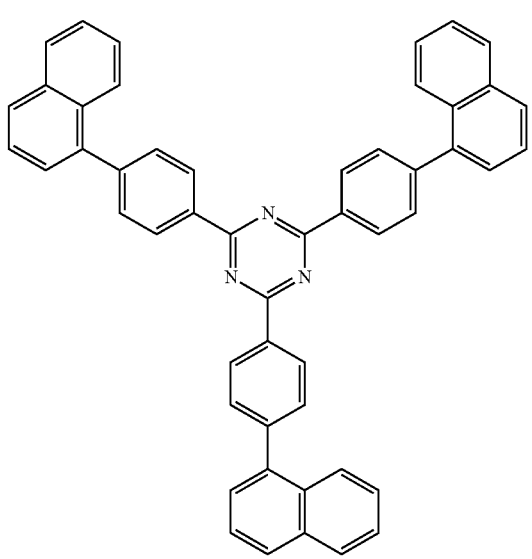

ZADN

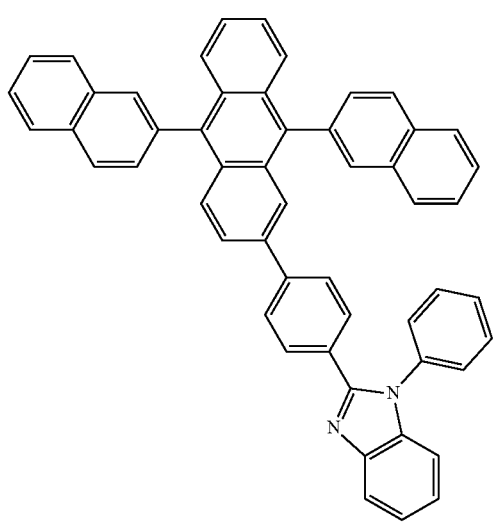

Examples 2-2 and Comparative Examples 2-1 to 2-3

Organic light-emitting devices were manufactured in substantially the same manner as in Example 2-1, except that compounds shown in Table 23 were used as a dopant in the formation of an emission layer.

Example 3-1

An ITO glass substrate was cut to a size of 50 millimeters (mm)×50 mm×0.5 mm. Then the glass substrate was sonicated in acetone isopropyl alcohol and pure water for about 15 minutes each, and cleaned by exposure to ultraviolet rays and ozone for 30 minutes.

Subsequently, PEDOT: PSS was spin-coated on an ITO electrode (anode) on a glass substrate to form a hole injection layer having a thickness of 90 nm. TAPC was then deposited on the hole injection layer to form a hole transport layer having a thickness of 20 nm. mCP was deposited on the hole transport layer to form an electron blocking layer having a thickness of 10 nm. Thus, a hole transport region was formed.

DPEPO (as a host), DMAC-DPS (as a sensitizer), and Compound 115001 (as a dopant)(wherein, the weight of the dopant of the total weight of the host, the sensitizer, and the dopant was 1 wt %, and the weight of the sensitizer of the total weight of the host, the sensitizer, and the dopant was 20 wt %) were co-deposited on the hole transport region to form an emission layer having a thickness of 25 nm.

Next, TSPO1 was deposited on the emission layer to form a first electron transport layer having a thickness of 5 nm. Then, TPBi was deposited on the first electron transport layer to form a second electron transport layer having a thickness of 20 nm. LiF was then deposited on the second electron transport layer to form an electron injection layer having a thickness of 1.5 nm. Finally, aluminum (Al) was deposited on the electron injection layer to a thickness of 200 nm, thereby completing the manufacture of a light-emitting device.

TAPC

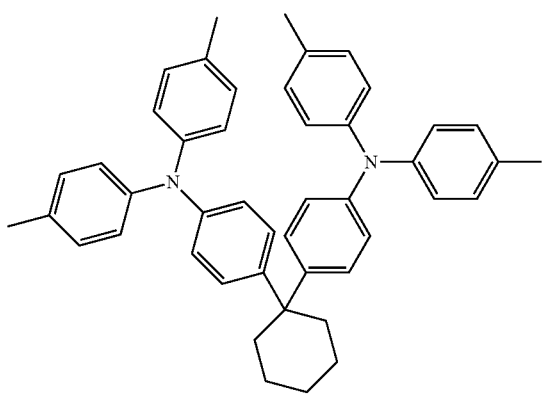

TCTA

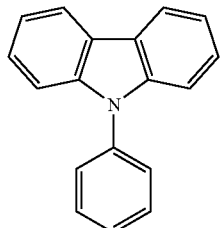
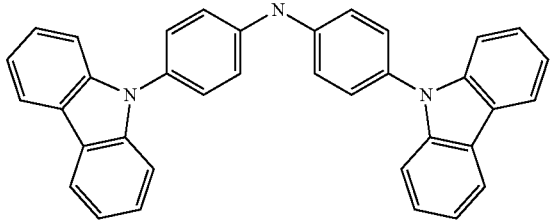

mCP

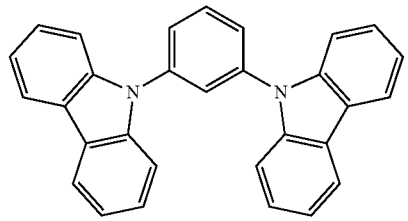

TSPO1

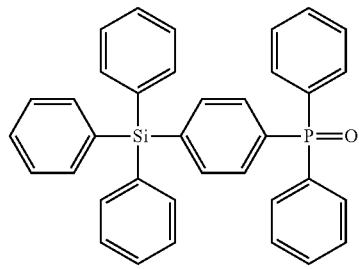

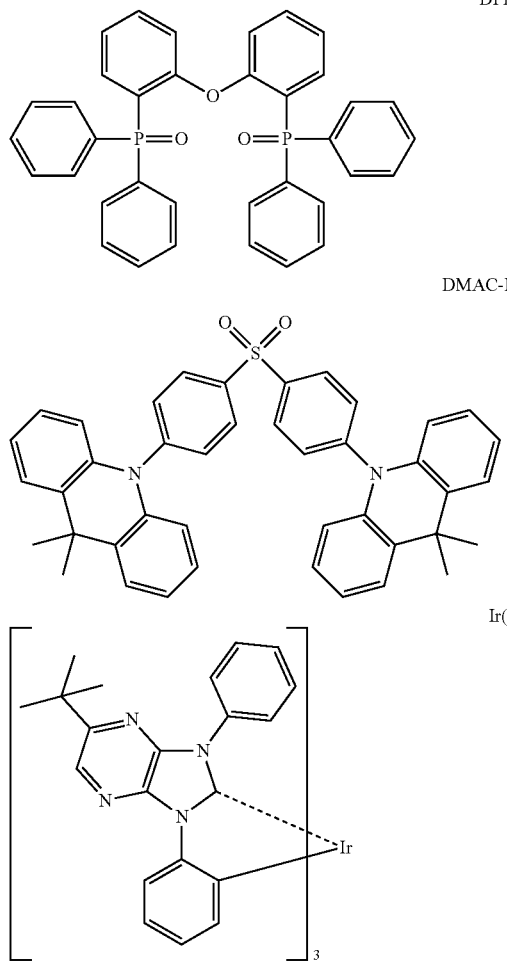

Example 3-2 and Comparative Example 3-1

Organic light-emitting devices were manufactured in substantially the same manner as in Example 3-1, except that compounds shown in Table 24 were used as a sensitizer and a dopant in the formation of an emission layer.

Evaluation Example: Evaluation OLED Characteristics

The driving voltage, maximum external quantum yield, electricity efficiency, current efficiency, CIE color-coordinate (at 1,000 nit), conversion efficiency, and FWHM of the organic light-emitting devices of the Examples and the Comparative Examples were measured by using a current voltmeter (Keithley 2400) and a luminance meter (Minolta Cs-1000A). The results thereof are shown in Tables 22 to 24. Here, Comparative Examples C1 and C2 were not operated and thus not be evaluated.

TABLE 22

| | Dopant | FWHM (nm) | Driving voltage (V) | $EQE_{max}$ (%) | Electricity efficiency (%) | Current efficiency (%) | CIEy | Conversion efficiency (%) |
|---|---|---|---|---|---|---|---|---|
| Example 1-1 | 115001 | 11 | 5.7 | 180 | 141 | 133 | 0.044 | 184 |
| Example 1-2 | 115002 | 15 | 5.7 | 179 | 175 | 175 | 0.061 | 175 |
| Comparative Example 1-1 | C1 | 22 | 5.7 | 100 | 100 | 100 | 0.061 | 100 |
| Comparative Example 1-2 | C2 | 21 | 5.4 | 124 | 126 | 134 | 0.068 | 120 |
| Comparative Example 1-3 | C3 | 21 | 5.1 | 193 | 373 | 351 | 0.171 | 125 |

TABLE 23

| | Dopant | FWHM (nm) | Driving voltage (V) | $EQE_{max}$ (%) | Electricity efficiency (%) | Current efficiency (%) | CIEy | Conversion efficiency (%) |
|---|---|---|---|---|---|---|---|---|
| Example 2-1 | 115001 | 24 | 3.9 | 138 | 234 | 144 | 0.052 | 194 |
| Example 2-2 | 115002 | 25 | 3.8 | 135 | 206 | 127 | 0.068 | 130 |
| Comparative Example 2-1 | C1 | 40 | 5.9 | 100 | 100 | 100 | 0.070 | 100 |

TABLE 23-continued

| | Dopant | FWHM (nm) | Driving voltage (V) | EQE$_{max}$ (%) | Electricity efficiency (%) | Current efficiency (%) | CIEy | Conversion efficiency (%) |
|---|---|---|---|---|---|---|---|---|
| Comparative Example 2-2 | C2 | 34 | 5.7 | 111 | 143 | 111 | 0.076 | 102 |
| Comparative Example 2-3 | C3 | 34 | 5.2 | 133 | 294 | 220 | 0.179 | 86 |

TABLE 24

| | Sensitizer | Dopant | Driving voltage (V) | EQE$_{max}$ (%) | Electricity efficiency (lm/W) | Current efficiency (Cd/A) | CIEy | Conversion efficiency (Cd/A/y) |
|---|---|---|---|---|---|---|---|---|
| Example 3-1 | DMAC-DPS | 115001 | 6.5 | 108 | 112 | 112 | 0.173 | 106 |
| Example 3-2 | Ir(cb)$_3$ | 115001 | 5.9 | 89 | 98 | 98 | 0.192 | 84 |
| Comparative Example 3-1 | Ir(cb)$_3$ | C3 | 5.8 | 100 | 100 | 100 | 0.165 | 100 |

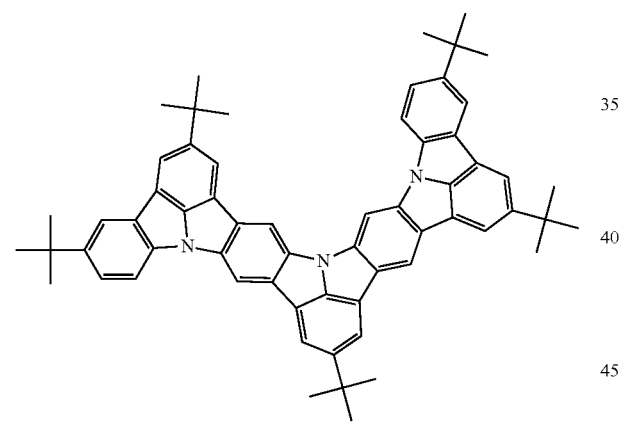

115001

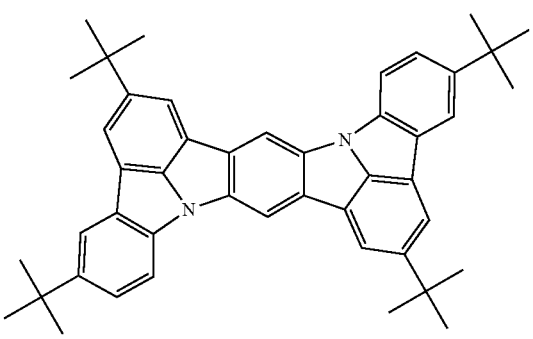

C1

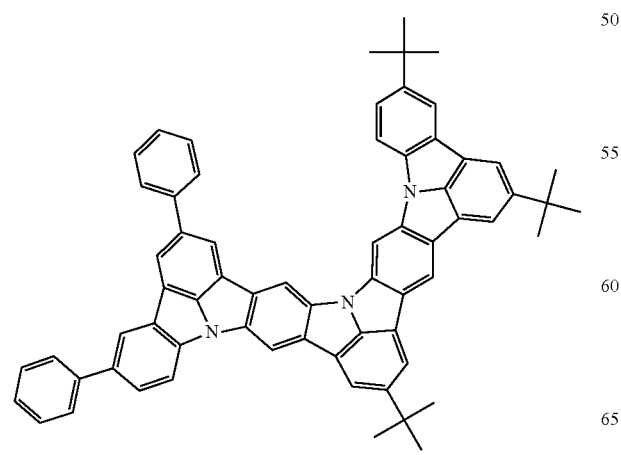

115002

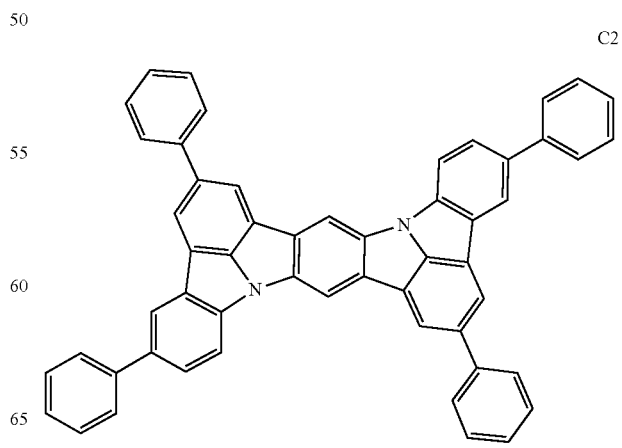

C2

-continued

3913
-continued

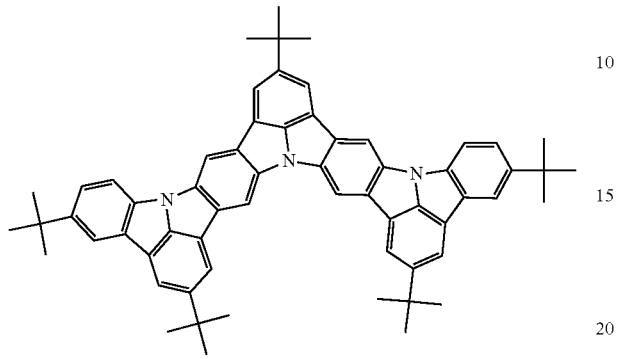

C3

Referring to the results of Tables 22 to 24, the organic light-emitting devices of the Examples were found to have high colorimetric purity and/or high efficiency, as compared with the organic light-emitting device of the Comparative Examples. In particular, Comparative Example 1-3 was found to have a relatively great FWHM and a significantly deteriorated conversion efficiency, i.e., efficiency at a desired CIEy, as compared with Examples 1-1 and 1-2. That is, even when 3 ICz(s) are included, a specific geometrical structure needs to be satisfied to provide an organic light-emitting device having high colorimetric purity and/or high efficiency.

In addition, referring to the results of Tables 22 to 24, the heterocyclic compound was found to be applicable to organic light-emitting devices that emit according to various mechanisms. On the other hand, Compounds C1 to C3 did not emit in devices having a similar structure as Example 3-1. Thus, comparative devices that correspond to Example 3-1 were not be manufactured by using Compounds C1 to C3. Likewise, Compounds C1 and C2 did not emit in devices having a similar structure as Example 3-2. Thus, comparative devices that correspond to Example 3-2 were not be manufactured by using Compounds C1 and C2.

As apparent from the foregoing description, an organic light-emitting device including the heterocyclic compound may have improved efficiency and/or colorimetric purity.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A heterocyclic compound represented by one of Formulae 11, 12, and 14 to 17:

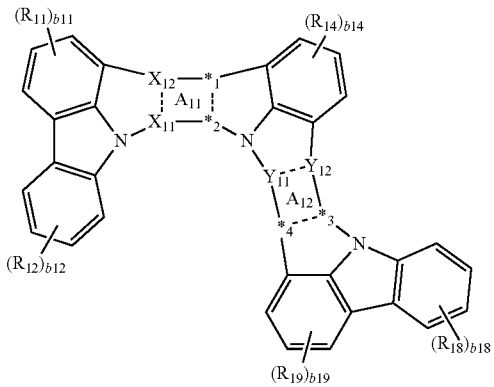

Formula 11

Formula 12

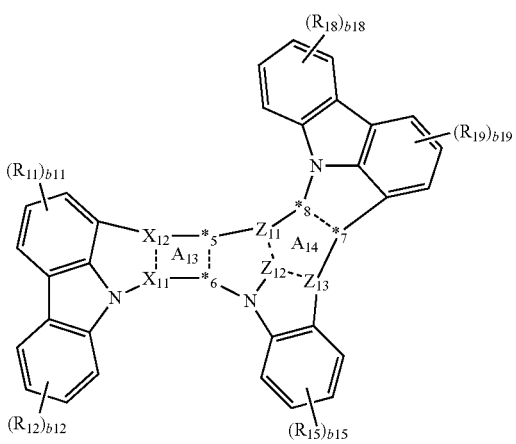

Formula 14

-continued

Formula 15

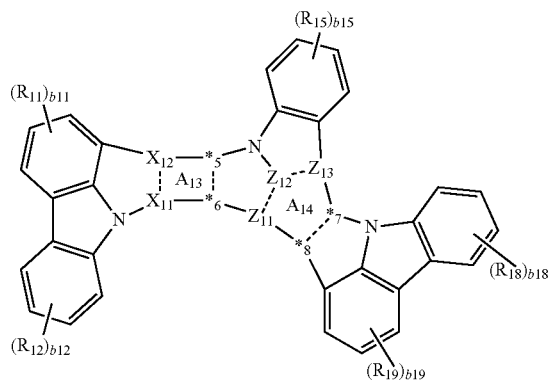

Formula 16

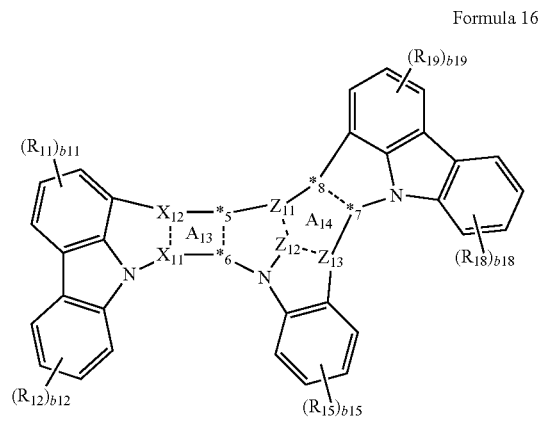

Formula 17

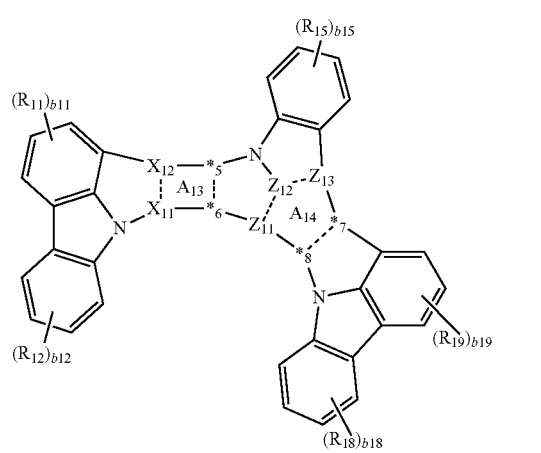

wherein, in Formulae 11, 12, and 14 to 17, $A_{11}$ and $A_{13}$ are each independently a group represented by Formula 2-1, $A_{12}$ is a group represented by Formula 2-2, $A_{14}$ is a group represented by Formula 2-3, 2-1

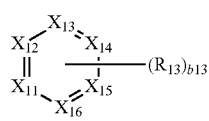

-continued 2-2

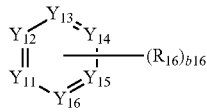

2-3

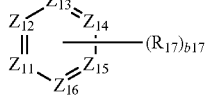

wherein, in Formulae 2-1 to 2-3, $X_{11}$ to $X_{16}$, $Y_{11}$ to $Y_{16}$, and $Z_{11}$ to $Z_{16}$ are each independently a carbon atom, any suitable two adjacent groups of $X_{13}$ to $X_{16}$ are respectively *1 and *2 in Formulae 11 and 12 or *5 and *6 in Formulae 14 to 17, any suitable two adjacent groups of $Y_{13}$ to $Y_{16}$ are respectively *3 and *4 in Formulae 11 and 12, and any suitable two adjacent groups of $Z_{14}$ to $Z_{16}$ are respectively *7 and *8 in Formulae 14 to 17, in Formula 11, ii) *1 is $X_{13}$, *2 is $X_{14}$, *3 is $Y_{14}$, and *4 is $Y_{15}$, or v) *1 is $X_{14}$, *2 is $X_{15}$, *3 is $Y_{14}$, and *4 is $Y_{15}$; in Formula 12, i) *1 is $X_{13}$, *2 is $X_{14}$, *3 is $Y_{13}$, and *4 is $Y_{14}$, ii) *1 is $X_{13}$, *2 is $X_{14}$, *3 is $Y_{14}$, and *4 is $Y_{15}$, or iv) *1 is $X_{14}$, *2 is $X_{15}$, *3 is $Y_{14}$, and *4 is $Y_{15}$;

in Formula 14, i) *5 is $X_{13}$, *6 is $X_{14}$, *7 is $Z_{14}$, and *8 is $Z_{15}$, iii) *5 is $X_{14}$, *6 is $X_{15}$, *7 is $Z_{14}$, and *8 is $Z_{15}$, or iv) *5 is $X_{14}$, *6 is $X_{15}$, *7 is $Z_{15}$, and *8 is $Z_{16}$; in Formula 15, iii) *5 is $X_{14}$, *6 is $X_{15}$, *7 is $Z_{14}$, and *8 is $Z_{15}$; in Formula 16, iii) *5 is $X_{14}$, *6 is $X_{15}$, *7 is $Z_{14}$, and *8 is $Z_{15}$, or iv) *5 is $X_{14}$, *6 is $X_{15}$, *7 is $Z_{15}$, and *8 is $Z_{16}$; and in Formula 17, iv) *5 is $X_{14}$, *6 is $X_{15}$, *7 is $Z_{15}$, and *8 is $Z_{16}$, $R_{11}$ to $R_{19}$ are each independently hydrogen, deuterium, —F, —Cl, —Br, —I, —SF$_5$, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkyl aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkyl heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent aromatic condensed polycyclic group, a substituted or unsubstituted monovalent aromatic condensed heteropolycyclic group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —Ge($Q_1$)($Q_2$)($Q_3$), —C($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), b11, b14, and b19 are each independently 0, 1, 2, or 3,
b12, b15, and b18 are each independently 0, 1, 2, 3, or 4,
b13 and b16 are each independently 0, 1, or 2, and
b17 is 0 or 1,
wherein $Q_1$ to $Q_3$ are each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkyl aryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent aromatic condensed polycyclic group, a monovalent aromatic condensed heteropolycyclic group, a monovalent non-aromatic condensed polycyclic group, a monovalent non-aromatic condensed heteropolycyclic group, a $C_1$-$C_{60}$ alkyl group substituted with at least one deuterium, —F, a cyano group, a $C_1$-$C_{60}$ alkyl group, a $C_6$-$C_{60}$ aryl group, or any combination thereof, or a $C_6$-$C_{60}$ aryl group substituted with at least one deuterium, —F, a cyano group, a $C_1$-$C_{60}$ alkyl group, a $C_6$-$C_{60}$ aryl group, or any combination thereof.

2. The heterocyclic compound of claim 1, wherein $R_{11}$ to $R_{19}$ are each independently: hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, a $C_1$-$C_{20}$ alkenyl group, a $C_1$-$C_{20}$ alkoxy group, or a $C_1$-$C_{20}$ alkylthio group;
a $C_1$-$C_{20}$ alkyl group, a $C_1$-$C_{20}$ alkenyl group, a $C_1$-$C_{20}$ alkoxy group, or a $C_1$-$C_{20}$ alkylthio group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a ($C_1$-$C_{20}$ alkyl)cyclopentyl group, a ($C_1$-$C_{20}$ alkyl)cyclohexyl group, a ($C_1$-$C_{20}$ alkyl)cycloheptyl group, a ($C_1$-$C_{20}$ alkyl)cyclooctyl group, a ($C_1$-$C_{20}$ alkyl) adamantanyl group, a ($C_1$-$C_{20}$ alkyl) norbornanyl group, a ($C_1$-$C_{20}$ alkyl) norbornenyl group, a ($C_1$-$C_{20}$ alkyl)cyclopentenyl group, a ($C_1$-$C_{20}$ alkyl)cyclohexenyl group, a ($C_1$-$C_{20}$ alkyl)cycloheptenyl group, a ($C_1$-$C_{20}$ alkyl) bicyclo[1.1.1]pentyl group, a ($C_1$-$C_{20}$ alkyl) bicyclo[2.1.1]hexyl group, a ($C_1$-$C_{20}$ alkyl) bicyclo[2.2.1]heptyl group, a ($C_1$-$C_{20}$ alkyl) bicyclo[2.2.2]octyl group, a phenyl group, a ($C_1$-$C_{20}$ alkyl)phenyl group, a biphenyl group, a terphenyl group, a naphthyl group, a pyridinyl group, a pyrimidinyl group, or any combination thereof;
a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl) phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, or an azadibenzothiophenyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a deuterated $C_2$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a ($C_1$-$C_{20}$ alkyl)cyclopentyl group, a ($C_1$-$C_{20}$ alkyl)cyclohexyl group, a ($C_1$-$C_{20}$ alkyl)cycloheptyl group, a ($C_1$-$C_{20}$ alkyl)cyclooctyl group, a ($C_1$-$C_{20}$ alkyl) adamantanyl group, a ($C_1$-$C_{20}$ alkyl) norbornanyl group, a ($C_1$-$C_{20}$ alkyl) norbornenyl group, a ($C_1$-$C_{20}$ alkyl)cyclopentenyl group, a ($C_1$-$C_{20}$ alkyl)cyclohexenyl group, a ($C_1$-$C_{20}$ alkyl)cycloheptenyl group, a ($C_1$-$C_{20}$ alkyl) bicyclo[1.1.1]pentyl group, a ($C_1$-$C_{20}$ alkyl) bicyclo[2.1.1]hexyl group, a ($C_1$-$C_{20}$ alkyl) bicyclo[2.2.1]heptyl group, a ($C_1$-$C_{20}$ alkyl) bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, or any combination thereof; or
—Si(Q₁)(Q₂)(Q₃), —Ge(Q₁)(Q₂)(Q₃), —C(Q₁)(Q₂)(Q₃), —B(Q₁)(Q₂), or —N(Q₁)(Q₂),
wherein $Q_1$ to $Q_3$ are each independently:
deuterium, —F, —CH₃, —CD₃, —CD₂H, —CDH₂, —CH₂CH₃, —CH₂CD₃, —CH₂CD₂H, —CH₂CDH₂, —CHDCH₃, —CHDCD₂H, —CHDCDH₂, —CHDCD₃, —CD₂CD₃, —CD₂CD₂H, —CD₂CDH₂, —CF₃, —CF₂H, —CFH₂, —CH₂CF₃, —CH₂CF₂H, —CH₂CFH₂, —CHFCH₃, —CHFCF₂H, —CHFCFH₂, —CHFCF₃, —CF₂CF₃, —CF₂CF₂H, or —CF₂CFH₂; or
an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

3. The heterocyclic compound of claim 1, wherein the heterocyclic compound is represented by one of Formulae 11-2, 11-5, 12-1, 12-2, 12-4, 14-1, 14-3, 14-4, 15-3, 16-3, 16-4, and 17-4:

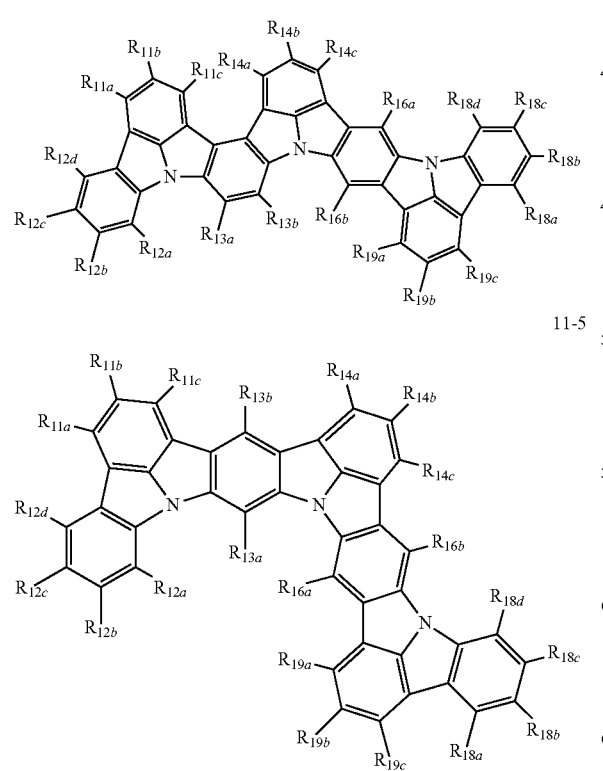

11-2

11-5

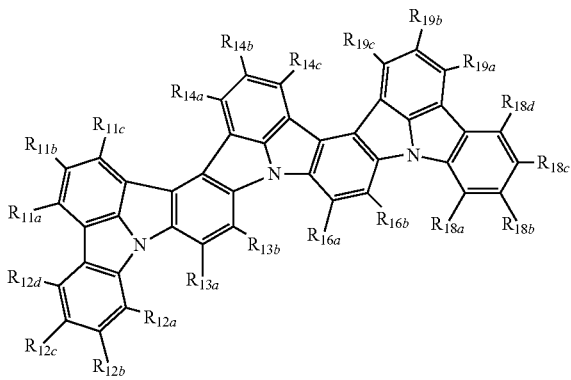

12-1

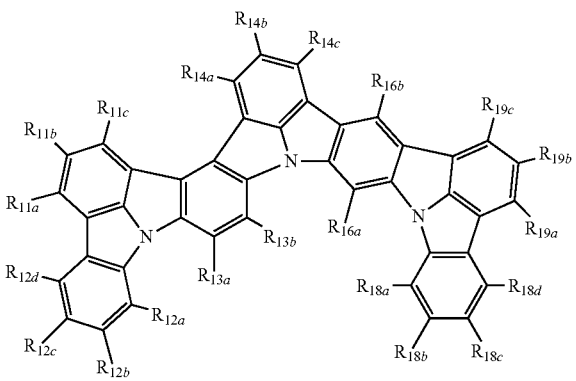

12-2

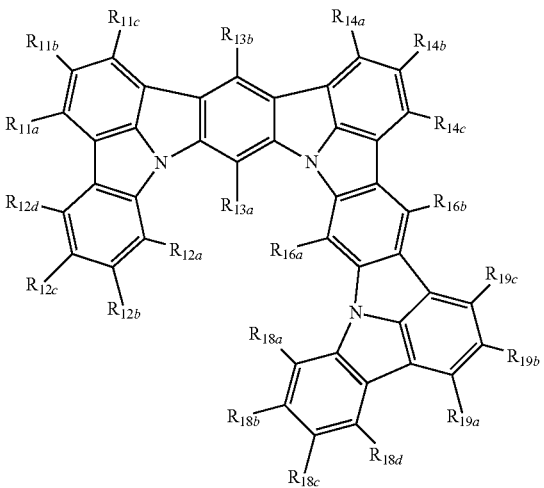

12-4

-continued
14-1
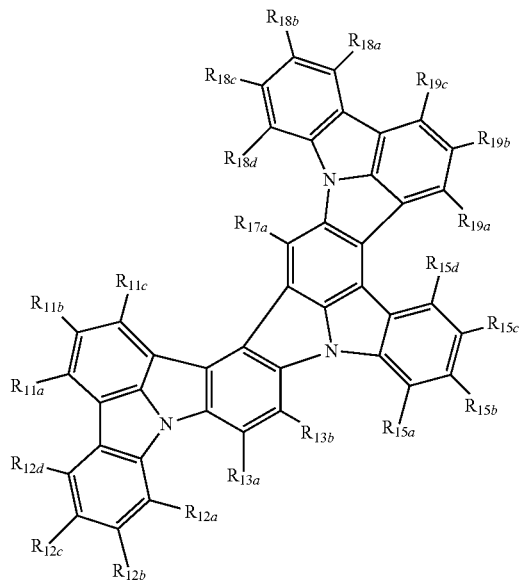
14-3
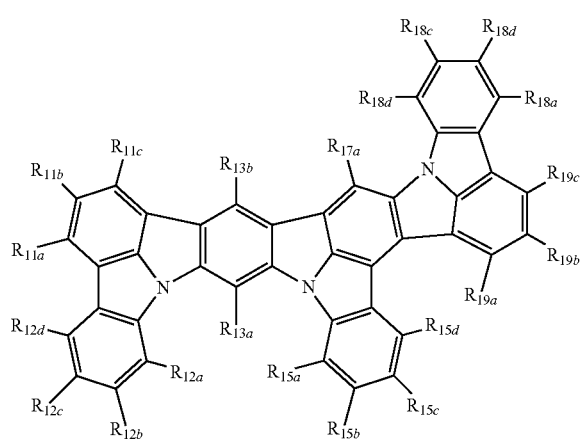
14-4
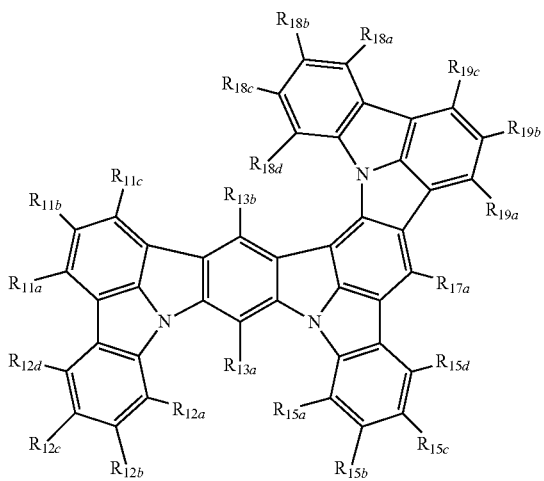
-continued
15-3
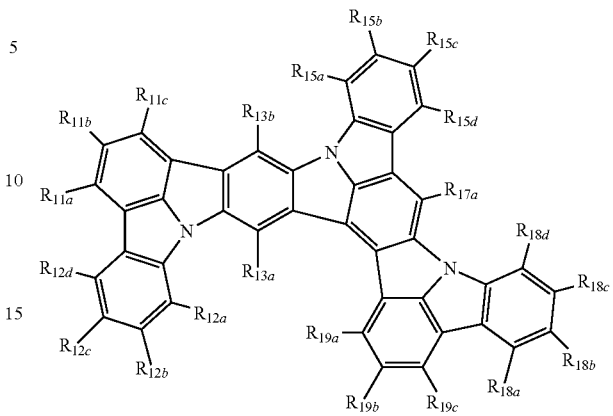
16-3
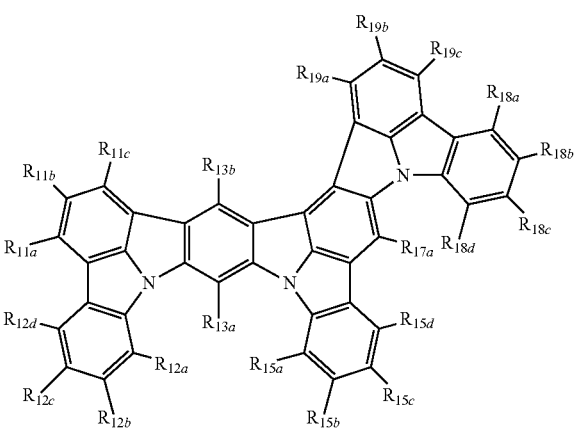
16-4
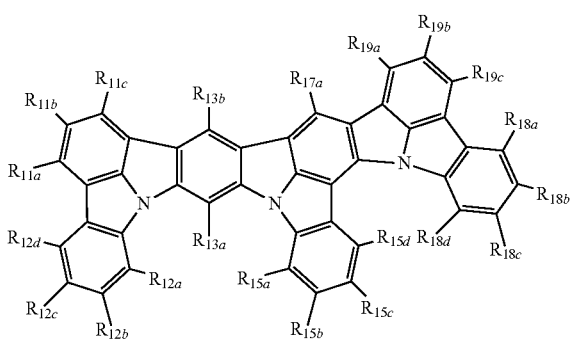

17-4

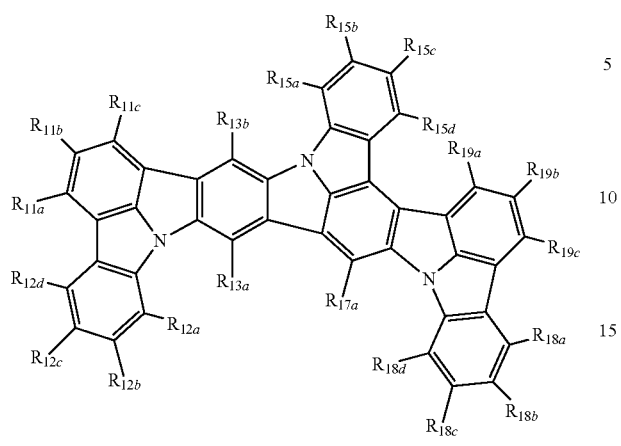

wherein, in Formulae 11-2, 11-5, 12-1, 12-2, 12-4, 14-1, 14-3, 14-4, 15-3, 16-3, 16-4, and 17-4,
$R_{11a}$ to $R_{11c}$ are each understood by referring to the description of $R_{11}$ provided in claim 1,
$R_{12a}$ to $R_{12d}$ are each understood by referring to the description of $R_{12}$ provided in claim 1,
$R_{13a}$ and $R_{13b}$ are each understood by referring to the description of $R_{13}$ provided in claim 1,
$R_{14a}$ to $R_{14c}$ are each understood by referring to the description of $R_{14}$ provided in claim 1,
$R_{15a}$ to $R_{15d}$ are each understood by referring to the description of $R_{15}$ provided in claim 1,
$R_{16a}$ and $R_{16b}$ are each understood by referring to the description of $R_{16}$ provided in claim 1,
$R_{17a}$ is understood by referring to the description of $R_{17}$ provided in claim 1,
$R_{18a}$ to $R_{18d}$ are each understood by referring to the description of $R_{18}$ provided in claim 1, and
$R_{19a}$ to $R_{19c}$ are each understood by referring to the description of $R_{19}$ provided in claim 1.

4. The heterocyclic compound of claim 3, wherein $R_{11a}$ to $R_{11c}$, $R_{12a}$ to $R_{12d}$, $R_{13a}$ and $R_{13b}$, $R_{14a}$ to $R_{14c}$, $R_{15a}$ to $R_{15d}$, $R_{16a}$ and $R_{16b}$, $R_{17a}$, $R_{18a}$ to $R_{18d}$, and $R_{19a}$ to $R_{19c}$ are each independently hydrogen, deuterium, —F, —$CH_3$, —$CD_3$, —$CD_2H$, —$CDH_2$, —$CF_3$, —$CF_2H$, —$CFH_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, a group represented by one of Formulae 10-359 to 10-380, a group represented by one of Formulae 10-359 to 10-380 in which at least one hydrogen is substituted with deuterium, a group represented by one of Formulae 10-359 to 10-380 in which at least one hydrogen is substituted with —F, —Si($Q_1$)($Q_2$)($Q_3$), —Ge($Q_1$)($Q_2$)($Q_3$), —C($Q_1$)($Q_2$)($Q_3$), —B($Q_1$)($Q_2$), or —N($Q_1$)($Q_2$),
wherein $Q_1$ to $Q_3$ are each independently:
deuterium, —F, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, —$CD_2CDH_2$, —$CF_3$, —$CF_2H$, —$CFH_2$, —$CH_2CF_3$, —$CH_2CF_2H$, —$CH_2CFH_2$, —$CHFCH_3$, —$CHFCF_2H$, —$CHFCFH_2$, —$CHFCF_3$, —$CF_2CF_3$, —$CF_2CF_2H$, or —$CF_2CFH_2$;
or
an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

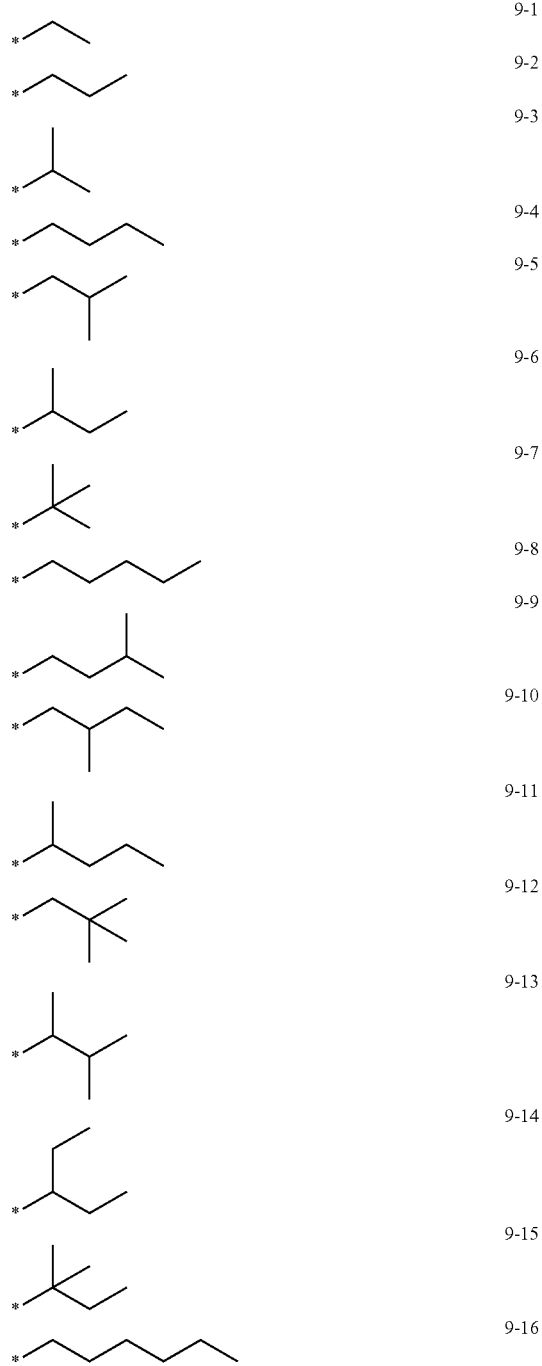

3925
-continued
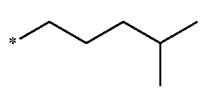
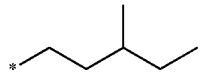
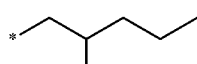
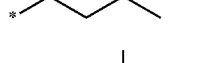
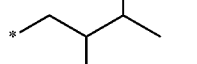
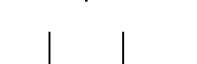
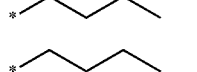
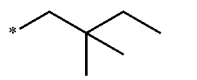
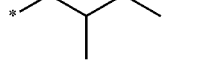
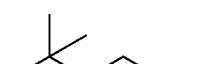
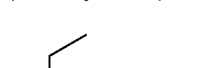
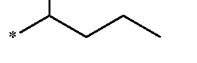
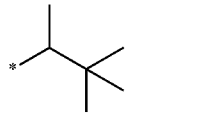
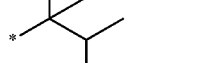
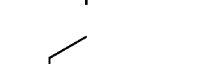
3926
-continued
9-17
9-18 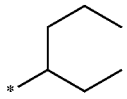
9-19 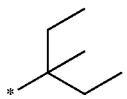
9-20
9-21 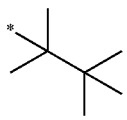
9-22
9-23 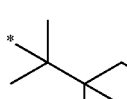
9-24
9-25 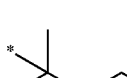
9-26 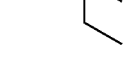
9-27 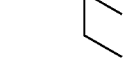
9-28 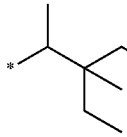
9-29 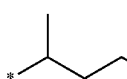
9-30 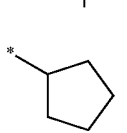
9-31 
9-32
9-33
9-34
9-35
9-36
9-37
9-38
9-39
10-1 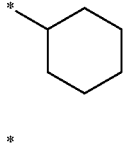
10-2 
10-3
10-4 

-continued
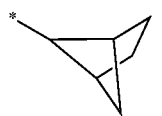 
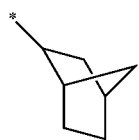 
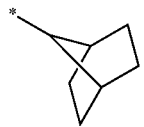 
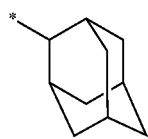 
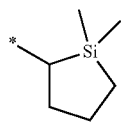 
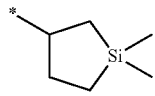 
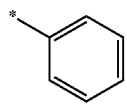 
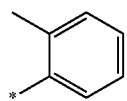 
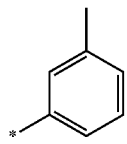 
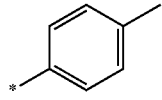 
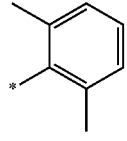 
-continued
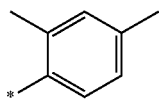 10-5
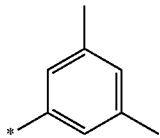 10-6
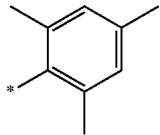 10-7
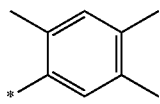 10-8
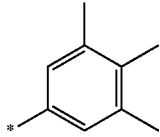 10-9
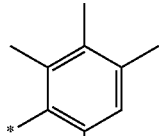 10-10
10-11
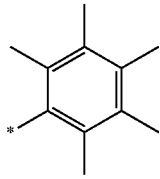 10-12
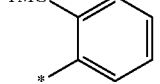 10-13
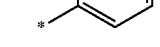
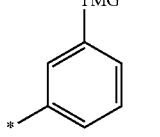 10-14
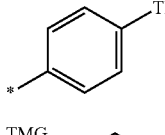 10-15
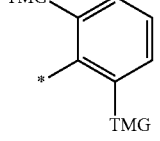 10-16
10-17
10-18
10-19
10-20
10-21
10-22
10-23
10-24
10-25
10-26
10-27

3929
-continued
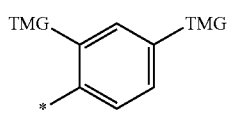
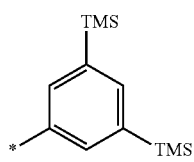
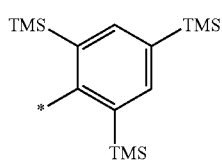
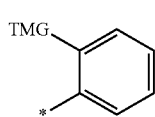
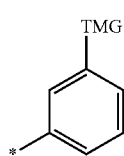
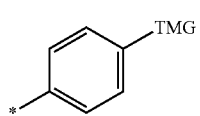
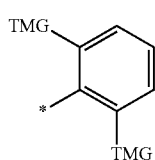
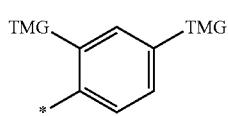
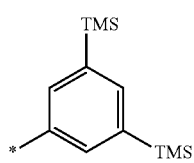
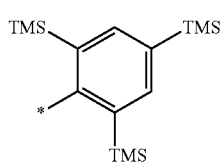
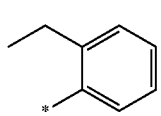
3930
-continued
10-28
10-29
10-30
10-31
10-32
10-33
10-34
10-35
10-36
10-37
10-38
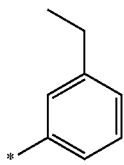
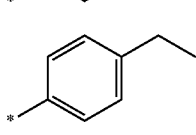
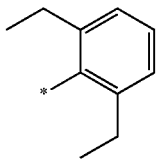
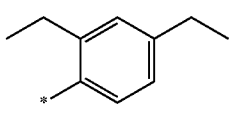
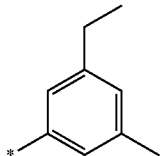
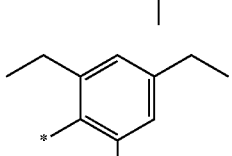
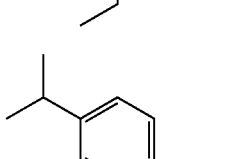
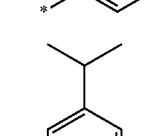
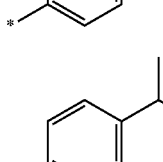
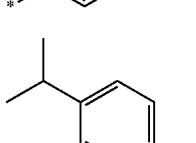
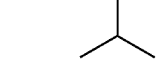
10-39
10-40
10-41
10-42
10-43
10-44
10-45
10-46
10-47
10-48

-continued
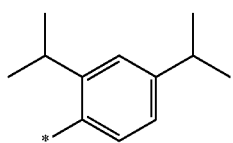
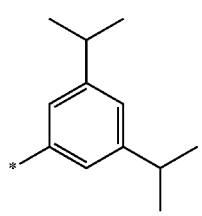
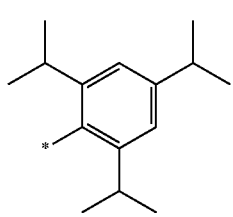
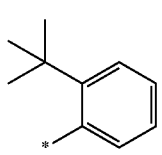
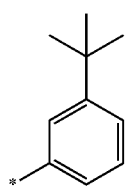
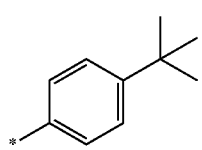
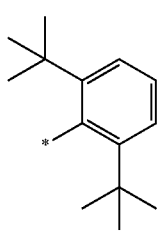
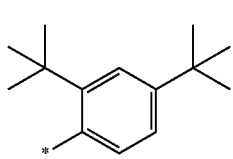
-continued
10-49
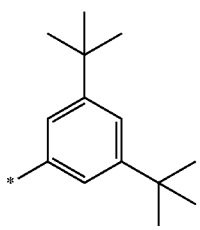
10-50
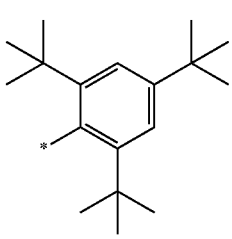
10-51
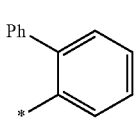
10-52
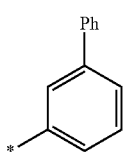
10-53
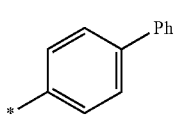
10-54
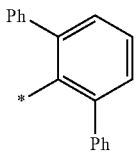
10-55
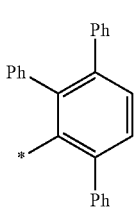
10-56
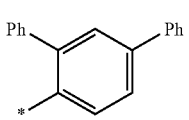
10-57
10-58
10-59
10-60
10-61
10-62
10-63
10-64
10-65
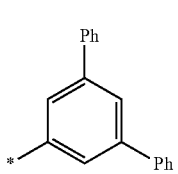

| | |
|---|---|
| 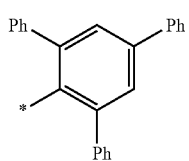 | 10-66 |
| 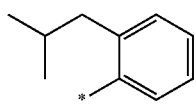 | 10-67 |
| 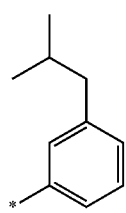 | 10-68 |
| 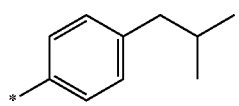 | 10-69 |
| 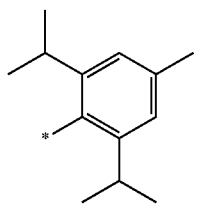 | 10-70 |
| 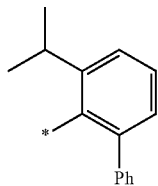 | 10-71 |
| 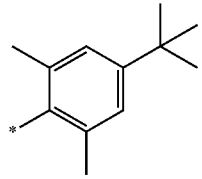 | 10-72 |
| 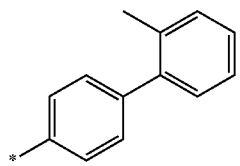 | 10-73 |
| 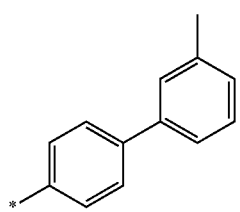 | 10-74 |
| | |
|---|---|
| 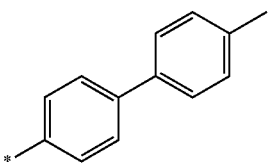 | 10-75 |
| 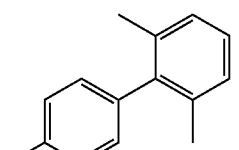 | 10-76 |
| 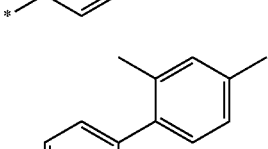 | 10-77 |
| 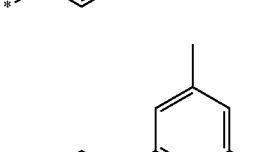 | 10-78 |
| 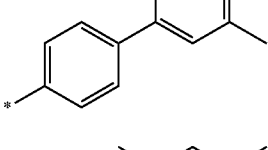 | 10-79 |
| 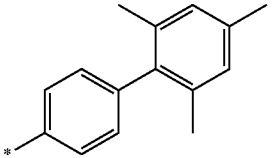 | 10-80 |
|  | 10-81 |
| 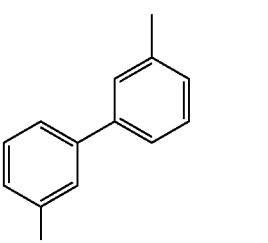 | 10-82 |
| 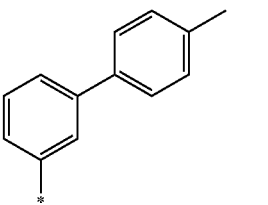 | |

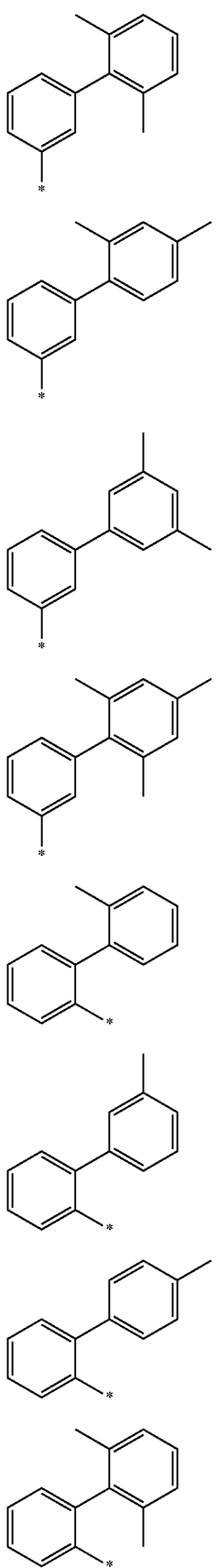
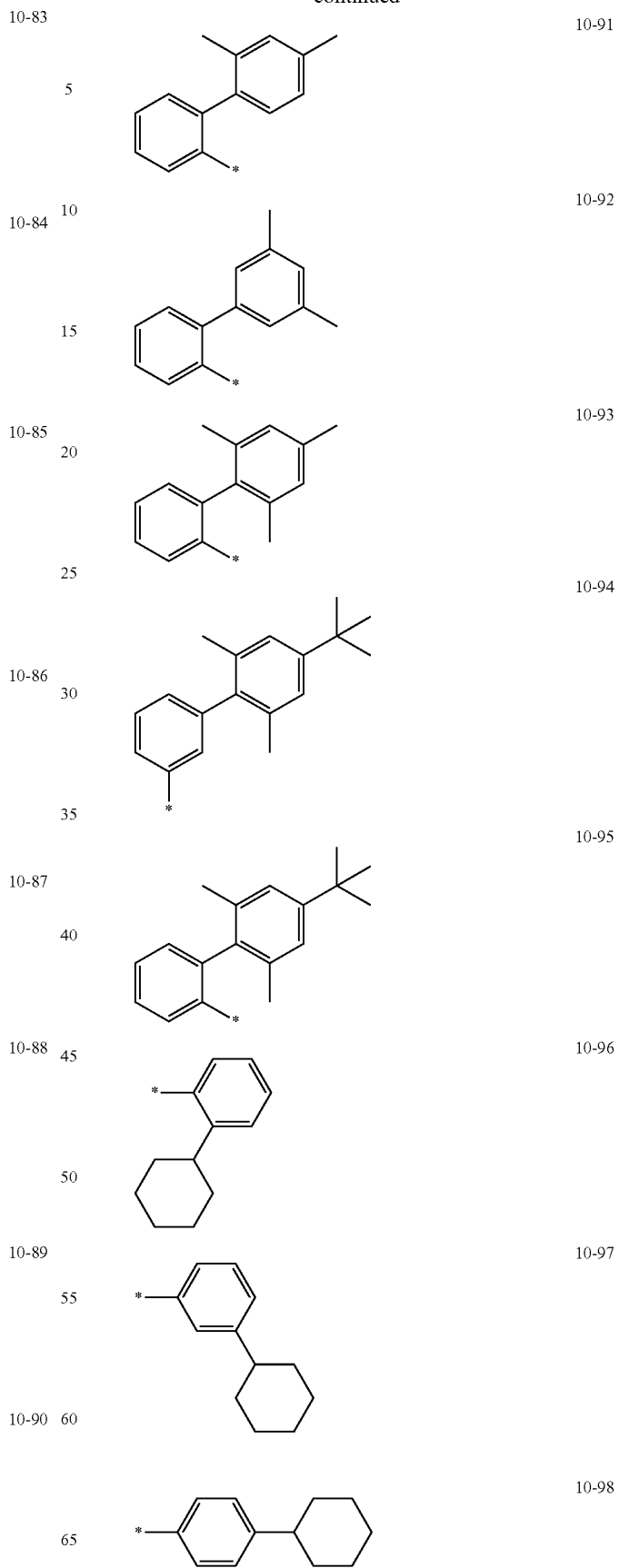

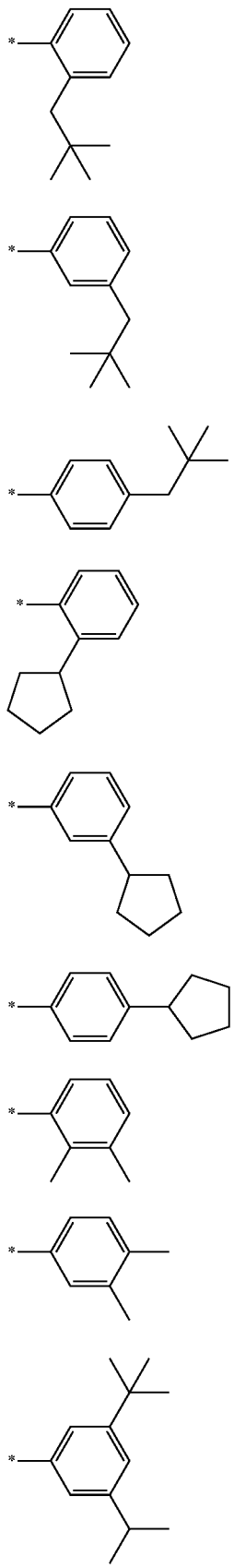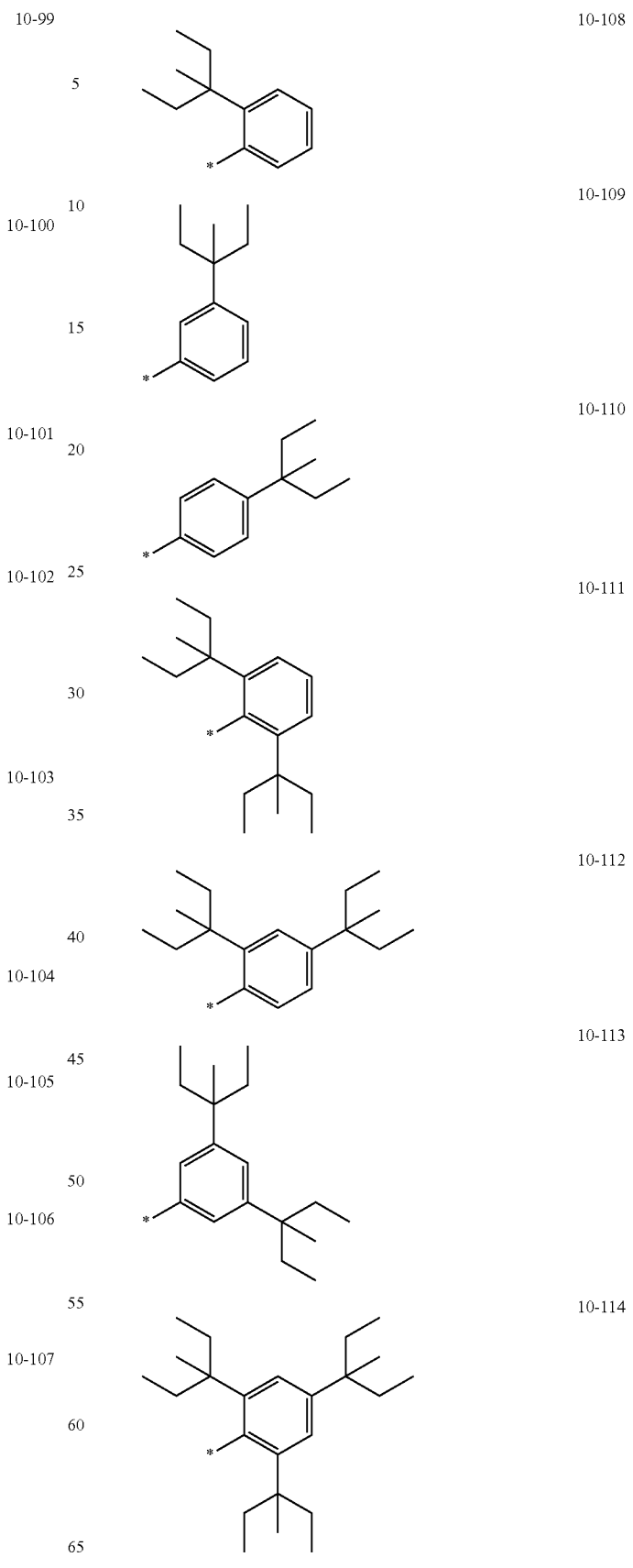

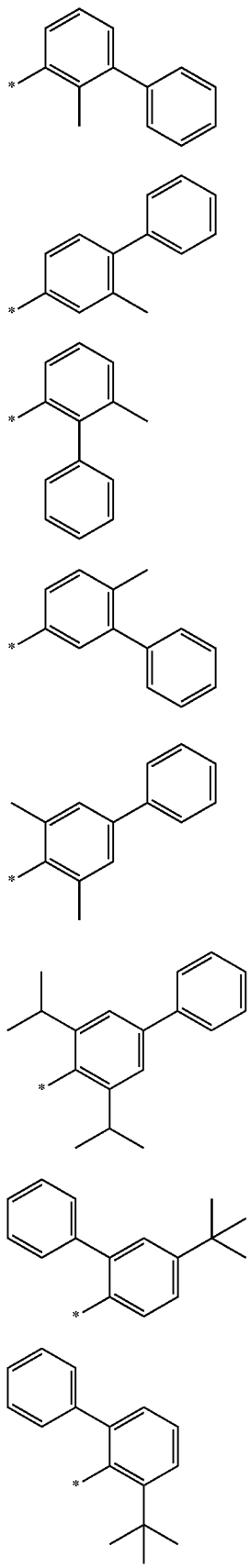
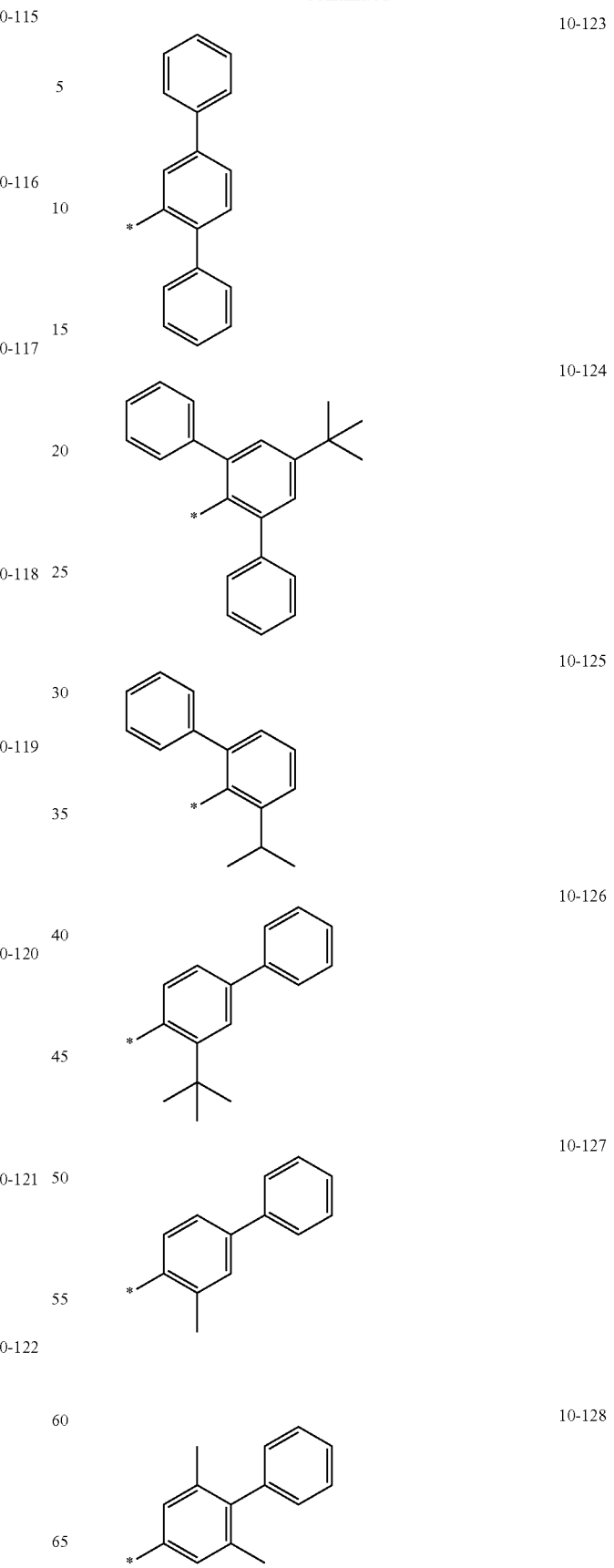

-continued
10-129 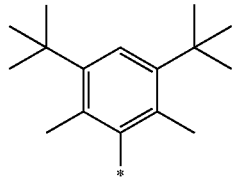
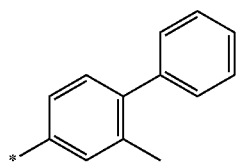
10-130 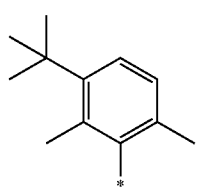
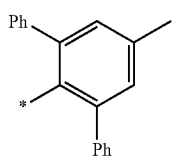
10-359
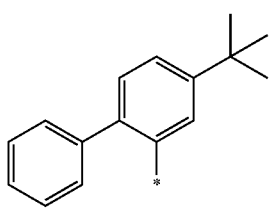 10-360 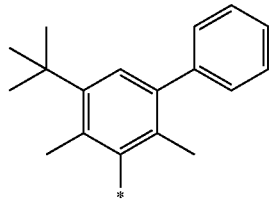
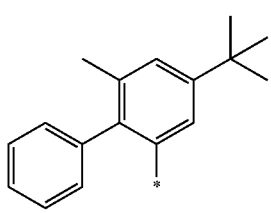 10-361 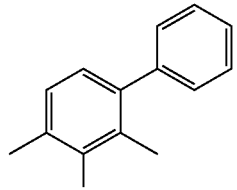
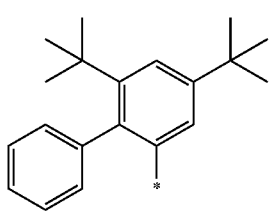 10-362 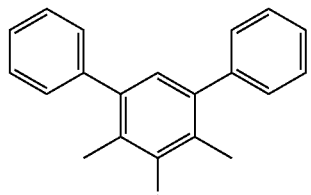
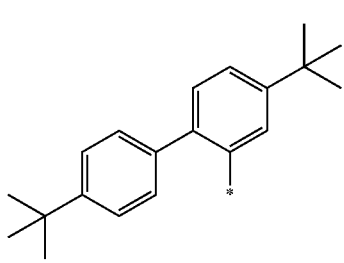 10-363 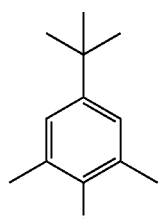
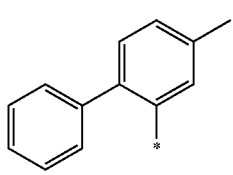 10-364 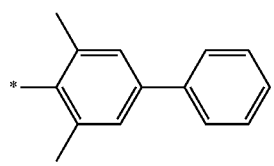
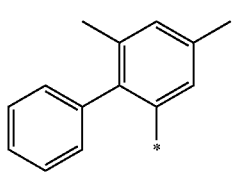 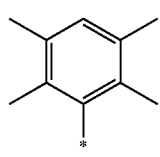
10-365
10-366
10-367
10-368
10-369
10-370
10-371
10-372

10-373
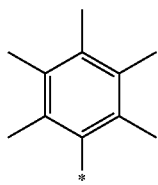

10-374
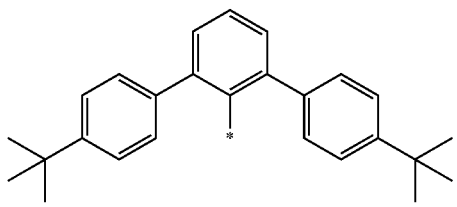

10-375
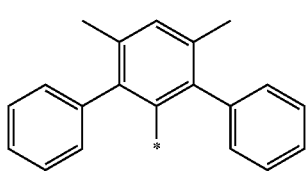

10-376
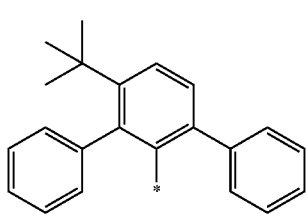

10-377
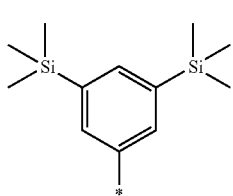

10-378
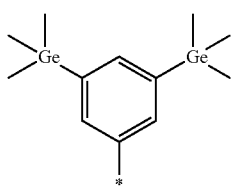

10-379
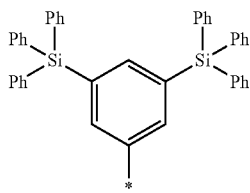

10-380
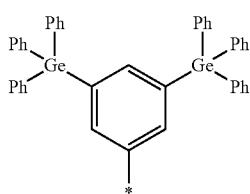

5. The heterocyclic compound of claim 4, wherein at least one of $R_{11b}$, $R_{12c}$, $R_{14b}$, $R_{18b}$, and $R_{19b}$ in Formulae 11-2 and 11-5, at least one of $R_{11b}$, $R_{12c}$, $R_{14b}$, $R_{18c}$, and $R_{19b}$ in Formulae 12-1, 12-2, and 12-4, and at least one of $R_{11b}$, $R_{12c}$, $R_{15c}$, $R_{18b}$, and $R_{19b}$ in Formulae 14-1, 14-3, 14-4, 15-3, 16-3, 16-4, and 17-4 is —$CH_3$, —$CD_3$, —$CD_2H$, —$CDH_2$, —$CF_3$, —$CF_2H$, —$CFH_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, a group represented by one of Formulae 10-359 to 10-380, a group represented by one of Formulae 10-359 to 10-380 in which at least one hydrogen is substituted with deuterium, a group represented by one of Formulae 10-359 to 10-380 in which at least one hydrogen is substituted with —F, —$Si(Q_1)(Q_2)(Q_3)$, —$Ge(Q_1)(Q_2)(Q_3)$, —$C(Q_1)(Q_2)(Q_3)$, —$B(Q_1)(Q_2)$, or —$N(Q_1)(Q_2)$, wherein $Q_1$ to $Q_3$ are each independently:
deuterium, —F, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCDH_2$, —$CHDCD_3$, —$CD_2CD_3$, —$CD_2CD_2H$, —$CD_2CDH_2$, —$CF_3$, —$CF_2H$, —$CFH_2$, —$CH_2CF_3$, —$CH_2CF_2H$, —$CH_2CFH_2$, —$CHFCH_3$, —$CHFCF_2H$, —$CHFCFH_2$, —$CHFCF_3$, —$CF_2CF_3$, —$CF_2CF_2H$, or —$CF_2CFH_2$; or an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

6. The heterocyclic compound of claim 5, wherein the remaining substituents are each hydrogen.

7. The heterocyclic compound of claim 1, wherein the heterocyclic compound is represented by Formula 11-5:

11-5

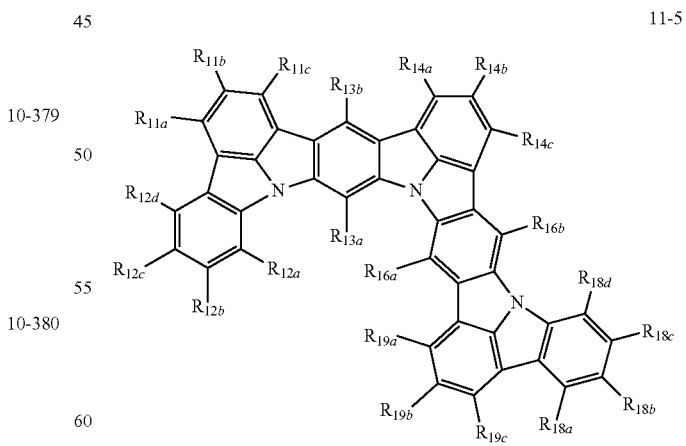

wherein, in Formula 11-5,
$R_{11a}$ to $R_{11c}$ are each understood by referring to the description of $R_{11}$ provided in claim 1,
$R_{12a}$ to $R_{12d}$ are each understood by referring to the description of $R_{12}$ provided in claim 1, $R_{13a}$ and $R_{13b}$ are each understood by referring to the description of $R_{13}$ provided in claim 1, $R_{14a}$ to $R_{14c}$ are each understood by referring to the description of $R_{14}$ provided in claim 1, $R_{15a}$ to $R_{15d}$ are each understood by referring to the description of $R_{15}$ provided in claim 1, $R_{16a}$ and $R_{18b}$ are each understood by referring to the description of $R_{16}$ provided in claim 1, $R_{17a}$ is understood by referring to the description of $R_{17}$ provided in claim 1, $R_{18a}$ to $R_{18d}$ are each understood by referring to the description of $R_{18}$ provided in claim 1, and $R_{19a}$ to $R_{19c}$ are each understood by referring to the description of $R_{19}$ provided in claim 1.

8. The heterocyclic compound of claim 7, wherein at least one of $R_{11b}$, $R_{12c}$, $R_{14b}$, $R_{18b}$, and $R_{19b}$ is —$CH_3$, —$CD_3$, —$CD_2H$, —$CDH_2$, —$CF_3$, —$CF_2H$, —$CFH_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 10-1 to 10-130, a group represented by one of Formulae 10-1 to 10-130 in which at least one hydrogen is substituted with deuterium, a group represented by one of Formulae 10-1 to 10-130 in which at least one hydrogen is substituted with —F, a group represented by one of Formulae 10-359 to 10-380, a group represented by one of Formulae 10-359 to 10-380 in which at least one hydrogen is substituted with deuterium, a group represented by one of Formulae 10-359 to 10-380 in which at least one hydrogen is substituted with —F, —$Si(Q_1)(Q_2)(Q_3)$, —$Ge(Q_1)(Q_2)(Q_3)$, —$C(Q_1)(Q_2)(Q_3)$, —$B(Q_1)(Q_2)$, or —$N(Q_1)(Q_2)$, wherein $Q_1$ to $Q_3$ are each independently:
deuterium, —F, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, —$CD_2CDH_2$, —$CF_3$, —$CF_2H$, —$CFH_2$, —$CH_2CF_3$, —$CH_2CF_2H$, —$CH_2CFH_2$, —$CHFCH_3$, —$CHFCF_2H$, —$CHFCFH_2$, —$CHFCF_3$, —$CF_2CF_3$, —$CF_2CF_2H$, or —$CF_2CFH_2$; or
an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, —F, a $C_1$-$C_{10}$ alkyl group, a phenyl group, or any combination thereof.

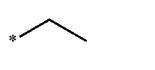
9-1

9-2

9-3

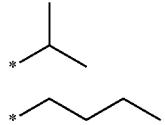
9-4

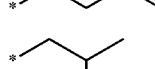
9-5

-continued 9-6

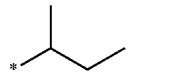
9-7

9-8

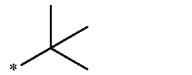
9-9

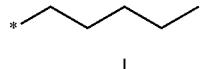
9-10

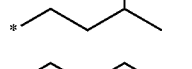
9-11

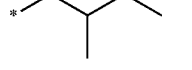
9-12

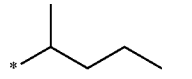
9-13

9-14

9-15

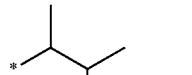
9-16

9-17

9-18

9-19

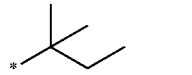
9-20

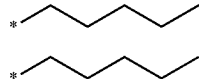
9-21

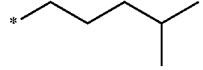
9-22

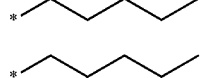
9-23

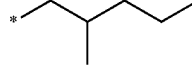

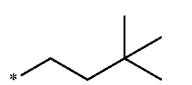

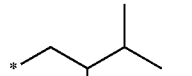

3947
-continued
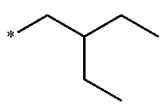 9-24
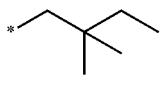 9-25
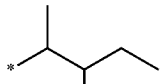 9-26
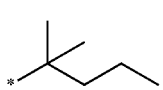 9-27
 9-28
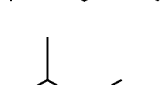 9-29
 9-30
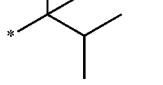 9-31
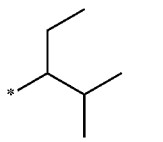 9-32
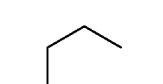 9-33
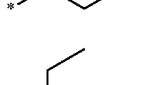 9-34
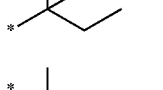 9-35
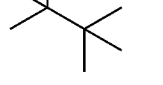 9-36
3948
-continued
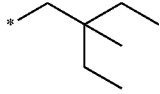 9-37
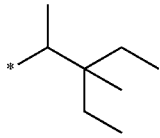 9-38
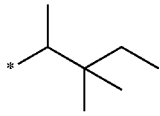 9-39
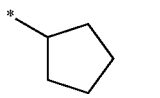 10-1
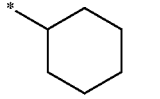 10-2
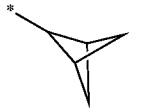 10-3
 10-4
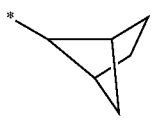 10-5
 10-6
 10-7
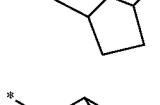 10-8
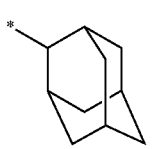 10-9

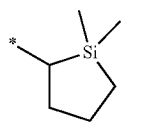
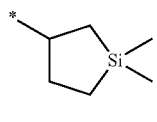
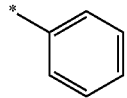
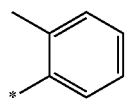
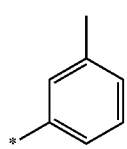
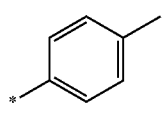
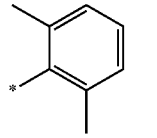
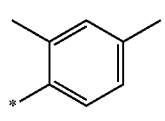
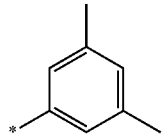
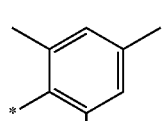
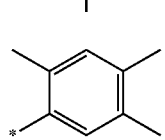
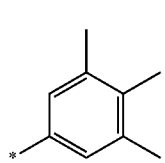
10-10
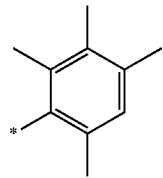
10-11
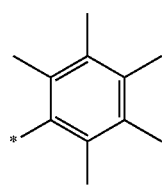
10-12
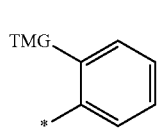
10-13
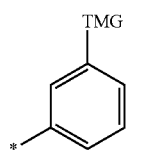
10-14
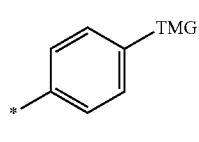
10-15
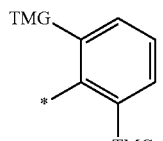
10-16
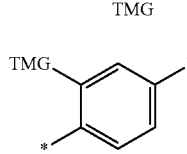
10-17
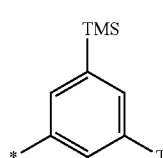
10-18
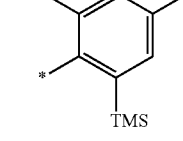
10-19
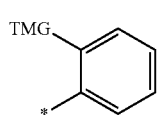
10-20
10-21

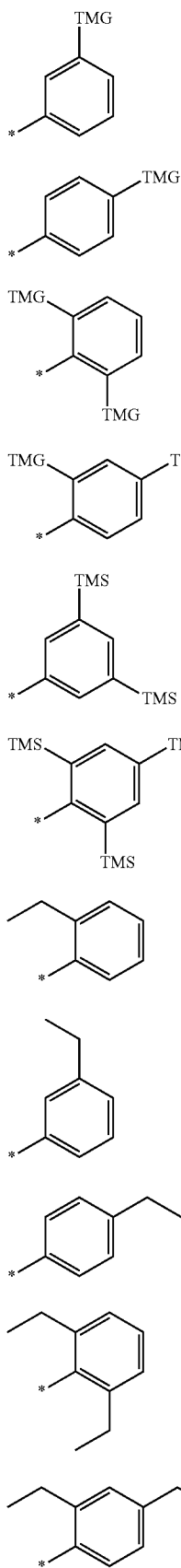
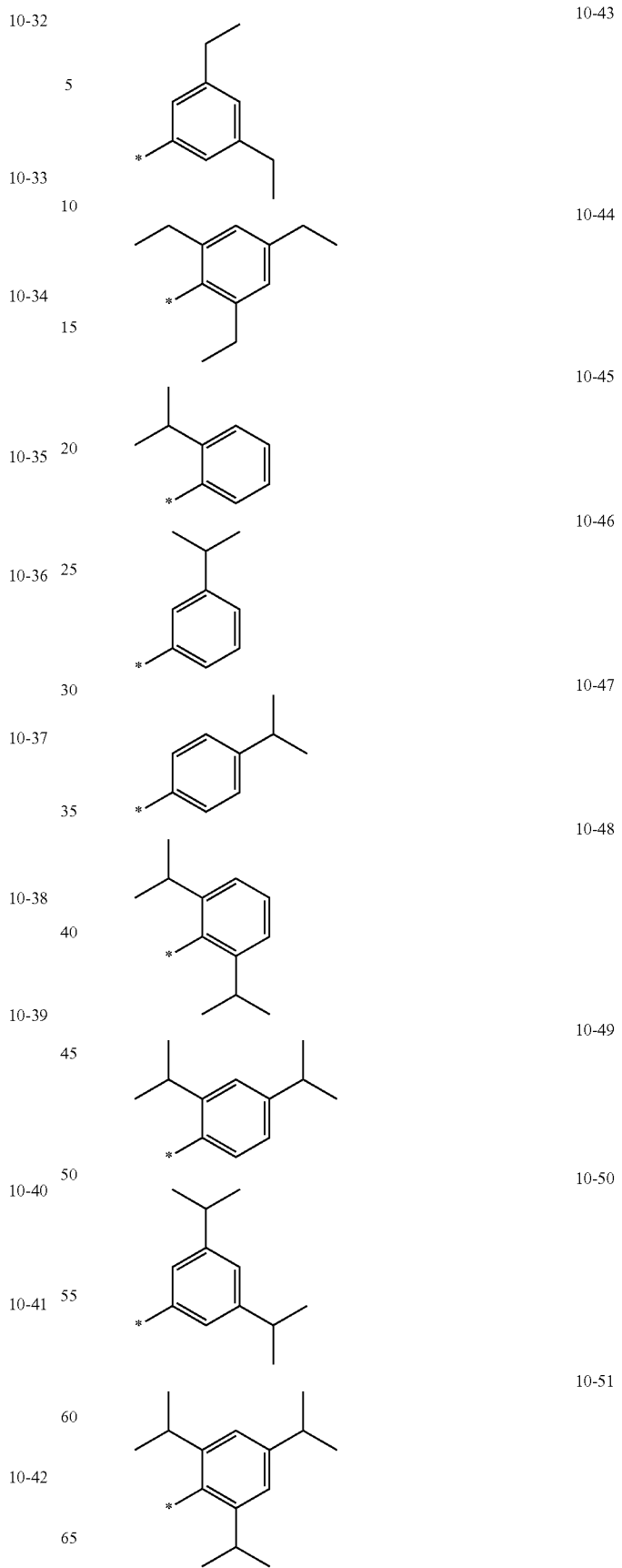

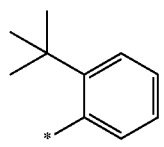
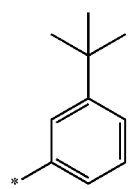
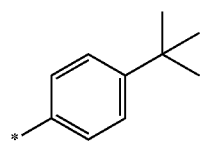
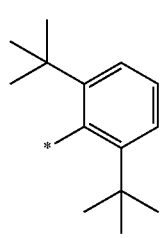
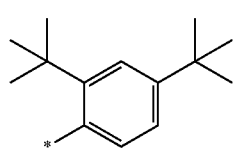
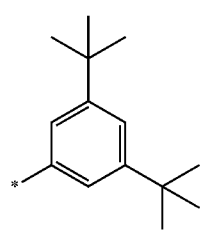
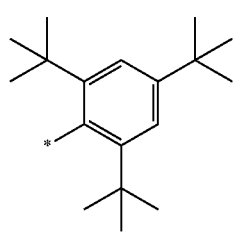
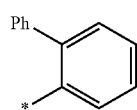
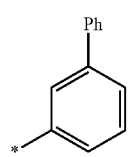
10-52
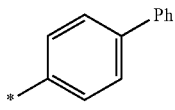
10-53
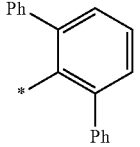
10-54
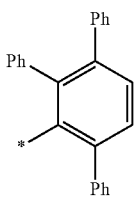
10-55
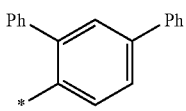
10-56
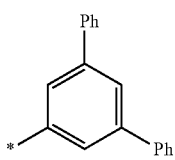
10-57
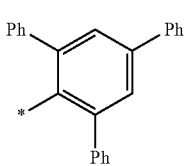
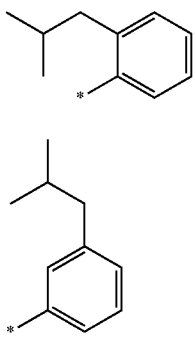
10-58
10-59
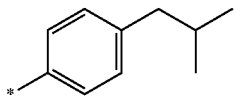
10-60
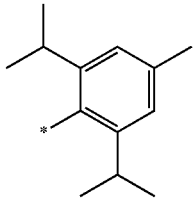

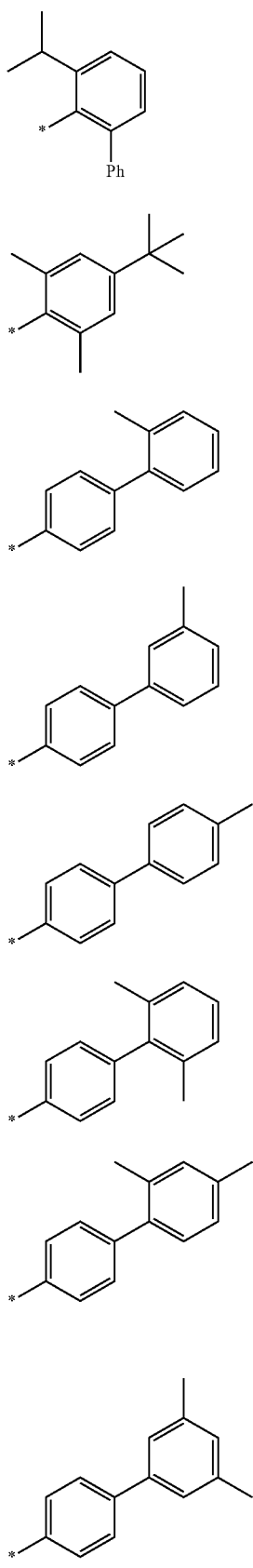

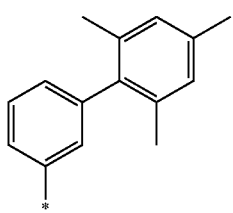
10-86
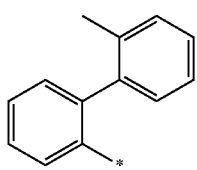
10-87
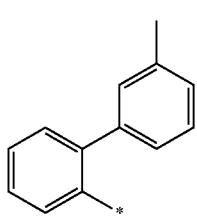
10-88
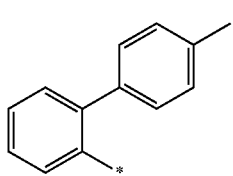
10-89
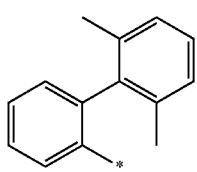
10-90
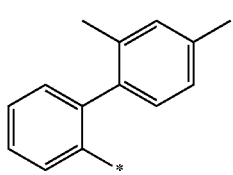
10-91
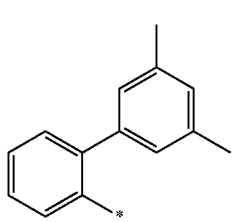
10-92
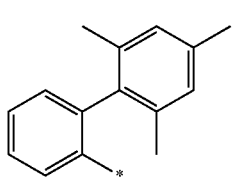
10-93
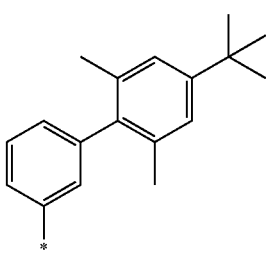
10-94
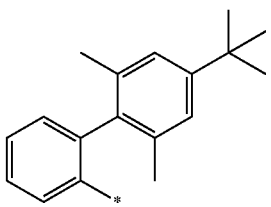
10-95
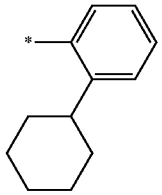
10-96
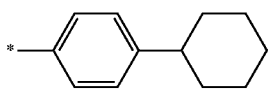
10-97
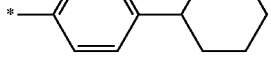
10-98
10-99
10-100
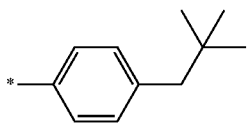
10-101

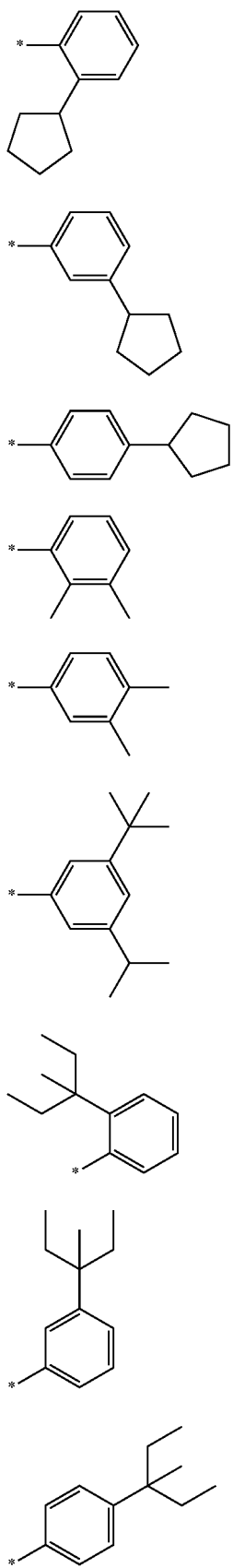
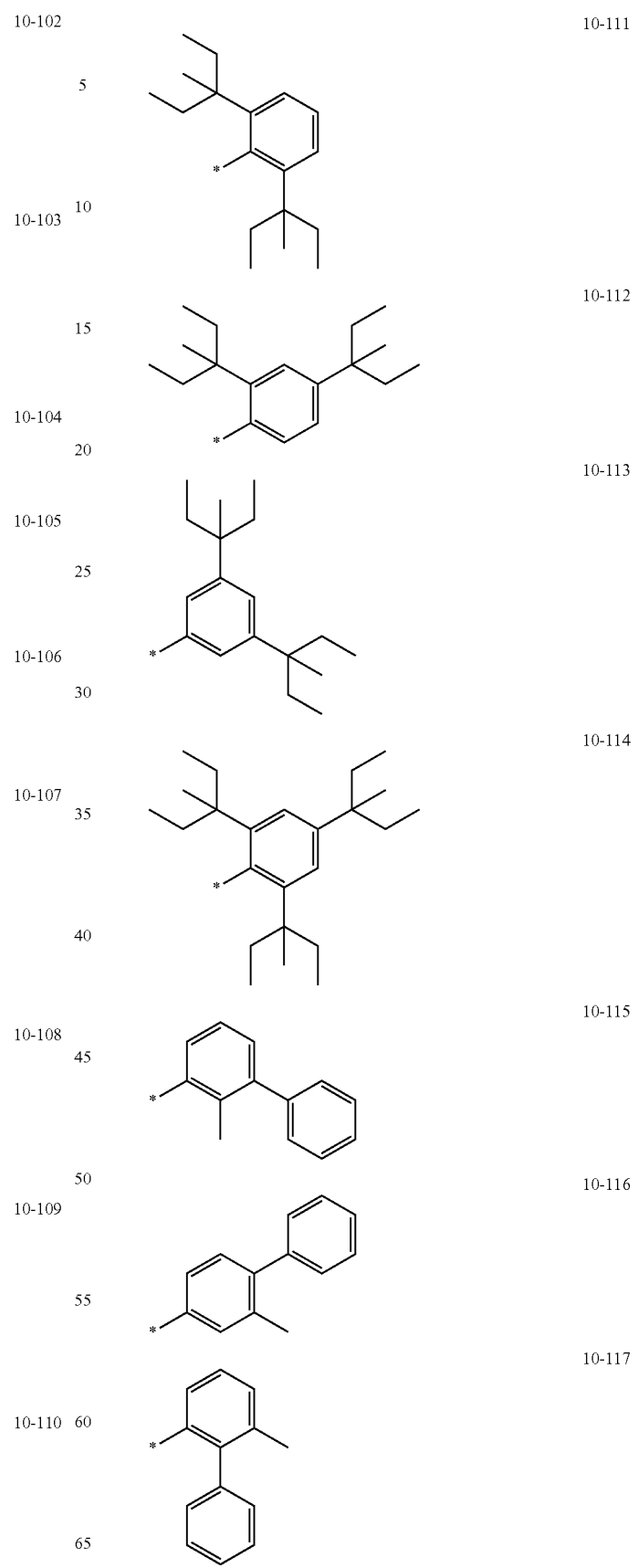

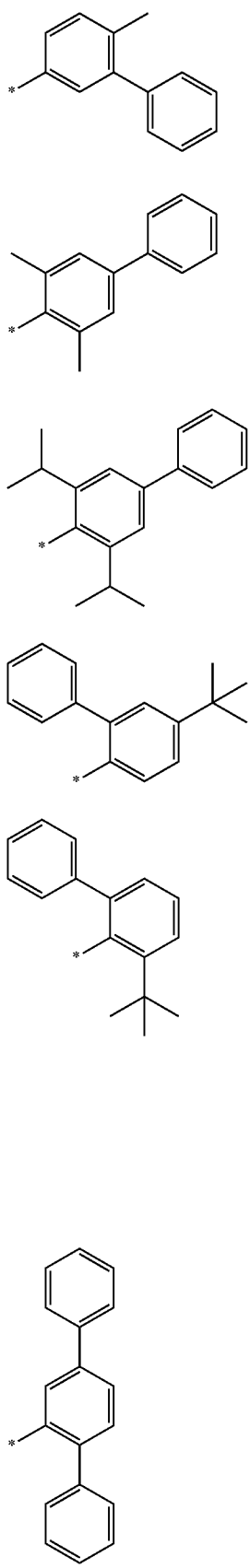
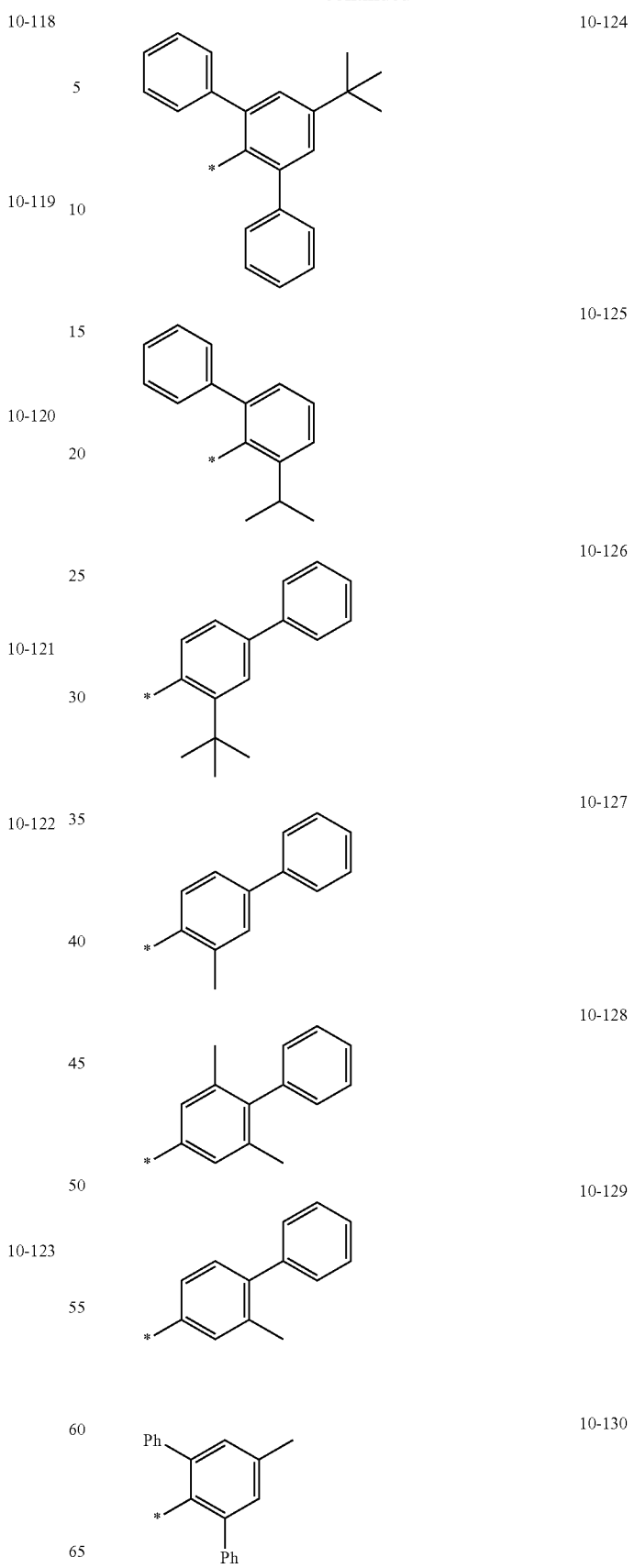

10-359
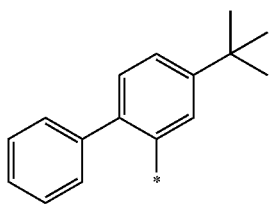
10-360
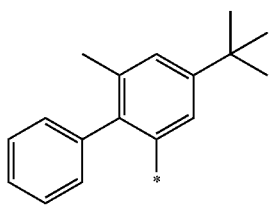
10-361
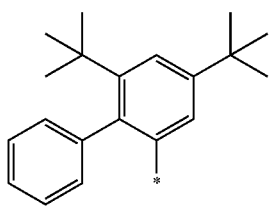
10-362
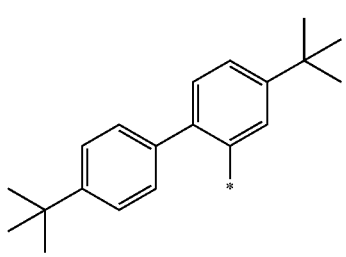
10-363
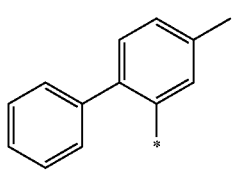
10-364
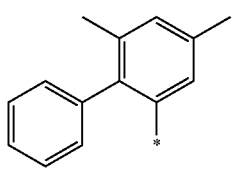
10-365
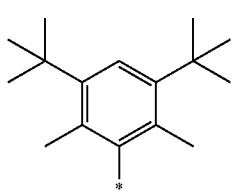
10-366
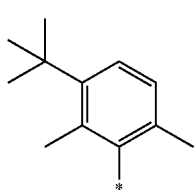
10-367
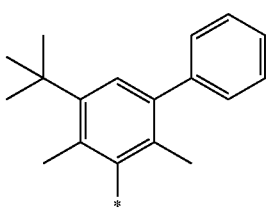
10-368
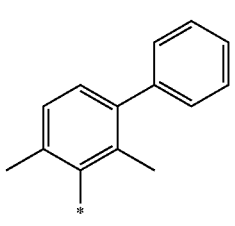
10-369
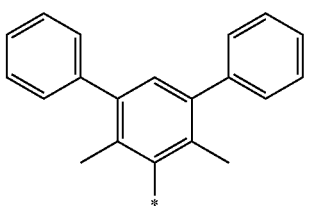
10-370
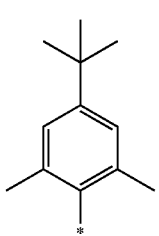
10-371
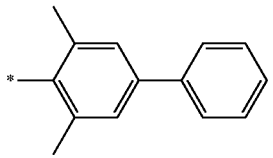
10-372
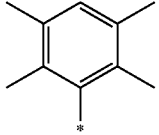
10-373
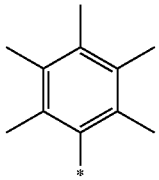
10-374
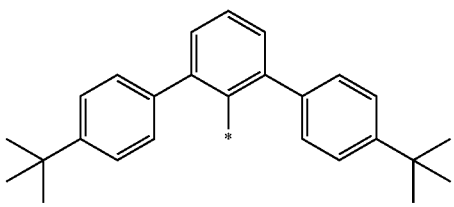

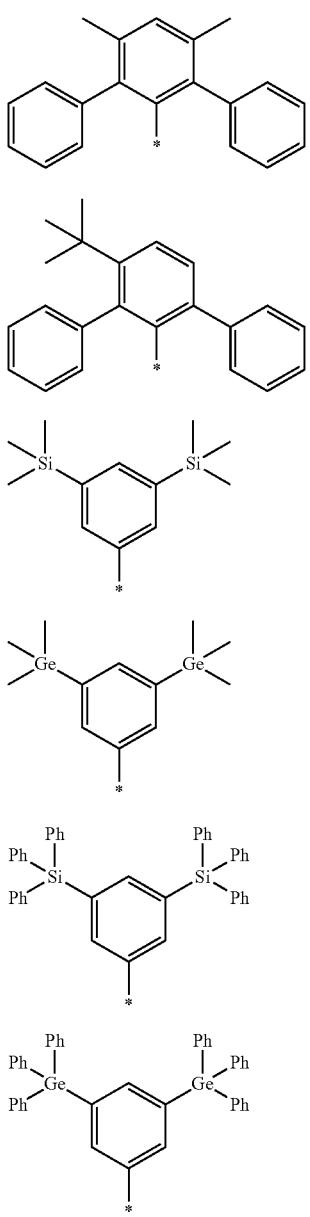

9. The heterocyclic compound of claim 8, wherein the remaining substituents are each hydrogen.

10. The heterocyclic compound of claim 1, wherein the heterocyclic compound satisfies Conditions 1 to 4:

$$\Delta E_{ST} > \Delta E_{ST2} + \Delta E'_{TT} \quad \text{Condition 1}$$

$$0 \text{ eV} < \Delta E_{ST2} + \Delta E'_{TT} \leq 1.0 \text{ eV} \quad \text{Condition 2}$$

$$0 \text{ eV} < \Delta E'_{TT} \leq 0.30 \text{ eV} \quad \text{Condition 3}$$

$$\Delta E_{ST2} > 0 \text{ eV} \quad \text{Condition 4}$$

wherein, in Conditions 1 to 4, $\Delta E_{ST}$ indicates a difference between a lowest excited singlet energy level calculated in an $S_1$ equilibrium structure of the heterocyclic compound and a lowest excited triplet energy level calculated in a $T_1$ equilibrium structure of the heterocyclic compound, $\Delta E_{ST2}$ indicates a difference between a lowest excited singlet energy level calculated in an $S_1$ equilibrium structure of the heterocyclic compound and a second lowest excited triplet energy level calculated in a $T_2$ equilibrium structure of the heterocyclic compound, and $\Delta E'_{TT}$ indicates a difference between a second lowest excited triplet energy level calculated in an $T_2$ equilibrium structure of the heterocyclic compound and a lowest excited triplet energy level calculated in a $T_2$ equilibrium structure of the heterocyclic compound.

11. An organic light-emitting device comprising: a first electrode;

a second electrode; and an organic layer between the first electrode and the second electrode and comprising an emission layer, wherein the organic layer comprises the heterocyclic compound of claim 1.

12. The organic light-emitting device of claim 11, wherein the emission layer comprises the heterocyclic compound.

13. The organic light-emitting device of claim 12, wherein the emission layer comprises a host and an emitter, the host is different from the emitter, and the emitter comprises the heterocyclic compound.

14. The organic light-emitting device of claim 13, wherein the emission layer emits blue light.

15. The organic light-emitting device of claim 13, wherein the emitter is a fluorescence emitter and/or a delayed fluorescence emitter.

16. The organic light-emitting device of claim 12, wherein the emission layer comprises a host, an emitter, and a sensitizer, the host, the emitter, and the sensitizer are different from one other, and the emitter comprises the heterocyclic compound.

17. The organic light-emitting device of claim 16, wherein the emission layer emits blue light.

18. The organic light-emitting device of claim 16, wherein the emitter is a fluorescence emitter and/or a delayed fluorescence emitter.

19. The organic light-emitting device of claim 16, wherein the heterocyclic compound satisfy Condition 5:

$$0\mu s < T_{decay}(HC) < 5\mu s \quad \text{Condition 5}$$

wherein, in Condition 5, $T_{decay}$ (HC) indicates a decay time of the heterocyclic compound.

20. An electronic apparatus comprising the organic light-emitting device of claim 11.

* * * * *